US007135558B1

(12) United States Patent
Yandell

(10) Patent No.: US 7,135,558 B1
(45) Date of Patent: Nov. 14, 2006

(54) **ISOLATED *DROSOPHILA* PROTEINS ESSENTIAL FOR SURVIVAL NUCLEIC ACID MOLECULES ENCODING ESSENTIAL *DROSOPHILA* PROTEINS, AND USES THEREOF AS INSECTICIDAL TARGETS**

(75) Inventor: Mark D. Yandell, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 1001 days.

(21) Appl. No.: 09/619,049

(22) Filed: Jul. 18, 2000

Related U.S. Application Data

(60) Provisional application No. 60/187,241, filed on Mar. 3, 2000, provisional application No. 60/186,663, filed on Mar. 3, 2000, provisional application No. 60/175,685, filed on Jan. 12, 2000, provisional application No. 60/175,763, filed on Jan. 12, 2000, provisional application No. 60/171,627, filed on Dec. 23, 1999, provisional application No. 60/171,590, filed on Dec. 23, 1999.

(51) Int. Cl.
*C07H 21/02* (2006.01)
*C12Q 1/68* (2006.01)

(52) U.S. Cl. .......................................... 536/23.1; 435/6

(58) Field of Classification Search ............... 536/22.1; 435/350.1, 6
See application file for complete search history.

(56) References Cited

OTHER PUBLICATIONS

U.S. Appl. No. 09/618,893, filed Jan. 2000, Anibal, Cravchik.*
U.S. Appl. No. 09/618,893, filed Jul. 2000, Anibal Cravchik.*
U.S. Appl. No. 09/614,150, filed Jul. 2000, Venter J. Craig.*

* cited by examiner

*Primary Examiner*—Suryaprabha Chunduru
(74) *Attorney, Agent, or Firm*—Lin Sun-Hoffman; Celera Genomics

(57) ABSTRACT

The present invention provides amino acid sequences and transcript sequences that are encoded by 511 genes within the *Drosophila melanogaster* genome that are essential for survival, the *Drosophila* proteins of the present invention. The present invention specifically provides isolated protein and nucleic acid molecules, methods of identifying orthologs and paralogs of the *Drosophila* proteins and methods of identifying modulators of the *Drosophila* proteins (e.g. insecticides).

8 Claims, 836 Drawing Sheets

Celera Sequence No. : 142000013384069
CCGGCCAGCTGAACGTGGTGGGCGCCGTGGGACTGGGCATCGCCTTTGTCCAGCTGTTCGGGCTGATCACCTCGATGCTGCTGTTCTGCACGGTG
AAGCACAAGCGGGCCTCGGACACCTACAAGTCATACTCCCCGTCGATTGATCCTCAGACCCGCACCAGCAGTTGGGAAGATTGAACGCGCCTGTG
ACGGTGGTAGGCGGACTTCTAAATTGGGGGGTTGCAGTCGGCCTCCCGAACTCCCTGTCGCTATCTCTATTCCTTTTGTTAACTCTCTTAGTTTC
TAATTTATTCTGCGAAATGTGCCAAAAATTAATTTAATTCAAAGTGTATTTTTTTTTGTTTTTTTGTTTGTAATCTGTAGGCGGAGACAAGTCGA
AACAAAATTGAACTGGCAGCAAAATGACAAATTCGCACTGGGCACAGTGTGAACATGTCATATTGCTGCCGGTGAAACAATCACATATTTAGTTA
GCAGTGTATCCATATTGTGATGTGCTCTCTAGTAGTATAGTATAAGGCCCAAGGCCCGAAACGCACCTGGAACAGGGTATAGTGCGTTCCATACT
TATCAGGCTGGCTGCTTAGCTGCAAGAGTACCTGACACATATATACAGCTAGTGTGAGTCGGAATCCTTGGACCTGGATATGCTTATGCTCGTAA
CCCTTCAACTAAACCAATATATCAACTACAATATATATTTATATATAATTATATAATACTTATGTTACTTTATGGAAATCTGTAGTATTCGAAAT
AGCAGAAACCGCAACTGCCCGAAAAGCGCGAGGAAAGCGAGAAGAGAAGAGAAAAGAAAAGAAGAGAAGACGAAGTGGAGAAAGAGGGAGCAAAT
AGTTAAAGCAAATATTACATTACTACTATGCGTATGATTATTTTATTCATACATACAAATATTTATATCGAAATGCATTCCTAAACAACATGTTC
GTGTTAAGTTACAAAATAAATTAAAGTATTTATTTAAATTACACGCCTTCTCAAAGGCCCACCAATTTGCCTCCTATGATATCCAATTGAGCCGT
GATCCCCTTCGTCACGCTGCGCGCCAACTCTTTGGGCTTCTGCAAGAGAGAAATGGGGGAAGAGAGTGGTCAAGAGAGGGAAAGCTGGCACTGG
AACTGACCTTGCTCAAAGCGAAGCGCAAGCGCACACGACGAGCGACTAATTGCATAAGCAGTGCCAGCGGGTCGTGGTACTGTCAATCTGGCTTG
AAAATAGCCAAGACTCAAGGACTTGCAGTAATACTGACAGCTAAGGCCGTAAGTTGATAGGCTCTTTCGTACGCATGTTTAAAGTATTGTTTAAA
TTTTGTTTGGCTGCTGAGCCGGTGCATCGCTGGGACCATTATGCAACGTGTGTGCGAATGGATTGACCAAGAAACAGGGCAAACAAACAAACCAA
ACACAATGGTCGCAATTTCGGCACTCCCTCACCTGAATAAAGGTGTTGAGCAGGTTGGAAAAGGCCTCGTAGCCGTTGACAATGGATCGCGAGAT
GCCGTCGAACATGTCACCGTTGTTGCCGTACTTCTCGTGCTCACTGATGGAGTCCAAAATGGGAACGGGCTGAAATCAAAACTGGGTCCTAGTGG
CTCTGGTCTTTGGTGGATATATATATGTATCACATCACTTACCTGCGCCAAATCGGCCAGCCTCTTTTGACTGTTGTCGTACACGCTCAGCACCT
TCGAGGGAATGGCCTCCTGCTCTAGATTCACCGATTCCGCCGTTTTAGCCGGAGTGGGCAGGAGAGAGATCTGCCGAAAAATAAGGGGAAGTCAC
TTGGATTTTTAAAGTATACCTCGGTTACTCACCTTGAACCCGGCGTCGCTGGCCTGCGCGTGGGTGGATTCCGCGGAGCTGTCGGCGGCATCGAA
AGCATCCTGGGCTCCGAAGTCGGCGGCCGAGACGCGGGCGTCGATGGGCGTGGCGCCATCGGGCGTGGCAGGAGCTATGGGCGTGGCACAGATGC
AGCGCATCATGGCCAAGAGCAGCAGCAGAGTATTCATCTTTTGAAGTTGCAGCATTTTCGTTAGTATGTGCGGAGAAGGGGGAAAGGGCCCAACT
ATGTGGTTTTATAACAAGGTGAAAACTTCCAAATCCAAATCCCAGGTTGAGCTTCGATCCGAAGTCTCTCGAGTCCAAAATTCAACTGAATAGCT
GCGTCTGCGCAACGATTTTATTGGTTTAACCCGACCACGAGAGTCGCCGCTTTGGACATTGAGCCACGATCGTTTTGGCTTTAGTTTGGGTTTCA
GTTGAGCACAGGTTTTCAGGGGGCAATCGGGGGTTAGCGCCTCGTGGAGCCGCTGCATAGTTATGTGTGATTATTACGTTGCATAAAATGCAAAC
TCTTTCAACGAAAATATTTTATTAAAATAATATAAATTTAATAAGATTGACCACAGAAGATTTAATTTGAATGTTTAAAATTATCTGGGATATTT
GATTCATTTAAGTAGTTCACTTAGTTCACTCTTGTTCAAAGCTCCAAGGCTTGTTCAACTTTAGGAAAACTAAAATTTTATCTAATATCTTCTTT
ATATCGCGAGAGCCGCCTAAATTTTTTCCTACAGTGTAGTGTATTGATCGTTATCGTAATGACAACAACAAATAGTCATAAAACTGTAACAATAA
CAACATAGGCGAAATCTGCAACTTGTTGCTGTCAACAAATGTTGCCGTCATTCTGTCGCAACAATGAGGAAGGAAACTCGGCTTACTTGGTTTAC
TCAGTTAGTTGGTCAATCGGTAGCCTCATCCCCCATCTACTCCCGCCAGTCCATCAGTAAAACCCCCGCGACACATATGCTGGTTGTGCAATTAC
GACCACACTGAAAGAAATTCAATACAATGACGTAAACATCGCCTGAACTAAAACACTTTTTATTGATAGGAAAATGAGTTTTCTCGTTTGCACGG
ATTTTTTGCCAGTGAATTTGTCAGGCAACAACACCACCGCCGCCCACTTTTACATTTCATGCAACTCAATCAATTAAGAGAGAGAGAGTTACTCA
GCAACAAGGC
(SEQ ID NO: 1)

Exon: 2050..1838
Exon: 1780..1658
Exon: 1589..1458
Exon: 1084..1001
Start ATG: 2050 (Reverse strand: CAT)

Transcript No. : CT18623
ATGCTGCAACTTCAAAAGATGAATACTCTGCTGCTGCTCTTGGCCATGATGCGCTGCATCTGTGCCACGCCCATAGCTCCTGCCACGCCCGATGG
CGCCACGCCCATCGACGCCCGCGTCTCGGCCGCCGACTTCGGAGCCCAGGATGCTTTCGATGCCGCCGACAGCTCCGCGGAATCCACCCACGCGC
AGGCCAGCGACGCCGGGTTCAAGATCTCTCTCCTGCCCACTCCGGCTAAAACGGCGGAATCGGTGAATCTAGAGCAGGAGGCCATTCCCTCGAAG
GTGCTGAGCGTGTACGACAACAGTCAAAAGAGGCTGGCCGATTTGGCGCAGCCCGTTCCCATTTTGGACTCCATCAGTGAGCACGAGAAGTACGG
CAACAACGGTGACATGTTCGACGGCATCTCGCGATCCATTGTCAACGGCTACGAGGCCTTTTCCAACCTGCTCAACACCTTTATTCAGAAGCCCA
AAGAGTTGGCGCGCAGCGTGACGAAGGGGATCACGGCTCAATTGGATATCATAGGAGGCAAATTGGTGGGCCTTTGA
(SEQ ID NO: 2)

Start ATG: 1 (Reverse strand: CAT)

MLQLQKMNTLLLLLAMMRCICATPIAPATPDGATPIDARVSAADFGAQDAFDAADSSAESTHAQASDAGFKISLLPTPAKTAESVNLEQEAIPSK
VLSVYDNSQKRLADLAQPVPILDSISEHEKYGNNGDMFDGISRSIVNGYEAFSNLLNTFIQKPKELARSVTKGITAQLDIIGGKLVGL*
(SEQ ID NO: 3)

Celera Sequence No. : 142000013384666
GCTGTCATAATGGCATAAAAGATTGAGATGGAAAACAAATTCATAGATAGCGAACAAATTGATGGTTACACTGCTAGAAAATTTTTTTTAGATT
TAGTAGCATACTTTAAAGAAATATGCAGTTATATCCTAATAGGATTAGTTATTAAGCTCCGTTTTTTTTTTGTTCTCTTTAAAAGTTTTAGTTTT
TTTAGATATAAATAATGGCGTTCTTTGTACACATTTTTCTCTGTGCACATTAAACGGCTCTATTTGCAATTGAACTGCAATAGTAACAGTCACGA
AAGGCAGTCAAAAACAAAGAAAAACGGCACTTCAAGTGCGCAATGGCCTCATTTTTGGGGGCAGTAAATGTAGCGCGTAGCCAAATTGCTCTGCA
TTTCGAAATATCAGACATTGCAATTATCTATCGAGTATTCACTAAATGTAGTTAATTTTGTAAGCTTTGGCTTTCGAGCTTTCAAAATTGGCGCG
TACTTTTAACAGTAACTGTTAGCAGTGTACTGTTAAGTCTGCATGCGATCTGGCAGCTCAGTTATAGAATTATTTTTGGCCAAACCAGAGTAACT
CATTTCGCTCTTGGATTGAAGATGTTTTTAAGGCCGCTTTAATGGCGTTGACAATTACAAAATTTCGAACTTCGAGGGGGATGGTGGTGGCCGTA
CAGCCCACAGTGGTGTTGAGCCCCAAAATACCAGATTCCCAGGATAACGAAAAGGTAATCAAAAATCTGTCAAATGTATAAACTCTCATCCTATT
TGTTACAATTCGGCGTTGCCAAATCGTGAAAAGGTGCTATTGACCAGCTGTTTTGTGAAATACGTGATACGTACGGGCTGAGCACAATTTGTTTA
AAATTTAAATCATGATAAAGTAGGTAATTATATTTACTTATTTGCACAGAAACCGTTTTCAAAATCGGAGCCGGGAAATGCAACTGTGAGAGTTA
ATGCAGGTGGTATAGTTCTTAACAAAATACCAGCGATTATAAGGCCAAGTATGAAGAGAGCAGCAACAACAAAGATGACTGGAGCCACGGCTGCG

FIGURE SHEET 1

GGAGCAACAACAACAACATCGTCAACAGGTGCAGTGGGATGTGAGTAACAACCAATCGAACACTAATATGAAATATAAACAAATGGTTTTTAAAT
ATTGTTCTTATACTTTAGATCCCGTTCTCAAAACACCCAAGTATGTGGTTCAGACTAGTCCGAGTGGATCCTCTGGCCATCAGCTCCAGATGCTG
GCGAGGAAGGACACTCAAAGTCTGGGAGTGGCCATCAATTCACTGCCGCCCAACACAATCATCAAAGCAACCACAAGACCTTCACAAACAGCGCC
TTTGACACCAAACTCAGCGGCTGTCACGCCAAGCACGCCGAGCAGTAGCAGGAATTCCACTCAGTCCACACCAACTGTGGTACCTGATGCGAGAG
TTTCCTCCGCCGTGCGCCAAGCTGTGTTCATCAAGAGGGAGCTACCCCAGCCGCAGAGGAGCATGCGAAATATGACACTTGGTTTGGTGGAACAG
GCGCCACTGCTTCATTTGGGTGTTGCGCCACAGCACCTGTCACTGCTGAAACGCCATATCTGCCGCAATGCTAATGTCACCCACTTGGACTGTTG
CTTGACTCTAAGGAAACTCAAACAAAACGAGCACTTCGCCCTGTTGGCCGAGCACTTTGAGCTGAGCGAATCAGATGTCGAGGACACATTTAAGC
GCACCCTTATCAAGCTGGCCCGTTACCTCCGTCCACTGATTCGTTGGCCAGATGCACGGCATCACAACGAGCGCTTCAAACATACCCCACTGAAC
TACCGAGCCAACCTGTTGCATGTACGCTCGTTGATCGAGTGTGTGGAAACGGACGTGCCGATAGATCTGGGATTGGGCAGCGGCAGCTATAAGTT
CATATTGTGCATCAATACAAATGGTAGTTTTTAGCGTAAACAGCGTACTTTCATTAACACTTCCCTCGCTTTTCAGGCATCATCAGCTATGTGTC
TAGCGCCTTTCCTGGTAGTTGCGATGATCTTCAATTGTTTGAGGCCAGCAGATTTCGGGATGTCATTCCCAATTACCTAACACTATGCGCGGAAC
CAGGCAAAGCAGTACGCCGTGCTCGCAGGTCGGGCTTCGGAGATCCTCACGACTCAGCGGATGAGGATGAGGCGGCGGCGGAACCAAAGCGATCA
CTTACCAAATTCGAGGCACAGCGTTTGAGTGGCCAGCTAGCAAGCCAGCAATCCCTATCCGTTGTAGACGGAGCACTGACTTCCAAGCGGGCTCC
AGCGATTCAACTACCCACATTCAACGCACAAGAACCCGCCTGTAGAGCCCAAATGAGAGATATGATAGATTATTTAAGGGAATTCCGCATGCTGG
ATAATTCGGCTATTAAGCAAAAGTCATTGCTGGGTTATCTTGATGAAATGATCGTGGTGGCTGCGGGTCTATGCAACCTTAAGCGCCAAGAGTTG
GAATCTTAAATAAGAAGTGCCATCCGCGAAGGTCTGTTTAAAGGCCAACCAGATGTTATTGTCCTAGTTATTTTAAGAATTTAATTTAATGTATT
GTTAATGCAATGTAGAAACTGACTATTAACAAGTACGATTAAAAGGGTATATTTTAAAGTATTTCAAAGAATAAACACTACGTGGTCATTCAAGA
GGTTTTTGCTTTTATCTGGAAACATACTCAAGTGCCTTATTTTCGAAAACATTATTAGTTTCTCGATTTCCACAGTCGTACTTGTCCTCTTGTTT
GTTCAGCTTCCCCATAGTTAAACACTTGCAGTTGTATTTCTTTTATATTTTTGCTTTATTTACTTTACAAAAATACAAGCAAAACTAAGTACATA
TTCAATGAAAGTTGTTCAATGAACCAGGGCAACATTGCCAATCGGAGTTTGCAATATTTGAATTTGAAGAATACGCGTATGTCGTACAATGTATA
GATATTCCAAGGGTAGGTGCTCCATCATATCCGTTTACTCTACCATCGTTGGTCGCTCTTTCTCTTAGGGGGTAATAATTAAAAACTTGCTTAGT
TAATAAGTGACTCTTCGTACTAATAGCTAAACATATTGTATATTGTGTGGTGTGGTGTATGCCTGACAAAACCAGCTCTAGCTCCTCATCCTGAC
ATTATAACAAGTAGTTGGTTGGGCTACCCTTTTCGTCTCAGAGCTTCTGAATGATGTCGAACTTCTTCTTGAGGTCCACACTCTCGTTCTTGGGA
TCGTACTTCTTCTTGGATGCCAATTTGGCGCGCATTTCGGCGGCCGTCATTGGTAAATGCAAGGTGCCCGCCTTATAGCCACTGGTCGGTGGGG
TGGTGTAGTGGGTGTGGTCATGCCATTTGTACCATTTCCATTGGTGTTATAAACACTGCCATTGTTGTTGATGCCAGCCTTAGTAGCGGACGGCG
GTGGCGGTGTGCTCATCAAAGTGTTATTATTAATCGGCGATGAGGGTTTACTTCCATTT
(SEQ ID NO: 4)

Exon: 1001..1085
Exon: 1159..1923
Exon: 1977..2479
Start ATG: 1001

Transcript No. : CT20444
ATGAAGAGAGCAGCAACAACAAAGATGACTGGAGCCACGGCTGCGGGAGCAACAACAACAACATCGTCAACAGGTGCAGTGGGATATCCCGTTCT
CAAAACACCCAAGTATGTGGTTCAGACTAGTCCGAGTGGATCCTCTGGCCATCAGCTCCAGATGCTGGCGAGGAAGGACACTCAAAGTCTGGGAG
TGGCCATCAATTCACTGCCGCCCAACACAATCATCAAAGCAACCACAAGACCTTCACAAACAGCGCCTTTGACACCAAACTCAGCGGCTGTCACG
CCAAGCACGCCGAGCAGTAGCAGGAATTCCACTCAGTCCACACCAACTGTGGTACCTGATGCGAGAGTTTCCTCCGCCGTGCGCCAAGCTGTGTT
CATCAAGAGGGAGCTACCCCAGCCGCAGAGGAGCATGCGAAATATGACACTTGGTTTGGTGGAACAGGCGCCACTGCTTCATTTGGGTGTTGCGC
CACAGCACCTGTCACTGCTGAAACGCCATATCTGCCGCAATGCTAATGTCACCCACTTGGACTGTTGCTTGACTCTAAGGAAACTCAAACAAAAC
GAGCACTTCGCCCTGTTGGCCGAGCACTTTGAGCTGAGCGAATCAGATGTCGAGGACACATTTAAGCGCACCCTTATCAAGCTGGCCCGTTACCT
CCGTCCACTGATTCGTTGGCCAGATGCACGGCATCACAACGAGCGCTTCAAACATACCCCACTGAACTACCGAGCCAACCTGTTGCATGTACGCT
CGTTGATCGAGTGTGTGGAAACGGACGTGCCGATAGATCTGGGATTGGGCAGCGGCAGCTATAAGTTCATATTGTGCATCAATACAAATGGCATC
ATCAGCTATGTGTCTAGCGCCTTTCCTGGTAGTTGCGATGATCTTCAATTGTTTGAGGCCAGCAGATTTCGGGATGTCATTCCCAATTACCTAAC
ACTATGCGCGGAACCAGGCAAAGCAGTACGCCGTGCTCGCAGGTCGGGCTTCGGAGATCCTCACGACTCAGCGGATGAGGATGAGGCGGCGGCGG
AACCAAAGCGATCACTTACCAAATTCGAGGCACAGCGTTTGAGTGGCCAGCTAGCAAGCCAGCAATCCCTATCCGTTGTAGACGGAGCACTGACT
TCCAAGCGGGCTCCAGCGATTCAACTACCCACATTCAACGCACAAGAACCCGCCTGTAGAGCCCAAATGAGAGATATGATAGATTATTTAAGGGA
ATTCCGCATGCTGGATAATTCGGCTATTAAGCAAAAGTCATTGCTGGGTTATCTTGATGAAATGATCGTGGTGGCTGCGGGTCTATGCAACCTTA
AGCGCCAAGAGTTGGAATCTTAA
(SEQ ID NO: 5)

Start ATG: 1

MKRAATTKMTGATAAGATTTTSSTGAVGYPVLKTPKYVVQTSPSGSSGHQLQMLARKDTQSLGVAINSLPPNTIIKATTRPSQTAPLTPNSAAVT
PSTPSSSRNSTQSTPTVVPDARVSSAVRQAVFIKRELPQPQRSMRNMTLGLVEQAPLLHLGVAPQHLSLLKRHICRNANVTHLDCCLTLRKLKQN
EHFALLAEHFELSESDVEDTFKRTLIKLARYLRPLIRWPDARHHNERFKHTPLNYRANLLHVRSLIECVETDVPIDLGLGSGSYKFILCINTNGI
ISYVSSAFPGSCDDLQLFEASRFRDVIPNYLTLCAEPGKAVRRARRSGFGDPHDSADEDEAAAEPKRSLTKFEAQRLSGQLASQQSLSVVDGALT
SKRAPAIQLPTFNAQEPACRAQMRDMIDYLREFRMLDNSAIKQKSLLGYLDEMIVVAAGLCNLKRQELES*
(SEQ ID NO: 6)

Celera Sequence No. : 142000013384697
TCGATTTGTTTATAGTCTTTAGCGGCTCATTGTCACCAATTTTTGCTCTCTTGCGAAAGATGTGAACTTGGGCGCAATATTGATTTTTCGATTTT
GGCTCATTGCTCGCATCACCGGGTGTTGTGCAAGATTCCCATTTGGGTCAGGCTCGGGAAAATGGGAAAGCTCTGGAATGGGGAAATGCGCATCT
TTTTCACTTACCACAATGAGAATGCAGGTGACCAGTAGGCCGTACTTCCAGGGTGTTATGGGAAACGACTTCTCCATGTTGCCACAATGTCGCAC
GTGAGTTTCCTTGGCAGTTATGCTTGTGAACCAAAGTATCTGGCTGCCGATAGAATGGAAGATATGACCTCCGAGTTCCGGAAACTCGCTCGATT
CGCACTATGCCACTGGCTTAGGGCAGGGCATTGTTTACTTGCGCCCAGAGTAGGTCTACACCCACATTAAACTGGGCTCGGAGCTCTGAGCCCTA
TTTCGGATTGGAACTCGTGGTGTTGATGCCACAAAAGCTGCCCTGCGACTGAGCGAAAAAATGAGAGACCCAAGGGCCCCTCTCGAATCTGAACT
TTTTGGTCTGGCGCGTTCTGCGTTCGCTGGCAAACTGAAAGCGGGAAAAGTTTTGTTTTTCTCTCTTCCCGTGAGGACTGTTGTTCCCCAATCAA
AATAAACCACACAGAGCGCACTCGCTCTCTCAAAAGAGAGCGTTGCACTTGGGTCAGAGCTCCAAGTCATGTCGACTGGCGTTTCCACACGGTGG TGTTTTCGAATTCTTATCGGGTCTGTCATGAGCGTACATATGTGAACTGCTGAATGATTGAATGGATTCGAGCTTAAGCAATTAGGAAAATATTA
ATGTATCCAGAGGTTTTTAGCACCGATGAAGCTATTAAACAACACAACCAAGGTTTAATTCTTTTTTCTTTCTTTTACGAGAGTGATGATGATGG
TGACAGTTTTGTGGAAGATTGCCTAGAATGCTGTGAATACCAGCAACGATTCACCGAGTTGCTATGCATTCTAGCGCTCCTTTAGCGGCTTTGAT
CTCCAGCTCCATTTTGATGGTGTTTATCAGGTGCACATTGGTGGCTCGATCCTTTCCTTCTCGGTGGCGGATGTCAGACTTGCCGGTGCCAATGT
GCACATTCAAGGCGTCGTTTCTGATTAAATTCTTGGTGCACAGATAACAAGGATAGGCCACCTCGCCAATGACCTCGATCTGGATGATTGAATTA
TTGGCCTCACTCAGGGACTTTTGCAGCGTGTCAATCTCCTCCAGGGCCGCCGTATGCGCCTGAGGCTGGCATACTGAGACATCACAAAGGACTTG
ACAATGTCACTGTCCAGAATGTGTCCAGTGAAGCCTCCGAAAGGTGGGCACTAGCTCGAAGTTTTGCTCCCTGAGAATCCTCTCCGTTTCATGGG
ATCCTGCCAGAAATGCCGTTGTGAAGTAAGTGATAACTATTATTTTTATAATTTTCCATACCCATAAGCCTCCAATCCAGTGGACCATCAGGATA
CTATCTATTGAATATTTGCCCTTAAATCCCATTTCTCTGAAAATAAATCAGCCACTTCTTCTTCGCCTTTTTTTTTTTTTTGGTTTGGGTATTGA
CCGATATTTCTTTTTGTGTATCGATATTGGGTCGAAAAACAAGGCATATCGATATATTATTATCTAATTATCAAGCCGCCAACGCCAAAATGTCT
GCTACGTTAAACTTAGAAGACGCTACAAAAAATCAACCAACAGTGCGAGGTTGCAATTGCAACGCTAAAAGGAAGGAGTTTTTCCTCCAATTTA
AAAAAAGAGTCTGGCGGCTGAACACATCAGAATCACTTTGAGCAGACTCCTGAGCTTTTTAAGGGATAAACACATGCTTTTGGCAATTATTGTCG
ACGACGAAAGCATGAACATCCCCAGCCGCACGCTGCGTGTCCACTGCTCTATGACATGGAGCACTGTCTGGCAAACTTTCGGAGATACTGTGAAG
GCCACTGGACTAACCCCAGGAATGGGCCAACTGTGTGTACGTGGAGGAACAATGCGGAAATTTAAAGCGGAGATGATAATGATTCGCAACTGGAG
ACTCTTCAGTGTAAGCGGAGAAGATTTCTTCTTAAGCTTATTGAAAGTGAAACAACTTAAAGACTTCGAGTTTCGATGCAGTGTTGCGATGAAGA
AACAGGGGTTTGGTCCTCTTCCTCCTATTAGGGCAAGTAAAAAACGTTTGCAAAGTTAAAATATTTGTATACTTTCAGGAAGAGCTTCCAGCTTC
CGCCTGCGAGGCTGAGCCTTCCTTTGTGTCCGTCGCTGATCCTGACCACACCTAAACATATTCTGGCACCGACCTGCGATCAGCATATGTAAGCG
GTCCGTTGCTCCAGCAGCCACATTTTGTACCAGTACCGCCCCCGTCCGACCACGAGCAGCAGCACCACCAGCAGATGCAACCGCGACCCCTACAG
CAGCAGGTCAGTTACGTCAATCCAACTTGCCACCCAATTCCGT
(SEQ ID NO: 7)

Exon: 1513..1487
Exon: 1300..1001
Start ATG: 1513 (Reverse strand: CAT)

Transcript No. : CT31974
ATGGTCCACTGGATTGGAGGCTTATGGCCTCAGGCGCATACGGCGGCCCTGGAGGAGATTGACACGCTGCAAAAGTCCCTGAGTGAGGCCAATAA
TTCAATCATCCAGATCGAGGTCATTGGCGAGGTGGCCTATCCTTGTTATCTGTGCACCAAGAATTTAATCAGAAACGACGCCTTGAATGTGCACA
TTGGCACCGGCAAGTCTGACATCCGCCACCGAGAAGGAAAGGATCGAGCCACCAATGTGCACCTGATAAACACCATCAAAATGGAGCTGGAGATC
AAAGCCGCTAAAGGAGCGCTAGAATGCATAGCAACTCGGTGA
(SEQ ID NO: 8)

Start ATG: 1 (Reverse strand: CAT)

MVHWIGGLWPQAHTAALEEIDTLQKSLSEANNSIIQIEVIGEVAYPCYLCTKNLIRNDALNVHIGTGKSDIRHREGKDRATNVHLINTIKMELEI
KAAKGALECIATR*
(SEQ ID NO: 9)

Celera Sequence No. : 142000013384626
GCAGCAACTAAGTTTGGAGGCATCGGAGAAAAACGAGGAGCGACTGTTGCTGGCCAAGCATTTGTCCGAAAAGACGAAGATGTACGAACTGACCA
AGCAGAAGCTGGAGGATGTTCAGGGTGACTTTGAGGCTACCCAGCACAAGCATGCCACCGTGCTGAAAGAGCTCCATCGCGAGCTGAACAAGTAC
AAAAGGGGAATTACGGAACCGAAGACACCAATCAGCTACTGCAGCAACTGTCAGCAGGCGATCAATGGGTATCCAACGGAGAATCCTCAACAACG
GAGTCATAGTCGCTCCAGTAGCCACGGCAGCATGCACAGCGGCAGTCGACGGGCCAGCGAGTCTTCCGAATCGGAAACGGTGGCCAGTAGTGCCA
CCACCGTGCAACAGCCGCCACCGCAGCAAGATCTCCAGGCGGTACCGTCCAAAAAAGTCCTCGTAGAGCGAATTCTGCGACTGCAGCAGGCCACT
GCCCGCCAAACCGAACGGATCGAGTTCCTGGAGAACCACACGGCCGCTCTGGTGGCCGAGGTGCAGAAGAAATCCAAGGTGGTGCAGCACTACAT
GCTCAGGGATCAGACTGCCGGCGCATTAACCACATCGCGGAGCGATCAGAACAAAAGCGAGTTGGTCAAGTACGGAAATGGTATCATGGCAGCCA
TCTATGGTGGTGGATCATCGAAGACGGGAGGCGAGAATAAAGCCATGTCCCTCGAACTTTCTCTAGAGATTAACAAGAAACTGCAAGCTGTGCTC
GAGGATACGCTCTTGAAGAATATTACGCTGAAAGAGAACCTCGATGTGTTGGGACTCGAAGTGGATAATCTCACGAGGAAATTGCGCTCCCTGGA
GGGCAGTTGCAAGTAAATGCCAGTCTTCTTATTCCATAGTATTCCATTCCAGAGTCTAACCCGCGTGTAGATAGTGTACAAATCAAATGTTCGTA
TGTTTAAGTGTATAATATATGTATTTAATATTTCAACAACGTCCCCAGGCTTATAATAATCCTTCGTAAAGCTTGGCGCTCACGGGTTTCGGCTG
GCCCACACCAAGGGCAAAGTTAACAGTTGGCTTTTCTCCATCCTTGGCTAATCTGGCCATTTTGTTGTCGGTCAGTTTGTAGTGGACCTTCATCT
GGGGATTGGGGTTGCCCGTTTCCTCCGATACCAGTTCGCGGAGCAGAGGCGGAAGTTCAATCTTGGTGGGCAGTATCACTGGTTCAACCTTCTTC
TTGTTGTTCAGATACTTTGCTTCCTGATCCTGCGGCACCAGTTCGTAGTCCGCCTTATAGCTGGTGCTGTAGATTTCCACAGGCTTTGGCTGCGT
TACGCCGCGCCACGTTTTCTCCACAGTGACCCGCACCTTGCGGATCTCGCCGGGCTGCTCGTCCACGGACTGCACCTTCAGAATCCGCATGTAGC
AGGGCTCCGGATATCGCTGGAACATGTTACGTATTAGCAGACGGCCCACACCCCAGTTGGGCAGGTTTGAGACCAGCTCCCACAGCGTGTTGCCG
CGAAAGTCTGTGGTGCGACCGATGTACTTGATCACTTTTTGGGCCATTTTACTGGGTTATTTCACTATTTTAATTGAATTTTTGTTGCAAGTTAT
AAAAACAGTGAGTTTGCCACTCACAGGGAAGGTCGAACAGCTGTGCCGGCTGGCTTAACAGGGCTGTTAAAACTTAACAGAAGGCTGTTATGAAC
AGTAAATTGTGTGTGTTGGCAATGCTGCGCGGCGATTTTAAAACCAGTTAAATTTTGAAAAAATTAAATAATTTTTTAACTTCCCAAATAATAAA
TGAAAACACACACACACATTTAAAATTTTAGTAACTAATAATCGCTTTAAAAGGTTTTAATCATGTTCTTGTCTCCTAGATCCAGATGTTTTGTC
TAGTATAATATTTATTTTTAAAACAATTTGGTTTTTTTCAGAGATTTAAAGATCACCTAATATTTAAGGAATATTTAAATAATATTTATACATCT
TTAAGTGCTGATAACTCACAGCCGCATGAGTCTGACTTGAATGCATTCATTATATTTACATAAATATGACTTTCAAACTAAGTTTAATATATAAA
ATCTAGTGATAGTTAATCCCTCACTAATATGGAGCTCGAATATGTTCGGATAGTTCCTCTCCTCCGCCAGTGTGTCCCACTTCCCCGCCACTGGT
GTCTAGGTGCTCATCGTAGGACTCCTCCTCGCCACCCAACTCCTGACCATCGTGCCCGTGGGCTGATGGATTCGTGCTCTCATGCAATCCGATCG
TGGCATGCTGGGCCGCCTTGGATGCATTCACCTGAGCCGCAGCTGCGGAATTGGCCGCCTTAAGGGCGGACTCCTTGGTGGCCGCATAGTCTACG
CGCGCCTGGTGCAACTGCTCCTCAACCTGCTCTAATCGGTTCTTGGACTGACCCACCATCTGGGATTGGGAGGCCAGTTGATTGTTCACCTCCGT
GGAGGTTTGCTCAGCCTGTTCGGCCACGGATTTGGCATTATTTACCGCAGCTGTGAGCACGGATATGTGATGATGCGCCGCTTGTGCCGTTTGCT
GTGCCAATCTCGCGGAGATCTTGGCCGCCTTCAGTTGCTCTAGCTCACGGGACAGAGATCTTTGGGCCTCGGCTGCCTGCTGCTCCAACTCCTGG
AGAACAACCTGCTTGCCCACCAGAGCCGCTTGTGCAGTGGCCGCCGCCTGAGAAGCCGCTTGGGCCAGTGTATTCTGGGCTATATAGGCCGCCTG
CTTGGCAGCTGCATGCTGGTTGGTCACTGCACTGTGAGCCTGATCCGCCGATCCCTGGGCAATGGAACGCAGGCCGCTGCCAATGCTATAGCCAC

FIGURE SHEET 3

CGGATCCCTTGCTGGAAACTGAGGAGCTACCTCCCGATGTGGTGTAGTAGCTTTTGGTGCTATGTTGTGGCTTCTCTGGCTCGGGAGGCTCTACT
GCCGGCAGATGGGGCTCAAAGTAACCACCTTGGTGGATTGGTGGCGGTTGCTGCGGTCGGTAGTGATAGCCATTCCTCTTGTGCAGGCGACCCAA
GGCATTGGACAAAAGGAGCACTAAAGGTATTTGGATATAAAATAAGATTTAACGTGGTTTTTAACCGAATAGGAATCCTAAGTTAGGACCTAAG
TAGGATTTAAGTTTTCAATATCCTGGTGTCTTTGTATCTATTTCTTTATAATTTGTATCTCTATATGTATATAAGACAAGTTCAAGGGATGTTGA
AGATTTCCGAAGAGAATCTATTCGATTCGGGTATGAGAATAGTAATCTTCACTTTTCAACTCTTGGAATTTAATTTTTAAAGAACGGATCACTAC
AACTTTTCACTTTGTTATAAAAGGGTATTCCCCGGCTTACCCAAAACAAGCTGGGCGAGAAGAAAACGTAATCCTTGGCCGTACATTTCGCTAGC
GCTGCTGGAACTGCATTGAACTTCAAATTGAATGGAAGTGTACAATTTATAAGTCTTTCAGAGCCGCCAGCCGAGCATAAAGTTTATCAAGTTGC
GGAAAGTCTGTTGCGGTTTTTAAATTTAACTGATCGCGGGCATGTTATGATTTTCCATCTCCAAGCTATTTGAATAGCTCTGCCCACTATTTGGA
GAGCTGGGTCCACACACATGGCACCTTTACACCCATTTCCATCCATACCATCCCATCGAGGAAGTTTAAAGTGACCGCCTTTGAGCCACAAAATA
TGGTGGCGTTTTTTTTTAATGGTTCGTTGGCACGCTTGTTTGAACCAAACGGACAGTGTAAAGTGGTCGGTCTGCTCGGGTTTGTTAATGTTTT
AAATTTAATTTGCATTTTATGTGCTGCACTACTTTGTAATTGAACCTTAAGTGGCTCTTTTGACGGGATTCAAGGTGCAACGATGCAGGGAAAGC
CATTTGAGGGATTACGCTTTCGTTTAGATTAACTAGCCCACGAAATTTGGCAATTTACGAACGGGGGAATTTTCCAATCAAAATTTGAATATTTT
TTTAATTGAAAAATTATATAATGCTAATAT
(SEQ ID NO: 10)

Exon: 3411..3366
Exon: 3060..2115
Exon: 1571..1001
Start ATG: 3411 (Reverse strand: CAT)

Transcript No. : CT32256
ATGTACGGCCAAGGATTACGTTTTCTTCTCGCCCAGCTTGTTTTGGTGCTCCTTTTGTCCAATGCCTTGGGTCGCCTGCACAAGAGGAATGGCTA
TCACTACCGACCGCAGCAACCGCCACCAATCCACCAAGGTGGTTACTTTGAGCCCCATCTGCCGGCAGTAGAGCCTCCCGAGCCAGAGAAGCCAC
AACATAGCACCAAAAGCTACTACACCACATCGGGAGGTAGCTCCTCAGTTTCCAGCAAGGGATCCGGTGGCTATAGCATTGGCAGCGGCCTGCGT
TCCATTGCCCAGGGATCGGCGGATCAGGCTCACAGTGCAGTGACCAACCAGCATGCAGCTGCCAAGCAGGCGGCCTATATAGCCCAGAATACACT
GGCCCAAGCGGCTTCTCAGGCGGCGGCCACTGCACAAGCGGCTCTGGTGGGCAAGCAGGTTGTTCTCCAGGAGTTGGAGCAGCAGGCAGCCGAGG
CCCAAAGATCTCTGTCCCGTGAGCTAGAGCAACTGAAGGCGGCCAAGATCTCCGCGAGATTGGCACAGCAAACGGCACAAGCGGCGCATCATCAC
ATATCCGTGCTCACAGCTGCGGTAAATAATGCCAAATCCGTGGCCGAACAGGCTGAGCAAACCTCCACGGAGGTGAACAATCAACTGGCCTCCCA
ATCCCAGATGGTGGGTCAGTCCAAGAACCGATTAGAGCAGGTTGAGGAGCAGTTGCACCAGGCGCGCGTAGACTATGCGGCCACCAAGGAGTCCG
CCCTTAAGGCGGCCAATTCCGCAGCTGCGGCTCAGGTGAATGCATCCAAGGCGGCCCAGCATGCCACGATCGGATTGCATGAGAGCACGAATCCA
TCAGCCCACGGGCACGATGGTCAGGAGTTGGGTGGCGAGGAGGAGTCCTACGATGAGCACCTAGACACCAGTGGCGGGGAAGTGGGACACACTGG
CGGAGGAGAGGAACTATCCGAACATATTCGAGCTCCATATTATAAAATGGCCCAAAAAGTGATCAAGTACATCGGTCGCACCACAGACTTTCGCG
GCAACACGCTGTGGGAGCTGGTCTCAAACCTGCCCAACTGGGGTGTGGGCCGTCTGCTAATACGTAACATGTTCCAGCGATATCCGGAGCCCTGC
TACATGCGGATTCTGAAGGTGCAGTCCGTGGACGAGCAGCCCGGCGAGATCCGCAAGGTGCGGGTCACTGTGGAGAAAACGTGGCGCGGCGTAAC
GCAGCCAAAGCCTGTGGAAATCTACAGCACCAGCTATAAGGCGGACTACGAACTGGTGCCGCAGGATCAGGAAGCAAAGTATCTGAACAACAAGA
AGAAGGTTGAACCAGTGATACTGCCCACCAAGATTGAACTTCCGCCTCTGCTCCGCGAACTGGTATCGGAGGAAACGGGCAACCCCAATCCCCAG
ATGAAGGTCCACTACAAACTGACCGACAACAAAATGGCCAGATTAGCCAAGGATGGAGAAAAGCCAACTGTTAACTTTGCCCTTGGTGTGGGCCA
GCCGAAACCCGTGAGCGCCAAGCTTTACGAAGGATTATTATAA
(SEQ ID NO: 11)

Start ATG: 1 (Reverse strand: CAT)

MYGQGLRFLLAQLVLVLLLSNALGRLHKRNGYHYRPQQPPPIHQGGYFEPHLPAVEPPEPEKPQHSTKSYYTTSGGSSSVSSKGSGGYSIGSGLR
SIAQGSADQAHSAVTNQHAAAKQAAYIAQNTLAQAASQAAATAQAALVGKQVVLQELEQQAAEAQRSLSRELEQLKAAKISARLAQQTAQAAHHH
ISVLTAAVNNAKSVAEQAEQTSTEVNNQLASQSQMVGQSKNRLEQVEEQLHQARVDYAATKESALKAANSAAAAQVNASKAAQHATIGLHESTNP
SAHGHDGQELGGEEESYDEHLDTSGGEVGHTGGGEELSEHIRAPYYKMAQKVIKYIGRTTDFRGNTLWELVSNLPNWGVGRLLIRNMFQRYPEPC
YMRILKVQSVDEQPGEIRKVRVTVEKTWRGVTQPKPVEIYSTSYKADYELVPQDQEAKYLNNKKKVEPVILPTKIELPPLLRELVSEETGNPNPQ
MKVHYKLTDNKMARLAKDGEKPTVNFALGVGQPKPVSAKLYEGLL*
(SEQ ID NO: 12)

Celera Sequence No. : 142000013384830
TATAGTATGGTAGACTTAATAACAGTTGGCGTTCTTTGTTAACCCATTAGTGCCGCTTTGTCAACTGATGTATGCGATTGGCCGCTCAAACGCCA
CGTAATTGCTTCAATCTGAGAGCCCCGCTATAACCTACAAAGTGCCGCTGATTAGCGGCATCTTTTGCTGGCCTAGCGGTACCTGGCACCCTACT
ATGTTGGGGTATTTTCGGTACTCAAGTACCCTACTCACCCCTCGCCCTGCGGCTTCAGCGCCAGCTCCTTGAAGTTCTCCACCGTCTTGGGCACC
GTCTTGCCGAACAGACCGATCTCGATGCGACCAGCGGGCTCGCCGCCAATGGTGATGTCAAAGAAAACCTACGCAATCGGAAGCGGTTTATTATT
AACAAGTCATCTCACTTGATTTATGGCGCAGCAAATGTGTGTGTGTGTTTGTGTGTGTATGTACGTGGTGTATGCAGAATGTAAGGACGAAAGTC
CAAGGAGCACGCACCTTCTCGGTCACTTTGGGACCCTTGCTATCGTCGGCAACAACGACGCCGGCCACCAGGGCTACCACGAAAACGGATAAGAA
CAGCTTCATCGTTCTAAATATTCACAGCGCTTCAGTTTATTCCTCAAGCGACGTCGCCAATGGATATTTCACGACTGAATTTTCGGTTTCTGTTA
GTGATGTAAGAAAACTTTGTTGCATCGCCAATCGATGTTTTCCATCGTTTTTATGTTTTTGTCGAAATATCGATGCTTAAGTGTGACCATTCGA
TGACGATGTCTGATGATCACACATTCGGGCGGAAAATTCAAATTCAAATAGTTAATACGCCGAAAGCATAAGTTAAGGTTTTCGTACGAAGGAAC
AAAGTAAGTTCGAAGAGTTGACTTTATTGGTATAGTTTTTAATATTTTAGGGATTAGAAGTCCAGTTTGCATTAGCACGTAGCATTCTCTCTTGT
TTTATTGACGGTTCTGTACACAAAAAGTAAGTAAAAAAATATGCTTTTATTTATTGGTGTACTGCTATTTGCGTCTGAGATTTGTCCATATCCTT
GGCTGCCTTCTCTGCTCTCTTCTTCTCCCTGCTGGCCAGAACTTTCTCCCTGGATTTCTGGGCCCTTTCAGCGCAATCCTTGGGTCGTGTCTTCA
GGGTCATATCATCCACGGCCGCCTGTTTACGGGCTGATCTCGAAATGCATCGTTCCATGCAGCTGATGGGCACAAATCTTCCAATGAAGCAACCG
CAGTGTGAACAATAGTGATTGATGTCCTGGCGGCCAGACCATTTTTTACTGAAATAAAGTGAACATTACGAAAGATTTATAAAGCTTCATGCAGA
TGGCCAACCAAAGTTTTGTGAATCCCAGAAATCTCTGCAGGCAAGTGACCAACTCCAGTTGCACCAAACTGGTTCCAGACTTCTCACACGAAGGA
CAACGGATCCAGGTGGGCTCCTCCTTCAGGTATCCCACTTGTGGCTTGTGGCTGACAATGATGGCCACAATCTGCGGTTCGTCCACGGTCATGAT
GCGAGTTCCAGCGAGAACGATCGGTGACTGAAAGATGGATCAAATTTGGAGAGATCATGGGAGGGAAAATCAAAATCAGAATCACTCTCCCGATT
TCTCTTAACCGAGGCGTTGGTCTGGTAATTAAGTTAGTGCATGGAAATCAAATGAGTTATTCTCTCTGCGTTACAAATGCCATTGGATGTACAGT GTAAAAAGTATAGTGTACATTTTGAGCATTACACATTAAATAGTAAACTTTTATTCGTTTCAAACAGCAGTATATTTATTATTATTATTGAATAT
AAATTAAATGACAAAACTGATCTACATTTGTTCATTGTGTTATAATAATTCGGATCCGATGATCCTTCTTCAGTGGGTATCTAAAGTTGTGGACG
GCGGTATACGCCCAGGTACTCCCCGCAGGCACCGCAGTGATGCCTCTTGGTGCAGCAACGCAGCCAGGAACGCACCACACGGGTCTTGGCCTTGG
TCCTGCAATAAGGACACGTAATGTCGTTGGGGCCGGGGCCCACGGCAAAGTAAAGTGGTTTCGGATCCTGAGCCATTTCGCACCGAAAGATGTTG
ACTGCTTTAAAAACAAACGCAGACTGAGGCTAGCGAAGAGAAATTGTAGGAATAAAATGTTCAAATGATATGCAAAGAGAAAAAAATCGGCCCAA
AAAAGAGAAAATGTGATATTTTTGGCTTTATTTTTGTTTCGATGGTATTGCAGTAGTGGGTGGGAAATTGAGTGTTTAGAAGAATTTTAATAAAT
ATGTGAACAATGCTGCCTAGGCGGTGGTTGCCTTCAATTTGAGTGGTTGCCTCCTCTTCATGGAACGTCCAAAGTAACAGCCGCAATTGCCGCAG
TAATGACTTCGATCGGTTTGTTTGCACGGCACATAGTAATTAAAGCAGCAGCAGCAGCAGAAGGTCCTGTAAAAGTATTTTATAAGTTTACGTTT
CCAAGAAATAGGAGAAAGTAAGGCAACCTACACAAAAAGACATCCCACAATGCGGTTTAGTTCACTGGCCCACCACTTCAGATCATTTTGCACCA
CACTCAGATCCTTGATTCCGCAGGCGGGGCACTCGATCTCCACGGGCTCGCGTGGCAGGTTGAGAAAAGTGCCTGCCAGGGGCGTGGCAAAGTTC
TCGTAGATCTTGCGCTCCTTTCGGTCCTCCAGAGCCTTGGCCTCCCGCTCCCTGATCTCCTGCTGCGTTTCCGCTTCCTTCTCCGGCAGCGTTGT
CGTCATGATCGCTCAACAATCGAACTGAAAGCGAAACGCTGCCAAGCACGCTGGCAACCTGTTTCCAAACTCAAAAGAGAACGTGAGTGCACAGA
GAGAAATAATATGGAATTTTTGGCCAATATATTCCCCCGGTTTTCCGCCCAAAAATATGCAGTTTTTTTGATCGAAAAAGTAAAAATAATGAGCC
AAATATGGAATGGGTTACATCGTTGAATTCATAATACAATTTTCTATCGACTGGTGTTGAAGCCTTAGATTTTCAAATTTTCGCCTTTTTTTGCA
TAATATCATGATGTTACCCCTTATAAAAAATGCGAAAATTAAAAAAAAAAAAATTTTGAAATCAAACTAAAAAGTATTTTCCTTCGTTAGTTTGC
TTAATTAGGTGCACAAAACAGTATTTATCATAGCATTGTGACTCTTTTTTCTGAACTTATGGAAAAAACACTGTTTATTGAAAATGTACTTGTGA
TAACTTTGAGTTTTTGAAAAAAAAAAAAAACTATGAATAAATTCTCAACAGTTAAGCTATATAAAAAAAGTATACTTTTGTTCTCAAATAGTGTTT
AAACAAGTACAGGTTTTATTTCTGTAAGTGTATTTTCCAACTCTGGCAAAGAGTATGAGTATGATTTTTGAAAGAGCATAGAAAGAGCAGCGGCG
AAATTGATTTACAGTGTGTCTTTAATTGAGTTAGACGCGTAATAGAATTATAGAACAGATAAATATTTGGCATTAATTTCGATTTAATTGGTCCG
CGGGATGGGCTACTTGGCCTTGCGCTGGATTCCCACTTTGCCGCCACACGAGCTGCAGTAAACGCCCTTGGTGGTCCACTCCCGATTGCAACCGC
ACCAGGTGCACACGCAGCAGATCCAGAAGAGCGGAAAGATGCTGGAAAATGAAATGGAATAGTTGGTGCAAGGAACGAGATCCCAGACAGTAGAT
GTCCCCTTACCAGGATAGCAGGCTGAGGCAGAAACTGGCGTCCTTGCAGCTGGCTG
(SEQ ID NO: 13)

Exon: 2761..2519
Exon: 2119..1910
Exon: 1547..1339
Exon: 1283..1001
Start ATG: 2761 (Reverse strand: CAT)

Transcript No. : CT32884
ATGACGACAACGCTGCCGGAGAAGGAAGCGGAAACGCAGCAGGAGATCAGGGAGCGGGAGGCCAAGGCTCTGGAGGACCGAAAGGAGCGCAAGAT
CTACGAGAACTTTGCCACGCCCCTGGCAGGCACTTTTCTCAACCTGCCACGCGAGCCCGTGGAGATCGAGTGCCCCGCCTGCGGAATCAAGGATC
TGAGTGTGGTGCAAAATGATCTGAAGTGGTGGGCCAGTGAACTAAACCGCATTCCTCAGTCTGCGTTTGTTTTTAAAGCAGTCAACATCTTTCGG
TGCGAAATGGCTCAGGATCCGAAACCACTTTACTTTGCCGTGGGCCCCGGCCCCAACGACATTACGTGTCCTTATTGCAGGACCAAGGCCAAGAC
CCGTGTGGTGCGTTCCTGGCTGCGTTGCTGCACCAAGAGGCATCACTGCGGTGCCTGCGGGGAGTACCTGGGCTCACCGATCGTTCTCGCTGGAA
CTCGCATCATGACCGTGGACGAACCGCAGATTGTGGCCATCATTGTCAGCCACAAGCCACAAGTGGGATACCTGAAGGAGGAGCCCACCTGGATC
CGTTGTCCTTCGTGTGAGAAGTCTGGAACCAGTTTGGTGCAACTGGAGTTGGTCACTTGCCTGCAGAGATTTCTGGGATTCACAAAACTTTGTAA
AAAATGGTCTGGCCGCCAGGACATCAATCACTATTGTTCACACTGCGGTTGCTTCATTGGAAGATTTGTGCCCATCAGCTGCATGGAACGATGCA
TTTCGAGATCAGCCCGTAAACAGGCGGCCGTGGATGATATGACCCTGAAGACACGACCCAAGGATTGCGCTGAAAGGGCCCAGAAATCCAGGGAG
AAAGTTCTGGCCAGCAGGGAGAAGAAGAGAGCAGAGAAGGCAGCCAAGGATATGGACAAATCTCAGACGCAAATAGCAGTACACCAATAA
(SEQ ID NO: 14)

Start ATG: 1 (Reverse strand: CAT)

MTTTLPEKEAETQQEIREREAKALEDRKERKIYENFATPLAGTFLNLPREPVEIECPACGIKDLSVVQNDLKWWASELNRIPQSAFVFKAVNIFR
CEMAQDPKPLYFAVGPGPNDITCPYCRTKAKTRVVRSWLRCCTKRHHCGACGEYLGSPIVLAGTRIMTVDEPQIVAIIVSHKPQVGYLKEEPTWI
RCPSCEKSGTSLVQLELVTCLQRFLGFTKLCKKWSGRQDINHYCSHCGCFIGRFVPISCMERCISRSARKQAAVDDMTLKTRPKDCAERAQKSRE
KVLASREKKRAEKAAKDMDKSQTQIAVHQ*
(SEQ ID NO: 15)

Celera Sequence No. : 142000013384826
GGTCACCTGCTGGCGGATCTGTTTTTGCAACTTCTGCATCTGCAGCATGAGCAGAGCCTCGTTTCGCATCTGGCGGTAGGAGTAATCCATTTTGG
CCAGTACCAACAGGATCTTAGTATTATGCCTGCGACGAATTTAACTAGTGCATGAGCTTTCAGTTCATTTCCACCTTACTTACTGCAGACGCGGC
TCGGTGAGGATTGAATAGAAAAGAACGCCGGCGGCTGAAATCTGACAGAGATTAGAGGTGTCCACGACGTAGATCAGCTTCTTGACATCCTCGAA
ATACTGCCTCCACAAGGGGGCCATACTCCCTCCAATTTCCAGGATCTGTATGGACTTGGGCAGATTTTTACCGCCATGAGGAATGTTAGCTGGAG
CTTCTGAGGGAGGAGGCTTATTTTTATCCCCATTTGGCGATTTTGTTGGGAAATGGATTCGGTAAATCCCAGTGCCAATGGTGGGCATGGAAAAC
GTGGTCTCATCGATGGATTCCGGATCCTGTAAAGCTTTCAAAAGGTGCGTTTTGCCCGCTCTTTTGGGGCCCAAGCAAATGCAGGTGGACATTTT
TGCTTTTACTTGGATTTTATTTATGGATCTAACAAAGGTAGCCTTGGTTACCAAAGTTTATTAATTAATTAATTAAATTAAAATTGTAAAAGTTA
GTTCAGTAAGCACGTACATGTTGTTATTTCTGGCTTATTTATATATAAAATATTTACAAATGGTTGAACATTTAATATCAATCGCGTAATCGAA
ATCTTGTGTCAGTAGTTCAATTATTTTCTGCATGATGGCGCTCTCAGGAAATCAGTGCAAACGTTTGAACTGCGTGCTTCGGGAGTCACGAAACT
CGGAACCATTCGGCCACACTTCATATTAGCACATCAATGCATAATGACTATCGATAAAACATCGATGTATTTTTCATCGTTTTTTCATGCTGTCT
CATCGTAAACAATATCAACATTGTTAAACGCTTTTAAATTCTCTCAAAAAATGAACCACACAGCAAACAAACCTCGACAAATCGGATTCGACAGG
CAGTTCTCAGCGGACGTGAACGGCGTTCCCACGGAGATAGTGTTCCACTGCTTTGCCAAGAAGTGGTTCTTAGTCATAACGCAGCTCGGCAAGAT
TCCCGGCATCTACAACGTGCACTTCGATGTCAAAAAGGACGAAAGAGTGGTTCCCTATTTGCACGGACCCGTGGACAATCCGGAGTTCCACGTAT
CGGTGCCAATCACGATGAACTGCTGCTTGGGCTTGGACACCGACGAGACTCGCAGCGCCATACAGTTTCTGGTCAACAGAACCGGACTCCACAAG
TGCCCGACGGAGTTCGTGGTGGGCTTGGGTCTCAAGAAAATCGACGGACCCAATCTTCGTGCCCTAGCTAAGGTCCTCGAGGAGACGTTATTCTA
GTCTGCGTTCGTTATATCCAATAAATATTAGCTGTGACAGTTTTTGTAAAAAAAAACCTTGAACATTTTAATCGTAGCCTTCAACCCGGCTGACCA
AATTATTGGCCATTCTACTGCAACCTCTTTCATGTGCTTAAAAACCCAAAATAGAATCTACTCACAAAAAGGCAGTGGAATGACCAATAACATAG TAAACCATAATAATTCTGCACCGTTGTGAAAGGAATGAGTCTCGATAATTTTTTAGCAAACGTCTTCTATATTTCCTCACATTTGTACATTAAAA
ACGTGTACGCAGGTCGGGAAACGGGTACACGTCCACCTCTCGAGGATTACAGCACAAACACAACGGATGTCCGGTTGTCGAGAAGTTCTCTAGAG
GATTTAGTCGAACAGACCGAAGCCCATGTCGTCGTCAGACTGGTCGGACTCCTCCTCCTTCTTCTTCTCCTCCTTCTTGGACTCGGCGGCTGGAG
CAGCGGCGGCGGCAGCAGGGGCAGCACCACCGGCGGGAGCGGCACCAACTCCGGATCCGATGTTGGTGATCAGGTCCTTGACGTTGATGCCCTCC
AGGGCCTTGGCGAAGAGACCGGGCCAGTAGGGCTCCACCTCGACGTTGGCGGCCTTCAGGATGGTGTTGATCTTCTCACCCTGGTGAATCCAAAA
AATAAGATCAGCACAAGTTGCAGCAGTGCGAAAGAAACCATAGGACCCGCAAATTGTCCAATACTTCCGGCCGATGGCCGCGGCTTTGGAGGATT
TGCTTCGTCCCCGATTGCAATATCGAAAAACTTACGGTGACGGCGACATCGTCATCGACGAGGATGAGGGAGGCGTAGACGCAGGCGAGCTCGGC
TTTGGTGGACATGTCGAAGTGCTGTGGCTAATCACTGATTGTGCAAGTTGCCAAAAATTAATTGTTTATAACAAATGGCCTTAGCTCGGGACGAG
AACAAGCACGCTGGTCAAAATCCTAAACCGGAAAGAGCAGTTGATATGCAG
(SEQ ID NO: 16)

Exon: 1001..1426
Start ATG: 1001

Transcript No. : CT33132
ATGAACCACACAGCAAACAAACCTCGACAAATCGGATTCGACAGGCAGTTCTCAGCGGACGTGAACGGCGTTCCCACGGAGATAGTGTTCCACTG
CTTTGCCAAGAAGTGGTTCTTAGTCATAACGCAGCTCGGCAAGATTCCCGGCATCTACAACGTGCACTTCGATGTCAAAAAGGACGAAAGAGTGG
TTCCCTATTTGCACGGACCCGTGGACAATCCGGAGTTCCACGTATCGGTGCCAATCACGATGAACTGCTGCTTGGGCTTGGACACCGACGAGACT
CGCAGCGCCATACAGTTTCTGGTCAACAGAACCGGACTCCACAAGTGCCCGACGGAGTTCGTGGTGGGCTTGGGTCTCAAGAAAATCGACGGACC
CAATCTTCGTGCCCTAGCTAAGGTCCTCGAGGAGACGTTATTCTAG
(SEQ ID NO: 17)

Start ATG: 1

MNHTANKPRQIGFDRQFSADVNGVPTEIVFHCFAKKWFLVITQLGKIPGIYNVHFDVKKDERVVPYLHGPVDNPEFHVSVPITMNCCLGLDTDET
RSAIQFLVNRTGLHKCPTEFVVGLGLKKIDGPNLRALAKVLEETLF*
(SEQ ID NO: 18)

Celera Sequence No. : 142000013384809
TACAACTCAGTCGCCGCACTTTAACAACAATATTTTATTTTTGTGTGTATTATTCAAATAGGTATACCTTCCGACAGCTCTAAGTCCAGTTCGGC
GAGCTTCTCGCGGACGTAGCCAGGCAGCGAGGCAGTGTGCTCCATGGCAGATGAAAAGTGTGGCTTTAGGGTTTTGTTCTATCCTCTTCCTTGGA
GGATTCGTCTAAACTTTGGCTGGTCGCAGTACACAAACACACCCAGACACCGCTACTTTCCCACTTCGTTGTCAAAAATCGATCGATTTGCCATT
TATTCTATTTCACATTTTGCCGACGCAAATAAATACATCCGTACTTGCGCAGCACCAGTACTTTGGGTTAGTTAGAAAACACGATATTACGAATG
TCTTTTACGAATTTGCACAATGAAAGTAAACAAAGAAAAATAGCAGTACAAATCGATTTTATGAACTAGCGAAAAATTGATAACTATTTCTTCAT
ACTCTTGGGACAACGGCCTTTTTCAATTTTCGAGATGCGGTCACACTGCCCAAGTAATCGAACCACGAATTTAAGTGTTATTTTTAATGATATTA
GGCATAGAACCATTACAATTAAAAAGCTCTATTATTTATTACTTTAATCGCTTGTCTCTTAAAATTCGATTCAACAAAAGCAATTGGTGGCATTT
TGCTAGGTAGCCCTGAAATACTGTAGAGACTATCGATATCTGCACCTAAGGCGCCTATTATCACATTCGGATTACGAAGACAAAGACATGCGAAA
CCTGGATACGATTAGTGGCGAAGAAAAGCAAAGTCCTGCCAACTTAGTCTAAATTGTTTCTAAGCCGGCTGCCTATACGCCTGCGTTTTGAGCAA
AGCGGTAGTATCTTTTTCGGAACCATCGATAGCTTGTCATCTCCAGTAAAAATGCGTGAGTTTATTTAAAAAAAACGCTAGGCATACAACTAATT
ATTCTTATGATGCAGAGAACTTGAAGATCCAAGAGGAAGTCAATTCATTGATGCGTCTAGGCCAGCACTTCGATGACCAGTTAAAGCTGGCTAGC
GTCGAGTTGGGCGATTTCTCGGACGATGACCTGGCGCTCCTTGACAAATGCGCCCAATATTATTCACTTTTGCACATTCACGACATCAATCTGAA
CTACTTGCGCGACTTCTATTGTGCCAAGAAGAGGGAATGCATAGAAAACCGGCAGACCACAGTGCAGCAACGCGTAGAGCTGCAGCGCATCCTCT
CGTCCATCGAGGAGGCGACTAGGGACGTAGTTATGTTGGAGAGGTATTGGTGAACAAATCCCTTTAATAGTTGAATCCCTGACCAAAACCATTCT
TCTGCAGATTTAATGCTGCTGCGGAAGAGCGGCTCATCCCGGATATCGTCGTAATGCAGCGAAACGCCCAACAGCTTGCAACAAAACAGGCCTTA
CTGGACCGGCAAAAAACCCTTAAGATCCCAAAGGATTTAGCATTGAAAGTGTCATCGAGAAGGTAGATTCGCTGGAGCAGCGCTAAAGAAGTGA
ATTGCTTTCGTTTTTAAAAAATTATTTAATTGTATTTACTCAGTAATGCAAAACACTTTACAAAAACATAAAATCTGCAAATTTTAAAGATGAAT
GTTGAGGTTTACAACTTGGAACACTACACAATCAGAGGGTGCACTTATTTTGGTTATTGTACGCATTTTAAAAACGTTCCAATTGTTGCTAGGTT
GTGTCAAATATTTATTTAAAGTATCATGATAGGAAAACTAGAAGACCAAATAATAATTTGCCAGCTGCTTAAAGCATACAAAAAGTGTACCGTGT
TCTTCCATGCCATTGCTCATATGTATGTATTTGTGTATTTCCAATGTGGTATATGTATCATATATATTGGTGTATAGATAGAATTAGTAATTTCA
TATTCTTTAAGTTCTTGCTTGTTGTTATGTATATAAAGGGCGGGTATGTGGCAGACAATCTTTTCGGCTAGCAACGCGCTCCACGCCACAGGCCT
ACTCCACGTTTCCGGGCATCTTTTAGCGGAACTCGGGCGCATCATCTTGCGTTATGTCACCGTACTTCCAGATGGCCAGATGCGCGACCCGAGCT
GCTTCCTGCGCGGCTTTGTACTGGTCCACTAGTTCCTTGAGCTTCCGCTCTCCACGCTGTTCGGCCAGAACAAGGCCCTCGGCTACAAGCTGCTT
TCCAAAATCGACTTTAGTAGTTGGATCGCGAAGAGTGGCCAAGTTCGGCGACCCAGTCACCTTTAGCTCGACATTGAGTTGAACCTTATGGTTCA
AAACGTCTTCGGAAAAGGCACGCAAGGCTTCTTCCTTATCTTCGTTGTCAGTTGGCAGGGCGACTAAGGCCAAAGCATACTCCGTAGCGTAGGGC
TTTTCGCTGCTGAAGGCTGGTGGCAGGGCTGCCAAACGGTTGGTCGGAAGTGTCTAAAAATGGAAACGAGTGTTAATACTGCCAGGAAAAAAATCA
CAATGGTTTTGGTATGAGTGTGTCGCAACTCGAATACTTTTG
(SEQ ID NO: 19)

Exon: 1001..1278
Exon: 1338..1512
Start ATG: 1001

Transcript No. : CT33406
ATGCGTCTAGGCCAGCACTTCGATGACCAGTTAAAGCTGGCTAGCGTCGAGTTGGGCGATTTCTCGGACGATGACCTGGCGCTCCTTGACAAATG
CGCCCAATATTATTCACTTTTGCACATTCACGACATCAATCTGAACTACTTGCGCGACTTCTATTGTGCCAAGAAGAGGGAATGCATAGAAAACC
GGCAGACCACAGTGCAGCAACGCGTAGAGCTGCAGCGCATCCTCTCGTCCATCGAGGAGGCGACTAGGGACGTAGTTATGTTGGAGAGATTTAAT
GCTGCTGCGGAAGAGCGGCTCATCCCGGATATCGTCGTAATGCAGCGAAACGCCCAACAGCTTGCAACAAAACAGGCCTTACTGGACCGGCAAAA
AACCCTTAAGATCCCAAAGGATTTAGCATTGAAAGTGTCATCGAGAAGGTAGATTCGCTGGAGCAGCGCTAA
(SEQ ID NO: 20)

FIGURE SHEET 6

Start ATG: 1

MRLGQHFDDQLKLASVELGDFSDDDLALLDKCAQYYSLLHIHDINLNYLRDFYCAKKRECIENRQTTVQQRVELQRILSSIEEATRDVVMLERFN
AAAEERLIPDIVVMQRNAQQLATKQALLDRQKTLKIPKDFSIESVIEKVDSLEQR*
(SEQ ID NO: 21)

Celera Sequence No. : 142000013384556
CATTCCCGAATTGGAGGAAGTATTCACGAAGGCATTCCTCATCGTGGTTATCCTTAAGACCGCCTACGAACAGCTTCTTCACGGATATATTGGTC
TCGCGCGATTCGCGTTCGGGACGGGGCAGAGCACGCTTGGCTTCCACAGTTCTGGAAGCGAAAGGCCTCATGGTATAGATCTATTCTTGGTACGA
TATGATCCCCCACCAAGTCTATACTCACTTGCCGTCGATGATGTGCGGACGGTTCTCCTGGGCCCTGTCGACCATGAGAGACTTTGTGTAGGTGA
TGAAGCCGAAGCCGCGAGATCTCTTGGTGGCAGCATCGCGCATCACCACAACATCGACCACCTTGCCCCACTGGCCGTAGAACAACTTCAGGTTC
TCCTCGGTGGTGTACGGGGCCAGCCCGCCGATGAAGAGCTTACGCAAGTGCTCCAGCTCGCATATGTCCTACCGGTGCAGAGGTGGTAAGTGGGT
TAGCCAAGTGGGTTGGCATGTGGTGAAGGGTGGTATGTGTGAAGGGAAACAAATATAGGTGCGTCACTTGCCAAGCCGCATACATGCACAGAAAG
GTACGCGTATGTACTTACATCTTCCTCGCGATCTGCAAGCACAATCACATCGGCGGACTCGTCCGATAGGGGCTCATCCTTCACCATTGTGTTAG
CAAATTAATTATCACTAAATTTAACCGAAATTAAGAAACGAAAACGACCAGTTTGCACGTCGAACGGTTGAAGCGAAGTGAAAATTGTGCTGTCA
GGAAGCGAATCATTGATTCGATACACCCACTCTCTCTGTTTGTTATCGATAAGTTGGTTAGGGGTATTCTTGAAATTTCTAAAGTGCCAAGTTTC
TTTACTATCGTAATAATAAATACATACACGAATTGGATATGCGATAGCTGTCAAATTGTAATATAGTTTTTCAGAAGCAAAGCGAAAACCGCCAA
CGTATACTAGCCCCTTTATGCATTCAATTGAGTATTCAACTTAAGTTCTAATGTCGGATTCGCCCCATGAGGAGCACCGCTTGTGCGGTCTGGGG
AATCACACGCTGAGGTCCCCGTACCGCGTAATCAGAAATCCGCACCTGCTGAAGTTTGGCCAGCTGATAAACTCGGAGCTGCGGTCTCAGCCACT
GTGCCTCTCGTGCTACACGCAACTGATCCAGCTCTACCGGCTGAAGAACAACAATGCGAAGAGACACCTGGCAAATAGACAGGCAGCCAGTGCTA
TTCTCTCGAGGAGCAGTAGTGAGAAATCTCATGAGTCCGCGGCTAGTGTGTCCACAACACAATCCTCGGAGGAGCAAGAATCAACCACTAGCGCA
GCGCCGGCGGCGGCGGCTCAAAGAGCAGGAAGCCAGTTGGTTGAGTCCAATTCTTCCGACGATACACTTTTCTCCGATGACTACGATCCCAGCTC
GAATCTGAGTTTGAATGCCGTGAATGGAACGCGGCTACCGAATGTCCAACCAATTCCGAAAAGGCGCCAGTTTGTGCATCTAAATCGTGAAGCTA
TGGCCATTTATCTGGCGGGAACTACTGGGGGATAATGTTTGTTTCATTTAGGATATTTTCATAAATTAAATTTGAAATAACACTGTTACCATCTA
TGTAACCATCTATCGATAGTTTCCGCCATGTTATTAGCAGCAGAAACAGCTGGCTGAGCACCAGGGCTGCATTATTGTTTGTTAGTTTTGCTGTT
TGGTTTTTAACAAATTTCCTGGTTTTCCCTCAAAAACCCTCTCTTATATAAATAAATCAAGTGCAAAATGCTGAGTCCATAACAACACACGTAAG
TTTGTTGGCAAGCAGTGAGTGATTTCTTCGAAAAGTGCAATTCCTGCAATCTGTTATGTTTTCACAATGACTTTTATTCGATCTTAATCTAAACA
GTTTAAAGCTCAAATAAATGTAATCAATTAGCAAGTATTAGCAAATGTTAATAGGCGTTGTTGTTTCTCGACGTCGCTGCTGCTGCTGCTGTTGT
TGTTGTTTTTGTTGTTGCTGGCGCTGGAACTGGTCATCGATGTCGATGAAATTGGCATCCTGCGTGTTATCCTTGGGCAGCGCTGCCGGCGTCGC
TGCCGCGGCATAGTAGTTTAGGCCCACGCCCACCGCCACGCCCCCAGTGACGCCTCCGGGGGGCATGGTCGTGGCAGCCTGACCCATTATAGAGC
TCATAAAACCATTGGCCACGACAAAGTTTCTGAAAAATTGATTACATCAATGTACAAAATAATTTCGAGCAACCCCCTCCGGCCCAAAAAAAAAA
AAAAAAAAAAAAAAAAAATATGGAAAAAAATGATATCGTCTAATTGGGTCTGTGTGCGCATAAATGTCGTAAAATTAATTTCGTGTTAATTTCAT
GTTGGCCATCAATTAAACTAGTGACATTTCACTAAATTACTTCCGTTTCGAAAATGCAGGTATAAATACCCAGTTAAAATCCTCTTCACGAGCTA
TTCATCAACCATTAATTTATGTTCATTTAATATTATTTAACTCAATCAAAATCGATGATATCTTTGTACATATGAAACAGAAAAA
(SEQ ID NO: 22)

Exon: 1001..1555
Start ATG: 1001

Transcript No. : CT33871
ATGTCGGATTCGCCCCATGAGGAGCACCGCTTGTGCGGTCTGGGGAATCACACGCTGAGGTCCCCGTACCGCGTAATCAGAAATCCGCACCTGCT
GAAGTTTGGCCAGCTGATAAACTCGGAGCTGCGGTCTCAGCCACTGTGCCTCTCGTGCTACACGCAACTGATCCAGCTCTACCGGCTGAAGAACA
ACAATGCGAAGAGACACCTGGCAAATAGACAGGCAGCCAGTGCTATTCTCTCGAGGAGCAGTAGTGAGAAATCTCATGAGTCCGCGGCTAGTGTG
TCCACAACACAATCCTCGGAGGAGCAAGAATCAACCACTAGCGCAGCGCCGGCGGCGGCGGCTCAAAGAGCAGGAAGCCAGTTGGTTGAGTCCAA
TTCTTCCGACGATACACTTTTCTCCGATGACTACGATCCCAGCTCGAATCTGAGTTTGAATGCCGTGAATGGAACGCGGCTACCGAATGTCCAAC
CAATTCCGAAAAGGCGCCAGTTTGTGCATCTAAATCGTGAAGCTATGGCCATTTATCTGGCGGGAACTACTGGGGGATAA
(SEQ ID NO: 23)

Start ATG: 1

MSDSPHEEHRLCGLGNHTLRSPYRVIRNPHLLKFGQLINSELRSQPLCLSCYTQLIQLYRLKNNNAKRHLANRQAASAILSRSSSEKSHESAASV
STTQSSEEQESTTSAAPAAAAQRAGSQLVESNSSDDTLFSDDYDPSSNLSLNAVNGTRLPNVQPIPKRRQFVHLNREAMAIYLAGTTGG*
(SEQ ID NO: 24)

Celera Sequence No. : 142000013384172
TATCTATACTCGCAGATGCACTAGCCTAAAAACGCAGCTATGTTATTTTTATATCTGTCACCCATACAGCAAAAGGGTACACGACTTGCAGAAAA
GTATGTTCAAGAAGAAGGACTCTTTAAAATGCATATATACATCACTAACTATGTATATATATCATATAGATTCTATAGAATTTGTTATGTACAAT
GGTTTTCTACATCTTAGCTAGGAAAATACGCAAGCAACAACTTTAGAACATTGTCTAATAACCAGATATTAAGAATCAATTACATATGCTGAAAG
TTATCTTTTAGGATTTGTCATTTTATAGTCAGCTTAAATATGTGGCTGCACCGCCTTGAATGATATTTATTACTTAGCTATTCCCACTCACCAAT
CCCAAAAATTCACTCCAGAACGAGGGAGCCACCAATGCGCTACTGAAACTGGACGGAACCAGCGTGGGAAATCGCTCGATAGCCGTGCGTTTGGC
CAAGAACATTAAATATGTAAGCAAAGACCTTCGAGTCACCAAGCTAGCTATCCAAACTTCAAATCGATTCTGTTTCCTATATATATATAGGATGA
AACGCAGAAGCCAAAGCCGCGCCTGGATATACCGGCCTTGGGCACAGGTAAACGCGAGGAGAAGGTCAGCAAAACGGAGGCCATTCGGGCCATTG
AGGCCAAGCTGAAAATGTTGGAGCGCCAGACAGACGACAATCTCGAGCTGAATACAGCGGGCAGGGGCGAGGCCAACGTGCCCTTCATCCAGCGC
TATCAGTTTAACAAGGATCGCGACGGTTCGCAGCGCTACGGAAAGTCATCGGCTCCCATATCATCACCAGCAGCGTCCCAAGCGCCACTAGGCTCA
ATCGACCCACACTCGACTTTGCCACCGTCTCACGCATTAGTCTGTAAAAATCATTAGTACTTAGGGCGCTACCTCAGCAGACGAGCCTTGCAGGT
GTAATTTACAATTAATTTATTAAAAAAAAAAGGTACAATCAGAGCGAACGTCTATTTGGGTGCGAACAAGATCTTGCCGCGCATGTGATCGGGCAG CGGCACGGTTCCGGGACAGGGCACCTGGCCGGGGATCTCGCAGATGCAGTGCCTGCCGCATCCGTAGCCAAAGTTGGCCGGATTGTCCTTGCTCT
CCTTTAGGCGCTCCTCTGCGTCCAGTTGCTCCCTGAAATTATGGAATAGGATGTGTATTAAGTTATAGCTTATGATGCTGAAAAGGTATCAGAAC
TGAGCTAGCTTCTTCTTAACTCCCAACTCATAGTTCTACAAAATGTGATACACGAATAGAATCTTGATGTGTGTTCTCACCGGGTTTTGCCCACC
ACCTTAACCAGGTGATCGATGATGTCGTTCCGATTCCGACTGTCCAAATCTATAAGCATATCGCGTCCATCGTCGAAGTAGCAGCGCACAAACGG
CGAGGGCGTCATGTTCTTCAGCGTGAGCACCTGGACCTCGGGATTCTTGAACTGGATCTGCGGTATGTTCCAGAAAACAAAGTCCCTGTGCGCAT
TGCATTTATTAGCGTATATTTCAGTTATTAGACAATTCTATGCCATAACTTACCGAGCGCCCGCGTGATGAGCACCATATGTGTTGTAGTTCACG
CTGAAAATGCGCACCTTGTCCTTCAGCACCAGCTTACCGGCATTCAGATACTTCAGGGTGCGGCGGATGGGCTCACGGCCCTTCATGAACGGCAT
TTTGCACTTTTAATTCAAATACGCCTAAGTAAAACAAAAGAAATCCAATAAAAGAGCGGCTGCTTGTGTAATGCGAACAGCTGATCGGTCGGCTA
GTGGCTCCCACAAGGCGCAAGCGGAACTATCGATATAAGCGCGGTATCGATGCAGACCAGAAATGTTTCCACTTAAAAGAAAAAATACGAATATT
TATATGTTTTTATATGGGCGTGGCAGTTTTGGGTGGTTTGTAGACGTAATAAAGAGACATCAGGAAGAAACCTGAGCTGCTTGCATAATCTTAAC
TTTCCAGCATTTGCTCTGACGAGCGTTAGAGTGGGTGTGGTAACATTTGGAAACAAACTTGCGTCTACGTCTCTAGAAGCTGCATGCTTCATCTC
AATATTCTAGCTTTTATAGTTCCTGAGATCGAGGCGTTCATACGGACAAATGGACAGACGGACAGGGTCGGAACAACTCGGCTATTGATCCTGAT
CAAGAATATATATACTATACATACGGAAACACTTCCTTCTGCCACTTACATACTTTTCAACGAATTTAAAATACCCTTTACTCCACGCGTAACGG
GTCTAAAAATGGGTAGAACTATTATTGACTAACATAATTAGAAAACGCGTTAAATCTTCAATCTTACATTTTTTAAATTAAAAAAAAATTTTTTT
TTTTGAGCATGGTCTAAAAAAGATAAATGCTTGCTTATATTTCATTTCAGTGGAGTACGTCTATTAAATGAAACAACACTTTCGATTTCTCTGGT
CATATATCGATAGATCCGTTAAGCCGAACCGGCTGGCTAATTTGTTTACCTCTTAAACTTAAACTTTAAAGCTTCTTATTCTACCACAATCAGCA
GGACATGGAAATAACACTCGCTCTGATAAAGCCGCACGTGCTGCGGAATACCTATGCAATGCAGCAGATCCGAGCCCTGATCTCCCAGAACTTCA
CCATTCTTGACCAGAAGGAGGTTTGCATTACGAAAGAACTATCTGAGCGA
(SEQ ID NO: 25)

Exon: 1710..1574
Exon: 1510..1316
Exon: 1172..1001
Start ATG: 1710 (Reverse strand: CAT)

Transcript No. : CT34069
ATGCCGTTCATGAAGGGCCGTGAGCCCATCCGCCGCACCCTGAAGTATCTGAATGCCGGTAAGCTGGTGCTGAAGGACAAGGTGCGCATTTTCAG
CGTGAACTACAACACATATGGTGCTCATCACGCGGGCGCTCGGGACTTTGTTTTCTGGAACATACCGCAGATCCAGTTCAAGAATCCCGAGGTCC
AGGTGCTCACGCTGAAGAACATGACGCCCTCGCCGTTTGTGCGCTGCTACTTCGACGATGGACGCGATATGCTTATAGATTTGGACAGTCGGAAT
CGGAACGACATCATCGATCACCTGGTTAAGGTGGTGGGCAAAACCCGGGAGCAACTGGACGCAGAGGAGCGCCTAAAGGAGAGCAAGGACAATCC
GGCCAACTTTGGCTACGGATGCGGCAGGCACTGCATCTGCGAGATCCCCGGCCAGGTGCCCTGTCCCGGAACCGTGCCGCTGCCCGATCACATGC
GCGGCAAGATCTTGTTCGCACCCAAATAG
(SEQ ID NO: 26)

Start ATG: 1 (Reverse strand: CAT)

MPFMKGREPIRRTLKYLNAGKLVLKDKVRIFSVNYNTYGAHHAGARDFVFWNIPQIQFKNPEVQVLTLKNMTPSPFVRCYFDDGRDMLIDLDSRN
RNDIIDHLVKVVGKTREQLDAEERLKESKDNPANFGYGCGRHCICEIPGQVPCPGTVPLPDHMRGKILFAPK*
(SEQ ID NO: 27)

Celera Sequence No. : 142000013384525
TTCGGCGCCACCGGCCCCTCTTCCTCAGTGGTCTCAGCTGCGGCGGGGTCTTCCTTTTTATCACTCGGCGTGCCAGGTCTTGCTGTGGATGGCGT
CGATTGTGTGGACTTTCGGTGGGCCCGGCTGGTTGTAGAGTTGGCGGTGCTGTTAGTAGTCGTGGTGCCAGTGCTCCCGGCTTCCGATTTGCTTC
CCGGTCCGGCGCTAGTTGTTGGTGTGCTGCTAGCGGTCGATTGCGAGGTGTTGCTATCCTTAGACGGCGTCGAGGCACGAGATTCGTTCCGCATC
TGTTCCATTTTCTTGGCCTTGGCGCTGCCTGGTATGTAAACACCTTAATTTACAACTCCAGGAATTGCGTTTGTTACTGAACTCACCTTTCTTAT
TATCCTTCTTGGAGCGCTCGCCGCACTGGCGAGCCAGTTCCTGACGTCGCTTGACGTTGTCATCGTTGTACTTGAGGACTCGGTTCTCGGGCACC
CACTCGTCCCAGCTGAAAATGAAATGGCTTTCATGCAGATCGGTGTTCATACTAGTAGCTTTGCTCACTTTTTACTCCAGCCCGCGTAGTGGATG
TAGTACTCAACCGGCGTCGCATCGGGTTTTGTTTTCAGAACCTTGGCCTCGTAGATGAGCGGTCCGTGGAAGCACAGAACCCGTTCCCCTGCAAA
TGGCGCCAATGTGTTTAATTTGATTTATAGTTGGGCTTAAGTTATTGCCCTACCATCCACGAACAGAGTGTTTGCATCGGTCCCCGTGCTATAGT
TTTCCACTTTAGCGGGTTTTACTTCTCCCATTTTATTTTCAATAATAGATAATTAACAAATCCTAGAGTGACCGTGCGTGACGCATAGGGCTATC
GGATGGGACAGTACCGATGCACTTATCGATTATTTACAGGGTATTGTCTTGGTAGATATTAACAATATTGATTTATTTATGACTATGTACATCAA
ACAGTCTGTTTTTATGGGTTGTTTTCTTAATGATTTTGAAGGCATCAAGTCTAGTGCTTCGCTGTCGTCGGCTGATCTTCCTGCTCCTCCCAGGG
ACGTGGACCGCGTTTGTTCTCCCAGTTCTCTATGTCCACGGACTTGACTTTGTCGTACTCCGACTCCAACGTCACATCCTTGCGGTTTTTCATGC
TTACGCCGTACTTTTTCATCTCCTCCGGCGTTACCGGCTGCTTCTTGGCGTACTGATACCTGTAAAGGGAGGAGACTCATGAGTTAGCTAAGGAT
TTCCCGGAGATTCTTGAATGCTAGCCTGAGGTTGGAGAACTGCTGCAGTCCAAAGGAGCCAGCCACCATCATGATGAGGAAGGGTATGCCATATT
TGAACGATTTTCGTGTGCTGTAATAGTTTAATTTATCCACGAGAGACATTGTTGTTATTTTGTGTTATGACATTTTGGCACATGCGGTTACACTG
CAAGTTGAGAACGAAGTGTGACCAGTTATATGATAATAAAAAAATTGGCGCAAAATTTGAACACCGATTTCTTATCATATGCAATGTAGTTATAT
TTTATTAAAATAACTTGGCGATAGTTTTAAAAATAATTGAATTTAAGCTAAACTATTAACAAGAATATTTAAAACATAACATTTTGTAATCGAAA
AAAGTTATTTTCAATTTGGCACACAGCACTTTATTTAGCCACACACACTAGGCGCCTATGTCAATCAATTTGTGCAGCTGGTGTCGTCTTTGAA
AATAGTTGTCCTTGAATCCAAATCGAAAGATTTGTTGTCCCTGCCAAGTGCGAGCAAGTTCTGAATAATTGCAAAACATTGTTTTCCGGCGCACG
CCTAATGCCCACCATTTGCATGGGGTTCGACGATAAGTTCAAGGTCCCCGCCGTCTCTTTGGTTTTCAAATAATTGACACTGACAATGTTGAAGA
GCGCCAAAACGCTGTTCACATGCACACGACATTCGATCCGGATCACCTTGGCCAATTGCAGGCTTTGGCAAGGCAAGTAGCTCGCGGCGAAGATT
TCCTTTTGCTGCCCACAGCTCCAACCAGTTCGCGATCGCTGCGGCTTCATTCACAAGGAGCCGGCGCCAATTGAGTCATCAGAGGCACCCCCCCC
CCCCCTCCCGAGAGACTGGGATAGTCCCACACCCCTTTCCCAATAGATTATATTTCAGTTTGCAATGCACCCTACGCACAGTCTTTTAGTTGAGT
GATTTGCCCAATGGGAAATAATATCATTACAATTAAAAGACCAAGGTTTTCATTTAGTATTGAACCTGATGAGCCTACAATGAGCTACATACCTA
AGAAGTAAAACTTCTCCAACAACCCGT
(SEQ ID NO: 28)

Exon: 1307..1276

FIGURE SHEET 8

Exon: 1199..1001
Start ATG: 1307 (Reverse strand: CAT)

Transcript No. : CT34684
ATGATGGTGGCTGGCTCCTTTGGACTGCAGCAGTATCAGTACGCCAAGAAGCAGCCGGTAACGCCGGAGGAGATGAAAAAGTACGGCGTAAGCAT
GAAAAACCGCAAGGATGTGACGTTGGAGTCGGAGTACGACAAAGTCAAGTCCGTGGACATAGAGAACTGGGAGAACAAACGCGGTCCACGTCCCT
GGGAGGAGCAGGAAGATCAGCCGACGACAGCGAAGCACTAG
(SEQ ID NO: 29)

Start ATG: 1 (Reverse strand: CAT)

MMVAGSFGLQQYQYAKKQPVTPEEMKKYGVSMKNRKDVTLESEYDKVKSVDIENWENKRGPRPWEEQEDQPTTAKH*
(SEQ ID NO: 30)

Celera Sequence No. : 142000013383769
CAAAATATATGTGTATATCCATATTTCTATATATATATATATATATACATATAAATATAAAGGAAAACAAGAAAATGAGCAGTGCGAAATGTAGC
AAGTGGAATAGAAAATACTCTCACGCTCAACACTTTTCTAACCCGTTTGTAATGCATATCTGTAGGGCCTACCGTTTTAATCTTCTATAAGAAC
TTTCCAACACTACCACGTCGACTGTGTGATGGAATGAGACTGTACTGAAGTTTTTTTTTGAAATTTATGTAAATAGCAGCAATAGTAAATAGTA
TCTAAACATGTCTGCAATAGAGCATTCCCAAGTCGTCGCAAGGCAATTTTACATTTATTTATACATTTTTTTTTTTGCAATTCTCTGTTGCATG
ATGGAAAAAGAAAGGCAACAAGAACATGCAAAGAAACGGCGAAATAAGAAGTGAAGAAGAAAAGCAGCGGCTATGAATGTGCAGTGTGTCCGTGT
GCATTTATGTATATGTATATGTAAGACTTTTGTGAGCGGGGAGTAGTAGTGAAATGTAAGAAAATGAAGAGAAAATAGCACAACAATAATAAAC
AAGTGCAGCAAAAGGAGCAGGAGTCGAACTCCCTGGGAAGTAAAGCACTCTTCTGAAAACGGTTGATGGGGGTCTTCAAACCCCTATAATTCCAA
ATGCAATGCATCTACTGAGGATTGCAGTGAACTCTGTAATTAGGTTTAAATTGTCAATTTTTTTGAATCATTTATAGTTTGATGGGCAATTGCAT
TGATTGGATTCCTAAACCATAGAACACTTTTCGTGGACTATTAAACATTAGGATTAAATTTTAAATTTATTCATAGATATTAATATACATATTCA
AGACGTTCATATTTTAGTTGAAAATAAGAACGACCTTCAGTTATTTACTTTATTTATCTCCTTTAGTAAGCCCTTTGCAGCACTGTATTCGCTGC
CACTTCTTGCCATGCCTCTCGTAACACTACACGTAGTGCAACCCACTCACTATGCCCTTTGCAACACTCTCCCTGCCTTGGTATCCCAATCCCTG
AAATGGACTTACGTCTTCGGAGTCGTCCTGCGACTGTAGGTTCTCGGAAGAACTGGATGATTGCATTTGCTGCTGTTGTTGTTGTTGCTGTTGCG
AGTTCTGATGCTGCTGCTGCTGCGGATTCTGATGCTGCTGCTGCTGCGCGATGGCGTCGCTGTCGCTGGAGGAGGCCGTCGACGAGGAGGTGGCC
GCCGCTGCTGCAGAGGCGGCAACTGCGGCCGAGGCAGAGGCAGCGACGGCTGCAGCGGCCGCCGCCGACTGATGGAAGTTGGAATTATTTGTCAA
CTGCTCCGAGCAGCGGACGCACGTGGGTATGCTATAGCCGGGCACCTGGAACAACTGTAGGGCGGGGGAATAGAATAGAACAGAACAGGACACGT
GAATTAGAGAGTGCTTCCAATTGGAAAAAAAAAAACCAATAATGCTCTTTATTTATTGTGGCAACTCAATCTTATTCCACACATACCCTCCCCCTT
CCATGCCAACTAGCCCTTTCTCTTTTCCACCAACTAGAAATAAGAGCCAAGAAGATAAACACACGCACACACACAGGCACGCACACATGGAGAGC
GAAAAAGAAAGAAAAGAAACTACAATAACAACAGCACCAGCAGCTCGTTGCTTTGTTGTTGTTGTTTTCATTTCATGTTATTTTTTTTCTTCGGT
ACAACGTTTTGTTATTCTTTCGCTTTTTGTTTTGCTTTGCCGCCGCTCTGCCAGCGGCGGCGGCAGAGGCGTCGCCTACAAAAAAGGGGTTATTT
GGTAATTGTTTAAATAATGAACTAAAAACCAAGCAAAGTTAGATCTGTTTTGTTAGTTTTATAACCGCTTAACTTTAAATTTTTGGGCTTAGATG
CCCAATATAGTAAACCCTCTGTCACTAAATTAACGCGCAGCCACTGCGTATTTGGCTGCCTTGGCGCAATTTCTGTCATTTTGTTTTAATATGTA
TTTCTTTTTGTGCGGTTCATGGGCGGCGGGAGGGGGCTGAAAGAGGGGGGCCTGTTCGGGGGAATAGGTTGAAAAGGAGTCAAAGTGAAAAGCGA
GTGGCGAGCGTAAGCAAAATGTAAAAATAATATTTTTTCAAGTTGTCGGCTTGAACAACTTTTCGGGCTGAGTTGGCTAAAAATAAAAATTGTTC
AGCAATAGTTTGGGGTCGCATGTGTATGTGTATTTCTTATTTCTGTGTGTGTGCGTTTGTATGTGTGTGGGGAAAGGGGGGCAATGCGCGCGCTT
TTGAACCCCGCCCCCTGCGCCAACAACCCGCCCGCACAATAACAGTAGCGCGAATTCAATTGTTTAAACTCCACCAAAAGAAAAAAAATCAATAG
AAATAACAAAGTGTATATACCTAAATCACATGTGTGTATATCTTTTTTTTTTTGTTAACATACCGTTGCCGTTTGGAAGCACAATCTACAGATGG
TGTCCATTATAACAGTAAATAAGGAATAGGATGGGGAGCAGGAGAAGGAGGATGCACTTTGTTGCTGACTTTTGCCCCCTCTGCGGTCGTTGTTG
TTGTTGTTGTCGTCCTTCTCCCTCGCAATTTACCGCTATCTTTACCGGTTAACATTCAGCGCCGTTTTTCTTTTTCGTTTATTATTATTTAGTTC
GTTTTTTTTCTATCTTTTTCCTTTTCCTTCCTACTATAAGTTTGTGAACACGATCCAAACGATGTGTGGTTGTATTTGAAACTAACTTTTTGGAG
TTTGGTTTGCGTTTGGATTTCGGTGATCGCTATATGGCATATTATGATGGCAAAAACAAAAAAAAAACTATATAAATGATATAGAAATTTGATTT
ATACGATATTTTCGTGGTACACACACACACGCGCGTTGTTTATGTTTGCCTTGCACTTGCACATACAAGCAAAAATGCGGCGCTGTTGTTGTTGC
TGCTTCGAAGTTCTGCTTCTTTTTTTTGCTTAATTCCTTTGCCCTTTTTTTGGCGTAGTTACACGTGAAAAAAAAAACAAACCAGCGCGTTCGAA
TGCGTTTTTTTTTTGTATTTTACAATTCACGACGAAGTTTTTGTCCGTCGTCTTTTTTCCCTTTTTTTTGGGGCCCGATGTTATTGTTGCGCTGT
ATGCGTGAGCCGTGTGTGTGTATGTGTGGGGAAAAAACGAATACGATAAGAATACGCGGTATAGTTGTGCTGCTCTAACCCACAGGTTGGCTTGG
CCGGTGCTCCTTGGCCTGGCCTATCGATATTTCTATCGATTTCCGTAATCGAAAACGAGGCGGGTAATGGAATCGTTGTTGAAAACAAGTTTTTT
AATTTATTATTTATTTAATATTTAATTGCAAGTCCGAAAGATTTATTTTATCATAGGTTATTTTATTTAAATAATTGATGGTGTTTTTTAGGCAG
CCATAGAATCATGAACTTTATTTTACAACAGAATAAATATAAAATCATTTTACAGAA
(SEQ ID NO: 31)

Exon: 2477..2439
Exon: 1384..977
Start ATG: 2477 (Reverse strand: CAT)

Transcript No. : CT35541
ATGGACACCATCTGTAGATTGTGCTTCCAAACGGCAACGTTGTTCCAGGTGCCCGGCTATAGCATACCCACGTGCGTCCGCTGCTCGGAGCAGTT
GACAAATAATTCCAACTTCCATCAGTCGGCGGCGGCCGCTGCAGCCGTCGCTGCCTCTGCCTCGGCCGCAGTTGCCGCCTCTGCAGCAGCGGCGG
CCACCTCCTCGTCGACGGCCTCCTCCAGCGACAGCGACGCCATCGCGCAGCAGCAGCAGCATCAGAATCCGCAGCAGCAGCAGCATCAGAACTCG
CAACAGCAACAACAACAACAGCAGCAAATGCAATCATCCAGTTCTTCCGAGAACCTACAGTCGCAGGACGACTCCGAAGACGTAAGTCCATTTCA
GGGATTGGGATACCAAGGCAGGGAGAGTGTTGCAAAGGGCATAGTGAGTGGGTTGCACTACGTGTAG
(SEQ ID NO: 32)

Start ATG: 1 (Reverse strand: CAT)

MDTICRLCFQTATLFQVPGYSIPTCVRCSEQLTNNSNFHQSAAAAAAVAASASAAVAASAAAAATSSSTASSSDSDAIAQQQQHQNPQQQQHQNS
QQQQQQQQQMQSSSSSENLQSQDDSEDVSPFQGLGYQGRESVAKGIVSGLHYV*
(SEQ ID NO: 33)

Celera Sequence No. : 142000013384157
CACCTCCATCGCACCCACACACACCTGGCCGATGTTACAGCACGCACACACGGACACAAACACAGGCAAAGACACACAGTCAGGCAGTCGCAGAA
ATGGTAAAATTGCATGTGTGTTGCGCTGCGCACATTATTGAATTTTCCACGGCGAGATGACGACGACGACGGTGTGCAATTACTCACCTTGGCGT
CGATTGGACTTGACTGACAATCAAGGATGATGGGCGAGAGCAGTGCAAAGGAGTGTCCTTTGAAGTTCGCGAAGGATAACGGTACGGCGACGTCT
ACGGTAACGGAACGTAACGGAACAGATCGGTTCGGTTCGGATCTCGCACACACACACGCACGCACGGAGCAGCTGCTGAAAAGTGCCTGCTGCCT
GTTACCGTTTTCGGTAGAAAAAGAGAGAGACGACTGAACGGAACAGAACGGGAGAAAGGCTCCACGTGGTGGCGATGGCGTTTGGCACGGAACCC
GCGAAGCGGGAGAGGATTCGGTCGCCAATGCGTTAAGGTCACACTGGCACACGGGCGAGGGGCACACTGGCAGGGCCAGCGGATCAGCTAGTATC
GCTACGATTCAAGTCTTAAATAATTTGTAAAATGAAAGAAACATATAATATTTAATAGCATAAATAAGTTTAATTTCATAAAAGCAATAGTTTTG
ATTCGCTCAAAGCTGAATGCATTATATATTTCTATGTAATATAATATTGATATGCTGTATTCAGTACAAAGAAATTGAGACACTGAGACAATTTC
ATAAAAATTTGAAATACTTGTCAAACTTATTCTTTTAAGTGTTTCCAAAATATCTATAAATATTAAATAGCTTGAAGTGAACGTTAGAATATTTG
TTTTGGACACTAAACGATATATCAGCAGATAACGCCTTCGAAATTCGGTCACGTCCAAGTCCCGCATCGTCTGGCCTCACTAACCAAGTGTAAAC
AAAAGTTGTGTTGTGAAGTTGTTTTCCTTTGGTCCAAAAAGGAATTGGTCATGTCGAAGTTGAGCGACACTAAGATCCCGATCACGGAGTTCCTG
GAGGCATACCGTCGCCAGCCGTGCCTCTACAACACACTGCTGGACTCGTACAAGAATCGTGTGTCCCGGGAGGAGGCCTACGGAGCGATCATCCG
GTCCCTGAAGATACCCCAACTGACAGTGTCGGACATAAAGCTAAAGATCAAGAGCGTGCGTACCGTGTACTCTAAGGAGCTGCGCATCTGGATGC
GTGAGAAGGAGCTGGGCAGGACCTACGAACCAAAGTTGTTTTGGTTTAGGTTGGCCGACTCCTTTCTACGCTCCGTTTCCCTCTCCCACTGCAAA
AGGGTAGGATTTCACGATGTTCTTATGTCAATGTTAACCTCTGACCCACCACCAGCAGGGAAAAAATAACAGTTCCAGTGCTCAATTAACGACGA
TCAAATCGGATGAGACGAGCAAGCTTCTTTGCACTGCCGCCGCAGATATCACTATGAGCGAGGATGCGCTAGAGGAAGAGGATGCAGAGGTAAAT
GGCGAGCCGGAGGAGTGTCCTTTGGAGGAAAGCAGGCCAACAGCAAGCATCTGCAAAGATGATTCCACGCTCTGCCTGGCGGATCAACCACAGCA
GGAGCACTATTCTCAGGGGTGCAGCAGCTCCCAGCAGCTTCCTCACACGATGGCACAACGAAAATCAAAGTACATTACAAGTCTGGACTCGGCCG
GAGAGGATGATCTTATTATATTCGGCCAGAGCATCGCCTCTCAGCTGCGAACCATTCCGGATTCATATTCTCGGTCCGTGGCTAAGCTGCGTATC
CAGCAGGTGCTGTTCGAGGCTGAAACCGGGCAGTTTCAGAGCACCGAGGTCAATAGCACGCAACTCCAGAATACCTTTTAAACCATAAGTCTAAA
TTTAAACACTGTGCTCAGTTCTGGCAAAATCCCCAAAAATATGCCACCCTGGCCTAATTTCCAGGGGATATTTATCAACCCGTTTGCCATTCAGT
ATATGTAGTCAAGCTAGTTCTAAGGATTGACGGTTAAGTATAAAATGTAAATAAAAATGCTATCAAGTAATTACAAATTGCTAGCTAAAACAAGT
ACTTTGTAAGTAGTAATACATATGTGGGTTAATTTTTGTATGGCGGAGGTTAATTCGCCTGAACTCCAAGTAATAATAAGCACATTTTAAAAAT
CAACGCATAAAATAAAATGACTAATTTAGTCATACATAAAAAACATATAACAATCAGAGTTGTACAATTATTAAACTTCCTCAATTTTCAAATCA
AAACCCGAATTTCAAAAAAAAGCAAATTATAGTGAATTATAACTATCGATACTTTTTGAACATTTATTCAAAAGTCACCATGCTGCGACTTACAA
CTTAAATTCGATTAAAGTGTTGTTTCATGCTCACACAACAAAATTTGTTGTTATTTTGCTAACATATTTATTAACACTTAACCATATCGATAGGC
AAAGCCGATTGTAATTCACAGTTGTCGTGGATTGGAGCGTTTGCAGTGTTTGGTCACACTATTTATGCTTGCATTTCGTCTGTGTAAATTTCATT
TCACAAAAACCGACATTGTTAAATTAAGCAAATAAGAGTGTTTAAGATCGAAGTGAGAAGAGCAGCAATATGCTGCATTTAAATATAATTGTGAG
TATGGCTAGTGGTATTTCCGAGAACGCATAAACACGCACACATACATTGGTGCGAGAAAAGACTCGCGGAAACAGGCACACGCACGCACACAGCC
AAATTCTCACCCACTGCATTGTTTCTGTTCTGACAGTGGCAATTTCTTTTCGCTACTCTCTTTTCGTCTATTTTTTTTCTTGTGCTGTATTACAG
TCACCAATGTAGTTTTCTTTAACTTTTAAATACGCT
(SEQ ID NO: 34)

Exon: 1001..1333
Exon: 1386..1886
Start ATG: 1001

Transcript No. : CT35724
ATGTCGAAGTTGAGCGACACTAAGATCCCGATCACGGAGTTCCTGGAGGCATACCGTCGCCAGCCGTGCCTCTACAACACACTGCTGGACTCGTA
CAAGAATCGTGTGTCCCGGGAGGAGGCCTACGGAGCGATCATCCGGTCCCTGAAGATACCCCAACTGACAGTGTCGGACATAAAGCTAAAGATCA
AGAGCGTGCGTACCGTGTACTCTAAGGAGCTGCGCATCTGGATGCGTGAGAAGGAGCTGGGCAGGACCTACGAACCAAAGTTGTTTTGGTTTAGG
TTGGCCGACTCCTTTCTACGCTCCGTTTCCCTCTCCCACTGCAAAAGGCAGGGAAAAAATAACAGTTCCAGTGCTCAATTAACGACGATCAAATC
GGATGAGACGAGCAAGCTTCTTTGCACTGCCGCCGCAGATATCACTATGAGCGAGGATGCGCTAGAGGAAGAGGATGCAGAGGTAAATGGCGAGC
CGGAGGAGTGTCCTTTGGAGGAAAGCAGGCCAACAGCAAGCATCTGCAAAGATGATTCCACGCTCTGCCTGGCGGATCAACCACAGCAGGAGCAC
TATTCTCAGGGGTGCAGCAGCTCCCAGCAGCTTCCTCACACGATGGCACAACGAAAATCAAAGTACATTACAAGTCTGGACTCGGCCGGAGAGGA
TGATCTTATTATATTCGGCCAGAGCATCGCCTCTCAGCTGCGAACCATTCCGGATTCATATTCTCGGTCCGTGGCTAAGCTGCGTATCCAGCAGG
TGCTGTTCGAGGCTGAAACCGGGCAGTTTCAGAGCACCGAGGTCAATAGCACGCAACTCCAGAATACCTTTTAA
(SEQ ID NO: 35)

Start ATG: 1

MSKLSDTKIPITEFLEAYRRQPCLYNTLLDSYKNRVSREEAYGAIIRSLKIPQLTVSDIKLKIKSVRTVYSKELRIWMREKELGRTYEPKLFWFR
LADSFLRSVSLSHCKRQGKNNSSSAQLTTIKSDETSKLLCTAAADITMSEDALEEEDAEVNGEPEECPLEESRPTASICKDDSTLCLADQPQQEH
YSQGCSSSQQLPHTMAQRKSKYITSLDSAGEDDLIIFGQSIASQLRTIPDSYSRSVAKLRIQQVLFEAETGQFQSTEVNSTQLQNTF*
(SEQ ID NO: 36)

Celera Sequence No. : 142000013384734
TACCTTTGGACCGACCGGGAGCTGTTGATGCACCTCCAGAACTACACTCCCCTGATCCTTCTCATCGATTTCGTGGAGAGAAGACCCGAACCAAGCG
CTTCTATGAGAGCTCCGAGCGCTATGAGATACTCATGCTGGTCTTCATCATGCGCAAGGGAGCGCCGTTTTGTGAGAACAAGCGCTTTCCAGCGG
AGTACTGGGTTAATCTATCGGTGGGACCAATTGCCGAGGCGTTTGACCGTCTGCAGGCGGCCATCGATATACCGGATCCCCAGCTGCCGATCCAC
ATGAGCGTTACAGATTTGACCAGCTGGAAGCAAATGTTCGACCTGGCCATGCTGGATATACGGCGTTTTGCGTACTACACCGATCCCTTGCAGCT
GGCCGATGCGGGCGTCTTTAACCGGATCACCTTTGAGCAGCGATTCGGAATGCAGTGGCAGGAGTAATGGGAATTGATGCACGTTACTGGATATA TATTCACGGGAAACAGCATGTAAGCACACCATCAGCACCAACACACTTTCCCAAATTGGGATGGATCGTGGGGAAGGCTACTGCATAAATCCGAA
CGAAAGCATTTAGTTAAGTATTAATAGGACGCACTAGAGCGCAACCGATCCATCCAATCCCACATAGACAGAGTTATTTGTTGCGTTAATGTCCC
TGCATAGCGAAATCTACTGTGCCTTCTCCAAAAACTCCAGATCCTTCTGCATTCCTTTCCCTCCAATCCGTCAACTTCATCTCTCCTCCGACTCC
TCAAATGTATCTGTAATACAAGCGACGTGTAGGACCCAAAATGCTTTAATGGAAATAAACGTTAGTTACTGTTCAAACGCCTGCCTATTTATCTT
TGTAAAATAGCGATAAATCATTCACAACACGCATTACTCACTATAAAAATAGCACTATGTACACTATGAAACTACACCTATGTTCCTAATGCGAA
TTCAACGAGATCCTCGACAGTCCCATTCTTAGGGATCGGATCATCCAGCCTCATGGCTGCCGCTTAGGAGCGCGATCCCGGTCAAAGATGCCCAG
CAGTTTCCCACGAGTCATCTCCATTGCCTCACGCAGTCCCAGCTGGTAAATTTCATCATGCATTGACTTTATTTTATCGATCAGATCCTCGGGAG
GGAGCTGGGCTAGTTCTGGAATAGAAAAGTAGGTAATGGATATGCTATTCTTTAATATACTATTCTTAAATCTCATTGACTTTGCAGCTACTTAC
CATTAATCTTAACCATATCATCATCGGTCAGATTGCTGGTGTAGTTGGTGCTGCGCGTGTACATCGGCGTGTCGCTCATGGAGAGGAACTCGTCC
ATTCCGGGAACTGGAGCAATCGAAAATAAAGATATGCGTTAAAAATGGCGCCAATTTCTTCGTGCTCACGTTTTCTACACTTACAACGCTCTGGC
CATTGGACAGGTGAGGGTCGCAGAGTTTCCATGGAGATGAGCTCGTCTTCCGGCGTTATGGGCCGCTCCTTGACCTCCGGGACATCCTTTTCGGC
CAATAACGTACTACTGCTGGACGCTGAAGCCTTCTCCACTTCCTCGTCCGCCGCTTTTAGAATGGTTTCTGCAAGAAAACCTCGTTTTATGGCGC
CTTTCATGTGATTTAAATATTTACTCACCTGTAGAAAGCAAATCCGTAGTTGTCTCTGCGTTGCTCATCGCGGATAATGTTGAAAAACTCCAAAA
ACTATTGAAAATAAACACGGAAAGATGCCAAAAAATCCGTGGGCTAATCACTTGCCACCTCGTTAAACAAAAACTATAGCGTTGCCACTTTCAAC
AATCACTATCGAATACTATCGATTTACCGCCAAGCCAGTGCTAGAAAGCACCAGGAAGTATAAAACAACTGATATTTTTGGTAAACAAAGAACTG
TTGTTATTGCTTTTCCTGGTTTTATTAATAGAAGTTAAAAATAAATGGCACAACAATTAGGAAATGAGCGTGCCTCGACTTATACTAAATTCAGA
GTGGAGAGCAGGCGTCGTAGCAGAGAAACGCGAACCTCTCCGCGACCTCTATCGTGCTCTCTTTTCCACTCACGGTCGTTTAACGGCGCATAGAG
ACAACTCTGCGCTAGGTCGCCTGCTCTCGTTCGCTCTGGCGCGCAAACGGCACTTGGCACACTTCGCACAGTGGCGCCAAAAAATATGTGCCCGT
AAAAAGCACATGTGCTGCGCAGTAGTTGTCCAGAACAACACAACACGGATGTCTAACCAGTTATTGAAATAAACTTATTCAAGAACATCTTAATA
ATAATATAAAATCTTAAGGAATAACAATATCTTATCAAGTTTTTATCAATTGGCGCCGCCGCCTGGTAGCACTGTTCGCATACGCAGACTTTTGG
CCACCACTGTTTTCCCATGCGCCCTCGCACTTTCTTTCGGTTTTCATTCGCTGCTCCGCTCTCACTCAGTCAACAAGCACTCATACACACGCGC
TCACCTGTTCCGCCGCCCCGCTACCCCGTCTCTCGACATTACTGCGACCGCTCCCGTTCCGTTTCATTATTTTTTTGTCGCTGTCATTCAGTTG
CCGTTTTAACTTCGCCGCGCGAGAAGCGGAAACTTTTGCCAGTCCGCTCGAGGAAAATAGAAAAATACTGCAGTGCTGCTGCAGTCGTGCAGCTC
GTACATTTCGTTTCGTTTCGTTT
(SEQ ID NO: 37)

Exon: 1683..1644
Exon: 1588..1415
Exon: 1340..1236
Exon: 1155..1001
Start ATG: 1683 (Reverse strand: CAT)

Transcript No. : CT36029
ATGAGCAACGCAGAGACAACTACGGATTTGCTTTCTACAGAAACCATTCTAAAAGCGGCGGACGAGGAAGTGGAGAAGGCTTCAGCGTCCAGCAG
TAGTACGTTATTGGCCGAAAAGGATGTCCCGGAGGTCAAGGAGCGGCCCATAACGCCGGAAGACGAGCTCATCTCCATGGAAACTCTGCGACCCT
CACCTGTCCAATGGCCAGAGCGTTTCCCGGAATGGACGAGTTCCTCTCCATGAGCGACACGCCGATGTACACGCGCAGCACCAACTACACCAGC
AATCTGACCGATGATGATATGGTTAAGATTAATGAACTAGCCCAGCTCCCTCCCGAGGATCTGATCGATAAAATAAAGTCAATGCATGATGAAAT
TTACCAGCTGGGACTGCGTGAGGCAATGGAGATGACTCGTGGGAAACTGCTGGGCATCTTTGACCGGGATCGCGCTCCTAAGCGGCAGCCATGA
(SEQ ID NO: 38)

Start ATG: 1 (Reverse strand: CAT)

MSNAETTTDLLSTETILKAADEEVEKASASSSSTLLAEKDVPEVKERPITPEDELISMETLRPSPVQWPERFPGMDEFLSMSDTPMYTRSTNYTS
NLTDDDMVKINELAQLPPEDLIDKIKSMHDEIYQLGLREAMEMTRGKLLGIFDRDRAPKRQP*
(SEQ ID NO: 39)

Celera Sequence No. : 142000012757653
GGAACTGGCCAGGGCGCCAATAACTGCGTGTAAAGATTTGGCCTGACTTTCGGCCGAGGGCGGGTATTCCGTAGACTGTATCAGATCCTTTGTGC
CCAGGTGGGTCGAGACGTGAGCAAGCGTTTCGGTGCTAAGTAGATAACTGGCGATCGCCTGGAGTCCTTCATTAGGGACCTTCGGTAACTGGTGC
TGCAGGAAGGCCTCAACGTAGGCACGGGCAATTTGTTGGCCCTTCTCGACCAGATCGCTATTGTGAGGCATCTGGAGGTCAGACTCCTCAATGCC
TAGCTGCCGACGACGATCCTCCTCCCGCTCTGCAAACGATTTCTCTGTAAAAGCACGCTGCAGCTCCGACAATTCAAAGGATTCGCCCAAACGCT
TGCCGAACGCGAAGAGCTCCGATCGCTGGTTCCACTCCACGAACCCAGAACGCCGCTCTGGCTTTTGTGGTCCTAGTTTCTTCTGCCGGTGGGCG
AGCTCACGTAACGTTGGCGAAACCCATCGCTTGATGTGGCGCCTCGTTTGCACTGCCGAAAATCACGATTACTGACTGGCATTAGGTGAATCCGG
GTTACTCACCAGTCGGTGAGCCCCTCCAAGAGCTTGACACGAGCCAGGAGACCAACAGCACTGCGTAAGAATGACATCTTTAAAGCGATCTTAAAA
ATAAGTAACGAATATGTTTTCGCGCATGGGAACTAGTGTTGCACGGGTTTTTGTGGCAGTGATGGCAGTCTAACCGTAAATATAATTTTTATAACT
TATAACTTAACTTATACATTTTAATAATATTTGTTTCTTGTTGTTTCTATATTTATTCAGAGATGTATAATTAAAAAAAAAATAATAATAACTAAA
TATGTTTCTTTATGAATTATAATTTTATCATTTAATCGAGTAATTATAACGAAAAATACTTTCAGCTTTTTATTTAGCGTTTTGTAGCTAAAAGG
CGCCAGTACTAAATTGCGTTGGTGGCACCCGCTCGTTTTCCAACACTCCCGCAATAGACGCCATGTACATGTCTGTGTTTGTGTATGCGCCAAGA
AAATTTAAGTCGCGGAATATTAACAAGGAATCCCTGCCAGAAACAGGGCATTGAGAGACCACAGAAGAAAATATACCCAACATGGCACTGCAGAC
ATACGGGGACAAGCCGGTGGCCTTCCAGCTGGAGGAGGGCGGCGAGTACTACTACGTGGGCTCGGAAGTGGGCAACTACATGCGCCACTTCCGCG
GCATTCTGTACAAGAAGTACCCGGGAATGACCCGCATCGTCCTGTCCAACGAGGAGCGCAAGCGGCTGGCTGAGTCCGGCCTCAGCTCCCACATC
TTAGCCAGCTCTGTATCGCTGCTCCGCGCCGTAGAGGTGGATGATATCATGGCCGGCAACGATGAAAAGTAAGTGGGCGTCTTACCTAAGTAATG
TCCCCAGAATAGTAACTAAATAGGGCCTTTCCTAAAAATTCCAATTAACTTCGTTGATATCTACTTCCTACTAGTCCTACTTAAACGTTTGTTTT
TAAATGTTTAATCCAATGGTATCAAGTAATCCTTTTATCAAATATAAGACATGTGTACATTTGGCTGAAGATTCTTCATTTTAGTAACATTGTTA
ATGACCACTTAGTTAAAAACCACTTATCATTCTGAAGTGAAGACGTATACAAACACACATAGCCACACACTGCCCAGTTATTTTGAAAAAAATATG
GAAAAATGTCATAGACATTTTTGGCAAAGCTGCCACAATAGTCTGTATGATTGACAACGATTTCCAATTGAGCACGGAGAATTGTATTATTGTCA
GAATGTTGGGTAAATTTTGCCTGCTTGCAGGGCCAATCAGTCAATTTGCTAACAGTTGATTTAACTAACCATGAATCTCCGTCCCAGGTATCGCG
CCGTCTCCGTGAACACTTCCGATACGCCAGTGCCGCGGGAGAGCAAGTCAAAGAAGCAGCCACAGTATGTGCCCACGATGCCGAACTCCAGCCAC CTGGACGCAGTGCCACAGGCCACGCCAATCAACCGAAACCGAGTGCACACGAAGAAGGTTCGCACATTCCCGATGTGTTTCGACGACACGGATCC
CACGGCTAGCCTGGAGAATGCGGCGCAGAAGGAGTGCCTGGTGCCCATTCGACTGGACATGGAGCTAGAGGGTCAAAAGCTGCGCGACACCTTCA
CGTGGAACAAGAACGAGAGCATGATTACTCCGGAGCAGTTTGCCGAGGTGCTGTGCGACGACCTGGACCTCAATCCCCTGCCCTTTGTGCCGGCT
ATTGCACAGGCCATCCGACAGCAGATCGAAGCCTTTCCCAACGATCCCCCCATCCTCGAGGAGACCTGCGACCAGCGGGTCATTGTTAAGCTGAA
CATTCACGTGGGCAACACCTCGCTCGTCGACCAGGTCGAGTGGGACATGTCCGAGAAGAACAACAACCCCGAGGAGTTTGCCATTAAACTCTGTG
CGGAATTGGGATTGGGAGGAGAGTTTGTTACGGCCATTGCCTACAGCATTAGGGGTCAGCTATCGTGGCACTGTCGAACGTACGCCTTCAGCGAG
GCCCCTCTATCAACGATTGATGTGCCCTTCCGGAATCCCAGCGACGCTGACGCATGGGCGCCATTCCTAGAGACGCTTACCGACGCCGAAATGGA
GAAGAAAATCCGCGACCAGGACCGCAACACGCGCAGAATGCGACGACTGGCCAATACCACAACTGGTTGGTGATCTTCCGCCGATCCAGCAATGT
GTCACTAATGTAATCCTCCTATTAAGTACCATTATGCATCCCAAATAAATGTGTGTCTGTCGATTTTAAAACCTATTGTCTTCTACGCGCTACTT
CCAAAAAAAATAGTTCCAAACGATGTTACAAAATAAGCTGATACTCTTTACTGCTTACGCTAAACTCGAATCCTTATTCTACATTATCCAATACT
AACTTTCTGCCGAATCGGGCTTGTCTTGGTCCTGATCGCCGTCGTAGAACTCGTTCTTAGCATCAACCAGCTTGTCCTCATCGGCTACGGATATT
CGCACGTCGGGATCACTCGCCTCCTCCCGGTTGCTGCGCAGCTCCTCCAAGTCCACATCAGGCGGGGTCTGCACCATTTGGACGCTGGGCGAGTG
CTGGCACATCTTAAGGTTTTCATACACATGCTTAACGATGAGTTCAAGATACTGCTTTGAGTTAGCATTATCTTGGCGTGAGTTAATCTCTGGAT
GGAGTGTAAAGTCGGGGGCGAAAAAGTCGTAATACTCGGTGGCGGGTAGGTCATTTTCAATGTCTTGGTCCACCAGCAGCGAGGTCTCGTGCGTC
CAGCAGCGGGCCACGTTCCGTAAGGTGTAGCCACCGCCTCCGACCACCAATGTGGGTACGTTCAGTTCCTTCACAAATTTGACACACTCACCATG
TCCCTTGGTGCTCAGGGAGAAGCAACCTAGTCGATCTCCAGCTAGTGAATCCGCGCCACACTGCAAAACGATAGCCGTGGGCCGGTAGAAGTCCA
TAATGGCAGAAATTATGGGTTTGAACACCTGAAAATAGCTCTGGTCATCAATGCCCTCCTTTAGCGGCACATTAACGCTGTAGTATCGTCCCGAT
TCGGCGCCTATCTCGTACATGTCTCCCGTGCCGGGAAAAAAGTAGTTTCCGTATTTGTGGAACGAAGCCGTCATCACTCGGTCCGTAAGGTAGAA
CGCCTCCTGCACCCCGTCGCCGTGGTGCACATCGATGTCGATGTAGAGCACCCGAGGATGGTACTTAAGCAGCTCCAGAATGCCGATGACGATGT
CATTCACGTAGCAGAATCCGCTTGCC
(SEQ ID NO: 40)

Exon: 1001..1398
Exon: 1893..2826
Start ATG: 1127

Transcript No. : CT1273
GCAATAGACGCCATGTACATGTCTGTGTTTGTGTATGCGCCAAGAAAATTTAAGTCGCGGAATATTAACAAGGAATCCCTGCCAGAAACAGGGCA
TTGAGAGACCACAGAAGAAAATATACCCAACATGGCACTGCAGACATACGGGGACAAGCCGGTGGCCTTCCAGCTGGAGGAGGGCGGCGAGTACT
ACTACGTGGGCTCGGAAGTGGGCAACTACATGCGCCACTTCCGCGGCATTCTGTACAAGAAGTACCCGGGAATGACCCGCATCGTCCTGTCCAAC
GAGGAGCGCAAGCGGCTGGCTGAGTCCGGCCTCAGCTCCCACATCTTAGCCAGCTCTGTATCGCTGCTCCGCGCCGTAGAGGTGGATGATATCAT
GGCCGGCAACGATGAAAAGTATCGCGCCGTCTCCGTGAACACTTCCGATACGCCAGTGCCGCGGGAGAGCAAGTCAAAGAAGCAGCCACAGTATG
TGCCCACGATGCCGAACTCCAGCCACCTGGACGCAGTGCCACAGGCCACGCCAATCAACCGAAACCGAGTGCACACGAAGAAGGTTCGCACATTC
CCGATGTGTTTCGACGACACGGATCCCACGGCTAGCCTGGAGAATGCGGCGCAGAAGGAGTGCCTGGTGCCCATTCGACTGGACATGGAGCTAGA
GGGTCAAAAGCTGCGCGACACCTTCACGTGGAACAAGAACGAGAGCATGATTACTCCGGAGCAGTTTGCCGAGGTGCTGTGCGACGACCTGGACC
TCAATCCCCTGCCCTTTGTGCCGGCTATTGCACAGGCCATCCGACAGCAGATCGAAGCCTTTCCCAACGATCCCCCCATCCTCGAGGAGACCTGC
GACCAGCGGGTCATTGTTAAGCTGAACATTCACGTGGGCAACACCTCGCTCGTCGACCAGGTCGAGTGGGACATGTCCGAGAAGAACAACAACCC
CGAGGAGTTTGCCATTAAACTCTGTGCGGAATTGGGATTGGGAGGAGAGTTTGTTACGGCCATTGCCTACAGCATTAGGGGTCAGCTATCGTGGC
ACTGTCGAACGTACGCCTTCAGCGAGGCCCCTCTATCAACGATTGATGTGCCCTTCCGGAATCCCAGCGACGCTGACGCATGGGCGCCATTCCTA
GAGACGCTTACCGACGCCGAAATGGAGAAGAAAATCCGCGACCAGGACCGCAACACGCGCAGAATGCGACGACTGGCCAATACCACAACTGGTTG
GTGATCTTCCGCCGATCCAGCAATGTGTCACTAATGTAATCCTCCTATTAAGTACCATTATGCATCCCAAATAAATGTGTGTCTGTCGATTTTAA
AA
(SEQ ID NO: 41)

Start ATG: 127

MALQTYGDKPVAFQLEEGGEYYYVGSEVGNYMRHFRGILYKKYPGMTRIVLSNEERKRLAESGLSSHILASSVSLLRAVEVDDIMAGNDEKYRAV
SVNTSDTPVPRESKSKKQPQYVPTMPNSSHLDAVPQATPINRNRVHTKKVRTFPMCFDDTDPTASLENAAQKECLVPIRLDMELEGQKLRDTFTW
NKNESMITPEQFAEVLCDDLDLNPLPFVPAIAQAIRQQIEAFPNDPPILEETCDQRVIVKLNIHVGNTSLVDQVEWDMSEKNNNPEEFAIKLCAE
LGLGGEFVTAIAYSIRGQLSWHCRTYAFSEAPLSTIDVPFRNPSDADAWAPFLETLTDAEMEKKIRDQDRNTRRMRRLANTTTGW*
(SEQ ID NO: 42)

Name: Snf5-related 1
Classification: transcription_factor
Gene Symbol: Snr1
FlyBase ID: FBgn0011715

Celera Sequence No. : 142000013384244
GTCGTTGAGGGTCTCTATGTATATGCGGTACTCGCGGTTCTTGCGCTCTCTCGGAATATCGAAGACGTGGTCAAAGGACATAAGGTAAGTGATAT
AGTCCAGTTTCTCCACCGACCGCAAGTTGAGGTACAGCTCGTAGCACTCGTTGAGGTCCAGATAGCGACCGCCGCCCTCCTCGTCAGTGAACTCC
ACTAGGGCACTCATGTCGTCCGGATTGTTGTACACCCGAATCATCTCGTCGAACTCGACGGACAGCGGCACGCTGACCTCCGCCGGATGGGACTT
GTAGAACTGCTTGATTTGCTTGAGGCGGGCGTAGAACTCATTGAACTCGTTGGGCCCCGAAAGAGCGGCAATCTCCGCCTTTCGTTCATTGTCCT
TGTCCTCGTAGAGATCGCGTAGCTGGGACGTAGAGTTGTGATGCAGTTCCATGAGGTATTTAAGCCGGTGCTCCGAATGGATGCGCTCCTTTTCG
CCCGGCTTTTTGGTCGCATGCTCGTCCACCATCAGTTTGACCAGGCGCTCGCGCTCCTCGTGTAGGCGCCGCTGTTGCTCCAGGAGCGTCTCCAT
GGCTCTTGAATGCGAGGATTTAATGCGGGGAAATATCAAATGGAGGCCTTTCACTTAGCGAAATCCCGAAGAAAACACAACTTTTCGTCAGCGTG
TGTACATTAAAAAATACACTTACAATAAAGCAGGGATGGCTTATATTGTCACATCATATTATTGTCAGGTTATTATACTCCGATCACACTGGCAA
TTAATGTGGATTTCGGGAATGCAGATGTATCAAATTAACGCTCGATTATTCGAGTAATATAGTAATGATATTTAAAGAGCCAAATTGATTTTTCA
TTATCATATATAGATTATATCGCATGATTTTTCTACCTAGTCGATTAAAGTGAAGCCTCTGTTACAAATGCGATAACAATTACATCGTCTATCGG
TGGTCTGACAGCGACAACAAATACACATTTTTACCCTCGCAATCGCAGGGTCACACTTTCGTGAAATCATATGATCGATTTGCAGTGAAAATTTT
CAGACGTTGGGCAGAAGGCAAAAGTAACTTATCGTTTTCCACTTTCCTCGTGTTGGGCCGCCGTTTCCAACTCAGTTCGGCTGTGAATGTATTAG

FIGURE SHEET 12

CTTAATTAAATTTCAATTATTTCCAGGCACGGTTGTTGTACGTGGGCTTCTTTAAAACACTTGAATTTCCTTTCGGTTTGTGCAGTGAAAAAAAT
CAGTCAAAATGGCACTGAGCGATGCTGATGTACAAAAGCAGGTAATTGAAAACTTGGATTGGGAACGGGCAGGCGATCAAGGTCGTAGGGAAACA
AGCAAAACGAGAGGCTTCGTTTGCCTTTTTGCCTTTGCAATTTGCCTTTGCAATAAAGATGGCGAAGTCATGGGATCTCCCAGGTCATGTGAACT
TTTCACCGCCAGTAGTCCAATTAGACTGACATCCTTCCAAATCGGCCCGGTCATTTGGGAGTTGCCGGAGTTTTGACATATTTGTTGGCTAATGA
AGACACATCAATTTATTTGTCCAGATAGTTTGCGTAAAAAGTGAGTAAAAATTCGTGCTGGTCATGTGACACGGCCCCCGCATTGGAGCAATGTG
TTGGAGCGAGACGACTAGCCCTGCACCCCACACTCGTACTCTCTGTCACACGACCAGCGGACCCCTTACGTTATCAAAACTTTAACGAAAATAAA
TAGAGGCTAGGGTCTTGGACGTCTCCCTTTTCCATTTATCATGTCCAGTTATCATGTGACACACAGGCAACTACTAAACAGGACGACTGTTTCAG
ATCAAGCACATGATGGCGTTCATTGAGCAGGAGGCCAATGAGAAAGCCGAGGAGATCGATGCCAAGGCCGAGGAGGAGTTCAACATTGAGAAGGG
ACGCCTGGTCCAGCAGCAGCGTCTCAAGATCATGGAATACTACGAGAAGAAGGAGAAGCAAGTTGAGCTGCAGAAGAAGATTCAGTCCTCCAACA
TGCTCAACCAGGCTCGTCTGAAGGTGCGTGTCGTCCAGTTGGTGGCCCTAACATATACCGGAAAACACCTTATTTTTAATCATTCGTAATGTACC
CTGTAGGTGCTGAAAGTGCGCGAGGACCATGTGAGCAGCGTGCTGGATGATGCCCGCAAGCGTCTCGGCGAGGTCACCAAGAATCAGTCCGAGTA
CGAGACTGTGCTGACCAAGCTCATCGTCCAGGGCCTGTTCCAGATCATGGAGCCCAAGGTGATCCTGCGCTGCCGCGAGGTGGACGTCCCCCTGG
TACGTAACGTCCTGCCTGCCGCTGTGGAGCAATACAAGGCCCAGATCAATCAGAACGTCGAGCTGTTCATCGACGAGAAAGACTTCCTCTCTGCT
GATACCTGCGGTGGTGTTGAGCTGCTGGCCCTCAACGGACGCATCAAGGTGAGTACTGTCCTTTCGGTGGAGAGAGAGCAATCCCAACTGATCTA
ACAAACCACTTCAGGTGCCCAATACGCTGGAGTCCAGATTAGACCTCATTTCGCAGCAGCTGGTGCCCGAGATTCGTAACGCACTTTTCGGCCGC
AACGTCAATCGCAAATTCACCGACTAAATTCTATAAGTGCAAAACAAAACATAACTAACCAGAAAGAGAACCAGCATCAACACCTATTCAGCAGG
AACAGTTCAAGTTATTACAACAGAAGCTCCACCCACTAAATATTGAACCCAAGTAAACTTATCCTTTGGCAGTCAGGAGGCAACAGCTAGGATTA
TATTTGATTGCAAAATACTTTTGCCGTTGTCTTTGTAAAGTGAAATTGAAACACTCAAGAACATTTCGGTCCTTGTGTACGCAACAGTTTTAATA
GTAACCACACTAAACGCGCATATATATTCTCCGATATATATGTCTGTATGCCAATACTTATTATATAGTTTAGAGGACACGATCCTAGGAGCATA
CGAAAGCATAATACGAGTTTGTTAAAGTTTGTTCGTTTTTTTTTACATATGCACATATTTCTGAGCAGTAGGTCTAGATATGTGCTTATATTGT
ATACATACACTTTAAAATTTTGCATACATTCCTGTCCAAGAATTTTTATTTCAGTTTTCCCCTCGTTTATTGTACATTATTTTCTGTAGTCTTTG
TTAACTTTTTATATGTCTATGTCGTTTATGTTCGTAATTATCAAGTGCAGCGTTCAGGAGGAACAACGGCAGTGGATCGCCCCTTTTACAGAGCC
GCTGGCAGGTTGCGCATGCGACCACACAGCATTGTTGCTCAGCGAAGCACCGAAATGGACCTAAACCCCCGATTTCGCTTCTTCGAGGGCAACGG
ACGCTTGTGCAACTGCCACTGGCTCAACGAAAGCCCCGAAAATCATCAATGTCTGTTGTTGTTGAGATACCGAGAGTAGAGAATACACACTGCTT
AGCACGCGACACTTAATACCCATTCATTACACATGCACCAACGACGATGAAGTTTTGCCAAGTAGCTAAGTTTGTTGACCTGACCATCAAGTGCA
GCTTTCACACCCTCATATAACTACTTAAAGAAAATATAGAAAAATGGAAATTAGTTTTGCAATTTAGGGGACTGCCGAACTGCCACCGTTTCCAC
CTGACGCTGCGCCATCATATCAGGCTCTAAAAATCAACACACCATGTTCAAACACACGACTAGCATACAGGAGCAGGAGCTACAGTAAATTTGAA
CCTTGTATTCGCATGTTCGCCAATGTTCATAGTGTATTCTTCAAGCTCATTTTCTAACCAAGTTACCAAGTT
(SEQ ID NO: 43)

Exon: 1001..1068
Exon: 1167..1276
Exon: 1806..2018
Exon: 2097..2423
Exon: 2485..2777
Start ATG: 1244

Transcript No. : CT1531
TCACACTTTCGTGAAATCATATGATCGATTTGCAGTGAAAATTTTCAGACGTTGGGCAGAAGGCAAAAGCACGGTTGTTGTACGTGGGCTTCTTT
AAAACACTTGAATTTCCTTTCGGTTTGTGCAGTGAAAAAAATCAGTCAAAATGGCACTGAGCGATGCTGATGTACAAAAGCAGATCAAGCACATG
ATGGCGTTCATTGAGCAGGAGGCCAATGAGAAAGCCGAGGAGATCGATGCCAAGGCCGAGGAGGAGTTCAACATTGAGAAGGGACGCCTGGTCCA
GCAGCAGCGTCTCAAGATCATGGAATACTACGAGAAGAAGGAGAAGCAAGTTGAGCTGCAGAAGAAGATTCAGTCCTCCAACATGCTCAACCAGG
CTCGTCTGAAGGTGCTGAAAGTGCGCGAGGACCATGTGAGCAGCGTGCTGGATGATGCCCGCAAGCGTCTCGGCGAGGTCACCAAGAATCAGTCC
GAGTACGAGACTGTGCTGACCAAGCTCATCGTCCAGGGCCTGTTCCAGATCATGGAGCCCAAGGTGATCCTGCGCTGCCGCGAGGTGGACGTCCC
CCTGGTACGTAACGTCCTGCCTGCCGCTGTGGAGCAATACAAGGCCCAGATCAATCAGAACGTCGAGCTGTTCATCGACGAGAAAGACTTCCTCT
CTGCTGATACCTGCGGTGGTGTTGAGCTGCTGGCCCTCAACGGACGCATCAAGGTGCCCAATACGCTGGAGTCCAGATTAGACCTCATTTCGCAG
CAGCTGGTGCCCGAGATTCGTAACGCACTTTTCGGCCGCAACGTCAATCGCAAATTCACCGACTAAATTCTATAAGTGCAAAACAAAACATAACT
AACCAGAAAGAGAACCAGCATCAACACCTATTCAGCAGGAACAGTTCAAGTTATTACAACAGAAGCTCCACCCACTAAATATTGAACCCAAGTAA
ACTTATCCTTTGGCAGTCAGGAGGCAACAGCTAGGATTATATTTGATTGCAAAATACTTTT
(SEQ ID NO: 44)

Start ATG: 146

MALSDADVQKQIKHMMAFIEQEANEKAEEIDAKAEEEFNIEKGRLVQQQRLKIMEYYEKKEKQVELQKKIQSSNMLNQARLKVLKVREDHVSSVL
DDARKRLGEVTKNQSEYETVLTKLIVQGLFQIMEPKVILRCREVDVPLVRNVLPAAVEQYKAQINQNVELFIDEKDFLSADTCGGVELLALNGRI
KVPNTLESRLDLISQQLVPEIRNALFGRNVNRKFTD*
(SEQ ID NO: 45)

Name: vacuolar H+-ATPase E subunit-like
Classification: enzyme
Gene Symbol: Vha26
FlyBase ID: FBgn0015324

Celera Sequence No. : 142000013384244
AATATCGAAGACGTGGTCAAAGGACATAAGGTAAGTGATATAGTCCAGTTTCTCCACCGACCGCAAGTTGAGGTACAGCTCGTAGCACTCGTTGA
GGTCCAGATAGCGACCGCCGCCCTCCTCGTCAGTGAACTCCACTAGGGCACTCATGTCGTCCGGATTGTTGTACACCCGAATCATCTCGTCGAAC
TCGACGGACAGCGGCACGCTGACCTCCGCCGGATGGGACTTGTAGAACTGCTTGATTTGCTTGAGGCGGGCGTAGAACTCATTGAACTCGTTGGG
CCCCGAAAGAGCGGCAATCTCCGCCTTTCGTTCATTGTCCTTGTCCTCGTAGAGATCGCGTAGCTGGGACGTAGAGTTGTGATGCAGTTCCATGA
GGTATTTAAGCCGGTGCTCCGAATGGATGCGCTCCTTTTCGCCCGGCTTTTTGGTCGCATGCTCGTCCACCATCAGTTTGACCAGGCGCTCGCGC
TCCTCGTGTAGGCGCCGCTGTTGCTCCAGGAGCGTCTCCATGGCTCTTGAATGCGAGGATTTAATGCGGGGAAATATCAAATGGAGGCCTTTCAC TTAGCGAAATCCCGAAGAAAACACAACTTTTCGTCAGCGTGTGTACATTAAAAAATACACTTACAATAAAGCAGGGATGGCTTATATTGTCACAT
CATATTATTGTCAGGTTATTATACTCCGATCACACTGGCAATTAATGTGGATTTCGGGAATGCAGATGTATCAAATTAACGCTCGATTATTCGAG
TAATATAGTAATGATATTTAAAGAGCCAAATTGATTTTTCATTATCATATATAGATTATATCGCATGATTTTTCTACCTAGTCGATTAAAGTGAA
GCCTCTGTTACAAATGCGATAACAATTACATCGTCTATCGGTGGTCTGACAGCGACAACAAATACACATTTTTACCCTCGCAATCGCAGGGTCAC
ACTTTCGTGAAATCATATGATCGATTTGCAGTGAAAATTTTCAGACGTTGGGCAGAAGGCAAAAGTAACTTATCGTTTTCCACTTTCCTCGTGTT
GGGCCGCCGTTTCCAACTCAGTTCGGCTGTGAATGTATTAGCTTAATTAAATTTCAATTATTTCCAGGCACGGTTGTTGTACGTGGGCTTCTTTA
AAACACTTGAATTTCCTTTCGGTTTGTGCAGTGAAAAAAATCAGTCAAAATGGCACTGAGCGATGCTGATGTACAAAAGCAGGTAATTGAAAACT
TGGATTGGGAACGGGCAGGCGATCAAGGTCGTAGGGAAACAAGCAAAACGAGAGGCTTCGTTTGCCTTTTTGCCTTTGCAATTTGCCTTTGCAAT
AAAGATGGCGAAGTCATGGGATCTCCCAGGTCATGTGAACTTTTCACCGCCAGTAGTCCAATTAGACTGACATCCTTCCAAATCGGCCCGGTCAT
TTGGGAGTTGCCGGAGTTTTGACATATTTGTTGGCTAATGAAGACACATCAATTTATTTGTCCAGATAGTTTGCGTAAAAAGTGAGTAAAAATTC
GTGCTGGTCATGTGACACGGCCCCCGCATTGGAGCAATGTGTTGGAGCGAGACGACTAGCCCTGCACCCCACACTCGTACTCTCTGTCACACGAC
CAGCGGACCCCTTACGTTATCAAAACTTTAACGAAAATAAATAGAGGCTAGGGTCTTGGACGTCTCCCTTTTCCATTTATCATGTCCAGTTATCA
TGTGACACACAGGCAACTACTAAACAGGACGACTGTTTCAGATCAAGCACATGATGGCGTTCATTGAGCAGGAGGCCAATGAGAAAGCCGAGGAG
ATCGATGCCAAGGCCGAGGAGGAGTTCAACATTGAGAAGGGACGCCTGGTCCAGCAGCAGCGTCTCAAGATCATGGAATACTACGAGAAGAAGGA
GAAGCAAGTTGAGCTGCAGAAGAAGATTCAGTCCTCCAACATGCTCAACCAGGCTCGTCTGAAGGTGCGTGTCGTCCAGTTGGTGGCCCTAACAT
ATACCGGAAAACACCTTATTTTTAATCATTCGTAATGTACCCTGTAGGTGCTGAAAGTGCGCGAGGACCATGTGAGCAGCGTGCTGGATGATGCC
CGCAAGCGTCTCGGCGAGGTCACCAAGAATCAGTCCGAGTACGAGACTGTGCTGACCAAGCTCATCGTCCAGGGCCTGTTCCAGATCATGGAGCC
CAAGGTGATCCTGCGCTGCCGCGAGGTGGACGTCCCCCTGGTACGTAACGTCCTGCCTGCCGCTGTGGAGCAATACAAGGCCCAGATCAATCAGA
ACGTCGAGCTGTTCATCGACGAGAAAGACTTCCTCTCTGCTGATACCTGCGGTGGTGTTGAGCTGCTGGCCCTCAACGGACGCATCAAGGTGAGT
ACTGTCCTTTCGGTGGAGAGAGAGCAATCCCAACTGATCTAACAAACCACTTCAGGTGCCCAATACGCTGGAGTCCAGATTAGACCTCATTTCGC
AGCAGCTGGTGCCCGAGATTCGTAACGCACTTTTCGGCCGCAACGTCAATCGCAAATTCACCGACTAAATTCTATAAGTGCAAAACAAAACATAA
CTAACCAGAAAGAGAACCAGCATCAACACCTATTCAGCAGGAACAGTTCAAGTTATTACAACAGAAGCTCCACCCACTAAATATTGAACCCAAGT
AAACTTATCCTTTGGCAGTCAGGAGGCAACAGCTAGGATTATATTTGATTGCAAAATACTTTTGCCGTTGTCTTTGTAAAGTGAAATTGAAACAC
TCAAGAACATTTCGGTCCTTGTGTACGCAACAGTTTTAATAGTAACCACACTAAACGCGCATATATATTCTCCGATATATATGTCTGTATGCCAA
TACTTATTATATAGTTTAGAGGACACGATCCTAGGAGCATACGAAAGCATAATACGAGTTTGTTAAAGTTTGTTCGTTTTTTTTTACATATGCA
CATATTTCTGAGCAGTAGGTCTAGATATGTGCTTATATTGTATACATACACTTTAAAATTTTGCATACATTCCTGTCCAAGAATTTTTATTTCAG
TTTTCCCCTCGTTTATTGTACATTATTTTCTGTAGTCTTTGTTAACTTTTTATATGTCTATGTCGTTTATGTTCGTAATTATCAAGTGCAGCGTT
CAGGAGGAACAACGGCAGTGGATCGCCCCTTTTACAGAGCCGCTGGCAGGTTGCGCATGCGACCACACAGCATTGTTGCTCAGCGAAGCACCGAA
ATGGACCTAAACCCCCGATTTCGCTTCTTCGAGGGCAACGGACGCTTGTGCAACTGCCACTGGCTCAACGAAAGCCCCGAAAATCATCAATGTCT
GTTGTTGTTGAGATACCGAGAGTAGAGAATACACACTGCTTAGCACGCGACACTTAATACCCATTCATTACACATGCACCAACGACGATGAAGTT
TTGCCAAGTAGCTAAGTTTGTTGACCTGACCATCAAGTGCAGCTTTCACACCCTCATATAACTACTTAAAGAAAATATAGAAAAATGGAAATTAG
TTTTGCAATTTAGGGGACTGCCGAACTGCCACCGTTTCCACCTGACGCTGCGCCATCATATCAGGCTCTAAAAATCAACACACCATGTTCAAACA
CACGACTAGCATACAGGAGCAGGAGCTACAGTAAATTTGAACCTTGTATTCGCATGTTCGCCAATGTTCATAGTGTATTCTTCAAGCTCATTTTC
TAACCAAGTTACCAAGTTCAATATGATGAATAACTACAAGATTAGCAAACAAATACAAGTAGCATATGCGTTATTATATAACATCGAGTACTATA
TACATTACATGAAATACAAAATGCAAGAAAAATTACTTTTAAACAAAATTTATGTTGAATAAAAAACAGTATTTCCAAAAACTAAACTTAACTGT
ATAACAACTTCCTTTTGCAATGTTCTAATGATCCTAAAAACAAGACATGGGGTAAACTATTTTAAGAAATTCAATCTAGGACTTCAAATAAGTCT
TAATTAAGTACACCCATATTCTTGATCAGCAGAGTCAACTTGCTCATGTTTGTATGAAAACCTAGAACATAAAAAAGCCAGAAGGTCTGGACTAA
ACTCGCAGATTCCTGTAACTTGGAAGCACCACGAGTTTGCTTTAGAAGATGCCTTTCCGTTGAACTAAAACTAGACGAGTAAAGCGTATCTCAAA
CATTGTATCTTCCGAACCAAAATAGTGCTGCATACTTTTCGGGATATGTCTTATTCAATGTAAGTAATACAAAAAGAAAAAAGGTAACTTCTTAA
AACTTGTAATATTTGTCACAAATGAATGACGACTAGATTTGGCCATGTCTGTAACAATAAACGTACAAAATATTCGAAGTTGCAGAAATGGGGAT
CCAGCATTCGGATTTGGTTTTTTGTCAAACTTTTAAATATAGAATCGGACCACATCTTTTTAAGACCTTAAAAAACTGATTTGAAGTTAGACCCC
TCATAATGCCAACTAAATTTGTTAAACAAAAATATGCCCCTATATGCCAATCAAATTTAAATACAATGCTTTCTCAGCGTTTCAGTTAAATACTT
TGGGTTGTTTAATGGTTTTATACGTATACATGTGCTAAGTCCATGTATCTTATATTTCGTAAATCCATAGATTTTGTTCGACGAAACTTTGCTAA
ATGATATTGATCTTTCAAATATAACTTGTTAATTTCCTTTCATCGCCGTGGCAAATCCTTCGAGAGTGAGTACTACTTGTTAAACGCATATATGA
GGAAAATTTATTGATGAATAATGCGAACATGCAAACGGAACACATCCCCGAATTCACACAAAGCATCTCTGTGGTATCTCTTTTGGTTTTTTATT
TGTTGCATCAACTCCGCGGAACTCCAGCTAC
(SEQ ID NO: 46)

Exon: 1001..1222
Exon: 1752..1964
Exon: 2043..2369
Exon: 2431..3876
Start ATG: 1190

Transcript No. : CT1535
GGCAGAAGGCAAAAGTAACTTATCGTTTTCCACTTTCCTCGTGTTGGGCCGCCGTTTCCAACTCAGTTCGGCTGTGAATGTATTAGCTTAATTAA
ATTTCAATTATTTCCAGGCACGGTTGTTGTACGTGGGCTTCTTTAAAACACTTGAATTTCCTTTCGGTTTGTGCAGTGAAAAAAATCAGTCAAAA
TGGCACTGAGCGATGCTGATGTACAAAAGCAGATCAAGCACATGATGGCGTTCATTGAGCAGGAGGCCAATGAGAAAGCCGAGGAGATCGATGCC
AAGGCCGAGGAGGAGTTCAACATTGAGAAGGGACGCCTGGTCCAGCAGCAGCGTCTCAAGATCATGGAATACTACGAGAAGAAGGAGAAGCAAGT
TGAGCTGCAGAAGAAGATTCAGTCCTCCAACATGCTCAACCAGGCTCGTCTGAAGGTGCTGAAAGTGCGCGAGGACCATGTGAGCAGCGTGCTGG
ATGATGCCCGCAAGCGTCTCGGCGAGGTCACCAAGAATCAGTCCGAGTACGAGACTGTGCTGACCAAGCTCATCGTCCAGGGCCTGTTCCAGATC
ATGGAGCCCAAGGTGATCCTGCGCTGCCGCGAGGTGGACGTCCCCCTGGTACGTAACGTCCTGCCTGCCGCTGTGGAGCAATACAAGGCCCAGAT
CAATCAGAACGTCGAGCTGTTCATCGACGAGAAAGACTTCCTCTCTGCTGATACCTGCGGTGGTGTTGAGCTGCTGGCCCTCAACGGACGCATCA
AGGTGCCCAATACGCTGGAGTCCAGATTAGACCTCATTTCGCAGCAGCTGGTGCCCGAGATTCGTAACGCACTTTTCGGCCGCAACGTCAATCGC
AAATTCACCGACTAAATTCTATAAGTGCAAAACAAAACATAACTAACCAGAAAGAGAACCAGCATCAACACCTATTCAGCAGGAACAGTTCAAGT
TATTACAACAGAAGCTCCACCCACTAAATATTGAACCCAAGTAAACTTATCCTTTGGCAGTCAGGAGGCAACAGCTAGGATTATATTTGATTGCA
AAATACTTTTGCCGTTGTCTTTGTAAAGTGAAATTGAAACACTCAAGAACATTTCGGTCCTTGTGTACGCAACAGTTTTAATAGTAACCACACTA
AACGCGCATATATATTCTCCGATATATATGTCTGTATGCCAATACTTATTATATAGTTTAGAGGACACGATCCTAGGAGCATACGAAAGCATAAT
ACGAGTTTGTTAAAGTTTGTTCGTTTTTTTTTACATATGCACATATTTCTGAGCAGTAGGTCTAGATATGTGCTTATATTGTATACATACACTT
TAAAATTTTGCATACATTCCTGTCCAAGAATTTTTATTTCAGTTTTCCCCTCGTTTATTGTACATTATTTTCTGTAGTCTTTGTTAACTTTTTAT
ATGTCTATGTCGTTTATGTTCGTAATTATCAAGTGCAGCGTTCAGGAGGAACAACGGCAGTGGATCGCCCCTTTTACAGAGCCGCTGGCAGGTTG CGCATGCGACCACACAGCATTGTTGCTCAGCGAAGCACCGAAATGGACCTAAACCCCCGATTTCGCTTCTTCGAGGGCAACGGACGCTTGTGCAA
CTGCCACTGGCTCAACGAAAGCCCCGAAAATCATCAATGTCTGTTGTTGTTGAGATACCGAGAGTAGAGAATACACACTGCTTAGCACGCGACAC
TTAATACCCATTCATTACACATGCACCAACGACGATGAAGTTTTGCCAAGTAGCTAAGTTTGTTGACCTGACCATCAAGTGCAGCTTTCACACCC
TCATATAACTACTTAAAGAAAATATAGAAAAATGGAAATTAGTTTTGCAATTTAGGGGACTGCCGAACTGCCACCGTTTCCACCTGACGCTGCGC
CATCATATCAGGCTCTAAAAATCAACACACCATGTTCAAACACACGACTAGCATACAGGAGCAGGAGCTACAGTAAATTTGAACCTTGTATTCGC
ATGTTCGCCAATGTTCATAGTGTATTCTTCAAGCTCATTTTCTAACCAAGTTACCAAGTTCAATATGATGAATAACTACAAGATTAGCAAACAAA
TACAAGTAGCATATGCGTTATTATATAACATCGAGTACTATATACATTACATGAAATACAAAATGCAAGAAAAATTACTTTTAAACAAAATTTAT
GTTGAATAAAAAACAGTATTTCC
(SEQ ID NO: 47)

Start ATG: 190

MALSDADVQKQIKHMMAFIEQEANEKAEEIDAKAEEEFNIEKGRLVQQQRLKIMEYYEKKEKQVELQKKIQSSNMLNQARLKVLKVREDHVSSVL
DDARKRLGEVTKNQSEYETVLTKLIVQGLFQIMEPKVILRCREVDVPLVRNVLPAAVEQYKAQINQNVELFIDEKDFLSADTCGGVELLALNGRI
KVPNTLESRLDLISQQLVPEIRNALFGRNVNRKFTD*
(SEQ ID NO: 48)

Name: vacuolarH+-ATPase E subunit
Classification: enzyme
Gene Symbol: Vha26
FlyBase ID: FBgn0015324

Celera Sequence No. : 142000013384852
CAAAGCCTGCAGATCGCTGTAAATTAAATTTTTACTAAAGGTATCAAAAGACTAAGGTCGCTATGAATCGTTGAAAATATCCAAAATGGCCAGAG
TTTGGATCAATGAAATTCGTTTAGTGTAAATTGAATAATACCATTTACTCGTAGAGTACAAGTGTACACTAGATTCATTGCAATATAAACTCCGA
GATCTCGGATTCATCTTTGTTTAAGTTTTATATCCATTTTTATAATTTGAATACAAAGTCTAGTGTAAGACAGTTATACCCGTTTCTCGTAGAG
TAAAAGGGTATACTAGATTCGTTTAAAAGTATTTTATAGATAGAAGGAAATTTTTTCCGACCATAAAAAGTATATTAATTCTTGATCAGGATCAA
TAGCCGAGTCGATCTGGCCTGGTCCGTCTGTCTGTCCGTCTGTGTGAACGTCGAGATCTCTGGTACTATAAGGTTGAGATTAAGCATACAGATTC
TTAAGACATAGAGGCAGCGCAAGTTTGTTGACCCATATTTTGAAAAATGTTTTGATATGTTTTTATAATTTTATTAGACTTGTAAATTTCTATCG
ATTTGCCAAAAAAATTTGCCACGCCCACTCTAACGCCCTAAAACCGCCCAAAACTGCCACGCCCACACTATTGCAAAATGTTTACATTTTTTTCA
TAATTTTATAAGTCTTGTAATATTCTATCGGTTAGCCAAACAATTTTTTTCACGTCCACTCTAACGACCTTAAGCTTCCAAACCGGTCACGCCCA
CACTTTTAAGCCATTTTTAATTTGTTTTTCATTTTATTCCCCATCTATCGATATCCCAGAAAAATTATGAAATTTCGCGTTCGCATTCGCACTAG
CTGAGTAACGGGTATCTGATAGTCGTGCAACTCGACTTAAGCATTCTCTCTTGTTTTACATTTCAGTTTTTGGCCACAAGCCGCCCGTATGCATG
ACCCACGCTTTCAAAATTTTTATTATATATTTCTTTTTTTTATTTTTTTCCCAACTTCAATCGATATGGAAGAAATTTCTCGTTTGCTCTTTCA
CTAGCTGAGTAACGGGTATCTGATATTTGGGTATCTTAACTTCGCTTGTTTTTTAGTGAAAGCCATTTTTTTCAAATGGTTTGTACACCTTTATG
AGAATGTTATTGCTTTTATTGTATCTCGTAAACTAAATATATGGTAGAAATGGTCTTGATCTTTTAAACACAAGTCATAGGGTTTTCCGTTTGGA
ATCCACAAGAGTATATGTCGTAAAAGTCCTTGTTCTGTTTAAGGCCCAGATAGAAGACATGCTCGGCCAGATCCTTCCCAAACTCACAGAAGTTC
TGAGCGTAAAGAGTAAAAAATATACGCTTGTTGTCAAGATGGTACTTTTGAAGGACGCCATTTTCCTGATCGTATATCCCACTGTTCTGTGGAGG
CGAGTTGATCCAGGCGCTGTAGTCTATCCAGGCCGCTCGGAAGCTCTTTAAGTAGATCACAGCCAGCATTCTGGCCTCATCCAGAACATTAACGA
ACTGCGGCAGCCTTAAACACTCCACATCTTCGCGAAACCGCGTGAAATCACGCTGACGCTCCAGACTATTAAAAAGCATCATGTACAAATGGACC
GTAAACGTGGAGTAGAAGTAGGACATGGGCTTGTTGCGGCTCTGAAAGAGGTACATGCTCCAATCCAGCATGGTGCGCTGAACCCCCCAATTCGTA
TGTTGAATTCAGTTTTCTGTGCTGCTCCAGATTGCGAACGTTGTGTTCGTAGCTCTCCCGGTAGATCCGCAGGTCCTTGTACTCCCGGCTCAGGT
CTCTAGCATGGAAGTAGACTCGCGGCGTTTTAAATTTCTGCTTATACGTGGCCAGCTTGCTGAGAATGGGATTCGACTCTCTGTCCTTCTGAAAC
CTGACGACGAAGCGGTCCAAAATGCCCAGAAAGTCATCCAGCTCGTGGGATTCTCCATTGAGCATGTTTTTTGTAACTATATACCCGAAAAGTGG
CTTGAAATACTCATAGGTCTCACGATAGCAGTCTTCCAGCGCGTGGTGCACGTTGCAGGAGATGAAGAAGTCCAGCGTCTTCTGCTTAGCCTCGA
ATGGCTCTGGATCGTTCTGCAGCTCGGTCAGCAACTGCATAAGATCGCCCATTTGCGGCATGTGTCCTTGGATAGGGTATATGCATTAGGCACTC
CCCCAACACAGGCTTTCCTCACTTACCCATGATCGAAAAGAGGGGTCGATTGCGGCTACAGACGTAGTCGAAATAGCTCTCGCAGGCATACTTTT
CGGTGTTGATGGAGCCCTGTATACGAACCGACAATTTTTCAAGTTCCCTTATCCGCAGCTCCGACAGGTGCCGCACGTATCCCACTTGGCAATGC
CCTGAACCAGTCAACATCAACAGAATAAGCGCTACGGATGCGCCGATTGCAAGACTTGAGGTTGTCATCGCAGAGCTCAAGTCACTGGCAACCCA
GCTTTTGCGCCAGCCTATCGGACCCCTCAACGGATGTCGGATTTCGTTGCACAGTAGTTCGAGAGAGAGTCACTTTTCAAATACGTCTATCACTG
GGCAACGAAACTATTTAACTTCAATTGAAATGTAAGCACAAAACTCCGTATCCCCTGGTATTAAATAACTAAAATAACTTATTGAATGTTTCAAT
TTTTAGTAAAAACTTTTTTATTACTTTTGACAATATTTAAAAAGATTTTCTGTCCAAGTGGACAATAATTAAATGATTGTGGGCTGACATTGACA
TAATTTATTTTTATCATAATGAACGTTTGAAAAGCATAGATAGTATTGAAAAATGCCCTATTAGTGCAACTCAGTATATGTTTTTATGGTGTGTT
TTCAACATTTTCAACTTATGCTTCTTCAACGTGTTTAACCAAAAATTTATCCGGACTTTAGAAGAACGTTTTGTTGCAGACAGTTACAAACAGTT
CTCCAAAATCACAATAATCAATCTTTACCGTTTTACCTTTTTTATTTTATCGCGCACATATAAACGGTCTAAAAACCAATTAAACGCTCACATTC
CTATTTTATCATTTTTACTTGAAAATGCAAAAACACCCGAAAGTTCTCGGGTTGTTTGTTGTTTTTATATTGTTGAATTATTAGAACGGATTTAT
ATATGATCTTATTACACTCGCACCACAGTGCATTGCTCAATTCGAGGTCTTATTTTAATTCAGTGAGTGAGTTCCTATGCTTAATTATATTTCCG
AAGCGATAAGAATGTCAAGTCCTATCAGGAAAATTTCTCTCCCACTGTTTTTACGATCGCGCTATTCTGGAATATGGGCTTTGCATCGTTTCACA
AGTATTACGAGTTATATCTGACTAAGCGTAGACAACAGTGTGCAGTTGCTTATGAAAGGAATGATTTAAATATACATATACATACATAATATACA
TATATTATATTATATTTGTTGGT
(SEQ ID NO: 49)

Exon: 2443..2212
Exon: 2156..1001
Start ATG: 2443 (Reverse strand: CAT)

Transcript No. : CT1569
ATGACAACCTCAAGTCTTGCAATCGGCGCATCCGTAGCGCTTATTCTGTTGATGTTGACTGGTTCAGGGCATTGCCAAGTGGGATACGTGCGGCA
CCTGTCGGAGCTGCGGATAAGGGAACTTGAAAAATTGTCGGTTCGTATACAGGGCTCCATCAACACCGAAAAGTATGCCTGCGAGAGCTATTTCG
ACTACGTCTGTAGCCGCAATCGACCCCTCTTTTCGATCATGGGACACATGCCGCAAATGGGCGATCTTATGCAGTTGCTGACCGAGCTGCAGAAC GATCCAGAGCCATTCGAGGCTAAGCAGAAGACGCTGGACTTCTTCATCTCCTGCAACGTGCACCACGCGCTGGAAGACTGCTATCGTGAGACCTA
TGAGTATTTCAAGCCACTTTTCGGGTATATAGTTACAAAAAACATGCTCAATGGAGAATCCCACGAGCTGGATGACTTTCTGGGCATTTTGGACC
GCTTCGTCGTCAGGTTTCAGAAGGACAGAGAGTCGAATCCCATTCTCAGCAAGCTGGCCACGTATAAGCAGAAATTTAAAACGCCGCGAGTCTAC
TTCCATGCTAGAGACCTGAGCCGGGAGTACAAGGACCTGCGGATCTACCGGGAGAGCTACGAACACAACGTTCGCAATCTGGAGCAGCACAGAAA
ACTGAATTCAACATACGAATTGGGGGTTCAGCGCACCATGCTGGATTGGAGCATGTACCTCTTTCAGAGCCGCAACAAGCCCATGTCCTACTTCT
ACTCCACGTTTACGGTCCATTTGTACATGATGCTTTTTAATAGTCTGGAGCGTCAGCGTGATTTCACGCGGTTTCGCGAAGATGTGGAGTGTTTA
AGGCTGCCGCAGTTCGTTAATGTTCTGGATGAGGCCAGAATGCTGGCTGTGATCTACTTAAAGAGCTTCCGAGCGGCCTGGATAGACTACAGCGC
CTGGATCAACTCGCCTCCACAGAACAGTGGGATATACGATCAGGAAAATGGCGTCCTTCAAAAGTACCATCTTGACAACAAGCGTATATTTTTTA
CTCTTTACGCTCAGAACTTCTGTGAGTTTGGGAAGGATCTGGCCGAGCATGTCTTCTATCTGGGCCTTAAACAGAACAAGGACTTTTACGACATA
TACTCTTGTGGATTCCAAACGGAAAACCCTATGACTTGTGTTTAAAAGATCAAGACCATTTCTACCATATATTTAGTTTACGAGATACAATAAAA
GCAATAACATTCTCATAAAGGTGTACAAACCATTTGAAAAAAATGGCTTTCACTAAAAAACAAGCGAAGTTAAGATACCCAAATATCAGATACCC
GTTACTCAGCTAGTGAAAGAGCAAACGAGAAATTTCTTCCATATCGATTGAAGTTGGG
(SEQ ID NO: 50)

Start ATG: 1 (Reverse strand: CAT)

MTTSSLAIGASVALILLMLTGSGHCQVGYVRHLSELRIRELEKLSVRIQGSINTEKYACESYFDYVCSRNRPLFSIMGHMPQMGDLMQLLTELQN
DPEPFEAKQKTLDFFISCNVHHALEDCYRETYEYFKPLFGYIVTKNMLNGESHELDDFLGILDRFVVRFQKDRESNPILSKLATYKQKFKTPRVY
FHARDLSREYKDLRIYRESYEHNVRNLEQHRKLNSTYELGVQRTMLDWSMYLFQSRNKPMSYFYSTFTVHLYMMLFNSLERQRDFTRFREDVECL
RLPQFVNVLDEARMLAVIYLKSFRAAWIDYSAWINSPPQNSGIYDQENGVLQKYHLDNKRIFFTLYAQNFCEFGKDLAEHVFYLGLKQNKDFYDI
YSCGFQTENPMTCV*
(SEQ ID NO: 51)

Celera Sequence No. : 142000013385194
GCGTCCTCCGGCGATGTGTCTGCCGAGGCGTTGGCATTCTCCCCCTCGAGCTCCGCCTCATCGTCGTCGTCTGGCAAGGGGCCGGGAATCGGTGT
CTCACCGTTCTTCAGGCAATTGTGGATGTAGGCGGCCTTCCACTTGGCGTACTTCCTGTTGTGCAGCGCCTCTTCGCTCAGTTCACCGAAGGTCT
GGAGAATGTCGTAGAGCACACCACTGGAGTAGAAGGCCTTAACGACGTTTCTGCGAAGAAGCACAATCTTATGAATCAGGAAAATCGATTCAGGG
TATTTCTACGAAGGGAACGCACTTTCCGAAGTTCTCCTCGCGATCCTGTTTGTCGGCGTACAGGAATAGTTTCAAGGCGTAGTTCTCGATGTGTG
CCTGGGCAGCCACCTCGTTGGTGATGGCCTCGTTCTCAGCATACTGTTTCTTCATCTGCTCCAGCCAGTCCATGATGCCTGGCGGTCGTAGGGAA
AACCAAAACAAAACAAACCACGGATGAGTCATAGGCTGGTAATATGCGTATCGGATTTTTCACTCACCCAGCAGCAGTTTGGTTTCTTCACCCGT
TTGGGTGGAGGCTTTGAGGCCCACCTGGAGAGCACTGGATTCGGAAGATGAGTAAATACGGGCAAAACAAGAAAAACTAATCTGTAGATACTCAC
TAGAGTCTCGCCCAGTAGGCGATGACCACATCCCGGGTATCATGTTCCTGGGCCAGCTTCAGAAAGTGTTGGATGGACTTCAGCGAGGGAGGACA
AGGCGGAAACTCCATCGTGGTGGAAAGAGGGCTTAATCTTTAGTTCTATGCTTAATTACGGATCTGGAAAATTATGCCGACAACAATGGAAATGA
CGAGCACGCAGAGTGACCAGATATCGCAGTTTCTCGAATGCCATGGAACCACCCCAGTTCCAAACTCTGGAACTAGCGAAATACTAAAGTTTGTA
CCTTCGGCTAAAGTTGTTGGTTCGGCGCTCAGTTGCGAATCTGCGACCAAAACGTTTGGAGTTTCTCAGGTAAGCACTGGACTCTGGGAACTGGT
TTTCGCTGTTATCAGTGCGACCAGTTGCACTTTGCACTTTGACCTGCATCCTTCACACCAGTCACATTCCAGGCACATCTCTGCACCACCGGCAA
CATGGTTCTCTCCAAGCCCCTGTACTCGCTCTTCGGCACTTATCTGGAGCAGCTCTTCAACCACCCGGTCCGCACCAAATCCATTACGGCGTAAG
TACACTATTCGCCTTATCATCCGGTTCGCCTCACCCACCGGCTGCTCCTTACTGCAGATGCGTTCTGGCCACCTCGGCTAATGTCACCTCCCAGC
GTTTGGCGGGCGCCAAGACCCTCAACCAGCAGAGCGTATTCGCCTACGGACTCTTTGGACTGATCTTCGGCGGTAGTGTGCCGCACTACTTCTAC
ACGACGGTGGAGCGACTCTTCAGCCAGGATGTGCGCTTCCGAAGATTCTTCCTGTTCCTGTCCGAGCGACTGGTCTATGCTCCGATTTACCAGGC
ACTGTCCCTGTTCTTCTTGGCCCTGTTCGAGGTGAGAATCCATAATCCGCAATCTCAGTTCCTAGAACTATAATTTGTAATCCCTTACAGGGCAA
GTCTCCCAGCACTGCATTGAAGAATGTTGAGAAGCTCTACTGGCCTCTGCTGAAGGCCAACTGGCAGTACCTGTCCGTGTTCGTGTACCTCAACT
TCGCCTACGTGCCCCCGATGTTCCGGTCCATCAGCATGGCCATCATCTCCTTCATCTGGGTGGTGTACATCGCCCAGAAGCGTCGCCGCTTCCAG
GACAAGCTGGCCGCCAAAGAGGCAGCCAAATAGGCTATACGACCCTTAAACCCTGTGGTAGTCGTCTTGGCCTAATATTCCAATTACTGCTTAGA
TTACGGCTGAACTGCTTCAAGTTCTTTATCTTCCCGCGTTCCGGCGGATTGCAAAAAGTCCGTGTGTATTTGAACACTTTAGATAAGCTAAAACT
AACTGGAGGGGCGCCTTATCAACCGACTGTTGTTATACCTTAAACCCTAAATTTTGTAAACTTTTCTTACCAAAATAAACTAATATACAATGTAT
AAGATATCTAGATATCCATGGCCAAATTTGGCCAACAGAAATGCTTAACAAGTAGCGACAATCGTCGATCTAACATCCCATTTCCATTGCGCACA
ATGGATCCCAATTTGAGAAATTCCAAGGCAACCTTTTGAGATGCAACAAATAATGTCTGTTTTTTTTTTATTAAAACGCAGCTTAGAACTAGCAA
ATAATCGAGCAAAGGCTTACAAACGAGAATTATTGGCTTTTTATCGGCGCTACAATATAATTTCGCTAGTAAATTCATGGGCAGATGACTAACTT
AGGGCTACGGAATGCAGTGTAAAACAAGTTAAATGCGCATAACAACTATCTTAAAACTAGGATTCTGACTAGAGGAGGTGACTACGATGATGGTG
ATGATTGTGGGGGGCACCTGTGCCTCAAGACTCGCCGCACATCCTGCGCAGCGACGCGGTTAACACTCAGAAGGCGGCCATCGACGGACTCCGGC
TGTTGCGCAGGGGCGTGAGAAGGGGCGTGGCAGGACTGCTGGCGCGGCTAAAGCAACTGGAGCAGCAACTAGAGGCATCCTCCACCTCGCCCTCG
GCGTTCGCCTTGTGGTGATAGGGAATCGGTCGCTTGCGAGCGCTGAAAGCATAATGAATAGATTAGTATGGGATTCGTGTAGCAAGCTTAAAAAC
CAAAGGGCAAATATGAAAGTAACTCACCAAACTGAAAATCGTAAGGAATAGAAAAGCAGTGGCTAAAAATCAAACAAAAGAAATCCTATAAAACC
ATATAATCGGTAAAGTGACAA
(SEQ ID NO: 52)

Exon: 1001..1019
Exon: 1109..1230
Exon: 1293..1551
Exon: 1611..1871
Start ATG: 1142

Transcript No. : CT1579
AACGTTTGGAGTTTCTCAGACATTCCAGGCACATCTCTGCACCACCGGCAACATGGTTCTCTCCAAGCCCCTGTACTCGCTCTTCGGCACTTATC
TGGAGCAGCTCTTCAACCACCCGGTCCGCACCAAATCCATTACGGCATGCGTTCTGGCCACCTCGGCTAATGTCACCTCCCAGCGTTTGGCGGGC
GCCAAGACCCTCAACCAGCAGAGCGTATTCGCCTACGGACTCTTTGGACTGATCTTCGGCGGTAGTGTGCCGCACTACTTCTACACGACGGTGGA
GCGACTCTTCAGCCAGGATGTGCGCTTCCGAAGATTCTTCCTGTTCCTGTCCGAGCGACTGGTCTATGCTCCGATTTACCAGGCACTGTCCCTGT
TCTTCTTGGCCCTGTTCGAGGGCAAGTCTCCCAGCACTGCATTGAAGAATGTTGAGAAGCTCTACTGGCCTCTGCTGAAGGCCAACTGGCAGTAC CTGTCCGTGTTCGTGTACCTCAACTTCGCCTACGTGCCCCCGATGTTCCGGTCCATCAGCATGGCCATCATCTCCTTCATCTGGGTGGTGTACAT
CGCCCAGAAGCGTCGCCGCTTCCAGGACAAGCTGGCCGCCAAAGAGGCAGCCAAATAGGCTATACGACCCTTAAACCCTGTGGTAGTCGTC
(SEQ ID NO: 53)

Start ATG: 53

MVLSKPLYSLFGTYLEQLFNHPVRTKSITACVLATSANVTSQRLAGAKTLNQQSVFAYGLFGLIFGGSVPHYFYTTVERLFSQDVRFRRFFLFLS
ERLVYAPIYQALSLFFLALFEGKSPSTALKNVEKLYWPLLKANWQYLSVFVYLNFAYVPPMFRSISMAIISFIWVVYIAQKRRRFQDKLAAKEAA
K*
(SEQ ID NO: 54)

Name: putative transporter
Classification: transporter

Celera Sequence No. : 142000013384359
ATTAAAGAGCTCCGCCATCTCCATCTTCATTCGCCATCCCAACCCATCGAACCCAAGCTCGACCTCGAAGAAAGGCCGCCACAGAAAGTCATCGA
ACTTTCTCCGTGTTCTTTCGCCGACTAATTTCTATATTAGGTGTCATGGTCTCGGCTGTCGGTGGTTCTATTAATTACCCCAACAGCTGCGATCA
TTTATAACTTAGTCGGGGTAGTCAATCTTGCGATCTGTTACAATTTGTAAGTGGAAAACCCGTGGAGTCAGTGGAGCTCCCAAGGTGCGCAAGGT
CGAACAAATTTGCCTAAACACAATCGCAAAGATTAGCAGCCAAATTGCCGTGTCAAGTGAACCTCTCGAAGTTGGGAACCCAGTGGCTCCTCCAG
AAGAAAGAAAAGATCCGACCCGACCCGGCTATTATACAATCGCGTGACTCTTCTCAGAGCTGCTGCGAATATTTGTTGCCCAATTCACCTTTGTA
AACGGTGACATGCGAACAGAATGGTTATGGATAGAATGGTTAGATGGATGGAGCTGCGGATGGTGCCAATGGTGGCCCCAAGCAGCGTCTGAGCT
GTAATTAATAGCAGCTTACGGGTTAGTCGCAAATTAGCCACATGACACAGCGCCAGCGAAGGCGTAGGAGTCTGGAGACATAACCGAGACGGTTC
CTCGTGGGCGGAACTGACCCCATCCGGGAGAACTCCTAAGCTCTTTAGCACTTCCCTTCGTTTTTACCAGCGACGGTTGAAAAAGTCGCTAACAG
CATCCGTTCGATTGGAGGCGTTGCGTTTGACGAGTTTTACAGCGTGGGTGTGTGTGCTTACCACTCTAATTTACTCGAAATACATTAAGTTTGAT
TTAAGTCGTAAATATGCTAATAAAAAGCATTTAACTCGGATTAAAACTCATTATTTATACTGCAAAACTTTACACTGTCTATTAGTCAACTTCTA
TAAACGAAGTGTGGATAAAATATTAAAACAAAAATATTTATGATTTATACATATGTCCATATGCTTTTTATTTCAGAAGTTTGTTTTTTTGGGGT
TTACTAAGTACTAGAATATATTAAACACTCGCAGCCAGCCTGCTCTGATCGCAACTAGTTGAGGGGATTCGATGTCTTGGCGCTCTCCTGGCGGA
TGGCGTTGATCAGCTCGTAGTTGACCAGGAAGGTGAAGCGCAGACCGGATATTTCCACTGTGCAGTTGTGACCGAGTCGAGCTTTGTTGGCGGAT
AGCAAAGGAGTGCCGTCGATAAAGATGGCCCTCTTTCCCTCGTTAGCGATGAAGAAATCCCCATTGCTGCGCAGCTTAATGGTTCCTTGGCGGCG
AGAGATCTTCGCAGCCGGTCCCTCGAGCCCCAGATCCACGTCCACCACACAGTCCTTGGCATCGCGACCAAATGTTATTTCCTTGGAACGCATTA
GGTACCGCACATGGCGGCCACACAAGCAGGCCAGTGTCTGGTTGTCGAACTCGGAGGCAGCGGTCGGACTAAGCACGGAATCCACCAGGACGGCC
CAGCGCGAGAGCTCGTTCTCCAGCAGGCGAATATTACGTTTGTTGCGACGATCTGCCAGAGCTCGCTCCATCTCGAGAGCTTCGTCACGTGGCTC
GTTCAGGTCGTGCTCGAAGATTTGATCTTCTGCATCCGAGAAGCTGAGTGGCTGCTGATCCGTGCCATATATAGGCTTCACTGACTGATCCGGCA
ACAGGGTGTACTGCTTGAGAAGAAGCCAATGGTTTTGCAAGGATTTGGCAGTGCGGGCGCAGTAGAAAACGGAGGCATTCTTATCCAGTAGCTCC
TGGAACTGCTCAAGTTTTGGTTGTTCCGACTGTGAATTGAATTACTGATTAGAAAAAGCTTAAATCATGATGAAAATAGTGTACTTACGCTCTTA
ATGGTGCCAAGCAGATCCTCCTCCTGCACGCTGTACAAAGCTTTGCGCTGAACGGACTCCACGAGTTCGGGGTGCAGGTTCCTTATGGCGGACAC
TGCAATCCTGGACACCGCAGGCTCATACAGCAGAGCATACCAGCGCTGCTGTAGTTCCTGCAGAGTAAACTTGCAGGAAAACTTAACGCCGCGAT
GGATTATCCGCAGATCGTTGGTCTGCTGGATGCCAATTATGAGGGCCAAGTCGTCAATGGGCTTCCAGCGGCCCAAATCCTTGGTGGCCATCTGA
CCCATGGGACGACCATTTCTACGCTGCGCCTTTTTGCTGGCAGGACGCACTGGGCGCGAACGGCGCTCGCTGGTCGTGGAGCGCTCCATGGCCGG
TGGTTTGGGATGCGCGACGGCAGTCACAATTGGGGCAACTGGAAGGGGAGTGGCCAAGGGAGCTGGCGTTGTGGGCGTGGCCAGTGACAGCGATG
CAACAGTGCTAGGTGTCCCCGGCAGCAGGGAATCAACTGAAAGCGGCGTCTGTGGCGTGGAAGTGGGTATGTTAAGAGGCGCTAACGTGGTGTGC
GGCACGCCCACCAAAGCTGGATAATTCTGGGAGGTGGTGCGAGGCCTGCTGCTGCGATTGGCGTCTGTTCCGCTGCGATTTGTGGGCACCGCAAT
GTTGTACTCAACTATTTCGTCATCAAAACGCTTCCTTTTAATCGTCCGCGATGAACTGTTTCGATGCAAAAGGAGCTGCCACTTAATCTGTCAAT
TTTGACATATGTCATCGTCTCACCTTCTTCGCTTTTGATCGTTTTGCTGTTCTATCTGCAGATTTGAAATGGGATTTCGTATCGGCGTTGAAATT
CCAACGGCACTGCTAGCTGTACTTCCTATTGTGGTTGTTGTTGTTGTGGCTGCTGGTGTTGGCATGGTTGTTGTTGCTGGCGACACGCCTACCTG
GATTAGTGTGCTCGCAGCTGCTGTGGGAATGGTGGACACTGTGGGGGGATTGGAGCGGTAACGGACACTGCACTGCTGGCGATCGCGGTTATTC
TTGATGCCTCCATCGCTCTAGCGGGCTGTTTATGGGCTAAAATGTATTTATTTTCGCGACGCACAGCTCAGCAGTGTGACCGCACCAGCAGGAAA
AAGTATATCACTTGCAGAGTTGCCACGTCTTCGAAATAAAGTGTCACTGCAAGAAAAACATTTGTTAATAGCTTATATAAATATATATAAAATTA
ATTTTCTTTCTTAACAGTTCACTTGCTTAATATATAATTAGCGAAAGTGAGAACATTAAGCTTGACTTTACCATTTTAAAAGTTACCATCATAGT
GTCACTGGCCTGCCAGATCTCCATGGGAAACACATGTTTCGCAACACTGCTACCCACACAAACGCATTCGCGAATATCTGGTAACCTCGCCACTG
GAGCCCTCTCGAAATTTTGTTTACTGGCATTTAAAATCAGCGAATTCGGGCTAAAAAGTCTTACTTATGCACCCAGCACCGATGCCCGGAGCGAC
TAGATGAGTGTCTGGATGAGCGGGCCCCGAAATTTCGCACTAGCCACACAAATTATACGGGAAACTATGAGGTAAATGGTTCTTTGCACGAAAAC
AAAAAGGCGACTGACTAAGATATGACTAATCGATTTGCAGTTTGCACTACGCGGAATCGGAATCTTCGCCGTCAGAGAGCAAAATGGACATCTCG
GAGACGCCGACGGACTCAACGGGCGTCTCGCCGCTGGCGGATGATGTTTTGCCCACCGCGCCGGAGAAGAATATCCTGAAATTGGAGCAGGCCAA
GCAGGATCACGATAAGGAGGAACTGGAGTTCAAGACGACCTCCGCGCTGGACAACAGAATACTGCGTCCAGAGCTGCTGCCCATGGAGGCGATGC
CACAACGACACAACATCATCGAGCGCACCCTGGCCAACAGCCATCCGCTGATGTCGCCAACCAACACGGACTCAGACTCGGAACCCTTTCAGCTG
AAGAAGCAGGAGAAACAGCTGCCGAGGAGCAACTTTCCGGACGTTGTGCCCACCACGGAGACGGTGCAGGTGAAGAACAACCTGAACCAATGCCG
GAACAAGCCGCAGGACGCCAAGGTCAGCCTGCTAAGG
(SEQ ID NO: 55)

Exon: 3027..2684
Exon: 2620..1894
Exon: 1834..1001
Start ATG: 2958 (Reverse strand: CAT)

Transcript No. : CT1834
CGGTCACACTGCTGAGCTGTGCGTCGCGAAAATAAATACATTTTAGCCCATAAACAGCCCGCTAGAGCGATGGAGGCATCAAGAATAACCGCGAT
CGCCAGCAGTGCAGTGTCCGTTACCGCTCCCAATCCCCCCACAGTGTCCACCATTCCCACAGCAGCTGCGAGCACACTAATCCAGGTAGGCGTGT
CGCCAGCAACAACAACCATGCCAACACCAGCAGCCACAACAACAACAACCACAATAGGAAGTACAGCTAGCAGTGCCGTTGGAATTTCAACGCCG
ATACGAAATCCCATTTCAAATCTGCAGATAGAACAGCAAAACGATCAAAAGCGAAGAAGTTCATCGCGGACGATTAAAAGGAAGCGTTTTGATGA CGAAATAGTTGAGTACAACATTGCGGTGCCCACAAATCGCAGCGGAACAGACGCCAATCGCAGCAGCAGGCCTCGCACCACCTCCCAGAATTATC
CAGCTTTGGTGGGCGTGCCGCACACCACGTTAGCGCCTCTTAACATACCCACTTCCACGCCACAGACGCCGCTTTCAGTTGATTCCCTGCTGCCG
GGGACACCTAGCACTGTTGCATCGCTGTCACTGGCCACGCCCACAACGCCAGCTCCCTTGGCCACTCCCCTTCCAGTTGCCCCAATTGTGACTGC
CGTCGCGCATCCCAAACCACCGGCCATGGAGCGCTCCACGACCAGCGAGCGCCGTTCGCGCCCAGTGCGTCCTGCCAGCAAAAAGGCGCAGCGTA
GAAATGGTCGTCCCATGGGTCAGATGGCCACCAAGGATTTGGGCCGCTGGAAGCCCATTGACGACTTGGCCCTCATAATTGGCATCCAGCAGACC
AACGATCTGCGGATAATCCATCGCGGCGTTAAGTTTTCCTGCAAGTTTACTCTGCAGGAACTACAGCAGCGCTGGTATGCTCTGCTGTATGAGCC
TGCGGTGTCCAGGATTGCAGTGTCCGCCATAAGGAACCTGCACCCCGAACTCGTGGAGTCCGTTCAGCGCAAAGCTTTGTACAGCGTGCAGGAGG
AGGATCTGCTTGGCACCATTAAGAGCTCGGAACAACCAAAACTTGAGCAGTTCCAGGAGCTACTGGATAAGAATGCCTCCGTTTTCTACTGCGCC
CGCACTGCCAAATCCTTGCAAAACCATTGGCTTCTTCTCAAGCAGTACACCCTGTTGCCGGATCAGTCAGTGAAGCCTATATATGGCACGGATCA
GCAGCCACTCAGCTTCTCGGATGCAGAAGATCAAATCTTCGAGCACGACCTGAACGAGCCACGTGACGAAGCTCTCGAGATGGAGCGAGCTCTGG
CAGATCGTCGCAACAAACGTAATATTCGCCTGCTGGAGAACGAGCTCTCGCGCTGGGCCGTCCTGGTGGATTCCGTGCTTAGTCCGACCGCTGCC
TCCGAGTTCGACAACCAGACACTGGCCTGCTTGTGTGGCCGCCATGTGCGGTACCTAATGCGTTCCAAGGAAATAACATTTGGTCGCGATGCCAA
GGACTGTGTGGTGGACGTGGATCTGGGGCTCGAGGGACCGGCTGCGAAGATCTCTCGCCGCCAAGGAACCATTAAGCTGCGCAGCAATGGGGATT
TCTTCATCGCTAACGAGGGAAAGAGGGCCATCTTTATCGACGGCACTCCTTTGCTATCCGCCAACAAAGCTCGACTCGGTCACAACTGCACAGTG
GAAATATCCGGTCTGCGCTTCACCTTCCTGGTCAACTACGAGCTGATCAACGCCATCCGCCAGGAGAGCGCCAAGACATCGAATCCCCTCAACTA
GTTGCGATCAGAGCAGGCTGGCTGCGAGTGTTTAATATATTCTAGTACTTAGTAAACCCCAAAAAAACAAACTTCTGAAATAAAAAGCATATGGA
CATAT
(SEQ ID NO: 56)

Start ATG: 70 (Reverse strand: CAT)

MEASRITAIASSAVSVTAPNPPTVSTIPTAAASTLIQVGVSPATTTMPTPAATTTTTTIGSTASSAVGISTPIRNPISNLQIEQQNDQKRRSSSR
TIKRKRFDDEIVEYNIAVPTNRSGTDANRSSRPRTTSQNYPALVGVPHTTLAPLNIPTSTPQTPLSVDSLLPGTPSTVASLSLATPTTPAPLATP
LPVAPIVTAVAHPKPPAMERSTTSERRSRPVRPASKKAQRRNGRPMGQMATKDLGRWKPIDDLALIIGIQQTNDLRIIHRGVKFSCKFTLQELQQ
RWYALLYEPAVSRIAVSAIRNLHPELVESVQRKALYSVQEEDLLGTIKSSEQPKLEQFQELLDKNASVFYCARTAKSLQNHWLLLKQYTLLPDQS
VKPIYGTDQQPLSFSDAEDQIFEHDLNEPRDEALEMERALADRRNKRNIRLLENELSRWAVLVDSVLSPTAASEFDNQTLACLCGRHVRYLMRSK
EITFGRDAKDCVVDVDLGLEGPAAKISRRQGTIKLRSNGDFFIANEGKRAIFIDGTPLLSANKARLGHNCTVEISGLRFTFLVNYELINAIRQES
AKTSNPLN*
(SEQ ID NO: 57)

Classification: hypothetical

Celera Sequence No. : 142000013384447
AGGTGGTATTAGGTGTTGCTGCTTTGGAGGCGTCAACTTCACGAGAAGAGCTTCACCGTTCTGGTCGAGATTTTCATAGTCTAGTGCCAGATCCC
TGTTGATCCTGAACAAAGTGGGCGTCTGCATTGGGATGAGTCTGTCCATTTTGTAGTTCATGAAGCATTCCGCTCGAAAGTGCCGGGCACAAACT
GTTTTGGCTGCCAGTTTGGACGGCGGTGCATTTGAAACGTCAGGGTTTGAACAATTCCTGACCCAATCTTTCAACCTCTTCGGATCCTTAACGGG
GAACTTGAAGAAGTGCATATTGGGGTTGCGGCTAGAACCCACCGGACAATCACGAAAACAACACTTAGTGCCGCCCATTTGTTTAAATATAAGCA
AACAACTTTTATGTTATTAGTGGTGGAAGTGTTAGCGTCAGCTGGTGATATCGATGGGAGGCATCGATAACAGAATTGACCGAAACCAAATGATC
GATATGACACTTCTTAATTAATGAGAGATTTTTTACTTGACTGGGCTTGTAGCAGGTTTTGCACAGAAGCAATTATTTTCCGGAATGTGAAATGT
CTGCTTTTTAGCTAATTACAACAAAAACTTTCCAATTTTTGTTCCCCAAACCCACTCAAGTGATTTCAAATTTTACCGTCCGCTTAAAATGGAAC
TAGTTTATTCCAGAGGAACCAGCTTGCACCACCAAGTCTCTGAAACTCTGGAAATATCGATAGTCTGGTGGAGAAAAGTATTCATAAATATAAAT
AAAAATTAACAGGTCATAAGCTGATTTGTTTATTATTTACTGTTAAAACAAGTAAAATAATATTGGGAACAATTAAATTTTCCATTTTCCTAATT
ACAGTATAAGCCTAGTGGGCGTTTTGATATCCAATTGTAATGTTTTAAGCAATCCCAGTGGGCTTTGCTCAATCGTTCGGACCACTTAGACGAAT
TTCCACCAAACTTAGTTCAGTATAATTTTTGAATTCGCCCGCACAGGTTGCGCACTTTTCGACCGTATCACAACACTGATCTACCCTAGTATTCA
CAGGAAGTTGCATCCCTGGCATCCAGAAGCCTCTAGAAGTTTCTAGAGACTTCCAGTTCGGGTCGGGTTTTTCTATAAAAGCAGACGCGCGGCGT
TTGCCGGTTCGAGTCTTGAAAAAAATTTCGTACGGTGTGCGTCGTAACAACAAGCAGCGTCTGAAAAGTTTTGTGAATTTCCAATTCTATACAAA
GCAAAGTGAAAATATCTGTATTTTTACCTTTATTCTGTGAATAGAACGAAAAACATACATACAAGGTGAGTAATGCAAATTACAAGAAAAGAGTG
AATAGTTTATCAGTGGCTATGGCCAAAATGTGCATTTTGCGTGGTCCTGTGCATCTCGAATGTTCTTGACCCAAATGTGAGATATTGATTTTAAA
TTTCTAGGAGCCAAGTTTAAGAATTTTTTTGATTAATTAAGAGGTGGCAACGTGCAAATTAACTCAAAATGCCGGTTTCTTTTATTTTTTGTCG
CTTGGACGCATCTTCCAGAGGTTTCTATGCTTTAGCATGAATTAAACATCGTGCCAAATAGGCCTTTTAATTATATATTACTGTCCTTTATTTAC
AATTACATGTGGTTTATAGAATACAAGATTAATTTTTGTTTAATGCAATGGTCTTTTAGCGCTAAATCGAATTATGCCGCTCTTTTTAGGGGGTG
ACAATGCGCAAATCACATTTGCCGCTCGAGAATGTTCTAGAGGTTTCTATGCTTTAGCATGAATTAAACAGCGTGCCAAATAGGCTTTTTAATTA
TAAATTACTGTCCTTCATTTACAATTACACGTGCTTTCTTTGCATTCCCATTTTAAATTGCACATGCCGCATACGCACACATGCACGCCCATGAC
TAATACTTTCAAGTAAAAATGTGGCGTCAGTAAGCAAATTCTGTTAAATCGGTTTTTTAATCCTATTTGCTCTATTTTAATTGGTTGGTTGCTAC
TAGCAACTTGCTAGGCGAATTAGTTTTCCTTTGGCTTCTAGATGCTTCCACAAACTTCCTTGGTGAAGTACGAATTTTCAATGCAATGCTCACTC
ACACAGACACGAGTTTGCACACAGCAGGGGTAGAAAAATTATCAACCGACCCAATTTGCATAATTATATTTAAATATTTAAATTTAAAACATTAT
TTTGCAACTTAAAATCAATTCTGTTGGCTAATTGAAATTAAAATTCCATTTTACGGGTTGCAAAGTGAATGCTATAATTTTGACCACCACTGTAC
TTGTATATGCGCATGTTAAATGAGGCATGTGCAAAAGAGAAAGAAAGAAAAAGAATAAAACCGGAGCAGCTGCTGAAAATGCAGCTGCTTTTCCT
TAGTGTTGAACCCACAGACTATAACTAATCCTAATGATTTTGTAAATCCATTGCAGATGCCAGAAGAAGCAGAGACCTTTGCATTCCAGGCTGAG
ATTGCTCAGCTGATGTCCCTGATCATCAACACATTCTACTCGAACAAGGAGATTTTCCTGCGCGAGTTGATCTCGAACGCTTCCGATGCCCTGGA
CAAGATCCGCTATGAGTCCCTTACTGACCCCAGCAAGCTGGACTCTGGCAAGGAGCTGTACATCAAGCTGATCCCTAACAAGACGGCTGGTACTC
TGACCATCATTGATACCGGTATCGGTATGACCAAGTCCGACCTGGTCAACAACTTGGGAACCATTGCCAAGTCCGGAACCAAGGCCTTCATGGAG
GCTCTGCAGGCTGGTGCCGACATTTCCATGATCGGTCAGTTCGGTGTGGGTTTCTACTCCGCCTACCTGGTCGCCGACAAGGTGACTGTCACCTC
CAAGAACAACGATGACGAGCAGTACGTGTGGGAGTCCTCTGCCGGAGGCTCTTTCACAGTCCGTGCCGACAACTCTGAGCCCCTGGGCCGTGGCA
CCAAGATCGTGCTGTACATCAAGGAGGACCAGACCGACTATCTGGAGGAGAGCAAGATCAAGGAGATTGTTAACAAGCACTCCCAGTTCATTGGC
TACCCCATCAAGCTGCTCGTAGAGAAGGAGCGCGAGAAGGAGGTCAGCGACGATGAGGCTGATGATGAGAAGAAGGAAGGTGATGAGAAGAAGGA
GATGGAGACTGATGAGCCCAAAATCGAGGATGTTGGCGAGGATGAGGATGCCGACAAGAAGGACAAGGATGCCAAGAAGAAGAAGACCATCAAGG
AGAAGTACACTGAGGATGAGGAGCTGAACAAGACCAAGCCCATCTGGACCCGCAATCCCGATGATATCTCCCAGGAGGAGTACGGCGAGTTCTAC
AAATCCCTGACCAACGACTGGGAGGATCATCTGGCCGTCAAGCACTTCTCCGTGGAGGGTCAGCTGGAGTTCCGTGCTCTGCTCTTCATTCCCCG
TCGCACGCCCTTCGATCTCTTCGAGAACCAGAAGAAGCGCAACAACATCAAGCTGTACGTGCGTCGTGTCTTCATCATGGACAACTGCGAGGACC

FIGURE SHEET 18

TCATTCCAGAGTACTTGAACTTCATGAAGGGTGTGGTCGACTCCGAGGATCTGCCCCTCAACATCTCACGTGAGATGCTGCAGCAGAACAAGGTC
CTAAAGGTGATCCGCAAGAACCTGGTCAAGAAGACCATGGAGCTGATTGAGGAGCTCACCGAGGACAAGGAGAACTACAAGAAGTTCTATGACCA
GTTCAGCAAGAACCTGAAGCTGGGTGTGCACGAGGACAGCAACAACCGTGCCAAGTTGGCCGACTTCCTTCGCTTCCACACCTCTGCCTCCGGCG
ACGATTTCTGCTCCCTGGCCGACTACGTGTCGCGCATGAAGGATAACCAGAAGCACGTGTACTTCATCACTGGCGAGTCCAAGGACCAGGTCAGC
AACTCTGCCTTCGTGGAGCGCGTCAAGGCCCGTGGCTTCGAGGTGGTCTACATGACCGAGCCCATCGATGAGTATGTCATCCAGCACTTGAAGGA
GTACAAGGGCAAGCAGCTGGTCTCTGTCACCAAGGAGGGTCTGGAGCTGCCTGAGGATGAGAGCGAGAAGAAGAAGCGCGAGGAGGACAAGGCCA
AGTTCGAGAGCCTGTGCAAGCTGATGAAGTCCATCCTGGACAACAAGGTCGAGAAGGTGGTGGTGTCCAACCGCCTGGTGGATTCGCCCTGCTGC
ATTGTCACTTCGCAGTTCGGCTGGTCCGCTAACATGGAGCGCATCATGAAGGCCCAGGCTCTGCGTGATACCGCCACAATGGGCTACATGGCCGG
CAAGAAGCAGCTGGAGATCAACCCCGATCACCCAATTGTGGAGACTCTCCGCCAGAAGGCCGATGCCGACAAGAACGATAAGGCCGTCAAGGATC
TGGTCATCCTGCTGTTCGAGACCTCTCTGCTGTCCTCTGGATTCTCGCTGGACAGCCCCCAGGTGCACGCCAGCCGCATCTACCGCATGATCAAG
CTGGGCTTGGGAATCGACGAGGACGAGCCTATGACTACCGACGATGCCCAGAGCGCCGGAGATGCCCCCTCGCTGGTTGAGGACACAGAGGACGC
TTCCCACATGGAGGAGGTCGATTAAGCGACCAGTCGAAACAAACAACCAAAATTCATTCTATCACTCGCATTCACATACACAATTTACTTGCGTT
TCGAACTTTTATACTGAGTTTACTACGGCCGAGTTAAATTTTGTATTCATTAACATTTTGCCGCGTTATAAGCGACAGACATACGCTTAACTCAT
AAAAAAGCAGGAATAACTCGTTAAATGGTTAGGTTCTCACAGAACATTCAAGAGCAGTTGTCGTTTTAAGAACTTATAATTTAGAATCCAAGTAA
TTTATGTAAAAAACTAAAGACTACATACGCGCCCTAGTTGGTAGAGCTATATAAAGAATCGAGTATATATATAATTAAGGTTTGATGACCCGATC
GATGATAAACATAAAACCAAATAAACAACAAGCAAATGTGTTTTAAAAATCTAACTTCTGAGCGAGTATTTATTGGGGGGAATAAACAATCTATG
AATCGGATTCTTTGCGCAGCAGCTGCTCAATGGCCTCCACCGTGGACACTCCCTTGGTTATCATTATTATCTTGTTTCGCGATCGAGATCCCTTG
TCCAAAGAAACGTCGCTCTTTCGAAGACCTAGAACTTTCGACAGAAACTTGACCAGTTCGGCGTTAGCTTCTCCCTCGCTGGGCGGAGCGGCGAT
TTGGACGCCCACTCCTTCAAAGCCAATTCCTGTGATTCCGTTCTGCTTAGCCCCCGGCTTGGCAAGGATTTGTATGCATATATTGCCGCTCTTAT
CGACTGAAATCGGACTGGCTTCCTTAGCCGGCATCGCTTTTGCATCGTTTTTCGCACTTTCAACGCCGGCCTTTGATTTCCCCTTGCTCTTCGAC
ATTATTTGGGCGTTGACCGATGTAAACAAGCGGCGCATTAGCTTCTTGGCAATTATTTTAAATATTTTGTGTTTTTAAATGCATTTTAATAGCAA
CTAGTGTTTAATTTTGCGAGGTCTACTGGCGTCTATCAGCTGATTCGTGGAGAAAACCAGGGATGCGCACATATAGGGATGAGCATATCTCGTGA
GTTCTCACTCACGAAACGAAGATAAAACTACATTTTTACATTCCATGTAACTTACAGATTGGACATGAATAGTACGATTCAAAAATGTATTTTTA
TTTTCCTGTTGAGTATTATTTAACGGTTTCTAAACACATTCCCCCCGAAGTCACCACAACATGTAAATAAAAGTATTAAAACAAAATATGATTA
GGTAAAAAATTATCATATATTCATCATTGTTATGTACTCATAGTTTCTTCTCTACTCGTCTTTGCATTAGAAAACAACGCTTTAACACTTTGCAC
TATTTAAAACTGCGCCGAGAAGCATCTTAAAAATGCATTTATCGCCTATAAATGAT
(SEQ ID NO: 58)

Exon: 1001..1300
Exon: 2432..4946
Start ATG: 2432

Transcript No. : CT2354
CGCACTTTTCGACCGTATCACAACACTGATCTACCCTAGTATTCACAGGAAGTTGCATCCCTGGCATCCAGAAGCCTCTAGAAGTTTCTAGAGAC
TTCCAGTTCGGGTCGGGTTTTTCTATAAAAGCAGACGCGCGGCGGTTTGCCGGTTCGAGTCTTGAAAAAAATTTCGTACGGTGTGCGTCGTAACAA
CAAGCAGCGTCTGAAAAGTTTTGTGAATTTCCAATTCTATACAAAGCAAAGTGAAAATATCTGTATTTTTACCTTTATTCTGTGAATAGAACGAA
AAACATACATACAAGATGCCAGAAGAAGCAGAGACCTTTGCATTCCAGGCTGAGATTGCTCAGCTGATGTCCCTGATCATCAACACATTCTACTC
GAACAAGGAGATTTTCCTGCGCGAGTTGATCTCGAACGCTTCCGATGCCCTGGACAAGATCCGCTATGAGTCCCTTACTGACCCCAGCAAGCTGG
ACTCTGGCAAGGAGCTGTACATCAAGCTGATCCCTAACAAGACGGCTGGTACTCTGACCATCATTGATACCGGTATCGGTATGACCAAGTCCGAC
CTGGTCAACAACTTGGGAACCATTGCCAAGTCCGGAACCAAGGCCTTCATGGAGGCTCTGCAGGCTGGTGCCGACATTTCCATGATCGGTCAGTT
CGGTGTGGGTTTCTACTCCGCCTACCTGGTCGCCGACAAGGTGACTGTCACCTCCAAGAACAACGATGACGAGCAGTACGTGTGGGAGTCCTCTG
CCGGAGGCTCTTTCACAGTCCGTGCCGACAACTCTGAGCCCCTGGGCCGTGGCACCAAGATCGTGCTGTACATCAAGGAGGACCAGACCGACTAT
CTGGAGGAGAGCAAGATCAAGGAGATTGTTAACAAGCACTCCCAGTTCATTGGCTACCCCATCAAGCTGCTCGTAGAGAAGGAGCGCGAGAAGGA
GGTCAGCGACGATGAGGCTGATGATGAGAAGGAAGGTGATGAGAAGAAGGAGATGGAGACTGATGAGCCCAAAATCGAGGATGTTGGCGAGG
ATGAGGATGCCGACAAGAAGGACAAGGATGCCAAGAAGAAGAAGACCATCAAGGAGAAGTACACTGAGGATGAGGAGCTGAACAAGACCAAGCCC
ATCTGGACCCGCAATCCCGATGATATCTCCCAGGAGGAGTACGGCGAGTTCTACAAATCCCTGACCAACGACTGGGAGGATCATCTGGCCGTCAA
GCACTTCTCCGTGGAGGGTCAGCTGGAGTTCCGTGCTCTGCTCTTCATTCCCCGTCGCACGCCCTTCGATCTCTTCGAGAACCAGAAGAAGCGCA
ACAACATCAAGCTGTACGTGCGTCGTGTCTTCATCATGGACAACTGCGAGGACCTCATTCCAGAGTACTTGAACTTCATGAAGGGTGTGGTCGAC
TCCGAGGATCTGCCCCTCAACATCTCACGTGAGATGCTGCAGCAGAACAAGGTCCTAAAGGTGATCCGCAAGAACCTGGTCAAGAAGACCATGGA
GCTGATTGAGGAGCTCACCGAGGACAAGGAGAACTACAAGAAGTTCTATGACCAGTTCAGCAAGAACCTGAAGCTGGGTGTGCACGAGGACAGCA
ACAACCGTGCCAAGTTGGCCGACTTCCTTCGCTTCCACACCTCTGCCTCCGGCGACGATTTCTGCTCCCTGGCCGACTACGTGTCGCGCATGAAG
GATAACCAGAAGCACGTGTACTTCATCACTGGCGAGTCCAAGGACCAGGTCAGCAACTCTGCCTTCGTGGAGCGCGTCAAGGCCCGTGGCTTCGA
GGTGGTCTACATGACCGAGCCCATCGATGAGTATGTCATCCAGCACTTGAAGGAGTACAAGGGCAAGCAGCTGGTCTCTGTCACCAAGGAGGGTC
TGGAGCTGCCTGAGGATGAGAGCGAGAAGAAGAAGCGCGAGGAGGACAAGGCCAAGTTCGAGAGCCTGTGCAAGCTGATGAAGTCCATCCTGGAC
AACAAGGTCGAGAAGGTGGTGGTGTCCAACCGCCTGGTGGATTCGCCCTGCTGCATTGTCACTTCGCAGTTCGGCTGGTCCGCTAACATGGAGCG
CATCATGAAGGCCCAGGCTCTGCGTGATACCGCCACAATGGGCTACATGGCCGGCAAGAAGCAGCTGGAGATCAACCCCGATCACCCAATTGTGG
AGACTCTCCGCCAGAAGGCCGATGCCGACAAGAACGATAAGGCCGTCAAGGATCTGGTCATCCTGCTGTTCGAGACCTCTCTGCTGTCCTCTGGA
TTCTCGCTGGACAGCCCCCAGGTGCACGCCAGCCGCATCTACCGCATGATCAAGCTGGGCTTGGGAATCGACGAGGACGAGCCTATGACTACCGA
CGATGCCCAGAGCGCCGGAGATGCCCCCTCGCTGGTTGAGGACACAGAGGACGCTTCCCACATGGAGGAGGTCGATTAAGCGACCAGTCGAAACA
AACAACCAAAATTCATTCTATCACTCGCATTCACATACACAATTTACTTGCGTTTCGAACTTTTATACTGAGTTTACTACGGCCGAGTTAAATTT
TGTATTCATTAACATTTTGCCGCGTTATAAGCGACAGACATACGCTTAACTCATAAAAAAGCAGGAATAACTCGTTAAATGGTTAGGTTCTCACA
GAACATTCAAGAGCAGTTGTCGTTTTAAGAACTTATAATTTAGAATCCAAGTAATTTATGTAAAAAACTAAAGACTACATACGCGCCCTAGTTGG
TAGAGCTATATAAAGAATCGAGTATATATATAATTAAGGTTTGATGACCCGATCGATGAT
(SEQ ID NO: 59)

Start ATG: 301

MPEEAETFAFQAEIAQLMSLIINTFYSNKEIFLRELISNASDALDKIRYESLTDPSKLDSGKELYIKLIPNKTAGTLTIIDTGIGMTKSDLVNNL
GTIAKSGTKAFMEALQAGADISMIGQFGVGFYSAYLVADKVTVTSKNNDDEQYVWESSAGGSFTVRADNSEPLGRGTKIVLYIKEDQTDYLEESK
IKEIVNKHSQFIGYPIKLLVEKEREKEVSDDEADDEKKEGDEKKEMETDEPKIEDVGEDEDADKKDKDAKKKKTIKEKYTEDEELNKTKPIWTRN
PDDISQEEYGEFYKSLTNDWEDHLAVKHFSVEGQLEFRALLFIPRRTPFDLFENQKKRNNIKLYVRRVFIMDNCEDLIPEYLNFMKGVVDSEDLP

FIGURE SHEET 19

LNISREMLQQNKVLKVIRKNLVKKTMELIEELTEDKENYKKFYDQFSKNLKLGVHEDSNNRAKLADFLRFHTSASGDDFCSLADYVSRMKDNQKH
VYFITGESKDQVSNSAFVERVKARGFEVVYMTEPIDEYVIQHLKEYKGKQLVSVTKEGLELPEDESEKKKREEDKAKFESLCKLMKSILDNKVEK
VVVSNRLVDSPCCIVTSQFGWSANMERIMKAQALRDTATMGYMAGKKQLEINPDHPIVETLRQKADADKNDKAVKDLVILLFETSLLSSGFSLDS
PQVHASRIYRMIKLGLGIDEDEPMTTDDAQSAGDAPSLVEDTEDASHMEEVD*
(SEQ ID NO: 60)

Name: Heat shock protein 83
Classification: chaperone
Gene Symbol: Hsp83
FlyBase ID: FBgn0001233

Celera Sequence No. : 142000013384244
CACGCTCTCGGACACTAGATAATTGCCAGCCCCAATATCGGTGATAGGCGTCGACTTTTGCCCCCACCCACCCCCGTCTCATATATACGTATATA
ACTATCGATGACGTCATGTGGGAAGTGCAGGTGCATTTGAAATGCAAATTGCTTTTGCTGCAAACCATCTGTCCATATACCGCTTATATAAGGCG
GGCACAGATCGCTCAGACTCAGTTCTGCATAATTTGAACGGAGTTTTTAGAACACGTACATATAGTTCGTAGATTTGGAATTTTTATAGAAATG
ACGAATCGAAACTAAGCGAATCCATTTTGGCAATCCATGGTCTTGGACCCGAAATGCTTTTAGCACTCCAGTGCGATGTTGTTGTTTGCATTGCT
CGTGGCCCAATTAATTTATATCCAAGTGCGTATTTCGATTTAGTACGGCGCATTGAAAGTCTCCGGTTGAAAAAGCCCAAGGTTATCACACATCC
CGACCAGAAATCGTACTCACAGCCAGTCTCCTCCTGGATTTGCGCGATCTCCTCGTTCCGCAGGAAAAGCGACGACTTATTGCCCATGGTGACGG
TGTGTTGTGCGCCGATCGGTTTGTTTAAACATTCAACAATCGCAGACGAGCATTGAATGGCATTCGATTTGGATTGGACCACAAGTCCGATTTGT
GTACAGGCTGAATGCAGGCGGAGTGACGGGAAAATGCCGAAAATCGGGTGCAAAAAAATACTGAACAGCCAGCGATGGTTGCACTAGAGACGGAC
TTTGTCAAGTGGTGGATGGTTTCCCTATAAATATCGATTCACATATTTTTTTGTATCTATTTAAAGTGCACATTTTTTAAGGGGTCATTTGTAAG
CATTTCCTTACAAACAACGACCAAAAATTTGATATATTAATTAATTTCTTAGAAATATCCAATCGTTTATGCAAAGCCTACAGTAATTTCGTCTC
ATCACTAGCTCGTAACTGGCAATCTCCCATCTCTATTGGCATTCGCAAAGAAAACAAAGTAAACATTTTTTTTTGCCGGAACGAGAATTACCGTT
ATGGATAAGTTAAATTCCACTCTAACTGCCGTCAAAAACCTGCGGTCCAACGTAAGGCTGTGCTTCGAGCACCTGGCCGATGGAACCGATGGGGA
GAGCGGCGAGGAGAGCCGGAATAAGTTCGTAAATGACTTCCAGGAGAGATTCGCAGCCATCAACTCGCAAATACGGTTAGTGACCAGTTAACCTA
TTCCAGTGAAGAATACATTTGAATTAAACCACTTTTAGTGAGGTAGAGCAGCTGATTAATGGACTGCCGGTGCCACCAACACCCTATTCTCTCGG
GAACACCGCCTACCTGGCGCAGGAAACTTCGCAGGATCGACAGGCTCTATACCCTCAGCTGGTGAACAGCTACAAGTGGATGGACAAGGTGCACG
ACCACAGCTTCTTGGCCTTCAACAATCTCAACCAGAACACACTCAGGCGCTCCTACAATTACTGCTCGCAGAAGCGCCAGCGACTGCCCTTCTCG
TCCTTCAACAACGATCCAGAGTAAGTACGAAGTGCGCAGCTTCACTTTAATATTAACATCTTTCTTCCTCTGATTCTTAGCCACATAGATAAGCT
CCTGAGTGAGATCAACACCCCTCCGCATACTTCGTACAGAATTTTTCGTCCCTTCGGCACAAACGCTGTCACCATCGTAACAATAAGTAACGTGA
TGAAGGCGGCTATTGTCTTCAAAGGAGTGCTTATAGAGTGGGTTACGGTTAAGGGATTCGATGAGCCGCTGGAGCATGACGACCTGTGGGCCGAG
TCACGTTACGAGGTGTTCCGCAAAGTCCAGGATCATGCTCACTCAGCAATGCTGCATTTCTTTTCGCCGACGTTGCCCGATCTGGCAGTGAAAAG
CTATATAACCTGGCTGAACAGCCACGTCAAACTTTTCCTGGAGCCCTGCAAGCGTTGTGGGAAATTCGTGGTGAACGGATTGCCTCCGACGTGGC
GGGACCTGCGCACTCTAGAACCCTTCCACGAGGACTGCCGAAATTGCTAAGGATTTTTAAGTAATTTAACGCCGATAGTTGTAACTTGTATACTT
CATTTATTTCAAAAACAAAAATTATATGTACTTTGAATGCATGCGGGCGGATTTTTAAAATCGCTGCGCCCGACTGAATAACTACAACGGTTTA
ATGCGTTTCATTGGCCAACCAGTGCAGAAGTCGTCCGCTTCGATTTCTGCACCTGCGTCTGAACGCCGTGCTGCACGCACAGTCGCTCGAAGTTG
GCGCGCAGTTTTGCGCGGAGCTCCTCTCGCTTTCGCTGCACTTGCTCCCGGTGGCACTTGAAGGCCATAACCACCTCCTGGGGAATGTAATATGT
CTCCTCGTCTTTGTCGTCGTATTCGTCGAAGTCGTCCTGCAATTAATAAAGTTTTATTACTTTAATTTCGATATGGCAAATCATTTGCATAGCCC
ACTCTGTCTAGAATATTTTCTGGTAATTAATTCCGACCCTAAGCTCTTGATGATAAGAGTCGACAGGGCTTGCCGCAAGTCTTAGATTATGTTTA
AAAAACAATAATTACAATTTTCTTTTTCTATTTTTCCACTTCCTATTTTTATAGAGACAATCTTGCGACTCACCCACATCTGCAACAATGAAAAC
TTGTGATCCAACTGCGACTGGTGACTGTAGAAGAGCAAGTCGTCTGAGTCCTCATCGTGGACGTCGTGATTACACAGTCCATCCGAGCAAGACAC
TTCCGAGCCTTCTGGTGACGAAATCGCGCTAGATGTCCGAGAGCCGGCATGCGAAGGTGGATCGCTGCCGTATCCAGAATCGCGCACATCCTGCT
CGCACGGGCAGTTAGGCATGGACGCCAGGCACTCCTCGCACTTATCGCCAACCGTTTTGGCGATGCTTGACGAAATGCAACTGGCCACGTCAAGT
TGATCGTGATCAGCATCCAGCGGCTGGACCCTAGCCGTGGCTTGCATCTGCTTTTGGTTGCCCATCTTTGTGAAGGCCGCTTTCTTCTGCTTCTT
TTTCT
(SEQ ID NO: 61)

Exon: 1001..1215
Exon: 1274..1540
Exon: 1601..2045
Start ATG: 1046

Transcript No. : CT2432
AAAACAAAGTAAACATTTTTTTTTGCCGGAACGAGAATTACCGTTATGGATAAGTTAAATTCCACTCTAACTGCCGTCAAAAACCTGCGGTCCAA
CGTAAGGCTGTGCTTCGAGCACCTGGCCGATGGAACCGATGGGGAGAGCGGCGAGGAGAGCCGGAATAAGTTCGTAAATGACTTCCAGGAGAGAT
TCGCAGCCATCAACTCGCAAATACGTGAGGTAGAGCAGCTGATTAATGGACTGCCGGTGCCACCAACACCCTATTCTCTCGGGAACACCGCCTAC
CTGGCGCAGGAAACTTCGCAGGATCGACAGGCTCTATACCCTCAGCTGGTGAACAGCTACAAGTGGATGGACAAGGTGCACGACCACAGCTTCTT
GGCCTTCAACAATCTCAACCAGAACACACTCAGGCGCTCCTACAATTACTGCTCGCAGAAGCGCCAGCGACTGCCCTTCTCGTCCTTCAACAACG
ATCCAGACCACATAGATAAGCTCCTGAGTGAGATCAACACCCCTCCGCATACTTCGTACAGAATTTTTCGTCCCTTCGGCACAAACGCTGTCACC
ATCGTAACAATAAGTAACGTGATGAAGGCGGCTATTGTCTTCAAAGGAGTGCTTATAGAGTGGGTTACGGTTAAGGGATTCGATGAGCCGCTGGA
GCATGACGACCTGTGGGCCGAGTCACGTTACGAGGTGTTCCGCAAAGTCCAGGATCATGCTCACTCAGCAATGCTGCATTTCTTTTCGCCGACGT
TGCCCGATCTGGCAGTGAAAAGCTATATAACCTGGCTGAACAGCCACGTCAAACTTTTCCTGGAGCCCTGCAAGCGTTGTGGGAAATTCGTGGTG
AACGGATTGCCTCCGACGTGGCGGGACCTGCGCACTCTAGAACCCTTCCACGAGGACTGCCGAAATTGCTAA
(SEQ ID NO: 62)

Start ATG: 46

MDKLNSTLTAVKNLRSNVRLCFEHLADGTDGESGEESRNKFVNDFQERFAAINSQIREVEQLINGLPVPPTPYSLGNTAYLAQETSQDRQALYPQ
LVNSYKWMDKVHDHSFLAFNNLNQNTLRRSYNYCSQKRQRLPFSSFNNDPDHIDKLLSEINTPPHTSYRIFRPFGTNAVTIVTISNVMKAAIVFK

GVLIEWVTVKGFDEPLEHDDLWAESRYEVFRKVQDHAHSAMLHFFSPTLPDLAVKSYITWLNSHVKLFLEPCKRCGKFVVNGLPPTWRDLRTLEP
FHEDCRNC*
(SEQ ID NO: 63)

Name: transcriptional co-activator
Classification: transcription_factor_binding

Celera Sequence No. : 142000013385192
TGCTTCGACGACCTCCTGGTTGACTACCAGACCAGGTACAAAATCGAAAAGATCAAGGTAATGGGTTGGACCTATATGGTGGCCTGTGGCCTCGA
AACGGACCACTACACGGACTTCTCCATCGACATTCCGGTCAAGCAACCGGAAGCTGATTCCGAAATTAGACGAGGATCCAGCGGTGACTATTTCC
CACGACTAGATTAGAGTACAATTGTAAAAGGTACATCTATTCAGTTCTGACTGTCCATTTTGGAAGTACCGAGGACGATGAGATGAGCGGCGATA
ATGTCAGCCAGCCCTACGCCCAAGTGCAAGATGTCGCCGTCCTGGTGATGACCGAGTTTGCCCTGGACTTACTTCGCATCATGCACGACATTCGG
TACAACTACGTGTTCTCGGAGTACGATACATTCTTAACGGGGAGCTTGAAGATAGGTGGGCTGCATTACCTTCACCGTTATCCTAATCCATCCAA
TGATATCTAAGGCATCTCCCATGGATCCGTGATGGCCGGCGTTGTTGGACTCTCGAAACCACACTATGATATCTGGGGTCATACCGTCAATATGG
CCTCCCGGATGTCCTCCACTGGATTGCTGGACAACATCCAAGTAACTCGGCACACGGCAAAGGTGCTGCGACAATTTAACATCCGCTGCAACTAC
CGAGGGCACACGGAGGTAAAGGGAGTGGGCAAGGTGCCCACCTACCTGGTGGTCGTAGACCCGGATCTCACATTCCAAGATCACGACCAAGTGAG
CATGAGTATGAAGGACTCAAAAAGCTGGGTCATCGACACTCTTTCACTGTCATTCACCCCGAGCTTCGTGCCCCCAAAGTCTTCCACTTCGGATG
AAGAGGAGGCTGAAGGAGAGCTCGAGGAAAATGTATCTGAAGGCGATGAACTGGAGGTCTCGATACATGAGCGCCAAAAGGGAGGCATCTTTCTG
GCCGGGAACCTTCATTAATTTAAATTTATTTTAATAGATATATATATATATATATATTTATTTAAGCATATATAACACACATATATAGATGTATT
CGTACAGTTCAAAGCAAATGTTTTTCTTGAGGTTAAATACGTTATGATTTGAGCACTCGCTGAAATCATTGCACAACTGGTGACCAAAGTATACG
TATGTTCATAATTCAGAGTCATACATAGTCGTTAGGTTATGTACATGCTACAGATAATACACTCATCTTGACGAATCTCCATCTCCATCACTAAG
AAAGCACCATCCGTGTGATCAGGTTCGGTTTCGTTTGGTTTTGTGCACAGTTTTTAGCTTAAGTAAGCATTGCAGTTGATTTGGGGCATGGGCAT
AGCCCTTACTCGTTGACAGAACTGGAGTTCAGCAGAGCCGTGTCCTCGGGAATGGGCTTCCGCTTGTAGGAGGGCTCAGTGGCTAGGTAGACAAC
CAGCGCCCCGAAGACCACGTACATTACTCCAATCACATTGGCCAACACACCAGCCGGTGGAAGAGTGGAGTAAGCCGGAGTTTTGCTAGAAATGT
CGTCATGGATTAGTCAAGTGATCGATCTAGAATGCATATACACCTACATGGCGAAGATGGCCTTCTCGGTTATGCCCATCAGGGCACTAGCAATA
GCCAGAACGAATCCAAAGAGTCCGAAGTAGATGTGCAGCGGCATCATGGCGATCCTGTAGTTCTCCCTCAACCCCGGCGCCAAAAAGGCCACAAA
TCCGGCCACATACTGCAGCGAGAAGACGATCACCGCGGAGAGCCCCAGCCAAGAGTGCAGGGAGTACATGTTGGGAATGGGCGGATTGGCCAAGT
TGTGGGAATCGAAGACCGTCTTCAGGGCAATCACCGTCAGAATGAATGCACCCATGTGGATGCCGGCGTGGGTAAGCTTCAGAGTCTTCTTGCGC
GTGGTGCGGAAACCACGATAGATCAGAATGGCTGTGGGATTGAATTGAGTTGGATTACCATTTCGAAGCTAGTCAATGGGAGTGGCGTGGCACCT
CTTCCGCTGCATTTACTCACAGTTGCCATACAGGTAAATGAAGCCAATGGTCATGAACAGCGGATGCCAGTTGAACTCCACGCCGGGATTTGAGG
TGCCGGCCAGACCGCCGAAGTGCTGGCCAATCCAGGTGGCCACCAGGACGATCATGGTCAGGCCGCACAGCTGGGTGAGCACATAGAGCACCTTA
AAGTTGATCAGCGCTGGATCCATGTTGGCCTTGCCGCTGCCTGAAAAATCCAATAAAAGCTGGGGATGAGCTAAAAATAGAGGCCATTTTACGCA
CAGCACGCATTGGCGATCTAATCGCATAACTCATTCAAGGGTAGAGATATCGGGGCATCGAAAGGGGAAGGGGATCTCAAGCACTCGTTTATATT
TTCCATACTTTTGGTTTATAGCCTCTGCTACGTAAACATGATTCAATTACATGTTCCACCTGCCCGCAGATTAAAATAACCCCCAAGCACTTGCT
GATAACATGCGACCAGAAGTTTAGGGAGCCAATAGGCTTCCCAAAAACCCACTTTAACAGTTGTACATCTGATCCGCTTCGATGGCAGCTGCACT
CGTTGGGTAAACAAACAGTTCCTTTGCCGCCAGCCATCCGATACTGCGATAAACAAGATCTCATCATATCGACTGGGCCCTGAGTTAATGGGAAC
GGCCTGTTCCCAGGCACTGGGACACACCCACGACCCCTTTCGCCGGCCACTCACCAGGCGTAATTTGGCTAATTCATGCGTAAACATTTGCGCTT
GTTTACCCAACATTAATTTTCAACGCCAGAGCGTTCTGCCCACTTTATCTGTCGCCTTATCAGTATGTTCTCCAGATAGTCCGAACATCTGATAT
TAAATCGCTTTAAATAGCATCGTACAAGTTCCTCGTGCTTGATGTTGCAGCATGATACATTAAATAAATTAAAGTTCGATTCATTTTACGGAACG
TACGGGTAGTGAAAGTAGCCGTGTTCATAGTTTGGTATAGTATAGATTGGACTTGACTAAGATAGTTTAAAAGGCTAGTAAACTTGTAGGTGCAG
ATGCACTCGATAAGGGCCGCTATCAGCCGCCCTAATTGGCGTTTGGTATGCAAATGGTGTTTTAATTTCGACTCGGGCGAATAATAAGCAAATGA
GCCAAACTGCCAAGTGTTGGCTTGTAAATTGGCTGATAAGTGCGCCGGAGACACTTGTAGCTGGCAATCGCAATTATAAATGCTGGTAACTGGCA
GCAGCCACGCGTCCCCGGTTACTCAATGGGCTCCAGTTGGAGTGCTCCATTTCGACGCAGCTCTGGGTTCCGAGTGAAATTAATTGGCACATTAG
CTGTGACTATGACTGTTAATTATTAGGGTTAAGTGGGCGTGCCAAAGACGCTGACCAGCAAAGCGTTGCAGCAGATCGTGCGCAAAATTTGAAAT
AAACAATCCACATAGGCGCACCAAAAGACCGAAAGTAAAACCCGGGCAGATGACTTTGGATGAATTTGGAAAAGCGTACAAGTCCGAAGACAGCG
GAGCAAAATAAATAAAGTCTGGAAAACCAAAGTGAAATTCAGCTGGTTACTGGTTACTGGTTACTAGTGGCTGCTTGCTGATCGCGGATCGTGAT
GCCGATGGTGATGGTGAAAACCGCGGCGGGAAAGGGGACGGCTGCAGTCTGTCTTTCGGTGCGTTTTGCTTTAACTTTTACTATAACTAAACAC
TCGGCTTGTTGGTTTATTTTACTTGGCACTAATCAAACTTGCAGCCAAAATCCAATGCCATGCACAGTCTACCTGTTGGTGGTGAAGTTGCCGCC
GCCGTTGGAGTGGCCAACTCAATGCCAGCGATGGTTGTTGCAGGTTGCACTTGTTCTGCTGTCGCAGGTGTTGCAGTTGTTGCTGGTGTCGCTGC
CGCTGGCTTTTCCCCATTAGTCACCGCGATCACTGTGGTCGCCGTGGAGATGGTGGTCGGAACGGCGGCCTGTGGCTGCTCCGGAATCGCTGGCT
CCACCTGGACAACTCCGCTCTCCGGCTTGGTCGCCTGCTCCACGTCCGCGTCCTTCGACATGGTCTGTGCACTTTAAATCAATAATTCACCAATG
GTTCAACCACAAAAAGACATGCAACGTATAATGGACGGTGTTAATTGCCCTAAGACACAGCACAAAAACACTGGTAAATGCTAGTAACTAACTAC
TAGTAACTAATCCGCACGACACCCCGTTAATACAACCGAACACTTCGGCGTGCAATGCGCAACTGAATTTAAAGTTTTCCAGCCGCCGCCCGGCG
ATGGTTAGGAAAAGCTTTTTCCGCTCGCAAATCTCTCGCATGCGACATCGCACACACATATTGCTCATTTCGGTGTGGATAATTGTTTGGTTCTC
GATGCGGATAGGATTCCAGTGGGGTTGGGTTTGCTTTTGACTTTGCCTTTGGCTTTGGGTGCCAACGAATGCTGGTTAGTATGCCGGACCAGGTC
GATCGCTTCTGGTTGGGAAGGGGGTGCATTGATGATTATTTGCATTTCGCATTCCTCGGATCTATTCAAACCATTGTCACTGCGCGGCATTTCAA
TTGCGACTTTGACTTTGATGTTCTGTGCATAGTAATGGGATGGTGCAGTGGAACTGCTTCAATTGGAACTACTTTTTGCCAGAAGGAGTGGAATC
CAAAACGTAAAAGGGTTTACAAAAAGTTTTTGGGTAAAATTTGTTAGTAACAACTATTTCAATATTGTTCTTAGTTTCGAAAGTACATCTACAGT
AAAGTGAAACCTTTAAGGACAACAAGTAGCTTTCCCTCTTAAAGAGCTTAAGTTCATGCTGTGCAATAATGACTGTATGTGCACTTCAACTCACC
CAGTGAGAACAACATGGCGTATACTTGATTGATGCTTCACTCTGCTCAGATAATGCCTGTTTCAATACCGCCTGCTCTTATCTTTAGCAGCAATT
AGTGACTTTAAAGCGATGACGATGGGTTTTTCGCGATTACTTCTGATTTTCGTGGCTACTGCCACGCACTTTACTCTACTTGTTGAACAAACTGC
TTAAAATGCAGGAAGCTGGGCCTTCCATATGGAGGAAAAGCCGTGGAAATTCTGCACAGGCTGCGTGGGCGTGAAAGCCCTAAAGCCCCGCCCAC
TCTGCCGCACTTGGCCATTTCATTTGGCATTTCCACGAGCTTTTCGTTGGAAGCTCAGAACTGTAAACGCCGAAGCACACATGCAAACAAACTTT
CGGGCTCACACCACTGTAGAAAAACCACTTGTTGGATATTATATTAATGGAAAGCCACAACCAAATTATAACTGTTTGTAAACTACATTTAAAGA
CGTAGTTGAAATAGAAACAGGTAAACTTACAGATTTGAAATGAATCAGTAATCCAATAATGTGTTTTGTTTGGAATATTTCCAAAATGTCTTCAA
CGGAAGAGGCAAGAACACAAACAGAAACGGCACAAACACAAAGAGATAATTTGGCAGCATAAGAGAGCGGAATGCTGTGCGAATTTACTACGTCA
GCATTATTATTAACAAGTTAAACTTAAAGCGGCACATTCATTGATACTTAATTTAGTACAGCAAGTCAAGGACACGGTCAAACTTTCACTATCAA
AGGGTTTTAAACTGTAACTCGATCTGTTAACCGCTTCGATTTCTGTTTACTCATTTGGAAAAAAGCGGGACAACCAGGGATGCGAGAATCATAC
TGTAGCTGCGTGTGCTGAAAAAATAGTGTGCATTTAATATACGTTCACATGATGATAGAAAGTACTGACTGTGTGAGTTTTAATTTAAAAATTT
ACAAACTTTATATTCATATTTAACTAGAGCTTGGAAAACATTTACTTCGAGACCCTGGATTCCCTTATGCCGCCAGTGTGGCCCATTGAGCACGA

FIGURE SHEET 21

CTGAAACACGCTAACGCCTTTAGCTCGGCAGCACTGGCAGCTCCAACAAAAAGCTTCAATTTAAAATAATATTTAGGTAGTCCCACAATAAATGC
TAACAAAATGCTCTCCAACCTGGTGGTGACCAAGCAGAAAGTGGTCCTCGTAATAGGTGAGTACACACTGACTACCCCATCGTCTGCCAAATAAT
GCGACCACCAATCTCCCGCCTCATCCACAGATGAGCTAAATCGGGAGCGCATTGCCCCCAAGTTCATCGGCAGTCTGCTGCACGAGCAGGGACAG
GGGGCGGATACCATCAAGGCCCTGCCCACCGGCGTCAGCCTTAAGCACGTGGCCACCTTCGAGGCACTGATCGACAAGTACGCCAACAACAACAC
TGGGAGTACTACGGATTCCAACTCCACTGGCTTTAACGTCATCCTGCCAACATTGGCAGACCTGCTGTGCTACCAGACGCCTGCTTTCATATTTG
GCTTCCTCAACCGCCTACGCCGCTCGGACAATGTGCGTCGGGTTTTCCTTTGGGCCTCCCCGCAGCACCTGCAGGATCCGCATGCCGACTACATC
CTGGCTGGCTGCGAGTACCTGGCCGAGCTGGTCCTCCGACTGGAATCGGACAAACTACTCTCGCTGATATCACGCAAGCCGGGCGGAGGGGTGTC
CAACAGGCGCTACTCCTGCGAAGTCAGCAAAACCCAGTTCAAGGTGACGCCGCTGGACGGAGGACTGCCTGCAGGTGCCTCCCCCAAGCAGC
(SEQ ID NO: 64)

Exon: 5647..5351
Exon: 4061..3781
Exon: 2225..2016
Exon: 1931..1568
Exon: 1510..1001
Start ATG: 4051 (Reverse strand: CAT)

Transcript No. : CT2537
AAATCGAAGCGGTTAACAGATCGAGTTACAGTTTAAAACCCTTTGATAGTGAAAGTTTGACCGTGTCCTTGACTTGCTGTACTAAATTAAGTATC
AATGAATGTGCCGCTTTAAGTTTAACTTGTTAATAATAATGCTGACGTAGTAAATTCGCACAGCATTCCGCTCTCTTATGCTGCCAAATTATCTC
TTTGTGTTTGTGCCGTTTCTGTTTGTGTTCTTGCCTCTTCCGTTGAAGACATTTTGGAAATATTCCAAACAAAACACATTATTGGATTACTGATT
CATTTCAAATCTTGCACAGACCATGTCGAAGGACGCGGACGTGGAGCAGGCGACCAAGCCGGAGAGCGGAGTTGTCCAGGTGGAGCCAGCGATTC
CGGAGCAGCCACAGGCCGCCGTTCCGACCACCATCTCCACGGCGACCACAGTGATCGCGGTGACTAATGGGGAAAAGCCAGCGGCAGCGACACCA
GCAACAACTGCAACACCTGCGACAGCAGAACAAGTGCAACCTGCAACAACCATCGCTGGCATTGAGTTGGCCACTCCAACGGCGGCGGCAACTTC
ACCACCAAGCAGCGGCAAGGCCAACATGGATCCAGCGCTGATCAACTTTAAGGTGCTCTATGTGCTCACCCAGCTGTGCGGCCTGACCATGATCG
TCCTGGTGGCCACCTGGATTGGCCAGCACTTCGGCGGTCTGGCCGGCACCTCAAATCCCGGCGTGGAGTTCAACTGGCATCCGCTGTTCATGACC
ATTGGCTTCATTTACCTGTATGGCAACTCCATTCTGATCTATCGTGGTTTCCGCACCACGCGCAAGAAGACTCTGAAGCTTACCCACGCCGGCAT
CCACATGGGTGCATTCATTCTGACGGTGATTGCCCTGAAGACGGTCTTCGATTCCCACAACTTGGCCAATCCGCCCATTCCCAACATGTACTCCC
TGCACTCTTGGCTGGGGCTCTCCGCGGTGATCGTCTTCTCGCTGCAGTATGTGGCCGGATTTGTGGCCTTTTTGGCGCCGGGGTTGAGGGAGAAC
TACAGGATCGCCATGATGCCGCTGCACATCTACTTCGGACTCTTTGGATTCGTTCTGGCTATTGCTAGTGCCCTGATGGGCATAACCGAGAAGGC
CATCTTCGCCATCAAAACTCCGGCTTACTCCACTCTTCCACCGGCTGGTGTGTTGGCCAATGTGATTGGAGTAATGTACGTGGTCTTCGGGGCGC
TGGTTGTCTACCTAGCCACTGAGCCCTCCTACAAGCGGAAGCCCATTCCCGAGGACACGGCTCTGCTGAACTCCAGTTCTGTCAACGAGTAAGGG
CTATGCCCATGCCCCAAATCAACTGCAATGCTTACTTAAGCTAAAAACTGTGCACAAAACCAAACGAAACCGAACCTGATCACACGGATGGTGCT
TTCTTAGTGATGGAGATGGAGATTCGTCAAGATGAGTGTATTATCTGTAGCATGTACATAACCTAACGACTATGTATGACTCTGAATTATGAACA
TACGTATACTTTGGTCACCAGTTGTGCAATGATTTCAGCGAGTGCTCAAATCATAACGTATTTAACCTCAAGAAAAACATTTGCTTTGAACTGTA
CGAATACATCTATATATGTGTGTTATATATGCTTAAATAAATATATA
(SEQ ID NO: 65)

Start ATG: 308 (Reverse strand: CAT)

MSKDADVEQATKPESGVVQVEPAIPEQPQAAVPTTISTATTVIAVTNGEKPAAATPATTATPATAEQVQPATTIAGIELATPTAAATSPPSSGKA
NMDPALINFKVLYVLTQLCGLTMIVLVATWIGQHFGGLAGTSNPGVEFNWHPLFMTIGFIYLYGNSILIYRGFRTTRKKTLKLTHAGIHMGAFIL
TVIALKTVFDSHNLANPPIPNMYSLHSWLGLSAVIVFSLQYVAGFVAFLAPGLRENYRIAMMPLHIYFGLFGFVLAIASALMGITEKAIFAIKTP
AYSTLPPAGVLANVIGVMYVVFGALVVYLATEPSYKRKPIPEDTALLNSSSVNE*
(SEQ ID NO: 66)

Name: cytochrome B561-like
Classification: electron_transfer

Celera Sequence No. : 142000013384816
AGCCCCATAATTCGTGGAGCAAACAACAAAAGAAAAATGTGGACATTGTTGTACACACAGGCAGAGTCACGCACACAGACGAACCCACTCGCTCG
CTCGCTCGCAGCTAAAGTTTGAGTTCGCGTGGTGCCTTGCACATTGTTTATAAACTTTAAGGGCAGCCAACGTGGAGGGGGCACTAAAAAAACAC
ACCCCACTTTAGCGGGCACAATTTGTTTTCAGGTTTTCAACTGCACATTTAACGCGTGTAAAACTTTTTGCGTTTGGGGCCCACTCTCACACATA
CAGGCGCAACACAGCACACACACGTTCAATCGAATTTTTCACATACGTTTTAAGGACGTTGCTCCTCGGAGATTGCCTAATTTTTGCGTTTTTCA
GATGACTCTGTACCCAGTCTATCTAAATTTCTGGTTTTCAGATACTAGAATATGCGTGCAATTTGCGGATTTGGACAGATTTTGGACCCGAAAAA
AAACTAATGCGGATCCAGTGTGACCACCGCTCGACCGTTCAAATATACCATGGGAATTCACGGCTTAAGTTAGGGATGTGATGGTCTCCGCGTGA
CTCGAGCTTGGTTTTAAAAAATGTGATACTCTGCAAGTTGTTTATATGTATGGATTTCATGAATTATTTATGTGTTGTAATAATAAACGTGTTTC
TTACACAATTTAATTGCTCAGCAATTCTACTTTTCTTTTTTGATTGCTTATATTTTATATTATATTTTTGATTGCTTAATTACTAAAATTATTAT
ATGTTTAAAAAACTTGTTTCTATTTTCATAGTTTTAATTTTTATACTTATATTTTATAACTTATAGAAATTTCTTGAAAACCCTAAAAATGACA
TGAGTTTGTTATTTATTGCTATGTTATAAAATAATTAGAAACCATTACAGCAAATATCGTTAATTTGTTTACTAGTGATAGAGTGTGGTAACACT
AGCATTTCCGTCCACACAATGTTAAGGTCACACTCAGAAGCTGCAAATTTCGAATTTCGACGGTCGCTATGAGTGGAGCTCTCGGAGATGTGGTG
TCCGAATACCTGGAGCGCGGCCCAGTGCTCGTGGTGGCGGACCTCCTTAGCCTGATAACGGTCTCGTCCTGCCTGGTGATCAAGGTTCCGCAGAT
AAACACGATACGGGCGAACGAGTCCTCGAAAGGTGAGCACCGCCCACACAACATCTGCAACCTATCCTCCCACTCATATGATACGGATTTATGAA
TTAGGCATCAGTGTTTTGGGACTGTGCCTGGAGCTGTTCAGTTATACGGTGATGTTGTCGTACAACTACACCAGTGGCTACGACTTCCTCTCGTA
CATGGAGTATCCTGTTTTGCTGCTGCAGGAGTACGCCCTGATTTACTACGCCTTCAAGTACCAGGATCTGCTGGGAAGGAGGACGCAAGTGGTGG
CCATACTGTATAGTATAGTGGCCACTCTCATATACATGAAGCTCTTTCCCATTATCATCCTTAAGTTCCTGGTGGTGAGTAAGCCTGTATTGATA
TCACCTAGTGACTGATTAGTCGGGTATTCTTGCCCAGATAACGACTTCGGCGCAGTTCAAACCCGTTCCCCGCTCTCTTTTCCAATTAACTAATT
ATGTTTCCGGGCAAACGGGTTTGGTTTGATTTGTTATTTGTTTTAGTTTGAAAAGGCGGTGCTCTTAACTGGGCAGCATCTTCGCTCAAGGTCAC
CGATGTTTGTTGTATAATATTTGAGCGGCTATTAATACTTTCAGTGCTCGGGCAATATATATAAATCTCGTGAAATTCATCTAAATGTTTGATTT
CCCGTCAGCCTTTCTGCACTCCCATTGGAGCCACGAGTAAGGTCCTCCAGCTGCTGGCTATTCTGAGGACCAAGGATGCCAGTTCCGTCAGTAGA ACCACATGGGCGCTCTCCGCCTTTACAAACATGAGTGAGATCACATCTTGCATTCCATCACTTGATGTCATCAATTAACACATCATATATGTATC
CCTTACAGCTCGAATCTACACGGTGTTCTTCCAGTCCCACGATTGGATGTTGCTATCAAACTTCCTGATTTCGACGTTCCTTAGCGCCTCCGTTT
TCACCGCCGCTTGCGTCTACAAGAAGAAGGCCAAGGCGGAGTAATTGGCCAGCCTGATTAGAAAAGCTCAACATAGACAAACACTGCGCTGGCTG
GAAATGCTTATCAGTCATTGTTTTAATTCTATTTGCTTATCTGTTTAAATTGATATTACAAATTCTTGTTTGAATCGGTTGTTGTTACTCGTTTA
ACTGTCCGCGTAGAAAGCCACCACAATTGCACCCACAACTGTTAGAATGGATACTGCATAGATTGCTCTACGTTGCCAATCGATCTTGGTCTTGG
CCGGTCCAGAACCCACAGTTTTGCGCTCCTTGTGCTTGCGTTTGCCGAACTTGGCCTCGAACTTCTCGAGTTCCAGGCGGTTTCTTTCTTCCTCG
TCGCGACGCTTTTGTTCCAGCTGCAGTTGCTCTGCCGCCTGGACGCGAATTTGCTCCGCCTTGCAGTTCGAGTCGCAATCCAAGAATGTCTGACC
AGCACGGTGTTTGTCACAGGCAATCTCCTGCTTGAGTCGCTTGCAGGCGCAGAAAATGCGAACCTTCTTGCGGCACAACTCGGGATTTGGGCACT
TGCCTGTGTGGCAGATGGCTGTGCAGCGATGTCCGCAAGGATACTGAAAAAATATATATATCACTGTAAGGCTTGATCGACAATGGTATATTACA
GCACTTACATTCTTCAAGCATCGATTACCGCAGCTCCGTAGCTTTTCTCTTCGCTCGATGATCTCCTGGACCGATCCCGTTTCATCATAATACTC
GTTGCACTTGTAAACCAACTGGTTGAGTCCACAGTGACACTTGGTCTTAATCACAAAGTTGCAGGGCGCACAGGGCGGTGGATGACATCCTTTGG
GACAGGCGTGAATACATCCGGTTGGTCGGGGAACGGTGCAACCCTCCTCGCAGTTGGCACAGCCAGTTTGCGCAGACATATCCTGGGGAAGCGGT
ACGAAATGGCAAACCAATGAACACTTGTGATTGCCGCACTTAAGCTGACGTGCACACGATCGCTGACAGGAAGTGGGTTTGGAGTTCCAGCATG
(SEQ ID NO: 67)

Exon: 1001..1172
Exon: 1240..1503
Exon: 2004..2134
Start ATG: 1019

Transcript No. : CT2591
CGAATTTCGACGGTCGCTATGAGTGGAGCTCTCGGAGATGTGGTGTCCGAATACCTGGAGCGCGGCCCAGTGCTCGTGGTGGCGGACCTCCTTAG
CCTGATAACGGTCTCGTCCTGCCTGGTGATCAAGGTTCCGCAGATAAACACGATACGGGCGAACGAGTCCTCGAAAGGCATCAGTGTTTTGGGAC
TGTGCCTGGAGCTGTTCAGTTATACGGTGATGTTGTCGTACAACTACACCAGTGGCTACGACTTCCTCTCGTACATGGAGTATCCTGTTTTGCTG
CTGCAGGAGTACGCCCTGATTTACTACGCCTTCAAGTACCAGGATCTGCTGGGAAGGAGGACGCAAGTGGTGGCCATACTGTATAGTATAGTGGC
CACTCTCATATACATGAAGCTCTTTCCCATTATCATCCTTAAGTTCCTGGTGGTGACTCGAATCTACACGGTGTTCTTCCAGTCCCACGATTGGA
TGTTGCTATCAAACTTCCTGATTTCGACGTTCCTTAGCGCCTCCGTTTTCACCGCCGCTTGCGTCTACAAGAAGAAGGCCAAGGCGGAGTAA
(SEQ ID NO: 68)

Start ATG: 19

MSGALGDVVSEYLERGPVLVVADLLSLITVSSCLVIKVPQINTIRANESSKGISVLGLCLELFSYTVMLSYNYTSGYDFLSYMEYPVLLLQEYAL
IYYAFKYQDLLGRRTQVVAILYSIVATLIYMKLFPIIILKFLVVTRIYTVFFQSHDWMLLSNFLISTFLSASVFTAACVYKKKAKAE*
(SEQ ID NO: 69)

Celera Sequence No. : 142000013384610
AGTATTTATTCTACTTTTACTCAGCCAATGCATCTTAAGCCTTCGGGACCTACTCTCGAAAAGAATCCGTCTAGAAACCTGCGACATGTTCAGG
AAAAACGTAAACGTACGCCCATTAGAGAAAAGATGGCTTCGCTTGAGAAGTTGAGGAATCTCCAAAATAGCAAGTTTGTTCTCTCCCGCGACGCT
TTTCAAAAAATTCAAAAAATTACTAGTGGCGGTCCCTATTACTTGACAAAAACAAAGATTAGACCATAGGCCTTGATTTGAATATCTCAAAATAA
AAAAATGCAATGCAAACACATTTGAATCGATTTTTCGCTTTATTACATTTCTTGTATCATAATCGTTTTGTTTTTCTGGTTTTGCCATTTTTTAA
ATATTGACGTTTTATATAACAATTCATAATTTTAGCTTACAATATTTTTGTTTTGTATTCTTAGAATCGTTTATGCCTTTTGCCATGAAAACACT
TCTCTCTCTAGCAAATATACAATTTTCGAAACTTGTGATTTTGCAATTATTTATTATGTATATTATATATATTATATGTATATAACTAAAAATGC
GTAAATTAATTTTTTTTTGTTTGTTACGTGGTTTGTGGGCACATTCCTTTTATCAAAAGGAACAAAACATGAAAATGTACATAAGTGTTATTGGC
AAATAGTTTACCATCTGTTTTAGATCTTGATACACATACGTGCATCATCGATATAAAGAACCTGAATTGTTTTTAAATTTCGAAGCGGCAGTTGC
AGTTCTGTATTTGCGCCTCATGAATTGCTCGTTTAACGTGTCTCTCTAAAAGGCAGGAGCAGCTGTGAAGTGCTCGAAGGCAAGGGTCGATCCGT
CCGCCGTTGGATCTTTATCCTTCCTGACCGTCCATTGATTGGCCATTGTCCTATTATCGAGAGCCCGCCGCTTATTGGTTGGTTGATTATTTTTT
CTCTCATCTATTTTTATGAAATGGCTGTTAAAAATTTTGGTTTGAACGCATCATTCCCATTCGGTGGTGCCCGGCGGCTTGGCTGTCAAGTCGTA
CAGCACCCTCGAGATTCCATCCAGCTTGGATATATCGCGTACAATTTGATTTAGGACCTTTGAGCAGGAAAAGATTAAATATACATTTTTCAGAA
AGATTGAAAACTGACTCACTTGCAAAGGCATTTGCACGGATCCGGGCTCAGCCGGCACACCAGTCATAAAGTCGTTCGTTATGAACGGACGCAGC
ACTACCGACCTTCTGCACGAGGGTGTGCGGTTAATGGGATCGCGGTCAAAGTGCACGGGTATGAGAACAACAGGCATCTGCGAGATCTTCCGGTA
TAGTCCAGCTTGCATTATGATCTAAAACGGTTATGATATAATACATTTTATTTATTTCTATGACAAATCCACTTACTTCATTGGCAATATCATCG
GCTTGCCTCAGCTGCGAAAGAACTACAGTATTCAGTGTGGTGTGCGTAATATCCGTCACTAGATACTGTACGGGTTCGCCGAAGATATAGCACAC
CCTGTTCACGTTGTGCAGAATTCGCGGTATGATTTTGGCGAGGAAGAGAAGATCCTGCCAGTTGGGCTCCTGGCTCGTGGATAGGCCTACTACGT
AGCTATATGACCGTTTATCACCTTGCACGCCCACTGATCGGATGGGCAGCAAAGTTGCCTGGATCTGCGAGTTCGATGAGATACGCATAAGGTCT
TTCTGTTCCGCCTCGCTCGTGGCCGCCGTTACGCGGTTGATCAAAGCATGGTTCTTCTGCAGTTTATTCTTGTAGTCTACAATCACGCGGATAAT
AACCTACAATTAAATAGTATATTTATTATAATAACTTTGACAGCAATTAATTGTTAACATGCCTGAGTTTCTGAGTAGTCCTTTTCCATGTATGC
CTCCTCAGCGCAAAGGACGCGGATTGCCAGGCCAGGACCCGGAAAGGGTTGCCTCTCCACAAGCTCTTGAGGCAGGCCAAGATCATTGCCAAGGT
CGCGCACTTCATCCTTATGAAAGTCGCAAAGGGGCTCAACCACACGTCCTGCGTTACGAAGCTCTCTGAAGAAATGAATTACAAAAAATAAGCTG
ATCACTAAAATTTGGTTAGGAATTTAGACTTTTGCTTTTTTACCTGATCAGATCCGTGTCATTGTGGTGCGTTTTGATTGTTTCTGCATTCGTGC
TCACCATGCTAGAGGCGGACTCGATCAGATCTGGTCGGAGGGTTCCCTGGGCCAACATAACTTCTTCGGGCTTTAGTTTCAATTCGGCTACTACA
TCATTGGTCACCTTGACGAATATATCACCAATTATCTTGCGTTTTTCCTCCGGATTGTATGTCTGACATAACATCGGCGTTTCCACCACGGAGTA
CTGTCCGGGCCTCTTGACCTGCGTGGTGCCTTTAAGGAACGTGTAGCCTTCTTTTCGGACGATTAAATCAATGCCAATATCGCGCAGTGAACGCT
CCACCTTTTCACTTTCCTTCTTGCGCATGAAACCTTGAAGTAAGGGATAAAATATTAGGTTTTAAAGTACAAATGATATAAATTCGGTATTCACC
GAGTTAATGAATTATTTGACGTAGAAAAAATATAAATGAATAAATTTCGCTAATCTGTCTACTGTCATACCATTATCTACATGCACGGCAATTAT
CTGATGAGGGTACAAAGCACGGCGGAGCAAAGCTGCACAGACACTCGAATCCACGCCGCCGCTGACCAGGAGCTGTAAAATGTAGATTGTATTGA
GATATTCATGTCTTGATTGAAAATTTATTTTCCCAAACTCACCAACACCTTATTGTTGCCCACTTTCTCACGGATATAGCGTATGCACTCCTCCT
TTCGACTACCCATGGTAAAGTTAGGTGTCAGTTCGCAGATTTCGTACAGGAAGTTCGATAGCATCTGTTTGCCATTGATAGTGAGGTCCACCTCA
GGATGGAACTGTACGCCGTAGATGCGTAGTACTTCATTGTAAATGGCTGTCACAATGCGGTTTGTAGACCAGCCACCAATCTTCAGATTCTCGCC
TACCCTCTCAACGCTATCTCCGTGGGTTAACAGCACGGACTGTGTGCGACTGAGGCGACTGCGGGAAACGAAGATGTTATGTTTGTTAATTGCAT GTATTAGAATAATTAATGGTAATGATAGATAATATGTTAGGCCACGTGTAGATCAGTTTATAAACTACTCTAAACTAAACTGTTCTTGGCTTTAA
AATTGTTCTGGCAGCATTGTATCAGCGCTTAGGTAAACGCATTTAAGCCTAAGCACTTTCTTGTTGCTGCTTGTTTTGGGAATCAATATTTCCTG
GCTCACCTAAAGAGCGGGCACGAGGTCTCGATCTCGATATTTTGTTGGCCATCCTCTCGAACATCCTTCTTGAGCACTGTGCCCCCGAACTCTTT
GTTGATTAGCTGCATGCCGTAGCAGATGCCCAGCATAGGTATTTTTAGCTTGAACAGATCGGGATCATAGCTGGGCGCATCCTCAGCGTAGACTG
AGTTGGGTCCGCCGGAGATGATGATGCCTCGATAGCCATTGTTGCGTATCGTGGCAGCTGGCGTATCCAGAGGAAGGATATCCGTCTCAACGAAG
AGTTCGCGTACCTTACGGTCGATAACCTGCGGAGAAACCAGGACCATTTTAAGAAGAGGTTAAAACTACTCTTGGTTTTAAGCTTACCTTGCCGT
ACTGTGCTCCCGCATCAAGTATAACAATCTTATCATGCCGCAGGCCATTCTCTGCTGTGCCCAGAAAAAATGTTTGAGTTCATTTCTTTATCGTTG
CAGCACTGAAAAGAGCAAAGATTTGAGTGTCAGTCAAGCAATCGCAGAAACAAACACCGAATCTCGACTGGCTGGTAAACGCGCTTCTGCTGCTT
ATTTATACTCCAATTGTGGCTGCAATCGACGCTACAGAAACAAGGCTAAAAGCTGGCTAGGAGGTGGGGAAAATAGGTTTCGGATTGGGGCAATC
GCGGAGATTGAGATTTGTGGTACAGAAGGCTCACATACCGGCAATATCTTGTGGAGCACTCGCAGAAACATTCAACATGCAGCTGGCCAGGACGC
TCTACGATAGACAATAAACATTGGCAAATATTTTCTTGTCACAGAAAGATGATTTGTGCAATGTGGAAAGAAATTTACAAGCGACGAAAAACAAG
GCCGAGAGACGCCTACCAAAAATGATTCGCTGTGCATCGCGACGATTACGTTCTGTGGGTATTATTTATTTGACCAAATATAAAACATTTACGTA
TATGAATAAGCCTATAACTTAATCTTAATAATACCTGTTTATTTAACCGTGGTTAGAATTTAAGACAGAGTGTATTCACAGCCAGCATAAAATCA
TAGATACCATAGGAAAAAGTGCTCCAAATGATCATAGTTTGGTTTTTAAAATAATATTAAATAGATATAATTTTTGTATAATTTTGGTCAACAG
ACTGAATTTGGATTAACAACATGAAAAACGAATTTTTGTGCCAGGAGTATCTGTCAATGCTATATACTTCTACATACTAAAGTAGATTATCAAAG
CATGGAAGTTAACATTTAATTTTATAGACACATTTGTCCCATCAAAGAATTTAGAAAAACAGCAGGTCAGGAACATGCTTTTCGAATTCCCGAAG
TAATCGGCGACTTAGTACATATATTTTAAAATACAAATTTCGATGCATGAGGATGAGGATGTGAGGAGGAAACGGAACGTAATGGTGATGGGGTC
AGGGGGGAGGGCGCCGGCTACTGACCGCCAGATGACAGGCGAAAATACTAAGAGGAGAGTGGCAGCGGAAGCGAGAGAGAGCGAAAGATGAGCGG
AGAAAAATGGCAGGTAAACGAAAACAGAGCTGAAAAGTGCACAAGTAAAATAGAAAACAAAAATAAACAACAACAATCCAGGAGACAAATCGACG
GTAGCAAGTCTTCTTGTTTGCCATTTATTTTCTCTTGAAGTGTGTAAAAACGCAGCAGCAGCAATATGAAAAGCCTCTCCGAAGGTTAGGAGTGC
ATTAGGTCACTGAAGCGATGCGATGTCTGTGATGTAAGCCGTGCTCCTCCTTTGGCTCTCTCTCATTTTTGATAACAACATGCAAGAGGTTATCA
GAAACGGCACAAACCACAGCAACAACAACTAAAGAGGGCGGCCGCGTGGTTGTAATTTAATACACATGCAGAAGGCACGCACACTTACACACGTG
GAGCCGCCAACAAGCGGCGCTTATAACCACAAAATGGCCACGGGATATATTTGCAAAACATTTAAAAAATTGCAAATGCGGAGAACAAAAAATCG
CAACAAAAGCAAAGGCAAATGCGGTTGAAGCTAATTTGCGAATTCAACGGGCGGGGTGCGGAATTGTGGGCGGAGCAGCACCGCATGGCGATTTG
GCTGGGATCGGGGATCTTTTTCGCCATATTGCGACTCTCACCTTCTCTCGTTTTAGCCTGGCTGCGGTTTTCCAGAACCGGGAAGTCCGTCGGCA
AGGCCGTGGAATACCGTGACAAGCAGCGCAAGACTTTGTCTTAAGACGAAATTCGCGATCCGTTGTTTGCGGTCCCCCGTTTTCCTTCCTCACGC
ACACACTCAAAATTTCTTCGGCTGCTGCAGCTTCTTTTCCGCGTATCCAGGGCTGCTCGACACAGCTGGCGATGAAATCCCTGTGATTTTCACGG
CTGCGTTATTATGGCCGCTTCCAGGGACTTTCCTTTTGGATTTCCTGCAGTTTTTCGCGAATTAAAGCCGAAAGATGACTTATTGACGAGCGGA
TGACCATATTTCGGATTTGGGAAAAATCCAGCTGTGCTGCAAACGAAAAATACCAGCTGTGAACGTTTTTGGTATTAATATTTACCAAATAAATA
AATTTATATTTATTTCGAAAACAATGAAAATTCCTTAATAACATTACATTACTTCTTTATTAGGAGTGCTTAAGTATTCTTTTAAATAATGAATT
ATAATTAAAATTATAATCTGTTTGTACAGTGTTGACAAACGAGCACTTTTTGTAGAACCATATACATTACCCGGTCACACTGAGCCCGCCAAAAC
AGATATGTTATTGCGCTTATTTAGAAAACCAAGAAAAAACACGAGAACACGTGAAAATACAAATCTACCCAAATGAAATGGGTCCTGCTCAGAAA
TCCGGAACAGATATTAGTATCGATGATGAGGAGGAAATACTGGCTCTGGAAAAACTACTGGGTGCAGCAGAAAACGAAAATACAAAATCTGCAGA
GTCAGAAAAAGCAAAACCCACCGCACCCATTTTGGTGCCAAAACTACGAGAAGACAACAGTTTGCTAATGCCTTCACCTTCGAGAAGATCGTGA
AACCGGAAAAGCAGAAGAATGCTGCTATCATTAAGGAACCAGAGCTGGACTCGTCCGACGACGAGGAGGTAAAGAACTTCCTGGAACGAAAGTAC
AATGAGTACGGCAGTGATATAAACAAGAGACTGAAGCAGCAGCAGGAGAACGCCTACGAGTCCAAGGTGGCGAGGGAGGTGGATCAGGAGCTTAA
GAAGTCTATCCACGTGGTTACATCCACCCCGCAACCCCTGAAAAATCCGCATAATCCTATTAAACGGCAATCGGCGGTGAGCACCACGTTTCAAC
GTCCTCCGCCAGTCGCTGCCGCCGTGGCATCTACATCCCAGTCAAGTGCTCCCGTATCTGCTGTTTTTACGGATCCAGTCTTCGGACTGCGCATG
ATCAATCCGCTAGTCTCCAGCTCACTGCTGCAGGAGCGCATGACGGGCAGGAAACCTGT
(SEQ ID NO: 70)

Exon: 5804..5457
Exon: 3805..3698
Exon: 3636..3332
Exon: 3098..2798
Exon: 2732..2636
Exon: 2503..2134
Exon: 2060..1868
Exon: 1808..1407
Exon: 1351..1160
Exon: 1102..1001
Start ATG: 3787 (Reverse strand: CAT)

Transcript No. : CT2988
ATATGGTCATCCGCTCGTCAATAAGTCATCTTTCGGCTTTAATTCGCGAAAAAACTGCAGGAAATCCAAAAGGAAAGTCCCTGGAAGCGGCCATA
ATAACGCAGCCGTGAAAATCACAGGGATTTCATCGCCAGCTGTGTCGAGCAGCCCTGGATACGCGGAAAAGAAGCTGCAGCAGCCGAAGAAATTT
TGAGTGTGTGCGTGAGGAAGGAAAACGGGGGACCGCAAACAACGGATCGCGAATTTCGTCTTAAGACAAAGTCTTGCGCTGCTTGTCACGGTATT
CCACGGCCTTGCCGACGGACTTCCCGGTTCTGGAAAACCGCAGCCAGGCTAAAACGAGAGAAGTGCTGCAACGATAAAGAAATGAACTCAAACAT
TTTTCTGGGCACAGCAGAGAATGGCCTGCGGCATGATAAGATTGTTATACTTGATGCGGGAGCACAGTACGGCAAGGTTATCGACCGTAAGGTAC
GCGAACTCTTCGTTGAGACGGATATCCTTCCTCTGGATACGCCAGCTGCCACGATACGCAACAATGGCTATCGAGGCATCATCATCTCCGGCGGA
CCCAACTCAGTCTACGCTGAGGATGCGCCCAGCTATGATCCCGATCTGTTCAAGCTAAAAATACCTATGCTGGGCATCTGCTACGGCATGCAGCT
AATCAACAAAGAGTTCGGGGGCACAGTGCTCAAGAAGGATGTTCGAGAGGATGGCCAACAAAATATCGAGATCGAGACCTCGTGCCCGCTCTTTA
GTCGCCTCAGTCGCACACAGTCCGTGCTGTTAACCCACGGAGATAGCGTTGAGAGGGTAGGCGAGAATCTGAAGATTGGTGGCTGGTCTACAAAC
CGCATTGTGACAGCCATTTACAATGAAGTACTACGCATCTACGGCGTACAGTTCCATCCTGAGGTGGACCTCACTATCAATGGCAAACAGATGCT
ATCGAACTTCCTGTACGAAATCTGCGAACTGACACCTAACTTTACCATGGGTAGTCGAAAGGAGGAGTGCATACGCTATATCCGTGAGAAAGTGG
GCAACAATAAGGTTGCTCCTGGTCAGCGGCGGCGTGGATTCGAGTGTCTGTGCAGCTTTGCTCCGCCGTGCTTTGTACCCTCATCAGATAATT
GCCGTGCATGTAGATAATGGTTTCATGCGCAAGAAGGAAAGTGAAAAGGTGGAGCGTTCACTGCGCGATATTGGCATTGATTTAATCGTCCGAAA
AGAAGGCTACACGTTCCTTAAAGGCACCACGCAGGTCAAGAGGCCCGGACAGTACTCCGTGGTGGAAACGCCGATGTTATGTCAGACATACAATC
CGGAGGAAAAACGCAAGATAATTGGTGATATATTCGTCAAGGTGACCAATGATGTAGTAGCCGAATTGAAACTAAAGCCCGAAGAAGTTATGTTG
GCCCAGGGAACCCTCCGACCAGATCTGATCGAGTCCGCCTCTAGCATGGTGAGCACGAATGCAGAAACAATCAAAACGCACCACAATGACACGGA
TCTGATCAGAGAGCTTCGTAACGCAGGACGTGTGGTTGAGCCCCTTTGCGACTTTCATAAGGATGAAGTGCGCGACCTTGGCAATGATCTTGGCC

FIGURE SHEET 24

TGCCTCAAGAGCTTGTGGAGAGGCAACCCTTTCCGGGTCCTGGCCTGGCAATCCGCGTCCTTTGCGCTGAGGAGGCATACATGGAAAAGGACTAC
TCAGAAACTCAGGTTATTATCCGCGTGATTGTAGACTACAAGAATAAACTGCAGAAGAACCATGCTTTGATCAACCGCGTAACGGCGGCCACGAG
CGAGGCGGAACAGAAAGACCTTATGCGTATCTCATCGAACTCGCAGATCCAGGCAACTTTGCTGCCCATCCGATCAGTGGGCGTGCAAGGTGATA
AACGGTCATATAGCTACGTAGTAGGCCTATCCACGAGCCAGGAGCCCAACTGGCAGGATCTTCTCTTCCTCGCCAAAATCATACCGCGAATTCTG
CACAACGTGAACAGGGTGTGCTATATCTTCGGCGAACCCGTACAGTATCTAGTGACGGATATTACGCACACCACACTGAATACTGTAGTTCTTTC
GCAGCTGAGGCAAGCCGATGATATTGCCAATGAAATCATAATGCAAGCTGGACTATACCGGAAGATCTCGCAGATGCCTGTTGTTCTCATACCCG
TGCACTTTGACCGCGATCCCATTAACCGCACACCCTCGTGCAGAAGGTCGGTAGTGCTGCGTCCGTTCATAACGAACGACTTTATGACTGGTGTG
CCGGCTGAGCCCGGATCCGTGCAAATGCCTTTGCAAGTCCTAAATCAAATTGTACGCGATATATCCAAGCTGGATGGAATCTCGAGGGTGCTGTA
CGACTTGACAGCCAAGCCGCCGGGCACCACCGAATGGGAATGA
(SEQ ID NO: 71)

Start ATG: 367 (Reverse strand: CAT)

MNSNIFLGTAENGLRHDKIVILDAGAQYGKVIDRKVRELFVETDILPLDTPAATIRNNGYRGIIISGGPNSVYAEDAPSYDPDLFKLKIPMLGIC
YGMQLINKEFGGTVLKKDVREDGQQNIEIETSCPLFSRLSRTQSVLLTHGDSVERVGENLKIGGWSTNRIVTAIYNEVLRIYGVQFHPEVDLTIN
GKQMLSNFLYEICELTPNFTMGSRKEECIRYIREKVGNNKVLLLVSGGVDSSVCAALLRRALYPHQIIAVHVDNGFMRKKESEKVERSLRDIGID
LIVRKEGYTFLKGTTQVKRPGQYSVVETPMLCQTYNPEEKRKIIGDIFVKVTNDVVAELKLKPEEVMLAQGTLRPDLIESASSMVSTNAETIKTH
HNDTDLIRELRNAGRVVEPLCDFHKDEVRDLGNDLGLPQELVERQPFPGPGLAIRVLCAEEAYMEKDYSETQVIIRVIVDYKNKLQKNHALINRV
TAATSEAEQKDLMRISSNSQIQATLLPIRSVGVQGDKRSYSYVVGLSTSQEPNWQDLLFLAKIIPRILHNVNRVCYIFGEPVQYLVTDITHTTLN
TVVLSQLRQADDIANEIIMQAGLYRKISQMPVVLIPVHFDRDPINRTPSCRRSVVLRPFITNDFMTGVPAEPGSVQMPLQVLNQIVRDISKLDGI
SRVLYDLTAKPPGTTEWE*
(SEQ ID NO: 72)

Name: GMP SYNTHASE LIKE
Classification: enzyme

Celera Sequence No. : 142000013384340
CAGGTTTTTTGTTTCTTTATTTTTTGGTTTCTCTAGATCCTCGAAGAAGCGGAGTTGAGTCCGCTTATATGGCCAGTCATGTGGCACGCATCAT
CATTTATCAAAGAACGCGGCAACAATTCGCAGGGCTGACAACAAGCCAAAAAACAACCTCCAATCTTTCGTAACGAAAGACACCCAACTTGTTCC
ACCCACAAAAGACGCCGCCGTTTTCGTGTCGCTACTATTTTTACCCACTCCCAGAAATTTTTGTTTTTGTTTTTTTCTTTTTTTTTCTGTCTATT
CGGTCTCCTGCGTTTCCTTGGATGCTTTATTGTTGTTGTCGACGCTTATCTGCCGTTTGACATTGATGTGCTGGGAGTACAGTGGTCGAAATGGA
GAAGTACACTTGATTATCTACCAAAAGTAAAAAAAAACCGTTAGTTTAAGTAGATTTATCGGATAGTTGCTTTATAATAGACCACACTGCGTATG
AGTAATATTTTACAGAGCTTATACATAAAATATTGCAAGTGGAATAGTTAACATTTCTCTAAATGATTTAAGTATTCAATTATTTTAGCCACTTT
GGTAGTAGGGGTTTCACTGTACGCGGCGCTTGTTGGTCCTGTCATGTAACGGTTAAATCTGCATGAAAAATTAATGCTGTGTTGTTGATACGGGG
AAAGTGGAGAGGGAAAATGGTCGCCGTATTGCGTATGTATGTATGTACATACATATGTACATTTATCTGCCTCTGCGAATTGTTGTTGTGTCGAA
ATTAGCATCTCGAACAGCTTGCGTTACTATTCCACCCGCAGATTTACAGTTACCCACTTACATATGCACACTTGGTTTACCCTTGCATTTGCTGT
TTTTAAAGACATTGATTTCGTGAGATTTTATTGTACTATTAAGTTGACCGTTACATTGGATTTATCTCTGTCTGGCTCATGGGTGGGAACAATTT
GCGAGAGTAAGTGGGTGAGCACGGGCGGCATAACGGGATACAGTGAACACTCAGTAGCTGGGACGCCATGGGGGATATGGACAGTGAAACTGGCG
CCGCTGCTGCGTCGACTGCGACGCCGACGGCGACTGCGACTGCAACTGCAACTGCAACTGCGACAGCGGCTCGTCTGCGTCGCGTCGCTGCAGCA
GCGCTGCCGCTGCGCGGTTAACCGTTTCGCGCCGATAGCCAAGCAGCGAGTTACCGTTACGCGATTGCTGCTGCTGAGCTGCCACCGTCAGCGTT
TCCCTTCCCGCTCTCCGAACAGCTCCACCAACTCCAACTCCCCTTCCCCCTCCACCACCAAAAATCGCAGCTCCATTTCCCCTTTTCGTTGTTGT
TTTTGCCGTTAACACTATATGCTGCGCAGTCCGCTTCGCTGTTAGGGGTGCTGCTGTTGCAGTAGCAGCTGTAAAGAGTTAACATGATTTTTTT
TAACTAAAAGAAGTACAAAATGTTAAAGGAATTTATCAAAATCCGAAATTGTACCCTCGTAAACCGGCTTACCTGCTGTCTTCTTCATCTGTGAT
CGATTTAATCCCTTCGTTTTCAGAACCATTCCATTAGATTCCGGCTTGGCTGTCAACGAAGAATGAGTTCCACATACCGCTTTGGATGACAGCTG
ATCGTCCAACGGCGGAGCCTTGCCACCCGAACCGGCTGCACTGCGTCTGACCAACGTTCGAACATTGGTCCGATTAGAGATAGATTGTTGTATCG
AGCCCTGGTGGCTCTGCAGCTTGGCGGTTTGTTTCGATCCCTCGATGGCAGACGGACTTATCGGGGACTCCTGCAGATGCTGCGCCTGCTGTTGG
AGGATCTCCGCCTTGCGTATCTGCTGCTGGGTGCGGAAGGCACGCTTGTAGGCCGAAACCTGTCAAGGATCATGGGATATCTATGAGATATATGT
GAGTTAGACATATTACCTACCTGCGAGGCACTCGCCACCAGCAGCTGATTGGCTCCCTTGACCTGGCCTGGTGTCCTGTCCTCCCGCTTCTGATT
CGCCTTTCTTTCCGGTTTCTTTCCGAGCTTTGGATGCGATTTCTTGGAGGCATTAGCCGCCGTCACGTCATCATCTTTGGCCGGCTGCAGGAAGG
ATCGATGGCTGGAGCGGCTAACCTGGTTGCTGGTCACCTTGGTCACTCGCGGCTTATCATGCAGAGTCTCAAGCAGCTGCTTCTTCTTGACATTT
TCCTTAGCCTTCTCCTTGACCGTGTCCTTGACCTCGTGGGGACTGATTGGCACATCCTCGCACTTGGGTTCCTCCACTTTGGTTGAGTTCTGCAG
ACTCTGTTGCTGCAGGTGGACGCGACGCACGGGTGCCAGGGTGGCTCTATTGGACTCATCTTGAACTGAAGCCGCTTCCGAATTTGCTTGCGAAG
TGTCGTGGGAAGTGGAACCGGAATTGGAATTGGCTTTACCATGCTCCGAATTCAATTTCGTCGATTCCAAAGTATCGTCTTTGGTTTTTCCCTCA
ATCGAGCGTAATTTTGTCGCAGATCCCGATGGGATTGCCCAATTTTGACTACTGGCATTTGAGTTACCCACCGAAGCGTTGTCTGATTTTGCTAC
ATTTGACATCAAACCCTTGCCGCACGGGCTACTTGATCTGGGGTACTTGGCCAATCTTCACCTGGATTAACATCCCAATCGCCTGATGTGTCTT
CCGAACTCTTTGCATATCCGAAATCGTTAACCGACCTTTTACCTAAGTCTTCTGCATATACAATTATTATAATTATTATCACTCACATACATATA
TGATTATATCATCTAGTTGACTTACCTTCATATCTACCCAAAGAATTATCCCAAGTGATTGTCGAGTTGCTGGGCCTGAAACTAGTCCGCGAACT
GCTGTCCAAGCTGGATCCCCGAGTGGTTACATCGAAGCCCCGTGGACCGGGTGGAGTGGCGGGTCGCGCTATGGATTCCAGCGATTCCATTAGCT
TAACGCCTCCGGACTCCAGGCTTCGGCTCCTCTGGCGATAGTTGGCGTGCAGGACATTGTGAAAGCTAAGCTGGCGCGGCTGTTGTCTCACCTCC
GAACGTCGCGTGGTGGCATTGGTTTTGGTGGTATTAATTGACATATCCGAGCTCTTCTCAATTCGGCTCCTTGGCGAATCACGGATACTGGCATT
GATTGGTCTCTGCTCGTTCCGATTGAAGGCATATGTGGCCACGGGTCCATCGGCGAATTGGATGTACTCGAACTGCTTGATGCGATCGCCCAAAG
TCTGAAAGCGGTGGCGCATCTCCGACGGCTGTTGTCCGTTTCTGGTGGTGGTGCTGTCATTTCCAGTGCCTAGTGGACCGAGTCCAGACCGCTTT
CGTCCACCGTCCAGCTTGGTCAGCACCGAAATGCGACGCTTGAGGGCGGCATCCACTGGCATCAGGGAGTCGCCATCGCTACGCGGCATTTGGAT
GCCCTGCGCCAGTGAGCTCTTCGCCATGGCGGCTATGTGGTGTTGCCTGCTTGGCGGCATCATTGCTACGGATCCCAAAATGGCTGCAGATGGAC
GGGGTGGCATGCTCATGGAACGGCCACTGAACATGCCCATATCGACCAGATGAGACTCCTCTTTGGAGTCCTTGCTTTTGCGCATCGATCGGCTC
TGGCGCTCCCGTTTCGCTTTGCTTTTGCGGAAGGATCCGACCAGGAATCCGGTGCGGGATGACTCGCTACTGCGCCCGCTGGAGCAGCTCGAACT
GGCGACCCTACGCACGGAACTTTGACCGTAAACGGAGGCGTAAGGACGAGCCGCCGTAAAGGACATGGAGCGTGAACGATTCGCCTGCATCATCG
AGTACAGAAATTGGCCGGAATTGCTATTGCTGGCCGCCGATGCCTGATCCGCTTGCATGATGTGGCTGCGCGGATAGATATCGTTGGCACTGGGC
TTCGCCTCCGCCCTCTTGATCCGTCGCAAAGGACCAGCGTTCTCAGTACGGAAACGTGGGTGTCGATTGTCTACAAATTGATTGTATACGATGTA
TTTTACTTTACTTATATATAAGAAATGTTAGTTATAACGGTGAACTTACGTGAACTATAGCCGCGCTCGTAATAGGATCTAACGGCACTTTCGTA

FIGURE SHEET 25

CAACTCGCTAGTGTTGCGCAAAAACCAGGGTTGCATTCGGGTATTCACTTTGATCAAACGATTTATCTGGTCGGGTTTCATCGTAACGCCGGATA
ATTTCTACGTCCGAATGTTGGCAATATTCGAATTTGGATAAATGGCACAGGTATTTGTGGCCTATAATAATAACTAGTTTGGCTTCTATCTATTG
GCTTGAACTTGAACAATTTTGCTTTCCAAATGCACTGAATCGAAGTTAATGTTTGAATTTTTATTTGCCTGTTGCTCAGACCACTTTTGTATTGC
TTGACAATTTAATGCTCTTAAAACTAATGGCTTGGGGCAAAACGGGAGAAAAGTAATCGAAAACGTAACTAACTGCGGTGTACTAAAACATGCCG
GTGCGTGAAAATGGATATGTCTGTCTGTATTTTGAAAAGAAAAAAAAGAAAATCACACGCACGAAACTCAAGTAACGTCAACGTTAAAGCCGAGT
AAAAAGAAGTGTTACATTTATTTCGATTTTGACACAACAATCGGAGTCTGCCGAGTTTATTCCCTCTATATCTATATATATTTCTAACACGCGCT
ACAAATCAATAAGTCAATATGAAGTCAGGCTAACTTTAATCCAAGGAATTCATCTGTGCATCAATGATCTTTGGTTAGTCCATATGAAGTCCAGC
AATCTTGAATCCAAGAATTCCCACAGTGAATGAACACACGAGCACCCAGCTTAATTTAACCTCGGTTGGCTCAGTTTGCGGATTTCGCGTGTCCG
TAACGAACGAAACGCCGAACTTAGTTGTATAATTATGTGTGTTTCAATCAAATTAGCCCACACCGGTCATACATAATGCACTACCATGCTCACTC
ATTCGTTAGTCAACGCTGCTAATCCGAGTCAACCACTCACTCCAACCCGCCGGGTAGCCAACGTCATGGACTCACGAAAAAGCAGTCATTTGACA
TTGATTTATCAGTGGCTGTCAAAGTGCCGTCATCCGCCACCCCCGCTTTTCCAGCCCGCTTTTCCAGCCCGCTTTTCCACCCACTTCCAAACACA
CCCCCCCACCACTTTGGCCGCTGGGCGTGGTCAAGGTAAAAATGTAATAATTAGCCGCAGTGATGTGATGATGTTCGGGGTCACCCCCTCGTTAG
CCATGGTATCGTATCTCTGGCCCATCGTGGTGCCTCGATTTTGAGCTTGGCCAGCAGCAATTTGTCAAAGTTTGGCCTGAAAAATGAATGCTGGT
CGTCCTGTTTGTGCACTCGAAGAAATTACGCAGTGAAAGTCATTAAGAGATATCCTTAAACTTCTGTTAAACTTCTTCTGGGGACACAAGAAAGG
TTTCATAGGCTTACTATACTATTTTTCATTACACACAGTCTTAATTATGCAAAATAATAAATAGTTTAAAGGTATATGCCTATTTTAAATTATAT
TCCTGATATTTAAGCGAATTTTTTAGTGATTCATAGCTAGTTTTCGGGCTTATTACCTGACATA
(SEQ ID NO: 73)

Exon: 4574..4040
Exon: 3965..2781
Exon: 2711..1921
Exon: 1864..1498
Exon: 1398..1001
Start ATG: 4166 (Reverse strand: CAT)

Transcript No. : CT3184
TAACACTTCTTTTTACTCGGCTTTAACGTTGACGTTACTTGAGTTTCGTGCGTGTGATTTTCTTTTTTTTCTTTTCAAAATACAGACAGACATAT
CCATTTTCACGCACCGGCATGTTTTAGTACACCGCAGTTAGTTACGTTTTCGATTACTTTTCTCCCGTTTTGCCCCAAGCCATTAGTTTTAAGAG
CATTAAATTGTCAAGCAATACAAAAGTGGTCTGAGCAACAGGCAAATAAAAATTCAAACATTAACTTCGATTCAGTGCATTTGGAAAGCAAAATT
GTTCAAGTTCAAGCCAATAGATAGAAGCCAAACTAGTTATTATTATAGGCCACAAATACCTGTGCCATTTATCCAAATTCGAATATTGCCAACAT
TCGGACGTAGAAATTATCCGGCGTTACGATGAAACCCGACCAGATAAATCGTTTGATCAAAGTGAATACCCGAATGCAACCCTGGTTTTTGCGCA
ACACTAGCGAGTTGTACGAAAGTGCCGTTAGATCCTATTACGAGCGCGGCTATAGTTCACACAATCGACACCCACGTTTCCGTACTGAGAACGCT
GGTCCTTTGCGACGGATCAAGAGGGCGGAGGCGAAGCCCAGTGCCAACGATATCTATCCGCGCAGCCACATCATGCAAGCGGATCAGGCATCGGC
GGCCAGCAATAGCAATTCCGGCCAATTTCTGTACTCGATGATGCAGGCGAATCGTTCACGCTCCATGTCCTTTACGGCGGCTCGTCCTTACGCCT
CCGTTTACGGTCAAAGTTCCGTGCGTAGGGTCGCCAGTTCGAGCTGCTCCAGCGGGCGCAGTAGCGAGTCATCCCGCACCGGATTCCTGGTCGGA
TCCTTCCGCAAAAGCAAAGCGAAACGGGAGCGCCAGAGCCGATCGATGCGCAAAAGCAAGGACTCCAAAGAGGAGTCTCATCTGGTCGATATGGG
CATGTTCAGTGGCCGTTCCATGAGCATGCCACCCCGTCCATCTGCAGCCATTTTGGGATCCGTAGCAATGATGCCGCCAAGCAGGCAACACCACA
TAGCCGCCATGGCGAAGAGCTCACTGGCGCAGGGCATCCAAATGCCGCGTAGCGATGGCGACTCCCTGATGCCAGTGGATGCCGCCCTCAAGCGT
CGCATTTCGGTGCTGACCAAGCTGGACGGTGGACGAAAGCGGTCTGGACTCGGTCCACTAGGCACTGGAAATGACAGCACCACCACCAGAAACGG
ACAACAGCCGTCGGAGATGCGCCACCGCTTTCAGACTTTGGGCGATCGCATCAAGCAGTTCGAGTACATCCAATTCGCCGATGGACCCGTGGCCA
CATATGCCTTCAATCGGAACGAGCAGAGACCAATCAATGCCAGTATCCGTGATTCGCCAAGGAGCCGAATTGAGAAGAGCTCGGATATGTCAATT
AATACCACCAAAACCAATGCCACCACGCGACGTTCGGAGGTGAGACAACAGCCGCGCCAGCTTAGCTTTCACAATGTCCTGCACGCCAACTATCG
CCAGAGGAGCCGAAGCCTGGAGTCCGGAGGCGTTAAGCTAATGGAATCGCTGGAATCCATAGCGCGACCCGCCACTCCACCCGGTCCACGGGGCT
TCGATGTAACCACTCGGGGATCCAGCTTGGACAGCAGTTCGCGGACTAGTTTCAGGCCCAGCAACTCGACAATCACTTGGGATAATTCTTTGGGT
AGATATGAAGAAGACTTAGGTAAAAGGTCGGTTAACGATTTCGGATATGCAAAGAGTTCGGAAGACACATCAGGCGATTGGGATGTTAATCCAGG
TGAAGATTGGCCCAAGTACCCCAGATCAAGTAGCCCGTGCGGCAAGGGTTTGATGTCAAATGTAGCAAAATCAGACAACGCTTCGGTGGGTAACT
CAAATGCCAGTAGTCAAAATTGGGCAATCCCATCGGGATCTGCGACAAAATTACGCTCGATTGAGGGAAAAACCAAAGACGATACTTTGGAATCG
ACGAAATTGAATTCGGAGCATGGTAAAGCCAATTCCAATTCCGGTTCCACTTCCCACGACACTTCGCAAGCAAATTCGGAAGCGGCTTCAGTTCA
AGATGAGTCCAATAGAGCCACCCTGGCACCCGTGCGTCGCGTCCACCTGCAGCAACAGAGTCTGCAGAACTCAACCAAAGTGGAGGAACCCAAGT
GCGAGGATGTGCCAATCAGTCCCCACGAGGTCAAGGACACGGTCAAGGAGAAGGCTAAGGAAAATGTCAAGAAGAAGCAGCTGCTTGAGACTCTG
CATGATAAGCCGCGAGTGACCAAGGTGACCAGCAACCAGGTTAGCCGCTCCAGCCATCGATCCTTCCTGCAGCCGGCCAAAGATGATGACGTGAC
GGCGGCTAATGCCTCCAAGAAATCGCATCCAAAGCTCGGAAAGAAACCGGAAAGAAAGGCGAATCAGAAGCGGGAGGACAGGACACCAGGCCAGG
TCAAGGGAGCCAATCAGCTGCTGGTGGCGAGTGCCTCGCAGGTTTCGGCCTACAAGCGTGCCTTCCGCACCCAGCAGCAGATACGCAAGGCGGAG
ATCCTCCAACAGCAGGCGCAGCATCTGCAGGAGTCCCCGATAAGTCCGTCTGCCATCGAGGGATCGAAACAAACCGCCAAGCTGCAGAGCCACCA
GGGCTCGATACAACAATCTATCTCTAATCGGACCAATGTTCGAACGTTGGTCAGACGCAGTGCAGCCGGTTCGGGTGGCAAGGCTCCGCCGTTGG
ACGATCAGCTGTCATCCAAAGCGGTATGTGGAACTCATTCTTCGTTGACAGCCAAGCCGGAATCTAATGGAATGGTTCTGAAAACGAAGGGATTA
AATCGATCACAGATGAAGAAGACAGCAGCTGCTACTGCAACAGCAGCACCCCTAACAGCGAAGCGGACTGCGCAGCATATAGTGTTAACGGCAAA
AACAACAACGAAAAGGGGAAATGGAGCTGCGATTTTTGGTGGTGGAGGGGGAAGGGGAGTTGGAGTTGGTGGAGCTGTTCGGAGAGCGGGAAGGG
AAACGCTGACGGTGGCAGCTCAGCAGCAGCAATCGCGTAACGGTAACTCGCTGCTTGGCTATCGGCGCGAAACGGTTAACCGCGCAGCGGCAGCG
CTGCTGCAGCGACGCGACGCAGACGAGCCGCTGTCGCAGTTGCAGTTGCAGTTGCAGTCGCAGTCGCCGTCGGCGTCGCAGTCGACGCAGCAGCG
GCGCCAGTTTCACTGTCCATATCCCCCATGGCGTCCCAGCTACTGA
(SEQ ID NO: 74)

Start ATG: 409 (Reverse strand: CAT)

MKPDQINRLIKVNTRMQPWFLRNTSELYESAVRSYYERGYSSHNRHPRFRTENAGPLRRIKRAEAKPSANDIYPRSHIMQADQASAASNSNSGQF
LYSMMQANRSRSMSFTAARPYASVYGQSSVRRVASSSCSSGRSSESSRTGFLVGSFRKSKAKRERQSRSMRKSKDSKEESHLVDMGMFSGRSMSM
PPRPSAAILGSVAMMPPSRQHHIAAMAKSSLAQGIQMPRSDGDSLMPVDAALKRRISVLTKLDGGRKRSGLGPLGTGNDSTTTRNGQQPSEMRHR
FQTLGDRIKQFEYIQFADGPVATYAFNRNEQRPINASIRDSPRSRIEKSSDMSINTTKTNATTRRSEVRQQPRQLSFHNVLHANYRQRSRSLESG
GVKLMESLESIARPATPPGPRGFDVTTRGSSLDSSSRTSFRPSNSTITWDNSLGRYEEDLGKRSVNDFGYAKSSEDTSGDWDVNPGEDWPKYPRS
SSPCGKGLMSNVAKSDNASVGNSNASSQNWAIPSGSATKLRSIEGKTKDDTLESTKLNSEHGKANSNSGSTSHDTSQANSEAASVQDESNRATLA

FIGURE SHEET 26

PVRRVHLQQQSLQNSTKVEEPKCEDVPISPHEVKDTVKEKAKENVKKKQLLETLHDKPRVTKVTSNQVSRSSHRSFLQPAKDDDVTAANASKKSH
PKLGKKPERKANQKREDRTPGQVKGANQLLVASASQVSAYKRAFRTQQQIRKAEILQQQAQHLQESPISPSAIEGSKQTAKLQSHQGSIQQSISN
RTNVRTLVRRSAAGSGGKAPPLDDQLSSKAVCGTHSSLTAKPESNGMVLKTKGLNRSQMKKTAAATATAAPLTAKRTAQHIVLTAKTTTKRGNGA
AIFGGGGGRGVGVGGAVRRAGRETLTVAAQQQQSRNGNSLLGYRRETVNRAAAALLQRRDADEPLSQLQLQLQSQSPSASQSTQQRRQFHCPYPP
WRPSY*
(SEQ ID NO: 75)

Celera Sequence No. : 142000013384562
TACTGTACTGGATTAACCAGATTGCAATCCCTGCTGCTGGTTTTTATTTTTCTGGACTTCTTTCAGCTTCACTCTTAATTATGCAAAAGTTGTTC
TCTTGGTTTGGCTTTCTGGGTTCTTTGGTTGCATATAAATAAATGTAAATGCGGGTCAATGAACTTTGCAGATTATCATATGATAACCAAATGTA
GATTGGGTCCGCATAGAGAAAGTATAATCTAATATATGTTTTTGATCAGGTAAGTATCAATAAATAGTTCTGATCAATAAAAGTTCATTGAATTC
ATTGTTTTAGTGTTTTAATTAAATACAGGAAATACAGGAAGAAAACGTGAAAATAAATTCCCGAATCGAAAGACAATAAAACTGCCCGCTTGAAA
TTGAATTAAATACAATTGTTAACTTGTTGTGATTTCTCAAAAAATTTCAAACACGTGCTGCTGTGACATTGACCCATCAATTGATCCCTTCGAGT
TAACTGGGAGTAAGTACAGCAGCGGTCAAGAAACTAGCTTCCAGAACATTGAATAATTTCAAAGTCAATAAAGCAAGTAAAAGTGCTTTGAAGTG
CTAATACATGTGAAAGGTATTTTAAAGGTAATTATAATTTAATACAATGAGTTCAAAAAACTTCTTAATATGCACATTGATAATTTCTTTCTAAT
TGATAATTTCTTTCTAATTGATAATTTCTTTCTAATTTATAATTTCTTCCTGGATTTGCGGACTTTTGTCTTAACAGAGGACAGTTTTAATATAA
AAAATATTCACTAAGAAGACGTAATGGAATTATTTTTGACAACACATTATTTATGGTGCACAGTTCAGCACTTAAACTTGTTTTTTCTTGGCTTT
GGGTATATGTATGTACATATATTCTTTTGGTTTGTGTTCTTAACACACTTGTGTCACTCTATTCCTTTTTTCGGCACTTGTTTCGAGTGCGTAGT
TGTACTTGTCTCGTGATTTCGGGGTCAAATCTGGCGTTCTTTTCTTTTTTTTTTTTTTTTGCGATTCAATTCCGTTCAAGCTGCACTCTCGAGGT
GCTTGACACACAAAGATTGTTGGGACCAACCGTTGCCAGAGCCTCAGTCACAGCCACAGAAAAGCGAAAAAAACACACGCAGGAGTGCGACCTGT
TCGACGGTCGACGCGAATCTAAAGTTTACTGAGCACGGCGCTTTTATCTTATACGATAGCCCGTGGTTACACCGCTCACCCATACAGATGGAAAA
GCCGAAAGCCGAGAAATGGAGAGCCAGTGAAACGTCGACGGCTTAGAGATTGAAACGCTGCTTTGCGTCGGCGCAGAGAATCGCAGATTCAGTAT
GCTAGTTCTATCGTAGAGCATGCAATGTAGTTGAACAGCCAAGCAAAGGAGGTAAAAAAAACAATAAAAAAGGAAGAAAAAAACAGCACATGTGT
GACCCACACGAAACGCACAGCGGGCGATTGCAATGAAATAATGGCAGGGCTTACCCGGCGTATGCGCAATTTTGATTCACGCTGCACACATACGC
AGCGATGTCACTACGTGTTTTTGACCCTAATTGCGCTGATTAACCCATTTCTTTCTATTTCGTATGCCACTGGGCACTTGAGCCACTCGACCCTA
GAGTTCACCCAGTCACTCAACCTGAAACACCCCCTACTTTTGGACCACCCCCCGTGGCGGAAGCGCCGAAGATAAGGGGCCACAAAAAGTGGCAA
AAAACAAACCATAATAAACCAAGTGCAGACGGACAGACAAACGCAGCATGCGGGCTCACAGGAGGGGCTTTAGCGGGTTAACCCTTTGGGGAAAG
CCTCATATCTAGGTCACCGATTAAAGTATTTATCAAATTTTGAATGTTTTATTTATACATTTACTTGTTGGTTCGAATTAACTTTGATTATTTGA
ATTGCTAATTATAATTTATTATATTTACTACATGCCAGTCTTCAGAGGGTTAATTTGGCATGGAAAATGGCATGTAACTCGAAATATTACTGCGG
CTAGGGCCCTGCCTTTGGCTAATTGCCACAAACCTCGTTTGGCTTTCATCCACACTTTTTTTGAGGATTAAAGATTTGATAGTTTTAAGGAGAAA
TTGAAATGGGTGTGAAAGGGAATTGGAACATAAGCTATAAACGAAAATAATCTGCTTTATTTACTGAAATTCGATTATCATAAGCCGATTTTCGG
AAAGTGTTAGGCTTTGCCTTCAATTTATAGAACAAGTTAACAAATTTAAAAGAGTATTTGTATATCGTATGCGTGGGTTTAAAAAAAAAAGCATC
ACGTGTCCATCTCTAATTTAAAGAAATATAAAGTGACATACAAATTTTCGTATAACAGTCTGCCAAAAAGTCGCCGCTGTTATACTCAATTTTTT
ACGGACACAGCGCCCTCTGACATTTACAAAGTGCAACTACTCGCTTTGCGCGCCAATTTCAAGTTGTTAATTCTGTGAAAACCCATAGAGTACCG
AAATCCCGCACATAATGCGCATTTGGCGCCATTTGAATGATAAAAATTCCAGGAATTTCAGTTCTTTTTCGTCGTGTATTAATGTATATTTAAAA
TTGATGGTCTTTGTTCAATAATATTGCCTTTTTTGATGCAAAAATAAGCTTTGCTTAAATAATAATCATTACATGGTAAAATATTTGTTTTCTTG
TTTGCATTTGCGTTTCGGTGCCTTGTTGTTCGGTTACGGATTACATAAAAATAAACAAATAATAAGCGTAAATTGTACCTAGCAGAAGTTTACAA
CTTTCAACTCTTAAACGATAGATCTTATAAATAAAGTTTTATGGATGAAATTAATGAGCGTGTTTGTTTTTGTGTGATATTTGTTTTCTTTTTTT
TTTTTTGTTTTTAGCCATTTTTTGTTCTGCTTATCATCTACAAATGATTAAGGGGTCTGATTTCGGGATCGGCCTCTTAAATTTAAATGACATGG
TTCCTCACGTTTTTAGATTATAATGCACATTTTTCGTTTGCTTGTTCGTTGGTTATCTTTAAAATTTGAACTAGAGTGCTTAAATAATTGAACTA
AAGCCGAAACCATAAAAACAATAATAACTAAACAAAAGCGTTAAATTCCAAATGAAATTGTCTGTTTTGCATGAATGCGAGTGTCGGGTGTGTGT
CTGCGTCGTGTGCGAGAAACTTAGTCTACGGATTAACAAATGAAAATCAACAAAAATCAACTTAAAAGCAGCATGAAATAAATACCCCTATACGT
CTATATATACAATACGATAACACCCAAACTTAGATAACGAACTGCACGATCATCCCACAACCTACAGCATCAGTCGCGAGCGCGACTTCTTTAGC
CGCCCGGTGGCACCGCCCAGGCCATCGCCGTTCCAGGACTTGGACTTGGCGCGAAAGTGGCGATAGGCCTCGTTGTAGGCGGGATCCAGCATGGT
GCGGTAGGCATGTGGTTCGCACAGCTCAACGTGCGACTCGAAGAACTCCTTGTAGCCGTTGTGCAGCAGATAGATCTCGGGATAGTGCAACGCCG
GATAGGCGTTGGTATTCCTCTCGCGATCCAGATTACGCAGGAAGCGGGACATTTTCGGTCCACGCTCCGAGGAGAATTCGCAGTGGAAGATAATG
ATGTTGCGCTTGTGTCCCGATTCGGCGTTCTGCTGCTGCTGCAGCTCAGTCTGTTGGACGGTGAGGAACTCATCGAGGATCTGCTCGGTGGTGTA
CAGGTTCTTGGCTCCCTCGATGTGGCCGCCCTCGAATTCGTAGGGGTAGCGGCAGTCGATGATGCGGTAGCTGGCCACCTTATCGCTGAACTCGC
CCTTAAGCAGGCGAGCCACTGTTTCGCTGGAGATGCTCTTCAGATCCCGATGACGACCCTCCATCAGGGGCAGGGCATAGGCTTTGCTGAAGTCG
CCGATTAGCTCGGGCTCGTTGCGGTTCTCGGAGCGGGCCAGGGCGGACATGATCTCGGCGTCGTTCAGGGACATGCACTTCCTCAGTGGAGGGGG
GTGGCTAATCGTGACCTGGCTGAGTGGGCTGGGTGCGGGGCAGTTCTCCTTCTCAACGGCGGCGCAGCGATGGCGTTTGCTCTGGATGGGCGAGC
AGTTGGCCGATGCTGGCGGTTCCGGGCGCTTGAAGCAATCCCGGGCAGTCTCTGGGGTCTTTGGTGGTGGGGTGGTGGTGCTGTTGGTGTTGCTC
TCCGTCATGCTGAGGCACCTTCTGACCGAAGGGCGGCGCATGGACAGACCCGCTGGCGATTTGGCAGCAGGCTGCTCCTTGATCTGGCCGCTGAT
CAGCGAGTTTAGGCCACTGGGGAAGCCCAGGGCGGTCTGTTGGCTCTGCGACTCCATCTCGAAGAGCTCCATGTACTCATCGTCCATGGAGGACT
CCATGGAGCATGTGGAGGACAGGCTGTTGAAGATGCGGAAGCTGCGCGCCGGCGTGTGATCACTTGATACTCCCATAGCTGGCAGAATTTTCGGC
TGGCGGACGATCTGGAAGCGCTGGGGCGAGCCCTCCGGCGAGAGCAGACCCATCAGCTCCGGACTGGCCGATCGCTGCTGATCCTGGGGCACAAC
GTCGTCGTCGTAGAACGACAGCTCCTCCTGGTCCATGCTCATCAGTTCCAGGGAACGGCGAGCACGACGAGATCCACTCATTTTGTTGATGCTAC
TCGAACTGCTGGTGTTATTACTGCAAGAGCAAACAAAGAGAGGGGGAGGATTAGTCAACTGTTCGGCATCGAGGAAGAGAGCTGCTTTTGCTTCC
CTAAACTCTCGCAAGAGCGGGTCATTAAACCCAGCTAAAAATACTGACAAACTGGTGGTGGTGGTGGCGTTGGTGGTGTAAAAACAACAAAAATA
CCCGAGAAAATACAGAGAGGGGTTGTTGTAATTGGGTGAAGAGGGAGCTGAACTAGAAATTTACTTTAATGCAGCTTCGAAAACTGGAATTTTTG
GGATTCGACTTGCGCACACGATATCATTGATACCATTTTTTTTTTTTTTGATAATTTTTACAATTCCCTAAAATTGCGAGGGAACCGTTGCGTAC
CGCCTTATCTTCTTCTTCTTGATTCTACTTAAGCATTAGCGGTTCTCCAAATGGAATTCCCTTTTGCTTTTCGCATGCATCTGCTTTTCAGCTTG
ACTTTTGCTTTTGGGTCACACGTCACGCAAGCGCAGCGATAATACAACAAAAACACGCCACAAAGAACCGCAAAGAACACGGAGGAAAAAAGGAA
CAAAAATCGAAAAAAAAAAAATGACTGACTGACGGACGACGGACAAAAAGCATTTTTTGCTGCTGCTTTTTTTTGGAGCCTCGCGGAAGCCGGTT
TAATGAATGAAAAACGGCAAGCGAGCAACAAAACAACAGCTGAGCGCCAAAATAAAAATCGGGCAAAAAGCAAACGTGCCGAGCGTGATAAAAAG
AACTCTTACTTTTGTTGGCCCCATCGTTTACATTTCTGTTTTTTGTATTTTTTTTTTGCTTTGCTGTTGTTGCTGTTGCTCTTGAACTTGCACTT
TTTATCGCGTATTTTCAACTGGTATTCCTGGTGCAAAAGGGGTTTGCTGTTGCTAATCCTTGGCGGCATAATTACCTGATATTGCAATCCATGC
TGCAGTTGTTTTCCTCCACAATAGTTTCCCACAGCATTTTGTTGGTTTTGTTGTGTTATGTGTTGCGTTGGTTGCTTCGAAGAGCCGAAGATGTT
TGATTTCGCTGGCGAGTCTGAAGCCGAAGAAATTGCTAAAACACAATTTGTTCTTGGTCACTCTGCACTCATTTACAGTTTGTTTTTAGAATTTG

FIGURE SHEET 27

AGATGGTAGTCCTTGGTTTTTGGCTAGTATTGCATTTTAGTTAATTTAGGTTTTTTTGTTTTTTTTTTTTGTTAATGTGTCCGTTTGAGCATGAT
TTTTTGTTTTGTATTTCGGAGTGTGGTTGTGCGAGGTTTTTCTTTTTCTTCAATAATTTGAACCGCACAATCTCAATTCACCGAACGAGGAACCG
AAAGGCTGAACAAGAAGAGCTGTTGACTCGACGACGAACTGAGAACGAATGTGCTGAATATGCCGAGCAGCTGGTTTTTATAACCGCACCCCGGC
CGATCACGATCAGCTGATGAGCTAATGGGCGCGAGCGAGATGGCGCGCGTTTTTTGTTCTCTCTGCTTCGCTCTTTAGCTCTTAGTTCTCAGCTC
CTTTCCTTTGCCTTCCCATCCTATCCTTTCCTTCCTATCCTTCCCAGAAGTGCCAATAGAAGAGGAAGGGAGACGGGCAACGAGCGACACCAACA
CACATAACGGGGACGGGGCCAGAGCCATGTGCGATGCGAAAAGGAAAACTGGGAAAATGGGAGAATCAGGATCATATGGACTCAGTTTTGGAAAT
CTCTGCTCATGTGGAGCACAAGAGTGCCGGCAACAGGTAGAATCCTTTCCCCTGCACTTCCCCTATCGCAAAATCCCGCACCGAATACCAATGTC
CCGAGAAACGAGGAGAATCTGGCGCCTTGGTGGTCGCCAGCTCTATGGAGGCCACTGATTTTGGCGCGCGAGCTTTTATACCGCGACGCGTACCG
CCGAAGGGGATCCGAAGTCGCCACAATTGGAGCCGAAGTGGAGCCGAGGAGGCTCCGAACCGAACACATGTGAAAATAGTGTGGAGCCCCAAGAA
GCGAAGAGGAAACGCTGAAGAACTGCGCGAATCTTTAAGCAGAATTTCAAGGCGGCATCGATTGTGTCGTTTGCAGGTAATAATGTGAGATCCAC
GCATTCCTGCTGCCCCCTGTCCCCCCTTGTAACCCCTCCCTGAAAACTACATATCAGCAGGTAGTGGCCGCAGTCATATGATCGCCGCACCGGCG
GGATGGGCGGTCGTGGAGGGGGCGTGGCTCCTTTGTGTTCTGCAGACGTAGACGCCAATGTCGTTAAATGAGCAAAGCTTCCAGCCACAGAGATC
CATTCACAGGTAGCACTCTACACGATGGACCGTGTGTCTTTAATGAGAATCCGTACAAACACAGATCTTAAGCTAGATAAACTACTACTAACAGT
AGCAAACACGTGGAAAATCATGATGTCAACCATGCGATATGACCAATAATCGATAATGTGAAGCTCAGACTAGTTGCCCACGCCGAAGCTCCACT
GTAGCCCCTCGTTTGTGTGCAATCGCGGCAAAGTTAAAGCAAAAATCGAGTTACATATGCGCCGATGCCCTGCGGGAGTCATTCTGGAGGATCCG
AGGGGTTCACTAAGGAGGGTTGGGGGTTTGCGAACACCCATGGGCTGTGCTGTGCAGTTCGAGTGTGTTTTTGTAAGGTTCGCGGCAAACAAATG
AAGGACAGGCCAGTGCAACCAGGCCATATCATTCACACCGCTTGAAGAGCAGGCGAAAGTAAATGATTTCGGGACCAACCACAGCCGAAGCCACC
AACCAAATGAGCTACGGTTTCATTCCGCTGAATTCCTTTGGCCAGCTTTTGTTGTTGCTGCAGGAAGA
(SEQ ID NO: 76)

Exon: 6478..5587
Exon: 4675..2532
Exon: 1011..1001
Start ATG: 5642 (Reverse strand: CAT)

Transcript No. : CT3224
ATTCTCCTCGTTTCTCGGGACATTGGTATTCGGTGCGGGATTTTGCGATAGGGGAAGTGCAGGGGAAAGGATTCTACCTGTTGCCGGCACTCTTG
TGCTCCACATGAGCAGAGATTTCCAAAACTGAGTCCATATGATCCTGATTCTCCCATTTTCCCAGTTTTCCTTTTCGCATCGCACATGGCTCTGG
CCCCGTCCCCGTTATGTGTGTTGGTGTCGCTCGTTGCCCGTCTCCCTTCCTCTTCTATTGGCACTTCTGGGAAGGATAGGAAGGAAAGGATAGGA
TGGGAAGGCAAAGGAAAGGAGCTGAGAACTAAGAGCTAAAGAGCGAAGCAGAGAGAACAAAAAACGCGCGCCATCTCGCTCGCGCCCATTAGCTC
ATCAGCTGATCGTGATCGGCCGGGGTGCGGTTATAAAAACCAGCTGCTCGGCATATTCAGCACATTCGTTCTCAGTTCGTCGTCGAGTCAACAGC
TCTTCTTGTTCAGCCTTTCGGTTCCTCGTTCGGTGAATTGAGATTGTGCGGTTCAAATTATTGAAGAAAAAGAAAAACCTCGCACAACCACACTC
CGAAATACAAAACAAAAAATCATGCTCAAACGGACACATTAACAAAAAAAAAAAACAAAAAAACCTAAATTAACTAAAATGCAATACTAGCCAAA
AACCAAGGACTACCATCTCAAATTCTAAAAACAAACTGTAAATGAGTGCAGAGTGACCAAGAACAAATTGTGTTTTAGCAATTTCTTCGGCTTCA
GACTCGCCAGCGAAATCAAACATCTTCGGCTCTTCGAAGCAACCAACGCAACACATAACACAACAAAACCAACAAAATGCTGTGGGAAACTATTG
TGGAGGAAAACAACTGCAGCATGGATTGCAATATCAGTAATAACACCAGCAGTTCGAGTAGCATCAACAAAATGAGTGGATCTCGTCGTGCTCGC
CGTTCCCTGGAACTGATGAGCATGGACCAGGAGGAGCTGTCGTTCTACGACGACGACGTTGTGCCCCAGGATCAGCAGCGATCGGCCAGTCCGGA
GCTGATGGGTCTGCTCTCGCCGGAGGGCTCGCCCCAGCGCTTCCAGATCGTCCGCCAGCCGAAAATTCTGCCAGCTATGGGAGTATCAAGTGATC
ACACGCCGGCGCGCAGCTTCCGCATCTTCAACAGCCTGTCCTCCACATGCTCCATGGAGTCCTCCATGGACGATGAGTACATGGAGCTCTTCGAG
ATGGAGTCGCAGAGCCAACAGACCGCCCTGGGCTTCCCCAGTGGCCTAAACTCGCTGATCAGCGGCCAGATCAAGGAGCAGCCTGCTGCCAAATC
GCCAGCGGGTCTGTCCATGCGCCGCCCTTCGGTCAGAAGGTGCCTCAGCATGACGGAGAGCAACACCAACAGCACCACCACCCCACCACCAAAGA
CCCCAGAGACTGCCCGGGATTGCTTCAAGCGCCCGGAACCGCCAGCATCGGCCAACTGCTCGCCCATCCAGAGCAAACGCCATCGCTGCGCCGCC
GTTGAGAAGGAGAACTGCCCCGCACCCAGCCCACTCAGCCAGGTCACGATTAGCCACCCCCCTCCACTGAGGAAGTGCATGTCCCTGAACGACGC
CGAGATCATGTCCGCCCTGGCCCGCTCCGAGAACCGCAACGAGCCCGAGCTAATCGGCGACTTCAGCAAAGCCTATGCCCTGCCCCTGATGGAGG
GTCGTCATCGGGATCTGAAGAGCATCTCCAGCGAAACAGTGGCTCGCCTGCTTAAGGGCGAGTTCAGCGATAAGGTGGCCAGCTACCGCATCATC
GACTGCCGCTACCCCTACGAATTCGAGGGCGGCCACATCGAGGGAGCCAAGAACCTGTACACCACCGAGCAGATCCTCGATGAGTTCCTCACCGT
CCAACAGACTGAGCTGCAGCAGCAGCAGAACGCCGAATCGGGACACAAGCGCAACATCATTATCTTCCACTGCGAATTCTCCTCGGAGCGTGGAC
CGAAAATGTCCCGCTTCCTGCGTAATCTGGATCGCGAGAGGAATACCAACGCCTATCCGGCGTTGCACTATCCCGAGATCTATCTGCTGCACAAC
GGCTACAAGGAGTTCTTCGAGTCGCACGTTGAGCTGTGCGAACCACATGCCTACCGCACCATGCTGGATCCCGCCTACAACGAGGCCTATCGCCA
CTTTCGCGCCAAGTCCAAGTCCTGGAACGGCGATGGCCTGGGCGGTGCCACCGGGCGGCTAAAGAAGTCGCGCTCGCGACTGATGCTGTAGGTTG
TGGGATGATCGTGCAGTTCGTTATCTAAGTTTGGGTGTTATCGTATTGTATATATAGACGTATAGGGGTATTTATTTCATGCTGCTTTTAAGTTG
ATTTTTGTTGATTTTCATTTGTTAATCCGTAGACTAAGTTTCTCGCACACGACGCAGACACACACCCGACACTCGCATTCATGCAAAACAGACAA
TTTCATTTGGAATTTAACGCTTTTGTTTAGTTATTATTGTTTTTATGGTTTCGGCTTTAGTTCAATTATTTAAGCACTCTAGTTCAAATTTTAAA
GATAACCAACGAACAAGCAAACGAAAAATGTGCATTATAATCTAAAAACGTGAGGAACCATGTCATTTAAATTTAAGAGGCCGATCCCGAAATCA
GACCCCTTAATCATTTGTAGATGATAAGCAGAACAAAAAATGGCTAAAAACAAAAAAAAAAAAAGAAAACAAATATCACACAAAAACAAACACGC
TCATTAATTTCATCCATAAAACTTTATTTATAAGATCTATCGTTTAAGAGTTGAAAGTTGTAAACTTCTGCTAGGTACAATTTACGCTTATTATT
TGTTTATTTTTATGTAATCCGTAACCGAACAACAAGGCACCGAAACGCAAATGCAAACAAGAAAACAAATATTTTACCATGTAATGATTATTATT
TAAGCAAAGCTTATTTTTGCATCAAAAAAGGCAATATTATTGAACAAAGACCATCAATTTTAAATATACATTAATACACGACGAAAAAGAACAAA
AAAAAAA
(SEQ ID NO: 77)

Start ATG: 837 (Reverse strand: CAT)

MLWETIVEENNCSMDCNISNNTSSSSSINKMSGSRRARRSLELMSMDQEELSFYDDDVVPQDQQRSASPELMGLLSPEGSPQRFQIVRQPKILPA
MGVSSDHTPARSFRIFNSLSSTCSMESSMDDEYMELFEMESQSQQTALGFPSGLNSLISGQIKEQPAAKSPAGLSMRRPSVRRCLSMTESNTNST
TTPPPKTPETARDCFKRPEPPASANCSPIQSKRHRCAAVEKENCPAPSPLSQVTISHPPPLRKCMSLNDAEIMSALARSENRNEPELIGDFSKAY
ALPLMEGRHRDLKSISSETVARLLKGEFSDKVASYRIIDCRYPYEFEGGHIEGAKNLYTTEQILDEFLTVQQTELQQQQNAESGHKRNIIIFHCE
FSSERGPKMSRFLRNLDRERNTNAYPALHYPEIYLLHNGYKEFFESHVELCEPHAYRTMLDPAYNEAYRHFRAKSKSWNGDGLGGATGRLKKSRS
RLML*
(SEQ ID NO: 78)

Name: string
Classification: protein_phosphatase
Gene Symbol: stg
FlyBase ID: FBgn0003525

Celera Sequence No. : 142000013384859
GCGACCCACGAACAACAACAAAATGTATGGTCAAGGCCAAACTAAAAGAAGGAAATCCCTATTGGTAACCCCAAATACCCTTTCCCCTACGAAAA
TACATTGTTTTCCTCAGTGCGTAGTGTGCATTACTAATAATCTATACAAATAGTTTTAATTCATTTTACTGAAACTAAACGAATTTGTATGATGC
TATCGAACACGATTTTTTGAAAAGTTATTAATAATCCAAGTTCCTTAGAGATTACTCAGATTACTCGGTTCTGTTCAATGTCCTCTAGTTAACTT
GAACCTAATTTCCTCCACATTTGAAACTAAACTAAACATGCGCATGTTCAATCCCAAGTCTCCTGTAGTTTCAGAGATCAGGACGTTTATACGGA
CGACAACGAATCTACCAGATCATTTATTTATAAAAATATAAAAGAATTAATATCGATTGGCTGCGACAAACACTCCCCACTCTCACTGCGCTACC
TCTTGGTTAGCTTTGTGCTAGTTTTAGTCTAGTTTCTAATGTTAATGAACTTTGAAAAAGGGGCGTTCCACAACCGCGCCCAATTCCGCGAGTAC
ATTATCATAAGACGGAATAATTATTCTATTTGCGACCAAGAGCCAAACAATGATAAGACGTATCGCACAAGCCGCGGAAACTCGGGAGGAAAATG
GGGGCGGTTGAAGGGTACATAATGATAAGCGACAGCCGCACCCTCAAGTATTTTTTAAACGATACTAAATATGTAGGCTTTTGTCAAATATTTCC
ATTTAAATTAGGGAAAAGAACACCACAATGTTGTTTGTTGTTTAATAAAGTATGGATTGGAGAGACCCAAAAATCCACTTTAAGGTTATCAGTTG
ACTGAATAGTACAAGCTATTCCTAGCATTACTGTCCAACTACTATTAATTGAAATATTAGGTGCCCATTTTTGGAATGGCAACAATCACTCACCT
AAATTGTCCACAAATAGCTTTGAGAAGCGATGTTCTGGTCGGGATTGATCCTACCGCTTGAGCACATTGATGAAGGTCTCGTGAGGAACGCGGAT
GTTGGCGAACATGCGCATCTTCTTCTTGCCCTCGGCCTGCTGCTTGAGCAGCTTCATCCGCCGGGTGACATCCCCACCATAAAGCTTGGCTGTCA
CATCCTTGCGATAGGCCTTGATGGTCTCGCGCGCTAGCACCTTGCTGCCCACGCATGCCTGGATTGCGATCTGTACCATCTGCTTTGGAATAAGC
TCCCGGAGTTTGAGAACCATCTGCCGTGCCACGCCCGTGGCCTTGGACACATGGACAATGCGGCAGAGCTCCTCCACGGGCTTGCCGTTCAGATG
GATGTCCAATCGAACCAAGTGCGATGGATGATAGCCGTGGTCCTCGTAGCTGAAACTGGCGTAGCCAGAACTTAACGACTTGAGGCGGTCGTGGA
AGTCCAGGATGATCTCGCTTAACGGCAGTACGTACTTCATTAGCACACGGGTGTCGTCGATGTTCACCGAGCTTTGCTGCAATCCCCGACGCTCC
ACACACAGGCTGATCACCTGGCCAACATACTCCGTGGGCGTGATGATTGTGCCCAAAACCAAGGGCTCATAGTACTCCTTGATGGAATGCGGTTC
CGGGAAGAGGGCTGCATTGGAAATGTCCATTGTATCGCGACCCTGTTGCTTGATCATCTTTGGATTACTCAAGACCAAACGATATGTGACGGAAG
GCGCGGTGATTATGGGCTCAGCGCCATGCTCCTGCTCCAGGCGCTGACAGAAGACCTCCATGTGCAGAAGTCCCAGGAAGCCCAAACGCCAACCT
TGTCCCAAAGCTGGGCTGGAATCAATTTTTACAGTTACCGCTGAGTCATTGAGTACCATTTTGTCGATGGCACTGCGCAGGGCGACATGTTTTGA
CTGGTCGGCGGGAAAAACTCCAGCAAAAACAAGCGGCTGTTGCGGTCGATAGCTTCCTGCGGCGGCGACTGCTTGGTTCTTCAGGTGAATGGTAT
CGCCCACAATGGATTCCTTGCTGTTGCGCATATTGCAAGCAATCAAGCCCACTTGACCAGCGGATACATCCGGAACAGGACACTCGGCTGGTCTC
AACACAGAGATGCTCTTGACGGAATACACCTTCTTGGTGGCTAGCGACTGAATATCCTGATTCTGCTCTAGCTTGCCATTCAGCACATAAATTAG
ATTAAGGGCTCCGCGATACTTGTCGAACCAGCTGTCGAAGATTAGGGCCCGAAAGTCGCTGTCCCGTTGAACTTGTGGTGGCGGCACAGTTTCTA
TGACCCTTTCTAAGACTTCAGATACGCCGGTGCCCAGCTTGGCGGACACGCGCAGCACCTCGTCCGGATCTATGCCAAACAGCAGCTTTAGATCC
TGACAAACCTGATCAGGGTTTGCATGCTTGATGTCTATCTTGTTGAGCACGGGAACCACTGCCAACTGACGCTGCTTGGCTAAGTGATAGTTGGC
CACGGTTTGAGCCTGGACACCATGGCATGCGTCCACCAGGAGTACCACGCCGTCGCAGGCAGCCAGAGATCGCGAAACCTGGGTAATGGGCAAAT
GATTAGCAGAAGAATTAGCAGACTTTTGACATGAAACACACTTCATTGGAAAAATCCACGTGACCAGGAGTGTCAATGAGGTTCAGCAGATAGAG
CTGTCCCTTGTGACGGTGGAAGATCGATGCGGTCTGGGCCTTGACCGTGATCCCACGCTCCCGCTCCACCTGCAGGTTGTCCAGTACCTGGTGCT
GCCCGCCATTACGCGCAATGGCTCCCGTGAGCTCCAGCAACCGGTCAGCCAGCGTGCTCTTGCCGTGATCGACATGCGCAATGATGCTGAAGTTC
CGAATGCGCTCCACCGGCATGTGGGCAAACTCGCGCAACAGATCCGCCTGCGAGGGCTCCTCCGTTTCGCCCTTGACCTGATTGGTGGTGCTCAG
GTTGCGGACGAGTAAGCTCTTTGACCTGGCCACCAGCCAGGCGGAGTGTCGTTTGTCCCCCGGGCGCTGCAGCAGCCAACGGATTGAAATCGCAC
GAATCATGGCTGAATTTACATTTCTTTGCCGGCAAAAAAAAATTGTTACCGCACACCATGTGCGCCGTGTGACCGTATGATGAAAAAATACCGAG
TAGCCGACAATCATGTGTAAGACAGCAGGAAAATACTGTCCATCTTGTGACAAACAGCGCCATCTGTTGGCAATCTACGAAAACCGATGTTTACA
CATGAACAAATATTTACAACTCAATAATCCTTTACTAATTTGTTCTCGGATGCAAATTAAACATATTCTTAAGCGAAAGATCGTAATGCTCCTAG
ATCTCAGATTGCCTATAGGTTTATATTCATAAATAAACAAGTAAGAAAGTCCGAAATATTGAGCTATATATCATAAATATTCTGTTTTTTCAACT
GCTTTCGTGAGGAAGTCATCGCTGCGAGATTCGATTTCTAGAAGCCGAGGTTCTTTTCTTGGAACAGCTTACAATGGTAAATGGTAATTGTAATA
GACCAGCAAGGGAGCTGGAGGAACTGCTGGTTCCAGAAAAAGGGGGTTTGACCTCAGCACAGTCAGAGAAAAAGCCGTTCTCAACGATCTCGATT
TAAGAACTTCGATCTCAAAATCTAGCCAAGATCGAATCATGCTCAGCATACTCAGGTCGAGATCGAACCATTCTCAGATTGCAACTGACTTTGCT
CTTATTTTTCGATCTCTTTCTTGGTTTTTTAACCTTACCCACACATCATCTTCTACAATCTGAAACCCGATACTGCTTCCGTCTAAAATATGTAT
CCAACATAGAGATCGTTTTCGTCTCGAAAAAATAAGTCTTCTTTTCATGAGAATGATTGATGGGATGGTAGGGATTATCCTGGCTGTGTCCCTGT
ACCGATTCCACAAGACCTTGATGCTAGACGTGTTGAGGAGACCATACACACGGACAATACTCAAGTATGGGTTGAACTAGGGATACTTGAGGTTG
TGAGGATCCTTAAGCTCTTTCGACGAACGCTTGACAAATATGTACAAGTAAAACTTTTGTTCTACTAACAATAATGCCAATGTGATTGGAAAAGC
TGATAGTGAAATCTCGCAATGTTACTCTTGTGCTTGCTTGTGTTTTCGAATGCATACGTTGAAT
(SEQ ID NO: 79)

Exon: 3149..2607
Exon: 2548..1181
Exon: 1129..1001
Start ATG: 3149 (Reverse strand: CAT)

Transcript No. : CT3280
ATGATTGTCGGCTACTCGGTATTTTTCATCATACGGTCACACGGCGCACATGGTGTGCGGTAACAATTTTTTTTGCCGGCAAAGAAATGTAAA
TTCAGCCATGATTCGTGCGATTTCAATCCGTTGGCTGCTGCAGCGCCCGGGGACAAACGACACTCCGCCTGGCTGGTGGCCAGGTCAAAGAGCT
TACTCGTCCGCAACCTGAGCACCACCAATCAGGTCAAGGGCGAAACGGAGGAGCCCTCGCAGGCGGATCTGTTGCGCGAGTTTGCCCACATGCCG
GTGGAGCGCATTCGGAACTTCAGCATCATTGCGCATGTCGATCACGGCAAGAGCACGCTGGCTGACCGGTTGCTGGAGCTCACGGGAGCCATTGC
GCGTAATGGCGGGCAGCACCAGGTACTGGACAACCTGCAGGTGGAGCGGGAGCGTGGGATCACGGTCAAGGCCCAGACCGCATCGATCTTCCACC
GTCACAAGGGACAGCTCTATCTGCTGAACCTCATTGACACTCCTGGTCACGTGGATTTTTCCAATGAAGTTTCGCGATCTCTGGCTGCCTGCGAC
GGCGTGGTACTCCTGGTGGACGCATGCCATGGTGTCCAGGCTCAAACCGTGGCCAACTATCACTTAGCCAAGCAGCGTCAGTTGGCAGTGGTTCC
CGTGCTCAACAAGATAGACATCAAGCATGCAAACCCTGATCAGGTTTGTCAGGATCTAAAGCTGCTGTTTGGCATAGATCCGGACGAGGTGCTGC
GCGTGTCCGCCAAGCTGGGCACCGGCGTATCTGAAGTCTTAGAAAGGGTCATAGAAACTGTGCCGCCACCACAAGTTCAACGGGACAGCGACTTT
CGGGCCCTAATCTTCGACAGCTGGTTCGACAAGTATCGCGGAGCCCTTAATCTAATTTATGTGCTGAATGGCAAGCTAGAGCAGAATCAGGATAT
TCAGTCGCTAGCCACCAAGAAGGTGTATTCCGTCAAGAGCATCTCTGTGTTGAGACCAGCCGAGTGTCCTGTTCCGGATGTATCCGCTGGTCAAG
TGGGCTTGATTGCTTGCAATATGCGCAACAGCAAGGAATCCATTGTGGGCGATACCATTCACCTGAAGAACCAAGCAGTCGCCGCCGCAGGAAGC

FIGURE SHEET 29

TATCGACCGCAACAGCCGCTTGTTTTGCTGGAGTTTTCCCGCCGACCAGTCAAAACATGTCGCCCTGCGCAGTGCCATCGACAAAATGGTACT
CAATGACTCAGCGGTAACTGTAAAAATTGATTCCAGCCCAGCTTTGGGACAAGGTTGGCGTTTGGGCTTCCTGGGACTTCTGCACATGGAGGTCT
TCTGTCAGCGCCTGGAGCAGGAGCATGGCGCTGAGCCCATAATCACCGCGCCTTCCGTCACATATCGTTTGGTCTTGAGTAATCCAAAGATGATC
AAGCAACAGGGTCGCGATACAATGGACATTTCCAATGCAGCCCTCTTCCCGGAACCGCATTCCATCAAGGAGTACTATGAGCCCTTGGTTTTGGG
CACAATCATCACGCCCACGGAGTATGTTGGCCAGGTGATCAGCCTGTGTGTGGAGCGTCGGGGATTGCAGCAAAGCTCGGTGAACATCGACGACA
CCCGTGTGCTAATGAAGTACGTACTGCCGTTAAGCGAGATCATCCTGGACTTCCACGACCGCCTCAAGTCGTTAAGTTCTGGCTACGCCAGTTTC
AGCTACGAGGACCACGGCTATCATCCATCGCACTTGGTTCGATTGGACATCCATCTGAACGGCAAGCCCGTGGAGGAGCTCTGCCGCATTGTCCA
TGTGTCCAAGGCCACGGGCGTGGCACGGCAGATGGTTCTCAAACTCCGGGAGCTTATTCCAAAGCAGATGGTACAGATCGCAATCCAGGCATGCG
TGGGCAGCAAGCTTTATGGTGGGGATGTCACCCGGCGGATGAAGCTGCTCAAGCAGCAGGCCGAGGGCAAGAAGAAGATGCGCATGTTCGCCAAC
ATCCGCGTTCCTCACGAGACCTTCATCAATGTGCTCAAGCGGTAG
(SEQ ID NO: 80)

Start ATG: 1 (Reverse strand: CAT)

MIVGYSVFFHHTVTRRTWCAVTIFFCRQRNVNSAMIRAISIRWLLQRPGDKRHSAWLVARSKSLLVRNLSTTNQVKGETEEPSQADLLREFAHMP
VERIRNFSIIAHVDHGKSTLADRLLELTGAIARNGGQHQVLDNLQVERERGITVKAQTASIFHRHKGQLYLLNLIDTPGHVDFSNEVSRSLAACD
GVVLLVDACHGVQAQTVANYHLAKQRQLAVVPVLNKIDIKHANPDQVCQDLKLLFGIDPDEVLRVSAKLGTGVSEVLERVIETVPPPQVQRDSDF
RALIFDSWFDKYRGALNLIYVLNGKLEQNQDIQSLATKKVYSVKSISVLRPAECPVPDVSAGQVGLIACNMRNSKESIVGDTIHLKNQAVAAAGS
YRPQQPLVFAGVFPADQSKHVALRSAIDKMVLNDSAVTVKIDSSPALGQGWRLGFLGLLHMEVFCQRLEQEHGAEPIITAPSVTYRLVLSNPKMI
KQQGRDTMDISNAALFPEPHSIKEYYEPLVLGTIITPTEYVGQVISLCVERRGLQQSSVNIDDTRVLMKYVLPLSEIILDFHDRLKSLSSGYASF
SYEDHGYHPSHLVRLDIHLNGKPVEELCRIVHVSKATGVARQMVLKLRELIPKQMVQIAIQACVGSKLYGGDVTRRMKLLKQQAEGKKKMRMFAN
IRVPHETFINVLKR*
(SEQ ID NO: 81)

Name: EF-Tu-like
Classification: translation_factor
Gene Symbol: waw
FlyBase ID: FBgn0024182

Celera Sequence No. : 142000013384340
TTAATATTATAATCGCATTCAAACGCATTTCGTTTCGTTTGTTATGCGCCCACACGCAGCACTTATGTATAGCATTTATTATGTAGGACTTATAG
CGAAAACAAAAAAAATTTCCTATGAATATACAAGAAATTAATCAGTTGTTCTTCAGATAATTGATAACTATCCTAGTGGGCTTTTCTCTGGCCCC
ACCTCCTCTCCACGGATTTTACTTGAGAATTGTAGTTTGCTTGGCCAGAACTGAATTGGAGTTCAGCTTCAAAAAAAAATTTAAAATAAGATAG
GAAGCTGCGAGATCCGATCCGCCTGGGCACCTTGCTCGTATCGTCCTCTTCCTGTCCTGGTGATTAGTTCTACATGTGTGTTCTCTTACTTTCAC
CACAATTGATTGCAATTGCGATGATTGATGGTGACTCATCCAGGCTATCCACAGATTTCGGTTATATACGTAAAACGCTGTCGCATACGTATTTT
CTTTAAGTCTAAACTTATGTTTACCGTGTGGTAAGCTCCCTTGCTTACCATCTAGATGTTATTGAGGTTTCTGGGATACTTCGGGATCGAAATCA
TCTATTCGCTATCTCTGCTTGTTTGTTTCTGGTGTGCTCGCTTAACTTACAAAGTAGTTTAAACGTAAATCTGCAAGAAAATGTGCGCAGTTTTG
AAAACTATTCAACGATTCAACAACGACTCACTTACCTTATATTTAAATATTTGGCTCTTGATTTTGTTGTTGCTGCGGTGTTTTGTTTGTTGTT
TGTTGTTGTTGCTTCGCTGTGGGTGCTTTTCGCTTCGGTGTCCAGGCTTTCTCGAGTTTAGTTTAAATGCGGCAAGCACACGAAAATAAATGTGA
TGAAAAATGACTTGAACGAATAACCAACAAATTCGAAAAGAAGCTCGTGGCTATTTGTGAGTGTGGCGTGTTTAGTGTTGTAGTGTTTCATCATC
GATTTGAACCATTTTAGTTGAAATTTTTTTTTGGCACGGGCAGCGCTAGCTTAGAAGGGCATATCCAATTCGTTGTTCTCCTCCTCCTCGATCAA
GTCATCAACATCGAATTCGCTGGGCGAGAAGCTGGTCTGTTGCTGCTGCGGTTGCAGCTGTTGCTGCTGCTGCTGCATTTGGATACGTTGCGGCT
GCTGCACGATTATGCTGTTGCGTGTGCATGTTGTCACCTTGGCGCCTAACATACGTGCATTGGCCAACGCGGCCGTCTTGAGAGGATTACGCAGA
TGTGTCGCCTGGGAGGCTAACGAAGATGTGGCGGCTGATGCTGTGGACGATGCGGCGTTAATTGTGCCCGTGGTACCGGGATCATTGTAACGTGG
ACGCTTATTCTGCAGCTTGGTTGCCCAGCATTCGGTGGCCCGGCGACGGGCATTGGCACAGATATTATCCCCGGATGAGGACGATGAGGAGGAGG
TGGAGGGAGCTGCTGCCGCCGATGAGGTGGAGGCCGGATTGGCCTTCTCCCCATTAAACATTATATGGCGGCGCTCTTCCTGGGTTTGCTTCATC
ATCTGGTGATAGTTGACCATCTGTTTCAGACGAGGCATACTATCAACTGTGCTGGACAAGATGGTCGCGGGTGCTGATGTTTGGTCATTCGACGA
TGATTTAGAGTGCGCCGCTGTTGTATTAACAAAGATATTATCAAGGGAAGCAGTCTTGTTATCGGCCAAGACATTTTTCTCCAGTTCGTGGGGAT
CACCGCCGGCTTGCAGACGCTGCTTTTGACGCAGATGCTGCAGCTCCTCCGCCGAACGTTGCTTGCGGAAATCAAAGACCAGCGGGTATATGTGC
TGGATAGCCGATTCAACGTGGTTTACGCTAGCCGCTAAATAAATATGACGAAAATTAGAATTAGAATTAGTTTTAGTACAGTTTGAGGATAACAA
CAGTACTCACCGGTGACTGTTACGCTGCCGGTGGAGAAGATCTTCAGGGTGGCCTTTGGATCGGGATCGCGCATCTTGTAAGTCACTCCAGGATG
CAGCTCGGGCTCGTAGCTGGCGTTCTCGCGATGGCGCTCCGAAAAGTTGACGATCTTGATGGCCCACGGCATGCTGCAGGTGCCCAGTACGTTGA
CAATGCGAAAGTTGAGGAAACGAGTGGGAAATCCCAGCTTGCCAAGGCATCTGGCATAGCGGCGTGCAGCGACCTTGGCCTAAAAAGATCATCAA
CTATTGAGATAACAAAAATGTATAATTTAATGCTAAATCATACCATTGACTCGGAAGTGGCACCAGTGCAGGTAATCCTCCCCGACGACCAAATC
GAGGCAGTGGTGTATGGATGGCGGAGCTTCATTGTCACCATTCCGTTCTCGCGACGGTACTCCACATTTGATCCCTGCAGCGCAATTTCGCGCAG
CTTCAGGTGACAGCCGACGCTAAACGAGCAGACCACATTGTTTATCACAATGTCCAGCTCGTGCTCATTATCAGCAATTGGCTGGTGAAGGTCAA
TGGGTTTGGCATTATTGCTGCTCTCTTCTTCGTCTTCAGCGACTTCCTTTTTCTCCTCGTCATCGTCATCAATCACAGTTATCGACTGCATGACC
TCCTCCTCCAATAGATCCATTTTGGCTGTGATCAGACCATTGCCATTGCTGGCGACGGTCGGCAGATTAGCCTTATTTTCGCTGCTAGTAAGGAA
CATATTTTTACTGCCGGTTGCCAGAACAATGGTATCCCCGTTGGCAAGTTTCCTTTGCAAACTGGGTCCGCCGGCCGTTTGCATTTTGCTGAATT
GCGAAAAATAGCGAACGGTACCGGCTGTTGAGGCTGTGCCAGATGAACCACCGACGACTTGTCCGCTCATTCTTCCGGTGGACGCCACTCCCGCC
ATTTGGCGATTGGTCATGAATGTGGAGGAGGGCGTTAGGTATACACGTGGGGCATTGGCCAGCACCGCCGAGGATACGACGCCGCCGGAGGTCAC
TACACCAACTCCGGAACCGCTGCTGGCCGCTTTAAGGCCGCCGTTCAAATTGGCCACCGGTATGCTGACCATATCGTTTTGCATCAGCTTGTGCT
TTCGATTCCCCTTCAACGAGCGCTGACTGGCCTTCTCCAGCTGCTTAATCTTGATCAGATAATGCTCGCGCTGCAAACGCAACTGACGTTTACAG
TCCTCCCTATATTCCTTCAAGAATCGTTCGTATTCCAAGCGCTGTTTCTCCTTTTTCTGGCGCAATTTACGTTCGCGTTTTACGCGATTTTGCTG
ACGACGATGCTGCTCCTTCTGTTGGCGCAATTTTTCTAGGACAAACTGTTTCTGTTGCTCAAAGAGGTGGCGCTTTCGCTCTCGCTGCTCCTCCA
GTTCTTTCTTCTGTTGCAACTGTCGTAGCTGTAGGAAGACTTTATCCTGTTGCAACTGTCGCTCCTGTGGCAAGTGTTTCTCCTGTTGCAATTGT
TTCTCCTGTTGCAAGAGTTTCTCCTGTTGCAAGAGTTTCTCCTGTTGCAAGAGTTTCTGCTGTTGCAAGAGTTTCTCCTGTTGCAAGAGTTTCTG
CTGTTGCAAGAGTTTCTGCTGTTGCAACCGTTTCTCCTGTTGCAACCGTTTCTCCTGTTGCAACCGTTTCTCCTGTTGCAACCGTTTCTCCTGTT
GCAACCGTTTCTCCTGTTGCAAGAGTTTCTCCTGTTGCAAAAGTTTCTCCTGTTGCAACCGTTTCTCCTGTTGCTCTTGTGGAAAGAATTTCTGC
AAAAGTAGTTTCAGATACTCATATAGCAACAGTTGCTCCTTTGAAAAGAATTTCTCCTGGTGCCAGAATACCACCAGTTGCAACTTTTGATATTT

FIGURE SHEET 30

TTTTAAATGTTTCTGTTGCTGCTTCAGTTGCAGGTCCTGTTCTGGTTGGCCTTCCTCATCAATACTGCTGTATACGTCTTCCAGTTTGTAAGCTC
CAAATACCTTATAGAGCTGTATGCTAAGGTCCAAACTAGATTTATCATCCCCTAAAGGATTTGTTACGAATTTCAAGAACTTCCTTTCCTTTGAG
AAGATAAATGGTTTATAATCCTCCTCAGAATCACAAATGTGATCGTCGTAATAAGAAGCTGGATCCTGATCGTCGTAATAAGGAGCTGGATCCTG
ATCGTTGTAATAAGGATGTGGATCTTGATCGGTTCCGAATTCAGGAGCTGGATCTTGATCGACTCCGCCTTCAGGAGCTAGATCTTGATCGGATT
CGCCTTCAGGAGCTGGATCTTGATCGACTTCGCCTTCAGGAGCTGGATCTTGATCGACTCCGCCTTCAGGAGCTGGATCTTGATCGACTCCGCCT
TCAGGAGCTGGATCTTGATCGGCTTCGCCTTCAGGAGCTGGATCTTGATCGGTTTCGCCTTCAGGAGCTGGATCCTGGGCAGATTCCTCAGAACT
TGAAGATGATTCGAAATCGGAATGGGAATCGGAATCGGAATCTAAATCTAAATTTGAATCTGAATCTGAATTTGAATCTGTATCGAAACTTGAAC
TATCTGAGTCTTCTTCGTCAGAGCATTCGCTTTCCGTATCTTCACGTTTTTCCTCCTCAGATTTGTCTTCCTCACTCTGCAAGTTTGGTTTAAAT
TTCTTAGAGTCTGTACAATCAAAAGGCCATTTACGCTTTAAGGATCTGCGACTTCCCAGAGACGATAAATGTGAACGTGGGTCTCCTTTGTCACC
GTCCAATAATGGTTTCTTCGAATACGAAGAATTCCCAGTGCCTAACGATTTTCGCTTATTCTGTTGCTTGTCTGGCGAATGATCGCGTCTATCAG
AAGAAGTATGTTCAGCCGGCGACTGTTGTTCGACGTCGTCGCTTTCTTCCTTCTGTTCGTCTGTAATTTCCTCTGACGACTCCTGTTGGCTTTGG
TCGCTTTTTCCTCGCGTTCGGTAGAAGTTTCTCGCCGGCGCGATAGCCACCCAGTAACTGGATCGATTAAGTAGTCCGAGTCCCCAGAAGACGA
TTCCTCATCTGAAGCTTGTCGCGACTCGCTTTCAGAGTCTTGTCTCTCCGGCGAAGATGACTCTAAAGATGAATCCGATTTTGATTTGGCCTAT
TGATTGGCTGATTGAATGGCTGATTGATTGGGTTATGGCGACGATCGTCGCTATCAACTTCTGATTCTCCTAAACGAGGGAGATGTACCTGACAA
GCGTAGGATCGTAAACGGGTATATATGTTTCTTTTTCTAGCGGCCTCTTCCTCATCAGATTCAGGATATTGGTACTCTCGATTCAAGGCCTGATA
CTCGTGATTTGAGTCCTGGTATTCGTGATTCCAAGCCTGGTACTCGTGATTTGAGTCTTGGTTGACGTGATTCAAATCCTGGTACTCGTCACTTG
AGTCCTGATCGCCGTGATTCAACTCCTGGTACTCGTCATTTGAGTCCTGGTTGCTGTGATTCAACTCCTGGTACTCGTCATTTGAGTCCTGGTTG
CCGTGATTTGATTCCTGGTACTCGTCATTTGAGTCCTGGTTGCCGTGATTCAACTCCTGGTACTCGTCATTTGAGTCCTGATCGCCGTGATTCAA
CTCCTGGTACTCGGTATTCAAGTGCTGGTACTCTTGGTTTGAAACCTGGTACTCGTTATTAGACTCCTGGTACTCGCGATTAACTTGATTCAAGT
CCTGGTTACCGATATTCAAGTCCTGGTACCCGGGATTCAAGTCAGATTGTGCATATTCCCTTGTTCTTCCTCTTGATGAAGTTGAATATTCTTGG
TGCAGCTGTTCGTCCTCGCTATTAGAAGAACTTAAGCGATCTGCGTATGATGAAAAGAATTTGTTTAAAAAACATTTTTATAATTCTCACATTAT
TTTACCACTAGAATTGCAGGCATCCCCGTACGACTCGTTACCGCTGCTGTTGGCTTCGTTCTTCTCAACTTCTTCGTTCGAAAACTGGTCAGCTT
CGTTGCGACTTGAAGTATCTTTACCAACGTCAGAGCCTTGCTCACGATTTCCGATGGTGCTTCCGCTTGATGAAGTTGAATATTCTTGGTTAAGC
TGTTCGTCCTCGCTATGAGAGGAACTTAAACGATCTGCGTATGTTGAAAAGAATTTGTGTAAAAAACATTTATATAAATTAACAATTCATTTTAC
CTCTAGAATTGCGAGCATCCCCGCCCGACTCGTTACAGCTGCTGTTGGCTTCGTTCTTCTCAACTTCTTCGCTCGAAAACTGGTCAGCTTCGTTG
GGATTTAGAGTATCTTTACCAATGTCAGGTCCTTGCTCACAATCACCGATGGCTCTTGGATTGGGGGATTGATTCGGCGATTGGTTCTCCTTATC
CGAATCTTCGTCCGGATGTTCAACCGGATGTTCCGGAAACAAATCCTCGTTCCTTAAGTCTCTAGCTACTTGGTATTCTTCAAGTATTCGAGTCG
GGGAACCATCCCCCTTTTTGACGCTACAGTTGTTTTAGGGAGACGAAGTTCAATTATATTTCATTGGGTATTTATGCTTACTGTTTGTGTGACTG
TGGCGGTGTGGATATGCGGCTCTTTATATCTACTGTATATCGTGTAATAGTTCTTTTTTTTTCTCTGTATGCCTACTTACGCACTGCCCATCGTT
AAAAAAATATTTCTTGTTATCTTTTTGGGTTTCTTGATAGGACTCTTGCTCTGCGTTTTCTTGCTAGCTTCTTAATTATATTTAATTGTATATAA
GGCTAAAGGTGATTCTTCCTTGGTGTTGTATTACATTCTTTCCATTGTTTCGTTCATGTGGATGTGTATGTATGTGTTTGTATGTGAGTATGTTT
GCACTTAAGGCCAAAAAATACTTTTTTATGTGTGATTTTGTATTAGAATTAATGTTTTCTTAGTGTTCTAGTTGTTGGGTTTGCTGGTTCTCTAA
TTCTATCTACTATGTTTATGATTATGTCTAGTCTTCCGTTCTTTTCTCCTGGTTAAATTTGCTTGTAGTTTTTAGTTGTTCCGTTTAGCAGTCTG
CAAGTAGAAGAGAATATAATAAAAGTTAATAATCGTAAAGTTGACATTTGGGAAAATGAAAACATGCAAATTGCCTTGATAAATACAAATGCATT
TATTAATTGGTTTGATAGCGCACCTAATAAACACGATGACACTATTTAATCTAATTTCCACTTTTATATATCAACCCGACCCCCGACAACCGGCA
CAAGTGAAGGGTCTAGGTCTAACCCTCTGGGAGTTTTCGTGGAATATTAGTAGTTCCTGTCATGTTAATAGAGATGGAACTCTGAGCCGGCCCTT
ATAGAGTGGCATGATTCACGAAGACTCACGAAGACTCACGCTTTGCCTACCCAAAAAAAAAAAAATAATACGTCTTATACATTTTTAAAATGTAA
TTTTTAAAACAAAAAAAATGAGAAGAGATCATGACCTACTTATAGTAGTTTTACAAACTAAAATATTGTATTTTACAGACGACTTCACTGTTAAC
GGGAGCTGCGTTTAACAGAGAGCGCTGTTCGTTAACAGTCCTTTTTATTAGGATCGCCTAAGTGCGCTGACCTTAACATAGATTTTCGCATGCCT
GCTAAGAGTATGCACGAAGAAGGGGCGGAGGAAAACGAAAAGGCGA
(SEQ ID NO: 82)

Exon: 6551..6541
Exon: 6388..6081
Exon: 6019..5801
Exon: 5740..2229
Exon: 2169..1911
Exon: 1839..1001
Start ATG: 6551 (Reverse strand: CAT)

Transcript No. : CT3310
ATGGGCAGTGCCGTCAAAAAGGGGGATGGTTCCCCGACTCGAATACTTGAAGAATACCAAGTAGCTAGAGACTTAAGGAACGAGGATTTGTTTCC
GGAACATCCGGTTGAACATCCGGACGAAGATTCGGATAAGGAGAACCAATCGCCGAATCAATCCCCCAATCCAAGAGCCATCGGTGATTGTGAGC
AAGGACCTGACATTGGTAAAGATACTCTAAATCCCAACGAAGCTGACCAGTTTTCGAGCGAAGAAGTTGAGAAGAACGAAGCCAACAGCAGCTGT
AACGAGTCGGGCGGGGATGCTCGCAATTCTAGAGATCGTTTAAGTTCCTCTCATAGCGAGGACGAACAGCTTAACCAAGAATATTCAACTTCATC
AAGCGGAAGCACCATCGGAAATCGTGAGCAAGGCTCTGACGTTGGTAAAGATACTTCAAGTCGCAACGAAGCTGACCAGTTTTCGAACGAAGAAG
TTGAGAAGAACGAAGCCAACAGCAGCGGTAACGAGTCGTACGGGGATGCCTGCAATTCTAGTGATCGCTTAAGTTCTTCTAATAGCGAGGACGAA
CAGCTGCACCAAGAATATTCAACTTCATCAAGAGGAAGAACAAGGGAATATGCACAATCTGACTTGAATCCCGGGTACCAGGACTTGAATATCGG
TAACCAGGACTTGAATCAAGTTAATCGCGAGTACCAGGAGTCTAATAACGAGTACCAGGTTTCAAACCAAGAGTACCAGCACTTGAATACCGAGT
ACCAGGAGTTGAATCACGGCGATCAGGACTCAAATGACGAGTACCAGGAGTTGAATCACGGCAACCAGGACTCAAATGACGAGTACCAGGAATCA
AATCACGGCAACCAGGACTCAAATGACGAGTACCAGGAGTTGAATCACAGCAACCAGGACTCAAATGACGAGTACCAGGAGTTGAATCACGGCGA
TCAGGACTCAAGTGACGAGTACCAGGATTTGAATCACGTCAACCAAGACTCAAATCACGAGTACCAGGCTTGGAATCACGAATACCAGGACTCAA
ATCACGAGTATCAGGCCTTGAATCGAGAGTACCAATATCCTGAATCTGATGAGGAAGAGGCCGCTAGAAAAAGAAACATATATACCCGTTTACGA
TCCTACGCTTGTCAGGTACATCTCCCTCGTTTAGGAGAATCAGAAGTTGATAGCGACGATCGTCGCCATAACCCAATCAATCAGCCATTCAATCA
GCCAATCAATAGGCCAAATCAAAAATCGGATTCATCTTTAGAGTCATCTTCGCCGGAGAGACAAGACTCTGAAAGCGAGTCGCGACAAGCTTCAG
ATGAGGAATCGTCTTCTGGGGACTCGGACTACTTAATCGATCCAGTTACTGGGTGGCTATCGCGCCGGCGAGAAACTTCTACCGAACGCGAGGAA
AAAAGCGACCAAAGCCAACAGGAGTCGTCAGAGGAAATTACAGACGAACAGAAGGAAGAAAGCGACGACGTCGAACAACAGTCGCCGGCTGAACA
TACTTCTTCTGATAGACGCGATCATTCGCCAGACAAGCAACAGAATAAGCGAAAATCGTTAGGCACTGGGAATTCTTCGTATTCGAAGAAACCAT
TATTGGACGGTGACAAAGGAGACCCACGTTCACATTTATCGTCTCTGGGAAGTCGCAGATCCTTAAAGCGTAAATGGCCTTTTGATTGTACAGAC
TCTAAGAAATTTAAACCAAACTTGCAGAGTGAGGAAGACAAATCTGAGGAGGAAAAACGTGAAGATACGGAAAGCGAATGCTCTGACGAAGAGA
CTCAGATAGTTCAAGTTTCGATACAGATTCAAATTCAGATTCAGATTCAAATTTAGATTTAGATTCCGATTCCGATTCCCATTCCGATTTCGAAT CATCTTCAAGTTCTGAGGAATCTGCCCAGGATCCAGCTCCTGAAGGCGAAACCGATCAAGATCCAGCTCCTGAAGGCGAAGCCGATCAAGATCCA
GCTCCTGAAGGCGGAGTCGATCAAGATCCAGCTCCTGAAGGCGGAGTCGATCAAGATCCAGCTCCTGAAGGCGAAGTCGATCAAGATCCAGCTCC
TGAAGGCGAATCCGATCAAGATCTAGCTCCTGAAGGCGGAGTCGATCAAGATCCAGCTCCTGAATTCGGAACCGATCAAGATCCACATCCTTATT
ACAACGATCAGGATCCAGCTCCTTATTACGACGATCAGGATCCAGCTTCTTATTACGACGATCACATTTGTGATTCTGAGGAGGATTATAAACCA
TTTATCTTCTCAAAGGAAAGGAAGTTCTTGAAATTCGTAACAAATCCTTTAGGGGATGATAAATCTAGTTTGGACCTTAGCATACAGCTCTATAA
GGTATTTGGAGCTTACAAACTGGAAGACGTATACAGCAGTATTGATGAGGAAGGCCAACCAGAACAGGACCTGCAACTGAAGCAGCAACAGAAAC
ATTTAAAAAAATATCAAAAGTTGCAACTGGTGGTATTCTGGCACCAGGAGAAATTCTTTTCAAAGGAGCAACTGTTGCTATATGAGTATCTGAAA
CTACTTTTGCAGAAATTCTTTCCACAAGAGCAACAGGAGAAACGGTTGCAACAGGAGAAACTTTTGCAACAGGAGAAACTCTTGCAACAGGAGAA
ACGGTTGCAACAGGAGAAACGGTTGCAACAGGAGAAACGGTTGCAACAGGAGAAACGGTTGCAACAGGAGAAACGGTTGCAACAGCAGAAACTCT
TGCAACAGCAGAAACTCTTGCAACAGGAGAAACTCTTGCAACAGCAGAAACTCTTGCAACAGGAGAAACTCTTGCAACAGGAGAAACTCTTGCAA
CAGGAGAAACAATTGCAACAGGAGAAACACTTGCCACAGGAGCGACAGTTGCAACAGGATAAAGTCTTCCTACAGCTACGACAGTTGCAACAGAA
GAAAGAACTGGAGGAGCAGCGAGAGCGAAAGCGCCACCTCTTTGAGCAACAGAAACAGTTTGTCCTAGAAAAATTGCGCCAACAGAAGGAGCAGC
ATCGTCGTCAGCAAAATCGCGTAAAACGCGAACGTAAATTGCGCCAGAAAAAGGAGAAACAGCGCTTGGAATACGAACGATTCTTGAAGGAATAT
AGGGAGGACTGTAAACGTCAGTTGCGTTTGCAGCGCGAGCATTATCTGATCAAGATTAAGCAGCTGGAGAAGGCCAGTCAGCGCTCGTTGAAGGG
GAATCGAAAGCACAAGCTGATGCAAAACGATATGGTCAGCATACCGGTGGCCAATTTGAACGGCGGCCTTAAAGCGGCCAGCAGCGGTTCCGGAG
TTGGTGTAGTGACCTCCGGCGGCGTCGTATCCTCGGCGGTGCTGGCCAATGCCCCACGTGTATACCTAACGCCCTCCTCCACATTCATGACCAAT
CGCCAAATGGCGGGAGTGGCGTCCACCGGAAGAATGAGCGGACAAGTCGTCGGTGGTTCATCTGGCACAGCCTCAACAGCCGGTACCGTTCGCTA
TTTTTCGCAATTCAGCAAAATGCAAACGGCCGGCGGACCCAGTTTGCAAAGGAAACTTGCCAACGGGGATACCATTGTTCTGGCAACCGGCAGTA
AAAATATGTTCCTTACTAGCAGCGAAAATAAGGCTAATCTGCCGACCGTCGCCAGCAATGGCAATGGTCTGATCACAGCCAAAATGGATCTATTG
GAGGAGGAGGTCATGCAGTCGATAACTGTGATTGATGACGATGACGAGGAGAAAAAGGAAGTCGCTGAAGACGAAGAAGAGAGCAGCAATAATGC
CAAACCCATTGACCTTCACCAGCCAATTGCTGATAATGAGCACGAGCTGGACATTGTGATAAACAATGTGGTCTGCTCGTTTAGCGTCGGCTGTC
ACCTGAAGCTGCGCGAAATTGCGCTGCAGGGATCAAATGTGGAGTACCGTCGCGAGAACGGAATGGTGACAATGAAGCTCCGCCATCCATACACC
ACTGCCTCGATTTGGTCGTCGGGGAGGATTACCTGCACTGGTGCCACTTCCGAGTCAATGGCCAAGGTCGCTGCACGCCGCTATGCCAGATGCCT
TGGCAAGCTGGGATTTCCCACTCGTTTCCTCAACTTTCGCATTGTCAACGTACTGGGCACCTGCAGCATGCCGTGGGCCATCAAGATCGTCAACT
TTTCGGAGCGCCATCGCGAGAACGCCAGCTACGAGCCCGAGCTGCATCCTGGAGTGACTTACAAGATGCGCGATCCCGATCCAAAGGCCACCCTG
AAGATCTTCTCCACCGGCAGCGTAACAGTCACCGCGGCTAGCGTAAACCACGTTGAATCGGCTATCCAGCACATATACCCGCTGGTCTTTGATTT
CCGCAAGCAACGTTCGGCGGAGGAGCTGCAGCATCTGCGTCAAAAGCAGCGTCTGCAAGCCGGCGGTGATCCCCACGAACTGGAGAAAAATGTCT
TGGCCGATAACAAGACTGCTTCCCTTGATAATATCTTTGTTAATACAACAGCGGCGCACTCTAAATCATCGTCGAATGACCAAACATCAGCACCC
GCGACCATCTTGTCCAGCACAGTTGATAGTATGCCTCGTCTGAAACAGATGGTCAACTATCACCAGATGATGAAGCAAACCCAGGAAGAGCGCCG
CCATATAATGTTTAATGGGGAGAAGGCCAATCCGGCCTCCACCTCATCGGCGGCAGCAGCTCCCTCCACCTCCTCCTCATCGTCCTCATCCGGGG
ATAATATCTGTGCCAATGCCCGTCGCCGGGCCACCGAATGCTGGGCAACCAAGCTGCAGAATAAGCGTCCACGTTACAATGATCCCGGTACCACG
GGCACAATTAACGCCGCATCGTCCACAGCATCAGCCGCCACATCTTCGTTAGCCTCCCAGGCGACACATCTGCGTAATCCTCTCAAGACGGCCGC
GTTGGCCAATGCACGTATGTTAGGCGCCAAGGTGACAACATGCACACGCAACAGCATAATCGTGCAGCAGCCGCAACGTATCCAAATGCAGCAGC
AGCAGCAACAGCTGCAACCGCAGCAGCAACAGACCAGCTTCTCGCCCAGCGAATTCGATGTTGATGACTTGATCGAGGAGGAGGAGAACAACGAA
TTGGATATGCCCTTCTAA
(SEQ ID NO: 83)

Start ATG: 1 (Reverse strand: CAT)

MGSAVKKGDGSPTRILEEYQVARDLRNEDLFPEHPVEHPDEDSDKENQSPNQSPNPRAIGDCEQGPDIGKDTLNPNEADQFSSEEVEKNEANSSC
NESGGDARNSRDRLSSSHSEDEQLNQEYSTSSSGSTIGNREQGSDVGKDTSSRNEADQFSNEEVEKNEANSSGNESYGDACNSSDRLSSSNSEDE
QLHQEYSTSSRGRTREYAQSDLNPGYQDLNIGNQDLNQVNREYQESNNEYQVSNQEYQHLNTEYQELNHGDQDSNDEYQELNHGNQDSNDEYQES
NHGNQDSNDEYQELNHSNQDSNDEYQELNHGDQDSSDEYQDLNHVNQDSNHEYQAWNHEYQDSNHEYQALNREYQYPESDEEEAARKRNIYTRLR
SYACQVHLPRLGESEVDSDDRRHNPINQPFNQPINRPNQKSDSSLESSSPERQDSESESRQASDEESSSGDSDYLIDPVTGWLSRRRETSTEREE
KSDQSQQESSEEITDEQKEESDDVEQQSPAEHTSSDRRDHSPDKQQNKRKSLGTGNSSYSKKPLLDGDKGDPRSHLSSLGSRRSLKRKWPFDCTD
SKKFKPNLQSEEDKSEEEKREDTESECSDEEDSDSSSFDTDSNSDSDSNLDLDSDSDSHSDFESSSSSEESAQDPAPEGETDQDPAPEGEADQDP
APEGGVDQDPAPEGGVDQDPAPEGEVDQDPAPEGESDQDLAPEGGVDQDPAPEFGTDQDPHPYYNDQDPAPYYDDQDPASYYDDHICDSEEDYKP
FIFSKERKFLKFVTNPLGDDKSSLDLSIQLYKVFGAYKLEDVYSSIDEEGQPEQDLQLKQQQKHLKKYQKLQLVVFWHQEKFFSKEQLLLYEYLK
LLLQKFFPQEQQEKRLQQEKLLQQEKLLQQEKRLQQEKRLQQEKRLQQEKRLQQEKRLQQQKLLQQQKLLQQEKLLQQQKLLQQEKLLQQEKLLQ
QEKQLQQEKHLPQERQLQQDKVFLQLRQLQQKKELEEQRERKRHLFEQQKQFVLEKLRQQKEQHRRQQNRVKRERKLRQKKEKQRLEYERFLKEY
REDCKRQLRLQREHYLIKIKQLEKASQRSLKGNRKHKLMQNDMVSIPVANLNGGLKAASSGSGVGVVTSGGVVSSAVLANAPRVYLTPSSTFMTN
RQMAGVASTGRMSGQVVGGSSGTASTAGTVRYFSQFSKMQTAGGPSLQRKLANGDTIVLATGSKNMFLTSSENKANLPTVASNGNGLITAKMDLL
EEEVMQSITVIDDDDEEKKEVAEDEEESSNNAKPIDLHQPIADNEHELDIVINNVVCSFSVGCHLKLREIALQGSNVEYRRENGMVTMKLRHPYT
TASIWSSGRITCTGATSESMAKVAARRYARCLGKLGFPTRFLNFRIVNVLGTCSMPWAIKIVNFSERHRENASYEPELHPGVTYKMRDPDPKATL
KIFSTGSVTVTAASVNHVESAIQHIYPLVFDFRKQRSAEELQHLRQKQRLQAGGDPHELEKNVLADNKTASLDNIFVNTTAAHSKSSSNDQTSAP
ATILSSTVDSMPRLKQMVNYHQMMKQTQEERRHIMFNGEKANPASTSSAAAAPSTSSSSSSSGDNICANARRRATECWATKLQNKRPRYNDPGTT
GTINAASSTASAATSSLASQATHLRNPLKTAALANARMLGAKVTTCTRNSIIVQQPQRIQMQQQQQQLQPQQQQTSFSPSEFDVDDLIEEEENNE
LDMPF*
(SEQ ID NO: 84)

Gene Symbol: Trf2
FlyBase ID: FBgn0026758

Celera Sequence No. : 142000013384055
TATTTTTTTTTTTAACATAATTTTGAATAGCATTAAAATTATTAGCTACAAATGAATAAAAAACGAGCGGGGGTGGGGGAAACAGAGGCTGCG
GGGCAGCTGGAAAAAAAATTAGTGCGAAGGACTAGAAGTAAAGGAAAGAAACGGGCGTACCATCCTTATGTCGGGGGAAGCCCTCTGGAACCCCC
ATTCTATCCCGTCCAGCACAAATGCGCATAATGAGCTCTGGTCAGCCAGCCTAGACGGCTGTGGGAGGTTGCCATCGCAGAGATTTACGCGCGAC
AAGTTTTTCTTGCCCTTTTCCACAACGTAATTCTTTTTCATGCCCTATCTATAGAATTTTGGGTGTATGCCATTTTGTATCAAAATAAAGGGTAT
GTCTTAGATTTTGATACTATATGTTACAACAAAATATGACACACCACTTATATGATGGAGATATATATTTATTCCTAGCATTTCATTAAAGTGTA
TAGTCTTTTAAAAATGTAGAGTAGAGTATTGGAAAAGTAGCTCAACCCGTCTTCTATTTTAGGTAACATTTTTTGTAGACTCGCAACATCCAGCT

FIGURE SHEET 32

AAACACTTTTCAGTTGATATCGCAAATCCTTTTCGCTGGCGCTTACATAATGATATGTGGCCGCAGATGCCAAGGGAGGGAACATTTAAAAAAAA
TGCATTTAAAAATAAAATGAGAAGGAAGTAGCGTCTGCTGTTTGCCTTTCTCCATTGAATATTGAGAATATGAATTAAATATAAACCTGCAGCAG
GATAATCATAAGCAAATCACTATATGCAATTAGGGAAATAGTTTAAACATAATAAACTAAAATCTATAAGTGGACAGAGTCGCAAAGATTTAGGA
AAACCATTTTTGATCGCTTGATCACCCAATAATTGAAAATATATGCTCGTATTATTTATAGTATATTTAAAATCATTTTTATTCCGTTATATCA
TGCTTGCTGTATTGTGTAATATATCAGTTAAACATAACTCTTAACTAGACAAAAAAAAAAATAATCGATTATATGGTAAATAGGGTGACCGTGAAT
AGTATGTAGCTCCACTTTTCAGAGTTTATAAATGGTGCATTTGATCCTCGACCAGCTTTTTGGGCCTTCTCTTGCGGCGTTTTCTTGCCTTTCGT
CGTAGGCGATCGAATTTCCGGATCCGGTCGCAAATGAAATGCTTGAGGTCATCGCCCTCGGCGGCCGATTGACGACTGCACGACATTGTGAATAT
TATTAGCGAGTTAAGGTAGACAAAAAATCTTATATCGTAGTCATCTAATGATGGTTTGCCCTTGGTTCGATGATTATTATTATTATTATTATCTTTCT
GTCGGTCTTCCCTTTCCCGTTCCCGTTCCTTTTGATAATTACTAAAGTTGTGCTTGCGCAACTTGGAGGCGGGATACGTAGTGGGCGATGGATGG
GGCTCAAAGGTCGAGCGCTGGCGCTTCGAACTGGACAAGTGTTGCCGAAAATAATCGTAAATGCTCATGTTCCTTATAACGATCGTGGTGGTGTT
GCTAATGTTTATTAACGGTCCCGATTTATGAGGCGCCACATGCTGTAGATTTAGCCAACTGCCGCCTGCCGCCTGCACGCGAGTTGGCAACGAAG
TGGCCACTATCTTATTGTAATTGTTATTGGCCAACATCGTTGTCGTATTCAATGTATAATGTAGCATTGGCTCATTGGTGTTATTGTTGCCGATG
TTATGGCATCGGACGTTGTTGTGTTGATGGTTCTGATAATCTTGATTGTAGTAAGGATTTTTTTGTTGGGTTATTGTTGATTGGTTGTATTGTA
ATCTACAGCAGTGACTGCAACCCGTCAATGATCAGCGACCAGCGGTCCCCAGAACATTTTCGATATCTTCGAGTCGTCCTCGGTTAAAAAGAACT
GACGGCCCAAATGCACAAACTCCTTGAGCGACAATTGGCCATCGCCGTTCTTGTCTATCACAGCGAATGAAACGGCAGCATCGTCTTCGGTCAGT
CCCAGACAACGGAAGAAGAGCTTGTATTGTTCGAGATCCAAATGGCCAGTGTGATCAAAGTCCACAGCCTAAGAAAAAAAAAAACCGGAAAAATTA
TTTTTCTGTTTATCGATAATAGCAACTTAACAATGAAACTAACCTTAAACAAGTAGGGCAGGAAGCGACCGATGCGTTTGGCCATCTTCTTGTCG
TTGAGACGATGGTGCAGATCGGTGAGGAACTGCTCGGCAGTTACCAGATTGTATGGGGTTATCTCCCCGAACTGCTCTTCCCAAGTATGCTTGAT
CACATCGTTGAATTCGGCAGCGACCTCTGGGGTCAAATGGCCCAGATCGCTAAAGCGTTTGGCCAGCAAACTAAAGTCGTCGAAGGACACGACGC
CGTCGTGATTAACGTCCAAAATGCGGTGGAGAGTACGCATTTTGCGGCGCCAGAATGCTGAGTCGCCCTAAAAATGAGGAAAAATATACATATTA
ATTGGTTTGCCTTGCGATTTTATTTTAAATTTTAATTATATTTGATTTAAAACATTCACAGGGCGTGCTAAAAGCTTCTTAAACTCTAAAGCTCA
TTGCAATTCTGCAACCAAGCCTTTTGCTCTTTTCAAACTTTAAAAGGACTTGAAAAGTAAAAGCTTGAAAGCTTTGCAGGACTTGACTGTCCTTA
TTAAAATGCTTTTATTAACATCAGCTTATCTCATAGACGCGCAGCGACTGCTTGTGAGCTTTTAGAAGCTTTAACCAAAAGGCTTTGAAAGGACT
TTAAGGAACTGCTTGATGGCAAGTATAGTCAGGATACAAGCAACTGCTTTAAGCTTCAATTCGCTTTTTTTGAGAAAGCTAAGATTTCGTATTAA
TAACCAAACAACAAAGCTTTGATCTTAAAACAGTCTGCACTCAAACCAGTTACTACTGTTAAATGGCCACTGTTAACCAGGTTACAATGTTGGAC
TATTTTTTAAATGCCGTAGAGCAGGTTCAAAAAACGACATTGAGCACGATAAACAAATTTCGAAACACGTTTCTCGGCCTGTCGAGCAAACACAA
TTGAAATTTCTCAGCCACGTGGACCGTGTGTTTTATGGATCTATTTAATGGATTATGCATTTCTCAAGCAGTTCACTCACCCGTTCGCTGCGCTT
GGAATCCATTTTCTGGCGACGACGCTCGAACTCATCATCCGAGTCGGAATCGCTATCACTTTCCACCTCCCGTCGCAATTTGGCCGCTCCGGCCT
TCTTTGAATATTGACGGACAGCCTGGACCACGGCAGTTGGCATTTGATGCCAAAGCAGTGAATGTGCTCCATGTCCACAGATAATGCCGCCAGAT
GCCAGGCGCTGAAATCAGAAAAAAAAAGGAAATTAGAAAAATGTGAAAATGCAAAATGTATTGGATAAGTTTCTCTATCATAATAATCATTTTGA
TTGTGCTTTAAAAAAAGAGATGCTAACGTGTCATTAATAATGTTACGCAATCATTATGCTATTGTTTTGTATTGTTTTTGTGTATATTTCGGTTT
TCACAGCCCCATGCTGAATGCTCTTTTTGTTGTTGATATGGTTGCTAGACGCCCCTTCGGTGTGTAAGCAATCATTATGTTTTTAATTACAACTCA
GCGCACTGCTGTTTTCCTGTGTTGTTTTTGTTGCGTGTTATTTTCTCATTGTTAAGGTCAGTTCTGTTTACTCACAAAACAATTCTAAACCTG
ATTCGTCGTTATCTGTTTTTTTTTACGAGTTTTCCATCTTTGGTTCGCCTTAAAAGTGCCAAAGAGTGACTGTCAAAATGTATCTCAAAAAACTC
GGTCTACAGTTTGAGAGGCGCTTGGTAATGGTAAAAAACCACGTGGCGATCATGTATGTAACGAATTTAAAAGAAGAAATTGTAAACCAGCAGGA
AAATAGCTTCCAATATATATAAAATATATGTAAATATAGGACACGGTATTTTACACATATATAATACATTCAATGTCCTTTGCTGCCAACATTGC
AACTTTGAAAATTAAAAAAGATAAATATTGATGCCAATAACCAGTTCGGAGAAAGGTTTTTTCCATCACCTGTGCCATTAGGAAAAGATAAAAAA
CAAAATTCGCTACTCTTTTAATTACAAGAAACCGAATTCTCTTGTAAACGTTTTGAATTTCAATGGCTCTCGATAAGAAAGAATCCAAGTACAGA
TGTTGCCAGCCACCGACGACGATGATATCATGCATCATACCATATAACATTATCATAAAGCCCGCACACTTATTGTATTGGACTGACTGCTTTGG
GACCTTTTTTCGGTTCCAGTTGCTTCGTTTGGTTAAACGAACTTTGGATTGTTTCTGTTTTTCGGTGTTTTTTTTTTCGTAAACAAGTTTCTCCA
AAATACGAATTAATGAATGCAAAAAACGGGCCTCCTTTCATTTGAATGTCTGCGCGTCTCGAAAATAAAGAGAAACACGTTTCGACCATAAGAAA
ATTAAACAAAAAACAATGCCAATGATTTATATGTGGAAGATGCAGAGAGTAAGAAGACGGCAAATAAAAATCAAAGTCGAGCAACAGGTCAATGT
TAATTTAGCAGCAAACAAGAAGTAGAAAAATTGCGAATAAAATCACTTTAATCATTTCCTGTGATTCTAAAACTTCTTTTTCCGTGGCGGTTAGA
GAAAAAGTAAAGGGAGGTGGGGTACTTTTGTTGTTATAATTTCCAATGCTTTTGCGCAAGATTTTCCTGCTACAGAATTTGCGCAGTTTTCCGAC
TTTCAAAATGAGGGGGTTGTTGTCGGTGAGAAGGGAAAACAAGCTTTCACCTGAATACACGGTGAAAAATACCAGTAAGTATTAATATTGGCTTA
GCTGGTTAAATTAATGTATGTTGTGTCAACATAATATCATAAATTTCGTTTCAAAACCGAAACTTTTATGCAAATACTATTGGACGGTATTTTTA
AAGCTAACAACATAGGAGTAAGATGAAACATGTTTATATATTAACTGAACTATTTTGTTGAATCTATTGATTCAATACCAACATTTCTTTGTGTG
TAATTTCCACTTGTTTATCTTACTGTATCTTGTTTTATTTGTTTCATTGAGGGATATGCCTCTTTCGGCGCCGGGTTTTCAATTTCTTATTGATT
GATTGAAGTGCTGCGCCCTTTAATGATTGATGTGCAAGAAATTTGCCAGCACCTAAACGTATTTTATAGTTAATCATCAATTGAAACCAAAAATC
AGCAATATATAATGCTGCTGCTAACAACAATAAATTAATAATGCGGGAATGAAAAGTTAATAAAAATTAGAGAATTAATAATCCCAAACTCTCTT
GTATTGCTAGAATTATAGTTGGGAATATCTATTAATATTAATCAAGAATTGAACTCGAGTTCTTACAGTTTCGAATGCACTGCTACAGTTTACTT
AGCACTGGCCTCGTTTCGTGAACATTCCCGCTCCCAATTTTCATTCTCCACTTCCCTTGCTTGTCTGTATTCACCCCTCTTCCTCACTATTTACA
GTTCTCCTTCCACCACTTACTGTTTTTCGAATTGCGATTCTATTTTTCTGCTTTGTTTTGAGTTTATATCATGCGGAACTGCTTTTTGGTTGGAA
CATCTTTTGTGGAACTGGTTTTAAACTCTTTATTTTATAACTGTTGCTTTTAAGTTTGTTTTAGGAACTGCTCTTTCCTGTCCGCTTTGTGATGC
TAAGTTTTTCTAACTGCTTGTTTCTGTCAATTCAATTAGTAACCTTAACTACAATGCACTGAAAGAAAAGATGCACTTACGTGACAATCGCTGTG
CGAAATGGGCGTGTTTGGGGGCGGGGAGGCATTCTGCTGCAGAACGCCGACAGTTGCGGCCATGTTGCGTTCCAGAATTTCTCTTGAAGTGCGCA
AAATACCACGGCTCACGATGGAGAATGCCATTTTGTTTTTCGCTCAAGTTTTAACCTCGGTTTTCTTAAATTTTTCCTCAATTTTCGCTACGTTT
TCCTTACAGTTTGAACTGCACTCGAGAAAATGTGCAACGTTGCTTTTTTTAGGGATTTTGTTGTTGAACTCTTGTTATTATTTCGATTGCAACG
CGCATTTAACAACCGGTTTTTCGAAGATGCACCACAAAAAAATGTTTGCCTTTATTTTTCTGCTTTGTTTTGTTACACTTTGTTTTTGAGTCCG
CTAATTTCTATTTTGATTTCTCTGTGGTTTCAGTTTTTTTTTTTTTTGGATATCTTTGCTTGGGAGTAAACACAACCGTTCGCTTAAGCGTTCGA
ATTCGTTTTGAAAACCATCGCTGCGCAAAGAAAAGAAGTCGACGTCGACGCCTGTAAAAGCAGAGCGGTCTTTCTGAGTGTGTGTGAGCGGGAGT
GCGCGTGTGTGTGTGTGGTTTTGTGTGATGAAGAGGGAGAGGACAGCATAAGAAGGGAGCAGGGAGAACAGCTGCTACTTGGAATGGTTACCACA
AGCAGGCAGTACACACTATTGAAGCCAAAATATTAGTAGTTACATTTTCAAATGTTCACGAAATCAAACTTTGAGCTGCATTAATATACACATGC
ATATGTGTCGCAAGAATATTTTTGAATATGAGCGTTCCCAAATGTTAAAACCAGCTTTAAGAGATGCGGAGGAATTAGTATTTAAGTTTTTTAGT
TCATATTTTTGCGCCCTTGGCTGTATATATGTAAGTACAAACACAAAGGCAAGACCATGTAAGCCGGTTGAAGAAGAAAATGGAGAGGAAGCAGG
AGCACAAGAAGAAGCAAAAACAAACACAAAACCCAGTGATTGTCAAACCTCGCTTAAATGGAGAACTGTATTCGTTTTCAAAATAAAGCCCAAAG
AAAATGCATTACATAAACATGGGATTACACACACATATACATACACGGACTACAGTTTTCCAATTGATAACGTAAACGAAGGAATCCAAAAACAA
AAGCCAAAACTCAAAATGAAAATATCATAAAATGTGCGTATTTAGGTCGCTGCGTGTGACAAACTGTCGGTCCAATACAATATGCCCCAAGACAC
CCTTCCCCCCTCGCTACGCACTTCCCCGAAAAGTGCCCTCTACGCACACACATACAAATGAAGTAACACAAATACCTACGCACTAATAGTTTCTG
TTTTTCCGTTGCTGTTCTACTTCATTGCTCCACAGCAAAACGCATGCTTACACCCACACGTGTGCGGTAAATATTATAGGATCATTACAACACTT
TAAAACTAATAACATTAAAAGATCGTTTTCAGTTACATACCAATTAA

FIGURE SHEET 33

(SEQ ID NO: 85)

Exon: 6267..5781
Exon: 3333..3121
Exon: 2442..2134
Exon: 2063..924
Start ATG: 5921 (Reverse strand: CAT)

Transcript No. : CT3375
AACGCTTAAGCGAACGGTTGTGTTTACTCCCAAGCAAAGATATCCAAAAAAAAAAAAAACTGAAACCACAGAGAAATCAAAATAGAAATTAGCGG
ACTCAAAAACAAAGTGTAACAAAACAAAGCAGAAAAATAAAGGCAAACATTTTTTTGTGGTGCATCTTCGAAAAAACCGGTTGTTAAATGCGCGT
TGCAATCGAAATAATAACAAGAGTTCAACAACAAAATCCCTAAAAAAAAGCAACGTTGCACATTTTCTCGAGTGCAGTTCAAACTGTAAGGAAAA
CGTAGCGAAAATTGAGGAAAAATTTAAGAAAACCGAGGTTAAAACTTGAGCGAAAAACAAAATGGCATTCTCCATCGTGAGCCGTGGTATTTTGC
GCACTTCAAGAGAAATTCTGGAACGCAACATGGCCGCAACTGTCGGCGTTCTGCAGCAGAATGCCTCCCCGCCCCCAAACACGCCCATTTCGCAC
AGCGATTGTCACCGCCTGGCATCTGGCGGCATTATCTGTGGACATGGAGCACATTCACTGCTTTGGCATCAAATGCCAACTGCCGTGGTCCAGGC
TGTCCGTCAATATTCAAAGAAGGCCGGAGCGGCCAAATTGCGACGGGAGGTGGAAAGTGATAGCGATTCCGACTCGGATGATGAGTTCGAGCGTC
GTCGCCAGAAAATGGATTCCAAGCGCAGCGAACGGGGCGACTCAGCATTCTGGCGCCGCAAAATGCGTACTCTCCACCGCATTTTGGACGTTAAT
CACGACGGCGTCGTGTCCTTCGACGACTTTAGTTTGCTGGCCAAACGCTTTAGCGATCTGGGCCATTTGACCCCAGAGGTCGCTGCCGAATTCAA
CGATGTGATCAAGCATACTTGGGAAGAGCAGTTCGGGGAGATAACCCCATACAATCTGGTAACTGCCGAGCAGTTCCTCACCGATCTGCACCATC
GTCTCAACGACAAGAAGATGGCCAAACGCATCGGTCGCTTCCTGCCCTACTTGTTTAAGGCTGTGGACTTTGATCACACTGGCCATTTGGATCTC
GAACAATACAAGCTCTTCTTCCGTTGTCTGGGACTGACCGAAGACGATGCTGCCGTTTCATTCGCTGTGATAGACAAGAACGGCGATGGCCAATT
GTCGCTCAAGGAGTTTGTGCATTTGGGCCGTCAGTTCTTTTTAACCGAGGACGACTCGAAGATATCGAAAATGTTCTGGGGACCGCTGGTCGCTG
ATCATTGACGGGTTGCAGTCACTGCTGTAGATTACAATACAACCAAATCAACAATAACCCAACAAAAAAATCCTTACTACAATCAAGATTATCAG
AACCATCAACACAACAACGTCCGATGCCATAACATCGGCAACAATAACACCAATGAGCCAATGCTACATTATACATTGAATACGACAACGATGTT
GGCCAATAACAATTACAATAAGATAGTGGCCACTTCGTTGCCAACTCGCGTGCAGGCGGCAGGCGGCAGTTGGCTAAATCTACAGCATGTGGCGC
CTCATAAATCGGGACCGTTAATAAACATTAGCAACACCACCACGATCGTTATAAGGAACATGAGCATTTACGATTATTTTCGGCAACACTTGTCC
AGTTCGAAGCGCCAGCGCTCGACCTTTGAGCCCCATCCATCGCCCACTACGTATCCCGCCTCCAAGTTGCGCAAGCACAACTTTAGTAATTATCA
AAAGGAACGGGAACGGGAAAGGGAAGACCGACAGAAAGATAATAATAATAATAATCATCGAACCAAGGGCAAACCATCATTAGATGACTACGATA
TAAGATTTTTTGTCTACCTTAACTCGCTAATAATATTCACAATGTCGTGCAGTCGTCAATCGGCCGCCGAGGGCGATGACCTCAAGCATTTCATT
TGCGACCGGATCCGGAAATTCGATCGCCTACGACGAAAGGCAAGAAAACGCCGCAAGAGAAGGCCCAAAAAGCTGGTCGAGGATCAAATGCACCA
TTTATAAACTCTGAAAAGTGGAGCTACATACTATTCACGGTCACCCTATTTACCATATAATCGATTATTTTTTTTTTGTCTAGTTAAGAGTTATG
TTTAACTGATATATTACACAATACAGCAAGCATGATATAACGGAATAAAAATGATTTTT
(SEQ ID NO: 86)

Start ATG: 347 (Reverse strand: CAT)

MAFSIVSRGILRTSREILERNMAATVGVLQQNASPPPNTPISHSDCHRLASGGIICGHGAHSLLWHQMPTAVVQAVRQYSKKAGAAKLRREVESD
SDSDSDDEFERRRQKMDSKRSERGDSAFWRRKMRTLHRILDVNHDGVVSFDDFSLLAKRFSDLGHLTPEVAAEFNDVIKHTWEEQFGEITPYNLV
TAEQFLTDLHHRLNDKKMAKRIGRFLPYLFKAVDFDHTGHLDLEQYKLFFRCLGLTEDDAAVSFAVIDKNGDGQLSLKEFVHLGRQFFLTEDDSK
ISKMFWGPLVADH*
(SEQ ID NO: 87)

Name: SARCOPLASMIC CALCIUM-BINDING PROTEIN
Classification: ligand_binding_or_carrier
Gene Symbol: CBP
FlyBase ID: FBgn0026144

Celera Sequence No. : 142000013384404
TCCGTCGGTTGTTGTGGTAACTTAACTATGTCCACCTTTCCGTTTTCCTGGCACACAAAACTACTAGTTTTTAGCGTTTCTTTTTTGGTTTATTG
TTTTTTGTGATATGATATCGATATCGATATCAGGAGGCGTTATTACGCTTTCCCTTCAACGCACAAACAAATACACCCCCACCAACAAAAGTCGA
TGGTTCGGATTATAGTATCGATAGACAAGCGCGATGCAAAGTGCCCACCTATTCGCGTCTCGAATGTGGGTGTTTCCACTGTACAAGCAATTTGT
ATACATGTGGAAAGCTCTTTGTCCAAATTGGTAAATGGCTAAATGTTTTTGAAAAAAAGATAATTAACAACCATAAAACTACAAGAAAATTACAA
AATTTAACCCAAGTGCATATGTATACATGAATGACAAAACGGTAAAACCATGCAAATGAATAACCATCCACGTCGAATAATACCTAGTTCACCCT
GATAAGGCACTCCCAATTTGTCTTATTAAACAGCTAATTTTGTTAGGGCTTAAAAATACCCAACGTTATGTATGTCTAGTGTTGTCTAGTTTCGG
GGGGCGGAAAAGCCAATTGCACACAAATATACAAAGTATTGCCGAAACGTTGATTCTTTCAATAAATAAGGCACATTTTAATGAACTTATGCTTA
TGCCAACAAAAGCGGTCGCTTATTTTTATTACTTATTGATATAAATTCCAAAACAGCTGACATTTTTAACGGTTACTTTGCCTAGTGTTGGCCAA
GACATCAATCTTAATAATAAACTCTCAAGTTGTCAAAATTATACTTGTATTTCTACTAAAAAGTCATAAATATACCCAAAAACTACTTAGCCAAT
AGTAACCCTGCTTAATATGGATTTTATTCACTTATTAACACGCCAATTGTCTCACTTTTCAAACACAACGGCTGATTGCCAGCACTGTTTGCGCT
GCAGTCCAGTGCTGCGCAACGCGGCGGGGACAAAAAACAATGGCGAGGCGAAACTAAAAAATTGTGTTGCTGACATCTGGTCGCTTGCAAAACTA
TTTCTAGCAGATTTTGTGATATTTCGTTGTGATCGGTCGATAAATCCGCCAGTTTTTTTTTTAATGGAAAGTGCTAACACATTGTAGCGGTTGGG
AAGATAGCAGGAAAGGTGAGCGAAAGGCAGAAGATTGCGAAAAATTCAATTAAATTTCCGCGACCGTCTGTTTTCTGCATCGGTGTGTGTTTGTG
TTTGCTCGCAAGTGTGTGTGGGTGCTCTGTGTATGACGTAAAGCGATAAAGCAAACGCATTCCCCCCACTCCTTGCATATGTGTGTGTGTGCAAG
TGTTGTGTTTCTCTCTCATCAGTTTTGCATCTAATTAGGAGCGGAAAGCATTGATTGGCTGCCAAACGCCGCGGTTTGTTGTTTTTTTCGCTGCA
TTTCGGCCAAAAGGCTTGCCGCAGCTGCATATGTGTCGCTATGTGTGTGTCAGTGTTGCACAGTGCCGCCAGTGCCCACAAAATGGGCGCACAAC
AACAAAAGCAGCAACTCGGTTGGGATTTTCGCGATCCTACGCTGGCTCGGAGCTCCCCTTTTCCTATTTCCAATTCCCAGCCAGCGGGCTGCCGT
TTTTCCTTTTTGTTATCCGTTGCCAGACGCAACGAAAACGACAGTTGGCATTTGAATTCAGCACAAACACACATACTAACGCCGACCCGCAAGCA
GCACACACACACACACTGGGACACTCGAAAAAAAAAAAACAGACGCTGTCGGCGACCTCGACAAGCAGTTGGGTTCGATTTAGTTGTCAATGCCT
TGAATTCGGTTCGGGGCTTAGTTTCCACAAGTTTATCGCTCGTCAAGAAACAACGAAATAAAATTATTTTCGACCTAAAAAATCTGACTAAATTG
TGTTTTTTGTTTATGTATTTATTTAGGCACATTTTGCACACCACAACGTAGTTACTACATCTACGACTAACGGAACTCCTCCTGCAAGCAGTGGA
AGTTGCTGTCCATCAAGCAGTACTCGGAGTTAACGCAGGATAAGCCGGGAGAAAGAGAAAGAGATCGGTGGAGAATAGAGATATACAGGTGGAGT CAAAGAGGAAGGATCATGGACATGATTACGGTGGGGCAGAGCGTCAAGATCAAGCGGACGGATGGCCGCGTCCACATGGCCGTGGTGGCGGTGAT
CAACCAGTCGGGCAAGTGCATCACAGTCGAATGGTACGAGCGCGGCGAAACGAAGGGCAAGGAGGTAGAACTGGACGCCATACTCACGCTCAATC
CGGAGCTAATGCAAGATACTGTCGAACAGCACGCCGCCCCGGAGCCCAAGAAACAAGCCACCGCGCCGATGAACCTCTCGCGTAATCCCACACAA
TCGGCTATCGGTGGCAATCTCACCAGCCGTATGACCATGGCCGGAAACATGCTGAACAAGATCCAGGAAAGCCAGTCGATTCCCAATCCGATTGT
CAGCAGCAATAGCGTGAATACAAACAGCAACTCCAACACTACGGCCGGCGGAGGTGGTGGCACCACAACGTCGACGACCACTGGATTACAGCGTC
CACGGTACTCGCAAGCTGCTACCGGCCAGCAGCAGACAAGGATCGCCTCGGCGGTGCCTAATAACACATTGCCCAATCCCAGCGCGGCAGCCAGT
GCTGGTCCGGCGGCACAAGGAGTCGCCACTGCGGCCACAACCCAGGGAGCTGGCGGCGCTAGTACCCGGCGATCGCACGCATTGAAAGAGGTGGA
GCGACTGAAGGAGAATCGCGAGAAGCGACGCGCCCGACAGGCCGAGATGAAGGAGGAGAAGGTGGCGCTGATGAACCAGGATCCGGGCAATCCAA
ACTGGGAGACGGCGCAAATGATACGCGAATATCAGAGCACGCTGGAATTTGTGCCGCTGCTCGATGGCCAGGCCGTCGATGACCATCAGATCACA
GTGTGCGTGCGCAAGCGTCCCATTAGCCGCAAGGAGGTCAATCGCAAGGAGATCGATGTCATTTCGGTGCCGCGCAAGGACATGCTCATCGTGCA
CGAGCCGCGCAGCAAGGTCGACCTCACCAAGTTCCTGGAGAACCACAAGTTTCGCTTCGACTACGCCTTCAACGACACGTGCGACAATGCCATGG
TATACAAGTGAGTATCCAATCCAAATAACAAGCTCCAAAACAACTCCATATATGGTCTGTTTGAATTACTAGTAGTGATTCTAAACAAACGCTCG
ATATGGTGACCACACATTCCAATGTCTTGGGGAGGCTTCTTCAATTACTAATGCGTATCCTTGCTAGCAAACGGCTTTATTTCAATTGAACTGAA
CTATAGAAAATCTTATTTCGTTATAGATGACCCTCTATAGCTATCATTCAATCTTAAACCTAATTTGTTGATGCAGTGGAATCATATATAGTATA
AAGCAGCATATCCTTTAAAGAAATCATTGCCCCATTTATCAGATTTCCATCGAGTAACCAAATGTGCCAGTCACTTTTCGAGCTCGTTTCGTTGG
CGCATCTCTGTTAGAGCGACCCATTGAGTCATGCCGACAGAGACGGCAACAGAGCCACACACATGCATCATGAAAGCGGTTGCTCCCGAAATAGC
CAAGTTCGTTGAATGACTAACTTGGAAGCCCCAGACGCTTCACCTGCCCCCGCCCGGCCACTCCGTCCGCCGATCTGCACACGAGCTCTCTAAAC
CCAATTCTCCAGCGGAAGAGATTTCGAAAAAGTAACTGCCTTGTGGCCCGGCATTTGTCCATTAGCAATTGTTTGGCTTCAATTGAATTAAAGCT
GCTACGGCTGCTGCTGCCCCTTTCCTTTCTCCGCCAACTTCTTGCTTAGCTTCTCTTTCCGGTTTTCGCACTCGTATGTATTGTGTGGCTGTCGG
GAATTGGTAATGCCATTAGTTGCGTCACGGCAATCGCTTAAGTATAGCCCAAAAAGTATACCCCATGAGTAATATAGCCCGGCATTAATGCACAA
AATCTCGCCGATGATAACGTAGTCTCGTGTTGACAAATCCAAATGGGTGAATCAACTGCTGACATCGTGCGTTATCAATACTCAGTATTGGCAGA
AAACAATGCAACTTACACATTTATTGATTACATTTCAATATGCGTTCCTTAATTAGTCGTATGTATAATTCTTATCGATAATCATTTTTACTAAG
CAACTGCTAACTTTGAATGCAAATCGATGTATTTATCTATGATTAATGCTAAAGTCTGAAACACAACAGTCCATATAGTATTGAATGCTTGCATA
TAGCACATATCTGCATTGAATAACCATGCTAATCTATAATCTTGCACTTCATCCGCGCAGATACACAGCCAAGCCGTTGGTGAAAACCATTTTCG
AGGGCGGAATGGCGACGTGCTTCGCCTACGGCCAGACGGGATCGGGCAAAACGCACACCATGGGCGGTGAGTTTAATGGAAAGGTGCAGGACTGC
AAGAACGGCATCTACGCCATGGCGGCCAAGGATGTCTTTGTGACCCTGAATATGCCGCGTTACCGCGCCATGAATCTAGTCGTCTCGGCCAGTTT
CTTTGAGATTTACAGTGGCAAGGTGAGTGAGACAACATACAACTTGGCATGATTATCATACTTAGCTGTATTAATCGATCGTTGTGTTGTTGCCA
TAGGTCTTCGATCTTCTGTCCGACAAGCAGAAACTGCGCGTCCTGGAGGATGGTAAACAGCAAGTGCAGGTGGTGGGACTCACCGAGAAGGTGGT
CGATGGCGTCGAGGAGGTACTGAAGCTCATCCAGCACGGCAATGCTGCCCGAACATCCGGCCAGACGTCGGCCAACTCCAATTCGTCGCGTTCGC
ACGCCGTTTTCCAGATTGTGCTGCGGCCGCAGGGCTCGACGAAGATCCATGGCAAGTTCTCGTTCATCGATCTGGCGGGCAATGAGCGGGGCGTG
GACACTTCCTCGGCCGATCGGCAGACGCGTATGGAGGGTGCCGAGATTAACAAATCGCTGCTGGCCCTCAAGGAGTGCATTCGTGCGTTGGGCAA
ACAGTCGGCCCACTTGCCCTTCCGTGTCTCCAAACTCACCCAGGTGCTGCGCGACTCGTTCATTGGCGAGAAGAGCAAGACGTGCATGATAGCCA
TGATCTCGCCGGGACTTAGCTCCTGCGAGCACACGCTCAACACGCTGCGCTATGCGGATCGTGTCAAGGAGCTGGTGGTCAAGGATATCGTCGAA
GTTTGCCCTGGCGGCGACACCGAGCCCATCGAGATCACGGACGACGAGGAGGAGGAGGAGCTCAACATGGTGCATCCGCACTCGCATCAGCTGCA
TCCCAATTCGCATGCACCGGCCAGCCAGTCGAATAATCAGCGTGCTCCGGCCTCTCATCACTCGGGGGCGGTCATTCACAACAATAATAATAACA
ACAACAAGAACGGAAACGCCGGCAACATGGACCTGGCCATGCTGAGTTCGCTGAGCGTAAGTATTTGCATATTTCTCACCTAGAAGTTACACACA
AGGCCATAATATAATATATATTCTATAATATATGTTATATAGCTTAGTAGGCTTAGTTTAGGGCATTTGGCATTGTCACTCACTTCCGTCAGTCA
GCATCTAGTCCCAGCTCAGTTTGCAACTCCCTTTAGTTCGGGTTACAAGTTATATGTTATAAATACATGTCGATACCATCACCATCCAACACAAT
GCTCCAGCTAGGCAAAGACAAGGCAAAGGCGAGAGCACGCGATAGCCACACGCCAAATGTGGCTGTTTACACCAATGTACAGACCCTGCGATCCG
TGTACAGCATGGTCAGCCAGGCGGCAGGCAGGAAAGCTGCTGCTGCTGCTGCCACCTCGATTCCCATGGCGCAAGTCAAAGATCACGAGGAACCG
TCACGCGTTTGGAACTGCAACAAGCCCAAGAAAAAGGAATATAAAACATATAACGTCTACTCCAAACAAGCGGACAAGTTAAGCGGCGAAGAGGG
ATCCAAGATGGGCATTCGACAGTGGGTCCATCCCCCGTATCCCGTTCATCGTGAGCGCAAGAAGCGCGACGGCCCGGGCAACTACGAATCCTTCT
ATGTGCCCTACGAACAAGACGATGGGATAATAGTGAAAGACAATCCCTGGACCGAGACAAAGGAGCTGGCAGTGAATCTACGTAGCCGATCATTT
AAGCGCTTGCCGACGGCGGGCGAACGGTATGCGCTAAATATCACCAAAATGGCCAGTCTGATTGAGAAGGTCAAGTCGCATCCGAATCACGACGG
TGTGTCGAAGGCTGCGAGGCAGATGTGTCCGTTGTTGCCGCCGCCGCCGCAGTTCGCCGAGGATCCCATTGATTCCGGGCGGCGCTTCGCCCTGC
TTCGCTCACGAACGGAGTTGTGCTTCTCGATTTTGGATTGCGATGACTTGCTGTACAAGTACGCGTGTCATCTGCCCTTTGTGCGCGATCCATTG
CAGCCAGATGCCGTGCGGCCAAAGATGAAACGATTGTCGTGCTCAATTGGGGGGAATTCGTGCACCATACTCAACTAGCCATCAATGATCTTATA
TATTTTATAACTTGTTCTCGTTGAATTCCAGTAAAATTCACGTGTTCCCCTTTGGGTCATACTCGTATGGAAATAAGTATAGGGCTTTTTCCCCA
TAGACAGATCCCTAATGAAACATACAACCTATAATGTTCATTTATACACACTGCACATTGCCATTTTGCAGGAACACGAGATGTCCGACGAGCTG
ATTGTGCAGCACCAGGCCATCGACGACCTGCAGCAGACGGAGGAGATGGTGGTGGAGTATCATCGCACCGTTAATGCCACACTGGAGACCTTCCT
CGCCGAGTCGAAGGCGCTGTACAATCTGACCAACTATGTGGACTACGACCAGGACTCGTACTGCAAACGGGGCGAGTCGATGTTCTCGCAGCTGC
TGGACATCGCCATCCAGTGCCGCGACATGATGGCCGAATATCGCGCCAAGTTGGCCAAGGAGGAGATGCTGTCGTGCAGCTTCAATTCGCCGAAT
GGCAAGCGTTAGTTCATTCCCGCATTCGACCCGTTCATCCACAATCACCAACAATCATCCACCACACCCAACCAGGCGTACACTTTACATTACAA
ATTCCCTCTGGCTTCCCAATGGACGTGTCTGTCGTGCAGTCCCCTAAAACAATCTCTCTATCACCTTTGCCCCAAACCGTCGAGTTTATGTCGCT
GCGAGTTTATGGTTTATTAAGTTTTAACTGATAAATAATAGTCGAGAGCCTATATTTTACAAACGAACTAAGCACGGGAACAGACCAGATACCA
CAGCATTAATACCATTATGAGAGCAACGCAAACCAATAAAAAGGAACTCAACTGAAAACTGAAGACAGGCTAGGCTGGCTGGCCACGACTTTGTT
TGGATTCGCCGTGAACTATGATTATATGAATATAATTGTAATTTCAGCGCAGTCGATACTCTAATTGTGTAAAAGAAAAAGACATTTACTATACA
ATATATATATATTTACTACTTACAAACATACGTTCTACTCTAAACAATGATATGAGATTCCATTTAATTTTTAACAAATAACCTTATGCGATTCG
ATTCGATGCGATTTGTTTCCCTCATTTTTGTTCATTTTGTAGAATTACTCGACCAGAGTTGTTTGTTCATGCCACGGCACAAATCTACTAGTTTT
TAAATTACGAACTAATCGCGCATTGTATTTATTTAAAGGCCACAAAACTGTATTTAATTTGTATTAATTTATTAAAGTACTACTGCACCAAATCC
GATTTACATACGTATTCCCATAGCCAGTAACTATTAATGATTTTCACACGCAAACCGAACTGCAATCTTAGACAGCAAGTGTTTTTTTTTGTGAA
ACTTTTTATGCCCCTTCTTTATAAATTTATATATCTACATATAAATTATTTACATTATATTTTTTTTGTCATTTTAAGCGACTTCGGTGAAGAA
TTTAAAATGCAAACTGTTTTTGCTATACGATTATTATGATTTAGAGATGATTTGCATTTCATT
(SEQ ID NO: 88)

Exon: 1001..1155
Exon: 1599..3142
Exon: 4336..4582
Exon: 4659..5471
Exon: 6722..7043
Start ATG: 2112

FIGURE SHEET 35

Transcript No. : CT3411
AAACTAAAAAATTGTGTTGCTGACATCTGGTCGCTTGCAAAACTATTTCTAGCAGATTTTGTGATATTTCGTTGTGATCGGTCGATAAATCCGCC
AGTTTTTTTTTAATGGAAAGTGCTAACACATTGTAGCGGTTGGGAAGATAGCAGGAAAGAGCCAGCGGGCTGCCGTTTTTCCTTTTTGTTATCC
GTTGCCAGACGCAACGAAAACGACAGTTGGCATTTGAATTCAGCACAAACACACATACTAACGCCGACCCGCAAGCAGCACACACACACACACTG
GGACACTCGAAAAAAAAAAAACAGACGCTGTCGGCGACCTCGACAAGCAGTTGGGTTCGATTTAGTTGTCAATGCCTTGAATTCGGTTCGGGGCT
TAGTTTCCACAAGTTTATCGCTCGTCAAGAAACAACGAAATAAAATTATTTTCGACCTAAAAAATCTGACTAAATTGTGTTTTTTGTTTATGTAT
TTATTTAGGCACATTTTGCACACCACAACGTAGTTACTACATCTACGACTAACGGAACTCCTCCTGCAAGCAGTGGAAGTTGCTGTCCATCAAGC
AGTACTCGGAGTTAACGCAGGATAAGCCGGGAGAAAGAGAAAGAGATCGGTGGAGAATAGAGATATACAGGTGGAGTCAAAGAGGAAGGATCATG
GACATGATTACGGTGGGGCAGAGCGTCAAGATCAAGCGGACGGATGGCCGCGTCCACATGGCCGTGGTGGCGGTGATCAACCAGTCGGGCAAGTG
CATCACAGTCGAATGGTACGAGCGCGGCGAAACGAAGGGCAAGGAGGTAGAACTGGACGCCATACTCACGCTCAATCCGGAGCTAATGCAAGATA
CTGTCGAACAGCACGCCGCCCCGGAGCCCAAGAAACAAGCCACCGCGCCGATGAACCTCTCGCGTAATCCCACACAATCGGCTATCGGTGGCAAT
CTCACCAGCCGTATGACCATGGCCGGAAACATGCTGAACAAGATCCAGGAAAGCCAGTCGATTCCCAATCCGATTGTCAGCAGCAATAGCGTGAA
TACAAACAGCAACTCCAACACTACGGCCGGCGGAGGTGGTGGCACCACAACGTCGACGACCACTGGATTACAGCGTCCACGGTACTCGCAAGCTG
CTACCGGCCAGCAGCAGACAAGGATCGCCTCGGCGGTGCCTAATAACACATTGCCCAATCCCAGCGCGGCAGCCAGTGCTGGTCCGGCGGCACAA
GGAGTCGCCACTGCGGCCACAACCCAGGGAGCTGGCGGCGCTAGTACCCGGCGATCGCACGCATTGAAAGAGGTGGAGCGACTGAAGGAGAATCG
CGAGAAGCGACGCGCCCGACAGGCCGAGATGAAGGAGGAGAAGGTGGCGCTGATGAACCAGGATCCGGGCAATCCAAACTGGGAGACGGCGCAAA
TGATACGCGAATATCAGAGCACGCTGGAATTTGTGCCGCTGCTCGATGGCCAGGCCGTCGATGACCATCAGATCACAGTGTGCGTGCGCAAGCGT
CCCATTAGCCGCAAGGAGGTCAATCGCAAGGAGATCGATGTCATTTCGGTGCCGCGCAAGGACATGCTCATCGTGCACGAGCCGCGCAGCAAGGT
CGACCTCACCAAGTTCCTGGAGAACCACAAGTTTCGCTTCGACTACGCCTTCAACGACACGTGCGACAATGCCATGGTATACAAATACACAGCCA
AGCCGTTGGTGAAAACCATTTTCGAGGGCGGAATGGCGACGTGCTTCGCCTACGGCCAGACGGGATCGGGCAAAACGCACACCATGGGCGGTGAG
TTTAATGGAAAGGTGCAGGACTGCAAGAACGGCATCTACGCCATGGCGGCCAAGGATGTCTTTGTGACCCTGAATATGCCGCGTTACCGCGCCAT
GAATCTAGTCGTCTCGGCCAGTTTCTTTGAGATTTACAGTGGCAAGGTCTTCGATCTTCTGTCCGACAAGCAGAAACTGCGCGTCCTGGAGGATG
GTAAACAGCAAGTGCAGGTGGTGGGACTCACCGAGAAGGTGGTCGATGGCGTCGAGGAGGTACTGAAGCTCATCCAGCACGGCAATGCTGCCCGA
ACATCCGGCCAGACGTCGGCCAACTCCAATTCGTCGCGTTCGCACGCCGTTTTCCAGATTGTGCTGCGGCCGCAGGGCTCGACGAAGATCCATGG
CAAGTTCTCGTTCATCGATCTGGCGGGCAATGAGCGGGGCGTGGACACTTCCTCGGCCGATCGGCAGACGCGTATGGAGGGTGCCGAGATTAACA
AATCGCTGCTGGCCCTCAAGGAGTGCATTCGTGCGTTGGGCAAACAGTCGGCCCACTTGCCCTTCCGTGTCTCCAAACTCACCCAGGTGCTGCGC
GACTCGTTCATTGGCGAGAAGAGCAAGACGTGCATGATAGCCATGATCTCGCCGGGACTTAGCTCCTGCGAGCACACGCTCAACACGCTGCGCTA
TGCGGATCGTGTCAAGGAGCTGGTGGTCAAGGATATCGTCGAAGTTTGCCCTGGCGGCGACACCGAGCCCATCGAGATCACGGACGACGAGGAGG
AGGAGGAGCTCAACATGGTGCATCCGCACTCGCATCAGCTGCATCCCAATTCGCATGCACCGGCCAGCCAGTCGAATAATCAGCGTGCTCCGGCC
TCTCATCACTCGGGGGCGGTCATTCACAACAATAATAATAACAACAACAAGAACGGAAACGCCGGCAACATGGACCTGGCCATGCTGAGTTCGCT
GAGCGAACACGAGATGTCCGACGAGCTGATTGTGCAGCACCAGGCCATCGACGACCTGCAGCAGACGGAGGAGATGGTGGTGGAGTATCATCGCA
CCGTTAATGCCACACTGGAGACCTTCCTCGCCGAGTCGAAGGCGCTGTACAATCTGACCAACTATGTGGACTACGACCAGGACTCGTACTGCAAA
CGGGGCGAGTCGATGTTCTCGCAGCTGCTGGACATCGCCATCCAGTGCCGCGACATGATGGCCGAATATCGCGCCAAGTTGGCCAAGGAGGAGAT
GCTGTCGTGCAGCTTCAATTCGCCGAATGGCAAGCGTTAGT
(SEQ ID NO: 89)

Start ATG: 669

MITVGQSVKIKRTDGRVHMAVVAVINQSGKCITVEWYERGETKGKEVELDAILTLNPELMQDTVEQHAAPEPKKQATAPMNLSRNPTQSAIGGNL
TSRMTMAGNMLNKIQESQSIPNPIVSSNSVNTNSNSNTTAGGGGGTTSTTTGLQRPRYSQAATGQQQTRIASAVPNNTLPNPSAAASAGPAAQG
VATAATTQGAGGASTRRSHALKEVERLKENREKRRARQAEMKEEKVALMNQDPGNPNWETAQMIREYQSTLEFVPLLDGQAVDDHQITVCVRKRP
ISRKEVNRKEIDVISVPRKDMLIVHEPRSKVDLTKFLENHKFRFDYAFNDTCDNAMVYKYTAKPLVKTIFEGGMATCFAYGQTGSGKTHTMGGEF
NGKVQDCKNGIYAMAAKDVFVTLNMPRYRAMNLVVSASFFEIYSGKVFDLLSDKQKLRVLEDGKQQVQVVGLTEKVVDGVEEVLKLIQHGNAART
SGQTSANSNSSRSHAVFQIVLRPQGSTKIHGKFSFIDLAGNERGVDTSSADRQTRMEGAEINKSLLALKECIRALGKQSAHLPFRVSKLTQVLRD
SFIGEKSKTCMIAMISPGLSSCEHTLNTLRYADRVKELVVKDIVEVCPGGDTEPIEITDDEEEEELNMVHPHSHQLHPNSHAPASQSNNQRAPAS
HHSGAVIHNNNNNNNKNGNAGNMDLAMLSSLSEHEMSDELIVQHQAIDDLQQTEEMVVEYHRTVNATLETFLAESKALYNLTNYVDYDQDSYCKR
GESMFSQLLDIAIQCRDMMAEYRAKLAKEEMLSCSFNSPNGKR*
(SEQ ID NO: 90)

Name: KINESIN-LIKE PROTEIN
Classification: motor_protein

Celera Sequence No. : 142000013384562
AAATAAGTTGAATTTTTGACTTTAAAGCTTAAAATTAAGGGTTTTTTGCTTAATTAAACTCAATTTTTTTATAAAATATAATTAAACAATATTTA
TTTTACTTATAAATCAAAAAACAAATTAAAAATATTAAATATACAAGAAAATAAACAACAAATTCCAAGTTTACACACTTTTGAGACTGTCAAGA
AACTCTTTACACATTTTGTTTTCCTACTTTGTTTTGTTCTTTTTCTTAGAACGAACTAGATTTTTCCGTTATTTTTGGCTTTGCATTGCTTTTTA
CAACGCTTTTATTGAAATTTGTTGACTTTGCCTGTGAAATTTTGCTGATCAAATTATTAAATTTAATAAAATGCCTGGAAAGAGATTAACTTTTG
AAGTTACCCAATTAATAAACTATAACCACCATGTATATATTTATCATTAACTAGGGCCTGCAGCAAGTCAAGAACTTCTATCTCAGGTCCGAGAA
GCTGCCCACGCCCATTCCCACTGGAGAATATCTGCTGATGATTGACTGGGTGTTCAACAAGAAACCGCAGGCTGCCACAAATGTTTACTTCACAT
TTGTGGAGGACCTAAAAGATAGTTAACGAATCAATCGTTCAGACCAAAATGTTTAAACTGAACTGTAATTACAAAATAAACAATATAAGTCTATA
TTGTTTTAGCCGATGAAAATTATATGGAATTTTGGCTTTGCCATCAACGAGAAATTGTTTCTATCCGTGATCTGTGGAATACAAATGCGACTATT
AAGTCTTTGTTCCTGAGACCATCAAGAGCACTTCCAGCAGCCAGCGCAATATCGTAATCGTAATTTAAAACAAACAATACAAAAATAATTACCAA
TTAAGCCCATTTTAAATTCACATTCCGTATTGCAAAGCACAAAATAGCCTTGTGTCCAGTGGTATCCAGAAAACCGGCCCATTTAATAAGCTTTT
AAAAACGTTGAGGGATGTGCAATAGTTAGTTTATTCGTCTCTTTGGGATTTTAGCACTGTTCGTTACACTCATCGCCCGCGTCTGCCTTTGTCCA
TACGGAGATTTTGTTGATATTTTTGCGAATCCTGACAAAAGCCCCACAAATCTGATCGCAGTGATCGCAGGCCTCGCCAATCATGCAAAGAAGCA
CGTCCAGCCAAGTTTTGTCCAGTTCGGCTGTGGACCTTTTATCCACTTTATATGTCCAACGACCTCCGCCCTTGTTCGGCGGATCCTCCCACATG
GGGCGAATGCCCTTCTTGAAGAGCATGTAATCACAGCCGCGGTTGAGCTTGGATGGCGTATCGATGCGGAAATACAGGTTCCAGAAGTCCTCGAC
GGTATTGAAGCTGTCAATCTCCTTCAGCATGTCCTCCCATGATATTTCAGGGTCGTACTTTACGCCCCACAGGGTCCATGTGTTCTGCAGCCGGT
GCTTGTTTGTGGCACCCAACGATGCCAGTTTGTTATTATCCAGAGAAGTCCCCATTTTAAATTCCGATGACTCTTTGGTTTGCCTTAAGTTTTCC ATTTCGCAGATACTCTATGCTGAAGCCCCCTTTTAAAATGCATTCGTAGAATTCGTAGAATTGTTTTTAATGGACTTACAATATTTACCGACGAA
TGTGGTCAAGCTTAGAGCATTTGATCATTTAATTATTGACGTTAAAGCAATGCACTGTCAATTAGGAAACAATCGTGATTACTAATGGCTGCATT
TATATGTAAAATACATTTGACAGGCAATCGAAACATATCGATATATCGCGTGATGCTATCGTGAGAGGTTGGCCCAGCGCTAGTATTGATTGTTA
AACAAAAAGGAATTTTGCACTAACTTGTGGGCCGCAGTTACTGCAAATTCGCGCCAGGATGGACATGATAAACAAGTTCTACTCATCCGCCGTAC
AGACGGTGTCCACACTGTCCGGCGTTCTGCCCGGGAACAATGTGACGCGGGAGTACGAGGTGCTGGAACAGGTGTGCACTGCCGGAGTGGGTGAG
TTTACCTGCATTGCTAGTTGAACATATTGTGGCTTGCTGATACCGAGTAATCCCACTGCCAGGTCTGATGTGGAAGGTGTACAATGGCCACAAGA
AGAGCACCAAACAGGAAGTGTCCGTCTTCGTGTTCGAGAAAAAGTCGTTGGAGCGCTGGTCGAAGGATGACCGGGAGACCATGCTGGAAACACTG
CGTCGCGGGGTTCAACAGCTAACAAAAATTCGACATCCTCACGTGCTAACCGTACAGCATCCACTGGAGGAGAGTCGGGACTCGCTTGCCTTCGC
CACGGAGCCGGTTTTTGCCTCCCTAGCCAACGTGGTCGGCGACAACGTCCGCTCCGAAAAGAAGCTCTATGATGTAGAGATTCGACACGGTCTGC
TGCAGCTCTTCGATGGCCTGCAGTTCCTTCACCAAGACGCCAAGATTGTGCACCGCAACATTAGCGCCGAGACAATCGTGATCAACAAGAACCGC
AGCTGGAAGCTGTTCGGATTTGATTTCTGCATTGCCAACCAACCGGCCACCG
(SEQ ID NO: 91)

Exon: 1522..1001
Start ATG: 1522 (Reverse strand: CAT)

Transcript No. : CT3489
ATGGAAAACTTAAGGCAAACCAAAGAGTCATCGGAATTTAAAATGGGGACTTCTCTGGATAATAACAAACTGGCATCGTTGGGTGCCACAAACAA
GCACCGGCTGCAGAACACATGGACCCTGTGGGGCGTAAAGTACGACCCTGAAATATCATGGGAGGACATGCTGAAGGAGATTGACAGCTTCAATA
CCGTCGAGGACTTCTGGAACCTGTATTTCCGCATCGATACGCCATCCAAGCTCAACCGCGGCTGTGATTACATGCTCTTCAAGAAGGGCATTCGC
CCCATGTGGGAGGATCCGCCGAACAAGGGCGGAGGTCGTTGGACATATAAAGTGGATAAAAGGTCCACAGCCGAACTGGACAAAACTTGGCTGGA
CGTGCTTCTTTGCATGATTGGCGAGGCCTGCGATCACTGCGATCAGATTTGTGGGGCTTTTGTCAGGATTCGCAAAAATATCAACAAAATCTCCG
TATGGACAAAGGCAGACGCGGGCGATGAGTGTAACGAACAGTGCTAA
(SEQ ID NO: 92)

Start ATG: 1 (Reverse strand: CAT)

MENLRQTKESSEFKMGTSLDNNKLASLGATNKHRLQNTWTLWGVKYDPEISWEDMLKEIDSFNTVEDFWNLYFRIDTPSKLNRGCDYMLFKKGIR
PMWEDPPNKGGGRWTYKVDKRSTAELDKTWLDVLLCMIGEACDHCDQICGAFVRIRKNINKISVWTKADAGDECNEQC*
(SEQ ID NO: 93)

Name: eIF4E-related
Classification: translation_factor

Celera Sequence No. : 142000013384566
AGGCCTTTCTACGTTGTGTTTAGCGAACTCGAAAGCGAACTGTCGCTCCGAACGGCGCACAAAACACTTTTAAGCGCGCGCGCTCTCGGTTTTT
CTTCGTGTGTGTGTGAGTGATGGGAGAGTGTGCACTGTTATCTTTTCAACATGTCGCCCGTTCTTTGTTAACCGTTTAAATGGCTGATAATTGAA
TATTCCCGATAATTGCCGCACTCAATGTGATACACACGTCCTCAATATGGGTATACTTTGTATAAAGTCGGGTTTCCTAGTCAGATAATCCCCAC
TTACTAAGAAGTAAATTTATCAAATGCAATATGGCCGCTCTTTTGAGATGCGCATCAGCTGTTCTTTGTTTTTGTTTTGGCCGTGGGAGAGCACC
ACGTCATGTGTTGCCAGGCGGTTTAATTATTGCTGACAATTTAATTCACATTTTGTCAAGTTGATTTGCACGTTCGAAGGGGGGATCAGTCACCC
ACTTTGATAACTGCTAATATGGCGACGGCTCTTTTTTACGTGTCGCTTGCAGAGCTCCAAGAATGACACTTGATAAGAAGGATACATGGTGGGAA
AACTTACAAATTACATAATTTGTTTGTTGATTGGGGAAACCCTACATTATCTCCGAACCCAGCAATAATATGTATTGTAAATAGCAACAGTCTCA
AGCTCGATGCTGCTGTGAATTACCAATATATCAAAACTTAAAACATTATCTTAGGAGGTAGATGGTTTATCTGCAGTTTATTTTCAATTCTCATC
GTTAGCTGATAAAACTCTCAGGAAACCACTTGAAATCCAAAGTGCAGCGTCCATATTTTGCACACGCTGACAACCCTGTCGTGAGTCACCTTCCA
GCAGGCGCAGCAACAACAGCACTGGCAGCGGCCATATTTGAATGACACCGAAATCCCGCACTGAGCGCAAAACAACACATGCCCATGCACGCTCT
CCAAAACCACACACACACAGCCATATCGATCGCATAGAAAGAGACGTACGCGACGCTATAAACAGCAGTTGATTTTCAGAGTTTCACCAAGAAGC
ACATAAAGCGATTGAATTATTAATAAAAGCACAGGCACTGGAAGTGAGTTTTAATATTACTAACTAACTACTTTGTGAGTGTTTAGTTACGAAAA
CTAGAAAATAATATTCTGGAAACTGTGTTTTTAAACCGACCACCATATAAATTTAAAAACCAAAACATTCCATTGGTGGTGGTTTTGTTGTTAAA
AAAGAGCACAGAAAATTCAAGAAAACGCTACGACGCAAAACGAAAAAACTCGCCCAAAATGAAAACAAAAGTGTCTGTTTTCCAATTGTCAATTG
TTGTGAAACTAATTTCCTTTGTTTTCGCCTCTCGAATTTGATTTTAATTTACAGTAAACCGTCGACATGAAATTTTTCGTTGCACTCGCTCTCTT
TGCGTGCCTCGGCTCTCTTGCCTTGGCCAAGGATGATGAATATTGCCAGAACACTGTAATCACCGCATGCTCTACGTCAGCCTTTTCGGGTGAGT
AAAGAGAGCGCCTCTAAGAGAGAGTGGCTAATCTGTGTTGTTGCTTTTTGTATCTTTGTAAAACATAATAATAAAAACAAGCGCTCACGGGCTTT
TTCACAGGCAAGAGTAAGTGAAATATAGATTGGATGTATTTCTGCACTATCTCAGATTTCGTGAAAATGAACACTTTCCAATTCTTACTGCATTA
CGGCCCTTACATTATTATTTTAAAGATACAAATACAAATTCAAAATTCTATTGCCTTGTTTAGTATGGCACTACCTAGTTAGGAACCATTAAGAC
TATGTCATTACTATTGGATGTGCTTCTGCTCTCCTATTCTAAGAGTGTGATCTTTATTATTTGCTTTTTCCCCGTAGCCAACTCCATTTGTAATG
CCCGTTTTGCTGGCATTGACCATATTGAGCCCGAGATCCAGTCCTACATCAACGCCAACTTGGCCAAGTCGTACGACTACCTCCTGCTGGCCACC
CACTTCAACTCCTACCAGAAGAACCGCCCCGGCTTCCAGAAGCTGTACCAGGGACTCTCGGACCGCTCCTTCGAGGACAGCATTGCCCTGATCAA
GCAGGTGACCCGTCGCGGAGGAATCGTTGACTTCAACACCCGCCACGAGTCTTCCGGCTCCGTGAGCACCAAGCGCGGCACTCTTGAGGTCGACG
AACTGCACTCCCTGGCTCTGGCTCTGGACACCGAGAAGCAGCTGGCCACCGGAGCCACTCACGTGCACTCCCGTGCCACCCACGCCACCGACGCC
GAGAGGGATCCCGAGCTGGCCCACTACTTCGAGGAGAACTTCCTGGGCAAGCAGGCCGAGAGCGTGCGCAAGCTGTCCGGCTATGCCAACGACCT
CGCCAAGCTGATGAAGGTCCCCGACCCATCCCTGTCCGTCTACCTGTTCGACGAGTATCTGCAGAAGCAGTAAGGAGTGGAGACCACCTCCTTTT
CCTCCTTCTTTTTCTAACACGCTCCTACACTGTCTCCTCAAAATTGCTCTCATAATTCCCTTATAAATTTGCTTTCCTTGGATTGTTCATCAATAA
ATCGCAGTGCAGCAGCAGCATTATCAAAGCAGCCACAAGTGAATAATTTACACCGCGAAATTCACCTTGATTTACCAGCACACCAGATTGTGATA
ATGTTATCATAAATAAGTTAGCAAGTTCGCCCCAGCAAATGTATCTTTAGTATGTACGTTACCGCTTGAACAAATAATAAACACATCAAAGAACC
TAATTATCAACTAGTAAAACAGCAGCATTTTTGACCTCTCTGATAAGGTTTGGGTTTGGGTCGAAATGTATCTGGTCCTCAATGAGGGGCGTCTGT
TTGCGTTTTTTCTCCGAGTGCTGCTGATTGCGGGCTGGCTGGCAGTGTACTTTGGATATCATATGGAACAATGAAATATACAAAGTCGAAATGGT
ATCGGAAACTACTCAGTTCTGCGATCACAACGGGTGTAATGTTCCATAATGTTGTGGTTTCTGATATTCTTAGAATGTGCCTTCAACTAAAAACC
ATATGTTTATGTACAAGCCATCAACGCTTGTCTAAAAATAAATAAATAAATGAGAATGTAAACCCATGTTGTAAATATCGTAGTATTGTATGCAA
ACTACGTTACCATTTTAAAATCATCTTTTGACCATTCAGAGACTGGAATCACTTAGGATCTAGTGGGATCTATCTATCTCAATATCAATTTATT
ACTTTCTTTCAATTGACAACCTAAATCGATGGTGAAAAGTGAAACCTATCTCTCGCAGTGATCTGTGGGGCTTAAAGGAGCCCGACTATCTAATC AGTGATACACTCCTCCGCCGCTGATACGAAGGGGCCACGTTTGTCATTCCATGCGAGATTCTCTCTGTCGCCTTATCACTGCCTGGTGCACACGG
CTTTGCCGCTCCGGAACCGGAGCAGATCCGCCGGGCGCCATCTTGGCCGTCTGCTGACTAAGTCGGAGACTCCACGATGACGTGGATGTCACATT
GTTGCGTAAGCCGATGCAATCTCGGATTTTAATTGTCCCCTGAATTTGCATCGCAGTTTCCCTATCTTCCTCTGCTCCCTCCTCACTCTCCTGAC
CTACAATAATTGTTGTGAATCCCTATTTGTGAATATGAGTTTTTTTTTATAATCCACATGGAAGCTCTATTAATTCTAGGAAATTCCGTAAGAT
CCTATAACAGCTGCTCAATTAACGTGTGAAATAGGTAAAAATGTATCTTTAATCACTTTTGAAAGTGGT
(SEQ ID NO: 94)

Exon: 1001..1088
Exon: 1385..1514
Exon: 1883..2774
Start ATG: 1397

Transcript No. : CT3604
CGACGCTATAAACAGCAGTTGATTTTCAGAGTTTCACCAAGAAGCACATAAAGCGATTGAATTATTAATAAAAGCACAGGCACTGGAATAAACCG
TCGACATGAAATTTTTCGTTGCACTCGCTCTCTTTGCGTGCCTCGGCTCTCTTGCCTTGGCCAAGGATGATGAATATTGCCAGAACACTGTAATC
ACCGCATGCTCTACGTCAGCCTTTTCGGCCAACTCCATTTGTAATGCCCGTTTTGCTGGCATTGACCATATTGAGCCCGAGATCCAGTCCTACAT
CAACGCCAACTTGGCCAAGTCGTACGACTACCTCCTGCTGGCCACCCACTTCAACTCCTACCAGAAGAACCGCCCCGGCTTCCAGAAGCTGTACC
AGGGACTCTCGGACCGCTCCTTCGAGGACAGCATTGCCCTGATCAAGCAGGTGACCCGTCGCGGAGGAATCGTTGACTTCAACACCCGCCACGAG
TCTTCCGGCTCCGTGAGCACCAAGCGCGGCACTCTTGAGGTCGACGAACTGCACTCCCTGGCTCTGGCTCTGGACACCGAGAAGCAGCTGGCCAC
CGGAGCCACTCACGTGCACTCCCGTGCCACCCACGCCACCGACGCCGAGAGGGATCCCGAGCTGGCCCACTACTTCGAGGAGAACTTCCTGGGCA
AGCAGGCCGAGAGCGTGCGCAAGCTGTCCGGCTATGCCAACGACCTCGCCAAGCTGATGAAGGTCCCCGACCCATCCCTGTCCGTCTACCTGTTC
GACGAGTATCTGCAGAAGCAGTAAGGAGTGGAGACCACCTCCTTTTCCTCCTTCTTTTTCTAACACGCTCCTACACTGTCTCCTCAAAATTGCTC
TCATAATTCCCTTATAAATTTGTTTCCTTGGATTGTTCATCAATAAATCGCAGTGCAGCAGCAGCATTATCAAAGCAGCCACAAGTGAATAATTT
ACACCGCGAAATTCACCTTGATTTACCAGCACACCAGATTGTGATAATGTTATCATAAATAAGTTAGCAAGTTCGCCCCAGCAAATGTATCTTTA
GTATGTACGTTACCGCTTGAACAAATAATAAACACATCAAAGAACCTAATTATCAACTAGTAAAA
(SEQ ID NO: 95)

Start ATG: 101

MKFFVALALFACLGSLALAKDDEYCQNTVITACSTSAFSANSICNARFAGIDHIEPEIQSYINANLAKSYDYLLLATHFNSYQKNRPGFQKLYQG
LSDRSFEDSIALIKQVTRRGGIVDFNTRHESSGSVSTKRGTLEVDELHSLALALDTEKQLATGATHVHSRATHATDAERDPELAHYFEENFLGKQ
AESVRKLSGYANDLAKLMKVPDPSLSVYLFDEYLQKQ*
(SEQ ID NO: 96)

Name: Ferritin 2 light chain homologue, FER2LCH
Classification: ligand_binding_or_carrier Celera Sequence No. : 142000013384859
CAACAATTGTAAATTTTTCGATCAAACGATTAAGATTTGTAAAAAAAGGTTGAGAAAATCGGATAAAAAGTTTGGAAACTATCGAGTTAAGTTTG
GTGTATGAAAAAAAAAAACTTATCACATTGCCACGTTTCTAAACGAAAACATAACAATTAAAAAAATAACATTTTTAATCGGTTTAGGGAAATAC
AAACCAAAAGGGGAAGATATTACCATTTAGAGGCGAAAGGTCAACAAGAAACACATGCTTTCTCTTTCTAAATGATTTCACATTTTATTTTGTAT
AGTTTCCTTTTATCATATTTTGTGCAGATATTTTCTTATAGCAGCAATTTTTGTATAATAAATATATTTTTGTCATTTAATTATTTTCTTTCTCC
GCGTTTTCTTTAATTTCTTTAGTTTACTGTCACTTAGCTTAACGAATAAGAATAGCGCAATTTATTGCTTCGCACAATTGAACATTGAAGAATTG
CCTATATATATATAAATGTATATATATTATGTCTCTCAAAGGTACTTGCATCTGAATAATTATAAAAACAAAAAAATAAAAGCGTAAAGAGGACG
AAGTTACGCACATTTCCCTCTGATCATAATCAACAATAATGGTGGGAGTAAAGTATAAGGTAAAATAATATAATATATAATGGAGATATATAAAA
GATCATAGAAATAGCCATATACATATAAATACATAAAAGCAATTCAATTGGATCATATCATCATCATCTTTTCATCTTTTCGGGCGAACAATCAT
CCTCTTTGGAATTCTTTTCGTTTAAGTAGGGAAAGTGGAAATGAAGCCGTCCATATATATGGTAATCTGTCCAGTTTTTGTCTACGCGTTTCTGT
TCAGTTCAAGCCTTGTTTGATATTGCTGCGTTTTAAGGCCTCTCCCACTGTGGAATCCATATTGCTGGCTCTGCCTTGATCTAAGTGTTTTCCTC
TGCCGTTCAGTTATAGTTAATTTTGAAATATACTCGTACTTGTGTTATTGTTAGTTATTGTTAATTGCACTGCTGGCGGCCACTAACTCCGGAAC
GGTGGACGAGGCGGCACTGCTCTGACTGACGGTGCGGGCATGATCCACATGGTTTTGGGTCGGCGCCGCAGACGGAGCCGCTCCCGAGGCTGCTG
GCATCGATCCCGAAGCTTCTCCCGACTGCACTGGCGTGCCCTCGCTCGCTCCGGATCCGTTTCCATTTCCGGGTACGGGCTCCACCGTGGGAAAG
ACGGGCGGCAAGGCAGGCGCGACCACGGGCGTCTGCACCATGGGTGTGGGAGGCGAACGATTCGCTGGCAACTGATGAGCAGTGGCTCCGGTCAT
CTGCATGTGGTACCTTTGGAGTGTAGATTGATGAACATTAAACAAGGACACAATATCAAACGATCTTTGGAACCCACTTGTAAATGTTCTCGGTG
CTTTCGACAACACCTTGGGTAAGATTGAGGCTCCGCCCCTTGATGCCCGACTCCTTGGCCGGTGGGGACCACCAGTTGAAGACGCGTCCCACCAC
AGGCACGTGGCGCAGGATGCCCTCCTGCCAGAGCTTCTCCTCCGATTCGCGCTGCAGATCAGCGGTAACCGCCTCAATGCCCTGAGCGTACAAAT
AAATTAACACATGTTACATTAATCCAGTACGAGGTGGTAGCCAACCTTTTTAACAATCTCCGACATGGTGTCCAATACCCGCGAGTTTTCCTGGA
CGCTCTTGCCCACCGTGACCACCAAGTCTAACAACTCTTCGACCTCCGTTTCATGGGTCACCATTCCGAATCGCACACAAATCAGACCATCGGTG
CCTTCGCCTAATGAAAAGGCATTGTCCGTGGATTTCAGGGCCTCCACCAGGTCGATGTTCAGCTTGTTTAGCTCTGTTTTGGCCTGGTCCGTCAG
CAGGGACTCCCAGCCCTCGGGCACGAAGCGAACACCGCCCATGCCCGCCCATTCGGGCAGTGGAACGAGGCGCAGCACGTCGCTGCACTCCACCA
GATGAATGAACCGTGCCTTGTGCTTGATGGTCGCGCGCAGGATGTCCACATGTGCCTCTAAGCTCTGAGCGAAGCTCTCCAGGTTCTCGGAGCTT
GGCGGCTGCTCACCCAACCCCAATTCCAGCGGACAGTAGCGAATGCAGCTGCCGTGCGTCGGGTGTTCAATTACCTCAAAGTCAAACTGGAAGAA
CATGGTGATTAGGCTCATACAAGGAGATGATTAATTCACACTGCATACATTGGGACAGTCGCGTTGCAAGATTTGACCCAGCCAGGAGTTGAGCC
GGTCGAAGTAGGAAGCATTGTTAATCTTCTCTAGCGGCTTGAGGCCTTCGGCCGTTTCCCGCTCAGCAGCGGCAGCGGCGGCGGAAGAGCCACTC
CCGCCCAGTGGAATGGTGGTGCTGCCGTCGAACTGATAGGCGACCACGGGGGCGGCGGCATCAAAAAGCGCCTGCACATCAAAGGGGCTCTGAAT
GACGTCCGACAAAGAGGCTCCGGTCTGCGCTCCTGGAGTATGGCTCTGAAAATGCCAAGGTCCTTTGGTAAACTAAAAACATTATCCATAAACGT
GTGTGCAATAATTTACCAACACCCGGATGCCCTCACACTTGGAGGCAATCTCGAAGAGAATACTGCACGTCTGGAAGGCCACATGCAGACGCTCC
GCAATCGCCTTCCGGCCCAGCGCCTGCAAACTGGTCCACAAGGACAGGGCATTAAGACGACGCGACAGTATGGGATCGGATTCGAAGGCACTCAG
AGCGCTGTTCTGCAGCGGACGGTGCAGCAGGACGATGGGCAGACTGGGCACACCCAGCCAGCTGCCCAAATTCAGGGCCATCGAGTGGAGTACCT
CCTCCACATGGCCCTGATTTTGGGCGCACACCAAGGCGGCCAGTCCGTGGCCACTGGCGTGCAGCCACATGTTGTGCGCCTTGCATACGTCCCTC
AGCCGGAGCAGGTTGTCCACATAGCCACACAACGAGGCTCCAATGTCGGCGACCACCAGCAGCGGAGTCCTGTTATTGCCCACATCCTGCTGAAT TTGCTTTTGCAGCAGCGTCACATCCATTGTCCCGGACTGACTGTGCTCCGGAATGACCTTAATAGCCTCCAGCGGTATGCCCAACTGGCGGCATG
CGTAGTGCAGCCTCATCGGCGTCGTATTCTCCGAGATGTAAAACGTAGGCTGCGCCAGGGCGGGTATGCCACCCTCCAAGTACCCCGGACACCTG
GCGACGATGGCCAGTCGCACCGTACGCAGCACCGCGTCTGCATTGTCCGCATGGAAGCTGCTCGCCGGGTGGGCAAAGTGAAACAGCGTGCCCAA
CCAGCGGGTGGCGTCCCCGGAAATGCTGTTCGTCACCCGGAGCAGTTGCTGACGGTCCAGATGCGACAAATAGGCCACAATGCTGTGCGATATGA
GAGCCAAGTGGGAGACGTCATCCAGGGCGGGCAGCGGGAACTCCGGATCATCGTCGCTGTCCGTGTAAGAAACCAATTGCTCCAGCGACTTAAGA
ATGTCGGAGGGCACGCGATGCTTCGCTGGCAGGAGGTCCTCGCTGGTCACCCGCTCCCCAGCCTCTTCCTCGTTCTCGACGGGATTTGGGCTCTC
CGGCGTGGTCGACACCTTAACGTTCTCTAAGCGCTGCAGCACCTGCGAAGATCGCAGCTCCAGCTCCGCCAGGCCCGATCGAATCTATGTGGCGA
ATACATGGCTAATTAGGTGGGATAGTGGACAAGGTAAACAACAGCGCTCCAGAAGTTGACGTGTCTTCCGTCGTCGTCAGCAAAAAAAAAAAAGA
TAGAAGCAGGGCGAAAAAAACCAAACACTCACACTGGAAGCGGCGATTTCGGCCACCGCTGGCGTTGATTGGCCCGGATCCGGCTCTTGGTCTAC
GAGTGGGCTCTGGCCGGGATCGTCCACCGATCTACCAGCCGCTGACATGGTTTCAGTGCGGTCTAAATCACTTTTAACTTATCGCCTGCGATGCA
AAATAATTGTTTTCGTTTCGTGCCACTGCGTCTGTGTGGGTGGGTGTGTGTGCGTGTGTGTGTGGGGCGGGCGAGTGTGTGTGTGTGTTGATGGA
AGAGAGGCTGATGTGGAATGGTGTGACCGTAGTGGGTGCGTCTGACTAAGATCGCAAATAGTGTGCGATTGTTGGCCCATGGTTCTGGTGATGGA
ATAGGTCGCAAGGAAGTTGGAAAACTATTATAATATCCGCCACTAAAAGACGTTGGACAGCAGCACACAAACGTACATACATAGCACCTACTCGT
AACCTTAAACGACGAGTTTTCACAGTGGTTTGTGTCACGGTTTGTGTCTCAGCGATTTTGAAGACAGCACCGCACGGTCATACTACACAGCCATC
GATAGTTGCGGAAAACTCATCGATGCTGCGAAAGTGCGATAGTATCGAATAAACATGAGTGTGTGCATGAGTGTGGGAATTTATTAAACAAAAAC
GAAACGCGGACAAACTATATTTATGTAATAAACACTAAGCCGCAGCGCCAACGAGTAATGAACAGTCCACGGCCAGGTCGTACTATTCAGGCGAA
CGCACCTCGCAATCGACTGCAATCAAAGTGCAATAGCTCAATCAATTGATTCGTTTTGCTCAACCAAAAACAAAATCTATTCCCAAATCGGTGCG
ATAGTTGCCAAAATATAAAAACTACACTACGCTAAAAAAAAAACAATACACTCACACACTGGCGTACAAGACAACAAAAGAGAAGAAGAAGAGCA
GACGCCAGATATAAAAAGCCCCCAAAAGAATTGGAAATAAGACCATACCCCTCCTTCTCCCTTGAAAAGGGACCTTAAAACTAGGCGACACCGAA
TAATTGAACTCAAGTAAAAAACCGGGAAAAGAGAAAAACACTTTCAACAAAATATCTAGAAGCCTTGTTATCGATTTTGTTCCGGGTTTTTTTG
TGTGAGTGTGTGTTGTGTGAAGCGCGCCCGCGGGTGTGTGGGTGAGTGTGCGTGTGGCTCTCGGCGCG
(SEQ ID NO: 97)

Exon: 4008..3833
Exon: 3694..2582
Exon: 2515..2234
Exon: 2176..1661
Exon: 1601..1408
Exon: 1343..1001
Start ATG: 3943 (Reverse strand: CAT)

Transcript No. : CT3725
AAACGAAAACAATTATTTTGCATCGCAGGCGATAAGTTAAAAGTGATTTAGACCGCACTGAAACCATGTCAGCGGCTGGTAGATCGGTGGACGAT
CCCGGCCAGAGCCCACTCGTAGACCAAGAGCCGGATCCGGGCCAATCAACGCCAGCGGTGGCCGAAATCGCCGCTTCCAGTATTCGATCGGGCCT
GGCGGAGCTGGAGCTGCGATCTTCGCAGGTGCTGCAGCGCTTAGAGAACGTTAAGGTGTCGACCACGCCGGAGAGCCCAAATCCCGTCGAGAACG
AGGAAGAGGCTGGGGAGCGGGTGACCAGCGAGGACCTCCTGCCAGCGAAGCATCGCGTGCCCTCCGACATTCTTAAGTCGCTGGAGCAATTGGTT
TCTTACACGGACAGCGACGATGATCCGGAGTTCCCGCTGCCCGCCCTGGATGACGTCTCCCACTTGGCTCTCATATCGCACAGCATTGTGGCCTA
TTTGTCGCATCTGGACCGTCAGCAACTGCTCCGGGTGACGAACAGCATTTCCGGGGACGCCACCCGCTGGTTGGGCACGCTGTTTCACTTTGCCC
ACCCGGCGAGCAGCTTCCATGCGGACAATGCAGACGCGGTGCTGCGTACGGTGCGACTGGCCATCGTCGCCAGGTGTCCGGGGTACTTGGAGGGT
GGCATACCCGCCCTGGCGCAGCCTACGTTTTACATCTCGGAGAATACGACGCCGATGAGGCTGCACTACGCATGCCGCCAGTTGGGCATACCGCT
GGAGGCTATTAAGGTCATTCCGGAGCACAGTCAGTCCGGGACAATGGATGTGACGCTGCTGCAAAAGCAAATTCAGCAGGATGTGGGCAATAACA
GGACTCCGCTGCTGGTGGTCGCCGACATTGGAGCCTCGTTGTGTGGCTATGTGGACAACCTGCTCCGGCTGAGGGACGTATGCAAGGCGCACAAC
ATGTGGCTGCACGCCAGTGGCCACGGACTGGCCGCCTTGGTGTGCGCCCAAAATCAGGGCCATGTGGAGGAGGTACTCCACTCGATGGCCCTGAA
TTTGGGCAGCTGGCTGGGTGTGCCCAGTCTGCCCATCGTCCTGCTGCACCGTCCGCTGCAGAACAGCGCTCTGAGTGCCTTCGAATCCGATCCCA
TACTGTCGCGTCGTCTTAATGCCCTGTCCTTGTGGACCAGTTTGCAGGCGCTGGGCCGGAAGGCGATTGCGGAGCGTCTGCATGTGGCCTTCCAG
ACGTGCAGTATTCTCTTCGAGATTGCCTCCAAGTGTGAGGGCATCCGGGTGTTGAGCCATACTCCAGGAGCGCAGACCGGAGCCTCTTTGTCGGA
CGTCATTCAGAGCCCCTTTGATGTGCAGGCGCTTTTTGATGCCGCCGCCCCCGTGGTCGCCTATCAGTTCGACGGCAGCACCACCATTCCACTGG
GCGGGAGTGGCTCTTCCGCCGCCGCTGCCGCTGCTGAGCGGGAAACGGCCGAAGGCCTCAAGCCGCTAGAGAAGATTAACAATGCTTCCTACTTC
GACCGGCTCAACTCCTGGCTGGGTCAAATCTTGCAACGCGACTGTCCCAATTTTGACTTTGAGGTAATTGAACACCCGACGCACGGCAGCTGCAT
TCGCTACTGTCCGCTGGAATTGGGGTTGGGTGAGCAGCCGCCAAGCTCCGAGAACCTGGAGAGCTTCGCTCAGAGCTTAGAGGCACATGTGGACA
TCCTGCGCGCGACCATCAAGCACAAGGCACGGTTCATTCATCTGGTGGAGTGCAGCGACGTGCTGCGCCTCGTTCCACTGCCCGAATGGGCGGGC
ATGGGCGGTGTTCGCTTCGTGCCCGAGGGCTGGGAGTCCCTGCTGACGGACCAGGCCAAAACAGAGCTAAACAAGCTGAACATCGACCTGGTGGA
GGCCCTGAAATCCACGGACAATGCCTTTTCATTAGGCGAAGGCACCGATGGTCTGATTTGTGTGCGATTCGGAATGGTGACCCATGAAACGGAGG
TCGAAGAGTTGTTAGACTTGGTGGTCACGGTGGGCAAGAGCGTCCAGGAAAACTCGCGGGTATTGGACACCATGTCGGAGATTGTTAAAAAGGGC
ATTGAGGCGGTTACCGCTGATCTGCAGCGCGAATCGGAGGAGAAGCTCTGGCAGGAGGGCATCCTGCGCCACGTGCCTGTGGTGGGACGCGTCTT
CAACTGGTGGTCCCCACCGGCCAAGGAGTCGGGCATCAAGGGGCGGAGCCTCAATCTTACCCAAGGTGTTGTCGAAAGCACCGAGAACATTTACA
AGTACCACATGCAGATGACCGGAGCCACTGCTCATCAGTTGCCAGCGAATCGTTCGCCTCCCACACCCATGGTGCAGACGCCCGTGGTCGCGCCT
GCCTTGCCGCCCGTCTTTCCCACGGTGGAGCCCGTACCCGGAAATGGAAACGGATCCGGAGCGAGCGAGGGCACGCCAGTGCAGTCGGGAGAAGC
TTCGGGATCGATGCCAGCAGCCTCGGGAGCGGCTCCGTCTGCGGCGCCGACCCAAAACCATGTGGATCATGCCCGCACCGTCAGTCAGAGCAGTG
CCGCCTCGTCCACCGTTCCGGAGTTAGTGGCCGCCAGCAGTGCAATTAACAATAACTAA
(SEQ ID NO: 98)

Start ATG: 66 (Reverse strand: CAT)

MSAAGRSVDDPGQSPLVDQEPDPGQSTPAVAEIAASSIRSGLAELELRSSQVLQRLENVKVSTTPESPNPVENEEEAGERVTSEDLLPAKHRVPS
DILKSLEQLVSYTDSDDDPEFPLPALDDVSHLALISHSIVAYLSHLDRQQLLRVTNSISGDATRWLGTLFHFAHPASSFHADNADAVLRTVRLAI
VARCPGYLEGGIPALAQPTFYISENTTPMRLHYACRQLGIPLEAIKVIPEHSQSGTMDVTLLQKQIQQDVGNNRTPLLVVADIGASLCGYVDNLL
RLRDVCKAHNMWLHASGHGLAALVCAQNQGHVEEVLHSMALNLGSWLGVPSLPIVLLHRPLQNSALSAFESDPILSRRLNALSLWTSLQALGRKA
IAERLHVAFQTCSILFEIASKCEGIRVLSHTPGAQTGASLSDVIQSPFDVQALFDAAAPVVAYQFDGSTTIPLGGSGSSAAAAAERETAEGLKP
LEKINNASYFDRLNSWLGQILQRDCPNFDFEVIEHPTHGSCIRYCPLELGLGEQPPSSENLESFAQSLEAHVDILRATIKHKARFIHLVECSDVL
RLVPLPEWAGMGGVRFVPEGWESLLTDQAKTELNKLNIDLVEALKSTDNAFSLGEGTDGLICVRFGMVTHETEVEELLDLVVTVGKSVQENSRVL

FIGURE SHEET 39

DTMSEIVKKGIEAVTADLQRESEEKLWQEGILRHVPVVGRVFNWWSPPAKESGIKGRSLNLTQGVVESTENIYKYHMQMTGATAHQLPANRSPPT
PMVQTPVVAPALPPVFPTVEPVPGNGNGSGASEGTPVQSGEASGSMPAASGAAPSAAPTQNHVDHARTVSQSSAASSTVPELVAASSAINNN*
(SEQ ID NO: 99)

Classification: enzyme

Celera Sequence No. : 142000013384455
GGTTGCCAAACGGAGAGCAGCATACCTTCCGGATAGCTGGCATCGATCACGATTACTTCCAAGCACTGTAGCAGCTCCTGGACCTCACTTAGTGG
CCCCTGCAGCTTTCGCTTTATCTGACGCACTGGACGCACTGCAGCCACTACTACCAGTAGATTCACATTGGTGGTGATTATCTTATCGGGAAATC
CCAAGCCGGAACGCACATCCGCCAGCTTAAGGACCGCACCAAGTGGCCTTATGGGCTGATGGAGTAACTGCTGGAGAATTGTTATTTGGCCAAAG
TCGTCATTGTCGTGGCGCACCACATAGCCGGATCCCTCGTTGACCACCAGGGCGCAGGAGACCGTCGCTTGGGGCTGATAACGCTGTTCTCCCGG
AGCAGCAAACGGTATGGACATCACTTTAGCGCCCACAATGTCTACCACATGGCCGATCTGCAGCATGGCCGCGTACTCATCCACACAGTCCCGCT
GGCCCCAGCACTTGCAATTGGTCAGGTGATTGGGGGAATCTCGGATGGTCAAGCTGAGAACCCCTCGTTCGGTGCCACTCATCTTGTCATAGAAG
ATGTTCGGCGAGGATTTGGAGACAATCAGGGCAACGGTGGAGAAACGGGTCATTGTGGGACGCATCTCTGCCAACCGCTGGAACTTAATACGCCT
TGCCATTGAAATTATTTAAGAAATCGCGACCAGTCAGATTGCAGTGCTTAAGAAAACCGTTACATTGCCGTTACCGCCGATTAGTAGTTATCGAT
GTTTGTAGTGATGGTACACCACAAATGGCCGTAGATTCAGTTAGTAACAGAAAGTATTGCTAACAACTTAGTTTGATAAAAACCACAATTAAAAC
ATTTACAGAAAGTTGCGCTTATTAATTGTAACCATTGGAATCGATAATAATCGGATGGCATCCGAATACCAGACGTACCATCCCTAATAAGCTGA
CACACACTACGCATATGTGCACCCGCGCACACACACACGCACACACAGAGGGGAACGGCACAGATTTACTGCGTTAAACAAACTCACTTGTCGCA
CTTTTCCACGAATGCCAGTGCGCTGAAAGTGAAACCCATCCGCCGGAGCATAGTAGGATTAGCCAGGACAACCGTTCAGCTCAGTGCCCCAGAAG
CATTTAATTGGAGGAGCAACAGTCGAGCAACCCGCGACCCGCAGACCCAGTCTTGGCAGCCCACAGCCACTCAAAATGGTCAAACTATTCGCGTT
GAGCATCTTTCACAAGGGCGCCAGCGAGGCGCGTCTCCTGAAGACCGCCTCGGACCTGCAGTCCTTCTCCTTTTTCCAACGTGGCACCGTCAACG
AGTTCATGACGTGAGTATGCATGTGGATGCCAAAGAACGGCGCAGGCTCAAAGAGTCATCAATGACGAACACCCCCCTAAACAACTCCTCCTCTT
GCAGTTTCGCTTCGAAGACGATTGTGGAGCGCACACAGCCGGCCCTGCGGCAATCGGTGAAACAGGATGCCTACATGTGTCATGTCTATGTGCGG
GCGGACAATCTGGCCGGTGTACTGATCGCCGATCATGAGTATCCGCATCGCGTGGCGCACACGCTTATCACAAAGATTCTGGATGACTTTACGGC
CAAGGTGTCGGCCGATCAGTGGCCCAATGGCACGGAGGCCACTATCTCATTTGACTTGCTGCCAGCGTTTCTAGCACGCTATCAAAATCCCGTCG
AAGCAGATCCGCTGACGAAAATGCAAAACGACCTGGACGAAACGAAGATCATACTGAAGAATACCATCGAGGCGGTGCTGGAGCGGGGCGAGAAG
CTGGACGACATGGTCAGCAAGTCGGAGAAATTGTCGCTGCAGAGCAAGGCGTTCTACAAGACGGCGAAAAAGACTAACTCCTGCTGCAGCTTCAC
CTAGACGACAGCTGCACCTCTCATCACCCCCCACCACACGCTAATCCTCTCAAGCAACAACCACAACAGGAAACACCAGAAAATGCAAATCAAAG
ACAACACAAAGGATAATGGATAACACGATAACACCAACAAACTACAACCAAACAAACTCCAAGGGAGCGGTGCGACTTGGGCTTTGATGATTGCT
TTTTATAAATGAATTAGTTAATTTTATATACTATATATATATATTATATTATATACTGTATGAATAGGATGGCCAGTTGCCAGTTACGATAGTCC
GCTAACCCAATGTCTACCTGTCTGTATATGTCTACGCTTTGGATATCTAAATGTTAATTACTACCAATACAGATTACGATCTAAACCCATGTGCT
TAACATAATCTTCTCTTCACTTATGTGTTGGCACGGCGGTCCAAAATTGGCCCTTTGCTAGCTATTGATGTTGTGGGCCTTCTTATCGCCTCCAC
GGCGGATCTATGTATACCAATCGGATCGGAAGGCTGCACCTATGTATACACATGCAGTCGCACTTCCGATCCGGGCAACTGGCGGTCGGAATGTG
TGGGCGTTTCAATAAAGAAGTATTATGGGAAATGTGAACCAAGCTCGTTTTCATTGCTCACATATACAAACCTTATCTTTGTCAATTTTGGCAAA
ATGTACAAACTATTTGTACGAGCTCTGTACATAGCACATGAACTTATTTTTATTTATGTAATACGTACCACTTTATCTTAAGTGCAAATTCCATT
CCTCCCAAAAAAGCAAAATCAATTTAAAAGTGATTTTCTGTTGGCGTTTATTTATTATATAGAAGACACCTATTTCGCTTCTTGTAAAGATTTCC
GTTACATTTTTCATATTTATGCGTTTTCCTTACGTTTTCGTGTTTAACCTTTTGGATTTTGGTTATGTTTAATGGGTTCGGTTTGTATAGCCTAG
TATAAGATAGGTAAATCGATTACAATTTAGTTTTCGCCCCCTCTCCATCGCAAT
(SEQ ID NO: 100)

Exon: 1001..1340
Exon: 1430..1904
Start ATG: 1216

Transcript No. : CT3893
GGGAACGGCACAGATTTACTGCGTTAAACAAACTCACTTGTCGCACTTTTCCACGAATGCCAGTGCGCTGAAAGTGAAACCCATCCGCCGGAGCA
TAGTAGGATTAGCCAGGACAACCGTTCAGCTCAGTGCCCCAGAAGCATTTAATTGGAGGAGCAACAGTCGAGCAACCCGCGACCCGCAGACCCAG
TCTTGGCAGCCCACAGCCACTCAAAATGGTCAAACTATTCGCGTTGAGCATCTTTCACAAGGGCGCCAGCGAGGCGCGTCTCCTGAAGACCGCCT
CGGACCTGCAGTCCTTCTCCTTTTTCCAACGTGGCACCGTCAACGAGTTCATGACTTTCGCTTCGAAGACGATTGTGGAGCGCACACAGCCGGCC
CTGCGGCAATCGGTGAAACAGGATGCCTACATGTGTCATGTCTATGTGCGGGCGGACAATCTGGCCGGTGTACTGATCGCCGATCATGAGTATCC
GCATCGCGTGGCGCACACGCTTATCACAAAGATTCTGGATGACTTTACGGCCAAGGTGTCGGCCGATCAGTGGCCCAATGGCACGGAGGCCACTA
TCTCATTTGACTTGCTGCCAGCGTTTCTAGCACGCTATCAAAATCCCGTCGAAGCAGATCCGCTGACGAAAATGCAAAACGACCTGGACGAAACG
AAGATCATACTGAAGAATACCATCGAGGCGGTGCTGGAGCGGGGCGAGAAGCTGGACGACATGGTCAGCAAGTCGGAGAAATTGTCGCTGCAGAG
CAAGGCGTTCTACAAGACGGCGAAAAAGACTAACTCCTGCTGCAGCTTCACCTAG
(SEQ ID NO: 101)

Start ATG: 216

MVKLFALSIFHKGASEARLLKTASDLQSFSFFQRGTVNEFMTFASKTIVERTQPALRQSVKQDAYMCHVYVRADNLAGVLIADHEYPHRVAHTLI
TKILDDFTAKVSADQWPNGTEATISFDLLPAFLARYQNPVEADPLTKMQNDLDETKIILKNTIEAVLERGEKLDDMVSKSEKLSLQSKAFYKTAK
KTNSCCSFT*
(SEQ ID NO: 102)

Classification: hypothetical

Celera Sequence No. : 142000013384012
TGTGTGGATTCGTGGAGCAAATCGAAGTTGGCAGGATTAAAGGCATTCGCGAACGCAGAGGCAGCAGCTAAAGGGCCACCCATGCACCAAAGAAA
CAAACTAGCTGGCCCAGCGGTTCATTTATCTGCGACTAACAAGCTAAAATCGGCGTAATTGGCAAGTTCAATGCACGACTAATATATTTGGCCAC
ACTTGCCAGTGTATGTTTGTTCGTGTGCGTGCCTGTTTGTGTGGTGTCGTCTCCGTACGTGTTTGTGTGTGTGTCCGCGACGAGTATGTGTGCGC ACATATTCGTATATCTGCAAGACTCGCGGATGAAACAGCGTGAAAAGTGAGCAAAATATCGGGGAAAAACGGCACGGTACGGCCACAGAACGGAA
CGGTACGGTGCGATACGATATCGAGAAAAGGCCATCAGCCAGAGTACTCCTCGATCCGGAAACGGATAATGGGGATATAGATGATACAGCCAATA
GCTCCCCGAAAGCCACAGCACACAATAGGTCGGTCGGTCGGTCGGTTGGTTGGGCGACGTCGCCGAGAGTTAAACATCAAAAATCAAACCCAGGA
ACCGACGGAGCTAAGTGTCAAGTGTTTGGTGTTGTGAAATTTTTCGTTTCCAGCTCTCCGTTCAGCGTTCAGCCAATTTGCCAACCTTTTCCCCT
CTTTAATTTGTTATCCCCGGACACCACAAGAGTTTCGATCAAAATTTTCAATTGAACGCAACATCGCCATAAACAAAAACATAAAGGTAAAATTC
GGCCACTACCCAAACAACAAAAAAATAAAATCATAAGAAAAAATCACGCAGTAACGTAGAAGAAGCAGCAGCCGAAGCCGAAAAAAGACGAAAAG
AAAACTTGTTTGAAAAGGCCGAACCGAAAGAAGAAAAAGAGCAGCAGCAGCAGCACAGCGGCCAAGTTTGGAAGAATTTCAGAATTTCAGCGTGC
TAGGAACGGAGCAGCGGACCGGCGACGTCACCAAATAAACGCCCATCACCATGGACGAGGATGACAACCTGTCCAATGCCGACATAAGCATAGAT
GACGAGGAGGTGGTGCGGGAGCAGACCCACCATCCGCCCATGCAAGAGGATCAGGAGCTGGATAACGAAGATGGGTCATCCGACGTGGATCTGTC
TTCGGTGTACGTCGTGCCACCCATAGTCTCGGCACCATCGCCCGCATCAGTGCGCATCGCTGGTGGATCCACAATTGGTGGCGGAGGGGTCGCAG
CTGGAGCAGTTCCAACAACCACCGATAACTCGCATTCCCCCTTCCACGATTGGGATTCCAGTGTGGCGGCCGCTGCTGCTCCACCGCCGCCACCG
CCCAGGACAGGACCAACTACAACTACAAGCTCCGGCACAGCCGCGGAATCGGGAGCCGCGTCCGCCTTATCCGACGATGCCGGCGCCAAGCCAAG
TTTCTTCTTTGGCGCCTCCTCGTTCAGTTTGCGCAGCCGCAAGGAGGTGGCCGCCCTGATCAACACGGAATGCTGCCGTGGCAGCCCCACACCCG
ATCTCGACTCCATAATGGATACCCTATTCAATCCGGGGACGCCCATCGACAATCTGGACAACATCGAGTGGATACGATGGCTCATTGCCGGCGGA
CGGACGCCGCAGGAGTTTGTTAAAATTGGTACGTCCCAATGTGTGCATATCGATAAGTGTGTTGCATTTTCTATCGCCAAACAGCTGATCGCAAG
TCCGTTGCCCCTGAAACTCTGACCGAGCATGTGTGTGTTACCTGCGTTATGTGTGTGTGTGTCTGTGAAATGTAATGGTTGTAGGGCACGCAAAG
AAAAGGTAGAGAGGAAGAGAGCATAAAAGCAAGGTGCAAGGCAGCGTGAAGAGTGCGAGTGCACCACCATGGCAACAGCAATCAAGCGCACTCTC
TCGCACACACAGCACACTCACTACACACACATATGCACTGATTAGGGGAGTCAACTTTAGCCCAATTTAATCTCAACTGCTCATCTATTTGCAAT
GCTGTATTTGTGCATAATTTTCATCACTACTTATTACTTTTTGTGCCAGGCTGCGTATGTCGCCAAAGTTGCTTTTATCGTTTATGGTTGTTTGT
CGCGTCTAGTCTTGTCTTGTCTTGTCCCACTTGTCAGCTCTGTCACACGCACACATACACACACTCGTGCAAACTGGCGGGCGGAGACGTACACG
CACAGTGGAATGCAGCTTGCACCTTGTGGCTTTGTATCAGCTGTTTCGGTACGCCTTGCGTAATAAATGTTTCCGCAGCATCCGTCCCAAAACCA
CACGAACACGAATGTAGATGGTGCTTGATTATATGATGGCACCTTTTGTCACCGCTAGGTGCTCCTTTTTTTTTTTTTGTGTTATATTTCTTTCAC
CTTTTTGTTTGTTACTCGTTGCAAGAACAATTGCAAAATTGCACTGGTGCGGAAAAAGTTGATTGACCGTCATTGTTGTTGATTTGACAAAAACA
CGCACAGTGGTCGCGAGGGGCGGATGTGATGTGGCCCACTGTAAGCTGTCAACGGCAATTGACCGAAAGACCGTTATGTTATTGGGTGGTGTGTA
TGTGTGTGCGTGCGTGCGTGTATGGGTGAGGGTGAGAGAGTGCACCTTTTTTCCGTTCCCATGTCATGTCACCTCCCCTTCCCTTCGCCACACCC
TTGCTCCTCCATTCGGACCTTGTCCAAAAGTTCTCAGTTAGAAAGAGACTGCTGAGCCAAGATAGTGAGAGCGAGAGAGAGTTGCTAACTTTCCG
TTGATCGATCGCTATTACAATTTTACAACATTGTCAATCAACTTTCCGCTGCACTGTGGTTGTTATTGGCCAATCCATTCGATTTCCTTCCGCAT
GCGGCGGCCGACAACGTTGACCTTTTTAGTCAACAAGGTCCGAGCGGAATACGTACATACATATGAACATACATATGTGTATAAACTACGAAACA
TAAAACAATCGTATGTACATAAATACATGTACATACGCCCCAGAACGCAGGCCGAAGACAAAAAATCAAAGAGTCACGCAACTAAAAGCAAGAAA
TTAACTAAGCAATGAGTGCATCATTTTATTTTTGGAACTCAAATCAAATCAATAGCAATAGCAAGGCAATGCGGTCGGTCAGAAAAAATCAGCTA
GCCTCGACTGGTTTTACAATTTCACCTCATCGCTCAAATTTGCAAGCGATATTTAATCGTTTTGTGATTAGAGGCGGGAACAATGCTTTGCAATC
GACCGATTATTTCGATGATTTTGCATATGAATTCGTTGAGTTCAATTGGTTAAAAACCCCAAATACAACTTCTTAGGTCAAATTACCGTGGATAT
ATTAATAAATTATTATTATTATACACATATACAAATCATGATTAACGTACCAACAAGATTGTCTTACGCATGCCTATAAAATTGTGCTTGTGCAC
TGATTTCTTGATGTCCTTTGTCTGTAATAACCGGATTCCAATGACCCATAATATTTAAGAAAATCGATAGTTGGCCAGGGCCTCTCACATAAATA
CAGAGCAAGGTCTTAACTTTTTAAGAACTTGCGGATGTGTCTGTTGGTTAAACATAACAAATTTTTTAGCTCTGTGATTCAATGTGGCGATGCCC
TTGCTCCTTATGTGTCCAAACCTATTTTATAGCTGGCTTCTCTTCTGCGTCTGCCATATACTCAATGAATTGCTTAATGGTTTTTAATTTTTGAA
ATTTTATCTTGCAGTGCGCAGCTATGACAACCACGCCAAATGCGGTCTGGTATGGGTACCGCATGTGGTGGCCTACAGGTGCCGCACTTGCGGCA
TATCGCCCTGCATGTCCATATGCCGGGACTGCTTCAAGAAGGGCAACCACACGAACCACGACTTCAATATGTTCCTGTCACAGGCGGGCGGTGCC
TGCGATTGTGGTGACACCTCGGTCATGAAGGCGGAGGGTTTTTGCAGTGATCATGGCATCAATAATCGGGTGAATCGCGATCCGGTGCCAAACAA
TCTTTTGGCAGTGGCCGAGGCCATAATGCCCAAGCTGCTCTTCCGCCTGCTGCAGCACTTCCGTGAGCACAGCGACACCCCACTGGAGGTGCAAG
CGATAACGTCGTACTCCTGCGAGGAGTTCGCCAACATGCTGATCGATCTGAACAACATGGGCGAAATAATGCGCAAAGTGATGACGCGCACGCTG
ATAAATCCGGAGGTGTATGCCTTCTTCATGGAAGCACCGTGCCAGGACACCCGGAATGGACGCTTCTTGAAGGCGAACCGAGAGAAGTACGAGGA
TGCCGTCAATAGATTCCCAAACCCAGAGCCACCCGATGAGTACAGAGATCTGCCCGCGCTGGGCGACAAATTGGTCCACACCACGCTACTCGAAG
AGTTCATCTTCTGGACATTTAAGTTCGAGTTTCCACAGACTCTGGTCTGCTTTCTGCTGAACATGCTGCCTGATCAGGATTACAAGGTTAGTCTT
GATGGGATCATATGATTTTTACATATCTATATCAATATTTATTCGTTTTCTGCCCTAAAAGGAACACCTCACCCGCACATTTGTGATGCACTACA
GCCGCATACCGTCCGTGTTGGAAATGTCCCGTGATCCGGACACGCTCAGCAACCGGGTGGTCCACATGAGCGTCCAACTCTTCTCTAACGAAAGT
CTGGCCCTCAAGATGGTCAACGAGCTGTCGCTGCTGCACGTAATGATTATTAGTCTGAAGCTAATGATGTCCAAGATACTCATACAGAATACATT
GCATGGTGAGAATTATTTTATATATCCGACTGTAGCTCTTTGAACATTTCCATTTTTCGTTCAGATCCCAACAAGAATTTTCATTTCGTCATCGA
CTGCACGCGTCAGGTGATGAAGGACCACTGCTACTGGCCACTAGTCTCGGACTTTAACAACGTCCTTTCACACGAATCGGTGGCCCTGGTCTTTC
TGCGGGACGACAATCTCATCGATATGTGGTTCCAGTTTCTCCAGATGCTCCAGGGCATGAATGTCAATGTGCGCGAGACGGCTTCTCATGTGGAA
TTCGAGCCAAATAGCTACTATGCGGCGTTCTCCTGTGAGCTTGAGGCCAGTGCCTATCCCATGTGGTCGATTATCTCGCATCTGCAGGATGGCAC
ACATGCCCATCTGGCAAAGAAGATCATCAACTACTGTGTGACGACGCTGCACGAGTGGCTAGACTCTATTTACTTTATGGAGGCGCGTCTATCTA
TGGTTGGTATTTTCAATCCGTTTATTGCAGTTTCAATAAAATCCTTTTATTTATCCGTGCAGGAGGAGATGATGCAGGCTTCGTTCCACTTTCCC
CTGCATCGTTATCTGGCTGCCTTTGTTTGCCAGGCGGTAACTAAAATGGGAATCAGTCTGAACGATGTGCTGCCCTCACGCCCCTATCTGCTGCC
CCTGCTGATGATCCATCCACTTCGCGTCCAGGTGAGTCTTCAATCCTTTATTTCGCTTATTTTCGCTTTAAATAGTAAGAAGGTCCTCGGTTCTC
TGGTTTCTCAGATTCACATTCGTTTTATTTCTTTTGTTATTTCAATATAATTTGTTTTTATATTCTTGTCTTGCCGGATTCTGCATCTCCTGC
GGTTCGTTCTCCTCTGATCTCACTTAGACTATGCGACAGTTAAACGCAAGTGTGTATTGATAGGTAGTGTACAACTAAAAAAAAGCTATGACATA
TGTGCGGGATGGAAACAGCACCGCTTCTCTCCGCTTTAGAATCTATTCTTTGGCACCTGAACGTGGGGCATGAAGTCGTAGGTGATGATCTTGGG
GCCCAGGAAGCCGCCGTAGCCGTTGCGGCCCTTGTAGTAAATGCCAATGCCGGCTAGTGGTACTGGTGGATTCGAGACCACGTCCTGGATGTCCA
TAAACGGCACTGTGCTCTGGGCGGCATCCTTGTCCAGTCCAGTGTTAGTGAAGTCGATGTACTGATTGTGGCGCGACAGAGGTATCGAGTGTGCT
ATTGTCCGCGTAGACACGTCGGCGTTGCTCAGACGCAGTTTCTCCCTGAAATCAAGGGGTTAGTTATTTAGTTTTTGCTATCCGAAAATAGAGGA
CACACTTACCTGCGTGCGCCGCTGACATCGGTATTGTCGTTGGACTTCCAATAGCTATTGTACTCCGGCCGGATGAGCTGACCCGTCCGGAAATC
AAACTCACTGTAGTAGGCCTCCAAATTCAGATGTGTGCCCACCACACGGAATCGCACGCCGGTAACGACAAAGGAATTGTCATCCGTATCCACAT
CGTCCAGATCGATGGTGCGTTTCTCGTAGCTCAACTTATGATAATCAACGCCATTCTTCACATGACGATCAAAGACGTTGTACTTTTCCACGGGT
TTCCATTCCAGAGTGCTTTGATTGACAATACCACGAGGCAGGAGTTCGCCCTCCTGGATTTGCAGATGGAAAATGCGATTTTGCTTTACAAAACG
CAAACCAGTCACGACTCTGAAGAATAATTAGTAAATATGTGGTTGATATTTCAAAATCAACAGATTCAACTAGAACTTACCGGTTGCGCTTGACA
TCGGCGATCGTGTCCCGCAGATTGAAGAAACGATCAGACTTCAGACCCTCCTCGTCGCACAGGCAGAAGCAGTAGCTGCAGTGCCAGAGAAGGTA
ACGCCACCAGCTGTCCACCTTGGTGGTGCCCCTGGTGCACTTACCCCGCTGGCCAAGGACGCGTCCGTTTTCGTACTCGATGAACTCATAGCGCC
GCGTGCTATTCTGTGGCGACGGCACACCCACATGTCGGAGTCTACGAACCTGCAGTTGTACAGACGACCACTACATTTCGGCTGACGGAACAG
TAGAGATCCTTAAAGCAGCCTTCACTGCGGGTGGACTGATAAAAGTCACACGTCTCTCGGCAAGTTTCCTCTTTATTCAAATCCACCTCGTTTTC
AATGTAGCCTTGAAGGAGGCGCGTGACCTC

FIGURE SHEET 41

(SEQ ID NO: 103)

Exon: 1001..1643
Exon: 3720..4456
Exon: 4527..4755
Exon: 4815..5446
Exon: 5522..5965
Start ATG: 1001

Transcript No. : CT3955
ATGGACGAGGATGACAACCTGTCCAATGCCGACATAAGCATAGATGACGAGGAGGTGGTGCGGGAGCAGACCCACCATCCGCCCATGCAAGAGGA
TCAGGAGCTGGATAACGAAGATGGGTCATCCGACGTGGATCTGTCTTCGGTGTACGTCGTGCCACCCATAGTCTCGGCACCATCGCCCGCATCAG
TGCGCATCGCTGGTGGATCCACAATTGGTGGCGGAGGGGTCGCAGCTGGAGCAGTTCCAACAACCACCGATAACTCGCATTCCCCCTTCCACGAT
TGGGATTCCAGTGTGGCGGCCGCTGCTGCTCCACCGCCGCCACCGCCCAGGACAGGACCAACTACAACTACAAGCTCCGGCACAGCCGCGGAATC
GGGAGCCGCGTCCGCCTTATCCGACGATGCCGGCGCCAAGCCAAGTTTCTTCTTTGGCGCCTCCTCGTTCAGTTTGCGCAGCCGCAAGGAGGTGG
CCGCCCTGATCAACACGGAATGCTGCCGTGGCAGCCCCACACCCGATCTCGACTCCATAATGGATACCCTATTCAATCCGGGGACGCCCATCGAC
AATCTGGACAACATCGAGTGGATACGATGGCTCATTGCCGGCGGACGGACGCCGCAGGAGTTTGTTAAAATTGTGCGCAGCTATGACAACCACGC
CAAATGCGGTCTGGTATGGGTACCGCATGTGGTGGCCTACAGGTGCCGCACTTGCGGCATATCGCCCTGCATGTCCATATGCCGGGACTGCTTCA
AGAAGGGCAACCACACGAACCACGACTTCAATATGTTCCTGTCACAGGCGGGCGGTGCCTGCGATTGTGGTGACACCTCGGTCATGAAGGCGGAG
GGTTTTTGCAGTGATCATGGCATCAATAATCGGGTGAATCGCGATCCGGTGCCAAACAATCTTTTGGCAGTGGCCGAGGCCATAATGCCCAAGCT
GCTCTTCCGCCTGCTGCAGCACTTCCGTGAGCACAGCGACACCCCACTGGAGGTGCAAGCGATAACGTCGTACTCCTGCGAGGAGTTCGCCAACA
TGCTGATCGATCTGAACAACATGGGCGAAATAATGCGCAAAGTGATGACGCGCACGCTGATAAATCCGGAGGTGTATGCCTTCTTCATGGAAGCA
CCGTGCCAGGACACCCGGAATGGACGCTTCTTGAAGGCGAACCGAGAGAAGTACGAGGATGCCGTCAATAGATTCCCAAACCCAGAGCCACCCGA
TGAGTACAGAGATCTGCCCGCGCTGGGCGACAAATTGGTCCACACCACGCTACTCGAAGAGTTCATCTTCTGGACATTTAAGTTCGAGTTTCCAC
AGACTCTGGTCTGCTTTCTGCTGAACATGCTGCCTGATCAGGATTACAAGGAACACCTCACCCGCACATTTGTGATGCACTACAGCCGCATACCG
TCCGTGTTGGAAATGTCCCGTGATCCGGACACGCTCAGCAACCGGGTGGTCCACATGAGCGTCCAACTCTTCTCTAACGAAAGTCTGGCCCTCAA
GATGGTCAACGAGCTGTCGCTGCTGCACGTAATGATTATTAGTCTGAAGCTAATGATGTCCAAGATACTCATACAGAATACATTGCATGATCCCA
ACAAGAATTTTCATTTCGTCATCGACTGCACGCGTCAGGTGATGAAGGACCACTGCTACTGGCCACTAGTCTCGGACTTTAACAACGTCCTTTCA
CACGAATCGGTGGCCCTGGTCTTTCTGCGGGACGACAATCTCATCGATATGTGGTTCCAGTTTCTCCAGATGCTCCAGGGCATGAATGTCAATGT
GCGCGAGACGGCTTCTCATGTGGAATTCGAGCCAAATAGCTACTATGCGGCGTTCTCCTGTGAGCTTGAGGCCAGTGCCTATCCCATGTGGTCGA
TTATCTCGCATCTGCAGGATGGCACACATGCCCATCTGGCAAAGAAGATCATCAACTACTGTGTGACGACGCTGCACGAGTGGCTAGACTCTATT
TACTTTATGGAGGCGCGTCTATCTATGGTTGGTATTTTCAATCCGTTTATTGCAGTTTCAATAAAATCCTTTTATTTATCCGTGCAGGAGGAGAT
GATGCAGGCTTCGTTCCACTTTCCCCTGCATCGTTATCTGGCTGCCTTTGTTTGCCAGGCGGTAACTAAAATGGGAATCAGTCTGAACGATGTGC
TGCCCTCACGCCCCTATCTGCTGCCCCTGCTGATGATCCATCCACTTCGCGTCCAGATTCACATTCGTTTTTATTTCTTTTGTTATTTTCAATAT
AATTTGTTTTTATATTCTTGTCTTGCCGGATTCTGCATCTCCTGCGGTTCGTTCTCCTCTGATCTCACTTAGACTATGCGACAGTTAAACGCAAG
TGTGTATTGATAGGTAGTGTACAACTAAAAAAAAGCTATGACATATGTGCGGGATGGAAACAGCACCGCTTCTCTCCGCTTTAGAATCTATTCTT
TGGCACCTGAACGTGGGGCATGAAGTCGTAGGTGATGATCTTGGGGCCCAGGAAGCCGCCGTAGCCGTTGCGGCCCTTGTAGTAAATGCCAATGC
CGGCTAGTGGTACTGGTGGATTCGAGACCACGTCCTGGATGTCCATAAACGGCACTGTGCTCTGGGCGGCATCCTTGTCCAGTCCAGTGTTAGTG
AAGTCGATGTACTGATTGTGGCGCG
(SEQ ID NO: 104)

Start ATG: 1

MDEDDNLSNADISIDDEEVVREQTHHPPMQEDQELDNEDGSSDVDLSSVYVVPPIVSAPSPASVRIAGGSTIGGGGVAAGAVPTTTDNSHSPFHD
WDSSVAAAAAPPPPPPRTGPTTTTSSGTAAESGAASALSDDAGAKPSFFFGASSFSLRSRKEVAALINTECCRGSPTPDLDSIMDTLFNPGTPID
NLDNIEWIRWLIAGGRTPQEFVKIVRSYDNHAKCGLVWVPHVVAYRCRTCGISPCMSICRDCFKKGNHTNHDFNMFLSQAGGACDCGDTSVMKAE
GFCSDHGINNRVNRDPVPNNLLAVAEAIMPKLLFRLLQHFREHSDTPLEVQAITSYSCEEFANMLIDLNNMGEIMRKVMTRTLINPEVYAFFMEA
PCQDTRNGRFLKANREKYEDAVNRFPNPEPPDEYRDLPALGDKLVHTTLLEEFIFWTFKFEFPQTLVCFLLNMLPDQDYKEHLTRTFVMHYSRIP
SVLEMSRDPDTLSNRVVHMSVQLFSNESLALKMVNELSLLHVMIISLKLMMSKILIQNTLHDPNKNFHFVIDCTRQVMKDHCYWPLVSDFNNVLS
HESVALVFLRDDNLIDMWFQFLQMLQGMNVNVRETASHVEFEPNSYYAAFSCELEASAYPMWSIISHLQDGTHAHLAKKIINYCVTTLHEWLDSI
YFMEARLSMVGIFNPFIAVSIKSFYLSVQEEMMQASFHFPLHRYLAAFVCQAVTKMGISLNDVLPSRPYLLPLLMIHPLRVQIHIRFYFFCYFQY
NLFLYSCLAGFCISCGSFSSDLT*
(SEQ ID NO: 105)

Classification: hypothetical

Celera Sequence No. : 142000013384425
TTATCCGGGCACTTACACATCACATTATAATCTTATATCTCTTACTCTCTTAATCCAATAGTATGATATTAATTTTTGCTCGATTTTTATAGAAA
GGCGATTCCCTGAAAAGATGCCAAACCGTGCTCATGGAAAGCGATGAAATGGAGCAGAAAACCTGCGTTGGGTATCGAAGCAAAGTCTCCATGGA
GTCCGCCGTTCTGTTCTCGGTACTGTTGTCCACCAACCATGAGCTTTCTATTGGAAAGATGCTCGATATGAGTGAGATTCACGAAAGAATGCGGC
GCGCCAAACAGTCATTCGAGGATACTGCTAGAGTTACTCCGTTCCGAACGAACATTGATGACCTAATCTCCGATTTGGATGTCTGTGCTAAGGTC
AAATCCAAACTTTGTCGAGTAATAAGTGATTGTAAAAAGTACTAGAAAGGATTAGCTATATCTTTTATCTATATTTAATACTTTTATTTCATTTT
AATCAATAGTATAAAATTATTTCTCTGGATTTTAGGTGACTATAAGAAGACTATTTTTGTAATATTTTTGAACCATTTAAGCTCAAAATACAACT
TACTATTCATATTTTAATATATAATTCCATGTTATCATGAATTTATTAGAATTTATATATACAAGTAAAGATTCGAAATTCAGCTTCGACCCGCT
CCTTACGATTGTTATCTATATTATCAATTAATACATTAAGGTTGCTCATCATAATTGTTAATTGTTTGCTCATAAAAGCGTTTAAAAATGAAAGA
TGGGAAATACTTTTTTAGCTTTCCCTTATTGTCTCTAAAGTAAGATCGTAGTCATGATACAAGCTCTTCCTAAATGTGTAGAAATAATGATACAT
TTGTATTATATATACATAAACGCGAAATATTAAAAAGAAACATTCCGAAAATTAAAGAATTGCATTAGTTTACAACAAAAACTATCGAATCTCTC
TAATCAAAACGACGCGCCAAGCCAAATTTAGTACATTATCTGTGCTGAATCATTTTCGCTGTGCCGCAATATTTAATTAACTGCAGCGATCATTG
CAGTTTTAGCCACCAGAGAAGCGTAACATAGAAATCAAAATGCAGAAGGTTGCACTGCTTCTAGTCGCCTTCCTGGCTGCGGCCGTGGCCCACCC
AAATTCGCAGGAGAAGCCCGGATTGCTGCGCGTACCGCTCCACAAATTTCAGTCGGCCCGCCGGCACTTTGCGGATGTGGGCACGGAGCTGCAGC AATTGCGCATTAGGTACGGCGGAGGTGATGTGCCGGAACCGCTGTCCAACTATATGGACGCGCAGTACTATGGGCCCATTGCCATTGGCTCGCCA
CCGCAGAACTTCCGTGTGGTTTTCGACACCGGCTCCTCGAACTTGTGGGTGCCGTCCAAGAAGTGCCACCTGACCAACATCGCCTGTTTGATGCA
CAACAAGTACGATGCCTCCAAGTCGAAGACCTACACCAAGAACGGCACTGAGTTCGCCATCCAGTATGGCTCGGGCAGCTTGTCCGGATACCTGT
CCACGGATACGGTGTCCATTGCCGGCCTGGACATCAAGGATCAGACATTCGCTGAGGCGCTCAGTGAGCCGGGCCTGGTCTTCGTAGCTGCCAAG
TTCGACGGCATCCTAGGCCTGGGCTACAACTCCATCTCGGTGGACAAGGTGAAGCCGCCATTTTACGCCATGTACGAACAGGGTTTGATCTCCGC
TCCGGTGTTCTCATTCTACCTGAATCGCGATCCCGCCTCGCCCGAGGGCGGTGAGATCATCTTTGGCGGCTCCGATCCCAACCACTACACTGGTG
AATTCACCTACTTGCCCGTTACCCGCAAGGCCTACTGGCAAATCAAGATGGATGCCGCCTCCATTGGCGATTTGCAGCTGTGCAAGGGCGGTTGC
CAGGTGATCGCTGACACCGGTACCTCACTAATTGCTGCGCCCTTGGAAGAGGCCACCTCTATTAACCAGAAGATTGGTGGAACTCCCATCATCGG
TGGTCAGGTGAGTACCATGCTCTAAGTTCTCACATGAAGCACTGCTAATCCTCTTAATTTCTTACTTTAGTATGTGGTTTCTTGCGATCTCATTC
CCCAATTGCCGGTAATCAAGTTTGTGCTGGGCGGAAAGACCTTCGAGCTCGAGGGCAAGGACTATATTCTCCGTGTGGCCCAGATGGGTAAGACC
ATCTGTCTGTCCGGCTTTATGGGCTTGGACATCCCCCCTCCAAACGGACCCTTGTGGATCCTCGGTGACGTTTTCATTGGCAAATACTACACCGA
GTTTGACATGGGCAACGATCGTGTGGGCTTCGCCGATGCCAAATAATCGAACAAAGAAAAGTATACTTAAAATTTAAATTGTAAACATTATCGAT
CGATCCCATTGCGGGTTTCTCCGAAGAATAATATATAAATTATCATTTTAGTAGATTTTCCATATATTTATTAGCGTAAGTTTATTAATTACAAT
AGGGCTTGCGCGGTCTGCACTTAATGAGACGAATAGTAAGTACGTGGCGATGACCGACGCTTCTAATCTTCCAAAATCGACTAACTTAAGTATAG
CAAGAGTTCTTATCTCTAAAGCTTAACAAGTTACAGTTTCTTATAGGTAAAGCTCGATCTATAGATGGGAAAAGCACTTGAGGCTTACGACTATA
TTTCGGGTGTTTTGTGATTGTGTTAACTCCTCCCCTTCTAAGACGAAGGCTGTCCACAGACTTTTTACAATTGGCAAATCTATTTGAAAGCGGAT
CTTACGGGTAACATTGGTTGTGCACTAAGTTCCCATACTGCCAACCTGGTACTGCGTTAAACCATCGAAGGGAAGGCAGCTCTGCGTGTCTGGAT
GATCCGAGAAGTTCGTAAATGCTGCTGATTCTCCATGTCATGGGTTCGCAACAAGGTTCTGGAGATGATCGTAG
(SEQ ID NO: 106)

Exon: 1001..2002
Exon: 2066..2441
Start ATG: 1085

Transcript No. : CT3996
CATTTTCGCTGTGCCGCAATATTTAATTAACTGCAGCGATCATTGCAGTTTTAGCCACCAGAGAAGCGTAACATAGAAATCAAAATGCAGAAGGT
TGCACTGCTTCTAGTCGCCTTCCTGGCTGCGGCCGTGGCCCACCCAAATTCGCAGGAGAAGCCCGGATTGCTGCGCGTACCGCTCCACAAATTTC
AGTCGGCCCGCCGGCACTTTGCGGATGTGGGCACGGAGCTGCAGCAATTGCGCATTAGGTACGGCGGAGGTGATGTGCCGGAACCGCTGTCCAAC
TATATGGACGCGCAGTACTATGGGCCCATTGCCATTGGCTCGCCACCGCAGAACTTCCGTGTGGTTTTCGACACCGGCTCCTCGAACTTGTGGGT
GCCGTCCAAGAAGTGCCACCTGACCAACATCGCCTGTTTGATGCACAACAAGTACGATGCCTCCAAGTCGAAGACCTACACCAAGAACGGCACTG
AGTTCGCCATCCAGTATGGCTCGGGCAGCTTGTCCGGATACCTGTCCACGGATACGGTGTCCATTGCCGGCCTGGACATCAAGGATCAGACATTC
GCTGAGGCGCTCAGTGAGCCGGGCCTGGTCTTCGTAGCTGCCAAGTTCGACGGCATCCTAGGCCTGGGCTACAACTCCATCTCGGTGGACAAGGT
GAAGCCGCCATTTTACGCCATGTACGAACAGGGTTTGATCTCCGCTCCGGTGTTCTCATTCTACCTGAATCGCGATCCCGCCTCGCCCGAGGGCG
GTGAGATCATCTTTGGCGGCTCCGATCCCAACCACTACACTGGTGAATTCACCTACTTGCCCGTTACCCGCAAGGCCTACTGGCAAATCAAGATG
GATGCCGCCTCCATTGGCGATTTGCAGCTGTGCAAGGGCGGTTGCCAGGTGATCGCTGACACCGGTACCTCACTAATTGCTGCGCCCTTGGAAGA
GGCCACCTCTATTAACCAGAAGATTGGTGGAACTCCCATCATCGGTGGTCAGTATGTGGTTTCTTGCGATCTCATTCCCCAATTGCCGGTAATCA
AGTTTGTGCTGGGCGGAAAGACCTTCGAGCTCGAGGGCAAGGACTATATTCTCCGTGTGGCCCAGATGGGTAAGACCATCTGTCTGTCCGGCTTT
ATGGGCTTGGACATCCCCCCTCCAAACGGACCCTTGTGGATCCTCGGTGACGTTTTCATTGGCAAATACTACACCGAGTTTGACATGGGCAACGA
TCGTGTGGGCTTCGCCGATGCCAAATAATCGAACAAAGAAAAGTATACTTAAAATTTAAATTGTAAACATTATCGATCGATCCCATTGCGGGTTT
CTCCGAAGAATAATATATAAATTATCATTTTAGTAGATTTTCCATATA
(SEQ ID NO: 107)

Start ATG: 85

MQKVALLLVAFLAAAVAHPNSQEKPGLLRVPLHKFQSARRHFADVGTELQQLRIRYGGGDVPEPLSNYMDAQYYGPIAIGSPPQNFRVVFDTGSS
NLWVPSKKCHLTNIACLMHNKYDASKSKTYTKNGTEFAIQYGSGSLSGYLSTDTVSIAGLDIKDQTFAEALSEPGLVFVAAKFDGILGLGYNSIS
VDKVKPPFYAMYEQGLISAPVFSFYLNRDPASPEGGEIIFGGSDPNHYTGEFTYLPVTRKAYWQIKMDAASIGDLQLCKGGCQVIADTGTSLIAA
PLEEATSINQKIGGTPIIGGQYVVSCDLIPQLPVIKFVLGGKTFELEGKDYILRVAQMGKTICLSGFMGLDIPPPNGPLWILGDVFIGKYYTEFD
MGNDRVGFADAK*
(SEQ ID NO: 108)

Name: Cathepsin D
Classification: endopeptidase

Celera Sequence No. : 142000013383905
CTTATTCCTTGTTCCAGGCTGCCAGGTATTTCATGAGGTCCGTGAGACTCTCGAAATCGGTGCGGCTGGCTGGTGGTTCGTCCTTGGTGATTCTT
GGCAGTGCATTGCCCATCTTGAGGCGGAACTCCTGGAACTGCGAACGAAACGAAAGATTTAAAGCGAAATTCATTGAACAAATCGGAGGCATGCT
CACATCCTTGGCTCCGGATAGCTTCCAGAAGCCGTAGCAGAAGGCGCCGGTGCCCATCACGGCGTACAGTGTGCCCCAGCCCAGCGCCCGCAGGG
CCAGGGTGGCGCCCTCGTCCATCAGGATCATGCCTTGCCGCGTTCCAGCCTGCTGGAGGACCTTGCTATCCGTCTTCTTGGCGGTGGCCAGCGTG
CGCGAGAAGCCGAACAGAGCGGACACCCCGCCCACCAAACCCAGAAAGGCGGCGGCTAGAAAGGAGGATGAAATGGAGTTGTACTTCAGTCAGTT
GCTGGCTGATATATATGCGTGTGTCTGTATGTGTTTGGAGAACCACCTACCCTGGATGCGGAACTTGCGCTCCTTCTCGGCGGCCACTGCATCCG
CGCTGGTGCCGGCCTCGCTCATCCTTCTCAATTGCGATTTATTGTTGTCGTAACTACTAATGCCCGAATTGGATCGCACAACACAGCTGATTGCT
TGACCGCTCTTGACAACCAACACTGGTGCCGCAGCTGCCACTGCCACTGACGCGTTCGCAGAGGTGCTAAGATGGCGGGAGGGAAGCTAGAAGTG
AAGTGCTAAAAGATAGTTCAAAATATTCAACAGGTACTGGCCTTTCTCACTGACTATGAGAGTCAATTTGATTTTAATGTGCTGCATTTAATTTA
TTTGTTAAATTACTAACTAATACTAATAGATATATTTATATAAAAGATATAGCTAAAAAACGTCAGTCTGGCAACCCTGCTACAACGACCGCAAT
ATGGTATGGTATTTCGCCGCTCGCCCTGCAGTCACACTTTTCGGTCGGCGTTGTCCGCATTTTCACATCGCATCGCGTCTGAAAAAACGGGCTAA
TTCGCATTCGCAATCGCCTGTAGGGCCCGACTGGTATAGAATGCACGCCCAGCGTGCCAGCAACAAACAGTGATTGTTTACCCAGCCTTCTATTT
GGGCTTTCGCGTTTTTCGAGCTCCTTCTTTTCCCTTCCCGGTCGTATCCCTTGCCTTTTGCACGAGGTGAAAAGTGTGACGACGCAGCAGAAAAA
GCAAAAGCAAAAAAAAGGTGGAACAAAAAAAAACCGCACACACACACCGAAAGCAGGCTCCACTTTGGTCTAGTGGCCACCAGTATCGCTGACGA
CCAGGATGAGCACCCCCACGGACTCGAAGGCGCCGTTGCGCCAGGTGAAGCGCGTACAGTTCGGCATTTTGTCCCCTGATGAAATTGTAAGTGCG GCTCACAGATTCATTCGATCGACGCCATATTGAAAAATTGAACAATATTGTAAACGCAAAAATAGCATTCCATCAATTCGCAATTCGTATATCGT
GGTTTTATATGGTCTATATGGGAAATGCTTATTTCATGTTCACATGCATTCCAGTAACGCGAGCAGGACAACAAATAACAGATAGTTCAAGTCCT
GTATCTTTAGGATCTTAAGCGAAACTCACTAAATATTCGATTAACTCGTAAAACCCTTGTATCAGAAATGTTTTCCAGCTGAATATCATTACTTC
TCAATAAAGTTTATGAATATATTACGTAAAGAAATTGTATATTTGTTATTAGTTTCCTGGGAAAGTTCCAAGTCATAGCAAAATAAAACACAATT
ATACCCTGCTTAGATTTTGGGAACTTGGAATCTATTATTTCGAATATCAAGTTATTGATGCGTATATCTAAAGGGTTCAAGACAAGGGAATTCAG
ATATATATATTCTATCTATGATCCTTCAAGCACCTGTTGGCCATATCAATATGACACGCACTTTAAGAATTTGACTTTATTTGATCCACATGTGT
TACTTCTTTCCTGCTTGCAGCGTCGCATGTCCGTCACCGAGGGTGGCGTCCAGTTTGCGGAGACAATGGAGGGCGGACGACCAAAGCTGGGCGGA
TTGATGGATCCGCGCCAGGGTGTCATAGACAGGACGTCGCGCTGTCAGACGTGCGCCGGCAATATGACCGAGTGCCCCGGTCACTTTGGACACAT
CGACCTGGCCAAACCAGTGTTCCACATCGGCTTCATCACCAAGACAATTAAGATTTTGCGATGTGTGTGCTTCTACTGCTCCAAAATGTTGGTCT
CGCCACACAATCCAAAGATCAAGGAGATCGTTATGAAGTCTAGGGGACAGCCGCGTAAGCGCCTGGCCTACGTCTATGATCTGTGCAAGGGCAAG
ACGATTTGCGAGGGCGGCGAGGACATGGATCTCACCAAGGAGAACCAGCAGCCGGATCCAAACAAAAAGCCCGGCCACGGCGGTTGCGGTCACTA
CCAGCCGTCGATCCGGAGAACAGGACTGGATCTCACCGCCGAGTGGAAGCATCAGAACGAGGATTCGCAGGAGAAGAAGATCGTGGTCTCGGCAG
AGCGGGTTTGGGAAATCCTTAAGCATATCACCGATGAGGAGTGCTTTATTCTGGGCATGGATCCCAAGTATGCGCGTCCCGATTGGATGATCGTG
ACCGTCCTGCCTGTTCCACCGTTGGCCGTACGGCCAGCGGTCGTGATGTTTGGTGCTGCCAAGAATCAGGATGATTTGACGCACAAGCTGTCCGA
TATCATCAAGGCAAACAATGAGCTTCGCAAGAACGAGGCCAGTGGTGCCGCAGCGCATGTGATCCAGGAGAACATCAAGATGCTGCAATTCCACG
TCGCCACACTAGTGGACAACGATATGCCCGGCATGCCCAGGGCTATGCAAAAGTCGGGAAAACCCCTTAAAGCCATCAAGGCGCGACTCAAGGGT
AAGGAGGGTAGGATTCGTGGCAACTTGATGGGCAAACGTGTCGACTTCTCCGCCCGTACTGTCATCACACCCGATCCAAATCTGCGTATCGATCA
GGTCGGTGTGCCGCGTTCCATTGCCCAGAATCTAACCTTCCCCGAGCTGGTCACTCCCTTCAACATCGATCGCATGCAGGAGCTGGTGCGCAGGG
GTAATTCGCAGTATCCGGGTGCCAAGTACATTGTGCGCGACAATGGCGAGCGTATTGATCTTCGCTTTCATCCTAAATCCTCTGATTTACATCTG
CAGTGCGGCTACAAGGTAGAGCGGCATTTGCGCGACGACGATCTGGTGATCTTCAACCGACAGCCCACGCTGCACAAGATGAGTATGATGGGTCA
CAGGGTGAAAGTGTTGCCCTGGTCGACTTTCCGCATGAACCTGTCGTGTACATCGCCCTACAATGCTGATTTCGACGGCGATGAAATGAATTTGC
ACGTTCCGCAGTCCATGGAGACGCGCGCCGAGGTGGAGAACATCCACATCACACCCAGACAGATCATCACGCCGCAGGCGAACAAACCTGTCATG
GGTATCGTGCAGGACACTCTGACTGCGGTGCGAAAGATGACCAAGCGCGACGTATTCATCACGCGCGAGCAGGTGATGAATCTGCTCATGTTCCT
GCCCACGTGGGACGCTAAAATGCCGCAACCCTGCATCCTGAAACCGCGTCCCCTGTGGACGGGCAAACAGATCTTCTCCCTGATCATCCCCGGCA
ACGTGAACATGATACGCACACATTCCACGCATCCGGACGAGGAGGATGAAGGACCATACAAGTGGATCTCGCCCGGTGACACCAAGGTAATGGTG
GAGCACGGTGAACTTATCATGGGGATCCTCTGCAAGAAGTCACTGGGTACATCAGCCGGATCACTGCTGCATATTTGTTTCCTGGAACTTGGTCA
CGATATCGCTGGTCGGTTCTATGGCAACATTCAGACCGTGATCAACAATTGGTTGCTTTTCGAGGGCCATAGTATCGGTATTGGTGACACTATTG
CCGATCCCCAGACCTACAACGAGATCCAGCAGGCCATCAAGAAGGCAAAGGACGACGTGATAAACGTTATCCAAAAGGCCCACAACATGGAGCTG
GAGCCCACGCCGGGTAATACTCTGCGTCAGACGTTCGAGAACAAGGTGAACCGTATCCTAAACGATGCTCGTGACAAGACTGGTGGTTCGGCCAA
GAAATCTCTCACTGAGTACAACAATCTAAAGGCTATGGTGGTGTCTGGTTCCAAGGGTTCCAACATTAATATATCCCAGGTAAGCTACTGACTAG
CGATTTTCATTCGAACTCATTTAATGTGCTGGCATTTTTATCTTCCAGGTTATTGCTTGTGTGGGTCAACAGAACGTGGAGGGTAAGCGAATCCC
CTACGGTTTCCGCAAACGCACTCTTCCCCACTTTATTAAGGACGATTATGGTCCTGAGTCGCGCGGTTTCGTGGAGAATTCGTATCTTGCCGGCC
TGACACCCTCTGAGTTCTATTTCCACGCTATGGGTGGTCGTGAAGGTCTTATCGATACTGCTGTAAAGACAGCTGAAACCGGTTACATCCAGCGT
CGTCTTATAAAGGCTATGGAGTCGGTGATGGTTAACTACGACGGAACAGTGCGTAACTCGGTGGGCCAGCTTATTCAGCTGCGTTACGGCGAGGA
CGGTCTTTGCGGCGAGCTGGTTGAGTTCCAGAACATGCCAACGGTGAAACTGTCGAACAAGTCGTTTGAAAAGCGCTTCAAATTTGACTGGAGCA
ACGAGCGATTAATGAAAAAGGTATTTACGGATGATGTGATCAAGGAGATGACCGACAGCAGCGAAGCCATCCAGGAACTGGAGGCAGAGTGGGAT
CGTTTGGTTTCCGATCGCGACAGTTTGAGACAAATCTTCCCTAACGGCGAATCCAAGGTGGTACTGCCGTGCAACCTGCAGCGTATGATCTGGAA
TGTGCAGAAGATCTTTCACATCAACAAGCGCCTGCCCACGGATCTCTCGCCCATTCGGGTGATCAAGGGCGTTAAGACATTGCTCGAACGCTGTG
TTATTGTCACGGGAAATGATCGAATTTCAAAGCAGGCCAACGAGAACGCCACGTTGCTATTCCAGTGCCTAATCCGTTCGACACTATGTACGAAA
TACGTGTCGGAGGAGTTCCGCCTGTCCACAGAGGCGTTTGAGTGGTTGGTCGGAGAAATCGAGACGCGTTTCCAACAGGCCCAGGCCAATCCCGG
CGAGATGGTGGGTGCCCTGGCTGCCCAGAGTTTGGGTGAGCCCGCTACTCAGATGACACTGAACACCTTCCATTTTGCTGGTGTGTCTTCAAAGA
ACGTAACATTGGGTGTGCCGCGTCTCAAGGAGATTATCAACATATCCAAAAAGCCCAAAGCGCCGTCGCTAACCGTTTTCCTTACTGGCGGCGCT
GCTCGCGATGCGGAGAAGGCCAAGAACGTACTGTGCCGCCTGGAGCATACCACGCTGCGCAAGGTTACGGCCAATACGGCTATTTACTACGACCC
GGATCCGCAGAGAACGGTGATATCCGAGGATCAAGAATTTGTGAATGTCTACTACGAAATGCCCGACTTTGATCCCACACGCATTTCGCCCTGGT
TGCTACGTATTGAATTGGACCGCAAGCGGATGACGGACAAGAAGCTGACAATGGAACAGATCGCCGAGAAGATTAACGTGGGCTTCGGGGAGGAT
CTCAATTGTATTTTCAATGACGACAATGCCGATAAGCTGGTGCTGCGCATTAGGATCATGAACAACGAAGAGAACAAGTTCCAGGACGAAGACGA
GGCCGTCGACAAGATGGAGGACGACATGTTCTTGCGCTGCATTGAGGCCAACATGCTGTCGGACATGACACTGCAGGGTATCGAAGCCATCGGCA
AGGTGTACATGCATCTGCCACAGACCGACAGCAAGAAGCGTATCGTGATCACTGAGACCGGAGAGTTTAAGGCCATCGGCGAGTGGCTGCTCGAG
ACGGACGGCACATCGATGATGAAAGTGCTGTCTGAGCGTGACGTGGACCCAATCCGAACATCCTCCAACGATATTTGCGAGATATTCCAGGTGCT
GGGCATCGAGGCGGTGCGAAAGTCTGTCGAAAAGGAGATGAACGCCGTGTTGCAGTTCTACGGCCTGTACGTGAACTATCGTCACTTGGCCCTGT
TGTGCGATGTGATGACGGCCAAGGGCCATCTGATGGCCATCACCCGTCACGGCATTAACAGGCAAGACACTGGTGCCCTTATGCGTTGCTCCTTT
GAGGAGACAGTGGATGTGCTAATGGATGCCGCCGCTCACGCCGAAACGGATCCCATGAGGGGCGTCTCTGAGAACATTATCATGGGACAGCTGCC
CAAAATGGGTACCGGCTGCTTTGACCTTCTGCTCGATGCAGAGAAGTGTCGTTTCGGCATCGAGATTCCCAATACGTTGGGCAACAGTATGCTAG
GTGGCGCCGCTATGTTCATTGGCGGTGGATCGACACCGAGCATGACGCCACCGATGACGCCGTGGGCTAACTGCAACACGCCGCGATACTTCTCT
CCACCCGGCCACGGTAAGTAAATCTATCCATTATGGGTTTTTGATTTACTCTCGACTCAGCAACGCTATATCTTTTGTTAATTAACTTTTTTGA
TGCGATTGCCTAATATATTCAATCTCTTTCTTTCTTGTGCTTGCAGTAAGTGCCATGACTCCTGGCGGTCCCAGTTTCTCGCCTTCGGCTGCATC
GGATGCGTCCGGAATGTCGCCTAGCTGGTCGCCGGCTCATCCGGGCTCATCGCCCAGTTCACCAGGACCTTCGATGTCGCCGTATTTCCCAGCCT
CGCCGAGTGTTTCTCCCTCTTATTCGCCAACGAGTCCGAACTACACGGCATCTTCTCCCGGTGGAGCCTCGCCGAATTACTCGCCCTCGAGTCCG
AACTATTCGCCGACGTCGCCGCTTTATGCAAGTCCACGTTACGCATCGACAACGCCAAATTTCAATCCACAGTCGACGGGTTACTCGCCATCTTC
ATCGGGATACTCGCCAACATCCCCGGTCTACTCGCCCACGGTGCAATTCCAGTCGAGTCCGTCGTTTGCGGCAGCGGTAGCAACATTTACTCGC
CGGGCAATGCGTACTCGCCCAGCTCGTCCAACTACTCCCCCAATTCACCATCCTACTCGCCGACATCACCATCGTACTCGCCGTCAAGTCCTTCG
TACTCGCCAACGTCGCCTTGCTATTCGCCCACATCGCCTTCGTACTCGCCAACGAGTCCGAACTACACACCCGTAACACCCTCATACTCGCCGAC
AAGTCCGAACTATTCAGCGTCGCCGCAATATTCTCCAGCCTCGCCAGCTTACTCGCAAACGGGGGTGAAGTACTCACCGACATCGCCGACGTACT
CGCCGCCGTCACCATCGTACGATGGGTCTCCCGGATCACCACAATATACGCCAGGATCTCCGCAGTACTCGCCGGCCTCGCCTAAGTACTCGCCG
ACCTCACCGCTGTACTCGCCCAGCTCGCCGCAGCACTCGCCCTCAAACCAGTACAGCCCAACAGGATCGACCTATTCGGCGACGAGTCCGCGGTA
CTCGCCGAACATGTCCATCTACTCGCCGAGCAGCACCAAGTACTCGCCCACCTCGCCAACGTACACACCGACGGCCCGCAACTACTCGCCCACGT
CACCGATGTACTCGCCAACGGCTCCATCGCACTACAGTCCCACGAGTCCGGCCTACTCGCCCAGCAGTCCCACGTTCGAGGAGAGCGAAGACTGA
GGAAGGGAGGACGGGGGTAGCTCCCCCAGCACGTCCCGATCTCCGGGGCGGTCAAGCCGTAGTTAAGTACCGACTACGCTCGATCGCCCGAACGG
GAAAGGTGAATTTAATAATATTATGTTTGTATACAGCAAATAGGTCTCTCATACAAAATTCAATACTGTTTGCAAAAGTAGCTTTAAACAAGTTG
TATAAATTAGCCTACAGTTTCGTATTTGGTTTTGTGGTAAAGTAAACATTTTGAATTGTTTGCGTTAACCAGAAAAGCGAATTCGAAGCCATTTA
TATTTGCACAAATTGTTTCAAGTTGCAATTCTCGAACTGTATTCGATAATGCGAATCTATTTCTTTGCACAACCCACTGTATGAAATTGTTTACT

FIGURE SHEET 44

AACTGGAAGACTCTTGTCACTCTTCTGCAAAGTACTTTCACATTTTTTGAATATCCCTATTCTTATTTTGCCTAATGTTAGTATAAAGACCCTA
GTTATTAAAAACAACAACAAAACAAGCCAACGTCAGACACTATTTGTAGCGTTTTCCATATACCCTTTAAATCCCTAATTAACCCGATCAGTTGT
TTTCGCCTGCACACAAATGTTACTTATAAAGCATAAGAATGCAGGCACCCACCCATACACTACACTATATATTCATATATATTTTTACGTCCGAC
ACATTTTTGTAAATTATGACAGAAAACAAAATAGAAAATTATAAAATAAAAACCACAAAAAAATACTCAACAACATTGGTTTATTTACTTTACTA
AACTGATATGCTCATTCTGGCAGACTACTGCAATTACTTGTAGTTGATTTAGGGATTTGAGAGCCAGTGCGGCCACTCTTGGATCTCGTTGTATA
GAGTCAGTCCGGGACTCTGGGTGCTGATCACCTGGGAGCCGGCGATCAGGGCGTAATCCTCGCTCAGCTCACCCTGCTGCACTCCGCAGGCCAGC
AGATCTTTGGCCGCCTGGAGAGCCGCATCCGATGGAAGTTTATCTATCGGAGATGTTGGGCATGTAG
(SEQ ID NO: 109)

Exon: 1001..1416
Exon: 2016..4259
Exon: 4324..6568
Exon: 6697..7807
Start ATG: 1336

Transcript No. : CT4016
TTGTCCGCATTTTCACATCGCATCGCGTCTGAAAAAACGGGCTAATTCGCATTCGCAATCGCCTGTAGGGCCCGACTGGTATAGAATGCACGCCC
AGCGTGCCAGCAACAAACAGTGATTGTTTACCCAGCCTTCTATTTGGGCTTTCGCGTTTTTCGAGCTCCTTCTTTTCCCTTCCCGGTCGTATCCC
TTGCCTTTTGCACGAGGTGAAAAGTGTGACGACGCAGCAGAAAAAGCAAAAGCAAAAAAAAGGTGGAACAAAAAAAAAACCGCACACACACACCGA
AAGCAGGCTCCACTTTGGTCTAGTGGCCACCAGTATCGCTGACGACCAGGATGAGCACCCCCACGGACTCGAAGGCGCCGTTGCGCCAGGTGAAG
CGCGTACAGTTCGGCATTTTGTCCCCTGATGAAATTCGTCGCATGTCCGTCACCGAGGGTGGCGTCCAGTTTGCGGAGACAATGGAGGGCGGACG
ACCAAAGCTGGGCGGATTGATGGATCCGCGCCAGGGTGTCATAGACAGGACGTCGCGCTGTCAGACGTGCGCCGGCAATATGACCGAGTGCCCCG
GTCACTTTGGACACATCGACCTGGCCAAACCAGTGTTCCACATCGGCTTCATCACCAAGACAATTAAGATTTTGCGATGTGTGTGCTTCTACTGC
TCCAAAATGTTGGTCTCGCCACACAATCCAAAGATCAAGGAGATCGTTATGAAGTCTAGGGGACAGCCGCGTAAGCGCCTGGCCTACGTCTATGA
TCTGTGCAAGGGCAAGACGATTTGCGAGGGCGGCGAGGACATGGATCTCACCAAGGAGAACCAGCAGCCGGATCCAAACAAAAAGCCCGGCCACG
GCGGTTGCGGTCACTACCAGCCGTCGATCCGGAGAACAGGACTGGATCTCACCGCCGAGTGGAAGCATCAGAACGAGGATTCGCAGGAGAAGAAG
ATCGTGGTCTCGGCAGAGCGGGTTTGGGAAATCCTTAAGCATATCACCGATGAGGAGTGCTTTATTCTGGGCATGGATCCCAAGTATGCGCGTCC
CGATTGGATGATCGTGACCGTCCTGCCTGTTCCACCGTTGGCCGTACGGCCAGCGGTCGTGATGTTTGGTGCTGCCAAGAATCAGGATGATTTGA
CGCACAAGCTGTCCGATATCATCAAGGCAAACAATGAGCTTCGCAAGAACGAGGCCAGTGGTGCCGCAGCGCATGTGATCCAGGAGAACATCAAG
ATGCTGCAATTCCACGTCGCCACACTAGTGGACAACGATATGCCCGGCATGCCCAGGGCTATGCAAAAGTCGGGAAAACCCCTTAAAGCCATCAA
GGCGCGACTCAAGGGTAAGGAGGGTAGGATTCGTGGCAACTTGATGGGCAAACGTGTCGACTTCTCCGCCCGTACTGTCATCACACCCGATCCAA
ATCTGCGTATCGATCAGGTCGGTGTGCCGCGTTCCATTGCCCAGAATCTAACCTTCCCCGAGCTGGTCACTCCCTTCAACATCGATCGCATGCAG
GAGCTGGTGCGCAGGGGTAATTCGCAGTATCCGGGTGCCAAGTACATTGTGCGCGACAATGGCGAGCGTATTGATCTTCGCTTTCATCCTAAATC
CTCTGATTTACATCTGCAGTGCGGCTACAAGGTAGAGCGGCATTTGCGCGACGACGATCTGGTGATCTTCAACCGACAGCCCACGCTGCACAAGA
TGAGTATGATGGGTCACAGGGTGAAAGTGTTGCCCTGGTCGACTTTCCGCATGAACCTGTCGTGTACATCGCCCTACAATGCTGATTTCGACGGC
GATGAAATGAATTTGCACGTTCCGCAGTCCATGGAGACGCGCGCCGAGGTGGAGAACATCCACATCACACCCAGACAGATCATCACGCCGCAGGC
GAACAAACCTGTCATGGGTATCGTGCAGGACACTCTGACTGCGGTGCGAAAGATGACCAAGCGCGACGTATTCATCACGCGCGAGCAGGTGATGA
ATCTGCTCATGTTCCTGCCCACGTGGGACGCTAAAATGCCGCAACCCTGCATCCTGAAACCGCGTCCCCTGTGGACGGGCAAACAGATCTTCTCC
CTGATCATCCCCGGCAACGTGAACATGATACGCACACATTCCACGCATCCGGACGAGGAGGATGAAGGACCATACAAGTGGATCTCGCCCGGTGA
CACCAAGGTAATGGTGGAGCACGGTGAACTTATCATGGGGATCCTCTGCAAGAAGTCACTGGGTACATCAGCCGGATCACTGCTGCATATTTGTT
TCCTGGAACTTGGTCACGATATCGCTGGTCGGTTCTATGGCAACATTCAGACCGTGATCAACAATTGGTTGCTTTTCGAGGGCCATAGTATCGGT
ATTGGTGACACTATTGCCGATCCCCAGACCTACAACGAGATCCAGCAGGCCATCAAGAAGGCAAAGGACGACGTGATAAACGTTATCCAAAAGGC
CCACAACATGGAGCTGGAGCCCACGCCGGGTAATACTCTGCGTCAGACGTTCGAGAACAAGGTGAACCGTATCCTAAACGATGCTCGTGACAAGA
CTGGTGGTTCGGCCAAGAAATCTCTCACTGAGTACAACAATCTAAAGGCTATGGTGGTGTCTGGTTCCAAGGGTTCCAACATTAATATATCCCAG
GTTATTGCTTGTGTGGGTCAACAGAACGTGGAGGGTAAGCGAATCCCCTACGGTTTCCGCAAACGCACTCTTCCCCACTTTATTAAGGACGATTA
TGGTCCTGAGTCGCGCGGTTTCGTGGAGAATTCGTATCTTGCCGGCCTGACACCCTCTGAGTTCTATTTCCACGCTATGGGTGGTCGTGAAGGTC
TTATCGATACTGCTGTAAAGACAGCTGAAACCGGTTACATCCAGCGTCGTCTTATAAAGGCTATGGAGTCGGTGATGGTTAACTACGACGGAACA
GTGCGTAACTCGGTGGGCCAGCTTATTCAGCTGCGTTACGGCGAGGACGGTCTTTGCGGCGAGCTGGTTGAGTTCCAGAACATGCCAACGGTGAA
ACTGTCGAACAAGTCGTTTGAAAAGCGCTTCAAATTTGACTGGAGCAACGAGCGATTAATGAAAAAGGTATTTACGGATGATGTGATCAAGGAGA
TGACCGACAGCAGCGAAGCCATCCAGGAACTGGAGGCAGAGTGGGATCGTTTGGTTTCCGATCGCGACAGTTTGAGACAAATCTTCCCTAACGGC
GAATCCAAGGTGGTACTGCCGTGCAACCTGCAGCGTATGATCTGGAATGTGCAGAAGATCTTTCACATCAACAAGCGCCTGCCCACGGATCTCTC
GCCCATTCGGGTGATCAAGGGCGTTAAGACATTGCTCGAACGCTGTGTTATTGTCACGGGAAATGATCGAATTTCAAAGCAGGCCAACGAGAACG
CCACGTTGCTATTCCAGTGCCTAATCCGTTCGACACTATGTACGAAATACGTGTCGGAGGAGTTCCGCCTGTCCACAGAGGCGTTTGAGTGGTTG
GTCGGAGAAATCGAGACGCGTTTCCAACAGGCCCAGGCCAATCCCGGCGAGATGGTGGGTGCCCTGGCTGCCCAGAGTTTGGGTGAGCCCGCTAC
TCAGATGACACTGAACACCTTCCATTTTGCTGGTGTGTCTTCAAAGAACGTAACATTGGGTGTGCCGCGTCTCAAGGAGATTATCAACATATCCA
AAAAGCCCAAAGCGCCGTCGCTAACCGTTTTCCTTACTGGCGGCGCTGCTCGCGATGCGGAGAAGGCCAAGAACGTACTGTGCCGCCTGGAGCAT
ACCACGCTGCGCAAGGTTACGGCCAATACGGCTATTTACTACGACCCGGATCCGCAGAGAACGGTGATATCCGAGGATCAAGAATTTGTGAATGT
CTACTACGAAATGCCCGACTTTGATCCCACACGCATTTCGCCCTGGTTGCTACGTATTGAATTGGACCGCAAGCGGATGACGGACAAGAAGCTGA
CAATGGAACAGATCGCCGAGAAGATTAACGTGGGCTTCGGGGAGGATCTCAATTGTATTTTCAATGACGACAATGCCGATAAGCTGGTGCTGCGC
ATTAGGATCATGAACAACGAAGAGAACAAGTTCCAGGACGAAGACGAGGCCGTCGACAAGATGGAGGACGACATGTTCTTGCGCTGCATTGAGGC
CAACATGCTGTCGGACATGACACTGCAGGGTATCGAAGCCATCGGCAAGGTGTACATGCATCTGCCACAGACCGACAGCAAGAAGCGTATCGTGA
TCACTGAGACCGGAGAGTTTAAGGCCATCGGCGAGTGGCTGCTCGAGACGGACGGCACATCGATGATGAAAGTGCTGTCTGAGCGTGACGTGGAC
CCAATCCGAACATCCTCCAACGATATTTGCGAGATATTCCAGGTGCTGGGCATCGAGGCGGTGCGAAAGTCTGTCGAAAAGGAGATGAACGCCGT
GTTGCAGTTCTACGGCCTGTACGTGAACTATCGTCACTTGGCCCTGTTGTGCGATGTGATGACGGCCAAGGGCCATCTGATGGCCATCACCCGTC
ACGGCATTAACAGGCAAGACACTGGTGCCCTTATGCGTTGCTCCTTTGAGGAGACAGTGGATGTGCTAATGGATGCCGCCGCTCACGCCGAAACG
GATCCCATGAGGGGCGTCTCTGAGAACATTATCATGGGACAGCTGCCCAAAATGGGTACCGGCTGCTTTGACCTTCTGCTCGATGCAGAGAAGTG
TCGTTTCGGCATCGAGATTCCCAATACGTTGGGCAACAGTATGCTAGGTGGCGCCGCTATGTTCATTGGCGGTGGATCGACACCGAGCATGACGC
CACCGATGACGCCGTGGGCTAACTGCAACACGCCGCGATACTTCTCTCCACCCGGCCACGTAAGTGCCATGACTCCTGGCGGTCCCAGTTTCTCG
CCTTCGGCTGCATCGGATGCGTCCGGAATGTCGCCTAGCTGGTCGCCGGCTCATCCGGGCTCATCGCCCAGTTCACCAGGACCTTCGATGTCGCC
GTATTTCCCAGCCTCGCCGAGTGTTTCTCCCTCTTATTCGCCAACGAGTCCGAACTACACGGCATCTTCTCCCGGTGGAGCCTCGCCGAATTACT
CGCCCTCGAGTCCGAACTATTCGCCGACGTCGCCGCTTTATGCAAGTCCACGTTACGCATCGACAACGCCAAATTTCAATCCACAGTCGACGGGT TACTCGCCATCTTCATCGGGATACTCGCCAACATCCCCGGTCTACTCGCCCACGGTGCAATTCCAGTCGAGTCCGTCGTTTGCGGGCAGCGGTAG
CAACATTTACTCGCCGGGCAATGCGTACTCGCCCAGCTCGTCCAACTACTCCCCCAATTCACCATCCTACTCGCCGACATCACCATCGTACTCGC
CGTCAAGTCCTTCGTACTCGCCAACGTCGCCTTGCTATTCGCCCACATCGCCTTCGTACTCGCCAACGAGTCCGAACTACACACCCGTAACACCC
TCATACTCGCCGACAAGTCCGAACTATTCAGCGTCGCCGCAATATTCTCCAGCCTCGCCAGCTTACTCGCAAACGGGGGTGAAGTACTCACCGAC
ATCGCCGACGTACTCGCCGCCGTCACCATCGTACGATGGGTCTCCCGGATCACCACAATATACGCCAGGATCTCCGCAGTACTCGCCGGCCTCGC
CTAAGTACTCGCCGACCTCACCGCTGTACTCGCCCAGCTCGCCGCAGCACTCGCCCTCAAACCAGTACAGCCCAACAGGATCGACCTATTCGGCG
ACGAGTCCGCGGTACTCGCCGAACATGTCCATCTACTCGCCGAGCAGCACCAAGTACTCGCCCACCTCGCCAACGTACACACCGACGGCCCGCAA
CTACTCGCCCACGTCACCGATGTACTCGCCAACGGCTCCATCGCACTACAGTCCCACGAGTCCGGCCTACTCGCCCAGCAGTCCCACGTTCGAGG
AGAGCGAAGACTGAGGAAGGGAGGACGGGGG
(SEQ ID NO: 110)

Start ATG: 336

MSTPTDSKAPLRQVKRVQFGILSPDEIRRMSVTEGGVQFAETMEGGRPKLGGLMDPRQGVIDRTSRCQTCAGNMTECPGHFGHIDLAKPVFHIGF
ITKTIKILRCVCFYCSKMLVSPHNPKIKEIVMKSRGQPRKRLAYVYDLCKGKTICEGGEDMDLTKENQQPDPNKKPGHGGCGHYQPSIRRTGLDL
TAEWKHQNEDSQEKKIVVSAERVWEILKHITDEECFILGMDPKYARPDWMIVTVLPVPPLAVRPAVVMFGAAKNQDDLTHKLSDIIKANNELRKN
EASGAAAHVIQENIKMLQFHVATLVDNDMPGMPRAMQKSGKPLKAIKARLKGKEGRIRGNLMGKRVDFSARTVITPDPNLRIDQVGVPRSIAQNL
TFPELVTPFNIDRMQELVRRGNSQYPGAKYIVRDNGERIDLRFHPKSSDLHLQCGYKVERHLRDDDLVIFNRQPTLHKMSMMGHRVKVLPWSTFR
MNLSCTSPYNADFDGDEMNLHVPQSMETRAEVENIHITPRQIITPQANKPVMGIVQDTLTAVRKMTKRDVFITREQVMNLLMFLPTWDAKMPQPC
ILKPRPLWTGKQIFSLIIPGNVNMIRTHSTHPDEEDEGPYKWISPGDTKVMVEHGELIMGILCKKSLGTSAGSLLHICFLELGHDIAGRFYGNIQ
TVINNWLLFEGHSIGIGDTIADPQTYNEIQQAIKKAKDDVINVIQKAHNMELEPTPGNTLRQTFENKVNRILNDARDKTGGSAKKSLTEYNNLKA
MVVSGSKGSNINISQVIACVGQQNVEGKRIPYGFRKRTLPHFIKDDYGPESRGFVENSYLAGLTPSEFYFHAMGGREGLIDTAVKTAETGYIQRR
LIKAMESVMVNYDGTVRNSVGQLIQLRYGEDGLCGELVEFQNMPTVKLSNKSFEKRFKFDWSNERLMKKVFTDDVIKEMTDSSEAIQELEAEWDR
LVSDRDSLRQIFPNGESKVVLPCNLQRMIWNVQKIFHINKRLPTDLSPIRVIKGVKTLLERCVIVTGNDRISKQANENATLLFQCLIRSTLCTKY
VSEEFRLSTEAFEWLVGEIETRFQQAQANPGEMVGALAAQSLGEPATQMTLNTFHFAGVSSKNVTLGVPRLKEIINISKKPKAPSLTVFLTGGAA
RDAEKAKNVLCRLEHTTLRKVTANTAIYYDPDPQRTVISEDQEFVNVYYEMPDFDPTRISPWLLRIELDRKRMTDKKLTMEQIAEKINVGFGEDL
NCIFNDDNADKLVLRIRIMNNEENKFQDEDEAVDKMEDDMFLRCIEANMLSDMTLQGIEAIGKVYMHLPQTDSKKRIVITETGEFKAIGEWLLET
DGTSMMKVLSERDVDPIRTSSNDICEIFQVLGIEAVRKSVEKEMNAVLQFYGLYVNYRHLALLCDVMTAKGHLMAITRHGINRQDTGALMRCSFE
ETVDVLMDAAAHAETDPMRGVSENIIMGQLPKMGTGCFDLLLDAEKCRFGIEIPNTLGNSMLGGAAMFIGGGSTPSMTPPMTPWANCNTPRYFSP
PGHVSAMTPGGPSFSPSAASDASGMSPSWSPAHPGSSPSSPGPSMSPYFPASPSVSPSYSPTSPNYTASSPGGASPNYSPSSPNYSPTSPLYASP
RYASTTPNFNPQSTGYSPSSSGYSPTSPVYSPTVQFQSSPSFAGSGSNIYSPGNAYSPSSSNYSPNSPSYSPTSPSYSPSSPSYSPTSPCYSPTS
PSYSPTSPNYTPVTPSYSPTSPNYSASPQYSPASPAYSQTGVKYSPTSPTYSPPSPSYDGSPGSPQYTPGSPQYSPASPKYSPTSPLYSPSSPQH
SPSNQYSPTGSTYSATSPRYSPNMSIYSPSSTKYSPTSPTYTPTARNYSPTSPMYSPTAPSHYSPTSPAYSPSSPTFEESED*
(SEQ ID NO: 111)

Classification: enzyme
Gene Symbol: RpII215
FlyBase ID: FBgn0003277

Celera Sequence No. : 142000013383748
CTCAATAAATTCGTCCCCCTCCATATAATAACCCCCCCCCCCCACAGAGAACAAAACCAAAAAACAAAAAAAAAAAAGGTATCGAGCAACTTCA
CAAAAGACCACCACACAACCCAGCCATCTCTTCGATCCGAATGGTTCGCTAGTATAGCCACAGTACAACTATGGTACACATTGGTTTTTAGGCCT
TAAGACTTTGGTAGATTTTAATTCAGAAAATGAAAAGATAAAAAGAACAAGCCACCAGCGCAACTACAACTACAACACACAAAGAGTGAGGCATC
CGATGAACAATGGATGTCAAAGGTAAATTTATTGTATGTCCGCGAACCTAAATTATTTATCCACTTGGTTTTTACCCTAAATCTGTCGCAACACA
AAACATGTCAAGAGAAAAGTGAAAAAAAGGTACTATATGCGATTGTTTGGCGTAAGTGCAAGTAGTTACATAAGTCGTGAAATGAGAATCAATAA
ATTGAACCTAATTTAAAACCGAAAATATACACAATGGGTGTTTTTAATGGGAATGTCGGGATTTTCAGCTTTTCTTAAAAACAAATTACAAAAGG
ATACCCATTGCCCAAATTGAAATTAACGCAGCGCTGGCTTAACAATAATAATTATTTATTTATTTTCAAAGTTTCTTCTTGTCTATAACAATTAG
TAATGACTTGAACGCACACACATCATATGATTTTCGTGATCGATTCGCGGGGGATAAGCACATGCAGGGCTATATATATTTATGTGTAGATAAAT
ATAAATATACACAATGCAAATAACTTTCGTTTAGAACAATATCAGAATTTTCAATTATGCGCCGACCAAAAGATGGTAAACTACTTTTGGTTCTA
ACAAAAATTATTGTCAAATCTCCGCCAGGAGTTTTCGTTCAATTAAGAATCAAAGACTACATGGTTAAGTGGGTTAATTGCTAACTGGAAACGTT
ATCGTGGCGATAAAACCTGCGCGGGTTGGGTTCACAAATCATAGGGTTTTAAAAATGTTTTTATATATTTCTCATATATATCTATATATGCATAT
AAAGAAGAGCTTAGAAGCATTCAGCTATGACACAGTAACAAAGAGGAAAAAAAAAAAAACAATTAGGGTAATTTAAATTTTTAATCCTAAGCCGGA
GGATTGACACTTAACACAGGGATCGAGGACGGGGAAGTTGGCAGCTGATCTACTTGTACTTCTTCATGAACTCGGCGTGGAACACACGGAACTTC
TCCATCATCAGCTTCAGCTTGTCCGTTTGCGGGAGGATCGTGCTTCGGAAATGCCACGTGCCGGGCTTCTGACCAAATCCACTGCCAGGAACAAT
GCAAATGCCTGGGAGAAAATTAAACAATAAATTGAGAGACTAACAAACGAGGTCAGCAAAGAAAACTCACCGCTCGTCTCGAGCAGCTCAAATGC
GTAGAAAACATCGGGGGCCATGCCCTTGGCCTTGGCCGCCTCGATCGCCTTGGGCGGATCTCGATCTGTGGAAAGACGTACATGGCGCCCTGTA
CGGGGTTAACCTTGTAGCCTTCGAAGCTGTTCAGTGCCTTGTGGACGAGCTCGGCCCGTTCTTTTAGAGCGGCCAGAATGCCATCGCGCTCCTTC
TTGTACAGATCGTATGATGGCTCTCCGGGCTGCGGTGGATTGACCAGGGCACTCACGGCCACCTGGCCAGCGGTGGTGCTGCAAAGCGCCGCCGT
TATCGACTTGGTCAGCATGGCCTTGACCTTGGGATCAAGATTGAGAACCTCCATGTAACCGCCGCGAATGCCGCACTCGCCCAGATAGCCCTTCG
AGGTGGACAGGAAACTGACCATTTCCAGATTACGATAGGGGTCGCCCATTTCGTAGGCCACCTTCTTGAACGACCAGAACTTGGAGTTCTTGTCG
TAGACATTGTCCTGGTACACCTCATCGGCCAGCACCAGCACCTTGTTATCGTGTGCGAACTTAATGATCTCCTCGATGTTCTCGCGGGTCAGTAC
CTGTCCGGTGGGATTGCCCGGATTGATCACGACCAGGGCACGCGGATTGCAGACCTTCTTCGCCTCATCGTAGGACCGTTGCAGCTCCTTCCTGT
CCAGGCTCCAACCGGTCTCCTCCTCCAGATAGTAATCCACCTTGGTCATGCCGTATTCGGAGATGGTGGCCGAGTACAGTGGGTACTGCGGAATG
GGCACCATGACACCAGGCGCCTTGCATCCCACCTCGGCGCTGAAAAAAGAAACGTAAAGGTAAGCTTCAAATGTATTTAGAATTCCTTAGTAAAT
GCTCAGTAGTATTTCATAAACAAAGTGTTTGAATAATACTACTGAGCAATAAACAATAATAATATTTATCTATCTGGCTGCCACATAAGTTGTCA
ACCCAAAAAATGGCACAATTTTGGGCCATATCTCTGGCAAATCTCTGGTTTTAACTGATAAGTCTCGACAGAAGAAGCGCCACATCATGGACAAT
AAAAATGTTGGCCCTGGCGACATACTTGATCATGGAGAGAATGCTCTTGATGCCGGGAGAGGCACCGCCGGTTAGATAGATGTCCTGCCAATTGG
AGGCGATGCCGCCATCCCTTTTCTCGATGTACTGAGCAACCTGGCGACGCACCACCTCCAGACCGGCGGAGTCGGTGTACGAGCCCACCGATTGA
CCCTGGCAGCCGTTCAAAATGGCACAGGCGCGCTTCTTGACGTCCTCGGGATAATCGGGTGAATCCAGCAGACGTGTCTCGAAGGTCAGCGCCAA
CAGCTGATAAGTAAAATATACAATACATTTAATGAAATCATATCATAAATGAAGGGGCCAAAACTCACCTGTCGCAGGAAGGTCAAGGGCTGCTG GCCCATCGCATGGCAATCACCGATGTTGGCACGGATCACCTGGTCGAATGGCTTCTTGACACCCTGCAATCAAATTCAATCGGAACGGAATTACA
AATTAGCCATATAAAATAACTCATTGTTTGCTCGCTGGCCAAATGAAAGTGTAATCGCTGCAGGCTGGCGGATCAAATGGGCATTTAATTTGATT
TGTGGCTTTCGCCATGCAAATTACACTCAAGTGGATTGCCAAGCTAAATTGAAGACCAGCCAGAGTACAGAGTAATCGATTAAGTATCAAATTCA
ATCAAATATTTATCAGTAATGAGCCATTGTGGATTCAGCAAATGGTATTCTCTTTCAAATAGACGCCTGCTAGAAATAACTATCAAATGACCATC
ATTATAGTTACTTAACAATGTGAACTAGTTTACATTCAGTAGCAAATCAATGGTGCAATCTGTTACGATCTTTATAATCCAGCACACTTTGGGGA
ATCCCAAATTAAAGTTTCTAAACGAATTAAAGTCATTGTAGACACAGGCAACCAGTAGTTTAGTTTCCCGCACGAATAGAGGTCACAATAATCGG
CTGTGGAAATTGTCAGCTGAACAAAACACACAATTTGCAGGGCACATGCTAGTTGCACTCGTTCATGGAAGACAACATCTCATCGTCTCGGGTTC
CATTTAACCACGCTCAAATGGCCAATTTACCACATAATGTCACGGAGGTTCGAGGAGCTGCGATGATATTGTGTGTTTTTTTTTTTTTTTTGAGA
GGCGAAACAATGCAAGTTGCGCCATGTAAGCGAACTGCAGCGCTGCCATTGACGTCACTCGGCAGTGGATGTGTTTTGCCTGACAATGTGATAAT
TGGAAAATTAAGGAATTCTGGGCTGTGGAAAAATCATCCAGTGCTCGAGTTTGGTTACTAAGAGTATAAAATCGTCAAGTTCTCACCGTGCAAAC
GTGTGTCACCTTATCGAATTCAGTTAATTATTTATTATTTATTTTTTTTTTTTTAATTTCGAAAATTACTGATAAAAGTGTTGCCGAGTCGCGG
CAACTGAACTGGCTTGTGTTTGTAGTTCGTGTGGAAATATGTATAGAAATGGGTCCTCTATCGCATCGCAAATCGAACAGTGCTGGTGAAAAAAA
ATGATATGCCAAAGTAGTTTCGAATATTTCAAAACCACAAAACCGCAGAGATAGTGTTAAGAAATCAATTAATAGCCCATCTAAACTCAGTTAGA
AATTGCTAGTTAAGTTTTTAGCATCGTTTTGGAAATGGCTACTAATTAACTGACCAGCGCTGTTCGCACCTAAAGAATATTGCTTGCATATTCCT
TTCTACCCTTCACTTCGCACTTGAAATCGTTGTAAACAAACTTTTTGTGCTAAGTGGCAATATAATTGATAACTACATATATATGCACAACATAT
ATACTCGTGCAGGCAGGTAAGAGTCGTATAATCATATAGGCGCTGTATAAAAGGCGTTAGCAACTCAAACATTATCGCCAATACGAATCGAAGGA
AAGTATAATAATATGTTGGCAAATGTTAATGCCAAAAGGAAGTCAAAGTAAACAGAGGGAAATGGGCATGATTAGGAATTAGAAATGATTATTAC
ACGGGCACAGAATTGTTAATAATCCTATATCGTAGTGAACAGGACGAAGTGAAGTACATAAATGCCAGTGATAAGAATGCCTGCTGCTGACAGAT
GATGAGTTTCTTTTGGACCATTGCCAAATCCGTATGTTGAATCTGTGGGCAAGTGGAGGAATTTGATAAAACGCAGAATGAACAGCACAGCAGAT
TCAGTCGTGCGGATAAGGAAATCAAATCGCAGCGGGAAAACTGGTGGGGGAAATCAACTGGCAGCGGCATTAAAAACGCAAACACAGAATGTGAA
AAGTCAGCGGGGCTCACAATGGATTTAACTATATGTATATACATATGTATATCTTTAAATATTCATCACATATTTGTGTACATATGTACATATAG
TATCGTTGCGGGTCACAAAAGTTCGAAGAGAATTTTGCAAAACAAATGAAGGAAAAAAAAAAATGGAAAGCAAGAAGTGCAGAGAGAAAGCATCGT
GTGTATACAACATGTTTTCCCCACAGACTCATGCGCATGTTCGGCCTTTGTTATGATTTTTCACTTTCCCAGTGATAAGAAAAGGTCCACGGAAT
CAGAATCCGAATCAGAATCACGCCCACGCTCGCCCACAATTTCCGCACTTATGTAAGCCAAGTTGAAGGTCGTTCAGTGAACCCGCATCGCATCG
CGTCGTTCGCTCTTCATCTAAATACTTTATTTAATTGATCCAAGAAGCACAATTTAGAATAATTACAAACATTAACTGGCAATTAAGAGCATGAC
TCGTTATGGAAAACGGCGAAGAAACGCCGTTTTTTTGTTTTTTTTTTTAGATGAGAAAACCGGTTAATTTGGGCCAACTGCCTGTGGAAAAAT
CATTCACATGCCGAGCAGTACTTAAATTAATTAGTTTATTGACTTGTTGTTTGCTCTAACCCAAAAAGTGTAATTTCCCCTTAGCCCAAAGTTCA
CTTATAAAGATATATATTCCGTTTTAGATAAGTCTCGATATTTTTATAGCGGTCTGATTACAATTTCAAGTCTTATCTGAACTTTTGGATTACTT
CTGATAGCTTTATTGTTGCCCAAAAATTGTTTGTGTTTAGTTGAAGTAAATAAAATTCCGAGCTCTATTTTTGGCAAATTTTAATGGGTTTAGTT
CAAGTGGTTCAAACACTACTCTAAATTCTTGATGTGTAATAAAAAACAAACAATTGTTTTGATCAACTTTGTGCTCTTTGGTAAACATTTTTCGC
TCAAAACTGAAATTAAACATATGGCATTTTACTTTCGTAAGCTTTTTATGCTCGTGGAATAAGAAATGGGTTTGGAAACTGGTTTTTTTTTTATT
CGACAAGCTTATTGTTTTTGCAAAAATGTGTTTTTTGCAAAACAAAACCTTATCGCATTGAATAAACAAAAGCTAAAGTTTTCTATGTTTGTTTG
TTGAAACTTTATACATTCGATAGATTTTTTATTGGATTGCTAGCTGAATTGGTACTCCCCTGGCTGGTTCTTATCACACTTCCATTCTTATCAAT
CCAAATTACTTCATTTCGTGGGCGTATTTTCCAACAGGTGTCCTTGAGAAAGGGGTGACCACGATTGCCAGCCGAAGGTGAATGATTCAGCGCTG
CGTGGCCGCTCCATTCAAGCGCGAATAAAAAAATGAAAAGGGCGGCAAAAAACAAACACAGACGCGCCTCACACTTGATACATACATACATACAT
AAACGTGCATGTGTATATAAGTAGATATACATAGAGACATAGCGTGCTTAGATATTAAAATGCGGGCTTTGAATTGCCATTAAATTGCCATTGAA
TAGAGGGAAGGGTAGGGGGGTGTGTGCAAAACACTAGTTAATGGCGTCGCACTTTGCCGCTTTGTTTGCCCGATTACTTGTGGATCAATTTCCCA
TGGCATTAACTAACACTCACCTTTTCCAGTTCCTTCTCGATTTCCCCAGCACGAATCACCAGAGGACCGCGAACGGCATATTCCATGGCAATAAA
GTTGGGATTTATGTTATCCAGTGTGAGCGCTTTCGACGACGACGGCATTTTGTGGCTGGTTGAAAAGGAACTGAGAAAAAAAAAGAAGGGGATGG
ATATTCACTTCAGCAATCAACAATCACTTCTTGTTCGATATATAACGTGTTTTAAATGTGTTTTAAAATATATTGTTTTTGTTATGCGGCTTTTT
CAGCGAACGAAACTAACCGGCGGACGTCTAACGGTTGAATGAAATCGCCGCTTGTTCCATGGCGCTGCGACGTCGCTGCTGCCGTCACCGTTGCT
GTTGCCGTTGATTTCGCCGCACGTCGATTGGCATTGTTGCTGTTGTTGTGCAGGAACGATTTCCAGCGGCGAATAACGTACTGTTGCTGCTGGCG
CTGGTGCTGCTGCAATGCGGCCGAAACTGTGGCGGCAGCAGGTTTAATTAGCATTCGACTCATTATTTCTGCAACGAGAAGAGCGTCTCAGTAAG
TAAATTACTCAAAATACAAAAAAAAGGAAAGAGACAGACCGCGCTTTAATCGCAAGAATTTAGCACCATGAGAACAGCGGAAAGAAGAAGAAGCA
GCGAAATGAAGGGTGTGTGCGTGTATAAGAGTCCGGCTCACAATTATAAGAGCGGCGAATTGAAAGGCTCAGCTGTTATCACTACACCGAAAGCA
ATTAGTTTCGAAGCAGGGAATCATTTAAATAACTTTGTAGCTAGGAAAACTTAAGCAACTATAGATATTTCGATGTGAAATATATATCATATTAT
ATTAAGCATTTTTATATGGTATTGTTAGCACGCGCTCAATATAATATTCAAGTACCTAAATACATTTTCTTCACTGTGCATTTTTGTATCTTATC
AAAGACAAGGCGTGGTATCATTTACTTTTTCAGAGCTTATCAATGTGATTGCTTGTGGTTCGATACTTTATTGCCTTTCTGTTTATCAAGAAGCT
AAAGTGTAAATATTTACGACCTTTGGAAACTTTGCAATTAAATTCGCCGTGCATTTATCCTAGACTCAAACCCAATTGCACTCGCCGCAAGGCGC
GCATTTCAAAACTGCAATCGAGCATTTCTTATCAGAGTTTTGGGGCTTTGCACAAGCAACTGCAAAGCTGAAAAATATATATTTTATTTGAGGAG
GAATATATATTTTTGGAAAATATAAAAACGGTTACCGGCTGAATAAAATGAATGGCCATAAAGCCTAATCTCAAGAACATTTATTGCTTGACCAT
CCAGAAAATTTAATTAAAAATGGGACCGTTTAGAATCTACTTGTGTGTGCTGCTATATATTTCACTATATTTCTTATCTTGGTGGAACTTTTTTT
TTAGAGGCAGTTAACGGATTTGTGGGCCATTTACCCAGGCATTATGTATACATATGTATGATTTAATAGCTATATTTCTCCATTAAATCCACTGG
CAGGGCATCCATTGGTGGGGGCCACTATCAGTTGAGCGTACTTTTGACTTTGAGCCAAATCGGCGCAGCTTATCAGTGACGTCCCATTCGCAGCT
TACGATTCCCTGTCTTTCAATTGAATATATGTATATAGCTTTTCTGATTTCTGCACTTTGAAACGCCAATTGCGTAATGCAAAAAATGAGCAAAC
GAACAAAGAATCTTTTAGAAACATGACAATGACCAAAGATCGACATTACCTCCAAAATACTATACTTTTCGCACTCAAAAATCAGCATCAATCAG
CCGCAGATTGTTTGCTTTCTTTTTAGCGACAGCGAATTTATTTGTTTTTAAATTAAAAATGTACTAAATGCCGGTCCCGAAAAATACACAAATGT
ATGCTATTTTATATACGCACATATGTATCTTTGGAATATATGAATGTATGTGTATATATATAGGTATATTGTTTAGACGAGACAAACTGAAACTT
GTTGGCAATAACTTTTTGGAAAACCGGTTGCGGTTTTGATGGCATTGATATAGACGAAAGGGTTAAGAATTAGGGGAAAGGGGTAAGAATTTGGG
AATGAGAAAACATCGATACAGTGATCTCTGCTTAATTAAGACAAATTCAATACGATGCCGATATATAGATATAGATAGATATAAAATAATATATC
CAATAGAATTTTTATATGATAACCATCTAAAGCAGCTGTGCATAGAACTTTTGCGTATTAATTTAAGAAACATTACCTCCAAATATTTATTTTAA
ATAAATTTTTCAAATTTAACATTTTTTTTTTTTTGAGACAACTTTTGTTAGTCACTGTTTATCTGCGATATATATATATGCAGCGTATCGCTTT
TGTTTGTGATTGTTTTGACAACAAAACTGGCTTATGCAACGAACTGTTAAAAAAAAAATCTGAAACAGAAAATTATGTGAACTGGCTGCACTTTGC
TTCAAAGACCCCGCTCCCCCCTGCACTTTCACCCCCCGCATTGGGGGGATTATCAGACAAACCAACTGGATAAGATAGTAACGATAAGGAATCCA
ATTAGAACACGGCCATTCGGATTTACTAAAATCACAACTTTTGCCAAACGTTAGTAAATTATATTAAATTATATTGTAACTCCGATTGACACGTA
GAGCGCAACGAACAACAGCAACACAAAAAGAAGCAGAAATAACGGGTAAAGGGGGTGTTTTGATGTGCTAATTGGGTTGCTAAACAGCTGTTGAC
GCCGCACAAATTGAGCACAAAAAAAAAAACAATAACACGGCACGCAATTCAATTAGGGAAACGCACGCAGAACGATAAACAAAATCAGGGTACTA
TTGTGTATTAGATTTTTTTTGGGCGCACAAATCACTTTCACTGTCACTTCCTCGCTGCTCCCAATTAGAATTTCTCGGCCACTGTGTTTATATA
TATGTACATATATGCACATGCATATATACATATATACGTCGGCAGTTCAAGAGCAAAAAATCGATTTTTCGCTGCACTTTTTAGTCGTTTCACCT
TGATGGGCGCAAGTGGGCGTGGCGATTATCTAACGGCGTTTGTTGTGATCCCAAGAACTTGCATAAACTTATTAATAAACGCGATATGTCTGTAT
ATAAAATACCTAATAAAAACGTGTGTGCTTGCTTGGCTGCGTGTGTGTGCGCGTACGTGTGTGTGTGTGTGCGAATATGTGCGGCGTGCGAGCTC

FIGURE SHEET 47

```
CAATCAGAATCGTATCAAAAATTCAAAGCTCTTTGGCCGCTAGACGCAATTAAGGAACTGACAACAAGAACTGAAACCGCACCGAGATGGAAAAT
GAAGTGCTGGCAGTATTTACCGACTATATGTTTTTCTTGCGGGCAAAAGTCACGATGAAGCGGGCAGCGATTAAGTTTTAAAAATATCACGTCTG
CAGCCCTCGCAGCCAAACTTTCGATAGACGGCGATAGATCGATAGACCAGCGATTTGCACCAACACTGGAAAGCTCAGAGCATTCAAAAACAAAC
TAATGTGTTTTATAAATAGCTCTTTTTAAATATCGATTAATTGCGATCTTAACTAACTTTCGTTTATTTCTATTAATTATGAACTTACTTCTGTT
TTTAAACATCTTTGCTCTTTGCTTGTTTTTCGTGTAAGGCTTTAAATTCACTTAAACAATTTTGCTGGCTTTGTGCGCATCTTCATATATCACTG
AAATTGATTGTTATAGGAGTGTCCCATTGAATTAGTTTTGTGTCGATTCAATCCTGGCCCGAAAATGTATGAACAAGCTATGCCCTACATTTTAC
CCATAGTCTACTTAGGTTTGTTTATATAGTATTCTTTTCAAGTTCGTTATGATAGCTCTTAGAAAATAAGATTTCTGTGAATATCTCCTCCGTAT
AAAAGAATTTTTATCAATAGTTTGGTAAGCTTTTTTTTCTCTTCTACAAAACCTTTTCGCATGTTTTTATTTCACTCGAAACTTATTGCTATTCAA
AAAAATGGGTTTTCTAACGCTAGAATTATGTACAGAGTGCATTTGGAAAAAATGATGGGTAGTAAGCCCTAGAAAGCCATGGCTACGTGCTGATG
CCCATGATGGATTCGATGGAGAAACTCAGCTTGGGCTTCTTGCCACTGCCGGTGGAGGCAGTGGTGACTGCGGGCGTGGTCATCGCTGGATTTGT
GGGCGGGATCGTTAGCGGTATCGTCGGCGGCATCGGGTGATAAATGTGCTGCTCCTGATGAACGGGTGCGCAGGCGGCGGCGGCGGCGGCAACGG
TGGCAAAGTACAAAGCGTTACCGCCCAGCGTCGCCTCCATGACATGGTTCAGTTCCGGATCGGCGAATGCCCGCCGTTTGCGCATGCGCTCCATC
AATG
(SEQ ID NO: 112)

Exon: 9739..9404
Exon: 6908..6668
Exon: 6530..6386
Exon: 2913..2824
Exon: 2758..2496
Exon: 2224..1401
Exon: 1338..1001
Start ATG: 6508 (Reverse strand: CAT)

Transcript No. : CT4436
CTTTTGCCCGCAAGAAAAACATATAGTCGGTAAATACTGCCAGCACTTCATTTTCCATCTCGGTGCGGTTTCAGTTCTTGTTGTCAGTTCCTTAA
TTGCGTCTAGCGGCCAAAGAGCTTTGAATTTTTGATACGATTCTGATTGGAGCTCGCACGCCGCACATATTCGCACACACACACACACGTACGCG
CACACACACGCAGCCAAGCAAGCACACACGTTTTTATTAGGTATTTTATATACAGACATATCGCGTTTATTAATAAGTTTATGCAAGTTCTTGGG
ATCACAACAAACGCCGTTAGATAATCGCCACGCCCACTTGCGCCCATCAAGAAATAATGAGTCGAATGCTAATTAAACCTGCTGCCGCCACAGTT
TCGGCCGCATTGCAGCAGCACCAGCGCCAGCAGCAACAGTACGTTATTCGCCGCTGGAAATCGTTCCTGCACAACAACAGCAACAATGCCAATCG
ACGTGCGGCGAAATCAACGGCAACAGCAACGGTGACGGCAGCAGCGACGTCGCAGCGCCATGGAACAAGCGGCGATTTCATTCAACCGTTAGACG
TCCGCCGTTCCTTTTCAACCAGCCACAAAATGCCGTCGTCGTCGAAAGCGCTCACACTGGATAACATAAATCCCAACTTTATTGCCATGGAATAT
GCCGTTCGCGGTCCTCTGGTGATTCGTGCTGGGGAAATCGAGAAGGAACTGGAAAAGGGTGTCAAGAAGCCATTCGACCAGGTGATCCGTGCCAA
CATCGGTGATTGCCATGCGATGGGCCAGCAGCCCTTGACCTTCCTGCGACAGCTGTTGGCGCTGACCTTCGAGACACGTCTGCTGGATTCACCCG
ATTATCCCGAGGACGTCAAGAAGCGCGCCTGTGCCATTTTGAACGGCTGCCAGGCGTCAATCGGTGGGCTCGTACACCGACTCCGCCGGTCTGGAG
GTGGTGCGTCGCCAGGTTGCTCAGTACATCGAGAAAAGGGATGGCGGCATCGCCTCCAATTGGCAGGACATCTATCTAACCGGCGGTGCCTCTCC
CGGCATCAAGAGCATTCTCTCCATGATCAACGCCGAGGTGGGATGCAAGGCGCCTGGTGTCATGGTGCCCATTCCGCAGTACCCACTGTACTCGG
CCACCATCTCCGAATACGGCATGACCAAGGTGGATTACTATCTGGAGGAGGAGACCGGTTGGAGCCTGGACAGGAAGGAGCTGCAACGGTCCTAC
GATGAGGCGAAGAAGGTCTGCAATCCGCGTGCCCTGGTCGTGATCAATCCGGGCAATCCCACCGGACAGGTACTGACCCGCGAGAACATCGAGGA
GATCATTAAGTTCGCACACGATAACAAGGTGCTGGTGCTGGCCGATGAGGTGTACCAGGACAATGTCTACGACAAGAACTCCAAGTTCTGGTCGT
TCAAGAAGGTGGCCTACGAAATGGGCGACCCCTATCGTAATCTGGAAATGGTCAGTTTCCTGTCCACCTCGAAGGGCTATCTGGGCGAGTGCGGC
ATTCGCGGCGGTTACATGGAGGTTCTCAATCTTGATCCCAAGGTCAAGGCCATGCTGACCAAGTCGATAACGGCGGCGCTTTGCAGCACCACCGC
TGGCCAGGTGGCCGTGAGTGCCCTGGTCAATCCACCGCAGCCCGGAGAGCCATCATACGATCTGTACAAGAAGGAGCGCGATGGCATTCTGGCCG
CTCTAAAAGAACGGGCCGAGCTCGTCCACAAGGCACTGAACAGCTTCGAAGGCTACAAGGTTAACCCCGTACAGGGCGCCATGTACGTCTTTCCA
CAGATCGAGATCCCGCCCAAGGCGATCGAGGCGGCCAAGGCCAAGGGCATGGCCCCCGATGTTTTCTACGCATTTGAGCTGCTCGAGACGAGCGG
CATTTGCATTGTTCCTGGCAGTGGATTTGGTCAGAAGCCCGGCACGTGGCATTTCCGAAGCACGATCCTCCCGCAAACGGACAAGCTGAAGCTGA
TGATGGAGAAGTTCCGTGTGTTCCACGCCGAGTTCATGAAGAAGTACAAGTAGATCAGCTGCCAACTTCCCCGTCCTCGATCCCTGTGTTAAGTG
TCAATCCTCCGGCTTAGGATTAAAAATTTAAATTACCCTAATTGTTTTTTTTTTTTTCCTCTTTGTTACTGTGTCATAGCTGAATGCTTCTAAGCT
CTTCTTTATATGCATATATAGATATATATGAGAAATATATAAAAACATTTTT
(SEQ ID NO: 113)

Start ATG: 600 (Reverse strand: CAT)

MPSSSKALTLDNINPNFIAMEYAVRGPLVIRAGEIEKELEKGVKKPFDQVIRANIGDCHAMGQQPLTFLRQLLALTFETRLLDSPDYPEDVKKRA
CAILNGCQGQSVGSYTDSAGLEVVRRQVAQYIEKRDGGIASNWQDIYLTGGASPGIKSILSMINAEVGCKAPGVMVPIPQYPLYSATISEYGMTK
VDYYLEEETGWSLDRKELQRSYDEAKKVCNPRALVVINPGNPTGQVLTRENIEEIIKFAHDNKVLVLADEVYQDNVYDKNSKFWSFKKVAYEMGD
PYRNLEMVSFLSTSKGYLGECGIRGGYMEVLNLDPKVKAMLTKSITAALCSTTAGQVAVSALVNPPQPGEPSYDLYKKERDGILAALKERAELVH
KALNSFEGYKVNPVQGAMYVFPQIEIPPKAIEAAKAKGMAPDVFYAFELLETSGICIVPGSGFGQKPGTWHFRSTILPQTDKLKLMMEKFRVFHA
EFMKKYK*
(SEQ ID NO: 114)

Name: putative aminotransferase
Classification: enzyme

Celera Sequence No. : 142000013383748
CTCAATAAATTCGTCCCCCTCCATATAATAACCCCCCCCCCCCACAGAGAACAAAACCAAAAAACAAAAAAAAAAAAGGTATCGAGCAACTTCA
CAAAAGACCACCACACAACCCAGCCATCTCTTCGATCCGAATGGTTCGCTAGTATAGCCACAGTACAACTATGGTACACATTGGTTTTTAGGCCT
TAAGACTTTGGTAGATTTTAATTCAGAAAATGAAAAGATAAAAAGAACAAGCCACCAGCGCAACTACAACTACAACACACAAAGAGTGAGGCATC
CGATGAACAATGGATGTCAAAGGTAAATTTATTGTATGTCCGCGAACCTAAATTATTTATCCACTTGGTTTTTACCCTAAATCTGTCGCAACACA
AAACATGTCAAGAGAAAAGTGAAAAAAAGGTACTATATGCGATTGTTTGGCGTAAGTGCAAGTAGTTACATAAGTCGTGAAATGAGAATCAATAA
```

ATTGAACCTAATTTAAAACCGAAAATATACACAATGGGTGTTTTTAATGGGAATGTCGGGATTTTCAGCTTTTCTTAAAAACAAATTACAAAAGG
ATACCCATTGCCCAAATTGAAATTAACGCAGCGCTGGCTTAACAATAATAATTATTTATTTATTTTCAAAGTTTCTTCTTGTCTATAACAATTAG
TAATGACTTGAACGCACACACATCATATGATTTCGTGATCGATTCGCGGGGATAAGCACATGCAGGGCTATATATATTTATGTGTAGATAAAT
ATAAATATACACAATGCAAATAACTTTCGTTTAGAACAATATCAGAATTTTCAATTATGCGCCGACCAAAAGATGGTAAACTACTTTTGGTTCTA
ACAAAAATTATTGTCAAATCTCCGCCAGGAGTTTTCGTTCAATTAAGAATCAAAGACTACATGGTTAAGTGGGTTAATTGCTAACTGGAAACGTT
ATCGTGGCGATAAAACCTGCGCGGGTTGGGTTCACAAATCATAGGGTTTTAAAAATGTTTTTATATATTTCTCATATATATCTATATATGCATAT
AAAGAAGAGCTTAGAAGCATTCAGCTATGACACAGTAACAAAGAGGAAAAAAAAAAAACAATTAGGGTAATTTAAATTTTTAATCCTAAGCCGGA
GGATTGACACTTAACACAGGGATCGAGGACGGGGAAGTTGGCAGCTGATCTACTTGTACTTCTTCATGAACTCGGCGTGGAACACACGGAACTTC
TCCATCATCAGCTTCAGCTTGTCCGTTTGCGGGAGGATCGTGCTTCGGAAATGCCACGTGCCGGGCTTCTGACCAAATCCACTGCCAGGAACAAT
GCAAATGCCTGGGAGAAAATTAAACAATAAATTGAGAGACTAACAAACGAGGTCAGCAAAGAAAACTCACCGCTCGTCTCGAGCAGCTCAAATGC
GTAGAAAACATCGGGGGCCATGCCCTTGGCCTTGGCCGCCTCGATCGCCTTGGGCGGGATCTCGATCTGTGGAAAGACGTACATGGCGCCCTGTA
CGGGGTTAACCTTGTAGCCTTCGAAGCTGTTCAGTGCCTTGTGGACGAGCTCGGCCCGTTCTTTTAGAGCGGCCAGAATGCCATCGCGCTCCTTC
TTGTACAGATCGTATGATGGCTCTCCGGGCTGCGGTGGATTGACCAGGGCACTCACGGCCACCTGGCCAGCGGTGGTGCTGCAAAGCGCCGCCGT
TATCGACTTGGTCAGCATGGCCTTGACCTTGGGATCAAGATTGAGAACCTCCATGTAACCGCCGCGAATGCCGCACTCGCCCAGATAGCCCTTCG
AGGTGGACAGGAAACTGACCATTTCCAGATTACGATAGGGGTCGCCCATTTCGTAGGCCACCTTCTTGAACGACCAGAACTTGGAGTTCTTGTCG
TAGACATTGTCCTGGTACACCTCATCGGCCAGCACCAGCACCTTGTTATCGTGTGCGAACTTAATGATCTCCTCGATGTTCTCGCGGGTCAGTAC
CTGTCCGGTGGGATTGCCCGGATTGATCACGACCAGGGCACGCGGATTGCAGACCTTCTTCGCCTCATCGTAGGACCGTTGCAGCTCCTTCCTGT
CCAGGCTCCAACCGGTCTCCTCCTCCAGATAGTAATCCACCTTGGTCATGCCGTATTCGGAGATGGTGGCCGAGTACAGTGGGTACTGCGGAATG
GGCACCATGACACCAGGCGCCTTGCATCCCACCTCGGCGCTGAAAAAAGAAACGTAAAGGTAAGCTTCAAATGTATTTAGAATTCCTTAGTAAAT
GCTCAGTAGTATTTCATAAACAAAGTGTTTGAATAATACTACTGAGCAATAAACAATAATAATATTTATCTATCTGGCTGCCACATAAGTTGTCA
ACCCAAAAAATGGCACAATTTTGGGCCATATCTCTGGCAAATCTCTGGTTTTAACTGATAAGTCTCGACAGAAGAAGCGCCACATCATGGACAAT
AAAAATGTTGGCCCTGGCGACATACTTGATCATGGAGAGAATGCTCTTGATGCCGGGAGAGGCACCGCCGGTTAGATAGATGTCCTGCCAATTGG
AGGCGATGCCGCCATCCCTTTTCTCGATGTACTGAGCAACCTGGCGACGCACCACCTCCAGACCGGCGGAGTCGGTGTACGAGCCCACCGATTGA
CCCTGGCAGCCGTTCAAAATGGCACAGGCGCGCTTCTTGACGTCCTCGGGATAATCGGGTGAATCCAGCAGACGTGTCTCGAAGGTCAGCGCCAA
CAGCTGATAAGTAAAATATACAATACATTTAATGAAATCATATCATAAATGAAGGGGCCAAAACTCACCTGTCGCAGGAAGGTCAAGGGCTGCTG
GCCCATCGCATGGCAATCACCGATGTTGGCACGGATCACCTGGTCGAATGGCTTCTTGACACCCTGCAATCAAATTCAATCGGAACGGAATTACA
AATTAGCCATATAAAATAACTCATTGTTTGCTCGCTGGCCAAATGAAAGTGTAATCGCTGCAGGCTGGCGGATCAAATGGGCATTTAATTTGATT
TGTGGCTTTCGCCATGCAAATTACACTCAAGTGGATTGCCAAGCTAAATTGAAGACCAGCCAGAGTACAGAGTAATCGATTAAGTATCAAATTCA
ATCAAATATTTATCAGTAATGAGCCATTGTGGATTCAGCAAATGGTATTCTCTTTCAAATAGACGCCTGCTAGAAATAACTATCAAATGACCATC
ATTATAGTTACTTAACAATGTGAACTAGTTTACATTCAGTAGCAAATCAATGGTGCAATCTGTTACGATCTTTATAATCCAGCACACTTTGGGGA
ATCCCAAATTAAAGTTTCTAAACGAATTAAAGTCATTGTAGACACAGGCAACCAGTAGTTTAGTTTCCCGCACGAATAGAGGTCACAATAATCGG
CTGTGGAAATTGTCAGCTGAACAAAACACACAATTTGCAGGGCACATGCTAGTTGCACTCGTTCATGGAAGACAACATCTCATCGTCTCGGGTTC
CATTTAACCACGCTCAAATGGCCAATTTACCACATAATGTCACGGAGGTTCGAGGAGCTGCGATGATATTGTGTGTTTTTTTTTTTTTTTTGAGA
GGCGAAACAATGCAAGTTGCGCCATGTAAGCGAACTGCAGCGCTGCCATTGACGTCACTCGGCAGTGGATGTGTTTTGCCTGACAATGTGATAAT
TGGAAAATTAAGGAATTCTGGGCTGTGGAAAAATCATCCAGTGCTCGAGTTTGGTTACTAAGAGTATAAAATCGTCAAGTTCTCACCGTGCAAAC
GTGTGTCACCTTATCGAATTCAGTTAATTATTTATTATTTATTTTTTTTTTTTTAATTTCGAAAATTACTGATAAAAGTGTTGCCGAGTCGCGG
CAACTGAACTGGCTTGTGTTTGTAGTTCGTGTGGAAATATGTATAGAAATGGGTCCTCTATCGCATCGCAAATCGAACAGTGCTGGTGAAAAAAA
ATGATATGCCAAAGTAGTTTCGAATATTTCAAAACCACAAAACCGCAGAGATAGTGTTAAGAAATCAATTAATAGCCCATCTAAACTCAGTTAGA
AATTGCTAGTTAAGTTTTTAGCATCGTTTTGGAAATGGCTACTAATTAACTGACCAGCGCTGTTCGCACCTAAAGAATATTGCTTGCATATTCCT
TTCTACCCTTCACTTCGCACTTGAAATCGTTGTAAACAAACTTTTTGTGCTAAGTGGCAATATAATTGATAACTACATATATATGCACAACATAT
ATACTCGTGCAGGCAGGTAAGAGTCGTATAATCATATAGGCGCTGTATAAAAGGCGTTAGCAACTCAAACATTATCGCCAATACGAATCGAAGGA
AAGTATAATAATATGTTGGCAAATGTTAATGCCAAAAGGAAGTCAAAGTAAACAGAGGGAAATGGGCATGATTAGGAATTAGAAATGATTATTAC
ACGGGCACAGAATTGTTAATAATCCTATATCGTAGTGAACAGGACGAAGTGAAGTACATAAATGCCAGTGATAAGAATGCCTGCTGCTGACAGAT
GATGAGTTTCTTTTGGACCATTGCCAAATCCGTATGTTGAATCTGTGGGCAAGTGGAGGAATTTGATAAAACGCAGAATGAACAGCACAGCAGAT
TCAGTCGTGCGGATAAGGAAATCAAATCGCAGCGGGAAAACTGGTGGGGGAAATCAACTGGCAGCGGCATTAAAAACGCAAACACAGAATGTGAA
AAGTCAGCGGGGCTCACAATGGATTTAACTATATGTATATACATATGTATATCTTTAAATATTCATCACATATTTGTGTACATATGTACATATAG
TATCGTTGCGGGTCACAAAAGTTCGAAGAGAATTTTGCAAAACAAATGAAGGAAAAAAAAAAATGGAAAGCAAGAAGTGCAGAGAGAAAGCATCGT
GTGTATACAACATGTTTTCCCCACAGACTCATGCGCATGTTCGGCCTTTGTTATGATTTTTCACTTTCCCAGTGATAAGAAAAGGTCCACGGAAT
CAGAATCCGAATCAGAATCACGCCCACGCTCGCCCACAATTTCCGCACTTATGTAAGCCAAGTTGAAGGTCGTTCAGTGAACCCGCATCGCATCG
CGTCGTTCGCTCTTCATCTAAATACTTTATTTAATTGATCCAAGAAGCACAATTTAGAATAATTACAAACATTAACTGGCAATTAAGAGCATGAC
TCGTTATGGAAAACGGCGAAGAAACGCCGTTTTTTTTGTTTTTTTTTTTAGATGAGAAAACCGGTTAATTTGGGCCAACTGCCTGTGGAAAAAT
CATTCACATGCCGAGCAGTACTTAAATTAATTAGTTTATTGACTTGTTGTTTGCTCTAACCCAAAAAGTGTAATTTCCCCTTAGCCCAAAGTTCA
CTTATAAAGATATATATTCCGTTTTAGATAAGTCTCGATATTTTTATAGCGGTCTGATTACAATTTCAAGTCTTATCTGAACTTTTGGATTACTT
CTGATAGCTTTATTGTTGCCCAAAAATTGTTTGTGTTTAGTTGAAGTAAATAAAATTCCGAGCTCTATTTTTGGCAAATTTTAATGGGTTTAGTT
CAAGTGGTTCAAACACTACTCTAAATTCTTGATGTGTAATAAAAAACAAACAATTGTTTTGATCAACTTTGTGCTCTTTGGTAAACATTTTTCGC
TCAAAACTGAAATTAAACATATGGCATTTTACTTTCGTAAGCTTTTTATGCTCGTGGAATAAGAAATGGGTTTGGAAACTGGTTTTTTTTTTTATT
CGACAAGCTTATTGTTTTTGCAAAAATGTGTTTTTTGCAAAACAAAACCTTATCGCATTGAATAAACAAAAGCTAAAGTTTTCTATGTTTGTTTG
TTGAAACTTTATACATTCGATAGATTTTTTATTGGATTGCTAGCTGAATTGGTACTCCCCTGGCTGGTTCTTATCACACTTCCATTCTTATCAAT
CCAAATTACTTCATTTCGTGGGCGTATTTTCCAACAGGTGTCCTTGAGAAAGGGGTGACCACGATTGCCAGCCGAAGGTGAATGATTCAGCGCTG
CGTGGCCGCTCCATTCAAGCGCGAATAAAAAAATGAAAAGGGCGGCAAAAAACAAACACAGACGCGCCTCACACTTGATACATACATACATACAT
AAACGTGCATGTGTATATAAGTAGATATACATAGAGACATAGCGTGCTTAGATATTAAAATGCGGGCTTTGAATTGCCATTAAATTGCCATTGAA
TAGAGGGAAGGGTAGGGGGGTGTGTGCAAAACACTAGTTAATGGCGTCGCACTTTGCCGCTTTGTTTGCCCGATTACTTGTGGATCAATTTCCCA
TGGCATTAACTAACACTCACCTTTTCCAGTTCCTTCTCGATTTCCCCAGCACGAATCACCAGAGGACCGCGAACGGCATATTCCATGGCAATAAA
GTTGGGATTTATGTTATCCAGTGTGAGCGCTTTCGACGACGACGGCATTTTGTGGCTGGTTGAAAAGGAACTGAGAAAAAAAAAGAAGGGGATGG
ATATTCACTTCAGCAATCAACAATCACTTCTTGTTCGATATATAACGTGTTTTAAATGTGTTTTAAAATATATTGTTTTTGTTATGCGGCTTTTT
CAGCGAACGAAACTAACCGGCGGACGTCTAACGGTTGAATGAAATCGCCGCTTGTTCCATGGCGCTGCGACGTCGCTGCTGCCGTCACCGTTGCT
GTTGCCGTTGATTTCGCCGCACGTCGATTGGCATTGTTGCTGTTGTTGTGCAGGAACGATTTCCAGCGGCGAATAACGTACTGTTGCTGCTGGCG
CTGGTGCTGCTGCAATGCGGCCGAAACTGTGGCGGCAGCAGGTTTAATTAGCATTCGACTCATTATTTCTGCAACGAGAAGAGCGTCTCAGTAAG
TAAATTACTCAAAATACAAAAAAAAGGAAAGAGACAGACCGCGCTTTAATCGCAAGAATTTAGCACCATGAGAACAGCGGAAAGAAGAAGAAGCA
GCGAAATGAAGGGTGTGTGCGTGTATAAGAGTCCGGCTCACAATTATAAGAGCGGCGAATTGAAAGGCTCAGCTGTTATCACTACACCGAAAGCA
ATTAGTTTCGAAGCAGGGAATCATTTAAATAACTTTGTAGCTAGGAAAACTTAAGCAACTATAGATATTTCGATGTGAAATATATATCATATTAT

FIGURE SHEET 49

ATTAAGCATTTTTATATGGTATTGTTAGCACGCGCTCAATATAATATTCAAGTACCTAAATACATTTTCTTCACTGTGCATTTTTGTATCTTATC
AAAGACAAGGCGTGGTATCATTTACTTTTTCAGAGCTTATCAATGTGATTGCTTGTGGTTCGATACTTTATTGCCTTTCTGTTTATCAAGAAGCT
AAAGTGTAAATATTTACGACCTTTGGAAACTTTGCAATTAAATTCGCCGTGCATTTATCCTAGACTCAAACCCAATTGCACTCGCCGCAAGGCGC
GCATTTCAAAACTGCAATCGAGCATTTCTTATCAGAGTTTTGGGGCTTTGCACAAGCAACTGCAAAGCTGAAAAATATATATTTTATTTGAGGAG
GAATATATATTTTTGGAAAATATAAAAACGGTTACCGGCTGAATAAAATGAATGGCCATAAAGCCTAATCTCAAGAACATTTATTGCTTGACCAT
CCAGAAAATTTAATTAAAAATGGGACCGTTTAGAATCTACTTGTGTGTGCTGCTATATATTTCACTATATTTCTTATCTTGGTGGAACTTTTTTT
TTAGAGGCAGTTAACGGATTTGTGGGCCATTTACCCAGGCATTATGTATACATATGTATGATTTAATAGCTATATTTCTCCATTAAATCCACTGG
CAGGGCATCCATTGGTGGGGGCCACTATCAGTTGAGCGTACTTTTGACTTTGAGCCAAATCGGCGCAGCTTATCAGTGACGTCCCATTCGCAGCT
TACGATTCCCTGTCTTTCAATTGAATATATGTATATAGCTTTTCTGATTTCTGCACTTTGAAACGCCAATTGCGTAATGCAAAAAATGAGCAAAC
GAACAAAGAATCTTTTAGAAACATGACAATGACCAAAGATCGACATTACCTCCAAAATACTATACTTTTCGCACTCAAAAATCAGCATCAATCAG
CCGCAGATTGTTTGCTTTCTTTTTAGCGACAGCGAATTTATTTGTTTTTAAATTAAAAATGTACTAAATGCCGGTCCCGAAAAATACACAAATGT
ATGCTATTTTATATACGCACATATGTATCTTTGGAATATATGAATGTATGTGTATATATATAGGTATATTGTTTAGACGAGACAAACTGAAACTT
GTTGGCAATAACTTTTTGGAAAACCGGTTGCGGTTTTGATGGCATTGATATAGACGAAAGGGTTAAGAATTAGGGGAAAGGGGTAAGAATTTGGG
AATGAGAAAACATCGATACAGTGATCTCTGCTTAATTAAGACAAATTCAATACGATGCCGATATATAGATATAGATAGATATAAAATAATATATC
CAATAGAATTTTTATATGATAACCATCTAAAGCAGCTGTGCATAGAACTTTTGCGTATTAATTTAAGAAACATTACCTCCAAATATTTATTTTAA
ATAAATTTTTCAAATTTTAACATTTTTTTTTTTTTGAGACAACTTTTGTTAGTCACTGTTTATCTGCGATATATATATATGCAGCGTATCGCTTT
TGTTTGTGATTGTTTTGACAACAAAACTGGCTTATGCAACGAACTGTTAAAAAAAAATCTGAAACAGAAAATTATGTGAACTGGCTGCACTTTGC
TTCAAAGACCCCGCTCCCCCCTGCACTTTCACCCCCCGCATTGGGGGGATTATCAGACAAACCAACTGGATAAGATAGTAACGATAAGGAATCCA
ATTAGAACACGGCCATTCGGATTTACTAAAATCACAACTTTTGCCAAACGTTAGTAAATTATATTAAATTATATTGTAACTCCGATTGACACGTA
GAGCGCAACGAACAACAGCAACACAAAAAGAAGCAGAAATAACGGGTAAAGGGGGTGTTTTGATGTGCTAATTGGGTTGCTAAACAGCTGTTGAC
GCCGCACAAATTGAGCACAAAAAAAAAAACAATAACACGGCACGCAATTCAATTAGGGAAACGCACGCAGAACGATAAACAAAATCAGGGTACTA
TTGTGTATTAGATTTTTTTTTGGGCGCACAAATCACTTTCACTGTCACTTCCTCGCTGCTCCCAATTAGAATTTCTCGGCCACTGTGTTTATATA
TATGTACATATATGCACATGCATATATACATATATACGTCGGCAGTTCAAGAGCAAAAAATCGATTTTTCGCTGCACTTTTTAGTCGTTTCACCT
TGATGGGCGCAAGTGGGCGTGGCGATTATCTAACGGCGTTTGTTGTGATCCCAAGAACTTGCATAAACTTATTAATAAACGCGATATGTCTGTAT
ATAAAATACCTAATAAAAACGTGTGTGCTTGCTTGGCTGCGTGTGTGTGCGCGTACGTGTGTGTGTGTGTGCGAATATGTGCGGCGTGCGAGCTC
CAATCAGAATCGTATCAAAAATTCAAAGCTCTTTGGCCGCTAGACGCAATTAAGGAACTGACAACAAGAACTGAAACCGCACCGAGATGGAAAAT
GAAGTGCTGGCAGTATTTACCGACTATATGTTTTTCTTGCGGGCAAAAGTCACGATGAAGCGGGCAGCGATTAAGTTTTAAAAATATCACGTCTG
CAGCCCTCGCAGCCAAACTTTCGATAGACGGCGATAGATCGATAGACCAGCGATTTGCACCAACACTGGAAAGCTCAGAGCATTCAAAAACAAAC
TAATGTGTTTTATAAATAGCTCTTTTTAAATATCGATTAATTGCGATCTTAACTAACTTTCGTTTATTTCTATTAATTATGAACTTACTTCTGTT
TTTAAACATCTTTGCTCTTTGCTTGTTTTTCGTGTAAGGCTTTAAATTCACTTAAACAATTTTGCTGGCTTTGTGCGCATCTTCATATATCACTG
AAATTGATTGTTATAGGAGTGTCCCATTGAATTAGTTTTGTGTCGATTCAATCCTGGCCCGAAAATGTATGAACAAGCTATGCCCTACATTTTAC
CCATAGTCTACTTAGGTTTGTTTATATAGTATTCTTTTCAAGTTCGTTATGATAGCTCTTAGAAAATAAGATTTCTGTGAATATCTCCTCCGTAT
AAAAGAATTTTTATCAATAGTTTGGTAAGCTTTTTTTTCTCTTCTACAAAACCTTTTCGCATGTTTTATTTCACTCGAAACTTATTGCTATTCAA
AAAAATGGGTTTTCTAACGCTAGAATTATGTACAGAGTGCATTTGGAAAAAATGATGGGTAGTAAGCCCTAGAAAGCCATGGCTACGTGCTGATG
CCCATGATGGATTCGATGGAGAAACTCAGCTTGGGCTTCTTGCCACTGCCGGTGGAGGCAGTGGTGACTGCGGGCGTGGTCATCGCTGGATTTGT
GGGCGGGATCGTTAGCGGTATCGTCGGCGGCATCGGGTGATAAATGTGCTGCTCCTGATGAACGGGTGCGCAGGCGGCGGCGGCGGCGGCAACGG
TGGCAAAGTACAAAGCGTTACCGCCCAGCGTCGCCTCCATGACATGGTTCAGTTCCGGATCGGCGAATGCCCGCCGTTTGCGCATGCGCTCCATC
AATGGCGAGCTGAACGTGGGAAATCGCTGTTTGTATTCTGAAAGAGAACGAACCAAAAGGAATGGTTGAAATTAGTGAGGGTTTTGGTGGGGGCG
TTATCACTACAAATTGCCGCGATTCGTTATGAATGGGTATTCCAAATTGAAACAATTTATTATTGGGTAATCCGAGACACGCGTCGCCTGACCAG
ACAGCCTGGCACCGTTTTTTTTTTTTGTTTTTTTGTTTCAACTTCGGACCGGTTTCGGGATCTCCACTTATTCGGATGGAACCAGATGGAAAAC
CCAGAAAGAAGTCAATTGCTGTTGCCACATTTGGCTCTTTTTGTGAGTCGGATGGGTTTTTCCGTTTTTGGTCGCGTCTCAGCTTACCGAATGTG
ACTC
(SEQ ID NO: 115)

Exon: 10119..9969
Exon: 6908..6668
Exon: 6530..6386
Exon: 2913..2824
Exon: 2758..2496
Exon: 2224..1401
Exon: 1338..1001
Start ATG: 6508 (Reverse strand: CAT)

Transcript No. : CT4458
GAATCGACACAAAACTAATTCAATGGACACTCCTATAACAATCAATTTCAGTGATATATGAAGATGCGCACAAAGCCAGCAAAATTGTTTAAGT
GAATTTAAAGCCTTACACGAAAAACAAGCAAAGAGCAAAGATGTTTAAAAACAGAAAAATAATGAGTCGAATGCTAATTAAACCTGCTGCCGCCA
CAGTTTCGGCCGCATTGCAGCAGCACCAGCGCCAGCAGCAACAGTACGTTATTCGCCGCTGGAAATCGTTCCTGCACAACAACAGCAACAATGCC
AATCGACGTGCGGCGAAATCAACGGCAACAGCAACGGTGACGGCAGCAGCGACGTCGCAGCGCCATGGAACAAGCGGCGATTTCATTCAACCGTT
AGACGTCCGCCGTTCCTTTTCAACCAGCCACAAAATGCCGTCGTCGTCGAAAGCGCTCACACTGGATAACATAAATCCCAACTTTATTGCCATGG
AATATGCCGTTCGCGGTCCTCTGGTGATTCGTGCTGGGGAAATCGAGAAGGAACTGGAAAAGGGTGTCAAGAAGCCATTCGACCAGGTGATCCGT
GCCAACATCGGTGATTGCCATGCGATGGGCCAGCAGCCCTTGACCTTCCTGCGACAGCTGTTGGCGCTGACCTTCGAGACACGTCTGCTGGATTC
ACCCGATTATCCCGAGGACGTCAAGAAGCGCGCCTGTGCCATTTTGAACGGCTGCCAGGGTCAATCGGTGGGCTCGTACACCGACTCCGCCGGTC
TGGAGGTGGTGCGTCGCCAGGTTGCTCAGTACATCGAGAAAAGGGATGGCGGCATCGCCTCCAATTGGCAGGACATCTATCTAACCGGCGGTGCC
TCTCCCGGCATCAAGAGCATTCTCTCCATGATCAACGCCGAGGTGGGATGCAAGGCGCCTGGTGTCATGGTGCCCATTCCGCAGTACCCACTGTA
CTCGGCCACCATCTCCGAATACGGCATGACCAAGGTGGATTACTATCTGGAGGAGGAGACCGGTTGGAGCCTGGACAGGAAGGAGCTGCAACGGT
CCTACGATGAGGCGAAGAAGGTCTGCAATCCGCGTGCCCTGGTCGTGATCAATCCGGGCAATCCCACCGGACAGGTACTGACCCGCGAGAACATC
GAGGAGATCATTAAGTTCGCACACGATAACAAGGTGCTGGTGCTGGCCGATGAGGTGTACCAGGACAATGTCTACGACAAGAACTCCAAGTTCTG
GTCGTTCAAGAAGGTGGCCTACGAAATGGGCGACCCCTATCGTAATCTGGAAATGGTCAGTTTCCTGTCCACCTCGAAGGGCTATCTGGGCGAGT
GCGGCATTCGCGGCGGTTACATGGAGGTTCTCAATCTTGATCCCAAGGTCAAGGCCATGCTGACCAAGTCGATAACGGCGGCGCTTTGCAGCACC
ACCGCTGGCCAGGTGGCCGTGAGTGCCCTGGTCAATCCACCGCAGCCCGGAGAGCCATCATACGATCTGTACAAGAAGGAGCGCGATGGCATTCT
GGCCGCTCTAAAAGAACGGGCCGAGCTCGTCCACAAGGCACTGAACAGCTTCGAAGGCTACAAGGTTAACCCCGTACAGGGCGCCATGTACGTCT

FIGURE SHEET 50

TTCCACAGATCGAGATCCCGCCCAAGGCGATCGAGGCGGCCAAGGCCAAGGGCATGGCCCCCGATGTTTTCTACGCATTTGAGCTGCTCGAGACG
AGCGGCATTTGCATTGTTCCTGGCAGTGGATTTGGTCAGAAGCCCGGCACGTGGCATTTCCGAAGCACGATCCTCCCGCAAACGGACAAGCTGAA
GCTGATGATGGAGAAGTTCCGTGTGTTCCACGCCGAGTTCATGAAGAAGTACAAGTAGATCAGCTGCCAACTTCCCCGTCCTCGATCCCTGTGTT
AAGTGTCAATCCTCCGGCTTAGGATTAAAAATTTAAATTACCCTAATTGTTTTTTTTTTTCCTCTTTGTTACTGTGTCATAGCTGAATGCTTCT
AAGCTCTTCTTTATATGCATATATAGATATATATGAGAAATATATAAAAACATTTTT
(SEQ ID NO: 116)

Start ATG: 415 (Reverse strand: CAT)

MPSSSKALTLDNINPNFIAMEYAVRGPLVIRAGEIEKELEKGVKKPFDQVIRANIGDCHAMGQQPLTFLRQLLALTFETRLLDSPDYPEDVKKRA
CAILNGCQGQSVGSYTDSAGLEVVRRQVAQYIEKRDGGIASNWQDIYLTGGASPGIKSILSMINAEVGCKAPGVMVPIPQYPLYSATISEYGMTK
VDYYLEEETGWSLDRKELQRSYDEAKKVCNPRALVVINPGNPTGQVLTRENIEEIIKFAHDNKVLVLADEVYQDNVYDKNSKFWSFKKVAYEMGD
PYRNLEMVSFLSTSKGYLGECGIRGGYMEVLNLDPKVKAMLTKSITAALCSTTAGQVAVSALVNPPQPGEPSYDLYKKERDGILAALKERAELVH
KALNSFEGYKVNPVQGAMYVFPQIEIPPKAIEAAKAKGMAPDVFYAFELLETSGICIVPGSGFGQKPGTWHFRSTILPQTDKLKLMMEKFRVFHA
EFMKKYK*
(SEQ ID NO: 117)

Name: putative aminotransferase
Classification: enzyme

Celera Sequence No. : 142000013384690
GAATCTCCGGTGTTCGCGACACTTTGCCGATTCAAATTTGAAAAAGTCGTTTTGCTGTTTAACATAGACGCATCCTTCGTTGTTCACCAGCTTTG
AATTGTGCGGCGAGTACTCAATGGACTTGTTGTTCGAAACGTATCTGTAGGTGGGCTTATCGTGTGCATTCAATCCAAACCAGTACTCGTGGTCG
TCTTGGTTTATTTTGCTTTTCATCTGGAATAGGGTAACTTCGGTGTTTAGATCAGCCAAGCACATGTGGAGGCTTTTGCAGATGGTCAGGGCACT
AAACCAAGAAGCCTATGGTATTGTAATTTTGAAATTTCCAATCTCAATGACTTAAGTTAAGTCTACTCACTGTTTTTTCACTGAAATACAGGCAT
ATGCCCTTACCGTTTGCCTCATCAGCACGCAAAAGCAGCAGCAGCCAAATGGGAAGACAGTAAAGCATGCGTAGTATTTGACTCATTTCTTTCGG
TTTGTTGTATTCACCAGTACTGATGGATTTCGAAAGTTGCTCGTTTTGGTATAGCTCACTAATGCCATTATACCATGGTGCAAACAATTAGGGTT
TGTGGTAAATTACCTTTCCATATTATTTGATATACCTTAACCTAAGCAGGTACCACAATTTTTTGCTAAATTATAATTTATATATTAATTCCCCA
TTTTTTTTTTTTGCAAAATTTCAAATCTAACTGATTTTTTTCTTGACAAAAGTTGGCAGCACCGTATATGTCTAACCAGTGGTTCGGTTGTAGTA
CCCCGACTATCGCTCTCGAAATAGAGCGCCACCTAGCCGATAAGAGTGCAACCACTTTACATCCACCAAAGGCATTGCCAACTGTAAATTTTTAG
ACACTTGTGGACTATATTTCTTACGAGTGGCGCTCTTCTCTTAGTTTTAGTTTGTGTGAAACGTAAACGTAATTTAGATCATTGAACGTTACGT
TGAACGTACTGTGACTACGACTCCACACGAGTTTATACGTTTCTGTGCTCTCGACGCAGTCGGACGTTTAAAAATAAACGCGCTCCACCAAAAAT
ACCTAGCCCGCTGGCCGCAAACGCAAATAAATCTGAACAAAAATTCGAATTCCATCCGGATCAAACAAACTTACAAACCCGAAAATTAGTTCTTC
GACTCCAACGGCCGAGAAAACCGCAACAGTTTCAAAATGTTCAGCTCGATTTCAGGTAAAAAAGAAAAGCCCAGCCGCCAATCGAAGTTTATGTG
AAAGTTTGGAAATTAGAAATCTTAGGTCTAAGCATGTGTACATATGTATGTATATATATGTACATATGATATACGAATGATATATGTATGTGTGC
AGTGAGTGGGTTACCGCACTGGAGGAAGGAAGTCACTCGACTCCAACTACAACTCCAACTGCACTTCCAAGTTACATCATCATCACCAGAGCAGC
GGTGGAGTCGGACAGTTGGAGCAGCTGGTGACCACGCGGGATTTGGATCCACGGTCGGGTGGGGTTGGCCAACCGGGCGTGTTCGATCCGATACG
GGTCGCAGTAGCTAAAACCTAATTATCCGCTACCGCGACTCTGGTGATGGCAATGATGGTGATGACGACGATGTGGATGATACGTAAGCCAATTA
TGGCGCAGTTATATGTAGCTCCAAATGGACTACAAGTTGCCGTTCTCGCTGGCACATCCCACACCCAAAACGATGATACGTATATAATTATAGCT
GCCCAGATACACACTACACACAACACGTATCCGAGGCATCCATATATACTTTGTATCTTCGAGCGGTTACGCTGCTGCTCTTTCCTTGGGGCTCT
GGCACACTTATATGTTCCTGATGTTCGGGGAAGTGGGTGCAAAGAACCAGAGTTCCATCAGCCAGCTCCGCTTTCGATCTCTGAAATCCTCCGGC
AGTAGATGCCACTTGAGAACCGCATGGTCAAGCATTGGCACTTGTGAGTTAGGCACTTTTGTTCTATTATACATAGATTGTATTCATACCAATTA
ATATTATCTGTTCCCACTCAATGCCAAGCAGATGCATCGAAATGTAAGTAACCCCAAATGGTGAACTTTCCACTCAATTACCTTGATAATGTTAC
TCAGTATTAGACATTCCTCACCGACTGCGTAGTTCAACATTTAGTAGCTGCATATTGTTCCTATTCAGCACTTTGATCTTATATGTTTAGCATGT
GTTTTGGGTCTATCAGCTAAAAACATTCCTTTGGAAACCAATGATTAAGAGCTTTTAAGTACATTCATTTTTTGATTTCTGCTTGAACAGATTGT
TTAAAAAACACTATTCTAGAACAAGTGGTTATCACTGTGGGGATTTTTAACAGCATGTTTCTGAAATATGAAAATATAATAGTTTTAAATTTTAA
ATTTATAATAAAGTGACTTCTTACAGGAATCAGCCATGTTAAGAGATACCATTATATATCATTCTTTGGGATCTTTGGATTATTGTTTTTTGTAA
CTTGAATGGAATGAAACCCAGTTGATCTTCATGTTGTTAAAACTCAAATTTATTTGGTGAAAGCTCAAATATTCCTCGGTTCCCTAAATGTCCAT
TGGTCCGCCCGTTTGGTGGTGGGTCCGTGCGTTCAGGCCGCCGGAGCTGGTGTTGCTTCGCCCTCGGGAGCTGCTGGTGCAGGAGTGGCGGCCTC
GGCGGCTGGAGCTCCTTCCGCTGGTGGAGCTGCCGCCGGAGTGGCTCCTTCCGCTGCCGCGGCATCCGGTGCGGGCGTGGCTGCTCCAGTTGCGT
CTGCCGCCGCGGGTGGACCCGTGCCGCCTGGCGGCACCGTTTGCTCCTGCTCGGCAATGGGTTCCGCGGCGTTTTCCATGCCATTCTCGAACACG
GGCTCCGTGGTGCCACCACCATCACCTGGAGTCGGCGCGCCCTCCGCTTCCTTCTCCTTCGAGACCCCGATTTCCGTTGAATTCGAATTGTCAGC
TGGCCGTGAATCGCTCTCCACACTTTGCTCTTTGATCCCCGTCTCTTGCTTATCCTTCTGGCCCGCGTCGTGGTGGAAGTGATGCAAGTGCTCGT
GGCTGTGTTTCTGGCCATCCCCACTGTCCTCGGCGGGAACGGCGCACTTCATCTGGTTCTGTTCGCAGATGAAGTACTTCTTCTCCTGGCAGTTC
ACGTCCAGGACGACGGTGACATTGGGCCTGATCCTGATCTCCAGGCAGTCGTCCAGGTTGGATCGTTGAGTCGGCTCCACAATATTGGAGTCGCC
CATGTAGCGCACCAGTTTACCGCTGCTGATGTACTTGAAGCGCCCCTCCGACTGCAGATCGTTGCCACCGAACCAGAAGTCATCGAAGCCCACCT
GTGACGTCACGTAGTGTACCACCGCCTTGAAGTCCTCCATCGTGGACACGTCGGCCAGGTTGAGGCCCTTGCGCAGGCAGTTGTTCTGGGCCCCG
AACCAGTTGATCTGCCAATACATTTCAAGCGATATATAGTTATTTCGGGACTCTATGGATGGGCTTATTCGAATCTATGATAGCTTTATTGGTAC
TAAAATGGCTGGCCAAGTATATTACAAGTGATGGGATGCTCTCTCACCTTTTTGATGCCCACATAGAAGCACTTTCCGTTTAGCTCCCTGAGATA
CGGTTTGCCACAGGGACCCTTGTCCTTTTCCTTCTTGCTCTGCTTCTTTCCGCAGCCGGAATGGACCGTCATCAAGGTCAGAATCACAATTGGTA
GGATCCTCATGGCTGCCAGCAAAACTGAGGCACCTGTCCGGTCAAACTGTAAGCATGCGTGCCGCCCCCTGTTCTATATATACCCTTTCGTGGGC
GTGGCATCTGCATTATCGAGGAGTGACCAATTTCCATTAGGGAATCGTCGTGTATTGTTCGCACAGAATTTTTATCGACTGCTGCAGTCCATCAA
ATTGATTAATTCTAATTGGACATGGTGATGCCCAGGGGTTGGTGCATCTGTCGTTGGTTTCTCAATCGCCCACAGTATTGAAACTATGCTGGTAC
TTGTCAGACTTCCATCTGGGATGAAGAAGTTCCCGAATTCACTGACATCTTAAAAGGGTTCAGTAAATAAATTACTCAATTGCTATCCGATTAAG
TGGTCAATAGGTGACCCTCCACTTAAAGTTCATCCCCATTATTTTGTATTTTTCAGAGATATAATTTCAATGCTCTGTATACTTATTACATGTAA
AATTCGAATAATTACATATTCATCATCAGGATGAATTGAACAGAAACTAAACTTTCATATAAGAAACTATAAAGTATCTTTGCATGTCAATAATG
CCATCTTTAAGAACTTATCTTATACACTGGCCCTTGATTTATTTGAAAGTTAGAAACTTGAACTTCGATTGAAATTTATTTAACTGCTCGTATAT
TTAATTTCATTCGTGTACCCAAGCCGACCTGCACTTGAATATATATTTTAAAATAACTTGTTATATTATTGCTGTCATTTATTTTTAATCGATAA
TAGTTGTGGGCTTCAGCTGGGCAAGTTGTGGAGATCAGGCTGCTGGCGGTGCCGGAGTCTCGGCTGCTGCGGCGGCGGGTGCTTCTGCTCCTGGC
GCGGGAGTGGGTGCGGGCGTGGCTCCGTCGGCGGCAGGAGTGGCGGCACCTTCGGCAGCTGGAGCTGCTCCGGCGGGTGCGGCTCCTTCTGCTGC TGGAGAAACAGCTTCAGCTCCGGCGGCAGGGGTGGCAGTTGCGCCCGGCTCACCAGTTCCGCCAACGGTATTTGTTTCTTCCGCTCCCGGTGTCA
CCGAGACGCCATTCTGACCAGGTTGATCGTCATCGGGCACGTCGAGCGCCCCGACTGCATCCTCCGAGTCCGGCTCCGGGTGCTCCACTGAGCCA
CTGGCAATGGGGTCCTGGCGGTCGTGGTCGCCATCGCCATCGCCATCGTCCTCTCCTTCGGCACTTCCGCCAATGTCGTGGTGGAAGTGATGCAA
GTGCTCGTGACTGTGGTGCTTCGGCTTCTTGCCACTATCCGTGCCCTGGCAGTAGCGTTCCGAGCAGATGAAGTATTGCCGCTCGTGGCAGTTGT
CTGCCGACACCATGTTGATCTCGGAGCGGATCCTCACCTCCAGGCAGTCGTCGCACTCGGAGTGCTCCAGTGGCAGGACGTTGCTATAGTTGCTG
TAGTAGCGCACCAACCGACCGTTGCTGATGTACTGGAAGCGACCCTCGTGGTACAGATCGTTGCCCCCGAACCAGAAATCCTCCGTGTTGCCCAG
GCCACTCAGGAACCCAATGGCTCCGTCGAAGTCCCTTTGGTTACTCAAGTCCGCCAGGGTCAGTCCTTTGCGTAGGCAGTTGTTCAGGGCGCCAA
ACCAGTTCATCTGAATGGGTTTCATATTATTTCATAAGCCCATGCGACAGATCAACTCTTACCTTTTTCACCGAAAAGTAGTAGCACTTGCCGTT
GATCCTGCGCAAATAGCGACGCGGGCAGGGGGGTCCTGATCCCAGGAGCTCGCCCCGCGGCAGGATGCTCAGCAGGGCCACGAGTGCAGTCAGGA
GATGCTTCATTTCGCTCGCTTCCGCCGGTGCACAGTGAGCCGGCTCAAATCGCCTCCTGTACTTATATCCTCCGCTGGCCAGCAGTGCGCCCAAT
CGATTTGGAGCTCGCTGGAGCTGGAGCGGCATCTTCGGCAGCATGGCCAATTCAATTACAAGTCCATGCCGCCGGAATGCCTACGCCAATGTCGT
GGGCTAATTTGCTCACCCGCCAGTGGGTCAGGTTTAGGGTCATTCAGTTTAATTGGCTATTAGATACACTCGAAGAAAACGAGCCGGAAAAGTCG
CATGGGGTGCTGTAATTGCCAGTAATGTTAACCCTCTAAATTCCTTGATGGCAATTCATCCGCCTAATAATGGGCATATTGCGAGTAACTATTAT
ATCATATATAGATGTTATAAAATTGTAATACAAGTTTAATGCAAATAAATTAAAAGATTATATATATGGTTTGAAATAAGCAATAATTCTTAGC
AGTATTCTAACTCATTCGAAGGTAGCAGAGCTTTCTTCTTCTGGAGTATGATGATGATAGATGGATATAAAATGCTTCAGTTCCTTTGACCCTGA
TCTGTCCTCCCATTTAGTTTGTATCTGCCGAAGTGAGTTAATTGCTGGCTATGAACTCGCTGGTAATCTTCAACAGCTCAAAAACGCTAAGAATA
TTAAGTTCTGTGATTCGAGCAACTGGAGTGACTTCATAGTCATTAGCATAACCCGCCCGAAGGGCTAGATGTCTGACCCGGCCTTGTTCTTTCCG
ATTATTGATTTACCTGGCAGGGTCGTGACATCAGCCATTGGATTGTCCGTGGCCAGGACACGAATCGCCCGCCTTTCCTTCTGTTGCCAGCTGAC
TCAGACGACCTTCGGTCGGATGACGATTGCGCCGGGTGGCCACAACAATTCGTGGGGCGTGTGAGTACCACGCCACCCCTTTCTGCCACGCGCGC
TACTCTCACATATATAATTCTTTCGTATATTGTATCTCGATTGTGCAGTTGTATCTCACATGACATCATCAGCAATGGCAACAACAACGGCGGCC
CCAGTAGCTCCATCGATTCATCACGGATTGTAGCTCTTTTTTTTAAGGCATCCAGAACTGGTGTGGAACGTGAGTCGGCAGACCTCAAATCGCAG
TAACTCATAGATATTCGTTCCATGCCCGTATGTGTGTCCGTTCCGAGCTGGGTTCCCATGTAGCCCAAGCTACAGCTACAGCTACAGGTTTTCCT
CTATCCGAGGCTTCTGCGCATTATTTCAGCTGCGAGTGCGACATCGACGAAAACAAAATCAGAGAGCAAAATCAAAATCCAAAACTAAAACCAAA
CCAAAACCAAAACAAAAACGACGCCAGAGGCTGTGAGAGAATCTGGGCTTATTGTGTTACCTTTTGGCCATGCTTCTAGCCGGTTTTCAGTGTTG
ACCACAAGTTGCCACAGTTTTGAATAAAGACTGAAGAACAAAATGCGTCGTATTACGCAAATGCCTTAAATAGGGCCGCTGGCCTTAGGAATTCC
GCGTGTGTAAGCCATTAAGATATATATGTACATATATCCAAAGGATTTGGCGGGGAATATTAAACACTGCGGTTGCCTTATACGTAAGGCCACCT
TTTTTAAGTTTAATAACTTATCATTCTACGAATGTATTTTAAGTATCTTTAAATACGATTTTAATTTGGAAAACAGCACAATATACTTAGCATGC
ATCTCTATACATATAGTTACATATTGTACAGTGTAGATTGCACGATTCCTTCCACTTAAATTGCTATTCTAGATTCTAGATTGTTAAGCAAGTCC
AATGCCACATACATACATTCCTTAGCCATTAGCCATTAGCATTTGAAATGTCTGAATTCCCTTTGATTCACCCTGTTTTTTTTGAGCAGTAAAAG
TAATTTTCAACACCTCGGCCGAGCCCACACATTCCATAATCTCGATACCCAGCAAGCGTAGAATAGAAACTATTATTTTCGCACAATTTTCGGCT
CCTGCGGTGGCGATTGGCTCATTAAATGCGAAATGCGAAATGCGAAATTGGCCGAAACTAAATTATTTGGAAATGAGCCGAGTGTATGGGGCCAT
TAAAGTATCTCTGCGGAGAGAACCGAATCAGAATAAACACATTCCCGATCACAATCAGAAAGCGTGAATAGACCGCACTAGAAACTTGGGGGCGA
TTTCATTCGCCGGCTGCCCATTATGACATCACATACGCCGAATAATTTGAATACTCGAGCTTTGTTTGCCTCATTCGCATACAAGCATACTGTAT
ATTACAAAGAAATTCCTCGGCTATTTCCGCCCGTTTCCGTTTCGCCCAACCGATTCGCACCCGGTTCCGAGTTGAGCGGCACAATGTTTCTATTT
GAGTGGACGCACACGTCACTCCCAGTGAATGCAGATTCGAGGGGACAGCAAAAGCTGGCGCTCGTTAATTTCTATTAAATTGCGAATATAAGTCT
CAAGTCTCGAATTTTAAGGCTGACGCCATGGGGCTGGCGATCACGATTTCAACAGCCCCTAGTTGCGCAGTTTCTATTAATAGGAAAGTGTCCCA
GTCTAATCGATCCGATTTAGTCATGTAAATAGTTCATGCTCCAGCTGCTTTGTTTATGTTTCGGCAATTACCTGTCTGGAATTTGGAATCTGAAA
TCTCAAATCTCGCATCTTCGATCTGATCGGCGCTCCACCCTGCTGATTGCAATCAGGCTATAAATTATAATTAGCGCCAGGCCAGAGCTTAGTTA
GCATTCAGAGGGCCAGTCAGCATGTTTCCTAGTCGCCAAAACCAAAGTAATCCCATCCAGCCAGCACAGTCAGGATCTAAAATGCACTCCTCATT
CAATCCCCAGCTTCCTTGAAGAACTTCGGTGACAAGACCGCCAACCTCTTCAGCAAGAAGAAGGATGAGGCCGAGAAGCTGGCCAACGAGAAGGC
TGCCGAGGCCCAGAAGCTAGCCGAGGAGCAGGCCAAGAAGGTGGGCCAGTCCGTACAGCAGACCAAGGGCGAGGCCGAGCAGTTGGCCGCCAGCA
CGGGTGAGTAACGAACATCCAAAAAATAATGAATGTAACACATAAAAGATGTCTTAGAGAATTAATTGGAGTTATTAATTCTAAAGACTTCCAAA
AACTCTTGCAACGAAGAATTGAATGAGTCCCGTTTGAGATAACTTTCAAAATCAACTTTCAGTTCTTGCTAAAAATGTTTTCTCATTAGCATTCC
ATTTCCAATTTATCTAAAACGCAAATCTTTTAAGCATATCAAACACAAGAGAACTTAATAAATGGAATTCTTTAGTGACGCGTTGACGTAAAACA
TGTTTCCAAGAATAAGATTCGCATTTTTGAAAACATTTCTTCATAAATATTGAAATATTTCTATAATTGTGAAAAGCAATTTAATGTGCTAGAGA
TTTATAACTAAACAGAACATCAATGCTATGTTTTATGCTGGAGCAAAGCCCGACCAATTCAATAAATATCTTTAGGAGCACTTTTAAAGATATTT
TGTAAGAATTTTTCCCACTAATATCTCTCTTTATCATACAGCCAAGGAAGCCGCTGCTCTGGCCACCGCGGAGGCTCAGAAGGCTGGACAGGCGA
TTGACCAGGGTGTGAACCGTGCCGCCGGAGCCGTCAACCAAGGCAAGCAGGCGGTGGACAACACGGTGGCCCAGGCGGCGGCCGTGGCCCAGAAC
TCCAAGCAGGTGGCGGCCAATGTGGCGGAGGCCTCCCAGCGAGCGGCCGCCAATGCGGTGGACCAGACCAAGAAGGCGGCCAACGACGCCATCAA
CAAGAGCGTGAAGGCCGCCGAGAACGTGGCGGACCAGAAGCTGAAGCAGGCGGAGGGCGCCATCGATGGGGCACTGAAGCAGACCAGTCAAACGG
TGGACCAGAAGCTGCAGGAGGCCAACCAGTATGTCGACCAGAAGCGCCAGTCCGTCGAGAAGACCGTCCAGGATGCGGCCGGACAGGCCCAGGAG
TCTGCCGGACAGCAGGCCAACGCCCTGTTGGGCAAGCTGCATCTGGGTCAGAAGTAGAGGCGTCTCCCTTCGCGGTGCCACCTAAAATATCTTGA
TGTGAAAATGCTTTAGATACAAAAACAAAAAAAATAGAAAGGAATTTGCT
(SEQ ID NO: 118)

Exon: 1001..1195
Exon: 8371..8553
Exon: 9067..9557
Start ATG: 1177

Transcript No. : CT4516
TCGACGCAGTCGGACGTTTAAAAATAAACGCGCTCCACCAAAAATACCTAGCCCGCTGGCCGCAAACGCAAATAAATCTGAACAAAAATTCGAAT
TCCATCCGGATCAAACAAACTTACAAACCCGAAAATTAGTTCTTCGACTCCAACGGCCGAGAAAACCGCAACAGTTTCAAAATGTTCAGCTCGAT
TTCAGCTTCCTTGAAGAACTTCGGTGACAAGACCGCCAACCTCTTCAGCAAGAAGAAGGATGAGGCCGAGAAGCTGGCCAACGAGAAGGCTGCCG
AGGCCCAGAAGCTAGCCGAGGAGCAGGCCAAGAAGGTGGGCCAGTCCGTACAGCAGACCAAGGGCGAGGCCGAGCAGTTGGCCGCCAGCACGGCC
AAGGAAGCCGCTGCTCTGGCCACCGCGGAGGCTCAGAAGGCTGGACAGGCGATTGACCAGGGTGTGAACCGTGCCGCCGGAGCCGTCAACCAAGG
CAAGCAGGCGGTGGACAACACGGTGGCCCAGGCGGCGGCCGTGGCCCAGAACTCCAAGCAGGTGGCGGCCAATGTGGCGGAGGCCTCCCAGCGAG
CGGCCGCCAATGCGGTGGACCAGACCAAGAAGGCGGCCAACGACGCCATCAACAAGAGCGTGAAGGCCGCCGAGAACGTGGCGGACCAGAAGCTG
AAGCAGGCGGAGGGCGCCATCGATGGGGCACTGAAGCAGACCAGTCAAACGGTGGACCAGAAGCTGCAGGAGGCCAACCAGTATGTCGACCAGAA
GCGCCAGTCCGTCGAGAAGACCGTCCAGGATGCGGCCGGACAGGCCCAGGAGTCTGCCGGACAGCAGGCCAACGCCCTGTTGGGCAAGCTGCATC
TGGGTCAGAAGTAG

FIGURE SHEET 52

(SEQ ID NO: 119)

Start ATG: 177

MFSSISASLKNFGDKTANLFSKKKDEAEKLANEKAAEAQKLAEEQAKKVGQSVQQTKGEAEQLAASTAKEAAALATAEAQKAGQAIDQGVNRAAG
AVNQGKQAVDNTVAQAAAVAQNSKQVAANVAEASQRAAANAVDQTKKAANDAINKSVKAAENVADQKLKQAEGAIDGALKQTSQTVDQKLQEANQ
YVDQKRQSVEKTVQDAAGQAQESAGQQANALLGKLHLGQK*
(SEQ ID NO: 120)

Celera Sequence No. : 142000013383916
AATTAAATTATTAAATTATTCAAAACAAGCAAAATACAACAACATACAACAACAAAACAAAACAAAAGAAGTAAAACTAAACACTACCAGCTAAT
TATGTTAGATAACTGAATGAGAAAAGCTAAAACAACAGCAATAGCAACAGCAAAGGCATAAGCTAAGTTTGATCTGCAACCAACACCTCTTACCA
CGAACAACGGCAAGCAATAACAGCAAGAACCCTTCCTTCCTCACCCCGATATAATTATGAAATTATATTATTTATAAAAACTGGGAACTAATTTA
CGGAACGATGGCCAGCGTCAATAGAACAACAATACTACAGCAAACAGCAATGCTCGGGGCAGAGAGAGGATGCGACTCAGCACATGAGACTAGAC
CCACTACACTGAAAGACGAACGAACATAGCGACGATATCGATTAGTATTGTTAAGTTTGGGTTAGGCTATATACTATAGATCCAGTCATGTTGCT
GGGTCGTCCCACATCTCCCCAGCCAAATCAGTGTTATCGATCGGATGCAAAGAATCGAACCGAAGACCTGTAGATTCTTTCGCCTCCGAAACGAC
AAACCAACAAACAAACTCAACTTCGGTTGGTTTAAAAATATATAAAAATTGATAAAAATAGTACAATGTTGTGTTTTTCTTTCTGCGCACGTACA
TATGTATGTATGTATATCGATCTTTCATATTTCGACTTGAACCCAATTATTGCAATGAAAGTACATATGTATTTGTAATTCAAAAATTATATTAG
CATACTTACACAGACCATTTGTGCAGTCAACCAATTGGTCGTCTCAATTTAATCTTCGGCAGTTCGAAGCTAAATTATTATAATTATTTTCTGTT
GTTAAAAGAGGAAAAAAACGTACGCTCATCGCTTCTAAAATTGTTGGTCAAAGTAGGCCACGATAAATACATCGAATGTCATTTCGACCGACTGG
CACACAACCTCGTTAGCCAATCTCAGTTCAGATCTCAACGTTGTAACATCAAAATTAAAAATTGTAAAAAGTGAAAGTCCGTTTTTATCCTTTTT
TACCAACCAACTTTGAAGCTAAACTAAATCGTTTTAAAATCATTAAACAGTAAACTAACATGGGCGATGAAGGCGGTGGCGGTGGTCATGGCAAG
GGAGACCTTAAGTCTTTCCTCATGGACTTCATGATGGGCGGCGTTTCAGCTGCCATAGCCAAAACGGCAGTGGCTCCTATCGAGCGCGTGAAGCT
CATTCTGCAGGTGCAGGAGGTTTCCAAGCAGATCGCGGCAGATCAGCGCTACAAGGGCATAGTCGATTGCTTCATTCGCATTCCCAAGGAGCAGG
GCTTCTCGTCGTTCTGGCGCGGCAACTTGGCCAACGTAATCCGATACTTCCCAACTCAAGCCCTTAACTTTGCCTTCAAGGATGTGTACAAATCG
GTTAGTTGTTTGGACAATCCTTATAATAATCATTTCACATACGCCTATAACATATAAAACATAAAACATACTACAGGTATTCCTCGGGGGCGTGG
ACAAGCACAAGCAGTTCTGGCGCCACTTTGCAGGAAACTTGGCCTCTGGCGGTGCAGCAGGTGCCACATCTCTGTGCTTCGTTTATCCACTGGAC
TTTGCCAGAACCCGGTAAGTTGATTCATTATATACACATTCAATTGGTTTTTCATTTATACACATATACATTAAAAATTGATAATTTTGAGTAA
TTGAGGAAAACAATTCGAACCTTTACATACTTACTATAGTCGTTCAAAATAATCGATGTCCAAATGAGATTATACATTAAGACGCTTTTTCTACA
ACTGCATTATTCACCCACATGAACTGTTTTCCCCATTTGATTTGAATTTGATTTACTTTCATTGGATTCGATTTTGTTATTAACTATTTATTACT
ATTCCAATTCAATCTTCCGCCGACAGTTTGGCCGCCGATGTGGGCAAGGGCGGCAATCGGGAGTTCAACGGCCTGATCGATTGTCTAATGAAGGT
GATCAAGAGTGACGGACCCATCGGTCTGTACCGTGGATTCATCGTGTCGGTGCAGGGCATCGTCATCTACCGAGCAGCATACTTTGGATTCTATG
ACACTTGCCGCGACTTTCTGCCGAATCCGAAGAGCACACCGTTCTATGTGAGCTGGGCGATTGCCCAGGTGGTCACAACCGTTGCCGGTATTGCC
TCCTATCCCTTCGATACTGTGCGTCGCCGCATGATGATGCAGTCTGGCCTGAAGAAGTCCGAGATGGTGTACAAGAACACAGCCCATTGCTGGCT
GGTGATTGCCAAGCAGGAGGGCATTGGAGCCTTTTTCAAGGGCGCCCTATCGAACATAATTCGCGGCACGGGCGGTGCTCTGGTTCTCGCCCTTT
ACGACGAGATGAAGAAGTACTTTTAGCCCCAGTGTGCCGCCGTTTGTGGTGGGCCAATTCGATCGCCAGCAGCAGCAGCAGCAGCCCCGGCCACA
GCAAATGTCACACCACGATGGCGTAGCACCAACCGAACACACTGTCCACCTCTTCGTCGAGGAGGACTTGCTCCCACGAGCCCAGTAGTAAATTA
ATAATTTGATTTGATAGGTCGCCCCACATGGTGGTCGGTCCCTCATTTCAGATTGTGTTCACTTTCGCAGTGGTTGAGAAAATACAAATAATATA
TTGAACTCAAATCTTTGTTGTGCGCTCTTTGTTTGTTTTCATCATCGCGTGTTTTTTGCTTTTTGGTGCATGTGTGTGTACGGATTAGGGTGGGC
CACATCTAACTAGGATCTAATTATCCTCTCAACAAGCTAAGCTAGTCGTTATATTCAACTATATGTGAAGGACAAACAAAAAAAATTTAATTAAT
TTACGTATATTATTTTGTCTCGATTGAATACATTTCAAAAAAATTACAAAATCATTATATGTACGCCATGAAATGATAAAAGGTTATGTACTATA
TGGGCTGCCCACCCTACTCGTTTTCGTAGATATGGTCTTGTGCGGGTGGATTTAAGACTTAAACGTTAGTTAGCCATTTAAATAAAAATAACATT
AAAAACAGAAAGCCATGTCGCTTTCCATTGTCAATCTGCTGCATACGTTAATTAACAACAAAAAACAAAAGTACAAAAAAAAGAGGCAAAATTAC
AAGTACTCGATCTGCACTTATTCTGTAAACAATTAGAAATAACTCTAGACTAAGATCCAGTCACTGAGTTGGCTGCACTTAGTGGGTAGCCCCGG
ACCTGTGGGCCAGGAACAGGAAGTACGTGCCCGCCGCGTAGGCCAGGAAATTGAAGAGTCCAAAGACACCGGCGGCGGTATTCGAACCGGAACCC
TTGCCCGTGGCATCCGACCATCTGGCCAGCTGGACGATGAATCCGATGAAGTACAGCAGCGTCAGCACAGCGGTGGTGATC
(SEQ ID NO: 121)

Exon: 1001..1425
Exon: 1502..1629
Exon: 1927..2406
Start ATG: 1105

Transcript No. : CT4708
AAAATTAAAAATTGTAAAAAGTGAAAGTCCGTTTTTATCCTTTTTTACCAACCAACTTTGAAGCTAAACTAAATCGTTTTAAAATCATTAAACAG
TAAACTAACATGGGCGATGAAGGCGGTGGCGGTGGTCATGGCAAGGGAGACCTTAAGTCTTTCCTCATGGACTTCATGATGGGCGGCGTTTCAGC
TGCCATAGCCAAAACGGCAGTGGCTCCTATCGAGCGCGTGAAGCTCATTCTGCAGGTGCAGGAGGTTTCCAAGCAGATCGCGGCAGATCAGCGCT
ACAAGGGCATAGTCGATTGCTTCATTCGCATTCCCAAGGAGCAGGGCTTCTCGTCGTTCTGGCGCGGCAACTTGGCCAACGTAATCCGATACTTC
CCAACTCAAGCCCTTAACTTTGCCTTCAAGGATGTGTACAAATCGGTATTCCTCGGGGGCGTGGACAAGCACAAGCAGTTCTGGCGCCACTTTGC
AGGAAACTTGGCCTCTGGCGGTGCAGCAGGTGCCACATCTCTGTGCTTCGTTTATCCACTGGACTTTGCCAGAACCCGTTTGGCCGCCGATGTGG
GCAAGGGCGGCAATCGGGAGTTCAACGGCCTGATCGATTGTCTAATGAAGGTGATCAAGAGTGACGGACCCATCGGTCTGTACCGTGGATTCATC
GTGTCGGTGCAGGGCATCGTCATCTACCGAGCAGCATACTTTGGATTCTATGACACTTGCCGCGACTTTCTGCCGAATCCGAAGAGCACACCGTT
CTATGTGAGCTGGGCGATTGCCCAGGTGGTCACAACCGTTGCCGGTATTGCCTCCTATCCCTTCGATACTGTGCGTCGCCGCATGATGATGCAGT
CTGGCCTGAAGAAGTCCGAGATGGTGTACAAGAACACAGCCCATTGCTGGCTGGTGATTGCCAAGCAGGAGGGCATTGGAGCCTTTTTCAAGGGC
GCCCTATCGAACATAATTCGCGGCACGGGCGGTGCTCTGGTTCTCGCCCTTTACGACGAGATGAAGAAGTACTTTTAGCCCCA
(SEQ ID NO: 122)

Start ATG: 105

FIGURE SHEET 53

MGDEGGGGGHGKGDLKSFLMDFMMGGVSAAIAKTAVAPIERVKLILQVQEVSKQIAADQRYKGIVDCFIRIPKEQGFSSFWRGNLANVIRYFPTQ
ALNFAFKDVYKSVFLGGVDKHKQFWRHFAGNLASGGAAGATSLCFVYPLDFARTRLAADVGKGGNREFNGLIDCLMKVIKSDGPIGLYRGFIVSV
QGIVIYRAAYFGFYDTCRDFLPNPKSTPFYVSWAIAQVVTTVAGIASYPFDTVRRRMMMQSGLKKSEMVYKNTAHCWLVIAKQEGIGAFFKGALS
NIIRGTGGALVLALYDEMKKYF*
(SEQ ID NO: 123)

Name: mitochondrial carrier protein; ADP/ATP translocase
Classification: transporter
Gene Symbol: Ant2
FlyBase ID: FBgn0025111

Celera Sequence No. : 142000013384605
GATGCGGCACGACGAGGCACATCCGCGGGAAATGGCGTCGTCGAGGAGGATTTGAGGCACCTGAGTGGTCTTGCCACATCCAGTGCTTCCTACAA
TGAGTATTACTTGGTTTTCCCGCACAGCCTGGATAATATCGTCGGCGTATTTCATGGTGGGCAGTTTTTTCCGTGCTTCTAGCCGTTTCTTGGCA
TTCTCCTCCAACTGGCGTTGCCCCAGTTCCAGCTGCAGTCTCTCGTCCAGCTTGGGGTTTACCCAGTCTAAGTCCGCGTTCCGTTCCTTGGTCTC
CGCAACGAATTCCTCAAAGTTTACACTCAAAAGATGGCGAAACTGTTGCTGAAATTTGGCATCCACATTTTTGTCATCCACATTTTGTCTGGACG
GTGCCCGGCTGTAGTCCTCCATTAACTCCTTCACACGCTCAAGCACTCCACTGGGAGCACTGACATTGCAGCCCAAGCGGATTTGCGGCTCCTTT
GATTCCGCATTCTCGCCTCTGTCCTTCTTTTGCTGCCGGGCAAGATTGCGATAGTACAAACCGATGTCCTTGCCCCTGAGACCCGGTGGGCGGTT
GCCCTTGCGGGCGTTGGAGCCGGATGAGTCCCTATCGCGCTGCATCCTGTCCAATTTATATAAAAGAATTCAGAAGAAGAATTCCCAACCCGAAG
TCAACAAAATTCATAGTGCTGTCGGACTGTCAAAATGCGCAAATCAGATAGACTAGGACTGCCAACTTAATTATATACACCTATTGTGTTACTTT
AATAATTAATTTTCAAATATAAATATTTTATTCAAACAAAATTGGTTGCATTTAGAACACGAAGCAAAATAAAATGAAAATCATAAACAAAGTTT
TAAAAATAAGTGAAAAACACCGGCTTGCTGCTTATTGTTTGGTTCGAATACAGGCTAAATCCCAAAAGTATATTTCCATAACCCTTGAAAATGAA
GCGGTTTGATTGAGCGATCCCGCTGCGGTCACACTAATTTCGATCAACTCAACGCGCTGAGTAAATCGAACCGCTTGTGCTTAGAATTTGTTTTT
TCGCAATTAACGGCCGTGAAGAGCCAGCGATCTGCATGCCAAGTGTCCAATAACTAGGCAGAACAGTGTTTGCGTTGCACAAAAGCCCGCTAGCG
GAGTGTGTTCCATGTGTCATTCCCGGCAAAGGAGCAACAAGTGGCCGAAAGTGGAAAGCAAGAGCAACAACTAAATAAGTAAGGAGTACCACACT
GCAAGAAAAAGTGTTCGGAGGGAACGGTGTGCACAGCTTGTCAGCTTGTTTTTTGTACAGAGCGTCGCGCAATAAAACAAACAAAAAGACATAGT
CCAAAAACAACAACCACAACAAAAGCCGTTTGATCGCGAGTTTGTGTGCGTGTGCGAGTGTGGCTCTATTTGTGTGAGAGTGGCAAGCCATTATT
TTTCTGGTCTTATGACGTAAACCACCGAAAAAAATCAAAAGTGAGCAGGCGACACAGATATCAAAACGAAGGTGAGCGCATTCTTACCAATTCTC
GTTTCGTTTCTTGGAATTCCAGCGGTTATTAGACGGTTTTATACTTGTTTACATTTTCGCAGTTGCAGCACACAACTAATGCCAGAGCGGGAGCG
AGAAAGACATATGTAGATCGTTCTGTGGAAGGAGTGTTGGTCGCGGAGGGTTGTGTTGTGATGTTGTGGAGGGGAGGGAAAGAGATGCAGTGCAT
GTAAACAAAATAGAGAAAGAGGCAATTGCAGTAAATTCTTTGGCAAAAGAAATCTTGTTGAAAGCATTTCCTCCGCAGATGCTTATGTGTACTGG
CGACCTGAAAAGAAATTGTTGCCCTGCTTGAACTTGTCGCTCCACTCTCCACTACCCACCTCCTCGCCCCCTCCCTCGCACACTCCTCTGCCCAC
ACACACACACACACACAACACTCCATTCACAATTGGCCTTTTGCGGAGTCATATATTAAATTTGATTTCTCTAGCCGAGCACTGTGAATGATTTG
CCGCCAGTTGGCACGCCCGTTCGCCACACTGCAGAAAATACCAGGGCACATATATATCTATATCTATATATCTATTAAATTTATCCTTGCATGCC
AAATATTGAAACGCAGCACTTTATAGCTCTCTTAGCTTAAAATGTAAATTTTACTCAATTTAAGAGCACTAATAACGAACGTTTATTTCATTTCC
TAATCAAATCTTACAGTTTAAGTACTTTGTTTTCCGTGTAGCGAGCCAGAACCATCCGCAAAACCTGTTGCTCGTTTGCCTTTTTATTGGATTTT
CTGTTTTCTACCTCTGCTGCTCAGCTGCTGCGATTCCGATTTCATTAGTGATTCATTAGATGCGTTGGACAAGCTAACGCAAAAAGCCAAAGCTT
GTTCCCAACGCATCCTTCAATACAAGGCAATTCAAATGTTCAAACGCTAACGGCCAGCCTCTCAGCCTGGTCAAATGAATCACTCCATATTCTCC
ACATATTCTAACCAATTTCTCTCGTGTTTTGTTTGGCTCTCAGTTTTGCGCTGTGAATAACGTGCTATTTCCTATTTTGGCTGGCCGCGATTATC
GCATCGTTTTGTAAATTTAGTGCGCATTATTAATGAATTTGTCCAATTTGCTGCGGTATACTTTTATCGTTTTTGTTTATAATTATAATCAGTCG
TTTTCACGCGGTGAGAGTTTTGGATAGCACAGTGGTCGGATTCTAATTTGGAAAATGGTTAAGCTTGAGAGTGTTTTAATCTGTAATATAAACTT
ATTGTACAAACCTAATTATAAATTGATCATTTTTGAGCTTACCAGTAATATTCACACAGTATTAAAATTATAATTCCTATTAGATTTCCACCCTT
AAAAAATTTTAAATGAAAGCCAACTCTCATGTGTTAATGTTCTTAAGCATGTAAAAGGAAAACAGCACCCTTTCCAAGTCGAAGAACCACTGTAA
TGGGCCTCGTTCCCTCAAAATACGTACATATGTACGTGTTAATTGAAAATTCCACACTCCGTTGAGGCTGAATCGACATTACGGCACCCCAGATA
ATTGTAAATAAACCCAAGCTGATAATGATCGACCACCTCCCAGCCATCCGTCCATCGATTGGATGCATTCGCTGGGAAGCCATCAGAAACCGCGG
TCTGTGCGCTGCTCTCGAACACTTGTAAACAAGGAACAGCTGTGCAAGTTGTCTCCCCCAAAATATTGAAGACTGCGCAGGCCCCAAAAATCGTT
GTTTGGTCTTTGTTTAGTTTTCGCCTAGCTATCCAACGAAATGCGCCTCAAAAAGCTGGGGTTAGACTTGAAATCTTTTGCATAGTTTATGAAAT
CGAACCCAATATTTCTGTTCTGTTCTTTGCAGAATGTCTCGTCACGAGAAAACGAAATCCACGGGCGGCGGGCTCCTGGACAGTCTGTTCGGAAG
ACCCTCGAAGTCCAAGGGAGGAACCATCAGCAGTGGCACCCTGGCCCATGGCGGACGACCCGTGTCCGCGGACAACTATGTGGTGCCGGGCGTGG
AGGACTTTGAGCAGTACATCCAGCAGCTAAGCGTTGCGGAGCTGGATGCGAAGTTTCTGGAGATCATCGAGGACATGAACATTCCGAAGGACAAG
AGGGAGCCCCTGTTGGCCAAATCGAAGGAGGAGCGACAGAAGATGATTATGTGGCACTTGAAAGGTAAAGAACATGGTGCAAGTACACGTTTTCA
AACAGAAAACCGCATTTGTGTTTGAAGATTGAGTATCGTTTGGCTAAGAACTATAGTTCTGGAATAGAAAGTCTAAGAATAATCTACATACATAT
ACGAATAATCTAAACTCGTCTGAACCGTAATGTTCCAAGCAACTTTGAAAGGCCAACCGGATTGGCAAAACTTTAACACCCTTTCCCTTTGCAAG
GGTATACAAACAGCAGACCATCGATTTTCGTGCAACTGGGTGACTCTGCCTTCTACTTTTTTTTTTTGCTTTTGTTGTGCTGCGGAATATTGCAT
TCCACTTGTGATAAGATAAGCAGGTAACGGAACTCGTGTCCGTGTGCTTTCCCCGTTTCGCTGTGTGCGTGACACTGCAAATTTCGCTTTCTGAT
TGCTTAGCGCCTTCTTAGCTGCCAATTTGCTCTGTGGCCAGGTTCTGTTCTATATTTCTGGCCAATTCCTAAACCGATTGAAGTGATGTCAACGA
TCCTTTGGATAAGTAAGCTCATAACATACATAAGTCTCTAAATGGTTTCCACTTCAATTAGTCAAGAGGTGATTACTTTGTTTGTTAACTACATA
TACTTGCTTAACTCTACTTCAATTTTGAGAATACTTTATTTCTAGAATTATTATAACGATATTATGTGCATCGCAGCGCGGTAATGATTCAGCTG
GAATCTTCCCTTGTGTTTGCTTCATTCATATCCAGCGAGATTAGTACGGTGTACTCTACTGTACTACAGTGATACTACCAATTATCACTGTAGCA
CATCGCCAGCTGTATCTTGAGCACATTTCAATGCCAGCTCAGCTTTCAGCTTCAGCTTCGTTCTTTGGGTCTCGCTCCAGTTAGTTCACCATGGC
CATGGTCCATTATCAGTCTTGCGGAGTGTGGAATCAAAGTTCCCTTATCGTTTGTAACGCCTAATTGCGCCACAGCCGCGGACTATCTGCTTGCC
CATTTTATCAAGTAATACCAAGTGCTATATTATACATAGTATGTATGTAAGTGGTACGCGGCGAATGCGTGACAAAGTCGAGCGGCAAAAAATGA
AAATGCAAAGACATTGAATTTCCACCACCGTGCACATTATACAATTTAAATTACGTCAAGTGGCAGTGAGAAAATGAAATGATTCTTTTATTTCG
CGCTTAGGTCTTTTTGTTGTATAAGCAAGTGCATCGTGAAGGCGAGAGAGAGATGTACTATGTACACTGAAAGTATTTTTACTAAACATCATATA
TAAATATAGCTAATGATTATAACCTACTATTTATAAATCTCAATGGCCTTGTTATTGAATATAAATTTAATATTTCAAATTTTAATTCAAATTTC
CTGTACCGACGAGGCTTAGTTCTCAGTGTAGCAGAGGCAGAGGGTGATTTTCCTTACACTTTGGAACGGCCATAAAATGCAAATATGCGAAAACA
TTAAACACATTATGACAAAATCGAGCTGAAAATAAATTGTGATGCCTGTCAGTAAACTTGAGCTGCGGCACAATCGTATCTCATAGGTGCAGATA
GCTGCGAGTGAGAGGTAAAAGCGACTGAAGTAAGTATTTGTGGGTCGTGTTTATTGTGGCAGAACCCACTTGTTGCGAAATTAAATTTAAAACAC
AAACAATGGACTGGCCGACAACAAAAAAGGCTCGCACAAAAAGCTGTTCATTAACACGCTTCGCTTGCCGTTTTGAGTTAATTAATAAAACAGTT
AGCGTAGTTTTGCTTTGACGGATAAACGTATAAGTGGTGGGCAGGTTTTGGCCAATTTGAGTGATGTCAGTGGTGCAGGTCAATCAGAAAAAGGG

FIGURE SHEET 54

GTGGGTGGTCGCACCGAAGGCCTCCCTTCCAAAGGTGGGACATGATGATAGCCTTTTAACTACCCCTATCTCTCACAGTTTTAGGGCAAAGTTAT
CACATAAAGCTGTGCAGCAACTATTTAGAACCTCCAAAGTGTAATCATTGAGCCACCTATATAGAATATGTATCATCCTTTATCATGAAATTTAC
AAACTTCAAGTTGGAAAATCTGGAGTGATGGCAAATAAACTTAAAAACACATTTGCGTATTATAATGTGTTGATATGTGTATAATGTTACACCTT
TGTTTAACATAACTTGTTAACGATTATATTCCAGATTAGAGCTTAAGTGGTAATTTCTCGTTAATTAAATGGTTTTCTTATCAAATTGCCATTGT
ACGTTTGTGGGAAAGTATTCCGATTTAGCAGACTAATGATAGGGTAGAGTGAATCATCGCTGATATGACTAAATTCAGGTGTGTTGTCGGTGGGA
GGCAAACCTCTTTCTTTCAAAATATAAGCCTTGAGCTATTTTGGAATGAACCCGTATACTTTTTATCATCGAAACAGCACAAACGTGAGTTGAAT
GGCAAAATGTACTTTAATTTACTATTGTGCCAACTTTTAATTTATGTCAAAAGTGTAACAAATCAAAATGTCCAATATTAGCCATAATTATCAAT
TGCTTAAGTTACGAACTGATCGGATTAGATATTAATAGGTGTTTATAGAACCATATTCCTATGTCTACTATGTAAAATACCGCTGACCACTAAAT
AGCTTTACAGAAATTCAATACGTGCGCTCATCCGACTCCAACTCCAATTTCTCTTCCAGGTAAAAACTCACTGGAGCGTAGCGCCAACTCCCGCT
TCGAGAAGCCCATAGACTATGTGGAATACCTGCAGAATGGGGAGCACAGCACGCACAAGGTGTACCAATGTGTGGAATCTCTGCGCGTGGCGCTC
ACCAGCAATCCGATCTCGTGGATCAAGGAGTTTGGAGTGGCGGGCATCGGGACGATTGAGAAGCTGCTGGCCCGGTCAAAGAATAATGCCAGCTA
CGAGAAGATCGAGTTCGAGGCGATTCGGTGCCTGAAGGCGATCATGAACAACACATGGGGTCTGAACGTGGTGCTCAATCCGGATCAGCATAGTG
TGGTGCTGCTGCTGGCGCAATCCCTGGATCCCCGGAAGCCGCAGACGATGTGTGAAGCCCTCAAGCTGCTGGCCTCGTTCTGCATTGTCTATGAG
CGGAATGGCTACGAGAAGGTTCTCCGAGCCATAACCACTATTGCAGCCACATCCTTTAAAGCGAGCGAGCGCTTTCGACCCATAGTGGATGCCTT
GTTTGCATCGGATCAGCAGGATCCCAAACGGGACTTGGCATGCCACAGCCTGATTTTTATTAATACTCTCACCAATACCCCCACGGATTTGAACT
TCCGCCTGCACTTGCGATGTGAGATTATGCGCATGGGTCTATACGATCGCCTAGATGAGTTCACCAAAATCGTGGAGGCCAGCAATAATGAGAAC
CTGCAGCAGCACTTCAAGATCTTCAACGAGATCCGCGAGGATGACTTCGAGGAGTTTGTGCAGCGCTTCGATAATGTCACCTTCAACATGGACGA
CGCCACCGATTGCTTCGATGTGCTGAAGAACCTGGTGACTGACACCACTTCCGAGCCCTACTTCCTGTCCATCCTGCAGCATTTGCTGTACATCA
GGGATGACTTCTACTTCCGACCTGCCTATTATCAGCTGATTGAGGAGTGCATCTCACAAATCGTCTTCCACAAGGGTTACTGTGATCCGAATTTC
GAGAACCGGAACTTTAATATAGACACCTCGCTACTGCTGGACGACATTGTGGAGAAGGCCAAGGCCAAGGAGTCGAAGCGGTCGGAGGAGTACGA
GAAGAAGATCGAGCAGCTGGAGAGTGCCAAGCAAGAGGCGGAAGCGAAGGCGGCTCATCTGGAGGAGAAAGTCAAGTTGATGGAGGCTAATGGTG
TGGCGGCTCCGTCGCCCAATAAGCTACCCAAGGTAAACATACCCATGCCACCGCCACCACCAGGAGGAGGAGGAGCACCTCCCCCACCGCCGCCA
CCTATGCCGGGACGAGCAGGTGGTGGACCTCCGCCTCCACCACCACCTCCCATGCCGGGAAGGGCAGGTGGACCGCCACCACCTCCTCCACCGCC
CGGAATGGGAGGCCCACCGCCTCCACCCATGCCTGGCATGATGCGCCCAGGAGGGGGACCTCCACCACCGCCCATGATGATGGGGCCCATGGTTC
CCGTTCTGCCTCATGGCTTAAAACCGAAGAAGAAGTGGGACGTCAAGAATCCCATGAAGCGGGCCAACTGGAAAGCCATTGTCCCGGCCAAAATG
TCCGACAAGGCATTCTGGGTCAAGTGCCAGGAGGATAAGCTGGCCCAGGATGACTTCCTCGCAGAACTGGCCGTGAAATTCTCTTCTAAACCTGT
AAAGAAAGAACAGAAGGATGCGGTGGACAAGCCAACGACGCTGACAAAGAAAAATGTCGATCTTCGTGTGCTCGACTCGAAGACTGCTCAGAACT
TGGCTATTATGTTGGGAGGATCGCTGAAGCATCTGTCCTACGAACAGATCAAGATCTGCTTGCTGCGCTGCGACACCGACATCCTGTCCTCCAAT
ATCCTGCAGCAACTTATCCAGTACCTTCCGCCGCCAGAGCACCTCAAGCGTTTGCAGGAGATCAAGGCAAAGGGCGAACCGCTACCGCCGATTGA
ACAGTTTGCAGCCACAATAGGTAAGGCGAATGGAGTTTGTAGTGCAGAAGGCGCAGAATAACTTTACTTAATTTCAGGGGAAATTAAACGCCTTT
CGCCGCGACTTCACAACCTGAACTTCAAGCTGACCTACGCGGACATGGTGCAGGATATCAAACCCGACATTGTGGCAGGAACGGCAGCATGCGAA
GAGATCCGGAATAGCAAAAAGTTCTCAAAGATCTTGGAGCTGATTCTGCTGCTTGGAAATTACATGAACTCGGGCTCCAAAAACGAGGCCGCCTT
TGGCTTTGAGATCAGTTATTTAACCAAACTGTCCAATACGAAGGATGCGGATAATAAGCAGACATTGCTGCACTACCTGGCTGACCTGGTGGAAA
AGAAATTCCCAGATGCACTAAACTTCTACGACGATCTGTCGCATGTTAATAAAGCGTCGCGGGTCAACATGGATGCCATCCAAAAGGCCATGCGG
CAAATGAATTCGGCGGTTAAGAACCTGGAAACTGATCTCCAGAACAACAAGGTGCCGCAGTGTGATGATGACAAGTTTAGCGAGGTGATGGGCAA
GTTTGCCGAGGAGTGCAGACAACAAGTGGACGTGCTGGGTAAGATTATCTCATCTGATCGGAACGAATATTACATGAGCAAAATCGAATTCTCTA
ACATCTCGTTTTAATTTCAGGCAAAATGCAGCTGCAAATGGAGAAGCTGTACAAGGACCTCAGCGAGTACTATGCCTTCGATCCCAGCAAATACA
CAATGGAGGAGTTCTTTGCGGACATCAAGACTTTCAAGGATGCCTTCCAAGCGGCCCACAACGACAATGTCCGGGTACGCGAGGAGCTGGAGAAG
AAGCGTCGTCTGCAGGAGGCCCGAGAGCAGTCTGCTCGAGAGCAACAGGAGCGCCAACAGCGTAAGAAGGCAGTGGTTGACATGGATGCCCCGCA
GACGCAGGAAGGCGTGATGGACAGTCTGTTGGAGGCGCTGCAAACGGGCTCAGCCTTTGGCCAACGAAATCGACAGGCCCGGCGACAACGACCGG
CGGGAGCGGAGCGGAGGGCACAGCTCAGCCGGAGTCGATCGCGGACGCGTGTCACCAACGGACAACTAATGACCCGCGAAATGATCCTCAACGAG
GTTCTAGGCTCCGCGTAGAAGTAATGGAACGAGCAATTCCCCTCTGTACATATATAAATAGATATCTGTAGCGATATAAGGGCCTGGGCTCATTA
GCCGTGAGTCCGTGTGCGTCGCCTTGCTTGCATATCAACTCAATTGGCGTGTCCAAGAGATTTGACGAATTGGATGCCCAGCAGGAAGGACTGTA
TCAAGAGCCGCAAAGTACTAATTAACTGGAACTAGAGTCACAGGTGGATTTTCCGAAATTATTAATTGCTGTAACGGAGTCCTTGGTTTATAGGA
TTGAGTTTTCCGTTTGAATTGATTGGAGTATTTATTTAATTGATTGTTTAATAAATAACATTTTGTTTAGAATTTATAATATGCAAATAACACAT
ACAAGATCACTTTTATTTAATTAAAATGATTGGCAGGCCTTTTAATTTCAGCTGTACATTTTATTTTACTGCTATGACTGTCCCAATATTAAAGT
ACCAATTTTACAAGTCGAATATACTATAAAAAAACTTCTAGTTGAAACTAAATTCATGTCAAGAAATTAGCAATGCATATCGATGAAAACTCCAA
CTTCGCTACCTATACGAAAAAACTAAATATATAGATATTTTTGATACGCTTTTACTTCTGAAATTATGTCGTTGTAAGTCTAAATACTTAAAAAT
GAAACTGAAAGCAACTTTAAGATTTATCTGTATCTTGTGGTCTTTACATACTGTATTCCTATTTTACTGTGGCATGTTCCAATCATTTTGCTGTG
CACTTCGTTTTCGAGGCACTCAGTAGAGCAGAGGCGAGATTTATATCAAAGCAAAATTCCTTTTGTATTTAATTTGTTTTTAAGCGAAACTTTTT
TGAACTTGTTTACCTTAAAATCCTATTTTAATCCGCGCTATACATAACATTGTTAATAAATGTCTATTTTTCGACAATGACGGTATATTGAAAAT
AAAACTACCAAATCAACTGCTTCTCAACCAATTGATTGGCAATAATCCTGGAATATTCCACAAGAAGGCTTGGCTGCGAATCCGAAAGCAATTTG
GGCTTTCCACCCATGTGTGACTTGCCGCCTTTTGTTGTTCTTCTCCACTCTAATTTGTTTTATTAACAAAGATATTTTATCGCCAATGTCGCGGC
ACCCATAAAGGTGCTTGATTGCGACGGCGAAGGAGGCGGTTGCTCGGCTCGTACAACGCAAAATGCACTTGCTGCGGGATCGGCTGGGGGTTGCG
GGTGGGCGGAAGGGGTTTCTGGAGGGGTTTGGCCCGGCAAACGGCCGTAAAACTCTCAAAAACGTTAAACGAACCGACAAACAGCGAATGCCGCA
CGACAATGATACGTCTACCATCCATACATATCCATCCATCCACACTCAAATCCGTCTGGCGTCGACGCTCCACCAAGCCACAGATATAGGTTGTT
AGATCGGGACTGGAACTTGGACATATCTGTAATGGTCTGATTGCCCCTTGAGTTTTATTTCGGAGTCTGCTTTATGGGCTATGGCGCTTGCTTTG
CTTTCTTTATGGATTTATTAACATAATTGAGGGAATATGTATAAATACCATTGAATTCGTAGCAGGTTGTTAATGTCAATGGCGGGGACAGATTC
TAATTTACGATGGCCAGATAGAGATGCATTAGAGTGTTTTACAGATTGAAATAAATCTTTCATTGCCGGAAGGGCAATTCGAAATGGATTCTCTG
CTTTCGATTCAACTAATCGTCGGGGAACGTTTGTATATTATAATATTATGTATTATGTTTGTAATTGATCAACACTTTCTATTTGATGAAAAAAT
ATTACAATCTTCTATCAAATCTTGCGTTTGTACGACCAAAATTCATGATTCATCTCGAATTTGCCGCCCAGGGGGAGTTACCATATGTTTACATA
GATCACTTAGGGATTAGCCTTTTTGTGCGCCCCTAATGACTTCCAGGTAAC
(SEQ ID NO: 124)

Exon: 1001..1496
Exon: 3358..3674
Exon: 6330..8285
Exon: 8343..8873
Exon: 8951..10356
Start ATG: 3359

FIGURE SHEET 55

Transcript No. : CT4728
AACGCGCTGAGTAAATCGAACCGCTTGTGCTTAGAATTTGTTTTTCGCAATTAACGGCCGTGAAGAGCCAGCGATCTGCATGCCAAGTGTCCAA
TAACTAGGCAGAACAGTGTTTGCGTTGCACAAAAGCCCGCTAGCGGAGTGTGTTCCATGTGTCATTCCCGGCAAAGGAGCAACAAGTGGCCGAAA
GTGGAAAGCAAGAGCAACAACTAAATAAGTAAGGAGTACCACACTGCAAGAAAAAGTGTTCGGAGGGAACGGTGTGCACAGCTTGTCAGCTTGTT
TTTTGTACAGAGCGTCGCGCAATAAAACAAACAAAAAGACATAGTCCAAAAACAACAACCACAACAAAAGCCGTTTGATCGCGAGTTTGTGTGCG
TGTGCGAGTGTGGCTCTATTTGTGTGAGAGTGGCAAGCCATTATTTTTCTGGTCTTATGACGTAAACCACCGAAAAAAATCAAAAGTGAGCAGGC
GACACAGATATCAAAACGAAGAATGTCTCGTCACGAGAAAACGAAATCCACGGGCGGCGGGCTCCTGGACAGTCTGTTCGGAAGACCCTCGAAGT
CCAAGGGAGGAACCATCAGCAGTGGCACCCTGGCCCATGGCGGACGACCCGTGTCCGCGGACAACTATGTGGTGCCGGGCGTGGAGGACTTTGAG
CAGTACATCCAGCAGCTAAGCGTTGCGGAGCTGGATGCGAAGTTTCTGGAGATCATCGAGGACATGAACATTCCGAAGGACAAGAGGGAGCCCCT
GTTGGCCAAATCGAAGGAGGAGCGACAGAAGATGATTATGTGGCACTTGAAAGGTAAAAACTCACTGGAGCGTAGCGCCAACTCCCGCTTCGAGA
AGCCCATAGACTATGTGGAATACCTGCAGAATGGGGAGCACAGCACGCACAAGGTGTACCAATGTGTGGAATCTCTGCGCGTGGCGCTCACCAGC
AATCCGATCTCGTGGATCAAGGAGTTTGGAGTGGCGGGCATCGGGACGATTGAGAAGCTGCTGGCCCGGTCAAAGAATAATGCCAGCTACGAGAA
GATCGAGTTCGAGGCGATTCGGTGCCTGAAGGCGATCATGAACAACACATGGGGTCTGAACGTGGTGCTCAATCCGGATCAGCATAGTGTGGTGC
TGCTGCTGGCGCAATCCCTGGATCCCCGGAAGCCGCAGACGATGTGTGAAGCCCTCAAGCTGCTGGCCTCGTTCTGCATTGTCTATGAGCGGAAT
GGCTACGAGAAGGTTCTCCGAGCCATAACCACTATTGCAGCCACATCCTTTAAAGCGAGCGAGCGCTTTCGACCCATAGTGGATGCCTTGTTTGC
ATCGGATCAGCAGGATCCCAAACGGGACTTGGCATGCCACAGCCTGATTTTTATTAATACTCTCACCAATACCCCCACGGATTTGAACTTCCGCC
TGCACTTGCGATGTGAGATTATGCGCATGGGTCTATACGATCGCCTAGATGAGTTCACCAAAATCGTGGAGGCCAGCAATAATGAGAACCTGCAG
CAGCACTTCAAGATCTTCAACGAGATCCGCGAGGATGACTTCGAGGAGTTTGTGCAGCGCTTCGATAATGTCACCTTCAACATGGACGACGCCAC
CGATTGCTTCGATGTGCTGAAGAACCTGGTGACTGACACCACTTCCGAGCCCTACTTCCTGTCCATCCTGCAGCATTTGCTGTACATCAGGGATG
ACTTCTACTTCCGACCTGCCTATTATCAGCTGATTGAGGAGTGCATCTCACAAATCGTCTTCCACAAGGGTTACTGTGATCCGAATTTCGAGAAC
CGGAACTTTAATATAGACACCTCGCTACTGCTGGACGACATTGTGGAGAAGGCCAAGGCCAAGGAGTCGAAGCGGTCGGAGGAGTACGAGAAGAA
GATCGAGCAGCTGGAGAGTGCCAAGCAAGAGGCGGAAGCGAAGGCGGCTCATCTGGAGGAGAAAGTCAAGTTGATGGAGGCTAATGGTGTGGCGG
CTCCGTCGCCCAATAAGCTACCCAAGGTAAACATACCCATGCCACCGCCACCACCAGGAGGAGGAGCACCTCCCCCACCGCCGCCACCTATG
CCGGGACGAGCAGGTGGTGGACCTCCGCCTCCACCACCACCTCCCATGCCGGGAAGGGCAGGTGGACCGCCACCACCTCCTCCACCGCCCGGAAT
GGGAGGCCCACCGCCTCCACCCATGCCTGGCATGATGCGCCCAGGAGGGGGACCTCCACCACCGCCCATGATGATGGGGCCCATGGTTCCCGTTC
TGCCTCATGGCTTAAAACCGAAGAAGAAGTGGGACGTCAAGAATCCCATGAAGCGGGCCAACTGGAAAGCCATTGTCCCGGCCAAAATGTCCGAC
AAGGCATTCTGGGTCAAGTGCCAGGAGGATAAGCTGGCCCAGGATGACTTCCTCGCAGAACTGGCCGTGAAATTCTCTTCTAAACCTGTAAAGAA
AGAACAGAAGGATGCGGTGGACAAGCCAACGACGCTGACAAAGAAAAATGTCGATCTTCGTGTGCTCGACTCGAAGACTGCTCAGAACTTGGCTA
TTATGTTGGGAGGATCGCTGAAGCATCTGTCCTACGAACAGATCAAGATCTGCTTGCTGCGCTGCGACACCGACATCCTGTCCTCCAATATCCTG
CAGCAACTTATCCAGTACCTTCCGCCGCCAGAGCACCTCAAGCGTTTGCAGGAGATCAAGGCAAAGGGCGAACCGCTACCGCCGATTGAACAGTT
TGCAGCCACAATAGGGGAAATTAAACGCCTTTCGCCGCGACTTCACAACCTGAACTTCAAGCTGACCTACGCGGACATGGTGCAGGATATCAAAC
CCGACATTGTGGCAGGAACGGCAGCATGCGAAGAGATCCGGAATAGCAAAAAGTTCTCAAAGATCTTGGAGCTGATTCTGCTGCTTGGAAATTAC
ATGAACTCGGGCTCCAAAAACGAGGCCGCCTTTGGCTTTGAGATCAGTTATTTAACCAAACTGTCCAATACGAAGGATGCGGATAATAAGCAGAC
ATTGCTGCACTACCTGGCTGACCTGGTGGAAAAGAAATTCCCAGATGCACTAAACTTCTACGACGATCTGTCGCATGTTAATAAAGCGTCGCGGG
TCAACATGGATGCCATCCAAAAGGCCATGCGGCAAATGAATTCGGCGGTTAAGAACCTGGAAACTGATCTCCAGAACAACAAGGTGCCGCAGTGT
GATGATGACAAGTTTAGCGAGGTGATGGGCAAGTTTGCCGAGGAGTGCAGACAACAAGTGGACGTGCTGGGCAAAATGCAGCTGCAAATGGAGAA
GCTGTACAAGGACCTCAGCGAGTACTATGCCTTCGATCCCAGCAAATACACAATGGAGGAGTTCTTTGCGGACATCAAGACTTTCAAGGATGCCT
TCCAAGCGGCCCACAACGACAATGTCCGGGTACGCGAGGAGCTGGAGAAGAAGCGTCGTCTGCAGGAGGCCCGAGAGCAGTCTGCTCGAGAGCAA
CAGGAGCGCCAACAGCGTAAGAAGGCAGTGGTTGACATGGATGCCCCGCAGACGCAGGAAGGCGTGATGGACAGTCTGTTGGAGGCGCTGCAAAC
GGGCTCAGCCTTTGGCCAACGAAATCGACAGGCCCGGCGACAACGACCGGCGGGAGCGGAGCGGAGGGCACAGCTCAGCCGGAGTCGATCGCGGA
CGCGTGTCACCAACGGACAACTAATGACCCGCGAAATGATCCTCAACGAGGTTCTAGGCTCCGCGTAGAAGTAATGGAACGAGCAATTCCCCTCT
GTACATATATAAATAGATATCTGTAGCGATATAAGGGCCTGGGCTCATTAGCCGTGAGTCCGTGTGCGTCGCCTTGCTTGCATATCAACTCAATT
GGCGTGTCCAAGAGATTTGACGAATTGGATGCCCAGCAGGAAGGACTGTATCAAGAGCCGCAAAGTACTAATTAACTGGAACTAGAGTCACAGGT
GGATTTTCCGAAATTATTAATTGCTGTAACGGAGTCCTTGGTTTATAGGATTGAGTTTTCCGTTTGAATTGATTGGAGTATTTATTTAATTGATT
GTTTAATAAATAACATTTTGTTTAGAATTTATAATATGCAAATAACACATACAAGATCACTTTTATTTAATTAAAATGATTGGCAGGCCTTTTAA
TTTCAGCTGTACATTTTATTTTACTGCTATGACTGTCCCAATATTAAAGTACCAATTTTACAAGTCGAATATACTATAAAAAAACTTCTAGTTGA
AACTAAATTCATGTCAAGAAATTAGCAATGCATATCGATGAAAACTCCAACTTCGCTACCTATACGAAAAAACTAAATATATAGATATTTTTGAT
ACGCTTTTACTTCTGAAATTATGTCGTTGTAAGTCTAAATACTTAAAAATGAAACTGAAAGCAACTTTAAGATTTATCTGTATCTTGTGGTCTTT
ACATACTGTATTCCTATTTTACTGTGGCATGTTCCAATCATTTTGCTGTGCACTTCGTTTTCGAGGCACTCAGTAGAGCAGAGGCGAGATTTATA
TCAAAGCAAAATTCCTTTTGTATTTAATTTGTTTTTAAGCGAAACTTTTTTGAACTTGTTTACCTTAAAATCCTATTTTAATCCGCGCTATACAT
AACATTGTTAATAAATGTCTATTTTTCGACAATGACGGTATATTGAAAATA
(SEQ ID NO: 125)

Start ATG: 498

MSRHEKTKSTGGGLLDSLFGRPSKSKGGTISSGTLAHGGRPVSADNYVVPGVEDFEQYIQQLSVAELDAKFLEIIEDMNIPKDKREPLLAKSKEE
RQKMIMWHLKGKNSLERSANSRFEKPIDYVEYLQNGEHSTHKVYQCVESLRVALTSNPISWIKEFGVAGIGTIEKLLARSKNNASYEKIEFEAIR
CLKAIMNNTWGLNVVLNPDQHSVVLLLAQSLDPRKPQTMCEALKLLASFCIVYERNGYEKVLRAITTIAATSFKASERFRPIVDALFASDQQDPK
RDLACHSLIFINTLTNTPTDLNFRLHLRCEIMRMGLYDRLDEFTKIVEASNNENLQQHFKIFNEIREDDFEEFVQRFDNVTFNMDDATDCFDVLK
NLVTDTTSEPYFLSILQHLLYIRDDFYFRPAYYQLIEECISQIVFHKGYCDPNFENRNFNIDTSLLLDDIVEKAKAKESKRSEEYEKKIEQLESA
KQEAEAKAAHLEEKVKLMEANGVAAPSPNKLPKVNIPMPPPPPGGGAPPPPPPPMPGRAGGGPPPPPPPPMPGRAGGPPPPPPPPGMGGPPPPP
MPGMMRPGGGPPPPPMMMGPMVPVLPHGLKPKKKWDVKNPMKRANWKAIVPAKMSDKAFWVKCQEDKLAQDDFLAELAVKFSSKPVKKEQKDAVD
KPTTLTKKNVDLRVLDSKTAQNLAIMLGGSLKHLSYEQIKICLLRCDTDILSSNILQQLIQYLPPPEHLKRLQEIKAKGEPLPPIEQFAATIGEI
KRLSPRLHNLNFKLTYADMVQDIKPDIVAGTAACEEIRNSKKFSKILELILLLGNYMNSGSKNEAAFGFEISYLTKLSNTKDADNKQTLLHYLAD
LVEKKFPDALNFYDDLSHVNKASRVNMDAIQKAMRQMNSAVKNLETDLQNNKVPQCDDDKFSEVMGKFAEECRQQVDVLGKMQLQMEKLYKDLSE
YYAFDPSKYTMEEFFADIKTFKDAFQAAHNDNVRVREELEKKRRLQEAREQSAREQQERQQRKKAVVDMDAPQTQEGVMDSLLEALQTGSAFGQR
NRQARRQRPAGAERRAQLSRSRSRTRVTNGQLMTREMILNEVLGSA*
(SEQ ID NO: 126)

Name: DIAPHANOUS/FORMIN HOMOLOGY
Classification: actin_binding

FIGURE SHEET 56

Gene Symbol: dia
FlyBase ID: FBgn0011202

Celera Sequence No. : 142000013384695
CTCGCGCAACAACATACCATCGGTCATGTACTTGAGCAGCGTCTTGGCCGTGGAGCAGTCCTCGAAACGGATGGAGTAGCCGACCTCTTCGCCCA
GTTTTACGTCCATCTCCTCCGAAACGCGCTGGGCCACGGACATGGCGGCAACTCGACGTGGCTGTGTGCAGGAGACTCCCTTGCGCCCCTTGGAT
ACTGCGAAGTCCACGCACCACTGCGGGATCTGGGTCGTCTTGCCGGAGCCAGTCTCGCCCACCAGCACAATACACTGGTGCAGGCTGAGCAGCCG
CATAAAGTCCGCCTGGTACTCGAACACGGGCAGCGCAATGCGCTTCTTGTAGAGATTCTGGTACCGTTGTGAGTACGGCGTGTTGGTCAGCGGGT
TCATCGTGGGCGGTTGCTTGTTGGGCACGAATCCGCCCAGGATTTGAGCCACTGTGCCGGCAGCGGCTGCCGCCGACGAGGAGGACGCCTCCGGG
TCCCTGGTGAGAAAGGAGCGTTACATTACTGCCGTATGTTGGCCTCGGGTCACTTACTTCTTCGCCTTGCTGCCGTAGGTCTCCCCCACTTCGAT
TCGACGCTTGGACATGCTAATTTATGGTGATTACTGCACTTAATTCTCAAAACGAAGCGTTTAGCACAAAAAAAAACACGCGCTCAGTGAGACCT
TTAGCATATACCGACCATGCTGATCGCAACTTTTAAAATACCAAAGTTTACTGTCTGTGTATACTATATAAGCCCATGGTTAGCGAAGATCACAA
CCAACAGCACGGCAGCAATTTGGCATTTAAAAAAAAACAGCAGTTCAAGCTTAAGTCTTTTGACGAGAATCTATCTATAGAATTCGGTTTTACTC
ACCAGTTTGAAGAATAGTTGTGAGCTCACAGTCTTAAAATTGACATTTGACAGCAATTTGATTGGAAACTGATTTTGATTTTTACAGTAACAAAC
TGTTACATGGATTCGGTATTTTCGGCTTGGGTTGGCGCTTTAGCGTCGGCCACACTATCACATTGTATCGATTCGGAGGGAGTTGAATTTTTGCA
CGTATTTGAAAGCGCAAAGATGCGAAACAAAGAGCAGGATATCGAATGAAAGAGCTCCTGCGAGACCAGGACTAGTTGCCTAACCACCATGGAAA
TACCCATTCAGGTAGCGGTGCGCATCTTCCCGCATAGAGAGCTCAAGGACTTGTTGAGGAGCTTCGGCCCCACAGAGCCCAAAAAGGATGCGCAG
GCGGTGGATGAGGGGGCGGACTCCAAGGACTCCGAGGCTCAAGTTCCGGCGGCTGAGAAGGACAATCCGTCAATTTCAGAGACGGACCCAAACGG
GAATGCTGAGCAGGACAGTGCGGCCGATTCGAAGACAATTCCAGATGCCAATGGCAACGACAGTGGTCAGAAGGATTACCCAGACTCCGCATATT
GCGTTCAGGCTATTCCCATCAGCGCTTCGGCCCTGGGATTGCCCAGTGCCCTGCCAGGCGGAGATCCCATGGACAGCATTGCAGCTGGACTGATA
CAAGTCGGTCCCCACACGGTTCCGGTCACCCACGCCCTGCCCAGCAGCAGCTCCCAGGAGCAAGTGTACCACCAGACGGTCTTTCCGCTCATCAC
CCTGTTCCTGGAAGGTTTCGACGCATCTGTAGTCACCTATGGCCAGAGGGGCCAGGGCAAAAGCTACACACTCTACGGAAACGTCCAGGACCCTA
CTCTGACGGATTCCACCGAAGGAGTCGTCCAACTTTGTGTCCGTGACATTTTCTCACACATATCGTTGCACCCAGGTGAGTTTACTAAAAGGATC
TTATAAGCATAGTTATCCATTTCCATTTTCACTTTAAGAACGCACCTATGCCATCAACGTGGGATTCGTGGAAATTTGCGGAGGTGATGTCTGCG
ACTTGTTGGGCATGGGAAACATACACTGCACCAACGTAGATGCCGTCTTCCACTGGTTGCAGGTGGGTCTGTCGGCCCGCCAATCGTTGCCGGCG
CACACCCTGTTCACGCTTACCCTGGAGCAGCAGTGGGTGTCCAAGGAGGGGCTGTTGCAGCACCGCTTGTCCACGGCCAGTTTCTCGGATCTCTG
CGGCACAGAGAGATGTGGAGACCAGCCACCGGGACGTCCTCTCGATGCTGGCCTGTGTATGCTGGAGCAGGTGATCAGTACTCTCACAGATCCAG
GCCTCATGTACGGGGTTAATGGCAACATTCCGTACGGTCAGACCACGCTCACCACTCTCCTGAAGGACTCGTTCGGCGGACGGGCTCAGACGCTC
GTGATCCTGTGCGTGTCACCGCTGGAAGAGCACTTGCCCGAAACTCTTGGCAACCTGCAGTTCGCCTTTAAGGTGCAGTGCGTACGTAATTTTGT
AATTATGAACACCTACTCCGACGACAACACGATGATCGTTCAGCCGGCTGAGCCTGTTCCCGAATCCAATTCCTCTGCTGGACCCTTGTCGCAGG
CGGGACCAGGGGACAACTTTGGCCTACAATTCGCAGCAAGCCAATGGTCCAAACTAGTTACCAACGCCGAGGGGCTATTTTCCAAGTAAGTGTAC
ACATTATTTCCGATGTGGGCCTTTTGACGACAAAAGAAATTTATAGGCTGATAGACTCCAAGCTAATTACTGAAGTGGAGAAGGAGCAGATCGAG
GAGTGGCTCTTCCTCAAGCAGGAGTGCGAGGAGTGTCTCAGCTCAACAGAGGCTATGCGTCAGCAAAAACAGTTGGTTCCCATTCTGGAGGCCGA
GGAGCCCGAGGACGTGAATTCTGAAGCAGCCAATTCGGAGTCGCCAAACTCCGACAACGAAAACGACACAGACAATGAGTCGCATCGGCCCGATC
TGGACGACAAGATAGAAAGTCTAATGGAAGAGTTTCGCGACAAAACAGACGCTCTTATACTTGAAAAACACGCTGAATATCTATCCAAGCATCCG
AAGGCGGTTATGCAAAGCCAAGACCGCGAGATTGAGGCACAGCCGCCAGAAGAAAATGGTGATGATCGAAAAGTCAGCATTGGCAGTAAGTCTTT
GCCTTGAATAACATTTTTTTATACAGTAACATGTTGATTCCTTGCTTTAATAGGTCGCAGGAGAAGTGTTCAGCCAGGTGCTAGCTTAAGTACTG
CTGAGCTTGCCATGCTTAATCGGGTAGCTTCCCAGCAGCCGCCTCCGCCCATCGATCCTGAGTCGGTCGTCGATCCTCTGGAAAGTTCTTCGGGC
GAAGGAATCCGTCAGGCGGCTCTCGCTGCCGCCGCCGCCACTGCTCCTATTGAACAGCTGCAGAAAAAATTGCGCAAACTGGTCGCTGAGATCGA
GGGCAAGCAACGACAGTTACGGGAAATCGAAGAGACAATCCAGGTAAAACAAAATATAATCGCCGAATTGGTCAAGAACAGCGATACACGCAGCC
ATGCAAAGCAAAGATTTCACAAGAAACGTGCCAAACTTGAGGCCGAGTGCGACAAGGCCAAGAAGCAGTTAGGTAAGGCGCTAGTTCAAGGCCGG
GATCAGTCGGAGATTGAGCGATGGACCACGATAATCGGACATCTCGAGCGTCGACTAGAAGACCTCAGCTCAATGAAGCATATTGCGGGTGAGAG
CGGACAGAAGGTGAAGAAGCTACAGCAATCGGTGGGCGAGTCGCGAAAACAGGCCGATGATTTACAGAAAAAGCTTCGAAAGGAGTGCAAGCTGC
GCTGCCAGATGGAGGCGGAGCTGGCCAAACTACGAGAATCCAGGGAGACTGGCAAAGAGCTAGTGAAGGCGCAAGGTTCTCCCGAGCAACAAGGC
CGCCAGTTAAAGGCAGTACAGGCTAGGATTACGCACCTTAATCACATTTTACGCGAGAAGTCGGATAACCTGGAGGAGCAGCCGGGACCAGAACA
GCAGGAGACCTTGCGTCATGAGATCCGCAACTTGCGCGGAACTCGTGACTTGTTGTTGGAAGAACGCTGTCATTTGGACCGCAAACTTAAGCGGG
ACAAGGTGCTGACGCAAAAGGAGGAGCGCAAGCTGCTCGAGTGCGATGAGGCCATCGAGGCCATAGATGCGGCCATAGAATTCAAGAACGAGATG
ATCACGGGCCACCGCTCCATCGACACGAGCGACCGAATTCAGCGGGAGAAGGGAGAACAGATGCTGATGGCACGCCTAAATCGTCTCTCAACGGA
GGAGATGCGAACACTTCTGTACAAATACTTCACGAAGGTTATCGATTTGCGCGACTCTTCACGAAAGCTGGAGCTGCAGCTGGTGCAGTTGGAGC
GTGAGCGGGATGCCTGGGAGTGGAAGGAGCGTGTTCTGTCCAATGCCGTGCGCCAGGCTAGACTGGAAGGCGAACGGAATGCGGTGCTGCTGCAG
CGCCAGCACGAAATGAAACTCACTTTGATGCTGCGTCACATGGCGGAGGAAACGTCGGCCAGTTCGGCCAGCTACGGAGAACGAGCTTTGGCCCC
TGCCTGTGTCGCCCCGCCGGTGCAGGCCAGTAGTGATTTCGACTACGATCATTTCTACAAAGGTGGCGGCAATCCAAGCAAGGCACTGATCAAAG
CGCCAAAGCCGATGCCCACCGGCTCGGCGCTAGACAAATACAAGGACAAAGAGCAACGCAGCGGACGCAACATCTTTGCCAAGTTCCATGTGCTC
ACCAGATATGCGTCAGCTGCCGCAGCCGGTTCCTCAGGGTCCACGGCCGAGGAATCCACGGCCCTGATTGAGTCAACCACCACGGCCACGGCAAC
CACTACGTCGACAACCACCACTGGAGCCGTAGGAAAAGTGAAGGACAAGGCCCTGGTCAGCTTCAGGCCGGAGCAGCTGAAGCGTCTGATGCCAG
CTCCGACGGCCACGAAAGTGACGCGTCAGAAGAACAAGATAATTATCCAGGACGCAAGTCGTCGAAACTAAATACGAATTTAACCATTTCCAGGA
CGATATTATAAGGTTAAGCCAAATAGCCATATACAATTAATAGCCATGAGCTGAAATCCAGCCACTTTAATAATTAAGGCGATAATATAAAAAAA
TGCTTAAAAATGTATAACAGATTACTCCCATATACATGCATACATTTTAATCAATAGTCCGACATATATACCAGCTTGAATTTATTAGTTTACTG
CTTGTCGTTTAACTTATTAAAGTGGCTGGAGTTCGATATCTTTTTAAGTGTGAAGCAATAGCTCAGATCCTGGTAACAAGAACTGAACAAGTTTC
GTCCACAGTCATGACACAAATAGACTACAACACATGGTTCTCATTCCGGCTCTTTAGCTGGGGAGCATTTATTTTAGAAACCCCCACACGTACAT
ACACCTAGCATATGAAAGTAACTATCCTCATGAGATTCAACCGTAAAGACTTGACCTGCTACTTAAGATACTCGCAAGACAAACCGTACACAAAA
CTCGCTCAAAGTGTTGACCTAAGTCTCCGCATTGTTTAACTTGTACATAACAATAATTATTAGGTAACCACTTAATTTTAATTGATTTTGTTAGT
TTTAGCTTAGTTGTAAACACTATTGTGTCTTCCCTCGAATTTTAATTGACCTTCGATACCAATTACAACATACGTACTCCATACCCAAGTGTTAA
CCTTTAATATTCTATCAAAAGCATTTACTCTGTACAACTTATAAATGCTTCAAATCGCAGTATTTGCGCTAATCCAATACTCATTTTGCATTAAC
TTAAAATTAAAATTCAATACTGTTTGGTTGTGTACAACGTATTTTTTATTGTCCATTGATATAGATGCAGTTTGCACTGTACTCCGAGTAACTTA
AATTGATATTAATGTATGTATGTTCCCTCAATATCAGCGTGTGAAAAATTATAAACACATTTGTAAGCATACATATTCCGCCAAATCGCTCGGCA
TGGCTTTGTGTGGATATTGTTGGTTAAGCAAATAAATATATACAAACTAAACTAATCAATCAGTGTTTAATCAGTGTTTTATATTCAAAATAAAA
TAGTTATCGTCTTATAAAGATAATTAAGTTCTACATTTGCAGCTGAAATCCAAGCAAACACAGTCCACAAGGCAACAGGTGAGAAATGTCCCAGA
AATTTCCCAAACAATCGCCCCTTCGGACACACACACACACAGAAAGCGCAAAGAGAGAGGATGAGAGGGAGAGAGAGAGAGCGCCGGTTTAAGCG
TTGTATCTAAATCCGATGGCGAGTATCTGAGCATCCGATTCAGTCTTGTTTGGACCGTCGAGCGATCGAGAACCGGATTTCAGCGCTAGTCGGCG

FIGURE SHEET 57

AATCGCGAGAGCGTGCGAGTATTTGTGTGTGCGTGTGAGCGTTTGTTTTGGGACACCGATACGGATACGGGTACGGATAGACGGATATACGGCAG
CGGTACGCGATTAGCAATCCGCCAACCGGTTGCAGCGGTGCTAGTGCACCACCCTACAAAAAAGTGAATAATAGTATGCAAAGTATCTGAAAGAT
AGTCAAGAGCAGAGCAAAGTATCTGTGTTTGTGTGTGCCGTGCTTTTGTGCGGAGTCGCCACCCCCGTGGATTAGTGGCACCCTGCTGCAAATAG
CCCACCACTCTCACAAGTGTGTGTGTGTGAGTGTTAACAATTAATCGCATTTAAAAAACAATTTGGCCAGCCGCAGTAACAATAACGGTAAGAAA
AGTCGGCGGTACCGTTGGGAAATTTTCACCGTTGTCTGGCAACTTCTTTGTGCCCGTCGTGTATGTATAGGTTGGGTGCAGAAGTGTGCGTGAGT
CCTGCCCACGCCCACCGAGTAGCGCTAGTCTGCGAAATCAACTGCAGGATGCTGTAGGTTGATATTTTATCGGTTAGATGATAATAGTCTTTGGT
CTTCCTTATGATTTTTCGCCAGACGTTAAGTTTTTTCAATTTGGGAATGCAAAAACGGTTACTTTATGCACCGTATCACATCACACACACTTGCA
AAAGGGTGTGAAAA
(SEQ ID NO: 127)

Exon: 1001..1785
Exon: 1844..2555
Exon: 2612..3030
Exon: 3094..5949
Start ATG: 1134

Transcript No. : CT4888
CACACTATCACATTGTATCGATTCGGAGGGAGTTGAATTTTTGCACGTATTTGAAAGCGCAAAGATGCGAAACAAAGAGCAGGATATCGAATGAA
AGAGCTCCTGCGAGACCAGGACTAGTTGCCTAACCACCATGGAAATACCCATTCAGGTAGCGGTGCGCATCTTCCCGCATAGAGAGCTCAAGGAC
TTGTTGAGGAGCTTCGGCCCCACAGAGCCCAAAAAGGATGCGCAGGCGGTGGATGAGGGGGCGGACTCCAAGGACTCCGAGGCTCAAGTTCCGGC
GGCTGAGAAGGACAATCCGTCAATTTCAGAGACGGACCCAAACGGGAATGCTGAGCAGGACAGTGCGGCCGATTCGAAGACAATTCCAGATGCCA
ATGGCAACGACAGTGGTCAGAAGGATTACCCAGACTCCGCATATTGCGTTCAGGCTATTCCCATCAGCGCTTCGGCCCTGGGATTGCCCAGTGCC
CTGCCAGGCGGAGATCCCATGGACAGCATTGCAGCTGGACTGATACAAGTCGGTCCCCACACGGTTCCGGTCACCCACGCCCTGCCCAGCAGCAG
CTCCCAGGAGCAAGTGTACCACCAGACGGTCTTTCCGCTCATCACCCTGTTCCTGGAAGGTTTCGACGCATCTGTAGTCACCTATGGCCAGAGGG
GCCAGGGCAAAAGCTACACACTCTACGGAAACGTCCAGGACCCTACTCTGACGGATTCCACCGAAGGAGTCGTCCAACTTTGTGTCCGTGACATT
TTCTCACACATATCGTTGCACCCAGAACGCACCTATGCCATCAACGTGGGATTCGTGGAAATTTGCGGAGGTGATGTCTGCGACTTGTTGGGCAT
GGGAAACATACACTGCACCAACGTAGATGCCGTCTTCCACTGGTTGCAGGTGGGTCTGTCGGCCCGCCAATCGTTGCCGGCGCACACCCTGTTCA
CGCTTACCCTGGAGCAGCAGTGGGTGTCCAAGGAGGGGCTGTTGCAGCACCGCTTGTCCACGGCCAGTTTCTCGGATCTCTGCGGCACAGAGAGA
TGTGGAGACCAGCCACCGGGACGTCCTCTCGATGCTGGCCTGTGTATGCTGGAGCAGGTGATCAGTACTCTCACAGATCCAGGCCTCATGTACGG
GGTTAATGGCAACATTCCGTACGGTCAGACCACGCTCACCACTCTCCTGAAGGACTCGTTCGGCGGACGGGCTCAGACGCTCGTGATCCTGTGCG
TGTCACCGCTGGAAGAGCACTTGCCCGAAACTCTTGGCAACCTGCAGTTCGCCTTTAAGGTGCAGTGCGTACGTAATTTTGTAATTATGAACACC
TACTCCGACGACAACACGATGATCGTTCAGCCGGCTGAGCCTGTTCCCGAATCCAATTCCTCTGCTGGACCCTTGTCGCAGGCGGGACCAGGGGA
CAACTTTGGCCTACAATTCGCAGCAAGCCAATGGTCCAAACTAGTTACCAACGCCGAGGGGCTATTTTCCAAGCTGATAGACTCCAAGCTAATTA
CTGAAGTGGAGAAGGAGCAGATCGAGGAGTGGCTCTTCCTCAAGCAGGAGTGCGAGGAGTGTCTCAGCTCAACAGAGGCTATGCGTCAGCAAAAA
CAGTTGGTTCCCATTCTGGAGGCCGAGGAGCCCGAGGACGTGAATTCTGAAGCAGCCAATTCGGAGTCGCCAAACTCCGACAACGAAAACGACAC
AGACAATGAGTCGCATCGGCCCGATCTGGACGACAAGATAGAAAGTCTAATGGAAGAGTTTCGCGACAAAACAGACGCTCTTATACTTGAAAAAC
ACGCTGAATATCTATCCAAGCATCCGAAGGCGGTTATGCAAAGCCAAGACCGCGAGATTGAGGCACAGCCGCCAGAAGAAAATGGTGATGATCGA
AAAGTCAGCATTGGCAGTCGCAGGAGAAGTGTTCAGCCAGGTGCTAGCTTAAGTACTGCTGAGCTTGCCATGCTTAATCGGGTAGCTTCCCAGCA
GCCGCCTCCGCCCATCGATCCTGAGTCGGTCGTCGATCCTCTGGAAAGTTCTTCGGGCGAAGGAATCCGTCAGGCGGCTCTCGCTGCCGCCGCCG
CCACTGCTCCTATTGAACAGCTGCAGAAAAAATTGCGCAAACTGGTCGCTGAGATCGAGGGCAAGCAACGACAGTTACGGGAAATCGAAGAGACA
ATCCAGGTAAAACAAAATATAATCGCCGAATTGGTCAAGAACAGCGATACACGCAGCCATGCAAAGCAAAGATTTCACAAGAAACGTGCCAAACT
TGAGGCCGAGTGCGACAAGGCCAAGAAGCAGTTAGGTAAGGCGCTAGTTCAAGGCCGGGATCAGTCGGAGATTGAGCGATGGACCACGATAATCG
GACATCTCGAGCGTCGACTAGAAGACCTCAGCTCAATGAAGCATATTGCGGGTGAGAGCGGACAGAAGGTGAAGAAGCTACAGCAATCGGTGGGC
GAGTCGCGAAAACAGGCCGATGATTTACAGAAAAAGCTTCGAAAGGAGTGCAAGCTGCGCTGCCAGATGGAGGCGGAGCTGGCCAAACTACGAGA
ATCCAGGGAGACTGGCAAAGAGCTAGTGAAGGCGCAAGGTTCTCCCGAGCAACAAGGCCGCCAGTTAAAGGCAGTACAGGCTAGGATTACGCACC
TTAATCACATTTTACGCGAGAAGTCGGATAACCTGGAGGAGCAGCCGGGACCAGAACAGCAGGAGACCTTGCGTCATGAGATCCGCAACTTGCGC
GGAACTCGTGACTTGTTGTTGGAAGAACGCTGTCATTTGGACCGCAAACTTAAGCGGGACAAGGTGCTGACGCAAAAGGAGGAGCGCAAGCTGCT
CGAGTGCGATGAGGCCATCGAGGCCATAGATGCGGCCATAGAATTCAAGAACGAGATGATCACGGGCCACCGCTCCATCGACACGAGCGACCGAA
TTCAGCGGGAGAAGGGAGAACAGATGCTGATGGCACGCCTAAATCGTCTCTCAACGGAGGAGATGCGAACACTTCTGTACAAATACTTCACGAAG
GTTATCGATTTGCGCGACTCTTCACGAAAGCTGGAGCTGCAGCTGGTGCAGTTGGAGCGTGAGCGGGATGCCTGGGAGTGGAAGGAGCGTGTTCT
GTCCAATGCCGTGCGCCAGGCTAGACTGGAAGGCGAACGGAATGCGGTGCTGCTGCAGCGCCAGCACGAAATGAAACTCACTTTGATGCTGCGTC
ACATGGCGGAGGAAACGTCGGCCAGTTCGGCCAGCTACGGAGAACGAGCTTTGGCCCCTGCCTGTGTCGCCCCGCCGGTGCAGGCCAGTAGTGAT
TTCGACTACGATCATTTCTACAAAGGTGGCGGCAATCCAAGCAAGGCACTGATCAAAGCGCCAAAGCCGATGCCCACCGGCTCGGCGCTAGACAA
ATACAAGGACAAAGAGCAACGCAGCGGACGCAACATCTTTGCCAAGTTCCATGTGCTCACCAGATATGCGTCAGCTGCCGCAGCCGGTTCCTCAG
GGTCCACGGCCGAGGAATCCACGGCCCTGATTGAGTCAACCACCACGGCCACGGCAACCACTACGTCGACAACCACCACTGGAGCCGTAGGAAAA
GTGAAGGACAAGGCCCTGGTCAGCTTCAGGCCGGAGCAGCTGAAGCGTCTGATGCCAGCTCCGACGGCCACGAAAGTGACGCGTCAGAAGAACAA
GATAATTATCCAGGACGCAAGTCGTCGAAACTAAATACGAATTTAACCATTTCCAGGACGATATTATAAGGTTAAGCCAAATAGCCATATACAAT
TAATAGCCATGAGCTGAAATCCAGCCACTTTAATAATTAAGGCGATAATATAAAAAAATGCTTAAAAATGTATAACAGATTACTCCCATATACAT
GCATACATTTTAATCAATAGTCCGACATATATACCAGCTTGAATTTATTAGTTTACTGCTTGTCGTTTAACTTATTAAAGTGGCTGGAGTTCGAT
ATCTTTTTAAGTGTGAAGCAATAGCTCAGATCCTGGTAACAAGAACTGAACAAGTTTCGTCCACAGTCATGACACAAATAGACTACAACACATGG
TTCTCATTCCGGCTCTTTAGCTGGGGAGCATTTATTTTAGAAACCCCCACACGTACATACACCTAGCATATGAAAGTAACTATCCTCATGAGATT
CAACCGTAAAGACTTGACCTGCTACTTAAGATACTCGCAAGACAAACCGTACACAAAACTCGCTCAAAGTGTTGACCTAAGTCTCCGCATTGTTT
AACTTGTACATAACAATAATTATTAGGTAACCACTTAATTTTAATTGATTTTGTTAGTTTTAGCTTAGTTGTAAACACTATTGTGTCTTCCCTCG
AATTTTAATTGACCTTCGATACCAATTACAACATACGTACTCCATACCCAAGTGTTAACCTTTAATATTCTATCAAAAGCATTTACTCTGTACAA
CTTATAAATGCTTCAAATCGCAGTATTTGCGCTAATCCAATACTCATTTTGCATTAACTTAAAATTAAAATTCAATACTGTTTGGTTGTGTACAA
CGTATTTTTTATTGTCCATTGATATAGATGCAGTTTGCACTGTACTCCGAGTAACTTAAATTGATATTAATGTATGTATGTTCCCTCAATATCAG
CGTGTGAAAAATTATAAACACATTTGTAAGCATACATATTCCGCCAAATCGCTCGGCATGGCTTTGTGTGGATATTGTTGGTTAAGCAAATAAAT
ATATACAAACTAAACTAATCAA
(SEQ ID NO: 128)

Start ATG: 134

FIGURE SHEET 58

MEIPIQVAVRIFPHRELKDLLRSFGPTEPKKDAQAVDEGADSKDSEAQVPAAEKDNPSISETDPNGNAEQDSAADSKTIPDANGNDSGQKDYPDS
AYCVQAIPISASALGLPSALPGGDPMDSIAAGLIQVGPHTVPVTHALPSSSSQEQVYHQTVFPLITLFLEGFDASVVTYGQRGQGKSYTLYGNVQ
DPTLTDSTEGVVQLCVRDIFSHISLHPERTYAINVGFVEICGGDVCDLLGMGNIHCTNVDAVFHWLQVGLSARQSLPAHTLFTLTLEQQWVSKEG
LLQHRLSTASFSDLCGTERCGDQPPGRPLDAGLCMLEQVISTLTDPGLMYGVNGNIPYGQTTLTTLLKDSFGGRAQTLVILCVSPLEEHLPETLG
NLQFAFKVQCVRNFVIMNTYSDDNTMIVQPAEPVPESNSSAGPLSQAGPGDNFGLQFAASQWSKLVTNAEGLFSKLIDSKLITEVEKEQIEEWLF
LKQECEECLSSTEAMRQQKQLVPILEAEEPEDVNSEAANSESPNSDNENDTDNESHRPDLDDKIESLMEEFRDKTDALILEKHAEYLSKHPKAVM
QSQDREIEAQPPEENGDDRKVSIGSRRRSVQPGASLSTAELAMLNRVASQQPPPPIDPESVVDPLESSSGEGIRQAALAAAAATAPIEQLQKKLR
KLVAEIEGKQRQLREIEETIQVKQNIIAELVKNSDTRSHAKQRFHKKRAKLEAECDKAKKQLGKALVQGRDQSEIERWTTIIGHLERRLEDLSSM
KHIAGESGQKVKKLQQSVGESRKQADDLQKKLRKECKLRCQMEAELAKLRESRETGKELVKAQGSPEQQGRQLKAVQARITHLNHILREKSDNLE
EQPGPEQQETLRHEIRNLRGTRDLLLEERCHLDRKLKRDKVLTQKEERKLLECDEAIEAIDAAIEFKNEMITGHRSIDTSDRIQREKGEQMLMAR
LNRLSTEEMRTLLYKYFTKVIDLRDSSRKLELQLVQLERERDAWEWKERVLSNAVRQARLEGERNAVLLQRQHEMKLTLMLRHMAEETSASSASY
GERALAPACVAPPVQASSDFDYDHFYKGGGNPSKALIKAPKPMPTGSALDKYKDKEQRSGRNIFAKFHVLTRYASAAAAGSSGSTAEESTALIES
TTTATATTTSTTTTGAVGKVKDKALVSFRPEQLKRLMPAPTATKVTRQKNKIIIQDASRRN*
(SEQ ID NO: 129)

Name: KINESIN-LIKE PROTEIN
Classification: motor_protein
Gene Symbol: cos
FlyBase ID: FBgn0000352

Celera Sequence No. : 142000013384776
ACGTTTTCAAGGGCAGGCAGCTTTGTAATTTAATTCAATTTCTATTTAATTGAACCAAAGGCGTCTTTAATGTGCAACTTTTTGATTTATGAGTC
CGCAACAGCAAGCGGCTGTCAAGCAACTTGTTCATTTCACTCCACTTCTTTCTTAGTTTCCCTCTCTTGCCTTCGGGAAAATTTAAAATCTTACT
ACGAAATTTCCATGCAAACGAAACATTTTCCGCCAGCCATGCCGCATTTTGCGTTTCCTCTTCTTTTTCTTCCTGTTTTTTTGGCACAAATTTAA
TTTGATTTGATTTTGGCCGCTGGACATGGCAAGCCCCAGGCAATTTGTCAAAAAGTTATATAGCTACTGTGTATTTTTATGTGCCGGCATATTTA
ATGACATTTTCCTCATTGCGACTTTTTTTTTTTGAATTTTCAAAAAATACAAAATACAATATCTTCTAAAATCCATGAGCAATGCCCAATTCTTG
AAGTTTTTGATGGCCATGCAAGTGATGTGCCATTTGTTGAGTAAGTATATCTGTGGGCAAAGATTTCTAGCTTAGGCGTGTGCAATGTATGAGGA
ATTAATTTGTGTAAAATTGGCAAACAATGGAGGAGATGGGCCGAGTAAAGGTAAGCAATTTGTTTGAATTCGCTTGGTAAATTAATTGCACAGGT
TTGGAAAATTAATGGACACCTGCAGATCCACCAGTGGCATTGTATGTTGGCCATTGTGTGGTTATTGAATTTAAGTTCCATAAGCATTCAAATGA
AGATGCTGTAATTTTGCAGGAATATATAAATAAGTATATGGCCGTTATTAAATGCTGACCCACATTTTGTGTACTGGCAAAGCCAGTTTTTTTT
TGTTGGTTGTTAAAAACCATTTTGATTCTTGGCAAATCTGGTTCAATTAACTGCAGCCCAAAATATCATTTAATATCGCGATATGACCACAAAAA
TCATATATAAGAAGTGGCGAGCCTGGTCACCACAGCAAAGCGACTGAAAGCGAAGTCTGATAAAGAACAATCCTTACAAAATACAAAAAAATATA
TATATTTAAAAAATACAATTGAGCAACCAAACATGGCCAACATTCTAAGTTTTACCATCTTTATGGCTGCCATTGCTATTGGACTGGCTTTAGCC
ACAACAACGACAGCAAGTACAAGGACACCCATGCCCACTTCCACTGAAAAATCCATGGAAAAGGACGATCCCATGGAGTCCTTGGAACGCCGTGA
CAAACGCCAATTGGTAAGTGATTATTGAAGCAAACTAGTCGTGGCAAACTTAGGTGTAGATTTTAGGTTAAATCAATCAATTTTTAAACATTTAC
CTTTCCTCTTAATCGTATTCCCAGACCGCCAATGGTGGCCAGAGCAGCCTGGCTGGTTCCAGCGGCAACTATCCCGTTTTCTTCGATGGCCTTAA
TGTGAATCCCCCGCTGCAGCCACTGCCGCCACTGCAGCAACTTCAGCCTCTGCAGCCATTGCAGCCGATTACGGTGGTGACTCCTGTGGCCTCCA
GTTCGAATGCCCAGAGCCAGCAGCCGCAGTCCGGCTGGCTGCCTCAGTTTAGCCAGAATCTTCCACTTATCGGAACCTGGGTGGGTGGCCTGCCC
AATTTGATCAACGGCCTGGGACTCGGTTCGCTAAACGGCGGCTTCGGCACTCTGGGCGGCCTGAATCTGGGCAACCTGGGACTGGGTGCAGTGGC
GCCGGTGGCCGCGGTGCCGGGCCAACTGCTCGGCTCGTCACCCAATCCCCAGACCACATGCCCACTCACCCAGAAGCTCAACTGCCGCTGTGAGC
CGCTCGTTCAGCTGCCGGGCCTGAAGCCCAGTTCCAATCCACTGAGGACGCAGCTGGTGCAGATCATGCGGCAGAATGCGCGGAAGAACGAGGAC
GGTTCGCAGGAGGTGCGCGTAATCCTGAGCAGCGGACATGTGATCTACCAGCGGACGGCCAAGGATCGCGGCCAGAGTGGCTACCTTGCCATGAG
AATTCAGTCGGGCAGGTACTTCAACATCTACTACAGTGTCAACGAGAAGGAGTACACGGTGCGGGCGGATGTCAAGGACACGCCACCCACCTCCG
ATTTTGACGACGAGCTGAGTGGTCAGTTCTAAAAATTGGTCAAAGGGATTTCCCTTTACTTACCTACAGTTTTTTTTTCTATACTTAATACTTAA
CTAGCCATTTTTTATATGAAATGCACTTAAACATATGTATTTGAATAAGCATTTAAACATATTTATGCTTATATGTTAAGCGTGCCCGATTTGAA
CCAAGCCGCCGAAATTCTTCGTAAACTCCATTAATCCCTTTTTTATTCGCAACTTTTTTTTTGAACTTAAACAACTACAAACTAGCTGCGAAAGA
AATAAACTACAATGAAACACATTTTCTGACGATTGCTCCTTGGGGACAAAAAGTTTAGCTACAAAGACAAATATTCATGGGGGTGCGGCAATAAA
CTTGTTTTTATTGCCGAAAATGTTGTTAAAGGGTTAACAAGGTGGCAACGGGGGGGAGGTTGTTTCTTAGCCCTTAGCCCAATTTCCAAAAAAGG
AACTTTCCTAATTACTGAAGCCACTTGGAAAAGAGATAAATAAATATTTACTCAGGCAATATTTAAGCAATAATTGTTCGCTTATTATTATCATT
TTTCAGTATCAACTGATAATTATTCGTGAATAAAAGTTTTAACAATGGATATAGAAGTCTTTGTATTTTATAACTATTAAGTGCTCAAGTTTGTA
TATATGGCATAAATAGTTATAATTTTGTTTGTTTATTAGTTGCAGCAAGCCGACACCAGTTGAATCTGCTGGTCATGGAAAAACCCACAGAGAAA
GAGGCCAGCAAACAAACAAAGAGCCAATGGGCAAATGGAAATCAAGCTGTAAAATGCCATATCCCTATCCCCCTCTCCACCGCCCCCCCCCCCT
CACATCTGCGCTTTTCCGCACTTCACTTTTCCCCATTTTGCCTTTCAAGTTGCGCTCAGAAGTTTCGCAATGAGCCGGGAAATGGAAACTGGCAG
GATATGCCCGGAAAAGCGAAGTCGAGTGCATGGTGGTAGAGGGGGGCGGGTTGCGGTGCGGTGTGTTGTATAATTAAAAGTTCCCTTTTGTGCCG
AGATTGGTGGATCCTCCCAAAAGGCAGCTACATTTTGATCCTTGCCAGCTGTGATTAGTCAGTGAACAGCAGGAGTTCTCAAATATAGTAAAGTA
GTCTTCCTTTTTTTTTGTTAACTGGAGGTTAACTGGAAGTTTAATATTAAGTAAAGGTTAAGTTGTAAGAAAAAAAAATAGATTACATTTTAAAC
TGCACATTAAAATTAAATTGTAAACATAAAAGAAACCAAGAACTATTATTTAGTTTATTATTTAGCTTTTCAGATTGCTTTTGAAAAGAAGCTAA
GTTTTGGTGTTTAAATTGTGAAATTGCGTGATTTTCGATTATGGGGCCCGATTTGTGGGGTGCTTAAAGCACTTTCGGTAAATAATTTACACAGT
TTGTGCATAAAAGTTGCTTCTGCTGGGGCCTTTTAACCGGGGCATGGAAGGGGGCGTGACTGGCAATGAAACCGCATTGCTCGGTGCACACGAAA
CTTTTCACAAATCATAAATGGTCCCAGGACACACACACAAACACACACATTGCAGTTTAGTTCAGTGACTACCCAGCTTTTCAGCCACCCGTTTC
CCCCCTGTATTTAAAAAGTCCCCCATTTCAGAATGACCACCTCCCCCCCCCCCCCCACTCCACCTTTGAGGGAGCCCCTCTCAACCAACCGCCTC
ATTGGTTATGCCAATTGCAAAAAGTCCTGGGCAACAATTGAAATTGCCGGACTCGTTGATGAGACTTTAAGCTCTGGCTGCAGTTGAAACCCCGC
CCCTAATTACGTATTACCAGATGACTGCCATTAAGTGTTCCACAACCCCCCGCCCCTCACTCCGCACCCCTTCCCCTGACCACAGCCCCTCTTTT
AAAGCTGAATCATCTTAAAGTGCTGGACAACAAGGACGCACCATTAAATCCACTGAATGCTCCACATTTCGGTTGGCTTTGGTTTGTTGATGTTG
CCAGTGTTGGGTGGCATGGCCCAAGGGTTGGGGGGCTGATTCCTGCGGGTTATATAAGCGTTGGCGCTGCTTCTGCACCCATTAGCTGATACGG
CGGATCAGCGCGAGGGAGGAGGAATCCAAACCCAAGCCCAAAGCCAAAGCCAGACCAGTCGCAACCGCAGACCCACGTGAGTGACCGGCGACGAC
TAGACAGTGCGAGTCCATGCTTGGATGCATACATACATACATACATATGTATGTGTGCGTCTGGATGTGACCCACGGCGATGGCCCCTGAAACCA
GGATGCACCTAGCCCAGAAGCAACCCTCCTGCGTTCGCCGCCCCTGGCTACCCTCGAAAAACTGCCGCATTGTGTGGCCAGAAAGCGAAACCGCG
ACTGCAACTGGCCCTGCAATAGAAAATGCACTGCAAAAAAACTGGGAGTATGTATTTAAAGTACTTGATAAAGTTGGATTATTAAATAACACAAT TAAATTTAATATTAATAGAGAAGTAGTATTCTTATCAAGATGAGAACTAAGGAGCTATGTTAATCTTGAACCAGGTGTGGCCAACTTTATTTTTC
ACAGTGTGGCAAGGATAAGCAAAGCGACCAGAAAAGTATAACCAGCAAAGATGGACCCATGGAGAACGGATGCGAATCGAGAGCGGAAAGCGTGA
CAGATAGATGGGTTGGAGCAGCAAGGGGTTAATGAAGGAGGGCATTTAGTTCGTGGTACTGTGGAAATGATTAAAATGTATTAGGTGAAATTAAG
TTGGCCAAACAGAGAAATGGGGGGGGGGGTTTAAATAAAGAGGCCAAAATGAGGTTAAAACGTTGCACAAAGCCAAATGGAGCCTGGCTGGGCG
AAAACAAATTCATTAGGCTGCAGTGGCATAAAAACATCATACCCACAAAAAGAAGATGCACAACGAAAACCGAACAAAGTTGATTTAAAGTATTA
TAATCTGCAACATTTTTGCGTATTTCGAGAATGCAGCTTGTTTACCCAGTTTGAAGTCAAGTTAGACTTATCTCTGGTTAATTGGTTTGCTCGAG
AGCAGGGCGCGCAAAGCTGCTGGGAAATCGTGGAAAAATCGTAAAGCTTAATAATGACACTCCCCACACAGCCCCTACCACCAGTCCAGCATTGG
GAATTCACAAGCCACTGTAAACAGGTGCAAACGTTGCGTTGCACAGCAATTTCAGCAACCCCTCTTAACTTTTGCGCCCAGCTTTCCACGTTTTC
CCTTGTTCAAATAGTTGTAAATGGGCGAAAATGCAAACAAAAAACAGTGATCCACTTGAAAGGCAAAACAAGAAAAATCATTCAAAGAGGCAACA
ATGCTGGGAAAACAAAAGGAAAACGAACGAAAACGAACTGCAAAGACAGCGACCACTAAATAAGTGAAGTGCGTGGACGACTGGACGAGTGGAAA
TGCGGAAAAGTGGGAAAGCGGAAAAGCGCGCGCAAGAAATTTGCAATGTGGCGAATAAATAAAGGATCAAGCGATTCCCCCATTCAAATTGGCGA
ATATTGGGCGGTTAAATGGAGATACATGCACGGATGTAAGGCAACTCGAAAAGGTGGCACAACAAATGAACGAGATAACTGGTTAACCACGAGTT
GTAAACGCGCAAGCTATTGTTATTAGTATGTTAAAAAGCGGAATAAACTTTTTGTGTTTAACTACAGCTCCATGAAATATGTATATGCTATATGT
AACAAACAATAAGCGAGAAAGTTTGTCGGCAACAAAAAAAAAAAGTAATAACCATTATGATATTATGAATGCAATTACATTCTTGACGACTCGAAA
GAATTTTAAATGTATAAATTATAACGAGATAAAAAAATAAAATATAAATCAAATTTACTTAACATTTATAACATTTCTAGTGCAATATTTACTTT
CACTATATGGGTTAATAAAATAAACTTGCCTGTTTCTCGATGTTAAACCCCATTACTTCCAATTGGCCAATCGATTAGAAATTCAACAAGAGTTT
GCCAAGATCTGAGTCACTTGAGGTCGGGCTTCTTATCTGGCCATGTAGGTATATTCCCGATAAGCCCTATCAGCGACATCGAGGCGGAAACACAA
AAAGACCATCAAATCGACCACTTTCACAGTTGAAAGTCAGAGCTGCTGAAGAACGGACAAGAAAATGGCAGGTAAATAGGTCGTAAGGCCAAGAT
GCCATAACAAAAAATGAAAACATTTAACTAGGTGGATGATATAAAACAGTTACCAATCTTTAAAGTACTTAATCAGTTGAAACTCAAAATAAATT
AATTCAATTTTGGAAACTAACTTGGCCTAGCCAAATAAACTAGTTTACTTGCCATGAACAACAGAATTAAAGAGTTATACCATTCGGTGTGCTGT
TAAATAATCGTTTCATTTTTCCATTATCCCCCAGACCACAGATGGATGCACTTCAGCAACGGCAGCGTGCCGCCGAATGCCGTGGTGGCTGGTCA
CGATTCGGACGGGGACACCATCTACGTGGGCCGTGCCTTCTTCTCCAACGACATGCTGCCGGCGAAGGTGATTCCCAACAAGGGCAAGGCCTACG
TGGCGTATGCGCGCGAGGAGCACGAGCTGGAGAACTACGAGGTGCTTTCCGGCTACAACTACGAGTGGCTGTCGGCGGAGAACGGGGAGGTGCCG
CCGGGCGCCGTCAAAGTTGGTCGGAATGTGGACGGCGAGTATTTGTATGCGGGCAGGGGTTATCATGCCGGCAGCTTAACCATGGGCAAGGTGCA
TCCATCCCACGGCTGCCTGTATATTCCCTACGATTCCGATGAGGTTAAGATCTTTGCCTACGAGGTGCTGTGCCAGCCGGAACGTTGGATCGACA
CCACCGCAACAAATATTCCGGATGGAGCTCTGGTTGCTGGGCACGATTCCAACGGGGACACCATCTACGTGGGCAGGGTGTTCCGCAATGGTGAT
CTGCTGCCAGCCAAAGTGGTGCCGGCGAAGGGGAAAGCCTATGCCGCCTATGCCCAGGCGGAGCACGAGCTCACCGACGTCCAGGTGCTGACGGG
ATCCGGATTCCGTTGGGTTCCGGCCTCGCACGGAAATGTGGCTCCCGGAGCCCTGTCCTCCGGTCCGAATGTCGACGGGGAGCCCCTCTACGTCG
GCAGGGCCATCTACTGCGACAGCTTGAGTGTGGGCAAGATCCATCCCTCGCACGGCTGCATCTACATCCCATTCGGTGGCGAGGAGGTGCGTCTG
GAGAATTACGAGGTTCTGGTGAGGATCTAGACGGACAGCTTTGCCTTTATTCCATTTTTTTTTTAATAAATCTATTTTTTACACACACAACAGAA
GTATACAGATTAAAGTATAAATTTAAGTTTAATTCGATCGACATCGAGCAACGTAACTGATAAAATTTATGGTAATGCACCCAGTAATTCTAAAA
AAAAAGTACCCCTTTCATAGAGTTTTGGTGATAATAGTTCAAAGTGGTTGTCATAGAAATTTCGAGGTATTGCGGATGTGAGGAATTTCTTCTAT
ATGCGGGCCTTATGTTATCACATCGGTTATCAATTAGCAACAATCAATTGATTAGTTGGCCATAAATTTGCGTCAACTTGTAACATAATTAACCA
TTTGCCTTCGCCCACTGACTTAACAAACACTGCATCGTAAAACTCAGACAGATATCGCAGTTATCAGAATGTGTACATATATGCACTCGATGCTT
TATAACTCGACCTTTCGTCTGCCGAGGTAAAAAGTTATAGGTATCGAAACTCTTTGTAACTTTCTTTGTATATTGAAAAGTTTATTAAAACGTTT
CATAAAGTTAAAGTCAATTCATTAGTGGCGGGCGTAGCGTTTTATTTCATAGCTTATTAATGTGCACACGTTGTAATCAATACATGTTTTAAGCA
CTTATTTGACAGCACAAAGTTTCCCATGGAAATACTTTTTTTCGCAATTTATTTTATAGGAAAGTTGCTAAAAGGCCTTAATCTTAACACTATCA
TTGGCGCCACCTATGAGATGATTATCTGCACTAACCGTGGCGCCACCTATGACGAGCTG
(SEQ ID NO: 130)

Exon: 1001..1248
Exon: 1355..1799
Exon: 3884..4585
Exon: 6212..6246
Exon: 6495..7134
Start ATG: 1078

Transcript No. : CT4928
CGAAGTCTGATAAAGAACAATCCTTACAAAATACAAAAAAATATATATATTTAAAAAATACAATTGAGCAACCAAACATGGCCAACATTCTAAGT
TTTACCATCTTTATGGCTGCCATTGCTATTGGACTGGCTTTAGCCACAACAACGACAGCAAGTACAAGGACACCCATGCCCACTTCCACTGAAAA
ATCCATGGAAAAGGACGATCCCATGGAGTCCTTGGAACGCCGTGACAAACGCCAATTGACCGCCAATGGTGGCCAGAGCAGCCTGGCTGGTTCCA
GCGGCAACTATCCCGTTTTCTTCGATGGCCTTAATGTGAATCCCCCGCTGCAGCCACTGCCGCCACTGCAGCAACTTCAGCCTCTGCAGCCATTG
CAGCCGATTACGGTGGTGACTCCTGTGGCCTCCAGTTCGAATGCCCAGAGCCAGCAGCCGCAGTCCGGCTGGCTGCCTCAGTTTAGCCAGAATCT
TCCACTTATCGGAACCTGGGTGGGTGGCCTGCCCAATTTGATCAACGGCCTGGGACTCGGTTCGCTAAACGGCGGCTTCGGCACTCTGGGCGGCC
TGAATCTGGGCAACCTGGGACTGGGTGCAGTGGCGCCGGTGGCCGCGGTGCCGGGCCAACTGCTCGGCTCGTCACCCAATCCCCAGACCACATGC
CCACTCACCCAGAAGCTCAACTGCCGCTTTGAAACCCCGCCCCTAATTACGTATTACCAGATGACTGCCATTAAGTGTTCCACAACCCCCCGCCC
CTCACTCCGCACCCCTTCCCCTGACCACAGCCCCTCTTTTAAAGCTGAATCATCTTAAAGTGCTGGACAACAAGGACGCACCATTAAATCCACTG
AATGCTCCACATTTCGGTTGGCTTTGGTTTGTTGATGTTGCCAGTGTTGGGTGGGCATGGCCCAAGGGTTGGGGGGCTGATTCCTGCGGGTTATA
TAAGCGTTGGCGCTGCTTCTGCACCCATTAGCTGATACGGCGGATCAGCGCGAGGGAGGAGGAATCCAAACCCAAGCCCAAAGCCAAAGCCAGAC
CAGTCGCAACCGCAGACCCACGTGAGTGACCGGCGACGACTAGACAGTGCGAGTCCATGCTTGGATGCATACATACATACATACATATGTATGTG
TGCGTCTGGATGTGACCCACGGCGATGGCCCCTGAAACCAGGATGCACCTAGCCCAGAAGCAACCCTCCTGCGTTCGCCGCCCCTGGCTACCCTC
GAAAAACTGCCGCATTGTGTGGCCAGAAAGCGAAACCGCGACTGCAACTGGCCCTGCAATAGAAAATGCACTGCAAAAAAACTGGGAGTATGTAT
TTAAAGTACTTGATAAAGTTGGATTATTAAATAACACAATTAAATTTAATATTAATAGAGAAGTATCAGAGCTGCTGAAGAACGGACAAGAAAAT
GGCAGACCACAGATGGATGCACTTCAGCAACGGCAGCGTGCCGCCGAATGCCGTGGTGGCTGGTCACGATTCGGACGGGGACACCATCTACGTGG
GCCGTGCCTTCTTCTCCAACGACATGCTGCCGGCGAAGGTGATTCCCAACAAGGGCAAGGCCTACGTGGCGTATGCGCGCGAGGAGCACGAGCTG
GAGAACTACGAGGTGCTTTCCGGCTACAACTACGAGTGGCTGTCGGCGGAGAACGGGGAGGTGCCGCCGGGCGCCGTCAAAGTTGGTCGGAATGT
GGACGGCGAGTATTTGTATGCGGGCAGGGGTTATCATGCCGGCAGCTTAACCATGGGCAAGGTGCATCCATCCCACGGCTGCCTGTATATTCCCT
ACGATTCCGATGAGGTTAAGATCTTTGCCTACGAGGTGCTGTGCCAGCCGGAACGTTGGATCGACACCACCGCAACAAATATTCCGGATGGAGCT
CTGGTTGCTGGGCACGATTCCAACGGGGACACCATCTACGTGGGCAGGGTGTTCCGCAATGGTGATCTGCTGCCAGCCAAAGTGGTGCCGGCGAA
GGGGAAAGCCTATGCCGCCTATGCCCAGGCGGAGCACGAGCTCACCGACGTCCAGGTGCTGACGGGATCCGGATT
(SEQ ID NO: 131)

FIGURE SHEET 60

Start ATG: 78

MANILSFTIFMAAIAIGLALATTTTASTRTPMPTSTEKSMEKDDPMESLERRDKRQLTANGGQSSLAGSSGNYPVFFDGLNVNPPLQPLPPLQQL
QPLQPLQPITVVTPVASSSNAQSQQPQSGWLPQFSQNLPLIGTWVGGLPNLINGLGLGSLNGGFGTLGGLNLGNLGLGAVAPVAAVPGQLLGSSP
NPQTTCPLTQKLNCRFETPPLITYYQMTAIKCSTTPRPSLRTPSPDHSPSFKAESS*
(SEQ ID NO: 132)

Celera Sequence No. : 142000013384694
GAGCTCCGCTGGCGATGATCGCACCCAGGATTCGACTGGCGCATCCGCCTCGCTGAGGGCGTTCATCTTCTTCACATAGTCCTCTGGTTTTTCGC
AGAAGTTAGAACACCACTGTCTCAACAGACGGTCCCTTTCGGTCTCCACCTTCGGTTTGGCCCTAGTCTTCTCTAAGGTCTCATTTCTCTCCCTT
TCGTGATGGCCACGTGGCGAATAGTCATCGCTGACTTGGTTTCTGGCTGCAGATCCATAGTATCCGTGTTGCGACCCCTTTGCCTGCCTGTGGGC
ATAGTGTCCGTGTCGTGGCTCGTGGGCATATCGACTGTCCTGAATTTGACGGTGTTCCTGATCATGTCTTTGTTCATACCGCCTACCCGAGCTAT
AGCCGGGATAATGGTGGTAGCCTTGACTGGAGCTGTTGGAAGTGTACCTCTGCCTTTCGGATGGAGGTCGGTAGTTGGACGAATAAGCAGGATAG
CGGTCTGGGTATTTATAGCTTTCATAGAGGAATGATGATCCGGATGCCGGGTACTGGTATTGGTAATGGGACTCCTGGCCACCATACTTCTGTGC
TTGTTCGTTGTAAGCATATCCCTCGTAGCCGTACGCTGGTGGTTGCTGGTACGGATCATAGCTAGGTACTGAGCTGGCATAAGGAGCCGGTGTCT
CCGGGTAGACGTAATCCAAAGACTTCGAGCTCTGAGAATGGGATTCATTTGAAGAATAGTTGTGAGAGGGAACACCTACTCCCGGTGGAGATAGA
TCTTCTTCTGGCGGAGGTGGCGGGGGCGGAGGAGCAGGCTGGACTGGAGGCGGTGGCAAAGGCGGCTGGTACATGGCGAAAAGTTTTGGGAAAAT
CTTTGGCAAAATCCACAATTATACTTTTTTCCACCCACACCTTTTACCGCGATTCGAATGATCTGGCAACTCGACCGGTTTGTTTACATTCGCAC
ATCCGGCAAGGCCGTGCCACATATGTTTCGATAGACAACGTAAGAAAATTATGTTACTTCCGCGGTATTTTTGCTGGAACCTCCAACGCTGCACG
ATGGCGTTTTACGCTGTAGCCAGTGGGCGGCGGTCTGGAGTCTACGGCTCTTGGGCAGAGTGCGAGGAGCAGGTCAAGGGTTTCAAGAACGCCAA
ATACAAGAAGTTTAAGACACGCCAGGAAGCGGATCAGTTCGTTAATGGCTGCAAGTCGTATGCTCCGCAGGATGTGGCCGTGCCGCTGGGCAAGG
AAAAGGCGTCACTGGCCAGTTGGAAAAACAGTATCGAAGTGAATAAGAACCCCAAGTACACAGATGAGTGGCCCGAAGAGGATCACGACCTAGCC
GAGGATGATCTGGTAGGCATGAATATACATACGTTTGCAAAGTCCTGACCTTTCATCCTTTCAGAATGCTGCCATGAACGAGGTTGAGGGAGATC
CAAAGCCATCTAACAGTAGCAATTTAGTATGAGACCGTAGTACATACTGTAGAAAAAGTTAAACATAGCTTCTTTCAGCCAGACATTCTCAATCG
CAAGCGGAAGGGCACAACCAGCGGCGATAAGCGGAACAAGATCCCACGTCATGCCTCTCAGGTCTCAGAAGCCACAGGACTCAAGCAAGTGGGTG
CCTTCCAGTTTGAAATCGATGCAGAGGGCTATGTCATTGTGTACACAGATGGCTCCTGCATAGGCAACGGACGAGCCGGAGCCTGTGCCGGCTAT
GGCGTTTATTTCGGCAAGAATCACCAGCTGTAAGTGGTAACTGCAGCACAATAACTTTGCTTTTAACCTATATGTTCTTTGCAGAAACGCAGCCA
AGCCCGTGGAAGGACGCGTTACAAATAATGTAGGTGAAATACAAGCGGCCATTCATGCCATTAAAACAGCTCTTGACTTGGGAATACAGAAGCTG
TGCATCAGCACAGACTCTCAGTTTTTGATCAACTCCATAACGCTGTGGGTTGCGGGTTGGAAAAAAAGGGATTGGAAGCTAAAGAACAATCAGCC
TGTTAAAAACGTTGTTGACTTCAAGGAACTGGATAAACTGCTTCAGGAGAACAACATCACCGTGAAATGGGTGCGTAACTAAATTTAAATAAGGT
CCTGGAAAATACTTGACTTCAGTTAATATCCCCAGAACTATGTGGAGGCCCACAAGGGCATAGAGGGCAATGAAATGGCAGACAAATTGGCGCGG
CAAGGATCCGCCTTGTATAAGCAGAAAAATGGTTGAAAAGCTATTTTAAATTTACCGTATTTTTAGTATGTAATTGATATGGCAACGCTGAATAA
ATTTTAGTTACGCGACAGCCCTGGTCCAAATGTTTTTATTTACAATTTACTTCAGTCGCTTTTAATATAAGTTAGTTTGCAAAAAATGCATTCCA
AGGGAAATAACCAGTGCTTACTGTTCACCTTGGTTTTGGGCTTACTGGAGGCGCGGGACATTGTTATGTAGTCGAACCACCTATCGTTCACGTG
GAAATGGAAAAAGCCGGCATGCACAGGTTTTTATATTGGAGAGCGGTTTATGGATTACCTGAATTAAAGTGATAAATGTTTATGCAGGACCCTTA
ATTACCGTCTGCGGTTCGATATACCCTTGGTGGGCAAGGACTGCGAGTATGCGCTGGTCCAGGATTTGCCCGCATCCGTTTACATAAGCACAGAC
GAACTGGATGACCTGCAGCGTTTGAAGAGGGTGCGTTATCTTGGGAATTAGTTACAAGGGTTACTATATAAAAAAATGTTCGTCTCCAGTTAAAT
GCCATCTATCCTAAGTTCGTCAACATTGAAGTAGCCACGGAACGGGCGCAGCCCTTCTCCGTTTTACTGCGCGGTACACCAAAGATTACGGAATC
GCTGGCTCTGCCCGTGCATTTTCGCTACCATGCCCCCAGTGATAAGCGGTGTGGTGATCTTGAAGTCTGAATTGCTTTCGTCCACTAGACTAATC
AATTAATCCTCACAGTTTGGCGGCAACGGTGGCCATACCCCTACCCGAGCTCTATCTCAACTGCCCGATGGCTGATAGTGCGCTCATCGAAAACG
AGTTGGTTGCCCGGCCCGATAAGCTGTACTGCCTGAATGCGCCGGAAAGCCGTTTCGACGAGAACCATATCAAGGATGGCCAACCCACGACCATG
GCTAATCTGGAGCGCTGCAACTGGAGGCGGGTGCACGTGGACTGCCAGCTAAAGATGCCGCTGCGTGCCGAGATTCCGGTAGGCCATGCTAGCGC
CTACGGTCCAGTTCTGTGCGGCACCATCCTGCTAGGTTGGTCTCTGGCCCTGTGGACCAT
(SEQ ID NO: 133)

Exon: 1001..1342
Exon: 1395..1451
Exon: 1504..1739
Exon: 1795..2065
Exon: 2126..2290
Start ATG: 1001

Transcript No. : CT4974
ATGTTACTTCCGCGGTATTTTTGCTGGAACCTCCAACGCTGCACGATGGCGTTTTACGCTGTAGCCAGTGGGCGGCGGTCTGGAGTCTACGGCTC
TTGGGCAGAGTGCGAGGAGCAGGTCAAGGGTTTCAAGAACGCCAAATACAAGAAGTTTAAGACACGCCAGGAAGCGGATCAGTTCGTTAATGGCT
GCAAGTCGTATGCTCCGCAGGATGTGGCCGTGCCGCTGGGCAAGGAAAAGGCGTCACTGGCCAGTTGGAAAAACAGTATCGAAGTGAATAAGAAC
CCCAAGTACACAGATGAGTGGCCCGAAGAGGATCACGACCTAGCCGAGGATGATCTGAATGCTGCCATGAACGAGGTTGAGGGAGATCCAAAGCC
ATCTAACAGTAGCAATTTACCAGACATTCTCAATCGCAAGCGGAAGGGCACAACCAGCGGCGATAAGCGGAACAAGATCCCACGTCATGCCTCTC
AGGTCTCAGAAGCCACAGGACTCAAGCAAGTGGGTGCCTTCCAGTTTGAAATCGATGCAGAGGGCTATGTCATTGTGTACACAGATGGCTCCTGC
ATAGGCAACGGACGAGCCGGAGCCTGTGCCGGCTATGGCGTTTATTTCGGCAAGAATCACCAGCTAAACGCAGCCAAGCCCGTGGAAGGACGCGT
TACAAATAATGTAGGTGAAATACAAGCGGCCATTCATGCCATTAAAACAGCTCTTGACTTGGGAATACAGAAGCTGTGCATCAGCACAGACTCTC
AGTTTTTGATCAACTCCATAACGCTGTGGGTTGCGGGTTGGAAAAAAAGGGATTGGAAGCTAAAGAACAATCAGCCTGTTAAAAACGTTGTTGAC
TTCAAGGAACTGGATAAACTGCTTCAGGAGAACAACATCACCGTGAAATGGAACTATGTGGAGGCCCACAAGGGCATAGAGGGCAATGAAATGGC
AGACAAATTGGCGCGGCAAGGATCCGCCTTGTATAAGCAGAAAAATGGTTGAAAAGCTATTTTAAATTTACCGTATTTTTAGTATGTAATTGATA
TGGCAACGCTGAATAAATTTTAGTTA
(SEQ ID NO: 134)

Start ATG: 1

FIGURE SHEET 61

MLLPRYFCWNLQRCTMAFYAVASGRRSGVYGSWAECEEQVKGFKNAKYKKFKTRQEADQFVNGCKSYAPQDVAVPLGKEKASLASWKNSIEVNKN
PKYTDEWPEEDHDLAEDDLNAAMNEVEGDPKPSNSSNLPDILNRKRKGTTSGDKRNKIPRHASQVSEATGLKQVGAFQFEIDAEGYVIVYTDGSC
IGNGRAGACAGYGVYFGKNHQLNAAKPVEGRVTNNVGEIQAAIHAIKTALDLGIQKLCISTDSQFLINSITLWVAGWKKRDWKLKNNQPVKNVVD
FKELDKLLQENNITVKWNYVEAHKGIEGNEMADKLARQGSALYKQKNG*
(SEQ ID NO: 135)

Name: RIBONUCLEASE H1
Classification: enzyme
Gene Symbol: rnh1
FlyBase ID: FBgn0023171

Celera Sequence No. : 142000013384605
TTTGTTGATTTATTAAAACATTGTTATCTTGGTTTGTGTAATCGTATCTTGAACTAACCACTTGATGTGTTCTTTTAGTTGTCCTGCCCCATATT
GGATCCGCCACGAAGCGCACCCGTGCCGACATGTCCACCATTGCTGCCCATAATGTGCTCCGCGGTTTGGCTGGGGAGCCCATGTTGTCGCCCGC
CTACTAGTAAATTCAAATGGGAAATATGGCTTTCTACCGCTAACCAGTTTGGAATGTCCGCCAAACAAAGTGCGAAAGGCCGCCGATGACCTTGG
CATGCCAGTAGATGTGAAAATAAAAAAAACAATTAAAAAACAAGTATTTGCTGTTGCAAATTTATTAAATTAAATATGTGGGAATCTAATCTATA
CCGTAAGATTAGCTCAACTGATTAATATGGAATAGGTAAAGCAATAGAATAATTGGTGCTAGAGAATGAGAAACATAATTTAAATACTAATATAG
TATATCGTAGGAAATAATATTGTACGTTTTAAGAAATGAGAGCAGAAAACATTGATTTAGTAATTCGCAAAGTTTAGCTCTGCACAATTGCAAAA
CCTACCACTTTTCCCCAAAATGTATCGAGGACCTTCAAACTGCTGATTTCGCATCCAAAAGTCCCAGGAACGGCTGCGGGAGCTTGTCGGATCAG
GATCGGAATAGGATCATCGCTTCTTAAAACTGGGTGCTTATGCCGCTTGAGAGTTCGCTCGCGAAACCCGACTTCGGTTGTAGTTTTTCAACCTG
CTCCCACTGATTATGGCTTTGCTGATCGAATATAATAATTGAAGGCCCCTGGGCATGGCCCGTTGGTTTCAAGGTGCTGGGGGCGAATCCCAGGG
ATTACTATGTGGGCATTTATCTGCAGAAAGAGAACTGCAACTGCAACTGCTGCAACCAGCAAGAAAGCAGACCGGCGACTGAGCAGGACAGTAGC
CCCATAAGGCAGTGGCTCTAAATGAATACTGCCCCCAGCTGACTACGCCGATGTGCCGGAAGTCAAGAGGTGCAAAGTCCCCTGTCAACAACGAC
GTGGTCGATTTGGCAGTGGGTTCGAGTCGTCGTTTCCACAAGTGATCCAAGAGGATGTACACCATGTTGTACAGTAAAGGATGTAGTAGTATATT
AAATTGAACGATTAATCAGTATACCTGTTACTCCAAAAGTAAACGGTATACTTCTTTCAAAAATAAGTAACGGAAGAAGAAAACGTTTTCATTG
CATACAAGTATATGTCTGTCCTTTCGAACAACTCGATCTCAGGACATAAAGCATTTTTAATTTTTCAAAAATATGTATGTAACAGTTGTGGGCGT
GGCAACGATTTGAAACAATCTTTTGCAGCGTAGACGTAATCTGTATGCCTAATCTAAAGATTACAGCTTTTTATAGTTCCTGTAGGCTATTGATA
TCAGTCCTAGTTGCTTTTAGGGCCCCCACCTAACAAATACTCGTACTTCTGGCCCCTTATCAGTATAAAGATTTTTGTCTTATCTCTTTAGTGGT
TGACAGACAGTGTCTAAAAGTATTTTGGCAAGATTTCATTAAGGTTTCTTGAAGGTTACAAATGAGTAGGTTAACGTTTTTGCTGTTTAGTTTTA
TCATGTTTCTGCGTAAATGTTGATCTTTAATGTCACCTTTTTAGTTGATTTATTTAAAGATCGTTATTTTTGCATAACTTTCAGTTGTCCTGCCG
CATATTGTGGCACCATTACTACCTATAATGTGATTCGTGGCTTGGCTGGGGATCCCATGTACCTAGTTGCCCACCTACTATTACATTTAAATGGG
TTTAGCCGCATCCCAGTAAATGTGAAATAGAGTAAAAAAACATTTTCCTGATGCAAATTGATTAATTAATGTGGAAATCTAATCTAATGGTATAG
TTTGACTGATTACTACGAAATATGTATGAAAATCGCTCATAGAAACGTAAATAAATAATGACTTTAATTATATAAAGCTATATATAAATAATCAA
TTTTATAATTGTAAACTTTTCTTTTTACTGTAATACTTTAATACTATCCCTAAAAATTGTATAGGAACGCGCAGGAAATAGTAATGTGAATTTCA
AGAGATGAGAGCAAATTAAAATGTAAAAGCTTAAGAGAACCTTTTAAGCCTAAGAGCGGGGCACAGAAAAAGCTTGAATTGTCATTTCGAAAATT
TCCACTTAGTTCAGCCCTGCAATTCGCCGCTACTAGTTGATATTAAGTGCTATATTTTCCCCCGAAATGTCTCGTGCGACCAGGGCTTTTAAAGT
GCTGATTTCGCATCCAAATGTCCCAGCACCGGCTCTGGAACTGCTCCGATCCCGTGGAGCGGAGACCATCATCTGCCAGAGTGTGCCGCCCTCGA
GGGATGAGATCCTGCAGAAGGTGCCCGGCGTGGATGCCATCTATTGGGCCCATTACCAGCCCCTGAATGCCGGAATCCTGGATGCTGCTGGATCC
CAGCTGCGTTGCGTGAGCACCATGTCCTCCGGAATCGATTTTGTGGATATTCCGGAGTTCCAGAAGAGGGGAATCCCATTGGGCCACACTCCCGG
GGTGGTGAAAAATGCAGTGGCCGATCTCGCCATTGGCTTGATGATTGCAGCCGGTCGTCACTTTCATGCCGGTCGCACCGAAATCGAGAGGTAAG
AAAAGCTGATGGGCGCTTTTTTCTCAGAAGCTTTTAATATTGAGAGCTTTTCGGATGAGGGTTGCCAACTAGTTGCACATGCCCTATATACGGCT
CTACTTCTACACTCTTTTGGAATATCAGATACTTAAGTACACCTAATACTTACCAATCATTAATACGTTTCATATGAAAACATAATATAATATAA
AAATATTTACAGGTCCCAATGGAAAATCGAGCAGATCAACTGGATGATGGGTCAAGAGATTCGCGATTCCGTCATCGGTTTCTTTGGCTTTGGCG
GTATTAGTCAGGCCATCGCCAAGCGATTGCAGTGCTGGGATGTGGCCAAGATCATCTACCATACTCGCACCCGAAAGGAAAACGATGGCGACTTC
AAGGCAGAGCATGTGTCGTTTGAACAACTTTTACAAGAAAGTGACTTCCTGGTGGTAGCTGCTCCACTTACAAACGAAACTAGAGAGAAATTCAA
TGGAAAGGCATTTAATCTGATGAAGAGGAGTTCTGTGTTTGTCAATGTGGCCAGAGGAGGTAGGATTTTAACTACATAACTGTATGAACGCTATT
GCATACCCGTGGATTTTTTCAGGTCTGGTAAATCAAACTGACCTTCATGACGCCCTGACAAATGGTACAATTTCTGCCGCAGGCTTGGATGTGAC
CACACCAGAACCACTGCCCGCCAATAGTCCTCTTCTCAATGTGCCCAATTGTGGTAAGCTAGAACATTTATTTCTCTTCCCTGAGTGAACTGAAA
TATTATTTATATATTTCCACAGTTATCCTTCCCCATATGGGCACTCAGACAATGAAGACTACCATTGAAATGGGATTGCTTGCTGCCAATAATAT
TTTGAACGCCATCGAAGGGAAGCCCATGATAAGGCCAGCCTACTGAGAACATGCAAAATTTGAATGGAAGAAACTTTACCTGTATCCTACTCGGA
TCGGAAAATCAATATTAAAAAATGATATTAAACATATAAATGTCGAACTTGTTAACCGCAACTATAATGGATTGATATTTTTTCTTGTTTAATTG
AATAAGTGAATAATTATGAAAATTATGAACGTAACCATAAAAGCTCTTCATGCGTTTTGTTGTCAGCTTTTTCTGTGATAGGGGGATCTGGTGCT
CTATAAAAGTCCGGCGACAAAGCCAACCGTTTGTCAGTCGTTTAAGAAACGCAGGGAATATAACGTCGGTGCTAATAGACTCCGATTTTTGAGCA
TTTAAGAGCTTCAGAGAGGAAGAGCAATCAAAAAGCTTCTAACTGCTCACGAAAAAAGAGAATATTCGAAACTCTGCTCTGTGTCAGTGATTATC
TATAAAGTGTGGCACTTGTAATTATTTTTCCTATCAAATAATATCTTTTCGTCACCAGAAGGACTTAAAATGTCAACAACAAAGCCGTTTAAAGT
GCTGATAGCACATACCGATGTTCCGCCAGAGGGAATTGAAATCCTGAAGGAGCAATGCGAGATCCTGCAAGTAATAAATGAACCTCCAAAAAATC
GGCCTGAAATTCTAGAAAAGATCAGGGGGGCTCATGCCGTTATTTGGGGTGGTCGGGACATACTCAATGCCGAGATTCTGGACGCCGCTGGTCCG
CAATTAAAGGCGGTATCCACCATGTCGTCGGGGATAAACAATGTGGATGTGCCGGAGCTAAAGAAAAGGGGTATCCCCTTGGGAAGTACTCCTGC
GATGCTGACTGTTGCGGTAGCCGATCTTACGGTGGGCCTGTTGATCGCCGCTGCCCGGAGGTTCCAAGAGGGTCGAAGGAAGATAGACAGGTAAA
GCAAAACAACCTGTCATTTTTTATTAATTACTCTGATATCGCAAAGTTTCGTATCCTTGATTACAGTGATAAATGGGATAAGGACCATCTTAACT
GGATGCTGGGTCAGGATATCCGTGATTCCACCGTGGGCTTCTATGGCTTTGGAGGCATTGGCCAGGCAGTGGCTAAGCGTTTGATGGGATTCGAT
ATTAAGCGCATGTTATATACCACCCGGAATCGCGTTAGCCAGGATATCGAGGAGCGGTTCAATGCCAAGAAGGTGGATTTCGAAACGCTTCTGGC
GGAAAGTGATTTCCTCATCATTGCATCCCCATTGACCAAGGAGACATTGGGATTGTTTAATGCCACCGTCTTTAATAAAATGAAAGAAACGGCAG
TACTGGTCAACGTTGGCAGGGGCAGTGAGTATATCCGAAAAAAGCAAACTAAAATGCCTAATGCCTTTCATTCTAGAAATTGTCAACCAAGATGA
TCTTTACGAGGCGCTTAAATCAAACCGAATTTTTGCTGCTGGACTAGATGTTATGGATCCGGAGCCCCTTCCTTCCAACGATAAATTACTTACTC
TAGACAATGTTGGTAAGTTATTATGTATCATCTACATAGGGTCAGAAACTATTTATATTTTTATCTCATTAGCGTTTTTTGGTATTTTTCTCAAG
AATGATAAGAACTGCCATTCAAAGAATTCTTTTGAAAACCTGACACTTTACGTTATAATCTATAGTTCCCTTACCATTAGGCACTTCATTTATCT
CGTTTGTTTCTTTTCATGAAGTGGTTACTCCTCATGTGGGCTATGCCACCCGGAGAACCCGTGTTGATGCAGCCAATTTGGCTTCGCGTAATGTG
CTCAAAGGATTGGCAGGAGAGCCGATGTTGTCACCCGCCTACTAAAATCTATCTAATCGGAAACAGAAATCAATGATTGAAAGTATGTGATTTAA

FIGURE SHEET 62

TTACAAAACTAACTTGTCGAAACGTTATTCACTTGTATTGTCAGCCTCTTCTTTAGCCACCAGGGGCAGATACAGTGGATCCCACTCCTCCCGCT
GCAGGGCCTTTAGATACTTCCTCCTCTCCTGGAGGACTCGCGGCACTAACTCCGGCTGCTCCCCCTTGTGTTTCTGTGATATTTCCAGGGCCCGC
CGCCAGTTGTGCATCCGCAGGGCTAGTCCGACTGCCTGTTCGATTTTCTTGCCGTGCAGCAGGATGGTCTCTGCCTCAAGCATCCTGCCCAGCAT
TAGTGAGTTTTCGGCCATCTGCTCGGCACTCGAGGGCGTCAGGGCCTTCAGGTGCTGCAGGTAGCTCACCTTGTCGATTTGCAGTGCTGCCGAGT
AGGCCTCCTCGCTGATCTGCAACTGGTGCTTCCTGGTCGCCACCGCCGCAAGAGTGGCCCACAAGCTGGAATGCTGGCCCATTCGGCAGATCTTC
AACGCCTGTTGCCACTGCCCTTCCAAAAGCGCACGATGCAGGATCTCGCAGTACATGTTAACATTGACGGGGAGTAGGGCGCCGGCGGAACGGAA
TGTGAGCACGGATTCCTCAAAGCTTTCGATGGTAATGTGTTTGCCAAATTCCCTAGGTGAAAGAGATTTTTAAGCAATTTAAAAAATAGTACAAT
TAATCTGGATTAACAGATAGCATTAAAAGTACAATGAAGCCTTGAAGTGATTTCAATTTAAAATAAAACCCGACATTCTAAAACAAGTTGAGTTA
GTAAGTACATCTATGTTCCTTACGTCGTATCCAATGTAATAGTGGTCAGGGCAATGATCGTAGGATCGGAGGCTCCTTCCCCGGGACAATACCAG
ATGCTGTAGCACGAGTCGTGTACTCCCACCAGAATATTTGTTTCGCTGGCCCACATAATGGCGGTGAGTTGGGTGCCGATCTTGTAGATCTCATC
(SEQ ID NO: 136)

Exon: 1001..1086
Exon: 2269..2404
Exon: 2474..2655
Exon: 2863..3194
Exon: 3313..3378
Exon: 4049..4460
Exon: 4532..4869
Exon: 4922..5047
Exon: 5247..5365
Start ATG: 1001

Transcript No. : CT5232
ATGTGCCGGAAGTCAAGAGGTGCAAAGTCCCCTGTCAACAACGACGTGGTCGATTTGGCAGTGGGTTCGAGTCGTCGTTTCCACAAGGCTTTTAA
AGTGCTGATTTCGCATCCAAATGTCCCAGCACCGGCTCTGGAACTGCTCCGATCCCGTGGAGCGGAGACCATCATCTGCCAGAGTGTGCCGCCCT
CGAGGGATGAGATCCTGCAGAAGGTGCCCGGCCTGCGTTGCGTGAGCACCATGTCCTCCGGAATCGATTTTGTGGATATTCCGGAGTTCCAGAAG
AGGGGAATCCCATTGGGCCACACTCCCGGGGTGGTGAAAAATGCAGTGGCCGATCTCGCCATTGGCTTGATGATTGCAGCCGGTCGTCACTTTCA
TGCCGGTCGCACCGAAATCGAGAGGTCCCAATGGAAAATCGAGCAGATCAACTGGATGATGGGTCAAGAGATTCGCGATTCCGTCATCGGTTTCT
TTGGCTTTGGCGGTATTAGTCAGGCCATCGCCAAGCGATTGCAGTGCTGGGATGTGGCCAAGATCATCTACCATACTCGCACCCGAAAGGAAAAC
GATGGCGACTTCAAGGCAGAGCATGTGTCGTTTGAACAACTTTTACAAGAAAGTGACTTCCTGGTGGTAGCTGCTCCACTTACAAACGAAACTAG
AGAGAAATTCAATGGAAAGGCATTTAATCTGATGAAGAGGAGTTCTGTGTTTGTCAATGTGGCCAGAGGAGGCTTGGATGTGACCACACCAGAAC
CACTGCCCGCCAATAGTCCTCTTCTCAATGTGCCCAATTGTGAAGGACTTAAAATGTCAACAACAAAGCCGTTTAAAGTGCTGATAGCACATACC
GATGTTCCGCCAGAGGGAATTGAAATCCTGAAGGAGCAATGCGAGATCCTGCAAGTAATAAATGAACCTCCAAAAAATCGGCCTGAAATTCTAGA
AAAGATCAGGGGGGCTCATGCCGTTATTTGGGGTGGTCGGGACATACTCAATGCCGAGATTCTGGACGCCGCTGGTCCGCAATTAAAGGCGGTAT
CCACCATGTCGTCGGGGATAAACAATGTGGATGTGCCGGAGCTAAAGAAAAGGGGTATCCCCTTGGGAAGTACTCCTGCGATGCTGACTGTTGCG
GTAGCCGATCTTACGGTGGGCCTGTTGATCGCCGCTGCCCGGAGGTTCCAAGAGGGTCGAAGGAAGATAGACAGTGATAAATGGGATAAGGACCA
TCTTAACTGGATGCTGGGTCAGGATATCCGTGATTCCACCGTGGGCTTCTATGGCTTTGGAGGCATTGGCCAGGCAGTGGCTAAGCGTTTGATGG
GATTCGATATTAAGCGCATGTTATATACCACCCGGAATCGCGTTAGCCAGGATATCGAGGAGCGGTTCAATGCCAAGAAGGTGGATTTCGAAACG
CTTCTGGCGGAAAGTGATTTCCTCATCATTGCATCCCCATTGACCAAGGAGACATTGGGATTGTTTAATGCCACCGTCTTTAATAAAATGAAAGA
AACGGCAGTACTGGTCAACGTTGGCAGGGGCAAAATTGTCAACCAAGATGATCTTTACGAGGCGCTTAAATCAAACCGAATTTTTGCTGCTGGAC
TAGATGTTATGGATCCGGAGCCCCTTCCTTCCAACGATAAATTACTTACTCTAGACAATGTTGTGGTTACTCCTCATGTGGGCTATGCCACCCGG
AGAACCCGTGTTGATGCAGCCAATTTGGCTTCGCGTAATGTGCTCAAAGGATTGGCAGGAGAGCCGATGTTGTCACCCGCCTACTAA
(SEQ ID NO: 137)

Start ATG: 1

MCRKSRGAKSPVNNDVVDLAVGSSRRFHKAFKVLISHPNVPAPALELLRSRGAETIICQSVPPSRDEILQKVPGLRCVSTMSSGIDFVDIPEFQK
RGIPLGHTPGVVKNAVADLAIGLMIAAGRHFHAGRTEIERSQWKIEQINWMMGQEIRDSVIGFFGFGGISQAIAKRLQCWDVAKIIYHTRTRKEN
DGDFKAEHVSFEQLLQESDFLVVAAPLTNETREKFNGKAFNLMKRSSVFVNVARGGLDVTTPEPLPANSPLLNVPNCEGLKMSTTKPFKVLIAHT
DVPPEGIEILKEQCEILQVINEPPKNRPEILEKIRGAHAVIWGGRDILNAEILDAAGPQLKAVSTMSSGINNVDVPELKKRGIPLGSTPAMLTVA
VADLTVGLLIAAARRFQEGRRKIDSDKWDKDHLNWMLGQDIRDSTVGFYGFGGIGQAVAKRLMGFDIKRMLYTTRNRVSQDIEERFNAKKVDFET
LLAESDFLIIASPLTKETLGLFNATVFNKMKETAVLVNVGRGKIVNQDDLYEALKSNRIFAAGLDVMDPEPLPSNDKLLTLDNVVVTPHVGYATR
RTRVDAANLASRNVLKGLAGEPMLSPAY*
(SEQ ID NO: 138)

Name: HYDROXYPYRUVATE REDUCTASE-LIKE
Classification: enzyme

Celera Sequence No. : 142000013384610
CATTTCGATGGTAGGTCTCCCAAGGCAACAGAAGCACAATCATCACCAGAACGAAGAGTATAAGCACTGGTATGATGTAGCCGTGCTTGCAGGAA
CAGATATTTCGCTCATCCTGGAGCCCTAGGCCGCAATTGGGACGCCGGCAACACGATGTGGTCAAAGGGGTTGGCTCTTCCGGTGCTCTGGGCAC
TGGCTGGTACTCTCCGGGTATCTCATGCACTACGCGACGCTCGGACATGGCAAGGGGATCAGGACTAATGCTGACTGGCCATTGTCAAACATTTT
TCACAGCCGAGCCTATTTATTATTCGCGCAGTTGTGGGAAAGTATCACCCGCCCACGCAAACAAATGGGCAGTGTTGGACAGCACAGCGCGGTAG
TCGTCTGCGCTGGCTGCTAAAAAAAAGCTAAAGGATAAATTAATCCAAGTCCCTGCTCAGAAAAATAAGTTGTCGTCAGTGCATTATTTCAGCAT
TTACTTCGATTTAAGTTTTAACGCCATAGAGTCCATTAATTCTCTTGAAGTTAATAAATGTTTATCGCTTTAATTCAAAACTGATAAACTTTCTA
TGGTCCTATTTATTTAACGACCCAATTTTGGCGGGAAACAAGCCGGCGGAACATTGCTGACGCGTATGCGTGACGCCAGCTAACACTGGTCGCCG
TGGTAAAGAATTTAGTCTGTCTTAAAATCTTCCGGCTGAGAGGGCTGAAAATTTTGACGGCTTCGAAGCATTTGCTGCAATATCAATTTCGTCGG
GTTTATTTCGAGTATCGCTTAATCAGGACGCGACCATGGCTGCGAGATTGATGAACGCCCAGGCACAGGTAGGTTCTAGAGCGGAGCCTGTGCCT
CCAGTCGGCCAATATATAACCACGGCTATATATACGTTTACGTATAGAATCTGTGAATGGAACCCCGAAATTCCAAGCTGCGATAAAGACAACTG GACAGAGCACTGCGCGAAAGTTTACAAAAAATCATTGCCCATTTCTTACACACCCAGCAGGATGTGGGCAGCGAAAAATAGCAAATTTTTCGCAC
AGCGTTTTCTAACCTAAAATCATAAAATTCGAAGTGGTTAGGTAACCGAGTTCGCAGTGTTTGTGATTCTACAGGCCCTGCATCCCAAACATGTA
TACTGAATACGCAGCAGTGAACCATGCGAAATCGTTAGCTCTCAACAATTAACAGCGATTCGTGGGGGTTCGATGGTTGGCATAGTTGCATTTAC
ATAATCGCCGGGGTCCAGTTATTTAACCAGGAGGCGAACACCCTCTAGAGCATATATCTTGTGGCGGAGGACCGTCTTATCTGTGACAGGTTTAC
TTACACTTTGATAATGCCAGCACTAAATATAGCTTAAAAAAGTTGCGCCGTTTAACTTGAGTATCACGCGCATTGGAGGAGTTTTGCCTTTCAAG
TGGGGTTTTTCCACGTCAGCTTCGAGAAAGGTTTCACTGTACTCTGCCCATAAGTTAACGACCTATTTGACGTAATTGTCATTGCAATTGTTTCG
ATTTGCGTGTATGTACATACAGTCGTGTCGTCACGTGGTTCTTCTAATTGGAGTGTTCTGTAGAATATTGTAACAATTTGAAAGGCTTACAAACA
AACTATATTTCCAGCTACTTTTTATTTTTTTATTCTGCAGTTCGAAGAACCTTAAAGCACTTTGGCTAGCACTTAAAATACTTTGATTGTTAAAT
GTAAACTTTCAATCATTTTACTAATCTCAAAAAAATATTTGGAAAAATTTCACTCTGAAGCGGTAAATGGATCAATGGATTATTTTTGGCTATTC
AAAAATTTCAAGACGATTAAAATTTATTAGCTTTAGCAATATATTGATCTTAAAACAAGTGAAAGCGGTGATAATAATGTTTTACATTTGTTATA
TATGTATGCAAGATTAAATGTACAGTAAAGAAGAATTTTCACAGATATGGTCCCCACATGATTGTACTCTTGTCAGAATATCTTTGGGAATTATC
ATTTCCTGATAGAGGAATCAATTTAATTAAAGTGACGAGGACTCGTCCTCTTGACATGATAATCAAGTGTTTATTGGGCTACCAAGCGAATAAAT
AAAATCTCACAGTGTGCGAAGTGCAAATAAACTAGAGAATCACATTGTGTTAATTACTTGATCTTGATTGCTAAATGTACCACTTCACCATATTT
AACAGTTCGACTTCTTATCTGCTTTCCAGGTGTGTCGACTGGGCAAGCATGTTGCGTCCGAAGCCACAGTGGTGCGTCAGTTCCACGCCTCCTGC
TACACCGCCTCCAAAGTGGCTCTGTCCAAGTTCGACTCGGACGTCTACCTGCCGTACGAGAAGCTGAACAAGCGCCTGGAAGTGGTGCGCGGTCG
CTTGAACCGCCCACTGACTCTCTCCGAGAAGGTGCTGTACTCGCATCTGGACGATCCCGCAAACCAGGACATCGTGCGCGGTACTTCGTACCTGC
GTCTTCGCCCCGATCGTGTGGCTATGCAGGATGCCACTGCACAGATGGCTCTGCTTCAGTTTATCTCCTCCGGACTGAAAAAGGTGGCTGTGCCC
TCCACTGTTCACTGTGATCATTTAATCGAGGCCCAGATTGGTGGACCCAAGGATTTAGCCCGTGCCAAGGACCTGAACAAGGAAGTGTACGATTT
CTTGGCCAGCACCTGTGCAAAGTACGGATTGGGCTTCTGGAAGCCAGGCAGCGGAATCATCCATCAGATCATTCTGGAGAACTACGCTTTCCCCG
GCCTGCTGATGATTGGTACTGACTCACACACCCCCAACGGTGGTGGCTTGGGTGGCCTGTGCATTGGCGTTGGTGGTGCTGATGCCGTCGATGTG
ATGGCCGACATCCCCTGGGAGCTGAAGTGCCCCAAGGTGATTGGTGTCAATTTGACTGGCAAGATCAGCGGCTGGACCTCGCCCAAGGATGTTAT
CCTGAAGGTTGCCGATATCCTGACCGTCAAGGGAGGCACCGGTGCCATCATTGAGTATCACGGCAAGGGTGTTGACTCTATCTCTTGTACAGGCA
TGGCCACCATCTGCAACATGGGTGCTGAGATCGGAGCTACCACCTCTCTGTTCCCCTTCAACCAGCGCATGGCTGATTACCTGAAATCGACAGGC
CGTGCTGGCATTGCCTCCGAAGCCCAGAAGTACCAGGCCAAGATTCTGTCCGCTGACAAGAACTGCGAGTACGATGAGCTGATTGAAATCAACCT
AGACACCCTGGAGCCCCATGTTAACGGACCATTCACTCCCGATTTGGGCCATCCCATCAGCAAGCTAGGCGAGAACTCGAAGAAGAACGGGTACC
CTATGGACATCCGTGTAGGTCTTATTGGCTCTTGCACCAACTCTTCGTATGAGGACATGGGTCGCTGCGCCAGCATCGCCAAGGATGCCATGAGC
CATGGCCTCAAGTCGAAGATTCCTTTCAATGTGACTCCCGGATCAGAGCAGATCCGTGCCACCATCGAGCGCGACGGCATCTCTGAGGTGTTCGA
CAAGTTCGGCGGTACCGTTCTGGCCAACGCTTGCGGTCCCTGCATTGGACAGTGGGATCGTAAGGACGTTAAGAAGGGCGACAAGAACACCATTG
TCACCTCCTACAACCGAAACTTTACTGGCAGGAACGACGCTAACCCGGCCACCCATTGCTTTGTCACTAGTCCCGAGTTGGTCACCGCTCTGTCC
ATCGCCGGTCGTCTGGACTTCAACCCGCTGACCGACGAGCTTACTGGTGCTGATGGCAAGAAGTTCAAGCTCAAGGCTCCCTTCGGCGACGAGCT
GCCCGCCAAGGGTTTCGATCCCGGCCAGGACACCTACACTGCTCCCCCACCCGTAAGTACATTTAAATTCCCAAACTGATTTATATTGTTCTTAA
GAATCAATATGGAAATCCCACAGAGCGGCGAAAATGTCAAGGTGGCTGTCGACCCCAAGTCGACGCGTCTGCAGCTGCTGGAGCCTTTTGACAAG
TGGAACGGCCAGGATCTGACCGATCTGACTGTGCTGATCAAGGTTAAGGGAAAGTGCACCACTGACCACATCTCCGCTGCCGGACCCTGGCTGAA
GTACCGTGGCCATTTGGACAACATCTCCAACAACATGTTTATCGGAGCCACCAACTACGAAAACAACGAGATGAACAACATCAAGAACCAACGCA
ACGGTAGCTGGGGAGGAGTTCCCGACGTAGCCCGCGACTACAAGGCCAACGGCATCAAGTGGGTGGCCGTCGGCGATGAGAACTACGGCGAGGGT
TCGTCCCGCGAGCATGCCGCTTTGGAGCCCCGTCACCTTGGTGGTCGTGCCATTATCGTCAAGTCCTTCGCCCGTATCCACGAGACCAACCTGAA
GAAACAGGGTCTTCTGCCTCTCACCTTCGCCAATCCCGCTGATTACGATAAGGTTTGCGACTCTTAGCTTCTGTGACTAAGGTCATATTAACCAT
ATCTTTGTACTTCAACAGATCCAGCCCACGAGCAAAATCTCCCTGCTCAACCTGAAATCCCTTGCGCCTGGAAAGCCCGTAGATGCCGAAATCAA
GAATGGCGACAAGGTCGAGAGGATCAAGCTTAACCACACCCTGAACGACCTACAGATCGGCTGGTTCAAGGCCGGCAGCGCTCTCAACCGCATGA
AGGAGCTGGCCCAGTAAATGGTCCTGGACCTACTTAAGACACCCAGTCAAGAAGCCTGATCCCAACCTTCTTCCTGTAGGTGAACACACTCAAAT
TCACAACGGAAGCAATCGAATTATGGTATTGTTATTCAATTCTTTTCAAATTGTTTATATTATATTTTGACTATATCGAGTGTGCAGCTTTAAAA
GTGAATTATGTAGCCGAACGATAGCGAGAAATTGTAAGAGTTTTATATATATAATTATACACAATTTTATTTTTAATTCTGGCTATGCATGCGTT
TCCTTCAATTTTTGTTCTTTTTGAATTTGTCCAAATGCTCTACAGATTGCCTCTACTATGAAACTGTTTTAAGTGCGAATAAAACTCAAGTAATA
TGTATTAAACCGATTCTTTCATTTAATAAACAACAGTTAAAACAAAAAAGCGGACAATAAGTGCCGTCAATTCATCCCGTGTCCTCTATATTTTC
TTCATTATTAACATAATTTTATCAATTATAAGACGTAAGACACAACAATTTGCACAATAAAGCATAATATCAATAATAGAATCTACTGGGGCAGA
TTACTTAATTATTCACCCATAGCTTTTGGAAAATATGTCGAATTGTCAATCAAATATAAATTATTAGTAAATCCAATTCTAGGACTATGAAACGC
AGAGCTCAAAGTAAAACTTCCGTTGCTTCCAGCACGGATTTCTTTTCACTCTCCGACAAGCCATCGTTGGGAAGAAGACGAGCCCTACTGGCTGC
AAAACTTAAGCGTCAGGAACAGAGTACAACGTCCTTTGACTCCAGCACAGGCTCCTACACTTATACAGACGCCACTTCTTTGCGAAAGACCCCCA
TCACCTTCTCACCTAGCCCGGAGTTCATGAAGACCGCCAAGGCTAAATTAAAGTTAATCGCATTGTATGAAGATCACAAATGCTTGTGGAATCAG
CGCAACAAAGATTTCTTCAATTTCGAGCTCAAAGACAGAATCTGGGATGCGATTGCCGATGAAATGAAAGCGGACTCGCCATCTGGGTTTTGGAA
ACATATGATTCACAAGCTTCGCTATAAAGTTGAGATGGAGCGCATACAAGAGCAGGGTGCAAAGTTTTCGGGTGAATCGCCGCAGCCAAAACTAT
TTTATTCAGATAATCTGCTGTTTCTAAATCACATGTTTGACCGAGAAGGGGGAAAACCCCCTCGAGAGATTGTATGTTTATAGTTAACGAACAAA
TCACTTTAGTATTTATTCTACTTTTTACTCAGCCAATGCATCTTAAGCCTTCGGGACCTACTCTCGAAAAGAATCCGTCTAGAAACCTGCGACAT
GTTCAGGAAAAACGTAAACGTACGCCCATTAGAGAAAAGATGGCTTCGCTTGAGAAGTTGAGGA
(SEQ ID NO: 139)

Exon: 1001..1086
Exon: 2215..3852
Exon: 3919..4422
Exon: 4484..5049
Start ATG: 2494

Transcript No. : CT5284
CACCCAGCAGGATGTGGGCAGCGAAAAATAGCAAATTTTTCGCACAGCGTTTTCTAACCTAAAATCATAAAATTCGAAGTGGTTAGGTGTGTCGA
CTGGGCAAGCATGTTGCGTCCGAAGCCACAGTGGTGCGTCAGTTCCACGCCTCCTGCTACACCGCCTCCAAAGTGGCTCTGTCCAAGTTCGACTC
GGACGTCTACCTGCCGTACGAGAAGCTGAACAAGCGCCTGGAAGTGGTGCGCGGTCGCTTGAACCGCCCACTGACTCTCTCCGAGAAGGTGCTGT
ACTCGCATCTGGACGATCCCGCAAACCAGGACATCGTGCGCGGTACTTCGTACCTGCGTCTTCGCCCCGATCGTGTGGCTATGCAGGATGCCACT
GCACAGATGGCTCTGCTTCAGTTTATCTCCTCCGGACTGAAAAAGGTGGCTGTGCCCTCCACTGTTCACTGTGATCATTTAATCGAGGCCCAGAT
TGGTGGACCCAAGGATTTAGCCCGTGCCAAGGACCTGAACAAGGAAGTGTACGATTTCTTGGCCAGCACCTGTGCAAAGTACGGATTGGGCTTCT
GGAAGCCAGGCAGCGGAATCATCCATCAGATCATTCTGGAGAACTACGCTTTCCCCGGCCTGCTGATGATTGGTACTGACTCACACACCCCCAAC
GGTGGTGGCTTGGGTGGCCTGTGCATTGGCGTTGGTGGTGCTGATGCCGTCGATGTGATGGCCGACATCCCCTGGGAGCTGAAGTGCCCCAAGGT GATTGGTGTCAATTTGACTGGCAAGATCAGCGGCTGGACCTCGCCCAAGGATGTTATCCTGAAGGTTGCCGATATCCTGACCGTCAAGGGAGGCA
CCGGTGCCATCATTGAGTATCACGGCAAGGGTGTTGACTCTATCTCTTGTACAGGCATGGCCACCATCTGCAACATGGGTGCTGAGATCGGAGCT
ACCACCTCTCTGTTCCCCTTCAACCAGCGCATGGCTGATTACCTGAAATCGACAGGCCGTGCTGGCATTGCCTCCGAAGCCCAGAAGTACCAGGC
CAAGATTCTGTCCGCTGACAAGAACTGCGAGTACGATGAGCTGATTGAAATCAACCTAGACACCCTGGAGCCCCATGTTAACGGACCATTCACTC
CCGATTTGGGCCATCCCATCAGCAAGCTAGGCGAGAACTCGAAGAAGAACGGGTACCCTATGGACATCCGTGTAGGTCTTATTGGCTCTTGCACC
AACTCTTCGTATGAGGACATGGGTCGCTGCGCCAGCATCGCCAAGGATGCCATGAGCCATGGCCTCAAGTCGAAGATTCCTTTCAATGTGACTCC
CGGATCAGAGCAGATCCGTGCCACCATCGAGCGCGACGGCATCTCTGAGGTGTTCGACAAGTTCGGCGGTACCGTTCTGGCCAACGCTTGCGGTC
CCTGCATTGGACAGTGGGATCGTAAGGACGTTAAGAAGGGCGACAAGAACACCATTGTCACCTCCTACAACCGAAACTTTACTGGCAGGAACGAC
GCTAACCCGGCCACCCATTGCTTTGTCACTAGTCCCGAGTTGGTCACCGCTCTGTCCATCGCCGGTCGTCTGGACTTCAACCCGCTGACCGACGA
GCTTACTGGTGCTGATGGCAAGAAGTTCAAGCTCAAGGCTCCCTTCGGCGACGAGCTGCCCGCCAAGGGTTTCGATCCCGGCCAGGACACCTACA
CTGCTCCCCCACCCAGCGGCGAAAATGTCAAGGTGGCTGTCGACCCCAAGTCGACGCGTCTGCAGCTGCTGGAGCCTTTTGACAAGTGGAACGGC
CAGGATCTGACCGATCTGACTGTGCTGATCAAGGTTAAGGGAAAGTGCACCACTGACCACATCTCCGCTGCCGGACCCTGGCTGAAGTACCGTGG
CCATTTGGACAACATCTCCAACAACATGTTTATCGGAGCCACCAACTACGAAAACAACGAGATGAACAACATCAAGAACCAACGCAACGGTAGCT
GGGGAGGAGTTCCCGACGTAGCCCGCGACTACAAGGCCAACGGCATCAAGTGGGTGGCCGTCGGCGATGAGAACTACGGCGAGGGTTCGTCCCGC
GAGCATGCCGCTTTGGAGCCCCGTCACCTTGGTGGTCGTGCCATTATCGTCAAGTCCTTCGCCCGTATCCACGAGACCAACCTGAAGAAACAGGG
TCTTCTGCCTCTCACCTTCGCCAATCCCGCTGATTACGATAAGATCCAGCCCACGAGCAAAATCTCCCTGCTCAACCTGAAATCCCTTGCGCCTG
GAAAGCCCGTAGATGCCGAAATCAAGAATGGCGACAAGGTCGAGAGGATCAAGCTTAACCACACCCTGAACGACCTACAGATCGGCTGGTTCAAG
GCCGGCAGCGCTCTCAACCGCATGAAGGAGCTGGCCCAGTAAATGGTCCTGGACCTACTTAAGACACCCAGTCAAGAAGCCTGATCCCAACCTTC
TTCCTGTAGGTGAACACACTCAAATTCACAACGGAAGCAATCGAATTATGGTATTGTTATTCAATTCTTTTCAAATTGTTTATATTATATTTGA
CTATATCGAGTGTGCAGCTTTAAAAGTGAATTATGTAGCCGAACGATAGCGAGAAATTGTAAGAGTTTTATATATATAATTATACACAATTTTAT
TTTTAATTCTGGCTATGCATGCGTTTCCTTCAATTTTTGTTCTTTTTGAATTTGTCCAAATGCTCTACAGATTGCCTCTACTATGAAACTGTTTT
AAGTGCGAATAAAACTCAAGTAATATGTATTAAACCGAT
(SEQ ID NO: 140)

Start ATG: 366

MQDATAQMALLQFISSGLKKVAVPSTVHCDHLIEAQIGGPKDLARAKDLNKEVYDFLASTCAKYGLGFWKPGSGIIHQIILENYAFPGLLMIGTD
SHTPNGGGLGGLCIGVGGADAVDVMADIPWELKCPKVIGVNLTGKISGWTSPKDVILKVADILTVKGGTGAIIEYHGKGVDSISCTGMATICNMG
AEIGATTSLFPFNQRMADYLKSTGRAGIASEAQKYQAKILSADKNCEYDELIEINLDTLEPHVNGPFTPDLGHPISKLGENSKKNGYPMDIRVGL
IGSCTNSSYEDMGRCASIAKDAMSHGLKSKIPFNVTPGSEQIRATIERDGISEVFDKFGGTVLANACGPCIGQWDRKDVKKGDKNTIVTSYNRNF
TGRNDANPATHCFVTSPELVTALSIAGRLDFNPLTDELTGADGKKFKLKAPFGDELPAKGFDPGQDTYTAPPPSGENVKVAVDPKSTRLQLLEPF
DKWNGQDLTDLTVLIKVKGKCTTDHISAAGPWLKYRGHLDNISNNMFIGATNYENNEMNNIKNQRNGSWGGVPDVARDYKANGIKWVAVGDENYG
EGSSREHAALEPRHLGGRAIIVKSFARIHETNLKKQGLLPLTFANPADYDKIQPTSKISLLNLKSLAPGKPVDAEIKNGDKVERIKLNHTLNDLQ
IGWFKAGSALNRMKELAQ*
(SEQ ID NO: 141)

Name: aconitase
Classification: enzyme

Celera Sequence No. : 142000013384610
ATGAATAAATATCAAAACATTTTTCAAAAGTTTGATTATTATCCTCGTTTTTCTCGATGTTTATGTAGGCACGCTCCATATCTGCTTTTAATCAA
AACATTGAACAACACAAAAAATGTAACAGTAACTATGTTTGGGATAGAATGATTGATAAATGAGTGCTTGCAACAGGTCCTGAAATTTATAGACT
GAACGGTTACCCGATATATATATATATATGTATGTATATGTTGTTAGTTATTCATTGGTTACAAATTAATTTATTTTATTGTATTGCTTATATAA
AGACATGAGTTTATAATTTAATGGTGGATACAGATTTTTTCTAATTTAAAGTAGCAACCGAAAGTTACAACAAAACTAGTATGTGTAATCTATAC
ATCCCACATTAGTAGTACAGAATAATTTAGTAATAATATATATACATACTTTATAATGGTACGAATTAATCCATTTGAAAATTTGTATGTTACAA
CTTTAGAACATTTGTTTGCCCAAAAATAAGGATTCATATTTTTAAATAAAATTCTTATAAAGGAATGTGTTTAGATGGTTAGAAAGAGCCACCAC
TATCTTAGAATATGTTGCTAAAGTTTCAGCGTTGCAAGCTTATTTCAGAACGTTGCCTCAATCATACTAACGCCCACAACTGTCACTGCTACAGT
TTTGGAAAAGGTTTTGATTTTATCATTTGTCTTGCACATTGTATCGATGTGCCAAAAATATGATGAGGCCAAACATATACAATGGTCATATCCAA
TAGTCAGAAATTAATAAAAACAAACAAGTTTTTAAAAATACCGCACATGCAATTAGTGCGCATAGTGACATCTGCAGTCGCTAAAAGAGACCCA
AGTGTTAAAAGCTTACTCGACTAGAAGCTATAAATGGCGATTAATTCCTCTAAGGGAATACCCTCGATGTCCTTATGAAGGCAGTGGAGTAGCAC
AGAAAGGTAAACAGTACCTACGACTGATTTATTGAGATTTGTGGAAAAAGTACTACAGCCACACTGAAAACTCAACTCTGCTGTTAAACAGCTGA
AGACAAGTAGACAGGCAGACAAACTCTAAAAATGAACGGAAAGTATGTAGTTAGCGCCATCCGAGCTCTCCGGTTGACCAATTTCAGCCAGTGCA
AAGGAGCCGCTAGCAGTTTCACTGTGCGCCACTATGGTAAGCCGCGATAGCCAGAATAAAAACGTGTGTTGCCATTTCATAACATCCCGCGATCG
GCGGTTCTTCTCCTGCAGCCTCTCCTCCCAAGCGATTCTACAAGAAGACTTCCGTACTGAGCGGCGACAGCGGCTATGAAGTGGTGTTGGATCAC
CGGAAACTGAAAACGCCCAAGGGCACACCCTTCATCGTCCGCAGCGAACCCCTGGCCATTGCTGTAGCCACTGAGTTCGACGCTCAGAAGGAAAA
CATCGAGCGTTCCCGCATGCACTTATCCGCGCTCTGCTTCACGGCCATTGACAATCCCAATCACCTCTCCAAGTTGGACATGGTCAACTACCTTC
TCAACTTCATCGCCACAGACACGGTGCTCTTCCAGTACGATGTGAGTGAATCAACTGAGAATTAGAGTGCACATTCCACAGACATATATCTTTTG
CAGGACGAAAAGGACCTGCAGGACCTTCAGGTGAATGAATGGACCCGGTGATCGCCTGGTTCAACCAGCGCTACGACACAAACCTGCAGAAGAC
CATGAACATAACGCCGCCTCAGGTCAGCGAGCAGGATAAAATGAATGTCGCAAAGCATTTTCAGTCCTACAGTTTGGAAACTCTGCATGGTAATG
CAGACCATAAGTCTGGAGTTCAACGTCTATTAAATATATTTTCCTCCAGGCTTCATTTTCGCTGTGGACACCTTAAAGTCGATTGTCCTTGCCTG
CGCCGTCATCGAGCAGATGCTTACCGTGGAGAAGGCTGTGGCCCTGGCGCGTCTAGAGGAAGAATACCAACTTAAGTTCTGGGGTCGCGTGGAGT
GGGCACATGATTTAAGCCAACAGGAGTTGCAAGCACGCCTGGCGGCTGCCGTGCTCTTCGTACACCTTAACTGTTCGGAAAACCTTGTTAAGCAA
AAGATAATTCTTTAAAATTAAAATACCTGTTCAACATACATATGAGCTGACTACCACAGGGTTATGGTAGCACGTATGTAGGTCTCCTAGGACCT
AGGACATAATAATAGATGTATATAAATCGTGCCTAGTTTGAAACTTATCAAGGTCAGGTCATCCTCCCTTTTTTTTTAGCTCTTACCGGTTTTTT
TTTGTTGTAATAATACGGTTTATATTATCATTTTTTCATACTTTCTTTAAGCACGAAAGTAACATACTCTTTTGACGTCTCTTATAACACAACTG
AATTTTAGTTCTGATTTTAATTAGTAAGCCACAAGGATTCTGGTACAGCAATACGTGGAGGCAGTGAACATAAGGAAGTACATTAAGTTTTTTGG
AACTACACATGTACAAATGTGTAGGATATATGTAACATTTTTAAATTTGAATGAGATTACTAAATTTTAGAAATATTTAGTTTGTTTAATCCTAA
TTTAAGGTTCGGTTTTTTTGCACCTTGACATAGAACCCTATTTTTGGAACCCATTGGCAAAACATGGACATTTATTTATCTTACTTAAGAAAAAA
TTAAGTGCTAGTGTAATAGGCGCTTAGAGGAAGTCTCAAAAAACAAAAATAATTAAGCAATTTTTTTTCGTAGGTGTGGTATATTCTGATAAATA
CTTGCTTGGTATTTTAAAATAGTTACGGTACAGTCCTACTGTACACTGCGGTCACACTGGTTCGGACGTGGGTGGCGCATCATCGGTGGTATTCT GTTGCTAATTAATCAAGTGCAAAACTACATTTTTCGCCAGTAAATCCGAGGAAAGCTAAGTTTGCAAGAAAACAAACGAAAGCAAAGGCAGTTGA
TAATATTACTGGCGCGTTTGGTAAGCAGCGTCGTTCGAGTGCGTGATTGTTCCAATGTTTGTGCTGGTGTGCGTTTGTGAGTGCCTTTTCACTAA
AAAAAAATGTAAAAAAAAAGTGTTGCCAAAGCAGTGAGGCATACATTTTCCCAGTCGCTTTGTTTC
(SEQ ID NO: 142)

Exon: 1001..1176
Exon: 1254..1561
Exon: 1619..1799
Exon: 1855..2105
Start ATG: 1077

Transcript No. : CT5298
TACTACAGCCACACTGAAAACTCAACTCTGCTGTTAAACAGCTGAAGACAAGTAGACAGGCAGACAAACTCTAAAAATGAACGGAAAGTATGTAG
TTAGCGCCATCCGAGCTCTCCGGTTGACCAATTTCAGCCAGTGCAAAGGAGCCGCTAGCAGTTTCACTGTGCGCCACTATGCCTCTCCTCCCAAG
CGATTCTACAAGAAGACTTCCGTACTGAGCGGCGACAGCGGCTATGAAGTGGTGTTGGATCACCGGAAACTGAAAACGCCCAAGGGCACACCCTT
CATCGTCCGCAGCGAACCCCTGGCCATTGCTGTAGCCACTGAGTTCGACGCTCAGAAGGAAAACATCGAGCGTTCCCGCATGCACTTATCCGCGC
TCTGCTTCACGGCCATTGACAATCCCAATCACCTCTCCAAGTTGGACATGGTCAACTACCTTCTCAACTTCATCGCCACAGACACGGTGCTCTTC
CAGTACGATGACGAAAAGGACCTGCAGGACCTTCAGGTGAATGAATGGGACCCGGTGATCGCCTGGTTCAACCAGCGCTACGACACAAACCTGCA
GAAGACCATGAACATAACGCCGCCTCAGGTCAGCGAGCAGGATAAAATGAATGTCGCAAAGCATTTTCAGTCCTACAGTTTGGAAACTCTGCATG
GCTTCATTTTCGCTGTGGACACCTTAAAGTCGATTGTCCTTGCCTGCGCCGTCATCGAGCAGATGCTTACCGTGGAGAAGGCTGTGGCCCTGGCG
CGTCTAGAGGAAGAATACCAACTTAAGTTCTGGGGTCGCGTGGAGTGGGCACATGATTTAAGCCAACAGGAGTTGCAAGCACGCCTGGCGGCTGC
CGTGCTCTTCGTACACCTTAACTGTTCGGAAAACCTTGTTAAGCAAAAGATAATTCTTTAA
(SEQ ID NO: 143)

Start ATG: 77

MNGKYVVSAIRALRLTNFSQCKGAASSFTVRHYASPPKRFYKKTSVLSGDSGYEVVLDHRKLKTPKGTPFIVRSEPLAIAVATEFDAQKENIERS
RMHLSALCFTAIDNPNHLSKLDMVNYLLNFIATDTVLFQYDDEKDLQDLQVNEWDPVIAWFNQRYDTNLQKTMNITPPQVSEQDKMNVAKHFQSY
SLETLHGFIFAVDTLKSIVLACAVIEQMLTVEKAVALARLEEEYQLKFWGRVEWAHDLSQQELQARLAAAVLFVHLNCSENLVKQKIIL*
(SEQ ID NO: 144)

Celera Sequence No. : 142000013384171
CCAGCTCCAGCAATTATATAGCCTCCAACGCCAGCAACTCAATCTCGACCAGCGCCAGCAACCCAAGCTCCACCGGCGCCAGCAATCCAATTACC
ACCAGCGCCAGCAACGAATCGGCCAGCAGTCGTCGAGCCAAGTTCAGGATAAATCAGATGAGTCGCGATGTGCCCGTTGGGCTGCCGGACACTCA
TCAAACCGTGAATCTGGAGGAGGCGGCCAACACCACCAAGGATTGCCTGCTGCATTTGTTGGAGAAATACAACGAGACCCGCATCCGCAATCCGG
TGGGTCGTCACCAGAGCATCAGCGTGGACTGGCGGGTCAGCGACAATCTGGAGTACCGCTCCATGAGCTCCATCAACGCCTTCTTCCAGCGCCAC
AACCCCAATGGCGGCGGCCACAACGTACGCCACATTCAAGCCCAGCTGGAGGAGAAGGCGGCGGGCAAGTAGGTGCCCATATCCACAGCCCTCTG
TATATATGCGATATATATATTTGTATGTAGAGTACAGATCAACTAATTGGCACATAGGTAAATCTACAAAGCGTCGAATGGAACAAATTAATATT
TATGTACTTGATGTAAGCAATAAATCAAATTAATTTATTGAATAAAACTGAAGCAATGATTCGTTTCTATTGACGCGGGATTGAATTTTGTTGGC
ATCCCACGATATTTTATAAAAATGAAATTAAAAATTAAAAACGCGATTTATGTACTACCAACTAGAAAATCAAAAACAATTTATTGCAGAAAAAC
AAATATTAACTTATAAAATGTACAAAATTGTTTTAGTAAACTACATTTTACTGCTACGTCTACAACCAAAGTAATGCGGATGTGTTGGTAATTTT
GAAACAGGACAATCGCGTTGTTTTTGTTTTGTTTATTGATGTATGAGTTGAATATGGTTTAATTATACATAGAGTGTCTATACATATAAATATTA
GGAGAATACTTTGGATTTGTTCTTAGTTAGGCCTTACAAATTAATGCTTTGTATAAGTGTTATGAAGAATAGGCTCTGCCTATGTGTATAGTATG
TATAATAATCTAGTTTTTGTACATGATAGTTTCAGGCAAAATTGTTTTCATAATTTGCCCAGAGATCATAGCAAATCATAAAAGACATTTTTAGC
ACTGGTTAAGAAATGAGAGCGCGACAATTTGTGTCCATTCGGCGGCATTCATATAAATAAGGCATCCAAACGTGCAGAAATTGACGAAGTTAATT
CAAAGGCATTCCTCTTTTTTTTTTTTGTTTTCCACTGGTCGAATTGGTTACAATGTTAGTAGGTCGCAAAAACAAAGCAGCAATGAGCCGAAATG
CGGCTTATTGGGGCATCGTTTTGGCGCCCTTAATATGCAAGACAAAACTCAATTCTACTCTCCCCTCAGTTTCAGTACTTGGATGAAGTGGCAGG
GCAGAGAAAGGATGAGTTTTGTTCACCCGGCAAATTTCAAATGCAAAAGTTGCCGGCGAAATTTGCAAGGATTTCACAAAGTTATGTAAAGTTAG
TATTCCATCGTTATAAAGGTTAAATTTCGGTTGGCTTCAAGATAGTTAAGACTAATTCCATTTAGCTTGCGGTCTCTCTCTTCTTGTTCAATAGT
TGTTTGTTGTTAAGAACTAATCACTTAGTTTATGGCATTTCTCACTAGAGAAATCTAAAAAGTTTCATTTAGCTCGAGCTTACTGGTTGACTTAC
AACTAATTACTGGTTACGAGTAGTTGAAGACTAACGATTAATATTCGCAACTGTCGCCCTTGCACTGCATAAAAAGGTTCGTAATAAAAAATTAG
GAAATACTACACAATCGCAGTGGCTTGTAAAAAATAAAATTACAAATTGCAATTCGGTGGGTTGGCCAGCGAATCTGGAGCATTAGTTGTGGCGC
GGCCGCTTCAACATCGCCCCAAAGTGTGCCCCCAACCCAAATCCACCGCTGGAGCTGGAGCTGGAAGTGGCGGACGAACTGGGAGAACTGGTGCG
CATGCGCTTTGCGGGCGATAGTTTCTTGGGTGCCTGGGCCAGACGTTTGCGCTCCTTCATGAATTCTGTAAACAAAGGAAGGAAAACGAGTGTTA
TTAATACGTGTTAGGTGGAATTGCCAAATCAAAGTCAGCTGCTGCATTTCCGGTTGCCCCTGTTCACAAGTCACTGATCCCTAAACAGCAGGCGC
CGCCTGTTTTTCTGTTTTTGCACATTTTGATTTCGGTTTCGGGTAGATTCCCAGATTGTGGCACGTGGACGGCAGCACTTCCCTACCAGAGGGTT
GCAGATCCGCACAGGGGTAGCAAATAAATGCCAGACGGCAGCCAGACAGTCGGTCTTTAGCCGGTTTTCAGGTAGTCCGGTGAAAGCAAGAGTGG
TGGTGCTACATAACTGCATAAATTATGAGCTCTAGCTTACTGGCCAAAGCAGCAAAAAGTGCACTTTAAGTAAAGCGAGTTGAGGCGTTGGGGGA
TTCAAAGGCTTCCCTACTGACCACCCGATGCGGGTGCATTTATTATGTTCCGAACAGACACAATTTTTTTATGATTATAATTACACATGCATGTG
CTAGTGGCATTTATAAAAAACGCTCAGTACAAAGCAATCAAAGGGAGGTTTGATAAGACCATGGACTCTGGATGGTGGTGCATTGAAAGCCGATC
CCCAGACCCCTCTCCCGTTTTCTATAATGAGGTCAGGCCATAGACAAAGCGGAGTCACAGCTGTTGGCATTTATAGATGCAGCCAGCCAGCCCGC
ATGCTATCGATCTGGAAACCAACCCCCGCGTTGTGGAGGATCAGAAGAGAATCATTCGGTTTAGGGAGATGAGGAGCTGAAACAGCTGCAGTCAG
CTTTGACTTACCCTTCTGGACGAAAATAAATCTCCCACAAAGCATTGGCTAATTGCTATAATTTGGGTCTAAGTTTCACGAAAAACGCCCACAAC
TAAAACGTGAATATAAACAATAAATGCGAAGGAGTGGACTTAAAACCAATCAAACAACCCCTTATGGAGTTTAGTATTGTAAGTACAAAATCCTG
CACAAAATATTGGTTTGGCATAAAATCATTGATGAAAATCGTTTTCATCGAGTTTGCAAAACAAAGAGCACGAATCTACTTTTATATCTCGAGCA
CTATATTCGGAAATTTTTAGATAATACTCTCTACTCTACAGATAATTTTGAAAAATAATATCGTATCAGTCCGATTACAAAACAAGCCTGATAAG
TTAAAAAAAAAAAAAAAAACACCCTCAACTTCCTCCTGAGAACCGAAAATAAACAGGGAATAAAAGGAAAGCTATGGGAAAACACTTTGTAACGTC
TATCGAAGTGAAATGAAGCCTGACCCTGGGAACCGTCAAGCTCTACTGATCAAAATGGTGTAGAACATCCCCCAAAACTCACCTGTGATTTTTGG
CTGTCTCTTGCGCAGGACTATGGAGGATGTGCTTGTCGTGCTGGAGGAGCTAAGCCGCATTGCCAGCGACTCGTCCTGGGAGTCGTAACAAGATT

FIGURE SHEET 66

CATTATCCGTGTTCGACTCTAGCGAGGAATTGACCAGATTGGAGCCAAAGTTCTCCCGTTCTGAGCGCTCGTTGACCAAAATGTCCATGTCGCTA
GGACTTGCATCCGCGGAAGGGCGTACGTGGGCGGCCCGTGTTAGGGTGTACATCTCTGGGGCGAAGCTCGACTCCTGGAAGCTGACGCGCTCCCA
AATGTAGGGTGATTTTTCAGCTAAAGGGCAGCCGGCGCGGAAGTCAAAGCCCCATTTTTGCGTGGCCAGTTCTTGATGGCGCTCCAGTTCGGAAT
TAAAGGGTCTAAAGAGGATATATTGTTAGCTATTGGTCAAAATCCAACTGTTATTATAGAAACTCACGTTTTGTTGGCTGTACCCTCGGCGGATT
TGGAGCTACCGAAGAGGTCACGCTTTATGCGATTCAACTGACGACCGCATGCCAGATTGCGACTCACCGCCGGGCTGCTGCTCATCTTGCAGAAC
TCACTGATCATCACAGGATTCAGGACTCGGGCACTGACCATGTTGAGTCAATATATATTTTTTTGGGATCCCCTAGTGTTTTCTACTCTGTTTTG
AGACGCACTTTTCTTGCCACTTGTTTGCGAATTACACGCCAAAGCGAACTGTCAAACTTTTGGCGCCAAAACTTTGTGTTCAGACAGCCCCAAAA
GAGAGAGAGGCAGTCTCCACACGAATACAAATCACGGTCTCCACACGCGAGCGTGTGTGTATGTGAGAGGGAGAGCGAGTGTTCTGTGTGTGCGT
TGTGCTGCAGCTTATTTTACGTCTTGCTGCGTTCAAAAGTGAAATTTCACGCTGCAATTGTTTATAAAAATAATTATAAACAAATGCCTTGGTCC
AATAGCACTTGGTCACTATCTTTGAATGGCGATTCGAACACACTGCACTGCTAGTCGACTCACAAAACGAAACGTTTGCGGGTCTCGTTGGAGTT
TTTGTATGAGTTAGCTGCCAATGGCAGCACCTTTGTATTATATTTGTCTTTACAACTTGAAGTCGTTTTTACAGCGATGTTTGTTAACCTTTTCG
GCTATGAGCGCACTGCGCACTAGATTTTTAAATATAGCGCTACCGATCGAAGCGAACCTCTCTCGACGAACTCGGAGAAACGAATAAAAGATAAA
TAAAACACTGGGCAAAAGCAAACGTCAAACAACCACCAGAGGCGTTGCCAACTGGAAATTCAGAGCGGTTCACGCTCTCTCTGTAGCAACCCTCG
AATTCGAAAAGATCGGAAAAGCAGCAGGAGCGAAAGAGATAGGGAAAAAGAATGCGCTTTTAATGTTAATCATATCGAAAGAGCAATGCACTTCC
TTTGAATTGTTCTTTAAACTTATATAGCAAACGTATAAAAAATACTCAGAAAAATAAAAGTTTCCTAACAAAATTTAACTAAGGCATCTGAGTTT
AAAAGTTTTGATATTATGAGCTTTAATATAATTATTGATTGTTGGAATCATCATATAGTACAATATATAATACGTATTCATTATTATTATTATTA
TTATTATTATCATTATTTTCATTATTTCCTGTCAAATAATATTCACAGCTCATAAGCCCATAGTTCATTTGTAAACAGTATTCAACCAGATTTTA
TTTTTAATGTTTTTGAAATAACCAATTTAATTATATTTTAAACTGTCCAAGGTTCCTTCATAGAGCGTATCAAGAAAGTCGTCACAACTTCCACA
ACCTCTCTCTCTCTCACCATATGTCTCCCACTCTCTCGCACGCCATCTACCCATCCCTGCCATTTCCATCCGTGTGTTCTGTTCGCTGCCTTCTT
GGTTGTTGTTGCATCGGTGGAGCTGTACTTTTAGTTGCGATTGCGATGGGAAGATACGAAAAAACGATGTTATGGTTTTGGTTTGTTTGGCCTCA
AACTGGATTTTTAGTCGTCGGAGGGAAGTGGCAGGGGGCATTTGGGGCACCAATTCTTTTCACTTTCCTCGTGTTGCCAAGGGGAAAATCGCGCT
TGCATTGTGGGGCACTGGTCCACCAAATATACATTTGTACGATGTATGTATGTATGTATGTAAAATAATGTGCACGTCTAGTTCGAATTTCCTTG
TGGTGTTTGCATAGCACTGGGTATTTCAAATTTCCGTTAT
(SEQ ID NO: 145)

Exon: 4645..3868
Exon: 3808..3408
Exon: 2060..1001
Start ATG: 4031 (Reverse strand: CAT)

Transcript No. : CT5316
ATTCGTTTCTCCGAGTTCGTCGAGAGAGGTTCGCTTCGATCGGTAGCGCTATATTTAAAAATCTAGTGCGCAGTGCGCTCATAGCCGAAAAGGTT
AACAAACATCGCTGTAAAAACGACTTCAAGTTGTAAAGACAAATATAATACAAAGGTGCTGCCATTGGCAGCTAACTCATACAAAAACTCCAACG
AGACCCGCAAACGTTTCGTTTTGTGAGTCGACTAGCAGTGCAGTGTGTTCGAATCGCCATTCAAAGATAGTGACCAAGTGCTATTGGACCAAGGC
ATTTGTTTATAATTATTTTTATAAACAATTGCAGCGTGAAATTTCACTTTTGAACGCAGCAAGACGTAAAATAAGCTGCAGCACAACGCACACAC
AGAACACTCGCTCTCCCTCTCACATACACACACGCTCGCGTGTGGAGACCGTGATTTGTATTCGTGTGGAGACTGCCTCTCTCTCTTTTGGGGCT
GTCTGAACACAAAGTTTTGGCGCCAAAAGTTTGACAGTTCGCTTTGGCGTGTAATTCGCAAACAAGTGGCAAGAAAAGTGCGTCTCAAAACAGAG
TAGAAAACACTAGGGGATCCCAAAAAAATATATATTGACTCAACATGGTCAGTGCCCGAGTCCTGAATCCTGTGATGATCAGTGAGTTCTGCAAG
ATGAGCAGCAGCCCGGCGGTGAGTCGCAATCTGGCATGCGGTCGTCAGTTGAATCGCATAAAGCGTGACCTCTTCGGTAGCTCCAAATCCGCCGA
GGGTACAGCCAACAAAACACCCTTTAATTCCGAACTGGAGCGCCATCAAGAACTGGCCACGCAAAAATGGGGCTTTGACTTCCGCGCCGGCTGCC
CTTTAGCTGAAAAATCACCCTACATTTGGGAGCGCGTCAGCTTCCAGGAGTCGAGCTTCGCCCCAGAGATGTACACCCTAACACGGGCCGCCCAC
GTACGCCCTTCCGCGGATGCAAGTCCTAGCGACATGGACATTTTGGTCAACGAGCGCTCAGAACGGGAGAACTTTGGCTCCAATCTGGTCAATTC
CTCGCTAGAGTCGAACACGGATAATGAATCTTGTTACGACTCCCAGGACGAGTCGCTGGCAATGCGGCTTAGCTCCTCCAGCACGACAAGCACAT
CCTCCATAGTCCTGCGCAAGAGACAGCCAAAAATCACAGAATTCATGAAGGAGCGCAAACGTCTGGCCCAGGCACCCAAGAAACTATCGCCCGCA
AAGCGCATGCGCACCAGTTCTCCCAGTTCGTCCGCCACTTCCAGCTCCAGCTCCAGCGGTGGATTTGGGTTGGGGGCACACTTTGGGGCGATGTT
GAAGCGGCCGCGCCACAACTAATGCTCCAGATTCGCTGGCCAACCCACCGAATTGCAATTTGTAATTTTATTTTTTACAAGCCACTGCGATTGTG
TAGTATTTCCTAATTTTTTATTACGAACCTTTTTATGCAGTGCAAGGGCGACAGTTGCGAATATTAATCGTTAGTCTTCAACTACTCGTAACCAG
TAATTAGTTGTAAGTCAACCAGTAAGCTCGAGCTAAATGAAACTTTTTAGATTTCTCTAGTGAGAAATGCCATAAACTAAGTGATTAGTTCTTAA
CAACAAACAACTATTGAACAAGAAGAGAGAGACCGCAAGCTAAATGGAATTAGTCTTAACTATCTTGAAGCCAACCGAAATTTAACCTTTATAAC
GATGGAATACTAACTTTACATAACTTTGTGAAATCCTTGCAAATTTCGCCGGCAACTTTTGCATTTGAAATTTGCCGGGTGAACAAAACTCATCC
TTTCTCTGCCCTGCCACTTCATCCAAGTACTGAAACTGAGGGGAGAGTAGAATTGAGTTTTGTCTTGCATATTAAGGGCGCCAAAACGATGCCCC
AATAAGCCGCATTTCGGCTCATTGCTGCTTTGTTTTTGCGACCTACTAACATTGTAACCAATTCGACCAGTGGAAAACAAAAAAAAAAAAGAGGA
ATGCCTTTGAATTAACTTCGTCAATTTCTGCACGTTTGGATGCCTTATTTATATGAATGCCGCCGAATGGACACAAATTGTCGCGCTCTCATTTC
TTAACCAGTGCTAAAAATGTCTTTTATGATTTGCTATGATCTCTGGGCAAATTATGAAAACAATTTTGCCTGAAACTATCATGTACAAAAACTAG
ATTATTATACATACTATACACATAGGCAGAGCCTATTCTTCATAACACTTATAC
(SEQ ID NO: 146)

Start ATG: 615 (Reverse strand: CAT)

MVSARVLNPVMISEFCKMSSSPAVSRNLACGRQLNRIKRDLFGSSKSAEGTANKTPFNSELERHQELATQKWGFDFRAGCPLAEKSPYIWERVSF
QESSFAPEMYTLTRAAHVRPSADASPSDMDILVNERSERENFGSNLVNSSLESNTDNESCYDSQDESLAMRLSSSSTTSTSSIVLRKRQPKITEF
MKERKRLAQAPKKLSPAKRMRTSSPSSSATSSSSSSGGFGLGAHFGAMLKRPRHN*
(SEQ ID NO: 147)

Name: cyclin-dependent protein kinase inhibitor
Classification: enzyme_inhibitor
Gene Symbol: dap
FlyBase ID: FBgn0010316

Celera Sequence No. : 142000013384447

FIGURE SHEET 67

GCGCAGGAATTCCCTAATGTTCCCGACCTACATGTACTTCTGATAGTTGCCGAGGTCAAATGTTGTTGTATTTGTATTATACCTCAATATTGGTA
TATTCAATATCTAATAGTACCCAATTCAATTGCAAAGATAGTCATTAAAAAAACCTAAATCACTTGCAAATTGACTTTTCTGCCGGAAAAGCAAC
CTTGACACACAAAGTTAATTAGTTTATCTGGAAGTCATGTGAGAAATTTGTAAATAAATAAATAGAAAATTTTTCGCAGTAATTTAAGTGGGCCT
AATCCCTTTTAAGCATCTTGGTTTTACGATGACACCGCAATAAGGTACAACTTTATATTGTTTTTGCAATCAGCTTGAGTCTTTATTAGGCATCA
GTCTTTCTCTCTAAGTTTCTTCGTGCAATAAATGAGGTTCCAAACTCCGTAGATTTTTCCTTCTTTGTTGAATCCAGATCCTGCAAAGAAAAAAG
AGCAAACCCCTAGGTCTGTCCAGGAATGTATTTTCGTGTTTGTCGACGGTCTGAGCTTTGGTGAAGCGTGAAAATGTGGCAGTCACTGAGTGGAA
TCGATGGGGGGATTGACGCGTGCCCAACTGGTGGGCCAAACACTTCGGATTGCTACGGTTCGTATTGCTATTGAGCCAAAGGGACCCGGAGCGCA
TCACTCCGGTCCAAAATGTAGGCGGATGTGTGTCTGTTTCGGGGAAAGATGGTCTTCTGTCGGCAAGACATATACATAGGTGTTAAATATGATTG
CATTAGTTTTATACTACGTATAAGGAAGCTTTGATTGGATCGAAGCGACTGAAGGCGACCCTCGTCCTTGAAATTCGGTAGCAGTGATTATAACT
CATAGCCCCCATTTGGAGCTAGGCTCCGCTCAGGTCTTTGAAAGTCTTGGGGGGCACAGTGCCCCTTTGATTTTCGGTTTGCTTTTGCTAAGTCC
AACTCTCGTTTTTGGAACTTTTGGGGTGGTGGATGGAGAAGGGGGCTTTGTGGGGTTTGGCACACACGATACACACATCACTGATTGATCACTGC
TCATGTTAACTTAAGTTCGTTCATGGTGTTGTTGTTGGTTGTGGTTGTTGTTGTTGGGCGTCTCTTTAAAGTCTCTTTCTCTCGCTTTCTCTCGC
TACTTTTCGCTTTGGGAGGTAAATAAAGTTCACATTTTCTCTCTTTCATTTTGTATTTTTGTGGTTTAAAATATTTAATTAGCATTAAGATCTCT
GCTGTATTGAAATTTGCTTAAGTCGTAAGTTTGTTTTTAATCTTAGTGTGGGTGGTGGGGGTGTTTGGTGAGCGGGACAGAGAGAAAGGGGAAAG
AGAGTTGTATCGACTTTAGACGATAGCCGGTTTTATCATATTAACTTTTTGCTTATACCGTAACGCATTCAATATTTCTCTTTAGATTTTCACAC
GCGAGAGGATTAGGATTACACTTTCCGATTCTAGCGAGGCCAGGAGCACGATCTCGTTTTAAACCTCGATGCGGCCTAGCGCCTGTTGTCCCGAT
AGCTTCGCTGGCCGCCGCCGCCGCCACGCTCGCGAAACGGTCGCGAATCCCGCGAAGATCCGCCGCCACCGCTGCGATTTCCGTACTCCCGTCGA
CGACCGCCCGCGGAGCCGTTGTTGCCGTCCCGATTCCGATAGCCGCCGGGTCCACCCATACCGCCACCGGATCCTCCACCGGCTCCCATGCCACC
GCCCGCAGCCGCCGCCTGGGCAGCAGCTAACCCGCCAGCTCCATTGCTACCGCCATTGGCTGCTCCGCCGTAGACGGGGAAGCCAGGCGGTGGCA
CTGTGGGTAGGCCAGCATTCTTCCAGGCAGCAAACTCCTCGTAGCTCGGCGCCTTGTCGAAGCCCGGTGGTGGTGGTCGCTGGGGAGGCGGATAA
TCCGGTAGAGGCGGGGCACCGGGTCCATCGTAGTACCGCACCGGTGGCGGCAGCTGCTCGTACATGGCAGCTGCTGCTCCCGGTGGAAGGGCACC
TGCTGCTCCCGCTCCAGCTCCTGGAATCGGCAGCTGGGCGAACGGAGGAACGAAGGGCAACGGCGGAAGTTGGCCGTGCATGTTGCGCATGTAGT
CCGCCACGTATGCTTCAGCAGCTGCCGCCGAGGACATGTAGCGTTCCCATGACGGCATGGCCATGTCGCCCGGTCCGCCGGGTGGCGCTCCTGCT
GCACCTCCCATCTGGCGGTACGGGGAACCGCTTCTTTTAAAGCCACCGCCCGGCGGAAGGCCCATGCCATGATGGTGACGGTACGGCCGATGGTG
TGGTGCTCCGTGGTAGCTCCTCTTGTGCCGCATCGGGCCCAGGTGGTCGTGATTTGATCCTCTGCCTCCGCCACGACCTCCCCCTCCATGGCCAC
GCGAGGATAGACTCCTGGGCGGCTTGTAGATCACGTGTATACCTTTTTCTCGCATAACTCGAGCCGTCTCCTTGGATTTCTTGAGTATGGGAGTG
AGTTCGATTTGTTCATCCTCGGGAAAGAGACGACACAGCTCGCCGCCAATCTTGGGCTCAATCTCCTGGCCATCGCGACCGATCTTCACCGGCTT
GCCCTCGTTCCAGGTGTTGTGCAGGTGCAGGGTGGCGTTGAAAGACAATTCCTTGCGGCAGATCCAGTCAAGCTCGATGACGCCGCCCAGTGCCT
TGGGCGAAATACTAGGCGGCAATACCCAGGCCACCTGAGGAATGTCCCGCCGTGAGGGGGCTGCCATCCGGGCGAATCCTGCAAATTTACCTAAA
AGCAAAATCGGATTATAATAGAGGTTTTGAAGACATAGACATTGTATGTATCTTATTCTTAAGAAACTAAGAAAGTATAAGAAATGAGAAACATT
GTTTACTCCTTGAACCTACCACTCTCGTTGACCGAGAAAATGAGCAGGACGTTTCTGGCCTCCTTGAAAGCCTGGTTAAGATTGGCGTCGTTCTG
CGGCAGCGTGGCCCACACACTCTTGTTCTTAGACAGCTGGACGTTGTCGCTATTGTTCGACTTGATGAGGAAGAACCGTGTGTCTCGGAATAGGT
AGTTCAGCTTGGTCATGTAGTCGTAGCCCTTCTGCGAATGTGAGTGCGTACCGCCACCGACAGAATCTTTTTCCGGCGTGGAGCTCTTGGAACTG
GGTTTGCCCCGGCCGTTGCCGCCACCATTTCCTCCGTTTCTCTTGTGCTGAGTGCCCGAATCCGAGTCAGAGGACTCGCTGTCGGACTCCAAAGT
TGGAAGGCTTGGTTTCTCGTCCTCAGCCTCGCTGAGATCGCTCTTGTGGCCAGCAGAATCGTTGGCATTGGAGGGTATCTTGGTGCGCGACTTCT
TGGCGGACGGCTGTCGATCCTCGGTATCCGGGGATTTGGATTTGACCTTATCCGACGCCTCAGATGAGGTTGTTTTCTTCGTCCCGCTATCCGTG
CGCTTCTTTTTCTTCCCACCATTTAGCTCCTCGGGAGTGGGTTCCCGTTTGGCTTTGTTCTTGGCGGAAGATTTGGAGGATTTGGTCTCGACAGC
GGGTTGAGGGCTTTGCTTGGCAGGCTTCTTGGTTTTCCGCTTGCTACTGCCCGCCAGGGAAGATGTGGCAGTGCTGACGGAGCTGATGCTCGGCT
CCGAGTCGGATGAGTCTCCACCATTCGATTCGGAAGCCTCACTCCTTGTGTTGAACTCAAAGTCTTGCAGCTCCTCGGCAATGTCCGCCTCGTTC
TCGTCGAGGCCCAGGTGCACTGCATCCAAGTCCGCCATCTCGCGCATCGGCAGCGTTTGTTTACCTGCTCCGAAATCGGAAATCGGAGTACCAGA
TGAATGGAGCACCCACGCACACGCACACACGCAAACCAAGAAAAATATATAGAGAAAAAAGCCGATCGATCGGCAAGGTAAGAAAAGGTCAGGGA
AATACAGGTATTCCCAAACTCACGGGCTGCTCTTGGCATTAATTGTGTGGACACCGGTCTAGCGCCACTTTTTGTTCACTTTTAACGCAATATAT
CCCTTTAATATCGCGAAATTACGCCAATTTTACAATGCTTACACACAAATTCTGCGTCACAGCGGCGACGAATTGGCGATGGCGTCAGAAGAGTG
CGGCTATATGTCTGCAGGCCGCGACTATCGGACCACTATCGATAGGCGGATGCAGCTGAAAAAGGTAGCTAGAAATAGCTGAAAATGCACTGCAA
TCGGTTATGTTATCGTTCCTAACGAAGCGAGGTAAACAAAATGCACCACAATCAGTCGGATTTCCCGACTTTTCCGCTTTCCTTGCTGGACGACA
GCGATCTAGAGCCACAGAGATGTTATATACCCGCGTGGGAGAACTCTACTGGAACTGGATGGTACCGTTGTCACCTTTGCGATGGCAGCTACGCA
GTTTGTTGGGTAACTCCGCGTGCAGGCAGTGAAACTTGTTGCTTCCTTGATGGAATTGTAACCTCCTTGACGCGGTTCTCCCCCACCAATCAGCG
GTTGGTGCTTCTGGAGCCACTTAAATTAGTTCCCTGCGTGAAGAGGATTTCATGCGTGATTACAGTCACCCAGGAGCTCCTTCAGCGACCTCCGG
TTTCCCTGGAGGATCTGAAGGACGATGTGCGAATCTTCCTGCGCCACCTGAAGCTTACCAAAGGATGCTCCGTGCAGCACAGACGCCTTGTGCAG
CTGGGCATTGCCAGTGTGGAGATATTCGATGCTCCAGGAGTTGCTGATGACGAGTGTTTTGAAATAGCCCACGATGCTGAGCTACTCCTGGCGGA
CATACGCCTGGGAATGCCCTTTTCTTTAGATTTTATCTTCAAGTATTTGCCACACAGCTTCGAGCGACCCATGGAGCAGTTGGAGAAGCTCCTGG
AAACCTCTAAAATCAGCTTTTCGCATAGATTTCCTACTACAGCATTGGTTGTGGGTCCGGTGGACTGTGGAAAAAGTGGTCTACTCAGTGAGTTC
CTGCGTCGTCATAGCTGCAACTGTTTTTACATTACAGCCAGCCAGGTGCTGCGCTCATATCCCGGCGAAACCGAAGAGGAGTTGAGGAGGATCTT
TCAGGCTGCTCAGACTTTCAAGGAGAAACTA
(SEQ ID NO: 148)

Exon: 4066..3919
Exon: 3772..2870
Exon: 2750..1001
Start ATG: 3934 (Reverse strand: CAT)

Transcript No. : CT5320
CCAATTCGTCGCCGCTGTGACGCAGAATTTGTGTGTAAGCATTGTAAAATTGGCGTAATTTCGCGATATTAAAGGGATATATTGCGTTAAAAGTG
AACAAAAAGTGGCGCTAGACCGGTGTCCACACAATTAATGCCAAGAGCAGCCCCAGGTAAACAAACGCTGCCGATGCGCGAGATGGCGGACTTGG
ATGCAGTGCACCTGGGCCTCGACGAGAACGAGGCGGACATTGCCGAGGAGCTGCAAGACTTTGAGTTCAACACAAGGAGTGAGGCTTCCGAATCG
AATGGTGGAGACTCATCCGACTCGGAGCCGAGCATCAGCTCCGTCAGCACTGCCACATCTTCCCTGGCGGGCAGTAGCAAGCGGAAAACCAAGAA
GCCTGCCAAGCAAAGCCCTCAACCCGCTGTCGAGACCAAATCCTCCAAATCTTCCGCCAAGAACAAAGCCAAACGGGAACCCACTCCCGAGGAGC
TAAATGGTGGGAAGAAAAAGAAGCGCACGGATAGCGGGACGAAGAAAACAACCTCATCTGAGGCGTCGGATAAGGTCAAATCCAAATCCCCGGAT
ACCGAGGATCGACAGCCGTCCGCCAAGAAGTCGCGCACCAAGATACCCTCCAATGCCAACGATTCTGCTGGCCACAAGAGCGATCTCAGCGAGGC
TGAGGACGAGAAACCAAGCCTTCCAACTTTGGAGTCCGACAGCGAGTCCTCTGACTCGGATTCGGGCACTCAGCACAAGAGAAACGGAGGAAATG
GTGGCGGCAACGGCCGGGGCAAACCCAGTTCCAAGAGCTCCACGCCGGAAAAAGATTCTGTCGGTGGCGGTACGCACTCACATTCGCAGAAGGGC

FIGURE SHEET 68

TACGACTACATGACCAAGCTGAACTACCTATTCCGAGACACACGGTTCTTCCTCATCAAGTCGAACAATAGCGACAACGTCCAGCTGTCTAAGAA
CAAGAGTGTGTGGGCCACGCTGCCGCAGAACGACGCCAATCTTAACCAGGCTTTCAAGGAGGCCAGAAACGTCCTGCTCATTTTCTCGGTCAACG
AGAGTGGTAAATTTGCAGGATTCGCCCGGATGGCAGCCCCCTCACGGCGGGACATTCCTCAGGTGGCCTGGGTATTGCCGCCTAGTATTTCGCCC
AAGGCACTGGGCGGCGTCATCGAGCTTGACTGGATCTGCCGCAAGGAATTGTCTTTCAACGCCACCCTGCACCTGCACAACACCTGGAACGAGGG
CAAGCCGGTGAAGATCGGTCGCGATGGCCAGGAGATTGAGCCCAAGATTGGCGGCGAGCTGTGTCGTCTCTTTCCCGAGGATGAACAAATCGAAC
TCACTCCCATACTCAAGAAATCCAAGGAGACGGCTCGAGTTATGCGAGAAAAAGGTATACACGTGATCTACAAGCCGCCCAGGAGTCTATCCTCG
CGTGGCCATGGAGGGGGAGGTCGTGGCGGAGGCAGAGGATCAAATCACGACCACCTGGGCCCGATGCGGCACAAGAGGAGCTACCACGGAGCACC
ACACCATCGGCCGTACCGTCACCATCATGGCATGGGCCTTCCGCCGGGCGGTGGCTTTAAAAGAAGCGGTTCCCCGTACCGCCAGATGGGAGGTG
CAGCAGGAGCGCCACCCGGCGGACCGGGCGACATGGCCATGCCGTCATGGGAACGCTACATGTCCTCGGCGGCAGCTGCTGAAGCATACGTGGCG
GACTACATGCGCAACATGCACGGCCAACTTCCGCCGTTGCCCTTCGTTCCTCCGTTCGCCCAGCTGCCGATTCCAGGAGCTGGAGCGGGAGCAGC
AGGTGCCCTTCCACCGGGAGCAGCAGCTGCCATGTACGAGCAGCTGCCGCCACCGGTGCGGTACTACGATGGACCCGGTGCCCCGCCTCTACCGG
ATTATCCGCCTCCCCAGCGACCACCACCACCGGGCTTCGACAAGGCGCCGAGCTACGAGGAGTTTGCTGCCTGGAAGAATGCTGGCCTACCCACA
GTGCCACCGCCTGGCTTCCCCGTCTACGGCGGAGCAGCCAATGGCGGTAGCAATGGAGCTGGCGGGTTAGCTGCTGCCCAGGCGGCGGCTGCGGG
CGGTGGCATGGGAGCCGGTGGAGGATCCGGTGGCGGTATGGGTGGACCCGGCGGCTATCGGAATCGGGACGGCAACAACGGCTCCGCGGGCGGTC
GTCGACGGGAGTACGGAAATCGCAGCGGTGGCGGCGGATCTTCGCGGGATTCGCGACCGTTTCGCGAGCGTGGCGGCGGCGGCGGCCAGCGAAGC
TATCGGGACAACAGGCGCTAGGCCGCATCGAGGTTTAAAACGAGATCGTGCTCCTGGCCTCGCTAGAATCGGAAAGTGTAATCCTAATCCTCTCG
CGTGTGAAAATCTAAAGAGAAATATTGAATGCGTTACGGTATAAGCAAAAAGTTAATATGATAAAACCGGCTATCGTCTAAAGTCGATACAACTC
TCTTTCCCCTTTCTCTCTGTCCCGCTCACCAAACACCCCCACCACCCACACTAAGATTAAAAACAAACTTACGACTTAAGCAAATTTCAATACAG
CAGAGATCTTAATGCTAATTAAATATTTTAAACCACAAAAATACAAAATGAAAGAGAGAAAATGTGAACTTTATTTACCTCCCAAAGCGAAAAGT
AGCGAGAGAAAGCGAGAGAAAGAGACTTTAAAGAGACGCCCAACAACAACAACCACAACCAACAACAACACCATGAACGAACTTAAGTTAACATG
AGCAGTGATCAATCAGTGATGTGTGTATCGTGTGTGCCAAACCCCA
(SEQ ID NO: 149)

Start ATG: 133 (Reverse strand: CAT)

MPRAAPGKQTLPMREMADLDAVHLGLDENEADIAEELQDFEFNTRSEASESNGGDSSDSEPSISSVSTATSSLAGSSKRKTKKPAKQSPQPAVET
KSSKSSAKNKAKREPTPEELNGGKKKKRTDSGTKKTTSSEASDKVKSKSPDTEDRQPSAKKSRTKIPSNANDSAGHKSDLSEAEDEKPSLPTLES
DSESSDSDSGTQHKRNGGNGGGNGRGKPSSKSSTPEKDSVGGGTHSHSQKGYDYMTKLNYLFRDTRFFLIKSNNSDNVQLSKNKSVWATLPQNDA
NLNQAFKEARNVLLIFSVNESGKFAGFARMAAPSRRDIPQVAWVLPPSISPKALGGVIELDWICRKELSFNATLHLHNTWNEGKPVKIGRDGQEI
EPKIGGELCRLFPEDEQIELTPILKKSKETARVMREKGIHVIYKPPRSLSSRGHGGGGRGGGRGSNHDHLGPMRHKRSYHGAPHHRPYRHHHGMG
LPPGGGFKRSGSPYRQMGGAAGAPPGGPGDMAMPSWERYMSSAAAAEAYVADYMRNMHGQLPPLPFVPPFAQLPIPGAGAGAAGALPPGAAAAMY
EQLPPPVRYYDGPGAPPLPDYPPPQRPPPPGFDKAPSYEEFAAWKNAGLPTVPPPGFPVYGGAANGGSNGAGGLAAAQAAAAGGGMGAGGGSGGG
MGGPGGYRNRDGNNGSAGGRRREYGNRSGGGGSSRDSRPFRERGGGGGQRSYRDNRR*
(SEQ ID NO: 150)

Classification: known_flybase_gene
Gene Symbol: BcDNA:GH01918
FlyBase ID: FBgn0027616

Celera Sequence No. : 142000013384171
ACACAATTTTTGAATTGTTTAGAAAAATAAGAACGATCTATTAAATGGCATAATTCAAAAATATCAAGTTTAAGCCATATACATGTATAAGTTAC
TTTTAAGTTTGACCAGTACAAAGTATATAGGAATTTATAATGGGGAAGCCAAGCTATATTATAATGAATAATTATTATTATTATAATGAATAATA
TCAAGATATCAGGGTTGTGCTTGCACCACAATTATGAAAAATAAAGTAATGACCCAGAAGTCTGTTATCATCTATTTATAAGCAGTTTGAAACAA
ATTAAAACCCACTTTAAATTTTATCAAATAAATATATTACCAATATACATTTAAATTTCGAACATTACATAGCAAAAAAATGTCAATTGAAATCA
ACAAATTTTTGAAAATGCGAGCCATATTTTCATTAAACGAGCTTGTATTTTTTGAACCCGAACCGTTTTTTTTTTCAAGTTTAAAAAGAATTAAC
TAACTCTAACAAAATCTAATATTTCAGTCGGTGTAGTAAAAACATAAACATAAACGATTTCAAATGTATCCTGAATACGCGGTAAACTTGTGTTT
ACCAACACCGCCTCTTAGACTATTCAGGCCTGCCAGATCTCCAAAAAAATATTATTTAGATAAGTTAGTGACACAAAAGGTTTAAGTCTTAACTG
CGCTTAGCTGGGCTTTAAACCCACTGCCTATTCTTTGCTAATTGGAGTATTGCAAATCAGTTTTGAATCTGATTTATTTGTCCCGCTTACCAATT
TTAATTGTGTAAATTCATTTGGTTTTACTTGGCCAACTTACAAATAATAGAATAATAAAAATGAAAGCCGTCTGTTTAATTATTAAAATAATGTG
AATTAATTGGATTATTAATCTGGGCGTTATTATATAGAAAAGAAACCTAACTAACCAATTGCGGAAATATCGATAGCATCGCAATAAAATCTATA
TTGTGCCACCTCCAATTCACACAGGTCGGTCACACTGGGCAGGCTTGCCAATTTCAAGAGCCGCGGCCACACTACTGCGAATTCTATACTGCAAC
TCGATCGTGCGTGTTCTGTATTTTTGGGAGTGCGTTGTTAGAAATTCGGCCACAAATAGAATCCGCTGTCCTGGAACGAGTCAGAAACCACGGGA
AATTGACTTCCGGACTAAATAGCGTTCTTGTGTGTCCATCCGTGTGCGTGTGTCCGCATTCTGCAGTGTGCGTGTGTGCGAAAGAGAGAGGGCGA
GCGGTGCAGCCGCAACTGGGAAATTCGATTGCCAATATTTCAGCAAGGAAGCTATGTCGAGCGGTCAGCAATTGATGGCCGATTCGCCAGCCTGC
AGCTCAAGTGACCATTCGCCGCTGGCCAAAAAAAGGCGTTTAGAGTTGTTGGGTGACGGAGTGGGGGCAATGGGAATGGAAGAGGAAGAAGCCGG
CGGAGCAACGAGCAGCAGTAGCAGCAACAACTACGAAAATCACGACAAAGCAGGCGGCGTTGACATTTCGGGCAAGTGCCAGAGCAAGACGACTA
GCGAGCACCAGCTGGAATTGTGCGTATCGTCGTCTACCTCTGACACATGCGGCGTTAATGCTGCGGCGAAGCGAGCCGAAAAGCAGAAACTGAAA
CAGAGCCAAGGAAGCGGCGACGACGTTAGTACCTCGTCAGCAGTGGAAAAGGAAGGAAGCAAGCGGCCGGAGAAGCGCAATTACCTGAACACCAC
CACAATAGAATCGCAAGAAGCCTCCTCCAGTGCATCCGCCACTAGCAACAGCAACAACAACGTCAGCTCCAGCAACAATAACAGTAATAACAGCA
CTAATAACCGACAACTGGAAGGAAGCAGCAACATGGCTGGAAACAGTGCCGCCGCCGGCGGAGATATCGATGAATCGCTGTACTCGCGCCAATTG
TACGTCCTGGGTCACGATGCGATGCGTCGGATGGCCAATTCGGATATCCTTCTGTCGGGACTTGGAGGACTCGGCCTGGAGATAGCCAAGAATGT
GATTCTGGGCGGCGTGAAATCGATCACCTTGCATGACACAGCAACTTGTGGGGTATGTGTGTGGGGCGAAGAAAAAATCGATAATTTTCCAGGCG
GACGCGGGAAATGCCCGGAAAGGCTGACTTGGCATCCCTGGTCTTAGTGAATCATTCAGTTTTTATTTGATTTATTTATCATAGACTTCGCGCGA
AATAAGGTTAGGTTAACATCTCTATTTGCTTGCAAAAAATTCGTTTTGTGTGTGTAATTCGGTTTTCCTTCTTTTTCTATTTGCCTCAAAATGTC
TGCGCCATGCGAAAAGTGTGTGAGCGGGACAACCGTATGCGCATCGCTCGCTGCCGTTGTGTTTGCATTCCCCTTTGCTCAACGCATTCGGTTTT
GTTTTATGCACTGAAAGATTCAACTTAAGATCTATGAGTTTCTCATAAACCGTAATATATCAATTATTTAGTTAATAGCCTTTCAATTTAAAGTT
TTCTTGTATCATAAAAACTTTTTTGTTCTAATGACAAATATGTCTTTGCTGTACACTCGGCACAGAACCAATTTTCCTTTGTTAGTCATGGCTCC
CGTCTGCTAATTTCATCACCGTTGATATATAATATTAATGATTATTCGTTTGTCTTGCAGCTCCATGACTTGTCGTCGCAATTCTATCTCACGGA
AGCCGATATCGGCAAGAATCGTGCGGAGGCCTCTTGCGCCCAGTTGGCCGAGTTAAACAACTATGTGCGCACCGTTTCGCACACGGGGCCGCTTA
CCGAGGAGTTCCTGCGCAAGTTTCGCGTTGTGGTACTGACCAACTCCGACGGGGAGGAGCAGCAGAGGATCGCCAAGTTTGCCCATGAAAATGGC ATTGCTCTGATCATCGCCGAGACGCGCGGACTGTTCGCCAAGGTGTTCTGTGACTTTGGCGAGAGCTTTACCATTTACGATCAGGATGGCACACA
GCCGATCTCCACCATGATAGCTAGTATCACGCACGACGCACAGGGAGTCGTCACCTGCCTGGACGAGACGCGCCATGGTTTTAATGACGGTGACT
ACGTCACCTTCTCGGAGGTGCAGGGCATGCAGGAACTGAACGGTTGTCAGCCCCTTAAGATCACAGTGCTGGGACCCTACACATTTAGCATCGGT
GATACCAGCAAGTTTGGAGAATATAAGAGCGGAGGAGTGGCCACCCAGGTGAAGATGCCCAAGACCATCAGCTTCAAGCCCCTGGCACAGGCCAC
TGAGGAGCCGGAGTTTTTGATCTCCGATTTCGCAAAGCTGGACTCGCCGGCCACGCTGCACGTGGCCTTCAATGCCCTCTCCTGCTACCGCAAGG
CCCATAATGGAGCCTTACCGCGTCCCTGGAACGAGGAGGACGCCAACAGCTTCCTCGAGGTAGTCCGAGCCAGCAGCAACGCGGAAGTCGACGAA
AAACTGGTGCTGCAATTCGCCAAAATCTGCTCGGGTAATACGTGCCCGCTGGACGCGGCCGTTGGTGGAATTGTGGCCCAGGAGGTGCTTAAGGC
CTGCAGTGGAAAGTTTACACCCATCTACCAGTGGTTGTACTTTGACGCCCTGGAGTGTCTGCCCACAGAGGGTGTCGAGGAGGCGGATGCCCAGC
CGGTGGGCTCGCGCTATGATTCTCAGATTGCCATATTTGGCAAGAAGTTCCAGGAGAAGTTGGCTGACTCGAAATGGTTTATTGTCGGCGCCGGA
GCCATTGGTTGTGAGCTATTGAAAAACTTTGGAATGCTGGGCCTGGGAACTGGCAATGGCCAGATTTTCGTCACAGACATGGATCTCATTGAGAA
GTCGAATCTGAACCGGCAGTTCCTGTTCCGCCCGCATGATGTGCAGAAGCCTAAATCAATGACGGCCGCCGACGCTATCAAACGGATGAATCCGG
AAGTGAATGTCACCGCATACGAGTTGCGCGTTGGCGCCGAAACAGAGAAAGTCTTTTCCGAAGATTTCTTTGGAAAGTTGGATGGTGTAGCCAAT
GCGCTGGACAACGTGGATGCTCGCATATATATGGATCGCAAATGCATCTTCAACCGCATTCCGCTCGTCGAGACCGGAACTCTGGGAACTTTGGG
CAACGTTCAGGTGATTGTGCCCTTTGCCACCGAATCTTATAGCTCCTCCCAGGATCCCCCAGAAAAGAGTATTCCCATCTGCACGCTGAAGAACT
TCCCCAATGCCATCGAGCACACTCTGCAGTGGGCGCGTGACGCCTTTGAGGGCGTCTTCAAGCAGTCTGCAGAAAATGCTGCTCAGTACATCGCC
GATCCTCAGTTCACCGAGCGAATCGCCAAGCTGCCTGGTATTCAGCCTCTGGAGATCCTCGATTCCATCAAGGTAAGGATAGAATTTACTTCTTT
GCCTAATATGTTGTACTTAATGGTAATTTATTTTTACAGAAAGCTCTGATCGACGACAAACCCAAGAGTTTCGCGCACTGCGTGGAGTGGGCCCG
TCTTTATTGGGAGGATCAATATGTTAACCAGATTAAGCAGTTGCTCTTTAACTTCCCACCTGATCAGATCACCTCCAGTGGTCAGCCGTTTTGGT
CTGGTCCCAAGCGGTGCCCCGATCCCCTGGTCTTTGATGTCAACGATCCCATGCACCTCGACTTTATCTACGCAGCCGCCAATCTTCGAGCTGAG
GTCTATGGCATTGAGCAGGTTCGCAATCGCGAGACGATCGCAGAGCTGGTACAGAAGGTTAAGGTTAGTTGTTCGAGATTAATACCGTCGGGGAC
CATTTCTGATATTATTGATTTATAGGTGCCCGAGTTTAAACCCCGTTCGGGCGTGAAAATAGAAACCAATGAGGCAGCAGCCGCCGCCTCGGCCA
ATAACTTCGATGACGGCGAGTTGGACCAGGATCGCGTTGACAAGATCATTTCAGAGCTGCTAAAGAACGCCGACAAAAGCTCCAAGATCACGCCA
CTTGAGTTTGAAAAGGACGACGACAGTAACTTGCACATGGACTTCATTGTGGCCTGCTCAAATCTACGCGCCGCCAACTACAAGATTCCGCCAGC
GGATCGCCACAAGTCCAAGTTGATTGCTGGCAAAATCATACCTGCTATTGCCACCACCACGTCGGTGCTCTCTGGATTGGCTGTGCTCGAGGTGA
TTAAGCTGATCGTCGGCCACCGGGATCTCGTAAAATTCAAGAACGGCTTCGCCAACTTGGCATTGCCGTTCATGGCCTTCTCTGAGCCGCTTCCT
GCCGCCAAGAACACATACTACGGCAAGGAGTGGACGCTGTGGGACCGTTTTGAGGTGACCGGGGAGCTGTCGCTGCAGGAATTCCTCAACTATTT
CGAGGAGAATGAGAAGCTTAAGATCACCATGCTCTCGCAGGGCGTGTCCATGCTGTACTCGTTCTTCATGCCCAAGGCCAAGTGCTCTGAGAGAC
TGCCGTTGCCGATGTCGGAGGTCGTGCGTCGCGTGTCCAAGCGTCGCCTGGAGCCACACGAGCGATCCCTGGTTTTCGAGATCTGCTGCAACGAT
GTGGATGGCGAGGATGTGGAGGTGCCCTACGTCCGTTACACGCTGCCCTAAGCCCGTCTATATTCCTAATTTAACCATTAAATTATTTTACGATC
CCGTTTTGTTGTCGGCGACGCGTTTTGGAATCGCGCAGCTCCAACGAAGGAGTTACTGTCTAGCTGTTTGCATTTTAATTTTCACAACACCATTA
CGAGAGCAGCCCAGATCTAGAAATTATATAAAATGTGTGTGAATCCTCTAAGGAATGGCAAAATAATACGCATCATACGAAATACAAAGACTCGA
CTAAAAGCAACACTTAAAATGCATCTGATGAAACTCTCTGCTCAGCATAGTTGTAAAGGTAACGAATTACGAAAAACCGAAGGCGGATTTTAATC
GCATTGATTAATTGGAAATTGAAAACTGAATGAGCCAGGCGGAAAATTTCTCTTCACTCATATATTTTTTTATATGGAAGCATAAACTAATTAC
GTCATTGTATTAAAAGGAGTAAAGCAAATGAATAAAGCTGTATATTTCATATGGTAATCGACCTGCTAGACGACTCAGATAATTTCGTTCAGCAC
TTGACGTCTGGTAATCTCATTTCCCCCGCCACTTCGGAAATTAAAATTGTAATGCATACTGCTCTGCCAGTGAAGTATATAGGGGATGCCATCTA
TCCGTACGCCAGTCAGTTTCAGAAAGTTACGTGACACAATTAAATATTTTATGCCCTCTCAAGACGTTTATACCACCCCCGCCCCGCACCCAAGG
AGGCTGCTGCCACCAAAGTGCAATTGGCAAGTGCCGTAAAGTTGCACCGCTCATGGAAAGCGTTGGGCGGAGTGGCGGCGTCCTCTTATAATTAA
ATATTACACGCAATGCAACTGAAGTATGGCCAAAGTTATGCAGTTTCGCATCTCACTCTTGGCCTTTTGCGGCTTTTTGGCAAACTTGCTTGAAT
TATGCAGTTAATGAAAACAAAGCGAGGCGAGGAAAGTGGCTGCGCCGATCAGCTTTGTATCCGTCGAATAAGTGTGTTCTGGGCAGGGTAATCAA
AGTTTTGGGTTTGTAGTTCGACTCCTTAGGGCTCTGATTGTTAGCATCTAAGTATTTAAGATTTACATATAAGATCGTCTTATTACTTAGAGCTT
ACTTTAAAAAGATGAGTGAACAAACTATTTACAAGGCAAAGTGGAAATGCTGGGTCAGAATTAAGATTAATACCTATCTAAATTTGAGGTGAAAG
TAGGTGACTAAGTTTTCAAATAGAGCTGGGAAAATTAGAGATACATTACAGGAGTACCACAAGAGATTTAGAATATGAATATTCCTGTTCTAACA
CCACATTACAGTACATTTTTATGTTTTTAAGATTAGTTTCTCAAAAATGAACAGACAATTTTGTTTTATGAAAAGAGTAATCCAAATATTATTC
CATATTATTCATTTCGTTCTATTGGTTTTGTTAAGCTGGACTTCTGAATCACTGAAATGTAAAGACTTACATGTACATTTTTCGATCGTACATTC
ATATGTGCAT
(SEQ ID NO: 151)

Exon: 1001..2047
Exon: 2626..4347
Exon: 4410..4718
Exon: 4776..6040
Start ATG: 1838

Transcript No. : CT5340
ATTTCAAGAGCCGCGGCCACACTACTGCGAATTCTATACTGCAACTCGATCGTGCGTGTTCTGTATTTTTGGGAGTGCGTTGTTAGAAATTCGGC
CACAAATAGAATCCGCTGTCCTGGAACGAGTCAGAAACCACGGGAAATTGACTTCCGGACTAAATAGCGTTCTTGTGTGTCCATCCGTGTGCGTG
TGTCCGCATTCTGCAGTGTGCGTGTGTGCGAAAGAGAGAGGGCGAGCGGTGCAGCCGCAACTGGGAAATTCGATTGCCAATATTTCAGCAAGGAA
GCTATGTCGAGCGGTCAGCAATTGATGGCCGATTCGCCAGCCTGCAGCTCAAGTGACCATTCGCCGCTGGCCAAAAAAAGGCGTTTAGAGTTGTT
GGGTGACGGAGTGGGGGCAATGGGAATGGAAGAGGAAGAAGCCGGCGGAGCAACGAGCAGCAGTAGCAGCAACAACTACGAAAATCACGACAAAG
CAGGCGGCGTTGACATTTCGGGCAAGTGCCAGAGCAAGACGACTAGCGAGCACCAGCTGGAATTGTGCGTATCGTCGTCTACCTCTGACACATGC
GGCGTTAATGCTGCGGCGAAGCGAGCCGAAAAGCAGAAACTGAAACAGAGCCAAGGAAGCGGCGACGACGTTAGTACCTCGTCAGCAGTGGAAAA
GGAAGGAAGCAAGCGGCCGGAGAAGCGCAATTACCTGAACACCACCACAATAGAATCGCAAGAAGCCTCCTCCAGTGCATCCGCCACTAGCAACA
GCAACAACAACGTCAGCTCCAGCAACAATAACAGTAATAACAGCACTAATAACCGACAACTGGAAGGAAGCAGCAACATGGCTGGAAACAGTGCC
GCCGCCGGCGGAGATATCGATGAATCGCTGTACTCGCGCCAATTGTACGTCCTGGGTCACGATGCGATGCGTCGGATGGCCAATTCGGATATCCT
TCTGTCGGGACTTGGAGGACTCGGCCTGGAGATAGCCAAGAATGTGATTCTGGGCGGCGTGAAATCGATCACCTTGCATGACACAGCAACTTGTG
GGCTCCATGACTTGTCGTCGCAATTCTATCTCACGGAAGCCGATATCGGCAAGAATCGTGCGGAGGCCTCTTGCGCCCAGTTGGCCGAGTTAAAC
AACTATGTGCGCACCGTTTCGCACACGGGGCCGCTTACCGAGGAGTTCCTGCGCAAGTTTCGCGTTGTGGTACTGACCAACTCCGACGGGGAGGA
GCAGCAGAGGATCGCCAAGTTTGCCCATGAAAATGGCATTGCTCTGATCATCGCCGAGACGCGCGGACTGTTCGCCAAGGTGTTCTGTGACTTTG
GCGAGAGCTTTACCATTTACGATCAGGATGGCACACAGCCGATCTCCACCATGATAGCTAGTATCACGCACGACGCACAGGGAGTCGTCACCTGC
CTGGACGAGACGCGCCATGGTTTTAATGACGGTGACTACGTCACCTTCTCGGAGGTGCAGGGCATGCAGGAACTGAACGGTTGTCAGCCCCTTAA
GATCACAGTGCTGGGACCCTACACATTTAGCATCGGTGATACCAGCAAGTTTGGAGAATATAAGAGCGGAGGAGTGGCCACCCAGGTGAAGATGC CCAAGACCATCAGCTTCAAGCCCCTGGCACAGGCCACTGAGGAGCCGGAGTTTTTGATCTCCGATTTCGCAAAGCTGGACTCGCCGGCCACGCTG
CACGTGGCCTTCAATGCCCTCTCCTGCTACCGCAAGGCCCATAATGGAGCCTTACCGCGTCCCTGGAACGAGGAGGACGCCAACAGCTTCCTCGA
GGTAGTCCGAGCCAGCAGCAACGCGGAAGTCGACGAAAAACTGGTGCTGCAATTCGCCAAAATCTGCTCGGGTAATACGTGCCCGCTGGACGCGG
CCGTTGGTGGAATTGTGGCCCAGGAGGTGCTTAAGGCCTGCAGTGGAAAGTTTACACCCATCTACCAGTGGTTGTACTTTGACGCCCTGGAGTGT
CTGCCCACAGAGGGTGTCGAGGAGGCGGATGCCCAGCCGGTGGGCTCGCGCTATGATTCTCAGATTGCCATATTTGGCAAGAAGTTCCAGGAGAA
GTTGGCTGACTCGAAATGGTTTATTGTCGGCGCCGGAGCCATTGGTTGTGAGCTATTGAAAAACTTTGGAATGCTGGGCCTGGGAACTGGCAATG
GCCAGATTTTCGTCACAGACATGGATCTCATTGAGAAGTCGAATCTGAACCGGCAGTTCCTGTTCCGCCCGCATGATGTGCAGAAGCCTAAATCA
ATGACGGCCGCCGACGCTATCAAACGGATGAATCCGGAAGTGAATGTCACCGCATACGAGTTGCGCGTTGGCGCCGAAACAGAGAAAGTCTTTTC
CGAAGATTTCTTTGGAAAGTTGGATGGTGTAGCCAATGCGCTGGACAACGTGGATGCTCGCATATATATGGATCGCAAATGCATCTTCAACCGCA
TTCCGCTCGTCGAGACCGGAACTCTGGGAACTTTGGGCAACGTTCAGGTGATTGTGCCCTTTGCCACCGAATCTTATAGCTCCTCCCAGGATCCC
CCAGAAAAGAGTATTCCCATCTGCACGCTGAAGAACTTCCCCAATGCCATCGAGCACACTCTGCAGTGGGCGCGTGACGCCTTTGAGGGCGTCTT
CAAGCAGTCTGCAGAAAATGCTGCTCAGTACATCGCCGATCCTCAGTTCACCGAGCGAATCGCCAAGCTGCCTGGTATTCAGCCTCTGGAGATCC
TCGATTCCATCAAGAAAGCTCTGATCGACGACAAACCCAAGAGTTTCGCGCACTGCGTGGAGTGGGCCCGTCTTTATTGGGAGGATCAATATGTT
AACCAGATTAAGCAGTTGCTCTTTAACTTCCCACCTGATCAGATCACCTCCAGTGGTCAGCCGTTTTGGTCTGGTCCCAAGCGGTGCCCCGATCC
CCTGGTCTTTGATGTCAACGATCCCATGCACCTCGACTTTATCTACGCAGCCGCCAATCTTCGAGCTGAGGTCTATGGCATTGAGCAGGTTCGCA
ATCGCGAGACGATCGCAGAGCTGGTACAGAAGGTTAAGGTGCCCGAGTTTAAACCCCGTTCGGGCGTGAAAATAGAAACCAATGAGGCAGCAGCC
GCCGCCTCGGCCAATAACTTCGATGACGGCGAGTTGGACCAGGATCGCGTTGACAAGATCATTTCAGAGCTGCTAAAGAACGCCGACAAAAGCTC
CAAGATCACGCCACTTGAGTTTGAAAAGGACGACGACAGTAACTTGCACATGGACTTCATTGTGGCCTGCTCAAATCTACGCGCCGCCAACTACA
AGATTCCGCCAGCGGATCGCCACAAGTCCAAGTTGATTGCTGGCAAAATCATACCTGCTATTGCCACCACCACGTCGGTGCTCTCTGGATTGGCT
GTGCTCGAGGTGATTAAGCTGATCGTCGGCCACCGGGATCTCGTAAAATTCAAGAACGGCTTCGCCAACTTGGCATTGCCGTTCATGGCCTTCTC
TGAGCCGCTTCCTGCCGCCAAGAACACATACTACGGCAAGGAGTGGACGCTGTGGGACCGTTTTGAGGTGACCGGGGAGCTGTCGCTGCAGGAAT
TCCTCAACTATTTCGAGGAGAATGAGAAGCTTAAGATCACCATGCTCTCGCAGGGCGTGTCCATGCTGTACTCGTTCTTCATGCCCAAGGCCAAG
TGCTCTGAGAGACTGCCGTTGCCGATGTCGGAGGTCGTGCGTCGCGTGTCCAAGCGTCGCCTGGAGCCACACGAGCGATCCCTGGTTTTCGAGAT
CTGCTGCAACGATGTGGATGGCGAGGATGTGGAGGTGCCCTACGTCCGTTACACGCTGCCCTAAGCCCGTCTATATTCCTAATTTAACCATTAAA
TTATTTTACGATCCCGTTTTGTTGTCGGCGACGCGTTTTGGAATCGCGCAGCTCCAACGAAGGAGTTACTGTCTAGCTGTTTGCATTTTAATTTT
CACAACACCATTACGAGAGCAGCCCAGATCTAGAAATTATATAAAATGTGTGTGAATCCTCTAAGGAATGGCAAAATAATACGCATCATACGAAA
TACAAAGACTCGACTAAAAGCAACACTTAAAATGCATCTGATGAAACTCTCTGCTCAGCATAGTTGTAAAGGTAACGAATTACGAAAAACCGAAG
GCGGATTTTAATCGCATTGATTAATTGGAAATTGAAAACTGAATGAGCCAGGCGGAAAATTTCTCTTCACTCATATATTTTTTTATATGGAAGC
ATAAACTAATTACGTCATTGTATTAAAAGGAGTAAAGCAAATGAATAAAGCTGTATATTTCATATGGT
(SEQ ID NO: 152)

Start ATG: 838

MAGNSAAAGGDIDESLYSRQLYVLGHDAMRRMANSDILLSGLGGLGLEIAKNVILGGVKSITLHDTATCGLHDLSSQFYLTEADIGKNRAEASCA
QLAELNNYVRTVSHTGPLTEEFLRKFRVVVLTNSDGEEQQRIAKFAHENGIALIIAETRGLFAKVFCDFGESFTIYDQDGTQPISTMIASITHDA
QGVVTCLDETRHGFNDGDYVTFSEVQGMQELNGCQPLKITVLGPYTFSIGDTSKFGEYKSGGVATQVKMPKTISFKPLAQATEEPEFLISDFAKL
DSPATLHVAFNALSCYRKAHNGALPRPWNEEDANSFLEVVRASSNAEVDEKLVLQFAKICSGNTCPLDAAVGGIVAQEVLKACSGKFTPIYQWLY
FDALECLPTEGVEEADAQPVGSRYDSQIAIFGKKFQEKLADSKWFIVGAGAIGCELLKNFGMLGLGTGNGQIFVTDMDLIEKSNLNRQFLFRPHD
VQKPKSMTAADAIKRMNPEVNVTAYELRVGAETEKVFSEDFFGKLDGVANALDNVDARIYMDRKCIFNRIPLVETGTLGTLGNVQVIVPFATESY
SSSQDPPEKSIPICTLKNFPNAIEHTLQWARDAFEGVFKQSAENAAQYIADPQFTERIAKLPGIQPLEILDSIKKALIDDKPKSFAHCVEWARLY
WEDQYVNQIKQLLFNFPPDQITSSGQPFWSGPKRCPDPLVFDVNDPMHLDFIYAAANLRAEVYGIEQVRNRETIAELVQKVKVPEFKPRSGVKIE
TNEAAAAASANNFDDGELDQDRVDKIISELLKNADKSSKITPLEFEKDDDSNLHMDFIVACSNLRAANYKIPPADRHKSKLIAGKIIPAIATTTS
VLSGLAVLEVIKLIVGHRDLVKFKNGFANLALPFMAFSEPLPAAKNTYYGKEWTLWDRFEVTGELSLQEFLNYFEENEKLKITMLSQGVSMLYSF
FMPKAKCSERLPLPMSEVVRRVSKRRLEPHERSLVFEICCNDVDGEDVEVPYVRYTLP*
(SEQ ID NO: 153)

Name: Ubiquitin activating enzyme 1
Classification: enzyme
Gene Symbol: Uba1
FlyBase ID: FBgn0023143

Celera Sequence No. : 142000012789666
TATTTTCTTTTTTTTTAGTTTTCTTCAAGAACCCACAAATTCCCGTTTGGCTAGCACTGCATTTCGCCATCTCTTTCTGATTCGCTCGCTGGAT
CGGCGTCCCTCTCTCTCTTCCCAACGCCCACTGTGCGTCGCAACTGGTTTAACGTTCTGATTCGACTTTTATGGCTGCCGCTGCAGCACGGCCGT
GGGTCGCCTCTGATCGGAATTTCAAAACAGTGGAGCGTGTTGTGGATGTTGGGGCAACAGTGGGTGGCATGTGTGGTGCACAGTGGTCACACACG
GCACAATTCGTGGTTGAAATGTGTGAGGGACTTTAAAAATTTTATAAGAAACCGATTGGTTTGCAAGTGAAACAATAAGCGGTGTTTTCATTTTT
TTGGTTAGCTTTTATTTGCGTGCAATACAAACTATGACAAAATTTGCCTAATAAATAGAGCCTAATTTTTGGGCCGCTCGATGAGCCTAAAGACT
ACGAGTTGCGGATCAAATGGATTGATTTGGACAAGGACATGGACCGGACATAAGGCTAGACAGTACAGATTTATACTATGCGATCGGATATCGTA
TACAATTTTGGTTCAGCTGCTCGGAAATCGCATTCGAGTTCGCGTTAAACATGTGTGTGTGTGTGTGGTGTGTGTGTGTGGTGTGTGTGTGGGTG
GGTGTGTGTGTGCATAGAATTCAGTTATATTGCTTATATAAATAACTCTGCTGCCTTGCAAACATAAGGAATTATTTTTGGATCACAATAAAATT
ATAAAAACATATATCTATATATATATATATGTATATACATATAGTATATAACGAAGGTAATAACGCAAAACCAATATGCAATGCACAGGTTTTGG
AACCACCAAGCATTGGGGCACTGGGAAGGACTAGATAACAAGAGCAGCACGGTCTGCAAAATATAACTAAGCGCGGAGACTAACAGCTAACAGAC
CACAGGAGTATTTCAAGTACAAAACATTATCGGCCGCAGCGGCGATCAGCTCAGAGCGTCTCCCTGGTGTCAAGCTCAACCAATGGCGGCACTGG
CTCCAACTCCGCACTCTGGCTTCTGCTCCTACTTAGGCTGGGACTGGGGTTGCTCCTTGAACTTGGACTGGTGTGGTGGCTTGCGTCTGCACTGA
TATTACTTGGCTGATTTTGTTCATGGTTGTTATGCGGCGACGAGGTTGCCGGGGTCAGAGGAGCCGGAAGTGCTGGCGTGCCGGGCGGGGAGAGT
GCTGGCGGAGTGAGTGGGGCAACGGCCACTTCCCTTGTCTGTGGCGGCCAGTGGATGGACCTTAAAACGCTTTGGCTGCTGCTGGAGGAAGTGGA
GGGACTTTCAGCATGGCCTGAAGCCAACGAGGATCCCGAGGTAGAGGCAATATTGTCATCGTCAGTCTTGGCCGTCTTCTTCTCCTTCTCCCTCT
TCTCGCGCTCCTTCTCCATGTCGGCTATCTTCTTTAAGTAGTTTTTGTCCTGGGTCGGACATTCGAGGTGGACGCAGTGGAAGATCTAAGAGCAA
GGAGAGCATTAGCTTATCGGACATGTTTTGTGGCGCTGCACTGCTACGTACCTCATTCGCTGTGTTGCGTGTGCCCACAATGCGGATATAGACCA
CTGGACGCGGAGTAAAGTGAAAGTTCTGCCAGGAGCGGGTCCTGTCGTTGCGGCGGTCCACGACCATTTGCCATTCCTTGCGGTTCGTCGAAATT TCGATGTAGAAGCTGTAGGTGCGATCATCGCAGTCCCACAGCAACAGCCTCATTGAGCCCAAATAGTAGGGTTGGCCCAAACGGACGACGATCTC
GCCGCTGCCCAATTGGTGGCAAGTATATCCCGAGTCCCAGTCGTAGCGCACATAATCGCCGTTGATAAGCGCGTTGCGGGTGCGACTCACGCCGT
CCGTCACAATGGCGCTCATCTCTACGGTGGCCACGTTCGTCTTGGGCGCCACAAAATGGTTAACTAAACGCGGCACCTTGGCCGTGTGCATGGCT
TCCAGACCCACAACATGGAATACCTATATATTAATGGAAAGGGAAAAAGTTAAAGAATGGGGAAAGTTTGAAGAGATCACTGCTGACTTACCCGG
TTTACAGTGTTCTGGGTGCCCACCAGTCGAATGAATCTGACGGGTCGTGCTTCGAAGTATAAGTATTGCCAGGAGCGGCAGTGGTAGTCGCTGTA
GTCGACCACGCGATCCCAATGCTGCTGGTCGCCGGACACCTCAACGTAGTAGGAGTACGCCCGGCTGTCTCTGTCCCAGAGCAGCATGCGAATGT
GATTGATCATGCAGAACGTGCCCAATTCGACCACAATGCCCGCATCTTTGCTGTCCGTAATGCAGTGGCGCGTATACCCGTTCTCCATGTCATAG
GTGGTCACATCTCCATCCAGCAGCGCGTCGCGACACTCTCCCTGGATGCAGCGCGACAAAAACGTCTCCGCGGCCACGTTTTCCTCCGGCCAGAG
CGCCGCCCTGTAGGGCAGCGCCTTTGAAGTGCTGCGCTCGTCGATGGCGTCGAGAATCTTGTCGGGATCCAGGATGCCCGAGGGACGCACCACCT
GCAGCAGATGCTCGAGGTTCATCAGTGGCAGGCGGACATAACTAACCACGGACTTGAAGTCCACGTTGCTATTGAAGCGGCTCCACTTCCACACG
GCCAAAAAGATCTGCACCTCGGGGGCGAAGAAGCAGTCACGCCGTAGTACCTCCTCCAGCGATTCCTGTAAGCATTACATACTCTTAGTGCCAAC
TTTACCAATTGGTTGTGAACTTACCTTGGATAGCGTATTGAAGCTGTTGTGCAGCAGCAGGTCGCCGGCATTGCGATCCATGAACATTAGGCAAA
CCTCGGTGAGTTCCTCTAGATTGTATAGACGCGCCGCATCAAGAATCATGCAGACATTGTCCAAGGCCAGATACTGGCGTAAATAATTCGATATG
GCCATCTCCAGATCCTGGAAACCATACTGATTGGCCATGCCCAGCACATCGATGGTGGAATCCTCGTCCAATGTGGACAGCAGCAGTGTGCCCGA
GTAAATGTAGCGCAGCAGCACCTTGAACGCTTCCAGCGGCACCTCAAGCGGTATTTGGCGCTGTGTGGTCTCCGCCATGCCGCCGTACAGCAGCG
CCCGGAAGTATTCGCTGCGTGCCGCGAGTATGACGCGGTGGGCGGTATGCGCTCCTCCTCGACGATGAACTCCACGTCCGCGTACTGTTCGTTC
ATGCAGAGGCGCGCCATGTCCGCTGAGAAGCGATCGCCCAGATCGACCACGTCGGTGTAGTCCTGCTCCATGGCGCCCTTCTTGCCGCCGCCGGA
CATCTTATGGTGTCCCTGGCTGCTCATCCTTCTCTTTTTTGTTTTTCTTCCGTGCGATGTGTATTTATGTGTGTAAGCAGCCAGAGGGAACAGTT
GACAATTAACGTTTCGTCTCGCCTGCTGCGTCAATCCATCGATGACAGTTAGTGATATCGATAATATCGATGGCACAATAGGGATTCTTCTATTG
CGGCGAAAAACTGTTATATGTGCAGTGTGACCGTAGGTGTGTATACCATTTAACGCGTACAACAACCATATCGACAGCCGTCTGCTAGCGAGCAC
ATGAACCACATGGTTGCATCCGATAACATTTAGCGAATACATGAACCAAATGGTGTCTGTCTAATATGCCACCACTATTAGCGCGTTTCGGGTTG
GTGTCTCTGCGCGCTCACTGGTCACACACGGTCAGTCTAGCCACAGCAGTTAGCGAGTGCAGTCACCACAGTGCGAGTGCTTATCGATAAAACCA
GCAAGTCATCGATTTTTAGACCGAAGCGCTCTGTCAACTGCTGCGCACGGTCACTCTACACAAGTATTTCGTACCGTTTGTACGAGAAAACAGAG
AAGAGAAAAACACAAGCTCAGCAACGCATCGATATTCGGCACAGTCCCAAAAGCAAACGAAGTGATAGAAGCTGCGTTTCTTAGCCAATTACCTC
TTCATTGCAATCATGAAGTTCCAATACAAGGAGGAGCACGCCTTCGAGAAGCGTCGCGCCGAGGGCGACAAGATCCGTCGCAAATATCCAGACCG
TGTGCCCGTAAGTACTCAAAAATATATATATAAATGCATATAGGTATAAAGAGACGTGTGTGTGTGTGTATATATGCGTGCGAGTGTGTGTGTAT
GTGCGAGCTTCTGTGTATGCGTTTGTTTTGCGTCGTTTTTTTCTCGCTCTTTTTTTTTGTGTTTGCACCGAAGAAAATCAATACTGCGCATATT
GGGTATTTCGATTGTTATTACAATATTATTGCACTGGCACATCAGGTGGCTGGGGAAATTTGTGCGATGGGTATTGCATAAAGTGCATTTTGCAT
TACTGGTGGGGGGAACAGGCGACAAGCTCTCAAAAGAAATTCAAACGAAAATTCTGCCCCCTGCATACACACATACGCACGCATACACGCGCACA
CAGGCACACAGATGTCGACAGGAAAAAACAAAAGCAAAAAAAGGGAGAGAACAAAGCAGC
(SEQ ID NO: 154)

Exon: 3525..2780
Exon: 2725..2087
Exon: 2018..1572
Exon: 1510..1001
Start ATG: 3352 (Reverse strand: CAT)

Transcript No. : CT5456
TTTTTCGCCGCAATAGAAGAATCCCTATTGTGCCATCGATATTATCGATATCACTAACTGTCATCGATGGATTGACGCAGCAGGCGAGACGAAAC
GTTAATTGTCAACTGTTCCCTCTGGCTGCTTACACACATAAATACACATCGCACGGAAGAAAAACAAAAAAGAGAAGGATGAGCAGCCAGGGACA
CCATAAGATGTCCGGCGGCGGCAAGAAGGGCGCCATGGAGCAGGACTACACCGACGTGGTCGATCTGGGCGATCGCTTCTCAGCGGACATGGCGC
GCCTCTGCATGAACGAACAGTACGCGGACGTGGAGTTCATCGTCGAGGAGGAGCGCATACCCGCCCACCGCGTCATACTCGCGGCACGCAGCGAA
TACTTCCGGGCGCTGCTGTACGGCGGCATGGCGGAGACCACACAGCGCCAAATACCGCTTGAGGTGCCGCTGGAAGCGTTCAAGGTGCTGCTGCG
CTACATTTACTCGGGCACACTGCTGCTGTCCACATTGGACGAGGATTCCACCATCGATGTGCTGGGCATGGCCAATCAGTATGGTTTCCAGGATC
TGGAGATGGCCATATCGAATTATTTACGCCAGTATCTGGCCTTGGACAATGTCTGCATGATTCTTGATGCGGCGCGTCTATACAATCTAGAGGAA
CTCACCGAGGTTTGCCTAATGTTCATGGATCGCAATGCCGGCGACCTGCTGCTGCACAACAGCTTCAATACGCTATCCAAGGAATCGCTGGAGGA
GGTACTACGGCGTGACTGCTTCTTCGCCCCCGAGGTGCAGATCTTTTTGGCCGTGTGGAAGTGGAGCCGCTTCAATAGCAACGTGGACTTCAAGT
CCGTGGTTAGTTATGTCCGCCTGCCACTGATGAACCTCGAGCATCTGCTGCAGGTGGTGCGTCCCTCGGGCATCCTGGATCCCGACAAGATTCTC
GACGCCATCGACGAGCGCAGCACTTCAAAGGCGCTGCCCTACAGGGCGGCGCTCTGGCCGGAGGAAAACGTGGCCGCGGAGACGTTTTTGTCGCG
CTGCATCCAGGGAGAGTGTCGCGACGCGCTGCTGGATGGAGATGTGACCACCTATGACATGGAGAACGGGTATACGCGCCACTGCATTACGGACA
GCAAAGATGCGGGCATTGTGGTCGAATTGGGCACGTTCTGCATGATCAATCACATTCGCATGCTGCTCTGGGACAGAGACAGCCGGGCGTACTCC
TACTACGTTGAGGTGTCCGGCGACCAGCAGCATTGGGATCGCGTGGTCGACTACAGCGACTACCACTGCCGCTCCTGGCAATACTTATACTTCGA
AGCACGACCCGTCAGATTCATTCGACTGGTGGGCACCCAGAACACTGTAAACCGGGTATTCCATGTTGTGGGTCTGGAAGCCATGCACACGGCCA
AGGTGCCGCGTTTAGTTAACCATTTTGTGGCGCCCAAGACGAACGTGGCCACCGTAGAGATGAGCGCCATTGTGACGGACGGCGTGAGTCGCACC
CGCAACGCGCTTATCAACGGCGATTATGTGCGCTACGACTGGGACTCGGGATATACTTGCCACCAATTGGGCAGCGGCGAGATCGTCGTCCGTTT
GGGCCAACCCTACTATTTGGGCTCAATGAGGCTGTTGCTGTGGGACTGCGATGATCGCACCTACAGCTTCTACATCGAAATTTCGACGAACCGCA
AGGAATGGCAAATGGTCGTGGACCGCCGCAACGACAGGACCCGCTCCTGGCAGAACTTTCACTTTACTCCGCGTCCAGTGGTCTATATCCGCATT
GTGGGCACACGCAACACAGCGAATGAGATCTTCCACTGCGTCCACCTCGAATGTCCGACCCAGGACAAAAACTACTTAAAGAAGATAGCCGACAT
GGAGAAGGAGCGCGAGAAGAGGGAGAAGGAGAAGAAGACGGCCAAGACTGACGATGACAATATTGCCTCTACCTCGGGATCCTCGTTGGCTTCAG
GCCATGCTGAAAGTCCCTCCACTTCCTCCAGCAGCAGCCAAAGCGTTTTAAGGTCCATCCACTGGCCGCCACAGACAAGGGAAGTGGCCGTTGCC
CCACTCACTCCGCCAGCACTCTCCCCGCCCGGCACGCCAGCACTTCCGGCTCCTCTGACCCCGGCAACCTCGTCGCCGCATAACAACCATGAACA
AAATCAGCCAAGTAATATCAGTGCAGACGCAAGCCACCACACCAGTCCAAGTTCAAGGAGCAACCCCAGTCCCAGCCTAAGTAGGAGCAGAAGCC
AGAGTGCGGAGTTGGAGCCAGTGCCGCCATTGGTTGAGCTTGACACCAGGGAGACGCTCTGA
(SEQ ID NO: 155)

Start ATG: 174 (Reverse strand: CAT)

MSSQGHHKMSGGGKKGAMEQDYTDVVDLGDRFSADMARLCMNEQYADVEFIVEEERIPAHRVILAARSEYFRALLYGGMAETTQRQIPLEVPLEA
FKVLLRYIYSGTLLLSTLDEDSTIDVLGMANQYGFQDLEMAISNYLRQYLALDNVCMILDAARLYNLEELTEVCLMFMDRNAGDLLLHNSFNTLS
KESLEEVLRRDCFFAPEVQIFLAVWKWSRFNSNVDFKSVVSYVRLPLMNLEHLLQVVRPSGILDPDKILDAIDERSTSKALPYRAALWPEENVAA

FIGURE SHEET 72

ETFLSRCIQGECRDALLDGDVTTYDMENGYTRHCITDSKDAGIVVELGTFCMINHIRMLLWDRDSRAYSYYVEVSGDQQHWDRVVDYSDYHCRSW
QYLYFEARPVRFIRLVGTQNTVNRVFHVVGLEAMHTAKVPRLVNHFVAPKTNVATVEMSAIVTDGVSRTRNALINGDYVRYDWDSGYTCHQLGSG
EIVVRLGQPYYLGSMRLLLWDCDDRTYSFYIEISTNRKEWQMVVDRRNDRTRSWQNFHFTPRPVVYIRIVGTRNTANEIFHCVHLECPTQDKNYL
KKIADMEKEREKREKEKKTAKTDDDNIASTSGSSLASGHAESPSTSSSSSQSVLRSIHWPPQTREVAVAPLTPPALSPPGTPALPAPLTPATSSP
HNNHEQNQPSNISADASHHTSPSSRSNPSPSLSRSRSQSAELEPVPPLVELDTRETL*
(SEQ ID NO: 156)

Classification: hypothetical

Celera Sequence No. : 142000013385193
ATATGTACCATGTAAATTCGTTTCTTCGATCAGAATTGATTTTGGCCCGAAAATCGTCTTCTAGCACAACACGCACACTTATACGCGTTCTCGTC
TCTTGTTTTTACTCACCCAAGCAAGCAAATTATATTTTTAGATTTCTTACGCTCTCAGCGGGAGTGAGCGGAAAGAGAGTAATTTTGGCCGTCAC
CAAAAAAGTGGCTGCATAGTGCCAAACCAATGTATGGCCGTTACGCATCTTGTTATTCTAGGGTCTTTGGTAAGACACAGGCGTGATGTCGCTTA
CGAATCAAATTATATATATGTATATACGTAATGTAAGGTAACTAATGGTAACGTACACTGTTATAAATATTAATGCCAAGCGCAGAACTTTCAAA
ACTGTTACTTGCAATATATTTACAGTTGCTTAAGCCTAGCCTAGTGGTCTAGATTATATAGCTAGATTATTTTGAACGATCCGATCCTGAACTTG
CAGCTACTTGGGTTCGTGATGCGAAAGCACAGCAAATGTGGGGGGTTAAGTGAGCATCGTATGATGACCACAATTCAAAGAACAGATTCCATAC
ACTCGTCTATGTGGCTAGAGAAAGAACTATCGATCCACGGGGAATTCAATTCTTAAGGATTTATTTAATCTCCAGCAGCCTTGCTTGCTACTCCA
ATGTCTTCCTCTTTCCGGTTTTAACAATATTTACACTTCTGAAGGCCTAAAAAGATCGCTGGCTTACAACATGTGATACATCATATACATATATA
ATCTAGTAATTATGTAATTATCGAATATTTCTGCATCATTAGATTTAGTTGCTTAACTCTCGCATAGTTTAAACTTGCATCTATGTATCTGCTGC
TCTCGCTGTAAACATAAAAGTCAAGGAAGAATCTCTTGAACCACATAACACATGCACTTGCTTTAAAACGGGAAACAGAGGAAGCAGAAAAAAAA
CATTACAACAAACTCGACTCCTAAAGCTACGTGTTATCCTAAATATCCGCTTAGCCGTCGACGACCATGCGTTCCGATCCGGAGTCGCACTGCTC
TATGACCAGGCGAGCGATGCGCTTGATCTCGCAGTAGGGACTCTCGTGCTCGATTAGCTCGTTGAGGATCTGGATGCCGTTCTCCTGCTCCACCA
GCTTGCAATATTTTTCGGGATAAACCTGTGACGGAATGCAGAAGTTAGTACACAATGCACCAACAATGGGAAAAGGAATTGCTCCCCCACCTGTG
TCAGATTGGCCAGGGCCCAAACAGCCCAATGTTGGCACTGGGGCGTCTCGTAGCAGCGCACCAGGCTGAGGATCGGCTCAAAGCTGCGGTAGTTG
ATGTTCCGCTCGCTCTTGATGTTCCACCGCTGAATGGCGGCCACCATGCGCTCCAGCACGTGCTCCCGGCTGGGCGTCTTGATCGTCCAGGCATC
CGCTCCGTCCGAGGCAATGTGCGCCAGCACTCCAGCCGCATTGTAGCTGACCTGGAAGCGCAGGTAGGCATGGTTAGCACTGGCCATCTCTCTCT
CCCGCACTCTCGCCACCACACTCGCACTAGCACCACCCACCTCGATGCCATCGCTCAGGGAGTCCAGCAGACGGGCAAACACCTCAATGAACTCC
TGGGTCATCAGCTTGGGCCGCAGCCACTTCACCTCGGCCACATTGCCCAGCAGGCCCATCATGTTGCGCAACAGCTCGTCACGATCCGGGAAGGT
CTGTTTTGGAAAAGGACAGTTCAGCTTAAGAAGTCTGGATACAGGAAGTTAACCTATTTCTTCATGAAACCAAGGAGTATACATTTGTTCGCTTT
CTCTATGCAGCTCTTAAATTAAATATTTTAGTTCCCAATCTTATCTTTGTTGCGCTGCGGATAATGGCAAGTTTTTGGAGAACTTACATGTAAAC
ACTTAAGGAAATACTCCATGCCACGTCCATCGAGGAATCTCTTACAATTAATAGCAGTCTCATCGGTTACGTTCCACATGGTGGACCAAGCCACC
TCCATCACATCGTCGAAAACGGAGCGAGTCAGCCGATCCTTTATCAACGTGAACATGGTCTAAAGTCAAGAATATCACCAATAAGTACAATAAGT
TCCGGCAAACAGTTGATAGGCAAGACACTTACACTAACTACGCCCAACTCGCCCAGGAAGAGCTTCTGTCGCCCATCCACCTGGCAAGCGAGTGT
GTTCAGCAGGTAGATTGCTATGCGCTGGACAAATCCCTCTTGCTCCGTCTTAGAAACGCCGTGCAGCAGGATCTTGATGAGACGCTCGTACTCGA
AGAGCTGAAAACCAGACATTTAGCTGTACTTAATATAATATTAGATTAGGCGGTGCTTACCACATCGACTGGCATGTGAAACTGGGTGAGCGTGA
GGTAACCATTCCGCAGCATGGTGTCGTCGGTGATGTGCATCTCCATGCCATTGAGCAGCGTGCGAATGATGTGATTGCGCAGTAGTGCTCCAAAC
TTGGATCGATCCCTGCCCTTGACAATGTAGAACAGCGTGGCACTAATGAAGATGAAATTTAGAATTAAATACTATTTTCACTTAACTTCAAAGCT
ATAAACCCACCTGCCGGAGATTTGCATGTGCTTGAACTTGAGATGCCGATCCATGGCGGAGAGCACAACATCCAGTGCTGTGTGTATGTCCTTGC
AGTTCTCGAAGCGGAAGAGATGGTACAAGTCGTTGAGAACTCTTGTCAGAAGCACTGGTCTGTCGTGGTAATAACGCGCCGCAGTAAGGATTTGC
TGCTCGTTGGCATCGCCAGCTACCTCCAAAGCTGGAATATCGTGTCTTTTGCAGGCCCAGTGGGCCGTGTGATAGAGGCCTAGGAACTGCAGCGG
TCGCTGGGTGCGGGACGCTAGCCCCGGGATGTCTGTGAGGGCAAAGTGTTGCTCCATTTTGGGGCTCTGCTGCATGCCACTGGTAGTTGTCGACT
CCTTGGTGGCCACACCGTTGCCGGCCAAATTCGTGCCAGAGATATCCAAATGTGTGAGATGTCGCAAGTTGTCCATCAGCATCTCCAGCGTCTGA
TCGGGCAGGTCGTAGGTGCCGTGGCCATTTCCGGAACTGGAGATGGATATGTCCAGTGTGCACAGACGCCTCAGGCAGCAGATCGCATGCAGCTG
GTTGGCGATGGGCCACACATTGAACAGGATGAGCGTGTGCAGATTGGGCAGCGAGCCCAATGCCTCAAGGCTGAAGTTGGCCAGCACGCAGGAGG
TCAGGTCCAGGTGGCCCAAGTCGTGGAGGTGAGCGAACTGCAGGCGGTGGTGCATCACAACACCGTTGAGCACCAGCCGCCGCAGATGCGGACAA
GTCAACTGGAAGTCCACTGGCTCCTTCTCGTTGGGCTCCGCGTACTGCAGCAGATGGGAACTGATGCCCAATTCCAGGGATCGCAGACTGTCGCC
GTAGTGGGCCAGAAGGTGGTGGAACCAACGGATATCATGTCACAGTACCACAAGGACAAAGCGAACAGTTTGTGCCGCATCAGAGTCTCCAAGC
CTGCAAAATGTATCAAATAGTATTTCAATATGTTTTAAACTTATTCAAGTCAATGTGGTTCAGCAATAAATATGCAATAGAAGGTTGATTGGATA
TCTATCAATTCGAAGGTAACACATTTACATAAGTGTAATTTTTCAAATGAACTTGCATCTGATTTTGTATAAACTTTTAGAGGTGCGGTTGCAAA
TATTTAAATTTAAGTTTGTCTGTTTGAAAGTCTGACAGATTCCAGTATAAATTCCGTTCAATTACTATTCAATGGAGCTCAACAACACCGGATGT
GGGCGGAGAACACTACGGATGGCGGGCAGAGCTCACCTATACTGCTTAGGGTGCTGTTGCGAAGATTGACGATCTTGAGCGAAGTGCGGTGTGTG
TCCTCGAAGAGGCGGATGACGCTGTCGTCCAGCGGGCGATTGAATCGCTGATAGTTCTCGAGGAAGCCGTCGCAGATCTCGTTGGGCAGCACAAT
GCCCGGATTGAGGCCGCGCTGGCCATCTGGCCGGTGGCTGCTAATGATGTCCAGATTGTTGCACAGCTTCTGGTAGGCGATCTCCTTGAGGGTCA
GCGGCTCCTCGTCCAGCGAGCCGTCCTCCATCAGCCGCACCTTGCAGCTCATCTTGGGGCCGCAGTTCTTGTGCTCCGCCAGTGGGGCCTCAATA
ATGGCCCTGTTGTCTAAAACGAAACGAGGCGATGGGAGGTATGATTAAACAAAATTTCAATAAGCGTGAAACTAGTTTTTGGGTATGTGGTCATC
ATTTCATCATTTTGTGAAATATTGAAATTACTGTTCTTTGAAATAAAAAAAGTGTTGAAACAGAATTCAGAAACGATATCGGAGAATATACATGA
TAATTTATTTCAAGTCATGAAATGACTACTTCACATTATGATTATTATAGAAATGAACTTATATTGCTGATAATAAAATTAAATTAAACACGGGT
TTTCTATCACAAAATACAAAACTATTGTAGACCGGCTTTTACTTTTAATCACGAGACATGCACATGTAATGCGTTCGATTTTTCAATTAATTTAA
ATGAATTTGATTTTGGCCCATTAATCCATCCAGGTGCTCAAACTCAATACTCTGTCGATTATACATGATTTTATAGCCCCTTATTTGAGATTACA
AGTCATGATGGAACGGATGAGTGATTCAACCTTTGAATCACATCAATGAATGAATGAAAGTGCCCTTTTCTTTTCAAGATTACAGACATGGATTG
CCATTGAAGTGTTTTCCATTGAGTGAATTAAATATTTTGTCACTTTCAAATGAGCCCTTAACATCAATGTTTATAAAATGAGCTTACAATGTATT
ATTATACTAAGATAAATGGGCAATGACTTGACATTCTAGATTATATACTTTTTGATGTACGATTTCTTTAGTTCTTTTGTAAGCTAGCCAGGAAT
TAATCAATTTAATTAACGAGTATAGTTTGTGTTTACATGTTGCACTTTTTCGACTAATTATTGTTTGGGTATAGGAAGCGGGCTTGCCCTTGCAG
TCGAACCCTTGCAGCTCCTAACTTTTGGAACTTGAGTTGCCATGGATGACTGGCCAATCTTGCCCAGACTTTTCAACGCAGGCACGTGCCATTGT
TTTAATCTGTTTTCGGCTCTTGGCTTCCGATAGTCATGTACCCCTGCTGTTACATAACCAAGGGTCATCTAATTGGGAAGAATGCGGTATTAATA
CGGGGACTATGATCCTGGTTACATCCAGGCAGATGGTTATGTCCATGTCGTGGCGTGTGTGTATGTATATGCACAAGTTCCGCGGATCTCAAAGG
TACATACATGCATGTAAAAAACAAATGGCTTGCGTGTGTCTGTGTGGGTGCGTAGTTATTGAAGAAAAAAGCACAAAAACACTAATAAAGCGTCG
GCCTGTCTGGCTTATCTGGCCAACAAAACTAAGCGGAGTGACCAAAATAACACGGAACTGCGAGCAGCGACAGTCAGCTGTCCGGATATTTTTAC
CCGGAGTCTCGGAGTTGCTGGCCGACTGGCCGTGGAGCCCCACGCTTTCTGTACCTTTTATTTTGCTTTAGTGTCGCCCCAAAAAAGCAGCCTCC
AAAATCCCTCGCTGCTTTTGCTTCTGTCGTTGCGTTTGTCTTTGCTTTTGCGTTTGCTTTGCCACTGCTGCTCTGTCTTTGCGTTCGTTTTGCCA

FIGURE SHEET 73

ACGGATTTTCCGAACTTCGAGCGATTTTTCCGCGATTGCGCAGCGTTTTACCGTTACACGCGGCACTCGAGCGCCAGAAAATTCCAATTGTTATT
CTCTAATTTTACGATTTGCGTATGGAAATCACTTCATTATTTTGGTTTCTATTTTCTTTCTTCTCGCCAGTGTGACCAGATGCCGAATGCGCTCC
AACACCCAATGCTGTCTACCTAACACTACTTCGCACTAAAAAATACCGAAAGTATCCTTTCATATTCGAAAGCTAATCCGAAAATTCTGGAACTC
CGAAATCCTGACTTTTGAAAATCTAAAGTTAGTGAATAAATGTTATGCAAAGGCTTGCAGTTAAGATATGCAATTACTTAATGTCATTAGCCCGC
GCAAGAAAAACAGACACTTGAATTGGAAACTATAGTTTATTTTGTAAGTTAAGCGCTGAAATAAATCAATTGTAAATGTACACATTGTTAGTCGG
CGGCGGCGTGCTTGCCTGGGTTCTAATTTGTAGTTCTCTTGCTCCGATAATGCGAAGAAAACCGACAATTGCTTCCCTCGCTGTAGGGATACTTT
TTAAAGACTAAATCACTGCGTTGCAGAATCATCATAATCATCATAATCGTATTGTATAATCCGGATGCCGTGCCGTTGGCTTTCGGACTGGCGTA
ATAAATAAACTTGCATCGTTTGCGTTTTAGGTGCTACGTAAAAAATGATAGAACAAATGCGGGGAGCCGCATGCAATTCGGATAGCTCCCCCTTC
TAACCGGACAGATCTCCCTGATCGAAGATGCCCTGGTCGTAGAGCTCGGCCACCACTCTCCGACCGCCGAAGAACCGGCCGTCGAGTGCCTCCTT
GCCCCGCATGGCCTCCGCTCCTGCCGAGAACTCCACGAAGATCTTCACGATGATCTCCGCCTCGTCGTCGTCCTCGTTCTCCGTCTGCTTCTCGT
TGAAGATGATCACGCGACTGACGGTGCCGAATTTACTGCACTCCTCCTGGATCTCCTCCTGCAGGGTCTCGTCCACATCCTCGGGTCCGACCATA
TTTCGCAGGATGATTACACGTGAGTCCACCGGCCGCATCAGTCGCTGCATTACCAACTGCCGCGCGCTCTGGCCCTTGATGGACATGTTCTCCTG
CTGCTGCAGCGTCTGCACGTCGCCCTCATC
(SEQ ID NO: 157)

Exon: 5870..5565
Exon: 4193..3837
Exon: 3515..2576
Exon: 2512..2341
Exon: 2284..2123
Exon: 2054..1893
Exon: 1710..1561
Exon: 1476..1231
Exon: 1165..1001
Start ATG: 4116 (Reverse strand: CAT)

Transcript No. : CT5498
TCACACTGGCGAGAAGAAAGAAAATAGAAACCAAAATAATGAAGTGATTTCCATACGCAAATCGTAAAATTAGAGAATAACAATTGGAATTTTCT
GGCGCTCGAGTGCCGCGTGTAACGGTAAAACGCTGCGCAATCGCGGAAAAATCGCTCGAAGTTCGGAAAATCCGTTGGCAAAACGAACGCAAAGA
CAGAGCAGCAGTGGCAAAGCAAACGCAAAAGCAAAGACAAACGCAACGACAGAAGCAAAAGCAGCGAGGGATTTTGGAGGCTGCTTTTTTGGGGC
GACACTAAAGCAAAATAAAAGACAACAGGGCCATTATTGAGGCCCCACTGGCGGAGCACAAGAACTGCGGCCCCAAGATGAGCTGCAAGGTGCGG
CTGATGGAGGACGGCTCGCTGGACGAGGAGCCGCTGACCCTCAAGGAGATCGCCTACCAGAAGCTGTGCAACAATCTGGACATCATTAGCAGCCA
CCGGCCAGATGGCCAGCGCGGCCTCAATCCGGGCATTGTGCTGCCCAACGAGATCTGCGACGGCTTCCTCGAGAACTATCAGCGATTCAATCGCC
CGCTGGACGACAGCGTCATCCGCCTCTTCGAGGACACACACCGCACTTCGCTCAAGATCGTCAATCTTCGCAACAGCACCCTAAGCAGTATAGGC
TTGGAGACTCTGATGCGGCACAAACTGTTCGCTTTGTCCTTGTGGTACTGTGACATGATATCCGTTGGTTCCCACCACCTTCTGGCCCACTACGG
CGACAGTCTGCGATCCCTGGAATTGGGCATCAGTTCCCATCTGCTGCAGTACGCGGAGCCCAACGAGAAGGAGCCAGTGGACTTCCAGTTGACTT
GTCCGCATCTGCGGCGGCTGGTGCTCAACGGTGTTGTGATGCACCACCGCCTGCAGTTCGCTCACCTCCACGACTTGGGCCACCTGGACCTGACC
TCCTGCGTGCTGGCCAACTTCAGCCTTGAGGCATTGGGCTCGCTGCCCAATCTGCACACGCTCATCCTGTTCAATGTGTGGCCCATCGCCAACCA
GCTGCATGCGATCTGCTGCCTGAGGCGTCTGTGCACACTGGACATATCCATCTCCAGTTCCGGAAATGGCCACGGCACCTACGACCTGCCCGATC
AGACGCTGGAGATGCTGATGGACAACTTGCGACATCTCACACATTTGGATATCTCTGGCACGAATTTGGCCGGCAACGGTGTGGCCACCAAGGAG
TCGACAACTACCAGTGGCATGCAGCAGAGCCCCAAAATGGAGCAACACTTTGCCCTCACAGACATCCCGGGGCTAGCGTCCCGCACCCAGCGACC
GCTGCAGTTCCTAGGCCTCTATCACACGGCCCACTGGGCCTGCAAAAGACACGATATTCCAGCTTTGGAGGTAGCTGGCGATGCCAACGAGCAGC
AAATCCTTACTGCGGCGCGTTATTACCACGACAGACCAGTGCTTCTGACAAGAGTTCTCAACGACTTGTACCATCTCTTCCGCTTCGAGAACTGC
AAGGACATACACACAGCACTGGATGTTGTGCTCTCCGCCATGGATCGGCATCTCAAGTTCAAGCACATGCAAATCTCCGGCAGTGCCACGCTGTT
CTACATTGTCAAGGGCAGGGATCGATCCAAGTTTGGAGCACTACTGCGCAATCACATCATTCGCACGCTGCTCAATGGCATGGAGATGCACATCA
CCGACGACACCATGCTGCGGAATGGTTACCTCACGCTCACCCAGTTTCACATGCCAGTCGATGTGCTCTTCGAGTACGAGCGTCTCATCAAGATC
CTGCTGCACGGCGTTTCTAAGACGGAGCAAGAGGGATTTGTCCAGCGCATAGCAATCTACCTGCTGAACACACTCGCTTGCCAGGTGGATGGCG
ACAGAAGCTCTTCCTGGGCGAGTTGGGCGTAGTTAGTACCATGTTCACGTTGATAAAGGATCGGCTGACTCGCTCCGTTTTCGACGATGTGATGG
AGGTGGCTTGGTCCACCATGTGGAACGTAACCGATGAGACTGCTATTAATTGTAAGAGATTCCTCGATGGACGTGGCATGGAGTATTTCCTTAAG
TGTTTACATACCTTCCCGGATCGTGACGAGCTGTTGCGCAACATGATGGGCCTGCTGGGCAATGTGGCCGAGGTGAAGTGGCTGCGGCCCAAGCT
GATGACCCAGGAGTTCATTGAGGTGTTTGCCCGTCTGCTGGACTCCCTGAGCGATGGCATCGAGGTCAGCTACAATGCGGCTGGAGTGCTGGCGC
ACATTGCCTCGGACGGAGCGGATGCCTGGACGATCAAGACGCCCAGCCGGGAGCACGTGCTGGAGCGCATGGTGGCCGCCATTCAGCGGTGGAAC
ATCAAGAGCGAGCGGAACATCAACTACCGCAGCTTTGAGCCGATCCTCAGCCTGGTGCGCTGCTACGAGACGCCCCAGTGCCAACATTGGGCTGT
TTGGGCCCTGGCCAATCTGACACAGGTTTATCCCGAAAAATATTGCAAGCTGGTGGAGCAGGAGAACGGCATCCAGATCCTCAACGAGCTAATCG
AGCACGAGAGTCCCTACTGCGAGATCAAGCGCATCGCTCGCCTGGTCATAGAGCAGTGCGACTCCGGATCGGAACGCATGGTCGTCGACGGCTAA
(SEQ ID NO: 158)

Start ATG: 384 (Reverse strand: CAT)

MEDGSLDEEPLTLKEIAYQKLCNNLDIISSHRPDGQRGLNPGIVLPNEICDGFLENYQRFNRPLDDSVIRLFEDTHRTSLKIVNLRNSTLSSIGL
ETLMRHKLFALSLWYCDMISVGSHHLLAHYGDSLRSLELGISSHLLQYAEPNEKEPVDFQLTCPHLRRLVLNGVVMHHRLQFAHLHDLGHLDLTS
CVLANFSLEALGSLPNLHTLILFNVWPIANQLHAICCLRRLCTLDISISSSGNGHGTYDLPDQTLEMLMDNLRHLTHLDISGTNLAGNGVATKES
TTTSGMQQSPKMEQHFALTDIPGLASRTQRPLQFLGLYHTAHWACKRHDIPALEVAGDANEQQILTAARYYHDRPVLLTRVLNDLYHLFRFENCK
DIHTALDVVLSAMDRHLKFKHMQISGSATLFYIVKGRDRSKFGALLRNHIIRTLLNGMEMHITDDTMLRNGYLTLTQFHMPVDVLFEYERLIKIL
LHGVSKTEQEGFVQRIAIYLLNTLACQVDGRQKLFLGELGVVSTMFTLIKDRLTRSVFDDVMEVAWSTMWNVTDETAINCKRFLDGRGMEYFLKC
LHTFPDRDELLRNMMGLLGNVAEVKWLRPKLMTQEFIEVFARLLDSLSDGIEVSYNAAGVLAHIASDGADAWTIKTPSREHVLERMVAAIQRWNI
KSERNINYRSFEPILSLVRCYETPQCQHWAVWALANLTQVYPEKYCKLVEQENGIQILNELIEHESPYCEIKRIARLVIEQCDSGSERMVVDG*
(SEQ ID NO: 159)

Celera Sequence No. : 142000013384767

ATCCTCCAGCTGGAGTTTCTCGCGCAGCTCACGCTGCAGCAAACTTGGCTTGATGATAAACGTGGAGATGCGACGCAGGATGTAGGAGAAGGTCT
TGATCAGCAGCAGGAAGTCCTGACGCGGTACGCCCACCAATCGCTCCAGTTCCTCGAGTGTGTACTCCGGTTCGGTGTTACTTGTGGGGTTCTCC
TCGGTGCTGCTGTCCACCCGGCCGGTGGTCGTCACACTGGTGCCCACTGTACTACTGGTGGCACTCGCCGATGCTACGCTGGGACTCATCTGCCG
GTGGGTGTAGAACAGAACCGTCGTAAAGGTCTCGTAGGGCAAGGCATTGATGATTTGATGCCCTCACGGGCTCTAAGATATAAATGCAAGAAAT
TAATCTCTATAAGAACATTGATATTACATACCTTTCCGTGATCTTTATCCAGTTAATGCTCATTGTGAGATATATTTAAAAATTTTTAAGGAACA
TAGAGTTATTAAGTCTTTACCAGCACTTCTTTTATTATGACTTTAATATTATTTGTTTATACAGACCAACAATATACAAAAAACTATCGACTTGC
CACGGTGCGGTGCTGCCACACAGTTACTACTGCCAATAATAACGGTAAGTGCTGACTAAAATACAAAAATATTACATTTTGCGATGTGATTTTAA
ACATATTCTTTATTAATTTTTTAGATTTAAATGTTTTATTAAATTAATTTATTTTTCTGTATTTAGGCCTGAATAATTTACCTTATAAAATTACA
ATGTTTTAAATAATATTTGCTGTTATGTTTCCTGCAAAATAAAATTCGTGAAAAAAAGCCGCACCAGCAAATATCAATACCAGATTGTCGACGGC
ACCGACGATCGACGATTCAATTTGTAGAAGATTATCAAGTACGAATAGTTTTCCAACTCATTAATATAATCGTCCTACCTGGCAACTCCGCTGAT
GCCTATCGATGCTCCGCTCGATAGCGCCAACAATCGATAAGCAGTATTTGTGTATTGGAAACGCGGCTTAACTTAATGCAGATTTTTCCGCTGAT
TCGGCTGCGAAAGATGCACTTTTAAGGCGCAGCGAGTGCACCCACGCCCCGAGTTCGAGTGCAGTTGCAGTCGGGAAAGCTTGACAAGTGCGCGG
AGCAAGGAGAGCGACGAGTTCGTTGAGCTACAGCGAAACGGAAAAGTGTAAAAGCGGGGTAAACAGGCGCAGCGGAGCGGATGATAAACGGAACT
CGGGATCGGAAAATTGGAAGCAAAACCAACCACCGATTATAAAAAATAGTCAGCATCTTAAAAGTAAGGATTTCAAGCTAAGGTTTCAGCGAAAG
CCCGAGAAAAACAAAAACCCCAACTAAACTAACGGAACAGTGCGTCGGGATATATGCATGTGTATGTGGTATACGTATGTGTGTCTTTGGCTGCG
TGCGATTGTATTGTTCCTGTGTAAATAAACAAAACCCGGCTCTTTAGTCTTCCACTAGTTCGTTTCGCGTTTCTCTGCGAGGAATTTTTGTTGAA
AAAACTCAATTTGGCATAGCATAACTTCCAGTTTATTTCCCTATTCTGCAAACTGTGTGTATCAGTGTGCTGGTGCTTCCAGCATGCCGTAAAAA
TCGATAGCGCGTCGTCGGTTGTTTATTTTATGCTTCGTCTGCATTTTGCAGCCCCTTTTTATCGCTCTCCCCTTTTCAGCCACCCTTGCACACAC
TCACACTCTCTCCGGCGGAGTCGTGTGATGCATACACACACACACACACAGACACATGCATACGCCTGATACGGGAAATTAAAAATAATACTTTT
TATCGCGGCATGCAAAAGGCAAAGCTGCAAAAACAGAAACAATTCCAATTCCAACAGCAATAATCTAGCCATGCAATCAATTTTAGCCAAACAAT
AAAAAGAATCGTTTGGTTTCAGTTTCCCCGCTTTTCTTTTCCGTTATTTTCCTCTCTATATTCGGTTTTATCGCATTTTCCGCTCATTATGGCAG
TTTAGCATATTTATGCTGGAAAAATATTGGGGTTTCTTCGCTTCTTACCTTTGTTTTACGTTTTGTTTTGCTGTCGGGCTGTAAAAACAGCAGTT
AATCCAATTAAGAAAAATAAAACTCTAAATGCCATCGCCACCACGAATTCGAAATCACCTTTTATCTACTCAAAAGATATTCATCTTATTTATTT
TCCAAGATAAATGTTAAATTATAAATATATTATAGAACCATACACTTGTTGAAATAGAATTTCTGCTAACAGCTGCGAGTTTTACAGTCATAACT
ATTATTATTATTTATTAACTTAGATTTCTACAGGCTGCGATTTTATAAAAATGATTCAATTTTTTATCTAGACTTTGTTATTAAAATTTCTACAT
AAGCAGAAAATAATTGCTGCAATGACAAATATTTCATTTTCAGCTTGTGTTTATCGTAGCTTATTTTTTGTTAAATGTATATTAAAGTATTTACT
CCCCTTCTCATGTAATATACATATATTGAAAAAACAGTACTTTTGTCTATTAGAATATATTTATACCCTCACTTATTGGTTCATCTCGAAAACTG
GTCGAGTAAACTGAGAATCTTGAGATAGTTTCTTGAATTGGATATAATTTGCATGGTTGGCCAATCTTTTGGGTCGGCTATGCCCGCCTCTTTGC
TTCGTAGAGGAGCTTGGGCACCGGGCACTTGCAATTGGCACCAGCTTCGGGCCAGTCAGTCCGCCAGACTTGGTCTTTGGGTCGAGATGTAGAGC
TGGATAGTGTGCCACACTATATAGGGGATACTACTGCGATACAGACACCGCGGACACGGCTGACATGCATTAATGCTGCGAATAATGCCTATTGC
AGACGGGGATAATGGAGTCACAGAAGCGGCCTTCGTTGGACTTACACACGGATGTGCCAGCAGGATTAGCAGCTGGAGGATCTGGCCTGGGAGCT
GCAGCTGAGATGTCGCCCACTTCCGGTTTCCTGCCGGACATGCCGCAGTGGAAGAAGGACCTCATCCAGCGCCGGAAAACGAACGTGGCCCGCAC
CCAGGCGGCGTCCATCACCTCGCCCACCGATGGCAGTTGTGGGGCTTTGGCAGAAGCCAACGCAGCTCCAGGTGCAATTGCAGGTGAGTGGTGGT
TGGACAAACTGGAATACTTTCACCTGACACGCAAATTAAAGGTATTTTCAAGCCAAGCATTTCTGTCAAGGCATGTTAGGTGCAAGTATTCGTAT
TTCTAATCGCTATTTCTTGCATTCTTGACAAACGAAATAATTGCACTTACTTTTGAGCTCCATACTTATCCCTTTTAAATGATACCGTTCGGTAC
TTAAAATAAATTCAACGAACTATAGACTTCGGAAAGGTTTTTAAAATATTTAAAAACTGCCGTAGCAAATAGTAATCAGGGTGAAATATATTGAC
TGGAAAAATGCGAAAGACTAATTGTGACTTACACAATCTGCAATTGCTCAGTTGGCGTTAACCAGCCATGAGTAATGGTAACAAGTGTTTTTAAT
TCATTTTGCCAACTTTTACGATTTCCAATACCAGTATACTTTTAAATTAGCCGCCTTACATATTCGCTTATCGATACGATATTCGCTTATCGATA
GCTCACAGAGTTGTCAGATTGCGGACGAATAAGATAAAAAAAACCAAGTTATGTTTTAATGTTCTGTCTTTATAACATTTGTATTTGCTTTCTTT
CTTCAATTTTTTTTCTAACAGATTTCACAGAACCGGCGACAATCAGTAGCACTAGTCAAAAGAGAAACATGATCGGTTCAGAGGAAAAGTCTGAG
AAATCTTCTATTTCCAATACCAATTCCGATTCCACTGGAGGTCATCACTCTGTTGTTGCCGTCTCCCTTTCGCCCGATGCGGCAGCAACAACAAA
TGTAACAGTAACACCAATACCAAAGCAGCGATCGAGTTTACTCAACACAAGAAGTCAGGAGAGGGAGATGGTGCGATATATTCTAAGCGAGAGTG
GAGAACGGGATGGAGAGCTTGAGAGCGGCGAACAGCCGGCTGGTGTGGTGAGTAACAGCCGGTGCGGTGAAGTTGAAACTGGCACAATTGGATCG
CCGTCGTCGTCAGCAAATCAAAATCCAAACCCAAATCATTTAAAAACGAAATGCAAACCGGGACAGAGCGTTGCTGAGGGCAAGCCTTCAGCTAA
AGAGACCATCGTCGATAACAGCAAAAGCTGCAGCAAAACCAAGAGTATTTCCGATAAATTGCAGAGCAACAAGTTTATAATTCAACAGCAGCAGC
AACAACAACAACAACAGCAGCAACAACAGCAACTGTCGCCCACAAAGGTAACGGTAAAACCGACAATGGTCGCCATGCAAGAGATGAAGAAGACA
ACCAAACAAAATGGCCAGCACCGACATCTAGCGGGCAAAATTGGCAGCGTAGCAGGAGGCGATGTGGATCCACAACATCCACCGACGAATCCCAT
ACCAGATTCATTGGACACCGGTGAGGATCTGAGCTACGGACCCGGAATTGTGTCCAAGCTGCGATGCCGCTACTTGAGCCTGGCCCTTCGCGAGT
CCCGCCAGCAGAGCAGCAAACAACGCCTCCAACGCTCCACCAGTCTGAACACCCTGCTCGACCGCGACGATGACGAGGTGGAAGTGGAGGAGCCC
GAAATGACCAACAGCCAGGTGCGTGCCAAATCAACACCGCCACCGATATTGGGGGCAAAACCGACACCGAAACCCAGCAGCCAGCATCAGCGTCC
CGTCAGTCTGGGCGCCAATGGAGCTGGATCAGCTGTTAACCCGCCCTCGAACTCGGATCAGGCCCAAACGGGCGCCGTTGCCAACGGAGGCGCAG
GATCTGGCCAACGTTCGCGTCACTTTAAGCGCGGCAACGAGGTGATGAAGCGGGCACGTTCCGTGGAGGCTCTGCTCTGCGAGAAATCGCCATGG
AACAGCCAGAGAATCAGCACTGCCGGCGCAGCTGCAGCAGCAGCACCTTCACCACCTGCTCCCAAGGCCACAGCCGCTGCTCCCTCACCTGTTAC
ATCGCCCACCTGCGTTACCATCGAGGACAAGATCCACAATGCCCGCGAACGACTGCACAGCGGGACGGATACGGCGCCACCCAAGCGTCTGACCT
CCATCATCGATGACACCGAGCGGCCGCCACCGGATCTGGTCAAGCAGACGCTCAAGATGTTTGAGGCGAGTGCTAATCGACGACCGCGCGCAGCC
CATCGTTCCAATGGTGTTGGCGGAGTGGCCAGCAAGGTGGCCAACTACAAATCGATCATTAAGGATCAGAAGCAACCATCATCAGCAGCGGCGAC
GCCACCGCCGACCGGCATGGGTTTTGCCTCCTCAACGCCGCTAAGGCATGTCCATCCGGATATTATACCCCGTCAGGTGGATTCGCCCGTATCGG
CGTTGAGTGTAATGATGCGTCGCATGGAGCTGCAGGAGCCCGAGACGCCGGAAAGGGAGACACGGGACGCGGAGGCCACACCGCAGAGCGAGGCG
CTAAGTGAGACTGAGCGAAATGATCGCGATGAAGGCGATGGCGAAGTCGATGACGACAACCACAACAACAACGACGACGATCACGACGACGGCGA
CGACGGCAGCGACAACAATGAGCAACGCGATAAAATGGGCGCGGCGGCGGCAGGCGATAAGCCTAAGCCCCCAGCGGAATCGGCAGCGGGAGGCG
CCCAACGATCATTCGCTGCCTCGACGGAGAACGCGCATGTAGCCAGCGGTAGTAGCAGCAGTACCAGTGCCAGTGTACGGAAGCTCAGCAACAAC
AACGACTCCAGCAGCGGACCAGCGGTGACCAAACAGATCGGTGTCATCCGTCCGCTATTCAATAGCCAGGGAGCCGGGAGCACGCCGCTAACGAG
TCGCGAGATCGAAAAGAATCGCATCAATGAGATGAAGAAGTCGACGGCCACAGATGCCGGTGGTTCGGTATCCGGATCCGGAACGGTTGCTGGTG
CTGGATCAGGAACCTCGCCCACCACTAGTCTCGACAGCGTGATAAACACCAAGGAAGCGGCCAGCAGCGAAACGGATGCCAGTGCCTCGCCACTG
TGGACATTGCGCAAGCTGAGGAATCAGAGCCAGACGGCCGGCGGAGGATCGGGTCCCAGTTCGAGCCTTCATTCCACAGAGAACACCTCGATGGT
GTTCAACTTTTCCAAGAGCACCAAGGAAGTGCCCGACTACATCGAAAGCGACGTTGTGATTTACAGGCGCAAGCGGGAGCTGCCAAAGGTGAGTC
CGGATTGGGTAAATGGTTACTACTACGAGGGACTACGATTTCCATTTCCGTTCCTTGACGCAATTCCTTCGTGCGTTTCGTTTTTTTTTTTTTTT
TTTTTACGAAATCTTTCCCGGAAGAGTCACATTTTCGACGTCTTATCGGCGGGCAGCCTTGCGGATTATTCATGCTTAACAATTACCCCATGCAT
TATTATTTTCGCCGATAGTAATTTGGTTTCTTTCGTCCGTCCCCAATATCTTTGTTGTTTTGGCTCATTTTCCGTTTCTTTCTCGCGTACTTTTT
TTGTATTATTATTATTATTTTTTTTTTTTTTTTTGTGTCATACGGCGGCGGCAGCCATGCCGTATAAACAAATATGAAACAAAGCACACAGAGA

FIGURE SHEET 75

ACAGCGATCATGCGCATTTCGAAAGTTCATCAAGGCAGGGCGAGAACGGAACTGAGGAACTGCGGAGAATTGGGTGGCGCAGTGACAAAGCGCCA
CTTGGATACTCTTTCTTTCTTTCTTTCGAGGGAACTCATGTGCCATATGTATGTACATATATCTTTATATCTTCGCCTTCTGGGAAATTAGTCAT
GTGTCGTGAATACGTCGTTAATAACGCCAATATTGCCAAGATGACTGACTAACTGCTCACATGCGATAGGGGATCTCCTCCAGCTGTTCGATCGC
TGATCGTGTTAATACCCATTTAGGAGTTTTACAGATTAGGAAGCAGTTGTTAGTTAAGGAACTTTGTGTTTTTAGTTGGTATTGCACCACCAGG
AAATTATTGGACTACATTTAATATATTTGCAATATATACAAGGGATCAGTAATGTAAAGGCCCCACTCTTTCAATTATCATTGAAATTAGCAGAA
CTACAGGTTTCCAATGACTTCTGATGGGTATGTGTGTGTGGCCATTTATTATCTGCCGGCAACCAAATCATTGTGTTGATCAATAAGTATCTGGC
CAAGATTACACAGCACAGTCGGTTAATCACAACAATACGGCGATCTGGCAGATCAGTTGGGGGATCTGCCACTGCCACTGCCATTGCTGGTGCT
ATTGCTTTAGGAAGTGGCAAACCCCTAATAGAGATCGAAGCTTGCATCACAGCTGCGAATAGTTCGATGTGATCTTCTGCTCCGAGTCAATTAAA
ATTCGCCTTGAATAGCTCGCCGATCGATAGCCCCGGATCGTGTGCGACATGAACAGATGCCCCTCCTATATGTATATGCATATACATAACTCGAA
ATATATATATATATATGTATATATACATAACACATATATCTGCATATTCTTTCCCAAGTCTGCTTTGTTCCCAGCCAGATGCAAGTCTCATCTGC
TGGCAGTCTTCTGCCTTCGGTCGCTTCTTCTTCGTTTGGGCTCTTCTGTGGCTGCACTTTTCGAGATCGGAAGAATGGGAAACCAGTTTTGAAGG
CATGCATATGGACATGAGAAGATATTTCTGCGCTTCCTGCTGCTGCCAGCAAAAGTCCGAGTCTGTAGAGATATGTATGTGTACACAGTGCCCAT
GAGATATTATGTGTCTGGTCTGTCTGTCTCTCGGTCGGCATGTCTGTGGGGAACTTTATTCTTGGGGCACAGCAGCTCCTCGGGATGCCGGTTTC
GATGGTATAGAATGGGATGGGATGCAAGGCAAGGCTGCTCCTTACAGCTGTTCCTGTTGCCTTGCCAGACATGTTTAAATACCCTTTATTTTGTG
ATGGCAATTGAGCTTTTTTTTTATTGTTTATACTCTGATAATCAATTCAGTAGCTCAACTTGAATGATTCTTGTTTATAGTAGATATCCAATACG
TATGGATTGTTTTGATATGAAAGAGACACACAGAACTTGTTAATATATATTTATTAATACCAAATTAGGAGTACAAAGCTCCACAATGGTGTCAA
ACCCAAATATTGTTCTTCGCAATTGGAAAAGCGAATGGTACAGACCATACTCTATAGAGTCTTTATAGCTCTCCCTTAGCTTTAGACTTAGCTTT
TCGGTGCGGTTGAGTTTTCCTCTTGCCTTCTTCTCGTTGGCAAACCCGTTTTGTTTGTGCTTTGTGCCGTTCTCCTCTCCCACTCCCTCTCCCTC
TCTCTCTCTCTCTCTCTCTCCCTCTCAGCTGCCATGTTTCTCTCTATGTCCATATCCATATCTCCATATCTCAATGGCTCCATGGCTCCATGG
CTCTCTTCGCCCTCTTCCTGCCACTGAACTCAATTTTGTCAATTCTTTTTTGAGGCTCACTTCTACTTACTGTGTTTGCTTTTGCTTTTTGCCTT
TGCCTTGTCTCTTTTATCTCGCTATGAACTTTATTATCTGCGGCATTGGTATATACATATATGGCATATATAGCATATGGTATGGCATGGTATAG
TATATGGCTGGGGGTCGATTTATGCCACAAAAAAAAAAAAAATACAAAAAAAATGGGCCAAAAACAGTGGGACAGTGGGTTTTGGGGAGGGTGGGGA
GGGAAGGCGTGGAGAGGAGAGGAGCGGTGCCGATAGAGTAGATATATGACATGGAACGGGACTGGGAACTGAAATTGGAACCGGGACCTGGACTT
GGTACTTGGTACACTGGTCTGGACCTCTGGAACCCCCGGCGTGAGTCACAGATGACCCATAACACAACGTCGATTAAGAATGGCTTTCCATGAAT
TTCACTTTTCGAACACATGGTGACCTGGAATTTGGACAGATTTTCTTGTGGAAGGGGTGAAGCTGATCCTCCTTTGTAAATTGTCGAGAGACAGC
CATTTAAATCCAAAAAAAAAAAAAAAGAACTGAAATGAAATACTTATGGTAAACGAGTTATGCATCAGCGAAAAGAGGAGGGTTGCTGGACGTTC
TGCAACTTCTGTAGGTAGTTAAAGCGAAATAAAGGCGTGTTTACCATTAAATGATAATATCTGAAGCAGCAGAAGAACATTGCAAATAGCTTTAA
CAACATTCGAAAGCAATAACACATTTTTAAGTGCCTTGTTTGCATTTTAACGAATTTCATTTCCCAGCTAACAAAACGTTTGCAATGAAGATAA
TGAATATTTTTGTTGGGGGGGTTGTATACTAATTCAAAATCAACATCTACTGTATTTTATTTATTATTTGAACTATTTGTGAACCCCCGGGGAAT
GCCAAGAGTCAAGCATTTATTGATTGTACTAATCGTTTTTTTTTTTTTATCATCTTATCCTTTTAGCCAAATGAACCTGGCTTCGTGCTCCTGGGC
GATCTCTCCGTGGAGACGTCGACGGACACGGACTACGACGACTACTCCATGTGCCCGCCATCGCCGTGCGATGTGGAGTTTGAGAATGCCAACAT
TGTGATCGACGGCAAGTCCAGCATACGCCAGAAACCCAAAGAGTCTTCGGTATGTACTACACCAAGGGATATTGCCGGGATTGGATTGGAGATCG
ACTAGATCTCAACTCAATTCCAAGCCATATGTATATGTATGCGGTCGTTACATACTCCACTACTAATGAGTGAGTCAGGTGCGGCGTTTTGTTTT
TTTTGCCACCGAATGGTAGATAGCATTGGTTTTTTTTTTCAATTCCAGTTTGGGTTGTGTATGTGAAAAGGATAAGATAAGATTACTTGGGCCCC
TTGGCAAGGAGGGAATGTACATACATACACATGTACACACACACGCACACATTCGAACTTTTGACCACTAACTTCGACGGGTGGTGAGGACGTT
GATAAGCGGGAATGTAAAGCATAAACAATTTTGCCTTATATAACATTTATATCGAGTGTGTGTGTGTGTGTGTGTCGGTCGGTCGTCGCCTGTCC
CAGGGACTATTAATCAACCCGCATTAGGTTTGTCTTATTTCGGGATTTGTTTGCCCATTTGGAGCTGCTTGTGTTGCGTCCCCAGATCTGTTCGC
CTGGCGCTAATTTATTTATTTATTCCTTTGCTCGGGTGCGTTCCATCAGTGTGACTGATATGGGAATCGCTACTCTACTATTGTCTTTAGCCTCA
GCAGCCATCGGCTGTATTTCGGAATCAATTCAATCGTTTTCCGTATCGCATCGCATCGAATTGCGTCGGTCTGTTGGGGTTTGTTCTCCGATAAG
GAAGGAGCTCGAATTCTGCAGTCATTGATTGGGGTTGACTCATTGATATGCCATTGTGATAAGGCATCAATCGATGAGTAAGTGCCGATTGGGGT
TGGGAGTCGCTTTTGAAGCAATCTATTTGCCATTAACCCAATGTCACGGTTATATGCATTTAAGAAAAATATCAAATGCATTATGCATATACACA
CCATATTGCCAAAAGTCCATCAATGAGTTGTATATTTTATTTATTTATAACAAGGCATTGGTCCAATGCTTTCGTCTAACCTTGAATTTTTATGG
CTAGCAGAGAAACTACTTAGTTTCGGATATATATTCGGTGATTTCTGGACCGCTAAATGTAAATCGAACGGCATCTGGTTATGCAAATTACATAA
AGACCAATAGTTAAACGAAACCAAAATAAAGGATAGAAAACCATAAACATATATCTTTAAGTGTCAAAATGTAAAATCCAAATAGTTATCACTAA
TTTCAATGGCGCTAGTATTATTGTAAATTCTACATTCGCTTTGTTATCAGCAATGCCAGCTAGTCATACATTTATGCCAAATTAAAAATAGTTTC
GTTTAAAGGGAAAGTGGTTGAGTGGCATGATTTCAGTTCACTACGGGTATTAATTATATGACTAAAACAGTTTGGCATGTAAAAATCTATAGCAA
AAATGGCATTTGATTATTAGTTATTATTATTATTATTCAACAAATGATTAATTATAATATGAACGCTGCGACGTGTGGGGATAGCGACTTCAGAT
TCTGCCACATTACTTGATACCTTGATTGAACCCATCGAAGTGAAAGTAATCTCAGAATCGATCACTGATCAAATTTCTTTCGATTTTCCCACAGT
TCCGCGTGCAGTTCAACGACACGCTGACGTCGACGTTTGAATACCCCTCCGAGGCATCGATGACCATCGAGGATCCGCCGTACGCCGATCCCTTT
GGCCATGTGAGCAAACACCATCAGATGCTGCTCGCCGAGCAGATGCATCTGTTGCAGCACCAGGAGCAGCTGGAGCTGGAGCAGATGCACCAGCT
GGGGCTGGCGCCGGAGCAGCACCATCATGTGACCGTCGACGAGATCATCGAGCTGCCCACATCGACGGCGGGACATGGACATGGCATCGGACTTG
GACACAGGTCGGGGGCGGCGGGGGGCGGTGGCACGATGCTGGGGAATTTACCGTTGGGTAAGTAATATCTGTTCCACCGAGTCCATCCAAGCGTG
CATTGTATTATTATTATTATTATTATTATTATTATTATTATTGTTGTTGCTGTACGCTGTACGAGATGTATGTTGTGTGTTGTTGTATGTGGCAT
GCAGCAGCGAATGATGATGGAATGGCTTTTTGTCTTTGTCTCTCTCTGCGCTCTCTATTATCGTCTCTATCTCTCTCTCTGTCTGCCTGATTGCC
TGCATCCAAGCCTCTCTATCTATCCATCTCTATCTATACCCGTCTCTATCTCTGTCACTTGCCTTGTCCTTACTCTTGACTTACCATCAACCAGC
GTTGTGTTCTTGAGTTTTGTTTGTTTGTTTACCATCATTAATACCCACTCATCCATCACACATCGTCGCGATCTCGTTTTTTTTTTTTTAACACTT
TCGTTTGCCTTGGGCGGATCGCGAATATACAATAGCAATTGAGAAACCCCAAAGACAACTCAAGACACTTGTTTAGCAATGAACGTAGAAAGGTA
GTGCCAATGAGCAGCAGGGAAATATACATAATGTAAATCAGCTGGATAACCATCCTTACAATGCTACTTATAAAATGTGATGATGTGAAGGAATT
TACATGCACCATCTTATGCTCATTTTAATATTTACACTGTTCCAAGTAAAATGTTTCCAAATTAAAGAAATCAATGTAAAGTTCTCGTATAAAAC
TGATTTAAACTAGAGTTTATAGGACTACGACGAACCCAGTTCGGAACTGGGTGACCCGCAAGCCCACATCCCATGCCTGGCTAAACTCTCGGGTA
TATAACAACGAAGGTTTCTGCACTTTACAGATGCTGATAATAGAGCCACAGAGCATCTTGTCTCCGTATCCGTTTCTGAGCCCGCTCCAAACTCC
GCTCCAGCCTCCGTCTCCGCTTCAGTCTCCGCCTCAACTTTCGTAACCGTCTCAGATCCCAAATGTCGTAGCGCCAGGACCTCGGGCAACGGCGG
CTGCTGGCCGTGGCCGAAGTTCCGTACGGTCCTTGGTGCTCAGTTTCGCCGGCTGACCAGGCGCATCAGGTGGGTGCAGCCATCAGCTAGCAGCA
GCCCCTTCCAATGCCCCGTTTACCGATCCCCGATTCACCTGCTCTTCTATATACATACGCTATGTCACAGCTCTCAACGAACCAAAAGCTAAACC
CAAGCCACCGAGTTCTCCAAATAGCAAACCATCGTGCTACGGTCTTTTCTGGCTGAAAGGCTTTCAATTTCGCCTCACGCATATTTGCAGATTAC
CCAAGTTTAGGGAGGGGTATTATCTTGCCACAGTCGCCACAACAGCAGTCAACGCAGCAGCAGGAGCAGCCAGAACCTGCAATAGCCACATCGGC
AACAGTGGCAGGATTAGCAGTGGCAATGGCAACCGAAGTGGAAATCGAGCCACCACTACCAGCACCACCAGTCACAGTCGCCAAGCGCCCGCAGC
TCCCGGCGAAGCCAGCACAGCAGCAGCAACAACAGGCGGCGCGTAGGGCCAGGCCATCGGTGCTGCTTAAGCCGCAGTACGCCTGCTTCCTTCAG
CACGACGATGATGCACCCAAATCCCAGCCAACTGCTGCTGGACGACCGCGCAAGGCAGCCTCGTTTTCATTGGGCAATCAACGGCAATCGAAGGA
GCAGCAGCAACATCATCATCATTACCAGCCACAGCATCAGCAGAGTAAATATGAACGCAACGATTGCAGTAGGAGTCGGGGCAGTTGCGAGAGTC
CAGCTCCAGAACACCAGCAGCGACGTCGTCGGCCTAGTCTGCCGTCGTCGCTGGCTTTGTCCAATGCCAGCTCGGCCCTGCTCCAGGCACGCATT

FIGURE SHEET 76

CCAGGCACCACGCTCTACTATGTCTGATGGCCACCCGATATGAAAAGCATTAGACTCCAAACTCCAGATAACCAGATATCCAGATAACCAGATAC
TCCAACTCCGAACCGATTTGAAACCGCCAGCGAAACGTAGGCATTGCCCAAGCTTTACTATATGTTTACAACTAGGCTAAAGAACACCCATCATC
CCTTGGATACCTCTTGGTGACCCCGTTCCGCTCCCAAAAAAAAAAAAAAAACAAAAATATATATTGGTTTGATGGCCGCTAAACTGTAAAGTGTAA
CCCTGTGCATATCCGACTCACTCCAAAACAAATAACTCAATGCGGAAACCAGGAACACCAAACCCGAACACACCAATCACAACACACACAAGAAA
ACAAACACTGGGGCAACCGGACACTCGAAACACACGTTTAATCGATTCATAGATGCGATTCACGATGCTTCCCGATGTCGATGCACTGCCGCCGT
TAATCGTTTATGCGATGCTCTGGATAACAATCAACAGTAATTCGCGAATTAGCGAGCGAAGAATACGCGAAGGATGATGGATTTTAGAACTAACC
TAAATGATGGATAATGCTGGTGTCCCCATGTTTCACTAAAACCAAACCATGTTCCTATGACTGCTGCTTGATAATGCCCTGCTCCCCCGTCTGTA
TTCATTATCCACAACCTTAGGTATAAGATGCTCCATAGTCTTTAGCAACCATTATATGATAGTTTACCTAGTAAATCGTATGCCAATCATCAGAT
TGAACTGTACTATGCCCACCCAGCCCATGTGGAAGTTAAAGATTATTGTAGAAAACTATTTAGGTCACCTATAAATGTTGGCAACGCCTAAGAAT
TAAGCTAACTACTCAGCTAGAGATCGCAGAAACCGAAACAATTGCGATAATTGATAACTAAGTGTTCATGGCAAATTTTGGGGTGTAACTAAACG
TTTAATAAACGAAAAGTAAAGCAACTAAAGCTGCAGACAAATCAAAGAACCTTTATGTAGCGGCTAATTTCGACATGTGTTCGGTGTAAACCAAA
CAAAAACGAATCACAGAACACTAGTTAGTGACTATTTTCATTTCAGTTACGTACTTAAGTATATATATTTGTGCACCCGTGTGAGTTGGCGTTAG
TTATGTGTTATGTGCTTATGTATGTTTGCTTTGTTTGGCTCAGTTCGGTTTGGTATGCAGTTGTGGGGCATGTATTGAATTGCAATTTGCGATTT
GAAATTGTAGCCATGTAGTTACGCTAACCTACCTTCTCGCCCCCGCTGTTTCACGCCACCCAAATGGTTTTTCATTTCAACAACAACCTTTTGTT
AAAGTCACCGCTGTCGCTTTGTTTGTTTGCTATTTGTTTACTTCTATTTCTATTTTTTGTTCATACCAATTTCTTTTTGCAGATATTATTTAAAT
GTAACAGAATACATAAGCAAAGCGTTGAAATAATATCTATTGTATACCAAAACCAAAAATATCTATGATAACAAACAAGCAAAGGCAATTAAACC
GATCCGTAAACTGAATAACCGATTAATAACTGCAGCCGCTCAACCCGAACCGCAATAAATAACTATCAAGTAAAGAATAGAACAACTTAACAATG
AAAAATGCAATATTCAATATGCGAAATGACAAATGCCTAATGCCAAATGCCAATCCAAATAACCCAATAACCGATTCAAGTGCGAGAACAGAAAT
GCCACACCTCTAACCCAGTGCACTTGCTCTGTCTGCTCCGCTGGGCAATCAAACTAATCGCCAATTCATATTATTATTAAGGTAACTAACCCAGA
TTAGAACAGACACTCGAACACACGCACACACCAGCCACCAACACCACTTGGCACATCCTAGTCATATCATCAACTTCCATCGCTCATCTCCACTT
CCATTTCTTTATCCACTGGTCATGTTTCGTTTTCATTTGCTTGAAAAGATCCAGGCGAGATCCTCCTTTATCCACAACACCGTCACCTCATCTCG
ATTATATATACATATAAATATATATATATATGTTCTGAAATATATATTTCCCAACTCGGAGCCACCTTATTTATCATTGTACTAACCCCAAATCC
TTGGAAGGATTTAAACCCACTTGAAATAAAGATATACAGTCGATTAATCTCGTTCTACACATAATTGCAGGCTCCACGGCTCTGGGCTTCTACAC
GCCCATGAAGGGCACGGCGATGGACAACCTATTCCAGCTGGGTGTCACCCGATACGCCCTGCCCGAGAGCAGCAGCAGTGGGAGCAGCAATGGCA
GCCACAGTCCAGGCAGCAACGGGAGCAGTCCAGCCGGAGCTGCGGGCAGCCGGTTGATGTTCAACGGGAATGGCAGCATTATGGGCATCGGCGAG
GGACTGATCAAGGAGGGCGACTTGGCGGCAACGGAAGCAGGACCTGGAACTGCAGATGGAGCAGGTGCCTCCAAGAAGGGTTCAGCTGTGGACGA
GGATGATTACCATCTGACGGCGACGCCGGGCGCCGAAGTTGTGTACAGCGAGGGTACACAGAAAACGGATTTGCTATATTAGGTCGTCCTGCCAG
CCAAAAAACCGGAGCGTCTAGCTCTTTTTCTACCGGTTTCCACCAAACTCCAAACCTTCCGAGCATAACAACCTACCACATCCTGATCGTTCCCC
TAATTGAAAAGCGTGCACTTAGGTGAAATATCAACTTCGGTTAGACGCGAAAACAGTAACGAAGGAAAGAAAAATAAAAACAACAAGGCAACGTA
AACCAAGTATGGCAAGAAATCCATAAAGATACGTATATAAATAGATATTATTTGTAAGTTTGTAAGCCTAGAGATCCGATGTGTATGTGTACAAC
AGCAAGCGTGTGTGTCTGTCTTCTTTATAAATATATATATATGGTTTTTTTTTTTTGATAAATTAATAATTATATTATTGTAATGTATCTACATA
CGGCACTGAATGAACAACTTTGCTGCTGCAATTGTATTTGTATTTGTATTGTGTATTCCATTTACGGCATTTTGATAGTAAATATACAACAACAA
CAAATCAACGTATTTCCGACTGCATCCCGAAGGTTACTGAAACCTTAATCCACGAAGTACGCGACGAGCGGTTAGTCCCGCCCGAGTATTAACTT
AATGGATTCTAACGATCCGATCTTGTGACCCATCATCATCCCTTTTCGCGACCCTTCCAAAACGAAAATGAAGAACATTCTAAGCTCCGCTTGCC
CATTCAGCGGAAGAAAGCAAAGGAAAATGTAACATTTGCCTCATAATTATTATATACATTTAGCGCTTATTGAATATTTTTTACAATTGTATTCC
GTAAATAAATATAAAATACATCAACATCTAGTCGCGTGTTTTAAGTTAAAGGAAGTTAAGGCCAAAGCAAAATGTTAGCAACAGTTTTTGTTAAA
AGTTAACATATATAATAATGGTAATTTAAATATTCAAATCTATGAAGTGACTTATTTTATAAGTCCACTTATGTTTGTTATATTTAATTGGTATT
TAGAAAAGGATTCATTTTAAATTAACACCGTTGAGGGTTCAATTTTGGTAGTGCGTCTTTGCTAACCATGCCGAGTGGGATCAAGTCCTTGCTAA
GTTAGGATGTTGTCTTAGCTAACTGTGCCATCCCTGGTCGGGGTGTGTCTTAGCTAACAATTACGTGTCGATAGATATAATGCTATCGATATGAC
AGAGTGTCGGGAACAATCGATAGCATTACTTCGATATCGGTACTAGTGCCACCTCCAGTTTTGTGATTGTGTCAAAAATACAGGGTTTTATTGTT
GCACTAGCAATTTAATCCGAGGAATATAAATTTTGTGTGGAGTTATGTTCGAGACGTCGTTGCCAGCGATTCAAGAGGCGAGCGGTCACACGTGT
ATGTGTTTCACTGGCGGTGCGGGCGCCAACTCCGCCAAAAAGCGTACTACTTTTAACCTTAGTTGACATTGAAATGTACCCGCTTAGTTGGATGT
CCACGATGGTGCGTGTGTGTGCGTATATGTGTGCTATGCGGCGTCTGTGTGCGCGAGTGTGTGTGTGGGATTGCAAAGGAGGATGGGAGAAACGA
GAGCAGAGCAAAAACAAAAACAAAAGGAACCTGCTGCACATAGTCGGTGCATGCGAGCGTGCTTATGTGTGTGTGCGTGCGTGCTAGCAAAACAA
CTGCAAGAAATCAGCAACAGTAGTAGAAGAAGAGAAGCTGTATCACTGATAAGGAGGCTAAACAACAACAAAAACAGCAACGATAATGTGCACCC
TTTCGAAATGCAAACAAAACAAAGCGTTGTAGTTGTGTAATCATTCGTTGTG
(SEQ ID NO: 160)

Exon: 1001..1298
Exon: 2853..3123
Exon: 3727..6263
Exon: 9471..9644
Exon: 11210..11552
Exon: 14808..15186
Exon: 15556..16722
Start ATG: 2862

Transcript No. : CT5502
TGTATTGGAAACGCGGCTTAACTTAATGCAGATTTTTCCGCTGATTCGGCTGCGAAAGATGCACTTTTAAGGCGCAGCGAGTGCACCCACGCCCC
GAGTTCGAGTGCAGTTGCAGTCGGGAAAGCTTGACAAGTGCGCGGAGCAAGGAGAGCGACGAGTTCGTTGAGCTACAGCGAAACGGAAAAGTGTA
AAAGCGGGGTAAACAGGCGCAGCGGAGCGGATGATAAACGGAACTCGGGATCGGAAAATTGGAAGCAAAACCAACCACCGATTATAAAAAATAGT
CAGCATCTTAAAAACGGGGATAATGGAGTCACAGAAGCGGCCTTCGTTGGACTTACACACGGATGTGCCAGCAGGATTAGCAGCTGGAGGATCTG
GCCTGGGAGCTGCAGCTGAGATGTCGCCCACTTCCGGTTTCCTGCCGGACATGCCGCAGTGGAAGAAGGACCTCATCCAGCGCCGGAAAACGAAC
GTGGCCCGCACCCAGGCGGCGTCCATCACCTCGCCCACCGATGGCAGTTGTGGGGCTTTGGCAGAAGCCAACGCAGCTCCAGGTGCAATTGCAGA
TTTCACAGAACCGGCGACAATCAGTAGCACTAGTCAAAAGAGAAACATGATCGGTTCAGAGGAAAAGTCTGAGAAATCTTCTATTTCCAATACCA
ATTCCGATTCCACTGGAGGTCATCACTCTGTTGTTGCCGTCTCCCTTTCGCCCGATGCGGCAGCAACAACAAATGTAACAGTAACACCAATACCA
AAGCAGCGATCGAGTTTACTCAACACAAGAAGTCAGGAGAGGGAGATGGTGCGATATATTCTAAGCGAGAGTGGAGAACGGGATGGAGAGCTTGA
GAGCGGCGAACAGCCGGCTGGTGTGGTGAGTAACAGCCGGTGCGGTGAAGTTGAAACTGGCACAATTGGATCGCCGTCGTCGTCAGCAAATCAAA
ATCCAAACCCAAATCATTTAAAAACGAAATGCAAACCGGGACAGAGCGTTGCTGAGGGCAAGCCTTCAGCTAAAGAGACCATCGTCGATAACAGC
AAAAGCTGCAGCAAAACCAAGAGTATTTCCGATAAATTGCAGAGCAACAAGTTTATAATTCAACAGCAGCAGCAACAACAACAACAACAGCAGCA
ACAACAGCAACTGTCGCCCACAAAGGTAACGGTAAAACCGACAATGGTCGCCATGCAAGAGATGAAGAAGACAACCAAACAAAATGGCCAGCACC GACATCTAGCGGGCAAAATTGGCAGCGTAGCAGGAGGCGATGTGGATCCACAACATCCACCGACGAATCCCATACCAGATTCATTGGACACCGGT
GAGGATCTGAGCTACGGACCCGGAATTGTGTCCAAGCTGCGATGCCGCTACTTGAGCCTGGCCCTTCGCGAGTCCCGCCAGCAGAGCAGCAAACA
ACGCCTCCAACGCTCCACCAGTCTGAACACCCTGCTCGACCGCGACGATGACGAGGTGGAAGTGGAGGAGCCCGAAATGACCAACAGCCAGGTGC
GTGCCAAATCAACACCGCCACCGATATTGGGGGCAAAACCGACACCGAAACCCAGCAGCCAGCATCAGCGTCCCGTCAGTCTGGGCGCCAATGGA
GCTGGATCAGCTGTTAACCCGCCCTCGAACTCGGATCAGGCCCAAACGGGCGCCGTTGCCAACGGAGGCGCAGGATCTGGCCAACGTTCGCGTCA
CTTTAAGCGCGGCAACGAGGTGATGAAGCGGGCACGTTCCGTGGAGGCTCTGCTCTGCGAGAAATCGCCATGGAACAGCCAGAGAATCAGCACTG
CCGGCGCAGCTGCAGCAGCAGCACCTTCACCACCTGCTCCCAAGGCCACAGCCGCTGCTCCCTCACCTGTTACATCGCCCACCTGCGTTACCATC
GAGGACAAGATCCACAATGCCCGCGAACGACTGCACAGCGGGACGGATACGGCGCCACCCAAGCGTCTGACCTCCATCATCGATGACACCGAGCG
GCCGCCACCGGATCTGGTCAAGCAGACGCTCAAGATGTTTGAGGCGAGTGCTAATCGACGACCGCGCGCAGCCCATCGTTCCAATGGTGTTGGCG
GAGTGGCCAGCAAGGTGGCCAACTACAAATCGATCATTAAGGATCAGAAGCAACCATCATCAGCAGCGGCGACGCCACCGCCGACCGGCATGGGT
TTTGCCTCCTCAACGCCGCTAAGGCATGTCCATCCGGATATTATACCCCGTCAGGTGGATTCGCCCGTATCGGCGTTGAGTGTAATGATGCGTCG
CATGGAGCTGCAGGAGCCCGAGACGCCGGAAAGGGAGACACGGGACGCGGAGGCCACACCGCAGAGCGAGGCGCTAAGTGAGACTGAGCGAAATG
ATCGCGATGAAGGCGATGGCGAAGTCGATGACGACAACCACAACAACAACGACGACGATCACGACGACGGCGACGACGGCAGCGACAACAATGAG
CAACGCGATAAAATGGGCGCGGCGGCGGCAGGCGATAAGCCTAAGCCCCCAGCGGAATCGGCAGCGGGAGGCGCCCAACGATCATTCGCTGCCTC
GACGGAGAACGCGCATGTAGCCAGCGGTAGTAGCAGCAGTACCAGTGCCAGTGTACGGAAGCTCAGCAACAACAACGACTCCAGCAGCGGACCAG
CGGTGACCAAACAGATCGGTGTCATCCGTCCGCTATTCAATAGCCAGGGAGCCGGGAGCACGCCGCTAACGAGTCGCGAGATCGAAAAGAATCGC
ATCAATGAGATGAAGAAGTCGACGGCCACAGATGCCGGTGGTTCGGTATCCGGATCCGGAACGGTTGCTGGTGCTGGATCAGGAACCTCGCCCAC
CACTAGTCTCGACAGCGTGATAAACACCAAGGAAGCGGCCAGCAGCGAAACGGATGCCAGTGCCTCGCCACTGTGGACATTGCGCAAGCTGAGGA
ATCAGAGCCAGACGGCCGGCGGAGGATCGGGTCCCAGTTCGAGCCTTCATTCCACAGAGAACACCTCGATGGTGTTCAACTTTTCCAAGAGCACC
AAGGAAGTGCCCGACTACATCGAAAGCGACGTTGTGATTTACAGGCGCAAGCGGGAGCTGCCAAAGCCAAATGAACCTGGCTTCGTGCTCCTGGG
CGATCTCTCCGTGGAGACGTCGACGGACACGGACTACGACGACTACTCCATGTGCCCGCCATCGCCGTGCGATGTGGAGTTTGAGAATGCCAACA
TTGTGATCGACGGCAAGTCCAGCATACGCCAGAAACCCAAAGAGTCTTCGTTCCGCGTGCAGTTCAACGACACGCTGACGTCGACGTTTGAATAC
CCCTCCGAGGCATCGATGACCATCGAGGATCCGCCGTACGCCGATCCCTTTGGCCATGTGAGCAAACACCATCAGATGCTGCTCGCCGAGCAGAT
GCATCTGTTGCAGCACCAGGAGCAGCTGGAGCTGGAGCAGATGCACCAGCTGGGGCTGGCGCCGGAGCAGCACCATCATGTGACCGTCGACGAGA
TCATCGAGCTGCCCACATCGACGGCGGGACATGGACATGGCATCGGACTTGGACACAGGTCGGGGGCGGCGGGGGGCGGTGGCACGATGCTGGGG
AATTTACCGTTGGATATTATTTAAATGTAACAGAATACATAAGCAAAGCGTTGAAATAATATCTATTGTATACCAAAACCAAAAATATCTATGAT
AACAAACAAGCAAAGGCAATTAAACCGATCCGTAAACTGAATAACCGATTAATAACTGCAGCCGCTCAACCCGAACCGCAATAAATAACTATCAA
GTAAAGAATAGAACAACTTAACAATGAAAAATGCAATATTCAATATGCGAAATGACAAATGCCTAATGCCAAATGCCAATCCAAATAACCCAATA
ACCGATTCAAGTGCGAGAACAGAAATGCCACACCTCTAACCCAGTGCACTTGCTCTGTCTGCTCCGCTGGGCAATCAAACTAATCGCCAATTCAT
ATTATTATTAAGGCTCCACGGCTCTGGGCTTCTACACGCCCATGAAGGGCACGGCGATGGACAACCTATTCCAGCTGGGTGTCACCCGATACGCC
CTGCCCGAGAGCAGCAGCAGTGGGAGCAGCAATGGCAGCCACAGTCCAGGCAGCAACGGGAGCAGTCCAGCCGGAGCTGCGGGCAGCCGGTTGAT
GTTCAACGGGAATGGCAGCATTATGGGCATCGGCGAGGGACTGATCAAGGAGGGCGACTTGGCGGCAACGGAAGCAGGACCTGGAACTGCAGATG
GAGCAGGTGCCTCCAAGAAGGGTTCAGCTGTGGACGAGGATGATTACCATCTGACGGCGACGCCGGGCGCCGAAGTTGTGTACAGCGAGGGTACA
CAGAAAACGGATTTGCTATATTAGGTCGTCCTGCCAGCCAAAAAACCGGAGCGTCTAGCTCTTTTTCTACCGGTTTCCACCAAACTCCAAACCTT
CCGAGCATAACAACCTACCACATCCTGATCGTTCCCCTAATTGAAAAGCGTGCACTTAGGTGAAATATCAACTTCGGTTAGACGCGAAAACAGTA
ACGAAGGAAAGAAAAATAAAAACAACAAGGCAACGTAAACCAAGTATGGCAAGAAATCCATAAAGATACGTATATAAATAGATATTATTTGTAAG
TTTGTAAGCCTAGAGATCCGATGTGTATGTGTACAACAGCAAGCGTGTGTGTCTGTCTTCTTTATAAATATATATATATGGTTTTTTTTTTTTGA
TAAATTAATAATTATATTATTGTAATGTATCTACATACGGCACTGAATGAACAACTTTGCTGCTGCAATTGTATTTGTATTTGTATTGTGTATTC
CATTTACGGCATTTTGATAGTAAATATACAACAACAACAAATCAACGTATTTCCGACTGCATCCCGAAGGTTACTGAAACCTTAATCCACGAAGT
ACGCGACGAGCGGTTAGTCCCGCCCGAGTATTAACTTAATGGATTCTAACGATCCGATCTTGTGACCCATCATCATCCCTTTTCGCGACCCTTCC
AAAACGAAAATGAAGAACATTCTAAGCTCCGCTTGCCCATTCAGCGGAAGAAAGCAAAGGAAAATGTAACATTTGCCTCATAATTATTATATACA
TTTAGCGCTTATTGAATATTTTTACAATTGTATTCCGT
(SEQ ID NO: 161)

Start ATG: 308

MESQKRPSLDLHTDVPAGLAAGGSGLGAAAEMSPTSGFLPDMPQWKKDLIQRRKTNVARTQAASITSPTDGSCGALAEANAAPGAIADFTEPATI
SSTSQKRNMIGSEEKSEKSSISNTNSDSTGGHHSVVAVSLSPDAAATTNVTVTPIPKQRSSLLNTRSQEREMVRYILSESGERDGELESGEQPAG
VVSNSRCGEVETGTIGSPSSSANQNPNPNHLKTKCKPGQSVAEGKPSAKETIVDNSKSCSKTKSISDKLQSNKFIIQQQQQQQQQQQQQQLSPT
KVTVKPTMVAMQEMKKTTKQNGQHRHLAGKIGSVAGGDVDPQHPPTNPIPDSLDTGEDLSYGPGIVSKLRCRYLSLALRESRQQSSKQRLQRSTS
LNTLLDRDDDEVEVEEPEMTNSQVRAKSTPPPILGAKPTPKPSSQHQRPVSLGANGAGSAVNPPSNSDQAQTGAVANGGAGSGQRSRHFKRGNEV
MKRARSVEALLCEKSPWNSQRISTAGAAAAAAPSPPAPKATAAAPSPVTSPTCVTIEDKIHNARERLHSGTDTAPPKRLTSIIDDTERPPPDLVK
QTLKMFEASANRRPRAAHRSNGVGGVASKVANYKSIIKDQKQPSSAAATPPPTGMGFASSTPLRHVHPDIIPRQVDSPVSALSVMMRRMELQEPE
TPERETRDAEATPQSEALSETERNDRDEGDGEVDDDNHNNNDDDHDDGDDGSDNNEQRDKMGAAAAGDKPKPPAESAAGGAQRSFAASTENAHVA
SGSSSSTSASVRKLSNNNDSSSGPAVTKQIGVIRPLFNSQGAGSTPLTSREIEKNRINEMKKSTATDAGGSVSGSGTVAGAGSGTSPTTSLDSVI
NTKEAASSETDASASPLWTLRKLRNQSQTAGGGSGPSSSLHSTENTSMVFNFSKSTKEVPDYIESDVVIYRRKRELPKPNEPGFVLLGDLSVETS
TDTDYDDYSMCPPSPCDVEFENANIVIDGKSSIRQKPKESSFRVQFNDTLTSTFEYPSEASMTIEDPPYADPFGHVSKHHQMLLAEQMHLLQHQE
QLELEQMHQLGLAPEQHHHVTVDEIIELPTSTAGHGHGIGLGHRSGAAGGGGTMLGNLPLDII*
(SEQ ID NO: 162)

Classification: known_flybase_gene
Gene Symbol: bif
FlyBase ID: FBgn0014133

Celera Sequence No. : 142000013384767
GATATTATTTGTAAGTTTGTAAGCCTAGAGATCCGATGTGTATGTGTACAACAGCAAGCGTGTGTGTCTGTCTTCTTTATAAATATATATATATG
GTTTTTTTTTTTTGATAAATTAATAATTATATTATTGTAATGTATCTACATACGGCACTGAATGAACAACTTTGCTGCTGCAATTGTATTTGTAT
TTGTATTGTGTATTCCATTTACGGCATTTTGATAGTAAATATACAACAACAACAAATCAACGTATTTCCGACTGCATCCCGAAGGTTACTGAAAC
CTTAATCCACGAAGTACGCGACGAGCGGTTAGTCCCGCCCGAGTATTAACTTAATGGATTCTAACGATCCGATCTTGTGACCCATCATCATCCCT
TTTCGCGACCCTTCCAAAACGAAAATGAAGAACATTCTAAGCTCCGCTTGCCCATTCAGCGGAAGAAAGCAAAGGAAAATGTAACATTTGCCTCA TAATTATTATATACATTTAGCGCTTATTGAATATTTTTTACAATTGTATTCCGTAAATAAATATAAAATACATCAACATCTAGTCGCGTGTTTTA
AGTTAAAGGAAGTTAAGGCCAAAGCAAAATGTTAGCAACAGTTTTTGTTAAAAGTTAACATATATAATAATGGTAATTTAAATATTCAAATCTAT
GAAGTGACTTATTTTATAAGTCCACTTATGTTTGTTATATTTAATTGGTATTTAGAAAAGGATTCATTTTAAATTAACACCGTTGAGGGTTCAAT
TTTGGTAGTGCGTCTTTGCTAACCATGCCGAGTGGGATCAAGTCCTTGCTAAGTTAGGATGTTGTCTTTAGCTAACTGTGCCATCCCTGGTCGGGG
TGTGTCTTAGCTAACAATTACGTGTCGATAGATATAATGCTATCGATATGACAGAGTGTCGGGAACAATCGATAGCATTACTTCGATATCGGTAC
TAGTGCCACCTCCAGTTTTGTGATTGTGTCAAAAATACAGGGTTTTATTGTTGCACTAGCAATTTAATCCGAGGAATATAAATTTTGTGTGGAGT
TATGTTCGAGACGTCGTTGCCAGCGATTCAAGAGGCGAGCGGTCACACGTGTATGTGTTTCACTGGCGGTGCGGGCGCCAACTCCGCCAAAAAGC
GTACTACTTTTAACCTTAGTTGACATTGAAATGTACCCGCTTAGTTGGATGTCCACGATGGTGCGTGTGTGTGCGTATATGTGTGCTATGCGGCG
TCTGTGTGCGCGAGTGTGTGTGTGGGATTGCAAAGGAGGATGGGAGAAACGAGAGCAGAGCAAAAACAAAAACAAAAGGAACCTGCTGCACATAG
TCGGTGCATGCGAGCGTGCTTATGTGTGTGTGCGTGCGTGCTAGCAAAACAACTGCAAGAAATCAGCAACAGTAGTAGAAGAAGAGAAGCTGTAT
CACTGATAAGGAGGCTAAACAACAACAAAAACAGCAACGATAATGTGCACCCTTTCGAAATGCAAACAAAACAAAGCGTTGTAGTTGTGTAATCA
TTCGTTGTGAACACACCACACACACACACACACAACACTTGTTTTAATAATACATTTTAATTCTATTATTTTTGATTTAATTTTTGCCTGTTAT
TCAAATCGATCTGTGTTTTTGCAGTTGGCATTCGTTATTAATTAAATCAGCCGCCAACAGCTGAGCGAGAGAGCAATCGAGAGCGACAGGAGAGG
ATCCACTTCCAATCGAATCGGGTGGAATCGAATAGCAGGGGCTTGGTAATTAAAAGGAAGACCGAACTGAACTGAACTAAACTGAAACGGAACGA
AGCGAAGCGAAGCGCGGCGAGGCGGCAAGAAACGAAAAGAAAAGAACGAAAGTCGGCAGAGTCGGAAAGTCGGCAAGTCTGATTGTCGGCAAAGT
CGCAAAGTCGGAGAGTCACAGTCTCAATCGCAGTCGGCGAGAGATTCCACTCGTGTCGCACGTCCGTTCGTTTCCACATTGTCGTTATAAAAATA
GCAACGCCTTAAACGATCGCATCAACCTCATCAACAGAACACCACCAGAAATCACCGCCCCCTCCTACGCCTCAATCGCCATCGCCACCGCATCC
CATCCCCATCATCTTCATTAGCAGGCAGCCTGACAGAGTAACTAACTGATCTTGATTGCGACCATAATCACCGTCATCATCATGTAATCCTTCAC
TAACCAATTGATTTCCGCTCGTCCACCAAATAGATTCCAAACTGCCGTTTCGGCAGCCGGCAAGATTTCACGAAATCTAATGGCCAAGGACGAGG
AGGATGATCTGCTGCCCGACAAGGATGCGGCCAAGGGCTTCTATGCCAAATACGAGCCCAAGGAGATTCTGGGCAGGTAAGAATCGAACTACACT
TGCCGTGATCTCAAACCTCTTATTAAATCCTTTTAAATTCAGTTGAAGTATTATTGATCCTGCACTTAACCATTCAAATACGTTTCTTTCTATTT
ACTTTGCGTAGTTAATTTTGCAAATTTAAGATCATAGAAACATTGATACTTGTATCCTCAGAAATCACTAGAACGTCCAAATATTGATTGTTTCT
GCTTTCCCAACCTCTTACTGCCAAGTCTGCAGTAATGCAGTTTGGGCTAAATGGTGCCAAGTGAGTCAGCCTCATCAAGCTTCCATGGCATGGAG
CAATGGCATGGGCTGCTTTTCAAGCGGCGCCTGTCTGCCGGCCTACTCACGCCACAACGAAGATCAGAATTTGCCAAGCAAATAGCAGAGACTAA
GCGAAAACAAGGGCTAATTACATATTACAATTCTAGGGATTAGAGATTAGATAAATACCCGATCATGGCAATGTCAAGTGCAGCAGAAGCAGAGC
TCTTTATCTACATGCAATGTTTGTCTTACAGGGGCATCAGTTCGACCGTGAGGCGATGTATCGAAAAGGAGACGGGCAAGGAGTTTGCCGCCAAG
ATCATCGACTTGGGCGCCACCACAGAGTCAGGCGAGACGAATCCATATCACATGCTGGAAGCAACCAGACAAGAAATCTCAATACTGCGCCAGGT
CATGGGGCATCCCTACATAAGTTAGTCTCACATAGCACCCACATGTACTTAATTCCACCACTAACCATCTACATTATCGTGCACAGTTGATCTGC
AGGATGTGTTCGAGTCAGATGCATTTGTTTTCCTCGTCTTCGAGCTGTGTCCCAAAGGTGAACTCTTCGACTATCTGACCTCTGTGGTGACGCTA
TCCGAGAAGAAGACGCGCACCATTATGCGACAAATCTTTGAGGGCGTCGAGTACATACACGCGAAGAGCATTGTCCATCGGGATCTTAAGCCCGA
GAATATCTTGCTGGACGAGAACCACAACGTTAAGATCACGGATTTTGGCTTCGCCAAGCAGTTGCAAGAGGGCGAGAAACTTACAAGTAATTATA
ACACAGCATCCTTCTGTATTCGCTAAGCTAAACTATATGTACTTTCCCCCTATTAGATCTGTGCGGAACGCCGGGTTATTTGGCTCCCGAAACGC
TCAAGTGCAACATGTTCGAGGGATCCCCCGGCTACTCGCAGGAAGTCGACATGTAAGAGCGAATAAACTAGCCACTTATTATTACACCTTTTTTT
GGCTCACTTAAATTATAGAAGCAATTTAAGCACAAAAAGTATCACATTTATTGTAATACGAATTGTCTGCTCAAATTACTAAATTGCTTATGTTA
ACAGCTAATTTTATTATTAAAAATTTTTGCTTACATAAAAAAAGAAAGGTCTAAACTTTTGTATCGATATTAGACCCGTTTTCCTTTTTTTTTG
TTTTATAGACGCAAATTTTGCTGATACATTTCATTAACTAGTGTTCCTCGTGTCAGGCGATTTGTTTTGATCTTTAGGTGTGCATTTTAATGAAT
GAGTCAGAAGCAGAAAGGCATAATAATCTGAAATCTGAGTAGTTCCGATACCGACGTCTATATTTCTTCGGTTCAGCAAAACGTAGGGCTTTTTG
TATTTTTGAGTTCTTTAACGTTTCCCACTGGTATCTACGTTACTTGGTTTCAGCAGAAATTTTTAATAGGAAAAATTGACACCTTTTACCCATTT
CTTTTTCGATTTCTTTTTGTTGTTCGGAGATGGGCCTGTGGCGTGATTATGTTTACGCTGCTCGTCGGTTGTCCACCTTTCTGGCACCGCAAGCA
GATGGTCATGCTGCGGAATATCATGGAGGGCAAGTACAGCTTCACCTCGCCGGAGTGGGCTGATATTTCAGGTTGGTCAAATTGATATGCACATG
CCAAACGTATGCTTATTTACTTGGTTTCGATTGATTGCAGAGGATCCCAAGGATCTGATACGCAAATGTCTAGTCGTTGATCCTTCGCAACGTAT
AACCGTCAAGGAAGTATTAAGACATCCATTCTTCAACCAAATGGTAAGTGCCGGAATTGTTGGCAGCCGCCGGGCTCCAATTACCACGACCACCA
CCACCACCACTACTACAACCGCCTGTACAAGAGGAAAATCAGTCAAATTAGTTCAATTAGTCGCCAAGAATGAGGTCCGCCTACGAGTCGTCTTT
TGTGCTCGGGCAGCAGTCTATAGTTTTCGGGTTCCTGTTCTTGTACATAGATACTAGATCTCTAGTTGATGGGTTTAACCTCGGGTGGGTTAATC
TTCTACACAACCAATCCACCAAAACAACCAAACACCTGGCCCTGCAAATGTTTCTAAACACAACGTACATCTAAGAACACACACTCTGATGGAAA
GAACACCCACCTGTGACTCACAAACCAACCACTCACAACAGCCTATTAACAGCTTCTTCTTACTGTTACCTCCTAAAAATACGATTATGATTTAT
AATTCGGTTAGGGTAGCAGCCTAACCCCCCGTAGTTTAGTTCAATTGTCAGATTTATAGCCTGACAGGATCAGTCATTAGTTTGGATCCCCCGCC
CCCCTTAAAAAGAAAAAGAAAGGAAAACCCTTCGGAACCTCTTGCGTTTTGTTAACTTTTTATTTCTATGATTACTATTTATTATACCAAACATT
TTCTTTCTTCTTTTCCTTACATATAAACTATATATCAAATCGAATCCAATTAATTTTAAACGAACCCAAACGAACGATAACGAACACACACTACC
ATCGATAGCTGTTCGAGCAAAACATTGATGGCCTCAAGCGCAGCCTGTCGACCAAGTCCCGACGAATGAGTCGCATCACTGAGATCGCACTGGTA
ACGAACCGTTCCCGGACTAACCCAAGCTCTCTCTATCTCTTAATCTCTCTGTGCTGTGTGTCTCCGTGTTCATATATTGATATCGGAGCCGTAAT
CGTAATCGCTCTAATAACGATTATCCCGATAATCCTGATAATCCCGATAATAAAATCAAGCAATCGGGCCGGCAGACCCAACTCATGACCATATG
CAACCCTGCCGGCCCAGCATTCGTGTGTCTGTTTTCCGTTGCATTCTGTTCTGTTTCGTTCTGTGCCGATCTAATATAACCCAGCTAAACTGTAC
ATCATAGTGCATATCAATTGTATACTATACATACTTATTTATTTAAAATCCGTTCAGGTCATCTGTGCCAAGCATAATAACTTTTAACCGGCCGG
CAATAGCCAGCGAAAAACGAAACAAAAACGAATACGTACCCGATCTGCTTCGTTTTTGTTTGCATCTGATTTGATTTGCTTGTCGACTGATCGAT
GCACCACAATGATAACAAAAAAAGAATATATATATATACATATATATAACCCTTCTCTATAATCCCATTCCTTGTTGTACTCGATGTTTTTTTGT
CGATTTTGTGTGTTTTTTGTACAAATCAACCGATTGCCTCGATAACTAAAAACGATAACACACGTCTGCAGCTCTGCGCTCGCCATTTGAATCAT
AATCTGTTAAGTTAATAACTGTGTCTGCATGCCAACCAACCAAAAAAAAAGCAAAACAAAAATCCAGCAGGGTTTCCCTTATCCCAACCTCCAAA
GAAAACCCCACAATTCCTATTTTGAGTCACTGCATGCAAGCGTGCATTAACCATTCAGTCAGCGAGAAGAAGATTTGAAGATTTGGCGATAGTAG
ATAGTAGAATTCACAGAATAGATACAATACCCCATCAAGGTGCATATAAGTATGAAACACGAAGGTATATATTATTGGTAGTCCACTAGGATGTT
GTACACTTCCCACAGATCAAATAAGTAGACTGTAAGTTGAAGTCATTTTAGGTATTATATTCATATACGTATAAGAACGTCCTGTGCTTCACCCA
ACCCAATTTTTAATTTAACCTCCGTGACTGATAAACCAATTTTAATTTCTTCCGGGCCCACTCTGCTGCTGCCTCTGACCCTCCTGCCCACTGCC
AATCTCATCCTTCCTCCGTCTCGCCTCGCCTTCGGTTTTTTGTTTATTAATCGCGGTGTCGACGGGATCAGGTGTTAATGGGTGATCGCCGGCAT
CCGGCCCCGCCCATCGCGCCCGCCCAAACGAACAGCAGGCATCTGCTGCAACCCGAGGCGTCATCGTATCGCTTTGGTCAGCTGAACAGTAGTTG
CGCCGGTGCCCCCAATTATCTGTACTGTGCGCCACAGAGCTCCTACTCGTCGAATCGAATGCGCGACGGGGCGCTGGACGATGCGGGTGCCAGTG
CTGCATCCGCCACCTGCCATGTCATGTCGCCATCCAACGCCTCCAATTCCTACGCCACCAACACCACAGCCAACACCTCGAACTCGGCCTTGGCA
TCCGCCTCCTCCCACAAAACGCTCACGGCGATGGTCTACTATCAGCAGCAACCGCAGCAGCATCAGACGCAGCAGCAGCAGCAACAGTACCAGCA
GCAACAGACGACACAGCTGCCGGTGCAGCTGCAGTTGCAGCATCCACTATTGCAGACCGGTGGCGATGGCAAGCAATCGGTGTATGCACCTCCTA
CAGTGCAGGCAGGTTTTCCATTGATATTCTTTGATCTTGCTTACCCAACACGAATGGCCCAGCGGGCGATGGCAGGAATCGCTAGGGAAACGTTA
AATTGCATACCACAGAGCAGGACGAGTGTGCCCCACAATTGCATTAGAGTTGCCTGAGATTTTTCATCATTAAAAGAATACTTAAAGCTTTGCTA
CGATCATTTTAAATGTTATATACAAATGCCTTTTCTTGACAAATGTTTATTTGAACTATTTATTTAATTGTGTATGTTTATATTTCCTTAAATA

FIGURE SHEET 79

TTATATTTAAATGTTAACTTATGTTGATTACTTTTGAAACATTTAACTTTCTATATTAATTTAAATAATAATTTCGTTTAAGACTATATATCAGT
CAGTTTTGTATGGAATTTTTCGTTTTTGCTAACGTTTTTTGACAGCCGCGTGGGTTATACCTAATATTTAGTTGCCACACGTACTATTACCGATT
AATTTCTAGTGCTTTTAGTTGATTCGAATCAGTCCACTCCACTCCATTAATCATCAGAGACAAGCTGCACTCGATTCACCTTCATTGTATCACTC
ATCCATTAATCCATTTCACACCATTATGTCGTTCGGCTGTCTCTTTCTAAATGATGTTCGATCCGTCGATGGATCGTTATATCTAGCGATCGATA
TGCTTTCCACTGCTGCTTTCCATTCAAACCAAATCATTCGTCTACTATTTAGCGTAAGACTTTGAAAGTACCTCTACTGCATTATACTATTACTA
TTACTATTACTATTATTATATTCTCTTATAGCTGACACTTAGTCATATCATAGCGAGTAAACACTATGTTTGTATTATATGCACCTTTCTTTAGT
ACATATCTCTCGGGTGAACTGGATGATATTTACAAGAACTGTATGTAGTTGACTTGCTTCTGCCGTTTATACCTCTGTGTTGTAGCCCCTATAGT
AAATATATAGTATATAGATCATTAATCCCGCCTATCAGTGTCTCTCATTTGTCTCATGTGTCTTGCGGAGGAAGTCAGGATATTTAGATAAGCTA
ACTAGCATGATAGACTTAAACTTAACTATCAATAACCCAACATCCACATTGAAAAAACTATGGTGCTTTTCGATCGTAACGTTAACGTTATTAAC
CATTGCTTCTAATTACGTTGTAATATCAACTGTAAGCTTTATTTTATTCGGATTTAATATACTTTTGGGTGTGCATATGCTGCCCATCTATAATC
GTATCAATTATGAAATAACGCCAAAATCGATTCACTGACGGATTATTTTGTTTAATTTCTCCTCTGTTGATGATGTTATACACGTTTTGTTTGTG
TGTCATGTCCTCTATATTGTCAGAGTCTCAACGCCCTTATAAGATGTGTGTCTATAAGTCGGTGTTGTGGAGACTCCCTTGTGAGTAAACCAAGT
CAAACTGAGATAGATTTGCATACAGTATTATATCCATACAACCACGCCCACTCCGCATATACCTAAAATTATCGTCTATGTATATTCGTTCTATC
TGCATAATGCTACACATATGTCTATATATATATATATCTATCTATGTATGTATGTATGTATATCGCGCCAGTTGTCAATGTTGTTGTTCACCTCA
AAATGTTTCTCTTACTGTAATTACCCCGCTAACCCATTGTCCTAACCTCTGACCCCTGACCCCAAACTGTTGGCTAATGGCTTTCGGTTATGGCT
TTGTTGTCTTCTGTTACGGCCTCCGCTTGACCATCTAAACTATAAAACATTCGAAACGAAAGTAACTAATGCCACCCAGAATCACTAACGAATCA
TCTATCGAAAAAACACTGACTGACCCAGTTGTTGTACTCTTCACTAAAAAATAACAACCATAAGAAAAGGACTAACACTGGCTGTCTACGATCCG
TGTTGTTGTTCCTCCTTTGTGCGAGGAAGTAACCATTAACCATTAGGCTATAGTTCACCAACTGCTAACCACGAGTCGAATTAACAAAAAAAAAA
AAAACCATAAACCCCTGCTAATTTAACCCGTGGCGTGTGCACCTCTAACCCAAACACGAAGCCAAAAGAAAGAGATCGATCCGCATTGCCGAGTA
TCCAGATGGTTTAATCCGTATCCTTTGCCCTCTCTCTCTCTCCCTCTCTCTCTCTCTGTCTCTCTCTTTCTGATGTTTAGCTGCGCAAACAAAGT
CGCTTCAACGCGCGCAAAAAGTTCCAATTCGCCATACTCGTGATACGGGCCATCATTCGGATACGGCGCCTACGCTTCACCGCCGAGCCGCTGCA
CGTTGAGGAGGCCATCCGGGATCCGTATCGCGTCAAGGTTCTGCGCAAAGGTGAGTTGCTACAACAATTCATATATCGAATATAGTACACTAATT
CAACTTTTGTTGTAGGTCATCGATGGCTGTGCCTTCCGTGTCTACGGGCATTGGGTCAAGAAGGGTGAGGGCCAGAATCGGGCCGCCCTCTTCGA
GAATACTCCCCGCACGGAGCTCCACGCGCTCTACATCAACAATCTCAGCCGATAGAAGGCGGTCGGGCATGGGGCATGGGCCATGGGCCATGGGG
AATGGGGCGTGGCGGAGTCGCGCTGATCTACACAAGCACACACACACACACACACACAGAAAGAAAGAAAAAAGAAAATAAGAGGAAACACAGTA
AGCAAGAAACCAAGAAACAAACCAACAAACGAATTAGCAAAAGCTACTACTATGAGAAGCAGGAAATTGCGATTGCAACAGGACACACCAAACAC
ACCAAAAAGGATTCAATCCATCCATACATTCGGATTCGCCTCGTTCTGGACGGACAGCCAACACGCAGGTGTACATATATACGTATGTATGTATG
TATGCATGCCTAGTAACATTACCTCCCCTGCCTTCTTCGTCCTTGTGATTTTGTTTAATACTTTTTAATTCGATTTTATTGCGTCTAATGCGCGC
CAGCCATCTAGTGTAATCAGTTAGTGTAGTGAATGTAGCGTTCAACCACGGCCATGCATACCACCCAGATGGTACATGGCTATCCAGTGGTCCAA
CGTTATGACCCGGCGCCAGAACGAGCCGAATCGGATGACGAGATGCGATTGATTGTTGGGTTGGGGGAATGTACACACCTCATCTCACCATACTC
CACACCCAACTAAGCCCACACAAGCAAGCGTACATGCATATGTATTTTCTGTTAATGATTCTATTAAATTATTTAATTGTATTGCTAAGCGTTTA
CATTTTAATTGTTATGTTGTAGTATACACAATAAATAAAAACAAACAAAAAAAAAAAAAAAAGAACGAAATAATAAGCTGAAAACAAATCCATTGC
CCATTGCCTCCTAGTTAGTTGAGCAACTTAAGGATTATGGCAATTAATAATGGCTTAAGATGTTAGATGTGCTTGTCGCAATTGTATTTCCGCTC
GCAGCAAGCGGGAAATTCGCGATTGATGTTCACAAAGTCGCGCTGCTTGCAGCCCGGTGGCGGAGCGACTGCATCGCAGGTTTTGAAGGTCACCA
AGCCATCCGC
(SEQ ID NO: 163)

Exon: 1001..1095
Exon: 1640..1755
Exon: 2219..2356
Exon: 2882..3060
Exon: 3127..3411
Exon: 3477..3567
Exon: 4115..4251
Exon: 4316..4413
Exon: 6437..6943
Exon: 9106..9264
Exon: 9326..9460
Start ATG: 2265

Transcript No. : CT5552
TTGCACTAGCAATTTAATCCGAGGAATATAAATTTTGTGTGGAGTTATGTTCGAGACGTCGTTGCCAGCGATTCAAGAGGCGAGCGGTCACACGT
TTGGCATTCGTTATTAATTAAATCAGCCGCCAACAGCTGAGCGAGAGAGCAATCGAGAGCGACAGGAGAGGATCCACTTCCAATCGAATCGGGTG
GAATCGAATAGCAGGGGCTTGATTCCAAACTGCCGTTTCGGCAGCCGGCAAGATTTCACGAAATCTAATGGCCAAGGACGAGGAGGATGATCTGC
TGCCCGACAAGGATGCGGCCAAGGGCTTCTATGCCAAATACGAGCCCAAGGAGATTCTGGGCAGGGGCATCAGTTCGACCGTGAGGCGATGTATC
GAAAAGGAGACGGGCAAGGAGTTTGCCGCCAAGATCATCGACTTGGGCGCCACCACAGAGTCAGGCGAGACGAATCCATATCACATGCTGGAAGC
AACCAGACAAGAAATCTCAATACTGCGCCAGGTCATGGGGCATCCCTACATAATTGATCTGCAGGATGTGTTCGAGTCAGATGCATTTGTTTTCC
TCGTCTTCGAGCTGTGTCCCAAAGGTGAACTCTTCGACTATCTGACCTCTGTGGTGACGCTATCCGAGAAGAAGACGCGCACCATTATGCGACAA
ATCTTTGAGGGCGTCGAGTACATACACGCGAAGAGCATTGTCCATCGGGATCTTAAGCCCGAGAATATCTTGCTGGACGAGAACCACAACGTTAA
GATCACGGATTTTGGCTTCGCCAAGCAGTTGCAAGAGGGCGAGAAACTTACAAATCTGTGCGGAACGCCGGGTTATTTGGCTCCCGAAACGCTCA
AGTGCAACATGTTCGAGGGATCCCCCGGCTACTCGCAGGAAGTCGACATATGGGCCTGTGGCGTGATTATGTTTACGCTGCTCGTCGGTTGTCCA
CCTTTCTGGCACCGCAAGCAGATGGTCATGCTGCGGAATATCATGGAGGGCAAGTACAGCTTCACCTCGCCGGAGTGGGCTGATATTTCAGAGGA
TCCCAAGGATCTGATACGCAAATGTCTAGTCGTTGATCCTTCGCAACGTATAACCGTCAAGGAAGTATTAAGACATCCATTCTTCAACCAAATGG
TGTTAATGGGTGATCGCCGGCATCCGGCCCCGCCCATCGCGCCCGCCCAAACGAACAGCAGGCATCTGCTGCAACCCGAGGCGTCATCGTATCGC
TTTGGTCAGCTGAACAGTAGTTGCGCCGGTGCCCCCAATTATCTGTACTGTGCGCCACAGAGCTCCTACTCGTCGAATCGAATGCGCGACGGGGC
GCTGGACGATGCGGGTGCCAGTGCTGCATCCGCCACCTGCCATGTCATGTCGCCATCCAACGCCTCCAATTCCTACGCCACCAACACCACAGCCA
ACACCTCGAACTCGGCCTTGGCATCCGCCTCCTCCCACAAAACGCTCACGGCGATGGTCTACTATCAGCAGCAACCGCAGCAGCATCAGACGCAG
CAGCAGCAGCAACAGTACCAGCAGCAACAGACGACACAGCTGCCGGTGCAGCTGCAGTTGCAGCATCCACTATTGCAGACCGGTGGCGATGGCAA
GCAATCGGTGTATGCACCTCCTACAGTGCAGCTGCGCAAACAAAGTCGCTTCAACGCGCGCAAAAAGTTCCAATTCGCCATACTCGTGATACGGG
CCATCATTCGGATACGGCGCCTACGCTTCACCGCCGAGCCGCTGCACGTTGAGGAGGCCATCCGGGATCCGTATCGCGTCAAGGTTCTGCGCAAA GTCATCGATGGCTGTGCCTTCCGTGTCTACGGGCATTGGGTCAAGAAGGGTGAGGGCCAGAATCGGGCCGCCCTCTTCGAGAATACTCCCCGCAC
GGAGCTCCACGCGCTCTACATCAACAATCTCAGCCGATAG
(SEQ ID NO: 164)

Start ATG: 258

MAKDEEDDLLPDKDAAKGFYAKYEPKEILGRGISSTVRRCIEKETGKEFAAKIIDLGATTESGETNPYHMLEATRQEISILRQVMGHPYIIDLQD
VFESDAFVFLVFELCPKGELFDYLTSVVTLSEKKTRTIMRQIFEGVEYIHAKSIVHRDLKPENILLDENHNVKITDFGFAKQLQEGEKLTNLCGT
PGYLAPETLKCNMFEGSPGYSQEVDIWACGVIMFTLLVGCPPFWHRKQMVMLRNIMEGKYSFTSPEWADISEDPKDLIRKCLVVDPSQRITVKEV
LRHPFFNQMVLMGDRRHPAPPIAPAQTNSRHLLQPEASSYRFGQLNSSCAGAPNYLYCAPQSSYSSNRMRDGALDDAGASAASATCHVMSPSNAS
NSYATNTTANTSNSALASASSHKTLTAMVYYQQQPQQHQTQQQQQQYQQQQTTQLPVQLQLQHPLLQTGGDGKQSVYAPPTVQLRKQSRFNARKK
FQFAILVIRAIIRIRRLRFTAEPLHVEEAIRDPYRVKVLRKVIDGCAFRVYGHWVKKGEGQNRAALFENTPRTELHALYINNLSR*
(SEQ ID NO: 165)

Name: Phosphorylase kinase gamma
Classification: protein_kinase
Gene Symbol: PhKgamma
FlyBase ID: FBgn0011754

Celera Sequence No. : 142000013383929
CTTGGCCAACTGCATCACGGCGTGCCACATGACCGGCCACCAGCGAGATCTGCTTACGTTCCTGCAGCACATCCAGCCGGGCATCGAAGAGTGCA
AAGCCGCGATGACCACTGTTATTATTCACCGGCGAGCGTGTAATCCGTTGCCACTCCTGCACATCGGTGCGCGTTCTGTCGCCGGTGTCCACCAG
ATGGTAACTGGTTATACCGTCGCAGATCACACAGAATCGTTCCGAAACGAAAACTATGGTGTAGTTGTAGTCACCCGACCGATGTAGTTCCCCAT
CGCCCTGATCCCTATAGTCCACCGTGAGGACAACGCGCTGGGCACGTGCGCGTCCAGTCTGTAGATCGTAGTTGCACTGCACCAGCTGGTGGCGC
TTGTTAAAGAAGTAGCTGCAGTGGCGCATCCATGGATCGGCTACCAGGTGATTGTGTCGGGCAAAGAGCTCCGTGTGCAGCAGCGAGAACTGATT
GCTGCTCGGATCCAGCACGTAGGCATCACATCCAAGTTCCTGGCGAAGAACAGGCACCGAATCGAATGCCAATTTGTAGCCAGAAAAGTCCGAGC
ACACCAGGTTGCGATCCACTTTCAGTTCCACCACCGGCATCTTGCTTTACTGCGCCAATGCTGAGTTGGATTATATTGGAGATTTCGAAAAAATA
GAGATAGATATTCCAAAACAAATCAAATCAAATCGGTAGTAGACCGGATAGAGATGGCAGATGACCGTTCGGCCGTGACTCGTATCGACTTTTTA
TCGACAAGTGGGGGATATGTACGATACCTTGGCAATTTTCAAATCTAATAAGATTCCTTTTTTTAGTTTGAAATTTAACTAAACAATTAAATAGC
TAAAAAGAAAACATTAGTTAGTCACATATTTTTTTATCGAATCGAAAGTTTAAGCAATGTATCGATATAGCCCACATCGGTATCTAGCTCATCTC
GATAGCGCCTGCCTATCGACGGACGGCCATCGGTAGTTGCGTGCCGTGGGAAAAACATAACGGGAGCGGAGCAGCTGTTGCCTGCTAATTGAAAA
ATTAGACACAAGAACGCAAAATTGTGAGTTTCGTGTGGAGTTTGGCCAAGTGAAAAGCGTTGGCGGGAGGCGACTACTCCACCACAACAAATCCA
GTAGTAGCTGCAATACGACTCACCCGACTCCACAAAGTTAGTTTAGTGACACAATTCGGTACGTGCGATAGGGCGAGGGGCAACTCAAAAGTTCA
AAATCTCAAGTATATCAAGTAATTCCGCATCGTCGTGTTCCGCCCACCCAAAATAATGCACATTGAGGATGCCAAGTGACGAGAGAGTAGAAGCG
ACGATGTCCACGGTGCGCCTGCCCATTGTGGGCATGACTTGCCAGTCGTGTGTGCGCAATATCACAGAGCACATTGGCCAGAAATCGGGAATCCT
TGGCGTGCGCGTCATTCTCGAGGAGAATGCGGGCTATTTCGACTACGATCCCCGACAGACGGATCCCGCCCGGATAGCCAGCGATATCGACGACA
TGGGCTTCGAGTGCAGCTATCCAGGGGATGCAGCAGATCCTCCCGAAACTCCCGCCAGCGCATGGACCAACATACGGGTGGTGGGCATGACCTGC
CAGTCGTGCGTGCGCAACATCGAAGGCAATATCGGCACCAAGCCGGGCATCCATTCCATTGAGGTGCAACTGGCGGCCAAGAATGCCCGCGTTCA
GTACGATCCCGCCCAGTATGATCCCGCCCAGATAGCCGAGCTCATCGATGACATGGGTTTTGAGGCTAGTGTGCAGGAACCTCGATCGCCATCCC
AATCGCCGTCGCCCGCCCCCGCCTCATCACCCAAAAAGAGGGCAACTCCTACTCCTCCACCTCCTTCATATGCTCAAAATGGTTCGGCAGTGGCC
ATACCCGTCGAACAGGAGCTACTGACCAAATGCTTTCTGCACATCCGAGGCATGACGTGCGCCAGCTGTGTGGCCGCCATCGAGAAGCACTGCAA
GAAGATCTACGGCCTGGACAGCATCCTGGTAGCCCTGCTGGCCGCCAAGGCGGAGGTCAAGTTCAATGCCAATGTTGTGACGGCCGAGAATATAG
CGAAATCAATCACGGAGCTGGGCTTCCCCACCGAACTCATCGATGAGCCGGACAACGGCGAGGCGGAGGTGGAGTTGGAGATTATGGGCATGACT
TGCGCCTCCTGCGTCAACAAGATCGAGAGTCATGTGCTTAAAATAAGGGGCGTGACCACCGCCTCCGTCACACTGCTAACAAAGAGGGGTGAGTG
TTTTTGTGTACTTAAGCTAAGTGGCTTTCTGGAACTAGTTTATCCCGAGAGAATTTCAAATCACGTTCTGGGTCATGCATTCGAATCGAATTGC
GAGTCTGGAAGCATTCCACAAGTGGCAGTGCCAATTGTTATGCAATATTTATAATAATAAACACCTGGAATGGGGCCATCAACCGATATGCACCT
GTTGCGCTTTATTCTTGCCCAACGAGCACAGGTGTTAAATTCGATCATATATCTTGTATATCTTAAGGGATCGAATAATGCAATGGGAGTAATGA
GCTGTAACAGAAGCAAACTATTGGCAATCGTTAATTGATGCAACTTGTGGCAATAACAAATATTAAATAAGCCATTCAAGGGAATTTCGTAGAAT
GCCCTTATTTGTTTTGCATTTCGCAGAAAGCGACAGCTGTTCCTTTTTATTAACCTACTAGCATCGAGTTCGAGTAGAATCGGTGCAAATGTTTT
TTTTTTTTTATTGTTCGCTTTTCACAATTTCCACAATTGAAAACTGGCCCAGCAATTGTTTATTGCAACTGATATACTCGATTTACTTTATGCT
TTTTTTTCTGGGGAGGGTGGCAGGTTCGTTGATAAGAAAGTGCGAGGAGCACTATACTCATATGCATGTATGTATGTATGTACTTTATAAACCAT
ACACTACTAACTATGCTTTCAGCAAACAATGCCAGTGGCAACTAGATTAAATAGCTGGAATTCACCACGCTCGTGTGCGTGGGCAGTAAAGCTAT
CTGGAACACTTGGATGAGGGGAATTCAATGGCAAGCCGAGAGTCGGGATATTTAAAATATTCAAGATATTCGCTAAAAAACACATAATATAATTA
TTGTTTTGTTGGGCGCTGGCAGCTCGAGTTTTATTTGCCAGATTATAGCGTGTTTTTTGCGAGTGTTCAGGAAGAACTTATATATACATATTTAT
GTATGCGATTAGCTGACAAAGAACAAATGAAATGATTTGAGCTCTTTGTTTTCATAAACTTTATACTGCCAATCGCATTTACCAATTAGCATTTA
AGCCATGAAACTGAAAGTCCGCCTGGCCAAAGAAAAATCAAAACAAAAGTGAAAGAGCTCCAATACGCCTTGAAATACAAGTACATACATATAAT
GTATGTACATATATATGTATGAATGTATAATAATTTATATACCCGCGATTGGCGGGCAAACGAGCGAGGAACTAATCTCGCTTTTGTCTGGAAAA
AAAGAGGGAAACCTCTCTCTTTTTCAGCTTTGCAGTCTTTCTGCTCCGCATGCGTGGCCACGAACTCCACTTCCACTTCGTACACAGCGAGAAAT
GGGGCTAACTATGATATAAGTATTATATAGAAGAGTGCTATCTACTTCGGCATATGATCAGCATATAAAATCTACTAATATTTAAAAGCACGAAT
CGTACAATGTTTAGCAAGTTTCTTTTATTTTATGTTAAGCACGCACTTTTTCTTCGAGTGCATTTCTAGTTTCATTCACCTTCACTTTGATTTAG
AGCTGTTTTTACTTTACTTTTGCTTTGCCAGCTCAAAAATGTTGATTTGAAATTAGTGAACTAGTGGCGAATTATGCAATAACTTGGCTTTGATC
CACCACATTCACATTGAATTCTGGCTGATTTACGAATATCGGTTTGCATACCCGTATTTATGTATGTACTAGATGTACGTGCGCCGTTTTGAGAA
GCTCAATTGCAAATTCAAAAATGAAAATGCATAAATGGGGAGCCTCGTAATTATGATTGCAATGGAACTGGTTTTCGATTTTTTCGCATTCGACA
TGGAGACATGCGCACGGTGGAGAAAAGCGAGCGAAACTGTTGCGATTAAATGACACTGAAAATAATTTCAGACATTCAAAAGTGGTATGAAAACA
GCGAGCCCACATGAATATCAATCGCTGGCAGCTGTATGATGGTATATAAAGTACAATATCGCTTGTTTTTTTAAAGTTTATTTGTTTATTTTGAA
TTTACATATATACTTATTAAGATACTTAATTGTATTGTAATCATTTTCGAAAAACAATTACGTACCAGTCATGCTTCTGAAAGAGTTCATAGATG
TTTTGGGCCAGCGAAGTTGGACTTCTGCCATATGGATTGGTCCAATTCCGTGCGGCTTCTTATCTTTCAATCAATTAGCACTTAAACTTCATTTA
ACTAGCTTAACTTGTTGTTTGCCAATTGTTACTTGGCTTGTTTGCAGTTTGTTTGCCGCAAGTCGGTAGTCGAAATTGGGAATGTAAACTGTTGA
GCAAAACATATGTTTTCCTCCGATTCTTATCGTCCGGCGATAAGTGAACGACAGAGAACGAACCACAGGCAATCTCAATTCAAATTGAAAATGTT
CTAAAATTGTAACAACGAATCGCGGGCGATAAGATGCAATGGGCGGGCAAATAAAAGAAAGAAAGAACAAAAAAACTGAATCGAGAGCCCTAGAA AATGTATATTTCGACGACTGCAGTGGAACTTGCATAACTCATAAGGGATAGATTAAGATACCCACATATATTACTTTTGCTACTTTACTTTTGAT
TCGTTGAAATTCGAAAATGAAGTTCGAAAAAGCAATTTCTTGTGTAAACACACGAAACGCATCAATTATCAATTGAAAAGTGGGCTAAGATCGAT
CGGTAGCACTGATAATTAGCGACAATTGTCACATTCGGTGTGATCAACCTAATCCTTCCTCAATTTTGCACACGACCCATCGTCTGGTGTCCACT
TGGTGGCCCTCTAATTGAACGATAAATAATGATATCATGGGTTCTGTCAGCTCCCAAGCGATTCCCTTTGCTTCAATCTATGCTATTAATTTGAA
GGCATATCTACAGATGACTCAAACAAACCGTTGCTCTAATCTAAACGTAAATTTGCCTAGTTACAGTTTACGCGATGACGAAACGAAACAGAATG
ATCTTTTGTTCTATTCCCACTTCTGATAAGAACGTTGAACTAACAACGATTGCAATGAGTAGGCAAAAAGTATGCAGGCTCACAAATGTTGATAG
ACTGAAATGTTGTGCCTGTTAATAAAATAAAAGTATTACTAAGCGCAGCCGATGGCTAAAACCAGTTTTCTTGGCCTCTGCGAACGAGCATAATA
ATTCTATAATTTCTTTAAAATTATTCTTGGCTTGAGGAATAACTCATTATAGAACTGTATGATGAGTATGGTATATGGCGATTGCTCGCTTATCA
ATGAATCCAATTGAAGCCAGTGACAATTTCCCCTCTTCAAATAAAGATCGGAAATGTGAAAAACTAATAAGACGATGAATGGGAGAACCTACTGG
GGGAATAACATAGCCAACAGATGGCAATAATGTCGAGAAATTCCAGTTGCGGGCCAAAGTTGTGGGCGACAACATGCTCTAATCATGTAGAGAAA
CGGCAGCGATTCAGTTTACACATTCTACATAGTTAAAAAGAAGCTATCTTATCTACAAATTGTGCTGGCGGGGAAAGGCAATGAACCTACAGCTG
CGATATTTTGTGACCAAGATTCCCGGAGCCTCTGAGCCCCACGGATTTTTCTATAATCCGACTGAATGATGCGATAGTTTTTGGCCACATGTCTG
CTATATGGGCAAATAATACTGCCTTAAGTTGTGAAATGAGGCAAATGTATGTAGCTCACAAACCAGAAACTATAAGCCATTGCTTATATCAAATC
TGTCGCCATCGAACCGGTTGTATGCTCCAATTTCAATACCAGAACAACCGGCATTATTTCCACTCAACGACGGTGTACAAACACTTTTCATTTGA
CGCCAGGGAAAAAGGAAACCCACAAAAATTCCCTAGGTTCCTCTGTCTATGTCCAAGGAAACATATGGAAACACTAGCCCTTCTCCTATAGAGTT
TTCGCTGGTGTCTTGTCAAAACACAGGAGTAGCCATATAAATGTGCTAACAAGCTCCAGAAACTGTGATGAAATTGATATGGCATTCAGATATGC
GAGTGCACATTCAGATTCACTTACACATACTCATGGAAATGAAATCGAATATACCTGAAAAGTAGTAATATTTCAATTCCCTAGATATACAAAGC
TCATGCGGCTTCATTATTTTTCTTGGCTTGTACGCTTGGCATAGCAAATATCGTTATTAAAGATCAGCAGTATATAGCTTTCACTTCAATCAACT
GAATCTTTGATAAATATCCTATGTGAATATTCACTGGCCATTTAAAGTGGCTTTCTCTATTTTTTTTTAACGACTGGTTCTGTAAAAGTTGCACA
TGAAACAAGTCCGGTTTTTCAGTGTACCAATTGAAACTAACTAGGCTGAAATGAGGAGGAATAATAAATACTACGTCACTATAATTAACTTATTC
GACTGATTTTAATAGATGATATTTAAGTTCTATCAACTTATAATCTTAATCTTAATTTTTACAGGCAAATTCCGGTACATCACGGAGGAGACGGG
TCCCCGGAGCATCTGCGAGGCGATCGAGGCGCTGGGATTCGAGGCCAAACTGATGACCGGCCGAGACAAGATGGCCCACAATTATCTGGAGCACA
AGGAGGAGATACGGAAGTGGCGCAATGCCTTCCTCGTCTCGCTAATTTTCGGTGGACCCTGCATGGTGGCCATGATATACTTCATGCTGGAGATG
AGCGACAAGGGACATGCCAACATGTGCTGCCTCGTGCCCGGCCTGTCGATGGAGAATCTGGTGATGTTCCTGCTATCGACACCAGTGCAGTTCTT
CGGTGGCTTTCACTTCTATGTGCAATCCTATCGTGCGATCAAACACGGCACCACGAACATGGATGTACTGATCTCGATGGTCACGACCATCTCGT
ATGTGTACTCAGTGGCCGTGGTGATCGCCGCCGTGCTGCTAGAGCAGAATAGCTCCCCACTGACCTTCTTCGATACGCCGCCCATGCTGTTGATC
TTCATATCGCTGGGTCGCTGGCTGGAGCACATAGCCAAGGGAAAGACCTCGGAGGCCTTGTCCAAGCTGCTGTCGCTCAAGGCGGCCGATGCCCT
GCTGGTCGAGATATCACCGGACTTTGATATCATCAGCGAGAAGGTGATATCTGTGGATTATGTACAGCGTGGCGATATCCTAAAGGTGATACCGG
GAGCCAAAGTTCCAGTGGACGGCAAAGTTCTGTACGGTCACTCCAGTTGCGATGAATCACTAATCACCGGGGAGTCTATGCCGGTGGCCAAGCGA
AAGGGATCCGTCGTAATCGGCGGTTCCATTAACCAAAACGGTGTGCTCCTCGTAGAGGCAACGCACACGGGTGAGAATACGACGCTCGCGCAGAT
TGTGCGATTAGTGGAGGAGGCCCAGACGAGTAAGGCGCCCATCCAGCAACTGGCCGATCGGATTGCCGGCTACTTTGTGCCCTTCGTTGTTGTAG
TGTCCAGTATAACGCTGATTGCTTGGATCATCATTGGTTTTTCCAATCCAAACTTGGTGCCCGTGGCCATGGAGCATAAGATGCACATGGACCAG
AATACCATCATCGTTAGTTATGCATTTAAATGTGCCTTGAGCGTGCTGGCCATTGCGTGTCCATGTGCTTTGGGCTTGGCCACGCCCACCGCTGT
AATGGTGGCCACTGGAACGGGTGCGATCAATGGCGTGCTGGTGAAAGGAGCCACTGCCCTAGAGAATGCCCACAAGGTGAGCGAGCGAATAACCA
TGCAAAACTTTAACCCACTTATACGCTTTTTACGCTTCCCAAATATTTTAGGTAAAGACTGTGGTCTTCGACAAGACCGGCACCATAACCCATGG
CACTCCGATGACCAGTAAGGTTACCCTCTTCGTCACAGCCCAGGTCTGCAGCCTGGCGCGTGCTCTGACGATCGTGGGAGCCGCCGAGCAAAACA
GCGAGCATCCGATCGCCTCCGCCATTGTGCACTTCGCCAAGGATATGCTGAACGTGGGCGCCACACCTCAGGCCGGCAGCTTTGGCAAGAGCAGT
CACTTCCAGGCCGTGCCCGGCTGTGGCATCCGCGTCACCGTCTCCAATTACGAGCAGACTCTGCGACAGGCGTGCAACGCCGATCGGATCATTAA
CTACGAGAACCTGCATCGCACTCATCCACAGGGTTCGGTGCCGGTGGACAATGGAGCCAGTATCGAACACTTGCTGCCGCAGCGCAGCGTACGCA
AGTCCATGGAGCTGAACAATCAGCAGTTGCTATCCGACTTGGTATTGGAACCGGAGGAAGAGCTCCTTACGGATCAGAAAATCATCGATTCACCC
GAGATTCTGGTGCTGATCGGCAATCGCGAATGGATGGAACGCAATGCCATCGAAGTGCCGCTGGAGATTAGCGATTGTATGACGCATGAAGAACG
AAAGGGACACACAGCTGTGCTATGCGCCCTCAACGGGCAGCTGGTGTGCATGTTTGCGGTGTCCGACATGGTCAAGCCAGAGGCCCATCTTGCCG
TCTATACACTAAAGCGAATGGGCATCGATGTGGTGCTGCTCACGGGGGATAACAAGAACACGGCAGCCAGCATTGCCCGAGAGGTGAGTGTCCAG
CGTGCTCATAGCAATACTGTTCCTAGGCTAATGAACTTATGTATATTCATTAGGTTGGCATCCGAACCGTGTACGCGGAGGTTTTGCCCTCGCAT
AAAGTGGCCAAAATCCAGCGGATACAGGCCAACGGTATACGCGTGGCCATGGTGGGCGATGGAGTCAACGACAGTCCGGCGCTAGCGCAGGCAGA
TGTGGGAATTACGATTGCAGCGGGCACGGATGTTGCCGCCGAGGCATCGGACATTGTCCTGATGCGCAACGATCTGCTGGATGTGGTGGCTTGCC
TGGACTTGTCCCGCTGCACGGTGCGTCGCATTCGGTACAACTTCTTCTTTGCCAGCATGTACAATCTGCTGGGCATACCGCTGGCCAGTGGCTTG
TTCGCACCGTACGGCTTCACCCTGCTGCCATGGATGGCGTCCGTGGCCATGGCCGCCAGCTCCGTGAGCGTGGTATGCTCATCGCTGCTGCTCAA
GATGTATCGCAAGCCCACGGCGAAGACGTTGCGCACGGCAGAGTACGAGGCGCAGCTGGCGGCGGAACGCGCAAGTGGGTCCGAAGACGAGCTGG
ACAAGCTGTCCCTCCATCGTGGCCTTGACGATTTGCCCGAAAAGGGTAGGATGCCATTCAAGCGGTCCAGCACATCACTGATTTCGCGCATTTTC
ATGCACGACTACGGGAACATCACTTCGCCGGATGCCAAATACGGGGAGGGACTGCTGGATCCCGAGGAGCAGTATGATGGCCGCACCAAGATCGT
GAGGAGTCGCTTCCATGCCAATGACAGCACCGAACTGCAAAAGCTGTGAGCTAAACGATGGCAACTAGCAAGCTACTAGCAACCACAATCAAACC
GAAGACCTTAAAACGACAAATTTTCAGTGAAATTGTTAGCGGACTATAAATTGAACCAGTAAGAGAGCGAATTATAAAAACCTATGTACATATTT
GCAAATTGTTTTGACAAAGGTTGAGCACTAGGATACTAGGGTTATCTTTGATCTACGTGCAGTCTAATATGAGTTTGTGTGACTCACATGTGGGA
AAAGATATAGGTATCTTAAGAAAATATTCTCGGTATGTAAATATATATAGCATAATCACGAAGTCATTCACTTTCATTTTAAGTATGGTTTTTTG
AACTACTGAGGTGCCTTTTTATGTTAAAGCCACTACATACTTGTCTTTTCTTACAAACGTTGTATTGGAGATTGTAGAAAACAAAGATGACATTT
CGTTACCACTGATTCTAGAGATCTTTTGTTCCAAAATCAATTTGTGACCGGTTTTCCATTTCTTAGTGCCGCACCCACACCGTCCCCCTTTTCTA
TACAATTGTTATTTTCCTATCTTTTTTATTTTATTAAGAAACCTACAACAACAAAAGTTCGATACGATAGCTTCTTCTTTTCCACTTGATTATAT
TATTATTATTATTGTATACAAATCTTTTTTTTTTTTGTTATAATCGTAAGTGCAATATTTTTATTATTAAGTTCAAATGAACAAAGGCAAAGGAG
TCCACAGACCAGGAGATAAAACCCAGACATTAATCATCATTGAACTATTGTTACTCATTGTTAATTCACATTATCATATATATGCACATATGCAA
AAGGTAAAATAAATCAAAAGACGAAAATCGAACAAAAAGACCATTTGACCCCATATCGGCATTAATCCTTAATTGTGCTATTCGCGGACGACGAA
CACTTGTAAGACAATTGGGCACAAGCATAAGGCAAATTGAAACGCAAAAGAACGATTAACATTCTTTATGTGTAACTTTATTGTTTATAAACAAA
AAGC
(SEQ ID NO: 166)

Exon: 1001..2273
Exon: 6715..7961
Exon: 8032..8448
Exon: 8554..8823
Exon: 8889..9644
Start ATG: 1334

FIGURE SHEET 82

Transcript No. : CT5824
AAAAACATAACGGGAGCGGAGCAGCTGTTGCCTGCTAATTGAAAAATTAGACACAAGAACGCAAAATTGTGAGTTTCGTGTGGAGTTTGGCCAAG
TGAAAAGCGTTGGCGGGAGGCGACTACTCCACCACAACAAATCCAGTAGTAGCTGCAATACGACTCACCCGACTCCACAAAGTTAGTTTAGTGAC
ACAATTCGGTACGTGCGATAGGGCGAGGGGCAACTCAAAAGTTCAAAATCTCAAGTATATCAAGTAATTCCGCATCGTCGTGTTCCGCCCACCCA
AAATAATGCACATTGAGGATGCCAAGTGACGAGAGAGTAGAAGCGACGATGTCCACGGTGCGCCTGCCCATTGTGGGCATGACTTGCCAGTCGTG
TGTGCGCAATATCACAGAGCACATTGGCCAGAAATCGGGAATCCTTGGCGTGCGCGTCATTCTCGAGGAGAATGCGGGCTATTTCGACTACGATC
CCCGACAGACGGATCCCGCCCGGATAGCCAGCGATATCGACGACATGGGCTTCGAGTGCAGCTATCCAGGGGATGCAGCAGATCCTCCCGAAACT
CCCGCCAGCGCATGGACCAACATACGGGTGGTGGGCATGACCTGCCAGTCGTGCGTGCGCAACATCGAAGGCAATATCGGCACCAAGCCGGGCAT
CCATTCCATTGAGGTGCAACTGGCGGCCAAGAATGCCCGCGTTCAGTACGATCCCGCCCAGTATGATCCCGCCCAGATAGCCGAGCTCATCGATG
ACATGGGTTTTGAGGCTAGTGTGCAGGAACCTCGATCGCCATCCCAATCGCCGTCGCCCGCCCCCGCCTCATCACCCAAAAAGAGGGCAACTCCT
ACTCCTCCACCTCCTTCATATGCTCAAAATGGTTCGGCAGTGGCCATACCCGTCGAACAGGAGCTACTGACCAAATGCTTTCTGCACATCCGAGG
CATGACGTGCGCCAGCTGTGTGGCCGCCATCGAGAAGCACTGCAAGAAGATCTACGGCCTGGACAGCATCCTGGTAGCCCTGCTGGCCGCCAAGG
CGGAGGTCAAGTTCAATGCCAATGTTGTGACGGCCGAGAATATAGCGAAATCAATCACGGAGCTGGGCTTCCCCACCGAACTCATCGATGAGCCG
GACAACGGCGAGGCGGAGGTGGAGTTGGAGATTATGGGCATGACTTGCGCCTCCTGCGTCAACAAGATCGAGAGTCATGTGCTTAAAATAAGGGG
CGTGACCACCGCCTCCGTCACACTGCTAACAAAGAGGGGCAAATTCCGGTACATCACGGAGGAGACGGGTCCCCGGAGCATCTGCGAGGCGATCG
AGGCGCTGGGATTCGAGGCCAAACTGATGACCGGCCGAGACAAGATGGCCCACAATTATCTGGAGCACAAGGAGGAGATACGGAAGTGGCGCAAT
GCCTTCCTCGTCTCGCTAATTTTCGGTGGACCCTGCATGGTGGCCATGATATACTTCATGCTGGAGATGAGCGACAAGGGACATGCCAACATGTG
CTGCCTCGTGCCCGGCCTGTCGATGGAGAATCTGGTGATGTTCCTGCTATCGACACCAGTGCAGTTCTTCGGTGGCTTTCACTTCTATGTGCAAT
CCTATCGTGCGATCAAACACGGCACCACGAACATGGATGTACTGATCTCGATGGTCACGACCATCTCGTATGTGTACTCAGTGGCCGTGGTGATC
GCCGCCGTGCTGCTAGAGCAGAATAGCTCCCCACTGACCTTCTTCGATACGCCGCCCATGCTGTTGATCTTCATATCGCTGGGTCGCTGGCTGGA
GCACATAGCCAAGGGAAAGACCTCGGAGGCCTTGTCCAAGCTGCTGTCGCTCAAGGCGGCCGATGCCCTGCTGGTCGAGATATCACCGGACTTTG
ATATCATCAGCGAGAAGGTGATATCTGTGGATTATGTACAGCGTGGCGATATCCTAAAGGTGATACCGGGAGCCAAAGTTCCAGTGGACGGCAAA
GTTCTGTACGGTCACTCCAGTTGCGATGAATCACTAATCACCGGGGAGTCTATGCCGGTGGCCAAGCGAAAGGGATCCGTCGTAATCGGCGGTTC
CATTAACCAAAACGGTGTGCTCCTCGTAGAGGCAACGCACACGGGTGAGAATACGACGCTCGCGCAGATTGTGCGATTAGTGGAGGAGGCCCAGA
CGAGTAAGGCGCCCATCCAGCAACTGGCCGATCGGATTGCCGGCTACTTTGTGCCCTTCGTTGTTGTAGTGTCCAGTATAACGCTGATTGCTTGG
ATCATCATTGGTTTTTCCAATCCAAACTTGGTGCCCGTGGCCATGGAGCATAAGATGCACATGGACCAGAATACCATCATCGTTAGTTATGCATT
TAAATGTGCCTTGAGCGTGCTGGCCATTGCGTGTCCATGTGCTTTGGGCTTGGCCACGCCCACCGCTGTAATGGTGGCCACTGGAACGGGTGCGA
TCAATGGCGTGCTGGTGAAAGGAGCCACTGCCCTAGAGAATGCCCACAAGGTAAAGACTGTGGTCTTCGACAAGACCGGCACCATAACCCATGGC
ACTCCGATGACCAGTAAGGTTACCCTCTTCGTCACAGCCCAGGTCTGCAGCCTGGCGCGTGCTCTGACGATCGTGGGAGCCGCCGAGCAAAACAG
CGAGCATCCGATCGCCTCCGCCATTGTGCACTTCGCCAAGGATATGCTGAACGTGGGCGCCACACCTCAGGCCGGCAGCTTTGGCAAGAGCAGTC
ACTTCCAGGCCGTGCCCGGCTGTGGCATCCGCGTCACCGTCTCCAATTACGAGCAGACTCTGCGACAGGCGTGCAACGCCGATCGGATCATTAAC
TACGAGAACCTGCATCGCACTCATCCACAGGGTTCGGTGCCGGTGGACAATGGAGCCAGTATCGAACACTTGCTGCCGCAGCGCAGCATTCTGGT
GCTGATCGGCAATCGCGAATGGATGGAACGCAATGCCATCGAAGTGCCGCTGGAGATTAGCGATTGTATGCACGCATGAAGAACGAAAGGGACACA
CAGCTGTGCTATGCGCCCTCAACGGGCAGCTGGTGTGCATGTTTGCGGTGTCCGACATGGTCAAGCCAGAGGCCCATCTTGCCGTCTATACACTA
AAGCGAATGGGCATCGATGTGGTGCTGCTCACGGGGGATAACAAGAACACGGCAGCCAGCATTGCCCGAGAGGTTGGCATCCGAACCGTGTACGC
GGAGGTTTTGCCCTCGCATAAAGTGGCCAAAATCCAGCGGATACAGGCCAACGGTATACGCGTGGCCATGGTGGGCGATGGAGTCAACGACAGTC
CGGCGCTAGCGCAGGCAGATGTGGGAATTACGATTGCAGCGGGCACGGATGTTGCCGCCGAGGCATCGGACATTGTCCTGATGCGCAACGATCTG
CTGGATGTGGTGGCTTGCCTGGACTTGTCCCGCTGCACGGTGCGTCGCATTCGGTACAACTTCTTCTCTTTCGCCAGCATGTACAATCTGCTGGGCAT
ACCGCTGGCCAGTGGCTTGTTCGCACCGTACGGCTTCACCCTGCTGCCATGGATGGCGTCCGTGGCCATGGCCGCCAGCTCCGTGAGCGTGGTAT
GCTCATCGCTGCTGCTCAAGATGTATCGCAAGCCCACGGCGAAGACGTTGCGCACGGCAGAGTACGAGGCGCAGCTGGCGGCGGAACGCGCAAGT
GGGTCCGAAGACGAGCTGGACAAGCTGTCCCTCCATCGTGGCCTTGACGATTTGCCCGAAAAGGGTAGGATGCCATTCAAGCGGTCCAGCACATC
ACTGATTTCGCGCATTTTCATGCACGACTACGGGAACATCACTTCGCCGGATGCCAAATACGGGGAGGGACTGCTGGATCCCGAGGAGCAGTATG
ATGGCCGCACCAAGATCGTGAGGAGTCGCTTCCATGCCAATGACAGCACCGAACTGCAAAAGCTGTGA
(SEQ ID NO: 167)

Start ATG: 334

MSTVRLPIVGMTCQSCVRNITEHIGQKSGILGVRVILEENAGYFDYDPRQTDPARIASDIDDMGFECSYPGDAADPPETPASAWTNIRVVGMTCQ
SCVRNIEGNIGTKPGIHSIEVQLAAKNARVQYDPAQYDPAQIAELIDDMGFEASVQEPRSPSQSPSPAPASSPKKRATPTPPPPSYAQNGSAVAI
PVEQELLTKCFLHIRGMTCASCVAAIEKHCKKIYGLDSILVALLAAKAEVKFNANVVTAENIAKSITELGFPTELIDEPDNGEAEVELEIMGMTC
ASCVNKIESHVLKIRGVTTASVTLLTKRGKFRYITEETGPRSICEAIEALGFEAKLMTGRDKMAHNYLEHKEEIRKWRNAFLVSLIFGGPCMVAM
IYFMLEMSDKGHANMCCLVPGLSMENLVMFLLSTPVQFFGGFHFYVQSYRAIKHGTTNMDVLISMVTTISYVYSVAVVIAAVLLEQNSSPLTFFD
TPPMLLIFISLGRWLEHIAKGKTSEALSKLLSLKAADALLVEISPDFDIISEKVISVDYVQRGDILKVIPGAKVPVDGKVLYGHSSCDESLITGE
SMPVAKRKGSVVIGGSINQNGVLLVEATHTGENTTLAQIVRLVEEAQTSKAPIQQLADRIAGYFVPFVVVVSSITLIAWIIIGFSNPNLVPVAME
HKMHMDQNTIIVSYAFKCALSVLAIACPCALGLATPTAVMVATGTGAINGVLVKGATALENAHKVKTVVFDKTGTITHGTPMTSKVTLFVTAQVC
SLARALTIVGAAEQNSEHPIASAIVHFAKDMLNVGATPQAGSFGKSSHFQAVPGCGIRVTVSNYEQTLRQACNADRIINYENLHRTHPQGSVPVD
NGASIEHLLPQRSILVLIGNREWMERNAIEVPLEISDCMTHEERKGHTAVLCALNGQLVCMFAVSDMVKPEAHLAVYTLKRMGIDVVLLTGDNKN
TAASIAREVGIRTVYAEVLPSHKVAKIQRIQANGIRVAMVGDGVNDSPALAQADVGITIAAGTDVAAEASDIVLMRNDLLDVVACLDLSRCTVRR
IRYNFFFASMYNLLGIPLASGLFAPYGFTLLPWMASVAMAASSVSVVCSSLLLKMYRKPTAKTLRTAEYEAQLAAERASGSEDELDKLSLHRGLD
DLPEKGRMPFKRSSTSLISRIFMHDYGNITSPDAKYGEGLLDPEEQYDGRTKIVRSRFHANDSTELQKL*
(SEQ ID NO: 168)

Name: copper-transporting P-type ATPase-like
Classification: transporter

Celera Sequence No. : 142000013384811
TCGCCATCCTCGCTGCTGCCCGTGTAGCTGGCGGAGCTGAAGGAATCCGTTGAGGAGGCACTAAGCGAGCGGCTCCTGTACCGACTTGTCTTCTT
CAGAGCCGAGGACTGCTTGGTGGCCGGCGGAGGAACCACCACGCTGGCATCCTGCGGCGCCGGTCCAGCCTGCTGCTGCTTGTCGCCGCCTCCGA
ATCCAGGATCAACTACCACAGTGTCTGCCAGGTTGTTCATGGTGGAAGTAGAGGGTAATCTGGGGATTTCCTTACTATCCCTTAAATTGGCTCCT TGCTCTAGCTCCTAGTGTTCCACCTTCTGCGACTCCAGAGCTTGCAATCCTTTTCCGCTGCTCCTTTGAATGGGCGCCTTGGATGTTATGTAAAG
TCTGAAATCCAAGCAGGATGCGCTGCAAATGGCTAGTGGTGTGGCCTGGGTCTATACGAACTGCACAATCACGTGATTTATCGACGTTGTGGAGA
CCACAAATTGCTAAATTAATTGTTTTAGTGCGAGTCTCCTTTGTTTCACCTCTCCACTATTGTTTTTGTTCTTCTTCTTCTTTTGCGAATGGGG
GGCTACACTTTGGATCCGGGGCTTGATGGGAGTTTCCGGAGAGGGGATGATGATGCAGCCGTCGGCTTTCGGGCGACGTTGTTTGTGTGGCGACC
AAGTGGGGGATCGTTTGGCGATCGCTTATTGAATTTGATTTTATCCGGAGAAAAGAGAACTAAACCGAACCGAGGACAGTAAGCGAGACACGCGA
AAATACCAAAAGCAGAAGGCGTTAGTGCTATTCTGCAAGTGTGGTAAGTTCCCACTGAAGAAAGGCCAAAGTAACGACTTTTTAACTGAAATCGT
CTAAAAATTAATTTTTATAATTTCTTACCATTAATTATGTGTTTATTTTTTAATGAGCAAAGTAAATAAAGTGTGATTTACAACTCCTCAGCTGC
AAGTCTTTTAAATCTGGTAGCTGGATAATTTAATGAGTCAAAAAGAAATTGGCAAAGTATTCGAGGTTTATTAAAAACAAATAGTTAACACATTT
GGCCTACATATCCTCCTGTAGGTAGCCGCACAGCTCGTAGTCGTCCGCCGTGTTGACCAAGTGCGCTTCCCTAAGAAGGCCCTCCTTGTAGGTCT
GTCTCTTGACAATCAAACGCGACAATTCCTCCGGTGCAAGTGGTCCTTGCTTGGCGTGTTTCTGGATGAAGTCCGCCGCCAGTTGTCGATCCACG
ACGGACATCTCGAGGCTGCGACTCCAGGCGAGCAGGGCCAGCGGTCGCTGCGGACTCAGAGCCAGCGAGGGTGACACCAGATGGCGATACAGACA
GCCACCCACGATGTCTTGCAGCTGCTTCACTTGGCCGGGAAAAGCGCAGGGATGGTAGAGCATTACGATGGCACCTTCCGCCAGATTACGCACGT
ATCGCTGAGGAGGCAAGTAGGAATAGGTGCCATATTCAGCGGGCATCGGGCGATAGGGGCCACTGATAATACAGATTTGAATTTGAAATTAGCAG
GAAACTATAATATTGTTCGCCTTACTTGGTGGCAGGCAGATGGGAGTAGCTAATGGACTCATTAAGGCACTTGGCAGGCGGCAGATAGGCGCTAG
GTAGAAAGTGCTCCGTAAGAATGGCTTCTCTGGACAAATCCGGTTGGTACAAGCTGTGATTACTACTGATGCATAGGAAATTCAGGCTGTCACGG
ATGTCGTTTGGATCGAAGTCCACGGCAAGATTGCTCTGAAAATTGTTAATAACAATGATAGAAAAAGATGACTAATACTAAGCATTCATCGGTAT
TTAGGGGAAGTATTAGTTATATTGCCAAACTCACCTTGCCATCATCACAGCTGCTTTGTTTAGTCTTGTGCGATTCATTGGGACCCTGCGGAAAC
AATTTACCCTGCCAAGTATCCTGTGTGGTGGACTTCCCCGACTTGGTTTTGTTATCGACCAGCGGTTTTTTCTTCACCAAGTGCGGCTCTCCGGG
AGCTTGTGGAAACCACTTGCCCTGCCAGCCATCCTTGGTTGTGAACTCCAGCGGAGGAACTTCCTCCGTGGTGCTCTTCATTTTTAATTCAATCG
CTTCCTGCTGTTGTCCAGGGGCATGGGGAAACCACTTGCCCTGCCAGCCATTCTTGCCGGGCGTCGCACCTAATGGAACCTGCACACGTTGCACA
TCATTGGAAATGTCGGGTGGGGACTTCCCAATCTTCCCTAGCTTCTCATCAGGATCAAGAGTTGGCTCCAACAGATTGGCCTGCGACTTCTTGAT
GGATTTCGCATCGATGAGGGCGAACCCAAGGCACAAGAGGGTCAAGTAATGCCAAATAAACATAATAATTGCAAGCAAAAGAAAAACAAAAGCGC
AAAATAAGCAAACAAAAATATAATTAAGAACTTGGCAAAACAGCTGTGGAGCTGCGTTTTTCAACACTGGTCAAAGCATGACTTTGTTGCAGGGT
AGCAACAGGTTGTTTGGAGTTTGCATAAATCTCCGATGATAATTATGTGTTGTTTTAATAACTAAATTAAAATTATTTACGCCAAATTAAAGTAA
ATAAAGTTAATTTAAAATGACTACTTAAATCAAGCAGATTTAAAAGGAAATCAATGTATATTTGAAATATTCAGACTGGATTCTAAGGTTAAATG
ACAAATTACTCACCAGAAATCGGCTCATAATAATAAATCATTTTATTTTCAAATGCCCCCTGCGAACGCTCCCCCGCATTGCACACACCAGGGGG
TATTTTACGAAGTGCCCACACCTGGCCACACTGGTCGCAGCTACAAAAAGAAGAAGAACAAGGGCCAACTTGATGGTCACTTGCTACTGCGCTTT
ATTAATTCATTATTTTCCAAAATAATGCACATATATACCCGCCCACAGCCGCTCTGCGCCCCCGCTAATCGAAAAATGTGAGTGGTAAGCGTTTT
TACCAGAGTCTTATCAACAATTTAAGCCTCAATTCCCTTCCGTTTCCGTGATTCGCCACCCAGAAAACAATAACAAAGGGGTGTTGTTGTTGCTG
TCGCTGCTGCTGCGCTGGAAAAACAACTCGCATAAAATTTTAAAACGCACAAAGAAGGCGAACGTGGAAAGTTAGGCCAACAACCCAGTCGCGAT
GTCGTGGTTCAATCCCTGGGATGGCCTCAAAACGAAAATGTGTCGCTACCTGCTGCAGCGATACCTGGGCCAGTTTTTCGAGAATAACTTGAACC
TGGAGCAGCTGAAGGTGGACCTTTACAATGGCAAGGCTGTGGTGGAGGACATTTTCCTAAAGGTCAACGCCTTCAACGATCTCTTCGAGGACCAG
GGCTGGGCCTTCGAGGTGGTCTCGGGCCACATTGGCCGCCTGACTGTCGTGGTGCCGTGGAATGCGCTGATGACCAACGACAGTAGCCTGGAGAT
CCACAATCTAA
(SEQ ID NO: 169)

Exon: 2431..1840
Exon: 1745..1546
Exon: 1487..1001
Start ATG: 2343 (Reverse strand: CAT)

Transcript No. : CT5902
CGCAGCTCCACAGCTGTTTTGCCAAGTTCTTAATTATATTTTTGTTTGCTTATTTTGCGCTTTTGTTTTTCTTTTGCTTGCAATTATTATGTTTA
TTTGGCATTACTTGACCCTCTTGTGCCTTGGGTTCGCCCTCATCGATGCGAAATCCATCAAGAAGTCGCAGGCCAATCTGTTGGAGCCAACTCTT
GATCCTGATGAGAAGCTAGGGAAGATTGGGAAGTCCCCACCCGACATTTCCAATGATGTGCAACGTGTGCAGGTTCCATTAGGTGCGACGCCCGG
CAAGAATGGCTGGCAGGGCAAGTGGTTTCCCCATGCCCCTGGACAACAGCAGGAAGCGATTGAATTAAAAATGAAGAGCACCACGGAGGAAGTTC
CTCCGCTGGAGTTCACAACCAAGGATGGCTGGCAGGGCAAGTGGTTTCCACAAGCTCCCGGAGAGCCGCACTTGGTGAAGAAAAAACCGCTGGTC
GATAACAAAACCAAGTCGGGGAAGTCCACCACACAGGATACTTGGCAGGGTAAATTGTTTCCGCAGGGTCCCAATGAATCGCACAAGACTAAACA
AAGCAGCTGTGATGATGGCAAGAGCAATCTTGCCGTGGACTTCGATCCAAACGACATCCGTGACAGCCTGAATTTCCTATGCATCAGTAGTAATC
ACAGCTTGTACCAACCGGATTTGTCCAGAGAAGCCATTCTTACGGAGCACTTTCTACCTAGCGCCTATCTGCCGCCTGCCAAGTGCCTTAATGAG
TCCATTAGCTACTCCCATCTGCCTGCCACCAATGGCCCCTATCGCCCGATGCCCGCTGAATATGGCACCTATTCCTACTTGCCTCCTCAGCGATA
CGTGCGTAATCTGGCGGAAGGTGCCATCGTAATGCTCTACCATCCCTGCGCTTTTCCCGGCCAAGTGAAGCAGCTGCAAGACATCGTGGGTGGCT
GTCTGTATCGCCATCTGGTGTCACCCTCGCTGGCTCTGAGTCCGCAGCGACCGCTGGCCCTGCTCGCCTGGAGTCGCAGCCTCGAGATGTCCGTC
GTGGATCGACAACTGGCGGCGGACTTCATCCAGAAACACGCCAAGCAAGGACCACTTGCACCGGAGGAATTGTCGCGTTTGATTGTCAAGAGACA
GACCTACAAGGAGGGCCTTCTTAGGGAAGCGCACTTGGTCAACACGGCGGACGACTACGAGCTGTGCGGCTACCTACAGGAGGATATGTAGGCCA
AATGTGTTAACTATTTGTTTTTAATAAACCTCGAATACTTTGCC
(SEQ ID NO: 170)

Start ATG: 89 (Reverse strand: CAT)

MFIWHYLTLLCLGFALIDAKSIKKSQANLLEPTLDPDEKLGKIGKSPPDISNDVQRVQVPLGATPGKNGWQGKWFPHAPGQQQEAIELKMKSTTE
EVPPLEFTTKDGWQGKWFPQAPGEPHLVKKKPLVDNKTKSGKSTTQDTWQGKLFPQGPNESHKTKQSSCDDGKSNLAVDFDPNDIRDSLNFLCIS
SNHSLYQPDLSREAILTEHFLPSAYLPPAKCLNESISYSHLPATNGPYRPMPAEYGTYSYLPPQRYVRNLAEGAIVMLYHPCAFPGQVKQLQDIV
GGCLYRHLVSPSLALSPQRPLALLAWSRSLEMSVVDRQLAADFIQKHAKQGPLAPEELSRLIVKRQTYKEGLLREAHLVNTADDYELCGYLQEDM
*
(SEQ ID NO: 171)

Celera Sequence No. : 142000013384570

FIGURE SHEET 84

CAATGTGTACCAGTCAGTAAGTTTTCGAACATCACAGGCGTAGAGGCGCAGCTCCCACATGGCTCCATTAGCAAGGTGGCGAGGATGGCAGATA
TGGCAACCTCAACGAAAGCGCTGGCCGTCAAGATCAGCTGCTTCCGCGAAAACCTATGTGAATTCACTAAGTAAGTTCTTCTTCCAGTTTGATTA
GTTCACTCACTTGCGATCCTTGGCGTCCATGTCAATGAAAAAGCAGTGCATCATAAGTGGCAGCATGGTCATGAATCCCAGGTATAGCCAGGAGT
ACGTGCTTAACTCGTCGCGGCATGGAGAGCATGCGTAACTTTGGTTCACCTGAACAATATAAAAGTAAATTATTTTCCAGGCGCCGTTCCGAAGG
ATGCTAGAACATTAACCCGAGATCCTCTGGGACAGACCCCGCAGCTGCTCCAGCTGTTGTTTCCTAGCGGTGATCGCCCACAGTAGGCTCCTGGG
CAGCGTTCCAACGCGTCGTACATTCTCATGAAATCAAAACAATTACTTCGTATTGTATATTACATTAAACAAAATAAAAACAATACTCCTATCGA
TATCGGACTTATCGTTATCAGTAGGACCACTGAATAAACGAATAGGTTGTTCGTGCACTTAAATTAATACTAATTTATAAAATGATAATACATCA
GAAGCACATGCGAAATGTATTAAAAATAAGGAAATTATTTTCTACAGATTATATAATGGGCCCTAAGACTGCTTTCTAATTTGATCAAATTAATA
ATACTATATGTTTTATATATTTATTTACAATTAAACATGACTAGTAGAGTGTACATTCTTACAGTGCATTTCAATGATTTGATTTTATTTGAAA
TCCCAATTGCCAGAAATTTAAATTTAGGGTCCCTTATATGTACCACATAAACCAGTTCGATAGGCGCGCTTTTGGCATGGCCTGATAACTCTGGT
AAAAAGCACCGCGCGAACCGGTTCAATTCATAACTAGTTCGCCCGAACTGCACAACCCTAGCAAAAGAAATAGCTTAAATATAATTTATTTAACG
CGAATTGGACAACGAGCGGGTAGAAAAAACCCTGTGGCCGCAACCGCGACGCTCGCAGGATACGCAGCTCTTCGCCGTCGGGCAGGCAGGTAAAA
AGCAATGGCAATTGGAGTTGACCGCAGAACAACAGCAACGGCAGACGCCATTTTGTCTATTGGCCGGCTGATTTGTAAGCTCAATATTCGCGAAA
TAGTTACCGCGACTAGCTTCGAGTGGCGCAGCCAAGTAAGGGCTCCCCGCTGTCCAGAGCAAAGGCGAAAGGAAGAGCAATCGCCCATTTTGAGG
CCTGCGAAAAGTTGGGACTCGGTCGTCAGTTCGCTCGATTCCATTTGCGAAAAATAAATGTACGTGCGCGTGAGGAAGTGTGTGTGCGCGTGAAA
AAACAGTGAAAAATAATAAAAAGCCGCACTGGCCGCCGTCCTTGGGTGACTTCCGTTAATCTCTTACAACTTTTAAAGCTATAGAAAGAATGTGA
GCAATTTACCGCCCTCGACACACCCAATGAACCGCTAATTTTGGCATCTTTCTATAACTTTATGCGTAGTATTTTCACCACCCTTCGCCTACAC
CCTTTCCCCGCCCCTTTTTCCACCAGTGGCTCCCACCCACCGACCGACATTCCGCTTAAGGATGATGCCGGGCGGAGAGAGATAGAGAGTGAGTG
CAAAATCCGTAAACTTGGACGTGATGTAATTTTCGGCAGGAAAATGTTCTTTGTTTGCCCAAAAAAATAACAATAAATAAATAAGAATGAAGAGC
GAGGCGTAAAACAAAAACAATTTTAAATTAAACTCAAACGCACACACAAAAAGAGAGGGTTCTGTGGGTGAGCGTGCGTGCGTGTGAGTGGGTGA
GAGCGTAATTTGTGTGCTTTTGGAGCATTATTTGGCGCTTGCTGCCCCGTCTATTAAATAATATTGATTTTTCATATTCCAACCCAGCGCTCTCT
TACACACACGCAGGACCACTCACACACCCAAAACTGAGCTTCGTACACATGTGGGCCTTTTCGGTCTCTCTCTTAGCGCTGTATTTATCCGCCTC
TTATTGCCTCTTTCGCTTCGTTGCACTTTATAGATTTTTGCAAACTGGCCGCTGACCAGGCATTGGGAAAAAGGACAATAAGAGGGAGCCCAGAG
CAAGAAGTCCAACTAACCGACCAACTGTGCCTCAAGAAACAGCAAATCAGCGGGGAACTCCCAAACTGGACAAGCAGAAGCCCGGATACCTCACA
TTTGCCATAAGACACCAGTCAAAAAACGACGCGCACTGCAGAACGCATTAGGATTAGCCCGGCACTAGAGCTCGTGCATTAACATCCGCTTCCGG
TGCTCCGCAGAACGAGTTGGCTGGAGAGGATACCCCGCCACCATGACGTTCGACACTCGTAGGCACACCACCGGACAGCCGGGAAGCACAGCGCC
CAGCTCAAGCAGCAGCACCACCAGCACAACAACCACCACAACGAGTCCGGCGCAGAGTGCCGGATCAGGATCGGGCATAGGAACAGGCACAGGAA
CAGTCGCCAACTCGAGTCTGCCAGGAGGAGGATCAGGTAGCTTGGACGGCAACCAGGATCAACAGCCGGCCACAGACAGTCAGAGCTCTGATGAC
GTGGCCGCTTCCTTGTCAGCGAACAGCGTGGACAGCACCATCACAATAGTGTAAGTGGTCGTGCTGCCGTATTTGCATGACTCCGCCCAATTAGT
CGGGTTTTGTGCGTAGCACCAGTATGACCGCCACCCCTAAAGATCCCCAACATTCGTGTGTTTACTTTTGCGTAGTAATTCTTCCACATGCATTC
TTTGTTTGTCTATGGTTGGGCCAGCACAATGTTCGTAATTCATTTAACTATGTTTCAGATGATTTTGGCCAGGCCACTGGTTAGTGACCATAAAT
GTGGCAATAAATGTTATCTTTCTTTTTCTTCGATAGGTGCACTTGGCTGCTGTCCAGTTTTAGCAATGAACTTACCAAGCTTTACTAATATTACC
TTACCCGGCTATTACTATCTCATTTTGAATGCCCGTCCACGGCCTATCTTATCGCTTGTCCATCAAAATAAGCTAACACTGAAAATTACAAAAAA
AAAAAAAAAAAAAATGTATGCGTTTTGGCATTTATTTTAATAGAAATAACCATTTAATAAACAGAAATGTTTATGGAAGGGTGTGCTTTGATTGA
CCCCCTAAGAACTTTTTTTTTATGTGTATTATTTAATTTGTTATTTTTAATATTGAATAATTGTCCATTTAATTAAATAGGCCTCCAGAGAAGC
TTATATCCTCGTTTCCCACGACGAAACTGAGATCACTAACGCAAAAGATATCCAATCCGCGTTGGGTGGTGCCGGTGCTGCCTGAACAGGAATTG
GAGGTTCTCTTAAATGCAGCCATCGAACTGACCCAGGCTGGTAAGTGTGTCCAAACGATTTATTTGATACCCTCTAAAGTCAATTTATTTGCAGG
TGTGGATCACGACTGCGAGCCATGTGTGGAGTTTTATCGCAATGGACTGAGCACTTCCTTTGCCAAGATCCTAACCGACGAGGCGGTGAATTCGT
GGAAGAATAACATCCACCACTGTATCCTTGTGTCTTGCGGCAAGCTTCTACATCTAATCGCCATCCACATGCAGCGAGACAATCCCTATCTGCTT
GACTTGCTGGCTATTGTTTTTGATCCGGAGAACAAGTTCAACACATTTAACGCAGGCCGTCAACCGGAGTGCTTCGCAGCGCCGGACTACATCTG
GGGTCAGTTGGACAGCAACAAAATGTACGCCCGTCCGCCGCCGGAGCCCAAGAATGCGCGTGGCTGGCTTGTGGATCTTATTAACCGCTTCGGAC
AGTTGGGAGGCTTTGACAATCTACTGGAACGGTTTAACATCGGACTGGAACTGCTGAAGCGCAACCAAAACAAGTGCACTGGCAAGAATATTAGT
GTCGAGGGTAGGGTTGAAAATGGGGCTCAGGATAATCGCCTCACCCTTGCCCTCATACACAGCCTCTTGCGTCCATTCGGTCAATGTTATGAGCT
TCTAATGCCTGCCACTATAGCCAAGTACTTTATGCCCACCTGGAACGTTGTGTTAGACCTTCTGGACAGCTTCACAGACGAGGAGTTAAAGCGAG
AAGTGAAACCTGAGGGACGCAATGACTACATCAATGGGATTGTAAAGTCAGCCCGCTTACTGGCCAGCCGCTTGACTGGCCAGGAGGAGCTAATC
CGAGATCTTGAGATGTTTCGCCTAAAGATGATCCTGCGTCTGCTGCAGGTGTCCAGCTTCAACGGCAAGATGAATGCCCTTAATGAGATCAACAA
GGTGCTCTCCTCGGTCGCATATTTCTCCCATCGATCCCAACCTTTGCCCCACTGTATGCCCGAAGACGAAATGGACTGGCTGACGGCGGATCGCA
TGGCGCAATGGATAAAGTCGTCAGATGTATTGGGTGTCGTGCTCAAGGACTCGCTACACCAACCGCAGTATGTGGAAAAATTGGAAAAGATCATC
CGCTTTCTTATTAAAGAGCAGGCACTAACGTTGGATGATTTGGATGCAGTTTGGAGAGCGCAGGCCGGCAAACACGAGGCAATCGTGAAGAACGT
TCACGATCTACTGGCCAAACTTGCATGGGACTTTACTCCCGAGCAACTGGATCACCTCTTCGAGGCGTTCCAGGTGAGTTTTCTGCTTTAAAAGT
GTATTAAGTAAGTTTAAGTTTTAAATTATGATTATTACATTTTCCGCGATGGTTTGTATATAAAATCTCATGAACAATGAAAACAATATTAATTT
TTATTTCAGGCCAGCATGACCACTGCCAATAAGCGGCAACGGGAAAGACTTCTTGAGCTAATACGCCGCTTGGCTGAGGATGACAAAAATGGTGT
GATGGCCCAAAAGGTGCTTAAGCTGTTTTGGACTCTGGCCCACAGTCAGGAGGTGCCGCCAGAGGTGCTTGATCAGGCGCTGGGCGCACACGTTA
AAATCTTGGACTACAGCTGCTCGCAGGAGCGGGATGCCCAAAAGACCATTTGGTTGGATAAGTGCGTTGACGAACTTAAGTCAGGCGATGGATGG
GTTCTGCCCGCCTTGCGTCTAATCCGGGATATTTGTTGCCTATATGATACCACGACAAATCATGCCCAGCGCACTCAAACGAGTACGAATCGTCA
GCAGGTGATTGAACGACTACAGAATGATTATTCCTTGGTCATTCTGGTCACCAATAGTTTGACTGCATACATGGAAAAGGTACGCCAAATGGTAA
CGGACTCACCAGGCCTGGATGCAACCAGAATCCTAATTGACGGAAGATTTCCGCATCACGTGCAATAGCGGAGCGACTGGAGTTCCTTAAGTTC
CTGCTGAAAGATGGACAGCTATGGCTGTGCGCAGATCAGGCAAAGCAGATTTGGCATTGCTTGGCGGTCAATGCAGTTTTTCCGGCAGATCGTGA
GGAGTGTTTTAGATGGTTTGGCAAGTTGATGGGTGAGGAGCCTGACTTGGATCCTGGCATAAACAAAGACTTCTTCGAGAACAACATCCTGCAAC
TTGATCCGCATCTACTAACCGAAAGCGGAATCAAGTGCTTTGAGCGCTTCTTTAAGGCTGTCAATTCCAAAGAGGACAAGCTGAAGGCGATACAT
AGAGGTTACATGCTGGACAACGAGGATCTAATAGGAAAGGACTACTTGTGGCGGGTCATTACAACTGGAGGCGAGGAAATCGCCAGCAAGGCCAT
TGATCTACTTAAGGAAGTGTCGACGGCATTGGGCCCACGTCTGCAGGAGAATATCGCAGAGTTTCATGAAATGTTCATTGGTGAGTGCTGCTCCC
GCCTGCGCACACACTATGGAAATATCGTTATATTGGGCAAGACGCAGCTGCAAGAGGAATTAGATGCCCCCGATCAGTCGGATAATACCAACGAC
GAGTCTAAAGATTCAAAAATGCGTTTCATCGAGGCGGAGAAGATGTGCCGAATTTTAAAGGTGCTGCAAGAATACGTAAAGGAGTGTGATCGTTC
TTTCAGCGGCGATCGTGTTCACCTGCCACTTAGCCGGGTTACACGGGGCAAAAACACCATCTTATATATCCGCTTCCAGAACCCTGGCAGATCTA
TCGACGACATGGAGATCGTTACACACAGCAACGAGACGATGGCCGCTTTTAAGAGAAATCTACTTAAGCGAATCAAGGGAACTTCGACGGCCAAC
ATAAAGGTTGATCTCTTCTATGCTAATGACGAGATGATCGGGGTTTCCGATGAAATAAACCCACTTTATCAGTACACTATCCGGGATAAGATGAA
TCTTACAGCAAAACTCACGCCCGTGGGTACGGGTCTAGCCAGCAGTCCCGACTCCTCGAGCGACTCGAGCACAGGATCTCCTCCGCGTCCCTGCC
CTGACATGCAGCGTGTGGAGTCAGAAGCACGCTACCCGGTGTGATCATCTCAGCAAACTACCAGTACACAGAGTTCTTTCTAAAACTGTACCAA
CTGGGCAGTGATCTCGAGCACGGTCGTCTTCGAGACAGTGCAAAAGTTTTACTACACCTGCTTCCCTGCGACCGCCAGACGATCCGTCAGCTAAA
GATTATGTGCAAGGTGCCGAAGGCTGCCGTAACGGTGGCTGTGACGGGTGACAAGATCGCTAAGGATGAGGAGGAGAAACTGTACCCCACTGAGC

FIGURE SHEET 85

AGGCGGGGATTGAAGATGAAGAGGTAAGACTATAGTTAGTCGAGTTAGTTCATTCAGGAAAGCTATAATGGTTATTTAATTTAAATTGTTTTCTG
TATCAATCTCTTAATATCTCTTCTTTTTAGGAACACTGCACGCCAGAGCAAATGTTTTTGCACCCCACACCTGCTCAAGTGCTATACAACCTTAG
TGTGTTGCACGGACTGCTGATTCCCGCGCTAGATCCACTAGGAGAAAGTGCCCTACTAGTGCAGTCTGCATGGATGCATTCTGGCTGCGCTCATT
TCGTGCTGGAACTGTTGACCAAAAACAATTTTCTGCCTAGCGCCGATATGCACACAAAGCGTGCGTCCTTCCAGTGTGTGTTGAGGTTGGCAAAG
CTGTTCCTGTACATAGTTGGCAGTGTATTGTCTCGTGTAGGCGATGAACCCATGATCTGCGACCTTGACAACGGATCCCGTTCCCAGGTTGACAT
CCTGAAGCAGAACTTCTCCACGATGCCCAGTAGCTCACAGGGAACATTGAGGGCGATCTCCGCGAAACTTGCTGTGATCCTTGCCCGCGAGATGC
TTTCAGCCAGCCCAGAAGGTGATCGGTGCCGAACGCTATTTAGCTCCACACTGCAGTGGTCATGTCCCGACATTTCAACCATTAAGGCGGTAGTG
CAACTGGCCTGGGCCTCGTCTTGCGGAAATCTTCAGGCTCTAGGCAATAGTAGCGGCGACTTTGAAGACGAGGTGATCGTGCCGGACGGGCAAGA
CTTTAGCATGTGCAAGGAGGCGCTAGAGGTTCTCACCATTTCGTTTATTCTGAATCCGAGTGCCAACGAGGCGTTGACTAGCGATCCGAACTGGC
CAAAGTTCATCACCTCCATTGTTCTGAAGAACCCGCTTCGCCACGTGCGTCAGGTGGCCTCTGAGCAGTTGTTTTTGGCTTCTACCTATTGCGCT
GGGGATCGGCGACCGTTCGTATACATGGTTAACTTGCTGGTTGGCGCGTTGAAGACGCTGGTTCCCCAGTACGAGTCAACTTGCGCTGAGTTCTT
CTCGGTGCTGTGTCGGACCCTTTCTTATGGATGCATCTACAACTGGCCGCTGCAGATTAGCGAGGGATTGTTAGGCGATGAGATTAAGTGGCTGC
AACGCATTCGCGAAAACGTCCACGCCACCGGCGACACACAAGTGCATGAGGAGCTCCTTGAAGGCCACCTCTGCCTTGCCAAAGAGCTAATGTTT
TTCCTTGGCGCCGATTCAAAGGCGCAGCTGAACGAGCTCATCCACGAACTGATCGACGACTTCCTGTTCACGGCCTCTCGCGAATTTCTGCATTT
ACGGCGTCATGGCAGTCTACGGCAGGACACCGTCCCGCCACCAGTTTGTCGCAGTCCGCACACAATCGCCGCTGCTTGCGATCTCCTCATTGCCT
TGTGCCAGCTCTGTGTTCCTAATATGAAGCTACTCACCAATACACTTATAGACTTCGTCTGCACGGGTGAGTGTTGGAATCGTAAGATCATTTCA
TGATTAAATGTTTCCTCAATTTTTTGTAGATACTGATCCGTTGCGCGAATGGGATTACCTGCCGCCGGTGGGCGCCAGGCCAACTAAAGGTTTCT
GCGGACTAAAGAACGCAGGTGCCACTTGCTACATGAATTCGGTGTTGCAGCAGCTTTACATGGTACCAGCGGTCCGGGTGGGTATTCTGCGAGCC
CACGGCGCTGCCACCACCGACGGCGAGGATTTCAGTGGCGATTCCGATTTGACGGGAGGCGGTCTTGGATCGGCCCTATTCTCGGGTCCCGCTTC
TGCCCTAGTCAGCCTCCCCTCGTCGTCGTCAACTATCGAAGACGGTTTGCACGATGTGCGAAAGAACTATCACGTTGTGATCCTGAAACATGTGC
AGGCCATATTCGCCCACCTGGGCCACAGTGCGTTGCAGTATTACGTTCCACGTGGTCTCTGGACACATTTTAAGTACAAAATTGTTTCATTGATT
GGCATCACAATGATATTAATATATTATAATTTTTGTTTGCTAGGCTACTGGGAGAGCCCGTGAATCTTCGCGAGCAGCAGGATGCCGTGGAGTTC
TTCATGTCCTTGCTTGAAAGTCTCGATGAAGGACTTAAGGCGCTAGGCCAGCCACAGCTTATGAATGCCACTCTGGGCGGTTCGTTCAGCGACCA
GAAAATCTGCCAAGAGTGTCCCCATCGCTACTCCAAAGAGGAACCATTTAGTGTATTTAGTGTCGATATTAGGAATCATAGCTCATTAACCGAAT
CTCTGGAGCAGTATGTCAAGGGAGAGCTGCTCGAGGGAGCCGATGCATACCATTGTGATAAATGTGATAAAAAAGTAATGTTCTCATCTCTGATA
TTCATATACAATTAATTTTTATTAACATCATTTTTGTGTCCAACAGGTAGTTACCGTTAAGCGAGTGTGCGTTAAGAAGCTGCCACCCGTGTTAG
CCATTCAACTAAAGCGTTTCGAATACGACTACGAACGCGTCTGTGCGATTAAATTTAATGATTATTTTGAATTTCCACGTATCTTGGATATGGAA
CCATACACAGGTGAGTTTAACCGTAATTCCATACGTATATATCTTCTTATTGGATCTTCTTCTCCATGATCAGTGTCTGGCCTAGCTAAGCTAGA
GGGCGAGGTGGTGGAAGTGGGTGATAATTGTCAAACAAACGTTGAGACGACGAAGTACGAACTGACCGGCATTGTGGTGCACAGCGGACAGGCTT
CCGGCGGTCACTACTTCAGTTACATACTCTCCAAGTGCGTACCATAACAATGTTACAGTTTTTTTAAGACTAATTCAATACAACACCTGCTCCA
GAAACCCAGCAAACGGCAAGTGTCAGTGGTATAAGTTTGACGACGGCGAAGTCACCGAGTGCAAGATGCACGAGGACGAGGAAATGAAGGCGGAG
TGCTTTGGCGGCGAGTACATGGGCGAAACCTACGACAACAATCTTAAGCGCATGCAGTACCGTCGACAGAAGCGCTGGTGGAATGCCTACATGTT
GTTCTACACCCGCTGTGATCAAACTCCCGTGCAGTATGAACCCAGCGTGGAGCAGTTGTCACTCGCAGAAAGTCGAAACATGGTTTTACCATTGC
CAAAGCCCATTGAGCGCAGCGTGCGGTGAGTGGAAATAGTGCTTGACCACTATACAGATACTTTTTAATTATTTTTTTTCGATTGCAGACACCAG
AACATTCGGTTTCTCCACTCCCGCAGCATTTTTTCCGTGGAGTTCTTTAACTTTATCAAAAAGTTGGTCAGCTGCAATCTACTTTCTGCTCGGAG
CAATAAGATCGTCAGTTTGTATTCAAGTGGTTTTATTTCCCGTTTAAAAAAACTATTATTTTTTTAACAGACTCCTGCTGCAGAAGAGCTTTCAC
TGCTGGGCGTCCAATTAGCATCGCAGTTTCTTTTCCACACCGGCTTCCGCACGAAAAAGTCTCTGCGAGGCCCCGTTATGGAATGGTGAGTAGCT
TGGGAGGTATTGACTCGGGTATAATTAGGATACATCTTCTGCTTTACAGGTATGACGCGCTCTCACACCACATACGTTCCTCGGCACTAGTTCGC
AAGTGGTTCGCTAATCATGCGCTCCTCTCGCCGCCATCGCGTTTAGGCGAGTACATTCTGATGGCTCCGTCTCCGGATGTCCGTACTGTCTTTGT
CAAGTTGGTGGTTTTTTTCTGCCATTTTGCCATCAACGATGAACCTCTGACTGGCTATGACGGCGCTAATCTCTGCGAGCAGGTACTCATCAGCG
TGTTGCGCCTCTTGAAATCCGAGGCAGCCGACTATGGCAAACACCTGCCCCACTATTTTAGCCTTTTCAGTATGTACGTGGGACTAGGAACACGG
GAAAAACAGCAACTGCTTAGGGTGAGAACTATTTACAATAAGATTGCTTGCCATTCTAAACGATTATGTTCGTTTGCAGCTCAATGTGCCGCTGC
AGTTTATTCAGGTGGCGTTGGATGATGGCCCCGGTCCGGCAATAAAATACCAGTATCCAGAGTTCAGCAAGCTACACCAAGTGGTTTCGCACCTA
ATACGCTGCAGCGATGTAAGCGAAAAATGCCAGAGCTCCAACCAGAACGCCCGTCCACTGTCCAATCCGTTCAAAGATCCCAATGTTGCGCACGA
GGAGCTGACGCCCCTGTCCACTGAGTGCATGGACCTGCTCTTTAACCGCACGGGGTAAGGTGCATGGCATTTTACTGATAACTGTGCTCAGTTCA
GAGAGCATTTCAAGCCATTTCCTTATGAAAGAAACGTACAGTGAGTGCTTACGATCCGTTTTGTCATTTTTTTTTCAGCTACATCAAGAAAGTGA
TCGAAGACACTAACGTGGGCGACGAGGGTCTGAAGCTGTTGCAATACTGCAGCTGGGAGAATCCACATTTCTCTCGCGCAGTGCTAACCGAATTG
TTGTGGCAGTGTGGGTTCGCCTATTGTCACGACATGCGTCACCACACTGATCTGCTTCTGAACATCCTGCTGATCGACGACTCGTGGCAGCACCA
TCGCATACACAATGCTCTCAACGGAGTGGCGGAGGAACGTGAGGGTCTGTTAGAGACGATACAGCGGGCGAAGACGCACTACCAGAAGAGGGCGT
ACCAAATAATCAAGTGCCTGACGCAACTTTTCCATAAGTCGCCGATTGCGCTGCAGATGCTCCACACAAATTCGAACATTACTCGGCACTGGAGC
ATTGCAGTGGAGTGGCTGCAAGGCGAACTAGATCGGCAGCGGGGCATCGGTTGCCAGTACAATTCATACTCGTGGTCGCCGCCGGCGCAGAGTAA
CGACAACACTAATGGCTACATGCTAGAGCGATCGCAGTCTGCTAAAAACACGTGGTCCATGGCCTTCGAGCTCTGTCCAGATGAGGTCAGCGAAA
AAACGGTATCTAAAACATAACAATTATATTAAAGAATACTTTATTCTATTGATCGTTCATTATAATAGGATGAAAATAATGAGCCGAACTTGGAG
ACGAACATGGATGAGAACAAATCGGAACCGGTGGCTCAGCCAGGAGGAGTGCTTGAGGGATCTACCGGCGGCACAGAGCAGTTGCCCGAAAATAA
GACGCCAACCACAAGCAGCCCGTCGACTGCCGCCTGGCCAGCGCGTGGGGATAGCAACGCTATTCCACGACTTTCGCGTCAGCTATTTGGGGCTT
ACACTTCGACTGGCAGTGGCTCCACTAGTGGAGGTTCCGCGCCAACTTCCGCCTTGACGACAACGGCGGGTAGTGGGGCTAACAGCGAAACAGAA
AGCAGCGCCCAGGAAACAACCGGCGAGACGACCATTAACGGACTGACAAACAGCCTGGACCAAATGGAGATAACGGCCAAAAAGGTAACTCGGGC
GAACAATGTCTAGGACAAGTGTCCATCTATAAGGTGTGTGTCCGTTGCCGCAATTGAAGAGTTCGAGACGTCTAAAAACAGTCCCAGAAAACTAG
TAAACACAACAAACACATTTTACACTGGAACTCCAATCTGTATCTTTCTATCTGTCTTCTTTAATACGTGGATAGAAGATATGTAGTTTAGTCAA
ACTAAACATGTCCTCCCGACGTTCTTTTCCATTTATATTTATGTTTACTAAAAGACACTATGTACTTTAACAAGAACGTTGGTTAATATAAAAAT
ATTGGTTCGCTTCGACTGTTTACCCTTCGGTTTTCGAAGATCCACCACCTTCTTATTTAAACTCTTCTTTAATATTTCTACCATACTACAACATC
ACCCTCGGTAACCCTTGCTGCGTTTCGGTGTTTAATCCTTTATTGTATATGAATTGTAACCACAAACGCAGGGTGTGCGAAGTCGCTCCAAAGGA
GGCAAGCTCCCCCGGTGCTGTTTCACCATCACCAGTTGCCGCCAGAGCAACAACTTAAACTGAAGCAGCAACAACAGCAGCAGCAGCAACAACA
GCATCAGCAACTACGTGGTGATATAAACAAGACTTCCTCAAGCCGCTTAATTTGATTTGACGCCAAGTTAGTTAGAGTTGTTGTTTCGTTTGAGC
TCAAAACGCCCGCCTTACTTTGTGTTTGTTGTTGTTTTCACGATCCCGGCACAAATGAGATGCACTTGCCATCCCCGGATCTGTCTTCCCCTTGG
CTTTTTATTTCCTTTACTGCAAGTTTTCTCTACTTATCCATGCAAAACCACGCACGCCACAATCAGTCCACACACACAAAATCACAGGGGTCCAA
CAAATTTGAATGTCAACGAAGTCAACGAAAACTAGTTGAAATACGATGGATATGTTTCTTAATTCGTACTTTTTTAAATAAAAAAACTAAGACTG
ATTTCTAATATACCGAATCTTAAAAATCATTGTTTTTTTGTATGTTATATTGAAAAGAGTGTTTTTGGTTCTTCAGCGAATTATTTCAACGAAA
ATATACAATACAAAATATCAGTATATACATTTCATATAAAAAAGATATCCTAGATTAAAGTACATAACTAATCGTATTAGACTTTGACCTATTAA
GATACTACTTTATGATCCACTTTTGAGGCGTGAATGAACCCGAAAACACTCGAAGCAAGATTGCATTACCGCTTAGCTGGCACCCGTAGCACTGG
GCGATAGATTGTCAACCTCCACTAACCGAACTCTTTTTGTTGGCTATTCACAGAAGTGCCGCAGGGTGATAATAAAAAAGCTAGTGGAAAGTAAG

FIGURE SHEET 86

GACGAAGAGGACGCAACTACTGCTACCACAGCGGCCACCACAGAGGTCACAACATCGCCAGCGACAGCTATCGCAACGGCAGCAACTTTAGAGCC
TGCCGGAATGAGTGAGCTCACGACGATGGTAGAGAAAAATCTTATAATAAGCCAAGAAAATCCACAAGCGAAAAGCTCATTGCAATAAAATGTAT
TCGCAACCTAGCTGGAGGAGAAGATGATGAGTATCCATAGTGTTAAATGTAACCAAAGCAGCCTGACAATGAGAACGGTGTGGACAGGTGTTTAC
TAGTGGGGATCCCCACCGTCGAAAACGAGACTTAATGGGTAAATACGAGAAAAAGAGCAGAATCCGTAGATATTAACAAAGGATACTTGGTTGGA
GCGATGCGAGTCAAGGAACGAAAGTCTGGTAGATAAGGAGATCAAAACCAGCAAAGGTGTTTATTAGCTATCGAACTTTATAATTACCTTTAATA
ATAAACAAATACACCAATTTTTTGTTTGGTTTTCTGTTTTGTTAAGCATTAAAAGGGATATGTTTATTTCTCCTCATTGTAAATGTGTCCCTTTT
AATGTATAAATCTAAAAAAAAAAAAATGAAAAGAACACCTTAAACTAACTCCCACAACACTACACAGAAACGGACGTAGGCAGAAAGAAACACACT
CATAATCTATAAGAAGCGTTAAGTTGCACGTTTACAGTACCATATAATTGTATTTATATAGTATATAAATGATGTATTACGTATTGAAGCCGAGC
AACACTTACTATACTAACCGAAAAAAATCAAAATGATGGACACTTAGATACGATACTAGGAAAAACTAATCGAAACGAATCGGCTGATTGTAAGA
ATTAGGGCAAGAAACCAAATTGCATCTTTAGTACTCAGTACTCGCCTCTGAAACTGTTTCCATAATCATATTTCAACGGCATGAACCGATTTAAT
GGGATGCTAATTAAAACAAAACAGTATAAACTCAAGAGCAGAATGGACTAAAGCAACACGAGCATAAAGAAAACTTGATTATGGTCATAAGTACA
TATATTTTAAATGATTAGTGTTTTGTATTAAGTGAAATTTGTTAAACATTTATTACATTTTTATGTTCTAAGTTGCGAAATAAATGCGAAGAGAA
AGCAAAGCGCGCAATGTCATTCATGCCTTCTCTCAGTTTCCATTTCCGTTTCCGTTTACCGACAGCAATCAACTCAAAGTCTAACTTTTATGCCG
CGAGATTTTGTACGGAACTCAATTTTAAATTATGTATTCACAAAGATGTATTACATTTGGGAAATTAATGTTCGTTACATCCATTAAATTCAGCG
AAAATGAAACAAATAAATCACTTTTTAAAACCATTACTTTTGGCTTCCTTACTTACCCACAAAAACAATTCATGGCTAACAGTTTTAGACGTTTA
ATGGGTTAAAGATAAGAAAATTCCATTAGATGGACACTTTTTTACTTAACGATAATAAATGCACTTCGTGATCCCTGAACCAAAAGCAGGCTAGT
TAATATTTAAAATATAATTTTGTTTGTAAATGCAACAACTC
(SEQ ID NO: 172)

Exon: 1001..1134
Exon: 2124..2710
Exon: 3312..3460
Exon: 3515..4728
Exon: 4855..6768
Exon: 6871..8236
Exon: 8295..8718
Exon: 8784..9099
Exon: 9167..9320
Exon: 9384..9534
Exon: 9597..9905
Exon: 9969..10080
Exon: 10141..10250
Exon: 10310..10661
Exon: 10720..10979
Exon: 11099..11690
Exon: 11754..12149
Exon: 13449..14051
Start ATG: 2418

Transcript No. : CT6055
CACAACCCTAGCAAAAGAAATAGCTTAAATATAATTTATTTAACGCGAATTGGACAACGAGCGGGTAGAAAAAACCCTGTGGCCGCAACCGCGAC
GCTCGCAGGATACGCAGCTCTTCGCCGTCGGGCAGGCAGATTTTTGCAAACTGGCCGCTGACCAGGCATTGGGAAAAAGGACAATAAGAGGGAGC
CCAGAGCAAGAAGTCCAACTAACCGACCAACTGTGCCTCAAGAAACAGCAAATCAGCGGGGAACTCCCAAACTGGACAAGCAGAAGCCCGGATAC
CTCACATTTGCCATAAGACACCAGTCAAAAAACGACGCGCACTGCAGAACGCATTAGGATTAGCCCGGCACTAGAGCTCGTGCATTAACATCCGC
TTCCGGTGCTCCGCAGAACGAGTTGGCTGGAGAGGATACCCCGCCACCATGACGTTCGACACTCGTAGGCACACCACCGGACAGCCGGGAAGCAC
AGCGCCCAGCTCAAGCAGCAGCACCACCAGCACAACAACCACCACAACGAGTCCGGCGCAGAGTGCCGGATCAGGATCGGGCATAGGAACAGGCA
CAGGAACAGTCGCCAACTCGAGTCTGCCAGGAGGAGGATCAGGTAGCTTGGACGGCAACCAGGATCAACAGCCGGCCACAGACAGTCAGAGCTCT
GATGACGTGGCCGCTTCCTTGTCAGCGAACAGCGTGGACAGCACCATCACAATAGTGCCTCCAGAGAAGCTTATATCCTCGTTTCCCACGACGAA
ACTGAGATCACTAACGCAAAAGATATCCAATCCGCGTTGGGTGGTGCCGGTGCTGCCTGAACAGGAATTGGAGGTTCTCTTAAATGCAGCCATCG
AACTGACCCAGGCTGGTGTGGATCACGACTGCGAGCCATGTGTGGAGTTTTATCGCAATGGACTGAGCACTTCCTTTGCCAAGATCCTAACCGAC
GAGGCGGTGAATTCGTGGAAGAATAACATCCACCACTGTATCCTTGTGTCTTGCGGCAAGCTTCTACATCTAATCGCCATCCACATGCAGCGAGA
CAATCCCTATCTGCTTGACTTGCTGGCTATTGTTTTTGATCCGGAGAACAAGTTCAACACATTTAACGCAGGCCGTCAACCGGAGTGCTTCGCAG
CGCCGGACTACATCTGGGGTCAGTTGGACAGCAACAAAATGTACGCCCGTCCGCCGCCGGAGCCCAAGAATGCGCGTGGCTGGCTTGTGGATCTT
ATTAACCGCTTCGGACAGTTGGGAGGCTTTGACAATCTACTGGAACGGTTTAACATCGGACTGGAACTGCTGAAGCGCAACCAAAACAAGTGCAC
TGGCAAGAATATTAGTGTCGAGGGTAGGGTTGAAAATGGGGCTCAGGATAATCGCCTCACCCTTGCCCTCATACACAGCCTCTTGCGTCCATTCG
GTCAATGTTATGAGCTTCTAATGCCTGCCACTATAGCCAAGTACTTTATGCCCACCTGGAACGTTGTGTTAGACCTTCTGGACAGCTTCACAGAC
GAGGAGTTAAAGCGAGAAGTGAAACCTGAGGGACGCAATGACTACATCAATGGGATTGTAAAGTCAGCCCGCTTACTGGCCAGCCGCTTGACTGG
CCAGGAGGAGCTAATCCGAGATCTTGAGATGTTTCGCCTAAAGATGATCCTGCGTCTGCTGCAGGTGTCCAGCTTCAACGGCAAGATGAATGCCC
TTAATGAGATCAACAAGGTGCTCTCCTCGGTCGCATATTTCTCCCATCGATCCCAACCTTTGCCCCACTGTATGCCCGAAGACGAAATGGACTGG
CTGACGGCGGATCGCATGGCGCAATGGATAAAGTCGTCAGATGTATTGGGTGTCGTGCTCAAGGACTCGCTACACCAACCGCAGTATGTGGAAAA
ATTGGAAAAGATCATCCGCTTTCTTATTAAAGAGCAGGCACTAACGTTGGATGATTTGGATGCAGTTTGGAGAGCGCAGGCCGGCAAACACGAGG
CAATCGTGAAGAACGTTCACGATCTACTGGCCAAACTTGCATGGGACTTTACTCCCGAGCAACTGGATCACCTCTTCGAGGCGTTCCAGGCCAGC
ATGACCACTGCCAATAAGCGGCAACGGGAAAGACTTCTTGAGCTAATACGCCGCTTGGCTGAGGATGACAAAAATGGTGTGATGGCCCAAAAGGT
GCTTAAGCTGTTTTGGACTCTGGCCCACAGTCAGGAGGTGCCGCCAGAGGTGCTTGATCAGGCGCTGGGCGCACACGTTAAAATCTTGGACTACA
GCTGCTCGCAGGAGCGGGATGCCCAAAAGACCATTTGGTTGGATAAGTGCGTTGACGAACTTAAGTCAGGCGATGGATGGGTTCTGCCCGCCTTG
CGTCTAATCCGGGATATTTGTTGCCTATATGATACCACGACAAATCATGCCCAGCGCACTCAAACGAGTACGAATCGTCAGCAGGTGATTGAACG
ACTACAGAATGATTATTCCTTGGTCATTCTGGTCACCAATAGTTTGACTGCATACATGGAAAAGGTACGCCAAATGGTAACGGACTCACCAGGCC
TGGATGCAACCAGAATCCTAATTGACGGAAGATTTCCGCATCACGTGCAAATAGCGGAGCGACTGGAGTTCCTTAAGTTCCTGCTGAAAGATGGA
CAGCTATGGCTGTGCGCAGATCAGGCAAAGCAGATTTGGCATTGCTTGGCGGTCAATGCAGTTTTTCCGGCAGATCGTGAGGAGTGTTTTAGATG
GTTTGGCAAGTTGATGGGTGAGGAGCCTGACTTGGATCCTGGCATAAACAAAGACTTCTTCGAGAACAACATCCTGCAACTTGATCCGCATCTAC
TAACCGAAAGCGGAATCAAGTGCTTTGAGCGCTTCTTTAAGGCTGTCAATTCCAAAGAGGACAAGCTGAAGGCGATACATAGAGGTTACATGCTG

FIGURE SHEET 87

GACAACGAGGATCTAATAGGAAAGGACTACTTGTGGCGGGTCATTACAACTGGAGGCGAGGAAATCGCCAGCAAGGCCATTGATCTACTTAAGGA
AGTGTCGACGGCATTGGGCCCACGTCTGCAGGAGAATATCGCAGAGTTTCATGAAATGTTCATTGGTGAGTGCTGCTCCCGCCTGCGCACACACT
ATGGAAATATCGTTATATTGGGCAAGACGCAGCTGCAAGAGGAATTAGATGCCCCCGATCAGTCGGATAATACCAACGACGAGTCTAAAGATTCA
AAAATGCGTTTCATCGAGGCGGAGAAGATGTGCCGAATTTTAAAGGTGCTGCAAGAATACGTAAAGGAGTGTGATCGTTCTTTCAGCGGCGATCG
TGTTCACCTGCCACTTAGCCGGGTTACACGGGGCAAAAACACCATCTTATATATCCGCTTCCAGAACCCTGGCAGATCTATCGACGACATGGAGA
TCGTTACACACAGCAACGAGACGATGGCCGCTTTTAAGAGAAATCTACTTAAGCGAATCAAGGGAACTTCGACGGCCAACATAAAGGTTGATCTC
TTCTATGCTAATGACGAGATGATCGGGGTTTCCGATGAAATAAACCCACTTTATCAGTACACTATCCGGGATAAGATGAATCTTACAGCAAAACT
CACGCCCGTGGGTACGGGTCTAGCCAGCAGTCCCGACTCCTCGAGCGACTCGAGCACAGGATCTCCTCCGCGTCCCTGCCCTGACATGCAGCGTG
TGGAGTCAGAAAGCACGCTACCCGGTGTGATCATCTCGCAAAACTACCAGTACACAGAGTTCTTTCTAAAACTGTACCAACTGGGCAGTGATCTC
GAGCACGGTCGTCTTCGAGACAGTGCAAAAGTTTTACTACACCTGCTTCCCTGCGACCGCCAGACGATCCGTCAGCTAAAGATTATGTGCAAGGT
GCCGAAGGCTGCCGTAACGGTGGCTGTGACGGGTGACAAGATCGCTAAGGATGAGGAGGAGAAACTGTACCCCACTGAGCAGGCGGGGATTGAAG
ATGAAGAGGAACACTGCACGCCAGAGCAAATGTTTTTGCACCCCACACCTGCTCAAGTGCTATACAACCTTAGTGTGTTGCACGGACTGCTGATT
CCCGCGCTAGATCCACTAGGAGAAAGTGCCCTACTAGTGCAGTCTGCATGGATGCATTCTGGCTGCGCTCATTTCGTGCTGGAACTGTTGACCAA
AAACAATTTTCTGCCTAGCGCCGATATGCACACAAAGCGTGCGTCCTTCCAGTGTGTGTTGAGGTTGGCAAAGCTGTTCCTGTACATAGTTGGCA
GTGTATTGTCTCGTGTAGGCGATGAACCCATGATCTGCGACCTTGACAACGGATCCCGTTCCCAGGTTGACATCCTGAAGCAGAACTTCTCCACG
ATGCCCAGTAGCTCACAGGGAACATTGAGGGCGATCTCCGCGAAACTTGCTGTGATCCTTGCCCGCGAGATGCTTTCAGCCAGCCCAGAAGGTGA
TCGGTGCCGAACGCTATTTAGCTCCACACTGCAGTGGTCATGTCCCGACATTTCAACCATTAAGGCGGTAGTGCAACTGGCCTGGGCCTCGTCTT
GCGGAAATCTTCAGGCTCTAGGCAATAGTAGCGGCGACTTTGAAGACGAGGTGATCGTGCCGGACGGGCAAGACTTTAGCATGTGCAAGGAGGCG
CTAGAGGTTCTCACCATTTCGTTTATTCTGAATCCGAGTGCCAACGAGGCGTTGACTAGCGATCCGAACTGGCCAAAGTTCATCACCTCCATTGT
TCTGAAGAACCCGCTTCGCCACGTGCGTCAGGTGGCCTCTGAGCAGTTGTTTTTGGCTTCTACCTATTGCGCTGGGGATCGGCGACCGTTCGTAT
ACATGGTTAACTTGCTGGTTGGCGCGTTGAAGACGCTGGTTCCCCAGTACGAGTCAACTTGCGCTGAGTTCTTCTCGGTGCTGTGTCGGACCCTT
TCTTATGGATGCATCTACAACTGGCCGCTGCAGATTAGCGAGGGATTGTTAGGCGATGAGATTAAGTGGCTGCAACGCATTCGCGAAAACGTCCA
CGCCACCGGCGACACACAAGTGCATGAGGAGCTCCTTGAAGGCCACCTCTGCCTTGCCAAAGAGCTAATGTTTTTCCTTGGCGCCGATTCAAAGG
CGCAGCTGAACGAGCTCATCCACGAACTGATCGACGACTTCCTGTTCACGGCCTCTCGCGAATTTCTGCATTTACGGCGTCATGGCAGTCTACGG
CAGGACACCGTCCCGCCACCAGTTTGTCGCAGTCCGCACACAATCGCCGCTGCTTGCGATCTCCTCATTGCCTTGTGCCAGCTCTGTGTTCCTAA
TATGAAGCTACTCACCAATACACTTATAGACTTCGTCTGCACGGATACTGATCCGTTGCGCGAATGGGATTACCTGCCGCCGGTGGGCGCCAGGC
CAACTAAAGGTTTCTGCGGACTAAAGAACGCAGGTGCCACTTGCTACATGAATTCGGTGTTGCAGCAGCTTTACATGGTACCAGCGGTCCGGGTG
GGTATTCTGCGAGCCCACGGCGCTGCCACCACCGACGGCGAGGATTTCAGTGGCGATTCCGATTTGACGGGAGGCGGTCTTGGATCGGCCCTATT
CTCGGGTCCCGCTTCTGCCCTAGTCAGCCTCCCCTCGTCGTCGTCAACTATCGAAGACGGTTTGCACGATGTGCGAAAGAACTATCACGTTGTGA
TCCTGAAACATGTGCAGGCCATATTCGCCCACCTGGGCCACAGTGCGTTGCAGTATTACGTTCCACGTGGTCTCTGGACACATTTTAAGCTACTG
GGAGAGCCCGTGAATCTTCGCGAGCAGCAGGATGCCGTGGAGTTCTTCATGTCCTTGCTTGAAAGTCTCGATGAAGGACTTAAGGCGCTAGGCCA
GCCACAGCTTATGAATGCCACTCTGGGCGGTTCGTTCAGCGACCAGAAAATCTGCCAAGAGTGTCCCCATCGCTACTCCAAAGAGGAACCATTTA
GTGTATTTAGTGTCGATATTAGGAATCATAGCTCATTAACCGAATCTCTGGAGCAGTATGTCAAGGGAGAGCTGCTCGAGGGAGCCGATGCATAC
CATTGTGATAAATGTGATAAAAAAGTAGTTACCGTTAAGCGAGTGTGCGTTAAGAAGCTGCCACCCGTGTTAGCCATTCAACTAAAGCGTTTCGA
ATACGACTACGAACGCGTCTGTGCGATTAAATTTAATGATTATTTTGAATTTCCACGTATCTTGGATATGGAACCATACACAGTGTCTGGCCTAG
CTAAGCTAGAGGGCGAGGTGGTGGAAGTGGGTGATAATTGTCAAACAAACGTTGAGACGACGAAGTACGAACTGACCGGCATTGTGGTGCACAGC
GGACAGGCTTCCGGCGGTCACTACTTCAGTTACATACTCTCCAAAAACCCAGCAAACGGCAAGTGTCAGTGGTATAAGTTTGACGACGGCGAAGT
CACCGAGTGCAAGATGCACGAGGACGAGGAAATGAAGGCGGAGTGCTTTGGCGGCGAGTACATGGGCGAAACCTACGACAACAATCTTAAGCGCA
TGCAGTACCGTCGACAGAAGCGCTGGTGGAATGCCTACATGTTGTTCTACACCCGCTGTGATCAAACTCCCGTGCAGTATGAACCCAGCGTGGAG
CAGTTGTCACTCGCAGAAAGTCGAAACATGGTTTTACCATTGCCAAAGCCCATTGAGCGCAGCGTGCGACACCAGAACATTCGGTTTCTCCACTC
CCGCAGCATTTTTTCCGTGGAGTTCTTTAACTTTATCAAAAAGTTGGTCAGCTGCAATCTACTTTCTGCTCGGAGCAATAAGATCACTCCTGCTG
CAGAAGAGCTTTCACTGCTGGGCGTCCAATTAGCATCGCAGTTTCTTTTCCACACCGGCTTCCGCACGAAAAAGTCTCTGCGAGGCCCCGTTATG
GAATGGTATGACGCGCTCTCACACCACATACGTTCCTCGGCACTAGTTCGCAAGTGGTTCGCTAATCATGCGCTCCTCTCGCCGCCATCGCGTTT
AGGCGAGTACATTCTGATGGCTCCGTCTCCGGATGTCCGTACTGTCTTTGTCAAGTTGGTGGTTTTTTTCTGCCATTTTGCCATCAACGATGAAC
CTCTGACTGGCTATGACGGCGCTAATCTCTGCGAGCAGGTACTCATCAGCGTGTTGCGCCTCTTGAAATCCGAGGCAGCCGACTATGGCAAACAC
CTGCCCCACTATTTTAGCCTTTTCAGTATGTACGTGGGACTAGGAACACGGGAAAAACAGCAACTGCTTAGGCTCAATGTGCCGCTGCAGTTTAT
TCAGGTGGCGTTGGATGATGGCCCCGGTCCGGCAATAAAATACCAGTATCCAGAGTTCAGCAAGCTACACCAAGTGGTTTCGCACCTAATACGCT
GCAGCGATGTAAGCGAAAAATGCCAGAGCTCCAACCAGAACGCCCGTCCACTGTCCAATCCGTTCAAAGATCCCAATGTTGCGCACGAGGAGCTG
ACGCCCCTGTCCACTGAGTGCATGGACCTGCTCTTTAACCGCACGGGCTACATCAAGAAAGTGATCGAAGACACTAACGTGGGCGACGAGGGTCT
GAAGCTGTTGCAATACTGCAGCTGGGAGAATCCACATTTCTCTCGCGCAGTGCTAACCGAATTGTTGTGGCAGTGTGGGTTCGCCTATTGTCACG
ACATGCGTCACCACACTGATCTGCTTCTGAACATCCTGCTGATCGACGACTCGTGGCAGCACCATCGCATACACAATGCTCTCAACGGAGTGGCG
GAGGAACGTGAGGGTCTGTTAGAGACGATACAGCGGGCGAAGACGCACTACCAGAAGAGGGCGTACCAAATAATCAAGTGCCTGACGCAACTTTT
CCATAAGTCGCCGATTGCGCTGCAGATGCTCCACACAAATTCGAACATTACTCGGCACTGGAGCATTGCAGTGGAGTGGCTGCAAGGCGAACTAG
ATCGGCAGCGGGGCATCGGTTGCCAGTACAATTCATACTCGTGGTCGCCGCCGGCGCAGAGTAACGACAACACTAATGGCTACATGCTAGAGCGA
TCGCAGTCTGCTAAAAACACGTGGTCCATGGCCTTCGAGCTCTGTCCAGATGAGGTCAGCGAAAAAACGGATGAAAATAATGAGCCGAACTTGGA
GACGAACATGGATGAGAACAAATCGGAACCGGTGGCTCAGCCAGGAGGAGTGCTTGAGGGATCTACCGGCGGCACAGAGCAGTTGCCCGAAAATA
AGACGCCAACCACAAGCAGCCCGTCGACTGCCGCCTGGCCAGCGCGTGGGATAGCAACGCTATTCCACGACTTTCGCGTCAGCTATTTGGGGCT
TACACTTCGACTGGCAGTGGCTCCACTAGTGGAGGTTCCGCGCCAACTTCCGCCTTGACGACAACGGCGGGTAGTGGGGCTAACAGCGAAACAGA
AAGCAGCGCCCAGGAAACAACCGGCGAGACGACCATTAACGGACTGACAAACAGCCTGGACCAAATGGAGATAACGGCCAAAAAGAAGTGCCGCA
GGGTGATAATAAAAAAGCTAGTGGAAAGTAAGGACGAAGAGGACGCAACTACTGCTACCACAGCGGCCACCACAGAGGTCACAACATCGCCAGCG
ACAGCTATCGCAACGGCAGCAACTTTAGAGCCTGCCGGAATGAGTGAGCTCACGACGATGGTAGAGAAAAATCTTATAATAAGCCAAGAAAATCC
ACAAGCGAAAAGCTCATTGCAATAAAATGTATTCGCAACCTAGCTGGAGGAGAAGATGATGAGTATCCATAGTGTTAAATGTAACCAAAGCAGCC
TGACAATGAGAACGGTGTGGACAGGTGTTTACTAGTGGGGATCCCCACCGTCGAAAACGAGACTTAATGGGTAAATACGAGAAAAAGAGCAGAAT
CCGTAGATATTAACAAAGGATACTTGGTTGGAGCGATGCGAGTCAAGGAACGAAAGTCTGGTAGATAAGGAGATCAAAACCAGCAAAGGTGTTTA
TTAGCTATCGAACTTTATAATTACCTTTAATAATAAACAAATACACCAATTTTTTGTTTGGTTTTCTGTTTTGTTAAGCATTAAAAGGGATATGT
TTATTTCTCCTCATTGTAAATGT
(SEQ ID NO: 173)

Start ATG: 429

FIGURE SHEET 88

MTFDTRRHTTGQPGSTAPSSSSSTTSTTTTTTSPAQSAGSGSGIGTGTGTVANSSLPGGGSGSLDGNQDQQPATDSQSSDDVAASLSANSVDSTI
TIVPPEKLISSFPTTKLRSLTQKISNPRWVVPVLPEQELEVLLNAAIELTQAGVDHDCEPCVEFYRNGLSTSFAKILTDEAVNSWKNNIHHCILV
SCGKLLHLIAIHMQRDNPYLLDLLAIVFDPENKFNTFNAGRQPECFAAPDYIWGQLDSNKMYARPPPEPKNARGWLVDLINRFGQLGGFDNLLER
FNIGLELLKRNQNKCTGKNISVEGRVENGAQDNRLTLALIHSLLRPFGQCYELLMPATIAKYFMPTWNVVLDLLDSFTDEELKREVKPEGRNDYI
NGIVKSARLLASRLTGQEELIRDLEMFRLKMILRLLQVSSFNGKMNALNEINKVLSSVAYFSHRSQPLPHCMPEDEMDWLTADRMAQWIKSSDVL
GVVLKDSLHQPQYVEKLEKIIRFLIKEQALTLDDLDAVWRAQAGKHEAIVKNVHDLLAKLAWDFTPEQLDHLFEAFQASMTTANKRQRERLLELI
RRLAEDDKNGVMAQKVLKLFWTLAHSQEVPPEVLDQALGAHVKILDYSCSQERDAQKTIWLDKCVDELKSGDGWVLPALRLIRDICCLYDTTTNH
AQRTQTSTNRQQVIERLQNDYSLVILVTNSLTAYMEKVRQMVTDSPGLDATRILIDGRFPHHVQIAERLEFLKFLLKDGQLWLCADQAKQIWHCL
AVNAVFPADREECFRWFGKLMGEEPDLDPGINKDFFENNILQLDPHLLTESGIKCFERFFKAVNSKEDKLKAIHRGYMLDNEDLIGKDYLWRVIT
TGGEEIASKAIDLLKEVSTALGPRLQENIAEFHEMFIGECCSRLRTHYGNIVILGKTQLQEELDAPDQSDNTNDESKDSKMRFIEAEKMCRILKV
LQEYVKECDRSFSGDRVHLPLSRVTRGKNTILYIRFQNPGRSIDDMEIVTHSNETMAAFKRNLLKRIKGTSTANIKVDLFYANDEMIGVSDEINP
LYQYTIRDKMNLTAKLTPVGTGLASSPDSSSDSSTGSPPRPCPDMQRVESESTLPGVIISQNYQYTEFFLKLYQLGSDLEHGRLRDSAKVLLHLL
PCDRQTIRQLKIMCKVPKAAVTVAVTGDKIAKDEEEKLYPTEQAGIEDEEEHCTPEQMFLHPTPAQVLYNLSVLHGLLIPALDPLGESALLVQSA
WMHSGCAHFVLELLTKNNFLPSADMHTKRASFQCVLRLAKLFLYIVGSVLSRVGDEPMICDLDNGSRSQVDILKQNFSTMPSSSQGTLRAISAKL
AVILAREMLSASPEGDRCRTLFSSTLQWSCPDISTIKAVVQLAWASSCGNLQALGNSSGDFEDEVIVPDGQDFSMCKEALEVLTISFILNPSANE
ALTSDPNWPKFITSIVLKNPLRHVRQVASEQLFLASTYCAGDRRPFVYMVNLLVGALKTLVPQYESTCAEFFSVLCRTLSYGCIYNWPLQISEGL
LGDEIKWLQRIRENVHATGDTQVHEELLEGHLCLAKELMFFLGADSKAQLNELIHELIDDFLFTASREFLHLRRHGSLRQDTVPPPVCRSPHTIA
AACDLLIALCQLCVPNMKLLTNTLIDFVCTDTDPLREWDYLPPVGARPTKGFCGLKNAGATCYMNSVLQQLYMVPAVRVGILRAHGAATTDGEDF
SGDSDLTGGGLGSALFSGPASALVSLPSSSSTIEDGLHDVRKNYHVVILKHVQAIFAHLGHSALQYYVPRGLWTHFKLLGEPVNLREQQDAVEFF
MSLLESLDEGLKALGQPQLMNATLGGSFSDQKICQECPHRYSKEEPFSVFSVDIRNHSSLTESLEQYVKGELLEGADAYHCDKCDKKVVTVKRVC
VKKLPPVLAIQLKRFEYDYERVCAIKFNDYFEFPRILDMEPYTVSGLAKLEGEVVEVGDNCQTNVETTKYELTGIVVHSGQASGGHYFSYILSKN
PANGKCQWYKFDDGEVTECKMHEDEEMKAECFGGEYMGETYDNNLKRMQYRRQKRWWNAYMLFYTRCDQTPVQYEPSVEQLSLAESRNMVLPLPK
PIERSVRHQNIRFLHSRSIFSVEFFNFIKKLVSCNLLSARSNKITPAAEELSLLGVQLASQFLFHTGFRTKKSLRGPVMEWYDALSHHIRSSALV
RKWFANHALLSPPSRLGEYILMAPSPDVRTVFVKLVVFFCHFAINDEPLTGYDGANLCEQVLISVLRLLKSEAADYGKHLPHYFSLFSMYVGLGT
REKQQLLRLNVPLQFIQVALDDGPGPAIKYQYPEFSKLHQVVSHLIRCSDVSEKCQSSNQNARPLSNPFKDPNVAHEELTPLSTECMDLLFNRTG
YIKKVIEDTNVGDEGLKLLQYCSWENPHFSRAVLTELLWQCGFAYCHDMRHHTDLLLNILLIDDSWQHHRIHNALNGVAEEREGLLETIQRAKTH
YQKRAYQIIKCLTQLFHKSPIALQMLHTNSNITRHWSIAVEWLQGELDRQRGIGCQYNSYSWSPPAQSNDNTNGYMLERSQSAKNTWSMAFELCP
DEVSEKTDENNEPNLETNMDENKSEPVAQPGGVLEGSTGGTEQLPENKTPTTSSPSTAAWPARGDSNAIPRLSRQLFGAYTSTGSGSTSGGSAPT
SALTTTAGSGANSETESSAQETTGETTINGLTNSLDQMEITAKKKCRRVIIKKLVESKDEEDATTATTAATTEVTTSPATAIATAATLEPAGMSE
LTTMVEKNLIISQENPQAKSSLQ*
(SEQ ID NO: 174)

Name: fat facets peptidase
Classification: endopeptidase
Gene Symbol: faf
FlyBase ID: FBgn0005632

Celera Sequence No. : 142000013384567
TTTACGTGTTCTCATAAGATATAGTTTATATTAATGTATATTCATATTTTTACCCATTCATTATCTCTTGGCGCATTTAGAATTTAAGTTTTTTT
TTTGCATTTTCCTTTTTTATTTTACGGTTTGGTATTACTTATAAACAAATTTCATATTATAGCTATAGTTTATTAGCTAGCGTTGTGTAACTTTC
CTCCGCAGGGCCATTACTTACATTGTTAAATCGAAACGTTAATGCAATTGTTTTGTTGTGTATGTCTAACGCAATTTATATGCTCTCTATCTTAG
TTACATGATTTTGTTGCGTAAACAAAGGGCTGCCCCAACTCCCAGCTCCCACATCTCGCATCCCATTTGCCCACCGCTCGGGAAATGCGCGCTTA
AGTGTTTAAAAATCGGAAAGATATATATGAACACAGGCAGCAAAGTGCAGACCACGAAAGTATATATATATATATATATATATATATATATATATAT
ATATATATATATATATATATATATATATATATATATAAATATATATATATAGATAGGGGAGTAGGCGGTACAGAAGGTTACATAATATAACATAG
GAGGGCCTTATAAGTCAGAGCGTTGCTTAAAGCTAGAGAACTGCACGTGGTAATCGCAATCATTTTACCATCAACTTAGGTTACAATGTGGGTGC
CTTGCTGTGTGGCATATGCTTTTGTATGGATTGGATTCGCTAGAGCTAGAGCCTATAGTCTAGGGTTAGGGACACTCGCTGAACGCGGTGTCCTT
TGTTTCTTTTACACAAATATTACACTTACAATCGAGTTATTATGTGTTCATGATCGGTTCTGCATGTTCTGCCTGATTTGGTCTGGGACTTCAAG
TTAACAAAGAAAAAGTTGAGCCGGCCAAGAGCAAATAGTCAAATGCAAAACAGAATTAAATGCCTGCGTGTCCTGCTAACCCTCCTCCCAAACCC
TTCCGCGGACCCCTAATCAACCGCCGATCTATTGGCCAATCTTCAGGCAGGGATCTCAAATCAATTGAACAGTGCGGTTTGTTGCAGTTTCTTGC
AGCCAGGTTGCAATCGTTTATGTTCTAATAGTATAAATTAAATTAATCATAGGCTAGTTAATTAATAATAAGCGCGCTCAACGTTCTAACATCTG
GGAGCAGAAACCAAAATGTCAAAAAACAAACGAAAATGTACACACAAAAAAAGAAAAGCGCTGCGCTTTGCTATGCTCTGCTCTTCTTCTCTCAC
TGCTCTTGTCCTCCGTTTCTGGCAGGGACCTGGTCATCCTGCCGCTTGGATACATTCAACGTGTTTTACCGCATATATAAAGCAAGTATTATATA
TATTAGGTATATATAACTATATATACTACATGTATAGTTTGTTGAGTTCTGTTGTTGTTTGTCTACTGTGTCGTGTCCAGCGTCGCAACCTAAAC
GATAAAATATTATTTGGCGTTCCCCACGCCACCGCCCCCTCCGCCGCTCGGCATACCGCCTACGCCCACTCCACCGCCGCCACCACCGCCTCCCT
GCCGCATCCGTATCGAAGGCCGACGCTCCGGCGTGTCGTACGGCGGTCTCGACGAGTTGGTGGCCGCCATCGAGTCGTCCATGTTGAGTCCGTTG
CCGCCGATCAGTTGGCTGCCGTTACCGCCTCCATTGCCGCCCAGCATCGCCAGCGTTTGGCCGCCCTGGAGTTGCTGTTGCGCTGCACTGCCTCC
TCCGCCACCCAGCGCCGCATTGACCTTGTGCTGCTGTTGTTGATGCGAGGAGGCGGCTGCCGCTGCTGCCACCGCCGCTGCTGCGGCCACCGCAT
CATGACCCGCCTGGCCGTCCGCTCCGTCCTGCGCCTGCTGAATCGCCTGGGGATTGCGAGGTCCGCCAAACTTAAGCAGGTTCCAGTCAAACACA
TAGTCGTAAGTGAAGCCCAAACGGTGGAACAAGTTGCGGAAGAGTTTGCGCAGGTGGCAGTAATCGGGACGCTGGTCGAAATGCATCTGGCGACA
GAAGTTCAGATAGTTGACGAACTCGCTGGGGAAGCCCTTGCACAGCACCACAATCGAGGTGGACAGCTTCTTCTCCGAGATCCTCTCGTACTTTT
GCCTCTTGTTGGCTGCCTTTAAGCCCTGCCAGGGCAAGGCGCCCAGATTGAAGTACATTAGGACGTAGCCCAGGGACTCCAGGTCGTCACGACGC
GATTGCTCAATGCCCAAATGTGTGTTGATGGAGGCATAGCGGGCAGTGCCCGTGAGGTTCTTGTTTTCCCGATAGGGAATGTGCTTCAGCGACCG
GGCATCGCGGAATTTCTTGGCCAGGCCAAAGTCAATGATGTACACCAGGTTGCCCTTTTTGCCAAGACCCATGAGGAAGTTATCCGGCTTGATGT
CGCGATGGATGAAGTCCCGCGAGTGTATGTAATCGATGCGGGAGATCATCTGGTCCGCCAGCAGCAGAACCGTCTTCAACGAAAAGCGGCGTGAA
CAAAAGTTGAAGAGGTCCTCCAGCGAGGGTCCGAGTAGCTCCATCACCATCACATTGTAGTCGCCCTCGCTGCCGCACCAGATTATGCGGGGTAT
GCCTATGCCACCCTGCATCGTCTTGTAGAACTTTGACTCGATGTGCAGCTGGGGGTGTTTGGTGCGGATGCACTCCAGCTTGATGGCCACCTCCT
CGCCAGTGTTGATCGTGGTGCCCAGGTAGATGTCGCCGAACGATCCCGATCCTATCTTGCGGCCCAGGCGATATTTGTTACCCACGCGCAGCTCC
ATTTTGTTACGTCTGTTTCTGTGGGTTTCTGTGTGGTAGAGTTCGGACTCCTCGGGTTCCTCGGATTTGCGTTGCCTTTCTGCGGGACCGGAGAA
TTGAAATTTAGTTTTAATTTTACAACACATTGCCTCGAAAAGAAGGCTGTACGCTTTTCTTACTCATAATACTACACGCTACACGAATTGATCGA
TCCCAGTTCAGATTAGCTGCGCTTAAAATATTATACAGATTTAAATATCTACGCCAAGGACTAAAACTTTTACTTTGTAATCGCGAAAGGATATT GAAAGGTTGCTACGATGCAGGCAAATTGTTGAATTCGATCAGAATGTAAATATTCGTAGTATTCTTAGTTGCTTTGACTAATCATAGAAATAGCA
GCGGCGTCACAGGTTTTTACGAGTAAATATGAATCAAGTGACTTCGAAAATTCGGCTATTGACCACTAGCAACAATGTGTGATATTATTAGAAGA
GATTATTTGCAAGCAACAACACAATATCGAACGCCTTGTTAGCGATAGTGATAAAATATTCGTCGGATTTTGTTTGCTACAACTTTTGATTCTTC
TGACACTATATTGTGACACGTGATGACAACCCTGCTGTTTTGTACAGTTTGCTAAAAGTCTAATTTTGAGAGCTAACGGAGCTTCGTGAGTATTT
TCCAACACTTCTCCACTTTTCTCACCTGGCACTGTCCTTTCGTCTGAGCTCCTTTCTTCTTCTTGTTCCGATTTGTTCAAGGCAGTCGCTTATGG
CTTTGTATTCGAAGGGTTCTGTAATAGGAGGTACTAAGTTAATTTTTTTTTAGATCCTCAACATGGTTAATCGAAATTCGACCCGTCTCGCGATC
ACTTATATATAGAGAGTAATCCCCTGTTTTTATCGCATCTGCAGCGTAAGCCCGAAAAACGTGCAGAATTCGCTTTTGTTTGTGGTGATAAGGAT
TGTGGCACACAGACATGAAAACAACGCACGGCAACAATCGATATCGAAAATAGAAAACCGTTAGCTAAGAATAAAACAAGAGAGAGAGAGCGGGA
GAGAAGTAAGCTTGGCTTACGTTGACAACACAAAAATAGCAGAGAAAAGCGTACCAAAAGCAATTCGAAATGCAAATGCACAGTGGGCAAAAATG
ATAAGAACCCGAACCTCGCACAAAGTAAAAGTTTATCTCGTATATTTATATTTAAGAGTGAGTGCGTCATTGCATTCGGCTGTGTGTATTGATTA
CGAATGGGGAAAACAACAGATTTAATAAGTGATGAGTAACGATAATTTATATGCACAGAGCAAAATAGCACTACTTTTTGACATTCGTCACATTA
TTGTTTTAGTCATTTTAATATTATATTGTACTATTATAAAATAAAGCAAATGTGCCGTAGTGCTTTTACATCCTTGAATAGATATAATTCTTTTT
TTCAAGTGTATTTTTTACGTGACGACACCAGAAACATGGAGGTGAATCAGCAATCAGGAAAAGACAACGAAGAGATTAACAACAAATAGATAAAA
GAGACGTGTGTTTGTGTATGCGTGGAGTAAACAATCGGCGACAAAAGGGAGAGAAGTAAAATAAAACGCAGCGACTGTGAAAATGCCACTTAAAT
GACACTTTCAGTGGTGGAAAGCACAAACAAATAGCGAAGATAAAGCGCATGGAAGTCAGAAAACGAAGCAACAAGCCGAAAGTTTTCACTTGCCG
GTCAAATATCACAAAAATTTAGTTTAATTGTTTTCGGCGGCTCTCACTCACTAACCCCTTCCCACTCCTCTTTCCCACATTCTGTGCGCTTTCTT
TTACCGCTCACGCATTTCGATCGCTCTCTCTCTTTCTCTCTCTCTCTCTCCTCCTTTTCCCGACTCTTTATCACTCACTCTGCGGTTCTAACC
TCAAAACCTGCCTGTGTTTGTTGTTGTTTTCGCCTTGGCTTTGATTTATTTAACCGAAATGTACCGTTTTTTATTTGTATCTCCCATGTTCTACA
CAGAAAGAAATCACTGTATAAGCACTGTAAGTCAAATTGAAATGTGGTATTAATTTTAGGAGCTTTAATTTGTTTACTGGAAGGCTAGCAGGGAA
AACGCGGTCTTTCCTATTGGTAACTAAATATTTCCCAGGGTATCCAGCAGTTGTTTCGGACCAGCGGGTAAACACGAATTGATTACAATTGCAAA
ACAGCTGCACGTTGCGTTGGCGGCTGCCGAAAAGCTTCCGCAAAAAAACGCACTGGAGAACAAAGAAGATACAAAAAACAGTTGTTCCAGCAGGC
GCCACAAAAGTAAAAAGCTTAAGTAAACAGGGAAGAGCAAATGGAAAAACCAAAAACCAGAGCAAAACCAACGGGGAAACCTCAGAAGGGGAAGG
AAACTTGCAATTAATTGTCAAACGCTAATGGCCTCCGAAAACTAACGGCACTCCACGAATGCACTGCGAATAACGGGGCTGATAAGGAGCAGCCG
ATAGCGGGTGGAGAAGGGAAACTTGAACGCACAGTGGAACAAATTCCGCACTTACCGTGGCTTGTTTTTCTTATATTCCTTGTTTCCTATTCCGC
TTTGCCCACTTCCTCTGCTGGCGACGCTGCTTTTCCTTCTTCTAATTCGACTGAAATCGAAATCGAATTTTTTAATTGGATTGATTCTGCCACAA
TAATTTTCATTTTCTTTGTTTTAGAGCCCAGACGTTGTTTTTGTTGTAGTTGCCACAGTCGCACACAAACACACGCACACAGTCGCACTTTTTGG
GGCCACACGCAAGCGCATTTTATGCAATAATTTTAATAATACTGCATTGCTGCCATATTTCAGTTATTTTTATCGTTTATCTTCGAGTCGGTTAT
GCTGTTCTTCTCTGATTTTATGGCCACATTGATTAGCATCTTGTTGCCAATCAACTCGAGAAAATTAAACGAAACCAAACGGAACTCGGACTCTT
ATTAAAAAAACCAAACTTATGCGAGTCGTTTGCCCTGGCAATAGATTCGTGCACACTAGTCGTCCCGCCCGCACTCGCACGGTTTCTACCGCGAG
CACGTTGCTATCCCTCCTGCTTCAGCATTTTCACACCAACACAAAGACGAGGGCACTCACTCACACACTCGCACTCTCAATGAGCACTGAAATGC
TGTTGGGAAATTCGAGTTTTCCTGCGCGTGGTAACCGCCGCTTTTTCGCTCGCAAACGGGTCTGTCGATCCGAAACGCTACTGACCACTTACGTT
TTGCATCAACGCTGCGCTTTCGTTTCAATTTTTCTGGCTATTTCACATAGATTTCGACGATTTTTACAAATTTACGCCATCTTGATATTCGCAG
TGTGACCGCGCCGATAATGAAGAAAATTACCATCTGGTATTTACTCCTCAGCGAATGTCTAGAAGATATGTAATTGTGAAAAACTGTGATTCATA
TACTAAGTTAAGATAGTCCAAAGTTGGTTTCGAAGTACCACATTAAGAAAATAGCGCAAGAGTATTGGAAAATCAAAAGAAAAACGAAATTATAT
CCTTGCAGCTAGCCATAAGTTCAAAGTTCGAGTAACTGGAAAGCTGTGAAATAGCCAAGTTGACAACGCTGTTTTTGTTATATGGGCACACTAGT
TCTTACATAGACCCAGTGCTGCCAGATGGACGAAAAATATTTTTGAGCTGCGCCACCTAGCGGATGAGTTGGCGAAAGTGGTATCCAGGTGGCGC
CCGAAACAAAAGGTGGCGCCTTATTTCAGAAATGCAATTGAAAATATCTAAAGTTATTGAAAGTTTTTGAATTATGCATTCAAAGGCCCATCTGC
TTAATTTTATTTTCAAAGAGAATACAATAAACAATACAAAAAAAAAAAAATCATTCTGAAATGATATTTATACTAATATACAAATTTGATAACTC
AATAATATGTAAATAAAATTTATGTCTTAATTTGCAATGTTCTTAAGAAAAGTTGTTAACTCTTTTTACAGGCTTGTGCTCCAAATTCTCGTGTA
AATAGAAATTGAAAATGGATTTCATTGGCATGTCTTGCAGTTATAGGTAGCATGCCAATTTTGATGTTACACAGATGTATCGAAATACCTGAAAC
GTATACTTTTATTGCAGCAATACGAATAAAGCAAAACACGTGTGAATTCCATTAGTCCGCCCAACCGCTTTCCCCATTTACCCTCACATCGTGCA
TTTTCCGGCTGTGTAACCCAAGAAACGATGACATAAAAAAAGGAAGCAGATCCAGTTATGTATGCATATATGAGAAAATGTGTTTTTTTTTTTT
GGGAGTATGTGCCAAGGTGTGTTTCTTTTTAAGTGGGGGTAGGGTAGAT
(SEQ ID NO: 175)

Exon: 6079..5983
Exon: 5370..5281
Exon: 3533..3446
Exon: 2834..1001
Start ATG: 2757 (Reverse strand: CAT)

Transcript No. : CT6302
TGCGAATATCAAGATGGCGTAAATTTGTAAAAAATCGTCGAAATCTATGTGAAATAGCCAGAAAAATTGAAACGAAAGCGCAGCGTTGATGCAAA
ACTCGAATTAGAAGAAGGAAAAGCAGCGTCGCCAGCAGAGGAAGTGGGCAAAGCGGAATAGGAAACAAGGAATATAAGAAAAACAAGCCACGAAC
CCTTCGAATACAAAGCCATAAGCGACTGCCTTGAACAAATCGGAACAAGAAGAAGAAAGGAGCTCAGACGAAAGGACAGTGCCAGAAAGGCAACG
CAAATCCGAGGAACCCGAGGAGTCCGAACTCTACCACACAGAAACCCACAGAAACAGACGTAACAAAATGGAGCTGCGCGTGGGTAACAAATATC
GCCTGGGCCGCAAGATAGGATCGGGATCGTTCGGCGACATCTACCTGGGCACCACGATCAACACTGGCGAGGAGGTGGCCATCAAGCTGGAGTGC
ATCCGCACCAAACACCCCCAGCTGCACATCGAGTCAAAGTTCTACAAGACGATGCAGGGTGGCATAGGCATACCCCGCATAATCTGGTGCGGCAG
CGAGGGCGACTACAATGTGATGGTGATGGAGCTACTCGGACCCTCGCTGGAGGACCTCTTCAACTTTTGTTCACGCCGCTTTTCGTTGAAGACGG
TTCTGCTGCTGGCGGACCAGATGATCTCCCGCATCGATTACATACACTCGCGGGACTTCATCCATCGCGACATCAAGCCGGATAACTTCCTCATG
GGTCTTGGCAAAAAGGGCAACCTGGTGTACATCATTGACTTTGGCCTGGCCAAGAAATTCCGCGATGCCCGGTCGCTGAAGCACATTCCCTATCG
GGAAAACAAGAACCTCACGGGCACTGCCCGCTATGCCTCCATCAACACACATTTGGGCATTGAGCAATCGCGTCGTGACGACCTGGAGTCCCTGG
GCTACGTCCTAATGTACTTCAATCTGGGCGCCTTGCCCTGGCAGGGCTTAAAGGCAGCCAACAAGAGGCAAAAGTACGAGAGGATCTCGGAGAAG
AAGCTGTCCACCTCGATTGTGGTGCTGTGCAAGGGCTTCCCCAGCGAGTTCGTCAACTATCTGAACTTCTGTCGCCAGATGCATTTCGACCAGCG
TCCCGATTACTGCCACCTGCGCAAACTCTTCCGCAACTTGTTCCACCGTTTGGGCTTCACTTACGACTATGTGTTTGACTGGAACCTGCTTAAGT
TTGGCGGACCTCGCAATCCCCAGGCGATTCAGCAGGCGCAGGACGGAGCGGACGGCCAGGCGGGTCATGATGCGGTGGCCGCAGCAGCGGCGGTG
GCAGCAGCGGCAGCCGCCTCCTCGCATCAACAACAGCAGCACAAGGTCAATGCGGCGCTGGGTGGCGGAGGAGGCAGTGCAGCGCAACAGCAACT
CCAGGGCGGCCAAACGCTGGCGATGCTGGGCGGCAATGGAGGCGGTAACGGCAGCCAACTGATCGGCGGCAACGGACTCAACATGGACGACTCGA
TGGCGGCCACCAACTCGTCGAGACCGCCGTACGACACGCCGGAGCGTCGGCCTTCGATACGGATGCGGCAGGGAGGCGGTGGTGGCGGCGGTGGA
GTGGGCGTAGGCGGTATGCCGAGCGGCGGAGGGGGCGGTGGCGTGGGGAACGCCAAATAATATTTTATCGTTTAGGTTGCGACGCTGGACACGAC
ACAGTAGACAAACAACAACAGAACTCAACAAACTATACATGTAGTATATATAGTTATATATACCTAATATATATAATACTTGCTTTATATATGCG

FIGURE SHEET 90

GTAAAACACGTTGAATGTATCCAAGCGGCAGGATGACCAGGTCCCTGCCAGAAACGGAGGACAAGAGCAGTGAGAGAAGAAGAGCAGAGCATAGC
AAAGCGCAGCGCTTTTCTTTTTTTGTGTGTACATTTTCGTTTGTTTTTTGACATTTTGGTTTCTGCTCCCAGATGTTAGAACGTTGAGCGCGCTT
ATTATTAATTAACTAGCCTATGATTAATTTAATTTATACTATTAGAACATAAACGATTGCAACCTGGCTGCAAGAAACTGCAACAAACCGCACTG
TTCAATTGATTTGAGATCC
(SEQ ID NO: 176)

Start ATG: 353 (Reverse strand: CAT)

MELRVGNKYRLGRKIGSGSFGDIYLGTTINTGEEVAIKLECIRTKHPQLHIESKFYKTMQGGIGIPRIIWCGSEGDYNVMVMELLGPSLEDLFNF
CSRRFSLKTVLLLADQMISRIDYIHSRDFIHRDIKPDNFLMGLGKKGNLVYIIDFGLAKKFRDARSLKHIPYRENKNLTGTARYASINTHLGIEQ
SRRDDLESLGYVLMYFNLGALPWQGLKAANKRQKYERISEKKLSTSIVVLCKGFPSEFVNYLNFCRQMHFDQRPDYCHLRKLFRNLFHRLGFTYD
YVFDWNLLKFGGPRNPQAIQQAQDGADGQAGHDAVAAAAAVAAAAAASSHQQQQHKVNAALGGGGGSAAQQQLQGGQTLAMLGGNGGGNGSQLIG
GNGLNMDDSMAATNSSRPPYDTPERRPSIRMRQGGGGGGGGVGVGGMPSGGGGGGVGNAK*
(SEQ ID NO: 177)

Name: discs overgrown
Classification: protein_kinase
Gene Symbol: dco
FlyBase ID: FBgn0002413

Celera Sequence No. : 142000013384566
TAAAAGTGAATACAATTTTTTGCAGTGCAGTTAGCGTCTCGCTTTACTTCCTCTTTATGGTTGGCTTTTTGTGTTTTCCAATCAGATTAGCATGG
TAAGGGGTTAAGAGTACGGGGTTACCACCGCTGGGAGGGGACCACATGAAAGGGTCAATAATGGGACTCGAGACGAAGATGCTGACATTTATCAA
ACGGAATATGCGATGCGTACAACCATTAGACACTGCCCACTGATGGACGTCGGACGATGGACAGGCGAGACGTGATCCCAGATACGGCTCATCAA
GTGCATTGTCGTGGGACAATAAAGGGTTAATCGGCTAACAGAGAGATTGCAATATTATCTTCTGAGCAAATTGGAGTTGGGAAGACAGCAAAAAT
TAGCGAAAGTAGATCCAAATATTAAGTGTATCAATTGTAAGGCGTATCACTTGATTCCGCACTCTACTCAACTCTCCAAGGACCTCTGTAATCTG
ATAGGCTTACTGAACCAACAGAGAGTAGAAACAAAGTTTTGCTTTATTGTGATTTTACGAAATAACCTACAACTTCACCATTCCCAAAAACACAA
TTTCTTTTTCCTTAAACATTCCAGTTTTAAACACCTTTTTTACAGTTTTTTCGTTGTAAGTTGGCCAAAATATGTCACAAGGCTGAAAAACGCAC
TTTTTTAGTCAGCTGGGGTCCTCAGCTAAAGACCCATATCAATATTTGCTTTAATTTGGAAAAATAATTTTTCGGCCAAATTTCGCATTTTTTGT
AAGGGGTAACATCATAAAAAATCGAAAAAATTTTCAAACCAAAAATTTCTCTAAATGAGTTACCCGTCGTTTAGGAATATTTTTACAAGTTCAAC
GAGGTATTCCACTCCACAATTGGACGTGTCTTTCCCAAGATATAGCACTTTTTCTGTGAAATCCCCATCGAAAATTATCAACAAGAATAAAATCA
CCCTCGTTTTCCATCTGAAAAAACTCCCTCAAAAACAAACGCATATACAGTTTATTTCGTTACATATATATTGTTATTTATTTAAGAACTTGCTC
GTCTAATTGACAGAAAAATATAAAGATATAGGATGTATTGAATGGGTTGTGCTGAGTGTCTTACTATGCGAATGAGCGATTCCACTTAAGCCTAG
GCGAAATCTCGGCGATTGCATAATGTGGAGCCCCCTCCCGAGGTGTACGGAAATCACAAGTGGTTGATAAGAAAGAACAGACGTGGAATTTTGCT
GTGCTGGTTTGAGGATCGCAGTCGAACGGATAATTTATTGGCCAGTCGCCGACTTGGCTGGTGATGATTTAATAGCGGACCCTCGGGAAGGCTCT
CTGGGCTGACAGATAACAGATAACTCGACTGGCTGATAATTTTGATGCGTGACTGGGCGCTGCGCCTTCTCTATCTCCACCTCCTTACAGGGTCT
TGTCGAACAGGAACTCGCCCAGTTCGCCGTTGGTGTCCATCATCTTCTTGAGAGTGGTCAGCTTGCCGGCGAGCTCGCGCTGTCCGTGGAGCTGC
TCCTCCAGATAGACACCGGTCAGGTAGTCCACCAGGTGGTAGTGGTTGTAGGGCTTGTTCTCGCAGGTCTGGATCAGCTTGCGGATGGACTTGGT
CACCTTGATCTCCAGGTCGAGGGCGTCGGACAGGGCGGCGGCACCATCGGTCCACTCCTGCTTGGCCACAGTCTGTGGGGGATTCGCCAGGATTA
GCTGGGCTTTTGGGTTTTCTAGGCGAGTCGTCGACTTACCGGCACATTGATCAGATCGCTGACTCCCTCGGTCAGTTGACCGCGCATGGACAGGT
ACTCCACCAGCTTGGATCCGTGCTCACGTTCCTCCTTGGCGGCCTTGAAGAAGTGCTCGGCGAATCCAGGGCGGTTGACGGTGTCGCGGGAGAAG
TAGGCGCCCATGGCCAAGTACTGGTAGGAGGCGTTGATCTCCTCCTGGATCTGATTGCGCATGCCCTTTATGCAGGCATCCTTCATGTCCACCCA
GTCCTTGGTAATCTCAGGAACAGCCAGGGAGCCTGCAATGGGATAAGGTTGGGTTAAGTCGGGGGACCACGATAACAATATATGGCTAGTATTCA
GCTTTAAAAAATTTATTTTTGTAATCAGAACTTAGGTAAATTTTAATATTTTAAAAACCTTTGCACTCTTGGTCTTGACCTTCATGGCTTAGGTT
TTGTTTTTCTTTTAGTTGATGCTCTTCTCGCTCCCTTTGAAGCTCTCTCACGAAACTCTTGCTTTCTTGCTTGGCTGAGGGGTAGGGCGTTGTTG
GTTATTGCATTTAAGAGGGCGTAATTGCATAAACCTTTGAAATTGCGCTTGAAATGCCGCTATTCTAGGGCACAAAAACCGTGTGCAAAACTGTA
ATGGCCTACTCTCCCACTCTCTCTCTCTGTTTTTGTAACTGCATTGGTAACGTGCGCAGCTCTCGCCGCCATAGTAACGGCATTTGTTTTCGTGT
AGTGCCGTGTGCAAAAAGCATGGTTCACCATGCTAGCTCACTCGGCCCGTAAAAGCCGTGTGCAAAGAGCGCCTTGAAATGTAACAACAAAAAGT
CAAGCTTATTTATACCGCAATATTCATGGAAATGAAAGCGAAATTCGCATTATTTAATTATGAAAATTTATGTATAAAAACTGGTTATCATTTCC
CCAAAGCGCAACGGAAGTATCAATAACTTTTAAATCAACTGGTTTGGTAACTTCACTTCATTGACGAAAGAGAGTGAAAGAGCGTCAAAGAGAAA
CGGCGCATGCTCTTTTCAACGCATTACAAATGTTTTGCTTCTCTTTGCGTATTGCGTCGAAATTTATTGTTTTTTTTCCGATGACCTGCCTTTGT
TTTGTTTGAAATTCTGATGAATAAAACGTAACATTAGTACTTACACTTGAAATCTCCATAGGCCTGGGCCACCACGGCCAACAGGAGCAGGCTAG
CAATTAGTTTCACCATCTTTGATCGTCGAACGTAGTCTTTACACAAAATCACAGAACAAAAATTTGTTTTTCACTTTAGTTTGATTTGCTTGAAA
TGCACAAATGAGAATGAGGCGACTCGAGTTGAGCTACAATGTTAAATAGGCGTTGAAATTGAAAATCTAGCTGCCTTTACACACACTGGCGCAGA
AGGCGTCGCCTGCTTCAATTTGATGGGCTTGATTGGGATTATTTCGACTTCTCGAATGCTTTCCAGTACCTTCTGCTGACAGCTTTAATCTGAT
TTTTCAGTGGAGCTAAGGCCTTTCTACGTTGTGTTTAGCGAACTCGAAAGCGAACTGTCGCTCCGAACGGCGCACAAAACACTTTAAGCGCGC
GCGCTCTCGGTTTTTCTTCGTGTGTGTGTGAGTGATGGGAGAGTGTGCACTGTTATCTTTTCAACATGTCGCCCGTTCTTTGTTAACCGTTTAAA
TGGCTGATAATTGAATATTCCCGATAATTGCCGCACTCAATGTGATACACACGTCCTCAATATGGGTATACTTTGTATAAAGTCGGGTTTCCTAG
TCAGATAATCCCCACTTACTAAGAAGTAAATTTATCAAATGCAATATGGCCGCTCTTTTGAGATGCGCATCAGCTGTTCTTTGTTTTTGTTTTGG
CCGTGGGAGAGCACCACGTCATGTGTTGCCAGGCGGTTTAATTATTGCTGACAATTTAATTCACATTTTGTCAAGTTGATTTGCACGTTCGAAGG
GGGGATCAGTCACCCACTTTGATAACTGCTAATATGGCGACGGCTCTTTTTTACGTGTCGCTTGCAGAGCTCCAAGAATGACACTTGATAAGAAG
GATACATGGTGGGAAAACTTACAAATTACATAATTTGTTTGTTGATTGGGGAAACCCTACATTATCTCCGAACCCAGCAATAATATGTATTGTAA
ATAGCAACAGTCTCAAGCTCGATGCTGCTGTGAATTACCAATATATCAAAACTTAAAACATTATCTTAGGAGGTAGATGGTTTATCTGCAGTTTA
TTTTCAATTCTCATCGTTAGCTGATAAAACTCTCAGGAAACCACTTGAAATCCAAAGTGCAGCGTCCATATTTTGCACACGCTGACAACCCTGTC
GTGAGTCACCTTCCAGCAGGCGCAGCAACAACAGCACTGGCAGCGGCCATATTTGAATGACACCGAAATCCCGCACTGAGCGCAAAACAACACAT
GCCCATGCACGCTCTCCAAAACCACACACACACAGCCATATCGATCGCATAGAAAGAGACGTACGCGACGCTATAAACAGCAGTTGATTTTCAGA
GTTTCACCAAGAAGCACATAAAGCGATTGAATTATTAATAAAAGCACAGGCACTGGAAGTGAGTTTTAATATTACTAACTAACTACTTTGTGAGT
GTTTAGTTACGAAAACTAGAAAATAATATTCTGGAAACTGTGTTTTTAAACCGACCACCATATAAATTTAAAAACCAAAACATTCCATTGGTGGT
GGTTTTGTTGTTAAAAAAGAGCACAGAAAATTCAAGAAAACGCTACGACGCAAAACGAAAAAACTCGCCCAAAATGAAAACAAAAGTGTCT
(SEQ ID NO: 178)

FIGURE SHEET 91

Exon: 3556..2895
Exon: 2027..1750
Exon: 1687..1001
Start ATG: 2961 (Reverse strand: CAT)

Transcript No. : CT6417
CATTTGATAAATTTACTTCTTAGTAAGTGGGGATTATCTGACTAGGAAACCCGACTTTATACAAAGTATACCCATATTGAGGACGTGTGTATCAC
ATTGAGTGCGGCAATTATCGGGAATATTCAATTATCAGCCATTTAAACGGTTAACAAAGAACGGGCGACATGTTGAAAAGATAACAGTGCACACT
CTCCCATCACTCACACACACACGAAGAAAAACCGAGAGCGCGCGCGCTTAAAAGTGTTTTGTGCGCCGTTCGGAGCGACAGTTCGCTTTCGAGTT
CGCTAAAACACAACGTAGAAAGGCCTTAGCTCCACTGAAAAATCAGATTAAAGCTGTCAGCAGAAGGTACTGGAAAGCATTCGAGAAGTCGAAAA
TAATCCCAATCAAGCCCATCAAATTGAAGCAGGCGACGCCTTCTGCGCCAGTGTGTGTAAAGGCAGCTAGATTTTCAATTTCAACGCCTATTTAA
CATTGTAGCTCAACTCGAGTCGCCTCATTCTCATTTGTGCATTTCAAGCAAATCAAACTAAAGTGAAAAACAAATTTTTGTTCTGTGATTTTGTG
TAAAGACTACGTTCGACGATCAAAGATGGTGAAACTAATTGCTAGCCTGCTCCTGTTGGCCGTGGTGGCCCAGGCCTATGGAGATTTCAAGTGCT
CCCTGGCTGTTCCTGAGATTACCAAGGACTGGGTGGACATGAAGGATGCCTGCATAAAGGGCATGCGCAATCAGATCCAGGAGGAGATCAACGCC
TCCTACCAGTACTTGGCCATGGGCGCCTACTTCTCCCGCGACACCGTCAACCGCCCTGGATTCGCCGAGCACTTCTTCAAGGCCGCCAAGGAGGA
ACGTGAGCACGGATCCAAGCTGGTGGAGTACCTGTCCATGCGCGGTCAACTGACCGAGGGAGTCAGCGATCTGATCAATGTGCCGACTGTGGCCA
AGCAGGAGTGGACCGATGGTGCCGCCGCCCTGTCCGACGCCCTCGACCTGGAGATCAAGGTGACCAAGTCCATCCGCAAGCTGATCCAGACCTGC
GAGAACAAGCCCTACAACCACTACCACCTGGTGGACTACCTGACCGGTGTCTATCTGGAGGAGCAGCTCCACGGACAGCGCGAGCTCGCCGGCAA
GCTGACCACTCTCAAGAAGATGATGGACACCAACGGCGAACTGGGCGAGTTCCTGTTCGACAAGACCCTGTAAGGAGGTGGAGATAGAGAAGGCG
CAGCGCCCAGTCACGCATCAAAATTATCAGCCAGTCGAGTTATCTGTTATCTGTCAGCCCAGAGAGCCTTCCCGAGGGTCCGCTATTAAATCATC
ACCAGCCAAGTCGGCGACTGGCCAATAAATTATCCGTTCGACTGCGATCCTCAAACCAGCACAGCAAAATTCCACGTCTGTTCTTTCTTATCAAC
CACTTGTGATTTCCGTACACCTCGGGAGGGGGCTCCACATTATGCAATCGCCGAGATTTCGCCTAGGCTTAAGTGGAATCGCTCATTCGCATAGT
AAGACACTCAGCACAACCCATTCAATACATCCTATATCTTTATATTTTTCTGTCAATTAGACGAGCAAGTTCTTAAATAAATAACAATATATATG
TAACGAAATAAA
(SEQ ID NO: 179)

Start ATG: 596 (Reverse strand: CAT)

MVKLIASLLLLAVVAQAYGDFKCSLAVPEITKDWVDMKDACIKGMRNQIQEEINASYQYLAMGAYFSRDTVNRPGFAEHFFKAAKEEREHGSKLV
EYLSMRGQLTEGVSDLINVPTVAKQEWTDGAAALSDALDLEIKVTKSIRKLIQTCENKPYNHYHLVDYLTGVYLEEQLHGQRELAGKLTTLKKMM
DTNGELGEFLFDKTL*
(SEQ ID NO: 180)

Name: Ferritin 1 heavy chain homologue, FER1HCH
Classification: ligand_binding_or_carrier
Gene Symbol: Fer1HCH
FlyBase ID: FBgn0015222

Celera Sequence No. : 142000013384573
TACCCGCAATTTAACTGCTCTAAGGTAAAAGAAAAATTTGTAAAGAAAAAAGAAAAATTTGTAAATTTGTAAATTTAATGTATTGCAACATATAT
AATAAACACGGTATGTGCCACACTGCGAAATATCAATGATTTTGACTTTGACTGACCACCGTATACGGACACACCCACAAGATCAGACCCACAAA
GACTCACCCACAAAGGCCTTCAGCTCGTAGTCTACTCCGCAAGACTTGCCCACATCTCCAGGAGCCGGCTGCAAGGACACAGAGGCTGGGCAATA
GGGCGGAACCTCAAAATAAAACGGATGGGCGTTCGGCCCCAGCTTTTTAATTAACCTTTCCTGAAGCCGGGTCATCGGGCGGTCCAGCTGCATGG
GCGGATAGATCTGCTCATGCGCCAGATACAGGTCCTTACGGAACGTTAATCCCAAAACATCTAGGTCTTCACGTCCGTACCGAAAGGCGGCAAGC
ACCTGGCCAAAAACCTTACGGTCCTTTACGTACTCTGGATCAATGAAGACAACACCGTCAATGGGATCCACGTGCGTGACATGGTCGACGAAGTC
CCGTTTGCCAAGGTAAACTGTTATCTTGCCGTTGGAGGAGCTCTTCTTAAACACCCGAGTCGCCTGGCGTCTGGAGCTGGCATCTCCACCAGTCT
CGTCGCCTGCGCTTCCGCCCCCAGTGCTCCCGGCAGCTGTTACATTGGTGCTGGAGCCATTGCTCACATTTGCTCCTCCACTTCCTCCACCACCA
CCGTTCATTATGTTATTTGGCGGTTATGCTTGTTATTCTGCTTTTCTGCTGTTCCTGCTTAATTGGAACTCCGTTAAATAAATATATGTGTGCGT
TGCGGGACTTGTGCTGCAATTTAATTTTTTATGTGTATACTTGTTCCGCCATTTACCAGCACTGCTTGACAGTCATTGGAAAAATACCAGGGAAT
ATTACATACTAACAAATTATGTACTTCTCTGGTATTTCAATTCAGTGCGAACAAACCGATATATGTTTGGTCGTACCATAATCGCAGCCTATAAT
TAATATTTATTTTGCATTTTTGGCACCTATTTATATTTCCTAAGTGTGCCCTGGCCCATAGTAAGTGACTTTTAATAATTTTTCTTTCAATACCA
TTAACAATTGCTTGAATTAACATTAAGTTTCCTACTAAGATAAAATGCAACTGCAGGTTGACTTGGCTTTTTAATGAAATATAATATATATATTA
TAAATTCCTTTAGAAACAGATGATTCATAGCTGATGATTGAGGAAACTTACCATTTGGAATGTATAAACACATGTAAAATCAGACCGTTGGTAAA
TATCTAATCATAGATTGTATCCTAAGTCTTAAATAAATACTTTATATAAACTGTTTAATATTTATTTTATTTTTTAAAGGCTTTTATTATTTTTA
TATGTATACATGTGCATGAACGGACTTTAAACCATATTTAGTAGTGGAATAGAGCTATAAAAATGAGATTGAAGTCTCTAAAATACTTTATTTAA
TCAGCCTTAGCACCGATAGAGCACAACGGTCACACTGTTCTGTCCCTCTTTTCCACGTGCATTTTATTGAACGAAACCACGCGTTGTTCAGTCCA
AACTTGACTTTGCTAATTTTGCCCAGAAAACCTCTAAAAGCTGTCAAAATGGCCCAAAAGAAAGCCGTCACCGTCAAAGGAAAAAAAGCTACGAA
TGGAGAGGAAAAGCCTTTGGCCAAACGGGTAACCAAGTCCACAAAGGTACAGGAAGAGGAGACAGTAGTCCCCCAATCGCCTTCCAAAAAATCCA
GAAAACAGCCTGTTAAAGAAGTGCCGCAGTTCAGTGAAGAGGACGAGTCTGATGTGGAGGAGCAAAATGACGAGCAGCCAGGGGACGACAGCGAC
TTTGAGGTAAGCTATAAAAAAAACGTGGTCTTCTGAATGGATATGGCTAACATTACATGCATAGTATGCACGTATATATAGATCTGCATGGATAA
GAATCCATTTTACGTTTTCTTTGCCACGTGGTTGTAAAGATTTTATAATTATAAGACGAGTGCACATAACCCACGATCCTCTGGTTTTATACCGA
CTCGGTTCATATATCGATAAAAAAAAAATTGTCTTTATTGGTGCTCTCCCATCAGCGGTTATAAGAAAATTGTCTACTTTTCAGACCGAAGAGGC
AGCGGGCTTAATTGACGACGAGGCTGAGGAAGATGAAGAGTACAATAGTGACGATGAGGAAGATGATGATGACGATGAGTTGGAGCCTGGTGAGG
TTTCCAAAAGTGAAGGCGCGGATGAGGTAGATGAATCCGATGATGATGAAGAAGCGCCTGTAGAGAAGCCAGTTTCCAAGAAATCAGAAAAAGCC
AACTCTGAAAAGTCCGAAGAAAATAGAGGAATTCCAAAAGTAAAGGTTGGCAAGATTCCGCTGGGAACGCCAAAAAACCAGATCGTTTTTGTCAC
AAACCTACCAAACGGTAAAGTAACTGGTTTATTATTTCATTTTTCAAGTATATTTAAACTTAGTATATTTGTTCCACATAGAGTATCTCCACAAG
GACTTGGTCGCATTGTTCGCCAAGTTCGGACGACTTTCCGCTTTGCAGCGTTTCACTAATTTGAATGGCAATAAATCAGTTCTCATTGCCTTTGA
TACGTCAACTGGAGCAGAAGCTGTTCTGCAGGCTAAGCCTAAAGCGTTAACCCTTGGAGACAATGTTTTGTCTGTGTCCCAACCGAGAAATAAGG
AAGAGAACAACGAACGCACGGTGGTGGTTGGCCTGATTGGACCTAATATTACCAAGGACGACTTAAAAACCTTTTTTGAGAAGGTAGCTCCCGTG GAGGCGGTGACTATATCCAGTAACCGCCTCATGCCCAGAGCTTTTGTACGTTTGGCGTCGGTCGATGACATACCGAAGGCTCTTAAACTGCATAG
CACTGAGCTGTTTTCTCGCTTTATAACGGTTCGTCGGATCTCACAAGAATCGATTTCACGTACCAGTGAACTTACCTTGGTTGTCGAAAATGTGG
GCAAACACGAGTCTTACAGCTCCGACGCTCTAGAAAAGATATTCAAAAAATTTGGTGATGTTGAAGAAATCGACGTTGTGTGCAGCAAGGCAGTT
TTAGCTTTTGTCACGTTCAAGCAGTCGGATGCCGCCACGAAGGCTTTAGCACAACTCGACGGAAAGACTGTTAATAAGTTTGAGTGGAAGCTTCA
CCGATTCGAACGCAGCACCTCGGGGAGGGCCATTCTTGTGACGAACTTGACTTCAGGTGGGTTACCCGTTTCGTAAAATTGTTTAAAATTATTAA
TCATTATCATGTAAAATTTCGTTGTAGATGCTACTGAAGCCGACCTGCGGAAAGTGTTTAACGATAGCGGCGAAATCGAAAGCATCATAATGTTG
GGCCAAAAAGCGGTAGTAAAGTTCAAGGACGATGAGGGTTTCTGCAAATCTTTCTTGGCTAATGAAAGCATTGTAAACAACGCCCCTATATTTAT
TGAGCCAAACTCTCTGCTGAAGCATAGATTGTTAAAGAAACGCTTAGCTATTGGTCAGACCCGCGCCCCGCGGAAGTTCCAAAAGGACACTAAGC
CAAACTTTGGTAAAAAACCATTTAACAAGCGCCCGGCACAAGAGAATGGTGGTAAATCGTTTGTTAAAAGGGCAAGATTTTAGAACTTGAACACT
ACAAGAATTAGCTTTAAGTTGCGTAGTACCATAAATACGGCCACAGCCCCGATAATTCCATACAACTTGATGTTATGGATTTAGTTGATAAGAGA
TACTCCATTAAATTTTTACCGGAGAAATGCTAGCCGTATTCAAGCAGATGTCGATTTTTATAAGCATCGGACATGGAACTAAATAAAAGTAAATA
AAAACCCCGATAAGAATTTTGTATTCAACGTCTTGGTTTTGGGTAACTAGATACTTCAAAAAACGATTTACTGCTTATATGAACGTATACAGGTG
CGATCTCCAGTATATTCCGTTTTTTTTTTGTGTTTGAATTTTATCTCGCTTCGGTACTCTCGTATATAGGTTCCTATCCCTTCCAAATGGCCCA
ATGTACAGCTGCGCTTGTTCAAAAAGCGAGAACTATATGAATTTCCTTTGTATAATTAATTTATTAGTAATACATTTTTGTAGTATTTTATAATT
TTTTGAATTTTTTTGTTCATACTCAGAAATCTAATATGGTTGGCTAACATATGTATAAACTTGTAAATGTTTGTATGTATGTTTATATTTTTTGT
AAATGCCATTTAGATTAGTACTTTAAATTTCAGTAATTGTTGGTTCAAAAAATTAGTTTATCCTTTTTATGTGTAAATATGTATAAAAAATCATC
ACTTGGATAAAAGCAACGTATAGGGAGTTTAGCCAACCTAAAAAAAACCCTTTCGATTAGGAATTTCCCAATCACTCTGTTTATATATAGTTCGT
TCAAGCTACAAAAAACTGTGCTCGTGACGCGTTTGGCTTACTGACAAGTTTTTGTGTGTTATATGTAAGTCTCTGTCTCATGTTGCTTTTGACCT
TGTTTTATAAGAAATATAATATCGCTATCGTAATATAGCTTAGGCAGAAAATCACTAATAAGGCAAATTAAAGTGAAGGGCACTGTGTGGGACTT
CTGAAAATACATAATGCAAACAAGCTTACTATTTAAACTTGACAACTTATATATCTCAGAGTTCGTTTAAGCCGTGCATAACTCATATACGTTGT
ATAGGCAAATTATAAGCCCTAGAATATTACTTTTTTTAGATATACTTTCACGAGAGCTTTTTCTTTCATGACGAATTGAAGTAGGTGACACTATC
TTTCACAAAGCTTATAAAATTATGCCTACACAAAGGATAAAAGAATACAAAAATAAAA
(SEQ ID NO: 181)

Exon: 1001..1105
Exon: 1249..1325
Exon: 1410..1906
Exon: 2175..2484
Exon: 2552..3286
Exon: 3353..3903
Start ATG: 1664

Transcript No. : CT6639
ACAAACCGATATATGTTTGGTCGTACCATAATCGCAGCCTATAATTAATATTTATTTTGCATTTTTGGCACCTATTTATATTTCCTAAGTGTGCC
CTGGCCCATAAAACAGATGATTCATAGCTGATGATTGAGGAAACTTACCATTTGGAATGTATAAACACATGTAAAATCAGACCGTTGGCTTTTAT
TATTTTTATATGTATACATGTGCATGAACGGACTTTAAACCATATTTAGTAGTGGAATAGAGCTATAAAAATGAGATTGAAGTCTCTAAAATACT
TTATTTAATCAGCCTTAGCACCGATAGAGCACAACGGTCACACTGTTCTGTCCCTCTTTTCCACGTGCATTTTATTGAACGAAACCACGCGTTGT
TCAGTCCAAACTTGACTTTGCTAATTTTGCCCAGAAAACCTCTAAAAGCTGTCAAAATGGCCCAAAAGAAAGCCGTCACCGTCAAAGGAAAAAAA
GCTACGAATGGAGAGGAAAAGCCTTTGGCCAAACGGGTAACCAAGTCCACAAAGGTACAGGAAGAGGAGACAGTAGTCCCCCAATCGCCTTCCAA
AAAATCCAGAAAACAGCCTGTTAAAGAAGTGCCGCAGTTCAGTGAAGAGGACGAGTCTGATGTGGAGGAGCAAAATGACGAGCAGCCAGGGGACG
ACAGCGACTTTGAGACCGAAGAGGCAGCGGGCTTAATTGACGACGAGGCTGAGGAAGATGAAGAGTACAATAGTGACGATGAGGAAGATGATGAT
GACGATGAGTTGGAGCCTGGTGAGGTTTCCAAAAGTGAAGGCGCGGATGAGGTAGATGAATCCGATGATGATGAAGAAGCGCCTGTAGAGAAGCC
AGTTTCCAAGAAATCAGAAAAAGCCAACTCTGAAAAGTCCGAAGAAAATAGAGGAATTCCAAAAGTAAAGGTTGGCAAGATTCCGCTGGGAACGC
CAAAAAACCAGATCGTTTTTGTCACAAACCTACCAAACGAGTATCTCCACAAGGACTTGGTCGCATTGTTCGCCAAGTTCGGACGACTTTCCGCT
TTGCAGCGTTTCACTAATTTGAATGGCAATAAATCAGTTCTCATTGCCTTTGATACGTCAACTGGAGCAGAAGCTGTTCTGCAGGCTAAGCCTAA
AGCGTTAACCCTTGGAGACAATGTTTTGTCTGTGTCCCAACCGAGAAATAAGGAAGAGAACAACGAACGCACGGTGGTGGTTGGCCTGATTGGAC
CTAATATTACCAAGGACGACTTAAAAACCTTTTTTGAGAAGGTAGCTCCCGTGGAGGCGGTGACTATATCCAGTAACCGCCTCATGCCCAGAGCT
TTTGTACGTTTGGCGTCGGTCGATGACATACCGAAGGCTCTTAAACTGCATAGCACTGAGCTGTTTTCTCGCTTTATAACGGTTCGTCGGATCTC
ACAAGAATCGATTTCACGTACCAGTGAACTTACCTTGGTTGTCGAAAATGTGGGCAAACACGAGTCTTACAGCTCCGACGCTCTAGAAAAGATAT
TCAAAAAATTTGGTGATGTTGAAGAAATCGACGTTGTGTGCAGCAAGGCAGTTTTAGCTTTTGTCACGTTCAAGCAGTCGGATGCCGCCACGAAG
GCTTTAGCACAACTCGACGGAAAGACTGTTAATAAGTTTGAGTGGAAGCTTCACCGATTCGAACGCAGCACCTCGGGGAGGGCCATTCTTGTGAC
GAACTTGACTTCAGATGCTACTGAAGCCGACCTGCGGAAAGTGTTTAACGATAGCGGCGAAATCGAAAGCATCATAATGTTGGGCCAAAAAGCGG
TAGTAAAGTTCAAGGACGATGAGGGTTTCTGCAAATCTTTCTTGGCTAATGAAAGCATTGTAAACAACGCCCCTATATTTATTGAGCCAAACTCT
CTGCTGAAGCATAGATTGTTAAAGAAACGCTTAGCTATTGGTCAGACCCGCGCCCCGCGGAAGTTCCAAAAGGACACTAAGCCAAACTTTGGTAA
AAAACCATTTAACAAGCGCCCGGCACAAGAGAATGGTGGTAAATCGTTTGTTAAAAGGGCAAGATTTTAGAACTTGAACACTACAAGAATTAGCT
TTAAGTTGCGTAGTACCATAAATACGGCCACAGCCCCGATAATTCCATACAACTTGATGTTATGGATTTAGTTGATAAGAGATACTCCATTAAAT
TTTTACCGGAGAAATGCTAGCCGTATTCAAGCAGATGTCGATTTTTATAAGCATCGGACATGGAACTAAATAAAAGTAAATAAAAACCCC
(SEQ ID NO: 182)

Start ATG: 437

MAQKKAVTVKGKKATNGEEKPLAKRVTKSTKVQEEETVVPQSPSKKSRKQPVKEVPQFSEEDESDVEEQNDEQPGDDSDFETEEAAGLIDDEAEE
DEEYNSDDEEDDDDDELEPGEVSKSEGADEVDESDDDEEAPVEKPVSKKSEKANSEKSEENRGIPKVKVGKIPLGTPKNQIVFVTNLPNEYLHKD
LVALFAKFGRLSALQRFTNLNGNKSVLIAFDTSTGAEAVLQAKPKALTLGDNVLSVSQPRNKEENNERTVVVGLIGPNITKDDLKTFFEKVAPVE
AVTISSNRLMPRAFVRLASVDDIPKALKLHSTELFSRFITVRRISQESISRTSELTLVVENVGKHESYSSDALEKIFKKFGDVEEIDVVCSKAVL
AFVTFKQSDAATKALAQLDGKTVNKFEWKLHRFERSTSGRAILVTNLTSDATEADLRKVFNDSGEIESIIMLGQKAVVKFKDDEGFCKSFLANES
IVNNAPIFIEPNSLLKHRLLKKRLAIGQTRAPRKFQKDTKPNFGKKPFNKRPAQENGGKSFVKRARF*
(SEQ ID NO: 183)

Name: RRM-type DNA binding protein
Classification: DNA_binding

FIGURE SHEET 93

Gene Symbol: mod
FlyBase ID: FBgn0002780

Celera Sequence No. : 142000013384692
AATGGTGCAAGAACCTCTTGAGAAATAACTAGCAAGTTTGAGGGTCGCATTAGCTAGCCCTACAGTGAAGAAATCCAATACATATACAATGATTC
ATTGTGAAAAACGGAAATCTGACAATCTCAAAAAATAAAATAATATTACTTCTATCCCTTTGGCGACGTTTCTTAATAAAAATCCCACCAAGCTC
ACCATTCGTTAGGTGGTACGAATTCAAAAATATTTATAATGAGTTTTCCATAAACAATTGTTTATTGAATAGTGTTTACTCTGTACCTCTCTGCA
CTTGCCACTTTGTTTGGGCATACATATATGCACATGTTTTGCAGAACGTAGATTTCAACAGGAATTGAAAATAAACATATTCAATCGATAGCACA
ACTGGGTAACTTTTGTTGCCTATGGCTCATTGTGTAAATATGTTCAGGCGGTTTGCCCTTAAATACCCAATTTGTGAATGCGGGAAAATTCAATT
GCTTTAATTTGTTGTTTTTAAGAACATAAAAATGGGTTCATATGTATCTGACAGATAAGAATGAACTTGAACTTCATGAATGAGTTTGTAGGAGA
ATAGAATTTTTGAATTTCATTTAAGATATTGTCTGAATGGTTGGATAAATTGAGTAATTTTTGTAGCAGAACTTTTCTGCTTTGTTCTTAGGAAA
TAGTGTTTAGTTGAGCAACTGAAGACGAATAAGAAAGAACGCGAACTCACAAGTTAAAAGAATAAAATATAAAGGCACGTGCATTAAATCAACGC
GTTTAATTGAATTCCTTTTGATTTTGGTTGCCAACTGGCTTTCCATTCAAGCAGACTTTCGCCTATCAAACAGTTTAACTTCATTCTGATATCTA
AATTCACCGAGAAAGTGTAGCAAAGACGATGACATTCAATTGAAAACGATCGATCGATTAGAATTCCAATTTGCATAGCAGTTACTGTCGGCTTG
TTCGCTTGTTTCAAGTGACACCTTTGTCGACTTTTCCCGGCAAAGACTCGAGTGGCTATCAGACAGAAGCAATCGAGAACCGCTTAATGAGAAAG
CCAAAGAAACTTGTTGAACTACAAGAAAAAGAAGCACAAGAAGGCAGAAGAACCCGGAGGGGGAGGCAAAAAACATTTTCCAGATAAGCGGCAGT
CGGAGTCGTGTGAATAAAAGCGTGTGTATTTGTTTTGTGGGTCAGCCTGTTCCAGCTAATTACCGTGAACTTGTCAGCGCACACAAAACGGCTGT
AAAATGACCAAAGTGAGGTAATAAACACGGCGAATTAACGAGAAACCCGAGTGAATAATGTCCAAACTGGTGAAGAGAATCCGCAGCATGATCAA
TCCAAGCAGCCAGCGGGATCGCGAAGATACCACCTCGGTATCCGCTTCAGAGGGCTTCATTGCTCGCAGGAAGTGCCACTCGCTGCCCCGAAGGA
GCAATAGACACTCGACCGCCCGGCGATCAAACAGTGGTCTGTGGAATCGACTGGTCACCAATGTCTTCGGACCGGAAGATTCATATGACTTTGAC
AACGAAGGCGACAGTGGTGGTGCCGTATTTTACACCGATTCGGTGAACGGTTCAAACTATGAGATATCTGCAGAAGTGAGTTAGTCGAACAAAAC
TGGATAACATTTTATAAGATTTTAAGACGATGTCGGCTGGAGGTTACAACTTTTTTTTTTTTACTATAGAACCATTATATTTTCATATTTCGGA
TACAGTTCTCTAAGTATGTTCATCTCCTTGGGTTTTAAATTCTTTGTGCCAATCATGCACTTCAAATACTGCATAGTATTTCACTATGAACTTTG
TTTGATTCAACTGCAGTTTTTGGCTTTTAATTAAATTGACTGCAGTCTATAAAGATGTCACACTTCTCCAAGAGGTGCCGCAGTATACGTTTTTT
ATTGTTTGTGTTTCAAAAACTTGAATCGAATTTAATTACGAATATGTGTATAACCTTTTTCTTATTCCCATTTTTTCTCACCCACAGGGCGAATA
CATCAAGCATCCCGTTCTGTACGAGCTCAGTCACAAATATGGTTTCACAGAGAATCTGCCGGAGAGCTGTATGTCCATACGGCTGGAGGAGATCA
AGGAGGCCATTCGGCGAGAGATCCGCAAGGAGCTGAAGATCAAAGAGGGCGCCGAGAAGCTCCGCGAGGTGGCTAAAGATCGACGATCCCTCAGC
GATGTGGCCGTTCTTGTCAAGAAGAGCAAAAGTAAACTTGCCGAGCTGAAGTCCGAGTTGCAGGAGCTCGAGAGTCAAATCCTCCTGACATCGGC
CAACACCGCCGTCAATAGTAATGGACAAGGTGAGCATCCATCAATTCCCATAGAGATTGGGTAACTTTTTCTACCGTCGTCTCGCTTTTCGTTTC
GAAAACCCACTAAAAGCCAGACATAAACTGTTGCAATTATACGAGAGCAAAAGTTTCATGCAACAAGTTTTGTGGGCAAGTGTAACGAGTCAAGT
GTATTCCCAATAAAAACGAGGGCGTGGCCAAGGGGCGGGGTCACTAACGAAGCTATAACCAAAACAAGCTTCAAGAAAAAGTTTGGACACTGCAA
TGAAGTTGAAAGATGTTCCTTTTTGTGTAGAAGATAAAGATAAGGTTGTTGGTTAATTCAATTTCAACCTGGTTGTAAAGTGTAATTCAATCAAC
CAAAATGTTTGGTATATCCTGGGCTAGTTCGGATTTCTAGGTCACGTGGTTTCCGGGCAAGCAATTTAAATAAAGGAATGAGTAAATTCTGTATA
AAACTGTTTATTATAAACAAAGATTTTGTAAAGATGTGTATTCAAAACTTTGTATTACTTGTTTCCAATGGACTAAAAGTATGAAGTAGTTTCCT
AAAATTAAGTGATATTTAGAGCAGGGACAGTTTAAAATTGCTTTATAATAAAGCTGTAATTTAGTAGCTAAAAGCTATAATTAATAATAGTTTCA
ATTATGAAACCATTGAAATTTTTTTGACCAAAATAAAAAGCCGAACAAAAATGAAAGTACTTACTTCCGAAAGAGAGTGACATCAAAACCTCAC
GAATGCTGCAATTGTTCGGGGCTTTGGGAATGGTTAAGTCCGTCTTTTACGAGTCTTTGTCACGCATTTTCTTTTACCTTTACCACATTTTTTTT
TGGCCCATCACCTAATGCTTCATGGTGGTGACAAGTGAACATTGTGCTGGGTGTTAATGATCTGATTATCGCTTTATATATGCCCTCGTATCTTT
AACAAAACACTTTGTGATAGTCTCGGCGACGGACGAAATGTTTTCTTCGTTTTCTTCGGTTTTTGTGAGCCAACCTATTGACACAACTGCCGTAA
GTGTGATACGTTTGGTTTGTTTACATTTCCGAATGGAGACAGCGTTCTGGCATTCTATATATCTGCTTCCGTGTTTGGCCAATCCCCCAACAGAA
GCATTTGCCCCACAAGAACCCCTCCAATGTGGCATTGTGTGGCGCCAGAGTCGACTTTTCATATGTCAGACGATTGACATGTTTGGCAGCTGTCG
AAGAATGCTGCACAAATGCCGATTCTCTTTGAATAAATAGCTGGCGCATATAGAACCAAACACACACATTTTTAGTTTGTGCCAAACAAATGGCC
TTTCAAAAATAAACAATGGGAGAAAAAGGGCATAAACAAGTTTTGGACATTTTTGCTGAGAAAATTTGGAACACCACTGCTGATTGATTGATTTT
TTGGTTACCGTTTATTTATTATTAAAATAATAATACAACAGCTGTTTCTAACTTGACAAGCGAAATTCTTTCTTTACGGTGGGTTTAAAAGTCCT
TATCCTAAACTGGTATTGATAGAATACTTATTGTGCTGTACTCTGTGTATCTAAATCTATGAAAGGTTTCTATCATTCAATACTTCTTACGAAAT
TCAGAATAAAATAGAATCTAATCTTTCCGATATCTTTCAGAATCGATCACTGCCTGCATTGATCCCAATGGCGGCTTCTTGGTCAGCGGTGCAGT
TGGTGGCTTGGGCGGCGGAAACACGGCTCTGGAGGGCGGCGCACCGGCCACTGCCAATGACAAAGTGCTCGCCTCGCTGGAGAAGCAGCTGCAGA
TCGAGATGAAGGTGAAGACCGGGGCGGAAAACATGATCCAGTCGCTGGGCATCGGATGCGACAAGAAGCTGCTGGCGGAAGCCCACCAGATGCTG
GCCGACTCGAAGGCCAAGATTGAGTTTTTGCGCCTGCGCATCATCAAGGTGAAACAGAACCGCGAGCAGGCCGATCGCCTCAAGGCCTCGCGCCA
GATGATCGACGAGCATGGCCAGACGATCGGCGGGAACAACAGCAGCCAGCCGCAGAGCCTGGAGACGACGCTGGAGGAGCGAATCGAGGAGCTCC
GCCATCGACTGCGAATCGAGGCAGCCGTCGTCGATGGAGCCAAGAATGTTATACGCACGCTGCAGACGGCGAATAGGGCACCGGACAAGAAGGCT
TTGCAGGAGGTGAGTTCTATCTTTTAAATCTGGGTTGATTATCTGTAGATATTTATATAGAAGTTTCGGGGAATCAAGGGTCATGTGGTAAAAGC
ATAAATCTACAAGAAATTTACAAACAATAATCTAGAAGCCTAGAATCTAAACTTTAGATAACTATATAATTTTGGATGGCAGTTGCTATGGTAGC
TTCTATTATGGAAGTTCTACTGTTCTTGGTAATTCAAAAAGAATCGGTATTTATGCTAATACTAGAGTTAATTAGAGCTGGCTGGCAGCCAGGTA
GACACATAAACCCTGCGAGTATTCCCCCGCTAAGCTGAAATCAGGTGTGCCTGCTGCCATATGGCCACACGACGTATGAATCATATTTGAATTAT
ACGTGCGTATACGTGATTTTTTCCCAACTTGTGGCAACGTCGTGTGAAACGAAACGGGAAGCGGTAAGGAGGCAATAAGCTAATTATGCGGCTGC
TTTAAATATTTTTCAGTTCGTCCGCTTTCGTTATAATTTCAAGTTTTATTTTTTTAGTTGTTTTTGTCGCTAACTGTCGTCTCATTAATTAAACG
GACGTGGAACGTCGCCATTACTAGAGTCGAAGAAAAATGATTTGGCAAGTGTGCTCAGGGCCTGCCCTAATAATTTTGGCATTAGCTTTTTAGTT
CATTTCAAATTTTTTAGTTAATGGCATTGCTGACAGAAAGATGGTCCCAAAATAAACGCAAGACGAGTATTTTTTTCAAATTTCACAATGCATTT
AACACTGAACGTACATGTGCAGGGACATAGATAAACTTTTTCTTATTTCCCAATGTCTGCGTTTCCTGTCGCGTGGCAAGCTCGCTTTTTTCCTC
GCCATGATTTATCTTTTCACCGATGCTCGTGCGGTTTTGTCTTTGGATTCAACATAGACGCATACGTACAGACACTTAGTTTCCGCTGAAGCTAC
TACAACAACATGTTGTCCGGCCTGCTGTGGCCTAAATATTCTATTTGCAGGCCCCATTTTCATAATTATTTGTTCTGCGATGCGGTTGCATCTGT
TAGATGCAGAAATAAAAAAGTCGAGAGCAGCAGTGCGTTTCATATCAATGGGAACAAGTTTTCCTTAACAAGACCTAGTGATGGAGTTCTGTATT
TTGGGATTTTCGGTTAGCAAGAACTTTCTATAGTACTGCTTTTTGTACTTTTCTTGCTGTGCATCCGAATATCGCAGAAGTTATTATACGATCTG
CTAAACAATAAACACAAAACTTCTGCCGCTGCCCTTTTGGCCATTTGGGAGCGTTTTGCTAAACATTTTTAGAACTATGCCGTACGCTGCCGTAC
ATAAGCATTGGATATATAAACCCGTCTATATGTCTGTGCCTCTGCTTAATCGGCCAAAAACGAGAAACGTATAAAACCGTCATAAGAAACGGAGC
GCAAAGTTCTCTGGCCAGCATATGGGAAAATGTGTTGTTCAATGTGCGTGTGCATGTGCGTTTCTCTAGCGAATTTTCTCAAGCAGCTTTTCCTT
GGCGTTCAGTTTGAGTTGGATCGCCGTTGGCTACGTGCGACGCCGCCTGGTCTTTTCCGATATTTTATAATTAGTTTTTAATTGCCGCGTCTTAA
CTTACGTTGCGTTTGTGTTCCTTTGTCTCTAGTGTTAAATAAAAAAAATCCACTGAATGTGGAATGAAATAATAATAACAATAATAATAATGAAA
TAATCGAAGTAAGCTCGCGAAAGGCACGCACACATGCTATATAAGTGGAATTCACTGGCTGAGCTTGTTATTACCTATTTGACATTACGCATACG

FIGURE SHEET 94

CAGCGTGTGCTGCAAGTTCTATGCGGTTATCCACCCGAAATTGCGTAATTCTCAGCTCTGCACTCAGTTTCTCTGAATTCTTTTTGGGGTCATCT
TGCAATTTTGGCGTAACGAAAAATAAATCTTGTTATAAATAAAATCACATAAATTTAGAAACACAAATTTTACAAAAGCTAAGAAAAACCGAAAG
TGTTTTCGTTCCGCCCCATCCATTTGCTAACCCCCGCGACTATAGTGTGTGTGCGTTTTTGTCGAATGAAGCTAAAAATAGTGAAAACAAAAAAG
CCAAATTAATATAGTTCAAACTGCCTGTAACGAATTTTACGGTTTATTAAAACAAAAAATAAACTATTTAACTAAAAAGTGGTGTACAAAATACA
GGACGATAAGCAAAAGTAATTGGATTTGAAAAAAAAACCGAGAAATTCAGATCATTATAAACACTAAAAGAATTGCTTGAATTTGCCTAAATTGT
ATACAATTCAAAGGAAAAGTTTTAAAAATTATAAACAATGTATGGGGATGTTACCACAAATTGTTGATATAAAATTACCTTTAAACAGTTGGAAT
TCAACATTTAAGCCGTTAATATATAGAATTTATTCAATGTTTGGTCGACAATAAGAACTATCAAAGCGGCTTCTCGATATTTTTAGCAGGAATAT
AAATTTCGTGTGTGACGTATATATATATATAAAAATATATATGTAGTATATAGTGCGTGAGTGTATTTATGTGAATATATCGATGGCACCATAAC
CACAGCCAAAATGTGTTTATGCCACGACCGCAAAACAAGTGTTTAGGGAGTCATGAGCACGCCCACGCCCACTTCGGGGGCGGTTCAGGGCCAGG
AGGTTCCACTGCCCCATGAACTGACCGCCGAGTGGACCGTGCGAGCACATCTAACTTTTGCCCGAGCTGGCGAAACGGTGCAAAAGGAGTTCAGT
GCTCCGGAGACTGTGCATCCGATGCGCGTGGTCTACAAGTGGTGTACGCCCTGCGAGGAACCAGAAACAGAACAGGATGTCGACAAGGCAAGTTG
TGACGGGAAAATCTTCCAACCTTTATTTATATCCTTAAAATCCTCTACAGACAGCGGCTACTGCGGGAACCAGCTTCCGTTCCACAAACTCCTCG
GCCACCACCAATGCGGACTCGGCATTTGGCAGCCCACATGCTTCGAGGGCTCTTAACAAACCACCTGAGCCCACTGATTGTGCTGCTCCTCTGGG
AGCCACTGCCCAAGTGTGTGGAACCCGCTGCCGGAGCACCTGCAACATTATGGTGTCCGCGGTGGCAGATTTCTTGCCTCAAGAGGCGGGAACCG
GGTCAGTGAATGAGCCCTTTGTTTATCACAGCAAAGTGCGAGCACAGCAGCTAAAGGATGCCTTCTCCCAGACAAGCGACACGGAGGAGCAGCCA
GCCAGGAGACGTCCAGCTTACGAGCAACGAAGGGCCACCACCGAAGCACTGATGAATTTTGCCAGCAAGCGACAAGCGGAGGAGGCTAACACCTA
TGCGGTGCGGTTTCAAATTCATAATTGATTTTTAACTTTCTAACTAATTGCAATTTTCAGCCAACCTATTCGCCCACGCCCACAACACCTTCGTC
TACATTTAAGTCGGCATCGATGTCGAGAATTCCACCGCTAGCTGGCAATATAAGCCAAGGAACAGCTCCTAAAATACCCAATTTGGGCGAGAAGA
AACACCGCACTGTTCACATCGATGTCTACTGCACTGGTTCAGAGGGTGATGAGGAGGAGGAAGCCGATGATGAGAGGCATGCAGATGAGGAGCCC
TCTAGCTCCTCCGACTCCGAGCTGGCTGGTAGCAAGCGATACGAACTGGACTCGAATTCCACCCCTCAAACCGTGCTGGACAATGAGCAGATGCT
ATTGCGCCATCAAAGAATCTCTGGGGGAGCTATGCCCAGGCGTTTGGCTCAGAATCATGGAAAAACAAAGTGGGGAACCAGCAGCAGCAAGGCA
ATCTAAATTTGGGGCATGCCATTACAAAGTGCAGCACAGCCGAGGAAGTGTGCGAGTCCAAGCAATTGCTTTTCCGCAAACACATTGGTGATCAG
CGGGCGGCCAAGTTGGCCAATCTACGTCAGAAATACATGCGCCAGCCCAGCGATGAGACCATCAGCAGCACATACCCGAACTCCTCGAGGTCAAC
GATGCCAAGGGATGCCACCTGCAGCAGCATTTCCAGTGCCGTGGGAGGAACAGATTGTGTGGATTCATCGTGGAAGGATACAGACGATCTAGATA
CACCAATAGCATCTTTTGGCTTAACCAAATCCGATAGCTTTGACTATGAAAACTCGCTTGATCGCCTGCGGATAAGCCAGATGGAGCGCCTATGG
TCCCGTCAGCACTCATTGGACCAGGGTCACGCACAAACCCATCTGGGGGGAGCACCATCCCCTCATGCTCTGCAGACAATCACGGAGGTGCAGTC
GCAACGAAGTTCCTTCCAGCGAAACGATACCATACCCTCGGAGTCGGATGGCTTCTCCGATACCAATGGATTCAATACCTATCCGGGAAGGCAGT
CGCAATTGCAGCAGATCTCGCACTTTCCTCGTAACCGGCCTGGTTTTCTGCAGTTCTTTGGACCCTCCGGTGGTCCCGGCGTGGTAGCACAACCC
ACTCCGCCAGCCACTGCACCTGTTCAACCCGCTGGGTCCGCTACTACGGATCCGTTTCGTATGCTCCACCCGAGTTTTCGATGGAAGAGCGAAGC
CCGCGATAATCTGAGCGTCCAGGTTGCTTCCGGATCACCCTCTTCCGAGCGCAGTTCGCCACAACTCTTGTCTGCTGCGACCACCGTGGTGCGTT
GTGGCAGTGAGGCGCCGCCAAGCACCACCTCTGCTAGTACTTTTGGAACTACAGTGACGCCTTCGCCAATTGCAGTGCGACGTTTTGAAATCTCA
CGCGACAGTCCAAGTCTTGCAAGTGAAGCATCCACTTCCGTTTCCGGGTACACCCACGAGCATTTGGAGAAGGCGCGTCGCTTCGGCAACGTTGT
GGCCATGAGAAAACCCGGCCATCATGTGGGACCCACCAAGAATCCGAATTGTCAATGCGAAAGCTGTCAGCGTTGGCTGGCCGAGAGGTTTCAGC
TGCGCGGAAGAGCCTTCTCACTAGGCGAGAAGCCCTTATTAAGACGTCCACAGCTATAAAATCATACCGGGCTTACTTTTCTTTGTCTTAGGCTT
GCATTTAACACACTGCTTTTCAGATTGATACGCTCCCTATTAACCCAACACCCAAAACCGAACCTAAATCCAACTTTATTTCCGATTAGTTGTAA
GCCATGTAAGCGAATGTTCCTCACGCAAAACACAATTTGTGCGCTGAATCAATTTAATGTTGTAATAAAATAAAGCAATAGTTTTAACTAGAAAT
GTATTTATTTATTTCGGCGAATGAAGAAAGAACTTATTTTAAATTATGTATGTTTTATAGGGTAAAAAATTATTTGGTATTGTGCCAGATGAAAT
GAAATTATTATTAATTCGTTATATTTTGAAACAGGCCCATGGACGTTTGTCGGAATCGTCGCGAAAACTAGATCTCTTGCGCTACTCCTTGGATT
TACGACGCCAGGAGCTGCCCGCCGATTCGCCCGCCGCCCAGCAATTAAAAACGGAGCTGCAGATCGTCCAGCTATCGACCTCCCCAGCTCCGGTC
ACCTACACGTCACTGCAGTCCGGACAAGCGGGCATACTCGGCGGAAAGCCGTACCAGTCGGTATCCTCGCTTGGACGCTGTGCCAGTGTCACCGG
AAAACTGGAGGTTCGCTTGCTGGGCTGTCAAGATTTGCTGGAAGATGTGCCCGGTAGATCGAGGAGGGACAAGGACAACAACTCAAGTCCGGGTG
ATTTACGAAGCTTCGTCAAGGGCGTCACGTCGCGCAGCAGTTCAAAGAGCTATTCGGTAAAGGATGAGACGTCCATTGAGATCATGGCGGTCATC
AAGCTGGACAATATCACCGTTGGCCAGACATCGTGGAAGCAATGCTCGCAGCAGGCCTGGGATCAGCGCTTCTCCATCGATCTAGACCGGTCGCG
CGAACTGGAGATTGGAGTTTACTGGCGCGACTGGCGATCCCTGTGCGCCGTAAAGGTGCTGCGCCTTGAAGAGTTCATCGACGATGTACGACATG
GCATGGCATTGCAGCTGGAGCCACAAGGTCTGCTATTTGCGGAGGTCAAGTTCTTGAACCCCATGATTTCACAGAAGCCAAAGCTGAGGCGCCAG
CGTATGATCTTCAACAGGCAGCAAGCGAAGAACATCTCGCGGGCCAAGCAGATGAACATTAATGTGGCCACATGGGGCCGCCTGCTTAAGCGGAA
TGCTCCTAACCATGTGCACATGGGATCGGCAGGATCAGGATCTTCTCTAACCGGTAGCTCGCCTATGGTGGTTGGTGGGTCTCGCGACTCTGAGT
CTCCGATTTCGAGGACTCCCTCATCCGACGCACTGGTGGAACCGGAGCCCTACACGCCCGGAGAGCAGGCACAGAACTTGGAATTCGATCCCGAT
GCAGGAATTAATGAACACGTGGAGACGCCAGGTGAATACCCGGATCCGGCGGCCAGTGGTCTGAGCGGAATGCGACCCCTGTCCATGCACATGCA
GGGAATTAGTGTGCTGCCCCCGGAATCGCCACCCGTGGCCACCGGAGCAGCTGGTCGGCCCAATACGCTCAGCTTACAGATGCCGGGTGCCAGTA
AAGGACAGGTGATCCAAGGCGGACGGACTGCGGCGCCTACAACGGCGCCACCGCCACCACCTGTGCTCAAGGCGACATCCACCACTCCGATATTG
GATCAGGAGGTAAGTTTGCTAATTTATTTTACAATGCGATCCGTGTACAGTTCAGTATTTGACCGACCCTGTATAAAGATCTGCGTATGTACTAC
TTAGCTGTGTACCCGTAGCTGGTTTGATCGTTGTGCCTGCCACTGCTCCTCCGCCCACTCTCTCATGTACTTATTCACCACCCACCCACTTATGC
ACACACAAGCACTCAATCTGTACAGTCATCACATTATGAAATTTTGGTGTTGGTTTTGCATTAAGTATCTCTCTAATCTGTACATTTGGAACGGT
AGCCGCACTTCATACAGAATCATGAATGTTCGCATAATTGGCAGAAAGTTTTACGAACTTGAGTTTGAAATACGAGATAGTTAAAAAGTAAATCT
AATGAAATATGAAATATTAAGAAAAAATTTCGAATAACTTTAAATCAGATAAATTATTTGACTTATCTTCTTAAATTTTCGAAATCTATGAAAAG
TGAACTTATTTTATTTCAAAATTCAAAGTAGTTTATGCCTTCTCTGCCTTTGAGTTTTCACATAATTCATCGTCATTATCGTTCACTCTTTCTCT
TTATCCTCCACTCGCTTTCTTCAAGAAAAGTCTTTCCCTTCCTTGCTTTGATAATCCTATCGCCTTCTTTATTCATCTGCCCATATTCTTCTTTT
TGTGGCCCATCGTCATCATGTTCTCTATCTATATCTCTCTCTCTCTGTATCTGTGTGTTTGTGTGCCCGTCTCGGTTTCCGTTTTCCGTTCCGTA
TCGTCATGATTTCGTTAATCGCCGACAGCTGCAGGATGCCCTGCACGAATTCGATTTCCTGTCGGACCTGGACTCACGTCCCACCACGCTGCGTC
GCCTGCTGAAGGAGCAGAAGATGGCGCTGGATGCCGGCGCGCTGGAGAATCTGCTGCTGCAGCAGCAACAGACTGAGCAGCAGGCACTGCAGCAG
CGCCAGCGCCAGGAGCAGCTGCGTCTGCAGCAGTTTCAGGAGGCGCAGCGCCAGGCGATCCTGGACCTGTGCGTGAAACAGAGAGAGCCCGCGGA
GCAGACATCACCCACCCTTGCCAACCAAACGCCGACGTTCCCACCGCTTGCCAGCAATCAGATCATGCCAAGCTTAAATGCCCGCCCTTGCCAAA
GCCAAAGCCCAAACCACAACGAATTTCAGTTGCAGCCGCAGCCACCACATCCCGCCCAGAAACCGACGAATCCCGAACCACCGTCCGCTGTGGAA
CAGCAGCTGCACCGTCCGGTCCTAATCCTGCCGCCCGTGGTGCTCCTGGGTGGTCGGGAGGAGGACCGTTCGGTGCCACCATCGCCACTAGTCGA
GTATCCCGAGGACGACGACGAGTATCTGTATCGTGGTAGCAACGAAAACCTGGGCACCAGGCTGCACTCCAGCCACAGTTCCAGTGCCGGCGATC
GTTTCTGTGTGGAGGTTAGGAGGTTTTTCATTTCCTGGTTTGGTTTCCGGTTTAATTTCTGTTTCTCCAATTTCTGATTTATTTTCTTTTTATGT
TTTAATTTCACTAACCTTATTTTCCTTTTGATTTCTTACATGTTTGTTTTGTTTTTATTACGCGTTGGGTTTTACCTGTTTCTTCTTTAAATGTG
TGTATGTTTTTGGTTTGGCTCTGGCCAAAAAAAAAAGAAAAACATTTGAAGCCCCAAAAATTGTGTATAAACATTTGACTCATAAACACACACAT
TCGCACTGTAATCAATGAGCGTTCACAAGCATCCCAAAAAACTAACCTAGTCGTAGTGGAACTAACTAAAAGTTTAGCTATGAATGTGACTAACC
ATTTAATTAACAGTGTTTAATAGTTTGATGTAGTTAAACATAGTTCCTATTGAAAGGAAGAGCTTTAAAATGGCAATCTTAATGGCACAGATGTA

FIGURE SHEET 95

AGCTGCACAGCTTAATTTAACGTAAATATAGCGTTTTTAAATGTTTAAATAACATATTTTCCAATAATAAGCAACTTGAGAGCATAAGAATTTGT
TTTAGACTTACAATTTCCCACTTATTTGAAAAGGAACCAATATGATCGACGCGAAATAAAAGCTAGAAGTGACAATTTTAAACTCTTTAAATAGA
CGCGCTTCTGGCGAATGACAGCGAAAAGATCAGAGGAAAGTAAAGGGGATATGTCTTGGGAGAATTGGGTCTTTAGGAGGCACCCGAAAGTGCGC
CACTTCACGTGCCAATGTTCGGGAAATGTTTATTTTTTCTCACCCACGCCCACCTTTCGTTTTGCCCTCCCTCTCACGTTGCAACGTCAGTGTT
CCCCATTTCCATTTCCATTTTCATTTTCATCGAAGATGTTTGTCCCTGTGTGTTCGCTTACCTTTGTATCTATGTGTGTCCCAGCTGTGTACTCA
TCGTTATGTGCGCTGTTGTCACATTTTCCTTTCGGCTGGTCATTTTTAGACCCAAAACAACGACGCAAATGCTTGGCCTCTGGTCATGACTTTGG
CACTTGTTCGCCTTCAGTTGGTCGGCGCGGTGTTGGCCATCCCGCCTAAGTGTCGTATCCGTATCGGTATCGATCGCAATGTAGAAAAGTTATGA
TTGTGCCAACCTTCCATGCGCTCGGCCAAGTCTTGAGGCAGATGTTTGCGGTCCAACTCCAACAGCAGCAGCAGCGCACTCATAATCAGCTCCAT
TACCTCGATTTGTCGCCCGCGCGAACCATCAACCAACTGTTAGTGTGTCCATGCGCATCCAATCCTGTACCTCCTGCTGTATGTGTGTTTCTTGG
GTTCAATCAAATCCCCGATCAATCTACCATACTATGAAGAACCATCCTCTTGCAGGCCCGTATTAGTCTTGTACATATAACCCTCGAACCGATCA
ATGCCAGCCGGACGACCAGTTGCCTGATCGAGGAGGTAGCCGAGCCGGATTCACAGCCGGAGATTAAGCCGGTGGCAGAAGCGCAGTCTGCCAAA
GTATCCGAGGCTTGTGTCGAAAGTATTCTCCCCGAGACAGTTGAAAAGTTAGAAACAGCAGACCAGGTCCAGCAGGTAATCGCCAGGGATTTAAG
TGAATGGATTCACCAAGCTCTCAAGTTGTAGCCACTAATAAATGTACACCTAACGCTACTTTCCTTGATGACTAAAGTTTATCTTTCTGTGCACT
CTAGGTTATACCACAGTTGGGGAAGCTTTACGTGGGCAGTAGCCAGCAGCAGTATGCGCAGCAGTCATCGCCCATCATCCAGGAGCCAGCTACTC
CTACTATTTACGGAAACAGCGCCGCAGCCGGAGCGCCGCAGTTCCCGCAGCCCGCCCAAAGGCAAGAGAAGCAGCCTCCGCAGCAGCAGCCCATC
TACGCTAACCAGTATGAGCTGAATGTGGCCAAGGCGGCAGCTGCAGCATCTGTTTACTCACCCAGCTCCTCCACCACCAGCAACTCCAATCAACA
GCAGCAGCAGCAGCGCCGGAATGTGGCCCGTGGACTGCAGTATCGTGAATCTGGAGGACTCGAGACTGGACGTGCTGGCAAGCAGCCACCCAATG
CGGGCATGTTGTCAATGGACAACTTCCGTTTGCTAAGCGTTCTTGGTCGCGGCCACTTTGGCAAGGTGATTCTGTCCCAATTGCGAAGCAACAAC
CAGTACTACGCTATTAAGGCACTGAAGAAGGGAGACATCATTGCCCGCGACGAAGTGGAGTCCCTGCTTAGCGAAAAGCGCATCTTCGAGGTGGC
CAACGCCATGCGCCATCCGTTCTTAGTTAACTTGTATTCGTGCTTCCAGACTGAGGTAAGTAGAGATAAGCTGAGGAGTTAGAAATTGAATAATA
ATCTGTTTACATTTTCATCGTGCTAGCAACACGTATGCTTTGTGATGGAATACGCTGCTGGCGGAGATTTGATGATGCACATCCACACGGACGTG
TTCCTAGAGCCGAGAGCCGTTTCTACGCCGCTTGTGTGGTTCTGGGCCTGCAGTACCTGCACGAGAACAAGATCATCTACCGGGACCTGAAGCT
GGACAATTTGCTTTTGGACACGGAAGGATATGTGAAAATTGCGGACTTTGGTTTGTGCAAGGAGGGCATGGGCTTTGGTGATCGCACGGGCACTT
TCTGTGGTACGCCCGAGTTTCTGGCACCGGAAGTGCTCACGGAAACTTCCTACACACGAGCTGTGGATTGGTGGGGCTTGGGTGTGTTGATCTTT
GAGATGTTGGTTGGTGAGGTATGTCGAATGGAACAAGCTTTAAAAATGCAGTTCATAATCATAATAATTAATGTTTACAGTCCCCATTCCCTGGT
GACGATGAGGAGGAAGTATTCGATTCAATTGTCAACGATGAGGTGCGCTATCCGCGCTTCCTATCGCTGGAGGCCATAGCCGTGATGCGTAGGGT
AAGCTGATTGATTGCAAAAGTAACTATTCGAAAGGAGAACTAATTTACAAATTTTTTTGGCAGCTTTTGCGCAAGAATCCAGAGAGACGTCTGGG
ATCTTCGGAACGGGATGCGGAGGATGTTAAGAAACAGGCATTCTTCCGGTCAATTGTGTGGGATGACCTGCTCCTGCGAAAGGTTAAACCACCAT
TTGTGCCGACAATTGTAAGTTAACTTGCACACTTCATTTATAAGGTTGCATATTTTAACATTGTTTTTAACTGCCTTGCAGAACCACTTGGAGGA
TGTGTCAAACTTTGACGAGGAGTTCACGTCGGAGAAGGCTCAGCTTACGCCACCGAAGGAGCCGCGACACTTGACCGAGGAGGAGCAGTTGCTCT
TCCAGGACTTTTCATACACGGCCGAATGGTGTTAGAAGCTCATTCTTAGTTCAAGGATTTACTAACGGGCCTAGCCCGATCCTTATAGCCTATGG
CCTGCTTTTGCTTTTACTTGTGTACGAAATTGGTTTCGAGTAATTTTACTTGGCTTAGTAGTCGATGTGAGTTCAATATTTATACATGAAGACAG
CATGATAATACAGATACAGGACATATATATTTATAAACTATATCTATATAGAAAATACATCTACTAACGAGAGAACTTTTGATTGTTGCTCACTG
GCCGAGAGACCAACACAAACCAAAATACCTAGTTGTCCATGTTGTGGAAAAGCAAGCATTTGTCAATCATCCATGCAACCGGTTTAGCATACAGT
GTACCCAGAAATCATCCCACATTGTCGTTGCATTGTACAGCATATAGAGTTGTTTCCTTTTCCAAACACGAGAACGCATTGAATAGTCTGACAAA
CCCTAGGAAAGCCTTATACGCCAAGTTGTAGTTTTGGAAACCGTTTTTAAGACCGGATACAAATAGATTTTATAGATGAGAAGTGTATGTCTAC
ACCCCAGAGCAGTCATTGCAACCTATTTTCATAATCAACATACAAGAACAAAGATATATTTTATACATATATTGCATGCACATCCCAGGAATCGT
CTTGCTAAACGAGCTCATCTTCTATACGACATACAAACATACATATTTATCTAGTAAAGTGAGAGAAAGTGAAATATTTACAGTTTTAACATGTA
AGCCCTGTAAATTGCCTTTTGCCGCGTTTTATCAACTCCCCAGCCCATTGCCCGAGTTGTGTTATAATTTAAACATATTTTTTACGTCATATACA
CACGCAAACATTTGTTATTTATTATTATTATAACTATTATACAAGAAAACTGTATTGCTTTGAGCATTTTTATTCGACGCTAGATCGATGATTGT
AAACAATTTGTTTTGCATGCGCGGTGTGCTTTAAACCAGATATGAGGATCAGAAAACAAATAACCGCTCGACGGGATAGAATTTGGAAATTCCGT
TGATGGATGGCATGCAATCGGATTGTTGTACTTCTAAGATCTATGTTGTATTTAATGTAACTTTTAGTTCGATTTAAGCTTGTAATAATCGATTA
TTGAAACGTAGTCTAAGCTATCATTATGTGAAGATAATTATTGATAATTACAATTATGATAACGATTTTGCACACCTCATGCGAATCGAAACGAG
TATAAACAATGCAGATCTTCTATTGTCATTTTTATTATGATTATGCTCACAACTTGCGGCTATAATCATCGATTTAATTTTAAATCTGTAAAGTC
GGATTGGTGCACATCCAATCACATTGTTTAGTTTCAAGTTGCGACTGTAATTTATATTTATGATATGATTTTAAATAAATGTATCTATCGCTATT
ATTTAACTGCTGTTTTTGTCGACTGGTTTTCGCTGAGACCTTCGCTCATTTGGTAATACAAAATATTGGCGGTATTGTCCACAACGGCTAAAAAT
ATGTTGCTGATAGGGAATAAAGTGGTTAAAAACATAAATATTATTTTCATAACATTTAATACGCACCGTTTTTTAAGCT
(SEQ ID NO: 184)

Exon: 1001..1595
Exon: 1988..2309
Exon: 3936..4474
Exon: 9820..11124
Exon: 14255..14875
Exon: 14942..15313
Exon: 15376..15483
Exon: 15549..15689
Exon: 15757..16464
Start ATG: 1293

Transcript No. : CT6660
AGTGGCTATCAGACAGAAGCAATCGAGAACCGCTTAATGAGAAAGCCAAAGAAACTTGTTGAACTACAAGAAAAAGAAGCACAAGAAGGCAGAAG
AACCCGGAGGGGGAGGCAAAAAACATTTTCCAGATAAGCGGCAGTCGGAGTCGTGTGAATAAAAGCGTGTGTATTTGTTTTGTGGGTCAGCCTGT
TCCAGCTAATTACCGTGAACTTGTCAGCGCACACAAAACGGCTGTAAAATGACCAAAGTGAGGTAATAAACACGGCGAATTAACGAGAAACCCGA
GTGAATAATGTCCAAACTGGTGAAGAGAATCCGCAGCATGATCAATCCAAGCAGCCAGCGGGATCGCGAAGATACCACCTCGGTATCCGCTTCAG
AGGGCTTCATTGCTCGCAGGAAGTGCCACTCGCTGCCCCGAAGGAGCAATAGACACTCGACCGCCCGGCGATCAAACAGTGGTCTGTGGAATCGA
CTGGTCACCAATGTCTTCGGACCGGAAGATTCATATGACTTTGACAACGAAGGCGACAGTGGTGGTGCCGTATTTTACACCGATTCGGTGAACGG
TTCAAACTATGAGATATCTGCAGAAGGCGAATACATCAAGCATCCCGTTCTGTACGAGCTCAGTCACAAATATGGTTTCACAGAGAATCTGCCGG
AGAGCTGTATGTCCATACGGCTGGAGGAGATCAAGGAGGCCATTCGGCGAGAGATCCGCAAGGAGCTGAAGATCAAAGAGGGCGCCGAGAAGCTC
CGCGAGGTGGCTAAAGATCGACGATCCCTCAGCGATGTGGCCGTTCTTGTCAAGAAGAGCAAAAGTAAACTTGCCGAGCTGAAGTCCGAGTTGCA
GGAGCTCGAGAGTCAAATCCTCCTGACATCGGCCAACACCGCCGTCAATAGTAATGGACAAGAATCGATCACTGCCTGCATTGATCCCAATGGCG

FIGURE SHEET 96

GCTTCTTGGTCAGCGGTGCAGTTGGTGGCTTGGGCGGCGGAAACACGGCTCTGGAGGGCGGCGCACCGGCCACTGCCAATGACAAAGTGCTCGCC
TCGCTGGAGAAGCAGCTGCAGATCGAGATGAAGGTGAAGACCGGGGCGGAAAACATGATCCAGTCGCTGGGCATCGGATGCGACAAGAAGCTGCT
GGCGGAAGCCCACCAGATGCTGGCCGACTCGAAGGCCAAGATTGAGTTTTTGCGCCTGCGCATCATCAAGGTGAAACAGAACCGCGAGCAGGCCG
ATCGCCTCAAGGCCTCGCGCCAGATGATCGACGAGCATGGCCAGACGATCGGCGGGAACAACAGCAGCCAGCCGCAGAGCCTGGAGACGACGCTG
GAGGAGCGAATCGAGGAGCTCCGCCATCGACTGCGAATCGAGGCAGCCGTCGTCGATGGAGCCAAGAATGTTATACGCACGCTGCAGACGGCGAA
TAGGGCACCGGACAAGAAGGCTTTGCAGGAGGCCCATGGACGTTTGTCGGAATCGTCGCGAAAACTAGATCTCTTGCGCTACTCCTTGGATTTAC
GACGCCAGGAGCTGCCCGCCGATTCGCCCGCCGCCCAGCAATTAAAAACGGAGCTGCAGATCGTCCAGCTATCGACCTCCCCAGCTCCGGTCACC
TACACGTCACTGCAGTCCGGACAAGCGGGCATACTCGGCGGAAAGCCGTACCAGTCGGTATCCTCGCTTGGACGCTGTGCCAGTGTCACCGGAAA
ACTGGAGGTTCGCTTGCTGGGCTGTCAAGATTTGCTGGAAGATGTGCCCGGTAGATCGAGGAGGGACAAGGACAACAACTCAAGTCCGGGTGATT
TACGAAGCTTCGTCAAGGGCGTCACGTCGCGCAGCAGTTCAAAGAGCTATTCGGTAAAGGATGAGACGTCCATTGAGATCATGGCGGTCATCAAG
CTGGACAATATCACCGTTGGCCAGACATCGTGGAAGCAATGCTCGCAGCAGGCCTGGGATCAGCGCTTCTCCATCGATCTAGACCGGTCGCGCGA
ACTGGAGATTGGAGTTTACTGGCGCGACTGGCGATCCCTGTGCGCCGTAAAGGTGCTGCGCCTTGAAGAGTTCATCGACGATGTACGACATGGCA
TGGCATTGCAGCTGGAGCCACAAGGTCTGCTATTTGCGGAGGTCAAGTTCTTGAACCCCATGATTTCACAGAAGCCAAAGCTGAGGCGCCAGCGT
ATGATCTTCAACAGGCAGCAAGCGAAGAACATCTCGCGGGCCAAGCAGATGAACATTAATGTGGCCACATGGGGCCGCCTGCTTAAGCGGAATGC
TCCTAACCATGTGCACATGGGATCGGCAGGATCAGGATCTTCTCTAACCGGTAGCTCGCCTATGGTGGTTGGTGGGTCTCGCGACTCTGAGTCTC
CGATTTCGAGGACTCCCTCATCCGACGCACTGGTGGAACCGGAGCCCTACACGCCCGGAGAGCAGGCACAGAACTTGGAATTCGATCCCGATGCA
GGAATTAATGAACACGTGGAGACGCCAGGTGAATACCCGGATCCGGCGGCCAGTGGTCTGAGCGGAATGCGACCCCTGTCCATGCACATGCAGGG
AATTAGTGTGCTGCCCCCGGAATCGCCACCCGTGGCCACCGGAGCAGCTGGTCGGCCCAATACGCTCAGCTTACAGATGCCGGGTGCCAGTAAAG
GACAGGTGATCCAAGGCGGACGGACTGCGGCGCCTACAACGGCGCCACCGCCACCACCTGTGCTCAAGGCGACATCCACCACTCCGATATTGGAT
CAGGAGGTTATACCACAGTTGGGGAAGCTTTACGTGGGCAGTAGCCAGCAGCAGTATGCGCAGCAGTCATCGCCCATCATCCAGGAGCCAGCTAC
TCCTACTATTTACGGAAACAGCGCCGCAGCCGGAGCGCCGCAGTTCCCGCAGCCCGCCCAAAGGCAAGAGAAGCAGCCTCCGCAGCAGCAGCCCA
TCTACGCTAACCAGTATGAGCTGAATGTGGCCAAGGCGGCAGCTGCAGCATCTGTTTACTCACCCAGCTCCTCCACCACCAGCAACTCCAATCAA
CAGCAGCAGCAGCAGCGCCGGAATGTGGCCCGTGGACTGCAGTATCGTGAATCTGGAGGACTCGAGACTGGACGTGCTGGCAAGCAGCCACCCAA
TGCGGGCATGTTGTCAATGGACAACTTCCGTTTGCTAAGCGTTCTTGGTCGCGGCCACTTTGGCAAGGTGATTCTGTCCCAATTGCGAAGCAACA
ACCAGTACTACGCTATTAAGGCACTGAAGAAGGGAGACATCATTGCCCGCGACGAAGTGGAGTCCCTGCTTAGCGAAAAGCGCATCTTCGAGGTG
GCCAACGCCATGCGCCATCCGTTCTTAGTTAACTTGTATTCGTGCTTCCAGACTGAGCAACACGTATGCTTTGTGATGGAATACGCTGCTGGCGG
AGATTTGATGATGCACATCCACACGGACGTGTTCCTAGAGCCGAGAGCCGTTTTCTACGCCGCTTGTGTGGTTCTGGGCCTGCAGTACCTGCACG
AGAACAAGATCATCTACCGGGACCTGAAGCTGGACAATTTGCTTTTGGACACGGAAGGATATGTGAAAATTGCGGACTTTGGTTTGTGCAAGGAG
GGCATGGGCTTTGGTGATCGCACGGGCACTTTCTGTGGTACGCCCGAGTTTCTGGCACCGGAAGTGCTCACGGAAACTTCCTACACACGAGCTGT
GGATTGGTGGGGCTTGGGTGTGTTGATCTTTGAGATGTTGGTTGGTGAGTCCCCATTCCCTGGTGACGATGAGGAGGAAGTATTCGATTCAATTG
TCAACGATGAGGTGCGCTATCCGCGCTTCCTATCGCTGGAGGCCATAGCCGTGATGCGTAGGCTTTTGCGCAAGAATCCAGAGAGACGTCTGGGA
TCTTCGGAACGGGATGCGGAGGATGTTAAGAAACAGGCATTCTTCCGGTCAATTGTGTGGGATGACCTGCTCCTGCGAAAGGTTAAACCACCATT
TGTGCCGACAATTAACCACTTGGAGGATGTGTCAAACTTTGACGAGGAGTTCACGTCGGAGAAGGCTCAGCTTACGCCACCGAAGGAGCCGCGAC
ACTTGACCGAGGAGGAGCAGTTGCTCTTCCAGGACTTTTCATACACGGCCGAATGGTGTTAGAAGCTCATTCTTAGTTCAAGGATTTACTAACGG
GCCTAGCCCGATCCTTATAGCCTATGGCCTGCTTTTGCTTTTACTTGTGTACGAAATTGGTTTCGAGTAATTTTACTTGGCTTAGTAGTCGATGT
GAGTTCAATATTTATACATGAAGACAGCATGATAATACAGATACAGGACATATATATTTATAAACTATATCTATATAGAAAATACATCTACTAAC
GAGAGAACTTTTGATTGTTGCTCACTGGCCGAGAGACCAACACAAACCAAAATACCTAGTTGTCCATGTTGTGGAAAAGCAAGCATTTGTCAATC
ATCCATGCAACCGGTTTAGCATACAGTGTACCCAGAAATCATCCCACATTGTCGTTGCATTGTACAGCATATAGAGTTGTTTCCTTTTCCAAACA
CGAGAACGCATTGAATAGTCTGACAAACCCTAGGAAAGCCTTATACGCCAAGTTGTAGTTTTGGAAACCGTTTTTTAAGACCGGATACAAATAGA
TTTTATAGATGAGAAGTGTATGTCTACACCCCAGAGCAGTCATTGCAACCTATTTT
(SEQ ID NO: 185)

Start ATG: 293

MSKLVKRIRSMINPSSQRDREDTTSVSASEGFIARRKCHSLPRRSNRHSTARRSNSGLWNRLVTNVFGPEDSYDFDNEGDSGGAVFYTDSVNGSN
YEISAEGEYIKHPVLYELSHKYGFTENLPESCMSIRLEEIKEAIRREIRKELKIKEGAEKLREVAKDRRSLSDVAVLVKKSKSKLAELKSELQEL
ESQILLTSANTAVNSNGQESITACIDPNGGFLVSGAVGGLGGGNTALEGGAPATANDKVLASLEKQLQIEMKVKTGAENMIQSLGIGCDKKLLAE
AHQMLADSKAKIEFLRLRIIKVKQNREQADRLKASRQMIDEHGQTIGGNNSSQPQSLETTLEERIEELRHRLRIEAAVVDGAKNVIRTLQTANRA
PDKKALQEAHGRLSESSRKLDLLRYSLDLRRQELPADSPAAQQLKTELQIVQLSTSPAPVTYTSLQSGQAGILGGKPYQSVSSLGRCASVTGKLE
VRLLGCQDLLEDVPGRSRRDKDNNSSPGDLRSFVKGVTSRSSSKSYSVKDETSIEIMAVIKLDNITVGQTSWKQCSQQAWDQRFSIDLDRSRELE
IGVYWRDWRSLCAVKVLRLEEFIDDVRHGMALQLEPQGLLFAEVKFLNPMISQKPKLRRQRMIFNRQQAKNISRAKQMNINVATWGRLLKRNAPN
HVHMGSAGSGSSLTGSSPMVVGGSRDSESPISRTPSSDALVEPEPYTPGEQAQNLEFDPDAGINEHVETPGEYPDPAASGLSGMRPLSMHMQGIS
VLPPESPPVATGAAGRPNTLSLQMPGASKGQVIQGGRTAAPTTAPPPPPVLKATSTTPILDQEVIPQLGKLYVGSSQQQYAQQSSPIIQEPATPT
IYGNSAAAGAPQFPQPAQRQEKQPPQQQPIYANQYELNVAKAAAAASVYSPSSSTTSNSNQQQQQQRRNVARGLQYRESGGLETGRAGKQPPNAG
MLSMDNFRLLSVLGRGHFGKVILSQLRSNNQYYAIKALKKGDIIARDEVESLLSEKRIFEVANAMRHPFLVNLYSCFQTEQHVCFVMEYAAGGDL
MMHIHTDVFLEPRAVFYAACVVLGLQYLHENKIIYRDLKLDNLLLDTEGYVKIADFGLCKEGMGFGDRTGTFCGTPEFLAPEVLTETSYTRAVDW
WGLGVLIFEMLVGESPFPGDDEEEVFDSIVNDEVRYPRFLSLEAIAVMRRLLRKNPERRLGSSERDAEDVKKQAFFRSIVWDDLLLRKVKPPFVP
TINHLEDVSNFDEEFTSEKAQLTPPKEPRHLTEEEQLLFQDFSYTAEWC*
(SEQ ID NO: 186)

Name: protein kinase C-related kinase
Classification: protein_kinase

Celera Sequence No. : 142000013385194
CCCCTGCCACCCTACGAGCACAAGCCGGCCAAGAACCAGGCGGAGGCAGACGCCACCCTAAAGGCGCTGCGGCGCCAGCAGGAGGTGGGCCAGCG
ACAAACTCTAGTCGCCATCAACACGGACTACATCACGGAGAGCATCGCGGTGCACAAGGGTGAGATTGTCACGCTGTGCGAGTGCCGCGAGTCCA
AGGATCAGCGCCAGTGGTTCTACGTGCGGACGAGGGACGGACGCGAAGGCTTCATTCCGGCCGAGGTGGCCGGCCATGGCTACCTGTAGACCTCC
ACCTTCTGGTATTGGTATGGGTCTCTAAGGGTCATATGAAAGGGATTAGAAAGCTTAATGTTAACTATGGACATCCTTTGTCATATTAACCAACC
ATCATATAATTGCTATATCTAGAATATCTTAATCTTTAAGATTTTCTCATGATTTTGTGGTAAATTACTTAGCTTTATATTTCGACTCTTTCCAT
TACTGAGTAAAGTATCATTCATGAAAAAATGGAGCCCAACCACCGTAAGTTGTCCAAAGAGCACCTTCTCCCTTTTAAGATTTCCAAAAGGACCC ACCCCAAAAACAAGTCAAGTTCTACATTTAAATGAATTAACTTAATACCCATCTTAAGCACTCATAGGCCACTAATTCCATTCGCGATCCTTAGT
ACGCTTCTAGTTGTAAACTGTATTCATATCGGTGTCCGTAATTGAATTGAATTGTATCTGTATCTGTGTATGTTTATGTGCGTGAGTGTGGATCC
TTCGCAGGATCTTGTATTTATCTAGCCTAGCATTACGAGTACTCTATGTAATAGAAAACTTGCTTAAATGAAATCAAAGACGAAAGCGAAGACGG
AACCTATTTATATAATAACTGTACTTGATGCTTCTAATAAATAACAGACATTTAAATAAATATAAAAAACCATTGCGTTACTATTGACCTGGGTA
AGTGGGTAGAAAAGCAATTGCATATTTATACATATTTGTATTATTCATTTTATTATACACGTTTCACTCAGAATTGATATGTGTATATGAAGATA
ACATAACGATTTTCAGGGTAGTTATAAATGGGTTAACGTTCCAATATTTGAACTAATTTTTTATTTTTTTTTAATGATCTCTATAAATGTATTGT
TTATGCACTCTAAAAATAAGTTTCTTATTAAAAATATAAATACCATATACTTAAGCTATTGATTTCAATCTGTATATGCATGGGTTCGATTTAAA
ATTATTGCAACCTCCGATCCGAGTTTGTCTCACAGGCACTCTGCAATTTTACCAGGAAGAGGTGTTGTAGGTACTTAATTTAATATGATTTCACT
TAGGGAGTTAGTCGCCTATATGAGCATAAATGTTAGCACAATTTGGGTCGAATGAAGGAGACATTTACAAAAGTGAGGACCGTTGCTGGGTTGTA
AAGGGCCCCTAAATAATAATTTACAATTGGTTGAGCTGACATGGCTTTGTTGAGCAAGAACTACAAGAAAACTACAATTACATATCGAATGCAAG
ACAAATGCTACGCTACACAGAAATACATAACAGCATGAACTGAAGTTCTAGGAAACAACTTAAACTTACGTACCAGTTGGGCAATTCTTACCCTA
CATACATAGACAAATTAAAATATCATGGCTTAAGATCTAACCACCGGGTGAAGTGACTGTTCCGGCTGCCTACTTTAGAAATTTCGGACTGGAAC
TAGGCGACGCCGTCGACACGTTGTCCAGGTTGGTGTTCGTGTTGTCGAAGCACTCGTGTTGTGGCTCCGGTTCCGTGGGCGGCAGCGGTTTGTTC
AGCAGCACAGTCATGTTCTTCACGTTGCTGGGCTTCTCCTCGTCCTGGTTGATGTTGAGCATGGCGTCGTTCATGCGGTGGTAGTGCGGCTTCTG
CGAGGTGCTGGGTCGTGAGTAGTCCAGGTGATCGTATTCATCTAGCGTATAGAATTCAGACAATTAGATCGTTGTTATCTTAAATTGGTCATAAA
AACATTGGACATGTGTGAGGACGAACAGAGCACTACACGGAATGGTTCTTTAACACTGGCTTACCCTCGGGAAACAAAATCTTGCTATATATTTT
CACTGATTCATGCCGTAATGTGTGCAAATGTAGAGTACATAGTTAATTGTGAAGTTACTAAGCCTGCCTGTGTAAAAGTCTAATGACATACCGGG
ATCCTTGTAGCCCTCCTTGTGCTTGATCTCGTCGTAGACATGCTCCTCTTTGAGGGATTCGTTGTACACAATCGGATTGGTCCGGTCCGCGTTCA
AGTTCTTCGTTAGCAGGTCGTGGTTGTAGTTGATCGAATAGCTACCCACTGTGGAGGCAATGTACTATGAGACACTGACCCAAAATATTGTGCTC
TAAACATCTTACCCCTGCCACTGGCATTGCAGTCATCGCCGTAGTCCGTGCTCATCGTGCTCCTCTGGTCAAAGTTGTTCATCTTGGAACGCATA
TTGTTGGGCAGGAGACGCGTTTCCGCCTGCATGCCGTACACGGGATTGTCGAAGTTGTGGTTGGGCGGCCAGCTCGGGGGATTCGTATCATGGGT
GTAGTGTACATGGGCGATTTCGGTTTTTAGATTGGACACACGTCGGCGGTAGTAAATGAACACTGCGAAGATTATGCACGCAAACAGGGTCATCA
GGACTAAGGTCAGAGCTACACTCGCCCGGCTCGCTGCAATTCAAAATGGATGAAATGAATTAGTAATGTTGAGGAATATATTCTGATCAATGAAT
TATCTTACAATTTTCGCTTTGGTCTGCAATACGTTGAGAGGCGATTAGCTCGTCGCAGTTATCGCCGGTGTAGCCACTCCTGCACACACAACCGT
GGGCCGCATGGCACTGGAAATTGGCCGACGGACAGGCACAGGTATTCATGCAGTGCTCGCCGTAGAATCCCTCCGGACAGACCTCATCGCACCGG
GTGCCCGACCAGCCGGTTTCGCAGATGCACATACCGTCGGCCTTGCGGCAAACCTTGTGGTGCACGCAGCGGCACCGCTGGGCGCATCCTTGTCC
GTAGGTGTCTGTGGGACAGGACTCGTTGCAGTTGGAACCTGTCCACCCTGGCAGGCACTGGCACTGGCCTGTAACGTGGTTGCACTCGCCGCCGT
GCTCGCAATTGCACTTGAGCTTGCAGCCGGGTCCGTAGAGTCCAGCAGGACATGGGTGCTCGCAGGTGAGACCTATGTAACCCGTGCGGCAGAGA
ATTTCACCTGTGATGTGATCGCAGCTCTTGTTGCCTGAAAAATATGTGAGTATTAGGGGGTGTTTTGCTTTCGCCTTGTAATCTTATCCAATATA
GCTTACCATGGAGGATCTCCGGGCACCGTTCCTTGCATTCCATGCCGTAGAATCCAGGTGGGCAGGGTTCCGCACAGTCGGCGCCAGTCCAACCG
GCTGAGCAGATGCAGTTACCGGAATCGGGGTCGCAGGAGGAGTTATTCAGGCATCTGCAAACTTTATCACAATTTTCACCATAGTAACCGCTCCG
ACAGTTGGTCTCGCAATGAACGCCTTGGGTTGTTCGATCGTTGGGTATCAGACAAGGCCAACAAAAACCAGAAACACAAAGGTGCAGAAACAGAA
AAGCAAATTAAATTAAGGAAATGAAACGTGGCCATGCAAAATAGGTGCGATAGATGCAAAAATGAAAGTAAGTGAAATGAGTTCAGTGCGCACTA
ATAAGGATATAAGATGGAACTGATTAACATGTTATAGGTAGAAAATCATTCATCAGATTTACACTTTGTCTTACAAAATTGTAAATATTTAATAG
AAAACTGCCTTCTTAATATCAACAGTTTGGTTTAAAAAAATAAACAAATTTTAAGGGGTTCCTTAATTACTGTTAAAAGAAAATCATGCAAGCTC
TACAATTTGGATATTTTATCTAAATTATTCAAGAATACACGTAACCCCTTTCTTATTGAACTATCAATTGATGGAAATCACGCCTTTTTTCTATG
ATTTTAGATCGGGGCAACCTATAAATCTCGCTAATGTCAACAGTGATCTATGAACTTGATGAGCTGAATTCAATGAGGTATATAGAAATCCCGCT
AGTACCTCCCCAATCCTGCTTGCACACGCATCTTCCATTGGTGGCATCGCAGGCCAGGCTGTTGTTGAAGTCGCACTGGCACTTCTGGGCGCAGT
CGTGTCCGAATTTGCCGGTATCGCACTTCCTTTCGCACCGCTCGCCCGTCCAGCCGGCGGCACAGGTGCAGCTTCCGTTCTGCGGATTGCAGGCG
GCGTTATTGTGGCAGTCGCACACCTTGGCGCAGTCCTGTCCGAAGTGGTTCAGATCACACGGCCGGTCGCACTTGATGTTTTTCCATCCGGCCGT
GCACAAGCACTGGCCCGTCTCCGGCTCGCACTTGGCTCCGTTCTGGCAGTCGCAGCGCAGGGCGCAGTCCTGACCAAAGGTGCCCGGCTCGCAAC
TCTCCTCGCAGGTGGGTCCGCGCCAGCCCGGCGCACATAGGCACGTACCATTGACCGGCGAGCACTTGGCTCCGTTCTTGCAGTTGCAGGTCAGC
TCGCAATTCGGGCCGTAGCGCAGGAAGGTGCAGGGTCTGGTGCACTGAGCACTGCTCCATCCGATGCTGCACTGGCAATTCCCCGTCTCCGGGTG
ACACAGATCCGTGTGCTCCATGTCGCACTCGCAGGTGCGGTTACAGTCCAGCCCGTACTTGTTCGCCTCGCAGATCCGCTCGGCGCACTTGGCAC
CCGTCCAGCCGGGATTGCAGATGCACGTTCCGTTCGCCCGATCGCACATGGCATCGTTCGCGCAGTCGCAGGTCATGCTGCAGTTGAATCCGTAC
GTGTTCAGCTGACACTCGTCGAAGCAGCGTTCTCCGCGATATCCGGGCGGACACTCGCACTGGCCGGTGATGTGGTGGCAGGGCGCTCCCTTGTA
GCACTCGCAGCTCTCTTGGCATCCAGGGCCGTAGCTGCCCACCGGACACTTGTTTGCACACACGTCGCCCGTCCAGCCTGGATTGCACATGCAGG
CCCCGGTCTCTGGCTGACACTTTCCGTCGTTCTGGCAGGGACAGTCCTGCTGGCACTGGGCGCCATGCTTTCCATCCGGACAGCGCATATCACAT
CTAGTTGGAGCGGAGTATTAGTATGGGTTTTGCGTTGGAGCAGGAGCAAAATGAAACGTAGAATGCAACGGCCTAAAATCCCAGCCACGAAAAAT
AATTGATTGCATTCTGCCTTTCATTTTGCCTGATCCTCGGCCAGAAGTTTGTGCCGCCAAAGAGGCCCCTTCGTCCACTTACAGGGGACCCGTGA
AACCGGGAGCACACTGGCATTCGCCGGACACGTGGTGACACTTGCCGCCGTTCTCGCATCGGCACTTCTCCGAGCAGTTGGCCCCGAAAAAGCCC
TCCGGACAGATGTCCGCGCAGCGTGCTCCGGTGTAGCCCTTGGCGCACTCGCAGTCGCCTGAAAAGGGCTCACATACCGCGTTGTTCAGGCAGTC
GCACTGCATCGAGCAGTTCCGGCCATACCAGCCGGGTGGGCAATCTACCGAAGAGTGACACAAACATGGTTAGCTGCGGTTACGGATCACAAGGT
ACGGGTTCGACAGTTAGTTGCTTTTTTCTTGCTTTTGCCTTTCGCTTGCTAGCCACGGGAAACCCAGGAGCCGGAAGAAGTTCCGCTCCCGGAAG
CTCCCGTTTTGGTGGTGGGGATTAGTGACCGATAGCCTGCTTGCACCTGTATAACTGAGCCGGAGTGAACTGCATGGGTGCATGAGAGAGAGAGA
GTGGAGTGTAGGTTGTGGGTGGTCGGAGTTAGATTTCGGGTTAAGATGGCATAAACAAAAAAAAAAACAAACAAAAGCTACAAAGCAACATATAA
CATATAGCAGAAATATAGCTACAAAGACACTACGTGCAGATCTTTGGTAGTCCAAAGACGGAATGCCCTTGCAGAGGCTATAAACTATATACATT
TAAACCTTAATAATAATCTTGTTTTTTGATATTATTATTTTGACTAGAATAGCATATGGTTTTCAGACAAATTTGATCATTTCCTTCTTGCTGAT
TGTAAAAACATTCAATTTTGATGAAAATTAAAAAGTCAGCGAGCAGATTAGTAATCCATTCGCCTTTCTTTCATGAAGTAGGAGTGCCTGTTTCT
CGTCCCCGGCAGAAAAACGTGAGCTCGGAACTCGTCTATGTTGAATTCGTTGGGTTTGTAGACAAAAGGTTCCTTGATCACCGACACTGAACTGA
CTTTTTTCACTAGCTCTTCGACCGGAGGTGCGTCCTTGGTCACTTTTTTTGTGATGCCAAGCATCTGCCAAATATCGTACTCCGACTCCTCCGCT
ACTAGTGACTGTGCCGCGAGGCTTTGGACACTTGGCGATGGGGTCGGGCAGAACGGCAAGCACTCCTTCTTCCTCGCCATGTCGTTCTCTACCTT
TTGCACCATCGGATGCTTCAGCGTCTTGGCAAACTCCAAAACATCGCCAATGCTGGGGAAGCGCTGTGTATCGGTGACAAAGCCGTTTTCGCCCA
AGAAAATGTTTCGCCTGACTGCCACGTTCGCCTCGAACTCTTCTTGCTCGTCCAAGTCGCAGTCGCGACAGTCAAAATGGGTGACCTTCATGTTG
GCGGTGAGGGCGCATATAAGTCTTGTACCTAGCTTAGCACCTAAAGGAATGGCCACCATTATCAGCCGACGAAGTGGATCGTGATGACGCAGAAG
ATCGCCTAGTTGGTCCACAATTGTCCGAGGATTCGCCTCGATGCCGGACACATTAAGCTCCTCCACGTGCTCGGTGCCCTTGATACCGTTGCACA
AAATGGACAGGGAGTCGCCGCTCAACTTATTGTGGGCCAATCCCAGATACTCCAGTCTGGAGAGGTTCGGTCGCTGCAGTGCCTCTCCGATAGCC
GACATTGCCCGCGTGTCCAGTCGGTTGTACTCCAGCTCAAGGATCTTTAGCATTTGCGGCCGCTCCAGCAGAATTCCCAACTCGGGGCCACAGTC
GTCAGTCATCTGGTTGTACCCAAAGTCCACTACCTCCAGCAAAGGCAATAGGCGCAGAGCCCGGCACACGGTGTATAGCTTAAAGCTATTAAGTC
TGCTGTTTCGAAGCCGGAAGATCTGCAGCTGCTGCAGTGCCACTAAACCTCTAGCCAGGCGAACCATGTCCTTGATCGAAAGAGCACGTTCCGC
TTGTGGTACTTTCTACCCAAAGCCGGACCCAGAAACTCCAGGTTCAGCGATACCAGATTGACAAAGTGGCGCACAAAGCTAAGATCGATGTGAAC

FIGURE SHEET 98

GCAGTCGTCCTCCGGATATTTTAATTGTTGTAGATGCGTCAGATATCTTTGCTTGTTGCGTTTGTCCAAAACCTTGTCATCGCCATCGTCTGGTT
CAGGCTCCACGCGGATATCAAAGGTGCCCTTTATACGCTGCCTTCGCTTCTTTTTCTTTCGTGGCTCTGGTTCCTTGGGCTTCCGCATCTCGGAC
CGTCGTCGCCTGCGCTCCTCATGCTCCGCCTCCCTGGCAGCCTTCAGATCACGCAATCGTTGGCGGGCGACGTTGCGTTCATGTCGACGTTTGCG
ACGCTCGTTGCCGGAGTCATCTTCATCGTCGGAAGCATTCAGCGTAAATTTTGTATTGAATCCAATTGCCCTTTTCTGGTCAGAGGCGATTGAAC
CCGCCCCCTCCTCTTCTTCCTCCCCCTCCTCATCGACGTCTTCTGGTGTCATTGGCTCATCACTGGAGATTTCCATGCCACCAGACTCCTCGGAT
GTTATTTCCGGTTCCGAGTCGTCTTCCTCACGTTTTGTTTTCCGAAAGGCATACTCCGACAGCGGCTGCAGGTGCCGAATGTCCATGCAGCGAAC
ATGATCCTTTATTAGCTCGGCTAGTTCGGTCATCTCTTTCTCTGGCCAAAGGGCGGCCGGACAGGCCTCCACCAGCTCCATGTACTTCAGGCTCA
GTCCCTTGCCGCGCCAGTCGTAATCCTGCAACCCCTTCAGTGCAAGGCATGTCTCGGAACTCTTAGCTAGGACCACCCGCCTCCAGTAGCTCGCA
TCCTCTACGCAGTAGCACTCACGCAGTGGCAGATCCACATCGAGTGAATCGTAGTGGATGCGCATCTTTCGCGGATCTTGAAGCACCTCGTCGGG
CACGTTGGCATTTCCACGTTTAGCCATCTGTCGGACGCAGAGATCCGCCAAAGTGGGCACTTGGTCGGCATCGTTAAACGCCTCTGCGAAGAATT
CCCGATTACGCTCCGAGAGTAAATTCCGATTGGCGGTCAGGGGCGGCTTGTAAAGCTCGTACACGGCCAGCATGACCGGATCATTCGGAATACTC
AAGCTATTGGTGTTCGGCAGCGGCAAGTAATCTGAGTCCTCATCCTCCATCCTATACGTTCCAAGATGTGTGTGGTGTAGAGCTATTTATGGTAT
TTTTTATTTTTTCCTATTTTTTTTTTTTGTTTGTATGCTTTTTGTTTGAGGAGTATTTGTTTGACTTTAATGTGTTGTCATATTGGAAGATTATT
TTCCTCTGGCTTTAGTGGGATCATTGATAACTGAATACATTTCAGGTGTCTTTTTTGGGTCTGAGAATCGACTAATTCGGTTCTGTAGTATGTAC
AAAATATTTTAGCTTTGCGTTGTCTGATACTTTATATACTTAAAAGAACATAATCTACAGTCGAGCAGCAGAACAATTAAACGTACAGTTAATTT
CTAATCTTTGCAAGGGCATTTAGAACTACAGAGCTTCAAAGCTGCTTAAGTGATTATACAAGCTCTTATCTACGGGGCTCGGCTCATCGCAGGCA
ATCCGGGGATATCGTGAACTTGAAGTTTCAAAATTGAAAAACCGCCGTTTCTGGGATAAGCCGCACCCTTGGAACACCCAAGGCGATTCATTAGG
GGCAAATTACGATTAGCTTAAAGGATCAACGAACTTATATCGCAGGCGGGTCCTCCGTAACCATGATCACACTTGCACTTCTCCGGGGAGATGCA
TCTACCGTGCTGGCAGGGTTCCGAACAATGCGGCACGCATTCTCCTGCGCTCGCGATGTAGCCATCTAAAAGCGGTTAAAAATGGTAATATGTAA
AGTAAAGTCAAACATCCAGACTCATCCAACTCACCACAACAGTCCCTCACAATACGGTTCTTTGCAATCGTCTTGGTTTTGTTGACCACTCGGTG
TTTAATGCGATAGGTGGAGCACCTCGGCGGGAATGTGACGCACCAGGTGGAGCCCCGTTCCTGGAACGATTGCAGTTCTGTGTAGACAACGTCTA
CGTTATATCTAAAGGTAAAAGTATTCATTAATTTAGTTCATTTGTCGTGATAGGGGATAAGCTTACAGTTCTCTTCTTTTGCAGATATTGGGTCC
ATCCAGATCTTTAAGATCCGCCTGAGCCAGTACCAGCTGGGCCAGGCAGGCTATGAGGATTACCGGCAACATGGTGGCAGTGGATTCCAGGTCCT
GGAATGAGTTACTCGTTCTGATGCAGCTTCACTGGCGGATCACATTGAACTGATAAACACAGTCAGTATAAACTAAAGGATGACTCAAGCCGAGA
TTAAACCGGATTCAACTGCAAGAACAAAGAGAGAATGAGTTTCAATAAAAAAAAACTTTCTCCGTATGATTTTACATACTACATATTATATGTAT
AATATATATGGGGTATAGATTAATAAATACATATTTTTGAAAAGAGCTAGATTTAATTGTTAGAAAACATCCATAGTATTTCCCGTCGGATGAGT
TTATGACGTAAAGCTTTTTCCGGGTCGTAGCCACCGGTCCAGGGTAGTCCAGTCTAAAAGTAGAAAATTTCCAACACAGTCAGAAATTGAAAGCT
GCTTAATATCCCCAGAGGTGCCAGGAATTCGATTCTTCTATAAATCAAGAGCGCAGCAGTAGAGGATGCACAACCAACGTTCACCCTTCAATGGA
GGCCCGGGAGGATTCGGAGCCAGTGCCTTCAACTTCAATGCACCACAGTTCGGCGACGGCGCTGCGTTCTCCGAGGGTCTCAACGGGATGCCCTT
TCTGGGCAAGATGCCCACCGAACCGATGATGCGCTCCATTAGCCGCCAACGCTCGCTGGTTGATGGGGCTGGGCTACCCAAGATGCCGGCACCTC
TTCCCGCGATGGCCCAGCAAATCTTGAGCGGCGCCGGAGTGGGACGTAGTCAACGCTTCCCAGTGCCACCTATCTCCACTTACTATGGGCACTAC
GAGGGCGACTTTTCGATGTCTTCAATGTCAAAGCTAAAGGACACTGCCTCACCCCCACAGACCCAATGGCAGGAGCATAAAACACCGCGTCTAGC
CGCACTTTCAGAAACCGACTCCGAGAGCGACATATGCAGTCAGCAGAACAGAGCGAAATTGCCTGAATCCCGTTGGCGTCGTGCCATTAACTACG
TAACGGCCGCTCTGCCGGAGCAACAGCGCCAACGCATGGAGGTGATGGTCAAGCGCTGTGGCCAGTCGGCTATCGCCAAGCATCTTCTGTTGGTG
CTGCATCTGATCGCCCTGGTGGTGGTTGTGTGTTTCCGCCAGGTCGCGCGACTTGGATGGCTCTGCGGCGACATTCGCTCTCGCCTAGGACGCGT
CAAGTACCAGTCGCGCAGCTACCTGCGCCACATGCTGTGGCGGCTGGCCATTGCCAAGAGTAACGACACCTTTCTCTTTCTCATCGTGGTGCTGG
TGACGCCCTGGCTATTCCTTCTCAGCCTTGTCGGCTTCGCCATATCCTTCGTCTTCTCCATGAGGACCACGTTGGCAGAGGGAGTCCGTCAGCTG
CGCCGTCGCGTATTTAGACCATAAGTGGAGGGAAATGGCTTTAGGAGCAGCACCCACAAGCTCCATCGCCCCCAAGTTATCACACAAGGACACT
AAAGCAGCGCATTCCACAAAATAACACATGACATACAGCAAGATGAAACCACTCGAATTTTAACTATATTTTGTGTTGCAGCAACGAAATAGAAC
TCAAGTAACGTTTGTGTTTCCATGGATTCAGGCTTGGGTTTATATTCCGTAGAGCAATATTGCATCATTCCCCATTTCGAATGTTGTTTTGATTT
TGGAAAATTGCGATCTGCTCAAAGGTGTTAAATATCTGGCCATCAGCTTATGTGTGATCTGATCAATAAATCGCAATCGTATTTATTTGTTTACA
GCTTAATCCGCTCGCTGGCCACTTGTTCGCCACTCATCAAACCCATTTATTGTGTGTATTATTTTTGCCATTTATTCTGCTCGATAAATATGAAT
GCGAACAAATCAAAACGAAAACATTTCCGCCGCTCATGGGGCAGAACCACAGATTGTGGGCCTTTGTTGTTCATGCTCTCCGTAATTTCACTTTC
AATTGCATCCCACCAGCAAAAAGCCCCATTTGTAGTATATTATATGATTCACTGGCTACCGACAGTCACATCTGCGTTCCACGGCATATGAAAAG
CGTTCAGTGACTCGGGAAAACCCAGGAGAACCTCCTCCAGTTTCCATTCAGTGCCCCAGGGCCCACTTCACAAATATTCAGAGGTCACATCTGGG
ATTTCTCAAATTTCAACTCAACATGGGGCTAAGAGATATTGAGAACTTGCCATTAATTATGTCAAGTCTACGTGTGAACTGGGCCAAGTAATATC
CGAATGTGGTTTACAATTACCAGTGACCCATCAAGAATGGATTGCATAAACGTGGATCGCTATCTGTAAAATTATCCAGGCCGAACCATTTGCAA
TTGATGCCAGCACGGTTTTTCAGGAAATAAAGATCCACTTTTAATACCAAACATTAGGTATAATATATATGACAATCGCGAACAAAAGAGAGCTG
TTTCTTTCAGTACTTGGTTATTTGGAACTGACATGAAGCACGGGCCAGCCATGTCTGGTCAGTTGGAAAGTACGTACAATTAACTGGGGGATTGT
CGTGATCCACAATCTATATTTATATTGCAAAGATAATTGTTGGTTTCATTTCTTGCCAGCGAGAAATCTGATTCACTTAATCGCACGGCAGGTGC
TCCCTTAACTCATCAGAAAGTGGTGTTTGTCAAGGCCGTCATTAGCAAGAAATCGCGTGATGAACTGCCAACGGCGCCAAATAAATTTTAAACGA
GAAATTGTTCGAAACCCAGTGTTAATAGAACGTTCACGTTTTAGAGCAGATCGTGAATGTGTTCGCCCTCTTAGATACATATTACAATCCTTAAG
ATAGCCGAAACGATAATATACAACTGGGGCAATATAACCTAAAGTAGAAAGAGATAACCATTTGGCATACCCCTCGACTTTGCTCAAGATTTTAC
AAGTGATAAGGGTGGATGATAAGACCGCCGCAGTCATTCTCATCCATTACAACAGCGATGAGGTTCACTGATATTTGTTCTGTTGTAGGTGACTA
ATTCAGTCTCTCTATATATAAGCAGATCCACGGAACGGAAGGTGCGTAATCCGGTCATGGACAAAGACTAATAGAATAATACCAAATCATCCCGT
AACATCATACAAATTTACGATGGACAACGAAATCGTGTGAACCAAACAATCCGGTCTAATTTAATTTGCAATTTGAATGCTAAATCTTTCATTTT
AACGATTAGCAGAGTCCACGTTTTTCAAACAAAGTATAAACCTTTGGAATCAAAAATATTAACCATAAACTAGGGTGTTACTCTAACCCATTGCC
ATTAAGTTTCATTTTGCCACTCAATCTTCCCTTCCGCATATGTAGATCATATTAAAATGCGAACTTGCACGAGACAACGAGCTTACATTTGCAAT
TTACTTATTTGTTTACATGCCTGATTGGTGTTTTAATGAGCTAAATGAATATGTCGTGGATGAGTCACCTTAGGTTAAACAATGCTAGACTATAG
TCTATAAACTATACGGATCTGTTAGTTGTATGTATAATAGGCGAGTGTGCGAGATTTTTCAATGGAAAACGTGTTCGGCACAGTTTGTTTTATCG
AGTATCGAATCCATGCACCATTCATCGATACCGCATACCCAGCATCTGTTCCAATGCTGAGTCACTCGGATTTCATTCACAAAAGTCTGGCTAAG
GCTCGAACTTCGGGTCAATCTACCGCTCAATTCGCAGGTTTGTATTTCAGACCTTTCCCAATATGTGTGTACTTTTGGCACACCTCATATTTATC
ATACCTCGCCCTTATCTGCGCCCAGTATTGGACAAGCAGAAACAACACGATGAGGCACACTGATAGTGGTTCTTAATCGGAAGGGGTCAACGAAA
AGTTGAGGGAGAACCATAAAATGTTAGCAAAGGTAATAGAAGATTGATTAGAAGTAAGTTGCGAGTCCGTTTCCGCTGGCAATCTGTCTATAATG
TATACATATGTAGGTACTTATATATGACTAATTTCCTGATTTTCGATGAAAGCTTTCGAAAGAAAAAAACAAAACAAAAACAAACCAAAGAAAAT
CTGCGAAATACTTTCGGACTAAGGAGAAAGCTTTGTTGTTAAAAAAACTCAATGGCATTCGTCTATTTCATTCAATTAGAATGATATGTATTTTA
TAAAGTATAAGCATTGCCTATTTTCGTTCCAATTAAACCTCCATCAGAGCTAAGAGTAGGTCTTATATTCTTCAAGTTGTGTGTATATATTTTGT
GATGTATTTTCAATTGATTCAGCACAGTGCATATGTAAACATCTGGATTTGACTTGGATTACTATAATCTTAAGCATAGGGGGAAAATGAGCCAG
CTATTCCCCCAACTTCAAGTACTGCGCACTTGATAAAGGCTAAACAAAGATTGTCGCTTCCCGCTTTATATAAACAGAATTATTCTACAAAGGAG
GAGCCCTCACTTGAGCTGTACTTTGGATAGCGAAATCAAAGTCGAGTTTACTGAATCCACAATACACATCTCCAATAACCGCAACGCATATGTTT
GGCGTTCAGTGGGCAATTTAACGCCTTGGCGAGGCGACAAAGCACATTTGGCAAAAACGATTATTAAGAATAATAAACGATTTCAATGGCAAGAA

FIGURE SHEET 99

ATAGATTTGGTATAAAAACAAGTTGTTCTGGCCCAGGAAATGAAATTATTGAAAGAATATCAGTTTGCACGAGGTCTAGGGTCTTACATTTGTGA
ACTACGTAAATGCTAGGCCAATCAAAACTTTCAGTGAACAGTTTAATTAAAGCAAAGAGGCAAAGGGTTCTCAAACGTTATTATTTTGGGATGGA
TGTTAGCTGCCATTATGAAGTATCAGTGAGAAACAGTGATTTCAGCTGTTTCGTATTCATTTCACAAGTGAGCCAAACACTCAACACCTCAGTTT
GTATTGGCCAATTAGCGGGCGAAGCTCGGATTTCTAGCCCGAATTTGGATAGAGCTAGAAGCTTTCTCGATTGATTCAGCGAAGAGAACCGATTT
CAGCTGAAAACCAAGAAAACATGTGTATATTATTCTAGTGGAAAGGCACCCACACATTGCAATGCAGACAGACGAACAAGAATTAAGCATAATCA
TCAGCAAAAGCGAAATGCACTTGCAACAATACGGAGAAAGCAAAGAAAAATGTTGGATAATGCAAACCCAAAGCGAAAAGATAGAGAACAGAGAA
TGTCGTAATCATAAGGGGAAAACTAACATCCCGACTCATGGGTTGCTCTCTAACCACCGCCACATTGGACAAGAAATCCCAGGAGGTTTCATCCC
AGCCACTCCCTGCCACTCCTCCACCCAGCATTATCAATAAAGCTGAGTAATCATGGCGACGACAAAGCCCGGCTCCATAAAGGAACCTAAACAGA
CATTGTGACATGTACGGCATGGTATGATATGATATGATACCGAGGGTGGGGAGAGTGCACCTCTGAGTGCCATTTCAGTTTTTAATTTTGCAATG
GCTTGTGGGACTTTTCGCTGTGCATTGCATTTCGAAGCTCGTGTCCTAAGCAGGCGTCATTGTTCATTAAATCACGTATGATAATAAAAATCAAG
TTCCATTGCCAGTGTCAGAAATATAAGGTTAAGCTTAAAATCGCTTGGTTAAGGAAACTGTGTGAAAAATAAAAATGCTTTGTATGGAAATATG
ATCGCAGTTTATTCCATACTTATTTAATGAATTCTATAAAAAATAAGAACGGTTTCTACATATATCTTAATTTGTGTGCACCCCCATATTCAGAA
GTAATATGAAATATCGCTGAACTGATACCTTAATCAGTACTCATAAAGAATTAAACGCAAAAAAATTTTTTGCGACTTGATCTAAATTATAAACG
GCTATTATTGTTATTTATTTTCGTGACGATGCATCGACTGTATTTTAATGTGTGCGTTAGTTAGGCAATTTCGATGTGTGTGAGTTTATGCTGGC
TGGGTTTTCATTTGATCCGTTGGCGTTGTTGTTGTTGCGGCTGTGACAGCTGGAAGCTTCAGCAGCAATCTGGAAACTGGAAAGAATCCACAAGA
TGCGGGTTTCCAGGGAGCGAGGTGCTGGTCGCAGGGGGTCGATGAAAGAGAAGTTTGCCGATTTGCTGCCAATTCCCCGAATGACAGATATAAAG
ATACATGCATGAGATACAAAGAAGAAGAAGTCGACGAAAGCGCAAAACTAAAGCCAAAGAAAGGCCATTAAATTGTGCGAAAGAGAAACCAGAAC
AGGTTTAACTGTTCTTGGTGTGCGCCCGATAAAAGCGCTAATTGACACGCACACAAGTGCACTACTGCGGTCATAAACAAACCGCTCGTTGGGAA
AGAAGAAAGGTGGAAGGGAAAGAGAGCTGACAAAGCTAACCAGGCGAAATTGCACATTTAACAGAAGAAAACTTATTTTTAACAACATAACAATG
ACTAAAATTAACGTTAAACTGCCACGATTGGGGTTAAAACTCACCTTGGCAAGAAGCACGGTGTAAACTGGTTTTCGGTTCTCACTCAAAACAAA
CCAAGAATGCACTCGCAATCGAATTCCACTCAATTTACACGTTTACGAAACTTTGGCCATTAAAACCTCGAGAGGATTTGTATTTTTAAATGCTT
ACAGCACCTTACCACATATATATATAGCTATATATATAAATTTGCTATTGTTTTTACTTTCTCACCATCCACAAAAACTTGTTTTCGTTGTCGCT
ACTCTCTATTTTGGCACTCTACTCGCAACTGAGCTGATTTAGCAATTAAAATGCAACCTCTTTAAATAAAAACAATTACTTTTCGTGCACTCCAC
TAACGACAACAATAAGGACAAACGGGCGCGACGCACAACAACGCAATTCTTTAATGCACTTAAGTATTTTCGTCGGTCAATTGGAGCTCGTTTGG
TTTTCGCAAGCACCGCAATTACTATTTACTTTATTTTATATTTGCGTACGCACACCACCGCACGAAGCAGAAATTTATTTAACTTATTTAAAATT
CAGCAAGAAACGGACAACCGACTTACTTAGCTGCACTCGCCAGTGTGACCGCTTTGCGAGTGTTGGATGAGCTAGTAGTGTGGCCCTAGCGCACT
CCCCAGGAAATACTCACTGTGAACAGTCACTCTTTCCACTTATAACACTTTTCACTTGAAAATAAATTTGAATTCTATCTTAAAACTACATTGTT
TATTTGCGGAGTAGATACGCCTGTACCACCTGGGATAAGCAGAATGAAAAACAGCTGGAGTAATTAAAACACTAGTCCCCGCTCATTTCAGATCT
CCACCGTCATGGACACGATCAAACTGTGGCACAGTGGGCAAGTTCGGTGCCTGGAGATCTCGGTGGGAGCTGCGCAGTGGTGGCAGGTGGTACAG
ATCCATATGTTGTTCGTCGGCTGGGTGATGGGTTTCCCGGAGGAGATGCACGCCGGGAAGCGAGCATTGCACTCGGGGCAGGAGGGGGAGCTGAA
AGGATCGGCATTCCATGAGTATCATCATTATAATCCAGCTTCTGACGTCGACCCTTCACTTACCTATCTGGCACGGGCACTCCGCAGGAATAGCA
ATCCACCCTATCGCCAGTGGTGTCCTCCGGATCGTACTTGGCGAAGATCCCAGCCGCCAACTCCTCGTACCGTTGAAGGGTAGCCTCGGGAAGAT
GAGCCTGTTGCTCCAACTTCATGAAAGCCTTGGAGCAGGTTCCGAAGGCCCGATCCGCACAGCTGGCCAGTGCCAACAGGCTGTAGATGTGCTCT
GGAGGCAGGACGTCCTCGTAGTCGCGCAGCCTCACCGCAGTGACCACCGCACTGTGGACGATCCCGAAGCGAAGCTGCCTCTGGGCTAGGAGCAT
GAAGTGGTAGGCCTCGGCGCAGTGCCAAAGCCTCTCGATGGCGGCCGCATCCTCCAGGGCAATGGAGTCCAGTAGGGTGTTCCTGCCGCTGGCGT
AGTCGATCTCCGTCGTGGCCACAGCCTTGAGGTGCTCCTCGGCCAGCAGAGCAGCCAGCACGTACAGCTTCTTGATTCTCAGCAGCGGAGCAC
(SEQ ID NO: 187)

Exon: 16478..15910
Exon: 9610..9377
Exon: 9318..9155
Exon: 9090..8965
Exon: 3481..3332
Exon: 3264..2764
Exon: 2693..2388
Exon: 2328..2182
Exon: 2092..2060
Exon: 1941..1001
Start ATG: 9477 (Reverse strand: CAT)

Transcript No. : CT6730
CTGGCGAGTGCAGCTAAGTAAGTCGGTTGTCCGTTTCTTGCTGAATTTTAAATAAGTTAAATAAATTTCTGCTTCGTGCGGTGGTGTGCGTACGC
AAATATAAAATAAAGTAAATAGTAATTGCGGTGCTTGCGAAAACCAAACGAGCTCCAATTGACCGACGAAAATACTTAAGTGCATTAAAGAATTG
CGTTGTTGTGCGTCGCGCCCGTTTGTCCTTATTGTTGTCGTTAGTGGAGTGCACGAAAAGTAATTGTTTTTATTTAAAGAGGTTGCATTTTAATT
GCTAAATCAGCTCAGTTGCGAGTAGAGTGCCAAAATAGAGAGTAGCGACAACGAAAACAAGTTTTTGTGGATGGTGAGAAAGTAAAAACAATAGC
AAATTTATATATATAGCTATATATATATGTGGTAAGGTGCTGTAAGCATTTAAAAATACAAATCCTCTCGAGGTTTTAATGGCCAAAGTTTCGTA
AACGTGTAAATTGAGTGGAATTCGATTGCGAGTGCATTCTTGGTTTGTTTTGAGTGAGAACCGAAAACCAGTTTACACCGTGCTTCTTGCCAAGT
TGAATCCGGTTTAATCTCGGCTTGAGTCATCCTTTAGTTTATACTGACTGTGTTTATCAGTTCAATGTGATCCGCCAGTGAAGCTGCATCAGAAC
GAGTAACTCATTCCAGGACCTGGAATCCACTGCCACCATGTTGCCGGTAATCCTCATAGCCTGCCTGGCCCAGCTGGTACTGGCTCAGGCGGATC
TTAAAGATCTGGATGGACCCAATATCTGCAAAAGAAGAGAACTATATAACGTAGACGTTGTCTACACAGAACTGCAATCGTTCCAGGAACGGGGC
TCCACCTGGTGCGTCACATTCCCGCCGAGGTGCTCCACCTATCGCATTAAACACCGAGTGGTCAACAAAACCAAGACGATTGCAAAGAACCGTAT
TGTGAGGGACTGTTGTGATGGCTACATCGCGAGCGCAGGAGAATGCGTGCCGCATTGTTCGGAACCCTGCCAGCACGGTAGATGCATCTCCCCGG
AGAAGTGCAAGTGTGATCATGGTTACGGAGGACCCGCCTGCGATATAATTTGCAGATGCCTGAATAACTCCTCCTGCGACCCCGATTCCGGTAAC
TGCATCTGCTCAGCCGGTTGGACTGGCGCCGACTGTGCGGAACCCTGCCCACCTGGATTCTACGGCATGGAATGCAAGGAACGGTGCCCGGAGAT
CCTCCATGGCAACAAGAGCTGCGATCACATCACAGGTGAAATTCTCTGCCGCACGGGTTACATAGGTCTCACCTGCGAGCACCCATGTCCTGCTG
GACTCTACGGACCCGGCTGCAAGCTCAAGTGCAATTGCGAGCACGGCGGCGAGTGCAACCACGTTACAGGCCAGTGCCAGTGCCTGCCAGGGTGG
ACAGGTTCCAACTGCAACGAGTCCTGTCCCACAGACACCTACGGACAAGGATGCGCCCAGCGGTGCCGCTGCGTGCACCACAAGGTTTGCCGCAA
GGCCGACGGTATGTGCATCTGCGAAACCGGCTGGTCGGGCACCCGGTGCGATGAGGTCTGTCCGGAGGGATTCTACGGCGAGCACTGCATGAATA
CCTGTGCCTGTCCGTCGGCCAATTTCCAGTGCCATGCGGCCCACGGTTGTGTGTGCAGGAGTGGCTACACCGGCGATAACTGCGACGAGCTAATC
GCCTCTCAACGTATTGCAGACCAAAGCGAAAATTCGAGCCGGGCGAGTGTAGCTCTGACCTTAGTCCTGATGACCCTGTTTGCGTGCATAATCTT
CGCAGTGTTCATTTACTACCGCCGACGTGTGTCCAATCTAAAAACCGAAATCGCCCATGTACACTACACCCATGATACGAATCCCCCGAGCTGGC CGCCCAACCACAACTTCGACAATCCCGTGTACGGCATGCAGGCGGAAACGCGTCTCCTGCCCAACAATATGCGTTCCAAGATGAACAACTTTGAC
CAGAGGAGCACGATGAGCACGGACTACGGCGATGACTGCAATGCCAGTGGCAGGGTGGGTAGCTATTCGATCAACTACAACCACGACCTGCTAAC
GAAGAACTTGAACGCGGACCGGACCAATCCGATTGTGTACAACGAATCCCTCAAAGAGGAGCATGTCTACGACGAGATCAAGCACAAGGAGGGCT
ACAAGGATCCCGTGAAAATATATAGCAAGATTTTGTTTCCCGAGGATGAATACGATCACCTGGACTACTCACGACCCAGCACCTCGCAGAAGCCG
CACTACCACCGCATGAACGACGCCATGCTCAACATCAACCAGGACGAGGAGAAGCCCAGCAACGTGAAGAACATGACTGTGCTGCTGAACAAACC
GCTGCCGCCCACGGAACCGGAGCCACAACACGAGTGCTTCGACAACACGAACACCAACCTGGACAACGTGTCGACGGCGTCGCCTAGTTCCAGTC
CGAAATTTCTAAAGTAGGCAGCCGGAACAGTCACTTCACCCGGTGGTTAGATCTTAAGCCATGATATTTTAATTTGTCTATGTATGTAGGGTAAG
AATTGCCCAACTGGTACGTAAGTTTAAGTTGTTTCCTAGAACTTCAGTTCATGCTGTTATGTATTTCTGTGTAGCGTAGCATTTGTCTTGCATTC
GATATGTAATTGTAGTTTTCTTGTAGTTCTTGCTCAACAAAGCCATGTCAGCTCAACCAATTGTAAATTATTATTTAGGGGCCCTTTACAACCCA
GCAACGGTCCTCACTTTTGTAAATGTCTCCTTCATTCGACCCAAATTGTGCTAACATTTATGCTCATATAGGCGACTAACTCCCTAAGTGAAATC
ATATTAAATTAAGTACCTACAACACCTCTTCCTGGTAAAATTGCAGAGTGCCTGTGAGACAAACTCGGATCGGAGGTTGCAATAATTTTAAATCG
AACCCATGCATATACAGATTGAAATCAATAGCTTAAGTATATGGTATTTATATTTTTAATAAGAAACTTATTTTTAGAGTGCATAAACAATACAT
TTATAGAGATCATTAAAAAAAAATAAAAAATTAGTTCAAATATTGGAACGTTAACCCATTTATAACTACCCTGAAAATCGTTATGTTATCTTCAT
ATACACATATCAATTCTGAGTGAAACGTGTATAATA
(SEQ ID NO: 188)

Start ATG: 703 (Reverse strand: CAT)

MLPVILIACLAQLVLAQADLKDLDGPNICKRRELYNVDVVYTELQSFQERGSTWCVTFPPRCSTYRIKHRVVNKTKTIAKNRIVRDCCDGYIASA
GECVPHCSEPCQHGRCISPEKCKCDHGYGGPACDIICRCLNNSSCDPDSGNCICSAGWTGADCAEPCPPGFYGMECKERCPEILHGNKSCDHITG
EILCRTGYIGLTCEHPCPAGLYGPGCKLKCNCEHGGECNHVTGQCQCLPGWTGSNCNESCPTDTYGQGCAQRCRCVHHKVCRKADGMCICETGWS
GTRCDEVCPEGFYGEHCMNTCACPSANFQCHAAHGCVCRSGYTGDNCDELIASQRIADQSENSSRASVALTLVLMTLFACIIFAVFIYYRRRVSN
LKTEIAHVHYTHDTNPPSWPPNHNFDNPVYGMQAETRLLPNNMRSKMNNFDQRSTMSTDYGDDCNASGRVGSYSINYNHDLLTKNLNADRTNPIV
YNESLKEEHVYDEIKHKEGYKDPVKIYSKILFPEDEYDHLDYSRPSTSQKPHYHRMNDAMLNINQDEEKPSNVKNMTVLLNKPLPPTEPEPQHEC
FDNTNTNLDNVSTASPSSSPKFLK*
(SEQ ID NO: 189)

Name: EGF repeat molecule
Classification: cell_adhesion
Gene Symbol: BcDNA:GH03529
FlyBase ID: FBgn0027594

Celera Sequence No. : 142000013384481
AAAATGCAAATCCAAAATCAATCGTACTCCGCCCCTCGTCCTCCGGCAATCGATTCGTCGATATTCGGGGATTCCCTTCCTGATTTGCATAAGTT
TCCAGATAGCGCGCGTGCGCAGTCGATCGGCGCACCCGAATCCGTAATGCGGAGCAAACCCTCCTCCCCGATGTAGTGCAGGTCCATTTGCATAA
CACTGGCTGGAGGAGCTGGTGATCCGGATGTCGAACTTCCTACCCGATCGCCCGCTCCGCCTCGGGACGATGTGCCAAAATTATGCAAATGTTTT
ACACCAATAATTTATGCAAATTACGATCCGCAAAGGATTTGGTGATCCTGCGCAGCGGATGTTACACGTAGATGTCGCCAGCTTCAAATCGAAAA
TGTTTTTTAGGGGTTTGCTCAAGTTCAGAATTTCTGCAAACGTTTTTTATATGGTAATTTTTTTTTGCAATGGGTCTTAGGAAATATTTGGCAT
TTTTAATTGTGTTTTTTTGCACGATTGTAATGCAGATTTTTTGCTCGATTGTAATTTTAATTTGCAAATTTGGGTTTTTATTTTTTGCATTTGAA
TGGATTTCGATTCGATTATTTCAAAAAGGACAGGCAGCTGCTCCAGCTTGATATCCTTTTTGCAACGCGCCAATTTCTTAAAAATCATTTCGATT
CCCAGTTTTGCCGAAATTTTTGTGCACACAATTTGCATAGAGATGTGAAGGAAAAGGGAACAAAGATGCGATTCTATACTTTAAACGTTCTAAGA
TTTGATTATATTTATGGTAATAGGCGAATAAGATTGCCGATGCCAATATTTAGTGTGAGAAAGTATTTTTGAAAATCTTTTTTGAAATCGCTTAT
GAAAAAAATACTGTAGACGTCGAAATATTTAAAATATTCATCTTAGAATATGTATTTTTTGATAGAATAGAAAATATATAGAGATAATAACAAAA
AATTTAAAATAATTAACTATACAGTTTCTTGTGCCCAGATAACTTATTTACCCACTTTCTGCACGTAACTTTGCCGTAATTTGCCGTAATATCTT
TGCAAATTGCCTGCGATTTTGGATAAAATTCTCTGCTGATCTGTGCTCTTCTTTCATTTGCTGTCCCTTTCTAACGCACGTTGGCCATGCGGGA
TTCCTTCACAAATACACGCTCCTCTTTCGCATTTTTTTTTACCGAAAAACCTCTCTTTTCTAGATAAATTTACATTACCGCTGGCGTTTTATTGG
TCGAGAAAAGCGAGCAAAAAAACGGAAACCAGCCGAAAACAAGCTGGGTTTTCCCAGAGCATTTTCCTGCGAAGGGTCGGTTAAAAAACTAGGGG
ATGAAGGTCGAACCACCACCACCAACGGACTTCTCATTTTATTCGTTTTTAAGAGAGCGAGAGCGGCGAGATCGGTTTTTTAAGAGAACCGGTG
GCGAGAGGGTTGCACTTGGGCATGGATTTGCGCAATTTTTGCTATATTAGCCGGAGGCCGCGGAAGAGTTGAAGCAGTTTGAGCCTCGCAGCCGA
ACTTTGAGGATCGCTGAGACGAGACGCCGTGCAAGAAAGTCGATCCAAAATCCGAAATTCGAAATCCGTGCTGTGATCTGTGCTGAATATAGTGA
AGAAATCTTAAAGAATTTTCAAAAAGAAATCCCAGTGCTGTGCTGAATATATCCGCGAAAGTGTGCCACAAAAAATGTCCAACCAAATGGAGTTTA
TTATGCAACTCTACATGATGAACTTGATGAAGCAGCAGCAGCAAATGCAGCTCCAGCTTCCGCAGCAGCAACAGCAGCAGCAGCTGGCTGGATAC
ACTTACACACAGAACGAGGATATCTCTAGCAGCACATCCGTGCAGCAGCAACAGCAGCAGCAGCAGGAGCAACTGCAGCAGCCACAGCCAGATCT
CCGCAAGACAAGAACGCACAAGCGCATTAGCTCGCAAAACACCAACTGTAGTAGTAGCCGTAGTTGTAGTCCCAATAGTAATTTGATTGCTTTTC
AACCACAACAATACCCAGGCGCTACAGCGGCAACTCCTTCCACTCCCAACAGCCACCCCAGCAACCTGGTCAACCAGATGCTGCTCCAAAGCCTG
CCGCCGCTGACGCAGCTCATGTTGCAGCAGCAGCAGCAGCAACATTTGCTGACCACCTCCAACCTTCTACTAACACCCACCCACACCCCCAGTTC
GCTGGGCAAGCAGGATCCACTGCAGCATCCGTTGTTGCTGGGCCAGTTTGCCGGCTCCGAACAGATGGCCACAAATAACTTCCTTCAATCATCCA
CAGTGACCTCCACGCCCATCGAGAGAGAGAAGGCAGCCACACCAGCACCCTCCGCCGGAGCAACTGCCGGCAACCTTTCGGCGGCCCAGGTCAAG
TTTGAGCAGGAGTCCGCCGACGACGATGAGGACGATGATAAGCCGCTGTCCAGCCTCACCAGCTGCAGCTCCTCGGGCCACACCAACGCCAGCTC
CGAGAAGCTGCTGTTGTCGGGCGTCCATCCGCTGGAGTCAACCACCGACAGCCTAGACTCACCCAGCATGGTAAGTGATCCGGGGATCTAGAAGG
ATCTTAACAGTTTCTTTTATCTCGTTTTATCACCATCAATTTTAAAGATACTGTCACTTGCAGTGGCAACTACGTAGTCAAAAAGCTATATATTG
CGCATTTTTGTATTAGTACATTTGATTTAAATTCTAAATTCATCCCAACAGCTTGGTTCGCCATACTTCACAAACCTTTTCCAGTTGCAAAATAG
ACCATTTTCCAATTTCCAATTCAGAAAGCACTATATTTGTTCCCTATTTTGCTTTGTTTTTTTTTTTTTTGGCTATGTCCCACGCTCTGTTGCT
GTAATTTGAGAAAAAACGATTCGTGATTTTTGAGATTTAAGTGTGAGAGTAGCCAGAAAGCTCGCGATTCCGGGGAAAAGAAACAGCTGTGTCGG
CAACGCGTGGGTTCTCTTGGTGGCTCGATCGCTGCCCAGCTGGGCACCAGGCAGTCTGAGCTGGGGATCTCACAGATGCATCCGTGTGTTGGTAT
TGACTCTAAAGTTCTTCCACCCTCTTTTTCCCACTGCAGTATACGCCCGTCAAGCAGCCGGCGGACTCATCGTACGGACTCATCACACCCGTCGA
CAGTGATCTGACCCCCAACACACCCCTCCAACCGACCCAAACAATATCCCTGCTGACGCCGCCGTCGAGTGAGCAGAGCAAGAGCCTGGTGAGCC
TCTCGGCGGCCAGCGGCCTGGATGCTCTGCTCCAGAACGAGGAGGTACTGAAGAACCTGCGGAAAGTGTCCTCCTACCTGGAGTGCGAGAACAGC
CTGTGCAGGCAGGAGAACCTGCGGGAGCACTTCCATTGCCACGAGGAGCCCTGCCAGGGCAAGATCCTGAGCAAGAAGGACGACATCATCCGGCA
CCTGAAGTGGCACAAGAAGCGCAAGGAAAGCCTCAAGCTGGGCTTTGCCCGCTTCTCCTCCTCGGACGACTGTGCACCAGCCTACGGAGAGGGTT GCGCCTACAACTGGAAACAGACCCACTACCACTGCGTCTACGAGCACTGTCCCAAGGTGTATGTGAGCACCAGTGACGTCCAGATGCATGCCAAT
TTCCACCGCAAGGACTCCGAGATCGTGAACGAGGGCTTCCGGCGCTTCCGGGCGCACGAGACCTGCCGCATCGAGGATTGCCCCTTTTTCGGCAA
GAAGATCTCCCACTACCACTGCTGTCGCGAGGGATGCACCCACACCTTCAAGAACAAGGCCGATATGGGTAAGTCTACTTGGAAAGCTTATTAGC
TGAACTTAGTTAATATATCATATATGTATTTCTCCTTGCTTAGACAAGCACAAAACTTACCATCTGAAGGACCACCAGCTGAAGATGGACGGCTT
CAAGAAGATCCTGAAGACCGAGGTATGTCCCTTCGACGCCTGCAAGTTCTCCACCGTCTGCAACCACATCCACTGCGTCCGCGAGGGCTGCGACT
ACATCCTGCACTCCAGCAGCCAGATGATCAGCCACAAGAGAAAGCACGATCGTCAGGACGGAGAGCAGGCGTACCAGCAGTTTAAGATCAAGCAG
GACGTGGAGGAGTCCTCCCTGGATGCCATGCCCCAGCAGCAGCAGCAGCAGCAGCAGCAGCAGCCCACCAGCCTTAGTCAATCCCAGAGCAGCAG
CTCTGTATGCGGCGGCAGCAACACCTCCACTCCACTCTCCTCTTTGTCCGCCGAGCACTTCCTGGCTCGGAAACGCGGCAGGCCACCCAAGAAAA
TCGTAAGTTTGTCTGTATATTTTGGGTAATTTTCCGCGACATTAAATAGGCATATTTTCTCAATCCACCACAGCAACTGCCAGCCGACGCTCAGC
AGTCGGAAGCCAAGCGCCTGAAAGTCGAAGACGAGTCCTCTAATCCCGCCATGCTCCTGCCCCAGTCCCAGCCAGCAGCCGCTGTGCATCCGCTG
ACAAGTGGACTCTTTCCCGGTCTCCTGCCCGCTGCCGCCGCTCCTGGAGTGGATCCCACAGCCCCTAACTTCCAGCTCACCCACCTGATGGCCCT
CTTCCAGTTGCAGAATCCCCTCTTCTACCAGAACCTCTATCCGGGAATGACCCAGAATTCCTCCATGCTCGGCAACCTGGCAGCACTTAGCGCCG
CATCGGCAGCAGCGGCGGCGGCAGCGGCGGCAAATGGAGCCGGAGTCCAGCAGCCGAAGGCAGAGTTTAGCTTTAAGCCAGAGTTTAAGGAGTAG
GAAGGATGCGTGTCCTTAGGGTATTTTGCCAGCTACTTAGTTTGACCGACGGACGTTGGACATTGTACATACGCGCTTTAAGCAGGTTTAGGTGG
GTTTTTTTGTGGGTTCAGGCAGATCCAGGACAAGGCATCCTTCCCTCCACAAAAACCAACTCAGCCACACTTTGAGAACCTAGAAGTCCCCTATA
CAAAGTGTAGCTGAATTGGCTTTTGCCAAACATTTTCCCCTTTAGCTTAGATTCTCTCAGTGCCACATTAATTTTTAAAATTTTCAGCCATTTTA
AATAAAAAGGAAGAACTTTCTGAATTTAAGTTTGACTAAACTGTGATGTTTTCATTAGAGTAGCCTCTTTTAATTGATAGAGCGAGTGCAGGCTA
TGCAGGATATGCAGGACTTAGGAGACTTGGATTGTCAATAACATAGCGTCTAAGCATTACATTGTATGTGATATACTAATAAATAATGGCTAATT
GTTTTTGCTTTATAATTTAAGGGAATAATATTATAATTCTAATTATAAACTTTAGTAAAATCAGCATTCTTCTATAATAAATAAGTCAACATTAC
CTGAATAAATTTTATTATGCCTCAGAGCTTATTATTTAAACACAAAATGCTTGAGTTATTGGGGGTTACTGGAAAATACAATATATAAAGTAACT
AACATATATGTATACCCAACCACACATAAAACACTTAAACATTTGATTAAATAATTTATGACTTTATTTTGTTTTCATGTAATTGTTGGTTTTAC
TCATATGCTAACAGAAATCAGCTACACAAACTCAGGACGCCTGATAAAAACCGTCCCGCTAAGCAATATTTAAGTACTTTACACAAAATCAATTA
TTTTTTCCTTTGCTTGTATTTTTGTATTTTTTATAGTTCATAATCGCATATATGTATATGTAAACAATCAATACAATCCAAATACCATAATCATA
AGCATAACAAAAGAGATTTCAGAAAGTTGTATCCTAGTCAAGAACAATGTACAAGCAAGTATCATCATTTTATACATTAGGTATTTGCTTTTAGT
TTACATTGCAAAGTGAAACCCTGCGTGAAATGTACAAATAAAGGTAAACTAAAAATAACATTAAGAACTAATGGTCTAGAACTCAAGAAACACGA
AAATCAACAAGTAAACTTCTAAGTAAATTCGTTAAATGTTATGTTAAAAGTAGGAGAAAACTTAAACAAACTACAGACTCAGTAATGCCTTTTGA
TTTTGCCTAAGGTTATAAGCTTCGATTTTGATGCGGTAGCCAAATTTATAAAACCTTGAAAAAGCAGTATCCAATTTATTCCTATAAGCATCTAT
ACTCGTCTAATTTTTTGGGTCATCAGTTTATAACGATTGCATAACTTCCGGTGCAATATCTATGGCAACATTTTGTGCGCACATCGACACATACA
CACAATTTGAAAACGAAGTTTAAGTTTGTATCTTATAGGTTGGGTTAATCGTATCTAAGCCGCAACAGAAGAGGTTATGAGTAGCGTTGGGTTTG
AAAGCTGCCCGTTCTGCCGGCGGGCCTTAATCGCGGTAAAATCCGCGCAGCAGTTTCCCAATAAATCAGAACCGTTAGCTGCGACCGGT
(SEQ ID NO: 190)

Exon: 1001..2540
Exon: 3080..3773
Exon: 3844..4277
Exon: 4349..5359
Start ATG: 1689

Transcript No. : CT6850
CCCACTTTCTGCACGTAACTTTGCCGTAATTTGCCGTAATATCTTTGCAAATTGCCTGCGATTTTGGATAAAATTCCTCTGCTGATCTGTGCTCT
TCTTTCATTTGCTGTCCCTTTCTAACGCACGTTGGCCATGCGGGATTCCTTCACAAATACACGCTCCTCTTTCGCATTTTTTTTACCGAAAAAC
CTCTCTTTTCTAGATAAATTTACATTACCGCTGGCGTTTTATTGGTCGAGAAAAGCGAGCAAAAAAACGGAAACCAGCCGAAAACAAGCTGGGTT
TTCCCAGAGCATTTTCCTGCGAAGGGTCGGTTAAAAAACTAGGGGATGAAGGTCGAACCACCACCACCAACGGACTTCTCATTTTATTCGTTTTT
TAAGAGAGCGAGAGCGGCGAGATCGGTTTTTTAAGAGAACCGGTGGCGAGAGGGTTGCACTTGGGCATGGATTTGCGCAATTTTTGCTATATTAG
CCGGAGGCCGCGGAAGAGTTGAAGCAGTTTGAGCCTCGCAGCCGAACTTTGAGGATCGCTGAGACGAGACGCCGTGCAAGAAAGTCGATCCAAAA
TCCGAAATTCGAAATCCGTGCTGTGATCTGTGCTGAATATAGTGAAGAAATCTTAAAGAATTTTCAAAAAGAAATCCCAGTGCTGTGCTGAATAT
ATCCGCGAAAGTGTGCCACAAAAATGTCCAACCAAATGGAGTTTATTATGCAACTCTACATGATGAACTTGATGAAGCAGCAGCAGCAAATGCAG
CTCCAGCTTCCGCAGCAGCAACAGCAGCAGCAGCTGGCTGGATACACTTACACACAGAACGAGGATATCTCTAGCAGCACATCCGTGCAGCAGCA
ACAGCAGCAGCAGCAGGAGCAACTGCAGCAGCCACAGCCAGATCTCCGCAAGACAAGAACGCACAAGCGCATTAGCTCGCAAAACACCAACTGTA
GTAGTAGCCGTAGTTGTAGTCCCAATAGTAATTTGATTGCTTTTCAACCACAACAATACCCAGGCGCTACAGCGGCAACTCCTTCCACTCCCAAC
AGCCACCCCAGCAACCTGGTCAACCAGATGCTGCTCCAAAGCCTGCCGCCGCTGACGCAGCTCATGTTGCAGCAGCAGCAGCAGCAACATTTGCT
GACCACCTCCAACCTTCTACTAACACCCACCCACACCCCCAGTTCGCTGGGCAAGCAGGATCCACTGCAGCATCCGTTGTTGCTGGGCCAGTTTG
CCGGCTCCGAACAGATGGCCACAAATAACTTCCTTCAATCATCCACAGTGACCTCCACGCCCATCGAGAGAGAGAAGGCAGCCACACCAGCACCC
TCCGCCGGAGCAACTGCCGGCAACCTTTCGGCGGCCCAGGTCAAGTTTGAGCAGGAGTCCGCCGACGACGATGAGGACGATGATAAGCCGCTGTC
CAGCCTCACCAGCTGCAGCTCCTCGGGCCACACCAACGCCAGCTCCGAGAAGCTGCTGTTGTCGGGCGTCCATCCGCTGGAGTCAACCACCGACA
GCCTAGACTCACCCAGCATGTATACGCCCGTCAAGCAGCCGGCGGACTCATCGTACGGACTCATCACACCCGTCGACAGTGATCTGACCCCCAAC
ACACCCCTCCAACCGACCCAAACAATATCCCTGCTGACGCCGCCGTCGAGTGAGCAGAGCAAGAGCCTGGTGAGCCTCTCGGCGGCCAGCGGCCT
GGATGCTCTGCTCCAGAACGAGGAGGTACTGAAGAACCTGCGGAAAGTGTCCTCCTACCTGGAGTGCGAGAACAGCCTGTGCAGGCAGGAGAACC
TGCGGGAGCACTTCCATTGCCACGAGGAGCCCTGCCAGGGCAAGATCCTGAGCAAGAAGGACGACATCATCCGGCACCTGAAGTGGCACAAGAAG
CGCAAGGAAAGCCTCAAGCTGGGCTTTGCCCGCTTCTCCTCCTCGGACGACTGTGCACCAGCCTACGGAGAGGGTTGCGCCTACAACTGGAAACA
GACCCACTACCACTGCGTCTACGAGCACTGTCCCAAGGTGTATGTGAGCACCAGTGACGTCCAGATGCATGCCAATTTCCACCGCAAGGACTCCG
AGATCGTGAACGAGGGCTTCCGGCGCTTCCGGGCGCACGAGACCTGCCGCATCGAGGATTGCCCCTTTTTCGGCAAGAAGATCTCCCACTACCAC
TGCTGTCGCGAGGGATGCACCCACACCTTCAAGAACAAGGCCGATATGGACAAGCACAAAACTTACCATCTGAAGGACCACCAGCTGAAGATGGA
CGGCTTCAAGAAGATCCTGAAGACCGAGGTATGTCCCTTCGACGCCTGCAAGTTCTCCACCGTCTGCAACCACATCCACTGCGTCCGCGAGGGCT
GCGACTACATCCTGCACTCCAGCAGCCAGATGATCAGCCACAAGAGAAAGCACGATCGTCAGGACGGAGAGCAGGCGTACCAGCAGTTTAAGATC
AAGCAGGACGTGGAGGAGTCCTCCCTGGATGCCATGCCCCAGCAGCAGCAGCAGCAGCAGCAGCAGCAGCCCACCAGCCTTAGTCAATCCCAGAG
CAGCAGCTCTGTATGCGGCGGCAGCAACACCTCCACTCCACTCTCCTCTTTGTCCGCCGAGCACTTCCTGGCTCGGAAACGCGGCAGGCCACCCA
AGAAAATCCAACTGCCAGCCGACGCTCAGCAGTCGGAAGCCAAGCGCCTGAAAGTCGAAGACGAGTCCTCTAATCCCGCCATGCTCCTGCCCCAG
TCCCAGCCAGCAGCCGCTGTGCATCCGCTGACAAGTGGACTCTTTCCCGGTCTCCTGCCCGCTGCCGCCGCTCCTGGAGTGGATCCCACAGCCCC
TAACTTCCAGCTCACCCACCTGATGGCCCTCTTCCAGTTGCAGAATCCCCTCTTCTACCAGAACCTCTATCCGGGAATGACCCAGAATTCCTCCA
TGCTCGGCAACCTGGCAGCACTTAGCGCCGCATCGGCAGCAGCGGCGGCGGCAGCGGCGGCAAATGGAGCCGGAGTCCAGCAGCCGAAGGCAGAG TTTAGCTTTAAGCCAGAGTTTAAGGAGTAGGAAGGATGCGTGTCCTTAGGGTATTTTGCCAGCTACTTAGTTTGACCGACGGACGTTGGACATTG
TACATACGCGCTTTAAGCAGGTTTAGGTGGGTTTTTTTGTGGGTTCAGGCAGATCCAGGACAAGGCATCCTTCCCTCCACAAAAACCAACTCAGC
CACACTTTGAGAACCTAGAAGTCCCCTATACAAAGTGTAGCTGAATTGGCTTTTGCCAAACATTTTCCCCTTTAGCTTAGATTCTCTCAGTGCCA
CATTAATTTTTAAAATTTTCAGCCATTTTAAATAAAAAGGAAGAACTTTCTGAATTTAAGTTTGACTAAACTGTGATGTTTTCATTAGAGTAGCC
TCTTTTAATTGATAGAGCGAGTGCAGGCTATGCAGGATATGCAGGACTTAGGAGACTTGGATTGTCAATAACATAGCGTCTAAGCATTACATTGT
ATGTGATATACTAATAAATAATGGCTAATTGTTTTTGCTTTATAATTTAAGGGAATAATATTATAATTCTAATTATAAACTTTAGTAAAATCAGC
ATTCTTCTATAATAAATAAGTCAACATTACCTGAATAAATTTTATTATGCCTCAGAGCTTATTATTTAA
(SEQ ID NO: 191)

Start ATG: 689

MSNQMEFIMQLYMMNLMKQQQQMQLQLPQQQQQQQLAGYTYTQNEDISSSTSVQQQQQQQQEQLQQPQPDLRKTRTHKRISSQNTNCSSSRSCSP
NSNLIAFQPQQYPGATAATPSTPNSHPSNLVNQMLLQSLPPLTQLMLQQQQQQHLLTTSNLLLTPTHTPSSLGKQDPLQHPLLLGQFAGSEQMAT
NNFLQSSTVTSTPIEREKAATPAPSAGATAGNLSAAQVKFEQESADDDEDDDKPLSSLTSCSSSGHTNASSEKLLLSGVHPLESTTDSLDSPSMY
TPVKQPADSSYGLITPVDSDLTPNTPLQPTQTISLLTPPSSEQSKSLVSLSAASGLDALLQNEEVLKNLRKVSSYLECENSLCRQENLREHFHCH
EEPCQGKILSKKDDIIRHLKWHKKRKESLKLGFARFSSSDDCAPAYGEGCAYNWKQTHYHCVYEHCPKVYVSTSDVQMHANFHRKDSEIVNEGFR
RFRAHETCRIEDCPFFGKKISHYHCCREGCTHTFKNKADMDKHKTYHLKDHQLKMDGFKKILKTEVCPFDACKFSTVCNHIHCVREGCDYILHSS
SQMISHKRKHDRQDGEQAYQQFKIKQDVEESSLDAMPQQQQQQQQQQPTSLSQSQSSSSVCGGSNTSTPLSSLSAEHFLARKRGRPPKKIQLPAD
AQQSEAKRLKVEDESSNPAMLLPQSQPAAAVHPLTSGLFPGLLPAAAAPGVDPTAPNFQLTHLMALFQLQNPLFYQNLYPGMTQNSSMLGNLAAL
SAASAAAAAAAAANGAGVQQPKAEFSFKPEFKE*
(SEQ ID NO: 192)

Celera Sequence No. : 142000013384570
AAAGATGGCACGGTGTGCATGGAAAAGTTGCCGTTGAATGGGAAATTGCTGCGACACGTTTTTGCCTTGGTCTGCTGGGATGGGATCTGTGACCG
GTCTGAGTCGGCGGTGGTCCGGTGTCTATGTCTCAGCCCCAGGTTTGTTTTCCGCATAAAAAGACACATTCATGCTGGCATTCTGCAGCCAACTT
TAGCCTTTGGGTGCTAACCGGCTAACTCGGCTGGCTTATGCAAAACTCCACATCCTCAGCTATTCCGCGACGATGTACCTTGTGCAACACCCCAG
ACACTATGGAGTCTGACCAGTTTATCCACCCGCCATGTGGTCATCTAGGTGCACCGTTCTCGAGGCGCGGTAAAAGTAAAAGTTAATGTGTGTGG
CCGGCGCGTGAAGAATGGCAATTACAGATCGATGATCGCCGTGAACCAGCTGGCTCATTTAGCCTCCTTAATTATGCCACGATTTCGCTCATCCA
ACTCATCTGCTTTCTGGCCATGGAGGTGCCCCATTGTGCGACTTACTTTGCTATTTTGTGTTTCTCTGGCCAAAATACGGAAAGTGGCAAGGCAG
AAAACATAAATGATTTTACGGGGGTCTAAATGAGTTAATTAGGTTTGCAGTCGAGAGGTCTTAACCAACACGAGTTGGCCATGGCAAAGCCAATG
AAGATATCAGAGAAGGGGTAATATGTAGGTGGATGGATACATTTGTACTACATGAACCATGCAACCCTAAAGGCTTTGGGTTTTGTTGAGTTATT
TTGGAAATCTGTTTTTCTCCATCATTAGCTAAGATTAAGCGTTTAAAAGATAATATATCTATTAGGAATCATGATTTAATAAGAAAAGATAATAC
ATATTTAAAAAAAAAAATTATTCCACAGACCATTGCTGAAAAATTTGAATAAAGCTTAATGTAATGCGTAGTGAATAACTCGCACCTTTATAACA
TACAAATACGGTCTCTTGGTCATGAGACTCTGGCTGTACGTATCCCTGATTCAAAGCTCGTTATGGATATGCTTGGAAATGTAAACAGTGAGATC
CTCAGGCAGCCCAAACATATCCAACTCCTTGGCTAATGCGAAGTACCGCCGCCTAAGAATGTGAGCCACTTCTTTGGGTTGTCGGTTCCTTGTAA
AGACTCCCTTTTGTTGCCGCCCACGCGGGTAATAGCTGCAGAGGATAATTTTAATTGGGTTTGACTCTTGTTCAAAAGCGTTTGAAATACAGAC
TCTGCGCGGTCCGAAAATCGGCGAAGTTCCAAACAAACTCTCCAATAAACCATCCTCTTCCGCGTAACTCGTCGAAAGCCTTGAAATGGCGAGAG
AAGAGCTCAACCTGGTATTCCTCCGACCAAATAAAGGCGGGAAGCTTTGGGGAAAGTCCGAATTAGAATCAATTATAGGCCTGAACAGGGTTCCT
TACTGAGTGCATGCCCTCCATAGTGTCGCCGCCGTACTCAAATTGGATGACAGGCTTTCCGAACCTATCCCGCCAACTCTGGGCCTCTATCGTCA
ACAGGTTAAGTATCATGTCAGTACGGCCCGAGTTCTGATACCAAGAGTTATAGCGATTGAAACCCACGATGTCCAGAAACTGCGCCAAATGGCAA
CTGGAAGAGTTGGCATTTATAGCCGCGGTTAGAGGTCGTCCGTGAGCTATTTCTCTTACATAGTTTACCAGGAATCTAAAGGTAAGACATCCGCG
TTAAATTTTTGATCTAAGATGTACTTTCTACTGACTCAAAGTATTTAAGGGCTCCCTGCTTGTTCGATCTCGGCTCGTTGGCTACCGACCATGCA
ACAACACTTGGATGGTTTCTGTCCCGGTGGATCAGTTGCTCCAGCGAGGACATGTGATTCTCCAGTAGCTGCGGCTCGAAGATATCTATATTGAC
AGCAGGGCATTCGTCAATAATCATAATACCATGCTGATCGGCAAACTGCATTGACTCTTCGGAATAAGGATAGTGAGAGGTGCGATATGCATTGG
CTCCAGTCCACTTCAGCAGGTTAAAATCTCTAGCAAGAAGCGCATTATCCAATCCCTTCCCGCGGATCTAGAATAAAGATTTTGATAAGCTTAAT
GACCAGATTTACCCAACAATCAAGCTCACATCGGAGTCCTCGTGCCGTCCAAATCCCCGCAGATAGAGGGGTTTTCCATTCAGCAGCAGGCTGTC
GTTGTCCCAACTTAAGCTACGTATGCCCACTGGGAGGCGGTAGGTATCCTGCAGAGATTCCAACTCCTTCTCATTGCTGGCCACAAACAGCTCGA
ATTGAAGATTATACAGGTAGCCGGGATCGGAATGCATTAGGTAGGGCCACCAGGGAGTTGCATTTGGCACCAGCAGAGTACCATGGTAGACCGCC
TTGTTGATCTGCTGGGCGGCCACATGACCATCTTTGTCCCTTAGTTGCACCCGAAGTTGGATGGGCTGGATTTGGAGGCCCTCCTTGCTAGCATC
CAACCACACGCGGTAGTCTATGCGGCCCAATCCTTCTTTAGTTAGTTGGGTGGTGACCTCCAAATCGCTTATGTGCAGCAGCGGGGTCGTGTACA
AGTGTACACTCCGGTGGATTCCCGCGTAGTTAAAAAAATCGAAAGTGTAACTCTGGATGGGCACGGTGCCGTCATCCGTAGCCACCTTGTAAACA
GAACCCTGAGGAATGGTGCGGTTGCTCAAACGATTGTCACACATCACCGTGATCCTGTTATCGCCGCCAAAGCTGAGCAGTCCCGAGATCTCTGA
CTCAAAGGGTAGGTGGCCAATGGAGTGACTTGTGGCGTTCCTTCCGTTGATCCATACCACGGCCGAATAGTGAACGCTGCTAAATCGCAACCAAG
TGCGTTGCATAGTCTTCCAGGAGCGCGGCACAAAAAAAGTACGCTCATACCATACGGTTCCAACGTGATCTCGTAAGTTATCTGTAGTGATGTCG
TTATAGGAGGCAGGCACTGGCATCGAAATAATCTCCCTTCCGGTTTTTCTCAAGGCATCCATAAACCACTTTTCCCTAATTCCCTGTAAGGGGTC
ATATGGATCACTCCTAACCAGTTGCCACATTCCATCCAAGCTCCGCACTTCACGGGTCTCCGAATCCCTGGGGTACAACAATCCCTTGGTTGGTG
TGGGCTTTCTGACATTATCATATTCAAACAAAGGGGAATCAGTTAGTTCTTTGCGATTGGCGTTCACCAAGAAGTCGTTTTCGGTGTAAGCCAAT
AGAACCTGGAGACTGCCAAGCAGTAAGCAGGTGACGGGCATCCAATGACTTTTCATCTGAAATCAGAATATTTCTATCGAGTTACAATTTAATGG
TTATCAAACATTTGTGAACCATCTTCTTCTTCACCCGGCCTTTGATAAGAGCAGTGTGACCAGCGCAAATATAGTGAACAAAATCCATCTATTAT
TTAATATGAAATTTTTTTACATAAACTTAAAATTGTAAACTTAAAAGAATTTAGGTTTAGGTTTGGCCTTCTACTCATGATAAAAAAAAATTGTTT
ACCGTGAAACATCATTGTTTGGAATCTGCGTTTGAAGGATCTACTCAAGAGGTTAAAATAATTTGCAAATATCTGTGTATATCTCCCGCTTAATG
TTCTTTCAAACTTGGTCACAATCATTTTATTCAATTACATTTATTTGAAAATTGAAATAGTCCGTGACATGGGAATCCGTGAGGGCAATCGATGG
TTTGGTAGAAAAAATCGGTGCTGTCATATAATATCGATAAGATAATTCACCATCTGGTAGCACGACTAAGTTCATACGTGTAATTATCGGTAGTT
AAAAATAAAAATATTAATACGCCTTGATAGAGGCAACCCTCAGTTTCAGAGTTGAAAATCTCGATGGCAATGCAAACAACTTCGTTCGGCTAACA
AAACCCGACTAAATTCCAACGTCAACGAGAGCATAGACGATATTTTCGGTTTCTTCCCAAGTGATACCGATTCCGAGAGCTACGGCCTTATATGT
AGAGTGGGGGCAGGCAGAGATCCCGGCCAAAATTAACATATTCCTGGAGACTATCAGCCAGCTGGCGGCCCTGGCGACCTCGACCGGCATCATGC
AGCTGCTCTTATCGTCCGTTTGCATGGCGCTGACCAGCGCGGTGATTGGATTTGCCTACTACCAAAAGCAGCAGTTCTATCCTGCGGTGGTCTAC
ATCACCAAATCGAACGCCTCCATGGGGGTGAGTAAATCCTATCATACAATCCAGTCCCATGCCTAAGCCTTGTTTTCGTTTGCTTCCAGGTCATA
TACATACAATTCTTTGTAATTGTCTTCATGTTCGGCAAGCTGCTAAGCAAGGTGACAATCAGCAAGAGTACCTTGCAC

FIGURE SHEET 103

(SEQ ID NO: 193)

Exon: 3353..2120
Exon: 2062..1746
Exon: 1690..1429
Exon: 1374..1236
Exon: 1176..1001
Start ATG: 3286 (Reverse strand: CAT)

Transcript No. : CT6960
AAGAAGATGGTTCACAAATGTTTGATAACCATTAAATTGTAACTCGATAGAAATATTCTGATTTCAGATGAAAAGTCATTGGATGCCCGTCACCT
GCTTACTGCTTGGCAGTCTCCAGGTTCTATTGGCTTACACCGAAAACGACTTCTTGGTGAACGCCAATCGCAAAGAACTAACTGATTCCCCTTTG
TTTGAATATGATAATGTCAGAAAGCCCACACCAACCAAGGGATTGTTGTACCCCAGGGATTCGGAGACCCGTGAAGTGCGGAGCTTGGATGGAAT
GTGGCAACTGGTTAGGAGTGATCCATATGACCCCTTACAGGGAATTAGGGAAAAGTGGTTTATGGATGCCTTGAGAAAAACCGGAAGGGAGATTA
TTTCGATGCCAGTGCCTGCCTCCTATAACGACATCACTACAGATAACTTACGAGATCACGTTGGAACCGTATGGTATGAGCGTACTTTTTTTGTG
CCGCGCTCCTGGAAGACTATGCAACGCACTTGGTTGCGATTTAGCAGCGTTCACTATTCGGCCGTGGTATGGATCAACGGAAGGAACGCCACAAG
TCACTCCATTGGCCACCTACCCTTTGAGTCAGAGATCTCGGGACTGCTCAGCTTTGGCGGCGATAACAGGATCACGGTGATGTGTGACAATCGTT
TGAGCAACCGCACCATTCCTCAGGGTTCTGTTTACAAGGTGGCTACGGATGACGGCACCGTGCCCATCCAGAGTTACACTTTCGATTTTTTTAAC
TACGCGGGAATCCACCGGAGTGTACACTTGTACACGACCCCGCTGCTGCACATAAGCGATTTGGAGGTCACCACCCAACTAACTAAAGAAGGATT
GGGCCGCATAGACTACCGCGTGTGGTTGGATGCTAGCAAGGAGGGCCTCCAAATCCAGCCCATCCAACTTCGGGTGCAACTAAGGGACAAAGATG
GTCATGTGGCCGCCCAGCAGATCAACAAGGCGGTCTACCATGGTACTCTGCTGGTGCCAAATGCAACTCCCTGGTGGCCCTACCTAATGCATTCC
GATCCCGGCTACCTGTATAATCTTCAATTCGAGCTGTTTGTGGCCAGCAATGAGAAGGAGTTGGAATCTCTGCAGGATACCTACCGCCTCCCAGT
GGGCATACGTAGCTTAAGTTGGGACAACGACAGCCTGCTGCTGAATGGAAAACCCCTCTATCTGCGGGGATTTGGACGGCACGAGGACTCCGATA
TCCGCGGGAAGGGATTGGATAATGCGCTTCTTGCTAGAGATTTTAACCTGCTGAAGTGGACTGGAGCCAATGCATATCGCACCTCTCACTATCCT
TATTCCGAAGAGTCAATGCAGTTTGCCGATCAGCATGGTATTATGATTATTGACGAATGCCCTGCTGTCAATATAGATATCTTCGAGCCGCAGCT
ACTGGAGAATCACATGTCCTCGCTGGAGCAACTGATCCACCGGGACAGAAACCATCCAAGTGTTGTTGCATGGTCGGTAGCCAACGAGCCGAGAT
CGAACAAGCAGGGAGCCCTTAAATACTTTGAATTCCTGGTAAACTATGTAAGAGAAATAGCTCACGGACGACCTCTAACCGCGGCTATAAATGCC
AACTCTTCCAGTTGCCATTTGGCGCAGTTTCTGGACATCGTGGGTTTCAATCGCTATAACTCTTGGTATCAGAACTCGGGCCGTACTGACATGAT
ACTTAACCTGTTGACGATAGAGGCCCAGAGTTGGCGGGATAGGTTCGGAAAGCCTGTCATCCAATTTGAGTACGGCGGCGACACTATGGAGGGCA
TGCACTCACTTCCCGCCTTTATTTGGTCGGAGGAATACCAGGTTGAGCTCTTCTCTCGCCATTTCAAGGCTTTCGACGAGTTACGCGGAAGAGGA
TGGTTTATTGGAGAGTTTGTTTGGAACTTCGCCGATTTTCGGACCGCGCAGACTATTACCCGCGTGGGCGGCAACAAAAAGGGAGTCTTTACAAG
GAACCGACAACCCAAAGAAGTGGCTCACATTCTTAGGCGGCGGTACTTCGCATTAGCCAAGGAGTTGGATATGTTTGGGCTGCCTGAGGATCTCA
CTGTTTACATTTCCAAGCATATCCATAACGAGCTTTGA
(SEQ ID NO: 194)

Start ATG: 68 (Reverse strand: CAT)

MKSHWMPVTCLLLGSLQVLLAYTENDFLVNANRKELTDSPLFEYDNVRKPTPTKGLLYPRDSETREVRSLDGMWQLVRSDPYDPLQGIREKWFMD
ALRKTGREIISMPVPASYNDITTDNLRDHVGTVWYERTFFVPRSWKTMQRTWLRFSSVHYSAVVWINGRNATSHSIGHLPFESEISGLLSFGGDN
RITVMCDNRLSNRTIPQGSVYKVATDDGTVPIQSYTFDFFNYAGIHRSVHLYTTPLLHISDLEVTTQLTKEGLGRIDYRVWLDASKEGLQIQPIQ
LRVQLRDKDGHVAAQQINKAVYHGTLLVPNATPWWPYLMHSDPGYLYNLQFELFVASNEKELESLQDTYRLPVGIRSLSWDNDSLLLNGKPLYLR
GFGRHEDSDIRGKGLDNALLARDFNLLKWTGANAYRTSHYPYSEESMQFADQHGIMIIDECPAVNIDIFEPQLLENHMSSLEQLIHRDRNHPSVV
AWSVANEPRSNKQGALKYFEFLVNYVREIAHGRPLTAAINANSSSCHLAQFLDIVGFNRYNSWYQNSGRTDMILNLLTIEAQSWRDRFGKPVIQF
EYGGDTMEGMHSLPAFIWSEEYQVELFSRHFKAFDELRGRGWFIGEFVWNFADFRTAQTITRVGGNKKGVFTRNRQPKEVAHILRRRYFALAKEL
DMFGLPEDLTVYISKHIHNEL*
(SEQ ID NO: 195)

Name: BETA-GLUCURONIDASE PRECURSOR
Classification: enzyme

Celera Sequence No. : 142000013384244
TCCTGCCGGTCCAGTGTAGAATTTATGTTAAGGGCATCCGCCCCCTGAAAGAGGCTTATACCTGGCGTGTTCATATTCGGCTAAGGGGACGCCAC
AAGCATCAAATTCAAATAAATTCCGAGGCGCAGGCGCTATTTTCGTAGGCAACTCTAATTTTCTTCCTCTTGCTTCTGTTGACACTTTGACATTA
ACATAGTAACGCGTGCTGTTAAGTGCAGTAAGCGCTTCTGTAGCGAAAACATTGCGTTCACACTACATACAGTCTAGAAGGGAATTAGGTTTTTA
TTCTATACTTGTACATAAACTGTAATTGTTAAATTTAAAAATAAATATTTTCCCAAAAAGTTGCCGATATGTCGAAAAGATTGTGGCCCCGACAA
TAGACCTGCCAGGCATACACAAGCTTGAAGATGATATTGTATGTATGTATTATCATGCCAACTATGGTTCCGTCGTATCATTGATAGGGGGAGCT
GTTGTGCATTGCAGAATGCAGTAGATTTGCTATTGGAATATACATACATATGTATGTCGTGTTAGTCCAGATGACAGGTATGTATTTTCAGACAC
GGCCAGTAATTTTTTATAGGATCACTTTATAGAAAGAATTTCTTCTACCTTTCAAATACATTTCAACGAATCGAAAAAATATAACTTGCTTTTTA
ATTTAATGGGAGTCCGCTCATTTCATAATATCGAACAGCTAAAAAATGTTACATTTCAAAGATATTCTAAAAATATGAATACCAACTAGACTCCA
GCAGGATAAAAATAAATCGCTTTAAATTGTTAACCGGCAATTTGTACCAGAATTTGCACATACATACATATGCATATATGTATGTATATATATCC
TAACACCGTTTTAGAAGAAAAACTCAAATGGATTGTTTTTAATTTTTATAATAAAACTTATTATTCAGTTAGTGTTGAGTGTCCTTGTTGCAATG
CAAAAACAACAGCATACTTTCTTTTTCAATTTTTTTCATTTTTATTAATTTTATACAGACTGTCCATTCATAAACGCACTTATATTGGGACATTT
ATCTAATTTCTCGGGATCTATTTGGAAAACCTTGGACAAACGTTTCCAACTTTGCGCATCAAAGTAGTAGAAGGTGCCGCGCTCTTTTGTACCAT
TTTTTTCATATTGATCAATGCCAGGAATTCGAGTTATCCATATTTCTCCTCCACGTGGTATCGCCACTCGCGACTATGCCTGCGATGGGAGCAG
AATTTTAGTATATATGTATGTTCTATATATGTTCATACGAAGCTTAGATAATAGCTACGCAAGAGGAAGTACTCACAATTCAGCAGCTGCCATCA
ATTGCATCATATCGCCGATGTTCGTGTAAAAAAGGAAAAAGAGCAGGTCTTCTTGCAGCTTTTTCAGTACCGGCGCTGTTAGTTTGTCTCTTATC
GCAAAGTTAATCAGATATTCGGGTGGCACGTTGAACTCAACGTCTTGTGCTCTGAAAAAAGTAAATGCAAATCCAATGTTACTAATTTGGTACAC
CTCTTACTCAATAGTACTCAATAAGCAATTAAATTATGTAAGTTTATTATGTAAACTGACCTGCAGGGCTGTGCTACGAAGGGGCCAGCGAAGGT
TGTATGCAAGCTCTCCTGCGAGTTCAGGTTCAGGCCTAAACCCGTGAGATCCGTACCCAAGGAGAGCGTCACCAGATTGGGATCCGTTTCTGCAG
CCCGAATGAACGTCAGCAGGCCAACCATGCCGAACTGGTTGTTCACCATGGTCGCTGGTATGTTTGTGACCTTCCCTATTTATGCAAAACGAACG AAAGGTAAATTTGTTACATTTTTAAATAAATAAAATATTTCATGGTACTATTATTTCTGGATAAAATGGGTCAAGGATAGTATAGCTGTTGGGCT
TTTGTGATGTACACCGAAATCACCGAATTATAATATGAAACAAATAATAATAGAAACCAAGAAATCCATTGATTAAATGGTATCAATCATCCATA
GAGTGTTCAATTCAAAGCTCCAAATGATCAAAAGGTCAAAAATAGCTCTCTCACATGTTGTGAGAAGTGTTCCAGCACTCACCATCTGGCGAAGT
TTGCACGCCGCTCTTTACAAGTTTATCGTTGCTGGAATTATCGTTCAGATGCTCGCCGCCCGCTCCGCTCCCAGACGAGCCGCTTCCACTCCCCA
GGCCGCCGCCTACGCCCATCATGGCATTGCTGTTGGGTACGCTGTTGACGCCGCCAATGCCGCTGTTACTGCCCACCAGTCCTACATGGGACCCG
CCGACAACGCCGCTGGCTGCATTGCCGCCGACTCCTCCGCCTCCTGAGCTACCAGCTCCTCCGCCGCCGCCTACTGCCAAGCCCCCTATACCACT
GCCAACGGCACCGAGACCATTGCCGCCTACAACGCCGACGTTGGAACCGCTGCTGCCGCTCGCTGATCCGCTGACCACTATCGAATTCATCGGCT
TTTCCGTGCCGTCCAAGTGGTTCTCTGTGGACGCACCTCCGGAGCCTCCTGTTCCGGCGACGCTCCCCACCGCGTTCGTTGTGCCGTCCGAGTTT
TGGGTGCCCGGTAACGCAGGGAAGTCCTCGTTAGACATCGTGAACTCCGATTGCTCTGACGTCGGTTGCTTCACCATGCCAACTGAAATCAGAAG
AGGAGCGAGATGGTCGCCCAGGGCGAATGAGTGAAGCGAAGAAATTAGTACTAAAGCAGTTTAAGCTCATACAATACACACGATTTTAGTTAATT
TCTTTTTCCTCAACCAATTAAAATCAATGAGTAGGTCCAAACAGCATTTGTTCAAGGTTTTAAGACATGTTACTGTGAATTTAAAGTTATCCTTC
ACCTATATATGAACTTATAAAAGGTTAAGTCGCTTGCTTTATGTGAACAGTTTCTTTTTATTCATTGATCATGTTTCAAAGTAAATGAGATTGCA
TATAATAATATGTTTGGAGTATAATCCGGAAACACAATTTCATTTCAAACTCTAAATTGCAAAAGCTCTTCATGGAATCAGAAGCCCGTATTCGG
TTGGACCAACGTAGCCAAAGTAAATGTCCTTGACTGAATCTAGTTTTTGCAGCGTTTGCCATACCCAAACCAACACCCGAGGTTAGTCCCAAATA
CAGCGTAGCATATCTAAGTGGGCTTAATGAGCTGATCACGAGACACCACGCTTACAACCGATTCTTAATCGTAGTTTTAAAAACAAAAATAAATA
AAAAGAAGTGGATTTTGATTTGAACTCACAAGAGGTAAAGAAATTACCATAGGGTTTGCTGCCCGGCGGCTGGAGCGGATTCGATTGGGGCAGTG
TCTGGTCGTTCTGGCCGCGCGCATTCGTCAGCGAGGGGAACTCCGTGGGATCGAGCAGGGCAGGCGTGGAGGTGTCGCTACCACCGCCGCCGCCG
AACACGTGGAAGTTATTCAAAGGACCGCCACCGCCTCCGCCCGTTCCGTAGCCGCCGCGACCCGTCTGCATGAAGTTGCCCATGTTCGACTGCGG
AAAGAGATAATGATTAGCCAAGTCTTAACAATTTATTTTTAGAATTAGGACTGACATCTCCAACTCAATCTTAATAGAGGGTATATTTTTTATGT
AATGTGAAAGCATTTGTAACTTCTGAAATTAATGTATATTCCGTTGTATCAAAAATATTTCCTTTATATAAATCTGATCGATCAGCGATACGATT
CTCTGATGCAATCCGAAGTATTGAAGTACTAAACCCACAGTCAATGGATATAGATATTGTTATATGTTTTACTTTGAGTATCTTGGACAAGACCG
AGTTGGAGGAGTTAGACTTTGTTGTAATGCCGCGCTGCTTACCATGGGGCCACTGCCCAATCCTTGCATGGCTCGCCGCTCCACAAACTGACGCT
GGCCGAAGAGGTTGGCGTTGCGGTTGCCGCTCGAGATGGCGGGTCCGCCGACCGACAGCTGGGCATTCCGGTTCGGCGACAGTTGGGGCTGCTGC
TGCTGTTGTTGCTGCTGCTGCGGCGCCTGTCCGTAGTTCGCCGTTCCTGGATAGGAGTTGGCGAAGTCTAAGGCAACAAATGTGAATTGGTGCTC
CGTCAAAAGCTTTGGGCGACAAGTGCTTACCGGTTTGAAACATGCCCGACGTGGGCGTCACATGGCCAGCCAGGGAGCTACCACCGAATCCGCCT
GTTGTCCGGCCAGCTAACGCCGCGTTCGCTATACTTCTCGGGGGTTGTTGAAAATTTAAATTCGCCATAATCTGCAATGGAAGGGGTTGTCGGTT
ATTAGGCTGTGGCCTTGCTTTGCTTATCTACCCATAAAGAAAAACCCATATCGTATCCGCGTCGACATCGAAGTATCACTTAAGCAGTAATCACT
TAAATGTAATAGTATAGGGATTTCCTTTTGGCAAAAACAAACTAATATATATTTATTTTGGAGATTATTACGCGTTATATAACATTACGGTTAAT
ACGAGCAATTGGGAATATGCTGGATGATTCGCAACATAAATTCTCGAAGCCATCTGCGCAGCAATCAGAGAACTGCTGTCAAATGTCTGAATCAG
GGAAACTCTTCGCCCATAAACAAGGGTTTACAATAAAAACTGTGTGATTCAGTGGAGGGGGACTATATTGATAACAAATTGGCTCCCCGCAGATA
ATTGTCGCACACTAAATGCGAGTATATGCGTATTGAGCAAACAAACCAACAACCTTGTGGGTTAGCAGCCTGGAGCCATATATATGAAAAGGTTA
TCTTAACGGCAAAATGGGATCCCAAAAAAGGGCCACCATCTATAGTATATCTATAAACAAAATAGCCCGCGCCAAGTGAATCCGTTAAATGGCCG
ACGCATCAGCTGTCGATTGGCGAAGCGAATTCGGACAGCAAACAGAGCAGAAGGAGAAAAGGAGAGCAAATTGAGAGGCAGAGCAAGGAGGTGGA
GAACGAGAAGCATGGGCAGAAAGGCTGTGGCAATTATTGCCGTTCCTCTTTGTCGTGGGCACACTCATGCACAGACCGTGTGGATAAGATGGAGA
CCAAGACAATGGCGATGGTGTGGGTGAGAAAACCAGAATGACTGCCACCAGGGTGCAAGGGAGTGGGTGGAGAGCGGGGCAATGCAAAAGGATAT
AAGCCTCAACTTGTCCCTCGATCAATTATGCAGGCAGTGGTCAGTGCAGTGCAAAAGGTGTACAGTAAAAACAGTTAACATTGTAAAATACAAAG
CTTTATACCTTATCTCCACTACTGGCCAAACCACTACCGAGTTAGTCGAATTTCGTTTACTTCACTACGAAAGCTCCAGTTAGGTTTTGATGCTG
CTTGCTAGTACCATAATATGTAAATAACCCTTCCTATGGTAAAGACCGGCTTTATCTTATCGAAACTTCAACGTGCGCTGAACTCGCCTGGAATG
CAAGATATACTAGCACAGGATGCCAGTGCATTTAATTTGAAAGGAGCAAATCTTCCTGGAATACGGGAGCTGTCGATTAAATTGATGTTTTACCT
GCACGCATGTAACTTTATCAGCTGACCTAACAGACGCTTCCCAACACTGGCGACCGCGCTTACAACAAAATTCAATGGCTAGCGTTAACTCTGGG
GACAAGTGTTTAACCAACCATTTAACCTCGGGCGATTCAGCAAGTACAAAATAAGAACGACGGATCCGAAAGGAGGAATGCGCGCAACTTACCTA
AATTAACGTTAGACGATACTGTCGCTTCTTGTTCTTCCACTGTTAACGCTCGCTTTCCACTCTGTCCAGCAACAACAACATACACTGATCGAATC
GTTCTCACCGCATTTAACATTCCAAAGCGGCCGGCGGGACGAGGACGTAGGAGTCGTTGTCCTGGCGCCGTAACCGTAACTGTGACGGATCACGG
ATCGGCGAATCAGCAGGAATATGAAAGTCCGCTAACTCCCACTGGGCAGCTGTTGGTTAGCTGTGGGTGTCTCGGTCACTAGCACTCACTCGCTG
GAAGCTGAAAGGATGCAACGGAGAAACGGGAGCTGGAACCGTAGCGGGTGTAGGAGCGGGAACGAGGTTAGTTAGTACTTTTCCGCGCCGAGTCG
TCCCTAAATAAATGGCATATATACCGCTGTGCGTGTGTGCATATGTATATGTGCCTCGTCTGTATGCAGCGTGGTCTTCGTGCCGAAGAGACAGC
GAGCGAGAGAGAGAGAGAGAGGAGAGGAGAGTCGAAGGATGTTGATGCCTGGCGGAGGCTAAAAGTTGTCCGTTTTTCTGCGCCGCTCTTGCGA
CCACTGTAGTTTCTATATTCACGCTTATGCAAATGTCGCGCACGTTACACTCGGCCGATTGGATTGGCCAGGGCTCTCGCTTTTTGTTAATGTTT
CCGTTTTGTATTTTATTTGTAAGTAAATAATCGCTCGCTATTGCGCTGTTGTCTCTGCTTCTTACTACACTGCTGCACAAGCACTGTGTCTGTGA
CCCTGTGCGTGTGTTTGTGTGTGTGTCTGTCTTTGTTTTCTCAGTTCATTGAAATTTCACCCGAAGCAGCGAATTGGGCAAATTCCCTGCTAGAT
TTGCGCGTCTTTTACGCCGCCGACCCGCAAATGCACTCGAACTTAATGGAGCCGGGTCCTTACGATCCACTATCGAGGGGCAGTAAACAATTCTT
TAGCGCCCGAAATGGCTTTAAATTGTACACAAAAAATGTTCCGCAAAAAACTTTGTGGCTGTCACGAATACAAACACACAAGAATTAGGGATGTA
AAAATCTGCTATCGAGACAGCGTTGGTATCGATAGTAGTTAGTTTGCAACGAGAGGGTTTGGTGCATTGATTACTGTATATTTCAAAGAATATTC
GAATTGTTTTCTTTAAAGACAACAATTTTATTCGCCTTTGCGATTGGTAAAATAGTTGTTTACTTTTAATCGATAGACAAAAACAGTTATTGGGC
TGCCATCTGGGGCGTCTATGCGAAGACCTCTTTGCGTATTTCAGTTATCGATTACTGTGACAGTGCCTAGACCTCCTAAACTCAACTTTATTGCC
CGGCCGCGAATTGTCTTGATTGCAGATTTTCCGATTTAAACAAAATTTACTTGGCATTATGGGCAGCCAAAACTCGGACGACGACAGTGGTGAG
TGGCTAATGGCTAAGTCCAGGCCTGAGTAACTAATATTTACACTGTTCACATATGTATGTAGGTTCATCCGGTTCGAGTCGAAGTGGAAGCCGCA
GTGTCACGCCGCAAGGAGGTAGTGCGCCCGGGTAACTATTTGATATTCAAACACGGCGGCGGGAGAGTGCTGATTACCTTCCCCTCGTTTTCCAG
ATCCCAACGCAGTCGCAGGTCGGGTAGTGGCAGCGATCGTTCCCGATCGGGCTCCAGGTCTTCCCGATCCCGGTCCGGCTCTGGGTCTCCGCGTA
GTGCCAGGTCCGGGTCTGCAGAAAGCCGCCACTCGCAGCTGTCTGGCTCCGCTCGTAGTAAGAGATCAAGATCTGCTCACAGTCGCAGGTCGGGA
TCTGCGCGTAGCCGTAAATCTGGAACTCCGGAATCTCCACAAAGTCACAGATCAGGTTCGTTGCAAAGTCGCAAGTCAGGATCGCCTCAGAGTCG
TAGATCTGGTTCTCCCCAAAGTCGCAAATCGGGATCTACTCACAGCCGCAGATCCGGTTCGGCCCACAGTCGCAGATCGGGATCCGCTCGGAGTC
GCAAATCTGGTTCGGCACA
(SEQ ID NO: 196)

Exon: 6714..5698
Exon: 4248..4116
Exon: 4057..3843
Exon: 3509..3278
Exon: 2647..2078
Exon: 1785..1581

FIGURE SHEET 105

Exon: 1476..1312
Exon: 1220..1001
Start ATG: 4248 (Reverse strand: CAT)

Transcript No. : CT7034
TGACAGCCACAAAGTTTTTGCGGAACATTTTTGTGTACAATTTAAAGCCATTTCGGGCGCTAAAGAATTGTTTACTGCCCCTCGATAGTGGAT
CGTAAGGACCCGGCTCCATTAAGTTCGAGTGCATTTGCGGGTCGGCGGCGTAAAAGACGCGCAAATCTAGCAGGGAATTTGCCCAATTCGCTGCT
TCGGGTGAAATTTCAATGAACTGAGAAAACAAAGACAGACACACACACAAACACACGCACAGGGTCACAGACACAGTGCTTGTGCAGCAGTGTAG
TAAGAAGCAGAGACAACAGCGCAATAGCGAGCGATTATTTACTTACAAATAAAATACAAAACGGAAACATTAACAAAAAGCGAGAGCCCTGGCCA
ATCCAATCGGCCGAGTGTAACGTGCGCGACATTTGCATAAGCGTGAATATAGAAACTACAGTGGTCGCAAGAGCGGCGCAGAAAAAACGGACAAC
TTTTAGCCTCCGCCAGGCATCAACATCCTTCGACTCTCCTCTCCTCTCTCTCTCTCTCGCTCGCTGTCTCTTCGGCACGAAGACCACGCTGCA
TACAGACGAGGCACATATACATATGCACACACGCACAGCGGTATATATGCCATTTATTTAGGGACGACTCGGCGCGGAAAAGTACTAACTAACCT
CGTTCCCGCTCCTACACCCGCTACGGTTCCAGCTCCCGTTTCTCCGTTGCATCCTTTCAGCTTCCAGCGAGTGAGTGCTAGTGACCGAGACACCC
ACAGCTAACCAACAGCTGCCCAGTGGGAGTTAGCGGACTTTCATATTCCTGCTGATTCGCCGATCCGTGATCCGTCACAGTTACGGTTACGGCGC
CAGGACAACGACTCCTACGTCCTCGTCCCGCCGGCCGCTTTGGAATGTTAAATGCGGTGAGAACGATTCGATCAGTGTATGTTGTTGTTGCTGGA
CAGAGTGGAAAGCGAGCGTTAACAGTGGAAGAACAAGAAGCGACAGTATCGTCTAACGTTAATTTAGATGGCGAATTTAAATTTTCAACAACCCC
CGAGAAGTATAGCGAACGCGGCGTTAGCTGGCCGGACAACAGGCGGATTCGGTGGTAGCTCCCTGGCTGGCCATGTGACGCCCACGTCGGGCATG
TTTCAAACCGACTTCGCCAACTCCTATCCAGGAACGGCGAACTACGGACAGGCGCCGCAGCAGCAACAACAGCAGCAGCAGCCCCAACTGTC
GCCGAACCGGAATGCCCAGCTGTCGGTCGGCGGACCCGCCATCTCGAGCGGCAACCGCAACGCCAACCTCTTCGGCCAGCGTCAGTTTGTGGAGC
GGCGAGCCATGCAAGGATTGGGCAGTGGCCCCATGTCGAACATGGGCAACTTCATGCAGACGGGTCGCGGCGGCTACGGAACGGGCGGAGGCGGT
GGCGGTCCTTTGAATAACTTCCACGTGTTCGGCGGCGGCGGTGGTAGCGACACCTCCACGCCTGCCCTGCTCGATCCCACGGAGTTCCCCTCGCT
GACGAATGCGCGCGGCCAGAACGACCAGACACTGCCCCAATCGAATCCGCTCCAGCCGCCGGGCAGCAAACCCTATGTTGGCATGGTGAAGCAAC
CGACGTCAGAGCAATCGGAGTTCACGATGTCTAACGAGGACTTCCCTGCGTTACCGGGCACCCAAAACTCGGACGGCACAACGAACGCGGTGGGG
AGCGTCGCCGGAACAGGAGGCTCCGGAGGTGCGTCCACAGAGAACCACTTGGACGGCACGGAAAAGCCGATGAATTCGATAGTGGTCAGCGGATC
AGCGAGCGGCAGCAGCGGTTCCAACGTCGGCGTTGTAGGCGGCAATGGTCTCGGTGCCGTTGGCAGTGGTATAGGGGGCTTGGCAGTAGGCGGCG
GCGGAGGAGCTGGTAGCTCAGGAGGCGGAGGAGTCGGCGGCAATGCAGCCAGCGGCGTTGTCGGCGGGTCCCATGTAGGACTGGTGGGCAGTAAC
AGCGGCATTGGCGGCGTCAACAGCGTACCCAACAGCAATGCCATGATGGGCGTAGGCGGCGGCCTGGGGAGTGGAAGCGGCTCGTCTGGGAGCGG
AGCGGGCGGCGAGCATCTGAACGATAATTCCAGCAACGATAAACTTGTAAAGAGCGGCGTGCAAACTTCGCCAGATGGGAAGGTCACAAACATAC
CAGCGACCATGGTGAACAACCAGTTCGGCATGGTTGGCCTGCTGACGTTCATTCGGGCTGCAGAAACGGATCCCAATCTGGTGACGCTCTCCTTG
GGTACGGATCTCACGGGTTTAGGCCTGAACCTGAACTCGCAGGAGAGCTTGCATACAACCTTCGCTGGCCCCTTCGTAGCACAGCCCTGCAGAGC
ACAAGACGTTGAGTTCAACGTGCCACCCGAATATCTGATTAACTTTGCGATAAGAGACAAACTAACAGCGCCGGTACTGAAAAAGCTGCAAGAAG
ACCTGCTCTTTTTCCTTTTTTACACGAACATCGGCGATATGATGCAATTGATGGCAGCTGCTGAATTGCATAGTCGCGAGTGGCGATACCACGTG
GAGGAGAAAATATGGATAACTCGAATTCCTGGCATTGATCAATATGAAAAAAATGGTACAAAAGAGCGCGGCACCTTCTACTACTTTGATGCGCA
AAGTTGGAAACGTTTGTCCAAGGTTTTCCAAATAGATCCCGAGAAATTAGATAAATGTCCCAATATAAGTGCGTTTATGAATGGACAGTCTGTAT
AA
(SEQ ID NO: 197)

Start ATG: 1018 (Reverse strand: CAT)

MANLNFQQPPRSIANAALAGRTTGGFGGSSLAGHVTPTSGMFQTDFANSYPGTANYGQAPQQQQQQQQPQLSPNRNAQLSVGGPAISSGNRNAN
LFGQRQFVERRAMQGLGSGPMSNMGNFMQTGRGGYGTGGGGGGPLNNFHVFGGGGGSDTSTPALLDPTEFPSLTNARGQNDQTLPQSNPLQPPGS
KPYVGMVKQPTSEQSEFTMSNEDFPALPGTQNSDGTTNAVGSVAGTGGSGGASTENHLDGTEKPMNSIVVSGSASGSSGSNVGVVGGNGLGAVGS
GIGGLAVGGGGGAGSSGGGGVGGNAASGVVGGSHVGLVGSNSGIGGVNSVPNSNAMMGVGGGLGSGSGSSGSGAGGEHLNDNSSNDKLVKSGVQT
SPDGKVTNIPATMVNNQFGMVGLLTFIRAAETDPNLVTLSLGTDLTGLGLNLNSQESLHTTFAGPFVAQPCRAQDVEFNVPPEYLINFAIRDKLT
APVLKKLQEDLLFFLFYTNIGDMMQLMAAAELHSREWRYHVEEKIWITRIPGIDQYEKNGTKERGTFYYFDAQSWKRLSKVFQIDPEKLDKCPNI
SAFMNGQSV*
(SEQ ID NO: 198)

Name: Regena
Classification: transcription_factor
Gene Symbol: Rga
FlyBase ID: FBgn0017550

Celera Sequence No. : 142000013384812
ATCTTAAAGGTTGCTATATTTAAAGGCAAAATCATATTTCACATACAAGGCCAGTTGAAAAATTCAAATCACTTGAATGATTAATGGGTAAATGG
GCAACCTTTTTCAAGTAGAGCCTAAGCCAAGTACTACCATTTAATAACAACTTGTAATTAATACGAAATGTTCTCTTTCTAGTTATTTTTGAAGT
GTTTTCCGCGTGGGTTTACAGAATCGACATTTACGGCTCATAACCCACTGCACTGAAATGACGGAGTATTTGTGCTTCCCGATAGCCATTAGAAA
GTGGAGCTGGTAGGCGGGGAGGGTAGTGTGGGGTGTTGCAAGTGGGTGGCTTTTGGGCGACTGGGTGGTGTGGGAGGTGTCAAGGGCGCGATAGC
TCTTTGACAGCCGGGAAAGCGGATATGGAGTGAACGACAGGTTTTCCCTCAGCTCTTCCGCCTGGTAGTTCGTGTTTATGTAAAATTAATTTGAA
GCTTTTAATCAAATATTAGCGGCAAAAAATGCTGCGGAGCTTGGTAGGAAAAACTGAGCCACAAAGCAGTGAAATTAAATACTTAACCTACTTTC
AGCAGTCACTTTATGGACAAAATAAGAACTTATTCTCACGCATTAGCATTGTTTTAAGAAAAAAAGAATTTGCCTAACTAAAACACCAATTTGCG
TTTGTAGCAACTTATTGTTCCCTCAAAAACGTTAATATAAAACTAAAACCGCACTGTAATAATGATGATACATACTAAAAATGTGAAGGGAAGAG
TTAGTGATTGAGAAACGATTTATTTACTTTTACCACTTGTATTATTTGCTTTTAAAAATATCTACCGCGTAAGTATCTTACATTGTAAAATAAAT
GTAGGAAATGACTGATGTTATCGATTATTTATAAAATTCAAATGTTTAAGCTTTCGCGCGTAACATGGTATTTTTTAGGCAGTTATTCGCGTCCT
CGGATCACAATCTGGTAACATCGAAAGTTCTAATTTTGTTTGTGTGCGTGCGACGTCGGTTTTTCGTCGTCGCGACTTTTTTAAAATAAACTGG
AGGCATTCGCAAATAATTTAAGCCTAATCGATCAGGAATTCGTACATAATGTCGGTTGTGATATCGAGCTCTTTGTCAAGAAGCGCTTGAATCGT
GGGTAAGAATAAAGTCGCACCTACAAAATGAACGAATTAGAACTTTTTGCCACGAGAATAGCAAGTGCATATGTGTGGGTGTATGTTAGTGTGGG
CATTTGTGTGTGTGTCTGTTGTGGTCTCTGAATGTGTGAGTGAAGGAGAAGGAAGTAGAGCTCCCCTTATTTCTCCAAAAACAACAAATACAGAG
AGTAAGAAGGAAAGAGTAGGAGAGAGAATAACTTGTAACAAAGTACCGTTACAACAATGGTAATACGGAAATGTGCAACAGAGAAACAAAAACAA
CACCAACAACAACGAGAAGTAGTACGAGTTTTGTGGGCCTTTCGTGCAGATACCACCAGTTTTCCCCCACCCCTCCCCGTCTTTTTCTGCACAAT TTCGAGTTTTCCCAGCTGCGCCACAGCAACAACAACCACAACAACGAGAGCAATTGTGACTTTTCCGCATTGCAGTTGCGCCAACTAACACCGAT
TTTTTGATTTGGGGCTTCGTGCCTAAGCGCTCTTCTTGCATTCAGCCCGCGTTTAATAAACAATTAATCGTCAAGCAATAAACAACAGCAAGCCG
CGCATAGAAATTTGAGCTTTTTCAAAATATTACACCATCCGATTACATAATATAGTTTACAAGTCGTGCTTTGCCGTTCCGTTTTGTTTCGCTTG
TTCGCCTTCTTCTTGAGGTCGTTTCTTGTGCTTCCTCTTCCAAGTGAGAATTCCCAACAACCTGTTAGAAGATTCGGTCCCATTGGGCGGCGCTC
TAGCTGGGTTTATGCGGGACTGTAATCAAGATCTATCAATGGAACTAAAAATTTAATTATAGTGTGTTAACAATCAGGTAGTAAACAAGTTAGCA
TTAGAAGCACATTCTAAAAAAAAAAAATGGATTTACCTCTTCATTTTTAACACGGCTTTTATGAATATATGATTCATTTTTATCATACGAATTTA
GTATCTAAGCTCCCAAATGTATTTCCGCCTGTTTTGCCTGTGCTTATCAGGAGTGTTTTCAATTCGCCTAATTATCGTTAATGGAGTTCCCGCAT
AAACGACTCACTATACACGCACGCAGTCAGCGAATTGAATTGATCGATGGTTTGTTCACCTTCTCCACCGCTTTCTTCCGCAGCGTTCTGCTCTT
TCCACCTGTGGGCAACTACCGCCGTTATCTCATCCACCAAACATGTGAGAAATACCGCCAGCAGTACGATCTGTTCACCTTCTCAGTGGGCCAAG
GGCCGCAGCGGCGCACCGTCCTCTGCTTTCGAAACCAGCTTCTGGATCCCAGCGGCTTTGAGAAGTGAGCATCTGATATCTGACAGTAGATTATT
GTTCATTTCAATTTGTCGTTAATGCACAATTAACAGCCGCAAGCAGCAGCAGCAGAGGGAGAAGGATAGAGAGCGAGAGGCAGCGAGGAGCTGGC
GGAGCAACAACAATTCGCACTATCACACGAACGGCAGAAGCAGCAGCGCCAGCAGAAGAAGCGCCACGGAGCTCTGTAAGATGGGCGTTAAGAAG
CATATCAGCGAGACTCCATGTGAGTAAATGGCCCAAAGCAAGCTGGCCGTACATATAAACAAAGGCTATCCCCTGTTTTTAATCACATTTTGGA
GCGATGCGTTTTTGGCTCCCCGTTTAGCAAGCAGTCATAAATTTAAGTGTTCGCAAATACGCAAAAAGAAGCCAAACAAAGAAATCGAAAATGTA
ACAGGGATAGCGACGAATATGAGAATACCCAGTAATACTGAAAATTAATTCACATATTTATCTATGTACATTTTTGCCATTAAATTGCACAGTTG
TGTTAGATACCCAGCAAATTGAAGCATTAATGAGCTTTCCAATCAGAAGTAATAACTAAATTCCGGCCAAGTGTATAGCAAACAGGTAGATTAAC
TAAAAATAACCAGATGCGCCAGCTGATCGACGTCGGCAGCGCCGTTGCCGTTCATTCAAGGTCGCCCTCTTTCTCGAGCGGATTTTTTGGTGATG
TTGCATCACGGCTCACCTCACTTCACTTCACTTGGCTTCACGCAGGTAGACGCTCAACTGGTCGACCGCTGCGCACGCTCACCAGCTCTGGACCG
CCCCCGCAGCCCCCCCTTGCTGCCTGGGATCCACCTGTCAAGTTCGTGTTGACATTCACGAAAATCGGGCATAGAGCGGATCGTAAAAAATTGGG
TCGACATGAGTGAATTTTGCTTTTAATTTATTTTATGCCGAATCCGTTGCTTCACCTTAGTCTCTATTTTATTCGTTTTGTTTTGAGCATTTGCC
AACTATTGTTGCTAATCGTCTGCTTAGCTCTCCCATTTGGCGATCTATCTTCGTATCATGTGAAGTATCTCACATTCGGCATCTTGTGTCTCTTT
CTCAATGTATCTCATGGATGGCGCCTTCTCTATCTGTATCTTGCAGTAAGCAAATCGAATTCGGTGGATTTATACAGGCCGCCAGCGTTGAGGAA
CAATAGCAATAACAACAACAGCAGCAGCGAGGAAGCAGCTGCAGTAAACGAAGCTATAACAACACCATTAGCTGCAGGAACAGCAACCACTGCAT
CTACAAGTCCTACCTCCAAAGAATCCCCAAACAGGTAGGTAAATCGATTTGCAACCCATCAAAGTTAGGAATAGATCATAAACTGCGTATATACC
TCTAACGAAACTGTTGATATTCTGTCGTGAGCTAATCTCGTTACCTCGTTTCCTTCACCGTTTATTATTATTATCTCTGTTTTGCTCCGCTCTTT
CGTAGAGAGGCGGACGCCTCAGCAGCAGCAGCGGCGGCGGCGACACGACGTGAACGCCGTCCCGATCGAGCGGTTTATGTGCCAAGGGCACGACG
CAGTCAAACTACACCACCGACTACTACAACAACAACAACGGCGGCGGCAGCGACAGCGGTTGCAACAACATCACCACCAGCAGCAGCAGCGGTGG
TCGCAGCAACAATTACAACAGCGCCGGATTCCCCGCCAGTTGCAGATACACAGCCGAGCAAAGCGGACGACGTCAACGGTCAGCCGCCGTCCAAG
TCGAAGAAAAGCAAATCGCATCGGGAGCGCAGAGAACGCGCAAAGAAAACGACAACAGCTACAACGGCCGATAACGCCACTGTACTGGTTATATC
AGCATCTGAGAACGATACTCAATCCAACGAAGAACACCGACCGGCAAAGCCAGCGGACTGTGATAAGGAGGTGTGTGTACTAAAACAAGACAAGA
ACGTATATAAGCGAATCTAAAGCCTATGAATTAGTTCTTATTAACAATAATTGTTCAGCGTAGCGCCATTCTCCATCAGCAGTTAGAATTTTTTA
ATACACATTTTAATAGCTGACCTTGCCTTTCTAACATACAGATCATGAGCGGCGCCCAGCGTACAAAGCCAGGCAATGGCAACAAATCAGCCAGC
AATGGCAAAAGCCAGGCATCGCCTCCGCTGCGCATCGAGGATGTGGTGGCGGCCAGGAGCACCAATGGCGAGGAGCCGGCCAAATGTGATAACGA
TGTGCGCGAGCTGCAGCGAGCCTCAAAGGTAAGTTATGCCGCATGGAATCAGCGAAATGTTTTAACTAACTTCCAAACGATTGCAGGAAATCAAT
CGCAGCAATCGGCGCATCATGAAACAAACCTTCAACTCAGATGTGCTGGAGATTCCCGAGAAAATAGAGACATCGGCAACAAAGGCCATCCCCAC
ATCCCCGCAAGCATCAGCCACAGCGAAACCACCTGTAGACAGCACCACCGAAGACGATGACGAGGAGGACGAGGACGACTGGGAGAAGATGTTCG
ACGAGAGCGGCGACTGTCTGGATCCCAAGTTACTCCAAGAACTGACTGAATCCGTGGGCAAGTGCAAAATAGAGCTGCCCAAAATGGACTATACG
GTAAGTAGATATAACTGGTTAACCAGCATCATCATCAAATTAAACACTCTGTTCCACAATTCGTACAGGTCTTTCACATTAAACAACAACTGCTC
AACGAAGAGGAATTTCCGCACGTTCTGGAGGTGTCCAATTTCCCAGTGGAGTTCAAAACTCCCGACCTGCTCATGCTTTTCGCCCAGTACAGGGG
CAGTGGTTTCGACATCAAGTGGGTAGACGATACCCATGCCCTGGCTGTGTTCAGCAGTTCCCGCATTGGTGAGTGCCTACAAATGCAACCGGAGA
TTGGTTCGGTAATGAAATAGAACGTTTCCTCCGCAGCTGCTGAGGTGCTGACGATGGGGCATCCGTTTGTCAAGTTGAAGCCACTTGCGGAAGCC
ACTCTGGAGTCACGACTGAAGGCAAAGAAGGCCGGCGCGGTGTCAATGCAGCCCTATCGCCAGCGTCCGGAAACCTGCACGGCCTTGGCCCGACG
ACTGGTATCGGGTGCACTGGGAGTCAAGCTGCCCACGGCGCCGCAGGAACGGGAGAACGAGAGGCGGGTACTACGTGAAGCCAAAGGTGAGTGCG
GGCCATGTAACTAAACTGGGTCAAGGATATACTTGATTTGGAATCATTGGCGCTGCCTTCCCTTGGTCTTTTATTAATCTGCCTTATCTTTTTAT
TCAGAACGCAAACTGCTAGCTGCCAAACAGCGGGACGAAGTCTGGGAGAGCTAGACCGCGGCCCGGAAGAAGGCCAGGTGCATTTTTCTCACCCT
TTTCTCATCTGCAATAAATGCGGCAGCAAACACAACACCATGTGGATCGACAACAAGAAACACCACCATTAACGCCCACAAAAACAATTCTCAAT
CAAAGCTAACACAGTAAATGAGTAATTCGCATGCTAAGCAATGTACTTTTAATGTTCGCTTTTTGTGAAATTAACACAGACTTTTGCTCAATTTG
TTGTAGTTTTAGAGGATGCAATGCATATTATATCATCTAGGCCGTAAGAGAGAAATATCTATATTTATTGGTCGTAGCAATTAAACGTGCAGAG
AGACGCGTGTACGTGTTGTTTTAACTCCAGCCGTAAACCTAATTTTTAAGCGCGAGCAATTTATATATTGATATACAGTTTGTCAAGAAACTGTT
TACACACTGTGAAATAAGTTGAATTTTTGACTTTAAAGCTAAAAATAAAGGGTTTTTTGCTTAATTAAACGCAATTTTTTTATAAAATATAATTA
AACAATATTTATTTTACTTATAAATCAAAAAACAAATTAAAAATATTAAATATACAAGAAAATAAACAACAAATTCCAAGTTTACACACTTTTGA
GACTGTCAAGAAACTCTTTACACAAAACACTAAATCGAAGTTTAATCCTAAATTTTTTAATTATTTTATTAAAATTTTAAAAGTTTTGGTATGTA
GTATGTTCCCCATTGGCTTTAGCTACAAGTTGAAGCCTTTTTTTCATGGATTGGACAAGTTTTTGCAGGTCATATTCAAACGGGATCTTTTCACA
CTCTTCGACTATTACAGTCATAAGCTGTTGTTGTGTTTTAGGTCCCTTTTTGCCACCTTCTTCTTTAAGTAGGTCCACAAATTTTCAATGGGGTT
CAGATCAGGACTCTGAGGGGGCGTATCGATCACTTTACCACAGTTATTAAGGCGCCAGGTGCGTACATTGCACTCTTTATGTTTCTGATCATGTC
CTGGTAAAACTTAAGATTTGGCTTGTTGTTGCTAACTAGCCCGAATTTTTCTGCACTGGCCTTCAAATTTGTTTTTTAACATTTCTAGATATTGC
ACGGCAGTTATTGTGCTCTCAATTAAGGCTAGTTTTCCCACTCCACGGGCTGGTGATACAGCCCCAAACCATCAGGTGACATTTTTCCAAATTTT
ATCGGTTGGAATGATATTTTGTTTTTCTAGCGCACTCAACGGTTTGCGCCATACTCTGCTTGGCCCGTCGTTATAAAAGAGCATCATTTTTGTTT
CGTCACAAAATATGACAGTCATCCCAGTACTCTTCCGCATGATCCATCATGCTCACAGCGAATTAATGACCGCTTTTCCATATTGGCATCTGATA
GCAAAGGGTTTTTCCTTGCAAATCTTGAAGAGTACCTATGGCGTAGGATGACTTGGCGCACAGTTTCGGTGTGACACAGTTAGGTGGCATTCTTG
CCTGATATCCAGAGCAAGTGATCTGACCGAGATTGCGGGGGTTCGCAATCACTATTCGCATAATAAAGCGGTCTACACGCTTTTTAATTTTAATT
TTCCGCCCACCACCG
(SEQ ID NO: 199)

Exon: 1001..1142
Exon: 2269..2439
Exon: 2507..2679
Exon: 3562..3739
Exon: 3901..4345
Exon: 4507..4683
Exon: 4742..5035

FIGURE SHEET 107

Exon: 5104..5293
Exon: 5357..5596
Exon: 5705..6330
Start ATG: 2646

Transcript No. : CT7070
CGACGTCGGTTTTTTCGTCGTCGCGACTTTTTAAAATAAACTGGAGGCATTCGCAAATAATTTAAGCCTAATCGATCAGGAATTCGTACATAAT
GTCGGTTGTGATATCGAGCTCTTTGTCAAGAAGCGCTTGAATCGTGGCGTTCTGCTCTTTCCACCTGTGGGCAACTACCGCCGTTATCTCATCCA
CCAAACATGTGAGAAATACCGCCAGCAGTACGATCTGTTCACCTTCTCAGTGGGCCAAGGGCCGCAGCGGCGCACCGTCCTCTGCTTTCGAAACC
AGCTTCTGGATCCCAGCGGCTTTGAGAACCGCAAGCAGCAGCAGCAGAGGGAGAAGGATAGAGAGCGAGAGGCAGCGAGGAGCTGGCGGAGCAAC
AACAATTCGCACTATCACACGAACGGCAGAAGCAGCAGCGCCAGCAGAAGAAGCGCCACGGAGCTCTGTAAGATGGGCGTTAAGAAGCATATCAG
CGAGACTCCATTAAGCAAATCGAATTCGGTGGATTTATACAGGCCGCCAGCGTTGAGGAACAATAGCAATAACAACAACAGCAGCAGCGAGGAAG
CAGCTGCAGTAAACGAAGCTATAACAACACCATTAGCTGCAGGAACAGCAACCACTGCATCTACAAGTCCTACCTCCAAAGAATCCCCAAACAGA
GAGGCGGACGCCTCAGCAGCAGCAGCGGCGGCGGCGACACGACGTGAACGCCGTCCCGATCGAGCGGTTTATGTGCCAAGGGCACGACGCAGTCA
AACTACACCACCGACTACTACAACAACAACAACGGCGGCGGCAGCGACAGCGGTTGCAACAACATCACCACCAGCAGCAGCAGCGGTGGTCGCAG
CAACAATTACAACAGCGCCGGATTCCCCGCCAGTTGCAGATACACAGCCGAGCAAAGCGGACGACGTCAACGGTCAGCCGCCGTCCAAGTCGAAG
AAAAGCAAATCGCATCGGGAGCGCAGAGAACGCGCAAAGAAAACGACAACAGCTACAACGGCCGATAACGCCACTGTACTGGTTATATCAGCATC
TGAGAACGATACTCAATCCAACGAAGAACACCGACCGGCAAAGCCAGCGGACTGTGATAAGGAGATCATGAGCGGCGCCCAGCGTACAAAGCCAG
GCAATGGCAACAAATCAGCCAGCAATGGCAAAAGCCAGGCATCGCCTCCGCTGCGCATCGAGGATGTGGTGGCGGCCAGGAGCACCAATGGCGAG
GAGCCGGCCAAATGTGATAACGATGTGCGCGAGCTGCAGCGAGCCTCAAAGGAAATCAATCGCAGCAATCGGCGCATCATGAAACAAACCTTCAA
CTCAGATGTGCTGGAGATTCCCGAGAAAATAGAGACATCGGCAACAAAGGCCATCCCCACATCCCCGCAAGCATCAGCCACAGCGAAACCACCTG
TAGACAGCACCACCGAAGACGATGACGAGGAGGACGAGGACGACTGGGAGAAGATGTTCGACGAGAGCGGCGACTGTCTGGATCCCAAGTTACTC
CAAGAACTGACTGAATCCGTGGGCAAGTGCAAAATAGAGCTGCCCAAAATGGACTATACGGTCTTTCACATTAAACAACAACTGCTCAACGAAGA
GGAATTTCCGCACGTTCTGGAGGTGTCCAATTTCCCAGTGGAGTTCAAAACTCCCGACCTGCTCATGCTTTTCGCCCAGTACAGGGGCAGTGGTT
TCGACATCAAGTGGGTAGACGATACCCATGCCCTGGCTGTGTTCAGCAGTTCCCGCATTGCTGCTGAGGTGCTGACGATGGGGCATCCGTTTGTC
AAGTTGAAGCCACTTGCGGAAGCCACTCTGGAGTCACGACTGAAGGCAAAGAAGGCCGGCGCGGTGTCAATGCAGCCCTATCGCCAGCGTCCGGA
AACCTGCACGGCCTTGGCCCGACGACTGGTATCGGGTGCACTGGGAGTCAAGCTGCCCACGGCGCCGCAGGAACGGGAGAACGAGAGGCGGGTAC
TACGTGAAGCCAAAGAACGCAAACTGCTAGCTGCCAAACAGCGGGACGAAGTCTGGGAGAGCTAGACCGCGGCCCGGAAGAAGGCCAGGTGCATT
TTTCTCACCCTTTTCTCATCTGCAATAAATGCGGCAGCAAACACAACACCATGTGGATCGACAACAAGAAACACCACCATTAACGCCCACAAAAA
CAATTCTCAATCAAAGCTAACACAGTAAATGAGTAATTCGCATGCTAAGCAATGTACTTTTAATGTTCGCTTTTTGTGAAATTAACACAGACTTT
TGCTCAATTTGTTGTAGTTTTTAGAGGATGCAATGCATATTATATCATCTAGGCCGTAAGAGAGAAATATCTATATTTATTGGTCGTAGCAATTA
AACGTGCAGAGAGACGCGTGTACGTGTTGTTTTAACTCCAGCCGTAAACCTAATTTTTAAGCGCGAGCAATTTATATATTGATATACAGTTTGTC
AAGAAACTGTTTACACACTGTGAAATAAGTTGAATTTTTGACTTTAAAGCTAAAAATAAAGGGTTTTTTGCTTAATTAAACGCAATTTTTTTATA
AAATATAATTAAACAATATTTATTTTACTTATAAATCAAAAAACAAATTAAAAATATTAAATATACAAGAA
(SEQ ID NO: 200)

Start ATG: 453

MGVKKHISETPLSKSNSVDLYRPPALRNNSNNNNSSSEEAAAVNEAITTPLAAGTATTASTSPTSKESPNREADASAAAAAAATRRERRPDRAVY
VPRARRSQTTPPTTTTTTAAAATAVATTSPPAAAAVVAATITTAPDSPPVADTQPSKADDVNGQPPSKSKKSKSHRERRERAKKTTTATTADNA
TVLVISASENDTQSNEEHRPAKPADCDKEIMSGAQRTKPGNGNKSASNGKSQASPPLRIEDVVAARSTNGEEPAKCDNDVRELQRASKEINRSNR
RIMKQTFNSDVLEIPEKIETSATKAIPTSPQASATAKPPVDSTTEDDDEEDEDDWEKMFDESGDCLDPKLLQELTESVGKCKIELPKMDYTVFHI
KQQLLNEEEFPHVLEVSNFPVEFKTPDLLMLFAQYRGSGFDIKWVDDTHALAVFSSSRIAAEVLTMGHPFVKLKPLAEATLESRLKAKKAGAVSM
QPYRQRPETCTALARRLVSGALGVKLPTAPQERENERRVLREAKERKLLAAKQRDEVWES*
(SEQ ID NO: 201)

Classification: hypothetical

Celera Sequence No. : 142000013384244
GTAACCTATGATGTCGCGCCATATCGATTCATTGTTTTTTTAGTGAACCACCCCTAATGAACGGAGCTTAAATCTAAAAAATAAACAATCATCT
GTGAACTTAGTTGCGCTTGCTTGCGAAATGCAGGCGGAGATTAAGGCCGACATCATCGTGGAGGCGATGGAGGTGCTAGTGAATCACATTCTATA
CGTGCGCGGTATATACCCCTCGCACATTTTTAAAATGAAGCGGATGTACAACTCGCCCATCTATGTGTCCATATTTCCACCGCTTAATAACTACC
TGGCCGGCGTCCTAAAATCCGCACAAGAACTTCTTCGCCGCCGGGAGCTGCAGTGCCTGGAGCTAATAGTGTATCAGAAGGAGAATGAGAAGTTG
GAGAGCTATAAAATGCAACTAGAAACCCAGAGGAGTGGCCTACCGGCAGAGGATCATTTGATGGAGTTCGAGCAGAACATGCGCTCTGTCATCTA
CAAAATCTCTCAGCGCTTAAACCAGGCGCCTAAACTGCCCGCCGGAAGTTGTCAGTTTAAGGTGCATCTGCACACTACCCAGGAGGCATTCATCC
GCTTCAGCCATGACTCCCAGTACCAGGAGTTTCCCTGGCTTCAGACCCAAAAAACTGAATCCCAAGCGACAGGGCGAACCGTTTACCTCCTTCCT
TTGGCTAGGGTAGATGATTTGGGACTGAAAATGGATGTCCTCATCGTTAATTAATGTTATATTCCTAAAACTGTTATCCATTTTATCGAAAACTA
CACGACGTTGGGTTTATTTTAAACTACAATTGATTCTAATCATGAATCGTTGGCTGATCCATGGTCTTTCTTTAATGAATAAAAGGACGCCCAAT
GGTTTTATGGCTTAACATTAGATTCCTTAAATAAAACCAATTTTAGTGTCATTCCGTTTTGAATTATAAAGACTGTTGAGGTTTTAGAGGAAGCG
TCATATAGAATTGACCGGTACTCAAGCGACCATAATCGTAGGCTTGTCCTCTAAAGTAGACCCTGGCGTTTTAGATCCTCGAACGTCTTTCGGTT
GACAACGTTTCCCAGCGAGTCCTCGAACTCTTCCTCCTGATCGGCTACCCAGCGCTCGCTCTGCTTTTGCGACTTGAGTTTTTCCCACAACGTGA
TTGCGTCCTCGATCTGGGTGACATTGGCGAAATGGGCGGTGTTCGGAATGCCGAGGCATCGCATGCCGTGCGCATGCCGCCACTCGGCGAAGTGT
CGTTGAAAAGCCTTAGGACCCTTGTAGGTGAAGTTTCCACATATCTCGCAATTATAGCTAATATTCAGGCCATGCAGTTTATACAACCAGTAGGG
GATAGGTTTACCGTCCCATCCGAGCGGCAAGTTCTTGGGATTGTACGGAACGTCGTCCGCGTCGGGATCATCTTCGTTGTCCGACTCGCTGGCCT
CCACATCGCTATCGTCCCGCTCGCCACCAGTCCGAGCCTGTTTTCTCTGCACATTCTCCTTGGTAGCCGCTCTCTGCTCAGACAACAGATCCGCG
TATTTGTAGAGCAGAGCCTCTAGCTGGGCAATCTCCTTGTGGCGTTCGTGCTCCCGTGACTGGGCACTAGCAGTCTTTGCGCTGGGCTTCTTGGC
CATCAGTGCGGGATCCAAGGTGCTTTTACCTTTTGTAGAGAATAAACGCTGTGCTCGCTCCTCCAGGGTGCCGCCGCACTTAAGACCCAGAGCCA
CCAAAGCCGACTTTAGACGATCCAGTCCTAGCGAGGCCAGCTCCTCCCAGCTGGAGAAGGCGGATAGATCAAGGTGGGCGCCGGTGTTGGCCAAC
GCCGACTCAGTTTCCTTAATCGAAAAACCCGGAAATGTGCCCATCAGCCACTGGCGCTGGAAGTCAAGTTCCACCTTTAGCAGTTCGCCCTCCAG
GTCGAGCAAGGGCTGGATTCGGAGGATGAAGTGGTGCAGGTAGTCGTTGAGGGTCTCTATGTATATGCGGTACTCGCGGTTCTTGCGCTCTCTCG GAATATCGAAGACGTGGTCAAAGGACATAAGGTAAGTGATATAGTCCAGTTTCTCCACCGACCGCAAGTTGAGGTACAGCTCGTAGCACTCGTTG
AGGTCCAGATAGCGACCGCCGCCCTCCTCGTCAGTGAACTCCACTAGGGCACTCATGTCGTCCGGATTGTTGTACACCCGAATCATCTCGTCGAA
CTCGACGGACAGCGGCACGCTGACCTCCGCCGGATGGGACTTGTAGAACTGCTTGATTTGCTTGAGGCGGGCGTAGAACTCATTGAACTCGTTGG
GCCCCGAAAGAGCGGCAATCTCCGCCTTTCGTTCATTGTCCTTGTCCTCGTAGAGATCGCGTAGCTGGGACGTAGAGTTGTGATGCAGTTCCATG
AGGTATTTAAGCCGGTGCTCCGAATGGATGCGCTCCTTTTCGCCCGGCTTTTTGGTCGCATGCTCGTCCACCATCAGTTTGACCAGGCGCTCGCG
CTCCTCGTGTAGGCGCCGCTGTTGCTCCAGGAGCGTCTCCATGGCTCTTGAATGCGAGGATTTAATGCGGGGAAATATCAAATGGAGGCCTTTCA
CTTAGCGAAATCCCGAAGAAAACACAACTTTTCGTCAGCGTGTGTACATTAAAAAATACACTTACAATAAAGCAGGGATGGCTTATATTGTCACA
TCATATTATTGTCAGGTTATTATACTCCGATCACACTGGCAATTAATGTGGATTTCGGGAATGCAGATGTATCAAATTAACGCTCGATTATTCGA
GTAATATAGTAATGATATTTAAAGAGCCAAATTGATTTTTCATTATCATATATAGATTATATCGCATGATTTTTCTACCTAGTCGATTAAAGTGA
AGCCTCTGTTACAAATGCGATAACAATTACATCGTCTATCGGTGGTCTGACAGCGACAACAAATACACATTTTTACCCTCGCAATCGCAGGGTCA
CACTTTCGTGAAATCATATGATCGATTTGCAGTGAAAATTTTCAGACGTTGGGCAGAAGGCAAAAGTAACTTATCGTTTTCCACTTTCCTCGTGT
TGGGCCGCCGTTTCCAACTCAGTTCGGCTGTGAATGTATTAGCTTAATTAAATTTCAATTATTTCCAGGCACGGTTGTTGTACGTGGGCTTCTTT
AAAACACTTGAATTTCCTTTCGGTTTGTGCAGTGAAAAAAATCAGTCAAAATGGCACTGAGCGATGCTGATGTACAAAAGCAGGTAATTGAAAAC
TTGGATTGGGAACGGGCAGGCGATCAAGGTCGTAGGGAAACAAGCAAAACGAGAGGCTTCGTTTGCCTTTTTGCCTTTGCAATTTGCCTTTGCAA
TAAAGATGGCGAAGTCATGGGATCTCCCAGGTCATGTGAACTTTTCACCGCCAGTAGTCCAATTAGACTGACATCCTTCCAAATCGGCCCGGTCA
TTTGGGAGTTGCCGGAGTTTTGACATATTTGTTGGCTAATGAAGACACATCAATTTATTTGTCCAGATAGTTTGCGTAAAAAGTGAGTAAAAATT
CGTGCTGGTCATGTGACACGGCCCCCGCATTGGAGCAATGTGTTGGAGCGAGACGACTAGCCCTGCACCCCACACTCGTACTCTCTGTCACACGA
CCAGCGGACCCCTTACGTTATCAAAAC
(SEQ ID NO: 202)

Exon: 2637..1001
Start ATG: 2512 (Reverse strand: CAT)

Transcript No. : CT7078
CTTTATTGTAAGTGTATTTTTTAATGTACACACGCTGACGAAAAGTTGTGTTTTCTTCGGGATTTCGCTAAGTGAAAGGCCTCCATTTGATATTT
CCCCGCATTAAATCCTCGCATTCAAGAGCCATGGAGACGCTCCTGGAGCAACAGCGGCGCCTACACGAGGAGCGCGAGCGCCTGGTCAAACTGAT
GGTGGACGAGCATGCGACCAAAAAGCCGGGCGAAAAGGAGCGCATCCATTCGGAGCACCGGCTTAAATACCTCATGGAACTGCATCACAACTCTA
CGTCCCAGCTACGCGATCTCTACGAGGACAAGGACAATGAACGAAAGGCGGAGATTGCCGCTCTTTCGGGGCCCAACGAGTTCAATGAGTTCTAC
GCCCGCCTCAAGCAAATCAAGCAGTTCTACAAGTCCCATCCGGCGGAGGTCAGCGTGCCGCTGTCCGTCGAGTTCGACGAGATGATTCGGGTGTA
CAACAATCCGGACGACATGAGTGCCCTAGTGGAGTTCACTGACGAGGAGGGCGGCGGTCGCTATCTGGACCTCAACGAGTGCTACGAGCTGTACC
TCAACTTGCGGTCGGTGGAGAAACTGGACTATATCACTTACCTTATGTCCTTTGACCACGTCTTCGATATTCCGAGAGAGCGCAAGAACCGCGAG
TACCGCATATACATAGAGACCCTCAACGACTACCTGCACCACTTCATCCTCCGAATCCAGCCCTTGCTCGACCTGGAGGGCGAACTGCTAAAGGT
GGAACTTGACTTCCAGCGCCAGTGGCTGATGGGCACATTTCCGGGTTTTTCGATTAAGGAAACTGAGTCGGCGTTGGCCAACACCGGCGCCCACC
TTGATCTATCCGCCTTCTCCAGCTGGGAGGAGCTGGCCTCGCTAGGACTGGATCGTCTAAAGTCGGCTTTGGTGGCTCTGGGTCTTAAGTGCGGC
GGCACCCTGGAGGAGCGAGCACAGCGTTTATTCTCTACAAAAGGTAAAAGCACCTTGGATCCCGCACTGATGGCCAAGAAGCCCAGCGCAAAGAC
TGCTAGTGCCCAGTCACGGGAGCACGAACGCCACAAGGAGATTGCCCAGCTAGAGGCTCTGCTCTACAAATACGCGGATCTGTTGTCTGAGCAGA
GAGCGGCTACCAAGGAGAATGTGCAGAGAAAACAGGCTCGGACTGGTGGCGAGCGGGACGATAGCGATGTGGAGGCCAGCGAGTCGGACAACGAA
GATGATCCCGACGCGGACGACGTTCCGTACAATCCCAAGAACTTGCCGCTCGGATGGGACGGTAAACCTATCCCCTACTGGTTGTATAAACTGCA
TGGCCTGAATATTAGCTATAATTGCGAGATATGTGGAAACTTCACCTACAAGGGTCCTAAGGCTTTTCAACGACACTTCGCCGAGTGGCGGCATG
CGCACGGCATGCGATGCCTCGGCATTCCGAACACCGCCCATTTCGCCAATGTCACCCAGATCGAGGACGCAATCACGTTGTGGGAAAAACTCAAG
TCGCAAAAGCAGAGCGAGCGCTGGGTAGCCGATCAGGAGGAAGAGTTCGAGGACTCGCTGGGAAACGTTGTCAACCGAAAGACGTTCGAGGATCT
AAAACGCCAGGGTCTACTTTAG
(SEQ ID NO: 203)

Start ATG: 126 (Reverse strand: CAT)

METLLEQQRRLHEERERLVKLMVDEHATKKPGEKERIHSEHRLKYLMELHHNSTSQLRDLYEDKDNERKAEIAALSGPNEFNEFYARLKQIKQFY
KSHPAEVSVPLSVEFDEMIRVYNNPDDMSALVEETDEEGGGRYLDLNECYELYLNLRSVEKLDYITYLMSFDHVFDIPRERKNREYRIYIETLND
YLHHFILRIQPLLDLEGELLKVELDFQRQWLMGTFPGFSIKETESALANTGAHLDLSAFSSWEELASLGLDRLKSALVALGLKCGGTLEERAQRL
FSTKGKSTLDPALMAKKPSAKTASAQSREHERHKEIAQLEALLYKYADLLSEQRAATKENVQRKQARTGGERDDSDVEASESDNEDDPDADDVPY
NPKNLPLGWDGKPIPYWLYKLHGLNISYNCEICGNFTYKGPKAFQRHFAEWRHAHGMRCLGIPNTAHFANVTQIEDAITLWEKLKSQKQSERWVA
DQEEEFEDSLGNVVNRKTFEDLKRQGLL*
(SEQ ID NO: 204)

Name: SAP61/PRP9/noisette
Classification: RNA_binding
Gene Symbol: noi
FlyBase ID: FBgn0014366

Celera Sequence No. : 142000013384244
TGGACTAAACTCGCAGATTCCTGTAACTTGGAAGCACCACGAGTTTGCTTTAGAAGATGCCTTTCCGTTGAACTAAAACTAGACGAGTAAAGCGT
ATCTCAAACATTGTATCTTCCGAACCAAAATAGTGCTGCATACTTTTCGGGATATGTCTTATTCAATGTAAGTAATACAAAAAGAAAAAAGGTAA
CTTCTTAAAACTTGTAATATTTGTCACAAATGAATGACGACTAGATTTGGCCATGTCTGTAACAATAAACGTACAAAATATTCGAAGTTGCAGAA
ATGGGGATCCAGCATTCGGATTTGGTTTTTTGTCAAACTTTTAAATATAGAATCGGACCACATCTTTTTAAGACCTTAAAAAACTGATTTGAAGT
TAGACCCCTCATAATGCCAACTAAATTTGTTAAACAAAAATATGCCCCTATATGCCAATCAAATTTAAATACAATGCTTTCTCAGCGTTTCAGTT
AAATACTTTGGGTTGTTTAATGGTTTTATACGTATACATGTGCTAAGTCCATGTATCTTATATTTCGTAAATCCATAGATTTTGTTCGACGAAAC
TTTGCTAAATGATATTGATCTTTCAAATATAACTTGTTAATTTCCTTTCATCGCCGTGGCAAATCCTTCGAGAGTGAGTACTACTTGTTAAACGC
ATATATGAGGAAAATTTATTGATGAATAATGCGAACATGCAAACGGAACACATCCCCGAATTCACACAAAGCATCTCTGTGGTATCTCTTTTGGT
TTTTTATTTGTTGCATCAACTCCGCGGAACTCCAGCTACCTCACTGCAGGTCGTAGTAGTCGACGTTATTGGCGGTCAGATGTTCTCTATTAATT
TGGAGCGTGCTGCTGTTTCCACTTCAAACTTTTATTAACATATATAGTATGGGTTTGCCGGTATATTGCAAACGGAACTAAGTGTAGATTCGTG AATGATATCAGACTGGACTGCAAACGTTTAGTTTCTAGCATGTTTTTTTACTCTCTCCTTTATTTGTTGGAATTTTTGAGTTTTATATAGGTGG
AGTTTTCAAAATGACATTAATTCATAGGGGTGAGTTTTATATATAGTTCGACTGGCTGTTGCAGGTGCTGGTTTCGAATTTTTGGATGGGGATGC
TAAAGGGCGGCTCCGTTTGTGTTCATCCTCATTTAGCCATCAACCAAGTTCTTACTCGCCATTCTTTTGTTCGTCCTCAGATTCGGATTCTGAAA
GAGAATAGAATACAAAATGTTAGTATGGGGGCTTCAATTGGTACAAACTGAAAAGATGTGCAGCTCCGGTTATGCTGTCCAAATGATTATTGGCC
AAATTTAACTATGGAAAGTTATCTGGACACCCAACCATTCAAATGCTTTGGCACAACTCCCCGCTTGGCTCAATCGAATGAAGCAACCATTCGGA
GCTTTTATGAGGGGATTGTGCATGCGGACTAGGACAAATGCAGCTGTCCAAACGATTATTGGCCAAATTAACCACGGCATTGGGTTATATGGGCA
CCCAATCATTCTTTCGCTTTTGCATACTGTACATGAACCCTTTAAAACTGGTTCCTAATAATGGGAACACTTTAAAAGCTTGGTAAGAAGCATGC
TCGGTGAAGTCAGCTATTTGTGTCCAAGTTTTCATTGGCCTTTGATGCTCGGATTTTGTGAGGCAACAAGGCAAGCAAAAACTCAAATGCTCTTG
CAATTTTGTACAATGAAAATGTCATCCAGGACAAGACCATTCTCAAAAAGTGCACTGTGTAAAGTTTCGAAGGAAGCAAAATTTGAATATTTATA
TTGTCCAGGTTTTCATTGGCCTACGTTGTTCAGTGAATGGAAATCAACGAGGCAAGCAAAAAACCCAAATTTCTCTTGCAATTACGTACCAGAAT
CAAGCTATTTAAGACAAGACCATTCTCAAAAATTGCACGCTGATAACATTTATCAAAACATACTAACCTTCTTCGGCTGACTGAAGCCATTCGAC
AAACTTTCGCATTTGTTCAAGGAAATGCATTTTGCCCTTGTTTGAGTGGCCCTCCTTGTACCAGCGCAAGATGATCTCCTCGGACAGGACCTCGG
TCTTGTAGAACAACAAAATGATTTTCTGGAAGGCCTTCATGAAGTTCATGTTCTCGTAGCAGAATTCCTGCACCTTCAAGATTAGGGCCAATTCC
GAACGGTCGGTCGAGGCGAAAGCCTGCAACAGTGGGCAGTAGTTCTTCAGATGACGAACAGCCTGATCGGTAACCAGCTCCTCCTTCTTGTTCCA
TTCGCCCAATGACATGATGGTGGACCAAATCTGGTAAAGATCATACATGAGATTTAGTAAGGAAATCATCCAGTTGGATTATTTACGCATCGACT
TACAATAACAATTATTTCATGATCGGGAATGTTGGTGCGCTGCGAGAAGTCCTTAATGTCTGAGGTTATCTCATTATATGGCTTCTCATCGTTGA
TATCATCGATGAGCGCCTGCTGCAACTCACGCTTCGCCTCCTGGCTAGCCTGAGCCTTATGTAGCTTGACGATCTCGTTAAGTTCTTTGTCAAGA
AAAACTTGTTTAAAATATTCCTCAGTACGTTTGTTCGGTGGGAAAAAGTCCATAAGTCTGGAAAAACGTGAAAAAGTGGAACCATTATTAATAAT
TTAAGTTAACGCATTCAATAATCAACCTTAAATGACGTATTGAGGTGTACGAAATTAAATCAGCACCCAAATGAAGCGAAAGGTCATTTGCGAAT
TGGGTAAAACTCCGTCGAACTTTCTTACTCTAGGAATATCAATTAAAGATGCACAACTGGATCATTGAGTCATCTTCCTGAGAACATTCCGGGGC
TAAAAACAAATCACAACTAAAAACTTACTTGCTTTCCAGTCCACCCTTCTTAAGCGCCTGAATCAGATATGCAATGCCCTTCTCTTGCTTGAACG
TCTGGAACAGCTCTAGTAGAAACTCCAATGCAATGCCATCCTTGATTAGGTGCTCGTTGTTTAGTACCAGTAAAACATTTGGCGGTACAGAACCG
TTGACTGTTGATCAAAAATAGGGTTAAATATAGGGTTAGTCAAATGTTTTCGCAAAACAAGTTTAGACGGCCGGCTAGCAATCCTGTCCTTGGGC
TCGTGGCCCTTAGATGTGGTTAGTTCATCCAAGAGTCAGTATACCAAGTGAAGGATTACTTTAGCCCCTCAGCTGCAAGTTGAACAAGTGTTTAT
CGAAACAACTAATTGAAAGACCGAATGGGCAGACGCAAGCAATGCACAGGAGGAACAGGAACATAAATGTTAAGACTTACCTAACCAGAGCGCTG
TCATACGCGCAAGCTTGATGCGTTCACTAGGAGTAAAGCCCTTTACGAATAATAGAACCTTTCCCATCTCCTCTTCGAACATTTTCTCAAGGTAC
TTGTACCGTCTGATGAGCTTGACAAATACCTGGAAAAGGTAAAGTGTGATTGCCCCTGTTAGCGGATGGTGAAATTTTACTGTGTTCTCACGCAG
GAGGCTTTTGTATTTGTTGTTGCAACATTAGAAATCTTTAGATTGCTGGCGGTAGTAATTTTACAAAATAAAGACAAGTAAAATGTGGCTTTTTA
TTTTGCATATTTTGACACCGATTGAGTTGTTGAGATGCATAACCGGTTCTAATAATATGCACTTTGATTCAATAGCGTGACCTTCGCAGTGGTTG
CATGCATATAGTATATATATATAGTGTTGAATAAAGAGTAGTTGTTGACACATAAGAAATCTTCAGAACGTTAGTGTTTAGGACAAACCAAAGAC
AAGTAAATGTGTTGATTGTTATTGCATATTCTTGACACCGATTACATTTTTGAAACTTTATAGTCAGCTCTAATGATATGCAGCCACTTCACGAA
TTTCATACTTTTAAGTGGATCCGAAGAAAATCATTTAGTAGTAAATAAACGTTTTAGCTTGGAAAACAACAAGAGCTCAACTTGTGTTGCAATCA
AACCAATTTTCGTTTACTCATAATCATAATTTAAGTATGACCTGCTAAAAGATTACAAACCTGCTCATGGTTGCGCATGCTCTCCATGCTCTCGG
GCGCATCGAAGATGCAGTAGCTTGTGCGCGGCTTTTCGCCATCCTGAGATATAGAACCACCAGGCACTGCAATTGAAACGAGGATGGAAAAGGGT
CAGTGAAGAGACTAAACACATTACTTGCAGCGGAAAACTTACCTAGTAGACCTCCTGCAATCAATATGTCAAAGAGAACTTCACCGTAGCGACGA
TAGTCGAGCTTGTTGCCCGCGCTGTCTAGATATTTAGAGATTTGTTCCAGGTCGCCTTCAGTTTTTTCGAGACCAGCAATGACCGCATCACGGAA
TCCCGTTGGGTCATATTTTTCTCTTTCATCTCTTTTTCTGGTCTTGATGCGTTGACCCGATAGCACTGGTCTTTCAGTTTTTTGACTCATACAAT
AAATTGCTGCAAAGGTAAATGTGGATCAGAGATGGAAGCGGTTTTGGTTTGCCCCTGTAAGTTTTTATTTCTGACCAGACTAAATTATCATGGCC
ACTAGATTCATTTTTAGATTTATCTTAATTTTAGTGTAAGATGACTAAGGTGGTCTCCAAGCGGTGGAAAACCGTTCCCTGTATATGTATTCTCG
TTGCGCTCATAATCAAACTACAACATTTTCACCTATGACCGGCGTTTAAGTGGAAACTCTAGTGAAAACTGAGCCTAAGAAAGCCTTAACCTAAA
AATGCCAGCGTACATGTGCTTTAAACACACACATTCAAGAGCGGAGAACGGGCACACTTCACATCTCTTTTTAATTATCTCTCTTTTTCACACAC
ACATACCCACTGTGCATTTTACAGTTTGATAATGTCGACAAAAGAAATAAAAAGAATTGAGAGGTGAGGCGACCAAGAAATCGACATAGAAACGC
AGAATAAAGTGAAATTTTGACGTGGTTACTTGTGTTAGGTAGCGCGCTGGGGAAATGAGGTCATTGTGCATGTAGTGCACATAAAAACGCGCCGA
TGACTGTGTGCTAGTTGGCCGGGAAAATTGTCATAGCAGCGAAAACGCAAAAATTAAATTATCTAGGCTATCAAGTACACATTGGTACATATAAG
GAACGGCAACTTACGCTTTCACCCAAGGATATTAAGTCTGGCCCTGTGTTTGCCGCTTCCGCGTGTCCTTGCAATCAATTGAAATCAGTCGTGTG
CGAGTGTAGTGTGTATGTGTGTGTGTGTGCCTGTTGCTTTTTCACAACTAACGAACGTGCGAGAATATGTAATTTAATTTAACCTCACGAAGC
GCTGGCTGGTTAATGCTTCTCACTCGAGTCGACGAAAAACAAAGAGACAGATGGCAGATCCCTTCTTTTCTTACCTCTCTTTTCTTATGAGCGAG
CTTTTGCACGGTAAAATTGACACGCACGCACACACACAACAACAAAGAAAAGGGGAGAGCAAATAGAAAATATAATTTTTTGTAACGGAATTTAC
TTTTATGCCTTCAAAATAAACGTTAACAATTTTGCTCAGACTACGTCCGGAATTCTATTTTTAACAGCTATCACAATCGGTTACTAGGTATATGT
GTTGTTTGCCTCGAATCCAGCGCCCCTCTGCTCGCACCACTTTGTTAAACGAAATTCGGAGAGCGAATGAGACGACACACGAGCGCACGAACGAA
GCGGACGAGCCGAGAACGAAGACATGTGGTTCGGCGCCATTTTGAAGCGATACACTGACATGGCGAAAGCGGAATGATGGGCACAGGGAAAACGA
AAATTAGGGGGAAACGGTGAGAAAAAATGTGGGATGGGGGTTCAAAGTGTGTATATTGCTGTCGCGCTTATTAAATAATGAGCAAGGTACAGTCG
AACAAAGGCCGACGGCCACCAAATGATTTTTTGCATGAATATATGACTGCCCGATGACTAATCTGGCCTTAGGTACGCACGCAGTTCGTACATAA
CCCCTTTTCCAACGAAAGCGCAGACAAAGGATTGGTCAAGGCCAGAGAAATGACCAGGACCGCGATTTTACTCGCCCTATTTGTCTTTCTGTGTA
CTTAGGTCTACTCTAGCGCTATTTTTCACTCCTATACTTACGATTAAAACAAAAAAATCTGTTTTGCTGCGAATAAAAGTAACTTTTTGCGTAGC
TGTTGGGCTGCTTCTTCTGGATGACTTGCGGTATGACCGTGGCCTGCTTCGTACGCAATGGTACAGAGCTCACTAAGGTGTCCAAAAGGTGGCAA
CATTTTGGTGAAGCTGTTGGCTGGCCCCACTAACCGGACCTGAAAATGGTGCAGCGCTGCCGGACATTTAACGGAATCAAAGATTCCACAAAAGT
CATGTTTGCATTAACAAAATTCATATTTAACCTTAACAAATTCAACAAATTAAGTTAAGTCCATTTTAGTAGCGTTGCGAGGAGTTTATTTTCGA
AAATACGCCTTTGTATATATTATATATTTTTCCTCCACTTTAAACAAAATCGAAAGGTGTCCATTTGTCAGCTATTTAAACAATATGGCATCGCC
GCCTTACTTGCTCAGTAAGAAAATTTAACTGTTTTTTTTTTGCGCACCTGAAAGCGGCGATAGACATTGTTTACTTTTAGTTTATATTTACATTA
TCCAAAAGCCAAATGAACTTTGAGCAGGTCAATATACCAGAGAAACTAGTGCCGGACAACTATTTGCAACTGGGACTGGCTGCGCAACGCAGTAA
GCAGCGCAGTTTTAAGGAGCTGCTCGAAAAGGTAATCAAACCGAAATTAAACCCAAATTAATTGATAACTCCATGGATAATTCTTCTTTTCAAGC
GAAAGCTTCCGAAAAATGGTTGGTCCGATGAACGTATCGAGGAGCTGGTGCACATGCTGGCTTCCTTGGACAGCAATAACTATCCACATAAGGTC
GGTTTAGGAGAGCGGGAGGCGCGTATAGCCTGCAGTAAGTAAGGGATCAGGAGGCGATATCCCCCGTAATGAATTTGTCATTCAGAACTCGTGGC
TCGCCGTCACTACAACTTCGGTCATGGTATCGGCAGATCTGGAGACTTACTAGAGGCACAACCCAAGGCAGCTGGCTCTACGCTGCTCGCTCGTC
TCACAAACGCCCTGATTCTGGACCTTATTCGGGGAATCGGACTGCCCAGCTGTGCTGGCTGCTTTTTGGTGCCAATGTGTACAGGCATGACATTG
ACTTTGTG
(SEQ ID NO: 205)

Exon: 6228..6122
Exon: 4471..4223

FIGURE SHEET 110

Exon: 4151..4051
Exon: 3449..3311
Exon: 3044..2879
Exon: 2622..2379
Exon: 2310..1968
Exon: 1229..1001
Start ATG: 4460 (Reverse strand: CAT)

Transcript No. : CT7116
TACGAAGCAGGCCACGGTCATACCGCAAGTCATCCAGAAGAAGCAGCCCAACAGCTACGCAAAAAGTTACTTTTATTCGCAGCAAAACAGATTTT
TTTGTTTTAATCCAATTTATTGTATGAGTCAAAAAACTGAAAGACCAGTGCTATCGGGTCAACGCATCAAGACCAGAAAAAGAGATGAAAGAGAA
AAATATGACCCAACGGGATTCCGTGATGCGGTCATTGCTGGTCTCGAAAAAACTGAAGGCGACCTGGAACAAATCTCTAAATATCTAGACAGCGC
GGGCAACAAGCTCGACTATCGTCGCTACGGTGAAGTTCTCTTTGACATATTGATTGCAGGAGGTCTACTAGTGCCTGGTGGTTCTATATCTCAGG
ATGGCGAAAAGCCGCGCACAAGCTACTGCATCTTCGATGCGCCCGAGAGCATGGAGAGCATGCGCAACCATGAGCAGGTATTTGTCAAGCTCATC
AGACGGTACAAGTACCTTGAGAAAATGTTCGAAGAGGAGATGGGAAAGGTTCTATTATTCGTAAAGGGCTTTACTCCTAGTGAACGCATCAAGCT
TGCGCGTATGACAGCGCTCTGGTTAGTCAACGGTTCTGTACCGCCAAATGTTTTACTGGTACTAAACAACGAGCACCTAATCAAGGATGGCATTG
CATTGGAGTTTCTACTAGAGCTGTTCCAGACGTTCAAGCAAGAGAAGGGCATTGCATATCTGATTCAGGCGCTTAAGAAGGGTGGACTGGAAAGC
AAACTTATGGACTTTTTCCCACCGAACAAACGTACTGAGGAATATTTTAAACAAGTTTTTCTTGACAAAGAACTTAACGAGATCGTCAAGCTACA
TAAGGCTCAGGCTAGCCAGGAGGCGAAGCGTGAGTTGCAGCAGGCGCTCATCGATGATATCAACGATGAGAAGCCATATAATGAGATAACCTCAG
ACATTAAGGACTTCTCGCAGCGCACCAACATTCCCGATCATGAAATAATTGTTATTATTTGGTCCACCATCATGTCATTGGGCGAATGGAACAAG
AAGGAGGAGCTGGTTACCGATCAGGCTGTTCGTCATCTGAAGAACTACTGCCCACTGTTGCAGGCTTTCGCCTCGACCGACCGTTCGGAATTGGC
CCTAATCTTGAAGGTGCAGGAATTCTGCTACGAGAACATGAACTTCATGAAGGCCTTCCAGAAAATCATTTTGTTGTTCTACAAGACCGAGGTCC
TGTCCGAGGAGATCATCTTGCGCTGGTACAAGGAGGGCCACTCAAACAAGGGCAAAATGCATTTCCTTGAACAAATGCGAAAGTTTGTCGAATGG
CTTCAGTCAGCCGAAGAAGAATCCGAATCTGAGGACGAACAAAAGAATGGCGAGTAAGAACTTGGTTGATGGCTAAATGAGGATGAACACAAACG
GAGCCGCCCTTTAGCATCCCCATCCAAAAATTCGAAACCAGCACCTGCAACAGCCAGTCGAACTATATATAAAACTCACCCCTATGAATTAATGT
CATTTTGAAAACTCCACCTATATAAAACTCAAAAATTCCAACAAATAAAGGAGAGAGT
(SEQ ID NO: 206)

Start ATG: 119 (Reverse strand: CAT)

MSQKTERPVLSGQRIKTRKRDEREKYDPTGFRDAVIAGLEKTEGDLEQISKYLDSAGNKLDYRRYGEVLFDILIAGGLLVPGGSISQDGEKPRTS
YCIFDAPESMESMRNHEQVFVKLIRRYKYLEKMFEEEMGKVLLFVKGFTPSERIKLARMTALWLVNGSVPPNVLLVLNNEHLIKDGIALEFLLEL
FQTFKQEKGIAYLIQALKKGGLESKLMDFFPPNKRTEEYFKQVFLDKELNEIVKLHKAQASQEAKRELQQALIDDINDEKPYNEITSDIKDFSQR
TNIPDHEIIVIIWSTIMSLGEWNKKEELVTDQAVRHLKNYCPLLQAFASTDRSELALILKVQEFCYENMNFMKAFQKIILLFYKTEVLSEEIILR
WYKEGHSNKGKMHFLEQMRKFVEWLQSAEEESESEDEQKNGE*
(SEQ ID NO: 207)

Celera Sequence No. : 142000013384564
GATGGCTGCAACTGCTCCGGTAATTATGCGCGTCATGGCGTCCTCGATCAGCACCGCCAAGCGGGCTGGCGGCATCATACGCGACGTGCTCAAGA
AGGGTGACCTGGGCATAGTGGACAAGGGCAAGAACGATCCGCAGACGGAGGCAGATCGCTCTGCCCAGCGTTGCATTATCGCCTCCTTGGCCAAA
AAGTTCCCCACCGTCAAGATCATTGGCGAGGAGGGTGGATCCGATCTGAATGTCTGCGACGACTGGCTGGTGAACGAGTTGGATGAGGAATTCCT
GCAGCACAGTTGCCCCGCTGAGTGGAAGGATGTCAAGCCCGAGGACTTTGTCATATGGGTAGATCCCCTAGACGGCACAGCGGAGTATACACAGG
GTGCGATCTGGAGATACCTGTAGAGCTCCTTATATAAAACTAAATGTTCTCCTTTCATCCGCAGGACACGTTGAACACGTGACCGTCCTGATCGG
CATAGCCGTGAAGGATGCTGCTGTGGGCGGCATCATTCATCAGCCATTCTACCAACAGCCCGATGGCGAAATGGGTCGCACCATTTGGGGCCTGA
AGGGTCTGGGCACGGGAGGATTCACGGCAGTCCCCGCGCCAGCCGGCCAGTTCATCATAACCACCACTCGCTCGCATTCCAATGCCCTGCATCAG
CAAGCCCTCAACGCATTCGCATCCACAGAAGTTCTGAAAGTCGGAGGCGCTGGGTTCAAAGTGCTCCAGCTGCTGGAGGGAAAGGCCCACGCGTA
CGTCTTCGCCACGCCGGGCTGCAAGAAGTGGGACACCTGCGCACCCGAGGCCGTTCTAGAGGCCCAGGGCGGCTGCCTCACCAACATCAACGGCG
AGCACTACGCCTACAATGCGGATGTGGAGCACGTGAATCGACAGGGAGTGCTGGCCAGCCTGGGACAGGACCATGCCGCGCTGGTGGAAAAGATT
CCCGCCGAGGTGCGGGCAGCAGTGGGAGCCAAGTGAGATAGCTTTGAATTCCAGCACTTTATTAGTTTATTTGCACTAAAAGTAAACACACATAA
ATTAAGCAATAACAGGTTAGAAATTTGAAAATTGTTAAAACTGGGCTCAGAATGCATTCTTTATTTATCGAAACTGCCGCTGTTGTTGCTCTGTG
TGCTGCTGTTGGCCACCGAGTTGTTCAGGTAGCGATTCCGCTTGGCCTTGGTCATTTTGCAGGAGTTTACGGAGGCCGCGAAGCGCAGCGACTTG
ACGGACTCTTGGAAACAGTCTTGGAACGGCGAGACGTTGATGAACATAAGCGTTTTCGAGTTGCCGCCCAGCGAGGGCATCAGCAGGTGCGTCAG
CTTGGAGTTCCTGTACGGGATGTGGTCCTGCTTCTGCAGCAGCGCCAGGATTACGTTGGTGAGCTCCGATAGCGAGCGATTGATGTTCTTTGTCT
CGGTCATCCGGGTGCTCGTCTTGGGAGACTCAGAGCCGGCCAAATCCACCAGGTTTATGGAACCCACGGAGATCTCTTGCTTTTCGGCATGGCGT
CCGATGAGCTCAAGCTTGGTAACCGCGTGGGAACGAGAGGAGCGCTCGTTGCCAGCTGTCGAGGCGGTGGCACGGTTCATCTTGGCCGTGTGCAT
GAGGTGGCGCAGGTGATTTGGATCCAGAACCGTCTCCTCCGTTATGTTGGACACGTAGATGTCGTTCTTGTTGTTCTTGGCCATTCGAATCTCCA
TGTCCTTCTGCTCGTTGCTCAGCAGATCGTAGAGCACCTCGTTGTAGATCTCCAGAAAGGTGGCCTTGATCTCGTACTCCCAGCCCAAGTTGCGA
TATCCCCGGATGGAGTCGAAGAGCAGATCCACCGTGCGCGGTATGACGCCCACACTCTCCGGCACTCCGTCCATTGTGTAGGTCTTGCCACTGCC
CGTCTGTCCGTAGGCAAAGATGCAGATATTGTAGCCATCCAGGGCCGACTGGATGAGCGGCGAGACCATCTCGAAGATGTCCGACTGCGAGGAGA
GCGGGTGGAAGACCTGGTCGAATGAGAAGATCTGCTGGCCCATCTTGCTTTTGGCCTGTGCGTCAATGCTCTGCAGCTCCACGGTGGACTCGTCG
TGATAGGTCCAGGTGCAACACATACGGTTCTCCTCGGACTCCAGCGGCGGTCGTATTCGACAGAAGACCCGGATGTTGCCGCGCAGGTCCATGAC
CGTGTTGTGCAGCTCTTTGCGCTCCATGTTCGACTGGAAGAGCTGCTCTTTGCAGGTCTCCAGCTCGGCGGCCTGCTGCTCATTGCAGCGCAGGA
GTTCCTCGGTGCGCTGGCGCAGATGCACCACTTCTGTGCTTAGAGCAGCATGCTCCGTTTTTACTTTCTGCAACACACACATTGTTGTTACATTT
AACCTGGGTTTCTGTTTACTTGAGTACTCACCTCATGTATTGCTTGCAGCTCGGATAGCTCCTCTTTGGTCCTGCCCAGCGTCGATGTGATTGTT
TCAATTTTGGCGGTATGCTGCTTCACCTGCCTCTGAAGACACTCGTTGTCGCTCTGGGTGTTCTTCAGCGAGGACTCCGTCTCGATAAGCTTGTT
CTGCGTCTCCTCCAGTTGCTGAGGCATGGACTCCAGCTCGCCCATGTCCTCTGTTTGCTTTTCGTACTTTGTCTTAAGCACCTTGTGCTTCTCTA
GCAGATCGTGGAAGCGGGCCTTGAAGTCGTAGGGAGCGATGCGCTTGGGAGCAGCAGCCGCGGCTCCTGACGAAGCTGCTGCTCCTGTTCCTGCT
GGTTTCTTGGCGGCTGCTCCTCCTGCAGCCCGTGGAGCAGGACGCGTTACTGGTGGTCTTTTGACAGCTGTTGCTGTTATTGACGAAGGCGCCGC
AGGACGCACTAGTCGCTGGCTGGAAACAGTGAGTGCACCGCCCAGGCGGGATACTTTGCTGGGAATGCTGGGCAATGAAGGAGCAGCCGCAGTGC GCTTGTTACCACGCAGTTCGTTGATGTCGCAAGCGCTACGGCTACGTCTCAGCTTGGCCCGGTGGCCCAACTTCATGGGCTCTGGGGAGGCGGCA
CGTGCTATCGGAAATTAGCAAGGACTTAAGGTGAATTCTTTGGAAGGATGCTTCTTTACTCACCTCCTCCTCCGCGACGCTCCAGCACCTGGGGC
AGATTGTTGAGGTCCCTTGAGAGGGGCGGCAATAAGTTGCCGCAGTATGTCTGGTTGGCATTGACATTGAAGGCGCCTGCTCCAGCGGCTCCACC
TCCCAATCCTGCGCGAATTCGATCTGTGGGCAGCACGGTTTTAATCGGCATTTGGGGTTTCTTCAGGCCCGACGGTTTCGGTAGCCGGGATTCCA
TCGCCAACTGTGTTGTGCCTAACTTAGAAGATACGTCTGCCTCCTTGCAACCGATTTTATCAATTAGTTTTGCGTTGTTGACAAGCGACGCCGTC
GATTCCCGCCGTTATTTTTGATTGCAGGGATGCTCTGGGGCAGTGTGACCATTTGTCGGGAGAGTACGGCGTTGCCAGCCAAGACGACTTCCAGT
TTGTCAATCAGATGTTTTCAGTGCTGCAGCTTTGGCCCTCGGGCACAAATTTTCGCCTTGACTCGTGCATCCCGCAGGTTTTCGGCGCGTGAAAC
TCACCCAAGCGGGTGTGAAATACGGTGGCTGTTGCATTCGAACCGTTCATTTTGTGGAAAAGTCGCGGCGGACTGTTCAACAGCCTGAAGAGTGA
AGTCTTGTGCGCAGCACTAGTGTCGTTGCCGGACGGTTGCGGCAATCCGGGGCGAACTTCTTGAAAGCGTTTTGCTTTCTTTTTGCGAGCTTGTG
CGGTGTGAAGGAAGGCCGCGCTATTCTGAAATTTATTTGTTGCCTCGAAAAAGCTGTGGAAATTGCGTTCCAGTTGGAAAGCAGTTGCGTGATCG
GGTCGTTGCCAGACCGGCCGCAGGTCTCACGCGACCATCTCTAGTTTGTTTTCATTCGGATTGGAAAAGGCTCGTTCCCATCGAACTGATTTTGT
GAATTTTAAAATTGGCTTCCCCCACGTCCGCCAATCCCCCCGAGATGTCGGGGCAGGCGGAGCTCAAGGAGCTGGGCATGTTCGAGCTGCGCCCG
CTGATCACTAACATCAGCTGCAAGCTGTCCGCGGTGACAGCGGGGCTGGACGAAAAGCGACAGTTCCTATGCCTCGTTTCTGAGGAAAACGAGAT
CCTGCTGCGCTACATAAGCGCCGCCTCCGGCCAGGAGGTGGTCAAGATGATATCCTGGTTCCGCAACCGCGTCATCCACGACGTCTGCTTCGATC
CGGCGGGCGTTTGGCTGCTGGTGCTATGTGAGTTTCAGCGTATGATGGCATGAGCACCACCCACTTTTTTGTGTTGGGTGGGTGGTTGCTGTGGT
GGTGCTGCTAAAATTACTTTGCCCCCATGTGTGCGTGTATGGTTATTGATTTTCTGCTGCCTCCCCTTTG
(SEQ ID NO: 208)

Exon: 3440..3104
Exon: 3044..2407
Exon: 2347..1001
Start ATG: 3326 (Reverse strand: CAT)

Transcript No. : CT7226
CAAAAATAACGGCGGGAATCGACGGCGTCGCTTGTCAACAACGCAAAACTAATTGATAAAATCGGTTGCAAGGAGGCAGACGTATCTTCTAAGTT
AGGCACAACACAGTTGGCGATGGAATCCCGGCTACCGAAACCGTCGGGCCTGAAGAAACCCCAAATGCCGATTAAAACCGTGCTGCCCACAGATC
GAATTCGCGCAGGATTGGGAGGTGGAGCCGCTGGAGCAGGCGCCTTCAATGTCAATGCCAACCAGACATACTGCGGCAACTTATTGCCGCCCCTC
TCAAGGGACCTCAACAATCTGCCCCAGGTGCTGGAGCGTCGCGGAGGAGGAGCACGTGCCGCCTCCCCAGAGCCCATGAAGTTGGGCCACCGGGC
CAAGCTGAGACGTAGCCGTAGCGCTTGCGACATCAACGAACTGCGTGGTAACAAGCGCACTGCGGCTGCTCCTTCATTGCCCAGCATTCCCAGCA
AAGTATCCCGCCTGGGCGGTGCACTCACTGTTTCCAGCCAGCGACTAGTGCGTCCTGCGGCGCCTTCGTCAATAACAGCAACAGCTGTCAAAAGA
CCACCAGTAACGCGTCCTGCTCCACGGGCTGCAGGAGGAGCAGCCGCCAAGAAACCAGCAGGAACAGGAGCAGCAGCTTCGTCAGGAGCCGCGGC
TGCTGCTCCCAAGCGCATCGCTCCCTACGACTTCAAGGCCCGCTTCCACGATCTGCTAGAGAAGCACAAGGTGCTTAAGACAAAGTACGAAAAGC
AAACAGAGGACATGGGCGAGCTGGAGTCCATGCCTCAGCAACTGGAGGAGACGCAGAACAAGCTTATCGAGACGGAGTCCTCGCTGAAGAACACC
CAGAGCGACAACGAGTGTCTTCAGAGGCAGGTGAAGCAGCATACCGCCAAAATTGAAACAATCACATCGACGCTGGGCAGGACCAAAGAGGAGCT
ATCCGAGCTGCAAGCAATACATGAGAAAGTAAAAACGGAGCATGCTGCTCTAAGCACAGAAGTGGTGCATCTGCGCCAGCGCACCGAGGAACTCC
TGCGCTGCAATGAGCAGCAGGCCGCCGAGCTGGAGACCTGCAAAGAGCAGCTCTTCCAGTCGAACATGGAGCGCAAAGAGCTGCACAACACGGTC
ATGGACCTGCGCGGCAACATCCGGGTCTTCTGTCGAATACGACCGCCGCTGGAGTCCGAGGAGAACCGTATGTGTTGCACCTGGACCTATCACGA
CGAGTCCACCGTGGAGCTGCAGAGCATTGACGCACAGGCCAAAAGCAAGATGGGCCAGCAGATCTTCTCATTCGACCAGGTCTTCCACCCGCTCT
CCTCGCAGTCGGACATCTTCGAGATGGTCTCGCCGCTCATCCAGTCGGCCCTGGATGGCTACAATATCTGCATCTTTGCCTACGGACAGACGGGC
AGTGGCAAGACCTACACAATGGACGGAGTGCCGGAGAGTGTGGGCGTCATACCGCGCACGGTGGATCTGCTCTTCGACTCCATCCGGGGATATCG
CAACTTGGGCTGGGAGTACGAGATCAAGGCCACCTTTCTGGAGATCTACAACGAGGTGCTCTACGATCTGCTGAGCAACGAGCAGAAGGACATGG
AGATTCGAATGGCCAAGAACAACAAGAACGACATCTACGTGTCCAACATAACGGAGGAGACGGTTCTGGATCCAAATCACCTGCGCCACCTCATG
CACACGGCCAAGATGAACCGTGCCACCGCCTCGACAGCTGGCAACGAGCGCTCCTCTCGTTCCCACGCGGTTACCAAGCTTGAGCTCATCGGACG
CCATGCCGAAAAGCAAGAGATCTCCGTGGGTTCCATAAACCTGGTGGATTTGGCCGGCTCTGAGTCTCCCAAGACGAGCACCCGGATGACCGAGA
CAAAGAACATCAATCGCTCGCTATCGGAGCTCACCAACGTAATCCTGGCGCTGCTGCAGAAGCAGGACCACATCCCGTACAGGAACTCCAAGCTG
ACGCACCTGCTGATGCCCTCGCTGGGCGGCAACTCGAAAACGCTTATGTTCATCAACGTCTCGCCGTTCCAAGACTGTTTCCAAGAGTCCGTCAA
GTCGCTGCGCTTCGCGGCCTCCGTAAACTCCTGCAAAATGACCAAGGCCAAGCGGAATCGCTACCTGAACAACTCGGTGGCCAACAGCAGCACAC
AGAGCAACAACAGCGGCAGTTTCGATAAATAAAGAATGCATTCTGAGCCCAGTTTTAACAATTTTCAAATTTCTAACCTGTTATTGCTTAATTTA
TGTGTGTTTACTTTTAGTGCAAATAAACTAATAAAGTGCTGG
(SEQ ID NO: 209)

Start ATG: 115 (Reverse strand: CAT)

MESRLPKPSGLKKPQMPIKTVLPTDRIRAGLGGGAAGAGAGAFNVNANQTYCGNLLPPLSRDLNNLPQVLERRGGGARAASPEPMKLGHRAKLRRSR
SACDINELRGNKRTAAAPSLPSIPSKVSRLGGALTVSSQRLVRPAAPSSITATAVKRPPVTRPAPRAAGGAAAKKPAGTGAAASSGAAAAAPKRI
APYDFKARFHDLLEKHKVLKTKYEKQTEDMGELESMPQQLEETQNKLIETESSLKNTQSDNECLQRQVKQHTAKIETITSTLGRTKEELSELQAI
HEKVKTEHAALSTEVVHLRQRTEELLRCNEQQAAELETCKEQLFQSNMERKELHNTVMDLRGNIRVFCRIRPPLESEENRMCCTWTYHDESTVEL
QSIDAQAKSKMGQQIFSFDQVFHPLSSQSDIFEMVSPLIQSALDGYNICIFAYGQTGSGKTYTMDGVPESVGVIPRTVDLLFDSIRGYRNLGWEY
EIKATFLEIYNEVLYDLLSNEQKDMEIRMAKNNKNDIYVSNITEETVLDPNHLRHLMHTAKMNRATASTAGNERSSRSHAVTKLELIGRHAEKQE
ISVGSINLVDLAGSESPKTSTRMTETKNINRSLSELTNVILALLQKQDHIPYRNSKLTHLLMPSLGGNSKTLMFINVSPFQDCFQESVKSLRFAA
SVNSCKMTKAKRNRYLNNSVANSSTQSNNSGSFDK*
(SEQ ID NO: 210)

Name: KINESIN-LIKE PROTEIN
Classification: motor_protein
Gene Symbol: ncd
FlyBase ID: FBgn0002924

Celera Sequence No. : 142000013384244

FIGURE SHEET 112

TGGACTAAACTCGCAGATTCCTGTAACTTGGAAGCACCACGAGTTTGCTTTAGAAGATGCCTTTCCGTTGAACTAAAACTAGACGAGTAAAGCGT
ATCTCAAACATTGTATCTTCCGAACCAAAATAGTGCTGCATACTTTTCGGGATATGTCTTATTCAATGTAAGTAATACAAAAAGAAAAAAGGTAA
CTTCTTAAAACTTGTAATATTTGTCACAAATGAATGACGACTAGATTTGGCCATGTCTGTAACAATAAACGTACAAAATATTCGAAGTTGCAGAA
ATGGGGATCCAGCATTCGGATTTGGTTTTTTGTCAAACTTTTAAATATAGAATCGGACCACATCTTTTTAAGACCTTAAAAAACTGATTTGAAGT
TAGACCCCTCATAATGCCAACTAAATTTGTTAAACAAAAATATGCCCCTATATGCCAATCAAATTTAAATACAATGCTTTCTCAGCGTTTCAGTT
AAATACTTTGGGTTGTTTAATGGTTTTATACGTATACATGTGCTAAGTCCATGTATCTTATATTTCGTAAATCCATAGATTTTGTTCGACGAAAC
TTTGCTAAATGATATTGATCTTTCAAATATAACTTGTTAATTTCCTTTCATCGCCGTGGCAAATCCTTCGAGAGTGAGTACTACTTGTTAAACGC
ATATATGAGGAAAATTTATTGATGAATAATGCGAACATGCAAACGGAACACATCCCCGAATTCACACAAAGCATCTCTGTGGTATCTCTTTTGGT
TTTTTATTTGTTGCATCAACTCCGCGGAACTCCAGCTACCTCACTGCAGGTCGTAGTAGTCGACGTTATTGGCGGTCAGATGTTCTCTATTAATT
TGGAGCGTGCTGCTGTTTCCACTTCAAACTTTTATTAACATATATAGTATGGGTTTGCCGGTATATTGCAAACGGGAACTAAGTGTAGATTCGTG
AATGATATCAGACTGGACTGCAAACGTTTAGTTTCTAGCATGTTTTTTTACTCTCTCCTTTATTTGTTGGAATTTTTGAGTTTTATATAGGTGG
AGTTTTCAAAATGACATTAATTCATAGGGGTGAGTTTTATATATAGTTCGACTGGCTGTTGCAGGTGCTGGTTTCGAATTTTTGGATGGGGATGC
TAAAGGGCGGCTCCGTTTGTGTTCATCCTCATTTAGCCATCAACCAAGTTCTTACTCGCCATTCTTTTGTTCGTCCTCAGATTCGGATTCTGAAA
GAGAATAGAATACAAAATGTTAGTATGGGGGCTTCAATTGGTACAAACTGAAAAGATGTGCAGCTCCGGTTATGCTGTCCAAATGATTATTGGCC
AAATTTAACTATGGAAAGTTATCTGGACACCCAACCATTCAAATGCTTTGGCACAACTCCCCGCTTGGCTCAATCGAATGAAGCAACCATTCGGA
GCTTTTATGAGGGGATTGTGCATGCGGACTAGGACAAATGCAGCTGTCCAAACGATTATTGGCCAAATTAACCACGGCATTGGGTTATATGGGCA
CCCAATCATTCTTTCGCTTTTGCATACTGTACATGAACCCTTTAAAACTGGTTCCTAATAATGGGAACACTTTAAAAGCTTGGTAAGAAGCATGC
TCGGTGAAGTCAGCTATTTGTGTCCAAGTTTTCATTGGCCTTTGATGCTCGGATTTTGTGAGGCAACAAGGCAAGCAAAAACTCAAATGCTCTTG
CAATTTTGTACAATGAAAATGTCATCCAGGACAAGACCATTCTCAAAAAGTGCACTGTGTAAAGTTTCGAAGGAAGCAAAATTTGAATATTTATA
TTGTCCAGGTTTTCATTGGCCTACGTTGTTCAGTGAATGGAAATCAACGAGGCAAGCAAAAAACCCAAATTTCTCTTGCAATTACGTACCAGAAT
CAAGCTATTTAAGACAAGACCATTCTCAAAAATTGCACGCTGATAACATTTATCAAAACATACTAACCTTCTTCGGCTGACTGAAGCCATTCGAC
AAACTTTCGCATTTGTTCAAGGAAATGCATTTTGCCCTTGTTTGAGTGGCCCTCCTTGTACCAGCGCAAGATGATCTCCTCGGACAGGACCTCGG
TCTTGTAGAACAACAAAATGATTTTCTGGAAGGCCTTCATGAAGTTCATGTTCTCGTAGCAGAATTCCTGCACCTTCAAGATTAGGGCCAATTCC
GAACGGTCGGTCGAGGCGAAAGCCTGCAACAGTGGGCAGTAGTTCTTCAGATGACGAACAGCCTGATCGGTAACCAGCTCCTCCTTCTTGTTCCA
TTCGCCCAATGACATGATGGTGGACCAAATCTGGTAAAGATCATACATGAGATTTAGTAAGGAAATCATCCAGTTGGATTATTTACGCATCGACT
TACAATAACAATTATTTCATGATCGGGAATGTTGGTGCGCTGCGAGAAGTCCTTAATGTCTGAGGTTATCTCATTATATGGCTTCTCATCGTTGA
TATCATCGATGAGCGCCTGCTGCAACTCACGCTTCGCCTCCTGGCTAGCCTGAGCCTTATGTAGCTTGACGATCTCGTTAAGTTCTTTGTCAAGA
AAAACTTGTTTAAAATATTCCTCAGTACGTTTGTTCGGTGGAAAAAGTCCATAAGTCTGGAAAAACGTGAAAAAGTGGAACCATTATTAATAAT
TTAAGTTAACGCATTCAATAATCAACCTTAAATGACGTATTGAGGTGTACGAAATTAAATCAGCACCCAAATGAAGCGAAAGGTCATTTGCGAAT
TGGGTAAAACTCCGTCGAACTTTCTTACTCTAGGAATATCAATTAAAGATGCACAACTGGATCATTGAGTCATCTTCCTGAGAACATTCCGGGGC
TAAAAACAAATCACAACTAAAAACTTACTTGCTTTCCAGTCCACCCTTCTTAAGCGCCTGAATCAGATATGCAATGCCCTTCTCTTGCTTGAACG
TCTGGAACAGCTCTAGTAGAAACTCCAATGCAATGCCATCCTTGATTAGGTGCTCGTTGTTTAGTACCAGTAAAACATTTGGCGGTACAGAACCG
TTGACTGTTGATCAAAAATAGGGTTAAATATAGGGTTAGTCAAATGTTTTCGCAAAACAAGTTTAGACGGCCGGCTAGCAATCCTGTCCTTGGGC
TCGTGGCCCTTAGATGTGGTTAGTTCATCCAAGAGTCAGTATACCAAGTGAAGGATTACTTTAGCCCCTCAGCTGCAAGTTGAACAAGTGTTTAT
CGAAACAACTAATTGAAAGACCGAATGGGCAGACGCAAGCAATGCACAGGAGGAACAGGAACATAAATGTTAAGACTTACCTAACCAGAGCGCTG
TCATACGCGCAAGCTTGATGCGTTCACTAGGAGTAAAGCCCTTTACGAATAATAGAACCTTTCCCATCTCCTCTTCGAACATTTTCTCAAGGTAC
TTGTACCGTCTGATGAGCTTGACAAATACCTGGAAAAGGTAAAGTGTGATTGCCCCTGTTAGCGGATGGTGAAATTTTACTGTGTTCTCACGCAG
GAGGCTTTTGTATTTGTTGTTGCAACATTAGAAATCTTTAGATTGCTGGCGGTAGTAATTTTACAAAATAAAGACAAGTAAAATGTGGCTTTTTA
TTTTGCATATTTTGACACCGATTGAGTTGTTGAGATGCATAACCGGTTCTAATAATATGCACTTTGATTCAATAGCGTGACCTTCGCAGTGGTTG
CATGCATATAGTATATATATATAGTGTTGAATAAAGAGTAGTTGTTGACACATAAGAAATCTTCAGAACGTTAGTGTTTAGGACAAACCAAAGAC
AAGTAAATGTGTTGATTGTTATTGCATATTCTTGACACCGATTACATTTTTGAAACTTTATAGTCAGCTCTAATGATATGCAGCCACTTCACGAA
TTTCATACTTTTAAGTGGATCCGAAGAAAATCATTTAGTAGTAAATAAACGTTTTAGCTTGGAAAACAACAAGAGCTCAACTTGTGTTGCAATCA
AACCAATTTTCGTTTACTCATAATCATAATTTAAGTATGACCTGCTAAAAGATTACAAACCTGCTCATGGTTGCGCATGCTCTCCATGCTCTCGG
GCGCATCGAAGATGCAGTAGCTTGTGCGCGGCTTTTCGCCATCCTGAGATATAGAACCACCAGGCACTGCAATTGAAACGAGGATGGAAAAGGGT
CAGTGAAGAGACTAAACACATTACTTGCAGCGGAAAACTTACCTAGTAGACCTCCTGCAATCAATATGTCAAAGAGAACTTCACCGTAGCGACGA
TAGTCGAGCTTGTTGCCCGCGCTGTCTAGATATTTAGAGATTTGTTCCAGGTCGCCTTCAGTTTTTTCGAGACCAGCAATGACCGCATCACGGAA
TCCCGTTGGGTCATATTTTTCTCTTTCATCTCTTTTTCTGGTCTTGATGCGTTGACCCGATAGCACTGGTCTTTCAGTTTTTTGACTCATACAAT
AAATTGCTGCAAAGGTAAATGTGGATCAGAGATGGAAGCGGTTTTGGTTTGCCCCTGTAAGTTTTTATTTCTGACCAGACTAAATTATCATGGCC
ACTAGATTCATTTTTAGATTTATCTTAATTTTAGTGTAAGATGACTAAGGTGGTCTCCAAGCGGTGGAAAACCGTTCCCTGTATATGTATTCTCG
TTGCGCTCATAATCAAACTACAACATTTTCACCTATGACCGGCGTTTAAGTGGAAACTCTAGTGAAAACTGAGCCTAAGAAAGCCTTAACCTAAA
AATGCCAGCGTACATGTGCTTTAAACACACACATTCAAGAGCGGAGAACGGGCACACTTCACATCTCTTTTTAATTATCTCTCTTTTTCACACAC
ACATACCCACTGTGCATTTTACAGTTTGATAATGTCGACAAAAGAAATAAAAAGAATTGAGAGGTGAGGCGACCAAGAAATCGACATAGAAACGC
AGAATAAAGTGAAATTTTGACGTGGTTACTTGTGTTAGGTAGCGCGCTGGGGAAATGAGGTCATTGTGCATGTAGTGCACATAAAAACGCGCCGA
TGACTGTGTGCTAGTTGGCCGGGAAAATTGTCATAGCAGCGAAAACGCAAAAATTAAATTATCTAGGCTATCAAGTACACATTGGTACATATAAG
GAACGGCAACTTACGCTTTCACCCAAGGATATTAAGTCTGGCCCTGTGTTTGCCGCTTCCGCGTGTCCTTGCAATCAATTGAAATCAGTCGTGTG
CGAGTGTAGTGTGTATGTGTGTGTGTGTGCCTGTTGCTTTTTCACAACTAACGAACGTGCGAGAATATGTAATTTAATTTAACCTCACGAAGC
GCTGGCTGGTTAATGCTTCTCACTCGAGTCGACGAAAAACAAAGAGACAGATGGCAGATCCCTTCTTTTCTTACCTCTCTTTTCTTATGAGCGAG
CTTTTGCACGGTAAAATTGACACGCACGCACACACACAACAACAAAGAAAAGGGGAGAGCAAATAGAAAATATAATTTTTTGTAACGGAATTTAC
TTTTATGCCTTCAAAATAAACGTTAACAATTTTGCTCAGACTACGTCCGGAATTCTATTTTTAACAGCTATCACAATCGGTTACTAGGTATATGT
GTTGTTTGCCTCGAATCCAGCGCCCCTCTGCTCGCACCACTTTGTTAAACGAAATTCGGAGAGCGAATGAGACGACACACGAGCGCACGAACGAA
GCGGACGAGCCGAGAACGAAGACATGTGGTTCGGCGCCATTTTGAAGCGATACACTGACATGGCGAAAGCGGAATGATGGGCACAGGGAAAACGA
AAATTAGGGGGAAACGGTGAGAAAAAATGTGGATGGGGGTTCAAAGTGTGTATATTGCTGTCGCGCTTATTAAATAATGAGCAAGGTACAGTCG
AACAAAGGCCGACGGCCACCAAATGATTTTTTGCATGAATATATGACTGCCCGATGACTAATCTGGCCTTAGGTACGCACGCAGTTCGTACATAA
CCCCTTTTCCAACGAAAGCGCAGACAAAGGATTGGTCAAGGCCAGAGAAATGACCAGGACCGCGATTTTACTCGCCCTATTTGTCTTTCTGTGTA
CTTAGGTCTACTCTAGCGCTATTTTTCACTCCTATACTTACGATTAAAACAAAAAAATCTGTTTTGCTGCGAATAAAAGTAACTTTTTGCGTAGC
TGTTGGGCTGCTTCTTCTGGATGACTTGCGGTATGACCGTGGCCTGCTTCGTACGCAATGGTACAGAGCTCACTAAGGTGTCCAAAAGGTGGCAA
CATTTTGGTGAAGCTGTTGGCTGGCCCCACTAACCGGACCTGAAAATGGTGCAGCGCTGCCGGACATTTAACGGAATCAAAGATTCCACAAAAGT
CATGTTTGCATTAACAAAATTCATATTTAACCTTAACAAATTCAACAAATTAAGTTAAGTCCATTTTAGTAGCGTTGCGAGGAGTTTATTTTCGA
AAATACGCCTTTGTATATATTATATATTTTTCCTCCACTTTAAACAAAATCGAAAGGTGTCCATTTGTCAGCTATTTAAACAATATGGCATCGCC
GCCTTACTTGCTCAGTAAGAAAATTTAACTGTTTTTTTTTTGCGCACCTGAAAGCGGCGATAGACATTGTTTACTTTTAGTTTATATTTACATTA
TCCAAAAGCCAAATGAACTTTGAGCAGGTCAATATACCAGAGAAACTAGTGCCGGACAACTATTTGCAACTGGGACTGGCTGCGCAACGCAGTAA

FIGURE SHEET 113

GCAGCGCAGTTTTAAGGAGCTGCTCGAAAAGGTAATCAAACCGAAATTAAACCCAAATTAATTGATAACTCCATGGATAATTCTTCTTTTCAAGC
GAAAGCTTCCGAA
(SEQ ID NO: 211)

Exon: 5853..5395
Exon: 5274..5145
Exon: 4471..4223
Exon: 4151..4051
Exon: 3449..3311
Exon: 3044..2879
Exon: 2622..2379
Exon: 2310..1968
Exon: 1229..1001
Start ATG: 4460 (Reverse strand: CAT)

Transcript No. : CT7240
CAATATACACACTTTGAACCCCCATCCCACATTTTTTCTCACCGTTTCCCCCTAATTTTCGTTTTCCCTGTGCCCATCATTCCGCTTTCGCCATG
TCAGTGTATCGCTTCAAAATGGCGCCGAACCACATGTCTTCGTTCTCGGCTCGTCCGCTTCGTTCGTGCGCTCGTGTGTCGTCTCATTCGCTCTC
CGAATTTCGTTTAACAAAGTGGTGCGAGCAGAGGGGCGCTGGATTCGAGGCAAACAACACATATACCTAGTAACCGATTGTGATAGCTGTTAAAA
ATAGAATTCCGGACGTAGTCTGAGCAAAATTGTTAACGTTTATTTTGAAGGCATAAAAGTAAATTCCGTTACAAAAAATTATATTTTCTATTTGC
TCTCCCCTTTTCTTTGTTGTTGTGTGTGTGCGTGCGTGTCAATTTTACCGTGCAAAAGCTCGCTCATAAGAAAAGAGAGTTGTGAAAAAGCAACA
GGCACACACACACACACATACACACTACACTCGCACACGACTGATTTCAATTGATTGCAAGGACACGCGGAAGCGGCAAACACAGGGCCAGACTT
AATATCCTTGGGTGAAAGCCAATTTATTGTATGAGTCAAAAAACTGAAAGACCAGTGCTATCGGGTCAACGCATCAAGACCAGAAAAAGAGATGA
AAGAGAAAAATATGACCCAACGGGATTCCGTGATGCGGTCATTGCTGGTCTCGAAAAAACTGAAGGCGACCTGGAACAAATCTCTAAATATCTAG
ACAGCGCGGGCAACAAGCTCGACTATCGTCGCTACGGTGAAGTTCTCTTTGACATATTGATTGCAGGAGGTCTACTAGTGCCTGGTGGTTCTATA
TCTCAGGATGGCGAAAAGCCGCGCACAAGCTACTGCATCTTCGATGCGCCCGAGAGCATGGAGAGCATGCGCAACCATGAGCAGGTATTTGTCAA
GCTCATCAGACGGTACAAGTACCTTGAGAAAATGTTCGAAGAGGAGATGGGAAAGGTTCTATTATTCGTAAAGGGCTTTACTCCTAGTGAACGCA
TCAAGCTTGCGCGTATGACAGCGCTCTGGTTAGTCAACGGTTCTGTACCGCCAAATGTTTTACTGGTACTAAACAACGAGCACCTAATCAAGGAT
GGCATTGCATTGGAGTTTCTACTAGAGCTGTTCCAGACGTTCAAGCAAGAGAAGGGCATTGCATATCTGATTCAGGCGCTTAAGAAGGGTGGACT
GGAAAGCAAACTTATGGACTTTTTCCCACCGAACAAACGTACTGAGGAATATTTTAAACAAGTTTTTCTTGACAAAGAACTTAACGAGATCGTCA
AGCTACATAAGGCTCAGGCTAGCCAGGAGGCGAAGCGTGAGTTGCAGCAGGCGCTCATCGATGATATCAACGATGAGAAGCCATATAATGAGATA
ACCTCAGACATTAAGGACTTCTCGCAGCGCACCAACATTCCCGATCATGAAATAATTGTTATTATTTGGTCCACCATCATGTCATTGGGCGAATG
GAACAAGAAGGAGGAGCTGGTTACCGATCAGGCTGTTCGTCATCTGAAGAACTACTGCCCACTGTTGCAGGCTTTCGCCTCGACCGACCGTTCGG
AATTGGCCCTAATCTTGAAGGTGCAGGAATTCTGCTACGAGAACATGAACTTCATGAAGGCCTTCCAGAAAATCATTTTGTTGTTCTACAAGACC
GAGGTCCTGTCCGAGGAGATCATCTTGCGCTGGTACAAGGAGGGCCACTCAAACAAGGGCAAAATGCATTTCCTTGAACAAATGCGAAAGTTTGT
CGAATGGCTTCAGTCAGCCGAAGAAGAATCCGAATCTGAGGACGAACAAAAGAATGGCGAGTAAGAACTTGGTTGATGGCTAAATGAGGATGAAC
ACAAACGGAGCCGCCCTTTAGCATCCCCATCCAAAAATTCGAAACCAGCACCTGCAACAGCCAGTCGAACTATATATAAAACTCACCCCTATGAA
TTAATGTCATTTTGAAAACTCCACCTATATAAAACTCAAAAATTCCAACAAATAAAGGAGAGAGT
(SEQ ID NO: 212)

Start ATG: 601 (Reverse strand: CAT)

MSQKTERPVLSGQRIKTRKRDEREKYDPTGFRDAVIAGLEKTEGDLEQISKYLDSAGNKLDYRRYGEVLFDILIAGGLLVPGGSISQDGEKPRTS
YCIFDAPESMESMRNHEQVFVKLIRRYKYLEKMFEEEMGKVLLFVKGFTPSERIKLARMTALWLVNGSVPPNVLLVLNNEHLIKDGIALEFLLEL
FQTFKQEKGIAYLIQALKKGGLESKLMDFFPPNKRTEEYFKQVFLDKELNEIVKLHKAQASQEAKRELQQALIDDINDEKPYNEITSDIKDFSQR
TNIPDHEIIVIIWSTIMSLGEWNKKEELVTDQAVRHLKNYCPLLQAFASTDRSELALILKVQEFCYENMNFMKAFQKIILLFYKTEVLSEEIILR
WYKEGHSNKGKMHFLEQMRKFVEWLQSAEEESESEDEQKNGE*
(SEQ ID NO: 213)

Celera Sequence No. : 142000013384892
CATTTACATAACCGAGCCAATATTGAAGTGGTTTATAATAGATTAATAAGATTGTCCCAAAATTTCTCTATTAAATGTCAAGAGGCTGTGCACCA
GCATATAAATGATTTGACCTATCCACCTTAATTGTAATTTTTAGATAATAGCCTTTTTTAAGTGCTTAGATTTTTTTCAATTACATAAAATTTT
TTTCCCAATCGGTATAATATTTTCATTATCATATTATTCATATTGATATTAATATCTAAGTAGATAAGGTTTAATTATTGGCCTGTACTCTTATT
ATTGTTAAGGTTAAAATAAAAAAAAATTGGATGTCATTAAGCGTGAAATAAATGAAATGAAATAAAATTTTGCGGAGTTTATTCTTCATGTAATT
TTAGCTAAAGTGTGAACTGTAGATTTGCCGTGTTTGTTTTACAGGCTTCTTAATTGACGTAAATATATGGGATATAATGTCATGAGTCAAGAGAT
TATCAAATATTAAATTTTCTGATTAAAATTAAACGAAAGTCCAAAAATACAAAAAAAAAAACAACTTACCGTAGGCAAAATAGTAATACTATTTG
TAACGTTCTGTGTCGAAATCATATTACCTAAAATAGTTTACTTTCCACTAATATGTACTTGGACCGCACCCTACCAAGAAAATAATAATTTCTAC
TATTGGCGACAGCTGTTATTTGTGCGAATACAAACATGCTCAAATTAATAAAAGTTACGCTTACAGTTTGATTTTAATTTTTACGTTTCATTTTA
TTTTTTAATAATCTCGAATCTTGATTTTGCTGAATGCTGGATTTACTGGCCATTACCTTTCCTGCCCATTAAATCGTTGTTAAACATTGAACATT
AATGAGAGTTTCGTCGCAGACTATTTCGTAGGCTTAGACAAGTAAATAAAATGTAATTGGGAATGTGAAATAGGTGGTACCTTGATTACAAATAA
AAAAGGTACGATTTCGAAAGCATTTTAAAAATAAACATTTCAGAGTATTGCTGTAAAAGTTGTTTTTCGTACTTTTTATTGTTTCTATGTGGTAG
TATTTTTTTAGCCGGTTGGCATACATTTTTCTGGGGTTGTTGCTGGCAGCTTTTTGTTACATTTTACTGAATTTTTAGTTTTACTTTGTTCGATA
TAAATATTCATACTCAAAAATAAGATACGGTTGTAAAATTAAAAATTGTAAAGGATTACATATGTTATTTTGCCGTAATTGTTTTGATGTTTTTC
TTACTTAAAGATTTTGTTTGCAATTTGTTTCATTCGCTTCGTATTTTTTTTTACAATTATTAAATTTGACGCTTTTGTTTACAACTTTTATTCTT
AAAACATAGAGGGTCTCGCATCTTAATTTCGCTTAATATTGTTCTCTTAATCCTTCGCTTTATATATATATATACTTTGCTTTAAAGTTAAGATT
TTAAGTAAGTTTTTAAATAATAATGGATTTTTTGTTTTCGTTTGTTGCCGGTATTGTTGGTTGGTAGGTTGTTTGTTAGTAGAGAGAGAGAGAAC
CGGTACGCTATAAAACTACGCTCCCATTGCCGGATTGTTATTGGAGAATTGCGCCCGCCACCCAAGCAGCCACCCACGTATCACCCGCTCACAAG
AGCGGAAAATGGATACAGTCCGGGTTCCTGGCGGTAGAACCGTAATTTCTGTGATTTGCTTTTTTTGTGTTAGTAAGTATTTAATAAGTAGATTA
CTGAGTTTGCTGCTCCGCGGGCGATTCCCTTAGGCGGCCACTTCGCTAGCCTCGGCCCCATTCTGAACCTCATCCTTTGTGCTGGCCTCATCAAG CTTAGCCTTTTTCTCCGGCGTGGCGACGGCCTCATCTGCCTTGGCTGCAGCCTCATCCACCTTCCGCTTTACAGCCTCAATGGCGGGAGCATCTG
TAAGGCGATAATAAAAATTGAACAATAAGAACATGAACGTGGAAAATTTGTTTGGCATTGATATCATTGATATCATCATACCTGTTGAGTCACCG
TTGGTGACCTCCTCGGAGCCATTCTCGACAGCAGGTAGAACAGCTTCGCTGCTCTCTTTTTTGGTGTCCTCCCCATCGGCAGCGGAATCCTCTTT
TTTATCCTCGTCCTTCTTCTCATCCTTATCGGCGGCAAAAGAAACAGTGGGCTCAGACGCCTTTTCACCATCGACTGCGTCGGTGGGCTCGGTCG
CGCTGCTGTCGGCGGCTCCGTTCTCCTTGGCTACGCTCTCCTCTTCGGCGCCACCGTTTTCTGTGATGCTCGCCTTCTCAGCTGCTACCTCCTCG
GCGGCAACTGCATCTTTCTTCACAGCATCAACTTCCTCAGCTGCGACCTTCTCGACAACAGGGGTCTCACTGTGGGTGATAATCAGAGACGAAAG
TCAGTATGCACTTATAATTTTTTCCGAAGGTGGCCGAACTGAACTTCGTATGCATAGCATTCTACTACATACAAAACTCTAAACAGTAAATCAAT
TAAAAATTATCAAAAACTAAAACTATTAATTATTAATTAATTAAATATTAATTGAATTTAAAAAAAAAAAAGAAAAATTTCAATATAGCGCCGGT
AGGTAACGTTTATGTTTTCATCCTCCACTTTCTATTCATAAGAGCCCCAGGACGTTCGGAATTAAAACTAAAAAAAAAGTGCATTGTTACATCTG
CCGGCGTTTTTCAAAAATGGGATCAACAACTCGTGCAAGCTGCGACGCAAAAGGAAGCGCGAAAAGGTGAGTGCGATTAGGCGGCACGCTCTTTT
TCATATAAATGGCATATATTCATTTGTTATTTCAGTGCTCTCTACCAACAGATGAGAACAGGGTAGAACCAAAAACACGCTTGCAGACGTGCAAA
ATGAAAAGCGAGACCCGTTTAAACTAAAACGAACAAAGATAGAAATAAAAACCAGTTTTAATGGGATTAATGACAATATAGTCGTTTCTCTCGCA
CTCATCTACCAACAGATACTCGCCATCTGAGGTAGATAGAATTCTATAGGGCGAACAAAAAGAGAGTTGCAAAGTAGCAACGCTAAACGACAAAA
ATAACGGTCCAAACGATACAAACAGTAGCATAACGTCATACAACCTGCGTCTTTCAAAGAAAACCGGAACAGCCTTAGGCATGAGTTTTGTTTTG
TTATGTATTATAAGCTGCAACATATAATAACTACTTAAAAAAAATATATACATAAGTGTTCATCGATAGGGAAAGAGGGAGTATTTTTGGTAATG
CCAATATAGATATGCGTGAAAATTTATACTGTTAATTTCAAGCTTCGAGCTTTAAGCTATCAAATGGGTATAAAAGGCAAGCCTCGAAATTTGAT
GTCTGGTGAGAAACGCAGCAAAGCAACATACGAGGTAGCACAGACAGATGAAATGAAACAGCACAAGAAAAGAGCGGCAACTTGAATGCTGCACA
CGCATACACACACACATGTCTATAGACTTTTGCGCATTTGGCCTGTCGTCCGCATACACTCAACGCATTACTCCGCCGCTACACACACACACACA
AATAATTCATCGTTGCTGTTTGCCGGCCGGAGAAAGAGCGAGAAGGCACCATGACGCCGCGCCAAATTAAACGGCGTCGGTTTTTGCGCGCACAC
CGTTTGCCTTTGGCGGGAACGAGACAACTACATTAGTGCCAACAAGCGGTTTGCGTATATAGACACAGAATTCAAAAGAAAATTTCCAAATCTT
TTCGGCAAATAACATAGATTTTCATTAGCAAAATTCGCTACAAGTCCATTGCTTAAACAAAATCCACAAACGTCCGAAAACAAGGCAAGCAAAGT
ACTCACTTCTTTTGCTCAGCCACATCAGCCATTTTGAATTACTGTTAGATATTACTTTTCAAACGCGAAGCGAGAAAACACGTTGTAACTGAGGG
TTTTTGGATCACCAAGCACGCCTTAAATATCAGCACAAAGATTTTAAAAGAACGAAATTTTTATCAATATAGTTTCCTCTTTAGTAGCTTTGCTAA
GAAAGTAGCTTGGTTGCTGGAGATTTTGCCGTACAATTAAGAACGTCCACACAGTCACAAAGAAAAACGCCGAATGAGAGAGCGGTGAGCGTCGG
ACCGGCTTTTAAAGCGCCGCCCTGTAGTGTTGGTAGACGTCGGTAGTCCGCTTGCGATAGTTCCGCCTCCGGAAAACATATCTTGTTTGTTATC
GTTATCACCCGTTCTCTATTTAATTCGGAGTTAGCTTATGCTGATAGATTTTTACAATTTTATTTTAATATATTAAAGAGATGAAATATAGCAGT
GACAAATATTTCAAAATAACGGTCCCCTAAAAAGGGCTGCCACCTTTTAACTATTATTTAGCGGCTACACAAATATAGCAGGTAAAATATTCAAA
TGCATTCCTATCCTTGTTTTTCTCATTGACCTGAGTGATTTTTCGTGTAATACACCTTCCCAATTCTAAGTTTTTTTTTGATCCGGTACTCCTA
AAAATTAAATAAACAAACACACAAACATGTATGTTCATATATATATATATACACATATCGTCATTTTTAAAAAATTCAAGCTTTTATTAAATTA
CATCAATCAATTTCCTTGTAAATTACACAGTCTACAAGATCTTAAAAATAATATCTTAAAGATATGTCATATGTATGTAATCAAACACATAAAAC
CGACGGAAATAATCCTCACCCCTCTGAAAACATTTTCAGGTAGTCAGATATGCACGCATAAGTACGTACATACATACATATGTATAGTGGCCTTG
TCTGCGTCCCTTGATCGGTATAATAGAAAAAAGAATTAGAGTGCGCTACCAGGCAGCTGGTAAATTTTCTGCTTCACTAAAATTTTACAATATTT
TAGGCTATTGGCAAGGAAAACAATACACTAGGACTGAGATTCCATTGCCGAAGAACATAGACGCTATTATACATACATATAATTACAAGTTTTCA
ATTTCATAAGTCAACATTTAATTTTAGGTCTCATGCTAAACTCCACTTATTGATCTATATTGATTGACGATCAATCCTCGGTCTCGAGCTTTTT
TAATATGGACTTTGGGCTGTAAAATTTTAATGGGC
(SEQ ID NO: 214)

Exon: 4070..3807
Exon: 2349..1982
Exon: 1897..1001
Start ATG: 3832 (Reverse strand: CAT)

Transcript No. : CT7302
CTCTCATTCGGCGTTTTTCTTTGTGACTGTGTGGACGTTCTTAATTGTACGGCAAAATCTCCAGCAACCAAGCTACTTTCTTAGCAAAGCTACTA
AAGAGGAAACTATATTGATAAAATTTCGTTCTTTTAAAATCTTTGTGCTGATATTTAAGGCGTGCTTGGTGATCCAAAAACCCTCAGTTACAACG
TGTTTTCTCGCTTCGCGTTTGAAAAGTAATATCTAACAGTAATTCAAAATGGCTGATGTGGCTGAGCAAAAGAATGAGACCCCTGTTGTCGAGAA
GGTCGCAGCTGAGGAAGTTGATGCTGTGAAGAAAGATGCAGTTGCCGCCGAGGAGGTAGCAGCTGAGAAGGCGAGCATCACAGAAAACGGTGGCG
CCGAAGAGGAGAGCGTAGCCAAGGAGAACGGAGCCGCCGACAGCAGCGCGACCGAGCCCACCGACGCAGTCGATGGTGAAAAGGCGTCTGAGCCC
ACTGTTTCTTTTGCCGCCGATAAGGATGAGAAGAAGGACGAGGATAAAAAAGAGGATTCCGCTGCCGATGGGGAGGACACCAAAAAAGAGAGCAG
CGAAGCTGTTCTACCTGCTGTCGAGAATGGCTCCGAGGAGGTCACCAACGGTGACTCAACAGATGCTCCCGCCATTGAGGCTGTAAAGCGGAAGG
TGGATGAGGCTGCAGCCAAGGCAGATGAGGCCGTCGCCACCGCCGGAGAAAAAGGCTAAGCTTGATGAGGCCAGCACAAAGGATGAGGTTCAGAAT
GGGGCCGAGGCTAGCGAAGTGGCCGCCTAAGGGAATCGCCCGCGGAGCAGCAAACTCAGTAATCTACTTATTAAATACTTACTAACACAAAAAAA
GCAAATCACAGAAATTACGGTTCTACCGCCAGGAACCCGGACTGTATCCATTTTCCGCTCTTGTGAGCGGGTGATACGTGGGTGGCTGCTTGGGT
GGCGGGCGCAATTCTCCAATAACAATCCGGCAATGGGAGCGTAGTTTATAGCGTACCGGTTCTCTCTCTCTACTAACAAACAACCTACCAAC
CAACAATACCGGCAACAAACGAAAACAAAAAATCCATTATTATTTAAAAACTTACTTAAAATCTTAACTTTAAAGCAAAGTATATATATATATAA
AGCGAAGGATTAAGAGAACAATATTAAGCGAAATTAAGATGCGAGACCCTCTATGTTTTAAGAATAAAAGTTGTAAACAAAAGCGTCAAATTTAA
TAATTGTAAAAAAAAATACGAAGCGAATGAAACAAATTGCAAACAAAATCTTTAAGTAAGAAAAACATCAAAACAATTACGGCAAAATAACATAT
GTAATCCTTTACAATTTTTAATTTTACAACCGTATCTTATTTTTGAGTATGAATATTTATATCGAACAAAGTAAAACTAAAAATTCAGTAAAATG
TAACAAAAAGCTGCCAGCAACAACCCCAGAAAAATGTATGCCAACCGGCTAAAAAAATACTACCACATAGAAACAATAAAAAGTACGAAAAACAA
CTTTTACAG
(SEQ ID NO: 215)

Start ATG: 239 (Reverse strand: CAT)

MADVAEQKNETPVVEKVAAEEVDAVKKDAVAAEEVAAEKASITENGGAEEESVAKENGAADSSATEPTDAVDGEKASEPTVSFAADKDEKKDEDK
KEDSAADGEDTKKESSEAVLPAVENGSEEVTNGDSTDAPAIEAVKRKVDEAAAKADEAVATPEKKAKLDEASTKDEVQNGAEASEVAA*
(SEQ ID NO: 216)

Classification: known_flybase_gene
Gene Symbol: l(2)k0581
FlyBase ID: FBgn0022155

FIGURE SHEET 115

Celera Sequence No. : 142000013384170
TGTCCTCATCGCCGATGTCTTCCTCGTCTTCCGAGTCCGGAAGCGCTTCCCTCGCAGCTTCTGCAGGATGTACGGATTAATCAGGCCGTCTTGGC
AGGCTTATAGCTAATAAAACCTTCGCAATATTTGTTAAAGTCGCTCATTCTTGTCTATTTTTAATTTGCCGCACGTGCATTAAATGACGACAGTG
CTGACTATTCAGCTAGATTTAAGCTAACTTGGGCTGAAGACACATTGAATACTTAATAGACGAGTTGAAAGGGATAAGAGTGCACTTCAAATGCG
TCAGCACTCTTTCTTTTATGACGAAATCCACTTATTCGACAACTGAATTTATTTTTAACTACTTCAATAATATGATTTTGAAGCCAAGTCACACA
CCACACCTTGCGATGCTTCTTCTTGGCTATGCAAACAAAGCCGTTCACAGTGAAGCGCCTTCAAATTACGGCGCGCATTGTGATCGTTTTAAATA
AATTAAAAATTATGGTTCCTTTGAAAAGTTCATGGTAATGGTAAGATAAAAGCGGCTACCTATAATTAACTCAATTGTCAATCATCAACAGTTCC
ACCATCATACTTGTACACCCGTACCACACACCCACCCATACAGCACAATAAGCAAGATTTCTTTGTTTTCGTTTAATATCGATCTGTAGTTTTAT
TCTTTATACAAAAATGAATTTCACAAGAAGCCGTTCCGAATACGACCTACATACATGTGCTGTCGCCATAAGTCAGTTGCCTAAATATTCTTTCG
GTTTGGAGTTGGATTTGCGTGTTCGTTGAGGTTTCTTGATTGCCTGACTTGACTATGTAACTCGTTTTGTGTTATGTATGGTTATATAAATATAT
ATTTACATATTTATATAGGTTCTGCCATTTTATATTTAACAAAGGACTCTTATTCCTGCGCAGCATCTCTAACAAGAAGAACTCTTCAACAAGCA
ACTATGCATTCAATAATTAGATATATGCGGGCTACATTTATAGATCCTATTCACATGAAGTCGTCATAGTCTTCGGTGAAGTCATTTCCGTACTT
TTGGTAACCGTCAATGTCCTGCAAAAGAGCGGATTAAATAAGTTCATTCGTTGATCTCGAACGGCGGCGATTGAAACACTCACGTCGTTTTCGGT
GCGGAGAGTGACCTTGCCCTTGCCCTTTCCAGCGGGCTTTTTAGCATTGGCCTTTTCCAGCTTCAGCTTTTCCGAGTGCAAGATTTCCACGTTCA
TCTTGACCTTTTTGATGTCAGCAGCGCTCACTAGATAAGGTGCGAAATCAAATCAGATAAGCCGTCTTTAATTGTCAGCCAGCTAATCACTCACG
ATTCACGCATAGGCTGCGCACCAGATCCTCAACAAATTGGGGGAAGTGCTCCGACTCGCGGAATTGGCCCACCTTCCAGCTGAGCGTTGCGCCAA
ATTCCTTGAACTCCTCCTTGGTCTCGGGGTTGAAGGCGTCAAGACCTCCGCACGTACTCGTCACACCGAACGCTTCCTGGGCATGCTTGAGATCA
GAGGCCTCCTGGATTTTTTGCAATCGCAGCTTCTCAGCCAACTTTTCTGCAGGCGATAGGTTGGCCAAACGTTTTGCCTCCGCTTCCTCCTCTAG
GAGCTGTTAATAACAGATGATAACAATATAGCCAATGATTGAGAAATGCTTTTGAGCCTTATCTCACCGCCTGCTGTTCCAGTTTGGCTTTTAGC
GCCTTATTTGGCTTCGGTTTGGCTGGTGCTTCTGTTTTCGTAGGCTTCTCCTCGTCCTTTTTTTCCTCCTCATCCTCCCAGCTGTCCTGTGGGCA
GCAAATAAACAAATGATTCGATCAGTCTGCTGCAAAAGTGCACACGTGTACAGCGAAACGAAAGTGAAACCGAGTGCAGAAAAACAAGTTTTGGC
CCATGGCATTTGTTGTTGGGCACTTGGATAGTTGGTTTGAATGCGGCACTGCTTTCGATCTCACTTGGATTTCGTTAGTCGCACCTTGATGTCCT
CATCCTCGTCCTCGCCCTCCCACTTGTTTACGCTGGCGGCGGCAGTCGGCCGGATGACCACCTCGCTGTCTGCTGCGGATTCTGCCAGGTAACAG
AATGAGTTCCAGGAACATGGTGAATAACAATGATTTCAAACGGTTAGTTGGCACAGTGGCTAAAAATACTCATCAAGGCTGGTTGCACGGCACTC
CAACAACAACAGCAATAGCAGCAGCAACAACAACAACAACGACGGAGACCACGTTTATTGTCCGCCGTGCAGATGACGCACCGCCCACTCTTCCG
CCCAGGCCAATCGCAACTTACCCCAATCGTCGGCCATGTTAATGGTTGCCTATTTGCTTGCGGGATTTGTGCTTCTGGATGGGATGGTGCTGGGA
TCGACTTGTTTCCAGCCTCGGCAGCGATTTCAGGAATTTTCCAAAACCAAATTTCTGTGGATCTGTAGTGTGCCCAAGGCGCGACTAGCGGAAAA
TGCGTGGGTAACGTCGCCGATAGTCTGTTGCCATCGAATATTCGTAGTGCGGCCAAGGTGATATCAAGTTATCGACAATTTGAAATTTGTTACCC
TACAATATTTCATTTTTCATTTTTTTCCTTTCTTGATTGTAAGATTGCTTATTTTATTTTCAAACACAAATTTGTCAACTTTGTTAAGAAATCTT
TAAGTTTTTAAAGATTTGAGTTACCCTACAAGTTTTTTTCAAAAAAAATTCGTGATAAATCTCCCTCTTCGTGGTGTTCTAAGAAACTTACTCTT
AGAGTTATAAGGAAAATTGATTCGACTCGATAAATTATATATAGTAGAGAGTATATACATACATAAGCATGTTCTTGATAAGAAGAACTAGCTGT
GTCGTTATATACCTCGAACTCCCCAATTGCTGACTAAGGCTATCTTATAGTCGAGGAATTCTTTCGATTGAGAGGCTAAGTCATCCTTATTGGAG
TTAGAATTGGTCTAGTTAAGATCTGGATTTGTTTGCAAAATGTGAATTATGTCAAACGTCTGCAATTCTCAATGGTTACATCTGTTTTTAACATA
ATCATGTTAAATGTGGCTTTTTGTCCCAAGAACGGTTTTAAAGATAATTGTGTACTTTCTTTACTTGACTGTTTTGGCGATTTTGTTAACAAAGA
ACAACATCCATTTCTGCATGCATAAAAAGTATCATTTTAATAACGTTAAATTAAATTGGTATTCTTACAGATTTGTATTTCATTTTACGTTCATC
TTCAGCGATATCATTGATTTTCTTCTTTATCCACTCATAATATGAGGAAGTTTTCGTGTAAACCGCTGGCCCATATCCGTAACTGGAGGGTCCCC
CTCCGTAGGACGTTATTCCGGCTAGGTAATAAAATTGATCAGCACCCCTGCCCACCGAAGCCATCAGCGGGCTACCGGAATCTCCCAGTCCGGTG
TCGGTGCCATCCCATCCCATGGCACATATCTGGATGT
(SEQ ID NO: 217)

Exon: 2457..2302
Exon: 2076..1985
Exon: 1796..1683
Exon: 1618..1330
Exon: 1265..1129
Exon: 1063..1001
Start ATG: 2317 (Reverse strand: CAT)

Transcript No. : CT7734
GCGCCTTGGGCACACTACAGATCCACAGAAATTTGGTTTTGGAAAATTCCTGAAATCGCTGCCGAGGCTGGAAACAAGTCGATCCCAGCACCATC
CCATCCAGAAGCACAAATCCCGCAAGCAAATAGGCAACCATTAACATGGCCGACGATTGGGAATCCGCAGCAGACAGCGAGGTGGTCATCCGGCC
GACTGCCGCCGCCAGCGTAAACAAGTGGGAGGGCGAGGACGAGGATGAGGACATCAAGGACAGCTGGGAGGATGAGGAGGAAAAAAAGGACGAGG
AGAAGCCTACGAAAACAGAAGCACCAGCCAAACCGAAGCCAAATAAGGCGCTAAAAGCCAAACTGGAACAGCAGGCGCTCCTAGAGGAGGAAGCG
GAGGCAAAACGTTTGGCCAACCTATCGCCTGCAGAAAAGTTGGCTGAGAAGCTGCGATTGCAAAAAATCCAGGAGGCCTCTGATCTCAAGCATGC
CCAGGAAGCGTTCGGTGTGACGAGTACGTGCGGAGGTCTTGACGCCTTCAACCCCGAGACCAAGGAGGAGTTCAAGGAATTTGGCGCAACGCTCA
GCTGGAAGGTGGGCCAATTCCGCGAGTCGGAGCACTTCCCCCAATTTGTTGAGGATCTGGTGCGCAGCCTATGCGTGAATCTGAGCGCTGCTGAC
ATCAAAAAGGTCAAGATGAACGTGGAAATCTTGCACTCGGAAAAGCTGAAGCTGGAAAAGGCCAATGCTAAAAAGCCCGCTGGAAAGGGCAAGGG
CAAGGTCACTCTCCGCACCGAAAACGACGACATTGACGGTTACCAAAAGTACGGAAATGACTTCACCGAAGACTATGACGACTTCATGTGA
(SEQ ID NO: 218)

Start ATG: 141 (Reverse strand: CAT)

MADDWESAADSEVVIRPTAAASVNKWEGEDEDEDIKDSWEDEEEKKDEEKPTKTEAPAKPKPNKALKAKLEQQALLEEEAEAKRLANLSPAEKLA
EKLRLQKIQEASDLKHAQEAFGVTSTCGGLDAFNPETKEEFKEFGATLSWKVGQFRESEHFPQFVEDLVRSLCVNLSAADIKKVKMNVEILHSEK
LKLEKANAKKPAGKGKGKVTLRTENDDIDGYQKYGNDFTEDYDDFM*
(SEQ ID NO: 219)

Name: eIF3 p35-like
Classification: translation_factor

FIGURE SHEET 116

Celera Sequence No. : 142000013384170

AAAAATAAAAGAATATTTAAAAAATCGTTGAAATCACCGATGACAAGCTCTAAATGCGCAAACTTCAAATTAAAGTCACAGATGAAAGAGTTCAT
TAAATACAAAAATAGTAAAGCCTATTCGTATTTTAACTGTTGTGTTGTAATTATGCATAAAGCGTATTAATTATGTATGTGTAACAAAAATATAA
GAGAAAAACAAATACAAACGAAAAGAAAAGAAAAACAAATAAAGAGTATGTATTACTAAACAAAACAAAAGCATATTTGCAGAATTGAAGGTGTA
GACACTGAGAGAAAAGGAAGCACACATTTCATTTAAATTAAGCGCCGAAGAAGCTGCAATAACGCATTAAAAAGCCAATCAAATTCAAAGTTTCC
TGCTTTTGCCATTAACATTATTATTAATATTATTTCCCTTATTATCATTTACCGATGCCAAAACATTGATTTAATTAACGAGCGGTTAAAAGAAT
GGCAAAGAAAGTTTATTTATAAGACCGAAGCGATAATGATTATTTAAATATGAAAGAATTCAACTAACTTCATATTAAGATGTCCTTGTTATGTC
GCAAAGAATTAATAAAAATAAAAGTGAAAAAACAATTGAAAACCAGAAAAAGCAAACATGACGAATTAATACAAGTTTAATAAATGCGATAAAAC
AAATGAAATGATATTTTCAAATGGGAACAGTATGGATTTGGTTAGTACTCTTGATGACTAAATTGGACTTGCAGAAATCGAGGCACGAAGACATA
TTTTTTCACTGCACTCATACGAGTACCGACCAATTTAATTTATTACGCATTTTATTGCACTGTGGCCAATGATCAGTTAAAATAAAGCAACGTTC
CACTTTGCTAGTGAACCTTATCAAAAATAAATAATTGATTATGTAACTCTTGCTCTTTAATCTCAACACCCAATTACCTCGTTGCGTCTATTTTT
CAATATTTCTTCAATTTAAAGCACATGATTTTGTTGAATTTATAATTTTTATTCACTTAAAAATGTAGCTCCAAATACACTTATAATTTTACGGT
GTTTAATATATGTATTTATCTTTAAATGTATGTGTGTATGTGTATCGTTAATAATTATGTTTATAGAAACTCATATATCGGAGCCACTCTACCGA
CAATGCACGAATGATTAGTGTGAGGCGCGGAATAGTTCGCCAATTAAAATGGTTTCGGATTAGGCGAGCCCAAATCCAAATGGGAACCTTCTCCT
ACTGCACGTATCCGCGACCAAGAGTAAGGATGGTATCAAAGAAGTGAATATTGAATCGGGTATGTCATCTGATTTCGCCATCGGCTGGATGTCTT
AGCCAATGGTTGCTGTAGTAAGTTACCGCGTCCAGGATGCGAATGTGATTGGTTTTGCTTGCTCGGTTTTACGGAAAAAAATTCATTTAAAAAGTT
CCATTTTGTGGTTTTGTTTTGCGGTGTAAAACTAGAAATCTAACTGTAAAGATCATCGTCGCCGTTGTCGCCGGGCGAGTTAACTGGCAAGTTGT
TACCAGATCCTGAGGTGTTGCCGGTTTGACCGGGGAATCTGCAATAACATATACACTATCATCAGTAACCTGGATTCCAACAAGAAATGCCTTTC
AATTCTCACCTGAAGTTCTGTCCGAATCCACGGGACTGCTGCAAAGTCTGGGCAAACATCTCGTACTTCCTGATGTCATTATCGGACACCGAACG
GCGAGCGAACTTCATGGCCTCCTCGAAGTGGGCGCTAGTAATCTCCGGCACTGGATCGTCCTCGTCCATCTGATTATATGGGTAAATAGTCAAAC
ATAAACATTCTTATTTTTTGCGCTAAGCTAAATGACTTACGTCCATCGCGGAGTTCTGATTTTCGGCGCGCTCCTTCTCGCGACGAATTTCAGCC
TCGATGGCCTGTCGGATGGCCAGCTTGCAAGCCCGCTGGCAGATCTCGGTCAGATCGGCGCCAGAGAAGCCCTGCGTCACCTTGGCGATGTAGGT
AAGGTCTACTTCCTTGGCCAGCGGCGACTTGCGCAAGTTAGCCTTCAGGATAGCCTCACGCGATTTGTCGTCGGGCAGCGGAATATAGATCAACT
GATCCAGACGGCCCGGACGGAGGATGGCCGGATCGATAATGTCCGGGCGATTGGTGGCTCCGATGATGAACACATTCTTCTTGGCTCCCATGCCA
TCCATTTCGGTAAGGATCTGATTGATCACACGATCAGCGGCGCCGCCAGCATCGCCGACATTACCGCCACGGGCTTTGGCGATCGAGTCCAGCTC
GTCGAAGAAGAGCACACAAGGAGCCGCCGAGCGGGCCTTATCGAAGATGTCGCGCACGTTGGCCTCAGACTCGCCGAACCACATGGTCAGCAGTT
CGGGACCCTTGACTGAGATGAAGTTCGCCTGGCACTCGTTGGCAATGGCCTTGGCCAGCAGCGTCTTACCGCAACCAGGGGGTCCGTAGAAAAGG
ACACCGCGACTGGGCTGCATGCCAAACTTCAAGAACTTGTCCGGATGCTCCACTGGGTATTGCACCAGCTCCTGCAATTCCTTCTTGACGCTCTC
CAGACCTCCGATGTCTGTCCAGGTGGTGTTGGGCACCTCAACAACAGTTTCACGCAGCGCCGATGGACTGGACTTGGTCATAGCGTAGCGGAAGT
TCTCCATTGTCACGGCCAGCGACGCCAGCACCTCGGCATCGATCTTATCGTCTTCCAAATCGATGAGGTCCATCTTCTCACGGATTTGCTGAAGG
GCAGCCTCAGAGCAGAGTGAAGCCAGATCAGCGCCCACATGTCCGTGGGATTCGGCAGCAATCTGCTCCAGGTCAACATCATCATGCAGCTTCAT
GTTCTTGGTGTGAATGCGCAGCACCTCCAGCCGTCCAGTGGCATCTGGAATGCCGATGTCAATCTCACGATCAAAACGTCCAAAGCGACGCAGGG
CCGGGTCAATGGAGTTGGGCCTGTTGGTAGCAGCCATAACGATCAGATGGGAGCTCTTCTTCATGCCATCCATCAGGGTCAAAAGCTGCGACACA
ATGCGACGCTCCACCTCACCGTGGGTCTTGTCACGCTTGGGGGCAATAGCGTCGATCTCATCGATGAAGATGATAGCCGGCGAGTTTTTCTCGGC
TTCCTCGAAGGCCTTGCGCAGATTCGATTCCGACTCTCCGGCCAGTTTGGACATGATCTCCGGTCCGTTAATCAGGAAGAAAAAGGCTCCGGTCT
CGTTGGCCACAGCCCTGGCAATCAGGGTCTTACCGGTACCCGGGGGACCGTACATAAGAATACCACGCGGTGGCTTCACACCAATGGCCTTGAAG
AGCGATGGATGCCGCAAAGGCAACTCAACCATCTCCTTGATCTGGGCCAGCTGCTTGCGGCAACCACCGATATCATCGTAGCCAACGGCGTTTAG
GGACTCCTCCTCCTCCTCGCGCTTAATTGGATCACCGTCGCAGAAGATTACCGTCTCGGGAGCTACGATGCAGTAGGGCTCCGGGTCGGTCAGCA
CCACCTTGAACTCAATAGGACGCATGGCGGCGCGCACAATAAAGTTGTCGCCCATGTGGATTGGCCGATAGGCCTCTAGGAAGTACGGCTTCAGA
TAGATCTCGAACAGGTTGCCGGTAACGCCTTCGGTGCTTTCGTCGATGGGCAGGATGCGCACCCGTTTGCCGTACTTGACGTCCGGGCAGGACTG
CACGGAAACCACATCTGAAAGATGGACGCACAGGTTGTTGCGCACCACGCGGTTCATGCGGATCTTCTCGTCGGGACAGGTGTCGTCCGAGAGCA
CGATGCACACCGTCTCCTTTCGGCGCTTGCCCTTCAGAATCACGGTGTCGCCACGGAAGAGCTGCAGCTCATCCATCTTCGCCTGATATAGTTTA
AGGGGGAAAAAGAACAGCCAAGTCATGTGAATTAGCCATGCGATGACGTGGCCTTTGGGAGAGTGAATCTTACCTGCGATAGCGACACCACAGAG
TTGTCGTCATTCTGCGCCTCTTCCACAATCAGTCGGTTGGGACGGTCCTTGCGCTTCAGGATCGCCGTAGCCAGATCTTCACTGTAGGGTAGAAG
AAAAAAGCATCGCGTAAGACTCGTCGCTAAAGAAATATCTTATGTCTTATATATAATTTGGCCTAACCGCTTATCGAACGAGTCTTTCGGCTTCA
TTTTCTCATCCTGCTCGCTGTGATATCCCCGCATAAAGTCCCTCGTATCCCCATCATGATCCATCTTATCGTTCTTGCCGCCAGACATTGTTTTT
TTTGTTTTTTTTTTTGTTTTTTTGGATTGCCTTTTTTGTTAGTTTTGATAAATTTATGGAAACTACTTTCACTAGTAATACGGAATGGAACTAAG
CATCTGGATAATTAGGCCTGCCGAATCATTTTTCGTTGCTAACGTGATGATGTCGATCAATCTTTATTGATAGATTTTTGAACATAAAAGGTTAT
CACCCTATATCGTTCATAAAAATCTATATTAATCGGAATAATAGTACAATTGTTTATTGTCTTTAGTTATAAAAGTATGTTTGTATTTCTTGTAT
TCGATGCCAACTTTTTTGGCGCCATTTGTTATAATAATTTCTAAACTTTGAGGTAAATTATGCATTTATTGTTACTTAAACGATATGTTTTTTTT
TACTTCTGGCGAGTTGAGGGAGCACAAAGACTTTTCTAGAATTAATGCAATATCAAAAAAGGTATTACTAATAGGTAGCATTGAAATAAGTGGTT
TCGGCATATAGTTTAGGATTTTCGCGATTTATTATAGAAATAGCTGCCATATATGTATGCAGTATTGTTTTTCGTATCCAAAGTTATAACTACAA
CAACCGGAAAATTGTATCCTCCAGCAAAGGATGACTTGTATTTTTGGGACAACAAAGGGAAATCGTAAGTTTTCAAGCGGCAACAACAACTGCAA
GGGCAGTAACACCAACAACAACAACAACGTACTGCAAATGGCGATTCTCGCTGGCGTTTTTTTTTCTTCGGTTTTTAGGTTTGCCCTAGTTTCGC
AACATTTTGCAACCGAGCAGTGGAAAAGTCGCGGTAAATGTCTTTGTCTCGCGGAAATCGGCGAAAGCCTTTCACAATTAAATAATAGTATGTCT
GCGATGTGGCCCTTGCGTATTTTTTTCGGCTCAATGACTGAGCGAAATTTGTGAATTTCGACTTGGACCGACACAGTCGGCGCCTATTTCGGCGT
CCAGTTCACTTACCCCTTGGAATCTGCCATGATAAACTAGTTGACGTTGAACTTTTTAACTTAATTGTACAATTCGGCGCGACTTGGACTATTCG
TTGAGCTGGAAATCGGCACTTTTAGTCAAATTCAAAGATGAGGCAGCAGAAACAGATTGGTGATGTGCGTTACCGGACATTCATCGATTGGGCTT
AGAAAATATCGATTACACGCTGCGATGGTTTGTAAAAGAAATTGAAGTGGCAACGCTAAAGGAAAGAGTGGCAATGTGTGCAGGTGCCTAACTTG
GCTATGCTCGCTGGCAGATGATCGCTGCTATGAAGCCATGCGTGATAACGTAGCTGCTTACGTTTTTATTGAAAAAGTGCAGCATACTTTTCGGC
TATGTCTATATCTAAAATATATGTAGGAAGTATGTAGAACTCAATCCGTCTATTTCACTTAGTTGTAGAAGTTTTGGTAGTAAGAAAAAATCTTC
ATTCATTCATTTCCCTAGAACACTCGGCCATCAACCTGTCCCTACAATAACTGCTCAATCGCAGCTTATGCTCGTAAAAACTTTTTAGTATTCAT
GGTTTTGGCATTAACGATGCCAATTATGGCAGCGTTTTATTTAGCTTTACTTTCAGTTTTATTTTTTAGTACTTAAGAGAGTGACAGCGACGTCG
GCAGAGAGGAGAGCAGCGTCATTGGGCGTGGTCGCTGCCCCCAAAAGAATGGGAGCAAACTCCATAGAAACGCAGAACGAATTCAACCAATCGCC
TGCAAGTCTCTTGTCTTCGAAGAGCGCCTGCGCAGAGAGCAAAAGAAAGTGGCGAGCGGAAACCAGTTTTTGTGACGATGAGGGTGACGATGAAG
AGGAGTGGGGAGTCGGGGTGGCTGATAAAGATGGCCGTCGCCTTCCGCGGCGCAGGAAGCAGCGAAGAGCGGGGGGCAGGGCAGCGGAACCGCCT
CAGACCCAAAGTCACAATTATGGGGCACTCATTCATTGCGGTGTATGATGCAAACAGCGCTCTCCTCGCTTTTCTCTCTTTTCCACCAAACTCTG
CTGTACAGTCCGACGTCTTTAGCTCTGATTTATTCACACGATTTTTTGTTTTATTTTACTATCTTG (SEQ ID NO: 220)

FIGURE SHEET 117

Exon: 5336..5278
Exon: 2506..1846
Exon: 1779..1625
Exon: 1558..1001
Start ATG: 2490 (Reverse strand: CAT)

Transcript No. : CT7776
CCGATTTCCAGCTCAACGAATAGTCCAAGTCGCGCCGAATTGTACAATTAAGTTAAAAAGTTCTTGAAGTTTGGCATGCAGCCCAGTCGCGGTGT
CCTTTTCTACGGACCCCCTGGTTGCGGTAAGACGCTGCTGGCCAAGGCCATTGCCAACGAGTGCCAGGCGAACTTCATCTCAGTCAAGGGTCCCG
AACTGCTGACCATGTGGTTCGGCGAGTCTGAGGCCAACGTGCGCGACATCTTCGATAAGGCCCGCTCGGCGGCTCCTTGTGTGCTCTTCTTCGAC
GAGCTGGACTCGATCGCCAAAGCCCGTGGCGGTAATGTCGGCGATGCTGGCGGCGCCGCTGATCGTGTGATCAATCAGATCCTTACCGAAATGGA
TGGCATGGGAGCCAAGAAGAATGTGTTCATCATCGGAGCCACCAATCGCCCGGACATTATCGATCCGGCCATCCTCCGTCCGGGCCGTCTGGATC
AGTTGATCTATATTCCGCTGCCCGACGACAAATCGCGTGAGGCTATCCTGAAGGCTAACTTGCGCAAGTCGCCGCTGGCCAAGGAAGTAGACCTT
ACCTACATCGCCAAGGTGACGCAGGGCTTCTCTGGCGCCGATCTGACCGAGATCTGCCAGCGGGCTTGCAAGCTGGCCATCCGACAGGCCATCGA
GGCTGAAATTCGTCGCGAGAAGGAGCGCGCCGAAAATCAGAACTCCGCGATGGACATGGACGAGGACGATCCAGTGCCGGAGATTACTAGCGCCC
ACTTCGAGGAGGCCATGAAGTTCGCTCGCCGTTCGGTGTCCGATAATGACATCAGGAAGTACGAGATGTTTGCCCAGACTTTGCAGCAGTCCCGT
GGATTCGGACAGAACTTCAGATTCCCCGGTCAAACCGGCAACACCTCAGGATCTGGTAACAACTTGCCAGTTAACTCGCCCGGCGACAACGGCGA
CGATGATCTTTACAGTTAGATTTCTAGTTTTACACCGCAAAACAAAACCACAAAATGGAACTTTTTAAATGAATTTTTTCCGTAAAACCGAGCAA
GCAAAACCAATCACATTCGCATCCTGGACGCGGTAACTTACTACAGCAACCATTGGCTAAGACATCCAGCCGATGGCGAAATCAGATGACATACC
CGATTCAATATTCACTTCTTTGATACCATCCTTACTCTTGGTCGCGGATACGTGCAGTAGGAGAAGGTTCCCATTTGGATTTGGGCTCGCCTAAT
CCGAAACCATTTTAATTGGCGAACTATTCCGCGCCTCACACTAATCATTCGTGCATTGTCGGTAGAGTGGCTCCGATATATGAGTTTCTATAAAC
ATAATTATTAACGATACACATACACACATACATTTAAAGATAAATACATATATTAAACACCGTAAAATTATAAGTGTATTTGGAGCTACATTTTT
AAGTGAAT
(SEQ ID NO: 221)

Start ATG: 76 (Reverse strand: CAT)

MQPSRGVLFYGPPGCGKTLLAKAIANECQANFISVKGPELLTMWFGESEANVRDIFDKARSAAPCVLFFDELDSIAKARGGNVGDAGGAADRVIN
QILTEMDGMGAKKNVFIIGATNRPDIIDPAILRPGRLDQLIYIPLPDDKSREAILKANLRKSPLAKEVDLTYIAKVTQGFSGADLTEICQRACKL
AIRQAIEAEIRREKERAENQNSAMDMDEDDPVPEITSAHFEEAMKFARRSVSDNDIRKYEMFAQTLQQSRGFGQNFRFPGQTGNTSGSGNNLPVN
SPGDNGDDDLYS*
(SEQ ID NO: 222)

Classification: enzyme

Celera Sequence No. : 142000013384690
AACCGGCTCCACCTCTCCGAGTTCAGCATTAAGTGTCTCATTAGCGATCTGTGGAGCTCGTGGTAACCACTGGTTGTGAGCCCAACAGCAGGCGT
ATAGTTTCTCTCTCTCTTGACACAATTTTACCACATCCTCAATTTCCTCGCCAGTGCGATGGATGTACTCCTGTGCAACAATTTGATCGAAATCC
GAATAGGTACCCAATTCCCAAGGGCTAAAAATTTTCGGAGATATTTTGGACAGATTTAACCTATCCAGCTGCACTCCCTTACTGTGGAGTAGGTG
CTTTAAACGTGGCAATAAGACGCATAGATTTACAGGCCAATTGCCATGGTCCACGACGTGCCTAAAGCAAAGGTGTAAGTTGTCTTCGCTTTTGT
ACAAGTCCTCGCCATCGTGAATACTTGTGTAATAGGAGAATTCTTGAAGATCTAATTGGTAGAGTATGCGCCAAATGGTTCTCATCAACCCTTCA
CTTGTGCAGATCAAATACTTAAGATTGTGATCCTATTTGAAATGAGATTTGGGTCATTCAAGCTTTGCATTCCTTACTTATATTTAATTGCTTAC
CTTGCTTCCTTCTGCAAAAAATATTTCCTTCGCTCTTTCGAGAAGAAATTGATTTTCTTTTTTCTCTACTGAACTGTTTTCATTTTCGGAATTTC
CTTCGGTCGTAACCCTTGCTCCATCTTCCAGAATTTTTGTCGATCCAGCTTCAATTTCAGTGTTTGGTCTGTTCGTAGAGTTTCTTGAATTATTA
GATGATTCAGCATGGATCATTTTAATCTTAGCCGGACTTTCCAGGTTATTATTTAAATTAACTGAACTGCTTTCTTTCGTTGGCTCTGAACTCTG
ATCCAACGCTTTCGGAATTGTATGCATTTCAGTTGCTTGTGTGTCAGTTGCTGTTGTTTGAGCTGTGCAGACACTTTCTATGTCAACCGAATTCG
AAGACAATTGTGGCTCATTTTCTTCAGCAGCAATGGTATTGGCAACAATATGCCCGGTAGATACGGAATACCTTTTATATTGTTCTTCTAGAAAT
GCTTGTGTTACTGGGCAGTTGATTCCTTTAAATAATTTATCGAGAAAGTTATGGGCCGTATAATTCCACCCGATCTTCAGTTTGCTAAATATAAT
CGTGTTGTATAAATGTGCTTGCTAATCCTTTAAACATTATTTTTTTACCTCGATAATTCATAAAGCCTCTCAGCATTTAGTTGAATATAATCTT
TTATGGGTTCCGTAACTTCTAGTTCATGCTGCAATTCCAGTGGCTGTGTGCCTTGGTTGGTAGTGACGTCTTCTGGGACAACTAATGCGTCTTCG
GGAAAAGGCTCTGGTTGAAATTGAGACGTGTTTTGTGTAGTCATCGGCTTACTGCTGATCGCTTCCTTTGCGACTTTAGTCCTTTTTCTGCTGCA
ATTATAAGGTTTATTACACATCCGGAAAAAAAGTAAAAATGTATGTGGTATACCTTTTCATTAAGATTTCTAAAGCATTTCTGCGAACAGGTAAC
GACATTTCGCTTTTGGACTGAAGGCAACTTTCCTTGAGCGGTGTTCTAGTGGTGCACGTCGCCAGGCAATCAGTTTCCTGTAGACAATCATTCAC
ATTTTTCCCTGGATAACTAAGCAATTGTTGTAGTATATGGCCGGTACATGGCTTGAATCGACATGCGAACTTTTCCCTCATCTCTGGTCCAGAAT
AGAAGCCTTTGTAGTAGTCGCGAATAACCTCATCCTTGGATTTTCCTCTATACTCAACGCACTTCTGCATATTATTAGCAATATCATCTAGATTG
CTCACATGACTTTTGAACAGCTCTAAGGATACAGGGTATGGTGGACACTCTTCTCCGGGCTTGTCGTCATTAGAACTAGGCGTCCTTGTGGATGG
TATACTTTCATGTTCAGCTATTGGTCTGCTGGAGTCATGACTTATTACTATTATATCTGAAAACAAATATATGTTTAACTTACTTCTCTTCGGTG
ATATTTTGCGTTTCTCGTACTACATTTCTGGATGACTGCAGACAACTTTCATCGCTTAGGTTTTCTGTGGTACAAGCCACCTGGCAATTTGGATT
CTTTGGGGGTAGCTCCTTGTTTTTCGGTGGAAAACTTAACAATTGTCTTATTTTTTTGCTGGGACACGGTTTAAATCGGCACTCGAACTTCTCCC
TCATGTCTGGTCCAGAATAGAAGCCCTCGTAGTAGTCCTGAATTACCTCCTCCTTGCTTTTTTCTTTGTACTCATCGCATTTTTGCATCTCATTA
ACAATATCATCGAGATTGCTCACATGACGTTTGAACATCTCTAAAGAAATGGGATTTGGTGGACAATTTTCTGTTGTTGTTTTAGGAGTGAAAGG
TACCTGGGACTTGGATTCGTTTACTGCTTTTGCATTATCTGTTCGATTCATTGTAAAAAGAGCCTTTTCATCAAGTGGCTTAGCTTTTTGTTTTA
GCTTAGCCAGCATCTTAGGATTGGGGCAATTGAATTTGTACTTGAATCTTTGACGAACATCATTGCGTGCATAAAATTTATTGTAAAACTGGCGG
AAAAATTTTTTGCATTGTGGGTGCGAAGGATCAGAAATTAATTTTGACAGTTGATGTTCGTCTTTAATGTGATTATTTACTAGAATTGCTCGGAT
AATCTCGTCATAGTTAATATATTGCCGAAAAGTTTCAAGTGATACGGGAAAAATAAAGCGCCCATGTCTAAAAAATTTTTTTTGAAAATTGTTAC
TTAAAAATTTAAAAAAATGGTAATTTATATTTTTCTTACTTTTAAGGTCCACTTCAACATCCGTCACAAAGGAAGTCCTAAAATTGTGGTTTTA
AAATTATGAAAACAATTCAGGTTACGCTAACTTACTCATATACATCGGTAGAATCTGTGATCTCTTCAGGTTTGGCTGGGGTCTCGTCCGAAGCT
CTGGTTTTTGAAGCAGGACTCTCTGGTGTCTTGGACATGGGCACTTCGAAACCTGACGGAGGAATCTCTAACTGGGGCGCTCTATCTGATTGTTC
TTCGGCAACCTCCTTGCTCTGATGGGGTTTAACTTGGGGACTTAAGACTTCAGATGACTTCTCAGGGGCTTTCGAACTGTGCAGATGGCGTTCTG

```
GCGAAGCTAATGCCGGCATACATCTGCTTAGTTTGTTGGCATCGTTCCTGAGATTAGCTTGGTTTTCGAAAGTTTCTAAAGTATTATGTGAACTC
GATAGCCCTTCAGTCGTGCTAATAGCTCCCGCAGCACAATTCTCTGGCGAAAGAGTAGCTAACTGGGACAGACCTTCACTCGGTTCGTGGGCAAC
CTCCATGCTGGGACTGGTTTGGATTTGTGAAGAGCCACTGGTATTCTGCGACCCTAATGACCCTTTGCTCTCAGTAATATATGAAGTGTTGGGCC
TGCGCGAATCAAGTCCTGGCGAGGGATTAGCTAACTGAGGGAGGCTTTTCCTAAGCTTTTCGGCAATATCTTTGCCGAGAATGGACAGCATGCAG
GCCTTGAAAGTCGACGTGCAAGGTTTTAATTTGTATGCGTATTTATATCGGATCCTCGGAGTAATGTAAAACGCCAGGTAATAGTCAAGGGCACA
TTCCTGGACATCCTTGCTCGCATAATTAGCATCCAGTTGCCTCATTTGCTCCACAATGTCCGATAAGTTTGCCATATTTTTCTTAAATACCTCGA
AGCTGACGATGGAACTGTGAAATATTTATAGTAAACAACGAGTATTTGGAAAGTGTCCCAAACTTACTTTTTCGTAAGGGATTTCATTGCAGTAA
GCTCCGCCACAGTCTTGACCGCTTTTTTGTCCAGTGGTTTCCCAGATTCAAGCAACTTTTCCAAAGGGATTTCTGTAGTTGCATTGAAGATATTC
GTAGGGGATCGCTTTTCTGGATACATGTAAAAGCGGTTGTAGAACCTTTGTAGTGTAAGAAGACGACGCTCATCGTCGGACAAGAGGACCAGGCA
GTGTTCTATGCTCCTGACAATTTTTTTGAACAGTAACATCTTATTGATGCACTGTAGGAATACATCAAAGGATACCGGAAAGATGAAGGCGCCAC
ATCTGAAATGAGTCAAAATTGGTTAATCTGCTCTGCTCGAAAATAATATTACCCACCTCTCCACATTAACAATTACGTCTGGAGATTCCGATCCT
GATGGTTTACATTCAACTGCAACGCCTTCAACTGCATCATGGGACTTCGCGGTTTCAGCGAGCGTCGTCAACTGGCTGCCTTCAACTAAGACTTC
GGGTTGCTCTACTTGAGATGGTCCTGCAGCTGCTACGTTTGCAACATCGTTTTGTGAAATTCCTCCTGGCTCCGGTACTTTAAGCAAGTTGTCGC
GTGTCCGCCTGGGACACGGCGCCACCTTGACAGGGAACCTTGCCCGTATGCTGGGATTCCGGTAGAACTCTTTGTAGTACCATCTGCTCCACTCG
ACCAACGTTCTATTGTCTCCATTGGCAGTTTTCAACTCACTTGCAATTTCAGACAAATTAACGATTAACTTTTGAAATGCCGCAAAGGACACTGG
ATACATGTTGCTCCTGAAATCAAACAATATTTAATGTTAAGATGTAAAAGATTCACAGTAACCTTACGACTTGTTCTATGCAAGTAACGTTATTT
GTTGTTTATCATAAACATCACATTTCAATACCGCGAAATAAACTAGGCTGAATATCACAGTGTGACTGTGCTGCAAAATGACAATATTTATCGAT
AGCGAACGACTAAATATTTTCACTACGAGAACTCGAACTTACTTAAAATTTTACAAGCCAGTTAATACTTTTGTGCTTTATTGTTTATTGTTTAT
TTATTTATTGTGCTGATTTAAACAGGGTTATAATTTCATAGCTAGCTAATTTTACATGTTATGATTTTCCAAATGACTCCAAATTTGTAAGGTGT
GCTAGGTATAGTAGGTGGTATATTCCAGCGGTCGCCGCACGGTCACACTCGAGCTGCGATTCGGAGGGCTAGAAAATCATCGATGTTTACGTACA
TCGATAGTTGGCAGGGCTTTGCTTTGTTTTGCAAATTCCAAGCGGAGTTGAGGCTGTGACAGATTGCGGGTGCGAGTTGTGAAGCAACATTGCGT
CATCATCAGCTCCTGGACAGAAAAGAGCTCAGGGAACGAGGCAGGTCCGCGCCCGGGGACAAGGAAAGCCTTTAGCCACGAGGACGCAGAGGGAT
CAAAGGCGGAGGAGGAGGCGGTGGCCGTGTCACGGGAGCTGGATCAAATGGCCAGCACCACTGGAAGTGCCCCCAGCCTGGGACCCCCCCAGAGC
GGGAGTGGTGGCTCTGGCACATTGGAGGGCACGCTAAGCAAGTGGACGAATGTGATGAAGGGCTGGCAGTACCGCTTCTTCGTTCTGGACGAGAA
TGCTGGACTGCTGTCCTATTACACGGTGAGTGGCTGCAGTGCACCTCCTGACTGAAACCCATATCGCACCCAGAACGAACTCCTCATGGCCCGCA
GCCTTATCTTATCTGCTATAGATACATTTGGATACACATACACACTTGTTGGTACCCCTTTATTGCGTGATTTGTTGACAGGAGATTACTTTTTT
GAGTCTGACTGAGGGGTCTGACTCTTGCGCCGCTGCGAGGCTTGATAGGCACTATTATAGAAGTCGTAAAAGCCGTAGAACATGCCAAGAATGAC
GGTGGTGAAGTAGAGAAGCACTAAGGGCGGCATGCCGCACAATACCAGCTGGAAAGCAACCTGCGTGAGGATAAGAACGAACTGCGTCATCTGAA
TCACTGTGATGCACTTCTTCACTGGAGTTAGGGCCTGCACCAAGGTCTTATCCGCCACTGCCGCCACAAAGTAGTACGAGTACATGATAACGTGA
ACGATAGAATTCAAGAACACGCAGAAGTAAGCAGCAGAACCTGTACAATTGAACGCATTTATGAAAATAGTCGGTCACCCAGCAGCCGGCTAGCT
TACCATTTTCGTTGAAGTTGATCAGTGCGTAGACCAGCGTTACCGTGGAGAAGTGATGAAAGATGTGCAGCTTGGACACCTGGTTTTGTTTCTTG
CGAAGCACAAAGATCACGGTTTCAATCAGCTCAGAGATCTTCAGCCAGAAGAGAAAGTAGGCCAAGTTGTAGTACCGCCTCACGAGCTCTGGGCT
GCTCCCGATGTCGCGGCACTTCCAAAAGATGTATATGGTGTTGTCCGTAATGTACAGGACCTGCGAGAGAAAAGCAATTAGCCGATGCTGCTGCT
GCTGTACAATTTATAAATATCCACCTCTTTGATAGCATATATGCAGGAAACCACCTGGATGAAATTATGTAGCAAGATAAGTCGCTTGAGCTCGT
AAGGTTTGCGCCATTCCATGAAACTATAAGCGAGGTATTAAAGGTCTTCTTTCTTATATAAGTAAGCCAGCGAACCCGCTGAATTGCTAATGTCA
AGTCCACTGACCCACATGCAAACAAGCGACGCTGACATTAGCATGTGAACTTACTGCGGACCCGCTTTGGTGACGAAGTACAGATAGAGGACCAG
CACTGTGATCATGTACCAGGGATCCTTATAAATCGTAGGAACGTTCACCACCGGCTGCAAATTTATACCTACAATTTTATTGAAACCATCAGACA
GTTTTTTGACAAATCCAAGAGGAGCTCACTTGCTGACGCCTCCATTTCGCTTCTTTGTGTTGAGCTTCCGCTGGCCTGTATCCTTTAGGTGGCGT
GGGACTGGTGGACTGCAGCTCTACCGCCTTGACCGCTGGCGAACATTTAAGCGTGAACAGCACGCCGAACACTGTTTTTATATTCCCCAAGCATT
GATTAGAATACATTAATTTATAGCAGGCGTAATAGCCCTTTGACAGTATGAGCTGCGATTTAATGAACCTTTCCTAATTCCGACTGCATTTCTGTT
ACAGTCGAAGGATAAGATGATAAAGGGCGTGAGGCGCGGTTGTGTTCGTTTAAAGGATGCGCTAATCGGAATCGACGACCAGGAGGACAACACAT
TCACAATCACTGTGGACCATAAGACCTTCCACTTTCAGGTAAGTGTCTCCTTAGTAAATGGAAATAAAGATTGTCTAAGGAAAGCTTGATCAATG
TTTTGCAGTTTCACTAATAGTTCATAATTCACCGTAATAGTTTAAGTACGACGTTGTTTGTTTTATGAACTGAAGAACCAACTCATTTTAAATTC
CACACTTGCATTGATTTTTTATGACGTCTAGTGGTATACGTAAGCAAAAACTATGTAGATCAAGAGGGCAGCACGTTTCTTTTTGCAATTCGCGT
TTTCGTCCCAAAAGATATAAAGCAAGCATGATGGCCTATCCGCTTTGCTTGCCAAGAGTTTTCGTCCTCTTACCGGAAAAGGGTATCCGGGCATC
GACCCAGAAACCACTGTCTGGTCCTCACGTTCCACCTTTTGTTTGACTTTGTTGCCTTGATGTAACGATAAAACTTTTTCCAATACCCATACACA
AGCAAAGGAGCCCACTAAACTTGCCAACTTTCCAAACGCTTGCAGGCGCGACACAACGAGGAGCGGGAGCAGTGGGTGCGCCGCCTGGAGGACAC
CATTCGACGCCACGCGAACCGGTCGCGTCTGTGGGACAGCCAAAGCGCTTTCTACATCGCCGGTGGCTACACGAAGGAAGGGGCGGGAGCGGAA
CAGGCGGCAGAAGACCCAACCACCTGGAGTTGGTGGCGCGCCGTGTTTCCGAGGCAGATGCCTACCTCCAGCTGATGATTGA
(SEQ ID NO: 223)

Exon:  6777..6680
Exon:  6623..6515
Exon:  6388..6295
Exon:  6235..5989
Exon:  5930..5600
Exon:  4573..4142
Exon:  4087..3773
Exon:  3719..2886
Exon:  2833..2795
Exon:  2727..1984
Exon:  1925..1479
Exon:  1420..1001
Start ATG: 6695 (Reverse strand: CAT)

Transcript No. : CT7814
TCAAGGCGGTAGAGCTGCAGTCCACCAGTCCCACGCCACCTAAAGGATACAGGCCAGCGGAAGCTCAACACAAAGAAGCGAAATGGAGGCGTCAG
CAAGTATAAATTTGCAGCCGGTGGTGAACGTTCCTACGATTTATAAGGATCCCTGGTACATGATCACAGTGCTGGTCCTCTATCTGTACTTCGTC
ACCAAAGCGGGTCCGCATTTCATGGAATGGCGCAAACCTTACGAGCTCAAGCGACTTATCTTGCTACATAATTTCATCCAGGTGGTTTCCTGCAT
ATATGCTATCAAAGAGGTCCTGTACATTACGGACAACACCCATATACATCTTTTGGAAGTGCCGCGACATCGGGAGCAGCCCAGAGCTCGTGAGGC
GGTACTACAACTTGGCCTACTTTCTCTTCTGGCTGAAGATCTCTGAGCTGATTGAAACCGTGATCTTTGTGCTTCGCAAGAAACAAAACCAGGTG
```

FIGURE SHEET 119

TCCAAGCTGCACATCTTTCATCACTTCTCCACGGTAACGCTGGTCTACGCACTGATCAACTTCAACGAAAATGGTTCTGCTGCTTACTTCTGCGT
GTTCTTGAATTCTATCGTTCACGTTATCATGTACTCGTACTACTTTGTGGCGGCAGTGGCGGATAAGACCTTGGTGCAGGCCCTAACTCCAGTGA
AGAAGTGCATCACAGTGATTCAGATGACGCAGTTCGTTCTTATCCTCACGCAGGTTGCTTTCCAGCTGGTATTGTGCGGCATGCCGCCCTTAGTG
CTTCTCTACTTCACCACCGTCATTCTTGGCATGTTCTACGGCTTTTACGACTTCTATAATAGTGCCTATCAAGCCTCGCAGCGGCGCAAGAGTCA
GACCCCTCAGTCAGACTCAAAAAAGAGCAACATGTATCCAGTGTCCTTTGCGGCATTTCAAAAGTTAATCGTTAATTTGTCTGAAATTGCAAGTG
AGTTGAAAACTGCCAATGGAGACAATAGAACGTTGGTCGAGTGGAGCAGATGGTACTACAAAGAGTTCTACCGGAATCCCAGCATACGGGCAAGG
TTCCCTGTCAAGGTGGCGCCGTGTCCCAGGCGGACACGCGACAACTTGCTTAAAGTACCGGAGCCAGGAGGAATTTCACAAAACGATGTTGCAAA
CGTAGCAGCTGCAGGACCATCTCAAGTAGAGCAACCCGAAGTCTTAGTTGAAGGCAGCCAGTTGACGACGCTCGCTGAAACCGCGAAGTCCCATG
ATGCAGTTGAAGGCGTTGCAGTTGAATGTAAACCATCAGGATCGGAATCTCCAGACGTAATTGTTAATGTGGAGAGATGTGGCGCCTTCATCTTT
CCGGTATCCTTTGATGTATTCCTACAGTGCATCAATAAGATGTTACTGTTCAAAAAAATTGTCAGGAGCATAGAACACTGCCTGGTCCTCTTGTC
CGACGATGAGCGTCGTCTTCTTACACTACAAAGGTTCTACAACCGCTTTTACATGTATCCAGAAAAGCGATCCCCTACGAATATCTTCAATGCAA
CTACAGAAATCCCTTTGGAAAAGTTGCTTGAATCTGGGAAACCACTGGACAAAAAAGCGGTCAAGACTGTGGCGGAGCTTACTGCAATGAAATCC
CTTACGAAAAATTCCATCGTCAGCTTCGAGGTATTTAAGAAAAATATGGCAAACTTATCGGACATTGTGGAGCAAATGAGGCAACTGGATGCTAA
TTATGCGAGCAAGGATGTCCAGGAATGTGCCCTTGACTATTACCTGGCGTTTTACATTACTCCGAGGATCCGATATAAATACGCATACAAATTAA
AACCTTGCACGTCGACTTTCAAGGCCTGCATGCTGTCCATTCTCGGCAAAGATATTGCCGAAAAGCTTAGGAAAAGCCTCCCTCAGTTAGCTAAT
CCCTCGCCAGGACTTGATTCGCGCAGGCCCAACACTTCATATATTACTGAGAGCAAAGGGTCATTAGGGTCGCAGAATACCAGTGGCTCTTCACA
AATCCAAACCAGTCCCAGCATGGAGGTTGCCCACGAACCGAGTGAAGGTCTGTCCCAGTTAGCTACTCTTTCGCCAGAGAATTGTGCTGCGGGAG
CTATTAGCACGACTGAAGGGCTATCGAGTTCACATAATACTTTAGAAACTTTCGAAAACCAAGCTAATCTCAGGAACGATGCCAACAAACTAAGC
AGATGTATGCCGGCATTAGCTTCGCCAGAACGCCATCTGCACAGTTCGAAAGCCCCTGAGAAGTCATCTGAAGTCTTAAGTCCCCAAGTTAAACC
CCATCAGAGCAAGGAGGTTGCCGAAGAACAATCAGATAGAGCGCCCCAGTTAGAGATTCCTCCGTCAGGTTTCGAAGTGCCCATGTCCAAGACAC
CAGAGAGTCCTGCTTCAAAAACCAGAGCTTCGGACGAGACCCCAGCCAAACCTGAAGAGATCACAGATTCTACCGATGTATATGAGACTTCCTTT
GTGACGGATGTTGAAGTGGACCTTAAAAAACATGGGCGCTTTATTTTTCCCGTATCACTTGAAACTTTTCGGCAATATATTAACTATGACGAGAT
TATCCGAGCAATTCTAGTAAATAATCACATTAAAGACGAACATCAACTGTCAAAATTAATTTCTGATCCTTCGCACCCACAATGCAAAAAATTTT
TCCGCCAGTTTTACAATAAATTTTATGCACGCAATGATGTTCGTCAAAGATTCAAGTACAAATTCAATTGCCCCAATCCTAAGATGCTGGCTAAG
CTAAAACAAAAAGCTAAGCCACTTGATGAAAAGGCTCTTTTTACAATGAATCGAACAGATAATGCAAAAGCAGTAAACGAATCCAAGTCCCAGGT
ACCTTTCACTCCTAAAACAACAACAGAAAATTGTCCACCAAATCCCATTTCTTTAGAGATGTTCAAACGTCATGTGAGCAATCTCGATGATATTG
TTAATGAGATGCAAAAATGCGATGAGTACAAAGAAAAAAGCAAGGAGGAGGTAATTCAGGACTACTACGAGGGCTTCTATTCTGGACCAGACATG
AGGGAGAAGTTCGAGTGCCGATTTAAACCGTGTCCCAGCAAAAAAATAAGACAATTGTTAAGTTTTCCACCGAAAAACAAGGAGCTACCCCCAAA
GAATCCAAATTGCCAGGTGGCTTGTACCACAGAAAACCTAAGCGATGAAAGTTGTCTGCAGTCATCCAGAAATGTAGTACGAGAAACGCAAAATA
TCACCGAAGAGAAACCAATAGCTGAACATGAAAGTATACCATCCACAAGGACGCCTAGTTCTAATGACGACAAGCCCGGAGAAGAGTGTCCACCA
TACCCTGTATCCTTAGAGCTGTTCAAAAGTCATGTGAGCAATCTAGATGATATTGCTAATAATATGCAGAAGTGCGTTGAGTATAGAGGAAAATC
CAAGGATGAGGTTATTCGCGACTACTACAAAGGCTTCTATTCTGGACCAGAGATGAGGGAAAAGTTCGCATGTCGATTCAAGCCATGTACCGGCC
ATATACTACAACAATTGCTTAGTTATCCAGGGAAAAATGTGAATGATTGTCTACAGGAAACTGATTGCCTGGCGACGTGCACCACTAGAACACCG
CTCAAGGAAAGTTGCCTTCAGTCCAAAAGCGAAATGTCGTTACCTGTTCGCAGAAATGCTTTAGAAATCTTAATGAAAAGCAGAAAAAGGACTAA
AGTCGCAAAGGAAGCGATCAGCAGTAAGCCGATGACTACACAAAACACGTCTCAATTTCAACCAGAGCCTTTTCCCGAAGACGCATTAGTTGTCC
CAGAAGACGTCACTACCAACCAAGGCACACAGCCACTGGAATTGCAGCATGAACTAGAAGTTACGGAACCCATAAAAGATTATATTCAACTAAAT
GCTGAGAGGCTTTATGAATTATCGAGGTAAAAAAAATAATGTTTAAAGGATTAGCAAGCACATTTATACAACACGATTATATTTAGCAAACTGAA
GATCGGGTGGAATTATACGGCCCATAACTTTCTCGATAAATTATTTAAAGGAATCAACTGCCCAGTAACACAAGCATTTCTAGAAGAACAATATA
AAAGGTATTCCGTATCTACCGGGCA
(SEQ ID NO: 224)

Start ATG: 83 (Reverse strand: CAT)

MEASASINLQPVVNVPTIYKDPWYMITVLVLYLYFVTKAGPHFMEWRKPYELKRLILLHNFIQVVSCIYAIKEVLYITDNTIYIFWKCRDIGSSP
ELVRRYYNLAYFLFWLKISELIETVIFVLRKKQNQVSKLHIFHHFSTVTLVYALINFNENGSAAYFCVFLNSIVHVIMYSYYFVAAVADKTLVQA
LTPVKKCITVIQMTQFVLILTQVAFQLVLCGMPPLVLLYFTTVILGMFYGFYDFYNSAYQASQRRKSQTPQSDSKKSNMYPVSFAAFQKLIVNLS
EIASELKTANGDNRTLVEWSRWYYKEFYRNPSIRARFPVKVAPCPRRTRDNLLKVPEPGGISQNDVANVAAAGPSQVEQPEVLVEGSQLTTLAET
AKSHDAVEGVAVECKPSGSESPDVIVNVERCGAFIFPVSFDVFLQCINKMLLFKKIVRSIEHCLVLLSDDERRLLTLQRFYNRFYMYPEKRSPTN
IFNATTEIPLEKLLESGKPLDKKAVKTVAELTAMKSLTKNSIVSFEVFKKNMANLSDIVEQMRQLDANYASKDVQECALDYYLAFYITPRIRYKY
AYKLKPCTSTFKACMLSILGKDIAEKLRKSLPQLANPSPGLDSRRPNTSYITESKGSLGSQNTSGSSQIQTSPSMEVAHEPSEGLSQLATLSPEN
CAAGAISTTEGLSSSHNTLETFENQANLRNDANKLSRCMPALASPERHLHSSKAPEKSSEVLSPQVKPHQSKEVAEEQSDRAPQLEIPPSGFEVP
MSKTPESPASKTRASDETPAKPEEITDSTDVYETSFVTDVEVDLKKHGRFIFPVSLETFRQYINYDEIIRAILVNNHIKDEHQLSKLISDPSHPQ
CKKFFRQFYNKFYARNDVRQRFKYKFNCPNPKMLAKLKQKAKPLDEKALFTMNRTDNAKAVNESKSQVPFTPKTTTENCPPNPISLEMFKRHVSN
LDDIVNEMQKCDEYKEKSKEEVIQDYYEGFYSGPDMREKFECRFKPCPSKKIRQLLSFPPKNKELPPKNPNCQVACTTENLSDESCLQSSRNVVR
ETQNITEEKPIAEHESIPSTRTPSSNDDKPGEECPPYPVSLELFKSHVSNLDDIANNMQKCVEYRGKSKDEVIRDYYKGFYSGPEMREKFACRFK
PCTGHILQQLLSYPGKNVNDCLQETDCLATCTTRTPLKESCLQSKSEMSLPVRRNALEILMKSRKRTKVAKEAISSKPMTTQNTSQFQPEPFPED
ALVVPEDVTTNQGTQPLELQHELEVTEPIKDYIQLNAERLYELSR*
(SEQ ID NO: 225)

Classification: hypothetical

Celera Sequence No. : 142000013384693
GCTTCAGAAGCGGCTCCTCCTTGCCTGCAAGCAGCTTGTCGGCTGAGTATATGTTGATCTGCCCCGCCTCGCAGCCGCCCACAATCAGGCCACTG
GGGTGTGGTCCCACTGGGGACCAGATGAGTTTTTGGAACCTGCGGGAGGAAAAGCCGGTTATGTGAACGACTTGATGCACAAATTGAAAGCCATA
ACTCACTTGTACTGGCTGGAAACGCTGGCCCTCAGCTCCAGATCGTATGTGGCATCGCTGAAGTTCGGTGAGTACAACTCCAGAGTGGAATTGGC
ATTGGAATCGAATTGTTGGGCGGCGGTGCCGGCGGCCAAGAGAATCTGCTGCTGCTGCGCCGGCGACCAGGCGATGTTCACCGTCTTTTGCAGTT
CCTTGATCTTCATCTTGCAATGTCCCTTCGTGCTGCTCGTGTAAATAAAGCGAAAAAACACAAATATTATGGGAGGTACAAGTTCAGAACGAAAT
TGTGTCACGTCCAATTGGAGTAAGCCCCGTCATCACTTTTCCCATTGGCTTCCCCATTGCAGATGTGGCCCAGTAGTGCCCGCCGGCCTTTAAGT
ATCTTTAATTATGCTAATTGCGCAACTTACACACAATTGTGAATGCAATTTGTACTCGCTTGCGCTGCAACGAGACTTTTTGATCTTGAATTTAA
CTGGAATCGTTAATATTTTTAAGAACCGTAGGAACGGCCAGTGTGACCGTGCTCTGAGCCAACGTAATATACCACAGGGCACGCACTGAAATACC AAATGCGTGCGACCAGAATATACTGCGAGTTTAACGGTATGCAATTTAAATATTCCGTTTCAATGTGCAATTTTAAAAATAGTTTTTATCAGTAT
ACATTATTAAAAATGATAGTCGAAATTATTTAAAGATTTATTTTCCATCGCATTTTATATTCGTAAACTAGCTTCAGCACTTTTAATATTAATAT
TTATTATGAACTCATTTTAAATTCCAGATCACTTTGCATTTATTTTTTGACTGGAACTGGACTCGAATGTAGATCTCTTTATTATATAGGTATCTTT
CATAAATATAAGCTATGTTTATTTAATACGCATGGTATGCATCCACTCATTTGGCAGACGATATGGCCGCCACACGCTGCTCCACCTTGGCCACC
TTGCTGTTGATAGTCTCCAGATTCTGGGCGAAAGTCTCCTGTACGGAATGCAGCAGCTCCTTGTTGTTCACCAAGCTAGTGGTGATGGTTCCCTG
CTTCTGCTCAATCTCTGCGATGATCTTGGCGAAATTGTTTGCTGCAGAGCAAGTTGATTAGTTACAGAAACAAGCACAATGCTAAAATGCTAAAT
AGAATTGCTTACCATATTTATGGAGGGCCTCGAGGGCTTGCATGCGTTCGATGACGTGCGGCAGTATTTCCACCACTGGCTCCGTGCGCTTCGCG
ATGTCGTATAGTTCCGTAATCTTCTGATCTCGTTTGGCGTCCTGGGCACTGCCGCTGGACTTTTCGGCGATAGCATCCATCTTGCCGGCCAGCGA
GGTCAGGCGCTGCTCGATGGTGTCCAGTTTATCAGGCTGTATCAGGGCCGCCTTGGTGCTTAGATGACGCACTGCCTCTAGTACATTGGTGGTGT
TGGTGGCGGCGGTAAGGCGGCTCAACTTGTCCGGCTGAGCGCCCAGCACCTTCTCCAGCTGCGAGATTCGCTGCTCTAGACTGGCTACGCGGGCC
GTGGCCGCCAGATCGGTGCCAGGCGTGGGTATGGCTGTGAGAACGCCGGACTGCTTGAACTCCTCCACCTGGCTAATGAGTGCTTTCACCTGCTT
ACTTCCAGGCGTCTGCTCCTTGCCCAGCACTTGCTCCAGCTTCAGCGACTCCAGCACCTTTCGGGCCGTGCTGATAACCGTGGCCACCGCATCGT
ACGACTGCTTCTCCTCGTCGGCTACCTTGCGGTCCACCTGCAAGGCGGCCACCTCGTTCAGAAGCTCGTTCATCTCGATCTGCAGGCGCTGGCAC
TTCTGCACCGGCGTCTCCTTCTCGCCCTGGCCAACCAGCTCGTAGTCGCTGGAGCCGCGCGTATCGTAACCCCGGCACATGCGTCGTCCAATGCG
ATCCGTGAAGTCCACACTCCCCTCGACCGTTGCTCCGCTGAAGCGCTTGTGAGCGACGCTCGGCGAGATGTGCAGTCGCTCGATGGCTTCGTTCT
CCGGCTCCTCTTCGTAGTAGTCGGATGTATCGAGCTCCGGGTCATCTGGAGTTTCGTACACGTCCGGCTGGTCATAAGCCTAAAAACATAAAGTA
CATATATGTATAAATGGGCAAAAACGAAAGCTTAAACGTCACTGCCATGGTGCGGAGTTCCGACTTACTATTCCCGGTAGGTTCTGGAACTTGGG
ATCGGCCATTATTGTGGGCACGTCGACGGCGGTGTTTGGAATCCTTTGGCAACGAAATAATTATAAACCTTCAAAAATCCTTTTTTACAACAATC
AATTCGATCTGATGTCATAAAAAAAGTTACCGTGCGCGGTTACCAAACAAATGCCAAAGTGCAGTTGTCATTGGAGTATTTATAAACAGAGGTAT
CTAAAAAGTCATTTAAAAAAGACAGTTATTACTTGTAACGGCTAATAAGCTAAGAGTAAATAGTATTGCAAAATATATCATCGATATAAATAAAT
TGTACTTGCACATTGTACTTTGTTAACTGGATTCATAGATGCAAACATTTATAAAAATAAATTAAAGCTTTTTGTGCTAATTTAAACCTATTTTG
ATTTTAGGAAAAACGATATACATTTAAAATCATTCATAAGCAATAGGTAAATAATTCCATGATCGACTTCCAATTGGTAAATCAATGAAGGTACA
CTTTTCTTCTGGTATTTTATAGACCAGTGAGGATAGAAAAAAGGCACGGTCCTACTGTACCTAGCACAGGTACTAAGTTAGTCAACACTGTAGTT
TTCGTGTAGTTTGCGGGCGAAGCGAGTGGGCGGTGGGAGCTGCTAGTTGGTTGTACTAATCTTAATATTTTGCATCCGAAAACAATAGAGTAATG
TCTGGCTTAGAGTACGGGTTGCATAGATACGATGATCTGCCGCTGGAGGTGAGCATATAATGTGAACGGACTGCCGCGGTCCCGTGACCAATCCA
TCATTTCGAGCGTATCTATATCTGCATATTCATATACCTGTTAGGGCAGTCAGCTGATTTTGTTTTTTTCTGTTCCGCCCCCAGATTGTTTTGAA
GATTTTCAGCTATCTCGGCTACTCGGACTTACAAGCGGCAGGATCCACCTGCCAGCGATGGCATGCGGCGCTGGATCAGGCGGAATTTAACCAGC
GCACGCGAGTCTGCTTCTCCAAGGTGGTGCTATCGGATCAATTGAGTCCTGGAGTGGATCTGATGCGCTGCGAGCGGCGTTTCCAGCACTTCCTG
TTCGAGGACGTGACACTGGGACAAGTAAAGGAATTGATGCGCTTCATGGGCAGGACCGCTCAGTCC
(SEQ ID NO: 226)

Exon: 2486..2349
Exon: 2264..1343
Exon: 1276..1001
Start ATG: 2384 (Reverse strand: CAT)

Transcript No. : CT7980
GACATCAGATCGAATTGATTGTTGTAAAAAAGGATTTTTGAAGGTTTATAATTATTTCGTTGCCAAAGGATTCCAAACACCGCCGTCGACGTGCC
CACAATAATGGCCGATCCCAAGTTCCAGAACCTACCGGGAATAGCTTATGACCAGCCGGACGTGTACGAAACTCCAGATGACCCGGAGCTCGATA
CATCCGACTACTACGAAGAGGAGCCGGAGAACGAAGCCATCGAGCGACTGCACATCTCGCCGAGCGTCGCTCACAAGCGCTTCAGCGGAGCAACG
GTCGAGGGGAGTGTGGACTTCACGGATCGCATTGGACGACGCATGTGCCGGGGTTACGATACGCGCGGCTCCAGCGACTACGAGCTGGTTGGCCA
GGGCGAGAAGGAGACGCCGGTGCAGAAGTGCCAGCGCCTGCAGATCGAGATGAACGAGCTTCTGAACGAGGTGGCCGCCTTGCAGGTGGACCGCA
AGGTAGCCGACGAGGAGAAGCAGTCGTACGATGCGGTGGCCACGGTTATCAGCACGGCCCGAAAGGTGCTGGAGTCGCTGAAGCTGGAGCAAGTG
CTGGGCAAGGAGCAGACGCCTGGAAGTAAGCAGGTGAAAGCACTCATTAGCCAGGTGGAGGAGTTCAAGCAGTCCGGCGTTCTCACAGCCATACC
CACGCCTGGCACCGATCTGGCGGCCACGGCCCGCGTAGCCAGTCTAGAGCAGCGAATCTCGCAGCTGGAGAAGGTGCTGGGCGCTCAGCCGGACA
AGTTGAGCCGCCTTACCGCCGCCACCAACACCACCAATGTACTAGAGGCAGTGCGTCATCTAAGCACCAAGGCGGCCCTGATACAGCCTGATAAA
CTGGACACCATCGAGCAGCGCCTGACCTCGCTGGCCGGCAAGATGGATGCTATCGCCGAAAAGTCCAGCGGCAGTGCCCAGGACGCCAAACGAGA
TCAGAAGATTACGGAACTATACGACATCGCGAAGCGCACGGAGCCAGTGGTGGAAATACTGCCGCACGTCATCGAACGCATGCAAGCCCTCGAGG
CCCTCCATAAATATGCAAACAATTTCGCCAAGATCATCGCAGAGATTGAGCAGAAGCAGGGAACCATCACCACTAGCTTGGTGAACAACAAGGAG
CTGCTGCATTCCGTACAGGAGACTTTCGCCCAGAATCTGGAGACTATCAACAGCAAGGTGGCCAAGGTGGAGCAGCGTGTGGCGGCCATATCGTC
TGCCAAATGAGTGGATGCATACCATGCGTATTAAATAAACATAGCTTATATTTATGAAAGATACCTATAATAAAGAGATCTACATTCGAGTCCAG
TTCCAG
(SEQ ID NO: 227)

Start ATG: 103 (Reverse strand: CAT)

MADPKFQNLPGIAYDQPDVYETPDDPELDTSDYYEEEPENEAIERLHISPSVAHKRFSGATVEGSVDFTDRIGRRMCRGYDTRGSSDYELVGQGE
KETPVQKCQRLQIEMNELLNEVAALQVDRKVADEEKQSYDAVATVISTARKVLESLKLEQVLGKEQTPGSKQVKALISQVEEFKQSGVLTAIPTP
GTDLAATARVASLEQRISQLEKVLGAQPDKLSRLTAATNTTNVLEAVRHLSTKAALIQPDKLDTIEQRLTSLAGKMDAIAEKSSGSAQDAKRDQK
ITELYDIAKRTEPVVEILPHVIERMQALEALHKYANNFAKIIAEIEQKQGTITTSLVNNKELLHSVQETFAQNLETINSKVAKVEQRVAAISSAK
*
(SEQ ID NO: 228)

Name: dynamitin-like
Classification: motor_protein

Celera Sequence No. : 142000013384768
GAAATGAGTTTTGTTTTGTTTTGTTTCTTCCGAGTGTTTGTGTGTTTATGTGTGTGGGGAGGGGGTGTATTCTGTGTGCGGCGTGTTTTGAGTGA
GAGAGATAGAGAGAGAGCGCGAGTTGCTGCGGGTCGACGGTCGAAGGGGGTGGTGGTGGAGTTGGTGGTGGGGGGCTTGGTTTATACGACAAGTT
TTGATTTATTATTAAATTTAAATACCTATGTATATAAATTACGTTTCTGTTTATTATAATTATTGTTGTTTCCATCTTAATCATTTTGTTTTCTT TCGCTTTTTATTTTTCATATTTTTTTTTTGTTTTTTGTATGTAGTGGGCAACTGCGGCATTTGTAAATTTCTTTATATTTAAATGTTCCTTTTGA
CTGTGTAAAAATATCGATTTCCATCTGATCTTGTTTTGTAGTTACTATTCATGTATGCATTTGCTTTTCGTTTTAGTTAAATTACGTTAACGCTG
CATTCTGAACTCTCTGTTGCTGCTGATTCTGCTGCTTGTTCTTCGGATTCTTGATCGGATTCTTCTGATTCTTCATCTTGGCGCGCTTTCTATGC
TATTGAAATGTTGTTTGTGGTGCTGCTTACTGCCTTCTGGATCGGGATCCTATATTCCGCTCTGATCTGATCGGTTATGTTCATGTTATGTCGGG
TTGTGTGTGTCTGTGTTGTGTGTATGAGAGTGGAGTGTGTTGGGTGTTCGCATCTCGTTATATGTTGTATATATATATATATATATATGTGTATATA
TATATATATATAATATATTATATGTATGTATAGTTAGTTGCTTAATAGTAGAATTTCTTGAATGTTGTTGTGGTAAAGTGTAGGTAATGTTGCTC
TATGTCTCTATGTCGACTCAACTGCACTACATACATATGTCTTTCCACCGGATACGCGGCGAACCGAAACGTGCCGAGCCGAACCGATCCCCGTT
TCTGACCCGCATCCGCATCCGTATCCGTATTTCGTTTCCTCACCTCCGCCTCATTCGCTGCGCAGTTTCTTTAGATCCGGTGACTTCTCCCCCAC
GCCCACACCCACTCCGCCGGCGTTCTTCAGCTCCATATCGCAGTGCAGGGCAGTACGCTTCTGTCCAATGGCTGGTGCCGAGTCTGCACCCGCTG
CTACCGGTGAAACCGCATCCACCGCCTTGTTCGCCGCCAGCTGCTGCAGTTTACTGTCCCTCACAATGCCGTTGCTGCTATTGCTCTCGTCAGCC
TCTAGCTCCGCCTCATTATCCTCCTCCTCGTCCAGCTCATCTTCCTCCTCGTCCTCCGCCTCATCCTCATCCTCGTCGCCCAGGACGCCGTTCCC
GTTACCATTTCCATTGGCTGGTGCTGCAGTCGCTTTGCTGGCTGGCTGTGGTGCTGCTGTAACCGCTTCCTCTTCTGCCAAAGGAGCAGGCTGAC
CGTTGTTGGTGATCGAATTGTTAGTTTTGTGGGGCTGGCTCGGCGACTGCTTTTGATTCTGATTCTGGCTCGAGTGCTGTGTGGGAGTCAGGATG
GGCAGGCTGTTGGTCTTGGGCGGCGCCTCCTGATTGCTTTCAGAGTCCGAGGCGAGCGGTGTTCCACTCGAACCGATGCCAATGCCAATGTCTAG
GGCGATGGGCTCACCGTCCTCTGTGGAAGTGGTGGCCGTTGTCTGTGTGGTGCCATCGTTGTCATCGATGATCGGCTCCTGGGAGGTGGAATCGT
TCGAAACAAAGTTGGAGTCACCGTCCTGCAGGGCGGCGCCAACGGCAGCTGCGTTGTTCTTGGCCTCGCCCGACTGTAGAGGCGTCAGAGCAGCC
GGGTTGGTGTTCTCATTCTCTGTCTCCGATTCTGTAGCAGTGTTGCGACCGCCTGGGGGATAGAAAGCATTGGATTAGCCATCAATGGTCAATTT
GTTAACTCGGCGAACTGCGGTCAGAGTAATCAAACAAAGAAACTCTGTGTTTGAAATTATTAGACATCCTAACACTTTTGAAAAGCTGCCAACAA
GTATAAGCTACTGATAATATGTTAAAAGTTAACTATTTTACAGTAGTAACTTTACAATTCCTCCTTTTTATTTAACATGACGCCACGAGTAACGA
ATAAATTGTAAATTGTAAATTGACCACTAGGCTACTACAAACATAATGTTTAATGGAAAATTCCGGATAGGAAAAATACTTGGTTTCTGGAAAAG
ACCACTCGGTTTGAGTGTTTTGTTGCAAGGGTGTATACTCAAGCCGCAGTTATCGGATCATCTTAGCTGCTTACCTGCTCCTTGGCTTTCGTCGT
CCAAATCAACACCCACACCATCGTTGGTATCGTCGCCATCGAGCACCTTGCTGCTGTTGCCGTTTGTGCTGAGTGAACCGGTGCCAGTGGAGGCG
CCGGATCCAGGCGGCGGCATATCGTCGAGCATCTCGGGACTGAGATCATTGGCCACATAGTGTGACCAGAGGGCCAGCTCCACGCGATGAGGCGA
CCAGTGCGGCGTATCCCCGCCCACCTCCGCATTGAGGCGCTCCACGGTGGCCTGAATGTGATTGACGAAGTTGAGGTACTCCTTGGTGGTGTAAT
CGATGCCCTCGATCTCTGGTATGGCCATCAGGCACTCGTCGGCCATGAATGGTGCCGAATCGGGAGCTGCGGCTGCCAGCAGTGCACTGGCCATT
GTGGTGCCAACGCCCTTGAGGTTCGATAAAGCTGTGATCGCCTGCTCCAGATTGGGCAGCTTGCGGAAGGCCTTCTTTGTCTCCTGGATGACGGC
GCGCGGTGTGTTGACCTTGACCAGGTAGGATAGCTGCGGATAGAATTTGCCGCGCGACTGCTTCCACTTCATCGACTGGACGAGCTCATCGTATA
CCATATGCGCGTCCTTGCCGCGTGCCTTAATCAATTTGGGCAGTTCATTCTGATACCACTGATCCAGGCGGATCAGCTCTTGCGGCTTCTTGCAG
CGCTTCTCGGCCTTTAGCTTAAGAACCTGGGGATAGAGCTGGTAGCAGTACTCGAACTGTTTGGTGCTCCCGGTCTCGAAGAACGAGACCGTCGC
CTTGCCGTTGGACATCTTCTGCGGATGCGGATGTGTCGTTGTCGCCTGCTAATGATTGGTGGTATCGCTGTATCTCCTTATCGTGGTATCTATCG
CCTTGGGGCCCAGGACGTTGGCTGATCCGCAAGTGACCGGCTGGCTATATATGCGGCAATATATGTACTTTGGTGTAAGCTACTATACGCCAAAT
CAATTTATTGCTTACTGTTTAGTCTCCTGCTTTTCCTGTCCGTTCCGAGCTGCTCCTGTCAACGTACTGCTATTCGTGCGTTGAGAGTTCCCGGC
GAGAAAGAAGCGAGTACGTGAGAGACAGAGAGAATGCGAGTGCGAGAGAGGGAGCACGAAGAAGCAGCAACGCAAAGGAGAGTGGATGAAAAGAG
AAGAAAAGAGGCACACAATTAGGTTTACAGTTACGATTACATATGCAAGGGGGATCGGTGCGGTGGCATAGGGAGGTAGTTCGATTGATTACTGT
TAATGCTGCTGCTGCTGCGGCCGTGTCTCTGTTGTTTGTTGTATTTACTCAATCCGATAATCGCTCACTATTTGCCAAAAATCTGCTCGCTTCCG
CCGCCGTTTGCACAGCACACAAATCGAATTTTTACAGTGCTGTCGTCGGGTTCTTTTTAGTCCGCCATGCACTCACACAGTCAAACTGACAGGCA
CACGGATGGACACACACACACTTACTCAGCACACTCGCTCTCGCACACCCAAAGAGAGCCAGGCGCTCATACACAGGCAAAAACACGCACACAAC
ACACACACTGACTTAAACACGCACACACTTATATACTGAGGCAACAACAGCAGCAGCAGAAAATTTCTTTTTCATCTAGGTTTTCAAAAAAAATA
CGAACGCGAGCATTAAATAAACGAATGCTACTATTTTCGCTGTTGTTGTTGTTGTGCTTTTTTCGTACCTCTTGTCTTTTTGGCAAACGGTGA
GAACAGCTTTTCACTAGCGCACTGCACGCACACAGATGAGTGGGTGAACAACAAATACCTTTTAGTTAGTCGCCGCCAGTCTTCCTTTCCGTCCA
CATCCAAACAACTACTCCAATGCTTTGCTGTTTTTCTGTGTTGCCTCTGCTTTGCTTTGCTTCGCTTCGCCTCTGTGCTTGTGCTGTGCTGCGTG
CTTCGTGCTGTGCCCGTGCTGTGCTGCTTCTTCTTCTTCCTCTGCTGTTTCAGTTTCTGCTTTCTGCCTGCAGGGGCGCCGTTGACAACTGACAA
ATAAAAAGGGGTTACTCTGTTCTCGAAATGAGCACGCCACCGAAGGCACAACAAAAAATTAAAAAGGATCGGAGCGGAGCGATGCAGCTGTGCGA
TGTGCTGCTAACTCGTGTGACGGGAATTGGGAATTGGGATTGCGAATGGGAATGGGAGGGAATACGAGAAGCGAATATGGGAATGACGAACGACG
ACGAACCGGGAACAGGAGTTGTCGTTCTATCTCGCCCGCACTCGGTGCCCGAATGTATCTGTATCTCTCTGGCACCCTCGGCGTTCCATTTCATT
TTGCCGGCGACGTCCGTGCTCTCTGCCGCCGCTCTGCCATCGCCTCTGCCGCTGCGTTTATGCGCAGTGCGTCATTACACGAATACCTGTTTAAA
GCGGAGGCATAAACGCGGCTTTGTCGATCAACATCCATGTTACCGAAACCCATGTTCGAGTTATAGAAACTTCGAGTAACAAATATCTATATTCT
AGCAATGTTTACCCTTATTAGCTTAGTTAGTAGTGCAATTATGTTTCATGTTTTTACAAACAGCAGAATGTTTTTAACAATAGTTATCTCTATATTCA
GGTCCTTCAATTAAATCAAAAAGGAATGGGTTTTGTGAGTGGGTTGGGCTCCAGTGAGACTTGTTAATAATTTAAGAATTCGCGATATTCTAGTG
TAAACAGCGCGTCACTGCATGTTCGCTGCTTTTGTTGTGCCAGTTGCCAGCGACAGCGGCGTCGTGTCATTATTCATATTCATGAGGGGGTGCGT
CAGGTTTGCTGAATTTTACTGACTTGTTTGCGCGAACCGAAATTATTTATGGTTCAGCACGAAGAGCGATAGAAATTCATGCATATGTTGTTGGT
TGGTTAAAAAGTTGCCCTTACATGCAGTTAAGTGCATATAATTTGTCTACTTGCGCATTTATTAAAAATGCATACATATTAAATAATGTACTTAA
TTACTCAGCGGTTTGAGGGTTGGAGCATTTACAGATGACACTGTAGTGATCAAATGGTAGCTATACATGTATAAATATCTAAAATATTACAAAAC
TATTCCAGCGTTCAAGCATTAACTAATTCGAGAACAGCTGCTGGTTCCATAATCGAGTACACACGTGTGCTACTCAAAGTCTAAGCTGAGAGAGC
GGTCGAGCGGCAACTTGATATTTAAAAAACAGAACCCTACTTAACAGTCGACTCAAGTTCGATCCCCCCGCAGGTACGCCCC
(SEQ ID NO: 229)

Exon: 4497..4049
Exon: 3299..3246
Exon: 3179..2260
Exon: 1857..1001
Start ATG: 3055 (Reverse strand: CAT)

Transcript No. : CT8088
AGATAGAACGACAACTCCTGTTCCCGGTTCGTCGTCGTTCGTCATTCCCATATTCGCTTCTCGTATTCCCTCCCATTCCCATTCGCAATCCCAAT
TCCCAATTCCCGTCACACGAGTTAGCAGCACATCGCACAGCTGCATCGCTCCGCTCCGATCCTTTTTAATTTTTTGTTGTGCCTTCGGTGGCGTG
CTCATTTCGAGAACAGAGTAACCCCTTTTTATTTGTCAGTTGTCAACGGCGCCCCTGCAGGCAGAAAGCAGAAACTGAAACAGCAGAGGAAGAAG
AAGAAGCAGCACAGCACGGGCACAGCACGAAGCACGCAGCACAGCACAAGCACAGAGGCGAAGCGAAGCAAAGCAAAGCAGAGGCAACACACAGAAA
AACAGCAAAGCATTGGAGTAGTTGTTTGGATGTGGACGGAAAGGAAGACTGGCGGCGACTAACTAAAAGCAGTACGTTGACAGGAGCAGCTCGGA
ACGGACAGGAAAAGCAGGAGACTAAACACCAGCCGGTCACTTGCGGATCAGCCAACGTCCTGGGCCCCAAGGCGATAGATACCACGATAAGGAGA
TACAGCGATACCACCAATCATTAGCAGGCGACAACGACACATCCGCATCCGCAGAAGATGTCCAACGGCAAGGCGACGGTCTCGTTCTTCGAGAC CGGGAGCACCAAACAGTTCGAGTACTGCTACCAGCTCTATCCCCAGGTTCTTAAGCTAAAGGCCGAGAAGCGCTGCAAGAAGCCGCAAGAGCTGA
TCCGCCTGGATCAGTGGTATCAGAATGAACTGCCCAAATTGATTAAGGCACGCGGCAAGGACGCGCATATGGTATACGATGAGCTCGTCCAGTCG
ATGAAGTGGAAGCAGTCGCGCGGCAAATTCTATCCGCAGCTATCCTACCTGGTCAAGGTCAACACACCGCGCGCCGTCATCCAGGAGACAAAGAA
GGCCTTCCGCAAGCTGCCCAATCTGGAGCAGGCGATCACAGCTTTATCGAACCTCAAGGGCGTTGGCACCACAATGGCCAGTGCACTGCTGGCAG
CCGCAGCTCCCGATTCGGCACCATTCATGGCCGACGAGTGCCTGATGGCCATACCAGAGATCGAGGGCATCGATTACACCACCAAGGAGTACCTC
AACTTCGTCAATCACATTCAGGCCACCGTGGAGCGCCTCAATGCGGAGGTGGGCGGGGATACGCCGCACTGGTCGCCTCATCGCGTGGAGCTGGC
CCTCTGGTCACACTATGTGGCCAATGATCTCAGTCCCGAGATGCTCGACGATATGCCGCCGCCTGGATCCGGCGCCTCCACTGGCACCGGTTCAC
TCAGCACAAACGGCAACAGCAGCAAGGTGCTCGATGGCGACGATACCAACGATGGTGTGGGTGTTGATTTGGACGACGAAAGCCAAGGAGCAGGC
GGTCGCAACACTGCTACAGAATCGGAGACAGAGAATGAGAACACCAACCCGGCTGCTCTGACGCCTCTACAGTCGGGCGAGGCCAAGAACAACGC
AGCTGCCGTTGGCGCCGCCCTGCAGGACGGTGACTCCAACTTTGTTTCGAACGATTCCACCTCCCAGGAGCCGATCATCGATGACAACGATGGCA
CCACACAGACAACGGCCACCACTTCCACAGAGGACGGTGAGCCCATCGCCCTAGACATTGGCATTGGCATCGGTTCGAGTGGAACACCGCTCGCC
TCGGACTCTGAAAGCAATCAGGAGGCGCCGCCCAAGACCAACAGCCTGCCCATCCTGACTCCCACACAGCACTCGAGCCAGAATCAGAATCAAAA
GCAGTCGCCGAGCCAGCCCCACAAAACTAACAATTCGATCACCAACAACGGTCAGCCTGCTCCTTTGGCAGAAGAGGAAGCGGTTACAGCAGCAC
CACAGCCAGCCAGCAAAGCGACTGCAGCACCAGCCAATGGAAATGGTAACGGGAACGGCGTCCTGGGCGACGAGGATGAGGATGAGGCGGAGGAC
GAGGAGGAAGATGAGCTGGACGAGGAGGAGGATAATGAGGCGGAGCTAGAGGCTGACGAGAGCAATAGCAGCAACGGCATTGTGAGGGACAGTAA
ACTGCAGCAGCTGGCGGCGAACAAGGCGGTGGATGCGGTTTCACCGGTAGCAGCGGGTGCAGACTCGGCACCAGCCATTGGACAGAAGCGTACTG
CCCTGCACTGCGATATGGAGCTGAAGAACGCCGGCGGAGTGGGTGTGGGCGTGGGGGAGAAGTCACCGGATCTAAAGAAACTGCGCAGCGAATGA
(SEQ ID NO: 230)

Start ATG: 628 (Reverse strand: CAT)

MSNGKATVSFFETGSTKQFEYCYQLYPQVLKLKAEKRCKKPQELIRLDQWYQNELPKLIKARGKDAHMVYDELVQSMKWKQSRGKFYPQLSYLVK
VNTPRAVIQETKKAFRKLPNLEQAITALSNLKGVGTTMASALLAAAAPDSAPFMADECLMAIPEIEGIDYTTKEYLNFVNHIQATVERLNAEVGG
DTPHWSPHRVELALWSHYVANDLSPEMLDDMPPPGSGASTGTGSLSTNGNSSKVLDGDDTNDGVGVDLDDESQGAGGRNTATESETENENTNPAA
LTPLQSGEAKNNAAAVGAALQDGDSNFVSNDSTSQEPIIDDNDGTTQTTATTSTEDGEPIALDIGIGIGSSGTPLASDSESNQEAPPKTNSLPIL
TPTQHSSQNQNQKQSPSQPHKTNNSITNNGQPAPLAEEEAVTAAPQPASKATAAPANGNGNGNGVLGDEDEDEAEDEEEDELDEEEDNEAELEAD
ESNSSNGIVRDSKLQQLAANKAVDAVSPVAAGADSAPAIGQKRTALHCDMELKNAGGVGVGVGEKSPDLKKLRSE*
(SEQ ID NO: 231)

Celera Sequence No. : 142000013384445
GGAGTTGATGAAAGTTTTGGAAGTCAATTAATTTGTTTGATTTTGGCAATTAATTCCAGTGCAGCGCAAAATAAAAAAAAAAATAAAAATATTTTA
TATAATTTATATAAATTTTATTTAAACATAGCTCAGCTTGCCGCGCTGTAGGAAAACTTCTACATACACGTTTATGCTTTATATACACATTCTT
GAAATGAACTATGTACGTATATGATGTCAGTTTTGTATCGAATACTAGAAGCAATTAAATAAATTTCTAACACAACGTACGCACTAAAGTATAAC
ACATATTAAATAAACGTTGCGGTTTTTTCTAGAATTTAAACATATTATCAACACATTTTACATATGCGTTGCTTGAATTTGTTGTTAAATAATAC
TTAATAATTACAAATGTTTTCGCCTTCTCAAATTAAATTTGGACAAAATTGAAGCTAGTTTGGAATGCATTTACAAATATTTGCCGTACAGCAAA
TCATAGCTTGCTTAACAACACTTTAAAACGTATAATATATATTTAGTCACAAGAAATGACTAAAAATAACAAAAAAACATTGATAGACGGATTAA
AATATTGCAAATGATTACGTTAAGGTGTGCAAGCACTTGGACTTCGTTTGAAAATATCTATTCTGAATCGGTTTCATGTTTGCTCGATCATCTGC
TTTGAGACAGTTAACATAGTTCCACTACATAATTCAACGTGTGTGTTTTTAGTGATTGGTGAGGACACAACTACAGGTTTTATAAGGACTTTTCT
TAAAGTTCATAGGTATATTTCACATAGGCTACCTTCCTTTAGCTATTGATGGAAATTGGTTCGTTTTTGCTTTTACTTTCCCTTCATTTGTTTTA
GCATAGTATATAAATTGGTGTATACATATAAATAGTCAAACTTATTTGTTTTCATTTAAATAGTAATAATATAAATATATATATATATATATATA
TGTATATATGTATGTATATAGCATTTTTCGTGTTTTGCTCAATGTTCAACATTATAATATAATTTTCTTATCTGCTTCCGTTTCATTTGTGTTTG
CTATTGCTGCCGTTTTTTTCATAAACTTTATATATGATTTCTGTAGCATCGTGTAAACAGTTTCAAGATCTTAATATTCACTTGCACGTTTATAT
AATATATAGAGCTATTGGTATATTTAATTTTTCATTACGCATTTGTGTCTGTGAGTGTGTTTTCTGTTTTCCGTCTATGAGGTTAGAGCGCTTAG
ACTGAGTGAGTGAGTGAGTGGTGAGTGGGTTGCACGTATGAGCTTCTTCTGGACCGCTTATAACGCACCAAATGGGTCGAGTGGGACGCCTTTAT
TGCTGCCATTCTGCGTTGGCTGGATGGGTTGCATGATGCCCGTTGCATTACTGTGCGGCGCCGCCATCATCGTCGGTTGCACCCCAGTCAAAGGG
GCTGCTGCCTGCCCCCCCATCATACTTGGCTGTCCCATCACCGGCATTCCCTACAAGAGTCGTTAAAAAAGGCGTTAAGAGCGAACATAAAATGT
TTGTTCAATTGAAATTCATGCACTGGAGGAGGGAATACTTATTAACTGCTATGACAGACGCAATGCTACAAAATCAGTGGCAGGAAAAGATTAGT
CGTTTGGGCTTAAAAGGAGGGGGCCCGCCGTGAGCTTGGAAAACAGTTGCTACATGGAATCATACGGAAGGTGGTTAGCTCTACAGACAAGTGAA
ATAGTAACTCCATTAAGAACTGAATGTCTACTAAACTTAAATATGTAGATTTAAATAATAATTTAACAGATACGAATGCAAGATTGTAATGCACT
ATAGTTCAGAGACGGAGACCATAGAGGGAGGAGAGGCATGTTAAACGCTTGTTACTGGTCACCAAGTGGGAATTGTTGGCATGTTTTTTTTTTTT
TTTTTTGCAAGTTAGAAGGAAGTGGCGTAGAGGTCACATTTATACGTTATAGTGCTGTGATGATAGAAGTTCGATTGTTAAACGAAATGATAGGA
AATAAAACTGAAAGAATTTCTTGATTTAAGGAAAACGGCAACTCAGGGCAAAACCAAAATTATATTTATTTATAATCTTTCATTCTGTTTGAGTA
ATTGTAATGGTTTCTTGTAATGTTTCATTTCGTTCGTTTTGGCATCATCTTACCTGCATATAATTTGGCATTACAGGATAACTAGCATGTATATA
CGGATGATTGATTGTGATTGGCGCAGGACTTACAGTCATGCCATGTGCCTACGTATTGCATATTGGTATATATATATATATAGGCATATTGATAGAA
TATATATTGATATATCACAAACACACATACACACACACAGACAGCATTGGCACAGGCGCAGCGTGAGTGGTCATACGTGATTCGTTTGTTGTTGT
TTGTTTGATTGGATTCAATATATATATTTAGTTGTGATTCAATTTGATTCGGTTCGGTTAACGATTTTCGATTTTCGATTTCGATTTCGATTTCGAT
TTTGCGGTATGCGTTGGGATAGTTGAGATATAAAGCAAACATAAAATAAAGAAAAGAAAGAAGTTGATAGTTTATATATACTCCGTTAAAATGCA
AATTAAAAATTAAAATAAAAGAAATTAAAACTATAAAATGGAAATATGTGTCTTGACGTATTTGGCCTGCGTGTTTTGTGTGTGTGGAGGCATAA
AACCCACCGTCGTTGCCCTTCTCTCCAGGATGCCCTAATGCTTATGATCTAGTGCTGTTTGCTGTGATTCTGTAGTTTACGGTGGGGTGTGTGGA
AACTAGGGCCAAGAATATGTGTGGACAAAATAAAGTCAAACTTACAACCCGCAGACTTGATTTGCGATTTGATTTTGGTCATCCAATTTACAATT
ATGATATACGAAATTTAAAAACACTTAGAATTTTAAAGGGGATTCTCACGACGAAGACATATTAATTATAAAAATTTACTTTAAATCTTATCAAG
ACAATTTATGCAAGCTAAAAAATAGTTCATACAGATCAAAAATGTCATGAAAACCAAGGAAACCAAGTAGCTCAAGTTGTAAATTTATACGGATT
GTGCAATTGGTAAATAAACATTAATTTTGATAATATCGTTCACATTAAATCAGGTAAAAAAAAGTGTACTTCGCATGAAGTGTAGCCTAAAGTGT
TGGGTGACACAAAATTGTTAGAAAATGATAGGAAAAAACAATGCATTAACAAAAATAAAGAAATGTGTCGTTTGTTTTCTTCTCTGGCATTGTTA
TAGTTCTTATTATTTTTTGTCTCTGCTTCGGCACAAATTCTAGTGTATTCGAATCTTTTGTTTTAGTCACTTTTTAAATTTGAACAAATTCGAGG
CAACGTAGATTCTTTCGAGTAGTATTCATTGTTTCTGAGTAGAGTAGTTCGGTAGACAGAAGAGTTAGAGTAGGCAAAACTCACCATTGGACGAT
AGCCAGCACCAGTAGTAGCCGCCATTGGTTGGGGTGTCCAATTAGCACCTGGTTTCGCTGTATTTTTAGGTGAATTCCATTGCACGGGTCTATGA
GAATAATGGGGTAAGAGAGTAATGATATATAGACGACGTCAATGAACACGGCATTTGAATTTTGGGTTTTTTTTTTTGGGTATCTAAATAGATTT
CTGCGTGATTTCGAACCATTTTTTTGATGGATTTTATGTACACGTATGGAACATGAATATGGGAGGGTCAGTTCGGAATGGTATTGGATAAATGG TAAGGGATCATCAAAGGATCTGTTTCTTCGGATGTGGAACATAATCTTCAGTCGATCAAAATCGACACGATTCAGCCATCTACAGCGAATGAACT
GGAAGGGATGTGACAACATGGATTCTGATCAACATTCTGGTTTGGTTTGGCTTCGCTTTCGAACGCACGCACACACAATCGTCAGTTTACTGGCT
CGATTTACTCACTTTGCACTTGCCGTTTTGTTAATATTTAAGTTATCAACGAGTGACATTAGTGAACTATCCAAGTCGCCGGTAATTATCTTTCC
AGTGCCAGCCGGTGGCTGCTGCTGTTGCTGCTGGTTCAGTTGATGCTGGTGTTGCTGCTGGTGCTGCTGGTGCTGCTGCTGTTGTAACGCTAGGA
TCGAACTGCTATTGCTGGAGTAACCTGCGGCGACAACGTTCATTTGATTGCTGTTGTTGCTGGCCGAGGCCGGCTTGAGGACGTCGCCCAAGGCA
TCGAAGCCTTGATAGGTTTTTACAATTCAGACAACATGGTTGTTTGGGGATAGCCATAGCCAATGCACCGTTTTTAGCAGACATTTATACACAGA
GACAAACACATTGGTATATATATATATATGGTAGATATGCATTAACAATGAAGCCGATGAGCCCAGAGGATTGGTTTTGATGTTTGTCGAGTTAG
CGTTGAGTTCGATTGACGTAGATATTCGATATTTCGGTTTTAATTCGTTTTAAGTTTTTTTTTTTTTCATTTTGCCAGCGTAATCATAAAACAC
ACAAATATGTTTTAGCGTTTTGTTGAGATTTTAAGTGTTCAATATGTATTTGTGCCACCAACATTAACATGATACAATGTGAAATTGTTTTTAGT
TTTGATATTTTGATTGGATTTTTACGTTCAGTACATAAGAACATAAGAGAGAGAAAAAGAGAAAAAAATAACATTTACAAAATAAATAATATGAAA
TTGCATTTTATATATAAAGATTTGGGATATATCGATCTCTAATGATTTTTGATATATGTAGGATTAATAATAGGTTGTTATTTACAAACACATGA
CAGACGTAAGATTATTTACAAAAGCTACCAAAGCAGAATAGTTTTTTGTTAATGAAATAAGTGCGTTTTTTTTTAGTGTAATTTAAGCATTATAT
CATCGTAAATACAATACGTCCTGATAGTTATGTGAAAAGTTCAGGTTCAAATAGCAAATAGGGAATCTGACACTAGAATTAGTTGACCTGAACTC
AAAAACGTAAATCAAAAGAATAGTTATCACACAGTTATCACATGAAACACACATTAAATACTTTTTTCCAAAAAATAAATTAAAACTATTTAGAC
AACAACACAGCTTTCTTGTCAATTACGAGACGAGTTTATAGTCGATTGCAGACAAAATAGCTACAAAACACGAGCAGACAACAGAGGGAAAAGCG
TGTTCTGTTTGGTGTGGATGAGCATCTGATGCACTGGGCGCAAGGCTCAGGAGATTTTGGATGCTGAGATAGAAAAGTCAGTGTCCGCTGCAGCA
CTACAAGCCAGTGATGGATCAAGCTTTGTACAAAAACAAAGCACGCGGAGGAACATATGCTTGTGTTTAATGGGTTTGTTTTCGTATTCGTTTTG
CGGCGAGGGTCTGCAAATCTTCACCTGGTGGAAACTGAGCTGCTGACATGGAAGGTGTCAATATCGCTTGCTGTTGCGGCAGTTGCGGCCGGTGT
TGCTGCTGCTGTAGTTGCAGCTGCTGTTGCTGCTGCTGTTGCACATATAAAGCCGCTTGCTGTTGTTGCTGCAGCTGCTGATCCATGAAATTTAT
ATTGTTGCCAAAGGGTGCAGCAACAGATTCAGCAGGGAGTGGGATTTGGGGCAAAGACATATCATCGAAAAATGGATTTGGCAACGACGTCGAAG
CTGTGTAAAATTTAACGCAAACATTCAGAGGATAACCATTAAAATAAATACTAAAAAATAAAAAGAAATTATTAAAAGTCCGAATATGATTCAAA
AACTAGCATTGAGGAATACAGGTAAGGGATTAGGTTCCTAACATAATCACGCATATTTCTAATCCAGTTTTAGAATTTCAAAGACCTATATATAC
GTAAAATGGAATTTTCTTAACTTTTTGTTGAACTTGTTTAATACATGAAATCAATCAGGCATATTAAATTACATGCTACATTTATATCAGTATAA
TTCAAACACATCAAAGTTGGATGATATTGCTAGCATTGTTATTGCCTTTGCCAATTAGTAAACTTAAACGAACCACTCCGATTTTTACTCAATTT
GGAATAGTTAGTAAATCATAAGCATTTTGTTAGTGACTGCATATTAAGTATTCAAATATGTATTCTTAGGATTAGATTGTAGCTTGCAGTTAGGA
ATGAATGAAGACTGTAGACCATTGAGTGACTTACCTGCCGGTTCCGTATTACCAAATACGGATGAGAAATTACTATCGGAAACGAATGCATTTGT
AGCAGCAGCGGAGGAAACTGATGCGCCATTGAAACCTATTTTTGTTTGTTTTATTTTGAAATTTGTTGGTGGTTTTGTCTCAGTTTAGTTGGGTG
TAGTGTGGGCGGTGGACAGTGGGCGATGGTCGTTTGGAAGATTTGCGATTGGTTTGGTTTTCGTAACCGAGGAGTTGTTTTCGGTATCGTTGTTG
AAGATGTTGTCATTACAGTTTCAGTTTGGAAAAAAACAGTGATGAAAAAATGAAGAGTAACAATACATTAGACAAGAATTTAAAAAAAAATCAAA
ACTTACAAAAATAATTATCGTAAATAATTAAATGGATACAAAATATACCATTATGATTTCAACTATGGATAATGATGCATGAAAACTTGTGCAAA
TAGACGTCTAAGCTGAAGTGATAGGAAGACAGACAAAGGGTGAGGGGCGTCTAGAGCGCCTAAAAAGTGCGCTCCTCATTGCTCTGATTTTTAGA
GTACGACAACATAAATACGTAAGATCACTACACTTACACAACGAATGTTACCTATGTACAGCACAAAATAAATTTAACTCATATCGTAATCGCTA
AACAAGAACTTAGGACGAAATAATAAGAAAATTATAACATGCTACCATTATTATGCATCCACAAATTATTGGCATTGAGTGCAGCACCTGTGGCT
CCTACAGCAGCTGCTCCCCCACCGCTGGCGTCAAACATGTCCGCGAAAGGATTGCCCAACTGCAGCAGATCGTCAGAGGCCTTGGTGGCTGCTGC
AGCAGCAGCGGGCTGCGCCGACGCGGCACCGAACAGATCAACTATCGGCTGGCCAGCCTGCGCGGCTGGCGGCGACGATAGAAATGGATTTGTTA
GTGCAGCGCTAGCGCCAGCAGCACCGCTGCTAGTGGGCGACGACACCTTGGACTAACAGGCAGATAAATGGACCAATTAGTTTGTGATTTATACG
TATACTGCTCACAATGAACTCACCTTGTATTGGTTCATAGCGGCTTCCTCTTCGGCCAAAACCTGGGCCTTAAGCTGCTCGTCAATGCCGTTGGT
GGTATCAAATTTGCTGGACGCAGCTGCAGTACCAAATGCCGAGCTGGTAGAAGACAGGGCAGATACAGCGGATTTACATTACGCTGATTACTAA
TGTTTCCCAGCCATCAAAAACAGGTGCAACGCAAAAACCAAGGAAAATCATAGAAAAACAAAAGAAAAGAATGTTAAAAATATATCGCAAATAAT
ACATTGATACATTAATGATAACAGTTCAGTAAATAAAGTATTTATACAAGAACTAAAATAATTTGTAAACTATCCATAATTCATTGCCAAATTTT
ACATAATTTATCTTATTATTTTATGTTGCATTATAAAATTTGAATAAAATGTACAAAATACAAGTGGTTGTTAGTAGGAACCCAATGTTTAAATT
ATGTTAGCATATAACAAATAAAAGTAATATCTAAAAGATAGATTTTGGAGCTTAGAAATAGATTAACAAACCTTGATGACTGCGTAGGAGTATTA
GCAGCGGATACTTTTCGACCCTCAAGCGTGGCCAAGTGCTGCTCCAAGGCATCTAACAACGAACTGGGCGCCTTGGTCAAATCGGGTATGTCACC
CTTGTCTATGCCCACATTCTGGAAGCAGAGAATAAAGCAAATGAAAATGATTTATTACATATGATAAATAGGATAACTCTTACCTCAGCCACTTT
TAAAAACTCTCCAACACGATCCATGCGCACTAAGAACTTTTTGTAAAGATCCAACGCATCGCGGGCATGTTTCTTGTTCATATCGAAATATTTTT
CAAGCAAATTTATGATGCCATCATTGTAGCAAGCAAACAATCGTATGAGATCGCGGAACAAGAGCATAAAGCTCATATTGATGACGCCTGAAAAA
TATTAAAGTCGTTATAGTTTTACAATATAATTTGGAAATATATTCATACCATTAGACAAGTCGTTGGATTGGCAGTCGAACTCCAAAAGTGCATC
CAATTGTGCCTGCAAAACTGGCAAAGTCTTTAGAAGTTTTTCCGCGTTCATGCTGCGTAGCGAGCCTTCCTCTTTGCTAAAATGATAGATTGCGA
AACAAATCAATCAGATGACAATTAAATGTGAGCTGGCGTTACTTACCCCCGTTTGACTTTGCAAAAGTCAAAGGCCATGGCTCGATAGGAGAGCG
ATTTCTCATTCAAATACTTGGCGTAGCGCCGAATAAAGGGAGACATATCGTAACCTGTTGATTTAACAAATTATAGTATTGGTCTCCAACAATAT
AGGTCACACAAATTTTGGACAATGCCAAATACGAAACTTAAGAAGAATGGTCTTTTGGTTAGTTAATTTCGCTCTAAATCATAAGTAAAACAAAT
TTTAGTAACAACCAGTAAGGAATTCAACGCCTATAGCCAAATAAGGAAAGTTGTATCCAATTGCTAATAGCTTCTGTATAATACTCACCCATTCT
GCCACCAGGAACGCCCATGCCACCATCTGTATATAAGGTTTATATTGTTTGATTTTGAATATTTAGTTTGGATAATTGCATTTTTCAGTTGTTGT
TAGCCAGCATGTAGTGTGCGGTATGTAGGTCAGTAAGCAGCGCATTTCGGTATTAATATTTTTGTTTTAGAGATTTTTGTTAAGTAAACAAAATT
ACAAATGATCAAGCCAAACGTTCGCGCGCATTCGCATGAGTTGAAAGAGAGAATGAGAGAGGAATGATCAAAATGTAGGTATTAGTTAATAATTT
GAAATAGGTAAATCGATTGAATAGTCGATGGGTTTGAAACAAATTTGGGAGGCTTAAAAGGGAGGCTTCGTTATACCTTGTACAGTTCCTTTGTC
CAGAAAGGAGCTGAGATTGAATGTAGAATTGCTAGAGGCAAGATATTGCATAAATCGCTGAAAAGATTTAGGAAAAACAATAGGAATGCTGTTAA
ATATTATTTAGATAATTATAAATCGCAATTAAATGGAGGGAACTATAAAAGTTGATGTGTTAAAAATTTAACATTTATTTATTTATTTTTCAGAG
AAGACAACTTTTTATGTCACCAAAAAAATTACTAAGAAATAAAACTGAACGAACAAAAACTGAAAGTAAAATACCACACAACGATATACTTGGTC
AGAGGTCATCCCAAAAGAGTAATTCTGCAGTAATAAGTTGCCATTAAAGGTACAAGAAGGAAAATAATAAGAATCTCATGATGTACGTGACCTAT
TCATCTGTATATTAAATCAAACAAAATAGATTACCTCATTTCGAACGCTTAAATGAAAGTAAAAATGTATTTGAAATACGCCCCTAAGCTTCGCA
CAAACACTAGATTCCGATAAATACACAAATACAAACCTCATTGCCATATGCCATCAGATGATGTGTGGTTATCAGCGACTTGTAGACGACGACCC
AGTTGGCATTCTGTGAACGCTCGATAAGTAAATTGGCCAGATGAGGTATCGACACATTCGGCTCGTTTGTGCAGTGCACCAAATCTGCAATTAAA
TAAAGGTATGAAACTTATATTAACACAAAGCAACCACAAACTAATTTAACATTTTACATTGATTTAAAATAATAAATGAAAATCATTTTATTAAG
CATAGCTTTATATTAGTTTCTTAACGCATATCCATACAGTAGATTAGAAAACAATAAAGAACGTTTTTTTTTTTTGTAATTTTCGGTTAGTGAAC
CATTTGCTCTTTTCCTTAATTTTGTACGTCCAACTCAACTTTACTTTTGGTTGCGATTAACTTTGACTTGATATTTATTTCCCAAGCATTTATT
GGAAAAATCAATCAGATTCGATATAACCGCCGACAACTATTAGTTATTATCCTCTAGATTTATTCAACAGTATATTTTTTTTACGAAAACTTAGT
TCATATGAGCAAAACAACAAATGTTTACATGTTAAGAAGCAACATAAAACTTTAAAAGTCAATTTATCTGTTCCAGAAACAAACAACGTTTCTG
TAAAGATTATTATTATTATAATAACCGAACCTCCCATAAATTTAATCATCTTGTTTTTTGCGTCCCGTTATCGGTCGCGACTCTTAGTCGTTGTT
TGCTTATCTGCGCTTTAAGCTTGCAGCCGCCATTCAAGCTAAATACTGACGGAAAAGTGTCGATGATAAGAGCTGAATCCCATTGTGTCTACTAT
CATGCGCTTCCATTTGAATCAATTCCCATTTCGGTTGGAAAGTGTTTGTCGCCGAGCAAGAAAAAATTGCATGGGATTCGAGGGGCGTTGCACAT

FIGURE SHEET 124

TTCACAAGCCATCGCAGATGTTCGCCGTCCTTTTGCTTCATTTTGTTTGGCTGACGGGCGCCAGGCCAGTGATTCATTTATACATAAATAAGAAC
AAATTTCAATAAACAGTAAATGTGGAAAATTGATCGGTCCTTGTAAACGAAACTGGTGAGTTTCTTAACGAGCACAGTGGCCTGGGGTGTCACT
TTATGACAAAACGTTGAAATCGCTGAGTAGTTAAGACATTTTGAATGAGTTATTTAGTTAAAATTCGTATCCGCCCTTTTTGAAATCTTCACTGA
TTCACATATATTTCGAAAATATTTACAGTGCTCGGATACCAAAAGCGATTGGCGACTTCTGTAGCGTAGTTATCGCTGGGGTCAATTCGCATGCT
TATGCTCTTAAATACATAAATAAATAAATGTGTCGGGTATCGAGACTCCACTGTAGTGGGGGACCATTGATACTTAATTTTAATTATTATTGCCC
ACTTGTGTAGCTGGTTGAAATATTCTGGGATCTTTTCAATCGGTGTAAAGCTCATTAAGTGCTGTTGTTTCCGTGAACACACAACTGGTTTTATC
ATAGGACAAAAGTTGTTAACAAAAGAAAATAGAGAAAATAGGTAGAAGAAATATATTTCATGCTACCTGCTGACGTCTTGTAAAATGTACGGACT
GACTTTTAACTCAGGTTTAATTTATTTAGACTTTTGGTAACTGAATTGAGCATAACGTTTTGGATAAAGTAATCAACTTGAATAAACAGCACATG
TGGCCAAATTTTGGGTTATATTGGAAATTGGTTTGCGGCAACTGCAATACAATGTTTATGTGACAAGTAACGCCCCACAATATTGCCCTCTTTTA
TTCCCATTTACTCGTAGCCATATCTGATGAGTCATCTGAAAAGTGCCAACAAGCTAAATAAAAGGGGGTCAAAATGCGAGCAAAACTAGCCAAAA
AAACAGATTCCAACGGGAATGAATGTCGTTAGGATATGGAGCTCTTTAGAAGTATTTGCAAAATTCAAACGTGTAAGCAAATCCAGCAAATTAGG
GAAGACTCTTGCATAAATTTAACAAGCAATGACACCGTGACAAACACAATCCCTGCTTTCGTAGGCGTTTTAAGCCATTCAAAGCCCCTACAAAC
ACACGTGCACCCGTGGGAAAGTGACGTAACATTAGAGAGAGAGAGAGAGTGTGTTGGTAGAAAGAGAGGGGAGTCCAATCAATGACGAACGGAGT
CCACAAACACCAGCAGCTGAGCCACAGATGCAATTTGAGGGTGGTGGTTTGTGTTTGTGGGACTTTGTGGACCGTAATCAGTGGTTTCGTTTTCA
GAAAACTTTGTGATTTATCGCACAAAAACAAAAGGCACGTGAAAATGGAGCGAGGAAGCCAAGAAACCCGAACTGGTTGCATCTGAATGTTGTTG
CTAAATTACTTTTGCAGCGTACTAACTGTGCCGATGGTTTTTATATTTAGGCTACATTTAAATTTTTTATTTTCTTTGCTAATTTGTTAGGCACT
CCTTACTTTAGTATATTATTCATTCCAATTTTTATTATTATTAAAATTTAAGTTAATTTCTAAACAGATTTTATTGCGACTTATGTTTGCAAATA
AAAATAAATTAATTTTAAAGCGTTACAAAGTAACAATAATATTTTCGTGTGTTTGATGGGTACATTTCCACTAGTAGCACAAGGCTGTGCCTCTT
TTCTCTCTGTGTTATAACAAGGAAATGTAACGGTGATTTACGCAATGAAAGACCAAGAGAGTGGGCAAGGGAAAGAGATAGACAGGGCAACTCAC
AGTCCAAGTGCTTCTTCTTCGGGCCAATGCATTCCTCCGTGGTGGCCTTGCAAACGGACTTGGCGAGTCCTTGGCCCGCAAGGCTGTGACGGGCG
GCCAGCAGCCTGTCGTTGATCGTTTGCCCTGCCATGGTCATGATGAAGCTGTTGCTGTTGTTGTTTCTGCTGCCGCTCGCTGGTTTTTATTTACT
TGATTAATTTAATTATGCACCAAAGGAGCTGACCACACCGACACACACACACACTCGAAAGCAGATACAGAGAGAGGGAGAGAGAGACACACACA
CACACGCGTATGGGGCGAGCGAGAGACAGAGAGGTATTGATTGATTGAGAATATTTCGAACGGAAAACTCTGCTATGCGAGCCTCACGATTAAA
CTAACAGTAAAGATTTAGTGGTTCCTACGTCACAATCACTACACAATTTATCGCCGCGGTTTATGCGCTCTCTAACCGGTGCCTAACGCTGAAAC
GCGATTTTTTAATTCTCTATTTTTCCTCTGCCACAAATCGATAATGGCGACTGGCAAATGGAGCGAGCGTATGAGCAATGTCCTAAAGCGTCCAC
AAAGTGGAGCTAACGCGTGCAATCGACTTGAGTTTACGGCGTTAGGTGGGAAAATATCGATTGCCATAACGTAAGCGAATACGAAATAGCTGAAC
TTAGCTTTTACGATGTGTTCATATAAGTTCTGAAAATAAAAAAAAATAATGATAAATAAATAAATAAAAATATAAAATATTAAGATACTATAAAT
AAATCTTTTTTTATAACTTAGCACTTAAAATTCCCCAACAGCAGTTAAAAAGTAGCTAGATTTGTCGGAAGTGTAGCCAAACGTAACGTAAGCTA
AGGGGCTGTCAACAGGAATTTTTAGTTTCGAGTAGGCGGTCATACTGGTCATTAAAATAAATAAAATTATACTAAAAAACAGTAGTTAGCACAAT
CAACAGTCTCGTAATAAAATTGTAAGATGTTGAATGGACAGATTGCACACAGTTATTTGGAGAACTCGTGCACGCTGATCATACCCCGCCCGCCT
GTCCTGAATCAGTCCTCAAAGTCGGCCCAGCCAGCAGCAGCTGCTGCTGCTTCTTCTTCCGCTGGTGAGGAGTTTGGTCAGGAAGCGGGGTCGGG
GTTGGCGGAAGCGGAGGCGTTGCATGTGGATCGCATAAGAAACTGCGATATATTCGTTGACGCGCACGATCTTTATTTCTACGCAGATGTTAAGC
TGTACAAGTGAGTCACATCCGGCAATCTGTCGTGCCCATGGTGGGCCATGGTGGCGAAATTCCAGCGATATCATTGCGTACTTGTACTCCCTTTT
CGGACAGATTCCACAGCCGTCGCACCTTCGACTTGCGAGAGCTGAAGACGCTGTTGATAAAGTTCAACACGACAGAGAATCACTACCAAATTTGC
CTGCGCTGTCTGCCCCTAACAGCGGGTGCCCAGGAAGGACCCGGTGGAGAAAGAGGCGGAGGCGGTGGTACGGGGGATGCAGCCAA
(SEQ ID NO: 232)

Exon: 12766..12256
Exon: 9679..9537
Exon: 9082..9007
Exon: 8671..8639
Exon: 8414..8312
Exon: 8246..8125
Exon: 8067..7874
Exon: 7808..7672
Exon: 7263..7149
Exon: 7082..6833
Exon: 1475..1001
Start ATG: 12391 (Reverse strand: CAT)

Transcript No. : CT8341
TTGTGGCAGAGGAAAAATAGAGAATTAAAAAATCGCGTTTCAGCGTTAGGCACCGGTTAGAGAGCGCATAAACCGCGGCGATAAATTGTGTAGTG
ATTGTGACGTAGGAACCACTAAATCTTTACTGTTAGTTTAATCGTGAGGCTCGCATAGCAGAGTTTTCCCGTTCGAAATATTCTCAATCAATCAA
TACCTCTCTGTCTCTCGCTCGCCCCATACGCGTGTGTGTGTGTGTCTCTCTCTCCCTCTCTCTGTATCTGCTTTCGAGTGTGTGTGTGTGTCGGT
GTGGTCAGCTCCTTTGGTGCATAATTAAATTAATCAAGTAAATAAAAACCAGCGAGCGGCAGCAGAAACAACAACAGCAACAGCTTCATCATGAC
CATGGCAGGGCAAACGATCAACGACAGGCTGCTGGCCGCCCGTCACAGCCTTGCGGGCCAAGGACTCGCCAAGTCCGTTTGCAAGGCCACCACGG
AGGAATGCATTGGCCCGAAGAAGAAGCACTTGGACTATTTGGTGCACTGCACAAACGAGCCGAATGTGTCGATACCTCATCTGGCCAATTTACTT
ATCGAGCGTTCACAGAATGCCAACTGGGTCGTCGTCTACAAGTCGCTGATAACCACACATCATCTGATGGCATATGGCAATGAGCGATTTATGCA
ATATCTTGCCTCTAGCAATTCTACATTCAATCTCAGCTCCTTTCTGGACAAAGGAACTGTACAAGATGGTGGCATGGGCGTTCCTGGTGGCAGAA
TGGGTTACGATATGTCTCCCTTTATTCGGCGCTACGCCAAGTATTTGAATGAGAAATCGCTCTCCTATCGAGCCATGGCCTTTGACTTTTGCAAA
GTCAAACGGGGCAAAGAGGAAGGCTCGCTACGCAGCATGAACGCGGAAAAACTTCTAAAGACTTTGCCAGTTTTGCAGGCACAATTGGATGCACT
TTTGGAGTTCGACTGCCAATCCAACGACTTGTCTAATGGCGTCATCAATATGAGCTTTATGCTCTTGTTCCGCGATCTCATACGATTGTTTGCTT
GCTACAATGATGGCATCATAAATTTGCTTGAAAAATATTTCGATATGAACAAGAAACATGCCCGCGATGCGTTGGATCTTTACAAAAAGTTCTTA
GTGCGCATGGATCGTGTTGGAGAGTTTTTAAAAGTGGCTGAGAATGTGGGCATAGACAAGGGTGACATACCCGATTTGACCAAGGCGCCCAGTTC
GTTGTTAGATGCCTTGGAGCAGCACTTGGCCACGCTTGAGGGTCGAAAAGTATCCGCTGCTAATACTCCTACGCAGTCATCAAGCTCGGCATTTG
GTACTGCAGCTGCGTCCAGCAAATTTGATACCACCAACGGCATTGACGAGCAGCTTAAGGCCCAGGTTTTGGCCGAAGAGGAAGCCGCTATGAAC
CAATACAAGTCCAAGGTGTCGTCGCCCACTAGCAGCGGTGCTGCTGGCGCTAGCGCTGCACTAACAAATCCATTTCTATCGTCGCCGCCAGCCGC
GCAGGCTGGCCAGCCGATAGTTGATCTGTTCGGTGCCGCGTCGGCGCAGCCCGCTGCTGCTGCAGCAGCCACCAAGGCCTCTGACGATCTGCTGC
AGTTGGGCAATCCTTTCGCGGACATGTTTGACGCCAGCGGTGGGGGAGCAGCTGCTGTAGGAGCCACAGGGAATGCCGGTGATGGGACAGCCAAG
TATGATGGGGGGGCAGGCAGCAGCCCCTTTGACTGGGGTGCAACCGACGATGATGGCGGCGCCGCACAGTAATGCAACGGGCATCATGCAACCCA
TCCAGCCAACGCAGAATGGCAGCAATAAAGGCGTCCCACTCGACCCATTTGGTGCGTTATAAGCGGTCCAGAAGAAGCTCATACGTGCAACCCAC TCACCACTCACTCACTCACTCAGTCTAAGCGCTCTAACCTCATAGACGGAAAACAGAAAACACACTCACAGACACAAATGCGTAATGAAAAATTA
AATATACCAATAGCTCTATATATTATATAAACGTGCAAGTGAATATTAAGATCTTGAAACTGTTTACACGATGCTACAGAAATCATATATAAAGT
TTATGAAAAAAACGGCAGCAATAGCAAACACAAATGAAACGGAAGCAGATAAGAAAATTATATTATAAT
(SEQ ID NO: 233)

Start ATG: 376 (Reverse strand: CAT)

MTMAGQTINDRLLAARHSLAGQGLAKSVCKATTEECIGPKKKHLDYLVHCTNEPNVSIPHLANLLIERSQNANWVVVYKSLITTHHLMAYGNERF
MQYLASSNSTFNLSSFLDKGTVQDGGMGVPGGRMGYDMSPFIRRYAKYLNEKSLSYRAMAFDFCKVKRGKEEGSLRSMNAEKLLKTLPVLQAQLD
ALLEFDCQSNDLSNGVINMSFMLLFRDLIRLFACYNDGIINLLEKYFDMNKKHARDALDLYKKFLVRMDRVGEFLKVAENVGIDKGDIPDLTKAP
SSLLDALEQHLATLEGRKVSAANTPTQSSSSAFGTAAASSKFDTTNGIDEQLKAQVLAEEEAAMNQYKSKVSSPTSSGAAGASAALTNPFLSSPP
AAQAGQPIVDLFGAASAQPAAAAAATKASDDLLQLGNPFADMFDASGGGAAAVGATGNAGDGTAKYDGGAGSSPFDWGATDDDGGAAQ*
(SEQ ID NO: 234)

Name: synapse-enriched clathrin adaptor protein LAP
Classification: chaperone
Gene Symbol: lap
FlyBase ID: FBgn0026210

Celera Sequence No. : 142000013384695
TTAAATGCAGGTGTGCCACAGGGTTCTGTCTTAGGACCTACATTGTTTAATATTTTTACACACGATATTCCACAAGCTACAAACTGTGTACTTTC
ACTGTTTGCTGACGACGCCGCTGTCTACAGTGCTGGTTTCTCGTACAGCGAGATAAATCAATCCATGCAGAGTTACTTAAATGAATTAGACATAT
ATTACAAAAAATGGAAAATTAAAATTAACCCTAATAAAACGAATGCTATATTTTTACAAAAGAAGGAAACCTCGTTATCTTCCTGATAGACAG
TTGCGAATACTAGACTCTCCAATACAATGGGTTGACAACATTCGATATTTGGGTATAATTTTTGATAAAAAACTAACATTTAAATACCACATCAA
CAACACAATTATGAAAGTTAATAAAATTATTTGCACACTGTACCCTCTAATAAATCGTAAATCTAAATTATCAATATCCAATAAGATCATAATTT
TTAAAACAATTTTTAATCCAATATTAATGTATGGGTCACCTGTTTGGGGTAGATGTGCTCAAACTCATATCAAAAAACTTCAAATATGCCAAAAC
AAGCTATTAAAATTAATAATGAACTTACCTTATTACACAAACACTAAGTACCTACATATAAAAGCAGGTGTACAAAAAGTTCAACAAAAAATACA
ATATTAACAATCTTTTGTTTCAAGTCTTAGTTTTTAAGTTAGTTGTAAGTCAATTAAGGTTTTTCTTCTCCCTTGTTTTCCTTAATAAATAATAA
ATATTGTTATACAAAAAACTAAAAACAGGTCAACTAGACATAATTAATAAATATTTCAGATGAAAGCCTTAGCTAAACACTGTAAATACCTAATT
ATACCATTAGCTTTAATGAAATGTACATATATATATAAGGGATAAAGCACAAATAAATAAATAAATAAAATAAATTCATTACTTACCAGGAGTTT
CTTTTACTACCAAAGCATATAGAATTAATGACATCGTCGAGGGGGAAAGTGCATTTGAAAATAATTTAATAGAATTTATTTTTAACAAAAATAGA
ATTACTAGGGGCTACAATTAAAAGTGTATAATTTATGCATGTACGTAGGTTTACATTTAATTTTTGCACGTTTCGATTTGATTTGCATTTCGGTC
GGCCTCCCAACCGCACTAAAAACTAAAGCCTAGCTATTTACACAGATCGATGCAGAAGTCATAGTTGAAAGTTCATAGTTTCCCCCTGGAATCCT
TCCAGGAGATTGTGCTGCAGCTCCAATTCTATATATCTCTATCTCTGGTTGCGGAAATGCCATGTTATCCGGAAAGTGTGGGGCTATAATGGCAT
ATCGGCAATTGGCTAAAATACTGTCATGGCCGATACTTGAATTTCTGGGTTGGCTGACCCAATTGCCACTGCGGTTTGATATGGTTTCCCGGGCC
ATGTAGTTCTCCATCGGATCGCCAGCCAGAATCCCCTTGCCAAGCATTTGGAAGCTGAATATCCACTCATGACAGCCTTCCAGCAATCGGGCGAT
ATGTAAAGTTTGTGCTGCTGTGCCGAAGGAGTCCGGCGATATTGCTTGGTGGCCAACCACCACCTCAGAAGTAGAAGCTCTCGCACTGCTGCTGC
TGCTGGTGGCGTTGTCGCTGCTGCAAGGCGATGTTGCTGCCGCTCAAGCTGCTGCTGCTGCCGCCACTGACCCCGCCGCTGACCCCGCCAGTGCC
ACCGGCGGCAGCGGCCGCCTCCAACTAGAATCATAAGTGCTGGTACTCGCCCATGTCGTACATGGCGGTCATGGGCATGGCGCCCATCACGCTGT
GCAGGTGCGAATAGGCCACGGCGGCGGTCAGTGGAGGCATTTGCATCTGGGCAGCGGCCGCCGCACTCACGCCTCCTCCGCCGCCGCCGCCACTG
CTCTTGGTGGCGGCGACATTGGCGATATTGCTGGCGGGATGTGGCTGGTGCGGATGGTGCTGCAGGCCTTGCTCGGCGGCGACATGCTGCAGCTG
CTGCTGATGCAGGCCGTTGTTGTTGCCGCTGCTGTTGCCGGGTGAATGCTGCTGCTGTTGCTGCTGCTGCTGGTGCTGCGCACTCTGGCTGGGCA
ACATGCTGCCCTCCATCTCGGAGTCGCTGGAGGAGTCAAGGTGCTGCTTGTCCGTGGAGCCGCTGCAATGGAGATGAACAGGTTGCGTGGTTAGC
GGAGGTTATTGATTTAGAATGCTAAAGCCAGCATAGGCTACTATACTACTATACTTCTACAACTAGCATTAATACATCATATTGAGCACTTCATG
ATCTTTATGTTCCAGGTCTCATCTATCCCTTATGTCGAATTGAAACTATCGCCTGCTCCGCCTGCTGAAGACGTGACCCGTGGCATATGGTTTTT
GGATGTCAGCATCGCTTACGCTAAAATGTGTCAATTGCTGCAACTAATTTAGTGCTGTCAACACACAAACGCACTCCAGTGCATAATTTATTTAT
AAACAAATGACAAATGACAGGGGCACAGGCATTGCAATTGAAACGAATTCCGGAAGGAAATCGTCTGCCGCTCGCGTTTCTATAAATGGTATCAT
GTTCGCCGTTGAGGTGTCGCCTCAGGGAATCCGAATGGAGTGAGGAGCATGCGAGATGAGGAAGCGAGATGGCATGCCCTCCCCGGGGCATTCGG
ATATGAGGCATCTGATTTCAGTCCCAGGATGACTTTCCACATTTCCAGGGGTTTGCTTCAAGTGGGTGCGAGTGCTGCACACCCCCGCTTGCATC
TTAAGTAGCTGACTTTTATTGTTTGTGGCTGAAACTCATTCGAAACTCGAACGCCACTTTGGGGTTAATGTGAGTCCTGCCCCCTGCACTAATGG
CTAATACCCGACCATAACAAGACCGAAACTCGAGCAAATGCCAATCTCCCTCCCGCAATCTCACCCACTCCGCTGGCAATCATCGGCAAAGTGTT
AATCTTGTCGCCAATTGCATGGCCGAGCACAATCAGTAATCGGTTATCAGCAGCCGCATCGCGGAACCAGTTTGCGAAGAAATTGATGACAGCCA
CGAGCAACATCAGCAAACAACATGGGGCACCTCCAGGATTGGACCCACCAAACTTTGCATACCCTACTGATAACGATACTTCTTTCATATACCTA
ATAGTAGATATTTGTTAAACTTGATATGTTACTTGGAATTCCTGATCTTAGTAGCCATTCAAAACCATTCCACTTGGACCTAATGTTTAAAAGCC
TTTAATGATAAAGAGACACTTGGTCACTAAACACATGTCGAATTAAAGGAATTATCGACAAATCCATTTGTCCAGCGAAGCAATCTTCATTGAGG
GTATTGTTATTTGGGGAAGGGGGGAACGAGGCTCGTTCGGGGCAATGCGAAACATTTAAGCGCACACTCGACAAATTTGCGATCTGGCACAAT
GGGACAGAGACGGAGGGCAGGACAGGACCGATCTGATGGCCGGCAGATACACCACTTCCCCAGCTGCCGCGGATTCCGATTCCTCATTTCTGATT
CTCCATTCCCGATTCCAAATCCTCGATTCCGAGCGGGGGATCTGCAGTAGGAGGAGTAGGAGGAGGAGCCCACATACGGCGCAGCTGTACGATAT
CGGCAATCGTGTAATTGTAGATTGTATCCACCGAGTGGCAGCCACCAACAGCGATGGCATGCCATCCACTTCTTGCAGCGTTTGCATGAACTTGA
ACTTGCTCCAGCGATCAGAGGCGCAGTGGTGGAGGAGGAGGAGGAGGATGAGGAGGAGAAGGAGGCGGCGGGCGCGAGACCATGTGACATGTGAT
GGACACTGCTCCCTACTTCCCCAATTTTCCGAAAACGAGTTCGCGCTGTGGACATTAAAGTGACGCTCGTTCCGATCCGCTCCGTTCCGTTCCAA
ACCGTTCGAGGCAAAAATCGATGGCCTAAGCACAGCAAACATGAGGAATGGCCCATCCCAGAGCGAAAAGTGGGGAGCAAACAAAGGGCAGCAGA
AGCATATAAACAATGATATCGAATTACCAGAGTTTCGTAGTTCTGCCCCCCATCTCTGGCGGCTCTGCAACACTTATTAACACATACAAACGGAC
AGCGCCCACTCTTGTCCCGTCCCATCTCCCATTCCCATCCCCATCCCCAGTCCACATCCACATCTACATCCCTGTCCGCATTTCCAGTGATTGCA
TTATAAACACACAAAAATGCCTCGGCTCGGTCTAGTTTGGTTTTACCGGGGCACCGAACGGGAGCAGCGAGTCTCAAGGACAATTCCTGGGCCAG
GAGTGAGTGTCGCATATAGTTTATAACAAAATGGAATGGCAACCGCTGAGGAGCAGCAGGTTTTGGGTCTCCGTCCTCGTGTGTGGTACCTTTGG
CTGAAGGTTCCTCGGGCTTTTCTTCCCGCACATTTCTTTTCATATTTCTTTTTGGGTCCAGAGTTGTGCCCAGTGAGGGGGAATTAATTTTTACT
TGTTTGCCCAATTGGTTTTTTGTAGCCGGGCTCTGTCTTAAGCAGATTCATTAGCTTGGTAATAATGCATGATCGGATTATGTTTAACTGGAAAC
GGAATCGGTGAGGGGTGAATCGGTGGGTTGGGCCACAAACGAGTTTGCCACGTGAGTGAGTTGGTCTATAAAGGTATTTAACATTTTGGCAAGAC
ATCTTTCGCATCGATCTGATGTCAATTGATTGGGAAAATAGAAGAATTGAGAATGGCCCATGACATAACCCCAACTAACTTTCACACGAATGAGT GGAGAACTGGGACTGGACTGTGGCTTCCAAGGAATTCCGTTGCTAATAAAAATTATAAGCCAATAAATCCTTAAAGAAAACAAACAAACAAACAA
GAGGCTCAGGGCCCTGCAAGATCGCTGAGATCGGTGAGATCGGGATATTTGGAGAGATACGGGCAGATCAGGAAGATCGGGAGGATCGAGAGGGC
CAAGGAACAGGTTGAGTTATCGCATTGCGCGATCGGTACACAAATCTCGGGACGTGTGCTCAGCAGGACACCCAACTAAACGGGCAACGGCGATC
CATAAGTGGAATCTGAAAAGGTGTTGATCATAAATTATCATTTAATTTACGCATGTGTGTGGCTGTTGTTAATGTTCGTGGCGACCCTCTGACAC
TCGAAAACGCTCGCTCGAGGATGGGGAACCTGGACCTGGGTCGGTCGTCTCACCTCGGCTGGGGCTTGGGGTTCTCCTGCTCGTCTAGCCGACG
TCTGGCTGGTTATTGTTGGGCATTGTCTACAACTATGTAAGATCCCAAAGATTAACCCAAAGTCCGAGCCCAGCGCTGTCATCGTTATAAGATAT
TTTATTATCGCTCCGGCGAAGATCCCGAAACTCGAAGGTGGAAAGCTGTACGTAGCCTGTGTGGCGTGTGGAGCATTTTATACTGGTCGAGAATT
GTTTTGACAGTTTCTTATAATTTTGTGGCCTTTTAATTGCCCGGCCCGAGGCAAATCGGCTGATTCCTGAGGAGAGCTAATCGCGTCCCCAGGCC
CCCCGCCGATGGCAATCCAACTTTTATGTAATCCCCAAGTCTTTTCAGCACTTTGAGGTTTACACACTTTTCGTGGGAGCACCTAGAGGAAGCCC
CATGGAAAACAATTGCTCAGGTCAAGTCGAATGAGCAGCTAAAGAAGTTTCCATAAAGAAACAAATATTTGTTTTATATATTTTCAACTATTGTA
ACTCAACCCATTGGATACGCAAAGATTTAAGAAAGGAAGTGGAACTGAGAGCACCTGAACTTCACTTGGAGTTTTTTTTCAGGAAATTCGAATAA
AGTAATGTATTGTAAATTACACCACAACAGTACTAATTTCATTTTCTATACCTTTTAGTAATGATATTAATGTAAATAACCAATCATCCTGTTTG
AGTAATGCAATAAAGCAGCATGCCCAGTTCTTCATTTTCGGGAGCTTTCCATACTCCTCGTTCGCACCAGATGAGATCTAATTATTGTCAAGAGA
GTGTACACTTGACACCCACTCCCGGAAAAGCGCGATGAGCGGTTGTCAGTGCGGATGGCAAGCGCCTCCGGGCGATTCCGTACCACCAGCCGGTC
CATCATCACCAACAACATCATTATCAACGCCATCGGAGCACGGATCGGGATGGAGAGGGAGCGGGCATGAACTGGGACAGCAGCGAGATTGGGAA
CGGGAACCGAACTGGCGAACTGAGCACACAAACACAAAGGCGAAGATGTAGAGTAGAGTAGAGAAGAGAAGAGACCCTCCGACGGGCAAAAGCGC
AAAATACATAATAATAAAAACAGAATGTACAATAAAACGAATAAAAATGAATAACGTGCTGGCGGGGATTGGAGCGAGGGACCGGCGGTGGGCAG
CGGGGAGTGCGGGGTTGTCAGGGCGAACGAATAAAGAACACACGCACATTTTGTGGTAACCCGATACCCTGGCCAGCTACCCTCCAGCCAACCGT
GGCATTCGACGAACGCAAAATGATGACGATGTCTGGGGGAGATGCGGATTCGATGGGCAGGGGCTGGGGTAGGGGCAGGGGTAAGGGCAAGGGAA
GGGGAGTGGGATGGACTTGGGACTGGAACTGGAAGTGGAACTCGGACTGGGTCGCCTCGGTGGTGAATACATACATGGAGATGCAGGGGCAGGGG
AAGCTCGTCTGCAATTGGGACTGTCTGTGTGCAAGAGAGGGAGGGAAGAACGCTTAAGGTACTGGATTCCCGGAGAAATGGCTCATAATGCCTGG
CAGATCAATCAAATGGCCCCTGAATTCTTCTCTTTCATAACGAGGATTCCTTGAAACAGCAAAGAAGCATCTCTGTCTTGGGTTAGATATTAACT
CATTGGTTTAAGGATCGTTATTCTGCTAGAAGGTTTGGCCATATGGATGATATCTTGAAATACTAAGTTATATAACAAAATTTAAGTTTAGGACA
ATGTTGAAACAGAAGAACATTTTGAAAATTTTTACATCCTTAATACAGGTATATAAGATTTGTAAAATTGTATCTTTTCAAGTATCTTTTACGAA
TGTTTGGCATTTGGCTTATGCTACCTTTCAACCTGAGGTCATTAATCGGATATTTATGTAACCGAAAGTCCCAGAATGCCAGAATGCTATTGTAA
AGGTTGGAAAGTTGATAGGAAAATATCGGATTACGGCTAGATTGTTTGGGTTAGTTCTTCAAAACTTTTCACCCAACTTTGCATTAAACAATGCG
ACGGAAACCCGATATTGTTATTGGCAGTATTTTCGAGCTCTCAGTAAGCAGTGCCCTTCAATTCAATTCAAAATTTACAAAATTCTTCGTAAAGA
GAATATGCACAAGACCTGGAATAAGGCGTTCCACAAGCGCAAGCTGGTGAGCTCAGAGCGTAATAATGCATCAGCATGCGAAACTATTCCCAATT
CTTCCAGTGGAGGAGCGTGTCCAAGCCCGGAAAGCTGGTGTACTACATGCAGCCGCTAATCGAGCACCTGTTCGACACCTGGATGCAACCACTGC
CCTTTCCGACGCTCCTCAAGTTCATCTACAGCTGGGTGCTGATCTTCTTCATCATGATTCCGATGCTCTATCCGCTGCTCGTCCTCCTCTCCTAC
TACGGCATATTCCAGTACGCGGCGGAGGAGCACTTCGGACTGAAGACGCCCGAGAAGTGGGACCTCCTGGGCGCCGCCGCCAGGCTGTGGCACTT
CGAGGTGACCAACAGGAAGTATCTCCTGTTCGTGTCCATGTACATTGATCGCTACCGAGTCGTTTTAACCGCCATATCTTCGACAGTCGACTATA
TGCGCATGGCTCTGTGGTTCGTCTTCAACTGAACCAACAGCCGGAGTCCTTCGATCCCTACTTGCGAATCCCGTTTGCGGGGGAGTTGGCTTAGT
AACTGCCTTTGGAGTGGATAATTTTAGGTCTTTGGGTGGAAGTGTTTCGTACGAAGAACTTAACCAATTAAAAGTTGAGCTGTATTCTATTCTGT
AATTCTATGGGTATGGATATAGGATGAATCGTTTGGTTCCATCTACCTAGTCTTTGAGCACTCTGTCCTCCATTCTCTTTTGGCCCAGCGAAGGT
AGTGCCTATGCAAACAATAACCACTTTGCCAGTTGCTGGGCCGTTCAAAGTGCCGCTTTGGATTCAGATTTGGCGCCGTTGTGGTTTGCTGGCTG
CCACAAAGCTGCATGGAACATAGATACACACACCCTCATGCAAAAGTAAAAAAACAGAAAACGAAAAGAGCGCAGAGGAGAGGAGCAAAGCGGAG
TGGGGAGGGGAGGGGAAACAATATGAAAAAGTTAAAGTAGCAGCACACTGAGTTGCTCATCGAGGCAACAGCCATAAACATATATCAGGTTACCT
CCAGGAGGAGCTGGAGGTATGCAGCTACGCAGTCCATAGTACGGCAAACTATCGCAGAGAACGAACGACGTGTATCTGTGAGATACTTTCGACGA
CTGGCCGTGCATGGGTGTGTGCGCGAGTGTGTTAGTGTGCCTTGCGGTTGCCACGGCATCCAATTTATAATATTTTTTGCATTATTTCTGTTTTA
CCATTTTTTATTTCCATTTTTATTACGACAATTTCTCGCTTTTCGCCTGCCGTTCGTGCGGCGAAACTGGGCGTAAGTGATATACCATTTAGCAT
AATGGAACTATCCTGGCGAAAGTTTGGGACTTTTGCCAATTTGACCCGGCTAATGATTGTCCCACCCAACTGGAATGGCTAGAAAGACAGCGGAA
TGGCCACTATCCCATTAGAAATTTGAATTTTCACTCTCTCGGCTGTTTGCACTTCACATGACTTCCAGCCGGATCGCAGGACAAACAAAAGGATG
CTCGTCGGCCAAAGGATGTTTTATGTTTGAGAATCTAACTCCTATCTTTCGAGGATCTACGCCATCCCTCTGCCTCAAAGTGGAAACATCCGAAA
GGAGTGGCTCAACTGCCCGAAACTATTTGCTTAAGCGGAAATGCAGATGTTCAGATGTTCAAATCGGGTGGCGGAAGGGAAGTGGAGGGAAGTGA
AGTGAAAGGACTGGGGTTTTTAATTAGTGACGAGGCCTGCGAGACATATGCCGGAGATATGCGTGTACCGAAGGCAAACATCAACAAATCAAATA
AAAATACAAATAAAATAAATATATAGGATCGTTTTGGAATCTGGAACAACATGTTAATGACTTTGTCAGCGACTCTTTCTTTCTTTCCCTCCGCA
TTTAACCACATCTCGTGTGCCAGTTGCGTGTTGTCCTTGGCACTAATTAGCCAGCCCCCCCATTGAACGCCCACCCACCCGATACCGCCCACTCG
GCGACCTTGAAAGTAAATGCCGTCAGCTTTTGTAATTGAAATTTTAAATGCAAATTAATATATTATTTTTTGCGGTGCCTTGCACGCGCTGACAC
TTGTCAGATGTATCGCAAATAAAGCATAAATATACTCGTATGTGCAGATGCCCCCCTCCCCCTGCCACCCGCAACTCATATGTACGTATGAAACG
CTGATATAAGCAATCTAGATATATCTATCTATCTTTGGAGTACGCCCAAAAATATCTCAGTTGTCCCCCCCCAGTGAATCAGACGGGGCAATCAG
CTTAGATCTATAGTAATTAGTGATTTGGTGCAACTCACTCTTTGTGTTCGGCAGCTCGATCTCTTTGTCGTCGGTTCTTGAACCAATTGGAAACC
TGTAAAAGCACAGAAATAGCTTAGATACATTTGTAAGCATTCGCAAGATTCTGCCCCATGATTAATGGGATGCAATTAACATCCTCTGCGAGGAA
TTTCAATTGAAATTTGTCAAAAGATGCGTTTGACATTTATATTTCACTTCAGCCGCTCGCATCTCTGCTCTTTGCATCTTGGCATCTGGGCATTG
CCATCGACTCACCTGCGTGGTGGTCAGTCCTGTGGCCTCGGCCAGATCGCGTTTCTCCCGCGGCGATGGATACGGATTGTGCGAGTACCAGTCCC
TCAGTACGGAGCGCGATTTTTCCTGCGGATGAAAAGGTGTCATTTTAATCAATACGTATGGAGATAAACCAATTATAAGCCCCTAAAATCAATGT
TGTCATATATCAAATTGTAACTAATATGAATACGAGTGAAGTGAAAGCACTTAATAGTCAAGCTTTTCTATCTATTAGAAACATATCTAAGAGCG
AACAAGAACCTACAGTTCTCTTTATTTGTGAATTATTTTGTTTTGCGAGATCTTTTAAAATTAATAATAAACCTAGATTGTATAGAAAGCAAAAG
GGTATTCCGTTTACTACCCAACTGTGTCAATCCTTTTTTCTTTATATTCCCAAATTGCGTCAAAACTGGATGATTCGTGGGCGTAACTAGGACT
CAGCCCACATTTCCGCGCGCTACTTGAGGCAACTGTAAGCCCGTCGAAGAGCAAACAAAGCGAATCCCGTCCAGGATGTGCCTCCGATAAGCCCG
AAAGGCGTTACCCCCAGCGCAATCAGGCGGTTCGCAGTCCATGCAATCAGACAGGCGAGCGGGCATTTGTACGATTTCCGCGCTTGCCACAATTA
AAGTGGAAAGCGGCCAGGACGACGTGGAGCTGGTGGCCCGAACTCACCTTAAAACAGTAGCTCGTCTCCTCGCCATCCCAGATGGTGCGGGGCAA
TGGAAATTTACGGCGAACACGATATTTGCCAACAGCACCCAAGGGTCTTCCGCGCAGTTTTTCGGCTTCCACATAATGCGCTACAGTCGTGGAGA
AGAAAGGAGGGGGAAGTCAGTTTGGTTGCGTTTCTGGCCCCAAAGATTTGGGCTTGGGCAGCGCAGCGGGCTGGAGGTTTGGAGGATCGGGGGGT
TGGACGGTTGGACGGTTGGAGGCTCACCTTTCAACCACAGGGCCTGGAGCTTGGCGTGATTCTGGGCCGAGAAGTGGTGATGCTCGAGCAGGCGG
TACAGCTCCTTGTATTGTCCCCGGTGGAATGCGACGACCGCCTTGGCCTTCAGCACGGACTCGTTCAGCTGCAGCTTATCACATTGTGGCAGCGA
CCAGAGGAAGCGGCCCAGTCTTTCGATGTTGCCCGCCTGCTGGAGAACCTGTAGGTGTCCGGGTAAAGATATACATTATAATGTCATCTAAATAT
TTCACTAAATCTATTGAAGCTATCATGACTAATGGTGATTTCCTTCCATAACTTATTCTTACACATTCTACTTATAGTTTGTGATTACCTCGCAA
ACACAGGCCACCTGCTCCTGGGTGAAGCCGAAGCTGGGCAGGTTCTCCCTGCCGCCGGAGCCTCCACCACTGACCACTCCGCCGCCGCCGCCGCC
GTTGCTGCTGCTGTTCAGATGGAGGCCACCGCCTGCTCCGCCGCCGTTGTGCGCCATGATGTCCAGAGTGCTGTTGTTGTTATTGCTGGTGCTGC
TGTTATTGTTGTTGTTGTTGTGCAGGGCCACCGATCCGCTGAGACCGGTGGGACTATAAGGAGGCGTGTGACGGGCGGTGAGAACGGCAGCCGCA

FIGURE SHEET 127

TTGGCCGCGGCCAAGTCGTAGAAATCTGTGGCGGGATGCTGTAACATTTTCTGCGGGAATCGGTTGCCTGGCTGGATGTTGGTGGGGTGGATTTC
AAGGACACCGCTACAAGTTGCAGAAGGGATCGATCAGTTGAACTGGTGAATGGTGTAACCTAAACTAGTAGTTGCCTAAATCTTTGGTGTTTTGA
GCGCTGCAATGATAAAAGTAATAGAAAATCGCCATAAGTTTATGTTTGCATATTGAAAATACAAATATACAATGTGTGTACAGGCTTAAAAAGCC
ACTGTATGCTAAATAGATAATATCTGTGTTGCTTGGAGCCATAAAAACCCACGATTGCAACACACAATTTTAGGAAAAACTCGCGCCACATTCTG
CGTTTAGTAATTAGCCCCCTAGTATTCATCTTTTTATTACCCCGCTCGATTAATATTTAAACAGCTCTCTAATTGAGACACATTAGGCTGTGAAA
ATCACCATTGAATGGCAAGTGATTCGAACAAATGCCAAACAAAACAAGCGCGTCTGCATGAGTTTGCCATATTCATAAGCATTAGAGATCCAAAT
TCAAATCCAAATTGAAATCGAAATCAAAACAGAAGTGTACAGTACAGTGGAGAACCTCGATCCGACCCCATGTTGTCAAACATGATTAACCGAGT
CCGGGGGCAATTATTAATGCGGCATGTTCGATGCTCGATAATCGGAAATACGGCTGGCCATTGCCATCGTGGAGCTCTCTAACCTGTCCGCACCC
AACCGACCAAGAGATCTCTTACGAAAATAAACTCTTTACACAATATAGTACGTGTATATGGGGCGCATGGTGTTTCGGTATTCCTCCGATTTCAC
ATTTCACATTTCCCATTTCACATTTCTGTATTCGGTTCTAAGAATATTTCTAAAATTACCAGGCGGCAGCGACGACGACGACCATGCCTCCGCCG
CCATCGCGAGGGAGTGAGCGAGAGGCGCGAACGTATCCCCCAGATAGAATATCTATGAGGTATAGACGATGTTTTCACATTTCAAAACAATGCAA
TCGATCTGTCCGAATAAACTGATATATGTAGATATATCAGCCACAGATATCTGCGTATCTAGGCCCCTCCCCCCCCCCCCCACAAAAGCTAAAG
CTAAAGATCGGGCTATATGCACACTGATTCTCGTGTATCGGAGTCGAGATATTCTTGGATCTGCTTTCGGTTTCAGTTCTCGTGTGTGCCGGCCA
GATTATATATACAAAAAAACAAGGAACAAGAAACAAGAAAATAGAGATTCGTTCTGGCTGCCGCTGTAACGAAAATACCAACGCCAAGTTGGCTG
CTCTTGAGTCATCGGCCTAGGCCAGATCCCCCGCAGCCGCCGCCTCGCCGAAGATTTCCATCGATTCGATTTCTTCAGCTCGCTGCGATTCTTCT
TTCTCCGCTGCTTGTATTTTGTATTTTCGATGGCCTGTTTCATGTTTGACGCAAGTAAACAAGCAAAATGCGAACGTGAAACGCAATACGCGATA
AATTTTCAATCTGTTTTGGCCAACAGCAATCCAGCAGTTCAGTTCACAAGTGGATAATATTCGATGGACACAATGCATTCTGGACATATTGCCGA
ACTATTAGAGCCGATTTACGCCTCATTCGATCGGATTCTGAGCTCTTCAGCCACATTGGACCATAGCATACTGGCATACCAAGGTTTATGGCCCT
GTACCGTTGCACGATCCCAAGTGGAAGTGGAAGTCCCTGCCCCAAAACGAAGAAGAACACCAGCAGCTACGACAGCAGCGGCCTCGAAAGATATT
CTATCTGTATCTTTTGGCTGCCTCTTCAGTTCGCCTTGTGGGAGATCTGTTATCGCGCGCCTGTAGCTGCCTGACTTTTGTGGCATTCGAATAAA
ATTAATTTAATTTATTTTACAAATTCTGTAATTTATTATCTATTGGTTTCTGTTTCTGTATCGTGTTTGCCCCATTCCCCTTCCCCTGTGCTTCT
TCCTACTTTTATAAGATTTTAATTTGAATGTCGTGGAATCCCTGGAAATCTGAAAGCGGACACCTAACTCTATTGGGCTGTTAATCAAATTGAAT
TGTTCGAGCTGCCGTGGCTGCAAGCGTTGTTCGCCTAATTAGTTTGTAATCAAAGTCAGCTTACGATTGACTTGTTGATGGATTCGATTCAACTC
GCAGGGCAGTTCCAAAGCCCTAAGTCCTAAGTGCACTTCGGGAACTCTGCAGGTGAAGTGTGCCCCAGCTCGAGGAGCACCCAGCTCAACTTGGA
GCATGGTGCCATCGCAATCGCAAAAAGCACAAACAGTGCGCCTGTTTCTCGCGGCTAACACCGAAATCATCTGCTCCGGCGTCTGTGTTTATACA
ATGTAATCGAATGGGAATGGGATTGAGACTGTGACTGGGGATTGGGGATTGGGGATTGGGGATTGAGGACTGGGAAGACGTGTGCCATGCAACCT
GTTGTGGGCCAGCCCCCGTTCCGGGTAATTCGAACGGCTTTCTGGCCGCTGGTCGGGATTAGTAAGCGCTGCTGCTGCCAAACGGTCGAGACAAT
CGCTGCTATCCGCCAGATACTATTTTTAACATTTTCCGTTTAATTGCCGCGTGAGGGAGCTACGCACAAAGAAATCGAATAGAGCGCGGCGCAAT
GAATGAAATTTGTCAATTTAATGGGTTGCACACACATGTGTCTCTGCCTCCGCAGCCGAATGTATCTGCATCTGCATGTCGGCTGCTTTTCGCCT
TGCTGCGCCGCATTTGCCAAACTTTGAATGAAACTGAAGTGCACTGGTCGAAAGTCCCGCCGGTGGGGAGCTCGTCCCCAAATTACGACGGATTC
TGCACGCCGGTGCGTAAAATGATCAAAGCTGCTGCGGCCAAACTTGCGTATCTGTATCTGTTTCTGCCCGAGTCCCGAATCTAGGCGAATGGAAT
GCGCAAATTTGTCAATTTGGCCACTTCCGAGATGGAATCCACATGGCTGGTATCTTGATGATCCGAAATAGGCAACCAGAACCGTACGCAACATC
TGCTCCCATCTCTGCACTCAATTAATCATTCGACTTCTGACGACAAACACGCGTTGGCCAATTCGTTTAAACGCTCCCAATCCCCCGAATATCGC
AAATATCGAATTTAGCCGGACAAAAGTGGGTCCACGCCCACTCATCCTCACACGAAGTACAAAAGTTGTCGGCCAAACAGTCGCTATAGTTAATA
ATTTCATAAATTTTGTGGCGAGAAACGAAATGATAAAGCCAAATGGTTTCATAAATAAACACTGTGTGCGTTGGTTTCGAGCACCAAACGGTTGG
AAAGCCTTTGCGATGAATGAATGACAACTGGAAACTACTTTTCCTTTGGATCAAATCCATCTCATATCTTTTCCTCTAATTAATAAATACATCTG
AGGTGGGTGGCCGTTGAGTAGCCAACTTGGAAACGTGGAAAACTTAGAAAAAAATTGAGCGGTGAATAAAACAACAGAATTTTTCTTTTGGTGT
GTAAACAAGTTTCCTTTCCAAATATAAGTGAACATGCAATTCCCGTGCTTTTGCCTTCGTTTCGATTCCCTCAGAATTGCTTCTCAAGTGCCTCG
AGTTGGTTTTCCGATGGCTTTTGGCCATTTGGAATTCGCCAATGCCACGCCGCCAAAAAGCGAAGTGCACTTTGGCTCTCAGCTCTCCTCATTGA
AATCGGCAAAACGTTGTGAATCTATGGACTTCGATGATAGATTGATCCATTAGAAAGCGGATAGAGATACGCCGTGACATTTATGGACTGCATTA
ATGTTTTCGCTGCACACGCTTTAAAGGCTATTTAAAGCACTAAAATATATTTTTAAATGAAGTCTTCAAATAGGCAAAGTGATTGATACTTTCTC
AGAGAACTTTAGGCTTTTCTAATCAAGAATAACGCTTTGCTGTAAGTTCCATTTTAACCGTATGGGATGTTTAATAAAAGGTCTATGTTCTATGA
TCTTATCTATAGGTGATAAGTGATTTCTTGAACATGTGGTTAGTTCTTCTAAGGCTTAGTTTGACCTATTGAAATTATTATTTTTCTGAAACTTT
TGTATATATTTATGGTTTTATAATTTTAAGGTTCCAATATGGAAATGTATAATCTAATATTAGCTATATTTATTCACATAATCGTCCCGAAATTT
ATCATAGTTATTATATCTCCTTTTTCAAGTATCAATGCCAATTTTATTTTAAATTAATCCCCCATATACCATTCGTTTTTCTTATTGTGAAAGAA
TATCCGTCCTACTTATGCATCTACATATATTTTTGCCATGGTTTCTAGTGTTCCACAGTAAACTTTTGCCGTCGGCAGCATGAAAACTGAATCTC
GCTGCTCACCTGTATTTTGATTATTTATTGTTGATACGTATCCGAGTTTGTTAGTTTTTGTTTGTTACTCTTTGTTTGGGTTTGTGCCTTTTGCC
TTGGCTTTCCGATTCGACTTGTGCTATATCCGCAAATGTTAGAGTTGGCCAAGAAGGCGCTGATTTCGGCTGTGCGGCATTTCCTTGATTTGCAT
TTTGGCCAAACTCTTCAAATCGAAGCCATGTGCCGTTCGCGCACGCACACACTCTTAGTCGCGATCACACTGGGCACTAACTAACACAAGCTTGC
CGTTGAATATTGCTCATACGCACTGTGCGAACACGTGTTGCAAATTACTTTTCGCGAAAACTTCGCTGTCCTGCGCGACTCGGACAAATTGCACC
TGCAAATTTGGTGGGCAAAGCTGCGACGACAGCACTGAGGCAGTGCCAACAAAAAATGGCCGCCCGCGGATTGATTAGCTCAATTTTGCTCGCTT
TTCTCTCGCTTCGTGTGCGTTTATGTGGCGCGATACTGATGCGTTCATTCAGGAAACACGCAAATTAAATATAACTTTGTGCGCGGGACGTCAAA
AGACCGCCGGATCCGGCCTGGATTACTAAGCGAGCGACGTGGGTAGAACGGGCAGCGAACCGCACGCGACGGAATCTCGAAAACAACTGAGAACT
CTCCGGTTCTCAAACCTAATCGAACCGAAAACGGCCGAGACAAAAGGCAGAAAATGGTTGGTGCCGCTGGCGGTGTGCGTGCGCCAGAGCGAGAT
GGCCGACTGGTCGTGCGAGTGTGTGAGTGAGCGAACACCAAGGGGGTGAACTGCACAGTGGGATGCACCGACACTTTGTGCGTCACTTTCCAAAA
ACGTTATAGGAAAATAATGGAATCAAGTGAAGCGAGACTTACATTCACTGACTTTTATAAAGTCACTGGGCACACACAGTTCATGATTACACATA
TATGAACTGATGATAACTCAGAATTCACTACGTTTTAGTTGTTTTCAATATCTTGCCTTTACAAGTGTTTTTATTTTTATTCTATTTTATTTTAT
TGTATTCTAATGTTTTCGTAGTAAGACATAGTACATTTTTCCGTTATTATATGCTATTGTATCTTCAAAACATTAGAAAATGGTTTTATATATTT
TTAAAGTGGCTTACAATTAAGTTAAGTTAAGTTAAGTTAATTGGACAAATATTTTTATAAACGTGTAGCCATTGAATTTGACACACGGTGCCAAT
CGACAACAGTTTGACAGCCACTGCGAGAGGGGCAGCGTGCGAAAGAGCGAGAGAGCGCATAAACAGGTTGACCGAAAGAACGCCCCCTCGGCTTA
CCTGTTCGCACACACACACACACACACACACACACATAGATGCCCTCACGCACACCGGCGCACTGGAGGACAGCAACGTGCTGATTGGTCAGCGG
AAACGCATGCCAGCAAAAAGGCATGCGCATTGGGCGCCATATTGAAAGGCGGAAATCGGAGGTGATTGCAACTGCATCGCTGCTCCTCCCCAGGA
ACTCCTCATCCTGGCTGAAAGGATGCCCGGTGCAATAGCTGCCATCCTACAATGCCGTTTGAATTACTCACCGCAATAGTTCCATGCATCTCTCG
TATAATTGCAATTACTGGCCTTTTCTCATATTCATTCACTCCACTTTTTTGGTTTAACTCAACCTTGTGGTCCTTCCACATTAGTGCGGTTTGCA
TTGTATTATTTAATGATTCCGAAGGAGATGAAGCCGTTTGGTAATTGAAGCCAACTAATTGTGTTAATGATTTACTAATATATTTAGTTTACTAA
ATATTTACTATATACACAGGCTCCTTTCGTCTTCAAGTCCTTGTTCATGATAACTGAAATAACTTGAACCTAATTTAATTTCAAACTATTAACAT
GATCTAGAGACACCTGTACAAAGTGCAGCGATGCGTTCAGAATGCCTAACTTTCTTTTTGAATACAAATAGTCAAC
(SEQ ID NO: 235)

Exon: 16841..15875
Exon: 11688..11204

FIGURE SHEET 128

Exon: 11068..10858
Exon: 10720..10593
Exon: 9997..9893
Exon: 9689..9634
Exon: 2152..1001
Start ATG: 11542 (Reverse strand: CAT)

Transcript No. : CT8839
GAATTCTGAGTTATCATCAGTTCATATATGTGTAATCATGAACTGTGTGTGCCCAGTGACTTTATAAAAGTCAGTGAATGTAAGTCTCGCTTCAC
TTGATTCCATTATTTTCCTATAACGTTTTTGGAAAGTGACGCACAAAGTGTCGGTGCATCCCACTGTGCAGTTCACCCCCTTGGTGTTCGCTCAC
TCACACACTCGCACGACCAGTCGGCCATCTCGCTCTGGCGCACGCACACCGCCAGCGGCACCAACCATTTTCTGCCTTTTGTCTCGGCCGTTTTC
GGTTCGATTAGGTTTGAGAACCGGAGAGTTCTCAGTTGTTTTCGAGATTCCGTCGCGTGCGGTTCGCTGCCCGTTCTACCCACGTCGCTCGCTTA
GTAATCCAGGCCGGATCCGGCGGTCTTTTGACGTCCCGCGCACAAAGTTATATTTAATTTGCGTGTTTCCTGAATGAACGCATCAGTATCGCGCC
ACATAAACGCACACGAAGCGAGAGAAAAGCGAGCAAAATTGAGCTAATCAATCCGCGGGCGGCCATTTTTTGTTGGCACTGCCTCAGTGCTGTCG
TCGCAGCTTTGCCCACCAAATTTGCAGGTGCAATTTGTCCGAGTCGCGCAGGACAGCGAAGTTTTCGCGAAAAGTAATTTGCAACACGTGTTCGC
ACAGTGCGTATGAGCAATATTCAACGGCAAGCTTGTGTTAGTTAGTGCCCAGTGTGATCGCGACTAAGAGTGTGTGCGTGCGCGAACGGCACATG
GCTTCGATTTGAAGAGTTTGGCCAAAATGCAAATCAAGGAAATGCCGCACAGCCGAAATCAGCGCCTTCTTGGCCAACTCTAACATTTGCGGATA
TAGCACAAGTCGAATCGGAAAGCCAAGGCAAAAGGCACAAACCCAAACAAAGAGTAACAAACAAAAACTAACAAACTCGGATACGTATCAACAAT
AAATAATCAAAATACAGCGCTCAAAACACCAAAGATTTAGGCAACTACTAGTTTAGGTTACACCATTCACCAGTTCAACTGATCGATCCCTTCTG
CAACTTGTAGCGGTGTCCTTGAAATCCACCCCACCAACATCCAGCCAGGCAACCGATTCCCGCAGAAAATGTTACAGCATCCCGCCACAGATTTC
TACGACTTGGCCGCGGCCAATGCGGCTGCCGTTCTCACCGCCCGTCACACGCCTCCTTATAGTCCCACCGGTCTCAGCGGATCGGTGGCCCTGCA
CAACAACAACAACAATAACAGCAGCACCAGCAATAACAACAACAGCACTCTGGACATCATGGCGCACAACGGCGGCGGAGCAGGCGGTGGCCTCC
ATCTGAACAGCAGCAGCAACGGCGGCGGCGGCGGCGGAGTGGTCAGTGGTGGAGGCTCCGGCGGCAGGGAGAACCTGCCCAGCTTCGGCTTCACC
CAGGAGCAGGTGGCCTGTGTTTGCGAGGTTCTCCAGCAGGCGGGCAACATCGAAAGACTGGGCCGCTTCCTCTGGTCGCTGCCACAATGTGATAA
GCTGCAGCTGAACGAGTCCGTGCTGAAGGCCAAGGCGGTCGTCGCATTCCACCGGGGACAATACAAGGAGCTGTACCGCCTGCTCGAGCATCACC
ACTTCTCGGCCCAGAATCACGCCAAGCTCCAGGCCCTGTGGTTGAAAGCGCATTATGTGGAAGCCGAAAAACTGCGCGGAAGACCCTTGGGTGCT
GTTGGCAAATATCGTGTTCGCCGTAAATTTCCATTGCCCCGCACCATCTGGGATGGCGAGGAGACGAGCTACTGTTTTAAGGAAAAATCGCGCTC
CGTACTGAGGGACTGGTACTCGCACAATCCGTATCCATCGCCGCGGGAGAAACGCGATCTGGCCGAGGCCACAGGACTGACCACCACGCAGGTTT
CCAATTGGTTCAAGAACCGACGACAAAGAGATCGAGCTGCCGAACACAAAGACGGCTCCACGGACAAGCAGCACCTTGACTCCTCCAGCGACTCC
GAGATGGAGGGCAGCATGTTGCCCAGCCAGAGTGCGCAGCACCAGCAGCAGCAGCAACAGCAGCAGCATTCACCCGGCAACAGCAGCGGCAACAA
CAACGGCCTGCATCAGCAGCAGCTGCAGCATGTCGCCGCCGAGCAAGGCCTGCAGCACCATCCGCACCAGCCACATCCCGCCAGCAATATCGCCA
ATGTCGCCGCCACCAAGAGCAGTGGCGGCGGCGGCGGCGGAGGAGGCGTGAGTGCGGCGGCCGCTGCCCAGATGCAAATGCCTCCACTGACCGCCGCC
GTGGCCTATTCGCACCTGCACAGCGTGATGGGCGCCATGCCCATGACCGCCATGTACGACATGGGCGAGTACCAGCACTTATGATTCTAGTTGGA
GGCGGCCGCTGCCGCCGGTGGCACTGGCGGGGTCAGCGGCGGGGTCAGTGGCGGCAGCAGCAGCAGCTTGAGCGGCAGCAACATCGCCTTGCAGC
AGCGACAACGCCACCAGCAGCAGCAGCAGTGCGAGAGCTTCTACTTCTGAGGTGGTGGTTGGCCACCAAGCAATATCGCCGGACTCCTTCGGCAC
AGCAGCACAAACTTTACATATCGCCCGATTGCTGGAAGGCTGTCATGAGTGGATATTCAGCTTCCAAATGCTTGGCAAGGGGATTCTGGCTGGCG
ATCCGATGGAGAACTACATGGCCCGGGAAACCATATCAAACCCGCAGTGGCAATTGGGTCAGCCAACCCAGAAATTCAAGTATCGGCCATGACAGT
ATTTTAGCCAATTGCCGATATGCCATTATAGCCCCACACTTTCCGGATAACATGGCATTTCCGCAACCAGAGATAGAGATATATAGAATTGGAGC
TGCAGCACAATCTCCTGGAAGGATTCCAGGGGGAAACTATGAACTTTCAACTATGACTTCTGCATCGATCTGTGTAAATAGCTAGGCTTTAGTTT
TTAGTGCGGTTGGGAGGCCGACCGAAATGCAAATCAAATCGAAACGTGCAAAAATTAAATGTAAACCTACGTACATGCATAAATTATACACTTTT
AATTGTAGCCCCTAGTAATTCTATTTTTGTTAAAAATAAATTCTATTAAATTATTTTCAAATGC
(SEQ ID NO: 236)

Start ATG: 1114 (Reverse strand: CAT)

MLQHPATDFYDLAAANAAAVLTARHTPPYSPTGLSGSVALHNNNNNNSSTSNNNNSTLDIMAHNGGGAGGGLHLNSSSNGGGGGGVVSGGGSGGR
ENLPSFGFTQEQVACVCEVLQQAGNIERLGRFLWSLPQCDKLQLNESVLKAKAVVAFHRGQYKELYRLLEHHHFSAQNHAKLQALWLKAHYVEAE
KLRGRPLGAVGKYRVRRKFPLPRTIWDGEETSYCFKEKSRSVLRDWYSHNPYPSPREKRDLAEATGLTTTQVSNWFKNRRQRDRAAEHKDGSTDK
QHLDSSSDSEMEGSMLPSQSAQHQQQQQQQHSPGNSSGNNNGLHQQQLQHVAAEQGLQHHPHQPHPASNIANVAATKSSGGGGGGGVSAAAAAQ
MQMPPLTAAVAYSHLHSVMGAMPMTAMYDMGEYQHL*
(SEQ ID NO: 237)

Name: sine oculis
Classification: transcription_factor
Gene Symbol: so
FlyBase ID: FBgn0003460

Celera Sequence No. : 142000013384695
ACGAAGACTTCGCGCAGAGCCGAAGAAACGAGAAACCGCAACTCGCTTGGCCGCTCTTCGGAAGAGTGCCCGCGAGTGGAAGACTACGCAGCCAG
TCTTCAGTTCGATTCTTCAAAATAGGTTTTTGATTTGGAGCTGCAAATGCTGTATTTTGCAAAAAGTTTCTTTTACTTGGCATGCTGATGGCAAC
TCTGTTAGGCTGTAATATCAGGTGGAAGACCAACATGGGAAAATCTAAAAGTTGGTCTTTCAAAAGTTCTAAAGAATTGCAAACTGATGGATCAC
AAAAGTGGCATTTGATGGAATTTTAGAGCTTATTCATTTAGATGTGTTACTATCTTTCCTTACAGTTTTTGATAGAGTATCCAATGTGCCACATG
GAATTCACATAGATTCAGCCCCAATCGACTTGGGTCCGTGGGGAAGTGGAGCTACTAACAGAGTGCACTTAAACGGAAACAGTAACAATTGAAAG
TGGCAATTTGGGGAGCGTACGCGCCTTAATTAGATTGCGGATTAAGATGGTCCCATCGAATCATATTCATGGGTGGATCCGCGGCGACTTCCACA
TGGAGTCGACTCTAATCAGCAGCAATTACTGTGCCAATTGCCCATGCCGATTCCGCTGATTTCGGCTTTCGATTGAAAATGAGAATGGCTCGTTG
GAAAAGTGGGATTAGCAGCAATGGAAACATGATGGAGGAGAATCGAATCGAGGCAGTCTTTTCGATCGTCTGCGCATCATGCCACAAAACCATGC
CCCATGACCAGTGAAATTGTGTTTGCCGGGCTTGTTTTCTTTTATTTCGTTTACTTGCCTCCTCTGCGTTTTCACACTTTTCACGAATCGACGTA
TCCATTGTTGGGCAACTTGGCTAATGGAATCGGCAAGCAGCCACCAGCGAACCATTAATTGAGCACGCTGGCGGCTTTAATAGTTCTAAAGCAGC
TGGATATTAGTGTCAGAGTCGCAGTGAATCGCGCAGCGGTACTCCGCTTTAATTTTCACAATTAACTTTATTTATTCGATCATAAACATGTGCAT
TTACGGGAGAAGAGAGCAGGACTACTTGGCTAGTATTTCGGCAGCTCGGAATAGCGCGGCGGCGTGGACCACAGCACGCTGGAGTTTCGCTTCAG CTGGCTGGGATCGATGTTCGGGAATATCTGCTTTAGGTCCGGTGTGGTGGGCGCCACCGAGAAAAAGCTGTCGATGATGTCGGTTGGGCAGTGGC
TCTGCATAGCAATTGCCTCTCCCCTTACGTGGCCTGAAAATAAACACATAAGTCAGAATCTATATTTAAGAACATTTCCTTTAGTAGTCCCAATG
GAAATCAGACTGTAATCTGGTGTATTTACTTGTATATATTTACGATGAATAAGGTATCTCGAAAATAACTCTTCGAAATGATCCACAAACTTACT
TCGACTCCAGGTGGGCGCTGGGGACGCTTGTGGGTGACCTTTCCCTCGTCGTCTGTCGAGTCGTCTTCGTGCAGCATCTCCCAGGTGTACTTGG
TTTTCGGCGGCGGCGGAAGCATCTTCTTGGGCTTGGCGCCGGTTAGCTGCTGCAGTTTCTGCTGCTCCAGCTCCTTGAACTTGGCCTTCTTGAGC
GCCTCGGCTTCCTCTTGCTGGCGCATCTTCCGCTGCAGCTCCTCCAGCTCTTGTCGTTTGCGCTCTTCAATTCGCTTTCGCTCCTCCTGCTTCTT
GGCGCGCTCGGCGGCCAGCTTGGCCATACGCTCTGCCCGCTCCCGCTCCTTGGCTTCGCGCTGCTGGGCAGCCTGCTGGTGCTTTTGCTCACGCA
GCTTCTTGCGCTCCTCCGCCAGATTGTGCAGGCCCTTGCGGAAGTCGTCTCCGCTGTTCTCGCGCGACAGCGTTTTTGTGGACGTGGAATTGACC
GACCTTAGGTTCGTACCGGTGGCCGTCTTCAGCAGACTAGTGGCCTTAGACGCGCTGGCAGGTCCCTTCTTGGGCTGCGCCGAGCTTAATGGTAG
TGTGCTTGTCGTTTGAGTCGGTGTGAAAAAGCGACCAACAGTCGGAGCAGGCAGCTTGCCAATTTTGGGAGTGTTGTTTGATCCTGGCGTGCCCT
GCTGAAGAGTAAAAAAAAATAACAATAAATGAATCACCTATCAAACAGTTCTAGAAAGCGCCAATTGATACAGAACTGGTGAATAGTCTAGCCTA
ATTCTGCCTGCTATCTGCCTGCTATATATGTGCAACTATACTGTACCTACCAGATCTTTTCCCCGCTTAGGGCGCATGCTGTTCTGTGCGTTTGC
CGCATTCTCGAACGCCTCCACGCGCATTTTCACTGGACTCTGAAGCAGTGGGCTGTAGAAGTGCAAAGATTGTTTAGAAGGATAACATGCATGAA
GAGGCAGGGTATCTACTCACTTGAAAAGCTCATGTGTACGGGTAGGCAGTTTTATAGCCTTTATGCTCGAGAGCAGCTTGGTCGTCGGCAGCTTC
TCCTCCACCGACTCGTCCTCCGTTAAGAGGCTGTCCTGCTTACTCAGAGGTTGTTTCTTGTCGTTGGAGTGCACCTCAAAAGTGGCATCTCCAGC
TGGTCCTATTGGACTATCGCTCGTCGGCGCAGGACCCAGTACGAGGGTGGCGTTGGAAATCGCCACGGTCTCATTGACAGCAGCCGGAGCAACTG
CAGCCACTGATTGCTCTGCAACGGGCGGATCTTCGAGTGCATCCTTGTATATGGATCGCTCCTGAACCGTTCGCGAATCGCTGCTACACTTGCGC
GTGCGCGACGAGACTGGCGAGCTCTTGTCCAGGTCGCTGAATCGTTCCACCTTTATGGGTCGGTGGCTTTCCACGTCCTTCTTCTTCTTGCGGAC
CTTCTTGGAGACCTCCGTGGATGTCGTCGTGTTGCTGGCCACCGTATCGTCCGGTCGCGCTGCCTCCGTTGTTACAGAGGAGACGGTGGTCACAT
TTGCCGTGGAGACCGCATTGGTTAACGGGGGCACTGCTTCGGTACTGAGTTTCTCGCGCTTTACCTTCACGCGGAGTGTCTTCGTGGTGTTCACG
TCCTCTGTGACTGAGGCCTCCTCCGGAGGCTTTTGCTGCTCAGCTGTTTCTGCTGCTGGCTCTTCTAGTTCCGGCTCCGCTAGTTTATTTTCCTC
TAACGCCTGTGCACTGGTGAAGCTGTTAAACTGGGAGACTCGCTGCTCGCTCTCAACCTTGACCTTTACGAGCTCCTCGCTGCTGGGCCGCCGCA
TCTTACGGTTGAGTGAGGGCTCCTTGAGTAATTTCTCGGTCTTCAGCTTAGCGGCTCGCTGTGGCCTTCCGGAGCCGAGGGTGGTGTCCGCCGAG
ACGGGCACAGGCGGAGGCGGCATCAGCGAGGCCGTGGAGTTGTGCTCGTCCTCGGCGATAGCCAGCAACTGGGAGTTGCTGACCCGAGTGCTTTG
ACGGGCCGACGTGTTGTTGGCCGTGGCGTCTGGAGCTGCTCAAATGGAATATCACAGGGGTTGTTGGTCGTTAATGCTTTAAAATGGCCAGGATA
CTCACCCTCGGGCTCATTCTGATCCTCGGCCAGTGAGGTGAGTCGCTTGGGGCGCTTTTTCGTTTGCTGCGGCGTCACCGAAGAGTTCTCCTGAC
TCTTCGCTGCCGGAGCACTGTCCCTCGGTTTGGCCTCCGCCTCCGGCTGGCCTGTGCCGTAGAAGAGGTGGTCCAGCTCCTCAAAGTGGGCCTAA
AAAACACATATGACGCCATGTTGACAGTGTCGGAATTTCGTCTCCTGATCCTGGCTTACCTTGCGCAGGACCTCGAGCTCCCTGCGCAGGTCCGA
AAGCGAGCCCAGCACGCCCAAGATGTCCTCCATATCTAGCGACTGTATCTGACAAACTGCAAATCCGGATTCGGTTCCTTCGATTTTATCGTTTT
TTTCAAATGGCGGCAATTGCGACGCGCGTCAGCATTTGATAACATGCCTTTAATTGTGCACTGTTGACAGTTAACAGCTCGTCGGGTGCTGTAAG
GCGCATTTATGCCTCTGCTTTCCAACACTGCACGGGCGATAAAGTTCCCGCGCAAAATGAAAAACACAACCAAAACTTGTTTTTGAGTGAATAT
TGGGAGATATTTATTTGAATTCTTTAAAATAATATTATTGGGTTATTTAAATAGTTACGTACTGGATTTCTAGCCCTGTAAATTTTGAAAGTATA
ACATTAGGTGAACCAGTTCCAATACGTTCCCGCCACTACCATCTCTAGAAAGCAGTGCTGCACGGCTCCCCAAAAAACATATTGTAAACAAATTT
GAGGGAAAATGGTAAGGGAAAGAACAAAAAGGAACATTTAAATTATAAATATAGATTACGGAAGAGAATTAATTTGCGTAAAGGACCGGAAATAT
TTCAAACAAGTTTCAGCAAACGTCCAGTGCTGCACAAGCACTTCCGACGATAGTATCGCCATGGCGAGCTGACCAGCAAGCCCATCTCTAGCACA
TTTGTTAAAAAATTTGCAACAAGCCAACGAAAATCGACCAGGAACGGTGGACAGCCAAAACCGCGCGCTCTGCGACGACCACCGTGGGATGCACA
TACGTATGCGCAGCCGTGCCGCGGAGTAGACACAGTGCCCGCGATCCGCGACCAGCGAACCGCCAAACCCCGAGAAGCCAGCTGCAGCAGATCCA
CAGATCGCGCCGCAGATCCAGATCATGGGCCTCGACTTCGACGCAGTGGAATACTGCAAAGGGGTGAAGACCCAGCAGTCCCAGCCGCCTTTCGC
CTGTCCCGTCCGCGGCTGCGACCGCAGCTACAAGACCATCATGGGTCTGCAATACCATCTTATGAAGTACGACCACGACAACCCACAGCCGCTCA
CGCCCGTGCTGACTCCGAGCCGCAAGAAGGCGCGCTCACGCTCCGGCGGCCACCACTCCACGCCTCGTCCGCACAAGGATCACCCCA
(SEQ ID NO: 238)

Exon: 3932..3765
Exon: 3701..3521
Exon: 3455..2396
Exon: 2332..2236
Exon: 2091..1425
Exon: 1268..1001
Start ATG: 3833 (Reverse strand: CAT)

Transcript No. : CT8873
AAATGCTGACGCGCGTCGCAATTGCCGCCATTTGAAAAAAACGATAAAATCGAAGGAACCGAATCCGGATTTGCAGTTTGTCAGATACAGTCGCT
AGATATGGAGGACATCTTGGGCGTGCTGGGCTCGCTTTCGGACCTGCGCAGGGAGCTCGAGGTCCTGCGCAAGGCCCACTTTGAGGAGCTGGACC
ACCTCTTCTACGGCACAGGCCAGCCGGAGGCGGAGGCCAAACCGAGGGACAGTGCTCCGGCAGCGAAGAGTCAGGAGAACTCTTCGGTGACGCCG
CAGCAAACGAAAAAGCGCCCCAAGCGACTCACCTCACTGGCCGAGGATCAGAATGAGCCCGAGGCTCCAGACGCCACGGCCAACAACACGTCGGC
CCGTCAAAGCACTCGGGTCAGCAACTCCCAGTTGCTGGCTATCGCCGAGGACGAGCACAACTCCACGGCCTCGCTGATGCCGCCTCCGCCTGTGC
CCGTCTCGGCGGACACCACCCTCGGCTCCGGAAGGCCACAGCGAGCCGCTAAGCTGAAGACCGAGAAATTACTCAAGGAGCCCTCACTCAACCGT
AAGATGCGGCGGCCCAGCAGCGAGGAGCTCGTAAAGGTCAAGGTTGAGAGCGAGCAGCGAGTCTCCCAGTTTAACAGCTTCACCAGTGCACAGGC
GTTAGAGGAAAATAAACTAGCGGAGCCGGAACTAGAAGAGCCAGCAGCAGAAACAGCTGAGCAGCAAAAGCCTCCGGAGGAGGCCTCAGTCACAG
AGGACGTGAACACCACGAAGACACTCCGCGTGAAGGTAAAGCGCGAGAAACTCAGTACCGAAGCAGTGCCCCCGTTAACCAATGCGGTCTCCACG
GCAAATGTGACCACCGTCTCCTCTGTAACAACGGAGGCAGCGCGACCGGACGATACGGTGGCCAGCAACACGACGACATCCACGGAGGTCTCCAA
GAAGGTCCGCAAGAAGAAGAAGGACGTGGAAAGCCACCGACCCATAAAGGTGGAACGATTCAGCGACCTGGACAAGAGCTCGCCAGTCTCGTCGC
GCACGCGCAAGTGTAGCAGCGATTCGCGAACGGTTCAGGAGCGATCCATATACAAGGATGCACTCGAAGATCCGCCCGTTGCAGAGCAATCAGTG
GCTGCAGTTGCTCCGGCTGCTGTCAATGAGACCGTGGCGATTTCCAACGCCACCCTCGTACTGGGTCCTGCGCCGACGAGCGATAGTCCAATAGG
ACCAGCTGGAGATGCCACTTTTGAGGTGCACTCCAACGACAAGAAACAACCTCTGAGTAAGCAGGACAGCCTCTTAACGGAGGACGAGTCGGTGG
AGGAGAAGCTGCCGACGACCAAGCTGCTCTCGAGCATAAAGGCTATAAAACTGCCTACCCGTACACATGAGCTTTTCAACCCACTGCTTCAGAGT
CCAGTGAAAATGCGCGTGGAGGCGTTCGAGAATGCGGCAAACGCACAGAACAGCATGCGCCCTAAGCGGGGAAAAGATCTGCAGGGCACGCCAGG
ATCAAACAACACTCCCAAAATTGGCAAGCTGCCTGCTCCGACTGTTGGTCGCTTTTTCACACCGACTCAAACGACAAGCACACTACCATTAAGCT
CGGCGCAGCCCAAGAAGGGACCTGCCAGCGCGTCTAAGGCCACTAGTCTGCTGAAGACGGCCACCGGTACGAACCTAAGGTCGGTCAATTCCACG
TCCACAAAAACGCTGTCGCGCGAGAACAGCGGAGACGACTTCCGCAAGGGCCTGCACAATCTGGCGGAGGAGCGCAAGAAGCTGCGTGAGCAAAA
GCACCAGCAGGCTGCCCAGCAGCGCGAAGCCAAGGAGCGGGAGCGGGCAGAGCGTATGGCCAAGCTGGCCGCCGAGCGCGCCAAGAAGCAGGAGG AGCGAAAGCGAATTGAAGAGCGCAAACGACAAGAGCTGGAGGAGCTGCAGCGGAAGATGCGCCAGCAAGAGGAAGCCGAGGCGCTCAAGAAGGCC
AAGTTCAAGGAGCTGGAGCAGCAGAAACTGCAGCAGCTAACCGGCGCCAAGCCCAAGAAGATGCTTCCGCCGCCGCCGAAAACCAAGTACACCTG
GGAGATGCTGCACGAAGACGACTCGACAGACGACGAGGGAAAGGTCACCCACAAGCGTCCCCCAGCGCCCACCTGGAGTCGAAGCCACGTAAGGG
GAGAGGCAATTGCTATGCAGAGCCACTGCCCAACCGACATCATCGACAGCTTTTTCTCGGTGGCGCCCACCACACCGGACCTAAAGCAGATATTC
CCGAACATCGATCCCAGCCAGCTGAAGCGAAACTCCAGCGTGCTGTGGTCCACGCCGCCGCGCTATTCCGAGCTGCCGAAATACTAGCCAAGTAG
TCCTGCTCTCTTCTCCCGTAAATGCACATGTTTATGATCGAATAAATAAAGTTAATTGTGAAAATT
(SEQ ID NO: 239)

Start ATG: 100 (Reverse strand: CAT)

MEDILGVLGSLSDLRRELEVLRKAHFEELDHLFYGTGQPEAEAKPRDSAPAAKSQENSSVTPQQTKKRPKRLTSLAEDQNEPEAPDATANNTSAR
QSTRVSNSQLLAIAEDEHNSTASLMPPPPVPVSADTTLGSGRPQRAAKLKTEKLLKEPSLNRKMRRPSSEELVKVKVESEQRVSQFNSFTSAQAL
EENKLAEPELEEPAAETAEQQKPPEEASVTEDVNTTKTLRVKVKREKLSTEAVPPLTNAVSTANVTTVSSVTTEAARPDDTVASNTTTSTEVSKK
VRKKKKDVESHRPIKVERFSDLDKSSPVSSRTRKCSSDSRTVQERSIYKDALEDPPVAEQSVAAVAPAAVNETVAISNATLVLGPAPTSDSPIGP
AGDATFEVHSNDKKQPLSKQDSLLTEDESVEEKLPTTKLLSSIKAIKLPTRTHELFNPLLQSPVKMRVEAFENAANAQNSMRPKRGKDLQGTPGS
NNTPKIGKLPAPTVGRFFTPTQTTSTLPLSSAQPKKGPASASKATSLLKTATGTNLRSVNSTSTKTLSRENSGDDFRKGLHNLAEERKKLREQKH
QQAAQQREAKERERAERMAKLAAERAKKQEERKRIEERKRQELEELQRKMRQQEEAEALKKAKFKELEQQKLQQLTGAKPKKMLPPPPKTKYTWE
MLHEDDSTDDEGKVTHKRPPAPTWSRSHVRGEAIAMQSHCPTDIIDSFFSVAPTTPDLKQIFPNIDPSQLKRNSSVLWSTPPRYSELPKY*
(SEQ ID NO: 240)

Celera Sequence No. : 142000013384847
AATGGCTTGCTGAATCCCTGACCTTTCCGCGACCCCTGCTCATTGCATTTTGCGGGAGAGGAGAGCCAAAGGCGACGACCGATTTTAACCTTGAC
AGCTCTCCCAGCTTTTTTACCCCACCTCACCTACGCCAACTGAGGCAATCACACACACACACGCTCGCAGATTATGGCTATTTGTTATCAATGC
GAATTACGGCACTCGGGCGTTTTAGCCAACATTTCACTTAAGACTGTTTGTGCTTATTTTAATCACGTAGGCCACCGAATTTGCCAAATAAACAA
AAAAAAACGCACATACAACGCACACACACAGACGCACGGGCAGCTATATGTGCATTGTTGTTGGTTTTTCCTGCGAGTATTCTCTTTTGTAAGAC
GTTTTAGGGTTGCAACTTTTAACCCTATTGACTGTTTTATACCCTGCCTTGAGCTCTATTACGCCCCTTGTTTATAAAAACCGCGTAAACTGTGC
AAAAAAAGGGAAAAATTCTTAACTCAGCACTAAAATTTCTTTTTGATAGCGATGGGCGTCGACCGATACTTAGCGTGCAGCGATTGACATGTACT
CGTTGTACAGCACTATTACCGGCGGGCAGTAGGTATCGATAGCTGAACGAGCCAACGTTAGTGGTGATTATTTTATACTGGCACTTATATACTAA
CGGTAATCAAAGCTTTTTATTTCGCTATTTTTATTTACTAGCTTTAATATTTAATTGCACAAGATTCGGAAACAAAAAGCTATTGGGAAAATTAA
CTCAAAGCGGCCATTAACCCCATAAGAATTACTTTAATACAACTTCAGTCGATCGTTTATCAATTAAGCAAGGTCTCTAAGAATGGCAAATACCC
TTATCGTCTATTCCAATACATTTATATATATATATTTTAAAGTCGATAGTCGATAGCGCGATGTGCCATCTCCATTATCAAAACTAAACAGATGC
TGGGCGGAAAATCAACTGGTTCCTCGTGATAACTTAATCCCACTAATAAGCGCAATGTCGTCCAGTGAACGAGTGGCCAAAGTGGTGCTGGTGGA
CATCGAGGGCACCACCACTTCGATTAGCTTTGTGCACGATGTCCTGTTTCCCTACGCCAAGCAGAATGTGGAAAAGTTCCTGAGGGATTCGTGGG
AAGAAGATGATATAAAGCGTATTGTCCAGGATCTACAGCAAGTGCCCCAGTATGCGGACTACAAGGCCCTGTTAAGTGGTCCACCTACGGAAGTG
GATGTAGATCTGATTGCAGGCTTTGTGCGCTATTTAATTGATCAGGATCTGAAGGTCACGCCAATGAAAACGCTGCAGGGCTTGATTTGGGCGCA
GGGCTACGCTAATGGAGAGCTGAAGGGCCAGTAAGTTCCCCATTCAATATTCTCCTATCATGGCCATATAAGTTTTACAATCTGAACTCTAGAAG
GTTATCAAAGAAAAGGCTTACTTAACGTCTGTTCCCAAAAATAATTTGGGTGTCTTTCTGAGATCCAATTATACAGCTTGGTGATTTTTTAAATA
TGTATGCTAGCTATATTCTCCGCACGGGAATGTTTAACTTTTGCTGATTTCAATAGTTATCAGATAACATTCAACATAGTAACCAAAAGTACAAC
GCAACAACTCATTATTATTGATAATTAATTAATTATCTATAAATGTTATTATAGTGTATACGAAGACGTCCCTGCAGCTTTTGAGGCTTGGCGTG
CTGCTGGCCTCCAGATTGCAGTCTACTCCAGCGGCAGTGTGGCTGCCCAAAAGCTGATATTCGGTCATAGTTTGGCCGGGAACCTGCAGCCGTAC
TTGAGTGCTTATTTCGACACCCATGTGGGCCACAAACAGGAACAGCAGTCCTATAAAAACATTGCCAAGCAATTGAAGGAGGACCCGAAGCAGAT
ACTCTTTCTCACGGATATTCCAGGAGGTGAGTGGCTGATCCACACGAATCCTCATCCGTAACATTTTTAATGTGAAATTATATTTTAGAAGCGGC
CGCCGCTCGCTGTGCGGGCTTGCAAGCCATAATTCTGAAGCGTCCTGGAAACGCCGCCCTAGCAGACGATCAAAAAACTGGATTCGAGTTGATTC
CGGACTTTAAACCACTTCACAACCTGAAAGTTCCGGTCAATAAATCCCAGGCTTAGGTCATTCCAAAAAAGTATACATATATTGTGACTATGTGC
TTGGGAATTAGGTGAATCTCTAGAGGAAAGCTCGATCTGCGCTGCACAGGTCGTCACCGCTGTCGTGGCTGGGCGTCTCGGTCGTGAGCCCCTGC
GGCCGTCGTTCGGACCGCTTGCTTCGTTGAGACTGCCTCGAACAGGACTTTTCTGAGCCATAGACCTTACGCAGTTGCTGCAGCTTAGTATCCGC
ATCGGGAACAGGAAACTCTGACTTTTTCTTCCTACGTTGCCGGCTCCCCTCGCACGAATGACGCAGTTCCTCGGTCCGGCAGGTGTGGGTGAGCT
TGCCCACTTCTGGACCCCAGAACGTGGGTCCTTCCAGAAGAAGGGGAGCGGATTTGACCCGTTGACGCATCATCTCCATATGCAGTTCGTACTGA
CGCTCCTGAAAAGCCTGCTCTGCCTTGCGAGTGGCCAACCGAATGGATAGCAGTGCCTTGTGGGATTCGCTAAAGAAAGAACACTGAATGTGTGC
GAAACTTAATATTTGGTGAACTACTCACTTCAAGGACAGTGATTTCCAAGCCGGCGTTTTCCTCACCTCCCAATCGAATTGCGGACGAGGATCAT
GATAAGTGCAGTTGTTCTTCAGCTCCTTAACCTTCTTCCTAGATACTTCAGCCCTCAAAGTTGCCGCTAGATTAGGACGAGATACCGGATGCAAC
GGGGACACACTGGGCGTTCTCCTCTGGACCGGTTCCTCCGGCAACTCATAGATGCTCAGCGGTGGTAGTGGCTTCTCATCCTTTACGCTAGACCC
TGGCTTTGGTTTCCTTACTCTTCCGCGTCTTCCTCGACCTCTTGCTGCGCTGGAAGCACTACTACTTCGCTTCGACGAGGTGGTGGGTGATTGAA
TCTGTATCTTGGGAATTTCCTCCTGCTTGCTGAGTGGGAAATAGTTGCTTCGCGCAGGCTGAGCTAGTTTGGAAGGCTTCGAATGAGCCTCTAAG
GCAATCCCTTG
(SEQ ID NO: 241)

Exon: 1001..1355
Exon: 1671..1919
Exon: 1988..2146
Start ATG: 1005

Transcript No. : CT8961
CGCAATGTCGTCCAGTGAACGAGTGGCCAAAGTGGTGCTGGTGGACATCGAGGGCACCACCACTTCGATTAGCTTTGTGCACGATGTCCTGTTTC
CCTACGCCAAGCAGAATGTGGAAAAGTTCCTGAGGGATTCGTGGGAAGAAGATGATATAAAGCGTATTGTCCAGGATCTACAGCAAGTGCCCCAG
TATGCGGACTACAAGGCCCTGTTAAGTGGTCCACCTACGGAAGTGGATGTAGATCTGATTGCAGGCTTTGTGCGCTATTTAATTGATCAGGATCT
GAAGGTCACGCCAATGAAAACGCTGCAGGGCTTGATTTGGGCGCAGGGCTACGCTAATGGAGAGCTGAAGGTATACGAAGACGTCCCTGCAGCTT
TTGAGGCTTGGCGTGCTGCTGGCCTCCAGATTGCAGTCTACTCCAGCGGCAGTGTGGCTGCCCAAAAGCTGATATTCGGTCATAGTTTGGCCGGG
AACCTGCAGCCGTACTTGAGTGCTTATTTCGACACCCATGTGGGCCACAAACAGGAACAGCAGTCCTATAAAAACATTGCCAAGCAATTGAAGGA GGACCCGAAGCAGATACTCTTTCTCACGGATATTGAAGCGGCCGCCGCTCGCTGTGCGGGCTTGCAAGCCATAATTCTGAAGCGTCCTGGAAACG
CCGCCCTAGCAGACGATCAAAAAACTGGATTCGAGTTGATTCCGGACTTTAAACCACTTCACAACCTGAAAGTTCCGGTCAATAAATCCCAGGCT
TAG
(SEQ ID NO: 242)

Start ATG: 5

MSSSERVAKVVLVDIEGTTTSISFVHDVLFPYAKQNVEKFLRDSWEEDDIKRIVQDLQQVPQYADYKALLSGPPTEVDVDLIAGFVRYLIDQDLK
VTPMKTLQGLIWAQGYANGELKVYEDVPAAFEAWRAAGLQIAVYSSGSVAAQKLIFGHSLAGNLQPYLSAYFDTHVGHKQEQQSYKNIAKQLKED
PKQILFLTDIEAAAARCAGLQAIILKRPGNAALADDQKTGFELIPDFKPLHNLKVPVNKSQA*
(SEQ ID NO: 243)

Name: ENOLASE-PHOSPHATASE-like
Classification: protein_phosphatase

Celera Sequence No. : 142000013384830
AAATTAGCTCATATTGTCAGGCTAGAGCGAATGGAGGTCATATGGAGATCGTCGCGTGTTCATTTTTTGCTTACGTGATGAATGTCATGAAACTG
AAAGCTTTCGATCTACTTAAAAATCAAATTTAAAAGGTAGCTACATTAAGATGCAAAAACTATTGAGTTATTAATACACAAACAAAGCAAACAAC
AAGGTGCATCGCAATTATCCTGATGATCTTGACAACAAGCGAATTAGATTAGATAGTCAGTGCGACCACTAAGAAATTCTATGGGAATGCCGTCA
GCTTCCAAATGTAAAGTGACTTGCATAAGTCAGCACAGTCCCCTTATGTTTGGGGTAGATTTTGTAGGTCAGGTGACAAAGGTGAACCAGGTGGC
ACTGAATGGAGCCGAACGGCCAGCCGGGTCACGTTTCCCCCAAATCCCACAATAATGGGGTTGGCGCTGTCTAGAACCGACCTTGGCTATAGCAA
TAGTCTACTATGCAATAAATAGTGTGCACTCGTAATGCGTTCCCAACAGGGGTTTCGGTACAGAAATCAATATCACCGCAATGGCCATCGGCAAT
TGACAACGGACAATGATTGAATGGGGGATAATGGGGCCTAGCTGGGCAGACCCCAACATCGGAATGGCATTTGTACAACTTCTGCCATAAACTAT
GCAAATCTGGCGTCTCCTGGGATATCCGCCGTTCGCAATAGCAAAATGTCGACTGCATTTCCGGCAGCCAATTTAATTAGTTGTTAGGCAAACAT
TCGGGTAATCAGTGGCTAAACAGCTTATTTAGCTGCATTTGGTCATTCAAGTTGGATTATGTCTGTGCAGCGTAAATATGCACAAAATGTTGCAC
ATTGTTTCGGCTGAAATATAATATTATCTTACAATGAGACATAGAAGCAGCGTTTAACGCGCACAAACATAATGGGCAACCGACATTTAAACAAT
CACTATAGCACTGAAAAAGTTGACAACCTCAAACTTCATACGTTTGGCAGCTCGGCCAGCATTTCAGTTCATTGATATACAGAACATTGTTCAGT
CTACATCAATTTTGAATTGTGAATATTCGGTAAAGATTATTGTGATAAAAATGGAAACCCCAAGCGAGTTAACTGAGAAACAGAACCAAGACCAA
CCTACCTACCAGCCGCGACTGAACGAGGTGGCCCAAAAGTTTCTCGCCGATTTGGACGCGGAGCGCAAGCGATTGTCCGCGGAGTTTCCACTTTG
CGCACTGCTAATCGACGAATGTAAAATCAATTTGGCTCTTTACAGGGTATTTTAATGGTACTTATCCCAATATTCCAGCTGTGGACCGTGTCTAC
TCCACTGGTCGCATTCCCGGCAAGGAGCCCTTCGCAGACGTGTACCAGCAGAAGCCGATGAAGATTATCCAAAAGGTCTTCGTGCCTGTTAATAA
GTTTCCCAAGGTGCGTTTTATACAATTAGCTGTCCCCTCCGTCCGCAAAATAAATCCGTACCCTTGCGCAGTTCAACTTCACTGGCAAGATCCTA
GGGCCCAAGGGCAACTCGCTGCGTCGCCTTCAGGAGGAGACCCACTGCAAGATTGTCATCAAGGGTCGCAACTCGATGCGCGATCGTAACAAAGA
GGAGGAGCTGCGCAGCTCAGGCGACCCGAGATATGCCCATCTTCACAAGGATCTCTTTTTGGAGGTCAGCGCGGTGGCCCCTCCGGCGGAGTGCT
ATGCACGGATAGCCTACGCCCTGGCCGAGATCCGTAAGTACCTCATTCCAGACGATAACGACGATGTTTGGCACGAGCAGCAGCGCGAGCTGATG
GAAATGAATCCCAAGTCGGCCAAGAAAAGTAACGGACTCAATATGGCGCCCTACAGGTAATGGTCATCTTATTCTCTCTGCATACCGATGCAACT
TGACTTACTTGACAAGCAAGTTAAGCATGTGGTATCCATCTGCTTGCCATTGGGCAAAGGGTAAAAATCCATTGTTATTTTGCAGATCGAATTTC
GACAAGGCGATTGGAGCCATCAGGAATAGGGCTCCCAAGTACAACAACCAGATTAGGCGAGTTACGGAAAATCCGCGCGAGTAAGTTACTTGTAA
AGTATAATTTTGTATCATTTAATGACCAAACCAGGAGTTACCGCGTCCTAGTAGTTCCTTGAATCCTAGCCAACATGCGTTAAACCAGCATTTAA
CATTTCGATCTTTATAGAGTCGCCTATATGGAGGAGGTGGAATATGATTATGATGAACATCTTATGTTCTGCTCCCCAGTCGTCCGTCTATAGGC
TATGAGTATAGCAAACGTAAGTGTTTGGTAGTGCCGGGGTCTGTTACATAAGATAGTTTTATGAGATGCACCTTAGATGGGAACCTTGGGATTTC
CATTAGATTATATTGTACTATCAAAACCAAAAACAGTGCATGAGTAAGATCTCAGATCAAACTCTATAATATACTAGAATGACTAATATTATACA
ACGATTTACTTCAGTTTAGTAATTACAAATAATAATCAACCAATTTTATAGCACCTACATCAATGACAGCGACAAACGCTACGCCATTTAAACGT
GGATATCCGTATCCAAGTATAAGCCCAATCCTGCTATGTGGACTGACTGAGTTTATACAATCCAAGGAAGCACATTAAAGAAAGCAGCATTTAAA
ATGATTCTTTTAATTAATAAACAAACATTTATAAAAAGCGCACTTGTTAAAATTATATCCTGAGTTCGTAATTTTCTATGAATTTAAAAAACTAA
TAAAATGAAAGGCAATGCATGAATTTTATAAATACTTTGTACTCAGATCTAACAATATCTTTTATATTCTTACTCCGTAACTTACGCCGACACGA
AAGCTTAATTTATTCTTTAACCGAAAAGATATTCCATGCTTTCAAGCTTTTGTGTAAAATACAATGTAAAATCGAAGTATGTAACGTAAGGAAAA
TGTAAAAAGTAAATAAAACCCAACGAAAAATGTTAAATGAATTTATATGCAAATTAATATTCAGTCATATATATATATATGTCATATATATGGCA
TATATGTCATATATCATTATGGAACATTGACTAATATCTTTAAGATCTCTTCTGAGAAATCTTGCCAAAAGATTTACGGGGTTTCGTGTCAGTTT
GAAATCGAAAGACACTATAGAAAAATCGAAAGTGGATCAATAAACTTTATACGGCGCCTTCGTGACTGATAATAATCAGTCCATAATCACGCGAT
TTATATCCTTCGATCGGTGGCACACTTCAGTCACATGCCACATGGATCGTAAAACGCAATCGAGACTATCGCTATGGACTTTGGACA
(SEQ ID NO: 244)

Exon: 1001..1255
Exon: 1314..1435
Exon: 1497..1861
Exon: 1986..2075
Exon: 2222..2317
Start ATG: 1096

Transcript No. : CT8995
CTCGGCCAGCATTTCAGTTCATTGATATACAGAACATTGTTCAGTCTACATCAATTTTGAATTGTGAATATTCGGTAAAGATTATTGTGATAAAA
ATGGAAACCCCAAGCGAGTTAACTGAGAAACAGAACCAAGACCAACCTACCTACCAGCCGCGACTGAACGAGGTGGCCCAAAAGTTTCTCGCCGA
TTTGGACGCGGAGCGCAAGCGATTGTCCGCGGAGTTTCCACTTTGCGCACTGCTAATCGACGAATCTGTGGACCGTGTCTACTCCACTGGTCGCA
TTCCCGGCAAGGAGCCCTTCGCAGACGTGTACCAGCAGAAGCCGATGAAGATTATCCAAAAGGTCTTCGTGCCTGTTAATAAGTTTCCCAAGTTC
AACTTCACTGGCAAGATCCTAGGGCCCAAGGGCAACTCGCTGCGTCGCCTTCAGGAGGAGACCCACTGCAAGATTGTCATCAAGGGTCGCAACTC
GATGCGCGATCGTAACAAAGAGGAGGAGCTGCGCAGCTCAGGCGACCCGAGATATGCCCATCTTCACAAGGATCTCTTTTTGGAGGTCAGCGCGG
TGGCCCCTCCGGCGGAGTGCTATGCACGGATAGCCTACGCCCTGGCCGAGATCCGTAAGTACCTCATTCCAGACGATAACGACGATGTTTGGCAC
GAGCAGCAGCGCGAGCTGATGGAAATGAATCCCAAGTCGGCCAAGAAAAGTAACGGACTCAATATGGCGCCCTACAGATCGAATTTCGACAAGGC GATTGGAGCCATCAGGAATAGGGCTCCCAAGTACAACAACCAGATTAGGCGAGTTACGGAAAATCCGCGCGAGTGGAATATGATTATGATGAACA
TCTTATGTTCTGCTCCCCAGTCGTCCGTCTATAGGCTATGAGTATAGCAAACGTAAGTGTTTGGTAGTGCCGG
(SEQ ID NO: 245)

Start ATG: 96

METPSELTEKQNQDQPTYQPRLNEVAQKFLADLDAERKRLSAEFPLCALLIDESVDRVYSTGRIPGKEPFADVYQQKPMKIIQKVFVPVNKFPKF
NFTGKILGPKGNSLRRLQEETHCKIVIKGRNSMRDRNKEEELRSSGDPRYAHLHKDLFLEVSAVAPPAECYARIAYALAEIRKYLIPDDNDDVWH
EQQRELMEMNPKSAKKSNGLNMAPYRSNFDKAIGAIRNRAPKYNNQIRRVTENPREWNMIMMNILCSAPQSSVYRL*
(SEQ ID NO: 246)

Name: KH domain RNA binding protein
Classification: RNA_binding

Celera Sequence No. : 142000013384830
TGACTCCCCACAAAAACAAAACACTCAACTGATTGCTCTCGGGAATATAATCTTAGAAGTACGTCCAGAATTTCTGTGGTCACTGGAACATGTGT
GGCACATGAGATTGCCACCAGACCCCAATACACATGCGTTTCATATAGATCCTATTGCTTTCATTAATGTATACACAGCGATTGTGGGGTCTGTG
AAAGGGGTACAATTGCACATATGTACGTCTTCATATATATGTACATATACGATTCCCCACATTTGAACGATATGAGATCGTCTCTTCAGTTCTTG
GTTTCTCTCGCTCTAAACAAAAGATTGGGGGACGTGAAGTCTAAGGATTGGCAGACATATGCATTTCTAGACAATGTTGTTGCATTTGAGTGCAT
TCGCTAATTGTAAAAGTTGCCAATTCATCAGCGTCTGAGATCTGAAAAATTATGCTATATATAATTAGTTACTAGAGGGCTGGTTTCGGGCTTTC
ACCTCTATATACATGGGATAGTATAGTATGGTATGTATATAGTAATCAATATTTAGTCCAAGGGTTGTGAAAGGAAACTTTCTATAAAGAACAGG
ATACTTGATCGAAAGATGAGCCAGTGGCACTTATTTAAGTATCAATCGACCCGATTAACTTCTGCAGAGACAGTCATGCACCTGTTCATTCAATC
ATATACAATTAGTTCCCAGCAGGCCCAAACAAACTGAATAAATATACAAATGAACTCGTCTGTGTGTTCTTTAATTTGTCGCAAGTGTGCAAATC
AGAAAAATGTGACGAACCGAGCGTTGTTTATCAACAACAAAGAGAAAAAACAGACAGAACATGGGCAATCTAAATCGAGAACGGCACAACATACA
AAGGCAAACAAATTGGCGAAGAAGGCACAAACCGGTTGCCACTAAGGGAAGTCAGAGCCAAAAGAAAGCGATGGAACCAAAACCGGTTCATTGAA
CCTGCACACCACCGGCATCATGGTATAGACACACAGAACGATTCCAGCTCTTTATCACACAAAAAATCATTCTTTATTTATGCCATTTCTGTTTT
TAGTTGAGCACAATTACTTGCTTACGGAACGAAATGTAAATAAACATGGCGAGCTATGGTAAATGCAAATGTCTGGAAAAATCGATTATGCGTTT
ATGCTTAGTTCAAATCGGTTATGTTGCTGATGGATGACATGCTCCCCAAACACTTTAGTCGGTGGCATCGGCCTTGGCCACGGAGAAGGCCTCCG
AAACGGGCAGGGTGCCGCTGTTGGCGATGACCACATCCTTGACGGGACGGTCGCGGGCATCAGTGGCCGAGTTCTCGATCTGGCGCACCACATTC
ATGCCCGACAGGATCTTGCCGAAGACGACGTGGCGTCCATCCAGCCAGCTGGTCTGCTTGGTGGTGATGAAGAACTGCGATCCGTTGGTGTCCTT
GCCAGCGTTGGCCATGCTCAGCCAGCCGGCGCCATAGTGCTTCAGCTTGAAGTTCTCATCCTCGAAGCGCTCGCCGTAGATGGAGCGACCGCCGG
TGCCGTCGCCCTTGGTGAAGTCACCGCCCTGGATCATGAAGTCCTTGATGATGCGGTGGAACTTGCTGCCCTTGTAGCTGCGGGGTATAAGAGCG
TTGCATGATGGTCAGTTTTGTCAGCATGGGAATTTAAATTTAAAAAAAAACTGGGTTTAGAACTCGAAACCTAACCAAAAAAGAACATGCATACT
TATAAATTCAGAGAAGAAAAAAGAAATACCCAAGAACTGCACTTTTATAGTATGGTAGACTTAATAACAGTTGGCGTTCTTTGTTAACCCATTAG
TGCCGCTTTGTCAACTGATGTATGCGATTGGCCGCTCAAACGCCACGTAATTGCTTCAATCTGAGAGCCCCGCTATAACCTACAAAGTGCCGCTG
ATTAGCGGCATCTTTTGCTGGCCTAGCGGTACCTGGCACCCTACTATGTTGGGGTATTTTCGGTACTCAAGTACCCTACTCACCCCTCGCCCTGC
GGCTTCAGCGCCAGCTCCTTGAAGTTCTCCACCGTCTTGGGCACCGTCTTGCCGAACAGACCGATCTCGATGCGACCAGCGGGCTCGCCGCCAAT
GGTGATGTCAAAGAAAACCTACGCAATCGGAAGCGGTTTATTATTAACAAGTCATCTCACTTGATTTATGGCGCAGCAAATGTGTGTGTGTGTTT
GTGTGTGTATGTACGTGGTGTATGCAGAATGTAAGGACGAAAGTCCAAGGAGCACGCACCTTCTCGGTCACTTTGGGACCCTTGCTATCGTCGGC
AACAACGACGCCGGCCACCAGGGCTACCACGAAAACGGATAAGAACAGCTTCATCGTTCTAAATATTCACAGCGCTTCAGTTTATTCCTCAAGCG
ACGTCGCCAATGGATATTTCACGACTGAATTTTCGGTTTCTGTTAGTGATGTAAGAAAACTTTGTTGCATCGCCAATCGATGTTTTCCATCGTTT
TTTATGTTTTTGTCGAAATATCGATGCTTAAGTGTGACCATTCGATGACGATGTCTGATGATCACACATTCGGGCGGAAAATTCAAATTCAAATA
GTTAATACGCCGAAAGCATAAGTTAAGGTTTTCGTACGAAGGAACAAAGTAAGTTCGAAGAGTTGACTTTATTGGTATAGTTTTTAATATTTTAG
GGATTAGAAGTCCAGTTTGCATTAGCACGTAGCATTCTCTCTTGTTTTATTGACGGTTCTGTACACAAAAAGTAAGTAAAAAAATATGCTTTTAT
TTATTGGTGTACTGCTATTTGCGTCTGAGATTTGTCCATATCCTTGGCTGCCTTCTCTGCTCTCTTCTTCTCCCTGCTGGCCAGAACTTTCTCCC
TGGATTTCTGGGCCCTTTCAGCGCAATCCTTGGGTCGTGTCTTCAGGGTCATATCATCCACGGCCGCCTGTTTACGGGCTGATCTCGAAATGCAT
CGTTCCATGCAGCTGATGGGCACAAATCTTCCAATGAAGCAACCGCAGTGTGAACAATAGTGATTGATGTCCTGGCGGCCAGACCATTTTTTACT
GAAATAAAGTGAACATTACGAAAGATTTATAAAGCTTCATGCAGATGGCCAACCAAAGTTTTGTGAATCCCAGAAATCTCTGCAGGCAAGTGACC
AACTCCAGTTGCACCAAACTGGTTCCAGACTTCTCACACGAAGGACAACGGATCCAGGTGGGCTCCTCCTTCAGGTATCCCACTTGTGGCTTGTG
GCTGACAATGATGGCCACAATCTGCGGTTCGTCCACGGTCATGATGCGAGTTCCAGCGAGAACGATCGGTGACTGAAAGATGGATCAAATTTGGA
GAGATCATGGGAGGGAAAATCAAAATCAGAATCACTCTCCCGATTTCTCTTAACCGAGG
(SEQ ID NO: 247)

Exon: 2384..2245
Exon: 2108..1984
Exon: 1597..1001
Start ATG: 2334 (Reverse strand: CAT)

Transcript No. : CT9017
TGGCGACGTCGCTTGAGGAATAAACTGAAGCGCTGTGAATATTTAGAACGATGAAGCTGTTCTTATCCGTTTTCGTGGTAGCCCTGGTGGCCGGC
GTCGTTGTTGCCGACGATAGCAAGGGTCCCAAAGTGACCGAGAAGGTTTTCTTTGACATCACCATTGGCGGCGAGCCCGCTGGTCGCATCGAGAT
CGGTCTGTTCGGCAAGACGGTGCCCAAGACGGTGGAGAACTTCAAGGAGCTGGCGCTGAAGCCGCAGGGCGAGGGCTACAAGGGCAGCAAGTTCC
ACCGCATCATCAAGGACTTCATGATCCAGGGCGGTGACTTCACCAAGGGCGACGGCACCGGCGGTCGCTCCATCTACGGCGAGCGCTTCGAGGAT
GAGAACTTCAAGCTGAAGCACTATGGCGCCGGCTGGCTGAGCATGGCCAACGCTGGCAAGGACACCAACGGATCGCAGTTCTTCATCACCACCAA
GCAGACCAGCTGGCTGGATGGACGCCACGTCGTCTTCGGCAAGATCCTGTCGGGCATGAATGTGGTGCGCCAGATCGAGAACTCGGCCACTGATG
CCCGCGACCGTCCCGTCAAGGATGTGGTCATCGCCAACAGCGGCACCCTGCCCGTTTCGGAGGCCTTCTCCGTGGCCAAGGCCGATGCCACCGAC
TAAAGTGTTTGGGGAGCATGTCATCCATCAGCAACATAACCGATTTGAACTAAGCATAAACGCATAATCGATTTTTCCAGACATTTGCATTTACC
ATAGCTCGCCATGTTTATTTACATTTCGTTCCGTAAGCAAGTAATTGTGCTCAACTAAAAACAGAAATGGCATAAATAAAGAATGATTTTTTGTG
TGATAAA
(SEQ ID NO: 248)

FIGURE SHEET 133

Start ATG: 51 (Reverse strand: CAT)

MKLFLSVFVVALVAGVVVADDSKGPKVTEKVFFDITIGGEPAGRIEIGLFGKTVPKTVENFKELALKPQGEGYKGSKFHRIIKDFMIQGGDFTKG
DGTGGRSIYGERFEDENFKLKHYGAGWLSMANAGKDTNGSQFFITTKQTSWLDGRHVVFGKILSGMNVVRQIENSATDARDRPVKDVVIANSGTL
PVSEAFSVAKADATD*
(SEQ ID NO: 249)

Name: peptidyl-prolyl cis-trans isomerase (cyclophilin)
Classification: chaperone Celera Sequence No. : 142000013384827
CCCTGGTATCCGAGATCGTCGGTGGGATTACCAACAAGTGCCGCCAAATAATCAAGCGCTCCCGCAAGTCGGCCGCCTCCTCTTGGTCGTCGGCG
TCAAGTGGGTCAATGCTTCGCACTAATGCCGAGCAACTTTCCCATGATAAGCGAAAGGCCAATAGACGCGAGGCTGCTGAGGTTGCTCAAAAAAT
GAGTTTTGGAATGCGCGAGTTAAATCTTACCCGCGCAACGCTTCGGGAAATATACGGAAGCTACGGGGCACCTGAAACAGATCATGGTCAGCTAG
ACATCGTCCACACTGAGTTTCCAAACAGTTCTGCAAAATTAAATAATATTGAAGACGAAGAATCTCGGGAAGCTCTTGAATCTCTGCAGCGTTTA
GACGAATTTATGGACCAGATGGATAACGACGGCAATCCTTCCTCACATACATTCCGTATTGACAATTAATCACAGAAATTTTTAAATGCAAATAC
AAAATAATCACTTTAGTGCACATGAAATTATATGTATTGAAATAAAAAGTTTGATGCAACAACAAATTTTACAGTTGTTTGGTATTTTGTATGGG
AAAGTTTGTGGCAATATATGGTTTTACTTGAAAGCGGATTGGACATGGTCACACTGCCCACAAATCACAACATTGCGTTATAAATGAAGCACATC
TAGTTTTGTGTTAAGAAAGTGGTTCACAATTTATATAGCAGGTTATGGTAAAACATCGATCGTTCCGAAAAATTCCGCTCGTTGGCACATTTTCT
AAATTTTTCGTGCGACAGCGGTGATTATTATATGATATTATTATGATTATATATACAAAAATTATTATAATTATATAAAAGTTGGCGACCATATC
AAAAAGGTTGCTATAAAAACAAATGGCAATTTATAGCGGAGTTTCACTCCCAAAGCGATGTTCTCCACCCATTCCAGTCAGTCATGGTAAATATA
CCTTCTAAAAAATATATGATTTTTCGATAGAGATACACGGGCACACTAGACCCACCGATCGCGACTTTGTGTGTGTTAAAATGACGCGCATATC
GTTTTGGGCTAATAATATTGTTCACGTTTTATAAAACAGATACACGGTTAAGCTCTGACCGGTCGTATTATTATCTGTGTGTTCTTGGTTGACAC
GTTTATTTCATTTATTCTCATTTAAAGCAACGATGTGAAGAACAGTGCGGGCGTTTCTCAACATAAGAATACATACAAACTTATGCGTGATGGTG
AGCAAATAAAATAGTTCAAAAAATTACTCGGCCACCGCCTTAACCGTACAAACGGAAATACATAAAGGTAAAGGGCTCAACAACAGTATTACTGA
TTAGGCAATTGATTTATATTTCAAACTTCTTAAATAAAGTGTCCACAAATATGTATGTTCTTAGCATAGAGGCGTAGTCGGTGAGTCAGCCACGC
CAACAGTTAACAGTCGTCATTTTGCTGTCTGTCTAACACGCAATTTGTGTGTGTATATGTGAATAAACAGATACCGGTATGCAATCGCAAAGCTG
GTCAACTGTAAAGATCGGTATGTACTCAAAATTAGGTCATCACCTTGTTATGCAGATACATTTGGGAAACAGTTGACTTACTTGGTATTGGTTAT
CAGCCGAAAAGCAAATGGTGATACGGTTTTGCACCTCAGCTTACTCACGGATACATACCTACGTACATAAATGTATGTATACGGTATACAGTCTT
AGAAAAAATATTAGTACCGACCAGCTAGCGTTTGCCTAAAACGCTTTTACAAAAATAAACGTATATGTTTTAAGTTGTTTTTTGTCATAATTAAT
ACATTTATTATTATTTATTTATGAATTTCAGAGCTTTAATAGTAACTAAATTGTTTAAACAAACTTAAAAAAAGATTTACAAATAAAAAAATATT
TCGTGTGCGTGACGGAATTGCTAGTTCATTAAAGGGAGGTCATATGTACATACATACACATTGCAAAGAGTACAGATCGCTCATCATTTCATTTT
TCCTAATGTACATATACATATGTACAAACATGTTTATTAAACTGCCTACATGCAAATCTTTGAAGTTTTAAGAAAATAAGCACAACTAGTTTGGA
AAATCTTGGGAGCCAAGATCTATCTGTCCACTGATTTTCCTATGACTTCAAGAATGTAAAACCCTTTTTGTTAAACAAATTTTGATTAAAGTATA
CCAGAATAATATTAAACGTATCGTCCGTATCTATAAAAGGTATTAATAGTATTACCTAAATTTAAATTCTCGGTTTTATTCATAAGAGTGAAAAA
ATATACAAGTTCCTTTTTAATTTTTTACTTATTGAAAATTTGATTAATTTTTATTATTATTTTCAGTTTAGAATAAATTCGGCCACAATTAATAT
ACTTATTTATTCATCAAAACCAAACCACCACAAGAGCATAACCAATCATGTTAAAGTTTATCAGAGGAAAAGGGCAGCAGCCCAGTGCTGACAGA
CAACGCTACATCGTAAGGTAAAACAAACAATTTTCTCTTTCCGTTCTATTTTTTTTTTTTTAAGTATTTGTAGCCGATTGGTATATTTTGTGGGG
TCATTTATTTTGATCTTGGGTGGTAAATACATTTTTATGGAAGTTAGAAGAAAGCTTATAATTTATGAGGAATAAATAAATACCTCCTTTTGAAT
CTTTTGTTATGTCTTCTCCTATGTGCATACTTTTGGGCATTAACATTTAGGTAAATTTTTTCCACCGCAACTACAAGTAAACCGCATACACACAC
AGTATTTTGTAGACTCGCGCCACAAAGCACCGCATAAAAAAGGTTACGGTGCTTTTTTGCTCGTTTCTTTTGTGCACTCCTTCTATGCGGTGCCA
AATATGAGGAGGTACCTGAAGCTTGGTTGATTTTGTGAGTGTCTTTTTCCACAGCATATTTTTGTGTATTGGCTACTTTAAAAATTCTATTATAT
CGTTGTGCTCGTAATGTTGTCCATTCCTTTTAAATATTTTCGAATTAAATATACCATAGATGTTTCCCTATTACCATAATAGTTTAATAAATATA
CGTATATGAAATTTTTTTTATCCTATGTTAGTATAAACATGTTATTCAACAAATAAAAGTAGGTCAGAGGTAATCGCCATCCAGCTCCAGAAAGA
GGGGGGAGCTGATAAGATTGCGTTTATGTACCTAATGGGTTGGGTAAGTGGCTTGGTTTCACAAACACCCTTATTTCAGGTACAAAATAAGTATG
TCATAGACGGCGTAAAATTGATAAGATTTTAAAGTCAAAAGAAAATGAGTTTATTCGCCTGTAACTGCGTTAGAAATCCAAATACACCCGCAATA
TTATATGTATAGAAAGAAAAAGTTTGATGCAACAACAAATTTAAAGTTGTTTGGTATTTTGTAATGGAAAGTTTGTGTCACTAAATATGGTTTTA
CTTGAACGCAGATTGGACATGGTCACACTGCCCACAAAATCACGACATTGCGTTATAAATGAAGCACATCTAGTTTTGTGTTGAAAATGTGGTTC
ACAATTTATATAGCAGGTTATGGTAAAACATCGATCGTTCCGAAAAATTCCGCTCGTTGGCACATTTCCTAAATTTTTCGTGCGACAGCGGTGAT
TAATTACAAAAATTATTATTATAATTATATAAAAGTTGGCGACCATATCAAAAAGGTTGCTATAAAAACAAATGACAATTTATAGCGGAGTTTCA
CTCCCAAAGCGATGTTCTCCACCCATTCCAGTCAGTCATGGAAAATATACCTTCTAAAAAATATATGATTTTTCGATAGAGATACACGGGCACA
CTAGACCCACCGATCGCGACTTTGTGTGTGTTAAAATGACGCGCATATCGTTTTGGGCTAATAATATTGTTCACGTTTTATAAAACAGATACACG
GTTAAGCTCTGACCGGTCGTATTATTATCTGTGTGTTCTTGGTTGACACGTTTATTTCATTTATTCTCATTTAAAGCAACGATGTGAAGAACAGT
GCGGGCGTTTCTCAACATAAGAATACATACAAACTTATGCGTGATGGTGAGCAAATAAAATAGTTCAAAAAATTACTCGGCCACCGCCTTAACCG
TACAAACGGAAATACATAAAGGTAAAGGGCTCAACAACAGTATTACTGATTAGGCAATTGATTTATATTTCAAACTTCTTAAATAAAGTGTCCAC
AAATATGTATGTTCTTAGCATAGAGGCGTAGTCGGTGAGTCAGCCACGCCAACAGTTAACAGTCGTCATTTTGCTGTCTGTCTAACACGCAATTT
GTGTGTGTATATGTGAATAAACAGATACCGGTATGCAATCGCAAAGCTGGTCAACTGTAAAGATCGGTATGTACTCAAAATTAGGTCATCACCTT
GTTATGCAGATACATTTGGGAAACAGTTGACTTACTTGGTATTGGTTATCAGCCGAAAAGCAAATGGTGATACGGTTTTGCACCTCAGCTTACTC
ACGGATACATACCTACGTACATAAATGTATGTATACGGTATACAGTCTTAGAAAAAATATTAGTACCGACCAGCTAGCGTTTGCCTAAAACGCTT
TTACAAAAATAAACGTATATGTTTTAAGTTGTTTTTTGTCATAATTAATACATTTATTATTATTTATTTATGAATTTCAGAGCTTTAATAGTAAC
TAAATTGTTTAAACAAACTTAAAAAAAGATTTCCAAATAAAAAAATATTTCGTGTGCGTGACGGAATTGCTAGTTCATTAAAGGGAGGTACATAT
GTACATACATACACATTGCAAAGAGTACAGATCGCTCATCTTGCATCTCATTTTTCCTAATGTACATATACATATGTACAAACATGTTTATTAAA
CTGCCTACATGCAAATCTTTGAAGTTTTAAGAAAATAAGCACAACTAGTTTGGAAAATCTTGGGAGCCAAGATCTATCTGTCCACTGAATTTCCT
ATGACCAAGAATGTAAAACCCTTTTTGTTAAACAAATTTTGATTAAAGTATACCAGAATAATATTAAACGTATCGTCCGTATCTATAAAAGGTAT
TAATAGTATTACCTAAATTTAATTTCTCGGTTTTATTCATAAGAGTGAAAAAATATACAAGTTCCTTTTTAATTTTTTACTTATTGAAAATGTGA
TTAATTTTTATTTATTATTTTCAGTTTAGAATAAATACGGCCACAATTAGTATACATATTTATTCATCGAAACCAACCCACCACAAGAGCATAAC
CAATTATGTTAAAGTTTATCAGAGGAAAAGGGCAGCAGCCCAGTGCTGACAGACACCGCCTACAGAAGGACCTTTTTGCTTATCGTAAGGTACAA
CAAACAATTTTCTCTTTCCATTCTATTTTATTTTTTTTTTTTCGTATATGTAGCCGATTGGTATATTTTGTGGGGTGTCATTTATTTTGATCCTG
GGTGGTAAATACATTTTTATGGAAGTTAGAAGAAAGCTTATAATTTATTAAGAATAAATAAATACCTCCTTTTCAATCTTTTGTTATGTCTTCTC

FIGURE SHEET 134

CTATGTGCATACTTTTGGGCATTAACATTTAGGTAAATTTTTTCCACCGCAACTACAAGTAAACCGCATACACACACAGTATTTTGTAGACTCGC
GCCACAAAGCACCGCATAAAAAAGGTTACGGTGCTTTTTTGCTCGTTTCTTTTGTGCACTCCTTCTATGCGGTGCCAAATATGAGGAGGTACCTG
AAGCTTTGTTGATTTTGTGAGTGTCTTTTTCCACCGCCTGTTTTTGGCTACTTTAAAAATTCTATTATATCGTTGTGCTCGTAATGTTGTCCATT
CCTTTTAAATATTTTCGAATTAAATATACCATAGATGTTTCCCTATTACCATAATAGTTTAATAAATATACGTATATGAAATTTTATAAGAATTT
TTTTTATCCCATGTTAGTATAAACATGTTATTAAACAAATAAAAGTAGGTCAGAGGTAATCGCCATCCAGCTCCAGAAAGAGGGGGGAGCTGATA
AGATTGCTTTTATGTGCTTAATGGGTTGGGTAAATGGCTTGGTTTCACAAACACCCTTATTTCAGGCACAAAATAAGTATGTCATAGACGGCGTA
AAATTGATAAGATTTTAAAGTCAAAAGAAAAAGAATTTATTCGCCTGTAACTGCGTTAGAAATCCAAATACACCTGCAATATGAATCAAACAAAA
TCAACTCATAACGAGATCTGATAGCAACTTCTTAAAACTTTTTTTGTATAAAAAATACAATTTATACAATTAGATAAGATTTACCAAACCTTTTTT
CGATCAATGTAAATATAGTATGATAGTAGGGACTGCTGTCTACAGTGATGTTTATAAGAGACATACTTAAGAGCAGCATTTAAAGCTTTGGGCGC
TTTTTGAACTTAATTTAAATTCAAACCTCAATATTTATTGAGGTTTTTATTCCCGTTAATTGTAAAGAAAAAATGCTGTATTAGATTCGGTAAAAG
TATGTAAATGGTTTAAGAAAGCGTTCCCGACTCTATAAAGTGGCAAGTAATCTGACGATTTACCAGATCTTGGGAACTGAAAAAACTAGAATGTT
TTGGAAAACCCTTTTACAATTAAGAAATGAACCAAACAATTTTGAATTATTAAGAATCTGTAATTGCTTTTTGAAACTTTTTAATATTTTTTTCT
TTTAGACGGCACAGCATGGCTTTCCTCATAAGCCTTCGGCTCTTGCGTATGATCCAGTTTTGAAACTTATGGCAATAGGGACGCAAACAGGGGCT
TTAAAAGTTTTCGGTCAACCCGGAGTTGAATTGTACGGTCAGCATACTTTGTTAAACAATTCAGCATCGGAGCTTAATGTACAATTACTTGAATG
GGTGTATGGAACTGGTCGCATACTTTCGTTGACGGCAGCGAATCAATTAATTCTATGGGAGCCAGTTGGAGCAACGTTGCTGCCAATCAAAACAC
TACCGTTTGACGGCAAACTTAAAAAAGTTTCATCGCTGTGCTGTTCTCTCAGTAAGGATCTGCTATGGATTGGAACAGAAGGTGGAAACATCTAT
CAACTGGATTTACATACATTTACCATTAAGGAGCCTGTAATTTACCATGACGTTGTGCTAGAGCAGGTGCCACCAGCCTACAAGCTAAATCCTGG
TGCAATTGAGTCAATCCGCCAACTTCCAAACTCCCCTAGCAAACTTCTAGTTGCATACAATCGCGGCCTTTGTGTTTTGTGGGATTTTGAAAGCG
CATCTGTCCAGCGAGCATACATAGCCCCTGGACATGGACAGAGCGTTGGTCTTACAGTGAACTTCGAAGGATCTGAATTTACCTGGTACCACGCT
GATGGTTCATACGCCACTTGGAGCATAGATAACCCAGAACCGCCGTCGAATGTTAATTATGTGCCTTATGGACCTGATCCATGCAAAAGCATAAA
TCGACTGTACAAAGGCAAGCGAAGGTTAATATAACTTAAACACAAAGTTTTTAGATGTGTACTAATTTCTCGTTCTTTTAGATCCAACGATGTA
ATTGTTTTTTCCGGCGGCATGCCACGGTCAGCATATGGTGATCACAATTGTGTGTCCGTTCACGCCAGCGATGGACACAAAGTGTGTCTTGACTT
TACGTCTAAAGTGATTGACTTTTTTGTGACCTTTGAAAATAATAGAGATGTCGCTGAAGTTCTTGTTGTACTACTTGAAGAGGAACTCTGCGCTT
ACGATCTTACTGACCCTAATATTTGTGCTATCAAAGCGCCATATCTTCACTCTGTCCATGCATCAGCTGTCACTTGCAATTACCTTGCTTCTGAA
GTCGTACAGTCGGTATATGAAAGTATTTTAAGAGCTGGAGATGAACAAGACATTGACTATAGCAATATTAGCTGGCCTATCACTGGCGGTACTCT
CCCGGATAACTTAGAAGAATCTGTAGAAGAGGACGCGACTAAGCTTTATGAGATTTTGTTAACTGGTCACGAAGATGGTTCTGTTAAATTTTGGG
ACTGCACTGGAGTGTTGCTTAAACCAATTTATAATTTTAAAACTAGCAGCATTTTTGGAAGTGAGTCAGACTTCCGAGATGACGCAGCTGCAGAT
ATGAGTGCGGAACAAGTCGATGAAGGAGAACCGCCATTTCGGAAATCAGGACTTTTTGATCCTTATTCAGATGACCCTCGTTTAGCAGTGAAGAA
AATAGCATTCTGCCCAAAAACCGGACAACTTATTGTTGGTGGCACAGCGGGCCAAATAGTTATAGCCGACTTCATAGACTTACCCGAAAAAGTGT
CTTTAAAATACATTTCAATGAATTTGGTCAGCGATCGTGATGGATTTGTGTGGAAGGGTCACGATCAGTTAAACGTGCGATCGAACTTATTAGAC
GGAGAAGCAATTCCTACGACGGAACGTGGTGTAAATATATCGGGAGTACTGCAAGTTTTGCCGCCAGCCAGCATAACATGCATGGCACTCGAAGC
AAGCTGGGGCCTAGTATCTGGTGGGACTGCGCACGGCTTAGTTCTCTTTGACTTCAAAAACTTTGTTCCAGTATTTCATCGCTGCACTTTAAACC
CAAATGATCTTACTGGAGCAGGAGAGCAGCTGTCTCGTCGAAAGTCTTTTAAGAAATCATTGAGGGAGTCATTTAGAAAGCTTCGCAAGGGTCGA
TCGACCAGGACCAACCAGAGCAATCAAGTACCAACAACGGTTAGTAAGATAATATATACTCAACTAGTCTTTTATATTAAATTCACAATCCTACA
GCTGGAAGCAAGACCCGTCGAGAGGCAAATAGAGGCTCGTTGTGCAGATGACGGGCTAGGATCCATGGTGCGATGTTTACTATTTGCCAAAACTT
ATGTTACTAATGGTAATCAACATTTTGTACTGTTATTAGTTTTGATGTAACGATAAAAAAAAAAAAAGGTAACGGAAATAGTCTCTGAACCACGG
CCTCGCGAGAATTGAACCCAAAAGCTAAAAACATACAGTGCTTTTCATTTTGGGACGCCCAGAGCTTTAATTATATTTTTGTGCAACAAATTTTT
ATGCATTGGATATATTGATCAAAGTTTTAAAGGTATATGTATTTATGATCAGTTTAAACAGCCGACTACATTTGACTATGTCCGTCCTTAGAAAG
AAATTCAGTCATTACAATATTCCTTGCTAGTCTATCGATATGCTATAAGTGTTAAAAGTGCTTTTGCATTTACTCTGGTTTGACAATATATTTTA
TTGATATTGATTTCGTTTCATTTACTAGTTGGAAAACAGTTCTTAAACTAATTAAATCATAGTCTTTTTGTTTTCGCGATTTCGATCTATATGGC
AAATTTTGTTTTTAAAATTTCACCTATCCTCCTACTATTTCTGTAATGGGTAACTCGACTGTAGCGTCTATTCTTTTGGTGTTCTGTATATGTAC
ATCTAATTTGTTGTATAATTTTTACATTTTCAGTCAACATAACGTCGCCAACTTTGTGGTCAGCAACAAATGCCAGTACAGTCTCGGTTTTCCTT
CTGCATTTGCCACCAGCGCAGACCGCGGCAACTGCCGTCCCGTCGGCAAGTGGCAATGCACCACCACACATGCCCCGCCGAATTTCTGCGCAGCT
TGCTAAAGAAATACAATTAAAACATCGTGCTCCTGTGGTGGGTATTTCTATTTTTGATCAGGCGGGTAGCCCTGTCGATCAGCTGAACGCCGGTG
AAAACGGGAGTCCACCGCATCGTGTACTTATTGCTTCCGAGGAACAGTTCAAGGTGTTTTCACTTCCGCAACTAAAGCCGATTAACAAATATAAG
CTTACCGCTAACGAAGGTGCTCGGATTCGCCGCATCCATTTTGGTTCGTTTAGTTGTCGCATATCCCCGGAAACACTGCAGAGTATGCACGGTTG
TAGCCCAACTAAGTCCACGCGTTCACATGGCGATGGAGAGGCGGATCCTAATATCAGTGGAAGCTTGGCTGTAAGTCGTGGAGATGTATATAACG
AAACAGCATTGATATGTTTAACGAATATGGGCGATATCATGGTTTTATCAGTACCTGAATTAAAAAGACAGCTGAATGCCGCAGCAGTGCGACGG
GAAGACATTAAGTAAGTCACGCATAGTGCTATTATTTTAATTTTTTGGACCTAATACTGTATTTTAACTTTTCAGTGGAGTTTCGTCACTTTGCT
TTACAAACTCTGGAGAAGCACTGTATATGATGTCTTCTTCTGAACTGCAGCGTATTGCTTTAGCCACGTCCAGAGTCGTGCAACCCACTGGCGTT
GTTCCAGTAGAACCATTAGAAAATGAAGAGTCTGTGTTGGAAGAAAATGATGCAGAGAATAATAAGGAAACCTACGCATGTGATGAAGTTGTGAA
TACATATGAAATTAAAAATCCATCAGGCATTTCAATATGCACAAGGCCTGCAGAGGAAAACGTTGGAAGAAATAGTGTTCAGCAAGTTAATGGAG
TCAACATTTCAAATTCACCTAATCAAGCTAACGAGACTATCAGCAGCTCTATTGGCGATATTACCGTTGACTCGGTGCGCGACCATTTAAATATG
ACGACCACCACTTTGTGTTCTATTAATACAGAGGAAACCATTGGTGAGTAATCATTTATTTACTAACATTATTCCACCTATTTTAATTTGCTGTT
TTGTACGTATCTACATTTAAATGTTTTCGTTTCGACATTAGTTACTTTCGGCAACATAATTCTTATAAAAATTTACTTTTTAAAAACTTGATTTT
AAGTATACGCACCAAACAACTTTAAATATATACTTTTATCTTATTTTAAAAGCACGGGCCCACATTATATCTGTACATAACTTTTTTTTTCTGTC
ATCTCTATGAAAATGTAGGTCGCCTATCTGTACTTAGCACGCAAACCAACAAAGCCAGTACTACCGTAAACATGAGTGAAATTCCAAATATTAAT
ATTTCTAATTTAGAGGACTTGGAATCGAAAAGGTGTGCTTCTACAAGAAACATTGACATAAGCTTTAACCTACTAATTTTTTTTTTTTACCTAAC
AGAAATACGACGGAAACGAGTACTAGTTCTGTTGTAATTAAATCTATAATTACAAACATTTCTCATGAAAAAACGAACGGAGACAACAAAATAGG
AACGCCAAAAACAGCGCCTGAAGAAAGCCAATTTTAACATTGACAGAAGCCGTAACCTACTAATTATTTTATACCTTTACAGAAATACGACGCAA
ACGAGTACTAGTCCTGATGTAATTTAATCTATAATTACAAACATGTCTCACTAAAAATCGAACGGGGACAGCAAAATAGGAACGCAAAAAAATTA
AATTAAATTAAACGCGATTTACATACAAACAGAAATGACAGAATGATAATATAAAATATTCATTTTTTATTTGGCTTAAGCGATGTTGTTGTTCC
AAAACCATATAATTATTTATGATTTTATGTAATGTTTTCATGTATTTTCGCGTAGTGACTTTATACCCTTTACCCGTATGATGAAACGAAACATG
ATATTTGTAGAAAGGTACAAAGGATAAAAGTTGACATTTAAGGCCGATTGTAAAATATTAAAACGCAACCTGGATAACATGCCGATTAATTACTT
CTGTTCGTCCGTATAAACACAAATACCGATAAATTGGTCCGTCCCCATTTAATAAATTGTATATTAAAATGGTCTTTATTTTGGATAAATAATTC
AAATTATATAGGAACATTTGGGTTTTAAGGGATAGAAACAGCGCTGGTGTCTTTCATTTCCGTTCGTATGACCGTTCAAAGATTATAAAAAAATT
GTCGTGCCCACATTTTTTAAATTTCTTTTATTTTCGGTTAAAATATTGTGATACAAAAAAATGCCCTTACAAAATTAGGACAACAACAATTTGCT
TTATTATGATGAACAAATTAGGAGTACAAAAAATAGCCTGATGCAAGGATGGGGAGAAAAAAGACCTTGAAGTTCAAAAGAATTTGTTGTATCAA
ATCCTCAATAAGAAAACTACTTAAAATTAAAAGCGTGTTTCAAATTAATTGTAGAATATTTCGTAAAATGAAATTGCAAACTTTTTTAGCACGAA
ATTACATGTATTTAATTCTTTGGCTAATACGTCAGTTAAAAAAGGCTACATTTTGATGATACTCACAAATGTAATTTTTGCATTCTACACAGGTG
CAATTAAAAAATTATGGTTTTTATGAGTTTTAGAGGGAAGAAAATATGTCAATATGAGAAGTAAGTTAATGAGCCTTCAAGTACTTTAGTACATA

FIGURE SHEET 135

ATGTAATTTAATTTTAGAAATCCTACGGCTTTATATTCAATTGTAAAGTATTTTAAAATTCCTGACGATTTGTAGTAATTGTTTTGTTCTTAGCT
TTTTTGCATTCTCCTCCGTTACTCCGTTACTCGTATAGTAAAAGGTATAGTATATACAATAGTATTGTAGATTCGTTGAGAAGTATGTTACAGGC
AGAAGGAAGCTTTTCCGACCATATAAAGTATATAATTGAGTATTTAGCTTAGGATTATTAATAAAACATGTATTTTATTTAACAAACTGGCTTTA
CAATATTTTGTGGAAGAACACCGATCTATTTAGTTGTAGGTCTCAAACTGAAAACTCCTAATTTTGACTTATTTAAAGATCATACCTCGGTTTTG
AGCCTTAGAGGTTTGTATGAGTGATTTTCTAGAATGATCTTTGTACTTCGTTACAATAAATTGTTTTCTTCTACTCTAATATAGTTGGAATCGAG
TAATCCCTAGATAAGAGTTAGGCTTAAAATAGTAAATTACAAATATTGAATTGGACATTACAATTGCATATTCTCAGCTTGCTGTATTGTAAAAA
TTAATTATTAACTCGAAGAGATTCGGCAATTAATACGTCCCTATTCGCATTGTTTTTACTTGGGGAAATTTTATTGAAAAACTAGATTCTCTGTT
ACAATCAGATATGAGAACAAGTTATTGCACCAGCACATCTCTCGGCCAGCTCAATTCAATTAAATAGCTAAGCACTTGTTGCGAATTCATGCTTG
GAGTGTTTACGTAAGATTTGTAAAAATAACTAAACTGGATTCTCCACATTCTTGCGTAGCTGTGTGATTCTACTGTCACAACTCTCCGTCGACGA
TTTCTAGAGCCATCTTCTTGCGGAAGTACAACATTTCCGACTGGGTAAAGGTAATTGGCACATCACACGTTATATACTCGGCGAACATGCAGCTG
AAGATACCGCAATCGCTGCCATCTAACTGTCGTGGTATATTCTGCACGCTCTCAATAACAAAATCGCTGGTATCAAACTGCTTTTTGGGCTTGAA
TATTGACTCTTCGCGTAGATATTTCTCTAGAGCGTCCAGCACTGGTCGGTTTGGCTTTCCCTTTGAGTCATAATACCGGATTGTCTTGTTCCGCA
AGTGTATGATGGCCATGCACCAGTGGACGCCGTTGCAGTGCACTGGTACCGGGATTATGTCCTTGCTGAACAAGTCCACTTTGCGAGTCCAGCGC
TTAATGCCTGCATGCCCAGCTTGCAGGAGGCGGGG
(SEQ ID NO: 250)

Exon: 1001..1302
Exon: 5155..5314
Exon: 6656..7434
Exon: 7493..8684
Exon: 8742..8847
Exon: 9439..10081
Exon: 10146..10588
Exon: 10849..10957
Exon: 11023..12525
Start ATG: 5231

Transcript No. : CT9059
ACCCACCGATCGCGACTTTGTGTGTGTTAAAATGACGCGCATATCGTTTTGGGCTAATAATATTGTTCACGTTTTATAAAACAGATACACGGTTA
AGCTCTGACCGGTCGTATTATTATCTGTGTGTTCTTGGTTGACACGTTTATTTCATTTATTCTCATTTAAAGCAACGATGTGAAGAACAGTGCGG
GCGTTTCTCAACATAAGAATACATACAAACTTATGCGTGATGGTGAGCAAATAAAATAGTTCAAAAAATTACTCGGCCACCGCCTTAACCGTACA
AACGGAAATACATAAAGTTTAGAATAAATACGGCCACAATTAGTATACATATTTATTCATCGAAACCAACCCACCACAAGAGCATAACCAATTAT
GTTAAAGTTTATCAGAGGAAAAGGGCAGCAGCCCAGTGCTGACAGACACCGCCTACAGAAGGACCTTTTTGCTTATCGTAAGACGGCACAGCATG
GCTTTCCTCATAAGCCTTCGGCTCTTGCGTATGATCCAGTTTTGAAACTTATGGCAATAGGGACGCAAACAGGGGCTTTAAAAGTTTTCGGTCAA
CCCGGAGTTGAATTGTACGGTCAGCATACTTTGTTAAACAATTCAGCATCGGAGCTTAATGTACAATTACTTGAATGGGTGTATGGAACTGGTCG
CATACTTTCGTTGACGGCAGCGAATCAATTAATTCTATGGGAGCCAGTTGGAGCAACGTTGCTGCCAATCAAAACACTACCGTTTGACGGCAAAC
TTAAAAAAGTTTCATCGCTGTGCTGTTCTCTCAGTAAGGATCTGCTATGGATTGGAACAGAAGGTGGAAACATCTATCAACTGGATTTACATACA
TTTACCATTAAGGAGCCTGTAATTTACCATGACGTTGTGCTAGAGCAGGTGCCACCAGCCTACAAGCTAAATCCTGGTGCAATTGAGTCAATCCG
CCAACTTCCAAACTCCCCTAGCAAACTTCTAGTTGCATACAATCGCGGCCTTTGTGTTTTGTGGGATTTTGAAAGCGCATCTGTCCAGCGAGCAT
ACATAGCCCCTGGACATGGACAGAGCGTTGGTCTTACAGTGAACTTCGAAGGATCTGAATTTACCTGGTACCACGCTGATGGTTCATACGCCACT
TGGAGCATAGATAACCCAGAACCGCCGTCGAATGTTAATTATGTGCCTTATGGACCTGATCCATGCAAAAGCATAAATCGACTGTACAAAGGCAA
GCGAAGATCCAACGATGTAATTGTTTTTCCGGCGGCATGCCACGGTCAGCATATGGTGATCACAATTGTGTGTCCGTTCACGCCAGCGATGGAC
ACAAAGTGTGTCTTGACTTTACGTCTAAAGTGATTGACTTTTTTGTGACCTTTGAAAATAATAGAGATGTCGCTGAAGTTCTTGTTGTACTACTT
GAAGAGGAACTCTGCGCTTACGATCTTACTGACCCTAATATTTGTGCTATCAAAGCGCCATATCTTCACTCTGTCCATGCATCAGCTGTCACTTG
CAATTACCTTGCTTCTGAAGTCGTACAGTCGGTATATGAAAGTATTTTAAGAGCTGGAGATGAACAAGACATTGACTATAGCAATATTAGCTGGC
CTATCACTGGCGGTACTCTCCCGGATAACTTAGAAGAATCTGTAGAAGAGGACGCGACTAAGCTTTATGAGATTTTGTTAACTGGTCACGAAGAT
GGTTCTGTTAAATTTTGGGACTGCACTGGAGTGTTGCTTAAACCAATTTATAATTTTAAAACTAGCAGCATTTTTGGAAGTGAGTCAGACTTCCG
AGATGACGCAGCTGCAGATATGAGTGCGGAACAAGTCGATGAAGGAGAACCGCCATTTCGGAAATCAGGACTTTTTGATCCTTATTCAGATGACC
CTCGTTTAGCAGTGAAGAAAATAGCATTCTGCCCAAAAACCGGACAACTTATTGTTGGTGGCACAGCGGGCCAAATAGTTATAGCCGACTTCATA
GACTTACCCGAAAAAGTGTCTTTAAAATACATTTCAATGAATTTGGTCAGCGATCGTGATGGATTTGTGTGGAAGGGTCACGATCAGTTAAACGT
GCGATCGAACTTATTAGACGGAGAAGCAATTCCTACGACGGAACGTGGTGTAAATATATCGGGAGTACTGCAAGTTTTGCCGCCAGCCAGCATAA
CATGCATGGCACTCGAAGCAAGCTGGGGCCTAGTATCTGGTGGGACTGCGCACGGCTTAGTTCTCTTTGACTTCAAAAACTTTGTTCCAGTATTT
CATCGCTGCACTTTAAACCCAAATGATCTTACTGGAGCAGGAGAGCAGCTGTCTCGTCGAAAGTCTTTTAAGAAATCATTGAGGGAGTCATTTAG
AAAGCTTCGCAAGGGTCGATCGACCAGGACCAACCAGAGCAATCAAGTACCAACAACGCTGGAAGCAAGACCCGTCGAGAGGCAAATAGAGGCTC
GTTGTGCAGATGACGGGCTAGGATCCATGGTGCGATGTTTACTATTTGCCAAAACTTATGTTACTAATGTCAACATAACGTCGCCAACTTTGTGG
TCAGCAACAAATGCCAGTACAGTCTCGGTTTTCCTTCTGCATTTGCCACCAGCGCAGACCGCGGCAACTGCCGTCCCGTCGGCAAGTGGCAATGC
ACCACCACACATGCCCCGCCGAATTTCTGCGCAGCTTGCTAAAGAAATACAATTAAAACATCGTGCTCCTGTGGTGGGTATTTCTATTTTTGATC
AGGCGGGTAGCCCTGTCGATCAGCTGAACGCCGGTGAAAACGGGAGTCCACCGCATCGTGTACTTATTGCTTCCGAGGAACAGTTCAAGGTGTTT
TCACTTCCGCAACTAAAGCCGATTAACAAATATAAGCTTACCGCTAACGAAGGTGCTCGGATTCGCCGCATCCATTTTGGTTCGTTTAGTTGTCG
CATATCCCCGGAAACACTGCAGAGTATGCACGGTTGTAGCCCAACTAAGTCCACGCGTTCACATGGCGATGGAGAGGCGGATCCTAATATCAGTG
GAAGCTTGGCTGTAAGTCGTGGAGATGTATATAACGAAACAGCATTGATATGTTTAACGAATATGGGCGATATCATGGTTTTATCAGTACCTGAA
TTAAAAAGACAGCTGAATGCCGCAGCAGTGCGACGGGAAGACATTAATGGAGTTTCGTCACTTTGCTTTACAAACTCTGGAGAAGCACTGTATAT
GATGTCTTCTTCTGAACTGCAGCGTATTGCTTTAGCCACGTCCAGAGTCGTGCAACCCACTGGCGTTGTTCCAGTAGAACCATTAGAAAATGAAG
AGTCTGTGTTGGAAGAAAATGATGCAGAGAATAATAAGGAAACCTACGCATGTGATGAAGTTGTGAATACATATGAAATTAAAAATCCATCAGGC
ATTTCAATATGCACAAGGCCTGCAGAGGAAAACGTTGGAAGAAATAGTGTTCAGCAAGTTAATGGAGTCAACATTTCAAATTCACCTAATCAAGC
TAACGAGACTATCAGCAGCTCTATTGGCGATATTACCGTTGACTCGGTGCGCGACCATTTAAATATGACGACCACCACTTTGTGTTCTATTAATA
CAGAGGAAACCATTGGTCGCCTATCTGTACTTAGCACGCAAACCAACAAAGCCAGTACTACCGTAAACATGAGTGAAATTCCAAATATTAATATT
TCTAATTTAGAGGACTTGGAATCGAAAAGAAATACGACGGAAACGAGTACTAGTTCTGTTGTAATTAAATCTATAATTACAAACATTTCTCATGA
AAAAACGAACGGAGACAACAAAATAGGAACGCCAAAAACAGCGCCTGAAGAAAGCCAATTTTAACATTGACAGAAGCCGTAACCTACTAATTATT
TTATACCTTTACAGAAATACGACGCAAACGAGTACTAGTCCTGATGTAATTTAATCTATAATTACAAACATGTCTCACTAAAAATCGAACGGGGA
CAGCAAAATAGGAACGCAAAAAAATTAAATTAAATTAAACGCGATTTACATACAAACAGAAATGACAGAATGATAATATAAAATATTCATTTTTT ATTTGGCTTAAGCGATGTTGTTGTTCCAAAACCATATAATTATTTATGATTTTATGTAATGTTTTCATGTATTTTCGCGTAGTGACTTTATACCC
TTTACCCGTATGATGAAACGAAACATGATATTTGTAGAAAGGTACAAAGGATAAAAGTTGACATTTAAGGCCGATTGTAAAATATTAAAACGCAA
CCTGGATAACATGCCGATTAATTACTTCTGTTCGTCCGTATAAACACAAATACCGATAAATTGGTCCGTCCCCATTTAATAAATTGTATATTAAA
ATGGTCTTTATTTTGGATAAATAATTCAAATTATATAGGAACATTTGGGTTTTAAGGGATAGAAACAGCGCTGGTGTCTTTCATTTCCGTTCGTA
TGACCGTTCAAAGATTATAAAAAAATTGTCGTGCCCACATTTTTTAAATTTCTTTTATTTTCGGTTAAAATATTGTGATACAAAAAAATGCCCTT
ACAAAATTAGGACAACAACAATTTGCTTTATTATGATGAACAAATTAGGAGTACAAAAAATAGCCTGATGCAAGGATGGGGAGAAAAAAGACCTT
GAAGTTCAAAAGAATTTGTTGTATCAAATCCTCAATAAGAAAACTACTTAAAATTAAAAGCGTGTTTCAAATTAATTGTAGAATATTTCGTAAAA
TGAAATTGCAAACTTTTTTAGCACGAAATTACATGTATTTAATTCTTTGGCTAATACGTCAGTTAAAAAAGGCTACATTTTGATGATACTCACAA
ATGTAATTTTTGCATTCTACACAGGTGCAATTAAAAAATTATGGTTTTTATGAGTTTTAGAGGGAAGAAAATATGTCAATATGAGAAGTAAGTTA
ATGAGCCTTCAAGTACTTTAGTACATAATGTAATTTAATTTTAGAAATCCTACGGCTTTATATTCAATTGTAAAGTATTTTAAAATTCCTGACGA
TTTGTAGTAATTGTTTTGTTCTTAGCTTTTTTGCATTCTCCTCCGTTACTCCGTTACTCGTATAGTAAAAGGTATAGTATATACAATAGTATTGT
AGATTCGTTGAGAAGTATGTTACAGGCAGAAGGAAGCTTTTCCGACCATATAAAGTATATAATTGAGTATTTAGCTTAGGATTATTAATAAAACA
TGTATTTTATTT
(SEQ ID NO: 251)

Start ATG: 379

MLKFIRGKGQQPSADRHRLQKDLFAYRKTAQHGFPHKPSALAYDPVLKLMAIGTQTGALKVFGQPGVELYGQHTLLNNSASELNVQLLEWVYGTG
RILSLTAANQLILWEPVGATLLPIKTLPFDGKLKKVSSLCCSLSKDLLWIGTEGGNIYQLDLHTFTIKEPVIYHDVVLEQVPPAYKLNPGAIESI
RQLPNSPSKLLVAYNRGLCVLWDFESASVQRAYIAPGHGQSVGLTVNFEGSEFTWYHADGSYATWSIDNPEPPSNVNYVPYGPDPCKSINRLYKG
KRRSNDVIVFSGGMPRSAYGDHNCVSVHASDGHKVCLDFTSKVIDFFVTFENNRDVAEVLVVLLEEELCAYDLTDPNICAIKAPYLHSVHASAVT
CNYLASEVVQSVYESILRAGDEQDIDYSNISWPITGGTLPDNLEESVEEDATKLYEILLTGHEDGSVKFWDCTGVLLKPIYNFKTSSIFGSESDF
RDDAAADMSAEQVDEGEPPFRKSGLFDPYSDDPRLAVKKIAFCPKTGQLIVGGTAGQIVIADFIDLPEKVSLKYISMNLVSDRDGFVWKGHDQLN
VRSNLLDGEAIPTTERGVNISGVLQVLPPASITCMALEASWGLVSGGTAHGLVLFDFKNFVPVFHRCTLNPNDLTGAGEQLSRRKSFKKSLRESF
RKLRKGRSTRTNQSNQVPTTLEARPVERQIEARCADDGLGSMVRCLLFAKTYVTNVNITSPTLWSATNASTVSVFLLHLPPAQTAATAVPSASGN
APPHMPRRISAQLAKEIQLKHRAPVVGISIFDQAGSPVDQLNAGENGSPPHRVLIASEEQFKVFSLPQLKPINKYKLTANEGARIRRIHFGSFSC
RISPETLQSMHGCSPTKSTRSHGDGEADPNISGSLAVSRGDVYNETALICLTNMGDIMVLSVPELKRQLNAAAVRREDINGVSSLCFTNSGEALY
MMSSSELQRIALATSRVVQPTGVVPVEPLENEESVLEENDAENNKETYACDEVVNTYEIKNPSGISICTRPAEENVGRNSVQQVNGVNISNSPNQ
ANETISSSIGDITVDSVRDHLNMTTTTLCSINTEETIGRLSVLSTQTNKASTTVNMSEIPNINISNLEDLESKRNTTETSTSSVVIKSIITNISH
EKTNGDNKIGTPKTAPEESQF*
(SEQ ID NO: 252)

Classification: tumor_suppressor
Gene Symbol: l(2)gl
FlyBase ID: FBgn0002121

Celera Sequence No. : 142000013384907
ACGAATCTCCAGAGGCCGGTCCTTTCCAGCCAGATTCTCGCCTCCAGCGCTCAACGAGGTGTACCGAAATTTCTCCAGCGCATCGCTTGCATTCG
AAATAAGCTCGCGCACAAAGACCTCGTGGTCGGAGTATAAGGAACGAGCCACAATGTCAAGTAGCTGGCGCGTCTCTGCCTGGAACTCATGCTTG
TCCACCACTGATCCTGATGCCTGCTTGGTCTCCGTGGAGTAGCGACGGAGCGAGAGAGCTGCAAGTGAAAAGATGAGTGTTATGTAAACATAAGA
ATCCCTCCGGGGAGCCGGTTGCTTATATTCAGTGCTTACCACCCGGCGAATGCTGCGATCCAATGGTGATATTGAACGCTGCTGGGGCGGATCGG
TGACTCTGCCTCAACACTTGGGCACAGCGACCGAGGCGGCACGCCTGGCCCAGCACTCCCATCGCTCGTACAGACATCTTGTTGTTTTAATGTTT
TGCCCAACTTTAATGTTACCCAACTACGAAGTTTGTTCCAGCGCACATGTGTGCACAGTGTAGCCAAATCAATCGATTGTAAGTATTCGATAATA
GTAAACTGGTAAAACCCTACTCATAACGGTGTTTTCTTCCAAATTTCTGGGCTGTAATGAATTTTGGACTCAAATGCTTAGTTGGTTTGAATAAG
AGTTACTACATGTAATGGAGAGTTCAGTTTCATCACATTATTCAGCTCAAAACTGAAGCAAACTGCCAGCTGACTAGTTCTCTAAAGATTTCGAT
CAGCAAGAGAGAGAGAGAGAGAGATAGAGATGTTTCAACTGTGAACAACAAACCGTAAATTCTGAAGGAATTAAGAACAGATTACGTTTCATTGTTT
AGCCAATGTAGATTGGATGCTGATTTTTGAGTTATGAAATAACAAATGTCTTCAAAGAAGACAGTAAATAAAAGAAAGTTAAATCAAATCCAATA
TTGAAAGACATCGATACCTCATATCGATATACGGTCCAATTGCTGACAGCCCTGCTCGTGAATGCAACTCTGCTGTAGCGCGTCAGCGTCGCGTT
GTAATTTTTGTTGAGTTTTTAAATAATTTTAATTAGCATCTGCGTGTCTTACTATTAGAATATCATGTGTTAAGTGTTTCCCATTCACGCCACC
ACACAAAAAGATCCAATCATGAGCGCCACCACCATCGACAACGTACGGGTGCTGCTTCAGTCGCTGCCTGCTGCCGCCGTAAACAGCGCCACTCA
GCCGGGCGATCTACAGACGCCGGGCAAGATTGCGGCCCCAGCGACTCCCCTTCGCGCCAAGAATCCCGCCCAATTACAGATCATGCCGGAGAAGG
TCGAGGAGATGCCGCCGTCACCTCCGGAGGAGTTCTGGAGGGACCTGCAGCAGTTTCACGAACGACGCGGGTGAGTTGCCGCGGCTCTCCTGTAT
TTGGAGACGACCTAACCCACTTTCCCTCTGCCCAAACAGCACTCCATTGACACAGCCCGCCAGGATCAGCGGTAAGCATGTCGACCTGTACAAGC
TGTACAACGAGGTAACCGAACGAGGCGGCTTTAATAAGGTGACCATGCGGGACGAGTGGGACGAGGTGTACAGCGCCATGGAGACATTGCGGGAG
CGCTGCGTTAACGGAACGGCTAGTATCAAGCACATCTACAGACGCTACCTGGACAAGTACGAACGGTTGAACTTCTTTGGCGAGGATCCAGACAA
GATGGAGGCTCTGGAGGCGGCTATTGAGATTGTAGAAATGGGCGGTGGACGCTCGCGATCTCGTTTTTTGGCTGGCGCCGGTGGTGGCCTAGGAA
GCATTTTTGGATCAGCACACTCTACGTTGCCGGCGGTGCCAATGGCCTACAACCAGCGCCAGCACTCTGTTAATGTGGAACGACGCCGACAGTAC
AAGATGTCCACGCAGTTGCACCGACACAGCAGCTACGAGAAGCTGCTGTTGTCTCTGCTTTCTCCGCTGCCCAATGAGCAGGACTTCGCCATAAA
CGTGTGCACACTTATGGCCAACGAGGCGCGCCACACCCTACAGCTGTCCGAGTGCCCCAAACTGCTTGATGTGCTGCTTGCTCACCTGGGAGTCT
ACGCTGACTTCACCATGCGCCAGCTGTTCCAGCACAGTTACACCGAGGTTCGACACCATTCGCAGCTCAGTTTCTGGCGCGACCTGCTACACGAC
AAGCCACAGGTCCTAGAGCTCTACACGGATGAGCAGGCCTGGCTGGACAACGGTCTGATAAGTAAGGAGGACGGTGAGAACTCTGCCGCTCGAAG
TGAACTGCTGGCGGCCTGCGACGAGTTGCACTTCCTTAATCTGCGCCGGAGCAACGGGACTGATGAGCGCATGGGCCAGCGAGTGCTTCAGATTG
TCCAGCTAGTCCGTACACTCAGCTTTCATCAGGAGAATCATGCACTCTTGGCCTCCAACCGCACGTTGTGGCGATATTTGGTCATGGGAGCAAAC
GTACGATGGAGTAAGTTTTTTTATCTGCTTAGAAATTATATTTTTTGGCGCTTTGAATGTACGAAGTATCAAGGTGCTATCATAAATACACTGC
AAGGAAATTGACTATTGCGTAGCATAGCAATCCCGAAAGAATCAATTTAAAATAAAATAACTGAAACACGTTTCGCTCGTTCTAGGCAACATTCA
CATCCAGGCCCTCGAGACCGCTGGCAACCTGGCTCAACAATTTGAGCTGCTAGACCCCACCACTGACGAGCTATCGCGGAATCTTTTAGCTACTC
TCTGCGAGGGTATTGACTCTAACGACCGCGCGGTGATCATGAGCTGTCTGGAGATACTCTATAAGTTGTGCGGACGAGAAGGCAATTCGCAGCAC
ATCAATCGTTGCCTTGGCCTGGACTTTTACCAGCGAGCCATGTTGCTCCTCTCGCTTACCGACGTCATGATGATTATCTTTACGCTGGAGGCAGT
TTACGCACTAAGTGCTCTTGGCGCTCGGCCATGTTCGATGCTGATGCAAGTACGTGGCCTAATAGACCAGCTGGTGACCCTTATCACAGTGGAGG
CTCAGTCATATGGCACAGGCGGTTGCATATTAATGCGTGTCGTAGAGGTTTTCCCCGGAAACATGGCTGCCTCGCTGGCTCAGAACATGCCCGCC ATTCTTGCTCCAGGTCCCACTTCCCTGACTACACTTCCAACATCGCTGCAAGTAGCTGTTAAACCGCCAGCAGTTTTACCCACGCCTACACCCGC
CCAGACGCAAGTGCTGCCTCACGGAGAGCAAACACCCTTGGTTACAGCTCTCCCCGGTCTGCCAATGCCCAGTCTGCCACAGGTTCAATTGCCTG
TACCCAGTCTGCCGCAGGTACAATTGCCACCAATCGCTGCCACCGTGACCCTTCCCAGTCTGCCCTCCGCCTCCCAGAGTTTTACACACGAGGAC
GAACAGTATGCGCTGGCTTGGCTGGGAGCCACGTATGAACGGGCTGGGAACGGTAACGATCTCCGTGTGGAACAAGCGGAACTATACAGAATATA
TTTATCGCATTGCCAGAAGGCGGGTAAGCTTTCAGTGGTTAATCACATGCAGTTTCCTCGTCTAGTGCGGCTTATATTTAATCAATCGGTGGGAC
CAGTAATTGTACGGCACCTGGACGGAATAGAGCTACCTGGGACGTACTACGTAGGCATTAGGATGCGAGCTCAGCCGCTAGCCATGCAACAGAGA
CCCACCCCCAGCATTGTTCCTGTTAAAAAGGACACGCCAATATTGCCCAAGCAACCATTTAGTGATCCTGTTCAAACGGAAGTGGCGTCTGAGGA
AAGCGTTTCTTCTGCAGTCACGCCACCCCCAAGCTCCTCGCTCATCAAAAGCTTGTTGGCCAACAAGGTAACTGAACGCCAACAGAAGCAGAAGG
CCCAAGCTCAGACGCCGCAGCCGCCAGCCCTTGTGGCTACCACGGCATCGGGCACAAATGCTACCCAGCCCATCAAGGTAACCTCAACAGCTATA
AGCGCCTTCGTGAACAACCCGCTAATGCAGCACACACCGGTGAAGGTGGGTCAGACTACCATTAAGCCGTTGCACCCCCAGATGGCCATCGAAAA
GAAGCCAATCACTGATTCGGCCCCGCCACCTCTCGCTCCATTGAGTGGTGCAAACGTAGTGACGAAAGACGCCAGCGGGCGCACTCTCATCATTG
CATCAGCAGCTGCCAAACGAAAATTAACCATTGACGAGGAGCAGAATAAGCGTCTGGCTTTAGATGCCGCTGCCAGCAGTTCCAGCAGCTCATCT
TCTGGCGGCAAGGAAGAAGCGCAGGTGACTCCCTCGAAGAATGCAGCCAATCTCTATGCGGATCTGGCGGCATCTATTTTGGAGGATGAGGATAT
GGATGACGTTCCACCGCTGGCCAAACCAAGCCAGGAGCAAAGCCAGCAGCACCCGCAACAGGCACAGCAGCTTCAACTCATTCCGGCTAAAGTGC
AACCAACCCAACGTCAACTTGTTTTCCCCGGTAGCAATGTGGTTTCTCCAGCTCCGCATTCCCAACTAAAACTTGCCACCACGGCCACCATAAAG
ACGGATCAGGGCTTGCAAACTGTGCCAGTGATCCTGCAGCCCAAGACTGCAATGGATTCCACGCCAGCTCCGCAGACGCAATATGTTCTGGCCAC
CAACCAGCAAGGCCAGACGTATCTTGTGGCCCAGCAGCCGACTATTCCGACATCCACGCAGTCGGCACCACCCACTCTGCTGGTGACGCAAACAC
CACAACAACAAACGAAGACCATAATAATCCTGCAGCAGCCAGGAGGAGTCTCTGCGGCGAACGTGGCTGGCACTCAGAAAATGATAATGACAACG
GCGCAGGGCCAGCAGGTCCTGGTTACCACCACCACAGCTCCACAACTGGCCCAACCGCGTACTTCTACCCCCCAGCAGCAAATCTTTATCGCACC
CCAGCGACCAGTTCCGGCGTTGGGTGCTGGCCAAATGTCGCCTTCACTGCTGTCGCAGTTGAACCAGATCCCGGCTACTATAAAGCTTCATCAGC
CCCAACCACAGCCGCAGCTCGTTTCGCCGCAATTAGCACCCCAGCAGCGATTAGTTGCCGCAAAGCCGGGCGCTTCATTGCCCATTCCTCAGCTC
CAGCAACATCAGTCTATCATCCAGCAACACATAATCTCGGGCCCCTCCACTCCTACTTCCACAGTTGGCGGTACGGTTGGTGGGAAAAGAGGCA
GGTAATTCTGGGCGGAATCAAGGAGACCACGCTAATTACCCAGACGTCGGCCACACCGGCTCCCCTGCAGCAAAGCCAGCTTAACTCGCAGACGA
TCATCACTCAGTCACCTACCAGCACGGCTATCGTAGGAGGCGTGGCTCTTCAGCAGCAACATCACATTCGATCTGTGTTGGACCAGCAGCAGCAG
CATCATCCATCCATCATCCAACAGAAGATAACCATGCCGGCAGTAAGTTGGGAACTGGGGCCGAAATTAAAGAATTATTATTTTTTTTTAAGTAT
ATATACAAGGGTCATTGAAAAGTATGTAAACAGCTTAAAATTTGATTTCATAATATGCCCATGCCCGTTCTAAATCCCATAAATCGCATCACATT
CACATTCCCCATTTTTAAATGTTTCCATCGCGTTTTCACTACTTGAGTGGCGGGTTTTACAGGATCTCTTTTCTAAATAGCCAACAGGTGTATGG
TAATAAGAATTGTGCTAAGATGACTAAAACAAATATTTTAATATATTATTTTAGATTTCCGAAGCGACCAAACCGAAAATAGCACCCGTTCCAGT
TTCACCAACTGTAACTCTCCTAGCAAAAAAGCCGGCGCCGCCACAACCTGCTCAAGTATCTAGCCCCAAGCCATCAGTCACCCAGGCTGTTGTGG
TAACGACGTCAGGAACTAGTGATTCAACGGAAGGCGGCAAAACAGTTGTCTTAGCAACCAGCGAGGCCAAGCCAGCGGAATCAGAGGTAGTAGCA
CAGACGGTTGTCCCACCTGCTGTCGTAACTACAGGTCCCAGCAGCAGTTCTTTGGTTGTCAGTCAGAGCGTCTACGCTGCTTCTGGCCCGAATGC
CAACCCCACGCCCTCTCCCATGCCCGTGGATGCAAATTGGTTGTACATCTGCGACTGGCGGAACTGTCCCCGCAAGAAATTCAAGTCTCTTAACG
AGCTGCAGTACCACGTGTGCAGTGTCCACTGTCCAGATCACCTTGATTCTGATGCCGACATTTATTGTCAGTGGGGCAGCGGACCCAACTTCTGC
GACAACAGAGCGCGCAAACGGTACTCATTGATGACGCATCTGATTGACCGGCACCTGACAACGGAGAACTTGCGCGCCAGTGTGCAACGTCGCCT
GGCAACTGGGATTCACAATGTGGCGCCCACCCAGGCTCCCGTGACCATAGTGCGCAACGAGGGTCATGCCCAACGATTGGCGGGAGGCGCTACTG
GTTCACCTTCGGGTCCTGCTTCAGCGGTTCCAGTCGTTGGCAGCGCCGCAATGCAAGCTATGAACCGACACACGACTGATTACACGAACGCTAAA
GAGCTGATGGACGAAAATGAGGGTCCAGTCACCAAGAGCATCCGTCTGACAGCGGCGCTCATTATACGCAACCTGGTCACCTACTCGGCTACGGC
CAAGAGAAGCCTGAAACGCTATGAGTCACGCTTGGCCAATGTCGCCTTTAGCAATGTGGAGGCTAGCGGAGTGCTCTCCCACATCATGTACGAAT
TGAGCCAGTAAGCCGATATAGCTTACCATCAATATGATTATTTAACTGACTTGTAAGAACGACACTAAAAAAATGTGAAAAGCAAACCATACCTT
GTTTGTCTAAATGATTCATACCATATAGCACCAAAATATGGGAGATTCGGGAGTAAGATTTTAATTTGACTTCTACAATTCTACGAGGCTTAGAA
TTAAAGAGCTATGGTGGACATTATCAGATATACTCCTGGTTAGCAAATAAACGTTTTGAATTAATCGTTCAAAACATACTTTGATTTACATTGTT
CTTATAAAATATTAATTAACACATCTGAGTTATAATCCGTTAAAAGAATCCGAACCGAAGAGTCCGCTAAATCTTCGTGTACTACAGTGAAACAC
TTTTTATCGCCTAACGTAAGATATTAGAATGGGATGAAATCAGGTTCATCATACAATAGCTTCTCCGTTCTTCAAAAAGTTTTCATCGTCCAAAA
TCGTATACTTGTTGCTCCTGTACGTGTCCAATTCAAAAATGTACTTCTTGCCGCAGTCCTTCATTAGCTTGTGGATAACTGGCTTGATGTTCTCG
ATGCCCGCGATACTGGCCAGTTCATTGTAGTAGACAAACTGAAATTACAGATAAAAGATTGTTTATATATGTTCTCTGCTTGTAAAAGTCTTTA
ACAAATAAGTCTACATAAGCTAATATTTTTAATTTCTTATACAGGGTATTGTGAACACTCACCTGTCGCTCGCCCATCTGATGTGCTTTCTTCTG
GTTGCGCACGCCGCAGCCCCACCGCTCTCCGATCTCCTGCTCCAGATCGGCAATCATCTGCTCCCGGGAGGGAAACTTCCGCTGACCTGTGAAGA
ACTTCAGCGTGAAGCGCACCTGCATGTCGAAGATGTGGGTGGGAATCACGTTGAAGGGCAGGCCCACAAAGGCCATGGTCGGGTGGTTGATGTTG
ATGCAGTGCTTCCACAGTGGCTGCACGAAGTTGTCTATCACCTGGACACCCACATCGGTGCTGAGGCAGGGGAATGTGTACTTGTAGCCGGTGCA
GAACATCACGTGGTCAAAGCTCTCCGTGCTGCCGTCCGTGA
(SEQ ID NO: 253)

Exon: 1001..1400
Exon: 1465..2480
Exon: 2651..5457
Exon: 5755..6831
Start ATG: 1159

Transcript No. : CT9107
CCTGCTCGTGAATGCAACTCTGCTGTAGCGCGTCAGCGTCGCGTTGTAATTTTTGTTGAGTTTTTTAAATAATTTTAATTAGCATCTGCGTGTCT
TACTATTAGAATATCATGTGTTAAGTGTTTCCCATTCACGCCACCACACAAAAAGATCCAATCATGAGCGCCACCACCATCGACAACGTACGGGT
GCTGCTTCAGTCGCTGCCTGCTGCCGCCGTAAACAGCGCCACTCAGCCGGGCGATCTACAGACGCCGGGCAAGATTGCGGCCCCAGCGACTCCCC
TTCGCGCCAAGAATCCCGCCCAATTACAGATCATGCCGGAGAAGGTCGAGGAGATGCCGCCGTCACCTCCGGAGGAGTTCTGGAGGGACCTGCAG
CAGTTTCACGAACGACGCGGCACTCCATTGACACAGCCCGCCAGGATCAGCGGTAAGCATGTCGACCTGTACAAGCTGTACAACGAGGTAACCGA
ACGAGGCGGCTTTAATAAGGTGACCATGCGGGACGAGTGGGACGAGGTGTACAGCGCCATGGAGACATTGCGGGAGCGCTGCGTTAACGGAACGG
CTAGTATCAAGCACATCTACAGACGCTACCTGGACAAGTACGAACGGTTGAACTTCTTTGGCGAGGATCCAGACAAGATGGAGGCTCTGGAGGCG
GCTATTGAGATTGTAGAAATGGGCGGTGGACGCTCGCGATCTCGTTTTTTGGCTGGCGCCGGTGGTGGCCTAGGAAGCATTTTTGGATCAGCACA
CTCTACGTTGCCGGCGGTGCCAATGGCCTACAACCAGCGCCAGCACTCTGTTAATGTGGAACGACGCCGACAGTACAAGATGTCCACGCAGTTGC
ACCGACACAGCAGCTACGAGAAGCTGCTGTTGTCTCTGCTTTCTCCGCTGCCCAATGAGCAGGACTTCGCCATAAACGTGTGCACACTTATGGCC
AACGAGGCGCGCCACACCCTACAGCTGTCCGAGTGCCCCAAACTGCTTGATGTGCTGCTTGCTCACCTGGGAGTCTACGCTGACTTCACCATGCG
CCAGCTGTTCCAGCACAGTTACACCGAGGTTCGACACCATTCGCAGCTCAGTTTCTGGCGCGACCTGCTACACGACAAGCCACAGGTCCTAGAGC TCTACACGGATGAGCAGGCCTGGCTGGACAACGGTCTGATAAGTAAGGAGGACGGTGAGAACTCTGCCGCTCGAAGTGAACTGCTGGCGGCCTGC
GACGAGTTGCACTTCCTTAATCTGCGCCGGAGCAACGGGACTGATGAGCGCATGGGCCAGCGAGTGCTTCAGATTGTCCAGCTAGTCCGTACACT
CAGCTTTCATCAGGAGAATCATGCACTCTTGGCCTCCAACCGCACGTTGTGGCGATATTTGGTCATGGGAGCAAACGTACGATGGAGCAACATTC
ACATCCAGGCCCTCGAGACCGCTGGCAACCTGGCTCAACAATTTGAGCTGCTAGACCCCACCACTGACGAGCTATCGCGGAATCTTTTAGCTACT
CTCTGCGAGGGTATTGACTCTAACGACCGCGCGGTGATCATGAGCTGTCTGGAGATACTCTATAAGTTGTGCGGACGAGAAGGCAATTCGCAGCA
CATCAATCGTTGCCTTGGCCTGGACTTTTACCAGCGAGCCATGTTGCTCCTCTCGCTTACCGACGTCATGATGATTATCTTTACGCTGGAGGCAG
TTTACGCACTAAGTGCTCTTGGCGCTCGGCCATGTTCGATGCTGATGCAAGTACGTGGCCTAATAGACCAGCTGGTGACCCTTATCACAGTGGAG
GCTCAGTCATATGGCACAGGCGGTTGCATATTAATGCGTGTCGTAGAGGTTTTCCCCGGAAACATGGCTGCCTCGCTGGCTCAGAACATGCCCGC
CATTCTTGCTCCAGGTCCCACTTCCCTGACTACACTTCCAACATCGCTGCAAGTAGCTGTTAAACCGCCAGCAGTTTTACCCACGCCTACACCCG
CCCAGACGCAAGTGCTGCCTCACGGAGAGCAAACACCCTTGGTTACAGCTCTCCCCGGTCTGCCAATGCCCAGTCTGCCACAGGTTCAATTGCCT
GTACCCAGTCTGCCGCAGGTACAATTGCCACCAATCGCTGCCACCGTGACCCTTCCCAGTCTGCCCTCCGCCTCCCAGAGTTTTACACACGAGGA
CGAACAGTATGCGCTGGCTTGGCTGGGAGCCACGTATGAACGGGCTGGGAACGGTAACGATCTCCGTGTGGAACAAGCGGAACTATACAGAATAT
ATTTATCGCATTGCCAGAAGGCGGGTAAGCTTTCAGTGGTTAATCACATGCAGTTTCCTCGTCTAGTGCGGCTTATATTTAATCAATCGGTGGGA
CCAGTAATTGTACGGCACCTGGACGGAATAGAGCTACCTGGGACGTACTACGTAGGCATTAGGATGCGAGCTCAGCCGCTAGCCATGCAACAGAG
ACCCACCCCCAGCATTGTTCCTGTTAAAAAGGACACGCCAATATTGCCCAAGCAACCATTTAGTGATCCTGTTCAAACGGAAGTGGCGTCTGAGG
AAAGCGTTTCTTCTGCAGTCACGCCACCCCCAAGCTCCTCGCTCATCAAAAGCTTGTTGGCCAACAAGGTAACTGAACGCCAACAGAAGCAGAAG
GCCCAAGCTCAGACGCCGCAGCCGCCAGCCCTTGTGGCTACCACGGCATCGGGCACAAATGCTACCCAGCCCATCAAGGTAACCTCAACAGCTAT
AAGCGCCTTCGTGAACAACCCGCTAATGCAGCACACACCGGTGAAGGTGGGTCAGACTACCATTAAGCCGTTGCACCCCCAGATGGCCATCGAAA
AGAAGCCAATCACTGATTCGGCCCCGCCACCTCTCGCTCCATTGAGTGGTGCAAACGTAGTGACGAAAGACGCCAGCGGGCGCACTCTCATCATT
GCATCAGCAGCTGCCAAACGAAAATTAACCATTGACGAGGAGCAGAATAAGCGTCTGGCTTTAGATGCCGCTGCCAGCAGTTCCAGCAGCTCATC
TTCTGGCGGCAAGGAAGAAGCGCAGGTGACTCCCTCGAAGAATGCAGCCAATCTCTATGCGGATCTGGCGGCATCTATTTTGGAGGATGAGGATA
TGGATGACGTTCCACCGCTGGCCAAACCAAGCCAGGAGCAAAGCCAGCAGCACCCGCAACAGGCACAGCAGCTTCAACTCATTCCGGCTAAAGTG
CAACCAACCCAACGTCAACTTGTTTTCCCCGGTAGCAATGTGGTTTCTCCAGCTCCGCATTCCCAACTAAAACTTGCCACCACGGCCACCATAAA
GACGGATCAGGGCTTGCAAACTGTGCCAGTGATCCTGCAGCCCAAGACTGCAATGGATTCCACGCCAGCTCCGCAGACGCAATATGTTCTGGCCA
CCAACCAGCAAGGCCAGACGTATCTTGTGGCCCAGCAGCCGACTATTCCGACATCCACGCAGTCGGCACCACCCACTCTGCTGGTGACGCAAACA
CCACAACAACAAACGAAGACCATAATAATCCTGCAGCAGCCAGGAGGAGTCTCTGCGGCGAACGTGGCTGGCACTCAGAAAATGATAATGACAAC
GGCGCAGGGCCAGCAGGTCCTGGTTACCACCACCACAGCTCCACAACTGGCCCAACCGCGTACTTCTACCCCCCAGCAGCAAATCTTTATCGCAC
CCCAGCGACCAGTTCCGGCGTTGGGTGCTGGCCAAATGTCGCCTTCACTGCTGTCGCAGTTGAACCAGATCCCGGCTACTATAAAGCTTCATCAG
CCCCAACCACAGCCGCAGCTCGTTTCGCCGCAATTAGCACCCCAGCAGCGATTAGTTGCCGCAAAGCCGGGCGCTTCATTGCCCATTCCTCAGCT
CCAGCAACATCAGTCTATCATCCAGCAACACATAATCTCGGGCCCCTCCACTCCTACTTCCACAGTTGGCGGTACGGTTGGTGGGGAAAAGAGGC
AGGTAATTCTGGGCGGAATCAAGGAGACCACGCTAATTACCCAGACGTCGGCCACACCGGCTCCCCTGCAGCAAAGCCAGCTTAACTCGCAGACG
ATCATCACTCAGTCACCTACCAGCACGGTCAGCACCGTTGGAGGCGTGGCTCTTCAGCAGCAACATCACATTCGATCTGTGTTGGACCAGCAGCA
GCATCATCCATCCATCATCCAACAGAAGATAACCATGCCGCCAATTTCCGAAGCGACCAAACCGAAAATAGCACCCGTTCCAGTTTCACCAACTG
TAACTCTCCTAGCAAAAAAGCCGGCGCCGCCACAACCTGCTCAAGTATCTAGCCCCAAGCCATCAGTCACCCAGGCTGTTGTGGTAACGACGTCA
GGAACTAGTGATTCAACGGAAGGCGGCAAAACAGTTGTCTTAGCAACCAGCGAGGCCAAGCCAGCGGAATCAGAGGTAGTAGCACAGACGGTTGT
CCCACCTGCTGTCGTAACTACAGGTCCCAGCAGCAGTTCTTTGGTTGTCAGTCAGAGCGTCTACGCTGCTTCTGGCCCGAATGCCAACCCCACGC
CCTCTCCCATGCCCGTGGATGCAAATTGGTTGTACATCTGCGACTGGCGGAACTGTCCCCGCAAGAAATTCAAGTCTCTTAACGAGCTGCAGTAC
CACGTGTGCAGTGTCCACTGTCCAGATCACCTTGATTCTGATGCCGACATTTATTGTCAGTGGGGCAGCGGACCCAACTTCTGCGACAACAGAGC
GCGCAAACGGTACTCATTGATGACGCATCTGATTGACCGGCACCTGACAACGGAGAACTTGCGCGCCAGTGTGCAACGTCGCCTGGCAACTGGGA
TTCACAATGTGGCGCCACCCAGGCTCCCGTGACCATAGTGCGCAACGAGGGTCATGCCCAACGATTGGCGGGAGGCGCTACTGGTTCACCTTCG
GGTCCTGCTTCAGCGGTTCCAGTCGTTGGCAGCGCCGCAATGCAAGCTATGAACCGACACACGACTGATTACACGAACGCTAAAGAGCTGATGGA
CGAAAATGAGGGTCCAGTCACCAAGAGCATCCGTCTGACAGCGGCGCTCATTATACGCAACCTGGTCACCTACTCGGCTACGGCCAAGAGAAGCC
TGAAACGCTATGAGTCACGCTTGGCCAATGTCGCCTTTAGCAATGTGGAGGCTAGCGGAGTGCTCTCCCACATCATGTACGAATTGAGCCAGTAA
GCCGATATAGCTTACCATCAATATGATTATTTAACTGACTTGTAAGAACGACACTAAAAAAATGTGAAAAGCAAA
(SEQ ID NO: 254)

Start ATG: 159

MSATTIDNVRVLLQSLPAAAVNSATQPGDLQTPGKIAAPATPLRAKNPAQLQIMPEKVEEMPPSPPEEFWRDLQQFHERRGTPLTQPARISGKHV
DLYKLYNEVTERGGFNKVTMRDEWDEVYSAMETLRERCVNGTASIKHIYRRYLDKYERLNFFGEDPDKMEALEAAIEIVEMGGGRSRSRFLAGAG
GGLGSIFGSAHSTLPAVPMAYNQRQHSVNVERRRQYKMSTQLHRHSSYEKLLLSLLSPLPNEQDFAINVCTLMANEARHTLQLSECPKLLDVLLA
HLGVYADFTMRQLFQHSYTEVRHHSQLSFWRDLLHDKPQVLELYTDEQAWLDNGLISKEDGENSAARSELLAACDELHFLNLRRSNGTDERMGQR
VLQIVQLVRTLSFHQENHALLASNRTLWRYLVMGANVRWSNIHIQALETAGNLAQQFELLDPTTDELSRNLLATLCEGIDSNDRAVIMSCLEILY
KLCGREGNSQHINRCLGLDFYQRAMLLLSLTDVMMIIFTLEAVYALSALGARPCSMLMQVRGLIDQLVTLITVEAQSYGTGGCILMRVVEVFPGN
MAASLAQNMPAILAPGPTSLTTLPTSLQVAVKPPAVLPTPTPAQTQVLPHGEQTPLVTALPGLPMPSLPQVQLPVPSLPQVQLPPIAATVTLPSL
PSASQSFTHEDEQYALAWLGATYERAGNGNDLRVEQAELYRIYLSHCQKAGKLSVVNHMQFPRLVRLIFNQSVGPVIVRHLDGIELPGTYYVGIR
MRAQPLAMQQRPTPSIVPVKKDTPILPKQPFSDPVQTEVASEESVSSAVTPPPSSSLIKSLLANKVTERQQKQKAQAQTPQPPALVATTASGTNA
TQPIKVTSTAISAFVNNPLMQHTPVKVGQTTIKPLHPQMAIEKKPITDSAPPPLAPLSGANVVTKDASGRTLIIASAAAKRKLTIDEEQNKRLAL
DAAASSSSSSSGGKEEAQVTPSKNAANLYADLAASILEDEDMDDVPPLAKPSQEQSQQHPQQAQQLQLIPAKVQPTQRQLVFPGSNVVSPAPHS
QLKLATTATIKTDQGLQTVPVILQPKTAMDSTPAPQTQYVLATNQQGQTYLVAQQPTIPTSTQSAPPTLLVTQTPQQQTKTIIILQQPGGVSAAN
VAGTQKMIMTTAQGQQVLVTTTTAPQLAQPRTSTPQQQIFIAPQRPVPALGAGQMSPSLLSQLNQIPATIKLHQPQPQPQLVSPQLAPQQRLVAA
KPGASLPIPQLQQHQSIIQQHIISGPSTPTSTVGGTVGGEKRQVILGGIKETTLITQTSATPAPLQQSQLNSQTIITQSPTSTAIVGGVALQQQH
HIRSVLDQQQQHHPSIIQQKITMPAISEATKPKIAPVPVSPTVTLLAKKPAPPQPAQVSSPKPSVTQAVVVTTSGTSDSTEGGKTVVLATSEAKP
AESEVVAQTVVPPAVVTTGPSSSSLVVSQSVYAASGPNANPTPSPMPVDANWLYICDWRNCPRKKFKSLNELQYHVCSVHCPDHLDSDADIYCQW
GSGPNFCDNRARKRYSLMTHLIDRHLTTENLRASVQRRLATGIHNVAPTQAPVTIVRNEGHAQRLAGGATGSPSGPASAVPVVGSAAMQAMNRHT
TDYTNAKELMDENEGPVTKSIRLTAALIIRNLVTYSATAKRSLKRYESRLANVAFSNVEASGVLSHIMYELSQ*
(SEQ ID NO: 255)

Classification: DNA_binding
Gene Symbol: BcDNA:GH12174
FlyBase ID: FBgn0027541

FIGURE SHEET 139

Celera Sequence No. : 142000013384103
GTGGCCGCAGTGGACTTGCTTCTCCTTCAGGATCTTCGCCACCTGGCGCGTCTTCAGAGCCAACCAAGCCAATGTGCGCTCTTGGTTGTACTTGT
AGAACTTCTGTTCGCCAGAGCTCTTCACATCTGCCACGCATTTAAGGTTCCCTGGGTCGAGGATCTCGTTAAGCAGACGACTGGTGCTGGCCTCC
TCCACGGCAATGTTGTCCAGCGATATTGCTCCTGATTGTGGTTAAAGATTTTCAAGAATACAATAGTATAGTATACCATCGAAAGCGAATGATAA
TATCTTACTTTGCGCACAATGTTTTCGGAGGTGATGAAGAGCCAGGAACGTGGGATCCACGGGCGCGGTCATGTAGATTCTGCCGTTGGAGCAGA
CCTCGCTGTCCACGAACCAACTGCGTCGGGGTTCCGTGAACGCCACCAGCTCCATCATTCTGCCATCGGGATGGGTTATGAACAGTGCCTCCTTG
CCATGTCCGGGATGGAAAAACATCTCCAGCCGAAGGTGTCCGTCGTCCGCATCTTTGGGCAGCAGTTCCTCCGACATGAAGAACACCTTCTTCAG
TGCCGAGGCCTTGCACATCTTGGCAGATCCCTCCGCATCCGGATCAGCTTTTGGTTTTCTCGCTCGCGTTTCCTTTTTGCCCATTTTCTCGAATA
ACTTGCCAAGCGTGAAGCAAAAGTCAATAACTGTGGACCGAACCAAAACAAACGATTTGCCGCCTTTTTGGTTATTGATAGAAGTCTATCGATTA
ATTTTGGTATTTTATATAGTCTGCTAATTTTAACTTGTTCCTATAAACTATTTTATCTATTTTATGCCAAATAGAAGAGCTTAAAAATTAAATAA
TCTCTGCCACTAACGTCCGCATCTTAATATTGCAACTAGTCTAAAATGGGTATTAACTTTGATTGAGAAGCGCGGTCACATTGCTTGAACAGATG
TTCACAGTGATGAAATTGTTTACAACAGTATATTGTTTTTAAACAACAAAATGAGCGTAGATATAGCCAGCACGATCAAGTTCCGGGATATTTGC
AGCCTGTTCGAGAAGATTAAGGCCACGCAAAAGGTGGCTAACAAGGAGGAGGTCCTCAAGAGCTACTACGAGTCCTTCTGTCGCCACCGCGAATC
CTTTCGCCGGCAAACCGGATTAAACAACGACCAGCCGGAGGACGGTGCCAGTAGCTTCTATTCCGTGCTGCGACTGCTGCTTCCGGGTGCGGACA
CTGGTCGGGATACCTATGGATTGCAGATCACCGCGCTGGGCAGGCTCTACATCAGGGTGCTCCAGCTACCCACGGACTGTGAGTGCAGAAACGTA
TTGGCAATGGCATTTAGGCTTATTTAGAATCTCTTTGTTGTCTCTACTAGCCAGCGATGCCATCAGGCTGCAGCACCGCAACGGAAACATGTACC
GGGACTACGGTGATGTTGTTTATTCCGTGCTTAAGCCAAGGTGCTTTAATCCGCCCAGCAATTTGAGACTGAAAGAAATCCATCAGATGCTGGAC
ACCATTGCCAACGAGGACACAGAAGGTGGGCGCTTTTAAACTGATCTGAACGACTGAACGTCTTAATGAGACCGCTCTTTGCAGTTAAGCAGCAG
CAACTCATCCGGTTTACGGAGCAGGCCTCGCCTGAGGAACAGAAGTGGCTAATTCGGTTGCTGCTTAAGAGCCTCGGGCTGGGGATCGGTGAGCA
AAAGATTTTCGGTGTGCTGCACCCCAAGGCGCAGGATATCTACCAGCGCTGCTCCGATCTGGGACATGTGTGCAATCTGCTGGCAGACCGAACCA
CCGACCTAGACGCCAGCAGCAGCAAGGACAGCAAGGCGGCGGTCAAGTTTGTAAACCTGAATTCCGTCATACGGCCATTCCACCAGATACGTCCC
ATGCTGTGCGAACGATTCCCCGGTGACATCCAGGAGCTGATGCAGTCGGATGTGCTCTATCTGGAGACCAAAATGGATGGCGAACGCTTTCAGCT
GCACATCGATCGGGGTCGTTTCATGTACATTTCCCGCAATGGAGTGGACTACACCAGAAACTTTGGTCACAGCTACGATCACGGCACCTTAACGC
CAAAGCTGAGGGGACTTCTGCCGCTGGGTCTGGAGTCTATCATACTCGACGGCGAGATGATGGTGTGGGATACCAACAAACTGCGCTTTCGGGAA
AAAGGCGAGAATACGGACGTGAAGAGCCTGAAGCCGGAGGGCAGCTGGCAGCCATGTTTCGTGGTGTACGATCTGCTATATTTTAATGGCCAGAG
TCTGCTGGACCATACCTACATTCAGCGGGCGTACAAATTGCAGAAACTCATAGTTGAACAGTCGGGTGTGCTGCAGTTGATGCGTGCACGCAAAA
TCGGTTCCGTTCAAGAGTTCAACGAGCTGTTCCAGCAGGCACTCGACTCCCACGCCGAGGGCATTGTGCTAAAGAAGCAGGGATCAAGATATCAG
CCTGGCGTTAGACTGGGCGGTGGGTGGTACAAGGACAAGGCTGATGTGAGTAGAGTCATTTTTAAGTAGAGTGCTTTAATATGAACTCACTTCAA
TTTTCCAACCAGTACATCAAAGGGCTGATCACCGAGTTCGATGTGCTGATCATCGGGGCATTCTACAATCGCAAGCGCACCTTTGTGGACTCATT
TTTACTGGGCGTTCTCCAGCCGGCGCCGCCAGGCAGCTCTAATCGTCCCGAAGTCTTCAGTATTGGAGTGGTTGCCAACAATACGAAACAGCGCG
GAGTGCTAAATCACACACTGAAACCACATTGGCATGATGTAGTCAATGAGCCACCGCCATTGTGGTTTCACTACAAGCCCAAGGAGAGGTCCGGA
TGCCCCGATCTGTGGATTGAACCGCAGAACTCGGTAATTTTGCAGGTGAAAGCTGCTGATCTGGCGCCCAATGGAGCATTTTTCACCCGAAAATC
GTTGCACTTTCCGCGCACTGAGATGAAACGGGATGATAAGACCTGGAGCGAGTGTATGACACTTAAGGAGTTTAACGATCTCTGCGGAGGTCCTT
TGGCCATCAAGAAGTTAAACAAGCGGCAACTGCGACTAGAGGATGTGACCACCAAGCGGAAACAGATGCGTATGACGCCCTCGGAGCGAAGCCGA
CTGGGATTGGCCGTCTATGAGAAGCGCTATGACGCTAGCACCTCCGCTAGCACTTCCAAACTTTTCGACGGTCTGAGCTTTTGCATTCTGAGCGG
ATCTGCCGGACGACACAGCAAGCATCAGCTGCAGGAGCTGGCTGTTAAAAACGGTGGCTGCATCGTGGAAAATCCCCTGCCCAATGATCCAAAGT
GTTTTTGCATCGCAGGCGATGAGACGTTTTTAGTTAAGCGGCTCATCCTTCAACAGCCACGCACCTGTGACATTGTGCGCATGGAGTGGCTACTT
AGGGTCTGTCAGAAGCAGGAGCTTGAACTAAAGCCTAGAGATCTTATTGCGGCCACTGAACCACTGCAGCAGGATCTGGCTGAATGTTTTGATCG
GCACGGTGATAGCTACACCAAAGACATTGCCAACGTGGAGGAGCTGCAGGATCTGCTTCAAGGCATTGAGTTGACAGCTGATAATGTGGCTGGCA
TAACCGCATCTAATCTCAATGCTCTGGAGGATCAGCTTCTGGATGGGAAAAAGAATCTGAACATGTTCCGCAACCTTAATGCGTTCTTCTACAGT
CCGCATGGTGATGAAGTGGCTAAGCTTCTGTTTCTTCAAAACGGCGGCCGGATAGTCGACGATTCCGATCCGCAACTAAATCTGGGATTTATCTG
TATGTCTTCTGACATCGATAACGACCACTTCGAGCACTGGCTGCACAATCATTCCAAGTTGACCACTGACAAGGTCTTAAACTCGGCGTGGATAC
ATCAGTGCCATCGCGAAGGCATCCTACTTCCTATGCATTCTTTCGTCTAACTCAATGAGTTTTTCACGCTTTATAGTTTTGTACAAAAATTACCT
GTTATCCTTGTTATAAAATTGTTGTTTCATTGACATTTTTCTTACCATAAAAAGCTTTAAACAGAAGTCATTCCGAATTTAATGTTATATCAAAA
AGATTTTCATGGATAATTTGCTTCAATAAAGTGAAACATAGAATAACAATAGTAGAATGACAATAAGTACGCAAAAAAGTTATTTTTCAATGATT
TCGTTTTTATTCACATAAAAAGAGATAACGAGCAGAATAGTATTGTTTCCGTTGGGAGGATTTTGGACAAGTTTTGGGGTAGTGTGGATATGGAT
ATTAGGATCGTTATTTCGCCAATTGATACGTTTGACAGTTCGGTTACAAAGTTCAGGGAGTTCTCTTCGGGATTTTCATTGGTTTATCGGTTCTG
CACTTTGGGCAATAAGAACATCAAAAATACATTTATTTTATTCATTGTAAAGTTAGATATATGTTTGTATATATATAACATAAATAATGTATATA
TAGGTGTATAACATTTAACACTAACAATTCTTAAGCGCGAGCTCTTCGCTCTCTCTCTCTCTCTCTCTCTCTATTTCTTTCTCTGTCTCTCTCCA
TCTCACTTGCACCTACTAACGCTATCTCTGTCGTTCATTGACTTGACTTTAACATTTAATTTAATGAGGAATATGCAATCTCTGAGATTGTTTAA
CACATTTATCGACTCTATGAACATATAGATTACGTATGTCAATCAAATTGTTTAAAATTTACCAAGCTAATATCAACAAAAAAAAAAAAACTTTA
TAGTTTAAGTTTCTCAGTTAGTTCGATTCATGGGAGTGGCAAAATTCGTGGTTGGAATATTTGTTGATGTTTATACATAAATAGTTGGGCTTGG
GCATACAAATGCAGAGTACTCTCGATCTTGATCTTTATTTGTGGGTATAACAATCGGTATACTAAACTTAGTCGTTACTTTTCAATGTTGTTTGG
TTGTGGGTTTGTTCTCTTATATTTTCACTTTTGTGTTTCTTATTCCGGCATGGTAAATAGGTTACAACGCTACACATAACAACTATCAACATTTA
GGGTATGCATAATAATAGCGATATCATAATAATAATAATAATAATAATAGTAATAACATCAGTTACAACTTTATTTGTGTGTGTTCGTCGTT
CCTTCAATATAATTGAAAATA
(SEQ ID NO: 256)

Exon: 1001..1313
Exon: 1381..1545
Exon: 1605..2515
Exon: 2578..4151
Start ATG: 1001

Transcript No. : CT9161
ATGAGCGTAGATATAGCCAGCACGATCAAGTTCCGGGATATTTGCAGCCTGTTCGAGAAGATTAAGGCCACGCAAAAGGTGGCTAACAAGGAGGA
GGTCCTCAAGAGCTACTACGAGTCCTTCTGTCGCCACCGCGAATCCTTTCGCCGGCAAACCGGATTAAACAACGACCAGCCGGAGGACGGTGCCA
GTAGCTTCTATTCCGTGCTGCGACTGCTGCTTCCGGGTGCGGACACTGGTCGGGATACCTATGGATTGCAGATCACCGCGCTGGGCAGGCTCTAC
ATCAGGGTGCTCCAGCTACCCACGGACTCCAGCGATGCCATCAGGCTGCAGCACCGCAACGGAAACATGTACCGGGACTACGGTGATGTTGTTTA TTCCGTGCTTAAGCCAAGGTGCTTTAATCCGCCCAGCAATTTGAGACTGAAAGAAATCCATCAGATGCTGGACACCATTGCCAACGAGGACACAG
AAGTTAAGCAGCAGCAACTCATCCGGTTTACGGAGCAGGCCTCGCCTGAGGAACAGAAGTGGCTAATTCGGTTGCTGCTTAAGAGCCTCGGGCTG
GGGATCGGTGAGCAAAAGATTTTCGGTGTGCTGCACCCCAAGGCGCAGGATATCTACCAGCGCTGCTCCGATCTGGGACATGTGTGCAATCTGCT
GGCAGACCGAACCACCGACCTAGACGCCAGCAGCAGCAAGGACAGCAAGGCGGCGGTCAAGTTTGTAAACCTGAATTCCGTCATACGGCCATTCC
ACCAGATACGTCCCATGCTGTGCGAACGATTCCCCGGTGACATCCAGGAGCTGATGCAGTCGGATGTGCTCTATCTGGAGACCAAAATGGATGGC
GAACGCTTTCAGCTGCACATCGATCGGGGTCGTTTCATGTACATTTCCCGCAATGGAGTGGACTACACCAGAAACTTTGGTCACAGCTACGATCA
CGGCACCTTAACGCCAAAGCTGAGGGGACTTCTGCCGCTGGGTCTGGAGTCTATCATACTCGACGGCGAGATGATGGTGTGGGATACCAACAAAC
TGCGCTTTCGGGAAAAAGGCGAGAATACGGACGTGAAGAGCCTGAAGCCGGAGGGCAGCTGGCAGCCATGTTTCGTGGTGTACGATCTGCTATAT
TTTAATGGCCAGAGTCTGCTGGACCATACCTACATTCAGCGGGCGTACAAATTGCAGAAACTCATAGTTGAACAGTCGGGTGTGCTGCAGTTGAT
GCGTGCACGCAAAATCGGTTCCGTTCAAGAGTTCAACGAGCTGTTCCAGCAGGCACTCGACTCCCACGCCGAGGGCATTGTGCTAAAGAAGCAGG
GATCAAGATATCAGCCTGGCGTTAGACTGGGCGGTGGGTGGTACAAGGACAAGGCTGATTACATCAAAGGGCTGATCACCGAGTTCGATGTGCTG
ATCATCGGGGCATTCTACAATCGCAAGCGCACCTTTGTGGACTCATTTTTACTGGGCGTTCTCCAGCCGGCGCCGCCAGGCAGCTCTAATCGTCC
CGAAGTCTTCAGTATTGGAGTGGTTGCCAACAATACGAAACAGCGCGGAGTGCTAAATCACACACTGAAACCACATTGGCATGATGTAGTCAATG
AGCCACCGCCATTGTGGTTTCACTACAAGCCCAAGGAGAGGTCCGGATGCCCCGATCTGTGGATTGAACCGCAGAACTCGGTAATTTTGCAGGTG
AAAGCTGCTGATCTGGCGCCCAATGGAGCATTTTTCACCCGAAAATCGTTGCACTTTCCGCGCACTGAGATGAAACGGATGATAAGACCTGGAG
CGAGTGTATGACACTTAAGGAGTTTAACGATCTCTGCGGAGGTCCTTTGGCCATCAAGAAGTTAAACAAGCGGCAACTGCGACTAGAGGATGTGA
CCACCAAGCGGAAACAGATGCGTATGACGCCCTCGGAGCGAAGCCGACTGGGATTGGCCGTCTATGAGAAGCGCTATGACGCTAGCACCTCCGCT
AGCACTTCCAAACTTTTCGACGGTCTGAGCTTTTGCATTCTGAGCGGATCTGCCGGACGACACAGCAAGCATCAGCTGCAGGAGCTGGCTGTTAA
AAACGGTGGCTGCATCGTGGAAAATCCCCTGCCCAATGATCCAAAGTGTTTTTGCATCGCAGGCGATGAGACGTTTTTAGTTAAGCGGCTCATCC
TTCAACAGCCACGCACCTGTGACATTGTGCGCATGGAGTGGCTACTTAGGGTCTGTCAGAAGCAGGAGCTTGAACTAAAGCCTAGAGATCTTATT
GCGGCCACTGAACCACTGCAGCAGGATCTGGCTGAATGTTTTGATCGGCACGGTGATAGCTACACCAAAGACATTGCCAACGTGGAGGAGCTGCA
GGATCTGCTTCAAGGCATTGAGTTGACAGCTGATAATGTGGCTGGCATAACCGCATCTAATCTCAATGCTCTGGAGGATCAGCTTCTGGATGGGA
AAAAGAATCTGAACATGTTCCGCAACCTTAATGCGTTCTTCTACAGTCCGCATGGTGATGAAGTGGCTAAGCTTCTGTTTCTTCAAAACGGCGGC
CGGATAGTCGACGATTCCGATCCGCAACTAAATCTGGGATTTATCTGTATGTCTTCTGACATCGATAACGACCACTTCGAGCACTGGCTGCACAA
TCATTCCAAGTTGACCACTGACAAGGTCTTAAACTCGGCGTGGATACATCAGTGCCATCGCGAAGGCATCCTACTTCCTATGCATTCTTTCGTCT
AACTCAATGAGTTTTTCACGCTTTATAGTTTTGTACAAAAATTACCTGTTATCCTTGTTATAAAATTGTTGTTTCATTGACATTTTTCTTACCAT
AAAAAGCTTTAAACAGAAGTCATTCCGAATTTAATGTTATATCAAAAAGATTTTCATGGATAATTTGCTTCAATAAAGTGAAACATAGAATAACA
ATAGTAGAATGACAATAA
(SEQ ID NO: 257)

Start ATG: 1

MSVDIASTIKFRDICSLFEKIKATQKVANKEEVLKSYYESFCRHRESFRRQTGLNNDQPEDGASSFYSVLRLLLPGADTGRDTYGLQITALGRLY
IRVLQLPTDSSDAIRLQHRNGNMYRDYGDVVYSVLKPRCFNPPSNLRLKEIHQMLDTIANEDTEVKQQQLIRFTEQASPEEQKWLIRLLLKSLGL
GIGEQKIFGVLHPKAQDIYQRCSDLGHVCNLLADRTTDLDASSSKDSKAAVKFVNLNSVIRPFHQIRPMLCERFPGDIQELMQSDVLYLETKMDG
ERFQLHIDRGRFMYISRNGVDYTRNFGHSYDHGTLTPKLRGLLPLGLESIILDGEMMVWDTNKLRFREKGENTDVKSLKPEGSWQPCFVVYDLLY
FNGQSLLDHTYIQRAYKLQKLIVEQSGVLQLMRARKIGSVQEFNELFQQALDSHAEGIVLKKQGSRYQPGVRLGGGWYKDKADYIKGLITEFDVL
IIGAFYNRKRTFVDSFLLGVLQPAPPGSSNRPEVFSIGVVANNTKQRGVLNHTLKPHWHDVVNEPPPLWFHYKPKERSGCPDLWIEPQNSVILQV
KAADLAPNGAFFTRKSLHFPRTEMKRDDKTWSECMTLKEFNDLCGGPLAIKKLNKRQLRLEDVTTKRKQMRMTPSERSRLGLAVYEKRYDASTSA
STSKLFDGLSFCILSGSAGRHSKHQLQELAVKNGGCIVENPLPNDPKCFCIAGDETFLVKRLILQQPRTCDIVRMEWLLRVCQKQELELKPRDLI
AATEPLQQDLAECFDRHGDSYTKDIANVEELQDLLQGIELTADNVAGITASNLNALEDQLLDGKKNLNMFRNLNAFFYSPHGDEVAKLLFLQNGG
RIVDDSDPQLNLGFICMSSDIDNDHFEHWLHNHSKLTTDKVLNSAWIHQCHREGILLPMHSFV*
(SEQ ID NO: 258)

Name: DNA ligase
Classification: DNA_repair_protein

Celera Sequence No. : 142000013384500
GGTATACGGCCACTCCGGCAAAGATAAAGGCCAGCAGGACCATGTCAGTCTGGCCTGATATTCTGTTGGTCTCCCTTTGCACTTTTATTCGATCG
TATTTGGCCTGGGCGGCTTGTCTCCGGTCAAATGATTTACCATAGTGATTTCGCGACCACTCGTCGAAGTCATAGATGGGCGTACGGCCCGCAGA
ATCAGATACACGCGATTTCTGAAATCGCGACTTGTAAAACTTAGTCTCCGCATCGTCCTCGACTACGGGTTCCGCTACATCGTGGACATCTTGGG
CATATTGGGCGCCTGCCGTATGTACGATTCCCTTGTCGTAAAGTCGACGCAGCCGGTAATTTCCCAGAATCTCATAAGCCTGATTGATCTCCCGA
AATTTCTTGGCTGCGTTCTCACTTCCTTGGTTCCTGTCCGGATGATAAAGCATCGAGAGCTTATAGTAAGCTGCCTTGATCTCGTTCTGCGTGCA
CTGACGCCTGATTCCCAGTGCGTCGTAGTGGCTCATCTGGTGGCGTTGACTGAGGTAGAGGCCACGCAGCAGAAGCAGAGGTCGCCACAACATTG
GGCTGTGCTGGTACATCTTGGATGTGTTCTTTCGCCCGCTTCACTTGTTTTGGTTTCGTTATATCACATGAAAATTAAAAACAAATCGAATCAGC
TGTTTGAACTTGAACTTGTTCACCCTCGCCATCGTTGTTATCGATAGATCGATAGTATTCTGAACCAATGGTGCAGGTACAGCAAAAAATTAGCT
GAAAGAGGAAAAAGAGCTTGTAATTGATTAATTTATAAAAGATAGATTTTGAAAATATTTACAGAATAAATGATTTTCAAAAAAGTTTTTACAGA
TATATCAGAAAAATATTTGTAATCCCTGGCTTAGTTAAAAATTTAAGACTTTAGTAAAGTTGAAATTCGTCAGCTGTTTGGGCTATGATGAAAAA
AGCAAAACGTAAGCTCCACGGTTCCAGTCAGCTGTTTGGCCGATTCGCTGCGAATGGCAACTGTTGCAACTATTTTGGTTTGAGTCTTCTCAATT
TTTATTTATATATAGAACAGGGCAGCAGCCGGTTCAATAGTCTCACGCAGCGTGCTTGATTTTCCCGCTAAACGCCTGCAACTGTATCTGTGTGT
ATTCGAGAGCGATCGAGAAGTTTCTGGTGGTCGAAATTTAGGCCAGAAGGCACAAAACCGAACTGAATAGTGAGTCATCCGTTAACAATAAAAAG
TTGCAGCTACAGTTTTTGTCTTTTTATACAGAAAATTGTGTAACCATGACAAACACCATCAACAGCGAGGAAGTGTCCGACGCAGGAAGCTACAA
AGATAAGGGCAACGAGGCGTTCAAGGCCTCCCGCTGGGAGGAGGCAGTGGAGCACTATGGCAAAGCCATTAAGGCGGGCTCTAAGCACAAGGAGC
TGGCGGTTTTCTATAAGAATCGTGCTGCCGCTTATCTGAAGCTAGGAAAGTATGAAAATGCGGTAGAGGACTGCACTGAATCTTTGAAAGCGGCT
CCGGGGGATCCCAAGGCACTGTTCCGTAGGGCTCAGGCGTACGAAGCTCTGGAGAAGTTCGAAGAGGCCTACAAAGACGCAACCGCTTTGTTTAA
AGCGGATCCCGGCAACAAAACCGTACAGCCCATGCTCCAGAGGCTTCATGTCGTCGTGGAAGAGCGCTCTGCCCGTAATGCCAAGACATCCACAA
AAGTCAAGCAGATGATGGATCTTACTTTTGATTTGGCCACGCCCATCGATAAGCGTCGCGCGGCAGCCAATAACCTAGTAGTTTTGGCCAAAGAG
CAGACTGGCGCTGAACTGCTTTACAAGGACCACTGCATCGCCAAAGTGGCCTCACTAACAAAGGTGGAAAAGGATCAGGACATTTATGTGAATAT
GGTGCATTTGGTGGCTGCTCTTTGCGAAAATAGCGTCGAGCGTACAAAGGGCGTTTTAACTGAACTCGGAGTACCGTGGTTCATGAGGGTTCTCG
ACCAAAAACACGAGAACTGTGTGTCCACCGCCCAGTTTTGCCTACAAACAATATTGAACGCATTGTCTGGGCTTAAGAACAAACCCGATTCGAAG CCGGAGAAGGAGCTGTGCACTAGGAACAACCGGGAAATTGACACTCTCCTAACATGCCTAGTTTATAGTATCACGGATCGCACGATTTCTGGAGC
AGCTAGGGATGGCGTTATTGAGCTTATAACCAGGAATGTCCACTACACAGCTCTAGAATGGGCCGAACGCCTGGTTGAGATCAGGGGACTGTGCC
GTCTGCTGGATGTGTGCTCCGAACTGGAGGATTATAAGTACGAGAGTGCAATGGATATCACAGGCTCATCATCCACAATTGCATCCGTTTGTCTG
GCCCGGATATATGAGAACATGTACTACGATGAAGCTAAGGCACGGTTCACGGACCAGATCGACGAATACATTAAGGACAAGCTTTTGGCGCCTGA
TATGGAATCCAAGGTGCGGGTCACCGTTGCGATTACTGCCCTGCTTAACGGTCCATTGGATGTGGGCAATCAGGTTGTGGCCAGAGAAGGTGAGT
TCTGTTATTGGATTTAGAAAATGGTACTTAATTAATGGTGAAATTTGTAACAGGAATACTGCAGATGATTCTAGCAATGGCTACGACCGACGATG
AGTTGCAGCAGCGAGTATCATGTGAGTGCCTAATCGCCGCTTCCTCTAAAAAGGACAAGGCCAAGGCTCTTTGTGAGCAGGGAGTAGATATTTTA
AAGCGGCTCTACCACTCCAAGAACGATGGTATTAGAGTACGCGCCCTGGTGGGTCTTTGCAAGCTGGGTAGCTACGGCGGTCAGGACGCGGCCAT
CCGACCATTTGGCGATGGAGCTGCCCTTAAGCTGGCGGAGGCATGCCGTCGGTTTTTGATCAAACCTGGAAAGGATAAGGATATCCGTCGTTGGG
CTGCCGATGGTCTGGCTTATTTAACACTGGATGCTGAATGTAAGGAGAAGCTCATTGAGGATAAGGCTTCCATTCACGCTTTAATGGATTTGGCC
CGCGGAGGAAATCAGTCCTGTCTCTATGGTGTGGTCACTACTTTTGTGAATCTGTGCAATGCGTATGAGAAGCAGGAGATGTTGCCTGAGATGAT
AGAACTTGCCAAGTTTGCTAAGCAACACATACCGGAGGAGCACGAGCTGGACGACGTAGATTTCATCAATAAGCGTATTACTGTGCTGGCAAATG
AGGGCATAACAACTGCTCTTTGTGCACTGGCGAAAACTGAAAGCCACAATTCACAGGAGCTGATTGCCAGGGTTTTGAATGCGGTTTGTGGACTG
AAAGAGTTGCGAGGAAAAGTGGTTCAAGAAGGCGGCGTTAAGGCGCTGCTTCGTATGGCGCTTGAGGGAACTGAGAAAGGAAAACGCCATGCTAC
CCAGGCGTTGGCTAGGATTGGCATAACCATTAATCCGGAAGTATCTTTCAGTGGCCAGCGATCGCTTGATGTAATCCGTCCTTTGTTGAACCTTT
TGCAACAGGACTGCACAGCGCTGGAGAATTTTGAGTCGCTAATGGCACTCACCAATCTAGCCAGCATGAACGAGAGCGTGCGCCAGAGGATTATC
AAGGAGCAGGGGGTCTCCAAGATAGAGTATTATCTGATGGAGGACCATCTGTACCTGACTCGTGCAGCTGCCCAGTGTCTGTGTAATCTGGTTAT
GAGTGAGGATGTCATTAAAATGTTCGAGGGCAATAACGACCGAGTGAAGTTCTTGGCGCTTCTCTGCGAGGATGAGGACGAGGAGACCGCAACAG
CTTGTGCCGGAGCTCTGGCCATTATTACTTCAGTGTCTGTCAAGTGCTGTGAGAAGATCTTGGCCATCGCCAGCTGGCTGGACATTCTGCACACT
CTGATCGCCAATCCCAGTCCGGCGGTCCAGCATCGAGGCATTGTGATTATTCTAAACATGATCAATGCTGGAGAGGAGATCGCCAAAAAGCTGTT
TGAAACGGACATTATGGAACTGCTGAGCGGTTTGGGGCAGCTGCCCGATGACACGCGTGCCAAGGCCCGAGAGGTGGCCACCCAGTGCCTGGCGG
CGGCGGAGCGTTATAGGATCATCGAGCGGTCCGACAACGCGGAAATCCCCGATGTGTTTGCCGAAAATTCGAAAATATCTGAGATTATCGATGAT
TAAGCGAAATTCGTTTGTAGTGCCTTTTGTTTTTCCTCCATTTCATCTTCTTTACTTTACTCACAGTGTCATCGCGAAATTTAACTTATTTTTCA
AAATATCAAATGTACTTAACTGTTTTATAAATATTGTTCGAATTTATTTCGTTTTTAAAGGTAGTTTGTTTTATTCCTTAGTGGGTAATATAATA
TATTATTTAGTTATTTCATGAATACGCGATTTTTTAATTTAACTAATTTAATACAGACCAAGCCTAATCCAAGCCTAATTGCTGCGGCCTAATGT
GATTTGGATTGTAATATGGATGGCCACTAGGATGGCCTAGTGTTTTCCCACCGACTCCATTTTCCCCGGTGCACTGCCTCGGTACGTTTTCTATT
CATTGCCACACATTAGTCGCCAGCTCGAGGTAGCTGACTTCCTCTAATGCAGAAGATGCTTCTGATGCGGCAGTGTTGCAGTGTCAGGTAGCCGG
GAATTCCGAGCCGAGCATCTCTTCCAGCTGATTGCTCAATCTCAATGAAGTGTGATTAAATAAATAATAGTTGCTTTAATTTAGTTTGGCTCAGC
GCAGTGGGAAATGGCCGAGGGTTTCGGTTGCTATGATTCGGTTGCCATGACTTAACGGCATTTATTCCGAAATCCATCCCGCTTTTTGTCTTTGG
CCATTTGGCATTCCTTTTCCCGCGATTATTTCGCATTTTCCTCTTCTCCTTAAACCATATACTGTGCTCAATTTGACCAATATAAATAACGTGGT
TAGAAGGTAAAGTAATGAGGAAGATGAATTCTTCAGGACCCTTATATGCTAAAGGGATATAAGCTGAAATAAAATATGTTGATGTAAGACCCCAG
AAGGAAACAAACTAATGCTTGGCAATATATTTAAAAAATTGGTGTATAAAAACAATTAAGTTAGGGGAATAAACATTTTAAAAAATGGTAAAAAA
AGACATTTTAAAAAATGTAAAAAGGATATTTCCGTGGAAATATATTAGCAAAT
(SEQ ID NO: 259)

Exon: 1001..1209
Exon: 1267..2559
Exon: 2619..4183
Start ATG: 1281

Transcript No. : CT9235
CGAATGGCAACTGTTGCAACTATTTTGGTTTGAGTCTTCTCAATTTTTATTTATATATAGAACAGGGCAGCAGCCGGTTCAATAGTCTCACGCAG
CGTGCTTGATTTTCCCGCTAAACGCCTGCAACTGTATCTGTGTGTATTCGAGAGCGATCGAGAAGTTTCTGGTGGTCGAAATTTAGGCCAGAAGG
CACAAAACCGAACTGAATAAAAATTGTGTAACCATGACAAACACCATCAACAGCGAGGAAGTGTCCGACGCAGGAAGCTACAAAGATAAGGGCAA
CGAGGCGTTCAAGGCCTCCCGCTGGGAGGAGGCAGTGGAGCACTATGGCAAAGCCATTAAGGCGGGCTCTAAGCACAAGGAGCTGGCGGTTTTCT
ATAAGAATCGTGCTGCCGCTTATCTGAAGCTAGGAAAGTATGAAAATGCGGTAGAGGACTGCACTGAATCTTTGAAAGCGGCTCCGGGGGATCCC
AAGGCACTGTTCCGTAGGGCTCAGGCGTACGAAGCTCTGGAGAAGTTCGAAGAGGCCTACAAAGACGCAACCGCTTTGTTTAAAGCGGATCCCGG
CAACAAAACCGTACAGCCCATGCTCCAGAGGCTTCATGTCGTCGTGGAAGAGCGCTCTGCCCGTAATGCCAAGACATCCACAAAAGTCAAGCAGA
TGATGGATCTTACTTTTGATTTGGCCACGCCCATCGATAAGCGTCGCGCGGCAGCCAATAACCTAGTAGTTTTGGCCAAAGAGCAGACTGGCGCT
GAACTGCTTTACAAGGACCACTGCATCGCCAAAGTGGCCTCACTAACAAAGGTGGAAAAGGATCAGGACATTTATGTGAATATGGTGCATTTGGT
GGCTGCTCTTTGCGAAAATAGCGTCGAGCGTACAAAGGGCGTTTTAACTGAACTCGGAGTACCGTGGTTCATGAGGGTTCTCGACCAAAAACACG
AGAACTGTGTGTCCACCGCCCAGTTTTGCCTACAAACAATATTGAACGCATTGTCTGGGCTTAAGAACAAACCCGATTCGAAGCCGGAGAAGGAG
CTGTGCACTAGGAACAACCGGGAAATTGACACTCTCCTAACATGCCTAGTTTATAGTATCACGGATCGCACGATTTCTGGAGCAGCTAGGGATGG
CGTTATTGAGCTTATAACCAGGAATGTCCACTACACAGCTCTAGAATGGGCCGAACGCCTGGTTGAGATCAGGGGACTGTGCCGTCTGCTGGATG
TGTGCTCCGAACTGGAGGATTATAAGTACGAGAGTGCAATGGATATCACAGGCTCATCATCCACAATTGCATCCGTTTGTCTGGCCCGGATATAT
GAGAACATGTACTACGATGAAGCTAAGGCACGGTTCACGGACCAGATCGACGAATACATTAAGGACAAGCTTTTGGCGCCTGATATGGAATCCAA
GGTGCGGGTCACCGTTGCGATTACTGCCCTGCTTAACGGTCCATTGGATGTGGGCAATCAGGTTGTGGCCAGAGAAGGAATACTGCAGATGATTC
TAGCAATGGCTACGACCGACGATGAGTTGCAGCAGCGAGTATCATGTGAGTGCCTAATCGCCGCTTCCTCTAAAAAGGACAAGGCCAAGGCTCTT
TGTGAGCAGGGAGTAGATATTTTAAAGCGGCTCTACCACTCCAAGAACGATGGTATTAGAGTACGCGCCCTGGTGGGTCTTTGCAAGCTGGGTAG
CTACGGCGGTCAGGACGCGGCCATCCGACCATTTGGCGATGGAGCTGCCCTTAAGCTGGCGGAGGCATGCCGTCGGTTTTTGATCAAACCTGGAA
AGGATAAGGATATCCGTCGTTGGGCTGCCGATGGTCTGGCTTATTTAACACTGGATGCTGAATGTAAGGAGAAGCTCATTGAGGATAAGGCTTCC
ATTCACGCTTTAATGGATTTGGCCCGCGGAGGAAATCAGTCCTGTCTCTATGGTGTGGTCACTACTTTTGTGAATCTGTGCAATGCGTATGAGAA
GCAGGAGATGTTGCCTGAGATGATAGAACTTGCCAAGTTTGCTAAGCAACACATACCGGAGGAGCACGAGCTGGACGACGTAGATTTCATCAATA
AGCGTATTACTGTGCTGGCAAATGAGGGCATAACAACTGCTCTTTGTGCACTGGCGAAAACTGAAAGCCACAATTCACAGGAGCTGATTGCCAGG
GTTTTGAATGCGGTTTGTGGACTGAAAGAGTTGCGAGGAAAAGTGGTTCAAGAAGGCGGCGTTAAGGCGCTGCTTCGTATGGCGCTTGAGGGAAC
TGAGAAAGGAAAACGCCATGCTACCCAGGCGTTGGCTAGGATTGGCATAACCATTAATCCGGAAGTATCTTTCAGTGGCCAGCGATCGCTTGATG
TAATCCGTCCTTTGTTGAACCTTTTGCAACAGGACTGCACAGCGCTGGAGAATTTTGAGTCGCTAATGGCACTCACCAATCTAGCCAGCATGAAC
GAGAGCGTGCGCCAGAGGATTATCAAGGAGCAGGGGGTCTCCAAGATAGAGTATTATCTGATGGAGGACCATCTGTACCTGACTCGTGCAGCTGC
CCAGTGTCTGTGTAATCTGGTTATGAGTGAGGATGTCATTAAAATGTTCGAGGGCAATAACGACCGAGTGAAGTTCTTGGCGCTTCTCTGCGAGG
ATGAGGACGAGGAGACCGCAACAGCTTGTGCCGGAGCTCTGGCCATTATTACTTCAGTGTCTGTCAAGTGCTGTGAGAAGATCTTGGCCATCGCC
AGCTGGCTGGACATTCTGCACACTCTGATCGCCAATCCCAGTCCGGCGGTCCAGCATCGAGGCATTGTGATTATTCTAAACATGATCAATGCTGG AGAGGAGATCGCCAAAAAGCTGTTTGAAACGGACATTATGGAACTGCTGAGCGGTTTGGGGCAGCTGCCCGATGACACGCGTGCCAAGGCCCGAG
AGGTGGCCACCCAGTGCCTGGCGGCGGCGGAGCGTTATAGGATCATCGAGCGGTCCGACAACGCGGAAATCCCCGATGTGTTTGCCGAAAATTCG
AAAATATCTGAGATTATCGATGATTAA
(SEQ ID NO: 260)

Start ATG: 224

MTNTINSEEVSDAGSYKDKGNEAFKASRWEEAVEHYGKAIKAGSKHKELAVFYKNRAAAYLKLGKYENAVEDCTESLKAAPGDPKALFRRAQAYE
ALEKFEEAYKDATALFKADPGNKTVQPMLQRLHVVVEERSARNAKTSTKVKQMMDLTFDLATPIDKRRAAANNLVVLAKEQTGAELLYKDHCIAK
VASLTKVEKDQDIYVNMVHLVAALCENSVERTKGVLTELGVPWFMRVLDQKHENCVSTAQFCLQTILNALSGLKNKPDSKPEKELCTRNNREIDT
LLTCLVYSITDRTISGAARDGVIELITRNVHYTALEWAERLVEIRGLCRLLDVCSELEDYKYESAMDITGSSSTIASVCLARIYENMYYDEAKAR
FTDQIDEYIKDKLLAPDMESKVRVTVAITALLNGPLDVGNQVVAREGILQMILAMATTDDELQQRVSCECLIAASSKKDKAKALCEQGVDILKRL
YHSKNDGIRVRALVGLCKLGSYGGQDAAIRPFGDGAALKLAEACRRFLIKPGKDKDIRRWAADGLAYLTLDAECKEKLIEDKASIHALMDLARGG
NQSCLYGVVTTFVNLCNAYEKQEMLPEMIELAKFAKQHIPEEHELDDVDFINKRITVLANEGITTALCALAKTESHNSQELIARVLNAVCGLKEL
RGKVVQEGGVKALLRMALEGTEKGKRHATQALARIGITINPEVSFSGQRSLDVIRPLLNLLQQDCTALENFESLMALTNLASMNESVRQRIIKEQ
GVSKIEYYLMEDHLYLTRAAAQCLCNLVMSEDVIKMFEGNNDRVKFLALLCEDEDEETATACAGALAIITSVSVKCCEKILAIASWLDILHTLIA
NPSPAVQHRGIVIILNMINAGEEIAKKLFETDIMELLSGLGQLPDDTRAKAREVATQCLAAAERYRIIERSDNAEIPDVFAENSKISEIIDD*
(SEQ ID NO: 261)

Classification: chaperone

Celera Sequence No. : 142000013383999
CGTTGGAAAAGCAAAGAAGCAACAAAAAAAAGACCGCAATTTGCCTTTGCAATTGGAAAATTAACAAACAAAACTCAAAAGTCAACACAACTTAT
GCCGCGTTCTCTTGCCTTTCGCGTTTATTATTTTTTAAAAATAAATACGTACTCGCGATGAGCACGAAAACAACCGGACCGCTACCGTCGACTAA
TATTTTGTTATTAACTATTTCCGCTGCACTTTTGTTTTAAATACTTCGGCCAAACACACAAAATACAACACATAAAGCGCAAAACAACAAAAAAC
ACACTGCCCACACGCACACAAAGAGAGCGCGAGAGCGCGCCAACCAAGTAGCGATAGATAAGAGAGAGAGAGAGAGAACTAGTTCCAGTGAAATC
CAAGCATTTTCTAAATTAAATGTATTCTTATTATTATAGTTGTTATTTTTGATATATATAAACAACACTATTATGCCCACCATTTTTTTGAGATG
CATCTACACAAGGAACAAACACTGGATGTCACTTTCAGTTCAAATTGTAACGCTAATCACTCCGAACAGGTCACAAAAAATTACCTTAAAAAGTC
ATAATATTAAATTAGAATAAATATAGCTGTGAGGGAAATATATACAAATATATTGGAGCAAATAAATTGTACATACAAATATTTATTACTAATTT
CTATTGAGACGAAATGAACCACTCGGAACCATTTGAGCGAACCGAATCGCGCGGAACTAACGACAGTCGCTCCAAGGTCGTCGAACAAAAGGTGA
ATGTGTTGCGGAGAGCGGGTGGAGACAGCGAAAGAGCAACTACGAAACGTGGTGTGGTGGAGGTGAATTATGAAGAGGGCGCGCGATTTGAAAA
GTTTGTATATAAAAAATATATCCCGGTGTTTTATGTAGCGATAAACGAGTTTTTGATGTAAGGTATGCAGGTGTGTAAGTCTTTTGGTTAGAAGA
CAAATCCAAAGTCTACTTGTGGGGATGTTCGAAGGGGAAATACTTGTATTCTATAGGTCATATCTTGTTTTTATTGGCACAAATATAATTACATT
AGCTTTTTGAGGGGGCAATAAACAGTAAACACGATGGTAATAATGGTAAAAAAAAAAACAAGCAGTTATTTCGGATATATGTCGGCTACTCCTTG
CGTCGGGCCCGAAGTCTTAGAGCCAGATATGCGAGCACCCGGAAGCTCACGATGAGAATGGCCAGACCCACGTAGTCCAGCGGCAGATCGGCGGC
GGAGAAGTTAAGCGTCTCCAGGATGACCTTGCCCGAACTGGGGCACGTGGTGTTCGACGATGTGCAGCTAATTTCGCCCGGCTCCACGTCCGCCC
ATTGGTTAATCAGCAGACCCTCGTTGGCGTAACGGAACCATGAGAGGTACGACAACCATTTGAGGTATACTGGCACCGAGCCCGAGTTCAAGAAG
AAGCCGCCAAAGAGCAGGAATGGTATGATAACCGGCGGACCCACAGACAGCGCCATCGAGGTCGAGGAGCTGGCGCAGGATATTAGATATCCGAA
GGACGTTGACACATTGGCCACCAGAGTGACCAGCGCCAGGCAGTTGAAGAAGTGCAGCACTCCGGCCCGCAGTCCGATCATCGGATAGGCAATCG
CCGTGAAGACCAGTGGCACTGTGAGAAAAAGCGGCAATTCGGCAATCGTTTTGCCCAGAAAGTATGTGTCACAGCGATAAAGTCGACTTCGGGCC
TCCCTCATAAAAACTGGCAGCTCTGAGGTGAACACCTAAATCGAATCGATTCATTAGAAAGTTAGTAAATTATTGAAATGCAAATGTATTCTAAA
CATGACTTACATTTATCGTGGCAAAGACGTTTTGAAAGGTCATGTTGGTCAGGAAGAGGAAGATGGCTCCGTTGATATTCATCACACCCACTTGC
GTGAGTTGTTGGCCCAAAAAGATGAGGCCAATCAAGATGGCAACCATCTGCAAATTAAAATGTTACTCGCATCTCATTAATATTCGCGAGTTAAA
TGAAATTTATTTATCTTCTGCAAAACTATAAACTATACATCTCATTGAAAAAAACTAAGAAGGGTGTGGAATCAGGCAATTCTATCTAAAATCTA
GCGAATTTGTTTCCAAGAATTGTAAGCGTTATATCATTTGTTTCCACTGGAACCACTCACCGTTGTCTGAATAAGTCGCACTTTTACGAGGAGTG
GTTCCTTGAGCACCGACAGCCAGGATCGCCACAGGACCGCCCGGAACTGCATGAACCAGGTGGCCTTGTAGGTGTACCCATTCTCCGGCTGCTCC
AGTGGCTTCTCCAGATTTTTGGTGGCCAACAACTGCTCCATATCCCGGGCTACTTTGCTAATGGCAAAATTGTCGCATATCTTGGCGATCCGATC
ACGGGACTCGATCTCCCGTCCGGGCACAACGGCCAACACCTGTACGTAAAAGTCCGCCGGATTGTAGTTGGTAGGACACTGGGCACCCACGCTGG
ATAGGAGTTGAGATGTTATGTAATACTAGATACCCTTAATAAACACATCGAACTCACTAGGAAAAGAAGTCGACGGCTTCGCTGGGAGTGCCCAA
GAAAGCTACCCTGCCCTCGGCCATCAGAAGGATCTTGTCAAAGAGCTCAAACAGCTCGGAAGACGGCTGATGAATGGTCAGGATGACGGTCTTGC
CCTTCTGCGACAGCTTCTTCAGCACCTGGACGACGCTGTGGGCGGTAAAGGAGTCCAGTCCGGAGGTGGGCTCATCGCAGATCAGAAGCGGCGGA
TCGGTTAGAGCCTCGGAGGCGAATGCCAGACGCTTCCTTTCTCCGCCGGACAGACCTTTCACCCTGCCGGGCACACCGATGATCGTGTGCTGACA
TTTGCTGAGCGAAAGCTCCTGGATCACCTGATCCACGCGGGCCACTCGCTGCCGATAGGTCAGATGTCGTGGCATCCGCACCATGGCTTGGAAAA
TCAGGTGTTCCCTGGCCGTTAGGGAGCCGATAAAGAGGTCATCCTGCTGGACATAGGCGCACCTGGCCTGCATCTCCTTGGCGTCCACAGGTTGG
CCATTGAGCAGTCGCATCCCGGATGGCGATACTTGGATGCCCTGCGGCGATCGAAAGGCAAGGGCATTCAGCAGGGTCGTCTTTCCGGCACCGGA
ACTGCCCATCACGGCCAAAAGTTCGCCCGGATAGGCCACGCCGCAAACTGAGTTTCAAATTGGTAATTGGACCCTTTATTAAGATTTCACACAGA
TCAGCCGACTGCGAATAGAAACTCACCGTTCTTGAGCAAATGTTTCCTGGGCGCCGGTATGTGTCGCTCGTTGCAGAATAGTCCGCGTGTCCGGT
TGACCAGCTGCCGCCATCCGGAGCCCGGCTGATTGACCGCCCCAAAGATGTCCATATTGTGCCAGGCATAGGTGAGGTTCTCGGCTAGTTGGCCG
CTCCCTGAACCGGAGTCCTCCGGCGGACTGGGTGGCCGGAGCGTGCCGTAGTTTTTGGCCTGCCCGAAGCCCTGGTTAATGCAGCTCTGCGAAGC
CGCTCCGCTGTCACCCTGCAATGATAGGGGATCTCAAATATCAACTACAAGCGTTATGCTCATCTAACCCCGAACAAAAAGTACCCCGAAGTATC
CTACGAAGTAGGTTTATACTTTTATTTATTTTTTGTGCATCTAGAAAAGGTTTCAAGCTGAAAACTTTTCAATTTCACGGCGTTCGTCCATAAAA
ATGAAGGCGTCTGTGCATAAATCTAGCCCAGCCTGGCCAATCCCTGCTCCGCCGTCCCTGTTTCCGGGCACTAACCCCCCCCCCCCCCCTCGGCT
TTATAAAGAAGGAGCCCATCTGTTTAATAAAAATGCCCAAGATCCGAGTTTTCCAAGTTTCCCAAAAAGGAGATGGCGAGGCCTATTTAAAATGT
GCAAATTAGGGCTGGCACTTGGTGGATGGCCTTGAAAGTGGGCGGTGGACGGTTGACGGGGTCACAGGTCGTTGGGCGATGGACGATGGGGCGAT
GGGACGATGGGTGGTGGCAGTGGCAAGGTTCCTCCCACCATGTTGCCACCTCATAAGACAATTGCGAGTGTAAATCGCTGGCATCTTTGGCTTTC
GTTTGGGGACTTTGAGCTTCGCCAGTTTTGTTTTTATTAAATATAAAACTTTAAGGATACTTTGGCTTTTTTTGGGTGGTGGGAAAACTCAATCT
CTTGTAGATAAGTGCAATGAGCAGTATAAAGCAGTCCATTTACTTGATCCAATTATGTTGAACGCAATAGTGTTCAAACTACTACTTCTGCAATT
GAGTTTAAGTTTATAAATCCGAAATACAAATTCTTATTTACGTTATTTTGTTTACGGGTAAAGTGATTTCCAAAACCACTGAGCTGTCAGTTTTC
GCCCAGGTGGGGCTTCCCTTTTCGAAATGGCGGTAACCGAAGACGTTTGCGGTATGGTCAAATCAAGCCATCCTCCCCGCCCCAACTTTTCGCCC
CATACCACTTCCGTTCGCGCATATTTTCATTTTCATAAACAATTTTCCGTTTTCCATTTGTGGGGTTTCTTGCCATCGCAGCGGCCTGCGGCAAA

FIGURE SHEET 143

GCATAAATAACAGGGATCCACTAATTGGCGTCGAGGCAAAAAAAAAAAAAAATGGAAAAAACAAGACAAAATGATGGCCACAATATGGAAAGCAT
TTTATCCGCCGCTGCTCTCATAATAATTTGTATAAATAATCATAAAAAAAATTAAGCAAAAAAATGCAAGCAAATGAGAAAGGCAAAATCCGAAG
AAGAGGGCCAAATAAAAAGCTGACATTCAATAAAAGCAAGAAAAAATAATGTCCACCTTGCACTCAGCGCCTGGCGGTCCTTGCTACAGTGAGCC
CTGCTAAGAACTTTCATTTTTTGAACTATTTAAAATTAAATTTATTTTTCAAAACGATTGGGGATTTGGATTTATCGTTTACATTGCTACATAT
AAAATCTAGCTAAAAGACCAAAGCCTGAAAACTGTTGCATTTCCTCCTTAGCGAGGCTTCACTGCTCATCTTCTGCTGCGATGCTTTGACAGCTT
ATTCTTCTAGCCACTCAGTGTCCAGTTTTTGGCCTGTTACCAAAAAAAAAGCACAATTGGTGACGTTACGAGAGGTAGACGCGAAAAAATGTAAT
ATCCGTTTTCAGGCACTCCTCGAGCAGAGCGAGATGGCCATATGGCTGGGAAAGAGATAGAGGGACATGGCGAAATTGTTTTCACAACAAATGAG
GCCGAAAAATGTTATTAAAAAGTTTTCTTTTCTTTTCTGTTTTCGCCGTCCCTTTCCCACTGGGTTTTCTTATCTCCCTGCCTCCTCTGGTTTAC
TCTCCCACCTTTTCCCTATTTTCGTATTTTGTTGAAATAAGTAGCGAAAGATGCTACATTTCATATTTATTTAATTTTTTGGCTTACTTTTTTTT
TTATTTACTTTGCGTGCTATTTTTGAATTACTTACGAAATACGAAGGAAACTCGAGGAGTGGGCGCTAGATGGCGCTGTGCAGGGAGGCGAAGGA
GTATCGTGATGAACTTGACAAATTGAAATGACTGAATAAAGAAGCGACTCAATTTGTTGTTCCTCCCGTTTTGTCGATTGTGCGAGTGGCTAATG
AGTGCACTCAAAAGTCATTCACTTTGATGAGAACGAAATACTGAAGGAGGCGCAATTATTCAGCGGAAAAGCTGACGACCACTCGATATTATTAA
GGAAATATCAGAGCGTAAACGGCCCAATATGTACATATATGCAACGAACATATAATTAAAGATGGCTTCAAATATTCCATACATATCATATTTTT
CAATACTTTGTTACCTTTACTGCGTTACTTACTTCCCAAAAGAATTAAAGTTCTTATCTCCTTGTATAACTTTTTGAGACTTTTCAAAATTGTTT
CAAAGAGCCCGGGGCTAGATATGCAAATCGTACTCACTTATTTATTTTGTTATACAAGCCGAGGTGCTAAGAATTTAAAGCAAGATACGCACGAA
GATACCTAGATATCAGATGCTGAGCCCAAAGCATTCGTCTAGCCAAATAATGACCCAGATAAGACTAGATTGTACATTTTTCGTCGAGCGAGACG
TGCAAACAACGAGGTATTAAGATCAGGTAGAAGATGCGAGTACACAACCAGAAATGGATACGGATACAGTATCTAGTATCTTGGCAAGCCTAGAG
TTATAGACACCCAGCAATGTTGTTGGCCAACTTAAGCCGACTCCTCCCACGCCACCACTGGTTATGCGTCCCTAATTACGATCTACTACATCCAA
CTATTTGGGGTCGATGTATAATGTAGTGTAGTGTAGTGTAGTGTAGCAAGAAAATATTTGAGAATGAAAGGTGGAAGAAATGAGGACTTCATGGT
AAGCTTAAAATATCTGGTTGTTATATTTTTTGTAAAAAAGAATATAGTCGAAAATGAATGCCTTTAGATGTCTTGATCATGATATGATCTCAAAA
ATTGTCTTATATAGCGAGAACAGCTACCAGAATAATCTGTTTCGTGTCACTATTTGTTTGTGCAATTGCGGTTTGGGATTTTTGTGGGTCGCAGT
TCTCACGCCGCAGACAATTTGATGTTGCAATCGCAGTTCCTATAGATCAAGTGAACTTAAGATGTATGCACATGTACTACTCACATTGTTCAGAT
GCTCGGCAGATGGGTGTTTGCTGCCTCCGCGAATTAATAGCTCCTGATCCTCTTGGCCCATTGCCGGGATTTTTCACACTTTCCCCTGCTTACCC
ACCCAAAACCAATCACCACCCCAATCACTCAAAAAACAAACAAAAATAAGAAGCGAGAGGAGTTTTGGCACAGCACTTTGTGTTTAATTGATGGC
GTAAACCGCTTGGAGCTTCGTCACGAAACCGCTGACAAAATGCAACTGAAGGCGGACATTGACGCTACGTAACGCTACAAACGGTGGCGAAAGAG
ATAGCGGACGCAGCGGCGAAAGAGACGGCGATATTTCTGTGGACAGAGAAGGAGGCAAACAGCGCTGACTTTGAGTGGAATGTCATTTTGAGTGA
GAGGTAATCGAAAGAACCTGGTACATCAAATACCCTTGGATCGAAGTAAATTTAAAACTGATCAGATAAGTTCAATGATATCCAGTGCAGTAAAA
AAAAAAAATGTTTTTTTTATCTACTTTCCGCAAAAATGGGTTTTATTAACTTACATACATACTAGTGACAACATGTTTATGTTTAGCTAATGTGT
TCCGTTCAAAATAATTAAAAATTCGACCACCTTTGCACCAATATGATAGTACCCCACCTGGGCAGTACTCATAAGCTGAGTGGCTGTCTTTGAAT
ACTGATTAGGTTGAGTGGGAAGCGTCTTCTTATCGTGAATAAGAGAGTTCTTGTTAATCCGCCTGTTGTCGTCCCGTTTCGGGGGTTTGCACTGT
ACTTTGCATGCATGATTTATCAAACGGCGACTGTTGATGATGCGCATTCCGCACTCCCCGTTTCCCGTACGCCTATCCGCACCCGTACTTCGGAC
ACTCCGGTCGTTGTCGTCATCGTTAGCACCTCATCTCAGGCCCCGGAATCATGAACTGCCGCCATCAGCTGTCCGGGCATTATCAATCTTCATCA
TCGGGGCCAGTTGGTCCAGGATATGGATCTCGACTGGGACGGGTTTTCCGGGAGGCTATCAATACCATTTTCACGGACGATGTGGTAACAGGTTA
GCAGTTGCAGTTGCCGAGGAATCTGCAGGAATTAATTTGCTGACGACGATTAAGTGGTCTTCAAATGAATATGGTTTTCTTTTGAGAGTTTAGCT
CAGAATAATAGCTTTTGATTCGATTTGCAAGTTAATTATGCATATGCATGTGATATTTGTAGAAGTCTCACTCAGCACT
(SEQ ID NO: 262)

Exon: 6869..6640
Exon: 3530..3257
Exon: 3182..2528
Exon: 2466..2151
Exon: 1947..1816
Exon: 1745..1001
Start ATG: 6711 (Reverse strand: CAT)

Transcript No. : CT9359
GTTTCGTGACGAAGCTCCAAGCGGTTTACGCCATCAATTAAACACAAAGTGCTGTGCCAAAACTCCTCTCGCTTCTTATTTTTGTTTGTTTTTTG
AGTGATTGGGGTGGTGATTGGTTTTGGGTGGGTAAGCAGGGGAAAGTGTGAAAAATCCCGGCAATGGGCCAAGAGGATCAGGAGCTATTAATTCG
CGGAGGCAGCAAACACCCATCTGCCGAGCATCTGAACAATGGTGACAGCGGAGCGGCTTCGCAGAGCTGCATTAACCAGGGCTTCGGGCAGGCCA
AAAACTACGGCACGCTCCGGCCACCCAGTCCGCCGGAGGACTCCGGTTCAGGGAGCGGCCAACTAGCCGAGAACCTCACCTATGCCTGGCACAAT
ATGGACATCTTTGGGGCGGTCAATCAGCCGGGCTCCGGATGGCGGCAGCTGGTCAACCGGACACGCGGACTATTCTGCAACGAGCGACACATACC
GGCGCCCAGGAAACATTTGCTCAAGAACGTTTGCGGCGTGGCCTATCCGGGCGAACTTTTGGCCGTGATGGGCAGTTCCGGTGCCGGAAAGACGA
CCCTGCTGAATGCCCTTGCCTTTCGATCGCCGCAGGGCATCCAAGTATCGCCATCCGGGATGCGACTGCTCAATGGCCAACCTGTGGACGCCAAG
GAGATGCAGGCCAGGTGCGCCTATGTCCAGCAGGATGACCTCTTTATCGGCTCCCTAACGGCCAGGGAACACCTGATTTTCCAAGCCATGGTGCG
GATGCCACGACATCTGACCTATCGGCAGCGAGTGGCCCGCGTGGATCAGGTGATCCAGGAGCTTTCGCTCAGCAAATGTCAGCACACGATCATCG
GTGTGCCCGGCAGGGTGAAAGGTCTGTCCGGCGGAGAAAGGAAGCGTCTGGCATTCGCCTCCGAGGCTCTAACCGATCCGCCGCTTCTGATCTGC
GATGAGCCCACCTCCGGACTGGACTCCTTTACCGCCCACAGCGTCGTCCAGGTGCTGAAGAAGCTGTCGCAGAAGGGCAAGACCGTCATCCTGAC
CATTCATCAGCCGTCTTCCGAGCTGTTTGAGCTCTTTGACAAGATCCTTCTGATGGCCGAGGGCAGGGTAGCTTTCTTGGGCACTCCCAGCGAAG
CCGTCGACTTCTTTTCCTACGTGGGTGCCCAGTGTCCTACCAACTACAATCCGGCGGACTTTTACGTACAGGTGTTGGCCGTTGTGCCCGGACGG
GAGATCGAGTCCCGTGATCGGATCGCCAAGATATGCGACAATTTTGCCATTAGCAAAGTAGCCCGGGATATGGAGCAGTTGTTGGCCACCAAAAA
TCTGGAGAAGCCACTGGAGCAGCCGGAGAATGGGTACACCTACAAGGCCACCTGGTTCATGCAGTTCCGGGCGGTCCTGTGGCGATCCTGGCTGT
CGGTGCTCAAGGAACCACTCCTCGTAAAAGTGCGACTTATTCAGACAACGATGGTTGCCATCTTGATTGGCCTCATCTTTTTGGGCCAACAACTC
ACGCAAGTGGGTGTGATGAATATCAACGGAGCCATCTTCCTCTTCCTGACCAACATGACCTTTCAAAACGTCTTTGCCACGATAAATGTGTTCAC
CTCAGAGCTGCCAGTTTTTATGAGGGAGGCCCGAAGTCGACTTTATCGCTGTGACACATACTTTCTGGGCAAAACGATTGCCGAATTGCCGCTTT
TTCTCACAGTGCCACTGGTCTTCACGGCGATTGCCTATCCGATGATCGGACTGCGGGCCGGAGTGCTGCACTTCTTCAACTGCCTGGCGCTGGTC
ACTCTGGTGGCCAATGTGTCAACGTCCTTCGGATATCTAATATCCTGCGCCAGCTCCTCGACCTCGATGGCGCTGTCTGTGGGTCCGCCGGTTAT
CATACCATTCCTGCTCTTTGGCGGCTTCTTCTTGAACTCGGGCTCGGTGCCAGTATACCTCAAATGGTTGTCGTACCTCTCATGGTTCCGTTACG
CCAACGAGGGTCTGCTGATTAACCAATGGGCGGACGTGGAGCCGGGCGAAATTAGCTGCACATCGTCGAACACCACGTGCCCCAGTTCGGGCAAG
GTCATCCTGGAGACGCTTAACTTCTCCGCCGCCGATCTGCCGCTGGACTACGTGGGTCTGGCCATTCTCATCGTGAGCTTCCGGGTGCTCGCATA
TCTGGCTCTAAGACTTCGGGCCCGACGCAAGGAGTAGCCGACATATATCCGAAATAACTGCTTGTTTTTTTTTTTACCATTATTACCATCGTGTT
TACTGTTTATTGCCCCCTCAAAAAGCTAATGTAATTATATTTGTGCCAATAAAAACAAGATATGACCTATAG

FIGURE SHEET 144

(SEQ ID NO: 263)

Start ATG: 159 (Reverse strand: CAT)

MGQEDQELLIRGGSKHPSAEHLNNGDSGAASQSCINQGFGQAKNYGTLRPPSPPEDSGSGSGQLAENLTYAWHNMDIFGAVNQPGSGWRQLVNRT
RGLFCNERHIPAPRKHLLKNVCGVAYPGELLAVMGSSGAGKTTLLNALAFRSPQGIQVSPSGMRLLNGQPVDAKEMQARCAYVQQDDLFIGSLTA
REHLIFQAMVRMPRHLTYRQRVARVDQVIQELSLSKCQHTIIGVPGRVKGLSGGERKRLAFASEALTDPPLLICDEPTSGLDSFTAHSVVQVLKK
LSQKGKTVILTIHQPSSELFELFDKILLMAEGRVAFLGTPSEAVDFFSYVGAQCPTNYNPADFYVQVLAVVPGREIESRDRIAKICDNFAISKVA
RDMEQLLATKNLEKPLEQPENGYTYKATWFMQFRAVLWRSWLSVLKEPLLVKVRLIQTTMVAILIGLIFLGQQLTQVGVMNINGAIFLFLTNMTF
QNVFATINVFTSELPVFMREARSRLYRCDTYFLGKTIAELPLFLTVPLVFTAIAYPMIGLRAGVLHFFNCLALVTLVANVSTSFGYLISCASSST
SMALSVGPPVIIPFLLFGGFFLNSGSVPVYLKWLSYLSWFRYANEGLLINQWADVEPGEISCTSSNTTCPSSGKVILETLNFSAADLPLDYVGLA
ILIVSFRVLAYLALRLRARRKE*
(SEQ ID NO: 264)

Name: white
Classification: transporter
Gene Symbol: w
FlyBase ID: FBgn0003996

Celera Sequence No. : 142000013384832
CGTTGCCAAGCCCCAAAAAGGGGGCTCACCAGAACGAGCACAGTAAAAGAGCAAGCTGAATATATTTTCTAAGTAAAATTTATTTATTATGTATA
AATAATTCTCTTTTAGCTCTCGCACAAGCGCTATTAACGTTAGTAATTTACAGTTCGCTCTGCAGTCCTCGTTGCCGAACCAGGGACTCACAGTC
GGGTATCCAGGTCACCTTTGGTGGGATTTAGGAGATCCCCCCTGCTGTAACCACTGGGTGTCCCTGGTCGGCTGCGAAGTGGAAATCAAACGAAA
CATAACGGCACAAATAGTTGGCTTAAACAATTACAATAACAATTGTGGAATATATAAATTTGCATACAGGCTAAAAGTGAAGTGGTCCCGTCTCC
ACAAGCATAGCTCCCACTTCACTTACGTTCGTATTCGTAATTTAGTTAGAAATTAGATTTCTTGTACTTGTTGAACATCGTTTGCTTTAGTGTTG
TTTTGCAGTTCCCATAGCTATCTATCCAATATATAAATACGAAAATCAATTGTAAAGAAGAGGGATATTCGGGCCGGTGCCACCGCTGCGCCATG
GTGGTTATTTGTTGACTTGGGCGCAATGGAGCCCCAACGGGTACAGAAGGAATGATTGGGATAGATGCGACTCGCTTCTGTGATTTTTGACTTTG
GCTACCCTTAAACCCATAAGAGAGATGCAACGCAGAGGTTACAATTTTTACAATAGAACGTTTGTTAATTTGTTGCTTAGGCGCTGCTTTATCCA
CTACTATATCTACCAGTTATTTATCATCCTCAGTTATACATTTATACAATCCTATTGCACACATACGATTCTCATATGTCTTGCTTAGCACCCCC
TCAAGATACATATACATAATCATATACATACATAGATATAGATATTTTGATACAGTTATAGTTAAAGTTAAAAAAATACCTCACACTTGATAATA
ATGAGTGTAAAGACCCGCCCGCGACTATGGTATGAAGTTAACCCCGACCAGCTCGAAAGAAAGTGATAGTGTAGGAGGCATAGGAAATAGAGGGT
CGAGAAGGCCTTGAGTTGGCGGTCCTAGACGGGCCCAATATCACTTTGGTATCTGGCGGTCAGGTAGTTGGCCGCCTCTGTCATTTGTTCCAGGC
ACTGGTACAGACCGTTAAGATGCCTCCGGCAGCGCTTGGCCAGCTCCGTGGCCTTGTCCCCCGAGCCCGGCTTCGATTTGGCGACGTCTACAATG
TCGCTGCCGTCGCTGCTTTGGGCGTTGTCGCTCTTGTTGCCATCGGACTCTAGCCCCGAGTCGTTTTCCTGCGATATGTCCGAGTCAGAGTCACT
CATGTTGCTCACCGAGTTGGTGGACATCATGGATGCGGTAGAGGTACGGCGCACATGACCCTTGACACTTCCGGATGCGGTTGTGCTTGGACTGC
CGCTGTTGAATTCAGTCTTGCTCTCGCTGGGATTGCAGCTCGAAGTGGAACTGGTACTGGCGTTGAGCTGCTGTTCGGAGTGCTGCTGGTCGTCG
TCCTCCTGGTTGGCGGTCCAAAGCAGATCTTTTTTCAGGGAGTTCAGCATGTTGTACAGATTGAACAGCTCGGAGGCGCTGAGAAAGTCTTGGAC
ATTTTTTGAATGCGCCGCTCCCCGCTTGCCGTGGGCACTGGAGGTCTGTGTCAGCTGGTTGGCGGTCGAGTCCTTGCCGGTTGCTGGGATGATGT
CAGTGCTGTCGCCGATCTGGGGATAAATTATGTAAAGTGGGAGCCATAAGTTGTTGGTTCCGGATCCGGATGGCTGGTCAAATGGGGGGCTGGGG
TTCTTGGGTTATGCGGTACCAACCTGCCGATCCATGAGCCTGCATGGCACCAGTATGGTGTCGTCCATAATGTTGACAGTCTTTACAAACTTTTC
CATCACATTGACAATGCTGTCTTTGGAGAACTGCTGCTCATCGTGACGGGCGATGCGGCGCAGGCAGTTTCTGAAAAACAGAACAATCGAAAGAT
GAGCTTGGGCCAGAGCACAATAAACCAGTAGAGCGTGTGCAGGGGAACCAGTTTGGATTGGACAATAGTCTGCGTGATTAGTGACTATGCCACAT
CACGCCAGACTGGACCAAGCGCTGGCCGTTCTAAAGCGTCGTTAAGTCTGCGGCGATCAGACTTCCGCCACTCGAAGCCATCTTTCTTTGATGCT
TTCGACTGGAGATGGGTGCGCCTCCTGCTGACCAACGTGGCATATGATATATATGAATTGGTTTCTATGCAAATCAGCGACTCGCTGGCGTTGTC
GCAAATTCAATTTGTATAAAATAGAAAACCAGTTGGTGCTTTATACCTGACATTGCTCGTGTGGCTCTTAAAACAAAGCACAGACGGACGGACAG
AAAGATTTCTATTTTGGTTTCCAAAGCCAATTTAACGCGTCCACGTGCTGTCGGTGGCGGGGTGCGAGGGTAAAGCCCGACTTTGCTCGCAAGCT
TCAATGTAATGGTTATACAATCCTGGCTGGTCGCATTAACTTTAATTTCACGAAAAGATCGCGTAACATCTCCAGGTCAAGCCCCATAAACTTGC
CTGAGCTCCCTCCATTAACCCGCCGGGAATATATGTTAGTTGCTGATATCTGGAGCTGGAGCGGCCAAAGTCTAGAGGCGGCTTGGCTTATCGTC
GCTAGACAGTTCCCAGACAGAGCTGAAGTTGCGTATCTCCCGCACCTCCTATTTAATGCGGCCAGATTGCTCGGGGCGGATCGGCATGTGGGCAG
CCAGTTCGGGGCCGCGTGATCGCAGCTAGTTGACAGAGCGAGCGCCGAGCGCACTGATAAATTTAGTTTCAGTGACTGCGCCATTTAAAGACCTC
TACCCTACAGTTCTATCCCTGGCCAGCGCCCGCCCCGATGCCATGGCAATCCAACTTAGAAAATCTAGATATCGATGACTGAAGTGTAACGCGCG
GCAGGCCGGGGTGGGGTGGCCACGCGAGTACTGCGTGCTCCGAACTCTGCTGACCGACATCGTCTCACTGTGGTCTAGAACCACAATAAGATCTA
GATCTAGAGAAGGCTGGCGCGGGTGTCAATGTTCTTTCCACTGGCACGGCCAGATGTCGTGGACGTCGACGGAGGATTCCCAGCCACTGAACAGA
GTGACTAATTAAGCTAATTGCAGCGGGTTCCAATCATGGAAATCCGCGTAGGAATGCGAAAACAATTACCATCTTATCAACGCTTTTCGCTTAGA
CACTCGACCATAATTGACTGCCATCTCGTGGAAACCTGAGTAATCGCCTCTATTTATTTTAAATTATAGATATTTTCTAGCCCTGACCACGACCC
TTGCTTCGCTTAGTCACTTAAGCTGGCCACACGATAGTTCAACTTATCACTGCATTTTGAATCCTTTCCTTGCGAATCCTCTGAACAGATCCCGA
AAGCCCAAAAACGCCGGCTTGGGCAACACGCCAGATGCTACCAGCCAATTGACCAGGCAATAGGTACACCTGAAGTGTTATGGAAATTTGGCTAA
GCCCCACAAGCGTCACGCGACATGCTCGCCAAGAAGGGCGGGGTAAGCAGCGGGAGAGGGAGGGTACCGCATACAACGCCGAAATCAGGCGACTT
TTTCGCTCAGCGGTAGCTAAGGGCGGTGAAGGAGTGCTGAAGGGGTGGTGGTTTGGTGGGTGGCTGATGACGAGCTGGCTTTATGTGGCAAGCGA
ATCAAACGCTTCTCTTCGCACTCTCTCTTCGGTCCGTTTCGCCGTTTTCTCTTTGCCGCCGAGTGGCGTGATGTTGCCCAGAAACTGTACAGCGG
CCAGAGTCGCCTCCATCAGCTGAGCAAGATGAATGAATCTCTAGCGATGCTCTGCCTTCCCCTCACCTTCCTACCATCGCTCATGCAACCATGTT
TAGTGGTATTTCTCGTATTTGCAATGTTGAGCAATGGCATATACATAGCCATACGAACAGAGTTGACCAATATTTGGTTTACTTTGGCTTTGGCT
GCGCCTCGACCTCCAGCATAATCGATTTTTGATACGCCCGCAAATTAGATATTCTACCTACTCGGTGGCCGGGTTGGCCGGATTGGCTCGGCCAT
CGGGCATAGAGCATTGACGACCGTAAGTTGGCGCTCAAGGCGACACCTGCCTCAAAAAGTGACACACTGCCAGCGCAACGAGGTGAATCAGAGAA
TTTTCTGCGATTTAAGCGCCCCAAGGAGGCGGGCAGCACCAGAAGCGATGAGTAATGGCTATGGCCGATAGCTGGGCTGGCGGACTGGTGTCAGT
GGACCGGAGGTGCGCACAGATAAGGCATCTTATCGCTTATCCCAAAGCTGTGATTTGCCTCCGCTGGCTCACTCGAAACATTTGGGCAAACAAAC
GGCAAAAAAAACACCAACATACTTCTGTATAGGTGTACAATATATAGCCGATTGTGTCATATTAGCGCTGGCTTGATTTTTTTATTTTATTTTAT
TTTTTTGTATTTGTTGTTGTATTTTTCTTTCGAGTTTGAATGGCCGTCCGTCCCCCTGTCCATCGAAAATCGTACGATAAATTTCTTGTATCTC
GTTTTTCGTTCGGCGGTGGTGGTGCAAACGAAAGAGAAAACGCTCGCGGGGTGCGGTTTGGATTCAATTTGAGAGGCGAGTAAATGGACGGAAGA
GAGCGATTCGGATGGGTTAGAGGAGAGGCAGTGCGGGGCTTGGGTGATGGATCGGGAACGGGGGGGGGGATCAATTTAGCATCACTTGGGCAAA

FIGURE SHEET 145

TTGAACTTAAACGCCTTAACTAGCGAATTCGGATTGCGACTTACCGACTTGTCTCCAGCTTGGTGAGGTCCGTGTATCCACTCATGATGACTGTG
TATTCCTGATGACTATGTACTGCTGCTGCAGGAAATATGTGGTTCGAGAAATTTTCTTTGGCCGCACCAACACTCGCGCACTTTCACTCGCGTTT
GGAATCGGAGTATTCCTGACAGGGATTACGAAATCGGCACAGGTGACTGGGCTGGCTTCAGCTCGGTTGCAGTGCAGGTCTGGCCTGAATTGGTT
TGGATTCGGAATAGGAGTAGCTGCTGCCCCGGCGGAACTGCTGTGTCTAGTGCGCTGCCTCCAATAAGTCGCGGCTGTTTTATGCCAAAAATTTA
CATGTACTCGATTAGACCCCGACTTTGGTTTGGCTTTGGCCGTCGATCTAGTCCGAACCAATTAAATATGGGAATTCTAAGTAGTCTGCACACGC
ACCGAGTTTAATTTAATTTCAGTTTCTGTTTCGACACGAGCAGTCAGCGAGAAGAATTTTGAAAAAATTACAGAGAGGGAAGCATTGCCAGTTGC
TTTTATAGTACGGGCCGAGTCAGGGCTGCGGAGGCTCCGATAGAACTATCGATTACTCAGCTCGGGGCAATCGATGTAAACATCAGCTGTCATGT
TCAATGTGGCAGCACCGGCCAACGCCGTTAATTAATTAGCTAATTCGAAAATGCTTAAATTTAAAAATAAATTAGGATAAGTGGCAAAATATTCA
ACATTGTTTTATTTTTTTTTAGTTTTGCACCAAATTATCAATATAGATTGTTGTAACATAACTTGGGCAAAAAATAGAGCGTGCCATTTAATTTT
CCTCTTATTACTACTAAAGTGCATTCAACAATTGCTGGAGAGTACATATGTAAATTGCACTGAGATTAGAGAACTTCCATTATTGCGAATCAATG
CTCTTCCCAGAACCACCTTTGCAACCACCCGGAAGCGCACGTCTGTTAGGACCGCTCGTGTCGCAGGACACTATCCACTTACTCCACAATCCCTT
CTGACCACGCTGCGTCCTTTACTGTGTCCCAAGTCGACACCGTTTCCGATGGGCCTCTGTACGCATGGCCGGGTCGAGTCCAAAGTCCAGCAGTC
CAGGTACCGTTAGTTCGAGCATTTCTTAGCTTGCAAATTGAAGTGGTCTTCAGTCCCTTAATAACATTTCGTTTTCGCCTAGAGCTGCACTTTAG
ATTTACATTTCTTTCCTTTTTGTGACCTAAAAAACAAAGAGGCGTTAAAGACAGTTGGAAGTACATTTTCTATAAAAGCTTACTGAATTCCCGAA
GTACGAAAAAACTCCATTTATTCCGGCTGATCTCTGCGCCCCTCAGGTCTCTTGGAATCCTTTGCACGCACAGGTACATTTCCCAAACTTGATCC
CGGGTCAATGCGTCGATCATGTTCAGCTCGGGGTCCCAAAAAAAGGTAATAACTCCCCGCCTTAAGTTCTCCGCCAAGTCGTCGAACATCTGTTA
AATTTAAATTAAAATTATTTTTGCATTCGTCGACAT
(SEQ ID NO: 265)

Exon: 5306..4795
Exon: 1970..1829
Exon: 1726..1001
Start ATG: 4835 (Reverse strand: CAT)

Transcript No. : CT9411
TTCCCTCTCTGTAATTTTTTCAAAATTCTTCTCGCTGACTGCTCGTGTCGAAACAGAAACTGAAATTAAATTAAACTCGGTGCGTGTGCAGACTA
CTTAGAATTCCCATATTTAATTGGTTCGGACTAGATCGACGGCCAAAGCCAAACCAAAGTCGGGGTCTAATCGAGTACATGTAAATTTTTGGCAT
AAAACAGCCGCGACTTATTGGAGGCAGCGCACTAGACACAGCAGTTCCGCCGGGGCAGCAGCTACTCCTATTCCGAATCCAAACCAATTCAGGCC
AGACCTGCACTGCAACCGAGCTGAAGCCAGCCCAGTCACCTGTGCCGATTTCGTAATCCCTGTCAGGAATACTCCGATTCCAAACGCGAGTGAAA
GTGCGCGAGTGTTGGTGCGGCCAAAGAAAATTTCTCGAACCACATATTTCCTGCAGCAGCAGTACATAGTCATCAGGAATACACAGTCATCATGA
GTGGATACACGGACCTCACCAAGCTGGAGACAAGTCGAAACTGCCTGCGCCGCATCGCCCGTCACGATGAGCAGCAGTTCTCCAAAGACAGCATT
GTCAATGTGATGGAAAAGTTTGTAAAGACTGTCAACATTATGGACGACACCATACTGGTGCCATGCAGGCTCATGGATCGGCAGATCGGCGACAG
CACTGACATCATCCCAGCAACCGGCAAGGACTCGACCGCCAACCAGCTGACACAGACCTCCAGTGCCCACGGCAAGCGGGGAGCGGCGCATTCAA
AAAATGTCCAAGACTTTCTCAGCGCCTCCGAGCTGTTCAATCTGTACAACATGCTGAACTCCCTGAAAAAAGATCTGCTTTGGACCGCCAACCAG
GAGGACGACGACCAGCAGCACTCCGAACAGCAGCTCAACGCCAGTACCAGTTCCACTTCGAGCTGCAATCCCAGCGAGAGCAAGACTGAATTCAA
CAGCGGCAGTCCAAGCACAACCGCATCCGGAAGTGTCAAGGGTCATGTGCGCCGTACCTCTACCGCATCCATGATGTCCACCAACTCGGTGAGCA
ACATGAGTGACTCTGACTCGGACATATCGCAGGAAAACGACTCGGGGCTAGAGTCCGATGGCAACAAGAGCGACAACGCCCAAAGCAGCGACGGC
AGCGACATTGTAGACGTCGCCAAATCGAAGCCGGGCTCGGGGGACAAGGCCACGGAGCTGGCCAAGCGCTGCCGGAGGCATCTTAACGGTCTGTA
CCAGTGCCTGGAACAAATGACAGAGGCGGCCAACTACCTGACCGCCAGATACCAAAGTGATATTGGGCCCGTCTAGGACCGCCAACTCAAGGCCT
TCTCGACCCTCTATTTCCTATGCCTCCTACACTATCACTTTCTTTCGAGC
(SEQ ID NO: 266)

Start ATG: 472 (Reverse strand: CAT)

MSGYTDLTKLETSRNCLRRIARHDEQQFSKDSIVNVMEKFVKTVNIMDDTILVPCRLMDRQIGDSTDIIPATGKDSTANQLTQTSSAHGKRGAAH
SKNVQDFLSASELFNLYNMLNSLKKDLLWTANQEDDDQQHSEQQLNASTSSTSSCNPSESKTEFNSGSPSTTASGSVKGHVRRTSTASMMSTNSV
SNMSDSDSDISQENDSGLESDGNKSDNAQSSDGSDIVDVAKSKPGSGDKATELAKRCRRHLNGLYQCLEQMTEAANYLTARYQSDIGPV*
(SEQ ID NO: 267)

Celera Sequence No. : 142000013384832
CTGGTCTGGCCCCGCGCTGCTGGTGGTGGCGAGTGGTGCGACGGTGGTGGTGGGTGACGGCAAAGTGGGTGTGGGATGTGCGTGCCCAGACAAAG
TAAGAGCGCTTAGAGTCTATTATCTATCCGGCAAGTGCTGACGCGTTGCGATCGCCCGTCGTCGATCGCTAAATCTGTGTACTCCGAAAAATCTG
GTGCATCAAAATGTGCTACGTTATTATCACCATCGCCAGTCTGGTGTGGTTCCTCTGTTCGCTGGTGGCCGACATGCTCTTTGCTGTGGCCCTGG
TCACGCCCAGGTGGCTGGTGGGCCCCGCCCAAGGAACAGACTCCACCGCCAGCTCTCACCACCAATCCTCGGTGGGCATCTACACGCGCTGCAAG
GTCATGCAGGAGGGCGGATTCCAATGCGGCCGCTTCGACTTGGACGGACTGGCCACGGACAGTAGCGTTTACCCCAACGAATGGAAAGCGGCAAT
GTTCTTCGTCATGCTGGGATTTAGTCTACTCTCTGTAACGGTGATCCTGACCCTGATCACCTGCTGCCGCCAGTCGGCCTGTGGCAAGAGCATAC
ACAACATGACGGCCTGCGCCCAGGTCGTAGCAGGTAAGCAACCATTACTGTGATATCCTCGCAGCATTTAAGTTTGCATTGTTTATAGGAATATG
TATGATGTTGGGTCTATTTCTGCATCCGATGGGATGGCGAGCGAACCGGATTCAACGTCTATGCGGCATGGATGCCGAACCCTTTTACCCCGCCG
ACTGTAGCATAGGTAATTCTTTGAAACTTTTCTTAGAAACTTACTAAACTTAATCCTTACAGGAGTTTCATTCTACTGCGGAATCATTGGGGTAC
TCCTAACATTTACTGCCGCCGGTATAAGCCTAAAGGCAGAGTCTTCCAATATGCGAACTCGAGTTCGCAGACGCGTGGAGGCGGGCAGTAAACTG
GTCTGTATTCCGTAGCTGCCTTTGAATACAATAAGAACACTATCTGACTTGGAGCGAGCATACTTAACTTCATTCTCGAATTAAATTTATCATTA
GCATAAATAAACTTTTAACATTCTACAGTATAGATACAAGGTGTGGGTGGATATCTATACGACCCTACTTGTTGCGCTTGCCCTTAGCTTTGCCA
GGAGGCTTGCCCTCAACATTAGGCTTTGCCTTAGGTATGTAGACACCATGGTTCGTCTTCTTTAGGTGGGCAAACAGCTTGTTCTTGGAGTCAAA
GACAAGCCTACAGGTAACACAAGTGTGTTGCGACTTGGTCGGGTCGAGGTCCTCATCTCCGCTTTTGGGAGCCACTGTTGCCTCCTTTGTATTCG
GTTCCGAAACAGTTTGCTCTAATAGCTTAACCTTCCTAGTCGTCGTCTTTTTGCTTTTACTCTTTTTGCTCGCTTTTTTGCCTTTACTCCAGTCT
TCATCCTCTGACTCGCTCTTGATTGCCTTCTTTTCTATTGGCTCATCTGGTTCGTCACTGCCTTCCGCCTGCGCTTGCTTGACAGCTGACTTCCT
TGCCTTTTTGTTTTTTTTGGTTCGTTTGGCTAGCGAAGATTCTTCTTCGCTTGGAACCCCGTCGAAAGATATCTGATCCTCAGAGACTTGCAATT
CTTCCAGCGATTCCTGTACGCCCATTAAACTGTCTTCATGGGGTTCATTGTGGAAAGCGTCCTCTTCTTCCTCCATTTCCTGACACAGCCGGTCG
ACATTTTCATTATGCTTCTTGCTTTCTTCGTGATTAGCACGCGCCTTGGCGTTTTTAAATGTCTTGTTGCATGCCACGCAGTAAAGATCGTCTAC ATACTCCACTTCGTACTCCTCGGCTTCCTGGCCGCCTTCATGGTCAAAGTCCTCGCCATCGTCGTCGTTCTCGTCTTCATCCGTGTAATCTTCTG
ACTTGCTATCGTACTGCTGCTCTAACTGCTTTAGCTGCTCCTCGTAGCCCTCGTTAAAGACATTATTTTTCCTGACGGCTGCCAGTTCTTCCTGG
CGCTTCCTTAACTGCTCTTTGCGCTTCTCCTCCTGCTTAAGTCGATTGGCCTCGACGCGTTCCTCAAGCATGCGCCTGTAGGCCTGCACTCTGGG
ATCCCTTTTTCGCACAAAGTTGACTAAGTTGCGAACCTAAGTAAATGAGGTAAGTAAAATGTGTCTCGGAAGAAAAAAAAGGGAATTCATCGCCC
ACCTCTTCGTTGCGTTCCTTGCGGGCAGCCTGAACGATCTTTTTCATCTCCTTCTCCACCTTGCGTAGGATAAAGCGCTCTTTTATTTCGCGAAC
ATCGTAGGGACACAGCCAGTCGTAGGTCTTCCGGGTACTGTATGCCTGCCAAAAGGCGTAGAACGGACCCACCACATCTTCGTAACTACTGTTTG
AATGACCAAAGTCAGGCGCCATCCCCAACCGGTCGTCCTTGTCCATGAACTCTAAGTCCTCCGAGGCGATTTGGACGAAGACATCGGTGTACACG
CGGTAAAAGCCGTGCTCATTGTCGCCATAGCCCTTGTAACAGGAGCTCGTGAAGAACTGGAACACGTCCAGGCAGTTCTCCGCATAATCGGAGTT
CTTGCCGCGCAAGATCTGCTCGCGATGGTTGTCGTACCAAGACCGTTCCTGAGGATCAGACAGAACTTCATACGCTTGCTGGATCAGCTGGAAGC
GCTCTTTGGCCTCCGCCAGTCGGTCGGGATTCTTGTCCGGGTGCCAGCGCAGGGCCATCTTACGGTACGCACTCTTGATGTCCCCATCGTTGGCG
TTTCTTTGGAGCTCGAGCTCCTCGTAATAGCAACGCATGTTTCTTAGAACAACAAATAATTTTGATAGAGTTGCCAGATGGGCGGAAAGACAGCT
GGCGCTCACAGATGCGTTGTCAGTGCTGCAAAGCGCTGGAAGGGGAACGTAAATATCTTGCAAAGTAGCTTACTTTTGGGCTGAGAGCGTTTTGC
GTTTATTGTAATAGCTGAAAAAAACGTTAGGAAAACAATAGAAGCCTATTCTTACAAGGTCTTGAAATTACAGTTACCCAGTTAAGTGGCTAAAC
TGCAAGTGGCATCTCCTAGCAGTCATACGTAACTGCGCATCCCGTCATTAGCTTTTTTACTTTCGACGGCGACGGACGTTTCTTTTCATCCGTGT
CCGCGCATCCTTAGTTGACTAAATTCTGCCGCATGCTTTTCTCACTACCACCGAAGCTCACACATCGCATACCTATACACAGGCAGAGAAAAAAA
ATAAAATCGGAAAGGTTCCTGTGAAAAGCAGCAGTTAAACACATCAGAAGTTGTAGTTTTTCCCAGGACGTAACGGTGCTTTTTTCCCTTAGTTT
CCGAAGCATTTATACATAATTTGCATAAACTAAATAATAATCGACTGGAATCGAAGCTCGACTATTGCCAATCACCCATAACGATACAAGCAAAG
TGCCAAAATGTCGTTTAGCATTTGAGTCTGCATACGAAAAGGAAAATAGCTTGACATAAAATTTACAGTTACGTGGGATTTACAACCGTGGGCTG
TAACACACAGACAGGCCTTCACATACACACACATACTTACGTCGAGTGAGTGCGGGAGTGGAGTCCTTGAAGCATCTCTGCTTACGAACAACCCC
CACAACATTGGGTGCGTCGGTACTCGGCGCGAAGTAATGAATAACGGCCAAAAATAACCGTCAACAAAAAACAAACAAACACAAGTATAGAAAGC
CGACGAAGTCCGTGTGTGTTCTGGTGTAGATTTACCATTGCCCTTTCATCTCTTGTGCGGGTGTGTGTGTGGGCGCCAAAATAAAAGAAGGC
(SEQ ID NO: 268)

Exon: 2797..2188
Exon: 2126..1001
Start ATG: 2793 (Reverse strand: CAT)

Transcript No. : CT9445
AAACATGCGTTGCTATTACGAGGAGCTCGAGCTCCAAAGAAACGCCAACGATGGGGACATCAAGAGTGCGTACCGTAAGATGGCCCTGCGCTGGC
ACCCGGACAAGAATCCCGACCGACTGGCGGAGGCCAAAGAGCGCTTCCAGCTGATCCAGCAAGCGTATGAAGTTCTGTCTGATCCTCAGGAACGG
TCTTGGTACGACAACCATCGCGAGCAGATCTTGCGCGGCAAGAACTCCGATTATGCGGAGAACTGCCTGGACGTGTTCCAGTTCTTCACGAGCTC
CTGTTACAAGGGCTATGGCGACAATGAGCACGGCTTTTACCGCGTGTACACCGATGTCTTCGTCCAAATCGCCTCGGAGGACTTAGAGTTCATGG
ACAAGGACGACCGGTTGGGGATGGCGCCTGACTTTGGTCATTCAAACAGTAGTTACGAAGATGTGGTGGGTCCGTTCTACGCCTTTTGGCAGGCA
TACAGTACCCGGAAGACCTACGACTGGCTGTGTCCCTACGATGTTCGCGAAATAAAAGAGCGCTTTATCCTACGCAAGGTGGAGAAGGAGATGAA
AAAGATCGTTCAGGCTGCCCGCAAGGAACGCAACGAAGAGGTTCGCAACTTAGTCAACTTTGTGCGAAAAAGGGATCCCAGAGTGCAGGCCTACA
GGCGCATGCTTGAGGAACGCGTCGAGGCCAATCGACTTAAGCAGGAGGAGAAGCGCAAAGAGCAGTTAAGGAAGCGCCAGGAAGAACTGGCAGCC
GTCAGGAAAAATAATGTCTTTAACGAGGGCTACGAGGAGCAGCTAAAGCAGTTAGAGCAGCAGTACGATAGCAAGTCAGAAGATTACACGGATGA
AGACGAGAACGACGACGATGGCGAGGACTTTGACCATGAAGGCGGCCAGGAAGCCGAGGAGTACGAAGTGGAGTATGTAGACGATCTTTACTGCG
TGGCATGCAACAAGACATTTAAAAACGCCAAGGCGCGTGCTAATCACGAAGAAAGCAAGAAGCATAATGAAAATGTCGACCGGCTGTGTCAGGAA
ATGGAGGAAGAAGAGGACGCTTTCCACAATGAACCCCATGAAGACAGTTTAATGGGCGTACAGGAATCGCTGGAAGAATTGCAAGTCTCTGAGGA
TCAGATATCTTTCGACGGGGTTCCAAGCGAAGAAGAATCTTCGCTAGCCAAACGAACCAAAAAAAACAAAAAGGCAAGGAAGTCAGCTGTCAAGC
AAGCGCAGGCGGAAGGCAGTGACGAACCAGATGAGCCAATAGAAAAGAAGGCAATCAAGAGCGAGTCAGAGGATGAAGACTGGAGTAAAGGCAAA
AAAGCGAGCAAAAAGAGTAAAAGCAAAAAGACGACGACTAGGAAGGTTAAGCTATTAGAGCAAACTGTTTCGGAACCGAATACAAAGGAGGCAAC
AGTGGCTCCCAAAAGCGGAGATGAGGACCTCGACCCGACCAAGTCGCAACACACTTGTGTTACCTGTAGGCTTGTCTTTGACTCCAAGAACAAGC
TGTTTGCCCACCTAAAGAAGACGAACCATGGTGTCTACATACCTAAGGCAAAGCCTAATGTTGAGGGCAAGCCTCCTGGCAAAGCTAAGGGCAAG
CGCAACAAGTAGGGTCGTATAGATATCCACCCACACCTTGTATCTATACTGTAGAATGTTAAAAGTTTATTTATGCTAATGATAAATTTAATTCG
AGAATGAAGTTAAGTATGCTCGCTCC
(SEQ ID NO: 269)

Start ATG: 5 (Reverse strand: CAT)

MRCYYEELELQRNANDGDIKSAYRKMALRWHPDKNPDRLAEAKERFQLIQQAYEVLSDPQERSWYDNHREQILRGKNSDYAENCLDVFQFFTSSC
YKGYGDNEHGFYRVYTDVFVQIASEDLEFMDKDDRLGMAPDFGHSNSSYEDVVGPFYAFWQAYSTRKTYDWLCPYDVREIKERFILRKVEKEMKK
IVQAARKERNEEVRNLVNFVRKRDPRVQAYRRMLEERVEANRLKQEEKRKEQLRKRQEELAAVRKNNVFNEGYEEQLKQLEQQYDSKSEDYTDED
ENDDDGEDFDHEGGQEAEEYEVEYVDDLYCVACNKTFKNAKARANHEESKKHNENVDRLCQEMEEEEDAFHNEPHEDSLMGVQESLEELQVSEDQ
ISFDGVPSEEESSLAKRTKKNKKARKSAVKQAQAEGSDEPDEPIEKKAIKSESEDEDWSKGKKASKKSKSKKTTTRKVKLLEQTVSEPNTKEATV
APKSGDEDLDPTKSQHTCVTCRLVFDSKNKLFAHLKKTNHGVYIPKAKPNVEGKPPGKAKGKRNK*
(SEQ ID NO: 270)

Classification: chaperone
Gene Symbol: BcDNA:GH03108
FlyBase ID: FBgn0027599

Celera Sequence No. : 142000013384832
GTAAGAAAGATCATCTCTGGCTGAAACAGTGCGTACTGACTTTTCATTGTACGGCCTCTCCGGCGTGTTGTGGTACGAGATCAGCAGCTCCTTGG
CCAGCATCTTGTCTGGGAAGTTGCGAATCAGGTACAGCCAGCACTGAATGGTTCTAGACATAGGGGCAATAGTGAGTTATTACATCTGGCCATCA
CCCCACACCCTCATACTCATTCTGTTCCATTAATATGGTTTGTTGCTCGCGATCATAGTAGTCCGGGTAGTCTTCTAGTATGTCCAGTTTGGAGA
GCATGGTCTCGTCCACTTCGTAGACTTCGCCTTCTATGTGGTTCCCCTCACCCGGGCGGGCGAGCAGAAATGGGATGTTGTAGCGGGTTCCGACA
ACCAGGGGAAACTTCGTTTCCGTTTTCCCCCTTCCAAGGAATCGGGCTTGGCCGTTCTCCTTTTTCGTCAGCCAGTGGTGATTGGGCTCACCGCG
CTTCAACGTGCCATACACAAAGACCCTTGCCGCCATTCTCAGCTTTTCAGCCATTGCGCTTCCCGCCGCCAGGCTTATCAGTTTCAAGCGGTATC GTGCTATCAAATCCGACCTGTAGATTGCGCAGTCGACATAACCCGTCCGCTCTTCTTCTTGCTGCCATTCGCACCGAATCTAGCCTCCGTACACC
GCGAGAAACTGAAGCCCTCGGCACTGGGCTGTGGAAAATTACCAGGGACTGCTGTCCAGCATCTTTACTTCTATAATAGAACGAGGGGCATTTTA
TTTTATTTTAAATTGCTTCAGTTTATTTGCTTTGTTTGTCGAAAACTATCAAATTACAGACTACGTTTGCTAAAACCTAAATAATGCGTATGGTA
CATATGTATCAGTTTATATCGTTTGCCCATATATACGGGTATATATCGATCAGTACATCTGCGTCTGCAAGTACGGTCTTAAAATGCAACTACGG
TAACATAAGATTAGTGGCCAGGCTATCCAGAGAACATCCAAACAAACGGGCGACACCACAACCCACGTTATTAGTTCTGGGCCTCGTAGGTGAGG
TCGTCCTGGGCCGGATGCTTGTGGGTGCGGCGATGGCGCATAATGTATGGATGGGTGGTTGAGTTCTCGTAGCTGGACAAGTAGCGCAGACTAAG
TAGGTTCTCCGGGTACTTCTGCAGCAGGTACACCCAGCATGGAACGGTTCTGGAAAGGAAATTGTGACCCATCACACCACATTGCTGAAATGACG
TCAGATCCGACTAATGCTCACCCTTCTCCAACGCCAATGTTCATATCGTGCATCTCGCGAGTGTAGATCTCCTCGCAATCCTCCAGGTTGTCCAG
GGAATTCAGCATTCGATCGTCCACCTCGTAGATCTCCCCTGTTACGTAATATCCCACTCCGGGCTTGTTCAGCAGGAAGGGAATGTTGTAGCGGG
TGGCGATCACTAGCGGCAGCTTTTGGGTGGTGGTCGCCTTGCACCAGAACTTAGCGAAGCCGTTGCCAGAGCTGGCCAGGATTGAGTTGCTGGGC
TGTCCGTACTTGAGGGCGCCGTACACGAAGAGCTTGCTCAAGGCGGAGGAGACTTTCTGTGGAGTGCGTGAGAGGTGGGTGTGGCGTAAAGACAG
ATAAGTAGGGTTAGGTTAGAGATCTGATAAACTGGTGGTATCTTGTGAGAGTTTGCTCTACTGGTATCAATCGATCGCCGTGGCTTATCAGGGAT
CAGGGATCCGAACACTTTCCACTGGCTAGCCCCCGCAAGTTATTGATAAGGTTCACGAAACGTCTCGGTGTTTGGCGAGATTCTCAGCTGAACCG
CTTTTTGGGCGAGAATGGGATGGCTCAACCGGTTTCGTGCATTCACACGTTTATTCTTAAAGTCTGTTATTGTTGCTAATATATGTACGTAGCTG
TTTCGTATTTTTGGGGCTGAGTGCGTGCCTCACAAACTGCGCAGCAGTTACGCCTCCACAGGTACATATGTATGGAGACACTCGCTATCTGTACA
CATGTAATTGGCACATTAATAATTGCTTAAATCGGTTTAATCATTGCAGTAAATGGATAACACACGCAAGCGGCCTTAAATCAATGTCATCAAAC
GGTTGCATCAAAGCATCTTGGCGAATCCGCTTACATAACCCAGAACAGGCATCAGCTCACACTCATACATATGTAGATATCTTAAAAATTCCAAT
AAACTATCTGATAACCCTCCGATGGATCGGATAACTTAAAATGCCTTAAATTTAGTTCCCAAGCTCTCAGGCTTTTACACGCTTTCCATTTGGGG
CTGCCCACTTGCCAAGGACGAAGGATAAGGGATGCGTATACACAAGCTAAAAGTGTGCATGTGTGCGTGGGCTTCACATTGTGCTGCACTCTTAA
TCAGCTTACCTTTGCTTGGCCCATTTTCTTGTCGAACCGCCTGCAGATAATTAAAATTGCAAATTGCTGCACTAAGCAAAGGCGAGAGAGCTCTT
CGGGATTGGATAGGATAGTGTGCACGAGCTCCAGCAGAGATACAACCGCGCCGATGGCCAGCAAAACTCCAACTAAATCGTGATGGAGAACAACG
TCGGCGGACACGGTGCTGCCGCCTGCCACTGTTGTTGTTGTTATTGCTTCTGGCACAGTGGAGCAAAGTCACAACGTGTTATTGGTTCAACTTAT
ATAAATATATTGCATATGAAAGTATTAGTCGACACTACGTGGAAAAGCAATTCTTAAATAATAATTATGGTATATATCCAATTTCATCAAAATTG
GAAAAAGGAAGAAAATATTATTTGCCCTGTTTACTGACTCTGCCCAGTGTGCCTTGTCGTCAAGACCAAGAGGCCCGCCTCTAGTGGAACAACAA
CAAGTAAAACAATAACACGCCACACGCGCAAAGCTAAAAATGACGGTTCTGCCGACTGGTCTTTATCTAAGAAATATCCTCTGGGGGGGGGTGTG
GGTAGTTGAAATACCCGAAATATTATAGGCCCCGCAAGCACAAACACTCTAAAATTCGGGCATTATCAATGGCCTAATAACATCTGAGCACAGA
AGTCCCTCTTGAGATCCACGCTCCCTCTATGATACCCCCCCCTAGCAGCATTTTAGTTCGCTGGCGACGCCTCTGGAGAACACGTACGCATGTCT
TCTTCAGTTTCTCTGCTGATCGGTGGGGATCGGAAATCGTATACTGTATATTGTAATATTCTGCACTTCCATGTGTCCGATTTGTTATAAACAAT
AACAAAGTCTCTTTGTAATTGATTGGTTGATAGGTGGGGGAGGGGGTGCGGCAACAACAACACCAAAACCAAACCAGTTGACATGCGCTCTTTAA
AATCAAAATCTCACTGCGCTCTCTGAATTGTGCCCTGCGAAAGGTAAGGCATTTTAGTTTTCGGACTCAATACGAACTATCAAGCGTAACTACAT
ATTGTATATTGTTGCCCATTCATTATGAAAGGGTAAGCACTCAATAAAGTTAGTGCTTCTCATATTTCCTCAGGTTAGATAAATCGATATAATAC
ATATGCATAATGCGTTTTTGAAGTTGGTATTTTAATATGGACAAATTATAGGTTACTTTATGAGGCGATTAAAGCTGTTTTTATATTTTATGTTA
TTCC
(SEQ ID NO: 271)

Exon: 2614..2385
Exon: 1576..1257
Exon: 1189..1001
Start ATG: 2399 (Reverse strand: CAT)

Transcript No. : CT9529
AAGCAATAACAACAACAACAGTGGCAGGCGGCAGCACCGTGTCCGCCGACGTTGTTCTCCATCACGATTTAGTTGGAGTTTTGCTGGCCATCGGC
GCGGTTGTATCTCTGCTGGAGCTCGTGCACACTATCCTATCCAATCCCGAAGAGCTCTCTCGCCTTTGCTTAGTGCAGCAATTTGCAATTTTAAT
TATCTGCAGGCGGTTCGACAAGAAAATGGGCCAAGCAAAGAAAGTCTCCTCCGCCTTGAGCAAGCTCTTCGTGTACGGCGCCCTCAAGTACGGAC
AGCCCAGCAACTCAATCCTGGCCAGCTCTGGCAACGGCTTCGCTAAGTTCTGGTGCAAGGCGACCACCACCCAAAAGCTGCCGCTAGTGATCGCC
ACCCGCTACAACATTCCCTTCCTGCTGAACAAGCCCGGAGTGGGATATTACGTAACAGGGGAGATCTACGAGGTGGACGATCGAATGCTGAATTC
CCTGGACAACCTGGAGGATTGCGAGGAGATCTACACTCGCGAGATGCACGATATGAACATTGGCGTTGGAGAAGGAACCGTTCCATGCTGGGTGT
ACCTGCTGCAGAAGTACCCGGAGAACCTACTTAGTCTGCGCTACTTGTCCAGCTACGAGAACTCAACCACCCATCCATACATTATGCGCCATCGC
CGCACCCACAAGCATCCGGCCCAGGACGACCTCACCTACGAGGCCCAGAACTAATAACGTGGGTTGTGGTGTCG
(SEQ ID NO: 272)

Start ATG: 216 (Reverse strand: CAT)

MGQAKKVSSALSKLFVYGALKYGQPSNSILASSGNGFAKFWCKATTTQKLPLVIATRYNIPFLLNKPGVGYYVTGEIYEVDDRMLNSLDNLEDCE
EIYTREMHDMNIGVGEGTVPCWVYLLQKYPENLLSLRYLSSYENSTTHPYIMRHRRTHKHPAQDDLTYEAQN*
(SEQ ID NO: 273)

Name: Calcium binding related protein
Classification: ligand_binding_or_carrier

Celera Sequence No. : 142000013384694
GCACGACACGCCGGAGCGAATGCTAGAGAAGGAGTGTATCAGTGAGATTGTGCCTTGGCGCGATTCCCGCCGCTGGCTGTACTGGCGTCTGCGAC
GTCTCCTGTTGGAGGACGCATATATTAAGAAGATCCTGCGCGCTCAGGACAACCTCTCCGTGGGTCAGGCCAAGCAGATGCTGCGTCGATGGCTG
GTAGAGGAGAAGGGTGCCACAGAGGTGAGACATTTTGAGCTTCCACTCCAGGAGACCACTAAATTATTCTCTTATGTATAATTAGGCTTATCTGT
GGGACAAAAACGAGGAGATGGTGTCTTGGTATGAGGAGCAGATCAATGCCGAATCTATTGTTTCCCGCAACGTGAACTCCGTGAGACGGGATGCC
ATTATTTCTACCATTTCGAAAATGCTCGAGGTAAGAGCAGCCCAAATCTTAATACCTATAAATTGGGAACTAACTCCTCTATTTATATATCTTTT
CAGGACTGTCCCGACGTAGCGCTGGACGCTGTTGTGGGTCTTTGCCAAGGTCTGACGCCAGTGAATCGAGGCGTGGTCGTACGCACATTAGCCCA
GATGCAGCTGAATGAGGAGACCTCTAACAGCAACCAGGGATGATTCTACGCTATGTTCTAAGTTCTTTTTAGGCCCTCTATTTCATCCTTCCCGT
TCCCGCCCTTCACCACATTTCTCAGTCCCGCTTTGCGCTTGTAAGATATCGCAAGGCGTGCATGATGTGCATTTTGTTTAGTTAAATTTGTTTAA
AAGTAATTAGCGTAAATCTAGTTATGTATTGGAGTTGTAGGCATGGGTTAATTTGTTGCCTAAGTGGCCCGATAAACTAGTTGTATCGTGTACAT ATTTGATTATGTATATCCCCTGAATACAAATCATTCCATTAGTTGTATAAGAACTAAAGTCCTTTGTACACAGAGCCTTTTGAATAATACGAGTT
ACTGAAAAAATAAATGTATGGTACACTACATTAACAAAACTCGCTGGATTGCAAAAGGGGTTTTTCGTCTTGTTCTGTTTTTCTTTTCTTTTGGT
TCCACAGGATCGATAATGTACATAATTTCATTTATTTTTATAATTTTAAAATGAAATCTATCGCAGTCGGGGGTTATATCCTCCGATTCACTGCG
TTCCTATATGCCGTTTTTTAATTAAGATGAGTGGGGGGAGATGGGATGGCGAGAGCCTGCTTCAGTTCAGGTTATCCATCCAATCGGGCTCGGCG
ACACTTATCTTCTCTATAATGGAATTAACCTGATAGCATAGCGACTGGATCTGCCTATCCCACTGAGGCAGTAGTTCCCGATTCTCGAAGTGCAC
AATGGCCGAGATCTGGTCGATGTGTCCGTTCATGCGACCTTCGGTAATCATCTGAGAGGCAATCTTCTCTGCTTTCACCGCGGGTATGTCCAGCA
GAGCGCCTAGCTCCTCAAAAGTTATGTTGTTGTACAGCTTACTAGCCGACAACAGATTGTGCTCGAAAACAGCCCGATCCAAGATCGAGGATCCA
TCGGAGGTGGCAGCCTTTTGGTGGTCCTGCAGCAGGGCCTCGAACTCCTGTAGCTCGGAGCGCCGAATGATGCGCTCCAAGTACATCTTTTCCAA
AATTCCATAGGCCGGCAAGTGCTGACAGCGTTCATCCTTGAACAGAGTGGCCAGCATGCGGGAACGCTGCTGTCCGGCAGAGGCGAGGACTGTGC
AGATGAGCGCTTTCTTCAGTGCCGTCATCCTCTCGCCTTGGTCCACGATCTTGCGGTAGGAGAGCTCGTTATATCGCTGGGCGGCCTCGATAAAC
TTGCGCCTGTAATCCAGGACACGAGCATAACAGACTTTATATAGAACCTAAAAGGTGCGATTTTTAACAGATTACCCATCTAAAATAGCGCTAGG
AAGCCATTTACCTGCAACTCCTCGGAATTAGTTTCGGCCTGCAGCAATGATGCCCGGTTGATGAACAGCTCCGCCTGCACCGAATCGTTGTCCTC
CAGATAGAGTCGAGCGATCTTTAAGTAGGTGCCCAACTTGCACTCCACGGAGTACTGTTTCTGACCCGTCTCCAGAGGAATGCCAACTAGCACTG
TGGCCGCATCGCGCCACTGCTGGTTGCGCTCATAGATGTTGGCCAGGTGGAAACGTATGCCAGCCACTTGCTCTTCGAACGAGATGACGCGCGGA
TTGACCTTTTCCAGGGTGAAGTGAGAAAGCATCTTGGACAGATCGTCAGGCAACTTGCTCAGCTCGCTGCCCACGTCGTTAAGGATCTGCCGCGA
GATCACCAGGCTGACGTGCTCGTTTACAATGGCCTCCACAAAGAGCCGGAGCCCATCGATCAGCTCTTGGCCGGTGTTCGTCAGCACAGTCTTCA
GCAGCTGGCGGTACTTGTCCGCCTGGTCCTTGTGCGTGCCAGTGAAGTTGATCAGGCCCATCAGCTGGCTACGCAGAGCTGCCGTCGAGATGCCG
TAGTTTGCGGCCATATTCACTTCTATACCCAATTACTTCGCACTAGCTAAAAACAACAACGCAAGCTCATCCCTGTTATCGATAGCTCGCAAATC
CGGCCGGGACAGTGCAGGACGCCTAGCTTTTATCTAGCTGGTGTTGGAAAATGTTCGATGGTGATACTCAGCTTACAAATTTAGTTCGCAATTTA
TATTTTATTTATTATTACCTATCTATCTATGACTTCTTTCCATAGATAGGTTTTGAGTAAAGACCAAACCACATGAAAATGTTGACATAAAAAAA
TGTATATCTGAGGATAAAATTTAAATATTACATAACATAATATAACATATTTAAAATACTATCTGCAAAGCGCAAGACTCTTACCAAGGCTTACA
TTTGTTCTACTCGTATTATCTTCCAATAAAATATTTATGGAATAAAATATGCCAATAAAATATTGGCAGTATTTCCTTTCAGCATTCGATTTTTA
AAGGAAGGCCTATAATGATTCGGTAAGGTTTAAAATTCACTTAATGCTTACACTTGTACATACTTTCCCAATAAATTATTTAAAATTGGCGCTTC
AATCCAAGCTGCAGTCTATCGGTGACTGCATTCTTGAAATATCGATACAAAAATGACAGTCGGTGCGCTGCAGTAAACAGTGAAAAAATATACTT
GTGTCGAGTCCAATTGGACTGCGAAAACTGCATTAAACAAAGAGGTCAAAGACAATCTGCAAGTGGTAGTAGCTAGAGAATTACTAGAAACTCGA
GATATTCAGTGCAAAGACCAATCCATTCGGATCCTTGTGGAAAAGGGTGGAGGCCAGGCCCACACATACATACACTTTCAGCAGCAGCGCAGCTC
GCCGAGTGAAGTGGAAAATGTATCCAAAGGAGTCCAATGGCCGTTTTGCGAGCAGATATGAACGGAAATTGCCAATTGACGACACCCAGGCGCT
GAGCTGCGAGATAACCGCCGTCCAGGAGGTCGCCGGACATACGGTAGCTAGATCGCGAGGGGGCAGAGCTGCTGACCCCAGCGAAAAATCAATAA
TTGTTGATGAT
(SEQ ID NO: 274)

Exon: 2526..1912
Exon: 1852..1001
Start ATG: 2484 (Reverse strand: CAT)

Transcript No. : CT9624
TTGTTTTTAGCTAGTGCGAAGTAATTGGGTATAGAAGTGAATATGGCCGCAAACTACGGCATCTCGACGGCAGCTCTGCGTAGCCAGCTGATGGG
CCTGATCAACTTCACTGGCACGCACAAGGACCAGGCGGACAAGTACCGCCAGCTGCTGAAGACTGTGCTGACGAACACCGGCCAAGAGCTGATCG
ATGGGCTCCGGCTCTTTGTGGAGGCCATTGTAAACGAGCACGTCAGCCTGGTGATCTCGCGGCAGATCCTTAACGACGTGGGCAGCGAGCTGAGC
AAGTTGCCTGACGATCTGTCCAAGATGCTTTCTCACTTCACCCTGGAAAAGGTCAATCCGCGCGTCATCTCGTTCGAAGAGCAAGTGGCTGGCAT
ACGTTTCCACCTGGCCAACATCTATGAGCGCAACCAGCAGTGGCGCGATGCGGCCACAGTGCTAGTTGGCATTCCTCTGGAGACGGGTCAGAAAC
AGTACTCCGTGGAGTGCAAGTTGGGCACCTACTTAAAGATCGCTCGACTCTATCTGGAGGACAACGATTCGGTGCAGGCGGAGCTGTTCATCAAC
CGGGCATCATTGCTGCAGGCCGAAACTAATTCCGAGGAGTTGCAGGTTCTATATAAAGTCTGTTATGCTCGTGTCCTGGATTACAGGCGCAAGTT
TATCGAGGCCGCCCAGCGATATAACGAGCTCTCCTACCGCAAGATCGTGGACCAAGGCGAGAGGATGACGGCACTGAAGAAAGCGCTCATCTGCA
CAGTCCTCGCCTCTGCCGGACAGCAGCGTTCCCGCATGCTGGCCACTCTGTTCAAGGATGAACGCTGTCAGCACTTGCCGGCCTATGGAATTTTG
GAAAAGATGTACTTGGAGCGCATCATTCGGCGCTCCGAGCTACAGGAGTTCGAGGCCCTGCTGCAGGACCACCAAAAGGCTGCCACCTCCGATGG
ATCCTCGATCTTGGATCGGGCTGTTTTCGAGCACAATCTGTTGTCGGCTAGTAAGCTGTACAACAACATAACTTTTGAGGAGCTAGGCGCTCTGC
TGGACATACCCGCGGTGAAAGCAGAGAAGATTGCCTCTCAGATGATTACCGAAGGTCGCATGAACGGACACATCGACCAGATCTCGGCCATTGTG
CACTTCGAGAATCGGGAACTACTGCCTCAGTGGGATAGGCAGATCCAGTCGCTATGCTATCAGGTTAATTCCATTATAGAGAAGATAAGTGTCGC
CGAGCCCGATTGGATGGATAACCTGAACTGAAGCAGGCTCTCGCCATCCCATCTCCCCCCACTCATCTTAATTAAAAAACGGCATATAGGAACGC
AGTGAATCGGAGGATATAACCCCCGACTGCGATAGATTTCATTTTAAAATTATAAAAATAAATGAAATTATGTACATTATCGATCCTGTGGAACC
AAAAGAAAAGAAAAACAGAACAAGACGAAAAACCCCTTTTGC
(SEQ ID NO: 275)

Start ATG: 43 (Reverse strand: CAT)

MAANYGISTAALRSQLMGLINFTGTHKDQADKYRQLLKTVLTNTGQELIDGLRLFVEAIVNEHVSLVISRQILNDVGSELSKLPDDLSKMLSHFT
LEKVNPRVISFEEQVAGIRFHLANIYERNQQWRDAATVLVGIPLETGQKQYSVECKLGTYLKIARLYLEDNDSVQAELFINRASLLQAETNSEEL
QVLYKVCYARVLDYRRKFIEAAQRYNELSYRKIVDQGERMTALKKALICTVLASAGQQRSRMLATLFKDERCQHLPAYGILEKMYLERIIRRSEL
QEFEALLQDHQKAATSDGSSILDRAVFEHNLLSASKLYNNITFEELGALLDIPAVKAEKIASQMITEGRMNGHIDQISAIVHFENRELLPQWDRQ
IQSLCYQVNSIIEKISVAEPDWMDNLN*
(SEQ ID NO: 276)

Name: COP9 complex subunit 4
Classification: endopeptidase
Gene Symbol: CH4
FlyBase ID: FBgn0027054

Celera Sequence No. : 142000013384822

FIGURE SHEET 149

TTCCCAATTCCTTCGAGGTGATGGCACCTTCGTTATCCTTATCCAATAAGCTATAGATATTCTTGAGCAGGTCCTGCTCTTCAACAGACAATTCA
TCCATTATGCTTTATATTATGGGAAGGAGAATATTATTATTATGCTAGTAGATATACTTTTTCGATAGGATTGATACTCAGTTGAGGTCTGATAA
GCTTTGAAGGAGTTCTACGATTGAAAATTGTTATTCAAAACATTCAATATAAATATTTTTGAAAAAAGCCAACTAAGAGTTAGCCTTCGGTCTTT
AACAGATATTAAACAATCTGCGTGCTCCATGAAGTTCATAAACTTTTACTGAAGATAAAGGCATTAAAAGAGCATTCTCACGCACAGTTTGGCAA
ACAAATCACGTGCTTTCCTGGACCCAAATGATATCATCTGGCGGAGAAACTCTTTGGCTTTACGCGTATTATTTTATAGTTGAACCAGAAATTGA
TGTCATCGGTGGCGGTAAAAAATGGGCGCCCAATCCGCCCAATGAGGAAATTCCAGGAAGCCGGGCAACTCCAACTGTCGGTGATGACAATTTGC
GTGGCATTTTAATTGAACTTTCTACGTGTTCGAGTGGTGTACTTTGATTTGATCCCCATCCACCGATTTTTCGTCGATTTGAGTCAATGTTAAAG
GCGTTGCCACAAACCGCAAACTGTCGTGTCTAGGAGGTTGGGGAGGGGCTTGGTGGCTGGGGCCTCGAAACGTGCCTGAAGTATTATTACCGCCG
TCTGTGATTGATGGCCTCATGCGAGTGAGTCAGTGGATTTTTATAACTCTACGCAGATCCCTTCCTTTCAATCAAGCGGCAAAAAATCTGGACAT
CGATCTCGCCGATATTAGCTAACTTCATTTCAACTTAACTGCCCGGAGTGCTTTGAATAAAGTGGATTTGAGGCGATGCCTTGGGATTCTTGGCC
AGATTAAGTCGATTTTTTTTTTTTACTTCAATGAAAAAAATGGCACGCAATTGTTTTTCATTATTAATGCATACTTTATTTGAAATCAACTAACT
CGCTATGGTTTGAATAAAATCATTTAAAATTGAAGGAAGACCATGGAATTCTATGGGTTGCTTATATTAACTACTGCAAAACTCTTAAAATTTAA
GCCTAATTACATAAGGTTCTACTGGAATGTTGCTTGTAGTTGGATTTTTGTTTATGCTCTGCTTTACACTAACTTTTACTTTCAACCATTTTTTT
CCCTACAGCAAAATCGATTAACGATTTTGTTTACTCATTAAGATTAGCTTACCGGATAAGGAAACATAAATAAAAAATTGGAATTCACTCAGCAA
ACAGCAACACTTAGTGTTGGGCCACACATTAAAAACTAATCGATAGACTCTCGTACTAAAGGCTTAAACATTTAAATCGGTAGATTTAAGCTAAA
ATCCTAACGCATAAGAGCTCTATAAAATGCAACAACGGAGTTTGTTTCGCTTACAATTATCGCTTAACTGATTTTATTACTTAGTTTAGGTCTAT
TGCCTTGCCTAGACATTGTACTAAAAAGTATTAAATTGTAGATCTAAATTTATTTTAATGTACTTGTGGGTCTAAAACGATAAATCCTCGTTTAA
CCATTGGGAACAATAACTGTTTGTCATTATGATATTCAACTGTTCATAAGACCTTCTAAATGAAATACCAGAAAAAACAACCGAGATATATATTT
ATTAGGAATACTACTACTTTTTGATATTTCAAATTCGTAAGAGCTTTGATAAATAGTTTTCCAAATTGTGTTGTTTTTCTATTCCGATTTTACCT
CCATTAATGGATTGTTTTCTAGTTCTTTCTCGGTTTACTTCTAACGCCTCATTATGTCCTCAATGCTGAACCCTGTTCTTCTCGGTGGTGCAGGC
GGTGGTGCTATGGGCGGTGCTGCCACTGGTGGTCCCTTTTCGGTGGTGGCTCCACTTGTTTCCGTACTCGGTGGTTTTCCCAGAAGCTGTCTGGG
GGGATGTCGCGACATATTCAAAGCATATATGCTGGGACTATCCACAAAGGTCCTTTGACCCAATCCAGGATGGTGGTGCGGATCCATCAAGTCCA
AGGTCGGTGCCGGAAGAATCCTCTTTCGCATGGGTATCGATCCCAGGAAGCTGGGCATAGCTTCATGCGGTGAATGCAAAGGTTGATTGGGTGGT
TTACCCGACTCCGGCTGGGTTATTATAGTGGGTGGTGTATGTGGTGGCGGTGGAACACCAGCCTTCGAAAGGTTCAAGCTCTTGTGGTGCAAGTC
GCGTCGAACGTGCAGAATGGGCAAATAGGGATCCCCGTTGGGTGGGAGTAAGTGTGGATGTCCTGGGTGCTGGTGGGTTGGCGGAGGAGCTCCAG
GTGGTGCAGGCGGCGGTCCAGCTGCCCCAGGTGGTACAGAATATCGCACAAAGGAAGGTGGAACGGGTAGGCTGGCAATGCCAGAGTTCCCGGGT
TCCTCCTGATGTTTCTCGCCATGTGGCCGCATTGTGTAGGTTTCACCACCCTCATGATGACAGTGGGTGACTCCCTGGCGTTCCGGCTTGGTGCC
CACTGACGACGATGATTGCGATGTGGCGGCAGCCTTACTCGCCTGGAAACGCGCCACTAGTGCCACTTCTGCCTGCTCCTCGTCCTCGGGATCAA
AGTCGTCGTCCTCTTCCCTGGGCAAATCGTGTACTCTTGGCAGATCCTGCAGTTCCTCTTCCTCGTCGAAGTCATCGAACTCCTCTTCGCTTTCC
TCATGATCGATGGCTGCCTTGCGCTTGAGTCTCATTCTTTCGGACTCAGATTTCTCACCCGATCCTCCAGACTCGCCCAAATTGTGAACTGGCGA
CTGGCGAGGCGAGTCCACTTCCAGCAACGAATCCTCCTCGTCGCCACTTAAATTTCTGGCCTCATCCTCTTCGCCCACATCCACATAGTCCCCGG
AGTTGACCTCACCCACTGCATGGGTCAAGGCATGGCGTCGTAGATCGCAGTTACGGCGGAAAACTTTGCCGCATGAAGAGCACTCGTAGGGCTTG
TGATCCGTGTGGGTGAGCAGATGGGTCTTCAGGTTGGAGCGCTGATTGAATGATCGACTGCAGACGGGGCACTTGTGGGGTGATTCCTCCATGTG
CAGGATCTTGTGGACAGCCAAGGTTCTCGATTGGCAGAATCCCTTGCCGCATTCCGTGCATTTGAAGGGTTTCTCCTTGGAGTGAATATACCTGG
GCGAATACAAGTGGAGAAACAATTAGACTTTATTGTTATAGCGTGGGCGTTTTCCTGGTAGCTGCAATTGGTAGCCCAGGTTGACAGTTATCTCT
GCTCAAATGCAGCCTTAACTTGAACCGATAAAGCTCACTGATATACAGCTTTACAATACTCTAACTAAGGATATAACTGGCTAGAGCAGACAATA
GAATAAATAATATAATACTATAGCATATAATACCTATCTTTCTCTTTCAAAATGAAACCTAACCTGGATTTGTTTTAACCTTAAACCCAATTCTT
TAAAGTTTTTCATTAAAGAAATCCTATGATTTTGTATCCTCTTAACTGATAGGGTATTTAACTTTCGTGTATGCGATCTGGCTGCATTAATTTTT
TATGTTTATGGCGGCCATCTTGGCAATGGCGTCCACTTGCTGTTGGATAGCAGCAGCCACAGTTAAAAGTTAAAGTCCCCATCTTCGACGGAGCC
ACAGATTCAGCATCGCATCGGAGGCAGCAGCTGCTGGTGGAAAAAAAAAAAATAAATGTATAAAAACCCAAAACAGGTTCTGCCTCCGAAGCACCG
AGATTCTTCTCCCATGCTCCGTGCGTTTCTGGTAAAAAAAAAATACAAAAAACTTAAGAAGAATTAGCCCCGCGGCAAAGCAAACAAACGACAAA
TGGACCGATACCGAACGATCAAAAGACAGAACGCTCGGACAGGCCGACACATTGAAGCCGGGATGCTGGACCTGCTGCCTGGCATCGGCATGGGC
ATCGGCACCGGGATACACAGACCCGATATATAGCCCCCAACCCCTTGGCCATCCCTCAATTTTAATGCTGGTGGAGGAGCCCCAAAGGAAAACCA
ACAGAGTTAATTAACTTTGTGTTGTACTCTGCGGCCGAGTTGAAGTTTTACTGGCCGTCAGAGGAGCTCTGATTTTGGGTCCGCTTTATGGGGAC
TTACTTATTTGAGTTGAGGTAGGAAAATTCGTCGTAAAGTTTAAACATTTCCTGGAAAATTCCTTATGGTAAAAGGGGTCTTTTGAAGCGATTGT
CTGATATATCTAAAATCAATAAAACTCCATCTACGAGTAGTGGTCGCCTTTCCCTTTTGGCCGAGATTACTGTCACACCTGTTCAGAATGTGTGT
ATAAACTGCCTAGTAAGCAATAAATTACATTGATCTAATTATCCTTTGCCTTTACAGGGTATTCCATTATTCGCCATTCGTTCACACTTTGAGCA
CAAAGAATAACTCCAGGCCTGATGGCAATTACCCGAGCAGACACTGCCCCCTTTTGTGATTACTTGTACCCCAACCTCGACTCACCTGTGATCCC
TCAGGTGATCCTGTCGCCGGAACGCCTTGCCGCAGATATCACAGGAATAGGGCCGCTCGTCCGTGTGTGTCCTCTCGTGGATGAGCAGATTGTAC
GACTTGGTGAATTGTCGATTGCAGAACTTGCAGATGAACTGTTTTTTAGGCCGCGATGCCCGACCAGGAGCACGTAGCAGGCGCCTATCGAGTCC
GGCATGCATTCCAGGACCCAGGCCAGGTGGAAATAGAGCTGCGGCGGCGGCTCCTGGTGGAAATGGAAAACTTCCGGCTCCCGTGGGCGATGGAC
CCGGTCCGGTGAGATATGGCGGAGGTGGCACGCCAGCTGGTCCGTACAACACTCCAGGCGGTGGCACACCAGGACCGCGGGTCCTCCAGGACCT
CGTCCTAACATTGCCGCCGCCGCAGCCGCCTCCCTTAGGGCCAACTCCTTTCGCTTGTCCGCCATCATGGCAATGATTTCGTAATTGGAATTACT
ACCCGGGCGCACCTTTCCGGTGGGCAGAACCGGCACAAAGGCAGAGATCTCGCGATGATGCGATGGTGGTGGCGGTGGCGGCGGACCATGCAGTC
CGGCCAAATGCTGCTGATAGGCCAGCTGTGTTTCATACGCTGAGATCCGGCTGGCCGATGAGTTGCGCGAATCGCCGTTGCCATTCTGGGAGCCA
CCATCCGATCCTCCGGATCCGCCGTTCCTATCCGCCGCACCAGGAAGACCGCCACCACCCACCGCCGCCGCTGCCGCCGCCATCGAGTTCATGAA
CTGATCCATCCGGGAAGGTCGCAGCATGGGTATCGCACCGCCTCCTCCGCCGGAGATCTCGCTGGATGAGCTTTCCGTGGGCATTATATTGGAGG
GGCTCTTCACATTCCGTTGGAACTGCCGGAGATAGGGATAGAACAGAAAAAGCCGAAAATAAAATAAGGGTAGTGGTAAATAACAATTAGTACAC
GATTGTGCTGGGTTAATTGGGCTCTCGTTTTTTTTCGAGGCTTATCTTAATTGCGAACCGAGTGCAATAAACAGATATTTCCACGTTGTATTCT
TTATTGCTCCTAGGGTAGTACTGGGTATGATAAAAACTGACGCAAACTGGTTTAAAATAGATATATTACTATTAACTTAGTTTCTTCTTGGTGGG
AAGTTTCCTTGTAATTGAAATATTCATGATCTTGGTTTGGCAAGGCACAGGAATATATACAATATATACTATAGAATATTTACTCTTTTTATCTC
AACCGGTTGTAACTCACTTTTTAGATGTGAAATTCTTCAAATTTGCTTTTTGCACTTCTTATCACAAAATTAAACAGCTTTATGGGCAATTAACT
TGCAAATAGCCAAGGATTATCACATTAGCTGATCTTTCAGAATTTATCCACGTGAACGTGATTTAGTAGTCACAAAAAAAAAAATAATGAAGAAA
ATATTTTTCTCGAAAATAACCCATACGATTCTGAGAACGTTTTGGTATCACAGTACGTATATTTTCACAGGGTAACTAAGCAGTTTATCACATTA
TGGCCCTCGTCTATGGGTTTGTTGCTGTGTTTTTTCCATAGGAATTTTATTATTATTGTTGGTTTATTATTATCAGCGGCGGACTGCCGACGACG
GCGAGTGAAACTAAACTGAAAACGAGTCGCAGTTTGGCACCGCGATCGGTTGCTTCCAGTGCGCAGGTTAGATAAGATTGTGCGTCTAAAAAAAC
CTGCCTCCGAACCTCTGAGACTGAGTAAGCAGCACAGTAGTAACGATATAAACACACACACACACACAGTTATATTATATATGTGCCTGTGAT
ATATGGCATATCGGCAGATACCCCGGCACACTCAGATACAGATACAAAGATACAGATACAGAGGCAGGCAGCCAAGTTGCCGTCGGTTTTGGTAA
ATGACTCGAACCGAACTCGACCGACTGCTTACTGGATTTACGCAACAGGAGCCTCGACTTCTGAGTGCCTCGAAAGAAGAAGGGGCAGAGGCAGG
GGCAGGGGCAGGGGATCGGTCCCGGAACGTGATCATCACGATAATAACAAAATAATGCACATAATAATGATCACAATGATGGCCGGACCATAAA
GTTTGTGGCCCCATATTGCAAACGCTTCTGGCTGCCATCTTCCCAACGCCTTGCACAGCAAAAAAAATGGCACCAATTTTGTACCCAATTCTATG

FIGURE SHEET 150

GAATTCTATTTTAAGATCTATCTTTTACGATAAGATTATATTTGTTATAATATTAAAGAATTTATAGTAATATGCTTTAAAATTTGTGGCTCGCA
AAGAGTGCGCCCCAGAGAGCAAAGTTTCCTCAGTAAGTCAACCTTTTTTTTCGGTGTACTATCCTCATTTAAATGTACAACCAGTTGAAAAAAAA
AATGCTTTAAAAATAACCCAGCTGTCGGTGCAATGACAGTTTTGCTTATCATTTTGCTAGAATCGTTCTCGCTGTCTCGGTTGATTTTAATGCAA
AATGCTGCAACGTCATTAAGACCAACATTAACATTCGGCTAACAACAAGTGAAGTGATCGTCATAGTTGGTTAAAAATGAGCTTAGCCAAGTTTT
TTGGAGAGGCGCCCATTGTTGAAGTTACCGTTCTTTCCGTACGGATGACTAGTCATTGTGGTGGTCTCTTATCTATGGAAATTATTTTGGCATTG
TCTGGCTGGAGAGTGCGCTGTCAGATTAGCTCTATAAAGTAGCTGAAATCATGACTTGATCATGAGTGTATCATTGTTATGGGGGAATGACTCTA
CGGACCACGTATAGTTCAAGTGGATGAGATATAAGCAGGTCCCAATTATTAATTCAAATAGCTGTTAGATGTGGGTAGGTCTTATCGTGCTATCA
TATCAGCGAGTCTTTAGTAGACAACGGAGCACGCAGTTAAGATATTAGGCAAATAGATGATCTAATTGTAATATTTACACTAGAAATGCTTACGA
AAGCCATATCGAAGCGTTTTTGTTTCCCTAATACGACTAGCACATGCCAAACTAATCTCCACGTTTATTAGATAGTAATTGGATAATTCTTTCAG
TTCAATACCTTTTAACTCTCACCCATGCGAGTTCTCGTGCCCTCACTGATAATCTGTCGCAGTCTATCTATATTCGATTCAATAAAGAACTTATC
TGATCTAATAAGTCCCCCAACTTAGGGAACCTTTGCTGTAGATGAGCGATGGCCCCGCCATGCCTCATTCGATTACGATCCCGATAATCCCATTC
CAATTTGGGCTCACGTATTTCTGGTAGCCTCGAAAAAAAAAAAAAAACTGAAGTGTAACCCGTTTTGGGTATTTATATATATTTTTTTCGATTTCA
GTACTTTTTCTAGGGATTGTTTCCACACTTTTGCATTTACGACCGCTTTGGACCCACGTTTCACCCCATACCCTGTGCACATACAATGTACAATT
CAGCGTTCATTATCTTTTTTGAAACATCGGCACTTTTGAAAACGTCAAGCCAAATAAGAAAAACAAATAAAATTCATGTAAATAATGGACATCAT
CAGCAAAAGCGACGGCACGTAGACTGCCGTAGAAATATTGAGAGAGAGTTGTGCGCACAGATACAGATACAGATGCGGAGATACAAAGATACTCG
TACTCAAAGATCCACAGATACGTTTGCGCAAACGGTTGCCCAGTAAATGAAGCCAAAGGCTTAAAGTTTCCAATATGTGTGCGTCTGAAGGTGCA
CTGGAAAAATTATTGTGCACTCTTGTGAATTATTTAATATTAAAAAAAAGAGTATATCAAATAATTCTGAATATATAGGGAAATGAACAAAAAAT
AATTAGTACGTACTTTTTTATGTAATATTGAAATGTGCATATTTAATTAGAGAGGTAATATTAATATCTTTTCTTTCTCTGTATCGTACATATAA
TAAAAAGAGCCAGAAGACCAACTACTGCTGGGAGGAAAATAAAAGATATCGAGGAGCAATTTGGCTGCCACTTTTTTCCCTCCTCTTCTTTTTGA
GCCGTCTTGCTTCTTTTCCTTGGATTTCTGGGTCCGGGATCGGTTCGTTTGCTGGGTTTTTGTGTGTAAACAACTGAGGCCAGCAGAAACCCAGG
GCCCAGCAGAGTGAAAAGGTTTTAGTTGATAAAAAAAAAAAAACAGAAAAATATACAAACACACACAGACACACACTGAGCAAACGGATTTAGTAT
TTGTATAGAAAACGCAGAGAGCTGAGGAGGCGAGTTTGTCCCTCTGATGATGGCCTACGATGGCTGGAAATGTCCATGCGTCTTACTGCCCAGTG
ATTATGTATTGAAAGGGGTATATCAGGATTTCCCGACCAAGCCATTATATAACCTTTAATATCTTAGAAGGATCTGTGTATTTACAGAAAACAGA
ATGTTGCTCAATGACAAGAAAAAAATAATTTTGAATTAAATTATCATTTAACGTTATATGAATCAGTAAGATCAATCCCATGTTACCTACTAACC
GGAGCTCAACTATTTTAAAGGTTCTTAGCAATGGTTTTTGAAATAGGGACCGTTAGCTAGAAATACCTACCACAATTTTAAGGCCGAGGTACACC
CGCGGTCTATCAGTAAACCTTTTATTTCGGACCTTATCTTCTGGGCCGAGTGCTTACCGGGCCCCCATATGCACTTCAGTTTGCTTACAAAACAC
CGGCCAACAACAACAAACAAGCCAGAAGATGACGACGAAGAAAAGTGGAGTGGTGGGAGGAGTTCCCCGGAGGAGGAGAATGGGTATGGGTATGG
GTATGGGTATTACGGGTGAAGGAATGGAAAAAGGGTCGCCGAGATCCGCTGTGCAGTGCGGAATGCTCTTGGCCAGGCTGTGTGTTTTAATCCCT
TCGGGATACTTTTTCTTCCACCGAGTGTGCATATGTTTGTGTGAAGGTAGCTAATAATCAAGACAGCGATGGAGAGGAGGAAAAACCGACGCAGA
CTTATAATTATAGTCGAAGAGGAGAACCAAAGAGACCTGCACTTCACATGCGTTAATCTGAAAACCCTTTCGGGCCCAAGCAGCATCTGAGATTA
TAGTCAAAGCTATTAAAAATCTAGCATAATCATTGCCCTCGGTGGAAAGCAAGTTGCGTTGTTGTTTTTCTCTTTTTTTTTTTTTTTTGCTCCCG
AGGTAGGCAGGCGATCTTCCTGCGCAGCCTTGTCTATAATTTTCTTGATTAATATCCATGAGATTTACACATTTGGAGTGCTGGCCAGAACCCTG
CACCTCAACCCTCCGCCACCCCCCGCGTTCCTGTGTGTGCTGGCCATTAATTTAAAAAGCTTTGCTAATTTCGCGGGGAAATCTGGAAACGAACA
ACTGCTAATGAAGTTTTATGGGTTCGGGAATGCAGCTGCAGCAGGATTGATAATGTCGTTAGCATAAATTGAAAATGCTTTCAAGTTACGACCAA
AGATTTGTTATGATTAAAGTATGGAGCACGCGGAGTGAGCAAGAATATCCACCAATGGATTTTTATTAAATGATAAATGGCGAGCTGCAGATAAC
CAGATTCCTCTGGTTGCTGAAATAAATATTTTTTTTTGAATTGAAACCTTCTTAGGATTAACTGAAGTTCAGACAGTTAGTTCCTAAAATTGAAT
TATTTCGGCTTAACTTTGACTCTTTCTAATCCCTCTTGAAGTAATCCACTTTGAATGCTAAGCCGATCTTCGTATAAATTCTATTGTCATATTGT
GCTGCTCCTTTCATTCGAACTAAATCCATTCAAAAATTTCACCCTTGAATAGAACTCTTAAGATCTTTTGTTGGTCGGATTGCTACTTTTTCAGG
CAATCTATTGTGTTATAATTTCAATGGGTCAATTCTTATTTATTGGAAGAGTTTATGCTAATAAGTGTAGAAGCACTAAGACTATGATTTATTAA
TTCAAATGCAATTGGATTATGCTAATTGCACACAAATCTTGGTACAAATTATTTATATATTTTTTTCTTCGACAACTTTTGGAACCCAGCCCAAA
ACTAAACATGTAAACTGATAATCACCTTTCCGCTGTCTGATTTCATTGATAGCATTAAAAATTCATATTCCCTAGACAACATCTAATTTCCCCAT
CAAAATTGATGAGTTCCCGTTCCAGAACAACAATAAATGAACTGGTCTATCAGGTGAATTATACACACGTGCCAAAACGAGGCGTGTCCATATAG
CCATTTCAATTTAAAACCCGAATATGGCGATCCCTAACGAGCCATTGTTCTGCGGTTTTATGGTAAATCTAAATTCATCAAGTATTTTGTCACGA
TTTTAATTAATTTCGATTTCAATTTTCCTGCCACAAGGCAATTACCAGCAACATTTTCCCCTGCTGCTGGTGCAACCGAAAAATGATAGTTGGTG
GCCCAAGATGGAGAGGAAAACCCACCCAAAGAGGTAAAGCGTAATAAACTTTTATGGTACTCCCTTTCTTATGCTAAAACTCTTTTTGGACACAA
AACCAAATGGCCCATAAAGCAAGACAATGAATATCCAAAATAGATCTCCACTGAGGCGAAACAAAAGCCAATAACTTTATAGAACCGCAACCAAA
AAATACAAAAAAAAAATAATAATAACTCAGACTGTGAGAGCGCGGGAGGCGTTCTACAAAAAAAAAAGCTTAAAAATGAAGGAAAAAGTAAAGCAT
TTAAAAGAAATCAAGAGATGTAGATGACGATGATGATGATGGTCTGAGGTTGAGGCTGAATCCGAATCCGAATCGGTATCTGAACCCAACAGAAG
CTTGCGGCAATTGCGTTTCCTCTTTGGCCACACGTTCTGGACAATTAAAGCCCCAGCCGAGCTCCGAATCTGAATCGAGCCAAGTTAAGACAGCG
ACCACGACCGAAAACCGAAAACAGAAAACCAAAAAAACCGGATTCCAAGCCGAGAAGGAGCGAAAAAGACGGCGAGAGCGACCACTGGCCACTGG
CACTGGCTACAAGTGAACTGGTTTACAAAGAAAAGAAACAGAAATGAAAGAAACATGTGAAAAATCACGATCTATAAAGCCGATGCACTTAATAC
CCTAGGCAAAATAAGTAAATAATACTATAGATCAAACTAGAGTAGACTTGTTGAAAAAAAAACACTGGAATAAATAAGAAGCTTATAAACTATCA
GCTTATTAAACTAAGTTTGCCTAAATTTCGTAAAATATATTTTTAAAACCTAACGCGATGCTTTGAAATTCTGTAAAATTAAAGTTTTTCAGAAA
TGTAACGTTATTAACACCGATTAATATTTTTAAATAATATTTTACAAATTGTGTACACCATTTTCAAACGAAGTACCCTTACCAAGAGCACCCAT
AAGAGACCCCCAGAATTCCAAGCGAAGGTTTTTCGAGTCCGGCTCGAACCGACCAACTCGAACTGAGCGCCACAGCAACAACAATGGGGCAAGCG
GGTGGTTCAGGATGGTGGGGAAGTTTGCGGGGGGATGGGGGACGTACTCCACCGTGGACTGTGCGGCACCACACTGAGTTCAGTGGCAATGACAG
TGGCACATGCAGTTGTAGTGGAAGCCGCTTGTCGGTCGACAGTCCGCCAACCGCCAACGTTGTTGCGCTCTCTTTCCTGTTTTTTCGCCCCGTCT
CATTCTATTTGTGGAGCAGGTTTTGAGATATATCTTGGGTCTTTCTCTCTCTCTCCTTCTCTGTCTGCGTACTCGTTATATTTTTGTACTCGCTG
CCTTTTTGGCCAACGCAAAAAATACCAAAATAAAAAAATAATAAACGTAATTAGCTAGCCCTACGCCACAAACAGAAAACAAAAAAAAAAAACAAC
AAAAAATAAAACAAGTAAAAATAAGTGGTGTGGAATTTTTGTGTTCATCTGGGAAGGCAGGGCCTGTTCTCGGCGGAATCTTACCTGTGGGTTAA
ACAGAAGAAAGCCCCAGGCTCTTTGGGCTTTATCTTTGCGTCCTAAAGTATCCAAGTAGTTGTTTCAATATGATTTTGCTGGTTTTTTGTCAGTT
TGTAAGCTTTGAAATGCTTGGCATTGTTTTTGGTTTTTAAAGTAGTAATTTATATCATTTAAGTGGCACTTGAATTGTATGTTGTTTTTTCTTGT
TGTATTTGTTTGAAGACTTCTGTTAATACGATTCTGTGAATTTAAAAGTAAATAATTTTATTAAAATTTTCAAAATATTTGTCGGAAATTTTTTG
TTATATTTTCAGGTTTGATTTTAATTTTAACAAGTATTTCACCGAATCATTCTCAAGTAAATGTATTTAAAAAAACACGCACACTAAGGGACAAT
TTTGAGATTCAAATCACGGCACGATCGCCCCAGGGGGTGGGGCTGAGGGGGCGGCAGGGGGGCGGTTACGGAGCAGCAGCAGCATCAACGGCAG
TCAGCTACCACAAACCACGTAGTTTTTTTCCTTCCAAAATCCACGTACAACTCGCGCACAAACACACGATGTATTTGTATCTCACAGATATGAAA
ACCGAACGAAGAAAAACCCGAACCGAAACCTCAACCTCAACGAACTGAAAACCGAACGAGAACGAGAGATACACGGCAGCTGAAATGTGTTTTTC
TACATTTTGTTTGAAATAGGAGCTGAAGCCAGTGCAGCTACCAATTCGCTCCTCAAGTAGTCCCAAACTCTTCCCACACACAGAGTCAGTTGCAG
TTGAAAAGCGCTTTTCTCGAGGCAACTGGCGATGCAACAAGTTCACTCACACACACACACACACTAGCGCTCTGGGCCCGCTCAATAAGATACAT
CGGCGGCGAAAGATACAGATAGATATAGAGCGAGAGGCACTCACAATGCAGTTCACTTTTCCAACAGCTATTACCAGCGATCCGCGCGCAGGTGC
GTTGGCCACGATCAACTCTCGAAGACTGAGCCACGAACCCAAGAAACAGGGCCCGAATGGAAAAAGAGAGAATCGAGAGAATCGCGGGCTGAGAA

FIGURE SHEET 151

ATGCGTAGAAAGAGACAAGCGACGAGTAGCGAGCAGTGGCACTAAAACCAGCTTAGTGCACTGTGGAAAAAGTTTTAACAATTCTTAAATATCTG
AAGAGTAAGGCTCTAATTTTCTGTAAATAACAACAGTATAAATCTATCTGCTTAAATATACTAGATAAATAATGGATGCATTTACATATTTTTCT
GAATTAACTAGTAACTTATATTCAGTTTGAATATAGTACGACATTTCTTTCAGTGGAGGAGAGGAATTAAACCGAACTCAACCCAAACCCAACCG
GCCGCCAGTCGCACGCTGCTAAATGGACGGATGGGCCCGTGGACGGACTTATATGGAGACTGGCACTGGCGGAGCGTGGAACGTGCATTCGTACG
ACGAGTTATTGTCAGTTAGAGCGCTACCTGTTTACCGACCGACTACCGACTACCACCGACTGCTTTTTTTTTTTGGCCCAGTCGAGAGGGTAGG
GTACAATTGGCCCGGGTGTTGCCAGATTGCCGTTGCTGCTGCTGCCCATGGATCGTTATGGTGGCTTCACCCGAAAAGGAGGAGGAGGGTGTAAC
TCTGGTAGTTCCCTGTTTATTGTTATGCCTTTTTAGTGGGGGTGTATTTTGTTCTTCGGCTTTTGTTGCGGTTTCATTTAGGGGAATGACTAATC
AGAAAGCATTTTTAGGGAGGCAAGGTGATAAGGTTTCTTCGAAGAAGGGGTTGCCAAGTCGAAAGTTGGGGTGAAATAAAGTGCATTACTCACAC
GACTATATATCTATATTATGACAAGTTCCAATGTTCTACTGATAAGTAAATATTTATTTGGAATAATTAGTTGGTAGCTTTAGGGAAAAATATTT
ATACATATGTATTTAAATATACACTGATGATTAATCGGCAGCCGAGTTATACAATTCATTTATGGAAATAGGTCGTA
(SEQ ID NO: 277)

Exon: 13422..13345
Exon: 12668..12435
Exon: 5437..4551
Exon: 3226..1001
Start ATG: 5404 (Reverse strand: CAT)

Transcript No. : CT9648
AGTCTTCGAGAGTTGATCGTGGCCAACGCACCTGCGCGCGGATCGCTGGTAATAGCTGTTGGAAAAGTGAACTGCATTAATCGTATTAACAGAAG
TCTTCAAACAAATACAACAAGAAAAAACAACATACAATTCAAGTGCCACTTAAATGATATAAATTACTACTTTAAAAACCAAAAACAATGCCAAG
CATTTCAAAGCTTACAAACTGACAAAAAACCAGCAAAATCATATTGAAACAACTACTTGGATACTTTAGGACGCAAAGATAAAGCCCAAAGAGCC
TGGGGCTTTCTTCTGTTTAACCCACAGTTCCAACGGAATGTGAAGAGCCCCTCCAATATAATGCCCACGGAAAGCTCATCCAGCGAGATCTCCGG
CGGAGGAGGCGGTGCGATACCCATGCTGCGACCTTCCCGGATGGATCAGTTCATGAACTCGATGGCGGCGGCAGCGGCGGCGGTGGGTGGTGGCG
GTCTTCCTGGTGCGGCGGATAGGAACGGCGGATCCGGAGGATCGGATGGTGGCTCCCAGAATGGCAACGGCGATTCGCGCAACTCATCGGCCAGC
CGGATCTCAGCGTATGAAACACAGCTGGCCTATCAGCAGCATTTGGCCGGACTGCATGGTCCGCCGCCACCGCCACCACCATCGCATCATCGCGA
GATCTCTGCCTTTGTGCCGGTTCTGCCCACCGGAAAGGTGCGCCCGGGTAGTAATTCCAATTACGAAATCATTGCCATGATGGCGGACAAGCGAA
AGGAGTTGGCCCTAAGGGAGGCGGCTGCGGCGGCGGCAATGTTAGGACGAGGTCCTGGAGGACCCGGCGGTCCTGGTGTGCCACCGCCTGGAGTG
TTGTACGGACCAGCTGGCGTGCCACCTCCGCCATATCTCACCGGACCGGGTCCATCGCCCACGGGAGCCGGAAGTTTTCCATTTCCACCAGGAGC
CGCCGCCGCAGCTCTATTTCCACCTGGCCTGGGTCCTGGAATGCATGCCGGACTCGATAGGCGCCTGCTACGTGCTCCTGGTCGGGCATCGCGGC
CTAAAAAACAGTTCATCTGCAAGTTCTGCAATCGACAATTCACCAAGTCGTACAATCTGCTCATCCACGAGAGGACACACACGGACGAGCGGCCC
TATTCCTGTGATATCTGCGGCAAGGCGTTCCGGCGACAGGATCACCTGAGGGATCACAGGTATATTCACTCCAAGGAGAAACCCTTCAAATGCAC
GGAATGCGGCAAGGGATTCTGCCAATCGAGAACCTTGGCTGTCCACAAGATCCTGCACATGGAGGAATCACCCCACAAGTGCCCCGTCTGCAGTC
GATCATTCAATCAGCGCTCCAACCTGAAGACCCATCTGCTCACCCACACGGATCACAAGCCCTACGAGTGCTCTTCATGCGGCAAAGTTTTCCGC
CGTAACTGCGATCTACGACGCCATGCCTTGACCCATGCAGTGGGTGAGGTCAACTCCGGGGACTATGTGGATGTGGGCGAAGAGGATGAGGCCAG
AAATTTAAGTGGCGACGAGGAGGATTCGTTGCTGGAAGTGGACTCGCCTCGCCAGTCGCCAGTTCACAATTTGGGCGAGTCTGGAGGATCGGGTG
AGAAATCTGAGTCCGAAAGAATGAGACTCAAGCGCAAGGCAGCCATCGATCATGAGGAAAGCGAAGAGGAGTTCGATGACTTCGACGAGGAAGAG
GAACTGCAGGATCTGCCAAGAGTACACGATTTGCCCAGGGAAGAGGACGACGACTTTGATCCCGAGGACGAGGAGCAGGCAGAAGTGGCACTAGT
GGCGCGTTTCCAGGCGAGTAAGGCTGCCGCCACATCGCAATCATCGTCGTCAGTGGGCACCAAGCCGGAACGCCAGGGAGTCACCCACTGTCATC
ATGAGGGTGGTGAAACCTACACAATGCGGCCACATGGCGAGAAACATCAGGAGGAACCCGGGAACTCTGGCATTGCCAGCCTACCCGTTCCACCT
TCCTTTGTGCGATATTCTGTACCACCTGGGGCAGCTGGACCGCCGCCTGCACCACCTGGAGCTCCTCCGCCAACCCACCAGCACCCAGGACATCC
ACACTTACTCCCACCCAACGGGGATCCCTATTTGCCCATTCTGCACGTTCGACGCGACTTGCACCACAAGAGCTTGAACCTTTCGAAGGCTGGTG
TTCCACCGCCACCACATACACCACCCACTATAATAACCCAGCCGGAGTCGGGTAAACCACCCAATCAACCTTTGCATTCACCGCATGAAGCTATG
CCCAGCTTCCTGGGATCGATACCCATGCGAAAGAGGATTCTTCCGGCACCGACCTTGGACTTGATGGATCCGCACCACCATCCTGGATTGGGTCA
AAGGACCTTTGTGGATAGTCCCAGCATATATGCTTTGAATATGTCGCGACATCCCCCCAGACAGCTTCTGGGAAAACCACCGAGTACGGAAACAA
GTGGAGCCACCACCGAAAAGGGACCACCAGTGGCAGCACCGCCCATAGCACCACCGCCTGCACCACCGAGAAGAACAGGGTTCAGCATTGAGGAC
ATAATGAGGCGTTAGAAGTAAACCGAGAAAGAACTAGAAAACAATCCATTAATGGAGGTAAAATCGGAATAGAAAAACAACACAATTTGGAAAAC
TATTTATCAAAGCTCTTACGAATTTGAAATATCAAAAAGTAGTAGTATTCCTAATAAATATATATCTCGGTTGTTTTTTCTGGTATTTCATTTAG
AAGGTCTTATGAACAGTTGAATATCATAATGACAAACAGTTATTGTTCCCAATGGTTAAACGAGGATTTATCGTTTTAGACCCACAAGTACATTA
AAATAAATTTAGATCTACAATTTAATACTTTTTAGTACAATGTCTAGGCAAGGCAATAGACCTAAACTAAGTAATAAAATCAGTTAAGCGATAAT
TGTAAGCGAAACAAACTCCGTTGTTGCATTTTATAGAGCTCTTATGCGTTAGGATTTTAGCTTAAATCTACCGATTTAAATGTTTAAGCCTTTAG
TACGAGAGTCTATCGATTAGTTTTTAATGTGTGGCCCAACACTAAGTGTTGCTGTTTGCTGAGTGAATTCCAATTTTTTATTTATGTTTCCTTAT
CCGGTAAGCTAATCTTAATGAGTAAACAAAATCGTTAATCGATTTTGCTGTAGGGAAAAAAATGGTTGAAAGTAAAAGTTAGTGTAAAGCAGAGC
ATAAACAAAAATCCAACTACAAGCAACATTCCAGTAGAACCTTATGTAATTAGGCTTAAATTTTAAGAGTTTTGCAGTAGTTAATATAAGCAACC
CATAGAATTCCATGGTCTTCCTTCAATTTTAAATGATTTATTCAAACCATAGCGAGTTAGTTGATTTCAAATAAAGTATGCATTAATAATGAAA
AACAA
(SEQ ID NO: 278)

Start ATG: 346 (Reverse strand: CAT)

MPTESSSSEISGGGGGAIPMLRPSRMDQFMNSMAAAAAAVGGGGLPGAADRNGGSGGSDGGSQNGNGDSRNSSASRISAYETQLAYQQHLAGLHG
PPPPPPPSHHREISAFVPVLPTGKVRPGSNSNYEIIAMMADKRKELALREAAAAAAMLGRGPGGPGGPGVPPPGVLYGPAGVPPPPYLTGPGPSP
TGAGSFPFPPGAAAAALFPPGLGPGMHAGLDRRLLRAPGRASRPKKQFICKFCNRQFTKSYNLLIHERTHTDERPYSCDICGKAFRRQDHLRDHR
YIHSKEKPFKCTECGKGFCQSRTLAVHKILHMEESPHKCPVCSRSFNQRSNLKTHLLTHTDHKPYECSSCGKVFRRNCDLRRHALTHAVGEVNSG
DYVDVGEEDEARNLSGDEEDSLLEVDSPRQSPVHNLGESGGSGEKSESERMRLKRKAAIDHEESEEEFDDFDEEEELQDLPRVHDLPREEDDDFD
PEDEEQAEVALVARFQASKAAATSQSSSSVGTKPERQGVTHCHHEGGETYTMRPHGEKHQEEPGNSGIASLPVPPSFVRYSVPPGAAGPPPAPPG
APPPTHQHPGHPHLLPPNGDPYLPILHVRRDLHHKSLNLSKAGVPPPPHTPPTIITQPESGKPPNQPLHSPHEAMPSFLGSIPMRKRILPAPTLD
LMDPHHHPGLGQRTFVDSPSIYALNMSRHPPRQLLGKPPSTETSGATTEKGPPVAAPPIAPPPAPPRRTGFSIEDIMRR*
(SEQ ID NO: 279)

Name: brother of odd with entrails limited

FIGURE SHEET 152

Classification: transcription_factor
Gene Symbol: bowl
FlyBase ID: FBgn0004893

Celera Sequence No. : 142000013384719
GCAATTGCTGCCGTAGCTCTTCATTAGATTGGATTGTATTGGATTGATTGAATTGGATTGGATTGGCCGGTTGTGAAAGAGGTCCTGACCCGGTC
CTGGGCCTCATTACTTCAAATAGAGCGCTGACCAAACGATTTAATTATACCGCCGACGCCCGACAGTTGGCCGGCACTCAGGTGGAGACCGGGTT
CGGTTATATTTCAAAACCTGACAACACACCGACCAGAGCGCTCAGTCGGCACGCATCCGCCGTGTGAGCCGCATCAGGATCAGCATTCCTTCGAT
AGCCTTCGAGCACAATTCGAGCACAAGAACTAACCAATATGACCAGAATGATAATACAAAACTCGGGCAGCTGGACACTTTGCGGAGCTGTACTC
CTGTTCGTCCTGCCGCTGATACCCACGCCGGAGGCACTGCAGCACACCGAGGAGGGTCTCGAGATGCTTTTCCGCGAGCGGTGAGTTGTCAACTC
CATTGACATCGAACCGTTCCGATGTCTATGTCTCCATCTTTTAGTTCCCAATCGGACTGGGAGAACGTGTGGCACCAGGAGACGCACTCCCGCTG
CCGTGACAAGCTGGTCCGCCAGCTATATTGGGCCTGCGAGAAGGACATTTACCGACTGACACGGCGCAACAAAAAGAGGACGGGCAATGATGAGG
CTTGGATCAAGAAGACAACCACGGAACGTAAGTTGTTGAATCGAAATCCATTCCAACCAAAGACGATTGGAATTTCAAGCGATGTACACATGTAC
ATCTATGCTATAGATCCATTGATATCGATATGATACCACCTGCTGTCTTTCCAGCTGATGGCTCCACCTGGCTGCACGTGAACTATGCCAACATG
TTTCTGCGAAGTCGTCGATCGGATGGAAACACTCCATCGATATCGAACGAATGCTGCACCAAGGCGGGCTGCACCTGGGAGGAATACGCCGAGTA
TTGTCCATCCAACAAGCGACGCAATCACTACTGATTGGCCATCGACGTTGGATCTGCTTAGATATATATATATATATATACGAACAAACAAATATAT
ATTCGCTTTTTTTTCGTGGTTGTTGTTGTTGATGTTCTTGTTGTGGTCAAATAAAATAAACAAAAGGTTTCGGTTAAATAAAAAGAAACTTTAC
TGGCTTTAACTACAAATTTCGCATAATAAAAGCTAGATTTGCATGATATAACAAATTATATTAATCAATCAATGTTATACAAATTTAACAGTAAA
ATTGTCTTTGCAGATTAGAATAGTATAATTAAAAAAAAAAAAAAAATTTCACTTTATTCGACTTACAATGATCCTACTTTAAAATGCCCTAAATA
TGTCCTTAAAGTTATCTACAATACATTTTATACCTCTTCAATTTTGGGGGCAGTAACAATCCTGTAGTGCAATATCACCTAGTCAACAATATCGT
CCTTTTCGTCCTTGTCGGTCACATCGATCTCCTTACGACTCTTTGCTGAACCCTCAGCCTTGCTGCAGTTGGGTGATTTTCGTGGCCTCTTCGAG
GCCGAACCCTTTTCATAATGGGTGTCCAGCATCTCGAGCAGGCTCAACTGGCGGCCACCTGAACCCATTGATTTCGTGGCTGTACTGCTCGTTTT
GGACGTTGTGCTGCTGTTGCTTATTTCTACGCTGCTTTTAGCCTCCAGACTAGCGGCCTCCATCATGGCATTGGCCTCCTCATCGTCCGACAGCA
TAAGAAGGGCCTGATCTTCCGAAGAATTTGAGTTATCTTGCGATAATTGCGCGGGCAATAGATCGGTACTTTGTTGCGTTATGGTGATTTGCGGT
CGGGCGGGTTGCTTGTTGAGTTCTGGCGAGGATTTCGCTGATGTTTCTGATTTTCCTTCGCCTAATCCAGCTACTCTAGAGCTTCCAGCTTCGGC
GGATGCTCCCTCTCCGGGCACATCTCTGACCTTCTTAAGTTCCTCTTTAATAAAATCATATAGCTTCTTTTTGGATGCCTTATTCTCACGCGGCT
CCTTGGAGCTCTTCTCCTTAATAAGCCTACTGTACGACCTTAAAATACTCCAAAGCTGCTGCACCGTAGTCCCGTCATTTCGAAACAACAGCCAC
ATTTCATGAAAATCATCCCTAAACTCCACATTTCCAAAGGTATAGTAGGCCAAAGGTCTGCCCAACTGGGCGCAGACCATAAGTTGCAGCAGGGC
TTTCAGATAGGAGTCACCGCCGAATGCGCCGCAACCCCAGTTACCAGTTGCCACACCCGGTGGCGGCGTCACCATCCAGTGAACAAATCCAATGT
ACGCCTTGTTCAGCTCCCTTTCCATGAGATCCTCGCGATATTGATGATGTGACTGGGCAAAATGTAGGGCATCGATTGCCACAATGGCCGTTTGT
CGACGACCTGAGCTATCTCTTGGCGTTGAATCCTCAAAGTTGCCGGACCACTCGAAGCTTCCGGCATATCCCGTATAGTTACTATACCTTTCGGC
GCCCAACATCACCAGGGCCTCGAATGGTCGCAGACACTCCGTAAAGAGTTTACCCACCAATAGCTCCGGACAGATAACAAAGCGTATCTCCTCCT
GAACGCAGCCATGTCCCAAGACACCGCCACCCAAATATTTGTTGGCAAAGTCTACTTGCAGCAGTCCAATGCCCTCATCCTCGATTGTTCCCTCG
GCATCCACGTGCAATGGCACATCACCCAACGGCGCCGCACTTTGGCTCCAGTCGATCAGATGTTCCGGCAATCCGCTCCGACGAACAAAGGTTAC
CACACCGGTGGGCACATTGCTGGCATCCCGCTCTGTGGGACACACGCGACGAAAATAGTGCATAATGCATTTAAGCTTCTCCAGAACTGCCGGTC
CCGTCGATTGGTAAAGCCTTTTGATGGAATCGAATATATTTAACATACTTCGACTGAAGATATACGAATCTGGTGGACGCTCACCTGTTAAAGTT
GATGTCTGGAAAAGTGCTGTACTCGGACTTCCTCTTGAGGGTGTTTCTCCGGGGAAAGGTGCACAGGAAGGCATTGGCCAACAGGCAGGAGATCT
GCTGTTGGCTCAGGCTCAATGAGGCGTTCTTGTGGTGCTTGAGCAGCGGAACTGGCGATTGAATCAAGTCCGGTAGCCGCAATGCCAATCGGATA
ATGCGCGGCAATAGATCCTCGAAGAAAACCCGTGTTTCGCTCTCGTCCAGTTCCTCGTCGAGAAGTTGATGAAGGGCACGAAAGTGCCACTGATC
CCTATAGGTGGTATTATATGATATTATCGCCGCCTGCAGTTCCTCACACGTCTTTATGGGCTGCAGAAGGGCTCGTTCGATCATTTCCCAGCGAA
AATCGATGGTGGTGCTGCCATCCGGATTCTCCCTCGGATATTTCGACTCGGGCGCACAGGGCAGACGCACATGCTCGGAGTCCCACTTTCCCGGT
GATTTGTAGGGGCGTGGCGGTGTTTCACGAATTGGCAGCTGGTACATAACCCGGTGGAGATTGCCGGCAGTCACTGGTGGCAAATTCTCCAATTC
GAAAGGCTGCCGATTACGATGTATAGCCTCCATGGAAACTCCACGCCACGAATCATCTAGGGAGTTCGCCAGATTTTCCGGCTCCTCCTCCGTTT
CTATTTCGGAAATCCCGCCATCCGGCGACTTCGACATCCTGGCGCAGTTTAAGCACAAAGCCTTGCCGAGTCGATTGGTCAGCACGGATGCACTT
GCTCTGCGGCGATTTGCCGTAGATTGGTAAACCTTTTGGAATATCGGAAAAATCAAGTGTGACCTGAATTCTTGCATACCGGTGTTTTGGGGATG
AGCGATAGCTGTGATGAATATCGCACTTTATAAATACCACACACTTCGATTGAAGCGTAGTGAATTGAAGCGTTTATATATCGAAATATATTCAA
ATATATGTTGGTATTCGTTTGAGAATGAATCAATAACAAATTCAAAATTGCATTGCCTTGAATTCGGCGGGCGAAAGTGTGACCATTACATGTGG
TATTTTACCTCTCATTGTCGCTAGTATTTAAATACCAGCACGAGAAATACCAACACTGTGTCCGTTGCAATGCGAATTGCAAATATAACCGCCGA
AGGAACAACAACAAACAAAAAGAAAAAAAAAACAAATCTTCCAGCAATTTGTCAACTATTTTCTCTAATTTTTTTTAAAGTGTAAAACTATCAT
AACGAGCGCCAAGTTTTACGTTAAGTGAAAGGATTTTTTCCTGTCCTTCGTGCGGTAAAAATAATAGTGCATATTACCAAGGAAAATCAAGTTAA
AGGCGTCTGCGAAACTTTTATAAATGTATTTAATACTCAAAAAGGTAAGAAGCGGCGGAAAGTAATTGCTGTTTTATGTTTTTATAATCACGTTT
GGCAAGAAAATGTTATTTCGTTGACGTCAGTGGTCAAATCAAATTTTTTCAGTTTTTAACCCTTAATGTGGCACTGTCACTCGCACCTATGTATA
TATTTATGTGATTGTGGTATTTTGCTCAAGCTTACGTGTTGAAAAGAGGAAGAGAAACCGCTGCATACACGTGCAAAGACTCTGAGAATGGACAC
AAGAGAGCGAGAGAGGGAGAGAGAGAGAGCGCAGTTGTTTGTTTTGAAAGCGTCGCAAAAACAATACAAAAAAGGTCATACATAATTTGCACACA
CACTTGCATCTGAGGAAAACGCAAAAGCAAATTCACAGCTAGCTAAAAACCAAAATAAATATAATTTATGAAATGTACTTTTGCTAAAGTTCAAC
ACACCTTTATCTCTCCGCGAAATTTGTTTGCACCATCTCTTTCTCTCCTTTTTGCGTAAACAAACGAAAAAGCTTTGCAAGGAGAAGCAAAAAAA
AAAA
(SEQ ID NO: 280)

Exon: 3849..2935
Exon: 2867..1001
Start ATG: 3782 (Reverse strand: CAT)

Transcript No. : CT9808
TCGAAGTGTGTGGTATTTATAAAGTGCGATATTCATCACAGCTATCGCTCATCCCCAAAACACCGGTATGCAAGAATTCAGGTCACACTTGATTT
TTCCGATATTCCAAAAGGTTTACCAATCTACGGCAAATCGCCGCAGAGCAAGTGCATCCGTGCTGACCAATCGACTCGGCAAGGCTTTGTGCTTA
AACTGCGCCAGGATGTCGAAGTCGCCGGATGGCGGGATTTCCGAAATAGAAACGGAGGAGGAGCCGGAAAATCTGGCGAACTCCCTAGATGATTC
GTGGCGTGGAGTTTCCATGGAGGCTATACATCGTAATCGGCAGCCTTTCGAATTGGAGAATTTGCCACCAGTGACTGCCGGCAATCTCCACCGGG
TTATGTACCAGCTGCCAATTCGTGAAACACCGCCACGCCCCTACAAATCACCGGGAAAGTGGGACTCCGAGCATGTGCGTCTGCCCTGTGCGCCC
GAGTCGAAATATCCGAGGGAGAATCCGGATGGCAGCACCACCATCGATTTTCGCTGGGAAATGATCGAACGAGCCCTTCTGCAGCCCATAAAGAC GTGTGAGGAACTGCAGGCGGCGATAATATCATATAATACCACCTATAGGGATCAGTGGCACTTTCGTGCCCTTCATCAACTTCTCGACGAGGAAC
TGGACGAGAGCGAAACACGGGTTTTCTTCGAGGATCTATTGCCGCGCATTATCCGATTGGCATTGCGGCTACCGGACTTGATTCAATCGCCAGTT
CCGCTGCTCAAGCACCACAAGAACGCCTCATTGAGCCTGAGCCAACAGCAGATCTCCTGCCTGTTGGCCAATGCCTTCCTGTGCACCTTTCCCCG
GAGAAACACCCTCAAGAGGAAGTCCGAGTACAGCACTTTTCCAGACATCAACTTTAACAGGCTTTACCAATCGACGGGACCGGCAGTTCTGGAGA
AGCTTAAATGCATTATGCACTATTTTCGTCGCGTGTGTCCCACAGAGCGGGATGCCAGCAATGTGCCCACCGGTGTGGTAACCTTTGTTCGTCGG
AGCGGATTGCCGGAACATCTGATCGACTGGAGCCAAAGTGCGGCGCCGTTGGGTGATGTGCCATTGCACGTGGATGCCGAGGGAACAATCGAGGA
TGAGGGCATTGGACTGCTGCAAGTAGACTTTGCCAACAAATATTTGGGTGGCGGTGTCTTGGGACATGGCTGCGTTCAGGAGGAGATACGCTTTG
TTATCTGTCCGGAGCTATTGGTGGGTAAACTCTTTACGGAGTGTCTGCGACCATTCGAGGCCCTGGTGATGTTGGGCGCCGAAAGGTATAGTAAC
TATACGGGATATGCCGGAAGCTTCGAGTGGTCCGGCAACTTTGAGGATTCAACGCCAAGAGATAGCTCAGGTCGTCGACAAACGGCCATTGTGGC
AATCGATGCCCTACATTTTGCCCAGTCACATCATCAATATCGCGAGGATCTCATGGAAAGGGAGCTGAACAAGGCGTACATTGGATTTGTTCACT
GGATGGTGACGCCGCCACCGGGTGTGGCAACTGGTAACTGGGGTTGCGGCGCATTCGGCGGTGACTCCTATCTGAAAGCCCTGCTGCAACTTATG
GTCTGCGCCCAGTTGGGCAGACCTTTGGCCTACTATACCTTTGGAAATGTGGAGTTTAGGGATGATTTTCATGAAATGTGGCTGTTGTTTCGAAA
TGACGGGACTACGGTGCAGCAGCTTTGGAGTATTTTAAGGTCGTACAGTAGGCTTATTAAGGAGAAGAGCTCCAAGGAGCCGCGTGAGAATAAGG
CATCCAAAAAGAAGCTATATGATTTTATTAAAGAGGAACTTAAGAAGGTCAGAGATGTGCCCGGAGAGGGAGCATCCGCCGAAGCTGGAAGCTCT
AGAGTAGCTGGATTAGGCGAAGGAAAATCAGAAACATCAGCGAAATCCTCGCCAGAACTCAACAAGCAACCCGCCCGACCGCAAATCACCATAAC
GCAACAAAGTACCGATCTATTGCCCGCGCAATTATCGCAAGATAACTCAAATTCTTCGGAAGATCAGGCCCTTCTTATGCTGTCGGACGATGAGG
AGGCCAATGCCATGATGGAGGCCGCTAGTCTGGAGGCTAAAAGCAGCGTAGAAATAAGCAACAGCAGCACAACGTCCAAAACGAGCAGTACAGCC
ACGAAATCAATGGGTTCAGGTGGCCGCCAGTTGAGCCTGCTCGAGATGCTGGACACCCATTATGAAAAGGGTTCGGCCTCGAAGAGGCCACGAAA
ATCACCCAACTGCAGCAAGGCTGAGGGTTCAGCAAAGAGTCGTAAGGAGATCGATGTGACCGACAAGGACGAAAAGGACGATATTGTTGACTAGG
TGATATTGCACTACAGGATTGTTACTGCCCCCAAAATTGAAGAGGTATAAAATGTATTGTAGATAACTTTAAGGACATATTTAGGGCATTTTAAA
GTAGGATCATTGTAAGTCGAATAAAGTGAAATTTTTTTTTTTTTTTTAATTATACTATTCTAATCTGCAAAGACAATTTTACTGTTAAATTTGTA
TAACATTGATTGATTAATATAATTTGTTATATCATGCAAATCTAGCTTTTATTATGCGAAATTTGTAGTTAAAGCCAGTAAAGTTTCTTTTTATT
TAACCGAAACCTTTTGTTTATTTTATTTGACCACAACAAGAACATCAACAACAACAACCACGAAAAAAAAAGCGAATATATATTTGTTTGTTCGT
ATATATATATATATATCTAAGCAGATC
(SEQ ID NO: 281)

Start ATG: 68 (Reverse strand: CAT)

MQEFRSHLIFPIFQKVYQSTANRRRASASVLTNRLGKALCLNCARMSKSPDGGISEIETEEEPENLANSLDDSWRGVSMEAIHRNRQPFELENLP
PVTAGNLHRVMYQLPIRETPPRPYKSPGKWDSEHVRLPCAPESKYPRENPDGSTTIDFRWEMIERALLQPIKTCEELQAAIISYNTTYRDQWHFR
ALHQLLDEELDESETRVFFEDLLPRIIRLALRLPDLIQSPVPLLKHHKNASLSLSQQQISCLLANAFLCTFPRRNTLKRKSEYSTFPDINFNRLY
QSTGPAVLEKLKCIMHYFRRVCPTERDASNVPTGVVTFVRRSGLPEHLIDWSQSAAPLGDVPLHVDAEGTIEDEGIGLLQVDFANKYLGGGVLGH
GCVQEEIRFVICPELLVGKLFTECLRPFEALVMLGAERYSNYTGYAGSFEWSGNFEDSTPRDSSGRRQTAIVAIDALHFAQSHHQYREDLMEREL
NKAYIGFVHWMVTPPPGVATGNWGCGAFGGDSYLKALLQLMVCAQLGRPLAYYTFGNVEFRDDFHEMWLLFRNDGTTVQQLWSILRSYSRLIKEK
SSKEPRENKASKKKLYDFIKEELKKVRDVPGEGASAEAGSSRVAGLGEGKSETSAKSSPELNKQPARPQITITQQSTDLLPAQLSQDNSNSSEDQ
ALLMLSDDEEANAMMEAASLEAKSSVEISNSSTTSKTSSTATKSMGSGGRQLSLLEMLDTHYEKGSASKRPRKSPNCSKAEGSAKSRKEIDVTDK
DEKDDIVD*
(SEQ ID NO: 282)

Name: PARG PROTEIN
Classification: enzyme
Gene Symbol: Parg
FlyBase ID: FBgn0023216

Celera Sequence No. : 142000013384721
TTGTATTGCTGCCAAAATACTGCCAATCATTTCGGTCTTAAGTTATGTACATACGTATGAACTTTGTTTGCCCACGGAAAAGCGTTGAAAAAGAA
AGTCATGTAGCTTGTTAATATGCAAGTCATTAGTATTAAACACTGGACGCGTTGCTCTAAAAATTGTTTGGGTACTTTCTTAAAAATTAAATGGC
TGATTAGTTACTTTTCGACCAATATCAGCAAGACATTTGGCTATTTAATAATGATTAATTGCCCGATTAACACACAGTTCAAGCCATTGAAGATT
CTGACTCGATCTCCTTACCCTACAAATTTCCTTGGCCATCATTATCTCTTCTATTTTGGCGTTGATTTTTTTTTATCAGCGTATAGACGTAGTAG
CTCTTTAAATAATTATCTTTAGACCATATACTAAACTACTTTTCGATTCATGACTTACGGTGGGTAAAGTTGGGAAGCTCCCATCCCTCAGACGT
GCAAGTAATGGCCAGAGATAACCGTTTGGTGCGATGAAAATATTTAGTTAATGATGGTGCGCAATCTGCATCGCCCACTATACACAACACAGCAA
CCACCCACCCACTGACTGATGACAGACGGGGCGTGGCAGGTGTGATAAGCGGAGCAATTGTGATGGACAGCGATCTGTAAATTGACAGGCGGCCA
AGGGCGGGGAAGGGTGAAATGTCAAGCAGATATTCCGGTGGGTAGTTGTGGGCCATAAATAACAATCGCGAGAGCTGCGAGCTGCGGCTCCATTC
ATTGTGGGTAAGCGAACACCGGGCCGTAAATACTTCCACTTGCCTGTCGATACGATAACATTGCGATTAGGCTTATCACCACTACTCGCTCGTTC
TAACGCCTTTCGCCATCCTTCGACGTCGAGCAAGCGCGCAGTCGCAGCGGGCAGAGCAGTGCGGCAAAGCGACAAAGCGGCGAGCGGCGAAACCG
TCAACGGCTTCTTAGCTAAGTTCGTTCACAGTCGACTTCAGTCTGAGGCTGTTGATCGCCGCTTGCGGACGTGGTCGCTCAATCCTGCTCGATTC
ATAACCGATTCAAAACCGATCCCATCCGAAACGACGTGCGTTCCAATTTTTTTTTTTTTGCAGTTGTTAAATGTTTAATGTGAGTTACGAGTGC
GCGAATGCAATGGAACAATAAAAGCAATAACGATCCGAAAGCTTCGCCAGAGACAATAAAAGCAATATCAAAACACTGATGTCTATATTATGAAA
AGATCTTACGAAACAATAAAATCCTTTTAAAGGCCAATGCAGCAAAATAGGATAAAGTTACCAGAGAAAGAGCTTCCTTTTTTTATACAGTTTGA
AAATCAATTTGCAACACAGAAAATCAATTAAAACTATTAATAATCTGAATGAGATATATTTGCGATATTGTTGGTTTAATTAATTATTTCGCAGT
GGCAATTGGAAATTTCCCTTAAATATAGCCAATTTGTGGGCTTATTGAACTCCAGACGAGGATCAGTACTTTTTTGCTTTTATTGTCTCTTTTGT
CTCTTATTGGAAAAAAATAAACAAAATTTACACGTAATATACATATATGTGCATATATTTTTCGTTAAATTAAAAGAAAGTTGAGTTTATGCATC
TTATACATATGCACATTCCTACAACGTAATGATTTTTAAAGTAAATTTAATATTTTTCTTCGATTTCAAGTGACGCGTAACGGATGTGAAGCGAT
CTCCGGGTTCCCAACATGACGGATAAAAAAAATGGTATTGTTAATTACTAAAAATAACCACAGATGCATAATTATAGTTTTTACAGAGGGGTGGC
GATTATACAGACTACTGAACCGAGATTTATGGCCCATATTTTTGTGAGGCTCGAGTTTTACTCATTGTTTCGATTTCTAGACATGCTATATAAGC
CACACAAAATACACCTCACCATAGATTGCAATAGTGTTCTTATTTAGTTTATTGCACCTATTTACTTCGATACTCCTCACCCTTCAGTTTTAATC
AGTGGCCGTTGGGTAACGTGCAAGTTATAAGAATTGGCGGAATACATCTCCACTTGCCAGTTATGACTCAACGGACGAACGATTTTCAGAACTCC
AGGTTCGCAACTACGATAATCGGTTCTCTTGGCCGCGTGTGCAGTTTGCAAATCTAATCGCTCTGATAAGGGACTTTGAGTGACTGGCCCCGGGT
TTTAGCCACTTGAGCGGCTCCAACACAAGCAACGAGCAGGTCCAAATGTGGATTTACTTTCGACGGTCCCCAAAAAAGAGCTGCCAAACTTGGTC
AATTGGCACGGACCAACCTTGCCTATATACTTGCCTATTCAAATCTCAAAAAATAAATAACTCGACTTGCCTACACCGATGCAAATTTTCCAATT TGTACAACTGTGTGCGCCTGCATTTCAATGTCAGACGCCGGCTTCATTTGCATATTCGTAGGCAAACTGCCAATGCGGGTGTTTAAAACAAATGC
GGCTAAAATTGCGATTACGATTTCGTTTGGTATACCAAACACACACACACACACACCACTTGCTGACAAATCGCTGGGAGAGCCTGTAGTAAATG
CAACCGCTTGCAATTAGTGAGTGAGTAGTTCGCCTGGAATTTGCCATTTCGTATTTGGTTGCTCCATGCGGAGCAGAACCCGGTCGAATTGGATG
GGGCGGTGCCGATATGGGGTCGTAATTGCCGCTTCGAACGGAACAAGACAATCAAAGTTTTGCTCACTACCGAAAACATCGAACTTATCTATCTG
ACAACTTCCATTGAATAATTCTGTTTCTTTGCCGCCGTAAAAAGCAATTGTAATTAAAACTGGGCCAAAGCGCCAGCTCCTGCGGCGCTTATCAT
TTCGCTGGACCAATAAACATCGCGCTCGTTCTAATCGCTTGTAAATCAGTTGGAATGCTTTTAGACCCTCTTCATGGCGATTATGTATGTTATTG
GGTAGGTGTGAAATTTACAACCTATTTGATGGCCAATCGATGAACAAACCGACGATTATGCGATATCAATGCCGATATGCAATGTCATTAAAGAA
TCACTCACTACTATATATAGCCAATCCAATTATGTTCATCCGTTCTCGAATTCCAGAAGAATTTCTCTGCATATCACAGTTAGCGATAGTTCAAC
GCACATCCTAACCACCTATCAATCAATCAATCAATCAATCAATCTATAGGTCCCAGGGCTCTTAGAGCTTAAGTAAAGAAATCTTGAGAAAGTGA
AATTGAGAACACTTTCACAGCACTTTCCCTCCGAAACTTTACAACTGCACTCAGGGCATACCAGGCTTATCTAATTATTTATAGGTAAAGCCCTC
AGTGTACTCATTTTTCAATTAGCTTGTTGAAAATTACGGAGTATCAGCGACTCCGATTGGTCTACGGCTTTTATGGAGCCCAATCGAGTGGATTG
AGTGGAGATCCGTCTGGAGATCAATTTTCCGTCCTTCGGTGACACTTGGCCAGTTCCCTGGCACTAAACACTACGCTATTAGCGGCTGCAAAATG
AATGAATGAATGAGTGGTTTTGAGTGTGAATGTGAGTGGCAGGCCTGGTCTACCAACTTCAAACGGCCACCGAAGCGGGTCAATGCTGTACACGT
CTGGTACTTGTATATTTTGTATATCTCTGTTTCCCTGCGATAAGGCGCTTTATGTTAATGGATGTTTGATGTGAAGTGTAGTGCGTGCAATAGCA
TTGTTTCCACGGTTTATGGAGCCATGTGATGGCTGCTATACATTACTGCCTCAAATAGCGGTCATAAACGCTGATAAAGCATCGATGGATTAGCT
GCGAACCGATTCTGGATCGCAGTTAGATAAGGCCCATTCATTGGTCGCCATTCGGGACTTTCGCAGTTCGCAGTTCGCTTCCTGAATCATCAACC
ATCGAACAGATACAGATCCAGTTGTCCGAACATGGCCATGACCATGACTAGCTGCACTAGGCACCAGCTGCAATTACCATTCGATCCACATGGAC
ATGACCATTAAAGCTCCAGCAGACATTTAGACGCAGCATTGTCAGTAATCAGCATGTTGTTTATGGCGTGGAAAGCCATACTCCCAGCCAGTTTG
TCAAAGTGTGGAGGCGATCGCCGAGAGAGCTATCTTCCCTAGCTGGGTTATCTGACGCCCGCCACTGGCGTAAACCTCGTAAAAGCTCGGGGCCT
AAGGCTGGATAATTTATGCCGGGCCACCGAATTCACACGCCCGCCGTTGAAGTAAAGGCCCGTTCAAATATAGAACAGTCCTTATCTGTGGCGGA
GGTGTCAAGCACAAGGCCACAAGTCTCGGTTTCGGTTTCTGATGAAATGTCGCCGATCCTCAGATCACTAACGAATCTCAGTGGCCATATGAAAT
GGAGCTGCCGGCGGAGCAAGTACCCCTGCTGGGTGGGCTCTCCAAGTTTTCGATTATTGCATTTCGAATTACTAACCTGGATCCTTCTTTCGTCC
GCAGAAATACAGCCAGCGGCTGAGCCTGTGGCTGAACCAGAGCCTTCTCCCGCGGCCGAAATAGCTCCTGCAAGTCCCGATGGCTCCGGTCCAAG
TGCTGCCGCTGCAGAAGAAGTCACCCCGAGTGTTGCGACCGTTGAAGACACTACCCCGATTGCAGCCCCTGCAGAGAGTCAACCGTCCGGCGAGA
GCAACGGCACGGCGGAGGCCAAGAAGCTGCCCGAGATCGCTAAAAAGAATGGCAAGGAGCCCGACCAGAATGACAAGGAGCCCGACCAGAATGGC
AAGGAACTGGCAGAGACCAATGACTTCAAGAACGTCTCCGAGACTGAGGGTCAGCAGAAGGTAATCGTCATTGGTGCTCTTTAACAAGTATTGAA
GCAAACACTGTACTTACCTTTTCATTGACACCCACAGAAACTGCCCTACCCCAAGTCCGTGTTCTTCATCATCAGTAACGAATTCTGCGAACGTT
TCAACTATTACGGCATGAGGAGTAAGTTAATCGCAAAGTATCTTACAATGAAATCTCTGCTAATCGCTCGTACTCCATTCAGCTGTTTTGGTTCT
GTATCTGAGTCGAGTTCTGGGCTATTCTGATGATACCGCCACCGTGGTCTTCCATATCTTCACCATGTTCGTGTACTTCCTGTGCGTTTTTGGAG
CCATCATTTCGGACTCTTGGCTGGGAAAATTCAAGACTATCCTGTATTTATCGCTGGTTTATATATGCGGATCGGTGCTGCTGACCCTAGGTGCC
ATTGGACCACTTAACCTGCCCATGGAAACGTTTACGATGTTGGGCCTGGCGTTAATTGCCCTTGGTTCAGGCGGCATTAAGCCGTGTGTGTCGGC
ATTCGGTGGCGATCAGTTTAAGGTGCCGGAGCAGGTGAAGCAGATCACTTCGTTCTTCTCGCTCTTTTACTTTTCGATCAATGCCGGATCGCTGA
TCTCCACCACGGTGACTCCAATATTGCGCGAGGACGTGTCCTGCTTTGACGACATTAACTGCTATCCATTGGCCTTTGGAGTACCGGCCGTACTT
ATGATTGTGTCGGTGATCATCTTCGTTTTGGGACGATCCCTGTACAAGATGAAGCCACCGGCCGGAAATATGGTGGTGCTTGTGAGCAGTACCAT
CTGGACAGCCCTGACCACCAAATGTAAGGAGAAAAAGACCAATCCGCGGGAGCACTGGCTGGACTATGCCGATAAAAAGTACGACCGCCAGTTGA
TTGACGATGTAAAGGTCCTTATGCGAGTCCTCTTCCTCTACCTGCCACTTCCGGTCTTCTGGGCACTGTTTGATCAGCAGGGCTCCCGTTGGACC
TTCCAGGCCACCCGAATGGACGGCGACATGGGCTCCTGGACATCAAGCCCGACCAGTTGCAAGTGCTCAATCCTCTGCTCATCCTAATCTTTAT
ACCGTTGTACGATGTGGCCCTCTATCCGGCCCTGAAACTAGTGGGTATCCGACGACCGCTGCAGAAACTCACCATGGGCGGCATCCTTGCGGGCA
TTGCTTTCATCATTTCCGGAGTGGTGGAGCTTAGCTTGGAGGTGAGTAATTGTTCGAAAATGCTTGTTGGCTTGGGACTTAAAGCTCTGAAAGTA
TTTAATTGGGAAGTTTTAAAGTATTTTTAACTGCTGTGCTTATATATATTGTATTGTACTGTACCTGCACCTGCACTTTCCGTTTTTCTTTCGTT
GCACGCCTTGCTGTCGTTAGAAAACCTATCCCGACCTGCCCTACAGCCAGAACATCCAACTGCGCATCTTCAACGCGGACAACTGCGACTACTTC
TTCACTTCGAACATTCCGGGAGCGGAAAATGTGACGGTGACCTCGTTGAATGCCTATACCAACAAGGATATTTACGCACCCGGTTCGCTGGACGT
GGAGTTCTCGCTCAGCAGTGCAAGTGAAGCTTGTACCATTAGCGCTGACAAAATACCTAAAGTCCTTACTGATAATACGGCTTGGTCTCTGTTCC
TCAATCCGCTAAATGGTAGTGGATACTACTGGGAGGAGGATTTTGTGGACAAGCCGAGCCAGAGCCATCCGCTGATCCGAAACGTCGCTAATGTG
CCGCAGGAGCTGTCAATTCGTTGGGAAAAGGCTAGCACGGGAGAGGTGGTCTATGACGACCTGGCTAGCAAAACGTTGCTCACGCGTGTGAATTC
GGCGGAGTATGTAGTCATGGTGGGCGAAAGGAACGTCGGAACATTCGATGTTCACACCGGCGGCGTGTACACACTCCTGATTAAAGATAACAACA
ACATTTACGAGGCCAATTTGGAGGAAGTGACGAGCCCCAACTCGGTAAAGATCCTTTGGCTGGTGCCGCAGTACGTGGTGATGACCCTCGGCGAG
GTGATGTTCTCGGTGACGGGACTGGAGTTCTCATACGCCCAGGCACCACCCAGCATGAAGAGTGTCCTGCAGGCCTGTTGGCTGCTAACGGTGGC
CTTCGGCAACGTCATTGTGGTCGTCATCGCCGAGGCCGCCTTATTCGAATCGCAGGCCAGCGAGTTCTTCCTGTTCGCCGGCCTCATGTTCGCCG
ACATGTTGATCTTCATGGTGATGGCCTACTACTATGTGCCCAACGATCCGAACAAGGTGGAGGAGGCCCAGCCCCTGACGGCGGGTGATGCCAAA
ACAGAGATTCCCGCTCTCGAAGGCGGAGTCGAGAACAAGGGCAAGGACATCAACGAGTAGACCTCAAACCGATTCGTCCTGCTTGCTCCCGCGTT
GTGTATTATATATATATATATTTGTACTTGTAGATGTGTATATGTATGTAAATCCTTAGTGGCCTTTGTCCATTTCCAAGCTAAGTGTAAGTGAA
GCTGCGACCGGGCATTGTTGCATATGAAAAGACATCCAACTAGTTAATCTAATAAAAGAAAATTAATAATATAATCCGTCGTTGTTACTATTCTT
GTTGTCTCTCTATCTGCTTTAATACTCTTAATTGTTTCTTTTCACCTATGACCTGGATTTTACTCAGTATGATAGTCTTATACGATATCATTCCG
GAGATTTCTGGTATTGCTCCGATCTAATATATTAGTACCAGCTTGCACGTATATCTTCCACCCTTGCAGCACACTTACCCATTGATCCCGAGCAG
TGGTAATACCCAGCTACGCGTCTTCAGCGGTATTCCCGACTGCGATTATCGCTTTAGTACGAACCTCGGAGCCCGGGAGAGCTTCACCTTAAGGG
GGCTGGACTTCTACTATTCGGGTAGCGTGGCCACGAACACCGACGGCATCTTCCAGTTAACATACACCGTGGAAAGTTTAACTGAAGGTATGTTA
CCACGTTATCGCGATCCTCCTATTCAAGAGAACTTGTTGATGTAAGAACTCGTGAATATGTTTAAAGCCCACCATCCTCTTTGGAGCGTTAAGCT
GTCAACACAAATAGAATCACTTCAGTGGTCACAAGGTTTTCGGATGTTTGAGAGTATCTTAGAATGGCTGATAAGCCATTAGTAGTAATTACTAG
TAACTTTTTTGGGTAGTATTTTGAATTGGGTATGGGTAGTATAGTTGAAATGGGTATTCTACCACAATTTGTACTTTATTCTGAATGGTGTACCC
CTTAGGTTGCGCAATCCTGGAGGGCGGAACACAGCAGTTGTATGAGGCCACCGCCCACTCACTGTTCCTGCGACCTTCGCACGCCATCACTAAGT
TTTGGTACGAGGACGAGGTGCAGAAGTCGAATCGCTCGTGGGCTTTTGTGCGAAACTTGGCGAATCTCTTGGCCACCACGCGTGTCGTTTGGCGG
GAGGATTCAGGGGATACGGTGGCCCTGGATTTGCCCGCCCGCAATCATGATCTCTACGAGCTAAGTACGGGCGGTTACAACGTTCAGGTGGCGGA
TCACAATCTTACCAGCATAGAGTTACGCGCTGGGGGCGTTTACGCCCTGCTGATCGGCCAGAGTCACGGAACATTCGTATCGCGAATCATAGAGG
TAACCAGCCCCAATTCGATGCACATGCTCTGGCTGGTGCCGCAGTACGTGGTAATGACCCTCGGTGAGGTGATGTTCTCGGTGACGGACTGGAG
TTCTCCTATTCCCAGTCGCCGCCCAGCATGAAAAGTGTCCTGCAGGCCTGCTGGCTGCTAACAGTGGCCTTCGGCAACGTTATCGTCGTGGTTGT
GGCGGAACTCAAGTTCTTCGACTCGCAAGCCAGCGAGTTCTTCCTGTTCGCTGGCCTCATGTTTGTCGACATGCTGGTCTTCATGTTCGTGGCCT
ACTACTATAAGCCATATGATGAGGTGGCTGCTCTGGCGGAGAGGGTAAGGGCCAGACGGGAACGGAAATGGCAGGATCTCGACCGATTCAAGAGG
GACTAGGAATACGGATGCCTGATTGTCATTTGAATCTGTCCGCTTATTATATCCTTATGTGCAGTTCTTTTACGATTCGAAATAAATATCCCCCA
AATATGGCAGAACAAAGACTTTTTAATATCCGCCATCATCCTTTGAATTGTTTTAATACGCTAAGTTGAGTGTTAAATAAGTTATATTAAATGTT
ACTGACCATTGCCTTTACATTTATCCAGCGCTCAACTTGTTTATTACCGCCAGTGGACTCTGCACTTAGTTTATCATTAAAATATAAGTCCACTG

FIGURE SHEET 155

CACTTAGTATATCAATAAAATATAAGTCTACTGCACTTAGTATATCATTAAAATATAAAATGTAGGTTTATATTAGTATAACTGTAACGAATATT
CAAGCTCGCGCGGAGTTGCCAGATCACAACTTAACAGCGTGCTGTTATGCGCATGTTGTCACCTGACATTCCGCCTTTTTAGTACCTTTTGCGC
TGACATTTGGTCGAGAAAAATATAAGAAGAGGAAGAGTTGAAAATCATATGACTTGTCGATCGATAGAGAAAAAAGGTTGAATTTTCACCGTCGC
TCCGTATCGAACTGCACGCCCTTCGCCACACAATTCGCGCAACTTTCGGTCGAGCGAGAGCAGTCCCATAGAAAGGAATCCAGCGCAATTCGCCA
CCTCTTCAACTTCCAGTCAGCTCCTCTGCGTGTGTGTGTGTGCGTGTGTCATCAAGATGAACAGCTCGGGCTTTATGTTTAACATCGATAATGGA
TATCTGGAGGGTCTGTGCCGCGGCTTCAAGTGCGGCATCCTGAAGCAGGCTGACTATCTCAACCTGGTGCAGTGCGAGACCTTGGAGGGTAAGTA
GTAGAGCCATCGCAAGCGTAAACCGAAAACCCCATTTTCCCACACGCCCCTGGGTCACATGACCAGCGATAACAGAGTGGTGCGTGTGTGTATAT
ATATACATGTACGGCTGTTAATGTATCTTTGCGCCGGTGTGTGTAAGCTTGTCTTGTGATTTGTTGACGTTTTTCAATT
(SEQ ID NO: 283)

Exon: 1001..1125
Exon: 1686..1744
Exon: 4470..4810
Exon: 4883..4961
Exon: 5023..6026
Exon: 6196..7181
Exon: 7601..7782
Exon: 8081..8864
Start ATG: 1726

Transcript No. : CT9935
GTTGATCGCCGCTTGCGGACGTGGTCGCTCAATCCTGCTCGATTCATAACCGATTCAAAACCGATCCCATCCGAAACGACGTGCGTTCCAATTTT
TTTTTTTTTGCAGTTGTTAAATGTTTTAATTGACGCGTAACGGATGTGAAGCGATCTCCGGGTTCCCAACATGACGGATAAAAAAAATGAAATAC
AGCCAGCGGCTGAGCCTGTGGCTGAACCAGAGCCTTCTCCCGCGGCCGAAATAGCTCCTGCAAGTCCCGATGGCTCCGGTCCAAGTGCTGCCGCT
GCAGAAGAAGTCACCCCGAGTGTTGCGACCGTTGAAGACACTACCCCGATTGCAGCCCCTGCAGAGAGTCAACCGTCCGGCGAGAGCAACGGCAC
GGCGGAGGCCAAGAAGCTGCCCGAGATCGCTAAAAAGAATGGCAAGGAGCCCGACCAGAATGACAAGGAGCCCGACCAGAATGGCAAGGAACTGG
CAGAGACCAATGACTTCAAGAACGTCTCCGAGACTGAGGGTCAGCAGAAGAAACTGCCCTACCCCAAGTCCGTGTTCTTCATCATCAGTAACGAA
TTCTGCGAACGTTTCAACTATTACGGCATGAGGACTGTTTTGGTTCTGTATCTGAGTCGAGTTCTGGGCTATTCTGATGATACCGCCACCGTGGT
CTTCCATATCTTCACCATGTTCGTGTACTTCCTGTGCGTTTTTGGAGCCATCATTTCGGACTCTTGGCTGGGAAAATTCAAGACTATCCTGTATT
TATCGCTGGTTTATATATGCGGATCGGTGCTGCTGACCCTAGGTGCCATTGGACCACTTAACCTGCCCATGGAAACGTTTACGATGTTGGGCCTG
GCGTTAATTGCCCTTGGTTCAGGCGGCATTAAGCCGTGTGTGTCGGCATTCGGTGGCGATCAGTTTAAGGTGCCGGAGCAGGTGAAGCAGATCAC
TTCGTTCTTCTCGCTCTTTTACTTTTCGATCAATGCCGGATCGCTGATCTCCACCACGGTGACTCCAATATTGCGCGAGGACGTGTCCTGCTTTG
ACGACATTAACTGCTATCCATTGGCCTTTGGAGTACCGGCCGTACTTATGATTGTGTCGGTGATCATCTTCGTTTTGGGACGATCCCTGTACAAG
ATGAAGCCACCGGCCGGAAATATGGTGGTGCTTGTGAGCAGTACCATCTGGACAGCCCTGACCACCAAATGTAAGGAGAAAAAGACCAATCCGCG
GGAGCACTGGCTGGACTATGCCGATAAAAAGTACGACCGCCAGTTGATTGACGATGTAAAGGTCCTTATGCGAGTCCTCTTCCTCTACCTGCCAC
TTCCGGTCTTCTGGGCACTGTTTGATCAGCAGGGCTCCCGTTGGACCTTCCAGGCCACCCGAATGGACGGCGACATGGGCTCCTGGGACATCAAG
CCCGACCAGTTGCAAGTGCTCAATCCTCTGCTCATCCTAATCTTTATACCGTTGTACGATGTGGCCCTCTATCCGGCCCTGAAACTAGTGGGTAT
CCGACGACCGCTGCAGAAACTCACCATGGGCGGCATCCTTGCGGGCATTGCTTTCATCATTTCCGGAGTGGTGGAGCTTAGCTTGGAGAAAACCT
ATCCCGACCTGCCCTACAGCCAGAACATCCAACTGCGCATCTTCAACGCGGACAACTGCGACTACTTCTTCACTTCGAACATTCCGGGAGCGGAA
AATGTGACGGTGACCTCGTTGAATGCCTATACCAACAAGGATATTTACGCACCCGGTTCGCTGGACGTGGAGTTCTCGCTCAGCAGTGCAAGTGA
AGCTTGTACCATTAGCGCTGACAAAATACCTAAAGTCCTTACTGATAATACGGCTTGGTCTCTGTTCCTCAATCCGCTAAATGGTAGTGGATACT
ACTGGGAGGAGGATTTTGTGGACAAGCCGAGCCAGAGCCATCCGCTGATCCGAAACGTCGCTAATGTGCCGCAGGAGCTGTCAATTCGTTGGGAA
AAGGCTAGCACGGGAGAGGTGGTCTATGACGACCTGGCTAGCAAAACGTTGCTCACGCGTGTGAATTCGGCGGAGTATGTAGTCATGGTGGGCGA
AAGGAACGTCGGAACATTCGATGTTCACACCGGCGGCGTGTACACACTCCTGATTAAAGATAACAACAACATTTACGAGGCCAATTTGGAGGAAG
TGACGAGCCCCAACTCGGTAAAGATCCTTTGGCTGGTGCCGCAGTACGTGGTGATGACCCTCGGCGAGGTGATGTTCTCGGTGACGGGACTGGAG
TTCTCATACGCCCAGGCACCACCCAGCATGAAGAGTGTCCTGCAGGCCTGTTGGCTGCTAACGGTGGCCTTCGGCAACGTCATTGTGGTCGTCAT
CGCCGAGGCCGCCTTATTCGAATCGCAGGCCAGCGAGTTCTTCCTGTTCGCCGGCCTCATGTTCGCCGACATGTTGATCTTCATGGTGATGGCCT
ACTACTATGTGCCCAACGATCCGAACAAGGTGGAGGAGGCCCAGCCCCTGACGGCGGGTGATGCCAAAACAGAGATTCCCGCTCTCGAAGGCGGA
GTCGAGAACAAGGGCAAGGACATCAACGATGGTAATACCCAGCTACGCGTCTTCAGCGGTATTCCCGACTGCGATTATCGCTTTAGTACGAACCT
CGGAGCCCGGGAGAGCTTCACCTTAAGGGGGCTGGACTTCTACTATTCGGGTAGCGTGGCCACGAACACCGACGGCATCTTCCAGTTAACATACA
CCGTGGAAAGTTTAACTGAAGGTTGCGCAATCCTGGAGGGCGGAACACAGCAGTTGTATGAGGCCACCGCCCACTCACTGTTCCTGCGACCTTCG
CACGCCATCACTAAGTTTTGGTACGAGGACGAGGTGCAGAAGTCGAATCGCTCGTGGGCTTTTGTGCGAAACTTGGCGAATCTCTTGGCCACCAC
GCGTGTCGTTTGGCGGGAGGATTCAGGGGATACGGTGGCCCTGGATTTGCCCGCCCGCAATCATGATCTCTACGAGCTAAGTACGGGCGGTTACA
ACGTTCAGGTGGCGGATCACAATCTTACCAGCATAGAGTTACGCGCTGGGGGCGTTTACGCCCTGCTGATCGGCCAGAGTCACGGAACATTCGTA
TCGCGAATCATAGAGGTAACCAGCCCCAATTCGATGCACATGCTCTGGCTGGTGCCGCAGTACGTGGTAATGACCCTCGGTGAGGTGATGTTCTC
GGTGACGGGACTGGAGTTCTCCTATTCCCAGTCGCCGCCCAGCATGAAAAGTGTCCTGCAGGCCTGCTGGCTGCTAACAGTGGCCTTCGGCAACG
TTATCGTCGTGGTTGTGGCGGAACTCAAGTTCTTCGACTCGCAAGCCAGCGAGTTCTTCCTGTTCGCTGGCCTCATGTTTGTCGACATGCTGGTC
TTCATGTTCGTGGCCTACTACTATAAGCCATATGATGAGGTGGCTGCTCTGGCGGAGAGGGTAAGGGCCAGACGGGAACGGAAATGGCAGGATCT
CGACCGATTCAAGAGGGACTAGGAATACGGATGCCTGATTGTCAT
(SEQ ID NO: 284)

Start ATG: 166

MTDKKNEIQPAAEPVAEPEPSPAAEIAPASPDGSGPSAAAAEEVTPSVATVEDTTPIAAPAESQPSGESNGTAEAKKLPEIAKKNGKEPDQNDKE
PDQNGKELAETNDFKNVSETEGQQKKLPYPKSVFFIISNEFCERFNYYGMRTVLVLYLSRVLGYSDDTATVVFHIFTMFVYFLCVFGAIISDSWL
GKFKTILYLSLVYICGSVLLTLGAIGPLNLPMETFTMLGLALIALGSGGIKPCVSAFGGDQFKVPEQVKQITSFFSLFYFSINAGSLISTTVTPI
LREDVSCFDDINCYPLAFGVPAVLMIVSVIIFVLGRSLYKMKPPAGNMVVLVSSTIWTALTTKCKEKKTNPREHWLDYADKKYDRQLIDDVKVLM
RVLFLYLPLPVFWALFDQQGSRWTFQATRMDGDMGSWDIKPDQLQVLNPLLILIFIPLYDVALYPALKLVGIRRPLQKLTMGGILAGIAFIISGV
VELSLEKTYPDLPYSQNIQLRIFNADNCDYFFTSNIPGAENVTVTSLNAYTNKDIYAPGSLDVEFSLSSASEACTISADKIPKVLTDNTAWSLFL
NPLNGSGYYWEEDFVDKPSQSHPLIRNVANVPQELSIRWEKASTGEVVYDDLASKTLLTRVNSAEYVVMVGERNVGTFDVHTGGVYTLLIKDNNN
IYEANLEEVTSPNSVKILWLVPQYVVMTLGEVMFSVTGLEFSYAQAPPSMKSVLQACWLLTVAFGNVIVVVIAEAALFESQASEFFLFAGLMFAD

MLIFMVMAYYYVPNDPNKVEEAQPLTAGDAKTEIPALEGGVENKGKDINDGNTQLRVFSGIPDCDYRFSTNLGARESFTLRGLDFYYSGSVATNT
DGIFQLTYTVESLTEGCAILEGGTQQLYEATAHSLFLRPSHAITKFWYEDEVQKSNRSWAFVRNLANLLATTRVVWREDSGDTVALDLPARNHDL
YELSTGGYNVQVADHNLTSIELRAGGVYALLIGQSHGTFVSRIIEVTSPNSMHMLWLVPQYVVMTLGEVMFSVTGLEFSYSQSPPSMKSVLQACW
LLTVAFGNVIVVVVAELKFFDSQASEFFLFAGLMFVDMLVFMFVAYYYKPYDEVAALAERVRARRERKWQDLDRFKRD*
(SEQ ID NO: 285)

Name: oligopeptide transporter
Classification: transporter
Gene Symbol: BcDNA:GH06717
FlyBase ID: FBgn0028491

Celera Sequence No. : 142000013384832
CCAAGATAACGAATGACTCTTCGTCCGACATGTCTCCGTTGTCGCGGTAGCAATGGCGGGTATTAATAATCAGATTTTACGACTGTGAACGCAGG
TGAGGGAATTCCCCTCTTTCGAAAACTAGACGGCAAAGTATTAGCCAAATCGATTAATTTGATATCGGCAATAGTAAGGATAAATGTATAATAAA
TGAGTTTTAGGGCAATGATTCATTAGGCGTGGGAATTACATCGACGCGTCACAATGGAATAAGCAATTGTCATGTTTATTGCATATATACCTTAT
ATACTACTGCGTTCCTTATCTCGTTTTGCTTTGCTGACAAGCTTTAAGGAAATAAAATTGTTTTCGGAGTAATATTTACTTTTAACTAATTTACC
AAACAACTTAGACCAGTGTGACCGCAATCGTTTCAAATGTGCCTTTTTTTGTGTCATTGATTGTCATATTGTCATAATCGGAAATGTTATCGACA
ATCGGCGAGCTCGTCTATCTAAATTTAAAAGCAGCTAATTTCAATAAAACTGATTACACGCCCAAAACTCGTGCATATGAAGTGCAGTTTGCACT
GCAAGGGCGGTGGAAAGTCCCGGCATCATTTATTCAAGCCCAGTGACGTGCATCCCAATTTACCTTCCTTTGTTGCTCAGCTGAGATTAATGGGC
GCGTCCTAAAGGCCTGAGCCTGACAAACCAGTTGCCAGCGAAATTACACCGAAATGTAATTGCCAAAACTCGCAAATTCTAATGGACGGCGCAGT
GCGTTCTGAACCCGCCAAACCGGATTCAGTACCTCCATTGTTCGGCTCAACTCTGTAGATGTGGGTTAATAAGGCTTTCGCGTGTTAAATATAGG
TGTGAGTGGAGCTCGCGACAAGGAACTGGTGGCTGGCCGAGATGCGACTTTCGTATTACCATAACCAACCGGTTCCTGGCTATGTGCACAGACCG
CATCCCCATCCTCATTTCCATCCCAATCCACACATTTTAGAATTAATACGTTCGTAACAATGATAATCATCATGCGGTTTATTACTCAAGAATCT
CTATGTGATCTTACGACTAATGCACGCGAATAAATAAAATTAAAAAAACTTAAACGAATACGATACGAAATTCCATTAAAGCTCAAGTGCATTCA
AGAAAACTCCTCAAACGGCTACAACTAGAAGACTCACACGTTCACTCTCGCACTCTATGATGCAGGATCTCCTCATCTGCTCTATCACATTCACA
CAAGGACTTAGGTCTAGGCCTGCGGATCCTCTGACCGCGATCTTACGCCTGTTGCTGGCGGAACAGACGCCTCTGCGTCTGGTGGGGTGGCTGGA
GGTCGCTCTGCAGGATAGAGGCGAAGTGCTGCTGCTTTAAGGAGCTGATTGTGGCGATCTTGCGGTGCCTGTTGGGCTGAGCGGCGGCCAGACCA
AGATGAAAGTAGGGCAGGTCTTCGTCCCGCGGCAGTGGCATCATCTTGTCCTCCTCCACCGGGGAGCCATCGGGTCGCACCCGGATCACCAAAGG
TCCGGTGAGGAATCTTTTGGACGGTTCTGAAGTCAGTGCGGCGGCCATTGGGAGCTCACTGCTGGACTGCGGCCCGTAGCCGTAGGCCTTGTCCA
TGTCCATGGCGTATTTGTGCTTCTGCTCGCCGCTCTCGAAGATTGGATTGGTGGCGGAGCCGGAGCTCTGGATGGGGTGGGCATGGGATGCTCCG
TGCGGAAGTTGCTGGCGCGTTAGGATGATCAGAGAGGACGCAGGAGGAGTTGGCAGGGGCTGTTGGAGCGGCTGCCTCGTTGTCACCAGGCTGGC
TCCGCTCGGATGGTCCCCCATAATCGATGACCAGACTGCGGAAGAAAAGAGCGATTAGATCGACACCGAGATTTAGAGCTCACGTCGAGCACGTC
GCGACTGCGCACTGCGGAAGTTCTGACGCGGAAATCAATCATTCTCCCACGCAGATAGAGGCACTTACTCAGCTCGTTGGCATCGCGCTGATACG
GATCTAGTGCCTCCAGCTGTACGTCGGAGAGCGTCTGCAGCTTGGCGGACCCGTAACCGAGCAGGTTGTGCTTGCACTGGTTCACTGGGAGGCCT
CCGACGGCGGCTGTTGACTTGCAGTGCACGCTTACCAATTGAGCGAATGTTGAGTAGAGGTGGGACATCTGCAAAGTAACAAAATTGGTGGTTAT
TTTAATGGCGTCTTGTGTTTAAGAATCAAGTTATAGAAATTAGAAAGCAGATCATCGCTTCTCTGTTCACCAGCCGAATATGGTATTGATTTGTC
ATAAACGAAAATCGGAGAACATATGTCGGTGATATTAGAAAAAAAAAGAAAAAAGAAAGTTCGAAGCAATCATACTTCGACCAGGTCTCTTGGGT
AACGCAGGGCAGAGGTGGAGCTGAAGCCTGGTGCTCTCAATGGGGGGATTTCGCAAGGTGCGTGTGTGTCAGCCGGGAGATGATTGCACTTTCGT
TGCACAAACGAAATGCATTTCGACAGCGCGGCCCGCGGGTTGAGCAACTGCCTCCCAGGGCGAGATTGGATGGCTGCCATCTGGTTCATGTGCCC
CAGTTCGGATGGGCTGGGTATGAGTATGGGTTTACGGTTCAGCGGCCAAAGCAACAGCTCATTGTCTATTCTCCGTGGCCAGCGAAGCGTCGAAT
GGACTTTTAATTAGCGCCGAATGTTCTACTGCGGTGACACATCTGCATCTGAGATTTGTGGGATTTCTCTGGTCGTCGGTGACGTCAAGTGGATC
GCTTCAGCTCCGATGCTAATTTAGTGGTGGTGATACAGAGCAGAAGCTCCCTGAAATTTCCGAATCCGGCATTGGTCACGACTTAGCACCTCTCC
CGACAGACAGCCAAACAATCGAAGAGTCGACGAGCAAACAGCAGAACAAAGAAATAAAAAGAAATGGGGAACTGGGTTACTTCACTAGGGGATCC
AGTATCGAGTCTGTAGCCTCCTTCTAGATATATGTATATATATATATATGTATTTGTATACACCCTTGATCTGCTTCAAAATCTAGCAAGAGC
TTCATTTGCATTGGCTCTGCTTTGGGTTTTACAATTTTACGCCGTTTGCATAATGCATTGGATATATCGGATCGGCGGACTCGGAGGGGCCAAAG
TTGGAGAGTTGGGTTGTTGGCGGGTTGGCTCACATTACCAATTACCGTTACCCACTCAGTGGGGCCACACAAACGTGTGCAAACTGCGAATTGCA
GTGGATACCATCGCACCACCTCAGCACCCCCCTGGGTGTGCATTTGCTCAGATGTGTACTTGAGTGGGGCAGCGATTAATTGAACGAATCGGTTC
CTTTGTGCCCACCCCTCCGCCAGTGGAAGCCACTCTGCGTCAGGAGCACGTTATCTGATTCGAATAACTCGGTCGGGATTTTATGGTCCAGGCCC
TGGCACAATTAAATATATAACCCAGTCAAAATTGCAAATTCAGCAAAACAGCAATTTATTTATGGCTTAGTGCGCAAATATTCCAAAAAGCCTTT
GCGGGAGTTGTCAAAGTCACGTACTTAATTCGCTTATATAATATACGCTCGTTTTTATAAAAATATGTTTACTCGAGATCGTCGCGGACAGGTTG
TAACTCATTAGCCTTCCAGCGAAGTGAGCTAAGCTAAGTTGAGCTGAGCTGGCATCGCCTGGTTTGTCCACAAGTCTAGCCTATAGACAGACTGA
TCTTGGCCCGAGCCATCTGTATCTGTATCTCAAACTTCCTTGTGGCTATGCGAGATACTCAGTCGACGCACAACCCCCGAGAAGCGAGACCCAGA
GATGGCCAAAAGCGGTCTCGTGGGTCTGCAGACGCGACTGCTTCCCGGGCCGCAAGTGGTGGTGGTAAACCCCTGGCCCATACCACATGCCATCC
CCAGCGGATTGGCGGTCAATAACCTGTTGATATGCGCAGGTTACATTATGAAACATCGAAATGGCCAACCACAGAGACCAACGCACAGACAGCCA
CGAAAATGAAAAATTTCATAACAGACAAAATAAAAAGCTAAAAGACGAAGTAATGATCGAAGTTCGATCGGGTATCGGATGGAAAAGGGTTCCA
TTACTACACACATGCTTGTGTATCCCAGCATATTTTACGTAAAAACAAAACGGTAATGCGAACATAACTTATTTATTGGGGCCCGGACCGCAAAC
CGGCCAAACGCGTTTGCACCCATAAAAACATAAGGGCAACAAAAAAATTGTTAAGCTGTTGTTTATTTTTGCAATCGAAAATCGAAAGCGCTCAA
ATAGCTGCGATCACTCGGGAGCAGGGTAAAGTCGCCTCGAAACAGGAAGCTGAAGCATCTTCTATAAATACACTCAAAGCGATCATTCCGAGGCG
AGTCTGGTTAGAAATTTACATGGACTGCAAAAAGGTATAGCCCCACAAACTGCGTCTCCACATCGCTGCGTTTCGGCAGCTAATTGCCTTTTAGA
AATTATTTTCCCATTTCGAGAAACTCGTGTGGGATGCCGGATGCGGCTTTCAATCACTTCTGGCCCGGGATCGGATTGGGTCACATTGTCTGCGG
GCTCTATTGTCTCGATCCGCGGATTTAAGGCGCAGTTCGCGTGCTTAGCGGTCAGAAAGGCAGAGATTCGGTTCGGATTGATGCGCTGGCAGCAG
GGCACAAAGATCTAATGACTGGCAAATCGCTACAAATAAATTAAAGTCCGGCGGCTAATTAATGAGCGGACTGAAGCCACTTTGGCGGAGTTCAT
TAACCAAAAAACAGCAGATAAACAAAAACGGCAAAGAAAATTGCCACAGAGTTGTCACGCTTTGTTGCACAAACATTTGTGCAGAAAAGTGAAAA
GCTTTTAGCCATTATTAAGTTTTTCCTCAGCTCGCTGGCAGCACTTGCGAATGTAAATTGAAACTGATGTTCCTCATAAATGAAAATTAATGTTT
GCTCTACGCTCCACCGAACTCGCTTGTTTGGGGGATTGGCTGGCTAATCGCGGCTAGATCCCAGGCGGTATAACCTTTTCGCTTCATCAGTTGTG
AAACCAGATGGCTGGTGTTTTGGCAACGACAGCCAGCGGACTCCCCTCGAACGCTCTCGAAATCAAGTGGCTTTCCAGCCGGCCCGCTGGGCCGC
TCGCCCACTGGACCGGTATTCCCAGGCCAGGCCACACTGTACCGCACCGCATAATCCTCGCCAGACTCGGCGCTGATAAGGCCCAATGTCAAGAC
CGCACTCCGCAGGCGTCTATTTATGCCAAGGACCGTTCTTCTTCAGCTTTCGGCTCGAGTATTTGTTGTGCCATGTTGGTTACGATGCCAATCGC
GGTACAGTTATGCAAATGAGCAGCGAATACCGCTCACTGACAATGAACGGCGTCTTGTCAACCATTCATATTCATGCTGACATTCATATTCATTC
CTTTGGTTTTTTGTCTTCGACGGACTGAAAAGTGCGGAGAGAAACCCAAAAACAGAAGCGCGCAAAGCGCCGTTAATATGCGAACTCAGCGAACT

FIGURE SHEET 157

CATTGAAGTTATCACAACACCATATCCATAACCATACCCATATCCATATCAATATCAATATCGCTATTATTAACGATCATGCTCTGCTGATCAAG
TATTCAGCGCTGCGCTAGATTCGACAGATTGAATCGAGCTCAATAGACTCAACAGACTCCACTCGACAGATGCGCAATGCCAAGGACAATTGCCG
TGTGTAAGTGGAGTAAACGAGGCGTATGCGCAACCTGCACCTGGCGGACGCGGCGTATGCGCAATGTGCAATTCGCTTACCTTCTCGTTGCGGGT
CAGGAACTCCCAGATGGGAATGGCCGATGACGAGCTGATCTGAATGTGGAAGGCGCCCAGCAGGCAGCAGGCCAAGATTACTTTCGCCGCAGTCG
TCATGGTGTCGTTGCTGCTTTTATGTTGCGTACTCCGCACTACACGGAGAGTTCAGGGGATTCGTGCTCCGTGATCTGTGATCCGTGTTCCGTGG
GTCAATTGCACGGTTCGGTTGTGTAACCTTCGTGTGGCGACTTTCTTTTTTTTTAGGGCCCAATAAAAGCGCTTTTGTGGCGGCTTGATAGATTA
TCACTTGGTTTCGGTGGCTAGCCAAGTGGCTTTCTTCTGTCCGACGCACTTAATTGAATTAACCAAACAACGAGCGTGGCCAATTCGTATTATCG
CTGTTTTCGGGTGTACGTGTGTCTCAGCTTGAAACGCAAAAGCTTGTTTCACACATCGGTTTCTCGGCAAGATGGGGGAGTCAGTCGGTCTAGGG
AGAGGGGCGCCCACCAGTCGATCACGAAAACGGCGAATTCCAAGCGAAACGGAAACGGAGCGAGCACTATAATCTTGCAGTACTATGTCGAACAA
CCGATCGCGGCGATGTCAGTGAGTCGTCTTCGGACAGCGCTGGCGCTCCACACGTATTTAAGCTCTGAGATCGGCTTTGGGAGAGCGCAGAGAGC
GCCATCGCACGGCAGAGCGAAAGCGGCAGTGAGCGAAAGCGAGAGGGAGAGCGGCAGCGGGTGGGGGATCGGGAGCCCCCCGAAAAAAACAGAGG
CGCACGTCGATGCCATCGGGGAATTGGAACCTCAATGTGTGGGAATGTTTAAATATTCTGTGTTAGGTAGTGTAGTTTCATAGACTATAGATTCT
CATACAGATTGTATCTGAGAGTCCTTCGAGCCCGATTATACACGACAGCAAAATATTTCAGTCGCGCTTGGGCAAAAGGCTTAAGCACGACTCCCA
GTCCCCCCTTACATTTGTCTTCCTAAGCCCCTGGAGCCACTATCAAACTTGTTCTACGCTTGCACTGAAAATAGAAATTAAAAACCAAAGTAAAC
AATCAAAAAGACCAAAAACAATAACAACCAGCACCGAGTCGAACATCAGTGAGGCATTGCAAAAATTTCAAAGTCAAGTTTGCGTCGTCATCGCG
TCTGAGTCCGATCAAGCCGGGCTTGTAATTGAAGTTGTTGATGAGCCGCGGGATTACTGGATTGTGGCGAATTCTGGTCAGCATACTTAACAGCA
GCCCGCTAATTAAGCAAAATAAACATATCAAATTCCAGAATGCGACGGCGCCATCATCCTGTTTGGGAATTCAATTCGCGGGCAGATCGTTTAAT
TCAATTAAAAGGTAGAAGTCGGTAAAAGGGAGCAGAAGAATGCGATCGCTGGAATTTCCTAACATCACGGACCCCATAAATTTGATAAGCCCGAG
CTCGCTGCGTTGAGTCAGCCACCCCACATCCCCAAATCCCCGCCAAAAGAAGACAGCTGGGTTGTTGACTCGCCAGATTGAGGTGCGGATTGCAG
TGGAGTGGACCTGGTCAAAGAAGCACCGTTAATGTGCTGATTCCATTCGATTCCATCCGGGAATGCGATAAAGAAAGGCTC
(SEQ ID NO: 286)

Exon: 6396..5781
Exon: 2158..1969
Exon: 1840..1001
Start ATG: 5894 (Reverse strand: CAT)

Transcript No. : CT9939
GAAGACGACTCACTGACATCGCCGCGATCGGTTGTTCGACATAGTACTGCAAGATTATAGTGCTCGCTCCGTTTCCGTTTCGCTTGGAATTCGCC
GTTTTCGTGATCGACTGGTGGGCGCCCCTCTCCCTAGACCGACTGACTCCCCCATCTTGCCGAGAAACCGATGTGTGAAACAAGCTTTTGCGTTT
CAAGCTGAGACACACGTACACCCGAAAACAGCGATAATACGAATTGGCCACGCTCGTTGTTTGGTTAATTCAATTAAGTGCGTCGGACAGAAGAA
AGCCACTTGGCTAGCCACCGAAACCAAGTGATAATCTATCAAGCCGCCACAAAAGCGCTTTTATTGGGCCCTAAAAAAAAAGAAAGTCGCCACAC
GAAGGTTACACAACCGAACCGTGCAATTGACCCACGGAACACGGATCACAGATCACGGAGCACGAATCCCCTGAACTCTCCGTGTAGTGCGGAGT
ACGCAACATAAAAGCAGCAACGACACCATGACGACTGCGGCGAAAGTAATCTTGGCCTGCTGCCTGCTGGGCGCCTTCCACATTCAGATCAGCTC
GTCATCGGCCATTCCCATCTGGGAGTTCCTGACCCGCAACGAGAAGATGTCCCACCTCTACTCAACATTCGCTCAATTGGTAAGCGTGCACTGCA
AGTCAACAGCCGCCGTCGGAGGCCTCCCAGTGAACCAGTGCAAGCACAACCTGCTCGGTTACGGGTCCGCCAAGCTGCAGACGCTCTCCGACGTA
CAGCTGGAGGCACTAGATCCGTATCAGCGCGATGCCAACGAGCTGATCTGGTCATCGATTATGGGGGACCATCCGAGCGGAGCCAGCCTGGTGAC
AACGAGGCAGCCGCTCCAACAGCCCCTGCCAACTCCTCCTGCGTCCTCTCTGATCATCCTAACGCGCCAGCAACTTCCGCACGGAGCATCCCATG
CCCACCCCATCCAGAGCTCCGGCTCCGCCACCAATCCAATCTTCGAGAGCGGCGAGCAGAAGCACAAATACGCCATGGACATGGACAAGGCCTAC
GGCTACGGGCCGCAGTCCAGCAGTGAGCTCCCAATGGCCGCCGCACTGACTTCAGAACCGTCCAAAAGATTCCTCACCGGACCTTTGGTGATCCG
GGTGCGACCCGATGGCTCCCCGGTGGAGGAGGACAAGATGATGCCACTGCCGCGGGACGAAGACCTGCCCTACTTTCATCTTGGTCTGGCCGCCG
CTCAGCCCAACAGGCACCGCAAGATCGCCACAATCAGCTCCTTAAAGCAGCAGCACTTCGCCTCTATCCTGCAGAGCGACCTCCAGCCACCCCAC
CAGACGCAGAGGCGTCTGTTCCGCCAGCAACAGGCGTAAGATCGCGGTCAGAGGATCCGCAGGCCTAGACCTAAGTCCTTGTGTGAATGTGATAG
AGCAGATGAGGAGATCCTGCATCATAGAGTGCGAGAGTGAACGTGTGAGTCTTCTAGTTGTAGCCGTTTGAGGAGTTTTCTTGAATGCACTTGAG
CTTTAATGGAATTTCGTATCGTATTCGTTTAAGTTTTTTTAATTTTATTTATTCGCGTGCATTAGTCGTAAGATCACATAGAGATTCTTGAGTAA
TAAACCGCATGATGATTATCATTGTTACGAA
(SEQ ID NO: 287)

Start ATG: 503 (Reverse strand: CAT)

MTTAAKVILACCLLGAFHIQISSSSAIPIWEFLTRNEKMSHLYSTFAQLVSVHCKSTAAVGGLPVNQCKHNLLGYGSAKLQTLSDVQLEALDPYQ
RDANELIWSSIMGDHPSGASLVTTRQPLQQPLPTPPASSLIILTRQQLPHGASHAHPIQSSGSATNPIFESGEQKHKYAMDMDKAYGYGPQSSSE
LPMAAALTSEPSKRFLTGPLVIRVRPDGSPVEEDKMMPLPRDEDLPYFHLGLAAAQPNRHRKIATISSLKQQHFASILQSDLQPPHQTQRRLFRQ
QQA*
(SEQ ID NO: 288)

Classification: known_flybase_gene
Gene Symbol: Reg-5
FlyBase ID: FBgn0015801

Celera Sequence No. : 142000013385196
GGAAAATACGGCGAAAAGTAAGGGGATTATTATGCTTTTGTTTGGGGTGCACATGAATGTACATACGTACATGCATATGTACATTAGTACGTAAT
GCTCTATAAGGTAAGGAACTACTCACCATGTACTGTTTGCGAAAATATGCTAGTTACGAAGTCTGCCTAATACTGTCCAAGTTGCTGTGGCGTCC
GTGTGGAAATGGTTATGCTATTGCATCACATTTATATATTCTGTAACTGAGCAAGTTGCTTAACAATTTGTTGCCTCTTTGTTGTTCTTTGTCA
CATATTTTAAAGGACGCGCAGTTTCCGTTTCCAATTGGATTCCGTTTTCGTTATGTTGTTGTGGTACCAACCGACTGCTTGTACCCTAAACTACT
ACAACTACAACAGCACCGTCACATTTGGCCCCCAGGAATGGGTAAATGGTTGTTATGCCTCGCAAATTTAATATATATATAACTTTTTTTCGTTT
CGCGACGCGATGAAAATCACTCGAGCTCTGAACTTGCAGTGTGACCGCGTTTGCTGAACTAGAGATGGCCAAGCATCGATTGCACTATCGATTAC
CTATGCATTCTCAAAAATTCGCATCCACAAAGTAGGAACTATCTGTTTCGACTAACGGTCATACTATGCAATAAATTCAAAATTTGTTTATACTT
TTTGCGGACGAAGAGTTATATATTTCATATTCTGTTTTGACAAAGGATTGCTGTTTGTTTATAATCGTAATACAAAGCATATGCTATTTTGGATA
TAGAACACTAGAATTCCCATAGGCGAACTTATTCAAATATCAAATTAATTGGTTCCTGAAAGCACCCGTAAATTCTTAGTGGCTGAAAAGTCTTA TTGGAAGTCAGAATAATTACTCCACACACTAAGCATCTTAGTTATGCTTTGCTTTGAGCTAATCCTGGTTCTAACTGCCACCGAAAAATGATTCC
ATTGTTTATGCCAGAAGTAAATAAAACAATTTCGAACGTTATACGTTAAATTACAAAGGGAAATCGCTTTATTACCAAATCAAAATCTAGCTATG
GGTACGCCACGCTTAGAAGTTCCTGCAAGGCGAAAAATGCGCGATTAGTGGATGTCCATCCCGGGGATTCTAGCACAAACTCACTTGGTAATGAT
GCCGTCCTTCTTGGCCAGACGCACGATGCAGTCGTCGGACTCGCCCATGCGACGGATCTCGCCGCAGATGGCGTAGGTCTTGGAACCGTCGGTCT
GGCGACCGGTCTCGGGGTCCACATCCACGATGCTCAGCTGCACGGAGGCGTGATCCTTGGCGTGGATGATCCTGTTGGACGCCGAGCTGCAGGGA
AGGGTATCGGCTGGTCAGTAATCCATTCGGCAAATTGTGCGGGGAACACGTGTTTCACTTACCATTTGCGGGGCACGTACAGATCAACATTCTCA
CCGGCGTCGTTCTCCATTTTATTGGGCTGAAAGGTAAGGGACACAATTAGCTTGCTTTTTATTCAGTTTTAGTGGCGGCCACTGCTGGTTTACTC
ACTTTTTTGTAGAAATTTACAAATCTAGCGACCGCAACTCGTCGGTGAAGGCGAAAAAGAGAAAGAAATGACAGCTGGACGTGAAGTTGGCTGCG
CTGCGCGTGGCGCCCCCTGTCGGAAGTTTTGCGTACCAGCTGGTTTTGGGGTGACCAGCTGGCAAAGGTTTTGGTATTTATTTAATTGTACATTT
TTGCAAGATATTTCCATTCCCCTTTAATGAATAGGCATGTTTCAATTTTGGTTATGCACCAAAATGTATTTTAAAATTAAATGATAATTAAAAAA
AAATTTCACTTGGTTTTGTAAGTAAATATCAATAGATTTAAATATATATTTTCCCGCATTAGTGGAAAATACCAAAATCTAATGAATGACATATT
AGATACATGTTCCAGCAGCGACTGGTCACACTTTCGAAGGCCTGAGCGAAGGCTGCAGATTTCGCGTCGGGAAAATTCTATTGCATATTTAGGGG
CGCATCAAGTAAATGGCTCCCATTAGAGTGGCTCAATATATATTATTCGCAAGCTCCCAACTGCACGGACTTACTTATTTAGCATGTGAGTATTG
ATTTTGCAACAGCCAGTCAGTCAGTCTGTGATTTTGTTTTCGCTGGATGGGCGTTCAGCGCGACTGCCCCTTTGACCTCGCTCGATGTCAGCAGCG
ATTTTCGTCAATGGATGCGGACCCCCACTTTTTATTGCCACTTCGCGTGTGTTTGTGCGGCTGTTGGGGCGCCCCAAGTGGGCGGCATTGTTTTC
ATCGCGCGCCATGTCGCGGAATTCGCAGTCCACGTTGCCTATTTATAGGCGTCGCTCACTCAATGAACTCTCTGATCGCATTTCATTGTGAGTTC
GGACTTAGCTTTTTCAGTTGGACGCCAACTTTGGAAGCAATCGGTTCGCTTCGCGTCGCTCGATTTCAAAAATCCCAAACGGCGTGACTTTTGCC
TTATTGTTGTTAGTTGTGTTTTTTCGACTGAAACTTCTTGAGGTGAGATTTCACAAGTGGTTATGCTGCTTGTTGACCTTTTGTGTGTGCAAAT
(SEQ ID NO: 289)

Exon: 1564..1523
Exon: 1451..1393
Exon: 1321..1130
Exon: 1067..1001
Start ATG: 1442 (Reverse strand: CAT)

Transcript No. : CT10101
CGACGAGTTGCGGTCGCTAGATTTGTAAATTTCTACAAAAAACCCAATAAAATGGAGAACGACGCCGGTGAGAATGTTGATCTGTACGTGCCCCG
CAAATGCTCGGCGTCCAACAGGATCATCCACGCCAAGGATCACGCCTCCGTGCAGCTGAGCATCGTGGATGTGGACCCCGAGACCGGTCGCCAGA
CCGACGGTTCCAAGACCTACGCCATCTGCGGCGAGATCCGTCGCATGGGCGAGTCCGACGACTGCATCGTGCGTCTGGCCAAGAAGGACGGCATC
ATTACCAAGAACTTCTAAGCGTGGCGTACCCATAGCTAGATTTGATTTGGTAATAAAGCGATTTCCCTTTGTAA
(SEQ ID NO: 290)

Start ATG: 52 (Reverse strand: CAT)

MENDAGENVDLYVPRKCSASNRIIHAKDHASVQLSIVDVDPETGRQTDGSKTYAICGEIRRMGESDDCIVRLAKKDGIITKNF*
(SEQ ID NO: 291)

Name: ribosomal protein S21
Classification: ribosomal_protein
Gene Symbol: oho23B
FlyBase ID: FBgn0015521

Celera Sequence No. : 142000013384819
TGAAGCAGCTGCAGTTGCTCTACAAAATGGCCACCAGTTCGAGCACCACAACCACCACAACAGTGCCTCCTGTCTTTACAGGAGGATCCCTTAAT
TTGGGTGGTCCAAGTGGCTTTAAGCTGCCACCTCCTGCTCTTAGCCAGGATACCAATACGCTGAGCAATCCTGATCCTCTCAAGAGCAAATCTGA
GATCACCAAGGAGCTTATGGATGTCAGTCTGGAGACGGACACTTAGGTTGTGCGCTTATCTAGTTACTAATTAACCTCTATATACAAATACTTGT
GTATTTGGGTGCTTAGCAAATCTGTGTGTAGTATGGCTTAGCTATCTTTTGTAAATAATATTATAAATAAAACTTAATTTAGTGAATCGCTTTAT
TGAACAGCCTGAATGTAGGCAATAGAAATTTTATGTCAAATCGAGGTCATGTAAAACTCATGTAGAATTGTATAAATGTAAACTAAAATTTACAT
TGGTTAAATATATTAAAAACTGGTTATAAATTAAACATTTAAAGTTTCTGACGTCATTCGTATTTTTTTATTTACAAATATAAACAACTTTATTC
TTTCTTTCTGAGTTACGCTTTATTATGAACTTAGAAATGTTTAAATTAATTACATAAATAGTCAAGTATATTACAAAGTTACATGCTGTATCAAC
GTAGCTACATTATCGGCATATCTTCATGTATTTCCCTACTTGCATAAGTATTTTGTTCATCTAAGCTAGACAGTAGTTATGGGCTATATTATAAA
TTAAACGAAACATATGGGACACAGCAGCTGATCGTGGATCGAAAATAGGATGAGGTCCTTCCACCAAGCCAACTGTGCGCTCTGTGGACATACAG
AATACTATAAATCATTTAGGCTACATACATATCGCCTACAGTTACATATGTAGGCGTACTAAAGTAAATATTACTTATAAATATAGTCAATTTCC
ATTTAGCAGACGAGTGCATCGGTGTACAGTGGTTTTTGGGTTTTTTTTTATGGGTATGAGATGTTTGTGTGTGTTGTGTTTGTGCGAAAAAAAA
CCATGCAGTGTCTATAAAAATAATGTCTTTCATATCATGTTTTTCTCTGTGTACTGAGTGTCCGGTGCCTTTCGGTCTGGAGTTCTCTGATTAAG
GGATTGCCAAATGAAAGCCCCGTAATCTCAATGTGGGAGTAACAACTACTTTAACTTGTGCGGATGATGATACCCGGTGGGTTGATATCTTCCTC
TTGGCTCTCATTTCCTTCCGCTCATCACGAACAGCAGTGGCACCGAATGAGTCTCACTGGCGATGTGCAATCACTTCTCGTTCTTGAGGGGCACA
CCCTCCTCCTGGGTGACGTCGCTGATTCTGACACGTTCTGGAGGATTGTTCCACGGCTGCAGTTCACCGCTGCCAAGGATGGCGAACACCACAGC
TGCCGAGATATAGGTGGCGGCCAGGATCCAGAACACAATTTGCCACGAATGGAAGGATTGCTATTGGTTTTAAAATAAAATATATAAGTAATATA
GTCTCTCTGATATTTTCAGCTAGATTTACTCACATCCTTGTAGGTGAGGGCTCCCACCATCGACGTGGAAAGGAAGCCACCAAAGGAAGACAGCG
TGTTGGCCAATCCGAAAATGGTTCCTCCAAAGTTCGGTGCAATATCCAAGCCATTGCCGAGATAACCAGCGGTGACTGCACCATGGGCAAACAGG
GCCAGCGAGAAGATCGTGACAGACCAGGTGGCATCGTAGCCCAGAAACACTTGCACTATCATCAAAAGACCGGGAATCACAAGAGCTGAAAATAA
GAGAAGATTGTTTATGTTATTCCTGCAATACCTTGAAATGATATTTTTGAATTTACTTACCAAAAGTAGTGAATAGTTTCCTGGTGGCCGTCGTG
CTCAAAGTACCCTTCTTGCGCAGGTAATCAGCCAGGTAGGATGAAGCCACAGCCATAACGTATTTACCCAGATAAGGCAGCGACGAGAACAAACC
ATTCTGTAGAAGAACAAATCTATTAGTAAATATAAGATACCCAGATAAGCCGTGTCCAACAAACCCACCTGTTTGATATCGAAGTGCAGAATCTT
GGACATGAAAGTGGGCAACTGATTGACCACAGTGAAGAATCCAAAGACGGCCAGTCCGTGACAGATGATGATTGCCCACACAGCTGGAGAGCAGA
GCAGCTGACCCCAGGGCACATGGCTCGGACGCTTCTTAGAGGTAGTGGTGCCAATGGCCTCCTCAATCTCCCGCCGCTCCTCGGCTGAAATCCTG
GGATGAGTGGCGGGTGTCTCATAGACAAAAGTGAACCAGGCCAAGGACCACAGCAGACCCACGGCTCCCGTCAAATAGAAAACACTGGCCCAGCC
AGCGACGGAGATCAGGTAGCCGCAGATGGGCATGGTGATTGCAGCACCAAGCGAAGAAGCTTTCGGGTCAAGAAAAAATATACGTTAGGGATAGG ACATTTTTATAATACAGGTATGCAGCCTCTATTAGGCTTTGTTCCTACGGACAAAGAACTGCTTGACTTACCCATCATGTTGGACATAAACTTGG
AGCGCTCCATGGGCGGAATCCAGACAGCGGCCACCGGGTGAATGGCTGGCCAGGATGCGCCCAGCATGAAGCCAAGAACAACTCGCACCACGATG
AGCACCACGTAGTTGATATGCGCCGCCAGCGGCGTGATCAGGGTGAGCAGACTGGCCCACAGCATGGAATGTCCAAAGACGCGGCGTCCACCGAT
CAGCTCGGCAAGACGACCGCCCGGCAGTTCGGTGAGGATGTAGCCCCAGAAGAAGCAGCCCAGCACGAAGTTGGTCTGGTAGCTGTCCCAGGGAA
AGCGCTCCTCGTACACATCCACTCCATCAGGCGATGCGGTGCTATTGGCCGCCGTACTATTCCCCACTAGAGTGGCATTCACCGCTGATGTGACA
TTGGGTCGGACCATGTCCACGATGGCAATGGTGAGGTTCACTCGCAGGGCGTAGTTCAGCATGAAGCCGAGCATGGTCAGCAGGTTCAGAACTTG
GCGGCATGACAGAAAGTCTGGAAGGGAAGGGAAGAGCGGTGTCCAATTAATAATAGAATCCAAGGCATTGGATTGGATTGGATTCATTGATACTG
TAGTACATGGCGAATAAGTCGGTGCTTCGTCGTCTGGGTCGTCGAAAGGTTAGGCACTTAAAATTCAGCTCTGGAATATTCCCAAGCTGCCGAAA
ATCAGGCGACCAGCGGCCAAAGCAAAAACCCACCCAAGAAGCGCCCCAATTTGTGATAAGAAAACTATACTACATTTAAATTGAACAGAATAACC
TTTTAATCGAAATTTAAAAAAAAAAATCCACCTGGATTATGATCGCCTGTAATTGCATTCAAAGCTAATACACGTTTTGTTTACAATCATTTTAA
CTGATTTGTTATCAACTCACTACATCCACTACGCCCACACTACACACTTATTAACTGATGTAATCTGTTGTTTTCATTACACGATGCAGCCCAGA
TAAAAGCATTAATTACCCATATTAATGAGCCAATAAAATCGCAATCGCACAAAACTTAACAGTCGTTGTCAGGTGACCTCAATAGCATATCGAAT
GGGCCATGAATTTGATTTGAGGATCGCCGGTTTGTGGGTGCAGCTGGATTTCAAAAGGAGAAGAAAACCAATCAAACGGAATCAGCTTCATTCGA
AGCCAAAGACATGAAGGCGAAGATCATTAAGTGGTGTCCACAATCAACACAAACTGGGCCTGTCACTTTGTTTTTTTTTTTTTTTTTTGGGACG
CTTATTAAGTGGCAAAGTGCATTGTACGGATTGGGTTGCATTTTTCGCAAATCACATTAATAAATTTCAAGTGGCATTGAACCGCAGTTATAACC
CGCTCTTCAATTTCAGGGAAATGCTCACAAGTGTCGGTGTAAATTTATAAGCCACCAACCCGATTGTAATAAATAATAAACTGGCTTCCAGCGAC
TTTCCCATGCAAAAAAAAACAAAAAAAAAAAACAACGCTATCAGCTGGGCGAAGCGACTATCGGGGCCAGTCTATCGCCTGTCTGGCCGGGACACG
CCCACTTCGCTGATTATTGCCCCAATATCATGTTAATGTCATGCAAAAAAAATACGAAAATAACGCCACTCGGCCGCTTGTCTAGACATCGGTGA
GCATCATCAAACGAGCGCGAAGCAACAATAAAACGAGACACTCAACTTGTATTCAAATTAGCACTCGAAAATAACCAAAATTCGAAACATCAAAA
AAGCGTTAAAAAAAAAATATACAAAATCTCTAGTCATGTTTGCTATAAATTCTTGATTCCATATAAAACCGATAACCAGAAAAACGTGCCCAAAA
TACACAAAATTATAAGTAATTCCACAGAATATCGGCAAGGTTTCGACTTAGACCAGTTTCTTCGCTCAAATCGCATAGAATTGGATCGAAGCAGA
ACTATATCCAAATTTTTGGGCGATCTATTGTGAACTCAGGAGGTGTTTGGAAAGTTTGGATCATTAACAAAGTAGCGCTCTGTTAATTTGTGGGC
CATGTCTGGACACCTGACACCTCATCATCAGCTCAAATCAATGCTAAATAAGCGTGTGCCGCAAATTACCGCCACTCCATATCGATAAGGATTGA
TTTATACGACTTCCACTTGCACGGGGGAAATAAATTATAATAATAAACTAATGTCATAAACCGGCAAGGACTATGAACTTAAAGTGGTAAATTCT
CTTATCTCAAATAGTAGCTAAAAATAATTCTCAATGTGTGTGGGAATTTCTAACTATAAATCAGGTTCGAAAACTTGCACTTAGATTGGTAAACA
AGTTTTAAGGGCCTCTATTTTCTATAATGAATCAATCCAGTTATTCAACTTATAAAATTCTATATCCATTAAGCACATATTTCGGATGATAATTA
AATTGAATAGAATTCGAGACAGAGCTCTAATTTGTCGGAATGAACTCATCAAGGGTTTTCTCTAACCGATCTTACTCATCAAACGAATTCTGAAG
TCTGTGACTCCTTCCGAGAATCTTAATGATTGAAACTCAACTCAGACTTCTTGATTAATTGTCGCCTCGAACGGTTCATTTGTTTAAAGCTTTGT
TTACGGACAAACTATTGCTTCGCATTTTCTTTTGTTGTTATCTTTTTGGCAATAAATTAAGTGAAGGCCAGACTTGATGTTTACAACCGAGAGGC
AGAAAAAACCGGCTAAAATCGTTCGAAATTATTTGGACCGACTGGATTTGGACAAACTTTTCTCAAAATTCTCAGAATTTCGCCTGTCTCGTGCA
TAAACTTATTTGATTTGGCTGCGTTTCATCTCGTTTCCTTATTTTATTTAATTTTATTTCGCTTTTTGGCAGCAATCTTTAGCCTTTATTGGCTT
TCGTTGATGCTCTACTTGAGTTTAAACAAGTTCGCCGCAGTCTGCGCCAACATAAAAATCCCATCAGAGAAAGGCAAAAACTTTATAAATAGCCG
GCAAGTAAATAAAACGAAATGAATACGGGCAAAACGTGATACTTAAATTACCGCTTTTTACGATCGAGCAACAAGTGAATCTGAGTTCGTTACTG
GGTTCATTGATTTCTCGGAAAATTCTTAAAATTTATTCGCCAAAACTGCGAATCAATTAAGTGGCACTTGAAGTTCAGATCAGCACGAAATCGAT
TATTTGCTTTGCCTTCAAATAATCATTTTTAATATTTTCGAAAAGACGCATATCCGGCACTTTTTGGGGGGTTGACGCAAAAGTATTTTCGAAAA
TGTCTTGTACGATTCTAAGTACATTCCGTCTGTTATTCTTTTTAATCTATTTCACTGGTTTATGTATATTTTGTTTTCCTTTACACTTTCGAATC
TATTTATACAGACGCTCTATCGTTCGAATGCGGGCACTGGGTACACACCCACCGATGATTATCTTCTATGTCCGTCCACTCTCGATTCTCTCTGG
CCATTCCTGACCTTCAAAATCGGAATGGGCTACATAGACTATACATTGTGTTGGTGAAAGTTAGCCACCGATATCGTCATCAGCTTCGATCAACT
GATATATATTTTCTCCTCGAATGGATGGAACGCATGTGATCGGCTTTCGGATTTTCTGGTGGAATGTCCTCAGCATTTGCGTGGGCACTATTGGT
CTGGCCCGAAAATTTTCCATTCATTCGACATACGAAAGAAAGGCCCGCAACCGACGTCACACAAATGCGCACTTTTCCGTCAAGGTGCCAAGTCA
TTTTCCTGTCACGGGATCGAAGCGGCGGGCGCAACGTGGCGTATGAGTTATGGCGAAGGCGCGCCAGCCACGAGCCCACTTTTCAGATTCGATTT
GCAGCGATTACAACAACTCCCACACAGCCCAAGATTTTCAATCGTATGTAGTCACAAACGATTTGTGCCCATGCCGGGGGAAATGCAAAACACTG
TTTTGCATTTTGAGATCAATCGATTGTTTCCGAACTTTTCCATGTGATCATTTCTACAGTAGATTGTCCTCGGCATTGTGTATTTGTGGGAATTA
ATCAATCAGAACTTCATAAGCATAACTTTACACTTTCAAATCACTGAAATAAATCATTTGCATATCTGTCGGTAATATGTTTCATTGCTTTCAAA
CGCCAAAAACGCACTGTATCGAATATTGTATCTGTATCTGTCGGATGGCATGACATTGCCGCGTCGCCTTCTAGCGGCAATTATTGGCTTTGTTG
TGCTGGCCAACTGCATTTCCGTTTGTAACTGATTTACGGAACTGGCCTCGTTGAAAGCGAGTGAATTGTAATGCCACGACGCCGACGACGACATT
GTTTGTTTTCGAGTTTCTGTTTCTGTGGAACTGGTTCTACTTCAACACAATAAGCAATAAGCTAATTAATTGCTGAATTATTGTGCCAATTTGCT
GTTTGTTGAGGGGCACACACAGCAGCCTCACTTATCACTTTTGTTGGACAATCGACCATTGTGATTAACTGGCCATCTCTCGAGGAACTCTCCCA
TCGCCATTGTCCTAGATTCGTGCCTTTGATTCGCACTGGGAAATCTTCCATGGAAATTTACAATTGGAACCCTGCACTTGTGGCGTTTGCCGTTC
AAAGTGCAATCGGTCTTAAGAAGGAGCAACTTGTATACATCGATTTACAGCACCAGCCCCCAGACTGATAAGTTTATTGTACGGAATGTCTGATG
TCTGAAGCTCAGGAAAGTCAAAACTTTTATTGACTTGGCTGCATTTGGCCATAAAGTGGCCCACGAAGTGGCCAGTTCGCGAATCACTTTAATCC
AGCATAAGATATGACCGGTATGAGCTGTTCTACACATGAATGTATCTTCAAGTTGTCATTTCCTTCGACCGTATCTCATAGATGCACGTGCCGGC
TAATGAAGAGCTACAGGTTGTAAACAACTTGTCAGGGGTCTCAGGCCCCGTGCTATGTAAACATTTATAGCTGGCAATAAACAATACACATATAC
GTATATATGTATAAAAAGGGGGCTCGTCGCCAAGTGTCAATTATTTTCTGGACCCATCAAAATTATCAGCAACTATTTTGCAAATAGTCGAAAAC
TACCGACGAACTTTGGCACTTGATAGCGCGACACGCGTTGCCTTGACTATGGAGAGTCTTATAAATATATATGTAGATTGGAATGGAAATACATA
CATGCTAATTTATAAATATGATTTCAGAACCATCAATGGAGGCTTGCCTCAGCACATTTGAATGATTAAAGGGTCTTGCGGGTCAAAGCCAGCAT
TCTTTTTTTTTTTTGTACTGTCTGGGACTTGTAGATTTGATTAGCGTTGAAACTTTTAATTGTAGAAATACTTGAAATTTCTGGTTATAAATTCA
ATAATAATTAAGTGTGCCATGTGCAACGGAAGTACAACGCAAGACATGAGATTATAATCAAATACGGCGTAAACCACTTTGAAAATTCCAAGAAA
TGGTTTCAGCTCAATTGAAAGCAATCTCGTTATTACACAAAAACCAGAAAACTAGACTTGACTTAATGCATATTAAGCCGACGGCTAGAACAATT
GAACCGTGTTGCGGAGCTTCAACAATGGAGTGCCAATTATGAGAATCATTAATAAAAGAACTAAAGGATCGAGTAAACACAAATCGATGTAAAGT
GACAAAAGTTTAATAACAATTTATCGTAAGCGAAATGAGCCGAACACATGCTCATTATTCATTACTTGGCTGTTTGATTAATTCCAGACGACGAC
CCACAGTCAGTCTGCCAAGGGTGAATACCCGACGGATTCAAATGTGGATTCAAATGAGAATCGAAAGCGGTTGCTCTGGGGAATTTACAAACGCA
AATGAATGTGATTGGCCAAGCTAAATACCAATTAAATTGAAAGCTTTTTTAGAAGTAGTTTATAATAAATTATGGGTTTTATGTCAAATTACAA
TTGAAGTGTAATTTCTCTCTGAAAGTAACACTCATTTATAAGCCAATTTAATATTTAATATTTGACTATATACGCGTTCATCAATTTGTAAATTC
CCACTTTTTGTGATACCTTTAAATAGCTTAAGCACCTTGAATTTTGTTTATACAAAGCACAATGTCAAAAAACAATAAAAACCTTTAAAAACCAG
ACATGAATCACACCTTCCTGTATTATTTGCAATTGACTGAGTGACTGAGTGGGTGTGAATTACACGAGCTTGTAATGAATAACCATACTATAAGC
TGTCTAATCGATATGAATTTCAGTTTGTTTTAGTGTTAATTGAATTTGTAATTGTCTCGTGCGACAACGTATCTAATTAGCACACTCAAAGTGAG
TTTTAATACCAACTCCCCCTAATTAGAGGCTATAAACGAGTGCATTTCGGAATCTTGGAATCTTGAGACGTATTTCTTACAATTTTTTAATATTT
TCCTGCTAATTGAACAATTTGCTCTTTGGTTAGAGCTCGCCGCTTCACTATCATTCATGATTGCTCACGGGATCGACGAAATGTGCACTCAAACA
TGCGATCAACCCACCCGCCACCACTTCATCCTCACCTCACCTGTCTGATTCCACGATTGTCTGGCTCTAAAGTGCTAAACATTTTCAAAAGTACG
AATTAAATAGTAAACAGTCGAATGACCGTCGTTGGTGGGCTATTAAAAATTCACAACACAACAACCACACACAAAAAGTGGTTCAATTAATTGCG

FIGURE SHEET 160

AAATTTTACTCGAAATTTAGTCCATGAACTAAGCTTTCCATACGCAAAAACGGAACTTGAATTGTTCAAAGACTTCAGGGGGGGGGGGATGTGTG
GTAGACTAGACCAACTAACGTGCTTAGTTAGCGTGACTGTGCTAATTTGTTTGCATAGTCTAATGCGTGGTACTACGTGGAAATGTCATAACCAT
GGCGTCATGAGGTCGCCCAACTGCGCACTCCAGCTGTCCCACGGCGTGGGCGTGTCCTTGTCCGTATCGATGACATCGCGAGGATTCGAGGAGTG
CCTGTCCTATGGTATAAGTTCCACCAGGTGTCAATGATCGAGAAGTTGTCAAGGTGTCGCGAGGTTGATACAATTAAATATTTATCACATTTTCA
TTGAAACAACTGGGTCAGGTTGTCATAGCGAAAAAATAAAACCCATTAGATACTTTCGATTATGTTATCTGTTATCAATATCTACATATTAGGAT
TTCTCTAACAAAATTGGTATATGGCCATTGAGAATAATCTGTAAATCGAACAGCTGACGAACCAAATGAATATTATAAGCTGATATATAAACTGA
AACAGTTTTTGATAATCTTGCTGAGCTTTAAGCATCTTATATCATATATCTTATATATTTTTTACTGCACACAAAAATCTCGAATATTCGAATTG
AAAATTGACATTAGAACGATGAACATTTGCAATTGACCGATGGAGGAACCGGAAAGTCAATCAGCATTCAATTGAATCACAGTGCCCAATTGATT
TGTAACCTCAATACAAGTTGTCTCGTTGACACCAATCAAAGTGGAGGCAGGAGGAGTCAAATCGATTTGTTTACGTTAACCGAGTTGCAATTCAA
TTGGCCATCAAACATGGGCAATTCTGCTCGACTTTCGAGCCCACTGACCCTGGCGCTCCCTCATTTTCCAGTGGCGTCATGCGGTTTCTGGCCGC
CTTATCGAGGAAAAAGAGGGGCTCGGCTGTTAAAAAAAAAAGGCGCTGCGGTTCACTGGGGGAGGCACATTGTTCTGGCATTTTCGACTGGCCAA
ACAGCAGGTGCAAACTGGAAACTCAATACAGTAACCATAGATGATCTCTAGCTATTTCGTATAAATATTAAATTTCAACTCGAAAGTTCTCAAAT
CATTATTTACTAATATTCAAATAATCAGTGTGCTGGCTATGATATAAGCAGGATGTTGGGTGGGCACCTATCATATCACATATGATATCATATCA
CGTTATCTACTTACTTCGCACTCTTTGCAGACCTCCTTTCTCCGTGTTGGACATGACGCCTCTAAGTGCCGGCTCTGCAAGTGGAAATATACCAG
AGGTTAGACGAATTTTATAAATTGGAAACGAAATATGGCAGGCGATGTGATAGACATCTAGAAAATGCGATATAAATAGTCTGCAGAGTTAATGA
AACTTTTTACGAAGTAACCAAAATCATGGTTATACCTTCTTTTTTTTTTTTTGGCTATCTTATCTTATCGCCGCCGGTGTCTCGTGTTTGTACCT
GAACGGTTAAACCGATATGCATATATATCATTTTCAGACGTTCTTTGATAACCACAATTGCACTGGCCTGTCATTATCTTTCTTTTGTTCAGTTG
TGCTGGCGCCGCTATAAATTATTGAAACACTGTTGCAGCAATGGTGGTGCAAAGGGAAATTCGTTGACTATATATGCGATTTGTTGCATGCTAAT
TGCCGCTAGACACGTGCATGTGCGGCACAGACAGGATCTTGGCCCTGGCAACATGTGTAACTTGGCGCAATCAATTAACTGCGAGTGCTTAGATG
GCGTTTGGTCAATTTGGACTGCAAATATTTGCTGGCGGCGTCCTGGCAACAACAAAAATGGCAACAAAACTATGCCCGCATGTGTGAGGAAAGGA
TATATGTATAAATATACATATATACAGACGAAATTATTGTCCTTGCCTGTGTGGCATGTTGCCTTGTTATTAGGCCCGATGAAAAAGCGGCATCT
GCCAGCCAGTCGTGTGGGCATTGACTATATACGACTTCTATATGGTCACATGTCGTCATACGTCATCTTCCTACAAGTCCGTATATGCGGGAAAA
ATAACTCAATTCGCCACTTTTATCGCGGGAAAGCAATTATGTTTACAGCATTAGTCATCAATAAGCCCAAATATATAAAGTACTTAAATATACTT
AAGTGGCTTGCATTGATTTCATATAAAATGCTCAAAATGTTTTGCTCATGAATGAAACTTTTAATTACAGTAATTATAAATGGCAAAATTGGTCA
GATATCAGTTTACAATTTTAGCCGCAGAATTAATTTGTATATCACGTTTATCTTAACTAACAAAGCACGATTAAATCACAATTTAATTTATGTCA
ACATGGCTATAGTTAGCCCTCGTTTAATTAGTAGTTTAAACGTTTTGCGCCTTGAAAAACCAATTAATCACATTAATAGCTGTAGGAAACTAAGC
AATTATGACACCACTAGCAGGTAAACGATCTATTTTAATTAGTTACTTACTGACCTAAAAAAACGGAAATAACACCTTTAATAAATATGCATCTT
AAAACTAAACTTTAAGTAATTGTAATAGAATCAGATTGTAAGCAACATTTGCATTGCACGAACTGGAAACCCACCTTGCACTCGACAATAACTAA
CAAATGTTAGTTGTTTATGGCAAATTATATAATTTGTTTGGCACCAACCGATTTGCAAACGGTTTTCGTATGATTAACTTTAGCTCCGATTTCCA
TAAAACAAAACACAGTGAACGAACGAACGAAAACCGCCAAGAAACCGCACGTGTTTTGTGTTTATTTTTATCTGTTCTTCTCGTTCTGTGTAATA
TCTCAGATATTGAAGTATTGAGATATTGAAAGATCGGTAGATTGGGGGGTGAAACACACTCGCACTCCCGAACAAGAAACGGTTTCAACAATGCC
GGATGGGACAGCTGTTGATTATTTTTGAAAACGTCAAGCGACGAGTTTTCTAGCGCAAGCGCAGGCAATTCTAGAACTGTTTCGAAATCGAAACT
CAAAACGCTGTTGCTGCCGTGGACAGTTGCTGCTGTTGTTGCTCTGCTGTTGCTGCGTGCTCGTTGGAAGAGCGTTGAAACTGAACTGAAAATGC
GGCCGCTCGTCTGCGGCTTTTTCTATACTCCGCCGCAGTCGCAGTCGCCGTCACCGTCGATGTTGCTGTTGCTGTTGTCGCAGCGACTGCTGTTG
TTGCTGCTGTTATTAATGTTGTTGCTGCTGCCGTCGTTCTCGTTGCTGCTGCTGCTTCTGTTATGCTGATATAAGTGTTGTTGCTGTTATTAGCG
TTGTTGTCGCTGCTGCTGCTTCTGTTATTGCTGCTGTGCTCGTGTTGTTGCTGTCGCTGCTGCTGCTGTTATTTCTGTTGTTATTTCTTTTGCTG
CTTCTGCTGACGTCTGTTTTGCTCAGCAGCATTACCATCTTTGATGAGAATAGTGTTAGTTCAAAATTGAGTTAAATTCGAATAACAATCTTACT
CCATTCGCCGACCTTCATTCAGATTCAGATGACAGGAGCTTATTTCGGTGATGAAGATTCGCGTGCAGCGCGGATTGGATAAACCCAACCCAAAG
GACACAGGATTCCTGAAGATGATGCGATCTGTATTCAAGTGCTGGTCATCTAAAGATCGTCACTCCGTGGATTTGCCCGCTTCCATTTCCAGCTG
GGATCGCGTCGAATCGCAGCGGATAGTTGATACCCATTTGCCATGCGTAGCCAAAAGTGCTTATCAGCACACGATTCGGCACAAAAAACTGCTGC
CGATACAGCAAAACGGTACCAAGTGCTCAATTTACGCGGCAATTTTGAAACATCAGTGGTTTTTTGTTTTGACAGATTTTTTTTTTTATTAATAG
CTTATTTGGACGAGAAGCTAAGATGCCAAGAGCAGATCAGTCTGCAAGCATGATGAAATTCCACAAATTTTCGCATTCAGAACTTGTCTTTGTGA
TATAAACTGTGATCTTTACATAGCTTAAATATAGAATACCATATCTATGAAATAAAAAGTACCGCATCAAATGGAGAATCGCGTCCAGCGCTCCA
CGAGACTGGGTCGCGGCGAGGCCCTGT
(SEQ ID NO: 292)

Exon: 12327..11855
Exon: 10524..10465
Exon: 3057..2542
Exon: 2434..2064
Exon: 1998..1866
Exon: 1795..1554
Exon: 1485..1001
Start ATG: 10504 (Reverse strand: CAT)

Transcript No. : CT10168
CTCTTCCAACGAGCACGCAGCAACAGCAGAGCAACAACAGCAGCAACTGTCCACGGCAGCAACAGCGTTTTGAGTTTCGATTTCGAAACAGTTCT
AGAATTGCCTGCGCTTGCGCTAGAAAACTCGTCGCTTGACGTTTTCAAAAATAATCAACAGCTGTCCCATCCGGCATTGTTGAAACCGTTTCTTG
TTCGGGAGTGCGAGTGTGTTTCACCCCCCAATCTACCGATCTTTCAATATCTCAATACTTCAATATCTGAGATATTACACAGAACGAGAAGAACA
GATAAAAATAAACACAAAACACGTGCGGTTTCTTGGCGGTTTTCGTTCGTTCGTTCACTGTGTTTTGTTTTATGGAAATCGGAGCTAAAGTTAAT
CATACGAAAACCGTTTGCAAATCGGTTGGTGCCAAACAAATTATATAATTTGCCATAAACAACTAACATTTGTTAGTTATTGTCGAGTGCAAGAG
CCGGCACTTAGAGGCGTCATGTCCAACACGGAGAAAGGAGGTCTGCAAAGAGTGCGAAACTTTCTGTCATGCCGCCAAGTTCTGAACCTGCTGAC
CATGCTCGGCTTCATGCTGAACTACGCCCTGCGAGTGAACCTCACCATTGCCATCGTGGACATGGTCCGACCCAATGTCACATCAGCGGTGAATG
CCACTCTAGTGGGGAATAGTACGGCGGCCAATAGCACCGCATCGCCTGATGGAGTGGATGTGTACGAGGAGCGCTTTCCCTGGGACAGCTACCAG
ACCAACTTCGTGCTGGGCTGCTTCTTCTGGGGCTACATCCTCACCGAACTGCCGGGCGGTCGTCTTGCCGAGCTGATCGGTGGACGCCGCGTCTT
TGGACATTCCATGCTGTGGGCCAGTCTGCTCACCCTGATCACGCCGCTGGCGGCGCATATCAACTACGTGGTGCTCATCGTGGTGCGAGTTGTTC
TTGGCTTCATGCTGGGCGCATCCTGGCCAGCCATTCACCCGGTGGCCGCTGTCTGGATTCCGCCCATGGAGCGCTCCAAGTTTATGTCCAACATG
ATGGCTTCTTCGCTTGGTGCTGCAATCACCATGCCCATCTGCGGCTACCTGATCTCCGTCGCTGGCTGGGCCAGTGTTTTCTATTTGACGGGAGC
CGTGGGTCTGCTGTGGTCCTTGGCCTGGTTCACTTTTGTCTATGAGACACCCGCCACTCATCCCAGGATTTCAGCCGAGGAGCGGCGGGAGATTG
AGGAGGCCATTGGCACCACTACCTCTAAGAAGCGTCCGAGCCATGTGCCCTGGGGTCAGCTGCTCTGCTCTCCAGCTGTGTGGGCAATCATCATC
TGTCACGGACTGGCCGTCTTTGGATTCTTCACTGTGGTCAATCAGTTGCCCACTTTCATGTCCAAGATTCTGCACTTCGATATCAAACAGAATGG TTTGTTCTCGTCGCTGCCTTATCTGGGTAAATACGTTATGGCTGTGGCTTCATCCTACCTGGCTGATTACCTGCGCAAGAAGGGTACTTTGAGCA
CGACGGCCACCAGGAAACTATTCACTACTTTTGCTCTTGTGATTCCCGGTCTTTTGATGATAGTGCAAGTGTTTCTGGGCTACGATGCCACCTGG
TCTGTCACGATCTTCTCGCTGGCCCTGTTTGCCCATGGTGCAGTCACCGCTGGTTATCTCGGCAATGGCTTGGATATTGCACCGAACTTTGGAGG
AACCATTTTCGGATTGGCCAACACGCTGTCTTCCTTTGGTGGCTTCCTTTCCACGTCGATGGTGGGAGCCCTCACCTACAAGGATCAATCCTTCC
ATTCGTGGCAAATTGTGTTCTGGATCCTGGCCGCCACCTATATCTCGGCAGCTGTGGTGTTCGCCATCCTTGGCAGCGGTGAACTGCAGCCGTGG
AACAATCCTCCAGAACGTGTCAGAATCAGCGACGTCACCCAGGAGGAGGGTGTGCCCCTCAAGAACGAGAAGTGATTGCACATCGCCAGTGAGAC
TCATTCGGTGCCACTGCTGTTCGTGATGAGCGGAAGGAAATGAGAGCCAAGAGGAAGATATCAACCCACCGGGTATCATCATCCGCACAAGTTAA
AGTAGTTGTTACTCCCACATTGAGATTACGGGGCTTTCATTTGGCAATCCCTTAATCAGAGAACTCCAGACCGAAAGGCACCGGACACTCAGTAC
ACAGAGAAAAACATGATATGAAAGACATTATTTTATAGACACTGCATGGTTTTTTTCGCACAAACACAACACACACAAACATCTCATACCCAT
(SEQ ID NO: 293)

Start ATG: 494 (Reverse strand: CAT)

MSNTEKGGLQRVRNFLSCRQVLNLLTMLGFMLNYALRVNLTIAIVDMVRPNVTSAVNATLVGNSTAANSTASPDGVDVYEERFPWDSYQTNFVLG
CFFWGYILTELPGGRLAELIGGRRVFGHSMLWASLLTLITPLAAHINYVVLIVVRVVLGFMLGASWPAIHPVAAVWIPPMERSKFMSNMMASSLG
AAITMPICGYLISVAGWASVFYLTGAVGLLWSLAWFTFVYETPATHPRISAEERREIEEAIGTTTSKKRPSHVPWGQLLCSPAVWAIIICHGLAV
FGFFTVVNQLPTFMSKILHFDIKQNGLFSSLPYLGKYVMAVASSYLADYLRKKGTLSTTATRKLFTTFALVIPGLLMIVQVFLGYDATWSVTIFS
LALFAHGAVTAGYLGNGLDIAPNFGGTIFGLANTLSSFGGFLSTSMVGALTYKDQSFHSWQIVFWILAATYISAAVVFAILGSGELQPWNNPPER
VRISDVTQEEGVPLKNEK*
(SEQ ID NO: 294)

Name: Na+-dependent inorganic phosphate cotransporter
Classification: transporter Celera Sequence No. : 142000013384407
AATTATTAAATTTTTGAAATTTTTTGAAAAATATAATCAGTTTTCTTTTGGATAGCAACAAAGAGAGTTGAACAATATTAGAATGCCATGCCCCA
CTAAACTCAAAATTAAATTTCCCATTTAACTATATTTAAACATGGAAACGGTAATTTTATCGAAAATTTCGATGACTTACACCCTTATCGAAAAT
GCGAACATTTTTATTTCGAATTTAAATAGTCATATGTGTTTATTGGCCGTACAATAAGGAAAAATCCTATTTCGACAATTGTTTTTATTTCAATG
ACTTCTGGAAAGCAACGTAGCCCATGTTCCTTTTCCCCAATAAAAATGCGTTTTGCAGATAAAGGAAAAATACATTGATTGTGGTAGCTATTTTC
ATTCTTATGAATACACACATAACATTTAAATACAAATACATTTACAATTGAAAATTTTCTCTACATATACAAAATATTTAATTTAAAAATAGGTG
AAAAAAAAAAACAAGAATAAATTGTTGTCCCTAGGTTCGTTAGCTTAGTAAACACAATTGATGCGCCAGCGGCAGCGGAAGCAGCAGCAAAAAGA
AGATCGAATTCACTCAACACAAATTAAAAAAAAAAATTGACTTTTCTTTTTGTTTATTAAAATGGCTATGGTGATCGGGAATTAAATTCTTCAAG
TAAGCAGCCTTTTTTTCTGTTTCCCATTTCTAAATAAGAAGACATTATTCTCAGACGAGACAGAGTATTGCTTAGTAAAAACAACTTGAGGTCGA
TTTCATTCAGTTTTAACTCTGCTTTCAGATTTCTTCTCATGATTAATATTTTTACACGCAATATCAATAAATTTATTCCTCACAGAATTGAAAGG
AGAAGTCAAAGCGTTATTTAGAACTATTATTACATGCCCATAAATATTTTTAATGTTAGTCGTACATTTAAAAGCAAATTGAATTTAGTTAATCT
CTTCCACAGGTTCCTCGCCTTTTTTGTTTTTTTTTTTTTTTTGGATTTTTTGTATTTTGTTTTGTTTTGTAACTTTAAAAGTTTCTTCAATTAA
TTGAGTCGCAAAATGAATTTTTGATTGATTTCATTGATTGATTGATTTGATCGATAGATACCGCCTTCTGTTTTCTGTTTCGTGCACTCTGAAAT
CTCTGATTTTGATTTTGAGTTCAATTTCAATTTGAATAACTTCTAACACACATACACACACACGGGTATTTAATATTGGTTGTTTGGAGAGAGAA
TTGCATATAACGCGCTTTGTGCTAGGGTTCGCTTGGTGTTCTGCTCGTGGATTGCATCGATTTATAGTCCGAGATATCGCTACATATATCGTCGA
ATATAGTTTGTCGGTTGGCCTCTACGTTCACGTAGCTTGCTTTCAAAATTCGTTGTGTTCTTGTGTAAAAAAGAGATCTCAAAACAAAAGCGAAA
ATTGCTGATTTCTTGATTGGTTGTCTCTGGTGGTAAGTAAGTTAGTTAGTTAGTTTGGTGTTCTAGTGCTGGCAAAAGTCCGGGAAAAAGTTTTT
GGGACTCGCAGACAGGGATTCGGATTCGAATATTGGTGGGGAGTTAGCTGAGGTTAGGTCCATCGACCCAATGACTCATAGAGCTTAATAGTTAA
ACTACAGATCGGCTCGTTATTTGTACGCGGCTACATGTATCCGTATCCGTATCTGAATCGCTACATCTTAAGTAAGTATGTATATGTATTTCCGA
TTCGGCATCGGCTGGTAATTACAGCTAAATATCTTGTATAATTGTATATATATAGACAGAGAATAGCGAACATTATTGCTCAGACCCATTAGAAT
AGTTGTTGGCTGCTCCCGATGCTGATCCTCCTCCTAGACGTGGCAACCGTTTTGAACTGTTTAATTAATACGGTGTATATACTTTATCATATATA
ATATTGGTGTTTTGCTGTTGCTGCTTGAAGACTAATAGTTAACGGGGCGGCGTCCACGCGGCTTGATCTTCTCCGATATCTGCCACATCTCCTCC
TCGCCCATAAAGTCCTTGAAGTTATCAAAGAAGCGTATAATGCGCTCGTTGCGTCGAAATGGATAGGCACTGCAGCAGAAAAAGAAAATTGCGTG
AAGTGAAGTGAAAGAAGTGATTATAATTGAATGAAAATTGATAATTACCATTTCTTAAAACGTTTCATGTTGTCAATTATGTTGTACTGCTGCCA
GCGCTTGGAGAAGTTTATGACGCCCTTGGACAAGTAGTCCTGGTTGCCCACATGCACAAACGTTAGATCCTGCAGAATTAGGCCGCTGGAACGAA
CGAATTGATAATTAGCTTTGGCTTTCGTGATTCTAACAAAAAAAGAAACATCAGATCAGATCCTTACATGTAGGGTATGCAGGGCGGATTAGTTT
CGGCCAGCGCCTGTCGATAGGCGCGAAAACTGGAGCTGGAATCGATGAGGGCGCAGAATGATCGCACCTCCTCGGTGATGCCTTTTTGCCACTCC
AATCTGCAGGACATGGTATATCAACATATCAATGGTATATCAATAGCTTCAGTGGGCCAGTAGAACCTACCTTCTTATGGGACCCGAATCGAGGG
CCGACAACAACGCCAGATACGAGTTGTAGTTGTTCATCTTGCGTAGATGCTTCATGATTTTGATAAACTTGTTCACATGCTTCTCCCGCTCCTTG
GCATCCTGCAGGCGCAGGATTTTGGAGCGCGCCCAGTAGGACATCTTGTTGAAGTGCTCGGTGAACTTGTTTAGGTTGGGCGACTTCTCCTCGCA
CTGATCTTTGGCAAATAGTAATACTTCGGGTATCTCGATCTTCGTGAACAGCTCCGCATCCAGCAGCGTCATCTGTTCGGCAATCTCCAGCGACT
TGAGGTCGAGCAGACTAGGCTGGTTTCCACCACCAGCTGTACCACTGCATCCACCACTGCCGGCGATTCCTGCTCCGCCGACACTACCGGCTCCG
CCCAACTCCCCAACAAAGCCGTACACCTTGGGCTCCTTGTACAGCGTCACCTTCTCCACGAACTTGTTGCGCAGCAACTTGGCCAAGTACAATTG
CCCAGAGCAAACCAACTGATAGACGAACTCCACCAGCAGGCTCAACAGCTGGCTGGTTAGATCCGTCGACCTGCATGGTGAACAATGAATGATAA
GCGGGTATGTACCAACTTAGTTTATTCCAAAAATGGTGGTTAGGCAACTCACGTTAGATCGTTGACGACTCGGACCAGCAGCGCAAAGGTCTCCT
TAGCGGCCTTCTGCTTGTTGTCCTGCACTTGACAGAAGAAGTATGTGTAGCGATGGGTCAGCTTCTCGATCACGTCGATCGGCTGGATGAAGGTG
CGAAAGGTGGTGATGAAGGCCTCGCAGAATGCTGCACGAACGGAATGAAAATGGACAGAGACAACAGAGGAGTTGGGTAAATGACCATGCGAACG
ATATTTGGTATGTTTTTGCTGCTTCTGCTTGCGCTGCGAATGCCTACCATTGTCGGCGACCTTTTGGACACGGCTGGCGTGCACGATGAGGGCAT
CGATGTAGCCGCCCTTCACCTCGGGCCCGTCCTCCTCTCTCTTCTTGAGTATCAGGTACCGTGTGATGTTGACCTCTTCCAGCATGTTGATCAGC
ATATCCGCTCGCTCCGCCTCCTCATCCTCGTCGACGTTCGCTGGCTTAACCGACTCGTGCACAGCGACCAGTGGTCGGGACTCCGCCGTTGGCTC
CTCCTGCTCCTCGAGCACTTGGGGCGTGGTTATTGGCTGGTTGTCGGCACTGCTCGCATCCTCGCTCATCTCCATTTCGGCGGCGGGCAACTGAT
GTGAGTGACAGTAGAAAGTCTGTCCATCATCGACGGCGCTCACATTCTCATTGCTGTCCAGCACGGGCGAACGGGGCTCCGGCATCGCATCCTCG
CTGGCCACTGCATCGTTCAGCTCCTCGCATACGGTGGCCATCCGGCTGTCCGGCCTGCCCGTCGACCCATTCTCGCCCAGCGTCGGCTTCGGACT
CGGCGGTGGCGTGGTCACAATGACGGGCTGCAGCGTGGGTGATGCTACCATGCTTGTCGCCTTGCGCTGCTTGTAGTTCTTTGGCGGCAGGGCAG
GTGGCATCTCGAGCTCCGGCGACAGTTCCTTGCTCATGGGCATAATGCTGTAAAGGTAACAAAAAAATAAGGTTAGTACCGCCTAGTAACTACTA
GCTACACACAACTTTACTCACTTCATGGTCTGGCTGTGCGAGATGTTGCGACTTATGTTGCAGGCGTGCATTGTGTGACGATGCTGCTCAATGGA TCGCGTGGACGCCGAACAGATTTCCATGTACGCCAGAACTGTGTGCGGTAGGGTAGGGAAGATGAAATCGTTAGCAACTCTTACGCTTCAGTGGC
GGGGGACAGAAACGAAAACTAAGCCGATCGATCGATCCTTGGACCCACATCCCGAAGGTCTTTGTCTGTTCACCAGATCTACAGGAATCGCAACA
TACAACACAGCACAACGAGTAACAGGACTGGATAGTAACACAGAGCAGGAGCTTTCGGGGCTTTGGACTGGAGATACTAGCTCTGGACGGACACA
GCGGGTTAGGCGGAGCGAAATGGAAGCCACAGAACTGTTGCTCAGTCCATGTACTTGGGACTAGAAACGGAAACTGCAAACAGGTGGCTGTTCGG
GCGTCAAGTCAATACGAATGCGGCGCAGCAGCAAAGTTATTAGCAGAGCAAGAAGCCAATAGCGAACTCGAAATGCTCTTTCCATCATGGTTATT
AACTGGATAGCAAAGGGTATTCACCTTATGTAAAGTATTATAAAAACGAAAGAGGATAGTTTAATAGCTATCTTTGTGTTTACACACTAGATTCC
CATTCGGTTGGACCATGGAAATCTCTGCTCAATGGTGAAATGAAGCCAAATTTAATCGAAAGGAGTGTCATTCAGTACTGAGGTAGGGAATAGAG
CATTGCGAGCTTTCCAAGGGCGCCGTGCAAAAAAAGTTTGTTTCGTGGGTGATTTTGTTTTATTTCGTTTTTGTTTGGCATTTGGCAGCAAAAGT
TGGCTTAGTGTTTTTGTTTCGTGTTGGTCCTCTAGTAACACACACAGACTTACCCGAAAAGGCCACACTTTGAAACACTAGATGTTGGTTGGAAC
GATAATTTAGATGGGTTAGACTCTTGCGTACAACAATTTGGCAAACTTTCTTGTCGCCAGCATTTCTAAGGGGTTTGCGATAATGCGGGTATGTG
CTATAAATAAAATGGTCTTAAAGAAACAAACAAATCTCGAAAAACGGACTGCTCTGCCTGGCTACCCATATAAAAGGTGATGACTGATTGACTGA
TTGCCTGGTTGACTGATTGATTTGTTTAACTAACTAATTGGAGGTCTGATTGTTGTGGTGTTTCTGTTTCGTCTGATTTTTGTTTGGGTTTAACA
ATGGAGTAGCCTATCAAATGGATCTGATGGAATGGATACTGCTGCAACAGGAGGACAGTGATGCAGGAAACCCTGAAAATGCGCTCAACAAAACA
CCCATTGACTCACCGCTCGGCCTGGCCTGGGCGGTTCCGAAAATGACAAAAAAAAAAAAAATGATATAAAAGTAATTTACACAATATACACAACA
ACAAAAAACACACACACGGTACGAGATGCAGAACCAAACCAAATCGAAAAAAAAACGGAAAAAAATAAGAAAGAAAAATAGGAAGAATCGATGTA
AATAAAGTGTGCATCGTGGGCAAACTGACTTACTGTGCTTCTTTTTTATTGGCAGCGGCGGTGGCTCCTGATCCAAGTGTCGCTGATCGAACGCA
CTGCAGCTGCCACTCCCCGCCAGCTGGAGGCGGGGTCCCTCGATCAGGCTGTGGTGCTTGGAGTGCCACTGCTGCAGTTGACCGGCGGACGCAGT
ATGCGGATGGTGATTGAGGTGATGGAGCGGCGACAGCTGACGCAGCTCGGCCACCTCCGACTGGCTGCTCCGATGGCTGGCCCAGCCGGAGGAGG
ACTGCACCTCGTCCAGCTCATCGCCAACTCCGGGCGAGTCGTGGCGGGTTAGGCTGCTCCGTTGGATGCTCTTTGGCGGCAAGGCGGGCGCCAGA
TCGGCCGGCGTCGTCGTCGTCTGCTGCTGCTGCTGCTGCTGCAGCTGCTCCACTTCGCTGCTGCCATAGCCGGTGGTTGTGCTGCTGCTGGTGGT
CGTGGTGGTGCAGCTGCTACTGCTCGAGGATATATGACGCTGGCTGTGCGACACCAACTGGCTAATCTGCTGGTACTCGCTACTGCTGCCGACCG
CCGTCGACTCACTGATGCTGAACGCAATCTCCGAATTGCTGCTGGACGACTTCGTGGAGGACTGGACACTGTAGTCCGTCGTCTGTGTGGAAGTG
CGAAACTCACGCATCGACACGAAACCTGGCGATGGAAGGAGAGTGGTGTTAGAAATGGTCAAAAATGCAGTTCTCGTTGTGGGGAACGGGTAGCC
AAAACCAAGCGGAAATTATATAATAAGCCGGAGGAAATCTGTGGAAAGGATCATTACGGAGGCGGGAGAATAAAGCCAACTATTTACAGCATCTA
GGACAAACATGTATACAATACGCCTAACGAAAAATTTGGAAGGGAATTCATTGGGCGCGTGCAACAGATACAAAATAATAAGCGGGATTTTAAGT
ACGATGATAGATGTTCTGGGTACCCGATTCGTTTGAGTGGCGATTGCTGTTAGTTTCCCCGTCACCAGACGCTGCAGCAGCTACACCTTCGCCTG
CTCCTCCAGTTCCACCAGCAACACCAGCTATACCACCACCAGTCGAAAGTGGTGTCTGCGTTTTGTCGTCGATTGCGGCGCCTGCGTAACCGGTG
GATTCTGTACGGGATTCGTTGATTGGGGGGCCACCACTCGAGTTGAGCTGAGTGAGGGGAGTGGCGAAGCCTTGCGGCAATACTCACTGTAGCT
GACCATCTTGTCCATGTCTTCGTCCATCATCGCAGCCAACTTTGGAAATGACCTCAGATGCTGATGTTGCTGTTGCTGGTCCTCCTCCTCGCGTG
AGTGATTCAACGCCGAGTCAAAGGAGCACTGACTATTCTCATCCGGTGACCGTGAACGCACGGATAGGCTGTGGAATGTGGGTGCACCAATTATT
GTAGTGATTGCTAGTGATTGCTTTAATCTGCAAGCCACTTACCGATCCACGCCATAATTCAGCAGCGAGATATTGGAACTGCAGTCCAGGTCCGA
GTTCAGACTAATATTATGGGACTGGGCGTAGGGCAGTGGACTGGCCTGATTGGAGGTGGATGTCGACGATGAGCAGCCTACGCCCACTGTACCAG
CTGATGCGCTCGGCTGGCTGCGTCGCTTTGGTGGCAACGGCGGCGGATTACTGGCCCTATTGGGTAGCGGTGGCTTCGGCGGTGGACTCGTGTCG
CGCAGGATACTTTCGGTGCTGTGGGAGCCGCGCATCGGGTTCACATTGTGCTGCTCCAGTATGTCGCGCTCCTTGGGCGTGAGCGCTATGTCCGG
CAACGAAGTACGCTGGGCAGCTGATTCGGCGGCCGAAACGCGCATGACTCCAGTACCGGGAACACTCGCTCCCGGCGAGGCGGTGACCGCACCCA
TGATCTCCGCCGCCGCTCCAATGCCGCCCAAGCCAGATCCACTGTAGCGAAAGGCGCACTGATCCTGCTCCTTCAGCTTGCCCTGCGCCAGCGTA
ACGAGATTCTGTGCACGATCATGAAACATCATCGTATTTATTATAGCAATACACTGTGTACTAGGTTAGTGTTAATTGGACTTACCCGCACAGCA
TCCTCGAGAAGATCAATGACTTCCCGCACATTCTCGTTGCTCAGGGAGGCGCACTCGCCGCTGTCCTCGGAGAGCATCACCTCGTCGCAGAGCTT
GATGAGCTTGCCCAGGCTCTGGTAAACCTGCAGCGTGGCGCTGCTCATGATGGCACTGTTTTCATTCAGGGTATAGGTTTGGATCACTGCGGCAG
CAAAGGAAAGCAACTGGATTAATTACAAAACGAGGAAATTGGGGTAGTAGATACTCACCGGAGTACATGCTGGCTATGGTTTCCAGAATGACCGT
TCCGTTGCCCGGCAACACCTCCAGCTTCTTCTTGAGTATAACATCCCGGAAGTGCTTCAGGGCATTCGAAATGTCCTTGACGTGCGTCTCCAGGG
TTTGGGTGGACCGTAGCACCTCCTCGGTGGTGGGCGGTGCCTTTGTGCCGTGCTTGGTGCGCGGACTGTGCGGCGAGTGGGAGCGACCCAGTGTA
TTGTTGGTGGTTCGCATCAGGGAAATCTTCTCGATGAGGTCGTCCTTAAAGGAACGCGCCCGGCGCGCTAGCTTGGTGCCCTTGAGACTGTTCTT
GTGGCCCGAGGATCCGGCACTGGGTGGTGCCGGTGGTACACCACCACCTCCGCCTGCTCCTGCTCCCCCTACCCGACTAGATCCTCCCGGCGTGC
CCTGCAGCTGCTGGTGCTGCGAGTGATGCTGATGCGTGGGTGGTGGCGGAGTGCAGGCGGTGGAGTAGCTGCCGCTGTTGATGCTATTGTTGCTG
CTGCTGCTGCAGCCGCCACCGCCCACTCCGATGCCACTGGAACAGGTGCCGGGCGTGGATGGAGAACTGATGCTGCCGTCTGCAAAAAGAGCAAG
AAATCGGGGATTATTAATCTAAGGTAGGTACACTTAATCAATTCATAGGCATTAGATAACAATATACGTTTTTGGGTAACAATAATAAGAGACTA
AGACTGGAATCTAGATCCTATATATATACACATATCATGGGCTTAGAGTCTTTCCTGTTCGAGCCGCATTCTTGAATGCCAATTTGAAAATCAAA
AGTTGCTCCATATAAAACCACAATCTTTTGCAATATATGGCAATGTTGGTATCGTTTCGTTTCTTACTTTTCTTCATTTGGTTAGGTAAGATGAA
TATCTTAAGGTCATCGTATACATCATTCTAAAGTGGCTAAGCCAGCAGCGAAAATGAAAATCTTTCAGAGTTAGCCAAACAGCTTGAGGAATCTT
GAAAAGATTCATCATTACCCCTTCACAACACAATATATGTACATATGTACTCATTCGAATCTTGAAACGTGTCTACTTAAATGTGAAATAATTGC
AATTGAAATCAACATATGTAATACGGAATTCCTAGCATTCCCCATTTCGGGAATCGTTCATGCGAGCCCAAACATTTTAGTTTCGGAACTTTTTT
AAAGATCCAAAACAGCGAGAAACCGATGAGCACCACCCACCAAGCGAAAAGACCGGCGAGTAGCTTTCACTTACGGCACACCGCATTCTTGAGCG
GCACAGGTGTGTCCATCTCCATATCGAACTCCCTATCCACGGTCACATTCACATCGACATCCACATCCATCTGCAGTGGAATCGCTGGCGTTGAT
AGCGCCAATCGTGCCAGCTTTTTGTATTTGCGACGTCTGTGGAATTTGATGCTATGCAACGTGTTGCCGGTGGCACTGATGCTGTTGCAGGTGTT
ACTGCTGTTGCAGTTGCAGTTGTTGCTTGTGAGGCTATGATTGTTGTTGGTGTCGCGCGGCGACCACGACTGCCGCTGAGTCTTCCAAAGACGAT
GATGATTGTGATGGTGCTGTTGATGATGATGATGATGGAGTTGGTGCTGATGGTCATCGTGGCTGGCACCGCTGGGATACGGATTCCGATTCCGA
TTCGGTTTCGGACTCGGATGTGGCGGCAATTGCTTGACCGTGTACGAATAGAAATGCCAGCGGTCGGCGAGCGCACAGTCGCTCAAAAAAGATTC
ATCAAACTGCGGCATAATGTTGCATAATGACAGCAGCAGCAGCAGCAGCAATAACAACAGCAGCAACAGCGACAGCAACACGCATAACAACAATT
TGTTGTGGCTTAAATATGCTTGGCCAAAAGACACACACGTTGGCCTAACTGATTTCTCCAAATAGCGATAAGCGATAGCAGCAACATCGTTTTCG
TATAAGATTGTTGATTTAAGCGATTGCCGTCGCGATTACAACATCAATTCATTTTTCTGTTTCGGCATGTTTTACATTGATTATTTCACTTTCAG
TTTTCGGTTGTTTCAGTGTTTTCGGAAAAAGTTTTAAGCACTGATAAAAGCTATATCCGATGTGCTCTGCCAGCAGGAAGTAGATTTCAATTGCT
TTCTCATCATGTTCGTTCACTTTTGCAATTCGTTCGATAGTCCGATAGGCAATTCAAGCGATTACCGATTCAAGCTTCCTGTGGCAACCGCAAGA
ATTGTTCTGGACACTCTTTGTTTGACTGAAATACAAGTATGCCAGCTTAGAGATCACTTCAATTGGCCATAGTGATTTCCGTATATTATTTTCTT
TAATGTTTAAAAGCCATCAAGCCCTAATTTCCGTTTCTTACTGCCTGCCCGATTGTGGTAAATTGAAGGTAATCAACTCCAAAGCCACTTGTCTT
TTGCTTTACTTATATTTCAAGTGCGATTTCCGCAATTTTCCCCAATAGCTTTCCATTCGCCGCACAGTCACTTTTGCATTTCTGAACTTGAAATT
TCAACAGGCTTCGGCTGATTGATTCAATCGCCGATAAGCGATAAGCTAACACTTTTGGCCTGCCACTCTCAGTGCAATTTCTTTCACTTTTCAAG
TGCAATTTGGCGCTCTTTTCTTTGATTTTTCATCATCCATCCATCCATCCATCTCGTTGGCGCACCGCCCCCGCAGTGGGCTATCTATCTGGTTG
GCCTCTGGGTGAGGAGATGTTGATTAAATAAATCACAAATAAAGATGATTATATTTAGACACTGGCGCTCTGCTGCTGCTGCTGCGGCGGCTGTC
GTCGTAGTCCGTTCGCGATGTTGTCGTTGTCGACTGGAAAGCGCACTGAACTATGAAAATCCGCAAAACGGGCAAAGCCAAAGACGACCGACCGA
CTGAAAGACCGACCAGGCGGCAAAAGCGAGTGTCCGAGTCTTGGAGACCCGCTAACCGGCCAACGGCAATGGCAACACATTAGCAATATAGCAAT

FIGURE SHEET 163

ACAGCAATAGCAGCAACAACAGACGCAGCAGCAGCAGCAGCAGCAACACGAGAGCCGCCGAGGGGGCAAAAAAAAAAAAGAGCCCCAAATGGCAC
TTGCCCACCTGGCAATCGCCCTCTCACCATCTCTCCTGATCTCTCCTGCTGCTCTCGCCACATCGCTCTTTCTCTTTCCGAGATTCATCAAACAA
ATCATACATGTTCACATCACTGATGGACCAAACGGGTGCTACAAACGTATCCATTCAATGTGGCTCGGAAATCGTGCAAATATTCAGTATATATT
TACGATAATATTTCTATTTTAAAATGACAAGTTACTTTACTGTTTATACTTGCAGGTACACCCCCCTTTCTCGCAGTGCAGTCCGCGGTTTGCGG
CTCTTTTCACCCGGGAGGCTGCTCTCCAACCGTCGGCCTCTCCGCCCAATTATCAATCAGCTGGCGCACCTGAGAAAGAGCCCGTGGCGAAGGGT
GAGGGGGCGGTAATTGGGGGCGACAAGGGAGTGGTAAAGGGGGGGGGTGAGGTGGATGCGGGGCAAGAGACAAGAAGACGCCGGGCGGATTTCT
TCAATTTGCAAGTGCCGCTCGTG
(SEQ ID NO: 295)

Exon: 10613..9290
Exon: 8629..8039
Exon: 7971..7781
Exon: 7703..7168
Exon: 7098..6929
Exon: 6390..5734
Exon: 4313..4202
Exon: 4132..3468
Exon: 3356..3188
Exon: 3110..2541
Exon: 2473..2348
Exon: 2270..2139
Exon: 2064..1001
Start ATG: 9380 (Reverse strand: CAT)

Transcript No. : CT10408
GAGTGGCAGGCCAAAAGTGTTAGCTTATCGCTTATCGGCGATTGAATCAATCAGCCGAAGCCTGTTGAAATTTCAAGTTCAGAAATGCAAAAGTG
ACTGTGCGGCGAATGGAAAGCTATTGGGGAAAATTGCGGAAATCGCACTTGAAATATAAGTAAAGCAAAAGACAAGTGGCTTTGGAGTTGATTAC
CTTCAATTTACCACAATCGGGCAGGCAGTAAGAAACGGAAATTAGGGCTTGATGGCTTTTAAACATTAAAGAAAATAATATACGGAAATCACTAT
GGCCAATTGAAGTGATCTCTAAGCTGGCATACTTGTATTTCAGTCAAACAAAGAGTGTCCAGAACAATTCTTGCGGTTGCCACAGGAAGCTTGAA
TCGGTAATCGCTTGAATTGCCTATCGGACTATCGAACGAATTGCAAAAGTGAACGAACATGATGAGAAAGCAATTGAAATCTACTTCCTGCTGGC
AGAGCACATCGGATATAGCTTTTATCAGTGCTTAAAACTTTTTCCGAAAACACTGAAACAACCGAAAACTGAAAGTGAAATAATCAATGTAAAAC
ATGCCGAAACAGAAAAATGAATTGATGTTGTAATCGCGACGGCAATCGCTTAAATCAACAATCTTATACGAAAACGATGTTGCTGCTATCGCTTA
TCGCTATTTGGAGAAATCAGTTAGGCCAACGTGTGTGTCTTTTGGCCAAGCATATTTAAGCCACAACAAATTGTTGTTATGCGTGTTGCTGTCGC
TGTTGCTGCTGTTGTTATTGCTGCTGCTGCTGCTGCTGTCATTATGCAACATTATGCCGCAGTTTGATGAATCTTTTTTGAGCGACTGTGCGCTC
GCCGACCGCTGGCATTTCTATTCGTACACGGTCAAGCAATTGCCGCCACATCCGAGTCCGAAACCGAATCGGAATCGGAATCCGTATCCCAGCGG
TGCCAGCCACGATGACCATCAGCACCAACTCCATCATCATCATCATCAACAGCACCATCACAATCATCATCGTCTTTGGAAGACTCAGCGGCAGT
CGTGGTCGCCGCGCGACACCAACAACAATCATAGCCTCACAAGCAACAACTGCAACTGCAACAGCAGTAACACCTGCAACAGCATCAGTGCCACC
GGCAACACGTTGCATAGCATCAAATTCCACAGACGTCGCAAATACAAAAAGCTGGCACGATTGGCGCTATCAACGCCAGCGATTCCACTGCAGAT
GGATGTGGATGTCGATGTGAATGTGACCGTGGATAGGGAGTTCGATATGGAGATGGACACACCTGTGCCGCTCAAGAATGCGGTGTGCCACGGCA
GCATCAGTTCTCCATCCACGCCCGGCACCTGTTCCAGTGGCATCGGAGTGGGCGGTGGCGGCTGCAGCAGCAGCAACAATAGCATCAACAGC
GGCAGCTACTCCACCGCCTGCACTCCGCCACCACCCACGCATCAGCATCACTCGCAGCACCAGCAGCTGCAGGGCACGCCGGGAGGATCTAGTCG
GGTAGGGGGAGCAGGAGCAGGCGGAGGTGGTGGTGTACCACCGGCACCACCCAGTGCCGGATCCTCGGGCCACAAGAACAGTCTCAAGGGCACCA
AGCTAGCGCGCCGGGCGCGTTCCTTTAAGGACGACCTCATCGAGAAGATTTCCCTGATGCGAACCACCAACAATACACTGGGTCGCTCCCACTCG
CCGCACAGTCCGCGCACCAAGCACGGCACAAAGGCACCGCCCACCACCGAGGAGGTGCTACGGTCCACCCAAACCCTGGAGACGCACGTCAAGGA
CATTTCGAATGCCCTGAAGCACTTCCGGGATGTTATACTCAAGAAGAAGCTGGAGGTGTTGCCGGGCAACGGAACGGTCATTCTGGAAACCATAG
CCAGCATGTACTCCGTGATCCAAACCTATACCCTGAATGAAAACAGTGCCATCATGAGCAGCGCCACGCTGCAGGTTTACCAGAGCCTGGGCAAG
CTCATCAAGCTCTGCGACGAGGTGATGCTCTCCGAGGACAGCGGCGAGTGCGCCTCCCTGAGCAACGAGAATGTGCGGGAAGTCATTGATCTTCT
CGAGGATGCTGTGCGGAATCTCGTTACGCTGGCGCAGGGCAAGCTGAAGGAGCAGGATCAGTGCGCCTTTCGCTACAGTGGATCTGGCTTGGGCG
GCATTGGAGCGGCGGCGGAGATCATGGGTGCGGTCACCGCCTCGCCGGGAGCGAGTGTTCCCGGTACTGGAGTCATGCGCGTTTCGGCCGCCGAA
TCAGCTGCCCAGCGTACTTCGTTGCCGGACATAGCGCTCACGCCCAAGGAGCGCGACATACTGGAGCAGCACAATGTGAACCCGATGCGCGGCTC
CCACAGCACCGAAAGTATCCTGCGCGACACGAGTCCACCGCCGAAGCCACCGCTACCCAATAGGGCCAGTAATCCGCCGCCGTTGCCACCAAAGC
GACGCAGCCAGCCGAGCGCATCAGCTGGTACAGTGGGCGTAGGCTGCTCATCGTCGACATCCACCTCCAATCAGGCCAGTCCACTGCCCTACGCC
CAGTCCCATAATATTAGTCTGAACTCGGACCTGGACTGCAGTTCCAATATCTCGCTGCTGAATTATGGCGTGGATCGCCTATCCGTGCGTTCACG
GTCACCGGATGAGAATAGTCAGTGCTCCTTTGACTCGGCGTTGAATCACTCACGCGAGGAGGAGGACCAGCAACAGCAACATCAGCATCTGAGGT
CATTTCCAAAGTTGGCTGCGATGATGGACGAAGACATGGACAAGATGGTCAGCTACAGTTTCGTGTCGATGCGTGAGTTTCGCACTTCCACACAG
ACGACGGACTACAGTGTCCAGTCCTCCACGAAGTCGTCCAGCAGCAATTCGGAGATTGCGTTCAGCATCAGTGAGTCGACGGCGGTCGGCAGCAG
TAGCGAGTACCAGCAGATTAGCCAGTTGGTGTCGCACAGCCAGCGTCATATATCCTCGAGCAGTAGCAGCTGCACCACCACGACCACCAGCAGCA
GCACAACCACCGGCTATGGCAGCAGCGAAGTGGAGCAGCTGCAGCAGCAGCAGCAGCAGACGACGACGACGCCGGCCGATCTGGCGCCCGCC
TTGCCGCCAAAGAGCATCCAACGGAGCAGCCTAACCCGCCACGACTCGCCCGGAGTTGGCGATGAGCTGGACGAGGTGCAGTCCTCCTCCGGCTG
GGCCAGCCATCGGAGCAGCCAGTCGGAGGTGGCCGAGCTGCGTCAGCTGTCGCCGCTCCATCACCTCAATCACCATCCGCATACTGCGTCCGCCG
GTCAACTGCAGCAGTGGCACTCCAAGCACCACAGCCTGATCGAGGGACCCCGCCTCCAGCTGGCGGGGAGTGGCAGCTGCAGTGCGTTCGATCAG
CGACACTTGGATCAGGAGCCACCGCCGCTGCCAATAAAAAAGAAGCACATTCTGGCGTACATGGAAATCTGTTCGGCGTCCACGCGATCCATTGA
GCAGCATCGTCACACAATGCACGCCTGCAACATAAGTCGCAACATCTCGCACAGCCAGACCATGAACATTATGCCCATGAGCAAGGAACTGTCGC
CGGAGCTCGAGATGCCACCTGCCCTGCCGCCAAAGAACTACAAGCAGCGCAAGGCGACAAGCATGGTAGCATCACCCACGCTGCAGCCCGTCATT
GTGACCACGCCACCGCCGAGTCCGAAGCCGACGCTGGGCGAGAATGGGTCGACGGGCAGGCCGGACAGCCGGATGGCCACCGTATGCGAGGAGCT
GAACGATGCAGTGGCCAGCGAGGATGCGATGCCGGAGCCCCGTTCGCCCGTGCTGGACAGCAATGAGAATGTGAGCGCCGTCGATGATGGACAGA
CTTTCTACTGTCACTCACATCAGTTGCCCGCCGCCGAAATGGAGATGAGCGAGGATGCGAGCAGTGCCGACAACCAGCCAATAACCACGCCCCAA
GTGCTCGAGGAGCAGGAGGAGCCAACGGCGGAGTCCCGACCACTGGTCGCTGTGCACGAGTCGGTTAAGCCAGCGAACGTCGACGAGGATGAGGA
GGCGGAGCGAGCGGATATGCTGATCAACATGCTGGAAGAGGTCAACATCACACGGTACCTGATACTCAAGAAGAGAGAGGAGGACGGGCCCGAGG
TGAAGGGCGGCTACATCGATGCCCTCATCGTGCACGCCAGCCGTGTCCAAAAGGTCGCCGACAATGCATTCTGCGAGGCCTTCATCACCACCTTT
CGCACCTTCATCCAGCCGATCGACGTGATCGAGAAGCTGACCCATCGCTACACATACTTCTTCTGTCAAGTGCAGGACAACAAGCAGAAGGCCGC

FIGURE SHEET 164

TAAGGAGACCTTTGCGCTGCTGGTCCGAGTCGTCAACGATCTAACGTCGACGGATCTAACCAGCCAGCTGTTGAGCCTGCTGGTGGAGTTCGTCT
ATCAGTTGGTTTGCTCTGGGCAATTGTACTTGGCCAAGTTGCTGCGCAACAAGTTCGTGGAGAAGGTGACGCTGTACAAGGAGCCCAAGGTGTAC
GGCTTTGTTGGGGAGTTGGGCGGAGCCGGTAGTGTCGGCGGAGCAGGAATCGCCGGCAGTGGTGGATGCAGTGGTACAGCTGGTGGTGGAAACCA
GCCTAGTCTGCTCGACCTCAAGTCGCTGGAGATTGCCGAACAGATGACGCTGCTGGATGCGGAGCTGTTCACGAAGATCGAGATACCCGAAGTAT
TACTATTTGCCAAAGATCAGTGCGAGGAGAAGTCGCCCAACCTAAACAAGTTCACCGAGCACTTCAACAAGATGTCCTACTGGGCGCGCTCCAAA
ATCCTGCGCCTGCAGGATGCCAAGGAGCGGGAGAAGCATGTGAACAAGTTTATCAAAATCATGAAGCATCTACGCAAGATGAACAACTACAACTC
GTATCTGGCGTTGTTGTCGGCCCTCGATTCGGGTCCCATAAGAAGATTGGAGTGGCAAAAAGGCATCACCGAGGAGGTGCGATCATTCTGCGCCC
TCATCGATTCCAGCTCCAGTTTTCGCGCCTATCGACAGGCGCTGGCCGAAACTAATCCGCCCTGCATACCCTACATCGGCCTAATTCTGCAGGAT
CTAACGTTTGTGCATGTGGGCAACCAGGACTACTTGTCCAAGGGCGTCATAAACTTCTCCAAGCGCTGGCAGCAGTACAACATAATTGACAACAT
GAAACGTTTTAAGAAATGTGCCTATCCATTTCGACGCAACGAGCGCATTATACGCTTCTTTGATAACTTCAAGGACTTTATGGGCGAGGAGGAGA
TGTGGCAGATATCGGAGAAGATCAAGCCGCGTGGACGCCGCCCCGTTAACTATTAGTCTTCAAGCAGCAACAGCAAAACACCAATATTATATATG
ATAAAGTATATACACCGTATTAATTAAACAGTTCAAAACGGTTGCCACGTCTAGGAGGAGGATCAGCATCGGGAGCAGCCAACAACTATTCTAAT
GGGTCTGAGCAATAATGTTCGCTATTCTCTGTCTATATATATACAATTATACAAGATATTTAGCTGTAATTACCAGCCGATGCCGAATCGGAAAT
ACATATACATACTTACTTAAGATGTAGCGATTCAGATACGGATACGGATACATGTAGCCGCGTACAAATAACGAGCCGATCTGTAGTTTAACTAT
TAAGCTCTATGAGTCATTGGGTCGATGGACCTAACCTCAGCTAACTCCCCACCAATATTCGAATCCGAATCCCTGTCTGCGAGTCCCAAAAACTT
TTTCCCGGACTTTTGCCAGCACTAGAACACCAAACTAACTAACTAACTTACTTACCACCAGAGACAACCAATCAAGAAATCAGCAATTTTCGCTT
TTGTTTTGAGATCTCTTTTTTACACAAGAACACAACGAATTTTGAAAGCAAGCTACGTGAACGTAGAGGCCAACCGACAAACTATATTCGACGAT
ATATGTAGCGATATCTCGGACTATAAATCGATGCAATCCACGAGCAGAACACCAAGCGAACCCTAGCACAAAGCGCGTTATATGCAATTCTCTCT
CCAAACAACCAATATTAAATACCCGTGTGTGTGTATGTGTGTTAGAAGTTATTCAAATTGAAATTGAACTCAAAATCAAAATCAGAGATTTCAGA
GTGCACGAAACAGAAAACAGAAGGCGGTATCTATCGATCAAATCAATCAATCAATGAAATCAATCAAAAATTCATTTTGCGACTCAATTAATTGA
AGAAACTTTTAAAGTTACAAAACAAAACAAAATACAA
(SEQ ID NO: 296)

Start ATG: 1234 (Reverse strand: CAT)

MDVDVDVNVTVDREFDMEMDTPVPLKNAVCHGSISSPSTPGTCSSGIGVGGGGCSSSSNNSINSGSYSTACTPPPPTHQHHSQHQQLQGTPGGSS
RVGGAGAGGGGGVPPAPPSAGSSGHKNSLKGTKLARRARSFKDDLIEKISLMRTTNNTLGRSHSPHSPRTKHGTKAPPTTEEVLRSTQTLETHVK
DISNALKHFRDVILKKKLEVLPGNGTVILETIASMYSVIQTYTLNENSAIMSSATLQVYQSLGKLIKLCDEVMLSEDSGECASLSNENVREVIDL
LEDAVRNLVTLAQGKLKEQDQCAFRYSGSGLGGIGAAAEIMGAVTASPGASVPGTGVMRVSAAESAAQRTSLPDIALTPKERDILEQHNVNPMRG
SHSTESILRDTSPPPKPPLPNRASNPPPLPPKRRSQPSASAGTVGVGCSSSTSTSNQASPLPYAQSHNISLNSDLDCSSNISLLNYGVDRLSVRS
RSPDENSQCSFDSALNHSREEEDQQQHQHLRSFPKLAAMMDEDMDKMVSYSFVSMREFRTSTQTTDYSVQSSTKSSSSNSEIAFSISESTAVGS
SSEYQQISQLVSHSQRHISSSSSSCTTTTSSSTTTGYGSSEVEQLQQQQQQTTTTPADLAPALPPKSIQRSSLTRHDSPGVGDELDEVQSSSG
WASHRSSQSEVAELRQLSPLHHLNHHPHTASAGQLQQWHSKHHSLIEGPRLQLAGSGSCSAFDQRHLDQEPPPLPIKKKHILAYMEICSASTRSI
EQHRHTMHACNISRNISHSQTMNIMPMSKELSPELEMPPALPPKNYKQRKATSMVASPTLQPVIVTTPPPSPKPTLGENGSTGRPDSRMATVCEE
LNDAVASEDAMPEPRSPVLDSNENVSAVDDGQTFYCHSHQLPAAEMEMSEDASSADNQPITTPQVLEEQEEPTAESRPLVAVHESVKPANVDEDE
EAERADMLINMLEEVNITRYLILKKREEDGPEVKGGYIDALIVHASRVQKVADNAFCEAFITTFRTFIQPIDVIEKLTHRYTYFFCQVQDNKQKA
AKETFALLVRVVNDLTSTDLTSQLLSLLVEFVYQLVCSGQLYLAKLLRNKFVEKVTLYKEPKVYGFVGELGGAGSVGGAGIAGSGGCSGTAGGGN
QPSLLDLKSLEIAEQMTLLDAELFTKIEIPEVLLFAKDQCEEKSPNLNKFTEHFNKMSYWARSKILRLQDAKEREKHVNKFIKIMKHLRKMNNYN
SYLALLSALDSGPIRRLEWQKGITEEVRSFCALIDSSSSFRAYRQALAETNPPCIPYIGLILQDLTFVHVGNQDYLSKGVINFSKRWQQYNIIDN
MKRFKKCAYPFRRNERIIRFFDNFKDFMGEEEMWQISEKIKPRGRRPVNY*
(SEQ ID NO: 297)

Name: GUANINE NUCLEOTIDE EXCHANGE FACTOR DC3G
Classification: signal_transduction
Gene Symbol: C3G
FlyBase ID: FBgn0026145

Celera Sequence No. : 142000013384832
CAGCGACAGATCAGGCGGTTCCGGCGGACGGTCATATACACCATATACGACGTGAAGGTCTGCTCCAGCATCATACAAGACATAGCCGCCAAGTT
GTCCCCGTACTTCAGCTCAACCCCGAACTCGTACTACAGCGACTCCCTCTTTTTCCTGTCCCTCGGCCTTCACAGGATCGCCGACAGGAGCCTAA
ACAGAGCCATTCTGCTAGATTGTGATATAGTCTTCCGATCCGATGTCCGACTGCTGTTCAATGAGTTCGACAACTTTCTGCCGCACCAGCTGTAC
GGACTGGCACCGGAACTGACCCCCGTCTACCGCCACATCCTCTACCGCTATCGCGTGCGCTATCCGAAGACCAGTTTCGGGAATCCCTACTATCC
GATCAACAACGAAGGGGGCAACCAACATAGCCGTGTCCACCACGGCTATCCAGGCCTGAACTCCGGCGTGGTCCTGCTGCTCCTAAACCGCATCC
GTAACTCAAAGTCCTACCTGGAGAAGCTGACCCACTCGGAGGTGCACACCCTGGTCGCCAAGTACTCCTTCAAGGGCCACCTCGGCGACCAGGAC
TTCTTCACCCTGCTGGGATACGAGTACCCGAACTTAATCTACAGACTGGACTGCATTTGGAACCGCCAGCTGTGCACCTGGTGGAAGGATCACGG
ATACTCACAGATATTCGACGCTTATTTCCGGTGCGAGGGCAATATTAAAATGTACCATGGCAACTGTAATACGCGAATTCCAGAATAAATAAAAT
TGTTATAGGAATATTAAATTAATTAAATGCAGGGTATTTTTATTTGGTATAACTATTGTAATGGAACGTTATGTAATATACGGTGAATTTAATCT
TAGTTTATAGACCATTATAAATGGTGATATATAAAAATGAAATTTAAAGATAAAAGACAGCCCACACCTATCACCATTTAAAATATCAAAACGAT
GTAAGAATGTTATCGATAGGCGAGAAGCAACAGAGTGGGAATATGCCGCACAGGGTGTTTCGTGTGAATGATTTCGCCTCTTGTTTCTTATCTTT
AACCTTCATTTCTGGCTCCGTTTGGCTATGAATTAGGAGCAGTCCCGAATAATCAGTCGAGCATACGTAGTTAACGATGGCGCCGAATGCAGCAG
TACCAGTGGAGCGATATGAGCCTGAGAACATCGGGATCAACGCCATTCTCCTGGGGCCGCCGGGTTCCGGCAAAGGAACGCAGGTGGGTCAAAAT
TACATAATGATGTGTTTTTTGTGACACGGACGCCATGTAGTCTATAAATAAATACAACGTGTTCAAGTGCGCGGTTTTTGTTTGCAAATAATCGG
TGAAGCTCGTTAATTCTCTTGGAAGAGAATTAAAACTGGTGAAGTTATATAAGACGATGTGTACATGGAAATGTATATGTATGTATCTACGTGCC
AAGTATGTACATATGCGTCAAGCAGTGTCTTTCTCTTGACCCTGAATCAAATCAAAGCCTTGGCGAGATGTGGCGAATTAAGTGGAACACCTTTA
GGCAATCGATTGGGTATTATGCAGACCATCTATTAAAAGGCTACCAGAACATTCCTGGCCTCAAGAAATGCATCTTATCTAGCCGATTGGTTACC
TTGCTTACCTTCCGATATGGTGCTAAATTGATTAATTGATTAGCTCTAACTGAAACTTATCAATGTTTTTAATTATGCCCATTTCAGGCTCCCCT
GCTGAAGGAGAAGTTCTGCGTGTGCCACCTGTCGACCGGCGACATGCTGCGGGCGGAGATTTCATCCGGTTCGAAGCTGGGAGCCGAGTTGAAGA
AGGTCATGGATGCCGGCAAACTGGTCTCCGACGACCTGGTCGTGGACATGATCGACTCCAACCTGGACAAGCCCGAGTGCAAGAATGGATTCCTC
CTGGACGGATTCCCCAGGACTGTCGTTCAAGCTGAGAAGGTAGCCACACGTGTGAAGCACTTTGGACTTTAGGTTATAATCCGTTCGAAACGCAC
TTTGCAGCTCGACACATTGCTGGACAAGAGGAAAACCAACTTGGATGCTGTCATCGAGTTTGCCATCGACGACAGTCTGTTGGTGAGGCGCATCA CTGGCCGCTTGATCCACCAGGCCAGCGGGCGTTCGTATCACGAAGAGTTTGCCCCTCCAAAGAAGCCAATGACGGACGATGTAAGTATCTCTATA
GGACGCTATCCAAGAACTCTAAATGAAAGCAGACCTTGTGTACTTGCAGGTCACTGGAGAGCCCCTAATCCGTCGCAGCGATGACAACGCCGAGG
CTCTGAAGAAGCGACTGGAAGCATATCACAAGCAGACAAAGCCGCTGGTCGACTACTACGGCCTGAGGGGTCTGCACTTCAAGGTGGACGCCGCC
AAGAAGTCCAGCGACGTCTTCTCCACCATCGACTCTATATTCCAACGCAAGCGTCCTGCCCAGATCCAGTTATGATTTGTTCCTGCGCAATGATC
AACTACTGATAACTGCCTCCTGACAATTTATTTCGAGACACACACAACGTTTAAGCCTAAAGTTATAGTTGCATCCGGAAATCCTGAACAAACGA
AATTACCTTTGCAGGTCGACTACTTTCCTTGTACAGATTTCTAAAGTGTATGTGTTTGTTACTTTTTACATTTCACTATTTGTAACTACAATACA
ATTTAATAAAAAAATCGAAGGAAACAAGTACATTTTACGAGACATGACTGCTTTAAACTGGGCTGCGTTCGAATGAGGATGGACGACGCCAAGT
TCAAACTTCCACACAATTGTTTTCCGGAAAGCTTCTGGAATATGATGCGGCTGACTCAGTTTCGAATCGAGGTTTTTAGCGTTTGATGGATAGCT
ACTAATTGTTCCGAGAACTATTTATTATTGCAATCAACTTTAAAGCGACTATTAAAGGGTCATGTTGCACGGGTCTCAAGTGTAACAAATGAGAA
ATTGCTAATGGAAATCGCTAATGAGATCGTTAAATCTGGTAAACAAATAACATATCGCCAAGTTAGCCCGTCCATCGTGGCTGCGAATCTCTCGC
AGAGCGACTTTCGATCGCCGTTTAGTACTCAGACGTCACCTGCCTAATGTTAATGTCAATTTAAGTGTGTATAACTATCGCACATATATTATATA
AATTTATAACGACGATTGACTAATCACTGGGTTGACTTTTCAGCAATAGCGATTTTCGCTTCAAAGTCTAAAGTGTGTGCAATCCCGTATGGATA
CGAGCCGAGCTCGAACACAGGCTCACAGCGCGCGGTTTGTGTTGTGTATTACACTTGAAGTTCAATCCCAGGTAAAAAGTGGGCCCAGGTATAAA
AGCCCACTTCATAGAAACATTTCTCAGTTAGTTCCAGCAGCTGAATTGCTTCACATCTATTCGCTCCGAGTCGCCCCACAAGTCGAGCCCCATTG
TAAGACCACCGCACCGTTTATAGTTTTTGGAGCCGATCGGCTCGGCTGGTCGACTGGTGGCTGGTAGTAGTCCACACACTCATGGACGCAGCCAG
ACGGGCAACCAGTTTCATTGTGTATAAACAGTGACATCTTTTCAGACAGCGAATGTGTTTCAGATACGCATACAAAGTGGCCTGCCTGGCTGTGC
ATTAATTTGCATACAAATCCCATAAGTCCACAGATACATTTTGCGAATGCAGTCGCGCTCGATGGCTAGTAAAAATA
(SEQ ID NO: 298)

Exon: 1001..1223
Exon: 1724..1951
Exon: 2003..2170
Exon: 2235..2687
Start ATG: 1122

Transcript No. : CT10496
CAGGGTGTTTCGTGTGAATGATTTCGCCTCTTGTTTCTTATCTTTAACCTTCATTTCTGGCTCCGTTTGGCTATGAATTAGGAGCAGTCCCGAAT
AATCAGTCGAGCATACGTAGTTAACGATGGCGCCGAATGCAGCAGTACCAGTGGAGCGATATGAGCCTGAGAACATCGGGATCAACGCCATTCTC
CTGGGGCCGCCGGGTTCCGGCAAAGGAACGCAGTTCTGCGTGTGCCACCTGTCGACCGGCGACATGCTGCGGGCGGAGATTTCATCCGGTTCGAA
GCTGGGAGCCGAGTTGAAGAAGGTCATGGATGCCGGCAAACTGGTCTCCGACGACCTGGTCGTGGACATGATCGACTCCAACCTGGACAAGCCCG
AGTGCAAGAATGGATTCCTCCTGGACGGATTCCCCAGGACTGTCGTTCAAGCTGAGAAGGTAGCCACACGTCTCGACACATTGCTGGACAAGAGG
AAAACCAACTTGGATGCTGTCATCGAGTTTGCCATCGACGACAGTCTGTTGGTGAGGCGCATCACTGGCCGCTTGATCCACCAGGCCAGCGGGCG
TTCGTATCACGAAGAGTTTGCCCCTCCAAAGAAGCCAATGACGGACGATGTCACTGGAGAGCCCCTAATCCGTCGCAGCGATGACAACGCCGAGG
CTCTGAAGAAGCGACTGGAAGCATATCACAAGCAGACAAAGCCGCTGGTCGACTACTACGGCCTGAGGGGTCTGCACTTCAAGGTGGACGCCGCC
AAGAAGTCCAGCGACGTCTTCTCCACCATCGACTCTATATTCCAACGCAAGCGTCCTGCCCAGATCCAGTTATGATTTGTTCCTGCGCAATGATC
AACTACTGATAACTGCCTCCTGACAATTTATTTCGAGACACACACAACGTTTAAGCCTAAAGTTATAGTTGCATCCGGAAATCCTGAACAAACGA
AATTACCTTTGCAGGTCGACTACTTTCCTTGTACAGATTTCTAAAGTGTATGTGTTTGTTACTTTTTACATTTCACTATTTGTAACTACAATACA
ATTTAATAAAAAAATCGAAGGAAACAA
(SEQ ID NO: 299)

Start ATG: 122

MAPNAAVPVERYEPENIGINAILLGPPGSGKGTQFCVCHLSTGDMLRAEISSGSKLGAELKKVMDAGKLVSDDLVVDMIDSNLDKPECKNGFLLD
GFPRTVVQAEKVATRLDTLLDKRKTNLDAVIEFAIDDSLLVRRITGRLIHQASGRSYHEEFAPPKKPMTDDVTGEPLIRRSDDNAEALKKRLEAY
HKQTKPLVDYYGLRGLHFKVDAAKKSSDVFSTIDSIFQRKRPAQIQL*
(SEQ ID NO: 300)

Name: Mitochondrial adenylate kinase isoenzyme 2,
Classification: enzyme
Gene Symbol: anon-Dak2
FlyBase ID: FBgn0024906

Celera Sequence No. : 142000013384074
TGCAAGTTCAAAGTCAGAAAATGACAAATAACCGAAAGGCACACAAAAAACAATCCTAAACATGTTTGCTTGCATGCCGAGACACGCACATACAT
CAATATTCATGTATAAACAAGCTTACAGTGTAGGAAATATAAAAAATTACAAAACTAGAACTGTGATTACCCACACACATGCACAACAAGATCTG
CCTACTACCTTAAATTTACTCGCTGCGATATGTGTAGCACATGAGCACACAACATATATGTTTTATAGCACTTTTAGGCGCTTTTTATTCGTTTA
TGCGTAAATAGAAAACGTGAACGACGTGACCAAGTGTGACCGTTGCTTATTTTCGTCGCAAATCTCGCGTGTGGTCAATTTGAACCGTTGTCAGA
AACTATAGGGTCTCGAAACATGTGCAAATAATTCATTTATATCATTCAACTTATGCTGCAAATAATTGCTATTATTATTATTTTAATTAATTATC
CACACTGCTTATGTTCTTCGCTCAAACAGGAGGTAATTAAATCATTGAAGGGATTTCAAAAATCTATGTATGCATTCACTACTAACTAGCTTGGT
CTTTTTTTTATTTTGCGCCGCTTTATAAATTTAAAAAAATATCATTTGGAATTACACACATCACTGTGTTAAATTAAAAAGAAGATTTTTAGTGA
TTGTTTTCTTTGAGATATTGAAGTCGCTATCTGCTCCTATATAAATATTATTTCGAAATTATCGATTTATAGTGCGCTATACTGACAAAAAATAG
GCTGAAATTCGCATGAACAAGCATATTGTGGTAAGACAAAATGAAATCAGAACTTCCCAAGAACTACGTTGGAAAATTACAAATGCCCAAAAGTA
TTGCTCCACAAAATATCGTAACGAAATATCGCGAAATTTGCAACACTTTTGTGCACATTCGGTGGCAACGCCGCCTAAGAAAATACCTATTGCCC
CAATCGATACCTATCGATGAGCGTGGGCAGCCCTGTTTGTGCATGTGCTGCCATTCGATTTGATAACCAGCACTCCGTGCACACGTTTTTCGGCT
TTCTAGAAATAATTGGGCTGCGATTCAAACTGTGAAGTGATTTTTTCTATATTTTTTTTTGTGTGCACAAAGGCTCTTGTAATTCGAGGATTTG
GCCATCGCGAGTGCGGGTGATTAAGCAGGCAGCTCCGATTGCCAGAGTTTTGCGGATGCATGGCAACACTGCCGCACGCCGGCCATGTTATTGTG
ATTTGTAAAAGGTGGAACGTAGACACGTGTTTAATTCGTGCAGCACTTTAGCGTTGAGAAAACGACAGTAAATCGCCAGCAAATAAGCAAAAACA
ATACACAACTCGCGTGTGCAGTAGATAGCTTTGAAAGCACCCAAAGATAGTGAGCAAAATAAGTTACCCAAGCGGTTCACAAAGGTAAGAAATCG
CAGCACGCGGAACATAACCTAGTACAAAAAAAGTGCGTGTGTGTGTTTGCCAAAACAGAGAGATGTGACGGAAAATGGTGTCATGTTCTGTTCTG
TGTGGATTTGTTCCAATGTCCGTGTCTTGAGCTCTATTCGCACCTCTTTCCCGGTACCATAGCCAACGTTTTAACTACCTTTTTTTGTCAACTT TTTGTTAAGTGTATGACTCTGCCTTGCCGCTGTTGTTGTTGTTCCGGCAAAGTGACAGTAAGTGGTTATGGAAAAAATTTGGAGTTCAATTCGGC
GATTACACAATGACAGCACTCACACACACACACACCCACAATCGCACGCATACACATGCCGAGCATAAGTGCGTCTGTGTGTGTTACAGCTTTCA
CCGTTAATGTTCGGTTTTTTACGCCTGAAAGAGAACAAAGGCGAAAAGGAGCTGCCACTCCCACAAAGAAAACATTGCGTCTATGCATACATAC
ATATGTATACACATATAAAGTAGTATATCCCCCGATTATACAATCCCCGCCCATTTTTGGCCACCATATGATCGGAAACCACGTTGCCAAGATTA
TAACAATGTGGACTTTTTCGGCTAGCTGGCAATGTTGTTGCACCTGATTTGTTGTTGTTTTGGTGCTCTCTTCTGGCTTGCCTCTCTGTGTCGCT
CATTCTCGCTTGTTCGGGGGAATTTCAAATTTTTAGGCTGTTGCTTCACCTCCCCGTTCGACGGCTTCCTCTTCTTTTGGCCGCACTGGTATTCG
AGTTTGGAGCAACAACAATGTGCAAGTTCAAAGTCAGAAAATAACAAATAACCGAAAGGCACACAAAAAACATGCCTAAACATGTTTGTTTGCAT
GCCGAGACACGCAGACACATCAATATTCATGTATAAACAAGCTTACAGTGTAGGAAATACAAAAAAAAAATAACAAAAACTAGAAGACCATTGCG
AAGTTGTTGTGCCCTTATCTTACATTTTGTCGTTTTAATTCAAGAGTTGATACGAATACGTGTAAAACTACACTTCTCCCTGCTCTTATGCATAT
CCATTTATTAAGAATTTTAGGCAAAATGTGGCAAGCTTTGTCAACAAGTTTTAATACTCTAAGCAAAGGGTATAAAACGTAATCTGAAAAATTCC
CGTCACCCGGTTTCGACGATTAGGAAATGCCACAGCTGTCTGGCCAGTTGCCCTTCCATGGCCATTTTATAGCACCCCACTAGGCCCCTTATCCC
CCACCCCCTGCATGCTCCCATCAACCGTTGATCTGTCGCTATATGTACATTTATACATATACATATGCATATACATATACATATGTACATACATA
CAATGTATGTTTGTGTTTCAGTTGCTTGTCGATTGAGCTTATCATCTGACCACTGTGTAACAGGAGGACCTTTGGGCCCTAACAAAGTGACGATA
TTGTGGATGGGGGAAGCGGGAGTATAGTGGGTAAATCGGTTCTATAGTGAGTAACTTAAAAGTACTAAAGATCTCATGGCTTTAAACTACTGTT
CGGCATGACTTGCACTTTTCGGGCCCCGGAAATTTTGACCAAATTCGAAGGAGCGTCTTACAATCCATTTGAATGGATTTTGATTAACGGTTTTC
GGATTTCTTTGTTCTAATGAGCTCGCCACTCTCTTTTCTTCTCTCCGGCTTTCTGTCTCGTTTCCGCTTGGTGGGATGAGTGTGTGTGTGGGTGG
AAAGGGGCGCTAAATAAAAACTTGCCACCACGCATCCTCTCTTTTTTCGCGGGTTGGTGGGGGTATGCCGATGCGGAAGAGCGGATGGAGTGAAG
AGCGGAGAATCGGTGCCGAAATAAAAAAAATAATACAAATAAAAAGCCAGAGGAATTGGCAATTAGAAGGCGTGCAAAGTAGTTTCCCTTCATAT
ATCGAGCAGTCGATATCTCGAATCTCTCGAACAATTTCGCCGGCATATCGAAACCCAACAAAAAAAGAAAGAAAATAAACAAAAGCATAGAAGAA
ACTCCAAAAAATAAGCCGAAGCGAATTGATGCCATAAAACGACATAAAATACAAACGAAACCGGAAGAAGCAACGAATTCAGTTTTATCCTAGTG
GTAATACAAAAACACACATTTATTTTGTGAATAGGTGATGAATTTCTGGCAAAGCTGTTGTTTTCGTAACTTTTAGTTTTGTTTTGTAATGATTT
CGTAACATTTGCCATTGCCATACGTAAACGTAACGGTTTCTTCTTGCGCCTCTCTTCCGTTCTTCGCCGACGCTCTTTTGCGTTCTTGCGCACGC
GCTCTTTGCATGCGATCTATCGCTCCATCTCTCTCGCTCTCTCCCGTTGCGTTTTTCCCTTCCGCGTGGCATTCAAAAATCGCTTTGCACCTTTT
TCGTCGTTCTCTCTCGTTGTCTCTCTCTCTCTCGGCATTTGTGTTGTTGTCTATATTTACGTATTTATTTGTTGCTATTAATACGCAAAAGTTCA
GAAAGGAAAAAACCAAAATCAAACACACTGGCAAACACACACACACACACGCACACTTATGCAGACGAGCACATGCAGGCGGGTCTCGTGACTTG
CAAAACCAATTCGAAACCTTTAAATAGGTTTTTCAAATATAACAACATGCATATGTCGTTATTTAAAAAACAACGTTCATGTGGATGGTGTTGA
CAAATTAGCCCTTTAATCTCACACTTTTCTTCAAAATTGATTTCATATTTGAAATTCTCGCTTAAATTTAAACGCAAATTCAAAGCTCTTTACTT
TGTTTTCAAAGTTATTCTACACAAAATTGCATATTGTGTACCGTTTCTTATCTTGAGCCATGACAAGCTTTTTAAAGTAATTATATACGACGCTA
CTTGATTTGTAAATTGTTGCCCTGATAAGAGGTGTTCACACATTATTTCCAATTGTAAATTAAACAACAAACCATAACTTTTCCAAATATTGCAC
AAACAAAAGCTACTTCATTTTTATTTCAGTATTAGTGTGATCAAAATAATCCTATTTGTGTGACAGTACACAAGTATATTTTCAAATCGCACAGA
CTAATATAACTTCTTCTCCCTTTCAGATCTTTCAATATTCAGCGAAAATGGTATCCGGTCGTCCTCTACTCTACCTCTCACTGCCCGGTGTAGCA
TTTATACTCGGCGTCTTTTGGTTTCGGCGTAGATATAAAAATTGTTTAGACAAGCCCGACGACGAGGACTCATCGGCCATCAATGACTCGTCGAT
TGAACCAACTGTGCAGGCGCGCAAGGCCAACGGAGTCCTGCAGAATGGCAAGCTGCCACAGCAGTCGGCCAGCAAGTCGATGAACATCAACGGAA
CTTTAGTTAACGGTAGCGGAAGCGGTAGCGGAAGTAGCAGTGATGAGAAGGACAGCCCCACTACCATGTTGTATGGTAAATCAGCACCAATCAAA
ATCCAGAGCAATGGACGCACTTCAAATGGCAAGCATCAGCAGCAGATCGATTCCGAAATACTGAAGTCAAAGATACAGGATGCCGAACACAAGAC
ACTCTGCTCCATAGACGAGGATTTCGAGAATCTATCGTCGCCACGTGATTTACCCGATTCGGTAAATACACGCGTATCCTTCTACAATCGTAAGG
CTACCCAAAAGACGGTGGAACCGGTGGTGATTAAGGCCACGCGCACACCCAAAATATCGCCAGAGAACTCCTTCCTGGATACCAACTACACCAAC
AAGGAGTGCGAGCAGAACAACAACTGTGAGCCCAAGGAGGAGCCCTCCAAGAAGGAGGCCGATCAGGAGGAGCTCGAGCAGGATCAGGAGCAGAC
GGTGCTGAAGGAGGAAGTGGTGGATAGCAATGGTAATCAGAAGCGCAATGTGGATGCGGCCAGTCCATCGCTGAGCATTTGCAGTGTGCAATCGG
GCGATTCTGGCAAGGGATCCAGCTTGCCGCGCTCGGAGGCGACACGCGTGAAAACCACCTACGAGTTCCTCTTCCCGATCAGCTTGATTGGTCAC
CTGTACGGCCGCAAGCGGGCGTTTATTAACCAAATCAAGGCCAAGACCCTGGCCAGCGTGTCTGTAGGCAAGAATCCCTACTCGGGCAAGGTGCG
CATCTGTACCATTGAGGGAACGGAGAGCGAGATTGATGCCGCCCTGGCCATGATCCGTCAACGTTTGCCGGCCAAGCGCTATCCGAACTTCACCA
TGCAACGCATCCACTTTGCGCTTCCCCAGACCATAGTTCCTCTTTCGACCGAAAGCCTCTACAATCTACAAGTGAGTGGTGATGGTGTGACGATG
ACAATGGTAACGATGCCGCCGACACGACATGGCTATAGCTGATTAGCTGGCTAATTAGCTGACTTGATTTGATGATTTTATGGTAGTATTCCTCC
CGTTGAATACGCAGAGACTATTTCAAATTCTCTAAGTGGTTAACACTGCTGTTCCTGTCGTGTCGGCGCAATCGGAAAGGCTTCGATTTCGAGTC
CCCATCCATCCATTCATCCATATATCTCTAATGCCTTGGCTAACTCCTCCTTCGCAGCTGAAACTGATTGAGGGCATCAACAACGATGTGGTAGT
GAGTGCGGTGCTATCTGGGTCGCATATTTTCATCCAGCACCCGCTGCATCCCTCGCATCCATCGTTGCCTTTGCTGCAGAAGCAGCTGTACGATA
GCTACTCCACCATGGAGGCGCCATTGCTGCCCAGTTTGGAGCTTAGTGCCGTGTGCGTGATACCCATCAATGATGTGTGGTATCGCGTCCAGATT
GTCGACACAGATCCCGAGGACGAGGAGCGTTGCGTAATCAAGTTTCTTGACTTTGGTGGCTACATGAATGTCGGCTTCAACACACTGCGACAGAT
TCGCACCGATTTCATGAATGTGCCCTTCCAGTCCACCGAATGCATCCTGTCCAACATTGAGCCCATCGGTGAGTGTGTGTGTGTGTGTGCGCGCA
TTATGCCCTTATACTTATTCCTTGATTCTCACTTTTTCCACGCAGGTGGCACCTGGTCCATTGAGGCGGCCGAAATCCTCAACAAACTTACCAAA
GGCATTGTCTTGCAAGCACAAGTCGCCGGCTATAATAGTCACAACCTACCAGAAATCTTTTTATTCGCATCCCTAGGTCCCAATGTGAGTATAAA
TTTCCGATTAGAGAGAGACGGAGTGATTATGAAGAGCGAGAGAGCAGACTACAGTGCGTGACATAATAGCAAAACGGTTACGAGCAGAAACTTGC
ATCTTACTTTAAACAAGCTAACTAAGCCATTTGATTTGTTATGCAACTAAACTTAAACTTGTACACACATATGTTACCTTTTTAAAAACAAGCGG
ATGCGCTATCGTCTGTTTTTAAAAAGGGGACAAACCCTTGTTGGAACAGAAAGTTTCTAACTCTTGTTTCTAATTGCAGAATGTAATCTTTATCA
ATAAGGAGCTGGTCGGCAGAAAGCTCGCCAAATGGGTGGAGATGAGTGACTAACAGCCTTAGTGAACAACTCAACTAGCAACCAAGAACTATATG
AAAACTTAAAAGCAAACTTAAACAACAATCACTCAAACCCAAATCAAGCAACTTGGCGGTGCAACAAAAAAGGAATGCTTGAGTATTGCGCAACA
GGCTCCAAGATGCGGATTCGGATTAAGGATTTCGTTAGCAGCTTTTGCAGTTAGCATGTAGCATGTAGCACACAGCAAATAGCAATTGCCCGATT
CCAAAAGAACTGGCAAGTGCAGAGGCCTCAAAACAAAGAAAATGAAACGTTTGTTACGTTGTTTAGATTGCGACTGAGCCCAGAGAGAGCCCCTT
AATCATTACATAACAAACAACACACACTCGCCAAATACACACACACACACACACACACACACGCATATATGAGTAAGAGCACCTAACACCACA
CTAACCCATACACATTACACAACAAGACAAACGTTTGTTTGTTGACTGTCCAGAATTGGATACCAAAATGGAGGGGGAAGTTAGGGATCAGCTGG
GTTATGCGTTTTGTGACCACATGGCAACACATGGGCGGGCGGGCATGCAACGGATCGACTGGAGCTGCAGATATTACTATACTCAGTTTATAAGT
AGGCATTACTAAATAATGTACATAGATTTTATAACGAGAACGAGATGCGAAAAAAAAACAAAGAACATACTAAATAGACCCAACTAAAATACCAT
GCGTTCATCAGATATACAGAAAAACAGAAACACAGAAACATAGAAACTCTGGATAAGAATGGAGAAAAACCTGACAAAACTTTAGTTTTATGCTG
CTATTTGCTGAGATCTGTAAATATTATATTAGGCCTTTTTAAACAACTGATAATATCTAATCGACGAGTTCATACATTTACATGCATTATACATT
TTTTTTTTTTTGTTAATTTGTATTCAAACTGTAATCAGAAAATGTATTCAAAATTCCCAACCCAAAAATAACTCACACCCGCACTAAAGCCACAG
AATGCCTAACAAAGAAAGAAACCATTTAAAAGCAGAGACAGAGTGACGTTACGAATTCTTCATAATTATATATGCGTGTGTGCCATTGTTAGACA
ACAAACCAACATTAAACATAACCAACATAACAAGCAAAACAACAAACACAATAATTAACAAAAAAAAAAGAAAAAAAAACAGAAATGGCTACTTT
TTCCCCAAAACAAACCCATTGTAAATAAAATCCATTTCGACAGACAAAGAAATGCAAAAACAAATGAGAAACAATGATTGTTGCTACCAAAACTA
GCCTATTGAAAAGAAGGAGTGAAAACCTCAAAATGCCTTTCTTTCAAACTTCTTTTGTATATGGAAGAGGAAACTTCTTGAAGCGACAAGAAGAA
GCAAGCAAGCGAATTGTTGCAAACTTATCGCTTAAGCTACCAATTCTGGGTGTCTAGCCTAGCAGCAATATTAGCTAGAATTGTTCTAAGTGTAG

FIGURE SHEET 167

CACAGCCACAACAGCATCAACAACACATCGATAACACAATATAACACACAAACACACACTAATAAATCAACAAAGAAATTAATCATATTTATTTT
GTTGAGATTGAAAATAGAGTTTATTTCACTGTATCATTCATTGTATTTACATTGACATTTTACATTGATCGGCAGCAACGGAATTACTATATA
AACATTTATAAATCGTTTCAAAAAAAGATTTCAGGCTCAATCACAATTCAGCTTAATAAGTCGTCGTCATCGTTCTCATGTCGTCATCGTCATAA
TTAAATTACTTAGATAATATAATGTACAAGTGATGATCCACACAATATCCATCTATTTGGTCAACATGAAAGACTTTGGAGGTGTTTTTTCTTCT
TCAACGGTAGTCTACAAATATTCTAGTTAACGCTATCATTATACCGTTATTATTATTATTATTATAACTATTATTATTATTACCTCTTTTTTTGC
TGTTTGTTTTTAGATCCTTCTTGATAATTAAAGCAAATTCATTCTAATTGTTATCCTAAACTAAAACAACTTTTGGAGGGGCTGCCCTCCACACA
CTGTAGTGCAAATTCGTTTAATGGTTCCTCGTTTTAATAATGTCGTTTAATGCCTTTGGAAATTCGAACTACATTTTAGTCTATGGAACACTAAA
TACATATTATTGGTTACTTTTAAATGAAGCATTCAACTAGATGAAGGGAGTAGGATTTCAATTTTTGCATGCACCAGAGTTGTCAACGTTCTCGG
TGTTCTATCGAATTCATTGTAGATTTGTCACTTGTACAATTGTTGATAAACTGATTAACTGATAACTGATTAACTGACATAGAGATAATGCAAAC
ACGACAGACATGATGTAGAGCACATATTGAAACTAATCTTAGTCGATAGCGAGAAGAGAAGAAGAGACGTGAAGTGAAGAGTCCTCCCTCAAAGA
TCATCGTAAGTGTGTGGTACTTCTATTTTTTTTTCTTATCTAGTAATGCTGAGAGACGAGAGTTACGAATAAGATTTAATTTATAGACGCATTCA
AGTGAGAATAATTTACAAATCTAGTTATTAACTAAATATAATGCAAGTACATTAAAATAAAATATTATTGAAAAGTAAAAAAAACGGTGTTTCAT
CTGGATCGTTGTGGGGGGGGGGGGGTGGTTCGTTATCCCAGGAAGTGATATCGCCACTTTTATGGATCCGCCCGGCTAAACGTGCCAACTAATTT
TATAATTCATGTACTTACCCGTGTCAGGGTAAGGTTCTTATCCGAAAAGCTGAATTGACGTGATGGCCGCGATAAGGAAGTTGCTAGCTTCATAT
TGTTTGCGATCCCCCCAATAATGTCCAATATCCGATTCCCATGATTCCCTCCATGCAATCGATCAAAGAAAGCCTTGATTGCCGCACTAATGTAC
TATTCGATGATCGTCTGGTTGGCTCGTTGGCTGCACGACGATCTCTTGGATATAAAACGATTGCGATATCGAACTTGCAGCTGGAGGTGGAGAAC
TCTGCGTCAGAGTTGGTGGCCAGAGATTTGCTTGTGAAACTGTGAAACTGGTCAGAAGCGGTCTTTGGATCGTAAAACTTTCATTGACCATTGAG
TGGAATTCTTCCGAATCTATATGTACCAGCCAGCCTAATTACCCCAGCGATTATCGACTCCTAATTGGTTTTGTCTACGGTTCTGTTTTCGTTTC
CTTTTCAATTGATTGGTCACTTCGTGGTGGTTTCACCTAATCAGTGTGGAAAATGTCCAGTCACGGCCGGTTCGGATAAGTTCATAAAGTGCTTT
TACTGTGTCTGGGTCTGGCGGGTCCGTCTATCTGAAGTTATTTACTACTGCTGACCATTTTGGCCTGCCGGTTTTTATCGAAGTACCAAGTGTTT
CACTCACCGCGTCGTACAGTGGACCCCGCCTATGTTGGCCGCAATGATCGATTTGGGTTGATAAGATCCTGGCATCCCCATATATAGTTATATCT
ATGTTCCCCTATCGCCGTATCTGCTCTCTATGTTCTATCAACGATCTTCGTGAGTTAATCAGCAAAAAAGAGCTCACGTTCGGGATTTCCTTACC
TACACGCAGAGAAAAAGATCACTTCATAAATTTATCCAGCGGCAGCTCATCAAGTAACGTGGAATTCCCAGCTTATCGCATTGGGTAATTTGAAT
GGAGCGCTGGTAGATAATTCACAAATGGAAAACATTTACCCAATGACTTATTTACTCGTTTTATAACATCTTGCAGCATTTTCTCTTCGAGTGCA
GACTATATTTTTGGGTAAACGCCGTGCTGATGTCTTCAGCTTCTCGGCGGATACTTCCTTATCCGAGCGCTGGAATCTCCGATATCATCAACGAT
CGCCCAACGAAGAGCAACCGAAGTTTGTTTTCCCCATTCCTAATCGAGCACTGGGGGGCTGGGGATTGGGGATTGGGTACTGCGTACTGGGTACT
GGGTACTGGGTACTAGGTACTGGGCACTTAGGTACCAGCCAGTCAGGTACTACCGCTGATTTTCTCTACAAAGCACGGCTATACGGCTATATGTG
TGTGAATAATTTCACGCTTATTACCTGCTGAGCGCTGGCAAAACGCTGCTTGACTTTGGCGGTTCTTAAAGCGGCCGGCACTCGCAATATTCTCA
GTTCCAGCCGCGGCATTCACGGCACCACAAGCGCGCCTCCAGCACCGCCAAGTAGCCAAAATCCACAGCCCAAATTACGAAAATATTACAGAAAA
CTAAACCCTGAAACTGCAGTTGGACGCTAACCCAACCAACCGTAACCAAGGGCTGGCCAAATGCAATGTGCTAATTACTATTAACAAAAAAAAAA
AAAATAAATAATTAGTAATTAAATAAGCAAAACGCGAGTAGCCGTCAACTGTTTTCATTAACCGGGAAAATTAACAAGTGGCTAGAAAAATGGAA
TTGAAAGGAGTTCAGCCATCGAATGGCAGCTCAAATGGAAGTGGAAATGGAGCCACCAATGCTGCATCAACGGAAGTAAGTGTTAGACCATGAAA
TCAGGCAATTAATAGTATCCCTAATGGAATTGCTTTCGAGTGGCACTTGAAGAACTCAAGTGGCCAGCGATTCAGATTAGAAGAAGGCAGTGTTC
AACAGTTGGAACATTAAGTATACGCCGTGTGGTGCATGAAAGTTTCACAATGTACACTGTGAAGAAACATTTCCCATGCAATAAACTTTATAAAA
CTTCAATGGACTTTTACCCCGAAATTATGCTTTGATTGGCCCTTCTTCACAACCGTCCTTGCAATTCGCTCAGTGTTTCTGGCTTTACAATCGCC
AAATGACTTTATGATCATTAAGGCTGTTAGACCTTAATTGCAGGCCAATCGACCGACAAACGAATATGCGATTTACGGTCCACCCCAATGTGGGG
TGAAAGACTTTGTCAGCCGGTTACTCCATGCATATCTTATACGCTTTACGATACCCAGCGACACATAAATGTATCTTAGAGCTATTTTCAGCCGA
AGAATGAACCGAAAACGTTAGTTATCTGGCCATAACTTAGCGTACGGCTCGAGATCAGCGAAAGCTATACTATAATAGGCT
(SEQ ID NO: 301)

Exon: 1001..1414
Exon: 4492..5676
Exon: 5948..6338
Exon: 6411..6608
Exon: 10622..10956
Start ATG: 4513

Transcript No. : CT10921
CCATTCGATTTGATAACCAGCACTCCGTGCACACGTTTTTCGGCTTTCTAGAAATAATTGGGCTGCGATTCAAACTGTGAAGTGATTTTTTCTAT
ATTTTTTTTTGTGTGCACAAAGGCTCTTGTAATTCGAGGATTTGGCCATCGCGAGTGCGGGTGATTAAGCAGGCAGCTCCGATTGCCAGAGTTT
TGCGGATGCATGGCAACACTGCCGCACGCCGGCCATGTTATTGTGATTTGTAAAAGGTGGAACGTAGACACGTGTTTAATTCGTGCAGCACTTTA
GCGTTGAGAAAACGACAGTAAATCGCCAGCAAATAAGCAAAAACAATACACAACTCGCGTGTGCAGTAGATAGCTTTGAAAGCACCCAAAGATAG
TGAGCAAAATAAGTTACCCAAGCGGTTCACAAAGATCTTTCAATATTCAGCGAAAATGGTATCCGGTCGTCCTCTACTCTACCTCTCACTGCCCG
GTGTAGCATTTATACTCGGCGTCTTTTGGTTTCGGCGTAGATATAAAAATTGTTTAGACAAGCCCGACGACGAGGACTCATCGGCCATCAATGAC
TCGTCGATTGAACCAACTGTGCAGGCGCGCAAGGCCAACGGAGTCCTGCAGAATGGCAAGCTGCCACAGCAGTCGGCCAGCAAGTCGATGAACAT
CAACGGAACTTTAGTTAACGGTAGCGGAAGCGGTAGCGGAAGTAGCAGTGATGAGAAGGACAGCCCCACTACCATGTTGTATGGTAAATCAGCAC
CAATCAAAATCCAGAGCAATGGACGCACTTCAAATGGCAAGCATCAGCAGCAGATCGATTCCGAAATACTGAAGTCAAAGATACAGGATGCCGAA
CACAAGACACTCTGCTCCATAGACGAGGATTTCGAGAATCTATCGTCGCCACGTGATTTACCCGATTCGGTAAATACACGCGTATCCTTCTACAA
TCGTAAGGCTACCCAAAAGACGGTGGAACCGGTGGTGATTAAGGCCACGCGCACACCCAAAATATCGCCAGAGAACTCCTTCCTGGATACCAACT
ACACCAACAAGGAGTGCGAGCAGAACAACAACTGTGAGCCCAAGGAGGAGCCCTCCAAGAAGGAGGCCGATCAGGAGGAGCTCGAGCAGGATCAG
GAGCAGACGGTGCTGAAGGAGGAAGTGGTGGATAGCAATGGTAATCAGAAGCGCAATGTGGATGCGGCCAGTCCATCGCTGAGCATTTGCAGTGT
GCAATCGGGCGATTCTGGCAAGGGATCCAGCTTGCCGCGCTCGGAGGCGACACGCGTGAAAACCACCTACGAGTTCCTCTTCCCGATCAGCTTGA
TTGGTCACCTGTACGGCCGCAAGCGGGCGTTTATTAACCAAATCAAGGCCAAGACCCTGGCCAGCGTGTCTGTAGGCAAGAATCCCTACTCGGGC
AAGGTGCGCATCTGTACCATTGAGGGAACGGAGAGCGAGATTGATGCCGCCCTGGCCATGATCCGTCAACGTTTGCCGGCCAAGCGCTATCCGAA
CTTCACCATGCAACGCATCCACTTTGCGCTTCCCCAGACCATAGTTCCTCTTTCGACCGAAAGCCTCTACAATCTACAACTGAAACTGATTGAGG
GCATCAACAACGATGTGGTAGTGAGTGCGGTGCTATCTGGGTCGCATATTTTCATCCAGCACCCGCTGCATCCCTCGCATCCATCGTTGCCTTTG
CTGCAGAAGCAGCTGTACGATAGCTACTCCACCATGGAGGCGCCATTGCTGCCCAGTTTGGAGCTTAGTGCCGTGTGCGTGATACCCATCAATGA
TGTGTGGTATCGCGTCCAGATTGTCGACACAGATCCCGAGGACGAGGAGCGTTGCGTAATCAAGTTTCTTGACTTTGGTGGCTACATGAATGTCG
GCTTCAACACACTGCGACAGATTCGCACCGATTTCATGAATGTGCCCTTCCAGTCCACCGAATGCATCCTGTCCAACATTGAGCCCATCGGTGGC
ACCTGGTCCATTGAGGCGGCCGAAATCCTCAACAAACTTACCAAAGGCATTGTCTTGCAAGCACAAGTCGCCGGCTATAATAGTCACAACCTACC
AGAAATCTTTTTATTCGCATCCCTAGGTCCCAATGTGAGTATAAATTTCCGATTAGAGAGAGACGGAGTGATTATGAAGAGCGAGAGAGCAGACT ACACATTTTCTCTTCGAGTGCAGACTATATTTTTGGGTAAACGCCGTGCTGATGTCTTCAGCTTCTCGGCGGATACTTCCTTATCCGAGCGCTGG
AATCTCCGATATCATCAACGATCGCCCAACGAAGAGCAACCGAAGTTTGTTTTCCCCATTCCTAATCGAGCACTGGGGGGCTGGGGATTGGGGAT
TGGGTACTGCGTACTGGGTACTGGGTACTGGGTACTAGGTACTGGGCACTTAGGTACCAGCCAGTCAGGTACTACCGCTGATTTTCTCTACAAAG
CACGGCTATACGGCTATATGTGTGTGAATAATTTCACGCTTATTACCTGCTGA
(SEQ ID NO: 302)

Start ATG: 436

MVSGRPLLYLSLPGVAFILGVFWFRRRYKNCLDKPDDEDSSAINDSSIEPTVQARKANGVLQNGKLPQQSASKSMNINGTLVNGSGSGSGSSSDE
KDSPTTMLYGKSAPIKIQSNGRTSNGKHQQQIDSEILKSKIQDAEHKTLCSIDEDFENLSSPRDLPDSVNTRVSFYNRKATQKTVEPVVIKATRT
PKISPENSFLDTNYTNKECEQNNNCEPKEEPSKKEADQEELEQDQEQTVLKEEVVDSNGNQKRNVDAASPSLSICSVQSGDSGKGSSLPRSEATR
VKTTYEFLFPISLIGHLYGRKRAFINQIKAKTLASVSVGKNPYSGKVRICTIEGTESEIDAALAMIRQRLPAKRYPNFTMQRIHFALPQTIVPLS
TESLYNLQLKLIEGINNDVVVSAVLSGSHIFIQHPLHPSHPSLPLLQKQLYDSYSTMEAPLLPSLELSAVCVIPINDVWYRVQIVDTDPEDEERC
VIKFLDFGGYMNVGFNTLRQIRTDFMNVPFQSTECILSNIEPIGGTWSIEAAEILNKLTKGIVLQAQVAGYNSHNLPEIFLFASLGPNVSINFRL
ERDGVIMKSERADYTFSLRVQTIFLGKRRADVFSFSADTSLSERWNLRYHQRSPNEEQPKFVFPIPNRALGGWGLGIGYCVLGTGYWVLGTGHLG
TSQSGTTADFLYKARLYGYMCVNNFTLITC*
(SEQ ID NO: 303)

Name: A-kinase anchor protein
Classification: enzyme_activator

Celera Sequence No. : 142000013384832
CCAGTGGTCCGCTGGTGGCTCGGCTCTCATTTTTGCATTTTTCTTCGGAAAAGTCCGCGCGCTGGAAAAGTCAACACAAGTTCACCTCTCCAAAT
TCGTGCGTGGGTGTGGGCGGAAGGTGGTGGTAGGTGGATGGTGGGCGGGAGTGGGTGGTTGGCGATTCGAGAGGGGGCGGTGCGTGGGTGGGTTT
ATTTTTAGCGCTGCTGCGACGGAAACGCGACAAGTCGGAGATTCTGCTTCCGCAATGTTGTTGTTTTTGCAGCCGTTATTATTAACAAATATTAC
GCTATCCACGGGCTCTTCTTCTTGCTTGTTTGCGTTGACAAATCTCGTTGCGCTTTCACAATCACATCAAATCGTGGGAAAACTGGTTTTCCCCC
CGTTTCTGAGCGGTTCACTCTTCGGTTCGTGATCGTTTGTGTCCGCGGGCAATGGAAAGTCTTTGTTTTTCACACGCGTTTATCACAACAGTAAA
TAAAATATCACTTTAGCCAGTTTAATCAACTCGGAGAGCAGAACTTTTAACCGTGAGAAATAACCGCATACTGAAGTGGCCAAAATCTGGGAAAT
CGCCATGGAGGAACTCGCGGAAAATACCAAATCCATGGCATGCAAGCTTTATTATCAGTGGCGTAGAAGAGGGGCCTTATCTGATTAATCCTCGC
TCTATAATTTTGAACCGCTTGCCATTTTTAAGGGCTCAGGATAATGAGATTTGTTATTCTTCCAGATTAATGTCATTAAATTAAAATCTTATGTT
TCCCCCTTATGTTTATAAGAGTAATCGCAAATATTCAATGAAGAAAAGAATATTTTATTTTATTGAACTGCCGAAATCAACAAATTAAACGAATG
TAATTAATTTAAATTTTAAATTATAACACCCAAAAAGTGTGATTCCCCGAAAATATCAGTTATTATACAACGTTATTTCGGAATTTGTAGAGGTA
TTTTCTGGCGCTCCCGCTGCGGTCACACTGAACACGAGTTTCGTTTCGGAGATTGAAAGAAATGGAGATTGACTTGGGATTTGCGGAAAAGAGCG
ACAATGGCGCCTGGCTGAGCAACCGCTACTTTCCCAGCAAGCTGGGAGGCCAGCCCGCATGGCTGGAACTGGAGGCCTTGCCGCCCACGTCGCAG
CTGCAGTGCAGCAAGTGCAGGGCACCCAAATCCTTCCTGGCTCAGCTATACGCTCCCTTCGAAGACGAGTACAACTTTCATCGGTCCATCTATGT
GTTCCTGTGCCGGAATTCCGACTGCCAGGAGGCCCAAAATGCAAGGTAATCCCTTCTAGCTCTGAAAACCAACTTGCAACCTAATCTTACCCATC
TTTCCAGCAATTTCACAGTCCTCAGGTCACAGTTGCCGCGAAAAAATAAGTTCTTTTCGGAGGAGGAGCCGAGCGACGTGGGTCAACCCCTGGTA
GGAACAGCAGCCATATTTTCAGAACATACTCATCATAATATGTTTTCTTAGCCCGCCGTTCCCTGCCTAAAGAAACTATGCGCCGCCTGCGGTTG
CCATGCTCCTCACGCCTGCAGCAAATGCAAGGCAATCCACTACTGCTCACCAGAGCATCAAAGGGCCCACTGGCCACAACACAAGCCAAACTGCG
GAGCACCAGAAGTAGCCACTGAGAAGCCCTTAACACAAATCGTTTTCCCAGAATTTGAGATTGTAATGGACAGCAACCCCGTGGAGTCTGGCGAG
GAGGACAAGGACGATGAGGCTCGCTTGGCGGAGTTCCAGGAGCTGGAGTCCAGCGGGAAGACGGGCGACTTGAGCAATGTTTCCGAGGCGGAGAT
GGACAAGTACTTCGGAAACTCGGCGGCCGCCGATGACAAGACCTTTCGTCAGTTCAAAAAGCAAACAGCAGCCGAACCCGATCAGATCGTGCGCT
ACAAACGTGGAGGCCAGCCCCTCTGGATCACGAATACCGTCAAAACGGTGGAGGACCAACTTAACAAGCTGCCCAATTGCATTGCTTGCGGAGGA
GAGCGTCAGTTCGAATTTCAGATTATGCCGCAAGCGCTGACTCTTCTGGAGGACGAAAACCTCGACTGGGGCGTCCTGGCCGTCTACACTTGCGC
CAAAAGCTGCCCCATCGACGGCTACGTGGAGGAGCTTCTCATCAAGCAGGACATTGTGGCGGAGGATCAGAGTTGACATTAAAATGCGTACATTT
AAATTTTATTCTTGTCAATTACGAAACACGTGAACATTTACTTCAGCTTGATGATGGGGAAGTAGCTGTGTTTGGAGAAGTCGAACTCTGGCTGC
CGCTTGACTTCCTTCTGGTGACCGCGAGCCAGCACATTCATCACCACAAAGTTAGTCCGTGCGATTTGCAGGAGGTCCAGCATCTGAAATTAAAC
GAAACGCATTTTAATCCAGGAAAACCAATTCAGAACTACCATTGACTTACCTCCTGATCTGGGTTTTGAATGCTTTCGAGAACATTGCGGGCCTG
GTCAAAGTGCTTGGCCGCATAGGTATATAGATCCTCGACGCTATGTCGCATCATGTGCTCCCGGACGTTTTTGAACTCTGCGTACGAAACTGGCG
GAGGACTGGTGAGTGTGGCGAAGGGCAGGAAGCGTCGGTTGTAGCGGATCTCCTCGTTGTCGAACTTGGACAGCGGCAGTCGCACGCGTCCGTCT
TTGGTCAGGGCGCCCATTGCTTTATACATTCCGCCGCAGAGGCTGAGTAGCGCGTGGTAGAAGACGATCTCGGCGCGGTACGGCCTTTGAGTCTT
TTTGTTCTTTTTCGGCTTGGCCGCCTTGCGGTTTTTAGCCGCTCCGCTGCCGCCCGACTGGGTCTTACTTTGGTGCTCGGCGTACTCCTCCTGGG
CCAGGAGGATGTTCTCCGTGCGCGTCAGCGCGGAGACCAGGAAGCCAATGAGGAACTCGTATGGATACCAGTAGATGTAGAGGAACTCATGCACA
GCATATAGTTCCAGCTCAAAGCCGGACATCAGGAAGATCAGCATCGCACGGAAACAGTTGTACAGCACCCATGTGGAGAAGTGGGTGCTGTGCTT
CAGAGCGGTGGCCATGGGCTCGTTGCCCTCCATGGCTCGTTCGTTGGCCAGTTGGTTCATCATAGAGTCCAATCGCGCTGCATCCACTTGGATGG
TGTCGAAGTTCTCTATCAGACGCGCCAGCTTATCCCGCTGTCTGGCGCGATTGAAGCCGCAGATGCGAATGAACTGCGTGAAGGTGTTCATGTTA
ATGCAGTAACGGAAGAAGTTCTCCAGGTGCTGCTGCACCTTGGGATCGGCAGCCACCGGATGCTTGGCATTCAATACGGGTGGCGAGTTGAAGAC
CTGAACCGAGTGGCGCAGGAACTGCTTCATGGGAAGCTTTCCGTGCGCCATACGCATGTTGGCGCTGAACAGGGTT
(SEQ ID NO: 304)

Exon: 1001..1280
Exon: 1338..1422
Exon: 1477..2401
Start ATG: 1012

Transcript No. : CT10985
GATTGAAAGAAATGGAGATTGACTTGGGATTTGCGGAAAAGAGCGACAATGGCGCCTGGCTGAGCAACCGCTACTTTCCCAGCAAGCTGGGAGGC
CAGCCCGCATGGCTGGAACTGGAGGCCTTGCCGCCCACGTCGCAGCTGCAGTGCAGCAAGTGCAGGGCACCCAAATCCTTCCTGGCTCAGCTATA
CGCTCCCTTCGAAGACGAGTACAACTTTCATCGGTCCATCTATGTGTTCCTGTGCCGGAATTCCGACTGCCAGGAGGCCCAAAATGCAAGCAATT
TCACAGTCCTCAGGTCACAGTTGCCGCGAAAAAATAAGTTCTTTTCGGAGGAGGAGCCGAGCGACGTGGGTCAACCCCTGCCCGCCGTTCCCTGC CTAAAGAAACTATGCGCCGCCTGCGGTTGCCATGCTCCTCACGCCTGCAGCAAATGCAAGGCAATCCACTACTGCTCACCAGAGCATCAAAGGGC
CCACTGGCCACAACACAAGCCAAACTGCGGAGCACCAGAAGTAGCCACTGAGAAGCCCTTAACACAAATCGTTTTCCCAGAATTTGAGATTGTAA
TGGACAGCAACCCCGTGGAGTCTGGCGAGGAGGACAAGGACGATGAGGCTCGCTTGGCGGAGTTCCAGGAGCTGGAGTCCAGCGGGAAGACGGGC
GACTTGAGCAATGTTTCCGAGGCGGAGATGGACAAGTACTTCGGAAACTCGGCGGCCGCCGATGACAAGACCTTTCGTCAGTTCAAAAAGCAAAC
AGCAGCCGAACCCGATCAGATCGTGCGCTACAAACGTGGAGGCCAGCCCCTCTGGATCACGAATACCGTCAAAACGGTGGAGGACCAACTTAACA
AGCTGCCCAATTGCATTGCTTGCGGAGGAGAGCGTCAGTTCGAATTTCAGATTATGCCGCAAGCGCTGACTCTTCTGGAGGACGAAAACCTCGAC
TGGGGCGTCCTGGCCGTCTACACTTGCGCCAAAAGCTGCCCCATCGACGGCTACGTGGAGGAGCTTCTCATCAAGCAGGACATTGTGGCGGAGGA
TCAGAGTTGACATTAAAATGCGTACATTTAAATTTTATTCTTGTCAATTACGAAACACGTGAACATTTACTTCAGCTTGATGATGGGGAAGTAGC
TGTGTTTGGAGAAGTCGAACTCTGGCTGCCGCTTGACTTCCTTCTGGTGACCGCGAGCCAGCACATTCATCACCACAAAGTTAGTCCGTGCGATT
TGCAGGAGGTCCAGCATCTGAAATTAAACGAAACGCATTTTAATCCAGGAAAACC
(SEQ ID NO: 305)

Start ATG: 12

MEIDLGFAEKSDNGAWLSNRYFPSKLGGQPAWLELEALPPTSQLQCSKCRAPKSFLAQLYAPFEDEYNFHRSIYVFLCRNSDCQEAQNASNFTVL
RSQLPRKNKFFSEEEPSDVGQPLPAVPCLKKLCAACGCHAPHACSKCKAIHYCSPEHQRAHWPQHKPNCGAPEVATEKPLTQIVFPEFEIVMDSN
PVESGEEDKDDEARLAEFQELESSGKTGDLSNVSEAEMDKYFGNSAAADDKTFRQFKKQTAAEPDQIVRYKRGGQPLWITNTVKTVEDQLNKLPN
CIACGGERQFEFQIMPQALTLLEDENLDWGVLAVYTCAKSCPIDGYVEELLIKQDIVAEDQS*
(SEQ ID NO: 306)

Classification: hypothetical

Celera Sequence No. : 142000013384832
TGTATGTTTCCCCGTGGGTGAAGTCCTTGGTTCCCTCCAGGCGACCGCGGGGCGGTGCCTTCTCGTAGTCGAAGGCCTTCTCTGACTTGCCGAAC
AGCTGGTTGGCCATCTCGATGTCCTCGCGGTAATTGCCCACGACCACCTTCTTGCCAGTGAGCGGGTCCGTTATGTCACCCAGCGGATAGACCAC
TTTTTCCACGTTGTGCGTGATGAGGCGGGTGAGGCGCTCTGGCAGTTCCCGTATCAGGACCACGTCCCCGGTCTTGCACACCTTCTGCGGATCGT
GGGCGAAGTAGAACTCGTCCTTCTTAAAGTACTGCGAGCAGAAGGGAAATTGTGTGAAATCTCCTGAGGCGAGATCTAATGTATATTATGCACAC
CATATTCAGGTTCTTGTCCAGCTCCATTCGGCGAATGCGGATCTTGGAGGCGTTCTGCTTGATGCAGGGCATGCACTGGCCCATTAGTAGGAGTC
CTCGCCTCGACATTACTTTAATTTAATTTAAGAGTTTAGAAAAATAAACAACCGGTTGGGAAACACAGCTGGTAGATCACTGGCGATAGTATCGA
TTGGGCCTGGAACTATCAATATTTCGATATTTTTTACTCAGCAGTTTCTGATTTTCAAAATCCCGCCAAATGCAATCAGCTTGCACGCGTCAGTT
AAAAAGTAGGGTAGTATGACTTTTCATCGCAAAAACAAGTGGATTCTAAGGACATAACATTTTCACCGTACTATAAACAGTGTATCAGTTTTACA
TAACATATCTTTTCAATTAAATAATGCTTTAATGGATTAAAAATGTTTACGTCAAAGTAAATACCTTTAAATTCATTTTGTTTATGAATAATACA
TATTTTTAATTCAAAATTGTAATAAGGAATTCGGCTCACGATGACATATCGCAAGATTTCCATTTATGTATCGATGTCTTCATGAAATACATTTC
TGTGTAGTCACACTTATCGATAGACCGCGCACTCCACGTGTTTTTCGTCCATTTTCTCGCAGCGCGCAACACGTGCGGAGGTTTCTCTCCGTCTA
TTAGTTGATTTAGCAGAAAACGTAGATAAAATGGCCGACGTGGGTAAGTCTGGCAAGTGATGAATTAAAAGAGTGCCCAAATAAACGGACTATGC
GCCCGCAGAAGTACGCAAGGAGAAGAAAAAGAAGAAGATCAAGGAGGAGCCCTTGGACGGCGATGACATTGGCACGCTGCAGAAGCAGGGCAACT
TCCAAATCAAGCCCTCCTCCAAGATCGCCGAGCTGGACACCTCGCAATGGCCGCTGCTCCTGAAGAACTTCGACAAGTTGAACATCCGTTCCAAC
CACTACACTCCGCTGGCGCACGGATCGTCGCCCCTGAACCGCGACATCAAAGAGTACATGAAGACTGGCTTCATCAACCTGGACAAGCCGTCGAA
CCCCAGCTCCCACGAGGTGGTGGCCTGGATCAAGAAAATCCTCAAGGTGGAGAAGACAGGCCACTCCGGCACGCTGGATCCCAAAGTCACGGGTA
AGTGAAGCGCGTGCTCGCCTACCGCCATACAAACCTAACCTCATTGTGTGCCGCGTGTTTTTTTTTCCTACAGGTTGCCTGATTGTTTGTATTGA
CAGGGCCACCCGTCTGGTGAAGTCCCAGCAGAGCGCCGGCAAGGAGTACGTGGCCATCTTCAAGCTGCACGGAGCCGTGGAGTCGGTGGCCAAGG
TGCGTCAGGGCCTGGAGAAGCTGCGTGGTGCCCTCTTCCAGAGACCTCCACTCATCTCCGCCGTAAAGCGTCAGTTGCGCGTTCGTACTGTCTAC
GACAGCAAGCTGTTGGACTACGATGAAACCCGAAATATGGGTAAGTCAGAAGTTTTGTTTATCCATTCTCGCTCAGAGTTGGTGCGTCGCTGCTG
GATTAGTTTATCCTGCAGAGGTGCAGCCTGCTTCAGCCAGTGAAACACCAGTATTTGCCTAACACAGCAAATGCACAATGTAATTGTTAAAACCT
CGTCTTTTTCTCTCCTCCAATTCTGCCCACTCACGTGCTCAGGTGTTTTTTGGGTTAGTTGCGAGGCCGGCTCCTACATCCGTACCATGTGCGTC
CATCTTGGTCTCGTACTGGGTGTCGGTGGCCAGATGCTGGAGCTCCGCCGTGTCCGCTCGGGCATTCAGTCTGAGCGCGATGGTATGGTGACCAT
GCACGATGTTTTGGACGCCATGTGGCTGTACGAAAACCACAAGGACGAGTCTATGCTGCGACGTGTGATCAAGCCGCTAGAAGGTCTGCTGGTCA
ACCACAAGCGCATTATTATGAAGGACAGTTCGGTAAGTTTGACATCCAGTTGCCGTTTGCGAAGTAGTACCCCATGATATTAAGCCGGCAGGTGC
CTGCAATCCCCACGGGCACCTGTGACTATGATTGGGAACAGCAAAGCTGCTGATGTGTGTATGTTGGGCAGCGCTCTTATCCTGCGCGCTCGACA
AAGAATATTCGGTCGACATTTCCTCTAGCAAAGGACCCCCTTATGATATCAACTAACAACCATCAATCTTTCTCCAGGTCAACGCCGTTTGCTAT
GGTGCCAAGATTACATTGCCCGGTGTCCTGCGCTACGAGGATGGCATTGAAATCGATCAGGAGATCGTCATTTGCACCACCAAGGGTGAGGCCAT
TTGCCTGGCCATCGCCCTCATGACCACAGCCACTATGGCCTCTTGTGACCATGGTGTGGTGGCCAAGATCAAGCGAGTGATCATGGAGCGAGACA
CATACCCGCGCAAGTGGGGATTGGGACCAAAGGCGTCGGCCAAGAAGGCGCTCATTGCCGCCGGCAAGCTAGACAAGTTCGGAAGGCCCAATGAA
AACACACCTAAGGAGTGGCTGACCGGTTATGTCGACTACAATGCCAAGAAGCCAGCAGCTCAAGAAGTCTCCCCCACAAATGGCTCCAGTGAACC
CAGCAAAGTATGTTATTGAAAATGAGTTTAACATGGTATTCACTTGCTAAATAATTGTGTTCCTTTAGCGCAAGTTAAGCACCTCCAGCGTTGAG
GAAACTGCTGCGGCGGCGGTATCCGAGGAGACTCCTTCCAAGGACAAAAAGAAGAAGAAAAAGAAGCACAAGGGCGACGAGGAAGCCCCAGAAGC
CGCTGAGGAGGAGGCAGAGCCAGTAGAAAAGGAGAAGAAAAAGAAGAAGAAGGACAAGGATAGGGACAGAGACGAAGCTCAGGAATAGGAAT
CAGAAGTTTCTATAGGATTAGGTTTAAAGAGAATTCTACGCTTTTTGTAGAGGCACCTACCGATTGCTAGCTGTTAGGTTTAAGGAGTGTTTT
TATGTGTAGAAGTGCATACAAATTACAAATGCATTTAAGTGACATTCGCAATGCAATAAATTGAACATTTTATTGTGGAACTCTATTGTAATGAT
GAACTCCAATTAAGAACACAAGTCCGTTTTAAGTTGAAGGCAGCCGTCGGGCTGACATATATTTATTCAATTTCTTCTTTTGATTTTAGAGTAGG
CAGAAATGGTTCTGTCAGCTCAACGTCTACTGAGTCTCTCTGATTTTACAGTTTTTTATATATTTGGACTTAGGCTAATCCGCGTAGCTGCGCTG
CCGGGTACGCCAGCAGCGGAGCGGCGTTCTTATGTATATCTTATATATCTAGGCTTATCGGGAGAGCGAGATATGTATGTACGTATGTAATATGT
ATTTGGTCGGCGTGTGAATGCTGACCATGCACTTATACTTTTTGCCTTCGAGTGGGTGATCATGTTACATCCGCCCTGGCCTAACTGCGTGCATA
AACATAAACATAAACATAGCAACAAAGTGCTGCCATAAGTTAATATGCTATTTTATTTAATTGTTCTTAATATTGCATAGGCACATACTACATCT
CCCTCCTTTTTGAAAAATAACGTAACCTAGTGAAGTTATTTTGATTATTAAATGCAAATTATTTTATTTTTATTTTTATTTTGTTTGTGTTTTTG
TTTGAACAACAATAGTTGATTTTATAATGCAAAGATAAAAATATACGTAGTGTATGGAAAATTTGTATAAATGATTAAGGAAAATATAAGTTTAA
ATTCAATCATGAATGAAATTTCTTTAATCTATCTTTATGAACTATTTGTTTTTTGTTTTTATTAGTAAGTAGCGTAATATTGTTATTATCTCCTA
TGCTTTCTATCTTATAGGGCCCCGTATATTTAAAGTCTAATTTATGACCTACCTCATTTCTTAGTAAAACTTTATCTCCTACTTCTAATTCTATG
TCTTTTATTTTTAAGTCATAATTTTCTTTATTTTTTTCTTTGTGTGCTTCAAGAAGTTTTCTTGCTCGAGCATATGCTACCTCTAACCTATATTT
ACTCTCCTTAGCGTAATCATCTATGTTATATATTGGTTCTATGCTATGTAGTTTATTAAAATGTTTTGGTAAATTACTTGTTCTACCGAAAACTA ATTCATATGGACAATAATTATGTACCATAGATTGGGTCGTGTTGAAGCAGTATACGAAATATTGAAGCCATACGTCCCAATCGGTTTTGTCCGTC
GATATGTAGGATCGTATATACTCGTTTAAAGTTCTATGACTTCTTTCTACTACTCCAACTGTCTGGTGGTGATGAGCTGTTGATGTTATATTTTT
TATTTTCAAATATTTACACAGGTCAGTAATTATTGAATTCTTATACTCTGTTCCCATGTCCGTTATGAACGTCTTCATTGGACCGTACTTTAGAA
TAAAAGATTCAAATATAGCTTCTGCGACTGTTTTTGCGCTTTTATTTGCTATTGGTATGGCAACTAAGTACTTGGTTAAATCACATATGAGAGTG
ACTGCGTACTCGTTACCATTTTCTGACTTGGGTAGTGGACCAATTGTGTCCCACAAACAACTCTATCGAAAGCATGTTCTGGTGTTTCAGTTATCG
GTCATTGGAGTCTTTGTGTGCTTTGTTGTTTTTGCATTTTTGACATTTCCTTACGGTACTCTTTTATGTATTTACTCATATTTTTCC
AGTAATAATGTCTTTTGACCTTGGCCAAGGTTTTTGTAATGCCTGTATGCCCTCCTTGTATTGGATCATCATGTAATGTAGACAATATAGCTTCT
TTTTCTTTTTCATTATTTATTTGGGTCACCGGGTTAAGTAGCGCTACTTTTAAATTCTTTAATATTTTATTGCCCATATTTTTAAATTTATCTAT
TGAAACGTGTTCAAAGATTTTTTTCCACGGTGCCATTTTGATTTGGCTGATATCATATATACCGGCCTGCAATTCAAGCCTTTGGAGAAATTGAT
CTAAATCAAGAATTCCATTAGTATAAAGATCACCAACATCATATCTTGCAATAATTTTCTTTCCATGTTTAAATAAACATATCGAGTCATTCAAT
TGCAATGTCACTACTTTTCGTACCTCGTCATTTGTTATGACTTCGTATACCGTTGGGCTCTGAAGCTATTTCTTTGGTTTGCTTTTGCAAATCCA
ATTGTTCTTTTCCTGCGCAGGATTTTTGTCTACTTTGAAATCTTGTAGTGACTTTTAATATATTTCCAGTTATATCTTTTAGCTCTTTGATGGTT
ATTCTTGATAACGCATCTGCTACATGATTGTCCTTGCCCTTTAGATACTCTACTGTAAAATTATATTCCTCTAGTTCAAGCCTTATTCTAGTTAA
TTTAGAGCTGGGGTTCACCATCGAGAATAAATATGTCAATGGTCTATGGGTCTGTTTCACAGTGAAATGTTTTCCGTAAATGTATGGTCTGAAA
TGTATTATTGCCCAATGAATTGCTGCTAACTCTTGGTCTGTTGTACTCTTATTGCTTTCACCTTTCGTAAAAGCTCTGGATGCATAAGCAACTGG
GGAGTTGGTGGCCATTATGGTTTTGAGTTAAAACTGCGCCACACGCTTGCTTGCTTGCATCTGTTGTTATGCAAAATTCTTTGCTGAAGTCTGGG
TACTGCAAGAGTGTTGGGTTAATTAGCTGAGATTTTAAATGTATGAATGCTTTTTGACATTCATCTGGCCACTCGAATGGAACATTCTTTTTACA
TAATCTTGTTATGTGCCGCGAATAGTCGGCGAAATTTTTTGATAAAACGTCTGTAGTAATTGCAAAATGCTACAAAACGTCTAGCGCTGTCCGCAT
CATGTGGAACTGGGTAGTTCTGAATGACATCATATTTTTTGGCATCCGGCAAAATTCCTTTGTCTGTGCATTTGTGTCCCAAAAATGTGACTTCA
TGCATGAAAAATGAACATTTTTCAGGATGTAACTTTAGGTTGTATTCCCTGCATTTACCAAAAACTTCAGTGAGGTTTTTAAGCATATGTTTTTC
GGAACAACCTATGACTATTAAGTCATCCATATAAAGGAATGCTTGAGACGGTTCTATTCCGGAGAATGCTATAGTCATCATTCTTTGGAATGAAT
TAGGCGCTATTTTTAAGCCAAATGGCAATCGCGTGAAACGATATGAGCCATTGCTGGTTGAGAAAGATGTTATATCTCTCGAGCCTTCATCCAGT
TCGATTTGATGAAAACCTGACATTAAATCAAGGCAGGAGAAATATTTTGCTCGACCCAAGTTGGTCCAAAATATCATCTATTCTCGGTAGTGGAA
ATTTGTCAGCTAAAAGTTTCTTATTAATTTGGCGATAGTCTATTACTAATCTCCATTTCTTTTTATCAGAATTCGGGCTTGACTTTTTGGGTACT
AATAGCAAAGGGCTATTGTACTGTGAAACTGATGGTTCAACTATTTTATCTTTTATTAATTTCTGAACTTGGGCTTGTATTTCTTCCACTTGACT
ATGAGGACTTCTATAATTTTTCGTGTATACTGGCTCATCATCTTTTAATCTCAACTGTTGGTTATAAAAATTATTAACTGGTATAGGTTCTGATT
CTAATGCAAATATATCTATATATTCGCTGCATATATTTTTCTAATTGTGATTTAAACAATTCGGGGAAATTTTTCTTTAATTGAGATAAGACAGTT
TTATTTCTGTGTTCACTATTTGCCTGAACTACATTGTAGTTCGAAAGTGGCTCATATTTTAGAGTGTCCATATTGACTAATTGGTCGGAATCGGT
TGTATTTAAAATTCGGACAAATGTATTACTTGATGTTGCGATTGGATTTGCAACATAAATACCAGTTTGAATTTCCTGGTTTGGAATTAAAATGT
TATCATCTTTTGATGATACTATTAATCTTCGGACAACTTGGGATCTTGCTGGTAATAACCGTTGTGTTAATACCAGAGCTGTATGCTATGGGAAT
ATATATTGGAAATTTCAAATTGTTTGGTCTAATTATAAACCAATCTTCTTCTTGGGTTTAAATCGATTTGGCAATTATATTTTTTTATGAAATCT
ATTCCGATTATTCCATCACACGGTATTGGAAAGTTTTTATCTACTAAATGAAAATCGTGTGGGATAACGTATTTACCTGTCTGTATCTCAATAAA
AGTCTGTCCTCGAGACTGAATTTTCTGTTGGCCTATGCCCTTGAATGTTTATTTTATTGGTTATTTGAATATTAGAAAATTTGTCAGAGTTCTCT
TTGAGAATAGAGATATCTGCACCTGTATCAAGTAGAAAAACTAGTTTTACGCCTGTTTTGGCATGAATGAATGTAGAAAATATGTTGAGATTATA
ATTGATGGTGTATACTCTACGATCTTCTTCTACTGAGTACCTAAAGGCTGTTGCGAGTTTCCCTGTTCTTGGATTACTCGTACATTGGCATTGTT
TCTGTTGTAGTTGTTCTGACTGTTGTTACGGCCTCTGTTTCCATTATAACGGCCTCTGTTATAGCCATTATAACGGTTATTATTTCCATTATAGC
GGTTTTGATAACCGTTATTCTGGTAACCGTTATTTTGGTAACCGTTATTTTGGTAACCGTTATGGTAGTTGCCTCTAATACTATTGTATTAAAG
CCTCTACCGCGGTTACTACCTCTATTGGCATTTCCGTATCCTCTATTGGGTCTGTTACCTCTAAAGTACATCACTTTATTGATGTCACCGGTAAC
TCTTGTACTCGTTCTTATGTATGCGCTTATCGCTGCATCCATAGTGGTGCAAGTCCCTGCTTCCAGTACTGTTTTGATACTTTCGTGCTCAGCAC
GATGTATCATGGTTTCAATTGCCTCTTTGGTGCTTAGACCAGTGGCATGTTCTAGAGGTATACCCTCATCGATATAGGAAGCTTCTAAAAGTTTT
CTCAGGCTATCAACTTCAGCGGTAAATTGCGTTGCAGTTTTACCTCTCTGCTGAACTGTTGCTAGCTTTGCTTTGACATTACTGGATGTCTCACC
GACAACTACTTTCTGCAATTTGTTTATAATTGCTGGAATTGTCGTTTCATTGTCAACTGAGTTCAAAATTGTGCCAACTATTTTTGACTTAATGA
CCTCAACTGCAATGTCTTCAAATGGTCCCTTAGCTAGGTCTACCAATTTGATTGCCTTAATGAATCTTTGTAAATGGATCTTTTGCCCATCAAAT
TCTGGCACTGTGCAGGCGACTTCCCTAATGTAAGACCTAATGGCAGCTGCTTCTTCTGCCATGGTTAAGTTATTTTCGGAGTCGGGCTGCGTTAT
TTGTTTTATCGTCGTTCTTCAGCCATTAATTTTGCTGGTATAGTTAGATCGGGAAGATCTTCCTCTTTAATGTCTTCCTTGACTATAGTCCTATC
TTCCTCGTCAGAGTTAGTGCTGTCTTCATTCAAATTTATTCTTAGGGGGGTGTTTACTATGGGTGGAATTTCTATCTGGAGACTGAATTTATTTT
TTATAAATATTAATTTTTCTCTTAATGTCACCAGTAGGTTCAAAGCCTTAGCACACTGTTTGCGTTCCAAATTCTTTCTATTTTGTTGGATCAAC
TCTCTGATTTCATTATAACTATTTACCAAGACTTGGGCATTCCTATTGATTGGTACAGCTTGGGTTGATCTGTTTTGCGTTAAGCACTTATAGGA
TTTTCTGAAATTTTCATTTTGATCTTTTATCTGATCAACAAGCTTTTCCCAGTCCATGCTGTGGTATACTCATAACTTCAAATTTATTCATTTGT
ATATATTTTTTTTTTAATGTAGATAAATTCAATATTACGGTTTTATATTTTTTTTTTTATTTATTATTATTTTTTTTTTCATATAATTTTTCTCATAT
TTTCATTCATAATTGACTTTATTAAAGATCTTCCTTAAATATTATCTATACCGTTAGCAGTGCTACGGTATCGTTTCTTAAGACACTTGTTATGC
AGTTTGTATATTTTTATTAATGCATTGGATACCATAATTAATGCAATTACAATTAGTATTATGGTTATCCAGAACAAGTCTGCATTTTGGACTTC
TACTTTATTTATTACATTGGCTGGAGAGTCCACAGTTTTAGTGTCTATTAGACCCATTTTGGGTATACTAATTTTATATTTTGGAGAATAGAATA
GAAAATTTCCTTTGGATATACTTTTATTTTCAGGTTTACTTATTTCATTTGTCTCTATAGACATTTATGTTTGGAATTATCTATTTATAAAATCT
TTCAATGTTCGCAAGAGTAAAAAAAAATTGTATTTTACATTGTTGCCTGCCTGATTCTAGCTATGGCTTCACGGGCCATATTGGGTTAACAGGGC
ATAATAGTATATGCTCCGTTTTACAATATTTCTTACAATTTTTCTTATCTATATATATTTTATATTTACTTTATATTTATATATATTTATTATTA
TATTCTGCTGTTGATGATGCTCATCAGGTGTCAGCTGGGCGTCGCCGGGGGTGGCACGCTGACACTCCCTCGCTGCTGTCTATTTCTTCGCCGCT
GAAGACGTCGATGGTCGCTCACAAGTCCCCAGGCAGTGGGGACTCCAGATTCCTTCGCAGCCAGGGGGGCAGGACTTCTTTGGTTTTGTTAATGC
TGGTGCTGGTGCTGGACATGCCTGGTATTTTGGAACTTCATTAATTGTGGGTATATTTTTAATATTATCTGAGTGAGTTTTCTCGAGCTTATGGG
TCTTTAATTCTTGCTGATATTGCAACAAGTGGTCTAGCTCTGCATGTAGCTTTAGAGCTTTCGACCAAACCGGTGGCGTTTGCTGACCGTATATT
AGCCACCTTACGTGGGCTATACGTTTATTCAGCTTAGTTTTCAAACCGCCACGGTGTTTGCCCATACTCAATAGAACTCTACTCACTCAGATTTT
TCCTTGGTTTTTGCAGTTCCATTTAATTAGTCCAGTCTTCTTCCAGTCCAGTGTTCCTTTGTTCCTTTGTTTTCACCAGCTTTGGTCAATTCGTC
CAGCGTTGGACGACTGTCACGGTCGCCATGTAATGATGAACTCCAATTAAGAACACAAGTCCGTTTTAAGTTGAAGGCAGCCGTCGGGCTGACAT
ATATTTATTCAATTTCTTCTTTTGATTTTAGAGTAGGCAGAAATGGTTCTGTCAGCTCAACGTCTACTGAGTCTCTCTGATTTTACAGTTTTTTA
ATATATTTGGACTTAGGCTAATCCGCGTAGCTGCGCTGCCGGGTACGCCAGCAGCGGAGCGGCGTTCTTATGTATATCTTATATATCTAGGCTTA
TCGGGAGAGCGAGATATGTATGTACGTATGTAATATGTATTTGGTCGGCGTGTGAATGCTGACCATGCACTTATACTTTTTGCCTTCGAGTGGGT
GATCATGTTACATCCGCCCTGGCCTAACTGCGTGCATAAACATAAACATAAACATAGCAACAAAGTGCTGCCATAAGTTAATATGCTATTTTATT
TAATTGTTCTTAATATTGCATAGGCACATACTACACTATCGCTAGTTTCTTAGGTCTTAGCTTTTCCTTAGGTTTTTCAGATAGAAAGGCAGGGA
ATACAGACAGCAAAGGTGAGTTAACATATTACTACGTTCCTTCAAGAGTGGCTTTCGTTTGCGTTATCTGATGAGCAATAACTTTCGCCCCTAGC
TGAAAAATGATACTTCTCATGTTGAATGCGAGATTGGTCTTACTGAAAATAACGGAAAATAGAAAAGCTCATTTGAGTTTCTAAAAACGTTGACC
TGGCCTCTTATTAACTTAATTTATATTTCTATTGTAGCTTGGAATACTGCTCAGAGGACAAAGCGGGAGTGACGGAAGATACGGTTAGTATCTAT

FIGURE SHEET 171

TTGATGACCATCTTTACGTTATATTAGTTCTGATGAGCATTAACTTTCGCCCCTATCTGAAATTGAAACTTCTCTTGTTGAATGCGAGATTGGTC
TTACTGAAAAACTAAAAAACTATAAGCACATGTGGGCTATCTATATCCAATATATTTTAAAACCCAATATATATTTACAGATCGGCGGAACGAAA
ACTAAAAACGTGCTTCGAATAAACATAGGAATTAAGGTAAGAATGCCTTAATTTATAGTTGAATTTCTTATTATCATGATGAGCATTAACTTTCG
CCCCTATCTGAAATTGAAACTTCTCATGTTGAATGCGAGATTGGTCTTACTGAAAAGAATTTCGATTTAAAAACACGAAAACAATTTTCTAAGCA
CTTTCTAACCAAATTTTGCCCATTCTCTTTACAGATTTGTTGATTAGGTTATGCAATATATGGACTATAACTTTAATAAAATAGGTAAATATTGA
ATAACTAAAAGTTATTAAAATGTTTTTAAGTGATGAGCTTTAACTTTCGCCCCTATCTGAAATTGAAACTTCTCCTGTTGAATGCGAGATTGGTC
TTACTGAAATGACTCACAATTAAAAACAAGCCTCAATCTTTTCGATTGCCTTTCTAATAAAATGCTACTTTTTCTTTACAGATAAGTTCAAAAAT
TTTTTTGAAAATCATTGAATGCCACAGGAATCTTAAAAGGTAAATGTATTCAAAATGAATTATTTCTTTGCGAGAATAACTAACTTCTTTGAAAA
TTAACTGATGTAAAAAAAAAACTGAATTATGTGGCATGATTTTCACATTAACCGCAACAAATCCTACTCCAATAGGTCCTACTGACAATTCTCAC
AAAAATAATGCATTTAGGCCAATACAATAACAACGATGCCTAACAATTGACTCTCCTTTGCCTTTTCAGTTCGCATGACACTTTATTGCGTTGAG
TAAACAAGGTAAAAATAAATTTAAAAAAACTCGTTTGCCCAGTTTCTAGTGAAAATGTTGAAATAAAAATACTGATTTATGTGGCATGATTTTCA
CATTAACCGCAACAAATCCTACTCCAATAGGTCCTACTGAATATATTCACAAGAAACTTAAGGTGTGTTTTAACCAGATGTGGTTCTAAGTGAAT
TTTTTCTTATATTTGCAGATGTGCTTTTGGCGACTTTCCACTGACTGTTCCAATTGAGTTCCATTTTATGCCCTTTTTTAGGTACAACACTGCCC
AAGACATCATATAATACTTTATAAGCAAATAAAAGAAACATACACAAAAAGCACAACTTCTTTTTAATTAGACAAGGCCATGTGTGCTCTTAACC
TAAAACACAGCTGAAATCTATAGACCGCTTGTTTTGGGCGGGCAATCGTGGGTCAGGGGTGCAAAAAAGCGCGAAAGAAGAGTGCCGACCTTCGG
ATGGATAACTTGTGCGTGTGCAAAATGAAGCT
(SEQ ID NO: 307)

Exon: 1001..1088
Exon: 1149..1517
Exon: 1594..1845
Exon: 2038..2312
Exon: 2548..2952
Exon: 3014..3407
Exon: 10866..10940
Exon: 11153..11198
Exon: 11386..11436
Exon: 11625..11667
Start ATG: 1076

Transcript No. : CT11195
ATTTTCTCGCAGCGCGCAACACGTGCGGAGGTTTCTCTCCGTCTATTAGTTGATTTAGCAGAAAACGTAGATAAAATGGCCGACGTGGAAGTACG
CAAGGAGAAGAAAAAGAAGAAGATCAAGGAGGAGCCCTTGGACGGCGATGACATTGGCACGCTGCAGAAGCAGGGCAACTTCCAAATCAAGCCCT
CCTCCAAGATCGCCGAGCTGGACACCTCGCAATGGCCGCTGCTCCTGAAGAACTTCGACAAGTTGAACATCCGTTCCAACCACTACACTCCGCTG
GCGCACGGATCGTCGCCCCTGAACCGCGACATCAAAGAGTACATGAAGACTGGCTTCATCAACCTGGACAAGCCGTCGAACCCCAGCTCCCACGA
GGTGGTGGCCTGGATCAAGAAAATCCTCAAGGTGGAGAAGACAGGCCACTCCGGCACGCTGGATCCCAAAGTCACGGGTTGCCTGATTGTTTGTA
TTGACAGGGCCACCCGTCTGGTGAAGTCCCAGCAGAGCGCCGGCAAGGAGTACGTGGCCATCTTCAAGCTGCACGGAGCCGTGGAGTCGGTGGCC
AAGGTGCGTCAGGGCCTGGAGAAGCTGCGTGGTGCCCTCTTCCAGAGACCTCCACTCATCTCCGCCGTAAAGCGTCAGTTGCGCGTTCGTACTGT
CTACGACAGCAAGCTGTTGGACTACGATGAAACCCGAAATATGGGTGTTTTTGGGTTAGTTGCGAGGCCGGCTCCTACATCCGTACCATGTGCG
TCCATCTTGGTCTCGTACTGGGTGTCGGTGGCCAGATGCTGGAGCTCCGCCGTGTCCGCTCGGGCATTCAGTCTGAGCGCGATGGTATGGTGACC
ATGCACGATGTTTTGGACGCCATGTGGCTGTACGAAAACCACAAGGACGAGTCTATGCTGCGACGTGTGATCAAGCCGCTAGAAGGTCTGCTGGT
CAACCACAAGCGCATTATTATGAAGGACAGTTCGGTCAACGCCGTTTGCTATGGTGCCAAGATTACATTGCCCGGTGTCCTGCGCTACGAGGATG
GCATTGAAATCGATCAGGAGATCGTCATTTGCACCACCAAGGGTGAGGCCATTTGCCTGGCCATCGCCCTCATGACCACAGCCACTATGGCCTCT
TGTGACCATGGTGTGGTGGCCAAGATCAAGCGAGTGATCATGGAGCGAGACACATACCCGCGCAAGTGGGGATTGGGACCAAAGGCGTCGGCCAA
GAAGGCGCTCATTGCCGCCGGCAAGCTAGACAAGTTCGGAAGGCCCAATGAAAACACACCTAAGGAGTGGCTGACCGGTTATGTCGACTACAATG
CCAAGAAGCCAGCAGCTCAAGAAGTCTCCCCCACAAATGGCTCCAGTGAACCCAGCAAACGCAAGTTAAGCACCTCCAGCGTTGAGGAAACTGCT
GCGGCGGCGGTATCCGAGGAGACTCCTTCCAAGGACAAAAAGAAGAAGAAAAAGAAGCACAAGGGCGACGAGGAAGCCCCAGAAGCCGCTGAGGA
GGAGGCAGAGCCAGTAGAAAAGGAGAAGAAAAAGAAGAAGAAGGACAAGGATAGGGACAGAGACGAAGCTCAGGAATAGGAATCAGAAGTTT
CTATAGGATTAGGTTTTAAAGAGAATTCTACGCTTTTTTGTAGAGGCACCTACCGATTGCTAGCTGTTAGGTTTAAGGAGTGTTTTTATGTGTAG
AAGTGCATACAAATTACAAATGCATTTAAGTGACATTCGCAATGCAATAAATTGAACATTTTATTGTGGAACTCTATCGCTAGTTTCTTAGGTCT
TAGCTTTTCCTTAGGTTTTTCAGATAGAAAGGCAGGGAATACAGACAGCAAAGCTTGGAATACTGCTCAGAGGACAAAGCGGGAGTGACGGAAGA
TACGATCGGCGGAACGAAAACTAAAAACGTGCTTCGAATAAACATAGGAATTAAGATTTGTTGATTAGGTTATGCAATATATGGACTATAACTTT
AAT
(SEQ ID NO: 308)

Start ATG: 76

MADVEVRKEKKKKKIKEEPLDGDDIGTLQKQGNFQIKPSSKIAELDTSQWPLLLKNFDKLNIRSNHYTPLAHGSSPLNRDIKEYMKTGFINLDKP
SNPSSHEVVAWIKKILKVEKTGHSGTLDPKVTGCLIVCIDRATRLVKSQQSAGKEYVAIFKLHGAVESVAKVRQGLEKLRGALFQRPPLISAVKR
QLRVRTVYDSKLLDYDETRNMGVFWVSCEAGSYIRTMCVHLGLVLGVGGQMLELRRVRSGIQSERDGMVTMHDVLDAMWLYENHKDESMLRRVIK
PLEGLLVNHKRIIMKDSSVNAVCYGAKITLPGVLRYEDGIEIDQEIVICTTKGEAICLAIALMTTATMASCDHGVVAKIKRVIMERDTYPRKWGL
GPKASAKKALIAAGKLDKFGRPNENTPKEWLTGYVDYNAKKPAAQEVSPTNGSSEPSKRKLSTSSVEETAAAAVSEETPSKDKKKKKKKHKGDEE
APEAAEEEAEPVEKEKKKKKKKDKDRDRDEAQE*
(SEQ ID NO: 309)

Classification: known_flybase_gene
Gene Symbol: Nop60B
FlyBase ID: FBgn0023184

Celera Sequence No. : 142000013384809

FIGURE SHEET 172

TGTATAGAAGGTGAACATATAATAGTGACTGCTACTCACGCTAAATTCTTGCCCAGTTCACTGCACCCTTGCAGTTTTGATAGTTTTGGCAGATT
AGGAGAGACGGCAAATGTGCAATCTAATATCTATTGACAATTGCTGCATCACACATATTGAAAATATTATCGATAAGCCTTATTAGTTTTTGCAG
TTTTGCAAGCAATACAGTGCGGATCCTGAGAGGTCTCACTGTGTCTTCAAGGTTCGCCTTTAGAAGTCAAATGGCTCGAAGAAGTCTAAGCGGAA
TGTAGAATGTAGCCAAATATAGAACACCTACCACAGATCGCATTAGTTTCTTTCTTTCCTACGATATTTACTCCTTCAAAATCGATGCGCAAATG
GTTTTTAAGGACCAGCGCCTGCGCAGCACTTGACCAAATTCAGGTAACGGCGAATCTTATTTTATCCACTTCAACCACATACGATAGAAAATATT
AGGGGAGAGATGTGTGCGTGACAATTAGATAGTGGATTGTACATCCGATAGCTCAGGTAAACAACAACCAAACATACCTAAAACTTAAACAACTC
TTTAATTTAACGTAAAAATAATCGATGACATTTTATGAGCGAGTTCCGAGAAAACGTTTAATAAATTATTACCCCATTGGGTGTTCGTGTTCGCA
CAACATAAGACTCTCATCTCTACATTTTATGAGTGAAACATTCGTTTGAGTGAAAGTCGATTTCCAACCCTGTTATGATTTGGCGGGAAACTTAA
ATACTTGGATGAAATTTTTTGTATAAAGAGACATTTCATATTTTGTATTTGTAGTACTTAAATTCTAGTTTTCTAGTTTGCAATGCCTCGTTCAT
CGTTATTATGGCCTGAGTGATTTCGAACTTTCTTTAGAGCCGTATGCTTAGTTCTGTTTTTTTGAAGACTTCAATGAGATGTTCATTAAATCGTA
GAGTGACAAATGCAGGAATATCAAATGACGTAATAGTAGAAGTCAAGGGTTTAGAAATGATTTGCCACGGTGCTCTGTTGTTCGCCGCGGTTTAC
TCGCAGGTTGCCCATGCATCCCTCAAACAGGATGTCTGCGATGGCCTTTCGTGCCAGAATCCGTTGCGTGGGGGACATTTCCTCGTACTGGATAG
CCCAGGATCTGGCCAGAACTTCGGAGGACTCGCTGAGTTGCATGGGTGCAGTTCCTCGTTCGTTCTCGGGATCTGTTTGAATCGAGGATGTGGGT
TCTTTCGTTTCCAATGAATTTCCCAAACTATTTTCCTCTTTGACTTCACACTGCCCTTCTTCCGGCTCTATGATCTCCAATTTTGGACTGAGCAG
GGAACCCTCTTCGGATTGCGGGGCGGTCGGTTCGGACTGGTAGTTGAAAGCGTTATCATCCTTGATCGGCCAATCACAAACGCTTTCCGTGTTGA
GATCTGGATTTTTCAAGGGGTATTTGTCCTATGAGGTACACAATTTATTTATTTTTAAGTATCATTCAATCATTGAGAATGTAATCTTACATCCT
TTTCCCTGCGAAAATCTTGCTTCTGTCTGCCGCCCCGACCTTTTCTGGTCCTGTGCTGGAAGGTCTCCTGGGTGAGGAGAAATCCCATGTAGTCG
TAGAACCAGAGCGTCGGCTTACAGAGATCGGAGTGCAGCCCCAGCTCCTTCTGCTTGAGGATTCGCATCTGCTCCCGCCTGTAATTGGTGCGAAA
TATGTTGATGCGCCTGCCGACTTCTGTGCGCGTAGCGTTCGGCTGTATCTCCCGTAGTTTCCTCTCCAGCAACTCATACGCCCGGTTTCGCAGCT
CCTTGTTCCGGTAATTGAGGTGGTGGACGTCCCACAGCTCCGGCATTCCCTGATAAAGGGCCAGAAACTCGCGCCAGAACTGCCGTTTGCCCGCA
CTAAACCGATCTGGCAGTGCAGCTGCCATCTGCCAGCACAGCATTCAGAAAGATACATTTAATTACCATATCCATTGGCATATAAACATAAATAT
TTACTTTTTCTGTTGTTCAAGCCAATCAGCTGTTGTTGATTACAGTTGGCCAGAGTTGCCACTTCTAGCGTCTAGTGTTGGTAAACACCTCACAT
ACTCCCACTGATTGTTGTAGTTGCTCTGGATCTGGATGCTCATATATGTATAAACTTATTTCCACCACCTGACGACCGGCGTTATGCTCTCCTCA
AGCGACAATCACAAACTGAATTGATGTAGAGCCGAAACGGGCGGGTGTGTGTGCATGTGTCTCGATTGAGTGATTGATTAGCCGACTGACCCGAT
GGGCATGTGCATGTGTGCGTGTGGAAATGCACAATAAATCATTTGATTCCCACATACTGCTTGAAAACAAAAACGTAGCTGAATCCGATTTTCTT
ATTGTATTAGTTTTAATTATATGGATTAAACAATGACTTACAGCTCCCCCGCAATTTAGGTGCACGTGTGTGCGGGAGAGGAAAGCAGCAAATAT
TCAGACTTTAACTAAGGGCAGACCTGCGCACTTACCCATCTTAGCCCCAATCAAGATTGTCGGCATAAGGAAATCATCAGCAAAGTATGAATTTA
TTTTAACTCGCTCTCCAAAATTTCACACTGATCAGGGAAAATTTTAAAATACACTCTGAATCAGGGAAATTCTCTCTTTAACAAGATAGAATTCA
ATGATTGACCTCTTTGTTCCGTTATTTTCATTTACATGCGCTTTGTCTCTTTCTCTCTTCTGGCTCGCCTGTGTGTGTGTGTGTGGGTGACCTCC
CGCCCGGCAAAAAAAGAAGAAGAAGCCCAACTAAGGGCAGACATGCGCACTTCGAAAAAAAAACAATTAGCGCGTATATTTAGCCGACTTTTTGT
TCTGGCGAGAATGTGTGGAAGGAAATGTAGCTGTTATAACATACAACACAGGTCAAAATAATAGGGTTACAGTCGGGAGCATAGTATAAAATAGT
TCCAACAGACCAATTGACAATTGACATTAGCTCATTCATCACAATATTTATAACCACATCAAATTTACTCACTAGAAACTTGGTTTGATTGCGT
TTATTTGGTTCGAATACAAATTATGTTCACCTTAGATCTAATGATTGATTGCATCCGACCGATGTGCATCTTCTAGATGCATCAGTTTGCAAAGA
TTACACTCTTTGGCTGCAGCTATTCCTCCTCCTCTTCGTTCTCCTT
(SEQ ID NO: 310)

Exon: 2181..2000
Exon: 1929..1516
Exon: 1453..1001
Start ATG: 1929 (Reverse strand: CAT)

Transcript No. : CT11349
GAGAGCATAACGCCGGTCGTCAGGTGGTGGAAATAAGTTTATACATATATGAGCATCCAGATCCAGAGCAACTACAACAATCAGTGGGAGTATGT
GAGGTGTTTACCAACACTAGACGCTAGAAGTGGCAACTCTGGCCAACTGTAATCAACAACAGCTGATTGGCTTGAACAACAGAAAAAATGGCAGC
TGCACTGCCAGATCGGTTTAGTGCGGGCAAACGGCAGTTCTGGCGCGAGTTTCTGGCCCTTTATCAGGGAATGCCGGAGCTGTGGGACGTCCACC
ACCTCAATTACCGGAACAAGGAGCTGCGAAACCGGGCGTATGAGTTGCTGGAGAGGAAACTACGGGAGATACAGCCGAACGCTACGCGCACAGAA
GTCGGCAGGCGCATCAACATATTTCGCACCAATTACAGGCGGGAGCAGATGCGAATCCTCAAGCAGAAGGAGCTGGGGCTGCACTCCGATCTCTG
TAAGCCGACGCTCTGGTTCTACGACTACATGGGATTTCTCCTCACCCAGGAGACCTTCCAGCACAGGACCAGAAAAGGTCGGGGCGGCAGACAGA
AGCAAGATTTTCGCAGGGAAAAGGATGACAAATACCCCTTGAAAAATCCAGATCTCAACACGGAAAGCGTTTGTGATTGGCCGATCAAGGATGAT
AACGCTTTCAACTACCAGTCCGAACCGACCGCCCCGCAATCCGAAGAGGGTTCCCTGCTCAGTCCAAAATTGGAGATCATAGAGCCGGAAGAAGG
GCAGTGTGAAGTCAAAGAGGAAAATAGTTTGGGAAATTCATTGGAAACGAAAGAACCCACATCCTCGATTCAAACAGATCCCGAGAACGAACGAG
GAACTGCACCCATGCAACTCAGCGAGTCCTCCGAAGTTCTGGCCAGATCCTGGGCTATCCAGTACGAGGAAATGTCCCCCACGCAACGGATTCTG
GCACGAAAGGCCATCGCAGACATCCTGTTTGAGGGATGCATGGGCAACCTGCGAGTAAACCGCGGCGAACAACAGAGCACCGTGGCAAATCATTT
CTAA
(SEQ ID NO: 311)

Start ATG: 183 (Reverse strand: CAT)

MAAALPDRFSAGKRQFWREFLALYQGMPELWDVHHLNYRNKELRNRAYELLERKLREIQPNATRTEVGRRINIFRTNYRREQMRILKQKELGLHS
DLCKPTLWFYDYMGFLLTQETFQHRTRKGRGGRQKQDFRREKDDKYPLKNPDLNTESVCDWPIKDDNAFNYQSEPTAPQSEEGSLLSPKLEIIEP
EEGQCEVKEENSLGNSLETKEPTSSIQTDPENERGTAPMQLSESSEVLARSWAIQYEEMSPTQRILARKAIADILFEGCMGNLRVNRGEQQSTVA
NHF*
(SEQ ID NO: 312)

Celera Sequence No. : 142000013384832
CAGTTTGCGTGTCTGCGAGCCTGCATTTGAAGGCTGTGCAGCAAAGGCATCTGACATGGAGGCACGAAGGAAGCCCTGTGTGTGTGTGGGTGTGT
GTTTTCGGCGGCGCCATTGTCGATAATAACGATGGACTGAGCCCCGGGTCGCAGGCTCTTTTGTGCGCGTAACATGTGTCAATTACAGGCGCCCA
CACCCACACACTCGCACACTGGCACACACGCACACACACAGAGAGCGAGCGGGAGGAACAGGAGCAGCCGGCACGTCCAGCACACACCCACACAC
GCATATGCGCTCACTTAGTTTCGCTCTCACACCGTCGATAACTCAAAAAGCTGCCAAAAAGTGTGCGCACATTTTTTATATGCGCCGTCCGAAAG TATGCACATATTTTTTATATTTGTGCTGCCGGCATTTGACAGCTAAGCGACGCTGCCCTATGTTAATTTATTTTCACACAGCATTTGCTTTTTGT
TTGCATGTGCGTCGGGAAGGGGGGAAATTACTTTCCGCCTCTGTTTTTGTTGGCGAATAAAAAATCTTAATTAAAAAATTTCGAATCGCTGTAAC
AGGTGGAAAGGCCAGCTGCTAAGTAGAACGGCCAAACTTTGCCTCTCCGAGAGATTTGGATTGCCGGGTGCTATAAATTAGCAGTTTCCACTTGT
TACGTAGAAAGCTATTATCAACTTATTATTTGAATTACTTCTTTCTGTATATAGTTGCGATGAAATGGGGTTTGTCATTAATTATTCCATCAGAT
TGATTGTGAAAGCTAACAGCGATCTGTAAACTTAACAGCCGTTAAGCGATCTCCTATAATGATCATCATCATCATCATCATCAAGTTCTTCACTG
AGTTTTGGAGGCTGTTCGTACATAGCTCTCCTCTCATTTTCCTCACTCTTTTGTGGTTCTATTGCTCTCTGCCGCTCTCCAACGCGAATGTCTGT
GGCTATAAAAACCGGGTCCCCACCGCAGCAGCAGTTATTTCTCCGATCCGACGTCGGGTGAACAGATCAGTCGTGCCGCAACTGCAGCTATATCT
TTACCTATGTGTTCTAATTTTCCGTGCCAGTAACCGTTCTGATCGTGCGAATAAAAAGTATGTCACTTGGGGGCGCTGCACTGGCATTGAAAAGT
GAATTACATTGATCGTGACATGGGAATGGAAAATGTCGCCGAGCCATGTAAATCGTTTGGCCTACCCGTCTACCAGCCAACCAACCAATCAACCA
ACCAACCAAAACCTGTGCCAAGAACTGCGTGTGCGCAGAAGCGTTTGGGAAAACTCTGTGACTGGCATACGAAATAAGTCAAGGTCTTCAGCATA
AGAAGACGCCAGAACATAAGTCATACTGGCGACTTATAGAGATAGCGCCCATTTCCCATCCATAATCGCGGGTAGCAATGAACTTTGAAGCCGGC
ACGTCACTTGATAGCTTCCTTAACCCATGTGGGCCCCATGGGCTCCGATTACATTACCTCGCCAATTATTCCCCTGTGCAAAACGTAACTGCATT
ATTAACAAGTGTTCCGACCACCTTTCCATTGTTGGCGCTTCGCGATAAGCCGGCACAACAAAGAGCAACAGACGCCGCGATATCAGTTGAGTTCA
GTTCTGCTGCTCGCACCAGGGCAGGTTCAATGTCTGGCGCGGTTTTATCGACCGATTGCCCACTCAGAGGGGTCCACTTAGCGAGCCGACCAATC
TATGAAATCGCACAGTTTAATGAAAGATTATTCACCTAGAGACTCGAAAAATTTCCATGCGCAAAGGTTTAAGGCTGCACTTTCTGTTGATATAT
ATAATGTCGCCGTAATAAAAACATTCACTTGGGTCGTAGATGTTTGTTGAAATAATTAGCCGTTTTCCCACATAAAACGCTTTAATAATGATGTA
AAAGTAATTAGCCGTTTTTCCCTAACGAGATCACTAGATAATATTTTTTATGCCCCTTTTTATATTGGCTTAAATAAGCTGTAGTCATCATCATA
GACAGAGGGTAGTGTAATGACTACAATAGGTGGGGACATCTGGCTTTCCATGCCAGTTTTTAAAATAAAATTTAGACCCCGTACTCAATTGCCAC
TGCTCCACTTGGGTCCGAATAAATGTTTTGAGTGCATGAAGGGGATTTTCACAGCCTAAGCACTTGTCACTCCCCCACAGCCCCTCCTAAACCAC
ACCATCCAACTGCTCATGGCGGCTGATAAGAACTTGCGGCCCACAAGCCATGTAGTAAATCGGTATCAGACAGCACTATGGTGCGCTTATCACTC
AGTTACTCGCAGGCGGTTGCCCTAGGCACAAGTGGAACTGAAATCGGAAGGGTGGCATCCACAAAGTGCTCTATTTGGCCATTCCCTAGCTGTCA
CTAATCATATCCGTACGATTGAGCAATATCTGACTAACTGTTTCGATCATGTTTGCTTTCACCCCCTGCCCTTTGAAGTGAGCGAGAACGAGAAG
CGTCCCGATCTGGAGGATCAGGATCAGGATCAGAATCAGGAGCAGGCTGGCGGCAGGAAAATGGAGATCCTGCTGGAACTAAACCTAAAGCAGAA
GCTGGCCACCCGACTAGGCACCATCCTGCTGGCCACAGTGATCTTCGGCGCCTTTTGCTGGGACAACGCGTTGGCCAGTCTAACACTGGGAGCAG
TGGTGGCTCTCCTGCTCAGAAATCCCACCTTCGTCTTTGCCTTGGTAATGACCGCGTCCAGGGACCTAAAGTGGGTATTTGAGTGGCTAATTTCG
CGGAGAAACCCCCCAACTTCCGTTCTCTTTTAGGGCTTTCCAGCGATTCGTGGCCCTCAACATCTACCTGCTAAGAAAGGATCGCGGCGGATTCA
CTGTGGCCCGCTGTTTCCAGGACCAGGCCAGACGCCGCCCCAAAAAGACATGCTTCGTGATGGACGATCGCCATTTAAGCTTTGCAGAGGCTCTG
GAGTTTAGCCAAAAGATAGCTGGATATTTTAGCGATCGCGGCCTGGAGAGGGGCGACTGTGTGGCCCTACTAATGGAAACGCGTCTGGAGTATCC
CTGCATTTGGTTGGGTCTCTCCCAGCTCGGGGTAATCACAGCCCTTATTAACTCCAATCTGCGCGGGGAGTCTCTGCTGCACTCCATCAAAGTGG
CCAATGCCAAGGCCCTAATTGTGGGCAGTGAACTCCTGGATGTGCTGGTATCACTTAGGGAGAAGGAGCAGTTGGACGAGGTGCCCATCTATCAG
TACACAGATGACGAGGTTCGCGGGGTGGCTGGACATGATCTTTTGCCAGGAGCTGTGGACTTGGTTACTGCTCTAAAGACCCAAAAGAAACTGGA
GCTACCGAGTGCTGTCTGTCCTGGAGAAGCTCGTTCCAAATTGCTCTACGTTTACACCTCTGGAACTACGGGCTTGCCCAAAGCAGCTGTGATCA
CCAACCTGCGGTTCCTCTTCATGTCTGCAGGATCCTACTACATGCTCAAGATGTCCAGCGACGATGTGGTGTACGATCCCCTTCCCCTCTACCAC
ACCGCTGGTGGAATTGTGGGAGTGGGCAATGCCATCCTCAATGGATCCACGGTGGTGCTGCGCAAAAAGTTCTCGGCCAGGAACTTCTGGCTTGA
CTGCGATCGCCACAACTGCACTGTGGCCCAGTATATCGGGGAGCTGTGTCGCTATCTTCTGGCCACCTCCTACTCCCCCGATCAGCAGAAGCACA
ACCTGCGTCTGATGTACGGAAATGGACTGAGGCCACAGATCTGGTCGCAGTTCGTCCGTCGCTTCGGTATTCCGCACATAGGAGAAATTTACGGC
GCCACCGAGGGAAACTCCAACCTGATCAACATCACCAACCGAGTGGGGGCCATCGGATTTGTTCCCGTCTACGGATCGAGCCTCTACCCTGTTCA
AGTCCTGCGGTGCGACGAGTACACGGGTGAGCTGCTCAAGGACTCCAAGGGTCACTGCATCAGGTGTCAGCCTGGGCAAGCGGGTCTCCTGGTGG
GCAAGGTGGACGCTCGGCGGGCCGTGAGTGCCTTCCATGGATACGCCGATAAGGGAGCCTCGGAGCAGAAGCTCCTTCGAAATGTCTTCACATCC
GGAGACGTCTTCTTTAACTCGGGCGACATGGTGGTGCGAGACATACTCGGTTACTTTTACTTCAAGGATCGCACGGGAGACACCTTCCGCTGGCG
GGGTGAAAACGTCGCCACCCAGGAAGTGGAGGCCATTATCACGAACTGTGTTGGCTTGGAGGACTGCGTGGTCTATGGCGTGCAGGTGAGTTTCA
GATATTTCCGATTTCTTTTTATTTAAGTTTGCATCATAAATAATTGATACCTTATCATCAAATGGTGGTCAGCAAGAAAGAATGGAATCTGGCTT
TAATTACCGTTTAATAGCAATCTGAAATGTGTTTATAGATCGCATATATAACTATTGTTTCAGTGTAGCTGAGGGAACTACCCATGTCGCTCTTA
GTCACTGGGTTTCTGGGTTGTGCCATGTAGATAACAAACCACCTGAAACCACAAGCCGCAAACCTTGATTTTCACTATCGGCCCGCATATCTTTG
CAGATCCCCCATGTGGAGGGCAAGGCGGGAATGGCGGCGATTGTGGATCCGGAGCGCAAGGTGGACATGGATTACCTGTCCGTGGTGCTGCGGGG
CAGTTTGCCTCCGTACGCTCGCCCCCTGTTCATCCGACTGCTGGACGAGATTCCGCGCACCGCCACCTTCAAGCTGAAGAAACGGGAGTTGGCCA
AAGAGGCGTATGACATCGGCCAGCTCTCAGATCCCATATACTACCTGAATCGGGACGGTATCTACAGACCACTCAGTCAGGAGCAGCACGAGTTG
CTGCGATCGGGAAAGGCGGGACTCTGAGGATAGAGGTCCCTTTTGCGCCCACAATTGTATTCCAGCCAATCCTCTGTGTATATTGCAAAACGCTT
GTCTGTCCCAATGTATTTTTAACGCTTAAACAACGACTGATTCCGAAAGACCAAAATACCTAAATGCCGAAATAGTGATAAAGTTCTTTCGCTGC
TGGCCCAAAATGCCGGGCGCGTTTCTTGGCCATAAAATGGCAGCTTAACCGATAATGGGAGCCAATACGTTTTACGGCCAGAAGATGCTGCTACC
GCCACAAGATATATCGAAAGTGTTAAATCCCCAAGATTAAGTTCTCGCTCATTGGCAGCTGCTGCAGTTGCTGCTGCTGTTGCTGCTGCTACTTT
TACAGTTGCTGCTGTGCTGTTGCAACATTAACGCCATTTCCGCTCGCTTGCGGCAGCTGCGACTTCGTTGGCCGTCGCCTAAGATAAACGATGTG
CAAAATCCATACAAAACAATGGCAGGAGCAGGAAGGCAAGGTCTTGCAACCGCAGCAGCGCAACATCGTCGACGGCCACCAATATCGATGTCGAT
GTCGATGGCGAAAAAGTTGTGGCAGGCAATCATAAAAAACGAAGAAATGGCAAACAAAGCTGGGCGCCATTTTTAAGGGAGCGAAAATGGCGATG
GCGCGCTGCTTCTGGGATGCCAAAGGTTCTTGGATGGCTAAAAGTTGTTGCATTCAGTTCAAAGTGAGTCCTTTTCGATTTCGCTGGATCGTAAT
TGGTATGATATTTCACTTGGAATATATGCAAGCTTTTTAGGGTCCTGGAATGTGCTTTTAAGATAATGCTATAATGCCTGATTAAGATTACTTGG
GCCGCCATACAAGGCAAACGACAAAGGTTTAGAAAGACACAAGCACTTGTTTCGGCACTGGGGGAAACTTCAGTTTTGCAGGGATCCCGGGATTC
CAATACACAATGTAAAAGCCGGATGCCCAAAATACACATAAAGTTGCAGCTGCAGCAGCTGCCGAACTCCCCGGCCA
(SEQ ID NO: 313)

Exon: 1001..1102
Exon: 2454..2730
Exon: 2789..4265
Exon: 4564..4872
Start ATG: 2531

Transcript No. : CT11417
ACGTCGGGTGAACAGATCAGTCGTGCCGCAACTGCAGCTATATCTTTACCTATGTGTTCTAATTTTCCGTGCCAGTAACCGTTCTGATCGTGCGA
ATAAAAATGAGCGAGAACGAGAAGCGTCCCGATCTGGAGGATCAGGATCAGGATCAGAATCAGGAGCAGGCTGGCGGCAGGAAAATGGAGATCCT
GCTGGAACTAAACCTAAAGCAGAAGCTGGCCACCCGACTAGGCACCATCCTGCTGGCCACAGTGATCTTCGGCGCCTTTTGCTGGGACAACGCGT
TGGCCAGTCTAACACTGGGAGCAGTGGTGGCTCTCCTGCTCAGAAATCCCACCTTCGTCTTTGCCTTGGTAATGACCGCGTCCAGGGACCTAAAG GCTTTCCAGCGATTCGTGGCCCTCAACATCTACCTGCTAAGAAAGGATCGCGGCGGATTCACTGTGGCCCGCTGTTTCCAGGACCAGGCCAGACG
CCGCCCCAAAAAGACATGCTTCGTGATGGACGATCGCCATTTAAGCTTTGCAGAGGCTCTGGAGTTTAGCCAAAAGATAGCTGGATATTTAGCG
ATCGCGGCCTGGAGAGGGGCGACTGTGTGGCCCTACTAATGGAAACGCGTCTGGAGTATCCCTGCATTTGGTTGGGTCTCTCCCAGCTCGGGGTA
ATCACAGCCCTTATTAACTCCAATCTGCGCGGGGAGTCTCTGCTGCACTCCATCAAAGTGGCCAATGCCAAGGCCCTAATTGTGGGCAGTGAACT
CCTGGATGTGCTGGTATCACTTAGGGAGAAGGAGCAGTTGGACGAGGTGCCCATCTATCAGTACACAGATGACGAGGTTCGCGGGGTGGCTGGAC
ATGATCTTTTGCCAGGAGCTGTGGACTTGGTTACTGCTCTAAAGACCCAAAAGAAACTGGAGCTACCGAGTGCTGTCTGTCCTGGAGAAGCTCGT
TCCAAATTGCTCTACGTTTACACCTCTGGAACTACGGGCTTGCCCAAAGCAGCTGTGATCACCAACCTGCGGTTCCTCTTCATGTCTGCAGGATC
CTACTACATGCTCAAGATGTCCAGCGACGATGTGGTGTACGATCCCCTTCCCCTCTACCACACCGCTGGTGGAATTGTGGGAGTGGGCAATGCCA
TCCTCAATGGATCCACGGTGGTGCTGCGCAAAAAGTTCTCGGCCAGGAACTTCTGGCTTGACTGCGATCGCCACAACTGCACTGTGGCCCAGTAT
ATCGGGGAGCTGTGTCGCTATCTTCTGGCCACCTCCTACTCCCCCGATCAGCAGAAGCACAACCTGCGTCTGATGTACGGAAATGGACTGAGGCC
ACAGATCTGGTCGCAGTTCGTCCGTCGCTTCGGTATTCCGCACATAGGAGAAATTTACGGCGCCACCGAGGGAAACTCCAACCTGATCAACATCA
CCAACCGAGTGGGGGCCATCGGATTTGTTCCCGTCTACGGATCGAGCCTCTACCCTGTTCAAGTCCTGCGGTGCGACGAGTACACGGGTGAGCTG
CTCAAGGACTCCAAGGGTCACTGCATCAGGTGTCAGCCTGGGCAAGCGGGTCTCCTGGTGGGCAAGGTGGACGCTCGGCGGGCCGTGAGTGCCTT
CCATGGATACGCCGATAAGGGAGCCTCGGAGCAGAAGCTCCTTCGAAATGTCTTCACATCCGGAGACGTCTTCTTTAACTCGGGCGACATGGTGG
TGCGAGACATACTCGGTTACTTTTACTTCAAGGATCGCACGGGAGACACCTTCCGCTGGCGGGGTGAAAACGTCGCCACCCAGGAAGTGGAGGCC
ATTATCACGAACTGTGTTGGCTTGGAGGACTGCGTGGTCTATGGCGTGCAGATCCCCCATGTGGAGGGCAAGGCGGGAATGGCGGCGATTGTGGA
TCCGGAGCGCAAGGTGGACATGGATTACCTGTCCGTGGTGCTGCGGGGCAGTTTGCCTCCGTACGCTCGCCCCCTGTTCATCCGACTGCTGGACG
AGATTCCGCGCACCGCCACCTTCAAGCTGAAGAAACGGGAGTTGGCCAAAGAGGCGTATGACATCGGCCAGCTCTCAGATCCCATATACTACCTG
AATCGGGACGGTATCTACAGACCACTCAGTCAGGAGCAGCACGAGTTGCTGCGATCGGGAAAGGCGGGACTCTGA
(SEQ ID NO: 314)

Start ATG: 180

MEILLELNLKQKLATRLGTILLATVIFGAFCWDNALASLTLGAVVALLLRNPTFVFALVMTASRDLKAFQRFVALNIYLLRKDRGGFTVARCFQD
QARRRPKKTCFVMDDRHLSFAEALEFSQKIAGYFSDRGLERGDCVALLMETRLEYPCIWLGLSQLGVITALINSNLRGESLLHSIKVANAKALIV
GSELLDVLVSLREKEQLDEVPIYQYTDDEVRGVAGHDLLPGAVDLVTALKTQKKLELPSAVCPGEARSKLLYVYTSGTTGLPKAAVITNLRFLFM
SAGSYYMLKMSSDDVVYDPLPLYHTAGGIVGVGNAILNGSTVVLRKKFSARNFWLDCDRHNCTVAQYIGELCRYLLATSYSPDQQKHNLRLMYGN
GLRPQIWSQFVRRFGIPHIGEIYGATEGNSNLINITNRVGAIGFVPVYGSSLYPVQVLRCDEYTGELLKDSKGHCIRCQPGQAGLLVGKVDARRA
VSAFHGYADKGASEQKLLRNVFTSGDVFFNSGDMVVRDILGYFYFKDRTGDTFRWRGENVATQEVEAIITNCVGLEDCVVYGVQIPHVEGKAGMA
AIVDPERKVDMDYLSVVLRGSLPPYARPLFIRLLDEIPRTATFKLKKRELAKEAYDIGQLSDPIYYLNRDGIYRPLSQEQHELLRSGKAGL*
(SEQ ID NO: 315)

Name: fatty acid transporter-like
Classification: transporter

Celera Sequence No. : 142000013384832
GAAATTGCAGCGAAACCCGGGATTTACGGATGCCAAAGCTGACTAATTCGTAGAGGCGCCTTCAATTCGCACTGCTCAGCTCGTAATTCGTGAAA
TTTGTAAACAACACGCGCACTTTTAACTAAATTCAACATCCCATTGATGATTACGGAGCAAGTATAGCGGCGAATGGGCGTGAAACTTGAGGACG
CACGCAAACGGAATGGGGTATTACCTCATTCGTACACAGTCACTTTCACGGTTTTCGGCTTTATCTATCACTGCACTATCGCTATTTTGACTGTT
TTTGCCGCACACTAAGCCATTTGAAGCGTATTTTACCCCGAAAATGCTTGGAAATTTCTCTCGCGCAAACGCTTCGTGTTGCCACTGAGCTGCAA
TTGCACCCTGTTTGGCGATCTGGCAGCGCCGGCGAAAAATGGCCGTTTAGGTCATCTGTGCCAGAAGAGAGCAGCACTATTTGCCTTCGCCAAGG
GCAAAAACAGAAACAACACACACTTATGCAAACACACACGCAGAGGGGGAAATAATAAGTTAAGTCGGCTGCTGCTTAGTTACTTTGCTTTACAG
CTGGTTTTCGGCAGGTGCAGCCTCAGCAAACGTTCTTTTCCGCACTTCCGCTGTCCGATTGCGCACTTTCTAACTGTTTGCACGGCGCTTTTCCT
CTCATGATTTTTCCACCAGCATTGTGTGGCCGTTCAACAAAACTCCAAAAATACCAAGGATGGGTGATTTTATACACCAGCAATCCGGTCCTCCT
ATACCCTTCCCTTTATAACATATAGAACTATTAGGTTTTCTTAACAGCTGTAGAAAATCGATATCAATTCACTACTTTCCAGAACACGACAACTT
TATTGTTCTAAAATGTAAGTGTAGGAAAATAATGAATATGTTATATTTAATATGCTGTATTCCGAGTCCGAGTGTGACCAGTTAATCATTTTTAG
AAAAGCATGCTTTTGCTTGCCTTGAAATAAATTCAGAAAGCGAGGCGTCGGCCACACTGTAAATCGTTTCTGCTTGTCATTTTGGCCTGAGTTTT
TTGCCGCAAATTGCAGGTAATTTAGCGAAAAACAGGAGTCGCAGGAAGCCAAACCCGTCGAAAACAAATCAGTCCGGTACCTATCAATCGGCGCA
GAGGTCATAGTAAGCCCCCGAACCGAAAACCCAGAAAAAGCACAAACATGCCGTCGCAGGAGGTGAGCGTAAACAAAGTGATAGTGCATCCATTG
GTTCTGCTGTCCGTGGTGGATCACTTCAACCGGATGGGAAAGATTGGCAACCAGAAGCGCGTAGTGGGAGTCCTTCTGGGCTGCTGGCGATCCAA
GGGAGTGCTCGATGTGTCCAACAGCTTCGCAGGTTAGTACTGCCTTTGAATATCCAAAGTCGTGGCCATAAAACAAAAGAATTCCCTCCCGACTT
CCAGTGCCCTTCGACGAGGATGACAAGGACAAGTCGGTGTGGTTCCTGGACCACGACTACCTGGAGAATATGTACGGCATGTTCAAAAAGGTGAA
CGCCAGGGAACGGGTTGTGGGATGGTATCACACAGGTCCCAAGCTCCACCAAAACGACATAGCCATCAACGAGCTGGTCCGGCGCTATTGTCCCA
ACTCCGTGCTGGTCATCATCGACGCCAAGCCCAAGGATTTGGGCCTGCCCACAGAGGCGTACATATCGGTGGAGGAAGTCCATGACGACGGCTCT
CCGACCAGCAAAACTTTCGAGCATGTGCCCAGCGAGATTGGCGCCGAGGAGGCGGAGGAGGTGGGCGTGGAGCATCTGCTGCGTGACATCAAGGA
CACAACCGTGGGCAGCCTGTCGCAAAAGATCACCAACCAGCTCATGGGTCTGAAAGGCCTGAATGCCCAGCTGCGGGACATAAAGCAGTATCTGC
AGCGCGTCGGCGACAGCAAGATGCCAATCAACCACCAGATTGTCTACCAGCTGCAGGACATCTTCAACCTGCTGCCCGATATAACCAATGACCAG
TTCACGGGCACAATGTATGTGAAGACCAACGACCAAATGCTAGTCGTCTACCTGGCCTCCATGGTGCGCTCGATCATTGCCCTGCACAACCTGAT
CAACAACAAGCTGGCCAACCGCGACGCCGAGGAGGGCAAGAGCGACAGCAAGGAGGCCAAGGAGAAGAATAAGGATAGCAAGGATAAGGACAACA
AGGAGACCAAGGACAAGGACGGCAAGAAGGCGGAGGAGAAGGCCGACAAGGGCAAGGACGAAGGCGGCAAGGGTTCGCGCAAATAGGAGCGGAAG
AAAAAGCGCAAACCCCGTCGCAAACGAAAGAAGCAGCGGGCGCAGGACTAGCTGCTGCTTCTTCTGTTCTCCAGGAAGTGGAACTCATCTGCAGA
CCATACGGCGAGGGTGTGCAGTGGCCTCAGAAATCAAGCATTGCTACCATTCATCGTTCATTTTCCACACGAAATTAAGCTCCCTCTTATTATTT
CGCGTAACTAACTAATGGCAAGTTTATGTAATTAAAAATTAAATAATTTAAATACTCCTATTGTTTGCTTTCCTCTAATATTGCTAGAAGCAGCA
TACCTAGTATTAAAACCGCTCAGGCTTGTGTTTTTGTATTTCGTAAAACCGAAATTATATTTTAAAACAAACTAAACTCGCTGGAGAGGCAACGT
AAATGGCTGACTTACGATTGCCTTTCCCCGAGCACAAAAACGGTTGAGTAATGCATTGTACAGGGCGTTCTCTATCTTAGAGCAGTTATTACTTA
GAAAGCATTTTACCAAATTTCACTTGACTTACAGCTGAGCTAGTTAACGCTTACGAACTAAGGCTAAGGGTTCCATTGCTAACACCATCGATGAC
CCAACAACTAGAATACTTAGGTTCACTATGTGCTTGCAAAGCAATCAGAAACTAGATCAAACATTGAGTTCCTGGCACCTCCTTTCCGAATTGTA
GCACTATGCACGGGAGTCCTGCAAAATGGCTGATTTGCAGGACTCCGGTGTAGACTGGAGGCTCACTTAGACCAGCCACTCGCTGGCCAGCGGGA
ACTTAAGCGGCTGGCAGCTGCTGAGTCGCAGCGAGCAGTTATTGTCCTCGGCAGCAAGTGGGATCCTGGTGGTCGCCATGGGATTGCTCTGCACC
GAGCAGAGGCTTAAACTATGGCTGTGCGACTGCCTAAGACTAGAGCTAATGATATCGCTGCTGATCCGATGCTGATGCTGATGGTGATGATGATG ATGATGCTGTTGCTGTTGCTGTTGGTGGTTCCGGCTCCGATACTGATCTTCCGACGGGCAGGAATGGTTGCAGTTGAGATTAGTTGAGTAGCAGC
TCCTTCCCTCGGCCCCTGAGGTTGTTGGTGACAAGCTGTTGCTGTTGCTGCTGCAGTTGAGGTTGTAGATCTTGATGCTCGTGCAGCTGGTGCGG
ATGTTGACGTGAACCTGGGCGTGGTCATGTCACACCGAGGTGCCCTGTTGGCCGGGCACCACCGATCCGCAGTTGTCCT
(SEQ ID NO: 316)

Exon: 1001..1362
Exon: 1430..2499
Start ATG: 1188

Transcript No. : CT11503
GCCACACTGTAAATCGTTTCTGCTTGTCATTTTGGCCTGAGTTTTTTGCCGCAAATTGCAGGTAATTTAGCGAAAAACAGGAGTCGCAGGAAGCC
AAACCCGTCGAAAACAAATCAGTCCGGTACCTATCAATCGGCGCAGAGGTCATAGTAAGCCCCCGAACCGAAAACCCAGAAAAAGCACAAACATG
CCGTCGCAGGAGGTGAGCGTAAACAAAGTGATAGTGCATCCATTGGTTCTGCTGTCCGTGGTGGATCACTTCAACCGGATGGGAAAGATTGGCAA
CCAGAAGCGCGTAGTGGGAGTCCTTCTGGGCTGCTGGCGATCCAAGGGAGTGCTCGATGTGTCCAACAGCTTCGCAGTGCCCTTCGACGAGGATG
ACAAGGACAAGTCGGTGTGGTTCCTGGACCACGACTACCTGGAGAATATGTACGGCATGTTCAAAAAGGTGAACGCCAGGGAACGGGTTGTGGGA
TGGTATCACACAGGTCCCAAGCTCCACCAAAACGACATAGCCATCAACGAGCTGGTCCGGCGCTATTGTCCCAACTCCGTGCTGGTCATCATCGA
CGCCAAGCCCAAGGATTTGGGCCTGCCCACAGAGGCGTACATATCGGTGGAGGAAGTCCATGACGACGGCTCTCCGACCAGCAAAACTTTCGAGC
ATGTGCCCAGCGAGATTGGCGCCGAGGAGGCGGAGGAGGTGGGCGTGGAGCATCTGCTGCGTGACATCAAGGACACAACCGTGGGCAGCCTGTCG
CAAAAGATCACCAACCAGCTCATGGGTCTGAAAGGCCTGAATGCCCAGCTGCGGGACATAAAGCAGTATCTGCAGCGCGTCGGCGACAGCAAGAT
GCCAATCAACCACCAGATTGTCTACCAGCTGCAGGACATCTTCAACCTGCTGCCCGATATAACCAATGACCAGTTCACGGGCACAATGTATGTGA
AGACCAACGACCAAATGCTAGTCGTCTACCTGGCCTCCATGGTGCGCTCGATCATTGCCCTGCACAACCTGATCAACAACAAGCTGGCCAACCGC
GACGCCGAGGAGGGCAAGAGCGACAGCAAGGAGGCCAAGGAGAAGAATAAGGATAGCAAGGATAAGGACAACAAGGAGACCAAGGACAAGGACGG
CAAGAAGGCGGAGGAGAAGGCCGACAAGGGCAAGGACGAAGGCGGCAAGGGTTCGCGCAAATAGGAGCGGAAGAAAAAGCGCAAACCCCGTCGCA
AACGAAAGAAGCAGCGGGCGCAGGACTAGCTGCTGCTTCTTCTGTTCTCCAGGAAGTGGAACTCATCTGCAGACCATACGGCGAGGGTGTGCAGT
GGCCTCAGAAATCAAGCATTGCTACCATTCATCGTTCATTTTCCACACGAAATTAAGCTCCCTCTTATTATTTCGCGTAACTAACTAATGGCAAG
TTTATGT
(SEQ ID NO: 317)

Start ATG: 188

MPSQEVSVNKVIVHPLVLLSVVDHFNRMGKIGNQKRVVGVLLGCWRSKGVLDVSNSFAVPFDEDDKDKSVWFLDHDYLENMYGMFKKVNARERVV
GWYHTGPKLHQNDIAINELVRRYCPNSVLVIIDAKPKDLGLPTEAYISVEEVHDDGSPTSKTFEHVPSEIGAEEAEEVGVEHLLRDIKDTTVGSL
SQKITNQLMGLKGLNAQLRDIKQYLQRVGDSKMPINHQIVYQLQDIFNLLPDITNDQFTGTMYVKTNDQMLVVYLASMVRSIIALHNLINNKLAN
RDAEEGKSDSKEAKEKNKDSKDKDNKETKDKDGKKAEEKADKGKDEGGKGSRK*
(SEQ ID NO: 318)

Name: 26S proteasome regulatory subunit S12
Classification: endopeptidase
Gene Symbol: Mov34
FlyBase ID: FBgn0002787

Celera Sequence No. : 142000013384496
AAGCCGTTCCGGAATTTGAGGGCCGTGACCGATGGAAACTCCTTGACGCCCGGCAACTTCATGGCTACATCCAAAGTTGAACATCGTTGCTTGGT
ACGTGGATCCCAGGCTTCTACGGTGCCTTCTTTGGTACCGGCTACCAGAAGATGGTGCTCTGGATTCACTTCACAGGCGTTCAGGCAGCTGCCAT
CCGTTTCAAAGGGTTGCAGGAACTGACCGCGCTCCAAATTGAGTCGGAAAATGTCCTGAAATCAAATCTTTAGAATAAACTAGACATTAGATAGA
CCTCAGTTCTTACCCTGCCCACTCCCACGATGAACATGTCGCAGCTGGGCTTGTGGTACTTCATGTCGCGTCCAAAGCGCGGTATCCTTAGTCTG
TAGTGCCGCCCGTGGGCCGCATGGATCTCCACATAGCGATCGCATTGCAGGAACACCATCTTGCTGTAGTCGTCGCTAATCACCTCAAAGGTGGT
CACCTCGGCGTCGAAGCAGCGCTCGAATTTGATAGACAGGTTGGACACCTCGAAGCACTTGACGCGCGGCTTGTAAGTGCCGGTGGCCAGGATGT
ACTGTTGGTCGGGACTCATGCGGATGCTGGTGCAGACGCCGGGCATATCGAAGTCCTGGATGAGCTCGATCTGTCTCCGGGAGTCCACTTTTTTC
ATGAGCTGTGACCGCTTTCGCCGATCCGTCAGCCACTGTGAAGGAGATACTCATGAGTTAACTGCTTGGCAACGGGTTTATCTTGCTACTCACAT
CTGGCACCGACTTGCCGGCGCTCAGGTTGTAGATCTTCACATCGTTAACTTCGTTTACGAACATCTTGAGGGACGATTTTTGCTCAAAATTAAAA
CATAAACAAACGAAGTCCGCAACACGTGCGCCCTCTATCGATAGACACGATTGTCGATAGCATCTGGCTGCGATAAGCACCTATCGCGGCAGTGT
GACCCTTGGCTTGCCAATTGCTCAGTGTGACCGCAGGAAACCAAGCAAAACAAGAGAACGCAAAAGCAGTGAAAAAAGACTACTGATTTGCATCG
ACCTACCAATTGAAAATAATCGCAATAATTGCCTCTCGGTGCAGCCCCGCAACCCCGCGAAGCCAGTGTGCGTGCTAGCACGAAAGTGAACTGCA
TTTTGCATCGCCAAATTGCCCAAAAATTGCAATCGAATTCCGCACAGCCAAACAACAATACGCACACATACACACAGTACCCCCCGCTCTGCGTA
ACCGCCCTACGTTACACATTCCGTTCGCTCCCTAAGGTGGACTAAAACTAAAGTGATCTAAAACGGTGAGTAATATTCGTTGTTTTTCCTTAAGC
CAATTAAACACTGATTAAATTATGCGAAATGGAAAACCGTCTGCGAAGGGGTGACGCAGTGCAGCTGTGGGTGCTCCGCAACTTTCCCTTGTGCT
CTCGCTCTCTCTTGTTTTTGTCGTTAGGCAGCAGCACTCCATTGTTGTTGTATACACCCCCTGATTGCTTTGATACCCTGCAATGGGGAGTTACT
GTTTGTGACCAAGTTAAGAAAATAAATATGATTTACAAAAATCGATTAATTCTGGGGATGTTTCAGGTTTTTATGGTGTATAATTTATTTTTTG
AATTTTTAGGGGATGGTGGGGCAAAAACGGCCGCCACTCTACTTAAAAATCGGTAGGTGAGGAGTTTGTTTAGTATACGCTATAAATAAATACTC
TAAATTAGTTTTTATAAGATGGATTATTATATGAGTGTATGAGTTATCATAGAAATATTTACCTGTGCTTATATATTAATTTATTATATGAATTA
TGCAAACAAGGTTTTTTCAAAATGTAGGCGAGCATGAATAAAAAATTATAATAAATCAGAAGTTTTCTTAGTAGTTGTTATCAGTTATTAATATA
TTTCTTTTTCATTTTGTTGTGTCTTATTGCGTTGTTGTCTTCAATGCGGGCTTATTTTATTAGTTTGAATGGATGTGCGCTTATTTGTAGATACT
CAAATATCAAATCGTATTCAGTTATATCTTAGAAATGGAATATAAAGCGCACATTTATAAAAGTATATTTATATTTAAGATTTTTTGCCAAAGGG
TATACATACTTCGTCTGTGTATAAATATATATTTCTCATACTCCTTTCGTTATTTTCCCTGTTATGGGTGCGCCGCTGTGTTCCTTTTATGAGGG
GCAATGATGATCCACTTCCATTCAACACATTTTGCAAATAAGTACATATGTACTTCGCCTCCATTGATTGCTCCACTGATGTTTGGCCTTTGGCG
CTTGACTGATAAGACTCGAGACCGAGACCTACTACTTAGTTAGTCTAAACTGCCCGTCATAGAGCCTATTAAACTGATATGCACTTGTCACTTTG
ACAAGCAATGATAAGCGATTATAACTGTATTTGATGATTTAAGTATGAGCAATTAAGAATCCATAATTGATACTCATCTTTTCACACTATATGCT
GCTAAGTCACATTCTTTTGTATGAAATTCATTCATATGAAGTAAGGCAGGATGATTACCCTAAATACAAACTAACTTGATGAATAACTTCGCGCG
TACTGCTCTTAATAATTGAATTCCCACGATTGCTTGCTCGGCGACCTTGATCCAAATCGCTTTCAGCTTGGGCGAAGGGTTCAATTCACTCTCTT CAGCGCCCCTTAACTGCGGACAAATCAAAGGCTTTCGAACGACACGGATACTGCGAATGGACAAAGTCAAGTGGCATGAAGTGGATATACCCGCC
GCTCTTGAAGCTTGCCTCTTTCTTATTTTTTTTTTTTTTGGCTTCAGTTGGCAGGCAAACAAACCCGGTCGGCTGTTCAAACACAAGCAGGCCT
TAAAAAGAAATATCGGGGCCAGTTCGAGAAAGGGGAACAAAATGTGGTGTCGACGCAGAACAAATTAATGCAGCGCCTCGGTTTGTTGATAAGCA
GCGACTACGGTTGGACATTCAAATGAGGAGCTGATAGTAGTAGTTAACACTGTTTGATTGGGTCAGAGTTCATTTCTGCCGGTGTCAAGATGAGC
AAAGTGCGCAGCGTGGTGAACAAACTGCACGAACGCATAGACTACTTTATTGAAAAATGTGTGAAATATTCTATATACTCAATGACTCTGCAATG
TAATAATAATAATAATTTCGCTTGCTTTTTAGGTCCCAACATGACTGCAGCGCCATACAACTACAACTATATCTTTAAATACATCATCATTGGTG
ACATGGGCGTGGGCAAGTCCTGCCTGCTCCACCAGTTCACCGAGAAGAAATGTGAGTAGACTGTGCTGAGTAATAATGTATGTAATAAGAACTAA
TCTCTACTTGCCGTCCTGCAGTCATGGCCAATTGTCCTCACACCATTGGCGTGGAGTTCGGCACACGCATCATTGAGGTGGACGACAAAAAGATC
AAGCTACAGATCTGGGACACAGCGGGTCAGGAGCGATTCAGGGCAGTGACACGCTCCTATTACCGTGGAGCAGCTGGTGCGCTGATGGTCTACGA
TATTACCAGGCGGTAAGCGAAGCAAGCTACTATTTGAGAAATTGCTTTACAACTTGACCATTCCAGCTCCACGTACAATCACCTGAGCAGCTGGC
TTACCGACACTCGCAATCTCACCAATCCCAGCACTGTGATCTTTCTCATTGGCAACAAATCGGATCTGGAGAGCACTCGGGAGGTTACCTACGAG
GAGGCCAAGGAGTTTGCCGACGAGAACGGCCTAATGTTTCTCGAAGCGAGCGCTATGACGTGAGTTTCAACTGGAAGCATAGTGTTTGAGCATAT
ACTGATTATCTTTTTTTTTATCGCCCAAACAGTGGCCAGAATGTGGAGGAGGCTTTTCTGGAGACCGCACGCAAGATTTACCAGAACATCCAGGA
GGGTCGGCTCGATCTGAACGCCTCCGAGTCCGGAGTTCAGCACAGGCCATCGCAGCCGTCGCGAACTTCGCTGAGTAGCGAGGCTACGGGCGCCA
AGGATCAGTGCTCGTGCTAAATGAATGATGGAACCTAACTTTACGCAAAACCTAGTTATACAAATCAACTTTTATTTTTAGCCGACTCGTAATCT
ACCGATGCCCAAGCAAAAACCAATGTATGTAGTTAAATAATTCGATTAAGCATCAATGTGTGAGCCAACAACAGCGACAGCAACCACAAAAAAAA
AAAAAAACAGAAAAAGAAAATATAAAGTCCTTTCGCTTAATAAGACGCAAGCATTGCAACATTTATTGTATCGGTTAAGCATAAATACTAGAAAA
TTAAACATGTTTGTTGGCGCAAACTAAAGTTTTGACCATGAAATTTCGAAAAGTTTATCGCACTAACACCATCCTTCGGTCTCAATTTATAGATG
AATTCGTTTGAGATATAGATCATGTTTTTGTTGGCTGATGAATCCCTGTATATAATATATATATGTATGAATTTTTGTATCTCCCTAATTTTTTG
TTGAGTATTTGTTGTTGTCGCGTGCAAGAATTGGAGGAAACGATCAATGTTATATGAATATTTACGATGTATTAATGGCATAATGCAATAGGAAA
TAAATAAAATGGTATTTATAAAACCCCTACCAATAGAAATGAATTTCTCTTTCAAATAATTTAAATTTTAATTTGCATATTTAACCATTCGTTTA
TATTTAATTCTACACCAAATCGCTGGATAATTTTATAATTTACCGGATTTCCATTTAATAGATTTAAATTTTATAAATATTTGGGTACTTACGAT
TTACTTAAATATTTTGTAAAAAGCTTTTTTAATCCATTTAGTGGAATACCCTCAACTTTGACTTGCGCATAACTTCATTCTTGTTTTATTTAGTG
ATGCTAACGTTGGGTTGGAAATCAGCTGATTATGACTATGAACAATAAAGTTTGTAAGTCAAACAACGATTTTTCGTATACTGTTCTTTTGTTTG
TTGCTGGTTGTCTAATTAATCATTTTAACTGGTTATCAGTCCAATTTTTGTTTTCTACACTACACTATTCTACACTATTTTCGATTTCCTTGAAA
TTTAGCGGGAAAAACTCTGAGCTAGCATCTTCGGTGGCATCGCTGTGTGCGCGCTTTTGTGCGAATGCCATGGTATGCAAATTAAATTTAATTTA
TTCCGATCATCATGAAAGTGACAAAGTAGCTGCTTAAGTAGCCAGGGAAGCGCACAACGTAATCTAATCTCGATCCATGATGCAAATCAAGCGCC
TCCTGTGCAAATCCTGCGGCCTGGGCACCCTTCTGGTGGCGGTCGTCTGGCTGCTGGCGCTGCTTTTCTACTCGCACAGCCTGCGCAGCTCCATC
CGCTCGGCAGGATGGAGGATCGACGAAGGGAACGCAACGCCACGGGCCGAGCTGAGCTACCAGGCCAGGGTCACCGTCGGATGCACTCCAAATGC
CAGCATTACCACTGGCGAATCGCCGGCGGCACCCAAGCCGCCCAGTGATCCGGAGCAATTGGAACTGTTGGGTGTGGTGCGCAACAAGCAGGACA
AGTACATACGCGACATTGGCTACAAGCATCACGCCTTCAACGCGCTGGTGTCCAATAACATAGGACTCTTCCGGGCGATCCCAGACACTCGGC
(SEQ ID NO: 319)

Exon: 1001..1300
Exon: 3168..3281
Exon: 3347..3527
Exon: 3582..3764
Exon: 3833..4603
Start ATG: 3176

Transcript No. : CT11521
CAAGAGAACGCAAAAGCAGTGAAAAAAGACTACTGATTTGCATCGACCTACCAATTGAAAATAATCGCAATAATTGCCTCTCGGTGCAGCCCCGC
AACCCCGCGAAGCCAGTGTGCGTGCTAGCACGAAAGTGAACTGCATTTTGCATCGCCAAATTGCCCAAAAATTGCAATCGAATTCCGCACAGCCA
AACAACAATACGCACACATACACACAGTACCCCCGCTCTGCGTAACCGCCCTACGTTACACATTCCGTTCGCTCCCTAAGGTGGACTAAAACTA
AAGTGATCTAAAACGGTCCCAACATGACTGCAGCGCCATACAACTACAACTATATCTTTAAATACATCATCATTGGTGACATGGGCGTGGGCAAG
TCCTGCCTGCTCCACCAGTTCACCGAGAAGAAATTCATGGCCAATTGTCCTCACACCATTGGCGTGGAGTTCGGCACACGCATCATTGAGGTGGA
CGACAAAAAGATCAAGCTACAGATCTGGGACACAGCGGGTCAGGAGCGATTCAGGGCAGTGACACGCTCCTATTACCGTGGAGCAGCTGGTGCGC
TGATGGTCTACGATATTACCAGGCGCTCCACGTACAATCACCTGAGCAGCTGGCTTACCGACACTCGCAATCTCACCAATCCCAGCACTGTGATC
TTTCTCATTGGCAACAAATCGGATCTGGAGAGCACTCGGGAGGTTACCTACGAGGAGGCCAAGGAGTTTGCCGACGAGAACGGCCTAATGTTTCT
CGAAGCGAGCGCTATGACTGGCCAGAATGTGGAGGAGGCTTTTCTGGAGACCGCACGCAAGATTTACCAGAACATCCAGGAGGGTCGGCTCGATC
TGAACGCCTCCGAGTCCGGAGTTCAGCACAGGCCATCGCAGCCGTCGCGAACTTCGCTGAGTAGCGAGGCTACGGGCGCCAAGGATCAGTGCTCG
TGCTAAATGAATGATGGAACCTAACTTTACGCAAAACCTAGTTATACAAATCAACTTTTATTTTTAGCCGACTCGTAATCTACCGATGCCCAAGC
AAAAACCAATGTATGTAGTTAAATAATTCGATTAAGCATCAATGTGTGAGCCAACAACAGCGACAGCAACCACAAAAAAAAAAAAAAACAGAAAA
AGAAAATATAAAGTCCTTTCGCTTAATAAGACGCAAGCATTGCAACATTTATTGTATCGGTTAAGCATAAATACTAGAAAATTAAACATGTTTGT
TGGCGCAAACTAAAGTTTTGACCATGAAATTTCGAAAAGTTTATCGCACTAACACCATCCTTCGGTCTCAATTTATAGATGAATTCGTTTGAGAT
ATAGATCATGTTTTTGTTGGCTGATGAATCCCTGTATATAATATATATATGTATGAATTTTTGTATCTCCCTAATTTTTTGTTGAGTATTTGTTG
TTGTCGCGTGCAAGAATTGGAGGAAACGATCAATGTTATATGAATATTTACGATGTATTAATGGCATAATGCAATAGGAAATAAATAAAATGGTA
TTTATAAAACCCCTACCAATAGAAATGAA
(SEQ ID NO: 320)

Start ATG: 309

MTAAPYNYNYIFKYIIIGDMGVGKSCLLHQFTEKKFMANCPHTIGVEFGTRIIEVDDKKIKLQIWDTAGQERFRAVTRSYYRGAAGALMVYDITR
RSTYNHLSSWLTDTRNLTNPSTVIFLIGNKSDLESTREVTYEEAKEFADENGLMFLEASAMTGQNVEEAFLETARKIYQNIQEGRLDLNASESGV
QHRPSQPSRTSLSSEATGAKDQCSC*
(SEQ ID NO: 321)

Classification: enzyme
Gene Symbol: Rab14
FlyBase ID: FBgn0015791

FIGURE SHEET 177

Celera Sequence No. : 142000013383801

TAGTCCTACCGTATTGGTTGAATCCGGAGAGATTGTAGGCCCATCTGCCCAGATTTGCTGTGGGGAAAAATTCGCATTACATATTTACGTAATCA
TAATATTCCGGCGTACTGCACTACGAAATTTGTTGCATGCAACGTGAGTCCGATTGTTGCCCGTTCGTATTACTTACAGAGAACTGCGGGTCCCT
TTCTGGCAATATAGTTCGACATGGTTTACGTAAAATCAGAAGTCGGGAAAGAGATATTCCTCCAGCCTTTTTATTTTAGGTATGAGAACGTTGGA
GATGGGTCTCTCGATAGCTATCGCACCCCGTTATCGATCAACGAGCACTACGGTTGCGTTTGTACAAATCGATTTCCGAAATGTAATACAGACAC
ACTGCACCTATCGATATATCGCACTCAAGAAAATTCGTTATTCTTTAGTTTTAGAGCTATTAAATATATTATCTTTTAACATTTTACCCTTTTGT
ATTTGTATTTAGATTGTTCAAAAACTTGGTGGAGACGGCAACCGAACTACAGTATAATTACATCTCCAAAGTTGGTCATTTTGCAATAACTTTTT
GTATAAAGTAAATAAAATCAATTCAAATTCTTGTAAACCCATTTAAGCCCATGTAAAAATCCGCCTTCATAAACAAAATACTTGTAGTTTATCAA
ACCGAATGATTGTGGCTTTCTCCTTTTGTAATTTGTTATGGGAAACACTCAAAAAAGGTTTTTAATTTGGGTTAAGTTATAATTTATGTTAACCA
ATAACCTCGATTAAATTAATTATAAAAATGATGCCTGAAGATATACAACTTTCACTTAACTTGCAACACGGGTATTGTATATTAAACAGCAAACA
AAAAAGGCAAAAATGTTGGTAATTAGCGGAGTGCTTCGACAAGCGGAAATCCCTACTTCTCATTTAAATAATATTTCCCCAATTTTTTGCGATAA
GCCCCCGCCAACGGTAAACCCTTCATTAAAATGATTGATAGCGTTTTTATTTTAAAGTACATACCTTCGCTTTATTATGACTACAAAATATCAAT
TTATACAAATTAAAGAACATATACAAATTCTTTATATATACAGTGCCCTCCCTTAAGAGTGAACACTCGAATATGTGAACTTTTTAGTAAAAGTG
AACGATTAATTTATGAAATTTTAGAAACTTTCGCTTAACTTAGTAAAAAAATTAAATTTTTTCAAACGTGGTGTTTTTGAAAAATATATTAAATT
GTTTATTTTTTCTGTGATTCGTTATAGTGAACAAATTCGATTCAGTGCACACCCTTGGTTCTCAATAGTCCACTGTTTCGAGTGAGCACTGTACA
TACACTAAGGCTGGCACGAACACGACACTAATTTAAGTTTGTTTCGGTTTTTGTTTCTGATTTCTGAACACACGTTATATATATACATATGTATA
ACATTGAGACCCGTTCCAGCCTTAGTTTATACATATATCACTGGGCACATAATGTAGTAACTCCCAATGCGCTGAGTGGCCGGGAGAGAGAAATC
ACTTATTGTTCTTAGCTGCAGTCAATGACAAAAACTCCACCTTTCGAGCCAAGTACTCATTATAACGAAGAAATGCATAGCTAAATGGGGCGAAT
AAAAAATTGGTCATTAGTATCGATTGGTTGTAAGGGTCGTAATTGGGGGAAAAAAGGAATTGCAGGGTGCACAATAATATAATAAATCCATTATA
ATGGCCGTCTAATGGTTGTTGATGGATCTTATCAAACAAAACTGATATATATACTGATGATATATATCTATATATCTAAAGGATTTATCATCTAA
TTGCATCGTGCATTCCCAACTCAAAGTTACAGTCCATATACTATGCAACACGCACCCTACGTAGTCGAAATCGATAGTGGAATGCTCGGCTTGCA
ACAGGGACCACACCGTCCAAAAGATATGCGATGCCAGCGCAAACTGATTGACCTGGACATAGAGCAGTTCGACTTCGTCGTTTTGAATGTTGCTG
CGCTGTAGGTACTCCTCAAGGTAGACCCTCAGCCACTGGAGCTGGAACTCGCGCTTCGGATAGCGCGAATAGTCGACCTCATCCACGCCGCACAT
CTCCGCAAAGTGGTTGCCAATGTCGAAGGCCTGGAAATTGTAATCGGCATACTCGTAGTCGATGAAGTTCACCGTATTCAGGCTCTGCGTATAGA
TCACATTTCCCAGCAGAAGATCGTTGTGGGAGAAGACAATCGGACTGTCCAGAGCCTCGAGGTATTCATATAGCTTGTTGAACTCCTCGCGCAGG
CGGCCGATAGGTAGAAACGTTTCTTTCACTCTGCAAATTGCAAATCAAACAATGAGCGAATGAACAAAGGACCGAAGATGCAAAGGATGTCTGGT
GTCGTTACCTTTTGTGTTTTTCAGCATCACTAAAACGTTCAGGTACTAAATCAAGAAAGCTCTGCGTCTTCTTCCAAATCATCGGCATGGGTTTG
GTCGCCGAACTATCCCCGTGCTTTCTCACCTTGCGATGCATCTCGGCCATGCGACGGGCGACCAAGGGCCAAATTTCTGGACAGAGCACACTGTC
CGTATTCAGGGTGGTTCCAGGTACGTATTCGTAGACGAGACCGTTCTTGAACGTGGCATACAGCGATGGCGCTAGCCCATACGTATGCAGTAGAA
GAAAGTTTTGCGTCTCCGCCTTGCGATCTATCAGTAGGTCCGTTTTGTTACCGTATATCCTGACGAGCACTACGTTATCGGAGTACTGTACAGGT
GACCCGTCGTCCGCTGCCCGATCGTCTGTGAACTCATCATCGTCCTCCTTCTCAATGATGACTGGATCCTCGGACTGAACGGGCGACAAACCCTG
CGTCTTGATAGGTAAATACGATCCGCCGTTCTCATCGTTCAGTTTGGAGATCTCCTTATGAAAACATCCGACCAGTTTGTTTGTGATGCCATCGG
TAAAACTCTAAAATAAGCACACAGAGAACAGCACCATTAAATCGTATACATAAAAACATAATACTCATCGATGTAGATCCAGTGAATGGGTTAGG
ATGGATTAATTAGTAGAGTAGCTACATGATTTGTGTGCTTTGTTTATTGTAAGTGAAGTTATTGCATCATCACCTAATACCAATTGCTATACGGT
AAGGTTCATTAGTAGCATTCAATGGAACGGTTTCGGGAATTCGCCTTTTAAGCCACAGCTCAAGAGCTACAGTAAAGGGCTTATGGCCACTTCCT
TATCGACTCCACATGCTTCTTATGTACATATGTATGTACATATATAAAAGAGTGAAGCACATGGGTGATAAACTTTGTGACACCAGCTATTTGCG
TGCTAAGCGTCTCAGAAAGACCACCTTCGTCTTGAATTATATACGCATACGGTGCTTTTTATAATGAAAACACAGAAACAGATAAGATAATGAAT
TGCTAAACAATTTAAATTCATATAATTCAAAGCGAAAAAGCCCAGAATGTGTGAAAGGTGAATGAAATAAAAGTGCGAAAATAGTAATTAGTTCA
TTTCAATCACTTCGATCTGCCCTGGTTTTATTCATTCACTGAGAAAAGTTTATTTATTGCATTTAATCAATATTTCCCAGTTATTTTCCCTTTGC
TCAGTGTTCAATGCACTTAAGATTAAAGTAGTGCTGTACAAACACGTGTGTTTCAGATCGCTGGCGATATAGTAAATTTTCCACTTCATATATAG
AACGACGTCTCTAGCGGCTATAAAAATGTCAATAGTTAACCCATTACTCGCATGACAGTTGTGAGGCATAAATAACCGTGAAACTTGAAGTAAAA
CTTAAACATTTGGTTTATGGTTGAGAAACGCTGCCTATGACGCCATGGTCCATGAATCAACTCAGATTTGTGCAAGTATTCATAGTATTCATAGT
AGTCATATTGTAGCATTTATTATCACAATTTCGCCTGACTGGCGCCAAAGATTTGTGACTCCCCATAAGGATGCCTCCCCTCCACTTGAATCCTG
AATCACGCGACAAATTATCTATAGCTTAGAAAACGGACATGACACGATTTAGACTGTGTACCATGTACCCATGTACTATGTACACCACTCGCTGA
TCAAGGGATGAACCACGTTTTATTGCCCACCAGCGATTTGGCAAGACTCAGCACTTGGCAATTCCGACTGGAGCTGCCATAAAGCTGATAAGTGA
GTTACGGACAAGCTGTGTACACCAATTAGACGTCATGCCTATGGTGCGGCATATACAGATAGCGAGGTCAAGGCGTACAAGTGGCTTCCGATAAG
GCAAAAACGCCCCATTTCAAAAAAACCGGAGTGATTAAAGGCAGCCTCAGGCATTTGTACATACATACATCAATCATACTCCTCTAACTCGACAG
CGTGAAATTATCAAATCGGGCCAAACGAAATCAAGCCCCTAAAAAGCGAGGGAAAAAACGTTTTTTTTCGGATCATCCGTAAATTACGGACGGA
CGGACGGATGGACGGTGTGTCGGTAATGGTTATCTGTAAAAACACTCGAGTCAATGCACCTGCTGTCAACACCTTCTATGTCAGGCATTTAAAGT
ATTGTGGTAATTAGAGAACGTGCGATTTCATTAGAACTAAGGCGACTAATTGGCACGAAGGCCTATTTCTTGGCTCACACCCGTTTCCAACCCGC
TCCGTTTGGTAGGGTGTGTGTGTGTGTGGGGGGGGGGGGGCACTTATTATTATTTTCCCCCCCGGAGTCGAGGGCTAGATTAGCAGCAAACTGGT
TTCTACTGCGACGCGGGGTCTGAAGTCTCCATAGTTCGCTTGGCGACTCGGAAACTCAGAAACGCTGTCCTAATACACCAACACCAGCGTAGTGA
ATAATGTTAATTTCGAATAACAATCCTATGCGTCTCTCTCTTCATTGATATAACAAAGTCTATTTACAATTATCATGGCGGCGCAGCAGCGAATA
TATATATATAATTACTATTTGAAGGTTGGCTGTTGTGCAATAACCCTGTTTCAAACAATGTTAGCAACTACTACGACTCTATATCTCTATATATA
TGTATATGAATGTATATAGTAAAGTATATATCCCACGTTCCGCACACCAGTTAGTGATCGTAATAAATGATAAGGAAACATACAGCGTCATCATC
ACCATCGCATTTTGGGCCGGATAACGATCTTCGATCTGCGGAACTACCCTGATCTGATGGAGAATGTAGAGAATATGACATTGATGGTTTCGTTT
TTTTGCATTGTATAGTGTGTTGTTTGGCTGGTGATTTAATTTGATTTGCTTTGATTTGATTGTTGGTATAATGATATTGTAGGGGGGTTATAATT
TTGAATGTTTTGATGAGGTTTACGTTACCTTAAACTCGACGTGGCTGAGGTCCCAGGTCGGTCGTATAACCTTCAACAGTTCCTTGGCCCCTTGA
ATTACGTCGGCCTCCTCAACAAATATGGGTACAAATGGTACAATTGCCTCTTTTCTGGATTTATCCTCCGGTTTGGCTCGAATATCGCGCGAATT
TTGTTCGTTTTCGTTTTTGTTTTCGCTCCCGCTTGGATTTGGATACGAATTGGAATTCGAATGTGAATTCAATTGGTTCTGGACCTGGTTCGATT
GCGATAGCGATAGCGTTTGCTGATTGACCGTCTGACGAACTAAGGATAAAGAATCTTTCATCACTTTGGGGTTGCCGCCACTTGTTGAAATCTGT
CCTGTGTAACTGTTGCTCTTGGTTTCTGTGCCCATTCTATTGTATTATATATGTGAAATACGAAAGTGTCAGGTCGGGTCATACATATAGAACGA
CAATAACATCAGCATGTAAAATGAGTAGGTAGGTAGGCGGTAGTTAAAAGCTAATCATCCGAATGCAAAACCAACCGAGAACCCAACCAAACCAG
CAAAGATATCCTCTCACCCCCCCACGCAACGAACCGCAGCCAAATGAAAAATTAAAAAACCCAGTAAGTATACTACGTCCATGTCCTCTCACTCA
TGCGCACCGAAACCAGAGTTTTGGATGGAGATGACCGCACCCAGTTAGTAGGATCTGCGTACCATGTGGGAAATAGCCCAAACACATCCACTTCA
CCACCACACGAATGAAACATTATTGTATCGTTCATACTAAATTTAATCTCAGTTTAAGGTTTATTTGTTTATATATCAGATATAGAAGATTGTGC
CAAAGTAAAGCAAAATCTACCTCCTAAACAAAAACTTATCTACATAATGATCAACACTTTTAGAGTCCCAAATGTGTAATTAACAATTATACGAG
AAAATATTCGCTAATTTGACAAGCAAATAATATATATGTACGTATATTCCATAAAAAATGATTACGGAAAATAAACCTTGAAATTGTGATAGTCA
ATTCGTTAACTGGTTTTCGCTTGATACAGGAAGTTCCTAATTTCAGTTATAGATAAACATGCTCTTTTACCCTCATTAAACACCAAAATTCGCAA
TATAGATAAAAGCTGCCTCAATGATACTTATTAATCATTAATCACGATGTAATGAATGATACAATTTGCAAACTAACAACTTGTTAATAGTTAAT

FIGURE SHEET 178

AATAATACATAATGCAGCTCTAACTACACAAATTCATGCATGTGTGTGTATGTATGATGGACGCTTTTTGATTACCATTCTTCTTAGACCTTATC
GTTGACATTATCTACTGACTAGATCCATCATCTTGTCTTCATTTTCGACTATATCACGAAAAGCTGATTTAAAAATAAACTTTTTATTCGTTTAT
GATAAGCAAACATCTCGAATATTATAGAATCAAGTTGGTAATACTGACAACGGCTATTAGGTGCTATTATGTTACCCCGTGCTGTATTATGTCTT
CGAATGCGGCACAGCCGGGCGGAAAGTACACGTAGCCGTGTGTACTCGAATTATACGAAGGTGCGTAAGGCGATGACTATAAATCGGAGAAGGTA
ACGAGACAACATACGTATATGTATATGCATGGGATAAGGTAAGGGGGTCAAAATAAGTCAATAAGATCGCCGTGTTAAGCCAATGTCTTAAAATA
CAGGGCCGGAGCGAGAGGGTGGCTAAGTTTTTAATTTGATCAAAGGCAATTTTAAATCGGAATTATGCTGTATCCACTAAATTTTATTACAATTG
AAACTGTTTTGGGGGGTGACGCCCCAAAATGACCCCGCCGACTCCGCTCCTGGAGCCAGGGAATGCACCCACACTCGCGCACAAATAAATAGGGC
GTAAAATGCTAATCTTGTGAATACGTGAATGTACATACATGTGTATGTACATACTCCACGCAAATCAAGTGTACATTATGTACATGCGAACGTAT
GTAAGATCGGAAATCAGGTGAAAAGCCCAGGGCCCAATAGCACAGGTGGGGGCGGGCGCGTTAGCACGGGACATTTGCTTTAATATTAACATGTT
TTCTGTTTCGCACTTTCTTCATTTTTTCATCTTTATTTTGGTTTTTTAGCCAGGCCAAAAGTTTACGCATACAGTGGCAATGTGTGTAGTACGTG
CAAGGGTACAACTGCATGTGTGTGCATAGTAGGTGGGATTAGGGCTCATCTGCACGGGCTAAGTTTCCCTTATATCCCGTTATACTACTCGAATT
CTGTAAACTTAAATGTTGTGAATGAAACTAAAATATAAATAAGCTACATTACTTTGCCAGTCACATTATAGACCTCTTTTAAGCCTCAAAAGCGG
CGATTCCATGCGGAATTTAGGTCGTGCGAAGGGGCCTTAAGCGCGTTCTGGGTTAAGAACCCCCGCCCACGACCCCCTTACCACAACGACCCATC
CCACAATCCGAGCATCCTTTTTCCTGAACCCGGTGCGATATTTGTTGGTTGATTCGAAGGATTCCCATACCAGATTTTGATTCCGATTCGGTGGT
TCTGAATTCAGATAGTGATTCGATTGGATTCGATTTCATTCGACTGGATTTGATTCGTGTTTCGCATGCAATTTGAGTTTTGAAAACGACAAACA
AGGTAAAATAATAATAAAATGTGTACCAATATGTCAAGCGTCAACGAATGCAAACGCACACTGAGGTGAATTGTTAGTTGTCTACACACGTTACC
TTCGGGTATTGATTGTTTTTTAAAAGAAAACACAAAAAAAAAGCCGCGAAAATCACACAACCAGATTATCGATTTTGGCCCCCGCTGAAATTGGC
GCACACAACACACAAATTTGACTGGGGAACGAACAGCGGGCGATGCAAACGATTCGGTTCCGACTTGGAATATATAGCTGCCGAACTATCGGTGC
AACAATCGGATCGCTCAACCGGTCGCTCCATCTGCAGGGAATACCAAAACGCCTCAGTTAAGTGGCGCGCGAATGAAGGTACTTGCGCTTAGCCA
CCAGCTGGGCACACTGCACGAGCCTGCATAGAGTTTTTTACGAAATTATCACAATTTAGGAGTTTTCCAATTAGAATTGGAATAAGTTCGTACTC
TTAACTTGCTAACAAGTTGATTTTTAATGCAAAACTTTTCGCAGACAACTTTTCGACAAGAACAGTGCTGCCAGACTGTCAGACCGGCACCTTAC
TGGCGTGTTTTTATCACATTTTCTAATATTTCCAAGCTATTGAAATATTCCAAAGCTTTCTATCTGCACATTCTTTTTATATAGGTGTTCCCAGA
AAATCGCCTTAGCATGGAGAGTCGTGCTAATACGGCGTTGCCAGACTGTCATTGCATTTCTTGTTGCTCTTTGCAAGAGCCCGCCAAATGAAATT
TTTATTTGAATACAATTTATTTTTTTCTTCCCCCGTTCTTTTGCTTGTATAATATCCCAACTGGAAAATGTGTACTTTTCAATTACGAAACATGT
ACAATATATAGCAATAAAGTCCAGTAAAATCGTGGTATGTTTACAATTACTTTTTTGGGCCTGATGATACGTTGCCATTAAAGTGCAATGTCATA
CCACTAATGTAAGTTTTTTAACCCTTTATACCCCCCAATAGCTTGCCCATAATCCTCCCGTGAACAATCTTGAATCCCAAATGCAAGAACAAAGT
TCGAATATTCAACAGGAGCTCCGCCTAATGTATGATGACGCATGTATTTTATACAGATCAAATATTTTCATACCGTTTTACAGGGTTCCGAAGAA
TAGAAAGTGGTAATTAAAAAAAGTATGCATTCGGTTCACCGAATTCAATTTGAATCGTTTTCCAAGTCAAATCAGGTTGGCTACAATGAGCAGAC
AGAATGTGGGCGGCGACACCAGATAGTGTCGCCGAATGCATGGAAAGCGATTCAATGCAACGGCCTTCCATCGAAGAAGT
(SEQ ID NO: 322)

Exon: 8295..5349
Exon: 5183..5119
Exon: 2952..2384
Exon: 2310..1861
Exon: 1600..1001
Start ATG: 5735 (Reverse strand: CAT)

Transcript No. : CT11537
TGGAGCGACCGGTTGAGCGATCCGATTGTTGCACCGATAGTTCGGCAGCTATATATTCCAAGTCGGAACCGAATCGTTTGCATCGCCCGCTGTTC
GTTCCCCAGTCAAATTTGTGTGTTGTGTGCGCCAATTTCAGCGGGGGCCAAAATCGATAATCTGGTTGTGTGATTTTCGCGGCTTTTTTTTTGTG
TTTTCTTTTAAAAAACAATCAATACCCGAAGGTAACGTGTGTAGACAACTAACAATTCACCTCAGTGTGCGTTTGCATTCGTTGACGCTTGACAT
ATTGGTACACATTTTATTATTATTTTACCTTGTTTGTCGTTTTCAAAACTCAAATTGCATGCGAAACACGAATCAAATCCAGTCGAATGAAATCG
AATCCAATCGAATCACTATCTGAATTCAGAACCACCGAATCGGAATCAAAATCTGGTATGGGAATCCTTCGAATCAACCAACAAATATCGCACCG
GGTTCAGGAAAAAGGATGCTCGGATTGTGGGATGGGTCGTTGTGGTAAGGGGGTCGTGGGCGGGGGTTCTTAACCCAGAACGCGCTTAAGGCCCC
TTCGCACGACCTAAATTCCGCATGGAATCGCCGCTTTTGAGGCTTAAAAGAGGTCTATAATGTGACTGGCAAAGTAATGTAGCTTATTTATATTT
TAGTTTCATTCACAACATTTAAGTTTACAGAATTCGAGTAGTATAACGGGATATAAGGGAAACTTAGCCCGTGCAGATGAGCCCTAATCCCACCT
ACTATGCACACACATGCAGTTGTACCCTTGCACGTACTACACACATTGCCACTGTATGCGTAAACTTTTGGCCTGGCTAAAAAACCAAAATAAAG
ATGAAAAAATGAAGAAAGTGCGAAACAGAAAACATGTTAATATTAAAGCAAATGTCCCGTGCTAACGCGCCCGCCCCCACCTGTGCTATTGGGCC
CTGGGCTTTTCACCTGATTTCCGATCTTACATACGTTCGCATGTACATAATGTACACTTGATTTGCGTGGAGTATGTACATACACATGTATGTAC
ATTCACGTATTCACAAGATTAGCATTTTACGCCCTATTTATTTGTGCGCGAGTGTGGGTGCATTCCCTGGCTCCAGGAGCGGAGTCGGCGGGGTC
ATTTTGGGGCGTCACCCCCCAAAACAGTTTCAATTGTAATAAAATTTAGTGGATACAGCATAATTCCGATTTAAAATTGCCTTTGATCAAATTAA
AAACTTAGCCACCCTCTCGCTCCGGCCCTGTATTTTAAGACATTGGCTTAACACGGCGATCTTATTGACTTATTTTGACCCCCTTACCTTATCCC
ATGCATATACATATACGTATGTTGTCTCGTTACCTTCTCCGATTTATAGTCATCGCCTTACGCACCTTCGTATAATTCGAGTACACACGGCTACG
TGTACTTTCCGCCCGGCTGTGCCGCATTCGAAGACATAATACAGCACGGGGTAACATAATAGCACCTAATAGCCGTTGTCAGTATTACCAACTTG
ATTCTATAATATTCGAGATGTTTGCTTATCATAAACGAATAAAAAGTTTATTTTTAAATCAGCTTTTCGTGATATAGTCGAAAATGAAGACAAGA
TGATGGATCTAGTCAGTAGATAATGTCAACGATAAGGTCTAAGAAGAATGGTAATCAAAAAGCGTCCATCATACATACACACACATGCATGAATT
TGTGTAGTTAGAGCTGCATTATGTATTATTATTAACTATTAACAAGTTGTTAGTTTGCAAATTGTATCATTCATTACATCGTGATTAATGATTAA
TAAGTATCATTGAGGCAGCTTTTATCTATATTGCGAATTTTGGTGTTTAATGAGGGTAAAAGAGCATGTTTATCTATAACTGAAATTAGGAACTT
CCTGTATCAAGCGAAAACCAGTTAACGAATTGACTATCACAATTTCAAGGTTTATTTTCCGTAATCATTTTTTATGGAATATACGTACATATATA
TTATTTGCTTGTCAAATTAGCGAATATTTCTCGTATAATTGTTAATTACACATTTGGGACTCTAAAAGTGTTGATCATTATGTAGATAAGTTTT
TGTTTAGGAGGTAGATTTTGCTTTACTTTGGCACAATCTTCTATATCTGATATATAAACAAATAAACCTTAAACTGAGATTAAATTTAGTATGAA
CGATACAATAATGTTTCATTCGTGTGGTGGTGAAGTGGATGTGTTTGGGCTATTTCCCACATGGTACGCAGATCCTACTAACTGGGTGCGGTCAT
CTCCATCCAAAACTCTGGTTTCGGTGCGCATGAGTGAGAGGACATGGACGTAGTATACTTACTGGGTTTTTTAATTTTTCATTTGGCTGCGGTTC
GTTGCGTGGGGGGGTGAGAGGATATCTTTGCTGGTTTGGTTGGGTTCTCGGTTGGTTTTGCATTCGGATGATTAGCTTTTAACTACCGCCTACCT
ACCTACTCATTTTACATGCTGATGTTATTGTCGTTCTATATGTATGACCCGACCTGACACTTTCGTATTTCACATATATAATACAATAGAATGGG
CACAGAAACCAAGAGCAACAGTTACACAGGACAGATTTCAACAAGTGGCGGCAACCCCAAAGTGATGAAAGATTCTTTATCCTTAGTTCGTCAGA
CGGTCAATCAGCAAACGCTATCGCTATCGCAATCGAACCAGGTCCAGAACCAATTGAATTCACATTCGAATTCCAATTCGTATCCAAATCCAAGC
GGGAGCGAAAACAAAAACGAAAACGAACAAAATTCGCGCGATATTCGAGCCAAACCGGAGGATAAATCCAGAAAAGAGGCAATTGTACCATTTGT
ACCCATATTTGTTGAGGAGGCCGACGTAATTCAAGGGGCCAAGGAACTGTTGAAGGTTATACGACCGACCTGGGACCTCAGCCACGTCGAGTTTA
AGATCAGGGTAGTTCCGCAGATCGAAGATCGTTATCCGGCCCAAAATGCGATGGTGATGATGACGCTAGTTTTACCGATGGCATCACAAACAAAC TGGTCGGATGTTTTCATAAGGAGATCTCCAAACTGAACGATGAGAACGGCGGATCGTATTTACCTATCAAGACGCAGGGTTTGTCGCCCGTTCAG
TCCGAGGATCCAGTCATCATTGAGAAGGAGGACGATGATGAGTTCACAGACGATCGGGCAGCGGACGACGGGTCACCTGTACAGTACTCCGATAA
CGTAGTGCTCGTCAGGATATACGGTAACAAAACGGACCTACTGATAGATCGCAAGGCGGAGACGCAAAACTTTCTTCTACTGCATACGTATGGGC
TAGCGCCATCGCTGTATGCCACGTTCAAGAACGGTCTCGTCTACGAATACGTACCTGGAACCACCCTGAATACGGACAGTGTGCTCTGTCCAGAA
ATTTGGCCCTTGGTCGCCCGTCGCATGGCCGAGATGCATCGCAAGGTGAGAAAGCACGGGGATAGTTCGGCGACCAAACCCATGCCGATGATTTG
GAAGAAGACGCAGAGCTTTCTTGATTTAGTACCTGAACGTTTTAGTGATGCTGAAAAACACAAAAGAGTGAAAGAAACGTTTCTACCTATCGGCC
GCCTGCGCGAGGAGTTCAACAAGCTATATGAATACCTCGAGGCTCTGGACAGTCCGATTGTCTTCTCCCACAACGATCTTCTGCTGGGAAATGTG
ATCTATACGCAGAGCCTGAATACGGTGAACTTCATCGACTACGAGTATGCCGATTACAATTTCCAGGCCTTCGACATTGGCAACCACTTTGCGGA
GATGTGCGGCGTGGATGAGGTCGACTATTCGCGCTATCCGAAGCGCGAGTTCCAGCTCCAGTGGCTGAGGGTCTACCTTGAGGAGTACCTACAGC
GCAGCAACATTCAAAACGACGAAGTCGAACTGCTCTATGTCCAGGTCAATCAGTTTGCGCTGGCATCGCATATCTTTTGGACGGTGTGGTCCCTG
TTGCAAGCCGAGCATTCCACTATCGATTTCGACTACGTAGGCTATGCATTTCTTCGTTATAATGAGTACTTGGCTCGAAAGGTGGAGTTTTTGTC
ATTGACTGCAGCTAAGAACAATAAGTGATTTCTCTCTCCCGGCCACTCAGCGCATTGGGAGTTACTACATTATGTGCCCAGTGATATATGTATAA
ACTAAGGCTGGAACGGGTCTCAATGTTATACATATGTATATATATAACGTGTGTTCAGAAATCAGAAACAAAAACCGAAACAAACTTAAATTAGT
GTCGTGTTCGTGCCAGCCTTAGTGTATGTACAGTGCTCACTCGAAACAGTGGACTATTGAGAACCAAGGGTGTGCACTGAATCGAATTTGTTCAC
TATAACGAATCACAGAAAAAATAAACAATTTAATATATTTTTCAAAAACACCACGTTTGAAAAAATTTAATTTTTTTACTAAGTTAAGCGAAAGT
TTCTAAAATTTCATAAATTAATCGTTCACTTTTACTAAAAAGTTCACATATTCGAGTGTTCACTCTTAAGGGAGGGCACTGTATATATATAAAGAAT
TTGTATATGTTCTTTAATTTGTATAAATTGATATTTTGTAGTCATAATAAAGCGAAGGTATGTACTTTAAA
(SEQ ID NO: 323)

Start ATG: 2561 (Reverse strand: CAT)

MGTETKSNSYTGQISTSGGNPKVMKDSLSLVRQTVNQQTLSLSQSNQVQNQLNSHSNSNSYPNPSGSENKNENEQNSRDIRAKPEDKSRKEAIVP
FVPIFVEEADVIQGAKELLKVIRPTWDLSHVEFKIRVVPQIEDRYPAQNAMVMMTLVLPMASQTNWSDVFIRRSPN*
(SEQ ID NO: 324)

Classification: enzyme
Gene Symbol: eas
FlyBase ID: FBgn0000536

Celera Sequence No. : 142000013384645
ATATTCGATCGATTGAGGGCGGTGCGTCGGGAGATCGTGATCCAGATGTACGATGCCAGTCAGAAGATTTGCCTGTTAGAGCCCATTGTGATGTT
TCTGGCATATAGTCGCTATCGCTTGTGTGAGGAGCCCATCGAGAAGTTCGATCTCAAGATATGCAATCAGCATTTGCAAGAGTGCCTCACGGGAG
TGCTTTGCTGTTACGAAGAACTGGAGGACTTGGAATCATCTAGAGAACCCACCGTTCGTGAGCTTGAGCGGCGCTGCTTCATAGAGAGCCTGTAT
CAATTGTTTAATCTGGGTTCTCCCGAGTCCTTTACACGCGCCCTCACCTTACCGGACTATGTGCGTCGGGATGCGACGTTTAAGCTTTGTTTTGG
GATCTGTTTGGCCTTCCAACAGGGCAATTTGTATAGAGTGCTCATGGGTGTGCCACAATTGCCGCATATTCTGTGCGCGGTAGCTGCCGCCAAGT
TGCAGGTGATAAGGAGGTACAGTATAACTTTTTCTATTGGATCTCTTATTGACATGATGCATTTTTAATGTAAATACATATGTATGTATGTATAT
TTGCAGGAGTTTGTTGCAGATTTTCACGCATGCCTACAACAACAAACAGCTTACGGTGCCGGTTCCTTACTTGTTGCGTTTACTGTTGTTCGATG
GGCCAACAGGATTGCAGGACCAATGTCGGCATTATAATATATCCTTAACAGCGGATAGGAAGGCGGTGCAATTTAATAAGACTGATTTTAACCAC
AATGCAGAGGTATTTACACCCCAACACGAGCGCTTTGTGGAGTCGAAGCTGAAGCGTATTTATATTCCAGAAGTTCTATTGCTAAAGAAATTTAA
CTAGTTATTTATGAGCAACAATTGTAAATAGCTCGAAATAATAGTAAAGCCATGGAGATTAATTTATTGTTATTGCGCATTTGTTTTCTTGTCGG
GTGGCAACCCTGGTGGCAGAACAACAAACCTATCGCTTATCGAAAGACAGAACGCCGCGGTATTTACAGCTAATAAATGGTTTGCCAGTTGGAGG
TTAATAAAATGCAATTTTTGAATAGTAGTTAAGATTACATTTGTGCTGTTTTGCGAAGTAATGCGAAGAGAATAACCAATCTCCGCTGAATAAAC
CGCTTAAGATATACACAAAGCGCGCGCAGGGTTGCATTGTGGCGCCTGTCGCTGCACACTACACACACACACACCCCACACACGCAACGCGAGAG
AAAGTACCGAGCCGTTTCTGGAAAATACAATTCCGCCATATTAACCGGCAAAATTCAAAATATTTACACTGCCCGAGGTGAGCGGGATCGAGGTG
GTCATCCAAAGCGAGAATTAACCCGCCATTGGGCAGCAGGAGAGTGGCGGGCGGAGCGGAGCGAGCGGTACGCATCATTCGCCGTCTGCCGCCGC
CGTCGCACAATAAACGATAGGCATTGGCCACAAAAAAGTGGAAAAAGAGGTGGAGGGAAAGGCCAGTTCAGTGCAGCAATACCGACGAAAACACG
TACGTTTGTCCACTTTGGAAGTCTGGCGAATATATAGAGATATATACATAATACGGATTTTTGGCCAGATACTAATTGCCCACTTTTTCCGCAGC
GCGCTCGCACACACAACACTAACACTCACGCACGAAGCAAGAGCGCCCACAAATACAAGCATACAGATACAGGCACACAGACAGGCAGACGGAGC
AGCCGCGATGACAAGTCATCATCATCACGTCGGCGTCGGAGGGAACTTCCAGCCTCAACTGCATCAGATACGAGCGCCCATCGTGAAGAATCTAT
CGCTGGCCGCTGCGGCGGTACCGTTGCCCCTGCACTCCGCCCCGTCGTCGGCATACTTCACTCATGCACACCAGCCTACGGCGGCTACCATAGTC
GAGCAAGATCCGTACACCGTTTTGGCGGGCGATCCGATGGGCGAGGAAAGCGAGAGCTTCCTGATCGAGGAGATCATCGACGACTATGATGATGA
GGCTAATATCGTCGTAGACTCAGGCGAATTCTTTGAGCACTATGAATACTATCCGGTGGATCGGCTGGACAGACTTACCTCGGTCACGGTGGCTA
CGGCAGATGCACTGCCGCCGCCGATCATCATGCAGCAGACCAGCGACGATGAGGAATTCATCGAGGAGGATGGACAGCAGATGACATCCTCCTGC
GATGGCGATGGCGATGAGGATGATGAGGCTACCGCGCCGGCTACGACAAATGCCTTCGAGATTGCCTCCGAGATGCTAACCACCATCGAGGCCAC
AAACATCAAGGAGGAGCAGCTCGAGAGCGACTTCTATATGAAGGCGACCGAGGATTCAAACAGTTCGAATGGCCAGCTGCAGGATTTTAAGCTAT
TTGGAAGCAGTCGCGTCGAGAGGCCCATGGGAAATTCAGCGGCCAAGCGCTGGAAGCAAACAAAGGTACCCATACGCATAACGCAGGATGAGTTC
AATGTCACCCTTTGGTCCTCGCTCAACTCGGAGGATGAGGACGAGGAGGAGGAGTTGGAGGAACCACCTGGTTGTGCTGGCACCACATCCGTGAC
GTCCTCCTCCGCCGCCCAGAATGAAGGATCACCCAGCATGCCAAAGCTTATTATTGACGAGCACATGATCAACCACGATGTTTTAAGCGATGGCA
TCGGCAACGAGTACGTCATCCTACCCGATCCATTCAGCGCCTCTGCGGTCACGGATGTGGAGGAGGTGGTTAATGCATTTATGGGCGATGTCAAA
GGCGAGGAGGACAGCCAGCCGCTAAGTGAACAGTTGATCTATGCGGAAAACCAGTTGGAAGAAGCTTATGGTAACATCGAGCTTATCGAGAACAT
GCCGAATAATGTGGAGCTGATACAGACACCGGGACCAGGTCCAGCCACTGTGTCGGTAGCGCTATCGAAGGTCAACGGATGTGTACCGAATCCAC
AGCCGGCTCTCCCAAAACTAGTGCTCCAGAACAGCAGCACCAATGTGCGACTGAAAAGTGCGGGAAATCAGTCAAAGGTGACAAAGAGGCAACTC
ACGGCGGCGGCTCAGGTGGCGACACCAAATCCCCCACCGCCACTAGTGGCTTCCAGCAATCCAGCCCGACCCCAACGACCCACAATTGTAACCAA
ATTACCGACTGCAGTGGCCAATCAGACGGCTGGTAATGCCATGGGAGCAGCTGGCGCGGCCGGCGAAGAGGATGAGGAGCCAAAGTTTCGCTGCA
CCCATCGCGGCTGCAACAAGGAGTTTCGCAACCACTCGGCCATGCGCAAGCACATGCACACGCACGGACCGCGCGGTCATGTGTGCAACGTCTGC
GGCAAGAGCTTTGTAGAGAGCTCCAAGCTAAAGCGCCACCAGCTGGTGCACACCGGCGAGAAGCCCTTTGAGTGCACCTTTGAGGGGTGCGGCAA
GCGCTTCTCGCTGGACTTCAATCTGCGCACCCACGTACGGATACACACTGGCGATAGGCCCTACCACTGTCCCATTGATGGCTGCTCCAAGTGCT
TCGCCCAGTCAACGAACCTCAAGTCCCACATGCTGACGCACACGAAGCCCAAAAGGAAGTGGCCGCGCGCACCGCAAGTGAGCAACAACAAGACA
CCGCTGGTGGCCAGATACGGGCGACTGGAGTTTGGCGAGGATCCTCGTCTAGTGTACGTAGAACAGAACGAGGAGGTGGCGTCGGTGCTGCTGGA
TGGCACGTCCCTAACATCCTAACTAGTAGTGCGCTTTAATGTGTGGCAGGTATTGGCATGAGATGGTTAAAATATTAAAGCTCCTTTGGCTCCGG AAGGCATTATTGTACAGTTAGTTGTAGCCAGTTTTTATCTGTATCTGTAACCTGTAACGAGCGGAGCGGCCGGACAAGATTGTCACCTGGTGAAC
ACATCCGCCCGCTGCCCGCCCTTTAAGTAAGTAGTGTAAGTTCATTCTCTAACAAAATAGGATTGCAGTGCAAAAGGAAGTTAGATGGTAGCCAT
TAATTAATTTCCTTCACGGATGAAGAGCAGTTCTAAGAGTTTAGCTTGTACCGTAGGCTAAGTGAGTCCCCCCGCAAAACCAAAACTGAACCGTA
ATCCCCGAAGAACTCAGCCAAACTGTCACCTTAAAAAGCCCCAATTTGATCTGATACTAATCGTGTGCGATCTTCGCTCGAATAACAAAACGCGC
ACTTTCTTTTCTACGAAAACAAAACAAACAAAAAAATAAGAAAAATACACAAAACTAGTTTTACCATATTCAATACGCATACACCATAGGCTATC
TATATATTTTTGTAATGAATTATAACACTTAGAGCATTGAAGTACGGATTTAGCATGTTCAACGTCTGTTGGCGCTAACAATAATTCACAAATGG
AAGCACATCAGTTAAGTCGGAATAAACAAGGGAAATACCTCTTCAAAATTAAACAAAAATAAACCAGGAAAACAATGCAACAACACTTGCGTATA
TCATTTATCATTTCTTTTTTTAACTATTTCACAGTGCGATTGTGTAAGCGTTAGATTTATTAACTGACTTTAAACTTGTAACTACTGCTAGATAA
CTACATTAAACGGTGAGGCAGCTATTGATGGACAGTCGCCGGGTGTTGTCCACTTCAGATTCGGATCAGCAAGCGATTAGATCGCCTCTTTGGAC
ATGTGTCGCCTACAGCTACGTTCCATTCATTGATTGCGGTGTATAAACGCGTGCGGATTAGATAAAGCATCGCGGCGAGGTACAGATACGCGGCT
ATTTTGGATATTGGAACGGAGAACAGTACACACGATTGGTCTGGGCATGGTCTGATCGGTATTTTAGGTGACCTTGAGCCCATGTCCTTGAACTC
CGGGAATAATATCCGCGATGGAGGCACTTGTTGGGCCAATCAATCCGGCCAGCGAGAGCAGCACGGAGTAGTTGAAGTACCAGAAAACGCAGAAG
AGTACCATGAAAATGACGTCTGCAATGAACCGAGAGCAATAATAACCCTGATAAGCGTATAAATTCTCCAGAAGCATGACGAATCCGTCGGATAT
TCCCAACTAGTTCGAGGGTGTGCTATTTTATTAACAGCAATTAACACTCACGTATCGTTATCCGCTCCCACTTTTCAACCATGTACAGCTCGGTG
ACCTGCAAGTTAATGGGGTTCATTTAAATCAAAATCCCGTGGAGCGCAGCTTCTCAGGTGGAATATGTGCGTAATTTTA
(SEQ ID NO: 325)

Exon: 1001..1519
Exon: 1615..3411
Exon: 3478..4209
Start ATG: 1718

Transcript No. : CT11601
AACGCCGCGGTATTTACAGCTAATAAATGGTTTGCCAGTTGGAGGTTAATAAAATGCAATTTTTGAATAGTAGTTAAGATTACATTTGTGCTGTT
TTGCGAAGTAATGCGAAGAGAATAACCAATCTCCGCTGAATAAACCGCTTAAGATATACACAAAGCGCGCGCAGGGTTGCATTGTGGCGCCTGTC
GCTGCACACTACACACACACACACCCCACACACGCAACGCGAGAGAAAGTACCGAGCCGTTTCTGGAAAATACAATTCCGCCATATTAACCGGCA
AAATTCAAAATATTTACACTGCCCGAGGTGAGCGGGATCGAGGTGGTCATCCAAAGCGAGAATTAACCCGCCATTGGGCAGCAGGAGAGTGGCGG
GCGGAGCGGAGCGAGCGGTACGCATCATTCGCCGTCTGCCGCCGCCGTCGCACAATAAACGATAGGCATTGGCCACAAAAAAGTGGAAAAAGAGG
TGGAGGGAAAGGCCAGTTCAGTGCAGCAATACCGACGAAAACACCGCGCTCGCACACACAACACTAACACTCACGCACGAAGCAAGAGCGCCCAC
AAATACAAGCATACAGATACAGGCACACAGACAGGCAGACGGAGCAGCCGCGATGACAAGTCATCATCATCACGTCGGCGTCGGAGGGAACTTCC
AGCCTCAACTGCATCAGATACGAGCGCCCATCGTGAAGAATCTATCGCTGGCCGCTGCGGCGGTACCGTTGCCCCTGCACTCCGCCCCGTCGTCG
GCATACTTCACTCATGCACACCAGCCTACGGCGGCTACCATAGTCGAGCAAGATCCGTACACCGTTTTGGCGGGCGATCCGATGGGCGAGGAAAG
CGAGAGCTTCCTGATCGAGGAGATCATCGACGACTATGATGATGAGGCTAATATCGTCGTAGACTCAGGCGAATTCTTTGAGCACTATGAATACT
ATCCGGTGGATCGGCTGGACAGACTTACCTCGGTCACGGTGGCTACGGCAGATGCACTGCCGCCGCCGATCATCATGCAGCAGACCAGCGACGAT
GAGGAATTCATCGAGGAGGATGGACAGCAGATGACATCCTCCTGCGATGGCGATGGCGATGAGGATGATGAGGCTACCGCGCCGGCTACGACAAA
TGCCTTCGAGATTGCCTCCGAGATGCTAACCACCATCGAGGCCACAAACATCAAGGAGGAGCAGCTCGAGAGCGACTTCTATATGAAGGCGACCG
AGGATTCAAACAGTTCGAATGGCCAGCTGCAGGATTTTAAGCTATTTGGAAGCAGTCGCGTCGAGAGGCCCATGGGAAATTCAGCGGCCAAGCGC
TGGAAGCAAACAAAGGTACCCATACGCATAACGCAGGATGAGTTCAATGTCACCCTTTGGTCCTCGCTCAACTCGGAGGATGAGGACGAGGAGGA
GGAGTTGGAGGAACCACCTGGTTGTGCTGGCACCACATCCGTGACGTCCTCCTCCGCCGCCCAGAATGAAGGATCACCCAGCATGCCAAAGCTTA
TTATTGACGAGCACATGATCAACCACGATGTTTTAAGCGATGGCATCGGCAACGAGTACGTCATCCTACCCGATCCATTCAGCGCCTCTGCGGTC
ACGGATGTGGAGGAGGTGGTTAATGCATTTATGGGCGATGTCAAAGGCGAGGAGGACAGCCAGCCGCTAAGTGAACAGTTGATCTATGCGGAAAA
CCAGTTGGAAGAAGCTTATGGTAACATCGAGCTTATCGAGAACATGCCGAATAATGTGGAGCTGATACAGACACCGGGACCAGGTCCAGCCACTG
TGTCGGTAGCGCTATCGAAGGTCAACGGATGTGTACCGAATCCACAGCCGGCTCTCCCAAAACTAGTGCTCCAGAACAGCAGCACCAATGTGCGA
CTGAAAAGTGCGGGAAATCAGTCAAAGGTGACAAAGAGGCAACTCACGGCGGCGGCTCAGGTGGCGACACCAAATCCCCCACCGCCACTAGTGGC
TTCCAGCAATCCAGCCCGACCCCAACGACCCACAATTGTAACCAAATTACCGACTGCAGTGGCCAATCAGACGGCTGGTAATGCCATGGGAGCAG
CTGGCGCGGCCGGCGAAGAGGATGAGGAGCCAAAGTTTCGCTGCACCCATCGCGGCTGCAACAAGGAGTTTCGCAACCACTCGGCCATGCGCAAG
CACATGCACACGCACGGACCGCGCGGTCATGTGTGCAACGTCTGCGGCAAGAGCTTTGTAGAGAGCTCCAAGCTAAAGCGCCACCAGCTGGTGCA
CACCGGCGAGAAGCCCTTTGAGTGCACCTTTGAGGGGCCCTACCACTGTCCCATTGATGGCTGCTCCAAGTGCTTCGCCCAGTCAACGAACCTCA
AGTCCCACATGCTGACGCACACGAAGCCCAAAAGGAAGTGGCCGCGCGCACCGCAAGTGAGCAACAACAAGACACCGCTGGTGGCCAGATACGGG
CGACTGGAGTTTGGCGAGGATCCTCGTCTAGTGTACGTAGAACAGAACGAGGAGGTGGCGTCGGTGCTGCTGGATGGCACGTCCCTAACATCCTA
ACTAGTAGTGCGCTTTAATGTGTGGCAGGTATTGGCATGAGATGGTTAAAATATTAAAGCTCCTTTGGCTCCGGAAGGCATTATTGTACAGTTAG
TTGTAGCCAGTTTTTATCTGTATCTGTAACCTGTAACGAGCGGAGCGGCCGGACAAGATTGTCACCTGGTGAACACATCCGCCCGCTGCCCGCCC
TTTAAGTAAGTAGTGTAAGTTCATTCTCTAACAAAATAGGATTGCAGTGCAAAAGGAAGTTAGATGGTAGCCATTAATTAATTTCCTTCACGGAT
GAAGAGCAGTTCTAAGAGTTTAGCTTGTACCGTAGGCTAAGTGAGTCCCCCCGCAAAACCAAAACTGAACCGTAATCCCCGAAGAACTCAGCCAA
ACTGTCACCTTAAAAAGCCCCAATTTGATCTGATACTAATCGTGTGCGATCTTCGCTCGAATAACAAAACGCGCACTTTCTTTTCTACGAAAACA
AAACAAAC
(SEQ ID NO: 326)

Start ATG: 623

MTSHHHHVGVGGNFQPQLHQIRAPIVKNLSLAAAAVPLPLHSAPSSAYFTHAHQPTAATIVEQDPYTVLAGDPMGEESESFLIEEIIDDYDDEAN
IVVDSGEFFEHYEYYPVDRLDRLTSVTVATADALPPPIIMQQTSDDEEFIEEDGQQMTSSCDGDGDEDDEATAPATTNAFEIASEMLTTIEATNI
KEEQLESDFYMKATEDSNSSNGQLQDFKLFGSSRVERPMGNSAAKRWKQTKVPIRITQDEFNVTLWSSLNSEDEDEEEELEEPPGCAGTTSVTSS
SAAQNEGSPSMPKLIIDEHMINHDVLSDGIGNEYVILPDPFSASAVTDVEEVVNAFMGDVKGEEDSQPLSEQLIYAENQLEEAYGNIELIENMPN
NVELIQTPGPGPATVSVALSKVNGCVPNPQPALPKLVLQNSSTNVRLKSAGNQSKVTKRQLTAAAQVATPNPPPPLVASSNPARPQRPTIVTKLP
TAVANQTAGNAMGAAGAAGEEDEEPKFRCTHRGCNKEFRNHSAMRKHMHTHGPRGHVCNVCGKSFVESSKLKRHQLVHTGEKPFECTFEGPYHCP
IDGCSKCFAQSTNLKSHMLTHTKPKRKWPRAPQVSNNKTPLVARYGRLEFGEDPRLVYVEQNEEVASVLLDGTSLTS*
(SEQ ID NO: 327)

Name: zinc finger protein
Classification: transcription_factor

FIGURE SHEET 181

Celera Sequence No. : 142000013384689
ATCGTTAATTGACTTGAATTGCGGCACCACATTCAGATAGCGGAAAGTACTGCCCATCTGGTCCGTGAACAGGAAGTCCGCGGAAGCCACCATAT
GTCCTCGATTAATCACCAAGTAGTTGGCATTTTGCAAGTAGGACTGGTCATCACCGTAAATGCATTTGAACGCAAAATAGATGTTGGACTTCATG
TAGGCAGCAGCCTCCTGCGGACTGAACATCTCATCCGCCACAAACTCCACAAATGGCCGCTTCGGAACTATAACTCCTTACACTATACTAGGGGT
TCAAAAGGCCAAACTTTGTGATTTACTCACAAAACGTTTTGTAGTAGACATCGCTCTGCGAGTACACGAGTCTTCCCTGCCCGCAATCGAAACAT
GTGCGATACAGCTCCAGATCCTTGCCATCTATGGTATATCCCACGGCATACAGGTTCCCCGCACAATCCCCATCGCGAATATGCTTGGTCACCGG
TTGCATTGGACTTAAACAGCGCATGGGCAGTGGGACCGAGAACTGTCCATTGTCCTGGCAAACAGTTTCTTTGAAAACCGAGGGACTGCAGTACA
CGAGTAGAGTGACACCGGATGGAACTGTTTCCAAGCGCTGCAGCTGGATAGATCCGCTCGCATCGCGATAGGTGAAAATTCCATTGGATTGCTCT
ACCATATATTGTAAAATTTGACAATCGCCGTGCACTTCCCAAGCTGTCGATCATGTGCCAAATCATGTGCCAAATTCACAATCTTAAAAAATAAT
TTTTCAACTCACCCAGAAAGCATATGAAATATATGTAAATAAATAATGTGATATAGGAGCAATCCATAGGAGCAATTTTCATATACTATGAAAAT
TTTGAAAAAATGCCAAATAAAGAAGTTAAATGTACTAAATTCCTAAATCGGAAGCTTCTATCGATACATTCTAGTTAGCAGTTAGTTCAACATAC
TATTTTATAGAAGCCATTTCGGAAGCAAATTTCGGAACCTATTAAATAAGTAACCACATTTTTTTGACAGTCCACTCGTGGATAACACTTTATT
GCTTCTATCACATACAAAAGTTGTTGTTTGGTTGCTAGTTGAACTCTGCTTCGAAACAATTGATCAATTCTTGTATTCGTGGTACTGTACTTCAA
GATAATAATCAGTATTTAAATTTTTTTTTGTTTTTTGGGTTTTTTCTTTCTACTTCAAACAATTGATATTGATGTGGTTCTACAAACAAATATAT
AATAGTTCTTTATGTGATAAGCATACGCCATAACGATAAAAGAAATTAAAAGTAGGAAAAGAACGAATCGAAATCCAATCGCATCGGAGAATTAA
ATGTGCATATGTAGTCGTATATCGTAGGTGGTATAAAATACATATAAAATAAACAAAACTTAAAATGAGAACTGAAAACGAAACTTAAATATTTT
GCACTAGTTCTTTAACAAAGATTTTAGGGAACAGGGTTAGAGGCTGCTTGCTTTTTACTTGTTCAAAATTGCTGCGCGAAATCTCATACAAATTA
AAACCTATATAGAAAACGGTTTCGATGTGCCATCTTACTGCGTGTAAATGCTATAAACTATACTTGATTGCTCGGGTGGTCTCTACTGCAGTGCA
TACGCGTTGCCAGAACATCGCTTAGTTGTTGTCCTGCTTGTTGATCAGCTTAAGGATCACCTTGCCGGCCTGCACCTCCAGCGCGTAGAGGCTGC
CGTCCTTGATCTCGTTGTTCAGCACCTCGTCGGTGATGGTCACAAGGATGCCCGATGGCCCCGATATGTACACGCAGCTCTTGTTGGCGTCGTTG
AAGATATTGGAGCCGCTGCCCGAATACTTGGAGTGCATCCCCCAATTGTTGAAGAGTGCTGCAGCAGCTGCAGTGGCTGCTCCACCGGCTCCGTT
CTCCTGGGCACTGGCCTTGGCCATGAACTCGTAGAAGCCGGGCATCTTGAAAAGCTTCTGCTGCAGCTCCTTGGCCGTGTTCGACAACAAGTAGA
TGGCATTGTAGCTGCATCCATCCACGCTGGCGTACAACGTTAGCCTGGGAGCAATAGTTCTGTTGGAAGGATCACAATTAGAACAAGTATTTGAG
TTTTTCAATATGGTTACACTCACTTGGCGCGCAAAATGTTGAACATGCGAATGCCATCGGCCAGGCCGCAAATTTGAATCAAATCCTCCTTGGAC
ATGCTAAAAATAATTCGAAATTATAAATAAGTCGGAAGAACAAACAAATTTCAAATGTGTGGTGTGGCACTAGTTAAAGATAGAACTATTACATA
CATAAACCTATAAAATGCATACATAAAGTAATAACGATCAAGTATCTGACGGAGTAGTCCAGCTATCTAATCAAGGTATTTAATAATCAAAAACT
TTATGGTTTGATTGGTCGTAATCAATTGGATGTGAAATCATATTGTTCCTTAGCTGTTTTCTTTTAGTTCCGCTATCTGTTATATGTCTGTCAAC
AAGATAACACAACTAACTGATTAAAAAATTATATGGTTTATCGCTTGATTGTAAGAAATGGTAATCAAAAACACCTAAGTACTCGTAGCTTAGCA
GACAAATAGGGGCGTGACGATAATTAAAACGCTTTTATATATAAGTCAGTGAGTTGGTTGTAACTTCAATCGAACGATGCTTTTAATTAGTTTTA
ATTAGTTTTTTAATATTAGTTTGATAAAAGAAAACTACTCGACTCTCCTACGATTTGGTTGGCATAAAATTGGGTCACTTAGAAGCAGAAAAACT
ATAACATTAATTCGGTTCGAATTCCAGATCACATACCGCATGATATCCGCTCCCGAGAACTGTGCAAACGTTGAAAGATAGGCCGTGAGGCGATG
ATTGGTCAGCCACTGCGTCACTTGCGAGGGCGTCGATTCCGGCATTATGTTCTGGCTCTGAAATGGACAATAGTAAGTCATTTATTTAGTAAGTC
TGCTTAGGGAGCAGTGGGCAATGGCACCTACATAATCGTCCATGTCAGCGGGCACATGCTGCGGTGAGACCATGTTTGTGGCGTCCATCAGCTTG
AGGGTGGGCGAGTTGGTCGATGTCACCGAGTTGATGGCTATGGGGCTGCTGCTGGTAGCCGGCGATGCTGCACTTGGCGCAAACGGAAGCATTCC
ATCGTACTTGGGTATGTGCACGGGCGAGTTTGGCCAAAGTTTCATACTGCAAGGAAGAGGATACAGGAGGAGATTAGTACAAGCCAGCTTTAAGT
GAGTTCTTGCAGATCCTACAAATCCAATAGAGCTCGTTCCGTATCTGACGTTGGCAGGAGCGACGATCCTTCAGATGCAAGCGCATGTTCACGAA
TGCGAGGAACTCCAGCGCGGAATTCACAATTCGAATTTCCCATGGTCCCGCTGCTCCCCGGGTAATCTGGTTTGCTCTTCGCCAAGCCTTGCTTA
GAAGGCACCCGATACGCCCAGTTGCGGCTGATTGGCCAGACAAACCCGTTTTCCTTTCCACCGGGGAAATTTTACAGATTTGCGTCTTTCGCCGC
CCCCCATGATTTCCGGTTTTTGTGGATGGATAATACATAAGCGTAGGCTTTTCTGCACCTGATCGATATAATCGATCTCAACAATACAAGACCTT
ATACAATCCCCATATCATTCGCCATCATTATCTATAGTGCTCGGAATGCAAACAAACGAAATCATTGAACAGAGACCAAAACCAAAAACCGGTTA
AAAGCAACTTTAAACTAAAAATAACTTGGAGCAGACGCAATAACAACAAAGACCGCAGCGCAAAGTGCTCTTAACTGATCTCTTAGCTTTCCACT
ATCCTTCGGATTCTCTCTATAAATCTCTCTGGATCTCTTTCTCCCCATTTCTCCGGATCTCTCACCGATCGAGGTGTTCTCTCTTTATATGAAAC
ACGTATACACCCGCTCTCAATTCGATTGATCTTTATGATTTTGTGATCATGCAAATGACAAACTGAATGATTTTCATTTGCTCTCGTTATGGAAA
ATTTCCAACCAAATATCTGTAAATAGCGTTTTTCTATGCACACTAGATTCTAAATAAAATACATATTTAATAGAACCACAAAAAACAACGTGTAA
TCGCTTGGTTTGTTTGTTTATGTTTTAAATTCGCAAATAAACAGAAAGCTTTTGATC
(SEQ ID NO: 328)

Exon: 3142..2977
Exon: 2907..2792
Exon: 2188..2114
Exon: 2054..1001
Start ATG: 3033 (Reverse strand: CAT)

Transcript No. : CT11653
GTACGATGGAATGCTTCCGTTTGCGCCAAGTGCAGCATCGCCGGCTACCAGCAGCAGCCCCATAGCCATCAACTCGGTGACATCGACCAACTCGC
CCACCCTCAAGCTGATGGACGCCACAAACATGGTCTCACCGCAGCATGTGCCCGCTGACATGGACGATTATAGCCAGAACATAATGCCGGAATCG
ACGCCCTCGCAAGTGACGCAGTGGCTGACCAATCATCGCCTCACGGCCTATCTTTCAACGTTTGCACAGTTCTCGGGAGCGGATATCATGCGCAT
GTCCAAGGAGGATTTGATTCAAATTTGCGGCCTGGCCGATGGCATTCGCATGTTCAACATTTTGCGCGCCAAAACTATTGCTCCCAGGCTAACGT
TGTACGCCAGCGTGGATGGATGCAGCTACAATGCCATCTACTTGTTGTCGAACACGGCCAAGGAGCTGCAGCAGAAGCTTTTCAAGATGCCCGGC
TTCTACGAGTTCATGGCCAAGGCCAGTGCCCAGGAGAACGGAGCCGGTGGAGCAGCCACTGCAGCTGCTGCAGCACTCTTCAACAATTGGGGGAT
GCACTCCAAGTATTCGGGCAGCGGCTCCAATATCTTCAACGACGCCAACAAGAGCTGCGTGTACATATCGGGGCCATCGGGCATCCTTGTGACCA
TCACCGACGAGGTGCTGAACAACGAGATCAAGGACGGCAGCCTCTACGCGCTGGAGGTGCAGGCCGGCAAGGTGATCCTTAAGCTGATCAACAAG
CAGGACAACAACTAAGCGATGTTCTGGCAACGCGTATGCACTGCAGTAGAGACCACCCGAGCAATCAAGTATAGTTTATAGCATTTACACGCAGT
AAGATGGCACATCGAAACCGTTTTCTATATAGGTTTTAATTTGTATGAGATTTCGCGCAGCAATTTTGAACAAGTAAAAAGCAAGCAGCCTCTAA
CCCTGTTCCCTAAAATCTTTGTTAAAGAACTAGTGCAAAATATTTAAGTTTCGTTTTCAGTTCTCATTTTAAGTTTTGTTTATTTTATATGTATT
TTATACCACCTACGATATACGACTACATATGCACATTTAATTCTCCGATGCGATTGGATTTCGATTCGTTCTTTTCCTACTTTTAATTTCTTTTA
TCGTTATGGCGTATGCTTATCACATAAAGAACTATTATATATTTGTTTGTAGAACCACATCAATATCAATTGTTTGAAGTAGAAAGAAAAAACCC
AAAAAACAAAAAAAAATTTAAATACTGATTATTATCTTGAAGTACAGTACCACGAATACAAGAATTGATCAATTGTTTCGAAGCAGAGTTCAACT
AGCAACCAAACAACAACTTTTGTATGTGATAGAAGCAATAAAGTGTTATCCACGAGTGGACTGTCAAAAAAAATGTGGTTA

FIGURE SHEET 182

(SEQ ID NO: 329)

Start ATG: 110 (Reverse strand: CAT)

MDATNMVSPQHVPADMDDYSQNIMPESTPSQVTQWLTNHRLTAYLSTFAQFSGADIMRMSKEDLIQICGLADGIRMFNILRAKTIAPRLTLYASV
DGCSYNAIYLLSNTAKELQQKLFKMPGFYEFMAKASAQENGAGGAATAAAAALFNNWGMHSKYSGSGSNIFNDANKSCVYISGPSGILVTITDEV
LNNEIKDGSLYALEVQAGKVILKLINKQDNN*
(SEQ ID NO: 330)

Classification: transcription_factor

Celera Sequence No. : 142000013384479
AACAATGGTACAACCTTATCGGCTTTTAAATTTAATTCAGTCTTCACAACTTCAATGCTTTAAGACTGCTAGTTTAATTTGGGTAATAAACTTCT
AACAGGGTAAAAGTGGTGTGACACTAGTTTTTGAATTTGATATGCTAATATTAAAATACCATCGTGGGGTACAAGGTACATTTTACTAAATAAAG
ATCGCTTGGAACATAAACCTTTCTGTTCTAAGCACAACACTGGATAACTATGCAGCCGCAATAAGTTAGAATAGTTATATATCTTTTGGATAGCG
GAGTGTTTGGCCAGGGTGCGAGGATCTAGATACAAATTGAAGCCATAATAGTTCCATTATGGGGCGCACCACATTGCTGTCCGGACACAAATGCA
CCGAGCCCCTCGTGATGTGAGTTTAGGAAGGGCAATTGGTAATTACCAGCATGAGGGCCACCTCCGCCATGGGGGTGACATACAGGCACTGGTGG
AAAAGCGGAATCGCATCCACGATTTCCACTTGGGAGCCCTTCGATGTCTTCTCGGCCAGCAAGAGTCCGTTGACCGCCTGGTGTGGATACTTGGC
CGCGTGGAATATCAACTTGGCGTACGCCCGCTCCGAGACCTTGTAGTCGCACATTTTCTCAGAATATTATCTCAATTTATTCGGCAAAAAATAAA
ACATGAATTGGAAATTCGACAGCTAGAAAGTGTGACCGCGACGCAGCTGTTCAAATATACCGCAAACGTCAAATATACAATGAAAAATACTAAAA
TGGATGAGCATGGAATGGATTCCACAAAAAATGTGATCAAAACTATATTTGTTAATTATGTCTTTAACATTGAAAATATATTTATAACTTAAGTT
CTAGAAAATGGTTTCTAACATAGGTTGCAGTAGTCTGGTCACATCGATATGGGCGCGCAAACAATATGTGGATTCCACTTCAAATTAATTTATTA
CTCAAACTAATATTTAATTCTAACGTGAATGATGGAAAACATAACTGAATATGTGTAACATTTTATTTCTTAACTGTCCGTCTGCGTCTCGCTCT
TGCTTGGTTTTTTTCTCCGGTTTTTATATATGTATATTGTAACTAAAAATATTTAGCAGTTCAGCTGAATGTCCGGTGGCAGACCAACCCGGCC
TTCCAATTGGATCCTTGAACACCATCAAACCACACCGATGGGGGAACTACGTCTGGCTTTCATTCAGTATTGCCTTGATGTCGTCGGCGTCAAGA
GTCTCGTACTTGAGAAGCGCCTCCGCAAGCGCTTTGTGCTCCCTGGTGTGTTTTCGCAGGATAGCCTTCGCCCGCTCGTAGCTGTCGCTGAGGAT
GCGCTTGATCTCCGCGTCCACGGCTTCAATGGTGTTGGGACCAAGGGTGTCACCGGTGCCCAGACCCTTTGACGCCTCGATGGTGCGAAGACCGA
CCTTGTCCGACATGCCCCAGTCCCTGACCATATGCGTCGCGATCGAGGTTGCCTGCTTGAGATCACTGCTGGCTCCCGACGTAATCTTGTCCGTG
CCGAAGACCAGTTCCTCAGCAGCACGACCGCCCATCATGGTGTCCATCATGGCCAGCAGCTGTGCCTTTGTGACATGGTAACGCTCCTTCTCCGG
TATGTAGGCGGTGTGTCCAAGGGAGGGTCCGCGGGGCATGATGGTCACCTTGTGCAGCGGATGCGACTCCTTGGTGTAGAAGGCCACAATCGCGT
GGCCGCCCTCGTGGTAAGCGGTTATGGTGTTGGCCTCCTCGTCCGGTAGACGAGCCTTGCGCTCGGGTCCCATAAGTACTTTGTCTCGTGCCGTT
TCCAAATGCTTCATGCTGACCGTTTCGGCTCCATCGATGGCAGCTCTGCCAAAATGTTAGAATTATTAGTACCGCTCTTCAAAATTGTGATTGAA
TAATACAACACAAGTTATTCCTTACCTTAACGCCGCTTGGTTAATCATGTTTTCCAGATCCGCTCCAGTAAAACCAGAGGTGCCGCGCGCCAGCA
TGTCCAAGTCTATTTCATCGTGCAAAATCTTCGTCAGATACAGAGACAATATCTCCTTACGTCCAGTGAAATCGGGCGTCGACACCATGACTTCT
ACATCAAATCGGCCGGGACGCAGCAGAGCCTGATCCAAATCGTCGCGACGATTGGTGGCTCCCAAAACAATGACGCCAGCGTTCTGATGGAAGCC
ATCCATCTCGGAGAGCAGCTGATTGATGGTCTGATTGGCGTAAGGATGCAGCACAGAGTTGGTTCGCTTGGCGCCCACCGAGTCGATTTCGTCAA
TGAAGATAACACAAGGGGCACGGGCCTTTGCTGCCTCTGCAAGATGATGTTCTTGTTTAGTTGAGCACTTTGGATAATTGAAATCTACTTACTGA
ACAGATCACGCACTCGTCTGGCTCCTTGGCCTACGAGCACCTCGTCGAACTCCGGTCCGGCAGCATGGAAGAAAGGAACTTTGGCTTCACCGGCG
ACGGCACGGGCCAGCAGTGTTTTGCCAGTACCCGGCGGGCCAACCAGGAGCACTCCCTTTGGAAGCTTTCCGCCCAAATTTGAGAACTTTTCCGG
ACTCTTCAGGAATTCAACGACCTCCTTGAGCTCCTGCTTGGCTTCGTCGCAACCCTTGACATCCTCAAAAGTGACGTTGATCTCCTCAGGGTCCA
CTTCAACCTGGTTGCCCAGTTGTATGCTGCTGAAAGAAAGGCATATCAGATGGGTAAAGCAAAACTAATAACGTGGAGGCTCACCGAAATACGGA
TCCATTGGAGGTTGTAAAGAAGCTCAGGAAAATGCCCAAGAACACGACGATAACGACGATAGTCTGCAAAGTCTGCGTGACAATTACTAGAATTT
ATTTATAACACTAAAGAAGACCAAGGCCTTCTGTGGTTTTCAAAGTAATCATGGTACACTTTGAATGAATTTAAACTCGTACCTTCAGATATTTC
ATAGTTTTTCCTGATTTTGGAGAGTCCTCCGAGTTAGCGGCGGCCAAGTAGCCCTCGGCAAAGGCAATTTTCAGGCTCTCCTGGAATACAAAACA
TTAGTACGGTTAACAATTGAGAGACCCTGTCGTCCTACGGCTTTATTAAATCCATGCTCTTCGGATTTGGCCAGCAGCCGTCTCAGTTTTTCAGC
CTGAAGGGGTGTGTCCCCATCCAGACGCTGGGGCGAGTTGGCCAGAGCATTCTTTAGTCGGGAGGTCATTGTGGGATTGCGCTTTTGTTCCGCCT
CAATGGAACGATCCGTCTTAAAGCCACGTATCTGATTTCTATAAAGAGCTAAATTTGAGATATAGTTCGTAGATACTTTCCGTATAATTACAGCT
GTTGTTGTGAGAAGAGCGGACGAAGAAGACCTGGTGTAATAGTTGGAATCACCTTGCTGAAAACATAAACCAGGATTAAGCGGAGCCTCGAAAGG
ATAATTTGCAATACGTACACATTGGCGCCTGTGGGCACGGAACCTGCTGCACCGGTTAGCGAAACTTCGAACTGATAATTTTGCAGCTGGACACG
ACCGATCTGTGTGGCCGACTCCTCCAACGTGACTCGGACATCGCGCATGGAGGGCAGCATGCTCGTCACCTTGGCCAGCACATCATCGACCAGCC
GCCGGTCGAGAATGCCATTCAGTCGAGCCGCCCTCTCCACCATGCCCTGTATACTGGCGCTCGAACGGCTCAGCAGGTTCCGCAGGTCGAGCACT
AGGTCATGACTCCGGCTGGACGTGGACGTGGACTTGGACAACCGGGCAGCTCCCGCGCTCCCGTGCAGCTTGGTTCGATTAACGGAGTAGTAGTG
CGGCTTTCTGCTGAAGTTGCCTAGGTACAGGTAGGGCTGTCACATCACATCACACGCAGTTCCCCGATTCCAAGTGTTGGGTGGTAGAAATGGAG
CAGTCAGGTGGGCGAATGAATGTATTGTCATCGGGCAGCACTTACCACGGAGTGTGTGGTGGTGGAAAACATTGCCAAAACTACAAATTTCAATA
AATTACAAGGGCAGGCTCAGGATCGCGGCCAGCAGACGACACAGCTGTAACTTTACTTGACAGCGAAAATGTCATAATCTCGTCGCGTCGTGCGC
GTTGCATCCCTGGTTCTGGTGGTGCGCGACTTTCCACCTCTTATCAAAGCACGCGTTCTCCAATTACTGGCAATTTTCAAAAGTGTATTCGTTTG
TCGACTGGTGGTTTTGATTTTATTCGATTTTTAATTTGGTTTATATATCTAAACTGCCTCTCCGTACAGTCAACGCTGCTGATAGTGTTGCTAAA
CTTACATAAATATATAAAATTTTGTATAAATAAAATGAATGATAATCAGCGCAAACTTTGCATTCTATAAAATGTGATTTGTTTACTACTAAGAT
CAAATGAAAGTCTATTCCAAATTTTACTTATATTGACAACAAATTCCATTGTATCAACTGTAAATGAATGTTGTCTTTGTTATTTAGTTTTAACT
TCTTAAAGAAAAAGGTTTTTAACCAGTTTAGGATAGACAAAGAGTCCCTATCGCAACCATCGTGCATAGATCGACCATCACTAGTTCTGGAGATG
TGCAGAAGTCACTGGCCCGTTTCGCCGGCGACCAGGGTTGGCAAATCGGCTGCGCCGGTAGTTGGTCCGTTATACATTTCACAAATTCCACATTA
AATTGTATCAGCATGGACTCCCCGCTGAACGATGGCTCTCACCATCCACCGCCGCACGCTCCCCACCCCCTGGTGAGTGCTCTACGGTCCTTAAA
CTGCCACTACCCAAACGTTTGCATCTATTTCAGGCGGACTATCAGTTTTCTGCGGAGGAGGTGAAGGCGTTACGTGAGTGCAACACTGAGTCTTT
CTTCCAGCGCAGCCTGCCTTTCGGCACTGGACTGGGCCTGCTGGCCTACTTCGGCGTCAAGAACGGCTATTTGCAGGGACACGTCAAGTACGGCG
CCGTGCCCAAGGTCGTGATGGGCGTCATTCTGGGCTACTTTGTGGGCAAGTTCAGTTACCAGCAGAAGTGTGCCGAGAAGATCATGCGCCTACCC
AACTCCCATC
(SEQ ID NO: 331)

Exon: 4045..3941
Exon: 3836..3439

Exon: 3381..3322
Exon: 3268..3079
Exon: 3025..2933
Exon: 2818..2745
Exon: 2686..2373
Exon: 2316..1926
Exon: 1850..1001
Start ATG: 3967 (Reverse strand: CAT)

Transcript No. : CT11787
TAAAGTTACAGCTGTGTCGTCTGCTGGCCGCGATCCTGAGCCTGCCCTTGTAATTTATTGAAATTTGTAGTTTTGGCAATGTTTTCCACCACCAC
ACACTCCGTGCCCTACCTGTACCTAGGCAACTTCAGCAGAAAGCCGCACTACTACTCCGTTAATCGAACCAAGCTGCACGGGAGCGCGGGAGCTG
CCCGGTTGTCCAAGTCCACGTCCACGTCCAGCCGGAGTCATGACCTAGTGCTCGACCTGCGGAACCTGCTGAGCCGTTCGAGCGCCAGTATACAG
GGCATGGTGGAGAGGGCGGCTCGACTGAATGGCATTCTCGACCGGCGGCTGGTCGATGATGTGCTGGCCAAGGTGACGAGCATGCTGCCCTCCAT
GCGCGATGTCCGAGTCACGTTGGAGGAGTCGGCCACACAGATCGGTCGTGTCCAGCTGCAAAATTATCAGTTCGAAGTTTCGCTAACCGGTGCAG
CAGGTTCCGTGCCCACAGGCGCCAATGTCAAGGTGATTCCAACTATTACACCAGGTCTTCTTCGTCCGCTCTTCTCACAACAACAGCTAAATCAG
ATACGTGGCTTTAAGACGGATCGTTCCATTGAGGCGGAACAAAAGCGCAATCCCACAATGACCTCCCGACTAAAGAATGCTCTGGCCAACTCGCC
CCAGCGTCTGGATGGGGACACACCCCTTCAGGCTGAAAAACTGAGACGGCTGCTGGCCAAATCCGAAGAGCATGGATTTAATAAAGCCGAGAGCC
TGAAAATTGCCTTTGCCGAGGGCTACTTGGCCGCCGCTAACTCGGAGGACTCTCCAAAATCAGGAAAAACTATGAAATATCTGAAGACTATCGTC
GTTATCGTCGTGTTCTTGGGCATTTTCCTGAGCTTCTTTACAACCTCCAATGGATCCGTATTTCGCATACAACTGGGCAACCAGGTTGAAGTGGA
CCCTGAGGAGATCAACGTCACTTTTGAGGATGTCAAGGGTTGCGACGAAGCCAAGCAGGAGCTCAAGGAGGTCGTTGAATTCCTGAAGAGTCCGG
AAAAGTTCTCAAATTTGGGCGGAAAGCTTCCAAAGGGAGTGCTCCTGGTTGGCCCGCCGGGTACTGGCAAAACACTGCTGGCCCGTGCCGTCGCC
GGTGAAGCCAAAGTTCCTTTCTTCCATGCTGCCGGACCGGAGTTCGACGAGGTGCTCGTAGGCCAAGGAGCCAGACGAGTGCGTGATCTGTTCAA
GGCAGCAAAGGCCCGTGCCCCTTGTGTTATCTTCATTGACGAAATCGACTCGGTGGGCGCCAAGCGAACCAACTCTGTGCTGCATCCTTACGCCA
ATCAGACCATCAATCAGCTGCTCTCCGAGATGGATGGCTTCCATCAGAACGCTGGCGTCATTGTTTTGGGAGCCACCAATCGTCGCGACGATTTG
GATCAGGCTCTGCTGCGTCCCGGCCGATTTGATGTAGAAGTCATGGTGTCGACGCCCGATTTCACTGGACGTAAGGAGATATTGTCTCTGTATCT
GACGAAGATTTTGCACGATGAAATAGACTTGGACATGCTGGCGCGCGGCACCTCTGGTTTTACTGGAGCGGATCTGGAAAACATGATTAACCAAG
CGGCGTTAAGAGCTGCCATCGATGGAGCCGAAACGGTCAGCATGAAGCATTTGGAAACGGCACGAGACAAAGTACTTATGGGACCCGAGCGCAAG
GCTCGTCTACCGGACGAGGAGGCCAACACCATAACCGCTTACCACGAGGGCGGCCACGCGATTGTGGCCTTCTACACCAAGGAGTCGCATCCGCT
GCACAAGGTGACCATCATGCCCCGCGGACCCTCCCTTGGACACACCGCCTACATACCGGAGAAGGAGCGTTACCATGTCACAAAGGCACAGCTGC
TGGCCATGATGGACACCATGATGGGCGGTCGTGCTGCTGAGGAACTGGTCTTCGGCACGGACAAGATTACGTCGGGAGCCAGCAGTGATCTCAAG
CAGGCAACCTCGATCGCGACGCATATGGTCAGGGACTGGGGCATGTCGGACAAGGTCGGTCTTCGCACCATCGAGGCGTCAAAGGGTCTGGGCAC
CGGTGACACCCTTGGTCCCAACACCATTGAAGCCGTGGACGCGGAGATCAAGCGCATCCTCAGCGACAGCTACGAGCGGGCGAAGGCTATCCTGC
GAAAACACACCAGGGAGCACAAAGCGCTTGCGGAGGCGCTTCTCAAGTACGAGACTCTTGACGCCGACGACATCAAGGCAATACTGAATGAAAGC
CAGACGTAGTTCCCCCATCGGTGTGGTTTGATGGTGTTCAAGGATCCAATTGGAAGGCCGGGTTGGTCTGCCACCGGACATTCAGCTGAACTGCT
AAATATTTTTAGTTACAATATACATATATAAAAAACCGGAGAAAAAAACCAAGCAAGAGCGAGACGCAGACGGACAGTTAAGAAATAAAATGTTA
CACAT
(SEQ ID NO: 332)

Start ATG: 79 (Reverse strand: CAT)

MFSTTTHSVPYLYLGNFSRKPHYYSVNRTKLHGSAGAARLSKSTSTSSRSHDLVLDLRNLLSRSSASIQGMVERAARLNGILDRRLVDDVLAKVT
SMLPSMRDVRVTLEESATQIGRVQLQNYQFEVSLTGAAGSVPTGANVKVIPTITPGLLRPLFSQQQLNQIRGFKTDRSIEAEQKRNPTMTSRLKN
ALANSPQRLDGDTPLQAEKLRRLLAKSEEHGFNKAESLKIAFAEGYLAAANSEDSPKSGKTMKYLKTIVVIVVFLGIFLSFFTTSNGSVFRIQLG
NQVEVDPEEINVTFEDVKGCDEAKQELKEVVEFLKSPEKFSNLGGKLPKGVLLVGPPGTGKTLLARAVAGEAKVPFFHAAGPEFDEVLVGQGARR
VRDLFKAAKARAPCVIFIDEIDSVGAKRTNSVLHPYANQTINQLLSEMDGFHQNAGVIVLGATNRRDDLDQALLRPGRFDVEVMVSTPDFTGRKE
ILSLYLTKILHDEIDLDMLARGTSGFTGADLENMINQAALRAAIDGAETVSMKHLETARDKVLMGPERKARLPDEEANTITAYHEGGHAIVAFYT
KESHPLHKVTIMPRGPSLGHTAYIPEKERYHVTKAQLLAMMDTMMGGRAAEELVFGTDKITSGASSDLKQATSIATHMVRDWGMSDKVGLRTIEA
SKGLGTGDTLGPNTIEAVDAEIKRILSDSYERAKAILRKHTREHKALAEALLKYETLDADDIKAILNESQT*
(SEQ ID NO: 333)

Name: paraplegin-like protein
Classification: endopeptidase

Celera Sequence No. : 142000013385217
GCACTCGATCACAATCAGGTCGAAACTGGAGTTGGCATAGGAAGCTGTAATGCATAAACATCACTGATTTTAATCTGCTGACTCACTGGCTAGTC
AAAAACAGCACACACACACCGCACCGCACGCAACTTACAAAACGAAAGGCGGTGCACATTTTCCAAAGCCACATCGCCGCCAGTGGCCGCCTTTA
GTTGCTCCACGCGCTTGTCCAAGTCGGCGCTGTCCGTCCATATGTATAGGGATTTTTGTAGACCCTTAAAGTTCTCCATTGTGGATGTGTTTCTA
GAATATCTCAAAAGTTCAAGCACCGAACGGAACCGATTTTTGATTTCACAAGTTAGATATGGCAATGCACCGAAAATCGAGCGGTGATATCGATT
GTACCTGCCTATCGGATTGCAAATGATATTCAGTGATTGTAGATTTTTCCACTTTACACTGTGACTGCTAAAATATATGAATAACTAAGTGTACT
CCACCAGATTCGTTTTTTAATGAGTTACAGCTTACATTCTGATACATAATTAACAGCTTTTAGTTGCATATTGTGTGTTTCTGCCACTAAACCTA
TTTAAACGGTTACATTTAAGCCTAAAGTCGCGAATTATCTTTTAAATTCACCCATGTGTACTTTCCCACGGCCCGTTTTAAAAATGCATGGACAG
TTAGACAAGAAGGTTGGTAGTTTGTACCTTGAATTTTAAATGTGGGCGCTCAAAATCGAAGTGTTCAATGAAAATCGATACCTTTCGCATCAGTT
AAAAGTATTTATAGATATAAGAAATAATATCTTTAACAGTGATGTGATGGGAATAAATATACAAATGTATTCAGAAACTGCAAAGTTAAAACAAA
ATATATTAGCTACTCCAAATTGGCTATAAAATAACCAAATGCCCACTGCCATCCAAATCCAACCAACAGTGCTGTGAAGCGACAAACATATCGCC
GGTAGGCAGCGACTATCATAAATAAGCGCCTATCGGACTATCGATACAACATCAACATCCTCAGTCGCTTTTTTAGTTGTAGCATATTATAAATA
TAACTCGAGCGCTAGTTGCAGCCTTAAACAGAAGCCAGCCGCCACTACCGCTAGTCGCTAGTCAAGATCTGCTCGAAACGCTGAAATATGTGTGA
TTAGTCGTGAATCGCAGCTAGCCGCAAATCCAGCTTGAGCTACAACAACAAAGCCAATCCGCGGTTAAGAGGAAGAGAGTGCGTGAGAGAAACGA
CAGCTGCTCTGCGTGTGTGTTTGTGCAGCAGGATAACAAAATAGAAAACATACAGCAGCAACAACAACAACAAAAACAGCACCAGCGAACAGTGT
ATAAAGTGCCAAACGAATTTGCCAAATAGCCAAAAACGAAATAATAGAAAAGATCCAAACAAAATTCCAATAAGTTCAATGCAAGGAGACATGTG CATAAATGAAGAGCTACAGCCAATTTAATTTAAACGCCGCCGCCCCGCCCGCCATTGCCTACGAAACTACGGTTGTAAATCCCAACGGCTCACCC
CTCGATCCTCACCAGCAGCAGCAACAACAGAGCCAGGATATGCCGCACTTTGGACTGCCCGGTCCGCAGCCGCCGTCGTCGCAGCAGCAGCAACA
ACAATTGCAAGTGCACCACCAACAGCAGCAGCAGCAGCAACAACAACAACAACAACAGCAGCATCAACAACAAATGCAGATGTCCTTGCTGCCGG
GTCCTTACCGGCCACACATCGAGGAGAAGAAGCTCACGCGGGACGCCATGGAGAAGTACATGCGCGAGCGCAACGACATGGTCATCGTTATCCTG
CACGCCAAGGTACGAAAGGATTTCCACTTTTAAGCCGGTATTATCAGGTGCTTGGTCTGGATTTAGTATTCAAGATATTCTAAAACATACAAGGG
AACTCCTGAGTCTTAAGTCTTAATTAAATTATTTGAAGCTTGAAATACATTATTTCAATATTACTAAAAATATATTAACCCAAACTGGAGAAACG
TAGGATATCCTAACTTTCATTTAAATTAGAAACTTGGTCAGTTTTGTACGTCGATTTCCTAAATTATTCGATTTTTTAGATTAAATAGATTAAAT
TCAGATTTTCTTTCTATTTCAAGTTTAACGATGTATCCTTTCTTTGAAAATTACTTGTATGCTTTACAAGATATTTATTTTTTTTTTATAATTTA
GTTTTAATCTAATCGGTCAGTCCGCAACGCCAAAACCACACCCACTATTTAAAGGTGCTAGTGTTTCCATTGTCCACTTTAAAGTGTTACATTTT
TGCGGTTTTTGGCGAACGCAGACATGAAAATGGAATAAAATTGTCGCGGTTGCTTTTAGCGGTGGCGATCTTCAAGCGACGACTGCCGCCAAATG
GGAATCCTTCACACTCGACTGCCCGCAAATTGAGCAACGCGAGCGCGGTCCAGTCCGCAATGAAAATAATTGAAATTAATTACAGAAAATTAACA
AAGCTGCATTGCTTGCGGTTTTGATATGATTTTCCGATAATCTGGACGGCAATTTGTACTAATTGAATTTTCCCTGCACCATCGTGCGCCTCTGT
CTGTCTGTCTGTGTGAATTCCAGGTGGCCCAAAAGTCCTATGGCAATGAGAAGCGATTCTTTTGCCCACCGCCGTGCATTTATCTGTTCGGAAGT
GGCTGGCGCCGGCGGTACGAGGAGATGTTGCAGCAGGGCGAGGGCGAACAGGGAGCACAACTATGCGCGTTCATCGGTATCGGGAGCAGTGACCA
GGATATGCAGCAGCTGGATCTCAATGGCAAGCAGTACTGTGCGGCCAAGACGCTCTTCATCTCGGACTCGGACAAGCGAAAACACTTTATGCTGT
CGGTGAAGATGTTTTACGGAAACGGTCATGACATTGGCGTTTTTAACTCGAAACGGATCAAGGTTATATCCAAGCCGTCCAAAAAGAAACAGTCG
CTAAAGAATGCCGATCTGTGCATAGCCAGCGGCACCAATGTAGCCCTGTTCAATCGCCTGCGTTCCCAGACTGTCTCCACCCGTTACCTTCACGT
GGAGAACGGACACTTTCATGCGTCGTCAACACAATGGGGAGCTTTTACGATACACCTGCTGGATGACAATGAGTCCGAGTCGGAGGAGTTTCAGG
TGCGCGATGGTTACATTCATTACGGAGCCACAGTCAAACTGGTGTGCTCCGTAACGGGCATGGCCCTGCCACGTCTGATCATCCGGAAGGTAGAC
AAGCAGATGGCCCTGCTGGAAGCCGACGATCCCGTTTCTCAGCTGCACAAATGCGCCTTCTACATGAAGGATACGGATCGGATGTATCTCTGTTT
GTCGCAGGAGAAAATCATACAGTTCCAGGCCACGCCGTGCCCCAAGGAGCCGAACAAGGAGATGATCAATGACGGCGCCTGCTGGACCATCATAT
CCACCGACAAGGCTGAGTACCAGTTCTACGAGGGCATGGGTCCTGTGGCGTAAGTATAGCTTACTTACAACTCAATGGATTAGTTTTCATTTCGT
GTTTTCTTCCAGTTCTCCAGTCACTCCAGTGCCAATCGTTAATTCCCTTAATCTCAATGGCGGCGGGGATGTGGCCATGCTAGAGCTGAGTGGCG
ACAACTTTACGCCGCATCTGCAGGTGTGGTTTGGCGATGTGGAGGCGGAAACCATGTACCGCTGCACAGAGACATTGCTATGCGTGGTGCCGGAG
ATTTCACAATTTCGAGGCGAATGGCTTTGGGTAGGTTTTCCAATGTAAATCTGTTTAATACGCGCTATAAATTTTACTTTTAATGGTCCTTGCAG
GTACGTCAGCCCACGCAGGTGCCCATTTCGCTGGTGCGCAACGATGGAATAATTTATGCCACCGGTCTGACCTTCACGTATACACCTGAACCAGG
TCCTCGGCCGCACTGCAATACACAGGCCGAGGATGTGATGCGAGCGCGACAGAACAATAACAATAATAACATCACTAGCATTAGCAACAATAATA
ACAGCAACAATGCGGGATCGCCGGCAGCCGGCGGTGGCTTGCAACAACAACAGCAGCAGCATCAGGCTCTGCCCTCCATCTCAGAAGTGCAATGG
AATAGTCATGGTAGCGGCTTATCCTGAGTGCAGGATTATTGCATCGCACACATATGTATCCTAAGTTATTTATAGTTTTTATCGAAGACCTTAGT
TTGTAGATTGACAATTTTTCTCATACTAATTTTCAACCCCTCGTGACGTAAACCAAAATGTGTCCCCTTCTCTCTAAAGTGAATCATACTTTACA
CATGTATCTAGTGCTAGTTCGGAACCAATAGAATTGTAAATGACACATAAAACTCTGTACATAACTCGAAAAGCTCACTGACATACATACATACA
TTTGTATGTGCATGAATATACCTTTACACAAAACATGTAATTCTAGTTAAATATACAATTGATGTAAGTTTATAGACGATTTTTAGATGCGGTTG
AAATATTTATGATTTTCTTTGCTATGAATTTCCAAAGATCTAAATGAAAAAAAAAAAATACTGCGAAATGCATCGGAAATTTTTATTATACACAAG
CCAGTAGCCACGCTACAAAAACATTCCATTTCCCTCTTTAGCTTTCTAAAAAGTCGAAGACAAAGTCAAAAAGGGAAAAATTTGTTTCTGTACAT
ACAGTTTTGTTGCATTTTTTTATTAACTTTGGAAATTCGTAGCATTAAAAATCCCAATAAAATATTTTGTAAAATAAAATCGCAACAAGACAAAA
CAGCGATTTATTTAAGTGTAAGCGAAATGCCTAACATAAATAAAAAAAAGAAATCCCAAATGATGACAAAGAATAATCAAATCATGTCAGCTTAT
GTTTTTGGTTTAGCGTGATTCTTCTGGTTCACCATTTTTCCTGTGGCCTAAGGTGGAGCGCTGGGGAGGATTGGTTGCCTTAAATTGCTGTGGGA
ATATTACCCAGTATCGTGTGAATATTTTTAAACAAAACAAGTGCAGCTCTTCCCACGATGGTTTGCCTCAACCCCCTCGGACGGCCGACTTTAA
TTATAGTTTGGTCTGGAATTGCTGAACGCGAAGCTAAGAAGCAAATATACATAGATATATAACACTATTGTTTCCGTTTTGGCCAAGTTAAGGAG
CAGAATATTCTCACAGCCCAAAAAGCCGCTGCCGAGCTGCTGTGAGAATTTTTACTGCCTTTGTTGAATATTTATGCATTCGTTGCTGCTGCTGT
CTTTACAGATTTACAAATTAAGATTCGCAGTTTTGAATTAATTATCGCTCACTTCCGCTCGACGGAATCAGAAGGTGAGCGCTGGCCAAGCATTT
AATCTCATCTTGCACTTGGGAGACATATTTCTTATCAGAGTCAGCCAATAGGAACTTGGCTGCAACCCCTAAGATTTACTGCACCGGGCGATGG
GAACGAAAGACTTAAACAACGAACTTTGGTTGCGTGAGGAATCAAACTACTGGCGGCCGCCTGTGTTCATTATGATGGAAAAACCACCACCAAAA
GTTCTGGCTCTGGCAATTGGAACTGCAACCTCTTAAGGTCGTCGCCGTCTTATAAGAAGCTGAATATGAAATTAGTTTGGAATTTTTAATGAACA
ATTCCTTCACATTTCCCCAGGCCCTCTTTCTCCACCACTGTTTGGATAGGCGAGTGCGATGATTGTGGTCGTTTTTAGAAAGGGGGAGACAGCAA
TTTCTAAAAGTTCTCAGGACTGCTACACAACCTCATACCGTCTACTAAAAAAGTTCATTATCTTGAAAAATCTAAGTCTACCTGCCGTCGTCTTT
AGTCTTTAGCTTGCCGTGCCGACTGCTGCCGTTT
(SEQ ID NO: 334)

Exon: 1001..1814
Exon: 2589..3469
Exon: 3528..3735
Exon: 3801..4829
Start ATG: 1431

Transcript No. : CT11789
ATCAACATCCTCAGTCGCTTTTTTAGTTGTAGCATATTATAAATATAACTCGAGCGCTAGTTGCAGCCTTAAACAGAAGCCAGCCGCCACTACCG
CTAGTCGCTAGTCAAGATCTGCTCGAAACGCTGAAATATGTGTGATTAGTCGTGAATCGCAGCTAGCCGCAAATCCAGCTTGAGCTACAACAACA
AAGCCAATCCGCGGTTAAGAGGAAGAGAGTGCGTGAGAGAAACGACAGCTGCTCTGCGTGTGTGTTTGTGCAGCAGGATAACAAAATAGAAAACA
TACAGCAGCAACAACAACAACAAAAACAGCACCAGCGAACAGTGTATAAAGTGCCAAACGAATTTGCCAAATAGCCAAAAACGAAATAATAGAAA
AGATCCAAACAAAATTCCAATAAGTTCAATGCAAGGAGACATGTGCATAAATGAAGAGCTACAGCCAATTTAATTTAAACGCCGCCGCCCCGCCC
GCCATTGCCTACGAAACTACGGTTGTAAATCCCAACGGCTCACCCCTCGATCCTCACCAGCAGCAGCAACAACAGAGCCAGGATATGCCGCACTT
TGGACTGCCCGGTCCGCAGCCGCCGTCGTCGCAGCAGCAGCAACAACAATTGCAAGTGCACCACCAACAGCAGCAGCAGCAGCAACAACAACAAC
AACAACAGCAGCATCAACAACAAATGCAGATGTCCTTGCTGCCGGGTCCTTACCGGCCACACATCGAGGAGAAGAAGCTCACGCGGGACGCCATG
GAGAAGTACATGCGCGAGCGCAACGACATGGTCATCGTTATCCTGCACGCCAAGGTGGCCCAAAAGTCCTATGGCAATGAGAAGCGATTCTTTTG
CCCACCGCCGTGCATTTATCTGTTCGGAAGTGGCTGGCGCCGGCGGTACGAGGAGATGTTGCAGCAGGGCGAGGGCGAACAGGGAGCACAACTAT
GCGCGTTCATCGGTATCGGGAGCAGTGACCAGGATATGCAGCAGCTGGATCTCAATGGCAAGCAGTACTGTGCGGCCAAGACGCTCTTCATCTCG
GACTCGGACAAGCGAAAACACTTTATGCTGTCGGTGAAGATGTTTTACGGAAACGGTCATGACATTGGCGTTTTTAACTCGAAACGGATCAAGGT
TATATCCAAGCCGTCCAAAAAGAAACAGTCGCTAAAGAATGCCGATCTGTGCATAGCCAGCGGCACCAATGTAGCCCTGTTCAATCGCCTGCGTT
CCCAGACTGTCTCCACCCGTTACCTTCACGTGGAGAACGGACACTTTCATGCGTCGTCAACACAATGGGGAGCTTTTACGATACACCTGCTGGAT
GACAATGAGTCCGAGTCGGAGGAGTTTCAGGTGCGCGATGGTTACATTCATTACGGAGCCACAGTCAAACTGGTGTGCTCCGTAACGGGCATGGC CCTGCCACGTCTGATCATCCGGAAGGTAGACAAGCAGATGGCCCTGCTGGAAGCCGACGATCCCGTTTCTCAGCTGCACAAATGCGCCTTCTACA
TGAAGGATACGGATCGGATGTATCTCTGTTTGTCGCAGGAGAAAATCATACAGTTCCAGGCCACGCCGTGCCCCAAGGAGCCGAACAAGGAGATG
ATCAATGACGGCGCCTGCTGGACCATCATATCCACCGACAAGGCTGAGTACCAGTTCTACGAGGGCATGGGTCCTGTGGCTTCTCCAGTCACTCC
AGTGCCAATCGTTAATTCCCTTAATCTCAATGGCGGCGGGGATGTGGCCATGCTAGAGCTGAGTGGCGACAACTTTACGCCGCATCTGCAGGTGT
GGTTTGGCGATGTGGAGGCGGAAACCATGTACCGCTGCACAGAGACATTGCTATGCGTGGTGCCGGAGATTTCACAATTTCGAGGCGAATGGCTT
TGGGTACGTCAGCCCACGCAGGTGCCCATTTCGCTGGTGCGCAACGATGGAATAATTTATGCCACCGGTCTGACCTTCACGTATACACCTGAACC
AGGTCCTCGGCCGCACTGCAATACACAGGCCGAGGATGTGATGCGAGCGCGACAGAACAATAACAATAATAACATCACTAGCATTAGCAACAATA
ATAACAGCAACAATGCGGGATCGCCGGCAGCCGGCGGTGGCTTGCAACAACAACAGCAGCAGCATCAGGCTCTGCCCTCCATCTCAGAAGTGCAA
TGGAATAGTCATGGTAGCGGCTTATCCTGAGTGCAGGATTATTGCATCGCACACATATGTATCCTAAGTTATTTATAGTTTTTATCGAAGACCTT
AGTTTGTAGATTGACAATTTTTCTCATACTAATTTTCAACCCCTCGTGACGTAAACCAAAATGTGTCCCCTTCTCTCTAAAGTGAATCATACTTT
ACACATGTATCTAGTGCTAGTTCGGAACCAATAGAATTGTAAATGACACATAAAACTCTGTACATAACTCGAAAAGCTCACTGACATACATACAT
ACATTTGTATGTGCATGAATATACCTTTACACAAAACATGTAATTCTAGTTAAATATACAATTGATGTAAGTTTATAGACGATTTTTAGATGCGG
TTGAAATATTTATGATTTTCTTTGCTATGAATTTCCAAAGATCTAAATGAAAAAAAAAAATACTGCGAAATGCATCGGAAATTTTTATTATACAC
AAGCCAGTAGCCACGCTACAAAAACATTCCATTTCCCTCTTTAGCTTTCTAAAAAGTCGAAGACAAAGTCAAAAAGGGAAAAATTTGTTTCTGTA
CATACAGTTTTGTTGCATTTTTTTATTAACTTTGGAAATTCGTAGCATTAAAAATCCCAATAAAATATTTTGTAAAATAAAATCGCAACAAGACA
AAACAGCGATTTATTTAAGTGTAAGCGAAATGCCTAACATAAATAAAAAAAAGAAATCCCAAATGATGACAAAGAATAATCA
(SEQ ID NO: 335)

Start ATG: 431

MKSYSQFNLNAAAPPAIAYETTVVNPNGSPLDPHQQQQQQSQDMPHFGLPGPQPPSSQQQQQQLQVHHQQQQQQQQQQQQQHQQQMQMSLLPGP
YRPHIEEKKLTRDAMEKYMRERNDMVIVILHAKVAQKSYGNEKRFFCPPPCIYLFGSGWRRRYEEMLQQGEGEQGAQLCAFIGIGSSDQDMQQLD
LNGKQYCAAKTLFISDSDKRKHFMLSVKMFYGNGHDIGVFNSKRIKVISKPSKKKQSLKNADLCIASGTNVALFNRLRSQTVSTRYLHVENGHFH
ASSTQWGAFTIHLLDDNESESEEFQVRDGYIHYGATVKLVCSVTGMALPRLIIRKVDKQMALLEADDPVSQLHKCAFYMKDTDRMYLCLSQEKII
QFQATPCPKEPNKEMINDGACWTIISTDKAEYQFYEGMGPVASPVTPVPIVNSLNLNGGGDVAMLELSGDNFTPHLQVWFGDVEAETMYRCTETL
LCVVPEISQFRGEWLWVRQPTQVPISLVRNDGIIYATGLTFTYTPEPGPRPHCNTQAEDVMRARQNNNNNNITSISNNNNSNNAGSPAAGGGLQQ
QQQQHQALPSISEVQWNSHGSGLS*
(SEQ ID NO: 336)

Name: J KAPPA-RECOMBINATION SIGNAL BINDING PR
Classification: DNA_binding
Gene Symbol: Su(H)
FlyBase ID: FBgn0004837

Celera Sequence No. : 142000013384832
TGAACGGAAGCATACAGGATCAGAGTTCAGCAAAGTGCAATGCCAAAGCGGACTACAACAATGTCCACGAGGTCGGGCCATCGACCAGTGCGGAG
GGGGCGCTGGCGCTCAATGCCGCCTGCAACTAGGGGCGTGGCTGTTGGCCCATATGCATATACAATACGAAGAGAGCCAGCAATTAGGGTGTAAG
GCATTTAGAGGAAACATCAACAGTACTTTAAAATTTAGCTTGAAATATGTTTAGCGAAATGTAGCTCTTCCGGTCAGCCAGAGTAACCGGAAACG
GAAACGTAAACGCCGGACGCGCATACAATACTCATCGACACACTCAAGTTGCCACTCGGACGAATGGACTGTTGTTTATTGTGCAATTCGCACGA
GACGAACTCACAGGCATTGCATTTTCAAGAAATTAGTATTACATAATTGTATCCGTATCTGTTAAGTACTCCGGGCGAAGAGATCAATTCAAAAT
GCGGTTGTGTCGTCGAAAAAAAAAACAAACTCGAAAATACTCATGCACAGACTCTGAATAAGTTCCCCTTTGCAGAACGCAATTTACTCATCAGTC
AGTATTCTCTATGGCCACTGTATTATTTTTATACCTTCATTTGTTAGCTTTAAGTTTTTTTACACAACTACTACTTATACTTGTGCTGCCACCA
GTTGGGCTGCCGTAGTTGCAGATCAATGTATCCATTGTCCATACATTGCGAGAATCTTTTATAATTCGTCTAAGCATAAGTTACTGTACGTCGTG
TTGTATAGCGCTGTAATATCCTGTCACCTGCTTCTGCTTAATTAATACCCTATATCGGGCGAGAGCAAGGTACGATTAAACCATTAGATAATGAA
ATACAAATACATAGTGTATAAACAGATGAACGACGTGCGTTTAAAGGGGGGTTCTCCGATCTCTCAGTCCCCGAAACAGGAATCAAAGTGGGCAA
CTCTGCAAATGCTTAGTATTTAAAAATCAAGGGTTCTATCAATATATTTCATCCACTTGAACTTTTAGAAAGCTGTGATAAATCGAAATGAAGGA
CCTGGACGGCTCCTTGGACACTCTGGAGAATGCCCGCTTCAACTACGTGTATATGAAGGACATTGCTCGCCTGGCAAAGGACTCGATCTTCTCGC
ATAACGAGCTGATTAGCATTGTAATGCTCTACCATAAGTTTGTGCTGGTCAATGGGCCGAGAGCAAAGTACATGACCATTCAGCAACTCTCTGCG
CTGATGGAGCTCTTGTTTGAGATCGTGGATCGCGATCTCATTGCGACCATTGTGTATAGAATAGCCCATACACCAGGTTCCAGGCCTCCTGACTT
CTTTTCCGACAAGCATATACACTTGGAGTCCTTTGTGCGGCTTTTCACCGTATACTTCACCAAAGATCTTCAGCTGAAAATGGAATTCGCATTCT
CGGTGGGCAATTCATAGTATTCATATGAAATTAGCCTAGACCATTTGCTTACATTGCAGGTCTACGATAAAAGCGATTCCAAGCAGTTGAATGGC
GAGCAAGTTGGGTTCTTCGTCGGCAAGTTCTTTGAGAGCGAGGATGAAGACGAATCCATTGAGCTGCGCTTGGTGAGGCACCATCCCCTACACTT
GTTCCATTGAAACACTGACACATTTCGCATTCCTTCAGGACATGAAGGAGATGCTGTTCCTCAAATTCGACTTGGACAAGGATACCAACATTGGG
GTTGATGAGTACTACGAGGTGGTCCGCCGACAGCCCATGCTGCTGGAGTGCTTTGGTCGCGTGTTTCCCCCGAATCCCCAGATGGAGGTCCTTGC
GCTGTGCGCCAATGTAATGTCTTGGTTTGACGATTCGCCCAATCCCAGGATTATGATAAAACCAGACGGCGGCAAGGCCAGCTAGCTAACAGGAC
GTCCAGGAACGCATTTTTATCTAACCAGATACTTAAATTGTGACACGTCTAGAAATTGAAAAGTGCAAATAATTTAGTGCATCATAAAGGTTTAC
ACTTTTATTAACTAGTTTTGTACGTTACTTTTGAATATTGGTTCTGAACGGTAAACTCGCTTCATTGAGGCTGCTTCGATAACGATACCGATTAG
TCAGTGTGTCCGGATTGTCTCATCCCTGCTGCACGCGACCCACCATTTTAGTAACACCGAAGAAACGGTAGCGAAATGGCCACGGAGGAGCACCA
GCGCCTGGCCAGCATCGTGAAGAGCTGCCACGAAAGCCTGCGCCAGTTGACTAAGGAGTATGGCGCCACAGCGGCCTGGCAGGAGCACACGAGTC
CCAGGAACGCCAAGCAACTGGCGGAGTACGCCAAGGCGATGAAGCAACTGGCGGCCATATGGGAGACCAACGATGGGAAGGTGGAGCTGCAGGCA
CGCAGCCGCATCAAGTGGGCCATCGACTACATCACCAAGTACTTCTTTACCGAGGGCATATATTTGCAGAAGCGCCAGCGGGAGCAGCGACTCCT
GGAATCCTACAGAGCCGAGGGAAAACTGGGCGAGGTGCAGTGCAGGCTGATGGAGGAGCCGCCGGACAGGCTGCACGTCCTGGATGTGGGCAGCT
GCTTCAATCCCTTTTCCAGTGCTCCGCACTTGGAGGTAACCGCCCTGGACTTGTGTCCCGCCACCGAAGATGTGCTGCAGGCGGATTTCCTCAAA
GTGGAGGTGGTACCCGGAATACGAGAACCTGAGCTGGAGGAGGGCAGCGTAAGAAGGCTACCAGCAAGCCACTACGAGTGCGTCATTTTCAGTTT
GCTACTGGAATACATGCCCAGCGCCGAGCAGAGACTACAGTGCTGCCTTCAGGCCTACGACCTGCTGCTGCCCGAGGGCATCCTTGTGCTCATCA
CACCGGACTCCCAACATGTTGGCAAAAACGCCCACCTCAT
(SEQ ID NO: 337)

Exon: 1001..1427
Exon: 1485..1592

Exon: 1654..1890
Start ATG: 1038

Transcript No. : CT11950
ATCCACTTGAACTTTTAGAAAGCTGTGATAAATCGAAATGAAGGACCTGGACGGCTCCTTGGACACTCTGGAGAATGCCCGCTTCAACTACGTGT
ATATGAAGGACATTGCTCGCCTGGCAAAGGACTCGATCTTCTCGCATAACGAGCTGATTAGCATTGTAATGCTCTACCATAAGTTTGTGCTGGTC
AATGGGCCGAGAGCAAAGTACATGACCATTCAGCAACTCTCTGCGCTGATGGAGCTCTTGTTTGAGATCGTGGATCGCGATCTCATTGCGACCAT
TGTGTATAGAATAGCCCATACACCAGGTTCCAGGCCTCCTGACTTCTTTTCCGACAAGCATATACACTTGGAGTCCTTTGTGCGGCTTTTCACCG
TATACTTCACCAAAGATCTTCAGCTGAAAATGGAATTCGCATTCTCGGTCTACGATAAAAGCGATTCCAAGCAGTTGAATGGCGAGCAAGTTGGG
TTCTTCGTCGGCAAGTTCTTTGAGAGCGAGGATGAAGACGAATCCATTGAGCTGCGCTTGGACATGAAGGAGATGCTGTTCCTCAAATTCGACTT
GGACAAGGATACCAACATTGGGGTTGATGAGTACTACGAGGTGGTCCGCCGACAGCCCATGCTGCTGGAGTGCTTTGGTCGCGTGTTTCCCCCGA
ATCCCCAGATGGAGGTCCTTGCGCTGTGCGCCAATGTAATGTCTTGGTTTGACGATTCGCCCAATCCCAGGATTATGATAAAACCAGACGGCGGC
AAGGCCAGCTAG
(SEQ ID NO: 338)

Start ATG: 38

MKDLDGSLDTLENARFNYVYMKDIARLAKDSIFSHNELISIVMLYHKFVLVNGPRAKYMTIQQLSALMELLFEIVDRDLIATIVYRIAHTPGSRP
PDFFSDKHIHLESFVRLFTVYFTKDLQLKMEFAFSVYDKSDSKQLNGEQVGFFVGKFFESEDEDESIELRLDMKEMLFLKFDLDKDTNIGVDEYY
EVVRRQPMLLECFGRVFPPNPQMEVLALCANVMSWFDDSPNPRIMIKPDGGKAS*
(SEQ ID NO: 339)

Celera Sequence No. : 142000013384826
TAACTGAGCTGTGTTTGAACTTACCCTCGTTGTACGCTTCGAAGGCCTTCATAAAGTCATTCAGACCCGCAGCGGCAGCTCCTTTGCGTGAGTAA
CCCTTAGGCCAGGTGGGATTAAGCTGAATGGTCTTCTCCGCATCTTCTAGCGCCTCCTGGAACTTTCCAGCCTTGGCGAATGCCGCCGAACGGTT
GCTGTAGAGCACATGGTTCTGGTCGTCCAGAGCGATGGCCTCTGTGTACGCCGCCACCGCCTCGTCGAACTTCTCGGCACTGAGCGCCTGGTTAC
CCTTTTCCTTGAGTTCGTTCACCTGCGAAAACCGCAAGGGTTTTGATTGGAAATGCCAACGCCTTTCCTTTGTCTCGGGCACTTACCTTGTCCA
TTTCTGATAAGGGAGAGGATAGCGCTGTCGAATTACAGTTTTTCCTGTATTTTTGTACGACTTTTTAATAAAACACGCTGCGAAATGTGCCGTGC
CAGGTGAAAATGCGAAAAATGCCGACTTTTCTAGAAGCAATCGATAGGGTTGTCAATGCTTCTGCGACTGAATTTAATCTTTTTCCAGACTGCGG
TTTAGAACTTAGCTCGTTCTCAAGCGGGGAACAAAACCAGCAAGCCTTCTTAAATAATTTTTTCCATTGCTTATATAAATTAAAAAAATTGTTGA
TCAAATATAAATAATACCTTGAGCTTTATAGAATTTAAATGTTATTTTATTGTATTGTTTATTTATGTTTATATTATATTATTATTTGCGTAAAT
AATTTTCTCAATTTCTTATTTTGAATTGTAAAATTTTTCTAGTCAAATGAAAAATAAGTCCTCAGGCTTTTAAGTGCATTAATATTTAAATATTT
GAAATTAATATTTAAAATGTTAGCATATTTTAAAACATTTAAATTAAGAACAGAGGTATCGAAAAACGATGCTGCCAAAAACACTAAATATCGAT
AACTAATCATCGATTTTATTTGCAACTCTAGATTCGAGGCTGGCAACGCCGTGCAAAATACGACCAGACGCTGCTTTTTTCGGTTTCCGAAAATA
ATTGAAAATTATCACTAAATAAACAGGCGGCTAACATAATTGCAGTTTGACCGCGTTGCAGAGACAAGCGGGTAGATAAGTTACACATTTTGGCC
ACAGCAACACCACAGTAAAGCCGCCAGCATGGCCGAGTACTTGGCATCCATTTTTGGCACGGAAAAGGACAAGTAAGTCGCATGGCACATTTATT
TTAACGTTGCCGGGATTAATAACTAAATGGCGTTGCATTTCCCAGGGTGAACTGTTCGTTCTACTTCAAGATCGGCGCCTGCCGCCACGGCGACC
GGTGCTCTCGCATCCACAACAAACCCACTTTCTCGCAGACGGTGCTTCTCCAAAATCTATACGTGAACCCCCAAAACTCCGCCAAATCCGCGGAT
GGCTCCCATCTGGTGGCCAACGTCTCCGACGAGGAGATGCAAGAACACTACGACAATTTTTCGAGGACGTGTTCGTAGAGTGCGAGGACAAGTA
CGGGGAAATCGAGGAGATGAACGTGTGCGACAACCTAGGCGACCATCTGGTCGGCAATGTGTACATCAAATTCCGTAACGAGGCTGATGCGGAAA
AGGCGGCAAACGATTTGAACAACCGGTGGTTCGGTGGTCGACCGGTGTACTCGGAACTATCGCCGGTGACCGACTTCCGCGAGGCTTGCTGTCGG
CAGTACGAGATGGGCGAATGTACCCGCTCCGGCTTCTGCAACTTCATGCACTTGAAGCCCATCTCGCGTGAGCTGCGAAGGTACCTCTACTCCCG
CCGCCGTCGTGCCCGCTCCCGTTCCCGATCCCCTGGACGCCGTCGCGGCTCCCGCAGCAGGTCCCGATCCCCGGGTCGAAGAGGAGGCGGCAGAG
GCGACGGTGTCGGCGGAGGAAACTACTTGAACAACGAGCGGGACAACATGCGTGGCAATGATCGCGGAAACGATCGCGATCGCCGCAAAGGTGGT
GGCGGAGGAGGCGGTGGTGGTGGTGGACGGTATTAAATATTCTGGACATTTTTTCTGTACGGTGGCAATTGAGAGAGAAAGCAACGGACAAGCAG
TAACGCAAAGCATCGTGTATTTTAGTCTCTGCGTTGGTTTTCCACGTTTTTATATCACTTTTGAGTAAACGAGATGGAAGGAGGAGGAGGAAAAT
GACGATGGGGAGTTCCACCACCTATGTACAAACCCCCCGCGAAATATTTTACCGAGCGCCCATTAGAATTGTAATTTACTATACATACATTCATA
ATAATAAAATTGAGTAATATTATACTGGAAGCCATAGTAAGAAATGGGTCTAATTGTCAAAAAGTCCAGGCACTCAAAATAAAAGACTCCTCACA
GGTATGGATAACATCCAGAAGACACCACCCCTTGTTAGGCCTGCAGTCTTATTTCGCTTTGTAAGATTGAATCTTACCACGTTGTTTTAATTATA
TTTCCATGCGCAGATGGCTTCACCAACTGAAAACGATCAACAGCGTAAATGATGCTGTCAACTGTCTTAAGACGAAATCTTAAAATCTTCAAAAA
TGCGTACATTTGAACAACGAAATTCTTGTTTTCCCCGACTTAGTCTTAGATTTTAATAGGTGCATATTTAGGGGCATATTTGTGATCAAGCTATG
TCAGTTGGCGGGCTTCCATCGTGATTAGTCGTTCCACCCTGAGGAACACCTCTGAAAGCCTCGCCTTCATTTTGCACTGCTGGCTTCTCCGCTTG
AAGATTACTCTGTGCGCGATGCGTCGATGGAGGTACGGGCGTGTCAGAGGAGTTGCTAGACGCCTCCCTGGCTTTCAGTTGCTTGGTCATGTCTA
TTTGCTGCTGCAGCGTGTAGGTATTCTCGTGTTTGCGCCGTTGTTGCTGCTCAACGTCCCTCAGGACACCATCGTGCAGTCTCAGGCTGGAAGTT
AGAGATCGGAGGCTATAACTTTATTCCGGAGTATTTGGCTTACTTACCGGTCTGCCGATTGTTTATAGTGCACATAACCTATGATCGCTGTGGAA
ATGGAGACCGCCAGTCCCAAAGTCACTCGCGAAGCGGTCGACATGACTGGGCACCGGTCTGCCGCTGGAGATTTCCGCCTAAAATGCCTGCACTA
GGAATTTGGCTGTCGGGTTGTGTTGTTTTGAAGTCGGTTCGGGTTACGACATGACTTTAAATTTGAAAGAAAAACAACAGCACCACACAGCTGAC
AAGAGAGTGGCCAGTTTACGGAAGCAAAGTTTTCCCTATCCAGAGTTAGTGCGCGGGAAAATCAAATTAATTCCCTTC
(SEQ ID NO: 340)

Exon: 1001..1212
Exon: 1281..2308
Start ATG: 1169

Transcript No. : CT11994
GTGCAAAATACGACCAGACGCTGCTTTTTTCGGTTTCCGAAAATAATTGAAAATTATCACTAAATAAACAGGCGGCTAACATAATTGCAGTTTGA
CCGCGTTGCAGAGACAAGCGGGTAGATAAGTTACACATTTTGGCCACAGCAACACCACAGTAAAGCCGCCAGCATGGCCGAGTACTTGGCATCCA
TTTTTGGCACGGAAAAGGACAAGGTGAACTGTTCGTTCTACTTCAAGATCGGCGCCTGCCGCCACGGCGACCGGTGCTCTCGCATCCACAACAAA
CCCACTTTCTCGCAGACGGTGCTTCTCCAAAATCTATACGTGAACCCCCAAAACTCCGCCAAATCCGCGGATGGCTCCCATCTGGTGGCCAACGT CTCCGACGAGGAGATGCAAGAACACTACGACAATTTTTTCGAGGACGTGTTCGTAGAGTGCGAGGACAAGTACGGGGAAATCGAGGAGATGAACG
TGTGCGACAACCTAGGCGACCATCTGGTCGGCAATGTGTACATCAAATTCCGTAACGAGGCTGATGCGGAAAAGGCGGCAAACGATTTGAACAAC
CGGTGGTTCGGTGGTCGACCGGTGTACTCGGAACTATCGCCGGTGACCGACTTCCGCGAGGCTTGCTGTCGGCAGTACGAGATGGGCGAATGTAC
CCGCTCCGGCTTCTGCAACTTCATGCACTTGAAGCCCATCTCGCGTGAGCTGCGAAGGTACCTCTACTCCCGCCGCCGTCGTGCCCGCTCCCGTT
CCCGATCCCCTGGACGCCGTCGCGGCTCCCGCAGCAGGTCCCGATCCCCGGGTCGAAGAGGAGGCGGCAGAGGCGACGGTGTCGGCGGAGGAAAC
TACTTGAACAACGAGCGGGACAACATGCGTGGCAATGATCGCGGAAACGATCGCGATCGCCGCAAAGGTGGTGGCGGAGGAGGCGGTGGTGGTGG
TGGACGGTATTAAATATTCTGGACATTTTTTCTGTACGGTGGCAATTGAGAGAGAAAGCAACGGACAAGCAGTAACGCAAAGCATCGTGTATTTT
AGTCTCTGCGTTGGTTTTCCACGTTTTTATATCACTTTTGAGTAAACGAGATGGAAGGAGGAGGAGGAAAATGACGATGGGGAGTTCCACCACCT
ATGTACAAACCCCCCGCGAAATATTTTACCGAGCGCCCATTAGAATTGTAATTTACTATACATACATTCATAATAATAAAATTGAGTAATATTAT
ACTGG
(SEQ ID NO: 341)

Start ATG: 169

MAEYLASIFGTEKDKVNCSFYFKIGACRHGDRCSRIHNKPTFSQTVLLQNLYVNPQNSAKSADGSHLVANVSDEEMQEHYDNFFEDVFVECEDKY
GEIEEMNVCDNLGDHLVGNVYIKFRNEADAEKAANDLNNRWFGGRPVYSELSPVTDFREACCRQYEMGECTRSGFCNFMHLKPISRELRRYLYSR
RRRARSRSRSPGRRRGSRSRSRSPGRRGGGRGDGVGGGNYLNNERDNMRGNDRGNDRDRRKGGGGGGGGGGRY*
(SEQ ID NO: 342)

Name: RRM-type RNA binding protein
Classification: RNA_binding
Gene Symbol: U2af38
FlyBase ID: FBgn0017457

Celera Sequence No. : 142000013384832
TCGATCTTCTCGCATAACGAGCTGATTAGCATTGTAATGCTCTACCATAAGTTTGTGCTGGTCAATGGGCCGAGAGCAAAGTACATGACCATTCA
GCAACTCTCTGCGCTGATGGAGCTCTTGTTTGAGATCGTGGATCGCGATCTCATTGCGACCATTGTGTATAGAATAGCCCATACACCAGGTTCCA
GGCCTCCTGACTTCTTTTCCGACAAGCATATACACTTGGAGTCCTTTGTGCGGCTTTTCACCGTATACTTCACCAAAGATCTTCAGCTGAAAATG
GAATTCGCATTCTCGGTGGGCAATTCATAGTATTCATATGAAATTAGCCTAGACCATTTGCTTACATTGCAGGTCTACGATAAAAGCGATTCCAA
GCAGTTGAATGGCGAGCAAGTTGGGTTCTTCGTCGGCAAGTTCTTTGAGAGCGAGGATGAAGACGAATCCATTGAGCTGCGCTTGGTGAGGCACC
ATCCCCTACACTTGTTCCATTGAAACACTGACACATTTCGCATTCCTTCAGGACATGAAGGAGATGCTGTTCCTCAAATTCGACTTGGACAAGGA
TACCAACATTGGGGTTGATGAGTACTACGAGGTGGTCCGCCGACAGCCCATGCTGCTGGAGTGCTTTGGTCGCGTGTTTCCCCCGAATCCCCAGA
TGGAGGTCCTTGCGCTGTGCGCCAATGTAATGTCTTGGTTTGACGATTCGCCCAATCCCAGGATTATGATAAAACCAGACGGCGGCAAGGCCAGC
TAGCTAACAGGACGTCCAGGAACGCATTTTTATCTAACCAGATACTTAAATTGTGACACGTCTAGAAATTGAAAAGTGCAAATAATTTAGTGCAT
CATAAAGGTTTACACTTTTATTAACTAGTTTTGTACGTTACTTTTGAATATTGGTTCTGAACGGTAAACTCGCTTCATTGAGGCTGCTTCGATAA
CGATACCGATTAGTCAGTGTGTCCGGATTGTCTCATCCCTGCTGCACGCGACCCACCATTTTAGTAACACCGAAGAAACGGTAGCGAAATGGCCA
CGGAGGAGCACCAGCGCCTGGCCAGCATCGTGAAGAGCTGCCACGAAAGCCTGCGCCAGTTGACTAAGGAGTATGGCGCCACAGCGGCCTGGCAG
GAGCACACGAGTCCCAGGAACGCCAAGCAACTGGCGGAGTACGCCAAGGCGATGAAGCAACTGGCGGCCATATGGGAGACCAACGATGGGAAGGT
GGAGCTGCAGGCACGCAGCCGCATCAAGTGGGCCATCGACTACATCACCAAGTACTTCTTTACCGAGGGCATATATTTGCAGAAGCGCCAGCGGG
AGCAGCGACTCCTGGAATCCTACAGAGCCGAGGGAAAACTGGGCGAGGTGCAGTGCAGGCTGATGGAGGAGCCGCCGGACAGGCTGCACGTCCTG
GATGTGGGCAGCTGCTTCAATCCCTTTTCCAGTGCTCCGCACTTGGAGGTAACCGCCCTGGACTTGTGTCCCGCCACCGAAGATGTGCTGCAGGC
GGATTTCCTCAAAGTGGAGGTGGTACCCGGAATACGAGAACCTGAGCTGGAGGAGGGCAGCGTAAGAAGGCTACCAGCAAGCCACTACGAGTGCG
TCATTTTCAGTTTGCTACTGGAATACATGCCCAGCGCCGAGCAGAGACTACAGTGCTGCCTTCAGGCCTACGACCTGCTGCTGCCCGAGGGCATC
CTTGTGCTCATCACACCGGACTCCCAACATGTTGGCAAAAACGCCCACCTCATGAAAAACTGGCGCTACTCCCTGGCCAGGATTGGACTGCTACG
GGTACGCTTCGAGAAGTTGCCGCACATATCGTGCATGGTGTTCCGCAAGGCCATCAGCCGGGAGCTCTCACAGCACTGGGCGAGCATTCACCGGG
AGGAGGGGATGTGCGAGGAAATTCGGATACCGCAGGACGATAGCTAGATAAGATTCAGCCCCCATAAATCGATGTAAATATGTCCACGTCTACTT
ATTTATGGCTTAACTTATCTGTGTTAAGTGCGAGTTAATAATAATGGTTGACGATTTATCTACTATCTATGGATGTCGTAAATGGACAAATGCTA
TTGCTTCTGTTCCGACTGTGGGAACAGCGCGCCGCTGGTCTGGCGCTTCTTCATCGCTGTGGTGGCGCCCTGCGAAATCTTCATGATGTTCGGCG
GGAGCGGTTTCTTGCGATCCGCCTCCCACTCGGCTCGGTGGAGCCGCTGACGGTGCTTGTACATGTTGGCGTTGGAAAAGAACGTCATGGGGCAG
TTAGGACAGGTGTACAGCACCTCTCCGGTGTGCGTTGATGTGTGCTCCTGTAAATTAGGTGTCGAATACTTAGATTTCTCTGTAAGTGAGCCCCA
CACTTACCCTCAGATCCTGTGGACGCTTAAATGCCTTTTCGCACATCCCGCACTTGAACTTTCGCTCACAGAGGTGGTTGTGGTAGATGTGGCGC
TTCAGGGCTCGGGAATTGGTGGATGTCTTGTTGCAGATATGACAGCGGTGCTCGTCGCCCGGCGGCTCGTGTACCGTTTTCATGTGCTGCTTTAG
TCCGGACAAGTGGCGCAGCCAGGTGCCGCAGATCTCGCACTGCACGGGATCGGGTTTTGGACGCGGTTTCTCGGAATGTTCAAGCTCGTGATGCT
TTTTGAGATTCGTTTGTGAACGTAGCGTCTTGCCACACTTATCGCAGATGATGGCCGCTTCCGGGTCGTGCATGTAACGCAAGTGCTCTTTCAGT
TTGCGTTCCGTAGGAATCCTGAAAGCATTAAGGGATTACTTGGGGGGTTGCTCATATGCCTCATACCTGATGGACAATTACTTCTTGTTGCACTC
CGGACAAGAGTATTTGAACTCGGATTTCGGGACATGCTTGGAAACGTCATGATACTCCATGGCCGCCTTGGTTGTGAAGCTCTTGGGGCACTTCT
CG
(SEQ ID NO: 343)

Exon: 1001..1947
Start ATG: 1039

Transcript No. : CT12002
ACCCACCATTTTAGTAACACCGAAGAAACGGTAGCGAAATGGCCACGGAGGAGCACCAGCGCCTGGCCAGCATCGTGAAGAGCTGCCACGAAAGC
CTGCGCCAGTTGACTAAGGAGTATGGCGCCACAGCGGCCTGGCAGGAGCACACGAGTCCCAGGAACGCCAAGCAACTGGCGGAGTACGCCAAGGC
GATGAAGCAACTGGCGGCCATATGGGAGACCAACGATGGGAAGGTGGAGCTGCAGGCACGCAGCCGCATCAAGTGGGCCATCGACTACATCACCA
AGTACTTCTTTACCGAGGGCATATATTTGCAGAAGCGCCAGCGGGAGCAGCGACTCCTGGAATCCTACAGAGCCGAGGGAAAACTGGGCGAGGTG
CAGTGCAGGCTGATGGAGGAGCCGCCGGACAGGCTGCACGTCCTGGATGTGGGCAGCTGCTTCAATCCCTTTTCCAGTGCTCCGCACTTGGAGGT
AACCGCCCTGGACTTGTGTCCCGCCACCGAAGATGTGCTGCAGGCGGATTTCCTCAAAGTGGAGGTGGTACCCGGAATACGAGAACCTGAGCTGG
AGGAGGGCAGCGTAAGAAGGCTACCAGCAAGCCACTACGAGTGCGTCATTTTCAGTTTGCTACTGGAATACATGCCCAGCGCCGAGCAGAGACTA CAGTGCTGCCTTCAGGCCTACGACCTGCTGCTGCCCGAGGGCATCCTTGTGCTCATCACACCGGACTCCCAACATGTTGGCAAAAACGCCCACCT
CATGAAAAACTGGCGCTACTCCCTGGCCAGGATTGGACTGCTACGGGTACGCTTCGAGAAGTTGCCGCACATATCGTGCATGGTGTTCCGCAAGG
CCATCAGCCGGGAGCTCTCACAGCACTGGGCGAGCATTCACCGGGAGGAGGGGATGTGCGAGGAAATTCGGATACCGCAGGACGATAGCTAG
(SEQ ID NO: 344)

Start ATG: 39

MATEEHQRLASIVKSCHESLRQLTKEYGATAAWQEHTSPRNAKQLAEYAKAMKQLAAIWETNDGKVELQARSRIKWAIDYITKYFFTEGIYLQKR
QREQRLLESYRAEGKLGEVQCRLMEEPPDRLHVLDVGSCFNPFSSAPHLEVTALDLCPATEDVLQADFLKVEVVPGIREPELEEGSVRRLPASHY
ECVIFSLLLEYMPSAEQRLQCCLQAYDLLLPEGILVLITPDSQHVGKNAHLMKNWRYSLARIGLLRVRFEKLPHISCMVFRKAISRELSQHWASI
HREEGMCEEIRIPQDDS*
(SEQ ID NO: 345)

Celera Sequence No. : 142000013384831
CTTTCGGGGGAGAGGTGGTGAAAATCCAGTGGGTTTATCCTCACACAAATATCCTCACATTAATGGCACATGCAATTTTCCCCTACATTTGGCAC
CTAGCACCCAGCTTTCACCCGCAGTACCGTTATACCGTTCCGTTTTACCGTTTTACCGCCGCGTTGTGTTCACAGGACCGCACAAGCTCAGACTG
AAGCGACGAAGTGAAGCTGCGTGAGCGAGCGGCTGGTTGCTTTTACGCTTTAATACTAAAAAAAAAGGAAAACGGTCCTTTTTGCTTTCGTTCGC
TCGCGCGCACAGCTTCCTTTGCTTCCTCTTTGTCGTCGGAGTGTAGACTTTCTCGCCGCTCTCTTTGCGCAACAATGAAACTCTTGAAAGTCTCC
AAAATGAACAGACCGTTTTAATATCTTGGCCATATTTCGAACGCATTCCGATAAACATTTACTCCAAAGTCAAGTATGTGAATCTGTTAAGGTAA
ATAGGGATGTAATCTGCCCATCCAATTACAATAGCATGCTTTTAGGCTGCTTATAAATTATCCCAGAGTTCTTCGAACCATATTTATGGCGGCGT
CCACATATAAATATAGTTAAGTTATCGCAACAGTCTTCAACGATCTTTGGTATTATCAGATGACCTGATTCCCTTGGTATTTTAAAATAAGTGTG
AATGAATCACATGAATGAATTCAAAATTTTCTAATAAGATTTCTACAAGTTTAAGAACATCACCAACCATCGTATGTTTAATGTCACCACCAAGG
GTGCCCGTATTACGACATAACGTGACCACATATTTTAGGGAATTTTTAAAAAATAAGCATAGAAATTATCTCTTATAACTAAAGTCATGTCCACT
TTGCTTTGAGTATTAATTTAATTTGAGAAATTATATTGCGTCGCGTAAGCTGCCACCACTGAGGGTGACCGTACTTGCGACCGGTGTGCCCGCAC
CGCGCAATCACCAGCACTTCGGCCGTTTCCCAGCACTGCCTCACCGAACGTCTGGCCAGCGACCATCTTGTGAAAAGTACTACGAGTGTGGAGAG
GAGTTGGCTTAGGAATTGTACAATTACTTCTGCGGCGAACAGTTAAAAAGCATTAAAAATGTCGATTTTTTCCGCCCGCCTGGCGTCCTCGGTCG
CCCGTAACCTGCCCAAGGCTGCCAACCAGGTACCGCACCGAATTCCAGAAATTAAATCGCCCGACGAAGAGTTGGCGAAAAAGTGTAATACATAA
CCGAATCGATGGGGTACTTTGCAGAAAATTAGTGCATCCGGGTGGTTCAAAGATCGATCGAACTGTGGATAAAGACTTTCTGGATGCGTAGCAAG
TATTCGGGTGGGATTTTGTACCATTTTCCAACAAGAATTTAGTGTTACGCAATGCGGCGAATTGCAAGGCGGCCGCTGAAATTGTGGGTTACATA
ATCAGTGCCAACCGAGAATTTGCTAAGCAAAACAGAGTTTTTGGTTATTTTTCAGTAAAAGTGTGCGAAGAACGCTGCAATGTCTTTGTTTTTG
TCCTCACATTACATAATTGTGATGTGGGTGAGATGCGGTGCCCGAAAAGTTTGAGGTTAGGTGCGGCTGTCAAGCAAGTGGTGAAGGTGGAAAGA
ATACAAAGTGGGGAAGTGCCGACATCCAGATACCCTGTAATCAGTTTTTTTTTTTATTAACTAGCTAGAAAGTACTGGAGAGAAGTTATTGAACG
ATCGTACCCTGCGGTTATCCAACGACACGGACCTACACCTTACATAATCTCGCATAATCATATCGATTAACCTACTCTCTTACAGGTCGCCTGCA
AAGCCGCTTATCCCGCCGCCAGTCTTGCTGCCCGCAAGCTCCATGTGGCCAGCACGCAGCGTAGCGCTGAGATCTCCAACATCCTGGAGGAGCGC
ATCCTGGGCGTCGCCCCCAAGGCTGATCTGGAGGAAACCGGCCGTGTGCTGAGCATCGGTGACGGTATCGCCCGTGTCTACGGTCTGAACAACAT
CCAGGCCGATGAGATGGTGGAGTTCTCCTCCGGACTGAAGGGCATGGCCCTTAACTTGGAGCCCGACAACGTCGGTGTTGTGGTCTTCGGTAACG
ATAAGCTGATCAAGCAGGGCGATATCGTCAAGCGTACCGGTGCCATCGTGGATGTGCCCGTCGGTGATGAGCTGCTGGGTCGCGTCGTCGATGCC
CTGGGAAATGCCATCGACGGCAAGGGTGCCATCAACACCAAGGACCGTTTCCGTGTGGGAATCAAGGCCCCCGGCATCATCCCCCGTGTGTCCGT
GCGCGAGCCCATGCAGACCGGTATCAAGGCCGTCGACTCCCTGGTGCCCATCGGTCGTGGTCAGCGTGAGCTGATCATTGGCGATCGTCAGACTG
GGTAAGATTCTGGAGATAACCAAACCATGACACACCATTTCTCAATTGCTAGCAAGCAAAATTTAACCAAACAATTTTGTATTTAATCTGCAGTA
AGACCGCTCTGGCCATCGACACCATCATCAACCAGAAGCGCTTCAACGAGGCCCAGGACGAGTCCAAGAAGCTGTACTGCATCTACGTCGCCATT
GGCCAGAAGCGTTCCACCGTCGCCCAGATCGTGAAGCGTCTGACCGACTCCGGCGCCATGGGCTACTCCGTGATCGTGTCGGCCACCGCCTCCGA
CGCTGCTCCTCTGCAGTACTTGGCCCCCTACTCCGGATGCGCCATGGGAGAGTACTTCCGCGACAAGGGCAAGCACGCCCTGATCATCTACGATG
ATTTGTCCAAGCAGGCTGTGGCCTACCGTCAGATGTCCCTGTTGCTGCGTCGTCCCCCAGGTCGTGAGGCCTACCCCGGTGATGTGTTCTACCTG
CATTCGCGTCTGCTGGAGCGTGCCGCCAAGATGTCCCCCGCCATGGGAGGCGGTTCCCTGACTGCTCTGCCCGTGATCGAGACCCAGGCTGGCGA
TGTGTCCGCCTACATTCCAACCAACGTCATCTCGATTACCGACGGACAGATCTTCTTGGAGACCGAGTTGTTCTACAAGGGTATCCGCCCTGCCA
TTAACGTCGGTCTGTCCGTGTCCCGTGTGGGTTCCGCTGCCCAGACCAAGGCCATGAAGCAGGTGGCCGGTTCCATGAAGCTGGAGTTGGCCCAG
TACCGTGAGGTCGCTGCCTTCGCCCAGTTCGGTTCCGATCTGGATGCCGCCACCCAGCAGCTGCTGAACCGTGGTGTGCGCCTCACTGAGCTGCT
CAAGCAGGGTCAGTACGTGCCCATGGCCATTGAGGATCAGGTGTGTATGCCAGGACTTACCTAGCAACTAACTTATATCCGTAGTGACAACGCGG
ATATCGCGATTCCCGTGTAAAACCCAACCTCTAATCACCCAACATCAAATCTTCCAGGTCGCCGTTATCTACTGCGGTGTGCGCGGTCATCTGGA
CAAGATGGATCCCGCCAAGATCACCAAGTTCGAGAAGGAGTTCTTGCAGCACATCAAGACCTCCGAGCAGGCTCTGCTCGACACCATCGCCAAGG
ACGGTGCTATCTCGGAGGCGTCCGATGCCAAGCTGAAGGACATTGTTGCCAAGTTCATGTCCACCTTCCAGGGTTAAGCATCAGCAGCAAACGAA
GAATAGGAGTAGCGGTGCGTGCAATTAACATCATAGATGGCTCGAATAATGCTGCCATCCCTGCGCGCCATCAACAACAACAAATAACAACCTAC
AACTTAAGATAAACAGAAATTATAAAACAAAAACAAGAGAAAACTCCTTTGCACATTCATGTTTTCCTGCGCATCCTGACTGGATCGATCGCCTT
CAATCCGTGGTTCGGTGCCATTATGCCGCAAAATCTTGGGAGAGAGAGAGCCGGCCCTGGCTACGGAGTGGACGGCGAGCCCCAGCCGGATGCAC
TTTCGAGTTTCAGCGAAAAATCCTTGCGGTTCCTCCAACCTCCAAAACGATAGATAATCCCCCGTTGTTCTTCTACCTAAAATATGTAATCAATA
TTTGAAATATTGTAATCGAGAATAGTCGAAATAATGTCTGAGGATGATTGTGAAACGATGATGAATTAAAACGATACTAAATTATACTCTAAATG
AGTCCTGCTCACACTTCTTTGCTGGGATTATTTCCTTTTGCTTTCTTTTTTAATTCCCGATTTTGGTAATATAATTTAAAGAATTCTTGACAAAT
TGTTATGTTCTAAGCCATTTGGAGATGTCTTGCCAGGAATCTTTGAGCATATTTTGTTAATAGGGGTTTTAAGCTTGGTTTCTTGAGGTTCTGTT
GCCGAAATGGATTTCCCTAACTAATCCTGGTCCTTTCGGCTCAGCTGATCCGCCAGACGACGAGCAGATGTCCTTTTGCGTAACCGTAACCTCTT
GACCCCCGTGCGAATTAGCCACCCCTTGAACTACCTGAACGACCGCCTGTCTGCTCCAAGGCGCAGGATTCAGAAAGGAACTCGAACCCGGTGGT
TCGGAGTGGTTCATGCTGTGCATATTTCGGTAACAGCAAGCCAGAAGCGAGAGCAAGAAGTTTCCAAAAAGAGAAGAAGAAACAGAGGGTACCAA
GACCCAAAAACTGTAAGCCCGATTTATACGGCATGGAGTTTTTATGACGCCGATTGCCACTGGCAGCCAACATAAAATATGCCAAAAGGGAGGAG
CAGCGGAGGTGCCGAGAAAAATGACTTTCTTTTTACTACATTTGTTTGACCGTAAACAAGAATTAATGAGAGTCATAAAACCGTCAAACTTAAAT
TTCGAACAGGCGCACAGCAAAGTCAGCAGGCCGTGTACAGTGGGCGCTCTATAAGGCGAACAAATGTTGAAACTCAAACTTTTTACCTAATGCAT
TAATTGCTACTAACGAAAACTATTTGAAATATTCGTTCGATAATTCGCTTATATGTTTCTTAAGAACTTAACTATAAGGTTGCCTTTATTTGGCT
TTGTATCGAGTAACTACTGTACATGAGAAAAGTGAGATAGACACCCACACACACACACGCACAACCATGTGCGAGCAATGTGCTCGGCAATTACC
GTTGCCCATGGAACACGGTACCAAAAAAAGGGAGAGAAAAGCGTTAAA
(SEQ ID NO: 346)

FIGURE SHEET 189

Exon: 1001..1169
Exon: 1796..2376
Exon: 2469..3270
Exon: 3383..4083
Start ATG: 1104

Transcript No. : CT12071
TCTGGCCAGCGACCATCTTGTGAAAAGTACTACGAGTGTGGAGAGGAGTTGGCTTAGGAATTGTACAATTACTTCTGCGGCGAACAGTTAAAAAG
CATTAAAAATGTCGATTTTTCCGCCCGCCTGGCGTCCTCGGTCGCCCGTAACCTGCCCAAGGCTGCCAACCAGGTCGCCTGCAAAGCCGCTTAT
CCCGCCGCCAGTCTTGCTGCCCGCAAGCTCCATGTGGCCAGCACGCAGCGTAGCGCTGAGATCTCCAACATCCTGGAGGAGCGCATCCTGGGCGT
CGCCCCCAAGGCTGATCTGGAGGAAACCGGCCGTGTGCTGAGCATCGGTGACGGTATCGCCCGTGTCTACGGTCTGAACAACATCCAGGCCGATG
AGATGGTGGAGTTCTCCTCCGGACTGAAGGGCATGGCCCTTAACTTGGAGCCCGACAACGTCGGTGTTGTGGTCTTCGGTAACGATAAGCTGATC
AAGCAGGGCGATATCGTCAAGCGTACCGGTGCCATCGTGGATGTGCCCGTCGGTGATGAGCTGCTGGGTCGCGTCGTCGATGCCCTGGGAAATGC
CATCGACGGCAAGGGTGCCATCAACACCAAGGACCGTTTCCGTGTGGGAATCAAGGCCCCCGGCATCATCCCCCGTGTGTCCGTGCGCGAGCCCA
TGCAGACCGGTATCAAGGCCGTCGACTCCCTGGTGCCCATCGGTCGTGGTCAGCGTGAGCTGATCATTGGCGATCGTCAGACTGGTAAGACCGCT
CTGGCCATCGACACCATCATCAACCAGAAGCGCTTCAACGAGGCCCAGGACGAGTCCAAGAAGCTGTACTGCATCTACGTCGCCATTGGCCAGAA
GCGTTCCACCGTCGCCCAGATCGTGAAGCGTCTGACCGACTCCGGCGCCATGGGCTACTCCGTGATCGTGTCGGCCACCGCCTCCGACGCTGCTC
CTCTGCAGTACTTGGCCCCCTACTCCGGATGCGCCATGGGAGAGTACTTCCGCGACAAGGGCAAGCACGCCCTGATCATCTACGATGATTTGTCC
AAGCAGGCTGTGGCCTACCGTCAGATGTCCCTGTTGCTGCGTCGTCCCCCAGGTCGTGAGGCCTACCCCGGTGATGTGTTCTACCTGCATTCGCG
TCTGCTGGAGCGTGCCGCCAAGATGTCCCCCGCCATGGGAGGCGGTTCCCTGACTGCTCTGCCCGTGATCGAGACCCAGGCTGGCGATGTGTCCG
CCTACATTCCAACCAACGTCATCTCGATTACCGACGGACAGATCTTCTTGGAGACCGAGTTGTTCTACAAGGGTATCCGCCCTGCCATTAACGTC
GGTCTGTCCGTGTCCCGTGTGGGTTCCGCTGCCCAGACCAAGGCCATGAAGCAGGTGGCCGGTTCCATGAAGCTGGAGTTGGCCCAGTACCGTGA
GGTCGCTGCCTTCGCCCAGTTCGGTTCCGATCTGGATGCCGCCACCCAGCAGCTGCTGAACCGTGGTGTGCGCCTCACTGAGCTGCTCAAGCAGG
GTCAGTACGTGCCCATGGCCATTGAGGATCAGGTCGCCGTTATCTACTGCGGTGTGCGCGGTCATCTGGACAAGATGGATCCCGCCAAGATCACC
AAGTTCGAGAAGGAGTTCTTGCAGCACATCAAGACCTCCGAGCAGGCTCTGCTCGACACCATCGCCAAGGACGGTGCTATCTCGGAGGCGTCCGA
TGCCAAGCTGAAGGACATTGTTGCCAAGTTCATGTCCACCTTCCAGGGTTAAGCATCAGCAGCAAACGAAGAATAGGAGTAGCGGTGCGTGCAAT
TAACATCATAGATGGCTCGAATAATGCTGCCATCCCTGCGCGCCATCAACAACAACAAATAACAACCTACAACTTAAGATAAACAGAAATTATAA
AACAAAAACAAGAGAAAACTCCTTTGCACATTCATGTTTTCCTGCGCATCCTGACTGGATCGATCGCCTTCAATCCGTGGTTCGGTGCCATTATG
CCGCAAAATCTTGGGAGAGAGAGAGCCGGCCCTGGCTACGGAGTGGACGGCGAGCCCCAGCCGGATGCACTTTCGAGTTTCAGCGAAAAATCCTT
GCGGTTCCTCCAACCTCCAAAACGATAGATAATCCCCCGTTGTTCTTCTACCTAAAATATGTAATCAATATTTGAAATATTGTAATCGAGAATAG
TCGAAATAATGTCTGAGGATGATTGTGAAACGATGATGAATTAAAACGATACTAAATTATACTCTAAA
(SEQ ID NO: 347)

Start ATG: 104

MSIFSARLASSVARNLPKAANQVACKAAYPAASLAARKLHVASTQRSAEISNILEERILGVAPKADLEETGRVLSIGDGIARVYGLNNIQADEMV
EFSSGLKGMALNLEPDNVGVVVFGNDKLIKQGDIVKRTGAIVDVPVGDELLGRVVDALGNAIDGKGAINTKDRFRVGIKAPGIIPRVSVREPMQT
GIKAVDSLVPIGRGQRELIIGDRQTGKTALAIDTIINQKRFNEAQDESKKLYCIYVAIGQKRSTVAQIVKRLTDSGAMGYSVIVSATASDAAPLQ
YLAPYSGCAMGEYFRDKGKHALIIYDDLSKQAVAYRQMSLLLRRPPGREAYPGDVFYLHSRLLERAAKMSPAMGGGSLTALPVIETQAGDVSAYI
PTNVISITDGQIFLETELFYKGIRPAINVGLSVSRVGSAAQTKAMKQVAGSMKLELAQYREVAAFAQFGSDLDAATQQLLNRGVRLTELLKQGQY
VPMAIEDQVAVIYCGVRGHLDKMDPAKITKFEKEFLQHIKTSEQALLDTIAKDGAISEASDAKLKDIVAKFMSTFQG*
(SEQ ID NO: 348)

Classification: enzyme
Gene Symbol: blw
FlyBase ID: FBgn0011211

Celera Sequence No. : 142000013384093
ACTTCTCGAGTAATACTTAGTGATAACTGCAACTTTATTTAACATGCTAAGCGCCAAAGCTTTATGAGTACATAATACCCATAGCTCGATAAAGC
AATCATAGAAGACTTACCACAGTCAAGCTTATAATCTATAGGACCCCATCGTTGATGGGTAAATGCTTTTTATGTACAATCGTAGTTCCCCTAAA
GACATGCCTTACAAATGCTAAGGGTTGCGTAGAGCCCTACTAGGTACGTGTTAGTAGTGTTAAGCGTGTGATTTAGTGTTAATATCACAAGGGTG
TGTGGGGGAGTGTGGCCTGATTGAGTCACCGGGATGATTCAGTTAGGCACTTTCTCCGAGACGGTATCAAGACCTTTCACCGTGTTAGTAGCTGA
ATCGCCTACAACTAAGGTTACATCACTGTGAAAAATCGAAAGAAGAGAGCACAGCAAAATACGGGTTGAGGGTTTAGTTTTAGTTCAGAGATGAT
AACCAAATGTAGATTAGTAAATAGAAAGTAAGTACAGATGAGATAAGATTAGAATCATTAGGAAGTTAGGCCGATTTGGTTGAAAGCAGAGCGGG
AAAAAACTTAATCACAAGCAATGGGTTAGCAGAGAATGCTTTTAAGGAAGAAGATGCAAATCGAGAGAGTTTGTGCATTCGAGTGTGTTCTGGAT
GGTTATATGGTTGAATGGTTGGAATCAAAAATCGGGAACATACCTGGCGTACGTCGAGTTGGCGTTCTTTATCGAAAAGCTGTTCTGGCTTGGCA
ACACAAAACGCTGCACCCACTGTAAACAGAGAATACCTTGAGTACCAGTTGATGAAGTAGGCATAAGCCCTCAAAGCCCCCAAGAACCATATGTG
GTCAGTCACGTAATTTGATAAAGTCAGTCCGTTCAGTGCGGTATCTGTGATGCTTTAAAATGTGTCAAAAAGTTCGCCTAATTTGTGATTCTCTA
AGCCCATTTGATAAGTGACCCAACTAGTTGCGGCCAAGTACTTACCCGGCTGTTCATCAAACGCTGATTGCCCATGCAGGCAGCCATGTGTATCA
CAAGGTAGAGGTTGAACAGTATATACAAAATGGCAAAAATACCTGCAATTGGCAAAAGGAAAAATACATTAGATTCGGTTTAAATTGTGGCAATT
GACTACTCACAGACTAGTGCCAGCAAGCCGCCTTTAATTTCCATATTCTCTACTTGCACCACCACAAAGTACAAATTAACGCCAATCACTACAAT
GGTGAGCAGTATGGATACGATTTTGTTGCCCCTGTGAATACAAAAATTTAAAGAATGCACGATAATCAATTAAAAGTGTCTGTATCACTTACAGT
CCATTAACAAACTCGCCCATTATGGCGGCGCACGAGGTGAAGGCGATGGTGGGTATGGCAGCGAATGGCAGCTGGAGCGACATCACCGCATTCAG
GATATCGTTCATGCTAGTCAAATCTTCCATCTTGCTGAACATGGCCAGGCAGAAGGTGGGAATAATGGCAATGCAGCGCGTGACCAGCACGCGAC
ACCAGCGCGGCCACTGCAGATTCAAGAAGCCTTCCATTGAGAACTGACCGGCATAGGTGCCCGTCATGGTGGAACTCTGGCCAGCAGCTAGAATG
CCCACACCCCAAATGTACATGGCGACAGCTCCAAATGTGCAGCCAAGGAAAAGTCCGCCCTTGTATAGATCTGCATCGATGATCGCGGTTCCATT
TACATTGTCCACAAAAGACATTTTGGCATCTTCGTACATCGACTTGTCTTTACACACTTCAACCTATTGGCCCACAAAGAGTTAGCAATCATTTT
ACACATAAATTCAAAAGTCTACTTACCACATCATTATTAGTTTTGCCATACATGCCATGGGCAAACACAGCCACCACAAACAGGTTAATGATGAA
GGACACAAACAAGGCTACCGACGCCTCGATGAAGAAGTAAAAATTCGCCTCACTAACTTTCTTTGTCTGGCGACGGTCTATATCGCGGGACTGTT

FIGURE SHEET 190

AACAGAAAATTGTTATGTATTGGTATCTAATTACGAAGTCACAAAAAGCTAGTTGTGCTATACCTTAACCAAGGCGGAATGCAGGTAGAGATTGT
GCGGCATAATAACAGCACCCACGACACCCACGGCCTGCAGCAACACATTCGAATTGCAGTTAGAGCACCAGGGCACAAACATTCCCTCGAGAACT
TCTCCTTGATTAGGGGCTGATACAATGTACTGAAAGATATGAAAAATAAATTAATTATGACTTAAAACCATTTAAAAAATGATTATGGGGAGAAA
ACAAATTGTTCCTAGCTTATATTGAGATTTGGTTAGAAATAACAAAATACTTGTTACTCGTAGAAAAATCCCCTCGAGGCACCCCCACTTTTTTC
CATTGTAATTATCTCCAAAAACCACCATCGGTAATTGTACAATTCTGCATTGTATAATCTAATTGATAAGACTGGCATTACACATCCCATCTGGA
ATTGTTAGTCATGTCCGGCAGCATCATGTGCCTGGCAAACAAAAGATGAAGTATCCAGCACCCACGCTCAGAACCCCATTTAGTGTGCGAGTGAA
GCTTATCTAATCATCTCCGTCTGGGGCAGAAAGCTCAAGTACAATTGTTTATAATCTGGCCCGTTAACATGATGCGGTCGTAAACTTAAGAGTAA
GAATATGGGGCTAGTTAACGGGCTAACTTCATCCAGAAATCGACAAGTCAAATGTAAATTTACTACTAGCGATCATTAAAATAAACCTAAACAGG
CATCTCACAAATTATTTGCCATTGCGGTCGTTGCAATTGTTTAAACAATTCGTATTTGCACTCACGTCTGGTAATTTATTCTCTTGACTACTTTA
TTGTCATTTGGCAAGGGGATTTTTTGCTGATTTTGGCGATTACTTTTTATAGTTAAGTTATTTTTTTCAACTTTGCATTTTAAACTTACCTCATA
GCCGAATGAGACAGCCATAATGGTGATGAGGGTGCCGAATAGGAACTCCAGCTTGCGTAGACCGTACTTGTCCAGAAACAGGAACGTGAACGTGT
CAACAATGGTGATCAACACTCCGCCCCACAAAGGCACTCTACAAAATGGGGAAAGCACCGCATGCATGAGTACTGGGTACTGCGATAATCCGCTC
ATTAGATTTGCTTACACTTTGTTGGACAGCAGGTATATGGCAATGGCCGTGCCAATGACCTCCTGCATGTCGGATCCAATAATGGCTATCTCTAT
CATTATCCACAGTATCCAACGTGGCAGACGCTTGTACTGTCTGTAGCACATCTCGGCCAGATGCAGGCCTGTAACCACGCCCAGTCTGCCAGGAA
GATAATAAACGCTTATATCATCATCTTTTTTGCAAGGTGTGGAGACCCAATTACCTTGCAGCCAAGCGTTGCATGAGCAGACCTAGGACTGTGGC
CCACAGCAAGACCCACAAGATCTTGTACTTGGCCGCCGCACCAGACTGCATATCGGATTCGATGTTGCCGGGGTCCAGATACGCAATGGACATAA
GAAAACCGGGTCCCGTGAAGGCCCACAGCTTGCGAAAGCTGAAACCCACCTGCAGATCACCAGATATTAGATAAAGTTTGAGTAGCATTGCTATT
CAAGCGGGTCTTACGTTTGTGCTATCATCGTCGGGTATGAGGACCTTCTCGTCGCTAAAGTAGGCCTGCTTGGCGGCGGGTTTCAGGTAGGTCGT
CTCGTTGAGTATCTGCTGGTGGTGCAGCTGGTTGCTCCGCTGACTTCCTCCGCCGGATGCGCCAGACGATCCGCCCGGTCCATCTCCACCGGCAC
CCGGCTCGTGGTAGGCCTCATTCGAAGACATGCTGCACAGAAGAGGCGAGGTTAGACTGGACCTAATTCGAGTTTCCACATGCTGCTATATTCCC
GTCCACTGCCCATTGTCGACTACTCTAATTTGTATTTTCTATTTGATTGTTTCACCTGGCATCAGCTTATGATTCCCACCATTTTCATTTAATTG
AGCATCTGTGTGTGATTCTAGCTCAATTAGCATTATCATATTGCACACAACAAACAAAATAATTTTGCGCTATAATTAAGTTTTTTGCACCATAT
AGTTTTATTTGGGGATTTCACCATAATCAAGAGCAAAGTCACAGTAACACGTTTTATTTTTTCCGAAACGCGCGTGGCAAAATATGAAAACAATA
AATAGTTCGAGAGGCATTAGCTCGGGGGTAACTGATAACGCGTCCATAATATTACTGAAATTTGCTTATATTATGCGGGTATATAAGGAAATAAA
ACGAGCTCAGTGATTCATGAAGTCCAGTAATTGAAATGCCTCTGCCCAATTTACCCAGAGAACTTGCAGATATTTCGCATTTGCAGTCGTATAGA
TATGGATGGTCGAAAACAAGACTACTTGAACATAAACACGAGTCCATTGACCCGTGTATCGATGTGAAATTTTGGACTGTTTATTTGGTAAAAGC
GATTACAAGTGCATTTCGTATACAAGATGCCTGAGCAGTCTTGGCTGCTCTTCAACGCAATACATTGAATGTAGAGCCAAGTGGCTCACCTTGAC
AAACGCGACTGCCCCACTGATGCTACATATCTGCTATAAGGCTTTCCACATCGCTTCATTGATGATTGAATCGGAGCAAGCAAAGACAAAGAGCT
CGAGAGCATCGTGCAATGTCTACTTCACATTATATGTGGCACTTGGACGGGTACATTTGGCATATACTATAAGTAACCGAGTTGGCCATATCAAG
CCGCCATTAATGGAGCTTAAATCGCGCTGCAGTGGCTCGAAGGAAATGTGTAACAACGAAATGTCGGAGGAGGGTGTTTAGTTCATTGGAACACT
TTTGTGTTATATTGTGTGGCGCAGACTGCTCTGTTTACCCAGTTGTATGGCAATACCCACGCCCCCAAAAGCGGAATTCTAGCCGATAAGTGTAT
AATCAGCCACATATTTATGTACGTGTTCCTTTGCCACTTTAGTGCCCAGTTGGACGCTGTAAATTATGACAATTGGTAATCAAAAAAAAAAAAAA
CGAACCATTTCCATTAAGAGTCCAAATTAAGTGGCACCAAAAAATATCATGAGTTTATTTAGAGAAAATATATATTTTAAACTGCGTACCATTTT
GCGCAGTCAGCGGGCAAAAGCAATTTATATTGTATATTGAAGCAGGCGAAACAAAACACTTGACAACAAAAAATTGACAAATGCAGATAACAGTA
ATTTGAAAATAGAAGAGCAATACTTATCAGCCCACATTGTTAAGTCGCTTGTTAAAAAAAAAAAAAACTAAAACAGTAATTATACGATTTCCGCTG
CCTAAAATAGTTATTTCTATGACAGTTCTCGCTGGCAATAAAAGTAGTGAATTGTGTCTGGAAAACTATCCATTGTTAGGGGATTTTAAAGTGCG
AATAGCTTGTCAACAATTGTTTTCTGTTTACGGTTATTTACGGTTAAGAATTATACATTACTCTCTTTGCCGGTTAGAGGGAGAGCGGACGGAGA
GAGGGTGCACCACGTTGTTTTGTTATTAGCGCACACCTGCGTGCGCACTCACACACACACACGAAATATTGATGGAGATGTAAATTATTGGGCA
ACTCAGGTTAAACAGCACTTCCTACCAGTTAATGGCTTACTTGCAACTGGGGGTTAACTAATTGGAGCCCTCGCCTTTATTATATCACAATCTCG
GCACTTGTGGCAGCTTATAAATGCATTTTCCTGCTTTTCTCGCGGAGCAATTTACGAAATTTACGAATTCCGTGACGTTGTACGGCCGAAACAAG
AGTGGTGATGGTCGCAGTAAACGAAGCAGAGAAATGACGAAGAAGCGGACGGTTTGGCTGCCAATTGCTGACTTAGTTAACGACAATTGACGAGC
GTGCAGGCAATTTGTGCTCAGCCGTGAGCGCAGCTCTTTGTTTATTAATTTTCCTCACAATATTTGAGATTCTGCCACCAGCTGCTTTCTTTTGC
ACGCACACTCACTCGCCTCTCACATGCACACTGTCTTTTCGTCTGTGCCCAATGTGGCAACCTGCGGCCACTCTCTCTTCTTTGACTTGCCGAAA
TCTGGCAACACTCGACAAGAGTACTAACCTTATCGGCCAAACTGAAGTTTTAACTCTGAGCCCACGCGATCGAGTGACTGACTATAGCATTTTGC
GGTAGCCCCTATTTATTCAAAATATCTCTCTCTCGCGTCGGCAAGTGAGAAAAAGAAAGACAGAAAGAGAGAGAGAGAGAGTGTGTGCGTGGGAG
AAAGACCACTGCTTTTTTTTGAGGGGAGATTTTTTGATAAGGCCTGAGATTTGGATTTTTGAAGGCCCCAGAAATACCGCCTAAGATTTGAACAT
GCATTTGAAATACCGGTTTGTACATCGACCGCAGGTTACCGTTAGAAATGTTATGCGGGATACATAGTTAAGTTGCATACCCTTTGAGTTACAAT
CACTAGTTAATAATATCTACGTTATTACCAACACGCACACTTTATCGTAATACCTCCTTGAAGTTTAATTTATACATCAACTTTATCAGTCAAAA
CTTTGATTTCGTCTGACACTTTTTTCGATTACGATCCGTCGCCAATAATTGCGATAAATCTTATCAAGTCTTTTTGGGATTGGCGCTCAAATTTA
CAATATGGCCGTACATCCTACTTATGTATGTTTTTTAACTAATTAATCACCACAATGCAAAGTACTCTTTCTTTGTTGAGCCCATATGCACTCAC
ATTTGCACCATGAATCATGTCAGTAGCTCGTTTCATGTAACAATTTCTACTTTGCCAGATTACGATGCGTTCGGAACAGGCAGATAAGAATTCGG
CCCATCCAAGAAAGGCCTTGACAGTTCTACCCCAAAATAGAGATATCCTCGTGATATTAGAAGGAACCCAACAATATGCTCGTTCTTATCTTCTT
ATAGAAATTTGTGAATTCCCGTATCCAATGAAATCATTTTACTTAGTAAAATGATTTGTTAGGCCTTAAAAAAAAACAAAAAC
(SEQ ID NO: 349)

Exon: 6018..5646
Exon: 3832..3625
Exon: 3564..3380
Exon: 3315..3151
Exon: 3078..2940
Exon: 2214..2059
Exon: 1990..1832
Exon: 1773..1001
Start ATG: 3831 (Reverse strand: CAT)

Transcript No. : CT12249
CAGTGTGCATGTGAGAGGCGAGTGAGTGTGCGTGCAAAAGAAAGCAGCTGGTGGCAGAATCTCAAATATTGTGAGGAAAATTAATAAACAAAGAG
CTGCGCTCACGGCTGAGCACAAATTGCCTGCACGCTCGTCAATTGTCGTTAACTAAGTCAGCAATTGGCAGCCAAACCGTCCGCTTCTTCGTCAT
TTCTCTGCTTCGTTTACTGCGACCATCACCACTCTTGTTTCGGCCGTACAACGTCACGGAATTCGTAAATTTCGTAAATTGCTCCGCGAGAAAAG
CAGGAAAATGCATTTATAAGCTGCCACAAGTGCCGAGATTGTGATATAATAAAGGCGAGGGCTCCAATTAGTTAACCCCCAGTTGCAACATGTCT
TCGAATGAGGCCTACCACGAGCCGGGTGCCGGTGGAGATGGACCGGGCGGATCGTCTGGCGCATCCGGCGGAGGAAGTCAGCGGAGCAACCAGCT

FIGURE SHEET 191

GCACCACCAGCAGATACTCAACGAGACGACCTACCTGAAACCCGCCGCCAAGCAGGCCTACTTTAGCGACGAGAAGGTCCTCATACCCGACGATG
ATAGCACAAACGTGGGTTTCAGCTTTCGCAAGCTGTGGGCCTTCACGGGACCCGGTTTTCTTATGTCCATTGCGTATCTGGACCCCGGCAACATC
GAATCCGATATGCAGTCTGGTGCGGCGGCCAAGTACAAGATCTTGTGGGTCTTGCTGTGGGCCACAGTCCTAGGTCTGCTCATGCAACGCTTGGC
TGCAAGACTGGGCGTGGTTACAGGCCTGCATCTGGCCGAGATGTGCTACAGACAGTACAAGCGTCTGCCACGTTGGATACTGTGGATAATGATAG
AGATAGCCATTATTGGATCCGACATGCAGGAGGTCATTGGCACGGCCATTGCCATATACCTGCTGTCCAACAAAGTAGTGCCTTTGTGGGGCGGA
GTGTTGATCACCATTGTTGACACGTTCACGTTCCTGTTTCTGGACAAGTACGGTCTACGCAAGCTGGAGTTCCTATTCGGCACCCTCATCACCAT
TATGGCTGTCTCATTCGGCTATGAGTACATTGTATCAGCCCCTAATCAAGGAGAAGTTCTCGAGGGAATGTTTGTGCCCTGGTGCTCTAACTGCA
ATTCGAATGTGTTGCTGCAGGCCGTGGGTGTCGTGGGTGCTGTTATTATGCCGCACAATCTCTACCTGCATTCCGCCTTGGTTAAGTCCCGCGAT
ATAGACCGTCGCCAGACAAAGAAAGTTAGTGAGGCGAATTTTTACTTCTTCATCGAGGCGTCGGTAGCCTTGTTTGTGTCCTTCATCATTAACCT
GTTTGTGGTGGCTGTGTTTGCCCATGGCATGTATGGCAAAACTAATAATGATGTGGTTGAAGTGTGTAAAGACAAGTCGATGTACGAAGATGCCA
AAATGTCTTTTGTGGACAATGTAAATGGAACCGCGATCATCGATGCAGATCTATACAAGGGCGGACTTTTCCTTGGCTGCACATTTGGAGCTGTC
GCCATGTACATTTGGGGTGTGGGCATTCTAGCTGCTGGCCAGAGTTCCACCATGACGGGCACCTATGCCGGTCAGTTCTCAATGGAAGGCTTCTT
GAATCTGCAGTGGCCGCGCTGGTGTCGCGTGCTGGTCACGCGCTGCATTGCCATTATTCCCACCTTCTGCCTGGCCATGTTCAGCAAGATGGAAG
ATTTGACTAGCATGAACGATATCCTGAATGCGGTGATGTCGCTCCAGCTGCCATTCGCTGCCATACCCACCATCGCCTTCACCTCGTGCGCCGCC
ATAATGGGCGAGTTTGTTAATGGACTGTAAGTGATACAGACACTTTTAATTGATTATCGTGCATTCTTTAAATTTTTGTATTCACAGGGGCAACA
AAATCGTATCCATACTGCTCACCATTGTAGTGATTGGCGTTAATTTGTACTTTGTGGTGGTGCAAGTAGAGAATATGGAAATTAAAGGCGGCTTG
CTGGCACTAGTCTGTGAGTAGTCAATTGCCACAATTTAAACCGAATCTAATGTATTTTTCCTTTTGCCAATTGCAGGTATTTTTGCCATTTTGTA
TATACTGTTCAACCTCTACCTTGTGATACACATGGCTGCCTGCATGGGCAATCAGCGTTTGATGAACA
(SEQ ID NO: 350)

Start ATG: 375 (Reverse strand: CAT)

MSSNEAYHEPGAGGDGPGGSSGASGGGSQRSNQLHHQQILNETTYLKPAAKQAYFSDEKVLIPDDDSTNVGFSFRKLWAFTGPGFLMSIAYLDPG
NIESDMQSGAAAKYKILWVLLWATVLGLLMQRLAARLGVVTGLHLAEMCYRQYKRLPRWILWIMIEIAIIGSDMQEVIGTAIAIYLLSNKVVPLW
GGVLITIVDTFTFLFLDKYGLRKLEFLFGTLITIMAVSFGYEYIVSAPNQGEVLEGMFVPWCSNCNSNVLLQAVGVVGAVIMPHNLYLHSALVKS
RDIDRRQTKKVSEANFYFFIEASVALFVSFIINLFVVAVFAHGMYGKTNNDVVEVCKDKSMYEDAKMSFVDNVNGTAIIDADLYKGGLFLGCTFG
AVAMYIWGVGILAAGQSSTMTGTYAGQFSMEGFLNLQWPRWCRVLVTRCIAIIPTFCLAMFSKMEDLTSMNDILNAVMSLQLPFAAIPTIAFTSC
AAIMGEFVNGL*
(SEQ ID NO: 351)

Classification: known_flybase_gene
Gene Symbol: Mvl
FlyBase ID: FBgn0011672

Celera Sequence No. : 142000013383801
CCAACCGTCGCAGCCAATGGATGGGTGATCTCCATCTATAACCATCAAAGGCCGGAGGAACGTCTCCCTTTACATCTGCATAAGCACTTTCTCTT
TCTCTTTCTGTTTCTGTGCCTGGAACATTTTGGGCAATACTAGTCCTCAAAAAACTAGTCTACAATATATTCAAGGTTTCTACGCAATTTACATT
ACTTTGCAGGCCCGCTGAAATCTACTCTAATATTAGGCTTGTATGATGTCGTTATTTGCTCTCGATTCTTGTTAATTTCTACGTAGTCTCATCTA
AATAATACTTCAAATAGTATATACATGGCCAGCCAAGTCAACAACAATTGTTGCAATGTCCGACGACAGCGTTGCGGTTGCTTCCCACCTCATCA
CGAAGCGCACCGAACCAACCAAGACTAACTTTCCGTATCTTATGATCGTGGCTATTATATATAGTTGATGTGTGTATTTACAAATGAGGACAAAC
CCAATTATCTCCAAGGATCTGGGGGATTCACGAATCGCAAACTGAATTAATGTAAATGTAAGTGTAAGTTGAATGAAATGCATTTTGTTTTTTTG
CGGGGGGATATTATATATGGATATATGGTACTGTGTGTGTGAGCGGCAAAAAATAAATAGATCGAGATATCACCCGCCACTGAGTTAAGTATTTT
TCACATTATCACGTTTCATTGAGTTTGTTTCGTGTGTGGGAGGGAACATATAAACTCGAACGCATTAATTGTAGTTTCATTATGGTGAATCTAAC
TTTAATAAATGGGAAATATGTACCAATATTTATAAATGTAGTGGTAACCTTCATAGTTGCTGAGAACGAATGACATCATGATGAATTTCTTCAAT
TTATAAAATAGTTCTTTCTTATTACTTTAGGGAGAAACTTAGCACTGAAGCACAAATAAGGTTCGCAGACAGTTGAGTGTCATTTTAATCTAACC
ATACTTAATCGTATTCATCTTAACATAGAACTTATAAAAGGTTTCTTTGTGATTTATCTTCATAATTCATGGAAATTTGATTACTTATGTTAAAA
AAAAAAATTATATATTATTTATATATATGCATTTACATATACATAATAGGTGATTTTCTTAGAGATTCCACTTCCAGGTAATCATCAAATTGTCA
CAGAAAAAAAAATAAATCAAAACAATTTATGCTTTGGTTTTCCAATCACAGAAATCTTCTGCAGACATTTTGCCCACGGCTGGCATGAAAATCG
CACGAAAAAATCCTCAAATTTCACAGAATCTCCACAAGATTTCGTTTTTTTTTTTTCGAAATGCACTAGGAACAATGGTTTCTCTTCTCTTCGAT
TAACTATGAAAACCTCTACTGAAAGTTCAAGAGATTTCTGTGATAGTTGGATTTTTAGTTGGACATTGATTGGTACACAAATATTTCTAATACAA
AAGAGTTACACCGCTCATACGGAGATGCTAAATATGAATGCAAAAAAAAAAAGGAAAAAAGAGATTCAAAAGAGCTCTATGCGCACTGCTTAAAA
AGAATACAAAAAAAAAAAAAAAAAAAAGATTAACCATTCCACCATGATTTTTAACTTATTCTTTGATCAAAATACGATTGATATTAACTTTTCCAG
ACAAATTTCTGAACAAATTGTGACGGTGTTCTGTTACCGGAAAGCGAAACCTCTAAAGCGGGCACACCCTTATATATATAAATTTATATTCAACA
CACATTGGCCAACCTGATAATAGATCAACCAACGTTATCATGTTTCTTTCCTCCATCGCGACAACGATCGTGTGTATAAATAGTGAAGAGTATTT
ACTGCTAAACCTATTGGTTCTCGTCATCATCTCCATCGCCGTCGTCGTCGTCGTGCTGCTCTTCCAGCTGCTGGTGCTGCTGCTGGGCAGCGGCG
GCAAGTAACGCGGCTTTCTGTGCCTGCGCCTGCATCGACGCCTGCATCGACGGTGCGGACATGGCTATTTTCCCGCTCGTCTTGTACTCGGTCAT
CTCCTATTAAAGGCAAAAGTGCACATGTCAATCGGGTCAATCCAAGCGGTCATTTATATATCTAAAACATACGCGTTCATATCGAGCCTTGTCCC
GCTCGGCCATCGACTCGTACTTCTGCTTGACCTCGGGATCCACATCGGACCACTTTCGTCCCAGCTCTTTGGCGATGTCGCCCACTCCGAACTCG
GGATTAAGTGCCTTCACCTTATTTCTCTCGTCATTGCAGAACCAGAAGAACGCAGACCTAAACAGCGGCAGAATAGAGCATAGTAAATCATTATT
ATTGATCTGATTCGCTTCATTATCTCTTGCAGTCACATTGATTTTTATGCACTATAGCGTATAATATGATAATTGACTTTGCTACGAACTCACAA
TGAACGTTTTGGAGCATTGGGGTCCTTGATCTGTTTCCTCTTCTTGCCGCGTCCCACAACCGCTCCCTTGGGCGGCACATAGTTCTGCATTTCCG
CCTCATATCGCTGCTTGTCCTTCTCGGCCATTTCGTGGAAGCGCTTCTTCTCCTTGTCCACCATTGTCTAGACGAACGGGATAGATGGCAATCCA
CTTTAAAACAAGGAGTCCTTACGTCATTTGATCATTTCATTTACTTACCTTCCACCGTTCGGCGCACTTCCGCGAGAATTCGGCGAATATCACCG
TCTCATCGGGATGTTTCTTTTTGTGCTCCTCTCTGCAAGTTTGTACAAAGTATGCGTAGGCGGTCATTCGGCCTCTGGGCTTGGCATCGGCCTTG
ACTCTGCTCATGGGGCTCTGTTGGTTTTTGGCCACGAAAACGAGAACGAGAAAGAGATCGAGAACGGAAACGGGATTAGCTGCTGACTAAGGGCT
AATGTAAGCATGTGGCATATTCAACTTACCGCCGAATTGATGACATTCTGTTGCTGCTGCTGCTGTTGCATCTGTTGTTGCTGCTGGTGCTGTTG
CTGCTGCTGCTGTTGTTGCTGTTGCTGTTGCTGCTGCTGGTGCTGCAGTTGCGCCGCTGTATTGGCATCGACCTGTCCCTGATTGGCGGCCGAAT
ACCACCACTGGGAGCCGGGTACGGCTGCTGCTGCGGCTGCCTGTGCCATATTTAGACGATAATCATAGCCCGTGGTGCCGGCTGCGTTCGATGTG
GCCACCACTTGGGCCATCGTCGTGGCCGGATTCGGAAAACTGCTGGCCATTTTGTATGTGAACAGCTGTTGGGTGCCCACGCCGGCTGTGGTATT
GGAGCTGTTCTGGTGCGCCTGCTGCTGATTCTGCTGGACGACCACCTGGTGTTGTTGCAACTGTTGCTGTTGTACTTGTTGTTGTTGCTGAGCAG CCAATTGCTGCTGATAGTGTTGAATTGTTTGCTGATCAATAGTTGGTTGATGGATGTTCATTAGCATTATTAGTGCGATGCCAGTCGATTGGGCT
ACAACAATACACTACAATCATTTGGCTTGACTCTCGATGTCTGGCATCGCACTAACCACTAAGATGGTCCTTAATACTAACGAAAGTGAAAACTG
TGCATTTTTTGTTTGTGAGTTATGCGGTTTAATGAGTGCCTGATGTTTTTGTTGACTACTTGCTCACAAAATGACTAAATAAATAAATACCGAAT
GCAGCGATTTTCTCTACATTGCGTTTACACATTGCTGATTTGTTAAAATATTTAACAGTTTTTACACTGGTAAAACTGAATTTTAGTAAGCTAAG
CTAAGCTTCTTTAAATTATTTATTAAGTGTGAAAAATATTGTTGCCTAAAGCAAAAAGCTTAAATAGCATTCTAAAATCCTCCATTCATCATTAA
TACATGCTAAAAAAAAAAAAAGTATCTGTCGGAACTGGGGCGTTATCCTTATTATTTACTTTCCATGTAAATAAATATGTAGATACTCGTTATCTA
CAGATACCGATAAATTGATGTCAATACCACACAATATAATACTAAATCCTGTCCAAAGTGAATTCTCTTGTTTCCCATTGAACGCGGAATTTCAA
TGTCAATAATCTAGCTTGTTTTGTTTACAAAGTAATAGTAATAATAGCACCAGCTGTTAACCCATAGATAAAAAGCTTTTACATGAATCGGGCAA
GAAAGTGGAACTATTGTTGGAGAAAGAAGAAGCAGAGCGAGTAGCACCGGTTCCGTTTTGTGAATCGGATTGGATTGTCTTCATTTCGATTCCGA
TTCCAGGGCTTAAAGTGCAAAACCAGGGCGCCACAGTTACAAAACATGAATGAACCCATTCTTTTTGCCGAAAATAGCCCCATCCTGCTTGTCAA
TTATGAAAAAGCAAAATACACTTTCCTACAACAGCCAAAAAAAAAAAATAAATAAATATTAGAGCCATTTTACGTGGGGATACATATGTATGTAAC
CACAGAAATATACATGTGCGCATAAATATTTGCATAGCCAAGTGTTTGCACAGCCATTCATTTGTATTTTATGCACACATGGATAAAAATAAGCC
AATTTCGGATTACGCAAGCCTGTGATTTGGGTCTTTTCATATACAGGTTTTATATGTGTATGTATTTTTTTATGTACATCATATTTTCCTTAT
TTTTGCACATTGTATCTATTTACGTACATCAATAGGCATGCAAAAAAACGTGCATCGCATTTTGCCAGCATATTTCATAAGAAACGAAAAGCAAT
GCGGTTTACCGTTTACATCAAGGCATTCACGATTCTTGGTATAAATGTACATATTTGTATATTTATACAAACTAATAAGAAAAATGGCGGACTTG
GATGCGCACGCAAAATACAATTTTGATTGTACAGCGTCGCTTTTTTGTTTGTATGCATACTTGCACATACATAGGCGTACACTTTTTGCATTTAG
TAACATGCCGATTTACTTAATAACTAAAAACAAAAGCGAGACGCAATGGATGTACAAGCGCTTGCATGTACATACGTATGTAAGTATGTATGCAG
CATATATATTCACAAAAAGTTTCCACTGCGGCTGAGAAAAGGCAATCAGGTGCCGAAATATCCAAATAAATAATAAATAAATAGGTGCCTGGCTT
TTTTGTTAATTATACATTGTCGTTTGGCGGGAAAATGATTAAAACGCGGCAACCTATACATAAACGCGCCCATGATTGTATGTGTGTTGTGCCAT
GAGTGTATATAAATGTGTGTTTGTGTGTGCGTGCGTGTGTGTTTTAAATAAAACGCCGTATACCTGCACACAAGCTTACCTGTATTTGATGAAAG
TGTTCCATAACTGTGAGATTTCGGATCTAGTCCGAATGTTTCAATCGTGGATTGGCTTTATACTGGGATTTCCGTTCTATATCTTTCACTTTTAT
TCCTAAATGGTTAAAGCATATATATTTAGTTTTAGCACAAGTACGTATGTATGTAATACGCACACCAACGCAAATTGGAGTCGAGTCTTAAGCCA
GTTTTTTTGTCTGTTTTCCTTTTTTTAATACTGTTCTACGCAGTTTGTTGTACGTCGTATTGTATTGATTATTGCATGTATGTATGCATGTACGG
CCACAAACGCGAATGTATGATGCACGTTACAAGGAAAAAAAGGAACACGGCACAAGCCAAAACTTCGAAATGAAATTCGAAAATTTAAGAATTTC
ACAATGCACGTTGTTTTTTTGTACTTCTTTTTTTTTGTCTAGGCCTTTTTCGCTTATTTGTTGTTTGATTTTATTTGTTTTTTTGGTTGGGAAAA
CGCGAAACGCGGGCGGCTTTGCGGATTTGTTTTGTCGTTTGTATTTAGCTTGTAAAAAATAAACAAACAGCGCTGCATACGCTGAGTTTATTGTA
TCGTATCGTATCGCTTGTGTTTTGTTGGTGTGGTATGGTATATATGCTATACAGTACACAGTACACAGCACACAGTATGGTATCGTATCAATGCG
AATGCGGAAAATACAATATATGAGGTTGGTTCGCGCGCCGCTCGTACCAACAACGAATGAATTGAATTGAATTGCCGTCTCTGCCTTACCTTCTC
ACTGTGCTTCCAAATCCAAACGGGCGGATAAATGTGTATGCGTTGCGTTGCGTTGGACTGTGTGCGCAATTCTTTGCTGGTGTGCGTGTGTGCGG
GAGAGCGAGAGCGCGAAGAGAGTCGTTATAGTCATTTTGTTGGTAGAATTAGTGTTGCTGAGAGAGCGCTCAGTGTCATATACATACATATGTAC
ATACACGTGGTGGAGGGAAAAGGCCTTATAAAACTTTTTGGCCTGTTACTTTCATACAAACATACGATCACGGGTATGTACATAAACGCTGGCGT
GCCAAACATACAAACTATGGAGTGTGTGGAGTGTGGGAAAAATACAGAACTGTATGTATGCATATGTACATTACACAGTTCTTAGGGCCAAAATT
TATTTTAAACATACATATCTTATTTTTAACTGCCAGCTACATTCGTTAATGCGACGAATTCTACAAAACCGATATGCATCAATGCAAACACATTG
ATACATAGCCAAGCATATACAACTGTGCTCATGCTAATAGTAGTGCATATGACCGCCACTTTCTAAATTGATGATTTTATATGAATGCTATGTTC
AATTTGTCAAGCGGTTTTTCAGAATGAATAAGTTCATATTAATTACTGAAATTATATGTTTTGTTAAAGAGCAGTGCAGGTACAAAAAGCCATTT
GTAACTGCTTTGCTTGTTTTGCGACACAGAAGACGAAGCGAAAAAAAAAATTAATTAACAAAAGGGAATACGGAAAAAAACCGTTTGATGCCTTT
CAGTGCTATTTCCACGAACGCAGCTGTATGTACATACGTGTGGAACACACAAACATATGTACATCGCAGCGACCCGCTACATACACATACACATT
TTCATTTTGTGTGTTCCCGTCTGACTGTACTTTCAATTCGAATTCGAAAGAGAAAAAAATGTTCTCTTATGTTTTAAAACAAATTCTCCCTCAAT
TCTCTCTGTCATACA
(SEQ ID NO: 352)

Exon: 5950..5860
Exon: 5322..5210
Exon: 3356..2880
Exon: 2772..2614
Exon: 2537..2374
Exon: 2242..2068
Exon: 1998..1001
Start ATG: 3185 (Reverse strand: CAT)

Transcript No. : CT12419
TCATTCGTTGTTGGTACGAGCGGCGCGCGAACCAACCTCATATATTGTATTTTCCGCATTCGCATTGATACGATACCATACTGTGTGCTGTGAAT
AAAAGTGAAAGATATAGAACGGAAATCCCAGTATAAAGCCAATCCACGATTGAAACATTCGGACTAGATCCGAAATCTCACAGTTATGGAACACT
TTCATCAAATACAGCAAACAATTCAACACTATCAGCAGCAATTGGCTGCTCAGCAACAACAACAAGTACAACAGCAACAGTTGCAACAACACCAG
GTGGTCGTCCAGCAGAATCAGCAGCAGGCGCACCAGAACAGCTCCAATACCACAGCCGGCGTGGGCACCCAACAGCTGTTCACATACAAAATGGC
CAGCAGTTTTCCGAATCCGGCCACGACGATGGCCCAAGTGGTGGCCACATCGAACGCAGCCGGCACCACGGGCTATGATTATCGTCTAAATATGG
CACAGGCAGCCGCAGCAGCAGCCGTACCCGGCTCCCAGTGGTGGTATTCGGCCGCCAATCAGGGACAGGTCGATGCCAATACAGCGGCGCAACTG
CAGCACCAGCAGCAGCAACAGCAACAGCAACAACAGCAGCAGCAGCAACAGCACCAGCAGCAACAACAGATGCAACAGCAGCAGCAGCAACAGAA
TGTCATCAATTCGGCGAGCCCCATGAGCAGAGTCAAGGCCGATGCCAAGCCCAGAGGCCGAATGACCGCCTACGCATACTTTGTACAAACTTGCA
GAGAGGAGCACAAAAAGAAACATCCCGATGAGACGGTGATATTCGCCGAATTCTCGCGGAAGTGCGCCGAACGGTGGAAGACAATGGTGGACAAG
GAGAAGAAGCGCTTCCACGAAATGGCCGAGAAGGACAAGCAGCGATATGAGGCGGAAATGCAGAACTATGTGCCGCCCAAGGGAGCGGTTGTGGG
ACGCGGCAAGAAGAGGAAACAGATCAAGGACCCCAATGCTCCAAAACGTTCATTGTCTGCGTTCTTCTGGTTCTGCAATGACGAGAGAAATAAGG
TGAAGGCACTTAATCCCGAGTTCGGAGTGGGCGACATCGCCAAAGAGCTGGGACGAAAGTGGTCCGATGTGGATCCCGAGGTCAAGCAGAAGTAC
GAGTCGATGGCCGAGCGGGACAAGGCTCGATATGAACGCGAGATGACCGAGTACAAGACGAGCGGGAAAATAGCCATGTCCGCACCGTCGATGCA
GGCGTCGATGCAGGCGCAGGCACAGAAAGCCGCGTTACTTGCCGCCGCTGCCCAGCAGCAGCACCAGCAGCTGGAAGAGCAGCACGACGACGACG
ACGGCGATGGAGATGATGACGAGAACCAATAGGTTTAGCAGTAAATACTCTTCACTATTTATACACACGATCGTTGTCGCGATGGAGGAAAGAAA
CATGATAACGTTGGTTGATCTATTATCAGGTTGGCCAATGTGTGTTGAATATAAATTTATATATATAAGGGTGTGCCCGCTTTAGAGGTTTCGCT
TTCCGGTAACAGAACACCGTCACAATTTGTTCAGAAATTTGTCTGGAAAAGTTAATATCAATCGTATTTTGATCAAAGAATAAGTTAAAAATCAT
GGTGGAATGGTTAATCTTTTTTTTTTTTTTTTTTTGTATTCTTTTTAAGCAGTGCGCATAGAGCTCTTTTGAATCTCTTTTTTCCTTTTTTTTTT
TGCATTCATATTTAGCATCTCCGTATGAGCGGTGTAACTCTTTTGTATTAGAAATATTTGTGTACCAATCAATGTCCAACTAAAAATCCAACTAT
CACAGAAATCTCTTGAACTTTCAGTAGAGGTTTTCATAGTTAATCGAAGAGAAGAGAAACCATTGTTCCTAGTGCATTTCGAAAAAAAAAAAACG AAATCTTGTGGAGATTCTGTGAAATTTGAGGATTTTTCGTGCGATTTTCATGCCAGCCGTGGGCAAAATGTCTGCAGAAGATTTCTGTGATTGG
AAAAACCAAAGCATAAATTGTTTTGATTTATTTTTTTTCTGTGACAATTTGATGATTACCTGGAAGTGGAATCTCTAAGAAAATCACCTATTAT
GTATATGTAAATGCATATATATAAATAATATATAATTTTTTTTTTAACATAAGTAATCAAATTTCCATGAATTATGAAGATAAATC
(SEQ ID NO: 353)

Start ATG: 376 (Reverse strand: CAT)

MASSFPNPATTMAQVVATSNAAGTTGYDYRLNMAQAAAAAAVPGSQWWYSAANQGQVDANTAAQLQHQQQQQQQQQQQQQQQHQQQQQMQQQQQQ
QNVINSASPMSRVKADAKPRGRMTAYAYFVQTCREEHKKKHPDETVIFAEFSRKCAERWKTMVDKEKKRFHEMAEKDKQRYEAEMQNYVPPKGAV
VGRGKKRKQIKDPNAPKRSLSAFFWFCNDERNKVKALNPEFGVGDIAKELGRKWSDVDPEVKQKYESMAERDKARYEREMTEYKTSGKIAMSAPS
MQASMQAQAQKAALLAAAAQQQHQQLEEQHDDDDGDGDDDENQ*
(SEQ ID NO: 354)

Name: HIGH MOBILITY GROUP PROTEIN BSS (BANG SENSELESS)
Classification: DNA_binding
Gene Symbol: bss
FlyBase ID: FBgn0000231

Celera Sequence No. : 142000013385217
AAAAGTAGTATATATGATGCATAGTCCTCTGTTTAATTATTAAATTTAAATGTTTAATCATAGAATTTGCATCCAAGAAACACAGTTACAAAGGT
TTTAACACTTACTATTCTTTCGGTTTTGGGTTTCTTTCACGATCCACTGATTTTTATATTTCTCCCTTTTGTTTTTCTTTATTTTAAATAAACGT
TAACATAGTAAAAATAATAAAGCGTACATTTCGCTACGAAAAGTTGATTCGTAATTGAACAAAAAAATTTATGAGTAATGAAAATGCTTTTACTG
TTCTCTCGATGAAAACAAACTATTGTAATAGTGTATTTTTCTTCTTTACAAAGAAGAATTTATCAGGCCGTGATGTTGAATATTATATATTTTAT
CTTTAGTTTATTTTATTCGCCTTGATCACTGGTTAGCGACTGTAATTTGTTTTTATAAGGTAGGATGATTTTTTGATTAGGTGAGTGGTAATAAC
ATAAAAATAAACAACTTCACATCAGGTTTTGGTTGATGCAATAAAACAATTTCCATGACCGCCCCTGCCGTTTTAGAAAAAATCTCGAAACAAAT
CTCGTATTGTGAACAGCTACTAGATATAAAGTCCATAATGAGGATAACTTAGCCTGACACTGACTAGTTTACACGAGGTCACTTGCTTGATCGCG
ATTTTATCGTGTAAAATCTGATTTAGTTGGCCACGTATAAACTAAAATTGCTTTTCGTGTGTTCTCTTTTCATATATCTTTAAACATATGTATAA
TTTATTATCCGTTTTTTTTACTTAGCTTGTTGGTTGGTATTTTTGTTGCTTTTGGCTTATAATGGCGGCTACAATTGTTTTCGTAATTTCCCCA
TTTTTCTTTTAGTTTTTAAAAAGTTTGTTGTCTGTGATATACGTAATTTATAAGTTTTCATTTTGGTAACTTGCTGCTTTCATTCACCATCGTCA
GTAACCAAAACTGCAATTTGAGGAACCTACTCCTGCCCAAAACGATCGATTTAAGCCAGAGTGGGAAACTGACGCTCATCGTTGACCTTGGGAGC
GGTGTTCTGTTGTCGCTCAAAACGCTTATTCGGCCCTGGACCGCTGTTCTGATTGTTGTTCTGGTTGTTTCCCGGACCGCGACGATCGATGGGTG
GCCTTTGATTTTGAGCGGATGAACCGCCGCCCTCGTTATTATGCTGCTGGCCATCCCGTGGGCCACGGTTTCCACCCTCACGATTATCTCGGCCG
CCCTCACGATTGCCGCCATCGCGGTTGCCACCCTCGCTGCGTGGTCCGCCTCCAAATCCACCGGGTCTGGGGCCTCCACGGCCACCGCGTCCACC
GAAACCGCCAGGTCCGCCACGACGACCATCGTTGAAATTGAACTGAATGTCCAGGACGCGCTGTTGCCTGCCCACACGCTGTGGATAAAGGGCAG
GGTCGTACTCGAGCTCCTCTTCGCTGTCGTTCTCCTTCTTCTTGTTGCTAGTTAGGACGACCATTTTCTTCCATTGTGTGGTGTCCTCACCTGCG
GGAAATATTGATTGTAGATTAATTTCTAGATGATAGGCCATCATTTAGAGTTAAGCTAAGATCGGTTTGATTTTCAATTTTATACTTCTTTTATA
CGGATTTTAGCTCAATATGATTTGTAACTTTGGTTGTTGGCTTGGCGAAAAGGTTTCTTAGAATAACGGAAGTTAAACTATCATTCCGTGGTATC
GAATTCAAATTATTAACCATAAAAAAATTATGCATTGTTCACGCACCTTCTCCAGCCTTGCGGATATTAAAGGTTGGCTTGATGCGCTGTCCTTG
CTGTGCCTTCCACTCGTCCAAGGTCAGCTCTTTGGCTTCCTCCTCGGCGGTAGCCTGCTCGTTTTGTGGTTCAGTGCCAGATTCATCGGCCTTGG
CGCCGCCCTCGGCATTGGTCACATTGGTTTCGCTTTCGTTCTTGTTCACATCATCAATAGCCTCCTTGACCGATCCCCAGTTGTGGGAGCCAGCT
CCATCGCGTTTGTCAATTGACTTCACACCTGTGCATAAAGAAAGTATCAAATATTAATAATGATTTATGTCTGCTTAAATTCAGAAACGTCAAGA
AGCGGAAAATCTGAGCTTCTATATTTGCAAATTTTAGCCACAGCTATAGTGCAACTTGCCTGCAAGCCCTAAAGTAAGTTTTTCTGCTTAATTTA
TTAACTGAATACTTTAATTATTAGCCAAATAATGGTCTATTTTATCAATACCCCACTAATTAGGTCAATTGAGAAGTAACCACGATAGGGGGACT
ATATTCACTGCCCTCGCTCGCATAGTCACAGATAAGCCGACAGTAGCAGCCCCAGTTCACTGTAATCAGATTCAGTGGGGGAACTATTCCAACCC
CTGTTTCCCCCCAATGATTATGCCTGCAAAGGCCTCCTACAAGCACTTGCGTTAGACGGGAATGCCGCCAAGAAGATGGGCGAACTATTTTTAAC
ACATTTTCTCTTTCGATTTGTGCCGCAGTGCTTCTTGTTTCTGTTGCTGCCGGCCGCTGTGATATTATAATTTTGGATATTCCAAAAACGAAGCG
GTCGGTCTAAGCAGGCAGTGGAAAACGGGGGAAAACGCGGCGAAATAGATTTCATTCAATGGAAAGAAGTGTGATGTAGCTTGTTGAATGTTCTG
TCCGACCATTAGTATTGATTTGACTCACTTATCCCCCACGTGAGTGGGAGATTTGCCTGTGTTGTTTGACCATTGCCCATAAGTTCATCGGGATT
TTGTGTGCCACAAATTGGTTTACACCGTTCTCCCGCACTTTTCGTGAAATTGCTTGGCATAAACAATATATATTTAAACTGATTTATAATGCAAC
TGTTTAAATATTACTATCCATTAAATAAGATTGGCAATCTGCTCGGAGCAGGCTAATAAATATTTTATACTTTGAAATACATTAAATTCATGATT
TAGATTAGCTATAGAAATCTTAAATCAATTGATGGAAATTTCACATAGTTTATTAAAAGGAATCGCATTTCAAACACCGAACGAATTCCAGTTTC
TTTTAAATATTTGTTGTGTACACAGAAGATTGGAATCATGTTGCTTGAAGGCGACTAATAATTTCTCATGACTATAAACATGGTAATTGGTTACG
CGTAAACTGTGGATGGAATTTGTTTTTCCTGCGTTGCCTGCTGAGTTTTATTTTCTGGTTGTCATGGAGTGTGGCTTTTGGTTTATTTGTTAATT
TTTTCGTATGGGCGCGCTCGTTTTATGGTTATGTCTACCCCTTGGTGGTTCAACTTTAGTTTCGATCTTATCAACAGAAACATTAACTATTCATA
TGCGAAAAAATGGTCATTAATCTAAACGATTTACTCCCTAAATATCCCATCTTCTCTATCCTTTTTACTAAGTATACTTCTCTGTAAAGACTTTA
ATGTGATCTACACTGTATCTACTTGACTTGACCCCTAACCCATTTGGTACCTTAATGCCTTAATGAAATGACCACACACTCACCAGTTCTATCGG
AACCCGACTGGCGGTCGAACTCGCGCTTCCTGTTCTGGCCATCGTAGTTGCGGTTCTGACGCTGGGGACGATCTCCGCCAGCACCTGGGCCTCCA
CCTGGTCCGCGGTAAGGTCGCGACTGCTGGCCATCGGGTGCTCCGACGTTTTCGCGGACATTGCGGCGATTGTTGCGCTGCTCACGAGTCTCGGC
ATTGCCATTCTGTTGACGGAAGTTTACGCTGCGCTGCTGCTGGCCACCTTGTCCTTGACCCTGTCCTTGACCGCTACCAAATTCACGTGTTCGGT
TGGCGCCACCTCCTTGCCGTGGAGCACCCTGTTGTTTGTAATTGCTGCTGGCGTTATTATTGAACTGCTGCTGTTTGTTGTCGGCCGATGGAGTG
AACTTCTTGCCATCGGTTTTGTTTAACGCATTATTGGGCTTGTTCTCCTTTTCGGCCTGATTTGGTTTCTTGGCATTGGGTCCACCAATATTGGA
TCCTGCGTTCGCCTTGTTATTGCTGTTGGCCACCTTGTTGGCGGTCGTTTTGGTGGCCGCTGCAGCAGCAGCTGACGGTTGCTTCTTCTTGCCAG
CTGCTGCTGCGGCAGCAGCGGCCGTCGGCGCCACAAGATTATCTAATGGATCGCTGACATCGTCGTCCATGAACAAAAGTTCATAACGATTTTTA
CCGGCGCTGTCCATGATTTTGTGGGTGGGTGTGTTTTTCGTTGCTAGCTGGCTGCCGCTTTAATTGCCTTTTTGCTCTGTAAAAAGAAATAAATA
CACACAGTTTTAGTGGGAATTGATTGATTTTCCTTTTTCGCCCGCCGCCTCTCACACCCTGTGAGATTCGATAGGATTTCTTTTTCGTGTCACAA
ACTATGGTCTAATATGGCATATATTCGCTGGATTTATGGTTTACGACATTAACACGTGGACTAACGTGAATTTACTCAATTTATTTAGGCCCTTT
GGGTGGATTTTTCTTACTTTTCTGCTGGCTGTTTGGTGGCTGCTGCTCTCTAACCTTAATTTTCAGTGTTTCTTCTTCGCCTCGCTGCTAGTATT
ACCTACACACACTGCCTCACGCGATTCCACACGCACATGGGCCAAATCACGCACACCACAGTCAGCACGAACAGAGCGCCCACATGTGTTCTTGG
TATACATAGAAAAACAGAAACTCACGTTTTTCAACGCGTTTCGCGGCGAATGTCGCAAATCGATTCGAATGGCAGCTGTGTTTAGCGGGCTCTCG
ATTTGGCGGGCACTTTTTAGTTTGAAGTGCAAGCCAATTTCATTAGTTGGAGAATATGTGAAAAATTGAGCAAATTATATAAATTGGTACAAAAT GTTGGAGCATATATTATAAGAATTCATAATTCAATACTTTAGAAATGAACGTATTAAGTTATTGCTTTTATACTTATATAGAATTAATTTTTTT
TCTTTCAGCCAAATTAAAAAAAAAATATCAATATGTCTGACGACTGGGATGATGAGGTTCGTATTGCTTCGTACAAAGAATATATGCTTACTAAG
CCTATCTATTTTAGCCCATTGTTGATACTCGCGGCGCCCGCGGTGGAGATTGGAGCGATGATGAGGACACGGCCAAGAGCTTCAGCGGCGAAGCT
GAAGGCGATGGTGTTGGAGGGAGCGGTGGTGAAGGCGGCGGCTACCAAGGAGGAAATCGAGATGTGTTCGGAAGGATCGGCGGAGGCAGAGGAGG
AGGAGCTGGAGGTTATCGAGGAGGAAATCGAGATGGAGGGGGCTTCCACGGTGGACGTCGCGAGGGAGAAAGGGACTTCCGCGGTGGAGAAGGCG
GCTTCCGCGGTGGACAAGGCGGCTCCCGCGGTGGACAAGGCGGCTCCCGCGGGGGACAAGGCGGCTTCCGTGGTGGAGAAGGCGGCTTCCGCGGT
CGGCTGTACGAAAACGAGGATGGTGAGTAAACCTTTTGGACGACATGTTAAATTTTGGGTTATGGTCATTTGAGTCATTCCTGCTGAATTCCATG
TGGT
(SEQ ID NO: 355)

Exon: 4514..4483
Exon: 4256..3504
Exon: 2023..1757
Exon: 1515..1001
Start ATG: 4194 (Reverse strand: CAT)

Transcript No. : CT12457
AGAGCAGCAGCCACCAAACAGCCAGCAGAAAAAGCAAAAAGGCAATTAAAGCGGCAGCCAGCTAGCAACGAAAAACACACCCACCCACAAAATCA
TGGACAGCGCCGGTAAAAATCGTTATGAACTTTTGTTCATGGACGACGATGTCAGCGATCCATTAGATAATCTTGTGGCGCCGACGGCCGCTGCT
GCCGCAGCAGCAGCTGGCAAGAAGAAGCAACCGTCAGCTGCTGCTGCAGCGGCCACCAAAACGACCGCCAACAAGGTGGCCAACAGCAATAACAA
GGCGAACGCAGGATCCAATATTGGTGGACCCAATGCCAAGAAACCAAATCAGGCCGAAAAGGAGAACAAGCCCAATAATGCGTTAAACAAAACCG
ATGGCAAGAAGTTCACTCCATCGGCCGACAACAAACAGCAGCAGTTCAATAATAACGCCAGCAGCAATTACAAACAACAGGGTGCTCCACGGCAA
GGAGGTGGCGCCAACCGAACACGTGAATTTGGTAGCGGTCAAGGACAGGGTCAAGGACAAGGTGGCCAGCAGCAGCGCAGCGTAAACTTCCGTCA
ACAGAATGGCAATGCCGAGACTCGTGAGCAGCGCAACAATCGCCGCAATGTCCGCGAAAACGTCGGAGCACCCGATGGCCAGCAGTCGCGACCTT
ACCGCGGACCAGGTGGAGGCCCAGGTGCTGGCGGAGATCGTCCCCAGCGTCAGAACCGCAACTACGATGGCCAGAACAGGAAGCGCGAGTTCGAC
CGCCAGTCGGGTTCCGATAGAACTGGTGTGAAGTCAATTGACAAACGCGATGGAGCTGGCTCCCACAACTGGGGATCGGTCAAGGAGGCTATTGA
TGATGTGAACAAGAACGAAAGCGAAACCAATGTGACCAATGCCGAGGGCGGCGCCAAGGCCGATGAATCTGGCACTGAACCACAAAACGAGCAGG
CTACCGCCGAGGAGGAAGCCAAAGAGCTGACCTTGGACGAGTGGAAGGCACAGCAAGGACAGCGCATCAAGCCAACCTTTAATATCCGCAAGGCT
GGAGAAGGTGAGGACACCACACAATGGAAGAAAATGGTCGTCCTAACTAGCAACAAGAAGAAGGAGAACGACAGCGAAGAGGAGCTCGAGTACGA
CCCTGCCCTTTATCCACAGCGTGTGGGCAGGCAACAGCGCGTCCTGGACATTCAGTTCAATTTCAACGATGGTCGTCGTGGCGGACCTGGCGGTT
TCGGTGGACGCGGTGGCCGTGGAGGCCCCAGACCCGGTGGATTTGGAGGCGGACCACGCAGCGAGGGTGGCAACCGCGATGGCGGCAATCGTGAG
GGCGGCCGAGATAATCGTGAGGGTGGAAACCGTGGCCCACGGGATGGCCAGCAGCATAATAACGAGGGCGGCGGTTCATCCGCTCAAAATCAAAG
GCCACCCATCGATCGTCGCGGTCCGGGAAACAACCAGAACAACAATCAGAACAGCGGTCCAGGGCCGAATAAGCGTTTTGAGCGACAACAGAACA
CCGCTCCCAAGGTCAACGATGAGCGTCAGTTTCCCACTCTGGCTTAA
(SEQ ID NO: 356)

Start ATG: 95 (Reverse strand: CAT)

MDSAGKNRYELLFMDDDVSDPLDNLVAPTAAAAAAAAGKKKQPSAAAAAATKTTANKVANSNNKANAGSNIGGPNAKKPNQAEKENKPNNALNKT
DGKKFTPSADNKQQQFNNNASSNYKQQGAPRQGGGANRTREFGSGQGQGQGQGGQQQRSVNFRQQNGNAETREQRNNRRNVRENVGAPDGQQSRP
YRGPGGGPGAGGDRPQRQNRNYDGQNRKREFDRQSGSDRTGVKSIDKRDGAGSHNWGSVKEAIDDVNKNESETNVTNAEGGAKADESGTEPQNEQ
ATAEEEAKELTLDEWKAQQGQRIKPTFNIRKAGEGEDTTQWKKMVVLTSNKKKENDSEEELEYDPALYPQRVGRQQRVLDIQFNFNDGRRGGPGG
FGGRGGRGGPRPGGFGGGPRSEGGNRDGGNREGGRDNREGGNRGPRDGQQHNNEGGGSSAQNQRPPIDRRGPGNNQNNNQNSGPGPNKRFERQQN
TAPKVNDERQFPTLA*
(SEQ ID NO: 357)

Gene Symbol: vig
FlyBase ID: FBgn0024183

Celera Sequence No. : 142000013384828
TTCCTCAAACGGTTATCTCGATCGTTAAATGATCAACACAGAAATGTATTCGATTTTATTATATATTTTTTATTTTAACACAATTGTTGTGTGTTTG
TGTGGCTCTTTCGTTTGTTGTAAATTATACAATTAATTAATATGTACTATATATAAATAAAGTATCTCAACTTTTCTATGATTGGTTCGCCTTGG
CATGTAAAAAATGTCCCCTTACGGCTTAATCGAGTCTTAGTGTCTACGGGAAAAGACTTACAAAAATACATATCGCATTGATTTATTGAACATTT
TCACTTATACATATGTCTCTATATTTATATTTATATATATTATATACCCTCTAATATAACATGGATATAGATGCACACGTGTTTCGTTCGCAATT
ACGATTCGATAAGTTTAAATTAGGTTAAACTAGTTTATACATGTACTAGAAGACAACCCTAAGAACTTATACAAATATTGATAGGGTTTGAAGCT
CTATATAAATTAAGATCGAAGAGTTAGATTAGAAATACGGACTTGTCTTATCAAATGTAGTGCCCCTTTGATTTTGTGTTTATTTCTTTTGGGTC
GGAAGTTTTAACGAATGCTAATTGAAGATCTGTCTTGTTGGGGCCCTAATGCGATATGATTCATCATATTATGTTATGTAATGCATTTTCAACTA
ACATATGTAGGTTATAAAATAAGCTAATAACTAGTGTTGGTATTATGAAGACTTATGCAACGAGAAATGCATACTGATTTCGGGATTCGCTTCTA
GGAATATTTCGTTTTATGGACATTTTAATTTATATTTCGATTTTATTTCTACCCCATTTGTGTTTCCCTAAATGTGTGGAATCGAAGCATTAACA
GTTCTGCACAAATTTGTGGTTTGTTCGCAGTTGCTTGGCTACATTAGTGTTTGCTTTAGTTTAAATAGTTCGTTTACGTAAGATCAAGATCACTT
TTTGCATTTACACAACAAACAACAAAAACGTCTTCCCCCGCGGCCCTTGCAATATTCCTCCATAAAAATATATATGTATATATATAATATATAGT
TTACCCATATATATATGGGTATATATCTCTGAATCGACTTTGGACGCCGGCTAGGCCGGCGCCTTGTCCCGACACTATCAACATCCGTACAACTC
TTAGTATATAAAAAGTCTTTTCAATTTCTACGTCATCATACCGCGGCTGGCGAAGATTCCTAGATGCGCCAGCCCTGGTCATCGTCCACGTTGGA
GTCTGTGTCTGAGGGCTCCTCGCCGTACATGTCGGCCAATTTGCGGAAGCGCGGTCCAAAGTTGGACAGGTAGTCGAAGTTGAGATCGCCGTCGT
CGGTGCAGGACGCCAGACTGGAGAGGCTGCCATCGGAGTTGCCGTCACCTTCGTACGCGTAATGCCGCACATCGTCCACGGTTGTGGCGCCCACA
TCCCGGTCGCAGTTCTCCTTCTTGTCGCCCAGGAAGTCGGCGATGTCGGGTATGTCGTTGGGGTCGCGCATGTTCCCCTGTAACGCATGAGGATC
TTTGTACAGCTTCTCCTCGTAGAAGGGCTGGGTGCGCAGGACATTCAGATCATAGTCCGTGTCCCGCTCGCCGCCACCCTCGTCCTCGTAATTAA
TGATCGTCTCGCGAATGTCGTCGATGTCCTTTTCGTGCCAGCCATTCTTCTGCTTTTTCTGCACCACCACTGCCAACAGGATGATCAGCAGTAGC
GCGAGGCATACGATGATCGCAATGATGAAGTTTCTATCAATTCCAAAACTGAACGCAACGGCCACCGACTGCTGGCAACCGCTGTCGATGTTTCG
GAACACAGAGGGCATTCCCAAGTTGTAAGTCTGCTCGTTAATTGTCAGGTTGCGAATGCAACCGAAGAAACCCTTCTGGTTGGGAACGTGCGTCC AATTGAGCTGCCGTCCCAGCTGTTCCAGATCCACTGGAGTGCCGCCCAACTGCAGCGGTGCGTTTACATTGAGGAACTCATTGGGGCCAATTGGG
GCGCCCAGTGTCTGGCAGGTGGATAGCCGGCAATTGTCCACAGTCATCTCAATGCTGGTACGCTGCAGGATAATGTCCAGTTGGTAGGTGCGGTC
TGCCACCATCTTGATGTGCTGATGGCGGATGCGAATGGCACCTGATCCGTAGTCCACAGTCAGCACCGGATAGCCATTGTCCAACTCCAGAGCTA
GGAAATCAGAAATGGCCAGCAGTGGATTGAAGTTAAGTGGTCCCAAGTACATGATCAGGCCCTGATCGATCTGGGGCGTGATCTCCAAGCTAATC
TTGGTGTTGTTGCAGGCGGCAATGGGCTCGTAGAAGGCATACCCCGAGCCATAGAATGCCACGGAGACGAGTTCGCAGTGGGGTCCGGTGAATCC
GTCTATGCAGTCGCACACGTCGTTCTCCCCGTACCGCGGAGATCCTCCGTTTAGACAACGCCTCATTAAAGGAGCCTCGCATACGCATTGCGCTT
GAACAAAGGCATTCACGCCCACGAACGATGTTGTATTGGAGTAGATCATGTATGGCACCGAGCTCTTGTGCAGCTCATTGGTGCACGATTCCTCG
CACTTGAACTTCTCAATCAGACACTCGTCGATGTTCACCATCAGCATTTGCAGGTCTAGTTCGTTTTCCAAACGCTGCTGATTCTGGGCCACTAT
TCCATTTAATTTCTCCGGAGCATAGTAGGGTGAGCCGTGGGCAGAGAAGCGTACATCGAGCGTATGATTCTCGTTTTGGAGCACAGTGAACACGT
CCACGTTGGATACCGACGTATTGAAAAGCTTGGCCAGCGAGAGCTGCAAGCGATCCTTTAGGGATAGCGCATCCGGTGACTGGAAGTCGCGTGGC
ACACTGATAAACTCCTCCTTGGTTACGTTGATGAATCGGATGCTGCCGCTCTTATCCACCGCCTCCTCGGGAAGCTCGCGGACCACCACGGTGAC
ATAAGCATCTACGGAGTGACGGGGCACGAACATGGAGTCCTCGGTGACTACGAACGACAGGTCGTACTCTCCCTCGGCGGTGTGAACCAGCATGG
TGATCATACCCGTGCTGGGATTAAGCCTAAACTGATCGTGCGGAAGATCTTTCCATTCAAAGTACTTGTCCTCCAAGTCCCAGTCATCGAGATCA
TCTACGAACACGCGACCAATATCGGTTTCAGGCGCTTCTCCCTTGTAATTGTAAATGAAGATGCGCGACGATCCCTCGCTCATGGCATTGTCGTT
GACATCGCCGATCACCAGGTGCAGAATGCTTACGGCACTCTGTCGCGGAACGCCAGAATCACTGATGCGAATGGGGATAAAGTACTCCTTTTGAG
CCTCGCGATCAAACTGGACGTTGGCGTGCAAATAGTCTCCATCCATGCTGAACTTGGTCTTGATGTCCGGTGTGGCTTCGCTGTCGATGCCGAAG
GTGAAGTTACCTGCCCCCGGAGTGTCGTCGTAGTCGTTGGCCTGCAGTTGCACAACATGTCCGGGATTGCGGTTCTCCTGCCAGTAGACAGGCAT
TTCGTTGATCAGGAACGGAGCATTGTCGTTGATGTCCTTCAACGTGACGGTGACCTCTTTCACTGTGCTGACCGTGGTTCCTACTCCATCCTCAT
CATTAGCCTTGATCAAAACCTGCCAGTTCTTGTGACCATTGGGCGGATCGCGGTCCAGCGTCTTGACCAAACGCAAGCAGCCACTGTTGTCAATG
GTCCATCGGTTTCCATCGTTCTGGTGAATCGAATAGACGATATGCTGATCTGCGTTGCGATCCTTGATATCCGGATCGTAGGCTTCGACAGTGAG
TATGCAGTCGTCATATGTGGTCTCCTCCAGAATGGTGACGCTGTAGTCCTGCTTAAACACCGGCGGGTTGTCGTTCACGTCTTCAATTTTGATAA
CCACCGTTGTGTAGTCGTCGTAGATTCCATCGAACGCACGCACCTTCAGCTCGTACTCCGTGATCGTTTCGTAGTCCAACTTCTGGTTGACCGTG
ATTTTGCCGGTCTTAAGACCAATCTTAAAGGCATCACCCACGTTACCGCTCTCAATGCTGTATAGGATCTGGGATGCGTTATCCTCGTCTTCGGC
CTTTACCTCAATGACCTCGGTATTCGTATTGGCATCCTCGAGCAGTCTTTCTGCCAGATATTTGTCCTGCTGGAAGTGCGGCTTGTGGTCGTTCT
TGTCTCCAATGGAGATGCGGAACACTTGGTGACCACGGTTCGGCTCGCCATTATCAAAGAGACTCGATGGCGAATTGTCGCTGGCAATAACCTTT
ACGTTATAGAAATCGCGTTCCTCGCGATCGAATGTCGTCAGGGCGGTTATGTTACCGGTATTGGGGTCGATGGTGAAGTACTCCCGATTGTCGGC
CAGCTCGAATGACACAATATTATTGGCTGAGGTGCCGTCCATGTCGAAGGCACGCACCTGCATAACAGGCGTGCCGGGTGGTTCGTTCTCCAGGA
TAGTGCCCGATTTGACCTCCGTGTAGTAGGGGATGTTATCGTTGACATCCTCCACCTGAATCTTGATCTGATGCTCTGTGCCCAGCTCGTGTGTA
TTCCGCACAATCATGGTGAGGGTGTAGTCTGTGATGGCCTCGTAGTCCAGAGTCTTGCCCAGGCTAATGGTCACCTCGTTGCCGATCTGATTGAA
CACGAATGTGTTCTTGCTGTTTGTCTGCTCCGTGCGGCCGGTGTTCAGTTCGAAGATTACCTCCGGCTTGTCCGGCATATTGGAAACGGCTCGTA
ACGTGGCGATCGGATGTGTAAAGTTCTTGAGATTCTCCTTCAGGTAAATGGGCGTATCGATCGGATTCACAAATGATGGCGGCTTAATTGAGGAC
TCCACCACCCGGATGCGCACTTCGATTTGTGCATCCTGTGGCGGATCTGGCACTACGTTATATGCCCGCACGATTATCGCATACGATTGGCCGGG
TCTCTTGTCAATCGGTCGTTTCAGGTAGATAATACCCGACTCCTTGTCAATCTTGAAGTACTGAAAGTCGCGCTCCCGCAGAATCTCGTATTCGA
CCAAACTGTTGTTGCCATCGTCGAAGTCACTGGCGCTGATAGTCATCACCACCGCGTCGGGCTGCAAGTAGAAGGTAAAGATAAAGCCACAGATA
TTTGGGTGTTTCTGGTTTCCTTCCTTCCACACAACTTTCCTGCAAGTTTGCCCAAACCAGGAGCAAGCACATGACCCCGCTCTAGTTTCCTGAAT
CTCCTTTTACTCAATGCTACCTGGGCGAAGGCCTAATTAGAACTGAAACCTTTTCGCAGAAAAGCTTCTCTGCTAACAAAGCTTTGCTAAAAATA
ACAGCGTTTGTTGTGTCGAGGAAAATAACACATAGAAGTTAGATAACTATCTGCTGTACTATCCCTTAACTACAAAGTAAAAAGACTTTCCGATA
TTGATTGCAAATCAAAGATGCTCCTGAAGATCCTCAGAATATCAGATCTAATCTAAGAAACCTTAATAAAATTATAATATATTTCTAACTAATCG
AAGTAATTACCGAAAAGGGCTCTCTATTGCGGTTTTGGTACAAAAACTGCACGCTATTACAAGTACTTAGCTAAATTTAGTTTTCTACCACTGTT
TTGTAGTTCGACAAGTTTTTCTGGTCGCAAACATGGAAATGGCGTAAAAGAAAAGGCGTTGGAAAGGGTTTCAAGGTTTTCTGTATCGAACCGGG
CGAGCAATGAACCCAAAACCCGTCTCCAAGTGGTCGCCCTCCTACGCCAAGCGAAAACTAGTTCCGCCCAAGAAGATGTGCGCCCATGAACTGGC
CAAGTGTTTAATTAACACCGTAGGACGTGCGACAGTGGGAGCCTCAGTCTATTGGAATGACCAGGTGGGCAGAGGGCAAATCTTATGGTGCCAGT
GATCCATAAATATCAGTAGTCAAAAACATGATAGTTTTAGTAACAGCATAAATAAGCAAAAATCAGCTAACAAATATTTTCTTTTAATTTTTAAG
CAAGATTTTATCTTAATATATTTTTGGTTAAAAGACATTTCTACTACTACACTCCAGTGAAAAGAGAAACTTGAAGCAACAATTGAGTTAGGTAC
ATGACATCACAAGAGGGGGCAAGACAGAAAGAATGACATCACTCTAGTACCAATTCACCAGCTTGGCCAACCCGCAGTAATCCGGGGTCCGCGAG
TTTGGCAAGCGGTGGTGGATAGAGTGGGCCAACTCGAACTCGACTCAGTGGGCCAGGAAACTCACCTGGGCATTTTCCGACATGGATTCGTCGTA
GCGCGCCTTGTTGAAGGCGGGTGCATTGTCGTTGATGTCCTCGATGGTAACGTTGAAGGTGCAAACGTCGTCCAGTGGGGGCAGACCATTATCCG
TGGCCTGGACGGTGACGAAGACGAACTTCTCGTGGATCGGCTCGTCACGATCGAATGTGTGGGTGGTGAAGATTACGCCCGTGCTGGGATTGATA
AAGAACTTGGGTCGCTCGAACGGCGACTGGACGATGCTGTATCGAATGACCTGGTCGGGATCAGGGTCGACGGCCTCTACGGTGAGAACGTAGGT
GTTTTCGGGCTGCTCCTCTTTGACCTTAGGAGCGTATCCGGCGCAGTTTTTGAAGGCGGGCTTACGATTGTCGCCGGAAAAGTTTTTGTCCGGCG
GCGAGTGAAGTGCGAGGGCGGGTGACAGAAGGCTGATGGCCACGATAACGCCCAGGAGGAGTCTCGCGGGGATTAGTCGCCTGCCAAGGTCGCGG
CATTTTCGCTTGTGCTGCTGGTGCGTCTGTTGCTGGGCGGGATTTAGGTGGCCGGCCTGCGGGGTCGCCGACATATTGATGCAGTGGTAGCTTCT
GGACATTCGCTGGACACTGGTGGACATACTCTCTAGCGGCGATCCGCCATCGCAGACTCTCTTTTTTTCAACCGCAACACTTTTGAGCACTTCTT
CGTGAATCACCCAGTATTATTTCACTCACACACCTTTTACTTTTGTTTGTGTTGCCCACTTCTACTTCCACTTCTTTTTTATTCTATTCTATTTG
CACTCTTCTTCTTGTTTCGTTTCTCTCAGTGTACCGTTTGTTTGGACTGCATTTTCATGGCAACCGCTCAATAATTATCAATCGAATCGAACTCG
TACAGTGCGCGCCCTGATTGTTAACTGACTTATTCCGATTTCGGTGCAGCTGCTCTGGCTGATATTTTCGTTCACTTTTATCTTTCACTCGTCCG
CTTGGGCACTCTCTTTCTCCGTTTCTGTTGCCTCCTCTCTTTCGCACCGCAAACAGGTAAGACCAGGTAAAAAAGTGGTTACACGCACACCGCCA
AGCGCGCGCATTTGTGTGCGTGTGGTTCGGTTCGCTGCGTTGGTATGTGTGTTACCAACGACTTTTGGTAAAAAGGCACTTTTCGATGGTATTTC
GTTGTGAACTTGTACTTTCTGGCGAATTATTTTAAATAAAAAGATCGCAAAACGTATTTTCTTTCACTTCGATCGCTTTTATTGTCGACTTACAA
CGAAGCTGCGGAGCCACACCGATTTTGAAACTGCGATCGACGCGCGAGACAACCGCTCAATTCAAAAGCAAAAACACAATGCAACAAAAACAACG
GGCGGCGTTAGAGATGTGAGACACCGTCGATTCCTCGGTCATCGATAATTAACGGTTAATAATCTCGATGTTTTCGTTTTATCGATACTATATAC
TGTCTACACTTCTCGATAAATACGTTGATGTGAATCAATTACACTGGATTTAATATAACAAATATTTCTTTAAAAATGGAAGCTGGAAGATAAAA
ATGGCCCAGCTTGGGCTTTCAAATAGAATTATTAACAACTATTTTTCACAAACAAACAGGTTAATTTTAAACGAGTTGATCAATACTTTAATACT
TATATAACTGAAAAATATTTAATAACCAAAACTAGCTACCATGTACAACAATAACATAATTTGCTTTAAAAAAGTTCTGATTGAGTTTGGTTTTG
AACAGGCAATGATATTTATTGGTCTCGAGGAACTATTTCTATAATGTATTACATTCTACATCGTTAAAAGTTTTTTATTGCAATTCAAGTAACG
CGCCAAGACTTTTGCCATTCACCCGTCGGATTATGGAGCAGTGTAGACTGCCCGTAAAATACGGTGAATCGCATCCGGTACAGGTACACAAATAT
TTCCCATCCCTAGCAAAGAGTGGAAAAAAAAGTGAATCGAATCGTCATCGTCTTGGCCCATTAATTGCGGAGAAAAAAGATTGCAGCGCCGAAAA
AACGGTCAAGGAAGAGTTCCAGCGACACCGCAACTTCCAACCACTCCACAAGAAGATCCCGTCGAAAGGTAGAACCCTAGGAACCGGAGGGGAAA
CCAGACCAAACCAAACAACCGCCCAGCCCCGATTTCGTGAATCACCAGTGGAACTATGGAGCAGACACCGATCACCGATGCGGAGAAGGTGCGCA
TCGTATCGGACTTCATCCTACATGCGCCGCCCGGCGAGTTCAACGAAGTGTTCAACGATGTGCGGGAGCTCCTCAAGAATGACACTCTGCTAAAG
GATGGGGC

FIGURE SHEET 196

(SEQ ID NO: 358)

Exon: 7558..6241
Exon: 5096..1001
Start ATG: 6867 (Reverse strand: CAT)

Transcript No. : CT12481
GTTGTCTCGCGCGTCGATCGCAGTTTCAAAATCGGTGTGGCTCCGCAGCTTCGTTGTAAGTCGACAATAAAAGCGATCGAAGTGAAAGAAAATAC
GTTTTGCGATCTTTTTATTTAAAATAATTCGCCAGAAAGTACAAGTTCACAACGAAATACCATCGAAAAGTGCCTTTTTACCAAAAGTCGTTGGT
AACACACATACCAACGCAGCGAACCGAACCACACGCACACAAATGCGCGCGCTTGGCGGTGTGCGTGTAACCACTTTTTTACCTGGTCTTACCTG
TTTGCGGTGCGAAAGAGAGGAGGCAACAGAAACGGAGAAAGAGAGTGCCCAAGCGGACGAGTGAAAGATAAAAGTGAACGAAAATATCAGCCAGA
GCAGCTGCACCGAAATCGGAATAAGTCAGTTAACAATCAGGGCGCGCACTGTACGAGTTCGATTCGATTGATAATTATTGAGCGGTTGCCATGAA
AATGCAGTCCAAACAAACGGTACACTGAGAGAAACGAAACAAGAAGAAGAGTGCAAATAGAATAGAATAAAAAAGAAGTGGAAGTAGAAGTGGGC
AACACAAACAAAAGTAAAAGGTGTGTGAGTGAAATAATACTGGGTGATTCACGAAGAAGTGCTCAAAAGTGTTGCGGTTGAAAAAAAGAGAGTCT
GCGATGGCGGATCGCCGCTAGAGAGTATGTCCACCAGTGTCCAGCGAATGTCCAGAAGCTACCACTGCATCAATATGTCGGCGACCCCGCAGGCC
GGCCACCTAAATCCCGCCCAGCAACAGACGCACCAGCAGCACAAGCGAAAATGCCGCGACCTTGGCAGGCGACTAATCCCCGCGAGACTCCTCCT
GGGCGTTATCGTGGCCATCAGCCTTCTGTCACCCGCCCTCGCACTTCACTCGCCGCCGGACAAAAACTTTTCCGGCGACAATCGTAAGCCCGCCT
TCAAAAACTGCGCCGGATACGCTCCTAAGGTCAAAGAGGAGCAGCCCGAAAACACCTACGTTCTCACCGTAGAGGCCGTCGACCCTGATCCCGAC
CAGGTCATTCGATACAGCATCGTCCAGTCGCCGTTCGAGCGACCCAAGTTCTTTATCAATCCCAGCACGGGCGTAATCTTCACCACCCACACATT
CGATCGTGACGAGCCGATCCACGAGAAGTTCGTCTTCGTCACCGTCCAGGCCACGGATAATGGTCTGCCCCCACTGGACGACGTTTGCACCTTCA
ACGTTACCATCGAGGACATCAACGACAATGCACCCGCCTTCAACAAGGCGCGCTACGACGAATCCATGTCGGAAAATGCCCAGCCCGACGCGGTG
GTGATGACTATCAGCGCCAGTGACTTCGACGATGGCAACAACAGTTTGGTCGAATACGAGATTCTGCGGGAGCGCGACTTTCAGTACTTCAAGAT
TGACAAGGAGTCGGGTATTATCTACCTGAAACGACCGATTGACAAGAGACCCGGCCAATCGTATGCGATAATCGTGCGGGCATATAACGTAGTGC
CAGATCCGCCACAGGATGCACAAATCGAAGTGCGCATCCGGGTGGTGGAGTCCTCAATTAAGCCGCCATCATTTGTGAATCCGATCGATACGCCC
ATTTACCTGAAGGAGAATCTCAAGAACTTTACACATCCGATCGCCACGTTACGAGCCGTTTCCAATATGCCGGACAAGCCGGAGGTAATCTTCGA
ACTGAACACCGGCCGCACGGAGCAGACAAACAGCAAGAACACATTCGTGTTCAATCAGATCGGCAACGAGGTGACCATTAGCCTGGGCAAGACTC
TGGACTACGAGGCCATCACAGACTACACCCTCACCATGATTGTGCGGAATACACACGAGCTGGGCACAGAGCATCAGATCAAGATTCAGGTGGAG
GATGTCAACGATAACATCCCCTACTACACGGAGGTCAAATCGGGCACTATCCTGGAGAACGAACCACCCGGCACGCCTGTTATGCAGGTGCGTGC
CTTCGACATGGACGGCACCTCAGCCAATAATATTGTGTCATTCGAGCTGGCCGACAATCGGGAGTACTTCACCATCGACCCCAATACCGGTAACA
TAACCGCCCTGACGACATTCGATCGCGAGGAACGCGATTTCTATAACGTAAAGGTTATTGCCAGCGACAATTCGCCATCGAGTCTCTTTGATAAT
GGCGAGCCGAACCGTGGTCACCAAGTGTTCCGCATCTCCATTGGAGACAAGAACGACCACAAGCCGCACTTCCAGCAGGACAAATATCTGGCAGA
AAGACTGCTCGAGGATGCCAATACGAATACCGAGGTCATTGAGGTAAAGGCCGAAGACGAGGATAACGCATCCCAGATCCTATACAGCATTGAGA
GCGGTAACGTGGGTGATGCCTTTAAGATTGGTCTTAAGACCGGCAAAATCACGGTCAACCAGAAGTTGGACTACGAAACGATCACGGAGTACGAG
CTGAAGGTGCGTGCGTTCGATGGAATCTACGACGACTACACAACGGTGGTTATCAAAATTGAAGACGTGAACGACAACCCGCCGGTGTTTAAGCA
GGACTACAGCGTCACCATTCTGGAGGAGACCACATATGACGACTGCATACTCACTGTCGAAGCCTACGATCCGGATATCAAGGATCGCAACGCAG
ATCAGCATATCGTCTATTCGATTCACCAGAACGATGGAAACCGATGGACCATTGACAACAGTGGCTGCTTGCGTTTGGTCAAGACGCTGGACCGC
GATCCGCCCAATGGTCACAAGAACTGGCAGGTTTTGATCAAGGCTAATGATGAGGATGGAGTAGGAACCACGGTCAGCACAGTGAAAGAGGTCAC
CGTCACGTTGAAGGACATCAACGACAATGCTCCGTTCCTGATCAACGAAATGCCTGTCTACTGGCAGGAGAACCGCAATCCCGGACATGTTGTGC
AACTGCAGGCCAACGACTACGACGACACTCCGGGGGCAGGTAACTTCACCTTCGGCATCGACAGCGAAGCCACACCGGACATCAAGACCAAGTTC
AGCATGGATGGAGACTATTTGCACGCCAACGTCCAGTTTGATCGCGAGGCTCAAAAGGAGTACTTTATCCCCATTCGCATCAGTGATTCTGGCGT
TCCGCGACAGAGTGCCGTAAGCATTCTGCACCTGGTGATCGGCGATGTCAACGACAATGCCATGAGCGAGGGATCGTCGCGCATCTTCATTTACA
ATTACAAGGGAGAAGCGCCTGAAACCGATATTGGTCGCGTGTTCGTAGATGATCTCGATGACTGGGACTTGGAGGACAAGTACTTTGAATGGAAA
GATCTTCCGCACGATCAGTTTAGGCTTAATCCCAGCACGGGTATGATCACCATGCTGGTTCACACCGCCGAGGGAGAGTACGACCTGTCGTTCGT
AGTCACCGAGGACTCCATGTTCGTGCCCCGTCACTCCGTAGATGCTTATGTCACCGTGGTGGTCCGCGAGCTTCCCGAGGAGGCGGTGGATAAGA
GCGGCAGCATCCGATTCATCAACGTAACCAAGGAGGAGTTTATCAGTGTGCCACGCGACTTCCAGTCACCGGATGCGCTATCCCTAAAGGATCGC
TTGCAGCTCTCGCTGGCCAAGCTTTTCAATACGTCGGTATCCAACGTGGACGTGTTCACTGTGCTCCAAAACGAGAATCATACGCTCGATGTACG
CTTCTCTGCCCACGGCTCACCCTACTATGCTCCGGAGAAATTAAATGGAATAGTGGCCCAGAATCAGCAGCGTTTGGAAAACGAACTAGACCTGC
AAATGCTGATGGTGAACATCGACGAGTGTCTGATTGAGAAGTTCAAGTGCGAGGAATCGTGCACCAATGAGCTGCACAAGAGCTCGGTGCCATAC
ATGATCTACTCCAATACAACATCGTTCGTGGGCGTGAATGCCTTTGTTCAAGCGCAATGCGTATGCGAGGCTCCTTTAATGAGGCGTTGTCTAAA
CGGAGGATCTCCGCGGTACGGGGAGAACGACGTGTGCGACTGCATAGACGGATTCACCGGACCCCACTGCGAACTCGTCTCCGTGGCATTCTATG
GCTCGGGGTATGCCTTCTACGAGCCCATTGCCGCCTGCAACAACACCAAGATTAGCTTGGAGATCACGCCCCAGATCGATCAGGGCCTGATCATG
TACTTGGGACCACTTAACTTCAATCCACTGCTGGCCATTTCTGATTTCCTAGCTCTGGAGTTGGACAATGGCTATCCGGTGCTGACTGTGGACTA
CGGATCAGGTGCCATTCGCATCCGCCATCAGCACATCAAGATGGTGGCAGACCGCACCTACCAACTGGACATTATCCTGCAGCGTACCAGCATTG
AGATGACTGTGGACAATTGCCGGCTATCCACCTGCCAGACACTGGGCGCCCCAATTGGCCCCAATGAGTTCCTCAATGTAAACGCACCGCTGCAG
TTGGGCGGCACTCCAGTGGATCTGGAACAGCTGGGACGGCAGCTCAATTGGACGCACGTTCCCAACCAGAAGGGTTTCTTCGGTTGCATTCGCAA
CCTGACAATTAACGAGCAGACTTACAACTTGGGAATGCCCTCTGTGTTCCGAAACATCGACAGCGGTTGCCAGCAGTCGGTGGCCGTTGCGTTCA
GTTTTGGAATTGATAGAAACTTCATCATTGCGATCATCGTATGCCTCGCGCTACTGCTGATCATCCTGTTGGCAGTGGTGGTGCAGAAAAAGCAG
AAGAATGGCTGGCACGAAAAGGACATCGACGACATTCGCGAGACGATCATTAATTACGAGGACGAGGGTGGCGGCGAGCGGGACACGGACTATGA
TCTGAATGTCCTGCGCACCCAGCCCTTCTACGAGGAGAAGCTGTACAAAGATCCTCATGCGTTACAGGGGAACATGCGCGACCCCAACGACATAC
CCGACATCGCCGACTTCCTGGGCGACAAGAAGGAGAACTGCGACCGGGATGTGGGCGCCACAACCGTGGACGATGTGCGGCATTACGCGTACGAA
GGTGACGGCAACTCCGATGGCAGCCTCTCCAGTCTGGCGTCCTGCACCGACGACGGCGATCTCAACTTCGACTACCTGTCCAACTTTGGACCGCG
CTTCCGCAAATTGGCCGACATGTACGGCGAGGAGCCCTCAGACACAGACTCCAACGTGGACGATGACCAGGGCTGGCGCATCTAGGAATCTTCGC
CAGCCGCGGTATGATGACGTAGAAATTGAAAAGACTTTTTATATACTAAGAGTTGTACGGATGTTGATAGTGTCGGGACAAGGCGCCGGCCTAGC
CGGCGTCCAAAGTCGATTCAGAGATATATACCCATATATATATGGGTAAACTATATATTATATATATACATATATATTTTTATGGAGGAATATT
(SEQ ID NO: 359)

Start ATG: 692 (Reverse strand: CAT)

MSTSVQRMSRSYHCINMSATPQAGHLNPAQQQTHQQHKRKCRDLGRRLIPARLLLGVIVAISLLSPALALHSPPDKNFSGDNRKPAFKNCAGYAP
KVKEEQPENTYVLTVEAVDPDPDQVIRYSIVQSPFERPKFFINPSTGVIFTTHTFDRDEPIHEKFVFVTVQATDNGLPPLDDVCTFNVTIEDIND
NAPAFNKARYDESMSENAQPDAVVMTISASDFDDGNNSLVEYEILRERDFQYFKIDKESGIIYLKRPIDKRPGQSYAIIVRAYNVVPDPPQDAQI

FIGURE SHEET 197

EVRIRVVESSIKPPSFVNPIDTPIYLKENLKNFTHPIATLRAVSNMPDKPEVIFELNTGRTEQTNSKNTFVFNQIGNEVTISLGKTLDYEAITDY
TLTMIVRNTHELGTEHQIKIQVEDVNDNIPYYTEVKSGTILENEPPGTPVMQVRAFDMDGTSANNIVSFELADNREYFTIDPNTGNITALTTFDR
EERDFYNVKVIASDNSPSSLFDNGEPNRGHQVFRISIGDKNDHKPHFQQDKYLAERLLEDANTNTEVIEVKAEDEDNASQILYSIESGNVGDAFK
IGLKTGKITVNQKLDYETITEYELKVRAFDGIYDDYTTVVIKIEDVNDNPPVFKQDYSVTILEETTYDDCILTVEAYDPDIKDRNADQHIVYSIH
QNDGNRWTIDNSGCLRLVKTLDRDPPNGHKNWQVLIKANDEDGVGTTVSTVKEVTVTLKDINDNAPFLINEMPVYWQENRNPGHVVQLQANDYDD
TPGAGNFTFGIDSEATPDIKTKFSMDGDYLHANVQFDREAQKEYFIPIRISDSGVPRQSAVSILHLVIGDVNDNAMSEGSSRIFIYNYKGEAPET
DIGRVFVDDLDDWDLEDKYFEWKDLPHDQFRLNPSTGMITMLVHTAEGEYDLSFVVTEDSMFVPRHSVDAYVTVVVRELPEEAVDKSGSIRFINV
TKEEFISVPRDFQSPDALSLKDRLQLSLAKLFNTSVSNVDVFTVLQNENHTLDVRFSAHGSPYYAPEKLNGIVAQNQQRLENELDLQMLMVNIDE
CLIEKFKCEESCTNELHKSSVPYMIYSNTTSFVGVNAFVQAQCVCEAPLMRRCLNGGSPRYGENDVCDCIDGFTGPHCELVSVAFYGSGYAFYEP
IAACNNTKISLEITPQIDQGLIMYLGPLNFNPLLAISDFLALELDNGYPVLTVDYGSGAIRIRHQHIKMVADRTYQLDIILQRTSIEMTVDNCRL
STCQTLGAPIGPNEFLNVNAPLQLGGTPVDLEQLGRQLNWTHVPNQKGFFGCIRNLTINEQTYNLGMPSVFRNIDSGCQQSVAVAFSFGIDRNFI
IAIIVCLALLLIILLAVVVQKKQKNGWHEKDIDDIRETIINYEDEGGGERDTDYDLNVLRTQPFYEEKLYKDPHALQGNMRDPNDIPDIADFLGD
KKENCDRDVGATTVDDVRHYAYEGDGNSDGSLSSLASCTDDGDLNFDYLSNFGPRFRKLADMYGEEPSDTDSNVDDDQGWRI*
(SEQ ID NO: 360)

Name: DE-cadherin
Classification: cell_adhesion
Gene Symbol: shg
FlyBase ID: FBgn0003391

Celera Sequence No. : 142000013384832
ACTTGCAATATTGGTATCAAACTCTCGCACACGCGAATTAATGCGAGACTATATCGGTTCGGAGCGTACTAGTTCGGATCGAATCGAGTAGTGGA
GGGAGCGGTGTGGACGCTGCGAAGCTCGAAAGAAGACTGAACGCGACCAGCCCGGTGGTTGTCAATATGAATACGTTGTGGAGTGGACTAGCAGT
GCTTTGGGATGTTGCAAACCATGCCGAAACGAAGCAAAACCACTGGCCTGGCTGCACGCCGTACTGTGGTAGGTATTCGGCAGGTGTTGGTACAG
ACATAAATATCTATTAGCTCGGCTAATCTAGGCGGAACTGGCCGTCTGGCCTAAGAGGCTTAGGCTGGGTCCAAGTGATGGGCCAAGTAGTTGAC
TTTTGACTACATGGGCGGGACTGCTGGGTACCACAAGATGCAAGTCCCAGGCCCAGGAACTCTTTGGCATATTTTGGGAAACATTAACTTTGCCA
TTTGGACGAGTTTTATTGACTTTGCTGCTTTTCAGCGAATAAGATATATTGGCATCATTATGGATGCAAAATTAGCAACGGATCGAATTGGTTTC
CATTACACAATGGTCCAGCTTTGCATTCGCAGCCACCGCGGCGGTGGTTTCCACTTTGTTTGCCTTAATTAGGTGGTTATCAATCTCCTATGCAA
ATCTATTGTTGCCCAATGTCGCGAATATTGGTAATTAGTGCAGTCTTTCCTGTGATTTTTGCACACGCTAAATTATGCATGTTACCAATTTTGTT
GCAAAAAAAATAATATGTTTGTGTCTTCCAGTCCCAACTGATGGTTTCAAAAAGGCCGCCAAAGTTGAAAATATCGATATCATGCAGATGATATAT
GGATACTTGTCCTGCTAAGGTAGTGCTGTCAGAGTTGCTTAAACTGATTAGTTATAATAAACCATCAGTTAATTCCAGGTATGAAAAAAAGCGTG
CATTATGTAAATTGCATAGTGAAATTAAATCGACAATTTGTAATCTCGCTGCGAATTTCCAGGAATCTCCAGCCCTGGCCGGCTTATCGATACAT
CTGGCACAAAAGGCGTGCAGAGTTGTTCTCCAAATTTCCTGTCGCGAATTTTATTCATTTATAATTAATTACAAGCCATGGCCGAACTGGACGAT
TTCTTCGCGAAAAAGGACAAGAAGAAGTCCAAGAACAAGACTAAGTTCGTGACCGCCGACGAGATGGTGAAGAACCTGGAGGACGGCACCAAGCG
CGAGGTGGTCAAGCCCAAAAAACCTGAGGTAGCCGCTGGCGGCGTGGCAGTAGTAGGCGAAAACGAGAATAGCGGCACCAAGGTGCCAGAGTCCG
CCCCGGTGAGTCCGAATCTCAGTCTGGTGAAATCAGCGCCCGTTGGCCACCTAGGGCATGTTTATAAGTTCATTGTTTTGCCGCTCCGTAGCCCG
TCGAGGAGGAATGGAAGGAGTTCGAGGAGGAGCAGCGCAAGGACTACAGTGGCTTAAAGATCGGCCAGCTGAGCACCATGTGAGTTTTCGAACGT
TACGCCGACCGCCTAATCCATGAGCAGGAGAAAAGGCCACTTCCATTGATTTACTTTCCATTTGACCCCGCATATTGCGAAAACTCGCTTTCTAT
AGCTCTTCGGCCCGTTCCAGAACTGCCCAGGAAAGTTCCGAGTCGCAAGCTGCTCGAGTGCCCTCTGCCCCGGACGGCGGCAACTACAATGAGGA
CGATGAGGACAGCAATGGGTATGACAACGCGGACGTAAACAAGGAGCGCGTCGGCCACGGACCCTGGAAGAAAGTTGTCCCAGCCGAGGAGGTAA
TGCAGATTCCGGTGCCCGTGGAGGTGGAAAAGCACTCGTCCAAGACCTACGTTTCACCCGCGCTACGATACAGCGTAAGTAAGAAGAGCGAGACG
ATCCAGATCGAGTTTAATCAACTTCTCTGCAGCAGCAGGCCGGAAGTGGACTGGGAGGCGGCCCTACTGGGGGGGCATTGCGTCCACGACGCGCC
GCCCCCGACATCACCAATACCGAGTTTTTCCCAACCTTAAGTGCGGCGCGTCCGGAGGAACAGCGCAAGAAGAAAAACGAACCCGCCTTCGAAGA
AGTCCGTCACGGAAGCCGTTTCCAGCGTGTTCCAGGAGTCCACGGCTGCCCCGGTGGCGGCCTCCAACCGATTCCAGTCGCTTGACGACGAAGCAA
GCTAGGTCAGCCCACGCCAACGGTGCTGTTGCTGGCCACTTGAACCGCTATCTACCACAGTGTCCGCTGCCGAGCTCAAGCCATCCAAAGGTTCT
ATGCCAGCACATGCAGATTTTCTAGGCTTTTTGATTCATATAAACCACCACTGCTACTCTTACCCTAAACCACAAACTACTATTGTTCATTTCGT
TTTGCATTTTGAAAAATGGATTAATGTAATACAATACGAATAATACCCATGCGTTGAAATCCGTTTATAAACGTTACTTTTTTATACGTTTCCGT
TTCTCACTTTTCCATGGCGAGGTCTTCCGGGCAGCTGTCCAAGTAGCTGCAAAATCAGTAAGAAAGATCATCTCTGGCTGAAACAGTGCGTACTG
ACTTTTCATTGTACGGCCTCTCCGGCGTGTTGTGGTACGAGATCAGCAGCTCCTTGGCCAGCATCTTGTCTGGGAAGTTGCGAATCAGGTACAGC
CAGCACTGAATGGTTCTAGACATAGGGGCAATAGTGAGTTATTACATCTGGCCATCACCCCACACCCTCATACTCATTCATCTGTTCCATTAATATGG
TTTGTTGCTCGCGATCATAGTAGTCGGGTAGTCTTCTAGTATGTCCAGTTTGGAGAGCATGGTCTCGTCCACTTCGTAGACTTCGCCTTCTATG
TGGTTCCCCTCACCCGGGCGGGCGAGCAGAAATGGGATGTTGTAGCGGGTTCCGACAACCAGGGGAAACTTCGTTTCCGTTTTCCCCCTTCCAAG
GAATCGGGCTTGGCCGTTCTCCTTTTTCGTCAGCCAGTGGTGATTGGGCTCACCGCGCTTCAACGTGCCATACACAAAGACCCTTGCCGCCATTC
TCAGCTTTTCAGCCATTGCGCTTCCCGCCGCCAGGCTTATCAGTTTCAAGCGGTATCGTGCTATCAAATCCGACCTGTAGATTGCGCAGTCGACA
TAACCCGTCCGCTCTTCTTCTTGCTGCCATTCGCACCGAATCTAGCCTCCGTACACCGCGAGAAACTGAAGCCCTCGGCACTGGGCTGTGGAAAA
TTACCAGGGACTGCTGTCCAGCATCTTTACTTCTATAATAGAACGAGGGGCATTTTATTTTATTTTAAATTGCTTCAGTTTATTTGCTTTGTTTG
TCGAAAACTATCAAATTACAGACTACGTTTGCTAAAACCTAAATAATGCGTATGGTACATATGTATCAGTTTATATCGTTTGCCCATATATACGG
GTATATATCGATCA
(SEQ ID NO: 361)

Exon: 1001..1335
Exon: 1422..1504
Exon: 1636..1879
Exon: 1933..2434
Start ATG: 1123

Transcript No. : CT12563
GCGAATTTCCAGGAATCTCCAGCCCTGGCCGGCTTATCGATACATCTGGCACAAAAGGCGTGCAGAGTTGTTCTCCAAATTTCCTGTCGCGAATT
TTATTCATTTATAATTAATTACAAGCCATGGCCGAACTGGACGATTTCTTCGCGAAAAAGGACAAGAAGAAGTCCAAGAACAAGACTAAGTTCGT
GACCGCCGACGAGATGGTGAAGAACCTGGAGGACGGCACCAAGCGCGAGGTGGTCAAGCCCAAAAAACCTGAGGTAGCCGCTGGCGGCGTGGCAG TAGTAGGCGAAAACGAGAATAGCGGCACCAAGGTGCCAGAGTCCGCCCCGCCCGTCGAGGAGGAATGGAAGGAGTTCGAGGAGGAGCAGCGCAAG
GACTACAGTGGCTTAAAGATCGGCCAGCTGAGCACCATAACTGCCCAGGAAAGTTCCGAGTCGCAAGCTGCTCGAGTGCCCTCTGCCCCGGACGG
CGGCAACTACAATGAGGACGATGAGGACAGCAATGGGTATGACAACGCGGACGTAAACAAGGAGCGCGTCGGCCACGGACCCTGGAAGAAAGTTG
TCCCAGCCGAGGAGGTAATGCAGATTCCGGTGCCCGTGGAGGTGGAAAAGCACTCGTCCAAGACCTACGTTTCACCCGCGCTACGATACAGCCAG
CAGGCCGGAAGTGGACTGGGAGGCGGCCCTACTGGGGGGCATTGCGTCCACGACGCGCCGCCCCCGACATCACCAATACCGAGTTTTTCCCAAC
CTTAAGTGCGGCGCGTCCGGAGGAACAGCGCAAGAAGAAAAACGAACCCGCCTTCGAAGAAGTCCGTCACGGAAGCCGTTTCCAGCGTGTTCAGG
AGTCCACGGCTGCCCCGGTGGCGGCCTCCAACCGATTCCAGTCGCTTGACGACGAAGCAAGCTAGGTCAGCCCACGCCAACGGTGCTGTTGCTGG
CCACTTGAACCGCTATCTACCACAGTGTCCGCTGCCGAGCTCAAGCCATCCAAAGGTTCTATGCCAGCACATGCAGATTTTCTAGGCTTTTTGAT
TCATATAAACCACCACTGCTACTCTTACCCTAAACCACAAACTACTATTGTTCATTTCGTTTTGCATTTTGAAAAATGGATTAATGTAATACAAT
ACGAATAATACCCATGCGTTGAAA
(SEQ ID NO: 362)

Start ATG: 123

MAELDDFFAKKDKKKSKNKTKFVTADEMVKNLEDGTKREVVKPKKPEVAAGGVAVVGENENSGTKVPESAPPVEEEWKEFEEEQRKDYSGLKIGQ
LSTITAQESSESQAARVPSAPDGGNYNEDDEDSNGYDNADVNKERVGHGPWKKVVPAEEVMQIPVPVEVEKHSSKTYVSPALRYSQQAGSGLGGG
PTGGALRPRRAAPDITNTEFFPTLSAARPEEQRKKKNEPAFEEVRHGSRFQRVQESTAAPVAASNRFQSLDDEAS*
(SEQ ID NO: 363)

Gene Symbol: anon-EST:fe2C9
FlyBase ID: FBgn0022343

Celera Sequence No. : 142000013385215
AATTAGCACATTCGTTTTCCTCTTTAAATAAGGAGAATCCACTTAAAGAAATCTGATAATCGCTGCATATTGTGCTATTTATTTTATGTTAAAAA
AGTATATTCGCAAGAGCATAAAAACAATCTGATCGGGTTAATCTTAACTTTTTCGCTGCTCCATTCTCATTGATTACTACAGCACAAAAAAAAAG
TGGGGAAAGCGTGGAATCCTAACTAGAAGAACGGAAGATAGAATAATGGATAAAAAACAAAGGGGCAGGGCAGCAAAAACTTAAATCATTGGCAA
ATACCTTTTTACGATGCGGATTTTAATCAAAGTTTTTGCCACCGCTGTCAGTTTCTTTTTTTACTTAAAATGGTAATAAAAAAAAAAGGGGAAA
CGACGATAAATAAACATTTTAAAATAATTGCTAACGGCGTGTTGTTGCGCTTTAGTGAACTTATTAGTCTACCCTCGCACCGGCCAATTTCCACA
ATTGATTAGTTTAAAATTGCATTTTTTGGACATTTAAATGGGAATCTAATTGATTGCCATTTTTATTGAGAGCACTTAACACTATACAATGGCAG
GTTTTGTATTTAAGCTATATATTCCTCGTTTATACAGTGTCAAATTAATTATTGATTTTATAAGCAGCTAAGAAAATGATTGTTTAATTTGGACC
GATTGATCATCGAGGACTTAAAATGGACTTAAAATAATTGGATATTAGCAACTTTGAAAAGATCCCGTTTACTCCCAAAACTTCAGAATCAACCC
ACGAACTTCTTTAAGCCAGTGTGACCCCACCCGCTCTTTAGCTCTCTTTCGCTCCATCTCGCTTCCGCACATCGATTGGCGAAAGCTTCGCTCGC
ACTCGATATCAGCTCACAACTTCGCTTGCAAGCTCGCCGCGGAAAGCTCGCGATCACACGGGTCGAAATCGAAATCGAATCGCGGTAGAGAGCTT
TTCGAAGTGCGAGCGTCGACGTTTTATTTCTGCGGCTCAGTCGGTTTTAGTTCGTTCTGTTGGAGAAAAGCAGCAATCACACGTTCGCAAGGTGA
ACGCGAAGACACAGCAAAGTAAGCCCTTCCCCCCCACCAACACACACACCCACCCAAAGCAAATAAGTAACAATAAATAATGGAATGGCTGGAAG
ACGGTTCTGGGCGATTTAAACAATTAGCGAAAGAAAGCGGCATTGAAATCCGTCTTGAATTCGCCCCGAAAAAGTGACGAAGCAGCGATCAAAGC
GCAGAGCGAAAACACGCACACAGACTGCAAGTGTGTTAGATAATAAGTGCAGCACAAGTCCACACTTGAGTAAAATAATCCCTAAAAAAGCCGAA
TATCAATTAGTTTTCCAAGGAGCTTGAAAAAGTGCGGTATGAAAACGTGAAAATTTGCGCGTGGAAAATTATTTTGCCTTGTCAGCTGACCCCCT
TCCCCGTGTTCGCTCCATCCCTGTCGCACCGCGGGTCTTGTGATCGCCGCCGCTCTTGCGCTCGCTTGCTCTCCCATTTCGAAACTCGAAACAGA
AGTGGGAGTTATTCGTATTCCGATAATGAAAAACCAATATGGAGAACGAGCGACGTAAAAAAGGCGGCCCAAAGATTTTTACCATTTCCCTTACC
CACTTTTTTTTCATTTGTCAGCTGACGGCAATGACAGTAGTCTTGTGATCAACGTCAAAAGCAATTGTCAAATATTCGAACTCGAATGGAGAGCG
AGAGAGCCAGAGCGGAGAGTTGCTCTCCCACTCCACCCTCTCTTGTTTTTCTTTGCTGATAATTATGAAAACCCGCATATTTTGAAAAACATGCA
TTTCAGTTACATTCCTCCGTTGAATTTGTCAACCTGTGGTTGTTTTTCACAGCTCTTATTTTATTTATTTAGCGATTAGTTTGACAAATTGCTC
TCTTCGAACTTTCAAAGCTCTGTCACGTGAAACGAAAGCTCTGCTTTTAAAGTTTTACGCAGCATAATCAAAGAGGGGGAGTTAAAAAAAAAATA
ATTAAATCAATCGAAATTATTAGCTGCTAACCTACAACTTTATAACCTATAATCGAAAAATTTGGGAGCTGTGGGCTCTACAAAAACTTAACCTG
TAAATGTAGCAGATACACCTGCCCCTTGTCAGCTGACAGAGGGCTGAGCAAGAAATTAGTGATAAGAAAATGTTCACCTTTATCTTCGCCCTTTT
GCAGCCAGCATTTAACAATTTTCCTCTTCTATTTTCCCTCCATTGCAGTCGAAAAAACAGAATAAAGCAAAATGTCCAACCTTAAGCGTTTCGAT
GATGAGGAGCGTGAGTCCAAATATGGACGTGTCTTCGCTGTCTCCGGTCCTGGTAAGCACCTAACTATACTGACTAACCATAACTCATGCTATCT
AAAAGTTAATAAAAATAAGTTAATAATACCTGTGAACTGGAAACCTTACTTTGATGATTAGTCTAGAACTTACACTTCTGTGTGAAATAATGGCA
ACTTTAGAAATGTGTCCACCTATTTGTGATTAATATTCAAACAACTCAAACATTTTGGTTTCATTATTCAAAATTAAATGTGAATAATTTTAATA
ATTAATTAATTGTTTCTTTAAACTTTTTTCTATAATTCTAACAAAAACATCATCAAGTATCATTAATAATAAAAAATTTTAAAAGAAAATGTTCA
ATGGAACCTATCTTCGTTTGCTGAGTTATAAAAACTTCTTGAATGAAATGTAGCCCCCCTAACCCGACCAACCGCTTCATTCCAGTCGTCACCGC
CGAGGCCATGTCTGGATCAGCTATGTACGAGTTGGTCCGCGTCGGCTACTACGAGCTGGTGGGCGAGATCATCCGTCTGGAGGGTGACATGGCCA
CCATCCAGGTGTACGAGGAGACCTCTGGCGTAACTGTCGGAGATCCGGTGCTGCGTACCGGCAAGCCTCTTTCCGTGGAGCTGGGACCCGGTATC
ATGGGCAGCATCTTTGACGGTATCCAGCGTCCCCTGAAGGACATTAACGAGCTGACCGAATCCATCTACATCCCCAAGGGTGTGAACGTGCCCAG
TTTGTCCCGCGTGGCCAGCTGGGAGTTCAACCCCCTGAACGTCAAGGTCGGCTCCCACATCACCGGAGGTGACCTGTACGGTCTGGTGCATGAGA
ACACTCTGGTCAAGCACAAGATGATTGTGAACCCCCGCGCCAAGGGAACAGTGCGCTACATCGCCCCCTCCGGCAACTACAAGGTCGACGATGTC
GTCCTGGAGACCGAGTTCGATGGAGAGATCACCAAGCACACCATGTTGCAGGTGTGGCCAGTGCGTCAGCCACGTCCCGTGACCGAGAAGCTGCC
CGCCAACCACCCCCTGCTCACCGGACAGCGTGTGCTCGACTCGCTCTTCCCCTGTGTCCAGGGCGGTACCACCGCCATTCCCGGAGCTTTCGGTT
GCGGCAAGACTGTGATCTCGCAGGTGAGAGTCCCACAAATTGAGAATTTAAGGAGCGATGCCTCGTGTAGCCTCCATACACTCAAGTTTCATAAA
AATACAATCCCTAATAAATCATTTACTTGCTTGCAGGCTCTGTCCAAGTACTCCAACTCCGATGTCATCATCTACGTCGGTTGCGGTGAGCGTGG
TAACGAGATGTCTGAGGTACTGCGTGACTTCCCCGAGCTGTCCGTGGAGATCGACGGTGTCACCGAGTCCATCATGAAGCGTACCGCCCTTGTGG
CCAACACCTCCAACATGCCTGTGGCTGCTCGTGAGGCCTCCATCTACACTGGTATCACCTTGTCCGAATACTTCCGTGATATGGGTTACAACGTG
TCCATGATGGCTGATTCCACCTCCCGTTGGGCTGAGGCTCTTCGTGAAATTTCTGGTCGTCTCGCTGAGATGCCTGCCGATTCCGGCTACCCAGC
CTACTTGGGAGCCCGTCTGGCCTCCTTCTACGAGCGTGCCGGTCGCGTTAAGTGCTTGGGTAACCCCGAGCGCGAGGGATCCGTGTCCATTGTCG
GAGCTGTGTCTCCTCCTGGTGGTGACTTCTCCGATCCCGTGACCTCCGCCACTCTGGGTATCGTGCAGGTGTTCTGGGGTCTCGACAAGAAGTTG
GCCCAGCGCAAGCACTTCCCCTCGATCAACTGGCTCATCTCCTACTCGAAGTACATGCGTGCTCTGGATGACTTCTATGACAAGAACTTCCCCGA
ATTCGTGCCGCTGCGTACCAAGGTCAAGGAGATCCTGCAGGAGGAGGAGGATCTGTCTGAGATCGTGCAACTGGTCGGCAAGGCCTCTCTGGCCG
AAACCGACAAGATCACGCTGGAGGTGGCCAAGCTGCTGAAGGACGATTTCCTGCAGCAGAACTCCTACTCCTCGTACGATCGCTTCTGCCCCTTC
TACAAGACCGTGGGCATGTTGAGGAACATCATCGACTTCTACGACATGGCCCGTCACTCCGTGGAGTCTACGGCTCAGTCTGAGAACAAGATCAC CTGGAACGTGATTCGTGAGGCAATGGGCAACATTATGTACCAGCTGTCATCCATGAAGTTCAAGGTGGGTTAACACGCAAATTTATCCATTGCCT
AGACACTGGGTGACCACATTTTTCAATCCATTTCAGGACCCCGTTAAGGATGGTGAGGCCAAGATCAAGGCTGACTTCGAGCAGCTGCACGAGGA
CCTGCAGCAGGCCTTCAGAAATCTGGAGGACTAGAGACCGCGCTGGCCCTACTTTTACACTCTAATCTTATATTTGTTATATAGTTAACGTTTAA
AAATGAAAGCAGTCAAAAACCATCCGAAAAAGCCTAATCAAACACCAACAATTCCGTGCTGCATTCGATGAAAAACAAAAGTCCAACAAATACCA
CAACTTCTTGGTGCCTGCGAGAGATGTAAACATTCCGGCCTGCGGTTAATACTTTCCCCTAACCACGCCCCCTCCGCCCCTTGAAGGGCAACTCT
AGGCAACAGCAACTACAACGTCCTGCTATGTACTTCCATTTACAACAACAACACCAACATACACTTGAATAAAAGTACACGGACACTGGCGCACA
CACAACACATACATAAAAGACACAAATACAAATGCATGCATAAATAGTATTATTGTTTAATGAATGGAAATTCTTGTTTATTTGTGAAAAAAGTC
ATGTTTTCTCCCTGTTTGTTTGTTAAATTTATGTAAATATTTAAAGTATGAAATATTAAATGTACGAATAAAGTGCAACAACAAATACATTTAAT
GTAATTGAAAGTGAATTTCACTGGCAGCAGAATGGATATTAAAAATGTGTCAACTCGATAAAAAGATAATAAGTTAAAATATTTTTTTGAATTTT
AAACCTTCATTATATAAACATACTTGACTATATGAAAGCTAAGAAAATGGGAATATATTGAAAAGCATAATCTAAAATCCTATATCATTCTCAGT
CATCACCTTAGTCTTTCCATAAACTTCTGCCCCATTTATTTTATTTATTTGACAATATTAGTAAAAATTGTACCAAGTGAAAAAATTGTATATAT
TTAAACCAAATGGAAAAGAAGTCCTGGGTTGCACCGCTTACCTCGTTCACCAACAGTAACGCAAGTAACGAAGACAGAGCCCGCAACTCGGGATC
GTTAAACCAAGATGGGGAGCCAAGGTCCGTGCCTCACCCAACGGTTCCGGCTAAGAAGTGCACATGTCCAACCTGCGCTTGCCAACGTAATGACC
ATAAATCCAATCCGGTACCCCCTCCCCCTCAATCACGCAAGCCTGTAGCCGAGCCGGAAAGTCCCCATGATACAGTCAATGACGAGGACAGTTTG
AAGGACTTGAGACGTTCGACGGACCAATCCCACAAGAGCGCTCACATCGCCTTGGAGAAGAATGAGGACTCGGGTTTTGTGATCGAGCAGGTGGT
TGATACGCACAAATATTCGTCGGATGAAGAAGAGGAGGAGGCGACGATGGGTCGCATTTTCGGAGTCTCCGGTCCGGTGGTCAATGCCGAGGAGA
TGGCCGGCGCAGCCATGTACGAGCTGGTTCGCGTTGGACACTCCCAGCTTGTTGGTGAGATCATTCGACTGGAGGGTGATATGGCCACCATTCAG
GTTTACGAGGATACTTCGGGTGTGAGCGTGGGTGATCCCGTCTACCAGACGGAAAGCCGCTCTCCGTGGAATTGGGACCCGGCATCATGGGCAG
CATTTTCGATGGTATCCAGCGACCATTGAGGTCCATCAGTGAACTAACCAACTC
(SEQ ID NO: 364)

Exon: 1001..1063
Exon: 2234..2332
Exon: 2746..3443
Exon: 3552..4529
Exon: 4597..5229
Start ATG: 2257

Transcript No. : CT12570
TTCGTTCTGTTGGAGAAAAGCAGCAATCACACGTTCGCAAGGTGAACGCGAAGACACAGCAAATCGAAAAAACAGAATAAAGCAAAATGTCCAAC
CTTAAGCGTTTCGATGATGAGGAGCGTGAGTCCAAATATGGACGTGTCTTCGCTGTCTCCGGTCCTGTCGTCACCGCCGAGGCCATGTCTGGATC
AGCTATGTACGAGTTGGTCCGCGTCGGCTACTACGAGCTGGTGGGCGAGATCATCCGTCTGGAGGGTGACATGGCCACCATCCAGGTGTACGAGG
AGACCTCTGGCGTAACTGTCGGAGATCCGGTGCTGCGTACCGGCAAGCCTCTTTCCGTGGAGCTGGGACCCGGTATCATGGGCAGCATCTTTGAC
GGTATCCAGCGTCCCCTGAAGGACATTAACGAGCTGACCGAATCCATCTACATCCCCAAGGGTGTGAACGTGCCCAGTTTGTCCCGCGTGGCCAG
CTGGGAGTTCAACCCCCTGAACGTCAAGGTCGGCTCCCACATCACCGGAGGTGACCTGTACGGTCTGGTGCATGAGAACACTCTGGTCAAGCACA
AGATGATTGTGAACCCCCGCGCCAAGGGAACAGTGCGCTACATCGCCCCCTCCGGCAACTACAAGGTCGACGATGTCGTCCTGGAGACCGAGTTC
GATGGAGAGATCACCAAGCACACCATGTTGCAGGTGTGGCCAGTGCGTCAGCCACGTCCCGTGACCGAGAAGCTGCCCGCCAACCACCCCCTGCT
CACCGGACAGCGTGTGCTCGACTCGCTCTTCCCCTGTGTCCAGGGCGGTACCACCGCCATTCCCGGAGCTTTCGGTTGCGGCAAGACTGTGATCT
CGCAGGCTCTGTCCAAGTACTCCAACTCCGATGTCATCATCTACGTCGGTTGCGGTGAGCGTGGTAACGAGATGTCTGAGGTACTGCGTGACTTC
CCCGAGCTGTCCGTGGAGATCGACGGTGTCACCGAGTCCATCATGAAGCGTACCGCCCTTGTGGCCAACACCTCCAACATGCCTGTGGCTGCTCG
TGAGGCCTCCATCTACACTGGTATCACCTTGTCCGAATACTTCCGTGATATGGGTTACAACGTGTCCATGATGGCTGATTCCACCTCCCGTTGGG
CTGAGGCTCTTCGTGAAATTTCTGGTCGTCTCGCTGAGATGCCTGCCGATTCCGGCTACCCAGCCTACTTGGGAGCCCGTCTGGCCTCCTTCTAC
GAGCGTGCCGGTCGCGTTAAGTGCTTGGGTAACCCCGAGCGCGAGGGATCCGTGTCCATTGTCGGAGCTGTGTCTCCTCCTGGTGGTGACTTCTC
CGATCCCGTGACCTCCGCCACTCTGGGTATCGTGCAGGTGTTCTGGGGTCTCGACAAGAAGTTGGCCCAGCGCAAGCACTTCCCCTCGATCAACT
GGCTCATCTCCTACTCGAAGTACATGCGTGCTCTGGATGACTTCTATGACAAGAACTTCCCCGAATTCGTGCCGCTGCGTACCAAGGTCAAGGAG
ATCCTGCAGGAGGAGGAGGATCTGTCTGAGATCGTGCAACTGGTCGGCAAGGCCTCTCTGGCCGAAACCGACAAGATCACGCTGGAGGTGGCCAA
GCTGCTGAAGGACGATTTCCTGCAGCAGAACTCCTACTCCTCGTACGATCGCTTCTGCCCCTTCTACAAGACCGTGGGCATGTTGAGGAACATCA
TCGACTTCTACGACATGGCCCGTCACTCCGTGGAGTCTACGGCTCAGTCTGAGAACAAGATCACCTGGAACGTGATTCGTGAGGCAATGGGCAAC
ATTATGTACCAGCTGTCATCCATGAAGTTCAAGGACCCCGTTAAGGATGGTGAGGCCAAGATCAAGGCTGACTTCGAGCAGCTGCACGAGGACCT
GCAGCAGGCCTTCAGAAATCTGGAGGACTAGAGACCGCGCTGGCCCTACTTTTACACTCTAATCTTATATTTGTTATATAGTTAACGTTTAAAAA
TGAAAGCAGTCAAAAACCATCCGAAAAAGCCTAATCAAACACCAACAATTCCGTGCTGCATTCGATGAAAAACAAAAGTCCAACAAATACCACAA
CTTCTTGGTGCCTGCGAGAGATGTAAACATTCCGGCCTGCGGTTAATACTTTCCCCTAACCACGCCCCCTCCGCCCCTTGAAGGGCAACTCTAGG
CAACAGCAACTACAACGTCCTGCTATGTACTTCCATTTACAACAACAACACCAACATACACTTGAATAAAAGTACACGGACACTGGCGCACACAC
AACACATACATAAAAGACACAAATACAAATGCATGCATAAATAGTATTATTGTTTAATGAATGGAAATTCTTGTTTATTTGTGAAAAAAGTCATG
TTTTCTCCCTGTTTGTTTGTTAAATTTATGTAAATATTTAAAGTATGAAATATTAAATGTACGAATAAAGTGCAACAACAAATACATTTAATGTA
A
(SEQ ID NO: 365)

Start ATG: 87

MSNLKRFDDEERESKYGRVFAVSGPVVTAEAMSGSAMYELVRVGYYELVGEIIRLEGDMATIQVYEETSGVTVGDPVLRTGKPLSVELGPGIMGS
IFDGIQRPLKDINELTESIYIPKGVNVPSLSRVASWEFNPLNVKVGSHITGGDLYGLVHENTLVKHKMIVNPRAKGTVRYIAPSGNYKVDDVVLE
TEFDGEITKHTMLQVWPVRQPRPVTEKLPANHPLLTGQRVLDSLFPCVQGGTTAIPGAFGCGKTVISQALSKYSNSDVIIYVGCGERGNEMSEVL
RDFPELSVEIDGVTESIMKRTALVANTSNMPVAAREASIYTGITLSEYFRDMGYNVSMMADSTSRWAEALREISGRLAEMPADSGYPAYLGARLA
SFYERAGRVKCLGNPEREGSVSIVGAVSPPGGDFSDPVTSATLGIVQVFWGLDKKLAQRKHFPSINWLISYSKYMRALDDFYDKNFPEFVPLRTK
VKEILQEEEDLSEIVQLVGKASLAETDKITLEVAKLLKDDFLQQNSYSSYDRFCPFYKTVGMLRNIIDFYDMARHSVESTAQSENKITWNVIREA
MGNIMYQLSSMKFKDPVKDGEAKIKADFEQLHEDLQQAFRNLED*
(SEQ ID NO: 366)

Name: vacuolar ATPase subunit
Classification: enzyme

FIGURE SHEET 200

Celera Sequence No. : 142000013384592

TGTTGGCATTTTGCAGAGGCTACATCTGCCACAAAAGCTTCCAACTCAATTAGAAGCCTTAGCGTCGTTTTCATGTTGTTTACCCACAGTTGGGA
TGCGGCGCATACTGAAAACGAAACTGAAATGCGAGTTCAATGTTTTGATTTTGAAATGGGCTCTGAAAATCCTTGAAAAGTGTCATCGGCCGGCC
ACAGCAGATTAATTTACAAAATAGTCGAAATTCTTCCGCAATAAAATGTGAAGAAAAACAAAAGCCTGCGGTATGGAGATGATCTATTTATGAGG
CGAAATCCACTGCCCGAGACGTGTCTCCTTGCGGCAAAGAGTCAACGCACTTCGCAGCTCATGAATTTTACTACAATTGCCGCTTTACGCACTTT
TATCTGAATATCTGTTGCCTGAAATTCTGTTTTCCTCCTTTTCTTTGTGCATTTTAATCTAATTTATTATTGCCGGCGAGGCGGAATTTTTCTTT
GCGTAAGTTTTGGACCGATTTTAATGCTCAAGGGGAAAATGCTTGACGTGTTAAGTCTGAAAACTTGTGGTTTCTAATATGTAATGGAATATAAA
ACATTATTTTTTTAGCTTATCTCCCACTTAAATGATACATTGTTGAACCCTCGTATCATATATAAATTTATATATTTTCATTAAATTGCTGTCA
AATAATTTAAGTTGAACCCCTATGTGACTAAAATAGAAACCATTTTAGTTTAAATAAATTTCTTTGAAAATCTAATTAATACAAAAATCTACTTC
TCTTTTGCGACATCTGGCGCTCAGAAAGTATACTAAACAGCACTGTGGCTTGAACTGCTTGCATGGTGGAGGTATTCGCTAGGAGCTGGCAGTAC
TAAAAGCAGAGAACACAACCGGAAGCGTTATTCCACAAAATGTGGCCTTTTAAATTATATGTGAAAATACGATAAGTACCTTAAAATACCGAAGG
CGCGCAGTTTTCAGTATAACAGCTGGCCGAGTAACTGGCCACACCATTCCAATTAGAAAGAAACCTATTTAAGCAAAACGCATCGATCTCTCCGT
AATTTTTTGTCCGCTGAGTAATCGGAAATCGGCAACGGAATAATGGGCAATTTCGACGGCGATTCTGGAACGGTTTTCGAGCAGAGCTATGCGAC
GACCAACGGAAACGGAAAGGTGCCGAATGGCAATGGGGCGGCAGATCTCAGTGCCCCGGAAAAACAGGAACTTCTCCGGAAGTTCTCGGCACCCG
CGTACACTGAAATTCGCACGCGACGCTGCCAGCCGAAGCCCGCAAACGACGCCCAGGTGAGCCAGGCATTTTCGCTCAGTGTGCGGGGTGAAACG
CGAGTTAAACACTTGGACGAAACGAAAATAACGAGCTAAAAGGCCATAAAAATTGGCCAAAAATGTGGTTCCATAGCTGGTTCCATTCACCCTCT
CGCTCGCTCTTCCAGCCGGCGAATTATTGATTTTGTGTGAGAGCGAGGGAGCGCGCATAAGAGAGAGGGAGAGAGAGTGAGAGTGAAGGCGTGCG
TCAGCTGGAGAATTTCGGCCCAATTTTTGCTGCCCTTTTTGGCGATTTTCCTCCGCTTTTCCCGCTTCTGGGTCATCGGGCAGCCACAGCTGTTT
TCCCTCCACTGCAGTGTTTTCCTCGCGTGTTTTCCTTTTCGCCGCGAGTGCTGACCATTTGGCGTATTTTGGCTACTTCCGGATGATAGAAACTA
TTAGAACTCTGCGGAAATATCCTATCATCATATACGATCAGAGAGTTATTTCATAAATTGTGATCATGAAAGGCAATTTGTAGTGTTGGAAATTA
AAGTATTGGGCAATATTATTTCACTTTCATTATTATAATTTTAAGTAGTCTATACATTCCTCTGAGATAGCTATCTTACAATTGACTAAGCCCTA
AGATAAGAACATCAGCATGTTAAAGTAACTTAGATTTCAGAAATTTCATAATACCTATTTTAGATGTGCGTTAAACTGTTTGGTACGCTAGTCCA
TTTTACCACATGCACTCTCTAATCTAGCCATTGTCTCTTCTTCGGCACTCCTGCACTCATTCGAAATTTTCCTAGTGACTGGAGTACGACCCCAA
AGCAAACACACACATAAGTACGTAGTTTGGGTGCACAATGTGTGGGGAGAGCGGCACAATGCTGGTCTGGTCATAATATTGTCATGCCACGCC
ATGCCCGGCTCGCCTTATCAGGCCCATTCCACCAGTCTTTTACGTAAAGCCTCGCAGAATGCGATTCGCTGGTGAATCACAATGCTCCGCAATCT
CCGAAGGCAGCGGTTTTGGGTGGGCGTTGATTTGTCGGTGATAAGAGTTTTGTTTTAAAATTCATGGACTCTCCCTGCGTCTGGGCTGCCAAAGA
ATAACTGTTGGCGGGTATACTTAACCGATTATCATATTTTTTATTATTCATAACTTTTTAAAAAGATAAGATAAACATATTATAACATTACATTC
ATTGGGTAATTCCGATACAATTCGATCTTTGGGGAGTGAGCAATTGTTAGTTTTCTTTTAAGTACCTAAAGATTTCATTATTGGTAGCTTTGTAT
TTCTTTTTTTCGGAAAGTAATACAATGGTTTACATAAAATTTATTTAATGAAATAGTTCCGTACCATGGCGACAACTTATTGAAATCATTCAGCT
TGATTTAATGGCAACTAAAGACCTTTTCAAATTTTTAATCACACGAAAATAATGTTAGCGCGTGCAAGTCTCATATCTCCAATATCAACGGATAG
AAAACTTTTATCAGCTCGGCAAGATTACAGTATGCATGATTTCAAAGGTAAAGGCTTAAATAAAAAAGAAATACTTAAGAATATGAAATTGCCAA
AGCAATTATCTACTGACTCACAGCTAATACTTCTTGGAATCCCCACAAAATCGGTTAGAACTTGGCGTGCGCTGGTCGATTGTCAGTCGTTATCT
TGGACTCCATGGATCCCCAACATATGGAAGTCATTATCTGGATCCCACACCATGCTCCCTACTTAGCTGTCCTTCTGTACGCGACCCATAGCGTA
ATTAGTATTACACTTTTTCTATTTATTTATTTATGTCGGTTTCGATTTTGATCTTTCTACGGTAGCTTCGAGCTCGTCTATATACCCTAACACTG
GGACTCCATTAAATAACTAGGCATCGCGTAACCCACTTGACTTTTCGCTCCCCGCACTCCGTCTCATCGTATTTAGTAAACAAGCCCGGTGGCAA
ATGATAATAAACACGAAATATTATTGTCGCCGACTCGTTATTGTTATACGATTAAGCTGACGTTCAACTATATATATTTTTCGGAATATATATCT
GCAGTTTGTGTTGCTCAGTTAATGAGATATATATATGTCTCGTATCGGATCCTTTGGCCAGCAAAATCAATAAGCAAATGATATATACACTTAAA
TAAGTACGTTAATTATAACGCTCTATTTGTTAGCTGGTGAGGTTGAAGTGTGCCAAGTTGGGCACACAAATACTATATACATTTATGGCTTCCCC
TGTATGATTTTTGTGTCTGTCTCTTTTTGTGTGACTTCATGTCGAACTCGGCTCATGTGAGCGGTGGAGCAAATTGTTCAGCAGTTATCGTGTGA
TTGTATTTATATATGTACATACGTACCTTGCATATATGGATCTTTTAGTTAAATGTTAATTGACTGATGAATTGACTGAACGCATAGAAAGGGCA
AGCAAGTGAGAATGTAGAATTTTTCATTTTTTTATAAAAGCGTTTACGCATGAGAACTATAAGTTTTGATATACATACTCGTATAAATGGGTATT
ACTGTGCTGATCCCTTTGAAGCGAACATGTTTACAATCTGTCTTACAATTTCCCATCTAGCCCGTCTAACAATATTGATTATTTGCTCTTTGATG
AGTGATTTTCAATGGAAATTATGAAGATTCACAGTGATACCAATGATAGCGATAACCAGCCAATAATCGTTCCTCTCCCCTCTTACAGAGTCCCA
GCTCGATCAACTACCATCCGGAAAAGAAGTCGATCCCCAATGGGCATGCCTCCATTCTGGATCAGGAGTCCAAGCCCAACCAGGCAGAGGGCAAA
CTTTCGCCGGAGCTGGAGCACTTCCAGAAAACCTCCTTTGAGGAGGTGCCTTTGCACACGGCCTGCCTTACGTATTTGGGATTCTATCTACTGAT
GATCCTGGGCTACATCAACCAGTTGCTCTTCGTGCCCAAAGTGGCCACCGAGAAGGGTCGGGATGGCTATGTAGCCCTCTACGATGCCTTCGAAA
GCTTCTACTCGAGGTACGTTTACAGGAGAATCAAGGATTGCTGGAACCGACCCATCTGCAGTGTTCCGGGAGACGAACTCACTCTAAAGGATCGC
GTAACCGATGATTATGGATGGAGTTTCAAGTTCACTGGAACGGAGACACGTTGCTTAAATCTGGGATCCTACAATTACCTGGGATTTGCCGCCGC
TACTGGACAGTGTGCTGATGATTCAGAGGAAAGTGCTCGGAGCTCTGGACTGGCATACTGCAGCTCCCGTTGTGAGCTTGGTGACAACGAGCAGC
TGCAAGAGCTGGAGGCTCTAACTGCCAGATACTTTGGCGTGGAGGATGCCATTGTCTTTGGAATGGGTTTCGCCACAAATGCGTTGAACCTTCCC
TCACTGCTGGGACCCAACAGTCTTGTGATTAGTGACGAAAAGAATCACGCCTCCATCATTTTGGGACTGCGTTTGTCCGGGGCCACCACCAAGGT
CTTTAAGCACAACAACATGCGCGATCTGGAGCGCGTCCTCCGTCAGGGTGTGTGCTATGGAAATCCCAAAAAAGGTGGTCAGCCATGGGACAAGG
TTATGATCTTGGTCGAGGGCATCTTCAGCATGGAGGGGTCCATAGTCCGTTTGCCCGAGGTTATTGCTCTGAAAAAGAAATACAAAGCATACTTG
TATTTGGATGAAGCTCACAGCGTGGGAGCCATGGGTTCCCGTGGACGAGGAGTTACAGATTATTTTAATGTGGATCCGAAGGAGGTGGACATTCT
GATGGGCACCTTCACCAAAAGTTTTGGCAGTGCTGGAGGCTATCTCGCTGGATCCAAGGTATGCTTGAGTGGCTACACTTTCGCATATTCCTCAC
TTATCAATAATCTTTTATCCTCCCCAGAAACTGATTGACTTTCTCCGCACCAACAGCCACGCCCATTGTTATGCTGCTTCGATCTCGCCACCCAT
CGCACAGCAAATCCTTACCTCCATGAAGACCATTATGGGTGAAGATGGCACTGACATTGGACGCAAGAAGATCCACCAGCTGGCCAGGAACACAC
GTTACTTCCGCCGACGTCTGGCTCAGCTGGGAGTGATCACATACGGTCACGAGGACTCCCCAGTCGTGCCCATGCTGGTGTACCTGTTTTCCAAG
ATTGGGTAAGAATGGGGTCATAAAACCAAAATAACTTTTGTCATTAGATTGTGCGTGGAGGAGCATTTCATTTTTTAAAAGATCAAACGGAAAA
AACTTCAATTATCCTGTGGAGTCTCTTTTTACTAAACTGCATTTTCTCTTTGTAGCGCTGTGGTTCGCACCTTGACGACTCGCCACATTGCCGCG
GTGGGAGCTGGATTCCCGGCCACACCCATCATGGAAGGACGCATCCGATTCTGCCTTTCAGCCGCCCACACCAAGGAGCAGCTGGACTTTGCCCT
GGAGGCGATAGACGAGATTGCCGATGATCTGGGCCTAAAGTATTCTCGCAAGCCACGCGATCCGAATCCCGTCATTTACTAGAATCACACGCACA
CACATAGAAGTTAAGCTTGGGGAAATGGTAACCTCCCCGATTGGTAAACCAAAACTACAACACAGTCCAGATAGTGCTAAATCAATCACGAACGG
TGGCTTACATTGACCAAGTTTCAGTTGCACTGGGCTTCTATTTATGACTAATTCTCTGGTTATATGCCTTAAAAGGGAAGATCACTACAGCAACA
GAAACAAAACACTACAGCACATAGCTTAAATGATAAAATATTATTAATTATTTAGCATTTACCTCTACGTAGTTGTTATTGTATATGTAAAATCC
AATCGTCTTCTTTGGTCGGCTGCTGCATTTTAAGTATTTATAGAAGAGAAAATGACAGCGCAATGTATTGGGCAAATCAGGGTTTGGTTACTTTT
ATAGCTAAGCTAAGGGAAGCCCCTTTTTCGTGGGAAAGCCTCGAGCACCTCGCTTCTACCAATTAAGCATACTAAGCTGAGCCAAATGTAACGTC
TAAAGAGTCAGCGATACAATTGTAAATCACTATTTGGGTAAGTCTTCGGGGGACCCAAAAATTGGGTCAACTTTAGGGCATTGTCAGGAAATATA
TATGTATAATAATTATGTATTATTGATCTTATTTTTCCACCAAAAAAATAAAGAAATTGTTGCTTTATCTAATAAACTATATTGGAATAGCTTAC

FIGURE SHEET 201

TGTAAAAGTATTCACTGTACGGGATTCTTAAGTCTACTAGTGTAAATATTTATTTAAAATATATAAAACTTGGCGGGCAGATGAATCTTAAAGTC
GAAAAATGTTTTGCCTTGTATTTTACATAAATTTTGACACAACTTATGCGACCTCTACAGTTAATTTACAGAAGTTGGATACTCGACGCAAATAT
AAAACACATATGTAGAGAATCCGCTAAGTCTAGGGCCTTAGTTCTTATTTTTGAGAAAATAAGAAGTACAGTGGCCATTAATTAAATAAAGCTAC
TTCTTGAACCATTTTTAATTAAGTAAATGCCTGACTTTTAAGCGATAATTAGAGATTAGCGATATCAATTAAATCGATATTGATAATATGTTATT
TTAGACGATTTGGAAGTAAAATAAATAAAATTTGTTTCAGTATCATTTTGGTTGCACTGCCTCCTTTCTTTAATTTAAAATACATAAACTCCATT
TGCAAGGGGTCAAGTTAATTTAAGTTTATGTAATAGGAATAGCAATCAATTGACAGTTCGACTTTCAAATCGTTCCTACCCAACACGATTTCACA
CTTAAAGCGTCGAAGCCGAACTACCAATCCTTTGAATAACAATTTTCTAATTAACAGTAACTCATGACATCTCTACATCGCTCCCTGTTTTCCTT
TTCCGGTGCTGACCACAATGGCAAATAAATTCCAATTGTAATTGTCTCTGCCTTTTAAGAAATTAAGACAAAAGGCGAACAACGCTCAGATCGAA
GGACAAGAAGGAGTTTCGAGAGCGGGTGGCTTGTAAAGAGCCGTGTTGGTTTATGGGCTTAGGCAATACTTTCAATTTTATATTCTGGACAATAT
TTATTGAGTGGTTCTTGTTGAATCTGTGGGGAGTACATGTAAACTGAATTTAAATATTTTGCATGAAAGAGAACATTCGCTCGTTAAAAGTGCAT
TTGAATTGTTTTTAAAGCAACACGTTACACAGG
(SEQ ID NO: 367)

Exon: 1001..1291
Exon: 3984..5093
Exon: 5158..5420
Exon: 5566..6443
Start ATG: 1088

Transcript No. : CT12625
AATTAGAAAGAAACCTATTTAAGCAAAACGCATCGATCTCTCCGTAATTTTTTGTCCGCTGAGTAATCGGAAATCGGCAACGGAATAATGGGCAA
TTTCGACGGCGATTCTGGAACGGTTTTCGAGCAGAGCTATGCGACGACCAACGGAAACGGAAAGGTGCCGAATGGCAATGGGGCGGCAGATCTCA
GTGCCCCGGAAAAACAGGAACTTCTCCGGAAGTTCTCGGCACCCGCGTACACTGAAATTCGCACGCGACGCTGCCAGCCGAAGCCCGCAAACGAC
GCCCAGAGTCCCAGCTCGATCAACTACCATCCGGAAAAGAAGTCGATCCCCAATGGGCATGCCTCCATTCTGGATCAGGAGTCCAAGCCCAACCA
GGCAGAGGGCAAACTTTCGCCGGAGCTGGAGCACTTCCAGAAAACCTCCTTTGAGGAGGTGCCTTTGCACACGGCCTGCCTTACGTATTTGGGAT
TCTATCTACTGATGATCCTGGGCTACATCAACCAGTTGCTCTTCGTGCCCAAAGTGGCCACCGAGAAGGGTCGGGATGGCTATGTAGCCCTCTAC
GATGCCTTCGAAAGCTTCTACTCGAGGTACGTTTACAGGAGAATCAAGGATTGCTGGAACCGACCCATCTGCAGTGTTCCGGGAGACGAACTCAC
TCTAAAGGATCGCGTAACCGATGATTATGGATGGAGTTTCAAGTTCACTGGAACGGAGACACGTTGCTTAAATCTGGGATCCTACAATTACCTGG
GATTTGCCGCCGCTACTGGACAGTGTGCTGATGATTCAGAGGAAAGTGCTCGGAGCTCTGGACTGGCATACTGCAGCTCCCGTTGTGAGCTTGGT
GACAACGAGCAGCTGCAAGAGCTGGAGGCTCTAACTGCCAGATACTTTGGCGTGGAGGATGCCATTGTCTTTGGAATGGGTTTCGCCACAAATGC
GTTGAACCTTCCCTCACTGCTGGGACCCAACAGTCTTGTGATTAGTGACGAAAAGAATCACGCCTCCATCATTTTGGGACTGCGTTTGTCCGGGG
CCACCACCAAGGTCTTTAAGCACAACAACATGCGCGATCTGGAGCGCGTCCTCCGTCAGGGTGTGTGCTATGGAAATCCCAAAAAAGGTGGTCAG
CCATGGGACAAGGTTATGATCTTGGTCGAGGGCATCTTCAGCATGGAGGGGTCCATAGTCCGTTTGCCCGAGGTTATTGCTCTGAAAAAGAAATA
CAAAGCATACTTGTATTTGGATGAAGCTCACAGCGTGGGAGCCATGGGTTCCCGTGGACGAGGAGTTACAGATTATTTTAATGTGGATCCGAAGG
AGGTGGACATTCTGATGGGCACCTTCACCAAAAGTTTTGGCAGTGCTGGAGGCTATCTCGCTGGATCCAAGAAACTGATTGACTTTCTCCGCACC
AACAGCCACGCCCATTGTTATGCTGCTTCGATCTCGCCACCCATCGCACAGCAAATCCTTACCTCCATGAAGACCATTATGGGTGAAGATGGCAC
TGACATTGGACGCAAGAAGATCCACCAGCTGGCCAGGAACACACGTTACTTCCGCCGACGTCTGGCTCAGCTGGGAGTGATCACATACGGTCACG
AGGACTCCCCAGTCGTGCCCATGCTGGTGTACCTGTTTTCCAAGATTGGCGCTGTGGTTCGCACCTTGACGACTCGCCACATTGCCGCGGTGGGA
GCTGGATTCCCGGCCACACCCATCATGGAAGGACGCATCCGATTCTGCCTTTCAGCCGCCCACACCAAGGAGCAGCTGGACTTTGCCCTGGAGGC
GATAGACGAGATTGCCGATGATCTGGGCCTAAAGTATTCTCGCAAGCCACGCGATCCGAATCCCGTCATTTACTAGAATCACACGCACACACATA
GAAGTTAAGCTTGGGGAAATGGTAACCTCCCCGATTGGTAAACCAAAACTACAACACAGTCCAGATAGTGCTAAATCAATCACGAACGGTGGCTT
ACATTGACCAAGTTTCAGTTGCACTGGGCTTCTATTTATGACTAATTCTCTGGTTATATGCCTTAAAAGGGAAGATCACTACAGCAACAGAAACA
AAACACTACAGCACATAGCTTAAATGATAAAATATTATTAATTATTTAGCATTTACCTCTACGTAGTTGTTATTGTATATGTAAAATCCAATCGT
CTTCTTTGGTCGGCTGCTGCATTTTAAGTATTTATAGAAGAGAAAATGACAGCGCAATGTATTGGGCAAATCAGGGTTTGGTTACTTTTATAGCT
AAGCTAAGGGAAGCCCCTTTTTCGTGGGAAAGCCTCGAGCACCTCGCTTCTACCAATTAAGCATACTAAGCTGAGCCAAATGTAACGTCTAAAGA
GTCAGCGATACAATTGTAAATCACTATTTGGGTAAGTCTTCGGGGGACCCAAAAATTGGGTCAACTTTAGGGCATTGTCAGGAAATATATATGTA
TAATAATTATGTATTATTGATCTTATTTTTCCACCAAAAAAATAAAGAAATTGTTGCTTTATCTAATAAACT
(SEQ ID NO: 368)

Start ATG: 88

MGNFDGDSGTVFEQSYATTNGNGKVPNGNGAADLSAPEKQELLRKFSAPAYTEIRTRRCQPKPANDAQSPSSINYHPEKKSIPNGHASILDQESK
PNQAEGKLSPELEHFQKTSFEEVPLHTACLTYLGFYLLMILGYINQLLFVPKVATEKGRDGYVALYDAFESFYSRYVYRRIKDCWNRPICSVPGD
ELTLKDRVTDDYGWSFKFTGTETRCLNLGSYNYLGFAAATGQCADDSEESARSSGLAYCSSRCELGDNEQLQELEALTARYFGVEDAIVFGMGFA
TNALNLPSLLGPNSLVISDEKNHASIILGLRLSGATTKVFKHNNMRDLERVLRQGVCYGNPKKGGQPWDKVMILVEGIFSMEGSIVRLPEVIALK
KKYKAYLYLDEAHSVGAMGSRGRGVTDYFNVDPKEVDILMGTFTKSFGSAGGYLAGSKKLIDFLRTNSHAHCYAASISPPIAQQILTSMKTIMGE
DGTDIGRKKIHQLARNTRYFRRRLAQLGVITYGHEDSPVVPMLVYLFSKIGAVVRTLTTRHIAAVGAGFPATPIMEGRIRFCLSAAHTKEQLDFA
LEAIDEIADDLGLKYSRKPRDPNPVIY*
(SEQ ID NO: 369)

Classification: enzyme
Gene Symbol: lace
FlyBase ID: FBgn0002524

Celera Sequence No. : 142000013384832
TGTACAGGTCGTGGTACAGGTGCCTGTCAATCTTCTTGCTGTCGCGGTACTTCTTCAACAGGCGGCGCAGAACGCGCTGGCGCTGCATCCACAGC
AGCTTGGTAGGCATGCGGGCGTTCGCAGTACCCTTACGCTTTCCGAATCCGCAGTGACGTCCCTTGCGGCGGGCCTCGGTGTTTTTGCGCACACG
GTAACGGGAGTGGACCACGACGGGCTTCTTGATGATCAGACCATCCTTGATAAGCTTGCGAATGTTCTGACCTGGAATGGGTTAACAACACAGTT
AGCTGGGCTGTCTATTCGACCATTTAGACCATTTCTACTCACGCGAGTTTGTGTTAGCGATCTCGTTGATTTCATTGGGATCCAACCAGACCTTC
TTCTTGCCGCATCGCAGCACGGAGGCTGCGAGCCTCTTCTGGAGCTTTAGAGAACTGCAAAGGAGGGTAACTTGTTAGTCCATCATTTCGAAAGT AGCGTGCTGGGATGCGCCTATCAGCTTGTGTGTGTGTGCATGAGCGTCGCATGTTCGGTTATTTCACAACTGCCGGGAAACAGAATGGCACTT
GTCCGCCCGGCAGCTGCATCATACGGCACGCGCTCGCCCGGCACACTTTGCAAACATTTAGACCCCGCGAGCGCAACTTTTCGCTCATATTTGCG
AACTCAAATCTACCTCATGCTGTCGACCTCGTCGTGGCTAGGAAAGAAAGAAAAATTTGACAGCCGGAAGTCAGCACCATTTTCTGAAGGGTGCT
ATCGATACATCGATAACGTACTCGGGGGTCTGGCAACGCCTCGGGGATGTACTAGTTTAAGCGGAGTGGCAAGATTTATTTAAAAAAAATATTTA
ATAACAACTACTTTGTGCGGTTTCCAGCAGCTTGGATGTGCAAGATCCGGCCATATTTATATTGTTCGAATTAAGTTAGAGCAATTAAGTAACGA
AGCTTGGTATATTTTATTTATCTACTTGCGGTCACACTAAATTGGCTAAGAAAAACAAAAACAACTTTTTAGCCCAGTTGCAGCTGTTCAGAGTG
CAATTTCTGCAATGCAGCACACGCTTATACGCTGCTTGGGCATGGCCCGGATATCCCTGATGCGTTTGCAGCCCAGACCCACAGTGGCAGCCTCC
GGGGGACAGGAAGCTGGGTCCATCTCGAAGCCAACACAACCGGTCAGTCGGTCTTTCGCCTCGCTGCCGCAGGAGCAAGACAAGAAGGAGCAGAA
TGCCAGAGAGAGCCTTAACCGCCTGCCTCGCCTAATGGACTTTCCAGAGATCGTGTGGCCATCGGCGCTTAACTCGTTAAAAAATTGGATCACCA
TACAGTTCATAATTCGACCCTACTTCGACAGCGAGTTTCAACTCAAGGACTTCATATACGGCGCCAAGCAAGCGCTGCAGGTGCGTCATGGTTTG
TCTATCATGAAGTGTAATGATATTAATTCCCTCATAGGTAGTATCCTCAAAACTGATGGGCGGCGACTTAGACTCCCTGGACAATCTTGTCTCGC
CCGAGGCGATCGCAGAGCTTAGACCGGTAATCCAAAAACTGTCAATGACGCAACGGAGGCAGCTAGAAATCAAGGAGAGCGACATATACCTCAGC
TTTCCCTATCAGGTAGGTATTATGTTTGACGATGCAAACGACAAGCTGCAGAAGCGTTTCGTAGAGATCACCATGGTGTTTCACGTAATGCGTGG
TCTATCCGAGATGCGGGAACGCGGCGAGGAAATACCCTGGAACATGGGGTAAGTTTGGACTGTCACTGCCCGAAAGCTGAGCTCCTCATACCCAT
TTGTTGCAGGACCCTTCCCGAGTACCAGGATAAGGTTTTCATCTGCAACTACCGTTTTGTAAAGGAGTTCACCGCTGGACACCAATCGGACTGGA
CCGTAAATGTGGCCAACCAGTTTAGGGCCATCGACCTTATTAACGAGACCATATAACATCGGCCCATGGCTACCATCATCCGCGCTGTTCGCCGA
CTCATAGCATATATTGGCGTAAGCCACCGCCTTCGTTGGAATAAAAGTTTCGTTTTCCGCATTTAGGTATAAAAAACTAAAATCTTTACTGTGGA
TCTCTGGTTTAAATTAGGTTCATGTGAAATTAGTGCATTTGGTGGACAAGCAAAGCGCTCAGTGTCCCTCGTGCTTTGCTCTGTAGATGCCTTGG
GGATCGTACTTGTTCAGGAGGAGCTTCCATTCGCCGGCTTTGTTGGCGCGAAGGTAGTTGATTACCTTTTGTGAGTTTTTGCGTTGGACTTCCGT
GCACTTTGAGCAGTCGGAATGAAGGGCGTCGGGTAAAAGGCGCTTAAGTTCACGACCCTCTGCTGTGCATGGGCCCTTGTCCATCAGGCACTTGA
GATAATTACCCAACACTCGGTTGTTGCCCAGAACTTCATCCACGTTGACACTGTCGTACTTGTTGGTGTAGGTTTTTCAGGAGCAGCTGCCGCA
AGACCGACACAAACACAGAACACTAGAGCTAGCGAGGCTTTCATCTTGGAGGATTATCTGGAAAGGCAGGTGGAAATTCAAATTATTAAAGGTA
AGCCACGAAACACATTTCCTAAAATGAGGGATTTTTGGTTGCCGGGTAAGCGGATAATAAGAAGGCGTCAGGCAGTCTCGGCTTTTCTGTGTTTT
CGACGCATGTCAAAGAATCATCCAAAGCGGTTAGTGGTCTGCCCACCAGCTCATGCATTATTTATGGCCCTTGGCATATATATCGCATATGCATA
CTAATTGGCAATCGTTTGGATTTAATATTTTGAAAAGATTTCACAATTTCACCGACACCACGTAGTTTAGCAGCTTTCGACTTATTTGCGTCC
AATATCCGAATCCATGCTAGCCCGTGGCCAGCTGTTTGGTTTTCGCAATCCTTGATGGGTGCTGCACCTCAATTCCTCGGGTGCTCGGCCTAACC
AGGGCAAACGAACCACGGCTTGAACAATGGCTTACTCACTTCTCTTCCGGTGATTTTCGGTGGCCCGGGTGCAGTTGTGGTACGATCAAAGGCGC
AACTCAAATTGCGAGCTGTTAGCTCGCTGG
(SEQ ID NO: 370)

Exon: 1001..1410
Exon: 1463..1758
Exon: 1815..2070
Start ATG: 1057

Transcript No. : CT12627
AAAAACAAAAACAACTTTTTAGCCCAGTTGCAGCTGTTCAGAGTGCAATTTCTGCAATGCAGCACACGCTTATACGCTGCTTGGGCATGGCCCGG
ATATCCCTGATGCGTTTGCAGCCCAGACCCACAGTGGCAGCCTCCGGGGGACAGGAAGCTGGGTCCATCTCGAAGCCAACACAACCGGTCAGTCG
GTCTTTCGCCTCGCTGCCGCAGGAGCAAGACAAGAAGGAGCAGAATGCCAGAGAGAGCCTTAACCGCCTGCCTCGCCTAATGGACTTTCCAGAGA
TCGTGTGGCCATCGGCGCTTAACTCGTTAAAAAATTGGATCACCATACAGTTCATAATTCGACCCTACTTCGACAGCGAGTTTCAACTCAAGGAC
TTCATATACGGCGCCAAGCAAGCGCTGCAGGTAGTATCCTCAAAACTGATGGGCGGCGACTTAGACTCCCTGGACAATCTTGTCTCGCCCGAGGC
GATCGCAGAGCTTAGACCGGTAATCCAAAAACTGTCAATGACGCAACGGAGGCAGCTAGAAATCAAGGAGAGCGACATATACCTCAGCTTTCCCT
ATCAGGTAGGTATTATGTTTGACGATGCAAACGACAAGCTGCAGAAGCGTTTCGTAGAGATCACCATGGTGTTTCACGTAATGCGTGGTCTATCC
GAGATGCGGGAACGCGGCGAGGAAATACCCTGGAACATGGGGACCCTTCCCGAGTACCAGGATAAGGTTTTCATCTGCAACTACCGTTTTGTAAA
GGAGTTCACCGCTGGACACCAATCGGACTGGACCGTAAATGTGGCCAACCAGTTTAGGGCCATCGACCTTATTAACGAGACCATATAACATCGGC
CCATGGCTACCATCATCCGCGCTGTTCGCCGACTCATAGCATATATTGGCGTAAGCCACCGCCTTCGTTGGAATAAAAGTTTCGTTTTCCGCATT
TAGGTATAAAAA
(SEQ ID NO: 371)

Start ATG: 57

MQHTLIRCLGMARISLMRLQPRPTVAASGGQEAGSISKPTQPVSRSFASLPQEQDKKEQNARESLNRLPRLMDFPEIVWPSALNSLKNWITIQFI
IRPYFDSEFQLKDFIYGAKQALQVVSSKLMGGDLDSLDNLVSPEAIAELRPVIQKLSMTQRRQLEIKESDIYLSFPYQVGIMFDDANDKLQKRFV
EITMVFHVMRGLSEMRERGEEIPWNMGTLPEYQDKVFICNYRFVKEFTAGHQSDWTVNVANQFRAIDLINETI*
(SEQ ID NO: 372)

Celera Sequence No. : 142000013384479
TCGTAATATAAGGTATTTTCATTGTTACCTTTATTACAAAAGTGGACTTAAAGGACATAAGTTTCCAAAATCATTTAGTATGCCTAAATTTGAGT
TACATTTGTATCTTCACCCGTACATATGGTCACCAAACATTTGCAGATGAGTGTAAGCTGCGCAGTACTTTAATAGCGCCCCTCGTAGGCCTAAC
TAAATGCGGCGATTACTTGGACGACCCGCGATCGCACCGCACTTAAGTATGGAGAAGCGCAAAAAGTGACCAAACCGGCTTGCCAACCGCTCTCT
GCTTCTTGCCCATCCGCATGCGGCTCCAGAAACTCGGAGCGCAGCTTTCGCGAAGCCACCGTCGCGTCACGGCCGCCGTCGTGGTCGTCACACAT
GCGCAGCAGCTGATGCGCGAGCGCTGACCTTGACCCTCAATTGGAGTCGCAGTCGCTTGCAGACTTGTTGCCAAGTGCAGCCGGCAAAGTTGAAG
TTGCCACCCCACCCCGGGACCGCTCTCTCTTCCTCTTGCTCTCTGCCTGCTTTTTCGCACAGCCAGTTTTCACCATTAGCGGCGACTGTACCTCG
CAGCACGCTGTACGTCCATACATACGTATGTATGCATTCACTTAGCGCGCGCGTATGTACGCATGCATGTGTGTGTGTGTTGTGTGTGCTGGTAC
GCGAACTGCACACAGAAAAGAACAGGGCAGGAGAGCAAAGAAAGCGGCGTGAGCACATAGCGAAAAGAGAGCCCCCAGCCCCATATTCCATCCAG
CCATCGCCATCAGCTGCCTGCGCCATGTGTTCCCGCAGCTGCAGTTGTGAAAATCGCCGGTAAACTGGTTGCGCGAGCGAGATGGAGAGAGTGCG
AAAGCGGGCGATCGCTCTCTCCCGCTCAGGGGCGGAGATGCCTCAAATTGGCAGGGGGCCTAATGAAAGATGTTACCCTGGAAGACGCTGCAAGA
ATTACCCCAAAGACATAACACATGGTGCGGGATTATTTTTTTTTTTGTCTCAAATCAGCAGCTCCAGCATTTTAATTTACAATTAAAAAACAATC
ACAGTGATATTTGAATTTTCATTTCCTTCATCGTACGTAGGTTTCGGTCTCGCATCTTTTGTGTCCCGTCCGTCCAACTGAACTGAACTGAAGGT GTGTGTGTGCCGTTGTCTTCTTCATCTGCCCACTGAGTGTTCTGAGTGCCGCTTGCTTGTCTGCTTCTTTAACCGCTTAGCTCATCCTCTCCAGC
GTTGCGTTCCGTTTTCAAAGTCGTCGTGTATGTCTACCATTGTTGATGTTCTCTTCTTGTTATTTGTCTGCTTCTCTGTTCTTGTTTGCTGCCCC
CTTTGGCTCCACAGCTATGAGCTACATAGCATGCTACCCCGCTTGAGAGATCTTGCCAGGCGTCTTGGCTGATGGGTGTGTGGTATGGTATGGAT
GTGGATGGAGTTAATGGTATAGGGGTGGGATACTGGTTACTGTCTACAGATCCTGTCTTACAGTCTTAGATCCTGGATAATTCCCAAGGCTCGCC
GGCAGCAGCTGGATGGAGTGGAGTTGAGTGGAGTCGAGTGGTAACGTGGCCTGATCTTCTAGCCGCCTGATTCTTCGCTTTTTCATTGGTTTTTA
TAATTTTTATTTACGTTTTTCTTTCGGTTGTTTCTGGCTGTGGAACTCCTAATAGGATCATTTGCTTTAAATAGTATTCTTTAAGGTATTTTTCT
TTATATAATCTTATATAGTTTCATTCCATTCGTTATAATGTAATTAGTAAATTCAAACACTTGCAGCATAATCATATAATCATATAGGTATAATT
ATAGTAGAGTGGTTTGCTTGGTGATTTCTTTTGTTGTTGCTGTTGTGGTTTAGTCTCATCTTACAAATTGGGTCGTCGTGTCTTCTTCCTCATCT
TCTACCTCATCCTCTTCCTCGTCGTCGGTGTCATCTGCTCTCTCGGCTGCACAGCTGCCGTTGGCTATCGTCTTCTGGTTCTGCTCCTCCGACCC
CCGCTCGAGGAGCCTTTGCCCTCTTCCTCCTCCGTGATTCCTTTTCTGGCGGCTTTCCCTCGGAAAGCCAATACTTCTTGTCTTCTTTCAGTTCT
CGGGACGTTGGCACCGCGCTGCAGGCTCGGCTTTTGGAATCAGCGATGGTTACTGGATGATGTTCAGGATTATGGATTCATATGCTGCATGTGTT
AATGGAGGGATGTGGATGTGGTTGTGGGTTCTTTATTTTGAAGGGGTTGATCTTGACTTGGGTGCTGCTGCTATCGCTTCTAGATGTTGTTGCTG
TTGGCTGGCTTTGTGAATGTTGTAGCAAATTGATTTTTCGTTTTTTTTTCATTTTTTTTCGTTCTCATCTTTTCTTCTGGTTGTTCTTCGTGTGT
TGAATTATTACTCATATTCCTCCTTCGATGATTACATTTATGAGGTGCCACGGGTGGGTGGTGGCGCCTAGTTCCGTCCGCCCTTCTCGTCGCAC
TCGCGCCTCAGATGTCCGCTCTTGCCGCAGCCGTAGCAAGTCTTCGAGGTCTCCGGGCAGTTCTTGGAGATGTGTCCGGTGCGGTTGCACTTGTA
GCACGACACATTGGTCGGTCCACGTTCGTTGACGGCCTCTGGGCAGTTGCGCACCCAGTGTCCGGTCTTGTTGCAACGGTAGCAGGTCGGGTTGT
CCGCCTGGGTGCAGTCCTTCGAGATGTGCCCGATGCCGTTGCAGCGGTAGCAGCGCTCGGCCTCCTCAGGGCAGGCACGTGCGAAGTGCCCAAAT
TGGTTGCATTTGTAGCACTTCTCGCGGTTGCGACGCATGCCGCCGCCATCGTTGCCGCGCATACCGCCGCCGCCGCCACCACCGCCTCCTCCAAC
GCCGCCCGGACCTCCGCCGCCGCCGAGACTGCAGTCCCGGGCAAAGTGGCCCGGCCGGTTGCACTTGTAGCACGTGGCAGACATCGACATCTTTG
CTTCGGTTTTGGTTAGACTACTGATCCGCAAATCCGACTCCGCTTCTTAAACTCAACTTCTCAACTTCCTCACACACTCACTGGTAACCACGGGC
CCTCGAGCACTACACACTGCTTGCGCTGGATGCGAAAAAATCACACAGACCAACAGGATCTCCGGCTTCCTCAGATTTCCTCGCCGTATTTTCGA
CGCCAAAAGTTAAAATGGCTGCCGCTGAGCGAATGAGTACCGATTTGCTGTGGTATCGACTACTCGCCAGAGTTGCTTCGGCTACGCTTGAATAC
AACACTGACCCTCCACGCGGTGCACATTGGTTCGAGGATATGCGATGGTGAGGCGAAATGTCAGTCTGGAATTGTGTAGTGTGCTGGTGTCGTAC
TACTTCCACTCGGCGTGCTTTGTCTCACAGAATCTACATTTCCATTTTGCTTTCTCACTTGGCGTGTTTAGCTTTTGTCTCGTGTCCTCCATATT
TAGGAGGCACTACATAACCCAATTTTGCGAACTCGATTTTGCCACTTTATAACCACACGTAACCAGTGTGTCCGTGGTGATGGACTGCAACTTAT
CGGCTCAGTCGTTAGGAGTACCCCTGGCAAAGGGCTATCGAAATATATATCTTTAAATTTATAAGGAAGTCCATTCAAATAATTGTTTTATTTTA
ATTGTTTGGACACAACATACGTTCACCTTTTTGAAATTGGCTATTTGCAGAAATTGATATCGATTGACACATTAGGGGTGCTTAGCAAAGAATAG
CTAACTGAAGACTTCATAAGAGAAAACGTAATACTCTAATAATAGAAAAGCACTCAGATTACGTAACAACTAATAAAATATTTTATGTGCATATA
TATAAAACGATTTATCAAAAGAACCTGGCTTTGTCAAAAAATCGATATTTCATAGTGGTGTACATTTTTAAGGACTTTCACAAATAATACGCTGA
GTACACTTATATTATTGTTATATTATCCCAAATATTGGGCAGCACGATTTTTTGAAATCTGGGTGACATCGATTACTATATGAAAAGGGTATTCC
TGCTTATCAGTATTTGCAGAGAAAAGGAATTATGAATAATATTTACCTCAAAAGCTATAAATTAGATAAAGTCATAATAATTTACTTTACTATTT
ATTAACTATATTAATT
(SEQ ID NO: 373)

Exon: 3101..1001
Start ATG: 2817 (Reverse strand: CAT)

Transcript No. : CT12687
AGATCCTGTTGGTCTGTGTGATTTTTTCGCATCCAGCGCAAGCAGTGTGTAGTGCTCGAGGGCCCGTGGTTACCAGTGAGTGTGTGAGGAAGTTG
AGAAGTTGAGTTTAAGAAGCGGAGTCGGATTTGCGGATCAGTAGTCTAACCAAAACCGAAGCAAAGATGTCGATGTCTGCCACGTGCTACAAGTG
CAACCGGCCGGGCCACTTTGCCCGGGACTGCAGTCTCGGCGGCGGCGGAGGTCCGGGCGGCGTTGGAGGAGGCGGTGGTGGCGGCGGCGGCGGTA
TGCGCGGCAACGATGGCGGCGGCATGCGTCGCAACCGCGAGAAGTGCTACAAATGCAACCAATTTGGGCACTTCGCACGTGCCTGCCCTGAGGAG
GCCGAGCGCTGCTACCGCTGCAACGGCATCGGGCACATCTCGAAGGACTGCACCCAGGCGGACAACCCGACCTGCTACCGTTGCAACAAGACCGG
ACACTGGGTGCGCAACTGCCCAGAGGCCGTCAACGAACGTGGACCGACCAATGTGTCGTGCTACAAGTGCAACCGCACCGGACACATCTCCAAGA
ACTGCCCGGAGACCTCGAAGACTTGCTACGGCTGCGGCAAGAGCGGACATCTGAGGCGCGAGTGCGACGAGAAGGGCGGACGGAACTAGGCGCCA
CCACCCACCCGTGGCACCTCATAAATGTAATCATCGAAGGAGGAATATGAGTAATAATTCAACACACGAAGAACAACCAGAAGAAAAGATGAGAA
CGAAAAAAAATGAAAAAAAAACGAAAAATCAATTTGCTACAACATTCACAAAGCCAGCCAACAGCAACAACATCTAGAAGCGATAGCAGCAGCAC
CCAAGTCAAGATCAACCCCTTCAAAATAAAGAACCCACAACCACATCCACATCCCTCCATTAACACATGCAGCATATGAATCCATAATCCTGAAC
ATCATCCAGTAACCATCGCTGATTCCAAAAGCCGAGCCTGCAGCGCGGTGCCAACGTCCCGAGAACTGAAAGAAGACAAGAAGTATTGGCTTTCC
GAGGGAAAGCCGCCAGAAAAGGAATCACGGAGGAGGAAGAGGGCAAAGGCTCCTCGAGCGGGGGTCGGAGGAGCAGAACCAGAAGACGATAGCCA
ACGGCAGCTGTGCAGCCGAGAGAGCAGATGACACCGACGACGAGGAAGAGGATGAGGTAGAAGATGAGGAAGAAGACACGACGACCCAATTTGTA
AGATGAGACTAAACCACAACAGCAACAACAAAAGAAATCACCAAGCAAACCACTCTACTATAATTATACCTATATGATTATATGATTATGCTGCA
AGTGTTTGAATTTACTAATTACATTATAACGAATGGAATGAAACTATATAAGATTATATAAAGAAAAATACCTTAAAGAATACTATTTAAAGCAA
ATGATCCTATTAGGAGTTCCACAGCCAGAAACAACCGAAAGAAAAACGTAAATAAAAATTATAAAAACCAATGAAAAAGCGAAGAATCAGGCGGC
TAGAAGATCAGGCCACGTTACCACTCGACTCCACTCAACTCCACTCCATCCAGCTGCTGCCGGCGAGCCTTGGGAATTATCCAGGATCTAAGACT
GTAAGACAGGATCTGTAGACAGTAACCAGTATCCCACCCCTATACCATTAACTCCATCCACATCCATACCATACCACACACCCATCAGCCAAGAC
GCCTGGCAAGATCTCTCAAGCGGGGTAGCATGCTATGTAGCTCATAGCTGTGGAGCCAAAGGGGGCAGCAAACAAGAACAGAGAAGCAGACAAAT
AACAAGAAGAGAACATCAACAATGGTAGACATACACGACGACTTTGAAAACGGAACGCAACGCTGGAGAGGATGAGCTAAGCGGTTAAAGAAGCA
GACAAGCAAGCGGCACTCAGAACACTCAGTGGGCAGATGAAGAAGACAACGGCACACACACACCTTCAGTTCAGTTCAGTTGGACGGACGGACA
CAAAAGATGCGAGACCGAAACCTACGTACGATGAAGGAAATGAAAATTCAAATATCACTGTGATTGTTTTTTAATTGTAAATTAAAATGCTGGAG
CTGCTGATTTG
(SEQ ID NO: 374)

Start ATG: 285 (Reverse strand: CAT)

MRGNDGGGMRRNREKCYKCNQFGHFARACPEEAERCYRCNGIGHISKDCTQADNPTCYRCNKTGHWVRNCPEAVNERGPTNVSCYKCNRTGHISK
NCPETSKTCYGCGKSGHLRRECDEKGGRN*
(SEQ ID NO: 375)

Classification: hypothetical

FIGURE SHEET 204

Celera Sequence No. : 142000013384774
TTTCCTTTCTTTTTCGAAATTTAGCCTGCTCATTGAAATGAATTATTAACTTGCTTATTTTTGGCAAGCTAAATTATTGATCAGCTGGCCTTTGC
AGCTATTATTTGTGTTTTACTTTTTTTTTTGCTAGCAAAACTATTGATTGAAAAACACAAGAGAGATATATGTTGCTTGTAGTTAACAAATGCGT
TTACATTAAGACCGCTGAATAATTGATTTTGAAACTCAGGAGATTCATTGAGTTTTTTTTTCTCATTTAAATCCATAACAAATTGACTTTAAGTG
CTGACATTAAGGCAACTGCATTATTGATTTTAAATAACTGGGGATCTCTTTGGACGAATATACACTGTAATAGGCAGATTTATTGCCGACTCACC
GGCGCCTTAGAAATTGGAGTGTTTGCAACCTTCGATATATGCAAATTTCGCAGGAGAAAAAAAAAGGGAAAATATTCAAGCGAAGGCAGGCTGAC
ATTGTTATGGGAGCATTTCTGACAGTTTCATTTCCTCTTTCTTTATTTTTTTTTTAATTTCTATGTAGCTTCCTACAACAAAATTCATTTTGTGC
AAAACGAAAAGCGGAACGCAAATGTTATTCCTGGATAATCGCGTCATTAGAGGGCATTAAAACTGATTCGACGAAGCGGTGCTAACGAAGAAATG
CAAATGTGTTCATTAGTTTCTTCTGTCGTGGGCATATGTGTCGGATACGTGATATAGCCAAATATATCACTCATACGCACTGGTGACAGCGCGTT
GTTGATACGCAGTTGCAGTGTTGCAGTGACTACAACCCCTTAAATACTCAAAGATAATGGACAAATATCTGGCAAGTGTATTGCGGATCCATCAT
GATTATATCCCTAATTTATAGTGCTATAAATTAAATGCTAATTACCTGTAAAGGGGCTGAGGCAGCCCAGCAGGCATAGGGCCAAAATCAGCTGG
GCGAGATAGTCAGTTGGCAGCCAAAGCAACGACGTCATTGGTGGCGGCCACGCCCCCAGTCGACCGGCCGCCTTAAGGCGTTGCAAGTACGATTG
TTGCTGTTGCTTTTGCTTTTGCTGCTGCATGTTTCGTATTGCTGCTGTTGTTGTTGTTGTGCAGCAGCCTCGTTGACGTCGCCATGTCGTTTGGG
GCCCATTGATTGTTATTGCTTTGGTTGCTGCTGCTGTTTTGATTGGTGTTGCTGCCGCTGTTGTTGTTGCTGTTGCTGTTGCTGCTGCTGCTGCT
GCCTTTGTCATTGTCAGGCGTTGATTTTGAACTTGGCGGCGGCGATGGCTGTGGGAGCTGCACTTGCAGCAAATGTTGCTGTTGCAGTTGCCTGG
CTTACTTCTTATGTTTGCTGTTGCAATTATCCTTTTTGTACTGCTGCTTCTTCTTGGCCTGTCCTTGCACTCTGTGTGCGTGTGTGTTTCGGTGT
GTGGAGAAAGGTGATATATTATTGGAAACTTCAATCAATTTCATGTTGTAAAACAGTGTCTTAAATGTACTAGTTACAATTCAGTTTTATATTAT
TTGAATATGGTTGAAAAAAATATCCAAAACAAAGTGTTTGAATGAATGCAATTCCTTTTAGACTGATTTATTGATAGATCGCATAGTTGGCTGCA
TTTATTAATTGTGTGCCTCAGAGATTTTTGATTGAATTTAGTTGATTTTGTTCGATATAAAATAAAATACCATGCTCTAGTGTTTACATTATATC
AGCAAATTCTGCCCACTGTTCTGTTGGCCAAAAAGTTTCTCTGCATTGTGTCGACAGACAGTTTTTGGCAGCAATTTCACCTCTGCCTCTTTGTG
TGTGTGTGTGTGTGTTTTTGCGTTTGATGGTGGGCATTTTGCAGGGGGTGGTTGCAGGGGGCGGCGGATCAGCTGTTCGGCAGTTCCGTGTTTGG
CAGCCGAATTGCTTGTTTACAAAGCTTCTTGGGGCATTTTCATTTTCATTTTTTTTTGCCATATTTTTTGGCTCTTTGCGGCTGCCAAAAACAGA
AAAGTGCACACACACACACACACCCACATACATCCAGTGCTTAATTCGAATCGTGTAATTTATTATTTGCATGTCCTGTGCGCCAAAAGAGAGCG
ACAAGTTCGAGTTTCACTTCACGCCGTTTTATGGATTTTCTTACAAACACACACTCATACACACACACACACGCACACACAGGGGCACACGCGTA
CCCGCATTGATTTTCCCTTTTCTATTTCGTTTTTTTTTTGTTTTTTTTTTTTTTGCTATTTTTGCTCTTTTCAAGGCTCTGCTACTTACATCTCAC
GTAAATTGTTTAACTTTGACACCAACAAAATTTCGCACGCAAGCACTAAAAATACTTGAAAAAAAAAAAATGAAGGGAAATGTGAAAACAAAACAC
AGCACGAATTTCCCAGCCAGCGAGCAGCAGTGGCAAGCAGCTAGCCTACACACCAGCCCACCGCGCCCCCTTCCCACGATTTCCCATTTTCCGA
GTCCTTTTTACAACCGACTGTTTGCTGATTGCTTTTTGCCCACCGTCTTTTGTGTTGCCTTTTGTTGATTTTGTTGATTTTTGCTGCTGCCACTA
CGCTGCTGCTGCTGCTGCTGCTGCTGCTGCAACTGCAACTGCAAGTGTGACGAACCACTCTCTCACTCCCAGTACGCTCTATGCAATCCGGGCAA
GATTCCGATTCCGATTCCGATTCGGATTGCGATTCCGATACCGATTCCGATTCCGGTTCTGATTCCGGCCAGAGCCACCGACTGCAGCGTGGGAG
AGTCAAGAGCCAACTGACGGCGCGTCGACGAGGCTGCGCCCCAACAAATGTTGCTGGCGTTGGGCGGTAGCAACATCGGCTCGCCACTATAGCAA
CATTGACGTTCCAACAGCAACATTTCCGTGGACAACACAACGTGTTGTAAGCTTTTGCTCGATTCGAAAGGGTTCATAGCTTTTGGGAAACATTC
TTAGTGTTCTTTCGAACCAGCCAAGAGCTTTTTAGTTCTGAATTAGACACATGATTTGATTCCGGTTTTAAGGAGGGCTTGAGCTTTTGCAAAAG
CTTAATAGCGTAGCTCAGAAACACAGCACCGGAAATAACGTTAGCTTTCAAAGAGAAAAAATCCCGCCAAGGATCACATTTAAATTAAATAAAAA
AGTGAATCTTATGGCTGACTTATGAGTAATAATTCAACAATACAATTTATGTACATGTAATGAAGAATTTTTTATATAAATGGAATTATTTCAAC
TATAAATTATAACACTAAAAACTGAAAAATGAAGGGAATTCCGAAATTTAAAAATTATTTGCAAACTTATAAAGATTAATATTTTCAAAATATT
CAGCTTTACTCAGCTCTTTGTCCCAATAAAAGCGTACAGAACATTTTTTAATAAGTAGTTTGGAAATGATTTTATTTCAATATATTTCATATTCA
TTCATTAGTTCATATTTTCTGTTTTATACTTTTACACAAAAATACTTGTGTGTGTGTGTGTGTGAGTGTGTCCGTGTGTTCGTGTTTGTCTCG
TAGGTTCTTCTATTGGTATTGGTGTGTCCTTGAGTAGTCCTTTGCTATCTCGGTCTGTCTGTCTCTGTGTGTTTATTTTTTTTCTGTATGTATTG
TAGTTGTCTTATATGCCATTAATCTGAGTTGGACATAACTAAGTGTTAAATACAAGTTGAGTTATCTCATTTAAATATTTGTTTACCATTTAAAT
GCATTTTCGGAAAAGTTTCATTGAATTTCTCGCTTCTTAGCTGATTTATTAGTTGTATACCCATGTTGACTTTTCTGTGTGGGTGACTCAGCGAT
ATTTGATTCATTTATTTAGGGGGTGCCAAGAGCTTTTTACATCTAAATCTTTTTAGGCTTGTATATAGGTGTGTATGTATATATATAT
(SEQ ID NO: 376)

Exon: 2927..2621
Exon: 2334..2274
Exon: 1401..1001
Start ATG: 2927 (Reverse strand: CAT)

Transcript No. : CT12689
ATGAACCCTTTCGAATCGAGCAAAAGCTTACAACACGTTGTGTTGTCCACGGAAATGTTGCTGTTGGAACGTCAATGTTGCTATAGTGGCGAGCC
GATGTTGCTACCGCCCAACGCCAGCAACATTTGTTGGGGCGCAGCCTCGTCGACGCGCCGTCAGTTGGCTCTTGACTCTCCCACGCTGCAGTCGG
TGGCTCTGGCCGGAATCAGAACCGGAATCGGAATCGGTATCGGAATCGCAATCCGAATCGGAATCGGAATCGGAATCTTGCCCGGATTGCATAGA
GCGTACTGGGAGTGAGAGAGTGTATTTTTAGTGCTTGCGTGCGAAATTTTGTTGGTGTCAAAGTTAAACAATTTACGTGAGATAGTGCAAGGACA
GGCCAAGAAGAAGCAGCAGTACAAAAAGGATAATTGCAACAGCAAACATAAGAAGTAAGCCAGGCAACTGCAACAGCAACATTTGCTGCAAGTGC
AGCTCCCACAGCCATCGCCGCCGCCAAGTTCAAAATCAACGCCTGACAATGACAAAGGCAGCAGCAGCAGCAGCAACAGCAACAGCAACAACAAC
AGCGGCAGCAACACCAATCAAAACAGCAGCAGCAACCAAAGCAATAACAATCAATGGGCCCCAAACGACATGGCGACGTCAACGAGGCTGCTGCA
CAACAACAACAACAGCAGCAATACGAAACATGCAGCAGCAAAAGCAAAAGCAACAGCAACAATCGTACTTGCAACGCCTTAAGGCGGCCGGTCGA
CTGGGGGCG
(SEQ ID NO: 377)

Start ATG: 1 (Reverse strand: CAT)

MNPFESSKSLQHVVLSTEMLLLERQCCYSGEPMLLPPNASNICWGAASSTRRQLALDSPTLQSVALAGIRTGIGIGIGIAIRIGIGIGILPGLHR
AYWE*
(SEQ ID NO: 378)

Celera Sequence No. : 142000013384832

FIGURE SHEET 205

CCGACATCAGCCCCATCAACGACCGCGAGGAGCTGACCGAGGAGGTGATGCGCTACCTGCCCTACCTGGAGGTGAATCCATCGAGCGACGGGCTC
ACCCTTAAGGTGGAGTCGTCCAGCCTGCTGGGAAAACCGCTAAACGAGCCCGTCTTCGACTCCGAAGACAACATTGTGAACGACGCCAACTTGCA
CTCGGCCAGCCATCAAATACCTCCATATGTGCCTGACAGCCACGACTGCTTCGCGGAGGACTGCGGCGGCGACAGCTCCTCGCACCAGGTGGAAT
TCGAGGTGGTGCGGCCCCAGACGGTGACCATGACCATGACCTGCACGCTGCCCTACGGCGGACCGGACGCTGGGCACACCACATTCCAGGCCGAC
GACTTCAACGCGATCCCGTCGGCCGCCGAGGACAGCGAATGCAGCATTCTGACCACCTCCAACTCGCCGCAGATTGGCTTCAACGGGAGCAGCTT
CGTGGAGGCGGACGCCATCGGGAGCACTTGTACATACGCGCAACAAGACTACACCGGAAGTGTAATTGAAACACACAATGATCTCAACTACGCCG
CACACGATAACAACGGAGCTCTGCTAGCCTACACATTTGAGGACTTGCCGCCTCAGCCAACCGGTAGTCATTTAGAGTTTAACACTAACAAATAC
GAGTTTGCAAGTTATTATAAAATGTGAGAGATATTTAAGTTTGTGTAATTTATAACTAATCTAATTGTACGTTTATAATTTTACACCAAATTATA
TATTAAATATGTATATGTATGCAGATAATACCATATATTCCATAAATTCTATATACATACAAAAAACGCGAGAATAAATGCTTTGCATTGAAAAT
ATTTACGTCGGAGCAGTCTCATTTACTGCGTAGTGGAATGATCGCTGATCGCTGGTTCCTGCTATGCGCGACGAATGGGAAGGAGATTAACCTTG
CGGCGATCAGCTAAGTGCTCCCAAATCCATTCAATAGGATCTCCAGCGGCTCTCGCGAATTATCTACATATGTTTATTTACACGTTACACAAATA
TGTTATATAAATCATTGGTGGCCAACAAAAGGGGATACAGAATGAGGCTAAACCATCATTAGTTGTTGCACACGATAAAATAATCCAGACAGTAA
GGTAGTATACATTCGTTTCTCTTTCCGCGGCCGATTTCCTGGCTCTCGACGAGCGCTGATTACAAGGTGCTCGCCTCGATATGTGGGATATTGTG
TAGGCCGGAGTCGGGATTGGACCAGAAGTAGTAGGGGGCGCCCTGGCTGAAGCAGAACTTCATGTTTAGTGTCTCCCCGTGATCCACGTAGTACA
TGAGATAGAAGTTGCACATCTCGTCCTCGTTCGTGGGACTGTCATCAATAAATAGTTGGATTAGGAGTGGTGCTAGAGCTGCGTTTCAAATCACT
GCGTACTTACCCTATTTTGGTAGTCCGATGGCGAGTGCTCTGCATAGTACACCTCACGGCGATCTTATCTCCCTCGATTATGGGGTCTGTGTTGC
TGGTGTTATAGAACATCTGGGGCGTGAGGGGATCTCTCTTGCCCAGCTGCAGCCACTCCTGTTCGCCGTCGCTGTTTGTCCTCACCCGGTAGCCG
GAAACGACCTTTCCCAGGCCGTGGGTGTGCACCCGGTACGCAAAAGGATGCAGCACCTTCTGCTCGTTCACCTCGCAGGCCGTTTCCAGGTGCTC
CGTCTTCATCGCCGGAATCTGTCCGTCAGTGCCCAGCAGCAGAGTGCCAGCCAGCTTTTTCCGACTGCCAGGATGGTACTGATTATTTTGAAAAT
CACGCATATTAAACGAAAGGAACTTACGGCTCTTCTGTGTAATCCAAAAACACACCAGAATCATCAGTGGAGCCATCTGAAGAAAAACACATTTA
AATTTCCTTATATTGAACGCAATCTATTACTTACCTTTGAACTTATCAATGTGCGCGTAGTGAACTTGCAGCACAAGGTACTTGATTGGCGAGTT
CTTGCCCACCTTGAAACCCACTCCCTCGGGCAGATTTAACTTTTGGGCGTCTCTGGCCCAAGCGTATACGATCTGTTGAGAGGTAAGTGTTAGTC
CAGTAGGTGAAATTGTCTATTAGCACATTTGGCAGTTAGTTAAAGGAAAAACTCGATAAACAGGTTCAAAACTCTTATTAAACTGTGCTGACTGT
CAAGGATTGACCTATTAAAACTTAGCCAGTTAACTCCTAATTATCCGCGCATTTCGATCTTTATTCATATGCCACATCAATCGTTTTGAAATGTT
ACTATATATGAGTTCGATTTTTGTGTCAAGAACAAGACAAAATTTGACTTTAAAACTATCTTTCCGATTTTTCCTTAAAATTTATAATTTGTCTA
TCAGAAAGCTGCCTAGTATGTCCGCTTCAATTTGCTGCAGATGCAACGAGAAGATTTGGCCACGGGCAGTTTGCAGCTTGGGTAAGACGTACCAT
CCGCACCACTTCACCTGCAAGGAGTGCGGCCTGGTGGTTGATCCTAAACTGTTTTTCGCGGTGGACGACGACGTGGTCTGCAGCGAGTGCTATCT
GGACAAGCATGCCGCTCGGTGCTCCGCCTGCCGGACTCCGATCCTAGAGCGCGGCGTGGCTGCTGCGGAGCGCAAGTGGCACGAAAAGTGTTTCC
GGTGCGTGAGCTGCAGCAAGTCGCTGGTCTCGGCGAGCTTCTTTGAAGTCAACGGATACCTGTTCTGCAAGGCGCACTTCCGGGAACTGTTTTCG
TCCCGCTGCGCAGGCTGTGAGAAGCCAATCGATCGTCGAGCCGTGGTCGCGCTGAGCACCAAGTGGCATGCCAAGTGCTTTAAGTGCCACCACTG
CCGCAAAAGGATCAGCGCACGGGAATTCTGGATCGAGAACGGTCAACCCATTTGCGCAGCCTGCCAAACTGTAGTCCCGAGTCCCCGAAATTTGT
CGGCCCAATAAATGTGTGGTGTCTATCTGGGGGCCTATTTGGACATTTCTTTTTCTTTTAATACCTGGGAATTGGAGTGGGGTCCGCAAGGACTG
GCAGACTCTTCTTGGGAAGCTCGGTTCATCTCGCCACAGTTCCTGTGAGCAAAAATGTGCGTGTTATTTACTAGTCTGAAAACATCACTTGCAAC
TCACCAGGTGGTCTTCGAGGTTCCGGGCTCTCCGCATCCGTAGAGCAGCATATGGTGGGCCGTGTTCATCGTGGCATTAGGATTGAAGCCAACTA
TTTAAGATAGAAAGGTTAGTTGAAGTATTTAAGGAATGAATCTCATTCGAAAGGACGTACCAATATAGTAGGTGGTAGTTGGGTCGACCTTGATG
GGCGTGCACAAGTACAGATCGGGCTATATATGTACACATATATATATTTGTTAGTTTTGTTAGAGAGAACAGGCATATTGGATAAGTCAACAAGT
ATTATTCAAATGGGAGTATGGCCTTCAGTGGGCCGTTTGCCCTTTTTCGCCACCCTCGTAAAAACAAATTCGTATCTACGGCGCAGGTTCGAGAA
GTGCAATCTACAGGTTTCGGTTTCAGGGCCTTACATGTGGGTGGCGAATTGTGTGTATTCGGGTACAACTGAACATATGGAAAAATTTGCACAGT
ACTCTTATGGGTTTTCCCCGCGCGGAAGATACGGGAAAAACCAGAGCCTATATCGAGGACTTTTCTAATCTGATTGGAATTGTATGCGCACAGCT
GCAGCTGGGCGAATCTGTTCATCCATATGGAGCGAACTCCATGATGTATATGTATGGCGTTTTTCAGGAACCTGGACTTACGGTCTGGGGCGAAA
CGTTGGGCATCAGGAATGGAAACGAAGCCGTTGCGCCTGTTGCGGAGTTCGACTCGAGATTCTGTTGATAAAGGGAGTTTTGGTAATCCCCCTCT
TTCACAAGGCCATCCACACTGATCACTCCGATAAGCAGGAGCAGCCCCACGGAAGCGGCTATTTCGGATATGCGTGGCATTTTCACCGTATTCGA
ACTATATTCGAGTGTGCACTGCACTGAATACTTTGTGGAAAACGAAAAAAAACCTTCCTGTTTGGAAGAACAATACGTTTTGTATTGCTCTCTCC
GATATTTTTCCACACGTAGCTAGGCCCAGTTTATATGTAAGTAAGTGCGTTCTAGGCAGCAATCGATACCCAGAGCCATTATATCGATGACGGCG
CCAGGGCTGCAGGCTAAGGGTTAGCGGGACATTCAAATATATATAACTTGTTCGCATTAAAGTACATAAAACCAAGTGTAATTTTCAACCTTTCG
AATACAGTGATTTAAAGACACCTCAACGCAAAAGGAAACCCCACAAAAGCCAGCCCAATTCAACGTGTCTGCGTTCCGTTCGACCCACTGGGGAA
TTCCCCTTTTCGCATGCGCCATTCAATTGATTTTCTACGAGCAGAGTTCCCAATGTTTACGGTGCGCTCATTTGGTTGTAGCTGTAGGCCTCGAG
TTGGAACCGCTGGGACTTGGAAAACATACGACGCTTAAATGGAGGATCAGGGCGACGTGACAGACCAAGCCGCTGGTAAGCTGAGTAGTTCGAAT
GCCCAGTGCTCCAGAAACCGATGTGCTAATGGTAAAGCTATATAGATGTACACTCAAGAGCGGTACTAAATTATTTACAAAAAATCGTGTAATTC
CCAGATGACCCCATTATGGGCAGCCACAGTCAGAGTCGCCAGAACTCGTCCGGCATGCTGAACATGATGGACGCCAGCTCCTTCAGCATGCCCCC
CCCCAATCTGCACTCCTCAAAGGTGATCAACCCGAACAAGGCGATATTCACAATCGACGCGAACACAGGGCAAATTTTTATAGTGAACAACAAGG
CCTGCCAGCTGCTGGGCTACACGTCGCAGGAGTTGAGGAACAAGGGATTCTTCGACCTGCTTAACGGCAAGACAGAGAGCCACATCTCCTCCCTG
GCGGAGATGCAGATCGAAGGCGATGAGGGCCGGGTCGTCCTGCTAAGTGGAAAGGTCATCGAGATGAAGACCAAGTCGGGCGGCAAGATCCTGGT
CTCTCTCTGGATCCGGCAGATCAGCAGCGATGGCCGACACATAGCCGTCGCGGAGCCTGTGGAGAGGCATATTTG
(SEQ ID NO: 379)

Exon: 4110..3787
Exon: 3348..3291
Exon: 3227..3140
Exon: 3082..3010
Exon: 2067..1935
Exon: 1881..1833
Exon: 1774..1436
Exon: 1368..1001
Start ATG: 3975 (Reverse strand: CAT)

Transcript No. : CT12811
GCCTAGCTACGTGTGGAAAAATATCGGAGAGAGCAATACAAAACGTATTGTTCTTCCAAACAGGAAGGTTTTTTTTCGTTTTCCACAAAGTATTC
AGTGCAGTGCACACTCGAATATAGTTCGAATACGGTGAAAATGCCACGCATATCCGAAATAGCCGCTTCCGTGGGGCTGCTCCTGCTTATCGGAG
TGATCAGTGTGGATGGCCTTGTGAAAGAGGGGGATTACCAAAACTCCCTTTATCAACAGAATCTCGAGTCGAACTCCGCAACAGGCGCAACGGCT
TCGTTTCCATTCCTGATGCCCAACGTTTCGCCCCAGACCCCCGATCTGTACTTGTGCACGCCCATCAAGGTCGACCCAACTACCACCTACTATAT

FIGURE SHEET 206

TGTTGGCTTCAATCCTAATGCCACGATGAACACGGCCCACCATATGCTGCTCTACGGATGCGGAGAGCCCGGAACCTCGAAGACCACCTGGAACT
GTGGCGAGATGAACCGAGCTTCCCAAGAAGAGTCTGCCAGTCCTTGCGGACCCCACTCCAATTCCCAGATCGTATACGCTTGGGCCAGAGACGCC
CAAAAGTTAAATCTGCCCGAGGGAGTGGGTTTCAAGGTGGGCAAGAACTCGCCAATCAAGTACCTTGTGCTGCAAGTTCACTACGCGCACATTGA
TAAGTTCAAAGATGGCTCCACTGATGATTCTGGTGTGTTTTTGGATTACACAGAAGAGCCTCGGAAAAAGCTGGCTGGCACTCTGCTGCTGGGCA
CTGACGGACAGATTCCGGCGATGAAGACGGAGCACCTGGAAACGGCCTGCGAGGTGAACGAGCAGAAGGTGCTGCATCCTTTTGCGTACCGGGTG
CACACCCACGGCCTGGGAAAGGTCGTTTCCGGCTACCGGGTGAGGACAAACAGCGACGGCGAACAGGAGTGGCTGCAGCTGGGCAAGAGAGATCC
CCTCACGCCCCAGATGTTCTATAACACCAGCAACACAGACCCCATAATCGAGGGAGATAAGATCGCCGTGAGGTGTACTATGCAGAGCACTCGCC
ATCGGACTACCAAAATAGGTCCCACGAACGAGGACGAGATGTGCAACTTCTATCTCATGTACTACGTGGATCACGGGGAGACACTAAACATGAAG
TTCTGCTTCAGCCAGGGCGCCCCCTACTACTTCTGGTCCAATCCCGACTCCGGCCTACACAATATCCCACATATCGAGGCGAGCACCTTGTAATC
AGCGCTCGTCGAGAGCCAGGAAATCGGCCGCGGAAAGAGAAACGAATGTATACTACCTTACTGTCTGGATTATTTATCGTGTGCAACAACTAAT
GATGGTTTAGCCTCATTCTGTATCCCCTTTTGTTGGCCACCAATGATTTATATAACATATTTGTGTAACGTGTAAATAAACATATGTAGATAATT
CGCGAGA
(SEQ ID NO: 380)

Start ATG: 136 (Reverse strand: CAT)

MPRISEIAASVGLLLLIGVISVDGLVKEGDYQNSLYQQNLESNSATGATASFPFLMPNVSPQTPDLYLCTPIKVDPTTTYYIVGFNPNATMNTAH
HMLLYGCGEPGTSKTTWNCGEMNRASQEESASPCGPHSNSQIVYAWARDAQKLNLPEGVGFKVGKNSPIKYLVLQVHYAHIDKFKDGSTDDSGVF
LDYTEEPRKKLAGTLLLGTDGQIPAMKTEHLETACEVNEQKVLHPFAYRVHTHGLGKVVSGYRVRTNSDGEQEWLQLGKRDPLTPQMFYNTSNTD
PIIEGDKIAVRCTMQSTRHRTTKIGPTNEDEMCNFYLMYYVDHGETLNMKFCFSQGAPYYFWSNPDSGLHNIPHIEASTL*
(SEQ ID NO: 381)

Classification: enzyme
Gene Symbol: Phm
FlyBase ID: FBgn0019948

Celera Sequence No. : 142000013384822
ATCGCTTTGAAGCGGCTAATTGAATTCCAGATTAAAGTGTAAAGCAAAATGGGGGGGAATAAAAAAAACTGATTTGTATTGCAAATTAAAATTTA
AGTGAAAACGAATCAGGCGCAAACACAAACAGGGACAATAGATTACAATATCCTGCGGCGCAGACAGCACGACATTAAAAAGGCACGAGGAGCAG
CGAGAGCTGGCGCGGAATGGGTATGGACATGGCAATGGAGGTGGAAGGGACGCGCCAGGACGACACAGGACCTTCGTGCAGCTGCTGCTCCTGCT
GATGGCACATGCGCCTGGGAGGGCTGCGTTTCGGGATTGGGACTGGGATGCGGGCTGGACTCCAGCGATGGCTGCCTGCCATCAGCGGCAGAAGC
AGCAGCAGCAGCAGCAGCTACAGCAGCAGCAGCAGCAGCAGCAGCAACGGCAACGGCAGCAGCAGCAACTACGGCAGCAACATCGGCAGCAGCAG
CAACACCAACAATATCCCAGGCTTGCGACCGTCAGGCCAACGGTTTCCGCTTGCTTACTGCTGGAACGGAAAAAGCCAAGGCACATATATCCATG
CACATCCACAGGCACATTCGGTCGGAGCCACATCCATGGGATAGTAGATACCGAACGCTGAGGGCCAATCCGAGAGCAGCAGGTAGGCGTGGACG
TATCTACCATTTCCAAACAACTTCAACCCCGCCACAGGCAGCTGCCGTTGGTCGGGCCGCTCGCCACCCTCGTCGCCCTCCTCCGCACTTCTCGG
CCGGTTCAAAAACGGGTCGCCCTGCCAGCAGTTGCAGTCAGTTATTAACGAGCGCTACTCCCAACAGCAACATCGCTCAGCGGCAGCAGCAGCAG
CAGCAAAAGCAAAAGCAAAAGCAACACTAACAACAGCAACACGAGTCACTCAAACGTGGAAGCGAGACAGGAATATCAGCACTCCACTCGCCTCG
TTTCACTTCGATTCTCAAGCGTTTGAGTCGGAGAGCGGCGAACGGCCAACGAATTCAGTTTGTGTCGAGACGTTGTCGGTGGCACGTCGCATCCA
AAAGAACGCTCAGTCAGCTGGGAAATATACTGAGAAAAGATACATTCGTAGATACAAGTGCTAAGCCAAAGTGAACCGTGCAGTTCGCGCAACTA
AACAATTTTAAGCCAAATAAAACTACACAAGGCCAACAAAGACAGTATAATGTCTTCCACATCGGCCTCACCCATCAGCAACATAACCGTGGATG
ACGAGCTCAACTTAAGCAGAGAACAAGGTGGGTTCAAGTTCAAAACTGGCTCAGAACAACTTGGCAAATGCCGACGGCAAAGCGCATTACTCTCT
AGCACTTTTTGACTAGTTTCAAAAAATGTTCCATTAATATTTGAAAGTAGTCTCACATAGCATTGCATTTATATGAATTGAAAACTAACCGTGGG
CATTTCTATTCCTTCCTTTTTAGACTTTGCTGAAGAGGATTTCATAGTGATCAAGGAGGAGCGCGAGACAAGTCTCTCCCCCATGCTGACGCCCC
CGCACACGCCCACCGAGGAGCCGCTGAGGAGAGTGCATCCGGCGATAAGCGAGGAGGCGGTGGCCACCCAGCTGCACATGCGACACATGGCCCAC
TACCAGCAGCAGCAACAACAGCAGCAACAGCAGCAGCAGCACCGCCTGTGGCTGCAGATGCAGCAGCAGCAGCAACAACATCAGGCTCCACAGCA
GTATCCAGTTTATCCCACAGCCAGCGCCGATCCCGTGGCCGTGCACCAGCAGTTGATGAACCACTGGATCCGCAACGCAGCCATCTACCAGCAGC
AACAGCAGCAGCAGCAACATCCGCACCATCATCACCACCACGGCCATCCGCACCACCCTCACCCACATCCGCATCATGTGCGTCCCTATCCCGCT
GGCCTCCATAGTCTGCATGCCGCGGTCATGGGTCGCCACTTCGGAGCCATGCCCACCCTGAAACTGGGTGGTGCCGGTGGAGCGAGTGGTGTACC
CAGCGGCGCAACTGGCAGCAGTCGGCCAAAGAAGCAGTTCATCTGCAAGTACTGCAACCGGCAGTTCACCAAGTCGTACAATCTGCTCATCCATG
AGAGAACCCACACGGACGAGAGGCCTTACTCCTGCGACATCTGCGGCAAAGCCTTCCGGCGACAGGATCATCTGCGGGACCACCGGTACATCCAC
TCCAAGGACAAGCCCTTCAAGTGCAGCGATTGCGGCAAGGGTTTCTGCCAGTCGCGCACCCTGGCCGTGCACAAGGTCACCCATCTGGAGGAGGG
TCCGCACAAGTGTCCCATCTGCCAGCGGAGCTTCAACCAGCGGGCCAACCTCAAGAGTCACCTCCAGAGCCACAGCGAGCAGAGCACCAAGGAGG
TGGTGGTGACCACCTCACCAGCCACTTCACATTCGGTGCCAAACCAGGCATTGAGTTCGCCTCAACCTGAGAATTTGGCACAGCATCTGCCTGTC
CTGGATCTATCCTCGTCATCCTCGAGCTCAGAGAAGCCCAAGCGGATGCTGGGCTTCACCATCGATGAGATCATGAGCAGATAGATTGAAGGACC
AGCGAAACCCGGTATCCGGTTTCTTTTGAGACATTCTAAAAGAGATTCAGAGAGCTGGACGTCCGCCAGGCATGGGAAATGCCTGGAATGGAAAA
CCAAGCGAGTCCAGCCCGCATTCTGGCCAAAGGTGCAAGTGGAAAATCCTCGCCAGCAACTCGTAATCGCAACCCAGTGAGCAGAAGAGTCATCC
TCCGTGCAATCGGTTCTATGTAGCAGATCCCAATTGCGTTAAACAAATGCCAAAGTCAAATAGCAGAGGAAAACTGATGAAAAATCCAATGAAAA
GTATTGCTAGCACAAGCCTCCTACAAATCGATTCCAAAACACACACACACACACACAACTGTAAACTATAAACTTTAATAAATAGCACATAATTT
ATATTGTAATCTAACTATTATTGTATGTACCTTATAGTCGTAGTAGCCCATTCAGTTCGTAGTGCTTATGGAGTAAACCAAATGTTATGTTACAA
TAGCTCAATCAAACAAACCTCAAACCCGCTTTGGTTATTGAAAGACTGTTTTAATTATTATATTTAAATAGTACTTGAATAAATCAATCGATCGA
TTGTGTAATGTTAAACCCCGACGAGTGTCATGATTACTTACTGTTTAGACTTAACAACTTAATTGTCGCTATAGCAATTGTGACTATGCACAACG
ATCTCATTGTCGTCTATATGTATGTCTGAAACATTCGTATTGATATGAAGTTATCACAAAAATACGTAAATATAAACGCAAAGTAATTTTCAACT
GAAATTTAATAAGACTTTTTATGAATACGGTGGATTTTGTGTTTCCAGGTATTTGGCAATGGCAATTTCGCCTTGATTTATCATTACTTCTACTG
GCAACTTGATAATCTTTATGGTGTACTAAGTTAAAGTTATCTGAAAAGATTTAAGCAGCAATTTTTTGATTACCTTCTACCACCTACTGACTGAT
TCAAGTTCCAAGCGGACTGAATGATTTTGATCTACTTTTAATCACTTTGAAATCTTTCTTATCCGCTGACTAAATCCCACGCCATTCCGATTTGG
GAATTTTCTCATGCTGCGAATATAACTCAGTAGACTGAACTCGTAGGACCATATAAGTTGAACCATCAAACAGCAGCTGTCAAAATTTATTAACC
ATCCGAATATAACTCAGTTTTTATGCAGATCTCGATTTGCGCATTTTTAAGCAGCTCTATTATTTTTCAGGTTGCCGATTAAGTAAGCAGAAGTC
TCGCCACCAAAAATATTCAAACTGTCGCAGAAGTTAATTTATGAAATCGAATCGAATTGAATTTGATGTCAGTTTTGCTATGATTTTGTCATGAA
TCGGTTTCGATTTCGGTAACACTATGGTTATTGTTTAACTTTGAGGTGTGGTCCAAATATTTATGGCCTGTGTTTCAGTTTTGGGTTTAGTTCAG TTTTCATTGTGGCTTCTCTTGAAAATCGGGAACGTGCCAAATGCCTTGCAAAAGGTATGTTTGATTTCCTTTAATGGTGGTTTTCTTTTCTAGTT
TCTTCCATTGGCAATTGCATTTCTCTTAGCACGCTTCTTACTCAGAACTGTCAATTTCAGAT
(SEQ ID NO: 382)

Exon: 1001..1262
Exon: 1449..3147
Start ATG: 1190

Transcript No. : CT12867
GAATTCAGTTTGTGTCGAGACGTTGTCGGTGGCACGTCGCATCCAAAAGAACGCTCAGTCAGCTGGGAAATATACTGAGAAAAGATACATTCGTA
GATACAAGTGCTAAGCCAAAGTGAACCGTGCAGTTCGCGCAACTAAACAATTTTAAGCCAAATAAAACTACACAAGGCCAACAAAGACAGTATAA
TGTCTTCCACATCGGCCTCACCCATCAGCAACATAACCGTGGATGACGAGCTCAACTTAAGCAGAGAACAAGACTTTGCTGAAGAGGATTTCATA
GTGATCAAGGAGGAGCGCGAGACAAGTCTCTCCCCCATGCTGACGCCCCCGCACACGCCCACCGAGGAGCCGCTGAGGAGAGTGCATCCGGCGAT
AAGCGAGGAGGCGGTGGCCACCCAGCTGCACATGCGACACATGGCCCACTACCAGCAGCAGCAACAACAGCAGCAACAGCAGCAGCAGCAGCACCGCC
TGTGGCTGCAGATGCAGCAGCAGCAGCAACAACATCAGGCTCCACAGCAGTATCCAGTTTATCCCACAGCCAGCGCCGATCCCGTGGCCGTGCAC
CAGCAGTTGATGAACCACTGGATCCGCAACGCAGCCATCTACCAGCAGCAACAGCAGCAGCAGCAACATCCGCACCATCATCACCACCACGGCCA
TCCGCACCACCCTCACCCACATCCGCATCATGTGCGTCCCTATCCCGCTGGCCTCCATAGTCTGCATGCCGCGGTCATGGGTCGCCACTTCGGAG
CCATGCCCACCCTGAAACTGGGTGGTGCCGGTGGAGCGAGTGGTGTACCCAGCGGCGCAACTGGCAGCAGTCGGCCAAAGAAGCAGTTCATCTGC
AAGTACTGCAACCGGCAGTTCACCAAGTCGTACAATCTGCTCATCCATGAGAGAACCCACACGGACGAGAGGCCTTACTCCTGCGACATCTGCGG
CAAAGCCTTCCGGCGACAGGATCATCTGCGGGACCACCGGTACATCCACTCCAAGGACAAGCCCTTCAAGTGCAGCGATTGCGGCAAGGGTTTCT
GCCAGTCGCGCACCCTGGCCGTGCACAAGGTCACCCATCTGGAGGAGGGTCCGCACAAGTGTCCCATCTGCCAGCGGAGCTTCAACCAGCGGGCC
AACCTCAAGAGTCACCTCCAGAGCCACAGCGAGCAGAGCACCAAGGAGGTGGTGGTGACCACCTCACCAGCCACTTCACATTCGGTGCCAAACCA
GGCATTGAGTTCGCCTCAACCTGAGAATTTGGCACAGCATCTGCCTGTCCTGGATCTATCCTCGTCATCCTCGAGCTCAGAGAAGCCCAAGCGGA
TGCTGGGCTTCACCATCGATGAGATCATGAGCAGATAGATTGAAGGACCAGCGAAACCCGGTATCCGGTTTCTTTTGAGACATTCTAAAAGAGAT
TCAGAGAGCTGGACGTCCGCCAGGCATGGGAAATGCCTGGAATGGAAAACCAAGCGAGTCCAGCCCGCATTCTGGCCAAAGGTGCAAGTGGAAAA
TCCTCGCCAGCAACTCGTAATCGCAACCCAGTGAGCAGAAGAGTCATCCTCCGTGCAATCGGTTCTATGTAGCAGATCCCAATTGCGTTAAACAA
ATGCCAAAGTCAAATAGCAGAGGAAAACTGATGAAAAATCCAATGAAAAGTATTGCTAGCACAAGCCTCCTACAAATCGATTCCAAAACACACAC
ACACACACACAACTGTAAACTATAAACTTTAATAAATAGCACATAATTTATATTGTAATCTAACTATTATTGTATGTACCTTATAGTCGTAGTAG
CCCATTCAGTTCGTAGTGCTTATGGAGTAAACCAAATGTTATGTTACAATAGCTCAATCAAACAAACCTCAAACCCGCTTTGGTTATTGAAAGAC
TGTTTTAATTATTATATTTAAATAGTACTTGAATAAATCAATCGATCGATTGTGTAATGTT
(SEQ ID NO: 383)

Start ATG: 190

MSSTSASPISNITVDDELNLSREQDFAEEDFIVIKEERETSLSPMLTPPHTPTEEPLRRVHPAISEEAVATQLHMRHMAHYQQQQQQQQQQQQHR
LWLQMQQQQQQHQAPQQYPVYPTASADPVAVHQQLMNHWIRNAAIYQQQQQQQQHPHHHHHHGHPHHPHPHPHHVRPYPAGLHSLHAAVMGRHFG
AMPTLKLGGAGGASGVPSGATGSSRPKKQFICKYCNRQFTKSYNLLIHERTHTDERPYSCDICGKAFRRQDHLRDHRYIHSKDKPFKCSDCGKGF
CQSRTLAVHKVTHLEEGPHKCPICQRSFNQRANLKSHLQSHSEQSTKEVVVTTSPATSHSVPNQALSSPQPENLAQHLPVLDLSSSSSSSEKPKR
MLGFTIDEIMSR*
(SEQ ID NO: 384)

Name: odd skipped
Classification: transcription_factor
Gene Symbol: odd
FlyBase ID: FBgn0002985

Celera Sequence No. : 142000013384622
TGATAAATAGCTTTTTATAAAAAGAACTATAACACACCTTTAGAAACTCTGGGGCTAGGTTCAAAATGGTTTTCGGTTTTAAGGTCCCAAATATC
TGTTTCACCAATTCCAGGCGGTCGTCTATGTAATGGGACATGGGATGCAGCTTTCGTTCCTCCTCGATCTTCTCCTTCTTAATGCTAATGGGCTT
GGGGATTTGGTCGCCCTTGCTGGATTTTTTCGCCTTCAAGCCACTCATTTTATCCAATTTGTTGTCAAAATAAAAACCAAGTAATTTCGGTCTTT
CGGGCAGCGTTGCCACTACTATTTATACCTTGTGGACAGTGGGACGAAGGCAACAATTTTGTGGGATTAGTGTGAATGGCTCTATTTTAAAATTC
AAAACGCAAAGAAAAACGAGCAGTATTACGAAAATGTATTTAATAAAAATTATTTCGTATACTAGGGAATGGCACATAGAATCAATAATTAAAAA
TGTACAATGGTGTATATTGCCTTTAGGACTGTATTATCCACTGTGCGCTGTTGTTAACAGTGTTATTGTTTTTTGTACAGAACAGCTGATTATCA
AGCGGTGTAGGTTGAATTAAATTGTGGGAGTGTTAGTTGTCTTAAAATTGTTAAGGTAAGTTGATGTATTAATTGAACTTGTAATCCATCAGTGT
AAAAGTGTTTACGGAAAGCGGTGATAGCAATTTTATATCAGCAAACAGTTTCTTGTCGTAGATATCATGTGAAATCCGTTAGTAAGGTGTTACGT
GAGAAATAGTACTTGTGGCAGAATTTTAGAGTTTGGCTTTTATTAATGGGGATCTGTTACTAGTGTAAGTTACATTTAAACACATTAGTCCAATA
TATATTTAGCATTTTCTATATTTTTGTTTTTTTGACATGCCGCTAGAAAAGTAACAGAAACTGTTAAGTAACAGTGATGGCACATTTAGGTTATT
TCATTGGGGAGCGTGTTTTGACAACTCTGCTGCGGCCACACTGAACATATGTTCCGGGGAGAATGGCTGCGATTTCGCGTCGGTAAAAATAGCAA
ATACTCGTTAATGTGCTGTGGGAACGCTTCCTCCCCGGCCCCAAAGTGGCCCCGAAGAAAGTGAGCAAATGTGCGCGCCGCAAGATAGTCGCCGC
CGAACAAACGATAGTGACGAAAGTGATTTAATTCAACTACCAGCACTCCCGCAAATACGATGAGTATGTCGCGCGGCGGCAACACAACTCTGGAC
TTGCAGCCGCTCCTGGCGGAGAGCGATGTCGGAAACAGGGAGCTGGAGGAGAAGATGGGCGGATCGGCGGATCGGTCATCGCTGCTCGATGGATC
CGGTTCGAAGGAGCTGAGTCACCGGGAACGCGAGGACTCGGCGTTGTTCGTCAAGAAGATCGGGAGCGCCTTGTTCTATGGCTTGTCCTCCTTCA
TGATTACGGTGGTAAACAAGACGGTGCTTACCTCCTACCACTTCCCCTCGTTCCTGTTCCTCAGCCTCGGGCAACTTACTGCTAGCATTGTGGTC
CTGGGCATGGGCAAGCGCCTGAAATTGGTGAACTTTCCCCCTCTGCAGAGGAATACCTTCGCCAAGATCTTTCCGCTGCCACTGATATTTCTGGG
AAACATGATGTTTGGACTGGGTGGCACAAAAACCTTGAGTCTGCCCATGTTCGCAGCCCTACGACGCTTCTCTATCCTGATGACCATGCTGCTGG
AGCTCAAGATCCTGGGACTGCGACCTTCGAATGCGGTTCAGGTCAGCGTATACGCAATGATCGGTGGAGCGCTGCTGGCCGCCTCTGATGATCTG
TCCTTCAACATGAGGGGCTACATCTATGTGATGATCACTAACGCCTTGACCGCCTCGAATGGCGTATATGTGAAGAAAAAACTCGACACCTCGGA
GATCGGAAAGTACGGCCTAATGTACTACAACTCGCTGTTTATGTTTCTGCCTGCCCTGGCCCTCAACTATGTTACAGGGAATCTAGATCAGGCGC
TGAACTTTGAACAATGGAATGACTCAGTGTTTGTGGTGCAGTTCCTGCTCAGTTGCGTTATGGGTTTCATCCTATCGTACAGCACCATCCTGTGC
ACGCAATTCAACTCGGCGCTGACCACCACCATTGTGGGATGCCTGAAAAACATCTGCGTAACATATCTGGGCATGTTCATTGGAGGCGACTACGT CTTCTCGTGGCTCAACTGTATTGGGATCAACATCAGCGTGCTGGCTAGTCTGCTCTACACGTACGTCACTTTTCGGCGGAAGCGGGCTCCCGATA
AGCAGGACCACTTGCCCAGCACCCGCGGCGAGAATGTCTAGCTTCATCTTAGCTCAAACTCAAGCCAAAGCCATACGATATGTTAAGTGTATTCC
GTACTGTGTACTTCAATTGCGATCTGCGATTCGCGACAACGTTCGTATTTGATTTTCCTACAACCACACAGCGCATCGTCTCTGTACATATATCT
AGCTATATTTCTATAAAAATGTAATTTAGCAATTATGTAATTTTAATCACTTTGTACATTTGTCTGCATGCAACTGTTTCCTGCATCGAAAGTGT
CATAAGAAATAGAAATACACAGACTTCCACTCCTCCGCCTACGGAATGGGTGGGCCAGATAAACAATTGTGTTCCGTCTTCTGTTCCATTTTGGG
TCATAATTGATAAGATTGCCTGCTCCGATAAGGCATACAACTCGGACGTTGCAAATTAAGCAGACATCTTGCTCTCTCTCACGTGCTTTTCTAAT
TACTTTTTTGTGTAAAATAAGTAATGTAGTGGAACTGCGTTGTGGGATTTGCCAATTACTTGTGCTTAATAGGTTGTTGTTTATCTATTCTGAGC
AAACACGTTGGCGCCTTGAGATTAATACAAAACAAAGTACTGCATTGCCGGACAATCCAGCAGCGTCATCACTCAACATCACTATGTAAAAAGCT
TTGGATAGGTTGCTCGATTACTGATTACTCTATATCAAAATTTTGGGTTTTTATGTTGAATAAAAAAAAAACAATATTATCAGCCAAGAACGTGA
TTGCGAGTGGTGATAGTATTTTTTAGAATAGTACGCCTTCCGATATTTTGTGTTATTTTCCGTTTCATTTGGTAATTGCCTCAAAAGGCTTTTGT
TTAGATTGTAGTGCTGAAGAATCTTTTTCTTTGTCTTAAAAGTAAATAAATTTGCGCAGCTGAAACTGTTTTGTTTTAGCGAAATAAGTATGTAT
ACTTTAAGATGGCTATCTATTTTCTTAGAATTAGATTTTACTTGGTAACTGCCTAGTTCCTTATCAAAAGATTAAGATTTAAATATCCCACATAT
ATGTTGCTAAACTTATCTTTTAAATGGTGACTACTCATTTATCCAAAGAAACAACAATGACGACATTGAATCGGGCATAAAGCGGCAGAATGAGG
TGCTAGTGCCCCGGCAGCACTTTGTTTGGGTTATTTTGGGAGCCCGCAATATATGATGGGCGGTGGTGAAGTGAGGGATTCGGAGTGGGGACAGG
TAATGAGGAAGCCGAAACAGGTTTGCACAGACTTAGCCGTGCGGTGAGGTAAATTGTTAGTCAGCATCAGCCCCGACCG
(SEQ ID NO: 385)

Exon: 1001..2594
Start ATG: 1200

Transcript No. : CT12909
GTTCCGGGGAGAATGGCTGCGATTTCGCGTCGGTAAAAATAGCAAATACTCGTTAATGTGCTGTGGGAACGCTTCCTCCCCGGCCCCAAAGTGGC
CCCGAAGAAAGTGAGCAAATGTGCGCGCCGCAAGATAGTCGCCGCCGAACAAACGATAGTGACGAAAGTGATTTAATTCAACTACCAGCACTCCC
GCAAATACGATGAGTATGTCGCGCGGCGGCAACACAACTCTGGACTTGCAGCCGCTCCTGGCGGAGAGCGATGTCGGAAACAGGGAGCTGGAGGA
GAAGATGGGCGGATCGGCGGATCGGTCATCGCTGCTCGATGGATCCGGTTCGAAGGAGCTGAGTCACCGGGAACGCGAGGACTCGGCGTTGTTCG
TCAAGAAGATCGGGAGCGCCTTGTTCTATGGCTTGTCCTCCTTCATGATTACGGTGGTAAACAAGACGGTGCTTACCTCCTACCACTTCCCCTCG
TTCCTGTTCCTCAGCCTCGGGCAACTTACTGCTAGCATTGTGGTCCTGGGCATGGGCAAGCGCCTGAAATTGGTGAACTTTCCCCCTCTGCAGAG
GAATACCTTCGCCAAGATCTTTCCGCTGCCACTGATATTTCTGGGAAACATGATGTTTGGACTGGGTGGCACAAAAACCTTGAGTCTGCCCATGT
TCGCAGCCCTACGACGCTTCTCTATCCTGATGACCATGCTGCTGGAGCTCAAGATCCTGGGACTGCGACCTTCGAATGCGGTTCAGGTCAGCGTA
TACGCAATGATCGGTGGAGCGCTGCTGGCCGCCTCTGATGATCTGTCCTTCAACATGAGGGGCTACATCTATGTGATGATCACTAACGCCTTGAC
CGCCTCGAATGGCGTATATGTGAAGAAAAAACTCGACACCTCGGAGATCGGAAAGTACGGCCTAATGTACTACAACTCGCTGTTTATGTTTCTGC
CTGCCCTGGCCCTCAACTATGTTACAGGGAATCTAGATCAGGCGCTGAACTTTGAACAATGGAATGACTCAGTGTTTGTGGTGCAGTTCCTGCTC
AGTTGCGTTATGGGTTTCATCCTATCGTACAGCACCATCCTGTGCACGCAATTCAACTCGGCGCTGACCACCACCATTGTGGGATGCCTGAAAAA
CATCTGCGTAACATATCTGGGCATGTTCATTGGAGGCGACTACGTCTTCTCGTGGCTCAACTGTATTGGGATCAACATCAGCGTGCTGGCTAGTC
TGCTCTACACGTACGTCACTTTTCGGCGGAAGCGGGCTCCCGATAAGCAGGACCACTTGCCCAGCACCCGCGGCGAGAATGTCTAGCTTCATCTT
AGCTCAAACTCAAGCCAAAGCCATACGATATGTTAAGTGTATTCCGTACTGTGTACTTCAATTGCGATCTGCGATTCGCGACAACGTTCGTATTT
GATTTTCCTACAACCACACAGCGCATCGTCTCTGTACATATATCTAGCTATATTTCTATAAAAATGTAATTTAGCAATTATGTAATTTTAATCAC
TTTGTACATTTGTCTGCATGCAACTGTTTCCTGCATCGAAAGTGTCATAAGAAATAGAAATACACAGACTTCCA
(SEQ ID NO: 386)

Start ATG: 200

MSMSRGGNTTLDLQPLLAESDVGNRELEEKMGGSADRSSLLDGSGSKELSHREREDSALFVKKIGSALFYGLSSFMITVVNKTVLTSYHFPSFLF
LSLGQLTASIVVLGMGKRLKLVNFPPLQRNTFAKIFPLPLIFLGNMMFGLGGTKTLSLPMFAALRRFSILMTMLLELKILGLRPSNAVQVSVYAM
IGGALLAASDDLSFNMRGYIYVMITNALTASNGVYVKKKLDTSEIGKYGLMYYNSLFMFLPALALNYVTGNLDQALNFEQWNDSVFVVQFLLSCV
MGFILSYSTILCTQFNSALTTTIVGCLKNICVTYLGMFIGGDYVFSWLNCIGINISVLASLLYTYVTFRRKRAPDKQDHLPSTRGENV*
(SEQ ID NO: 387)

Name: nucleotide-sugar transporter, putative
Classification: transporter

Celera Sequence No. : 142000013384645
GAATGATATATGTTCTGCAGCCATGCAATATATATAAGTACAATTTATTAAATTTTTTAATCTAACATTGCTGTGGTGAGTATGGGGGTTGGGTC
ATAGCGTTTAGTATAAGTATTTTAAGTTAAGTACTTTTCTTGAGTGACATGGACTGGTAACATTAACATATGGCACAATATTTTAATTATTTTTA
CAAATAGCATTTAATTTTAAACTAGCATTAATTTCTTTTTATATTTTTGGATACCCCGTCAGAAGGACGAAAGCACCGGAAGGACAGAAGGACAG
GAGTCATCGCCGGGGATAAATTGGAGTTTTGCAGCATTTAAATATAGCCGACTGTCCCACCCACTGTCCCTCCCACTGAAATCTTAATGTTGCAG
ATCTATTGCAGAAATCTTATTGTTAATAAAGCGGTTCATGACATGGATTGGTTGTGGTATTGGTACTAAAGAGGGCGGATCTTAAACTCCTCCCA
CTGTTATGTTATTATCTCAAAAACAGTGGAAAATTTTTAATGATTTTTTAATTTAATGAAATATTCCTGAAATGTCCTTAAGGTCTGAGGAGTTA
AGGTTTGAGGAGGTCTAGCGTGCAAAATGTTGGGGAGCCGATTATTCTATCGCATTATTTTTTTACTTTCTTGAGCCCTATAAGTAGTACATAGA
TAGTTAGATCTGCCATTTTGAAACATTTTTGCATTTTTATTCTTGGGAATTTACTCCCAAATAACGTTAGCGCAAATTTATTAATTAATGTATTT
ATTAAATAAATTTATTATACTGATAACATATTAATATAGCAAAAAAAAATACGTTTTTGAATATATGTGCATTCTTTTTAAACTGCTGCACACAT
TTATTATTTTTTTGGACTCTTACAATACTTTTTCAAAAATTTTAAATATAACTGCGACTTTGAGCGATACTTTCACTTTTCCCGTGACGCCAACC
GATATGCACAGCGCTTGCAGCCCTGGCCAATTTTGATGTGTTTCAGCATTGTACCCTGACAACCCTGCTCTGTAAAACTAGGAAAAACAGAAAAT
TTTATTTTCAATTGTTAAATATCCAAACGTAAACAGCCGGAAAATGTCACGACAAGCCTCTCGTTTGGACGCCAAGAAAGTGGTAAGTTGGCCAA
AGAAGAGAGAACAGCGCAAGATCGGTATCGTTAGTCATTTGGAGGCATAGATCTAGTTGTAAGGTTAGATTTGTGCCATAGTGCCTAAGAACGAA
TCTTTGACGTGCCATCCACCCTCAAAATCGGCTTCATTCACTTTTCCAGTAAGTGTGTGTGTTGGGGGCTTGAGGTTGAGACACGGACACACAGA
CAGGCACAAGCCGACGTGCAATCAGGCAATGGAAAACCATTTCAGCGCCACCAGTCGCCCCTCAGCCACGCCCAGAATGTGCACCACCGCCTCTG
CCGTCGGTGCTGCCGCCAGCGCCGCCGCCGCCGCCGGCAACAACAATAACAACAGCAATAGCAGCAGCAACAACAACGCAACAACCGGCAACAAT
TTAAGTGTTAGCACTGCAGCCGGAGGAGCCACAAATGCCGCAGCAACGGCACAACCCATCCAAGTGATACCAATGCCCATGCTGCCCACCGGAGC
GGCGCAAATCATAATTGGCCAGCAGCCACAGGGTCAGGCGACGGCGACGGGTCTGCAGCCACAATTGATACCGCTGCAGGCCAACCAGATTATGC TGCAGGCTGCGCAGCAGCAGCCACAGATGCAGGTGATGCAGCTGCCCGATGGCCAGACTATATTCTATCAGACGCCCACCATTGCCGCCTTGGAT
CCGAATGCAGCGGCCAACGCCGCAGCTGCCATGGCAGCCCAGCCGACGCCGCACTACCTCAATATCAATGGGCAGCTGGTGCAGATCAATCCAGC
ACCGAGCGCTAATCAGGCGGCACCCACAGCTGGGCAACAGATTATAATGGTGCCGCAGACAGCGATGGCAGCGGTGAATGCAGCGGCCGCCAATG
CCGGAGTAGGCGCCGGAGTGGGCACAGTGGTTACCCAACAACAACAGCAGCAGCATCAACAAGTACAATCCCAGACCCAAAACCAGCAGCAGCAG
CAACAGCAGCAGACGGTGGCGGCGGTGGCTGCCAGTGCTGCAGTCAATAATATAAGCGCCGATGTCAGCACAAGTACAACTGGAACGAATACGAA
CAGCGAGGACGAGAGCTCCAAGGGCGAGGCGGACGAGGAGCCGCTCTATGTGAATGCCAAGCAGTACAAACGTATTCTCATTCGGCGGCAGGCCA
GGGCCAAGCTAGAGTCGCGCATACCCAAGGAACGGTGCAAGTATCTGCACGAATCTCGTCATCGCCACGCCATGAATCGGGCTCGTGGCGAGGGT
GGTCGCTTCCATTCGGCACAGGAGAAGGGCGACCAAGATTCGTCCGGCCCGGAAGGCGGCAGCATGCCAATGGCGTCCAGTGGCGGCGTCACCCT
CAGCCGTGGCACGGCACGTGCTCCGCCCAAACTGATCGCGCCACATCAAACGCCCAGCATTACCATAACGGCGATCAAATCGGAATAGTCGCCTC
CTAGCTGTAGGATACAAACTAGATAAGATTGTAGTCATAGCGTTTAGTCCTAAGCCAGTCGCTCTGTGTCCATTTGTCCTCAATCACACCACTTT
AGTCGGCTCACATAGTTTTCATTTTTTTTTTTTTCAAAATTAAGTCTTCATATATTATTTTCAAAGGGAATTTTTGGGTTTTTCTATTTATTTT
CATTCACTTAGATTGGAAAAGTGATAAGTTCAAGAAAGAGATAATTGTTTTACTTATTATATTCATTTTCTAAATCGTTTCTAATTTCTAATATT
TATTTTCTGTTAGCCAGCTGTTAAAAATTGTTTGTAATTATTAAATAGAGAATTTATTTCATTTACTAGACATTTTCAAAATTTACACAAGTAAT
GCAATTATTAATTTAGGGTTTATAGTTCATTTCAAAATGGAATGGGGAAAGGGCTGCCAATAGTCACCGCAAAACAACAGAGCTCAACAATATAA
GATTCAACAAGGGTGAATGATATAGTCGCCTTCCCCGACTATCAGATACCCGTTACTCAGCTTTTGGAAATGCGAACTCGAAATTTCAAAAGTTC
ATAAATTTCAAACAAATTTTTTGGCAAATCGATAGAAGACTAATAAAATTATGAAAAAATATCCAAAAAATTTTCAAAAGTGTGGGAGTGGCAAT
TTTGTGCGGCTTGTGGGCGCTGCGTCGTGGTCTCTATCATTAACCTCAATATCAACCCTTTAGCGTTTATATTTCCTGAGATCTCTTTTAAACGG
ACAGACGGACATGGTTACATCGACTCGGCTACTGATTCCGATCAAAAATATATATACTTTATATGGTCGGAAACGCTTCCTTCTGCCTGTTACAT
ACTTTTCAACGAATCTAGTATACTCTTTGAATCTACGAGTAACGGGTAAAGCACCATTGAGGACCATTTGCCGCATAATAAATGCAACACAGTTT
ATAAAATTAAAAAAAAAAAGCATATACATTTACTGCGGAACTC
(SEQ ID NO: 388)

Exon: 1001..1127
Exon: 1285..2558
Start ATG: 1359

Transcript No. : CT12939
GTACCCTGACAACCCTGCTCTGTAAAACTAGGAAAAACAGAAAATTTTATTTTCAATTGTTAAATATCCAAACGTAAACAGCCGGAAAATGTCAC
GACAAGCCTCTCGTTTGGACGCCAAGAAAGTGTAAGTGTGTGTGTTGGGGGCTTGAGGTTGAGACACGGACACACAGACAGGCACAAGCCGACGT
GCAATCAGGCAATGGAAAACCATTTCAGCGCCACCAGTCGCCCCTCAGCCACGCCCAGAATGTGCACCACCGCCTCTGCCGTCGGTGCTGCCGCC
AGCGCCGCCGCCGCCGCCGGCAACAACAATAACAACAGCAATAGCAGCAGCAACAACAACGCAACAACCGGCAACAATTTAAGTGTTAGCACTGC
AGCCGGAGGAGCCACAAATGCCGCAGCAACGGCACAACCCATCCAAGTGATACCAATGCCCATGCTGCCCACCGGAGCGGCGCAAATCATAATTG
GCCAGCAGCCACAGGGTCAGGCGACGGCGACGGGTCTGCAGCCACAATTGATACCGCTGCAGGCCAACCAGATTATGCTGCAGGCTGCGCAGCAG
CAGCCACAGATGCAGGTGATGCAGCTGCCCGATGGCCAGACTATATTCTATCAGACGCCCACCATTGCCGCCTTGGATCCGAATGCAGCGGCCAA
CGCCGCAGCTGCCATGGCAGCCCAGCCGACGCCGCACTACCTCAATATCAATGGGCAGCTGGTGCAGATCAATCCAGCACCGAGCGCTAATCAGG
CGGCACCCACAGCTGGGCAACAGATTATAATGGTGCCGCAGACAGCGATGGCAGCGGTGAATGCAGCGGCCGCCAATGCCGGAGTAGGCGCCGGA
GTGGGCACAGTGGTTACCCAACAACAACAGCAGCAGCATCAACAAGTACAATCCCAGACCCAAAACCAGCAGCAGCAGCAACAGCAGCAGACGGT
GGCGGCGGTGGCTGCCAGTGCTGCAGTCAATAATATAAGCGCCGATGTCAGCACAAGTACAACTGGAACGAATACGAACAGCGAGGACGAGAGCT
CCAAGGGCGAGGCGGACGAGGAGCCGCTCTATGTGAATGCCAAGCAGTACAAACGTATTCTCATTCGGCGGCAGGCCAGGGCCAAGCTAGAGTCG
CGCATACCCAAGGAACGGTGCAAGTATCTGCACGAATCTCGTCATCGCCACGCCATGAATCGGGCTCGTGGCGAGGGTGGTCGCTTCCATTCGGC
ACAGGAGAAGGGCGACCAAGATTCGTCCGGCCCGGAAGGCGGCAGCATGCCAATGGCGTCCAGTGGCGGCGTCACCCTCAGCCGTGGCACGGCAC
GTGCTCCGCCCAAACTGATCGCGCCACATCAAACGCCCAGCATTACCATAACGGCGATCAAATCGGAATAG
(SEQ ID NO: 389)

Start ATG: 202

MENHFSATSRPSATPRMCTTASAVGAAASAAAAAGNNNNNSNSSSNNNATTGNNLSVSTAAGGATNAAATAQPIQVIPMPMLPTGAAQIIIGQQP
QGQATATGLQPQLIPLQANQIMLQAAQQQPQMQVMQLPDGQTIFYQTPTIAALDPNAAANAAAAMAAQPTPHYLNINGQLVQINPAPSANQAAPT
AGQQIIMVPQTAMAAVNAAAANAGVGAGVGTVVTQQQQQQHQQVQSQTQNQQQQQQQQTVAAVAASAAVNNISADVSTSTTGTNTNSEDESSKGE
ADEEPLYVNAKQYKRILIRRQARAKLESRIPKERCKYLHESRHRHAMNRARGEGGRFHSAQEKGDQDSSGPEGGSMPMASSGGVTLSRGTARAPP
KLIAPHQTPSITITAIKSE*
(SEQ ID NO: 390)

Classification: transcription_factor

Celera Sequence No. : 142000013384615
TTGGCGGGCTCTCCGAAATTCACAATAATTGCACGAACGAGTCGTGCGTTGTTTTCTCTGCTCGATTTCATTGTTTATGGGGCATAATATGTGGG
GATGCCGGGCCAAAAACGAAATTAATCACGAAAACGCACTCACCGTCGAAAAATCAACGAAAAGAAAGAAATTTGACAGATGGGTCGCGGTTAGG
GATGGCAAAGAGGCAGTGCTGGAGGTGGTATTTCGTAACGATAGTTAACGATGTTATCGGTTGTACTTGTCAGGGGTGAAGAGCATTGGATTCTA
CGTTTATAAATGGTTTTGATAGCTCATTTTCCTTCTTCTACGCTTATTTTTTTCCTATGAAATTGTTTAAATATTTACTGTTTTGTTTATGTCTT
CCTGTAACTGTTTAATTTAATTCAGCTAGTATCGATAACACTGTCATCTCTAAGTCGTGAACTGTCAAATTCAAAGCATGTGCTTTGCAACACTT
CAAGGGAGTGTGTCTTTGCTAAAATCGTGGTCTTGTTTTCACTGTTACAATTCAATATTTTCCAATTGGAAACCAGTTTAAATTTTTCCCAACTC
GTGAAAAATAAAAATAATTTTAAATTTTCGTTAAACGTTTTTATTACGTTTTAAAAGCATATTTTTCACATGTCAACATACTGATAGTTATAATT
TAATAACGGTTCTTAATACCTTTGTAAAAAATGAAATACAGATCAAGGATCTAACGAAAGGCCATTAATAAAGTAGATATGTAAGTAATATAAAA
AATATAGACAAATAGTTTTAATAGAATCAATAGCAATTCAGTGATTGAATTCATATTTTTACCAGCGTTGAAGAAAGTTCAGTAACATCTGTTGA
TCATCCGCACTAACAGAATGTTACCGAAAAGCTCAACGAAATACAGCCCGCTGTTAACTAACATGGCGCTTCGCCAACAGCAACAGGTTTCCTAT
GGTCCACGATCCCCACATATGTGGAGAATGGAAATTCAGTCGCGTGTGAGCAGCCCACTTTTAACGTTGTGGTGTCTCTGGGGATCAGATCCAAA
ATTCAAAAAAGTCCAGTTTGGCCTCTTGATTAAATCAATTCTTCCACTTCATTCAAGATGATGAACAGCCTAAAGAAATTGCCCGTGCGCATGGT
GAGTTGGCCACGCCCCCCTAACCGACACCTTTATACATACATATATGCCTACAACTAATTCCTTTTTCTTTATTAATTAACTTTTTAGCTGGCTA
ACGCTGCACGTCAGCAAAGTGCTGCGATGTCCTCGGCAACTGGTCTCCCCCCACCCCTCACCTTTCTCACCGACGATGAGAAAATGATGAAGGAG ACTGGTGAGTATACCCTTTGGATCTAAATAGATCATAGTGTTAATGGTACTGTACACGGAGTTGTAGTCCCCATTTGATAGGCGTGTTTTTCTC
CATGTCGAATTTTAGATATTTTATGGTGTTTAGAACTTGCTTGGTGTTACGTAACACCAAGCATCGCATTTTAATGATGCTCTTGTTATTTAT
TAATTTTCCATTGTGCTAACCAGCTGAAGTCTTGCTGCACTACTATGTGTGTATTCGTATTTTTCGAGTTTTGTTCTTTTTTTTTTCCTTTTTTG
CTGATAAAGTTTATTCAGTTGAGGGAAACGCGGAGGAGGCCGCTTGCCAGATAAGCACATTTTTATTTTGATAGTAGAAGTAAAATGTCACTAAG
TATTAGTGGGTAGGTTTGTCCATTTTCTTTATGACGTTTGTATGTTTAAATATTACAAGATATACAATTTCCGATTTGATCCTTATTGTAAAATG
ACGATCAACGATTATTACCTTATAATTAATTCCTTATTAAATTAATTTTTCTGGCGATTATTATATAATTTGTAATGATTAATCCCTTAAATTTT
TTGTAGTGTAATAAACCTAATATTTTTAAGGTAAATGAGGTCCTTGAATGTGTTTCTATGTTTATAATTTATTCCCTTTGGTGAAAAATATTTTT
ATCTATATAAAATAATTTTTAATAAAACTATTTCAGTATTTAATAATAGTATGCTTAAAAGTTACAAAATATTAATGATTCATCCCACTGAGGTC
CTTAGGTGACAATTTTGTTATGTACTGCCATAATAAGGTTAGCTCTTAAAAATCATACGATTTCTTAAAGCTGGTTACATGCATGTTTAATGAAT
ATAATTAAATTTAGAAAGTTACAAATAATATAATAATATAATATATATAATAATATTTCGAATATCGTGTTGTGTCAAATGTGTTTAAAAGTGTT
CACTTAAACTAAATGAATATATGTATTCTTAAAAAGTGCACAATTAATGGCCGAAGAGCTAAAGCTGCCAGCTTGGCAAGTTCAAGGTCTAACCT
TATAACAAGCTTTTTTCCCGATGGAAAAATTTTCCTCCCACCTGCTTAATTCTTTAAAAAATTATAATTAATTGATAATAATAATAATTTACCAG
TGAGAAAACTTACCCAGGTGGGCTGAAGGAAAAAGGGGTGGGCCCCGCACACACGCCCACCCTGCTCACACACACACACACGCGTGTTCTAAAAA
TAGCTTTTGCCCACCGCCAACGCTGAACATCGAGTTTCGTCGCTGATATTTCTCGGTTGGCCGTGGTGTTCCTCGTTGAGCGGCCGGCACATAAA
GAAAGCAATTTACCAAAGCGCGAGTTCGAGCCCTCAAATTATAAGCCTCTCTCATCCAAGATCCTCTCATTTCCCCTCCCACAGAGTACTGTTAT
TGCGTGCGCGGAATGTTTCTTATTAAACTTATATAGTGTCCTTAAGGATATCCTTTAACCACGAGTTTTCACAGGTCAGTCAGCTGTACGGTTCT
GGTTTTAAACGTCAACCGAATAGCGTTACACCAGTGATAGAGCAATAAATGCGGCTGTGCCATTCCCCCTGTCCACCTGTGGCCACTGTTCTAGT
GGCCACGCCGGGCAATCCGGGGCGTGGCACTTGGCCGGGCGCCCTTCCCTAGAGAGTTGAATTACCTGAGTGGGGGAGGACGACGACTTGTTGT
TGTTGTCCCCCTGCAAACCATCTAATTCCTAGTTGGGAAGGTTACATTTCCTTTTTATCACCGATCACCTTGTTTTTCCTCCATAATAATTAATA
ATCCTCGTCTCGCTTATCAGTCCCTCAACTGGACTCAATCTATATGGCTTCCCATATATATACATATGTACATATGTATGTGTGTTACATACAAA
TAATTCTAAGTGGGAAAGTATGTGTCTATATGGCCTAACTGTTGCGTAATCTGAGCTGAATGCAAAGTGGCTAAGTGCATGAAGTCAAACTGGTT
TTTTTTTATATTTTTCAATCATATATCATAGGCTTTGGCACAGTTAACACATTTTAAATTAAATTATTACATTAAATTTTCTGTTTTAATATGTA
TTTCAAAGTGCTTGATTTTTTAAGTAAGCTTTAAGTACGTAAAAGAATAGCAAACACACATTTACTCGAACGATTATTACCTTCAAGAACCAAGT
ACAGTTGCCCAAAAAAAAAAGCAAAATTTCAATTTCAGTCTATATCAGACTAAAGAAATGACCTGATTTTATTGAATTTCATATTTCCACTATAAG
CCAAACTCCAAAAAGGACATGTAAAATTTACCATCAAGCCCATTGGGACACGACACATCTGTTCGAAATTTTCCGACTGACCCCTGTCCATATGT
TGGAAAACTAAATGAATATATAAAGTTAGTTAATTATTTAAGCAATTCCCATGAAAAGTGAGCGAAAGAAAGTATTTCCAAATGTGTGCAAAACG
GCAGGAAAGTGATTGAAGAAGGGGCGACGGAGGTGTGGGAGCTTCTGTGGGTGTGTACCAGTTGGATTTCCAAGCAGAAAAACAGAAACACAAAG
TCAAGAAAAAAGAAAAAAATGCTTAAAAAAGATCAATAATAAATACGCTGAGAGAATAATAGAACTGCCGAAAGAAGACAGCTGCGAGAGCCCCA
CGCGATCGTAGAATCTAGTGATAAAAAACGAACACACGAAGACTTTTTATCTGAGAGACAAACGCGTGTAGAAAAAATACATACCTCAACCTACAC
AAGCAAGAGATCAACAGCAAACATCGCGCCCCTTAGAAGAAAAAGAACTCCAAAAAAAATAAAAATCAAAAAAGCTTAAGTTTTTACCTTTTTTC
AAAAACGTGCAGTTAAAAGCTTATCGAAGCTTTACAAAAACTTTGACATTAAGCTCTTTCACCGATCGTTACATTCTATATCTACACATATACAT
ATACACATATGAGTTATACTTAAGGTCTAGGAATTCTTATGTGTTATAATATATTTAAAAAATAAAAAACCTATTTTAAATGTATCTAAATGTAT
GCAAGCATATTTGACGTATATGAGTTATTTCACATGTTTCATAAACCATGGAAACTTTCCTTTAAACTTTCAGTTGCCAAACTGGCTCAGGAGCA
GATCCAGCCCTTGGTGAAGAAAATGGACTTTGAGCACAAATTCGATCCCTCCGTGGTGAAGGCGGTTTTCGAGAACGGCCTGATGGGCATTGAGA
TCGACACCGAGCTGGGAGGCAGTGGCTGCAACTTCATGACCAACATCGTCGTGGTGGAGGAGCTGTCCAAAATCGATCCTGCCGTCGCCGCTTTT
GTGGACATTCACAACACACTGGTCAACTCGCTGATGATCAAGTTCGGCAATGCCGAGCAGAAGGCGAAGTATCTGCCTAAGCTGGCCCAGGAGTA
CGCCGGTAGCTTCGCCCTGACCGAACCCGGTGCAGGATCCGATGCCTTCTCCCTGAAGACCGTCGCCAAGAAGGACGGCTCCCACTACGTAATCA
ACGGCTCCAAGATGTGGATCTCCAACTCTGATGTGGCGGGAGTCTTCCTGATCTTTGCCAATGCCAAGCCAGAGGATGTAAGTATATATTGTTTT
AAAGCCATTTAAATTTAGAAATAAATCATATTTTTATTAGTTTTTTTTTCGATTATACCCCCTAGCTTCGTTTTCACTTTTTCGCAGACCACTGA
ATGATTTCAAAATATTTTCCGTTGCTAATCTTTATGTTATTCCAACTGATTGCCAACTAATCGCTCTCAGATCAAAGTTCACTTGATTGCAGTTC
GTTAAATATTAAAATATGCAAATGAGTTTTCTTTTCAAATATAACGTTTGAGGAAACAAATTTCATATTCCAATTATTCGACTGCATAATATAAA
CTTTCTTCAATTATATTTTACTGAACAAAAAATCTGATTGCGTAATTCTTTCAAACTAAAACCTTATCGTTATCTTGTTTTTTGCAGGGCTACCG
TGGCATTACCACCTTCATTGTGGACCGTGAGACTCCCGGTCTGATCGTGAACAAGCCGGAGGACAAGCTGGGCATCCGTGCCTCTGGAACCTGCC
AGCTCACCTTCGACAACGTGCGTGTGCCCGAGGAGAACATCCTGGGAACCTTCGGCCATGGCTACAAGTATGCCGCCGGCTTCCTGAACGAGGGT
CGCATCGGTATTGCTGCCCAGATGGTGGGCCTGGCCCAAGGAACCTTCGACGCGACCATTCCGTACCTGCTGGAGCGCAAGCAGTTCGGTGATGC
CATCTATAACTTCCAGTCGATGCAGCATCAGATCGCCACCGTGGCCACGGAGATCGAGGCCGCCCGCCTGATGACCTACAATGCTGCACGTCTGC
AGGAGCAGGGTGTGCCCTTCCAGAAGGAGGCGGCCATGGCCAAGTACTACGCCTCCGAGGTGGCCCAGAGGGCGGCGATCAAGTGCGTCGACTGG
ATGGGAGGCGTTGGCTTCACCCGTGATTTCCCGCAGGAGAAGTACTACCGTGACGTGAAGATCGGAGCCATTTACGAGGGCACCACCAACATGCA
GCTGAGCACCATTGCCAAGTGCATCAAGAAGGATTATGCGGCCTAAAGACTACCCCGATACTCCTCCTTCCCCCAACATATCCCCCACACAAGCT
GAGATATCGTACGTCAGATACGTCAAGTGCATTTATGCGTGGGAACCGCTGGAACAATTTTGACGGCCATCCGTTATCGGTTCTCACCATGTTAA
CGTAGCATTTACCACTTAGTTGATTCTGTTATGCATATTGTATAAAATACAATTAAAATATATACACATATAAAATTTAAATAAAACATATAGTT
GTATAGTATGGTTAATTCACTAATGACTGCCTCCTCCATCCGTTGTGGTAAATGCGGCCAGCAGAATGTTGATCACTGTGATCATGAAAACTCCC
ATTACGAGCAGATCGTTGGTTCTTTCGTAACTTCGGTTCCTAAATCGCTTGAGACGTCGCTGCGGAGATTTTTTATTTAGTGAATGGACTAATTG
AAGCTCTACTCACATACTTTAAAGATCAGCATTATGCCAACTAAAAGCTGCAGCACCAGGGAAAGTATCACCATAATCATGCTGTATATGTACGT
GGAAGCCTTGTCGTTATAGGTGATCAGGAATCGCAACTGATTCGCATTCGCCGAAAGCAAAGCTATATCCATTAGGCCTACAAAAAGTAGTTTGA
ATATCAGAGTTACAAGTTGTGGTTAGCGTTCTTTAAACTTTAAGTATTGTAACTTTCGAATAGTGATTTGCATTACGTTCTTACCTTCAGCTACA
TTTTTGTTGGCAGCATAGCTATTCTCTGTCGAAAGATCGCTGGAACATTTCTTGTTCGATTTTTTGGATTCTTGTAATTCACTGGTGGCCCTGGA
TGGGAACTGGTCGTCTTTTATATGGCTTTCATGCACCTGAATATCCAAATCCCTGCCAGAACCGCAACATGGTCCACTGGTTGTACTGGCGAAAC
TTTCCCCGGAGCTGGGGGAATCCTCCAAAGATATTTTCACCTCGCCGCTGTCCATTGTTCGAGTTCCAACCGATTAATAAGCATTTAAATGCTCT
TCTTTTAAAAAAATGCGAAAAGCTTTTCTTGTTTTTGAGCATGAAAGCCGCAACTGCGGTTTAGTAACTGATAAAAGGGAATGACACTGACCGAA
CTACCCTAAAAAAAAAAAAAAAAAACTGGGCCATAAGCCGACCTGAAAAGTATCTGATGGGTTGAGATACGCACTAAGCATGTTTGCCTTAAAGT
ATGCTACACAATCTTATTTAAAATGAAGGTAAA
(SEQ ID NO: 391)

Exon: 1001..1138
Exon: 1229..1334
Exon: 4444..4922
Exon: 5313..6158
Start ATG: 1103

Transcript No. : CT12987

FIGURE SHEET 211

CAGCCCACTTTTAACGTTGTGGTGTCTCTGGGGATCAGATCCAAAATTCAAAAAAGTCCAGTTTGGCCTCTTGATTAAATCAATTCTTCCACTTC
ATTCAAGATGATGAACAGCCTAAAGAAATTGCCCGTGCGCATGCTGGCTAACGCTGCACGTCAGCAAAGTGCTGCGATGTCCTCGGCAACTGGTC
TCCCCCCACCCCTCACCTTTCTCACCGACGATGAGAAAATGATGAAGGAGACTGTTGCCAAACTGGCTCAGGAGCAGATCCAGCCCTTGGTGAAG
AAAATGGACTTTGAGCACAAATTCGATCCCTCCGTGGTGAAGGCGGTTTTCGAGAACGGCCTGATGGGCATTGAGATCGACACCGAGCTGGGAGG
CAGTGGCTGCAACTTCATGACCAACATCGTCGTGGTGGAGGAGCTGTCCAAAATCGATCCTGCCGTCGCCGCTTTTGTGGACATTCACAACACAC
TGGTCAACTCGCTGATGATCAAGTTCGGCAATGCCGAGCAGAAGGCGAAGTATCTGCCTAAGCTGGCCCAGGAGTACGCCGGTAGCTTCGCCCTG
ACCGAACCCGGTGCAGGATCCGATGCCTTCTCCCTGAAGACCGTCGCCAAGAAGGACGGCTCCCACTACGTAATCAACGGCTCCAAGATGTGGAT
CTCCAACTCTGATGTGGCGGGAGTCTTCCTGATCTTTGCCAATGCCAAGCCAGAGGATGGCTACCGTGGCATTACCACCTTCATTGTGGACCGTG
AGACTCCCGGTCTGATCGTGAACAAGCCGGAGGACAAGCTGGGCATCCGTGCCTCTGGAACCTGCCAGCTCACCTTCGACAACGTGCGTGTGCCC
GAGGAGAACATCCTGGGAACCTTCGGCCATGGCTACAAGTATGCCGCCGGCTTCCTGAACGAGGGTCGCATCGGTATTGCTGCCCAGATGGTGGG
CCTGGCCCAAGGAACCTTCGACGCGACCATTCCGTACCTGCTGGAGCGCAAGCAGTTCGGTGATGCCATCTATAACTTCCAGTCGATGCAGCATC
AGATCGCCACCGTGGCCACGGAGATCGAGGCCGCCCGCCTGATGACCTACAATGCTGCACGTCTGCAGGAGCAGGGTGTGCCCTTCCAGAAGGAG
GCGGCCATGGCCAAGTACTACGCCTCCGAGGTGGCCCAGAGGGCGGCGATCAAGTGCGTCGACTGGATGGGAGGCGTTGGCTTCACCCGTGATTT
CCCGCAGGAGAAGTACTACCGTGACGTGAAGATCGGAGCCATTTACGAGGGCACCACCAACATGCAGCTGAGCACCATTGCCAAGTGCATCAAGA
AGGATTATGCGGCCTAAAGACTACCCCGATACTCCTCCTTCCCCCAACATATCCCCCACACAAGCTGAGATATCGTACGTCAGATACGTCAAGTG
CATTTATGCGTGGGAACCGCTGGAACAATTTTGACGGCCATCCGTTATCGGTTCTCACCATGTTAACGTAGCATTTACCACTTAGTTGATTCTGT
TATGCATATTGTATAAAATACAATTAAAATATATACACATATAAAATTT
(SEQ ID NO: 392)

Start ATG: 103

MMNSLKKLPVRMLANAARQQSAAMSSATGLPPPLTFLTDDEKMMKETVAKLAQEQIQPLVKKMDFEHKFDPSVVKAVFENGLMGIEIDTELGGSG
CNFMTNIVVVEELSKIDPAVAAFVDIHNTLVNSLMIKFGNAEQKAKYLPKLAQEYAGSFALTEPGAGSDAFSLKTVAKKDGSHYVINGSKMWISN
SDVAGVFLIFANAKPEDGYRGITTFIVDRETPGLIVNKPEDKLGIRASGTCQLTFDNVRVPEENILGTFGHGYKYAAGFLNEGRIGIAAQMVGLA
QGTFDATIPYLLERKQFGDAIYNFQSMQHQIATVATEIEAARLMTYNAARLQEQGVPFQKEAAMAKYYASEVAQRAAIKCVDWMGGVGFTRDFPQ
EKYYRDVKIGAIYEGTTNMQLSTIAKCIKKDYAA*
(SEQ ID NO: 393)

Classification: enzyme

Celera Sequence No. : 142000013384678
CAGTTGGCTGGTTTTCCTCACACACACACACACAGCATGCATACATACATACATATGTATGTATGTATATGGCGAAAAAAGAAGAAACTCATAAG
CTGACGCTTACTGAAGCTTCCTTCGTTTCGCCTTCGTCCTTGTGCCATCGTCCTCGTGTATCCTTGGCTTCGGCGGCAGTCGCCCTTGCAGAAGG
TTACGCCGCTGGGCTCGAGCGGTTGGATGAGGGGGGCGTTGGTTCTGTGGGTGGTGCTCTGGCACGTGTCCCGTTATGTGGTAGCAACTGCGGCA
GGACTCTGCGGCTTTTGTGGGGCAGTCACAGTGAGAACACTCGTCACAAAACTGAACTATTTTGTTGTCATTGCTGCGAAATGCAATCGAATAAT
GATCGTAGATAACTCTTTTTTTATAGTATCTTAGAATTGTGTATCTTCTATCTAAGAATATATGAAAGTACTTCAGTACAGTAAGGATCTCGGTT
TGCTAAAAATCCTGTTCAAAACTTGTAGTCCTTGAGTTCTTCACTTGGAACCCCTAACTAGTTAGCCCCAATTGTTTACAGTGCAGCCGACACTG
GCGGCGACAAAGGGCTTTGGTTTAGCGTGCTGCCATATGTTTCCGGCAAGTGCTCGCCCACCGCCACCCACTACTCCTTTATGGGCCATGAAAAG
CGTTGAAATCCGCAATGCCAACAAGTAAACTGCTGGCCAAGCGGGGTTGCCAAGGCATCGGTGATTTGTGGACCCCAAGGCCAAGAATGGAATGA
GGATGGCACCATGGAACGCTGAAACGATGGCTCTGTAATTTGAGCCGACTTCCTTTCGAGCGGGGGCGACACCTTCTGTCGACGCCGAGCGCCCT
GATTTATCCGCAGCCCATAAAAGAATATATAAAGCCACACTCGCATTTGTTATACACTGTGTTCCATTTTCATGTTTTTATTGTTTTCGAAAATC
AGCTAATTTAACTTAGTGTTTGTGTGGGGGTGTGTGTGTGTGTGCGTGTGTTTTTTTTTTTTGTTTTTTGGATTACATTTCGAGGGTTTTCTAAC
AGTATTACATACAGATGTGCATACAATCAGATTTCTAAACATATATATATGCGTTATATTTAAGTATTTATAGGTTTAATTAGTTAAGGTATC
CGAACAGTACAATATCAGCTTAAATAAGTCGAGCCTTTTCTCGCATATACAACTAGATATATGTATATAGATAATGTATATATTTCAATAATAGG
AATAAATAAATATACAACAATCAGGAGTCGGAGCCAAAGTTATTATTGGAATAGCTGGAGGTCGATCCGAGGCCTTCAATTTGTTTGATTGCCTG
GAAATTATGTTAATTTTTCGCCCGATCATGAGGGGGATGCTGCCAGCAGACAGGGGTTGCAAAAATAAGATACAGATACGAATAAACAATGGGGTG
GATCTGCCACCATGTACCAATTCTAAATTCCAGCTATTCCTCTAAGAAACTCATATAACTTAGGGTTTTTCTTTTTGCTCCCCTCATAAACTTTA
AAGTTTTTTCTTTGCTTAAAATATGTACAGACCATATACAAGATAACAAAACAAAAAATATCAGCTAAGAGCAAGTTGAGAATAAATGTACGAAA
ATCTAAAGCCTTTTTCGAGTGTACGAATATCGTAAATATAAGAAGAAGTTTATCAATATTTGCATAATGCGTGTGTGTTCGTGTTTATGTGTATA
GTATTTCATTTGGTCGAAGCTCTAAAAAAATTAAAATTCATTTCCAAGTTGCTGGGTGCTGTGTGCTGGGTTGGCATTTTGTTTTCGCCTGGCTTC
GATTTTTAAATTTATGTACAAAATTCGTGCTGCAATTAAACGTAACTCGCTTAAACAACTAATGCGACAAGGTATCTACAAGATATATATATATA
TATATTCGTATATATAAATATGTGTTTATATTTATTTGGGTATATGTATAGAAATATACGCATTGTGCCAGTGCGAGCTTGTTATTTTCATTATT
TTCATTCCGCTTTGTTTGCTTTTGTTTATATATGCCCAAGTATTGTTTTGTATCTTTATGCCTGACACGCTCGCTCAAAGCGGCGCAAAATCGTT
AAAATTTTATCGCCCCGATGAGGAACGTGAGTGTGTATCGGGTATCGGGTATCGGGCTGTATCTTTCGCTATACGCGAGTGTGTTCCTTTCGAAA
AATCTAGCAGCTAGCCCAACCACCACCAACGCTACCACCGAATTTTCACACTTCGTGGCAGTTTTTCCTCAGGGTGTGGGCCAAACACTTTCGGC
ACTGAGTGTGTGTTGTTGTAATCAAATATTCCTGATGCGATTTCCGTTTTCGTATCGGTTTGTGGTTTTTCCTCTTCTGCGTTTGTTTTTTCGAA
ACAAATTGGTTTTTACTATCGCGCATTTGAAATTAATTTTGCTATTTATTAGTAGAGATCTTTTTCTCTTGTTTACGCTTGGACTTTCCCCAAAA
AGCAAAAGGCCAACCGAAGAAGATCTATCTACTAAAGGCATGTGTTTGTGTTCGTCTGACCTTATCGCGGTTTAACACATATTTTGCTGTTGATA
TTTTATAATTAATTTTGTTGTTGCTTTTTTGCCTGCTTTCGAAAATGCCAGCGAACGCCAGCGCTTTTGATTAGTATTATTATTCTCCTCCTCGC
TTCTTCTCTCTTTCTCTCACAGTTGGGTTATTTATTAATGAATATTGTTGCTGGCATTTTTGAAATTTGCTTGGATTATTTATTTAGTCGCGTAC
TAATTCGATTGCAAATGTTTGCATATATGTATGCAAATGATGCGGTTTTCGCATCCAACAGATACATTCCGCTGTGTTGTAGATATTGCTCAGTG
TTGTTCGGGTTAGTTCTAAGGCTTACGATCCATTCTAATGGTTGATTAAATTGCACTTCATCTTCGGGAGCGAGGTTTGGAAAACTTGCGCTATA
GGAGTTGTTTATACGGTTGATCATCACCTCAGTTGCTGTCGGTATTTCGCAGATTCTCCAGCGGCGCCACAAGATACATTTGCGTTCCGCACAGC
CAAAGAAACGCTGCAAAAGAAACGAAAAGAGGAAGAGAACGAATGAAAATGTTATTCGCCTTTCTATGGGTGAAAATACAAAATGATGTAATGAC
TCTACTCGGCCGATGTTCATTAAAAGGCCAAGCAAAACAGAAAAAAAAAAAACAACAACTGAACCAAAACAAAAAACGAATATCAAAACAAGAAT
GTTTGTCAAAGTGCAATGAAACGACTACAAGATACTCAGTGTTAGCGATCCAATGGATTTGTAAAAAACACATTCCACATTTCTTTGGAGTAATT
TGATTGATATTATTGAAAATTATGCTATATATGCTATATATTCATTTGAAATTTGTAAAGCGACAGTTTTCGTAATGCAAATTAGCTTCTGCTT
TTCTACACTTAAAGCCGGAATAGCTAATAAAATCCAGATGCTGAAACGGACAGACAGACTTTCATATCTGTCATCATCTCAAAACGCCGAGTTAG
ACGAGTTCAAAATACATTTAGTGCTCTACGACGACAAAAGGGGTATACAAAAAAACACAGCGAAAAAGTCAAAACTCAGTGTAGTAACGTCTAAA
ATAAAAGCAAAACGTCTGAAACGTATGAATGACCGACCAAGACCGCTGCCGAAGTGACGAACGACAAACAGAGCGAGATGGGTGGCTGTTTGGGG GCAGAGGGAAAGAGAGAGAGAGAGGGCGAGAGAGTACGTGGAAGAAGATACATTATTTGTGTATAATGACTACTTGAGAAAAGCCAAAGCAGAAA
AGAAACAAACAACACAAACAACACAACATCGGCAAGAAAATCGAGGCAAGAAGAAAACGCAAAACACGAAATGTAATTTGTATAATTTGAGTCTC
AATTCCATCAAGTGTGGGAAATGCGCCAAAAAGAAAAATTATATAGCCAACTCATAAGGGAAGTGGAAAGCACCGAAGAACTAGGGTTCAAGACA
ACTGGCTCCAACAGAAGAGTTTGTTTTCCTAATGTAGCGTAGAGTTTAAAAGGTCACAATGAATCGCTAAAAAGAAAAGCAATCAAATGAGGAAA
CTTGAACATCAGATCACCAGAATCAGGTGGTAACCAAATCATCTCACCTACTGGCCATCGAAGAGATCACATTCCAACAACAAAAAAAACCATTA
AAAAACTAGGAATATAATATGTAGATACATATAATCTCAGAGCTAAAAAACAATATTGAGGAACGAAGAAAGTTCCAAAAACGGGAAGTTCGAGT
TTTGTTAGTTTAACTTAAGTTAAGTTACTCAACAACAGAGGATTCTAGTTATAGATTCTAGTTATAGATTCTAGTTATGAATGACTCCACATATA
TTTCATAATTGTACGCTTATCAGATACCCTTAACCAATAGAAATCAGTGCAACACACTCACCTTGTGACTAAGCGGAACTCGCCACCGGAGCATT
GGCAATCTGTACGGGTGGCTTGGCCATGGTTTCCGGGACTGCGGACACACTGGAAACCGCGGATGGGATGGTCAGCAGAGTACTGGCCGCCGAAA
CGGTAATGGGCGTCTCCTTGGGCTCTGGCCTCAACGCAACCGCTGTGGTCGTTTTGGCCAACTCCGGGGATTTGGCCGCATTGGAACTGAGAACG
GGTGGTGCCTCCTCGGCGAGAGCGGCGGCCTTGGCCTCGGCGCGAATATTCAAATTGGCCGCCACTTGATCGATGGTCGTGGGTTTCTTGGTCAT
TGCCCGCGGCGAGGTGGCTGCACTGCATCCAGAGCTGCCGCTTGAGCTGCTGCTGCTGCTGCTGCTTGTGTTGGTGGGGCTCAATGATCCCGGAT
TGCTGGTGGAAACCTTCGGCTTTTCCTCAGCACGAACTGTCAACGGTTTGCTAATGCTGGCTGCTGTGCTGGCAGCTGCTGGCTGATTGCGGAAT
GCCAAAGCCGATGGATTGGGTATGCTCCGAACTGAGGCATTCTGTGGTCTTACCAAAGCATTGGCATTCTTGGGTTTGGCGGAACTACTACTGGT
GCTACCACTGCCGTTTCCACTGCTGGCGGCCTTTATGGAGATCTTCTCCCTGGCCGTTGCCGATTCCGAGAGCATATGCAGATTCTGTAGATCAT
CGCCGTTGGTTGTACCATTCGAGTTACTGCCAGAAGTGGTCGATGGTCCACCATTGCTGTTTGCCGATATATTCTGTTTGATTTTGTTTAAGGCT
GCCTCCAGGCTGTTGCTGGTGCTGTTGTTATTGTTATTATTATTATTATTGTTGTTATTGTTGTTGTTGTTGTTGTTGTTGTTGTTGTTGCCAGC
GGGCGGTGAGTTGGGCGCCAATTTGGCGTCATTGTTGCTCCTACCCGGGTTAGCTGATAAATCAAGTATATCGGCATCCTTGGCTAATGCTGTTC
CTGTTCCTGTTCCTGCTCCTGCTCCTGCTCCCGCTGCTGTGGTTACCGATGTGGTTGCTGTTGCTGTTACAGCCGACTGCACTGCTGGCCGAAAC
TCGCGCAAACTCGTTTTGGACTTGTCCAATGCGGCAGTGCCATTGGTTTTGCCTTGGCAGCCAGCTGCTGGCGGGGATTTCTTTGAATTGGCTTC
CACCTTTGGGCTCGACTTTGATGGAAACGAGTGCTGTGGAGCGGCTGTGTTGCGCAGATTTATTAATGCAGGCGGTGATGTGCGATAAGCATTTG
AGTTCGAGGAGTTGCCCTTGTTGTTCCTCTGGCCACTGAGCGCAACTGACAGTGGCGGCGACTTGACAATCGCCGGAATCGTGGTCATCGGCATG
GGCAGCGGCAGCGGCAACGGCATTGGCATTGTCGGCATTTGGCAGCTCCGCTTGGCCGCACCATGTCCATGTCCTGCATGTTTGGGCAGAGCCGC
TGGTGGTCCCATCAAGCGGGCACTGGACGTTGCCGGCGGGCTAAGAGGTGGCATCGTTAGACCCTTGCCTCCTGCACTCTGCTTATTCACCGGCA
ATCGCACTATTTCCAGTGCAGGCACATGGATATTTGGCTCCGAGAAGGAATAAATCGACGGCGTAGCTCTGGGCCTTGGCGTAATCGTCACTTGG
CTCGAACTGCTGGCCGGGCACAACATTGGCAACGTTGGCTTGCTGCCCAGGTCGGGTAGACCATAGGATCGCATCTGGGGATTGGGCAGAAAGGC
GGCCGCTTGACTTTTGGCCTGGTTGCTAGTCTGCATATGCAACTTGGCCGCATAACTGCTGGCCATCGCCTGAGCCTGGCTCAATCTCGCCTGCT
TGGCCGGATGCGATTCGTCCAGGGACATGGATCGCTTTGGCATCTTGTTAGCCGCACTGGCAATCGAACTGGGTGTGGACTGGTAGCGTTGCATG
TGATACATATTCCGGTGGGTTGGAGCCTGTGGCACCGCAAAGTGTCCACTGTTGGGCTTACGATTATTGTTGCTACTCAGCGGCGGTTTGGCGGG
ATTCGTTTTAGCCAGACTTTGCTGTAGTACAGCTTGAGGTTGCTGTGGCATTTGCTGTTGCTGCTGCTTGGGTTTTCCGCCGGCCACCGTATGTG
GAGCAGTTGGCGTCGTGCTGGGTGTATAGGCTTTGAATAAACTGGGCGGCAGAGGTGGCGATGTGGGCAAGGTTAGGTCCTTTATTTTTGGCAGC
ACCACAAACTGTTGCTGTTGCTGCTGCTGCTGCTGTTGTTGCTGCTGTTGTTGTGGTTGTTGTTGTTGCTGCTGCTGCTGCTGCTGCTGTTCTGG
TTCGGCGGTGGGCGTGGGCGGCGGTGTGGGTGCTCCACCCACCACCAGGCTGTTGATACTCCGCGCCTCCTCGCCCAATGTGCGATTCAGTGCCT
CGGAAGTGCTAGTACTGTCCAGTTTCAACTTCTGCAGATCCAACTCTCCACTGGCCAGTGAATGCGACCTCTTGAAATCCAACTTATGATTGGGT
TTTGCCGTTATCTTAACCTTCATTTTCCCATCGGTTTGCGAACTGATCTCCGCGTGCAACTTCTTCCGCTTGCCATTCGCATCCTTTGGCTCCTT
GGAGTGCTTCTTCTTGCGCTTGCGATGGGAACTGGACGTGCTGGTCGATGTACTGGCATCGGCTGTGCCCAGACTGCTGCTGGATCCATTGGTCG
AACTGGAGCACGAAGACATGGGCGAGGCATTGGGACTGTATTTGCTATCGGGATTGGATGCACTTTGCTGCAAAGGCTGCTCAATGGGCTTCAAG
CCAATATTCTTGGCGTAGGTCTCCAGATCGAGTTGTTGGGCTGAGCAAGATAAGGAGCAGGAGGTATCCTCCAGTCGCGGACCAGCCGATAATGG
CATACTCAGCTTGCTCTTCATGCTGTTCAGTTCGATCTTCAGTTTGGGCAAATGGCCAACTCCCTTTCGATTCGCTGTCTTCAGCTCAAAATCCT
CGGCATCAACGTAGGACTTTCGGAGTTGCGAGGGTGGAATGCTGACCACTATATTAGTATTGGCCTCCAGCGGCTGTTGTTCCCGTTCTCTTGGC
AGAAGGAACTGTTCTTGTTCCGGTTCACTTTTAACTTTGGACACGGCGTAATCACTGTACCGCATGTCATTGCTTCGCAGACTTTTGAAGTTGCT
CACCGGACTTTCAGGTTCCGCTTCCCGTTTACTCGACGTCAATCGTTTGTTTTTCGACGAGGGAGAAACTTTTGGCGGAGTCTTACACCGTACTT
TGGAACGCGGAGAACCGGAGTCTATTTCCGATTCCAGGTCCTCGGCAAAGGTCACCGATTTGGCCGACTTGGAGCGACGTACCGAATGCTCTGGT
TCAATGTCCTGGTTAATCCTGGATAGGTTGTTCTCATCGTTTTTTGTTTGCTCGTTGTCGTAAAGCAGAATCCGGTAGCAGAAGGCCATGGGCGA
TTCCTAAATGGATTCGGAGAGGGGAGAAATAGATGGAAAAAAGGGCAGGTTGACAAGGGTGGAAAATTGAAAGTGGACATTGAACGCTAAACTGC
CGGCACAATTGGATTGGGTTTCCCCTTGCGAAAATCTATCGGGTTATTGGGATAAACCGCAAAAAGGGACAATATACCGCCCGCCTGAAGAGAAG
AAAAAAGGGCGTATATAACACTTAAAACTGACCGATAATGATAAGATGGATATGTTTTCAAGGTCTAATTTGGCAGTCGGATGACCGCAGAATCA
AGTGAGAAGTTTCAACCCTGTTTTCTCTCCATATTGTTACGTAGTTTTTTTGTTTTACGGAATCAAAAAGTTACCCTTATGAAGAATACATTTCA
ATACACTAATTGAGAACTAAAATACTAGCATAAGTACTTTTTAAAGTTAATTTAAAGATTTTACAATTGCATTGTCCCTTCATTGCAGTTAAATC
CCTTTGCATTTTTAACCCATTGTCATTATAAGAATGCACTAATATTTCTTATTAAGTAAAACAAACTTACCCGGCTCCAGTTGTAACAGTAGGCA
ACGTCCATCAGGGTGAAATTGGTAGGCAGTACCTCATCCTTGTAGGTCACCTCCACTTCCACCAGACCGTTGTCCGTCTCTATGTTGTACTTGGA
GCAGAGGAACCTTTTCAGTAACTCCACAGGTAATCCGGCGGCACATTGCAGGTAAATAGTGGGAGGCACCTCACCAGGACCACACTGATGCAGCA
TGGCGGGATGGTATTCCAGGGATAAGCTAATTGATATAAACGAAAAGTAAAGCAAAAAGTTTATTAGTAAAATTAGTTTTACACGTTTAAGCATT
GTTAGCATTTAGCTGAAACCTACCTTATAAGTTCCGTGGTTGTGAAGAACTCCGGTTCATCAGTCGTTTGTTCATCCACCAAATCGTGCTGCTCC
TTGAAATCTGCCAGCTCCTTGCACTCCCTTTGATAGAGTCCCGGCACTAGCTTATAGATTAGCGATCGCAACGTATCATCCGATTTCAGATTCAA
TTCATTGATTTCCTTGCCTCCGCTGGCTTTACATTCCGGACAATATACCGCTCGCAGCAGGTGCTTTAGTATGCAACTCCGGCAATCTGTTGAGA
AATGATAGATCAAACCGAATAACAATATGTTTAATGATCAAGGAAAATGTGTATTTTAGCTTAAGAACTACCAGAAGCTGTGATTACATTGTTTA
GTAATGATCTTAAAGTTTAAGATCTAACTTGGGCAGTCAATATTGTAAATCATGACAACCTTAAATTAACTTTATAAATGAACTTTAAAATGGTA
AAAGTGATCAAACAAATAATGATCAAATTACATGCAATTAATACAAGATATTGGTTTTATGCGTATATTAAAGGTACTCTTTGGAATCTAAGACT
ACTTACAGGTATGATAACAGTAATCCACAGTGGTTGGATCGATCATATAACCGCGACAAAGTCGGCACGTTATCAGATCATGAAACTGCCGGACA
TCCCGAGAAGCTGGGGATGCGGCATCCATAGCGGCGTTTGATTCCATTGTGTTGTGCGTGTTTTGCAGGTGCATCTTTCTGCCTATTCTATCTGC
CTCAATACTTACTCCTAGCAGCCTCTTTCAATGGGGTCCTGGAAGAGGAACAAGGATGGGGGTTAGGACTCGGCATATCCATGTTTGGCATGTGC
TCGCTCAACAAGTGACACTAGTGTGACAACTGATGATGGCTAATCAACTGTTAGGGTCTTTCCATAATTATGACGAGGGCACAAAGGAAACGGGG
TAACAGGGGCCAAGTAAAACCTAGGAAAAAGACACACAACTGTGAGAACCAACAGCCAGCACACAATCCCATCAACAAGCACCATCACCATCATC
GTCATCATCATTGTTGTCGACATTTGTGGTTGTCGCTCGTCAACAAAAAAGCCACAGAGCCAGATATATCAACCGTGTATCTGTATCTTGTCCCA
AAAGATATGGCAACGTCAGCACACTCGCACAATACAGAAAACTTTAGACTAGTAAGGCAGCCATCCATATCCATGAATCGGAACAATGTGCTTGC
AGCTCACAAAAATATGAATAAAAAAATAGAATAAAAAACAAAACAGAACACAAAAGTAGCAACTTTGTGGGCGGGTGGAAAGCAGGGGGGTCTGC
GGGCACTGGGAGGTGGGGTCTTTGGTCTTTCGTACGCCCTTCGTGCCACAGAGGGCACCTACCGAGAGAAGCCGAGAAGAGCCGAGAGAAGCGCA
CAGAAAGCGATGTGCACTCGACGGTGTACTTGAAGCTAGTTTTAGCTTGGCGCCCCCCTTTTCTGCCCCATCGCTTCAGACCCCTCTTTATCTAC
CATAAAACTACGAAAATTACGCTTTTGTGCCCTGCACACCAGTGGAAACTGAATTTTCATCATTATGGCGATGCCCGGACGATGATTGCGAGTTG
ATGGCAGGCAGCCGAGAGTTCAGGGCAAAGTTCAGGGCATAGTGGATCAGCAGGTTGTTCGGATAGCTCCTAGGAAACCAAGGAAAACTTCAAGT

FIGURE SHEET 213

TACTCTTGGGACTATTGTTGAAGTACTTGTGTGTAACAATTAGTGTACCTAAGATTTTGAAATGTAAGTCAATATTCGAAAACCCCTTTTAAAAA
GTTCCATAAAAGCGTATAACTCAATACAATATTCACTACATATATATTTCTATATATTTTTGACATTATATTAATTACCAACATAAATAATAAAA
AGAAATGCCTTTAATCGGATCAACAAGATCTGCATTACAAAGTGACTACTTGGGGTACAACTGTTCAACTGTAGAAAGTACAGTAAAACCATCTA
ATTATCATCAGTATGATAAATAATTGTGCGCAAAGCAATTTCTTTTAGCTGAATGCTTTTTCTTCATTTTCATTAAAGATTCCCGCATTTGCATA
ATTAGAAACAAAATTGCGTGTAAATGATGATTTCTTCTGGAATAGGCCATCTTTATTCCCCTCAATTCAGTCAGTCGGCAAGTTGAAGTTTGTTG
AATTGTGACTGAATTTGGCACTGCATTATTCATTATTTAACTAAGTATTCTTCAAATTTAAGCACTTTTAATCCACAGCCACCCCATCTAAACCG
CCCATCGCATAGCGCAACCAAAAGTCGCATCGCTTCGCCCATTTTTTGTCTCCGTTGCCTTTCGATTATTTTCGTTTGCCGCTCACGCGAAAATG
GCACGCAAAGAGGAGGGTGGCATAGTTGGGTAAAGGGGAGGCAGAAGAACGGAGGCTGTGCTAGCAAAACAAAAAGCGAACAAGACAAAAACAAA
AGACCGAGCGGCTTGAACTAAAGTTGGGCAGAAAAGTGGGTGGTTGGCGTTCGTGTGCCTACGCCCACTCAGCTGGAAAATGACAATCCCACGTT
TGATGACGCTCTTAAATTGATGACGTCGCTGGCGAGCGCTTTTCTTGATTTTCCTTAGCCCGCTTTCTGTTTATACGCCGCAATTTCGTAAAAGG
CGCGCACTTGCACACCAACCCACACACACACACATGGTCACAGCTTGAAAGTGTCGGCAATCCAATAACAACAATAACAGTTCGACCGGCACGGG
CGCCCGCAGGGTGGTTGAACACACACACACTCGCCACTTCTCTCCCACTCTCTATCGCTCACACACACACACACGCAACAAGCTGGCTGTCCGAA
AAATGAACTCACAAAAAAGACGAAAACATGGACGAAAATCTACGTAAAATCGCAACAACTCTGGAGGTACGATTTTTCCGCGGCCGCGTCCAGAG
TTCAACTGAAATCCAATTCGAGAAATCCCAACTGCCACTTGCGCGCTCAATTCGCCGTTAGGCGAGAGCGCACGACACACACAAAATTGTATCTA
TTCGCCGCGGCGAGAGAGACGACAAACAAACTTTCTACTTTTGCGCGGGCGCATTTTCGCCGACTGTCGACGTTTTCGCCGCACGACGAAAATTC
CAATACGCGGCGAGAATAACACGCACGCACACCAGGGCATTTGTGTTTACAAAATTTTCACCCATACATGTGAGAGGGAAAATTTCATGTTCCCT
TTCCTTTTTGGTTTTTATTTCCCGCATACGTACTCAAAGCAATTGCGTTGTTACTTGAAGAGTTTTCCTCTGTAGCATATTCCCTTTGGATTTTC
CATTAAAACAAATCCATTCGCCGACACCGAACACACACGCTTTCGATTACTCCACTGCCTTTTCGTCTTCTTCTTCTGTCACTTCAGCTGCTGTT
ATCGATTTCTCGTACACGCACAGATTTTCGCTGCTTCTCTGTCACTCACTCTCGCGCTCTCTCCCTCTCGCACTCGTTTGAGCTCGCGCCACGAC
AAAAATATATTCTCCGTTCCGTTTCACAAAGTGCACGGCACGAAAAGTTTCCACAGACTGATTCAAATTAGACCTGCTGGCGCTGTCGCTGCCCA
AAATCGCTCGGCTCGCATGAGAGAGCCGCACGAGTGAAACACGAGAGAACCACCACTAACCTATCACATCGCTGCACGAGCGAGATGACAAGAGG
GGGGCGCTCGGCATCAGCAGGCTGTCTGCGTCGCACTCTCACGAATTGAGGTTACTCTGTAACTGTGTGGGTGGCGTCGTTTCTAATTGAATCCA
ACTGTCAAATGAGAGAGATTAACGCACATATTCGTATGTATGTGCGTGCAGTGTGCCCGTGTATTGGCCTTGGCGTTTATAATTAACACAAAAAT
GCCCGTTTTCGCAGATTTTTTCTCCTTTTTTTGTTGGTCTGCCGTTGGCATTTCATT
(SEQ ID NO: 394)

Exon: 11692..11603
Exon: 9538..9317
Exon: 9016..8764
Exon: 8671..8431
Exon: 7888..4432
Exon: 3050..1001
Start ATG: 9479 (Reverse strand: CAT)

Transcript No. : CT12997
AGTTGAACTCTGGACGCGGCCGCGGAAAAATCGTACCTCCAGAGTTGTTGCGATTTTACGTAGATTTTCGTCCATGTTTTCGTCTTTTTTGACCC
CATTGAAAGAGGCTGCTAGGAGTAAGTATTGAGGCAGATAGAATAGGCAGAAAGATGCACCTGCAAAACACGCACAACACAATGGAATCAAACGC
CGCTATGGATGCCGCATCCCCAGCTTCTCGGGATGTCCGGCAGTTTCATGATCTGATAACGTGCCGACTTTGTCGCGGTTATATGATCGATCCAA
CCACTGTGGATTACTGTTATCATACCTATTGCCGGAGTTGCATACTAAAGCACCTGCTGCGAGCGGTATATTGTCCGGAATGTAAAGCCAGCGGA
GGCAAGGAAATCAATGAATTGAATCTGAAATCGGATGATACGTTGCGATCGCTAATCTATAAGCTAGTGCCGGGACTCTATCAAAGGGAGTGCAA
GGAGCTGGCAGATTTCAAGGAGCAGCACGATTTGGTGGATGAACAAACGACTGATGAACCGGAGTTCTTCACAACCACGGAACTTATAAGCTTAT
CCCTGGAATACCATCCCGCCATGCTGCATCAGTGTGGTCCTGGTGAGGTGCCTCCCACTATTTACCTGCAATGTGCCGCCGGATTACCTGTGGAG
TTACTGAAAAGGTTCCTCTGCTCCAAGTACAACATAGAGACGGACAACGGTCTGGTGGAAGTGGAGGTGACCTACAAGGATGAGGTACTGCCTAC
CAATTTCACCCTGATGGACGTTGCCTACTGTTACAACTGGAGCCGGGAATCGCCCATGGCCTTCTGCTACCGGATTCTGCTTTACGACAACGAGC
AAACAAAAAACGATGAGAACAACCTATCCAGGATTAACCAGGACATTGAACCAGAGCATTCGGTACGTCGCTCCAAGTCGGCCAAATCGGTGACC
TTTGCCGAGGACCTGGAATCGGAAATAGACTCCGGTTCTCCGCGTTCCAAAGTACGGTGTAAGACTCCGCCAAAAGTTTCTCCCTCGTCGAAAAA
CAAACGATTGACGTCGAGTAAACGGGAAGCGGAACCTGAAAGTCCGGTGAGCAACTTCAAAAGTCTGCGAAGCAATGACATGCGGTACAGTGATT
ACGCCGTGTCCAAAGTTAAAAGTGAACCGGAACAAGAACAGTTCCTTCTGCCAAGAGAACGGGAACAACAGCCGCTGGAGGCCAATACTAATATA
GTGGTCAGCATTCCACCCTCGCAACTCCGAAAGTCCTACGTTGATGCCGAGGATTTTGAGCTGAAGACAGCGAATCGAAAGGGAGTTGGCCATTT
GCCCAAACTGAAGATCGAACTGAACAGCATGAAGAGCAAGCTGAGTATGCCATTATCGGCTGGTCCGCGACTGGAGGATACCTCCTGCTCCTTAT
CTTGCTCAGCCCAACAACTCGATCTGGAGACCTACGCCAAGAATATTGGCTTGAAGCCCATTGAGCAGCCTTTGCAGCAAAGTGCATCCAATCCC
GATAGCAAATACAGTCCCAATGCCTCGCCCATGTCTTCGTGCTCCAGTTCGACCAATGGATCCAGCAGCAGTCTGGGCACAGCCGATGCCAGTAC
ATCGACCAGCACGTCCAGTTCCCATCGCAAGCGCAAGAAGAAGCACTCCAAGGAGCCAAAGGATGCGAATGGCAAGCGGAAGAAGTTGCACGCGG
AGATCAGTTCGCAAACCGATGGGAAAATGAAGGTTAAGATAACGGCAAAACCCAATCATAAGTTGGATTTCAAGAGGTCGCATTCACTGGCCAGT
GGAGAGTTGGATCTGCAGAAGTTGAAACTGGACAGTACTAGCACTTCCGAGGCACTGAATCGCACATTGGGCGAGGAGGCGCGGAGTATCAACAG
CCTGGTGGTGGGTGGAGCACCCACACCGCCGCCCACGCCCACCGCCGAACCAGAACAGCAGCAGCAGCAGCAGCAGCAACAACAACAACCACAAC
AACAGCAGCAACAACAGCAGCAGCAGCAGCAACAGCAACAGTTTGTGGTGCTGCCAAAAATAAAGGACCTAACCTTGCCCACATCGCCACCTCTG
CCGCCCAGTTTATTCAAAGCCTATACACCCAGCACGACGCCAACTGCTCCACATACGGTGGCCGGCGGAAAACCCAAGCAGCAGCAACAGCAAAT
GCCACAGCAACCTCAAGCTGTACTACAGCAAAGTCTGGCTAAAACGAATCCCGCCAAACCGCCGCTGAGTAGCAACAATAATCGTAAGCCCAACA
GTGGACACTTTGCGGTGCCACAGGCTCCAACCCACCGGAATATGTATCACATGCAACGCTACCAGTCCACACCCAGTTCGATTGCCAGTGCGGCT
AACAAGATGCCAAAGCGATCCATGTCCCTGGACGAATCGCATCCGGCCAAGCAGGCGAGATTGAGCCAGGCTCAGGCGATGGCCAGCAGTTATGC
GGCCAAGTTGCATATGCAGACTAGCAACCAGGCCAAAAGTCAAGCGGCCGCCTTTCTGCCCAATCCCCAGATGCGATCCTATGGTCTACCCGACC
TGGGCAGCAAGCCAACGTTGCCAATGTTGTGCCCGGCCAGCAGTTCGAGCCAAGTGACGATTACGCCAAGGCCCAGAGCTACGCCGTCGATTTAT
TCCTTCTCGGAGCCAAATATCCATGTGCCTGCACTGGAAATAGTGCGATTGCCGGTGAATAAGCAGAGTGCAGGAGGCAAGGGTCTAACGATGCC
ACCTCTTAGCCCGCCGGCAACGTCCAGTGCCCGCTTGATGGGACCACCAGCGGCTCTGCCCAAACATGCAGGACATGGACATGGTGCGGCCAAGC
GGAGCTGCCAAATGCCGACAATGCCAATGCCGTTGCCGCTGCCGCTGCCCATGCCGATGACCACGATTCCGGCGATTGTCAAGTCGCCGCCACTG
TCAGTTGCGCTCAGTGGCCAGAGGAACAACAAGGGCAACTCCTCGAACTCAAATGCTTATCGCACATCACCGCCTGCATTAATAAATCTGCGCAA
CACAGCCGCTCCACAGCACTCGTTTCCATCAAAGTCGAGCCCAAAGGTGGAAGCCAATTCAAAGAAATCCCCGCCAGCAGCTGGCTGCCAAGGCA
AAACCAATGGCACTGCCGCATTGGACAAGTCCAAAACGAGTTTGCGCGAGTTTCGGCCAGCAGTGCAGTCGGCTGTAACAGCAACAGCAACCACA
TCGGTAACCACAGCAGCGGGAGCAGGAGCAGGAGCAGGAACAGGAACAGGAACAGCATTAGCCAAGGATGCCGATATACTTGATTTATCAGCTAA
CCCGGGTAGGAGCAACAATGACGCCAAATTGGCGCCCAACTCACCGCCCGCTGGCAACAACAACAACAACAACAACAACAACAACAATAACAACA ATAATAATAATAATAACAATAACAACAGCACCAGCAACAGCCTGGAGGCAGCCTTAAACAAAATCAAACAGAATATATCGGCAAACAGCAATGGT
GGACCATCGACCACTTCTGGCAGTAACTCGAATGGTACAACCAACGGCGATGATCTACAGAATCTGCATATGCTCTCGGAATCGGCAACGGCCAG
GGAGAAGATCTCCATAAAGGCCGCCAGCAGTGGAAACGGCAGTGGTAGCACCAGTAGTAGTTCCGCCAAACCCAAGAATGCCAATGCTTTGGTAA
GACCACAGAATGCCTCAGTTCGGAGCATACCCAATCCATCGGCTTTGGCATTCCGCAATCAGCCAGCAGCTGCCAGCACAGCAGCCAGCATTAGC
AAACCGTTGACAGTTCGTGCTGAGGAAAAGCCGAAGGTTTCCACCAGCAATCCGGGATCATTGAGCCCCACCAACACAAGCAGCAGCAGCAGCAG
CAGCTCAAGCGGCAGCTCTGGATGCAGTGCAGCCACCTCGCCGCGGGCAATGACCAAGAAACCCACGACCATCGATCAAGTGGCGGCCAATTTGA
ATATTCGCGCCGAGGCCAAGGCCGCCGCTCTCGCCGAGGAGGCACCACCCGTTCTCAGTTCCAATGCGGCCAAATCCCCGGAGTTGGCCAAAACG
ACCACAGCGGTTGCGTTGAGGCCAGAGCCCAAGGAGACGCCCATTACCGTTTCGGCGGCCAGTACTCTGCTGACCATCCCATCCGCGGTTTCCAG
TGTGTCCGCAGTCCCGGAAACCATGGCCAAGCCACCCGTACAGATTGCCAATGCTCCGGTGGCGAGTTCCGCTTAGTCACAAGCGTTTCTTTGGC
TGTGCGGAACGCAAATGTATCTTGTGGCGCCGCTGGAGAATCTGCGAAATACCGACAGCAACTGAGGTGATGATCAACCGTATAAACAACTCCTA
TAGCGCAAGTTTTCCAAACCTCGCTCCCGAAGATGAAGTGCAATTTAATCAACCATTAGAATGGATCGTAAGCCTTAGAACTAACCCGAACAACA
CTGAGCAATATCTACAACACAGCGGAATGTATCTGTTGGATGCGAAAACCGCATCATTTGCATACATATATGCAAACATTTGCAATCGAATTAGT
ACGCGACTAAATAAATAATCCAAGCAAATTTCAAAAATGCCAGCAACAATATTCATTAATAAATAACCCAACTGTGAGAGAAAGAGAGAAGAAGC
GAGGAGGAGAATAATAATACTAATCAAAAGCGCTGGCGTTCGCTGGCATTTTCGAAAGCAGGCAAAAAAGCAACAACAAAATTAATTATAAAATA
TCAACAGCAAAATATGTGTTAAACCGCGATAAGGTCAGACGAACACAAACACATGCCTTTAGTAGATAGATCTTCTTCGGTTGGCCTTTTGCTTT
TTGGGGAAAGTCCAAGCGTAAACAAGAGAAAAAGATCTCTACTAATAAATAGCAAAATTAATTTCAAATGCGCGATAGTAAAAACCAATTTGTTT
CGAAAAAACAAACGCAGAAGAGGAAAAACCACAAACCGATACGAAAACGGAAATCGCATCAGGAATATTTGATTACAACAACACACACTCAGTGC
CGAAAGTGTTTGGCCCACACCCTGAGGAAAAACTGCCACGAAGTGTGAAAATTCGGTGGTAGCGTTGGTGGTGGTTGGGCTAGCTGCTAGATTTT
TCGAAAGGAACACACTCGCGTATAGCGAAAGATACAGCCCGATACCCGATACCCGATACACACTCACGTTCCTCATCGGGGCGATAAAATTTTAA
CGATTTTGCGCCGCTTTGAGCGAGCGTGTCAGGCATAAAGATACAAAACAATACTTGGGCATATATAAACAAAAGCAAACAAAGCGGAATGAAAA
TAATGAAAATAACAAGCTCGCACTGGCACAATGCGTATATTTCTATACATATACCCAAATAAATATAAACACATATTTATATATACGAATATATA
TATATATATATCTTGTAGATACCTTGTCGCATTAGTTGTTTAAGCGAGTTACGTTTAATTGCAGCACGAATTTTGTACATAAATTTAAAAATCGA
AGCCAGGCGAAAACAAAATGCCAACCCAGCACACAGCACCCAGCAACTTGGAAATGAATTTTAATTTTTTAGAGCTTCGACCAAATGAAATACTA
TACACATAAACACGAACACACACGCATTATGCAAATATTGATAAACTTCTTCTTATATTTACGATATTCGTACACTCGAAAAAGGCTTTAGATTT
TCGTACATTTATTCTCAACTTGCTCTTAGCTGATATTTTTTGTTTTGTTATCTTGTATATGGTCTGTACATATTTTAAGCAAAGAAAAAACTTTA
AAGTTTATGAGGGGAGCAAAAAGAAAAACCCTAAGTTATATGAGTTTCTTAGAGGAATAGCTGGAATTTAGAATTGGTACATGGTGGCAGATCCA
CCCCATTGTTTATTCGTATCTGTATCTTATTTTTGCAACCCCTGTCTGCTGGCAGCATCCCCCTCATGATCGGCGAAAAATTAACATAATTTCCA
GGCAATCAAACAAATTGAAGGCCTCGGATCGACCTCCAGCTATTCCAATAATAACTTTGGCTCCGACTCCTGATTGTTGTATATTTATTTATTCC
TATTATTGAAATATATACATTATCTATATACATATATCTAGTTGTATATGCGAGAAAAGGCTCGACTTATTTAAGCTGATATTGTACTGTTCGGA
TACCTTAACTAATTAAACCTATAAATACTTAAATATAACGCATATATATATATGTTTAGAAATCTGATTGTATGCACATCTGTATGTAATACTGT
TAGAAAACCCTCGAAATGTAATCCAAAAAACAAAAAAAAAAAA
(SEQ ID NO: 395)

Start ATG: 150 (Reverse strand: CAT)

MHLQNTHNTMESNAAMDAASPASRDVRQFHDLITCRLCRGYMIDPTTVDYCYHTYCRSCILKHLLRAVYCPECKASGGKEINELNLKSDDTLRSL
IYKLVPGLYQRECKELADFKEQHDLVDEQTTDEPEFFTTTELISLSLEYHPAMLHQCGPGEVPPTIYLQCAAGLPVELLKRFLCSKYNIETDNGL
VEVEVTYKDEVLPTNFTLMDVAYCYNWSRESPMAFCYRILLYDNEQTKNDENNLSRINQDIEPEHSVRRSKSAKSVTFAEDLESEIDSGSPRSKV
RCKTPPKVSPSSKNKRLTSSKREAEPESPVSNFKSLRSNDMRYSDYAVSKVKSEPEQEQFLLPREREQQPLEANTNIVVSIPPSQLRKSYVDAED
FELKTANRKGVGHLPKLKIELNSMKSKLSMPLSAGPRLEDTSCSLSCSAQQLDLETYAKNIGLKPIEQPLQQSASNPDSKYSPNASPMSSCSSST
NGSSSSLGTADASTSTSTSSSHRKRKKKHSKEPKDANGKRKKLHAEISSQTDGKMKVKITAKPNHKLDFKRSHSLASGELDLQKLKLDSTSTSEA
LNRTLGEEARSINSLVVGGAPTPPPTPTAEPEQQQQQQQQQQQPQQQQQQQQQQQQQQFVVLPKIKDLTLPTSPPLPPSLFKAYTPSTTPTAPH
TVAGGKPKQQQQQMPQQPQAVLQQSLAKTNPAKPPLSSNNNRKPNSGHFAVPQAPTHRNMYHMQRYQSTPSSIASAANKMPKRSMSLDESHPAKQ
ARLSQAQAMASSYAAKLHMQTSNQAKSQAAAFLPNPQMRSYGLPDLGSKPTLPMLCPASSSSQVTITPRPRATPSIYSFSEPNIHVPALEIVRLP
VNKQSAGGKGLTMPPLSPPATSSARLMGPPAALPKHAGHGHGAAKRSCQMPTMPMPLPLPLPMPMTTIPAIVKSPPLSVALSGQRNNKGNSSNSN
AYRTSPPALINLRNTAAPQHSFPSKSSPKVEANSKKSPPAAGCQGKTNGTAALDKSKTSLREFRPAVQSAVTATATTSVTTAAGAGAGAGTGTGT
ALAKDADILDLSANPGRSNNDAKLAPNSPPAGNNNNNNNNNNNNNNNNNNNNNNNSTSNSLEAALNKIKQNISANSNGGPSTTSGSNSNGTTNGDD
LQNLHMLSESATAREKISIKAASSGNGSGSTSSSSAKPKNANALVRPQNASVRSIPNPSALAFRNQPAAASTAASISKPLTVRAEEKPKVSTSNP
GSLSPTNTSSSSSSSSSGSSGCSAATSPRAMTKKPTTIDQVAANLNIRAEAKAAALAEEAPPVLSSNAAKSPELAKTTTAVALRPEPKETPITVS
AASTLLTIPSAVSSVSAVPETMAKPPVQIANAPVASSA*
(SEQ ID NO: 396)

Name: SUPPRESSOR 2 OF ZESTE PROTEIN
Classification: transcription_factor
Gene Symbol: Su(z)2
FlyBase ID: FBgn0008654

Celera Sequence No. : 142000013384592
CTTGACCAAAAACAAAGTGGCCAAGGTGGCTTGCTTCGCTGAGTGGGTGGATGGTGCAGCAGGGCGCAGATTTGCCGACACTTTTTACTACGCGA
CTTTCGAACTGGAGAAAGCGGCGCGACTCGACGCGAGAAAACGAGAAGCGCGAACGGAGAGACGAGACGAGAGATTTATTTGGCTGCGCGGCTTC
GTCTCTTCGGCTTTTTGGCGCTCACAATTATTGCACCACCACAGGCACTCGCTCACGTACATACATTATACATATACACAGATATCTGTATTGGA
TTTTTTTTCCAAAGTTTGGATTTTGATGATATCCTGCGGGGTATACAGCGATTTTCGAACTGGCTTTGAAACTTGAAACTAAACTTTATGGCCAG
CCAAAAGCACTTTAAGCCTTTTAAGTGTGAAAATTAATATTGCACTTTGAGTTGGTACTGGTTTTCCCTTATGTGTTTTATCGGTTTAGCGGATT
GCATTGGGCAGAATAGAATTTTCGTTTGGACGCGATTTCTGCTCGGAACGCATCCACACTCGCCAGATTCTCGCCACGAACTGAGTGCGCTCTGT
GGGGCCAGATAGCTGCTCTTGGGGCACGATTCCTTGATACCTCGCCATTCGAACTTGCTTCCTCTCAATTCGAATTTGGCCAAAACCGTTGGGGT
TGCTTTGAGCCAGTGATGCCAGATGGGTTCGTTACCCTCTGTTAACCGCTTCCACAACAACGCTAGCGGTTCAGAATGTTGGCAGTTTGCAGAGC
TATCGATATAAAGGTCAAAGTGCAACCGTTCTGAATTGCCGCCCTGTTTTCAAATATAAAGCGGTTTATTTGAATCCTAATGCATTCAACAAGGT
AGTGTCTAAAATGTCCTACAAATAGTATGTTTTCTGGTTATCTTCAGTCGCATATTTTTGTATACTTGTTTCAAGACATGCAATATTTTATGACC
ACATTTACCACGTTGCGCACCTAATGATGAATCCCATTGAAAATGAAACATTTGAATTGATTTCAGTTTTATTTACAAAAGTATATATAGTAGCA
TATGTGCCATAGTATAAGACCACATATACTTACACACACACACACATACATAACCACATAGGAACAGCCATACACAAAATCATAGAATGCCCTTA GGATATAAGTCATAAAATCATGTATCCAATAAGAACCCAAATTCTGGTGACAATAACAAATCCAGCCTACCCTAATGTAAACATTAACATCCGCT
GCCGAATCAGTTATTCCCACCAAAGGGTCAAAACCGCTTACGCAGCCCAAGTTCTCGGCTGATCAGTACCCATGAGTGATCCACTCAAGAAGGCA
CCCAATCCAACAGACATAAACATCCGCAGCCGCATTCGCGACTCCCACCAGAGGGTCGAAACTGCTAACACAGCTTTAAGGGTCAAAACTTTCCA
CGTAGCTCAAACTCGGCTGATCTATATCCATGCGCAATCCACTCAAGAGAGCGCCTAATTAACGTAAACATAAATGAGAGCCTATGTACGCTCAA
TATGAAGAAGTAAATAAGCTCAGCCAAGGGTTTGCTAAGCGTTCGCTTTGCAAATTAGATTTAGATTTTATTCATACTTCAATTGTGTAAGACGT
GAATTTGTCTCCGACATTCGCTTAAGTTTTTGATCAATAAAAATACTTTTTTTTATAAACCAACAAACCGCGAAGTTGTAATTATATTTATTTAC
TCATTCAATTCAACTTGATTTGTTTAGTTTACGATTTTGCGATCGTTTATTTATTAACATCAAATCATGGATATAAGCGTAGTTCTGAAATTATT
TAAAATTAAATTCATAATTTTAAAATGATTATTGCTTTTAAAACTACAAATAAAACATAAATAGATTAGTTTTTTTTTTGTTTGCTTTTCTTTT
AGTTGTTTTTTGTTTGTTTTTGTTTTCAATCCAGCCTTAATCGTATGAACACTTACATGTTATTTATGCCTAAGCTAACGAATAATAATATTTTT
CTACCTTGCGTGGTTGCCTTTTGAATGTACATAAAATATTTTAAGCCATATAAAGAATTGTACACTTATATAATAATATATTATATGCGTTTCAG
TTACGGTTAATTCTTGTTTTTGTGCGTTTTGTATTGTTTTGTTTTATGTACAGAATTTATTTGCTTAGCAAATTATGGCAAATTAGTCTAATTAA
AAAAATTTTACAATGATGTATATATGAATACATATAGTCTGTTCTGGGGTTTCAATTCATGAATATTTAATTCTTTACTTCTTCAATTGCCATTT
TCTTTTTGTCACTCCATGTCAGCTGTGGACTTGTCTTGTTTGTTGATTCATTGTTAGTAGGATTAATGGTCGAATGAAATGCATTAGTAGAGTTA
GATAGATTCCCTCGACTTATATGCTAATTTTAGTTGATTAGTCAAGTACTGTGCTCTGGGCCGCTACTGCCCCCTCTTCTGTTTGTCAGTTTTAG
TTTTGTTAGTTGCTGCTTGGTGATTGGTGATATCAAATGATTGACTGACTGGTTGAAAGCTAAACATGTATGATTGCGAACATATTTTGTTGTTT
CATTTTTGAGGCACCCAACTTGGTTTGTGAGAGCGTCACACCACTGAATTCTGGATAGTGTTGTGCTCCTTTTCAGCAGGTATTAGTCTAATGGT
TAATTCAGTTTTGTCTGGTCTGCTATACTATAAGTGTATGTGTATATATATATATATAAGCTTGAGCGCTTTATAGATAGTGTACATTTAAAATT
ATATTTCTGTTTTTTCTATAAATACACAAAGTTAAATATTAAGCTGAGCGAGGAAAATGATTATATCGCGAGTTGAGAATCAAGAGCGCGTAGAT
AATTTCAAATTAAATATGTTTGTAGCATAGGAATTAGGCAACTAATAACTTTTCACTTAACAAAAATAATTTAAATATAAGAAACACTTAACGTA
GACTGTTTGGGCGGGTGTGGTGAGTGTGAGAGGATGATGGCCAAGAGCAGTGAGGCGAATCTCTCAGGGATTGCTTCTACTGCTGCAGCTGGTCA
CCGAATTGTTGCTGCTGCTCTTGCCGCCCTTGTTACTGGCGGCAGTGTTGCAGCATGTGGTTGTGGAGGAGATGCCGCTCCTGGCCCCCGTCTCA
TCGCCCTCATCGCCCAGGTACTCGTCCGGCTTGTGACTAGAGGCGGGAGGCGTCAGAAGACTTTCGGGAGCGCGCAGCGCGGTGGCCGGGGAAGC
TTGAATCCTAGCGCGCATGGCATGCGCCGCATCCTGGGCCATAAGCACTTCGTCCTGAAAGATAGAAGTTTCAATAAGTAACTGACGGAATAAAG
TACGCTTTATATTCAGAGTGAATCGAATACATATTTGGACGTATGCACACTTCTGTATACACTTAGATATACTTACATACATATCCATGGTAGTT
GTGTGCGTTTGGATAATGTGCGAGTCGTCGGTGACAATATTGGGGCAGATTAGTCCCAGGCCAAATTTGTTGCTGACTTGCTCATTCTGCTCGTT
CAGCTGCAGGTAGGGGGCCTTCTGGGAGATCACTCGGAAGAATGGCTCCATCCAGCGAGCACAAGGCTGAATCACCTGCCAATCCAGACCAGAAC
AGCGTAAAGCCATCTCCCTAAAAACGAAAAATATTCGGTAAGATAACCATGTCGTATGGGATGCAACTTCCATTCCAACTTACCGACTAAATGTA
TGACTGATGGCGGCCGCTGCCAGCACCGAGTAGGAATAGTTGGCCATGCCCACGTCCAGGGTGCACAGATCTAGCAGCTGTGAGGTTTGCACAAA
CTCAAAGCCAGAGAATTGCGGGTAGATAAAGGCATCGTCCGCCTCCGCGCTCTTTTGCCTGCCAATCTGGGAGAACGAGGCCGGAGTGCGGTTGT
TCACATTCAGTTGCATATAGACGCCCAGCCAGCCGGTAATGGTGATGGGGCTGATGTCCCAGTCGAGCGCCTGCAGCAGAATCTTCTCGTGGTTA
AGGATGTCCCGCTCTGTGCAGGCGCCATCCGTCACATAAGCAAACTCCCCGATCTTTGGCGGATAAATCTCCTCTACCTTGGCGGCCACAAACAG
GCAGGTGATGCCGATCAACTGCAAGTGCGTCTTCTGCACCTTATGCGCCACATGCAAATAGCGATCCAGGTAGTCGACGGCCAAGTAGAAGGTCT
CCCGATGCAGCTTGTAAACTTCACAGACCTCGATCAACCAGTCCAAGAGAATGGCACGCATACGTGGTTGCAGTCCGGGATGCTGTTCCAGCATC
GAAATGCTGCGCAGACGCGAGTCCTGCTCATCCCGGTGACACATCAGGCGCCAAACATCGGCGGCGTTAGCCCAGGCGAGCGCAGGAAGTGGGCA
CTGGCGCAGACCGTTCTCCACAGCCGGCGACATGGGCGTCCGCATGTTAATCATCAGGTCACTGACCGGATGATGGATCTGCTCCTGATGTTTTG
GCAGGCCGGGAGTACGCTCTCCATTCACCGCCTGCTGCTGGCTGCAGCCGGAGGAGGCTGGAGAAATTGTGGAGGAGTAGATCTCCACGTCGTCG
TCCTCCTCCTCAACGTCATCCTCATCATCCTCGTCGTACGAGTAGTCCTCGCAGCTGTCGTCCAAAAGGTCATCATCCTCCGTCTTCTGCGTGAC
CACCGTACTGGTCACCACCTGCTCCGCAGCGTAGCGCACCACCACTGGCGTCTGCTTGCTTCCACGATCCGGACTCGGCGGACTGTCCGGGCTGT
CCGGCAGCGGACTGTGTGGCGCCTCCGACAGATCCTCGGCCGGTGAGCTACGTATGCTGAGCAGCTCCTGGGTACTCTGGCCATCAACCGAGACA
ACGGGCGAGGTGTAGACCGAGGAGGCAACCGATGACAGATTGCCCTGCTCGCTGCCGTACAAAGCGGGCAGTCGCTGCTGGCGCTTAGCTGATGG
AGGCTCAAAACCGAGTTCAGGGTCCTGAAAATGAAGGACAGATGTTTGAATAAGTAAATCATACAAGTGAATGCTTTAAATTGAAATGAACTAAG
ATAGTAGACAATCAAATATAATTACTAAGCTATATTCAGATATTACTTTCTTAAATAGTAGTTCATATTTCTCAAAGGTGTCAGCAATTATTACC
ATTTCAATAAATTTGCGCTTCTGTTCCAACTTCATAATAACATGAACAAATGAGTGGAGAGGATACTCAAGACAATAACAGGATCACACGACTGG
CGGAATTAGAAACGTGCTCCGAATTTAATTAGCGAAGGAGGTTTGGGGAAATTTATGTGGGCACGCCTGTCAAAATTGGTAATCCTTGATAGATG
GACTGCTGGCTGGACCGAATGCACCCGCACAAAATGAGGAGCCAGGACTTCACACAAAAGATCAAGGACTATGGAATGGCATGGAGGTAAGACAA
TAGCACTTGGTTGGATTTTCTCGTGGGAACGAACGGGTTTCGTTTTGCTCTTTGTTTCTTTTGAATATTTTTGGTATGATCAACATATAGACACG
ATATCGTTATTGCACTTTTAACTTTAATGTTATAAATTTAGTAGCAGTCTTTGGAAATAATTTTGTTGCGTCGTTTCTCTTTGGTATGATTAAAT
AATTGTGCAAACAGATTTTTTGGTTATAGCATTTAAACAATTTTGGCTTCGTTTTGTTTTTTTGGTAGTTGTTGTTGTTGTTGGTGGGTGATCTT
GGCAAATCCGGTTCTTAAATTAGTTCTTTGCACTCGTTCTTGGTGGTTTATATAAATATATTTATCAGTCTTAACATTTGCTACTTGGCAACGAA
TAATTTTGGAATTTCGAATTTCGTTTCAGTTTGTCTGGGTATGTATTATTATTTGGCTAACTCCGCTCTTGGCTTGATCGAGTACCAATCGCGTT
GACGTGCGCTGTGCAACTGAGCTCGACGTTCTCCGTTCCAGATCGCCGATCCCCGAATTCCCCGATTACCGATCGTCGTTATCCTGCCCAACGAA
TGCAACGGTCTCGAAAATAGGGGTTGCTTTTCTCTGCAACAACAACAGCGGTAAAAACAGGATCGCCAAACTAACGTGCCGTCCCTTTCCAACGG
GGGTTGCTTGCCTAAGATATCCCCGTATATCTTGAGACGACAACTTGTGTTGTTTTTGTCTTTGCAGCAGCATTGCATTTTTCGCCTCTGGGTGT
TTATCGGCCCAACAACAAATCCCACTGACGGCTGTGGCTCCTGGATCCTTTTTACAATTATTTTTGTCAACATTTTCGTTCAGGTAGACGCAAGA
CGTTTGGAAAATCACTACCTACATCATAATCCTCAAAATAGCGACACATAATATAGTACATAGGAAGTATATAAATTACGATTTGCTAGCTTTTG
GCTCGAGCTGCCAGCGGCTGCATTAAGAATCTCCTGCATCTTAAAGGCTACTCAAATAATAAATTATCTTTTGACATTGATCAGAGGGATGGAGG
CGGTGCCAAAGCCAAAAGTAGAGCGATCCTAATGGAACCTCATAAGATTACAGCACAAAAATGACAAAAACAAAAAAACGAAAATGGAACCGAAA
ATCGAAAATCGAAAACAATTGAGATCCTTGACCATTGTTCTTCTTGCAGACAGATGATTGAAAACAGAAGCCAAAATCAGAAAGTCCATAAAGTA
CAATAAAATGTAGTCAGCATGGGACACAGATGTCTGAGATTGCTGATACCATAAAAAATACATAAATGAACGTATTTCGCTTAAAAAACTATTGG
GAATGTTTTGAAAGTTATCTCAAGAAACCCATAATTTCTTGGCTTTCTCTTTTTTTTTTAATGCATAGTAAAAGATATTTATTTATAAGATACTG
AAATATATCAAAAATAGCATTTAAAGCTATTCTGAAAGTTTTGGAAGCTTGGATTTCCATGTTTTAAATGTTTGGCACAATTATTTGCATTTATA
TATACTTTGAATGAAAAATATACATCAAAAATATTTGAAATTGCCCAATATCTGCACATAAAACTAAGCAATACAAAAGATATAAAATCCACATA
ATATTCGCATCAGTTTCTCTACAATTTCCTTTGGTTTACGATTGCAATTGATCTCTTCTTTGATTGAAAAAGGTGTGCAGTGCACACCATATAAT
TTATCAAATACTGACTGCATTTCGTCAACTTTCTTAACAGTCAATCTCACACATCGTAAAAGCTTAACAATATCAACCAACCCTGCTGGCCATTA
AAGATTTTCACATAATTTCTTGGGCGAAAAATGGGGGGAAATATTGCGATATTTATGTGACAATTTTAATTGTCTGAGTAGGTTTGCCTTCTCTC
GACAAACATACCGAGCAGAACTCCCCTCCTGAAGTCGAGAATAAATACTTTTTTTTTTTTTTTGTTCAGGCAAGACAGGAAGGTCCAAGACGCAT
GACAAATTTAATTTCTCATTCTTCTGGCCAACAAACTGCAACAACCCTCCGGAGGAGAAGATGATGTAGGTATAACCGGGAACGGCAATCGTAGA
ATGAAAATGAAAATGAAAATGGACATGGATATGGACATGGACACATGTCAAGGCACCCAGATGCAATGTAATTAAAATCAAAGCGTGCAATGGCC
TAAGAAGCCATCTCCCTGGACAATGGAAATTCCGTTCCTCTAGCCTTATTATTTCACTTCATTTTTGCTTTTGGTGCGTGGACATTGCATCTGCC
GTTTGGATTTGGTCAAGCGTTATGGAATCACAAAGATTATGCACGAAAATTCTCAGTTTACTTAACGACTTGACGGATTCGAAGAGAAAGATCGT
CGGAGTGAGTGTGAGAAATTAGTGAACTGTAAAGTGGGCTGGAATCTGGACCAATATGGACCCGAAGGGTTGCATTCCAAGTTTAACAAGGGTTA

FIGURE SHEET 216

AACTGGGTGGTTGCCCTTAAGCCACCGCCGTCGCCGCTGCCTTCAAGGATTTAAGTCTCAACTCCAAGCAGGCAGCTGCTGCAATCGTCCTTCGC
ATCTCGATCAGCTCCTTCAAAATCGAAGCCCACAAGGAAGGCACCCAAAACATCTCTCGAAATCTCACTGGGAGGGAGACCATGGGTCGCCGGCG
ACAGATGATGCAGTTCCTCAAGTTATGGGTACATACAGAAAGCAGACAAGAAGCAATTCGATTGTTAGGCGACAACCTCTGCTGCGTCGCCGACC
TCAATACTCGATGTCCTGGTGCCCCATTGTGTCGCTCTCCCTCTCCTTTTCGCCTACCCTATAAAGTCCTGCGCTTATGTGTCGTAATCTTTCGA
CGGCCGTCTGCTCGAAACCGAAACACCTTTAGTTTTCAGACCTTGGCGTGGGTCCAGGTGTAACTTTTTCACCGCTGTTTTCGTGTAATATGCTG
CATTGTTGTTTCCATTTATTTTTCTTTTCTTACAGTTTTTTTCTTTTTTTTTCAATTCTCCCCCAAGTCCTTTGATAACATTTAATTTCATACTA
CAATGTGCGGTAGTTGTTAATATTTTTACAGTTTGAAAAGATTATGATTTTCTTGAAATTCAGGATCAAGCTAGAGGTTTTTTCTTCAGATATTT
CATTTTTCATGAAGGACTCATAAAAGTCTGATGATCGTTCAAAATTAGCTAAAGTCCTGTCTACTTTTTGGGACATCGCTGCTGCTCTGCTTTTA
ATAAATGATATGCAAACAACATGCCAGTGGACAAATCCCCGAAGGACCATAACAAACACTCATATTTCAAACCAATTCAACTGACCCCTGGTCAG
TCCAGAAAGGGTTAATCCAACACAACACTTTCGCGGTGACATTGCTGGTTTTATCATCGCGGAAAATGGAAAATTCGGTGGGTCAGGGGGACGTT
GAAATTGCTTGGACATGTAATTAATCATGCAATTGGTTAGATCCATGACAAAACGAATTAAAGCATATCACATTGGTGAAACGGGAGGAGGGTAA
GTGGACAAAGGACAAACCGCGAATGAATTTTGAATGCGAAAAATGAATTTTGATTAATTGTCAGGAAAGACAATTTTCTTTAGGGGATATGCCAA
CTTCTTAGGTGTAAGCCTTTAATAATTGAATATCTCTTGATATATTTACTGCAATTACGTTTTCCCCTGTTTTATCTAATAATTTACCTTTTAAA
ATTATCTGCTCAAAAACTAGTTTCTTATCAGTCGAATCTTAATGTAATTAATCTGAAAACAGATCGCTGCCCAAGTTTACCATTATCTCTTGTTT
ACCTCCAGCTAAATAAAATCCTCTGTAAAATGAAAAAAGAAAACTTTGAATTACAAAGCAGGCGACGCATGATCCCAAATCGGGATGCAATCTGG
GAAAGTGAAACTTGAATTCAGTTTCCCACAATATCCCGATACTGACTTGACAGAAATCAAGACCCACACTTGATTGCATCGAAAGGAAACCCGAG
CGAAAGCAAACCCAACTCCCCTTTTCGGGACAAAAGAAACAAAGAAGTTTCCCAAAAAAAAAAAAATAACAAGGAACTTTCGGCGATTTCATGCCT
GCCATGTAAGGAGTAAGAAAAAGGGGTTTACATTACACTGACAAATTGGTAAAATAATACCATAATTTTGATCCTGTGCCAGCAGCAAAACAAAT
ATTGTATAATATTTCAAGACCGCATTCCGATGCAGACGCGTTCTCCGTGTCCCGAAAAGCAGATGACACAAGAGTTTTAAGAAGGAAAAGCCTGA
TGATTTGCATAAAAGTTTAACGGAAATCTAATGAGCAGACGTCGCAGGATCGGCCAAGGCATTTGCATAAGGATAACATGTCCCGAAACGGGGTA
GCAAAATGCAACCCAGTTGGAAAGAATTTTTTTTGTTATGCTCCGAATCTTCTGCAGAAGCAAATGTCGTCTCGATGAATATTTAATTAGAGACG
AAAAGAAAAGGGAAAAACTCGGCCCAGTGATCCTTGAAAAGGATAAGGCGTTGCTCAACCCCTCCGTCGGTTCGTTCGTGTGTTGCGGTTTCAGC
TCTGTCCCATTCCGGTAGTCACCACGATCCCTTACCCATCACCGTCCCCCCATCCCGATGCCAATCCCTTAAACTGTCTTGATCTAGTTCTTCTG
CCTCAAGCTAACCTATAACTATCGCAATTTCAAATTCTTACCACGGCCCTAACGGACATTTGCCGACGCCTTGACTTTTGGAAAAACCCACCCCT
GGAGAACTCGGACTTGGACTCAAGGTGTGCGCGCATGCGCAACGACGCCTTCTGTCCTTGTTCTGCGTCTCCTGCTCCTGCGCCTGCTTCTGGTC
CGGCTCCTTTGTCCTGGCATGCATATGCTCGGCATACTGCCAAAGACCCCTTCGGGGAATTCCCTTACTCAACAAAGTTCGCCTGAGAGGGGGCC
AGACATTTCCTTGCCATCCACTTTTTTCGTACCAGAATGACATTTGTTTGGCACGGAAGCAGGCGCAAAAACCATTGCAAAAACAAAAAACTCAA
AAAAAAAACAGCAAAAAAAATAACCAAGGCAGATATCATTTGTTTGGCAACAGACTGTTTGTATACCCTGGTCACTACATTTTAATTTTACGATA
TATTCTCAGTACAAACCAAGGCACCTTATAAATAATATAAATTTCTATATTTCCACTTTATCAATAAGATATGCTGAGTTCTAAAACAGTCCTTT
TAACATGCCTAAGATTTAATATATGAAAACTTATAGATATTCATAATCTTGCAAAGATAAAGATACCCATCTAGAGGGTACCAAACTATCAAACA
AGAAAACAATTTCTGCAAGTTCATTGCACGTATAGGAGAATATTCTCTCCCCTACATACATATTTCATATGGCACTGGAGAAAAAAATCCTTTGC
ACCAACACAGCTGCCCATCGTGAGGAGCCGCCAGGAGATGAGAAGGAAGCCATTGTTCTCCGCCTTGATTGCAGCTACTTGAGAGGAGATCTGAC
TTCAAGGCTTCCAAGGATGCTGCTAAATGAGCCCTTTTCAGTAAGTAGCGTTTATTTTTGGGCTCATCTTTGCATTGTGCCCGCGCAAAAGTGCC
AAGAAGTAGCTGTCTACGTGCTCAACGGCTTATTTGGCCAAAACTCAAGCAGCGAAAGATCAAATGAAGATCGGCAGCCAAACGAGTGGAAGCCA
CCAAAGGGCTGTCCATTCAAATGGAAGTACAAATAAAAGATCGTTTGCCAAACATAATAATAAAAATGGAGAATTGTTTAGCGATCGCTGATCAA
TGAAAACAATTGGGAAACTATAATCAAATAGATAAATATATAAAATGGCTATTGCTCAAATTCAAAAAGAAATATCACCTGCACGGTTCAAATAT
GTATGTACATTGTTTAGTTATAATCTCAAATTTACATTATTATTATTAACAGAGTTCACAAGCAATCAGATTATTCAGCTTGGAAATAAATCTTT
GAGCTTATAAACAGCCTAACCTTCAATTAATAGATTAAATTAATAGATTCTTATTTAGGCTAAAATGAAAGTGGCAATCACTGATCGACGAGAAT
TTAGAGAACAGAGAATTCCCAGAGTTCAAGAGTTCGTTAAATAGAAACATTTAATTAATTTCAAATGCATAGGCACTTTTTGAAACACACTAGAG
CTAATCATCGGCTTCCTAGAATGCCAGAATGCCTCTTGCCATTTCCCTGATAAGATTGCAAAAATCAACGAGGTCACATGACATGATAAAGCACT
TCATTCATAAAACTTATCTGCGCTGTGTCTGGCTTTATGTTTAAATTACGATTCGTTTTGGATTACGTACCTCGTTTGAATCGCTGCTTAAACGC
CGTTTACGTTTATTGCCATTGGAAGTCGCGGCTGTGGATGCTGCAAGATTCTGGCTATCACAAGAGCACATCTCGTCGGTTCTGGAGGCTGCTGA
GGTTCCTGGTAGCTCCTCTTCACTTCGTTGCGACGCTGAAGAGAACGATGTTGATGGGATTGGATCTGGATGTGGAAGGATAGCGATTGGGCTAT
CGCTGCTGCTACTGATACTACTGCTGCTGACGACGACGACTATGCTGCTGCTCACTTCTCCGTTGCTGGGGGCGGTTGTGACTATGCTGCCATTT
GGCTCAGTGCTGCTGGTAGAACAAACACTGCAAAAGAAAGTGAGTGGAATTAGCAGTGGGGTACTAAATAATAATACTAAATAATTTAAATTATA
TAGTTGAATGTCCCCAAAGAGCAGCTATTTGATAGAATACTTCAACATAGCTGCCTATATTTTTGTAGATTTAAAAGACATGATTGTATCAAAAA
CCCTTCCATTTAAAGAATCCCCCATATTTTTGTAAACCCAAACCCAAACTCTGGAGCGCAGTTATTTCCAATTTCTCCACTTTTTTTTTTTTTTT
GCAAAATAGAGAAATTCAATATGCCACGGAGGCAGGGCAGCAAATCACATAGGGGCGTTCTAAAATAGATACAAACGAAACGAACATAAATTCAT
TGAATTTTGACACGGCATTCGAATTTCGAATCGCGATGCAAGACTCGAGATTAAGGCGCCCAACGGATATATTAATATTTAACATCCGGGAAATT
GAAATCGAGATGACTGATCGGGGGGGGAAATGGAAATGGAAATGGGATCGTTGTGAGGGCCCCGGGGAAAGCCTTTCCTCCTCGAGATTGAGCAA
TTTTGGCAAATTTGCATGCACATTAGCATAATGCAGGAGGCTGGCAAACGGGAAGAATACAATTTTCCATACTTTCCAAAGGACAGATGTTATAT
CCTTGCGTCGCAACTCTCAAGTGTTGCGATCCAAGCAACTGCACTTTAAGCAATTCGATGCGCGAATTTTTGCAATTTGAGCGAGGAGCTCAGGA
GAACGAGAGAAAAAAAAACGAAATCTAACCCTTGGGACCAAAAACCCTTCTTAAGGAACTCGTGAAAAGGGATAATAGAAAAAAAAAAATAAAAAA
GGGCTGCTGCCCATACATAAATTCAAATGCTTTAGCCATTTCTTTCTTGGCCAGAGGCTCGGCATTGCAGCCTCCTGTTTTGATCCTTGCCCTGC
ACTATCGATCGGGTTTAATGGTTTAATGAACAAGAAAAAGTAATCACGTAGTAAATTACGAGGAAATGAAATCGCTTTAAAAATGAGTTATGGCG
AGAAAGGACTAATGGAGCGTACGTGCACGCGGCCTGCAACTTTTTCCCGCTTTCTTTCATTGTACTCAGGGTTTCGGGGTCAGGGGTTTCCAGTC
ATCTCCGCGGCTTAAGGTTCAAACTGAAATTTGTCATTTCGAGGTGAAAGTTTCCTTTCCTTTGCGGCAAATGCAGATACTTTGTTTCGGTTTCG
TTTCCCCTTTTCTATTCCGTTTCAAATCCGAATCCCTGTAGGTAGCAAAAGGCTAGGGTGACTATCTCGGAGATGATATGATGAAAAAATTCGAA
GAAGTATTTCCTGGAATCTGGTCCAGTGGATAATAAGTGGACTATCGAAGGATCGATCTTTCTCACATGATAAATTATAAAGCAACGGCGACTTT
TCGATTAGAAATTAGTTATTTATGCGTTTAACTTGGTATCAACGAAACAGTTATGTTTCGGAATTTATGTGTTTGATCCTAAACTCTTAAGGTTA
CAAGAATTTTGTCATTTTTTGAACATTTTTATGTGAGTTCCTTGTACTACTTGTACTACCATGCCCTCAAAAGTATGCAATGGAATCTGGAAAAC
CTGAACTTCCGTGACATTTTTTTGATAAATTCCGTTATAGATGGCAGGGAAATAGCTTCGCAACACATACCAATAATTATGTCGCACACAAGCTG
ACCACGAAATATGTCCATAAAATGGACTATCACTTAAGTGATCGCAGTGATCAGTGGGTGATGATGATGATGATGATGATGATGTTGAATGCCAA
AACGGGGACGCAACTGACAAAACCAAATGACTAGGCAATTATGCAATTATGGTCATGCGCAGGCAGCTACTACAAGCAAAAAGAATGAATATATA
GTGCAGGGTGAAAACATATTAAACTCAATTAATTTTTGTCCAGGACATGACTGCAAAAGCCACAAAAAGTGTGTGTCTGCAGTGACAGCATTATC
AAGAGCCGACCAAACAAACCCCCTTCATAACCCAACCCCCTGAATGACCAAACTGACCTGAACCGTCCCACAACTAAACACTTTTCTAATGACAT
TTTCGCGCGCAATTATATACTAATCACACGCAGGACCTCGGAAAGGTCCTGTAAAGGTATGCAAGAGTGTTGAGGAATGCGGCACTTGGTTATCA
ACGCTGCCTCGACTTTAACACCTACAAACAGATGGCTTTTTTTTTTTTGTTTTGAAAATTGACAGTGAAAATGCATTTTAGATTATCGCACTTGA
GTCAGAAGGTTGGAACAGTAGGATCCCGAGTGGTTATAGCTCCTGCGGGTCCAACTTTCCCGCGGCGTATTCGGGCATAACCAGTTGGGCTCTGT
CGCTTTATAATTACGAAATAGCTATTAGATAAACATCACTTTTGGTTAAGAGAATTAAAGGGAGACGCGCTGCCTACCAGGATAGTGTTGTTAGT
GGTTAAAAAGGAAGTCGATCGGATGTCGCCACAGGAAGTCGCCGAGCGTTAGAAACAAATGGTAGCTCAGTCCGTTGGGGAGTCAGTCGCCTCTT

FIGURE SHEET 217

GGCTTTCATGTGGGGTGCTAATTAGTTTGGTCAGGGCTGCGGAGGAAGTGGAAGTCACGAAAAGTGTTTGATGGGAAAAGGAAATGTCTAAGATC
ATAAGAGATGTCAAGAAAAACATGCAGGTTCGCTTGAAACTAAGATTTTTACAAACTCAAATCGAACTTGGGGTTTGCAAGAATAATTTACCTCT
TAAAACATCGAAAATTAAATTAAATTATTTAAAAGTAAGCCAGTAGAATTTAAAATGAATAAAGTACTCATAAGCTTACCTCTTGGCATTTAAAC
CCATAATTGTACGGCCTTGAGAAGCCGTCAAGGTTCTTTATCCTGAATCTTGTTTTTAAGCTGCTCGTCAAAAGCAGAAATGTTTTGCATGAAAT
GTACAATTTAAAGAGGACTGCAAGTAAATTAAACAAAATATAAACTTAATAAAATATAATAAACAACATTTAAATAATATTGTAAAGCAATCATT
AAAAACTAAAAATGGCATATAAACTAATTGGATAAGAGTTTCTAGGATATGGTCATCACATGCGACGCGTTTTCGAGTTTTTACGACTTCACAAA
ACCTATCAACAGTTAGTAAAACATTATCTGTAGATCCTTGTGGAAAAAACAACATATGATCCTTGAGGGAAACTCACACACAGCATGTGGCCGAA
AAGTCTCCTTGCATCGAAAACCCCAAACAAATTTGTTTACGTGAGTTTTTCTCGAAAAACATATATATACACCAACTTTTTGCTTTTAGCAAAAC
GAAGAAAGAAAGTAAATATTTTTCTTTGGGGTGCAAAGTGTGTCTAAGATATTCAAATTACTTAAATAGAAAGATGGGTGGAAGACCATTTTGG
AGTTGGGTCATCTTAACAGGTAGTCACGGAATGGTCATCTTTTTATCATAATAGAATTTCCACGAGTCTCGATTGATGCCTTCTGCTGCAGTTTC
AGCTTCAGCTGCTCCCCTTGAATTTCCTTTACACTTGAAAAACATAACTATACAATTCAAACAACTGAAAGTGCTATTAAATTATAGAAATCAAT
AGAGTTCTGTTGTTGCAAGTACGATGTATTGTTGATAAATACTTTTTTAACTCCGTAATGCTTGACTTATGAGATAATTTAATTTTTTGAGTGTA
CCGATGTCAGGTGCATCGCATTCGGCGCATGCGCAACGTCCGCATTTTCTAGTGGTTTACAACGCTTAATTATATCGAGGAGCCGAGTCCTTAGT
GCCCCTGTTGCACCTGTTGTGGCTAGAGTTGATCGCTGACCTTCTGTTAGAACTGTAAGTATGGGTTCGATGCGATGCGGGGCAGGTGAGTAGAG
TCGATGGGATTGGAGAAGGGGAGTGGAGTGGCAGCTGTTGAAGATCCTACCCCAACTAAAAGGATTCTGGCAATGTCTCTGCTGTTGCTTTTGTA
ACTTCAATTGACTTCCCCCTCGCTAATTGTATCCTGTCGCGTTTCCTTTTCCCCTAGCCCTACCCCTCCCTCCCCTCCTCGCTTCCTTTCTTCCT
TCATTTATTTTCCTTTTTCCGTGTGACATATGGGCCTGGCGTTATATTCGCCACGATTTATGGACCTCCCTTCGGCCTACCATTCAGTTCGACAC
CTTTTTTTCCTACCCCATATGCGAATGCTTTTTAGCCAACGACTTTCTTTCCCCTACTTTCTTGTTCTTACGCAACGGATTGTCTATTTTCCTCA
CTTTTTGCCTCGCTTTTCTTTTGCGTTTTCCGGCCTTTTCTCATGCACAATATTTTGCTGTTTCCAACCATCATTTTCACACTAATTGCGGATAT
GCCTTCTAATTAATTGGGTTCCCTCTGCTTCCCCGAAGTCCTTTTAGAGCATTTTTGCTTTCTTAGTTTTCAACCCCCTAACTATTCTACTTACA
ACAAAGAAATTTCCTTACACAGAAAAATAAGTCTCTTTGGTCATTTAAGAATATGTTAAAAATCTTAAAACAATTAATAAGATCATCATTTAAAT
CGTAATCCCAATATAAAGATCTGGGTTTTGTAAATATTCGAGCTCAAAAAACATTATGAAACAATTTGTATCTTTAAGATACAGCAGAAACCTAA
AAACGCAATAGAATAGACATTTATCTCTCAGTTGTAATCATGTTACACATCTAACATCATTTATAGTCGGATTAATGTAATCTTTTTTGTAAATC
ACAAAACGTCCTAAAATTAATATTCGTTAATAAGGATGCGATAATATCCTTTAGTTTTACAAAACAGTTGACAGCGGCTCTTGGCAAACAAATGA
CTGTATTATCGCTAGAGCAATCCAATTCTTGTCCAAATACCAGTGACTAAGATAGATTCCTACCTAATTGCAGGAACTGCCCACACGCAGGCTGC
GGCTGCAACTTCCTCTAATGAAGATTAAGTGAAGAAGGCTGCGAGTTCGGGCGAAATCCGCGGCGACAGGTATACAAATATGAATAATGCCGCGG
ATCGAGCGGATAAACTCGGGGGTTTCCTTTGCGCACAGCGCCTAATTAAAGGTGTACGATGCATGAGTGAATCTGTTTACCTGGACGGGGTCCTT
CAAGGTCATTTAACTGGAAAACCGAGTGTCGAAAATAAAGTCGACCGTATTTTTTTCCCTCATCTTCGGAATATTTGCTTTGTGCGGAAGATTTC
CCACAAGGAAATGGGACCAAGTCTCGAGATACAATATGAAATGCAACTTGAGGCAATGCAAAGAAGAATGCGCAAAATGCGCAAAGAAGAGCGCA
AAAAAAATTATATACAAATATGTATGTATCTCGAGTATATGCCAGACTATATACATATGTACATATGTAGAGGGAAAACAGGTCTCGAGTTATCC
GGCGTCTTCAACTGTCTGGGCCTGCAATTTTTGTGCGTCCTTTTTGGGCTGCATTTTGGGCTCCTCTGCACATGCGGCGAGATACATTCCTGAGA
TACTCGAGATAAAAATGCACATGCATCTGGGCATTTGTGGCGTTGTCCATGCCAATGCCGCCTCCTCTCCATTGTTGTGGTTTGGCCACCACTCT
TGCAATTAGTTGGAACTCGGTGGACCGAAAGTCTGCAGGAGTTGTGTAACAACATAGCTACATAATGCTGATAGGGTAAGAGGGTGAAGTTCATT
AGGAAGATATTTTCTCAAATCGAAAGCCTAATCATATTTGCATAATATGAAACTATAAATAATACTACTAAAAGTTTAAACCAATACACGAAGAT
TGCTTTATAAGCATCATTGAATTGAACCCGATCTTTGATGCTTCCTTTTCATACTCATGAATGCGTTTAAATTCTAATGGTCAATTGGCCCAAGT
TTGCTGTGTTGCTTCAGTCGCATATGCCCACCCTACCCAGAACTACAGGGTACTGCAAACGAGAACAGGAAAGTCGATCCTCGCCTGCGCGCATC
AGTGTATCTGTGAGTCCGAGTATCTGAGTATCTGTGTGCCGGGTATCTAAAGAGCGCCGCCTGGGCAAAACGGCGTGTGAAAGTAAAGTCGGCCC
AGCCGATGGAGGAGAACAAATCAAAGTTCTTGAATGGAGCGGCAGCGGCGGCGATGGCGACGGCGGCGTTCCAGTTCCAAGAATCGATGGCCTTG
AAGTAGCCGTTAGGACATCGGGACGCGCTCAATTGACTATTTAGTTTATATTTAGCAGCGTCTAAAAGGATGCCCACAGCGAGTCAGCTAGCTCA
AGTGGCCTGCGTCCTGTCTCTTCCCCGCTCCACAAATCGCCAGTCGGACGGACTATCCTTTGTTTGTCTGGGAATAACTGGAAACTGTTTATCAT
TGTTGTTTCTGCTCCTCATACATACGGCTTCACCTCATTCCGATTCCGAATCGGATTCTTCTGCCGCAGCGACAAAAATGTGTATGGACTATAAA
AAAAAAATGCCCACATATACATACATATGTACATATGAACCATTTATTTAAGGAGTTACTATTCACAACTCATCCTTTTGGAGAACATGTAATAT
TTGTAAAACATTCCGCACTTGTAATTGAGAAATATTGTTGGTATTTTACTAGGAATTCGGGTTAATATGGCCAGTTGATATGTGTGGATTCCTAT
AACCATTTACGTATGTATGTACATATGATGAGAAAATATTCGAGATCAGTTTGGGTTCCCATCTCGTCTAGAAAATCCTTTGATGACATACCGCT
TTCGAAGGTGGCAAGCACTTGGAGGATCATGAGCAGAATTGAAAGGTGTTGACTAGGATTTGAATAGATCATATAAGGAGTGTTTAGGTGGGTCA
AACAAAAGAAAATGTTGGGAAAATATACAAAATTCACGACACTGAATCATCAAAAACTTGATGCTCTTACTTTTTTCAAAATCACTTCTAAGAAA
AACAATTTATTTCCCCATGGTTTAAACTGGCCAAATCTAAACATAAGCGGCTGATTTTCGGCACGATCATGACATAATCGAAAAATTAAGTATAC
AAAAATCCACCCCATCAACAATACACCACCCACCCCCCACGCACACCCCCGCCGCGATCGCTCCAAAAGTTTAACGGCGCAAAAAGCGAACACGC
AAACTAAAAAACGTCAAAAGAATGCAAAAAATAAAGAAGAAAGCAAAAATTGCGAAGAAAACAACAACAAAATGAATGTGGCAGGTAAATGGAAG
CAGAGGAGAAGAGGAAAGAACGAAGATGGCGCGAAGCAAGGTGGAGACGAAGGGGAAGCGAAAGCAAAACGCCGAGAAATATCAATGAACTCCAT
TCTCCACTTGGCAGTCTATCTCGCTCACTCATTGGTTGGGAGCACGTACATAGAGTAACTACTCACAAAAATAAATATAACCACGATTTTACAAT
AATTAAAATACTATTATTAATTCTACATATGTAAACATACATACATATGTATGTACGTAGATTGTGGGTAAGGGCTAAATGCCACTACCAATCTT
TTTCTTCGTGTACCAAAGATATTTGCGCCACTTTTGACATAATTCATTATTTTGTTCTTCACTCGTTTACTCCATTTTGCTTTGAACCTCTGCTT
CGTGTTCGTCAAGTTTTCGAAAGGTCCGTCGACTGATCGGCGATTTTCCGAATTTTTTCGACGTCGCAGTCAAATGCTCTCTTTTTTTTCCGTTTT
AGAGCGCAGTACTAAAACGTTTTTGTTTGTTGTTGGTGTTGGGAAGGGGAAAATAACTTGACTCGCTGTTCTGATTGGAATAAAACGGAAGAGAG
CGAGAGAAAGAGAGCTTACTCTCTCTCTTAGCGAGCGCATTTCTTCCAAGTTTGTGCTTGTGTGTGTGTCATTGGAGGAAGCGTATAAAAATGAA
ATGAGCATGGGAAAAGAATGGAGAAACGCAAAGTGGCGCGAATTAGGCGTTTGGGCTGGGGCAGTTTTGTTTTACCGCCCAAAATCTATGCGAAT
GGCGGGAAAAAGTGCAATTCGGGCGGGAGAAAGATTAGAAAGTTGGCCCAAACAGCAGGGTAAACCATAAGCTGCATCTCAAGCCTTCTATAGTA
AGAAAAGCTGTAATAGTTCACTGAACTCCCGTTACGCATTAGAAACTCAGTGCACTTTTAGACGTGATTAGAAGCTTTCATTTATTTCATAGGAT
TTTCCAATTTGTTCCCATTGGATAACGGTTTAATTCTAATAGGACACTTTTCCTTATAGGGGGAACACTAAAACACTGTGTGGGGGAGACAATTT
GTAGTTGGACACCCCGTCTCTTGCCAATCAGAAAGCAACGGTTAAATCCTACAGCGTGTCAATTTTCTTATAAGAGGATGTTGTATTTGTAGCAA
AAAATGCAAAGACACGACGGCAAACGCAGCATTCTCTCCCGCTCTTTCCTTCACTGTTCCACACACACTTGTCACCGCACACGCGTCATAAATTT
TATTCCACTCTGAATAACGTATTGCCTTTTATCCACTAAAACCATTGTGCAATTGGTTTTACCTTCTAGTAAGCGGAAAAATGCTTAACATAATA
TCCCCGGTGTTTTCACTTGTTTTTCTTAAAGGGAATTGAACAACGTTTTTCGAGAGTTTTTCGTCGTCGTCGTCGCCGGCCACGAAAAAACTTCA
CGAGCAGCGGAGCGGCGGCAGCAAAGTGATCGCTTTGGAACCGAAAAAAAAATTGGTGGAACTGGGTATCAAAAGCAGCGACGTCGACTGCGGCG
AGTGTGCATGAGGAACGCGCCAAAACAGGCGGATCCGAAGCGCCAAAAAATGCAACAAACACAGGGGGCAACTTTGTTGTACTCTAGGGGAGGGA
CGGAGATGGGGCGAGCATCTCCAGCGCAAAGAACAGAGCGTGAGAAAGCGAGACGGGGCGATGAAGCCGCTGGTGGCAAGCTTGGCATTTTATTG
AATGGAGTCTGCAATTGGAGTCCCCAGTCCCCAACAGGCTAGTCAGACTACAATTGGAGGTTCGACGTCCAGTCAGCTGGGTGGTCGAAAAACAG
CTGACGAGGATGCCAGAAGGGCGGATTTAGTCGGATATATCGTGGTTATATATAAATACCTAAGATTTATTTCTATGTCATATGCCAATTTTAAT
TCAAATATGACCTTCAGAAAATAAATATTTAAATTTTAATATGAAACTATTTTTTTAATATATTTTTAAAGCGCTCCAAAATCAATTCAAGGTT
AAAATAAATTTATCTTGAAGGGTATTCATAAATCTTTAAAATTTAATTATTTATTTATTCTTCAGAAGCCTGAAATTACATGGTTTAATATGCT

FIGURE SHEET 218

TTTCTAGTAGTTTTTATGAACTGCAGCCAAATAACATATGACAAGATGACTGAGGTCGAACTAGGTGGTAACGCTGCTTTGAAACCAAACAAACC
ACTGCCACTTTGTTGTTTTCATCGATTAACATTCGAGCATTTTTGGCACCAACTTCGAGCGCTTATAAATCAGGTAAGCTAAATGAAAAACCATG
CGTGCCTATAACCAATTGAAAGATCAAAACTCGCAGAATCTGATTTTTCACTAAAATCGAAAATCCCGTTCAATTCGGCCAAATTAGAATCGATT
GAACTTGATGATTTCCCGCGCGCGGGAACCCGACGTCGGCGCGCGCTGCTGACAGCGATGACAGCTGCGCGCGCAAAGAGAAGGCGCGGAAGAGA
GCGCGAGAGGGGCAGGGGAACAGAGAGAGAAAGAGGCAAAAACGTCGACGTCGCTGCTCACGTTTTTTTTCCATTACTTTTCGACTGCTACAATA
TCGATGGAGAAAACGGGGTCTAAAGGAAATGGCTTAAAAAGCAAGTTCACGAACTTTTGAACCCTGCACCTGCTGCAAATCGAATGGGCCAATTG
GCCGGCATCACTCACCTGCTGTTGGGCAGGATTCGGGCAAATTCTCAGCGGGATTGCACACTGAAAAACACACGCGGACTGGAATGGTGATGAAA
AAAATTGCACACACCGCCGCACACATACACACGCACGCCAGCCAGCAAGACAGTATAGCCTCCTTTTTGTCACCTTTTTCGACAGATTTATCGTG
GTTCTGCGGTCTTTTTCACGGCTAGCTCAACCCCACGGCAGTCAAGGCCAATTCGATGCGATCCCCGCGATTTTTCAGCGACTCCAAAGTAACAC
AATGATCGCAAGTGGCACTGTGACGAGATCGAAATCGAGAGAGCGATGAAAGAGCAAAAAAAAAGGCCATAATCATCTGGCCACACGGCGCAAAG
AGAGAGTCGGAGTTTAGTGGCAGCGGCGTTGCCACTACGGCCGATCGCGTTGCGGGATTTTTATTGGCGCGTTATTCAAATTTTGAAAAATAACT
TCTATGTTAGCCTGACTTTTACTGCTCTGCATATTTAGTTCACTATTTTTCCGGGCTGATCATATCTGGAAATCGGGTATTTAAAATAATAAAAG
ATGTGCAACGTGCTTAATGTTAAATGGGGTTTTAGAAAAGAAATTGTATTATATAAATTTTGCTTTGATTGTTCGATTAACGGATATTAAATAAT
TGGATTTTCCGTTGGGAGCGTAATTTGAAACGCATATTTGATACGCTTATATTGTTTTTGTTTTATTGTTATATTCTTGTTTTTATCATGCGACT
ATCTAGTAATTAAATTCAAACAGAATACTCAAGTAAGAATTTTGTATTTTAGGAAATACTTAAAGTATTTTCACTCGATTTAATTTTTGGCGCAC
TTTTCAAACAATAACGGATGTCACTCAAATGATTTAATGGTTTTCAACTTTAATGCTCTTTTTTGTTGCTTAACTCACATATTGATTTTGTTTTA
TTATAGCAAATTTCGTATAATAAATGTTAGAATTACACGAACACTTTACTTTTCGATTTGAATTTGTTTGATTTTAATCCACCTCACTGAATTGC
AGATTTTTTCGGCGTGCTGTTATTTATCCACAAAATAATAATTTTTAGGCAGTAATAACTAACAATTAGCGAATATTTGTCTTTAGGGAACTTTG
CTAATTTTCATGTTCATGCTAATGTTAGCTATTGGTTTTGAATTTTATATTTAATATTAAAAAGTTAAATAATTAACTTCTGATAAATATTTTTT
AATATAGCTTGTATTTTTAGAACTCTTATTAATTCACTCAATCACTTTTGATAATAAATTTCCTCACACAAAC
(SEQ ID NO: 397)

Exon: 22253..21961
Exon: 15027..14900
Exon: 12092..11756
Exon: 4964..3694
Exon: 3627..3402
Exon: 3284..1701
Exon: 1036..1001
Start ATG: 14919 (Reverse strand: CAT)

Transcript No. : CT13013
TCACAGTGCCACTTGCGATCATTGTGTTACTTTGGAGTCGCTGAAAAATCGCGGGGATCGCATCGAATTGGCCTTGACTGCCGTGGGGTTGAGCT
AGCCGTGAAAAAGACCGCAGAACCACGATAAATCTGTCGAAAAAGGTGACAAAAAGGAGGCTATACTGTCTTGCTGGCTGGCGTGCGTGTGTATG
TGTGCGGCGGTGTGTGCAATTTTTTTCATCACCATTCCAGTCCGCGTGTGTTTTTCAGTGTGCAATCCCGCTGAGAATTTGCCCGAATCCTGCCC
AACAGCAGTCCTCTTTAAATTGTACATTTCATGCAAAACATTTCTGCTTTTGACGAGCAGCTTAAAAACAAGATTCAGGATAAAGAACCTTGACG
GCTTCTCAAGGCCGTACAATTATGGGTTTAAATGCCAAGAGTGTTTGTTCTACCAGCAGCACTGAGCCAAATGGCAGCATAGTCACAACCGCCCC
CAGCAACGGAGAAGTGAGCAGCAGCATAGTCGTCGTCGTCAGCAGCAGTAGTATCAGTAGCAGCAGCGATAGCCCAATCGCTATCCTTCCACATC
CAGATCCAATCCCATCAACATCGTTCTCTTCAGCGTCGCAACGAAGTGAAGAGGAGCTACCAGGAACCTCAGCAGCCTCCAGAACCGACGAGATG
TGCTCTTGTGATAGCCAGAATCTTGCAGCATCCACAGCCGCGACTTCCAATGGCAATAAACGTAAACGGCGTTTAAGCAGCGATTCAAACGAGGA
CCCTGAACTCGGTTTTGAGCCTCCATCAGCTAAGCGCCAGCAGCGACTGCCCGCTTTGTACGGCAGCGAGCAGGGCAATCTGTCATCGGTTGCCT
CCTCGGTCTACACCTCGCCCGTTGTCTCGGTTGATGGCCAGAGTACCCAGGAGCTGCTCAGCATACGTAGCTCACCGGCCGAGGATCTGTCGGAG
GCGCCACACAGTCCGCTGCCGGACAGCCCGGACAGTCCGCCGAGTCCGGATCGTGGAAGCAAGCAGACGCCAGTGGTGGTGCGCTACGCTGCGGA
GCAGGTGGTGACCAGTACGGTGGTCACGCAGAAGACGGAGGATGATGACCTTTTGGACGACAGCTGCGAGGACTACTCGTACGACGAGGATGATG
AGGATGACGTTGAGGAGGAGGACGACGACGTGGAGATCTACTCCTCCACAATTTCTCCAGCCTCCTCCGGCTGCAGCCAGCAGCAGGCGGTGAAT
GGAGAGCGTACTCCCGGCCTGCCAAAACATCAGGAGCAGATCCATCATCCGGTCAGTGACCTGATGATTAACATGCGGACGCCCATGTCGCCGGC
TGTGGAGAACGGTCTGCGCCAGTGCCCACTTCCTGCGCTCGCCTGGGCTAACGCCGCCGATGTTTGGCGCCTGATGTGTCACCGGGATGAGCAGG
ACTCGCGTCTGCGCAGCATTTCGATGCTGGAACAGCATCCCGGACTGCAACCACGTATGCGTGCCATTCTCTTGGACTGGTTGATCGAGGTCTGT
GAAGTTTACAAGCTGCATCGGGAGACCTTCTACTTGGCCGTCGACTACCTGGATCGCTATTTGCATGTGGCGCATAAGGTGCAGAAGACGCACTT
GCAGTTGATCGGCATCACCTGCCTGTTTGTGGCCGCCAAGGTAGAGGAGATTTATCCGCCAAAGATCGGGGAGTTTGCTTATGTGACGGATGGCG
CCTGCACAGAGCGGGACATCCTTAACCACGAGAAGATTCTGCTGCAGGCGCTCGACTGGGACATCAGCCCCATCACCATTACCGGCTGGCTGGGC
GTCTATATGCAACTGAATGTGAACAACCGCACTCCGGCCTCGTTCTCCCAGATTGGCAGGCAAAAGAGCGCGGAGGCGGACGATGCCTTTATCTA
CCCGCAATTCTCTGGCTTTGAGTTTGTGCAAACCTCACAGCTGCTAGATCTGTGCACCCTGGACGTGGGCATGGCCAACTATTCCTACTCGGTGC
TGGCAGCGGCCGCCATCAGTCATACATTTAGTCGGGAGATGGCTTTACGCTGTTCTGGTCTGGATTGGCAGGTGATTCAGCCTTGTGCTCGCTGG
ATGGAGCCATTCTTCCGAGTGATCTCCCAGAAGGCCCCCTACCTGCAGCTGAACGAGCAGAATGAGCAAGTCAGCAACAAATTTGGCCTGGGACT
AATCTGCCCCAATATTGTCACCGACGACTCGCACATTATCCAAACGCACACAACTACCATGGATATGTATGACGAAGTGCTTATGGCCCAGGATG
CGGCGCATGCCATGCGCGCTAGGATTCAAGCTTCCCCGGCCACCGCGCTGCGCGCTCCCGAAAGTCTTCTGACGCCTCCCGCCTCTAGTCACAAG
CCGGACGAGTACCTGGGCGATGAGGGCGATGAGACGGGGGCCAGGAGCGGCATCTCCTCCACAACCACATGCTGCAACACTGCCGCCAGTAACAA
GGGCGGCAAGAGCAGCAGCAACAATTCGGTGACCAGCTGCAGCAGTAGAAGCAATCCCTGAGAGATTCGCCTCACTGCTCTTGGCCATCATCCTC
TCACACTCACCACACCCGCCCAAACAGTCTACGTTAAGTGTTTCTTATATTTAAATTATTTTTGTTAAGTGAAAAGTTATTAGTTGCCTAATTCC
TATGCTACAAACATATTTAATTTGAAATTATCTACGCGCTCTTGATTCTCAACTCGCGATATAATCATTTTCCTCGCTCAGCTTAATATTTAACT
TTGTGTATTTATAGAAAAAACAGAAATATAATTTTAAATGTACACTATCTATAAAGCGCTCAAGCTTATATATATATATATACACATACACTTAT
AGTATAGCAGACCAGACAAAACTGAATTAACCATTAGACTAATACCTGCTGAAAAGGAGCACAACACTATCCAGAATTCAGTGGTGTGACGCTCT
CACAAACCAAGTTGGGTGCCTCAAAAATGAAACAACAAAATATGTTCGCAATCATACATGTTTAGCTTTCAACCAGTCAGTCAATCATTTGATAT
CACCAATCACCAAGCAGCAACTAACAAAACTAAAACTGACAAACAGAAGAGGGGGCAGTAGCGGCCCAGAGCACAGTACTTGACTAATCAACTAA
AATTAGCATATAAGTCGAGGGAATCTATCTAACTCTACTAATGCATTTCATTCGACCATTAATCCTACTAACAATGAATCAACAAACAAGACAAG
TCCACAGCTGACATGGAGTGACAAAAAGAAAATGGCAATTGAAGAAGTAAAGAATTAAATATTCATGAATTGAAACCCCAGAACAGACTATATGT
ATTCATATATACATCATTGTAAAATTTTTTTAATTAGACTAATTTGCCATAATTTGCTAAGCAAATAAATTCTGTACATAAAACAAAACAATACA
AAACGCACAAAAACAAGAATTAACCGTAACTGAAACGCATATAATATATTATTATATAAGTGTACAATTCTTTATATGGCTTAAAATATTTTATG
TACATTCAAAAGGCAACCACGCAAGGTAGAAAAATATTATTATTCGTTAGCTTAGGCATAAATAACATGTAAGTGTTCATACGATTAAGGCTGGA
TTGAAAACAAAAACAAACAAAAAACAACTAAAAGAAAAGCAAACAAAAAAAAAAACTAATCTATTTATGTTTTATTTGTAGTTTTAAAAGCAATA ATCATTTTAAAATTATGAATTTAATTTTAAATAATTTCAGAACTACGCTTATATCCATGATTTGATGTTAATAAATAAACGATCGCAAAATCGTA
AACTAAACAAATCAAGTTGAATTGAATGAGTAAATAAATATATACTTTTGTAAATAAAACTGAAATCAATTCAAA
(SEQ ID NO: 398)

Start ATG: 402 (Reverse strand: CAT)

MGLNAKSVCSTSSTEPNGSIVTTAPSNGEVSSSIVVVVSSSSISSSSDSPIAILPHPDPIPSTSFSSASQRSEEELPGTSAASRTDEMCSCDSQN
LAASTAATSNGNKRKRRLSSDSNEDPELGFEPPSAKRQQRLPALYGSEQGNLSSVASSVYTSPVVSVDGQSTQELLSIRSSPAEDLSEAPHSPLP
DSPDSPPSPDRGSKQTPVVVRYAAEQVVTSTVVTQKTEDDDLLDDSCEDYSYDEDDEDDVEEEDDDVEIYSSTISPASSGCSQQQAVNGERTPGL
PKHQEQIHHPVSDLMINMRTPMSPAVENGLRQCPLPALAWANAADVWRLMCHRDEQDSRLRSISMLEQHPGLQPRMRAILLDWLIEVCEVYKLHR
ETFYLAVDYLDRYLHVAHKVQKTHLQLIGITCLFVAAKVEEIYPPKIGEFAYVTDGACTERDILNHEKILLQALDWDISPITITGWLGVYMQLNV
NNRTPASFSQIGRQKSAEADDAFIYPQFSGFEFVQTSQLLDLCTLDVGMANYSYSVLAAAAISHTFSREMALRCSGLDWQVIQPCARWMEPFFRV
ISQKAPYLQLNEQNEQVSNKFGLGLICPNIVTDDSHIIQTHTTTMDMYDEVLMAQDAAHAMRARIQASPATALRAPESLLTPPASSHKPDEYLGD
EGDETGARSGISSTTTCCNTAASNKGGKSSSNNSVTSCSSRSNP*
(SEQ ID NO: 399)

Name: cyclin E type II
Classification: cell_cycle_regulator
Gene Symbol: CycE
FlyBase ID: FBgn0010382

Celera Sequence No. : 142000013384592
CTTGACCAAAAACAAAGTGGCCAAGGTGGCTTGCTTCGCTGAGTGGGTGGATGGTGCAGCAGGGCGCAGATTTGCCGACACTTTTTACTACGCGA
CTTTCGAACTGGAGAAAGCGGCGCGACTCGACGCGAGAAAACGAGAAGCGCGAACGGAGAGACGAGACGAGAGATTTATTTGGCTGCGCGGCTTC
GTCTCTTCGGCTTTTTGGCGCTCACAATTATTGCACCACCACAGGCACTCGCTCACGTACATACATTATACATATACACAGATATCTGTATTGGA
TTTTTTTTCCAAAGTTTGGATTTTGATGATATCCTGCGGGGTATACAGCGATTTTCGAACTGGCTTTGAAACTTGAAACTAAACTTTATGGCCAG
CCAAAAGCACTTTAAGCCTTTTAAGTGTGAAAATTAATATTGCACTTTGAGTTGGTACTGGTTTTCCCTTATGTGTTTTATCGGTTTAGCGGATT
GCATTGGGCAGAATAGAATTTTCGTTTGGACGCGATTTCTGCTCGGAACGCATCCACACTCGCCAGATTCTCGCCACGAACTGAGTGCGCTCTGT
GGGGCCAGATAGCTGCTCTTGGGGCACGATTCCTTGATACCTCGCCATTCGAACTTGCTTCCTCTCAATTCGAATTTGGCCAAAACCGTTGGGGT
TGCTTTGAGCCAGTGATGCCAGATGGGTTCGTTACCCTCTGTTAACCGCTTCCACAACAACGCTAGCGGTTCAGAATGTTGGCAGTTTGCAGAGC
TATCGATATAAAGGTCAAAGTGCAACCGTTCTGAATTGCCGCCCTGTTTTCAAATATAAAGCGGTTTATTTGAATCCTAATGCATTCAACAAGGT
AGTGTCTAAAATGTCCTACAAATAGTATGTTTTCTGGTTATCTTCAGTCGCATATTTTTGTATACTTGTTTCAAGACATGCAATATTTTATGACC
ACATTTACCACGTTGCGCACCTAATGATGAATCCCATTGAAAATGAAACATTTGAATTGATTTCAGTTTTATTTACAAAAGTATATATAGTAGCA
TATGTGCCATAGTATAAGACCACATATACTTACACACACACACACATACATAACCACATAGGAACAGCCATACACAAAATCATAGAATGCCCTTA
GGATATAAGTCATAAAATCATGTATCCAATAAGAACCCAAATTCTGGTGACAATAACAAATCCAGCCTACCCTAATGTAAACATTAACATCCGCT
GCCGAATCAGTTATTCCCACCAAAGGGTCAAAACCGCTTACGCAGCCCAAGTTCTCGGCTGATCAGTACCCATGAGTGATCCACTCAAGAAGGCA
CCCAATCCAACAGACATAAACATCCGCAGCCGCATTCGCGACTCCCACCAGAGGGTCGAAACTGCTAACACAGCTTTAAGGGTCAAAACTTTCCA
CGTAGCTCAAACTCGGCTGATCTATATCCATGCGCAATCCACTCAAGAGAGCGCCTAATTAACGTAAACATAAATGAGAGCCTATGTACGCTCAA
TATGAAGAAGTAAATAAGCTCAGCCAAGGGTTTGCTAAGCGTTCGCTTTGCAAATTAGATTTAGATTTTATTCATACTTCAATTGTGTAAGACGT
GAATTTGTCTCCGACATTCGCTTAAGTTTTTGATCAATAAAAATACTTTTTTTTATAAACCAACAAACCGCGAAGTTGTAATTATATTTATTTAC
TCATTCAATTCAACTTGATTTGTTTAGTTTACGATTTTGCGATCGTTTATTTATTAACATCAAATCATGGATATAAGCGTAGTTCTGAAATTATT
TAAAATTAAATTCATAATTTTAAAATGATTATTGCTTTTAAAACTACAAATAAAACATAAATAGATTAGTTTTTTTTTTTGTTTGCTTTTCTTTT
AGTTGTTTTTTGTTTGTTTTTGTTTTCAATCCAGCCTTAATCGTATGAACACTTACATGTTATTTATGCCTAAGCTAACGAATAATAATATTTTT
CTACCTTGCGTGGTTGCCTTTTGAATGTACATAAAATATTTTAAGCCATATAAAGAATTGTACACTTATATAATAATATATTATATGCGTTTCAG
TTACGGTTAATTCTTGTTTTTGTGCGTTTTGTATTGTTTTGTTTTATGTACAGAATTTATTTGCTTAGCAAATTATGGCAAATTAGTCTAATTAA
AAAAATTTTACAATGATGTATATATGAATACATATAGTCTGTTCTGGGGTTTCAATTCATGAATATTTAATTCTTTACTTCTTCAATTGCCATTT
TCTTTTTGTCACTCCATGTCAGCTGTGGACTTGTCTTGTTTGTTGATTCATTGTTAGTAGGATTAATGGTCGAATGAAATGCATTAGTAGAGTTA
GATAGATTCCCTCGACTTATATGCTAATTTTAGTTGATTAGTCAAGTACTGTGCTCTGGGCCGCTACTGCCCCCTCTTCTGTTTGTCAGTTTTAG
TTTTGTTAGTTGCTGCTTGGTGATTGGTGATATCAAATGATTGACTGACTGGTTGAAAGCTAAACATGTATGATTGCGAACATATTTTGTTGTTT
CATTTTTGAGGCACCCAACTTGGTTTGTGAGAGCGTCACACCACTGAATTCTGGATAGTGTTGTGCTCCTTTTCAGCAGGTATTAGTCTAATGGT
TAATTCAGTTTTGTCTGGTCTGCTATACTATAAGTGTATGTGTATATATATATATATAAGCTTGAGCGCTTTATAGATAGTGTACATTTAAAATT
ATATTTCTGTTTTTTCTATAAATACACAAAGTTAAATATTAAGCTGAGCGAGGAAAATGATTATATCGCGAGTTGAGAATCAAGAGCGCGTAGAT
AATTTCAAATTAAATATGTTTGTAGCATAGGAATTAGGCAACTAATAACTTTTCACTTAACAAAAATAATTTAAATATAAGAAACACTTAACGTA
GACTGTTTGGGCGGGTGTGGTGAGTGTGAGAGGATGATGGCCAAGAGCAGTGAGGCGAATCTCTCAGGGATTGCTTCTACTGCTGCAGCTGGTCA
CCGAATTGTTGCTGCTGCTCTTGCCGCCCTTGTTACTGGCGGCAGTGTTGCAGCATGTGGTTGTGGAGGAGATGCCGCTCCTGGCCCCCGTCTCA
TCGCCCTCATCGCCCAGGTACTCGTCCGGCTTGTGACTAGAGGCGGGAGGCGTCAGAAGACTTTCGGGAGCGCGCAGCGCGGTGGCCGGGGAAGC
TTGAATCCTAGCGCGCATGGCATGCGCCGCATCCTGGGCCATAAGCACTTCGTCCTGAAAGATAGAAGTTTCAATAAGTAACTGACGGAATAAAG
TACGCTTTATATTCAGAGTGAATCGAATACATATTTGGACGTATGCACACTTCTGTATACACTTAGATATACTTACATACATATCCATGGTAGTT
GTGTGCGTTTGGATAATGTGCGAGTCGTCGGTGACAATATTGGGGCAGATTAGTCCCAGGCCAAATTTGTTGCTGACTTGCTCATTCTGCTCGTT
CAGCTGCAGGTAGGGGGCCTTCTGGGAGATCACTCGGAAGAATGGCTCCATCCAGCGAGCACAAGGCTGAATCACCTGCCAATCCAGACCAGAAC
AGCGTAAAGCCATCTCCCTAAAAACGAAAAATATTCGGTAAGATAACCATGTCGTATGGGATGCAACTTCCATTCCAACTTACCGACTAAATGTA
TGACTGATGGCGGCCGCTGCCAGCACCGAGTAGGAATAGTTGGCCATGCCCACGTCCAGGGTGCACAGATCTAGCAGCTGTGAGGTTTGCACAAA
CTCAAAGCCAGAGAATTGCGGGTAGATAAAGGCATCGTCCGCCTCCGCGCTCTTTTGCCTGCCAATCTGGGAGAACGAGGCCGGAGTGCGGTTGT
TCACATTCAGTTGCATATAGACGCCCAGCCAGCCGGTAATGGTGATGGGGCTGATGTCCCAGTCGAGCGCCTGCAGCAGAATCTTCTCGTGGTTA
AGGATGTCCCGCTCTGTGCAGGCGCCATCCGTCACATAAGCAAACTCCCCGATCTTTGGCGGATAAATCTCCTCTACCTTGGCGGCCACAAACAG
GCAGGTGATGCCGATCAACTGCAAGTGCGTCTTCTGCACCTTATGCGCCACATGCAAATAGCGATCCAGGTAGTCGACGGCCAAGTAGAAGGTCT
CCCGATGCAGCTTGTAAACTTCACAGACCTCGATCAACCAGTCCAAGAGAATGGCACGCATACGTGGTTGCAGTCCGGGATGCTGTTCCAGCATC
GAAATGCTGCGCAGACGCGAGTCCTGCTCATCCCGGTGACACATCAGGCGCCAAACATCGGCGGCGTTAGCCCAGGCGAGCGCAGGAAGTGGGCA
CTGGCGCAGACCGTTCTCCACAGCCGGCGACATGGGCGTCCGCATGTTAATCATCAGGTCACTGACCGGATGATGGATCTGCTCCTGATGTTTTG
GCAGGCCGGGAGTACGCTCTCCATTCACCGCCTGCTGCTGGCTGCAGCCGGAGGAGGCTGGAGAAATTGTGGAGGAGTAGATCTCCACGTCGTCG TCCTCCTCCTCAACGTCATCCTCATCATCCTCGTCGTACGAGTAGTCCTCGCAGCTGTCGTCCAAAAGGTCATCATCCTCCGTCTTCTGCGTGAC
CACCGTACTGGTCACCACCTGCTCCGCAGCGTAGCGCACCACCACTGGCGTCTGCTTGCTTCCACGATCCGGACTCGGCGGACTGTCCGGGCTGT
CCGGCAGCGGACTGTGTGGCGCCTCCGACAGATCCTCGGCCGGTGAGCTACGTATGCTGAGCAGCTCCTGGGTACTCTGGCCATCAACCGAGACA
ACGGGCGAGGTGTAGACCGAGGAGGCAACCGATGACAGATTGCCCTGCTCGCTGCCGTACAAAGCGGGCAGTCGCTGCTGGCGCTTAGCTGATGG
AGGCTCAAAACCGAGTTCAGGGTCCTGAAAATGAAGGACAGATGTTTGAATAAGTAAATCATACAAGTGAATGCTTTAAATTGAAATGAACTAAG
ATAGTAGACAATCAAATATAATTACTAAGCTATATTCAGATATTACTTTCTTAAATAGTAGTTCATATTTCTCAAAGGTGTCAGCAATTATTACC
ATTTCAATAAATTTGCGCTTCTGTTCCAACTTCATAATAACATGAACAAATGAGTGGAGAGGATACTCAAGACAATAACAGGATCACACGACTGG
CGGAATTAGAAACGTGCTCCGAATTTAATTAGCGAAGGAGGTTTGGGAAATTTATGTGGGCACGCCTGTCAAAATTGGTAATCCTTGATAGATG
GACTGCTGGCTGGACCGAATGCACCCGCACAAAATGAGGAGCCAGGACTTCACACAAAAGATCAAGGACTATGGAATGGCATGGAGGTAAGACAA
TAGCACTTGGTTGGATTTTCTCGTGGGAACGAACGGGTTTCGTTTTGCTCTTTGTTTCTTTTGAATATTTTTGGTATGATCAACATATAGACACG
ATATCGTTATTGCACTTTTAACTTTAATGTTATAAATTTAGTAGCAGTCTTTGGAAATAATTTTGTTGCGTCGTTTCTCTTTGGTATGATTAAAT
AATTGTGCAAACAGATTTTTTGGTTATAGCATTTAAACAATTTTGGCTTCGTTTTGTTTTTTTGGTAGTTGTTGTTGTTGTTGGTGGGTGATCTT
GGCAAATCCGGTTCTTAAATTAGTTCTTTGCACTCGTTCTTGGTGGTTTATATAAATATATTTATCAGTCTTAACATTTGCTACTTGGCAACGAA
TAATTTTGGAATTTCGAATTTCGTTTCAGTTTGTCTGGGTATGTATTATTATTTGGCTAACTCCGCTCTTGGCTTGATCGAGTACCAATCGCGTT
GACGTGCGCTGTGCAACTGAGCTCGACGTTCTCCGTTCCAGATCGCCGATCCCCGAATTCCCCGATTACCGATCGTCGTTATCCTGCCCAACGAA
TGCAACGGTCTCGAAAATAGGGGTTGCTTTTCTCTGCAACAACAACAGCGGTAAAAACAGGATCGCCAAACTAACGTGCCGTCCCTTTCCAACGG
GGGTTGCTTGCCTAAGATATCCCCGTATATCTTGAGACGACAACTTGTGTTGTTTTTGTCTTTGCAGCAGCATTGCATTTTTCGCCTCTGGGTGT
TTATCGGCCCAACAACAAATCCCACTGACGGCTGTGGCTCCTGGATCCTTTTTACAATTATTTTTGTCAACATTTTCGTTCAGGTAGACGCAAGA
CGTTTGGAAAATCACTACCTACATCATAATCCTCAAAATAGCGACACATAATATAGTACATAGGAAGTATATAAATTACGATTTGCTAGCTTTTG
GCTCGAGCTGCCAGCGGCTGCATTAAGAATCTCCTGCATCTTAAAGGCTACTCAAATAATAAATTATCTTTTGACATTGATCAGAGGGATGGAGG
CGGTGCCAAAGCCAAAAGTAGAGCGATCCTAATGGAACCTCATAAGATTACAGCACAAAAATGACAAAAACAAAAAAACGAAAATGGAACCGAAA
ATCGAAAATCGAAAACAATTGAGATCCTTGACCATTGTTCTTCTTGCAGACAGATGATTGAAAACAGAAGCCAAAATCAGAAAGTCCATAAAGTA
CAATAAAATGTAGTCAGCATGGGACACAGATGTCTGAGATTGCTGATACCATAAAAAATACATAAATGAACGTATTTCGCTTAAAAAACTATTGG
GAATGTTTTGAAAGTTATCTCAAGAAACCCATAATTTCTTGGCTTTCTCTTTTTTTTTTAATGCATAGTAAAAGATATTTATTTATAAGATACTG
AAATATATCAAAAATAGCATTTAAAGCTATTCTGAAAGTTTTGGAAGCTTGGATTTCCATGTTTTAAATGTTTGGCACAATTATTTGCATTTATA
TATACTTTGAATGAAAAATATACATCAAAAATATTTGAAATTGCCCAATATCTGCACATAAAACTAAGCAATACAAAAGATATAAAATCCACATA
ATATTCGCATCAGTTTCTCTACAATTTCCTTTGGTTTACGATTGCAATTGATCTCTTCTTTGATTGAAAAAGGTGTGCAGTGCACACCATATAAT
TTATCAAATACTGACTGCATTTCGTCAACTTTCTTAACAGTCAATCTCACACATCGTAAAAGCTTAACAATATCAACCAACCCTGCTGGCCATTA
AAGATTTTCACATAATTTCTTGGGCGAAAAATGGGGGGAAATATTGCGATATTTATGTGACAATTTTAATTGTCTGAGTAGGTTTGCCTTCTCTC
GACAAACATACCGAGCAGAACTCCCCTCCTGAAGTCGAGAATAAATACTTTTTTTTTTTTTTTGTTCAGGCAAGACAGGAAGGTCCAAGACGCAT
GACAAATTTAATTTCTCATTCTTCTGGCCAACAAACTGCAACAACCCTCCGGAGGAGAAGATGATGTAGGTATAACCGGGAACGGCAATCGTAGA
ATGAAAATGAAAATGAAAATGGACATGGATATGGACATGGACACATGTCAAGGCACCCAGATGCAATGTAATTAAAATCAAAGCGTGCAATGGCC
TAAGAAGCCATCTCCCTGGACAATGGAAATTCCGTTCCTCTAGCCTTATTATTTCACTTCATTTTTGCTTTTGGTGCGTGGACATTGCATCTGCC
GTTTGGATTTGGTCAAGCGTTATGGAATCACAAAGATTATGCACGAAAATTCTCAGTTTACTTAACGACTTGACGGATTCGAAGAGAAAGATCGT
CGGAGTGAGTGTGAGAAATTAGTGAACTGTAAAGTGGGCTGGAATCTGGACCAATATGGACCCGAAGGGTTGCATTCCAAGTTTAACAAGGGTTA
AACTGGGTGGTTGCCCTTAAGCCACCGCCGTCGCCGCTGCCTTCAAGGATTTAAGTCTCAACTCCAAGCAGGCAGCTGCTGCAATCGTCCTTCGC
ATCTCGATCAGCTCCTTCAAAATCGAAGCCCACAAGGAAGGCACCCAAAACATCTCTCGAAATCTCACTGGGAGGGAGACCATGGGTCGCCGGCG
ACAGATGATGCAGTTCCTCAAGTTATGGGTACATACAGAAAGCAGACAAGAAGCAATTCGATTGTTAGGCGACAACCTCTGCTGCGTCGCCGACC
TCAATACTCGATGTCCTGGTGCCCCATTGTGTCGCTCTCCCTCTCCTTTTCGCCTACCCTATAAAGTCCTGCGCTTATGTGTCGTAATCTTTCGA
CGGCCGTCTGCTCGAAACCGAAACACCTTTAGTTTTCAGACCTTGGCGTGGGTCCAGGTGTAACTTTTTCACCGCTGTTTTCGTGTAATATGCTG
CATTGTTGTTTCCATTTATTTTTCTTTTCTTACAGTTTTTTTCTTTTTTTTTCAATTCTCCCCCAAGTCCTTTGATAACATTTAATTTCATACTA
CAATGTGCGGTAGTTGTTAATATTTTTACAGTTTGAAAAGATTATGATTTTCTTGAAATTCAGGATCAAGCTAGAGGTTTTTTCTTCAGATATTT
CATTTTTCATGAAGGACTCATAAAAGTCTGATGATCGTTCAAAATTAGCTAAAGTCCTGTCTACTTTTTGGGACATCGCTGCTGCTCTGCTTTTA
ATAAATGATATGCAAACAACATGCCAGTGGACAAATCCCCGAAGGACCATAACAAACACTCATATTTCAAACCAATTCAACTGACCCCTGGTCAG
TCCAGAAAGGGTTAATCCAACACAACACTTTCGCGGTGACATTGCTGGTTTTATCATCGCGGAAAATGGAAAATTCGGTGGTCAGGGGGACGTT
GAAATTGCTTGGACATGTAATTAATCATGCAATTGGTTAGATCCATGACAAAACGAATTAAAGCATATCACATTGGTGAAACGGGAGGAGGGTAA
GTGGACAAAGGACAAACCGCGAATGAATTTTGAATGCGAAAAATGAATTTTGATTAATTGTCAGGAAAGACAATTTTCTTTAGGGGATATGCCAA
CTTCTTAGGTGTAAGCCTTTAATAATTGAATATCTCTTGATATATTTACTGCAATTACGTTTTCCCCTGTTTTATCTAATAATTTACCTTTTAAA
ATTATCTGCTCAAAAACTAGTTTCTTATCAGTCGAATCTTAATGTAATTAATCTGAAAACAGATCGCTGCCCAAGTTTACCATTATCTCTTGTTT
ACCTCCAGCTAAATAAAATCCTCTGTAAAATGAAAAAAGAAAACTTTGAATTACAAAGCAGGCGACGCATGATCCCAAATCGGGATGCAATCTGG
GAAAGTGAAACTTGAATTCAGTTTCCCACAATATCCCGATACTGACTTGACAGAAATCAAGACCCACACTTGATTGCATCGAAAGGAAACCCGAG
CGAAAGCAAACCCAACTCCCCTTTTCGGGACAAAAGAAACAAAGAAGTTTCCCAAAAAAAAAAAAATAACAAGGAACTTTCGGCGATTTCATGCCT
GCCATGTAAGGAGTAAGAAAAAGGGGTTTACATTACACTGACAAATTGGTAAAATAATACCATAATTTTGATCCTGTGCCAGCAGCAAAACAAAT
ATTGTATAATATTTCAAGACCGCATTCCGATGCAGACGCGTTCTCCGTGTCCCGAAAAGCAGATGACACAAGAGTTTTAAGAAGGAAAAGCCTGA
TGATTTGCATAAAAGTTTAACGGAAATCTAATGAGCAGACGTCGCAGGATCGGCCAAGGCATTTGCATAAGGATAACATGTCCCGAAACGGGGTA
GCAAAATGCAACCCAGTTGGAAAGAATTTTTTTGTTATGCTCCGAATCTTCTGCAGAAGCAAATGTCGTCTCGATGAATATTTAATTAGAGACG
AAAAGAAAAGGGAAAAACTCGGCCCAGTGATCCTTGAAAAGGATAAGGCGTTGCTCAACCCCTCCGTCGGTTCGTTCGTGTGTTGCGGTTTCAGC
TCTGTCCCATTCCGGTAGTCACCACGATCCCTTACCCATCACCGTCCCCCCATCCCGATGCCAATCCCTTAAACTGTCTTGATCTAGTTCTTCTG
CCTCAAGCTAACCTATAACTATCGCAATTTCAAATTCTTACCACGGCCCTAACGGACATTTGCCGACGCCTTGACTTTTGGAAAAACCCACCCCT
GGAGAACTCGGACTTGGACTCAAGGTGTGCGCGCATGCGCAACGACGCCTTCTGTCCTTGTTCTGCGTCTCCTGCTCCTGCGCCTGCTTCTGGTC
CGGCTCCTTTGTCCTGGCATGCATATGCTCGGCATACTGCCAAAGACCCCTTCGGGGAATTCCCTTACTCAACAAAGTTCGCCTGAGAGGGGGCC
AGACATTTCCTTGCCATCCACTTTTTTCGTACCAGAATGACATTTGTTTGGCACGGAAGCAGGCGCAAAAACCATTGCAAAAACAAAAAACTCAA
AAAAAAAACAGCAAAAAAAATAACCAAGGCAGATATCATTTGTTTGGCAACAGACTGTTTGTATACCCTGGTCACTACATTTTAATTTTACGATA
TATTCTCAGTACAAACCAAGGCACCTTATAAATAATATAAATTTCTATATTTCCACTTTATCAATAAGATATGCTGAGTTCTAAAACAGTCCTTT
TAACATGCCTAAGATTTAATATATGAAAACTTATAGATATTCATAATCTTGCAAAGATAAAGATACCCATCTAGAGGGTACCAAACTATCAAACA
AGAAAACAATTTCTGCAAGTTCATTGCACGTATAGGAGAATATTCTCTCCCCTACATACATATTTCATATGGCACTGGAGAAAAAAATCCTTTGC
ACCAACACAGCTGCCCATCGTGAGGAGCCGCCAGGAGATGAGAAGGAAGCCATTGTTCTCCGCCTTGATTGCAGCTACTTGAGAGGAGATCTGAC
TTCAAGGCTTCCAAGGATGCTGCTAAATGAGCCCTTTTCAGTAAGTAGCGTTTATTTTTGGGCTCATCTTTGCATTGTGCCCGCGCAAAAGTGCC
AAGAAGTAGCTGTCTACGTGCTCAACGGCTTATTTGGCCAAAACTCAAGCAGCGAAAGATCAAATGAAGATCGGCAGCCAAACGAGTGGAAGCCA
CCAAAGGGCTGTCCATTCAAATGGAAGTACAAATAAAAGATCGTTTGCCAAACATAATAATAAAAATGGAGAATTGTTTAGCGATCGCTGATCAA
TGAAAACAATTGGGAAACTATAATCAAATAGATAAATATATAAAATGGCTATTGCTCAAATTCAAAAAGAAATATCACCTGCACGGTTCAAATAT

FIGURE SHEET 221

GTATGTACATTGTTTAGTTATAATCTCAAATTTACATTATTATTATTAACAGAGTTCACAAGCAATCAGATTATTCAGCTTGGAAATAAATCTTT
GAGCTTATAAACAGCCTAACCTTCAATTAATAGATTAAATTAATAGATTCTTATTTAGGCTAAAATGAAAGTGGCAATCACTGATCGACGAGAAT
TTAGAGAACAGAGAATTCCCAGAGTTCAAGAGTTCGTTAAATAGAAACATTTAATTAATTTCAAATGCATAGGCACTTTTTGAAACACACTAGAG
CTAATCATCGGCTTCCTAGAATGCCAGAATGCCTCTTGCCATTTCCCTGATAAGATTGCAAAAATCAACGAGGTCACATGACATGATAAAGCACT
TCATTCATAAAACTTATCTGCGCTGTGTCTGGCTTTATGTTTAAATTACGATTCGTTTTGGATTACGTACCTCGTTTGAATCGCTGCTTAAACGC
CGTTTACGTTTATTGCCATTGGAAGTCGCGGCTGTGGATGCTGCAAGATTCTGGCTATCACAAGAGCACATCTCGTCGGTTCTGGAGGCTGCTGA
GGTTCCTGGTAGCTCCTCTTCACTTCGTTGCGACGCTGAAGAGAACGATGTTGATGGGATTGGATCTGGATGTGGAAGGATAGCGATTGGGCTAT
CGCTGCTGCTACTGATACTACTGCTGCTGACGACGACGACTATGCTGCTGCTCACTTCTCCGTTGCTGGGGGCGGTTGTGACTATGCTGCCATTT
GGCTCAGTGCTGCTGGTAGAACAAACACTGCAAAAGAAAGTGAGTGGAATTAGCAGTGGGGTACTAAATAATAATACTAAATAATTTAAATTATA
TAGTTGAATGTCCCCAAAGAGCAGCTATTTGATAGAATACTTCAACATAGCTGCCTATATTTTTGTAGATTTAAAAGACATGATTGTATCAAAAA
CCCTTCCATTTAAAGAATCCCCCATATTTTTGTAAACCCAAACCCAAACTCTGGAGCGCAGTTATTTCCAATTTCTCCACTTTTTTTTTTTTTTT
GCAAAATAGAGAAATTCAATATGCCACGGAGGCAGGGCAGCAAATCACATAGGGGCGTTCTAAAATAGATACAAACGAAACGAACATAAATTCAT
TGAATTTTGACACGGCATTCGAATTTCGAATCGCGATGCAAGACTCGAGATTAAGGCGCCCAACGGATATATTAATATTTAACATCCGGAAATT
GAAATCGAGATGACTGATCGGGGGGGGAAATGGAAATGGAAATGGGATCGTTGTGAGGGCCCCGGGGAAAGCCTTTCCTCCTCGAGATTGAGCAA
TTTTGGCAAATTTGCATGCACATTAGCATAATGCAGGAGGCTGGCAAACGGGAAGAATACAATTTTCCATACTTTCCAAAGGACAGATGTTATAT
CCTTGCGTCGCAACTCTCAAGTGTTGCGATCCAAGCAACTGCACTTTAAGCAATTCGATGCGCGAATTTTTGCAATTTGAGCGAGGAGCTCAGGA
GAACGAGAGAAAAAAAAACGAAATCTAACCCTTGGGACCAAAAACCCTTCTTAAGGAACTCGTGAAAAGGGATAATAGAAAAAAAAAAATAAAAAA
GGGCTGCTGCCCATACATAAATTCAAATGCTTTAGCCATTTCTTTCTTGGCCAGAGGCTCGGCATTGCAGCCTCCTGTTTTGATCCTTGCCCTGC
ACTATCGATCGGGTTTAATGGTTTAATGAACAAGAAAAAGTAATCACGTAGTAAATTACGAGGAAATGAAATCGCTTTAAAAATGAGTTATGGCG
AGAAAGGACTAATGGAGCGTACGTGCACGCGGCCTGCAACTTTTTCCCGCTTTCTTTCATTGTACTCAGGGTTTCGGGGTCAGGGGTTTCCAGTC
ATCTCCGCGGCTTAAGGTTCAAACTGAAATTTGTCATTTCGAGGTGAAAGTTTCCTTTCCTTTGCGGCAAATGCAGATACTTTGTTTCGGTTTCG
TTTCCCCTTTTCTATTCCGTTTCAAATCCGAATCCCTGTAGGTAGCAAAAGGCTAGGGTGACTATCTCGGAGATGATATGATGAAAAAATTCGAA
GAAGTATTTCCTGGAATCTGGTCCAGTGGATAATAAGTGGACTATCGAAGGATCGATCTTTCTCACATGATAAATTATAAAGCAACGGCGACTTT
TCGATTAGAAATTAGTTATTTATGCGTTTAACTTGGTATCAACGAAACAGTTATGTTTCGGAATTTATGTGTTTGATCCTAAACTCTTAAGGTTA
CAAGAATTTTGTCATTTTTTGAACATTTTTATGTGAGTTCCTTGTACTACTTGTACTACCATGCCCTCAAAAGTATGCAATGGAATCTGGAAAAC
CTGAACTTCCGTGACATTTTTTTGATAAATTCCGTTATAGATGGCAGGGAAATAGCTTCGCAACACATACCAATAATTATGTCGCACACAAGCTG
ACCACGAAATATGTCCATAAAATGGACTATCACTTAAGTGATCGCAGTGATCAGTGGGTGATGATGATGATGATGATGATGATGTTGAATGCCAA
AACGGGGACGCAACTGACAAAACCAAATGACTAGGCAATTATGCAATTATGGTCATGCGCAGGCAGCTACTACAAGCAAAAAGAATGAATATATA
GTGCAGGGTGAAAACATATTAAACTCAATTAATTTTTGTCCAGGACATGACTGCAAAAGCCACAAAAAGTGTGTGTCTGCAGTGACAGCATTATC
AAGAGCCGACCAAACAAACCCCCTTCATAACCCAACCCCCTGAATGACCAAACTGACCTGAACCGTCCCACAACTAAACACTTTTCTAATGACAT
TTTCGCGCGCAATTATATACTAATCACACGCAGGACCTCGGAAAGGTCCTGTAAAGGTATGCAAGAGTGTTGAGGAATGCGGCACTTGGTTATCA
ACGCTGCCTCGACTTTAACACCTACAAACAGATGGCTTTTTTTTTTTTGTTTTGAAAATTGACAGTGAAAATGCATTTTAGATTATCGCACTTGA
GTCAGAAGGTTGGAACAGTAGGATCCCGAGTGGTTATAGCTCCTGCGGGTCCAACTTTCCCGCGGCGTATTCGGGCATAACCAGTTGGGCTCTGT
CGCTTTATAATTACGAAATAGCTATTAGATAAACATCACTTTTGGTTAAGAGAATTAAAGGGAGACGCGCTGCCTACCAGGATAGTGTTGTTAGT
GGTTAAAAAGGAAGTCGATCGGATGTCGCCACAGGAAGTCGCCGAGCGTTAGAAACAAATGGTAGCTCAGTCCGTTGGGGAGTCAGTCGCCTCTT
GGCTTTCATGTGGGGTGCTAATTAGTTTGGTCAGGGCTGCGGAGGAAGTGGAAGTCACGAAAAGTGTTTGATGGGAAAAGGAAATGTCTAAGATC
ATAAGAGATGTCAAGAAAAACATGCAGGTTCGCTTGAAACTAAGATTTTTACAAACTCAAATCGAACTTGGGGTTTGCAAGAATAATTTACCTCT
TAAAACATCGAAAATTAAATTAAATTATTTAAAAGTAAGCCAGTAGAATTTAAAATGAATAAAGTACTCATAAGCTTACCTCTTGGCATTTAAAC
CCATAATTGTACGGCCTTGAGAAGCCGTCAAGGTTCTTTATCCTGAATCTTGTTTTAAGCTGCTCGTCAAAAGCAGAAATGTTTTGCATGAAAT
GTACAATTTAAAGAGGACTGCAAGTAAATTAAACAAAATATAAACTTAATAAAATATAATAAACAACATTTAAATAATATTGTAAAGCAATCATT
AAAAACTAAAAATGGCATATAAACTAATTGGATAAGAGTTTCTAGGATATGGTCATCACATGCGACGCGTTTTCGAGTTTTTACGACTTCACAAA
ACCTATCAACAGTTAGTAAAACATTATCTGTAGATCCTTGTGGAAAAAACAACATATGATCCTTGAGGGAAACTCACACACAGCATGTGGCCGAA
AAGTCTCCTTGCATCGAAAACCCCAAACAAATTTGTTTACGTGAGTTTTTCTCGAAAAACATATATATACACCAACTTTTTGCTTTTAGCAAAAC
GAAGAAAGAAAGTAAATATTTTTCTTTGGGGTGCAAAGTGTGTCTAAGATATTCAAATTACTTAAATAGAAAGATGGGTGGGAAGACCATTTTGG
AGTTGGGTCATCTTAACAGGTAGTCACGGAATGGTCATCTTTTTATCATAATAGAATTTCCACGAGTCTCGATTGATGCCTTCTGCTGCAGTTTC
AGCTTCAGCTGCTCCCCTTGAATTTCCTTTACACTTGAAAAACATAACTATACAATTCAAACAACTGAAAGTGCTATTAAATTATAGAAATCAAT
AGAGTTCTGTTGTTGCAAGTACGATGTATTGTTGATAAATACTTTTTTAACTCCGTAATGCTTGACTTATGAGATAATTTAATTTTTTGAGTGTA
CCGATGTCAGGTGCATCGCATTCGGCGCATGCGCAACGTCCGCATTTTCTAGTGGTTTACAACGCTTAATTATATCGAGGAGCCGAGTCCTTAGT
GCCCCTGTTGCACCTGTTGTGGCTAGAGTTGATCGCTGACCTTCTGTTAGAACTGTAAGTATGGGTTCGATGCGATGCGGGGCAGGTGAGTAGAG
TCGATGGGATTGGAGAAGGGGAGTGGAGTGGCAGCTGTTGAAGATCCTACCCCAACTAAAAGGATTCTGGCAATGTCTCTGCTGTTGCTTTTGTA
ACTTCAATTGACTTCCCCCTCGCTAATTGTATCCTGTCGCGTTTCCTTTTCCCCTAGCCCTACCCCTCCCTCCCCTCCTCGCTTCCTTTCTTCCT
TCATTTATTTTCCTTTTTCCGTGTGACATATGGGCCTGGCGTTATATTCGCCACGATTTATGGACCTCCCTTCGGCCTACCATTCAGTTCGACAC
CTTTTTTTCCTACCCCATATGCGAATGCTTTTTAGCCAACGACTTTCTTTCCCCTACTTTCTTGTTCTTACGCAACGGATTGTCTATTTTCCTCA
CTTTTTGCCTCGCTTTTCTTTTGCGTTTTCCGGCCTTTTCTCATGCACAATATTTTGCTGTTTCCAACCATCATTTTCACACTAATTGCGGATAT
GCCTTCTAATTAATTGGGTTCCCTCTGCTTCCCCGAAGTCCTTTTAGAGCATTTTTGCTTTCTTAGTTTTCAACCCCCTAACTATTCTACTTACA
ACAAAGAAATTTCCTTACACAGAAAAATAAGTCTCTTTGGTCATTTAAGAATATGTTAAAAATCTTAAAACAATTAATAAGATCATCATTTAAAT
CGTAATCCCAATATAAAGATCTGGGTTTTGTAAATATTCGAGCTCAAAAAACATTATGAAACAATTTGTATCTTTAAGATACAGCAGAAACCTAA
AAACGCAATAGAATAGACATTTATCTCTCAGTTGTAATCATGTTACACATCTAACATCATTTATAGTCGGATTAATGTAATCTTTTTTGTAAATC
ACAAAACGTCCTAAAATTAATATTCGTTAATAAGGATGCGATAATATCCTTTAGTTTTACAAAACAGTTGACAGCGGCTCTTGGCAAACAAATGA
CTGTATTATCGCTAGAGCAATCCAATTCTTGTCCAAATACCAGTGACTAAGATAGATTCCTACCTAATTGCAGGAACTGCCCACACGCAGGCTGC
GGCTGCAACTTCCTCTAATGAAGATTAAGTGAAGAAGGCTGCGAGTTCGGGCGAAATCCGCGGCGACAGGTATACAAATATGAATAATGCCGCGG
ATCGAGCGGATAAACTCGGGGGTTTCCTTTGCGCACAGCGCCTAATTAAAGGTGTACGATGCATGAGTGAATCTGTTTACCTGGACGGGGTCCTT
CAAGGTCATTTAACTGGAAAACCGAGTGTCGAAAATAAAGTCGACCGTATTTTTTTCCCTCATCTTCGGAATATTTGCTTTGTGCGGAAGATTTC
CCACAAGGAAATGGGACCAAGTCTCGAGATACAATATGAAATGCAACTTGAGGCAATGCAAAGAAGAATGCGCAAAATGCGCAAAGAAGAGCGCA
AAAAAAATTATATACAAATATGTATGTATCTCGAGTATATGCCAGACTATATACATATGTACATATGTAGAGGGAAAACAGGTCTCGAGTTATCC
GGCGTCTTCAACTGTCTGGGCCTGCAATTTTTGTGCGTCCTTTTTGGGCTGCATTTTGGGCTCCTCTGCACATGCGGCGAGATACATTCCTGAGA
TACTCGAGATAAAAATGCACATGCATCTGGGCATTTGTGGCGTTGTCCATGCCAATGCCGCCTCCTCTCCATTGTTGTGGTTTGGCCACCACTCT
TGCAATTAGTTGGAACTCGGTGGACCGAAAGTCTGCAGGAGTTGTGTAACAACATAGCTACATAATGCTGATAGGGTAAGAGGGTGAAGTTCATT
AGGAAGATATTTTCTCAAATCGAAAGCCTAATCATATTTGCATAATATGAAACTATAAATAATACTACTAAAAGTTTAAACCAATACACGAAGAT
TGCTTTATAAGCATCATTGAATTGAACCCGATCTTTGATGCTTCCTTTTCATACTCATGAATGCGTTTAAATTCTAATGGTCAATTGGCCCAAGT
TTGCTGTGTTGCTTCAGTCGCATATGCCCACCCTACCCAGAACTACAGGGTACTGCAAACGAGAACAGGAAAGTCGATCCTCGCCTGCGCGCATC

FIGURE SHEET 222

AGTGTATCTGTGAGTCCGAGTATCTGAGTATCTGTGTGCCGGGTATCTAAAGAGCGCCGCCTGGGCAAAACGGCGTGTGAAAGTAAAGTCGGCCC
AGCCGATGGAGGAGAACAAATCAAAGTTCTTGAATGGAGCGGCAGCGGCGGCGATGGCGACGGCGGCGTTCCAGTTCCAAGAATCGATGGCCTTG
AAGTAGCCGTTAGGACATCGGGACGCGCTCAATTGACTATTTAGTTTATATTTAGCAGCGTCTAAAAGGATGCCCACAGCGAGTCAGCTAGCTCA
AGTGGCCTGCGTCCTGTCTCTTCCCCGCTCCACAAATCGCCAGTCGGACGGACTATCCTTTGTTTGTCTGGGAATAACTGGAAACTGTTTATCAT
TGTTGTTTCTGCTCCTCATACATACGGCTTCACCTCATTCCGATTCCGAATCGGATTCTTCTGCCGCAGCGACAAAAATGTGTATGGACTATAAA
AAAAAAATGCCCACATATACATACATATGTACATATGAACCATTTATTTAAGGAGTTACTATTCACAACTCATCCTTTTGGAGAACATGTAATAT
TTGTAAAACATTCCGCACTTGTAATTGAGAAATATTGTTGGTATTTTACTAGGAATTCGGGTTAATATGGCCAGTTGATATGTGTGGATTCCTAT
AACCATTTACGTATGTATGTACATATGATGAGAAAATATTCGAGATCAGTTTGGGTTCCCATCTCGTCTAGAAAATCCTTTGATGACATACCGCT
TTCGAAGGTGGCAAGCACTTGGAGGATCATGAGCAGAATTGAAAGGTGTTGACTAGGATTTGAATAGATCATATAAGGAGTGTTTAGGTGGGTCA
AACAAAAGAAAATGTTGGGAAAATATACAAAATTCACGACACTGAATCATCAAAAACTTGATGCTCTTACTTTTTTCAAAATCACTTCTAAGAAA
AACAATTTATTTCCCCATGGTTTAAACTGGCCAAATCTAAACATAAGCGGCTGATTTTCGGCACGATCATGACATAATCGAAAAATTAAGTATAC
AAAAATCCACCCCATCAACAATACACCACCCACCCCCCACGCACACCCCCGCCGCGATCGCTCCAAAAGTTTAACGGCGCAAAAAGCGAACACGC
AAACTAAAAAACGTCAAAAGAATGCAAAAAATAAAGAAGAAAGCAAAAATTGCGAAGAAAACAACAACAAAATGAATGTGGCAGGTAAATGGAAG
CAGAGGAGAAGAGGAAAGAACGAAGATGGCGCGAAGCAAGGTGGAGACGAAGGGGAAGCGAAAGCAAAACGCCGAGAAATATCAATGAACTCCAT
TCTCCACTTGGCAGTCTATCTCGCTCACTCATTGGTTGGGAGCACGTACATAGAGTAACTACTCACAAAAATAAATATAACCACGATTTTACAAT
AATTAAAATACTATTATTAATTCTACATATGTAAACATACATACATATGTATGTACGTAGATTGTGGGTAAGGGCTAAATGCCACTACCAATCTT
TTTCTTCGTGTACCAAAGATATTTGCGCCACTTTTGACATAATTCATTATTTTGTTCTTCACTCGTTTACTCCATTTTGCTTTGAACCTCTGCTT
CGTGTTCGTCAAGTTTTCGAAAGGTCCGTCGACTGATCGGCGATTTTCCGAATTTTTTCGACGTCGCAGTCAAATGCTCTCTTTTTTTCCGTTTT
AGAGCGCAGTACTAAAACGTTTTTGTTTGTTGTTGGTGTTGGGAAGGGGAAAATAACTTGACTCGCTGTTCTGATTGGAATAAAACGGAAGAGAG
CGAGAGAAAGAGAGCTTACTCTCTCTCTTAGCGAGCGCATTTCTTCCAAGTTTGTGCTTGTGTGTGTGTCATTGGAGGAAGCGTATAAAAATGAA
ATGAGCATGGGAAAAGAATGGAGAAACGCAAAGTGGCGCGAATTAGGCGTTTGGGCTGGGGCAGTTTTGTTTTACCGCCCAAAATCTATGCGAAT
GGCGGGAAAAAGTGCAATTCGGGCGGGAGAAAGATTAGAAAGTTGGCCCAAACAGCAGGGTAAACCATAAGCTGCATCTCAAGCCTTCTATAGTA
AGAAAAGCTGTAATAGTTCACTGAACTCCCGTTACGCATTAGAAACTCAGTGCACTTTTAGACGTGATTAGAAGCTTTCATTTATTTCATAGGAT
TTTCCAATTTGTTCCCATTGGATAACGGTTTAATTCTAATAGGACACTTTTCCTTATAGGGGGAACACTAAAACACTGTGTGGGGGAGACAATTT
GTAGTTGGACACCCCGTCTCTTGCCAATCAGAAAGCAACGGTTAAATCCTACAGCGTGTCAATTTTCTTATAAGAGGATGTTGTATTTGTAGCAA
AAAATGCAAAGACACGACGGCAAACGCAGCATTCTCTCCCGCTCTTTCCTTCACTGTTCCACACACACTTGTCACCGCACACGCGTCATAAATTT
TATTCCACTCTGAATAACGTATTGCCTTTTATCCACTAAAACCATTGTGCAATTGGTTTTACCTTCTAGTAAGCGGAAAAATGCTTAACATAATA
TCCCCGGTGTTTTCACTTGTTTTTCTTAAAGGGAATTGAACAACGTTTTTCGAGAGTTTTTCGTCGTCGTCGTCGCCGGCCACGAAAAAACTTCA
CGAGCAGCGGAGCGGCGGCAGCAAAGTGATCGCTTTGGAACCGAAAAAAAAATTGGTGGAACTGGGTATCAAAAGCAGCGACGTCGACTGCGGCG
AGTGTGCATGAGGAACGCGCCAAAACAGGCGGATCCGAAGCGCCAAAAAATGCAACAAACACAGGGGGCAACTTTGTTGTACTCTAGGGGAGGGA
CGGAGATGGGGCGAGCATCTCCAGCGCAAAGAACAGAGCGTGAGAAAGCGAGACGGGGCGATGAAGCCGCTGGTGGCAAGCTTGGCATTTTATTG
AATGGAGTCTGCAATTGGAGTCCCCAGTCCCCAACAGGCTAGTCAGACTACAATTGGAGGTTCGACGTCCAGTCAGCTGGGTGGTCGAAAAACAG
CTGACGAGGATGCCAGAAGGGCGGATTTAGTCGGATATATCGTGGTTATATATAAATACCTAAGATTTATTTCTATGTCATATGCCAATTTTAAT
TCAAATATGACCTTCAGAAAATAAATATTTAAATTTTAATATGAAACTATTTTTTTTAATATATTTTTAAAGCGCTCCAAAATCAATTCAAGGTT
AAAATAAATTTATCTTGAAGGGTATTCATAAATCTTTAAAATTTTAATTATTTATTTATTCTTCAGAAGCCTGAAATTACATGGTTTAATATGCT
TTTCTAGTAGTTTTTATGAACTGCAGCCAAATAACATATGACAAGATGACTGAGGTCGAACTAGGTGGTAACGCTGCTTTGAAACCAAACAAACC
ACTGCCACTTTGTTGTTTTCATCGATTAACATTCGAGCATTTTTGGCACCAACTTCGAGCGCTTATAAATCAGGTAAGCTAAATGAAAAACCATG
CGTGCCTATAACCAATTGAAAGATCAAAACTCGCAGAATCTGATTTTTCACTAAAATCGAAAATCCCGTTCAATTCGGCCAAATTAGAATCGATT
GAACTTGATGATTTCCCGCGCGCGGGAACCCGACGTCGGCGCGCGCTGCTGACAGCGATGACAGCTGCGCGCGCAAA
(SEQ ID NO: 400)

Exon: 20737..20583
Exon: 15027..14900
Exon: 12092..11756
Exon: 4964..3694
Exon: 3627..3402
Exon: 3284..1701
Exon: 1036..1001
Start ATG: 14919 (Reverse strand: CAT)

Transcript No. : CT13099
ACTTTGCTGCCGCCGCTCCGCTGCTCGTGAAGTTTTTCGTGGCCGGCGACGACGACGACGAAAAACTCTCGAAAAACGTTGTTCAATTCCCTTT
AAGAAAAACAAGTGAAAACACCGGGGATATTATGTTAAGCATTTTTCCGCTTACTAGAAGTCCTCTTTAAATTGTACATTTCATGCAAAACATTT
CTGCTTTTGACGAGCAGCTTAAAAACAAGATTCAGGATAAAGAACCTTGACGGCTTCTCAAGGCCGTACAATTATGGGTTTAAATGCCAAGAGTG
TTTGTTCTACCAGCAGCACTGAGCCAAATGGCAGCATAGTCACAACCGCCCCCAGCAACGGAGAAGTGAGCAGCAGCATAGTCGTCGTCGTCAGC
AGCAGTAGTATCAGTAGCAGCAGCGATAGCCCAATCGCTATCCTTCCACATCCAGATCCAATCCCATCAACATCGTTCTCTTCAGCGTCGCAACG
AAGTGAAGAGGAGCTACCAGGAACCTCAGCAGCCTCCAGAACCGACGAGATGTGCTCTTGTGATAGCCAGAATCTTGCAGCATCCACAGCCGCGA
CTTCCAATGGCAATAAACGTAAACGGCGTTTAAGCAGCGATTCAAACGAGGACCCTGAACTCGGTTTTGAGCCTCCATCAGCTAAGCGCCAGCAG
CGACTGCCCGCTTTGTACGGCAGCGAGCAGGGCAATCTGTCATCGGTTGCCTCCTCGGTCTACACCTCGCCCGTTGTCTCGGTTGATGGCCAGAG
TACCCAGGAGCTGCTCAGCATACGTAGCTCACCGGCCGAGGATCTGTCGGAGGCGCCACACAGTCCGCTGCCGGACAGCCCGGACAGTCCGCCGA
GTCCGGATCGTGGAAGCAAGCAGACGCCAGTGGTGGTGCGCTACGCTGCGGAGCAGGTGGTGACCAGTACGGTGGTCACGCAGAAGACGGAGGAT
GATGACCTTTTGGACGACAGCTGCGAGGACTACTCGTACGACGAGGATGATGAGGATGACGTTGAGGAGGAGGACGACGACGTGGAGATCTACTC
CTCCACAATTTCTCCAGCCTCCTCCGGCTGCAGCCAGCAGCAGGCGGTGAATGGAGAGCGTACTCCCGGCCTGCCAAAACATCAGGAGCAGATCC
ATCATCCGGTCAGTGACCTGATGATTAACATGCGGACGCCCATGTCGCCGGCTGTGGAGAACGGTCTGCGCCAGTGCCCACTTCCTGCGCTCGCC
TGGGCTAACGCCGCCGATGTTTGGCGCCTGATGTGTCACCGGGATGAGCAGGACTCGCGTCTGCGCAGCATTTCGATGCTGGAACAGCATCCCGG
ACTGCAACCACGTATGCGTGCCATTCTCTTGGACTGGTTGATCGAGGTCTGTGAAGTTTACAAGCTGCATCGGGAGACCTTCTACTTGGCCGTCG
ACTACCTGGATCGCTATTTGCATGTGGCGCATAAGGTGCAGAAGACGCACTTGCAGTTGATCGGCATCACCTGCCTGTTTGTGGCCGCCAAGGTA
GAGGAGATTTATCCGCCAAAGATCGGGGAGTTTGCTTATGTGACGGATGGCGCCTGCACAGAGCGGGACATCCTTAACCACGAGAAGATTCTGCT
GCAGGCGCTCGACTGGGACATCAGCCCCATCACCATTACCGGCTGGCTGGGCGTCTATATGCAACTGAATGTGAACAACCGCACTCCGGCCTCGT
TCTCCCAGATTGGCAGGCAAAAGAGCGCGGAGGCGGACGATGCCTTTATCTACCCGCAATTCTCTGGCTTTGAGTTTGTGCAAACCTCACAGCTG
CTAGATCTGTGCACCCTGGACGTGGGCATGGCCAACTATTCCTACTCGGTGCTGGCAGCGGCCGCCATCAGTCATACATTTAGTCGGGAGATGGC TTTACGCTGTTCTGGTCTGGATTGGCAGGTGATTCAGCCTTGTGCTCGCTGGATGGAGCCATTCTTCCGAGTGATCTCCCAGAAGGCCCCCTACC
TGCAGCTGAACGAGCAGAATGAGCAAGTCAGCAACAAATTTGGCCTGGGACTAATCTGCCCCAATATTGTCACCGACGACTCGCACATTATCCAA
ACGCACACAACTACCATGGATATGTATGACGAAGTGCTTATGGCCCAGGATGCGGCGCATGCCATGCGCGCTAGGATTCAAGCTTCCCCGGCCAC
CGCGCTGCGCGCTCCCGAAAGTCTTCTGACGCCTCCCGCCTCTAGTCACAAGCCGGACGAGTACCTGGGCGATGAGGGCGATGAGACGGGGGCCA
GGAGCGGCATCTCCTCCACAACCACATGCTGCAACACTGCCGCCAGTAACAAGGGCGGCAAGAGCAGCAGCAACAATTCGGTGACCAGCTGCAGC
AGTAGAAGCAATCCCTGAGAGATTCGCCTCACTGCTCTTGGCCATCATCCTCTCACACTCACCACACCCGCCCAAACAGTCTACGTTAAGTGTTT
CTTATATTTAAATTATTTTTGTTAAGTGAAAAGTTATTAGTTGCCTAATTCCTATGCTACAAACATATTTAATTTGAAATTATCTACGCGCTCTT
GATTCTCAACTCGCGATATAATCATTTTCCTCGCTCAGCTTAATATTTAACTTTGTGTATTTATAGAAAAAACAGAAATATAATTTTAAATGTAC
ACTATCTATAAAGCGCTCAAGCTTATATATATATATATATACACATACACTTATAGTATAGCAGACCAGACAAAACTGAATTAACCATTAGACTAAT
ACCTGCTGAAAAGGAGCACAACACTATCCAGAATTCAGTGGTGTGACGCTCTCACAAACCAAGTTGGGTGCCTCAAAAATGAAACAACAAAATAT
GTTCGCAATCATACATGTTAGCTTTCAACCAGTCAGTCAATCATTTGATATCACCAATCACCAAGCAGCAACTAACAAAACTAAAACTGACAAA
CAGAAGAGGGGGCAGTAGCGGCCCAGAGCACAGTACTTGACTAATCAACTAAAATTAGCATATAAGTCGAGGGAATCTATCTAACTCTACTAATG
CATTTCATTCGACCATTAATCCTACTAACAATGAATCAACAAACAAGACAAGTCCACAGCTGACATGGAGTGACAAAAGAAAATGGCAATTGAA
GAAGTAAAGAATTAAATATTCATGAATTGAAACCCCAGAACAGACTATATGTATTCATATATACATCATTGTAAAATTTTTTAATTAGACTAAT
TTGCCATAATTTGCTAAGCAAATAAATTCTGTACATAAAACAAAACAATACAAAACGCACAAAAACAAGAATTAACCGTAACTGAAACGCATATA
ATATATTATTATATAAGTGTACAATTCTTTATATGGCTTAAAATATTTTATGTACATTCAAAAGGCAACCACGCAAGGTAGAAAAATATTATTAT
TCGTTAGCTTAGGCATAAATAACATGTAAGTGTTCATACGATTAAGGCTGGATTGAAAACAAAAACAAACAAAAAACAACTAAAAGAAAAGCAAA
CAAAAAAAAAAACTAATCTATTTATGTTTTATTTGTAGTTTTAAAAGCAATAATCATTTTAAAATTATGAATTTAATTTTAAATAATTTCAGAAC
TACGCTTATATCCATGATTTGATGTTAATAAATAAACGATCGCAAAATCGTAAACTAAACAAATCAAGTTGAATTGAATGAGTAAATAAATATAT
ACTTTTGTAAATAAAACTGAAATCAATTCAAA
(SEQ ID NO: 401)

Start ATG: 264 (Reverse strand: CAT)

MGLNAKSVCSTSSTEPNGSIVTTAPSNGEVSSSIVVVVSSSSISSSSDSPIAILPHPDPIPSTSFSSASQRSEEELPGTSAASRTDEMCSCDSQN
LAASTAATSNGNKRKRRLSSDSNEDPELGFEPPSAKRQQRLPALYGSEQGNLSSVASSVYTSPVVSVDGQSTQELLSIRSSPAEDLSEAPHSPLP
DSPDSPPSPDRGSKQTPVVVRYAAEQVVTSTVVTQKTEDDDLLDDSCEDYSYDEDDEDDVEEEDDDVEIYSSTISPASSGCSQQQAVNGERTPGL
PKHQEQIHHPVSDLMINMRTPMSPAVENGLRQCPLPALAWANAADVWRLMCHRDEQDSRLRSISMLEQHPGLQPRMRAILLDWLIEVCEVYKLHR
ETFYLAVDYLDRYLHVAHKVQKTHLQLIGITCLFVAAKVEEIYPPKIGEFAYVTDGACTERDILNHEKILLQALDWDISPITITGWLGVYMQLNV
NNRTPASFSQIGRQKSAEADDAFIYPQFSGFEFVQTSQLLDLCTLDVGMANYSYSVLAAAAISHTFSREMALRCSGLDWQVIQPCARWMEPFFRV
ISQKAPYLQLNEQNEQVSNKFGLGLICPNIVTDDSHIIQTHTTTMDMYDEVLMAQDAAHAMRARIQASPATALRAPESLLTPPASSHKPDEYLGD
EGDETGARSGISSTTCCNTAASNKGGKSSSNNSVTSCSSRSNP*
(SEQ ID NO: 402)

Name: cyclin E type II
Classification: cell_cycle_regulator
Gene Symbol: CycE
FlyBase ID: FBgn0010382

Celera Sequence No. : 142000013384450
TTATACGCTTGTCCTTGATGATGTTGCTATTGCCATAGAGCGGCTTCTTGTAGACTATCTTGGATGCCTCCAAATGGATGGCTAGCAGAAGTGTC
AGCAGCAGCAGGGAATTTTTAAAGGCGCCTGATATATGAAATATATACGATATGAAATGTGTTCTTTAGCTAATATTACTTTCAAAGCTTACCCA
TCTTGGTATCTACGGAAACACTGAATACTTCTGCCTTTGCGCCATCCATTTTATATAAGCCATTTTCTTACTTGGCTTGCAGTTTTTCAAGATTT
CGGTCTTCCATTTTAGTCGGCCCCCAACGAAGTTCAAGTTGTGAGAACCGGCAAAATTGTGTCAGGGTTAAGTCTGATTAAGCAGAATTTTCACA
CAAAGCGAGTGGAATTCATTCATTTGGAGGAAAGTGAGAAGAAAGAAAAAGAATTACTTCCGAAAATTATGCGTAATCAATAAACCCAAAAGTTG
TGTCTTGAGCTGCACAAAGTTTACCTTACCGTTCTAAACTACTTTCCAAAATCTTTTTAAATATCCCGCCAAACTGCAATGAAACTGTTATGATT
ATAATAACATAATGGATAACATAAATAAACGGCCGATTAAACAGCAATTATTATCCAAATTATACAAGTTATAATATGGTAATATTAACAAACAT
TTCAACATAAGCAAAGCTTTGGTTTTTAATCTAATTATAGATTTAATTTAATTTTCATTTTTTGGTTTGTTTTTCGTTAAGTTAGTATTTTTTGC
GCTGTTTATGGAACTTAACAGAAATACCAATCAATATTGGGCGGCCAACATTTGAAATATAAATACAGATTATCGATATGTATCTTGAACGAAGT
TTTAAATGTTTGTTATTTGTTAAACTCAACAATCCTATAGATTTATGCCATAAAAATGTCAAAATTATCGTTGCTTCAAATGATTTAAGTACAAA
ATTCGAGTTTCGATAAACGGTTAACAGTGCCGTACTCACCACGGTGCGCCCAACAGCACGCACACACAGCCGGCTGTGGTGGGTTCGCTGGACAG
GCAGTGTGGTGAATATACTAGTTGCTGGAGCTTGCCGCAAAAAAAAAAAAAAAAGAAAACAAAACAGATCGAAAAACACAGCAAACAACAAAATTA
TACGCCATTAATTACCCGATAAACTTACCGATGGCCGATAAGCAACGGCTAAGTGATCCGTAACACCCAGCGATAAGATCCAGATAAGATTGGAA
TTAAATTTTGGGTTTGCCATCCGCATCGAAATCGCCGCAATCGGAATTTACTTGTACACCAGCCAACTCGCCGTTCAAGACGTCCAAGTTTTTTT
TAATCCAGAAATCCCATACACTGCCAAAATGCCCGAATATGTGCCGGCACGGGGCTTCAAGGAGATGGAAAATCTGATCAAGCTGTACGAGAACC
AGCGCAGCCCCATCTACATCTACTTCTACGGCGAGAAAGACAAGGACGGACGCAGCTGGTGTCCGGACTGCGTGGCGGGTAGGTGACGAATTCTC
CTCGCCCAGCGGGGCGTTACTAGTCCAGTTGGGCACTCTACATTCTGCTTATCACGCTTCTCATTTGTGGGTTTCAGTTAGTTACTTTCTACCCA
GCTAACTTGAGTTACTTTTGATTTGATTTTCGCTCTCCATTGAGAGTTCCATCTACATTGTACATTGTCCTCATCATTTCGATTCATTTCATCGC
AGAGTTATAACATAACATAAAGAAGTGACATACATTAAGTTAATCCCATTATCGCTGATATTTTCCAGCCGAGGAAACTATCATGAGTGCCTTTC
GCAACCACGCGCCGGCGGATTGCATGATCCTGGTGGTGGACGTGGGTAGCCGGGAATCCTGGATAGGCAAGGACAACATGTTCCGAAAGCCGCCA
TACTCGGTGGAAGGCATACCGACCCTTATACGCTGGAAGGGCGTGGAGCGCCTGGATGGGGATCAGCTGCTCAAGTCGAGTCTTCTGGAGCTCTT
TTTCGAGGAGACCGATCCGAAGAAGTCCAATTTTGTCGCCCAATAAAACGCGATTTGGCTTTGGCTTAAACTCACTCCCACTCTCAGTCTCTCTC
TCTATCACTCTCTCTCTCTCTCTCTCGCTGCGGCTCTCTTTCTCTTTGCTGCTTTGCGCTCAACTCGGTGGAAAGAACGAGTGAAATTGTCGTTG
GGAGGGGTGGTGCTAAAAAAGGGGGAATGGAGAAATGGGGAGAACAGAATGAGTGGAGCATTTCTGGCTGGCAGCGCGTCGCTCGGCATTTAC
TCGTTTATTTGCACGCATGTCGTCGACCAGGACGAATCGTTTGGCAGAGCGCGGCTGAAAAAGGAATCGAAAACGGGGCTATAACGGTAATAGCG
GCACACGCGTCCAACGGTAAACACGCGTGCCAACGCGCCATCTCGCTCGCACGCGCTAATGCCGCGATTTAAGTTTTGTTTTATTTTTTGCAAGT
GTTCGAATCAAAAAGCCTAACAAAACACAAAACCCGAAACAGTTCTCAAGAAATACATAGGTAAATGCAAAGTAAGATATGTATATATGTAGCTA
AACATAGCGGAAAAGCGCAGAGTATCATTGAATTTGAAGCACACGACCGCACAGTTTTGCAAGCTGATTAACTGTAAACATGCTGAACATAAACA
ATGGATAAAAAAACATGATAGATCCTGCCTAAAAGTGAATGGTTATAAATTAAGAATGGGCTTGCAACGGTAAATCCTGTTGCGTTTTGCTTTAA
CTGTTTGAAAATAAAAAAAAATATATATTTAATAATAGAATAATAAAAGGTTTCGTAAGTAAAGTAACATCAAAACTAAACTAAAGGTAAATGTA TAAATTGATCAAATGTTTTAAAAAGTAATACGTTCAATATTTAGCCAATGCAAAACCAGGCAAACGCAATTTACCGTAACTTCTTAGCCAAAAAC
CCTGTTGCTTCGGCCGCGTTGCATATTAATTGTGTGGCAAGACTGTTGCTTCTTCTCGTTCGATTTGTTTGGTAACTTTTACGTTAAATCATTGA
C
(SEQ ID NO: 403)

Exon: 1001..1503
Exon: 1779..2041
Start ATG: 1395

Transcript No. : CT13113
CAACAGCACGCACACACAGCCGGCTGTGGTGGGTTCGCTGGACAGGCAGTGTGGTGAATATACTAGTTGCTGGAGCTTGCCGCAAAAAAAAAAAA
AAAGAAAACAAAACAGATCGAAAAACACAGCAAACAACAAAATTATACGCCATTAATTACCCGATAAACTTACCGATGGCCGATAAGCAACGGCT
AAGTGATCCGTAACACCCAGCGATAAGATCCAGATAAGATTGGAATTAAATTTTGGGTTTGCCATCCGCATCGAAATCGCCGCAATCGGAATTTA
CTTGTACACCAGCCAACTCGCCGTTCAAGACGTCCAAGTTTTTTTAATCCAGAAATCCCATACACTGCCAAAATGCCCGAATATGTGCCGGCAC
GGGGCTTCAAGGAGATGGAAAATCTGATCAAGCTGTACGAGAACCAGCGCAGCCCCATCTACATCTACTTCTACGGCGAGAAAGACAAGGACGGA
CGCAGCTGGTGTCCGGACTGCGTGGCGGCCGAGGAAACTATCATGAGTGCCTTTCGCAACCACGCGCCGGCGGATTGCATGATCCTGGTGGTGGA
CGTGGGTAGCCGGGAATCCTGGATAGGCAAGGACAACATGTTCCGAAAGCCGCCATACTCGGTGGAAGGCATACCGACCCTTATACGCTGGAAGG
GCGTGGAGCGCCTGGATGGGGATCAGCTGCTCAAGTCGAGTCTTCTGGAGCTCTTTTTCGAGGAGACCGATCCGAAGAAGTCCAATTTTGTCGCC
CAATAA
(SEQ ID NO: 404)

Start ATG: 395

MENLIKLYENQRSPIYIYFYGEKDKDGRSWCPDCVAAEETIMSAFRNHAPADCMILVVDVGSRESWIGKDNMFRKPPYSVEGIPTLIRWKGVERL
DGDQLLKSSLLELFFEETDPKKSNFVAQ*
(SEQ ID NO: 405)

Celera Sequence No. : 142000013384645
TAAGATCAAATAACAATATTTAACTATGGCGCCACGTTTGACTTACCTCGGATAGCAATCTCTTGAGGCCCTCGACCTCATCCTCGCCGGCGTTT
AGCTCGCCACCGGGCAATTTGAAGAACGTGGTGCCCAGCTGCAGGAGCAAGACATGTGGCAGTCCGTGCTCGTGGACCAGAAGCACTCCCTCGAC
GGAGCGCCGCATTCCGATCCGGTCGAATTCCTCGCGCATCCGCTGGAATCGGGATGGCACCGACGGATCCTTCTCAAAGAGCGGCTCCTTGGTGC
CGAATGTGTAGTTCGTAAGGGGGTATCTGAAACAATCGATCGATCTATGATGTGCGTCTATGAATGAAATGTGTTGTACCCACAAGTTGATGGTG
CGATTGATGGTTAGCGCCTGGTTGGTGTACTTCTGGGTACCGTTGTTATTGCTGCTGGCTGCATCCGCTTGGCCTTGGCTTCCGCGGCGCGGCCA
ACCGGAGCCCGATTTGTTTGAGACTTGCGAGGACGCCATTTTGTTATACACACACCCCTGTGGGAAAATTTGCGGGACAAGCTGGCCGACTTTCT
ACCAAATCCTTTGGTTGTGCGTTGGAAACTTGTATTCCAATAATATTATAATCCTTAACTGTTTATTTACAAGTTATACTATAAATGTAAACCCG
TTTTAAGCCGCTTAATTACACTTTTCTGTCCAGCGCTTGTGCAAAAAAATTAACCGGCTGGACGAGGGCTGCACGTGAATTGATTGATGATGAGC
AGAACTGGTTCGTTGAACTAGATTATGGAATTAATCGATTTCGTACTTTGTGTGAAATAAACTTGTAATGACCTTTTGCTTAATATTTATTAAAG
ATTTATTCAATTTTTTGTTTTATTTTTAAATGCAGTTTTAAATTATTGTTTGTTTACATATGTAACGACAGCCCTGGTGTTTCTTGTCTAATGGC
AACGCTCTGAAATTGCGCAGCAACCCCATCTGGCCACACTGACCCATTAGTTTTTTGTTTATGTTGGGTTGTCGGAAAAATCGGCTGTTTTCCGT
GTGTCCGTCTGCCATGAAAAGCTGCTAAAAAGCTAAATATAAAAATCAGCGCAGCACACACGTTCCGCTGCCTGCATTGTTTGCCCATTCTAATG
GGAAATTATGTGAGTGCGAGTCAGGAAAACGCATCGTGTGTGTATATATACATATATACATAAGTATGTAACTGCGCCCGTTTGTTTGTGTGTGT
TTTTGTGTGCATGGTGCAATGGAAAAGTGATTATTATAAATGAAAATCAGTGAAATGTGTAAGTGTGGCACCGCAAACGCTTTGAACTTTTCCAT
TTTCATGTTTTCACCTTGTCTTCTCTTCTCTTCTTCACCCACCTCCCCCGTAGTCAACCAACTCCCACTTGTGCGTGTGTAGGAAGGCAGAAGGG
TGTTTTGCATTCGTGTGCGTGCCAGATAAAAAGACTTTGAATTTCTGGAGGATATTAGTGTCAACTGTGTGGGGTATAATACGCCGTAGGCCCTA
ATATGCAGGCAAGTCCATTAATTACGCCAAAGGTCACAGGTTAGGCACGCAGCCAGGATCCAAGGAGCAATAATAATGTTGTATGAAGGCGACCT
GTAAGCGAGAGCGAGAGAGCTGGTGTTTTGGTGTGAGTGCGTGGTAGAACAAAGAGGACGAAAAACACGGCTAACGAATTCGCCGCACGACACAC
TCGCCGCATGGCGAATTCAAACGTATCCCAGTGAACGAATGAGAAACAAAAGGATATCTTATTGAAACTGATTAAACTAAAGACTGCCGAATAGT
TATATAAAATCCAAAACCATGTCTGCGGCCGAACTCGAGGCGGAGGCTTCAGCCCAGGAGCAACAATCCCAGCAACAACAACAAAATCAATCACA
AAGCGAGGAGATAAATACAAACACTGCCATCAATGCAAATGCAACCACAACAAATAGCTACAACAATAATTTAGATACGGAAACCCAGCTTCAGA
TGCACCAGGATCCGCAGCAGCAGCAGGAACTCGAGGGCAATAGCAACAATGGCATCACAGGACTCGGCCTCAGTCTGATGAACTCCTCACCGCCG
CCGCACAGCTACCGACATTCGCGGGCCTATCGCCACTTCAAGAATCCGCCACAGCCCCACATGTGCATCCGCACCACCACGGAGGCGGGCGAGGA
GCTCTTCATCAATGTCCTCAGCTGGACGCGCATTGTGATACCGCAGGAGCCCAGCGATCCCATTCCCCTTTACGGAGGCATGCGGGTAAGATTCC
TTAGATTAAGTGTCCTCAAACATTCACGTCGGTGTTTCCTTTATTAGTTATTTATGTTAATGTTCTTATTCATTAAGGTACCGCCTGGCAGCCCA
CGCAGTCCTCCCATTGTCTTTGCCGTAATGGCCAATCCGGAGGTGCTCAAAGACTCCGGACGTCACAGCAAAGATCCTGAGGAGCGACGAGCTAT
GGTGGAGCTGATGTGCGACTTTGTGGAGGCTATGAATCCAGGCGTGAAATTAGTCAGGTATATAATAACACTATTAGTTTACTGCCCGATTAAAA
ACAAGAATAAAAATATATGTAATACATCTCCAGAAACGCCGTAATACTCAAGGATCGCGATATCTCCGGCGAGCTGAAGGATGTCTGGAATGCCG
TTCAGGCGCAGCGCGATCGCGAGAGGGAGGAGCAGATGATGCAGCAGCGCCAGCAGCAGCACTACCAGAACATCACCACGCAACAGATGTTTCCC
AAATCGCCGGATGCATCGCGGGCAGCTAGTGCTGGTGCTGCAGTGAACGAGGCCAGCTCGCCGCCGGCTCACTTGTCTGAGCCGCTGCTGGTAGA
GCAGGGAAATGGCAATGGCAATGGCATCACCCTGGCCGTGTTTGCCCAGCAGCTGGACAACAAAGTGGCCAGCGAGCAGGGTGAGCAGCAGGAGC
AATCGCCAGTTTCGGAGGATGCTTGCGTGGATCAAACGGATGCAGGCAGCTCGCTGAATGGATCAACAACTGTGCTGGACAATCAGCCGGTGGCA
GTGGAGAACGAACCAGAAGTAAAGGTTGCACCACCGGCAGCCACAAATGGTGCTAGCACTCCCACACCCAGCCACGCAACACCCACAGTAACAGC
CACAGCCACATCATCGCCCAGTCCAACTCCAACTCCCGTTGTTGCTCCCGTCGTTACAGCAACTCCTCCACCTGCTGCTCCCGCAAAGAAGGAGA
AACTGGGCGGCTTCCTGCCCAACGGCTGCATCTTCCCGCGCTTCAAGAACAACAAGCACAAGGACAAGGACAATAGTCACAAGGAGGGCAAGAGC
AAAGAGAAGACCCTGCTGAATGCGCTGAAAAAGAGCAAAGAGAAGAAGGTGGCGCCCAGTGAACAGCCGACAGAAAAAGCCGCCGCCTCGGACAA
CGGAACAACGCAGTACGAGAAGAACTGCATCAACAATCTGGAGTGCGAGGTGCAGAAGCTGGACTTGAACAGCGGCACCAATGGCGACAATAGCA
TGTTCATCAAGCTGAAAGTTTCGCCGGCCAATGCCACAGCAGCGGCAGCGGCGGCCAAGTAGAGATAATCCTGAATTTACACACAAAAAAAAAAT
AAATAAAATCTCGTAGGTAAGTGGGAAGTTAGGACGATAGAGAGCCAGAGGAGGCGGCACTCTACCAGTGAACAGTGTCACTGTGTCAGCACTTA
GGGCTTAGAGTCGTGGATAGAGTCGTGTAGCATATACAAGATTTATATATACAGATATATATACAAGCATTCACACACCCGTTTTTACACCGTTG
GTCAATTTTTTGGATAGCCACTCAGAACCAGGACTAGATGAACTAACAGTTGTGCCATGCTCCAGCTCATAGACATTTATAGACGACAGCGCTTC TCCCAGGATCTTCCCCGGCATTTAACTGACAGAATGATAAACGTATTTACATAGTTCAATATATGTATGATTCGCATACAGTTTGCCTTATATAC
AACAAGCCCGAGAGAGCGACAAGAACCTAGCAAGAACCAGTTGATAAACACGAGAATAAATGTATTTAAAAACATAATCGTCGAATGAAACTCAT
GCGCCAAATGAACTTACCAGACTAACTACTAGCTCCATTCCCAAATTGTCACATCATCTCATCGTGAACCATACACCCACCAGGCATTTGCCCAT
CGATTCATCCATCCATCCATCCATCCATCCATCCATCCATCCATATCCATATCCATATCCGTGCAAAAGTATTAAGAAACTTCGCAGATCCAAGA
ACCCTAACCCTGGATCGATTGATCTCCACGCTTTGAAGTTGAGGGGCAGTGAAAACAGCGGAGGGAGTTTAAAGCCGGCTCTTTAGTGCCACGA
CTAACTTATGTACCTTAGTATAGCCGAATGCGAAAACAGTATACAGATCCGCAATGTCGCTATTATGATTTATATTTTAAAGTTTAACTTTTAGT
TTCCCCTTTTGGATACCGAAACGGGGAAACTACATTTCATTCTATTTATTTTCCGTTCGTGCTTGTTGTGTTGTAATTGTGTAATACTACTGTTG
GAATTTTTAACTTTTAC
(SEQ ID NO: 406)

Exon: 1001..1293
Exon: 1384..2270
Exon: 2358..2527
Exon: 2599..3577
Start ATG: 1824

Transcript No. : CT13259
TTTTTGTTTATGTTGGGTTGTCGGAAAAATCGGCTGTTTTCCGTGTGTCCGTCTGCCATGAAAAGCTGCTAAAAAGCTAAATATAAAAATCAGC
GCAGCACACACGTTCCGCTGCCTGCATTGTTTGCCCATTCTAATGGGAAATTATGTGAGTGCGAGTCAGGAAAACGCATCGTGTGTGTATATATA
CATATATACATAAGTATGTAACTGCGCCCGTTTGTTTGTGTGTGTTTTTGTGTGCATGGTGCAATGGAAAAGTGATTATTATAAATGAAAATCAG
TGAAATGTTCAACCAACTCCCACTTGTGCGTGTGTAGGAAGGCAGAAGGGTGTTTTGCATTCGTGTGCGTGCCAGATAAAAAGACTTTGAATTTC
TGGAGGATATTAGTGTCAACTGTGTGGGGTATAATACGCCGTAGGCCCTAATATGCAGGCAAGTCCATTAATTACGCCAAAGGTCACAGGTTAGG
CACGCAGCCAGGATCCAAGGAGCAATAATAATGTTGTATGAAGGCGACCTGTAAGCGAGAGCGAGAGAGCTGGTGTTTTGGTGTGAGTGCGTGGT
AGAACAAAGAGGACGAAAAACACGGCTAACGAATTCGCCGCACGACACACTCGCCGCATGGCGAATTCAAACGTATCCCAGTGAACGAATGAGAA
ACAAAAGGATATCTTATTGAAACTGATTAAACTAAAGACTGCCGAATAGTTATATAAAATCCAAAACCATGTCTGCGGCCGAACTCGAGGCGGAG
GCTTCAGCCCAGGAGCAACAATCCCAGCAACAACAACAAAATCAATCACAAAGCGAGGAGATAAATACAAACACTGCCATCAATGCAAATGCAAC
CACAACAAATAGCTACAACAATAATTTAGATACGGAAACCCAGCTTCAGATGCACCAGGATCCGCAGCAGCAGCAGGAACTCGAGGGCAATAGCA
ACAATGGCATCACAGGACTCGGCCTCAGTCTGATGAACTCCTCACCGCCGCCGCACAGCTACCGACATTCGCGGGCCTATCGCCACTTCAAGAAT
CCGCCACAGCCCCACATGTGCATCCGCACCACCACGGAGGCGGGCGAGGAGCTCTTCATCAATGTCCTCAGCTGGACGCGCATTGTGATACCGCA
GGAGCCCAGCGATCCCATTCCCCTTTACGGAGGCATGCGGGTACCGCCTGGCAGCCCACGCAGTCCTCCCATTGTCTTTGCCGTAATGGCCAATC
CGGAGGTGCTCAAAGACTCCGGACGTCACAGCAAAGATCCTGAGGAGCGACGAGCTATGGTGGAGCTGATGTGCGACTTTGTGGAGGCTATGAAT
CCAGGCGTGAAATTAGTCAGAAACGCCGTAATACTCAAGGATCGCGATATCTCCGGCGAGCTGAAGGATGTCTGGAATGCCGTTCAGGCGCAGCG
CGATCGCGAGAGGGAGGAGCAGATGATGCAGCAGCGCCAGCAGCAGCACTACCAGAACATCACCACGCAACAGATGTTTCCCAAATCGCCGGATG
CATCGCGGGCAGCTAGTGCTGGTGCTGCAGTGAACGAGGCCAGCTCGCCGCCGGCTCACTTGTCTGAGCCGCTGCTGGTAGAGCAGGGAAATGGC
AATGGCAATGGCATCACCCTGGCCGTGTTTGCCCAGCAGCTGGACAACAAAGTGGCCAGCGAGCAGGGTGAGCAGCAGGAGCAATCGCCAGTTTC
GGAGGATGCTTGCGTGGATCAAACGGATGCAGGCAGCTCGCTGAATGGATCAACAACTGTGCTGGACAATCAGCCGGTGGCAGTGGAGAACGAAC
CAGAAGTAAAGGTTGCACCACCGGCAGCCACAAATGGTGCTAGCACTCCCACACCCAGCCACGCAACACCCACAGTAACAGCCACAGCCACATCA
TCGCCCAGTCCAACTCCAACTCCCGTTGTTGCTCCCGTCGTTACAGCAACTCCTCCACCTGCTGCTCCCGCAAAGAAGGAGAAACTGGGCGGCTT
CCTGCCCAACGGCTGCATCTTCCCGCGCTTCAAGAACAACAAGCACAAGGACAAGGACAATAGTCACAAGGAGGGCAAGAGCAAAGAGAAGACCC
TGCTGAATGCGCTGAAAAAGAGCAAAGAGAAGAAGGTGGCGCCCAGTGAACAGCCGACAGAAAAAGCCGCCGCCTCGGACAACGGAACAACGCAG
TACGAGAAGAACTGCATCAACAATCTGGAGTGCGAGGTGCAGAAGCTGGACTTGAACAGCGGCACCAATGGCGACAATAGCATGTTCATCAAGCT
GAAAGTTTCGCCGGCCAATGCCACAGCAGCGGCAGCGGCGGCCAAGTAG
(SEQ ID NO: 407)

Start ATG: 734

MSAAELEAEASAQEQQSQQQQQNQSQSEEINTNTAINANATTTNSYNNNLDTETQLQMHQDPQQQQELEGNSNNGITGLGLSLMNSSPPPHSYRH
SRAYRHFKNPPQPHMCIRTTTEAGEELFINVLSWTRIVIPQEPSDPIPLYGGMRVPPGSPRSPPIVFAVMANPEVLKDSGRHSKDPEERRAMVEL
MCDFVEAMNPGVKLVRNAVILKDRDISGELKDVWNAVQAQRDREREEQMMQQRQQQHYQNITTQQMFPKSPDASRAASAGAAVNEASSPPAHLSE
PLLVEQGNGNGNGITLAVFAQQLDNKVASEQGEQQEQSPVSEDACVDQTDAGSSLNGSTTVLDNQPVAVENEPEVKVAPPAATNGASTPTPSHAT
PTVTATATSSPSPTPTPVVAPVVTATPPPAAPAKKEKLGGFLPNGCIFPRFKNNKHKDKDNSHKEGKSKEKTLLNALKKSKEKKVAPSEQPTEKA
AASDNGTTQYEKNCINNLECEVQKLDLNSGTNGDNSMFIKLKVSPANATAAAAAAK*
(SEQ ID NO: 408)

Celera Sequence No. : 142000013384676
CTTTTCACCGAATACCACACAAAGCTGACGACGGGATGTTTCGCCACCCGTACTTCTCCCTTAGGGGTGGTTTCCTGTCACGAGCACAGGGTTGC
TAAATGCGCGGCAAAGGCGGCCGAAAGTCCTGTGCTCGGCTTGAGAGCTCCACTGGCGAAATGTTTGTTTTTATTGATATTAATTTTTCTTCTGC
TTCTCCTCCTCCTTCAGCTGTTTCTCCCTGAGCTTTTCCTCCTTCTTCAGCTGTTTCTCCCTTAGCTTCCGCTCTTTCTCCCGCTTCTTCACGAT
TGCGGGATCATCGCTGTCCTCATTGGGGTCCTTCTCCTCCTTCTTCACCTCTTCATCGGGAATTTGTTCAAGACCCTATAGAGAAAGAAGCTTTA
CACCTGAGGCAGCAAAAAAAAATCTGTAAGGAACTACAGGAAAAACCAAAAACGACCATTTCAACTATCACTTCCGAACTGCACGTTTCGTTTAT
TCACTTTTGCACTTAAGCTTAAACGGAAAACTTTACTTAATTAAAATTAGTTCGTTTTCTCATCCGGTATGGCATCCAGACCCTGCAAGAAGATT
GGTTCGGTTTTTTGTAAATGATTTAAGCTTATAACTCTTCGAATAAGCGTAAAAAAATGGATGGTATGAATTCGTAGGAAATAAAGTAACATTAA
CTACCGCCACCAATGATCAATAAACAATAAAAACGAAATTAACCAAGAAAACTAAGATTTTAAATGCAATTACCTTATAATATAGAAAACTTTAA
AACTAATATTTTATTAGTGAAGAAAGCTAGTTCATAACACCAAAAACAATCTATTTAACATACTTCAGAGAAAAACATAAACAACGAAACCAAAA
TGAGCGTGCATAATAATGAAGTGCGTGCTGTGAGATAACAAAACTGCTGCCAAAAATAGGGTAAAAACGTGATGGTTGGCCTGCCGCACAAAAAT
CAGTTGTAGGCAGGCCAGACTATAGCACAACACTTACGTTCATCTTGTAGGGATTGTCGGTCAGTCGGAAATCGCGCTGGTACATAACTCGGCTG
AAACGCTCGTCCATGTTGCGCCGGAAAGCCTGTTGAGCAAACGATTAGCAAACAATTAGTAACTCCGTAGTGTTCCGTCGAACTCGTTGCGAAAA
GCAGGCGGTTAAATAATGTTTAACAGATTCCGATTGGTGCACAAACAGCTGCGGTTATATAAGAATTTCGGGCTGCTGGGCCAGAAGGCCAGCGT
GGGACTCACATTGCCGATCATCAGCTTGTCCAGGCCGTACATGGCGTATATGGGCACCGAGAGGAGCGTGGTGATGATCACCGCACCAGGTAGGA TTTCGAACCACATATTGTCAATGGAAATAGATTGTTATGATATTTACTGCAAGACGACACCCAGTGTGACCGTGGATAGTCCGTTCCAATATACA
GGTAGCCTTACAAAATATACCAAAAACTTGAATGTTGAACTAGAGGTGGGCCAGTAACGATAAGAAAGTAACGGTGACTGAATTCTATTCTGCTA
CTGCGTTTAGAAAAACGTCAATGTTGATTTGAAAATAGTTTTTGACCAATAGTTGGCTTAAATAATTTGTAAATAGATCTGATATATCTAGTAGA
GCTGATAAATGTACGCAATGTTTATAATCAATTTCAAAGCTCGAAAGTATATAGAAAACAAATTCCAGTGTAAAGCTGCGTGACCGTTTTACGCT
CTATTCGGGTTGGTATTTTTCCCAATGCACTTTTCGTACATCCAGCTGGACCATTTTTTTGCACTCAGATCTCGGTCTTACCAATCCGATTCTTC
ATTGAACAGCTACGAAGGAATTCGCAGAGAGTTCTGAGCGCAGCAATAGCAGCAAGAAGACTACCAACAAAGAGCAGAGCGACAAATCAGCGGAG
AGCAGGATGGCCACCAGCGGTATTGTCGAGTCATTTCCCACGGGCGCACTGGTGCCCAAGGCGGAGACGGGAGTCCTGAACTTTCTGCAGAAGTA
CCCGGAGTACGATGGACGCGACGTCACCATAGCCATCTTCGATTCCGGCGTCGATCCCCGGGCAACGGGACTGGAGGTGAGTTGGCACTTTTTCG
CACTCTCTATACCGGTTACAAAGAACTTGTACAGTTATTCTTCCAATATTTACAATATTTCGTCTTACCTATTCTATTACGATTTAATCCTTCTA
CTGTGTCACGACTGCTTCTTACTCCCGTTTCTCATTATAACCGATCCAATTTCAATCTGCTCCTACGCAACAGACGCTGTGCGATGGAAAGACCG
TTAAAGTAATAGAGCGGTACGACTGTTCCGGATGCGGCGACGTGGACATGAAGAAGAAGGTGACGCCGGACGAGAACGGCAACATTAAGGGCCTG
TCCGGAAACTCGCTCAAGCTGAGTCCGGAGCTGATGGCTCTGAACACAGATCCGGAGAAGGCGGTGCGGGTAGGCCTCAAGAGCTTCAGCGATTT
GTTGCCCTCCAAGGTGCGGAACAACATTGTGGCCCAGGCCAAGCTGAAGCACTGGGACAAGCCGCACAAGACGGCCACTGCAAACGCCAGTCGCA
AGATTGTTGAATTTGAGTCACAAAATCCAGGTGAGCTAAGTGATTGATTACTTGAGGCAAAATTACCAACAACATATGTATCTTTGCAGGAGAAG
CCTCAAAACTGCCCTGGGACAAGAAGATATTGAAAGAGAATCTAGACTTTGAGCTAGAGATGTTGAATAGCTACGAGAAGGTGTACGGCGACATT
AAGACCTCCTACGATTGCATCCTTTTTCCCACGGCCGACGGATGGCTGACAATCGTCGACACCACGGAGCAGGGCGATCTGGATCAGGCTCTGCG
CATTGGCGAGTATTCCCGCACGCACGAGACCCGCAATGTGGACGACTTTCTTTCCATATCGGTAAACGTCCACGACGAGGGCAACGTACTGGAGG
TGGTCGGCATGAGCTCACCCCACGGCACCCACGTATCGTCTATTGCCAGCGGCAACCATAGCTCCCGGGACGTGGATGGCGTGGCGCCGAATGCT
AAGATCGTTTCTATGACCATCGGTGATGGTCGACTTGGGTCTATGGAGACCGGCACGGCACTAGTGCGTGCCATGACTAAGGTGATGGAACTATG
TCGCGATGGCAGACGCATCGATGTGATCAACATGAGCTATGGCGAGCATGCCAATTGGTCAAATTCCGGGTAAGCAAGTGCGAAAGGCCGGCGGA
ACTAATCCCAAAGTTGGTGATGTCTTTTAGTGTGTCTGGGTCAGGGTCTGGGTCGGATGAAATGCGTCGCAGAAGAAAGATGTGTGCGTCTAGGT
AAATTTCATGAGAAATCCAAATATTCACACAGTCCAATCCTCTTGTCTTCGACACGTTCCAGCCGACACACACCTAACTGATAACCATCAAAATT
CATGAAAAAATACCTAATCTATATCTCTAATCTCTTGCAGCCGCATTGGGGAGCTCATGAACGAGGTTGTCAACAAGTATGGCGTGGTGTGGGTG
GCATCGGCCGGCAACCATGGTCCGGCACTTTGTACTGTGGAACTCCGCCGGACATCAGCCAGCCCAGTTTGATCGGCGTGGGCGCGTACGTATC
ACCCCAAATGATGGAGGCCGAGTATGCGATGCGAGAAAAGCTGCCCGGGAACGTGTACACCTGGACATCGCGAGATCCCTGCATCGACGGAGGTC
AAGGCGTTACCGTATGCGCTCCGGGCGGAGCCATTGCGTCCGTGCCACAGTTTACTATGAGCAAGTCCCAGCTGATGAACGGTACCAGCATGGCG
GCACCTCACGTCGCCGGCGCAGTGGCGCTGCTCATCTCCGGTCTGAAGCAACAGAACATCGAGTATTCGCCGTACAGTATTAAGCGAGCGATCAG
CGTCACTGCCACCAAACTGGGCTATGTAGATCCCTTTGCTCAGGGCCATGGCTTGCTCAATGTCGAGAAGGCATTCGAGCATTTGACGGAGCACC
GCCAGTCCAAGGATAATATGCTCAGGTGAGTGCTGTGGAACGCCAGATCTCAGGATCTCTAAACAAAAAACGATTAAATTTCGCGTTCGCATTCA
CACTAGCTGAGTAAGGGCTAACTTGTTTTATAATTTAGTAGGTATATCGTTAAGATGACCGAATAGTAAACAATTGTCAAAGCAATCTTGTAAAA
TTCCAACCAAATAATAAATTTCTTTCGTTTTAATCTTATAGGTTCTCCGTGCGCGTGGGCAACAACGCAGACAAGGGCATTCATTTGCGTCAGGG
CGTGCAGCGTAACTCCATCGATTACAACGTTTATATAGAGCCCATCTTCTACAATGACAAGGAGGCGGGTGAGTAGAGACTATAGAGACCCAATT
CCAGCTCTTACCGTTCCAATTTTACAGATCCCAAGGACAAGTTTAACTTCAATGTACGGCTAAATCTGATTGCCTCGCAGCCGTGGGTGCAGTGT
GGAGCTTTCTTGGATCTCAGCTATGGCACCCGCTCCATTGCCGTGCGCGTCGATCCCACTGGACTCCAGCCAGGCGTTCACAGCGCTGTGTAAGG
GACTCTTGAGCCAAAAACGCTTCCCCTTCTAATCGCATTTATAAAAATTTATCCAGGATTCGGGCTTATGACACTGACTGCGTACAGAAGGGTTC
TCTCTTTGAGATTCCTGTCACGGTGGTGCAGCCCCATGTGCTGGAGTCGGATCAGAACACGCCCGTCTTCGAACCCGCCTCTTCCAAGGGAGACA
ACAGCGTGGAGTTTCAGCCAAACACCATTCAAAGAGACTTCATCCTGGTGCCAGAACGTGCTACTTGGGCGGGTGAGTGTTATTCCCTGAAATAT
GTTCACAAAGTGAGTCACACTTCATCCTTATGCAGAGTTGCGTATGCGTATAACCGATCCCAATCGTGGCGAGGACATTGGAAAGTTCTTTGTAC
ACACGAACCAACTTCTTCCCAAGCAATCCTGTCGTAAGCTTGAGACCATGAAGATCGTATCGGTTGGCTCGGAAAACGAATCTATAATGGCTTTT
AAAGTTAAGGTTGGTAAATCGATTGAAACCTTTCCAAGTCATTATACTGATTAAAACCCACATTTGTATGACAGTCTGGCAGGATTCTGGAGCTA
TGCATTGCCAAGTACTGGTCCAACTACGGCCAGAGTCACCTGAAGTACAGCTTGCGTTTCCGTGGCGTGGAAGCGCACAATCCCAATGCCTGTGA
GTCATTTGTAAAATGGTAATAGCTTTTGTTGAACTAAAGAAACCATTGTTTTGTAGACGTCATGCATGCGGGCAGGGGAATTCATAAGCTGGAGA
TTGAGGCCCTGGTTGCCGAGGATGTGCAGCCCCAGCTACAGCTAAAGAATGCCGAAGTGGTGCTAAAACCGACCGAGGCCAAGATCTCGCCGCTA
AGCGCCACACGAGACGTCATCCCAGATGGACGTCAGGTGTATCAGAACCTGCTGGCCTTTAACTTGAACGTGGCCAAGGCCGCAGATGTGTCGAT
ATACGCACCGATCTTTAACGACTTGTTGTATGAAGCGGAGTTTGAGTCACAGATGTGGATGCTTTTTGATGCAAACAAGGCCCTGGTGGCCACCG
GCGATGCTCACTCCCACACTTCCTTCACAAAGCTCGATAAGGGCGAATACACAATCAGACTGCAGGTGCTCACGAGAAGCGCGACCTGCTGGAG
AAGATCTCGGAGGCAAATCTGGTGGCCTCATTCAAGCTGACTAGCCCCCTCACCCTTGATTTCTATGAGAACTACAATCAGTGCATAGTGGGAGG
TCGTAAATACGTCTCGAGTCCGCTAAGGCTGTCCACTCGGGTGCTTTATATCGCTCCTATTACCCAAGAGCGACTTACCAAGGCCAATCTGCCCG
CTCAATGCGCCTGGCTGAGCGGCAATCTGGTATTCCCGCAAGATGAGGTCGGACGGCGAGTGGCTCAGCATCCATTTACTTACATCCTCAATCCC
GCTGAGAAAAAGTCACACACGAATGGCTCGAGCAACGGTTCCAGCGCTGCAGGATCCACAGCTACGGCAGCTGCTGTCACCACTGCTAATGGCGC
AAAACCGAAAGCTCCGGCGACTCCACAAGCGGCCACCTCAGTGACCAATCCTGCGGCCGGCGATGGAATTTCTGTTCAGAACGACCCGCCTGTGG
ACAGCAGTGGGAGTCCCGCCTCACCCAAAAAGGGCAAGGCCAATGCCGACGATTATGCCGAAAGTTTTCGCGACTTTCAATGTTCGCAGATTGTC
AAGTGTGGTAGGATTTTAAAAAATAGAGCACTATTTTCTGATTAGTTTAACATACGATCCTCTTACAGAACTGGAAATGGCAGAGAAAATCTATA
ATGATGTAGTCGCTGCCCATCCCAAGCATTTGCAGGCAAACCTGCTACTTATCCAGAACATCGAGTCCAATCAGCTGAAGTCGCAACTGCCGCTG
ACTTTCGTCAATGCTCAAAAGACATCGCCACCAGAGGCAGGCGAGAGCGCCGACAAGCAAAAGGAGGATCAAAAGAAAGTACGAAGCGCCCTGGA
GCGAATTGTTAAGCTGGCCGACAAGGTGATCCAGGAGACCGATTCCGAGGCACTGCTCTCCTACTACGGTCTGAAGAACGACACTCGTGCCGATG
CAGCCAAGATAAAGACGTATGTTGTTTAATTGGGTTAGGCATTCCAGTCAGAAATGAATTCTTTTCTTCTTTAGCAACATGGACAAACAGAAAAA
CACTCTCATTGAGGCGCTAAGCAAGAAGGGCATTGCTGTGGCAAAGCTGGCTGTATTAGACGACTGTATCAAGGATAGCCTGGCTGAGATCAACG
AGCTGTATACCGAGATTATCAAGTTCGTGGACGCCAACGACTCCAAGGCCATCCAGTTCGCTCTGTGGCACGCCTATGCCCATGGCCACTACGGT
CGCATGTACAAGTATGTGGTTAAGCTAATCGAGGAGAAGCGAACCCGCGATCACTTCGTGGAGCTGGCCGCCATCAACGGCGCCCTGGGTCACGA
GCACATCCGTACTGTCATCAACCGTATGATGATCACTGCCTTTCCCAGCAGCTTCCGTTTGTTCTGAGCACTTTCCGACAGAATACGCAACAAAT
ATTCACGCTTCGAAGCGATCATTGTTTTGTATAACTAATGTAATCCATATGTATATGAATAAATGCTATTAACTGAAATTCAATATTGTTAGTCA
TTTCATTAAAACTAAATTATTAAATTTAACTAAGATTAATGATCGATTGATTTTCCGGTAAGAAAAAAGGAAATGAGAATTGAACAATTTTATTA
AGGAGTGAATTTTAAAATCCCGCCAAACCGTTACGATGTTGAACATAGCATTTTCCAGCACTGGTGCCTGGTAATTGAGCCGACTCCGCGTGACG
GTCATACTTATTGCAGCAAAAAAACAAAAAACAATGCAGACGCACACGAGAGTGTAAAATGGGTAAGTTTGACAGAAAAAGAGCTGTTTAAAACT
GGAAAATTGTCTTATTGTGCGGCTAATAATATGAACTCGTGGGTGACATGTGAAAAGTGCAAGAATAACGACTTCCAACTGCAGTTTCCTGCTAC
GTAGTTGCGATGAGGCTTCCGCCTGCGTGTGCAAGTGTGTGTGTGCGTGTATGTATTGGCCGATCGATTTTATTTTGCATATTCAAGGACAGCGA
AGTCCTGCGGGAAAGTGCGGCCGGGATTAGAGGAAACGGGAATCGGGGCGGCGCCGGAAACTAGAGCGAGCTCCCGTTCCCAAGCCGAATGACTC
AGTAATCGCCCATGAAATCCCCGGAACGATATCAGCTTACAATCTGTGTACATGCATTTGTTGCTTAAGTTCCACCCCGCATCCCAGTCCCGCTT
TCACTCCCACTCCAACCTACCCCTTGCCCACCCACTGTGTCAACTCCGGAGAGGACAAACAATGGCCCCTTGCAGCCGGATGACAAATGCGGGTG
CAGCGACATCAAGAAAGAACCTTCGAATTTGGTGACGCGACTATCAGATACTCTTACTTTCTTCGTTTGCCTATGAAGTTCATTATCATTTTTGT

FIGURE SHEET 227

GTCATTAAAGCGATTTATAATTAGATCAATCAGACTAATTCAACGTATTGTGACTTATAAATCAGTATAACCTATGAAAGTTTTTTAACCACCC
ATTAATTTCTGGTTAGGATTCAATTGAAGT
(SEQ ID NO: 409)

Exon: 1001..1324
Exon: 1815..2071
Exon: 2259..2595
Exon: 2655..3204
Exon: 3461..4015
Exon: 4222..4343
Exon: 4398..4554
Exon: 4617..4822
Exon: 4881..5044
Exon: 5110..5221
Exon: 5282..6277
Exon: 6339..6666
Exon: 6725..7200
Start ATG: 1907

Transcript No. : CT13277
GGATTGTCGGTCAGTCGGAAATCGCGCTGGTACATAACTCGGCTGAAACGCTCGTCCATGTTGCGCCGGAAAGCCTGTTGAGCAAACGATTAGCA
AACAATTAGTAACTCCGTAGTGTTCCGTCGAACTCGTTGCGAAAAGCAGGCGGTTAAATAATGTTTAACAGATTCCGATTGGTGCACAAACAGCT
GCGGTTATATAAGAATTTCGGGCTGCTGGGCCAGAAGGCCAGCGTGGGACTCACATTGCCGATCATCAGCTTGTCCAGGCCGTACATGGCGTATA
TGGGCACCGAGAGGAGCGTGGTGATGATCACCGCACCAGCTACGAAGGAATTCGCAGAGAGTTCTGAGCGCAGCAATAGCAGCAAGAAGACTACC
AACAAAGAGCAGAGCGACAAATCAGCGGAGAGCAGGATGGCCACCAGCGGTATTGTCGAGTCATTTCCCACGGGCGCACTGGTGCCCAAGGCGGA
GACGGGAGTCCTGAACTTTCTGCAGAAGTACCCGGAGTACGATGGACGCGACGTCACCATAGCCATCTTCGATTCCGGCGTCGATCCCCGGGCAA
CGGGACTGGAGACGCTGTGCGATGGAAAGACCGTTAAAGTAATAGAGCGGTACGACTGTTCCGGATGCGGCGACGTGGACATGAAGAAGAAGGTG
ACGCCGGACGAGAACGGCAACATTAAGGGCCTGTCCGGAAACTCGCTCAAGCTGAGTCCGGAGCTGATGGCTCTGAACACAGATCCGGAGAAGGC
GGTGCGGGTAGGCCTCAAGAGCTTCAGCGATTTGTTGCCCTCCAAGGTGCGGAACAACATTGTGGCCCAGGCCAAGCTGAAGCACTGGGACAAGC
CGCACAAGACGGCCACTGCAAACGCCAGTCGCAAGATTGTTGAATTTGAGTCACAAAATCCAGGAGAAGCCTCAAAACTGCCCTGGGACAAGAAG
ATATTGAAAGAGAATCTAGACTTTGAGCTAGAGATGTTGAATAGCTACGAGAAGGTGTACGGCGACATTAAGACCTCCTACGATTGCATCCTTTT
TCCCACGGCCGACGGATGGCTGACAATCGTCGACACCACGGAGCAGGGCGATCTGGATCAGGCTCTGCGCATTGGCGAGTATTCCCGCACGCACG
AGACCCGCAATGTGGACGACTTTCTTTCCATATCGGTAAACGTCCACGACGAGGGCAACGTACTGGAGGTGGTCGGCATGAGCTCACCCCACGGC
ACCCACGTATCGTCTATTGCCAGCGGCAACCATAGCTCCCGGGACGTGGATGGCGTGGCGCCGAATGCTAAGATCGTTTCTATGACCATCGGTGA
TGGTCGACTTGGGTCTATGGAGACCGGCACGGCACTAGTGCGTGCCATGACTAAGGTGATGGAACTATGTCGCGATGGCAGACGCATCGATGTGA
TCAACATGAGCTATGGCGAGCATGCCAATTGGTCAAATTCCGGCCGCATTGGGGAGCTCATGAACGAGGTTGTCAACAAGTATGGCGTGGTGTGG
GTGGCATCGGCCGGCAACCATGGTCCGGCACTTTGTACTGTGGGAACTCCGCCGGACATCAGCCAGCCCAGTTTGATCGGCGTGGGCGCGTACGT
ATCACCCCAAATGATGGAGGCCGAGTATGCGATGCGAGAAAAGCTGCCCGGGAACGTGTACACCTGGACATCGCGAGATCCCTGCATCGACGGAG
GTCAAGGCGTTACCGTATGCGCTCCGGGCGGAGCCATTGCGTCCGTGCCACAGTTTACTATGAGCAAGTCCCAGCTGATGAACGGTACCAGCATG
GCGGCACCTCACGTCGCCGGCGCAGTGGCGCTGCTCATCTCCGGTCTGAAGCAACAGAACATCGAGTATTCGCCGTACAGTATTAAGCGAGCGAT
CAGCGTCACTGCCACCAAACTGGGCTATGTAGATCCCTTTGCTCAGGGCCATGGCTTGCTCAATGTCGAGAAGGCATTCGAGCATTTGACGGAGC
ACCGCCAGTCCAAGGATAATATGCTCAGGTTCTCCGTGCGCGTGGGCAACAACGCAGACAAGGGCATTCATTTGCGTCAGGGCGTGCAGCGTAAC
TCCATCGATTACAACGTTTATATAGAGCCCATCTTCTACAATGACAAGGAGGCGGATCCCAAGGACAAGTTTAACTTCAATGTACGGCTAAATCT
GATTGCCTCGCAGCCGTGGGTGCAGTGTGGAGCTTTCTTGGATCTCAGCTATGGCACCCGCTCCATTGCCGTGCGCGTCGATCCCACTGGACTCC
AGCCAGGCGTTCACAGCGCTGTGATTCGGGCTTATGACACTGACTGCGTACAGAAGGGTTCTCTCTTTGAGATTCCTGTCACGGTGGTGCAGCCC
CATGTGCTGGAGTCGGATCAGAACACGCCCGTCTTCGAACCCGCCTCTTCCAAGGGAGACAACAGCGTGGAGTTTCAGCCAAACACCATTCAAAG
AGACTTCATCCTGGTGCCAGAACGTGCTACTTGGGCGGAGTTGCGTATGCGTATAACCGATCCCAATCGTGGCGAGGACATTGGAAAGTTCTTTG
TACACACGAACCAACTTCTTCCCAAGCAATCCTGTCGTAAGCTTGAGACCATGAAGATCGTATCGGTTGGCTCGGAAAACGAATCTATAATGGCT
TTTAAAGTTAAGTCTGGCAGGATTCTGGAGCTATGCATTGCCAAGTACTGGTCCAACTACGGCCAGAGTCACCTGAAGTACAGCTTGCGTTTCCG
TGGCGTGGAAGCGCACAATCCCAATGCCTACGTCATGCATGCGGGCAGGGGAATTCATAAGCTGGAGATTGAGGCCCTGGTTGCCGAGGATGTGC
AGCCCCAGCTACAGCTAAAGAATGCCGAAGTGGTGCTAAAACCGACCGAGGCCAAGATCTCGCCGCTAAGCGCCACACGAGACGTCATCCCAGAT
GGACGTCAGGTGTATCAGAACCTGCTGGCCTTTAACTTGAACGTGGCCAAGGCCGCAGATGTGTCGATATACGCACCGATCTTTAACGACTTGTT
GTATGAAGCGGAGTTTGAGTCACAGATGTGGATGCTTTTTGATGCAAACAAGGCCCTGGTGGCCACCGGCGATGCTCACTCCCACACTTCCTTCA
CAAAGCTCGATAAGGGCGAATACACAATCAGACTGCAGGTGCGTCACGAGAAGCGCGACCTGCTGGAGAAGATCTCGGAGGCAAATCTGGTGGCC
TCATTCAAGCTGACTAGCCCCCTCACCCTTGATTTCTATGAGAACTACAATCAGTGCATAGTGGGAGGTCGTAAATACGTCTCGAGTCCGCTAAG
GCTGTCCACTCGGGTGCTTTATATCGCTCCTATTACCCAAGAGCGACTTACCAAGGCCAATCTGCCCGCTCAATGCGCCTGGCTGAGCGGCAATC
TGGTATTCCCGCAAGATGAGGTCGGACGGCGAGTGGCTCAGCATCCATTTACTTACATCCTCAATCCCGCTGAGAAAAAGTCACACACGAATGGC
TCGAGCAACGGTTCCAGCGCTGCAGGATCCACAGCTACGGCAGCTGCTGTCACCACTGCTAATGGCGCAAAACCGAAAGCTCCGGCGACTCCACA
AGCGGCCACCTCAGTGACCAATCCTGCGGCCGGCGATGGAATTTCTGTTCAGAACGACCCGCCTGTGGACAGCAGTGGGAGTCCCGCCTCACCCA
AAAAGGGCAAGGCCAATGCCGACGATTATGCCGAAAGTTTTCGCGACTTTCAATGTTCGCAGATTGTCAAGTGTGAACTGGAAATGGCAGAGAAA
ATCTATAATGATGTAGTCGCTGCCCATCCCAAGCATTTGCAGGCAAACCTGCTACTTATCCAGAACATCGAGTCCAATCAGCTGAAGTCGCAACT
GCCGCTGACTTTCGTCAATGCTCAAAAGACATCGCCACCAGAGGCAGGCGAGAGCGCCGACAAGCAAAAGGAGGATCAAAAGAAAGTACGAAGCG
CCCTGGAGCGAATTGTTAAGCTGGCCGACAAGGTGATCCAGGAGACCGATTCCGAGGCACTGCTCTCCTACTACGGTCTGAAGAACGACACTCGT
GCCGATGCAGCCAAGATAAAGACCAACATGGACAAACAGAAAAACACTCTCATTGAGGCGCTAAGCAAGAAGGGCATTGCTGTGGCAAAGCTGGC
TGTATTAGACGACTGTATCAAGGATAGCCTGGCTGAGATCAACGAGCTGTATACCGAGATTATCAAGTTCGTGGACGCCAACGACTCCAAGGCCA
TCCAGTTCGCTCTGTGGCACGCCTATGCCCATGGCCACTACGGTCGCATGTACAAGTATGTGGTTAAGCTAATCGAGGAGAAGCGAACCCGCGAT
CACTTCGTGGAGCTGGCCGCCATCAACGGCGCCCTGGGTCACGAGCACATCCGTACTGTCATCAACCGTATGATGATCACTGCCTTTCCCAGCAG
CTTCCGTTTGTTCTGAGCACTTTCCGACAGAATACGCAACAAATATTCACGCTTCGAAGCGATCATTGTTTTGTATAACTAATGTAATCCATATG
TATATGAATAAATGCTATTAACTG
(SEQ ID NO: 410)

FIGURE SHEET 228

Start ATG: 417

MATSGIVESFPTGALVPKAETGVLNFLQKYPEYDGRDVTIAIFDSGVDPRATGLETLCDGKTVKVIERYDCSGCGDVDMKKKVTPDENGNIKGLS
GNSLKLSPELMALNTDPEKAVRVGLKSFSDLLPSKVRNNIVAQAKLKHWDKPHKTATANASRKIVEFESQNPGEASKLPWDKKILKENLDFELEM
LNSYEKVYGDIKTSYDCILFPTADGWLTIVDTTEQGDLDQALRIGEYSRTHETRNVDDFLSISVNVHDEGNVLEVVGMSSPHGTHVSSIASGNHS
SRDVDGVAPNAKIVSMTIGDGRLGSMETGTALVRAMTKVMELCRDGRRIDVINMSYGEHANWSNSGRIGELMNEVVNKYGVVWVASAGNHGPALC
TVGTPPDISQPSLIGVGAYVSPQMMEAEYAMREKLPGNVYTWTSRDPCIDGGQGVTVCAPGGAIASVPQFTMSKSQLMNGTSMAAPHVAGAVALL
ISGLKQQNIEYSPYSIKRAISVTATKLGYVDPFAQGHGLLNVEKAFEHLTEHRQSKDNMLRFSVRVGNNADKGIHLRQGVQRNSIDYNVYIEPIF
YNDKEADPKDKFNFNVRLNLIASQPWVQCGAFLDLSYGTRSIAVRVDPTGLQPGVHSAVIRAYDTDCVQKGSLFEIPVTVVQPHVLESDQNTPVF
EPASSKGDNSVEFQPNTIQRDFILVPERATWAELRMRITDPNRGEDIGKFFVHTNQLLPKQSCRKLETMKIVSVGSENESIMAFKVKSGRILELC
IAKYWSNYGQSHLKYSLRFRGVEAHNPNAYVMHAGRGIHKLEIEALVAEDVQPQLQLKNAEVVLKPTEAKISPLSATRDVIPDGRQVYQNLLAFN
LNVAKAADVSIYAPIFNDLLYEAEFESQMWMLFDANKALVATGDAHSHTSFTKLDKGEYTIRLQVRHEKRDLLEKISEANLVASFKLTSPLTLDF
YENYNQCIVGGRKYVSSPLRLSTRVLYIAPITQERLTKANLPAQCAWLSGNLVFPQDEVGRRVAQHPFTYILNPAEKKSHTNGSSNGSSAAGSTA
TAAAVTTANGAKPKAPATPQAATSVTNPAAGDGISVQNDPPVDSSGSPASPKKGKANADDYAESFRDFQCSQIVKCELEMAEKIYNDVVAAHPKH
LQANLLLIQNIESNQLKSQLPLTFVNAQKTSPPEAGESADKQKEDQKKVRSALERIVKLADKVIQETDSEALLSYYGLKNDTRADAAKIKTNMDK
QKNTLIEALSKKGIAVAKLAVLDDCIKDSLAEINELYTEIIKFVDANDSKAIQFALWHAYAHGHYGRMYKYVVKLIEEKRTRDHFVELAAINGAL
GHEHIRTVINRMMITAFPSSFRLF*
(SEQ ID NO: 411)

Name: tripeptidyl-peptidase II
Classification: peptidase
Gene Symbol: TppII
FlyBase ID: FBgn0020370

Celera Sequence No. : 142000013385212
ACAAACTATATTTCTTAATGTCTCGACTCGCTAGTTCAGTCTGAAATAGGGCTGCTGGTATCTGCCTATGGGCATCCGATCCTTGGTCCTCAGTC
GTCGCACTGCCTCTCGTATGAATTTGGGCTGCAGGGCACCGGATTCACCTTGGGCCTCCATCACGTCGAGGGCTTCCTCCACAACCTCGCCGACG
AAGACCTTCGCAATGCCGGACATGGCTATCACAACATTCTGGGACACGGAACAGCCGGTGATAGTTTGCATTAGACGCTTGACGGCGGCCTTGGG
AAAGGCAGAGCGACGATACATTTCGTAGCGATCCAGCTGTTCTTCCGTAAAGTTGGAAACGAGAACCCTGGAGTGGAATAAAATAGTTTTTATAG
GATTACCCCTTCGAATCGCTTTAAGCTAACTTACTGCATTCGTTCGCGCTCCTCCTCCTCCAGTTCCTTCTTCGTCTTGAGCTTTTTGTGCGCCG
GCTCGCCAGAGTCACCATCTCCGTCCGTGTTCTTGTTGTCGTTGTCCCCATCCGCATCCTTGCCATCACGATCCGCATCGTTTCCCGGATCCGAG
GTGTCGCTGTCCTTCCGCTCGCCGGAGGCCGACTGGAAGAATTTCAGGTCGACATCGTCGCCGTCGCTTAGGGAGTTGCTTTTTTGCTGCGTGGG
AAAGAGGATTTCGTCCATTTAAATGAAATTTGAAAAGCACCAGCGAATAATAAACAAAATCAACCAGGGATGGAGTTGCACCATATTCGCTTTTT
GCAACACTCAAAAGTTCCGCACCACATAATAGATGAATATAATTCAAAATATCGGATTAAATATATTAAAGGTATATCATAGTTGTTTATAAGGT
GGCTTTGAGATTTTAATAAATAATAAATATATAAATATACAATATTCGATAAACTTTTATTTTTGTAGTGTTTTTTTTTCTTCAAATTAGTGCT
CAAAGTCAAATTATGTAAATTTCAAATTGAACATTCACTGGTTCCGATAGTCCACAGCACGTTTTACAGCACTGGCCTCTGACACCTCGTGTTTT
TGTTCTTTTCTCCGCATCGCCATCGCCAGGCAAGAGTGCGCGCTACATTTTCGTTTATTTCATCGTTCAGCCAGCAACCAAGGCACTGCGAAATG
TCTGCAACCGAGACTCTGAATGTGGAGGCGGCAACGCCCGAGATCGGCGAGGAGGTCAAGAAACAAAAGAAGCCCAAGCCGAACAACAAGAAGCT
CCGCCAAGGTGAGTGACCTCATGCGAGCAGTGCACTGTGGTAATTGCATTTGCACGACCCTCTCCGCCTCAACCACCCACCACCCACTGAACTAA
CCACTTGCCCACAGAAGCGGCAGCCAAAATAGCCTCCGGAGAAGGCGGCGACGAGGAGCTGACCACAAACGGAGATGCCAAACCGGCAACACCGG
CCGCTCAGCCGGCAAAGAAGAAGGGGAACAAGGGCAAGAAAAGCGGTCAGACTGATCCGCCCACCATACCCATTGCTAAGCTTTATCCGGACGGC
AACTTCCCCGAGGGCGAGATCGTGGAGCACCCCACGCCCAAGGATATGCCCGACGATCGTACGGCCAAGGACCGATTCACATCGGAGGAGAAGCG
TGCTCTGGACCGTATCAACACGGACATCTACCAGGAATTGCGCCAGGCGGCTGAGGCCCATCGTCAGACGCGTCAGTATATGCAGCGCTACATTA
AGCCGGGCATGACCATGATCCAAATCTGCGAGGAGCTGGAGAACACTGCTCGGCGCCTGATCGGCGAAAATGGTCTGGAGGCTGGTTTGGCCTTC
CCGACTGGTTGCTCTCTTAACCATTGCGCCGCCCACTACACGCCCAATGCCGGAGACCCCACTGTACTGCAGTACGACGATGTGTGCAAGATTGA
TTTTGGTACCCATATCAAGGGGCGGATCATTGATTGCGCCTTCACCCTGACCTTCAACAACAAGTACGACAAGTTGCTGCAGGCCGTCAAGGAGG
CCACCAACACGGGCATCAGAGAGGCGGGCATCGATGTGCGCCTATGCGACATCGGCGCCGCTATCCAGGAGGTCATGGAGTCGTACGAGATCGAG
TTGGACGGCAAAACATATCCCATCAAGGCGATTCGCAACTTAAATGGACACTCCATCAGCCCGTACCGTAAGCAAAAATCTATTTATTATAAATA
TTTTAAATATGCTTATGCTTTCCTTAATATTTTTTGTTTAAATTTATTGTGATTTGTGCAAACACTTAATGAAGTCTAAAATTAAATTCTCAGGC
ATTCATGCTGGAAAAACGGTGCCCATTGTGAAAGGCGGAGAGTCCACTCGCATGGAGGAGGATGAATTCTACGCCATTGAGACGTTCGGCTCGAC
GGGTCGCGGTCTGGTCCATGACGATATGGACTGCTCGCATTACATGAAGAACTTTGATCTGCCGTTTGTGCCGCTGCGCCTGCAGTCATCCAAGC
AGCTGCTTGGCACCATCAACAAAAACTTCGGCACCCTGGCCTTCTGCAAGCGTTGGCTGGACCGCGCCGGTGCCACGAAGTACCAGATGGCTCTC
AAGGATCTGTGCGACAAGGGCATTGTGGAGGCTTATCCGCCGTTGTGCGACATTAAGGGCTGCTACACGGCTCAGTACGAACACACAATTATGCT
GCGACCCACCTGCAAAGAAGTCGTTTCCCGTGGCGACGACTACTAGTGGGATGAGGAACTGGACAGTGACCGATTTTCGGCGATGTATGGCTTGC
ATTATATACGGTTTTTGATATAAGTTCATTCTATTGTTGATTTTTTGTGAGCATGCGCCAACCGAATTATATATACAATGTATTATGCTCAGAAT
ATAAGCGGAGTGAGATTATTTTCGAAGTTGTTCTTGTCTTGGCAGATTGCTACGGAGCTCACGCCAGTAAAGTGAATAGTTGTGATTGATAGGCT
CCTTATCTAATAAGAATGACCTGTATATGTAGACAAATCCTTTGCCTGTAAGATAGTACAGGATCTCTATGTAACTGACTATGCTGAAACCGTAC
ATAAGCGAGAGAATGCCTCCAAAGCGATCTAAAGGGTTAGTTAATATTTTTTAACTACTCGTCTTAGTTATTTACTGTACTCACTTAGCAGAACA
ACCCAACTGCTAACCATTTGAGATTTTGTGGCTTGGGCAAAGCGCAGTTTAAAGAAAAGCTTTATAATGGCTAATGGTCGCTCGTTGGTCAATCC
CTTTCTAAAATATTCGATATTCATTATTTATCAAAGAAATTGTGGTACATCACTTACAGCAACCCGGTAAAGTAACCACTGCTATTATAAGTCCG
TCTCAAAGGAGCCACGTTGGTGGTGATACTCATGCTAACTCCGTTGCAGGTGGGCAAACAGTGCTCGCACTGCCTCTGGACCAAGTTCTCTTCCT
TGTTCTGCAGGTAGGCGAAGTCACTGTAGCCATACCAAATGCTCTTCCATCTCATTAGGCATGGAAGATCGGGAAGCATACAATAGTCGAGATCC
ATGGAACTGCCGGTCAAGGGCGGAGATACACAGCCGCAATGATCGATCATGCTCTTCATGCGGCATACCAGAAGGCACTCGTCCAGGGAGTAGTA
CGATCTGTAGGAACGATGTTCACCAGGTATTCCGCGGATTGGTTTCTAATTACTTACTGGTTCAGCAACCGCATGCCTTCTTCGGGATAGTAACA
ACGTCGTATATGTGGCGGGACTCCGCGAACCCCATCGCCTGAACTAAAAAACATCGGCTGGATGGGAATCTCCACTATGCTGTAGTGATCCACCA
GCACCTCTCCCAAAGTCGTAGACTGAATGGTGGCGTAGTCCTCTTGGGGGAAAATTATGAGCTAAGG
(SEQ ID NO: 412)

Exon: 1001..1243
Exon: 1345..2157

Exon: 2279..2867
Start ATG: 1138

Transcript No. : CT13300
TCCACAGCACGTTTTACAGCACTGGCCTCTGACACCTCGTGTTTTTGTTCTTTTCTCCGCATCGCCATCGCCAGGCAAGAGTGCGCGCTACATTT
TCGTTTATTTCATCGTTCAGCCAGCAACCAAGGCACTGCGAAATGTCTGCAACCGAGACTCTGAATGTGGAGGCGGCAACGCCCGAGATCGGCGA
GGAGGTCAAGAAACAAAAGAAGCCCAAGCCGAACAACAAGAAGCTCCGCCAAGAAGCGGCAGCCAAAATAGCCTCCGGAGAAGGCGGCGACGAGG
AGCTGACCACAAACGGAGATGCCAAACCGGCAACACCGGCCGCTCAGCCGGCAAAGAAGAAGGGGAACAAGGGCAAGAAAAGCGGTCAGACTGAT
CCGCCCACCATACCCATTGCTAAGCTTTATCCGGACGGCAACTTCCCCGAGGGCGAGATCGTGGAGCACCCCACGCCCAAGGATATGCCCGACGA
TCGTACGGCCAAGGACCGATTCACATCGGAGGAGAAGCGTGCTCTGGACCGTATCAACACGGACATCTACCAGGAATTGCGCCAGGCGGCTGAGG
CCCATCGTCAGACGCGTCAGTATATGCAGCGCTACATTAAGCCGGGCATGACCATGATCCAAATCTGCGAGGAGCTGGAGAACACTGCTCGGCGC
CTGATCGGCGAAAATGGTCTGGAGGCTGGTTTGGCCTTCCCGACTGGTTGCTCTCTTAACCATTGCGCCGCCCACTACACGCCCAATGCCGGAGA
CCCCACTGTACTGCAGTACGACGATGTGTGCAAGATTGATTTTGGTACCCATATCAAGGGGCGGATCATTGATTGCGCCTTCACCCTGACCTTCA
ACAACAAGTACGACAAGTTGCTGCAGGCCGTCAAGGAGGCCACCAACACGGGCATCAGAGAGGCGGGCATCGATGTGCGCCTATGCGACATCGGC
GCCGCTATCCAGGAGGTCATGGAGTCGTACGAGATCGAGTTGGACGGCAAAACATATCCCATCAAGGCGATTCGCAACTTAAATGGACACTCCAT
CAGCCCGTACCGCATTCATGCTGGAAAAACGGTGCCCATTGTGAAAGGCGGAGAGTCCACTCGCATGGAGGAGGATGAATTCTACGCCATTGAGA
CGTTCGGCTCGACGGGTCGCGGTCTGGTCCATGACGATATGGACTGCTCGCATTACATGAAGAACTTTGATCTGCCGTTTGTGCCGCTGCGCCTG
CAGTCATCCAAGCAGCTGCTTGGCACCATCAACAAAAACTTCGGCACCCTGGCCTTCTGCAAGCGTTGGCTGGACCGCGCCGGTGCCACGAAGTA
CCAGATGGCTCTCAAGGATCTGTGCGACAAGGGCATTGTGGAGGCTTATCCGCCGTTGTGCGACATTAAGGGCTGCTACACGGCTCAGTACGAAC
ACACAATTATGCTGCGACCCACCTGCAAAGAAGTCGTTTCCCGTGGCGACGACTACTAGTGGGATGAGGAACTGGACAGTGACCGATTTTCGGCG
ATGTATGGCTTGCATTATATACGGTTTTTGATATAAGTTCATTCTATTGTTGATTTTTTGTGAGCATGCGCCAACCGAATTATATATACAATGTA
TTATGCTCAGAATATAAGCGGAGTGAGATT
(SEQ ID NO: 413)

Start ATG: 138

MSATETLNVEAATPEIGEEVKKQKKPKPNNKKLRQEAAAKIASGEGGDEELTTNGDAKPATPAAQPAKKKGNKGKKSGQTDPPTIPIAKLYPDGN
FPEGEIVEHPTPKDMPDDRTAKDRFTSEEKRALDRINTDIYQELRQAAEAHRQTRQYMQRYIKPGMTMIQICEELENTARRLIGENGLEAGLAFP
TGCSLNHCAAHYTPNAGDPTVLQYDDVCKIDFGTHIKGRIIDCAFTLTFNNKYDKLLQAVKEATNTGIREAGIDVRLCDIGAAIQEVMESYEIEL
DGKTYPIKAIRNLNGHSISPYRIHAGKTVPIVKGGESTRMEEDEFYAIETFGSTGRGLVHDDMDCSHYMKNFDLPFVPLRLQSSKQLLGTINKNF
GTLAFCKRWLDRAGATKYQMALKDLCDKGIVEAYPPLCDIKGCYTAQYEHTIMLRPTCKEVVSRGDDY*
(SEQ ID NO: 414)

Name: methionine aminopeptidase
Classification: peptidase
Gene Symbol: und
FlyBase ID: FBgn0025117

Celera Sequence No. : 142000013384676
TGTCCTTAGCCTCGGCCATAGCGGAGGAGAATGAATCCCCGAGAGGTGTCTCGGTTGAACGGTGGGAACTGAAGAAGGCGGCGTTGGCGAAGACG
CTGCTGATTTGTTTGCCTGTTGACCGACGAGCGACAACTGTGCTCATTTATCAGCTGCCGGCCAACTCAAAAGCTCCGCTGCGCACGGAAAGCTT
TCGCTTGCGATCAGCTGTTTTTGCAGCTTTGCCTTTTGCGCCCGCCATTCGCGTATGTAAACAACATAGCGAAAATTGCTGTAATTGCATGTTTT
TGTCGCCAAATGTTGCGTATTCGCACTGATAGCACCGCACCCAAGTTCATAGTACGTATACGCTCAATTGGCGCTGATTGCCGGCTGGCATATCG
GCATCGAAATCAGAGCGCTATGTGCACAACATCATGATTTGGGGTCGTCGTTGTCAAGTTCATCAGTGAATCGAATGCACAAACATGGGTTTGAA
AGTCGAAGGGTTATGATTATTGCTCACAGATTAGGTCGCCACTCGGAAACAGCTCTGCTCCACTGGCAATCAAATCGTTTCAAAGCATTTCCATT
CCATCTGGCTTATTCCACATATTAGTTATTATTAAGCGTGTGATGTGTATCTTAATTGTCATGCAAGAAAAACATAAATAAATAATGAATGTTTC
TTTGTGGAAGTTGTTCTTGTAAATTTTACAACAAATGCCACATAATATTACCCTTATCTTTATCGGGATATTCAAAAACGTTTGCGATTGCGCAG
GCGATAAGAAACACCAATAAAAGGGCACGTAACTACCAAATAAACTTAATAGTTTTATTTAACCAGCTCTGTTATCTATAACGTGTAATCTTTGA
AAGTTTTCCTAGACTTAAAATTTTTCATTAAAATGCAATGCAACAAAGTGCAAAGAGCAAGTGCAAGGCTAGCTATTAACTTAAACAATTCATAC
TGGACTGGTCGTGAAGAAGTGATGAAAAAATGATGGGGCCAGCAGGCCTTAAAACTTAACAGCAAGGCCATTGTCGAAAGAAGATCATTCCTTTC
CAACAACAAGGCTTATAGGACGGAGCTGGAAACACTCTCGATGACCTCAAACGCATTGTCTATTTCCGAACTCTCCAGCAAACGGTTGACAGCAA
TGCGAATGCTGGGACGGACTGGTTGGCGTTCCCTGTTCTGCAGGTAGGCAGCCTGTACCACAGCCACTCCACGAGCAATGCACTGGGAAAAGTGA
GTAGAAATGTATAGTTTTCATAATTGCATGGGGAAATAAAATGCCTACCTTATCAGCCAGCTCTGTTAGAAGTTTCAGTTCCTTGTCAAAGTTCT
CGGCGGGCTGGGCAAGATACAAGTGCTTCACTGGTGACACCTCATCGCCGCGCAGGGTTAGCTTGCTGAATCGCAAAAACTTCTGGTGCAACGTC
TTAGACTTTGCCTGCAGCTGCTCGAAGATTTGTGGTTCTCGTTCGAAACGATCCAACGCTGAAATAGCCGCCTGGGTGAGCATGGGCGGCAGCGA
GGCCGAGAAGATGTAGCCCAAGCCAGAGAGGCGCTGGTGCTCGGCTATGAAGTGCGAGCCAACACAGAAGCCACCGACTGTTGCCATCGAACCCT
CCATGCCGGCCGATATCAGATCGACTTCATCACGCTAAAAGAAAAATACCAGTTATAATTTTAGTTTTTCTTTCCGGTTTACCACCTACATCGAC
ATTAAAGTGCTCCGTAACTCCGTGACCACCCTGGCCCAATGTGCCAAAGGAGATGCTTTCGTCGATGAACAAACGCAGCTTGTACTTCTGACGCA
AGGCCACCAGGTCGGGAAGTGGGCAAATCTCGCCCGTATTCATATAGATACCCTCGGCGACGAGGAAGCGACGTGTCTTAGCCGCCTTTTTCGGA
TTTTTCTGGTCTCGTTTTTCTTGCTCAATCAGCAGACGTTCTAGATCCTCAACGTCATTGTGCTTAAAGAAAACGATTGTGCTTCGTGAAGCATC
CAGACCCTTCTGAATGGCAAAGTTGACAGCCTCATCCCTACAAATAACAAGTAATTAGTCGCCAATCTGAGTAGGTGAAGTAGACAATCCTACAC
AAAGATAAGGTCGCCACGTTTGGCATACGCCGGAATGGCACTGGCCACGGTCGAGAAGCCGTAGGAATAGACAATGGCCTCCTCCAGGCCCATGA
ACTTGGCAATACGATCCTCCAGGTCCAGATGCACGTCCATAGTGCCGTAGAAGCCCCGAGGTCCGCAAGATCCAACTCCGTACTTGCGCAGCGAC
TTGCAGGCCTCCTCCAGTATCTCCTGGTCCTCGAGGAAGCCAAGATAGTTGTGAGAGCCAAGATTTAGGCAGTCGTGTCCATCGACCTGGATGCG
CTTGCCCACCCTGGACTGCACAACGCGGGTGTGCAGCAGGGGATGATTGGGATCGGTGTCGGCCACCAAGGGCTCTGGTTCATAGTCGGCGATTA
TTCGGTCTTCCTCCTCCTTGGTCAGCTGTCGGCGACGACCTCCTCCTCGTCTGTGGAGCAGCAACCAAATCACGGTTATGAGCAGTAGGGTCTCC
AAGACGAGAGCAAACGTGGGGGTCTGTGGAAGGAGTAGAAACTGGAGTAAGCTAAATGTGGTGAAAAAGGCGAATGCAAACTTACGTTTCGGAAA
ATACTGCCGATTTCGTTGAACAATTGGATGGCCACCATTTTGACAGTCTGGTTCCGTGCCCTTTCTGTGAAAAATCAATTGAAACCGCCTTAATT
CCCTGAAGTTATGTGTCATCTAGCCGACGCTTTCTTATCGCGGGTATGCCCCATACATATGTAGAATTGAAGCATTCGACCATACGGTACGGAAA
TCTTTTCAATTGGGTGTGTATGCTGACATAGGCTAATTGCCAGTGGGCGAAAAATGTGCAACCACGCCCTTCTCCAACATTCTCTTACATTAAAT ATCCATTTAAATCGAGCACTCACCACAAAACTCAGTTAACTATAGGCAAAATGCGTGAAATATCCGCCGAAACAGATGGATGAACGAATGTACTA
AAAAATACCAATACGCGGATATCTTTAAGATGTGCGCCAAATTGGCGGCGATGGAGGAACAGTGGAATATGGAACTAGGGGACGTTTTTATTTAT
TTTTTGTTATTCAAAAACCTGGTCCTGTCGACCTGTCCCGCCCACCTGCCCCACCGACCTGTCCCGCCGATCTGACCCACCGACCTGTTCCGCTG
ACGTGTCCCACTGACCTGTCCCACCGAGCTGACTCGCTAACAACAAAATACAACAAGTTACAACAGATTTTAAATTTTTATTAAAAATTACCTAG
ATTTTATCAATATTTTTATGATACTGAACTCAAATAAACTTGCTACGTAACGGTTCTTTTCTAGTTATCATTTCAAATATATGATCGATTACTAT
TTTATATCGATAGGCAGAGCAGCGATCGCAGTGTGACCGTGCGGTGGGAAATAACGAAATCGAATTCAATTCAAACCGCCGATCCATTCAGTTTC
CATTGAACTGCTGCTGCGATCGGTCAACCGATGTGAATGAGCCGCGTTACTGGCGCCATCTGAAATTCGAGTTCGCGAGATAAAAACCGCGAGAA
GACAAAGAACACCGCAAAAAGCCGATGTAAACAAAGAGATATAGTTAGTTCTGCATTTTGCAAGAAAACTTTATCACATTACACGCGAATCGAAA
CGGATACTTGTATGTGCACAAAGTGAAATCAGCTGGACAACAAGAGTATTTTGCAATTGCCTTGGTTTATTTTCAGCCACTTGCGGCTGTCGTTT
TCTGTGAAATTAACACTTTTTTCTATTGGCAGTGATGGGAAGTGTATATTTGGGTGTACCTGGCTGGTAGTCTAGATACAACAATTTACGCTATG
TGTCGCGATCTAGTCTAGGTACAAGTATTCACTCTTCCTTGCAAATGTCCTTGTTTTAATATATAGTAAATTCTATTGCATTTCATATAATTATT
TACTATTTACCTATATCACTATTCAAT
(SEQ ID NO: 415)

Exon: 3017..2969
Exon: 2724..2651
Exon: 2588..2089
Exon: 2032..1705
Exon: 1649..1284
Exon: 1222..1001
Start ATG: 2698 (Reverse strand: CAT)

Transcript No. : CT13338
TTTCGGCGGATATTTCACGCATTTTGCCTATAGTTAACTGAGTTTTGTGAAAGGGCACGGAACCAGACTGTCAAAATGGTGGCCATCCAATTGTT
CAACGAAATCGGCAGTATTTTCCGAAACACCCCCACGTTTGCTCTCGTCTTGGAGACCCTACTGCTCATAACCGTGATTTGGTTGCTGCTCCACA
GACGAGGAGGAGGTCGTCGCCGACAGCTGACCAAGGAGGAGGAAGACCGAATAATCGCCGACTATGAACCAGAGCCCTTGGTGGCCGACACCGAT
CCCAATCATCCCCTGCTGCACACCCGCGTTGTGCAGTCCAGGGTGGGCAAGCGCATCCAGGTCGATGGACACGACTGCCTAAATCTTGGCTCTCA
CAACTATCTTGGCTTCCTCGAGGACCAGGAGATACTGGAGGAGGCCTGCAAGTCGCTGCGCAAGTACGGAGTTGGATCTTGCGGACCTCGGGGCT
TCTACGGCACTATGGACGTGCATCTGGACCTGGAGGATCGTATTGCCAAGTTCATGGGCCTGGAGGAGGCCATTGTCTATTCCTACGGCTTCTCG
ACCGTGGCCAGTGCCATTCCGGCGTATGCCAAACGTGGCGACCTTATCTTTGTGGATGAGGCTGTCAACTTTGCCATTCAGAAGGGTCTGGATGC
TTCACGAAGCACAATCGTTTTCTTTAAGCACAATGACGTTGAGGATCTAGAACGTCTGCTGATTGAGCAAGAAAAACGAGACCAGAAAAATCCGA
AAAAGGCGGCTAAGACACGTCGCTTCCTCGTCGCCGAGGGTATCTATATGAATACGGGCGAGATTTGCCCACTTCCCGACCTGGTGGCCTTGCGT
CAGAAGTACAAGCTGCGTTTGTTCATCGACGAAAGCATCTCCTTTGGCACATTGGGCCAGGGTGGTCACGGAGTTACGGAGCACTTTAATGTCGA
TCGTGATGAAGTCGATCTGATATCGGCCGGCATGGAGGGTTCGATGGCAACAGTCGGTGGCTTCTGTGTTGGCTCGCACTTCATAGCCGAGCACC
AGCGCCTCTCTGGCTTGGGCTACATCTTCTCGGCCTCGCTGCCGCCCATGCTCACCCAGGCGGCTATTTCAGCGTTGGATCGTTTCGAACGAGAA
CCACAAATCTTCGAGCAGCTGCAGGCAAAGTCTAAGACGTTGCACCAGAAGTTTTTGCGATTCAGCAAGCTAACCCTGCGCGGCGATGAGGTGTC
ACCAGTGAAGCACTTGTATCTTGCCCAGCCCGCCGAGAACTTTGACAAGGAACTGAAACTTCTAACAGAGCTGGCTGATAAGTGCATTGCTCGTG
GAGTGGCTGTGGTACAGGCTGCCTACCTGCAGAACAGGGAACGCCAACCAGTCCGTCCCAGCATTCGCATTGCTGTCAACCGTTTGCTGGAGAGT
TCGGAAATAGACAATGCGTTTGAGGTCATCGAGAGTGTTTCCAGCTCCGTCCTATAAGCCTTGTTGTTGGAAAGGAATGATCTTCTTTCGACAAT
GGCCTTGCTGTTAAGTTTT
(SEQ ID NO: 416)

Start ATG: 76 (Reverse strand: CAT)

MVAIQLFNEIGSIFRNTPTFALVLETLLLITVIWLLLHRRGGGRRRQLTKEEEDRIIADYEPEPLVADTDPNHPLLHTRVVQSRVGKRIQVDGHD
CLNLGSHNYLGFLEDQEILEEACKSLRKYGVGSCGPRGFYGTMDVHLDLEDRIAKFMGLEEAIVYSYGFSTVASAIPAYAKRGDLIFVDEAVNFA
IQKGLDASRSTIVFFKHNDVEDLERLLIEQEKRDQKNPKKAAKTRRFLVAEGIYMNTGEICPLPDLVALRQKYKLRLFIDESISFGTLGQGGHGV
TEHFNVDRDEVDLISAGMEGSMATVGGFCVGSHFIAEHQRLSGLGYIFSASLPPMLTQAAISALDRFEREPQIFEQLQAKSKTLHQKFLRFSKLT
LRGDEVSPVKHLYLAQPAENFDKELKLLTELADKCIARGVAVVQAAYLQNRERQPVRPSIRIAVNRLLESSEIDNAFEVIESVSSSVL*
(SEQ ID NO: 417)

Classification: enzyme

Celera Sequence No. : 142000013384826
TCAATATAAAACAAAAGAGAAAAGCTTGCAAGGGAATTATTAAGATGCCTGCAAATGACAAGTATGCAAATCGTTATCTAAATATTTATACATAT
ATTGATTATTGCAATTGCATCTAAACGAAATTCATGTTTAATGTTTTTGATTGTAAAATCCAATGGAGGACCGCAAGAGCAGAAATCTCATTAAA
TAATAGACAAATAATTAGACAGATCCACAAAATCTCCTTGATTAATCACTGTTGAGCAACTTAAAATTTATTAACGATAGGAAAAATTTCCCTAT
TGAAGAAAACGAAGCAAAAAATTTCAGAATATTATTATACTTATAGCAGAATTTTTTGAATGATTCTGGGTAATATTACGTTTCGTTTGTGTACCA
TAGATAAACTGAGAGGGGCTACTTCATGTTGTGCCGCTTCCTGAAGAGAAAGCGATCTTTGTAGCACCAAGTATTAACTAATCTGAAGCAGCAGC
AGCAGTAGCCGCCAGCCATAAATCTGCTAATGACTCTCTTCAAATGCGAGAGCGGTCTGCCGATAAAGAACAAAGAATTGTAAACTAAAATATACAC
TATATAGATACTGATACTGAAAACCGATAATGGAAACTGACATCAAATACTTATTACCATTAAACTCTCGATCCTTTCGTAAAAACCAATGTGCA
TGACAGCTGGAAATTTAGGCATTTCCAAAGTGCAATAGTTAAATGTTACAAAATTCCACACAAATTCCATTTAACACTCACAGACAAAACAAAAG
CAACTGCAAGAGCAAGAAAACCAAGCCACAACTACATATAGCAAGTGCAGGAATTTAACTGTAAACGTAAACCAATATGTATTTAAATAAATATA
AATTGAAACCATTTGAAAGGTGTTTAAAACGTTTCCACGATCTGGATATAAACACTTGGCAAGCACAGTTGTATTTTACGTATTTATCTTTATTA
CGATTAGCGCACGGGTTAACATAGGACCTAACAATAATTTTAGATTTAAATCAAATTTCATTTAACTTAAATCTCGCATTAATGTTGACCGAACT
CAATTCGGTAACCAGATACTTAAAAGAGAATGGTATCTCGATCATCGATACAGAACTGTTATCCCCGCACAAGCGACACGTATCTGGCTGAGAAG
AGAGTCCTCCCGTCTCATTTCGCTTAACAATGCGTTGCAGAGGCGCCAGAATGGAGCCGCACTTGTGGCACACCAGGGTGTGCGTCTTATCGGAG
TTGTGGAACAAGCGATCCTGCAGCAGGAAAGCAGCACCGTGAGAGATCAAAGCATCCCGTTCCATCTCACCGAATCTGACGCCTCCACCGCGTTT
TCTGCCCTTAATTGGCTGATGGGTCCGAGCTTCCACCGCTCCCGTAGATCTTACTTGCCACTTGTCAAACACCATGTGCCGAAGACGCTGGTAAT
GCACCACTCCAAAAAATATGTCAGCAGTCATCTCGCGGCCATCTACGCCGGAATACAGCCTCTCCGTTCCGTAGTAATTGTAACCCCCAGCCTCT AACATTTTGCCAAAATAGTCAATAGCAGTATTCTCTTCGGAGAAGCGAAAAGGCGTGGCATCGTAAACATTTCCGTGGATTGCAGCCCCCTTTCC
CGCCATCGTTTCTATCATCATGGCGATTGTCATTCGGGAGGGGAAGCCGTGGGGATTGAACACAATGTCTGGAATCAAACCAGATTCCGTAAATG
GCAAGTCCTCTGCAGGATATTTTTGTGAGCAAATTCCTTTCTGACCAGCTCTTGATGCAAACTTGTCTCCAATAGTGGCAGGTCGTGGAACCCTC
AGTGTGATGGCCACCATTTTTTTGGCGACAAATCGAAGCTTCCCAACTGTCGGATGCTCTCTACTATGCAATCCTCCTTTTCATCCATTTTCAC
AACTTTATAAGTGGCGACCTCTCCGTCAAAGTAACAGTACAGGGGCGAACCATAGCTCAATTTGGAGCCCGGATGTGGAAGACCATCCGTGTCAA
GATGCTTTATTAACTCCGGCATGTGTGGATGCCTTGCGAAGTAACTGCTCTTCTTGTCCAACGTCAAAAACTTTGTTTTGTAGATACTTCCATAG
GCGAATCCTCGTTCATAAGCAGCCTTGTTGATGATCATAGCATCTTCCATGTCGTAGCCCGTGTAGGAAATGACAGCTACAATAGCATTTGTGCC
CATTGCAAAGTCATCCAGCTGGATGTTGTCGTAGTGTACTGGTCGGAAGAGAGGAGTCCCTGGCGTCTGAAGGCGGTATAACTTGTTGGCCGCTT
GCTTAGGCCAATTCAAGCATGGCGTTCCCATCGTCTGTTTTCCCATCTGACACTGGTACATGTTACGTGGCGATTGATTGTAGTCCGGCATGGGT
ATCAAGTTGGCCAAGTTGCTCATGAAGTGGGTCTTAGCCAACTCCAAATGAGTGGTGAAGTCAGGATACATTTCCTTTGCATCGATGGCGATCTC
CATATAAAGCTGTTCCAGTGTTCCGATGTACTCCACCCTTTTCCACTTTAGGTTCCAAACGGGCCTCATCATCCTGGCAGGACCCGTTGCAATGT
AAAGCCCTGGAAACTGACCGTTCTTCTTGAAGGGTATAAAGCCGATTTCCATCATCTGGGGAAGGGTGCCGAATATCTTCCCGTAGCGCAATTCG
TCAACTATTTTTTCGGCTTCTGATTGATGAATGTGACCCAAGTGTTTGCCATCTAGGAAGACGACGTAAAGTTTTTCGCCCAAATATCTTCGGTT
TGACAAGGGCATCATGCCCATATCTATAAGATGCTTGGGAATGGCCTGAAAAAAAAAGTAATCGGTTAAAATTTCTAATAAAGTCTACCATTAGC
TGTACCCACCTTCACCAACTTGGGATCGGGACGCATCGAAATCTCGCAAGTTAGAGTCAAATGATTTAACAGTCCGCACGGTGTGCCATCAGGAG
TGTGCACTGGACAAATAAAACCCCAGGCATCCGGGAGCAGCTGCCGCGCCTCAGTGGTTCTCATCGTTGTAAAATAGGAACCACGGTGGATGGCG
CGAAAGTGGGACATGTAACGCATCCTGTTAATGTTCTCCGCCATAATGACTAATCCGCTATTTTGCATTAATCCCAGGCCAGTGCGACTCGCAAT
ATTTCCAGTTGCTAAAAACGACTCTATGGCCCGGCCAACTCCTCCTGCTTGTCGCATGCACTGCGTCATCACAGCACTGGTAACTAGGGCATCAG
GTGAAGTCAGTTTTTTTGAAGGCAACGTCGGACTTGCGAGACCCAGGATTCGACTCGCTCACTTAGGTATTTCTGATAGAGATGGCCTGGCAGA
AGCACTTCCTGCATCATAGCTGAGTCGACGTTCTCCACTTTGTACTTGCCCTGTGCGCATTGGAAAAGCTTCTGAATCATAAACACAATCAACTG
GAACTTATCCTCATAGGTATCCAGGTGAATCATTACTCGCTCCCTAAGAATAAAGTCTGTGACATCATCATCCGGTTGCCATTCCGGAACTTCTG
GGAAGCGGGCACGGAACAGATTGCCAATGAAGCTCTTGCACTGGGCGTGCGTATAGACGTTTTCATTTTGAACTTCCCTCAACATGGCTTGCACG
CAGGACACATAGTACTGGTCGGACTCGTAGCCTTGCACCAATCTGTTGTATATTTCCTCATCTGTATAATCCATTAGGCACTTGAGGATCAGGCA
AACTGGTACGTATGATAGTCTCTTGACGTGAGAAAACATAAACTTTGCAGTTCCATTGTTTAAATAATGTACTACATTGCTCAGGGATGATTCGT
CCTCACGGACCGTTTGCACTAACATACCCAAATCGCTAAAATTCTGTCCACGATCCTTCCAGGATGAACGTTTTACACATATGGGATGGTTCCTC
CGGGTCATGATCAACATACGTACAATCTTCTCATTTCCTCGGATCACAAAAATGCCCCCCCACTCGCTGTCGTGCTCTCCATGTTTTACCATTTC
TTCCGGAGTAGCCTGTCCCAGATTGCAGGCTTTGGAGCGCAACATGATGGGCACTTCTCCTAGGTCCATGTTTATGGGAGTCTTTTGCACTCCAT
TGACACTCCACCCCAATCGGACCGAGCACATTCCCGAGTAGGAGACATGGAGCTGCCTGGAGTCCGTGGGGTAAATCTCTCGGGTGCGCACATCA
ATCACATCTTGCGGCACCTTTGGCTTCGCTATCCATATTGATTCTACTTTCATTGAAATCTTTTCGCCGGCAGGACTCAGCCAGTGGTTCGGGAT
CATGTGTTTGGCCGAGTTATCCAGTCCCACGGTCAGCATCTCGTCGAAGGAATCCACATGTGGACCTCCCAAATTGGCCAAATGCTAGCCATAGA
AGTAAATCTATTAGCACGAAACCTTGCTATAGGTACAAGATTGATATTTACCCTGCTGAGTTTTTAGGTATCTGCTTAAACTCCGGGCGGGAAT
TGGTCAGCACTGGAATGGTCTTCATTTGTTGCATCTCCTCCAGCATGTTGTAAGTATTATTCTTTCAGAATGCCGACCAAAAATATTAAGAAACC
TATTGCCTTCCTTCGCACGTGTTGTTTGGAATCGAACCGTTTTGAATGCGAACCAGTCAGTGGTGAGGCAGTCGCAAAGAACTAGTTCATATATT
ATATTGTTCATATAACTGAATGAAATAAGAATATAGATGATTGGGATAAAAATTTTCGGTAAATAAAGAACCATCACTAAAAATTTGTATTCAGA
TTAATAGAACACACTAAAATAACCTTAAAGTTCGGTGAATTGTCGTATGGTTCCGATTCGTGTTCAGCTCATCTTTAAATAACTGGGCTGCCAAC
CGAATGCAAGGAACAGCTGATATGTGCGCGCTTGATAAGCCTGATAACCCAATTTTGAATTGTATCCAAGTTGTATAAAAGCAAATATAATTTAT
TTGCAACGTCTGACATATTGTGCACATACGGCAATAACCATTTAGCATTTGCAAAGGCATCCGGTATGTAGAACACAACTCCTGCGGAAATGAGA
CTTTGCAACAGGATGTGCCAACGTGTTGCTCTGGCAATGAAGTTGTTGCATTGTTGTGAGCCACATAGGTGGCGTATGTATGCACATATGTATGT
ATGTGCATATTAATCTGAAGCACCCTCCCCAAAATACGCCATCTAAAGCTTCTAAGAAGCAGTTTTGTCGAATACTTGGGCTTAAACCCCACTGA
CTGGCACATTAATGTCTAATGACTGCGAGAATATGAAAATTTTACTAACATTATATTTCGTCTTAAGATAGGTGTTAATCAAGGCTGATGCCAGA
TTTCTTAATTTTTCTTGTATTGGAATTGCCAAATTACTTTGTTGGGTTTTAACGTGAAAACATGAAGTGGTTGTGGGAACATCAAGAAAATATCA
TCAATTTGAGATGGTTCAGGGGCTAATGGAAAAGGAAAGAACCCCAATCTGAACGCAGTCACTCCGGTTTATTATTCCATTATAATGAACACAAT
GGATTTCTTGCAACTTATTTTGGGCAGAGCGTCCTTGATGCCTGGTTCTTGTATCCTTGCTACTTTCAACTTTCGCTGCA
(SEQ ID NO: 418)

Exon: 4590..4422
Exon: 4359..2860
Exon: 2800..1001
Start ATG: 4511 (Reverse strand: CAT)

Transcript No. : CT13358
TCCAAACAACACGTGCGAAGGAAGGCAATAGGTTTCTTAATATTTTTGGTCGGCATTCTGAAAGAATAATACTTACAACATGCTGGAGGAGATGC
AACAAATGAAGACCATTCCAGTGCTGACCAATTCCCGCCCGGAGTTTAAGCAGATACCTAAAAAACTCAGCAGGCATTTGGCCAATTTGGGAGGT
CCACATGTGGATTCCTTCGACGAGATGCTGACCGTGGGACTGGATAACTCGGCCAAACACATGATCCCGAACCACTGGCTGAGTCCTGCCGGCGA
AAAGATTTCAATGAAAGTAGAATCAATATGGATAGCGAAGCCAAAGGTGCCGCAAGATGTGATTGATGTGCGCACCCGAGAGATTTACCCCACGG
ACTCCAGGCAGCTCCATGTCTCCTACTCGGGAATGTGCTCGGTCCGATTGGGGTGGAGTGTCAATGGAGTGCAAAAGACTCCCATAAACATGGAC
CTAGGAGAAGTGCCCATCATGTTGCGCTCCAAAGCCTGCAATCTGGGACAGGCTACTCCGGAAGAAATGGTAAAACATGGAGAGCACGACAGCGA
GTGGGGGGGCATTTTTGTGATCCGAGGAAATGAGAAGATTGTACGTATGTTGATCATGACCCGGAGGAACCATCCCATATGTGTAAAACGTTCAT
CCTGGAAGGATCGTGGACAGAATTTTAGCGATTTGGGTATGTTAGTGCAAACGGTCCGTGAGGACGAATCATCCCTGAGCAATGTAGTACATTAT
TTAAACAATGGAACTGCAAAGTTTATGTTTTCTCACGTCAAGAGACTATCATACGTACCAGTTTGCCTGATCCTCAAGTGCCTAATGGATTATAC
AGATGAGGAAATATACAACAGATTGGTGCAAGGCTACGAGTCCGACCAGTACTATGTGTCCTGCGTGCAAGCCATGTTGAGGGAAGTTCAAAATG
AAAACGTCTATACGCACGCCCAGTGCAAGAGCTTCATTGGCAATCTGTTCCGTGCCCGCTTCCCAGAAGTTCCGGAATGGCAACCGGATGATGAT
GTCACAGACTTTATTCTTAGGGAGCGAGTAATGATTCACCTGGATACCTATGAGGATAAGTTCCAGTTGATTGTGTTTATGATTCAGAAGCTTTT
CCAATGCGCACAGGGCAAGTACAAAGTGGAGAACGTCGACTCAGCTATGATGCAGGAAGTGCTTCTGCCAGGCCATCTCTATCAGAAATACCTAA
GTGAGCGAGTCGAATCCTGGGTCTCGCAAGTCCGACGTTGCCTTCAAAAAAAACTGACTTCACCTGATGCCCTAGTTACCAGTGCTGTGATGACG
CAGTGCATGCGACAAGCAGGAGGAGTTGGCCGGGCCATAGAGTCGTTTTTAGCAACTGGAAATATTGCGAGTCGCACTGGCCTGGGATTAATGCA
AAATAGCGGATTAGTCATTATGGCGGAGAACATTAACAGGATGCGTTACATGTCCCACTTTCGCGCCATCCACCGTGGTTCCTATTTTACAACGA
TGAGAACCACTGAGGCGCGGCAGCTGCTCCCGGATGCCTGGGGTTTTATTTGTCCAGTGCACACTCCTGATGGCACACCGTGCGGACTGTTAAAT
CATTTGACTCTAACTTGCGAGATTTCGATGCGTCCCGATCCCAAGTTGGTGAAGGCCATTCCCAAGCATCTTATAGATATGGGCATGATGCCCTT
GTCAAACCGAAGATATTTGGGCGAAAAACTTTACGTCGTCTTCCTAGATGGCAAACACTTGGGTCACATTCATCAATCAGAAGCCGAAAAAATAG
TTGACGAATTGCGCTACGGGAAGATATTCGGCACCCTTCCCCAGATGATGGAAATCGGCTTTATACCCTTCAAGAAGAACGGTCAGTTTCCAGGG CTTTACATTGCAACGGGTCCTGCCAGGATGATGAGGCCCGTTTGGAACCTAAAGTGGAAAAGGGTGGAGTACATCGGAACACTGGAACAGCTTTA
TATGGAGATCGCCATCGATGCAAAGGAAATGTATCCTGACTTCACCACTCATTTGGAGTTGGCTAAGACCCACTTCATGAGCAACTTGGCCAACT
TGATACCCATGCCGGACTACAATCAATCGCCACGTAACATGTACCAGTGTCAGATGGGAAAACAGACGATGGGAACGCCATGCTTGAATTGGCCT
AAGCAAGCGGCCAACAAGTTATACCGCCTTCAGACGCCAGGGACTCCTCTCTTCCGACCAGTACACTACGACAACATCCAGCTGGATGACTTTGC
AATGGGCACAAATGCTATTGTAGCTGTCATTTCCTACACGGGCTACGACATGGAAGATGCTATGATCATCAACAAGGCTGCTTATGAACGAGGAT
TCGCCTATGGAAGTATCTACAAAACAAAGTTTTTGACGTTGGACAAGAAGAGCAGTTACTTCGCAAGGCATCCACACATGCCGGAGTTAATAAAG
CATCTTGACACGGATGGTCTTCCACATCCGGGCTCCAAATTGAGCTATGGTTCGCCCCTGTACTGTTACTTTGACGGAGAGGTCGCCACTTATAA
AGTTGTGAAAATGGATGAAAAGGAGGATTGCATAGTAGAGAGCATCCGACAGTTGGGAAGCTTCGATTTGTCGCCAAAAAAAATGGTGGCCATCA
CACTGAGGGTTCCACGACCTGCCACTATTGGAGACAAGTTTGCATCAAGAGCTGGTCAGAAAGGAATTTGCTCACAAAAATATCCTGCAGAGGAC
TTGCCATTTACGGAATCTGGTTTGATTCCAGACATTGTGTTCAATCCCCACGGCTTCCCCTCCCGAATGACAATCGCCATGATGATAGAAACGAT
GGCGGGAAAGGGGGCTGCAATCCACGGAAATGTTTACGATGCCACGCCTTTTCGCTTCTCCGAAGAGAATACTGCTATTGACTATTTTGGCAAAA
TGTTAGAGGCTGGGGGTTACAATTACTACGGAACGGAGAGGCTGTATTCCGGCGTAGATGGCCGCGAGATGACTGCTGACATATTTTTTGGAGTG
GTGCATTACCAGCGTCTTCGGCACATGGTGTTTGACAAGTGGCAAGTAAGATCTACGGGAGCGGTGGAAGCTCGGACCCATCAGCCAATTAAGGG
CAGAAAACGCGGTGGAGGCGTCAGATTCGGTGAGATGGAACGGGATGCTTTGATCTCTCACGGTGCTGCTTTCCTGCTGCAGGATCGCTTGTTCC
ACAACTCCGATAAGACGCACACCCTGGTGTGCCACAAGTGCGGCTCCATTCTGGCGCCTCTGCAACGCATTGTTAAGCGAAATGAGACGGGAGGA
CTCTCTTCTCAGCCAGATACGTGTCGCTTGTGCGGGGATAACAGTTCTGTATCGATGATCGAGATACCATTCTCTTTTAAGTATCTGGTTACCGA
ATTGAGTTCGGTCAACATTAATGCGAGATTTAAGTTAAATGAAATTTGA
(SEQ ID NO: 419)

Start ATG: 80 (Reverse strand: CAT)

MLEEMQQMKTIPVLTNSRPEFKQIPKKLSRHLANLGGPHVDSFDEMLTVGLDNSAKHMIPNHWLSPAGEKISMKVESIWIAKPKVPQDVIDVRTR
EIYPTDSRQLHVSYSGMCSVRLGWSVNGVQKTPINMDLGEVPIMLRSKACNLGQATPEEMVKHGEHDSEWGGIFVIRGNEKIVRMLIMTRRNHPI
CVKRSSWKDRGQNFSDLGMLVQTVREDESSLSNVVHYLNNGTAKFMFSHVKRLSYVPVCLILKCLMDYTDEEIYNRLVQGYESDQYYVSCVQAML
REVQNENVYTHAQCKSFIGNLFRARFPEVPEWQPDDDVTDFILRERVMIHLDTYEDKFQLIVFMIQKLFQCAQGKYKVENVDSAMMQEVLLPGHL
YQKYLSERVESWVSQVRRCLQKKLTSPDALVTSAVMTQCMRQAGGVGRAIESFLATGNIASRTGLGLMQNSGLVIMAENINRMRYMSHFRAIHRG
SYFTTMRTTEARQLLPDAWGFICPVHTPDGTPCGLLNHLTLTCEISMRPDPKLVKAIPKHLIDMGMMPLSNRRYLGEKLYVVFLDGKHLGHIHQS
EAEKIVDELRYGKIFGTLPQMMEIGFIPFKKNGQFPGLYIATGPARMMRPVWNLKWKRVEYIGTLEQLYMEIAIDAKEMYPDFTTHLELAKTHFM
SNLANLIPMPDYNQSPRNMYQCQMGKQTMGTPCLNWPKQAANKLYRLQTPGTPLFRPVHYDNIQLDDFAMGTNAIVAVISYTGYDMEDAMIINKA
AYERGFAYGSIYKTKFLTLDKKSSYFARHPHMPELIKHLDTDGLPHPGSKLSYGSPLYCYFDGEVATYKVVKMDEKEDCIVESIRQLGSFDLSPK
KMVAITLRVPRPATIGDKFASRAGQKGICSQKYPAEDLPFTESGLIPDIVFNPHGFPSRMTIAMMIETMAGKGAAIHGNVYDATPFRFSEENTAI
DYFGKMLEAGGYNYYGTERLYSGVDGREMTADIFFGVVHYQRLRHMVFDKWQVRSTGAVEARTHQPIKGRKRGGGVRFGEMERDALISHGAAFLL
QDRLFHNSDKTHTLVCHKCGSILAPLQRIVKRNETGGLSSQPDTCRLCGDNSSVSMIEIPFSFKYLVTELSSVNINARFKLNEI*
(SEQ ID NO: 420)

Classification: enzyme
Gene Symbol: RpI135
FlyBase ID: FBgn0003278

Celera Sequence No. : 142000013384281
ATGTGGAATAAATTAATTATATTAATACGCTGGAACCACACAACATGCGCCCAAAACGATGATGATAATGATGATGGTGTGCAGGTGGTTCCGCT
CTTTTCATCTTGTAGTTGGTGTTGTTGTTGATTTTGTTGTGCTGCACTCCAAACTTCCACCACTCGCACTTGCACTTTCGCTGCTGCTTCCTCGA
CTTCTCCTCCTCCTCCTCCAGCAGAATCAAGACCATCCCGATCCTGATCCTCTTGCCCAGACAAGCGATCCTTCTTAGAAGCACTTGCGGTCGCAC
AATGGAGGGGCCGGACTCGTCGTACTCCTGCTTGGAGATCCACATCTGCTGGAAGGTGGACAGCGAAGCCAGGATGGAGCCACCGATCCAGACAG
AGTACTTGCGCTCTGGCGGGGCAATGATCTTGATCTTCATGGTCGACGGTGCCAGGGCGGTGATCTCCTTCTGCATACGGTCGGCGATGCCAGGG
TACATGGTGGTGCCACCGGACAGCACGGTGTTGGCATACAGATCCTTACGGATATCCACATCACACTTCATGATGGAGTTGTAGGTGGTCTCGTG
GATGCCGCAAGCCTCCATTCCCAAGAACGAGGGCTGGAACAGGGCCTCGGGGCAGCGGAAACGCTCGTTGCCGATGGTGATCACCTGTCCGTCGG
GCAGCTCGTAGGACTTCTCCAACGAGGAGCTGCTGGCAGCGGTGGCCATCTCCTGCTCAAAGTCGAGGGCAACATAGCACAGCTTCTCCTTGATG
TCACGGACGATTTCACGCTCAGCGGTGGTGGTGAAAGAGTAACCGCGCTCGGTCAGGATCTTCATCAGGTAGTCGGTCAAATCGCGACCAGCCAG
ATCCAGACGCAGGATGGCATGGGGAAGGGCATAACCCTCGTAGATGGGCACGGTGTGGGAGACACCATCGCCGGAGTCCAGAACGATACCGGTGG
TACGACCGGAGGCGTACAGCGAGAGCACAGCCTGGATGGCCACATACATGGCGGGTGTGTTGAAGGTCTCGAACATGATCTGGGTCATCTTCTCA
CGGTTGGCCTTGGGGTTCAGCGGGGCCTCGGTCAGCAGCACGGGGTGCTCCTCGGGTGCCACACGCAGCTCATTGTAGAAGGTGTGGTGCCAGAT
CTTCTCCATATCGTCCCAGTTGGTCACGATACCGTGCTCAATGGGGTACTTCAGGGTGAGGATACCACGCTTGCTCTGCGCCTCATCACCCACGT
ACGAGTCCTTCTGGCCCATGCCGACCATCACACCCTGGTGACGGGGACGTCCCACAATCGATGGAAGACGGCGCGGGGAGCATCGTCTCCGGCA
AATCCGGCCTTGCACATGCCAGAGCCGTTGTCGACAACCAGAGCAGCAACTTCTTCGTCACACATTTTGTAAGCTGCAATGGAAAGAATGCGGAT
TTCCCATTAGTTTTTGGTTACCTTATTTGGTAATGTAGAAATGGCAAAAAAAAAACTGAGAATTTGCGTGGTTTCCTTGGACTGCGCTGGTCTAC
CAAAGTACAATTGTCATAACAAACTAACTTGTTTTTCGTGTACAATTAAAAATCACTCAATGCAATGTACGTTTTTTTAGTACAAAATTTTAATC
TTGGACAAAAAAAATTTCATAAAAAAATACTTTTCCGATTGAAAACTGATTTTCACTTGCGATCGAATTGTAATAAGAAATTAAAAGAACAGTTA
CAAAATAGAAGGCCCCGCCCCGAAAAATTAAAACCACAATACGAATATGCCGAAAAGGGAGGGGAGAAGCTTCTAGACGACACTTAACGAATGCC
GGTGCAAAAGAAAGCCGCAAAGAGAGCACAGTTGCCTGTGTGTATGCGCCCTTAAAATGGCGGCTGCCTAAAACTCGAATTGGAACCCGAAATTA
ACATTACAAAATAAAAAAAAAAAAAAACACTAAACGCACTCTAGAAAATTTAACAATTAAGAGCCACGAAACTTTTCAAAGCTAGTTAAACTTTA
CCTTTTTGTTCGATTTAACAAATTCAAGGCGTGAAAACTACTGTAAACGCAAGTGGCGAGGCTGAGCTAAGCGACCGCACGGTTTGAAAGGAATG
ACTGGAATAAACCGACTGAAAGTGGCTGGTGAATGTTGAATGCCAGTTAACTGCGTTTTTCAATCGCTGCCTGCGTCGACGTCGCCATAGGCGTC
GCTCGCTCTCGCCATCTCGCTCGCTCGCGCCATGGTCGCTATGGGTGCGAAGGAGAGCGCTGGTGTGTTGAATTGCGGCGGCCAAGTTTTGTGA
CCATATATGGTCATGTTTCGAGGCGAAAAGCAAACCGTCGTCTGGCTTTCGCTCTCTCACACACACATACACTCTCTCTCGTTATTTTGCGCGTG
AGTGTGTGTATATGAACGAATGCTCGAAGGTTTTCTCCATTTTTGCAACTACAACTTTGAAAAACCGGCAAAAAATTTCTGCTTCAGCCAAAACGG
CTGCCTACGTCACTATTTTCAAGAACCTGATCTAGTTTTACAGATTATAATATGCATATACTGTATGTATGTACATTTATGGATGATCTGGTGTT
TTAGGGCGTGGGAAAAAAAGAAAGTGTTGGCGAATTGATTTGCAATTCGTAATTTGGCATATCTTTGGGTGAAATCGTGACACGCCCACATCAGC
GAGCTTGGCTTTAAACACTATATTAGATCCTAACATTTGAGTTGGGGCTATTGAATTGCTTTGGTTTTTATAATTTCGTATAATTTGTATGTATA
TATCCTGAAATCTGCAGTTGTAATCCTGATTCTTGAGTTATGGTATTTGAAACCCTGGTTTTGTTAATTTTGATGTCTTTCGACCTATTGGTATT TTGATTGACAATTTAGGGCCAAACTTGGGTATTTTTGGAGTTTTGGTCAATACAATAACTCTTTAGCTCGTGGCTAGTATTTTTTGATCACTTTC
AGCACTGGCACATAAAAAAATGTTTTGTTTACAAAAAAAATCACACATTTTCCGCGGCTTTTCTCGATTATTGCTTTTTCTTGGTGGGAGTGGTT
CGATGGTGTTTTGTTGTTGGGAAGGGGAAAGCTACTTACATTTGGTGTGTTTTATTAAAATTAATTAAATAAATATAAATTAAGTCTTTCGGTTT
GGTGTCTCTGGATTAGACGACTGCTGGCTGATGGAGCGGCTTTGTGTCGGGAGGAGTATCCACACAGCACAAGAACTCAAACGGTAGTGATATGA
AAACTGGTCCCGCAGCCCGTTTTATAAAGCCCGCTTAGCGCTAAAACCTTATCAGCCGCAATGCTCTCCGCTCTCAAGTCGCGTTCAAAACTTTT
ACCATATATGGGTATGAATTGTTCGCCGATTGGGTTTTCATTTACGGAGAATTTCCTCCGCAACTGGGTGTTCGTGCTTGTGTGTGTCTTGTATA
TCGCCATGAAGAGTGTACTTCCATGGGTCCTATCAGTTGCGGCATGTGATTCAATTTGGGGGTTACTCATATTCGATACTTCAGCTGGTTATCTT
TATGCTGTGATGGTCACGGTGCTTTTACACATTTTTTCCCCAACTACTCATTGTATGCCAAAACATACATATGTACATGTGTTTATAGTGGGTTT
ATTAGTAATGTCCAGCGATATTAAAACATTACAGTTAAATAATATTCATATTAGCTTACGTTTACTGCTATCTGCACTTCAAATTGGTTATTCCA
GGGACATTTTGTGCAACACACATCTTCTAGTAGGGCATTCACTAGTCGTAGAAAACACACCTAACTTAAGCCGGTTTTAACAATAACGGCGAAAC
AGCTGCCAGACGAGAGAAAAGTACACAGCAAGAAGCATTTCTATAATGATGCCGTCCTAAATATGCAGCATTTTTGCTCAAATTGATCATTTCGT
TGCATCGCTCAGGTGGTATAGTATTTGGCTATTGAATGTGATTGCTATCTTAATAGTTTGAATAGTAATAGTGCAAATATTCATTCATAAAAAA
TAGGTAATCGATTTTTTCAGTGCAGTCTATGCGTTTGCGCAACAGAGACGAAGAGAGAGACGCCTCACACACAAGCACATGCGGTCTAAGCTGCT
CTCCCTCTTTTTCTCTCTCTCTCTGGCTTGCGGCAGTTTTCCAGAGGCTGTGACTCAGTAAGCATTTCTTGTTGTTACCCTAACGATAAGCGTCC
GATTCCTAATTCTCTTTCAAATAATTTGTT
(SEQ ID NO: 421)

Exon: 3210..3080
Exon: 2113..1997
Exon: 1395..265
Start ATG: 1395 (Reverse strand: CAT)

Transcript No. : CT13368
TTCTTGTGCTGTGTGGATACTCCTCCCGACACAAAGCCGCTCCATCAGCCAGCAGTCGTCTAATCCAGAGACACCAAACCGAAAGACTTAATTTA
TATTTATTTAATTAATTTTAATAAAACACACCAAATACTTTCAGTCGGTTTATTCCAGTCATTCCTTTCAAACCGTGCGGTCGCTTAGCTCAGCC
TCGCCACTTGCGTTTACAGTAGTTTTCACGCCTTGAATTTGTTAAATCGAACAAAAAGATGTGTGACGAAGAAGTTGCTGCTCTGGTTGTCGACA
ACGGCTCTGGCATGTGCAAGGCCGGATTTGCCGGAGACGATGCTCCCCGCGCCGTCTTCCCATCGATTGTGGGACGTCCCCGTCACCAGGGTGTG
ATGGTCGGCATGGGCCAGAAGGACTCGTACGTGGGTGATGAGGCGCAGAGCAAGCGTGGTATCCTCACCCTGAAGTACCCCATTGAGCACGGTAT
CGTGACCAACTGGGACGATATGGAGAAGATCTGGCACCACACCTTCTACAATGAGCTGCGTGTGGCACCCGAGGAGCACCCCGTGCTGCTGACCG
AGGCCCCGCTGAACCCCAAGGCCAACCGTGAGAAGATGACCCAGATCATGTTCGAGACCTTCAACACACCCGCCATGTATGTGGCCATCCAGGCT
GTGCTCTCGCTGTACGCCTCCGGTCGTACCACCGGTATCGTTCTGGACTCCGGCGATGGTGTCTCCCACACCGTGCCCATCTACGAGGGTTATGC
CCTTCCCCATGCCATCCTGCGTCTGGATCTGGCTGGTCGCGATTTGACCGACTACCTGATGAAGATCCTGACCGAGCGCGGTTACTCTTTCACCA
CCACCGCTGAGCGTGAAATCGTCCGTGACATCAAGGAGAAGCTGTGCTATGTTGCCCTCGACTTTGAGCAGGAGATGGCCACCGCTGCCAGCAGC
TCCTCGTTGGAGAAGTCCTACGAGCTGCCCGACGGACAGGTGATCACCATCGGCAACGAGCGTTTCCGCTGCCCCGAGGCCCTGTTCCAGCCCTC
GTTCTTGGGAATGGAGGCTTGCGGCATCCACGAGACCACCTACAACTCCATCATGAAGTGTGATGTGGATATCCGTAAGGATCTGTATGCCAACA
CCGTGCTGTCCGGTGGCACCACCATGTACCCTGGCATCGCCGACCGTATGCAGAAGGAGATCACCGCCCTGGCACCGTCGACCATGAAGATCAAG
ATCATTGCCCCGCCAGAGCGCAAGTACTCTGTCTGGATCGGTGGCTCCATCCTGGCTTCGCTGTCCACCTTCCAGCAGATGTGGATCTCCAAGCA
GGAGTACGACGAGTCCGGCCCCTCCATTGTGCACCGCAAGTGCTTCTAA
(SEQ ID NO: 422)

Start ATG: 249 (Reverse strand: CAT)

MCDEEVAALVVDNGSGMCKAGFAGDDAPRAVFPSIVGRPRHQGVMVGMGQKDSYVGDEAQSKRGILTLKYPIEHGIVTNWDDMEKIWHHTFYNEL
RVAPEEHPVLLTEAPLNPKANREKMTQIMFETFNTPAMYVAIQAVLSLYASGRTTGIVLDSGDGVSHTVPIYEGYALPHAILRLDLAGRDLTDYL
MKILTERGYSFTTTAEREIVRDIKEKLCYVALDFEQEMATAASSSSLEKSYELPDGQVITIGNERFRCPEALFQPSFLGMEACGIHETTYNSIMK
CDVDIRKDLYANTVLSGGTTMYPGIADRMQKEITALAPSTMKIKIIAPPERKYSVWIGGSILASLSTFQQMWISKQEYDESGPSIVHRKCF*
(SEQ ID NO: 423)

Name: ACTIN
Classification: cytoskeletal_structural_protein
Gene Symbol: Act5C
FlyBase ID: FBgn0000042

Celera Sequence No. : 142000013384645
GGAAAGAATTTTGGTTGGATTCAAATACGAAGCAGCTTTGGTAACAACTAAGGTTCTGGGTTAGTCATGATTCACCAACAGGTTAGACTTAGTTT
TGTGGCAAAATTTAACCAATGACGTCCAAGTTCTAACTAAAGTAATATCGTTACTTGTTATTTTATTTTGGATATTCTCGAAAGTTTCTGGAA
TTCTCAAGAAAACTTAAACAATATAGAGTCGCATTATATGGAAAACTCATTGATTCATTCTTATGTTTGTTATTTTGTTATTAAATTCCAATTGA
TGATGCCAGTGTCTAAATAAAAACGAAGACCTAATTTTCAACCAAAAATCAGGTTTTCTGGGCTTGTCCGTATTAAACATTTTTGATAATTATTT
ATAATATATTGTTATTTTTTGCTGGCTTCAAAACATCAACAAATTGTGTATGATAAATGACGATGACGTTGTTGTTGATGGCGATCGCGCTGTGG
GAATCAGATGAAATGTCAATTAAGTTTGCATTTATATCTTTGATTGAAGCTCTAAGATTTGCTTTGCCATTTTATGCGGAAGTTAAGCTCGGTCA
GTTCTTGAAAAAGTTCCCATGGGAGCAAGTTATTTGTTTTTTGACAATAAGAAGCGTTTATTTAAAATGGCTTATTATGGCCTCAATGATTCCTA
ATAGGCGTAACTTACTGGTTATAAACTTGTTTAATATCGTTTCATTTTAAACCTGGATGACAGAAAATGAATTTCGGTTCAAATACAAATATTAC
AATAGAAAGTATGATATTTAGCTCCGATAAACATTTAACAATTTTAGTATTTTAATGGTGAAATGGTAAATTCCGCGCATGAAAAGAGATAGAAG
AGATGACATATATGGAAACCTTAAAAACGTAACGGTTGCTTGGGTTTTATAACAATCAGTCAGTGACAGGCATTTCCAGAGTTGCCCTGTTCAAC
AATCGATAGCTGCCTTCGGTCGCTCGTCACTAACTTTCCTTTAGGCAACGGCCACACTGTCTGGCCACCAAAATCCCAAACTTAATTAAAGAATT
AAATAATTCGAATAATAATTAAGCCCAGTAACCTACGCAGCTTGAGTGCGTAACCGATATCTAGTATACATTTCGATACATCGAAATCATGGTAG
TGTTGGAGACGGAGAAGGTAAGGCGAGAAACGGCGAGCCCGCATGGTTTCGATTTCGGCTGAGCCCGTGGCAGGAACAACAAAAACAGGGTTGTTGC
ACAAGAGGGGAGGCGATAGTCGAGCGGAAAAGTGTGCAGTTGGCGTGGCTACATCATCATTGTGTTCACCGATTATTTTTTGCACAATTGCTTAA
TATTAATTGTACTTGCACGCTATTGTCTACGTCATAGCTATCGCTATCTCTGTCTGTCTCTATCAAGCTATCTCTCTTTCGCGGTCACTCGTTCT
CTTTTTCTCTCCTTTCGCATTTGCATACGCATACCACACGTTTTCAGTGTTCTCGCTCTCTCTCTCTTGTCAAGACATCGCGCGCGTGTGTGTGG GTGTGTTCTTCTTTAGCTACATATACATAAATAGGAGAGCGGAGAGACAAATATGGAAAGAATGGAAAAAGAGTGAATTACTGCAATTAACCAGT
CGCGAACAGTTAAATCATATTTTTGTCGGCCATTGCAGTAAATAAACCGTTGGCTTTCCCTCTTCACTTTCCACCTCCTTTCTTTGACGTTAATT
TTTTTCAGTTAATCGCGCCGCTGCTTTGAACTCGAACACGAATTTTAGCCGCAACATAAAATAAAATCAAGTAACTCTTTTAACTCAAATATAAA
ACAACAATTCCAATTCTTTCAACAGGCAATCTGTGTTTTTATGTCAGATACGTGCGCGTGTGTGTGTGTGCTGTAATTCCATCGCCCCTTTCGAT
TCCGAGTTCGTTAGGAACAGCATTAGTTCGCCTATTTTAGTAGTAGCCTAGTCCGATTTTAAGTGAAACAGGATACTCCAACACCATATACTCAA
TAATTAGTTACAACACCCACTCAACCATACAGCAACAACAAGTTTAACGAGTTTTTTGTATTATCATTACTTAGTTTTTTGGTTAATAATACACA
AGTGAAGAGCGAACTGCAGGGGGAGCGAGATATCACGAAACAATCCAAAATCCACACACACTCAAACAGAAATCAAAAGCTTCGCTCTCTCGCACA
CACACGCACCAACCAACTATCAACTATCACAAACACCGCGACAGAGAGAGAGCGGCAAGTGAATCACGGCGAATCGAAACCGATCCGAACCCACT
CCGGAGCCGAAAAAGAACTGATCCTACCATCAAACGCATCCAATAAACACGGCCGCCAACATGCAGAGCGACTTTCACAGAATGAAGAACTTTGC
CAATCCCAAGTCCATGTTCAAAGTAATACTCTCAGTGCGCCTGTCGCTAAGCCAAGCTAATCTAATCTTCTGATTCCCCTTCCCATCCATTGCCA
TCTTCTCCCGCAGACCAGCGCCCCCAGCACCGAGCAGGGTCGTCCGGAACCACCAACTTCGGCTGCAGCGCCCGCCGAGGCTAAGGATGTCAAGC
CCAAGGAGGACCCACAGGAGACTGGTGAACCAGCAGGCAACACTGCAACCACTACTGCTCCTGCCGGCGACGATGCTGTGCGCACCGAGCATTTA
TACAAACACCCGCTCATGAATGTCTGGACGCTGTGGTACCTTGAAAACGATCGGTCCAAGTCCTGGGAGGACATGCAAAACGAGATCACCAGCTT
CGATACCGTCGAGGACTTCTGGAGCCTATACAACCACATCAAGCCCCCATCAGAGATCAAGCTGGGTAGTGACTACTCGCTATTCAAGAAGAACA
TTCGGTGGGTTTGCTGTTTATTGCAATTCTGCCAAGATAACCTTTACTAACTGATATCTCATTTGCAGTCCCATGTGGGAGGATGCAGCCAACAA
ACAGGGCGGTCGTTGGGTCATTACCCTTAACAAAAGCTCCAAGACCGATCTGGATAACCTATGGCTCGATGTGGTAAGTGCACAAAGAAACGAGT
GGTGAGCGGATGGTCTATTTATAGTGAATGTACATTCTTGAAATGCAAAAATATAGAAATAGGTGTATGATTTTGCAATATAAATTATAACTTAT
AGAAAATATCAGCTAAAAATACGCTAGTGCTAGCTTTTGTCTTAGGAACATTCAATAGTGAGCTTATATCATAAATATTTTTCGCATATGAGTAA
CTACAACTGTTTTGCCTTCCAGCTGCTCTGCCTGATTGGTGAGGCCTTCGATCACTCTGATCAGATCTGCGGCGCTGTTATAAACATTCGCGGCA
AGAGCAACAAGATATGTAAGTTTTCACGCACACCCAACTTCAGCGGAATTCCTTTGTTTAACGATTAATGCTTTCCAGCCATCTGGACTGCCGAC
GGAAACAACGAGGAAGCTGCCCTTGAGATTGGTCACAAGCTGCGCGATGCCCTGCGTCTGGGACGCAACAACTCGCTGCAGTATCAGTTGCACAA
GGACACGATGGTCAAGCAGGGCTCCAACGTGAAATCGATCTACACTTTGTAGGCGGCTAATAACTGGCCGCTCCTTATTCGGTCCGATCCCACAC
TGATTATTTTGTCTTTCATTTATTTATCGTTATAAGCAACAGTAGCGATTAATCGTGACTATTGTCTAAGACCCGCGTAACGAAACCGAAACGGA
ACCCCCTTTGTTATCAAAAATCGGCATAATATAAAATCTATCCGCTTTTTGTAGTCACTGTCAATAATGGATTAGACGGAAAAGTATATTAATAA
AAACCTACATTAAAACCGGATACTTTTGATCTTTGATTTTGGAGATATTTTAAAATAGAAAAAGTTAACCTATATTGTTTTTGGGATAATTACT
TGTTGTATTACTAAAACGAGCTTGTATCCTAATATGGGCACCTAAAGCAAAACTTCCAAATTTGGAATTCAATTTGTTGCTAAAAATACGTTAGC
AATTTCTAGGGTGGCCAAAAAAAAATGTGTATCGATATATCGATAGGTTTCCTAAATAGACATTAAAATAATTTTAGCTTTTTACTTATATTGTT
AGAGTAAATACGTTTGTATTTAAAAAATAAGTCAGTATTTTTTTTTTATTAACCTATTATTGAATTTTATATGAGTGAGAGCTTTTCCATTCAGC
CAAGAACGGTCACACTGCATGTGACATGTTTCAATTGTGTAGGCGCAGTCACACTGGTCGCGTCGCTCGTAGATATCGTGTAAGGATATGTCTCC
GTGTTTAGCTAAATAAAATACATAAAATATATGTGCAATTCTAACAAGCATAGCCATTTAGCGTAGAGTAGTGGAACGAACAGCTCGTACCGGGC
CAGTAACAACAAATTAACAAGCAAACGCACTAAAGTTTGTCGCGGAATAAAGATATAATAATAGACCAGCTAACCAACACAAACAAACACACACA
CGGCCAGAAGTTCGTTGGCGTTGAAAGGGAAAAATGAAACGAAATGAAAGGAGAATAACAGTGCAATAGATTCGGTTTACATTGTGCAAAAAATC
GAAGTAGCCCCTGCCAACAGGGTCGCTAAAAATAAAGAAGGCGACAGCCTCTGTTTATCGTTGGGAATAAACAAATATATGGCCAGCGGAGGAGA
ATCATAACAAAGGCGCAAGACTAGCCAGCATAAAAGACAAAGGAGCTCTCCTCCCCCGCGTCCGCCACCCCCCTCCCTTTTTGGGGTTGAAAACC
CCCCACGCGTTGCGGTGCAGCATCGCCCCGACTATGCGATACCCTGCAATCGAGTTTATAGTGCTATAG
(SEQ ID NO: 424)

Exon: 1001..1157
Exon: 2070..2397
Exon: 2484..2854
Exon: 2919..3018
Exon: 3253..3340
Exon: 3404..3819
Start ATG: 2341

Transcript No. : CT13384
GCCACACTGTCTGGCCACCAAAATCCCAAACTTAATTAAAGAATTAAATAATTCGAATAATAATTAAGCCCAGTAACCTACGCAGCTTGAGTGCG
TAACCGATATCTAGTATACATTTCGATACATCGAAATCATGGTAGTGTTGGAGACGGAGAAGTTTTTGGTTAATAATACACAAGTGAAGAGCGA
ACTGCAGGGGGAGCGAGATATCACGAAACAATCCAAAATCCACACACACTCAAACAGAAATCAAAAGCTTCGCTCTCTCGCACACACACGCACCAA
CCAACTATCAACTATCACAAACACCGCGACAGAGAGAGAGCGGCAAGTGAATCACGGCGAATCGAAACCGATCCGAACCCACTCCGGAGCCGAAA
AAGAACTGATCCTACCATCAAACGCATCCAATAAACACGGCCGCCAACATGCAGAGCGACTTTCACAGAATGAAGAACTTTGCCAATCCCAAGTC
CATGTTCAAAACCAGCGCCCCCAGCACCGAGCAGGGTCGTCCGGAACCACCAACTTCGGCTGCAGCGCCCGCCGAGGCTAAGGATGTCAAGCCCA
AGGAGGACCCACAGGAGACTGGTGAACCAGCAGGCAACACTGCAACCACTACTGCTCCTGCCGGCGACGATGCTGTGCGCACCGAGCATTTATAC
AAACACCCGCTCATGAATGTCTGGACGCTGTGGTACCTTGAAAACGATCGGTCCAAGTCCTGGGAGGACATGCAAAACGAGATCACCAGCTTCGA
TACCGTCGAGGACTTCTGGAGCCTATACAACCACATCAAGCCCCCATCAGAGATCAAGCTGGGTAGTGACTACTCGCTATTCAAGAAGAACATTC
GTCCCATGTGGGAGGATGCAGCCAACAAACAGGGCGGTCGTTGGGTCATTACCCTTAACAAAAGCTCCAAGACCGATCTGGATAACCTATGGCTC
GATGTGCTGCTCTGCCTGATTGGTGAGGCCTTCGATCACTCTGATCAGATCTGCGGCGCTGTTATAAACATTCGCGGCAAGAGCAACAAGATATC
CATCTGGACTGCCGACGGAAACAACGAGGAAGCTGCCCTTGAGATTGGTCACAAGCTGCGCGATGCCCTGCGTCTGGGACGCAACAACTCGCTGC
AGTATCAGTTGCACAAGGACACGATGGTCAAGCAGGGCTCCAACGTGAAATCGATCTACACTTTGTAGGCGGCTAATAACTGGCCGCTCCTTATT
CGGTCCGATCCCACACTGATTATTTTGTCTTTCATTTATTTATCGTTATAAGCAACAGTAGCGATTAATCGTGACTATTGTCTAAGACCCGCGTA
ACGAAACCGAAACGGAACCCCCTTTGTTATCAAAAATCGGCATAATATAAAATCTATCCGCTTTTTGTAGTCACTGTCAATAATGGATTAGACGG
AAAAGTATATTAATAAAAACCTACATTAAAACCGG
(SEQ ID NO: 425)

Start ATG: 429

MQSDFHRMKNFANPKSMFKTSAPSTEQGRPEPPTSAAAPAEAKDVKPKEDPQETGEPAGNTATTTAPAGDDAVRTEHLYKHPLMNVWTLWYLEND
RSKSWEDMQNEITSFDTVEDFWSLYNHIKPPSEIKLGSDYSLFKKNIRPMWEDAANKQGGRWVITLNKSSKTDLDNLWLDVLLCLIGEAFDHSDQ
ICGAVINIRGKSNKISIWTADGNNEEAALEIGHKLRDALRLGRNNSLQYQLHKDTMVKQGSNVKSIYTL*
(SEQ ID NO: 426)

FIGURE SHEET 235

Name: eIF4E
Classification: translation_factor
Gene Symbol: eIF-4E
FlyBase ID: FBgn0015218

Celera Sequence No. : 142000013384826
CCCGATGATGTAGATTTTAAGGACAGCGGAAAAATAAGCTCCTTGAAGGCCCTGGGTCCATTTATAGCCGGCAAGGAGAATAGCCGCAACACGGT
TTACCTCAGCGATGTTCCGGATATTTGCAAGGATAAGCCGTGCATGCTGGGCGTGGACGAAGCAGGGCGTGGTCCCGTCCTGGGACCTATGGTAT
ATGGGATCTCCTACTGTCCACTGGAAAGTAACAAGGCTTTAGAGGACCTGGGATGCGCCGATTCCAAACAACTAACCGAGGGGAAACGTGATATC
ATATTTAACGATATCAACACCAAGGAATATGCGACCAGTTGCGTTGGCTGGGCCGTGGAGATCATATCGCCGAACACGATCAGCACCAGCATGTA
CCGGCGGTCGAAGTGCTCCCTGAACGAAGTTTCCATGGACTCGGCCATGGGCCTTATCCAACAGGCGATCGATGCGGGCGTCAATATAGCCGAGG
TTTATGTGGATACGGTGGGTCCGCCGGAGAAGTACCAGGAGAAGTTGCTCAAACGTTTCCCCAGCTTTAAAATCACCGTGGCGAAAAAAGCTGAC
TCCACCTATCCAATAGTCTCTGCTGCTAGTATATGCGCCAAAGTTACCCGTGATCATGCCCTCAAGGTGTGGAGCTTCCCCGAGGGCTTGGTCAT
TAAGGACAACGAGTTCGGCAGTGGATATCCGGGAGATCCGGTCACAAGAAGATTTCTGACCGAGTACATCGATCTAGTGTTTGGATTTCCACGAC
TTGTGCGCTTCAGTTGGTCCACCGCGGAAAACGCACTGGCGGACAAGGCCTATGACATGGAGTTCGACGAGCCGGATTCCGAGAAGCCCAAGTAC
GCCGGCACCAAGCTCACAAAGTTCTTTAAGGGCACAACAAAATCCGGCGAAATAATTCGCGAGGAGTGCCGCTTCTTTAAGCAACGCCATCTGGA
AAGTGTCATGGAGTTTTAGCAACAAATGAAAATAAAATTAAGTTCAGGAGTATCTATATTTACAAAGAATAAAGTTTAATTTAAGTACTTTAGTA
TTAAATTTTAAAATGCTAAAATACAAAAAACACCCAGGCCCAAAACGAAAACAGATTAATTTTTATCTTTAATGTATTTTTGCTGATGTTCTTGT
GTTTCCGCCAATCTCGTGTTCTTAATAATTACGTTCGATTACTGACTACGTGGGACTGCAGTTACACTGTTCTGAATGTATGCGTGAATCGGTCT
GATCTGATCTCTTGGCATCCCTTTTTTGGAGGACAACTGTGGAATTGGGTAAAGGACTTTTGGTGGGGAGGGCGGGGAGTTGGCTGGCATCTTTG
ATCGATACAATAACAAAATGCAAAGTTATACTAAACGATTTTCGTATAAAAAGGGACGACCTTAGAAACATGGAGCTTATGATTAAGATTAAAAT
GAGGCGAGTCGCATCCCGCTGATCTGAAGAGAACAACAACCATGTTGAAGCCCCCAAAAATCCCAGGTGCATATCGATATTTTGTGACTCGAAAC
TAAGCGTACGAAATAGACGTGGACAAAAGCGGGAGGATCTCATCTCAAGAGGTATACCTTAAAGAACTAATTAGAATTTAAAGCAATTACAAATA
CGATTGCAGGGCGGGATAGCTAAGAAAGGAGTTACCTAAGGTCCGGACTCCAGATCCAAATCGACTTATGTTGGTAGAATTGTAACTGATCATAT
TTCACTTCTTTAAAAAATATAGTTAAATGCAATTTTTGAATCAAAAGTAAAAACTTCTCGTTCCGTAAGAAAGTGAAAAACTACCGATTTCATTT
TTACCAAATAATGAGCTGGAAAAGGAATCTTGACTATTTTAAGCGTTGGCTCAATACACGAAATCCAGTTGTGGCTGCTCCGGCAATCAGAACTT
TCGCAGGTCCAACACGAAAACGCTACCGTCGGAGGCACTGGCACCCACCTTAGTGCCCTTGGAGTTCCAGCACACCTCAAAGATTCCGCCCGTGC
CCTTGTAACTGTGCACTAGCTGTCCCGTTTGCGTGCTCCAAATGTGTACGCACTTGTCGAAGCTGCCGGAGGCCAAATGCTTTCCATCCGGACTG
AAGGCCACCGAATAGACTGGCTCTGTGTGCTTGGTGAGCGTGTGGATACAGCTGCCCCTCTCCACGTCCCACAGTCTTACCGTGGAATCGAACGA
AGCGGATGCGAGGATCAGGTTTGTGTTTGGATTATTGGTTCCCGGCCCCGTGGGCGACCATTTTATCGTATAGATCTCCTTTGAGTGAGCCTGCA
GATCGTGGCAGCAACGATCTCGGTTCATGCTCCAGATCTTGAGGGTCATGTCATCAGAGCAGGACGCCAGCAGTTGGCCCTGCGGACACCACTTG
ATTGCATTCACCTCGTTTGTGTGTCCTTTAAAGGTCTTGATGGGTTCATTTACACCCAACCGGCACACATGTATCCGCTGATCCGTACTGCAAGA
GGCAAAGGCCTGGTTTGTCTGCCAGTCCACATCCAAGGCTGGAGCACTGTGAAAGGCAAATTGCTGGGTGCATTGGCCCGTGGATGCGTCCCAGA
TGATCGTCGTCTTGTCCACGCCAGCCGAGAGGATGTAGTTGCCGCACTTGTTCCACTTCAGAGCAAAGATCGGACCCTTGTGTTGTCCCAAAGTA
GAAGCAAGTCGACCGTCGGTTTTCCAAATTCGGGCGTAACCATCGTAGCTGCCGGTGGCGAGCAAGGAACCATCGCACTGCAAAAACGAGAATAG
ATTAAGTAAGGATCAGAAATCAAACTTTGCAAGGCTTAAGTGCCAAGATCTTCGACTTACATTCCAGTCCAGAGAGGTGACGTCCTTGTTGCTAG
GCACCTCAGCGCCGCCTTTCTGGATGCAGTGGCGCAGCACCAACTGGTTGGAGTTAGTGTTTGCATCGGACATGTCCCATATCCTAGCAGTGCTG
TCTCCCGAACCGCTTGCCAGTAAATCCCGGCTAGGATTCCATGCGCAGATAAACACCTCGCTTTCGTGGCCGCGTAATACACGAGCCTTGGATTC
GGGTATTTCGATGTTCTCGTCAATGTCCATGGGAACAAGAGCTGCGGGAGTCCCAGCACCTCCGCTGGTAGACGAGGAGATGGTTCCACTGGGAG
CAGAGCTTTGAGCATTGGACGAACCAGACTGCACGTTGTTTCCTTGGGCTCCTACGCGAATCGTAACCGCTCCACTTGGCGCCTTTGATCCTGTT
GCAGTCGAAGCTCCGCCCGATGCTGCTGCGTCCGGATTGGAGGTTGATACAGTTCCACCAGCGGGCGTCAGCCCGCTTGTAGGTTGTTCTACGCT
GCTGGAAGTGCTGCTATTGCCATTTGTGGATGTTGAGGAGGCTGCATCATCGGTACTGGTAGCATTTGCATTGCCTGCATTGCCACTAGATGAGC
TTCCCGCTTCATTCGAGTTCTGGGATTTCTTTTGACTTGCCCCAGGTGCTGCCAAATCTCCACCAGCTGGTGTGCTTGTGCTATTAGATCCTCCA
GTACTGGCCTGGTTCCCTCCAGCTCCATTGTTTCCGGCGTATGTGCCGCCAGCATTATTTGCCGCATTTCCACTGGAGTCTACCTCGCTTGCCGA
CTGATCGGTTGGTGTGCTTGTGCCCGTGGTGCTGCCAGCAATTTTGTTTCCACCTGCTGAGCCCGCCACTCCGGTACCCGGTTCTATTTTTATCT
CAGGCTTGGCATTGTTGTTCTGGTTGCCACCGGCAGGGGCAGAAGAGTCGACTGCCCCGGGTTTTCCCGGCTCTGTTTTCACAATGGGCTTGAGT
GGCTTCACCTCCGGCATGACAGCGTCTATTAGAGAGAGTCCTTCAATGGGTCGCGCCACCTCGCCGTCTTCGCCTACGCTCCACTCCACTTCAGT
GTACAGAAGACCCTTCTGCAGGATGGTGAGCAAAGCGGCAGGTGGAACCAATGCGCCATTGATATTACTTTGCGAGATGTGTGACTCAATGCCAA
ACACGTAGGCCGAGTGCAGAAAGCCTAGAAAACGGGATTGCATGAGATTAGGGCGGGCTGTTATCTTGCGATTGGAGGGTTTTACTCACCCGACT
CCTGCAGGTATCGGTAAACCAGAAAGTTCACCTCGTCGCTGGAAAAACTCATGACGGAACGCGGTTGGCTCCTTCTCCTACTACTAGCGCACTCC
AAAATCCACTCCTATCTCCAATGCCAATTATGTTTTTACGGTGCGAAAATCGGAACTGTGCTGCGTAACACATGCGTCTGCATTCGGCACGCTTA
TCACTTCGGCGCAAGCCACGGTATCCGGTGCTACTCCTGGTACTTGGATCGATCTGGTCGGTCCTGTGTTTTCAATTCTGCCAGTTTGCTGCTTG
CCGCAAGAGCACTTCACATATTTTTTCCACAAATAAAACCGAGGGATCGAAAACGCGTTTCTGAAACGCGCAAAAAAATGGCGGAGTAATCTCAA
GGTGTGCGCTGCGAGAGGTTGCGCAGCCTTGTGTTTTGTGACGTCACAAGTTTTGACAACAACTTAATCAAATTTGAGTCATATTTTTGTATTGC
ACCAAGCGTTACCTTAAAGGATAGAACGGAAATTTATTAGCCATAAAAACAATTAAGAAGATATTTTTGGATTTCTGCTTGGAGCAAAAGGTAAA
AAATTCTTAAAGCGAATTGTCGTCTCTCTTCGTCCATCCCTGTGTACCCATCCCTCGAAGTAATCATTGTATTTCAACCCAACGCTCTACTGGTC
ACACCAATCGTTCCACCCGCGCCCGCTAGATGGCTCCACTCTTAGGCAGCGAGAGCGAAGAAAAATCAATAGAAATTTTCATTTAGTGAATTGC
CCTGCACTTGGTAATAGTTAACAAACAAATTAGCGGCAAATCAGCGAGGCGAAGCTCCAGCGAGTTGGAGTTCCATAAAGTGCAACACGCAGGGT
CAAACATTCCGCAGCCAACACCCCGGATTCCGATTCCAAGCGAAGCCAACTTCAGAAGTCAGAGATTACTCTCTCTGCTCCGCCACAGAAATTCC
GCAACGCTAACCGATTTTGTCCGCTGGCGAGTAAAAAAAATCGGAAAAGTAAGCTCAAAAAAAAAGAACAGCTAACATACGCCCATTAATGTTTT
TGGAGGCTTCTTCGGTGCTTTTTTTTTGGGCAAAACGCCCTCGTCATCCAGCGGTGAAAAAAGTGACGTGACATGAAAGCAAAGAAAGAAGAGA
ACCGAAGAGCGCAGTGAAAAACAGAAAATAAAACGAAACGGAAAGCAAAGTAAAAAGTATACTACAGAAACAAAAGCCGGTGGTCGCGCAAATCC
AAATAATAATGCCCAAGTGCACATCGACTTCGCCAGGCGATAAAAAGTGGGCGAGCGAGGTCACAGAATCTTTATCAACGGGCAAAACGCTGCCA
AGTTGAAAATAAATCGGTTGCCAAAAATGCGGGGGTACAC
(SEQ ID NO: 427)

Exon: 4455..4080
Exon: 4014..2816
Exon: 2737..1001
Start ATG: 4137 (Reverse strand: CAT)

FIGURE SHEET 236

Transcript No. : CT13462
TCCGCCATTTTTTTGCGCGTTTCAGAAACGCGTTTTCGATCCCTCGGTTTTATTTGTGGAAAAAATATGTGAAGTGCTCTTGCGGCAAGCAGCAA
ACTGGCAGAATTGAAAACACAGGACCGACCAGATCGATCCAAGTACCAGGAGTAGCACCGGATACCGTGGCTTGCGCCGAAGTGATAAGCGTGCC
GAATGCAGACGCATGTGTTACGCAGCACAGTTCCGATTTTCGCACCGTAAAAACATAATTGGCATTGGAGATAGGAGTGGATTTTGGAGTGCGCT
AGTAGTAGGAGAAGGAGCCAACCGCGTTCCGTCATGAGTTTTTCCAGCGACGAGGTGAACTTTCTGGTTTACCGATACCTGCAGGAGTCGGGCTT
TCTGCACTCGGCCTACGTGTTTGGCATTGAGTCACACATCTCGCAAAGTAATATCAATGGCGCATTGGTTCCACCTGCCGCTTTGCTCACCATCC
TGCAGAAGGGTCTTCTGTACACTGAAGTGGAGTGGAGCGTAGGCGAAGACGGCGAGGTGGCGCGACCCATTGAAGGACTCTCTCTAATAGACGCT
GTCATGCCGGAGGTGAAGCCACTCAAGCCCATTGTGAAAACAGAGCCGGGAAAACCCGGGGCAGTCGACTCTTCTGCCCCTGCCGGTGGCAACCA
GAACAACAATGCCAAGCCTGAGATAAAAATAGAACCGGGTACCGGAGTGGCGGGCTCAGCAGGTGGAAACAAAATTGCTGGCAGCACCACGGGCA
CAAGCACACCAACCGATCAGTCGGCAAGCGAGGTAGACTCCAGTGGAAATGCGGCAAATAATGCTGGCGGCACATACGCCGGAAACAATGGAGCT
GGAGGGAACCAGGCCAGTACTGGAGGATCTAATAGCACAAGCACACCAGCTGGTGGAGATTTGGCAGCACCTGGGGCAAGTCAAAAGAAATCCCA
GAACTCGAATGAAGCGGGAAGCTCATCTAGTGGCAATGCAGGCAATGCAAATGCTACCAGTACCGATGATGCAGCCTCCTCAACATCCACAAATG
GCAATAGCAGCACTTCCAGCAGCGTAGAACAACCTACAAGCGGGCTGACGCCCGCTGGTGGAACTGTATCAACCTCCAATCCGGACGCAGCAGCA
TCGGGCGGAGCTTCGACTGCAACAGGATCAAAGGCGCCAAGTGGAGCGGTTACGATTCGCGTAGGAGCCCAAGGAAACAACGTGCAGTCTGGTTC
GTCCAATGCTCAAAGCTCTGCTCCCAGTGGAACCATCTCCTCGTCTACCAGCGGAGGTGCTGGGACTCCCGCAGCTCTTGTTCCCATGGACATTG
ACGAGAACATCGAAATACCCGAATCCAAGGCTCGTGTATTACGCGGCCACGAAAGCGAGGTGTTTATCTGCGCATGGAATCCTAGCCGGGATTTA
CTGGCAAGCGGTTCGGGAGACAGCACTGCTAGGATATGGACATGTCCGATGCAAACACTAACTCCAACCAGTTGGTGCTGCGCCACTGCATCCA
GAAAGGCGGCGCTGAGGTGCCTAGCAACAAGGACGTCACCTCTCTGGACTGGAATTGCGATGGTTCCTTGCTCGCCACCGGCAGCTACGATGGTT
ACGCCCGAATTTGGAAAACCGACGGTCGACTTGCTTCTACTTTGGGACAACACAAGGGTCCGATCTTTGCTCTGAAGTGGAACAAGTGCGGCAAC
TACATCCTCTCGGCTGGCGTGGACAAGACGACGATCATCTGGGACGCATCCACGGGCCAATGCACCCAGCAATTTGCCTTTCACAGTGCTCCAGC
CTTGGATGTGGACTGGCAGACAAACCAGGCCTTTGCCTCTTGCAGTACGGATCAGCGGATACATGTGTGCCGGTTGGGTGTAAATGAACCCATCA
AGACCTTTAAAGGACACACAAACGAGGTGAATGCAATCAAGTGGTGTCCGCAGGGCCAACTGCTGGCGTCCTGCTCTGATGACATGACCCTCAAG
ATCTGGAGCATGAACCGAGATCGTTGCTGCCACGATCTGCAGGCTCACTCAAAGGAGATCTATACGATAAAATGGTCGCCCACGGGGCCGGGAAC
CAATAATCCAAACACAAACCTGATCCTCGCATCCGCTTCGTTCGATTCCACGGTAAGACTGTGGGACGTGGAGAGGGGCAGCTGTATCCACACGC
TCACCAAGCACACAGAGCCAGTCTATTCGGTGGCCTTCAGTCCGGATGGAAAGCATTTGGCCTCCGGCAGCTTCGACAAGTGCGTACACATTTGG
AGCACGCAAACGGGACAGCTAGTGCACAGTTACAAGGGCACGGGCGGAATCTTTGAGGTGTGCTGGAACTCCAAGGGCACTAAGGTGGGTGCCAG
TGCCTCCGACGGTAGCGTTTTCGTGTTGGACCTGCGAAAGTTCTGATTGCCGGAGCAGCCACAACTGGATTTCGTGTATTGAGCCAACGCTTAAA
ATAGTCAAGATTCCTTTTCCAGCTCATTATTTGGTAAAAATGAAATCGGTAGTTTTTCACTTTCTTACGGAACGAGAAGTTTTTACTTTTGATTC
AAAAATTGCATTTAACTATATTTTTTAAAGAAGTGAAATATGATCAGTTACAATTCTACCAACATAAGTCGATTTGGATCTGGAGTCCGGACCTT
AGGTAACTCCTTTCTTAGCTATCCCGCCCTGCAATCGTATTTGTAATTGCTTTAAATTCTAATTAGTTCTTTAAGGTATACCTCTTGAGATGAGA
TCCTCCCGCTTTTGTCCACGTCTATTTCGTACGCTTAGTTTCGAGTCACAAAATATCGATATGCACCTGGGATTTTTGGGGGCTTCAACATGGTT
GTTGTTCTCTTCAGATCAGCGGGATGCGACTCGCCTCATTTTAATCTTAATCATAAGCTCCATGTTTCTAAGGTCGTCCCTTTTTATACGAAAAT
CGTTTAGTATAACTTTGCATTTTGTTATTGTATCGATCAAAGATGCCAGCCAACTCCCCGCCCTCCCCACCAAAAGTCCTTTACCCAATTCCACA
GTTGTCCTCCAAAAAAGGATGCCAAGAGATCAGATCAGACCGATTCACGCATACATTCAGAACAGTGTAACTGCAGTCCCACGTAGTCAGTAAT
CGAACGTAATTATTAAGAACACGAGATTGGCGGAAACACAAGAACATCAGCAAAAATACATTAAAGATAAAAATTAATCTGTTTTCGTTTTGGGC
CTGGGTGTTTTTTGTATTTTAGCATTTTAAAATTTAATACTAAAGTACTTAAATTAAACTTTATTCTTTGTAAATATAGATA
(SEQ ID NO: 428)

Start ATG: 319 (Reverse strand: CAT)

MSFSSDEVNFLVYRYLQESGFLHSAYVFGIESHISQSNINGALVPPAALLTILQKGLLYTEVEWSVGEDGEVARPIEGLSLIDAVMPEVKPLKPI
VKTEPGKPGAVDSSAPAGGNQNNNAKPEIKIEPGTGVAGSAGGNKIAGSTTGTSTPTDQSASEVDSSGNAANNAGGTYAGNNGAGGNQASTGGSN
STSTPAGGDLAAPGASQKKSQNSNEAGSSSSGNAGNANATSTDDAASSTSTNGNSSTSSSVEQPTSGLTPAGGTVSTSNPDAAASGGASTATGSK
APSGAVTIRVGAQGNNVQSGSSNAQSSAPSGTISSSTSGGAGTPAALVPMDIDENIEIPESKARVLRGHESEVFICAWNPSRDLLASGSGDSTAR
IWDMSDANTNSNQLVLRHCIQKGGAEVPSNKDVTSLDWNCDGSLLATGSYDGYARIWKTDGRLASTLGQHKGPIFALKWNKCGNYILSAGVDKTT
IIWDASTGQCTQQFAFHSAPALDVDWQTNQAFASCSTDQRIHVCRLGVNEPIKTFKGHTNEVNAIKWCPQGQLLASCSDDMTLKIWSMNRDRCCH
DLQAHSKEIYTIKWSPTGPGTNNPNTNLILASASFDSTVRLWDVERGSCIHTLTKHTEPVYSVAFSPDGKHLASGSFDKCVHIWSTQTGQLVHSY
KGTGGIFEVCWNSKGTKVGASASDGSVFVLDLRKF*
(SEQ ID NO: 429)

Name: transducin (beta) like 1 protein
Classification: signal_transduction
Gene Symbol: ebi
FlyBase ID: FBgn0023444

Celera Sequence No. : 142000013384830
ACCTTCTCCCAGATTTTTGTTGGAACTTATAGCCGTTTCCAGGAAAAGACTCGAGCAGGGAGATTAAGTGCATGTCGCAATCGAAGAGAACGTTG
GCAGATTTGACCATTGTTATTTGAGGCTTCATCGACACTTTGATTAACTTTAGTTATTTTCTATGAACTGTATCTGTGTTGTGGGTTGCTAATTG
TTTGAAACTTCTTTCTTGCAGACGTCGATGAGGCCTCCAAGAAGGAGATCAAGGACATTCTGGTGCAGTACGACAGAACCCTGCTGGTCGGCGAT
CCGCGTCGCTGCGAGCCCAAGAAGTTCGGCGGTCCAGGTGCCCGTGCTCGCTACCAGAAGTCGTACCGTTAAACTACTCTGTCTGGTTTTCAATT
TGGATTAGAGCTATTTTTTACAATTTGAAAATGGTTTGCACGCACGTGCGAATAAAACGGAATAATTAACTGTACAAACGAGTAGTTTTGTTCTA
TAAAGTGGGTGAAATATGTATAACAAAACCTTTTTTGGAACTAAGTGACGGTTTCCAGAAGAATTGAGTTTTCGAAAAATTAATTTTTGAAGCAG
ATGATATTCAGTTTGAGAACATAATTTTATAAAGAGGTGTTTATATCTTGGAAGGAGTAATATTTGAAAATTCTTGAACAATGTTCGGTAGGTTT
GCGCCTCTGCTAAGAACAATCACTGAGTATGGTATCTTTTTGGTATTTAATTAGATGGACTTATTTCTGAACTCCGCCAACGGCCACTCTATAAT
GCAGCCATCGTTTGTTTTTCAAAACGTATAGCTAAATTTCGGGTTAATAATATCTATCAAATGTTTATTTGAAAATTTAAAATTCTACAAGTAAT
TTTTTCCCCTATAAGCACTTATATATATATTTATTTTTATATTCATATTTTATTCCTTTGCAAATTTTTTCGACTTAAGATTTCCTCGAATTTCC
CACTGCAGCTACAAAGTAGCTAAGTTGCCTACACAGCCACGTAGTTAGTCATGGGAGCTTTGTTTGGAAAAACCAGCAAAAAGACGGCTCCTAGT
CGGATCACCGACCAGGACAAGGCGGTTCTGGTAAGTTGGTGGTAACTGAGTAGCCAGAAAGTTTGCCCAAACACTTAGCCACTTCCCCATTGCAG
CAATTGAAGCAACAGAGGGATCGTCTGAAGCAGTACCAAAAACGCATCGAGACGCAGTTGGAGAATGATCGCCTCCTGGCAAGGAAGTGCCTACA GCAAGGTCGCAAGGAGTATGTGTCATACCCATATGTGATCTAAACATGTTCAACTAAACCGATTGCTTTCATTTTAGCCGGGCCAAGCTGCTGCT
GCGCAAGAAGAAGTACCAGGAGAGTCTGCTGACCAATGCCGACAAACAGCTGGAAAACCTGGAGAAGCTGGCTGCGGACATTGAGTTCGCCCAGG
TGGAGATGAAGGTGCTGGACGGCCTCAAAGCGGGCAATGCTGCTCTGAAGAAGGTGCACGAAATGCTTGACATCGACGAAGTTGAGCGAATCATG
GACGAGACACGCGAGGGCATCGAAAAGCAGCAGGAAATAGACGCCATACTGACGGATGTGCTGACCACGCAGGACGAGGAGGACGTTTTGGCCGA
GCTGGATGCCCTGGAGGCGGAGGAAGAGCAGCAGAAGGGTGCACAGCTGCCGGATGTGCCCACCGAAGATCTGCCCATTCCCGCTGAGATCGAGT
CCGTCGAGGAGCCGGCAAAGACCAAAGCAACCAAGAAAGTCCTGGTGGAGGCATAGAACCTATAGTAAAACGAAACCAATGCCATTTTGTATGTA
TATATGTCGTTCAACTAAATTTCTCGATAAGTCCAATGTGAAATACATATTTTAATAGATTATGCTTGACTAAAGAACACATAGACTCGCATGTC
TACTTGTGTATTGTCTTTGTTGATCGACGCAGGTCCTCCTTCACCTTGCTGCGCAGCATCTTATTGGTCTCGTTCAGCTTCTCGATCTCCTCAAT
CAGGATCACGTTCTCCTTGAACAGCTTGTCGTACTTCTTCTGCACGGATTTGTCCTCGGCCACCGACTTGTATCGGTCCAGAACATTCTCGATCT
GCCTGCGCTGCCGCATAAACTCGTCCCTGACCTCCGCGTCCAGAGTGACGAATCGCTTTAGCTCGTCGTCGGAGGCGTGTTTGCGGAACAGTTCT
TTCACCGCCTTCTTGAGGGCCTCGGCCGAGTTGATCTCCCCGGCCACGTAGTAAATATCCGAGCAGATGGAGTGCAGGCACTCCCGAGAAGCCTT
TGCCCGATGTCGCTCCGTCCGAAGTTCGGCCACATTACTGAGGTATTTATCCCGCATCTCCTTTAACTGCAGCTCCAACTGCACGTTGTTCTGAT
TGAGACCCTCCAGCTCCGCTTCCATTTCGATGATGTGCTTGCGCTTGTCGTTGATCTGAAACTCACGCGGCTCAATCTGCGCCTTGAGCTCGGCA
ATCTTGTGGCCCAGCACCTGCTTGTACTTGTCCAGCTCCTGGTTCTTGTGCAGCAGGTCTTGGATGCGTTTTTCCTTGCCGTTGATGGCGTAGTC
GCGATCGGCAATGTCCTTCTGTAGATCCTCGATGTTGCGCATCTGTTTCTGGATGTTGCGCTGCGACTTGTGGTGCTCCTCCTTTAGGATCTCAA
CTTCCTCTAGGAGATTGTCAATCTCTCGGCTCTGCGACTCGAATTTCTTCTGCAAGACACCCGCTTTACCTCGCCACATTTGGGTTTCATTTCGC
TCAGTGGTCAA
(SEQ ID NO: 430)

Exon: 1001..1075
Exon: 1141..1250
Exon: 1313..1766
Start ATG: 1001

Transcript No. : CT13482
ATGGGAGCTTTGTTTGGAAAAACCAGCAAAAAGACGGCTCCTAGTCGGATCACCGACCAGGACAAGGCGGTTCTGCAATTGAAGCAACAGAGGGA
TCGTCTGAAGCAGTACCAAAAACGCATCGAGACGCAGTTGGAGAATGATCGCCTCCTGGCAAGGAAGTGCCTACAGCAAGGTCGCAAGGACCGGG
CCAAGCTGCTGCTGCGCAAGAAGAAGTACCAGGAGAGTCTGCTGACCAATGCCGACAAACAGCTGGAAAACCTGGAGAAGCTGGCTGCGGACATT
GAGTTCGCCCAGGTGGAGATGAAGGTGCTGGACGGCCTCAAAGCGGGCAATGCTGCTCTGAAGAAGGTGCACGAAATGCTTGACATCGACGAAGT
TGAGCGAATCATGGACGAGACACGCGAGGGCATCGAAAAGCAGCAGGAAATAGACGCCATACTGACGGATGTGCTGACCACGCAGGACGAGGAGG
ACGTTTTGGCCGAGCTGGATGCCCTGGAGGCGGAGGAAGAGCAGCAGAAGGGTGCACAGCTGCCGGATGTGCCCACCGAAGATCTGCCCATTCCC
GCTGAGATCGAGTCCGTCGAGGAGCCGGCAAAGACCAAAGCAACCAAGAAAGTCCTGGTGGAGGCATAG
(SEQ ID NO: 431)

Start ATG: 1

MGALFGKTSKKTAPSRITDQDKAVLQLKQQRDRLKQYQKRIETQLENDRLLARKCLQQGRKDRAKLLLRKKKYQESLLTNADKQLENLEKLAADI
EFAQVEMKVLDGLKAGNAALKKVHEMLDIDEVERIMDETREGIEKQQEIDAILTDVLTTQDEEDVLAELDALEAEEEQQKGAQLPDVPTEDLPIP
AEIESVEEPAKTKATKKVLVEA*
(SEQ ID NO: 432)

Classification: hypothetical

Celera Sequence No. : 142000013384676
TACGCCTTGCAGTGGACGAAGTGGTCAAGGCCACCATGGCGACAATTACAACGACATCGCCCAATGAAACCCGCCAGGCGACTGACCATTTGACT
CCGGTGGCCTCGCGTCAAGAATTGAAAGATCAGCTCCTACAGCGTAGCAAGGAGGACAAGATGCGGCATCAGCTGAACACGCCCACCACCCAATT
CGGACGAGCTCTACAAAAGACTCTGCAGCTTATCGAAACGCAGATTGTACAGGATCATCTCCGTGCGCTGCAGGATGCACCACCTATTCACGAAC
TTTTTGTGTTCAGCGACATTGCTACCGTGCGGCGAAACATAATTGGTGCTCCGCGGGCTGCACTGCACACTGCCCTGAATAATCCACATTTTTAC
ATGCAGTGCAAGTGCTGCGAGCTACAAGATCAATCACTGCTGGTTGGCACACTGCCCGATCTCTCCGTGGTTTACAAGCTGCACCTGGAGTGCGG
TCGCATGATCAACCTTTTCGACTGGCTGCAGGCCTTTCGATCTGTTGTGAGCGACAGCGACCACGAGGAAGTGGCCCAGGAACAAATCGATCCCC
AGATCCAGTGAGTAAAAAAATGGATTTCTCTCTGTAATATCATCAATTTCATTTGGTTTTCCTTTCAACCAGGGCCCGATTCACGCGTGCCGTAG
CCGAGTTGCAGTTTCTGGGGTACATTAAGATGTCGAAGCGCAAGACGGATCATGCCACTCGATTAACCTGGTAGCTCGCTCGGGCTATGAATAAC
CAAAATCCCTTAGGTATTTTTATCTTTTCTATTTATTTATATTGGGGCAAATTTCATGTGTGGGACGTTATGAATAAATAAAACATCAATCGATT
TGTCTACTCTGTACGAAATGCATTAACTTTGTTTGCGAGTGAAGCGCGTTCTTGTATTTTTTAAGTAAAGCCCAGCAGCTGGCAAGGCAAGCGTA
CTAAATATCAATTACCAGTCTTCCCGACTAGCGGTTACCACGTTCCCTGTTCACATTAGTTTCAGAGTCTCGATGGCGGCAGCGATGCGTTCGAT
CTCTGCCCGCGACTCGCAGAGTTTTGTCTCGTTGGCCTCCTGCACCTCGGCGGGAACCTTAGTTGCGTAGTCGGCGGCCTGGATGGCCTGAGTTA
GCTTGCCCACCGTCTGCACCAGCTGGTCGCTCTTCTTCTGCAGCTTGGCTATCTCCTTGTCCGCCTCCACGAGTCCCTTGAGCAGCAGGTGCACC
TCGCACTGGCCCGTCACGGTGAGGATCGCACAGCCCTGCGGTGCGGGACTGTCAAAGACCACATTGGAGCAGTAGGAGATTGTGGCCAGATCGCT
GGCGTAGCGTTTGAGTATTTCACTGGGCACCGAATCCGTGCATACTATATACACCTCGGTTTTAACCTTGTTGGGCAGATTATAGTCGGAACGGG
CAGATCGGATGATTCGCGCCGCCTTCTGCACAAATTCAACGTCCGATTCTATCTTTGTGCTGCGCCAGGATGTATTGCCTAGTTATGAGGAAGTT
AAATTTATTTGAATTCTATCATCATGAAGAAATCAAATGCGACTTACTGGGATAGCTAGCCACGCAAATGCTAGGAGCGGGATTTGCCCTCGGAA
GCCGCTGGTAAAGTTCCTCCGTGATGAAAGGCATGAACGGGGAGAGTAAGCGCAGTCCATAATCTAGACATACGTAGAGCGTGCGCCTTGCGGCG
GTCTGCTGCTCCTCGCTGCCGCTCTGGAAGATCGGCTTCAGACACTCCAAATACACGTCGCACAGATCGTAGAGCCAGAATGCGTAGCAGGCGCT
GGTCGCTGCAGCAAAGTCGTACGACTCAAAGCCGGTGTTGCAAGCTTCTATGGCAGCTGCCAAGCGTGACAGGATCCAGGCGTCCATCTGGTTGA
TCGCTGCAGACGCACTTAGCTCCGTGTCAAACTTCTCAGAGCCGGTGAAGTACAGCAGGGCGAACTTGGTGGCGTTCCACAGCTTGTTGCAGAAG
AAACGATATCCCAGAACGCGATTGATGTCCAGGTTGATGTCGCGCGCTTGCGTGATATAGGCGCACAGCGCGAATCGAAGTGCATCCGAGCCGCA
CTCGGGAATTCCCTGCGGATAATCCTGTTTCTGTCCAGCCTTAGCCTTTTCGATCTCCCGAGGATCCAGGTTGGAGCCCACAAGTTGAGCATGCA
GTCCCTCGAGCGTAATGCCACGAATAACATCCATAGGATCGATAACATTTCCCAGGGACTTGGACATTTTGCGTCCGTGCGCATCCCTCACCATG
GGGTGAAGATAGACCTCCTTAAACGGCAGTTTGCCCAGCAGCTTCTGTCCAAAGAATACCATGCGAGCCACCCAGAAGAAGAGAATGTCGTGACC
CGTCTCCAACAGCGATGTGGGATAGAACGTTTGCAGATCCTTAGTTTGGTCTGGCCAGCCAAAAACGGAGAAGGGAAAGATTCCCGAACTGAACC ATGTGTCCAGGACATCTTCGTCTTGTTTCAGTACTATCTTGCTGGCGTCCACTCCAAAACGTTCGGCTGCCTTGGTCAGAGCCTCCGCTTCGCTG
CGTGCTACAATCCAGTACTGCTCGTCGTCGTTCTAAAAATGAAACAAATAGGAAAATTTTAATTTGTCTAATTTAAAAGTGTTGTCTATAATTTA
TAGAGTTATGTTTTGGTTTTTACGCACCACACTTCCATGAGCAGACTAAGATATCCAACGAAATATATTACCCATACAAATTATTATTATCCAA
AGTAGATTTACTCACCGATCCAGTTTGAAGAGAAGGGTCGGTGAAGCTGACATGGTATGCCGGAATCCGGTGACCCCACCACAGCTGCCTCGACA
CGCACCAGTCGCGAATACCGTCCATCCAGTGGTACCACGTCTTGGTGTGATGCTCCGGAATGATCTTTAGTTCTCCGGAGCGCACTGCCTCAGTG
GCAGAGGCTGCCATGTCCGAGCAACTAACATACCACTGCGGCTTAATCAGCGGCTCCACCACGTCCTTGGAGCGACTGCAGATGGGCACCACCAT
CGGGTTGTTCAATGTCTCGCGGTATAGATTCAGGGCCTTAAGCTTCTCCAGGATTTTCTTGCGGCACTCGAACCGCTTCATTCCAGTAAACTCTC
CGTAGTCGCCGATTATGTAGCCGTCGTCGTTGAAGATTGTAATGAAGGGCAAATTGCAGCGCTTGCCCACCTCGTAATCGTTGGGATCGTGGGCT
GGGGTGATCTTCACAGCACCCGTACCGAAAGCCATGTCCACGAACTCGTCACAGACGATTGGCAGGCGGCGCGTGGAGAACGGATGGACTACGAA
CTTGCCATGCAGGTGCTTGTACCGATCGTCTTGGGGATGCACAGCCACAGCAGTATCGCCCAGCATAGTCTCGATACGGGTGGTGGCTACAATGA
TCTCTTCGTCACTGCCTTCCACCTTGTAGGCGAACTTTATTAGAACACCAAATTCCACTTTGTCCTCGTATCCGGGAATGGAGAGGAATGTGCGA
CCGGGAATCTCCACCTTGTCCACTTCAATGTCCGAAATAGCCGATCGTAGGGTGCACGACCAATTGACCAGTCGGGAGCTACGGTAGATGCTGCC
CTCCTCGTGCAATCGGACGAAAGCCTCGGTAACGGCGCGACAGAGCTTGGGGTCCATGGTGAAGGCCACTCGGGTCCAGTCATAGGAGGAGCCCA
GGGACTTCAGCTGCTCATAGATGCGACCGCCCTTTTCCCGGCGCCAGTCCCAGATGCGCTCAATGAACTTTTCGCGACCTAGGTCGTGCCGCGAT
AGCTTCTCGTCGCGCCACAATAGCTTCTCTACCACCACCTGGGTGGCGATGCCGGCGTGGTCGCAACCAGGCACCCATAGAGTGGTTCGTCCCTT
CATGCGGTGGTAGCGCGTGATGGCGTCCTCGATGGCGTTGGTCAGGGCGTGACCCAAATGCAGAGAGCCCGTCACGTTTGGTGGTGGAATGATCA
TCACAAACTTGCCATTGGGATTGGGGGCGTCTATGGATGCGCGCTAAATGTTCAAAGAGTATTAGAAACCAGCATTTAACCAAAACCAAGGATAA
ACTCACTCCGTACTCGGGCGTGAAGAAGCCCTCCTTCTCCCACCAGCTGTACCACTGTGCTTCCACATACCGTGGACTGTAGGCATCCGGCAAGG
CTCCACTCAGATCCTTCTTCTCACCGGGCGCGGTTTGGGCCGTGTACACGGCAGCCTCTTTCACCTCCTTGGTGCGCTTCTGCAAAGTAAAGTAA
TTCGAGCATTACATATAAGTAGCACTCGCTTTCACCAGTAACAATGGGCAGCAATTACTGCCTCTCACTTGGCCACATAACCTCGATTTGAGATC
ACAAAATAGGAGGCACTTTTGGGATGGATTTTTCACTAACCTCGGGCTTCTCCTTCTTCTCACCCGCTGCTGGAGCAGCCGCAGCCTTCTTGTCC
AGCTTCGCCTGCAGCTTGGCCAGCTTCTCCGCCTTCAGACGCTCCTTTTCCAGTTGCTTGGCCGTCTTGGGAGGATCACCCCCGGCTCCGGCTGG
TGCGTTGGCATCGTTCTGCTGTTCAGCCTCGGGCATTTTTCAGTTGATCTCAGGATTAAATCTGGATAGTGCAACTGTAAGTTAAATGACGAAAT
GGACGAAGTACATTACTCACATGCAGTTAGACTGGAGTCGCAGAAAAACATATGAAAACGTGTGCAGTTTGGGACCAGGGTTGCCAACAGATATT
ATTATTTTGAATTCCATTTGGCACATAACATTTAATCATTTTTAAAAGGTATAAAAACTGAATTTATGATTTATATTAAGTGTATTTTAAAATTC
TTATGTAAGATTAATATTTTGTATACATAAATTCTTTAATATTCATTTATTTTTAAACGGAAAAACAATAGAATTTTATCACCTTTTAAAATATA
AGGTGCTTCAAATATTTAGAAATCAATGATAATATATTTTACGATAACTAAATACGACTATATTTTAACATGTTGTATAAATATTTTAAAAGTTT
TTAAATTTTTCCAGTATGAAAAAGATTTAAATTATATAAAACAATCTGAAATTGCTTACTCCGGAATCAAAACTTAAATGGTCAAGTTATTCCAA
AATATATTTTTTATATCTTAAATGCTTTATTTTGTTAAAAGCTTTAACGAAAATGTAGTTTAACAGCACTGTCGGAATTCGATAGGCCTGCTCAA
AATTTAGATTGCGTTATCGCTGCAATCTGGTCACACTTACAGTCGTGTTTTTTGGTGTTTTTGTATGGGAAGATTTTTGCGAAAAATAAATTCAG
AAGCTAGTGTATTGTGTGTTGTTCCTTTGTGAAATGTAAAGTGGGACGAACATCAGAGATCGGTAAATACTATCACAGTGTACCACCCCATAAAA
TGACAAACTATTCCGTTTAGTGTAAGTGCTCCCATTCGAGTGTGTGTCCATTGGACTGCAGAGGAAGCGTCTGATAAGCAGCCATCTTCCTATAA
GAATGGCAAGGAAATTCCTGCCAAATTTATATAAATTCTAAGAACTACTGTCGTGCAGCGATAGCATGGCCGTTCTAGCCGCTCACGAGATCGAA
AAACAATAGGTTTAGCAACACAACAACAACAACACACTCGCAGACATGTGCAACCGAAAGCTAAT
(SEQ ID NO: 433)

Exon: 4670..4411
Exon: 4259..4092
Exon: 4033..2771
Exon: 2597..1568
Exon: 1503..1001
Start ATG: 4596 (Reverse strand: CAT)

Transcript No. : CT13504
TAATGTACTTCGTCCATTTCGTCATTTAACTTACAGTTGCACTATCCAGATTTAATCCTGAGATCAACTGAAAAATGCCCGAGGCTGAACAGCAG
AACGATGCCAACGCACCAGCCGGAGCCGGGGGTGATCCTCCCAAGACGGCCAAGCAACTGGAAAAGGAGCGTCTGAAGGCGGAGAAGCTGGCCAA
GCTGCAGGCGAAGCTGGACAAGAAGGCTGCGGCTGCTCCAGCAGCGGGTGAGAAGAAGGAGAAGCCCGAGAAGCGCACCAAGGAGGTGAAAGAGG
CTGCCGTGTACACGGCCCAAACCGCGCCCGGTGAGAAGAAGGATCTGAGTGGAGCCTTGCCGGATGCCTACAGTCCACGGTATGTGGAAGCACAG
TGGTACAGCTGGTGGGAGAAGGAGGGCTTCTTCACGCCCGAGTACGGACGCGCATCCATAGACGCCCCCAATCCCAATGGCAAGTTTGTGATGAT
CATTCCACCACCAAACGTGACGGGCTCTCTGCATTTGGGTCACGCCCTGACCAACGCCATCGAGGACGCCATCACGCGCTACCACCGCATGAAGG
GACGAACCACTCTATGGGTGCCTGGTTGCGACCACGCCGGCATCGCCACCCAGGTGGTGGTAGAGAAGCTATTGTGGCGCGACGAGAAGCTATCG
CGGCACGACCTAGGTCGCGAAAAGTTCATTGAGCGCATCTGGGACTGGCGCCGGGAAAAGGGCGGTCGCATCTATGAGCAGCTGAAGTCCCTGGG
CTCCTCCTATGACTGGACCCGAGTGGCCTTCACCATGGACCCCAAGCTCTGTCGCGCCGTTACCGAGGCTTTCGTCCGATTGCACGAGGAGGGCA
GCATCTACCGTAGCTCCCGACTGGTCAATTGGTCGTGCACCCTACGATCGGCTATTTCGGACATTGAAGTGGACAAGGTGGAGATTCCCGGTCGC
ACATTCCTCTCCATTCCCGGATACGAGGACAAAGTGGAATTTGGTGTTCTAATAAAGTTCGCCTACAAGGTGGAAGGCAGTGACGAAGAGATCAT
TGTAGCCACCACCCGTATCGAGACTATGCTGGGCGATACTGCTGTGGCTGTGCATCCCCAAGACGATCGGTACAAGCACCTGCATGGCAAGTTCG
TAGTCCATCCGTTCTCCACGCGCCGCCTGCCAATCGTCTGTGACGAGTTCGTGGACATGGCTTTCGGTACGGGTGCTGTGAAGATCACCCCAGCC
CACGATCCCAACGATTACGAGGTGGGCAAGCGCTGCAATTTGCCCTTCATTACAATCTTCAACGACGACGGCTACATAATCGGCGACTACGGAGA
GTTTACTGGAATGAAGCGGTTCGAGTGCCGCAAGAAAATCCTGGAGAAGCTTAAGGCCCTGAATCTATACCGCGAGACATTGAACAACCCGATGG
TGGTGCCCATCTGCAGTCGCTCCAAGGACGTGGTGGAGCCGCTGATTAAGCCGCAGTGGTATGTTAGTTGCTCGGACATGGCAGCCTCTGCCACT
GAGGCAGTGCGCTCCGGAGAACTAAAGATCATTCCGGAGCATCACACCAAGACGTGGTACCACTGGATGGACGGTATTCGCGACTGGTGCGTGTC
GAGGCAGCTGTGGTGGGGTCACCGGATTCCGGCATACCATGTCAGCTTCACCGACCCTTCTCTTCAAACTGGATCGAACGACGACGAGCAGTACT
GGATTGTAGCACGCAGCGAAGCGGAGGCTCTGACCAAGGCAGCCGAACGTTTTGGAGTGGACGCCAGCAAGATAGTACTGAAACAAGACGAAGAT
GTCCTGGACACATGGTTCAGTTCGGGAATCTTTCCCTTCTCCGTTTTTGGCTGGCCAGACCAAACTAAGGATCTGCAAACGTTCTATCCCACATC
GCTGTTGGAGACGGGTCACGACATTCTCTTCTTCTGGGTGGCTCGCATGGTATTCTTTGGACAGAAGCTGCTGGGCAAACTGCCGTTTAAGGAGG
TCTATCTTCACCCCATGGTGAGGGATGCGCACGGACGCAAAATGTCCAAGTCCCTGGGAAATGTTATCGATCCTATGGATGTTATTCGTGGCATT
ACGCTCGAGGGACTGCATGCTCAACTTGTGGGCTCCAACCTGGATCCTCGGGAGATCGAAAAGGCTAAGGCTGGACAGAAACAGGATTATCCGCA
GGGAATTCCCGAGTGCGGCTCGGATGCACTTCGATTCGCGCTGTGCGCCTATATCACGCAAGCGCGCGACATCAACCTGGACATCAATCGCGTTC
TGGGATATCGTTTCTTCTGCAACAAGCTGTGGAACGCCACCAAGTTCGCCCTGCTGTACTTCACCGGCTCTGAGAAGTTTGACACGGAGCTAAGT
GCGTCTGCAGCGATCAACCAGATGGACGCCTGGATCCTGTCACGCTTGGCAGCTGCCATAGAAGCTTGCAACACCGGCTTTGAGTCGTACGACTT
TGCTGCAGCGACCAGCGCCTGCTACGCATTCTGGCTCTACGATCTGTGCGACGTGTATTTGGAGTGTCTGAAGCCGATCTTCCAGAGCGGCAGCG AGGAGCAGCAGACCGCCGCAAGGCGCACGCTCTACGTATGTCTAGATTATGGACTGCGCTTACTCTCCCCGTTCATGCCTTTCATCACGGAGGAA
CTTTACCAGCGGCTTCCGAGGGCAAATCCCGCTCCTAGCATTTGCGTGGCTAGCTATCCCAGCAATACATCCTGGCGCAGCACAAAGATAGAATC
GGACGTTGAATTTGTGCAGAAGGCGGCGAATCATCCGATCTGCCCGTTCCGACTATAATCTGCCCAACAAGGTTAAAACCGAGGTGTATATAG
TATGCACGGATTCGGTGCCCAGTGAAATACTCAAACGCTACGCCAGCGATCTGGCCACAATCTCCTACTGCTCCAATGTGGTCTTTGACAGTCCC
GCACCGCAGGGCTGTGCGATCCTCACCGTGACGGGCCAGTGCGAGGTGCACCTGCTGCTCAAGGGACTCGTGGAGGCGGACAAGGAGATAGCCAA
GCTGCAGAAGAAGAGCGACCAGCTGGTGCAGACGGTGGGCAAGCTAACTCAGGCCATCCAGGCCGCCGACTACGCAACTAAGGTTCCCGCCGAGG
TGCAGGAGGCCAACGAGACAAAACTCTGCGAGTCGCGGGCAGAGATCGAACGCATCGCTGCCGCCATCGAGACTCTGAAACTAATGTGA
(SEQ ID NO: 434)

Start ATG: 75 (Reverse strand: CAT)

MPEAEQQNDANAPAGAGGDPPKTAKQLEKERLKAEKLAKLQAKLDKKAAAAPAAGEKKEKPEKRTKEVKEAAVYTAQTAPGEKKDLSGALPDAYS
PRYVEAQWYSWWEKEGFFTPEYGRASIDAPNPNGKFVMIIPPPNVTGSLHLGHALTNAIEDAITRYHRMKGRTTLWVPGCDHAGIATQVVVEKLL
WRDEKLSRHDLGREKFIERIWDWRREKGGRIYEQLKSLGSSYDWTRVAFTMDPKLCRAVTEAFVRLHEEGSIYRSSRLVNWSCTLRSAISDIEVD
KVEIPGRTFLSIPGYEDKVEFGVLIKFAYKVEGSDEEIIVATTRIETMLGDTAVAVHPQDDRYKHLHGKFVVHPFSTRRLPIVCDEFVDMAFGTG
AVKITPAHDPNDYEVGKRCNLPFITIFNDDGYIIGDYGEFTGMKRFECRKKILEKLKALNLYRETLNNPMVVPICSRSKDVVEPLIKPQWYVSCS
DMAASATEAVRSGELKIIPEHHTKTWYHWMDGIRDWCVSRQLWWGHRIPAYHVSFTDPSLQTGSNDDEQYWIVARSEAEALTKAAERFGVDASKI
VLKQDEDVLDTWFSSGIFPFSVFGWPDQTKDLQTFYPTSLLETGHDILFFWVARMVFFGQKLLGKLPFKEVYLHPMVRDAHGRKMSKSLGNVIDP
MDVIRGITLEGLHAQLVGSNLDPREIEKAKAGQKQDYPQGIPECGSDALRFALCAYITQARDINLDINRVLGYRFFCNKLWNATKFALLYFTGSE
KFDTELSASAAINQMDAWILSRLAAAIEACNTGFESYDFAAATSACYAFWLYDLCDVYLECLKPIFQSGSEEQQTAARRTLYVCLDYGLRLLSPF
MPFITEELYQRLPRANPAPSICVASYPSNTSWRSTKIESDVEFVQKAARIIRSARSDYNLPNKVKTEVYIVCTDSVPSEILKRYASDLATISYCS
NVVFDSPAPQGCAILTVTGQCEVHLLLKGLVEADKEIAKLQKKSDQLVQTVGKLTQAIQAADYATKVPAEVQEANETKLCESRAEIERIAAAIET
LKLM*
(SEQ ID NO: 435)

Name: valyl-tRNA synthetase
Classification: enzyme

Celera Sequence No. : 142000013384624
TAGTGGCAAAGACTATATTGATTTATGTTTAATCTATGTTCGAGAACGAAGCGCATCGAAATGCTTTTAAGACGTATTACACAACCAACTGTAAT
TATTATCTGATATTTCAAAGATTTAAACAACTTTTATACGTAAACAAAAATCACATAAAAATTAAAAAAAAACAACAAAAACGAAACGAAAAA
CATTTATTTCAAAATAAACGAATCGAGACAGTGAGGCGTGGGGCAGTCTGCGATAATATGCAGGGCGGTCAAACCTACAGATATAATTACAAATA
TTGATGTGCATACAATAAACTTATGCCTTTCCCTACAACCCGAAAAGTCCTCTTCCTTGGCCCGGAATCGAAAAAAATGTCAAAAAAGAAACAAA
AATGGGCCAACACAGCTGGCGAGGCGAAAGCGAAAAGTTGCCAGCATATACACAAATATATTTCTGTAACTTCTATAATACACCAAGCGCCTGAT
AAGCGCTAAAGAATAATATCTAAAACGAAAACGGATCAAAAACAAAGTACTTCAATGAGAAATAAAACGATATTTAAAGAATTCAAACTACCATG
TTCTAACGGGATGAATTGGGCGTTGGGTATTTATATTTTGAAACCTATAAACTTATATTCGTATTAAATACCAATGTATTATTATTTGTTATTTC
GCCTTTCTAGGGCGAAATAACAAAGACAATGCTTTTTTCCCTTTTCAGATTACCCTTTTATAGAAAAGCAACAAAAAATTAATCTGTAATTAATT
TTATATAATATTGATTTTACGGCTATAAACAAAAGTTTGTCAACAAGTTTACAATTTTCGAATCTTTAATGTTTATATTAATATTATAAAGCCAT
AAAAGGATTGGTAATTTTTTAATTTAAAATTCAATTTTAGTGTTGTGCTTAGCTAACGAGCCTTTACAACACTGCCCGCCAGCAATGCGATACTT
GTATCGAGCCGTCGTCTATCGAAACGTCGGCCAATCGAAATTGTTCATCCCTGGAAGAAGACAAGAAAAAAATAATATATAATAATAGAATATTC
CACCGTGATAATATTGCCAAGCATTGTTTTCCGCGTCTTTGCCGTCGGTAATTGGGCAACAGTCAGAACGACCAAAAAGCCGAAGGGCCCCGAAC
AGCAGGATAATCGGCAGAAAGTACGAGGCATCATCGACAGGCCAACTAAACCACAACGACAACCACATCCGCAGTCAAATCCCAATCCAAATCCA
CGTCCAAATCCCATTTCGAGTGAAACAGCGAGTGAGACAGCGAAATGCCACTGTTCGGGAAGTCACAGAAGTCGCCAGTGGAGCTGGTCAAGTCG
CTGAAGGAGGCGATCAACGCCCTGGAGGCGGGCGACCGCAAGGTGGAGAAGGCGCAGGAGGACGTCAGCAAGAACCTGGTCTCGATCAAGAACAT
GCTGTACGGTAGCAGCGATGCCGAGCCGCCGGCGGACTACGTGGTGGCCCAGCTGTCCCAGGAGCTGTACAACAGCAACCTGCTGCTGCTGCTCA
TCCAGAACCTGCACCGCATCGATTTCGAGGGCAAGAAGCATGTGGCGCTCATTTTCAATAATGTGCTGCGCCGCCAGATTGGCACCCGTTCGCCC
ACCGTCGAGTATATATGCACGAAGCCGGAGATCCTGTTCACCCTGATGGCCGGCTACGAAGATGCGCATCCGGAGATCGCACTGAACTCCGGTAC
CATGCTGAGGGAGTGCGCCCGGTACGAGGCGCTGGCCAAGATCATGCTGCACTCGGATGAGTTCTTCAAGTTCTTCCGCTACGTGGAGGTTTCCA
CCTTTGACATTGCCAGCGATGCCTTTTCTACGTTCAAGGAGCTGCTCACGCGCCATAAGCTGCTGTGCGCGGAGTTTCTGGACGCCAACTACGAC
AAGTTCTTCTCGCAGCACTACCAGCGCCTGCTCAACTCGGAGAACTATGTGACGCGGCGTCAGAGCTTGAAGCTGCTTGGGGAACTGCTGCTGGA
CCGGCACAATTTCACCGTGATGACGCGCTACATATCCGAGCCGGAGAACCTCAAGCTAATGATGAACATGCTCAAGGAAAAGTCGCGCAACATTC
AGTTCGAGGCGTTTCACGTCTTCAAGGTGTTCGTGGCCAATCCCAACAAGCCGAAGCCCATTCTGGACATCCTGCTGCGCAACCAGACGAAGCTG
GTCGACTTTCTGACCAACTTCCATACGGATCGCTCCGAGGACGAGCAGTTCAACGACGAGAAGGCCTATCTGATCAAGCAGATAAAGGAGCTGAA
GCCGCTGCCCGAGGCTTAGTTGGACCTCCACCTCGGCTCCAACTTCAGCTCCAACTCCAGCTCCAGCGTCCCGGGGGCAAAGGACCGTAGCCAG
AAGCCAGAAGCGATCGATACGGAAGCAGAGAGAGCGATGGTGGGTTAGCAGGATGTGAACATGTTTTGTGTGTGGGTTAAAGCAAATATATATTA
TATACTATATTTTGTGACGCTGATGACTCTACACTTGTGAGTAACTAAACAATAATTTAGACAACAACAAAAACAACACTGATGATGATAATGAT
AAAAATAACGATAAAGCGAATTAGAAAACAAGAAAAAGTACGAGTAAATAGCGTAACGCCGAAAAATAAAACTGTACCGAGAGTTTCGAATTTAA
CATAGCCACATTTAGACATTCTGGGCCTAGAGATCCGCTATCCTATTATACAGATATGTTTAACCATTCGTCGATCCTCCGCGAAGTAATCCCCC
TTCCTTTCCAGACCCTTTTTTCGATATCCATTTAACTAGTTGTTGTATTTAAAATTTGATCGTTTTTGAAACGAGATATCCCTTCACCGCCTTG
ACCTGCCACGCCCCTTTTGCGCCCCAAAAAAAAAAAACTGAAGATTCACAATGAGTTTTGACTTAAAAATGTAATTCCACGCAAAATTCATGAAA
AGAACGAAAACTAAATACTGCATAAAAATAATAATAATTCATAGTGATAATTGTCTGTGCATCCTTCGGCATGGACTCTACTATATATACACTGA
TATATATATATAGAAAGAGCAAGAGAAAGAAAAAGAGAGAGAAAGCATTCAACACACACACACTACACACATGCATACGTACATAGTTAAAAG
GGAAGTAAAACAAGAAACAACAACATTGCAAGCAACATAATAACTATACGATTATTATAATTTATATTATTCCCAAATTAAAGATAACAGCCAAA
CAAATCAGCAGTTTTTCCACTGTGGGCGGTGGTTTTCTCAGGGGGCGTGCAGCTCCCCCCTGAGTCATGTGCAAAAAATCGTGCCAGGGCGGCAA
CCTCACCCAAAAAACGTCGATCAAGGGCTGGGGAGATGATTCACACGCTGGGAATGCCACCGAAACCAAAAGAGATTTCAAATCACGTTTCAAGG
TGTGCCTAAATGAGTAAATGAGTCCATTCCAGGACTCAGCCTGCTGTAGGAATCCCATGAAGGAGTTTTCAAATGTGTGCAGGCTTCTACTTTAA
TCGTTGTCGACTAGGTTTTATTACAATTATCTTAATAAATGAATTCGAGAGTTCTTAGGCTAGCTACATATGTATATATTAAGGATGGCTACATC
TATCGTCGCTTCTTCTTCTCCAGCTTACGAATCTTGTGCAGGCGCGTCCGGACCGGCTCGCCCTCCCGCTCCGTCACTTCGCCGGACTCCGGATT
ACTTTGGCCATCCGGGTTATTCTCCATCAATACTGCGGCCGAAATGCAAACGAACTGGAAGAGAGCACCCACATAAAGCCCGTATCGGATTAGCA
AGCTGAAGATGTCCTCGTCGCCGTACTTGTCCAGGGCTGCGGCGGCGCCCAGACTGTCCGCGGAAGCCGACATCGCTGCGCTGGTATTGTTTATA AACAAAACCCGCGAGGATTAGACAAAAAAAAATAACAACTACAAAAAGTTTGTTTTTTGTATTGGGTAGAGATGGTACCCTGAACCAACAGTTCA
GGTGGAAACTATCGATAACTTTTTAGGTCAAAGTTTTAAGGTTGTTAGCTCATTAACGGCAAGTATTTAAAGGCTTGCACAAAATCTTCGCTTG
ATTTTATTTAAATTCAATTACCTGGATTATTAAATACATTTTATAAAGTTTAACACTAGTGAAATAAATATCCCATCCCCAACACATTCTTCAGG
GTTACCGTTTAAGGTATGTTCAAAACTTTATGGTATATTCCGGAGCCCTAC
(SEQ ID NO: 436)

Exon: 1001..3231
Start ATG: 1280

Transcript No. : CT13526
CTGGAAGAAGACAAGAAAAAAATAATATATAATAATAGAATATTCCACCGTGATAATATTGCCAAGCATTGTTTTCCGCGTCTTTGCCGTCGGTA
ATTGGGCAACAGTCAGAACGACCAAAAAGCCGAAGGGCCCCGAACAGCAGGATAATCGGCAGAAAGTACGAGGCATCATCGACAGGCCAACTAAA
CCACAACGACAACCACATCCGCAGTCAAATCCCAATCCAAATCCACGTCCAAATCCCATTTCGAGTGAAACAGCGAGTGAGACAGCGAAATGCCA
CTGTTCGGGAAGTCACAGAAGTCGCCAGTGGAGCTGGTCAAGTCGCTGAAGGAGGCGATCAACGCCCTGGAGGCGGGCGACCGCAAGGTGGAGAA
GGCGCAGGAGGACGTCAGCAAGAACCTGGTCTCGATCAAGAACATGCTGTACGGTAGCAGCGATGCCGAGCCGCCGGCGGACTACGTGGTGGCCC
AGCTGTCCCAGGAGCTGTACAACAGCAACCTGCTGCTGCTGCTCATCCAGAACCTGCACCGCATCGATTTCGAGGGCAAGAAGCATGTGGCGCTC
ATTTTCAATAATGTGCTGCGCCGCCAGATTGGCACCCGTTCGCCCACCGTCGAGTATATATGCACGAAGCCGGAGATCCTGTTCACCCTGATGGC
CGGCTACGAAGATGCGCATCCGGAGATCGCACTGAACTCCGGTACCATGCTGAGGGAGTGCGCCCGGTACGAGGCGCTGGCCAAGATCATGCTGC
ACTCGGATGAGTTCTTCAAGTTCTTCCGCTACGTGGAGGTTTCCACCTTTGACATTGCCAGCGATGCCTTTTCTACGTTCAAGGAGCTGCTCACG
CGCCATAAGCTGCTGTGCGCGGAGTTTCTGGACGCCAACTACGACAAGTTCTTCTCGCAGCACTACCAGCGCCTGCTCAACTCGGAGAACTATGT
GACGCGGCGTCAGAGCTTGAAGCTGCTTGGGGAACTGCTGCTGGACCGGCACAATTTCACCGTGATGACGCGCTACATATCCGAGCCGGAGAACC
TCAAGCTAATGATGAACATGCTCAAGGAAAAGTCGCGCAACATTCAGTTCGAGGCGTTTCACGTCTTCAAGGTGTTCGTGGCCAATCCCAACAAG
CCGAAGCCCATTCTGGACATCCTGCTGCGCAACCAGACGAAGCTGGTCGACTTTCTGACCAACTTCCATACGGATCGCTCCGAGGACGAGCAGTT
CAACGACGAGAAGGCCTATCTGATCAAGCAGATAAAGGAGCTGAAGCCGCTGCCCGAGGCTTAGTTGGACCTCCACCTCGGCTCCAACTTCAGCT
CCAACTCCAGCTCCAGCGTCCCGGGGGCAAAAGGACCGTAGCCAGAAGCCAGAAGCGATCGATACGGAAGCAGAGAGAGCGATGGTGGGTTAGCA
GGATGTGAACATGTTTTGTGTGTGGGTTAAAGCAAATATATATTATATACTATATTTTGTGACGCTGATGACTCTACACTTGTGAGTAACTAAAC
AATAATTTAGACAACAACAAAAACAACACTGATGATGATAATGATAAAAATAACGATAAAGCGAATTAGAAAACAAGAAAAAGTACGAGTAAATA
GCGTAACGCCGAAAAATAAAACTGTACCGAGAGTTTCGAATTTAACATAGCCACATTTAGACATTCTGGGCCTAGAGATCCGCTATCCTATTATA
CAGATATGTTTAACCATTCGTCGATCCTCCGCGAAGTAATCCCCCTTCCTTTCCAGACCCTTTTTTTCGATATCCATTTAACTAGTTGTTGTATT
TAAAATTTGATCGTTTTTGAAACGAGATATCCCTTCACCGCCTTGACCTGCCACGCCCCTTTTGCGCCCCAAAAAAAAAAAAACTGAAGATTCACA
ATGAGTTTTGACTTAAAAATGTAATTCCACGCAAAATTCATGAAAAGAACGAAAACTAAATACTGCATAAAAATAATAATAATTCATAGTGATAA
TTGTCTGTGCATCCTTCGGCATGGACTCTACTATATATACACTGATATATATATATAGAAAGAGCAAGAGAAAGAAAAAGAGAGAGAAAGCATTC
AACACACACACACACTACACACATGCATACGTACATAGTTAAAAGGGAAGTAAAACAAGAAACAACAACATTGCAAGCAACATAATAACTATACG
ATTATTATAATTTATATTATTCCCAAATTAAAGATAACAGCCAAAC
(SEQ ID NO: 437)

Start ATG: 280

MPLFGKSQKSPVELVKSLKEAINALEAGDRKVEKAQEDVSKNLVSIKNMLYGSSDAEPPADYVVAQLSQELYNSNLLLLLIQNLHRIDFEGKKHV
ALIFNNVLRRQIGTRSPTVEYICTKPEILFTLMAGYEDAHPEIALNSGTMLRECARYEALAKIMLHSDEFFKFFRYVEVSTFDIASDAFSTFKEL
LTRHKLLCAEFLDANYDKFFSQHYQRLLNSENYVTRRQSLKLLGELLLDRHNFTVMTRYISEPENLKLMMNMLKEKSRNIQFEAFHVFKVFVANP
NKPKPILDILLRNQTKLVDFLTNFHTDRSEDEQFNDEKAYLIKQIKELKPLPEA*
(SEQ ID NO: 438)

Classification: known_flybase_gene
Gene Symbol: Mo25
FlyBase ID: FBgn0017572

Celera Sequence No. : 142000013384676
ATTAACCTCCATGGTTTTATCTTCTTGCCAAGTGCCTTATTCTCAACCTTTAGCGCTTCAATTTCGGCCAGTGCCTTTTCGTATTTGGCTTCCC
ATGCCTGTAGCTCCTTGGTATTCTGTGAGATGGTAAATGGGTAACTCTGCTGAAAGGACGTATTCCTGCACAACTTACACGATCTTCGGCCTTCT
GAAAGTCGTCCAAATCATCGTAGATGTCCAGTTCAAGGGATCTGTCCATTTGGTCAGGCTTCTTTGAACCTGCAGGCTCTATATCGTACAAATCG
TGATAGATATCCAAATCCATGGATTTATCCTTAACGTTGGACTTCATCCCGCCCGCGTCCTGGTCTTCCAAATCCATCAAGTCCTCCAGAGCTTC
GGGCAGCACCAGTTCTCCGCCAGATTTCGTGGCATATGCAGGCGTTTCCATACCAATCGCTTACGTTTCTTCTTGGCTGCCCTTTAAACAAGGAT
ACATAAAATGAATTGTTAGAGTTACTGTTTTTTAATGGAGCTACTTTATTGATTACCTGTTCAGTCATAAATTGATCAAAATTCGAAACACAAAA
GAATTTCAATGTTCTTGATTTTTGTTTCAGGGAATAAAAGTTCCACTAAAGCTCAATGGTCACTGTCCTGAGCATTTCCTCCAAACTGGCGTGCA
ATTTGTTTCCCTGCCGTGTATTTGTATAAATGTAATTATTATTATTATTCTATTTAATATTGTTAGAAAATCCCGTGTTGCCGCCAATCGATAAC
AGAAGATGCAGTTGATTATCGGAAGCAACAGCTGACCGGCTGAAAATGTGGCAACCCTGATAGTGGATATCGATATCCAGCAGCAACATTTGGCG
CCAAAACGAATATTTTAAAAATTTTATTATGCACTTACGTGTTTTCCCAAGAATATAATTTTAAAATCAATCTAGTTCCCATTTCGTATTACTGT
ACACTTAAATTCGTTAAAAAAAAACATCACAATACAAACAATAATACTCGAGAAACACTACACAATGGCAGACATTCCGGAAAAAAGTTCTTACT
ACAAGAAGGAAAGAAGAAAGTTCGCTCTGATCACTTACCTACTAACCGCGATATTCCTGATCCTTGCGCTGTTGCAATGGGCCACTTTCCGCTTT
GTGTACGTATGTATTTTCACATTACTTCATCCTCACTGCACTTTTTCTTAATTTTCAGAAATTTTCTAAGGGAATTTTTTACTTCGTACCATTGG
TTGAGCTGCCTTTTTTTTGGAATAGGCCTGATACTCCTCGTACTTTTCATATTTTTCGAGGTACTGCGCTTTAATAAAATGGTAAACTGGTTGTT
TGCCTTTCTAATTGTAAGTCTACAATGTGAAACATAACCTGGGTGGCAGTATGAACTTATTCTTTCCAGTTTGAATGCATTGTACTGGGGATTGC
ACCGCTGGTTGCCCGCCACTACAAGTATCAGTTTCTCTTCAGCTTCCTTATATGGACCGTAGCATTGGCGCTTTTTATTGTCTGTGGTTCCTTTC
TTCCGGTAAGAAGAGTCCACATGAAAGCCATTTGATTCAAATCTGAAGCTTCACATTTTTATTGTTATCCCCTTAAGCTGGATCTTACTTTGGAT
GTTGTGGTGCTATTTGTGCTTGCAGTGGTTTCCATTATCGGCGCCATATACTTCGTGATGCTCTACATCGTGGCTAATGTCGCATACTCGTTTAT
AATCGCCCGTTGCTTTATAGTGATCAGCATCTTGATGGTTAGTACTGAGTCATACATTTTTGAATTAGTTTCTGTCATTTAGTTTCCTCCTTACA
GTTTGTCATGTATCACGCGCAGATTATAAACGGTGGAAGGTTCGCCGAGATGCGCACGAAGGACTACTTCCTGGCAGCCATCATACTGTTCCTCG
ATTTCCTGCTCCTCTATCTTTTCTCATTCCAAGTGGCCCCAAAATGGTCGGATCGTTGCGATGGCGAACGTTCAAAAAACTTGGTGCTGTTCACA GAAACTACGACGAATTCGTATCCACCAAAATGGTGGCGTACGAGCACGAAGGGTATGATTTCTTATTATTAGTTCATGTTAGATGAAATATTCAA
TTAATTTATACTTTTCACACTTGTTTTCAAAGATACCCCCTAAAGTCGTTAGCCAACACTGCCGCCCGTTTGGCGCCAAACACAACAGCCAGCTG
ATTTCATTTCGCGTTCCTACCGGTGAAGAAACTTTAATTGGCACAGAGCTGACCTAAACAAATAAATAAATAAACGCAACCCGGCGACTTAAAGA
CTCCACGACATCGGGCCGCAGTGCAAAGCCAGCGATGGATCCCACCATTTCAGTGTCCAAGGTGAGTGGCTTCGGCTTCCAAACTGGACATAGAT
GTTTAACTACTTATTTTTGTTGTCTGCAGGGCTGTTTTGTCTACAAAAATGGCGCTACGAGAGCAGGGAAAAAGGCGGCCAGCAAACGGAAGCGT
CCTGCCGCAGAATCCAGTAGTCTTCTTGGCAAAGAGGTAGTGCAGCAGCCCTTCTATGAGGAATATCGCAAGGCCTGGAATCAGATAAACGATCA
CATTGCCGACCTGCAGCACCGCAGCTATGCCCGCACTCTGGAGCAACTGGTGGACTTTGTGGTGGGGCAGGCAGAGCGCGACACCCCGGACGAGG
TGCTGCCCACCGCCGCCTTGCTAACGGGCATTAATCAGCCGGATCATCTCAGCCAGTTCACGGCACTTACCCAGCGACTCCATGCCCAACGTGCT
GCAATGGTATGTGTGCTGCAGTCCAGGGATTGCGCCACTCTCAAGGCGGCCGTTGAGACATTGGTTTTCGGGCTCGTAGAAGATAATGCAGAAGT
GGAGCAAATGGAAGACGAGGACGAGGACGAGGATGGTGCCGAACGGGATCGCAAGCGGCTACGTCGCTCGCAGTGCACCATGAAGCAGTTGAAGT
CTTGGTACACGAACAATTTTGACTCGGAACAGAAGCGCCGCCAGCTGGTCGTCATCCTTCCCGACTTTGAGTGCTTTAACGCAAGCGTGCTGCAG
GATCTTATTCTAATTTTGAGCGCTCACTGCGGCTCGCTTCCATTCGTCCTGGTCCTGGGAGTGGCCACGGCCATGACAGCTGTCCATGGGACACT
ACCATACCACGTCAGCAGCAAGATTCGTCTAAGGGTGTTCCAGACTCAAGCTGCTCCCACGGGCCTTAATGAGGTAATATTCCTTAACTCTGTGC
TAGTTTATGTACTAATCGGTTTTCTAACAACCTTTAGGTGCTGGATAAAGTTCTGCTGTCGCCCAAGTACGCTTTCCACCTGTCGGGAAAGACAT
TCAAGTTCCTGACGCACATCTTCCTATACTACGACTTCTCCATCCACGGCTTTATTCAGGGCTTCAAGTACTGCCTGATGGAACACTTCTTTGGT
GGGAATGCCTTTGCTCTTTGCACAGACTACAGCAAAGCATTGGGACGCATAAAGCAGCTGACCCACGAGGATATGGAAACCATCAGAAGGCTCCC
ATCGTTTCGTCCGTACGTCGAGCAGATCAATGATTGCAAACGCATCATAGCCGTGCTCACGGACGATGACTACCTAAAGAAGAAACTGCCGCAGT
TGCTGCGCGACTGCCTGCTCCACTTCCTGCTTTTCCGCTGCTCTCTGGAGTTCCTTACAGAGCTGGTTGGTGATTTGCCGCGCTGTCCGCTGGGA
AAGCTACGCCGGGAACTGTACGTCAACTGTCTTAATCGTGCGATCATTTCGACGCCGGAGTACAAGGAGTGCCTGCAGATGCTAAGCTTTCTGTC
CAAGGACGAATTTGTTGCTAAAGTGAATCGAGCCCTGGAAAGAACCGAACAGTTCCTGGTTGAAGAAATTGCTCCGCTGGAATTGGGCGAGGCCT
GCACTGCTGTGCTGAGACCTAAGTTAGAAGCTATACGCCTTGCAGTGGACGAAGTGGTCAAGGCCACCATGGCGACAATTACAACGACATCGCCC
AATGAAACCCGCCAGGCGACTGACCATTTGACTCCGGTGGCCTCGCGTCAAGAATTGAAAGATCAGCTCCTACAGCGTAGCAAGGAGGACAAGAT
GCGGCATCAGCTGAACACGCCCACCACCAATTCGGACGAGCTCTACAAAAGACTCTGCAGCTTATCGAAACGCAGATTGTACAGGATCATCTCC
GTGCGCTGCAGGATGCACCACCTATTCACGAACTTTTTGTGTTCAGCGACATTGCTACCGTGCGGCGAAACATAATTGGTGCTCCGCGGGCTGCA
CTGCACACTGCCCTGAATAATCCACATTTTTACATGCAGTGCAAGTGCTGCGAGCTACAAGATCAATCACTGCTGGTTGGCACACTGCCCGATCT
CTCCGTGGTTTACAAGCTGCACCTGGAGTGCGGTCGCATGATCAACCTTTTCGACTGGCTGCAGGCCTTTCGATCTGTTGTGAGCGACAGCGACC
ACGAGGAAGTGGCCCAGGAACAAATCGATCCCCAGATCCAGTGAGTAAAAAAATGGATTTCTCTCTGTAATATCATCAATTTCATTTGGTTTTCC
TTTCAACCAGGGCCCGATTCACGCGTGCCGTAGCCGAGTTGCAGTTTCTGGGGTACATTAAGATGTCGAAGCGCAAGACGGATCATGCCACTCGA
TTAACCTGGTAGCTCGCTCGGGCTATGAATAACCAAAATCCCTTAGGTATTTTTATCTTTTCTATTTATTTATATTGGGGCAAATTTCATGTGTG
GGACGTTATGAATAAATAAAACATCAATCGATTTGTCTACTCTGTACGAAATGCATTAACTTGTTTGCGAGTGAAGCGCGTTCTTGTATTTTTT
AAGTAAAGCCCAGCAGCTGGCAAGGCAAGCGTACTAAATATCAATTACCAGTCTTCCCGACTAGCGGTTACCACGTTCCCTGTTCACATTAGTTT
CAGAGTCTCGATGGCGGCAGCGATGCGTTCGATCTCTGCCCGCGACTCGCAGAGTTTTGTCTCGTTGGCCTCCTGCACCTCGGCGGGAACCTTAG
TTGCGTAGTCGGCGGCCTGGATGGCCTGAGTTAGCTTGCCCACCGTCTGCACCAGCTGGTCGCTCTTCTTCTGCAGCTTGGCTATCTCCTTGTCC
GCCTCCACGAGTCCCTTGAGCAGCAGGTGCACCTCGCACTGGCCCGTCACGGTGAGGATCGCACAGCCCTGCGGTGCGGGACTGTCAAAGACCAC
ATTGGAGCAGTAGGAGATTGTGGCCAGATCGCTGGCGTAGCGTTTGAGTATTTCACTGGGCACCGAATCCGTGCATACTATATACACCTCGGTTT
TAACCTTGTTGGGCAGATTATAGTCGGAACGGGCAGATCGGATGATTCGCGCCGCCTTCTGCACAAATTCAACGTCCGATTCTATCTTTGTGCTG
CGCCAGGATGTATTGCCTAGTTATGAGGAAGTTAAATTTATTTGAATTCTATCATCATGAAGAAATCAAATGCGACTTACTGGGATAGCTAGCCA
CGCAAATGCTAGGAGCGGGATTTGCCCTCGGAAGCCGCTGGTAAAGTTCCTCCGTGATGAAAGGCATGAACGGGGAGAGTAAGCGCAGTCCATAA
TCTAGACATACGTAGAGCGTGCGCCTTGCGGCGGTCTGCTGCTCCTCGCTGCCGCTCTGGAAGATCGGCTTCAGACACTCCAAATACACGTCGCA
CAGATCGTAGAGCCAGAATGCGTAGCAGGCGCTGGTCGCTGCAGCAAAGTCGTACGACTCAAAGCCGGTGTTGCAAGCTTCTATGGCAGCTGCCA
AGCGTGACAGGATCCAGGCGTCCATCTGGTTGATCGCTGCAGACGCACTTAGCTCCGTGTCAAACTTCTCAGAGCCGGTGAAGTACAGCAGGGCG
AACTTGGTGGCGTTCCACAGCTTGTTGCAGAAGAAACGATATCCCAGAACGCGATTGATGTCCAGGTTGATGTCGCGCGCTTGCGTGATATAGGC
GCACAGCGCGAATCGAAGTGCATCCGAGCCGCACTCGGGAATTCCCTGCGGATAATCCTGTTTCTGTCCAGCCTTAGCCTTTTCGATCTCCCGAG
GATCCAGGTTGGAGCCCACAAGTTGAGCATGCAGTCCCTCGAGCGTAATGCCACGAATAACATCCATAGGATCGATAACATTTCCCAGGGACTTG
GACATTTTGCGTCCGTGCGCATCCCTCACCATGGGGTGAAGATAGACCTCCTTAAACGGCA
(SEQ ID NO: 439)

Exon: 1001..1142
Exon: 1199..1343
Exon: 1400..1525
Exon: 1598..1747
Exon: 1807..2047
Exon: 2123..2341
Exon: 2405..3208
Exon: 3268..4505
Exon: 4571..5236
Start ATG: 2315

Transcript No. : CT13534
AGAAACACTACACAATGGCAGACATTCCGGAAAAAAGTTCTTACTACAAGAAGGAAAGAAGAAAGTTCGCTCTGATCACTTACCTACTAACCGCG
ATATTCCTGATCCTTGCGCTGTTGCAATGGGCCACTTTCCGCTTTGTAAATTTTCTAAGGGAATTTTTACTTCGTACCATTGGTTGAGCTGCCT
TTTTTTTGGAATAGGCCTGATACTCCTCGTACTTTTCATATTTTTCGAGGTACTGCGCTTTAATAAAATGGTAAACTGGTTGTTTGCCTTTCTAA
TTTTTGAATGCATTGTACTGGGGATTGCACCGCTGGTTGCCCGCCACTACAAGTATCAGTTTCTCTTCAGCTTCCTTATATGGACCGTAGCATTG
GCGCTTTTTATTGTCTGTGGTTCCTTTCTTCCGCTGGATCTTACTTTGGATGTTGTGGTGCTATTTGTGCTTGCAGTGGTTTCCATTATCGGCGC
CATATACTTCGTGATGCTCTACATCGTGGCTAATGTCGCATACTCGTTTATAATCGCCCGTTGCTTTATAGTGATCAGCATCTTGATGTTTGTCA
TGTATCACGCGCAGATTATAAACGGTGGAAGGTTCGCCGAGATGCGCACGAAGGACTACTTCCTGGCAGCCATCATACTGTTCCTCGATTTCCTG
CTCCTCTATCTTTTCTCATTCCAAGTGGCCCCAAAATGGTCGGATCGTTGCGATGGCGAACGTTCAAAAAACTTGGTGCTGTTCACAGAAACTAC
GACGAATTCGTATCCACCAAAATGGTGGCGTACGAGCACGAAGGATACCCCCTAAAGTCGTTAGCCAACACTGCCGCCCGTTTGGCGCCAAACAC
AACAGCCAGCTGATTTCATTTCGCGTTCCTACCGGTGAAGAAACTTTAATTGGCACAGAGCTGACCTAAACAAATAAATAAATAAACGCAACCCG
GCGACTTAAAGACTCCACGACATCGGGCCGCAGTGCAAAGCCAGCGATGGATCCCACCATTTCAGTGTCCAAGGGCTGTTTTGTCTACAAAAATG
GCGCTACGAGAGCAGGGAAAAAGGCGGCCAGCAAACGGAAGCGTCCTGCCGCAGAATCCAGTAGTCTTCTTGGCAAAGAGGTAGTGCAGCAGCCC TTCTATGAGGAATATCGCAAGGCCTGGAATCAGATAAACGATCACATTGCCGACCTGCAGCACCGCAGCTATGCCCGCACTCTGGAGCAACTGGT
GGACTTTGTGGTGGGGCAGGCAGAGCGCGACACCCCGGACGAGGTGCTGCCCACCGCCGCCTTGCTAACGGGCATTAATCAGCCGGATCATCTCA
GCCAGTTCACGGCACTTACCCAGCGACTCCATGCCCAACGTGCTGCAATGGTATGTGTGCTGCAGTCCAGGGATTGCGCCACTCTCAAGGCGGCC
GTTGAGACATTGGTTTTCGGGCTCGTAGAAGATAATGCAGAAGTGGAGCAAATGGAAGACGAGGACGAGGACGAGGATGGTGCCGAACGGGATCG
CAAGCGGCTACGTCGCTCGCAGTGCACCATGAAGCAGTTGAAGTCTTGGTACACGAACAATTTTGACTCGGAACAGAAGCGCCGCCAGCTGGTCG
TCATCCTTCCCGACTTTGAGTGCTTTAACGCAAGCGTGCTGCAGGATCTTATTCTAATTTTGAGCGCTCACTGCGGCTCGCTTCCATTCGTCCTG
GTCCTGGGAGTGGCCACGGCCATGACAGCTGTCCATGGGACACTACCATACCACGTCAGCAGCAAGATTCGTCTAAGGGTGTTCCAGACTCAAGC
TGCTCCCACGGGCCTTAATGAGGTGCTGGATAAAGTTCTGCTGTCGCCCAAGTACGCTTTCCACCTGTCGGGAAAGACATTCAAGTTCCTGACGC
ACATCTTCCTATACTACGACTTCTCCATCCACGGCTTTATTCAGGGCTTCAAGTACTGCCTGATGGAACACTTCTTTGGTGGGAATGCCTTTGCT
CTTTGCACAGACTACAGCAAAGCATTGGGACGCATAAAGCAGCTGACCCACGAGGATATGGAAACCATCAGAAGGCTCCCATCGTTTCGTCCGTA
CGTCGAGCAGATCAATGATTGCAAACGCATCATAGCCGTGCTCACGGACGATGACTACCTAAAGAAGAAACTGCCGCAGTTGCTGCGCGACTGCC
TGCTCCACTTCCTGCTTTTCCGCTGCTCTCTGGAGTTCCTTACAGAGCTGGTTGGTGATTTGCCGCGCTGTCCGCTGGGAAAGCTACGCCGGGAA
CTGTACGTCAACTGTCTTAATCGTGCGATCATTTCGACGCCGGAGTACAAGGAGTGCCTGCAGATGCTAAGCTTTCTGTCCAAGGACGAATTTGT
TGCTAAAGTGAATCGAGCCCTGGAAAGAACCGAACAGTTCCTGGTTGAAGAAATTGCTCCGCTGGAATTGGGCGAGGCCTGCACTGCTGTGCTGA
GACCTAAGTTAGAAGCTATACGCCTTGCAGTGGACGAAGTGGTCAAGGCCACCATGGCGACAATTACAACGACATCGCCCAATGAAACCCGCCAG
GCGACTGACCATTTGACTCCGGTGGCCTCGCGTCAAGAATTGAAAGATCAGCTCCTACAGCGTAGCAAGGAGGACAAGATGCGGCATCAGCTGAA
CACGCCCACCACCCAATTCGGACGAGCTCTACAAAAGACTCTGCAGCTTATCGAAACGCAGATTGTACAGGATCATCTCCGTGCGCTGCAGGATG
CACCACCTATTCACGAACTTTTTGTGTTCAGCGACATTGCTACCGTGCGGCGAAACATAATTGGTGCTCCGCGGGCTGCACTGCACACTGCCCTG
AATAATCCACATTTTTACATGCAGTGCAAGTGCTGCGAGCTACAAGATCAATCACTGCTGGTTGGCACACTGCCCGATCTCTCCGTGGTTTACAA
GCTGCACCTGGAGTGCGGTCGCATGATCAACCTTTTCGACTGGCTGCAGGCCTTTCGATCTGTTGTGAGCGACAGCGACCACGAGGAAGTGGCCC
AGGAACAAATCGATCCCCAGATCCAGGCCCGATTCACGCGTGCCGTAGCCGAGTTGCAGTTTCTGGGGTACATTAAGATGTCGAAGCGCAAGACG
GATCATGCCACTCGATTAACCTGGTAGCTCGCTCGGGCTATGAATAACCAAAATCCCTTAGGTATTTTTATCTTTTCTATTTATTTATATTGGGG
CAAATTTCATGTGTGGGACGTTATGAATAAATAAAACATCAATCGATTTGTCTACTCTGTACGAAATGCATTAACTTTGTTTGCGAGTGAAGCGC
GTTCTTGTATTTTTTAAGTAAAGCCCAGCAGCTGGCAAGGCAAGCGTACTAAATATCAATTACCAGTCTTCCCGACTAGCGGTTACCACGTTCCC
TGTTCACATTAGTTTCAGAGTCTCGATGGCGGCAGCGATGCGTTCGATCTCTGCCCGCGACTCGCAGAGTTTTGTCTCGTTGGCCTCCTGCACCT
CGGCGGGAACCTTAGTTGCGTAGTCGGCGGCCTGGATGGCCTGAGTTAGCTTGCCCACCGTCTGCACCAGCTGGTCGCTCTTCTTCTGCAGCTTG
GCTATCTCCTTGTCCGCCTCCACGAGTCCCTTGAGCAGCAGGTGCACCTCGCACTGGCCCGTCACGGTGAGGATCGCACAGCCCTGCGGTGCGGG
ACTGTCAAAGACCACATTGGAGCAGT
(SEQ ID NO: 440)

Start ATG: 997

MDPTISVSKGCFVYKNGATRAGKKAASKRKRPAAESSSLLGKEVVQQPFYEEYRKAWNQINDHIADLQHRSYARTLEQLVDFVVGQAERDTPDEV
LPTAALLTGINQPDHLSQFTALTQRLHAQRAAMVCVLQSRDCATLKAAVETLVFGLVEDNAEVEQMEDEDEDEDGAERDRKRLRRSQCTMKQLKS
WYTNNFDSEQKRRQLVVILPDFECFNASVLQDLILILSAHCGSLPFVLVLGVATAMTAVHGTLPYHVSSKIRLRVFQTQAAPTGLNEVLDKVLLS
PKYAFHLSGKTFKFLTHIFLYYDFSIHGFIQGFKYCLMEHFFGGNAFALCTDYSKALGRIKQLTHEDMETIRRLPSFRPYVEQINDCKRIIAVLT
DDDYLKKKLPQLLRDCLLHFLLFRCSLEFLTELVGDLPRCPLGKLRRELYVNCLNRAIISTPEYKECLQMLSFLSKDEFVAKVNRALERTEQFLV
EEIAPLELGEACTAVLRPKLEAIRLAVDEVVKATMATITTTSPNETRQATDHLTPVASRQELKDQLLQRSKEDKMRHQLNTPTTQFGRALQKTLQ
LIETQIVQDHLRALQDAPPIHELFVFSDIATVRRNIIGAPRAALHTALNNPHFYMQCKCCELQDQSLLVGTLPDLSVVYKLHLECGRMINLFDWL
QAFRSVVSDSDHEEVAQEQIDPQIQARFTRAVAELQFLGYIKMSKRKTDHATRLTW*
(SEQ ID NO: 441)

Name: Origin recognition complex subunit 3
Classification: DNA_replication_factor
Gene Symbol: lat
FlyBase ID: FBgn0005654

Celera Sequence No. : 142000013384826
ATTAATTTGTCCAGTTACGGAATCATATTCGGCTATTCCATGATAGCTTTTGCCAGTGTCTTTCTCATCACCGGCATCACGCTGACTGTGACGAA
AAAGTGGGTGCGGCGAACTCCCGAGGATGAGGACATACTTACCAACTAGAGCAAAATAGTTTTTAAGCTTTGCCAAAGTGCCAGGAATTGTTAAC
TCTCCTAGTTCATTCTGATAGTCGCCCGTCAAATGCTGTTCTTTGTCAGTTATGCGTTATGTAATATGTAAGTGATACGAATCGACGTTCGTCTT
GCAGTTTGTGATAGCAAAACCTACTCTAAAAAAAAAACTAAAAACTACTCTAACTCTAAAAAAAAAACCTTACTCTATCTGCATATTACACGAAT
CATTCACAAGTTGAAACTTTCTGTTTGAGACTTAAGTTATCGTACTTGATAAACAATACTTCATACAACTAAAACACTCCGTGCATTTTATTTTA
ACGTTTTTATTTGAATTTTCATTTATTTTGAAAAGATAGTTTTTTACAATTTCTGTATGCTTTTCTGCAGGACTTTTACTTATCGTATACGATTG
TTGGATGCTTTAACGATTTGCTTTATAAATGCATTATTCAAATGTTGTTTTGTAAATTAATAAATAAAAATAATTGTATACGTATATATATTTAT
TTATATATATGTATATATATTGGTGTATATGTAAGATATATGGCAAAAATTTTACATTTTCTCAAAGATCACATTCCTCAATTTAGCCATAGACT
TTTAGTCGAGAAAAATCTACGCAAATATTTGTGACATCCATCAAAAACTCAAATTAATTTTTGCACGCACACTAACACATCCAAAAAAACAGTGG
GGGATTATTAATCGAACAAAAAATAATAAACAAAGTGGATACAAAAAATAAATGATAATCATCTCTCGCTTATTACTATGGTGGGGATGGAGGGC
AAGTCTAGGCACTCTTGAAATTCTTTAGTTCCCTTCGTCCAGCGATCGGAGCAAGCAAACCCATTTCAAACCATTTCATAGCCGATTTGAATGCT
TTTCACTTGATTCTACCGCTGGCCCGATTCGTTGTGAGTATGTGTGTGTGTATAAAGAGCGACGTTGCTACGTACTAAAAAATTTGCATAGTA
TATGTTGCGTTGTTCTTGGTGACTAAAATAGTTATAAATTTAGTATAAGTTTAAATAAAAATCAATCACAGTTGTTTGGGCGGAAGTAGTTAGTT
TTAAGTATTCGCATTTCTGGCCTAACTAAGTATTTGCAGCTAAGACTAAAGATCTACGATGTAGTTTAGTAAATTAGGTAGTGGTCGTATTTTAT
ACTTGAGTATTGTTGCTTCCCATTTTGATAAGCTTCCTCTCTATTTCCGATGTTGTGTCATGTTGTGGTCTGTGCTGTGGTTACGTTACCAATTC
CCTTAAGTGACTAGACTGGGTTCTGATTATTTGAATGTGTATTTTGAGGTTACGTTGCTCACGTCCTGTAGGCTTAAGTATTGACTCTGTGATAT
TCAGTTGTTTCAGTGGCTCGTGTATTTTACCATCTGAAGTTGGTGGACCTGCTAGTTTGTGTTTTTCTAAAAAACTGTCTTCGCTAGTTAAATGC
ATGTTAGTTCCTACTAAATAGCTATTGTTTCTGCTGTTCTGACAAATGGTTTCTCACGGTGGGTTTTCGTTTACATTTACCCTTTTGTGCCCGGC
GAATCTTTACCCTTCGAAACACTGTGATCGAATTTATATAACGCTACACCACCCGATCTATGCAAATTTCCGAACGCAGAATTAGCTCTTCACCT
GGGCACACTCATACATCAGCACTTCGAACAGCAATCGAACTAGAGAGAAGAGTGTCGTATTGGACCCCCAATGTCCACTTCCGTTCCGGTTTCCA
ATTAGCTTGTCGAGTCTAGCTGGTCTTGTTGTGCTGCTGCTGCTGCTGCTGTTGCTTCATCATGACAGCGGGATCGATCACGTAGTTGTTGGCCT
CCGCCAATTGTTGGACAGGTAAAGGCGGCAGTTTGTCCTGCGGATGACGGTGGCTTACGGTAGATCCTTTTCTGGCCTTGCTTAGGGTTCCTGCT CCTGCAGAGGAGTTGGCAACTCCATTTGTGGTGGCACCTGAAGGTTGCGCACTGGAAGTGGGCATCTCCTGGCCAGTCTTCGGATTTATAACAAC
CTTAGTCTGTTTCAGCAAGGAGCGATCGTTGCAGAGCGCCGAGATCAGCGGCAGATCTAGATGCTTGCTCTTCTCCCGAAGAAGCGCAATGTCTA
GCGCTTGGGCCTGTGCCTGGGCATGAGACTGGGCTACCATTGAAGCCTGCAGCTGGGCCAAAATGCTGTTGTTTCCCCGGTTCAATCCCAGACCA
AGACCCAAGTCAGGTCTCGGACGCTCACCTGCCCACTGGGCGCCGCTGGAGGTCTTTGTTAGCGGTGAGTTCGCATGATGCGGATTCAACGTTGG
GGGTTTTCGTGGTGGAATCGGGCTCATCCTGCTAGGAATTGGCTTAGAGGGTACTGAAAATCGGAGAGATTAATAAGATATCGAAATGAATCTAA
ATGTAAAGTTACTCACTTGGAGGTGGCTTTTCACTGGGCGCCGGCATGGGTGGTTTCTTTAGCCGTCTGTTTACATACGGTGGTGGTGGCGGCGG
TGGCAGTCGTTTTCCCTTGGGCAGCAAATCTAGTGAGTTCAGAATATTGTCATCTGATCGCGATCGCGCAAACATCGAGGAAGACGAGGAGCCAG
CCCCCGCCGCAGCAGCTGCTGCTAGAGCAGCCGGGTGAAGGGGAGGAGGCGGTGGAGGCTCATACGAGGAGCATAGGCTGGCCATCGAAGGAGAG
TACAGGGGTGAGTATCCGGGTCCTGGAAGCTGCACATATGTATCCGATAGATTTTGGGTGGATGCATATCGTGAGTGGGTCGACAGAGTCAGTGG
TAGGTAGGGGGTGCTTCTGTAAATCGCCGGCGACACCTGCATGGCCAGATATGGGTGGTGCGGTGGGGGTGGTGCTGCTTGGGCCATTGCCGCCA
GTAAGGATCCCTGTTTGGCATCCAGATACTCTTGCTGGCTTACAGCTGGATCCTGGATGGGGTAAATTACGTAATCCACATCGCTGTAAAGCTGC
TGCTGGTAGAGCTCCAATTGTTTTCTAGCCATTTCCCTCTCGTAAAGGTGACTCGCCAAATGGGGGTGATTCGGTGGGGGCGGTGGTGGAGGCTG
CCGCGGCAAACTGGGCGGTGGTGGTGCCAGGAACTGCCGAGGTTTAATAACCGGTAGTAGTACACATGACTGCTGATGATGCAGTGATGCCGTGC
TCTTGTGCAGACCGTAAGGAACTATTCCAATGGCTGCCGATCCAGAATGTCGGTGGTGTGACGGCACGTGATGATGGTGCAGTGAAGCCTGGGAT
CCGCCGGCATAGTTGGAGTTATGCAGCGATTGCTGACTCAACTGATGGCTGCAAACCGATCCATTGGAGGAGGCAACTGATGAACAATGGTGCGG
TGCCGCGTAACTTGGCTTGGCCCCATCGGGAATCAGGCTGGTGTGGGCTTTCAGAATACTAATCTGTGGCCTGGTGGTGATAAATCTGGCTGTAA
CCTCCTCGGACTTTAAAGAACTCATCGAGCCGGCAGCACTGGGCGCAGGATGTGCCGACGAACTGACAGATATCAGGGATGTGGGTCTAGGCTTG
CTAGAGATGGAATATGGCGGTGGATCTCTTCGTCGAATAGCCGGCGGTGGGGCTGGAATTGGTGCTGGCGGTACCGGTGGACTACATGGCGGTGA
ATCTGGTTTGGGAGCTACCACAGCTATAGGTTTAGGGATAGGTTTGGCGATAGGTGGGCCACAGAGACCAGTTTTCTCATGCCTAGCACTGTAGG
GTGGTGGTGGTGCTGGTGGTTGGTCTACCTCCTCTTCTCCTTGATCTCCTAGTGGTAACGTCACGTAATCACAGTCCGAGTGAAGGCTACTAGAT
ACTGTTTTCCGACTGGGGTAGGTCCCCCTGCCCACAATCAAATTGGTTAACTCTTCTGCGGAGAGCAAGGAATGTTTGTTGTCTGTTGGATCGCT
GCCATCGCCTCTAAAGGAACTCCCTGTGCTGACGTTAGAATCCGATCGCGGTCTGAAGTCTTCTTTCTTTTTTCCATCTACGGAATCAGAATGTT
GCACGTGGGTTTCTTCTAGTTTTGGGGCTGGAACATCCCGTAGTGCGAACTCTTTTCCGACTCGGCGATCTCCGATGATTGTCCAGTTAGCTCA
CTGCTGTGCATGGTGTAAACGCCTGAGGTTTCCGTGGGTGGAGCTCCGTGCGCCAAAGTATAAACCCCAGATGCGCCCGATACACTCTCCGTTTC
TTCTCTTGCCGATGTGGAGAGAAAATCGTCGGGACTCGTTTCGCTCAAGGCCGAGTTTTGAGCGGTGTGACTAAAGCCAAGCTCCAAACTAGATG
AAGTGGAGTGCACAGGTATGGGAGCACCTGAAGAGGAAGCGCCTGCTCCATTTACAGGAGATGTTACCACCACAGTGCTACAAGTGGATGAGCAC
TGAGAGCCGATGTTATGCTGCGAACTGGGTGAATCAGTGGCGGTAGATGAATCATTGGCAGTTGTTCCCATGGAATTTCTCTGAACAGAGGAGTT
CGTGACGATCGTGGCCCCGTTAGAACTCGCGTCTTGTGGCCTCACACTCAAGGCAGCCAGTTGTTCTTCCAAATCCTTCAGAGACATCTGACCCA
CGCTCGAAGTTTGTCTGCTCACACTGGGTCTGTCCAAAAGATGAGCCAAGGCCAAACTTTCCGTTGACGGAGCAGCTAAGGGTGCTGGTGGTGTA
TTGATCATGATCTCCAGCTCGTCTTCGGAGTGCACTCGATCACTTACTATCCCAGAGGTTGTGTTGGAGCTGGTACTCGAGATAACCGATATTCG
CTGCTCGTTTTTACTTTTGTAGGGCAAGAGCAGACTTCTGGAACAAGCGTAGCTGGCATGTAGCCTTTGTGATTCGGCAGCCTCCTCCTCCTCGC
GTTTGGATACCTCCTTTAGCCTGGCAGCCAGTTTCATGCTCCACTGATGTGTATCCTTGCAGAGGGTCAATAGGAGTTTATTTTTCTCATCGGAT
GCGGCGTACAGGGTGATTCGGCTCTCTCCAGATCGTATTTCAAACTTTTTCCGCTCGAAGGAGAGCTTCGTGATATTCGGCCACAGAAAGGTTGT
GGTTTCGGGATTGGAAGAGCTGTTGGTAGACTCTCCTCCCAGAATCTTGATTCCCTTGGCATAGACCACAAACCAGGCACTACCAGATCCCTGCT
CGCTTTTGGCCAATCGCATCCTGTAGGTATGGGCATTGATGGTTTCATGAAGACTGCATGCCTGTTGAATATATAGCAGCTCCGCCTCTGCCGTG
GCCATGCCCAAATGCTCCCGATGACAGGCTCTCATTGCACTTCTCGCCCAGGGAGTGTGCAGTCCACTGGGTAGGTAATCCTCGATCCGGTAGTA
ATCTGCTCCATTCGGTGGCAGGCTGGGTGGTAATGGTATTGTTTCTCTCTTTGATGTGGACGCCACATATGTCGAGAGTCTAAGCATCCTCTCAT
TAGCACGTTTGCTGATCTTGGGTAATGTAGTGGTGGCACTTAGACCTCTTCCTCCGTTAGAAGGAGATGCCGATGTCTCCTCTCCTGAATCATCC
TTGGAATTACTCGTGCCCGGAGGAGCATCACCCAGGTCCGCCTGAAGAGCAAGTCCAGCAAGGAAGACCAGTGCCTGCTCCGCCTGTTCTCTCGG
CAAATCGCGCTGCAAGATGTTGTGGCGCAGCTGCAGGTAGTAATTATGGCGGGACGTCTCATCTTTCAGCATGAACGGGCTCTCGATGTAGAACT
GCACGCGAAAGTGTAGCTCCAGGAGCGGTCGTCCGTTGGCATCCAGCCCCTAAATAAAGACATGTCGCATTACTTAACACATCATGATAATTACT
TTTTTAATAAATATTTACGTGGGTGTGCGATGATCGCCAGCTCTTTGGGCCATATTTTGAGAGCTTGCTCTCGGGATCTGCGAACATGTACTCGC
CATCTGCAACATACGAAACAAGAGATTGGTTATAAAAATGGTTTGATTGATCAGATTTTGGGTCTGCTATTCCATCGAACATTCTTTTTTTAATT
TCAATTTTTTTAAAAGTTAAAACGGAGGTGCATTCATTAAGGATATATAAATAACCAAACAGAGACCTACAACTGCTTTCATTGAAATATCAAAT
TACTTGTCAAGTCGGATGCCATGCCTTGGCTGAATTTCCGGTTGGGCTAAGGAACTTTTTGGCGCGCAGCCGCCAAGGTCGCTAATCAAAATTTT
AAATGAACTTTCGGCTATGCAAGAGGGAGCGCTCCTCTTGCGTCCCAAATCGGGCTCAAATCGGATCGAGACCCCGACCAGACTTCTGTCAGTTT
GTCAGGCAATAAACAAGCAACCCATTGACATCAACAAGAGTCAGAGACTCCAGCAGATGAAGACGATGATGATGACGACACGTCAGGTTGTCAGA
GGCCCATTGCCTGATGCTCGAAGACGAGACCGGTACCGGACCGCGCTACATAGCTCCGACCCGAGCCAAGCAGAAGGGCCCAAGGGCATGTCGGC
GGTGCTCGAGAAGGCAGAGAAAAAACAACAGCGAAATCAACACACACTTCATCGAACGAAAAATTGGAATTCCTGCATACAAAATGAAGAGCAGC
AAGATGAAAAATAATAATTATGAAAAAAGCAGGCAGGCAGGTTGAAGGAGGCCATGGAATAGAGGCACCTCAGCATCGAATCCACAACACAGCAG
CAGCAGCTACAATATCATAATAATCATCAGCGGCCGAATAAGTGCCTATCAATGACGACGTCGTCGACGCAAAGCTGGAATGGAAGTGGCAACAA
GTGGATGGCCAGGGGAGTAGAGCTCTTCGAGTTTGGTTCACTCAAAAAAATGATTAGGGAATACTAGCAAAATATTTTGTTGCCAAACCTAATCA
CCCCCCACAAGTTTGTTCTGGGAAAGTTTTGCCGTAGCATAGAGCGTTGTTCAGTTTATTTGGATTTACGAGAAAACCCATTTCTTTTGCACAGT
GTAGAAACGGAGTCGAAGCGAGAGCGAGTGTTGCATACCAAGCCCAAAACGCAGCATCGAACAAAACCCGCAGAGAAAGAGGAAAAAACAGGTAG
AAAGACAGGTAAGCAGCGCTGGAAAAAAGAGGCAGCTGAAACCCAAGTCGTTCGGTTTTTAGCCGCAGTTTTTAGACTCCAGCCTCAAAACTCAA
AGCGATTTCTTTTCGCATTCAAATTTCACTCCACTCCAGAAGTTTTCGGCCAAAGGCTCTCCAATGGAATTCGTTCTTGTGCACGTATCGGAATC
CTGGTATTCTACGAGCTGCGGGCAGGTGTTAGGGCCAAAACAGTCGGATCTCGGGAAGCCACTCGTCTACGGCGGCCTGATGTGATGGATCCTCA
CGCAATCCCAGCGTTCCATTCTACCTTGCCCGCTCCCAACGGCAAAGACCTAATAATTAACATATTTTCCATCGCATTCCTCAACGCTCACAATT
AACACGCACGCACTCGGTTTTTGGAGAAGGGTTTCGAGGGGCAGCGAAATAAATCTTCAATTTGAAACACATGCAACACAAATTACAGCCTCAAA
AGCAAAGGCAGCTGGCCAGGCAGAGGCAGAGGCGGGGGCAGGGGCAGAGGCAAGGCTCATCAAGCAGAGGAATTCCTGAGGTAATGGCAGGAGAA
GGAGGAGGAGGTGGGGGGCAGGAGATGGAGTCTTAAGTTGAAGATGGAGAAAGAGAATGAGACGCAGTCAGGGACAGCTGCGCCCAATCCCATGC
CATGGCTTGGAATTCTTCAGATTCAGATTTATTTTCAAGAAGGTCGCAGTCCGAGCTGAAGTGGCCATAATAACCAAAAAAAAAAAAAAAAAATTT
CGCAGGCGAAACTAAGCGAAAAACTACTCCTGGCTTTAACGTAAGACTAAGACTTGTGAAATATTAATATATTAATTAATAACAATAGAATGCTA
GAGGACAGACCACCATTAGAGAATATTAACTTCAATATATGTTAAAAGCCCACAAAGTCCAATAAGTTTATAAAAACAAAATATAAAATATTTTT
AAATTGCCAACTTCGGATATACCCGGTAAGTTGGATGTGGAGGCTACAGGGTATCCTAAGAATGGGCAGCAACATAAATTTATGTGTGTGTCTGT
GCATCGAAACTGGCTAAGGAAAGAAGAACGAAAGACGAAAAAAAAAAACGTAAAAACCAAAAGAATTTTAATTTCCGATGTTATCAGATGCACG
CAGCCCAAAGAGGAGAGGCGGCAGCTCCAGGGGATCAGGGGATGGACAGCCGATGCAAGGCCGAGTGTTCACGTCCAAAGATTGAAGACGAAGAC
GAAACAGCCAACGCCGTATAATAATGATTATGAGCCATTAACATTAAATGGAAAAGAAAATGCTGGTCTACAGATTTCAGCTACAAAGGGGGTGG
GGCTCCACAAAAAAGGGTGGGGAAAATCATGAGCCCGGAGCCAAGGGGGAGCGAAAAATGTGCTTTTCTGGCCCGGAATGCAGCTGAGGAGTGGA
ATTCAAGGAATGCGACAGCCTAAAAATAACACCAAAAGGGGAGAATGTCGCTTGGTAGATGACCACTGGATGACAATGTTGCCAAATGGCCATCG
GCCCAGTGCCACTTAAAGTGCTGCGATCTCAAGGAGCAGCTTAAATTTGCATGAAAATGCAATTTATTGACACTGGGCGGCCATAAAATGTAAAT

FIGURE SHEET 244

TCATTTCCATCCCCGTTAAAAGCAAAAGAGCAGACCCAACTTAATTGTGACCCTCTTTTCGTTCATTTTGAGGGAAATATCGAAAGACCAAAACA
ACGAACTCGGAAACATGGAAGGACCAAAAGTCTCAGATTAGCTATCCGAAGTATTCCAGGATAAGTCAGCAAGCATAAATCTGGCAAATGCAATA
GCAAATTGAATTGCCAATAAGAATTTCTTCCTTTAGTTTAAATACTTTTTGATTGATTTTTCGACTAAATAATATACTTAAAGTTTGCTAAATAT
ATGTACTCTGGATGAGGGATTGGGTCTCGGAAACATACCAAGTCCAGGCCAGAAGAGCAACAACAATATATAGCCGCATACCAATCACAGATACA
CCGTCCACCGACATTGGCAGGAATCCTTGGCCACAAACCCGAGCACCAGCGCACACACGAAAGCAGAATGCAAACTGCCAATTTCATAGTTGCGC
CTGAGGAATCCTCTGCGAGGCGAGGACGTTGGCATGCCCAGCCCGATTCTCATATTCAGTTAAAGCTGCATCTACAGCTTCGGCAGCGACTCCGG
CTTCAAGCTGCATACCAAATTCTTAGCTGAAGATGTTGTGGCAACTTCAACGCTCCCCTGCCTCCTGCCGAGAAATTGATGCCAAGCCAACCAGC
TTCGAAAATTTACGTGTTGTGTTCTTGGGCTTTTGCTCTAACATCGGATCACAAAATAAAGGGTATACCGGAATAGTCATTTGGGTTAAATAACA
ACAATCTCCCTAGGCGATTCGATGTTTTAATGTACATTACTTAAACAGGCGACATTTGGCGTGGCGTTTGAAATAAACGATAAGAATCTTTCCCA
TACAATTTCTTTTGTACAATAATTAATATACTTTTCCCTTTAAGAGTAAGAAAACTTCGATTACCAGAAAATCAAATTCCTCTCTCCTTTCTTGT
TTGCTTCTCCCCGGACCCCTCGTTTCCCCGTTTTTGGTTGCTTGTGGGTCTTTGGAGAACACATATATCTGTGGCCAATGCCAAAGACGTTGTCT
GCTTGTTCCCCAGGTTTCAGCTCAGACTCCGGAGCTCTGGGCTCCTCCATCCTCAATCCTCCATCTTCCATCCTCGAAACTCCATCCTCCGTGGC
TGTCGTTCGATTCGTTTGTGTTAATGCAACGCGCGACGGCTACCTGAATTACTGAACACGCGTCTTGTGTCTGCTCCCCTGCATCTGCAGCTCAA
CGGCTGCTCCTTTGCTGAGCCCCTCTTCTGTATTCCTGAAATTGTTTGTTCGCCATGAAGGCGACGCGTTCCCTGCCTTTTTGTTCGTTTTATGT
GCCATTTTTTGTGTTGCTCCGCTGTGTTGGTATTTTTATGTGTTTTGGCAGATCGCTTTGGCCAGAAAGGAGGATGGAGGCTGAGTCCTCTGCCG
CTGCTGCTGCTGCTGCTTCTGCTGCTGATGATGATGAGCAGCTTTTAGAGCGGACTGGTTTATGTTTATTAGTTGTATTTTTCAGGCCTTATCGC
TAGCATTTGGCTACTCCACAACTCGGAAACAAACTGGACGCAACTGACTTGAAATCCCCCCCCAGAACCGAAATGGACTTACCTATGAGCACAGC
CAGACCGAAGAGTTCGGTGTCCAGCATCCCTTGCGTGGCAAAGTGCAGACATGTCTGCGTGTAAACCTCTCGAACTCGACTCTTGGCATCGACTA
GGAAGTACAAGGTTTTCGGCTGCTGCTGCCCCAGAAGTCTGCAAATTCCACACAAAATTAAGCAACACCATTTTTGGGCGGCCTTTCCACCTTAA
ACACTCACCTCAGGGCCAGGAATCGCGAGCCTGGTGATAGTTGCTCGGCTGAGGACGCGCATACTTCCAAAGGCGCGCTGACGGTGCAAAATGCT
CGCATGCTGCATCATTTTCCGTATACAGCGCGCGCGTTCGAAATACGTTGCTATTTAAAGTAAAAGAATAACAAAGATTAATATCTGTATAGATG
AATAAAGAAACTAAACTACATAGCAGGATTCGATTTTGTAAATTTTGCAAGTGAGTGTGTGGTGGTAGGCACATTATACAAATTGAAACGCATTC
AATTACGTTTTATGTACGTATTTACGTATTACGTATATGTAAGAAAACTCATTTTAAAAGATTTTTTTTACAATTCTTGCAAATAGAAATTGTC
GCATTCAACGCGTCATTTCTAACCGCATTTCTGGCTCATCAGATGCGATAAAGCTGCCGCTCGATCGGATCGGTTAGGCACCATTCTTTCAGGCA
AATTGATGCCGCTGGAGCCGCCCCAGACGAAGTTGGAGACGAAAGGCGGAAGATGGCAATGGCTATGGCGATGGCGATGGCGCCCGCCTCTTTG
GGCTCACCGACTGCCGAACAATTTCACCAATCAATAACGAAAGACTCAGGCGACAAACTTGATTAGCGGGCAGGGGACTTGGACTGGCAGAAAAA
CTGAATAGTGAATAGTGAATACCTGGGGACTCTTAGCGGTGCGTGCGTGGCACGCAAGCTCCCTCCCCCTCTTGATGCGTTGCGCATAAAATTAT
TAAAATTCAGTTAAAGAAAGTTCCAAATGCCTGAGCTAAGAGGCAGACAGACACCGAAACTGGACTCGTGATGAAAGAAAAGTATTTTGTGCATA
AATTAAAATCAAATCGAATCAAATCAACTTTTTTGAATAGAGCGCCGGCAGCGGCGACAACAGTTTCTACCAACCCGGCGGAGACGCATAAATTT
CAATATTGGCGCATTTTCTGTGTCTAATAAATTTGAACGTTCAATAAATTTATTCAGAGTCAAATCGAGAGTCGAAGTCCAACTCGAAAGCCGAT
AGAGAGGGTTAGTGGCATCTGCATGCCACACCATAGATAGACCGAGAGACGGATGCTGAAAGAACCGCCCTGACTTATAAATATACGATCGGACC
GATCGGAGGTATGCCTCCGCCACCACCGCCTCCCAACCGAAAAGCGATCATCAATCAAAGAGCACATTTGACATAAATTAGAAACCAAAGAATAT
CTGGGAACACCATAGCTTCCTCCCCTTGAAAAGACCGCTCCAAAAAAGCTTTTCAAAAGCAATTATATTTAAGCTGATTTCCATGCGCACCTTGG
TCTCGGCTTAGGTGATCTGGAGAACAGGCTCAGACACATACTTTATGCCCGATCACAGACGATTACGAAACGAGAATCGAAATTCCAGGTCTCTA
ATGTGCTGCGATTGACTTATTACCGAGGAATTTATACGGATAAACATAAAAACTACATTGTTGAGCTCTCAAGAGGAACTGGATTAAGCGATCAC
TCACATATCTCACATGTTGAGTGACTGGCCAATAAAGAGTTGAAGTATTTTTTGAGGGCTTGGTCACATTTCTTGCACAATATTAGTAAGTGCTT
ACTATAAATATTAAATCAAATGATTTTTACCATTAGCAAGGAAATTATCCTTGTCAATAAGGCATAATGATATGTAATTCAGTGAGACAATAAGA
GGAAACCGTAAATTTTCTTTGACAAACCCTCTTATCGATTCCGATAACAATAAAAGGAAGCTAGTCGGCAGATTGCACGAAATGAATAGAAGCTC
AGAAGGAAACGAACGCGGCTTTAATGCAAAAATTGCCATTAATGGCAAGAAGGAGAACGCTGTCTGATTGGCGAGATTTCTGCGGAAGTAATACC
TCTGTCATAAAGTTATTAGACGATAAACCTTCACTATAGACTACTTCGCAGAAAACTACTTGCAATCACTTCTTTTCAATTCCAAGCCCCCACAA
TGCCGGTCATTATGTAATCGACAAATCGAATATCCAAAAATACCGAAAACATATGTGCGATCGCGATTTCTTTGAGGATGAGTCAACGAAAGCGT
TTTAATTAAAAATTCAAACAAATTCAAGGTGTTTAAAAATTTCAATCATTGAAAATCATCCGCATTCCATTGGCTAACAAGAGCGGAAAGCAAAG
AAAGCCGTGGCAAAGCTAATTATTATAGCCAACCTACGAGTTGGGGGTACAAGGAGAGAGAGAAATATTGTCTTCTCAAAAATAAAAGAAGTGTA
AGATTTATAATATTTCGGTATGCAACGAGTATCCAGGATTTCACCGTGCACTGCTGGCAATTAAAGTCGAGGCAAAGAAGCGAGCCAAGTGGAGC
TGAGCGACCGCAAGAGACACGCTAATCAGCAATTAGCAAATGGCAATAAATATTTTGTTTATGATTAAGCGAGGGGCGAAGGTGTCCAGTGGCGG
GAGGGGGGTTGGCTGTTAGGAGTTTCGCGAGTGGGTCGGCTTTCCGAGAGAGCTTGGAATGCAGACACTGATGGAGCACAAGAAGGCAGAGGGGG
CAGATGGGGGCTGGAGCAATAAAATCTCACGGGCTCTGCCGCGATCAAAGTCAATTAAATGGCGCAAGCGCCAGCAGTGAATGCTTTTCTGCTGG
CTAAGCGAATGCCAAAGGGGTAAAGAGAGCAAAAACCAGAGAACTAAGTTGGCGACTGAGCAACAGAGACGTTCCGCATACGCCACGTTGTGCTG
CGACAGCAACTAAGCACAGAAAGAAAGCACTGTAAAAAGTTTAGCATTTAATATACGAATTTTATTTCATTTAAAAATGTATTATATAAAAAAAA
AACCCATTCCTAATTATACAGTCATCTAAACTCGTTGTTGTTGTTGATAAGTTCCATAAGAAAATTAAGAACTTTAATATTTATTTCGGTTTTCT
TTTCTCCCTGTGAACGACCGACTACTATGTCAACTGCACATGCCAATGCACTGAGCTCATTCGGGGCGTGTGTTTGTCAAGCGAGTTCCAACAAT
CGCCAAAGTCGAACGATCGATTCGATCGATCAGACCCGAGACCCCAGACCTCACAGAGGTCCAACTACGAACTACGTATCGTGGGGCTGGCGGGG
CAGTCGGAGGTGCCGGAACCAAGACCTATAGAGTCGAGACTACGATAAACGTTTCAACCGCATGTGCAGGCCCATTGAAATGCTGAACGAATCAG
AAATTGAAAATATCCATATGGATTTCAGCGCGGAATGCGAGTGCGCATTGAGCAGATCAATAAACATGGCAGCGCAAACGGTCGTAAGTTCGAGC
AGCGAGGAATGCGAATCAAATTGGCTCTAAAGAGGTCTCAGAGATCACCAAGCTGGATAGCTAACTCGGGGATACCACATGTAACTGTCTTTAAT
CACCTAAAAAAATATATTAAAGAATTTAATATATGTGTCCATTTATCCACTTAGGCTCTGATGGGAAGTAGCCAAAATATTTTATGTGGATCTCA
TCATATCAAGCATAACATCGAAAAGCCCTCAGTTCTAAACTTGAATCTGGATTTAGCATGTAGCCCTCACTATCTATCTACCTCTTTATCTTTCT
TTAGCGAAAGCGTATGAGAAGCCCGTTTAAACCCACACACTCCACGTAAAGATCCCTCAACATTCTTCGCAGTCTTGAATTCTTTGAGAAAATGG
CAAGGCGATCTTTTGAGTCTGCGGTAAGTGCTCGCGTACCGCGCGGCTCTCAAGCTCGATTCGCATTTTATTGAAAGTGTTTCGAGCGCTCTCAG
CTCGCCAACTAATGAATGACGATCGGATCGGATCGGCGAGCGGTAACTTTTGACGTGGAATATTTTGCTCATGAGTTGGACGGCCGAGACCGGAA
TGGACTTAAAGCCGGAGCGGGTTCTACGTGAGTCTGGGCCTTTTAATTACCGATAGAACGGCAACTGGCGTCAATGGGACGGCCAGAAATAGTTC
AGTTCGAATCTGTTTGCTGGCATTTTCACACGCTGGCCAACGCGGCGGATGCGCGTCATTCAAAACGGGGCCCACAAGTGGTATTCCGAAAGGGG
TGTGGCTCCCGGGTGTTGTCGCGCAAATGAGTTTAGCCTCAGCCTCTGCCTCTGGCTCAGCCGATTTCTGGCTGATCAGGGGTAAAAAGTCCCCG
AAATGCCCATTTTCGGAACGATTGTTGAAATTGCCTAATGACGCAAATTATGTAAAGAGCCATCAATTTGGGTGTACCTCATAAAGCACACGGTG
TTTTAAATTCGCGAACTCCAGACACCTTTAAAGCATTATGTGGATAATATATATTGTTTTGAATTGAAATCATCGCAAGTAATTATGAAAGCAGT
TTTCTGTATGCCGGGCTTAGTGTGCCATCAAATCGCCAAATAACTCGTCGTCTCTTTGCCAAACTGCGAATATCGAATAGGAGAAAACAGAAATC
AGGGAACAAGCGACTGAGAAATAAAACAGCAAAGCGGCAAATGCCGAATTCCGAGCTGCGGAATTCCACTTGTTGTGCCAGTTATGGCCAAACAA
TTTGATGTCTTTGAAATGCGTGAAATGTCCCCGCCGACCGCCGATGATAATAATGAAAATGGTCGCTTGCTCGGTTGGCTGGATAGCTGTGAGGA
GCAGCCAGGGCGGAGTGGGCCAAAAGAAAGCAGCCCACACGTCGTCGCTCGGCTTCAGTTGGCTAGGCACCACAAAATCGCACCACATCGCACCA
CTCTCCTCCACTGCGCACCACACCCCGCAGACGCGAAATGCCCAACTGGGCGAACGAAGGTGGTAACGGTGGCGGAGGCGATGGCCTCCACAATG
AGAGCAGCAAACAGCAAGATACAAAAACAAAAAAGAAGCCGCAACGTGTGCCGCATGCCAAATCGGAGGCGTGCGAAACTATGCTGCCATAATAC

CGTAGAAAAATTAGCAGTCCATACAGGGTATCTTGGGTTAAATGAATGCGCTATAATACGAGTAACCAATAATTCTAAAGTTTAAGGTATTTTGA
TTATGGCTAGAATAATTCTTTGACCAATTCTAAGTAAAGAGGCTTTTAAGTTTTTGCCTATCTGGCAATATGTTGTTGAAACAATATTTTTTTAC
GAGCATAGAGATAAGTACATTTTTTTAATCCTCGAAGGTCGTTCATTAGTGTATCCTCTATATCTCTGAGCCAGCCTCGACTCCGATTGTCATTC
GAAATTTGTTTAATTTGTTGTACATTTTAATTGCCTGAATTGTTCGAGGCAATGAGCAACCAGAGTTTTCAATGTTCGCACACGCATATCAACTG
CGTGCAGGAATTTCAGTTTACGAAATTAATATTTTGAGTTTGTATGATCATTGCTGTTGCTGTTGTCAGCTTCAATGCAAAAGCCCATTGCCTGA
GGTCAAGTGTGATGTGGAGATCAAGAGATACGCACGGAGATGGAGATGTAGACGTCAGTGCTCAATCGAAAAAACCACAAGCGAACTAAAACTAC
GATCCGGGGAATACATGTGTACTTGCCGAGATATAGATACGTCTGTCCGCAGATACAGTTACCCATATGTATATGATTGCCTGGTGGCAAAATCG
TTTAACGATTAGCGTTTAACCGCTTAAAGCTTATCGACTGATACCCAAAGCGTGTGTTTTCACCCGTTTGTTTATCTTTCGCTGATTTACATTCA
AGATGTCTGATTGCCAAGCGGTTTCTGATTTCAGCAATTGTTCCAGGGATCCCGATGGACGGTTGAAATTCCAAACCCGGGAATAACAATAGAAC
TCTGTGGAGCTTCCATTTTCACTTAATTGCATCGCCGTCGATCGTTCTGACAACCGTTTAAGTCGCCTATTAGCCATAGAACCTATCAAATTGAC
TAGCTCACTTGGAAATTGGATCCCGAGATAAGTGAAACCCTGTGCAAAGATACTTTAGGGCCGCATAGAAAATGTCAAAAAAAATTAATTAAATG
TGACCGGTATTTAAAAAGTCGGTCAGGCCTACTATATAACTACATATGTATGCACATGTGAATGTACATATATATTTGACACAATAGTACTCTAA
ACAGCTTCCCCATTTCAATATACCCTCCGTAGAGTGTCAAGTTTGACTGACATTTGATATTCCATGGCCCGAAATGGGTTAATTGCACAATTCGC
TGAATTTTTGACTCTTAGCGGGACGCAAAAAAAAAAATTTAAAGAAAAAAGCTGGCGACAACAACGAAATGTTAAACAATCGTTGGACGTTGGCG
ATTTTATGGTTGACAGATAAGAAATTTGCTGGCATTTGTTTTGTTTGCCGTTTTCAGGGAGTCATTAAAATTCCGGGGAAATGGCCCCATATGGG
TACACCACTCTATATCTGCACGTGTATCTGTCCTTTTCTTACCTTAAGCCGCTGCAGAAGTCGGCATTGTTAATGCTGTATCTGTATCTGCTTCT
GTTTCGGTTTCGCGTAATCCACAATAACTGGCTTTTTAATTTTGGTTTGGTAGTTTTGTTTAACTAAAGCTCACTCTTCGTGCACTCTTAAAACC
GATCTATTGATTTGGCTATCGATAAGTGCCTAACAGTAAAATTTTCGTTTCGTTGTTGTTACTTTCTGACCTCTTCCACTTCCACGACGCGCGCT
GCGACTGCGCAGTCAACAGCGATCGGGTCGCATTCCAGCGTCGCACATACTTTAATCAAAACTCACTAACACCAGAACAATTGCACACGCGGGCG
AGCGCAACTGAGAGTATCTGTGTGCGTGGAGTCGTTGTTGTTGCGCGAAAGAATGCCGTTTGCTGGGTTGTTGTTTTTGCTGTTGCTGACTGCTT
TATTTGTTGTAGTTGTAGTTTCCAGTGGGCAGTTGTTGTTGCGGCTGAATTTTTTCTTTTTGACCAGCACCAACTTTTCGGAGTTGACTTCAGCT
TTTTTACACTACTAGTCGTAGATATTTTCGTGGTTTTAAGGCGCGTTTTCCCAAAATCAGAACTAGTTGCACCAACACCAACAAAAATCACTTTT
GTAATTGAGGCGAGTGCGAAAACGAAGCGCGCTGTTTTTGTTTCAGTGAAAACCGAACTTCACTTTAAGCAACTGAATCTGTGTAGCTCTGTGTG
TGTCTGGGCGATCTGGTGTGCGTGCGGTGTGCATTTAAGATCTGAAGAACAACTTTTCCGAATGTTAGGTCTCGAATAAATTCATTAAACCGAAT
TTATATTTCCCAGTGGAAAGCACATGCTTTGCTGTCCCGACGATCTGTTCGGTTACCGTTGACGTTTAGCGATATACTGATTTTGCCCCTGCTCA
GCGAAACCGAACACAACGAAGATCGAGTCGAGATTTCGTTAAAACTTAACGAAGCCGCGTTTAACGAAAAGAGAGCCCAAGAGAGAATTCGAATT
CGAAAGAAGCGCACACAGCGATACACAAACCCGATGGCAACAACAACAACGGCTACGAAAATGTAAATAGCAATAAGCAATAAAAGAAAAACAAA
CTTCAAAGGAGAATCCCAGTAGCCAACTACATAGTGTGTGCGTCCGTGTGAGTAGTGGAATTCCAATGGCTTATCTCGCGAGACGACGATTCCGA
TTCTCAAGGGCTTAAAGGATACCCTGTTAGGATAGCAGATTTAAGTAAAATGCATATGAGAATTTTAACAAAGGTACCTTTCTTTCTAATTCTGC
TTTTTATCACATGCTATCTTGTAGTTTACATTGTATATTACAATTACATTATGAGTTCTATCTTTTGGCATTCACTTTTTGCCAAACTATGGCGG
AAGCCTATTGGATTCAAATCTAGCTTTCAGTATCCCTGCGCTAGCCATCGATGCGACTATCTTATAAATAAACTCTCTGGGCAAAACTCCAGATA
CAGATGCACTGGACGAGGGAGAATCGGAATCGGAACTTGAGGGTCTGAAGACTCTGCCTCTATCGGCGTCCTCTGCTGCTACGATATCGTCACTT
GGGCGCATTCCTCAGCATAATGTGAGCTTGATTTGCTGGATTCTTTTTGCTCCCTCTTCCCTCTTTTTCTCTTCTTTAGATTTCCTCCTTTTCAT
TTCCCCTCCTCCACCTCTTCAACCATCATTTGCTTCAAATATGCGGCATACACACGCCCCACGAAAGGGCGGGGATCAGTGTAAGCCAAGTAAGG
TTTTAACCAGTTCGTCCAAGGGGCTACTTAGAAAAATCCACAGAAAACAAAATTTAGATTATATGGAAAAAAGTCTAAATGATATAAAAATCGTA
ACTA
(SEQ ID NO: 442)

Exon: 17909..17048
Exon: 10785..10649
Exon: 10583..10438
Exon: 6083..6004
Exon: 5939..2582
Exon: 2523..1001
Start ATG: 10740 (Reverse strand: CAT)

Transcript No. : CT13612
AACAGATCGTCGGGACAGCAAAGCATGTGCTTTCCACTGGGAAATATAAATTCGGTTTAATGAATTTATTCGAGACCTAACATTCGGAAAAGTTG
TTCTTCAGATCTTAAATGCACACCGCACGCACACCAGATCGCCCAGACACACACAGAGCTACACAGATTCAGTTGCTTAAAGTGAAGTTCGGTTT
TCACTGAAACAAAAACAGCGCGCTTCGTTTTCGCACTCGCCTCAATTACAAAAGTGATTTTTGTTGGTGTTGGTGCAACTAGTTCTGATTTTGGG
AAAACGCGCCTTAAAACCACGAAAATATCTACGACTAGTAGTGTAAAAAAGCTGAAGTCAACTCCGAAAAGTTGGTGCTGGTCAAAAAGAAAAAA
TTCAGCCGCAACAACAACTGCCCACTGGAAACTACAACTACAACAAATAAAGCAGTCAGCAACAGCAAAAACAACAACCCAGCAAACGGCATTCT
TTCGCGCAACAACAACGACTCCACGCACACAGATACTCTCAGTTGCGCTCGCCCGCGTGTGCAATTGTTCTGGTGTTAGTGAGTTTTGATTAAAG
TATGTGCGACGCTGGAATGCGACCCGATCGCTGTTGACTGCGCAGTCGCAGCGCGCGTCGTGGAAGTGGAAGAGGTCAGAAAGTAACAACAACGA
AACGAAAATTTTACTGTTAGGCACTTATCGATAGCCAAATCAATAGATCGGTTTTAAGAGTGCACGAAGAGTGAGCTTTAGTTAAACAAAACTAC
CAAACCAAAATTAAAAAGCCAGTTATTGTGGATTACGCGAAACCGAAACAGAAGCAGATACAGATACAGCATTAACAATGCCGACTTCTGCAGCG
GCTTAAGCAACGTATTTCGAACGCGCGCGCTGTATACGGAAAATGATGCAGCATGCGAGCATTTTGCACCGTCAGCGCGCCTTTGGAAGTATGCG
CGTCCTCAGCCGAGCAACTATCACCAGGCTCGCGATTCCTGGCCCTGAGACTTCTGGGGCAGCAGCAGCCGAAAACCTTGTACTTCCTAGTCGAT
GCCAAGAGTCGAGTTCGAGAGGTTTACACGCAGACATGTCTGCACTTTGCCACGCAAGGGATGCTGGACACCGAACTCTTCGGTCTGGCTGTGCT
CATAGATGGCGAGTACATGTTCGCAGATCCCGAGAGCAAGCTCTCAAAATATGGCCCAAAGAGCTGGCGATCATCGCACACCCACGGGCTGGATG
CCAACGGACGACCGCTCCTGGAGCTACACTTTCGCGTGCAGTTCTACATCGAGAGCCCGTTCATGCTGAAAGATGAGACGTCCCGCCATAATTAC
TACCTGCAGCTGCGCCACAACATCTTGCAGCGCGATTTGCCGAGAGAACAGGCGGAGCAGGCACTGGTCTTCCTTGCTGGACTTGCTCTTCAGGC
GGACCTGGGTGATGCTCCTCCGGGCACGAGTAATTCCAAGGATGATTCAGGAGAGGAGACATCGGCATCTCCTTCTAACGGAGGAAGAGGTCTAA
GTGCCACCACTACATTACCCAAGATCAGCAAACGTGCTAATGAGAGGATGCTTAGACTCTCGACATATGTGGCGTCCACATCAAAGAGAGAAACA
ATACCATTACCACCCAGCCTGCCACCGAATGGAGCAGATTACTACCGGATCGAGGATTACCTACCCAGTGGACTGCACACTCCCTGGGCGAGAAG
TGCAATGAGAGCCTGTCATCGGGAGCATTTGGGCATGGCCACGGCAGAGGCGGAGCTGCTATATATTCAACAGGCATGCAGTCTTCATGAAACCA
TCAATGCCCATACCTACAGGATGCGATTGGCCAAAAGCGAGCAGGGATCTGGTAGTGCCTGGTTTGTGGTCTATGCCAAGGGAATCAAGATTCTG
GGAGGAGAGTCTACCAACAGCTCTTCCAATCCCGAAACCACAACCTTTCTGTGGCCGAATATCACGAAGCTCTCCTTCGAGCGGAAAAAGTTTGA
AATACGATCTGGAGAGAGCCGAATCACCCTGTACGCCGCATCCGATGAGAAAAATAAACTCCTATTGACCCTCTGCAAGGATACACATCAGTGGA
GCATGAAACTGGCTGCCAGGCTAAAGGAGGTATCCAAACGCGAGGAGGAGGAGGCTGCCGAATCACAAAGGCTACATGCCAGCTACGCTTGTTCC
AGAAGTCTGCTCTTGCCCTACAAAAGTAAAAACGAGCAGCGAATATCGGTTATCTCGAGTACCAGCTCCAACACAACCTCTGGGATAGTAAGTGA TCGAGTGCACTCCGAAGACGAGCTGGAGATCATGATCAATACACCACCAGCACCCTTAGCTGCTCCGTCAACGGAAAGTTTGGCCTTGGCTCATC
TTTTGGACAGACCCAGTGTGAGCAGACAAACTTCGAGCGTGGGTCAGATGTCTCTGAAGGATTTGGAAGAACAACTGGCTGCCTTGAGTGTGAGG
CCACAAGACGCGAGTTCTAACGGGGCCACGATCGTCACGAACTCCTCTGTTCAGAGAAATTCCATGGAACAACTGCCAATGATTCATCTACCGC
CACTGATTCACCCAGTTCGCAGCATAACATCGGCTCTCAGTGCTCATCCACTTGTAGCACTGTGGTGGTAACATCTCCTGTAAATGGAGCAGGCG
CTTCCTCTTCAGGTGCTCCCATACCTGTGCACTCCACTTCATCTAGTTTGGAGCTTGGCTTTAGTCACACCGCTCAAAACTCGGCCTTGAGCGAA
ACGAGTCCCGACGATTTTCTCTCCACATCGGCAAGAGAAGAAACGGAGAGTGTATCGGGCGCATCTGGGGTTTATACTTTGGCGCACGGAGCTCC
ACCCACGGAAACCTCAGGCGTTTACACCATGCACAGCAGTGAGCTAACTGGACAATCATCGGAGATCGCCGAGTCGGAAAAGAGTTCGCACTACG
GGATGTTCCAGCCCCAAAAACTAGAAGAAACCCACGTGCAACATTCTGATTCCGTAGATGGAAAAAAGAAAGAAGACTTCAGACCGCGATCGGAT
TCTAACGTCAGCACAGGGAGTTCCTTTAGAGGCGATGGCAGCGATCCAACAGACAACAAACATTCCTTGCTCTCCGCAGAAGAGTTAACCAATTT
GATTGTGGGCAGGGGGACCTACCCCAGTCGGAAAACAGTATCTAGTAGCCTTCACTCGGACTGTGATTACGTGACGTTACCACTAGGAGATCAAG
GAGAAGAGGAGGTAGACCAACCACCAGCACCACCACCACCCTACAGTGCTAGGCATGAGAAAACTGGTCTCTGTGGCCCACCTATCGCCAAACCT
ATCCCTAAACCTATAGCTGTGGTAGCTCCCAAACCAGATTCACCGCCATGTAGTCCACCGGTACCGCCAGCACCAATTCCAGCCCCACCGCCGGC
TATTCGACGAAGAGATCCACCGCCATATTCCATCTCTAGCAAGCCTAGACCCACATCCCTGATATCTGTCAGTTCGTCGGCACATCCTGCGCCCA
GTGCTGCCGGCTCGATGAGTTCTTTAAAGTCCGAGGAGGTTACAGCCAGATTTATCACCACCAGGCCACAGATTAGTATTCTGAAAGCCCACACC
AGCCTGATTCCCGATGGGGCCAAGCCAAGTTACGCGGCACCGCACCATTGTTCATCAGTTGCCTCCTCCAATGGATCGGTTTGCAGCCATCAGTT
GAGTCAGCAATCGCTGCATAACTCCAACTATGCCGGCGGATCCCAGGCTTCACTGCACCATCATCACGTGCCGTCACACCACCGACATTCTGGAT
CGGCAGCCATTGGAATAGTTCCTTACGGTCTGCACAAGAGCACGGCATCACTGCATCATCAGCAGTCATGTGTACTACTACCGGTTATTAAACCT
CGGCAGTTCCTGGCACCACCACCGCCCAGTTTGCCGCGGCAGCCTCCACCACCGCCCCCACCGAATCACCCCCATTTGGCGAGTCACCTTTACGA
GAGGGAAATGGCTAGAAAACAATTGGAGCTCTACCAGCAGCAGCTTTACAGCGATGTGGATTACGTAATTTACCCCATCCAGGATCCAGCTGTAA
GCCAGCAAGAGTATCTGGATGCCAAACAGGGATCCTTACTGGCGGCAATGGCCCAAGCAGCACCACCCCCACCGCACCACCCATATCTGGCCATG
CAGGTGTCGCCGGCGATTTACAGAAGCACCCCCTACCTACCACTGACTCTGTCGACCCACTCACGATATGCATCCACCCAAAATCTATCGGATAC
ATATGTGCAGCTTCCAGGACCCGGATACTCACCCCTGTACTCTCCTTCGATGGCCAGCCTATGCTCCTCGTATGAGCCTCCACCGCCTCCTCCCC
TTCACCCGGCTGCTCTAGCAGCAGCTGCTGCGGCGGGGGCTGGCTCCTCGTCTTCCTCGATGTTTGCGCGATCGCGATCAGATGACAATATTCTG
AACTCACTAGATTTGCTGCCCAAGGGAAAACGACTGCCACCGCCGCCACCACCACCGTATGTAAACAGACGGCTAAAGAAACCACCCATGCCGGC
GCCCAGTGAAAAGCCACCTCCAATACCCTCTAAGCCAATTCCTAGCAGGATGAGCCCGATTCCACCACGAAAACCCCCAACGTTGAATCCGCATC
ATGCGAACTCACCGCTAACAAAGACCTCCAGCGGCGCCCAGTGGGCAGGTGAGCGTCCGAGACCTGACTTGGGTCTTGGTCTGGGATTGAACCGG
GGAAACAACAGCATTTTGGCCCAGCTGCAGGCTTCAATGGTAGCCCAGTCTCATGCCCAGGCACAGGCCCAAGCGCTAGACATTGCGCTTCTTCG
GGAGAAGAGCAAGCATCTAGATCTGCCGCTGATCTCGGCGCTCTGCAACGATCGCTCCTTGCTGAAACAGACTAAGGTTGTTATAAATCCGAAGA
CTGGCCAGGAGATGCCCACTTCCAGTGCGCAACCTTCAGGTGCCACCACAAATGGAGTTGCCAACTCCTCTGCAGGAGCAGGAACCCTAAGCAAG
GCCAGAAAAGGATCTACCGTAAGCCACCGTCATCCGCAGGACAAACTGCCGCCTTTACCTGTCCAACAATTGGCGGAGGCCAACAACTACGTGAT
CGATCCCGCTGTCATGATGAAGCAACAGCAGCAGCAGCAGCAGCACAACAAGACCAGCTAGACTCGACAAGCTAATTGGAAACCGGAACGGAAGT
GGACATTGGGGGTCCAATACGACACTCTTCTCTCTAGTTCGATTGCTGTTCGAAGTGCTGATGTATGAGTGTGCCCAGGTGAAGAGCTAATTCTG
CGTTCGGAAATTTGCATAGATCGGGTGGTGTAGCGTTATATAAATTCGATCACAGTGTTTCGAAGGGTAAAGATTCGCCGGGCACAAAAGGGTAA
ATGTAAACGAAAACCCACCGTGAGAAACCATTTGTCAGAACAGCAGAAACAATAGCTATTTAGTAGGAACTAACATGCATTTAACTAGCGAAGAC
AGTTTTTTAGAAAAACACAAACTAGCAGGTCCACCAACTTCAGATGGTAAAATACACGAGCCACTGAAACAACTGAATATCACAGAGTCAATACT
TAAGCCTACAGGACGTGAGCAACGTAACCTCAAAATACACATTCAAATAATCAGAACCCAGTCTAGTCACTTAAGGGAATTGGTAACGTAACCAC
AGCACAGACCACAACATGACACAACATCGGAAATAGAGAGGAAGCTTATCAAAATGGGAAGCAACAATACTCAAGTATAAAATACGACCACTACC
TAATTTACTAAACTACATCGTAGATCTTTAGTCTTAGCTGCAAATACTTAGTTAGGCCAGAAATGCGAATACTTAAAACTAACTACTTCCGCCCA
AACAACTGTGATTGATTTTTATTTAAACTTATACTAAATTTATAACTATTTAGTCACCAAGAACAACGCAACATATACTATGCAAATTTTTTAG
TACGTAGCAACGTCGCTCTTTATACACACACACACATACTCACAACGAATCGGGCCAGCGGTAGAATCAAGTGAAAAGCATTCAAATCGGCTATG
AAATGGTTTGAAATGGGTTTGCTTGC
(SEQ ID NO: 443)

Start ATG: 908 (Reverse strand: CAT)

MRAFCTVSAPLEVCASSAEQLSPGSRFLALRLLGQQQPKTLYFLVDAKSRVREVYTQTCLHFATQGMLDTELFGLAVLIDGEYMFADPESKLSKY
GPKSWRSSHTHGLDANGRPLLELHFRVQFYIESPFMLKDETSRHNYYLQLRHNILQRDLPREQAEQALVFLAGLALQADLGDAPPGTSNSKDDSG
EETSASPSNGGRGLSATTTLPKISKRANERMLRLSTYVASTSKRETIPLPPSLPPNGADYYRIEDYLPSGLHTPWARSAMRACHREHLGMATAEA
ELLYIQQACSLHETINAHTYRMRLAKSEQGSGSAWFVVYAKGIKILGGESTNSSSNPETTTFLWPNITKLSFERKKFEIRSGESRITLYAASDEK
NKLLLTLCKDTHQWSMKLAARLKEVSKREEEEAAESQRLHASYACSRSLLLPYKSKNEQRISVISSTSSNTTSGIVSDRVHSEDELEIMINTPPA
PLAAPSTESLALAHLLDRPSVSRQTSSVGQMSLKDLEEQLAALSVRPQDASSNGATIVTNSSVQRNSMGTTANDSSTATDSPSSQHNIGSQCSST
CSTVVVTSPVNGAGASSSGAPIPVHSTSSSLELGFSHTAQNSALSETSPDDFLSTSAREETESVSGASGVYTLAHGAPPTETSGVYTMHSSELTG
QSSEIAESEKSSHYGMFQPQKLEETHVQHSDSVDGKKKEDFRPRSDSNVSTGSSFRGDGSDPTDNKHSLLSAEELTNLIVGRGTYPSRKTVSSSL
HSDCDYVTLPLGDQGEEEVDQPPAPPPPYSARHEKTGLCGPPIAKPIPKPIAVVAPKPDSPPCSPPVPPAPIPAPPPAIRRRDPPPYSISSKPRP
TSLISVSSSAHPAPSAAGSMSSLKSEEVTARFITTRPQISILKAHTSLIPDGAKPSYAAPHHCSSVASSNGSVCSHQLSQQSLHNSNYAGGSQAS
LHHHHVPSHHRHSGSAAIGIVPYGLHKSTASLHHQQSCVLLPVIKPRQFLAPPPPSLPRQPPPPPPPNHPHLASHLYEREMARKQLELYQQQLYS
DVDYVIYPIQDPAVSQQEYLDAKQGSLLAAMAQAAPPPPHHPYLAMQVSPAIYRSTPYLPLTLSTHSRYASTQNLSDTYVQLPGPGYSPLYSPSM
ASLCSSYEPPPPPPLHPAALAAAAAAGAGSSSSSMFARSRSDDNILNSLDLLPKGKRLPPPPPPPYVNRRLKKPPMPAPSEKPPPIPSKPIPSRM
SPIPPRKPPTLNPHHANSPLTKTSSGAQWAGERPRPDLGLGLGLNRGNNSILAQLQASMVAQSHAQAQAQALDIALLREKSKHLDLPLISALCND
RSLLKQTKVVINPKTGQEMPTSSAQPSGATTNGVANSSAGAGTLSKARKGSTVSHRHPQDKLPPLPVQQLAEANNYVIDPAVMMKQQQQQQHNK
TS*
(SEQ ID NO: 444)

Name: expanded
Classification: known_flybase_gene
Gene Symbol: ex
FlyBase ID: FBgn0004583

Celera Sequence No. : 142000013383801

FIGURE SHEET 247

TAGTCCTACCGTATTGGTTGAATCCGGAGAGATTGTAGGCCCATCTGCCCAGATTTGCTGTGGGGAAAAATTCGCATTACATATTTACGTAATCA
TAATATTCCGGCGTACTGCACTACGAAATTTGTTGCATGCAACGTGAGTCCGATTGTTGCCCGTTCGTATTACTTACAGAGAACTGCGGGTCCCT
TTCTGGCAATATAGTTCGACATGGTTTACGTAAAATCAGAAGTCGGGAAAGAGATATTCCTCCAGCCTTTTTATTTTAGGTATGAGAACGTTGGA
GATGGGTCTCTCGATAGCTATCGCACCCCGTTATCGATCAACGAGCACTACGGTTGCGTTTGTACAAATCGATTTCCGAAATGTAATACAGACAC
ACTGCACCTATCGATATATCGCACTCAAGAAAATTCGTTATTCTTTAGTTTTAGAGCTATTAAATATATTATCTTTTAACATTTTACCCTTTTGT
ATTTGTATTTAGATTGTTCAAAAACTTGGTGGAGACGGCAACCGAACTACAGTATAATTACATCTCCAAAGTTGGTCATTTTGCAATAACTTTTT
GTATAAAGTAAATAAAATCAATTCAAATTCTTGTAAACCCATTTAAGCCCATGTAAAAATCCGCCTTCATAAACAAAATACTTGTAGTTTATCAA
ACCGAATGATTGTGGCTTTCTCCTTTTGTAATTTGTTATGGGAAACACTCAAAAAAGGTTTTTAATTTGGGTTAAGTTATAATTTATGTTAACCA
ATAACCTCGATTAAATTAATTATAAAAATGATGCCTGAAGATATACAACTTTCACTTAACTTGCAACACGGGTATTGTATATTAAACAGCAAACA
AAAAAGGCAAAAATGTTGGTAATTAGCGGAGTGCTTCGACAAGCGGAAATCCCTACTTCTCATTTAAATAATATTTCCCCAATTTTTTGCGATAA
GCCCCCGCCAACGGTAAACCCTTCATTAAAATGATTGATAGCGTTTTTATTTTAAAGTACATACCTTCGCTTTATTATGACTACAAAATATCAAT
TTATACAAATTAAAGAACATATACAAATTCTTTATATATACAGTGCCCTCCCTTAAGAGTGAACACTCGAATATGTGAACTTTTTAGTAAAAGTG
AACGATTAATTTATGAAATTTTAGAAACTTTCGCTTAACTTAGTAAAAAAATTAAATTTTTTCAAACGTGGTGTTTTTGAAAAATATATTAAATT
GTTTATTTTTTCTGTGATTCGTTATAGTGAACAAATTCGATTCAGTGCACACCCTTGGTTCTCAATAGTCCACTGTTTCGAGTGAGCACTGTACA
TACACTAAGGCTGGCACGAACACGACACTAATTTAAGTTTGTTTCGGTTTTTGTTTCTGATTTCTGAACACACGTTATATATATACATATGTATA
ACATTGAGACCCGTTCCAGCCTTAGTTTATACATATATCACTGGGCACATAATGTAGTAACTCCCAATGCGCTGAGTGGCCGGGAGAGAGAAATC
ACTTATTGTTCTTAGCTGCAGTCAATGACAAAAACTCCACCTTTCGAGCCAAGTACTCATTATAACGAAGAAATGCATAGCTAAATGGGGCGAAT
AAAAAATTGGTCATTAGTATCGATTGGTTGTAAGGGTCGTAATTGGGGGAAAAAAGGAATTGCAGGGTGCACAATAATATAATAAATCCATTATA
ATGGCCGTCTAATGGTTGTTGATGGATCTTATCAAACAAAACTGATATATATACTGATGATATATATCTATATATCTAAAGGATTTATCATCTAA
TTGCATCGTGCATTCCCAACTCAAAGTTACAGTCCATATACTATGCAACACGCACCCTACGTAGTCGAAATCGATAGTGGAATGCTCGGCTTGCA
ACAGGGACCACACCGTCCAAAAGATATGCGATGCCAGCGCAAACTGATTGACCTGGACATAGAGCAGTTCGACTTCGTCGTTTTGAATGTTGCTG
CGCTGTAGGTACTCCTCAAGGTAGACCCTCAGCCACTGGAGCTGGAACTCGCGCTTCGGATAGCGCGAATAGTCGACCTCATCCACGCCGCACAT
CTCCGCAAAGTGGTTGCCAATGTCGAAGGCCTGGAAATTGTAATCGGCATACTCGTAGTCGATGAAGTTCACCGTATTCAGGCTCTGCGTATAGA
TCACATTTCCCAGCAGAAGATCGTTGTGGGAGAAGACAATCGGACTGTCCAGAGCCTCGAGGTATTCATATAGCTTGTTGAACTCCTCGCGCAGG
CGGCCGATAGGTAGAAACGTTTCTTTCACTCTGCAAATTGCAAATCAAACAATGAGCGAATGAACAAAGGACCGAAGATGCAAAGGATGTCTGGT
GTCGTTACCTTTTGTGTTTTTCAGCATCACTAAAACGTTCAGGTACTAAATCAAGAAAGCTCTGCGTCTTCTTCCAAATCATCGGCATGGGTTTG
GTCGCCGAACTATCCCCGTGCTTTCTCACCTTGCGATGCATCTCGGCCATGCGACGGGCGACCAAGGGCCAAATTTCTGGACAGAGCACACTGTC
CGTATTCAGGGTGGTTCCAGGTACGTATTCGTAGACGAGACCGTTCTTGAACGTGGCATACAGCGATGGCGCTAGCCCATACGTATGCAGTAGAA
GAAAGTTTTGCGTCTCCGCCTTGCGATCTATCAGTAGGTCCGTTTTGTTACCGTATATCCTGACGAGCACTACGTTATCGGAGTACTGTACAGGT
GACCCGTCGTCCGCTGCCCGATCGTCTGTGAACTCATCATCGTCCTCCTTCTCAATGATGACTGGATCCTCGGACTGAACGGGCGACAAACCCTG
CGTCTTGATAGGTAAATACGATCCGCCGTTCTCATCGTTCAGTTTGGAGATCTCCTTATGAAAACATCCGACCAGTTTGTTTGTGATGCCATCGG
TAAAACTCTAAAATAAGCACACAGAGAACAGCACCATTAAATCGTATACATAAAAACATAATACTCATCGATGTAGATCCAGTGAATGGGTTAGG
ATGGATTAATTAGTAGAGTAGCTACATGATTTGTGTGCTTTGTTTATTGTAAGTGAAGTTATTGCATCATCACCTAATACCAATTGCTATACGGT
AAGGTTCATTAGTAGCATTCAATGGAACGGTTTCGGGAATTCGCCTTTTAAGCCACAGCTCAAGAGCTACAGTAAAGGGCTTATGGCCACTTCCT
TATCGACTCCACATGCTTCTTATGTACATATGTATGTACATATATAAAAGAGTGAAGCACATGGGTGATAAACTTTGTGACACCAGCTATTTGCG
TGCTAAGCGTCTCAGAAAGACCACCTTCGTCTTGAATTATATACGCATACGGTGCTTTTTATAATGAAAACACAGAAACAGATAAGATAATGAAT
TGCTAAACAATTTAAATTCATATAATTCAAAGCGAAAAAGCCCAGAATGTGTGAAAGGTGAATGAAATAAAAGTGCGAAAATAGTAATTAGTTCA
TTTCAATCACTTCGATCTGCCCTGGTTTTATTCATTCACTGAGAAAAGTTTATTTATTGCATTTAATCAATATTTCCCAGTTATTTTCCCTTTGC
TCAGTGTTCAATGCACTTAAGATTAAAGTAGTGCTGTACAAACACGTGTGTTTCAGATCGCTGGCGATATAGTAAATTTTCCACTTCATATATAG
AACGACGTCTCTAGCGGCTATAAAAATGTCAATAGTTAACCCATTACTCGCATGACAGTTGTGAGGCATAAATAACCGTGAAACTTGAAGTAAAA
CTTAAACATTTGGTTTATGGTTGAGAAACGCTGCCTATGACGCCATGGTCCATGAATCAACTCAGATTTGTGCAAGTATTCATAGTATTCATAGT
AGTCATATTGTAGCATTTATTATCACAATTTCGCCTGACTGGCGCCAAAGATTTGTGACTCCCCATAAGGATGCCTCCCCTCCACTTGAATCCTG
AATCACGCGACAAATTATCTATAGCTTAGAAAACGGACATGACACGATTTAGACTGTGTACCATGTACCCATGTACTATGTACACCACTCGCTGA
TCAAGGGATGAACCACGTTTTATTGCCCACCAGCGATTTGGCAAGACTCAGCACTTGGCAATTCCGACTGGAGCTGCCATAAAGCTGATAAGTGA
GTTACGGACAAGCTGTGTACACCAATTAGACGTCATGCCTATGGTGCGGCATATACAGATAGCGAGGTCAAGGCGTACAAGTGGCTTCCGATAAG
GCAAAAACGCCCCATTTCAAAAAAACCGGAGTGATTAAAGGCAGCCTCAGGCATTTGTACATACATACATCAATCATACTCCTCTAACTCGACAG
CGTGAAATTATCAAATCGGGCCAAACGAAATCAAGCCCCTAAAAAGCGAGGGAAAAAACGTTTTTTTTTCGGATCATCCGTAAATTACGGACGGA
CGGACGGATGGACGGTGTGTCGGTAATGGTTATCTGTAAAAACACTCGAGTCAATGCACCTGCTGTCAACACCTTCTATGTCAGGCATTTAAAGT
ATTGTGGTAATTAGAGAACGTGCGATTTCATTAGAACTAAGGCGACTAATTGGCACGAAGGCCTATTTCTTGGCTCACACCCGTTTCCAACCCGC
TCCGTTTGGTAGGGTGTGTGTGTGTGTGGGGGGGGGGGGCACTTATTATTATTTCCCCCCCGGAGTCGAGGGCTAGATTAGCAGCAAACTGGT
TTCTACTGCGACGCGGGGTCTGAAGTCTCCATAGTTCGCTTGGCGACTCGGAAACTCAGAAACGCTGTCCTAATACACCAACACCAGCGTAGTGA
ATAATGTTAATTTCGAATAACAATCCTATGCGTCTCTCTCTTCATTGATATAACAAAGTCTATTTACAATTATCATGGCGGCGCAGCAGCGAATA
TATATATATAATTACTATTTGAAGGTTGGCTGTTGTGCAATAACCCTGTTTCAAACAATGTTAGCAACTACTACGACTCTATATCTCTATATATA
TGTATATGAATGTATATAGTAAAGTATATATCCCACGTTCCGCACACCAGTTAGTGATCGTAATAAATGATAAGGAAACATACAGCGTCATCATC
ACCATCGCATTTTGGGCCGGATAACGATCTTCGATCTGCGGAACTACCCTGATCTGATGGAGAATGTAGAGAATATGACATTGATGGTTTCGTTT
TTTTGCATTGTATAGTGTGTTGTTTGGCTGGTGATTTAATTTGATTTGCTTTGATTTGATTGTTGGTATAATGATATTGTAGGGGGGTTATAATT
TTGAATGTTTTGATGAGGTTTACGTTACCTTAAACTCGACGTGGCTGAGGTCCCAGGTCGGTCGTATAACCTTCAACAGTTCCTTGGCCCCTTGA
ATTACGTCGGCCTCCTCAACAAATATGGGTACAAATGGTACAATTGCCTCTTTTCTGGATTTATCCTCCGGTTTGGCTCGAATATCGCGCGAATT
TTGTTCGTTTTCGTTTTTGTTTTCGCTCCCGCTTGGATTTGGATACGAATTGGAATTCGAATGTGAATTCAATTGGTTCTGGACCTGGTTCGATT
GCGATAGCGATAGCGTTTGCTGATTGACCGTCTGACGAACTAAGGATAAAGAATCTTTCATCACTTTGGGGTTGCCGCCACTTGTTGAAATCTGT
CCTGTGTAACTGTTGCTCTTGGTTTCTGTGCCCATTCTATTGTATTATATATGTGAAATACGAAAGTGTCAGGTCGGGTCATACATATAGAACGA
CAATAACATCAGCATGTAAAATGAGTAGGTAGGTAGGCGGTAGTTAAAAGCTAATCATCCGAATGCAAAACCAACCGAGAACCCAACCAAACCAG
CAAAGATATCCTCTCACCCCCCCACGCAACGAACCGCAGCCAAATGAAAAATTAAAAAACCCAGTAAGTATACTACGTCCATGTCCTCTCACTCA
TGCGCACCGAAACCAGAGTTTTGGATGGAGATGACCGCACCCAGTTAGTAGGATCTGCGTACCATGTGGGAAATAGCCCAAACACATCCACTTCA
CCACCACACGAATGAAACATTATTGTATCGTTCATACTAAATTTAATCTCAGTTTAAGGTTTATTTGTTTATATATCAGATATAGAAGATTGTGC
CAAAGTAAAGCAAAATCTACCTCCTAAACAAAAACTTATCTACATAATGATCAACACTTTTAGAGTCCCAAATGTGTAATTAACAATTATACGAG
AAAATATTCGCTAATTTGACAAGCAAATAATATATATGTACGTATATTCCATAAAAAATGATTACGGAAAATAAACCTTGAAATTGTGATAGTCA
ATTCGTTAACTGGTTTTCGCTTGATACAGGAAGTTCCTAATTTCAGTTATAGATAAACATGCTCTTTTACCCTCATTAAACACCAAAATTCGCAA
TATAGATAAAAGCTGCCTCAATGATACTTATTAATCATTAATCACGATGTAATGAATGATACAATTTGCAAACTAACAACTTGTTAATAGTTAAT
AATAATACATAATGCAGCTCTAACTACACAAATTCATGCATGTGTGTGTATGTATGATGGACGCTTTTTGATTACCATTCTTCTTAGACCTTATC
GTTGACATTATCTACTGACTAGATCCATCATCTTGTCTTCATTTTCGACTATATCACGAAAAGCTGATTTAAAAATAAACTTTTTATTCGTTTAT

FIGURE SHEET 248

GATAAGCAAACATCTCGAATATTATAGAATCAAGTTGGTAATACTGACAACGGCTATTAGGTGCTATTATGTTACCCCGTGCTGTATTATGTCTT
CGAATGCGGCACAGCCGGGCGGAAAGTACACGTAGCCGTGTGTACTCGAATTATACGAAGGTGCGTAAGGCGATGACTATAAATCGGAGAAGGTA
ACGAGACAACATACGTATATGTATATGCATGGGATAAGGTAAGGGGGTCAAAATAAGTCAATAAGATCGCCGTGTTAAGCCAATGTCTTAAAATA
CAGGGCCGGAGCGAGAGGGTGGCTAAGTTTTTAATTTGATCAAAGGCAATTTTAAATCGGAATTATGCTGTATCCACTAAATTTTATTACAATTG
AAACTGTTTTGGGGGGTGACGCCCCAAAATGACCCCGCCGACTCCGCTCCTGGAGCCAGGGAATGCACCCACACTCGCGCACAAATAAATAGGGC
GTAAAATGCTAATCTTGTGAATACGTGAATGTACATACATGTGTATGTACATACTCCACGCAAATCAAGTGTACATTATGTACATGCGAACGTAT
GTAAGATCGGAAATCAGGTGAAAAGCCCAGGGCCCAATAGCACAGGTGGGGGCGGGCGCGTTAGCACGGGACATTTGCTTTAATATTAACATGTT
TTCTGTTTCGCACTTTCTTCATTTTTTCATCTTTATTTTGGTTTTTTAGCCAGGCCAAAAGTTTACGCATACAGTGGCAATGTGTGTAGTACGTG
CAAGGGTACAACTGCATGTGTGTGCATAGTAGGTGGGATTAGGGCTCATCTGCACGGGCTAAGTTTCCCTTATATCCCGTTATACTACTCGAATT
CTGTAAACTTAAATGTTGTGAATGAAACTAAAATATAAATAAGCTACATTACTTTGCCAGTCACATTATAGACCTCTTTTAAGCCTCAAAAGCGG
CGATTCCATGCGGAATTTAGGTCGTGCGAAGGGGCCTTAAGCGCGTTCTGGGTTAAGAACCCCCGCCCACGACCCCCTTACCACAACGACCCATC
CCACAATCCGAGCATCCTTTTTCCTGAACCCGGTGCGATATTTGTTGGTTGATTCGAAGGATTCCCATACCAGATTTTGATTCCGATTCGGTGGT
TCTGAATTCAGATAGTGATTCGATTGGATTCGATTTCATTCGACTGGATTTGATTCGTGTTTCGCATGCAATTTGAGTTTTGAAAACGACAAACA
AGGTAAAATAATAATAAAATGTGTACCAATATGTCAAGCGTCAACGAATGCAAACGCACACTGAGGTGAATTGTTAGTTGTCTACACACGTTACC
TTCGGGTATTGATTGTTTTTTAAAAGAAAACACAAAAAAAAAGCCGCGAAAATCACACAACCAGATTATCGATTTTGGCCCCCGCTGAAATTGGC
GCACACAACACACAAATTTGACTGGGGAACGAACAGCGGGCGATGCAAACGATTCGGTTCCGACTTGGAATATATAGCTGCCGAACTATCGGTGC
AACAATCGGATCGCTCAACCGGTCGCTCCATCTGCAGGGAATACCAAAACGCCTCAGTTAAGTGGCGCGCGAATGAAGGTACTTGCGCTTAGCCA
CCAGCTGGGCACACTGCACGAGCCTGCATAGAGTTTTTTACGAAATTATCACAATTTAGGAGTTTTCCAATTAGAATTGGAATAAGTTCGTACTC
TTAACTTGCTAACAAGTTGATTTTTAATGCAAAACTTTTCGCAGACAACTTTTCGACAAGAACAGTGCTGCCAGACTGTCAGACCGGCACCTTAC
TGGCGTGTTTTTATCACATTTTCTAATATTTCCAAGCTATTGAAATATTCCAAAGCTTTCTATCTGCACATTCTTTTTATATAGGTGTTCCCAGA
AAATCGCCTTAGCATGGAGAGTCGTGCTAATACGGCGTTGCCAGACTGTCATTGCATTTCTTGTTGCTCTTTGCAAGAGCCCGCCAAATGAAATT
TTTATTTGAATACAATTTATTTTTTTCTTCCCCCGTTCTTTTGCTTGTATAATATCCCAACTGGAAAATGTGTACTTTTCAATTACGAAACATGT
ACAATATATAGCAATAAAGTCCAGTAAAATCGTGGTATGTTTACAATTACTTTTTTGGGCCTGATGATACGTTGCCATTAAAGTGCAATGTCATA
CCACTAATGTAAGTTTTTTAACCCTTTATACCCCCCAATAGCTTGCCCATAATCCTCCCGTGAACAATCTTGAATCCCAAATGCAAGAACAAAGT
TCGAATATTCAACAGGAGCTCCGCCTAATGTATGATGACGCATGTATTTTATACAGATCAAATATTTTCATACCGTTTTACAGGGTTCCGAAGAA
TAGAAAGTGGTAATTAAAAAAAGTATGCATTCGGTTCACCGAATTCAATTTGAATCGTTTTCCAAGTCAAATCAGGTTGGCTACAATGAGCAGAC
AGAATGTGGGCGGCGACACCAGATAGTGTCGCCGAATGCATGGAAAGCGATTCAATGCAACGGCCTTCCATCGAAGAAGT
(SEQ ID NO: 445)

Exon: 8295..8075
Exon: 5736..5349
Exon: 2952..2384
Exon: 2310..1861
Exon: 1600..1001
Start ATG: 5735 (Reverse strand: CAT)

Transcript No. : CT13670
TGGAGCGACCGGTTGAGCGATCCGATTGTTGCACCGATAGTTCGGCAGCTATATATTCCAAGTCGGAACCGAATCGTTTGCATCGCCCGCTGTTC
GTTCCCCAGTCAAATTTGTGTGTTGTGTGCGCCAATTTCAGCGGGGGCCAAAATCGATAATCTGGTTGTGTGATTTTCGCGGCTTTTTTTTTGTG
TTTTCTTTTAAAAAACAATCAATACCCGAAGAATGGGCACAGAAACCAAGAGCAACAGTTACACAGGACAGATTTCAACAAGTGGCGGCAACCCC
AAAGTGATGAAAGATTCTTTATCCTTAGTTCGTCAGACGGTCAATCAGCAAACGCTATCGCTATCGCAATCGAACCAGGTCCAGAACCAATTGAA
TTCACATTCGAATTCCAATTCGTATCCAAATCCAAGCGGGAGCGAAAACAAAAACGAAAACGAACAAAATTCGCGCGATATTCGAGCCAAACCGG
AGGATAAATCCAGAAAAGAGGCAATTGTACCATTTGTACCCATATTTGTTGAGGAGGCCGACGTAATTCAAGGGGCCAAGGAACTGTTGAAGGTT
ATACGACCGACCTGGGACCTCAGCCACGTCGAGTTTAAGAGTTTTACCGATGGCATCACAAACAAACTGGTCGGATGTTTTCATAAGGAGATCTC
CAAACTGAACGATGAGAACGGCGGATCGTATTTACCTATCAAGACGCAGGGTTTGTCGCCCGTTCAGTCCGAGGATCCAGTCATCATTGAGAAGG
AGGACGATGATGAGTTCACAGACGATCGGGCAGCGGACGACGGGTCACCTGTACAGTACTCCGATAACGTAGTGCTCGTCAGGATATACGGTAAC
AAAACGGACCTACTGATAGATCGCAAGGCGGAGACGCAAAACTTTCTTCTACTGCATACGTATGGGCTAGCGCCATCGCTGTATGCCACGTTCAA
GAACGGTCTCGTCTACGAATACGTACCTGGAACCACCCTGAATACGGACAGTGTGCTCTGTCCAGAAATTTGGCCCTTGGTCGCCCGTCGCATGG
CCGAGATGCATCGCAAGGTGAGAAAGCACGGGGATAGTTCGGCGACCAAACCCATGCCGATGATTTGGAAGAAGACGCAGAGCTTTCTTGATTTA
GTACCTGAACGTTTTAGTGATGCTGAAAAACACAAAAGAGTGAAAGAAACGTTTCTACCTATCGGCCGCCTGCGCGAGGAGTTCAACAAGCTATA
TGAATACCTCGAGGCTCTGGACAGTCCGATTGTCTTCTCCCACAACGATCTTCTGCTGGGAAATGTGATCTATACGCAGAGCCTGAATACGGTGA
ACTTCATCGACTACGAGTATGCCGATTACAATTTCCAGGCCTTCGACATTGGCAACCACTTTGCGGAGATGTGCGGCGTGGATGAGGTCGACTAT
TCGCGCTATCCGAAGCGCGAGTTCCAGCTCCAGTGGCTGAGGGTCTACCTTGAGGAGTACCTACAGCGCAGCAACATTCAAAACGACGAAGTCGA
ACTGCTCTATGTCCAGGTCAATCAGTTTGCGCTGGCATCGCATATCTTTTGGACGGTGTGGTCCCTGTTGCAAGCCGAGCATTCCACTATCGATT
TCGACTACGTAGGCTATGCATTTCTTCGTTATAATGAGTACTTGGCTCGAAAGGTGGAGTTTTTGTCATTGACTGCAGCTAAGAACAATAAGTGA
TTTCTCTCTCCCGGCCACTCAGCGCATTGGGAGTTACTACATTATGTGCCCAGTGATATATGTATAAACTAAGGCTGGAACGGGTCTCAATGTTA
TACATATGTATATATATAACGTGTGTTCAGAAATCAGAAACAAAAACCGAAACAAACTTAAATTAGTGTCGTGTTCGTGCCAGCCTTAGTGTATG
TACAGTGCTCACTCGAAACAGTGGACTATTGAGAACCAAGGGTGTGCACTGAATCGAATTTGTTCACTATAACGAATCACAGAAAAAATAAACAA
TTTAATATATTTTTCAAAAACACCACGTTTGAAAAAATTTAATTTTTTTACTAAGTTAAGCGAAAGTTTCTAAAATTTCATAAATTAATCGTTCA
CTTTTACTAAAAAGTTCACATATTCGAGTGTTCACTCTTAAGGGAGGGCACTGTATATATAAAGAATTTGTATATGTTCTTTAATTTGTATAAAT
TGATATTTTGTAGTCATAATAAAGCGAAGGTATGTACTTTAAA
(SEQ ID NO: 446)

Start ATG: 223 (Reverse strand: CAT)

MGTETKSNSYTGQISTSGGNPKVMKDSLSLVRQTVNQQTLSLSQSNQVQNQLNSHSNSNSYPNPSGSENKNENEQNSRDIRAKPEDKSRKEAIVP
FVPIFVEEADVIQGAKELLKVIRPTWDLSHVEFKSFTDGITNKLVGCFHKEISKLNDENGGSYLPIKTQGLSPVQSEDPVIIEKEDDDEFTDDRA
ADDGSPVQYSDNVVLVRIYGNKTDLLIDRKAETQNFLLLHTYGLAPSLYATFKNGLVYEYVPGTTLNTDSVLCPEIWPLVARRMAEMHRKVRKHG
DSSATKPMPMIWKKTQSFLDLVPERFSDAEKHKRVKETFLPIGRLREEFNKLYEYLEALDSPIVFSHNDLLLGNVIYTQSLNTVNFIDYEYADYN
FQAFDIGNHFAEMCGVDEVDYSRYPKREFQLQWLRVYLEEYLQRSNIQNDEVELLYVQVNQFALASHIFWTVWSLLQAEHSTIDFDYVGYAFLRY
NEYLARKVEFLSLTAAKNNK*

FIGURE SHEET 249

(SEQ ID NO: 447)

Classification: enzyme
Gene Symbol: eas
FlyBase ID: FBgn0000536

Celera Sequence No. : 142000013384541
AGTCCTTGTTATAACTATACCATCACCCGTAGTGACCTCCATCCGTCCGGAGTTTGCTGTGCTAGCCTCGGGCTTCTTGTCTGGCAGTCTGGTGC
ACATGAGCGCCTACGAAGAGGCCATCAGCATACCCACGTTGCACATCTACGGACAGACGGATGAGATCATTCCCAAGGAGATGAGCGAGTCCCTG
GCTGCGCGCTTCAAGAACGCCGAGGTGCTGGAGCACAGCGGCGGACACTACTTCCCGGCCACGGCGCAGCAGAAGCAGACATTCATCAACTTCTT
CCAGGATCGGCTGCAGGAGTACCTGGAGCACGAGGAGTTGCAGCAGAGCGGCAATGCCTCATTCGTGGATAGCGGAGCGGAGGACGACAACGATG
CCGAGGTGGCGGCCATGACGGCCGAGCTGGACGAGAGTGATTAGCCGAGGGACGGGGGTTTTTTCGTTCGTTTTTAATAATAATTAAATCTTATT
ATTACAAAAATAATGATTTGATTATAAATTATAATATAATTAGATCCCAATATTAGTTAAATATTCACTCTGCTCACGAAGGATCAAGCGGATCG
GGTATTGAAATGTCTGCACGTTCGCTCAGTTCGCACATATTGTTTTTATGACTTTGTGTATTTTCTCAACAAATTCGTATAAATTTCATTAAAAA
GAAACAATCAAGGGGTTAGGGTAAAATTAAAGCCGAATATTATCAATCCCATTCCAAAGTTCAATTTTGTGTCGGAACCATAGTAAATTAATTGT
TCCTTGCTATTAACAACGAAAAATGCATATTTAGCTATTGCAGTTGAGACGGCAGCTTTTGCTTCTTCACCACGCTGGGAAGTTGAGAATCGCAG
ACAAATAGATCTTCCTCCTCCTTCGTCCGGTCCGACCATCAACTTCGATTTCAATTTCATACATTTCGTTTGCGTGGGACAAGCGAGCGACAGAG
TTAGCGGATTTATTTTGTCTCGATTTGCTGCTGCTGTTGATTTTGATGATGTGTTTGCTGCTGTTTGTTGTTCTCGTAGGGGTGATTGACTGACT
GACTGCTGTGGCTGCATCCTTATGCCACCTGCTCCTGTCCGTTCGAGGCCTCTTGGTTTTTCATGACTTCGGGTAAGTCTGGTGGTGCCGAGTAG
GGTGTCATGTCCAGTGTCTCAAAGTCGCCCACCTCGTTCCTTAAAGACAGATAGCTATGTTGTACTACTACGCTGAGCTGTAAGCTTGTAAGCGG
CACACGTGCCGCACGCCCGCCTTGTCCGCTAGATAACCCGCAACCGGCTTATCAGCGACTCTCACCTGAATGTCAAGCCCAGCTGTGCCGGAGCC
TGCGCCTTGGCCGTGGACACCGTCACGCCGTAGTCCTGCAACGTGCTGTCGTCCTCCATGACATCGTTGTCCTGATTGTATAACCGCTGGTCCAC
GGGCTGCACCTTTAGTATGCCTGCGATCGATGGGGTTGTATGATCAGTCATGGAGTTACCCAATAATGGCGCTGCTCTATAAATAGAAGCCAACA
CTTACCCTCAATCATTCGCTTCAGCTCGGCCACCGTTGTGTTCTCCTTGGCGTCCGTGAAGATGGTGGTCTTTTGCCGCCTGATCATAAGGAACA
CGTCCTGCAAAAGAGAGGGTTAGCCATTAGATTTGATTCGATGCGAAGTGATTCGTTTCGGTCAAAGTTCAGTGGCGCTTTTTCAGTGTGTCATG
CTTTCTGATCTTGCCATCACACAGGCGACATTTGTGCACATGCATTAAGAGCGCGACGGTGTCTATGGCAGCAGCATCTGCGATGCACTGCATCC
TTGCTAGGCTGCACGACACCGGCACGAGCACTCACCATATTGAGGAGTTTGTGGCGCTGGCTGCGACTGAGGCTGCTACGCGGATGTGGGTTAAC
CAGGTGCGTGGGCTAGTGCGCTGTGTTCGGCAACTGACGGCGTGGGTGGCGCTTCCTTTGGCGGTCGCGGGCGGACGTTTCGATCGGCTGGAATT
TTCCTACTTCGCTTGCACCACCGCTGCTGGGCGCTTCTATTTTTTGCTCTGTGCCGCTCGACCGGAGTTGGGGGCGGGCGCAGGTGGGCGTGGCG
TGCGGTTCGCGGTACGATGAGCGTGCGTGAGTGTGTATGTTTGTGCAACAGCTTCCTCGGTTGCCCCCCACTTGTAGGTTTTCGTAGTTTTACGA
TTTTTTCTAGCCTTTTGCTGCTGCTTTCTCAACTAATTAGAGCTGTCAAACCATCGATGGTCGCATCGATAGTGAGCTATCGATAGTTCAGGGTC
AGCGGCCTTCGTTGTCTAATGCCATCGCTAATCCGATATTATTGCAGGGCTTTTAGCAAGGGATTGTCTAAAGCCTTGGTGAATTCTATTAATGT
GTATTAACAAATACTTCACAATTCCGTTTAATGTATATTTTCCATTAGTTTATAAATAAAATAATTCGCATAAGTAATGAGCTTTTGCAGCCCTG
GTTATTGCCAAGAAAATGTACTAGAAAATACCGCCATAGCTGTCAGTGTCACTTTTCCCGTTTCTCCTGTTTTATTTGCCACGAAATGGTTTTGC
TAGACAATTCGAACGTAAATAAATGAAATACCTTTAAAAGAAGCCGATAAGTAACCGTATCTCCTTACAGTTTATCCTGCGCCTGGAGAAGATCG
CAAATGCGGCCAAGAAGGACTCCTCCTTCACGCTGACGTTCAAGCGATGTGAGTGTTCGACACCGAAAAACATGGTACACTAGGAACTAATTTAC
AATTTATTTAATGTGCCGCAGATGATGGCAACGATAAGCCCGTGCCGAGGGAAGGACGGCCACCGCTGCCCAAGCCGGAGACCTACATGTGCCTG
ATGCGCGCCCAGTCCAAGTCCCAAAAAGTAAGCCCGATTGAAAGCTCCACGTTTCGACTCCTTACCAAATAAACCTATTTTTCCGGCAGATTTCC
ACCGTTGTCCGGCAGGAGGATGTGCCCGCCATGATGAGCATGTACTCGCAGTTCATGAAGAGCAAGATGGACGGGCTAAAGCGGGTTAAGAAAGT
CAAAAGCAAGGCCAAGGCGACAAAGGGTTAATCGGGGCATAGTCTTAGTTAGATTTTATTTGACTGTTTACTGGTCGTTTGTTTTAAACCTTAAA
TGCATCATTTTGTACGGAAAGCACGCTATACTTCTTATTTCTATCATCAATCTGACGCAGATCGAGCAGCCACTTCG
(SEQ ID NO: 448)

Exon: 2212..1841
Exon: 1619..1526
Exon: 1445..1301
Exon: 1179..1001
Start ATG: 1843 (Reverse strand: CAT)

Transcript No. : CT13840
AAAGCAGCAGCAAAAGGCTAGAAAAAATCGTAAAACTACGAAAACCTACAAGTGGGGGGCAACCGAGGAAGCTGTTGCACAAACATACACACTCA
CGCACGCTCATCGTACCGCGAACCGCACGCCACGCCCACCTGCGCCCGCCCCCAACTCCGGTCGAGCGGCACAGAGCAAAAAATAGAAGCGCCCA
GCAGCGGTGGTGCAAGCGAAGTAGGAAAATTCCAGCCGATCGAAACGTCCGCCCGCGACCGCCAAAGGAAGCGCCACCCACGCCGTCAGTTGCCG
AACACAGCGCACTAGCCCACGCACCTGGTTAACCCACATCCGCGTAGCAGCCTCAGTCGCAGCCAGCGCCACAAACTCCTCAATATGGACGTGTT
CCTTATGATCAGGCGGCAAAAGACCACCATCTTCACGGACGCCAAGGAGAACACAACGGTGGCCGAGCTGAAGCGAATGATTGAGGGCATACTAA
AGGTGCAGCCCGTGGACCAGCGGTTATACAATCAGGACAACGATGTCATGGAGGACGACAGCACGTTGCAGGACTACGGCGTGACGGTGTCCACG
GCCAAGGCGCAGGCTCCGGCACAGCTGGGCTTGACATTCAGGAACGAGGTGGGCGACTTTGAGACACTGGACATGACACCCTACTCGGCACCACC
AGACTTACCCGAAGTCATGAAAAACCAAGAGGCCTCGAACGGACAGGAGCAGGTGGCATAAGGATGCAGCCACAGCAGTCAGTCAGTCAATCACC
CCTACGAGAACAACAAACAGCAGCAAACAC
(SEQ ID NO: 449)

Start ATG: 370 (Reverse strand: CAT)

MDVFLMIRRQKTTIFTDAKENTTVAELKRMIEGILKVQPVDQRLYNQDNDVMEDDSTLQDYGVTVSTAKAQAPAQLGLTFRNEVGDFETLDMTPY
SAPPDLPEVMKNQEASNGQEQVA*
(SEQ ID NO: 450)

Name: Elongin B
Classification: enzyme
FlyBase ID: FBgn0023212

FIGURE SHEET 250

```
Celera Sequence No. : 142000013384593
CTGGCTATCCCTGGGTGTGTAGAATATGAAGCACATTGGGTACGAAATGCGCTGATCGTCATGGACCATTTTATACGTATAGATGACATATCGGG
GCTGGTGTCCTGGCAATGTATCCTGCAGCTCGTCCACCGAAATATCGTCGATGAACTCGTCCAGCACCACCGTTTGCTTCTCCCGGTCGACTTTC
ACTGCAAGGGACAATGGAGTGGTCATAAAAACTACACACATCTGTTACCATGACAATCAAGGCTTACATATCAAAGCCGCATTATTTTTGCTCTT
GCTGAATCGAAACTTCTTCAATTCCTCCAGAACTTCGTTGCTTATGTCGCATATCTGGTTATCACTCTGTATGAAATCGATATAATTGATTAATG
AATTGGAATCACCAAAGTTATCTGCTAACAACAATCGTCGATTGAAAAACAAAAACAAAAACACGCCCACACTCTATTAGTCATGTTTTCATTTT
GGTAATTGATTTCCGACCCTATATACACTTCCTACCATAACTTTAGCTATGAAGTTAGGGATGCGATCTGTAAAGTGTGCTGCACTACCGAATTT
TTGGCAGTTAATTGTAGGAATGCAATATCACTTGTCCTTAAGGAATCGTTTAAATACTGTCGTTTATTCTGAGTTTTGTTTTGTTGTTCCTGCAG
TGAGACCGTTCACTGAACGCCAAATAATATTCTGTGCTGCATCAAAAATATGTGAAGTGTTGTTAAACGACGTTTCTGATAAATTAAAAAATAAT
AACAATATTTGCTAAAGGTTTTTTTTTCATTAAGCTTTTTTCTTTACGGCAACATTGGTATTATTTATGGAATTTATTAAAAATAATTGAAATGT
ATTTTTTAGATTGAAATAGGAACGCTCTTTTTTAAAAATGTTTTGTAGATATACTTAAAACTTATCATTATTTTATAGTAGGTAAAAATCGTTCG
TATACGATATTTGGATCATGTTTGTCCTCTCTAGTGGCTGATGGACTGTCAAAAAAGTACCGTTACTTTAGGGTTGTTACAGAGAGCACTAACTT
ATAAATAGTTAATACTATAATCTATGTGCTTAATGTCGTAGTTACAATGAGCTTGAATTTATATGAGAGCAACATCCTTAATTCCTGCTGGAAAG
CGGGAGGGCGCAAACCGAGGAAATCGGCATTTGGCCAACTTAATCGAAATGAGATCGCTGATGTGGATGTAGTCGCCTGCTGGTAATTAAATATT
AAATATAATGAATTTTTTTAACATTTCATTATATTCAATTGTTTTCAACATTTATCTACATTTCAGCAAGCAAATCACCGAATTAATTGAGGAAA
ATGCATTAAGAAAACGCCAGAAACGATCCAATGTTTTGGCCGCAAGAAACCGGCAAAATGTTATTTTCAAGGACATTTCCCGCTTGGTTTTTGGA
GTTGCGGATATTTTTAGATGCCAAGTGGATCTACTTTTGGGTAAGTATTAGTCCGAATATTACGTAACATTGATATATAATCACGAATTCTTACA
GGGGACACGAAGGTATTACTTGACCAATGTACACGTACCAACTTGGATTACGTTCTCACCACAACAAAATCCGTAGTGGTCAACAAATCAGAGAT
TCGAATCCAACGCAAAGGAAAGCGGGTGATCACCAAGAAATCTAAAGTAACAGTATCAAAACGTCCCAGACTGCAGGAATCGGATCTATTGGATG
AATTCTCACATGAATACTACGAGAAGATGCTATCCGAATGCCAGATGTGGCAAACGGAGTGCACACAACAGGTGGTGGAGGACCTGAACGAGGTT
AGTCGTCAATATACTGTTGGACTGCTTCCTTATATGATTTCATTTTTCGCAAAAAGTCTATTGAACAACCCCGGAGTTGCACTCAGTCAAAGTCG
TATCATTCCATTACAATCACCGAAGAGATTGAACTTCCCGAAGATCATAGCTTAATTATGCCATCAAATGGTTTTGGCGAAGCCGAGGGCGCGGA
CTTAACCATTTTTCAAGAGCTTTACCCCAAAGATGGCACACGGAACTCACGTAAGAATTCTCAATTCAATTGAAAATGTAATAAACTATTTTTTT
GTATTATAGTAAAGCGACACTCAATAGCTCAGGATCCAACTGACATCTTACCGGATAAAATGCCCAGATTGGATGATTGCGATGTTTTCCAAGCT
GACAATGCTATCATGACCCAAATCTTTCCGCATAACATTGAACCAGCTGAAGTAACTCAGATAGTTTGTGAACCGTCGTTGCCATCCGTTTTAAA
TTCTTTTGGAGAAATAACATTTAGCCACCCGAAAAATCGGAAAAGAAAGCTAATAGTAGACAAACGAATTGAATACACCCGGGAGCAGCTGGTGA
AGCATAGACAGAAATATATGGAAGAATACCTTTCAAGGAATGTGATAGTGCCAAAATCCTCGGATTTACGGAAACCCCCTAAGGAACTTCTCTGT
AAACTGTATAATAAGTAGGAGCCTTATACATTTTGCTATTTAAAACTTTTTAATTTTTTGATGTAGTGTAAGTTTTTTAGCTCTTCATAACCACT
CCGGACCTAAGCTCAGTAATGAAGAAAAGGAATTCGAGGCAGAAAACACATTGAGAACCATATTTGGCTGCGAGTTTACCGAGAATCTTTCTAAA
GAGATATTTGTGCGACCATCGCAGGCTACAAAATGTAGGGATAAAGCGGCACATATCTATCAGCCCGAACCGCTTGAAGTGGAAGACTGTGTGCA
ACCTCAACTTCAGCCACGTGATGATGTAAATCAGAATTATCATAATGAAATGAATGAGCACGGCATATACCGTGAGGATAATCATGATGGTGAGT
TCAGCCAATGTTTACAACATGCTATCGTAAATAAAATATAATCTCATTGCAGATACCTACAGCGTAATGATGAGTCTCTTAAGCATTTGGCGTAA
TAATCCGAAAATCACGGGAATCGATGCCATTGATTTTATAAAAACGTTTGATAGTCGCATCAAGGCTTCGTTAGCCTTTCTCCATTTGTTGTGTG
AGTTCGAAAAAGAACAAAATGTGTGTTGGAAATAACGTATAGCTTAAATTTCAGATCTTGTTCGAGACCATTTTATAGAGATATCAAAGCGAGCT
AATTCGCTGGAAATGTACCAAATTACTCTTGGCAAAGAGTCCGCTAAGCTAATAGACAATCTTATGCTGAGTGAGACTCTGTGAATATTTTAGA
TAATTTTTTTCAAGATTACCAAACAACTTTGTAGTTGACAATCTTCCACATTTTTGTTGTTGTTTTGTTTTCTGTTATTGCTATTGTGTTATAAC
ATATAAGTTGAGCCAATCTCTAACCTAGATGGCTTTAATCTACTCTTTTTCCATACAATCTTATGGTACAATTGAGCAACGATGTCCTGGATAAT
TCGTTTCATTTCAAGAATTGAAAAATTCTATAGATGTTACTTGTTGCTGTCTATAAAAATAGTTTTTTTTCATTATCATATTAGTTTCGTGTAC
CCATTAAAAGTTGTTTGTTATCTTTGTTACTATTACGTTATCGTAGCTATAATTCATTAACATTTGGAGTAATTCTCTAAACCGTAATTGTTGTC
TTTGTTACAAAATCTCAATTTCTCTGACAACACCAAAAAATAAACAAGTTACAAAAACAAAGGAATACAGAGTGTTTGGCACAATTGCTTAAATT
CCGATCTGCTGGGCCAGACCCGAATAGATGTGCAGCGTGCAGAATCCAATGACGGCCGCCACCAGCGCTTTAACAGCCACCGTTAGCCAAGGTCC
AATGGTCAGAATGTGGAGCATGCCCTCCAGCCAGACGCCTTTGAAGACAGTCACCGCCAGAAGTAGACTAACCAGCGGCTTTAATGCCTTGTTCA
AATCGTGACGGGTGAAGAGCCAGATCAGGGTGGCCGTAGTGATGTGCTGCACCAGAAGCACGTTCGATTCCAGACACTTGAGGATGTAGATCCAA
CTGAACTCGGTGCCTCGGGCACCCACCCACAGCATGATACCTCGGGAAAGAATCACTTCGGCGGTGGCCCCTGCGGAAGTATACG
(SEQ ID NO: 451)

Exon: 1001..1222
Exon: 1302..1465
Exon: .1522..1802
Exon: 1862..2045
Exon: 2100..2484
Exon: 2537..2844
Exon: 2903..3075
Start ATG: 1092

Transcript No. : CT13940
AAAAAAGTACCGTTACTTTAGGGTTGTTACAGAGAGCACTAACTTATAAATAGTTAATACTATAATCTATGTGCTTAATGTCGTAGTTACAATGA
GCTTGAATTTATATGAGAGCAACATCCTTAATTCCTGCTGGAAAGCGGGAGGGCGCAAACCGAGGAAATCGGCATTTGGCCAACTTAATCGAAAT
GAGATCGCTGATGTGGATGTAGTCGCCTGCTGCAAGCAAATCACCGAATTAATTGAGGAAAATGCATTAAGAAAACGCCAGAAACGATCCAATGT
TTTGGCCGCAAGAAACCGGCAAAATGTTATTTTCAAGGACATTTCCCGCTTGGTTTTTGGAGTTGCGGATATTTTTAGATGCCAAGTGGATCTAC
TTTTGGGGGACACGAAGGTATTACTTGACCAATGTACACGTACCAACTTGGATTACGTTCTCACCACAACAAAATCCGTAGTGGTCAACAAATCA
GAGATTCGAATCCAACGCAAAGGAAAGCGGGTGATCACCAAGAAATCTAAAGTAACAGTATCAAAACGTCCCAGACTGCAGGAATCGGATCTATT
GGATGAATTCTCACATGAATACTACGAGAAGATGCTATCCGAATGCCAGATGTGGCAAACGGAGTGCACACAACAGGTGGTGGAGGACCTGAACG
AGTCTATTGAACAACCCCGGAGTTGCACTCAGTCAAAGTCGTATCATTCCATTACAATCACCGAAGAGATTGAACTTCCCGAAGATCATAGCTTA
ATTATGCCATCAAATGGTTTTGGCGAAGCCGAGGGCGCGGACTTAACCATTTTTCAAGAGCTTTACCCCAAAGATGGCACACGGAACTCACTAAA
GCGACACTCAATAGCTCAGGATCCAACTGACATCTTACCGGATAAAATGCCCAGATTGGATGATTGCGATGTTTTCCAAGCTGACAATGCTATCA
TGACCCAAATCTTTCCGCATAACATTGAACCAGCTGAAGTAACTCAGATAGTTTGTGAACCGTCGTTGCCATCCGTTTTAAATTCTTTTGGAGAA
ATAACATTTAGCCACCCGAAAAATCGGAAAAGAAAGCTAATAGTAGACAAACGAATTGAATACACCCGGGAGCAGCTGGTGAAGCATAGACAGAA
ATATATGGAAGAATACCTTTCAAGGAATGTGATAGTGCCAAAATCCTCGGATTTACGGAAACCCCCTAAGGAACTTCTCTGTAAACTGTATAATA
```

ATGTAAGTTTTTTAGCTCTTCATAACCACTCCGGACCTAAGCTCAGTAATGAAGAAAAGGAATTCGAGGCAGAAAACACATTGAGAACCATATTT
GGCTGCGAGTTTACCGAGAATCTTTCTAAAGAGATATTTGTGCGACCATCGCAGGCTACAAAATGTAGGGATAAAGCGGCACATATCTATCAGCC
CGAACCGCTTGAAGTGGAAGACTGTGTGCAACCTCAACTTCAGCCACGTGATGATGTAAATCAGAATTATCATAATGAAATGAATGAGCACGGCA
TATACCGTGAGGATAATCATGATGATACCTACAGCGTAATGATGAGTCTCTTAAGCATTTGGCGTAATAATCCGAAAATCACGGGAATCGATGCC
ATTGATTTTATAAAAACGTTTGATAGTCGCATCAAGGCTTCGTTAGCCTTTCTCCATTTGTTGTGTGAGTTCGAAAAAGAACAAAATGTGTGTTG
GAAATAA
(SEQ ID NO: 452)

Start ATG: 92

MSLNLYESNILNSCWKAGGRKPRKSAFGQLNRNEIADVDVVACCKQITELIEENALRKRQKRSNVLAARNRQNVIFKDISRLVFGVADIFRCQVD
LLLGDTKVLLDQCTRTNLDYVLTTTKSVVVNKSEIRIQRKGKRVITKKSKVTVSKRPRLQESDLLDEFSHEYYEKMLSECQMWQTECTQQVVEDL
NESIEQPRSCTQSKSYHSITITEEIELPEDHSLIMPSNGFGEAEGADLTIFQELYPKDGTRNSLKRHSIAQDPTDILPDKMPRLDDCDVFQADNA
IMTQIFPHNIEPAEVTQIVCEPSLPSVLNSFGEITFSHPKNRKRKLIVDKRIEYTREQLVKHRQKYMEEYLSRNVIVPKSSDLRKPPKELLCKLY
NNVSFLALHNHSGPKLSNEEKEFEAENTLRTIFGCEFTENLSKEIFVRPSQATKCRDKAAHIYQPEPLEVEDCVQPQLQPRDDVNQNYHNEMNEH
GIYREDNHDDTYSVMMSLLSIWRNNPKITGIDAIDFIKTFDSRIKASLAFLHLLCEFEKEQNVCWK*
(SEQ ID NO: 453)

Classification: known_flybase_gene
Gene Symbol: BG:DS02740.10
FlyBase ID: FBgn0028525

Celera Sequence No. : 142000013384828
AAGACTCCGAAAATCCCTTTTGATCTCTGACAACTAAAAAATGTAAAACTATATCCACAAATTGGTGTTTTAAGCCTAACAAATACTAAAAAATC
TATTTTGCATCGGCCGGGAATCGAACCCGGGCCGCCCGCGTGGCAGGCGAGCATTCTACCACTGAACCACCGATGCTTATGACTCTTTTGAAACA
ATTCTGCTGAAGATTCTACAGAAGTCTCGTTCTTATGATCATTTGGGAACTAAGAGTATCTGATATCCCTCCCCTCATCTGACTCCGTGGCGCAA
CGGTAGCGCGTCCGACTCCAGATCGGAAGGTTGCGTGTTCAAATCACGTCGGGGTCAATGCATTCGTTTTTTTGTCCACATTTCCGATGGAAACC
TAACGTTGAATGGTTTGACCTTGACAACAAGTGGGTCTACAAAAAAATAAATGTAGTTAAGATATGCATGCGAGAGATGTTTTTCATTTTTTATTT
TATAGTATCCGATAATATAGATATATTTGAATTGTACATTAATATGCGTGTACCTAGAATCTGCGCATTAGAAACAATTTGAGTGTTAAATATAC
TCTTAAAACTAAATACATAACAAAATAATAAACATTTCAAGTTTTGCGATTGCTGATTTGTTTATGATTGGGCTTCTACTCCCCCACAAGCTCCC
CTGTCAATTTCCTGTCCATACAATCCGTCTCCTTTGCTAATTATTTGCTATAACTGTGTGTATCTGTTGCTCCACGTTTTCGTTGGTAGTTGTGG
TTCCTATTGTACGACAATTTAAATCACTCGAATTTAACTGAATCTCTGGTTTTAAAAGCGTCCGGTTCAACCCCCACCCCCCTCGTCAAAAATGC
TACGTAATCTCAATTTAAAAACGGTAAAATGTTCGCATGTATGGAGTTACACTAAAGTTACTTGATAAGGAAAATCATAAATTACAACTCATCTT
GAATTTGCTCAATAATAATAAGTTTGTTTCTCATTTGATCTGTCTGTCGCCTAAGGATCAGCTTCGGCTACGACATCGGCGGAAGCAGCAGGGGC
TATGGGTTCCTCCGCGGATGGAGCCTCCGTTTGGAGTTCAGCCGGCGGCGCTGGAACCGATTCCTCATGGGGCGCAGCCTCGGTTTCAATGACTG
GCGGCGCCGGCCGGGGCGGAGAACCTTGAGGTTCTTTCGGGGGCTGAGTTGGAGTCTGTGGAACTGCTGGCGGTGGCAGCTCGTCATAAAGGGGC
GTGCAGGCGGCTGAAGTTTCTGTTTGTGATTTCGCAACCAAAGGATCGCCGGTCACGTCGGCTGGCTTTGCGAAGTTTTCATTCTCCGCCGGCAG
CTTTTCTTGCGGAGGACTGTTAGCAGACTGAGATGCTCGTTCGCCTGGCTTCTGGGCCTCCATTCTCGCCTCATAGTCTTGAAGTTCCTGATCCC
AATCCTCCTCGGTGTCCACTCTAGTGGCCGCAGCCGGCGCACCGGTGTTGGTGCTACCTAATTCGGTTTCAACGTTTTTGGGCTTGGGTTCCGTC
TCCGAAGCCGCCTTGTTGCCTTCATCCGTCGAACTTATTGAGTGGCGGTTGCTGTCATCTCGCGATCCCCGCCTGTTTCCGAATCCCGGACGTTC
ACGATCCTCTCGCGGTCCTCCGCGTCCGCCCCGTGAATTGTTGCCACGACGGTCGTCCATCATTTCGCCTCCACGCTCGCCACGGAATCTATTAC
CGCCTGGCCCACCGGGACCACCACGCCGCTTGAAGTTGTTTCCGCCCTCGTCCTCATCGTCGCTCCAACGTCCGCGACCTCCAGGACCGCCACCT
CCTCCTCCGCCCACGCCGCGAACACCGCCTCCACTTTGACCTCCACGTCCTCGTTGGTTGTCATTGAAGGGATTCCGAGGATTAAAGAAACCTGA
AACGAACGTTAGCATAAATTGCACAAATTAGTTTACATAAAATGTTCCTTATATAGTTGCAATAAAAAAAAAATTAATAAAGTTAAATTAATTAT
TATTTATATACACCTGGTAAACATAATATTTACACGCATAAAAAAGATGCCACCAAATTCTATTATCGTTTTTTCTTCTTCTTTCGTCTTTGCTT
CAAATTCCCACGATTCTCACCTGGTCCCTGCTGACGTCCGCCCGGACCACCGCCGCCGGTTCCAGCACCGCCGGGTCCACCACCGCTGGGTCCAG
CACCACCTGGCCCACCTCCTTGGTTGCGCATAAACATGGGCCCAACGCCGTTGCCACCGTTACCAGCTGGTCCACCCATGCGCTGGTTGAAAGAA
GCCGGCGGCGGGATGCGCATCTGCATCAAGCTGGTGGGCTGATTGAACCGATTGTGATTCATGTTGGGCGGAAAAAGTCGCCTCCGGGGCCTCC
ACCGTTATGGTTTCCACGCGGTCCCATTCCTCGTGGTCCACCCGGTCCACCGCGATTATCAAAGTCTGCAATGCGTTTTAGTTTAGTGAGCTGCG
AAGATTCGTACCATTTATGTCGACTCACCCATAAAGTCCGGTCTTGGCATACCGTGCTCAATGGGATTAAGGTTCAGACGCGCTCGTGCCTCGTT
AAAGGCTGCGTTCGGTCCGAGTCCAGATCCCGGACCACCACCACCTCCTCCATTTTCGGCGCGCCAGCGTTCTGCCGCTTCAACGACATCATCTC
GTCCGCCCCAGCGCGAGTTGCCCGGTCCCCTGGAGCGATCCCTATTATCCCGATCGCGCTCCCTGTCCCGCTGCTGGAACATCTCGTTGGCCATG
GCCGCCGGCGATAGGTCCACATTGCTGGGCGACGGATTAAAGTTGGCTTGCTGTTGCGGCGGCAGAGGTGGGGCGTCTTCCAGGTCCATTTCAAT
GTCCATTTGATCATCGCTCACGTTGCCACTATTGCTAATCTGCCCACCGCTCGGTATGGGTGGCGGCACAGCTCCAGGCGGAGGAAATGGAGCTC
CCGGTGGCAAGGCCATAGGATGTGGTGGTCCCCCAATGCCTGCAGGAAAAAAAATTAAAATTAAAGCTTGAAGTTCAATTTTACGAGATTATTAT
CTACCTGGAAAGCCAGGAGGCATCATTGTCGGTGGCATCATCATTGGAGGAGGCATGTTGGTCGTTGGCATCATCATCGGTGGCGGCATATTTGT
TGGCGGCATCATTATGGGCGGTGGCATATTAATGCCCATGGGTGGGGCCATCGGAAATTGTCCCCTTACCATACCCATGAGCCCCGGAGGTGGGG
CTCCCGGACCCGGTGGAGGACCCACTGGGCCGACTGGACCAACCGGTGGTGGTTGGGTTGTATCGATACCAAATATCAGATTTGGCGGTGGAACA
CCAACACTTGGCGCACCAGCTGCCTCCGCAATGGATGCACCCTTGTGCTCCTTGGCAGCATTCTTGGCCTGGTTAATCTTCTGCTTCATTTGGAT
GGGCATAGTATCTTCGTCGAACATACCACCCTCCTCCAGCGCGTCGAAGTCCGTATCCGAACTGAGTTTGGACCAAGGAATGTAAGTAACACCCA
ATTCGAGGTCCCAGTAGTCCTTCCACTCCTTGCTTTTCACACCCTTGCCGGCGGCCCATGAAATGGTGATGGCTCGTCCCTGCAGCTTGTGGTTC
TTCAGAGCTTGCATCGCCTTGTGGGCGTCTTGGCGTCGGTTCATTACAATAAAAGCGCATCCACGCGGCACAATCTGATCGATGCTCACTATATC
GCCATATTCGCCAAAGGTATCGGACAGCTCCTCCTGGTAAACAAGCTTAGACAGGTGGCCCACCCACAGCGTAGTGCTGCATACTGAAAGCAAAA
GCATTGGAATGCCGCATTAGTTTTTGGTGTCTGAACATGTTGTCAATATGCCCATTTGCCTTGTTGAGGTGTGAGTGCCACTGTTGGGATAGTGT
TTAGAATTCCTTATCCTTAAGTATATTTACCAAGATTTAAACTATGATCTATGTACTTCATTAAGAAGCCAGTTCTTGGTAATTAAGCTTAAGTA
TATATTAGTGTAGAACACAACGTTTGTTTGCATCCTTATGTATATGTATGTAAATCGGGTCTCAAAAAATATTGCTCGAAAACGCATATTATATA
GGGGGATATTCTAAGATCAAGAACCACTAAAGCTAAACACACACACGTCAACCGAGCCAAAGGAGCTGCAGAGAAAAGGAAGTAAATCTTTAGGA
TTATCAAAAACAAAAACAAAAAAAAAAAAGAAGGAAAAACAGGAAAGCACACAATGCAAATGGATCTTAAGAAGCACCATCTTGTGGCCTTTAAG
ATCCATTTATCATTCCCGTCATAGTTACCACTGAGATGCTCCTTTTTGATGTCGGGCAATCCCTTCTTGCGCCGCTCACGCTCGTGTTCCCGATC
GCGTTCCTTGTCTCGATTGCTACGATCCATGCGATCCCGGTCCCTTGATCCGCGTCGCCGGCTGGACCGTGGTGATCGGCTGCGCGATCGGGAAC GAGTGCCACGCCGACGTCGATCGTTGCCCGTGCCTCCTCCGGCGCCACGTCCTCGCGGAGATCTCGTCCGGCTGCGACTGTTCCGGCGACTGCGC
TTGTAGCGATCACGGTCGGGCGTCGGGCTGCGGGAATCGCCACCATCCAGATTGATCACCTATCGGAGATGGGAGTGTTTGCAAGAAATTTGAGA
GTGATACGTGATAAAAATTTTGTTAAGAATAAAAAAAAAAAGTTCAGTGGGATAGAGAGGATTCGGGATTAGTGGCTGGCCACAGGGCGAATACG
TTATTATCGACTCAATAAACTGCATTCTTTGGCGTGTGTTGACGTGTGGTTCTGTTTCGCTTTCGACTTTCATTCATCTAGTTATTTCGGACTAA
TTGGCAATTTGCGTTTTCGAGCAACATTTTTATTTACATATTAGGAACTTACCAAACGTTGTTCTAGCATCGGGTAACGAGTTGTTCCGCCGGAT
ATTATGTGGATTTTAAAACCTTACCTTTGGCTTCATTTGCATATTTTTTAAATATTTTACTATTGGTTCGACTTATTCAAATATTGGCAATTGTT
TTATAGTTCAAATATATGTTGGGGACATATAGATCGACTTATGAAACTGATTTAGGGTTTGCCCAAAAGCATCATCTTTTGATTTTAAACATTTT
TTTTACAACAAAATAAAATTTAATTTTAAATGGATTGGGAATTGAATTGTTTGCATATTCAAGATATATAGTATTAAAGTTATTGATTAAATAGT
GCAAGACCACCCCGTTACAACTAGTTGAATCAATTTGGATTCGAACACGCTAATATCCCATCAGCTATAACAACATATTGAACACATTTCCAGGA
TTAACTGCACGTCAGCACAAGGCAAATAGTATCACCCGTTTTACATCTAATATGTTTATACTTTAGACCAAAATTAATGGCGAAGTCTTGGTGAA
AAGCATACACAAGTCGGACCCCAGGAACTAAGATAGATTGGAAAAGTAGAAGGGTATACCTCTATGGTCTGTTGCTCCGATATGAACTCGACATC
CTTGTTAAGGTCCATGCTGTCGTTCATGTTCATGCCCATGCCCATGCCCGGCGGCATACCAGCATTTCCCTGAAAGCAAATCATAATGAAAATAT
GTACATCGTCATGAAATCATAAGATGTACCTTCATTACGTTCTGGAAATGCTGCTGCAGTGCCTCGTCCTGATAGCGATGCTTCTGGTTCTCCTC
CTGCGGCTTCAAATTTTGGAAGTTCTGCAGCGTATGGAGCTGCCGCAGCACATTCGGATTGTTTAGCAGCTGCTTGATCTTCTTCTCCTGAAAGA
GTTATTTAAAAGGTTATTCAAAATGGGATCGATCTAATGTGAGCAACAAAAGCAACAAATAGAAACTTAAGATAAACAAAACTATCTAAATGAAG
AGATGTGTTAATGGGGTTCGCCATACGTCTAACAGGTTTGAAGAAGTGGGCGGTGAGTCGTCGCCCATACAGTGGTGATCATCTGCCATCAGCAT
CTGCAGGCCTTCATCTTCTTCCTCGATGATCTCCCGCACCTGGTAGTCAATGTCGTGCGAGCTCTTGACATATTCCCGTTTGTGATGATGCGACT
TGCTGGTCTTCGACGAGCACGAGACCACCGACTGTCGTTTGGAATAGTGTTGCTCCGAGTAGTGACGCTTGGAGCTGCTGCTGCCACCGCCGAAC
TTCTCATGGCCCAGCTAGCGATTGGGCGAAGGGCAAAATGGGCGGTTAGTGGGCAAGACATGAGAGACAGAGAAATGTAAATGCAGCAGAATTGT
AGACGATGTTAGTTAAGCCATTATCCAATACTAGACACCTGTAGAAGCCTCAACCGAAAGCATCACTTACCGACAAGTCGGGCATGGCACCGCCC
ATCTTATCGTCGCCCCCGGAGCTGTTCATGCTTATCTCCATTCCGGAGCTGTTTAGACCGTTCGGACCGCTCGATATGTCCGCCAGGCTAAGAGC
ACCGCTGCTGCTGGGTCCTGGACCCACGCCGCCGCCCTGTCCTCCACTGCCACCCACCGGAGGCATCTGGTGGTAGATTGGGTGGTTTGGGTCGG
CCAGGTCGAAGATCGGCTGAATGACCTCGGACTTGAAGACGTTGTTTTTCTGCCACAGGTTCAGTACCCGGATGATGCGACTCTTGTCCTCCGGA
GCGCACCGGAACAAGTTGGCAAAGGTCTCCGTGAGATTACGCTGGAATCGGGGCGCGAACAGATCCTTGTCCATACCGTACTGGTGGCGCGACTG
GCGCACTATCGAGTCGATTACATACAGCCCGGGTACTTTGTACTCCGGCTTGCACTTCAAGATGAACTTCTCCACACTCTGGACGACGTGCTTAT
ACAGCTTGATGGCCCGCATCGCCGACTTGGTGATGGCGGCCATCTTCGCTTTGGAAATGGGCGGTCGGCTGTCATAGAGTCCGGAGAGCTAAGGA
GAAATATAGATGTTACAGTACGGCTATAGTTTACGGATATCTGGGACATGGAGTTATCGTTATCGGGTGCTGGCCAAAAAGCAACCCTGAGCGGT
GCTGTTCGGTGCTCTGCCTGCGCCTCCAGCAGGATCTGTATACCTCCCGCACATTGGACAATCCGAATACCGACTTCAAGCGGACATTGTGCAAC
CACGCCGGCTGCTCCATAACGAACCTCGTTTCTAATGCATCTATAGCTTACCTCATTGTTGAAGGCAACCACGGTTTCCATGTTCAATTGCTTGG
TTCACTCACGGCACGCACACACAATATTTAGTTTTGCATACTTTGGTTGGTCAACACAATCGTTTAAAACTGGCGAAAAACAATTTTCTCGACCT
TTCTGCGGTTTCCACGGCTTTAAAAAAACTTTTTACAAAGCGTGAAAAAAATGGCTGCCCTAAAGCCTGAAGCGTTGCCAGACCTGTAAAGTTG
ACATTTTCAAGGCATTTCTGGAAATTGTGCTGTTAATGGCAGTGTGACCGTATGTGGTGCATAACGTTTCGGTATTAAAAAATTTTCCAAATATT
TATAAAAAATAAAACGAAATAGAATTTTCATTATGGAATCCAAAAGTTTCATATAAAAAAATAATGACAACAAAATAAAAATGACCTTAAATAAA
TTTAAATGAAATCAAATCTTCTTAAATGTACTACCTTTTAAAAATAATCGCTATCGGCGGTGTCGATCTTTTTAGCATTGTGTCGATGACAATAC
ATCTGGCAACACTGGTCAATATTAAACATATATTAAACAAATTAAAATGAGCTCAAACCACCGTCCTCTGGACGATTCGGATATCCTCCTAATAC
AAACCATCCGCGAGACGCCGTCGCTGTACGATCCCCAGCTGCCCTCCTTTCGGCTGTCGCAGCGCAAAGAGGAGGACTGGGCAAAAGTGGCGGAT
TTGCTAAACATCTCCATCTCAGACGCTCGGCGACGGTGGACGTGTCTGCGGGATCGCTATTCGCGGGAGCTTAAGCAGAAGCGCCTGCATCCGTC
CGGCGAGTTTGGTCACAATGACTTCTTTCGGAAGATGGACTTCCTGCGGGACTTTGTGCGCAAGAGACGCGAGCGCAGAGGACGCGAACGGGATC
GGGAACAAAAGCCAACCGGGTGGATGAAGGTTGATTTACAGCGACGGCGTCGTACCCGCCTGCCTATTGACACAGAGACCTTGATCGAGGAGCAA
GGTTCGCACGCCTACGATGAGGGCGAGGAGCAACACGACTACGACGCTAAGCTGGAGTCTCATACCACACAATCGGAGACGTATTCGGTGGTCGT
GGAGGCGGACGATGGGCAGGAGCCCGAACAGGAGAGCTTCGATGAGTTCCTGGGGGATGCGGAGTGCGAGCAAAAGGTCAAGGTGGTCACAATTC
ATCCGGAAATCGCTGCTCCGA
(SEQ ID NO: 454)

Exon: 7381..7177
Exon: 6928..6341
Exon: 5787..5635
Exon: 5579..5475
Exon: 4619..4304
Exon: 3788..3045
Exon: 2984..2499
Exon: 2440..2111
Exon: 1896..1001
Start ATG: 6883 (Reverse strand: CAT)

Transcript No. : CT13962
CTTTAGGGCAGCCATTTTTTTCACGCTTTGTAAAAAGTTTTTTTAAAAGCCGTGGAAACCGCAGAAAGGTCGAGAAAATTGTTTTTCGCCAGTTT
TAAACGATTGTGTTGACCAACCAAAGTATGCAAAACTAAATATTGTGTGTGCGTGCCGTGAGTGAACCAAGCAATTGAACATGGAAACCGTGGTT
GCCTTCAACAATGAGCTCTCCGGACTCTATGACAGCCGACCGCCCATTTCCAAAGCGAAGATGGCCGCCATCACCAAGTCGGCGATGCGGGCCAT
CAAGCTGTATAAGCACGTCGTCCAGAGTGTGGAGAAGTTCATCTTGAAGTGCAAGCCGGAGTACAAAGTACCCGGGCTGTATGTAATCGACTCGA
TAGTGCGCCAGTCGCGCCACCAGTACGGTATGGACAAGGATCTGTTCGCGCCCCGATTCCAGCGTAATCTCACGGAGACCTTTGCCAACTTGTTC
CGGTGCGCTCCGGAGGACAAGAGTCGCATCATCCGGGTACTGAACCTGTGGCAGAAAAACAACGTCTTCAAGTCCGAGGTCATTCAGCCGATCTT
CGACCTGGCCGACCCAAACCACCCAATCTACCACCAGATGCCTCCGGTGGGTGGCAGTGGAGGACAGGGCGGCGGCGTGGGTCCAGGACCCAGCA
GCAGCGGTGCTCTTAGCCTGGCGGACATATCGAGCGGTCCGAACGGTCTAAACAGCTCCGGAATGGAGATAAGCATGAACAGCTCCGGGGGCGAC
GATAAGATGGGCGGTGCCATGCCCGACTTGTCGGAGAAGAAGATCAAGCAGCTGCTAAACAATCCGAATGTGCTGCGGCAGCTCCATACGCTGCA
GAACTTCCAAAATTTGAAGCCGCAGGAGGAGAACCAGAAGCATCGCTATCAGGACGAGGCACTGCAGCAGCATTTCCAGAACGTAATGAAGGGAA
ATGCTGGTATGCCGCCGGGCATGGGCATGGGCATGAACATGAACGACAGCATGGACCTTAACAAGGATGTCGAGTTCATATCGGAGCAACAGACC
ATAGAGGTGATCAATCTGGATGGTGGCGATTCCCGCAGCCCGACGCCCGACCGTGATCGCTACAAGCGCAGTCGCCGGAACAGTCGCAGCCGGAC
GAGATCTCCGCGAGGACGTGGCGCCGGAGGAGGCACGGGCAACGATCGACGTCGGCGTGGCACTCGTTCCCGATCGCGCAGCCGATCACCACGGT
CCAGCCGGCGACGCGGATCAAGGGACCGGGATCGCATGGATCGTAGCAATCGAGACAAGGAACGCGATCGGGAACACGAGCGTGAGCGGCGCAAG
AAGGGATTGCCCGACATCAAAAAGGAGCATCTCAGTGTATGCAGCACTACGCTGTGGGTGGCCACCTGTCTAAGCTTGTTTACCAGGAGGAGCT GTCCGATACCTTTGGCGAATATGGCGATATAGTGAGCATCGATCAGATTGTGCCGCGTGGATGCGCTTTTATTGTAATGAACCGACGCCAAGACG
CCCACAAGGCGATGCAAGCTCTGAAGAACCACAAGCTGCAGGGACGAGCCATCACCATTTCATGGGCCGCCGGCAAGGGTGTGAAAAGCAAGGAG
TGGAAGGACTACTGGGACCTCGAATTGGGTGTTACTTACATTCCTTGGTCCAAACTCAGTTCGGATACGGACTTCGACGCGCTGGAGGAGGGTGG
TATGTTCGACGAAGATACTATGCCCATCCAAATGAAGCAGAAGATTAACCAGGCCAAGAATGCTGCCAAGGAGCACAAGGGTGCATCCATTGCGG
AGGCAGCTGGTGCGCCAAGTGTTGGTGTTCCACCGCCAAATCTGATATTTGGTATCGATACAACCCAACCACCACCGGTTGGTCCAGTCGGCCCA
GTGGGTCCTCCACCGGGTCCGGGAGCCCCACCTCCGGGGCTCATGGGTATGGTAAGGGGACAATTTCCGATGGCCCCACCCATGGGCATTAATAT
GCCACCGCCCATAATGATGCCGCCAACAAATATGCCGCCACCGATGATGATGCCAACGACCAACATGCCTCCTCCAATGATGATGCCACCGACAA
TGATGCCTCCTGGCTTTCCAGGCATTGGGGGACCACCACATCCTATGGCCTTGCCACCGGGAGCTCCATTTCCTCCGCCTGGAGCTGTGCCGCCA
CCCATACCGAGCGGTGGGCAGATTAGCAATAGTGGCAACGTGAGCGATGATCAAATGGACATTGAAATGGACCTGGAAGACGCCCCACCTCTGCC
GCCGCAACAGCAAGCCAACTTTAATCCGTCGCCCAGCAATGTGGACCTATCGCCGGCGGCCATGGCCAACGAGATGTTCCAGCAGCGGGACAGGG
AGCGCGATCGGGATAATAGGGATCGCTCCAGGGGACCGGCAACTCGCGCTGGGGCGGACGAGATGATGTCGTTGAAGCGGCAGAACGCTGGCGC
GCCGAAAATGGAGGAGGTGGTGGTGGTCCGGGATCTGGACTCGGACCGAACGCAGCCTTTAACGAGGCACGAGCGCGTCTGAACCTTAATCCCAT
TGAGCACGGTATGCCAAGACCGGACTTTATGGACTTTGATAATCGCGGTGGACCGGGTGGACCACGAGGAATGGGACCGCGTGGAAACCATAACG
GTGGAGGCCCCGGAGGCGACTTTTTCCCGCCCAACATGAATCACAATCGGTTCAATCAGCCCACCAGCTTGATGCAGATGCGCATCCCGCCGCCG
GCTTCTTTCAACCAGCGCATGGGTGGACCAGCTGGTAACGGTGGCAACGGCGTTGGGCCCATGTTTATGCGCAACCAAGGAGGTGGGCCAGGTGG
TGCTGGACCCAGCGGTGGTGGACCCGGCGGTGCTGGAACCGGCGGCGGTGGTCCGGGCGGACGTCAGCAGGGACCAGGTTTCTTTAATCCTCGGA
ATCCCTTCAATGACAACCAACGAGGACGTGGAGGTCAAAGTGGAGGCGGTGTTCGCGGCGTGGGCGGAGGAGGAGGTGGCGGTCCTGGAGGTCGC
GGACGTTGGAGCGACGATGAGGACGAGGGCGGAAACAACTTCAAGCGGCGTGGTGGTCCCGGTGGGCCAGGCGGTAATAGATTCCGTGGCGAGCG
TGGAGGCGAAATGATGGACGACCGTCGTGGCAACAATTCACGGGGCGGACGCGGAGGACCGCGAGAGGATCGTGAACGTCCGGGATTCGGAAACA
GGCGGGGATCGCGAGATGACAGCAACCGCCACTCAATAAGTTCGACGGATGAAGGCAACAAGGCGGCTTCGGAGACGGAACCCAAGCCCAAAAAC
GTTGAAACCGAATTAGGTAGCACCAACACCGGTGCGCCGGCTGCGGCCACTAGAGTGGACACCGAGGAGGATTGGGATCAGGAACTTCAAGACTA
TGAGGCGAGAATGGAGGCCCAGAAGCCAGGCGAACGAGCATCTCAGTCTGCTAACAGTCCTCCGCAAGAAAAGCTGCCGGCGGAGAATGAAAACT
TCGCAAAGCCAGCCGACGTGACCGGCGATCCTTTGGTTGCGAAATCACAAACAGAAACTTCAGCCGCCTGCACGCCCCTTTATGACGAGCTGCCA
CCGCCAGCAGTTCCACAGACTCCAACTCAGCCCCCGAAAGAACCTCAAGGTTCTCCGCCCCGGCCGGCGCCGCCAGTCATTGAAACCGAGGCTGC
GCCCCATGAGGAATCGGTTCCAGCGCCGCCGGCTGAACTCCAAACGGAGGCTCCATCCGCGGAGGAACCCATAGCCCCTGCTGCTTCCGCCGATG
TCGTAGCCGAAGCTGATCCTTAG
(SEQ ID NO: 455)

Start ATG: 251 (Reverse strand: CAT)

MAAITKSAMRAIKLYKHVVQSVEKFILKCKPEYKVPGLYVIDSIVRQSRHQYGMDKDLFAPRFQRNLTETFANLFRCAPEDKSRIIRVLNLWQKN
NVFKSEVIQPIFDLADPNHPIYHQMPPVGGSGGQGGGVGPGPSSSGALSLADISSGPNGLNSSGMEISMNSSGGDDKMGGAMPDLSEKKIKQLLN
NPNVLRQLHTLQNFQNLKPQEENQKHRYQDEALQQHFQNVMKGNAGMPPGMGMGMNMNDSMDLNKDVEFISEQQTIEVINLDGGDSRSPTPDRDR
YKRSRRNSRSRTRSPRGRGAGGGTGNDRRRRGTRSRSRSRSPRSSRRRGSRDRDRMDRSNRDKERDREHERERRKKGLPDIKKEHLSVCSTTLWV
GHLSKLVYQEELSDTFGEYGDIVSIDQIVPRGCAFIVMNRRQDAHKAMQALKNHKLQGRAITISWAAGKGVKSKEWKDYWDLELGVTYIPWSKLS
SDTDFDALEEGGMFDEDTMPIQMKQKINQAKNAAKEHKGASIAEAAGAPSVGVPPPNLIFGIDTTQPPPVGPVGPVGPPPGPGAPPPGLMGMVRG
QFPMAPPMGINMPPPIMMPPTNMPPPMMMPTTNMPPPMMMPPTMMPPGFPGIGGPPHPMALPPGAPFPPPGAVPPPIPSGGQISNSGNVSDDQMD
IEMDLEDAPPLPPQQQANFNPSPSNVDLSPAAMANEMFQQRDRERDRDNRDRSRGPGNSRWGGRDDVVEAAERWRAENGGGGGPGSGLGPNAAF
NEARARLNLNPIEHGMPRPDFMDFDNRGGPGGPRGMGPRGNHNGGGPGGDFFPPNMNHNRFNQPTSLMQMRIPPPASFNQRMGGPAGNGGNGVGP
MFMRNQGGGPGGAGPSGGGPGGAGTGGGGPGGRQQGPGFFNPRNPFNDNQRGRGGQSGGGVRGVGGGGGGGPGGRGRWSDDEDEGGNNFKRRGGP
GGPGGNRFRGERGGEMMDDRRGNNSRGGRGGPREDRERPGFGNRRGSRDDSNRHSISSTDEGNKAASETEPKPKNVETELGSTNTGAPAAATRVD
TEEDWDQELQDYEARMEAQKPGERASQSANSPPQEKLPAENENFAKPADVTGDPLVAKSQTETSAACTPLYDELPPPAVPQTPTQPPKEPQGSPP
RPAPPVIETEAAPHEESVPAPPAELQTEAPSAEEPIAPAASADVVAEADP*
(SEQ ID NO: 456)

Classification: RNA_binding

Celera Sequence No. : 142000013384826
GTTTTCCCGGCTCTGTTTTCACAATGGGCTTGAGTGGCTTCACCTCCGGCATGACAGCGTCTATTAGAGAGAGTCCTTCAATGGGTCGCGCCACC
TCGCCGTCTTCGCCTACGCTCCACTCCACTTCAGTGTACAGAAGACCCTTCTGCAGGATGGTGAGCAAAGCGGCAGGTGGAACCAATGCGCCATT
GATATTACTTTGCGAGATGTGTGACTCAATGCCAAACACGTAGGCCGAGTGCAGAAAGCCTAGAAAACGGGATTGCATGAGATTAGGGCGGGCTG
TTATCTTGCGATTGGAGGGTTTTACTCACCCGACTCCTGCAGGTATCGGTAAACCAGAAAGTTCACCTCGTCGCTGGAAAAACTCATGACGGAAC
GCGGTTGGCTCCTTCTCCTACTACTAGCGCACTCCAAAATCCACTCCTATCTCCAATGCCAATTATGTTTTTACGGTGCGAAAATCGGAACTGTG
CTGCGTAACACATGCGTCTGCATTCGGCACGCTTATCACTTCGGCGCAAGCCACGGTATCCGGTGCTACTCCTGGTACTTGGATCGATCTGGTCG
GTCCTGTGTTTTCAATTCTGCCAGTTTGCTGCTTGCCGCAAGAGCACTTCACATATTTTTCCACAAATAAAACCGAGGGATCGAAAACGCGTTT
CTGAAACGCGCAAAAAAATGGCGGAGTAATCTCAAGGTGTGCGCTGCGAGAGGTTGCGCAGCCTTGTGTTTTGTGACGTCACAAGTTTTGACAAC
AACTTAATCAAATTTGAGTCATATTTTTGTATTGCACCAAGCGTTACCTTAAAGGATAGAACGGAAATTTATTAGCCATAAAAACAATTAAGAAG
ATATTTTTGGATTTCTGCTTGGAGCAAAAGGTAAAAAATTCTTAAAGCGAATTGTCGTCTCTCTTCGTCCATCCCTGTGTACCCATCCCTCGAAG
TAATCATTGTATTTCAACCCAACGCTCTACTGGTCACACCAATCGTTCCACCCGCGCCCGCTAGATGGCTCCACTCTTAGGCAGCGAGAGCGAAG
AAAAATCAATAGAAATTTTCATTTTAGTGAATTGCCCTGCACTTGGTAATAGTTAACAAACAAATTAGCGGCAAATCAGCGAGGCGAAGCTCCAG
CGAGTTGGAGTTCCATAAAGTGCAACACGCAGGGTCAAACATTCCGCAGCCAACACCCCGGATTCCGATTCCAAGCGAAGCCAACTTCAGAAGTC
AGAGATTACTCTCTCTGCTCCGCCACAGAAATTCCGCAACGCTAACCGATTTTGTCCGCTGGCGAGTAAAAAAAATCGGAAAAGTAAGCTCAAAA
AAAAAGAACAGCTAACATACGCCCATTAATGTTTTTGGAGGCTTCTTCGGTGCTTTTTTTTTTGGGCAAAACGCCCTCGTCATCCAGCGGTGAAA
AAAGTGACGTGACATGAAAGCAAAGAAAGAAGAGAACCGAAGAGCGCAGTGAAAAACAGAAAATAAAACGAAACGGAAAGCAAAGTAAAAAGTAT
ACTACAGAAACAAAAGCCGGTGGTCGCGCAAATCCAAATAATAATGCCCAAGTGCACATCGACTTCGCCAGGCGATAAAAAGTGGGCGAGCGAGG
TCACAGAATCTTTATCAACGGGCAAAACGCTGCCAAGTTGAAAATAAATCGGTTGCCAAAAATGCGGGGGTACACTCTACTTCCACCAGAAAATG
TCAAAGTTCGCCAGCCATTGGGTGCACTGGCCGGAAAATCAATCACGTAGTCCACTATTTACCGTTTAAAAGTTCTGAGTTTATTAAACATTGGA
TTTTTTATACATATAAATCGTTATCAGCGCTTGATGCTCAGTGAAATGTGTGGTGCATACATATTTTGTGGCGTTTTCGTTATCAAAAGTAAAAC
TGCAATACGGACTTTCAAAATAGAAGCTGTATCAATGTGTTGGCATGCACAATAAGCTACTCCCTGGCTAAATACAAATTGTTATCCAAAATACC
TTTTGTTTGAATAATATACGTTTGTTAACACAAATACTAAAACGTAATCATAATACTAAGTTTTCCCATTCCCACAACCCACAATAAATAGAGTA TCGTTTCCCCTTTCAGGTCCCAAGGAACGGCCGAGATCCAATCGAAGTAAAAAGAGCTTTGCAGAACCAGAGCGGAGAGCAACTATATATCTTAG
GGTCCGACGTCGAGTTCGAGCGATAAGAACGCCTCGAGACTCGGCCGCCATCCATTGACGATTTTCTTGCGCCCCCAGTTTGCATAAAACCAGCG
AAAATTAACAAGCTAACTACCATGGCGCCGGTGCGGGGGGATGGCATGAGAGGCCTGGCCGTCTTTATATCGGATATAAGGAACTGTAAGTGCAG
ATCTCTTGGGTAACCAGCATTAAATCCAATTGAGCGGGTCGCAACAAGAGATTTTCCATAGGGGCGGAATCAGCGCCATTACTTGATCAATTACC
AGGAGCAGCGCACTGACAAAAACGTGGGGCGGTACAAAAACGCAGGAACAGTAAGCTCTCTGCCAGATGAATTACAAAATATTGGCTACTTTTCT
TCTCCATTCCTATGTAAATGTTTTCGTAGTCGTTACATTAGAAAGATATGAGAAAGTTATATATATAGTTATATATATGGGTACAACACAGCAAA
TAGTTATATCAATGTGAATCGGTTGCCTCTCAGTATTAATAAATACTTACAATTTTGATAGTTTGATGACTTACTGTAGTACTTCGAAGCGTGCA
TATGTGTGTGCGCAAGAGTCCGACGCTTCACTGTATGGTATTATTATCACAGCTCGTTGTTTGCTGTATGCTCGGTTACTAGTTTCTGGTTTGTG
GACAACATATAGGAGAGCAGAGGTTCCGCTGCGGATCGGTGACTGGTACTAATTGACGCCTATGTGAATCGGAGAAAATCCGCGACATGGAGAGA
GCTGAAGGGTGTGAAGTCGTCTCTCCGATCGATCAATCGCGGGGTGGAAAGGAAAGCGAAGCTTCCGCAGACGAATCACTGTTGTTTTACTGTGA
ATCTCCCTTATACCCGCATAAGACACAAATTTCTATACTAATATTCACCCATTTGCCCACAGGCAAAAGCAAAGAGGCCGAAGTCAAACGCATAA
ACAAGGAGTTGGCCAATATACGAAGCAAATTTAAAGGAGACAAAACCCTCGACGGCTATCAGAAAAAGAAATATGTCTGTAAGCTGTTATTCATA
TTTCTCCTCGGCCATGACATCGACTTCGGGCACATGGAGGCGGTCAATTTGCTGTCCTCCAACAAATACTCAGAAAAGCAGATTGTGAGTACCCC
AAAAAATTGCTTCAATAATCATTTGTTTATTTAGCGAGTCGAAATAATTGAACTGAAAGCAGACGACTCTGCTTGTGGGAAAAGGGAATTTCATT
CAATTAAATTTAACTTGTCGTTGTTTGAAGTTTGATAAAAATAATTAAAAAATTGGTTTTTTAAATTTAATGTTACTGATAAAATCTGTTTTTTG
AACTTTAGGGTTACCTTTTCATCTCAGTGTTGGTGAACACCAACAGCGACCTTATTCGGCTGATCATCCAATCTATAAAGAATGATTTGCAGTCG
CGTAATCCTGTGCACGTTAATCTGGCACTACAATGCATTGCCAACATTGGAAGTCGGGATATGGCCGAGTCCTTTTCCAACGAAATACCCAAGCT
ACTCGTCTCGGGCGACACCATGGACGTGGTGAAGCAGTCGGCGGCGCTATGCCTGCTCCGCCTGTTCCGCTCCTCGCCGGACATCATTCCCGGTG
GTGAGTGGACTTCGCGCATTATCCATTTGCTCAATGATCAGCACATGGGAGTGGTCACAGCGGCCACCTCGCTGATCGACGCCTTGGTGAAGCGC
AATCCGGACGAGTACAAGGGTTGTGTTAATTTGGCTGTTTCACGCTTATCCCGGATCGTAACAGCCAGCTACACGGATCTTCAGGTACGATTTAA
TGCATTTTTTAAGGTAAGAAACTTCTAATTACTAACTAAATTCGCATTGCAGGATTACACATATTACTTTGTGCCGGCTCCATGGCTATCGGTGA
AACTTCTGCGATTGCTGCAAAACTACAATCCAGTGACCGAAGAGGCCGGTGTGCGGGCCCGCTTGAATGAAACTTTGGAGACGATTTTGAACAAG
GCGCAAGAGCCGCCAAAGAGTAAGAAGGTGCAGCACTCTAACGCAAAGAACGCCGTGCTCTTCGAGGCCATCAACCTGATCATTCACAGCGACAG
CGAGCCGAACCTTCTTGTCCGCGCTTGCAACCAGTTGGGACAGTTCCTTAGCAATCGGGAGACCAACTTGCGCTATCTGGCTCTGGAGTCCATGT
GCCACCTGGCCACATCGGAGTTCTCGCACGAGGAGGTGAAGAAGCACCAGGAGGTGGTCATTTTGTCAATGAAAATGGAGAAGGACGTGTCCGTG
CGCCAAATGGCGGTGGATCTTTTGTATGCCATGTGTGATCGTGGTAATGCCGAGGAAATTGTTCAGGAGATGCTCAACTATCTGGAGACGGCCGA
CTACTCTATTCGTGAGGAAATGGTGCTCAAGGTGGCCATTCTTGCCGAGAAGTACGCCACGGATTATACCTGGTAGGTGTTCTCTTTTTTAGCTT
GTGCTTAAAAGTCTATGTGCTTTATGACAACCGCTATATTACCAGGTATGTGGACGTTATCCTCAATCTAATTCGCATTGCTGGCGACTACGTGT
CTGAGGAAGTATGGTACCGCGTCATTCAGATCGTGATCAATCGCGAGGAGGTTCAAGGCTATGCCGCAAAGACTGTTTTTGAGGCGCTACAGGCC
CCTGCCTGCCACGAAAACATGGTTAAAGTGGGCGGCTACATCTTGGGCGAGTTTGGCAACTTAATCGCCGGAGATTCCCGCTCAGCACCACTGGT
ACAATTCAAGCTACTGCACTCCAAGTACCACTTGTGCTCGCCGATGACCCGGGCCCTTCTTCTGTCCACGTACATTAAATTTATCAACCTCTTTC
CGGAAATTCGTACCAATATCCAGGATGTGTTCCGCCAGCACAGCAATCTTCGATCCGCAGATGCGGAACTGCAGCAGCGAGCTAGCGAATATCTC
CAGCTTAGCATAGTGGCATCGACAGACGTTTTGGCCACCGTCCTGGAGGAGATGCCATCGTTCCCGGAACGCGAGAGCTCAATTTTAGCAGTGCT
AAAGAAGAAGAAGCCCGGCAGGGTGCCGGAGAACGAAATTCGCGAGTCGAAGAGCCCGGCACCCCTGACTTCTGCAGCGCAGAACAACGCCCTTG
TGAACAATTCACATAGCAAGCTGAATAACAGCAACGCAAATACGGATCTGCTTGGATTAAGCACTCCGCCATCAAATAATATTGGCAGTGGTAGC
AATAGCAACAGTACGCTCATTGATGTTTTGGGCGACATGTACGGCAGCAATAGTAACAACAACTCAAGTGCCGTGTACAACACGAAGAAGTTTTT
GTTCAAGAACAATGGTGTTTTGTTTGAGAACGAAATGCTGCAGATCGGTGTGAAGAGCGAGTTTCGCCAGAATTTAGGACGATTAGGCCTTTTCT
ACGGCAACAAGACACAGGTTCCCCTGACAGTAAGTAAATTAGTTTCTGAAACATTCCAGGCATTACATTGCTCTCTTTTCAGAACTTCAATCCTG
TGCTGCAATGGTCTGCCGAGGATGCGCTTAAGCTGAACGTGCAGATGAAGGTGGTGGAGCCAACCCTGGAGGCCGGCGCCCAGATCCAACAACTG
TTAACCGCGGAATGCATCGAGGACTACGCCGATGCGCCAACAATCGAGATCAGTTTCCGCTACAACGGCACCCAGCAGAAGTTCAGCATTAAACT
GCCATTGAGCGTTAACAAATTCTTTGAGCCTACCGAAATGAATGCGGAATCATTCTTTGCACGATGGAAGAACCTTAGCGGGTATTTAATAAGGT
GTCTTTTGATAATATTCAATATTAATTGTGCATTTGTAGTGAACAACAACGGTCACAGAAAGTGTTCAAGGCTGCACAGCCACTGGATTTGCCCG
GAGCCCGCAACAAGCTTATGGGCTTTGGAATGCAACTGCTGGACCAAGTGGATCCCAATCCAGACAACATGGTCTGCGCGGGCATCATTCATACG
CAATCGCAACAGGTGGGCTGCCTTATGCGATTGGAGCCGAACAAGCAGGCTCAGGTGAGTAATTTATTGTTAGATACTTGGAACATAATGCCTAT
TGCCTATTTCTCAAATTATCAATAGATGTTCCGACTGACAGTTCGGGCAAGCAAGGAGACCGTAACTCGGGAAATCTGCGATCTGTTGACGGATC
AATTCTAAGCCACAACAATCATGGACGGGGTGATGGAGACGGAGCTGCGAAGCCATGGAGCAACGGCAACCACTTTACAATGCACAATCCCAATT
ACCTAGAGAAATATCAAAGCATACAAGGCCCTAGAACTGTACGCGTTTAGTTATGCCAGGCACACTCCTACACTCTTCTTAAGTACCTTTCATCT
TCTCCAACAGCGAGTTGATTTACCCACTGTCCTGTTTATTTGAATATTATGTTTGTAAACCTACTCTTACTTTAACCATTTTCAATTTCATGTTC
CCAAACTTTTTTGTAAATGTTAAGCTCAAAAAGTTCATAGTAGAGAAACGAGAGAACATAATTAGATTATGTTTATATGTATGACAAATTATATA
TTGTTGCATCATTTCGAGGCAGTAGCAATTGGATATTATATACCTATATACAGATCTACATACATTCATACAAACCACATACATATACCTAGTAT
ATACGTCGTTGTAATAAAAACAGAAATCAATATAAAACAAAAGAGAAAAGCTTGCAAGGGAATTATTAAGATGCCTGCAAATGACAAGTATGCAA
ATCGTTATCTAAATATTTATACATATATTGATTATTGCAATTGCATCTAAACGAAATTCATGTTTAATGTTTTTGATTGTAAAATCCAATGGAGG
ACCGCAAGAGCAGAAATCTCATTAAATAATAGACAAATAATTAGACAGATCCACAAAATCTCCTTGATTAATCACTGTTGAGCAACTTAAAATTT
ATTAACGATAGGAAAAATTTCCCTATTGAAGAAAACGAAGCAAAAATTTCAGAATATTATTATACTTATAGCAGAATTTTTTGAATGATTCTGGG
TAATATTACGTTTCGTTTGTGTACCATAGATAAACTGAGAGGGGCTACTTCATGTTGTGCCGCTTCCTGAAGAGAAAGCGATCTTTGTAGCACCA
AGTATTAACTAATCTGAAGCAGCAGCAGCAGTAGCCGCCAGCCATAAATCTGCTAATGACTCTCTTCAAATGCGAGACGGCTGCCGATAAAGAAC
AAAGAATTGTAAACTAAAATATACACTATATAGATACTGATACTGAAAACCGATAATGGAAACTGACATCAAATACTTATTACCATTAAACTCTC
GATCCTTTCGTAAAAACCAATGTGCATGACAGCTGGAAATTTAGGCATTTCCAAAGTGCAATAGTTAAATGTTACAAAATTCCACACAAATTCCA
TTTAACACTCACAGACAAAACAAAAGCAACTGCAAGAGCAAGAAAACCAAGCCACAACTACATATAGCAAGTGCAGGAATTTAACTGTAAACGTA
AACCAATATGTATTTAAATAAATATAAATTGAAACCATTTGAAAGGTGTTTAAAACGTTTCCACGATCTGGATATAAACACTTGGCAAGCACAGT
TGTATTTTACGTATTTATCTTTATTACGATTAGCGCACGGGTTAACATAGGACCTAACAATAATTTTAGATTTAAATCAAATT
(SEQ ID NO: 457)

Exon: 1001..1318
Exon: 2107..2365
Exon: 3103..3314
Exon: 3524..3979
Exon: 4043..4632
Exon: 4701..5634
Exon: 5688..5971
Exon: 6025..6229

FIGURE SHEET 255

Exon: 6296..6873
Start ATG: 2326

Transcript No. : CT13966
CCCGCGCCCGCTAGATGGCTCCACTCTTAGGCAGCGAGAGCGAAGAAAAATCAATAGAAATTTTCATTTTAGTGAATTGCCCTGCACTTGGTAAT
AGTTAACAAACAAATTAGCGGCAAATCAGCGAGGCGAAGCTCCAGCGAGTTGGAGTTCCATAAAGTGCAACACGCAGGGTCAAACATTCCGCAGC
CAACACCCCGGATTCCGATTCCAAGCGAAGCCAACTTCAGAAGTCAGAGATTACTCTCTCTGCTCCGCCACAGAAATTCCGCAACGCTAACCGAT
TTTGTCCGCTGGCGAGTAAAAAAAATCGGAAAAGTCCCAAGGAACGGCCGAGATCCAATCGAAGTAAAAGAGCTTTGCAGAACCAGAGCGGAGA
GCAACTATATATCTTAGGGTCCGACGTCGAGTTCGAGCGATAAGAACGCCTCGAGACTCGGCCGCCATCCATTGACGATTTTCTTGCGCCCCCAG
TTTGCATAAAACCAGCGAAAATTAACAAGCTAACTACCATGGCGCCGGTGCGGGGGGATGGCATGAGAGGCCTGGCCGTCTTTATATCGGATATA
AGGAACTGCAAAAGCAAAGAGGCCGAAGTCAAACGCATAAACAAGGAGTTGGCCAATATACGAAGCAAATTTAAAGGAGACAAAACCCTCGACGG
CTATCAGAAAAAGAAATATGTCTGTAAGCTGTTATTCATATTTCTCCTCGGCCATGACATCGACTTCGGGCACATGGAGGCGGTCAATTTGCTGT
CCTCCAACAAATACTCAGAAAAGCAGATTGGTTACCTTTTCATCTCAGTGTTGGTGAACACCAACAGCGACCTTATTCGGCTGATCATCCAATCT
ATAAAGAATGATTTGCAGTCGCGTAATCCTGTGCACGTTAATCTGGCACTACAATGCATTGCCAACATTGGAAGTCGGGATATGGCCGAGTCCTT
TTCCAACGAAATACCCAAGCTACTCGTCTCGGGCGACACCATGGACGTGGTGAAGCAGTCGGCGGCGCTATGCCTGCTCCGCCTGTTCCGCTCCT
CGCCGGACATCATTCCCGGTGGTGAGTGGACTTCGCGCATTATCCATTTGCTCAATGATCAGCACATGGGAGTGGTCACAGCGGCCACCTCGCTG
ATCGACGCCTTGGTGAAGCGCAATCCGGACGAGTACAAGGGTTGTGTTAATTTGGCTGTTTCACGCTTATCCCGGATCGTAACAGCCAGCTACAC
GGATCTTCAGGATTACACATATTACTTTGTGCCGGCTCCATGGCTATCGGTGAAACTTCTGCGATTGCTGCAAAACTACAATCCAGTGACCGAAG
AGGCCGGTGTGCGGGCCCGCTTGAATGAAACTTTGGAGACGATTTTGAACAAGGCGCAAGAGCCGCCAAAGAGTAAGAAGGTGCAGCACTCTAAC
GCAAAGAACGCCGTGCTCTTCGAGGCCATCAACCTGATCATTCACAGCGACAGCGAGCCGAACCTTCTTGTCCGCGCTTGCAACCAGTTGGGACA
GTTCCTTAGCAATCGGGAGACCAACTTGCGCTATCTGGCTCTGGAGTCCATGTGCCACCTGGCCACATCGGAGTTCTCGCACGAGGAGGTGAAGA
AGCACCAGGAGGTGGTCATTTTGTCAATGAAAATGGAGAAGGACGTGTCCGTGCGCCAAATGGCGGTGGATCTTTTGTATGCCATGTGTGATCGT
GGTAATGCCGAGGAAATTGTTCAGGAGATGCTCAACTATCTGGAGACGGCCGACTACTCTATTCGTGAGGAAATGGTGCTCAAGGTGGCCATTCT
TGCCGAGAAGTACGCCACGGATTATACCTGGTATGTGGACGTTATCCTCAATCTAATTCGCATTGCTGGCGACTACGTGTCTGAGGAAGTATGGT
ACCGCGTCATTCAGATCGTGATCAATCGCGAGGAGGTTCAAGGCTATGCCGCAAAGACTGTTTTTGAGGCGCTACAGGCCCCTGCCTGCCACGAA
AACATGGTTAAAGTGGGCGGCTACATCTTGGGCGAGTTTGGCAACTTAATCGCCGGAGATTCCCGCTCAGCACCACTGGTACAATTCAAGCTACT
GCACTCCAAGTACCACTTGTGCTCGCCGATGACCCGGGCCCTTCTTCTGTCCACGTACATTAAATTTATCAACCTCTTTCCGGAAATTCGTACCA
ATATCCAGGATGTGTTCCGCCAGCACAGCAATCTTCGATCCGCAGATGCGGAACTGCAGCAGCGAGCTAGCGAATATCTCCAGCTTAGCATAGTG
GCATCGACAGACGTTTTGGCCACCGTCCTGGAGGAGATGCCATCGTTCCCGGAACGCGAGAGCTCAATTTTAGCAGTGCTAAAGAAGAAGAAGCC
CGGCAGGGTGCCGGAGAACGAAATTCGCGAGTCGAAGAGCCCGGCACCCCTGACTTCTGCAGCGCAGAACAACGCCCTTGTGAACAATTCACATA
GCAAGCTGAATAACAGCAACGCAAATACGGATCTGCTTGGATTAAGCACTCCGCCATCAAATAATATTGGCAGTGGTAGCAATAGCAACAGTACG
CTCATTGATGTTTTGGGCGACATGTACGGCAGCAATAGTAACAACAACTCAAGTGCCGTGTACAACACGAAGAAGTTTTTGTTCAAGAACAATGG
TGTTTTGTTTGAGAACGAAATGCTGCAGATCGGTGTGAAGAGCGAGTTTCGCCAGAATTTAGGACGATTAGGCCTTTTCTACGGCAACAAGACAC
AGGTTCCCCTGACAAACTTCAATCCTGTGCTGCAATGGTCTGCCGAGGATGCGCTTAAGCTGAACGTGCAGATGAAGGTGGTGGAGCCAACCCTG
GAGGCCGGCGCCCAGATCCAACAACTGTTAACCGCGGAATGCATCGAGGACTACGCCGATGCGCCAACAATCGAGATCAGTTTCCGCTACAACGG
CACCCAGCAGAAGTTCAGCATTAAACTGCCATTGAGCGTTAACAAATTCTTTGAGCCTACCGAAATGAATGCGGAATCATTCTTTGCACGATGGA
AGAACCTTAGCGGTGAACAACAACGGTCACAGAAAGTGTTCAAGGCTGCACAGCCACTGGATTTGCCCGGAGCCCGCAACAAGCTTATGGGCTTT
GGAATGCAACTGCTGGACCAAGTGGATCCCAATCCAGACAACATGGTCTGCGCGGGCATCATTCATACGCAATCCGCAACAGGTGGGCTGCCTTAT
GCGATTGGAGCCGAACAAGCAGGCTCAGATGTTCCGACTGACAGTTCGGGCAAGCAAGGAGACCGTAACTCGGGAAATCTGCGATCTGTTGACGG
ATCAATTCTAAGCCACAACAATCATGGACGGGGTGATGGAGACGGAGCTGCGAAGCCATGGAGCAACGGCAACCACTTTACAATGCACAATCCCA
ATTACCTAGAGAAATATCAAAGCATACAAGGCCCTAGAACTGTACGCGTTTAGTTATGCCAGGCACACTCCTACACTCTTCTTAAGTACCTTTCA
TCTTCTCCAACAGCGAGTTGATTTACCCACTGTCCTGTTTATTTGAATATTATGTTTGTAAACCTACTCTTACTTAACCATTTTCAATTTCATG
TTCCCAAACTTTTTTGTAAATGTTAAGCTCAAAAAGTTCATAGTAGAGAAACGAGAGAACATAATTAGATTATGTTTATATGTATGACAAATTAT
ATATTGTTGCATCATTTCGAGGCAGTAGCAATTGGATATTATATACCTATATACAGATCTACATACATTCATACAAACCACATACATATACCTAG
TATATACGTCGTTGTAATAAAAACAGAAATCAATAT
(SEQ ID NO: 458)

Start ATG: 538

MRGLAVFISDIRNCKSKEAEVKRINKELANIRSKFKGDKTLDGYQKKKYVCKLLFIFLLGHDIDFGHMEAVNLLSSNKYSEKQIGYLFISVLVNT
NSDLIRLIIQSIKNDLQSRNPVHVNLALQCIANIGSRDMAESFSNEIPKLLVSGDTMDVVKQSAALCLLRLFRSSPDIIPGGEWTSRIIHLLNDQ
HMGVVTAATSLIDALVKRNPDEYKGCVNLAVSRLSRIVTASYTDLQDYTYYFVPAPWLSVKLLRLLQNYNPVTEEAGVRARLNETLETILNKAQE
PPKSKKVQHSNAKNAVLFEAINLIIHSDSEPNLLVRACNQLGQFLSNRETNLRYLALESMCHLATSEFSHEEVKKHQEVVILSMKMEKDVSVRQM
AVDLLYAMCDRGNAEEIVQEMLNYLETADYSIREEMVLKVAILAEKYATDYTWYVDVILNLIRIAGDYVSEEVWYRVIQIVINREEVQGYAAKTV
FEALQAPACHENMVKVGGYILGEFGNLIAGDSRSAPLVQFKLLHSKYHLCSPMTRALLLSTYIKFINLFPEIRTNIQDVFRQHSNLRSADAELQQ
RASEYLQLSIVASTDVLATVLEEMPSFPERESSILAVLKKKKPGRVPENEIRESKSPAPLTSAAQNNALVNNSHSKLNNSNANTDLLGLSTPPSN
NIGSGSNSNSTLIDVLGDMYGSNSNNNSSAVYNTKKFLFKNNGVLFENEMLQIGVKSEFRQNLGRLGLFYGNKTQVPLTNFNPVLQWSAEDALKL
NVQMKVVEPTLEAGAQIQQLLTAECIEDYADAPTIEISFRYNGTQQKFSIKLPLSVNKFFEPTEMNAESFFARWKNLSGEQQRSQKVFKAAQPLD
LPGARNKLMGFGMQLLDQVDPNPDNMVCAGIIHTQSQQVGCLMRLEPNKQAQMFRLTVRASKETVTREICDLLTDQF*
(SEQ ID NO: 459)

Classification: known_flybase_gene
Gene Symbol: alpha-Adaptin
FlyBase ID: FBgn0015567

Celera Sequence No. : 142000013384593
ACAATGAATCTCAATTAGACTTACCCGTATATGTAGTAGAAGAAGCTAATCAGATAGACGGCCAGTTTAATCCAACCCTCACGCATGTTCCGGTA
CAAAGTATCGGTTTTCAGGACCGTGGTGGGATCATAAAGTCCGGGTCCCGACATCACAGGGCGGTTTTTGTAACTGAAAGCGATAGGGGTATTAC
AAAGCATGAGTGCTTAAGGGTGCTTATGTTGGGCTTGGGTGAATCTTGATCTCCTCGGATCTCAAATCACATTATATCACACGGTCAAATGAGTC
ACTTACCGCCAAATATGATAGGCTATGAGGGGTATGTTGATGCATAGCGAAAACCATTCGCCGCAGAACAAGAAGAGCAAGTTCAGAAAGATGTG CAGAAGGTATTCGGGCAAAACCAGCTGAAATGCAAACACATACATTACAGGGCGCACTGCGGGTGTAAGCAGTAAGTTTACTGACCGGATTGAGG
CTATTGCACTGATCAATTGGGTTCTTATAATCCGTTTTAAGTTCGTCGAATGCAATGACATGAAATATGGCGAAAAATATCAAGAATGCATCCCC
GATCAGGGCCACTATGTACGTGAAGGCGGTGAAGTTGAAGGCCATCTTGTAAAATCGCTGGAGCACGTCTTCCAGGTGCTAATCAAAGTGACTTG
CTAATTATTATCGTAAAATTCGGCTTTGCAATTGTAGCGCTGGGACTCACTTGTTTTTTTTTACAAGGGCGGCGATGATGACAGCTGTGCGCCA
GGGATGCACTAATCTAAACGATCAGGCAGCACAGATGTACGGTCACATTGCAAATGAGGCTAATAAATAATCAGCTATCCATTATAAATCAAATA
TAATTTCATTTAAAGAAGCAATTTTAATTTCTAACGAATTATAATGTTTTGTATTAATTTTAATTCTCTGGTAATTTTCTCTACGCACAAAAAAT
ACCACTAACAGTTAGCCGATGCGGTCACACTACATTTCCAAATCGAACCGCCATTTGTGTTGCATCTCGAAATCTGGAAAAAATTCGATCCAAGT
GTTCTATGAGCTTCTGTTTTTTAATAATAATAAATAAATAAATTCGATAATCAACTGACACCAGAAAAGAGCGGAACACAATGTCGCAGTTCAAT
TTTGTGAGCGATTTGCAGAATGCTCTCATCATGGACGGCGAGACGCGCGGACCTGCGCCCAGGTGGAAGAAGAAGCTGGAGGCGTCTCTAAATGG
AAGTGTGAATACCACTCGGTCGGTGCTATCCGTCTCGTACAACACCAGTTTCTCGGGTGTCCAGGCGCCCACGAAAACTCCGGGCAAGAGCAGCG
AGGGCAAGACCAAGAAGTCCAACACCACGCCCTCTAAGACGCCAGGAGGCGGAGATCGCTTTATTCCGAATCGGGCGGCTACCAACTTTGAGTTA
GCACACTTTCTGGTAAGGATTCCACTCATCCCTCCATCCCGCCCTGTAAGGGCATCCTTATTCCAGACCCCTTAAGAATTTATTGACCACCTGAC
CATCTATTAGGTGAACAAAGACTCCGGCGATAAGTCCGATGAGGAGAACGACAAGGCCACCTCGAGCAACAGCAACGAGAGCAATGTCCAGGCTT
CGGCTCACAAGGGCGACCGGCAGAAACTCATCTCTGAAGTGGCCCAGGTCGGTGACTCCAAGGGCGGGCGCATTTTGTGCTACCAAAACAAGGCT
CCCGCTGCTCCAGAAACACACAACAATCCCCTGAAGGTCGTGTACTCCATTAAGACACCCATATCCACAAAGAGTGGCTCACGCTATATACCCAC
CACATCCGAGAGGATTCTGGATGCACCTGATTTTATTAACGATTACTGTAGGTCGAAGAAAACTTTTCTTTTCTTTTTTTCTACTATTGATCTCT
TCCAGATTTAAATCTTATGGATTGGAGTGCCGACAATATAGTGGCTGTGGCCTTGGGCAGTTGCGTCTATTTGTGGAACGCACAGACCGGAAATA
TCGAGCAGCTTACGGAGTTTGAGGAGGGCGACTACGCAGGCTCGCTATCGTGGATCCAGGAGGGGCAGATACTTGCCATCGGCAACAGCACCGGT
GCCGTGGAGCTGTGGGACTGCTCCAAAGTGAAGCGTCTGCGAGTGATGGATGGACACAGTGCCCGAGTGGGATCCTTGGCCTGGAACTCATTCCT
GGTTTCCTCTGGCAGCCGGGATGGCACCATTGTCCACCACGATGTGCGTGCACGTGAGCACAAGCTTTCCACATTGTCCGGACACACGCAGGAGG
TTTGCGGCCTAAAGTGGTCCACGGATTTCAAGTATTTGGCTAGCGGAGGCAACGACAATCTGGTGAATGTTTGGTCGGCGGCCAGCGGTGGCGTG
GGAACTGCCACCGATCCCTTGCACAAATTCAACGACCATCAAGCTGCAGTGCGTGCCTTGGCCTGGTGTCCCTGGCAACCAAGTACTCTAGCCTC
TGGAGGCGGCACCGCCGATCGCTGCATCAAGTTCTGGAATGTGAACAATGGCACTTTAATGAAATCCGTGGACTCCAAGTCGCAGGTCTGTTCTC
TGCTCTTTTCTCGCCACTACAAGGAGCTGATCTCTGCGCATGGTTTTGCTAACAACCAACTGACCATTTGGAAATACCCAACAATGGTGAAGCAA
GCCGATTTGACTGGACACACGTCACGAGTTCTCCAGATGGCCATGTCTCCGGACGGCAGCACAGTGATCAGCGCCGGAGCTGATGAAACCCTGCG
TCTTTGGAACTGCTTCGCTCCCGATCCGTTGGCGTCCAAGAAGGCAGTTTCGACCAGCAAGGGCAAACAGAGCGTGTTCCGACAGAGCATCCGTT
GATATGCTCAGACCTTTAGAACTGTTTTTACCCCCTTGATTGCTAAGTTTAAGCTTCAATACTTACTACTGGTATGTTTTCCAGACTAGACAATT
ATTTCTTGAATGCATATCCAATTTTTATGTTCTCGTTTAATGTTTCGTACTTTGTAATTACGGATAAATCTCTGATTATGTGCCCCCGCCGACGA
TATATGAATAATTAAATTTTGTCAGTTACTTTTATTGCTTAGAGTTAAGTTTGTGTGCGTATAAATAAAATGCTTGACATTCTGCATCCTTGTAT
GCTTTATTTCGCTCTAAACATTTTGCGTTAACACAAGGAATTCTATTCGTTTCGGATTCCCACGTGCCGGGACAGTAAGTACATAAGGTTCCATT
TCCTGGATGCATTTTGAGAACGTGTGTGTCTAGGAATAATATTGCATACAATTCTGGGGCAGAAAAGGCGTGCTTCTGGGGACATCGATATAACC
ACATCGGGAATTTAAGTTGTGTTAATCATAGGTATGTTTATGTTTAGTCTAAATCGTATGTACAGATTGGATGGGCATTCAGGCAACTGTCATGG
GATTGCCACCGTTGTAGCTGACAAAATAGCGAGGATCACCAAAGCGATCGTACATCTGCAAGAACAAGAGGTTCGCAAGAAAAAAGCGGGTTAAA
TTAAAAATATTACAAAATTGTTAGGTACAAGAACAAAAGCCTCATTAAGCGATAAAATAAGCAAACAACATAGCAAGAACAAGTAAACAATAAAG
GGGGGCATACTTTCAAGTCTAAATAGAGTTACAAACCTTCTTTTCAATCCATTACAACATCGAATTCAACATTTAATTTTTGTTTGCTAATTTTT
TTTTGTAGAATAAAATATTTATTTTGCAACATTATTTCATTCAGTCAGAACATGAAAACATCAATTAGATTTAGCTAGCTTAGTACTACGGTTTA
TGATTCAATTTTGTATAATAGATTAGTTGGTCGATTCACGCACACGCGCACG
(SEQ ID NO: 460)

Exon: 1001..1437
Exon: 1531..1852
Exon: 1906..2852
Start ATG: 1126

Transcript No. : CT13999
CCATTTGTGTTGCATCTCGAAATCTGGAAAAAATTCGATCCAAGTGTTCTATGAGCTTCTGTTTTTTAATAATAATAAATAAATAAATTCGATAA
TCAACTGACACCAGAAAAGAGCGGAACACAATGTCGCAGTTCAATTTTGTGAGCGATTTGCAGAATGCTCTCATCATGGACGGCGAGACGCGCGG
ACCTGCGCCCAGGTGGAAGAAGAAGCTGGAGGCGTCTCTAAATGGAAGTGTGAATACCACTCGGTCGGTGCTATCCGTCTCGTACAACACCAGTT
TCTCGGGTGTCCAGGCGCCCACGAAAACTCCGGGCAAGAGCAGCGAGGGCAAGACCAAGAAGTCCAACACCACGCCCTCTAAGACGCCAGGAGGC
GGAGATCGCTTTATTCCGAATCGGGCGGCTACCAACTTTGAGTTAGCACACTTTCTGGTGAACAAAGACTCCGGCGATAAGTCCGATGAGGAGAA
CGACAAGGCCACCTCGAGCAACAGCAACGAGAGCAATGTCCAGGCTTCGGCTCACAAGGGCGACCGGCAGAAACTCATCTCTGAAGTGGCCCAGG
TCGGTGACTCCAAGGGCGGGCGCATTTTGTGCTACCAAAACAAGGCTCCCGCTGCTCCAGAAACACACAACAATCCCCTGAAGGTCGTGTACTCC
ATTAAGACACCCATATCCACAAAGAGTGGCTCACGCTATATACCCACCACATCCGAGAGGATTCTGGATGCACCTGATTTTATTAACGATTACTA
TTTAAATCTTATGGATTGGAGTGCCGACAATATAGTGGCTGTGGCCTTGGGCAGTTGCGTCTATTTGTGGAACGCACAGACCGGAAATATCGAGC
AGCTTACGGAGTTTGAGGAGGGCGACTACGCAGGCTCGCTATCGTGGATCCAGGAGGGGCAGATACTTGCCATCGGCAACAGCACCGGTGCCGTG
GAGCTGTGGGACTGCTCCAAAGTGAAGCGTCTGCGAGTGATGGATGGACACAGTGCCCGAGTGGGATCCTTGGCCTGGAACTCATTCCTGGTTTC
CTCTGGCAGCCGGGATGGCACCATTGTCCACCACGATGTGCGTGCACGTGAGCACAAGCTTTCCACATTGTCCGGACACACGCAGGAGGTTTGCG
GCCTAAAGTGGTCCACGGATTTCAAGTATTTGGCTAGCGGAGGCAACGACAATCTGGTGAATGTTTGGTCGGCGGCCAGCGGTGGCGTGGGAACT
GCCACCGATCCCTTGCACAAATTCAACGACCATCAAGCTGCAGTGCGTGCCTTGGCCTGGTGTCCCTGGCAACCAAGTACTCTAGCCTCTGGAGG
CGGCACCGCCGATCGCTGCATCAAGTTCTGGAATGTGAACAATGGCACTTTAATGAAATCCGTGGACTCCAAGTCGCAGGTCTGTTCTCTGCTCT
TTTCTCGCCACTACAAGGAGCTGATCTCTGCGCATGGTTTTGCTAACAACCAACTGACCATTTGGAAATACCCAACAATGGTGAAGCAAGCCGAT
TTGACTGGACACACGTCACGAGTTCTCCAGATGGCCATGTCTCCGGACGGCAGCACAGTGATCAGCGCCGGAGCTGATGAAACCCTGCGTCTTTG
GAACTGCTTCGCTCCCGATCCGTTGGCGTCCAAGAAGGCAGTTTCGACCAGCAAGGGCAAACAGAGCGTGTTCCGACAGAGCATCCGTTGA
(SEQ ID NO: 461)

Start ATG: 126

MSQFNFVSDLQNALIMDGETRGPAPRWKKKLEASLNGSVNTTRSVLSVSYNTSFSGVQAPTKTPGKSSEGKTKKSNTTPSKTPGGGDRFIPNRAA
TNFELAHFLVNKDSGDKSDEENDKATSSNSNESNVQASAHKGDRQKLISEVAQVGDSKGGRILCYQNKAPAAPETHNNPLKVVYSIKTPISTKSG
SRYIPTTSERILDAPDFINDYYLNLMDWSADNIVAVALGSCVYLWNAQTGNIEQLTEFEEGDYAGSLSWIQEGQILAIGNSTGAVELWDCSKVKR
LRVMDGHSARVGSLAWNSFLVSSGSRDGTIVHHDVRAREHKLSTLSGHTQEVCGLKWSTDFKYLASGGNDNLVNVWSAASGGVGTATDPLHKFND

HQAAVRALAWCPWQPSTLASGGGTADRCIKFWNVNNGTLMKSVDSKSQVCSLLFSRHYKELISAHGFANNQLTIWKYPTMVKQADLTGHTSRVLQ
MAMSPDGSTVISAGADETLRLWNCFAPDPLASKKAVSTSKGKQSVFRQSIR*
(SEQ ID NO: 462)

Name: fizzy
Classification: cell_cycle_regulator
Gene Symbol: fzy
FlyBase ID: FBgn0001086

Celera Sequence No. : 142000013384668
GGGCTATCCGGAGTTCGGACGCCTGCTCAATGAAACTGGTCGACCGATGGTATACTCCTGCAGTTGGCCCGCGTATCAGGAGGATGCAGGAGAAA
TGCCCGATTATGAGTCACTCAAGCAGCACTGTAATCTGTGGCGCAACTGGGACGACATCGAAGACTCGCTCGAGTCCCTTATGCAGATCATTGAC
TACTTTGCCAAGAATCAGGACAGGATTCAGCCGCATGGCGGACCAGGACATTGGAACGATCCAGATATGCTGCTGCTGGGAAACTACGGCTTGAG
CTACGATCAAAGCAAGCTGCAGATGGCGATTTGGGCCATTATGGCAGCTCCTCTAATTATGTCCAATGATCTGGCTGCAGTGCGTCCCGAGATCA
AGGCTATACTCCAGAATCGGTTGGTTAAGCTTCGATATCTTATCTTCTTGGACTTATTGGTAAACTTTTGTTATTTGCAGTGCGGTTATTGCTGT
GGACCAGGATGAGCTGGGCATCCAGGGGCGCCGTGTTTTGTCCCGCAACCAAATCGAAGTCTGGAAGCGTCCCATTACGCCAGTAACCAAGAGTG
GACATCACTCCTATGCTGTCGCCTTTGTCAGTCGCCGAGATGATGGCGCTCCCTACAGGATCCCCTTCACGGTCAAGGAGCTCGGATTGACGAAT
CCCAAGGGTTATAATGTGCAGGATCTGTACGATGCCAGCAGCAAGTTGGGCGTCTTCCAGTCTGAGAGTCAGTTCATCACACGCGTCAATCCCAA
TGGTAAAATCCGTTGCAAAACACTAACTAGCCCTGACTTACTTCATTTTCCCCTCCCCCAGGCGTAACTTTCTACAAGTTTACAGCGTTGTAAGC
CCAAGATATGCAAATCAGCCGCTGCCATCAAATCGAATATGCTCTTATATACACACTATTTCCACATTGTCCATTGACGTTGCATCGATGATCTG
TGTAATAAGTTAATTCCGACAATAAATACCAGGTAATCACTGAAGAGTTTGACTTTGTTGATTTTTATTGTTTATTAAACAATTGATTGTGTGCA
TTACACACAGGTATAAGTATTGTACAATTATAGGCATAGATTGCAGTACCGACGCTAGTTAAGACTTGTTCCATGATATAAATAAGGTCTGACTG
GATGAAAGAGTTAATTCGCAAGCTTGTATAAATAAGAAGTGTAGTACTATATACGCGACAAGGACCCGAATAAGAGCAAAAAGGATAGCGACCCC
TCGGGATCATACCAGTTATAAATAGATACCATCTACAGCTACTGCTTACATGGGTTTGGTCGAGAGAGTTAGAGTTATTGTCAAGTTGTAGGCGA
AACCGAAACCAAACCGAAGGAACCATAGCCCGGGGTTAGTGCACCCCATTGCTGATGGTCGGTGTGCGCTCGTAGGTGCGTCTATGCAGCGCATC
CACGTCCTTCAGGTAGTAGGTGCCGGGAAACAGTGCGGAGATGCTGCCCGTTGGCGTGTAGGGCGCCGCATGGTTGTTCTTCTCCCGCACCTCCA
TCAGCGCGGAGAACTGCTCGGGCGCAACCTTCTCCCGTGAATTCAGCAACGGCTGCACGTAGTCCAGCTGCGAGACGAACTTTTCGAAAGCAGCT
GCATCCTGGGTCACGCTGATCGAGTACATGGAAGCAGCCAGTCCGGATCCGTAGGAGAACAAACCAATGCGCTTTCCCACCAGCTCCTGGGCTGG
TCCGCTAATCAACAGAGACACCAAACCGGAGTACACCGAGGGTGTGTACATATTGCCCACTTGGTTGGCCAGCAGCAGCGATTTCTTGGTCTTGC
TGGCAAAGATGTTGGCGGACTGCGTCATGAAGGCCTTCTCCACATCGCGATCAAAGTAGGTGCTCTCCAGGGTAGCGGTATTAAAACGTTCCAGG
TCGGGAAACTGCTTCGTTCGCTCCTCCTCACTGCTCAGCAGGAAATCGTTGAAGCTCAGGCGACCCACAGATTTTTGCACCAACTTGCAGAACGG
TGTGTGGAATAGGATAGCATCGAAGGTGCTCAGGCTGGCCGGCTGCTTGGAAGTATCCTTCTGCTGCTGGTCGAACTTCTTGCGATACAGCCTGT
AGCAGGTGTCCAGAGCAGAAAGGTAGCACTGAATAGAGAGCTTTCCATCTACCGTTGGGTATTCGGAGCTGAGGTCCGGCTTGTAAAAGTCGTAG
GCGTGCTCCATGTGCGTTGCGCGTAGTCCACGATCGAGGATAAGCGGCGCATTTGGACCCACCAGCATAGCCACAGCACCCGCACCACCAGTTGG
GCGCGCTGCACCCTTGGCGTACACGGCGATATCAGCACAAACGGCCAAAGCCAGGCGGCCGTCCCAGCTAGAAGATTCCACCCAATTGACGGCAT
TGAAGAGCGCCGCCGTGCCGCCGTAACAGGCGTTCGTGGTGTCGATGCCCTCGATGTCCGTGTTCCCGCTCTCGGCGAACAGCTGCATCAGCACG
GACTTCACCGACTTCGACTTGTCCACAATGGTCTCGGTGCCCACCTCCAGTCGTCCGATCTCCGAGTGCTTCACATGTTGCCGCTCCAGCAGGCG
GCTCACAACCGTCAGGCAGAGAGAGTTGACATCCTCGCGGTCCGAGCAGAAGCCCATCTTGGCCTGGCCCAGGCCAATTGTGTACTTGCCCGCGG
AGGCACCATCGAAGGTCTCCAGCTCCGTTTGGTCCACGTACTGGGAGGGGAAGAGAATCTCGATGGCGCGTATGCCAACGTTCTCGGGCCAGTGG
GATGCCATGATTGTATCCGGTTATCTATTTAATCCTGAGCTCTGTAAGAGAGACAATTTGTATACTTTTAGTGGGAGCTTTGGCATGAGAGTAAA
TATTTAATTCAATATCTTTGTTATTAACAACTATAACAATCACTATTTGCGTTTCGAAATTGCTTCATGATGTTGGGAGCTAAGGCCTTGTTTAA
TTTAATTTAAGCAGAGTTCTCGATGTGGCCCGAATTCCACTGCCAATTGGCATTGGGAAACTTTCTCCCCGCGCAATCACGGCGTATTTATAATG
CTTACAAATTGGACGAGGGCAGAGACAACCTGTTGCACGCTCGAGCTGCGTTGGACGTGTGTAAGCCAGTGACTTTGGCTGCGGCTGAAGAAGTC
ATCAAAGTCTGCCAGCCAGAGGCCCCCGTCTTGGGGGCCAACTGATTTCCCTGGCTGAGAAACTGAGCGTGTAGAGAGAGAGAGAGAGAGGGAGA
GAGAGCCGCCGGAGCGGAGAAAGTTTCCCCCGCTCAGGCGAGCTCCACAAAAGAGAACACTAAACCGCTGTGAAGTAAGCCAAAACACACGCATC
GCAATAAATGTAAGCCAACAAGACAAGCCCAAAGAGCCAAAGGGACAGGGGCGTGGATGCTGTGGCTACACGCAGAGAATTTATGATTACATTTA
TTTACAATAGATAATCATTTCTTTTAAACTTTTTTGTCAGAGAACAAGCTACAAAAATGATTACTTTAACACAATAACTCTTTTTTCAAAACCG
CTTCCCCTGAAACTTCTCTACATTTTCACACATTTTAATTTCAGTTAGGCGCAAATTATAATTAAATCAAAATGATGATCGAAATATTATGATTT
CCTATCGAAATAGAATGGAATTTTGCTCGGTGGAGCATTGTGGGACAGGCTGGGAGCGTCTTCACCCATAAGTGGGTCATGCCCACCAAGCACTA
AGCACCAACCACCACTCTCCCTCAATCACACGCGTCCATATTGTATAACCGATAAGAGGTGCGAGTGTGGCCCAAACCCGAAAAGCGGTTGACAT
ATTTACCGTTACGTTTAGCACCTGCGACTACTGGCCTATTGACTATAGATTTTCACTTTTCGGCCCGGAACTTTGTGGATTTGTGAAAAAAGGCT
GGGTAGCGCGAAGCTCACTCGATCGGATCTCTCCGCGGACTGACGGCACTGGAGGCGCTGCACTGGCATATGAATATGACCATGACGACGGAATT
GGCAGTGGAGAAGCAGACACCTAGCCAACGAAGCCACCTAGCCACCGAGCAAACACAGAGGCGAGAATAGGCGCTGTAAGTCAATGCCAATTGCT
GAAAGCGCTCGGCGAACAAATAGCGATCGTGCATAATTACGGGAAATATTTATCGCTTAGATACGGCCAGCGAGCACGAAACACAATCGTCGGGG
ACTAAGAAGCCGCCAGACTATATAGATATGCACATCGATAGTCGTGGCCTTTTGCGATGGGGTAAAGATCAAAGGCTGTCCATCGCTGATAAGGC
CGAAACAAAGCGGCTTCCTTAAAAATGCCACCGAATAAGATGTGACACTCTGTCCATTTCAGTGACAAAAACTGGGAAGTGACTTCCAATAGCTT
TTCTCCGATTAATTACTTAAGACGTGCCCTTAGGAATTATTAATAGAAAATTATTTATAATTTGAGTTCTACTAATTTTCCTACTGGTATAACTT
AAATTGGATTATCATCTTTTCTGAACACTATCTTGAAACGTGATTTCAAATCACCTGAACACAATTGGTAATTGATAAAATATTCTACAGAAATC
ACTTAAAGTAAGATAATAACAAGACTACTTTAAGTAGTTGTGATATTACTTGAGTCGTACTTAAGTTAATTAATACAGTTTAGTTAAAGTAAGTA
AAATTAACAAATAAGAGAATACTTTGTCCTATTGTGCAAAAGAGTATGAATCATTATCCAAAGTCATGAAACTCTAATTTCAAGCAATTTAAGTG
ATTTAAGTCATTAATTCCTCGAGTGCCTGCGTGGAATACAGCTCACCCGGTGTTCCTAAGCAGCCCGTGGATTTAAGAATGGAAATTGATGCGCT
GTTTATGCGGAAAAGGAGTCATCGAAGGGAAGGGAACGGGGCACTGTTGTGGTTTTGTGGGCTTATTTTTAGCACT
(SEQ ID NO: 463)

Exon: 3921..3822
Exon: 2796..1001
Start ATG: 2763 (Reverse strand: CAT)

Transcript No. : CT14107

CCGATCGAGTGAGCTTCGCGCTACCCAGCCTTTTTTCACAAATCCACAAAGTTCCGGGCCGAAAAGTGAAAATCTATAGTCAATAGGCCAGTAGT
CGCAGAGCTCAGGATTAAATAGATAACCGGATACAATCATGGCATCCCACTGGCCCGAGAACGTTGGCATACGCGCCATCGAGATTCTCTTCCCC
TCCCAGTACGTGGACCAAACGGAGCTGGAGACCTTCGATGGTGCCTCCGCGGGCAAGTACACAATTGGCCTGGGCCAGGCCAAGATGGGCTTCTG
CTCGGACCGCGAGGATGTCAACTCTCTCTGCCTGACGGTTGTGAGCCGCCTGCTGGAGCGGCAACATGTGAAGCACTCGGAGATCGGACGACTGG
AGGTGGGCACCGAGACCATTGTGGACAAGTCGAAGTCGGTGAAGTCCGTGCTGATGCAGCTGTTCGCCGAGAGCGGGAACACGGACATCGAGGGC
ATCGACACCACGAACGCCTGTTACGGCGGCACGGCGGCGCTCTTCAATGCCGTCAATTGGGTGGAATCTTCTAGCTGGGACGGCCGCCTGGCTTT
GGCCGTTTGTGCTGATATCGCCGTGTACGCCAAGGGTGCAGCGCGCCCAACTGGTGGTGCGGGTGCTGTGGCTATGCTGGTGGGTCCAAATGCGC
CGCTTATCCTCGATCGTGGACTACGCGCAACGCACATGGAGCACGCCTACGACTTTTACAAGCCGGACCTCAGCTCCGAATACCCAACGGTAGAT
GGAAAGCTCTCTATTCAGTGCTACCTTTCTGCTCTGGACACCTGCTACAGGCTGTATCGCAAGAAGTTCGACCAGCAGCAGAAGGATACTTCCAA
GCAGCCGGCCAGCCTGAGCACCTTCGATGCTATCCTATTCCACACACCGTTCTGCAAGTTGGTGCAAAAATCTGTGGGTCGCCTGAGCTTCAACG
ATTTCCTGCTGAGCAGTGAGGAGGAGCGAACGAAGCAGTTTCCCGACCTGGAACGTTTTAATACCGCTACCCTGGAGAGCACCTACTTTGATCGC
GATGTGGAGAAGGCCTTCATGACGCAGTCCGCCAACATCTTTGCCAGCAAGACCAAGAAATCGCTGCTGCTGGCCAACCAAGTGGGCAATATGTA
CACACCCTCGGTGTACTCCGGTTTGGTGTCTCTGTTGATTAGCGGACCAGCCCAGGAGCTGGTGGGAAAGCGCATTGGTTTGTTCTCCTACGGAT
CCGGACTGGCTGCTTCCATGTACTCGATCAGCGTGACCCAGGATGCAGCTGCTTTCGAAAAGTTCGTCTCGCAGCTGGACTACGTGCAGCCGTTG
CTGAATTCACGGGAGAAGGTTGCGCCCGAGCAGTTCTCCGCGCTGATGGAGGTGCGGGAGAAGAACAACCATGCGGCGCCCTACACGCCAACGGG
CAGCATCTCCGCACTGTTTCCCGGCACCTACTACCTGAAGGACGTGGATGCGCTGCATAGACGCACCTACGAGCGCACACCGACCATCAGCAATG
GGGTGCACTAACCCCGGGCTATGGTTCCTTCGGTTTGGTTTCGGTTTCGCCTACAACTTGACAATAACTCTAACTCTCTCGACCAAACCCATGTA
AGCAGTAGCTGTAGATGGTATCTATTTATAACTGGTATGATCCCGAGGGGTCGCTATCCTTTTTGCTCTTATTCGGGTCCTTGTCGCGTATATAG
TACTACACTTCTTATTTATACAAGCTTGCGAATTAACTCTTTCATCCAGTCAGACCTTATTTATATCATGGAACAAGTCTTAACTAGCGTCGGTA
CTGCAATCTATGCCTATAATTGTACAATACTTATACCTGTGTGTAATGCACACAATCAATTGTTTAATAAACAATAAAAATCAACAAAGTC
(SEQ ID NO: 464)

Start ATG: 134 (Reverse strand: CAT)

MASHWPENVGIRAIEILFPSQYVDQTELETFDGASAGKYTIGLGQAKMGFCSDREDVNSLCLTVVSRLLERQHVKHSEIGRLEVGTETIVDKSKS
VKSVLMQLFAESGNTDIEGIDTTNACYGGTAALFNAVNWVESSSWDGRLALAVCADIAVYAKGAARPTGGAGAVAMLVGPNAPLILDRGLRATHM
EHAYDFYKPDLSSEYPTVDGKLSIQCYLSALDTCYRLYRKKFDQQQKDTSKQPASLSTFDAILFHTPFCKLVQKSVGRLSFNDFLLSSEEERTKQ
FPDLERFNTATLESTYFDRDVEKAFMTQSANIFASKTKKSLLLANQVGNMYTPSVYSGLVSLLISGPAQELVGKRIGLFSYGSGLAASMYSISVT
QDAAAFEKFVSQLDYVQPLLNSREKVAPEQFSALMEVREKNNHAAPYTPTGSISALFPGTYYLKDVDALHRRTYERTPTISNGVH*
(SEQ ID NO: 465)

Classification: enzyme

Celera Sequence No. : 142000013384045
ATCAGACACACACACACACATTCACACGTAACTCTAAATACTATATGTATAAATGAAAGTTCTTTTTTTGTCGGCTTCCCACATTCCCCGATTGT
TCAGATATTGGCCATAGGCGGGGCCTTTCCTGGGGTTTTTCTTCCACACCCAGATAACGGCTATCTGGTACTGGTTATAGTGACTGCGTTTGGGG
CGCTAAAGGCTATAAATCGTCTAGATTTATTTACAATTAATTTTATTTGATTTGTCATACGTTTCTCAGGCCGAATTTCATTTGCAAAGTTCTAA
TTTCTGCTGTTTAATATAATGCACTTGCGTTTTAAGGCAATTTATGGATTACTATTTGCGAAAATCAAAATTTCTTTTTTTGCAATTAACATTAT
ATAAAAAATGTTTTTTTAATTAGTCGAAATCATTTTTAAAATGTTAATTCTTGTATGTCATAAGCGCAAAAGTATGAGTTGTACTTAATCTAAAT
TCTAAAACAAGTTAGTCATTAAAAATACTACGAAACAATAACTCAGAACAGAAAAATTTAAACATGTTATCTAGAGCAATATAGAAATTAATTTG
AGCAATATTACATCAAATATCTCAAGTTTTAGAAGTTCTTCCACATTTATTTTACTGTGTACGCACAATATCATACTTATATGCTTATGTGTATA
TCTTTCTATCCGTGATCTGCCCCCCAGAGACCCCTGGCCCCGCCCCCACCCTGTGTAGCCCCCTTGCTGATAGCTGTGTTGTTGTTTTTGTGGCT
GCTGCTCCCCCACATAAAGCTGACAATAAAAACAAAACTACGCTCACTCATTCACACACTCATGCCGTCACACTCGCAACCCAGAGACGCGCTCA
CACTTGCACTCACATCACACACACACACAATACACACACTCACACACTATCTGCTGTAACTAAAGACCCAACAAAGCGAATATGAATATTTTGCA
CAGAATTTTGCGCTTTGTTCTCTTCTCTTCTCGTTTTTTTTTTTGTTTTTGTTGAAGTTCTTCGCGTTTTTGTTTTGGGTGGGTTCAAAGTTCTT
AGAGCAGGGCGCACTTGTGCCGCTTGGGTCCTCGAACGACAGGACATAGCACGGATCGTATGGCCTCGTCGAAGACCGTCTTCAGACCCTTTTGG
GTCAGGGCCGAGCACTCCAGATACTTGACCGCAGCTATTTCCTTGGCCATCGCCAGTCCTTGGGGATAGGTGATCGGTGTTAGCTTCTTGTCCTT
CAGCTTCTCGATCGTCTGCTTATCGTCGCGCAGATCCAGTTTGGTGCCGACCAGGATTATCGGCACACTCGGGCAATGATGACGCACCTCGGGAA
ACCATTTGGCTCGCACATTCTCAAACGATGCCGGATTCACCAGTGAGAAACAGATGAGAAAGACATCCGTTTGCGGATAGGATAGCGGCCTCAGG
CGATCGTAGTCCTCCTGTCCAGCCGTATCCCAGAGGCCCAGATTGATGGGCTTGGCATCCACCATCACATTCGCCGAATAGTTGTCGAACACCGT
GGGTATGTACTCGCCGGGGAAGGCGTTGGTCGTATAGCTGATCAGCAGACAGGTCTTTCCCACCGCTCCGTCGCCCACAACCACACACTTGATGG
CCTGCATGATGAAGGCTACTGTACTGGTGGTACTACTGGGCAATCGATGGGTTCAGCAGCTCGATGGGTTGCTTGTGCGCTGGGGGCAGAGGGTT
TTTCAGTGGATCAGCTGGTTTCGTGCTCGATTTCCAGTGGCTCAACTGGTTTCTTTGTGGCAGCTTAACTTATAATTACTTTGGGGTAATTCAT
TCAATTCAGTAGGTCAGACAGTTTTTGAATGCTTCGATATTTGTACTTTTGAACTATTTTGTACTTTTCTTTTTTCTGTTCAACAGACAAATTTT
AGTCACACAATTTAGTTTTGCCTTGTATCGCAGCTCAGCTAGTTTTTCTAATTGTATAGCTTTTGCTTTTCGCGTTGGCGTTTTGCTTTTATTGT
TTTTTTTTTTGGCGATTATACAATAATTTGCTCACGCACTAATACAAATTCTGCCCACACACACACACACATTCAAGCAATCGCGTACAGAGAG
AGATGCGAATTTGAAGTGGAGTTTGATTTATCGCGAAAGTTGTCAAATCAATATTCTTAATTGAAAGCAGAACCGTGACGGCGTTCTTTCTGTTC
GGTCGGTATATTATTTATGAATTAATTGGGCCCGCATATGTGGGGATTTGCTGATTTTCTGTGGCAGAAACGGAAAAAACACGCCCAAACGCTGT
GAAATCTTCGCGGCGATTGAAGAAAATTTCTGCCTCCGCTGGCAGTTGTTGTACTTGTTTTTTCACTGTAGTTTTCGCTCTTTCAACTGGCTTGT
ACGGCTGTCTCGCTCGTTCGCGTGCGTTAGTCGCTTAAACGAAGCGCTGCGCGCATACGCTCTCCCACACAAAGAGCGAGCGAGCGAACGTGAGC
GAGAGCGGCACTGGCACAGTGCAGTCCCATAAAATTAGTCACAGTGAGTCATTCGCTCGGTGACGTTAGTCGTGGCAATCCACAGAGAGCAGAGC
GAGACAGAGATAGTGAGTCTCTTTACTTGACCTTGCTTTGGTCGTTTTTGTAGAGTTTTCTATATTCGTTCGACGGTTTTCCACGAATTTCCCGA
CCGTTGCTGTTGTTTTGAGCCAATTTCCACGCGACTAGAGGCTATCAGAGATGTGCGGTACCCAACTCAGGTACAAATCGCCCGTAGCTTATCGC
GGTACAATTACAGTGCCACACCAAAAACAAGCAAAACGTTGATATCGCGCGATATAAATATTAATTGAACAATATTTTTTTATTGATGAATCAA
TTATGTGACCTAAATATGTGTCACAGTCTTTGGATGAATATACTTAAATGGAAGTATTCATATTTTAAAATTGGAAACTCAAATTTAGATTCTGG
AATTACTTTTAATTCTCCTTAATTCGGGCCATATTAATTTACGACCGTTACATCCCATCTAATTCTTAAACGAATTATTAAATTTTTCATGACCA
GCGATATTTGCTGCCGTTGACTGTTTTAATGGACCACAAAATTGCGTGTGTCGGCAAAAACCAAAGCCCAAGGAATAACAAACAAATAACATTGG
CAAACAGTGCAAAATATCGACAGTAAAAACCGAAAAGCAAAAACAGAACCCAAACCGAATCCACCGAATCCGCCGCATCCGCATTCAGCCAAAAG
TGATAGCCGAAATATTTCGTGTTTGTGTTTTGGCTTCCGCCCCACCAACCAGAAGCCCAAA
(SEQ ID NO: 466)

FIGURE SHEET 259

Exon: 2291..1001
Start ATG: 1622 (Reverse strand: CAT)

Transcript No. : CT14366
GCGAAGATTTCACAGCGTTTGGGCGTGTTTTTTCCGTTTCTGCCACAGAAAATCAGCAAATCCCCACATATGCGGGCCCAATTAATTCATAAATA
ATATACCGACCGAACAGAAAGAACGCCGTCACGGTTCTGCTTTCAATTAAGAATATTGATTTGACAACTTTCGCGATAAATCAAACTCCACTTCA
AATTCGCATCTCTCTCTGTACGCGATTGCTTGAATGTGTGTGTGTGTGTGGGCAGAATTTGTATTAGTGCGTGAGCAAATTATTGTATAATCGCC
AAAAAAAAAAAAACAATAAAAGCAAAACGCCAACGCGAAAAGCAAAAGCTATACAATTAGAAAAACTAGCTGAGCTGCGATACAAGGCAAAACTAA
ATTGTGTGACTAAAATTTGTCTGTTGAACAGAAAAAAGAAAAGTACAAAATAGTTCAAAAGTACAAATATCGAAGCATTCAAAAACTGTCTGACC
TACTGAATTGAATGAATTACCCCAAAGTAATTATAAGTTAAGCTGCCACAAAGAAAACCAGTTGAGCCACTGGAAATCGAGCACGAAACCAGCTG
ATCCACTGAAAAACCCTCTGCCCCCAGCGCACAAGCAACCCATCGAGCTGCTGAACCCATCGATTGCCCAGTAGTACCACCAGTACAGTAGCCTT
CATCATGCAGGCCATCAAGTGTGTGGTTGTGGGCGACGGAGCGGTGGGAAAGACCTGTCTGCTGATCAGCTATACGACCAACGCCTTCCCCGGCG
AGTACATACCCACGGTGTTCGACAACTATTCGGCGAATGTGATGGTGGATGCCAAGCCCATCAATCTGGGCCTCTGGGATACGGCTGGACAGGAG
GACTACGATCGCCTGAGGCCGCTATCCTATCCGCAAACGGATGTCTTTCTCATCTGTTTCTCACTGGTGAATCCGGCATCGTTTGAGAATGTGCG
AGCCAAATGGTTTCCCGAGGTGCGTCATCATTGCCCGAGTGTGCCGATAATCCTGGTCGGCACCAAACTGGATCTGCGCGACGATAAGCAGACGA
TCGAGAAGCTGAAGGACAAGAAGCTAACACCGATCACCTATCCCCAAGGACTGGCGATGGCCAAGGAAATAGCTGCGGTCAAGTATCTGGAGTGC
TCGGCCCTGACCCAAAAGGGTCTGAAGACGGTCTTCGACGAGGCCATACGATCCGTGCTATGTCCTGTCGTTCGAGGACCCAAGCGGCACAAGTG
CGCCCTGCTCTAAGAACTTTGAACCCACCCAAAACAAAAACGCGAAGAACTTCAAC
(SEQ ID NO: 467)

Start ATG: 670 (Reverse strand: CAT)

MQAIKCVVVGDGAVGKTCLLISYTTNAFPGEYIPTVFDNYSANVMVDAKPINLGLWDTAGQEDYDRLRPLSYPQTDVFLICFSLVNPASFENVRA
KWFPEVRHHCPSVPIILVGTKLDLRDDKQTIEKLKDKKLTPITYPQGLAMAKEIAAVKYLECSALTQKGLKTVFDEAIRSVLCPVVRGPKRHKCA
LL*
(SEQ ID NO: 468)

Classification: enzyme
Gene Symbol: Rac2
FlyBase ID: FBgn0014011

Celera Sequence No. : 142000012746884
TCGTTTATCTTTGGCAGCGCAGCCGTTCTTGTAAACATCCTAAAGGCTGACCTAAGCAGATTTGACTGCCCTCTTTCAACGCTACCTAATCTTAA
GAACCCAAGAGCGAGGCTCTCCCGAAAATACAAATATTGTTCAAATACTGAGGCTTCTCCTCAATCCAATTTGCATTTGATTTTTAGTCTTAAGC
TGAGATCCAAAGAATAAAGTCGTGAAACTATTTCTCCTAAAAACTATTTTTTATTTCTTGGCGTTGTCCTTAGTCAACTGACGGGACATTAGTTC
GACTCATAAATAAAACAACAATTTTACTATATATATACTACATAATAGTCATACCCATGGGGAAACCTCTTACTTCTCGGCTATCGCAAGGAAAG
TATATGCCTGAACTGCGCTATATAGAGAAAAGCGAAAAGCTCTCGAGAATTGGCACACGACCGATAAGCCCGCCGAAGCAATCAATGGACAATTG
ACCTTCGTAATTGAAGGGGGGCAGGTTGTGGACCACTCACCTAAGCTCATGGCGGTCTTGAAGTATTCCGGCGGAACATAGCGTCCGCCCATGCG
CAAATAGGTATCGCAATCGGACACATAGCTGGGGCATTCGGCCTGCGGACAGGGGCACGTGGATGAGGACGGTGGACCGCAGCCGGTGCTGGCTA
GTGGCATGTATACCGAGTTCCCGTTCCCATGGCACTCGATGCCCAGTATTACGGATTCCGCAGAGCTGTTCTTCACCAGTAGCTGCAGCTTGAGC
ACGGCTATCCAGAATTTCTTGAGCTCGCCGAAGGTGAGTTTGTAGCCCAGTTTGTAGCGCATATCACGTACATCCTCCTCGGTGAGGGAGAGCAG
CACCTCGCCGTCGATGGCCTCCTGGCGCAGGCAGTCGAGCAGTGTTCTCGAAAAGTGCTCCATGCAGGTGGCCCAACTGGTCACATTCTCGATGG
ACCACTGGGCCACGAGTAGCGGATCCACGGGCTCTGGATCTGGCGATCCATTGGTCAGGTGCTTATCTGTCGCCGCGTCGAGGTAGTGCGTCCGG
GTCTCCTGATCCATTGTGACCAATCCACCGCCCTCGGAACGTGGCTGAGTCACCGGATCGCCAATTTCACCGTCGCACATCGCGCTTTCTTTTTT
TTCCGTTCGATGTTCTTCTGGCTGTTTCTTATTCGTTCCAATTTTGCGATTTATCCAAAATCCAAAACAATTGTGCGGCCGAACTCAGATGGAGT
GCAACATTTTTTCACTGCTGGCTGCTGTTGCTGCTGCGGCGCATAATTAACACCTCACTTATTGCGCGTCCAGCGTTTGTTGATGTAAAAGCACA
TTTAATTTTTGGTTTGGTTACTTGTTAAATTCAGACTACTCAGTTGTTCCGTTCAGAGAGCAAGCGAGAGAGCAGAGCGGAGTCAGCAACTATGC
TGGGGGCGGGAGCGAGATAACAAGGCCGAACAGCTGACTTCGGCCATCGATAGTTTTTGGACAACGCCAACGCTATCGATGAACAGTTACTTCGG
TCTTAACTGCGTGTTCACACCGAAAAATTTTCGAGAATTTCGCTCTCGTAAAAGTCAAAAGGTTTAAAACTCTTATCGTTAGCTTAATATTATTT
TAAATAAAACAATTTGAGGTGTCTGGCGAGTAGAAATTATTTAAATATTAACGCTTGACTGATATAAATCTCGTTCGATATATACGAAACCATGG
TGAAAATGTGGAAGAGTGGAAACGGCCTCCAAAGCGAAGATATCGAAGCCACAGCTTCGCTTCGTTAGCATTTTGCGAGCGGCAAAGTGATTTAA
TTGTCCTCGTGCGAATGTCTAGACAGAAGTAATCCTCGAATAATATGAAGAAAGCCAAGCCGCTGCTGCACGACCATCTAATAACGATCCGAGTA
AAGAAGGTGTGTCCAAATCCGTTGTTTATATCCACAAACTAGCCAGCTGCCCGATAGCCGGTAAATTCCCATGAAAGCAGCACAAAAAAAAAAAA
AAAAACACACAAAAACCCTTTGCAGGGCGGCGATTTTGGGCAAGGGAAAACAAGGTTAGGTCGCAGGCTACCCGCATCGTGTGCTAATTGCGTTC
TACTTTCGATTTCAGTATCTGGAGGAGCACATCGGGGAAACCTACCTGGATGTGAAACAGATGACCAGGGAGTTGATGCAAAAGTATCCGGAATA
TTCACGACGCAAATTCGGACCATTCAGACAGCTGGTGCACCAAGGTAAACATGGAACATTGTGGTTATTTGTTTTTAACAAATATTTCTATTACA
GCATTCTCGATCATTTCGGAAAGCTATAACTTGGACAAGGTAAGCAGTTCCGAGGAAGATTGTGTTAGCGAGGACTCCGAGCCACCACCCACGAA
TAGTGTGATGAACAATATGATGAACAGCCTGTATAGT
(SEQ ID NO: 469)

Exon: 1412..516
Exon: 365..355
Start ATG: 1125 (Reverse strand: CAT)

Transcript No. : CT14406
CTCCGCTCTGCTCTCTCGCTTGCTCTCTGAACGGAACAACTGAGTAGTCTGAATTTAACAAGTAACCAAACCAAAAATTAAATGTGCTTTTACAT
CAACAAACGCTGGACGCGCAATAAGTGAGGTGTTAATTATGCGCCGCAGCAGCAACAGCAGCCAGCAGTGAAAAAATGTTGCACTCCATCTGAGT
TCGGCCGCACAATTGTTTTGGATTTTGGATAAATCGCAAAATTGGAACGAATAAGAAACAGCCAGAAGAACATCGAACGGAAAAAAAAGAAAGCG
CGATGTGCGACGGTGAAATTGGCGATCCGGTGACTCAGCCACGTTCCGAGGGCGGTGGATTGGTCACAATGGATCAGGAGACCCGGACGCACTAC CTCGACGCGGCGACAGATAAGCACCTGACCAATGGATCGCCAGATCCAGAGCCCGTGGATCCGCTACTCGTGGCCCAGTGGTCCATCGAGAATGT
GACCAGTTGGGCCACCTGCATGGAGCACTTTTCGAGAACACTGCTCGACTGCCTGCGCCAGGAGGCCATCGACGGCGAGGTGCTGCTCTCCCTCA
CCGAGGAGGATGTACGTGATATGCGCTACAAACTGGGCTACAAACTCACCTTCGGCGAGCTCAAGAAATTCTGGATAGCCGTGCTCAAGCTGCAG
CTACTGGTGAAGAACAGCTCTGCGGAATCCGTAATACTGGGCATCGAGTGCCATGGGAACGGGAACTCGGTATACATGCCACTAGCCAGCACCGG
CTGCGGTCCACCGTCCTCATCCACGTGCCCCTGTCCGCAGGCCGAATGCCCCAGCTATGTGTCCGATTGCGATACCTATTTGCGCATGGGCGGAC
GCTATGTTCCGCCGGAATACTTCAAGACCGCCATGAGCTTAGCCGAGAAGTAA
(SEQ ID NO: 470)

Start ATG: 288 (Reverse strand: CAT)

MCDGEIGDPVTQPRSEGGGLVTMDQETRTHYLDAATDKHLTNGSPDPEPVDPLLVAQWSIENVTSWATCMEHFSRTLLDCLRQEAIDGEVLLSLT
EEDVRDMRYKLGYKLTFGELKKFWIAVLKLQLLVKNSSAESVILGIECHGNGNSVYMPLASTGCGPPSSSTCPCPQAECPSYVSDCDTYLRMGGR
YVPPEYFKTAMSLAEK*
(SEQ ID NO: 471)

Celera Sequence No. : 142000013384043
TGGCCGACTATGCCCGAACAAAACAGCCGGGAGCCGTTCATCCTTTCGCCCAGTGGTGGCGAAATGTTCCAGGTGCTGGTCACCCTGCTACACAA
TCTGGAACGGGAACTCTCCGCCAATCTGTTCACCCAAACGCTCCGTTTGATAGCCCATCAAATCGATGACTTCATGCTCGAGAGCATGGTCATGA
ACACGAAGTTCTCAGCTGCGGGAGCAGCGCAATTCAATTATGACATGACACGCAATTTATTCGCGCTCTTTGGACAGTATACACGTCGTCCCGAG
CTGCTCTTCAAGCGGTGAGTCATCTCTACATTTGCTATGGTGCACAATAAACATAAATCTGACACCTTTCATTTCCATTCGATTCGCCAGAACAC
ACGATGCCTGCAAGCTGCTGGCGGCGGCACGAGGAACAGCTTTGTTGCTGCTGGAAACGCTGCGTGGTAATCAATCGGTGGAGGAGAAGACGAAG
CCGCTGAGGGAACTGCATGTGCTCAGCATGGACAGCAAACAGTGCATTGAGGTTCTGGAGCGGAGGATGGACATAAAGATGTTTTAGGTGATGGA
AATTAATTTAAGCTAGTTAATTGGGCCCTAGGAACTTTTGAAATGATATACAACGTTCGGACGCCGTTTTTTTGCGAAATAAAATCATTAACACC
CAAAATGAAAGTTAAAAGATGTTTATCGTAATTTACATTCATTTTATTTGAAGAAAGGCATGTGTATAAACATAGTTATCATGACGGAGATTTAA
CTAATTTGTATTTAACCAGGACACAGTTTCGAACTCGTGCGAATGCTAGTAACAAACGACCAAGTTGTATGAATGAGATATAATTTTGAGTACAT
ATTTACAATTAAATAGCAATTCGTTGCTCTAGGCGCACAAGTCTTGAATGTTTTTTGTGATAATTAAACATTTAGTTGGAATTGTGGTCTCAATG
TTTGGTTTAATTTGTAAAACGTTGACACAAAAACATGCGGTAACTTTAACTTTAATAATAAATTGATCTAAAAATACATAGCGTAAAATAGCATA
TAAACCGGCCTGATCGGGCTCGAATCGCATATCAATACTGATTCATGGCTGATCAGGGCGTATTGTATATCCCTATCGTCGGATGACAAACAATT
GCAGTTAGTAAATACCAATTTGCGACTCGAGACGCACATCACACATCATCATCACATCGTGGAACGGACCAAGGCGCATTGCCCGCAGAGAGTAA
CTTTTATGTCTACACTAAATAACCGATAATAATCCGATCTGCGGGCGCCGTTCGCCTTTGTATCCCCCCCTTTCTATTCAAAGTTCTGATAATTC
TCGGCGCTGACGAACTGTGCCCGTTGCTGGGGTGTCATGTTGAGATTACCGCGGTTCTTGTTGTTGTAGGCCCAGATGACGCCGGTGGAGATCAG
GGCAATGGTCAGCCAGCCCATGAAGAACAACTGCAGCCACATGTGCTCGCCGCCGCTGTGATCCACGATAATTCCAGCCACGATAGTGATGACCG
CCAAGCCAAGATTCTGTATCGATTGGCAGAAGCCGTAGGCCGTGCCCAATTGGTATTCCGGAATGATGAGAGCCACCAGAGGCCACAGGCTTGCG
GCCAGCATGGAATACGACAGTCCCATGATGATCATGCCCACATAGGGTGTCAGCTGGGTGAACGTAAGCAGGGCATGGGCTCCAATGGTGGTCAG
TGTCGCTGTGAACACCCAGGTCACATTCCTACCCAGTTTGTCGATGATGAAACCAAAGACCGGAGACGATACGGCTGCAATTAGATACACCAGCG
AGTCCACGGTGTTGGCCTCAGCAGGCGAAAGCCCGAAGCGATCAACAAAGAAATTCTGTCCGAGGGCAATGAATGGGAAGATGGCCACATAGTAG
GCGACGCAAATGATGGATACCATCCAAAAGGGTGGTTTGAACGAAAAGACATCGGTGAGTTTCGGTATCTGTCCAGCCGGGTTGTTGTTACGCTG
CAAAATCCGCTCGGCCCTCTTGTCCATCCAGCCGAGGATGAGGGCACAGGTCATCGACATCACACAGGTGAGGGTAGCCAGCAATAAGACGACGC
CTAGAGCGGTATGTCCCTTGTAAAAATTGCTCACATACTCATAGATGGGCTGCATCACCCAGAAGTTGACGGTGCTGCCGAATCGGGCAACCGAC
AGCTGCAGGCCGAATACCATGTTCAGTTCCTTGCCCTTAAACCAGAGCACCGCATAGCTGTTCTGGGCCACCGCCAGTGATTCGGCGCCAATGCC
GAAGATAAACCGTCCCAGGATCATCATCCAGAAGGCGTCCAGAATGCCGCCGCAGGCAAAGATCAACTGACCCACCAGCAGGATCATCATGTAGA
TAATCGTGCCCAGTCGAATGCCAAACAGTCGATCGATCAGGAAACCTCCCACGAAGCACAGGACGACATTGGGCCACGAGTAAATCGAGTAGATG
AGTGTGAACTGGGCGGAGGTCAGATTAAGATCTTTCTTGAAATAGTTCTGCAGGGCGCCGGGTGCATCGTAACAGAAATAGGAGCCGAATCCCAG
CAGGCACATGAACACCAGAGCCATGAACCGGTGGCTCGTGCTCGAGGGCATGCAGCAGCCGCCGGACGGAAGGCTCAGTTCATTGTCACGCCGAC
CGGCCCGACTGACCACTTGGTCCTCCTCCGTCGGTCGCGACACCTCCTCATTGTCCACGATGCGTTCCTCGTCCTCGCGCGCCATCTCCACTCAC
CGCTGGCACAATCCGCACTGACCAGTTGGATGTGGAGCCGAATCCCGCAGAATGGGCGTATGCAAAACTATGTGATATGATTAATCGGCTTTCTG
ATTTCCTGCCGCAGTTGTTTTTTCTTTTGCTTTCGTTTTTCTCTTTTCGTATTTGCCGTTTCTGCAAAATATTTGTATCAATTTCTGCGAACGAG
TGAGCGAGTTGAACTCTTCTGCTTTGTCTTGGCTTATCTCGCTGCTTTTGTTTTTGTTTACTGTACTAGTACCCTTTGTCTAACAACTATTGTTG
TTGTTGGCTGTGTGGGCTAGTTAGTTGTCTCTGGGTTCACTGGTTATCAGCAGTTTTTCCACTCCACTTGCAGCTGAAGTTCGCAGTGCGGTGTT
GGGCAACAAATGTTCGGTGACGTGTGCAACCGCACTTTATTGCTGATCGAATAAAACTAAATTCTTTCCTCTGCCTAATTAACGTTAATTACGCA
TATACAATGGCGGGGCTGCCAACTCGCTGTAGAGCAGGGTTGTCGACGCAGCTACAGGTGCATTCGAACAGCTGGCAGGCGATAACGATCACAAA
TATGAACGGTATTCCTGTTTTGCTCTCCATTATAATCGAAAGTTTACTCTAATTGAAATGCAAATTTTAGTAAGCCATGATTATTTATATAATAG
AATTATATAAATAAAAATAAAAACGCTTGATTATATTAATAAAACAAGATAATCATTAATTGAGAAACTATTTAAGTACAAGAGCTCAACGACGC
AGAAATCTCTTGCATCTTGTTTTGATTTAATTTAGTATAGCCTGACAACCCTAATCCAGCAACGCCGAGTTGAAGCATGTTTTCATACTTTTTAC
CGGGTAAAATGTATTTAATTATATAATTCAGCGGCCCTTGCAGCAATGGATCCCATCGACACCACCAAGCGAAAGCCCAGACGCACCTACGGCAC
GCCATCCTACACGTATCGCAATCGATTTGCCTATGCCCTCTTGGCCGCCGGAACTGTGCTCTTCGGCATTTGGAGGTGAGCAGATCTTCGAACTT
AACGTATAAATGTGGTTTTAATGCTTGCCACCGCCTCGTTTTCAGCCTGACTCCCATCCAGCGCATTGCCAACGAGAAGCTGTCCCAGGCGGTGG
CCCAAACCGAACAGGAGCGCGATAGGAAAGGACTCTTTGAGTTCGGCGCACCAAGGACTTCGCAGTTCATCAGGGACGCCATCAAGGAGAGCGAG
GAGCAGAGGAACAAATAATGGATCGCAAGACGCGGCGAGCCAACTTCAAAAACCTGCAGCCTCGGTAATTTTAATTGAAATAAAGGCCAATAAAA
TGAATGTCATTATCTAACCGAACACTTTGTTTTCCTTTCATCCGAAGTTTGACGCGAAGCACCAAAGCAGCCGCAGATACATTATCGTTATCCAA
CTTCTTTGCCACACCCGAAAATGCTGAAGAAGTTCCGTCATGTCTCGCCGACATTCCTGTTCAGCCCGATCCTCCTGCGCCAAAAATCAAACCAA
(SEQ ID NO: 472)

Exon: 3275..1001
Start ATG: 2745 (Reverse strand: CAT)

Transcript No. : CT14536
CGACAACCCTGCTCTACAGCGAGTTGGCAGCCCCGCCATTGTATATGCGTAATTAACGTTAATTAGGCAGAGGAAAGAATTTAGTTTTATTCGAT
CAGCAATAAAGTGCGGTTGCACACGTCACCGAACATTTGTTGCCCAACACCGCACTGCGAACTTCAGCTGCAAGTGGAGTGGAAAAACTGCTGAT AACCAGTGAACCCAGAGACAACTAACTAGCCCACACAGCCAACAACAACAATAGTTGTTAGACAAAGGGTACTAGTACAGTAAACAAAAACAAAA
GCAGCGAGATAAGCCAAGACAAAGCAGAAGAGTTCAACTCGCTCACTCGTTCGCAGAAATTGATACAAATATTTTGCAGAAACGGCAAATACGAA
AAGAGAAAAACGAAAGCAAAAGAAAAAACAACTGCGGCAGGAAATCAGAAAGCCGATTAATCATATCACATAGTTTTGCATACGCCCATTCTGCG
GGATTCGGCTCCACATCCAACTGGTCAGTGCGGATTGTGCCAGCGGTGAGTGGAGATGGCGCGCGAGGACGAGGAACGCATCGTGGACAATGAGG
AGGTGTCGCGACCGACGGAGGAGGACCAAGTGGTCAGTCGGGCCGGTCGGCGTGACAATGAACTGAGCCTTCCGTCCGGCGGCTGCTGCATGCCC
TCGAGCACGAGCCACCGGTTCATGGCTCTGGTGTTCATGTGCCTGCTGGGATTCGGCTCCTATTTCTGTTACGATGCACCCGGCGCCCTGCAGAA
CTATTTCAAGAAAGATCTTAATCTGACCTCCGCCCAGTTCACACTCATCTACTCGATTTACTCGTGGCCCAATGTCGTCCTGTGCTTCGTGGGAG
GTTTCCTGATCGATCGACTGTTTGGCATTCGACTGGGCACGATTATCTACATGATGATCCTGCTGGTGGGTCAGTTGATCTTTGCCTGCGGCGGC
ATTCTGGACGCCTTCTGGATGATGATCCTGGGACGGTTTATCTTCGGCATTGGCGCCGAATCACTGGCGGTGGCCCAGAACAGCTATGCGGTGCT
CTGGTTTAAGGGCAAGGAACTGAACATGGTATTCGGCCTGCAGCTGTCGGTTGCCCGATTCGGCAGCACCGTCAACTTCTGGGTGATGCAGCCCA
TCTATGAGTATGTGAGCAATTTTTACAAGGGACATACCGCTCTAGGCGTCGTCTTATTGCTGGCTACCCTCACCTGTGTGATGTCGATGACCTGT
GCCCTCATCCTCGGCTGGATGGACAAGAGGGCCGAGCGGATTTTGCAGCGTAACAACAACCCGGCTGGACAGATACCGAAACTCACCGATGTCTT
TTCGTTCAAACCACCCTTTTGGATGGTATCCATCATTTGCGTCGCCTACTATGTGGCCATCTTCCCATTCATTGCCCTCGGACAGAATTTCTTTG
TTGATCGCTTCGGGCTTTCGCCTGCTGAGGCCAACACCGTGGACTCGCTGGTGTATCTAATTGCAGCCGTATCGTCTCCGGTCTTTGGTTTCATC
ATCGACAAACTGGGTAGGAATGTGACCTGGGTGTTCACAGCGACACTGACCACCATTGGAGCCCATGCCCTGCTTACGTTCACCCAGCTGACACC
CTATGTGGGCATGATCATCATGGGACTGTCGTATTCCATGCTGGCCGCAAGCCTGTGGCCTCTGGTGGCTCTCATCATTCCGGAATACCAATTGG
GCACGGCCTACGGCTTCTGCCAATCGATACAGAATCTTGGCTTGGCGGTCATCACTATCGTGGCTGGAATTATCGTGGATCACAGCGGCGGCGAG
CACATGTGGCTGCAGTTGTTCTTCATGGGCTGGCTGACCATTGCCCTGATCTCCACCGGCGTCATCTGGGCCTACAACAACAAGAACCGCGGTAA
TCTCAACATGACACCCCAGCAACGGGCACAGTTCGTCAGCGCCGAGAATTATCAGAACTTTGAATAGAAAGGGGGGGATACAAAGGCGAACGGCG
CCCGCAGATCGGATTATTATCGGTTATTTAGTGTAGACATAAAAGTTACTCTCTGCGGGCAATGCGCCTTGGTCCGTTCCACGATGTGATGATGA
TGTGTGATGTGCGTCTCGAGTCGCAAATTGGTATTTACTAACTGCAATTGTTTGTCATCCGACGATAGGGATATACAATACGCCCTGATCAGCCA
TGAATCAGTATTGATATGCGATTCGAGCCCGATCAGGCCGGTTTATATGCTATTTTACGCTATGTATTTTTAGATCAATTTATTATTAAA
(SEQ ID NO: 473)

Start ATG: 531 (Reverse strand: CAT)

MAREDEERIVDNEEVSRPTEEDQVVSRAGRRDNELSLPSGGCCMPSSTSHRFMALVFMCLLGFGSYFCYDAPGALQNYFKKDLNLTSAQFTLIYS
IYSWPNVVLCFVGGFLIDRLFGIRLGTIIYMMILLVGQLIFACGGILDAFWMMILGRFIFGIGAESLAVAQNSYAVLWFKGKELNMVFGLQLSVA
RFGSTVNFWVMQPIYEYVSNFYKGHTALGVVLLLATLTCVMSMTCALILGWMDKRAERILQRNNNPAGQIPKLTDVFSFKPPFWMVSIICVAYYV
AIFPFIALGQNFFVDRFGLSPAEANTVDSLVYLIAAVSSPVFGFIIDKLGRNVTWVFTATLTTIGAHALLTFTQLTPYVGMIIMGLSYSMLAASL
WPLVALIIPEYQLGTAYGFCQSIQNLGLAVITIVAGIIVDHSGGEHMWLQLFFMGWLTIALISTGVIWAYNNKNRGNLNMTPQQRAQFVSAENYQ
NFE*
(SEQ ID NO: 474)

Name: permease, putative
Classification: transporter

Celera Sequence No. : 142000013384043
AGAAGAAGAATAATATTCAGAAAGAAGTTCATCAAAGGAATTCACAAAGGAGAAGCATTCAATGCACTCCCAAAAAACGTGGTCGAAAACCAAAG
CAACCGGCTAAGAAACTGCAGTCAAGAATTTCCACCGATCAGCTAGGAAGCACACCATCGCCATCCAAGCTGCCTGCCAAATATCCCGCCCATTT
TGTTCATCAACTTCCGCCCGCTGAGGATTCCAGCTGTGCCACTCGAAGACGATCCTTATCTGCTCCAGCTATGCAACTTAGCGATCTAAGCCTCA
CACCCGATGAGATCCAAACTCCGGAGCGGCGCGGTGAAATCGTAAACAAATCGCCATCGGATCTCGACTCCGATGTCTCCTTGAACTTCTCGCTG
TCCGATTCCATTGGCGAGATCTTCGGCACCAAGGACATCAGCAGCATTCTGACCATGCAGCGGCCGCGTCAGTACATTTTGCTGGAGGAGCATCT
GCCCACACTGGCCACCATGTTGAACGTTGACTTGGAGCGACTGCGCTGCGTGCTGGATATCACTCAGGGCTTGAGCCACGAGCAAATCCTGCGCT
TTCCGATAAAACATGAAGAGGATGAATTGGAAGTACCTTAGATATGATGGGGAACTTATAGCAGTAGTATAATGTTTTCACTTTGAATAGTTTTA
ATGTCCAAGTCCAACATATTTAATTCCCATAAGATCCTTGTTGCTTTAACTTAACATTTAAAATGTATATCTCCCTTTTTTTTTGTATATTTTTA
AGTGGTATTTAATTGTTGTTGTTTTTTGTTGTTGTTGTTTCTTTTTCGTTATTTTGCCTTAGACTTTCAGAGTGCACAATTTTTGTTTAAACCAT
TTACTTTTTTGTATATTTTAAATTACTAATGCTAAACGTTATCTAGACTTTATCATACTTCATAATTGGTTTCCTTTCCTCCACGACAATACAGC
AGCAATCGATCGGGGTTTTTTTTGTATCTGTTACTAAGTTTTCTTTTTTGTTTACTGTGTTTCTCATTTAACGTATATACAACCGCGTGAATTT
GGAGTTGCAGCTCCCTAGTAGTCGCTGTCGTAGCTTCCGTCCTGCTGCGCCTGCGTCGAGTCATCGGAACGCTCCGAAGTGGGCTCCAGATCAAC
GTCCAGGGCCGTAGTGTTGGCCGGACAGCAGCTGGGATGAGCCATTGAGTCGAAGGCATCTTTGATTTGATTGTTGGCACCTTTGGGATCTAGGT
CGGTGGCCCAGCTGAAGTGCATCAGCGCCAGATCCATGTTGCCGAGCGTCTTGTGGATTTTGCCGATCAGATAGAACACCACCGACTCCTTGGGC
ACGACTTCCTTGAGCTCCTCCAGTTCGCGCAGCGCCTCCTGGTACTTGCCCAGCGAGAAGTAGATGGAGCCGCGATGGAATCGCGTCAGCGGGTT
CTTGGGGTCCAGCGTGGCGGCCGTGTTTAGCGTCTGCAGCGACAGATCCTTCTTCTTCATGTAGAATTGCATGGCGCCGATGTGCACGAGAATAA
CCGAGTTCTGTGGATTGATTTCAGCGCCTTCACGTAGTGAATCTCAGCCAGCTCGTATTTCTCCTGCTTGGAGTAGATGGTGCCGATGCCGTAC
CAAGCATTGTAATGCCGCGGATCTCTAACCACTGCTGCACGGAAGTAGTCCATGGCCTTATCAAATTCTTCGGTGAGTACGAGTTCGTGGCCCAA
CAGTGTGTAGCTGTAGACGAAGTCTGGATCCACTTGGACAGCCCGCTTGAAGAACTTGATCGCGGTTTCGTGCTCCTTTTGCAGCGAAAAGCAAT
TGCCGGACACACACCAGGTAACCGGGCTGGTTTTGTCCTGGTTAATCAGATCCTGGGCGAGAGCTGACAGCTCAACCTCGCGCTGCAAATGCCAC
AGGGATGACGAGTATATCTCCATGTAGTCCAAGCGACATGGCTCTGTCTTGTGGATGGTCTCAAATATCGCCACCGCCGCCTCATACTCACGCAT
CTCGTACCTGGCCAGTCCGATGAGCGACTGCACCCAGCTGGAGTTCAGGTGGTGCTTTGGTATCGTCGTCTCCAGCTGCTTTATGGCCGCCTTGC
ACTGGAAGTTCGAGAGCAGCTGATAGGCTTCAGCTAAACCCCGCAGCAGGGCCATCAGCCCATCGGCCGATTGTTTCTTGAGTCCCATCAGCTGG
TGGGCCATCGTCTGGGCATTGTTTAGGCTATTGTTCAGCAGTACTTTGGCCTCCTCGGCGGCACTGCGTCCACCGCTGTTGTTATTCGCTCCCGA
GGAAGTAATAGTCTCCACCTTCTCCTTGCGCTTCTCGGAGAGGTGGTGGGACTTATCCTCGATCAGTTCGTTATTTAGGCAGATCTTGGTCATCC
GTGACTTGGCTTTGCGGGGCGGCGAACGTGGCTGCACGAACTTGTTGGCTATGTTGGGCGATTTATTGTTCTCCTTCACCGAATACGAGTTGCTG
AACAGCCGCGAACTGCGACGCACTGCAGCATTCGGATTGGGCGGCACATTCATATTGCCATTGTTGCCCACATTATTGTTGTTCGGAGTGCGGGG
CGTTATGTTTCCGGCTTGCGTAAAGACGGCGGGTTTATTAAGGCTGCCCTCTTTGCGATTGATGAGTCCGCCCACATGTGTCTTTAGCTTTTTGC
CCATCATCTTCGGCTCCTGGTTGACCTCGACCAACATCTGTGGCATCGGCGAATAGCTTATATTCATAACGGGCGTGTGGTTGCCAATGAAGGAT
CCATCGTTGCCGGTGCACGGACTAGTTAAAGGCATGATGCCGAAGCTCGGTGTTGGCGGTGAGATGGCCGATAGGTATTTGAACTGTTTGCGAAA
CGGAGTACCGCTGCTCATGTCGTAGAGCTGCTGGTTCTGCTGATACTGGCCGGCCGGGTCCTGCGGAGCTCCCATAGGTGTGTCCTCCAGCATCG
CCAGCATGCTGGAGTTTTGTACCAAACCCCCGCGCAGCATGCTGATCGAACTATTGAGATTGTTGTTATTATTATTATTGTTGATGGGCGTCACC ATGTTGCTGTTGTGGTGCTGGTTCTGATTCTGGTTGATCTGTTGTTGCTGCTGATCCACGGGCGTGGTCAGAATGTAGTTGGAGACATTGCTTAG
GTTGGTGATCAGCGACTGGCGCTCCTGATGCTGTTGACCCTGCTGCTCGGCTCCGAACAGCACCATTGCATTGGCATTTACGCTGCTGCCCTGGC
AGGTATTGAACACATCTGTGCTGTGGATTTGGAATATGGCCGCCGCATCTGTATCCTGGCCCAGCAGGCACAGATCCGCGAATGCGTGCCACATG
AAGGGGTTCAGTTTGAGGGCGCGCCTTAAAGCACTAACGGCCAGTTTATTGCGCTCGGTCCTCATGCAGATCTGGGCCATTAGCTGATAGGCGAA
GCAGGCCAGATCCCCGAAGTCCCGCTGCAGCTCATCGCAGTTCTTGGCGTCCGCGAATCCCGTGGAGATCAGGGCACTCTCCGCCTCAGCGTATT
TTTTCAGCTCGTAGGCACATTTGGCCTGCAGAAAGCGGCACTGCGGCGAGCGGCGTGCCTTCTCCTTGAGCAGCCAATATGCCTGGTGCACCTGA
TTGGAGCGGAAGTAGCTGGTGGCCAGCAGGAATATCGTCTCGTCGCTCTCCACTGCAAGGACACGGTGAAAGAGAAAATCAGTGATATACCCGGT
CAGACAAACGAGACCTTGACCTATACCTTCTGAGCACAGGCGTTCCGACAGGAAAACGGCATCCTTGAAGTCGTAGTAGTTCAGGCAATGCCATA
TGGCGGCCTTTGGGAGCGAAAAAAAAGAAGGGAGAAAATTTGGTTTTTTATAGAGGCCAGGTGGACCGAGGAGCTATTGATTTACCTGCACGGGC
TCTTGAATCATCATGTCTGGGCGGTATGTGCGACTTTCTAGGGGCGCTCTATGAGATGTACGTTCACTGTACTTCAGGGCTTTACAATAATTCAA
ACATGCAGTGTGTAGAACTCAAACAAACTATCATGTCGCCCCCCACTCGTACACTCTTCTGTTTGTATTTGTATTCGAATTGTTTTCTTTTGGCC
AAATTTTTTCCAACAATATCGAATGGGAAAAAGTAAAAGTTTGGCCTGTGTGCTGGCTGGCTGTGTGGTATGTGAGTGTCGTATGTAACCCGATT
GCGGATGCGGCGATGCAAGTGGCGATGGCGGTGTCTCTCGCTCCCTGGCCTCCACTCCACTCCACCTTCCACTTCCACTTTTTCTTTATATTTGA
TATTGCAATTGGTTTGAGTCGAGCCTTCGCTTCGCTTCGCCCTCTGTACACACACACTGCGAACGGGGGGTCGGTTTTCTACTATCGTTTTCGGG
GCTTATCTCTCGTTAAAGACGCACACGGGGCTGATCTGCGATTGGCGGCGACACTGGACTACACCTTGGCCACATTTTAGCTACTTGAAACACGC
TGCATACGCGTTGCATTCCATTTTATTTGAAAAACCAAAGCTAAAATAATTGCGAGCTGTCAAAGTATCGATTGCACGCGACCCTGCCAATCGAT
TGTTTATATGGTTGAGGAGGACCGTATCGCACTAGCGCAAAAGTACCAAGCTCTTGACACGAAGCTATTATAAGCTGTTTCCACTGATACATAAC
TTTGCATTTTTTTAAATGCCAATTTAAATTGTAAATTAATATCATTAAAGAAGGTCATAAAATTAGATATGTATCCCAGCTACTCAAATATATAC
ATAACTAGACTTCCTTACAGCGCGCTTTTATTAAATACCTAATACTACTAGCTTAAACGAGATTTAGTTATAGTTTTTTATCCAATTCTACTGCG
AATCGCTGGAACTGGAGCTTGAGCTATCCGTGGACATGACCTCCACATCGTCCTGGGCGCGCGTCTCCAGGGCCACTGTGTTCCCAGAGGCGCCC
ATGGTCATGTGCAGCTCTCCGAGATTCCAGTTAAACTGGTTCTGGAAGGCATTGGGCACCTCGCCGCCGGCGCCACTGCCACTCCCACTTCCTGC
GCTACCGGACAGCGTTCGCTGCTGCTCCGAGGGCATGCCGCTGTTCTGGTGGGTCACTGTTCCGCCGTTGATGTTCTGCTCGGATTTACCCAGCA
GCCCGTTGCGCATCTCAATGTCCGTGGGATAGGGACGCCGCAGGTCACCTATGCACCAGGTGAGCGGAGCACTGACCGCATTGGCGGAGCTAATC
CGATGTGCGTATTTGATGAGCTCCTCGGATGAAACCGGTCGTTTGTTGGCCTGATTGATGCTGGCCAGTTTCTGTCGCGCTTGGAAGATGGCCGT
GGACAGTATGAGCTCCGCATCCTTTAGCGACTTTTGCAGCTTCTGGATCTCACGGTCCTAAGCGGGAAAATCCAGATTATACCTTATTTTTGGGG
AATGCAAAACTTCTACTTACGTGCACCTCGACCTTAGCGCGCAGTTGGTCCATCGCCTCCTCCACTTTCGCCTGCTCCTCCGCCAGTTCCAGCAT
TTTGCGAAATTCCTCATCTTTGGCCACCAGCAAATCCA
(SEQ ID NO: 475)

Exon: 4548..3886
Exon: 3807..3732
Exon: 3662..1001
Start ATG: 3909 (Reverse strand: CAT)

Transcript No. : CT14558
GGTCGCGTGCAATCGATACTTTGACAGCTCGCAATTATTTTAGCTTTGGTTTTTCAAATAAAATGGAATGCAACGCGTATGCAGCGTGTTTCAAG
TAGCTAAAATGTGGCCAAGGTGTAGTCCAGTGTCGCCGCCAATCGCAGATCAGCCCCGTGTGCGTCTTTAACGAGAGATAAGCCCCGAAAACGAT
AGTAGAAAACCGACCCCCCGTTCGCAGTGTGTGTGTACAGAGGGCGAAGCGAAGCGAAGGCTCGACTCAAACCAATTGCAATATCAAATATAAAG
AAAAAGTGGAAGTGGAAGGTGGAGTGGAGTGGAGGCCAGGGAGCGAGAGACACCGCCATCGCCACTTGCATCGCCGCATCCGCAATCGGGTTACA
TACGACACTCACATACCACACAGCCAGCCAGCACACAGGCCAAACTTTTACTTTTTCCCATTCGATATTGTTGGAAAAAATTTGGCCAAAAGAAA
ACAATTCGAATACAAATACAAACAGAAGAGTGTACGAGTGGGGGGCGACATGATAGTTTGTTTGAGTTCTACACACTGCATGTTTGAATTATTGT
AAAGCCCTGAAGTACAGTGAACGTACATCTCATAGAGCGCCCCTAGAAAGTCGCACATACCGCCCAGACATGATGATTCAAGAGCCCGTGCAGGC
CGCCATATGGCATTGCCTGAACTACTACGACTTCAAGGATGCCGTTTTCCTGTCGGAACGCCTGTGCTCAGAAGTGGAGAGCGACGAGACGATAT
TCCTGCTGGCCACCAGCTACTTCCGCTCCAATCAGGTGCACCAGGCATATTGGCTGCTCAAGGAGAAGGCACGCCGCTCGCCGCAGTGCCGCTTT
CTGCAGGCCAAATGTGCCTACGAGCTGAAAAAATACGCTGAGGCGGAGAGTGCCCTGATCTCCACGGGATTCGCGGACGCCAAGAACTGCGATGA
GCTGCAGCGGGACTTCGGGGATCTGGCCTGCTTCGCCTATCAGCTAATGGCCCAGATCTGCATGAGGACCGAGCGCAATAAACTGGCCGTTAGTG
CTTTAAGGCGCGCCCTCAAACTGAACCCCTTCATGTGGCACGCATTCGCGGATCTGTGCCTGCTGGGCCAGGATACAGATGCGGCGGCCATATTC
CAAATCCACAGCACAGATGTGTTCAATACCTGCCAGGGCAGCAGCGTAAATGCCAATGCAATGGTGCTGTTCGGAGCCGAGCAGCAGGGTCAACA
GCATCAGGAGCGCCAGTCGCTGATCACCAACCTAAGCAATGTCTCCAACTACATTCTGACCACGCCCGTGGATCAGCAGCAACAACAGATCAACC
AGAATCAGAACCAGCACCACAACAGCAACATGGTGACGCCCATCAACAATAATAATAATAACAACAATCTCAATAGTTCGATCAGCATGCTGCGC
GGGGGTTTGGTACAAAACTCCAGCATGCTGGCGATGCTGGAGGACACACCTATGGGAGCTCCGCAGGACCCGGCCGGCCAGTATCAGCAGAACCA
GCAGCTCTACGACATGAGCAGCGGTACTCCGTTTCGCAAACAGTTCAAATACCTATCGGCCATCTCACCGCCAACACCGAGCTTCGGCATCATGC
CTTTAACTAGTCCGTGCACCGGCAACGATGGATCCTTCATTGGCAACCACACGCCCGTTATGAATATAAGCTATTCGCCGATGCCACAGATGTTG
GTCGAGGTCAACCAGGAGCCGAAGATGATGGGCAAAAAGCTAAAGACACATGTGGGCGGACTCATCAATCGCAAAGAGGGCAGCCTTAATAAACC
CGCCGTCTTTACGCAAGCCGGAAACATAACGCCCCGCACTCCGAACAACAATAATGTGGGCAACAATGGCAATATGAATGTGCCGCCCAATCCGA
ATGCTGCAGTGCGTCGCAGTTCGCGGCTGTTCAGCAACTCGTATTCGGTGAAGGAGAACAATAAATCGCCCAACATAGCCAACAAGTTCGTGCAG
CCACGTTCGCCGCCCCGCAAAGCCAAGTCACGGATGACCAAGATCTGCCTAAATAACGAACTGATCGAGGATAAGTCCCACCACCTCTCCGAGAA
GCGCAAGGAGAAGGTGGAGACTATTACTTCCTCGGGAGCGAATAACAACAGCGGTGGACGCAGTGCCGCCGAGGAGGCCAAAGTACTGCTGAACA
ATAGCCTAAACAATGCCCAGACGATGGCCCACCAGCTGATGGGACTCAAGAAACAATCGGCCGATGGGCTGATGGCCCTGCTGCGGGGTTTAGCT
GAAGCCTATCAGCTGCTCTCGAACTTCCAGTGCAAGGCGGCCATAAAGCAGCTGGAGACGACGATACCAAAGCACCACCTGAACTCCAGCTGGGT
GCAGTCGCTCATCGGACTGGCCAGGTACGAGATGCGTGAGTATGAGGCGGCGGTGGCGATATTTGAGACCATCCACAAGACAGAGCCATGTCGCT
TGGACTACATGGAGATATACTCGTCATCCCTGTGGCATTTGCAGCGCGAGGTTGAGCTGTCAGCTCTCGCCCAGGATCTGATTAACCAGGACAAA
ACCAGCCCGGTTACCTGGTGTGTGTCCGGCAATTGCTTTTCGCTGCAAAAGGAGCACGAAACCGCGATCAAGTTCTTCAAGCGGGCTGTCCAAGT
GGATCCAGACTTCGTCTACAGCTACACACTGTTGGGCCACGAACTCGTACTCACCGAAGAATTTGATAAGGCCATGGACTACTTCCGTGCAGCAG
TGGTTAGAGATCCGCGGCATTACAATGCTTGGTACGGCATCGGCACCATCTACTCCAAGCAGGAGAAATACGAGCTGGCTGAGATTCACTACGTG
AAGGCGCTGAAAATCAATCCACAGAACTCGGTTATTCTCGTGCACATCGGCGCCATGCAATTCTACATGAAGAAGAAGGATCTGTCGCTGCAGAC
GCTAAACACGGCCGCCACGCTGGACCCCAAGAACCCGCTGACGCGATTCCATCGCGGCTCCATCTACTTCTCGCTGGGCAAGTACCAGGAGGCGC
TGCGCGAACTGGAGGAGCTCAAGGAAGTCGTGCCCAAGGAGTCGGTGGTGTTCTATCTGATCGGCAAAATCCACAAGACGCTCGGCAACATGGAT
CTGGCGCTGATGCACTTCAGCTGGGCCACCGACCTAGATCCCAAAGGTGCCAACAATCAAATCAAAGATGCCTTCGACTCAATGGCTCATCCCAG
CTGCTGTCCGGCCAACACTACGGCCCTGGACGTTGATCTGGAGCCCACTTCGGAGCGTTCCGATGACTCGACGCAGGCGCAGCAGGACGGAAGCT
ACGACAGCGACTACTAGGGAGCTGCAACTCCAAATTCACGCGGTTGTATATACGTTAAATGAGAAACACAGTAAAC

FIGURE SHEET 263

(SEQ ID NO: 476)

Start ATG: 640 (Reverse strand: CAT)

MMIQEPVQAAIWHCLNYYDFKDAVFLSERLCSEVESDETIFLLATSYFRSNQVHQAYWLLKEKARRSPQCRFLQAKCAYELKKYAEAESALISTG
FADAKNCDELQRDFGDLACFAYQLMAQICMRTERNKLAVSALRRALKLNPFMWHAFADLCLLGQDTDAAAIFQIHSTDVFNTCQGSSVNANAMVL
FGAEQQGQQHQERQSLITNLSNVSNYILTTPVDQQQQQINQNQNQHHNSNMVTPINNNNNNNNLNSSISMLRGGLVQNSSMLAMLEDTPMGAPQD
PAGQYQQNQQLYDMSSGTPFRKQFKYLSAISPPTPSFGIMPLTSPCTGNDGSFIGNHTPVMNISYSPMPQMLVEVNQEPKMMGKKLKTHVGGLIN
RKEGSLNKPAVFTQAGNITPRTPNNNNVGNNGNMNVPPNPNAAVRRSSRLFSNSYSVKENNKSPNIANKFVQPRSPPRKAKSRMTKICLNNELIE
DKSHHLSEKRKEKVETITSSGANNNSGGRSAAEEAKVLLNNSLNNAQTMAHQLMGLKKQSADGLMALLRGLAEAYQLLSNFQCKAAIKQLETTIP
KHHLNSSWVQSLIGLARYEMREYEAAVAIFETIHKTEPCRLDYMEIYSSSLWHLQREVELSALAQDLINQDKTSPVTWCVSGNCFSLQKEHETAI
KFFKRAVQVDPDFVYSYTLLGHELVLTEEFDKAMDYFRAAVVRDPRHYNAWYGIGTIYSKQEKYELAEIHYVKALKINPQNSVILVHIGAMQFYM
KKKDLSLQTLNTAATLDPKNPLTRFHRGSIYFSLGKYQEALRELEELKEVVPKESVVFYLIGKIHKTLGNMDLALMHFSWATDLDPKGANNQIKD
AFDSMAHPSCCPANTTALDVDLEPTSERSDDSTQAQQDGSYDSDY*
(SEQ ID NO: 477)

Classification: known_flybase_gene
Gene Symbol: Cdc27
FlyBase ID: FBgn0012058

Celera Sequence No. : 142000013384416
CCCGCTCCTGCTCGCCCATTTGCAGAAGTCGCTGCGATTTCCGCGACAGCTTGGAGTGGTCTATGGTTTTTAGGGAGTCAAGCAGGGCGGGATGG
GCACTTGGCTTCACAACCGGCAGTTTTCGCCATACCTCCAGCTCCAGATCCTCGGAGTCCTGTGCGGGAATCGTGTACTTGAAGTATGGCTTTAG
GTGACGATAGAAGAGCACTGACTCAGCGATGGCCACGGCAATTACTGGAAAATTGTATTCATTATGGAATCTAATTTAAAAATATTAAAATGCAA
CGTTATTTCTACCCGGCGTCTTGGGCTCCGTTTCGTCGATGTAGAGACTTTCAATGGCCGCTGGAATCCCCGGCAGTGGCTGCTCGTGCTTGAGT
TTAAGACCACGGAAAACCTTCAGCGTGGCAGTGGGCTCCTCGGCGGCATTGTCCAGTGAAATGTCCGCCGCCAGCAGCCGGACATATCCGTCGCA
CTGCACGTCGCTCAGGGCCATGCAACTGGTGAGGGTGGTGAGATGCGGTGGAGGAGCCTCCTCCGCCGTGTCCACGTGAAGCCAGTTGGGAGCAC
CGGCCATGGCAGGATCTTGGTGAAAAATTTGCAGCACAGTGTGAAAACGAACAGGTGATTCAGGACATGCTTTTGTTTTGGTTTTTCTTGTCCTT
AGCAACCGGGATGACAGCACATTTTTTGTTACTTATTTGGGTTTTTTCTTAAAAACACAAAATGATCGTCAGCATTATTCTTAAATGCTAACAGG
GTAAAGCTACGTATAACTAAAAAATCATTTGGCAAAAGGTAAAACTGTGATCAAATTACTGATGATAGAAAATTTTATTTAAATTGGCCGCCAAA
AATGCATTTTGTCTGGTCACACTTAAGGCCGGCCTGCTAAAGACGTGCAAGCATCGACAGTATGTGTTATCGATAAGTGCGAGGGAATATTCGAT
ACCCACGTCAATTGCTTATCGCAAAAAACATTCGTTATAAATATCATCTCAGCGACGCCAGCAGTTGAATTCAATATTTAACATTTTGTATACAT
AAGTGACTGACTACGGCCCTATTTAACTGCAAGTAATGACGGAGCTAAGGGACGAGACACCGCTCTTTCACAAGGGCGAGATAGTCCTTTGCTAC
GAGCCGGATAAATCGAAGGCCCGTGTTCTTTACACCAGCAAGGTAAATACACATGCACACACACACACGCGCGCGCATTGAAATGTCAAGCAA
ACGTCGTAGGCGAAGTTTTCACAAATGATTTTCCGTTTCCCGCAATTTTCCGTACATGCCGCAGGTGCTAAACGTCTTTGAGCGCCGGAACGAGC
ATGGCCTGAGGTTCTACGAGTACAAGATTCACTTCCAGGGCTGGCGTCCATCCTACGATCGCTGTGTGCGCGCCACCGTTCTATTGAAAGACACC
GAGGAGAATCGCCAGTTGCAAAGGGAGCTGGCCGAAGCTGCCAAGCTGCAAATGTAAGATAACCCCCTAGACATGCGTGGAATACCTCTCTAACG
AGTTCCCCCTTCTTTTTCGCACAGTCGTGGTGACTACTCCTACAAGGGCACACCCGATAAGCCATCGGCCAAGAAGAAACGCGGCGGAAAAGCGG
CCCACGTTGAGGAGCCAATAGTGGTTCCAATGGACACGGGACATCTTGAGGCGGAGCACGAAATGGCGCCCACTCCACGAGCAGCGGGCAACCGG
ACGCGGGACAACAGCGGTGGCAAGCGAAAGGAAAAACCCCCGTCCGGAGATGGCCGATTAAAGGGAAACCGGGGCAGACAAACAGAGACCTTTTA
TAACAATGCCATAAATGATGTATCGGTCTATAACCATGTGCCACAGGAGGATCGCATTATGATGCGAGTCAGCGAGCGATTGCGAGAGCTTATAG
AGTACGATCGGAATATGATCAAGGTACTAGGCAAACAGCACGCACTGCCCGCCCGCGTGCCCATCGTGACCATCATGGAAAACTTCGTCAAGCAG
CAGGCCGTGGAGCTAGCCATTAGCATTAAACAGGACAGCTCGAGGGCCAGGAACACGCAGAGTCGCAATGCCAGAATGGAGCGGGAATACGATCG
CGTTATGTCCACGTTGGTTACCACTCAATATCAGACTTAACAACCCACTTATACTCTTACTTATTAACAGTGTCTGCATGCTGAAGGAGGTGGTA
GACGGATTGCGTATCTACTTTGAGTTCCACGTGGATGACCACTTGCTGTATACGGAGGAGAAGGAGTATGTCCACAACTACCTCACAGACGACAA
CATGCGCAACTGCAGCCTAATATTGAACAAGTCGTACGAGTATATCAATCCCAGCGGTGACACGGAACTGATCGGTCTGGACGGCACGCCAGTGG
TAGAAGGGTCGGGCGACACCAATGGACAGATCGGAGTTATTAATATCGGCGGTCCGGAGTACGAGAAGCAGTTGCAAAAATGCCTGCTCTACATT
GTTACCGCCAGCGGGAAAAACACTGCGCAGGCCTATGAGAGGACTTCCCCATATACGGCTGCCTACAAACTGCCCGTGGAGATGCGTGGATTTCT
GAACGAAACATTCAAGTGGCGGCTTTTGTCAGCGGAATCGCCGCCAGAAAAGTCCATGGTCTTTGGCGCTCCCCACCTGGTTAGGCTAATGAGTA
TGTACAATCTTTCTTGCATTCTATAACACACATTAATTCATGGTACTTGCAGTTAAAATGCCCATGTTCTTAAACGCATCGCCGATCAGCAACAA
GAAGCTAGAAGATCTACTTCCCCACCTCGACGCCTTCATCAAGTAAGTCTAAGACCCCTCCCTAGTCCATCACGAAGCTAATCTGTTGGTTTTTC
AGCTACTTGGAGAACCACAGGGAGTGGTTCGACAGGGAAAACTTTGTTAACTCCACTGCCCTGCCCCAGGAAGATCTGCAGCGGGAGCTGTTGGA
CTCCCTGGATGGGATTGCTGCTTAGCTTTAGTTGATCGTAGTTATCTAGTTTATTTATTATTACGATTAAAGCTTATGCTCTTTTATTTAAAGAT
TTGTAATTGTCGTTTTGGTTTCTTCAACTACACACTTTGTAAACAACGCACTTCTATAAAAAAGTTTCCTAATGTGATCGTATAATCGAATAATG
CCTATAACTATATATGTTAAATATTGAAAATACGATTTTAACATTTTTTTTGTTTTTTTTTTTTTTTTGCTTAACCTAAGTTTTAGTTGAGTA
GTACATGCTAGTATTTTTGTCATGCCTTGTTTTTTGTGCTCAAATATATTTAAGAGTTGGAAAGTTGTTGTCTTTTGTATTAAGGATTTGCGGAC
CTTGAGTTGGAATGTGCAGGGAATTCTTAAGATTTGTATAATTTCTCAAAATATTGCAACTGTAACAACTATGTGTGTGCTGATTTGTGTTTCAG
ATCCTGCTTAGAAATTCGAAATTGTCGCTTGGACGGCTTGGAGTTGGATGCATTCGCGTTTGTAACATGTGTAAACTTGGGACGTTAACTTGGAC
GATGACTGAACTGGACTGGACTGCCGGCCCTCACTTCTGTCGCTTGGTGGCACTGCTGGCCGTGGGTCGCATGAAGCTGCTCACGGATCGACTGC
TGCTAGTGCTCCTCTGCTGCGGACTGGGGTTCGCACTCATCCTGGCCTGCTGCTGCTGGTTCAGGGCATTTTCACCAGCACCACGCTGCGAGCG
GCGCTCATTCGGGACTGTGACTGGGGTTGGGACTGGGACTGGTTTTCCTTAAAACTGGTGCTACCATGGATACTCGATTTCGGAGCCGTGTTGGA
CATCTTGCTGCGCACCAAGATCACACTGGGTCCCACACTCGACCCGCTACTGCTGCTCCTGCTGGCGGGGACTCCACGTCCCTGGGTAGGTCGCA
GATTCTGGGCGGCCAGTGGTCTTTTGCTGGGCGAGGAGTCAACGGACACAGTGGCTCCCGCTCGCTGAACGGCGG
(SEQ ID NO: 478)

Exon: 1001..1182
Exon: 1300..1478
Exon: 1545..2102
Exon: 2161..2657
Exon: 2713..2797

FIGURE SHEET 264

Exon: 2853..2970
Start ATG: 1081

Transcript No. : CT14600
AGCGACGCCAGCAGTTGAATTCAATATTTAACATTTTGTATACATAAGTGACTGACTACGGCCCTATTTAACTGCAAGTAATGACGGAGCTAAGG
GACGAGACACCGCTCTTTCACAAGGGCGAGATAGTCCTTTGCTACGAGCCGGATAAATCGAAGGCCCGTGTTCTTTACACCAGCAAGGTGCTAAA
CGTCTTTGAGCGCCGGAACGAGCATGGCCTGAGGTTCTACGAGTACAAGATTCACTTCCAGGGCTGGCGTCCATCCTACGATCGCTGTGTGCGCG
CCACCGTTCTATTGAAAGACACCGAGGAGAATCGCCAGTTGCAAAGGGAGCTGGCCGAAGCTGCCAAGCTGCAAATTCGTGGTGACTACTCCTAC
AAGGGCACACCCGATAAGCCATCGGCCAAGAAGAAACGCGGCGGAAAAGCGGCCCACGTTGAGGAGCCAATAGTGGTTCCAATGGACACGGGACA
TCTTGAGGCGGAGCACGAAATGGCGCCCACTCCACGAGCAGCGGGCAACCGGACGCGGGACAACAGCGGTGGCAAGCGAAAGGAAAAACCCCCGT
CCGGAGATGGCCGATTAAAGGGAAACCGGGGCAGACAAACAGAGACCTTTTATAACAATGCCATAAATGATGTATCGGTCTATAACCATGTGCCA
CAGGAGGATCGCATTATGATGCGAGTCAGCGAGCGATTGCGAGAGCTTATAGAGTACGATCGGAATATGATCAAGGTACTAGGCAAACAGCACGC
ACTGCCCGCCCGCGTGCCCATCGTGACCATCATGGAAAACTTCGTCAAGCAGCAGGCCGTGGAGCTAGCCATTAGCATTAAACAGGACAGCTCGA
GGGCCAGGAACACGCAGAGTCGCAATGCCAGAATGGAGCGGGAATACGATCGCGTTATGTCCACTGTCTGCATGCTGAAGGAGGTGGTAGACGGA
TTGCGTATCTACTTTGAGTTCCACGTGGATGACCACTTGCTGTATACGGAGGAGAAGGAGTATGTCCACAACTACCTCACAGACGACAACATGCG
CAACTGCAGCCTAATATTGAACAAGTCGTACGAGTATATCAATCCCAGCGGTGACACGGAACTGATCGGTCTGGACGGCACGCCAGTGGTAGAAG
GGTCGGGCGACACCAATGGACAGATCGGAGTTATTAATATCGGCGGTCCGGAGTACGAGAAGCAGTTGCAAAAATGCCTGCTCTACATTGTTACC
GCCAGCGGGAAAAACACTGCGCAGGCCTATGAGAGGACTTCCCCATATACGGCTGCCTACAAACTGCCCGTGGAGATGCGTGGATTTCTGAACGA
AACATTCAAGTGGCGGCTTTTGTCAGCGGAATCGCCGCCAGAAAAGTCCATGGTCTTTGGCGCTCCCCACCTGGTTAGGCTAATGATTAAAATGC
CCATGTTCTTAAACGCATCGCCGATCAGCAACAAGAAGCTAGAAGATCTACTTCCCCACCTCGACGCCTTCATCAACTACTTGGAGAACCACAGG
GAGTGGTTCGACAGGGAAAACTTTGTTAACTCCACTGCCCTGCCCCAGGAAGATCTGCAGCGGGAGCTGTTGGACTCCCTGGATGGGATTGCTGC
TTAG
(SEQ ID NO: 479)

Start ATG: 81

MTELRDETPLFHKGEIVLCYEPDKSKARVLYTSKVLNVFERRNEHGLRFYEYKIHFQGWRPSYDRCVRATVLLKDTEENRQLQRELAEAAKLQIR
GDYSYKGTPDKPSAKKKRGGKAAHVEEPIVVPMDTGHLEAEHEMAPTPRAAGNRTRDNSGGKRKEKPPSGDGRLKGNRGRQTETFYNNAINDVSV
YNHVPQEDRIMMRVSERLRELIEYDRNMIKVLGKQHALPARVPIVTIMENFVKQQAVELAISIKQDSSRARNTQSRNARMEREYDRVMSTVCMLK
EVVDGLRIYFEFHVDDHLLYTEEKEYVHNYLTDDNMRNCSLILNKSYEYINPSGDTELIGLDGTPVVEGSGDTNGQIGVINIGGPEYEKQLQKCL
LYIVTASGKNTAQAYERTSPYTAAYKLPVEMRGFLNETFKWRLLSAESPPEKSMVFGAPHLVRLMIKMPMFLNASPISNKKLEDLLPHLDAFINY
LENHREWFDRENFVNSTALPQEDLQRELLDSLDGIAA*
(SEQ ID NO: 480)

Name: LETHAL-3
Classification: tumor_suppressor
Gene Symbol: msl-3
FlyBase ID: FBgn0002775

Celera Sequence No. : 142000013384580
GTTGTAATGAGAGCAAATCATCGGTCAGCATTATACACAAAAGTTAAAAGTATCGAGTTCTAATTAAAATGCTTCATTTTAAATGTTAAAGGTGC
GTTCGTCACTAAGCTAGTGCTTAGAGTATCAAAACGGAAGTGGCTTGCAACATGTTGATGCAAACAGTATTATTAGCACTGGTGGCGAAAAGCGA
TAAATTAGTAGCGCTCAATAAATACGTCAGCCACTCAGACAATTGGGGCTTTTGCCACATTAATCAAAACCTCAGGTGGATGCAGTCTCACCTGC
AACAAGCCTCCCATTTTCTTCCGCCTCCTATTCTGGTTTTACCCAATTTCGTTGTGCTTCGGTTGCATTTGGAGTTTCAATTGGTGCACGCAGTG
GTTAAATGCAACGAAAATCTTTATTTCATCGTGCATGTGTGCAATTAAGCTGCCTGATTGATACATTTTGATTGATTAATGGGATTCAAAGTACG
TGCGTGCTGTCTAAGCAATCAGCCGACACTTCGCCCGGTAAAATACGGAGCTGCGATTCTTTAAGGTAAACAATTCGTAGGAGGCGGTAATGTTT
GCAAATTTTGTAGCGTTTTTCAACAGATTTCATGATGATATTTGTTCGTTTACTACAAGAAATGTGCAATATGCTTTACTCAGTTTATCATATTA
ATACAAATAAAAAATTGTAAACAAATAAGAATAACAAACCTTAACTAGCAACAGCTGATTAACGTAAATGAAAAAAAGCTGAAAGATATGCAACG
CAAAAATACCATAAATTCGGTATTTTCCGGTTCGTACACCATTCAACTCTTGCTCTCTAACCAAGTAGATGTAACATAATTTATTTAAATATTTG
TATTTTATACAAACGATTTAATTGAATGTGAACAGAGTGCAGTGTAAAATGTTCACAAGCACCCGAGATCAAAAGTAAACACAACACCGCAAGTT
GGTATTATGCAGACATACGAATGCGGCAACACTAACGTATTTGCCAAAAAATGCGCATAAATATCGAAGTGAATTTGATAATATAAAAAAACCAA
GTTAACTACGCTATCGAAAATGTCTGTGCTGCGATTCCTGGTGACGCGCCAGGCCTTGGCTGCCTTAACCAGACCAAGGACCCTCAACATTATCC
AAAATCCAGCGCAAATCGCCTACGCCTCCACTTTGTGCAATCAAAATAGCAATCATAATGCCAAGGATCTGACCAAATCGAGTGCCAATTTAAGT
CTGATGCAAACTAGGGGCCATAAACGTTTTGGTCATCAGGAGGAGAAGACGCCCAGTGTGACAAAGTACTTCCACATGTTCATTCTCAGTTTATT
CCTCATTTCGGTAATGGACTGGGGCAAGTGAGTAAACTAACCAATAAAGTATTTTCAACCAAGTCCAAACTACTGAATTGGAATCTATTTTTAGA
GTGAAACGCATGTTGACGCCAAAAGTGGACGCAGATGCTGGACAACGTCCGTCATCGGCGGCCGACGTTAATGGCGAGGATAAGTCATCCGAATC
CGAATCGGAAGATAGCGAGGACGAGGAGGCAGGATCCGATCTGCACCTGCACGAGGGCAAGAAGATCCGCGAGAAAGTCGGTTTCCGCGAGAGGA
AGGTATAAAGCTGCTTGACGATGCTATAACTCTGTAAAAAGTATCATTATATTCTGCTTAAATTCTGGGTCTCACAATAGTTCCAATTTTTGGTT
ATGTTACTAATTGTGAGGACCGGAAAAATCGTAACTTTTCTTTTAATATATTTTAAACTTTCGTATATTATGTTAAACCAAAATGTTTGATTTTT
ACTTTTTCTTTTATGTTTGTGACGTCTTGTTTTTGACCCACCATCAAACACATTAAACACACACACACCGCGAAGATCATTGAGTATGAGAACCG
AATCAGGCAGTTCTCCACCCCCGACAAGATTTTTCGTTATTTTGCCACCGTAAGACTGCAGGATGCGACCCAAACGATTGTCTGCATGACTCCCG
AGGATTTTCTTCGCTCCATTTATCCGGGAATCAAGCAGCCAGATGGTAAATCACTCATTCAAATGAGCATATGTAATTATATCTTTAGTTATTGG
ATTAACTTGAGTAAGGATATTTTTTTTTATTGTATTAGTTGTTTTGGTTGGCATAACTTACTTTTCATAATTTGAATAATGCTCATAATTGATGC
ATTTTCGTAAGCTAAACTCACGTTGTTTGCCTTAGATAATTGAGTATGAGAACCGCATACGGCAGTTCTCCACGCCGGACAAAGTGTTTCGCTAC
TTTGCCACCATACAGGTGCCCGTGGCGGATGATCGTCATGAGGTCTACATGACTCCGACCGACTTTCTAACAAGCATGACGCCCGGCATGAAGCA
GCCAGATGGTATGTGCAAGAAAAAACCCAGGGAAAAACTTAAGAAAGCCAGTAGTTGTAGCACTTACTAACTGACATTATGATTAGAGAGCTCCT
GCAATAATAGCTATATATATTTTAGGATTGGGCCTGGACCAATATCGTCGCTATGATCCCAAGGTGAGTCTAAAATGCATTTGTAATACAAGTTA
ATAATCCCTATTTTTCCCTACTAGTCTGTTGGCGAGCAGCTCAATTTGCATCTGGAGAAGAATAGCATTTTTTACAAACTAGGCTCTTACGGACT
GATCACATTCTCAGACTACATCTTCCTGCTCACAGTCCTCTCGAGTAAGTGATAAGTATTCCCATTAGGATACATTCCAATAACCACGTTTTCTT
TATAGTTTCACGACGCCACTTCGAGATTGCCTTCCGCATGTTTGACTTGAATGGGGATGGTGACGTGGACTGCGAGGAATTCGAGATGGTGGCCA

FIGURE SHEET 265

CCTTGGTGAGGCAGCAAACCAGCATGGGAACCCGACACCGCGATCACGCCAATACAGGGAACACTTTTAAGGTAATGAAACTCATTTGCCCTAGA
TTTTAATCAATAAGAGTACCTCGAGCCGTACTAAATACGATTCCTTGTGTATTTTTGTATATTCTCTGTCTTTTCGCTTTGACCCTATATATTGA
ACGCGTGTCTAAACTGTGTACATATCAAATCTTAACTCCCCTCTGTTTTTGACGTACTTACAGTCCTTGAAGGTACTTTGTGTGATAATGCTTAT
TGACTTATTTTGGCTTTTCAAATTTTCTTTCGAAAACACCCGAACACAATCTCACTCAAGTTAAACTAAATCATATTTCACGTAGTTAATTCCAC
GATGCACCTGCTCCCATGCACACAAATTACTCTTTTTTATATCCAACTTGTCGTTTCTATTTTTGGAAATATTAATTGCTTAATTTTAAATTGTT
TTCTTAGGGTGTGAACTCGGCTTTGATCACATATTTCTTTGGACCCAATATGGATGAAAAGTTGACAATAGAAAAGTTCCTGGATTTCCAGGAGC
AACTGCAAAGGGAGATCTTGTCACTCGAATTCGAAAGAAAAGAACCGAATGATGAGGGGAATATAACAGAAGCGGATTTTGCAGAACTCCTACTG
GCCTACGCTGGATATCCGTTAAAAAAGAAACAAAAGAAGTTGAAGAGGGTTAAGAGGAGGTTTAGGGACCATGGCAAAGGCATCTCCAAACAGGA
CTATCTGGATTTCTTTCATTTTCTGAACAACATCAATGACGTGGATACTGCCCTTACTTTCTACCACATTGCGGGTGCCTCGATTGACCAACAAA
CATTGCAACATGTGGCCAAAACGGTGGCCATGGTCAATCTTTCGGATCATGTGGTGGATGTGGTCTTTACCATCTTTGATGAGAATAGTAAGTTC
GTAATTGAGTGTAATTAGAATAACAATCTTAATTCATTCGGCAAACCTCTTTCAGATGACAACCAACTCAGCAACAAGGAATTTATTTCGGTAAT
GAAGAATCGCGTGCAGCGCGGATTGGAGAAACCCAAAGACACAGGATTCCTAAAGATGATGCGATCGGTGTTCAAGTGCGCCAAGGAAACCAAGC
CTGTGCTGCTGGACATCTAAAGATCGTCACTATGTGGATTCTCCCGCTTCAAGCGCCCCAATCTTAGTCACTTTTTCCTACGCTTACGCTTTTTA
CTATTTATTTTTGTAGTTAACGTTTACATCAATCGATTTTAGCTCAATCTTTGTAATTGTTCGACCCCCGGCAGGTTGACGACTGTCTTCTGTAT
ATTTCACCGTCTCTTGTGCACTTAACTCGTTTATTTTTTAATAAAAATATTATATTTATAAATAAGTACATCTTTAGGAATTTTTGCTGTAGCTC
ATCATTCAGTTCTTGGATTATGGCGCACGTTACATTTTACATTTCAAAAGTGTATTATAAGTGCTTAAAAAAGAATATGAATGAATAAATTAATA
GTGATATAAAACACTTTAAAAAGATATGAATATATTAATAAGGAATGTTTTAATGATCCTTAATAGCTAATTTATATGAAATATGGGATTTTCAA
TCCTCTTTATGCATTAAAAAGAATGACCAAGAGTTTACAACTCTCGCGCAGTTAATATTAATTGTGGGCTCAAAACATTTTCTATGCCACATCTA
CGTCATCCTGCTCCTCGTCCGCCACATCATCAATGCTCATCCCGTACAACTCCAAGTCGTGCTTTTTAAGATGGGCCGTATAAGCATCCAACTCG
GTGAATCGTTGCTGACACTCGCAGCACTCTAGGCAATCTTCCACAGAACTGTCGCCATCGTCGTCACTCTCGTAAATGGACGACTTGCGGCTACT
CAGCTGATCCTGATGATTGTTCTTGTGATCCGAGTACTCCAGATAGTCCCTGAATTTGGAGGGACACCTCAGGCACTTGTACCAGCGATCCCTGA
CATGGGTGACCATGTGTTTCTTGAGCGTGGAGCACTCCCTGAAGGGTTTCCTGCATTTTGAGCAGCTAAATGGTTTCTCGCCAGTATGGATCATA
TAGTGGCGTTTAAGATTATGACGAGTTCCGAAAGGACGATGACACAAAGGACACGGATAAGATCTGCGAG
(SEQ ID NO: 481)

Exon: 1001..1357
Exon: 1425..1617
Exon: 1881..2040
Exon: 2496..2533
Exon: 2590..2704
Exon: 2761..2921
Exon: 3333..3792
Exon: 3856..4010
Start ATG: 1065

Transcript No. : CT14629
ATGCGCATAAATATCGAAGTGAATTTGATAATATAAAAAAACCAAGTTAACTACGCTATCGAAAATGTCTGTGCTGCGATTCCTGGTGACGCGCC
AGGCCTTGGCTGCCTTAACCAGACCAAGGACCCTCAACATTATCCAAAATCCAGCGCAAATCGCCTACGCCTCCACTTTGTGCAATCAAAATAGC
AATCATAATGCCAAGGATCTGACCAAATCGAGTGCCAATTTAAGTCTGATGCAAACTAGGGGCCATAAACGTTTTGGTCATCAGGAGGAGAAGAC
GCCCAGTGTGACAAAGTACTTCCACATGTTCATTCTCAGTTTATTCCTCATTTCGGTAATGGACTGGGGCAAAGTGAAACGCATGTTGACGCCAA
AAGTGGACGCAGATGCTGGACAACGTCCGTCATCGGCGGCCGACGTTAATGGCGAGGATAAGTCATCCGAATCCGAATCGGAAGATAGCGAGGAC
GAGGAGGCAGGATCCGATCTGCACCTGCACGAGGGCAAGAAGATCCGCGAGAAAGTCGGTTTCCGCGAGAGGAAGATCATTGAGTATGAGAACCG
AATCAGGCAGTTCTCCACCCCCGACAAGATTTTTCGTTATTTTGCCACCGTAAGACTGCAGGATGCGACCCAAACGATTGTCTGCATGACTCCCG
AGGATTTTCTTCGCTCCATTTATCCGGGAATCAAGCAGCCAGATGGATTGGGCCTGGACCAATATCGTCGCTATGATCCCAAGTCTGTTGGCGAG
CAGCTCAATTTGCATCTGGAGAAGAATAGCATTTTTTACAAACTAGGCTCTTACGGACTGATCACATTCTCAGACTACATCTTCCTGCTCACAGT
CCTCTCGATTTCACGACGCCACTTCGAGATTGCCTTCCGCATGTTTGACTTGAATGGGGATGGTGACGTGGACTGCGAGGAATTCGAGATGGTGG
CCACCTTGGTGAGGCAGCAAACCAGCATGGGAACCCGACACCGCGATCACGCCAATACAGGGAACACTTTTAAGGGTGTGAACTCGGCTTTGATC
ACATATTTCTTTGGACCCAATATGGATGAAAAGTTGACAATAGAAAAGTTCCTGGATTTCCAGGAGCAACTGCAAAGGGAGATCTTGTCACTCGA
ATTCGAAAGAAAAGAACCGAATGATGAGGGGAATATAACAGAAGCGGATTTTGCAGAACTCCTACTGGCCTACGCTGGATATCCGTTAAAAAAGA
AACAAAAGAAGTTGAAGAGGGTTAAGAGGAGGTTTAGGGACCATGGCAAAGGCATCTCCAAACAGGACTATCTGGATTTCTTTCATTTTCTGAAC
AACATCAATGACGTGGATACTGCCCTTACTTTCTACCACATTGCGGGTGCCTCGATTGACCAACAAACATTGCAACATGTGGCCAAAACGGTGGC
CATGGTCAATCTTTCGGATCATGTGGTGGATGTGGTCTTTACCATCTTTGATGAGAATAATGACAACCAACTCAGCAACAAGGAATTTATTTCGG
TAATGAAGAATCGCGTGCAGCGCGGATTGGAGAAACCCAAAGACACAGGATTCCTAAAGATGATGCGATCGGTGTTCAAGTGCGCCAAGGAAACC
AAGCCTGTGCTGCTGGACATCTAA
(SEQ ID NO: 482)

Start ATG: 65

MSVLRFLVTRQALAALTRPRTLNIIQNPAQIAYASTLCNQNSNHNAKDLTKSSANLSLMQTRGHKRFGHQEEKTPSVTKYFHMFILSLFLISVMD
WGKVKRMLTPKVDADAGQRPSSAADVNGEDKSSESESEDSEDEEAGSDLHLHEGKKIREKVGFRERKIIEYENRIRQFSTPDKIFRYFATVRLQD
ATQTIVCMTPEDFLRSIYPGIKQPDGLGLDQYRRYDPKSVGEQLNLHLEKNSIFYKLGSYGLITFSDYIFLLTVLSISRRHFEIAFRMFDLNGDG
DVDCEEFEMVATLVRQQTSMGTRHRDHANTGNTFKGVNSALITYFFGPNMDEKLTIEKFLDFQEQLQREILSLEFERKEPNDEGNITEADFAELL
LAYAGYPLKKKQKKLKRVKRRFRDHGKGISKQDYLDFFHFLNNINDVDTALTFYHIAGASIDQQTLQHVAKTVAMVNLSDHVVDVVFTIFDENND
NQLSNKEFISVMKNRVQRGLEKPKDTGFLKMMRSVFKCAKETKPVLLDI*
(SEQ ID NO: 483)

Celera Sequence No. : 142000013384580
AAAAGAAGTTGAAGAGGGTTAAGAGGAGGTTTAGGGACCATGGCAAAGGCATCTCCAAACAGGACTATCTGGATTTCTTTCATTTTCTGAACAAC
ATCAATGACGTGGATACTGCCCTTACTTTCTACCACATTGCGGGTGCCTCGATTGACCAACAAACATTGCAACATGTGGCCAAAACGGTGGCCAT GGTCAATCTTTCGGATCATGTGGTGGATGTGGTCTTTACCATCTTTGATGAGAATAGTAAGTTCGTAATTGAGTGTAATTAGAATAACAATCTTA
ATTCATTCGGCAAACCTCTTTCAGATGACAACCAACTCAGCAACAAGGAATTTATTTCGGTAATGAAGAATCGCGTGCAGCGCGGATTGGAGAAA
CCCAAAGACACAGGATTCCTAAAGATGATGCGATCGGTGTTCAAGTGCGCCAAGGAAACCAAGCCTGTGCTGCTGGACATCTAAAGATCGTCACT
ATGTGGATTCTCCCGCTTCAAGCGCCCCAATCTTAGTCACTTTTTCCTACGCTTACGCTTTTTACTATTTATTTTTGTAGTTAACGTTTACATCA
ATCGATTTTAGCTCAATCTTTGTAATTGTTCGACCCCCGGCAGGTTGACGACTGTCTTCTGTATATTTCACCGTCTCTTGTGCACTTAACTCGTT
TATTTTTTAATAAAAATATTATATTTATAAATAAGTACATCTTTAGGAATTTTTGCTGTAGCTCATCATTCAGTTCTTGGATTATGGCGCACGTT
ACATTTTACATTTCAAAAGTGTATTATAAGTGCTTAAAAAAGAATATGAATGAATAAATTAATAGTGATATAAAACACTTTAAAAAGATATGAAT
ATATTAATAAGGAATGTTTTAATGATCCTTAATAGCTAATTTATATGAAATATGGGATTTTCAATCCTCTTTATGCATTAAAAAGAATGACCAAG
AGTTTACAACTCTCGCGCAGTTAATATTAATTGTGGGCTCAAAACATTTTCTATGCCACATCTACGTCATCCTGCTCCTCGTCCGCCACATCATC
AATGCTCATCCCGTACAACTCCAAGTCGTGCTTTTTAAGATGGGCCGTATAAGCATCCAACTCGGTGAATCGTTGCTGACACTCGCAGCACTCTA
GGCAATCTTCCACAGAACTGTCGCCATCGTCGTCACTCTCGTAAATGGACGACTTGCGGCTACTCAGCTGATCCTGATGATTGTTCTTGTGATCC
GAGTACTCCAGATAGTCCCTGAATTTGGAGGGACACCTCAGGCACTTGTACCAGCGATCCCTGACATGGGTGACCATGTGTTTCTTGAGCGTGGA
GCACTCCCTGAAGGGTTTCCTGCATTTTGAGCAGCTAAATGGTTTCTCGCCAGTATGGATCATATAGTGGCGTTTAAGATTATGACGAGTTCCGA
AAGGACGATGACACAAAGGACACGGATAAGATCTGCGAGTGCGACTCATGGACTTTCCAGCTATATTTCCATCGTTGCTCAAGGAAGATGAGGAG
TTGGCACTGCTGCAGCTGCGAGGAAGTGGCGGGCGACTTGGCTGCGTGTGTGAAGGAACTTTTTCCGGTGGAGATTGAATAGGTGGTATTAAAGT
AACCATTAAACTGGGTTGTGTTGCCACTTGTGGCTGCTTCTCATTTTCTAGAGCCGCTTCCTCTATTTCGTCATCATCCCCTTCCATCTCATCCG
AATGTTCCTCCGTTGTTTTTTCGCCCAGTTCCTCTGGTTGAGGTTTTACCATAAGATTCTTGCTTTCACAATCCGCACACCTTGTAGAGTCCTGC
TCCAAAGGTGCTCCCAAGTGACAGATCATGCAAATGAATTGTGGATCGTGTGAGTGCCTTCGACGATGCTTTTTAAGATCGCTGAATTCCCGAAA
ACGTCGCTCGCACAGATCACAAGGGAATGGTCTTTCACCTGGGGAAAATTTAGTAGAAAGTGATAAGTGGAGGTATTTGAATATTTTATGCGAAG
TTTCGTACCTGTGTGGATCATCATATGACGTCTTAGATTGTAATTAGATTGCACTTTCTTCCCGCAGTCAGGACATTCGTACATATGCCTTCCCC
TTCTGTTGGCACCTGGACGCCTCTTTACTAATCTCCTCGACCCAGAAGATTTCCTCTTGATGACATTGTCTGTCTTCTGTTCGTCCTCCTGGTCG
GAGGGCACGATGATCACCAGTTCCTGTGGATTCTGGCTTCCATCCTGTCTCTGCTCATTCAGGACGCAGCTTACAGCGTTTGATGGAAGACTTAC
ATCCTCATCTACTTCACTATCTTCATCGTGATCACTATCACTCAGTTCGATTTCTGCGACAACCCTGTGCACCCGTCTGGGAATCAGTTCGATAT
CTGGTGTTACCCTCCTAATGGATGAATTCCAATGGGCTAGACTCCTGGCTGCGCTGATTATGAGACCCCGAGGAGATTGAGCCTCCTCCTCGTCC
AATTCGATTACCTCTTGATCTCTTCGCTTTTCGGCCTCCCGCCTTTCCTTCTCTCTTTTCTCCCTTTTCTCTTGTTCCATGATCCTTTTGATTTC
CAACTCCTTTTCCCTCTGCTGCTGGCCGATTTGCCACAGGAAACTCTTGATTTTCACATCATCAATGGATATGAAGTTCTCCTCGGGCTCCTGGT
ACTCATATCTGACTGGATCGGGCGGTATTAACCCGCAGGCGGCGTCGCAGCTAGCGTCGCAGCAGGCGGAGGCAGAACAGCAGGGCAGCAGAGTG
CAGTCCTTGCAGCAGTCCACGCAGGATGATGGTTTATTCAGAGCCAGCTCCATCAAATCTGCAATGTTACAATAAACAATTTAGAAAAGTTTAAG
AAAGGAACGTAAGAATTGCACTATCATTGTACTATCAGAAAAAAACATTGCATACATGTAGGCGTGTTTTATATAAATCACATTCTACTATGGAT
AAATCGGCACTTATCAGTATTTCCAAGAAGCGTACTTTCTAGTATCGAATAATCACAATAAAACCTCTCAAACCATAAAAAAAGAATATATTATA
GGGCACTACATTTCCATCGATCACATTGAATAGCCTGTATTGGTTTATATTAATATCCTGGACAAGTCGCATACGAACCATTGATAACCCAGGAG
ATTCCGATCGAATGAATTCTGCGATTGCACACACACCCCTCTCTCACACTTTACAAAGCTTCGCTCCTTTCTTTCGTTTTTTATCCGCAATTTGT
GCGCTCGGCGCTGCGTCTGCCGTGCGAAGAAGTGAAGAAGAAACTGGATTCGCGATTCGCGATTTGCGGCTTGCCGAGCAGCAACCTCTCGGCAA
AAACAACAAAACGCCGCAAAAGTCGAGCTTCGAGTTGACGCCGACTGCGCTGCCCGGCTTGTGAATCAGCGAAGCGAGCAGAGCAGCAGCAGCAA
CAACAACAACAACCATGTGGGCAGCGCTTAAGGCTTTTTTTTTGTGTGCACGAACGTGAGCCTTTAGCCCCCCTTTCCCACCACTGCCCATTGGC
GTGTTAACTTGATTTTTCTTGGGGCCACGCAAGAGCGAAACACGAAAAACAAAGAAAATGCCCCACAACAACAACAAGGGCAACAACAAAAACAA
TGCAATTACAGCCGGAGCAACAGGCGCAGCAGCAACAACAACTCACGATTTTCAAGATTGCTCACAAGAGCAGGGGCGTAGGCAGGACATGAGAA
GGGGTGAGGTTACCAGGAGTGAAAGGAATTCCTTACTATATATACTTGTATATAACAACGATCTAATCTTCAATGAAATGCCAAAAAAAAGATAA
TTTGCTTT
(SEQ ID NO: 484)

Exon: 2808..2004
Exon: 1938..1001
Start ATG: 2808 (Reverse strand: CAT)

Transcript No. : CT14635
ATGGAGCTGGCTCTGAATAAACCATCATCCTGCGTGGACTGCTGCAAGGACTGCACTCTGCTGCCCTGCTGTTCTGCCTCCGCCTGCTGCGACGC
TAGCTGCGACGCCGCCTGCGGGTTAATACCGCCCGATCCAGTCAGATATGAGTACCAGGAGCCCGAGGAGAACTTCATATCCATTGATGATGTGA
AAATCAAGAGTTTCCTGTGGCAAATCGGCCAGCAGCAGAGGGAAAAGGAGTTGGAAATCAAAAGGATCATGGAACAAGAGAAAAGGGAGAAAAGA
GAGAAGGAAAGGCGGGAGGCCGAAAAGCGAAGAGATCAAGAGGTAATCGAATTGGACGAGGAGGAGGCTCAATCTCCTCGGGGTCTCATAATCAG
CGCAGCCAGGAGTCTAGCCCATTGGAATTCATCCATTAGGAGGGTAACACCAGATATCGAACTGATTCCCAGACGGGTGCACAGGGTTGTCGCAG
AAATCGAACTGAGTGATAGTGATCACGATGAAGATAGTGAAGTAGATGAGGATGTAAGTCTTCCATCAAACGCTGTAAGCTGCGTCCTGAATGAG
CAGAGACAGGATGGAAGCCAGAATCCACAGGAACTGGTGATCATCGTGCCCTCCGACCAGGAGGACGAACAGAAGACAGACAATGTCATCAAGAG
GAAATCTTCTGGGTCGAGGAGATTAGTAAAGAGGCGTCCAGGTGCCAACAGAAGGGGAAGGCATATGTACGAATGTCCTGACTGCGGGAAGAAAG
TGCAATCTAATTACAATCTAAGACGTCATATGATGATCCACACAGGTGAAAGACCATTCCCTTGTGATCTGTGCGAGCGACGTTTTCGGGAATTC
AGCGATCTTAAAAAGCATCGTCGAAGGCACTCACACGATCCACAATTCATTTGCATGATCTGTCACTTGGGAGCACCTTTGGAGCAGGACTCTAC
AAGGTGTGCGGATTGTGAAAGCAAGAATCTTATGGTAAAACCTCAACCAGAGGAACTGGGCGAAAAAACAACGGAGGAACATTCGGATGAGATGG
AAGGGGATGATGACGAAATAGAGGAAGCGGCTCTAGAAAATGAGAAGCAGCCACAAGTGGCAACACAACCCAGTTTAATGGTTACTTTAATACCA
CCTATTCAATCTCCACCGGAAAAAGTTCCTTCACACACGCAGCCAAGTCGCCCGCCACTTCCTCGCAGCTGCAGCAGTGCCAACTCCTCATCTTC
CTTGAGCAACGATGGAAATATAGCTGGAAAGTCCATGAGTCGCACTCGCAGATCTTATCCGTGTCCTTTGTGTCATCGTCCTTTCGGAACTCGTC
ATAATCTTAAACGCCACTATATGATCCATACTGGCGAGAAACCATTTAGCTGCTCAAAATGCAGGAAACCCTTCAGGGAGTGCTCCACGCTCAAG
AAACACATGGTCACCCATGTCAGGGATCGCTGGTACAAGTGCCTGAGGTGTCCCTCCAAATTCAGGGACTATCTGGAGTACTCGGATCACAAGAA
CAATCATCAGGATCAGCTGAGTAGCCGCAAGTCGTCCATTTACGAGAGTGACGACGATGGCGACAGTTCTGTGGAAGATTGCCTAGAGTGCTGCG
AGTGTCAGCAACGATTCACCGAGTTGGATGCTTATACGGCCCATCTTAAAAAGCACGACTTGGAGTTGTACGGGATGAGCATTGATGATGTGGCG
GACGAGGAGCAGGATGACGTAGATGTGGCATAG
(SEQ ID NO: 485)

Start ATG: 1 (Reverse strand: CAT)

MELALNKPSSCVDCCKDCTLLPCCSASACCDASCDAACGLIPPDPVRYEYQEPEENFISIDDVKIKSFLWQIGQQQREKELEIKRIMEQEKREKR
EKERREAEKRRDQEVIELDEEEAQSPRGLIISAARSLAHWNSSIRRVTPDIELIPRRVHRVVAEIELSDSDHDEDSEVDEDVSLPSNAVSCVLNE

QRQDGSQNPQELVIIVPSDQEDEQKTDNVIKRKSSGSRRLVKRRPGANRRGRHMYECPDCGKKVQSNYNLRRHMMIHTGERPFPCDLCERRFREF
SDLKKHRRRHSHDPQFICMICHLGAPLEQDSTRCADCESKNLMVKPQPEELGEKTTEEHSDEMEGDDDEIEEAALENEKQPQVATQPSLMVTLIP
PIQSPPEKVPSHTQPSRPPLPRSCSSANSSSSLSNDGNIAGKSMSRTRRSYPCPLCHRPFGTRHNLKRHYMIHTGEKPFSCSKCRKPFRECSTLK
KHMVTHVRDRWYKCLRCPSKFRDYLEYSDHKNNHQDQLSSRKSSIYESDDDGDSSVEDCLECCECQQRFTELDAYTAHLKKHDLELYGMSIDDVA
DEEQDDVDVA*
(SEQ ID NO: 486)

Name: zinc finger protein
Classification: transcription_factor

Celera Sequence No. : 142000013385212
AATGTTAGTGTAAATAAATTACCTTTATCGGTAAATCCATGTGCTCGCTGCTGCAGCTGGACCCATACATAACCTCAAACCAGAATGTAAATTCT
GGAAATAAAAGAAAATGGCATCAATACAGTGTGTACAAGGAGTACTTCCAAATATTTTATATATTTGATTAGGTTTCAGTTTACAATTTTCTGCA
CGGTTATGAGCTCAGTACAGGTCTGTGTAAAAGATCATCAGAGAAGCATAGACCAACCAAAAGTATTAATATCTTACCTCCAATGTGACAATGGC
GTCTCCAGTGGGCTCAGTGCCCAAGGTGTCTCAACGGGCTCACATGTTGTCCCGAGGTGTCTCACATGCACCATGCACGTGGAGTGCCCGGATTT
CGATTTATCCAAATGCTTAGGGTTTCAATATTGTTCACTGCAAGAAATACAGAACTTTTAGAACATATTCTTGCCAAACCCAAAGAAAGTTCTTG
AAGTTATATGCCATCAGATCGCCGAATCATCTTAAATGAACAAATATATAACGAGGCACTGAAAAATACAGCGCCAAGTCGAGAATTTGTTCCTT
CAGTCTCGTCATCTGTTTCATCATTTGAGGCATAACACTCTTCCATTTAAGCACTTTAATTCACTTGATATAAAACTATTTACGAAGAGCACACA
ACTTACCATTTCGAGTCTTGAAATAAAATGAACGAGTTTCGTCATCGCACGTGGAAGGAAAAATTCTGTGAAAAGATGGCGGCCAACTATCGATG
TCTCTGAATGCAACCATGGTAGTATCGTATCGGAAAAATTGTTTGGTTTTTGCCTGATATATATTGTATAAGAATGTGCAATAATTAACTTAACC
GAATAAATGATATTCCATTTAATTTTCATTAAATCATTCATAAAATACTTAATATATGAAAAACTTTCATATTTATATGTTAATTCGATGTATCG
ATTGCCTATCGCTGTCTTCGGTGATCTAGCCCAAACAGCTGATTTTACCAAAATACTTACCACACGTGTGCCACTTTTTAAGTTATATTGTTTAC
AGTTTTTGGGAATTACAGCTTACAATGGTATATATAAATCTTTAATATTTAATTAAACCCGACCTAACATCTTCAGTTCTTTTGCAGGGAAAACA
CAAGAAAACGCAGAAGGTTAAGAAACAACGTAATGCACAGCTTAAACGCATCATAAAACCCACAGACGCGCGGCTTAAGGATCAGATTCGAGTGA
AAAGAAAGAAGGCCGAGGATCCGCACCAGATCAAGGTGCACGAGGCCACCCAGCAGAGCTCCGCTCTGTTCTTCCAGTACAACACCCAGCTGGGA
CCGCCGTACCACATCGTTCTGGACACGAACTTCATTAACTTTAGCATTAAGAACAAACTGGATATTGTGCAAGGTATGATGGACTGTCTGTATGC
CAAGTGCATACCCTATATCTCCGACTGCGTGCGTGCCGAGCTGGAGAAGCTGGGCAACAAGTACAAGCTGGCCCTGCGCATCATCTCCGATCCCA
GATTCGAGCGACTGCCGTGCCTGCACAAGGGCACCTATGCGGACGATTGCCTCGTGGAGCGGGTGCGCCAGCACAAATGCTACATTGTGGCCACC
AACGACAAGGACCTTAAGAATCGCATCCGGAAGATTCCCGGCGTGCCCATCATGTACGTGGCTGCGCATAAGTACGCGATTGAGCGTATGCCAGA
AGCGTATGGAGTCAAGGCGTAGACCTTTTTTACTTCTTATCCTAAGTGTACATTTTTAAATATATTCTTACATGTAAGCAGCAAGCAATGCGTTT
CGTATTTCCTGTTGTTTTTAGTAGAATGCTTTTACTGCATTGTCTGGATCAACAAAGGAGACATAAGTTCTATTAAGTTACAAATAGTTTAACT
ACAACAGAATCTCCAAATCGACCAATGTCCACAACAATAACAAACACGAAGCGATTACATTTAAAAGTTTATGACTTTATTCAAAAACTCTGGAT
TGATTGGCCTCGAAAGTGTTCACTTAGGCATCGGCGTGCAGACGAGGAGTGGGCTTGGACAGGAAGTCCGAGTATGCCTGGTAAGGAGTGGAGCC
CAGAGGCATCTCCTTCCACAGATCGGGGGTCAAGTACGCGTACGTCTTGGCGATGGCGGCATATGTAGCCTTGGCGAAGTTGCCGAGGGTTCCAG
TGGAGCCACGGGCCGAGGTGTAGCAATCCTCAATACCGGCCATGGTCAGCAGCTTCTTGGGCACGGGGGCCGAGACAATGCCAGTACCACGGGGA
GCGGGGATGAGGCGCACGGAGACGGAACCGCACTTGCCGGTGACCTTGCAGGGCACGGTGTGGGGCTTGCCGATCTTGTTGCCCCAGTAGCCACG
GCGCACGGGCACCACGGAGAGCTTGGCCAGAATGATGGCACCACGGATGGCGGTGGCCACTTCCTTGCTGCACTTAACGCCCAGACCAATGTGGC
CATTGTTGTCGCCGATGGCAACGAAGGCCTTGAAACGGGTACGCTGACCAGCACGGGTCTGCTTCTGGACGGGCATGATCTTCAGCACCTCATCC
TTCAGCGAGGATCCCAGGAAGAAGTCGATGATCTCGAACTCTTTGATGGGAAGCGAGTACAGGTAGATCTCCTCCAAAGACTTGATCTTGCCCTC
GCGCACCAGGCGTCCCAGCTTGGTCACTGGCACCCACTCCTTGGAGTCCTCCTTTCCACGTCCACGGGCCCA
(SEQ ID NO: 487)

Exon: 1001..1072
Exon: 1133..1732
Start ATG: 1409

Transcript No. : CT14682
AAATACTTACCACACGTGTGCCACTTTTTAAGTTATATTGTTTACAGTTTTTGGGAATTACAGCTTACAATGGGAAAACACAAGAAAACGCAGAA
GGTTAAGAAACAACGTAATGCACAGCTTAAACGCATCATAAAACCCACAGACGCGCGGCTTAAGGATCAGATTCGAGTGAAAAGAAAGAAGGCCG
AGGATCCGCACCAGATCAAGGTGCACGAGGCCACCCAGCAGAGCTCCGCTCTGTTCTTCCAGTACAACACCCAGCTGGGACCGCCGTACCACATC
GTTCTGGACACGAACTTCATTAACTTTAGCATTAAGAACAAACTGGATATTGTGCAAGGTATGATGGACTGTCTGTATGCCAAGTGCATACCCTA
TATCTCCGACTGCGTGCGTGCCGAGCTGGAGAAGCTGGGCAACAAGTACAAGCTGGCCCTGCGCATCATCTCCGATCCCAGATTCGAGCGACTGC
CGTGCCTGCACAAGGGCACCTATGCGGACGATTGCCTCGTGGAGCGGGTGCGCCAGCACAAATGCTACATTGTGGCCACCAACGACAAGGACCTT
AAGAATCGCATCCGGAAGATTCCCGGCGTGCCCATCATGTACGTGGCTGCGCATAAGTACGCGATTGAGCGTATGCCAGAAGCGTATGGAGTCAA
GGCGTAG
(SEQ ID NO: 488)

Start ATG: 349

MDCLYAKCIPYISDCVRAELEKLGNKYKLALRIISDPRFERLPCLHKGTYADDCLVERVRQHKCYIVATNDKDLKNRIRKIPGVPIMYVAAHKYA
IERMPEAYGVKA*
(SEQ ID NO: 489)

Classification: hypothetical

Celera Sequence No. : 142000013383795
GCCGTCCACTAGCTGCGGACAGGAATATAATCGGATTTGGTACAGAGTTCTTGTGAGGATGTAGTTGATATACGTACGCCATGCTTGTTGAGAAA
GGCACAGTAGGCCTCCGCCTCGCCGGGACCTTGGACGCACTGGATTCCCATGGAGAGCAGCAGCGTTTCGCACTGCTTGAGAACATGGTTGAACC
GGCTGCGTCCCTTGTCGCCCTTGGACGGCTGACTTTGGGTGCACTCAGGCGAATTCTTGGGCTTCACTCCCCGAAACTGGAGCTCATTCCTTTTG GCTATCACCTGGCTCTTGAGTTTTGGAGCAACTCCCTCCAAAACGAAAACCGGAGTAACTTGCTCCCAAATCAAGTAGCAAGTGCGAAAGAAGAG
GTTCCTGTTGGTAAAGCGTAAATATTAATATTTTAAAAGAATATAAGGTATTAAGAATTTTTTAAACCTACTTTAAATGATGCCTTGGATGCACA
AAGTAGTCCACAACATTAAGAGATTCGCACACCCAGCCGGCCAGGTCGATGGCCACTTTCTTTCCCCGCAGTTCATTAATGGGTTTACGTTCACA
ATGGGGCGTTAAAACACCCCATAATTCCTTGACGCCCATTTAAATAAGCTAAACAAAAACCCCGCGAGAAATTCGCAACAAATTTAAACAATCGC
TTCTTCGTCAGAGTTGCCCAATCAGTTACTTTCTAGCTACTTGAAGCTATATTCAAAAGCAGCCAAGTGCAAAGTTGTGACAATAATTGGCAATG
ATAACTTTTTTAACAATAATACATGATGCTATTTTCAATAACAAATATTATACATATAAATGTCATCTTATTCGATTTTAAGAACACATTTCGTT
TTTAGCTTTTTTTGAGCTTGTCTCTAGCTACATTTGACAGCACTGCGACTTCCGCCAGTCACTGCGAAGCATGCTCGATAACCGATAGCGGGCTT
TGTTTTGACAGCTGCACAAGCGACCGCTGCGAATGGCCAGTGGTCAGCAGTCTCTTCTTCTTCCACGTCGACGTGTCGTGTCAGCCAAAAGAAAG
TCGAAATAAAATATTGAATTGAAGCTGCCCCTTTGCGAGTAGGCCCGACAAAATTCAGAAGCTGCCAGTCGTCCGTACGCCAAACCACACACAAC
CACCACCGGCAAGATGGTTCTCGCGGATTTGGGTCGCAAGATAACAACGGCGCTGCACTCGCTCAGCAAGGCGACCGTAATCAATGAGGAGGCAC
TGAATTCCATGCTGAAGGAGATCTGCGCAGCGCTCCTGGAGGCTGATGTGAATATCCGACTGGTTAAGCAGCTGCGCGAGAATGTGCGTGCCGTT
ATTGATTTCGATGAGATGGCCGGTGGCCTGAACAAGAGGCGAATGATCCAATCGGCTGTGTTCAAGGAGCTCGTCAAACTGGTCGATCCCGGCGT
GAAACCCTACCAACCCATCAAGGGCAAGGCCAATGTGGTCATGTTTGTGGGTCTGCAGGGCTCCGGTAAGACCACCACCTGTACCAAGCTGGCCT
ATCACTACCAGAAGCGCAACTGGAAGTCGTGTCTCGTGTGCGCGGATACCTTCCGTGCTGGTGCCTACGATCAGGTCAAGCAGAACGCCACCAAG
GCGCGCATTCCGTTCTACGGCAGCTACACGGAAATCGATCCCGTGGTCATTGCCCAGGACGGTGTGGATATGTTCAAACGCGAGGGTTTCGAGAT
GATCATTGTGGACACCTCGGGTCGGCACAAGCAGGAGGAATCACTGTTCGAGGAGATGTTGGCAGTGTCCAATGCCGTCAGTCCCGACAACATAA
TCTTCGTGATGGACGCCACCATCGGACAGGCTTGCGAGGCTCAAGCGAAAGCCTTCAAAGACAAGGTGGACATCGGTTCGGTGATCATAACCAAG
TTGGATGGCCACGCCAAGGGAGGCGGAGCTCTGTCCGCAGTGGCAGCCACACAGTCGCCCATCATCTTCATCGGTACGGGCGAGCACATCGACGA
TCTGGAGCCCTTCAAGACGAAACCCTTCGTGAGCAAACTGCTTGGAATGGGTGACATCGAAGGACTGATAGATAAGGTGAGACATGCCACACGAG
CTTAAAATTATACCGCACTACAATACAATTGAAAACACGTACTGAATATAAACTCATTTTGCACAGGTAAACGAGCTGAAGCTAGACGGAAACGA
TGAGCTGTTAGAAAAGATCAAGCACGGTCATTTCACCATCCGCGACATGTACGAGCAGTTCCAGAACATCATGAAGATGGGCCCCTTCTCCCAGT
TCATGAACATGATACCCGGTTTCTCGCAGGACTTTATGACCAAGGGCGGCGAACAGGAGTCGATGGCGCGCGTTAAGCGTATGATGACGATGATG
GACAGTATGTCGGATAATGAACTGGACAATCGCGACGGAGCAAAGCTCTTTAGCAAGCAGCCAAACCGCTGCGTTCGTGTGGCCCAGGGAGCTGG
TGTCATGGAGCGCGAGGTCAAGGAACTGATTGCACACTATACGAAATTTTCGGCGGTAGTAAAGAAGATGGGCGGCGTTAAGGGACTGTTCAAGC
AGGGCGACATGACCAAGAATGTGAATCCAACACAGATGGCCAAGCTCAACCAGCAGATAGCGAAGATGATCGATCCCCGGATGCTGCAACAGATG
GGCGGCGTTGGTGGTATCCAAAATATGATGAGGCAACTGCAGCAAGGAGCTGCGGGTGGTTTGGGTGGCCTGGGGAACCTGATGAGCGGTTTTGG
TGGCAAGTGAGCAGGTGGCGTGTAAATTTAACGATTTTTATATGATTTTGTTTTCGCGTAGTTCGTAATTTGTTAGCCATTTGTTTCCATTTGTC
CAAGGCCACAAAAATTGATACGCGTTGTGGAAGCGAATATAGCGTATATAGCCTATAAAGCCCATATAGATGTGCAAACAGTTAACAAATTCGGT
TTTTGTACGGCTTGGCAGCCACAGTGTCAGTTTTTATAGTTTAAACAGTTTTCTGTACACGAACTAATGGAATTAGCATGCCTATCAGAATACCA
GTAAGGCAATTGAACTAGATATAAACAATAAATAATTAATATATGAACTTGGCTTTAAATTGGTTGTGTTTATTGGGTTTAATCTCGGGCAACGA
AAAGCAGAAATCCAGTCACCCTGTTGACCTAACACATACAACTAAAACAAAAAACAAGTTGCGAACAGGTGCCCAGAAAGATCGAAAGGATGCCA
ACGCAGCAAGGAAACCAAAATAAACAAACAGGCTGGCGGGCAAATTGTTAATGCTGTTTTTGGGGGAGGGTCTGTACACATACTCAAATGTATGC
CTAGTGGGGTTGTACACTCAAAAAAAAAAACCTGACAGAAATTTATTTTTATTTGTCTGAATCATAATGGGTTATCATAGTGGATTATTTTGCAA
ATCTTTGGAAATTTATATTCAATTTCTCTTTTTAAGTTTTGACAACACTTTTTTCTGCGTGTGGTGTTTGGTGGCTCAGCTTTTCTGGTGGGGCT
GACAGCATCCCTCGATTCTGTCCCGGAAGTTGTGCTTCGTCTGGGATTTTGGGGTTGTCACTTTCTCTCTCCCTTGCGTGCTGAAAACTCCATAA
TCCCAGCCACTCTGCCTTTTGCAATAACAATGAAATGGCGATTGCCTGCCATAAAAATGTCTATTAAGCTGTCAGGTTCTGACACTCATAAAACC
ATCAAACAAGTCAAACGAACAGGATAGCAGCAAAATCAGCAGGACGAACCGCTGTCAAAGTTTTCGGCCTCATCCTGGCGGCTTCCCCACGCACA
CATAGGCTCACATTCTCGCTAGGAGATTATACATGTGTATGTGTGCTGCGTCCTTTCATATTTCTTGCGCCCCCCACAAAAGGACTTTATTTATG
GGTGGGTGGGATGAAAAGATACAGATACACGCCCCCACACAGAGTCCAAATTATTTTATGAGCGCAGAGGCAGAATGCCTTTGGCATCCTTGGCA
GGATAACCCTTCTCCAGAAGGATATTTCCTTAGATTTCCAACCCCAGCGTAAGATTTGCTGAAAAAAGCGAATCGAATATTCTACATACTAAATT
CC
(SEQ ID NO: 490)

Exon: 1001..2071
Exon: 2157..3087
Start ATG: 1154

Transcript No. : CT14984
TCTCTTCTTCTTCCACGTCGACGTGTCGTGTCAGCCAAAAGAAAGTCGAAATAAAATATTGAATTGAAGCTGCCCCTTTGCGAGTAGGCCCGACA
AAATTCAGAAGCTGCCAGTCGTCCGTACGCCAAACCACACACAACCACCACCGGCAAGATGGTTCTCGCGGATTTGGGTCGCAAGATAACAACGG
CGCTGCACTCGCTCAGCAAGGCGACCGTAATCAATGAGGAGGCACTGAATTCCATGCTGAAGGAGATCTGCGCAGCGCTCCTGGAGGCTGATGTG
AATATCCGACTGGTTAAGCAGCTGCGCGAGAATGTGCGTGCCGTTATTGATTTCGATGAGATGGCCGGTGGCCTGAACAAGAGGCGAATGATCCA
ATCGGCTGTGTTCAAGGAGCTCGTCAAACTGGTCGATCCCGGCGTGAAACCCTACCAACCCATCAAGGGCAAGGCCAATGTGGTCATGTTTGTGG
GTCTGCAGGGCTCCGGTAAGACCACCACCTGTACCAAGCTGGCCTATCACTACCAGAAGCGCAACTGGAAGTCGTGTCTCGTGTGCGCGGATACC
TTCCGTGCTGGTGCCTACGATCAGGTCAAGCAGAACGCCACCAAGGCGCGCATTCCGTTCTACGGCAGCTACACGGAAATCGATCCCGTGGTCAT
TGCCCAGGACGGTGTGGATATGTTCAAACGCGAGGGTTTCGAGATGATCATTGTGGACACCTCGGGTCGGCACAAGCAGGAGGAATCACTGTTCG
AGGAGATGTTGGCAGTGTCCAATGCCGTCAGTCCCGACAACATAATCTTCGTGATGGACGCCACCATCGGACAGGCTTGCGAGGCTCAAGCGAAA
GCCTTCAAAGACAAGGTGGACATCGGTTCGGTGATCATAACCAAGTTGGATGGCCACGCCAAGGGAGGCGGAGCTCTGTCCGCAGTGGCAGCCAC
ACAGTCGCCCATCATCTTCATCGGTACGGGCGAGCACATCGACGATCTGGAGCCCTTCAAGACGAAACCCTTCGTGAGCAAACTGCTTGGAATGG
GTGACATCGAAGGACTGATAGATAAGGTAAACGAGCTGAAGCTAGACGGAAACGATGAGCTGTTAGAAAAGATCAAGCACGGTCATTTCACCATC
CGCGACATGTACGAGCAGTTCCAGAACATCATGAAGATGGGCCCCTTCTCCCAGTTCATGAACATGATACCCGGTTTCTCGCAGGACTTTATGAC
CAAGGGCGGCGAACAGGAGTCGATGGCGCGCGTTAAGCGTATGATGACGATGATGGACAGTATGTCGGATAATGAACTGGACAATCGCGACGGAG
CAAAGCTCTTTAGCAAGCAGCCAAACCGCTGCGTTCGTGTGGCCCAGGGAGCTGGTGTCATGGAGCGCGAGGTCAAGGAACTGATTGCACACTAT
ACGAAATTTTCGGCGGTAGTAAAGAAGATGGGCGGCGTTAAGGGACTGTTCAAGCAGGGCGACATGACCAAGAATGTGAATCCAACACAGATGGC
CAAGCTCAACCAGCAGATAGCGAAGATGATCGATCCCCGGATGCTGCAACAGATGGGCGGCGTTGGTGGTATCCAAAATATGATGAGGCAACTGC
AGCAAGGAGCTGCGGGTGGTTTGGGTGGCCTGGGGAACCTGATGAGCGGTTTTGGTGGCAAGTGAGCAGGTGGCGTGTAAATTTAACGATTTTTA
TATGATTTTGTTTTCGCGTAGTTCGTAATTTGTTAGCCATTTGTTTCCATTTGTCCAAGGCCACAAAAATTGATACGCGTTGTGGAAGCGAATAT
AGCGTATATAGCCTATAAAGCCCATATAGATGTGCAAACAGTTAACAAATTCGGTTTTTGTACGGCTTGGCAGCCACAGTGTCAGTTTTTATAGT
TTAAACAGTTTTCTGTACACGAACTAATGGAATTAGCATGCCTATCAGAATACCAGTAAGGCAATTGAACTAGATATAAACAATAAATAATTAAT
ATATGAA
(SEQ ID NO: 491)

FIGURE SHEET 269

Start ATG: 154

MVLADLGRKITTALHSLSKATVINEEALNSMLKEICAALLEADVNIRLVKQLRENVRAVIDFDEMAGGLNKRRMIQSAVFKELVKLVDPGVKPYQ
PIKGKANVVMFVGLQGSGKTTTCTKLAYHYQKRNWKSCLVCADTFRAGAYDQVKQNATKARIPFYGSYTEIDPVVIAQDGVDMFKREGFEMIIVD
TSGRHKQEESLFEEMLAVSNAVSPDNIIFVMDATIGQACEAQAKAFKDKVDIGSVIITKLDGHAKGGGALSAVAATQSPIIFIGTGEHIDDLEPF
KTKPFVSKLLGMGDIEGLIDKVNELKLDGNDELLEKIKHGHFTIRDMYEQFQNIMKMGPFSQFMNMIPGFSQDFMTKGGEQESMARVKRMMTMMD
SMSDNELDNRDGAKLFSKQPNRCVRVAQGAGVMEREVKELIAHYTKFSAVVKKMGGVKGLFKQGDMTKNVNPTQMAKLNQQIAKMIDPRMLQQMG
GVGGIQNMMRQLQQGAAGGLGGLGNLMSGFGGK*
(SEQ ID NO: 492)

Classification: known_flybase_gene
Gene Symbol: Srp54k
FlyBase ID: FBgn0010747

Celera Sequence No. : 142000013384547
AGCATAAAGCTGCATACGACCTCTCCTCCAGTGACGGAAAGAAGGCTCTGGACATTGCAGTGGACCAGGAAAACGCAGACATTGTAACGCTGTGA
GTAAGAAAGCAGAGCTTCAATCCGGCAGATACATAACCATTCTTGTTTCAGACTCCGATTGACACAACTGAATGACGAGATTGGACCCAACGACG
AGTACAATGGCGAAGATGAGACGTACAAGAACGTAATGAAGGACTTCTCCAAGTTACCAGCCAGCCAGACGCGAGTTCTGCGCCAGCGGCACGAC
TCAAATACACTCGAATCGCAGCGCAGCTCGCTTACAAACTCCGACTAGCAGTGGCAGAAGGGCCGCAAGAGTTAGGACCTTACTGGATATTATGG
AATAATTTGTTCCAATTATTAGGATAGCGTGATATTGGATTGTTATTGGCTTTATAACGCATTAACCAGGAATGTTAAACGGTTTCGACCTCTAA
GGATGTCGTTGCGGGCTTGTTTCCCTTGGTAATCTCATTTGAAAAGCGCTTCCGATTATACAAGAAAATATTATTCATTGCATTTGGCATTCGAA
TGGCAGGCACGATCGTTCGTTTTCTCTTAGGCGCATTTTGAATCCGTTTTTGGCGATTAGCTTAAGTTTAAAGTATTCGTAGAGCAGTTGAGTTT
ATTAAAAATACGTATATTTGCCTATAAAATTGTACATCGTCTTATGTGGTATTTATTAAACGATATTGTAAAATGTACGTCTAGCTATATGTATC
TTGTTACAGAGCTGTTCCAAATGTTCCGATTTGTATTTGTTTGCTAAACTGTTTAATGCTGCATGTTTCTAAATGTTTTAACGCTATCATGTTGA
TGATTTTTGGTGCCAACTGTTGTGAGCACTCTAGGTTCGCGAATAAAGTTGTAAAATATTCAGATCAATCAAAGTTGGTCTCTTCAGGTGTAAAA
CATGGTGGTCCAATCTGCGGTGTATTGGTAAAACATGTCCAGGGACTATTCTAGGCCACAGCTTGAAACTCGTTCGTCTCGGATATGTAGTCTGT
GAGCTTGTTCTTCACCTTGTGCATTGTGGTTACATGTCTCTGGACCGCACTGCGATCGTTAAACTGACGGCCGCACTGTTTGCAGGAGAACATGA
CGCCAGCGTGGGTGACCAGATGGCGACTGAGGCCCGAAACATGATTGAAGCTACGATGACACAGATGACACTTGTGCGTCCGAGAGTTGCCCATA
TGCACGCGGCCAATGTGCTGCTGCAGGTTGGACTTCTGGGCAAAGCAGCTCGAGCATTGGGGGCACTGATGGCGCTTTACTCCCGTATGGGTGTC
CATGTGACGCTTGAGCACTTCGCGCTGGGAGAAGGACAGTTCGCACTCGCTGCACTTGAAGGGTTTCAGGCCCGTGTGGATAATCATGTGGCGTT
TGAGCGAGCTGGCGCACGACAGTTGCAGTGCGCAGCTGGGACACTTGAGCGTGCCGCCCTTTCCACTTTTCAGTCCCTTAATGTGGGTGTTGTGG
TGGCGCGTCAGAAGTTTCTGCGTAGGAAATGCCACCGGGCACAAATGGCACTGGAACGACTTCACCGTGTCCGTAATTCGACCGGTTTTTGGTTG
AGGACAACTGGACTCCTGCTTGAACACCAACTCACTCGATCTCTTTCGTTTGAGGGGCGTCTGCTCATCTCTATCGTTCTGTTCTTTTTCCTACA
GATAATAAGATCCAAGTTGAATTCGAGTTCAATTTAAAATCACACGGTTAGTTACCACTATAATGACATTTTCATGGAAGCTGAAGACCTGTTGC
TCCTGAGATATCTCCTCGCCCAGATTAAACACGACCACGTCTTCGATTTCCTCTGGCTTTTCGCCACTGAACTGAATTTCGCCGTCTTCTTTGAC
TAAGCAAAGAATTTAATGAAATGAAAATTTTTTCACATTTTTTTTGCCAAATTATACCCACTTACTGTTATAGGAGGTGATTCCGTTGTCCTGGT
CAAATTCGGGAGTGGAGTCCTGGTTTTGATCCTCTGAGCTGGCAGAGTTTATGATGTAAATCTCTCCATTGTCTGTGTGCACTACATCTGATCCA
ACCATGTTGATTTCCCTGAAGTCTTCACCGCTTTCCGCGGGCACTTCCTCGTCCAGTTCGAGGCCATCTATGTTTACATCGCTATTATTTGCGGG
GTCGGTATTGCAGCCCAATATGAATTCCTCTTCTTTTGCATCCTTCCTGGCCTCTGTCGCCTTTAGATTGGCGTCGACCAAGCTGGGTCGTCGCT
TTGGAAGAGCTTTAGTTTTTGACCTAGAAGGGGAGGCATCTTCCTTGACTTGCGGCTTGGTCTCTGGTTCGGACCCATCCAAAGACTCCCACCGA
CCGGCCTTTTTCTCGGTAAGATACACCTCCAATTCGCCCAACAGCATGGCCAGCTGCTCTTTTCTTATGTCCTCGCTCACCTCGTTTCGCAGGTC
ATCTCTAACCTGGCTGCGCACCTCCTCGGCCAGCTCCTTGCGAACCTCACTGCGCACCTCCTCCGCTAGTTCCTTGCGCAGTTCGGTGGTCAGTT
TCGCTCGAAGTTCTAGACGAGATTTGACCAGCCGTTTGTGCATTTCCGCCGCCTGTTCTTCCTTAAAATCTTCTCGCCACTTTTCGTCCTCAAGC
TTGCGCACTTTGTCCTGCACCTCGATGAAGGCAATAGAGTCCTCGAACTCCAGCTCGTCCTCGTCATAATCGTCCGGATCCTTGGAGAAGACGCG
GCTTCGCTTCCCGAGACCCAGAAGTCGGATATGCTTGCGAAGCTTCTTCTCCGCCCATTGGCAGCGCTGCCGGAACAGGAATGACTTCTCCAGCT
GATAGCGGCACTCCTGGCAGATCCTCTTCGGCAGAGTATCCGTCGCCTTGGCGTCCAGTGCGACGCAGGCCATCAGGCGCACGGGTATCGAGAGC
TGGGTGTCGTCCTCGTCGAAGATCGCGTACGCATCCTGGTGCTCCTTGAGGCAAAGGCGGCACAGGGTCGCCAAATCGGGATACGACGGCTGTGC
ATCCATGAAGGCGTCTATTTTTGGTAAATCAACGTATTTACTCGGTGGCGTCTCTGCATCGCAAGCAATGTGACCGCAGACAGGTTCGCTAAAAA
TACCTCCTCTCGAAACGAAAGCAATACAGTCACACTGTTCGTAAATAAACAATTTGATATATACGGCCCATAAACGTATCATAACTTAATTTATT
AATGTAAGGTTTAAAGGTATTGATTTTCATACAAATCCAATGCATACCGAATGTGCATATTTAAAGTTTAATAGAATACAATGACAATTAAAATA
GGTGATGGCTTAGTCAAATATGCGTGCACAAAAAAAGGTACTATTCTTATAATATAGAGGATTAAACTAAATTCGTTGTTACGTGGCTACGTCAC
GGTGTTATTTAGCTTATCCGCTCCTCTTAGACGACAGCGCACACAACTTTTGAAATCGGCGTACGAACTGCTGCATTTTGTCTTGAAGGAACTGT
GCTTTCGGCACAGGTTATCGGTCGTCTGCTTGGGGCTCATAAAGCGCACTTTCTTTCGACACGGCGATGGGGTTTTTACATCCTCTAAGGCAGTT
GTGTTGGCACCCAGAAAGGTGTCCTTGCTATAGTCGTTGCGCAGATGACTCAGCTGCGGGTCGTTCATGTTGATCTCAACCATGGGCACAGCAAC
TAGTGGCGTTGCAGCTGGCTGTCTGCTGGCTTCTGGTTCATCGTCTATTACATTTGAGAAATATATAAGTCGTGCAATTGCAAAGTAAGTGGGCT
GGTCTTACCCAGTAACTCCACCACGCTGTTATCGCTCTGCTCCCTTAGCTCCTGGCCCATGTCTGTTTCGTAGAAGCCAGCGGTCTGTTCGTCAG
GCAGCGGACTGCTTAAGTTCATCTTCATCTCATAGGTCGCCTCATTGCGCTTGCGCACAAAGTACCGTTCCAGTTCGACAAACACGTCGTCCAGA
ACGCTCAGTCGCAACTGCTGCTTGGCTTCGGGTATGATGACCTCTTCGAGTTCCGCCCGCAGCTCCAGCTCGATTTCCGCCCGCACAGCTTGCTT
GCAAGTGCTGAGCAGCTCCTTTTTATACGCGTCGATCTCGCTGCTAATGAGCTGGGCGGCCTGCTGGCGCCACTGGGCATTGTTCTCGGCGCAGC
CAGTTTGCGTGCATCCTTCCCCGGAGCCCCGCTCCTCCTCCACTTCACTCAGCTGCGACTTGACACCCTGCCGCTGCAACGCCTTGTGGCGCCTC
AATTTGCGATCGGCTGCGAGGCAGCGTCGTCGGAAGCAGTGCATCTCCTCCAGTTGCAGCCGACACATGGTGCATATGTGCTGTGGCAGACCGTC
GCCGGGCTCGATCTCCAGCGATGTGCAGACCATTATCTGCAGAGCAGTCGATCCATTTGCACCGAAAACGGGGAAATTGGGTTCCTTCGACAAGC
ACAGGCGACAAACATTCATGTTGAATTTCAAGGCAATTCGGAGCGTGGCAGCCGGACACCTGATTAGGCACGATTCGGAATGATGGACAATCTAG
CAATCTTTCCAAGCAACCAGTTTAGAATATGAAACAAAAAAACATTTGAAGACAAATAACTAAAATTGGAAGCGGAGGAATTTCCTACTAGGAAA
CATCAACAAGTCTAGCCGATTTGTTATCGATATTTTCAGTGTGGCCATGCGGTTGAGAGAATGCATTTTAGTATTTCAAGGCTGGCTGCTCTGCC
ATTGATGTGCCCGTATTTCAGCAAGGCGCTTGGCGGGAGAATTTCAAATAGTCAAAATTTTACAACGATACTATAGCGCTCATTTGAATAACCTG
AAATGCAGCAATAACACACATTCATTTATCAAACATTTCTTTATATTTCATTAAATATTAAGTATAAATACGCAGTTAACTATTAAGTATTATA
TACACAATTACAATAAGATATTCAGTCACTATAATGCTTCTTCTATATACAAAGTACGATATATATTATATCAAAGGGCTTGAACTCGCCGCCGC
ACCTCAATAAATTATGCAATTCAATTCCATGATAATATACAGTAACAGTCGTCTGTGTTCTCCGGGAGTTTGCCGATTGATTTTCTCAGGATGAT TTAGGATCTGCGCCGAGGATTGCCTACTTACAGCTAAAATGTTTGCAAAAACAATAAGTCAAGGACATTTAACAGTGTTTTCATTTCGTTTCGCA
TCGTTTTGATTTCATACTCATTTGCTCTTTGCTTTATCGCTTGGGTGGGGTGTTTTGTGTGTGGGTTTTTGATTTGTGGTGGTAAATAAATAGTA
TCGATCGATTATTAACGATATTCAACATTGAAATACATCAATCATTAGGCATATACATAACTACAGGATATAATACAATACAGGATCGTTGGGAT
CAGGATCGCTCTTCCAGGATTCCATCTCAATCGTGGCGCCAGCTCTGCGGCAGAACGTAGTCCTTGACCTTGTAGAGCGCATTGGCATACCAATG
GATGCCATTCTGCTGCTGCGCCGAGCTCACCACCTTCGGCGAACTGTGCAACTGCTCCTTGGCGGGCAGCCACGCCTCCAGCGTGGACAGCAGGC
GCATGGGAGCCAGTCCCCAGTG
(SEQ ID NO: 493)

Exon: 4627..3809
Exon: 3749..3421
Exon: 3169..1966
Exon: 1899..1766
Exon: 1705..1001
Start ATG: 4484 (Reverse strand: CAT)

Transcript No. : CT14997
AATTTTAGTTATTTGTCTTCAAATGTTTTTTTGTTTCATATTCTAAACTGGTTGCTTGGAAAGATTGCTAGATTGTCCATCATTCCGAATCGTGC
CTAATCAGGTGTCCGGCTGCCACGCTCCGAATTGCCTTGAAATTCAACATGAATGTTTGTCGCCTGTGCTTGTCGAAGGAACCCAATTTCCCCGT
TTTCGGTGCAAATGGATCGACTGCTCTGCAGATAATGGTCTGCACATCGCTGGAGATCGAGCCCGGCGACGGTCTGCCACAGCACATATGCACCA
TGTGTCGGCTGCAACTGGAGGAGATGCACTGCTTCCGACGACGCTGCCTCGCAGCCGATCGCAAATTGAGGCGCCACAAGGCGTTGCAGCGGCAG
GGTGTCAAGTCGCAGCTGAGTGAAGTGGAGGAGGAGCGGGGCTCCGGGGAAGGATGCACGCAAACTGGCTGCGCCGAGAACAATGCCCAGTGGCG
CCAGCAGGCCGCCCAGCTCATTAGCAGCGAGATCGACGCGTATAAAAAGGAGCTGCTCAGCACTTGCAAGCAAGCTGTGCGGGCGGAAATCGAGC
TGGAGCTGCGGGCGGAACTCGAAGAGGTCATCATACCCGAAGCCAAGCAGCAGTTGCGACTGAGCGTTCTGGACGACGTGTTTGTCGAACTGGAA
CGGTACTTTGTGCGCAAGCGCAATGAGGCGACCTATGAGATGAAGATGAACTTAAGCAGTCCGCTGCCTGACGAACAGACCGCTGGCTTCTACGA
AACAGACATGGGCCAGGAGCTAAGGGAGCAGAGCGATAACAGCGTGGTGGAGTTACTGGACGATGAACCAGAAGCCAGCAGACAGCCAGCTGCAA
CGCCACTAGTTGCTGTGCCCATGGTTGAGATCAACATGAACGACCCGCAGCTGAGTCATCTGCGCAACGACTATAGCAAGGACACCTTTCTGGGT
GCCAACACAACTGCCTTAGAGGATGTAAAAACCCCATCGCCGTGTCGAAAGAAAGTGCGCTTTATGAGCCCCAAGCAGACGACCGATAACCTGTG
CCGAAAGCACAGTTCCTTCAAGACAAAATGCAGCAGTTCGTACGCCGATTTCAAAAGTTGTGTGCGCTGTCGTCTAAGAGGAGCGGATAAGCTAA
ATAACACCTGTGACTGTATTGCTTTCGTTTCGAGAGGAGGTATTTTTAGCGAACCTGTCTGCGGTCACATTGCTTGCGATGCAGAGACGCCACCG
AGTAAATACGTTGATTTACCAAAAATAGACGCCTTCATGGATGCACAGCCGTCGTATCCCGATTTGGCGACCCTGTGCCGCCTTTGCCTCAAGGA
GCACCAGGATGCGTACGCGATCTTCGACGAGGACGACACCCAGCTCTCGATACCCGTGCGCCTGATGGCCTGCGTCGCACTGGACGCCAAGGCGA
CGGATACTCTGCCGAAGAGGATCTGCCAGGAGTGCCGCTATCAGCTGGAGAAGTCATTCCTGTTCCGGCAGCGCTGCCAATGGGCGGAGAAGAAG
CTTCGCAAGCATATCCGACTTCTGGGTCTCGGGAAGCGAAGCCGCGTCTTCTCCAAGGATCCGGACGATTATGACGAGGACGAGCTGGAGTTCGA
GGACTCTATTGCCTTCATCGAGGTGCAGGACAAAGTGCGCAAGCTTGAGGACGAAAAGTGGCGAGAAGATTTTAAGGAAGAACAGGCGGCGGAAA
TGCACAAACGGCTGGTCAAATCTCGTCTAGAACTTCGAGCGAAACTGACCACCGAACTGCGCAAGGAACTAGCGGAGGAGGTGCGCAGTGAGGTT
CGCAAGGAGCTGGCCGAGGAGGTGCGCAGCCAGGTTAGAGATGACCTGCGAAACGAGGTGAGCGAGGACATAAGAAAAGAGCAGCTGGCCATGCT
GTTGGGCGAATTGGAGGTGTATCTTACCGAGAAAAAGGCCGGTCGGTGGGAGTCTTTGGATGGGTCCGAACCAGAGACCAAGCCGCAAGTCAAGG
AAGATGCCTCCCCTTCTAGGTCAAAAACTAAAGCTCTTCCAAAGCGACGACCCAGCTTGGTCGACGCCAATCTAAAGGCGACAGAGGCCAGGAAG
GATGCAAAAGAAGAGGAATTCATATTGGGCTGCAATACCGACCCCGCAAATAATAGCGATGTAAACATAGATGGCCTCGAACTGGACGAGGAAGT
GCCCGCGGAAAGCGGTGAAGACTTCAGGGAAATCAACATGGTTGGATCAGATGTAGTGCACACAGACAATGGAGAGATTTACATCATAAACTCTG
CCAGCTCAGAGGATCAAAACCAGGACTCCACTCCCGAATTTGACCAGGACAACGGAATCACCTCCTATAACATCAAAGAAGACGGCGAAATTCAG
TTCAGTGGCGAAAAGCCAGAGGAAATCGAAGACGTGGTCGTGTTTAATCTGGGCGAGGAGATATCTCAGGAGCAACAGGTCTTCAGCTTCCATGA
AAATGTCATTATAGTGGAAAAAGAACAGAACGATAGAGATGAGCAGACGCCCCTCAAACGAAAGAGATCGAGTGAGTTGGTGTTCAAGCAGGAGT
CCAGTTGTCCTCAACCAAAAACCGGTCGAATTACGGACACGGTGAAGTCGTTCCAGTGCCATTTGTGCCCGGTGGCATTTCCTACGCAGAAACTT
CTGACGCGCCACCACAACACCCACATTAAGGGACTGAAAAGTGGAAAGGGCGGCACGCTCAAGTGTCCCAGCTGCGCACTGCAACTGTCGTGCGC
CAGCTCGCTCAAACGCCACATGATTATCCACACGGGCCTGAAACCCTTCAAGTGCAGCGAGTGCGAACTGTCCTTCTCCCAGCGCGAAGTGCTCA
AGCGTCACATGGACACCCATACGGGAGTAAAGCGCCATCAGTGCCCCCAATGCTCGAGCTGCTTTGCCCAGAAGTCCAACCTGCAGCAGCACATT
GGCCGCGTGCATATGGGCAACTCTCGGACGCACAAGTGTCATCTGTGTCATCGTAGCTTCAATCATGTTTCGGGCCTCAGTCGCCATCTGGTCAC
CCACGCTGGCGTCATGTTCTCCTGCAAACAGTGCGGCCGTCAGTTTAACGATCGCAGTGCGGTCCAGAGACATGTAACCACAATGCACAAGGTGA
AGAACAAGCTCACAGACTACATATCCGAGACGAACGAGTTTCAAGCTGTGGCCTAG
(SEQ ID NO: 494)

Start ATG: 144 (Reverse strand: CAT)

MNVCRLCLSKEPNFPVFGANGSTALQIMVCTSLEIEPGDGLPQHICTMCRLQLEEMHCFRRRCLAADRKLRRHKALQRQGVKSQLSEVEEERGSG
EGCTQTGCAENNAQWRQQAAQLISSEIDAYKKELLSTCKQAVRAEIELELRAELEEVIIPEAKQQLRLSVLDDVFVELERYFVRKRNEATYEMKM
NLSSPLPDEQTAGFYETDMGQELREQSDNSVVELLDDEPEASRQPAATPLVAVPMVEINMNDPQLSHLRNDYSKDTFLGANTTALEDVKTPSPCR
KKVRFMSPKQTTDNLCRKHSSFKTKCSSSYADFKSCVRCRLRGADKLNNTCDCIAFVSRGGIFSEPVCGHIACDAETPPSKYVDLPKIDAFMDAQ
PSYPDLATLCRLCLKEHQDAYAIFDEDDTQLSIPVRLMACVALDAKATDTLPKRICQECRYQLEKSFLFRQRCQWAEKKLRKHIRLLGLGKRSRV
FSKDPDDYDEDELEFEDSIAFIEVQDKVRKLEDEKWREDFKEEQAAEMHKRLVKSRLELRAKLTTELRKELAEEVRSEVRKELAEEVRSQVRDDL
RNEVSEDIRKEQLAMLLGELEVYLTEKKAGRWESLDGSEPETKPQVKEDASPSRSKTKALPKRRPSLVDANLKATEARKDAKEEEFILGCNTDPA
NNSDVNIDGLELDEEVPAESGEDFREINMVGSDVVHTDNGEIYIINSASSEDQNQDSTPEFDQDNGITSYNIKEDGEIQFSGEKPEEIEDVVVFN
LGEEISQEQQVFSFHENVIIVEKEQNDRDEQTPLKRKRSSELVFKQESSCPQPKTGRITDTVKSFQCHLCPVAFPTQKLLTRHHNTHIKGLKSGK
GGTLKCPSCALQLSCASSLKRHMIIHTGLKPFKCSECELSFSQREVLKRHMDTHTGVKRHQCPQCSSCFAQKSNLQQHIGRVHMGNSRTHKCHLC
HRSFNHVSGLSRHLVTHAGVMFSCKQCGRQFNDRSAVQRHVTTMHKVKNKLTDYISETNEFQAVA*
(SEQ ID NO: 495)

Name: zinc finger protein
Classification: transcription_factor

FIGURE SHEET 271

Celera Sequence No. : 142000013384288
GCTGGCAAGAAGACACGCATCATGTGCCTGCTACGGGAGATGTACGGATCCGGCGTTGAGCGGTTGAGGAGCGAGACCATGACATTCACCACGCC
ATCCAATCGGAAGGTAGAGGTGATGACGGTCAGCAGCAACTACCACTTGGAGGTGAATCCCTCCGACGCTGGCATGTACGACCGCACGGTGGTGA
TCGATCTCATCAAGCAGGTGGCCCAGACGCATCAAATTGAGATTAGTGGCCAACGGGAATTCAAGGTGATTGTAATTTCGGAGGGCGACGAACTC
ACCAAGGATGCCCAGCACGCCCTGCGCCGTACGATGGAGAAATATGTGGCCACGTGCCGGATAATCATATCGGTGAACTCCACATCTCGGATCAT
TCCGGCCATACGGTCGCGTTGCCTGGGCATACGGGTGGCGGCTCCCAACGAAACGGAGATCGTGTCCATCTTGCAGAACACTTGCAAGCGGGAGG
GACTCGCACTGCCCGTGGAGCTGGCCAAACGGGTTGTGGACAAGTCGGAGCGCAATCTCAGGCGAGCACTTTTGATGCTGGAGGCCGCCAAGGTG
GCCAAGGCGCCGTTTACCGCCAATCAGGAGATTCCCGACCTGGACTGGCAGGTGTTCCTGCGTGAGACAGCATCTCAGATTATCAGTGAGCAAAC
GCCTGCCAAACTGGAGAAGATCCGCGAACGCCTGTACGAGCTACTCACGCAAGGCGTTCCACCTAATCTCATATTCCGCGGCCTGGTCGAACAGC
TGGTTAACAATTGTGATATGTCCATCAAGGCAAAGACGCTCGAGTTCGCCACCGAGTACGAGCACCGGATGCAGTCCGGCGCCAAGCACATTTTT
CATCTTGAAGCGTTCGTCGCTCAGTTTATGAACATCTATAAAAAGTTCCTTTCTGAGCTGGACATGACGGATGATTTTTAAACGATTTACACGCT
TTAGCATTTAATTCAAAAAACTTATTAAATAAACTGATTTAAACGAACTATTAACGTTCTTCCTGAAGATCCGTTCGCATCTGCAGAACGGCCAT
GCTCATCTTATCATCGGTGGTGCGCTTTATGGTCTCAATATATCTTTGAACTTCTTCTTCGAGTTTAAAGTAAGCCTAAAATAGGAATAGATTTG
GAATATGATTGGAATGTATTTTGAGTAGAACGAAATTTATATGTATGACTTACCATTTCATAATCAAGATCATCCTTGCCATTAATCTTTAAACC
GTGCAGCAGCAAATCGATCGTGCTGATGGGGAAGCAGAGCTGTGGGTTTGCTATGTTCACCGCGTGTTTGAATTCGAAATACTCGCTACCTGCTC
CCAGCATGCCGGCGATTATTTCACATCCCAGATCTGCGGCTTCCAGCAGACGATTGTGTTTCACAAGTAAGTGGAGCAGTTCCCGGGAGTGGGAT
AACTTGTAGGAGTTTATCAGCCACTGGGGCAAGAAGGCGTTTAACCCGAGAAGCCTTTGAACCACGCTCTTTCTTATCAAGGTGGAGTCTTTTGC
CTCGTTATCCACAACCAGTTTTGAAGTAAAGTCCAGGCCATATCGGCAGCATTACTTCGATGAGGTAGATCTGTTATAAGACATATAGTAAGCC
TCTTTTTTTCATACACGTTAAAAAATCCCTACCTGCCATGTCGTTGTTTTGCAGCCAGTTCCAGGCGTCCGACGACTTGTCCTCAGTGGCAGCAA
CACAAGCGGATGTCAGACTCTCGAATATGGGGAGCACAGAGAACGAGTGTCCCCGCGAAAGTTTCAATGCCGCGGTGTACAGGCCGGAACTAGCC
AGCAGGTATGATAGCTCCTCGGGTGTGGCCCGCTCGTAGGCAGCTGTATCTTTGCGGTAGAAGGAAAGCTCACGTAAAGCTTCTGCGTGCACCAG
TTCCCTTCGGATATCAGCCAGCTCTAGAACAACCACCTCCTGGCCTCTCTTGTCCTCGTCACATTTGGGCTCACCATCGTCGTTATCCTGATCTA
TGGTAATCACCTGCTCATCACCAAGAACAGGCTTGGCAATCCATCTGTAGCGGCTGTCAACTAGGTGCAAACAGTTTAGGCAAATTAACAGCGAG
GAGCAACGTTTCTCTAGCGCGTTTGGTGCATCGCTGTCTACTTGAAACCGCATGGCCTGCTCATACATAACCGTAGAAGCTGTTCGGAAACAAAT
TATTAATGCAAGAAGAAATGGAAGAAAATAAAGTAATTTTTATGCAAACCTTTTCTCATGTTACCCTTGTTCGTATGGAATGCATACAAAAAGTT
GTAGACTTCGTTCTGATCGATGCTCATTGATCGTGCCCGGGATTCAACAATGCTCTCGAACTCGTCTTGCAACCCGATGTAGGAGAACTGCATAA
GCAGTGGCAGACATTTATTCTGGAACAGCGTTATGACCAACTGGCGAAGGCAATCCTTACGCCTTGAAATATCTGCATTGTTGACTAAGGCGGTG
TACGCCTCCACGTAGTGTCCCAACTGCAGATGATTATTGAACACTATTGACTGGAACATGGGCAACTGAGGATCATCTGGCTGCAGCACCCTAAT
GGCCATGTCAGCCAGTTGAATAATGTAGTCCAATGCGGAATGCTGTTCAAAGAGCTGGATAACCTTAAGATAGTAGTGAACAATTGCCAGTTTTG
TGTCTTCGGGGGAAATTGTATCGCCACGGCTGACGCTATTCTGTAATTTGCCGTATAGAGGGGTATTTTTCAGTACATGCTCAAAGAGGAAGTCA
TCCTCCACAATGCCAGACTCCGCCTCGTGAAAGAGATGCACGGCCTTGTGGGCCTCACCGCAATCCAATAGAGATACGGCTAGCATAAAGCGTCC
TGCGGAAAAAAAGGATTAATTTCAAAGCTGGGAAAACTAGCAAATAATGCATACTGGCATGTTTTTGTACGGAACACCAGTTTGACAAAATGCGC
ACGTAATCCTGAACAATGATGTGATGACAGGTCCCAAATAACCATTCCGGAAATACGTAAATCGGAGATCCCGGCCAACTAAGAGATGTTTGAAA
CTTAAAACATGATCAATTTTTCTATATATTATACGCACAGCATCTTATTGATGTATCCAACAAGTTGGAGCAAAGACTGGCGTAGATTCAATTGC
TCCGAGTCCAGCGACAAACTGTCATGCTTCAGCAGCATAGTCAAGGCGCTGAACAGACCTTTCGATTCCAGGAACAGTCGGAGCAGAGTGGTCTG
ATCGTTCCCATTATGTTTCAGATGGCTGGAGTATGGTCGATTATAGCCGCTGAAAAGTTGGGCGCGGCTCAATCGTTGAATAGATGCCTCGCTAA
AATTAAAATAGAAGTTAGAACTGTGCAATACAATCAATTATATATCCTTACAATCCAGCTGGGGTACTCGATGAAATGGGTGTCTCGGCAATCCA
AACCAGTGTATAATATGAGTTCAAATAATTTAAATTTGTTAAAACATTTTCGCTTTCCATTTCGTTCTGACCATAAGCCATGTACTGCAATACCA
AAAGGTTTCGGCAAACAGAAAACCTAGGGACACATGATTTAATAAATGATAAACCAAGTTCAAAGTTTTTAAACTATTACGAAAGCTCACCGTA
TCATTGCCATTTGCTTCACTGTTTCGGACAAAATAGAAAGTCCATATTCGCTACCCATTAGAGCCCCAGACGACTGCAAGAAGCGCGTAGAAAGG
GAGTAATCTATAAAGTAGAAATGAAATATATGAATCATTTTCAAACATTATATATATTTATAAGTAATTTACCATGCGGCGGTTCATCTGGATCA
ATCATACACAGCACATCGAGCAGCATTTCCAAAGCGGGTTCAAGATTTGGTATATTCTGCAGCTTCTGTTGGATTTGCCTCACACAGTTTGATGG
CAATATTGGACCATTATCATCGATCATACTGATTCTAGCCACCAGCTTAGATATTACTTCAACCGGTGACTCCCGCTGGTAAAGCTGTTTATCTA
GCTCGATTTTAATGTCCTCCGAAATTAGTTTATCAAGCAGTGTCACCACATTCATGAGCTCCACAAAACCCTTGGCCATTTCGGGATCGTTGCGA
AATAGTGGCGCCACATATGTCGCCACTTCATCGTTATGCTCGCCGATGAGCAACAGGTGCTCGAGCACTTCGCAGGGGCGCAGCAATGCGAATGA
TTGCCTTCTAACCAAACATACTGCATCCATTCCACCAAGAACGGCGAGTCCTGTCGGCTCGGAAAGCTTAATGTGATACTGTTCGCAGCAGGAGT
AAAAGCGATCCCACAGCCGAGTGGATATCTCCAAGTACTCCTCATCGGTGACCACAAAGTCTTTCAGTTCGTTTTGGATTTCATCTTCCACGGCC
TGGCATACCTGCTCCTTGAGCACTGACATGGAAAGTTGCTTTACATCGAATTGCAGGTTAACGCGTCTGAACATCTACGATACAAAAAATTCAAA
TTACTAAACTATTCCAATAATTCATAATAAAGAATGTTTTGGTTATACTCACATATAAAGCCTTGGCAATTACATTTCGGTCAAATCGACCAGGA
TGAAATATATAGCTGCAGTAAGTTTCGCGTGGATCCACTCCCTGCTCCATGGTGAGACAATACCGATCCGGTGGCGGTTCTAGAGCAGCCGAAAC
CCATTTGATTGCGTTGTTGGAGGCAAAATATGCTGCCGAGACATGGAAATCGCCTTCAGCGTTGCTCCAAAGGGCCCAGATGTGCGAGGATGTGG
CATCGAAGTCGACCAAATCCGTTTGCGGCGCCGGCACCATGTTCTGCACCAAATTGATAACGCTGGCATCGTCGGCATCGGGCATTATGCTAACG
CATATAAACTCAGCTCGGGAATTGTGCGAGAGAAATAGACAGAAGTTTTGATCGCTTATTTTTCGGAGCTGGCTGTTTTGTGCTGTTAAAAAAA
GAATATAATCCCATTATATCTAGATCATAAATCTAAATCGTAATAATATTTTATACTCACGTCCTTGAGCTGCTGAGTCCTGTCCCAGTTCGGTG
GAGCAGTTAATGCTGGCTACAGTCTGCAAGTTATCCACTGACCATAGACGCAGCTCATTATTGCGATACAGAACCAGAATGAAAATTTCCCCCCC
GATTTCACTGAAAGCCATGGACGTGGCTGCCTCCAACGTTTCAGAGCGGCCGCTACAATGATTAATGAAACATTAGGGATTTGCCATTTATCGAG
GTTTATCCACTTACGTGAGGGCACCCTTGAGATTCGACAGAAACCATGGCATTAGCTTCGGCTCCTTGATTTCGTGGGTGATAGTATGGCCGGTG
GAGCATTTCATAACGTGAAGCAGTAGTTTGCTCTGATACGCCACCGCAAAGTAGGCTGACTGGGAGTCTTGAGTGAGGTACGATACAGCCGCGTT
GGGCATAGTTCCAAAGCCATCCGTGACATAGTAAGTGCTGGGATCATTGATCTTGTCATTGACGTCGTAGAAAATGGACTGGGATAGCAGATCCT
CTGGAGAAGCTGCGCCACCTTCCTGCCCAGCGACCTTCAAGGGAAACACATAGCGATGCACACTGCTGACCGTGACCACCAGCAGGGTGACGGAT
GTACCTTGCTCCGTGAGTGATACATTCAGCACAGCGGAGTCGGTGAATCGCAGACGCAGGTGATTCCTCTGCAGGGAGATGTCCAAACTAACCTC
TGATAGTTCCAGGACATCCTGGTATGTCCGCCTGCAAATCAGTGGCCATGTGAAACTAATTTAACGATTCTGATTTGCACTTACCAATATATGAA
ACGGTTTCTGGTCTGAACATTTTTCGTATTCTTGTAGCAATAGCCGCCGGAGGTTTCGAAGGTTTTTAAATCCTGCAAAGTGCTCTGGGTTCCTA
CATTTTGCGGAGGAGCATTTGGTTACTCAGAATTTCTCTGGCAATCTTGCACGAAACTCACCCGTGTTAATTTTCACCTCGATCCACTCCGCCGG
ACTGAGGTTCCGCGGTATGACCTCGCGGTAGCTCATGTTGGCTTGCAGTTTGGATGTGGGCATCTTGCTAGCACAACAAATTAATATAAAAACCT
CAACGAAAACGGAAAATTATTGGCGGCACCGGCGTAAACACGCTCAGTAGTAGTGTTGGAAAACGCTTACGCCAGCGGTGCACACCAGGCAAAAT
AGTCGACATAGCTTTTTATACTCACATACAAAAGTTAATTACAGAAGTTAGTTAAAAATTGTACATTTTCCTAAATGTAATTTCATGACAATAAA
GTTTATTATAGCAAAGCAGGAATGATATAAGATGCCTTTAAATCTTGTGATATTAAGAAAGTTGTCGCTAGCATTTTAACAATTGCCACATATTG
GTCACACTGCATTGCACGTGTGTTTCCATTTGTTGATGCGGCTTTATTATTTAGTTTATTTTTTAAAATAAAAACTGTCTCTGGCCTAAAAATGA
GTGAACAGCAGGATGAGACTGTAGTCTGCCTGCCCGGGGAGCGACTCTGCAGAACCGAGGACAGCATAGTCCTGGGCATAGGCACCTACGAGCAG
AATGGCTACATTTACGCCTCCAAGTCTGGAATTGTCAACATCGAAGATTCGGGTGATAAAGTAAGTAATCCTGGCATTTCGTTGACTCTGGGAAC

FIGURE SHEET 272

CAATTAATCTCCATTTCAGTGCCAGGTGGTTAGTGTGCATAAGCCCGGATTTCATCTAACCATCCCAGCCACCGGAGACGTGGTCACAGCCAGAG
TTCTCGTCACAACTCCAAAATTCGCCAAGTGCGCCATTTTCTGCGTACGAAATGTGCTGCTGGAAAGCAGCTACCGCGGACTTCTGCGCAAGGAG
GATGTCCGGGAGACCGAAAAAGATCGCGTCGATATCTACAAGTCCTTCCGGCCGGGCGATGTCATCCTGGCGAGGGTCATTAACCAACTGGAGCA
GTCCTTCCTCCTGACCACCGCCGAAAATGAACTCGGCGTGGTCATCGCCTATGCCAGTGATTACCGGAAGACCCGGGTGCCCATGGTGCCGGTCG
GCTGGAGCGAGATGCAGTGCCCCCAGACCACGATCAAGGAGCCACGGAAAGTGGCTAAAGTTCTGCCTGAGAGTTCAATAA
(SEQ ID NO: 496)

Exon: 6111..5952
Exon: 5887..5785
Exon: 5731..5240
Exon: 5182..5001
Exon: 4927..4518
Exon: 4444..3778
Exon: 3712..3607
Exon: 3538..3377
Exon: 3321..3079
Exon: 3023..2905
Exon: 2849..2235
Exon: 2169..1648
Exon: 1591..1194
Exon: 1120..1001
Start ATG: 6048 (Reverse strand: CAT)

Transcript No. : CT15225
CGGTGCCGCCAATAATTTTCCGTTTTCGTTGAGGTTTTTATATTAATTTGTTGTGCTAGCAAGATGCCCACATCCAAACTGCAAGCCAACATGAG
CTACCGCGAGGTCATACCGCGGAACCTCAGTCCGGCGGAGTGGATCGAGGTGAAAATTAACACGGGAACCCAGAGCACTTTGCAGGATTTAAAAA
CCTTCGAAACCTCCGGCGGCTATTGCTACAAGAATACGAAAAATGTTCAGACCAGAAACCGTTTCATATATTGGCGGACATACCAGGATGTCCTG
GAACTATCAGAGGTTAGTTTGGACATCTCCCTGCAGAGGAATCACCTGCGTCTGCGATTCACCGACTCCGCTGTGCTGAATGTATCACTCACGGA
GCAAGGTACATCCGTCACCCTGCTGGTGGTCACGGTCAGCAGTGTGCATCGCTATGTGTTTCCCTTGAAGGTCGCTGGGCAGGAAGGTGGCGCAG
CTTCTCCAGAGGATCTGCTATCCCAGTCCATTTTCTACGACGTCAATGACAAGATCAATGATCCCAGCACTTACTATGTCACGGATGGCTTTGGA
ACTATGCCCAACGCGGCTGTATCGTACCTCACTCAAGACTCCCAGTCAGCCTACTTTGCGGTGGCGTATCAGAGCAAACTACTGCTTCACGTTAT
GAAATGCTCCACCGGCCATACTATCACCCACGAAATCAAGGAGCCGAAGCTAATGCCATGGTTTCTGTCGAATCTCAAGGGTGCCCTCACCGGCC
GCTCTGAAACGTTGGAGGCAGCCACGTCCATGGCTTTCAGTGAAATCGGGGGGAAATTTTCATTCTGGTTCTGTATCGCAATAATGAGCTGCGT
CTATGGTCAGTGGATAACTTGCAGACTGTAGCCAGCATTAACTGCTCCACCGAACTGGGACAGGACTCAGCAGCTCAAGGACCACAAAACAGCCA
GCTCCGAAAAATAAGCGATCAAAACTTCTGTCTATTTCTCTCGCACAATTCCCGAGCTGAGTTTATATGCGTTAGCATAATGCCCGATGCCGACG
ATGCCAGCGTTATCAATTTGGTGCAGAACATGGTGCCGGCGCCGCAAACGGATTTGGTCGACTTCGATGCCACATCCTCGCACATCTGGGCCCTT
TGGAGCAACGCTGAAGGCGATTTCCATGTCTCGGCAGCATATTTTGCCTCCAACAACGCAATCAAATGGGTTTCGGCTGCTCTAGAACCGCCACC
GGATCGGTATTGTCTCACCATGGAGCAGGGAGTGGATCCACGCGAAACTTACTGCAGCTATATATTTCATCCTGGTCGATTTGACCGAAATGTAA
TTGCCAAGGCTTTATATATGTTCAGACGCGTTAACCTGCAATTCGATGTAAAGCAACTTTCCATGTCAGTGCTCAAGGAGCAGGTATGCCAGGCC
GTGGAAGATGAAATCCAAAACGAACTGAAAGACTTTGTGGTCACCGATGAGGAGTACTTGGAGATATCCACTCGGCTGTGGGATCGCTTTTACTC
CTGCTGCGAACAGTATCACATTAAGCTTTCCGAGCCGACAGGACTCGCCGTTCTTGGTGGAATGGATGCAGTATGTTTGGTTAGAAGGCAATCAT
TCGCATTGCTGCGCCCCTGCGAAGTGCTCGAGCACCTGTTGCTCATCGGCGAGCATAACGATGAAGTGGCGACATATGTGGCGCCACTATTTCGC
AACGATCCCGAAATGGCCAAGGGTTTTGTGGAGCTCATGAATGTGGTGACACTGCTTGATAAACTAATTTCGGAGGACATTAAAATCGAGCTAGA
TAAACAGCTTTACCAGCGGGAGTCACCGGTTGAAGTAATATCTAAGCTGGTGGCTAGAATCAGTATGATCGATGATAATGGTCCAATATTGCCAT
CAAACTGTGTGAGGCAAATCCAACAGAAGCTGCAGAATATACCAAATCTTGAACCCGCTTTGGAAATGCTGCTCGATGTGCTGTGTATGATTGAT
CCAGATGAACCGCCGCATGATTACTCCCTTTCTACGCGCTTCTTGCAGTCGTCTGGGGCTCTAATGGGTAGCGAATATGGACTTTCTATTTTGTC
CGAAACAGTGAAGCAAATGGCAATGATACGGTTTTCTGTTTGCCGAAACCTTTTGGTATTGCAGTACATGGCTTATGGTCAGAACGAAATGGAAA
GCGAAAATGTTTTAACAAATTTAAATTATTTGAACTCATATTATACACTGGTTTGGATTGCCGAGACACCCATTTCATCGAGTACCCCAGCTGGA
TTCGAGGCATCTATTCAACGATTGAGCCGCGCCCAACTTTTCAGCGGCTATAATCGACCATACTCCAGCCATCTGAAACATAATGGGAACGATCA
GACCACTCTGCTCCGACTGTTCCTGGAATCGAAAGGTCTGTTCAGCGCCTTGACTATGCTGCTGAAGCATGACAGTTTGTCGCTGGACTCGGAGC
AATTGAATCTACGCCAGTCTTTGCTCCAACTTGTTGGATACATCAATAAGATGCTTTGGCCGGGATCTCCGATTTACGTATTTCCGGAATGGTTA
TTTGGGACCTGTCATCACATCATTGTTCAGGATTACGTGCGCATTTTGTCAAACTGGTGTTCCGTACAAAAACATGCCAGACGCTTTATGCTAGC
CGTATCTCTATTGGATTGCGGTGAGGCCCACAAGGCCGTGCATCTCTTTCACGAGGCGGAGTCTGGCATTGTGGAGGATGACTTCCTCTTTGAGC
ATGTACTGAAAAATACCCCTCTATACGGCAAATTACAGAATAGCGTCAGCCGTGGCGATACAATTTCCCCCGAAGACACAAAACTGGCAATTGTT
CACTACTATCTTAAGGTTATCCAGCTCTTTGAACAGCATTCCGCATTGGACTACATTATTCAACTGGCTGACATGGCCATTAGGGTGCTGCAGCC
AGATGATCCTCAGTTGCCCATGTTCCAGTCAATAGTGTTCAATAATCATCTGCAGTTGGGACACTACGTGGAGGCGTACACCGCCTTAGTCAACA
ATGCAGATATTTCAAGGCGTAAGGATTGCCTTCGCCAGTTGGTCATAACGCTGTTCCAGAATAAATGTCTGCCACTGCTTATGCAGTTCTCCTAC
ATCGGGTTGCAAGACGAGTTCGAGAGCATTGTTGAATCCCGGGCACGATCAATGAGCATCGATCAGAACGAAGTCTACAACTTTTTGTATGCATT
CCATACGAACAAGGGTAACATGAGAAAAGCTTCTACGGTTATGTATGAGCAGGCCATGCGGTTTCAAGTAGACAGCGATGCACCAAACGCGCTAG
AGAAACGTTGCTCCTCGCTGTTAATTTGCCTAAACTGTTTGCACCTAGTTGACAGCCGCTACAGATGGATTGCCAAGCCTGTTCTTGGTGATGAG
CAGGTGATTACCATAGATCAGGATAACGACGATGGTGAGCCCAAATGTGACGAGGACAAGAGAGGCCAGGAGGTGGTTGTTCTAGAGCTGGCTGA
TATCCGAAGGGAACTGGTGCACGCAGAAGCTTTACGTGAGCTTTCCTTCTACCGCAAAGATACAGCTGCCTACGAGCGGGCCACACCCGAGGAGC
TATCATACCTGCTGGCTAGTTCCGGCCTGTACACCGCGGCATTGAAACTTTCGCGGGGACACTCGTTCTCTGTGCTCCCCATATTCGAGAGTCTG
ACATCCGCTTGTGTTGCTGCCACTGAGGACAAGTCGTCGGACGCCTGGAACTGGCTGCAAAACAACGACATGGCAGATCTACCTCATCGAAGTAA
TGCTGCCGATATGGCCTGGACTTTACTTCAAAAACTGGTTGTGGATAACGAGGCAAAAGACTCCACCTTGATAAGAAAGAGCGTGGTTCAAAGGC
TTCTCGGGTTAAACGCCTTCTTGCCCCAGTGGCTGATAAACTCCTACAAGTTATCCCACTCCCGGGAACTGCTCCACTTACTTGTGAAACACAAT
CGTCTGCTGGAAGCCGCAGATCTGGGATGTGAAATAATCGCCGGCATGCTGGGAGCAGGTAGCGAGTATTTCGAATTCAAACACGCGGTGAACAT
AGCAAACCCACAGCTCTGCTTCCCCATCAGCACGATCGATTTGCTGCTGCACGGTTTAAAGATTAATGGCAAGGATGATCTTGATTATGAAATGG
CTTACTTTAAACTCGAAGAAGAAGTTCAAAGATATATTGAGACCATAAAGCGCACCACCGATGATAAGATGAGCATGGCCGTTCTGCAGATGCGA
ACGGATCTTCAGGAAGAACGTTAA
(SEQ ID NO: 497)

Start ATG: 64 (Reverse strand: CAT)

MPTSKLQANMSYREVIPRNLSPAEWIEVKINTGTQSTLQDLKTFETSGGYCYKNTKNVQTRNRFIYWRTYQDVLELSEVSLDISLQRNHLRLRFT
DSAVLNVSLTEQGTSVTLLVVTVSSVHRYVFPLKVAGQEGGAASPEDLLSQSIFYDVNDKINDPSTYYVTDGFGTMPNAAVSYLTQDSQSAYFAV
AYQSKLLLHVMKCSTGHTITHEIKEPKLMPWFLSNLKGALTGRSETLEAATSMAFSEIGGEIFILVLYRNNELRLWSVDNLQTVASINCSTELGQ
DSAAQGPQNSQLRKISDQNFCLFLSHNSRAEFICVSIMPDADDASVINLVQNMVPAPQTDLVDFDATSSHIWALWSNAEGDFHVSAAYFASNNAI
KWVSAALEPPPDRYCLTMEQGVDPRETYCSYIFHPGRFDRNVIAKALYMFRRVNLQFDVKQLSMSVLKEQVCQAVEDEIQNELKDFVVTDEEYLE
ISTRLWDRFYSCCEQYHIKLSEPTGLAVLGGMDAVCLVRRQSFALLRPCEVLEHLLLIGEHNDEVATYVAPLFRNDPEMAKGFVELMNVVTLLDK
LISEDIKIELDKQLYQRESPVEVISKLVARISMIDDNGPILPSNCVRQIQQKLQNIPNLEPALEMLLDVLCMIDPDEPPHDYSLSTRFLQSSGAL
MGSEYGLSILSETVKQMAMIRFSVCRNLLVLQYMAYGQNEMESENVLTNLNYLNSYYTLVWIAETPISSSTPAGFEASIQRLSRAQLFSGYNRPY
SSHLKHNGNDQTTLLRLFLESKGLFSALTMLLKHDSLSLDSEQLNLRQSLLQLVGYINKMLWPGSPIYVFPEWLFGTCHHIIVQDYVRILSNWCS
VQKHARRFMLAVSLLDCGEAHKAVHLFHEAESGIVEDDFLFEHVLKNTPLYGKLQNSVSRGDTISPEDTKLAIVHYYLKVIQLFEQHSALDYIIQ
LADMAIRVLQPDDPQLPMFQSIVFNNHLQLGHYVEAYTALVNNADISRRKDCLRQLVITLFQNKCLPLLMQFSYIGLQDEFESIVESRARSMSID
QNEVYNFLYAFHTNKGNMRKASTVMYEQAMRFQVDSDAPNALEKRCSSLLICLNCLHLVDSRYRWIAKPVLGDEQVITIDQDNDDGEPKCDEDKR
GQEVVVLELADIRRELVHAEALRELSFYRKDTAAYERATPEELSYLLASSGLYTAALKLSRGHSFSVLPIFESLTSACVAATEDKSSDAWNWLQN
NDMADLPHRSNAADMAWTLLQKLVVDNEAKDSTLIRKSVVQRLLGLNAFLPQWLINSYKLSHSRELLHLLVKHNRLLEAADLGCEIIAGMLGAGS
EYFEFKHAVNIANPQLCFPISTIDLLLHGLKINGKDDLDYEMAYFKLEEEVQRYIETIKRTTDDKMSMAVLQMRTDLQEER*
(SEQ ID NO: 498)

Name: KIAA0197-like
Classification: hypothetical

Celera Sequence No. : 142000013385213
CACAAAAAGGCTTCATCTTGTAATCTATAATGGATGTGTTTAATTTATTATCTTATTATCGATATGTTCGGGAATAAAATATGTATAATTTTAT
ATATACTAACTATTATAGCAACTATATCATAACTATAATTTTCCCTTGGCGAATTCCAGTGTGATGGTCCTGGGATCGAAATCAGTTTTATTTTA
ATACACCGAGTTAACCACAAAAGTGGCATGCCCAACTCATCTAATGAAAGTTTTTGCCCATTCGGGCAGATTATTTTACATTTCATTAATGTGTC
GAAAAAGGGAAATGCTTTCAATGAAAGCTGCTCCCAGGCCCAGCTGCCTGTGTTCCCCATCATCATCATCATCATCCTCATTCTCATCGTCGCAA
CCATCATCATCATCATCATCTTTGGGTCCCGGGAATCTGGAATCTGTGTTATTGATCAGTGCTGCGCAATTAACTTAGCAACTTATGATTATGAT
TATGCTGCCGAATGGGTGGTGAGTACGAGGCATTACTCATGTATGGCGGTAAAACCAACAGGTTGACAGGACCTCTGTTTCGTTTCCATTCCGTT
CCAATGCACTGAGCATATTTTGGAAACTGTGAAATCAATATATTTGATATTAAATATTATCTTATGAGGTTATTTAATGTATAAAATGTGGCTTT
TACTTAGAAGTGTGCAACTAAAAAATTATTTATATAAGTAAGTATAAGTTGTTGGAAATTACTTATACGTTTATATAAGTATATCGTTCAAAATA
TATATAGGAAAGATAATGATATTAAAACGTTGTTTTTGCTTGCAGATTTCCATCGTTTGCTGCGTGACAAATGCACCTTATTTATTTCTCAGTGC
AGGGGTTGCTTATCCACCACTGCGTCGGTGGAGTGGGCAGCTGTTTCGCTGCCGCCGCCGAGCGATAGTGGTGGTGTTGGTGGTGAGTTGTG
TTGCAACTTCAACTTGTTCCTGAGGGCCGTGGACGTCGATGTCGGCGAGCAGAAGCAACCTGACTCTGACTCGACTCGGTTATTCGCTCACCACT
CGCGCTTGAATACGGACGTGTTTTCGGTTCGAAGTCAAAGTCAAAGTAGAAGGCGAATCACAACGGATCGGTCGAAAGTTCAGAAACTCGTCAAT
TGACATAAATTGAGTGCAATTTGCAGTGTGCGAAATGTGTGTCTAAGTGAAGCCAATCGACCAGCCAACAATTCGCCAGCTTCGCCGCCTCTTGT
CGCGTGTTTCGCTCAATTCAACTACTTAATTAGTAGACATAAACAAATCGTGCTTTGAGTCCGACATGGCCGACGAAAGTCTGCACACCGTGCCC
CTGGAGCACAACATAGACTACCACATCGTGACGCTATTCGAGCGCCTGGAGGCGATGCGTAAGGACTCGCACGGCGGTGGCCACGGGGTCAACAA
TCGCCTGTCCAGCACCCTGCAGGCTCCCAAGCGGAGCATGCAGGCTGAGATTCGCACGCTGGAGTTTTGGAGGTAAGTCAAGCCTGCCCTAGGAC
AAATACTTATATAGATATACGGGATTAACTATGTTATTTAATGACTGAAATTCGGAAAAACGTCTTTTGCCAAAAACTTGATATTTACAAGCGGC
ATTTTTGTCATAACTTCGCTAAAACTTCTCATATTGATGAAAGAATAACTGTTTTGAGCAGCTATTTACCAGAGCTATCGAACCCTATCACTTTT
TGAAGGATTTAGGAAAATTAATTTTTGGGTGAATTTTCACATTTTTTGTAAGGGGTAACATCATCAAAATTTGAAAAAAAATGGCAAAAAAAATTG
AATTGTCGTTTTTAAATACAGTTCGATTAGGAATTTAATTGCGAGTTTAACGAGGTATAACATTCAATATTCAGACAACTATTTTAAATGTTCTG
ATAAAAAAACTGATAATTTTTGTGCAGAAAATTAGAGTAATGATTTGGGAAAAATGTCATTTTTACTAAGATTTTTTTAAGATTTTAAATAAAAC
CACAATCTGTTGTGTATGATCAAATACTTACAATTAGAGAGGGTAAAACATGATTGTATCTCGTATGCATATTAACTAACCCTTTTTAATCTAAA
CTAAATCTTCAATCTAAATGGCGGGGTTTTTTTCGCGTGTATATCATCTTCGAACCTTTTGTTTTTGTAGTCATTATCTGCACTTGCTTTCAATT
TGCTCAACTTTAGATGGCAATTGTTGGATGTCAGCTGGCTTTGTCTGAACGCTAAGTAATTGAAATCCAAGTGTTCTCCAGACGCACATCATCAA
GATAATCGCCAAACTAAACACGGCCAAAGTTTCGAGCACTTTGTGGCCCATACAAGGACCTTTTGCTCAGGGAACTGGCAAATAACAAACATTTC
ATCACGAGCTGATGGAGTAATTAAATCTTAGCCAGCAGCATGTCGAGCGCTTAAATTCCGGCTAAACTGCGGGACCCTTTTGTCTCAAGTCCTCC
GACTGACCATTTAAAATGAAAAACTTGAACTTAGTGGGGAGCAGAGAACTTAGGCAGAAGTTGAGATACATATTTAGTTCCAATTAAAGTGAAGT
GCCGCTGCCAAATTAAACAGCTGAATACATGATTTTATGGAAATTCATAAAGCCCTCGATTTGTTTGCATTTTCGTTATCGTGCAGCGGACTCTG
CGCTTTTTAGCTTAATGTGAATCAACTGAATTCGGCAGCATTGCAGCTGCTCATCAGAACGCTTCCCCTAGAGCTCCCCCATCCGCTCCAGAACC
CACTCGCAGTCCCTCCAGCTCCTCCTCAGCCTGCCCACCCGCCCCCTGCTTAATTGTCACTCCACGACTTGAGGGCAACAAAAAAGAGCTTTGTG
TGCAACTTGATTTGTGCCGTACAGTAGATACCAGCTAACTTGGAAAAGTCTAGGGCTGCACGACAAAAACTTTGAAACGGATTTCATTTGATTTC
AGTATGAATCCTTTGGCTCAACACGCTTAGCCTTACTATACTTAAGCGCTGAAATATATGTTTATGCAACCAATATTCACTGTACTGTACACATT
CCACATGCAGTCGGTGGAGCCACATGCAAACCAAACCCAGTTGCGGAACCATGCTAACCCCGGGCTCGTTCGCCTTCTTCCATTCCTCTTCCATT
CCAGATCCATCATCAGCGAGTGTCTGGCCTCCTTCATGTACGTGTTCATCGTCTGCGGTGCCGCCGCTGGCGTCGGAGTGGGGGCCAGTGTGTCG
TCCGTGCTTTTGGCCACGGCTCTGGCCTCCGGCCTGGCGATGGCTACACTGACGCAGTGCTTCCTCCACATCTCGGGTAAGTCGAAGGAGACAAT
AAACAAGCGCAAAAACATCAACAGAATGGGGCGACAAGTGTCTCTTTTCGGGTTGCCCATTGGAATTGCGTGGAAACTGCCGTTTTCAAGGGAG
CCCCATGACCATAACCAGCCAGCACACGGAACCCCCTTTTTTTTTGTTTGCTATACTTTCGAGAAGGCAATGCACTCGGTGCGGCTCCACCTACT
CCAGCTCCTTGGAATCTTATCGCCCCCGGGCCAAGTTCCACCACTTCTTTCTTTTTCCCTTATTCCCTTGCATTTATTCTGGTATTTATGTATTT
GTTCATTTGCGTTGACATTCAAGGCAATTAAATGTCTTTACAAGTAAAAAAAGAAAAAGAGAATGAAAACAGACCAAAGACCAAAGTAATGTAGT
TGGGACCCCATCGTGAAAAGCGTCTTGAAACATGTGTTCTTGATTTTCCTGCAACTCCCCCATTTTGTGTTGGCTTGCAATTCCCCGCCTTTTCA
CAGCCAATTGGTTGTGCATTAAGTTATGATGTTGTTCTATACGAAATGCCTTCCGAAGAAGTGTCAAATTGATATTAAATGTTGCTCCCCTTTGG
GTGGCCACCACCAGAGATTGACGTCAGTATCTAAAGATATGCTTTCCCCTTCATAGGCGCCCACATCAATCCCGCCGTAACCCTGGCTCTATGCG
TAGTGCGATCCATATCTCCGATCCGGGCTGCCATGTACATAACCGCACAATGTGGCGGAGGAATCGCCGGAGCTGCTCTGCTTTATGGGTAAGTT
TTTTCGTATTTATTAAGTTACACATATCTTAAGTAGACAAATCATTGGTTTGAAAACAAGTAAGCCAAAATCATAAATAAACATTGCCCAATAAA
TGGAGTTTAAAGCGATATCCTTTTGAAAAGCCTCACATGAATAATTTAACCAATTGATTGAGCAAAGCCATTGATAGTCGAGGCTATCTATTATG
CACATCAAATCCCCGCATTAAAAGCCTTATGTTGTCGCATACAGCACGCCAAACTCAATTGAACAGGAATTCATTTTAAATTTTCGGTGTGCAAG AGTGTATTTAAATCTGTGTATATTTGCACGCCTGACCACAGCAATTGCTGCATTATGCGAAGGACATCGTGCATCCTGCGTGTGGAATTGCCCAA
AAGCAAACTGAAGAGTCTCAAATTAAATCCAACAGGCTGTCCAAAGAACCTAGTCGTAAATCAAAAGATTGTGGACAGGCACGGGGAGAGAGGA
CAGAGGGATACTAGGATAAATCGGATAGAGACAGATGAAACGCACTTTTGGGCGATGACTGTACAACAAGGACTCACGACAGGAAGCGTGAAATG
CGTAGAAATGGGGAATCCTACAAAAGAAATGTGCAGGTAACCTAGGACGAACACACACATACACATGCATATGCACAATCACCTGCAGGAAAAAG
GACGCAGGTAGGCTAGGATTCTCTATCTGGCGAAGAAACATCTGCCCCTATGCTCAGATGTTTGCGTAGTGATTTCCCGCTTCGAAAATGAAATT
TCTTTGTGATGCCTAGATAAAGGACCCTCTAGGCCAAGGATCTACACGCACACCAGCTAGCCAAAAATCTGTCTGCCTGTCACGGTTTTTCCTTT
GTGTAACCAAAAATCGCAGGACGAAGGACGAACGAAACGGGAAAGAGGAGTATATATGTATATATATCTGCGCATGCGCACCATTTTTCAAATGT
CGCTCCAGTTTTTGTTGTGCGTTGAACTCCTTTTGGCAGCAATGTTAATGTTAATGCCTCTTCCCGATTGTCTGCTCGACATCTGTTTCGACCC
TCGAAGAGAAGCCTCTTTTTAAGTGCGTTGGCATCTTTACTTTCTACAGATCCGATCCAAGAATCAGGAGGCGGAGAAAGGACGAGGAGAAACA
TGTTTCAGCTGCTGCGATCAGGTTCGGGGTTTTTTTCTTTCTTTCTACTCCTCCGATATGGATTTCTTAGGGTCCAACGAGTTCATCGAGTGTT
TTAGTTGGAACATATGTTTACCTAAAAAAAAGGAGATTGGGGAACCGCTCAGCTCCTTCCCCACAGCTGCCTGTGTGTGCTGATTAATTGGTTT
AGATTCAGCCCATATAGCATATATATGTAGGTTATAGCTGCGCCTGGCGATTTCTCCGAAATCGTCGTGATTTTATGAAGGGTGTTAAACTTAAT
TTATCCATGATTTTCTTAAGCTTTGAGCCAGTAACCCTTACACATAACCATATAATAAGCAACTTTAGTTGGGATTAGCAAGGGATTTATAGCTT
ATATAGTAAAGATAAAAGATTCTATGTAGAATGTTTGGAATGCAGGAAAACGATTAGTTCCCTCGCTGCCAACAATGTGTGACAAAGAGCATTTT
TAAAAAATCTAGGGGCAAGACACCCACTCTCCAAGGACCTGCCACTTCAGCTGCTCCTCCACTGGCTTCTCCACTTTTCCGCTGTCACATGTCAC
TTGGCACTTACCCTAATTGCGATGCAAATGCCACATGTGGCCAAGTGGCTAAAAAAAAGTACCACAGAGCTAAAACCGAGTATGAACTTCATTAT
CTTATGTTAAACAAAGAGCGATTGAAGAAACATTTGTGTACTTGGAATGGGTAATATGCGGGGGCGGGGGAAACGAACCTGAGTATCGATATCCG
GCTCAGGAATATTTGAATAGTCTTTAGCTGCTCCTCGAATTTCAATGATTTCTTCCCGTTCTCAATTCATATTATTATTATTATTATGGCCTTTT
TTTGGTGGTACGAAGAACGCACGCCGAGCACGTTCCAAAAATGCGAGTAGCCTTTGAAAATGTGGAAAGATAAAAATCAGGTAGAGGCCGCCGCC
AAAGGCAGCGGGGCAGCCAAGCAATGCAAAGAAACCAGAAAGCAGAAGAACATAATTAACATTTCCCTTTCGGATGGGCCTTTGTGCCCAGGTTC
TCCTGGCACTGCCGGCTACTCCAGGCTACTGCGCCTGCGCAGGATGCGTGGTGCGGAAACTTGAAATCAAACACGTGTCCGCTTCTGCGATCTGG
TTGGTCATTCGAGGAGCAGCTGGAAAAAAAAAGTGATCGGTGAACACCTGCTGCCCGAAAACAGAAAATTACTGTTGCCGAGGATGCACGACGAA
TGGAACGGAGAACAGGATTTCAAAACGAACAAATTTAAATTTCAAGCAGCTAACTGCAACAAAGCGAACTGGACAACTCAACAAAAAAAGAGAGT
GAGATCTGTACCTGCACTGAGAGAAAATCAATGGTCATTACTTAGGGTCAATGATTTGCCATCATATTATTTAAAGTCGCTCTAGGATTAATCAC
ATTACATTTATGATGGCTGATTTATATTCTATAATAATATCTGAATAAGATTTTTTATTTTCTCAAGGCAAAATCAGAAACCCTAACTTTCTAT
TCTTCTTGTGTGCCTCGTCGATTTGCATCTAGCATGGAAATGCACTTCCTGCCGTTGAAGGGATGGTTTTTAGAAATCGAAATCGTAATCAATTC
GTGTCACATGGGCAATTCAATTACTAAATCCGTTTGCCAGTGGATTCCGTTCCCCTTTCTTTATTTGCTACTACTCACTACTACGGCAGGCTTAT
CGCACTTGGCTTGGAAATAGCATCCTGCCAGTGTTTCCGGTTGCCTGCACTTGGTGGCCCCCGCATCCTCACCACCATCCTCATCAACAATGCTG
CACAGGTGGTCCAGTTATAGAGTTATGTTGCCGGCATTCAGAAAAAACACCTGGAAAGCGGGGTCAAAAGTAGTGCATTTAAAATGAACTTTTTA
TATGGGATGAACTCAAGGAAGCAGGATCAATCCTCATTGTTTCTACAAATCGAAAGTTATAGGTATGATGAGTTCTGATTATTGTTTAATTTCAG
TGGTTCTAAAAATACATCTAAAGCATGAAGAGTCTCTAGTTAACTTAGATTTAAGACAAGTGCGAAGCTACTACATGTAGTAACTTCATTTGGCG
GTCGCATCGGGAATTCAAGTGCTCCATTCCCAGTCCCTGGCAACCCAATGAGCTTGGAAGCCAGCCACAAGCCAAAAAGACCGAAAAGCAAACGC
AACCAAACCAGGAGCATTGCAAATGGCACATGGCAATCCGCAGCTCACAGTTTGCAGTTCGCAATCCGCAATTCGCCTTTCACCCGGATACGCGG
TGGCCACCAGTGCGAGAAAATGGGCAATGAGTCGACTTCGCTTGGGGATAGGGATGAGGATAACGATTCCGGTTCACAGTTCAAGTTTGCAGTTC
GGCTGCCACTTGTTTCTTTTGGCACTTTTTTTTTGTATTCCGCAAACAATTTGCGCAGGAAGAGCAGCTGAAAGCCGCCCAACATTCTGCCATTT
CCGGCTACTTAGTTGCTTCCTCCCCAGCGCTAACAGCTGAGTGTTTGTTTATCCCCGTGGATGAGTGCCTGTTGGCCACTCGTGCCATGTGAAAT
TAGCACTCTATGGATTTATGAGCAAACAAGGGTCACTTTCTATTCCAAACCAACCGAACATATCGTTTCGAAGCGATCAAATTTTAATCAAGACT
TGGGAGCAACTGTGCCCAGGAATTTCGTAAGGCAGTCGAGGATTAAGTCCTACTAATCCGTTGCTGCCACAGAGCTGGTGAACCTTACGCCCACC
ACAACTCACCTCAATCCGCAGTGCAGCCGGAACTTGCAGCAATTTCCTATTTGCTGAAGTACTTTTAAGTGCATTCCGAAAGCACTTATTTCCGG
ATTTCAAAGTGGGCGGATTCGGTGTGGTAAAGGATTGCGGTATGTCTATATAAATACCCACTCTGCTCCGCATTGCAAAATGTTATCTCACGGA
GATTCCTGTGACAACAATCAACTTCTGGAAAGCCATAATATATGGTGCCCTCGAGGAACTTTGCATCTGCATTCGGGAAACAAATTATCCGGCAG
TTTCAAATCGCAAGGATTCAAACTCATCTGGCCCAAAAGGTGCTCAACAACTTTGGTAATTGAAACTTTGACAAGCTAAATGATGTTGAGGCAGT
TGCCGGGTAGCGCAGATTAATGGAATTGACTTTGGCGGGGTGTGGATGGTTTGGAGGGTTGATTGCCGAACTGTCAGGACGATAAATAATAAATT
AAACAAATTGTCATCGGCGTTTAGCTACGAAAACTTTGTGCTCCGATATCGAAATGGTGCGGTTTTTGTACAAGCAACTTGCAACTATAAATATT
TATATACTCTATATACTATATACTTATAACTCCTTTCCTTTCATTTATTTTACAGCGTAACTGTGCCTGGTTACCAGGGGAATCTGCAGGCCGCC
ATCTCACATAGCGCTGCTCTGGCCGCCTGGGAAAGATTCGGTGTGGAATTCATCCTCACCTTTCTGGTGGTTCTGTGCTATTTCGTATCCACGGA
TCCCATGAAGAAGTTCATGGGCAATTCGGCCGCCTCGATTGGATGTGCTTACAGCGCCTGCTGCTTTGTGTCGGTAAGTTGACTTCCCCCCTCTC
CCCAACTCCAATCTCGCAACCCAGGAATGCCGGTCAGAAATCAGAAATCAGCTAAATGAAAACCAGAACCCGCCAAAACCGAAAACGAGCCGAAA
ACAAACAACTGAAACGCACCTGCCGACTGTGACGCTGTCATTTTGATGTTGGTGCAAAATCGCAGCATGACAACGGACGAGCTGGTATCAACTGG
GTAAACTCAGGTAGAGACTATCCCACAATCGTGGGACGCTGGAAGGTCGAGCTGCTGGGTTGCAGGAGATAATTAATTTAGCAAAGGAACTCCGT
GGACGGAGCTGCATTGCTGGCATAACGGACGGACAGACAGACGATGGCGACATCCAAAGAGGATGCCATCACACGGCCAAGTTTTCGAATGGGGA
ACCGATTAAAGTCAAGTTAATATCGACGCAGGATTGAATTACGATTAAGGAAAATCATGGATAAAGCGGAGTTTAATGTCCTTAGGGTTCCACGA
GTATGCTATACAATGCCCACTTTAAATTCCTTTGAACTCCTCAAGGATCATTTAAATTAAGTTATTTCATACTTAACTCTTCGACTTAGAAACTG
CTGCGAACTTCTTAAACTCTTCAAATTGTTTAAACAGTTTACTCCCCGCTTTGTTTGCCAACTTCTTTCACAAGTATCCTTTGATGAAGAATATT
CCCAGCTAGAAGTTGACACAAACGACATTGACTGGCTGACTTGTGCAGGCCGTGAAGTACTTTCCTTGCTTGGCAGATGTCTAACCAAATCCTTC
CTCCTCCCTCTTCTCCTTGCAGATGCCGTACCTGAATCCAGCCCGCTCCCTGGGTCCTTCGTTTGTGCTTAACAAATGGGACAGCCATTGGGTGT
ACTGGTTCGGACCACTGGTGGGCGGCATGGCCTCTGGCCTGGTGTACGAGTACATCTTCAACTCGCGCAACCGCAACCTGCGCCCACAACAAGGGC
AGCATCGACAACGATTCCAGTTCGATTCACTCGGAGGACGAACTGAACTACGACATGGATATGGAGAAGCCCAACAAGTATCAGCAGTCGCAGGG
CACCTACCCGCGTGGCCAGTCCAATGGCAATGGCGGAGGACAGGCGGCCGGAAATGGTCAGCACCAAGCTGCCAACATGGGCCAGATGCCGGGCG
TAGTGGCCAATGCCGGTCAGGGCAATTACTGCCAGAATCTGTACACTGCTCCGCCGCTCTCCTCGAAGTACGATCAGCAGCAGGAACCTCTGTAC
GGTGGAACCCGCTCACTGTACTGCCGTTCGCCCACTCTGACCAGAAGCAACCTGAATCGCTCGCAATCTGTGTACGCCAAGAGCAACACGGCCAT
CAATCGAGACATTGTGCCGCGTCCAGGTCCTCTGGTGCCCGCCCAGAGTCTTTATCCCATGCGCACCCAGCAGCAGCAGCAACAGCAACAACAGC
AACAGCAACAAGTGGCACCCGCACCTCAATCTTCCCATTTACAGAACCAAAATGTCCAGAATCAGATGCAGCAGCGCAGCGAGAGCATCTACGGA
ATGAGGGGCTCCATGCGCGGACAGCAGCAGCCAATCCAGCAGCAACAACAACAGCAGCAGCAGCAGCAGCTTCAGCAACAACAGCCCAACATGGG
AGTGCAGCAGCAACAGATGCAGCCTCCGCCACAGATGATGTCCGATCCTCAGCAGCAGCCGCAGGGCTTCCAGCCAGTCTACGGCACACGCACAA
ATCCGACGCCGATGGACGGAAATCACAGTATGACCGACGTGACCCGCAGCAAATGTACGGCGTGACGGGACCAAGGAATCGCGGACAGTCGGCG
CAGTCGGACGACAGCTCCTATGGCTCATATCACGGCTCGGCTGTCACGCCGCCAGCTCGTCATCCCAGCGTGGAGCCATCACCTCCGCCACCGCC
CATGCTGATGTATGCCCCGCCCCCACAGCCGAATGCAGCCCACCCGCAACCCATTCGCACGCAGTCGGAGCGAAAAGTTAGTGCTCCAGTTGTGG
TATCCCAGCCGGCAGCGTGCGCCGTGACCTACACAACCTCGCAAGGATCAGCGGTGACAGCCCAACAGCAGCAACAACAACAGCAGCAGCAGCAG
CAACAACAGCAGCAGCAGCAGCAACAGATGATGATGCAACAACAGCAGCAACATTATGGAATGCTGCCGCTGAGGCCCAACTGAAAGCGGCTGTC
ATGGGGTCCGGTGACAACGCCGCCGCCAGGGATCCACGCCCTCGCCCTCCAGCCCGGAGGCACCATGACCCTGCACCGCTGCAGCCTAGCCAAGC

FIGURE SHEET 275

AGAGCAGTTTGTTTTAGTCGTAGTCGTACGTAGTAGCATTCGGGCATCGCATCCAAAGGAAATGTACACAAGTCTCAGCCCCATATAGTCTAGCA
TAGTCCTAGTTTAGATAGACGCAGCATAGCCACATTGTATTAATTGAGAGTCAACGCGACGAGGAACTCACACCTAGCAGCAGACAACGACGATG
CGATCTAGCAAAGATCATGTACGCTTAAGGAACTAATAAGGGTTATCATTCACCGAAGGCTAGACTAAACGAGTGATCTAGATGATCTAGACTGA
AAGACAGGTGCATTTAACTAAGCTACTTCCCTTAAGTTTTGTTCAACTCTTCCAATATTAATTTTGTCAAAAGAAACTTACCTTTTTTTAAAACA
GCCTTTTGTTGCAACTCTTATTTGTTTTGGCAAATCATTTGGTTATTCATGTTTCTTGTAAATGCAAAACTAGACTGAACTTACCTAAAGCATTT
TGTACGTTATATTTCAAAGTTCATACATATATGTATATGTACTCTTCCCATTTTCCGCGGACATTCAAAGATTTTCGTTTACTTTTCGATTTTAA
TTTGTATATAGTCCATATAGACGTAAGCTATTCATGTAAATCTTACAACCCTAGGATCGGAAGTCGATACAAATATATGTATATGCTTACTTATT
AAAATAGTTGTATTTTCTTAGTGATAAACCCGTTTGCTAATAGTTGTTAGAGCCTAAGAGAACAGCGCAAATATATTGTGTATCAAAATAAAGAC
AAGTTCATCCAAACAAAGAAAGAGTTACGTTCTTATATTATTTACCAAAAAACTGTAAAATGTGTATATTTTATTATACAGAGGTGGTCAAAAG
TATTTACACAACATGCTTTCTTTTCATTTGTCAACTAAATATGCGTTTTTGGTTGGCATCAACAGTTGATATAATTGTTATATTATCATTTAATT
ATGAATACTGAGAATCCTACCTACTATTCAAGGCCTTTTTTATGAAGTTGATAGTCTTATTTCAATATGACCTTGAATACATTTAAATACCTATT
ATTTTGTGTGGTTTTTTTGAACACGTGAATTTTTAGAAAAATACAAATAACACTTAAAGCATTTTACGTTGAATAGATAGTGATTAATATCAATC
GTTGGTCAATGAATAGCTTGAATACTATCATAATCCAAATAACCATGCGCTTGGAAGATACAGTCCATGTGGGATTAATTCACGAATGCCGATTC
AAAGCATCATCTATGGATGGCCTGTTGGTCATCTGTCTCCAACGCCGAGGACATGAAGGAGAAGTACAGTCGAAGCTCGGCCAGAGGAAAGTGGG
GTAGCTCCTTTCGTACCTTTGCGAAGTCGGTGCCGTATTGCTCGAAGGCCTTGGTAAGACGGATGAGATCCTCGGCCTTCCAGCGATGGTAGCGA
CATCCTCGAGCTGTCTCAGTCTTCTCCAGACGTCGATGTGCCAGGGGCAGGTCGTATCCGTGACGCCGCAGGATGAACAGCGCCTGCTCCTCCTC
GATATCATAGAGACTGGCCGCATAGTCAAGGTATTCGCGAACAGCCTTGTCATCTTGGTCCTGCAGTTGCGGCGACCACAGGATCGAGGCTCGAT
GTTGCAGCTGCTGCAAATCCTGTTCCCGCTTCCACGGCGGCACAAAATCCGGCAAGGTGGCTGCCTGTTTTCGCCAGTAATGTATGTCTCGTTTC
TCCTTGCGTGCCGACATCCTTCGTTCAAAACAAAAAGAAAAAAATAAATAATCTACATGAAGATAGCACCG
(SEQ ID NO: 499)

Exon: 1001..1497
Exon: 3140..3306
Exon: 3952..4078
Exon: 8606..8813
Exon: 9618..11896
Start ATG: 1301

Transcript No. : CT15229
AGAAGCAACCTGACTCTGACTCGACTCGGTTATTCGCTCACCACTCGCGCTTGAATACGGACGTGTTTTCGGTTCGAAGTCAAAGTCAAAGTAGA
AGGCGAATCACAACGGATCGGTCGAAAGTTCAGAAACTCGTCAATTGACATAAATTGAGTGCAATTTGCAGTGTGCGAAATGTGTGTCTAAGTGA
AGCCAATCGACCAGCCAACAATTCGCCAGCTTCGCCGCCTCTTGTCGCGTGTTTCGCTCAATTCAACTACTTAATTAGTAGACATAAACAAATCG
TGCTTTGAGTCCGACATGGCCGACGAAAGTCTGCACACCGTGCCCCTGGAGCACAACATAGACTACCACATCGTGACGCTATTCGAGCGCCTGGA
GGCGATGCGTAAGGACTCGCACGGCGGTGGCCACGGGGTCAACAATCGCCTGTCCAGCACCCTGCAGGCTCCCAAGCGGAGCATGCAGGCTGAGA
TTCGCACGCTGGAGTTTTGGAGATCCATCATCAGCGAGTGTCTGGCCTCCTTCATGTACGTGTTCATCGTCTGCGGTGCCGCCGCTGGCGTCGGA
GTGGGGGCCAGTGTGTCGTCCGTGCTTTTGGCCACGGCTCTGGCCTCCGGCCTGGCGATGGCTACACTGACGCAGTGCTTCCTCCACATCTCGGG
CGCCCACATCAATCCCGCCGTAACCCTGGCTCTATGCGTAGTGCGATCCATATCTCCGATCCGGGCTGCCATGTACATAACCGCACAATGTGGCG
GAGGAATCGCCGGAGCTGCTCTGCTTTATGGCGTAACTGTGCCTGGTTACCAGGGGAATCTGCAGGCCGCCATCTCACATAGCGCTGCTCTGGCC
GCCTGGGAAAGATTCGGTGTGGAATTCATCCTCACCTTTCTGGTGGTTCTGTGCTATTTCGTATCCACGGATCCCATGAAGAAGTTCATGGGCAA
TTCGGCCGCCTCGATTGGATGTGCTTACAGCGCCTGCTGCTTTGTGTCGATGCCGTACCTGAATCCAGCCCGCTCCCTGGGTCCTTCGTTTGTGC
TTAACAAATGGGACAGCCATTGGGTGTACTGGTTCGGACCACTGGTGGGCGGCATGGCCTCTGGCCTGGTGTACGAGTACATCTTCAACTCGCGC
AACCGCAACCTGCGCCACAACAAGGGCAGCATCGACAACGATTCCAGTTCGATTCACTCGGAGGACGAACTGAACTACGACATGGATATGGAGAA
GCCCAACAAGTATCAGCAGTCGCAGGGCACCTACCCGCGTGGCCAGTCCAATGGCAATGGCGGAGGACAGGCGGCCGGAAATGGTCAGCACCAAG
CTGCCAACATGGGCCAGATGCCGGGCGTAGTGGCCAATGCCGGTCAGGGCAATTACTGCCAGAATCTGTACACTGCTCCGCCGCTCTCCTCGAAG
TACGATCAGCAGCAGGAACCTCTGTACGGTGGAACCCGCTCACTGTACTGCCGTTCGCCCACTCTGACCAGAAGCAACCTGAATCGCTCGCAATC
TGTGTACGCCAAGAGCAACACGGCCATCAATCGAGACATTGTGCCGCGTCCAGGTCCTCTGGTGCCCGCCCAGAGTCTTTATCCCATGCGCACCC
AGCAGCAGCAGCAACAGCAACAACAGCAACAGCAACAAGTGGCACCCGCACCTCAATCTTCCCATTTACAGAACCAAAATGTCCAGAATCAGATG
CAGCAGCGCAGCGAGAGCATCTACGGAATGAGGGGCTCCATGCGCGGACAGCAGCAGCCAATCCAGCAGCAACAACAACAGCAGCAGCAGCAGCA
GCTTCAGCAACAACAGCCCAACATGGGAGTGCAGCAGCAACAGATGCAGCCTCCGCCACAGATGATGTCCGATCCTCAGCAGCAGCCGCAGGGCT
TCCAGCCAGTCTACGGCACACGCACAAATCCGACGCCGATGGACGGAAATCACAAGTATGACCGACGTGACCCGCAGCAAATGTACGGCGTGACG
GGACCAAGGAATCGCGGACAGTCGGCGCAGTCGGACGACAGCTCCTATGGCTCATATCACGGCTCGGCTGTCACGCCGCCAGCTCGTCATCCCAG
CGTGGAGCCATCACCTCCGCCACCGCCCATGCTGATGTATGCCCCGCCCCCACAGCCGAATGCAGCCCACCCGCAACCCATTCGCACGCAGTCGG
AGCGAAAAGTTAGTGCTCCAGTTGTGGTATCCCAGCCGGCAGCGTGCGCCGTGACCTACACAACCTCGCAAGGATCAGCGGTGACAGCCCAACAG
CAGCAACAACAACAGCAGCAGCAGCAGCAACAACAGCAGCAGCAGCAGCAACAGATGATGATGCAACAACAGCAGCAACATTATGGAATGCTGCC
GCTGAGGCCCAACTGAAAGCGGCTGTCATGGGGTCCGGTGACAACGCCGCCGCCAGGGATCCACGCCCTCGCCCTCCAGCCCGGAGGCACCATGA
CCCTGCACCGCTGCAGCCTAGCCAAGCAGAGCAGTTTGTTTTAGTCGTAGTCGTACGTAGTAGCATTCGGGCATCGCATCCAAAGGAAATGTACA
CAAGTCTCAGCCCCATATAGTCTAGCATAGTCCTAGTTTAGATAGACGCAGCATAGCCACATTGTATTAATTGAGAGTCAACGCGACGAGGAACT
CACACCTAGCAGCAGACAACGACGATGCGATCTAGCAAAGATCATGTACGCTTAAGGAACTAATAAGGGTTATCATTCACCGAAGGCTAGACTAA
ACGAGTGATCTAGATGATCTAGACTGAAAGACAGGTGCATTTAACTAAGCTACTTCCCTTAAGTTTTGTTCAACTCTTCCAATATTAATTTTGTC
AAAAGAAACTTACCTTTTTTTAAAACAGCCTTTTGTTGCAACTCTTATTTGTTTTGGCAAATCATTTGGTTATTCATGTTTCTTGTAAATGCAAA
ACTAGACTGAACTTACCTAAAGCATTTTGTACGTTATATTTCAAAGTTCATACATATATGTATATGTACTCTTCCCATTTTCCGCGGACATTCAA
AGATTTTCGTTTACTTTTCGATTTTAATTTGTATATAGTCCATATAGACGTAAGCTATTCATGTAAATCTTACAACCCTAGGATCGGAAGTCGAT
ACAAATATATGTATATGCTTACTTATTAAAATAGTTGTATTTTCTTAGTGATAAACCCGTTTGCTAATAGTTGTTAGAGCCTAAGAGAACAGCGC
AAATATATTGTGTATCAAAATAAAGACAAGTTCATCCAAACAAAGAAA
(SEQ ID NO: 500)

Start ATG: 301

MADESLHTVPLEHNIDYHIVTLFERLEAMRKDSHGGGHGVNNRLSSTLQAPKRSMQAEIRTLEFWRSIISECLASFMYVFIVCGAAAGVGVGASV
SSVLLATALASGLAMATLTQCFLHISGAHINPAVTLALCVVRSISPIRAAMYITAQCGGGIAGAALLYGVTVPGYQGNLQAAISHSAALAAWERF
GVEFILTFLVVLCYFVSTDPMKKFMGNSAASIGCAYSACCFVSMPYLNPARSLGPSFVLNKWDSHWVYWFGPLVGGMASGLVYEYIFNSRNRNLR

HNKGSIDNDSSSIHSEDELNYDMDMEKPNKYQQSQGTYPRGQSNGNGGGQAAGNGQHQAANMGQMPGVVANAGQGNYCQNLYTAPPLSSKYDQQQ
EPLYGGTRSLYCRSPTLTRSNLNRSQSVYAKSNTAINRDIVPRPGPLVPAQSLYPMRTQQQQQQQQQQQQVAPAPQSSHLQNQNVQNQMQQRSE
SIYGMRGSMRGQQQPIQQQQQQQQQQLQQQPNMGVQQQMQPPPQMMSDPQQQPQGFQPVYGTRTNPTPMDGNHKYDRRDPQQMYGVTGPRNR
GQSAQSDDSSYGSYHGSAVTPPARHPSVEPSPPPPPMLMYAPPPQPNAAHPQPIRTQSERKVSAPVVVSQPAACAVTYTTSQGSAVTAQQQQQQ
QQQQQQQQQQQQMMMQQQQQHYGMLPLRPN*
(SEQ ID NO: 501)

Classification: known_flybase_gene
Gene Symbol: bib
FlyBase ID: FBgn0000180

Celera Sequence No. : 142000013385213
TTTATCGGAATGGTCAGATCGGAATTTAAAAAAAAAAAACTTTAATTTCTCCCCAACTCAAATTGAAACACACAAACAAATGAATGTACTTAAACC
CTTTTTTTTTGCTAGCGAGTATGCGATCAAAACTAGAGAAACATATGTACGTTTTTTCCCTTATAATTGATGGCAATCTGGTCCCAATAAATCCT
TCTCACCCATTTCGCGCCTGCTAATTGCCAAACAAAATGCAATAATTCAACCCAAAAGCACGCTTTCTTTTCCTAGCACAAATACAATACCCCTT
TAACGGCCGCAATTTCCCTTTTTCACCCTTTTGTTTGCCAGGTCACCCGAAAAGTTTTACCGAGCAGGGTTGTCGCATGACCCCCCGCAACCCAC
AACCACAGCAGCAATCGCTTTTTATTCTCTTTTTATATGATTGTTTCATATTTATGAGGATTATATGGCTGATGCTGAGTGCTGAGAATCAGAGA
AAAATTGAGTTGGACGTGTGGTAATTTATTTTTCGGCTAAGGGGACGGACTTGTAGTTAACTGTTAGTTTTCCGAGCTCAAGATCGCACAGATTA
TAAAGAATTTACTGTGCAATACTAATTAAATTTATCTTTATCATTATTTTACTTAAACGGAATTTGTATAAGCCAAAAAACAAAATTTATTAATA
ATCTCCAACTAAAAATGTGTATCAATGAAATTATTTTCTTATGGAATTAAATTTCAATAGTTTATGCCCGCCTTTGTATTTAACATCTAAACATT
AGAATTAAATAAAGTATTTAAAAAAAAATTTAGCGTATAAAAAGCATGGATTGATTCCAAGTGCATTTTACGAATTTGCATTGAATCACGATAAT
AATATTCACTTGTAATACTTAATTAAATAATTTAATTCGGAACCCATATTAATTTACCGAGTTCGAGGCGGGTTGGCAGTCCGATTGCATGACGT
AGCAACGCCGCCACTTTCCAGCACTGGCCGATTGCCAGCCAAAATGGCGCCCGCCTGCTATCGCATTGCTCGAGCAGATATCGGTTCGGCAGCGC
ATCACACACACAACGCGAAAAAAAAAAGAAAAATACGGGTGGCCTGCAAGCGAATATCTCCGAAATTCATTGAATCCCGACGCCGAGATTTGTGC
TCCGATCCGAGAAACCCATTAGCTTCCGTGCACCGTCCGCCCAAGCCAGCAAAATAACCAAGTTCAACATACGCCTGGACAACATAATGTCGAAG
AATAAAAAACTGTCGCTGTCGGGCGGCGATACGACGGAGAAATTTATTTACAAACCCAAGGATCTGATATGGTAAGCCGGGACCGTGGACTCATC
AATATATTCGCTGTATTCTCAGCTGCGCTGCGCCGTGAAGAAACAAGAAAAAAAAAAAAAACGAGAGATGAAAATCAAAGCAAACACCTAACCTCA
ATTGCGCACCGTTGGCGCTCGGAAAAAAAAAATATGAAGAAAAAAAGAGCCAGTGAAGTGTGCATAAAAAAGCAATTAGCGCTGCCTTTTTGACAG
CCACGCAGCGCAGTATCCATGTAGCTCCATCCGAATGACGACCATAATTCCGGAGCTACGTGCGTGGATTCCGGGCGCGCGACGTCGACTTCGCT
GCGTTGGCGCTTTTTTCGCGCGCGCGCCCTTTTTTCTTGCTTTTCCTCCTTGCGGCCAATATGAGTTTTCCCTGTTCTGATAGCGCATTTTCTTT
GCAGGGCCAAAATGAAGGGCTTCACTCCGTGGCCAGGAATGGTAAGCATTGCAGTTGGCGATCGGAATGTTTACGCCGCGTCGACGTCGCGTCGC
TGCCGCCTTCTCTGCTGCCATGTTGTTGTGTTTGTTTTCGACTGTACTTTTCGATTCAACGCTGCCGGCTTCGCTGCCGCCGCTCTGCCCGCAGC
CACGCACTTGCACACATTGCCCCATTGCCGTTGTGGTTGTTGTTGTTGCCGCTGTGCTGTTGTCGCTGCCGGCGGAGGAAATGGTCTCTTCCATG
GAGCCGCTATCGGGGGCCACGAGCAGCAGCTTTTGATCGTGTGTACAGCCGCTGGAAAGCAGCATGTGCACTCGGAGGAGGGGGAGTGACGCGCG
GCAGGCGTGGAGTTTGAACACAGACGTTGCCAAGGATATCAGTTCCCAGTTTCGTTATTCTATGCCGTTCAAAAGGAGTTTTGTTAATATATTAA
CTTTTATTTGACATTAACATTCTCATCGGTAATCTTGTGATATACCAATCGGTTCTTTAGAGTTTTGTGAAATGTGCTAATGATAGTGAATCACC
TCAGCTAAGGTTTTATCAAATCAAATTGGTTTTGTGCAAGTTGCTAGAAAAATGAGGATATATTTTTAAATCCTTATAATTCCTAGCTCAAATGT
AAAGTTAAAGAGTGGTTTTCGATTGAAATTGGAAGTGAAAAAGCAACATTTGCATATGTTTTGTTTCGTGCGTGATAAAGTCTTGTAAATGGGTT
ATCACAGAATAGATTAGTTCGAGGGAATTCATAGGCACATCCTTATAGAGTAAAATGCATTGTCTGCTTAAAATGTTTCTGAAGACTTTAAAGAT
ATGATGTGGTGGAAGCTAATGTTGATTTCTCTCCTTAGATTGTCGATCCTCCACTTGATCTGCTCAGCCAGCAGCGTCGGGCGAATACCAAATGC
GTGTTTTTCTTTGGATCTAGGAATTTGTAAGTAAAATGCACGCCAACCCCAAAAAGCGCCTGTAATAACATGGGTAATATTTAACAGTGCCTGGA
TTGAGGAGAACAACATCAAGCCCTTCGAAGGACCGTGGAAGGAGGAACTGGCCAAGGTGAGCAAGCCCGCTGCTTTCCGACACGCCATGACGGAT
ATCGAAAAGTACATCGACGACCCCGCCGAGGTGGACGAGCAGGTGAACAAAAGCTGCGGTGCGCCGAATCACGCAACCGAGGCTGATTTTGACAA
GATCCGGGATGGCCTGGACAGCGAGGAGATTGTGGGAGAGGAAGCAACTGCCGATGGCAACAATGGAGTGGTGGCCCATGTGGTGGGCAGCCCCG
ATGAGGGCGATGGCTTGGATGTGGAAATCAATGCAGATTCATCAGCGTCACCAGTCACGTCGCCGGCGGTCACAACGAAGGCAGCTGGCAAGCGG
ACGCCGAAAGCAAAGTCCGTGGCCGCTACATCGGTCAAGTCGACAAAGGGATCGGCAAAATCAGCACAGAAACGGCGTACCTCTGCCCAACAGTC
GCCCAGTGGGCCATCGAATGCCAAGCGAGGCAAGCGTGATGTTTCCGGGGAGGCATTGCAGGACGCGGATGAAGCCAGCTCCACGCCCACTGGCA
GACGTCGGGTCGAGACTGACGCACTCTTGGCCTCAATCGCTGCCAAGCGTGCACCGAATGCAATTGCTCTGCTTGACCGACCGGTTGTCACGCGG
CCAGAGGCCCAAGTCATCGACATGAGCTCGCGCTCCAACACACTGGCCGATCGCGATATCGTGCCTTCAGAGCAGACCTTCGGCTTCCTGGGTCT
TGGAATGATGGGATCCACCATAGTCAAGGATTTGATCTACACGGGTCACAAGGTTGTGGTCTGGAACCGCACCATTGACAAGGTAAAGTTTTACG
ATAGCAAGTTCACACATGAATCCTACAACAATCTCGTTTTGTAGTGCCAACCGTTTGCCGAAGCCGGCGCTGAGGTTAAGGACACTCCCATGGAT
GTTGTGGAAGCTGCCGACGTTATCTTTTGCTGTGTGTCCGATCCAAAGGGCGCCAAGGATGTAAGTCATAAAAGGTTTCATTTATATACATATTT
AATTTGGGAAATGCCTAAAACACAACGTGGTTAACAAAACTTAAATTTTGGCCTTGGGGTTCCTATAAAATTCAAATGACTCATCCGCGCTTGTT
AACTTAAAAAGTACATATGAATGAAAGCACGCAGTTTAAAATGACGATTTTCTGACGCTCTCTTTGCAAAGCGATCTTCCTTACACTGTATAAAA
TTAAAATATATTAGAATACAAAATAATTGTGCAACTGGGAGGGATGGCGTAATTTAACATTCTTCTTATTTATGCATTCGTTTTATTCGATGTTT
AGCTCGTATTTGGCAACTGCGGCGTTCTGCAGTTGAAGGACTTGAACAATAAGGCCTACGTTGAAATGTCTACAATTGATCCGGACACATCGTTG
GACATTGGCGAGGGCATCAAGCAGTGCAACGGTCGCTATCTTGAGGCACAAATTCACGGCTCTCGGCAGGAGGCTGCCGAAGGCATGCTCATCAT
TCTCGCCGGTGGAGATCGTTCAGTGTTCGAGGAGTGCCACTCGTGCTTCAAGACCATTGCCAAGAACACCTTCTTCTTGGGGAGTAAGTACAGCC
TGCACTGCTGACCATTTCCTTTGAAACAATTTATTAAAATATGTCGTTTGTTCACATCTAGCAGATATCGGTAACGCCTGCAAAGTAAACCTAAT
TTTGCAAACCATCTTGGGAGTGAGTCTGGTCGGGTTGGCTGAGGCGTTAGCACTTGGTAGGTTTTATTGTATATTGTTAGCAGTAAGCAGCCTTA
ACTAATTGATCTTTTTTTTTATTGCTTTTGCAGCTGATCGGTTCTCGATCTCTCTGAACGACATCATAGACATTTTCGATTTGACTTCAATGAAA
TCACCCATGCTGCTGGCTAAGGGCAAAGGTATGGATAGCACCGTGGCTATTTCCTAGTGTTTATCTTATCCTATTTTGAATTCCTTTGCAGAAAT
GGCCAAGGGTGACTTCAATCCCCAGCAGCCTTTGAGCCACATGCAACGCGACTTGCGCTTGGTGTTAAACATGGCTGAGAACCTGGACCAGTCCA
TGCCCGTCACCAGCATCACCAACGAGGTGTTCAAGCACACCAAGCGCTTGGGCTACAGTGAACACGACTCGAGCGCCGTATTCGTAAGATCCAGA
TTTTAACATTTAGTTAACACGACTAACGTTTAAACTATGTTTTATCAATTAGTTTAAAGCGTACACCGAACAGAACGACAGAACCGACAAACGAC
TGACTTAAAAAAAAAAAACTAAACAGGACAGTAATAGAAACGCATAACCCTCACTTATTCACCCACCAATCCAAACTGACAGAGGCGTTCGTTCA
CAAGGAGTTCTCCTGCCCTTGTGATTGGCAGCGCCACCACCCCAACCTTCTGCATCTTCCCCAATCGCCCCATATGCAAAGCGTTTAATGCAATA
TGTCTACGATTCGCCGGGAATCGCAGAACCGTGTCGTCCTGCTTTCAACGCAGGAGCCACTGAAGAGCGCTTGGGTGAGTGTGTTCAACAGCTGG
CGGATGAAGAGCACAATCTTTCCGGGATCACTTCAATCAAGTTTAGAGTTTTTTTGTATTTTATTCTTTGACGGGTGAAACGCAATCCCCAGAGA
GGAGGGAGGAGGCCAGGGCGCCGTGTTTCCGATTTTATATGTGTAAGGTTTTGCTTTCCAAATATCATTTTTACGCATGTCCATACATAACTTGT AAGTGTATAGAATACTGCATCCGAATAAAATGTACAAAGCATACTTGTGAAAGACAACGCCGATTTTGAGAAACCGAGCGAAGTATGGAACCCTC
CAATGTGTGTCGATCCAACCTCCCAGCCTCCCACTTTTTGTGCATTTACTCCAGTCCTAAAATTGTATACATTTAAAATCCCCTTTTTTTCTATG
AGTAAATAGTAGGCTAATCGATCATACTGCGTAGAATGGCAAACATATTTGGAGTGACGGTAACGATAGATTGGTTTAGTTTTAGCCATCTCTCC
CCATCATCTGTCACTGCAACAAACGAGACACAACCTAAAACGGAAAAAACGGTACAGAACGCACCACAACCGATACGCAAACGATACGAAAACGT
AAACTACACAACAACCGGAAGAAAACAAAATAGAGTAAACTTTGATCGAACCCTTTGCGTGGGTCGCTATTAATAATAATAATAAGAATATATAA
TAAATAATATATTTTACTTATTATTTAGTCTGTATTTTGTTGTAAAACAAAGATTA
(SEQ ID NO: 502)

Exon: 1001..1306
Exon: 1722..1751
Exon: 2604..2686
Exon: 2748..3597
Exon: 3655..3765
Exon: 4088..4358
Exon: 4435..4521
Exon: 4594..4683
Exon: 4747..5041
Start ATG: 1304

Transcript No. : CT15275
CCGCCTGCTATCGCATTGCTCGAGCAGATATCGGTTCGGCAGCGCATCACACACACAACGCGAAAAAAAAAAGAAAAATACGGGTGGCCTGCAAG
CGAATATCTCCGAAATTCATTGAATCCCGACGCCGAGATTTGTGCTCCGATCCGAGAAACCCATTAGCTTCCGTGCACCGTCCGCCCAAGCCAGC
AAAATAACCAAGTTCAACATACGCCTGGACAACATAATGTCGAAGAATAAAAAACTGTCGCTGTCGGGCGGCGATACGACGGAGAAATTTATTTA
CAAACCCAAGGATCTGATATGATGAAGGGCTTCACTCCGTGGCCAGGAATGATTGTCGATCCTCCACTTGATCTGCTCAGCCAGCAGCGTCGGGC
GAATACCAAATGCGTGTTTTTCTTTGGATCTAGGAATTTTGCCTGGATTGAGGAGAACAACATCAAGCCCTTCGAAGGACCGTGGAAGGAGGAAC
TGGCCAAGGTGAGCAAGCCCGCTGCTTTCCGACACGCCATGACGGATATCGAAAAGTACATCGACGACCCCGCCGAGGTGGACGAGCAGGTGAAC
AAAAGCTGCGGTGCGCCGAATCACGCAACCGAGGCTGATTTTGACAAGATCCGGGATGGCCTGGACAGCGAGGAGATTGTGGAGAGGAAGCAAC
TGCCGATGGCAACAATGGAGTGGTGGCCCATGTGGTGGGCAGCCCCGATGAGGGCGATGGCTTGGATGTGGAAATCAATGCAGATTCATCAGCGT
CACCAGTCACGTCGCCGGCGGTCACAACGAAGGCAGCTGGCAAGCGGACGCCGAAAGCAAAGTCCGTGGCCGCTACATCGGTCAAGTCGACAAAG
GGATCGGCAAAATCAGCACAGAAACGGCGTACCTCTGCCCAACAGTCGCCCAGTGGGCCATCGAATGCCAAGCGAGGCAAGCGTGATGTTTCCGG
GGAGGCATTGCAGGACGCGGATGAAGCCAGCTCCACGCCCACTGGCAGACGTCGGGTCGAGACTGACGCACTCTTGGCCTCAATCGCTGCCAAGC
GTGCACCGAATGCAATTGCTCTGCTTGACCGACCGGTTGTCACGCGGCCAGAGGCCCAAGTCATCGACATGAGCTCGCGCTCCAACACACTGGCC
GATCGCGATATCGTGCCTTCAGAGCAGACCTTCGGCTTCCTGGGTCTTGGAATGATGGGATCCACCATAGTCAAGGATTTGATCTACACGGGTCA
CAAGGTTGTGGTCTGGAACCGCACCATTGACAAGTGCCAACCGTTTGCCGAAGCCGGCGCTGAGGTTAAGGACACTCCCATGGATGTTGTGGAAG
CTGCCGACGTTATCTTTTGCTGTGTGTCCGATCCAAAGGGCGCCAAGGATCTCGTATTTGGCAACTGCGGCGTTCTGCAGTTGAAGGACTTGAAC
AATAAGGCCTACGTTGAAATGTCTACAATTGATCCGGACACATCGTTGGACATTGGCGAGGGCATCAAGCAGTGCAACGGTCGCTATCTTGAGGC
ACAAATTCACGGCTCTCGGCAGGAGGCTGCCGAAGGCATGCTCATCATTCTCGCCGGTGGAGATCGTTCAGTGTTCGAGGAGTGCCACTCGTGCT
TCAAGACCATTGCCAAGAACACCTTCTTCTTGGGGAATATCGGTAACGCCTGCAAAGTAAACCTAATTTTGCAAACCATCTTGGGAGTGAGTCTG
GTCGGGTTGGCTGAGGCGTTAGCACTTGCTGATCGGTTCTCGATCTCTCTGAACGACATCATAGACATTTTCGATTTGACTTCAATGAAATCACC
CATGCTGCTGGCTAAGGGCAAAGAAATGGCCAAGGGTGACTTCAATCCCCAGCAGCCTTTGAGCCACATGCAACGCGACTTGCGCTTGGTGTTAA
ACATGGCTGAGAACCTGGACCAGTCCATGCCCGTCACCAGCATCACCAACGAGGTGTTCAAGCACACCAAGCGCTTGGGCTACAGTGAACACGAC
TCGAGCGCCGTATTCGTAAGATCCAGATTTTAACATTTAGTTAACACGACTAACGTTTAAACTATGTTTTATCAATTAGTTTAAAGCGTACACCG
AACAGAACGACAGAACCGACAAACGACTGACTT
(SEQ ID NO: 503)

Start ATG: 304

MMKGFTPWPGMIVDPPLDLLSQQRRANTKCVFFFGSRNFAWIEENNIKPFEGPWKEELAKVSKPAAFRHAMTDIEKYIDDPAEVDEQVNKSCGAP
NHATEADFDKIRDGLDSEEIVGEEATADGNNGVVAHVVGSPDEGDGLDVEINADSSASPVTSPAVTTKAAGKRTPKAKSVAATSVKSTKGSAKSA
QKRRTSAQQSPSGPSNAKRGKRDVSGEALQDADEASSTPTGRRRVETDALLASIAAKRAPNAIALLDRPVVTRPEAQVIDMSSRSNTLADRDIVP
SEQTFGFLGLGMMGSTIVKDLIYTGHKVVVWNRTIDKCQPFAEAGAEVKDTPMDVVEAADVIFCCVSDPKGAKDLVFGNCGVLQLKDLNNKAYVE
MSTIDPDTSLDIGEGIKQCNGRYLEAQIHGSRQEAAEGMLIILAGGDRSVFEECHSCFKTIAKNTFFLGNIGNACKVNLILQTILGVSLVGLAEA
LALADRFSISLNDIIDIFDLTSMKSPMLLAKGKEMAKGDFNPQQPLSHMQRDLRLVLNMAENLDQSMPVTSITNEVFKHTKRLGYSEHDSSAVFV
RSRF*
(SEQ ID NO: 504)

Classification: hypothetical

Celera Sequence No. : 142000013384043
GATCGGGTCCTTGGCATTACGGAGAATCTGGTGGACTTCCTCCACTTTGGCGCGCTCTTCACGCTTGGTGGTGATCAGGTTCTTGAGCCGTTCGT
TGCTCAGCGAGTTGAGAATGTTGTCCATATCGGTGGCTGGCAGTCGGTTGGCAAAACCGTGACGCTTGCGTATTTTGTGGTGAACTCCCTTATTA
ATGCCCAATAGTGGACGGGAGGTTGGCGAGATTTTCGTTGGTTGTTTAAGCGAATTCTTGGATATGGACGGCCGCCTTCTTGACTTTGTGACCGC
TTCTCCACTGTGGGAATAGAAGGCCATGGTGGGAATGCTGCTGCTCAGCGTCACCTTGCGCATCTTGCTCTGCGGCGAACCAGAGTCGGCGTCCG
CTGAAGGAGCAACCGGGGTGGACGTTTCTGGGTGCTGTCGCTTTTGAGGCTTATGATTGGATGCTTCTTCGTCCGATTCGGGCACTTCGACATCA
ATCTTCATACTACTTCCTGGGCTTTCTGGCCTTTTTGCTGTGGCAACTTCGGAAGATTTCGCTGTTTTATTGTTGGTGTTTCCTGTGTTTCGTTT
TACTGCATCGTCATTTGACTTGAACACTTCTACCGGGGACTTGGATCTGCTTCTGCTGTTTTCTAGCTTAACTGCTGCTGTTTTTTCTTCATCAT
ACGACCTCATGTTCTCATGTAGATGGGCAGCAGCCTTCAGCGTCTTGCAGTTTATATCCGCCGACGTGAAGGGTCTTCGCCTATTCCTGGTTTTT
GGACTGATGATTTGCGAGCTCCTTGTTTCACGAACTTCTGTATTCTTCCTGGAGTTCTTACTGCTAGAAGGTTTCTCGTCGTCCGACTGGGACTC
TTCAGCTGGGCTCGTTTTCTTCGGTTTAGTTGTATGCACTTGGGCAGTGGTCTTTAGGCTGTGGTTGTGTTTCTTCTTTGATTTTTCTAACATTG
ATCTTGAATCCTGACCCTTCATTAGCATAGCTGCCACCTTGCTTAGCCTAGTCTGAAAAGATTCTGGCGAGGAGAACGCATCTGGATCCTTTTGC GCACTGAAGGTTCGTGGACTGCGTCTGATGCTATTTCTGGCTCTGGAAGAAGGAGTTCCTTCAGAGGAAGAGGTGGGCGACGACATTGAAGAATC
CGCTCGCTTTCTTTGGACCCTCGTCTGACGGGGGCTGCTGTTGCGACTATTGCTGCTGCTGTTGCTATTTAGCCGCATGGTGGCTGTAAACAATT
GGGGCAGCTGCTCCGCCGTGGCAGTCATGACTCCGCCACGGGTTTTTTGTTCTCCTTGTTGGTTTCCGGGCTGCTGTTCGCACTGCTGCTTGAC
TTGCCGGGGACTGCGGCGAAGAGACTCCTGCCCTTCCTGTTGGCCGCCACATGGGTCTTTAATGGCAAGACACCCAGACTGTCTACGTCCGCATC
ATCCTCGTCGTCGTTGATTTGGCGCAGCCTGGATCTGGGACTGCCAAACAGTTGCCGCTTGCGCTCCGAAAGGCGCGGAGTGGCCATGCGACTGG
GACGCCCACTACCCGTCGGGGTCTCCATGATCGCGCGCAAATCTTTTATTTCGCATTAACTTTGTCCAAATTGTGACTCCTTCGCGCTTTTTTGT
AGCTGCCTAGTGTTGGGGGTGGTTGGATCGTTCAGGGTCTCTTCGGTCGTTTGCCAACACATGCCAGATCGTCTATGTTTTTACTGCAATGTTTA
TATATATTAAATGCATTACATTGTTTTTAAATTTTTTTTACATCAATGTTTATAAAAATCAAATACATTGCAATGTAAATATTTTCTGTTAGTTA
TAATTTTTTTACCACATTTTACATTTAACATTTTTCTTCGAAGCGATCAAGTCAGCTTGCAGTTTTTCGTAAATTATTTGGACTTATTCTACGAT
TTCTGTAAAATAAATAAGTAATGTTAATTATATTCTTGATCCAAGACAAAGTATTCAATATAGTACCACTTAACGAGTTACGATCATGATCGCTA
GACATTCTATGTTTTCTAATCTTCATATATTTTAAAGATTTCCGTATTATTTTAACTATCCGGTATTTTTACAGAGCTAAGGTGATCATATAACG
GGAAAACTCTATCTGGTATTTCCACCCAAGTCAGACTCAGTCACACTCTTCCAGACGTCACACGGTCATATTGCGGACGAAGTGCGAATCGATTT
GGAAAAATCTGCTGCTCGGCCTGGAAAGTAGAAAGTATAAAGCTCTGCGTTTATAATTTAATTTGCAGCCAAAGCCCGCTGCCGATCAGGTAAGT
TAGCTCCCCCACATTATCCGTACCGCCATTTGAAAGCCACGCCAACGAGAACCGTGAGAAAATGTGAACTCTAGCCGCCGCCATCTTTTTTTATG
TATGCGTTAGGCCACAACGCCAATAATGCGATTTAAAACCGAGTTTATTAAGATTACTCGCGCTCCTTGTGCTGCTGCCTTAATGTTTATCCTTT
GCTCGTATTGGTTAAAATAGAAAACAATTGCACTGTCTTCTCTCTTCTCTTGAGGTATCGCGTTTGTTCGTCGCCGTTGTCGTCCTCCAACCGCG
GTATATACATACAAACATATAGGCAAATATATATAAATATATTTTCGACGCAGCCGCCGCCGCCGCCGCCGCGTAGATATCCATTTTCCGGGATT
ACCCCACCCAGAGTGATATAAACGATATAACCGTGGACGACCACGCAGCGGAACCCGCTGCCGCCATGCCCGGAGCCGGCACGTTCAAGTTATTC
ATCGGGAATCTTGACGAGAAGACACAGGCCACCGAGCTGCGTGCACTGTTCGAGAAGTACGGTACCGTCGTCGAGTGCGACGTGGTGAAGAACTA
TGGCTTCGTTCACATGGAGACGGAGCAGCAGGGTCGCGATGCCATACAGAATCTGAACGGTTATACGCTGAACGAGTTCGCCATCAAGGTGGAGG
CGGCCAAGAGCCGGCGGGCGCCCAATACGCCGACCACGAAAATCTTCGTGGGAAATCTAACGGACAAGACGCGGGCGCCGGAGGTGCGGGAACTG
TTTCAGAAATACGGCACCGTCGTCGAATGCGACATTGTGCGCAACTATGGTTTTGTCCATCTGGACTGTGTCGGTGATGTGCAGGACGCCATTAA
GGAGCTGAACGGTCGCGTTGTCGATGGCCAGCCGCTCAAGGTTCAAGTGTCGACCAGTCGGGTCCGCCCCAAGCCGGGCATGGGCATGGGCGATCCGGAGC
AGTGCTATCGGTGCGGAAGATCCGGGCATTGGTCGAAAGAGTGTCCGCGACTGTACGGCAGTGCCGGAGGCGGACGCGAGCCGCCATCGCCCCTC
AGCGCCGGCGGCTACAGAGATCGCATGTACGGTCGTGACCCGTATCCGCCGCCACCACCGCCGCCGCCGTTCCTGCGTGACCGCATCATGGATGG
CTTTAGGGTAAATTCAGCATCCATTTGCCCCCCCGATCAAATCATCCATTGTGCCAAGTATTATTCACATTCTGTGCTGCTACTAATCTAAATCT
TGTTTTCCCGCCCGCAGGACTATGACTACTATGACCGCCGCTTCGAGGACTCACGCGATCTGTATGAGCGTCGCTATCAGACCTCGCGAATGCGC
GACTTCCCACCGCCGCCCATCTCTCGCCGCGAACCCATGCCTCTACCGCCCACCTTAAGCGGCAGCCTGCGCTCCTGCAGCGTTTCTCGTGGATA
CGACACTATGTTCAGCCGGCGCTCGCCTCCGCCGCCGCGTAGCAGCAATGGAATGAGTCGCTACGGGTAGGTAACCCTGCAAGTGGATGAAATGT
CGCACTTTCTTTTCCAAATATGTGTGTACTAAAGTTAATTCTTATCAGATGACTACGTTTTCCATACTTACTTACATATTAAGACCTAGATAGTG
CTTTGCTTATATGATGAAATTATAAAATGAAACGATGAAAGATAACATTCGTATATCTCCATCGAACCTATTTTGAAATCAGTTTTTAATGAATT
ATTTTCTATCTCCTCCCAGCTCGCCCACTCCACACGGTTACGAGGACTTTAGTCGCGATGCATTCGACGAACGCATGATTTCGTCGCGCGGAATG
CGCGGTCCATCGCCGCCGGGTCGCAGATATGCGCCCTACTGAGATGAGTTTTACTATCACGGCAGCAGCTGAGTAGCGGTTGCACTACCCATGCC
CCTGCCAATGGGTCACACATTCTACCACACGACCAGCAATCGAAGAACGGCGCCTGTGGACTGCTGGCTGCTCTGCTGGTCGCCAGCGGCGGCCT
ACTACCATCACCACCAAGCACACCAGCAGCACATGCTGATGCCGACGACAATTTCACAACTGTGGCTGCCGCCTTGGTAAACCACATACATGTTA
CTAAACCCAAACTAACCATTACTCGTACACTTAAACAAGAAGATGGAAATACGTGTTTAAGCATCCTCCCTATATGCAAAACACGCCAAAAAAAA
AAAAGAACTAGACAACGACGTGCAACCTCTACACATTCAACCGTAGTACCAATAAACGCATAATCAGTCGAAACTGTGCAAAAATAAACACTGTA
TTTTAAAGCTAGTTTAAGGGGCAGTATTGCAACGATGTGTCTTAGATCTACGGATGCTCCATAGCCAGCCGTCGTTACGCATGTGAAATCGAGTG
CTGGCTGCCGTGCTTGCCCAAAATGGGCTGATCAGGAGACAGATCTTCCGGTGGGCTACCATTGTGCGTGTCCGGTGAGTGGTCGTCCAGCAGCT
TGCTACCATTGTGCTTGTTCAGTTCTTTCAGCTCGACAGGTGTGGTCTTTTCGAATGTTGGCGGGATTAGTAATCGACTGAAAAGATAACATGTT
ATTTATTGTGGGGAACCGCCTTAAAAACGAATAGTATTTCAGCTTACTTGCTGCACTGTAGCCAAAACATGGAGACCAGCATCATGGCCGAAGTA
ACGCCGAAGGTCCAGAACGTACCTAGGCGCGTGTAGATGGATCCCACGAAGACTGGACCAAGGACGCGGGACAGACAACCCGAACCGGTCATCCA
GCCCATCCAGACGCCCTGCGGCCGAGGTCCCAGAACTTTGGAGAATATGGTCTGGATGAGAGTCACCCCAATGGGATATCCTATCGATGTGAAGG
CAAATCCAATGATGAACTGCGTTAAGGTCAAGGCCGGCAGTTCGCCGCACCATTTCTGCGTTGTGGGGCAGCCCAAGAAGATGGGATCGCTTTCG
CTTAGGTTCCAGCTGGCATTGAATGGCTGCGCCAACTTTGGCGGATCCGGACCCCAAGGCACGAAGAGCACGCGACCGAGAAACATCAGCGAGAA
TCCGCCCCAGATGAGCACATAACGCTCGGCTATAATCTTGCACATGGGCTCAATCAAAACGAACGTGACCAGGGAGACAATAGCTGCGGTGGTCA
TCATGATGCCCATGTACCATAGGGCCTCGTCGTTGGACCAAGCGAACATATCCATTGTCAGGGATGTGCCCAGACTGCAAGGCGAGGAAGCAATA
GTTTAAAAAAAAAAAAAACCCACTCTGAGGATTACTCACGTCTCCAACAGC
(SEQ ID NO: 505)

Exon: 1001..2274
Exon: 2525..3427
Exon: 3533..3771
Exon: 4010..4560
Start ATG: 2726

Transcript No. : CT15293
GTCTGAAAAGATTCTGGCGAGGAGAACGCATCTGGATCCTTTTGCGCACTGAAGGTTCGTGGACTGCGTCTGATGCTATTTCTGGCTCTGGAAGA
AGGAGTTCCTTCAGAGGAAGAGGTGGGCGACGACATTGAAGAATCCGCTCGCTTTCTTTGGACCCTCGTCTGACGGGGGCTGCTGTTGCGACTAT
TGCTGCTGCTGTTGCTATTTAGCCGCATGGTGGCTGTAAACAATTGGGGCAGCTGCTCCGCCGTGGCAGTCATGACTCCGCCACGGGTTTTTTG
TTCTCCTTGTTGGTTTCCGGGCTGCTGTTCGCACTGCTGCTTGACTTGCCGGGGACTGCGGCGAAGAGACTCCTGCCCTTCCTGTTGGCCGCCAC
ATGGGTCTTTAATGGCAAGACACCCAGACTGTCTACGTCCGCATCATCCTCGTCGTCGTTGATTTGGCGCAGCCTGGATCTGGGACTGCCAAACA
GTTGCCGCTTGCGCTCCGAAAGGCGCGGAGTGGCCATGCGACTGGGACGCCCACTACCCGTCGGGGTCTCCATGATCGCGCGCAAATCTTTTATT
TCGCATTAACTTTGTCCAAATTGTGACTCCTTCGCGCTTTTTTGTAGCTGCCTAGTGTTGGGGGTGGTTGGATCGTTCAGGGTCTCTTCGGTCGT
TTGCCAACACATGCCAGATCGTCTATGTTTTTACTGCAATGTTTATATATATTAAATGCATTACATTGTTTTTAAATTTTTTTTACATCAATGTT
TATAAAAATCAAATACATTGCAATGTAAATATTTTCTGTTAGTTATAATTTTTTTACCACATTTTACATTTAACATTTTTCTTCGAAGCGATCAA
GTCAGCTTGCAGTTTTTCGTAAATTATTTGGACTTATTCTACGATTTCTGTAAAATAAATAAGTAATGTTAATTATATTCTTGATCCAAGACAAA
GTATTCAATATAGTACCACTTAACGAGTTACGATCATGATCGCTAGACATTCTATGTTTTCTAATCTTCATATATTTTAAAGATTTCCGTATTAT
TTTAACTATCCGGTATTTTTACAGAGCTAAGGTGATCATATAACGGGAAAACTCTATCTGGTATTTCCACCCAAGTCAGACTCAGTCACACTCTT
CCAGACGTCACACGGTCATATTGCGGACGAAGTGCGAATCGATTTGGAAAAATCTGCTGCTCGGCCTGGAAAGTAGAAAGTATAAAGCTCTGCGT
TTATAATTTAATTTGCAGCCAAAGCCCGCTGCCGATCAGGTATCGCGTTTGTTCGTCGCCGTTGTCGTCCTCCAACCGCGGTATATACATACAAA CATATAGGCAAATATATATAAATATATTTTCGACGCAGCCGCCGCCGCCGCCGCCGCGTAGATATCCATTTTCCGGGATTACCCCACCCAGAGTG
ATATAAACGATATAACCGTGGACGACCACGCAGCGGAACCCGCTGCCGCCATGCCCGGAGCCGGCACGTTCAAGTTATTCATCGGGAATCTTGAC
GAGAAGACACAGGCCACCGAGCTGCGTGCACTGTTCGAGAAGTACGGTACCGTCGTCGAGTGCGACGTGGTGAAGAACTATGGCTTCGTTCACAT
GGAGACGGAGCAGCAGGGTCGCGATGCCATACAGAATCTGAACGGTTATACGCTGAACGAGTTCGCCATCAAGGTGGAGGCGGCCAAGAGCCGGC
GGGCGCCCAATACGCCGACCACGAAAATCTTCGTGGGAAATCTAACGGACAAGACGCGGGCGCCGGAGGTGCGGGAACTGTTTCAGAAATACGGC
ACCGTCGTCGAATGCGACATTGTGCGCAACTATGGTTTTGTCCATCTGGACTGTGTCGGTGATGTGCAGGACGCCATTAAGGAGCTGAACGGTCG
CGTTGTCGATGGCCAGCCGCTCAAGGTTCAAGTGTCGACCAGTCGGGTCCGCCCCAAGCCGGGCATGGGCGATCCGGAGCAGTGCTATCGGTGCG
GAAGATCCGGGCATTGGTCGAAAGAGTGTCCGCGACTGTACGGCAGTGCCGGAGGCGGACGCGAGCCGCCATCGCCCCTCAGCGCCGGCGGCTAC
AGAGATCGCATGTACGGTCGTGACCCGTATCCGCCGCCACCACCGCCGCCGCCGTTCCTGCGTGACCGCATCATGGATGGCTTTAGGGACTATGA
CTACTATGACCGCCGCTTCGAGGACTCACGCGATCTGTATGAGCGTCGCTATCAGACCTCGCGAATGCGCGACTTCCCACCGCCGCCCATCTCTC
GCCGCGAACCCATGCCTCTACCGCCCACCTTAAGCGGCAGCCTGCGCTCCTGCAGCGTTTCTCGTGGATACGACACTATGTTCAGCCGGCGCTCG
CCTCCGCCGCCGCGTAGCAGCAATGGAATGAGTCGCTACGGCTCGCCCACTCCACACGGTTACGAGGACTTTAGTCGCGATGCATTCGACGAACG
CATGATTTCGTCGCGCGGAATGCGCGGTCCATCGCCGCCGGGTCGCAGATATGCGCCCTACTGAGATGAGTTTTACTATCACGGCAGCAGCTGAG
TAGCGGTTGCACTACCCATGCCCCTGCCAATGGGTCACACATTCTACCACACGACCAGCAATCGAAGAACGGCGCCTGTGGACTGCTGGCTGCTC
TGCTGGTCGCCAGCGGCGGCCTACTACCATCACCACCAAGCACACCAGCAGCAGCACATGCTGATGCCGACGCACAATTTCACAACTGTGGCTGCCGCC
TTGGTAAACCACATACATGTTACTAAACCCAAACTAACCATTACTCGTACACTTAAACAAGAAGATGGAAATACGTGTTTAAGCATCCTCCCTAT
ATGCAAAACACGCCAAAAAAAAAAAAAGAACTAGACAACGACGTGCAACCTCTACACATTCAACCGTAGTACCAATAAACGCATAATCAGTCGAAA
CTGTGCAAAAATAAACACTGTA
(SEQ ID NO: 506)

Start ATG: 1476

MPGAGTFKLFIGNLDEKTQATELRALFEKYGTVVECDVVKNYGFVHMETEQQGRDAIQNLNGYTLNEFAIKVEAAKSRRAPNTPTTKIFVGNLTD
KTRAPEVRELFQKYGTVVECDIVRNYGFVHLDCVGDVQDAIKELNGRVVDGQPLKVQVSTSRVRPKPGMGDPEQCYRCGRSGHWSKECPRLYGSA
GGGREPPSPLSAGGYRDRMYGRDPYPPPPPPPPFLRDRIMDGFRDYDYYDRRFEDSRDLYERRYQTSRMRDFPPPPISRREPMPLPPTLSGSLRS
CSVSRGYDTMFSRRSPPPPRSSNGMSRYGSPTPHGYEDFSRDAFDERMISSRGMRGPSPPGRRYAPY*
(SEQ ID NO: 507)

Name: RRM-type RNA binding protein
Classification: RNA_binding
Gene Symbol: lark
FlyBase ID: FBgn0011640

Celera Sequence No. : 142000013384256
AAATGCATCTGAATATTCTCGAAAATATCTTCAAATGGCTTTCTCGAATCATTCTTTTAGCAAAACATTGGCGCCTGGCGCATCATTTTCGGAGT
GACCATCGTGCTGTTCGCCTTGGAATTCCTGGTATTCGTCTTCTTGGGATCGGGCAGCGAGCAGCCGTGGAACAAGGCCGGAACTCCCAAGGATC
CCGAGGCCAAGGACGAAAAGACTCCGTTGAAGGAGCTGCCAACTAAGCCCTAAGCCAACAATCTCGCCCCGAATCTTCTGCCTCAATTACTCGAC
GAACTGCTGCTTATTCGGATAACTCTTGGATAAAGCCAGTTCAAAGTGGAATGGTCAATGCTGGACTGTAAATACCAATTACAAGTGTACAATGC
CCACCCTGAATAGCGAATTCATTGAACATACGTTCGCTATTTAGGGCGTGCACTGTAGTTTTTAGATCGCTGTAAACCAATAGTTAGTAGCCGTA
TCCATTACGGATAAACACTTCAGCCCGCCTAATGTACTTAACACTCTTGATTTCAAAAGTTGTCTACAAATAAAGCGACGTAATAGTGGATGCAC
GGGGGTTCCTAAACAAATTCTGGTGGGGAAGGGAGAATGGGTCTCAGCCTCAATTTCGATGGAAATTCTGGGTGAATGACCCCATTTTCCTGTTT
ATATTTAGCGCTAGCAATAAGCCATTCCACAGAATCTCAGAGGATTTAGTTACAACTCTGTACGTATAAAAAAATATATAAACAGGGGATCTGTT
CTATCTGTTTGGTTGAAGATATGAACAATTGCATGATGTAACTAAATGGCAAAAGATGTAAGGCTAGAGGATGATCCTAACTCAACAATGCAAAG
ATTGGGTTGTGAAATTGATTGTAACATCTAAGAACCAACTTTCTTTGCATCCTTATCACAATTTAAACTCCGATAACCTGCGGCGCCAAAAGACA
GAGTCCGTTATCGATATTCCGGCAGAAACATATGATTTCATGTAATCAGTTTGCCTTTGCCGGTTTCAACGGATTGCGGAAAATGTTGAAAGCAC
GGAACGTTTGTTTGCTGTCCAGGAGGTGGAAGAGTGGCGCCAAGAAGCGATGGAATGTCCTGCAGAACAAGAAGAACAACTGTGACCGAGCGCTG
GAGAACTTCGATGACTTCTACGGAAGTGTCTACGGCACCCGGTGGAAGAACATGCGGGCGGCGCTTCTCACGAGGCACAAGTATGTCGCCCTGGT
CAACAATTTCGGGGACACGGAGCAGACGTGCGCCATGCTGGAGTCAGATGGAGCCATCAACATGAAGTCGCTTATTAACCTGGCGCAGGATCGGG
TAAAGGACAGCACGGAGACGGTGCCGGAACAAGGCAAATCACGTCATGAAATTGAAAGCAAACTGGATGCACTGCTGCGGAAACAGCAGGAGCGC
GAGGTGGCCTCCATATACCCGAGCTCGCCAGAAGATGGTTCATCGGCGCCACTGCCGCTGGAACTGAAGTTTGACAACGTAGAGGAAGATCAGCC
GGAGCAAGTGAATAATCCCTTCAAGCAGAGCCTGACGAAGGCTTTGGAGGAGGATGTGAAGCTGGACGAGCATCGGTTGGTGGATCCCCAATTTG
GCACAGGCGGACTGTATGAATACATGCCTGCCCACAGCATCAAGGGCATGGAGGACTGGGTGGCAGAGTCGGAGCACTACAAGTACTACCAAACC
AGCGCCGACTTCCCGCTCGCCATTGAACCGGAGCCTTCCTTTCACTACCCCGAGCATCTGTCCCTGTACACATATGAAATGGGCAACTGCTCGGA
CTTCAAGGGACCCAAGAAGTGCATGACCGGTGTGCTCTCCCACTTTATGATGGATGGTGCCTCGACTTTGCCGCCTCTCTTCCTGCAGGTGAAGC
CTGGCGAGCGTGTGCTCGATGCCTGTGCCTCTCCCGGCGGCAAATCGCTGCTTATGCTGCAGACGCTGCACTTGGACCACCTGGTCTGCAATGAC
ATCCAAGAATCCCGCCTAAACAAGCTGCGCAAAGTGATGCAGGAGTACCTGTTCGACTACAAGGAGCGCTGGGCTGGAAAGCGCCTCATCCTCAG
CCAGAGTGACGCCCGCAATCTGGACCAGTACGAGCAGTTCGACAAGATCCTGGTCGACGTGCCCTGCACCACGGATCGCCATGTGCTCAACGAGC
AGGACAACAATATTTTCAAGCCGACGCGCATAAAGGAGCGCCTGCGGATACCAGAGCTCCAGGCAGGCATCCTGGCCAACTGCTTGCGTCTCCTG
CGACCAGGCGGCAGTTTGGTCTACTCCACCTGCTCGCTGTCGCCCATCCAGAACGATGGTGTCGTCCACATGGCTCTGCAAAAGGTCTTCACGGA
GTACGGCATCACAACTACCATCAAGGATCTGAGTCGCCACACGGCGCTCTTCAGCGATGTCTTCAAGTTCGAGCACCCAAAGGGACTCAAGTATG
GACAAATGGTGGTGCCCTACCTGCCGGCCAACTTTGGACCCATGTACTTTAGTAAAATAACCAGAAATGTGTGATTAAATGAAAGTTGTTGGCTG
ATTAACAAGACTATATAACTGTTGCCCCAATAAATAATAAGAGTTGTAAACTAAAAAGGTACCTTTATATTTAACATACTGCTTCCTTTGGTAAC
CAGTATTTTCTACTGCTGGAATTACATTTGCTTGTCGGTCTTCTTTTTCTTTTTGCCCTTGATGGGCAGAGGACCGGGATTCTTGAAAATGGTGC
TGGAAAGTATAGTCAGGCTCCTTAAGTTAAGTTCTAGTTAATTGAAGTTTAAATTGTACTCACTGGCAAGTGGTGCATATGGGACTGTATTTGCA
GAAGACCGAGAGGCAAACCGAGCAGACGTAGCCAATGTCGATCAGCTCACGATGGCAGAAGCAGGAGGCGCGGTAGTCCACTTTGGGCGGTGGCG
GCAGGACCAATTTGTGACGGATCTGCGGGGCGGGCAGGAAGACCCACAGGAGGTACTGCAGCAGGCCGTCCAGCTGGGTGACCTTGAGGAACTGT
CCGGAGGTAATGTCACAGCCTTGCTGTAGCAAACTGAGGGTCTTGTCCAGGGCGCAGGTATCGATCGTGATGCCCAGTTTCTGGGCGGTGAAGAA
GACGTTCATGAACGTCATGTACTGCGAGGCGCACTCGTTGCTGCCTGTGACGACCAGGATGCGGGAATGCATCTTGACGCCAGGAGCCAGATTCC
TCTGGAGCTGTACGGGAGTATTTTGTTTTAGATTTGGTTTCCCAAGGCGATTCCTAGCTATTCTCTACCCTTGATATGTAGCACAGCGCCATGGA
CATGCTGCCGGCCAGGAGACTCTCACAAGGAGCGCTGAGCCGTGGTGCGTTCATCAGGATGCTGCCCAGCTGCTGCTTCACCGTCTTCTCCACCA GATTAAACGCCTCGTACTGCCCATCCACTTGGCGCAGTTCCACTTGTCTTCTGGGCAGCGGATACAGGAAGTTTCTGTAATGGAAGAGCCATTAG
GTGGCGTACATGTGTGGCAGCCTCTACTC
(SEQ ID NO: 508)

Exon: 1001..2544
Start ATG: 1033

Transcript No. : CT15305
TTGCCTTTGCCGGTTTCAACGGATTGCGGAAAATGTTGAAAGCACGGAACGTTTGTTTGCTGTCCAGGAGGTGGAAGAGTGGCGCCAAGAAGCGA
TGGAATGTCCTGCAGAACAAGAAGAACAACTGTGACCGAGCGCTGGAGAACTTCGATGACTTCTACGGAAGTGTCTACGGCACCCGGTGGAAGAA
CATGCGGGCGGCGCTTCTCACGAGGCACAAGTATGTCGCCCTGGTCAACAATTTCGGGGACACGGAGCAGACGTGCGCCATGCTGGAGTCAGATG
GAGCCATCAACATGAAGTCGCTTATTAACCTGGCGCAGGATCGGGTAAAGGACAGCACGGAGACGGTGCCGGAACAAGGCAAATCACGTCATGAA
ATTGAAAGCAAACTGGATGCACTGCTGCGGAAACAGCAGGAGCGCGAGGTGGCCTCCATATACCCGAGCTCGCCAGAAGATGGTTCATCGGCGCC
ACTGCCGCTGGAACTGAAGTTTGACAACGTAGAGGAAGATCAGCCGGAGCAAGTGAATAATCCCTTCAAGCAGAGCCTGACGAAGGCTTTGGAGG
AGGATGTGAAGCTGGACGAGCATCGGTTGGTGGATCCCCAATTTGGCACAGGCGGACTGTATGAATACATGCCTGCCCACAGCATCAAGGGCATG
GAGGACTGGGTGGCAGAGTCGGAGCACTACAAGTACTACCAAACCAGCGCCGACTTCCCGCTCGCCATTGAACCGGAGCCTTCCTTTCACTACCC
CGAGCATCTGTCCCTGTACACATATGAAATGGGCAACTGCTCGGACTTCAAGGGACCCAAGAAGTGCATGACCGGTGTGCTCTCCCACTTTATGA
TGGATGGTGCCTCGACTTTGCCGCCTCTCTTCCTGCAGGTGAAGCCTGGCGAGCGTGTGCTCGATGCCTGTGCCTCTCCCGGCGGCAAATCGCTG
CTTATGCTGCAGACGCTGCACTTGGACCACCTGGTCTGCAATGACATCCAAGAATCCCGCCTAAACAAGCTGCGCAAAGTGATGCAGGAGTACCT
GTTCGACTACAAGGAGCGCTGGGCTGGAAAGCGCCTCATCCTCAGCCAGAGTGACGCCCGCAATCTGGACCAGTACGAGCAGTTCGACAAGATCC
TGGTCGACGTGCCCTGCACCACGGATCGCCATGTGCTCAACGAGCAGGACAACAATATTTTCAAGCCGACGCGCATAAAGGAGCGCCTGCGGATA
CCAGAGCTCCAGGCAGGCATCCTGGCCAACTGCTTGCGTCTCCTGCGACCAGGCGGCAGTTTGGTCTACTCCACCTGCTCGCTGTCGCCCATCCA
GAACGATGGTGTCGTCCACATGGCTCTGCAAAAGGTCTTCACGGAGTACGGCATCACAACTACCATCAAGGATCTGAGTCGCCACACGGCGCTCT
TCAGCGATGTCTTCAAGTTCGAGCACCCAAAGGGACTCAAGTATGGACAAATGGTGGTGCCCTACCTGCCGGCCAACTTTGGACCCATGTACTTT
AGTAAAATAACCAGAAATGTGTGA
(SEQ ID NO: 509)

Start ATG: 33

MLKARNVCLLSRRWKSGAKKRWNVLQNKKNNCDRALENFDDFYGSVYGTRWKNMRAALLTRHKYVALVNNFGDTEQTCAMLESDGAINMKSLINL
AQDRVKDSTETVPEQGKSRHEIESKLDALLRKQQEREVASIYPSSPEDGSSAPLPLELKFDNVEEDQPEQVNNPFKQSLTKALEEDVKLDEHRLV
DPQFGTGGLYEYMPAHSIKGMEDWVAESEHYKYYQTSADFPLAIEPEPSFHYPEHLSLYTYEMGNCSDFKGPKKCMTGVLSHFMMDGASTLPPLF
LQVKPGERVLDACASPGGKSLLMLQTLHLDHLVCNDIQESRLNKLRKVMQEYLFDYKERWAGKRLILSQSDARNLDQYEQFDKILVDVPCTTDRH
VLNEQDNNIFKPTRIKERLRIPELQAGILANCLRLLRPGGSLVYSTCSLSPIQNDGVVHMALQKVFTEYGITTIKDLSRHTALFSDVFKFEHPK
GLKYGQMVVPYLPANFGPMYFSKITRNV*
(SEQ ID NO: 510)

Classification: hypothetical

Celera Sequence No. : 142000013384256
ATCACACAAAAATAGCCATCACACAGCTGTCTCTTGTCTTTTGGCTCTCTTCGCTGTTGTTGTTGTTGTGTGTGTACAAACACCCACAGCCTGC
ATCACACACACACGCTCAAATTCGTGACAGCACCACCCACCCCTCACCAATAACCGTTAATTCCGCAGACACTTTCAGCCGGCGAACGGGAGAAG
AGAATTTGCGAATAATAGCAAAGCCCCGTTTAAATGAACGTTTTTAGCAACAATCAGGCGTTACTCACCTTCTTTTGCTGCTGATGAATTTGCAA
GGATCTGCAGTTGTATTCCAATTAGAACTGACGAGAAGCTGCGTAGCGAACACCGGCGAAATGGCGAAAATAATAACTTGGCGTGGCCTTTGGTG
GGACCAGGCGTACATTCGTGGAAATAGTCAAGCGAGTTAACCCTTATGTGGGTGGCAGAATACTAAAAATATATGATACAACAAATTTTAGACTT
AAGAAAACGGATGTTTAAATGTATAAAATATGATGGAAGTGCAATAGCCAAGCTTATAAACTAATTCTTAAATTATTTGCAATGCATTTAGGACT
TTTCGATATACACGTAAATAAACTATATTTTGATTGAACACGGTACATTTCTACTAGAGTTCACCTTCAGATATTGACGCTATTTCTTGTCCTGT
AAATTATTTTGTTAAATCGTTCACATTGTATGTCTAATAAAGATGTTTTCCAATAAAAATGTTATTCCCTTTTCACTTAGTCTAACATATTCATTA
AATAATCAATGTTTTATTTTTTATTTAGTTATTTTAATTAGTTCTTAATTATAAAACTGCTCTAGATTCTCGATATTTTGCGGAATCCGGCGCAT
GGTCACACTGACGAACACGTATTTTCATTATTCTTGCGAAGCGCATCGCTTAAAACTTGATTACGCTCGGATAACAAGATGCACCCGCGTCTCAA
GTGACTGAACAGGTAGCGAAGTGACCCTGGATGAGCGTGGGTAGGCAGCCGGCACCTCTGGAAAGCCCTAATCCCAGGTCCGCCAGCCGTTTGCA
GGTTATGTCCGCTTGTGTACACTGTGACGGGGAACCGAAGAAGCAACAGGAGCGGATTCCTGGCAGAAGAGACAACCGCTGTACGAGATACCGCC
CCTGACCTGCGCAACATGATCGAGGTGCTGTGCCTGCTGCTGGGCAGGATCCTGCTGCTCCTGGTCGGCGGCTACGAACTGATGTGGCGGCTCCG
AGAGCGACTGAATGCACTGGCCGTCCGGTCATATGACCTTTGGCGCAGCAAAGCGGCACGTGAGGCGCACGAGCGGCGCGTGCTCGCTGACTGCC
GCTCCCAGTTGACGAAGACGCCGCAGCATCTGGTCCTGGTTATCTCCCCCGTAGATGCCGGCGTGGATGCGGTGCTCCTCAGCAGGATCTTCGAC
TTTGCCCTGGACGTGGGCATCAAACACGTCAGCCTGTACGACAGGCGGACGAAAGGCAGGGGATACGTGGACATGGCCGATCTCTGTCGATCCAC
CAACGCGGACACGGGCAGCTGCTTAAAGTGGCCACCCGTAGCCAGTCCCAGCAAACTGGAGAACCAGCCCAAAAACGGACAAAAGACAAATGGTT
ATGTGAACGGTTCACATTCCCCTCAACTGCAGGTGAGTGGCGGCGTCTGATAAGCCGTGATTAGTAATGGACTTTAGAACGATGTCGGAAAATGT
CTTACAAGTATTACACTTTTTGTTTCAATTGTTAAATAAAAGAAGTAATGAGCTGGAGATTTAATTTAGTTCATCATTCACATGAGATACAAAAA
ATTCTTCGTGCTGAGAACCAGTTTTACCTTTGTATCCATTAAAACCTATGTATAGCAACGTAATCGATTCCCGGAACTAGTCGTTGCCTTATCAG
TTTCTAATTGACTTTTCGGCTTCGGCGTCTTTCAGCTCCATCAAATCAGCGCCTCCGACGGCCATGCCCTGATCGCCGACGTCTGCCGCGAGTTG
TACGAAGACAGTAAGACGGAGTTGGTGCAGAGCCTACTTAAGCAGAAGCGCGAAGCGCTGACGGAGCAGATCAGCGACATGCTGAGCAAGCGACT
CGGGTTCGAGGCCCCGGAGCCGGAGCTGGGCATCGTGTTCGCCCGGCAGACGTGCACCTACGGCCTGCTTCCCTGGCACGCGCGCTTCACCGAGT
TCCACACGCATCCCAGCGGACGCCACTTCGACGTGGAGACGTTCGCCAGCATCCTGTGCAAGTACTCGCGGTGCGAGCAGCGGTGGGGCACGTAG
GCACATCGTTCGCGTGGGTAGCGACACCCTTATATTAACTAGTTACCTTAACATTATGTAAATTATCGCCAGGAATTCCTTTTAGTTCGTAAGAG
TAAACTGCAAAAGTGTATTGTTCACATGAAAGTGTCTTTTGCTGGAGAGGATCGCGCGTTTCTAATGGCGGTGCAACGCAGCAGCTCGTATCTTG
TACATAATATTCGATCTTTATTGAGTGACGTTTTGCTGTGCTTAAGGCGCAACTAGATGAGTATATGTAAGTGGGCAGACTTAAGCGCT
ATGGTTAAAAGTATTGTATTGCTTTTCGTTCAAGTGTCATCTCCGGCGCTCAGCCGCTCTACTCCCGACCGGGCTCAGCGTGGCGCTTGGACAGG
AGATTGACGTCGGTCAGATACGTGTTCTTGTCGATGTTGTGCGGACCGGGACCCGTGGGCATCCGCTCGTGGAGGCCGTGGAAGGAGTTGCGCAG
ATCCTCGAGGGAGTCGGCCAGGCCCTTCTTGATGCTGGCGAACTCGGTGGACATGAGCGACAGCTTGCCCAGCAGATAGTTGAGGTTCTCGTCCA TGTCGATCATGTGTTTCTTGGTCTCCTCCACGCGGCTGCCGAGACCCATCATGGTGATGAGAGTGCTGTTGTTGTAGCCATCGGAAGCGGACTGG
ATATCTCCGAGCATCAGCCGGCTCTGGCTGATCTCGCCGGCCATGATCTCGATGCGGTGCCACACCTGGTTCAGCTCCGTTTCCAGCAGTCCGCT
GATGTTCTTGTTCGCCTCCTGCTGGATGCTCACCACCGCTCCGTCCAGCGACGAGAAGCGCTCCTTCAGCAGTCCGCTCAGCGTGGCCATTTCCT
CCGCCAGCAGCTTGCCAACCCGCTGCACCACGTTCAGTGTGCCGAAGTCCACCTTGCGCTGCGTGTCCAGCACGACCTCCGAGTTGGTCATCATG
ATGTTGTTGAACTTACCGAGCGCTTCGAGTCCCTCGTTCAGCTTGGCATT
(SEQ ID NO: 511)

Exon: 1001..1647
Exon: 1936..2280
Start ATG: 1156

Transcript No. : CT15363
GGCACCTCTGGAAAGCCCTAATCCCAGGTCCGCCAGCCGTTTGCAGGTTATGTCCGCTTGTGTACACTGTGACGGGGAACCGAAGAAGCAACAGG
AGCGGATTCCTGGCAGAAGAGACAACCGCTGTACGAGATACCGCCCCTGACCTGCGCAACATGATCGAGGTGCTGTGCCTGCTGCTGGGCAGGAT
CCTGCTGCTCCTGGTCGGCGGCTACGAACTGATGTGGCGGCTCCGAGAGCGACTGAATGCACTGGCCGTCCGGTCATATGACCTTTGGCGCAGCA
AAGCGGCACGTGAGGCGCACGAGCGGCGCGTGCTCGCTGACTGCCGCTCCCAGTTGACGAAGACGCCGCAGCATCTGGTCCTGGTTATCTCCCCC
GTAGATGCCGGCGTGGATGCGGTGCTCCTCAGCAGGATCTTCGACTTTGCCCTGGACGTGGGCATCAAACACGTCAGCCTGTACGACAGGCGGAC
GAAAGGCAGGGGATACGTGGACATGGCCGATCTCTGTCGATCCACCAACGCGGACACGGGCAGCTGCTTAAAGTGGCCACCCGTAGCCAGTCCCA
GCAAACTGGAGAACCAGCCCAAAAACGGACAAAAGACAAATGGTTATGTGAACGGTTCACATTCCCCTCAACTGCAGCTCCATCAAATCAGCGCC
TCCGACGGCCATGCCCTGATCGCCGACGTCTGCCGCGAGTTGTACGAAGACAGTAAGACGGAGTTGGTGCAGAGCCTACTTAAGCAGAAGCGCGA
AGCGCTGACGGAGCAGATCAGCGACATGCTGAGCAAGCGACTCGGGTTCGAGGCCCCGGAGCCGGAGCTGGGCATCGTGTTCGCCCGGCAGACGT
GCACCTACGGCCTGCTTCCCTGGCACGCGCGCTTCACCGAGTTCCACACGCATCCCAGCGGACGCCACTTCGACGTGGAGACGTTCGCCAGCATC
CTGTGCAAGTACTCGCGGTGCGAGCAGCGGTGGGGCACGTAG
(SEQ ID NO: 512)

Start ATG: 156

MIEVLCLLLGRILLLLVGGYELMWRLRERLNALAVRSYDLWRSKAAREAHERRVLADCRSQLTKTPQHLVLVISPVDAGVDAVLLSRIFDFALDV
GIKHVSLYDRRTKGRGYVDMADLCRSTNADTGSCLKWPPVASPSKLENQPKNGQKTNGYVNGSHSPQLQLHQISASDGHALIADVCRELYEDSKT
ELVQSLLKQKREALTEQISDMLSKRLGFEAPEPELGIVFARQTCTYGLLPWHARFTEFHTHPSGRHFDVETFASILCKYSRCEQRWGT*
(SEQ ID NO: 513)

Classification: hypothetical

Celera Sequence No. : 142000013384044
ACATGACACTATTTCGGTTTTAAGCCCGCCACGCCCACAAACTCACCTCCTTATTGCCGGACATGCCGCTGACGTAGACTTTCAAGACCATTTTC
GCAGATTACTGTGTCCTCGCACCGCAAATGAAATAATATTTGCAACTAAAATCTGCTGGCTACTTTCACGGCGATTAAAAATATTTATAGATCT
TTTCTTTTCCTGCTTTCTTCCGTCCTGCGCCCCTACGTAATGTTTTTCCACTGGTGACGAAGGCACACGCACTGGGCAAGGTCGTTGGTTTTATT
GGCTGTAAAAACGGCAAAGACGCGGATAAAAAAATTGCCTGGCGACGCTTATAAAAGTGCAAAAATATTTGATATCAGGAGTGGAAAATATTTCC
TACTTTGTCGTTGAATTGAATGGTGGGACCGCGCATTGACGGCTATAGAAAACCTTCCGGCTTATCAAATATACTAAATATGATGCTTGATTAAA
ATACTAAAAACTTTGAACTTAAGTGATATTTCAAAATTAAATATTTTTAAGACAACTTAAATTTTATTATGCTCCCATGTAAGGTTTTCATTTTT
TAAACGTTCTTCGATTAATAATCGTAATAATAAAATAATAATTTATAAAAAGCATAAGATAGGCTTTTTAAGGTTTTTTAAAAGATAGAAGAAAA
GGATTCTTATTATAGAACAAATTATTTTTAATTTGGCGTCGATGAGTTAGCGGCTTCAAGGAACGGTGGAATTTAGAACATGAGGGTGTTTTTTA
TTTATTAATTTTTTGTTACTTGGAGTTGAATTCCATAAAAATAAAAATGCAATAATGCTAACTTTCTACAAACGACTTAAGGTTATAGGACTCAA
GAAAGTACATAGAATATGCAATTGAAAAATGTTCTCCCCAGACTTTTCGGTTATTTGAAGTTTTTGCTATATTTGGTAGAACCATAAAGTATTTT
TTGGTATAGATCCGTTAGCAGGGCAACCAATATTAGCGGTCGCCATGCGGTCACTCTGTTCACGTCCCGTCACGCAAGCATCGTCGTCCATTTTT
GCTAAGAAGCGAGACGAAAATTTGTAAATTATATCTAGCGAGTCGCCGAGGACGAACAACTATTGACAGTGCATTTCAGTGGCCTTTGGAATACT
GCTCAAACAACCAGCAAGCAATAACATTACTTATATCTAACCGAAAACCTAAATTAATCACCCAAACTGAAGTACGGACGTGAATGTAAGTGGGT
ATGTGCCAGCGGACTAGTGGCACAATAAAAAAGTAAATAAAGCGCGTGTGAAGTGGTGCAGAAAGCAAAAAAGCAGTCGGAAGGAAAAATCAAAA
TACGCATTAATGTAAGTGCGATTGTTGGAAAAGCTGTTTAACTTTTTGTTCCTCTGAAAAGCTGATAATGATATGCGATGCGACCATTTTTAAAA
TTTCATGAAATCAACATTCCAACTCACAACGGTGTGCGTGTGCGTTTCTTTGTGTGCGTGCGTGTGCAGGCTAGAGTGGGACAACCAGTGTGATC
GCTTTGGCTGCTGCCATTTCGTTTGCTTTTTTTTAAACTAATCTCTGGCATTTGTCACGTAAAAGAGTATAACGTTAAACCCAAAAACGTTTTGT
ATATGGCTTTAAATATTTAATAATTGTGGGCAGAGACAGCAACACCAGCAGCAGACGCATACACACGTGTTGCGGTTTATCGAGAGGGCAGTGTG
CGTGTGTTAGTGCGGAAAACAGCTGGTACAGCTGCCGCTGCAGCGACGAAGAAGAAGAAAAGAAAGAAAGGGGAAGAGTGAGAAGAACACGCATT
ATTATCCTGCGTAGTTTTCTTTTATCGGTGGTTGTTCTGCTATTGGGTTACAGTTTACACTTTTCTCTGTTTTCTTTATTTTCCCTCTGCATTGC
TATGCATTTTGCCTTTGCGTGGTGGTTTTTTTTATTTTCATTGTCGGTCGTCCTTTAATTGCGCTGCGCCACTTCGTTTCGTCGCTTTCTTTGGC
TGGTTTCTCCTTCTCTTCGGAGTTTCTGGATTCGTATTCCGATTCGGTATCGCCCTTTTCCTGCGACAACAGCAGCTGGGTGCACGGTATCGGAG
CTGTCGGCGATAGCCGAAAGAAGCTAGAAACCCCAAGGAAGCCAACATCCTTTTAATTGTCGTGGAAACTATAATAGTCTCATAAAAATTAGGTT
TTTAAAATGGTTTTGTCATTCTATTCTAGAAAAAGCTATGAATATAAGAATATAACAATATGTTTAATTGCTTACTAATTTTATTGAACAATATA
ATTTAATCGTGACGAAATGGGGGAAAAAAAACATTTTTTTGTTGTCTTGAATTTTTTTTCCTCTCTTGTCATGATTATTTAGGTAAAACGGACGT
CATCAAAGTCATTAAACTTACGCGAACTTCGCATTTAAAAGTTTTTTACTGGCATTTCTATTTTTAATAGCTTTCTGGGGAAAATATCGGATAAT
AGCTTTTCAAATTATGCATTGCTAGCAACTTTGACTAGCGAAAAGTATTTACTAAAAATTTTTGTACCTTCCTATTTTCGGCGCTCTTTTTAAGC
AAAGGCCCTTGTTTTGTAGCGTTGAAGCCTCAAATTATTTCCAAAATCACGCCCCATAAGCGATAAGATAAGAGAGCGTACAATTGTTGCCCACG
ATACATACAAGGCGAGAAAAAGTCCAAATTGCCAGCATTGGCGGCCATAAATCGCTGCACCATTTTCTTTTATCGGCTGCGTGTGCGTGAGTGCA
CGCCTGTGAATCCTGTTTTTTCCTTGAAACCAGTTTGCGTCCGTCTTTTCTTTGCCAGCAAGGTGTTCACTTCACCTTACTCATTCATTGTTTGT
TTGCCCATTGCAGCCGACGCTTGATCTTCCATCTGCAGCATCCATCATTTGGAATCGAGGCAATAATCAGCATCTACCGACAATCAAGCAAGCCA
TCTATCTATCAGAAGACCACCGGGTAGTAGAACCTCAATCATAGCGATGGCCTGTGCAACCCTGAAACGAGCCCTAGACTGGGAGTCGATGAACC
AGCGGCCTCCGAAGCGCCGGCGTTGCAATCCCTTTGGCCAGGCTGGGAGCAATGCAGGTCCAGCGTCGCCATCCCGCGACGGTCCCAGCACCTCG
GCTGGTCTGCCCCACACGCCCAGCAACCGATTCGCCAAGGATAGCACCGAACCTAGTCCGTTCAGTGAGTCGTCGCTGGCCAAAATGTCACCAGG
TTAGTAAATCAGGTCGATGCTGGAAAAGGACGTCGGATTCCTTTTATGCATATTACCTTAATACACCTTTCTTCTTTTCGAAACACAGACAAAA TGGCCGAGAGCTTGTGCAATGAGATCAAGAGACTGCACAAGCGCAAACAGCTGCCGATCACTTCGTCGGCCTTGGAACGCATGCAGGATTCGGAG
TCCAGCGGATCGGAGATGGGTCCAGAGAGTCCGCGCCGCCCGGACAGTCCACAGAACCTGATGCGCCACGGCGAAAAGGCCCTGTTCACGTTCAA
GCAGGTGCAGCTCATTTGCGAGAGCATGATCAAGGAGCGCGAGAATCAGCTAAGGGAGCGCTACGAGTCCGTGCTGACCACCAAGCTGGCCGAGC
AGTACGATGCCTTTGTCAAGTTCACATATGATCAGATACAGCGTCGCTACGAGGCAGCGCCTAGCTGTGAGTTCAAGTTACCATCGGTCATGGTT
ATAGTGCTAATTACATTATATTTTTATTTCAGACCTGTCGTAAAGCTGTGTACACAGCTGTAGCCTCAGAAAGAAGAAATTAATAATTGCACTAC
GATCTTATGTGACGGTAGATCTACCGCGACAACAACAGCCCTCATAAACTATAACAAACAACAAATAAGGAAACTAAAGCAAACGCAAAACAAAC
CAACAAAAAAAAAAAACCTAAAAAGCAAAAAACCTAAAAACAAACAAAAAAAAAAAAAACAAACTACAACATACATCGTGTTTAATATATTTTGAA
ATACACGCGAAGAAAACGGTTATAGTTTATGCCTAGATTTACATATATATATTGTATCGGTTAGCAGCAAAGGGATGAATTATTTAAAAGCAAGC
AAAAACCACAAAAGAGAGAAACCAACAAACCAACTTGTTAAATTTATGTTTTTCACATAACGCAAATTCTAAATAAAATGACAAATATCAAATTA
TGAACTATATGAACTATAAGCACACCGCCACTGCAGACATATACATATGGGTGCATCCGTAGAGAGAACGATTCAATGAAACCTCAAACGTAGCT
TCGTACATAACAGACCGACAGAATTGGCAAATATATAATGTTAGGCACATGATGTAGCATATAAGGTATGATGTAAAACCTATCAAACTACATAT
ATTGTTTTTTTGGAAATTGTAATTTATGAAGCGAAGCAACAAAGATAACTCACAACTCATGAAGAACACTTTTCATAGTTTATTTTTGCATATTA
GTTGTAACACTAAGGCGAGAAACGAACGCTTGAATTTGCCTATTTTCTCGAGTATCGTTTGTTAATTGTTCTTCCTTTGATGCGAATTATTGCA
AAGTAATGTAAACACACAAAACAATTGAAATGTTTCGATTTGCTTTACACCATACAAAAATGAATAACGAAAAGAAAAGGCAAACAACAAAAAAG
GTATAAAAGTTATTCATTAAGTTAAATTGAACGCTTTCTTATAAAATACGCTTGACAGAAGATGTTTCATGTTCATTGCAATATTTT
(SEQ ID NO: 514)

Exon: 1001..1341
Exon: 2864..3229
Exon: 3320..3676
Exon: 3738..3748
Start ATG: 2992

Transcript No. : CT15373
TCACTCTGTTCACGTCCCGTCACGCAAGCATCGTCGTCCATTTTTGCTAAGAAGCGAGACGAAAATTTGTAAATTATATCTAGCGAGTCGCCGAG
GACGAACAACTATTGACAGTGCATTTCAGTGGCCTTTGGAATACTGCTCAAACAACCAGCAAGCAATAACATTACTTATATCTAACCGAAAACCT
AAATTAATCACCCAAACTGAAGTACGGACGTGAATGTAAGTGGGTATGTGCCAGCGGACTAGTGGCACAATAAAAAAGTAAATAAAGCGCGTGTG
AAGTGGTGCAGAAAGCAAAAAAGCAGTCGGAAGGAAAAATCAAAATACGCATTAATCCGACGCTTGATCTTCCATCTGCAGCATCCATCATTTGG
AATCGAGGCAATAATCAGCATCTACCGACAATCAAGCAAGCCATCTATCTATCAGAAGACCACCGGGTAGTAGAACCTCAATCATAGCGATGGCC
TGTGCAACCCTGAAACGAGCCCTAGACTGGGAGTCGATGAACCAGCGGCCTCCGAAGCGCCGGCGTTGCAATCCCTTTGGCCAGGCTGGGAGCAA
TGCAGGTCCAGCGTCGCCATCCCGCGACGGTCCCAGCACCTCGGCTGGTCTGCCCCACACGCCCAGCAACCGATTCGCCAAGGATAGCACCGAAC
CTAGTCCGTTCAGTGAGTCGTCGCTGGCCAAAATGTCACCAGACAAAATGGCCGAGAGCTTGTGCAATGAGATCAAGAGACTGCACAAGCGCAAA
CAGCTGCCGATCACTTCGTCGGCCTTGGAACGCATGCAGGATTCGGAGTCCAGCGGATCGGAGATGGGTCCAGAGAGTCCGCGCCGCCCGGACAG
TCCACAGAACCTGATGCGCCACGGCGAAAAGGCCCTGTTCACGTTCAAGCAGGTGCAGCTCATTTGCGAGAGCATGATCAAGGAGCGCGAGAATC
AGCTAAGGGAGCGCTACGAGTCCGTGCTGACCACCAAGCTGGCCGAGCAGTACGATGCCTTTGTCAAGTTCACATATGATCAGATACAGCGTCGC
TACGAGGCAGCGCCTAGCTACCTGTCGTAA
(SEQ ID NO: 515)

Start ATG: 470

MACATLKRALDWESMNQRPPKRRRCNPFGQAGSNAGPASPSRDGPSTSAGLPHTPSNRFAKDSTEPSPFSESSLAKMSPDKMAESLCNEIKRLHK
RKQLPITSSALERMQDSESSGSEMGPESPRRPDSPQNLMRHGEKALFTFKQVQLICESMIKERENQLRERYESVLTTKLAEQYDAFVKFTYDQIQ
RRYEAAPSYLS*
(SEQ ID NO: 516)

Celera Sequence No. : 142000012746884
CTATCCAGAATTTCTTGAGCTCGCCGAAGGTGAGTTTGTAGCCCAGTTTGTAGCGCATATCACGTACATCCTCCTCGGTGAGGGAGAGCAGCACC
TCGCCGTCGATGGCCTCCTGGCGCAGGCAGTCGAGCAGTGTTCTCGAAAAGTGCTCCATGCAGGTGGCCCAACTGGTCACATTCTCGATGGACCA
CTGGGCCACGAGTAGCGGATCCACGGGCTCTGGATCTGGCGATCCATTGGTCAGGTGCTTATCTGTCGCCGCGTCGAGGTAGTGCGTCCGGGTCT
CCTGATCCATTGTGACCAATCCACCGCCCTCGGAACGTGGCTGAGTCACCGGATCGCCAATTTCACCGTCGCACATCGCGCTTTCTTTTTTTTCC
GTTCGATGTTCTTCTGGCTGTTTCTTATTCGTTCCAATTTTGCGATTTATCCAAAATCCAAAACAATTGTGCGGCCGAACTCAGATGGAGTGCAA
CATTTTTTCACTGCTGGCTGCTGTTGCTGCTGCGGCGCATAATTAACACCTCACTTATTGCGCGTCCAGCGTTTGTTGATGTAAAAGCACATTTA
ATTTTTGGTTTGGTTACTTGTTAAATTCAGACTACTCAGTTGTTCCGTTCAGAGAGCAAGCGAGAGAGCAGAGCGGAGTCAGCAACTATGCTGGG
GGCGGGAGCGAGATAACAAGGCCGAACAGCTGACTTCGGCCATCGATAGTTTTTGGACAACGCCAACGCTATCGATGAACAGTTACTTCGGTCTT
AACTGCGTGTTCACACCGAAAAATTTTCGAGAATTTCGCTCTCGTAAAAGTCAAAAGGTTTAAAACTCTTATCGTTAGCTTAATATTATTTTAAA
TAAAACAATTTGAGGTGTCTGGCGAGTAGAAATTATTTAAATATTAACGCTTGACTGATATAAATCTCGTTCGATATATACGAAACCATGGTGAA
AATGTGGAAGAGTGGAAACGGCCTCCAAAGCGAAGATATCGAAGCCACAGCTTCGCTTCGTTAGCATTTTGCGAGCGGCAAAGTGATTTAATTGT
CCTCGTGCGAATGTCTAGACAGAAGTAATCCTCGAATAATATGAAGAAAGCCAAGCCGCTGCTGCACGACCATCTAATAACGATCCGAGTAAAGA
AGGTGTGTCCAAATCCGTTGTTTATATCCACAAACTAGCCAGCTGCCCGATAGCCGGTAAATTCCCATGAAAGCAGCACAAAAAAAAAAAAAAAA
ACACACAAAAACCCTTTGCAGGGCGGCGATTTTGGGCAAGGGAAAACAAGGTTAGGTCGCAGGCTACCCGCATCGTGTGCTAATTGCGTTCTACT
TTCGATTTCAGTATCTGGAGGAGCACATCGGGGAAACCTACCTGGATGTGAAACAGATGACCAGGGAGTTGATGCAAAAGTATCCGGAATATTCA
CGACGCAAATTCGGACCATTCAGACAGCTGGTGCACCAAGGTAAACATGGAACATTGTGGTTATTTGTTTTTAACAAATATTTCTATTACAGCAT
TCTCGATCATTTCGGAAAGCTATAACTTGGACAAGGTAAGCAGTTCCGAGGAAGATTGTGTTAGCGAGGACTCCGAGCCACCACCCACGAATAGT
GTGATGAACAATATGATGAACAGCCTGTATAGTCAACCAAGAAAGCCGCTGGCGCCCAAGCCAATCAGCGAGCCCATCGATATATCCAGTGGAGA
CGAGAACGAAGATGACTCCAATACAAAAACCACCAACGGAGATGGGGTAGCTGCTGCTGCTGCTCCTCCTCCTCCTACTCCAGCAGTGCAGGGCA
GTGCTTTGAAACGCCTGATGGAGGAAGTGCCGGAGATCGCAGTGGCTGCAAAGAAAGGTGGGTTATCAATCCATTAGTCTATGACTTGGTTAAAT
GACATTCTTCATTAGTAGCTAAACCGAATACTATTCACGTTAGCAGTTCGGAGGCCATTCAAAAGCGTGAGTTTTTTTTAAATACTTTTGTAAA
ATCAATGAAACCTAAACTTTTTGTTTTAGTGCACCAAGTTGTGGGCAACAGAGCGAAAAATCTTTCAGAGGACGCCGTTCCGCGTTCCAAAGATC
ACCGTAATGTGCCTGGCTTATATCAGCAGTTGCACCAAAACCAAAGTCGCGATCGCCTTCGGAAGTTCAAAAGGGATCTGGAGGTGCAGCACCCA ACGGAAAGTTTCCGGGACATTGGTGGCATGGATAGCACTCTTAAGGAGTTGTGTGAAATGCTGATCCATATTAAGTCGCCGGAGTTCTACTTTCA
ATTGGGTCTATTGCCTTCGAGAGGTTTATTGCTTCATGGGCCGCCAGGCTGTGGCAAAACCTTTCTTGCTCGTGCCATTAGCGGGGTGAGTTTA
TAAATGAACATTGAATCGTTAATTCATATATTAATCATCTCTGCTTTACGACACAGCAACTAAAAATGCCTCTAATGGAAATTCCGGCCACAGAG
CTAATTGGTGGCATCTCTGGTGAGTCGGAAGAACGGATTCGCGAGGTCTTTGACCAGGCCATTGGCTACTCGCCTTGTGTGCTTTTCATCGATGA
AATCGACGCCATCGGAGGAAATCGTCAGTGGGCGTCCAAGGATATGGAACGTCGCATTGTCTCGCAGCTGATAAGCAGTCTGGACAACCTGAAGG
CCAACGAGTTTGGCCAATCAGTAGTCGTCATAGCGGCCACCACGCGTCCCGATGTCCTCGACCCTGGACTACGTCGCATCGGTCGCTTCGATCAC
GAAATTGCCATACACATCCCATCGCGGAAAGAGCGGCGTGAAATCTTGCGCATCCAGTGCGAGGGCTTGTCCGTCGATCCCAAGCTAAATTATGA
TAAGATTGCAGAGCTAACACCGGGATATGTCGGTGCTGATCTAATGGCTCTCGTAAGTCGTGCAGCTTCTGTGGCCGTAAAGCGTAGGTCCATGA
AGAAGTTCCGTGAACTGCACGCTGCTAGTGAAAAGAATATGACAACGGTCACTTTGGATGACGACGAGCCCAGCGAGGACGCAGGTGAAACACCT
GTGCCTGATTCAAAAGGTGAAGAAACTGCAAAAGATGCAGAGGCAGAACAAAAGGTAGATGGTGACAAGGAAACATCTGCTAAGGATAAATCAGA
AGGCGACTCGCCAAATATTGAAACCCCCAAGAAAGCGACCAACGGCAACTCATCGATAAAGTCGCCGCAGAAAACACCGAAGAAATCAGCGGAGA
AACCAACTGACGCAGCGATGGATGTAGACAATGTTGCTCCCGAGGAGCCGAAAAAAGCCGTTGAGCAGGAGGTGGATTCCTCCTCCTCCAACGAC
GAGTACTACGAACCCACACTGGCCGAACTGACCAATTTTCTTGACAACCCCCCTGAAGAGTTCGCCGACCCAAACTTTTGCCTCACTCTCATTGA
TTTCGTAGATGCCATTAAGGTGATGCAGCCTTCGGCCAAGCGCGAGGGCTTTATAACAGTACCAGATACCACTTGGGATGACATTGGTGCCCTAG
AGAAAATTCGCGAAGAGCTTAAGTTGGCTGTCTTGGCACCAGTTAAGTATCCAGAGATGCTGGAACGTCTTGGGCTGACAGCTCCGTCAGGCGTT
CTGCTATGCGGTCCGCCGGGTTGCGGCAAAACTCTTTTGGCCAAGGCTATTGCCAATGAGGCTGGCATCAATTTCATATCGGTGAAGGGCCCCGA
ACTTATGAACATGGTAAGATAATTGAAATGTTGTATATTTCTTGCATTGCTCATCATGTCCGTATATTGTATAGTATGTCGGCGAGAGCGAACGA
GCTGTGCGTGCCTGTTTCCAACGTGCCCGGAACTCTGCACCCTGCGTCATCTTCTTCGACGAGTTCGACTCCTTGTGCCCCAAGCGATCGGATGG
TGGCGATGGTAATAATTCGGGCACTCGTATCGTTAACCAACTGCTGACCGAAATGGATGGCGTCGAGGAGCGCAAGGGTGTATACATATTGGCGG
CCACCAACAGACCGGATATCATTGATCCGGCCATCCTGCGACCGGGTCGCCTGGACACCATTTTGTACGTGGGTTTCCCCGAGCAGAGCGAACGT
ACCGAGATTTTGAAGGCCACCACAAAGGTAGAATATTGTGGTTACATATTTTATTCGGTAAATTGAAATCTATTTTTTGTTCTTTTCCATCGCAG
AACGGAAAGCGTCCGGTTCTGGCCGATGATGTAGATCTCGATGAAATTGCTGCCCAAACCGAGGGCTATACTGGCGCAGATTTGGCAGGATTGGT
CAAGCAGGCCTCCATGTTCTCCCTGCGACAATCTCTAAACAACGGCGACACAAATCTCGACGATTTGTGCGTACGCAGCCAGCATTTCCAGGAAG
CTTTGCAGCAACTTCGGCCCTCAGTTAACGAACAGGTAAGAATGCCCCAGTACATTGTTAATTATAATTGTTTAACATGTATTTATTTAATAAAC
AGGACCGCAAAATATACGATAAACTGCGCCTGAAATATGCTGCACCAAGGGTACCCACTCTAAATGATAAGTAAACCGATCAACAATAATGAGTT
TGTTGATTTAGCACCATCGCGAATCAATTTAATTGTAAGTTTCGAAAATTAACTTTTAATTTTCGATACAAAATGCGATATGTTACCCAAAAAAA
CAAAACCATTTAATCTATCTTGTAAAATGCGTAGAAGAGATATGTATTTAGTTTTTGGATTGTTTTAATTTTTTGTAGTATCTTACAAAATAAAA
GTTAAACTATTTGGGTTCATCGCAGTTTAGTTTGACTTACACATTTAATTTCACGTTGCCACACTAATCACAAAACAAAGTTCTAAGCTTATAGG
AGCACCAGCGACACTGGCGAAGAAATGGTAGGTTTGCCACGGCTGGTCAGAATCGCGCCATCTCCACCGCCCTGTCCATCACGACTAAGTCCGGA
TTGTTTTATCGGTGGATACTGAGGCTCCATTTGTCGCGGGAAGAGTCCGGGCGGCAGGGCTTGAATGCCCTCGGGCAGATCTAGGGCTTCACGTG
CCTTTAAACTCCTTTGCAGCCGTAAGATGTTCTCGTGCTGCGCGCGAATCGTTGTGCGCTTCGATCGCTTCTTCTTGGACGTGGTTTTGGCAAAA
TCGCCACCAGCCGTATTGGTCTCTTCCGTGGTCGTTGACGTATTCTCGATTGCCACGCCCTCATTACTGCTTTCGTGACGAGACGGCCACGGCAG
TGGTGGCTCCTTTTCACGGACAATCTGATGTCGCAGATCAAAGGAGCGCTTGCACATCTCTCGTATACCGTACCAACTTTCATGGCCAATTTGAC
TGATCATCTCCACTGGCGGCTGAAAGCCGAGCTCTCGAGATGGCAGCTCCATTACCAATGCCATCGGTACTTTCAACACTCCATATACGTAGTCC
ACAACGGAACCGGCAATGGTTCGCTTGGTCAGACAGCTGGTTCGGTACTCCCGGCCATTGTAGGACTTGATTGCACTCTTGCCGGA
ATTCGCCAGGGAGCTCAATTCACGCCAATAAATCGGATTGTCACGGCAGTAGCCCCAAGGGTACATGATACTTGGCCATACGAGTGCAGGGACA
AAAAGAACAGGAGGTTCGAACTCATCCTGTCGAGAATGCATCTCATGGCCCGCGTTTCCGGCTCGGAAAACGGACTTTCACCCTTGTATGTATTA
CGGTTGATCTTGCTGGGTCCGCTGTTCCAGAAGATGTCGTAATTTCGGTTGCAATCAGTGCCCACAAAT
(SEQ ID NO: 517)

Exon: 1001..1142
Exon: 1342..1465
Exon: 1518..1862
Exon: 1916..1966
Exon: 2025..2365
Exon: 2432..3718
Exon: 3780..4112
Exon: 4181..4405
Exon: 4468..4769
Start ATG: 1086

Transcript No. : CT15413
CTTCGCTTCGTTAGCATTTTGCGAGCGGCAAAGTGATTTAATTGTCCTCGTGCGAATGTCTAGACAGAAGTAATCCTCGAATAATATGAAGAAAG
CCAAGCCGCTGCTGCACGACCATCTAATAACGATCCGAGTAAAGAAGTATCTGGAGGAGCACATCGGGGAAACCTACCTGGATGTGAAACAGATG
ACCAGGGAGTTGATGCAAAAGTATCCGGAATATTCACGACGCAAATTCGGACCATTCAGACAGCTGGTGCACCAAGCATTCTCGATCATTTCGGA
AAGCTATAACTTGGACAAGGTAAGCAGTTCCGAGGAAGATTGTGTTAGCGAGGACTCCGAGCCACCACCCACGAATAGTGTGATGAACAATATGA
TGAACAGCCTGTATAGTCAACCAAGAAAGCCGCTGGCGCCCAAGCCAATCAGCGAGCCCATCGATATATCCAGTGGAGACGAGAACGAAGATGAC
TCCAATACAAAAACCACCAACGGAGATGGGGTAGCTGCTGCTGCTGCTCCTCCTCCTCCTACTCCAGCAGTGCAGGGCAGTGCTTTGAAACGCCT
GATGGAGGAAGTGCCGGAGATCGCAGTGGCTGCAAAGAAAGTAGCTAAACCGAATACTATTCACGTTAGCAGTTCGGAGGCCATTCAAAAGCTGC
ACCAAGTTGTGGGCAACAGAGCGAAAAATCTTTCAGAGGACGCCGTTCCGCGTTCCAAAGATCACCGTAATGTGCCTGGCTTATATCAGCAGTTG
CACCAAAACCAAAGTCGCGATCGCCTTCGGAAGTTCAAAAGGGATCTGGAGGTGCAGCACCCAACGGAAAGTTTCCGGGACATTGGTGGCATGGA
TAGCACTCTTAAGGAGTTGTGTGAAATGCTGATCCATATTAAGTCGCCGGAGTTCTACTTTCAATTGGGTCTATTGCCTTCGAGAGGTTTATTGC
TTCATGGGCCGCCAGGCTGTGGCAAAACCTTTCTTGCTCGTGCCATTAGCGGGCAACTAAAAATGCCTCTAATGGAAATTCCGGCCACAGAGCTA
ATTGGTGGCATCTCTGGTGAGTCGGAAGAACGGATTCGCGAGGTCTTTGACCAGGCCATTGGCTACTCGCCTTGTGTGCTTTTCATCGATGAAAT
CGACGCCATCGGAGGAAATCGTCAGTGGGCGTCCAAGGATATGGAACGTCGCATTGTCTCGCAGCTGATAAGCAGTCTGGACAACCTGAAGGCCA
ACGAGTTTGGCCAATCAGTAGTCGTCATAGCGGCCACCACGCGTCCCGATGTCCTCGACCCTGGACTACGTCGCATCGGTCGCTTCGATCACGAA
ATTGCCATACACATCCCATCGCGGAAAGAGCGGCGTGAAATCTTGCGCATCCAGTGCGAGGGCTTGTCCGTCGATCCCAAGCTAAATTATGATAA
GATTGCAGAGCTAACACCGGGATATGTCGGTGCTGATCTAATGGCTCTCGTAAGTCGTGCAGCTTCTGTGGCCGTAAAGCGTAGGTCCATGAAGA
AGTTCCGTGAACTGCACGCTGCTAGTGAAAAGAATATGACAACGGTCACTTTGGATGACGACGAGCCCAGCGAGGACGCAGGTGAAACACCTGTG
CCTGATTCAAAAGGTGAAGAAACTGCAAAAGATGCAGAGGCAGAACAAAAGGTAGATGGTGACAAGGAAACATCTGCTAAGGATAAATCAGAAGG
CGACTCGCCAAATATTGAAACCCCCAAGAAAGCGACCAACGGCAACTCATCGATAAAGTCGCCGCAGAAAACACCGAAGAAATCAGCGGAGAAAC CAACTGACGCAGCGATGGATGTAGACAATGTTGCTCCCGAGGAGCCGAAAAAAGCCGTTGAGCAGGAGGTGGATTCCTCCTCCTCCAACGACGAG
TACTACGAACCCACACTGGCCGAACTGACCAATTTTCTTGACAACCCCCCTGAAGAGTTCGCCGACCCAAACTTTTGCCTCACTCTCATTGATTT
CGTAGATGCCATTAAGGTGATGCAGCCTTCGGCCAAGCGCGAGGGCTTTATAACAGTACCAGATACCACTTGGGATGACATTGGTGCCCTAGAGA
AAATTCGCGAAGAGCTTAAGTTGGCTGTCTTGGCACCAGTTAAGTATCCAGAGATGCTGGAACGTCTTGGGCTGACAGCTCCGTCAGGCGTTCTG
CTATGCGGTCCGCCGGGTTGCGGCAAAACTCTTTTGGCCAAGGCTATTGCCAATGAGGCTGGCATCAATTTCATATCGGTGAAGGGCCCCGAACT
TATGAACATGTATGTCGGCGAGAGCGAACGAGCTGTGCGTGCCTGTTTCCAACGTGCCCGGAACTCTGCACCCTGCGTCATCTTCTTCGACGAGT
TCGACTCCTTGTGCCCCAAGCGATCGGATGGTGGCGATGGTAATAATTCGGGCACTCGTATCGTTAACCAACTGCTGACCGAAATGGATGGCGTC
GAGGAGCGCAAGGGTGTATACATATTGGCGGCCACCAACAGACCGGATATCATTGATCCGGCCATCCTGCGACCGGGTCGCCTGGACACCATTTT
GTACGTGGGTTTCCCCGAGCAGAGCGAACGTACCGAGATTTTGAAGGCCACCACAAAGAACGGAAAGCGTCCGGTTCTGGCCGATGATGTAGATC
TCGATGAAATTGCTGCCCAAACCGAGGGCTATACTGGCGCAGATTTGGCAGGATTGGTCAAGCAGGCCTCCATGTTCTCCCTGCGACAATCTCTA
AACAACGGCGACACAAATCTCGACGATTTGTGCGTACGCAGCCAGCATTTCCAGGAAGCTTTGCAGCAACTTCGGCCCTCAGTTAACGAACAGGA
CCGCAAAATATACGATAAACTGCGCCTGAAATATGCTGCACCAAGGGTACCCACTCTAAATGATAAGTAAACCGATCAACAATAATGAGTTTGTT
GATTTAGCACCATCGCGAATCAATTTAATTGTAAGTTTCGAAAATTAACTTTTAATTTTCGATACAAAATGCGATATGTTACCCAAAAAAACAAA
ACCATTTAATCTATCTTGTAAAATGCGTAGAAGAGATATGTATTTAGTTTTTGGATTGTTTTAATTTTTTGTAGTATCTTACAAAATAAAAGTTA
AACTATTTGGGTTCA
(SEQ ID NO: 518)

Start ATG: 86

MKKAKPLLHDHLITIRVKKYLEEHIGETYLDVKQMTRELMQKYPEYSRRKFGPFRQLVHQAFSIISESYNLDKVSSSEEDCVSEDSEPPPTNSVM
NNMMNSLYSQPRKPLAPKPISEPIDISSGDENEDDSNTKTTNGDGVAAAAAPPPPTPAVQGSALKRLMEEVPEIAVAAKKVAKPNTIHVSSSEAI
QKLHQVVGNRAKNLSEDAVPRSKDHRNVPGLYQQLHQNQSRDRLRKFKRDLEVQHPTESFRDIGGMDSTLKELCEMLIHIKSPEFYFQLGLLPSR
GLLLHGPPGCGKTFLARAISGQLKMPLMEIPATELIGGISGESEERIREVFDQAIGYSPCVLFIDEIDAIGGNRQWASKDMERRIVSQLISSLDN
LKANEFGQSVVVIAATTRPDVLDPGLRRIGRFDHEIAIHIPSRKERREILRIQCEGLSVDPKLNYDKIAELTPGYVGADLMALVSRAASVAVKRR
SMKKFRELHAASEKNMTTVTLDDDEPSEDAGETPVPDSKGEETAKDAEAEQKVDGDKETSAKDKSEGDSPNIETPKKATNGNSSIKSPQKTPKKS
AEKPTDAAMDVDNVAPEEPKKAVEQEVDSSSSNDEYYEPTLAELTNFLDNPPEEFADPNFCLTLIDFVDAIKVMQPSAKREGFITVPDTTWDDIG
ALEKIREELKLAVLAPVKYPEMLERLGLTAPSGVLLCGPPGCGKTLLAKAIANEAGINFISVKGPELMNMYVGESERAVRACFQRARNSAPCVIF
FDEFDSLCPKRSDGGDGNNSGTRIVNQLLTEMDGVEERKGVYILAATNRPDIIDPAILRPGRLDTILYVGFPEQSERTEILKATTKNGKRPVLAD
DVDLDEIAAQTEGYTGADLAGLVKQASMFSLRQSLNNGDTNLDDLCVRSQHFQEALQQLRPSVNEQDRKIYDKLRLKYAAPRVPTLNDK*
(SEQ ID NO: 519)

Classification: enzyme
Gene Symbol: smid
FlyBase ID: FBgn0016983

Celera Sequence No. : 142000013385213
GTCTACTAATTCAAATTAAATGTAGTTTAGTTACATTTATAAGCTGATAATTCAAAAGCTTAAATGCGGCGATTTTAATAATTAATTTACCACAT
TAATTTAGCGGATTACTTCTCAAAGAATCGAAAAACAAACAATTGAAAAAGGGACTAAATCGATTGGCAGCAATCATCTCTAAAAAAAATTTTGT
TTATTTCTGACAACCGCATATAAACAAAATGAAAAGAGCATTAACCGGAAATATCTGCGCATTTATTGCATTATTACTGATAATCGAGAGATTAA
ATGGTATTAGTGCAATGATAACATATTTGCAAGCAAAAAAAAAGAGACAATCAAATTTTATATTTAAAGGTAGACAGATAAAATCAGTACCTTTT
ATTATCCAATTAAATATTGATTTAGGTGGCTATTTTTTGTCTTATTAAATATGGATAGAGCTTTACATTTTAACACATATTCGTTGAATAAATTA
ACAACAAAGATTGAACATAAATATTTATGGAAATTGTAATTGAAGCTTTTAAACGTATAGCCTTAATATTAAACATTATTAATATTATATTATTT
TAAGATGAAGGTTTTCCTTACAAAAGTAAAGACGAGAAAGTAAAACATAAACATTTGTCATAAACATTTAAATGAGCCCGCGTGGTGTGCAGATT
CAGCCGACTTCTATTCAGCTGTTGGCTGAATTTGGCTTGCATGCGCACACGTTCCACGTTCCACAACAACATATTGAAATCCAAAAGCTGCTTCA
CCACTTGGCAAGCGATCGTTAACAAGTTACACCAGAAATTTATATATACTAAAAAAATAATAAGTTACTTAAAAATTTAGTAATAATTATGTGGA
TATAAAAAATGTACATTATTTTTCTCTACGCGCCGTTGTCCGAAGTTAACAGCAAGATAACATGCGATATTAGGCACCTACGTTCACACTGGCAT
CAAATTTCGATAACTGACAAAGATCGATAGCCATCTGCGTTTCGTTCGCCACTAAGGCTTGCTTTTCAAATCAAACGGTAAATTCTGGCGGCGCC
AAGCAGGCATTGACTCCAATTTCGCATCGATTACGAGAGTACTGTCTACGTTTGTCTACAGTTTCACCGACACATTCAGCGTGCTAACACGCTCG
ACAAATTCTCGTGCTCGCGTTTCGTTAGGGAACGATAAAAATTGTGTAAAAATTCAGTAAAGTGAATTTCCATTCGAAAAAGCCAGCACACGCAT
TCAAAAGGGCAAAGGTACAAAGGTAAGTGCGTGTGTACTCTTTTCTTCCTTTTCGCGGTTTTTCCCACTGCTTTTTACTAGCGTTCATCAATTTG
ACCGCCTCTTCGTGATCTCCTCTTCTCGTTCCCCTCTTTCCGCGAATCGGCAAATGGCGGCTGCTGCAGCTGTTGCCAACCAAAGGCGTAGTTCT
TAACTCGCGGGGGCTTGAGCGATTGGGTGCCCCGTTAAAAATAATCTTGTAAATTAGTTGGCTTATGTTGGCTAACACATAGGAATAACATATCG
AGTTGCTGGCCACAAAGAAAACCCCTTTTTTGAACTCATGGTTACGCCCCTGTTGCACGCCGAAAGGAATATAAAAGACAGAGATAAAAAAAAAG
AACCCAAGCAGCCCTTGATTCTGCTTCTTCCTGACATTGACTCACATTTTCCTTTTCAGTTTCACACATTTCATCGCAGCAGCAAACATCTAAAC
TTTTAAAGAAAAAACACAAAACTCAAAAAAAAAAAAAAAAATGAGTAAGGCGGATTCTAACTCACGACAGGGCTCCTACAAGGCCAACAGCATTAA
CACGCAGGTAATGTACACAAGATCCTCCGCAGAACTGCGTTCGGAACTAACCTCACTTTTTGCCCTAGGACTCACGCATGCGCCGCCATGAGGTG
ACCATCGAGCTGCGCAAGTCCAAAAAGGAGGACCAGATGTTCAAGCGGCGCAACATCAACGACGAGGATCTAACGTCGCCGCTCAAAGAGCTCAA
TGGCCAGTCGCCGGTGCAGCTGTCCGTGGACGAGATAGTGGCGGCCATGAACAGCGAGGATCAGGAGCGCCAGTTTCTGGGCATGCAGTCTGCCC
GCAAGATGCTCAGTCGGGAGCGCAATCCACCCATCGACCTGATGATCGGCCATGGTATTGTGCCCATTTGCATACGCTTCCTGCAGAATACCAAC
AAGTGAGTAGTGGCTTTAGAATGTTGATGAGAGCATTATTGAATATCCCCTGATTCGCCGCTACAGCTCAATGCTGCAGTTCGAGGCCGCTTGGG
CGCTTACCAACATCGCCTCTGGCACATCCGACCAAACGCGCTGCGTTATCGAACACAATGCTGTGCCGCATTTCGTGGCTCTGCTCCAGTCCAAG
TCCATGAACCTGGCCGAGCAGGCAGTCTGGGCTCTGGGCAACATTGCCGGCGACGGAGCCGCCGCCCGCGACATTGTCATCCACCACAACGTAAT
TGACGGAATCTTGCCACTGATCAACAATGAGACACCGCTCTCTTTTCTGCGCAACATCGTCTGGCTGATGTCCAACCTGTGCCGGAACAAGAATC
CATCGCCGCCATTCGATCAGGTGAAGCGGCTGTTGCCCGTCCTGTCGCAGCTTCTGCTTAGTCAGGACATCCAAGTGCTGGCCGACGCCTGCTGG
GCTTTGTCCTACGTCACGGACGACGATAACACCAAGATCCAGGCTGTGGTCGACTCGGACGCAGTGCCGCGCCTGGTCAAACTGCTGCAAATGGA
CGAGCCGAGCATTATTGTGCCCGCCCTGCGCAGCGTTGGCAACATTGTGACTGGCACAGATCAACAGGTAGGAAAACAAATGATTTTAATCCTTA
TTGTTATAACATGCCTGACCGACCTGTTTTTTTTTTTTTTTTTATTAGACTGACGTTGTAATTGCATCTGGAGGTTTACCAAGGCTGGGACTCC
TTCTACAGCACAACAAAAGCAACATTGTGAAGGAGGCTGCCTGGACGGTCAGCAACATCACAGCAGGTAACCAGAAGCAGATCCAGGCTGTGATT
CAGGCCGGCATCTTCCAGCAGCTGCGCACCGTGCTGGAGAAGGGTGATTTCAAGGCTCAAAAAGAGGCTGCCTGGGCGGTGACAAACACCACGAC
ATCTGGCACTCCCGAACAGATCGTCGATCTAATTGAGAAGTACAAAATATTGAAGCCTTTTATCGATTTGCTGGACACAAAGGATCCGCGTACCA TCAAGGTGGTGCAGACGGGCCTATCCAATCTGTTTGCCCTGGCGGAGAAACTTGGTGGCACCGAGAACCTATGCTTGATGGTCGAGGAGATGGGC
GGTCTAGACAAGCTGGAAACTCTGCAGCAGCACGAGAACGAGGAGGTCTACAAGAAGGCCTACGCCATCATTGACACATACTTCAGCAACGGCGA
CGACGAGGCCGAGCAAGAGCTCGCACCTCAGGAGGTCAACGGAGCCCTCGAGTTCAATGCCACCCAGCCCAAGGCTCCCGAAGGTGGCTACACGT
TCTAATCGCCCACCCCACACATTCCAAACTCCGCTCACACGCCTTACAAACAACTACACCTTCGACCGCGCTCACACACTATGCCATTGTCAAAC
ATACGCATACTCATCATCACATCTTACAAACATTCCCAAACACTTTGGAGGTATGCATGGAAACACAGGCGAATGCATTAGCTTAAAGTCATAAT
TGAATCGGGTTGGCAAAATCCACTCGCATGAATCCCCATTTAACATACCCGTATTCCTCGCGTTAGACTAGACTTCACAGATTGCAGCATGGATC
TTTCTGGCAGTGTTCCTCGTTCACGATGCAACCGCTCGGGCAGCTGCGCTGGCTGGGATCCGTGGATCATAGTATTTCCAGAATCCGTCTGTACA
GGGGGCACCTTATGTTTGCGTGTACTAGGCTTTTATTGGATACGTTTCGAGCTCATTTCGGATATATTTTAGGCTGTTTAGTATTTATTTATGT
ATACAGGAAACGCTTTTAATCCTCCACCTTCGCGCAAGCATTACAACAACAACAACAACAACAACAACTCATTCCCTTCACACCAGTGTCCTCAT
TCCCGAATCGCATGTTTATATTCAAAGTTGTCAATAAATAATGAATTGTTTGAATGATTAATTAAATTTCATGTGTATTTAAGCTGCATTTGAGC
ATTGCGAAAATTGGAGCCTATTTTTGGGCCTTGGCATTTTTTTTTGTATATTATTTGGAATGCTATTGGGATATACACCGATGCAGGCAATCGAA
TTTAAAATGTTATCCCTTCGATGCGCTGGCGCCTTTTGTCCGTAAATCCGCGATAAAAAGTCATGCAGTCAATACATGTTTTTTTTTTTGTCTTG
TACATTTAAATCGCATTTGGGCCGTAAGCGGATAGCCGGAAGATTAAGAGCTATCTACCGCAGCCACGCCCACTCGAGCAGCGGTGGACAGCGAC
CCCAAAAAAGTTCCAGATTAGATATAATGATTAAACAACCGACGAGTGAGTAGTGAGTAGTAGTCTACTACTGGCACAGAACGCGCACCACGCAC
AACTCAATCAAGATGAATCGCAGCGTTCGTGGTTATTGCAGTGATCCAGAGGGTAAGCTTAATCAGTGGAGCGACGACGTCACATCAACAACCAT
GTCCACGTACGATCTTGTTCCCATCGGATGCAGTGCGTCGAATTCGGCGAATCGTGTGTGTGTGTGGCAAAACAAATTATAAAAATAGATTAAAA
ATTCAGCATGGGCAAAGTAGTTGCCGAAAATTCGAACTGAATTGTGGAAGCATTGGCCGCCATCCGGAGCTTTTGCCTCCGCGTTGCCCAAATTG
TCGTCACCGATGGATCGGATCTATGTATTCAATTGGTTCTTTCTCGAGCTATTTTATTATTTCCGAGCGCAAGCGTTTAGTCGACTTTCTGCCGA
AGCTGCGTGCGGGCGTGAATCTCTAAGGGCAACTAATTTATATAATTGCAAAACGATCTGAACTGACATTACGCATTTGAAACTTAAAAATTTCT
AACGATTTTTAAAAAAGGTAATAGAGAATAGTGCAAGTGATGTGAAACCAATCGGTAGTTTCGTAAATTGCCTTGTGTGTAAATCAATTCGCATT
TTCACTGAATGTGT
(SEQ ID NO: 520)

Exon: 1001..1257
Exon: 1675..1812
Exon: 1874..2187
Exon: 2252..2822
Exon: 2900..4144
Start ATG: 1750

Transcript No. : CT15419
ACTAAGGCTTGCTTTTCAAATCAAACGGTAAATTCTGGCGGCGCCAAGCAGGCATTGACTCCAATTTCGCATCGATTACGAGAGTACTGTCTACG
TTTGTCTACAGTTTCACCGACACATTCAGCGTGCTAACACGCTCGACAAATTCTCGTGCTCGCGTTTCGTTAGGGAACGATAAAAATTGTGTAAA
AATTCAGTAAAGTGAATTTCCATTCGAAAAAGCCAGCACACGCATTCAAAAGGGCAAAGGTACAAAGTTTCACACATTTCATCGCAGCAGCAAAC
ATCTAAACTTTTAAAGAAAAAACACAAAACTCAAAAAAAAAAAAAAAAATGAGTAAGGCGGATTCTAACTCACGACAGGGCTCCTACAAGGCCAAC
AGCATTAACACGCAGGACTCACGCATGCGCCGCCATGAGGTGACCATCGAGCTGCGCAAGTCCAAAAAGGAGGACCAGATGTTCAAGCGGCGCAA
CATCAACGACGAGGATCTAACGTCGCCGCTCAAAGAGCTCAATGGCCAGTCGCCGGTGCAGCTGTCCGTGGACGAGATAGTGGCGGCCATGAACA
GCGAGGATCAGGAGCGCCAGTTTCTGGGCATGCAGTCTGCCCGCAAGATGCTCAGTCGGGAGCGCAATCCACCCATCGACCTGATGATCGGCCAT
GGTATTGTGCCCATTTGCATACGCTTCCTGCAGAATACCAACAACTCAATGCTGCAGTTCGAGGCCGCTTGGGCGCTTACCAACATCGCCTCTGG
CACATCCGACCAAACGCGCTGCGTTATCGAACACAATGCTGTGCCGCATTTCGTGGCTCTGCTCCAGTCCAAGTCCATGAACCTGGCCGAGCAGG
CAGTCTGGGCTCTGGGCAACATTGCCGGCGACGGAGCCGCCGCCCGCGACATTGTCATCCACCACAACGTAATTGACGGAATCTTGCCACTGATC
AACAATGAGACACCGCTCTCTTTTCTGCGCAACATCGTCTGGCTGATGTCCAACCTGTGCCGGAACAAGAATCCATCGCCGCCATTCGATCAGGT
GAAGCGGCTGTTGCCCGTCCTGTCGCAGCTTCTGCTTAGTCAGGACATCCAAGTGCTGGCCGACGCCTGCTGGGCTTTGTCCTACGTCACGGACG
ACGATAACACCAAGATCCAGGCTGTGGTCGACTCGGACGCAGTGCCGCGCCTGGTCAAACTGCTGCAAATGGACGAGCCGAGCATTATTGTGCCC
GCCCTGCGCAGCGTTGGCAACATTGTGACTGGCACAGATCAACAGACTGACGTTGTAATTGCATCTGGAGGTTTACCAAGGCTGGGACTCCTTCT
ACAGCACAACAAAAGCAACATTGTGAAGGAGGCTGCCTGGACGGTCAGCAACATCACAGCAGGTAACCAGAAGCAGATCCAGGCTGTGATTCAGG
CCGGCATCTTCCAGCAGCTGCGCACCGTGCTGGAGAAGGGTGATTTCAAGGCTCAAAAAGAGGCTGCCTGGGCGGTGACAAACACCACGACATCT
GGCACTCCCGAACAGATCGTCGATCTAATTGAGAAGTACAAAATATTGAAGCCTTTTATCGATTTGCTGGACACAAAGGATCCGCGTACCATCAA
GGTGGTGCAGACGGGCCTATCCAATCTGTTTGCCCTGGCGGAGAAACTTGGTGGCACCGAGAACCTATGCTTGATGGTCGAGGAGATGGGCGGTC
TAGACAAGCTGGAAACTCTGCAGCAGCACGAGAACGAGGAGGTCTACAAGAAGGCCTACGCCATCATTGACACATACTTCAGCAACGGCGACGAC
GAGGCCGAGCAAGAGCTCGCACCTCAGGAGGTCAACGGAGCCCTCGAGTTCAATGCCACCCAGCCCAAGGCTCCCGAAGGTGGCTACACGTTCTA
ATCGCCCACCCCACACATTCCAAACTCCGCTCACACGCCTTACAAACAACTACACCTTCGACCGCGCTCACACACTATGCCATTGTCAAACATAC
GCATACTCATCATCACATCTTACAAACATTCCCAAACACTTTGGAGGTATGCATGGAAACACAGGCGAATGCATTAGCTTAAAGTCATAATTGAA
TCGGGTTGGCAAAATCCACTCGCATGAATCCCCATTTAACATACCCGTATTCCTCGCGTTAGACTAGACTTCACAGATTGCAGCATGGATCTTTC
TGGCAGTGTTCCTCGTTCACGATGCAACCGCTCGGGCAGCTGCGCTGGCTGGGATCCGTGGATCATAGTATTTCCAGAATCCGTCTGTACAGGGG
GCACCTTATGTTTGCGTGTACTAGGCTTTTTATTGGATACGTTTCGAGCTCATTTCGGATATATTTTAGGCTGTTTAGTATTTATTTATGTATAC
AGGAAACGCTTTTAATCCTCCACCTTCGCGCAAGCATTACAACAACAACAACAACAACAACAACTCATTCCCTTCACACCAGTGTCCTCATTCCC
GAATCGCATGTTTATATTCAAAGTTGTCAATAAATAATGAATTGTTTGAATGATT
(SEQ ID NO: 521)

Start ATG: 333

MSKADSNSRQGSYKANSINTQDSRMRRHEVTIELRKSKKEDQMFKRRNINDEDLTSPLKELNGQSPVQLSVDEIVAAMNSEDQERQFLGMQSARK
MLSRERNPPIDLMIGHGIVPICIRFLQNTNNSMLQFEAAWALTNIASGTSDQTRCVIEHNAVPHFVALLQSKSMNLAEQAVWALGNIAGDGAAAR
DIVIHHNVIDGILPLINNETPLSFLRNIVWLMSNLCRNKNPSPPFDQVKRLLPVLSQLLLSQDIQVLADACWALSYVTDDDNTKIQAVVDSDAVP
RLVKLLQMDEPSIIVPALRSVGNIVTGTDQQTDVVIASGGLPRLGLLLQHNKSNIVKEAAWTVSNITAGNQKQIQAVIQAGIFQQLRTVLEKGDF
KAQKEAAWAVTNTTTSGTPEQIVDLIEKYKILKPFIDLLDTKDPRTIKVVQTGLSNLFALAEKLGGTENLCLMVEEMGGLDKLETLQQHENEEVY
KKAYAIIDTYFSNGDDEAEQELAPQEVNGALEFNATQPKAPEGGYTF*
(SEQ ID NO: 522)

Name: Pendulin

FIGURE SHEET 286

Classification: known_flybase_gene
Gene Symbol: Pen
FlyBase ID: FBgn0011823

Celera Sequence No. : 142000013384539
AACATTGCAGTAAAAAAAAACAGAAGCAAAGGGGAGCAACAAAAACAGAGAGAGGGCAAAATAAGAGAGAGGACAACCAGACAGAGCGAGATGCC
AAACAACAGCTGTTCTTCTTGCCAGATGCGAAATGGGCAATTTAATGAAATTTATCTAGATTTCACTCACTTTTCACTTGCCAAACGTCGTGTTT
GTGCACTTTTCACAATTGTCGCGGCGTCACACGTTTATTTATTTACATTTCTCTGCGTTTCAGGCGCTCGCACGCTCAATTAGCGCGCTTTCCGC
TTTGTGCCACACATTCTGTGCCAGCCACAAAAAAGCCCGCAATTCGCACTTTCATGTGTTTTCGGCTATTTCTGCGATCGTTTTTCCTGCACTTG
CACTGCTCAATAGCTAATGTTTAGTTAATTGACACTTTCTAAGCGTTTTGCGTATATTTTTTACGAATTATTTTGGCAAAACGACGCGGTACCAG
CGTCAACGTCCGCATTCTTCAAAATCGGCGAATGAACTGAACAAAACGAACTGCGCAAGTTGGGCAATAGGAACAGCTGACCGCGCTGCCAGACT
GCCGAACGGAAACTCGCTGCGAGAGTCTGGCAGCACTTGCAACCATCGATATAAACTATTGGTAACGAATATTTAAAGAATTAACTTTATAGTTC
CATTGAAAATACATACATAAAACAACTATAATTATGATACCTAACATAAAACATCGTAATATCTTATTTATAGTTATCTTTTGTATGCAATATTC
AATTTTAAGTTAATTAGATAAACACCAAACGTTTTTTATTTGTGAAAATAGAAAAAGAATTCAATAGAAACAAGTTTTCAAGGCAATCTGCATA
TTCTTAAATCCAACTTTATGGGCACTTTTGAATATTCATTTATTTTGCAGCCCTAGCAATCGCTGAGCGATAACCATAAGTTGACTATCGATAGC
AGCAGAGCGATATGCAAAACAAACGAAAAAAGTAAAAGAGCGGTGTAAAGCAGACAACATAGTTTACATTTTTTGCAACAAGTTTTTCAACTTAA
AGCCAACTCCCATCGTCCAATGGAGGTGGACCAGATTCCCCTGGCCGACGTGGTCTTCGTCATCGAGGGCAGCGCCATCAACGGAGCCTACATCA
ACGAACTAAAGACCAACTACATCCTGCCGACTTTGGAGCACTTCACCACTGGCTCCATCGACGAGCGGGAATACCTGATTGCGGAGCGCTTTGCC
ACTCTGTACGGTATTGTGGTCTACCGTACAGCGGCCAATCTGCTGGAGCCAGTTTGTTCAACCTATGGTCCCTTTCTGCAGCCCCAAAAAGTGAT
GGAGACGATCGAAAGATTGCCACTAGTGGGAGGCGGAATGGAGTCCTGTGCCCACATGGCCGAAGGATTTGCTGCGGCCCACGGCTGTTTTGATG
ACATCAGCGAAAGGCGCCAGTTGCTCGATCAGACCAGCGTCCAGAGGCACTGCATTCTCATCTGCAACAGTCCGCCGTACCAGATGCCCACAACG
GAGTCGTGGAAGTATCCGGGCAAATCATGTGAGCAGCTGGCGGCGCTCTTCAACGAGCGCAAAATCAATCTCTCCATTATTGCGCCACGCAAGAT
GCCGGTGTTGTTCAAACTTTTCATGAAGGCCGACGGAGATCAGCCCATTACGAGCAAAAACTATGCCAAGAACATAAGACACCTAGTGCTTCTAA
AGGGATACAGCCTCAAGGAGAGAGCACCTAGTCCCAACAGCATGGCGGCCCAAATGGCTGCACCCAATGCGGCACAGGCTACAGTGCAGCAGCAA
CAACAACAGCAACAAAATCAAGCTGGTCAGCAACAACAAGGGCAGGGCATGCCCATGGACACCACTCCAGCCCAGCAGCAGCAACAGCAACAACA
ACAGCAGCAGCAACAGCAACAACAAGGCAATCCTCAGCAGCAGGTCATGAACATGAACACGATGCAGCAACAGCAGCCCGGTCCAAATCCCCCAG
CGGGCTTACTCAATCCACAGCAGCAGCAGCAACTATTGCAGCAGCAGCAGCAGAATCAATTCGTTTCCAATCAAATGCAGAATCAGAACTTCCAG
CAAAACGTGGGACCCGGCCAAAACCGCTGGATGTATCCCAACCAGCCTGGTCAGGCGCGTCCGCCCTTCATGCAGGGAGCAGGCAATGTGGGCGG
TGTGGGCCAAGGCGGCGGCATGCAACAGAATCCAAATTCTGCTCTGATATCGCGCATTAATGCGCCGCCGCCGAACCAAACTGTGACCTCGCTGC
AGCAGCAGCAACAGCAGCAGGCGCAGCAGCAGCAGCAGCAGCAACAACAGGCCCAACAGCAGCAGCAACAAAGGATGCAGATGCTGAGCCAGCAG
CAGATGCTAAATCACCAGCAGTTGCAGCAGCAACAGCAACTGGCCCAGCAACAGCAACAGCAGCAGCAAGGACAGCAACAGCAGCAGGTAAATCC
CAATGCAGGAAACAATATGATGCCGGCTAGCAATGCCGGCAACATGTCTAATCCGCAGCAGCAACAACAAGTAGGACAACAGTCGAATCCGC
AGCAGCAGGGCAATCCGCAGCAGCAACAGCAGGGAAATTCGCAGCAGGAGCAGGCCTCCTTGAGGGAAAAGATATGGACCGGAGTGCTGGAGTGG
TCAGAGAAGCCAAAGTCCGATCAACAGAAGATTCCCCATACACTCCAGTGTACCGTGTGCACCAACATCAAAGATGGCGAGCCCGAGATCAAGGC
TGAGAACTGGCCGCCCAAGCTGTTGATGCAGCTAATGCCCAAGCACCTAGTTGGCAATATTGGTGGGCAGTTTCTCAAGGACTCGAAAATGGTTG
TTTTTCGACCCACTCCAGGAGAGGCACTCGATTCGCTGGCCAAGATGATGACCTCCGGCTATGCTGGCTGCGTCCACTTCTCCTCCATCCCCAAC
TCACCAGCCTGTGACCTTAAGGTTCTCATCCTACTCTACACGCCCGATCGCAACGCTTTTCTGGGCTTCATTCCCAATAATCAGGCAATGTTTGT
GGAACGTCTGCGCAAAGTCATACAGCAAAAGCAGCACGGCAACATGCAACAGCAGCAGCAACAGCAGCAAATGATGCAGCAGCAAGGCAAGTCGC
CCATGGAGCTGCAGCAGCAACAGCAACAACAACAACAGCAGCAACAGATGCAACAGGATAACTCGCAGCAGCAACACTACAACCAGTTCCAACTC
AATATGCAGATGGGTGGTGGAGGTCCTGGCGGCGGACCTGGTCCCGGTCCCGGCGGCATGCCCATGCAACAGAATCAAATGCAGATGAACATGAT
GCAGCAACAGCGAATGCCACTGGGCGTAGGTGTTGGCGTGGGTGTTGGTCCCGGTGGCGTGCCCAATCCAAACCTCCAGCAGCAGTTGCAACAAG
TGGCGCCAAACGTCGCCGCAATGCAGCAGCAGCAGGCGCAACAGCAGCAGCAGCGCATGGTGCGTCCCATGATGAGCAACAACAACCCGGGGCTG
CGCCAGCTCTTGCAGCACCAGACCACGCCAGGCAATCAGTTCCGGCCGCAAATGGGTGGCCAGAATCCCAATCAAATGGGAGCAGGCGGTCCAAT
GGTCGGCAATCGCAACTTTGACGACGGAAACTATGAGTTCATGTAGGCTACTTAAGAGTATCGTATAAAAAACCAGAATTAAGACAGTAAAATAT
TTTATAAAATCCAACTGCAAGTCTTTTTGGGGTAGTGGCAAAATCTATTTCCCAAAATCGAAATATTAATTTCTCCATTTTCATAACATTTCGT
TTATTTAATTAGTAAGAATCAAGGGAAATCCGAATTTGCACAAGACTTATATTAATCACAGAACATAATCTCCGAGAAAGTCCACTAGTTTGCTC
CACCGCCGCCGCCCCCCGAGGATGCGGAACTTGCACTTCCAGCGCTAGCGGCAAACACCTTGCGAAGATTCTGCAAGATGCTGAACAGAACCGTT
CCCGCGCTGCCCAACGTTTCCAGAACATCGAATCCGGTGCTGTCGATGGCTGTCTCCCGATCCTCCTCCGTTTCGATGGCCGGGGAGCTGATGTT
CCCGCCATTGTGGTGAGTTTCGTGGACGCCATGGTGTCCAATCAGCCGATGAGTATTGCTCTTCACATGGGAGTCGTTCACGCCGCCACCGCCAA
CTGTGTTTATCAGGTGCTTCACCGGCTCCAGGACCGGAATATTTAGCTTAATGCGATGCCATGCATCCGCAGTTTCGGTGAAGCCCTCATGCTGC
TCGCCAGTGGCCTTCATCTCATCATCCAGCTGGTTTCGCTCGCTGACCGGATCGTCGTCCGTCTCCAGGGACAGCTCCAGACTCATGTTTCCCTT
ACCAGGCAGTTGCAACAAACTGCCGAAGAGCTGTTGCAGATGCGCCGAGTTGGTGGCCTCCGCCTCATTCTGCTCGAAATCGAACTCTTCACGTA
CTCCCGACTTGGGCTTCTGGTTCACAAAGCTGGTCACATGCAGCATTCCATTCTTGGTGCCAGAATCACTGGAGTTGGTGGGCTTGGCGGACGTC
GTCGTCGTCGTCGTCGTCAGCAGTAGCAGCCACAAAAACTGCAGATACATTCGGAGAAATGGAATCTATAATTGGCGCTTAATGACCGGCTGCAC
G
(SEQ ID NO: 523)

Exon: 1001..3656
Start ATG: 1065

Transcript No. : CT15479
CAGACAACATAGTTTACATTTTTTGCAACAAGTTTTTCAACTTAAAGCCAACTCCCATCGTCCAATGGAGGTGGACCAGATTCCCCTGGCCGACG
TGGTCTTCGTCATCGAGGGCAGCGCCATCAACGGAGCCTACATCAACGAACTAAAGACCAACTACATCCTGCCGACTTTGGAGCACTTCACCACT
GGCTCCATCGACGAGCGGGAATACCTGATTGCGGAGCGCTTTGCCACTCTGTACGGTATTGTGGTCTACCGTACAGCGGCCAATCTGCTGGAGCC
AGTTTGTTCAACCTATGGTCCCTTTCTGCAGCCCCAAAAAGTGATGGAGACGATCGAAAGATTGCCACTAGTGGGAGGCGGAATGGAGTCCTGTG
CCCACATGGCCGAAGGATTTGCTGCGGCCCACGGCTGTTTTGATGACATCAGCGAAAGGCGCCAGTTGCTCGATCAGACCAGCGTCCAGAGGCAC
TGCATTCTCATCTGCAACAGTCCGCCGTACCAGATGCCCACAACGGAGTCGTGGAAGTATCCGGGCAAATCATGTGAGCAGCTGGCGGCGCTCTT
CAACGAGCGCAAAATCAATCTCTCCATTATTGCGCCACGCAAGATGCCGGTGTTGTTCAAACTTTTCATGAAGGCCGACGGAGATCAGCCCATTA
CGAGCAAAAACTATGCCAAGAACATAAGACACCTAGTGCTTCTAAAGGGATACAGCCTCAAGGAGAGAGCACCTAGTCCCAACAGCATGGCGGCC
CAAATGGCTGCACCCAATGCGGCACAGGCTACAGTGCAGCAGCAACAACAACAGCAACAAAATCAAGCTGGTCAGCAACAACAAGGGCAGGGCAT GCCCATGGACACCACTCCAGCCCAGCAGCAGCAACAGCAACAACAACAGCAGCAGCAACAGCAACAACAAGGCAATCCTCAGCAGCAGGTCATGA
ACATGAACACGATGCAGCAACAGCAGCCCGGTCCAAATCCCCCAGCGGGCTTACTCAATCCACAGCAGCAGCAGCAACTATTGCAGCAGCAGCAG
CAGAATCAATTCGTTTCCAATCAAATGCAGAATCAGAACTTCCAGCAAAACGTGGGACCCGGCCAAAACCGCTGGATGTATCCCAACCAGCCTGG
TCAGGCGCGTCCGCCCTTCATGCAGGGAGCAGGCAATGTGGGCGGTGTGGGCCAAGGCGGCGGCATGCAACAGAATCCAAATTCTGCTCTGATAT
CGCGCATTAATGCGCCGCCGCCGAACCAAACTGTGACCTCGCTGCAGCAGCAGCAACAGCAGCAGGCGCAGCAGCAGCAGCAGCAGCAACAACAG
GCCCAACAGCAGCAGCAACAAAGGATGCAGATGCTGAGCCAGCAGCAGATGCTAAATCACCAGCAGTTGCAGCAGCAACAGCAACTGGCCCAGCA
ACAGCAACAGCAGCAGCAAGGACAGCAACAGCAGCAGGTAAATCCCAATGCAGGAAACAATATGATGCCGGCTAGCAATGCCGGCAACATGTCTA
ATCCGCAGCAGCAGCAACAACAAGTAGGACAACAGTCGAATCCGCAGCAGCAGGGCAATCCGCAGCAGCAACAGCAGGGAAATTCGCAGCAGGAG
CAGGCCTCCTTGAGGGAAAAGATATGGACCGGAGTGCTGGAGTGGTCAGAGAAGCCAAAGTCCGATCAACAGAAGATTCCCCATACACTCCAGTG
TACCGTGTGCACCAACATCAAAGATGGCGAGCCCGAGATCAAGGCTGAGAACTGGCCGCCCAAGCTGTTGATGCAGCTAATGCCCAAGCACCTAG
TTGGCAATATTGGTGGGCAGTTTCTCAAGGACTCGAAAATGGTTGTTTTTCGACCCACTCCAGGAGAGGCACTCGATTCGCTGGCCAAGATGATG
ACCTCCGGCTATGCTGGCTGCGTCCACTTCTCCTCCATCCCCAACTCACCAGCCTGTGACCTTAAGGTTCTCATCCTACTCTACACGCCCGATCG
CAACGCTTTTCTGGGCTTCATTCCCAATAATCAGGCAATGTTTGTGGAACGTCTGCGCAAAGTCATACAGCAAAAGCAGCACGGCAACATGCAAC
AGCAGCAGCAACAGCAGCAAATGATGCAGCAGCAAGGCAAGTCGCCCATGGAGCTGCAGCAGCAACAGCAACAACAACAACAGCAGCAACAGATG
CAACAGGATAACTCGCAGCAGCAACACTACAACCAGTTCCAACTCAATATGCAGATGGGTGGTGGAGGTCCTGGCGGCGGACCTGGTCCCGGTCC
CGGCGGCATGCCCATGCAACAGAATCAAATGCAGATGAACATGATGCAGCAACAGCGAATGCCACTGGGCGTAGGTGTTGGCGTGGGTGTTGGTC
CCGGTGGCGTGCCCAATCCAAACCTCCAGCAGCAGTTGCAACAAGTGGCGCCAAACGTCGCCGCAATGCAGCAGCAGCAGGCGCAACAGCAGCAG
CAGCGCATGGTGCGTCCCATGATGAGCAACAACAACCCGGGGCTGCGCCAGCTCTTGCAGCACCAGACCACGCCAGGCAATCAGTTCCGGCCGCA
AATGGGTGGCCAGAATCCCAATCAAATGGGAGCAGGCGGTCCAATGGTCGGCAATCGCAACTTTGACGACGGAAACTATGAGTTCATGTAG
(SEQ ID NO: 524)

Start ATG: 65

MEVDQIPLADVVFVIEGSAINGAYINELKTNYILPTLEHFTTGSIDEREYLIAERFATLYGIVVYRTAANLLEPVCSTYGPFLQPQKVMETIERL
PLVGGGMESCAHMAEGFAAAHGCFDDISERRQLLDQTSVQRHCILICNSPPYQMPTTESWKYPGKSCEQLAALFNERKINLSIIAPRKMPVLFKL
FMKADGDQPITSKNYAKNIRHLVLLKGYSLKERAPSPNSMAAQMAAPNAAQATVQQQQQQQQNQAGQQQQGQGMPMDTTPAQQQQQQQQQQQQQ
QQGNPQQQVMNMNTMQQQPGPNPPAGLLNPQQQQLLQQQQNQFVSNQMQNQNFQQNVGPGQNRWMYPNQPGQARPPFMQGAGNVGGVGQGGG
MQQNPNSALISRINAPPPNQTVTSLQQQQQQAQQQQQQQQAQQQQQQRMQMLSQQQMLNHQQLQQQQQLAQQQQQQQQGQQQQQVNPNAGNNM
MPASNAGNMSNPQQQQQQVGQQSNPQQQGNPQQQQQGNSQQEQASLREKIWTGVLEWSEKPKSDQQKIPHTLQCTVCTNIKDGEPEIKAENWPPK
LLMQLMPKHLVGNIGGQFLKDSKMVVFRPTPGEALDSLAKMMTSGYAGCVHFSSIPNSPACDLKVLILLYTPDRNAFLGFIPNNQAMFVERLRKV
IQQKQHGNMQQQQQQQQMMQQQGKSPMELQQQQQQQQQQQQMQQDNSQQQHYNQFQLNMQMGGGGPGGGPGPGPGGMPMQQNQMQMNMMQQQRMP
LGVGVGVGVGPGGVPNPNLQQQLQQVAPNVAAMQQQQAQQQQQRMVRPMMSNNNPGLRQLLQHQTTPGNQFRPQMGGQNPNQMGAGGPMVGNRNF
DDGNYEFM*
(SEQ ID NO: 525)

Celera Sequence No. : 142000013384273
CTATAACATTTTAAACAGGCGTGTTTCGATAGTGCGACGTAAGATAGTGTTAGCCTTGGTAATGGCGAGCAATTAGATAAAGATCACTCAGCTCA
AGGTCTCAGAGAAATCTCGAGCTAATCAAACATCTCGATGGAATCCCGCTTTCTGGACGAAAAATTGTTTTCCCACCCGTAGCAATAAGAAAAGG
CGAAACAAAACTGTCAAGCAGAGTGGACACATGTAGCACGATCACTTTTTTTGTTCCGGCGATAGTGTGTTTAGCTAGCCTGGGTCGCCAGCTTC
GGCTCCAGCTCTAGTACCAGGTTCATCTTCATCTGCAGATCAGTAGCTGAAATCAGGATCAATGTGAGCCACATCCAGGCTTAGGTTTATCTCTA
CCGCCTGCTCTCGTCTAGATCTGTCGGATGTCAGGTTGCATAGTTGGGCCGGCAATTGCATGTCGCGATCGTCCAGCGCCGAAGATCTGCCTCAA
CCTCAAGCTGAACCTCATCCGCGTCCACATCCACATCCTCAATCCTGAGTCGCTAAAACTTGAAAGCCGCATTCGATGGCTGGCCGCTGACAGCG
CGGAATTGTCGTTCGCATTGTCAGCTGGCATGGGCGTCGAAGGAGGGGCGGTGCTGAGCCAGGGGGGTTTATCCGCCGACTTTTGCCGACGATAT
ACAAAAGATGCAACTGTCGCTGCTTGTTGCAGCAGTTGTTTCTGCTTTCTGTAGCTGCCCAGCTTGACAGTTGCTGCAAGAGCAAAAAAATGCGC
TTGGGAAACTGCCACTGGCGATGCCGCTGCTGCTGCCACCGCGAGCTGGCTTAAATCAAATATTGAAATGCCTCAGAGCAGATCGGCGACCCTGA
CCCGTGCCCGTGCCCCTGTCCCTGCCCCCCCACTCCACCTCCCCGGATACCAGCTAATTGCCCCACACATGGTCCAAATAATTGCCCCAGCAACA
ACAGCCCGTACCAATGAATTCCACTTGGCTTTTATTTTTTGTAATTTTTTACTCATTGTCGTTTTGTGTTTTTTTTTTATTGATTTGTTTTCGAT
TGCATTCGCATTTTTCTGCTCGCTTTTTTGTTCTTGTTTTCCTTCGCATTAATACTTTACAAAATTGAATGTCTATGAGCTAGTATAAATTAAT
TAAATATTATATTCATATCGAGCTATTTATATACTTAGTTTAACTAGCCAGCTAAGTGCATTTAATTAGTTAGTAATACCTACATGGATGGGGTG
GTTTAAGTTAAATGTGTTTACAAAAAAAAATATTTCGTGTGCAAAATTTCATAAATTCCAAGCAACTAAAATCTTTTTCTGTACTTCGTGGGGTT
GGTATGAATTTAATCTAAAACTAAAAGTTAATTTAAGCTTATTTATGTACAAAAAAGAATTTGTTGTTTTGTATGACCATGGAAATGGAAAAACA
ATAGTGGAATTTTTACTGTTGCATTCCAAATGTTTTCCAGCCCTGGTTACCGATTTTCTCGAACTATTATACTGTCCACTTCGCATACGTTTTGG
TCCTGCCCAAAGCAGTATGCAAGCAGTTCAAGCAGTGCTCGCTAGAGAGAAGGAAGGAGCTGCGCGCTTTTTGAATTTTCAGTCTTGTTTTCAAT
GATTTAAAAAGATTTTAAACGACAGCATGAGGAGGGATTCAGCAGAAAGGGGGCGCGCTTCGAAGACTTTAAGCTACACTAAAGTATTTTAAATC
GATTACTATTATCTAGGGGTACAAAAAATGGGGGCTTTGTAATTTACAAAATATTTTGCTTCGATTGGGAGCTGGCTTACATGACTAAAAACTGG
GCAAACACATGTTGTATTCCTCACTTCTTCTTGAAATCTATTCGTTAATATTCCTTGTGTAATACTGCTAAAAAAAAAGTGAGAGCTTAAAGGGT
TTTGCATGGTACACTTCAGGGGCGGTTAGTCGTATCTTTAACTAGGCTATAGTCTAGGTTCTTAAGGTGCTAATAACAAAGGCTAAGCGTAGACA
AAATACATAACACATACAAAGAACGAAGAGGGCGGCTTCAGAGGACGGACTGGGCTGGAGGCGGGCAGTGTCCTTACAGACACGTGTAGATGAC
CTTTTTGGTCCGACACAGCTTGCACTTCACCTCGCAGCACCAGTGGAAGGTGCAGGCGCACCGCTCCACAACGACGACCTCGTCTCGCCGATAGC
CACGCCCACAGCACATCAGCCCACAGCCGTCGACGCCCAGCGAGGTCTCATTGCACTGGCGGCCATGGGTTCCCAGGATGCCCTGCCGCAGGTTC
TTCTCGCAGAAGCTCGGCGAAGGCTCCAGATAGACAAGGTCCTTCGAGCCGGGTGGCTTGTGCTCGGGATTGTGCGGGTTCAGTTGGAAGTGATA
TCTGCAAGGAACAAAACAAGAAGGTAATGAGTAAACATGCTATTTTGTGAGATTACTATAATTTTAAGGCTGTGTTTTTTTTAAGAAATGAAGTT
ATGATTGTTAACAAAAAATATCGTGGTGATTCTTTACCTATTATGCTTGCGTCCCTGACGACGTCCATTTCGTCCGCCCCTTTGACCAGCCTGGG
GCAAACTGTTGGGCGACGGCATGTTCGGGTGATGGATCTTGCTGATCGGGTGGCTGTTCTCTAGCAGGATGTCCGGCATATGGTCGTTCAGCATA
CGCTCCTCCTCCTCGCCGTAGACCAGACCAGACTGCGGAATAATCAGGCCGTTGGAGCCCACGGAATTCGAGCCGGCTGCATTCGGACTAACTGG
GGCCAGAGCGTTGGTGGCCCGGAGACTGTTGGTCACTTGCACGCGGGTGGCTCCATCGAAGCGGGCCTTCAGATTGTCGCCAATCACACGGAAGT
TGGCCAGTCGCATCCAGCAGGTCTTCACTGTACACGATCCGGACATGCCATGGCATTTGCACTCCTGTCGCATCTCCGCTTGGACGTGCTGTAGA
TGAGAAAAGAGCGGGGAGAGATTGTTCATTAGTATGACTTTATTAGGCTTCTTGCGTATCGACTCGCAATATGTTTTTCACTTAATTATTTTGCT
GTTTTTTCTTGGCCGGTTGTTTTTGCCGTTTTGCTGGCTGAATGGCTGGATGGGATGGCTGGCTGGCTGGGAGATTGGCGGCCCGCCTGCCACGT TGTTGCAGTTATTAAAAATCAATAAATGTTGTTGCAACTTGCTGTGCGCTTGTTGCATGTCCCCCCCGAAGTTGCTGTTTGTAATTGTTGTGCGC
GGACCAAAAGTAAGAAATCAACGCAGTTGGGGGCCTTCTCAGTTAGTTCGGTTAGCAGCGGCCGCAGCAGCCCGATGATCATCATCATGCTGATC
GCAATGATTACGGAGCTGCGGCCCATAACAAGTAATAAAATAATAACACAGGCGGTGGGCTCTGCTCCCTCCCCAAAAACGTCGGAGGACTAGGC
CCGGATCCGGAGGGATCGGTCGACTCTAGCTGGATACAGTGCATGTAGTGGATGTTGGCGCAGTGTGCTACTTTCTACGCCCCACTAAAATGGAT
AGCAGGAGTGACGGTGCACAGTGGTTTGGTCAGGCCAAAAAAGTCCATTGCAATATGTGAAAAACTAACTATTATCCCACCATTAAAACTCATTT
ATCGGTAATTAAGAAAACAGCTCTTTTTACATTTCTGTATAATCACAATTTTCTCAACATTCGACCACTGTACCCCTAAAACTAGAGTCCTACTA
TTTTCTTGCATGTGGAGGGGAACTGGAAGCTGTCAACGAGTTAATATACGAGCGACACAAGCGCAAACGAGTGCAGAAATCCCCCCACATTCTCA
TTCGGATGAAAGAGACAGCTGGAGGGGGAGCGAAAGAGAGAGCGCTAATCTCTACAAGCTAGGCCAATTGGCGTTCGGCTCCAATTAATTGTGGG
GACGGAAATTGTCGTCGCTGGTTTTTATTAGCGCTCCAGTCGTAAATCGCCCAGCCAGGCTTAAAACCGAACATTTGGACTACTTATTACGAGGT
ACACTGCGAAAAGAGCATATGAAATAAAGCCAAATCATACCTCATTTCTTATAGTATTGTATAGTAGTATTTTGGCTCTATTTGTATTCGTTTCT
CAGTGTATTAATGCTGGGTATCTAAACTTACCGCTCGACCCGCCTCGTTGTTGTGCAGATTCATCTTCTCGCGCAGATTGCGACCCCTCTCGCCG
GTATCGACGAATTCCCGGGAGAACTTGAACCCGAATCCGATGTTGTCGGAGCAGCCGCCCCACTCCCAATCCCGCACGCCGGCCACACTGCCCGC
CTGGTGGTTCGCTTGTGGAGATCTCGACTGGTGGCTGTAGTCGCAGGTGCAGGACTCTATCGTTCCTTCACTGCAGGCCCTGGCAATCGAGTGGG
TCACCGCCGCGCTGGTGATTGCGTAAATGAAGCTCGTCTCTCGGCAGCCTAGAATGATTACAAATAAAATATTTTAGTTAGTCAAATGTAACATA
TTTTTAGAAAATTAAAATACAGAAATATTTTTTAAGCGAGTGGAATGTCCACATGGCTGATTTCATGAGTTTTCTTCTCTGTGCAGTCATTATTT
TCGCCTTCTGGGTGTTCCACTTGGCACCGAAGACCAATACCGCGACCAAGACAAGATCTCAATCTCGACCAAGTGAAGTGATGGCCGGAGACGTC
GTGGGCAAGAGTTGAAATTTTCGTTATGAGTAATGGCACTTGTCTTCCAAAGCCTGGTCAATTATGACACTTCAAGTTATCAATGCCACGATGGC
ACGGCGAAAAAGAGAGATGAACGCACCAAAACCTGACACAGATTAAACGCTCAACTATAAATTCCAACTTAACACTTTGGGCCCATCTCGGCACA
ATCCATTTTGAGTGGACAGTTTCCCCTTGTGGTCTTTACATTTATTTTTTATTTTTAGTAACTGCCTCCGTTTCTGTTTCGGTTTCTGCTCTGAG
AGCGAGACCATCACAGATAAAGAACAATGAAAATTGAATTTACATGTTGCAGATAATTTTTCAAGTGGTTTCGCCTCGGTTCATAGCTCAAGATA
TGATATATATATAGGGATGGTCCCGCCGGTCAGGTAGCTGAAAATTCCTGGGTAGCGCGTCTTGTCAACCTTGTTTGGAATTTCCAGTTGCGTTG
CGAAGAGCGTTTCAAGTGTAGTATTTATTATTAAATGAATAACTCTTTCCCTATTTGAAATGAGTAGTAACATTTAGAATTTGAAAGGAGCAAGC
CCAACAAAAATCACTGCCTAACTTATTTTCGTTGAGGTGTTGATTGACGCATCTGTGATTGAGTAGTCTGCACTTGAAGATTGACACATTCTAGC
GCTCTCCGTATCACGGAAAACAACTTCCGCTTGGTGTTAGGAATTTTGCCGCTTTTGATTTCGATTTCCTGGAATTCGACCACGAAATAATTTGG
TTTATTTTTTCGAAACTATACCGAAGTGAGCCTCCAATTCCCGGTTAATGTTTGTTTGTTTGTCGTTGGTGGTTTCGTTTTTCCTTAAATAATTT
CACGTATGTAACGAAATTGAAGGCGCACACAGGTAAATTGTGTGTAAATATGTGCAAGATGTTTGGGCCGCGATAAGACGTCGGCGCATGCGCAA
ACGGTATGGGAATCACAGAGGCGGGGGTGCGAGAAGGGATCGGAACGGGGGGCGGAGGAGCGGACTCAGGGGCGTGACACAGTCATTGGTGACTT
TGTTTTTTTTTTTTCTGATGATTAGCTTAGCAAGAATTCGCGTTACCTTTTGGAAGCGAAATGTTGTTTGCATTTCGTACTCTCCTTTTGTGGCT
TTGCTTTCCTCGTTTTATGTGTAAATAGCGAACAAAAGATAATAAATACGAAATATAAAATAAAAAGCGGGGGTGGTGCACCCTGAGCAATTAAG
CAAAGAAAGGGTGTGGCCAAAATGGAGCAACCAAAAAATAAATTTCCGCATGTAATGCGATATGTTTCTGTCTTTCTGTTTTATATAATTGCCAA
AACGGATTTCCGCTGCGAGTGGGCGTGGCTCGAGCTGATTGAAATTGAGAGCAGGACGAAAATCAGAAGCAGGGTGCCTTGCTGATCCTCAGCCC
AGCACCAAAAACCGGGAGTACAGCTCATCTCGGGGTTAAGCTGCTTAGTGACAGCAGCGTCAGCAGTTCCCGGAATAGTTTAGACCTCTTGATAT
AAAACCCACAGGAATATAGGCATAGGAATATGCGAGACACTGGGACTCAGGGACACCCGGGGCGGCTTCGTCACGAACTGATGATTGCCAAAAAG
GGATCTGTACGAGGAACCCAACGAAAATTTACTAATAGAGACAGCCTGTTAAAGCGTGTGGCGTGGCAAATTGACAAGGTGTCACCAATTAGAAA
ACAAGTTAGGCCAGCCCTAGGACTAAAAACGACAAAAAAAAAAAAGAGAACCCAGTCAAGAGACAGGAATTTCGGTATGCCCCGCTGGCAGGGTT
CCTACTTCTTTCAGTTTCCAGCAGTTTGGAAGCCACTGACTCAACTCCGAACCCCAAGTGTTAATGGTGCGCTCTAGGTGTTAATTAGGGCCAAG
GGCACGGCACGGCAAATACATTAAAAATTTGATTGTGGAAAGCGATGAAAGTGCTGCGATAAAAAGCTGTCACCAGGGCAATAATTTCCCTTTTC
TTTTAAAGTACTCCATAAAATGTCGAGAGCTCATAAAAAGGATGTTGGCGGAGAGTCAAAATAACTTGATAAGGTCAAGAGCCTGGCTATAAAAG
TCAGCTGCCGTTGACAGACGGACGCAGCGTAATCGGAATATCGAAGCCACGCGACGCTTGCCACGCCCACTATGAACATATATATAGGGACATCA
GGTAGTTTCAGTTTCAGTTGCAGGATCTCAGGAAACAGGACAAAACAGTAGCTAATAAAACAGCAGGCGAGGGCGGGAGTCGTATGGATTTCCAG
CTAAAAACGCGCTAGGACAAAAACTGCGCATGCGCGACTTTTGTTTACATTGATATAAGAAAAACTGGCCGTTCTCCTGGGATTTTGCTGGCGCA
GCAGGCGAACTAAACTCCCAGAAGACAAGCACGTTTGATTGATTTGAATGACTGAGTGAGTGACAACAGTGGTTCAGTGGTTCCAGTGGTGCTGC
CAACTTGTGCTCATTAGCATAAACACGCTGAAACCGAAACGCAAGTGGAGCAAGTGCAGCGAGCACAGAGCCAACTCTTTGTTCCTCCGACCCGA
TCCGATCCGATTGTCCGTCCAGGGGAAAGTGGCCCCTTCAAAAGGGTAGTCAACCCATATACAAAATATATACATGCTGCCAAGTGCTCAGATCG
TATTACAATAACAAACAAGCGCCACATACATATACCGAAGAGGTCCAGGGGAGTGACATTTCATAACATAAATAAAGGGCCAGTCAAAGGGAAAA
ACTGGATTCGAGCTGGGTTATGCAAGCAATTTGTGTGGTAGCCTTGTTTTCTAGTAGCTAGCTAAGGCAAAAAAGAAGGCGTTGCCAAGAATAGA
TCAGTGGATCATATTTCCCATGGTAAAAGGAGTCTTAAGTGAGTTGCAAGTACTGCGGCAGTTATTAAATGAAGTGTTATTTTTAATAAAGAAAA
AATCATATAGTTAGCTCACCTCGATCAACGATTTTGCCGAATAGATTTTTGCCCCTCGAGAAGTTTCTCGTCGAGCAGTTCCAGCGGCGATTTCT
GAACTGGTGTTGGCACTCGCTAATGGCCAAGTTGGCGCCCTTGACCAGGGCTCCCAGTACACCGGGATTGTCCCTGACCAGGCGTCGCTGTTTCC
TTCTCAACGTAGAGTGGATCGCTGGGTCCATGTACATGATGGGCGTAATGTTGTTGGGTTCGCCGACCTTGGCAATGCCCCTGAAAGAAAATGAG
CCAGAAAACCGAAAGTTAATAGAGCAATCTTCGGAAAGAGGTTGTCAAAACTATTAAATGCTTGGCTGAGTTTTTCGCCTAATTATGAGAACAAG
AATAAAGGGGACGAGGATTTCCACCAGCTGAACGATATTTTTTTTGTCATATTTTCCAGGGGCTTATGTGTCTTTCCACTTGACTTGAGATCGAG
CTGTTTTTCTTTTGGCAGTGCGTATCTTTTTTTTCGTTTTTTCATTTGCGGCTTTTCTGTGTCTTTTCTATTTCGAATATTTGTTGTTTCTGGGC
GGTATACGTCAATTGCCGGCGTTACTCAAGCATAAACCACACAGAAAACGCATATATAAATTAGGTACACTCACACGGGGATGGACAAATATTTG
CAGACACCTGTCGGCTAACGCTTTTCTTCTCTGTGACCTGTCATAATTTATTTTCTTGTTTCAATTGTTGATCTTTATAATATTTTTTCTGCGCT
TCATTAGCAACAACTCGTATATATACATTTATTTTTTCACATAACAAACAATAAACAAGTATAAACAAATGTTTATTGACAGGCAGCGGAGAATG
CAAATTAATTGCCAATTCAATTGAATGCTGATTGCGGTGGGAACCGAACGTTGCGCAATGCAACGAAAATTAATAAAAGTACTTAAATAAAATAA
AAACTTGATCGAAAGTGTAACATCTGTGGGTATCCGCAGGTCAGCGATTGCCAATCGATTTCAATTCCCAGGCGGATTAAATCGATGGCCCGAAC
TGAGATTTATGCGACGGCAATCCGAAGTCGTAGCCGCAATTTGTGTCGTTGTGTTTTATGTATTTGTGTTGATTTTTATTGTTCAGGCCGAAAT
TTATGCCGTTATAAAAAGTTATTAAGGCTTAGCTGAAGTTTTGCACATGATAAAAGTCAAACAAGCAACTCATCAAAGCCGGGGAATCTCTGGGA
GCTGGGTAATAATATCAATGACAAATATCAGTTAGTCCCAAAATGGTTAAAAAGCCTTAGTAAATAATTTGTATTTAACGAAACAAACCATTTGT
TGTTTAATTTTAATCGTATTCGTTCACAATACTTTAGATCAATTTACACTTTCAATAAATTTGTAAAATGCATATCAACAATTTTTCCGCATGCC
AAACGAAAGACTTAGGCAACGAACTTGATTTACTTCATCAATAACTGTTGTTGCATCTCTGCGGTAGATCCCCAAGTCTTGACTTCCTTATCGAG
TCTTTATTGCTCCCCTGCCATTCACCCAAAACCCCATTCATATCTAAAACTGTGTCACACACACACAAAGTTTATCCCAAGTAAAAGTTGAATGC
GCGCTTAGAATTTTTAATTGCTTTCATCAGGCGAGAAGATGAACGAAGTTGAGAAGAAGTCGAAGCTTTATTTCAGTTTTAAGTGTGTGTGCATT
TTGTGGCTTCCGCATTTGGTGCGTGACGCACAAGACCTTTAAACTTTTTTTTTCTTTTGATTTTGTTTGCTTTGTAGGTTTGTTGCTGTGGGAAA
TGTTTCTCGAAATGTTTCGGCGCGTGCCTTGTTGTTGTTCGTTGACTTCTGCTTTTCAATTTTTCCCCGGCTGGTGTTTGCAGATATTATTTTCG
CCCGCCCGCTAATTGCCCAATTTAATGGAAAATATTCAATGAACTTACCACCACATGGAGCCCCGGCCCCTTCCGGATTTCTGTTTGCCCTCGAC
TTGGCTGAGACTGCTGCCGCCGCTGCACAGGGCCATCAGGCAGATGACGAAGATATAGCTGATATCCATTATTGCTGATCGGGTTTATCTGTTCG
ACGGCACACACACTCTCACACTGACACACGGGGTATGATAGATACTTCCCTTCGAGTTGTTGTTTGTTTGCGAATGGTTTGGTTATATTGAATGT
ATCGAGCAATTTCGCGTTCAATTAGCGCACTATAAATGAGGCATAATCATCATTAGCATGCGTATGCCGATATTGCTGCTCATATTTGTGCGATT

FIGURE SHEET 289

AATTCCGCTGGATCACACGGCAATCATGGGACACAACAAGAACTTGTAAGTTTTCCACGCATATACAAATATATATTGTATCGTAAATTTGGCTG
TTTCGATAGAATACACTCGGCTCGCTCTAGTTATAGATGGCTAGTTATAGATCGGTTCGATCGCGGCGTTTCGAGCGGAGGAGTGAAGATTGTTG
CCCGGTTCAGTGCCAACGCTTAACTGAAACACACGGTGCGTTCTTTCGTCCGACTCTGCGTTTGTCAGCAGCGACCCGAGATCCCCGATCCGATC
GCATCGTCGGTCTTCGTCTTCGGATCGCATACACGACCGCCCGATGGTGTGTGTGTGCGAGTGGGGTGGAGCTATACCCTGACTCCTGCATTGCA
GCTGCGTGCGCCAGAAGAGCACCGCTATATGGCGCGGTGATCGTTCGTTCTCCCTGTCTCTTCGTAAACGTTTCTTGTGTGTTGCGCTTTGAAGT
GTGCGTGCGTGTGTGTGTGTGCGGTATATAGCCAGCATGGCCCAATAAGAAATGGCGGAAATGGAAAAACTCTGCCCGGCATTTTCGGTGTAATC
GATTGTATTGCCCGATTATTTGCGCAACCTCATGAATTTCGTCATAGCTTTGACTACATTTAATTATACATATTTGTCGCAATATTTTCGCCTAT
TTCTGTAAGATATTTATGGGATTGGTTTTTTATGGTGATTTTGTTACGCTTACTGTTCGGCTAATAAAGGCTTTGAACTATTATTTTCGACTGTT
GAATTTGGGTTTTATCTTTAGCTTATGGGTGAAAAAGTGGTATTACTACTTTTAACTTCTAGCTTTTGGCTATGAAAGTATTCTTAAATCGATAG
CAACTAAATTTAGCTACTCTATAAATATAAATATTTAGAAACAATTAACAAGAAGTTTCTTTAATATGCCTGTTTCCTTAAACCTTTCCATACAT
TTGCCGTGTCAGAACAAGTTTTCTGCTGCTTTTCGGAGTAAATTTCGGAGTAGTCTTATATACTGCACTTGGATGCAGCCAGCTCCCTCACTCTC
AGGGGATTGTTACCACACACTTTGGCATTCCGAACCGAGTTTATGTCTTACCTTTTCCTCATCCATTGCTTGGCCGCTTCCACTAATTGGACAGT
TTGTGCAGCCCAAGAAGAGCTGGTATCCCACCCCACCTTTAGGGGCTATCTTCCCCACCTA
(SEQ ID NO: 526)

Exon: 10081..9549
Exon: 7870..7620
Exon: 4418..4117
Exon: 2938..2508
Exon: 2376..1001
Start ATG: 9664 (Reverse strand: CAT)

Transcript No. : CT15493
ACTGAACCGGGCAACAATCTTCACTCCTCCGCTCGAAACGCCGCGATCGAACCGATCTATAACTAGCCATCTATAACTAGAGCGAGCCGAGTGTA
TTCTATCGAAACAGCCAAATTTACGATACAATATATATTTGTATATGCGTGGAAAACTTACAAGTTCTTGTTGTGTCCCATGATTGCCGTGTGAT
CCAGCGGAATTAATCGCACAAATATGAGCAGCAATATCGGCATACGCATGCTAATGATGATTATGCCTCATTTATAGTGCGCTAATTGAACGCGA
AATTGCTCGATACATTCAATATAACCAAACCATTCGCAAACAAACAACAACTCGAAGGGAAGTATCTATCATACCCCGTGTGTCAGTGTGAGAGT
GTGTGTGCCGTCGAACAGATAAACCCGATCAGCAATAATGGATATCAGCTATATCTTCGTCATCTGCCTGATGGCCCTGTGCAGCGGCGGCAGCA
GTCTCAGCCAAGTCGAGGGCAAACAGAAATCCGGAAGGGGCCGGGGCTCCATGTGGTGGGGCATTGCCAAGGTCGGCGAACCCAACAACATTACG
CCCATCATGTACATGGACCCAGCGATCCACTCTACGTTGAGAAGGAAACAGCGACGCCTGGTCAGGGACAATCCCGGTGTACTGGGAGCCCTGGT
CAAGGGCGCCAACTTGGCCATTAGCGAGTGCCAACACCAGTTCAGAAATCGCCGCTGGAACTGCTCGACGAGAAACTTCTCGAGGGGCAAAAATC
TATTCGGCAAAATCGTTGATCGAGGCTGCCGAGAGACGAGCTTCATTTACGCAATCACCAGCGCGGCGGTGACCCACTCGATTGCCAGGGCCTGC
AGTGAAGGAACGATAGAGTCCTGCACCTGCGACTACAGCCACCAGTCGAGATCTCCACAAGCGAACCACCAGGCGGGCAGTGTGGCCGGCGTGCG
GGATTGGGAGTGGGGCGGCTGCTCCGACAACATCGGATTCGGGTTCAAGTTCTCCCGGGAATTCGTCGATACCGGCGAGAGGGGTCGCAATCTGC
GCGAGAAGATGAATCTGCACAACAACGAGGCGGGTCGAGCGCACGTCCAAGCGGAGATGCGACAGGAGTGCAAATGCCATGGCATGTCCGGATCG
TGTACAGTGAAGACCTGCTGGATGCGACTGGCCAACTTCCGTGTGATTGGCGACAATCTGAAGGCCCGCTTCGATGGAGCCACCCGCGTGCAAGT
GACCAACAGTCTCCGGGCCACCAACGCTCTGGCCCCAGTTAGTCCGAATGCAGCCGGCTCGAATTCCGTGGGCTCCAACGGCCTGATTATTCCGC
AGTCTGGTCTGGTCTACGGCGAGGAGGAGGAGCGTATGCTGAACGACCATATGCCGGACATCCTGCTAGAGAACAGCCACCCGATCAGCAAGATC
CATCACCCGAACATGCCGTCGCCCAACAGTTTGCCCCAGGCTGGTCAAAGGGGCGGACGAAATGGACGTCGTCAGGGACGCAAGCATAATAGATA
TCACTTCCAACTGAACCCGCACAATCCCGAGCACAAGCCACCCGGCTCGAAGGACCTTGTCTATCTGGAGCCTTCGCCGAGCTTCTGCGAGAAGA
ACCTGCGGCAGGGCATCCTGGGAACCCATGGCCGCCAGTGCAATGAGACCTCGCTGGGCGTCGACGGCTGTGGGCTGATGTGCTGTGGGCGTGGC
TATCGGCGAGACGAGGTCGTCGTTGTGGAGCGGTGCGCCTGCACCTTCCACTGGTGCTGCGAGGTGAAGTGCAAGCTGTGTCGGACCAAAAAGGT
CATCTACACGTGTCTGTAAGGACACTGCCCGCCTCCAGCCCAGTCCCGTCCTCTGAAGCCGCCCTCTTCGTTCTTTGTATGTGTTATGTATTTG
TCTACGCTTAGCCTTTGTTATTAGCACCTTAAGAACCTAGACTATAGCCTAGTTAAAGATACGACTAACCGCCCCTGAAGTGTACCATGCAAAAC
CCTTTAAGCTCTCACTTTTTTTTTAGCAGTATTACACAAGGAATATTAACGAATAGATTTCAAGAAGAAGTGAGGAATACAACATGTGTTTGCCC
AGTTTTTAGTCATGTAAGCCAGCTCCCAATCGAAGCAAAATATTTTGTAAATTACAAAGCCCCCATTTTTTGTACCCCTAGATAATAGTAATCGA
TTTAAAATACTTTAGTGTAGCTTAAAGTCTTCGAAGCGCGCCCCCTTTCTGCTGAATCCCTCCTCATGCTGTCGTTTAAAATCTTTTTAAATCAT
TGAAAACAAGACTGAAAATTCAAAAAGCGCGCAGCTCCTTCCTTCTCTCTAGCGAGCACTGCTTGAACTGCTTGCATACTGCTTTGGGCAGGACC
AAAACGTATGCGAAGTGGACAGTATAATAGTTCGAGAAAATCGGTAACCAGGGCTGGAAAACATTTGGAATGCAACAGTAAAAATTCCACTATTG
TTTTTCCATTTCCATGGTCATACAAAACAACAAATTCTTTTTTGTACATAAATAAGCTTAAATTAACTTTTAGTTTTAGATTAAATTCATACCAA
CCCCACGAAGTACAGAAAAAGATTTTAGTTGCTTGGAATTTATGAAATTTTGCACACGAAATATTTTTTTTTGTAAACACATTTAACTTAAACCA
CCCCATCCATGTAGGTATTACTAACTAATTAAATGCACTTAGCTGGCTAGTTAAACTAAGTATATAAATAGCTCGATATGAATATAATATTTAAT
TAATTTATACTAGCTCATAGACATTCAATTTTGTAAAGTATTAATGCGAAGGAAAACAAGAAACAAAAAAGCGAGCAGAAAAATGCGAATGCAAT
CGAAAACAAATCAATAAAAAAAAAACACAAAACGACAATGAGT
(SEQ ID NO: 527)

Start ATG: 418 (Reverse strand: CAT)

MDISYIFVICLMALCSGGSSLSQVEGKQKSGRGRGSMWWGIAKVGEPNNITPIMYMDPAIHSTLRRKQRRLVRDNPGVLGALVKGANLAISECQH
QFRNRRWNCSTRNFSRGKNLFGKIVDRGCRETSFIYAITSAAVTHSIARACSEGTIESCTCDYSHQSRSPQANHQAGSVAGVRDWEWGGCSDNIG
FGFKFSREFVDTGERGRNLREKMNLHNNEAGRAHVQAEMRQECKCHGMSGSCTVKTCWMRLANFRVIGDNLKARFDGATRVQVTNSLRATNALAP
VSPNAAGSNSVGSNGLIIPQSGLVYGEEEERMLNDHMPDILLENSHPISKIHHPNMPSPNSLPQAGQRGGRNGRRQGRKHNRYHFQLNPHNPEHK
PPGSKDLVYLEPSPSFCEKNLRQGILGTHGRQCNETSLGVDGCGLMCCGRGYRRDEVVVVERCACTFHWCCEVKCKLCRTKKVIYTCL*
(SEQ ID NO: 528)

Name: wingless
Classification: signal_transduction
Gene Symbol: wg
FlyBase ID: FBgn0004009

FIGURE SHEET 290

Celera Sequence No. : 142000013384554
TTATTAATTTTGTTTTTACCTTTGACATTCGTTGGCTTAAATCCAAAGCGTTTTAACCCTCCGCTTTTAGCCAAGTTGAAGGTTTCGTTGAAGAT
TAAAAACAAACTTGCTTGGAGTCCAACCATTTGTTATTCCCTTACTGCGAACATAACAAAAACTATTCATATTTCGATATGATGGACTAAAATAT
TCAGATTAAAAGCGACTAACAATGGTGAAATGGTCGATACTATGCCCTGATATTTAATCAGGGTCTATTGTATTTTTGGTTCTACACTGTACTTT
TAATTTGCGCAAATAATTGATTATTCAGCAATTTTCTTACCAATTTGAATGTTTGAATGTTTGAATGTTCTTTGAATGTTTTACGTAGGCCTTT
ATGTAAACTGCCTGCTTATTCAATGTCATTTACAAACAGCCGCGTTTGAAGCTAAAATTACTTCGTTAGTCAATCTTCTGTTTATGTTTTTTAA
AGCTAAGCCATATTTTTTAAAGTGCTTGAATTACTTCTGGGTGGGGGATAATCAAAATAGATATCGAGATCAGCTTGGTAACAACAAATGTTTAT
AAATAAGTCGAGCTACTTCCAGTTTATGTTGGAGTAGAATGTACATATATCTGCCACGTGCTCGGATCGATTTACAAAAAAACGTTGACCAATGT
GCAAGGCCAAGAAACTCCAAGAATCGGCCACTTGTTGCTCTTTTTGTTCTCTGCTCCCCCGTCTACCACGGTTTCTCTCCTCTTCTCTCTTTCTC
GGTATTCTCTCTGTACATTTCACAAGAGCCGCCGGAGTTTAAGTCTTCAAGTGGCGCTCCATTCGCTTCATGTAGCGATGCCGGCCGGTACAAAA
AATAAGCATAAAATGGAATAATTATAAGGGGAAGCAGAACAAGCAAAGAGTGTACACCGAAAGAAAATGCATAAATTCTGAACTTTAAAGAACCC
TTTTTTTTAATGTCATATATAGCACGCCAAAAAGTATGCCACACTCGATTTTATCCCGGTACTTTAGTCACTTTAAGCATGAGTTTTAGTGGAAC
TTTTATTACAGTGTAAGCAGAGGCGAGTTGTAGAGGAAAGTAAAAGGTTTCTGCCGACAAAAAAGAGCACGGAGCATGGGGAGAAAAGGGAAAGA
GCTCTGCAGTCTGGAAATCGTATGACGATGTGGAATGTTGGGACATGGAAATGGAAGTGCAGTTTACTGGCATTGCCAGACGCTTTGGCTTTCGG
CTGGCAACAAAATTCACATAAATAAAACTTGAGCCGAGTCAGTCGGAGTCGGAGCCTTAGCTAAAATCGGAGTCGGACTGGAAATCGGGGTATGC
ATACGTATGTACACATGGCTGGTGGCATGATCGCCAGAAATGAGAGAGTTGGAGTTGGAGCCACCAACTATAAACACCGCATCCCCTTACACTCG
GAGAAATCGAAGAAGATCCGACAAAGTCGAACCATGATTACGAGCCTTAAGTGTTTACAACTCTCAATTAAGGCTGCAAAGTATATTGTGATTTA
AATTATTTTTCAGTTTAAATTTTGATTATTCTGCACTTTAGTTTTGAATTTTATATTCATAGCTTTTTAATAGATATTTAAAATACGGCAACTCT
TACAAAAATGATTAGTTTTGATATGATGGAAAGCTTAATTTGTGACGTGATGTTAATAGTTGACTAATTCTAATAATTCGCCGGCAATATGTATG
AATGTTTAAGCCTTTCATGAATCATAAAAATAAATACAAGTTGATAAAAAGAGTGACTAAAAGATTTATAACTACAAATACCTCTAGCATTTAGA
ACTTCTAGGAATAAACCATTTTTATGGGCTTGTAAAAACTTACATATGTCCAAAGGAGTGCCGATTTTTCCTGACACATTCAAGAACTTTAAAGG
ATTTCCGTTTAGCACCGAATTAATGGAACTGCCAAAGTGTCCCATCCCGATTCCCATGCCAGATCCTGTACCAGGACTAATGCTGTTGGCTGCCG
CAGGAGCCAGATGCTTCAGCTGATCGAGGGTGGGTCCCAGAGTACTGGCTTTCAGACGCTCTAGCAGCGCCGATCCGCTCAGATTGTGCATTATC
TCGCTGGCAGTGGGCGTGGCAGCGGTCACATGGGCGGCATTTACCGCCGCCGCATTGCAGAATTTGCTGATGCTCAGTATGCAGGTGATGAAGAG
CAGGTGGAACGATGAGGTGAAGCTGAAGCTGATTAGCTGCTGCACTTTGCTCTGGTAATGTGTGCTGGCGCTGTAGAAGAAGCCACTGGTTTTGG
ACGGTTCTCTACAGCCACTGCTGCTGCTGCTTCTGCTGTTGGCACTTTCATTTGTTGTTAACTCTGACTGGGTGGTGGTTTGAAAATATTCC
GTGAAATGCGGCATGCAGGTTGTGGCCATCTTTTGCAGCTGCTCTAGAATATATATACGGTAGAAATTGCACTTTAGGCTCAGTGGGTCACACACGC
TTTTCACTCTGGTTCGATTTGCCAACTTATTTATACACGTCCATTAAATAATAAGTTTAGGCGAATACACGCAACGTTTGCCAAAAAAACGTTCA
CAAAAGTGAGAGAATGAATCGACTGTATCGGGATGAGAGTGTAAGGCATAGGTACGATAAACATGCGGAAAAGGCGATGAAGGGAAAAAGAAACA
TACGATGTTGCGAAAAAACAGCATAAGAGCACAGAAAACACGAAATACACACATAAAACTGCAAGCTAAGGGCGACGCCTTTGGTCAAAGCGAGG
GTTAGCCCCTTATGCTGTCCCTCTCACTCATTTTAAAACATTAAAATAATTTTTTATTTGGATATATCTGCTATCAGCGGTATAACGGTTGATAA
GCCAGGTAAGCCTGGTAAGTCATGCGCAGCCACTACCCATTGACACCATTATTCCAGCTCGGAATGGGTTCTGGTTGTTCAAATCTTGTATTTAC
TTTATTGAATGGCAAAACACATGTTGGACTAAAATTTATGCTGTTTTTTCACATGACATATTGACGTAACGTTCGGCCAAAATAGATTCATACAT
TTTTTTTTAATTAACACTTATTTCCGCTCGACAAATGCGATGAGCTGGCCTTAAAGCCCCGGCTTGAACTTTTTTTTATTTGCTTTGAACTTTTG
CTTTCCGAAACTTTTTTCGCATTCCGAAATTTCTCGGTTTAACGGTGAAGTTATATCCAAAGCATGGGGCGTATGAGCGATAAGCGACCAGCGAC
GACCTAGCGACACGCACTGCGAGTACAAACTGCCGGAATATCGCTTCCGAAGTGAGCGGACCAATGGAACCGTCTTAGAAACTTCGGCAGTGCTC
GTCTTTCGTTCGGCAACGAACCGACGATCGCCACGCGTACCATATCACACCTGCGAAGAGAAAAGAGAGTGTCGACGTCATCATCGGGGGGAGCC
CCAAAGCGTTGAAAATCAAAAGCCTCGATCTCCAACACAAAGAGAAGACAAAGCTACCAGTGCGCAAATAAGCTGACATTGAATCAGAGCTAACA
GGTGGTTCTCTCTTCGGCCGCTCTCTTAGAACGTGTATCAATCTATTTTGGAGGTGTGTTCCACTATTTGTCGTTTCGGCATCCAATTAGTGAGG
TAGCAATTTCTAAAATTACAGGTCTAAATTGTTTGTTGGCCCGGGTCAATCAGTCAAGGCTTCGATTGAAACTAGTAATGGGCTTTGTAGCATAG
ACACACGTAAATCACAATTGGTCAATAAATGTTAAACCATTTACTGTAGCGGAAATTGATCTATTGACAGCACCTGTACCTCTGCATTTCAATTC
ATAACATGGTTTCCATTTGAATAACAAAGATGCTTGAGAAACACGATGGGCTTTTAGCAAGTCTGGATATCATCAAAGTGTAAAATCATCAAGCT
TTGATGAATTATTCCCCTTCGGTACATTTCCAATTGAGATTTCTTCAAGGAACAGAAATATATGTGCATTTTTAACAGCTGTGCATCTGAAGATG
AAACGAAATGCTACAAATTCAGCAAAAAATTGTAAATTGGACAATGTTGGAAATAAAAACTGGAAAAATAGCTGGCAACTTACCACTCACACTTT
GAAATCAATCAAATTAAAATCCCATCCACAAAGTCATGTAATTATATCACAGGAGTACGCTACACATAAGTATGTTCTGAGTTTATTATTCATCA
TATTTTCTTTTTAGTGGGGAAACATATACATATGTATGTACACTTAACAAATACAGT
(SEQ ID NO: 529)

Exon: 3237..3039
Exon: 2404..1849
Exon: 1020..1001
Start ATG: 2404 (Reverse strand: CAT)

Transcript No. : CT15529
CTAGGTCGTCGCTGGTCGCTTATCGCTCATACGCCCCATGCTTTGGATATAACTTCACCGTTAAACCGAGAAATTTCGGAATGCGAAAAAAGTTT
CGGAAAGCAAAAGTTCAAAGCAAATAAAAAAAAGTTCAAGCCGGGGCTTTAAGGCCAGCTCATCGCATTTGTCGAGCGGAAATAAGTGTTAATTA
AAAAAAAATATGGCCACAACCTGCATGCCGCATTTCACGGAATATTTTCAAACCACCACCCAGTCAGAGTTAACAACAAATGAAAGTGCCAACAG
CAGAAGCAGCAGCAGCAGCAGTGGCTGTAGAGAACCGTCCAAAACCAGTGGCTTCTTCTACAGCGCCAGCACACATTACCAGAGCAAAGTGCAGC
AGCTAATCAGCTTCAGCTTCACCTCATCGTTCCACCTGCTCTTCATCACCTGCATACTGAGCATCAGCAAATTCTGCAATGCGGCGGCGGTAAAT
GCCGCCCATGTGACCGCTGCCACGCCCACTGCCAGCGAGATAATGCACAATCTGAGCGGATCGGCGCTGCTAGAGCGTCTGAAAGCCAGTACTCT
GGGACCCACCCTCGATCAGCTGAAGCATCTGGCTCCTGCGGCAGCCAACAGCATTAGTCCTGGTACAGGATCTGGCATGGGAATCGGGATGGGAC
ACTTTGGCAGTTCCATTAATTCGGTGCTAAACGGAAATCCTTTAAAGTTCTTGAATGTGTCAGGAAAAATCGGCACTCCTTTGGACATATTGACT
AAAGTACCGGGATAA
(SEQ ID NO: 530)

Start ATG: 200 (Reverse strand: CAT)

MATTCMPHFTEYFQTTTQSELTTNESANSRSSSSSSGCREPSKTSGFFYSASTHYQSKVQQLISFSFTSSFHLLFITCILSISKFCNAAAVNAAH
VTAATPTASEIMHNLSGSALLERLKASTLGPTLDQLKHLAPAAANSISPGTGSGMGIGMGHFGSSINSVLNGNPLKFLNVSGKIGTPLDILTKVP
G*
(SEQ ID NO: 531)

Celera Sequence No. : 142000013384153
CATCAGTACGCACCAAGAATTCGCAATGATTAACAAAACGGTAGACACCGAGATCTACAATCACAAATATGATAACATAGTTACAGTACACAACA
CTTTCTTCGTAAAAAAACCATTTGTTGTAGTTGCTATCGAATAGTCGAAGTGAGAACTGACTGCTAAATGGCTGAAATAATTGTGACAAATACTA
CCCAGTCTTCAAATTGAAACGCGGAAATGGAACAAAATGTGATGTTGCACTTTTACTTTGCTCTTAAAAAAGTTTTTACTGTAAATAAAATACA
TGTACTGGAATTTTTGTGTAAAATCGACATCGAATTAATTCGATTCCATCAAACACAGCTGACGCAAACATCTGTTAATCTCTTATACAAAGTAA
AGGAGAGTTGTATACCTTTAAAAAACTTTAAAACATTTTTTTATTATGGTATCTTTTTCTAGCTTTTTAGTAGCACACAAGGACGAGGTCCGTG
ATATAAAAATTTTGTTAAAGAGAAGAAGAAGCATTAAATAGTTAAGTGGAAGATAATATATAAAAAAAGTATCCCTCTGTATCCCTCTTTCATCA
AACCTCTTCACGCAACGACGACAATTGTGGTGAACATTTCGTTGCAACCCATCACAAGCAATAAATCAACTGATGACAAGTATACACACATGTTG
ATCCGCAGGCCTGTGCAAAAGTTCGTCAAACATCGATGAGGTGCCACGTGGAACTTACATTTTGCTACGTTGAGATCAAACTTTTTTTTTATTTC
TTTCCGGGCACTAATAAGTGTTTCAATTTATGGACGTTTTGTAAAAATTGCAATAAATTTGTTTATTTACTCGCACATCAAAAAGCAGTTCGTAT
GAGAATGAGAACGTGTTAAAAATTTGGTTGAAATAAAAATGTCGTGTTTCATTTCCATCGTTTCAGTAGCAATAAAAAACGAATCCGATGGCGTA
GATATCGATATACCTGCATTCCCTTTCAAACGTGTTATCGTATTGTTCAGCCAATTGTGCAACGTGTTTGAGTAAATCTGCGGGCGAAAGACTAA
AAATGAAAGTAGAGGCATTGGACAAATTCTGGGCTGACAAGAGCCGCTACGATCTTGCCGAGAAGCGATTCTACGAGGGTCCCCAGAAGGTAAAA
TCTCTAAGCAATCACAGCCATAAGTACTTAAGTTGTTAGCCAGTTTCACGTGGCCGGTAAATCAGTTCAAATGGTTTCGGCAATGTTTATTGCAA
ATCTGTTTGTTTTAACAGCAAGGACGCCGAAACACACATGTTCTAAACTTCAATACATACGTAGAATGATCTATTAAAAGATTTCTATATTTATC
TGCCTTTGATTTTCAATTGCTGTGTTCATATTGCACATTACATTGGTATATTCTTGTAGCTGTATGTAACAGGTGAACGTTTAACACTTTTAAAA
AATATAACTATGTGCGTAAAGTGTATACAAAACAGAGTGTGAGAGAAAACTAACTCTGGCAAGCCAAATTTTGAATACACTTTCCGTTTGGCAAT
TGGTATAAATACAAAATATAGTATGCAAAACATAAGTACTTAACATGACACCTACACAACAAAATTCGTTTATTCAATGGAAATGTGCCAAAAAC
AAATCGATGTATACAAAGTTAAAACCTATTGAAATTCAGGGAAATACTATAGTTAAGTAAAGGTTTAAACACGTTGTATTCTATCTACACAAATA
TACTACACAAAATGCATAGCACTGCATTGTATAATATTTAAACTACGTACAATTTTTGGGCTGATTAGAGTGAGGCTTATCAGTATTTCAGCATG
CTTGCATGACAACAGACTTGAAGTAGATGCCCGTACATAAAACATCTCATTTTGCTTAAAAATTATTATCCCTAGAATCCTTTGTCAACCATTCG
ATACACCAAATGTCAGTTCACACAAGTAATCAATGGTGTTGTCTTATTTTTAAAGGTAACTGATCGCAGCCACTACAGCCCATTAGTAAGCGAAA
TCGCAAAGGCTAGGGAACACATACAGAACTCGCTGGAAAAGGTAACTATTGTGATAAATCTTTGTATTTCAACATTTGATTTGTTCACATTCCTA
GGTTTCTTTCGGTTTCTTTAAAACTTTGTAGAGAATTGTATAATTATTATTTACAATATATTTAGTCTGTACTTATGATCAACATATCCCAATGA
GGACTTGAATTTGAATTATTAATCAAGCCTTTTGTGTGTGTTCCAGATCGATGGCGTTACTCTGGACGATGGCTTAAATTCCGAGCTGGCCAAGC
GTCTGGCCCAATTGGAGGGTGAACACAAGGAGTTGAAGACCCAGGTTTCCTTGTTGAACGAACTTTTGACTGCCACAGTGAAGCGCTTGGAAACT
CAGCTGAAATTGACGAATGGAGTGTCGAAAGAGCCCGAGGTCGAAGCGAAAAAACCAGAAGCGAACGACGACGATGACGATGTGGATCTATTTGG
ATCGGACAGCGAGGAGGAGGATGGAGAGGCCGCCCGCATAAGGGAGGAAAGGCTGGCAGCCTATGCTGCCAAGAAGGCCAAGAAAGTTCAAATTA
TTGCCAAGTCGAACATCATTCTGGATGTTAAGCCGTGGGACGATGAGACCGATCTGAAGGTTATGGAGACGGAAATCCGCAAAATCACCCAGGAC
GGTCTACTGTGGGGAGCTTCCAAATTCGTGCCAGTTGCCTTTGGCATTCAGAAACTGAGCATTTCATGCGTGGTTGAGGATGATAAGGTTTCCAT
CGATTGGCTGACTGAGGAGATCGAGAAACTGGAAGACTTTGTCCAAAGTGTTGACATCGCTGCGTTCAACAAAATCTAAGGGGTAACATATAATT
TTTCAATTCACGATCGGATTTGCCGCATTACAAATGTGTTTGGGAGTCGTCTAAATAAATATTTTGATAAAAACCAACTTAAAAAACTGCATTTA
AACTGGGAGTAATTGGTAAATAGTTTACTTTAGGATATTTTTTATGCAAACGATATGTTTTGAATTCGCTAAAAGGCCATATTATTTCAAAATTT
ATAAGAAAAGAAGATATATATTAGTTTAAGTCATGTATTCGCCATTCTTTGATTAATTAAATTCATTTACGCACGAGTATAAAAACAATGCAAAT
TACCTATTAAATAAATATTCCAGGTCACAGCTAAATTATGCACATATTAATAATGATTAAACTGAGGGACTAGTTTCATAAGGCTCTACAAATTA
TAAATAGTTAATCATAAGTTATTTAACCATCCTAAAGCATAACTTCGTTTTCGGGTCTCGTCGACGTTTGGCGCTTAAACTCACAGCTGCCAGGA
GAATGTCGAAGAGTGGTCATCGCGGTGCTGGTTGGAGCATAGGATTTGGTCACGCCAGCGCGGGTTCTAGTCGATGCAGTGCTCGGATTTGATTG
CAGACCTTAAAGATTAAATAAATACAAATTACATGTAGTATATTCAACTAACTGCCAGTTAATTGATGCCACTGAAACTTACCAAACTTAAACAT
AATTTCGTTATAAATTCTGCGCTTAAACACAAATATAATGAAGACAAAGATTCCAAGTAGCACATTAAACGAATCGCTGATGGTCCAAAAGAACG
TTTTCTTGTGATCATAAAACAAAATGCTAACTATTTCCAACAGCCATGTGATGCCCATTACGAAACACAGTTTCGTGTTCATAACGAATCTGGTT
TTGTCCTGAAAGAATCGCCTTTTCAAAACTGGCTTGTCGCTGTTCAAGCTCTGCATTTTGTATATTTCATTTTTTACTTTGTTGCAATACTTCAT
TGTGAGCACGAATAGAACTAAGTTTATAATGAAAAGTATGCCAACTGGACCCGAAAAGAACAATAAGCTGGCTGAACCAAAAGAATCATCTGGAA
TTAATACAAAAATATACAAATACTTTAATATTTAAATCGTAATTTAATTAGATTTTTAACTTACA
(SEQ ID NO: 532)

Exon: 1001..1134
Exon: 1956..2036
Exon: 2232..2960
Start ATG: 1048

Transcript No. : CT15788
CCAATTGTGCAACGTGTTTGAGTAAATCTGCGGGCGAAAGACTAAAAATGAAAGTAGAGGCATTGGACAAATTCTGGGCTGACAAGAGCCGCTAC
GATCTTGCCGAGAAGCGATTCTACGAGGGTCCCCAGAAGGTAACTGATCGCAGCCACTACAGCCCATTAGTAAGCGAAATCGCAAAGGCTAGGGA
ACACATACAGAACTCGCTGGAAAAGATCGATGGCGTTACTCTGGACGATGGCTTAAATTCCGAGCTGGCCAAGCGTCTGGCCCAATTGGAGGGTG
AACACAAGGAGTTGAAGACCCAGGTTTCCTTGTTGAACGAACTTTTGACTGCCACAGTGAAGCGCTTGGAAACTCAGCTGAAATTGACGAATGGA
GTGTCGAAAGAGCCCGAGGTCGAAGCGAAAAAACCAGAAGCGAACGACGACGATGACGATGTGGATCTATTTGGATCGGACAGCGAGGAGGAGGA
TGGAGAGGCCGCCCGCATAAGGGAGGAAAGGCTGGCAGCCTATGCTGCCAAGAAGGCCAAGAAAGTTCAAATTATTGCCAAGTCGAACATCATTC
TGGATGTTAAGCCGTGGGACGATGAGACCGATCTGAAGGTTATGGAGACGGAAATCCGCAAAATCACCCAGGACGGTCTACTGTGGGGAGCTTCC
AAATTCGTGCCAGTTGCCTTTGGCATTCAGAAACTGAGCATTTCATGCGTGGTTGAGGATGATAAGGTTTCCATCGATTGGCTGACTGAGGAGAT
CGAGAAACTGGAAGACTTTGTCCAAAGTGTTGACATCGCTGCGTTCAACAAAATCTAAGGGGTAACATATAATTTTTCAATTCACGATCGGATTT
GCCGCATTACAAATGTGTTTGGGAGTCGTCTAAATAAATATTTTGATAAAAACCAACTTAAAAAACTGCATTTAAACTGGGAGTAATTG
(SEQ ID NO: 533)

Start ATG: 48

MKVEALDKFWADKSRYDLAEKRFYEGPQKVTDRSHYSPLVSEIAKAREHIQNSLEKIDGVTLDDGLNSELAKRLAQLEGEHKELKTQVSLLNELL
TATVKRLETQLKLTNGVSKEPEVEAKKPEANDDDDVDLFGSDSEEEDGEAARIREERLAAYAAKKAKKVQIIAKSNIILDVKPWDDETDLKVME
TEIRKITQDGLLWGASKFVPVAFGIQKLSISCVVEDDKVSIDWLTEEIEKLEDFVQSVDIAAFNKI*

FIGURE SHEET 292

(SEQ ID NO: 534)

Classification: translation_factor

Celera Sequence No. : 142000013384153
GGTGAGGTAAGCAATGGATCCTTTAATCGTCTAAGTACTCTACGCACCATAAATCACCTGGAAAATGTCAACGATACGCAAGTATTTATCTTTTC
AATTAACTTAAGTCTAGTTATTAGCTGACTTTTTTCCATATATTCTTTCATGACACAAACTAAAATCGCAAACATAAATGTCATTTTTATAATAT
ACAAATCTCCTCTATCGCAAGTACTATTTATTTATTCTAATACAAATATATTAATTTTGTCATTCTCCAATCGGAATAAGTATAAATAAAGTATA
AATCCATTGGTTAAGAAAAGAAAAATCAAAAAAATAATTTTTATTCATTTTAATGTTATTAGTTAGTTTCTAATGTGATCTTTCATTAAATATTT
AATACTTATAAATTATAAATGAAAAGATATTCATAAAAATCGCAGACAATCAAATTAAAGCTTAACTCAGATGTTCTTCTTTCATACACGTTCGA
AATCTTCCTGTCGTTCCTAAGTCCCGTTCACACAGGCAGCTGCTTCATCTGAAATGCAGTTCATATATTGTTTTTGTTATAATTAAACGGTGATT
TTAACCCGGCCGGAGTGGAGTTGCTCATTGGAAATGCTTTTCTAAATTAATTTAAATTTAAAATAACGGCAACAGCAGCTAACACAACAAAAATG
TGAAATATTTGGGTATACATATACACCTACAGGATTTATAAGAGGAAAATTTAAATGCCGATTTTTTTTAAATAAAATAATTCTTGCCTAAATAT
GTGGACTAATTTTAAAACGTTCATTTGTTTTTGTTAAGCCATGTATAAATTTCTACAATATTATTGTTCGTCATTTTGAACTTGCAAAATTTGTT
TCATTCCAACGTTCCAAATCAGGGCAATACATATTTATTATCTACACCGAGTGAAAATATTTTCCGAGTCATCAGAAATTTGTATTATTGATAGC
ATGTTGTAAGGCGACTCGACTATTTTGAAGCTAAGTGAAATTTTATATTGAAACGCAAAGTTGAATACGTGAGCAGTATATGAAAATCGGTGAAT
ACAGTGACTTCATTAGTCAGCCGAAAGCAAAAGAGAGCGAAATACATTTTTTAAACAAACTAAACTAAAATTTCACTGTGAATAATGATGACTGA
AAAGTTAAATTCTGGGCACACTAATTTAACAAGCAAGGGGTTTGTATATTTTATATTTATTTATATTTTTTTTTCACAAGAGGACCCAAGCTTG
GTGTCCCAACAAACATAATATGCATGCGTATTCATCAGCCCATATTTATGATTAGATGCCGAAAAGACAAGCCGTTTTATAGTTTAGAACGTCAA
TTTTTGCAAATGATTGAGCATGTAAAAGCCGAAGATCTGTATTTTAGCAACATCATGTAGTTAGGCTGTTTTCACTCAACAACTAAACCTGCAGA
ACATGTTATCTAATGAAAAAAACCAAACAATGTGATTCCCGTATTTATATTACTTTATTGTATGTAGTAGCGGAACATGTGTACATATGTATAAA
AGAGTTATCTACATATGTAGTTGCACTCGTGGACTTATTTACCGCTAAAAATGTTGCTAAATATAATTGCACTGACTTAAATCATTTAGAAACTA
ACACTGTATTTAGGTAAAACTTCTATTGGGTGATTCTCAACTTTTGAGATCAGAACAAAACAGGTATTTTTTTTTTGCATTTCAGCGCCATGAAC
AGTTATTCGTGGGCTGCCATTTTAAAATTTGGAGTAGCGTTTCTTTTTCTCTCCTCCATAAATGTGCGAAAGAGAAAAAATGTTGAGTTCAATCG
CTTTTAGATTGTTCAGTTCTTAAATATTCAAGACATTATCCATCTTTGTTTACGATTTAAAATCAATATTAACATTATTATTAATATACATTAAT
ACATGGCTTAGACTTTAGCTTAAAATGCACTTTACATAAAAGAACTCATTTACAAAATTTTAAAAATCAAAAATTTTTAATATATATATATGCTT
ATATATGCCATCCATATATATATGGATGTGAATGACCTACATATATCGTAATACTTTAATTACCATTTTATTTTTTTTCTTTTCATCCAGGATTA
TAAATGATCTTCAAATTGCTGGAAACACAAGTGACGATATGGGCTGGAAATCAAAGCTGAAGCTGCCGCCAAAGGACAACCGATTCAAAACAACT
GTGAGTTTGCCGACAAATCAATCGGAATTTATACAATTTAAAGCACAAACAAACTAACAAATAAATGTATTGCCATTGCCTTACTCAGGATGTGA
CCGATACGCGAGGCAATGAATTCGAGGAGTTTTGCCTTAAAAGAGAACTGCTTATGGGTATATTCGAGAAGGGATGGGAGCGCCCTTCGCCAATT
CAGGAAGCAGCTATTCCTATAGCATTAAGTGGAAAAGATGTGCTGGCTCGGGCCAAGAACGGCACAGGCAAGACAGGAGCCTACTGCATCCCAGT
TTTAGAACAAATCGACCCAACCAAGGACTACATTCAGGCACTTGTGATGGTCCCCACCCGAGAGTTGGCGCTACAAACCTCACAGATATGTATTG
AGCTGGCGAAACATCTTGATATCCGGGTAATGGTCACAACGGGAGGTACCATTCTAAAGGATGACATTCTTCGTATTTATCAAAAAGGTGGGTTT
TGATGATAGTTAAATAACCTAATATCGGTTTAATTGCAACTTTCTAAATTTTCCCTACGCCTGCAGTACAATTAATTATTGCCACTCCCGGACGA
ATATTAGATCTGATGGATAAGAAAGTTGCCGATATGTCGCATTGCAGAATATTAGTTTTGGATGAGGCCGATAAGCTATTGTCGCTTGATTTTCA
AGGCATGCTGGATCATGTTATACTAAAGTTACCAAAGGATCCACAGATCTTGCTATTTTCCGCAACATTTCCACTAACAGTCAAGAATTTCATGG
AGAAGCATTTACGCGAGCCTTACGAGATCAACCTGATGGAGGAGCTAACACTGAAGGGTGTCACTCAGTACTATGCATTCGTACAGGAGCGCCAG
AAAGTACACTGCTTGAATACGCTCTTTTCGAAGCTGCAGATCAATCAGTCTATCATATTCTGCAATTCCACGCAACGTGTCGAGCTATTGGCCAA
AAAGATCACAGAGCTTGGATATTGCTGTTACTATATACACGCTAAGATGGCCCAGGCACACAGAAATCGAGTATTCCACGATTTCCGCCAAGGAC
TCTGTCGCAATCTGGTGTGCTCCGACCTGTTCACCCGTGGTATCGACGTGCAGGCCGTGAATGTAGTAATCAATTTCGATTTCCCACGAATGGCA
GAGACATACTTGCATCGAATTGGTCGCTCAGGACGTTTCGGTCATTTGGGTGAGTTTAATTGCATTCTCATATTATAGTTTAGCCTATTTACAAT
CTTCGTTTCTCATTTTAAGGTATTGCTATTAATCTGATAACCTACGAGGATCGGTTTGATCTGCATCGGATTGAAAAAGAACTTGGAACCGAAAT
AAAGCCTATTCCGAAGGTCATAGACCCCGCCCTTTATGTCGCAAACGTTGGCGCATCCGTTGGCGATACTTGCAACAACAGTGATCTGAATAATT
CTGCGAACGAGGAGGGCAACGTTAGCAAATAAAACGGATATGCCCTGTGTAACGCTAGTATCTGAAATAGAGTCTAAATCGTGGAATCAATAAAA
ACAGATGAACTATTTCAGAAATCAAAATTGTATTAAATAAATGGAAAGCAATTCAATTTTTAAATGCGCTCTTAAGATAACTGAAATGACTGGTC
TATAAAAAAAAAGGCTCGTTCACTTTGTGGGTTTTGGTGCTGAGAAGTATTAACATTAACTATTGGGGATTTGGTAAGGAAAGTTAGTCGAATGCT
ATTAAAAGGCAGGCTAAGGTCGTTTAATATCAATCCAGTTTTTAGTAAAGGGTTTAAATCAAATAAAAGGTCTAAAAGTAATTACAGGATTTTCG
GACAAGAGAAGTACACTTGGATCAAGCTAAATCCTAGATTTACTTACATGGAAGAATTACCATTGGCAATTACCCGATTTACTAGATTCCAAAAA
AAAAGTACAAAGGGATCATTATAATTTAAATAAAATTTATTTATTAGCATCCAAAATTGTAAGCTTTGCTTGTCAGAATATTTACAATAAATGTA
CAATATTAAACAAATCATATATATAGGATAGGGTCATAAATTTCAAAACTTTACGTATTAAATATGTTCGATGAGGAGGAAGAGGAGTCGGATTG
GTCAAAGTCGATTTTCGCATAGGTATTCCCATCCTCCGGGCATGCGGACACCGGCGGCGATTCGCGTGATCCTCTCTTCAGGTATTTAGCTGGAT
TTTGGCCACTGCAATGGGGAAGATCTAGGCTGGCGTAGTGCAGCTCCGGCTGGGATATGCGAGACGACGACCTTGAGGGGAAATTCAAATCTTTA
ATCTGTAGAATGTTCTGTGGTGTACTTGGATCTGTGCCAGTGCTACGCGAATCGGCGGCGGCGGCTGGCTTTGCTGAATTTATATTGAATTTGGT
GAGTGAGCTGCTGCTCACCGCGGTGGCGGTGGCATTATCGGGAATCGTATTCACACTCTCTGTAAGTCTCTGCGAACGCTCCAAGTTATCCTTGT
GTATACCCTTTTGGTATAGCTTCGATGAGATGAGTGAGCTGTCGCTTTTAATTTGCAGAATTTTGTAGCCGGCTTCGTTAAATTTTGTGAAATCA
TTCGATTTGTCCTTGATTT
(SEQ ID NO: 535)

Exon: 1001..1179
Exon: 2086..2185
Exon: 2274..2652
Exon: 2727..3374
Exon: 3440..3769
Start ATG: 1133

Transcript No. : CT15802
AAACGCAAAGTTGAATACGTGAGCAGTATATGAAAATCGGTGAATACAGTGACTTCATTAGTCAGCCGAAAGCAAAAGAGAGCGAAATACATTTT
TTAAACAAACTAAACTAAAATTTCACTGTGAATAATGATGACTGAAAAGTTAAATTCTGGGCACACTAATTTAACAAGCAAGGGGATTATAAATG
ATCTTCAAATTGCTGGAAACACAAGTGACGATATGGGCTGGAAATCAAAGCTGAAGCTGCCGCCAAAGGACAACCGATTCAAAACAACTGATGTG
ACCGATACGCGAGGCAATGAATTCGAGGAGTTTTGCCTTAAAAGAGAACTGCTTATGGGTATATTCGAGAAGGGATGGGAGCGCCCTTCGCCAAT TCAGGAAGCAGCTATTCCTATAGCATTAAGTGGAAAAGATGTGCTGGCTCGGGCCAAGAACGGCACAGGCAAGACAGGAGCCTACTGCATCCCAG
TTTTAGAACAAATCGACCCAACCAAGGACTACATTCAGGCACTTGTGATGGTCCCCACCCGAGAGTTGGCGCTACAAACCTCACAGATATGTATT
GAGCTGGCGAAACATCTTGATATCCGGGTAATGGTCACAACGGGAGGTACCATTCTAAAGGATGACATTCTTCGTATTTATCAAAAAGTACAATT
AATTATTGCCACTCCCGGACGAATATTAGATCTGATGGATAAGAAAGTTGCCGATATGTCGCATTGCAGAATATTAGTTTTGGATGAGGCCGATA
AGCTATTGTCGCTTGATTTTCAAGGCATGCTGGATCATGTTATACTAAAGTTACCAAAGGATCCACAGATCTTGCTATTTTCCGCAACATTTCCA
CTAACAGTCAAGAATTTCATGGAGAAGCATTTACGCGAGCCTTACGAGATCAACCTGATGGAGGAGCTAACACTGAAGGGTGTCACTCAGTACTA
TGCATTCGTACAGGAGCGCCAGAAAGTACACTGCTTGAATACGCTCTTTTCGAAGCTGCAGATCAATCAGTCTATCATATTCTGCAATTCCACGC
AACGTGTCGAGCTATTGGCCAAAAAGATCACAGAGCTTGGATATTGCTGTTACTATATACACGCTAAGATGGCCCAGGCACACAGAAATCGAGTA
TTCCACGATTTCCGCCAAGGACTCTGTCGCAATCTGGTGTGCTCCGACCTGTTCACCCGTGGTATCGACGTGCAGGCCGTGAATGTAGTAATCAA
TTTCGATTTCCCACGAATGGCAGAGACATACTTGCATCGAATTGGTCGCTCAGGACGTTTCGGTCATTTGGGTATTGCTATTAATCTGATAACCT
ACGAGGATCGGTTTGATCTGCATCGGATTGAAAAAGAACTTGGAACCGAAATAAAGCCTATTCCGAAGGTCATAGACCCCGCCCTTTATGTCGCA
AACGTTGGCGCATCCGTTGGCGATACTTGCAACAACAGTGATCTGAATAATTCTGCGAACGAGGAGGGCAACGTTAGCAAATAAAACGGATATGC
CCTGTGTAACGCTAGTATCTGAAATAGAGTCTAAATCGTGGAATCAATAAAAACAGATGAACTATTTCAGAAATCAAAATTGTATTAAATAAATG
GAAAGCAATTCAATTTTTAAA
(SEQ ID NO: 536)

Start ATG: 133

MTEKLNSGHTNLTSKGIINDLQIAGNTSDDMGWKSKLKLPPKDNRFKTTDVTDTRGNEFEEFCLKRELLMGIFEKGWERPSPIQEAAIPIALSGK
DVLARAKNGTGKTGAYCIPVLEQIDPTKDYIQALVMVPTRELALQTSQICIELAKHLDIRVMVTTGGTILKDDILRIYQKVQLIIATPGRILDLM
DKKVADMSHCRILVLDEADKLLSLDFQGMLDHVILKLPKDPQILLFSATFPLTVKNFMEKHLREPYEINLMEELTLKGVTQYYAFVQERQKVHCL
NTLFSKLQINQSIIFCNSTQRVELLAKKITELGYCCYYIHAKMAQAHRNRVFHDFRQGLCRNLVCSDLFTRGIDVQAVNVVINFDFPRMAETYLH
RIGRSGRFGHLGIAINLITYEDRFDLHRIEKELGTEIKPIPKVIDPALYVANVGASVGDTCNNSDLNNSANEEGNVSK*
(SEQ ID NO: 537)

Name: DEAD-box helicase
Classification: RNA_binding
Gene Symbol: me31B
FlyBase ID: FBgn0004419

Celera Sequence No. : 142000013384326
ATCACCAAGAGCAGTGCCTACGGAGCCTGCTACCTGGGTGCGGATAGTGCGGACTTCGATCTTCCGAGAAACTATGCCGACAACGTCACAGTACT
GTACACGTACACCGATCCTCGAAAGAAAGCCAAAGCCACCAACGGCTGTAACTGTTAGATAAATTGTGTTTGACAACCCATTCCGCAATACACTT
CCCAATTGCCAAATTCGCAATCAATATTCCAGTTAGTGGTACGGATAGGTAGTATTATAGCTTATCAAAAAATAAATAATTTTATCCTTTGACGA
AATCCGCTGGAAAGTAAAGAAGTTTCCCTTTCAATCTTGCATCAAACTCACCTACATATACTTTCTAAACTTTTTTTGTTGGGTTTGTTAGAAAT
ACGTATGAAAATTTTATTCGATAATGTTCATTGTATTAATTGTATGTGTCTCAATTGTTGGCTGTCGTGGCTTCTTTTCATGTATGTGGGCATAC
ATGTGCGGCATCTTCTTTGTAATACTTTGATTGTGTTTAAAGCCAATTTGTTTTTATTTTCGCAGTGCTGTCAATTCAATTCTTTGGCTAATTTG
ATTCTCGAATCGGGAAGCAGAACATAAATGTATCTGTTTGTAGCGAAGGAATACATAGGCCAAAAACATAATATCTTAGGGAGCTTAGAATAGAG
TATTTGGGATAATGTACGAGTAGCTGAATCGAATGCCGTAGCAAGTGAATCAAAATTACATCTACATGTATATATATATAATTGCTTGGATAAAA
CATTTAACGTACTGTAAGATTGAATGCGACATACCAAAAGAGATTTTCAATAAAATCGAATTCAAATAGAACCAAGACCGCCACTTTGACTAAAA
AAACTGTCAAAGTTTCGGCAGCATAGCCAAGAAAACTTGGCTTTTCGGCTTCTACGTCGCTGTTTTCCTGGGGACTAATTCATCTGCGATTAAGT
GTAACCTATTTGTATGCGATTAGCTTAAATGCATCCCTTTCCGGGCGACTTCAATTGTTTATGCTCTGCCGCAGCTTCTGGGGATCCTGGTAGTG
CGACGAGGACGATATGACCGAGGGATGCTGAGGCGGTGGAAAACACCGCACGTGCTCCACATTTGAGCCCTCGCCATCGCCGCCCTTTAGATACT
TGTTGAGAATGGAGAAGATTTGTGAGTTTAATACTTGGAACCGACGAATCCGATCCACCATTCGCTTCAATTGCTGTTAAGGAATATTCAAATTG
TACTTTGGGCACTTTGGTAGTTATGTTAGAACTTACAATGCCCTTTACGTCCTCATCCTTGCCATCGACGCGCTGTACCCGCAGAATGTGGTAGC
AAAAGTCCAGAGCCTCGAAGCGACGCTGCTGTCCCAGCAGTACGATCATGACGCAGCCAGCCCAGTTCAGACCTTCGCCGAAGAGCTCCTCGATG
GTGTACTCCGTTCCCCTGACTGGAATGCAATAAACGAACTGCAGAGCCGACCAAAGGCGATGGAACTCCGAGCACTCATCCACGTGGATAATCCC
GTTGGCCGGTGGAGGACCACACCACACAGGGTCGTCCAAATAGCTCTTCACGCGGTTGAGAATAACTTCAAAAATGCTGAGGCCACAGCAAAGAC
GCTCACGAGTCAGCAAATCTCCCTCTCGTGCTATCATTGCTTGCTGTTGGTAAAGATTATTATTATAAAGTTAATCAATTAAGTTTGGGGGCTCA
CCTTTGCAGTGCCAATCTTTTCCACGTTTGAAACTATCTGCAGATTGGCAAACTGTGCTTCAAGACGCTTTTGCTTAGCCTCCGGTTTTTCATTC
TCTGAAATGGGTAGAGATGTAAGTAAGAAAAACTACCCATGAAAGCATCCACTTGTACATACCTTTGCAAAAAGGTCTGGGAAAGATGTTCTGGA
AGAGGGCGGCGTGCAGTAGATCGCACACCTCCTCCTGCGAGAGCGCCTGTTCGATCAGCAGGCAAAAGATAATGCTGTTGCCAAACTCCCGGAAA
GACTGAAATAGCTCTGTCTTCGCGTCCGGATATTGCACGATGTCTGTAAGATGAGCCTGATAGTAGCTGAGCACTCCAGGCGAACCATATTCGCA
ACGGGGTAGTTTGCATGACTTGGGCATGGCAATCATCAGCGTCTTGGTGAACTGCAGCAGCGAGCCCTGGATCAGTGGCTTAACAATGTCCTTCA
GTATAATGTCCATGACGACTGCTATGCCCTGATAGCCCAGCAGGCGGCACATGGCATGGAAATGCGGTGAACCTACAAAGCCAGTGTACTGGCCA
TACTGTGTGGAATAGGCAGCATTCAGCTGCTTGGAACCCCACAGATAGTAATGGGACATTTGTGGCGGCTTCTCACGCTGAATAGCCTGTGACGA
CGAAAGATTCACTTTGGTTCGAATGAAACTGCAAGAGATAATAGTAATAATAAGTATTTTAAACAATAGAAAATTGGCGGCACACCCACCGATTC
GTGGCTGCATTATAGCAGTAATTGACCAGAAAGTCGTAGTTCAATTCCACAAAGACGTGCAGTGTTATTCTGCCGTAAGGCGCCAGTACATTGTG
GTTAGCCTCCTTTACCATGCCGTCAAAGTTATCCAGGGCCAAGTACTTGCTTAGCAACTTGTGGCAAATTCGATTCGCCTCTAGCAGGCCTTCGA
GTTCCTGAAATTAAGCGAATTAGAGACCGATTCTAGACATCTGTAGGATTCCACTTACCACAATGCCGGTTATATCGTTGCCCTCGAAACGACTG
ATGGCCAACTCAATGCTCTTGTGCATGTTGGCGTTTATGCGTTGTGTGATCAGTTTGTTCAAGTCAATAGAACGGCCTTAAACGAATGGAGAAAC
CATTAACCAAAAGATCATGATGCAATGGGTGTTTTGCTTACCCAAAAGTTGGACATGTCGTTGTTTTAACAAGGTCTCATAACGATTATTGCGGG
GATACGACTGGAAGTTGAAACCGAGTACCTCGCACTCCAAACGGAATCGCTTGTCCAAGAAGATGCTGCCCGCCAATTGCTTGTAATGGGCAAAG
ATCTGCTCGCTCAGCTTGTAGACAAACTGATCGAAGCACAGATTGACTTCGGCCTCCACTTCGTCGTACAGGAACTGCTTTCGGAAGACAGTGAG
TGCGTAGTACGCCGAGTCGTTGTACAAGTCCAGGGGATACAAGACAAATCTGTGTGAGGCACTTAGTTAGTTCAGATCATTTCACCTATTCGCCA
TTTACTTACTCCATCATTGAGGGCTCCTTCGTTTGCAGAATGTGATCGGTTAGGATCCAGGGCATGGACATTTCAATCGGAAACTGAATGCGCTT
CTCCATGGTGATCAGATCCTTGCACTCCTCGTTGTGCTGATGCCGCACCAAGCACTTGTTAACCTTACGACCCATGGTCATCTCCAAGTAGAACT
CGCGATACCACAGCTGCGAGAGATCGCAGCACTTCTGAAGCGTGTCGCTGAAGTTGAGCAAGTAGCTCCAGTAGAACGATGTCTTGTGGAACGTG
TCGATCTGCAGCAAACAGTTTCCGTCGATGTCCTTGCGCAAAGTGCGCTTGCCGCCGCTTTTGTCGGCAATCAGAGACTCCAGCATGGTGCGCAC
CATGTATAGCTGAGTGGAGGAAGGTCCCACATTGAGGCGAGGCACCTGGATGCGGAAGCCGCCGTCGGGATCCTTCTTGCCCTTGGCCACTGGAT CGTCGGTGGGCTCATAGCCCTTTTGCCAGTCCGCCGATGTCTCTCGCACCGACATGATGATGCTCCGGATAAGATCCTTCTTATTTTTTACGGCC
TTTCGCAGCGGTTCACGAAGCGAAAGCTGCACGAAGTCCTGCAGCTCGGAATAGATGTTACGCCGGATAGCCTCGCACAATACGGTTTCAATGCG
CGCCATTAGCACCTGCAGTCCCTTTATCATGGCGATGACCTCGATCAGCGCGAACTTCTCTTCCGAGGTGTAATTGTAGCGGGTGGCCCGCTCGT
ACTCCTCAGCCTCCACGGGGCACTCCTTGTTCTGGTGATGATCAGTCGGATGCAGGAGCTTCCAGGAGTACAACTCGGTGACCACACTGGTCCAC
TCGGACAGCAATTGAAGGCCGCGCAGAGCCAGGTCGGCCGTAATCCGGTTCTCGGCATCAGAGGGATTCTCCTTGACGGTGGTGGTCACCTCGTT
TGTGTATCGCGCCAGCTCCGAAATGTACTTGACGTGATCCTCGCGTATCTGCGGCAAATGCACCATTAGATCCGCCTGTGGGCTGATGGCGTTTG
AGCTGGACAGCGGCCACTTGCTGGAATCGAAGTGCTTGCTGCGCTTTATGTAGTTGAAGGGAGCAATCTGCATGTCGCCGAAGAGGGGCACCACT
TCCAGGTTCTTAAAGATGCGATCGATGCGATCCAGCCGTATCTTCTTCTTTTGATCAAGTTTGTTGATATTGCACGCATCGCTGTCCATAAGGAA
CAGGCCAAAGCCCATAACTTTTACCAGCATGTGCTTCTCCTCAGGGGTCAAGTACATCTTTGTCTCGAACATATGCACGCAAATGTTGACCACAT
CTGAGAGCAGATCCTCGTAGCCCACGATCTTCTCCAGCGTGTCCTTGACCGTGTCGCGAATCTTGTTCTGCGTGGCCAGGAACATGGACAGATTC
TGCGACTCCTGCAAGGTGTGCGAGTCCGACATCACTTTGAGGAACTGCGCAGCTCGCCTGTAGGTGGAGTAATCGTTCTTCACGCTGGACTTCAT
GTTCTTCAGCTCGTCCAGCACGGCAAACATGTTGATAAACTTGCCTAGCGTCAATAGGTACGCCTCGGACACGAAGTCCTTGCGCTTCTCGGCGT
GGCACAAGCGCTTCACCTCGCCGGAGAAGGCCTCGATGGCCTTGCGTTGGAAGTACATGAAGTTGAGCAGCTTGTTCACCTCCGGGGCTAGCACC
TCGACCGTCTTCTCGTAGATCTCCACGCGATTCGGCTGCTCATTGGACTTGGGCTGCGGAATGGCGCGCGAGCAGCAGCGCCAGGTGTAGAGCAT
TACTGCGTGTTTCTGCCCCTCGTCCAGGAGCACATTCTGCGGGCGGAGAGAAGGGGTTCAGAGCTGTGAGTAATGCTAATGCGATAAGCCGGATA
CGCTAACTCACCAAGTTGGCATGGGTGGTGGCCTCCTCGATGTACTTGGCGATACCCGTGACAAATCCATTGCGATCCTCGAAATTCGTATCGAA
GTTTGCCTTGTAGATAATCGAGCAGGGCTGCGCCTCGATGCAGGGCTGCTCGTCCGGCAGGGATAGCTCGTCCAACACCTCCACGTTGGACAGCG
CGTCGGCTAGCGTAATCTTCTCCGTCATGCTGGGCTGCTTATCATGCTCCAGCAGCGCGAAATGGTTAAATTCTAACAAGGCGGGGCCCCAATCC
AATCGACACAAATTTTTTTCGCCACAAATACAACACGACTTTTACCATTCGCCTGGGTGCGTGGACACGTGGCCATAATTAGCACATTTTTGCTG
GCGGTTGGCGTCTACGATGTGCTTATGCTTATATGGCTGCGCACCGCTAATTTCGATAAGAGAAAGATAATCGATAAATACGGCGCATTGGCGGC
ACATCACATCACTAGCGTCTGTGGTTCCGTTTCGTTTTAGCGAACTCAATTTCTCCTATTTTATATTGCATTTTCCGTTAAGAGTAGCCTACAAT
TCTGCAAGATGTCGATGTTTTGGGGTAAGTCGAACTGATCTCACTTGCCCCCTCCGGGCTGGTTGTGCCAACGAGCTCTTGGGTGCTCCGACCGC
GCTTTTATTGCCACCACGTGCTTGCCGCTCGATTTACCGGCAGCGTGGAGCGGCGCCATTTGCACGCCGATGTAAAGTAAACCATGTTTTTGACC
AACTGTGTCCTCTTCCAGGTTTGAACATGAAGCCTGAGCGCAAGTACTCGCAGACGATCATCAAGTCGTTCCACATCTCGGGCGTGGCACTCGAC
AAGGGCCAGGAGGCCAAGTTGTACCTCGCTGCCGAGAAGCAGGAGTACATCGTGGCCACCGTGACCAAGGCCATTCCACAGGTTGCGCTCGACCT
GAACTTCAGCAAGGGCGATCGCATCATGTTCTACACCGCCGGTAAGACCTTTTATGTCCACTATGTTCGCATGTTTATCCGTTTCTGACGCTTTC
GTTCGTTTCACAGGCGACGCCAGCGTTTCTCTGTTGGGCTACTTGCACGACATTGATTCCGAAGATGATGAGGATGACGATCAAATGACGATCGA
GAATTTGCTGAACTCCAAGGCGATCAAGAATAGCAAAAAGTCTGAAGATGATGAGGATGAGAATGAGAGCGGCGAGGAGGACGAGGAGGATACTG
ATGACGATAGCCAGATAATCGAGGAATACGAGTCCTTCCTCGAAAATGGTGAGGAGGAAGATGACGACGATGTTGATGAGGATAACGAGGAGA
(SEQ ID NO: 538)

Exon: 5458..5142
Exon: 5071..3240
Exon: 3184..2892
Exon: 2831..2719
Exon: 2664..2465
Exon: 2403..1868
Exon: 1806..1712
Exon: 1658..1272
Exon: 1213..1001
Start ATG: 5348 (Reverse strand: CAT)

Transcript No. : CT15834
AAAAGTCGTGTTGTATTTGTGGCGAAAAAAATTTGTGTCGATTGGATTGGGGCCCCGCCTTGTTAGAATTTAACCATTTCGCGCTGCTGGAGCAT
GATAAGCAGCCCAGCATGACGGAGAAGATTACGCTAGCCGACGCGCTGTCCAACGTGGAGGTGTTGGACGAGCTATCCCTGCCGGACGAGCAGCC
CTGCATCGAGGCGCAGCCCTGCTCGATTATCTACAAGGCAAACTTCGATACGAATTTCGAGGATCGCAATGGATTTGTCACGGGTATCGCCAAGT
ACATCGAGGAGGCCACCACCCATGCCAACTTGAATGTGCTCCTGGACGAGGGGCAGAAACACGCAGTAATGCTCTACACCTGGCGCTGCTGCTCG
CGCGCCATTCCGCAGCCCAAGTCCAATGAGCAGCCGAATCGCGTGGAGATCTACGAGAAGACGGTCGAGGTGCTAGCCCCGGAGGTGAACAAGCT
GCTCAACTTCATGTACTTCCAACGCAAGGCCATCGAGGCCTTCTCCGGCGAGGTGAAGCGCTTGTGCCACGCCGAGAAGCGCAAGGACTTCGTGT
CCGAGGCGTACCTATTGACGCTAGGCAAGTTTATCAACATGTTTGCCGTGCTGGACGAGCTGAAGAACATGAAGTCCAGCGTGAAGAACGATTAC
TCCACCTACAGGCGAGCTGCGCAGTTCCTCAAAGTGATGTCGGACTCGCACACCTTGCAGGAGTCGCAGAATCTGTCCATGTTCCTGGCCACGCA
GAACAAGATTCGCGACACGGTCAAGGACACGCTGGAGAAGATCGTGGGCTACGAGGATCTGCTCTCAGATGTGGTCAACATTTGCGTGCATATGT
TCGAGACAAAGATGTACTTGACCCCTGAGGAGAAGCACATGCTGGTAAAAGTTATGGGCTTTGGCCTGTTCCTTATGGACAGCGATGCGTGCAAT
ATCAACAAACTTGATCAAAAGAAGAAGATACGGCTGGATCGCATCGATCGCATCTTTAAGAACCTGGAAGTGGTGCCCCTCTTCGGCGACATGCA
GATTGCTCCCTTCAACTACATAAAGCGCAGCAAGCACTTCGATTCCAGCAAGTGGCCGCTGTCCAGCTCAAACGCCATCAGCCCACAGGCGGATC
TAATGGTGCATTTGCCGCAGATACGCGAGGATCACGTCAAGTACATTTCGGAGCTGGCGCGATACACAAACGAGGTGACCACCACCGTCAAGGAG
AATCCCTCTGATGCCGAGAACCGGATTACGGCCGACCTGGCTCTGCGCGGCCTTCAATTGCTGTCCGAGTGGACCAGTGTGGTCACCGAGTTGTA
CTCCTGGAAGCTCCTGCATCCGACTGATCATCACCAGAACAAGGAGTGCCCCGTGGAGGCTGAGGAGTACGAGCGGGCCACCCGCTACAATTACA
CCTCGGAAGAGAAGTTCGCGCTGATCGAGGTCATCGCCATGATAAAGGGACTGCAGGTGCTAATGGCGCGCATTGAAACCGTATTGTGCGAGGCT
ATCCGGCGTAACATCTATTCCGAGCTGCAGGACTTCGTGCAGCTTTCGCTTCGTGAACCGCTGCGAAAGGCCGTAAAAAATAAGAAGGATCTTAT
CCGGAGCATCATCATGTCGGTGCGAGAGACATCGGCGGACTGGCAAAAGGGCTATGAGCCCACCGACGATCCAGTGGCCAAGGGCAAGAAGGATC
CCGACGGCGGCTTCCGCATCCAGGTGCCTCGCCTCAATGTGGGACCTTCCTCCACTCAGCTATACATGGTGCGCACCATGCTGGAGTCTCTGATT
GCCGACAAAAGCGGCGGCAAGCGCACTTTGCGCAAGGACATCGACGGAAACTGTTTGCTGCAGATCGACACGTTCCACAAGACATCGTTCTACTG
GAGCTACTTGCTCAACTTCAGCGACACGCTTCAGAAGTGCTGCGATCTCTCGCAGCTGTGGTATCGCGAGTTCTACTTGGAGATGACCATGGGTC
GTAAGGTTAACAAGTGCTTGGTGCGGCATCAGCACAACGAGGAGTGCAAGGATCTGATCACCATGGAGAAGCGCATTCAGTTTCCGATTGAAATG
TCCATGCCCTGGATCCTAACCGATCACATTCTGCAAACGAAGGAGCCCTCAATGATGGAATTTGTCTTGTATCCCCTGGACTTGTACAACGACTC
GGCGTACTACGCACTCACTGTCTTCCGAAAGCAGTTCCTGTACGACGAAGTGGAGGCCGAAGTCAATCTGTGCTTCGATCAGTTTGTCTACAAGC
TGAGCGAGCAGATCTTTGCCCATTACAAGCAATTGGCGGGCAGCATCTTCTTGGACAAGCGATTCCGTTTGGAGTGCGAGGTACTCGGTTTCAAC
TTCCAGTCGTATCCCCGCAATAATCGTTATGAGACCTTGTTAAAACAACGACATGTCCAACTTTTGGGCCGTTCTATTGACTTGAACAAACTGAT
CACACAACGCATAAACGCCAACATGCACAAGAGCATTGAGTTGGCCATCAGTCGTTTCGAGGGCAACGATATAACCGGCATTGTGGAACTCGAAG
GCCTGCTAGAGGCGAATCGAATTTGCCACAAGTTGCTAAGCAAGTACTTGGCCCTGGATAACTTTGACGGCATGGTAAAGGAGGCTAACCACAAT

FIGURE SHEET 295

GTACTGGCGCCTTACGGCAGAATAACACTGCACGTCTTTGTGGAATTGAACTACGACTTTCTGGTCAATTACTGCTATAATGCAGCCACGAATCG
TTTCATTCGAACCAAAGTGAATCTTTCGTCGTCACAGGCTATTCAGCGTGAGAAGCCGCCACAAATGTCCCATTACTATCTGTGGGGTTCCAAGC
AGCTGAATGCTGCCTATTCCACACAGTATGGCCAGTACACTGGCTTTGTAGGTTCACCGCATTTCCATGCCATGTGCCGCCTGCTGGGCTATCAG
GGCATAGCAGTCGTCATGGACATTATACTGAAGGACATTGTTAAGCCACTGATCCAGGGCTCGCTGCTGCAGTTCACCAAGACGCTGATGATTGC
CATGCCCAAGTCATGCAAACTACCCCGTTGCGAATATGGTTCGCCTGGAGTGCTCAGCTACTATCAGGCTCATCTTACAGACATCGTGCAATATC
CGGACGCGAAGACAGAGCTATTTCAGTCTTTCCGGGAGTTTGGCAACAGCATTATCTTTTGCCTGCTGATCGAACAGGCGCTCTCGCAGGAGGAG
GTGTGCGATCTACTGCACGCCGCCCTCTTCCAGAACATCTTTCCCAGACCTTTTTGCAAAGAGAATGAAAAACCGGAGGCTAAGCAAAAGCGTCT
TGAAGCACAGTTTGCCAATCTGCAGATAGTTTCAAACGTGGAAAAGATTGGCACTGCAAAGCAAGCAATGATAGCACGAGAGGGAGATTTGCTGA
CTCGTGAGCGTCTTTGCTGTGGCCTCAGCATTTTTGAAGTTATTCTCAACCGCGTGAAGAGCTATTTGGACGACCCTGTGTGGTGTGGTCCTCCA
CCGGCCAACGGGATTATCCACGTGGATGAGTGCTCGGAGTTCCATCGCCTTTGGTCGGCTCTGCAGTTCGTTTATTGCATTCCAGTCAGGGGAAC
GGAGTACACCATCGAGGAGCTCTTCGGCGAAGGTCTGAACTGGGCTGGCTGCGTCATGATCGTACTGCTGGGACAGCAGCGTCGCTTCGAGGCTC
TGGACTTTTGCTACCACATTCTGCGGGTACAGCGCGTCGATGGCAAGGATGAGGACGTAAAGGGCATTCAATTGAAGCGAATGGTGGATCGGATT
CGTCGGTTCCAAGTATTAAACTCACAAATCTTCTCCATTCTCAACAAGTATCTAAAGGGCGGCGATGGCGAGGGCTCAAATGTGGAGCACGTGCG
GTGTTTTCCACCGCCTCAGCATCCCTCGGTCATATCGTCCTCGTCGCACTACCAGGATCCCCAGAAGCTGCGGCAGAGCATAAACAATTGA
(SEQ ID NO: 539)

Start ATG: 111 (Reverse strand: CAT)

MTEKITLADALSNVEVLDELSLPDEQPCIEAQPCSIIYKANFDTNFEDRNGFVTGIAKYIEEATTHANLNVLLDEGQKHAVMLYTWRCCSRAIPQ
PKSNEQPNRVEIYEKTVEVLAPEVNKLLNFMYFQRKAIEAFSGEVKRLCHAEKRKDFVSEAYLLTLGKFINMFAVLDELKNMKSSVKNDYSTYRR
AAQFLKVMSDSHTLQESQNLSMFLATQNKIRDTVKDTLEKIVGYEDLLSDVVNICVHMFETKMYLTPEEKHMLVKVMGFGLFLMDSDACNINKLD
QKKKIRLDRIDRIFKNLEVVPLFGDMQIAPFNYIKRSKHFDSSKWPLSSSNAISPQADLMVHLPQIREDHVKYISELARYTNEVTTTVKENPSDA
ENRITADLALRGLQLLSEWTSVVTELYSWKLLHPTDHHQNKECPVEAEEYERATRYNYTSEEKFALIEVIAMIKGLQVLMARIETVLCEAIRRNI
YSELQDFVQLSLREPLRKAVKNKKDLIRSIIMSVRETSADWQKGYEPTDDPVAKGKKDPDGGFRIQVPRLNVGPSSTQLYMVRTMLESLIADKSG
GKRTLRKDIDGNCLLQIDTFHKTSFYWSYLLNFSDTLQKCCDLSQLWYREFYLEMTMGRKVNKCLVRHQHNEECKDLITMEKRIQFPIEMSMPWI
LTDHILQTKEPSMMEFVLYPLDLYNDSAYYALTVFRKQFLYDEVEAEVNLCFDQFVYKLSEQIFAHYKQLAGSIFLDKRFRLECEVLGFNFQSYP
RNNRYETLLKQRHVQLLGRSIDLNKLITQRINANMHKSIELAISRFEGNDITGIVELEGLLEANRICHKLLSKYLALDNFDGMVKEANHNVLAPY
GRITLHVFVELNYDFLVNYCYNAATNRFIRTKVNLSSSQAIQREKPPQMSHYYLWGSKQLNAAYSTQYGQYTGFVGSPHFHAMCRLLGYQGIAVV
MDIILKDIVKPLIQGSLLQFTKTLMIAMPKSCKLPRCEYGSPGVLSYYQAHLTDIVQYPDAKTELFQSFREFGNSIIFCLLIEQALSQEEVCDLL
HAALFQNIFPRPFCKENEKPEAKQKRLEAQFANLQIVSNVEKIGTAKQAMIAREGDLLTRERLCCGLSIFEVILNRVKSYLDDPVWCGPPPANGI
IHVDECSEFHRLWSALQFVYCIPVRGTEYTIEELFGEGLNWAGCVMIVLLGQQRRFEALDFCYHILRVQRVDGKDEDVKGIQLKRMVDRIRRFQV
LNSQIFSILNKYLKGGDGEGSNVEHVRCFPPPQHPSVISSSSHYQDPQKLRQSINN*
(SEQ ID NO: 540)

Name: SHYC-like

Celera Sequence No. : 142000013384668
CAGCGGCTGCGACGGCACCACCGCCGCCCACCGGCATCGAGGAGAGCTTCTCGCGACCCTCCTTGATCAGGTCGTCGATGCTCTTGCCAGCCAGC
TCCTTGATGACCTTGGTCAGACGCTCGGCGTCGACCTCAACGCCCACAGAGCTGAGGATCTTCTCCAGATCGCTGTTGGCGGGCGAGTCCTTGCC
ACCGAGGACGGCCAGAAGGTAAGCAGCCACGTAACGCATGTTTAAGTCTTGGGTTCTTGACACGAAACGTGAATTGGCAAAATGTACGAAAAACA
CAACTTTCCTTTGCAAGTTGTCGTCGAAAAAGAGGCGGAAGTCAGTGTGGCCGCGCGGTCGAGGCTCGAAAATACCAGCTCATACTTATATATAC
CAAAGTATACCACATCCTTATCTAGCAATACCCCTAATGAAACGATAAATTCAAATATTATTTTCAATTTTGCTTTTAAATAAAAATTAGAGCAA
TATTATTGATTTTTGAACAATTTGGTGTGTTTTTTTTATATTTACAACATCAAAAGTATTTATATTAGCTTAATAATATGACCTTTCTTACAGC
ATGGAAATGTTATCAGTTGCAACACTGGGTTTCAAACTTGGCTATCGTAATAGTGGGAAGCACTTTGCTCTTGCAGTAGGCGGTCACACCATTTG
AAACGGTTCTGTTAGGCGAGGTCTAACATACTGTTAAGTGCTGGAAAGAGAGCAAAATGAGAGTGATCGTAAGCTAAGAGAAGGAACTAGGGATG
CGTAAAAGTTAACAGCTGGCTATCGATGATTAACATGACCATCGTTTTAACAGCAGAACTTAACTGTTATTTGTACACATAAATATAAAACTGTA
ATAAAACTCGAAAAAGCTGTATAAAAAATAAATTTTTTTCGAAAATATGTTTAATATGAGATATTTATTATTCTTCAAAAACACTTTAAATTTAA
GTTGCACCCCCACTTGAAATAAATTGCAGAAAAGACATGAGACCCATCTTATTGTATGCTGTATATATAATTGCATATATAAATGATTGTTGTAC
AAAATTTTGAAATTGTATAATGCATTCCTGAACTTTGTGTATCACATTTCGATTTGGAGGGCCTTCAAACGCCCTCGAGAATCGTTTCACATGTA
ATGGTCATCAGATAGTTGATCGGCAGTAGTATTCACACTTAACTTACGACTACAAACAAATTAAGGTATTCTTTATTCCGGATCCGTATCCCCGG
ACACAATAACTGGACTGTCGCGAAAAAATAAACAAAATGCTTCACTACACTTAAAGGAACATTGGTAACAAGAACGAAGCGCGGCCGCAATGATC
AGTCCACTGCCACTTTCACTTCCACATCCATAATCCATAATCCATAATCCATAATCCATTATCCATTATCCTTCTGGGCATCGAGACTATAGGGG
TTCCTGCTGAAAGTAATCGTGCTCCAAACAGGCCAAGGCGGATGGTCGCAGGTGGAGGTCGTAGGAAAGCATTTTCTGCGGGCAAACATAGGGTA
TGCGTTAGTCTAGACCATGCAACAAGATATGTATCTTCATTTTCATACTCACATTCAACAGATCATCGGCGTACTTGCACAGGTGTGGGCAAAAG
TCTTTTGGTCTCTTTGGATGCCGCTGGGGAAAGTGTTCCAGGGCCACGGAAATGGTCTGTGGCCACTGTTGCTCGGTGGGTCTACCGGTCAGTCT
GCGTGAAATCGCATAAATGTAATTAAAAATCACCGATTTCAATGGCAGTATTTGTGCACTCACTCGAAGATGCGGTCCAGCTGATTCTTTTCGGA
GGTGCCCCGGGAATAGGGCGCGCCGATTGAACATCTCGAAGATGATGCAGGCGGCACTCCAGATGTCCACGGTGCTGTTGTAGGGCTGGGCGAGCA
GAACCTCGGGTGCGCGGTACCACAAGGTGACCACCACGGAGGTGAGCTTCATCTCCGAACCGTAGGTCTTGGCCAAGCCAAAGTCGGCGATCTTG
AGGTGGCCCTGCGAGGAGACCAGCAGGTTTTGCGGCTTAAGATCCCGATGGATGATACGGTGTGAGTGTAAGAAGTCCACACCGGTCAGTAGTTC
CCTTGACAAGCGCTGCAATAGGAAATAATTTCATATACCATTTTCTGAAATTTTGATATCATTTTGAGACCCACCTGAATTGTGGGCGGCGACAT
GCCCGATTTGGGAAGTCTGTCTATAAGATCCGAAAGATCCTGCTCCACATGTTCGAAAACCAACAGAATCAGCAATTGGCCGTCGCGCTCCAGAA
ACTGGCATACTTCGTACAGTCTGAAAGAGAGGGGAAGTGCAATCTTTGTATGTACAAATTGTTTGATTTTGTGTGCGACAGAGAGCGATGTATGG
GGGAAATGTTGAGAGATATAAAAAAAATGTGTCATAAAATGCTGCTGGTTGTGGTGCGCCAATACGCCATTGGCCATACTTTGTTCGTTTCGGGA
ACTACGCGAAGCACTCGAGACAAACACATGCGCACATGGCGATCAAAGAGCCAAAGAGAGCGTCCAGTAAGAGAGGCTACAGATCGTTTTCGGAC
AGAGGCAAAACGTAAACGTTAGCAGAGCAGATTAGCATTATGTTATGTTAGCATTATGTTAGAATCAGTTCGGGCAGTTATTTTAACATTGCCTT
TGAATTACTTAAAAGGCACAGTTTTATTGAAACCTTCTACTGTTACACTTGCTTTAGCAACTGGCACATTGGGTTTTTAAAAATACAGATAAATA
CAAGAAACTTAATTTGCCATTGATTTATTTCTTGTACCCCTCCAACACTTTTGGCTTCAAACAAAATAACAGCTGCACTTTGTAGCCATTTGCAA
CTTAACTTAACATTCTGTTGTGCGAGATCTCTCTCTCTCTCTCTCTCTGTCGATCTCTTTGTACTGTATTCGCGTCGCGCTCTCACGCTGCTA
AAGTGCAAGCGAGTGCGCACATCGATAACGCGCGACAGCAACATGTGGTTATCGAGCTGCTCTGTTAATTCAAATTCCTAACGGCCGCCGCAAAC
AAACATAATGCCAATACAAAATCGCCCACATTTGCGAACTGCAGTGATCAGTTATCAGCGGGAGCGGATCGACTTGCTTCAGACTTACTTGACTT GACTGGCATATGTCAGAAGCGAGGGCGTTCGCCGGGGGCAAATCGTCGGAATATTACGGCTATAGCATGCACAGATAAACACAAGCGCGCTGACA
TTGCGATGCGGCTCTTTACAAATGAGTTTGGCAAATAGCTTTGGCGCCGCCACTTGGCCCCAATGGCGGGTGATAACACCCCTCATATACAGCTA
GCTAGCTATAGTTCTACATAAAGTACTCAACTCCAAGGCCATTTAGAAGCCCACTGCCCTTGTGGCAGCGTGTAAATCACCCATACTCACTTGAC
AATATTCGCATGATTGCTGGCATTCAGCTGCTTCAGCAGCGAAATCTCCCGCAGCGTGGACATTGGCACACCGTTCTCGTTCAGCGATATCCTAA
CCTTCTTCAGCGCCACTATGTTGCCGGTGATCACATCGCGGGCTCTGTAAACCGTTCCATAGGCACCTGAAAAGTGGATCGAAATTGTACATCAA
AATGCTTACAACGGGAAATAAATGCGAAAGACAGCCGAAAATAGAATAAAATAAAGTCAGCTGTGCCGATAAGATAAATGGCAGAAATCAGAGAG
GCGAGAGAAAGAGAGAAGGTGCCACTTAGCTTCTTCATATCATTATGGTGTATTTATACTTTTCATATTCAACATCGTATTTATAGCCCTTACGA
TTGAAGTGACTTGATTTATTTGCCTTGTTCGATGAACTAACTGTTTATAATGATTGAATGAATAGACAATGAATGCATTTAGCCCAAAAGAATCG
TATTGCAATGCATGCAATAATTGCATATATTAGAGACTATATTATATGCACTCAAAATTAGTCAAAATATTGCACGAAATTCAGACTAATTTCCT
CATGAAACTGTTGCTGTCTCAGGTACAACGTGATCTTAATTTCTACATGTTCACGGGCAAAGAAAAACGACAAGAGACGAGCAAAATTCCCAATC
AGAATCAAATTCTGGCATGCCAGAGAAATGTCACCGAAAATTTATCACCCGTACGGACAAATGGACAAATGGACAAACGGACGGACGGACGGACA
TGCGTGGGGGGTAGAAAAGCTAGAAGGCACCGGCTATTTCGGTTGACACTGACATACAGAAACAGCAGATATGTACTGATACACCCGAAATAAAC
GCAACTTGAGGGGGGGGGGGGGTGAATTTGGTTTTCCGTCCCTTTGTCACCGTCTCTAGACCACCTGGCTTATGAACTGTGCCGCTGTTGCTACA
TTCAAGTACAAGGCCGTGAGCTCGACTCGTTTTTGAACGTCGGCAACTGGTCTGTCCAATTGGAATTGTCAAAAAAATATACAAATATACAAGCA
AAATAAACTCGAAAAATTGCGCAAAGAAAACAACAAAGCAAAGCACTATGGGAAATTTACGCACTTTATCTGGCCGAAAACCGATTAATATATGT
AATATTAAATGCATGCATTTAGTTACAACGGTGACTACTGTTAGGCAATGCAAAAAAGTTAATTGAATGACTATCTGCAAACTAAAAAATATATA
TTATATATCATTAAAAATATGGGCTAGTGTAAGGCAATGCAAAAAAAGTTTGGAGTTAGTTTGGCCACAAAAAGTGGTCAAATTTTCCATAGTAC
AAAGTAGCAAAAATGAGACTGAGCGAAAGCGAATAATAATTGAATGAATGTGCACAGAAAGGCAGACAGCCGAAAGTTTGAGTGTATGTGTGTGT
GTGTGCGTTGTATAACAGATGAAATTGTGCGGACCCATGACTCGCACAACACCCAGTAACAATATCCATCATTAGCATTCGCCTGCCCATGATGA
TCGGCATGATCGGTGACGTAATTGATTTGGGCTTTATTTACAGCAAACAAGCGATCGTAATTACTGACCACAAAAAAAAAAGACCATGAGCCACT
TGTCAGATCATCATGGATGTGAGATCGGCAGAAACACGTAGTCCGCCGAGAGTGGACCTAAAAGTATGCAGGTAGAAGGTGTAGGATCCAATACA
GGGGAGTTTTCCATCCAATATTTCCCCTTTTCGCGGAATTTCCACGCTTAATTAGTAAAGGGGTAAAAAAACAACAACATTCCTCCAAGTGCACT
TGTCATTTCAGCTTCATAACAATGTCGGAGCTCCCGATTGATCGTAAACAGTAGTGAAACCAAATAGCCCAGACTTTGTAAGCAAATTAAAGTAA
TCAAACGTTAACAACAAGCGACCAGCAAACGAAAGCCTCTCGTGCGAAGAGAGCCGGACCTATCCCAACAACAAAGCAACCGCGTCCCATTATTA
AATCCCACCCAAGTCGCTCACCTTCGCCGATGATGTTGAGCTCCTGGTAGTTGAACGGATCGCCATCGCCGAACTTCTTCGCCTGGGACATTTTC
TGCCGCTTCAGCTGGCGTACATATGACATTTAGCTGGATTTTACGGTTATTTGCGTATTCCTCTAATATTCCGGGTAATCGAAACCGTTAGTTGC
ACCAGCTGGAAGTGAAGGGGTGTTTTTTTTTGGTTATCGATCGTCTGCATGTCACGTATCGATATGTCCTTGTGTCCCCACGCGATAGTTCACA
CAGATCGTAGCGTGAGAGGGAGAGTGCGAGTGCGTGAGAGAGAGAGGGAGGGCCTTACCTGATTTCATACCTGTTGCCTTTTCTAGATAACCCCA
AAACTGGCGATAAAGACTGGTGTGACAGGTGCGCTAATGGAAGAAGTCTGGCTATATGCTCCGCTATGCTTTTCTATCTCCGAGAACCGAAAACC
GAAACATATACATGGACAACTACATATGTATGTATGTATGTAGATGGCGGCGGTCGTTGAACCGCGTTTAATGTTTTCGTACATACTCCGTTTTT
ATGTCTAACCAATCGCAGAACGGCAAAGGCCAACACTAGTTATGACTTATTCATGTTATTCAGTGACGCTGCTCGCCGTCTCCGTTTTGCGGCTT
CGTTCGTGCATCCTGTTGCTCTTATTCGAGCTTGACTGTGAACGCTGTACTGGTTATCTACTGTCGCGTTAGTTGGCGTGTGTCCACTATTCTCT
CCTATCTAAAGTGCTACCACTTTTCTGTCAGTGCATTTTTTTTGCCCGAAAAATATACATATACCGCAAAAAAGAACCCGAATACAATGTATTTT
GTTGCTGGCATTTGTCAATTAATTCTAATCGCGAGACAAGCGAAACAACAATAATAAGCGACACAGTCACAAAACTGGGTAGAAAGAGAGTGTCC
AGAATTGTGAAAGGTATTACGAGGTATTACGAGCTGTATATTTGGGTCTAAAATACATAGTTATTGTTGCACCAGTTTTCGCCCCCTCTCTCTCC
CTCGTCATCCCTCTCTCGCTCACCATTTGCGCTCTACTGATAAGGAAATTTCGGCTTCACTTTACTTTTTTTTCGGTGAACTTCAATGCCAATGT
TGTCGTTTTTCTTTCAACCGTTGTGCGAAATATTAGTTAAATATTAAGAAAATGTGGTTTTTATTTGCGAAGACTCGAACACACACACAACGCCG
CTAAGTGATTTCGCTTGAGAGATCGGTCTTACACACACACACATACACAAACACAAACGCACACACCGAGTGGTACACACACACAGGCGCAGGTA
TTATGTATACATATATGATTTTTATTCGCTTTGACGAAATTTTGGCATTTGTTGATAATCCAGCTAGAACCGCACGATAGGAGCAACGCGACGCG
AATTTTCGGTGCGAACACGGTTCAGTTGCCGGCAGTCGCACTTTAATTAAGTTTTTAAAACGTCTTATAAATTTTTACCAATATTCGTAAGAGTT
GAGTGATTTTGTGTTTTGTTGTTGGCACAGCTCTGGAAACTGTTTTAGATGGTCTACTTAACAGTGGCTTCTCTTCGCCTGTTATCGCCCGCTGT
TAGCAAACAGACGGCCGCTAACATTGTGCTGTATACGTCCAATCGGTTAAACGGTTAATTTCGAAATTGCTGCCAGCGATCGTTATTGAATGTTA
TTCCAATTCGATAACGTAAGTGTTATTGTGTTATACTAATGTTATTGATTTCTGGGAATTTGATATTTTCAACTTGTAATAATGCCCAAATTTAT
TTTTTTTGCAATGTGAATTTCAGGCATTTATATATGTAACATATATAAATTACAAATAAATAAATAATAATAAACATAATGAAAATAATATTTGA
AAAAAATTTTTA
(SEQ ID NO: 541)

Exon: 6327..5759
Exon: 5610..5437
Exon: 3581..3416
Exon: 2300..2165
Exon: 2102..1774
Exon: 1708..1573
Exon: 1500..1001
Start ATG: 5539 (Reverse strand: CAT)

Transcript No. : CT15896
TTATTATTGTTGTTTCGCTTGTCTCGCGATTAGAATTAATTGACAAATGCCAGCAACAAAATACATTGTATTCGGGTTCTTTTTTGCGGTATATG
TATATTTTTCGGGCAAAAAAAATGCACTGACAGAAAAGTGGTAGCACTTTAGATAGGAGAGAATAGTGGACACACGCCAACTAACGCGACAGTAG
ATAACCAGTACAGCGTTCACAGTCAAGCTCGAATAAGAGCAACAGGATGCACGAACGAAGCCGCAAAACGGAGACGGCGAGCAGCGTCACTGAAT
AACATGAATAAGTCATAACTAGTGTTGGCCTTTGCCGTTCTGCGATTGGTTAGACATAAAAACGGAGTATGTACGAAAACATTAAACGCGGTTCA
ACGACCGCCGCCATCTACATACATACATACATATGTAGTTGTCCATGTATATGTTTCGGTTTTCGGTTCTCGGAGATAGAAAAGCATAGCGGAGC
ATATAGCCAGACTTCTTCCATTAGCGCACCTGTCACACCAGTCTTTATCGCCAGTTTTGGGGTTATCTAGAAAAGGCAACAGGTATGAAATCAGC
TGGTGCAACTAACGGTTTCGATTACCCGGAATATTAGAGGAATACGCAAATAACCGTAAAATCCAGCTAAATGTCATATGTACGCCAGCTGAAGC
GGCAGAAAATGTCCCAGGCGAAGAAGTTCGGCGATGGCGATCCGTTCAACTACCAGGAGCTCAACATCATCGGCGAAGGTGCCTATGGAACGGTT
TACAGAGCCCGCGATGTGATCACCGGCAACATAGTGGCGCTGAAGAAGGTTAGGATATCGCTGAACGAGAACGGTGTGCCAATGTCCACGCTGCG
GGAGATTTCGCTGCTGAAGCAGCTGAATGCCAGCAATCATGCGAATATTGTCAAACTGTACGAAGTATGCCAGTTTCTGGAGCGCGACGGCCAAT
TGCTGATTCTGTTGGTTTTCGAACATGTGGAGCAGGATCTTTCGGATCTTATAGACAGACTTCCCAAATCGGGCATGTCGCCGCCCACAATTCAG
CGCTTGTCAAGGGAACTACTGACCGGTGTGGACTTCTTACACTCACACCGTATCATCCATCGGGATCTTAAGCCGCAAAACCTGCTGGTCTCCTC
GCAGGGCCACCTCAAGATCGCCGACTTTGGCTTGGCCAAGACCTACGGTTCGGAGATGAAGCTCACCTCCGTGGTGGTCACCTTGTGGTACCGCG
CACCCGAGGTTCTGCTCGCCCAGCCCTACAACAGCACCGTGGACATCTGGAGTGCCGCCTGCATCATCTTCGAGATGTTCAATCGGCGCGCCCTA TTCCCGGGCACCTCCGAAAAGAATCAGCTGGACCGCATCTTCGAACTGACCGGTAGACCCACCGAGCAACAGTGGCCACAGACCATTTCCGTGGC
CCTGGAACACTTTCCCCAGCGGCATCCAAAGAGACCAAAAGACTTTTGCCCACACCTGTGCAAGTACGCCGATGATCTGTTGAATAAAATGCTTT
CCTACGACCTCCACCTGCGACCATCCGCCTTGGCCTGTTTGGAGCACGATTACTTTCAGCAGGAACCCCTATAGTCTCGATGCCCAGAAGGATAA
TGGATAATGGATTATGGATTATGGATTATGGATTATGGATGTGGAAGTGAAAGTGGCAGTGGACTGATCATTGCGGCCGCGCTTCGTTCTTGTTA
CCAATGTTCCTTTAAGTGTAGTGAAGCATTTTGTTTATTTTTTCGCGACAGTCCAGTTATTGTGTCCGGGGATACGGATCCGGAATAAAGAATAC
CTTAATTTGTTTGTAGTCGTAAGTTAAGTGTGAATACTACTGCCGATCAACTATCTGATGACCATTACATGTGAAACGATTCTCGAGGGCGTTTG
AAGGCCCTCCAAATCGAAATGTGATACACAAAGTTCAGGAATGCATTATACAATTTCAAAATTTTGTACAACAATCATTTATATATGCAATTATA
TATACAGCATACAAT
(SEQ ID NO: 542)

Start ATG: 641 (Reverse strand: CAT)

MSYVRQLKRQKMSQAKKFGDGDPFNYQELNIIGEGAYGTVYRARDVITGNIVALKKVRISLNENGVPMSTLREISLLKQLNASNHANIVKLYEVC
QFLERDGQLLILLVFEHVEQDLSDLIDRLPKSGMSPPTIQRLSRELLTGVDFLHSHRIIHRDLKPQNLLVSSQGHLKIADFGLAKTYGSEMKLTS
VVVTLWYRAPEVLLAQPYNSTVDIWSAACIIFEMFNRRALFPGTSEKNQLDRIFELTGRPTEQQWPQTISVALEHFPQRHPKRPKDFCPHLCKYA
DDLLNKMLSYDLHLRPSALACLEHDYFQQEPL*
(SEQ ID NO: 543)

Name: Cyclin-dependent kinase 4/6
Classification: protein_kinase
Gene Symbol: Cdk4/6
FlyBase ID: FBgn0016131

Celera Sequence No. : 142000013384668
CAGCGGCTGCGACGGCACCACCGCCGCCCACCGGCATCGAGGAGAGCTTCTCGCGACCCTCCTTGATCAGGTCGTCGATGCTCTTGCCAGCCAGC
TCCTTGATGACCTTGGTCAGACGCTCGGCGTCGACCTCAACGCCCACAGAGCTGAGGATCTTCTCCAGATCGCTGTTGGCGGGCGAGTCCTTGCC
ACCGAGGACGGCCAGAAGGTAAGCAGCCACGTAACGCATGTTTAAGTCTTGGGTTCTTGACACGAAACGTGAATTGGCAAAATGTACGAAAAACA
CAACTTTCCTTTGCAAGTTGTCGTCGAAAAAGAGGCGGAAGTCAGTGTGGCCGCGCGGTCGAGGCTCGAAAATACCAGCTCATACTTATATATAC
CAAAGTATACCACATCCTTATCTAGCAATACCCCTAATGAAACGATAAATTCAAATATTATTTTCAATTTTGCTTTTAAATAAAAATTAGAGCAA
TATTATTGATTTTTGAACAATTTGGTGTGTTTTTTTTATATTTACAACATCAAAAAGTATTTATATTAGCTTAATAATATGACCTTTCTTACAGC
ATGGAAATGTTATCAGTTGCAACACTGGGTTTCAAACTTGGCTATCGTAATAGTGGGAAGCACTTTGCTCTTGCAGTAGGCGGTCACACCATTTG
AAACGGTTCTGTTAGGCGAGGTCTAACATACTGTTAAGTGCTGGAAAGAGAGCAAAATGAGAGTGATCGTAAGCTAAGAGAAGGAACTAGGGATG
CGTAAAAGTTAACAGCTGGCTATCGATGATTAACATGACCATCGTTTTAACAGCAGAACTTAACTGTTATTTGTACACATAAATATAAAACTGTA
ATAAAACTCGAAAAAGCTGTATAAAAAATAAATTTTTTTCGAAAATATGTTTAATATGAGATATTTATTATTCTTCAAAAACACTTTAAATTTAA
GTTGCACCCCCACTTGAAATAAATTGCAGAAAAGACATGAGACCCATCTTATTGTATGCTGTATATATAATTGCATATATAAATGATTGTTGTAC
AAAATTTTGAAATTGTATAATGCATTCCTGAACTTTGTGTATCACATTTCGATTTGGAGGGCCTTCAAACGCCCTCGAGAATCGTTTCACATGTA
ATGGTCATCAGATAGTTGATCGGCAGTAGTATTCACACTTAACTTACGACTACAAACAAATTAAGGTATTCTTTATTCCGGATCCGTATCCCCGG
ACACAATAACTGGACTGTCGCGAAAAAATAAACAAAATGCTTCACTACACTTAAAGGAACATTGGTAACAAGAACGAAGCGCGGCCGCAATGATC
AGTCCACTGCCACTTTCACTTCCACATCCATAATCCATAATCCATAATCCATAATCCATTATCCATTATCCTTCTGGGCATCGAGACTATAGGGG
TTCCTGCTGAAAGTAATCGTGCTCCAAACAGGCCAAGGCGGATGGTCGCAGGTGGAGGTCGTAGGAAAGCATTTTCTGCGGGCAAACATAGGGTA
TGCGTTAGTCTAGACCATGCAACAAGATATGTATCTTCATTTTCATACTCACATTCAACAGATCATCGGCGTACTTGCACAGGTGTGGGCAAAAG
TCTTTTGGTCTCTTTGGATGCCGCTGGGGAAAGTGTTCCAGGGCCACGGAAATGGTCTGTGGCCACTGTTGCTCGGTGGGTCTACCGGTCAGTCT
GCGTGAAATCGCATAAATGTAATTAAAAATCACCGATTTCAATGGCAGTATTTGTGCACTCACTCGAAGATGCGGTCCAGCTGATTCTTTTCGGA
GGTGCCCGGGAATAGGGCGCGCCGATTGAACATCTCGAAGATGATGCAGGCGGCACTCCAGATGTCCACGGTGCTGTTGTAGGGCTGGGCGAGCA
GAACCTCGGGTGCGCGGTACCACAAGGTGACCACCACGGAGGTGAGCTTCATCTCCGAACCGTAGGTCTTGGCCAAGCCAAAGTCGGCGATCTTG
AGGTGGCCCTGCGAGGAGACCAGCAGGTTTTGCGGCTTAAGATCCCGATGGATGATACGGTGTGAGTGTAAGAAGTCCACACCGGTCAGTAGTTC
CCTTGACAAGCGCTGCAATAGGAAATAATTTCATATACCATTTTCTGAAATTTTGATATCATTTTGAGACCCACCTGAATTGTGGGCGGCGACAT
GCCCGATTTGGGAAGTCTGTCTATAAGATCCGAAAGATCCTGCTCCACATGTTCGAAAACCAACAGAATCAGCAATTGGCCGTCGCGCTCCAGAA
ACTGGCATACTTCGTACAGTCTGAAAGAGAGGGGAAGTGCAATCTTTGTATGTACAAATTGTTTGATTTTGTGTGCGACAGAGAGCGATGTATGG
GGGAAATGTTGAGAGATATAAAAAAAATGTGTCATAAAATGCTGCTGGTTGTGGTGCGCCAATACGCCATTGGCCATACTTTGTTCGTTTCGGGA
ACTACGCGAAGCACTCGAGACAAACACATGCGCACATGGCGATCAAAGAGCCAAAGAGAGCGTCCAGTAAGAGAGGCTACAGATCGTTTTCGGAC
AGAGGCAAAACGTAAACGTTAGCAGAGCAGATTAGCATTATGTTATGTTAGCATTATGTTAGAATCAGTTCGGGCAGTTATTTTAACATTGCCTT
TGAATTACTTAAAAGGCACAGTTTTATTGAAACCTTCTACTGTTACACTTGCTTTAGCAACTGGCACATTGGGTTTTTAAAAATACAGATAAATA
CAAGAAACTTAATTTGCCATTGATTTATTTCTTGTACCCCTCCAACACTTTTGGCTTCAAACAAAATAACAGCTGCACTTTGTAGCCATTTGCAA
CTTAACTTAACATTCTGTTGTGCGAGATCTCTCTCTCTCTCTCTCTCTCTGTCGATCTCTTTGTACTGTATTCGCGTCGCGCTCTCACGCTGCTA
AAGTGCAAGCGAGTGCGCACATCGATAACGCGCGACAGCAACATGTGGTTATCGAGCTGCTCTGTTAATTCAAATTCCTAACGGCCGCCGCAAAC
AAACATAATGCCAATACAAAATCGCCCACATTTGCGAACTGCAGTGATCAGTTATCAGCGGGAGCGGATCGACTTGCTTCAGACTTACTTGACTT
GACTGGCATATGTCAGAAGCGAGGGCGTTCGCCGGGGGCAAATCGTCGGAATATTACGGCTATAGCATGCACAGATAAACACAAGCGCGCTGACA
TTGCGATGCGGCTCTTTACAAATGAGTTTGGCAAATAGCTTTGGCGCCGCCACTTGGCCCCAATGGCGGGTGATAACACCCCTCATATACAGCTA
GCTAGCTATAGTTCTACATAAAGTACTCAACTCCAAGGCCATTTAGAAGCCCACTGCCCTTGTGGCAGCGTGTAAATCACCCATACTCACTTGAC
AATATTCGCATGATTGCTGGCATTCAGCTGCTTCAGCAGCGAAATCTCCCGCAGCGTGGACATTGGCACACCGTTCTCGTTCAGCGATATCCTAA
CCTTCTTCAGCGCCACTATGTTGCCGGTGATCACATCGCGGGCTCTGTAAACCGTTCCATAGGCACCTGAAAAGTGGATCGAAATTGTACATCAA
AATGCTTACAACGGGAAATAAATGCGAAAGACAGCCGAAAATAGAATAAAATAAAGTCAGCTGTGCCGATAAGATAAATGGCAGAAATCAGAGAG
GCGAGAGAAAGAGAGAAGGTGCCACTTAGCTTCTTCATATCATTATGGTGTATTTATACTTTTCATATTCAACATCGTATTTATAGCCCTTACGA
TTGAAGTGACTTGATTTATTTGCCTTGTTCGATGAACTAACTGTTTATAATGATTGAATGAATAGACAATGAATGCATTTAGCCCAAAAGAATCG
TATTGCAATGCATGCAATAATTGCATATATTAGAGACTATATTATATGCACTCAAAATTAGTCAAAATATTGCACGAAATTCAGACTAATTTCCT
CATGAAACTGTTGCTGTCTCAGGTACAACGTGATCTTAATTTCTACATGTTCACGGGCAAAGAAAAACGACAAGAGACGAGCAAAATTCCCAATC
AGAATCAAATTCTGGCATGCCAGAGAAATGTCACCGAAAATTTATCACCCGTACGGACAAATGGACAAATGGACAAACGGACGGACGGACGGACA
TGCGTGGGGGGTAGAAAAGCTAGAAGGCACCGGCTATTTCGGTTGACACTGACATACAGAAACAGCAGATATGTACTGATACACCCGAAATAAAC
GCAACTTGAGGGGGGGGGGGGGTGAATTTGGTTTTCCGTCCCTTTGTCACCGTCTCTAGACCACCTGGCTTATGAACTGTGCCGCTGTTGCTACA TTCAAGTACAAGGCCGTGAGCTCGACTCGTTTTTGAACGTCGGCAACTGGTCTGTCCAATTGGAATTGTCAAAAAAATATACAAATATACAAGCA
AAATAAACTCGAAAAATTGCGCAAAGAAAACAACAAAGCAAAGCACTATGGGAAATTTACGCACTTTATCTGGCCGAAAACCGATTAATATATGT
AATATTAAATGCATGCATTTAGTTACAACGGTGACTACTGTTAGGCAATGCAAAAAAGTTAATTGAATGACTATCTGCAAACTAAAAAATATATA
TTATATATCATTAAAAATATGGGCTAGTGTAAGGCAATGCAAAAAAAGTTTGGAGTTAGTTTGGCCACAAAAAGTGGTCAAATTTTCCATAGTAC
AAAGTAGCAAAAATGAGACTGAGCGAAAGCGAATAATAATTGAATGAATGTGCACAGAAAGGCAGACAGCCGAAAGTTTGAGTGTATGTGTGTGT
GTGTGCGTTGTATAACAGATGAAATTGTGCGGACCCATGACTCGCACAACACCCAGTAACAATATCCATCATTAGCATTCGCCTGCCCATGATGA
TCGGCATGATCGGTGACGTAATTGATTTGGGCTTTATTTACAGCAAACAAGCGATCGTAATTACTGACCACAAAAAAAAAAGACCATGAGCCACT
TGTCAGATCATCATGGATGTGAGATCGGCAGAAACACGTAGTCCGCCGAGAGTGGACCTAAAAGTATGCAGGTAGAAGGTGTAGGATCCAATACA
GGGGAGTTTTCCATCCAATATTTCCCCTTTTCGCGGAATTTCCACGCTTAATTAGTAAAGGGGTAAAAAAACAACAACATTCCTCCAAGTGCACT
TGTCATTTCAGCTTCATAACAATGTCGGAGCTCCCGATTGATCGTAAACAGTAGTGAAACCAAATAGCCCAGACTTTGTAAGCAAATTAAAGTAA
TCAAACGTTAACAACAAGCGACCAGCAAACGAAAGCCTCTCGTGCGAAGAGAGCCGGACCTATCCCAACAACAAAGCAACCGCGTCCCATTATTA
AATCCCACCCAAGTCGCTCACCTTCGCCGATGATGTTGAGCTCCTGGTAGTTGAACGGATCGCCATCGCCGAACTTCTTCGCCTGGGACATTTTC
TGCCGCTTCAGCTGGCGTACATATGACATTTAGCTGGATTTTACGGTTATTTGCGTATTCCTCTAATATTCCGGGTAATCGAAACCGTTAGTTGC
ACCAGCTGGAAGTGAAGGGGTGTTTTTTTTTTGGTTATCGATCGTCTGCATGTCACGTATCGATATGTCCTTGTGTCCCCACGCGATAGTTCACA
CAGATCGTAGCGTGAGAGGGAGAGTGCGAGTGCGTGAGAGAGAGAGGGAGGGCCTTACCTGATTTCATACCTGTTGCCTTTTCTAGATAACCCCA
AAACTGGCGATAAAGACTGGTGTGACAGGTGCGCTAATGGAAGAAGTCTGGCTATATGCTCCGCTATGCTTTTCTATCTCCGAGAACCGAAAACC
GAAACATATACATGGACAACTACATATGTATGTATGTATGTAGATGGCGGCGGTCGTTGAACCGCGTTTAATGTTTTCGTACATACTCCGTTTTT
ATGTCTAACCAATCGCAGAACGGCAAAGGCCAACACTAGTTATGACTTATTCATGTTATTCAGTGACGCTGCTCGCCGTCTCCGTTTTGCGGCTT
CGTTCGTGCATCCTGTTGCTCTTATTCGAGCTTGACTGTGAACGCTGTACTGGTTATCTACTGTCGCGTTAGTTGGCGTGTGTCCACTATTCTCT
CCTATCTAAAGTGCTACCACTTTTCTGTCAGTGCATTTTTTTTGCCCGAAAAATATACATATACCGCAAAAAAGAACCCGAATACAATGTATTTT
GTTGCTGGCATTTGTCAATTAATTCTAATCGCGAGACAAGCGAAACAACAATAATAAGCGACACAGTCACAAAACTGGGTAGAAAGAGAGTGTCC
AGAATTGTGAAAGGTATTACGAGGTATTACGAGCTGTATATTTGGGTCTAAAATACATAGTTATTGTTGCACCAGTTTTCGCCCCCTCTCTCTCC
CTCGTCATCCCTCTCTCGCTCACCATTTGCGCTCTACTGATAAGGAAATTTCGGCTTCACTTTACTTTTTTTTCGGTGAACTTCAATGCCAATGT
TGTCGTTTTTCTTTCAACCGTTGTGCGAAATATTAGTTAAATATTAAGAAAATGTGGTTTTTATTTGCGAAGACTCGAACACACACACAACGCCG
CTAAGTGATTTCGCTTGAGAGATCGGTCTTACACACACACACATACACAAACACAAACGCACACACCGAGTGGTACACACACACAGGCGCAGGTA
TTATGTATACATATATGATTTTTATTCGCTTTGACGAAATTTTGGCATTTGTTGATAATCCAGCTAGAACCGCACGATAGGAGCAACGCGACGCG
AATTTTCGGTGCGAACACGGTTCAGTTGCCGGCAGTCGCACTTTAATTAAGTTTTTAAAACGTCTTATAAATTTTTACCAATATTCGTAAGAGTT
GAGTGATTTTGTGTTTTGTTGTTGGCACAGCTCTGGAAACTGTTTTAGATGGTCTACTTAACAGTGGCTTCTCTTCGCCTGTTATCGCCCGCTGT
TAGCAAACAGACGGCCGCTAACATTGTGCTGTATACGTCCAATCGGTTAAACGGTTAATTTCGAAATTGCTGCCAGCGATCGTTATTGAATGTTA
TTCCAATTCGATAACGTAAGTGTTATTGTGTTATACTAATGTTATTGATTTCTGGGAATTTGATATTTTCAACTTGTAATAATGCCCAAATTTAT
TTTTTTTGCAATGTGAATTTCAGGCATTTATATATGTAACATATATAAATTACAAATAAATAAATAATAATAAACATAATGAAAATAATATTTGA
AAAAAATTTTTATTACATACGATAAAATGTGAAAATTTTAAAACTGTCGTGGTCAACTACAATTGGTCGGCCATAATTAGTTAACTCCAAACATG
TGTGTCATTGACTTTTAGCATTTTTAGGATTTGGTAAACTTAAATTTTTATAACCCTGCAAAATAATACAAAATTCTGGAATAAAATGTCTTAAT
GATCTAGATTGGCGGCATAATTCAATTTGTAACTCAATCCGGCGATAAAGTCACTCGTTGAATGTATAATTTATTGACATGAGTTGAATGCCAAA
AGTCGCTCAACATTTTTTTGAGTGAAAGCTTGCTTACCGATTTCCAACGATCTGGCCGCACTGCCAATTTCGAAATCGAATCAAGGCATTCGCAG
TGGGGCGCGTAAATTTAAAAACAATGTTGCAAATACATTGTGAAACCAATAAACGCATTTAACAAACCGCCTATCACAAATGTTACCCATTGGAT
TGGCGAAAATTTCCATGTTTTTTTTTGGGGAAAAAGCGCGATTAATTAGTAACGAAATCAAATTAGAGCACAGTGACGAAGTCAGCCGAGTGCTA
ATTACCACCAGCGGGTATCAGGCACCTAAATTATGCATGACGTACGCC
(SEQ ID NO: 544)

Exon: 6933..6526
Exon: 5610..5437
Exon: 3581..3416
Exon: 2300..2165
Exon: 2102..1774
Exon: 1708..1573
Exon: 1500..1001
Start ATG: 5539 (Reverse strand: CAT)

Transcript No. : CT16072
CTCTTACGAATATTGGTAAAAATTTATAAGACGTTTTAAAAACTTAATTAAAGTGCGACTGCCGGCAACTGAACCGTGTTCGCACCGAAAATTCG
CGTCGCGTTGCTCCTATCGTGCGGTTCTAGCTGGATTATCAACAAATGCCAAAATTTCGTCAAAGCGAATAAAAATCATATATGTATACATAATA
CCTGCGCCTGTGTGTGTGTACCACTCGGTGTGTGCGTTTGTGTTTGTGTATGTGTGTGTGTGTAAGACCGATCTCTCAAGCGAAATCACTTAGCG
GCGTTGTGTGTGTGTTCGAGTCTTCGCAAATAAAAACCACATTTTCTTAATATTTAACTAATATTTCGCACAACGGTTGAAAGAAAAACGACAAC
ATTGGCATTGAAGTTCACCGAAAAAAAACTGGTGCAACTAACGGTTTCGATTACCCGGAATATTAGAGGAATACGCAAATAACCGTAAAATCCAG
CTAAATGTCATATGTACGCCAGCTGAAGCGGCAGAAAATGTCCCAGGCGAAGAAGTTCGGCGATGGCGATCCGTTCAACTACCAGGAGCTCAACA
TCATCGGCGAAGGTGCCTATGGAACGGTTTACAGAGCCCGCGATGTGATCACCGGCAACATAGTGGCGCTGAAGAAGGTTAGGATATCGCTGAAC
GAGAACGGTGTGCCAATGTCCACGCTGCGGGAGATTTCGCTGCTGAAGCAGCTGAATGCCAGCAATCATGCGAATATTGTCAAACTGTACGAAGT
ATGCCAGTTTCTGGAGCGCGACGGCCAATTGCTGATTCTGTTGGTTTTCGAACATGTGGAGCAGGATCTTTCGGATCTTATAGACAGACTTCCCA
AATCGGGCATGTCGCCGCCCACAATTCAGCGCTTGTCAAGGGAACTACTGACCGGTGTGGACTTCTTACACTCACACCGTATCATCCATCGGGAT
CTTAAGCCGCAAAACCTGCTGGTCTCCTCGCAGGGCCACCTCAAGATCGCCGACTTTGGCTTGGCCAAGACCTACGGTTCGGAGATGAAGCTCAC
CTCCGTGGTGGTCACCTTGTGGTACCGCGCACCCGAGGTTCTGCTCGCCCAGCCCTACAACAGCACCGTGGACATCTGGAGTGCCGCCTGCATCA
TCTTCGAGATGTTCAATCGGCGCGCCCTATTCCCGGGCACCTCCGAAAAGAATCAGCTGGACCGCATCTTCGAACTGACCGGTAGACCCACCGAG
CAACAGTGGCCACAGACCATTTCCGTGGCCCTGGAACACTTTCCCCAGCGGCATCCAAAGAGACCAAAAGACTTTTGCCCACACCTGTGCAAGTA
CGCCGATGATCTGTTGAATAAAATGCTTTCCTACGACCTCCACCTGCGACCATCCGCCTTGGCCTGTTTGGAGCACGATTACTTTCAGCAGGAAC
CCCTATAGTCTCGATGCCCAGAAGGATAATGGATAATGGATTATGGATTATGGATTATGGATTATGGATGTGGAAGTGAAAGTGGCAGTGGACTG
ATCATTGCGGCCGCGCTTCGTTCTTGTTACCAATGTTCCTTTAAGTGTAGTGAAGCATTTTGTTTATTTTTTCGCGACAGTCCAGTTATTGTGTC
CGGGGATACGGATCCGGAATAAAGAATACCTTAATTTGTTTGTAGTCGTAAGTTAAGTGTGAATACTACTGCCGATCAACTATCTGATGACCATT
ACATGTGAAACGATTCTCGAGGGCGTTTGAAGGCCCTCCAAATCGAAATGTGATACACAAAGTTCAGGAATGCATTATACAATTTCAAAATTTTG
TACAACAATCATTTATATATGCAATTATATATACAGCATACAAT
(SEQ ID NO: 545)

FIGURE SHEET 299

Start ATG: 480 (Reverse strand: CAT)

MSYVRQLKRQKMSQAKKFGDGDPFNYQELNIIGEGAYGTVYRARDVITGNIVALKKVRISLNENGVPMSTLREISLLKQLNASNHANIVKLYEVC
QFLERDGQLLILLVFEHVEQDLSDLIDRLPKSGMSPPTIQRLSRELLTGVDFLHSHRIIHRDLKPQNLLVSSQGHLKIADFGLAKTYGSEMKLTS
VVVTLWYRAPEVLLAQPYNSTVDIWSAACIIFEMFNRRALFPGTSEKNQLDRIFELTGRPTEQQWPQTISVALEHFPQRHPKRPKDFCPHLCKYA
DDLLNKMLSYDLHLRPSALACLEHDYFQQEPL*
(SEQ ID NO: 546)

Name: cyclin-dependent kinase 4/6
Classification: protein_kinase
Gene Symbol: Cdk4/6
FlyBase ID: FBgn0016131

Celera Sequence No. : 142000013384627
TGGGGATGCTTATAAGGAACTTGGACCAAATATGGTATATTCTCACCTTGAACTCCTTCGCCGCCGCCGGATACTTGGTACAATCTAGGCGACCC
ACTCGAACGTTGGTGGCATGCAAAGCCTGAGCCACCAGAGCAAAAATGGGCTCCGTTTTCTTGCAGTAGCCGCACCACGGGGCATAGAACATGAC
CAACCATTGGCCCTCGTGTCGCACATCGATGAACCGGTCACTGAGCTCCAAAACCTTCGAGGATAGCCCCGTCGAACCCAGAGTCAGAAGCAGAG
CTGTTGGTTTTGTAAATCATTTAGCATCAGCTTGGATTTTTTCTATTGTTCGTAATTTATTTACCACTTATGAGGCCGAAAATCCACATAGAATT
TGGCGACATCCTTGCAGCAGGTTTAATTTGTACTTCCAAGTGTAATTTACGTGCCCCTTATTTGCTATATCATGCTTTCCGTTATTTTAATAGCT
TCTTTACTTAATTTAATTAGTTGATTGGTTTAATTTTCAGTTCCAAATTATTTTCCTTCGGACCACAGCAACAACAAAAGAAAACATTTGCAAAA
ACCACCCCCTTTAGACTGACCAGATGTGGAAAATATCCAAAATACTTAAGGAGATACTCTTTAGTCCAATGCGTAAATTGAACAAGTTTATTTAT
TAATTTTGTAGTTGTTTGGATTATGTTTTTAAAAGATTATTGAACTCAAGATTTTCATTCTACTATAACCTTAAAACTAAAATGAATTCGAAATA
AAAACTAATTAAATTTTTTTATATGCATCTCTAAGAATTTATCTTTAATAATGACATAGTTAATAATTACATTTATAAAAGAATTTTTAATTTTG
AAAATAAGTTTTTGAGCGGCCATAGAGCGGCTGCCTAAGGGTTAATCTGGTATATTTTTAGTCAGATGGCAACTCTTCAGCTTTGTTTACCTCAC
AAAATAGACTATCTGGCAACTCTTAGGCACACACGTGCATCTCCAGAGGAATTTTGTTTCAGTTGTTGTTCCTTATTTCTTCTTAACTAAATAAT
TGTATTAACTAAATAAAATGACGAATAATGCGAAGAAGGAACCCCAGCAAAGGGGCAAGCATCAGGTGCATAATGTGCGCTTCTACACTATAAAG
CCGCGTGAAATTGTCAGCTTGGCGTATAGTAAATCGAGCAAGTGCCTCGCTCTGAGTCGGTAAATTATTGAAAATTAAAAAAAACCTAATAATTA
CTGTGCAGTAAACTAATAAGTACACTCTTTGCAGTGCAACACCCGTCATTGAGCTATGGAACCTGGAGCACGCCCCGTATTTGGATCGTGTAATC
CACCTGCCCACCGATTCTCATGTGGAATCTATAGCCTGGGCGGGAAACCGCTTATTTTCCGTGGATTTAAGTGGTAAACTGATCGAGTGGGATGT
GATTAAGCTAAAACAACGATATGAGCACTCGCCCACTGGCAATGCTCTCTGGAGTATCGATGTGAATCCCGCGGAAACGGATATTGCCATTGGCT
CAGAGGAAGGGCACATCAACATCCTGAGTATTGAGAATGACGAAATCACCTATAAATCCCTATTTAACAAGCAAAAAGGTCGCGTTCTCTGCATC
AAGTTTGATAAGACTGGAACTAAACTGGTGACCGGCACTGAGGGATTTGTTCGCATTTGGAACGTCCTCAAGGGAACCACTCTGCACACGATGAC
CCTATCCGAAAAGAACGTAATAGTTTGGTCCCTGCAGGTGCTATCCGATAATACGATTATTGCCGGTGATTCAGCGGGATTTGTTACCGTTTGGG
ATGCGGATAACGCGACACAGATAGATTCCACACGAGTTCTGGATAAAAACGTATTTGCCCTGGCTGTGAATAATAAGGAGGATCGATTAGTTTGC
AGTGGAATGCAGCCGCCGCTCATCCGGATTTTCAGCAAAACCAAGATAAAGCGGGAAGAGTCCACCAGCGAGCGTTGGATTAAATTCCTACAGCG
CGATGCCCACAAACACTATGTGAAATCCCTGTTGGTTATCGACGATCAAATTTATTCGGGAGGCAGGGATGGCATATTGACCATTACGTCCAGTG
AACGAATGCAGGCACATTTGTCGCAGCATGCTCCCTTTCTGAAAGGTTCCGTAGCTTCCATGGCAATCAGTAAAAAGCTTTTGCTTTTGCGATAT
CCCAACAGCGTGCACCTGTGGCGCTTGGGTTCTGTGGCCCCGCAAGGCGAGGACAAGAAGAAACCCTGGGCACTGCCCGTCGGCCACACGGAGGA
ACAACTTCTGGAGCTGCCACCCCAGAAACTTCTCCAACTAAATGTCAAAGAGCACAACTTTATACAGTCTGCTGCCATTTCATCAGATGCAAACT
GGATTTGCTACTCTACCTTAAAGGAACTCCGAATCAGTCGTTTGAAAAGTGATCCCCTGCAGGTGGAGCGTCTGGTAGACGATCTTCCCGAGGAA
CTTCAACCAGCCAGTCATATAATTTTCACAAAGCAGGGAGATCTAGTGCTGCTCAACCCGCAGAACAATCATCTAAGTTGGTTTACTTTAGAGGA
AGATCTGGTTACATTCAAATATACCATCGATTTGAGTGAGAAGTGTAAGAATACGATTAGCCACGTGGTTATCTCTTCGCATGGCGAATACATTG
TGGCTGCGAGCTCAGACCACATAATATCAGTTTGGAAACTACATGGAAAACAATACAAGCACCTGCTGAACCTACCAAGACACCGAGCAGGTACC
ACCGCCCTATCCATGCACGAGGATTACCCACGCGTGGTGGTCGCCTACGCCAATGGCCAGCTGGTGGAGTACGATTTGGTCAATCGGATATTCAC
CTGTGAAACTAATGAGTACCTGATACCCGAGACCAGGCGCCATTGCATCAATGGAATCAGCCTGGATCCACAAAATCGTAATATATTTATTGTTC
ACACCGAGGGCAATTTGTATGTGTTGGAGAGGGATCAGCATCTGGATCCCAAAGAGCTTGTGAGCAACAGCAAGTCTAAAAAGTTATCAAATGGA
AACCGCTCTTCAGTTGATGGCGGCTCAAAAGGCCTGAGCCTCAAGACGACTCTGTCACGACAGGTAAGATTGGTAGGTCTGTTTACGCACAAGAC
TTTCATTTTGTAACACTTTGGCTCACAAGGTAATCTTAATTCATCCATGAAATAAGAATGAGAGGATTAAAATCTCCTTTTAGGCTTACCGACTA
CCCACTTTAACGTTTTCCGTCCTTTCTATAGCTGCCACAAATCCCAAACCCGCCCCTTATTACTTGCAAACACTTTCACACCTCAATTTTTTTCC
TTGCAGCACCTGGTGCACGTGTCTCGCCTGAGCCCTAACGAACTTGTCAACGTCAGCATTTCGACAAACAATCTGTTGGCTCCGCTGCCGCCGCC
GTACCAGCGGAAGAAGTTCGGTGCCTCGTAAATGGAGCGCCGCAGGATGAAGTTGAAGTGGAGTGGAGTGGCGAAGCTCCAGCATCACTTTGGCT
TACCCAGTAGTTTCCACTTAGTTACCAAATAAAATCAAAAGTATAAAACAATGGTGGAGTGGATTTTTCGCAGGCTTGTGCGGCTCGCACTCTGC
ATTCGCACGGAAATTTGTCAAATGTATTGCCAAAAATTTGTCTCCGGCCGTCTCGTCGACGACTACAATGTCTCTCGTTCCCATTCCCATTCCTG
TGATTTCTTGCAGGCGCTTCTACGTGGATTGTGCAACATTTCGCTTCGTTTTGTGTCGCCGGCATTTACTGTAATTGTTGTTGCTGTTATTTTTT
GGTTTTACACTGTCTAGCCAATGTCTAGACAAGTGCATACCACACAGACAGTCGAAAACACACGCACACAGTGGCGGCAAGCGGCGGTCGAGGGG
GTCTTTTGGTGGAGTCCTGGGGGGACGTCGATGCACAATTCAACTTTTAGCTCAAAAACTCATTGGCCGGCTGGGTCCGCTACCCCGCCGCTCCA
CCATTTCCACCATTGTGGCCGAATGGTTTGGGTGGGCGTTCTGTTTCTGATTCTCGGCAAAAAAGTCCGAGTATCCCGCAGCCATATTCGAATGC
CAGCAGAGGCCTGGACTTGGGCTGGGTCATGACCACTTTGGGATCAAAAAGGTGATTAAAACTTTACAATCGCAGCTCGGGGTGGTGATTCGTAT
CAGACGGCTTGCTGCATCGCCGGAATTAAAATGGATGGAAAGTATTAAACAAAACTAATTTAGAAATCGCTTCGCTTATAAACTAACTTTATAAG
CCAAGGCTGCAGGACTTTCCTCCAATTGCATGCATATCGCACATACTGAAAGGGATATAACCATTTACATATTATAAGTTATTAGGTTCCTCAAA
TATTGTGTTCAAATTTGATTTTAAGGTATTCAAAATTCGGTTTGGCCTTGTCAGTCGTTTTCCATCTTGTTATGTGCATTG
(SEQ ID NO: 547)

Exon: 1001..1199
Exon: 1270..3103
Exon: 3332..3451
Start ATG: 1063

Transcript No. : CT16106

FIGURE SHEET 300

ATTTTGTTTCAGTTGTTGTTCCTTATTTCTTCTTAACTAAATAATTGTATTAACTAAATAAAATGACGAATAATGCGAAGAAGGAACCCCAGCAA
AGGGGCAAGCATCAGGTGCATAATGTGCGCTTCTACACTATAAAGCCGCGTGAAATTGTCAGCTTGGCGTATAGTAAATCGAGCAAGTGCCTCGC
TCTGAGTCGTGCAACACCCGTCATTGAGCTATGGAACCTGGAGCACGCCCCGTATTTGGATCGTGTAATCCACCTGCCCACCGATTCTCATGTGG
AATCTATAGCCTGGGCGGGAAACCGCTTATTTTCCGTGGATTTAAGTGGTAAACTGATCGAGTGGGATGTGATTAAGCTAAAACAACGATATGAG
CACTCGCCCACTGGCAATGCTCTCTGGAGTATCGATGTGAATCCCGCGGAAACGGATATTGCCATTGGCTCAGAGGAAGGGCACATCAACATCCT
GAGTATTGAGAATGACGAAATCACCTATAAATCCCTATTTAACAAGCAAAAAGGTCGCGTTCTCTGCATCAAGTTTGATAAGACTGGAACTAAAC
TGGTGACCGGCACTGAGGGATTTGTTCGCATTTGGAACGTCCTCAAGGGAACCACTCTGCACACGATGACCCTATCCGAAAAGAACGTAATAGTT
TGGTCCCTGCAGGTGCTATCCGATAATACGATTATTGCCGGTGATTCAGCGGGATTTGTTACCGTTTGGGATGCGGATAACGCGACACAGATAGA
TTCCACACGAGTTCTGGATAAAAACGTATTTGCCCTGGCTGTGAATAATAAGGAGGATCGATTAGTTTGCAGTGGAATGCAGCCGCCGCTCATCC
GGATTTTCAGCAAAACCAAGATAAAGCGGGAAGAGTCCACCAGCGAGCGTTGGATTAAATTCCTACAGCGCGATGCCCACAAACACTATGTGAAA
TCCCTGTTGGTTATCGACGATCAAATTTATTCGGGAGGCAGGGATGGCATATTGACCATTACGTCCAGTGAACGAATGCAGGCACATTTGTCGCA
GCATGCTCCCTTTCTGAAAGGTTCCGTAGCTTCCATGGCAATCAGTAAAAAGCTTTTGCTTTTGCGATATCCCAACAGCGTGCACCTGTGGCGCT
TGGGTTCTGTGGCCCCGCAAGGCGAGGACAAGAAGAAACCCTGGGCACTGCCCGTCGGCCACACGGAGGAACAACTTCTGGAGCTGCCACCCCAG
AAACTTCTCCAACTAAATGTCAAAGAGCACAACTTTATACAGTCTGCTGCCATTTCATCAGATGCAAACTGGATTTGCTACTCTACCTTAAAGGA
ACTCCGAATCAGTCGTTTGAAAAGTGATCCCCTGCAGGTGGAGCGTCTGGTAGACGATCTTCCCGAGGAACTTCAACCAGCCAGTCATATAATTT
TCACAAAGCAGGGAGATCTAGTGCTGCTCAACCCGCAGAACAATCATCTAAGTTGGTTTACTTTAGAGGAAGATCTGGTTACATTCAAATATACC
ATCGATTTGAGTGAGAAGTGTAAGAATACGATTAGCCACGTGGTTATCTCTTCGCATGGCGAATACATTGTGGCTGCGAGCTCAGACCACATAAT
ATCAGTTTGGAAACTACATGGAAAACAATACAAGCACCTGCTGAACCTACCAAGACACCGAGCAGGTACCACCGCCCTATCCATGCACGAGGATT
ACCCACGCGTGGTGGTCGCCTACGCCAATGGCCAGCTGGTGGAGTACGATTTGGTCAATCGGATATTCACCTGTGAAACTAATGAGTACCTGATA
CCCGAGACCAGGCGCCATTGCATCAATGGAATCAGCCTGGATCCACAAAATCGTAATATATTTATTGTTCACACCGAGGGCAATTTGTATGTGTT
GGAGAGGGATCAGCATCTGGATCCCAAAGAGCTTGTGAGCAACAGCAAGTCTAAAAAGTTATCAAATGGAAACCGCTCTTCAGTTGATGGCGGCT
CAAAAGGCCTGAGCCTCAAGACGACTCTGTCACGACAGCACCTGGTGCACGTGTCTCGCCTGAGCCCTAACGAACTTGTCAACGTCAGCATTTCG
ACAAACAATCTGTTGGCTCCGCTGCCGCCGCCGTACCAGCGGAAGAAGTTCGGTGCCTCGTAA
(SEQ ID NO: 548)

Start ATG: 63

MTNNAKKEPQQRGKHQVHNVRFYTIKPREIVSLAYSKSSKCLALSRATPVIELWNLEHAPYLDRVIHLPTDSHVESIAWAGNRLFSVDLSGKLIE
WDVIKLKQRYEHSPTGNALWSIDVNPAETDIAIGSEEGHINILSIENDEITYKSLFNKQKGRVLCIKFDKTGTKLVTGTEGFVRIWNVLKGTTLH
TMTLSEKNVIVWSLQVLSDNTIIAGDSAGFVTVWDADNATQIDSTRVLDKNVFALAVNNKEDRLVCSGMQPPLIRIFSKTKIKREESTSERWIKF
LQRDAHKHYVKSLLVIDDQIYSGGRDGILTITSSERMQAHLSQHAPFLKGSVASMAISKKLLLLRYPNSVHLWRLGSVAPQGEDKKKPWALPVGH
TEEQLLELPPQKLLQLNVKEHNFIQSAAISSDANWICYSTLKELRISRLKSDPLQVERLVDDLPEELQPASHIIFTKQGDLVLLNPQNNHLSWFT
LEEDLVTFKYTIDLSEKCKNTISHVVISSHGEYIVAASSDHIISVWKLHGKQYKHLLNLPRHRAGTTALSMHEDYPRVVVAYANGQLVEYDLVNR
IFTCETNEYLIPETRRHCINGISLDPQNRNIFIVHTEGNLYVLERDQHLDPKELVSNSKSKKLSNGNRSSVDGGSKGLSLKTTLSRQHLVHVSRL
SPNELVNVSISTNNLLAPLPPPYQRKKFGAS*
(SEQ ID NO: 549)

Name: WD-40 repeats containing protein

Celera Sequence No. : 142000013384256
GAACCAATCGATATTTGCAGTAGGGTAGCGCAATAAACTTACGTTTTATTTATTGAAAACAAATCGGTGTCACCACCAGCCGCCTTCGATAGAGC
TGTTATCGTTATCGCAGCCACCTATCGTTTAATTCGCTGGGCGTTTCACAATTTTTTGGGAAACACAACAAAGCTTCACAAAGGACACGATGCT
CGTTCTGGTACTCGGCGACCTGCACATCCCGCACCGGTGCAGCAGCCTGCCGGCTAAATTTAAGAAGCTGCTGGTGCCGGGCCGCATACATCACA
TCCTGGCCACCGGAAACATCTGCACCAAGGAGTCCTACGACTACCTGAAGTCCCTGGCCAATGATGTGCACATAGTGCGCGGCGACTTCGACGAG
AACCTGACGTATCCGGAGCAGAAGGTGGTCACGGTAGGCCAGTTCCGGATCGGTCTGTGCCACGGCCACCAGGTGGTTCCCCGCGGAGACCCGGA
GGCGCTGGCCCTCATCCAGCGGCAACTGGACGTGGACATCCTGATCACGGGGCACACGTACAAGTTCGAGGCCTACGAGCACGGCAACAAATTCT
ACATCAATCCGGGATCGGCCACGGGTGCCTTCAACCCACTGGACACCAATGTGGTGCCTTCGTTCGTGCTGATGGACATTCAGAGCACCACGGTG
GTCACGTACGTGTACCAACTGATCGGCGACGAGGTCAAAGTGGAGCGCATCGAGTACAAGAAGATCTAGGGTCCTAGTATTAGCCACCAGCCATT
CCCCTCCAATCCAACCCTTGACCCCTGCATTCTGAGCTCGGCTTCATTAAAGAAATTGTAAATGTACGTAGCAATAAATCAAGTTCTCATTTTTT
TATCTGATAAAAAATGCTAGCACCTTGTTTAAATAGAGAATAAAAGTACGAACGGACGAAAGTGAAGTTTTAGATTTAATGCAATAATAAACGAT
TACAAAGTAAGGAAAAACACCCCCAGAAATTGTGATACTCCCACAATAATCTGATAAAAAAGTTTAAATTTTATTAAATAGAATATAAAAAGGAG
TTACATCTGATGATCGAGTAAAGAGTCTGCTCAAAAGTTCGGATTTCATGCTCAGTTTCTCATTGCAACACACTCTCGATATAAATACATTGGGT
TCGGTTTGTGGCCATCGCTTTTCCATCGAAATAAATTATATAAATACTTTCCACGAGCCAGGACAGCAATGTTTGGCAACATCATCAATACGAAA
TGTTTGATCTAAAAATCTTTGAATTACGAAAACTTTGCACTTAGATTAAATACAATTATGATTGCTGCTGACGACAGTTGGAAAAGCAACGAACA
GGATCCCCGAGGAGGAGAACCGCCTTAGCCGAGGCTGTCCACGCACACAGTCTTCAGGGTCTTGCCGGCAATCGTGGTCTTATACTGCTCCGGTA
AAGCCAACTCGGTCTGGAAATCACAAAAAAAATAAATAAATGACTGAAGACAAGAGACAAATTTTTGAACTCACATAATCGCCGCTGTCGTCGGG
CAACAGGATGTTCATCTCCGAGGACTTGGAGTTGACGATCTCCACGCCCAGCGAGTCCTTGGACAGATACATCTGGCAGCCGTCGGTCTTGTCGA
TCGATACCGTCGGCACCGAGCCGAGCACCTGCATCTGCACGCTCTGGCAGTTGACGAACTCCACGGAGGCCACCACGGAATCGAACAGCAGGGAG
CACTTCTTGCAGGAGTCGAAGACGATGTTGTTCACCTTGCCCTTGACGGTCAGAGTGGATCCCTCACACTTGAACACATACACCACGTTGTTCAT
CTCGGCGTTCTCCACCAACAGCCCGGTGTTGTTCTTCTGGTACTCGATGATCCACTTCTTTCCGTCGCGCTCGAAAACGGGCGCCTTGGCTTGCG
CAGCTGATGGAGCAGCAACGGCCTTGCTGCCGCCCGACTGGGCTGGCGATTTGAACGGAGCCGGTCCAGTGCGTAGAGATGGATTTTTATGGGTC
TGCATGTCGCCAGTGACCTTCTTCAAGCCTGCGGGTTTATCAAAAGATACATTTTCTTACTATAGGAGCACTTAACCATTTTTGCAGTTGCTGCT
CACCCTTGGTGATGTCGGCACCCTGGTTGATCTGGGCGAAGAGGGCGCTGCGATCATCTCCGGCGCTATCCAGCTTGAGGGCACTCAGATCCAGC
ATGGGCGGCGGTGGGGGCAGACCACCGGGTGGCGGTGGTGGCGGGGCACCTCCGGCGGGGGCCGCTCCCTTGCCGGACCACACCAAGCCCGTGGT
GTGGTACTGCCGGATGTAGGCCTGCAGTTCGGTGAGCGTCTGCACCCAGGCGCGGGCCCACTCCACATGCGTAACATCCTTCTCCTTCCACTCCT
TGAGCACGCGGTTCGTGTAGAACTGGCCGGCGTCGTTCATCTCCTTGACATAGGGACCCGGGGTCTTCTCCACGCACACCCAGCCCAAGGCGGGA
ATGCTTTCGCTGATGGCCGACAGGTGGTTGAAGAAGGGCGAGGAGCGGTGCTTCTCGCGGAAGTCCTGGATGGCGCTGATCTGCGTCGAGGTCGG
CTTCAGAAGCTCCGCCTGCTTGGGCTGCGCCGGCTGGGCGATCTGGGTGGCCAGCGTCACGTACTGCAGTTGGGAGCTGTTGCGGAATTGAACGA
TGGCATTATTACACTTTTACCATAGATGACTCATCCAGACTGACTCACCCAAAGGCGCTCTTCACGAGCTCCGCATGCTGCGCCACATCGCCGCC
AATTTTGGCGGAGAGAGTTAGGTATTGGCTCAGCGGACCCGCCACAATGTCCTCGAATCCGGCGACACTCATGTTGCTGCTGGGCGGCGAGGGAG GTGGAGGTGGTGTCTCTGCTTTTTCAAAAACTGGAAGAGCTTCTTCTTCTTCGGCTGGCGGAGGCGGGAGTGTGGGCGTGGGCAGTTCTATCGGC
TGTGGCGCTGTTAGAGTCCGTTCCAATCGGTCGACGAGGGTCTCCAGTCGCTCGCAAATGCTCTCCAAGTGGTCGACGGCGGCCGAGGGCTTGGC
TTCCGGCTCGTTATCTGAACCAAAATGACGCGGAGGAGAACGGCAAATGTTTAGTTCGTTTTGGCAATTATCTCGAATTATTCAAATAACACTGA
GTTTTATAAAGAAAATAACTTGAGTGAGATGATGCTTCAGCGTGATAAACCCCAGTGAATCGTGCACTCACAATACCTGACAAAAAAGGCGATAT
AAACTAAGGCGTCTCGAGAGGAATACCTCATCACGAGCTTGTGTATGATGATGAACTGGTGCGCTTAATACTTATAAAGTTCAATATGCAAAAAG
AGCTAATCCCAACGAGTGAAAGTAATAATCCACATGCAAAAACGGCACAAGACAACGAAAAATCATAAGAGAGAAGAACTAAGTTGAACCTTTAA
ACGGAAGCACTTGACTTGCGAACTTATTGGCCATCAGGAAGTTACGTGAATCGCTAGACTCTCAAAACTTCTTCACAGCGAAAACGAACACATAA
AGAACACAGAAAGTCAAGCATCCGCTTAAATAACTGCTGAGATCGAAAAAAAAAAGCAAAAGAATCGGACTCTATCGAAGCTCGCATACCCCGCA
CGGCCACGCTATGCTCCACAGCCGCATGGGCGGCCCGCAGGAGCTCCGTGTAGAGACGCTGGCGCTTCAGCTCCAGCTCGTCGCGTCCCACCGGC
GTGACCGGGGGCTCGATGCAGCCGCTGGACATGGAACGAGGACAGAGGAGACGATGTACTGGCAATTCAAAGCGGGGCTGGGAATGCAGGGGTCG
ACCTGTTCTGGTTTCAGCTTAACTATATGGATATTTTGGGCGTGAAACCAAAACAGGATCTTGGGTAAGCATACATGTCGTTCAGGCGCTCGTCG
TCGAACCACGAGGGTAATCCGTGGGCAAAGAAGAGTGTTTCCGAGACGACATCCCCCTCGATGTAGGGTGCACACATGCTCTCCCGCTTGGGTGG
CGGCAGTGAGTCGGAGAACACCTCGTCGTCGTCCAGCAAGGAGCCCTGATTCTGGCTGGCCAGCAGGAGCAGTGGCAGTGGATCCGGCTCGATGA
TCTCCGCCCGGTTGCTGATATTCACCTTCTTCTTGATCGACTGATGCGTTGAGTTGTGCCTGGACAGGCAGCTCTTGGTGGGCGGCGGCTGAGGA
GGCGGTGTGGTCGGCGTGACCGTCGCCACCACCACCACTTCGTCCGCCTCCTCCGCGTCGCCGCTGGTCATCGAAGCAGGTGGTGCCGTGGATGT
GGAAGAGTGCGTTGAGCGGGCCAGTGGCTCCGGTTCTTTGGGTGCTAGTGCTGGATTTGCTGGTGATGATTTGCTAGCCGCTTCAGCCTGAGTTG
GTTGGGCTGTGGAAGTGTTGCTTAAGATTACTCTACATGAAGCGACGAATTACCAAGACGATCATCAAGGAAAGCGCCGATACTTAAGTTGATTA
CTTCACTTCACTCTCTGCTCACCTCGCTTCCTGTCTTCATTATGTTTATTTATCGCATTTAAAAGCATTTACCATGGTCACTGGCAGATTGAGTA
GTTAGTTTTTACTGCTCACCTTATTATTATAGAATCTATAGAATCTTGAATTTTCTGTCTAAATTATTGACCTTCATTTTAGTTTCTATATTCGT
CACTACTATATACTATACGTTCACTTTGATGGATGAGCACGATCTAAGTGCTCAACAAAAAGTGTGTATGCAATGTCATTAGCTATTCCTCATTA
ATCAACTGAGAATCGGCGCAATTCCTTGATATTCATATGTATAAAATTCACAGAAATAAACCGAAGAGAAAGCACAGTGAAGACAACTCATAAGT
AAATAGAAAAGGACACTCAAGGCAGCTTGAAGTGCCCGGATTGAAATGAAAGGAAAGATCAGAAGTGGTGGTCAGCTGCAGTGGCATTGCAGTGA
GTGAGAGCCGGCCGGATAGGGGCCTTCGTTCCGGAGAGCAGACAAAAGCCGAGACAGCTGTTGAGCTCGAAGGCCGGAGAACGCGAATAGATGGG
GTGGTGGGTAAATACTTAGCGTTGCGTCAGTACCAGTGTTTGGCTGGGTGCTTGTGGGCACATCCTCGGGATTATGCGCTTCCAAGAGCTCCTTT
TCTGGTTTCACAGGCTCTGGCTCCTCCTTCGGAGTTCCTGGCTTGCCGTTCAGCTGGGGTTCCTCCTTTTCGGTGACCTGTCCGCCGTTCTCCTC
CTCTGCGTTCCGCTTTTCCTTCTCCTTCTTGCCCGCCTTGGGGTTCGATCGGCAGCAGGAGAACATTTTGCAGGCGTGTGGCTGGGCTTTTCCGG
TGCTCAACACTCTAGGTACGAATCAAGCACATTATGTAAGTTCCGTGGCTCGACTGCGGATGCCCGTGAAGCTCAAGCGGCGGTCACAACACTGA
CGGCACACCAAACCAAATCGAATCAGTAGAAGCAGTAACAGCAGCAGCCATATAAGACACTCAACGGGTTTCCAACGAACGTGGCCACTCCTTGC
TCACTGTGTACATATATTCAGTGTATGGCCCAAATTTAGTGGCACATTAATAAGGTCCTCCGAGTTGTCCGCGCCTTCAACTGGGTCAAGTGACT
GCCGACCAAGCACAGAACCAAATGGCACACAAATGCGATTACACACGGAGAACAGAACACACCCTAAACGAAGCGCACGCCCACGCACTCGGGGA
TTCGATTCGATTTCGAACTCGAACTCGAAGGTCTCAACAGGACTCTGTTAGGAGAGCTCCGCGCTGTTAACTGCTGAGTTTCGCCGCCTTGTTGG
GCTACTCCGCGCTGCTTTTGACCATTTGGGGCCAGCCACCGACTGGCAATGAAATGTGTTTCATTAATAACCGCTTTTGGCCTGACATGCAGGAT
TTTGTGCAAGCTCCGGCGATGTCTTGCACTTTTGCAGCAGAGAAAGCTTACGGTCCAGGCGGAAAATGGAAAACTCTCCGAGAGAGTTGCGCAGA
CACCACTGTGATTTCGTGATACCCTTCTCGCCACGGGTGGCGCGACTTAAGTGAGGGAAAACCACGGCGATCCCATAGTTTTATCAGCCCTGTAA
GGCAGGGTTCGCCTATCAATTAGTTGTGACAACACCGAGTTATCTTTACTATTTGGAAAGTTTCCAGGAATGATCGGTAATGAAACTATGATTCC
ATTTTGAGCATTACCATAACGTTTGTAAGCCATAGAGAGTAGAGAGATGCAATGATCATATCTTAGCCGGCTATAAAAACAGTTTTAAAATGTTC
AGCTTTTTGTGAAGTAATCTGCCGCAGAAGAGTATAAAAACGTCGACGTAACTGAAACTCCCATATCGTTTGCTTGCCAGTTTTTGTTTTGGCCT
TAGTGCAATGGGTTTATTGCACCGGCAACGTTGTTTTTGTTTTTAAGTAGCTTTAAACAAATGGCTGGCAATTAGAGTGGGAAATGCATCAGTAG
CCGTTGGATTGGAGGGAGGGGCTAAGCCGCCGAGGACAAGTAAGCCGAGATTCAACTTTCGCCTGGCGATACTAGTTCTCCTTGCAGTCTTGATG
CGTTTTCTGCGGCAGATGCGTTTGTTGCGTGCAGAAAGCAAAGAAGAAATGGGGAAGAAAAACTAGAAACCAAGATTAAATGTCTGCAGCTGAGG
AACCGTTATTCCCGCTGCGAGAGTGTGAGTGAGCTCGAATTACCAGGGGTGGGGGGTGTTCGTAATGGTAGAAGAAAAATCGCCCACCTTATAAG
GCGAGGTGTTATTTCTTCCACCGAAATCGAGTGAGTGGTAATATCTGCCGATTTTCAATCGCGATTCGCTGATAAAAGCGTTTTGGCCAACTTT
TTGACTCATTCGCGCACGAATACAAGCAAACGTGTTTGCTCTTGCGTAAACTACATACATGCATACATACATATGCATATCAACTATGTGTCTGT
GAGTCAGCGAAACAAAAACAAAAAATGGCCACAACAGCTGAGTAGTTACTTTTTTTTATCGGGGGTTAACAATCGCAATGGGAGCTGCTAAGGGT
TAATTTGCATACACTTGCTGGCAATGAATTAGTTGTGTCTTTATGCCATGGAATCGGATATGAAATCATCGTTAAAAATACACCATGTAGATTTA
ATTTTACAAGCAACATGAATCACACAAAAATAGCCATCACACAGCTGTCTCTTGTCTTTTTGGCTCTCTTCGCTGTTGTTGTTGTTGTGTGTGTA
CAAACACCCACAGCCTGCATCACACACACACGCTCAAATTCGTGACAGCACCACCCACCCCTCACCAATAACCGTTAATTCCGCAGACACTTTCA
GCCGGCGAACGGGAGAAGAGAATTTGCGAATAATAGCAAAGCCCCGTTTAAATGAACGTTTTTAGCAACAATCAGGCGTTACTCACCTTCTTTTG
CTGCTGATGAATTTGCAAGGATCTGCAGTTGTATTCCAATTAGAACTGACGAGAAGCTGCGTAGCGAACACCGGCGAAATGGCGAAAATAATAAC
TTGGCGTGGCCTTTGGTGGGACCAGGCGTACATTCGTGGAAATAGTCAAGCGAGTTAACCCTTATGTGGGTGGCAGAATACTAAAAATATATGAT
ACAACAAATTTTAGACTTAAGAAAACGGATGTTTAAATGTATAAAATATGATGGAAGTGCAATAGCCAAGCTTATAAACTAATTCTTAAATTATT
TGCAATGCATTTAGGACTTTTCGATATACACGTAAATAAACTATATTTTGATTGAACACGGTACATTTCTACTAGAGTTCACCTTCAGATATTGA
CGCTATTTCTTGTCCTGTAAATTATTTGTTAAATCGTTCACATTGTATGTCTAATAAAGATGTTTTCCAATAAAATGTTATTCCCTTTTCACTT
AGTCTAACATATTCATTAAATAATCAATGTTTTATTTTTTATTTAGTTATTTTAATTAGTTCTTAATTATAAAACTGCTCTAGATTCTCGATATT
TTGCGGAATCCGGCGCATGGTCACACTGACGAACACGTATTTTCATTATTCTTGCGAAGCGCATCGCTTAAAACTTGATTACGCTCGGATAACAA
GATGCACCCGCGTCTCAAGTGACTGAACAGGTAGCGAAGTGACCCTGGATGAGCGTGGGTAGGCAGCCGGCACCTCTGGAAAGCCCTAATCCCAG
GTCCGCCAGCCGTTTGCAGGTTATGTCCGCTTGTGTACACTGTGACGGGGAACCGAAGAAGCAACAGGAGCGGATTCCTGGCAGAAGAGACAACC
GCTGTACGAGATACCGCCCCTGACCTGCGCAACATGATCGAGGTGCTGTGCCTGCTGCTGGGCAGGATCCTGCTGCTCCTGGTCGGCGGCTACGA
ACTGATGTGGCGGCTCCGAGAGCGACTGAATGCACTGGCCGTCCGGTCATATGACCTTTGGCGCAGCAAAGCGGCACGTGAGGCGCACGAGCGGC
GCGTGCTCGCTGACTGCCGCTCCCAGTTGACGAAGACGCCGCAGCATCTGGTCCTGGTTATCTCCCCCGTAGATGCCGGCGTG
(SEQ ID NO: 550)

Exon: 7538..7506
Exon: 7432..7402
Exon: 3054..2709
Exon: 2641..2094
Exon: 2023..1500
Exon: 1438..1001
Start ATG: 7538 (Reverse strand: CAT)

Transcript No. : CT16203

FIGURE SHEET 302

ATGTACGCCTGGTCCCACCAAAGGCCACGCCAAATCCTTGCAAATTCATCAGCAGCAAAAGAAGATAACGAGCCGGAAGCCAAGCCCTCGGCCGC
CGTCGACCACTTGGAGAGCATTTGCGAGCGACTGGAGACCCTCGTCGACCGATTGGAACGGACTCTAACAGCGCCACAGCCGATAGAACTGCCCA
CGCCCACACTCCCGCCTCCGCCAGCCGAAGAAGAAGAAGCTCTTCCAGTTTTTGAAAAAGCAGAGACACCACCTCCACCTCCCTCGCCGCCCAGC
AGCAACATGAGTGTCGCCGGATTCGAGGACATTGTGGCGGGTCCGCTGAGCCAATACCTAACTCTCTCCGCCAAAATTGGCGGCGATGTGGCGCA
GCATGCGGAGCTCGTGAAGAGCGCCTTTGGCTCCCAACTGCAGTACGTGACGCTGGCCACCCAGATCGCCCAGCCGGCGCAGCCCAAGCAGGCGG
AGCTTCTGAAGCCGACCTCGACGCAGATCAGCGCCATCCAGGACTTCCGCGAGAAGCACCGCTCCTCGCCCTTCTTCAACCACCTGTCGGCCATC
AGCGAAAGCATTCCCGCCTTGGGCTGGGTGTGCGTGGAGAAGACCCCGGGTCCCTATGTCAAGGAGATGAACGACGCCGGCCAGTTCTACACGAA
CCGCGTGCTCAAGGAGTGGAAGGAGAAGGATGTTACGCATGTGGAGTGGGCCCGCGCCTGGGTGCAGACGCTCACCGAACTGCAGGCCTACATCC
GGCAGTACCACACCACGGGCTTGGTGTGGTCCGGCAAGGGAGCGGCCCCCGCCGGAGGTGCCCCGCCACCACCGCCACCCGGTGGTCTGCCCCCA
CCGCCGCCCATGCTGGATCTGAGTGCCCTCAAGCTGGATAGCGCCGGAGATGATCGCAGCGCCCTCTTCGCCCAGATCAACCAGGGTGCCGACAT
CACCAAGGGCTTGAAGAAGGTCACTGGCGACATGCAGACCCATAAAAATCCATCTCTACGCACTGGACCGGCTCCGTTCAAATCGCCAGCCCAGT
CGGGCGGCAGCAAGGCCGTTGCTGCTCCATCAGCTGCGCAAGCCAAGGCGCCCGTTTTCGAGCGCGACGGAAAGAAGTGGATCATCGAGTACCAG
AAGAACAACACCGGGCTGTTGGTGGAGAACGCCGAGATGAACAACGTGGTGTATGTGTTCAAGTGTGAGGGATCCACTCTGACCGTCAAGGGCAA
GGTGAACAACATCGTCTTCGACTCCTGCAAGAAGTGCTCCCTGCTGTTCGATTCCGTGGTGGCCTCCGTGGAGTTCGTCAACTGCCAGAGCGTGC
AGATGCAGGTGCTCGGCTCGGTGCCGACGGTATCGATCGACAAGACCGACGGCTGCCAGATGTATCTGTCCAAGGACTCGCTGGGCGTGGAGATC
GTCAACTCCAAGTCCTCGGAGATGAACATCCTGTTGCCCGACGACAGCGGCGATTATACCGAGTTGGCTTTACCGGAGCAGTATAAGACCACGAT
TGCCGGCAAGACCCTGAAGACTGTGTGCGTGGACAGCCTCGGCTAAGGCGGTTCTCCTCCTCGGGGATCCTGTTCGTTGCTTTTCCAACTGTCGT
CAGCAGCAATCATAATTGTATTTAATCTAAGTGCAAAGTTTTCGTAATTCAAAGATTTTTAGATCAAACATTTCGTATTGATGATGTTGCCAAAC
ATTGCTGTCCTGGCTCGTGGAAAGTATTTATATAATTTATTTCGATGGAAAAGCGATGGCCACAAACCGAACCCAATGTATTTATATCGAGAGTG
TGTTGCAATGAGAAACTGAGCATGAAATCCGAACTTTTGAGCAGACTCTTTACTCGATCATCAGATGTAACTCCTTTTTATATTCTATTTAATAA
AATTTAAACTTTTTTATCAG
(SEQ ID NO: 551)

Start ATG: 1 (Reverse strand: CAT)

MYAWSHQRPRQILANSSAAKEDNEPEAKPSAAVDHLESICERLETLVDRLERTLTAPQPIELPTPTLPPPPAEEEEALPVFEKAETPPPPPSPPS
SNMSVAGFEDIVAGPLSQYLTLSAKIGGDVAQHAELVKSAFGSQLQYVTLATQIAQPAQPKQAELLKPTSTQISAIQDFREKHRSSPFFNHLSAI
SESIPALGWVCVEKTPGPYVKEMNDAGQFYTNRVLKEWKEKDVTHVEWARAWVQTLTELQAYIRQYHTTGLVWSGKGAAPAGGAPPPPPPGGLPP
PPPMLDLSALKLDSAGDDRSALFAQINQGADITKGLKKVTGDMQTHKNPSLRTGPAPFKSPAQSGGSKAVAAPSAAQAKAPVFERDGKKWIIEYQ
KNNTGLLVENAEMNNVVYVFKCEGSTLTVKGKVNNIVFDSCKKCSLLFDSVVASVEFVNCQSVQMQVLGSVPTVSIDKTDGCQMYLSKDSLGVEI
VNSKSSEMNILLPDDSGDYTELALPEQYKTTIAGKTLKTVCVDSLG*
(SEQ ID NO: 552)

Name: Adenylyl cyclase-associated protein
Classification: enzyme
Gene Symbol: BcDNA:LD24380
FlyBase ID: FBgn0027062

Celera Sequence No. : 142000013384665
ATCTCATCTCATATGAAAGCAATATCATATATGTATGTTAATATTAAATAGATATTAAACATAAAAATCCATCCCACCCACATTCCGCTGAAAAA
TGAAAACACTCGCTTTTGCCGAAGTGGAATTTTATTGTAATTAAATTTGTTGGGTGTACAAAGGTATGTTTTAAGGACTTTCTCTCTGCATTTAT
TACAATTTCTTCAAATGGTTTTAATTGCTGGGCTTTTGCTTCGAAGACGGGCAATCAAGTTTCAAGAATCCTATTTTCTTTAATCATACAAATTA
TGTTTTATTTCGCTTTAATATATAAGGATACATATATATATCTGCTATATATAGAAGTGTGTTGACTTGCGTATATTTCGTGAAAAGTAAAAGTT
TTCTTCTTCGCAATTTCCCTTGAACTAACATTCCAATTCGGGTTTTGGTTATGTTTTTTTTTTCTGTTTTACTCTCATTATTTTGTTTGTTTGTT
TTTTTTAAATAATTTTGCATTTTCTGCATACATGTGGTTTTGTGTTTTGCAATTTTTTCAATGATTTTTCCTTGGGTTTTTATTTGTTTTTAGTT
TTCGATTTGTTTAATAAAAAAATATGTATTTCACTGCCCAGAGCGAAAGCCATTTCTTACTTCCGCTTGCGTTAATATATCATTTTATGTATGTA
TGGTGTAAAAACATCATTTACTGGTAAAACTCTCGATATCCTTTGTAACAGAAATCGGAACGCAAATGAAATCGAGGCGACTTACCAGCTCCTTC
TCATTAAATACATATATGTTCTTGCAAATGTTTATAAATGTATGCATGTTTTTCCTTCTCTCGGATAATAGTGTAATCATAAAAATCCTGTCTGC
TTTTTTGTTGTTTATTAATATGCTTCATAAGTTGTTTACGCTTTAGCGCTTTTCATGTGTTTCTTGTATTTCTCATATATGTTGTGGTTGTTTAA
TATGTGTGTTGCTGTGTGTGTGTTTTTGTGTTTATATATATTATTTTTTTTTGCTGTTTTTACATAGGTTTTGCCATTTTTTTGTAGTTTTTTC
GATTTATGTTTTGTTTTCATTTGTCAACATATTTTTTCAGCTGTTGGTATTCTGTATTTTCTCTCTTTTTTCAAAGTAGCAAAAACTTGACTCTC
ATATTCTTGCGGTTTTCTTTTTCTTTCTTTCTTTCTATTCTTCTGTTCTCTGCACAGTTTGCTTTCCATTTTTTCGTTTTTATTTTAACTCTTTT
GCAATTTTTTTGTTTTTTCTTTGCTTTTTTAAAAGTGTATGGTTGTCGCGTTTCTTTTTCTAAACAAAGCTTTCTTAAAGTTTGAATTTGAGAAA
AAAGAATTGAAAAAAATTACATATCGCTTTCGTGTTTGTTGTTGTTTGAAAGTGTGGATGGAAAAAGTGTACGAAAAACTCAATATGTATGTAAC
ACTAGAAACTTCTTTAAAATTTTTAAAACACAATTTCAATACTTGCAAGAAGCGGTTTACATGTATGCTTTGCTTTAATCTGTTTATTTTGCAAT
GGTTTTTTGGTGTTTTCATTATACGCATACAAAATAATATCGATCCAGTTAAAGCAATAACGAAATTTTTTTCATTTCACATTTTTCCGTTTTTT
TTTTTAATTAACATGTTTATGTAAAAAAAAAAGAATTTATAAGTGGACTGCAGAATTTGATTGCGTGACTTTCTTCTTTTGCTTCGTGTACTTGCG
TAAATGCGTTCGAAATTAAATGATTGAAATTGCTTTTGTTGATGTTTCTGGGATTAGAAAAGAAAAAGCCGTAGATTTTTCGCTTTGTTTTTCTG
TGTTAATTGTGTGTCCTTGGCAATCCTCCCCTGCGCAAAGCATCAGTGAATGCGAATTTTTGTTGTTCATGTATTGAAAGATTAGTGGAAAACTG
CAAGGACAAAAGAGAGGCGAGTTTAGACAGCTTGAACTTTTCGGAAAATTTGTAGACTACTTACTTTTTGGGTGTAAAGTGTTCTTGTAAAATGT
TCATACGCTTGAGCTGTTCGAGCTTAGTTGGCGGGCTCGGTGACGCGGTGCACCTGAAGCACGGCACAGCCTCCTCCACCTTGGCCTTAAGGGC
CTCCTGATCCTCGATCATGTGCAAGAGCTCAGAGTTTTCGATCTCCAACAACATGCCGGTGATCTTACCAGCCAAATTGGCGTGCATATGCTCAA
TCATCGGATACAGACGCTCGCCCAGGATCTGTTTCTGCTCCTGCGGCTTGGCGTTGGCCAGCAACGAGGCAATGAGCTTCTCAGAATCTGCAAGA
AAAATAGCAATGGTGCCATTAGTGACAAATTGTGCATATTTTCAGTCGACCTAAAACTTACTCTTTCCTTGCAATTGCTGTGGAATTGGCTGGGT
CTGATGCAACTGTGGCACTGGAGGATTGCGCATGTTTGAGGTGTACTTATAGTTGGAAGTACGCTGCTGGGCACCGCCAGCGATTTGGGCTCCGG
GGATCTGCATGTTGGGTGCTGCAGTTTGCTGGCCAGTAATAGCGCGTGCTCCAGTGTTGCGCATGTTGTTAGCCGCAGCAGCGGCGGCATGTGTG
CCCTGCACCTGAGGCTGTGCCCCGCGAGCGCCAGCAGCAGCCGAACGGAACTGAGTGGGCACCGCACCGGCTGTGCCCTGGAAGCCACCAGCAGC
GGCAGCTCCGGCCTGGACACCCTGTATGGCTGCTGGGGGACGCACCTGGGGCACCCAGCGGGGTGTGTTTCTCATCTGAGTGGCCACCTGGGAAC
CGAAGAAACGCTGATTTGACGGAAGGGTCGGCACAAAGAAGCCGCTAGCCGCGTTGGGCTGGTAGATCTGTCCCAGCTGCTGCATACGCATGCCG
GTCATGTGACGCATGTACTGCGAGGCGAGATGAGCCTTGCGCTCCTCCTTCCTTTGGGCCAAAGCAACGTACAACGGCTTACTGCCGACGACGCG ACCGTTCAGCTCGGTGACGGCGCAGGTAGCCTCGCTTGCGGCATTGAAGCACACGAAGCCGAATCCCTTGGAGCGACCCTCCTCATCGGTCATGA
CCTTGGCCGATGTGATGTTGCCGTATGGAGAGAACGCGATGCGCAGACGATCGTCATCGATTGTGTCGTCCAGGTTCTTAACGTACAAGTTAACG
CCGAACACAGACTCGTGACGCTTCTGCTTCAGTTCCTCGAACTTGCGCTTCAGCTCCTGCTGGCGTTCGGCCTTCTTCTGGGCACGAGCCACGTA
CAGGGACTTGCCCTCTCCCATGTCCTTGCCATTGAGAGCCTGAACGGCCGCCTCAGCAGCCTCTGTTGTCTCGAATGCAACGAATCCGAAGCCCT
TGCTCTTGCCATCCTCCTTGGACATGACCTTGTAGCTGGTTATCTTGCCGTAGGGCTCAAAGAATTCCTTCAGTTTTTCATCGTCGAAATCCTCA
GTGAAGTTCTTCACATATACATTGGTGAAGAGCTTAGCCTTCTCGCCCAGCTCCTTCTCGCGCTCCTTGCGCGGGATGAACTTACCCACGTAGAC
CTTCTTGCCGTTGAGCAACATGCCATTGACTTTGTCGATGGACGTGTTTGCGGCCTCCTCGGTCTCGAAGTGGACGAATCCATAGCCCTTTGAGT
TGCCCTTTTCATCGGTGGCTACCTTGCAGCTTAAAATGTTGCCGAAGGCGGAGAAAGTGTCGTAGATTGCCTTGTTGTCGATGGCCCTATCTAAG
TTCTTGATGAACACGTTGCCCACACCTGAGCGACGAAGAGAAGGATCACGCTGAGACCACATAATGCGAATGGGCTTGTTGCGAACCAGGTCAAA
GTTCATGGTGTCCAAAGCACGCTCAGCTGTTGATGAAAATCGGGAAAACATTTGGTTACTACCGACACGATTTGGGTATATCAAGATCATTATAA
GTTGAAGGGGCTTAAATAACAATGTGACTCTTCAACTTCTGCACTGGCCATGAGCAAAAGCAGCGCAGTGCATGGTAAGTCAAGTCTGATCTTTT
ATCTGGCAACTATGAATCTTAGTCGTGTCAAAAAGGGTTGAATCTGACCAACCAATGGGTAGGAGTTGCTAGATGTCTAAATACAAGGACAATCT
TATCAGTCTAATCATGTGATACATTGAGTGTTTGTTATGCAGATGGTATGCAAAACCCATCAGCATGGTAAGTCGCATTGCTTTCTCTGGCAACT
ATGAATCTTAGTCGTGTCAAAATGGGTTAAATCTGACCAACCAATGGGTAGAAGTTGCTAGAAGCTTAGATAAGAAAGGGCATAATCCTTCGAGT
CTAATCATATGATGTATTATTTAGTGTTTGTTATGCTTCTACTTCTGTGGATGGCATAGATCAGCCATCTACATGGTAAGTTGCATTGCTTTCTC
TGGCAACATTGAATCTTAGTCGTGTCAAAAAGAGATAAATCTGACCAACCAATGGGTAGGAGTTGCGAGATATGAATCGAAAAAAGAAAAACATT
TAGGGTGTTACTAGTCTAGAACGAGATGGTATCATTTTTGAAAGGTCTGTTTTTCCAACCTAACCTTAACAGCTAGAGTTCAAGAAACTTGCTGG
AATGCGACAGACTTTCACACGCAGCGTAATCATCACCAACCGCCAGCTTTGTGCCATTGTGCGCTTAATTGAATAAACAAATGTAAGCGAACAAC
GGGAATCGAAGAAGCACCAACTATGCGCAGTGAAAGTTTTGTTTTCGTTTTTGTAAAAACAAGATTTTGATGGTTAAAAGAGAGGCCGAAAAGC
AGTTCACTGACATGTCAAGAATTTGGAAGTGTTGATGGATGGAATGCGGAGAGTATGGAAGATATGAGAAAGTGAAAGCAAAACAAAAGTTGGAG
GCAGTACGAAAACTAAAGAGCGAACGTGCGGAAACTCAGTTAATGGAATATAACCTAAAATAGATGAAGGCCAAAAAGAAATGGTCCAAACAACA
ATGAACACATGTTTTTGCGCGTCGGCGTGTGCGTGCGCGCAAGTTTGCCGCTTGGAAACAACACACATCACACGAATAAAACGAGAAGAACGGGC
AAGGAAACAATGAAACCACCAATGGGCGGGGCTGCGATAAGCAGTTTGGGCAGTATGGAACCATATTATTCCATCATAATTGCAATTTTGTGCGA
AATTGAGACGGAAATTTCTAGGCGAACAGTTGATGAGTGCCACGAGCCAGCTGTTTAGCCCCCATCATCCCCCCGCACAAATCGTATACATCCAG
AATAACTGGAACTGATATAATCATGTGTGTGTGTACACACTGGCGGGAATTGAGTGCGTGTGTGTGTGCGCGACGAGATTAACGTAAGCAGTG
CACTGTGGAACAAGTTATGAAACACTTGGAAGCCGTTTATCTGGTCTCCTATGAAAGACATCTTTCAATAAAGTCCAGTTTGGACTTGCGTTTAG
CCCCACTGTATGACATGCGCTAGTGTGCGTGCGTGTGTGAGTAAGCGAGTGCAAAACTGCACACGTGTTTTCTTTGTTTCGCGCGGAAGGGGGCT
ACTTTTGCGGGCAGTAAGACTAAAAAAATTACACTACTTTTGCGGGGATTACTCACCATCGGCTGGCTGCTGGAAGTTGACGTAGGCATAGCCCA
ACGAGCGACGGGTAATCACATCGCGGCAGACACGAATGGACAGCACTGGACCAGCAGACGAGAACTTGTCAAAAAGTCCCGATTCGTTGACGTCC
TGTGGGAGATCACCGACGTATAGAGAAGCCATATTTGGTGATCAGGTCTACCTGCAATTTTTAACAATTAATTTCCACTTTTTTGACACTGAATT
TTGGGTTTTTTCTTAATCTTTACGGACCGGATGGATTCGACCAGGCAGGCGGTGAAATAGAAAGAAAAAAAGCGGCGTGGCTTTCGGTCTTCTAT
TCGTCTCTCTGTCTGTGTGTCTGGGTGGCAACACTGGTACATGTGACAGTCGGTAGACATGGCAACGTTGGCATTTGCTTTGTTGTTGCTCTTTG
CTCTCCCCTTTTATTTCTCTTCGTGTTGGAAAATTTCCACACAGACACAAAGATAGACACGCGTTTGCCTGATCGAATTTTGGGGAATTCTTTGA
TTTTCTCGAAAATATGCGACAACTAGTTCCTAGACCACTATTTTGCGGGCAATCTGGCGTTTATAGACGCCATCTTTGAGCGAAGAACGACCGCA
AACAAAGCAAATTTCGATGGGAAAGGAAAATTTCCCTATTCGCTTTGTCGTGCGTTGCGCCCTCTCACTCTCTACACCATTGTAACCAATAGCTT
TACACTGTACTTACTTCTCAAACACGCTCGATTTTTTTTGCTACTTTTTACAATTTTTTTTGTTACGTTTTTGTGTTTTAATATTTTTTTTTATT
TTTTATATGTTTTTTCTTCACAAAAAATATGTGATAAGCCGTGTGCTGAAAGCGAATCCACGACCGCTCACGTAAACGGACTCTACACGACTCAT
AGAGAGGAGATTCGTTAGCGATGACCCCACAAAGTATCGATTAAATCCCACTGCACAATGCTGCCACATAGGGTTAGAGACAAATAAATGTCACT
AAAAAATCCGTGAGGACAATTTACTAATTACGAAGCATTATTTTGAATTTCAAAAAAGCCAGCCATCACACATAAAAAATTTTTATATTTAGCTA
ATTCCCGAAACATGAAATACTTGTGCATTTTCAGGGGTTCTTTGGTAACTCTGCTTCATTTATGTTCTGATATTTTCGCCAATGTCCTTGAATAC
TTTGTCTCATAAAACACAATCCAAAATTAGGAATGCAGTTTTTTTTTCTTTTAAAAATGAGCGTAGACTTTTAGAAAATGATTTTTTGGCACTGC
ACAGATATTAGCGTATGCTCCGAAAACCGAATCCCATCTTTGTAATTCCCCACTGTGCGAACTTACCTAAATCAGAGAATAAAGCGATGAGGCTG
CAAGTCGACACTCCGAGAAGTGCTTGAGTACTTCTTTTCGTTCTCGATGGAAATCGGCACTACAGAGATTGAAGAATTTTTTAAGTTTTTTTTTT
GTGTTTTTGTTTTTACGAAATAGACCACATTCAAGGATGGCTGAGGATAATTTTTTTTTTCTTTTTCCCGTTTTGAACGTCTGGTGCATGTGCCC
TATCTGGCGATCGAGTACCTAATGAAGCGGTGTGAGGCGTCGGTGCCTGACAAGCTTCAAAGCGAAGTGTCACTTTGGGCGCCTACTGGCGTGTC
CTGAGTAAAATCTTAAAAGATTTGACATTTCGGAAACATTTATTTGGGCATTATATACTTCATTAAACATATTTCGATCTGGTTTGGCCAAACAT
TTACTTGGCTTGAGAATTAGTTTGCTTTCAACTCAATTTTGATTTTTCGTAGCATTTAATAGTTAAACATAAAACGTACTGGCTTAATTCATTAT
TGTGTAGTTTTG
(SEQ ID NO: 553)

Exon: 6422..5823
Exon: 5751..5567
Exon: 3826..2342
Exon: 2272..1965
Exon: 1897..1001
Start ATG: 5732 (Reverse strand: CAT)

Transcript No. : CT16411
ATTCGCTTTCAGCACACGGCTTATCACATATTTTTTGTGAAGAAAAAACATATAAAAAATAAAAAAAAATATTAAAACACAAAAACGTAACAAAA
AAAATTGTAAAAAGTAGCAAAAAAAATCGAGCGTGTTTGAGAAGTAAGTACAGTGTAAAGCTATTGGTTACAATGGTGTAGAGAGTGAGAGGGCG
CAACGCACGACAAAGCGAATAGGGAAATTTTCCTTTCCCATCGAAATTTGCTTTGTTTGCGGTCGTTCTTCGCTCAAAGATGGCGTCTATAAACG
CCAGATTGCCCGCAAAATAGTGGTCTAGGAACTAGTTGTCGCATATTTTCGAGAAAATCAAAGAATTCCCCAAAATTCGATCAGGCAAACGCGTG
TCTATCTTTGTGTCTGTGTGGAAATTTTCCAACACGAAGAGAAATAAAAGGGGAGAGCAAAGAGCAACAACAAAGCAAATGCCAACGTTGCCATG
TCTACCGACTGTCACATGTACCAGTGTTGCCACCCAGACACACAGACAGAGAGACGAATAGAAGACCGAAAGCCACGCCGCTTTTTTCTTTCTA
TTTCACCGCCTGCCTGGTCGAATCCATCCGGTAGACCTGATCACCAAATATGGCTTCTCTATACGTCGGTGATCTCCCACAGGACGTCAACGAAT
CGGGACTTTTGACAAGTTCTCGTCTGCTGGTCCAGTGCTGTCCATTCGTGTCTGCCGCGATGTGATTACCCGTCGCTCGTTGGGCTATGCCTAC
GTCAACTTCCAGCAGCCAGCCGATGCTGAGCGTGCTTTGGACACCATGAACTTTGACCTGGTTCGCAACAAGCCCATTCGCATTATGTGGTCTCA
GCGTGATCCTTCTCTTCGTCGCTCAGGTGTGGGCAACGTGTTCATCAAGAACTTAGATAGGGCCATCGACAACAAGGCAATCTACGACACTTTCT
CCGCCTTCGGCAACATTTTAAGCTGCAAGGTAGCCACCGATGAAAAGGGCAACTCAAAGGGCTATGGATTCGTCCACTTCGAGACCGAGGAGGCC
GCAAACACGTCCATCGACAAAGTCAATGGCATGTTGCTCAACGGCAAGAAGGTCTACGTGGGTAAGTTCATCCCGCGCAAGGAGCGCGAGAAGGA
GCTGGGCGAGAAGGCTAAGCTCTTCACCAATGTATATGTGAAGAACTTCACTGAGGATTTCGACGATGAAAAACTGAAGGAATTCTTTGAGCCCT ACGGCAAGATAACCAGCTACAAGGTCATGTCCAAGGAGGATGGCAAGAGCAAGGGCTTCGGATTCGTTGCATTCGAGACAACAGAGGCTGCTGAG
GCGGCCGTTCAGGCTCTCAATGGCAAGGACATGGGAGAGGGCAAGTCCCTGTACGTGGCTCGTGCCCAGAAGAAGGCCGAACGCCAGCAGGAGCT
GAAGCGCAAGTTCGAGGAACTGAAGCAGAAGCGTCACGAGTCTGTGTTCGGCGTTAACTTGTACGTTAAGAACCTGGACGACACAATCGATGACG
ATCGTCTGCGCATCGCGTTCTCTCCATACGGCAACATCACATCGGCCAAGGTCATGACCGATGAGGAGGGTCGCTCCAAGGGATTCGGCTTCGTG
TGCTTCAATGCCGCAAGCGAGGCTACCTGCGCCGTCACCGAGCTGAACGGTCGCGTCGTCGGCAGTAAGCCGTTGTACGTTGCTTTGGCCCAAAG
GAAGGAGGAGCGCAAGGCTCATCTCGCCTCGCAGTACATGCGTCACATGACCGGCATGCGTATGCAGCAGCTGGGACAGATCTACCAGCCCAACG
CGGCTAGCGGCTTCTTTGTGCCGACCCTTCCGTCAAATCAGCGTTTCTTCGGTTCCCAGGTGGCCACTCAGATGAGAAACACACCCCGCTGGGTG
CCCCAGGTGCGTCCCCCAGCAGCCATACAGGGTGTCCAGGCCGGAGCTGCCGCTGCTGGTGGCTTCCAGGGCACAGCCGGTGCGGTGCCCACTCA
GTTCCGTTCGGCTGCTGCTGGCGCTCGCGGGGCACAGCCTCAGGTGCAGGGCACACATGCCGCCGCTGCTGCGGCTAACAACATGCGCAACACTG
GAGCACGCGCTATTACTGGCCAGCAAACTGCAGCACCCAACATGCAGATCCCCGGAGCCCAAATCGCTGGCGGTGCCCAGCAGCGTACTTCCAAC
TATAAGTACACCTCAAACATGCGCAATCCTCCAGTGCCACAGTTGCATCAGACCCAGCCAATTCCACAGCAATTGCAAGGAAAGAATTCTGAGAA
GCTCATTGCCTCGTTGCTGGCCAACGCCAAGCCGCAGGAGCAGAAACAGATCCTGGGCGAGCGTCTGTATCCGATGATTGAGCATATGCACGCCA
ATTTGGCTGGTAAGATCACCGGCATGTTGTTGGAGATCGAAAACTCTGAGCTCTTGCACATGATCGAGGATCAGGAGGCCCTTAAGGCCAAGGTG
GAGGAGGCTGTGGCCGTGCTTCAGGTGCACCGCGTCACCGAGCCCGCCAACTAAGCTCGAACAGCTCAAGCGTATGAACATTTTACAAGAACACT
TTACACCCAAAAATTTCCACTAATCTTTCAATACATGAACAACAAAAATTCGCATTCACTGATGCTTTGCGCAGGGGAGGATTGCCAAGGACAC
ACAATTAACACAGAAAAACAAAGCGAAAAATCTACGGCTTTTTCTTTTCTAATCCCAGAAACATCAACAAAAGCAATTTCAATCATTTAATTTCG
AACGCATTTACGCAAGTACACGAAGCAAAAGAAGAAAGTCACGCAATCAAATTCTGCAGTCCACTTATAAATTCTTTTTTTTACATAAACATGT
TAATTAAAAAAAAAAACGGAAAAATGTGAAATGAAAAAAATTTCGTTATTGCTTTAACTGGATCGATATTATTTTGTATGCGTATAATGAAAACA
CCAAAAAACCATTGCAAAATAAACAGATTAAAGCAAAGCATACATGTAAACCGCTTCTTGCAAGTATTGAAATTGTGTTTTAAAAATTTTAAAGA
AGTTTCTAGTGTTACATACATATTGAGTTTTTCGTACACTTTTTCCATCCACACTTTCAAACAACAACAAACACGAAAGCGATATGTAATTTTTT
TCAATTCTTTTTTCTCAAATTCAAACTTTAAGAAAGCTTTGTTTAGAAAAAGAAACGCGACAACCATACACTTTTAAAAAAGCAAAGAAAAAACA
AAAAAATTGCAAAAGAGTTAAAATAAAACGAAAAAATGGAAAGCAAACTGTGCAGAGAACAGAAGAATAGAAAGAAAGAAAGAAAAAGAAAACC
GCAAGAATATGAGAGTCAAGTTTTTGCTACTTTGAAAAAAGAGAGAAAATACAGAATACCAACAGCTGAAAAAATATGTTGACAAATGAAAACAA
AACATAAATCGAAAAAACTACAAAAAAATGGCAAAACCTATGTAAAAACAGCAAA
(SEQ ID NO: 554)

Start ATG: 620 (Reverse strand: CAT)

MASLYVGDLPQDVNESGLFDKFSSAGPVLSIRVCRDVITRRSLGYAYVNFQQPADAERALDTMNFDLVRNKPIRIMWSQRDPSLRRSGVGNVFIK
NLDRAIDNKAIYDTFSAFGNILSCKVATDEKGNSKGYGFVHFETEEAANTSIDKVNGMLLNGKKVYVGKFIPRKEREKELGEKAKLFTNVYVKNF
TEDFDDEKLKEFFEPYGKITSYKVMSKEDGKSKGFGFVAFETTEAAEAAVQALNGKDMGEGKSLYVARAQKKAERQQELKRKFEELKQKRHESVF
GVNLYVKNLDDTIDDDRLRIAFSPYGNITSAKVMTDEEGRSKGFGFVCFNAASEATCAVTELNGRVVGSKPLYVALAQRKEERKAHLASQYMRHM
TGMRMQQLGQIYQPNAASGFFVPTLPSNQRFFGSQVATQMRNTPRWVPQVRPPAAIQGVQAGAAAAGGFQGTAGAVPTQFRSAAAGARGAQPQVQ
GTHAAAAAANNMRNTGARAITGQQTAAPNMQIPGAQIAGGAQQRTSNYKYTSNMRNPPVPQLHQTQPIPQQLQGKNSEKLIASLLANAKPQEQKQ
ILGERLYPMIEHMHANLAGKITGMLLEIENSELLHMIEDQEALKAKVEEAVAVLQVHRVTEPAN*
(SEQ ID NO: 555)

Classification: RNA_binding
Gene Symbol: pAbp
FlyBase ID: FBgn0003031

Celera Sequence No. : 142000013384618
ATCCTTTGTTAATCATGTTGCTATTTTTCAAATTTATATTCAAAAAAAAAGTATTGAACATTATAAAATTGTGAACTTCCCTTCTCAAAATATTT
TAAAATGTGAGAAAGTAATCAAGCTTTGTCTAAAAACTCCCTTTTTTCTACTACCTTTTTAACTCATTTAATCCGCTCATAGAATATACTCCCAT
TTATCATACTCTTTCTACTCCGGTTTTTTGGCCTCTTAAGAACGCTTGCTCTCCCTCCGCTCTCTTGTTTAAACAAATACAAATCAAAACCGAAA
GCAAGAGCAAAGTGCAATAACGAAAACCACAAGCAAAGAGTGTTGTACAATTGCAGTTTTTGTTTTGCTTTAGCGTTCGCTAGGCAGCGCAGTCG
GATATACTGCCTCTTCGCTACTTCTGATGAGTTTTCTTCTTCTTCTGAATTTACCTGCTCGACAAGATCTTTGTGTACCCACACATACACGCGTA
CACAGCCTGCCCACACACTCTTAGTTGAAACGAGAAAGAACGTTTTGTAAGAGTACCAACTGAGACATACCCTTCACATTGTTTGTGCATCTAAA
TATGTACTTTATGTTGTAAGTAAATATGAGTTATAAAATAGTGTTACTTCAGCAATTAGTGCGCTGGTACAATATTTCAGTTTTTTCAGTATGCG
AAAGCCAATCAATTAAATTTTTACAACCTTAAAATCTAGATATGTTAACTATGCTCCTTGATGCATTTATGTAGACGCAATTCATGGTCCGAGTA
TACTCTTCCTCACTCAGCTATTACAGGGTAGGTAAAGAGCGGGATTTTTTAAAATATTTTTTTTCTCTCAAGTGTGCCTCCTTCATGCACGTGCA
TGTGCAGGAGAGGGAGCGAGAGAGATTGCGATTGCACTGGCTGCGCGCCTACGCTGCCGCTCTGCCGACGTCGCGGTAGAGGCTCTGTTGCCGTA
GTTTGAGGCCCCAGTGCGAACAGTTCATTTTAGCCGCGGAGCCAGTAAGACGTGTTTCCTGCCCTCTTTCTTTGAGTCTGCGACACGTTTTAAG
TGCTCTTCCATAATTGACAACAGCAAAAGCAAAGAATAAAAAAATAACAAAAAATAAAAAACGAAATCCATCGTGAACAGTTTTGTGTTTTTAAA
TCAGTTCTAAACACGAAAAGGGTTGATGAAAAACGCAGAAGAATCCGAAAAACTAACTAACCGAGCAAAAACTTGACTTGAGTGTTGTTTGACAA
ATCAGGAAAGATAAAAAACAAATCATAAGAAAAAACTGCACGAAAAATGAAAAAGTTTCTAATATTCAAAATCTTGCACAAGAAATACAAAATCA
ATTAAAGTGAACTCTAACCAAAAGTTGTACACAAAATAAAAAGCAAAACAAAGCAGCGAAGAACAATCACAAGAAGAGCAAAGTGCCAACAAAGT
GCAGGAAGGAAGGAAGCGGATAAGGACAAAAAGGAAGCCAGCACACACACACACCCACACAATGGCCGTGCCCTTTATTTGCCCGAGGGCGGCG
CCGATGACGTAGCGTCGAGTTCATCGGGAGCCTCGGGCAACTCCTCCCCCCACAACCACCCACTTCCCTCGAGCGCATCCTCGTCCGTCTCCTCC
TCGGGCGTGTCCTCGGCCTCCGCCTCCTCGGCCTCATCTTCGTCCTCCGCATCGTCGGACGGCGCCAGCAGCGCCGCCTCGCAATCGCCGAACAC
CACCACCTCGTCGGCCACGCAGACGCCGATGCAGTCTCCACTGCCCACCGACCAAGTGCTATACGCCCCTCTACGAGTGGGTCAGGATGTACCAGA
GCCAGCAGAGTGGTAAGTCTACAAAGATCTCAATTCTCCACTCTTAAGAACTTTGAAATTGTGTGGGTTAATCAGGATATCCATTTAGTTTACCT
CAAATACATTTGCAGATACAAAAATAAGTTTCGATTCATATACGGTTATTAATTGCGAAATGTTTAAGAAGTTCCCACACAGAATAACTGCTTAC
GCATGTTGGTAATATATTTTCTAAAATGCTTATAACCAACACTTTATTTAAGCCCACTTGTTTTGCTATTAACAAGAAGGATTTTCATAGGATCT
CCTTGTAAAAGTAAACAAAAAATGTTATTAACTTGAAATTGCTTAAAGAATAGTAAATTTATTTCTTTCGAAAAAACAGCATTTTAAATGTTTGA
AGATATTTTCAAACTAATAGATTTGATCAATAAAAAATGGCGAACAATTTTTTCTATACAAGCGACTTTAAAGGTTTCATATTTTTGATTACCG
CTTTTAATATCATTTAGTTTAGTTTAAGAAAGTTTCTGGACAGCCGGAGGGTTTCCCTCATTTTAAAATGGGTCAGCAATTAGCCAAGTTGTGAC
GTTATTTGTTAACTGCTTCAGTTCCCCTTGTGCAAGTTTCACTTTTCAAGGTTGTTGATTCATCCAGTTTCGAGTAACTGCGTCAACTGCATCCA
GGTTGTTTTTGTTTACTTTTACCCAGTTTTTTTTTATTTTATATATGGTCAATTCAGCACTTTGTCAGCTTATCAGCAAAAAAAAAAGTGTAAA
AGGCAGAGCGGAAGGCAAATTTCTCGGCCACATTCGAAAGGAAGCCGAAAAAACGGTAATTCAATAAAAATTAATCGAACAAGTTCAAAAAGGGG AAAATTGAGAAGTAATTGAGAAGTTTCGATTGGAGGAGAGAGCAAACTTAATAAACGAAGTCACAAAACTGCAAAAACTCAAAATCATGTGGGGA
ATTACTGGATCAAATTCCCAAAGTGGGAATCTTACAAATTAAAAAATTTTGTATTGAGACAAAAATCTACTTATGTTATAAATAAATGAAAATAA
AGTAGAAATGGTGATAACTAGCTCGATAAATCACATTAAGATCAATTTCCTTCGGTCATGATTATCTAAACTAGGCTGATAAAACTTTTAGTGTG
CTATGGCTTTAAGAAAGAAACGCCGAGACACATGCAAGACAACTGCCGAGTTGGCTGTCATGCGATATTGTTCGTAAATATGGTCAAAAAATTGG
GCGTGTGCTGGACCAGCAAGAAAATAAAGACCTGGCTGAAACCAGGGAAACATAACCCAGCGGCAATAAAACAGAGCTGGGAGCACAGAGCTAAG
CACGTTTAATTGGCACGCGCCAAACTCGAGTCGAATGTCTTACTTTTGAGACTTTTGAGTGAGTGTGGTGTGCCTGTGTGTCTGGGTATCTGCAA
GATATCTATCTATCTCGAGCGTACTGCTCGTATATCTTACCACTCGACTAACCCAAATTATTAAACGCCATTTGACCTTAGGCAACTAGTTTTCC
GATTTTCCAAAAGGGGGCCAAACGGGTTGAGGGTGTGGGCCATTTGCAAAGTGTTTGACTTAACGGTTGTTTAAGTAGCTTTTGTGCTCGGCCAC
GTTGAGTGCGGTCAGTTTTTATTGTTTTTCTTTTTTTTGCGCGCGCTTTTCATGTTTGCTTTGCGGTTTTTCATTCGCGTTCCTTAATTTTGT
GTTGCCTTTGCATAATAGATTTTGTCGCTGTCGATGATTGCCAGCTGCGCTCTTTGGTTCCACCGAACAACCGAATTGTTACTTTATATTATTTT
GCTGTTTTATTTGGTTTGTTACCTTTTTTGCTGTCAGCAACAGTTGGTCAGACGAAAAAAAAGCGTTCCCTTCTCGAAATTACAGTGAGTCACTT
TTGGGCGCTTCAATCTGTTTTCGTCTATAATATCATAATTTATACAGAGATACTTTTTTTTCGCTTACGAGAGCTGATGCCCAGTGAAAATTCGA
TTGCGGGGCATTTATTTTGAAAAACGAGCTAAAAAGACTTGACGTTATCGTGAAAGTTTCGATTTAAAAGTAATTTTCCCTTATCTCATTTTCCC
GAACCACATCTAAGCCCCTACTCAACGCACGCCGATCATGTACTTTAGTTAGCCACTCAAGAGGATAATTTATCTAATCGTGACACATCCCGAAA
CTAGTGAACAATGCTTGAAGCCCTTGAAACAAGAAAGGGATAAACTGTAGTTAACCAAGAAGCGAGAACCCTTTTTCCTGGTTCCCCCAGCTATG
CCATACATACACACATACATGCAAGCCAGATTCACGGAATACTTTTAGCCAGAAACGCGCTTAGTCATCAGCCAGCTATCAACCCTAAAAGCCTA
AAAATGCGAGGCGCAAACAACCCCGACAAAAATTCCTAAATACCAACAGAGCTTTTCCCTACCAAAAGCAAAAAAAAAAATGCGGCAGGGAGCCT
TTTGTTTTGGGAGAGGATTATGCATACAGCATCCAGAGCCCACCACGTAACCCATTCCCAATGGCGACCAACAAAAGGTGCAATGACAGCAGCGG
TTCCCTAATCAGTGATGGGAACAGGTACATTTTATCTGTTGGCTAATTGGATGCAGATTAAAAGATGCGTAAACCTAGCGGTTATTATGTAAACT
ATTATGGACTATTACTTTTTTGGTTCAACATTTAGTTATTAACATAGATTTTTGTTATCATAGATAATAATATGTACCTATGTAGGTACAGTGCA
GAGTACAAAAATGTTCCCCACCGTACTCAACTCCAAGTTTTGGTCGCTCTGCTTTGGCTTGCAAATTCGCATCATTCGCTTTGCTGTTGCCAACA
GCTGTTCTGCTGCTAGGCGTTGTTTTTCGCTGCCGGCGTCTCTGCCGCACTTGACATTTTCAACCATTTTGTTTTGCTCGGCAACTTCGTGTAGG
TGGACTTTAGTAGAAAAGAGGAGCCATAATGGCGGCAAAAATGGCGACTCCTGCCGCATCCTGCCTGGCAACAAAACACAGCTGACTGCTGCGCA
GATAGAGCGAGATGAAGCCTACGCCTGGAGAAAGAGAGGGAGCGCAAAAACTCCGATTAACCGCAAGTTTTGAACTCCTCTTTTTTCTGCACAGC
ATCACAAAGGGGGTGGGAAAATAGGAGGAGGGTTGGATGGGAGGAGGTTTGCCTCCGCTTTTCATCATCGTCATTTCCATCTCGATTTGCTTGGC
CTGTTGCCAAGCTGATTTATACGTACAGGCGGCTTTTTATATTTACATACTTTGCATTGCTTTTTTCTGTTTCTCTCGTTGTCTGCTTTATTTT
TTCGCTTTTCGTTGGTATTACGGCTTCGCCTTTACATTGACCGTGATTTTTGGTTTCCTTCTGGTTTTGTTTTCGATTTTTTTATTTTTCCCTTG
CAAATACATATGCAGCTTTTTTTTGTTGAGTTGCGTCCTCTGTAATTGTTACATTTCATTTAAGTTTTATATTGTCTTACAGCTCAGTTTTTTAT
GACTTTACTGCTTTCATAAATTTGGCATAAACATTCTTGACGATCTGCCCGAAACAGCTGCGACAAATCCAATCGGAAGTCTTTACTCGAAAATG
ATTCGCTCATAAAAGTTGAGAGTGGGTTATGAACAAAAAACTTGAAAACCAGCTGTCAAACACAATTTCTATCTGAGCCCAAAACTTTTGAAGAA
ATAGTTTCACTAAAAATACACTTCTAAAAAGGTATAAAATTTATTTTATTAGTATTTTGGATTGCCAAATATTTCCACCCATTTATATACATACA
TTTATATACATTATATACATATGTTCAGCATATTGAAAATTAAATAATCCAGTTTGTTTACATTTCACACCACTCAGCGCAATGAACTTTACACA
TTTTTCAAGTTTAAATGCCCGCCAGGCACTTTGCCTAATAAGAAAAAATATTACCTGAATGCGAATATAAACTTGACACTTTTGAGCCACTATAA
GCGACGGGACACGGCTGAATCGGGCTCAGACGGTAGTCAGCCAGGATGCCTAAGTTGGCTTTTGATTAAGTCTCCGCTGAGGCCGTGCTAAATTG
TTTGCACTGAGGCGTTCGGGTTAAGTTCAGGGGGCAGTGGGGGGTGTTAGGGATAGAACGTGCTCAAGTTTTTGTTATGAAATTGAGCCTAGACA
AGCTAGGCAAAACCCCATCTGCGCTGACAACTCGACTCCTTTTCAGGAACTAAGGACAATGCAACTTGTGCGACACGCTCAAGGCAGAAGTGGAA
AAGGATATGTATCAAAAGGCGGAAAACTAAGAACAGGATATACTCCTCGGCACAAAACAGACGGCAGACATCATACCTGGCTACTTGTTATAATT
GGCAAGCTGGCAAACGCTCCAGACACCAGTTAACTTTCAAATTTTCCTCGCGATGAGCTCTCAAAGGAACATTCGTTGAAGGTGTTCTCCGATTC
CCAAAGGGAAAATGTTCCTTCGCGATTTACCTTCCACATTTAAAGAGCGCTGGGTGAGATCAAGTTTAAAGGGGCTTAAATGAGGAAGGATAGT
GGAATGGCATCTGATTTATTTGAAAGAGTTGAAAAACAAAAACACCTTTTGTTGTATATTATTTTTAACAAAACCCATTTCATTTGGCAATTCCA
ATTTTAATGTTCAACATTAAGTAAACTACTGAAATATGAACTCTGTTTAGAACTCCCCCTCCTATTTATCTACTGCTCGGGTTGAGTATCAATAT
CAACTTATTTGGTAAACAAATCAAATGCGCTTACTAAATGTGCAAAGTGCCAACGACAATTAAATCAACAAATAAGCTCGTGTAATTGTGTACGC
CAAAGGCAGTCGGTGGGTGGGTGTTTTCAGTGGTCTCGGTGGGTTGGTGGTTTGGTGGGTTGGTGGGTTGGTGGGGCACATCCGATCCACTGGAT
CGAGTATAGATAACCCTACGGGCACGCAAGCTCCGAGTGGTTGTGGATTGGATGACGCAGCGAAGACAGCCAGTCTGGCCCAGTCGCAAATGCAA
TTCCCATTCATTTATTAATAACTTTTTGCCGCGGCTGTTGAGACGTGCAGTTTGCCGTTTTGCGGCTGCAGTTTTGCTTTTTTTCTCTCTTTTTA
ATTATTTTAATTGCGTTGCATCTGATCGAATGCTGGCGTACAGTTTTATTTATTGTTTAATTGTAATTTTCGCATTTACGTTGTTAATTGCAGCG
TGGTACTGGGCGGAGATTCGGTTTAATCAACTACTAAATGCTTTTGGCTCGTTGCAAAGATTTTGAATTTGGTTAAGTGGCGATGGCATTTATGG
CCATACTTCAGTGCGGAAGTATGGAAAATTCGTGATTTTCATAAATAAGAACTAATGAGCTTTAGCAATTAACAAGAAATTAATAGAAATGTTTA
GTTAATCTGTAATATTTTACTAAATCTCCCAACTACACAGTTTCAAATTACAGTGTAGAACATTTTCTTTAAGACTTCTTTATATTTGTTTGAT
CCTTTTTACACGCTGATTCAGCCAGTTATATTTTACTGTCTTCCCAAACCATTTTCAAATGTTCCTCTTGCTCACAAAACACATGCTCGCCATTT
TCCACTCTTCCGGAAAATCCTTTGGATCCCCGGAAAATATGCAAACAACTGCAAAGACCAAAGACTTGTGTTTCGCTCAGTTTCCTGTCAATCGA
TGTGCATCGTATAAGTTCCTTGGGAACGTCGTCTCATGCCTGATTTTCCTTTTGGCTTTTTATAGCCTTTTAAGCTGTTTTCCTTTTGTTGTGTG
GAGTGAAGAGAGGAAATTGAAAAATTGCATTTGTCTGTCGCTGATAAAATATTGAGCAGCTTGCTGCACATTCTCCCTGGTTTTAGCTGGGCTGT
CGTGATAAGCGTTTGAGCTATTTCCAGAAAAACGCTCTCATGGAGATTGGCAAAGAATGAAAATGCGATGTGGGTGGGAGAATTTCGGAATTCCA
TTCAGCTGTCCCTCAAAGGGTTTCCTCATTCTTTAAAGCCGTTTCCAACGGCTCTTAATTCCTGAAATATTTAATTAAATTCTTGCATATTAGCT
TTATGTGGGCTTTAATAATGGCTCGCGTGTTTGCTGGCCCCGTTTTTGTTTATATTAGTTTATAACCTTGCTGCGGGAAGATTAAAATATTTTAA
ACGCATCACGATGCGAACATAACTGGACTGGGTTAGATCATCAAAGCTTAGATTTAGAATTGCCGACGATATGAGCTTTAATATCTTCATACACT
TGACCTCTGTTTTTATTATCGAGAATTTCTGCTGACTGAGTGAGTTTAGTGATAATTGTATTGTTTGTATTCTTGGAGACCCACAAGATTGATGC
GTGAATTTGATTCAATCGGGATTTGCCAAATCATCAAACAAAGAAACTTTCTCCTTGCCATCGAGACATTACGCAAGTTAATTAAATTGCCATGC
TAAGAATCATCCTTATAACATCTCACGAGAACTTTCTCTTTCTGTTTACATGAATCACTTGTGACATTATCAAATTTGTCATTAGCTTCCGCATA
TTTTTCACCACTCACTTTTGGATATTTCCTTAATTCACAAACTTCTCGCATTCCACAAATGGCTAATTAGCGGCTTACCGAAATTGGCCAATAAC
AGCGGGATCTGATCTATAGATTGAGACTCGTACATAGATCGACACCTGATTGACATGCAGTTCGAGACAAAAACTGATCGAATTGTGCAAAACCC
CAAAAAAGGCATTTGTAAAACAGTCTTTTGTCATATATAGAAAAAGCCAGAACACAGAGATTCTTAATCAGGAGTCGTCGGCATTGTTTTCGGAA
TTCTCTCCCAATTTCCTGAAGATCAATTAATTAGTCACTTGCCTTGGCCATGAGCAATTTTACCGTTCGACTGTGCGGGGAGAAAATCGGCAGCT
GTTGTTGCCTAATTAAATCGAGGTGACAGGCCAGACAGACGGACGATCAAGTGAAACTCGAGTTGACCAACCAAATTAGTAATCTCGCATCGTGA
CAGACGACAAATCGCCTTAAATGAACGACTTCAAATGTAATTTTTGTGGGATTTTTATTTACTGTTTTTGGTTGTGGTTACAGCTGCTTATTCTG
CTTCCTCTTCGTGTGTGGGCGTTATGTGGTTGGTAACTGTAAAATGAGTTTATACACATTTTTTTTTTTTTGGCCAAGTTATTCGGCATTATTCC
GACGTGCATCATATCATGTTGTAATCTTGGACTTTGCTTAACCCCAGTTTTGAGTTCGGTATGGAGTGTTTCTTTGTTCTGTCATCTTGAGCTTG
TTTCGGTTCTGTTTTTCATGTTTTCATTTTTAAATTAAATATTCATCAATAAATGTCAATGTCAAGTGAAGTTGCCGCTGGCTTTCGAGAGGTTT
CGAGATTTTGGGAGAAGAGATTGCAATTTGCTGAAAGACTTGGAGTTGTGATGGCACAAATGAAACATGCGGTTATTCTGTGAATCCATGACGGA
TTTATACATCACGTATGCTATATATTTATTTTTGATTTCAAAGATTCCAGTTTCAACTGGAATTAGCTTCTTTATTTTCTTAAAGTTCGTGGCTA

FIGURE SHEET 306

GCCTATGAATAAATATGTTGAATATCATTTTATTATTAACAAAAACTCCGTTCCGCAGGTCAGGTTGTTAGCCACCACTTCCTTCCTATATCTCA
GCTGGTCAATAGCTTCCTCCCTCGATATCTGGCCGATTCATATGGCATTTCCCATTCCGTTCCACTGACCAAGTTATAGAACTCGCACTTTGCAA
ACTCGTTTAGCCCCCGATACCGATTGCGATCCCAAGTGCGACGCAATTGTTCGAGTTGGGCCGTTGGAGATACGAGCCACTCGAGTACGGGCTCG
TATTTATTCATACTTACCCGTGCAGTGCCGGTGGTGACTCTAGTATATTTTTATGTGTAGTTTTCTTGTGCATTTTTTCTTTTTTTTTTTTTTTT
GCATTTAGTCAGCACTTCAAGGTTATAATGAGCAACATATGCTGCGGGTACGCCAGCCAGCAAACTGCAACTGCAAATGCAATCAACTGCAAAGG
CACAACTAAAAATGCATTTCAACGTTGCCGACGACGATTTGTTCTTTTGTGTGGCAACTAAAGCGAGGCATTTTTCACGTTTTTCCGCTGCCTCC
GAGCTGTTCTTGAGCTTTTTCTGAGGCGTTCTGCTTAGTTAAACTTTTGCCTGATTGATGTTTGTCAGCTGCTGCCCAGCGGCCTTAGAAACGGT
TGCAACATCGCCTAGAACCGATGGAGAATTAAAGTGAATTATACACATAATTGCAATTTTTTTTATTTCAGTCGCCGTTGTTATGTCCAGATGCG
ACTGGCACTCGTAATTCAATTAAACATTTTGCCCATATTGTCGCCCGTGGAAATATAAGCGAATGCAGCAATTCGAATAAAACAATACTCCTAAC
AATTGGTCACGTTTCGTCACCAACAACTGCAGTGCTAACAACTACTGCATCGCCCGCATTGAGTTGTGATCATAAAATTCTTCCACCTTCCCACC
TTATAGAGATGGCGAGGAAAACTCGAAAATATATCACAGAAATCACAAAACCACATTTAAATGAAAATAAATTTTCCCTTGCAATGCGTGACTCA
ATAGACGTGTTTAAAGAAATTAACACTTTTTTCTCTAAGGGTACACCCCTTGTACATTTACGAATTGATTTAAATATCTCATCATCACCTATTTA
ACGTGTGAATTATATAACGCATATAAGCATTAGGTGCTATAATTAAGCGTTTATAAATCAAGATAAATCAAACATTTTCTTGCCTCACAAATTG
GAACAAAAAATCGTTTTAAATCATTTAATCACGCCTTTTTAAGTTTAAACAATTGTTTTATGCGAAAAAAAGAAACGTACACTATTGTTAAGCCA
GGTTCCCGTTTTTATAGAGAATTTCAAGCACGCTCACCTAAACAAAGATTAAATCACCATAGATAGTAGTTTGTAAACGTTTCGTTCTAATCGTA
GATTAAATCGTAATCTATGGCAAAATGCGCTATCTATCTTAGCTTATTTTAGCTCACGCAGTCACCACCAAATAAAAATATATGTTAAATATGAG
TAAGCGATTACTTACTACAGTTACAGTTACAGTTTGTAACTGTATAATTTCATAATAGATATTGTATACGATGAGAAAAGCCTATACAAATTAAA
ACAAATGTTCTTTAAGACAAATTTGGAAAGTTTATAATACATTTTAACATGTAGAACCAAATGAAGATGAGCATACATCTGTAGATTTGATTAAA
ATTAATATAGAGAAAGAATAAGACATCAATTCTTTCTCCACTCATGGCTCGAAAAATTGTATCACCTTAAGTGGTGATGGTATTTTTCTGTGTGT
ACCAGCATCGACATAGCATGGCTAGTTATATAAGTTGGCCAGGCAGTAATGATCCCTGCCGTTGGCTTCGCTTCGTTTCTGAAGCTGATGCTGAA
GCTGAGGCAAAACCTGGCAGATTTTCAAGGTTAACAGCGACTTTACGATGGCGCGCGGTGAGCGCACGTGAGTTGCCTCAGCTGCTGGCCAGCAG
CAGCAAACTAGTTTCAAATGCCTGGCACAGTATCTTTCAGATACAGATGGTAAGGCTGCGGCAAGGAGTGGCTCTTAACTCGCTTCGCCTCGGTT
CGCTTCGGTTTCGTTTGCTTTGGTTCGGATCTTGGCCCGCAATTAAATACCGATTTTTTGCGCTCTTGCAACTGCAACTGCGAATGCAACAGCTG
TGGGCTCGTTTCGACTCGATTCGAGTTCAAGGCTATTGGGTCAAATTGCAAATTAGTCGCCTGCAGGTTGACAGTGAGTGACATTATTGTGTATC
TGCACACTGCACACTGACCACCGACAAAGCGACAGAAAGACAGACAGACATGGATGTATGTATTGGGTAGATTGTCGGGCATTATCTGCGGTCAA
TTATCGTTCTTGCTGGCTGCTAATCGGTAAGATACACGTACTTCTGCCGCCGGCTGCTGTCGATTTGTATAAATTTTGCATTACAATCAATCATT
TGTCGCTGGGCAATGGCTTTTTAAGTAAATAAACATTAAGAAATCATACAGATGAAAATGTACACCCAACTAATGGGGAGCTCACAATTTATGCG
CATACCAAGTGGCCAGCTCGGCAGCGCATTTACCTATCAACGCTTTTGTTGTCGATTTGCATGAAATTGCAAGTAAAAAAAAAAAACAAAAAAAA
AACAGGGAGGAGAATACAAAAATTGAAATACAACTGGAAGTCAAATCGCAGATACAGATACGCTTCTCGTTACATGCATAAATGATGCTAAGCTG
GAAAGATTTCGAAGACAGATACAGATACTTTTCAAGTTGGGCCACTCAAGTAGACCCTCTTGGCAATGTTTGTTGCTAAAGATACAAAACAAAAA
AAAAAAAATAAAATACTTTGCCAAGTGAGCACGAGAATTGCCAATGACGTGTAAACAACTTGGATACAAATGCGCCTGCAGGCGGCTTGTAAGAT
ACTTAAGGCTGCGAATAACTTGAATATTAGTGGCCATTGTTCATGGATATGTATCAGAAGTGCAATATGTCGATAAAGTGGTGTATTTAGGAAGT
TTAATAGTATTTGTTGGAAGCCATATCAATTTATGATGAAAGCCCTAAATGGATAGTTATATTGTTAAATAAGCCATATTACTTAATTAAGGCCC
TTGGAGCAAAGGGAGCCGAAAGCCATTAAAAATTGCAACGTTCCAGTTTTAGTCGTTTATTTACATTTACATTTATCTTTAAAACAGCATTATGT
GGCTTCCTGCTGCACCGGCCGAAGATATTTTATTTTATTGTGCACTGCAAGCCTGTAACTGGTAGGGGCTGCCTGATCGTTTTATGGGTGGTTTT
ATGATCAGAGAGGACTTGCCATAATTGCGGCGGGTTTTACAGTCAGTCGGCTAAGTGGCAGTTGGCAAGACAATGGGATCGCCAGCGCCCCGACC
TTAGACACTTCCCTACATTGTCACTGACTCAATTTCAGACCCGGCCAATGCCGCCTTTGTTTACCTTATCCATTGTTGGGTGATCTTTATTACGG
GTATATGTAAGCGAACTGTACATCATCAAAATATTAAATATTTTAGACTTTTCAATAATATTAGTAAGTTCGTTTGATTTTCTTATTATGTGCCA
GCTGTATTTAAATTATTATTCGCTTAACTTTCGTTTCAGCCCCGCAAATCTTCCAGTATCCGCCGCCAAGCCCCTCTTGCAATTTCACGGGCGGC
GATGTGTTCTTTCCGCACGGCCATCCGAATCCGAACTCGAATCCCCATCCGCGCACCCCCCGAACCAGCGTGAGCTTCTCCTCCGGCGAGGAGTA
CAACTTCTTCCGGCAGCAGCAGCCGCAACCACATCCGTCATATCCGGCGCCATCAACACCGCAGCCAATGCCACCGCAGTCAGCGCCGCCGATGC
ACTGCAGCCACAGCTACCCGCAGCAGTCGGCGCACATGATGCCACACCATTCCGCTCCCTTCGGAATGGGCGGTACCTACTACGCGGGCTACACG
CCGCCACCCACTCCGAACACGGCCAGTGCGGGCACCTCCAGCTCATCGGCGGCCTTCGGCTGGCACGGCCACCCCCACAGCCCCTTCACGTCGAC
CTCCACGCCGTTATCGGCGCCAGTGGCGCCCAAGATGCGCCTGCAGCGCAGCCAGTCGGATGCGGCCAGACGGTGAGTAGCCAGCGATGCAGGGT
GCCAAAAGATACACTGCCTGGGTGGTGCAAAACCAATCAAACTGGAATTTAGATTCAGATCGATGAGCATACAGAATAAGAGGGAAAGTTCCAAA
CTATGACATGATAGGATGCAATTTAGACCAACTAAAATATACAAAGCTATACAGCGTGTATTCAAATTAGAGATTAATATAAACTATGCTAGGCG
TTGAATATAATTGAAGAATAATATGAACTTTAGTTAAGTGTAATACTTAAATTCATTTTCATTGATGTTTATAATTATTATATAATATTTATTAT
AATAATTAATAATCCCACTGAGAGAAATATAGTTGTAAAGGAACGAAGACTAGAAATCGTTACACACACGCTGTGAAATTGATTCGTACTGAAGT
ACCAAGCAAAATAGCTAGATTATTCATCGCAATCTCGACACCTTTCGCCCCACCCGACCCCCTTTTTCCAATTCCCATGACACAACGGCAAGTTT
TTAATTAATGAAATCGCAAAGTTGTCGCTGGATTATGTGCACACACAAGTGGCATATAGTGCTATACAACCCGAATCCGAATCCGAACCGACTGA
TAATTGCTCATGACGTTCCCAAGTCATCTGTCTATATGTGCAGCGATATTTATAGTGCCCATTATGCGTCTCTTCCCACAGCAAGCGATTGACCT
CGACGGGCGAGGATGAGCGCGAGTACCAGAGCGATCATGAGGCCACTTGGGACGAGTTTGGCGATCGCTACGACAACTTTACGGCCGGCCGGGAG
CGTCTGCAGGAGTTCAATGGACGCATCCCGCCCCGGAAGAAGAAGAGCTCCAATAGCCACTCGAGCAGCAGCAATAATCCAGTCTGCCATACCGA
TAGCCAGCCCGGTGGTACATCCCAAGCGGAGAGCGGTGCCATCCATGGCCACATCAGTCAGCAGCGACAGGTGGAGCGAGAACGACAAAAGGCGA
AGGCCGAGAAGAAGGTAAGAAATGGCCACCAATCTTGGAATGCACAACGCATACAGAGAAAGGGTATTCTCGTTTCGGTGAATCAGCATCACTAC
CCAAATCTAGTTAGCATTCATTGCCTGCCAACTTAATCTAATATACTTTAGGTTTTAAAAAATGTTCAAAAAACTTGAAAAGAACTATACAATCT
TGCTGCAAACATACATAGCAAAATATTTCCAACAGGCAGAGGCCCCTTCTTTGCTTAAGTCGCCCAAAACTGTCCAACAATTAGAATACAAAAGA
GGATATGAGTTGGGGAGTTCATTAACTCGGGACTTCACACATCTGCTAGCAGTTCGTGCCTCCTAAGTCCGTGGCACGTGGCAAACATTTTTCAA
AGGCTCAACTAGAGAGAAGTGCTAAAAATACGCGGCAAGGAATGACAAATTGCCGTACGCGAAAGGAGTCGCAGATTCGGATGCAGATACGAATA
CGATACGCTAGCAAAATGTATCTGTATCTGTATTTAGTGGAGTGCGGCCCGGGCATGTATAACACTTTTGCACATGCTAAATGTGCGATAAAAAT
TAATTGCGCAGTGCGAAGTGAAAGAGTCGCTCTTGTCACTTGTCTCCGCTTTATGTTAATCAAGGCAGGCGCCTCTATAGAGCCACATGTGCCCC
CTCCCCCCCCCCCCCCCCTTAAGTCGGGCCTTTGTGTATCGGCCCTCATTGAGCTCACTTTTTTACGCGTCGCGTTTTTTTTTTAGTTTTAGTTT
CTTGCGCGTTTGCCTGCGCAGTTGAAAGAAATGCAAACTTGAAGAAATTCAATCGCAATCGCATGACACACACATTGACTCAGACCTGATACCAT
TTCCAGTCCATTTCAGTCCTACATTATGTTATTCCTATTCCACTGCGATTTTGTTTTTATTGTAATTCATATGGGCTCCGGGCTGGCCGTTCTTA
TCGCTCATCGCATTGTGGGGGCTCATCCTTGGGGAAGCTGCCGACTGATCGGGAAGCTATATAGCGGCTCCCTCGGCTCCCTCGGCTCGCTGGGA
TCTGACCTTATCCGAGACTCACTCAGCTGCTAAATGAGAGCGTGAGAAATTCCGTAATCTGAAAGGCAACAGGCATGCAAAAGCTAGTGGTTCTG
CAGATGTAAATACATTTTAAAATATTCTAATTAACTATAGCTTAGTCAAGGATTAGAGAGTGGAAAACTTATAAGTAAGGAAAGGGAATGAATGC
TATACACATTAAACATAATTGCCAAACATAAATTCTAGCATGTGACAAACTGTACCTACACATCTAGTATTAAAATGTGTTACTTAATTCATAGA
TACTAAAGCACATTTTATTCGCATAATGGTGTGTATTTCACCATAATTTATTCTCCTTTCAATGCCAAAAATGAAATCAAAATATGGCCACATGT
TCGATGGCCTTTCATACCATTAACCGCATAGAAGAAGCCACAATAGTCCTATCAAAATATAGACTAAAATTCGAGCGAAAACAGCAGAAAAGCAA
ATTTGCATAATAAATGTGGGGTCAGTTGGATTTTTGGTGGTTGCAGTTCCACCACCTCATCATTCACACGTGCCGCACTGCAACCGTTGAAGCGT

FIGURE SHEET 307

GGACTATTGGACAAATAAATGGTGTAAATTATAAAACCATTGATGCGGGTTGGGGGGGAGTCAAGTGCGCTGTATAGAAAAATAATTACACCAGT
GACCGGACAAAAGTTGACCGCCCATTTGGGTCAGGCCACATGAAGTTCATCCGTCGGGCAGTCAATAGTTTCGCTTGATTTACGGTTCAAAAGAG
GGGTGGTTCGGTCACGTGTGTGGTTTTAGATATTTAATGCCGCACAGGGGAGCTATTGGTTGAACTGAATGATTTCTTGAAATGCGTTATATTAA
AGCAACTTGTTCTTTATGTTTAAGATTTGCCTTCACGTGCACCTGAATATAACTAAATGCTATTGTTTTATTCTCCTTTCAGAAACCACAGAGCT
TCACTTGGCCAACTGTTGTGACCGTTTTCGTTTTGGCCATGGGCTGTGGCTTCTTTGCGGCGCGATGAAAGCGCAGGAGACGTGTAATCGAATGA
TCTATAGTGAAATCAGCTAGCCCTTAAGATATATGCCGATCTAAACATAGTTGTAGTTAAACCGTACATAAGTGCAACGAATTTATTGAACTGCA
GGAGCGAAAGCAGAAAGTCATTAATTCGTAAACGGATTGTTAGATACACAAACAGCCAACATACACGAAGAGTGTGCCTAAGATTAAGAAGGTTG
ACGGGACACAAGAACAATATATTCTATCTGTCTATGGTAACTGCATTTGTATTTCTAAAACGAAACGAAAGATAACAATCTTAACTGCTCAAAGT
AATGAAAACTCTTAGACTGGCAAGAGACTCAAATCACACTTATTTTTTTGCTGATCCATATTTTTGTACAACCTTTTGAGCGATATTTACAAATT
ATACTAGTACAAAAAAAAGAGAGAGAGAGATAAGCAAAAGAAAACTGCCACTTTTGAGATACTTTTGATAATCTTTGATTTGCATTTAATCATTT
CCACACTTGCATTTTTTATAAACAACAAACAAAATTACTTCCATTGTAGAACAAAGTAAACTGCAATTTCAATGTCTTCGCATTTGTAATTCCGA
ATTGCAAGAAAAACAAAAATATTTAAATATGTTTAACTAGTAGAATTTTTAAACGTAAGTCCACAAAAACAAGCACATCTAGCTTTAATTGTT
GAAACAAAAGCAGAAAAAACGCAACAAAAAAAATGAATGAAAATCATTAAATTAATTTTGTATATAGTTTTTATGCCATTTTTGTGATGTTTTGTG
TCTACGGTTTATGTCATGTTATTTAGTTAAATTTCTTATGATTTATGTTTATTTGTAATATTTTTTGTCATTGTTTGTTCATCATCATATTCAA
ATTGGTCTCACAATATAATAGTTTTAAGCTCCACGCCCGGGAGATTGATGGCAAAACGATTGAAATTTGGCCAGAAGAGAGATAGTTTTCCCCAT
TCGTACACAGTCTTTTTTGGAATGCACATTAATGATCTCTCACAATGGAAATTAATGAAAATTGATCTCCGCAGCTAGCCAAAGTTAAAAAAGAA
ATGAAGAGGAAAACATATTCTATAGGCAATTTTCACTATATGCTAGAATTTCCCGGGCGTTTCAATGCTAATCGAATACAGTGACATGAAAGCAA
ACATAGCGAAAATATTAAGAAAATCAATCAAAAAGAAAGAAAAACCAATTCCCAAAAATCGCATTGATCTCATGGATTTATACAATACAATTACA
TCAACCGTTTTTTTACAATGAGAAATGTTATAAAAAGCAGAAAGTGAAACACAGAAACATAAACAAAAATTAACGAAAAGCTTAGATATAAGTTC
GCCAAGCGTTTTAGTTCTATTTTCTAGAATGTCTAAGTTGGTTTAGTGAGTTTATTAAGCTGTCTTCGGACACAAGTTTATTTGTATATAAGCAA
TATTATTTGTGTAGCCTAAGTGACAGTCCCAATCAAATCCAATCCAATATCACCCAGTCCCGGACATTTCCCAGCAAAACAATAGACTATTCTCG
CGTTCACATGTATCAATCTTAATTTGAATTACCACAAAATGAAATGAAATACTAAAACCATACACAAATGAAAAATTATTTTTGTAAATTGTTTG
CATCAAGTGAGCAAGGGGATTAGATTAAGGAATCATCCTTGCTTTATCCCCTGCTTATTGCTAATTAGTTTTCACAATGATCTCGGTAAAGTTTT
GTGGCCTTGCGCCCAAAAGTCGTACAGATTTTTGGTTTGCCATAAATACTCGAACAAAAAGTTAATGAAAAACGAAGCAAATGGAAAAAAAATCA
GAATGAAACACAAGAAATTTATATTTTTGACCCAATGCTACTTAATCCGTTTTTGTAATTTAAGTATCTTTACTCGACCTTGTATATAGCGCAGT
TCGAATCACAGAATCAAATGCCATTTTTGTATAGAATTTTATTTGGTGCCAAAACAGTGACAGATAATTAAATGTCTATGAACCCGTGTATTTCG
CATATTATACATTTATACATATATCGTAACTTCAATGATAAGTTTGATTCTGAAATTTTGTCAACTCAATTTAAGAAACATTTCTGTTGTAGTTT
AGTGATTGCTAGCAGAAAGCACTTTGTTTAATTGTACATTTTATATTATGCTGTAATATTTTAATATACATAAATATCATTATTGATCTCATGAA
TATGTTCATAAGACAACAAAAATTATATATATGAATACATCTATGTGTATGTGTAAATGAAATAAAAGCGCATAATTATTATGTAAGATTTATGG
AACAAATGAAAATAAAAGTGAAAAAAATATTTGAAAAAATTAAAAGTTTGTATATGATTTGAATGGGTTGTCATGGCATACAAGCGTTTTTTTA
TAAGGTTATTACTCTTCATAAATTCATCAATCTCAAACATTATTATTATTTAATTATGTTGAATAACCAAAGAAAAGTAAGTAAAAGTATTTATT
TAGTATATTTTACATCGCAAGACATTTTACATATTTATAAAACTATCATTTTTCATTACCAATATTTTATTAAGATGGACGCAAATAAATGTAAA
GGAATATTTATATATTTATTTATTTGAAATATTTTACATGGCAACTTATTTTACATGGATTATGGCAAGCTGATCACATGTAAAATACATTTTAC
AAGGCCTACTTTCAGGCAGGTATGAGAAAAGATCACTGAAGCATTGCGTGTGAGAGAGAGAGAGTTTTCCTCCTACCCTGAAAAACGAACCTTTT
GTTATTGTTCAGGGTTGAAGTGTGCGTGAGGAAATATTTTTCTTCGATTTAAATGGCCACTTGGACGGCATATAACCAGGCGAAAGCTTAAACCA
ATTTGTAGTTTCAATTCCTTTCGTGGCTACGGATTAAGTGGCCATAATTGCTGCTCCTGCAGCCGCGCCACGTGACTTGGTAACGGGATACTGTG
CCGGCCACGTTGCTCGTGTCACAAAAATGATGTGTTATTAGCGGCTTAAGCAGGCGATGGCGATTATAATGAAACGCGGCACCAGGCTGGGCAAT
TATGTTAACCTGGCCACCGAAAAAACCTCAGGCTCAGCGGTCATGACATCCGTTTCCGCCTTAAATCACGCGACACATGCAAGTGTCAATCAAAAC
GGTATATTTAATCAGAAACTGATATTTTCATTGAATGCAGGCGCGTGTGCGAATCAGTTGAACGGACATCAAAAAGCAACTGCTAATCGGAGATT
GGAAATCTTACA
(SEQ ID NO: 556)

Exon: 1001..1817
Exon: 13055..13562
Exon: 14237..14549
Exon: 16518..18867
Start ATG: 1487

Transcript No. : CT16413
ACGTGTTTCCTGCCCTCTTTCTTTGAGTCTGCGACACGTTTTAAGTGCTCTTCCATAATTGACAACAGCAAAAGCAAAGAATAAAAAAATAACAA
AAAATAAAAAACGAAATCCATCGTGAACAGTTTTGTGTTTTTAAATCAGTTCTAAACACGAAAAGGGTTGATGAAAAACGCAGAAGAATCCGAAA
AACTAACTAACCGAGCAAAAACTTGACTTGAGTGTTGTTTGACAAATCAGGAAAGATAAAAAACAAATCATAAGAAAAAACTGCACGAAAAATGA
AAAAGTTTCTAATATTCAAAATCTTGCACAAGAAATACAAAATCAATTAAAGTGAACTCTAACCAAAAGTTGTACACAAAATAAAAAGCAAAACA
AAGCAGCGAAGAACAATCACAAGAAGAGCAAAGTGCCAACAAAGTGCAGGAAGGAAGGAAGCGGATAAGGACAAAAAGGAAGCCAGCACACACAC
ACACCCACACAATGGCCGTGCCCTTTTATTTGCCCGAGGGCGGCGCCGATGACGTAGCGTCGAGTTCATCGGGAGCCTCGGGCAACTCCTCCCCC
CACAACCACCCACTTCCCTCGAGCGCATCCTCGTCCGTCTCCTCCTCGGGCGTGTCCTCGGCCTCCGCCTCCTCGGCCTCATCTTCGTCCTCCGC
ATCGTCGGACGGCGCCAGCAGCGCCGCCTCGCAATCGCCGAACACCACCACCTCGTCGGCCACGCAGACGCCGATGCAGTCTCCACTGCCCACCG
ACCAAGTGCTATACGCCCTCTACGAGTGGGTCAGGATGTACCAGAGCCAGCAGAGTGCCCCGCAAATCTTCCAGTATCCGCCGCCAAGCCCCTCT
TGCAATTTCACGGGCGGCGATGTGTTCTTTCCGCACGGCCATCCGAATCCGAACTCGAATCCCCATCCGCGCACCCCCCGAACCAGCGTGAGCTT
CTCCTCCGGCGAGGAGTACAACTTCTTCCGGCAGCAGCAGCCGCAACCACATCCGTCATATCCGGCGCCATCAACACCGCAGCCAATGCCACCGC
AGTCAGCGCCGCCGATGCACTGCAGCCACAGCTACCCGCAGCAGTCGGCGCACATGATGCCACACCATTCCGCTCCCTTCGGAATGGGCGGTACC
TACTACGCGGGCTACACGCCGCCACCCACTCCGAACACGGCCAGTGCGGGCACCTCCAGCTCATCGGCGGCCTTCGGCTGGCACGGCCACCCCCA
CAGCCCCTTCACGTCGACCTCCACGCCGTTATCGGCGCCAGTGGCGCCCAAGATGCGCCTGCAGCGCAGCCAGTCGGATGCGGCCAGACGCAAGC
GATTGACCTCGACGGGCGAGGATGAGCGCGAGTACCAGAGCGATCATGAGGCCACTTGGGACGAGTTTGGCGATCGCTACGACAACTTTACGGCC
GGCCGGGAGCGTCTGCAGGAGTTCAATGGACGCATCCCGCCCCGGAAGAAGAAGAGCTCCAATAGCCACTCGAGCAGCAGCAATAATCCAGTCTG
CCATACCGATAGCCAGCCCGGTGGTACATCCCAAGCGGAGAGCGGTGCCATCCATGGCCACATCAGTCAGCAGCGACAGGTGGAGCGAGAACGAC
AAAAGGCGAAGGCCGAGAAGAAGAAACCACAGAGCTTCACTTGGCCAACTGTTGTGACCGTTTTCGTTTTGGCCATGGGCTGTGGCTTCTTTGCG
GCGCGATGAAAGCGCAGGAGACGTGTAATCGAATGATCTATAGTGAAATCAGCTAGCCCTTAAGATATATGCCGATCTAAACATAGTTGTAGTTA
AACCGTACATAAGTGCAACGAATTTATTGAACTGCAGGAGCGAAAGCAGAAAGTCATTAATTCGTAAACGGATTGTTAGATACACAAACAGCCAA
CATACACGAAGAGTGTGCCTAAGATTAAGAAGGTTGACGGGACACAAGAACAATATATTCTATCTGTCTATGGTAACTGCATTTGTATTTCTAAA
ACGAAACGAAAGATAACAATCTTAACTGCTCAAAGTAATGAAAACTCTTAGACTGGCAAGAGACTCAAATCACACTTATTTTTTTGCTGATCCAT ATTTTTGTACAACCTTTTGAGCGATATTTACAAATTATACTAGTACAAAAAAAAGAGAGAGAGAGATAAGCAAAAGAAAACTGCCACTTTTGAGA
TACTTTTGATAATCTTTGATTTGCATTTAATCATTTCCACACTTGCATTTTTTATAAACAACAAACAAAATTACTTCCATTGTAGAACAAAGTAA
ACTGCAATTTCAATGTCTTCGCATTTGTAATTCCGAATTGCAAGAAAAACAAAAATATTTAAATATGTTTAACTAGTAGAATTTTTTAAACGTA
AGTCCACAAAAACAAGCACATCTAGCTTTAATTGTTGAAACAAAAGCAGAAAAAACGCAACAAAAAAATGAATGAAAATCATTAAATTAATTTTG
TATATAGTTTTTATGCCATTTTTGTGATGTTTTGTGTCTACGGTTTATGTCATGTTATTTTAGTTAAATTTCTTATGATTTATGTTTATTTGTAA
TATTTTTTGTCATTGTTTGTTCATCATCATATTCAAATTGGTCTCACAATATAATAGTTTTAAGCTCCACGCCCGGGAGATTGATGGCAAAACGA
TTGAAATTTGGCCAGAAGAGAGATAGTTTTCCCCATTCGTACACAGTCTTTTTTGGAATGCACATTAATGATCTCTCACAATGGAAATTAATGAA
AATTGATCTCCGCAGCTAGCCAAAGTTAAAAAAGAAATGAAGAGGAAAACATATTCTATAGGCAATTTTCACTATATGCTAGAATTTCCCGGGCG
TTTCAATGCTAATCGAATACAGTGACATGAAAGCAAACATAGCGAAAATATTAAGAAAATCAATCAAAAAGAAAGAAAAACCAATTCCCAAAAAT
CGCATTGATCTCATGGATTTATACAATACAATTACATCAACCGTTTTTTACAATGAGAAATGTTATAAAAAGCAGAAAGTGAAACACAGAAACA
TAAACAAAAATTAACGAAAAGCTTAGATATAAGTTCGCCAAGCGTTTTAGTTCTATTTTCTAGAATGTCTAAGTTGGTTTAGTGAGTTTATTAAG
CTGTCTTCGGACACAAGTTTATTTGTATATAAGCAATATTATTTGTGTAGCCTAAGTGACAGTCCCAATCAAATCCAATCCAATATCACCCAGTC
CCGGACATTTCCCAGCAAAACAATAGACTATTCTCGCGTTCACATGTATCAATCTTAATTTGAATTACCACAAAATGAAATGAAATACTAAAACC
ATACACAAATGAAAAATTATTTTTGTAAATTGTTTGCATCAAGTGAGCAAGGGGATTAGATTAAGGAATCATCCTTGCTTTATCCCCTGCTTATT
GCTAATTAGTTTTCACAATGATCTCGGTAAAGTTTTGTGGCCTTGCGCCCAAAAGTCGTACAGATTTTTGGTTTGCCATAAATACTCGAACAAAA
AGTTAATGAAAAACGAAGCAAATGGAAAAAAAATCAGAATGAAACACAAGAAATTTATATTTTTGACCCAATGCTACTTAATCCGTTTTTGTAAT
TTAAGTATCTTTACTCGACCTTGTATATAGCGCAGTTCGAATCACAGAATCAAATGCCATTTTTGTATAGAATTTTATTTGGTGCCAAAACAGTG
ACAGATAATTAAATGTCTATGAACCCGTGTATTTCGCATATTATACATTTATACATATATCGTAACTTCAATGATAAGTTTGATTCTGAAATTTT
GTCAACTCAATTTAAGAAACATTTCTGTTGTAGTTTAGTGATTGCTAGCAGAAAGCACTTTGTTTAATTGTACATTTTATATTATGCTGTAATAT
TTTAATATACATAAATATCATTATTGATCTCATGAATATGTTCATAAGACAACAAAAATTATATATATGAATACATCTATGTGTATGTGTAAA
(SEQ ID NO: 557)

Start ATG: 487

MAVPFYLPEGGADDVASSSSGASGNSSPHNHPLPSSASSSVSSSGVSSASASSASSSSSASSDGASSAASQSPNTTTSSATQTPMQSPLPTDQVL
YALYEWVRMYQSQQSAPQIFQYPPPSPSCNFTGGDVFFPHGHPNPNSNPHPRTPRTSVSFSSGEEYNFFRQQQPQPHPSYPAPSTPQPMPPQSAP
PMHCSHSYPQQSAHMMPHHSAPFGMGGTYYAGYTPPPTPNTASAGTSSSSAAFGWHGHPHSPFTSTSTPLSAPVAPKMRLQRSQSDAARRKRLTS
TGEDEREYQSDHEATWDEFGDRYDNFTAGRERLQEFNGRIPPRKKKSSNSHSSSSNNPVCHTDSQPGGTSQAESGAIHGHISQQRQVERERQKAK
AEKKKPQSFTWPTVVTVFVLAMGCGFFAAR*
(SEQ ID NO: 558)

Gene Symbol: W
FlyBase ID: FBgn0003997

Celera Sequence No. : 142000013384553
ATAATATGGAAAATCTCAATTTAAATTTGTTGTTGGCTGTTGCTTTGCTTGTTGTTGCTGCCGCTGCTGTTGTTGTTGTTGTTGAATTTCACGCG
AAAGCAGGCAAGACAACAACATAAAATCACAAACACTTGCACGCACATACGTCACACACACCCGCACACACACTTGGACAGCTGAGACATAAACA
CACGGAGAGCAAATCGCAGCGAGAATGGGAGAGAGAAAGAGACAGAGAGCGATAACAAATTTGTTTTCTGGTTTTTCTTCACGATTTTATTACAC
GCTTTTCGAATGGCTAACCATATTTTGATTCACATTTAATTCGCTCCAATCACAGTGTGTTCCGTGCGCTTGCTAATTTTCGATTTTCCACCGCA
GAACTCCGCCCGTTTTGCTGCTGTTTTGGCAATCGTCTCTCTCCTGGCTAAAAACATATGATTTCGGTTGACGGAATCACGATAAAAACACATAA
ATGCGAACAGGGCGCGCGCAACAACTTCCCACGACAAACTCTCGCTTCGGAATTTGGAACGAAACTGCCACTTTTGCAGCGAATCGCGCTTAAAT
ACCCGTCTAAAGATGGGAACGCATGGCGAACCGGTTCGATAGTTCGTGAGCGAACAGCCTTCGCACAGTGGTATGCAATCAAACTGAGCAGTAGA
TTAAGTACTTTTGTTTAACAAACCGGATAGCTCGAACTTTGAAAATAAGTTTTGGATCGGCAGGAATTAAGACTGTGCACAATTAATGCTTTTAA
TGGTGACTCAACACTTTGTGACGTCAGTAGTAGCATAAGTTCAAAATAATTAATTTGAGTATAGCTTTTGTTTAATGTATTGTATAGAATAACTA
GTAATACTGCTTTTTTGACTGCGATAAACATTTACGTAATAAAAACTGCATATATTTGCTTTGTGACAACCCTATTTTATTTTGCGTGCGTCACC
TTACATTTTGCTACCTTGCTGCATCAGCTGTTTGTGTTGTGCGGCGAAGAATGGATTTGACGCTGGACAAAAAGCTGCAGGGATTCCAGTTGGTG
GCACAAGAAAAGGTATAATAATGAATCGGAAGAGTGAAACTATTAACTACCTGCAATTCGACTGCAGCTTTGTTCCATACTATGTAGCATACCTG
GAAAGAAGGAGTTAATTTTGGAGCCCGACTTGATAAAGCCACTGGAACATGTTGTCACTGCCTCCTGGCTGAAGTAGGTGTTTAATCCATATTTT
ATGGATATTTACGTCTTATATATACCCCTTAACAGGTTGAAGGGCATACAACGGATCTACAAACATGATGCGGCACAATCTTTGCCCCGATCCGC
CGATCAGGTGCACATCTACATGATCCGCAGTGTTTTGGGTACATTTCAGACACTTCTCAAGCAATTGCAACCCGTGGCCTCAGAGGAAATGCCCG
ACATCTCCATGAAAATGTATCACATAGTCTGTGTGCCCAGTTGTTACTCCTATTTTCAAACCCTGCTGGAACAGGCTGGTTTGTACGGACTGGTG
CAACTTCATCACTTTAACTGGGACTTCATCTATTTTGATCAGGGAGTTCTCAGCTTGGAGCTGCCCAATGTGAGTAGATGTACATTGAACATTCA
GAAAAGAGTCTTTTATACTGGATATTCTTATTATTCAGCTTTACGAGTGTCTCTACCTGCAGAAGAACACATCTCCATTGCCTGCGGTGGCCCAG
AGCCTGCGATTGCTTCAGATGATTTGCGGACAACCGTCTTTGATTCTGAGCTTTGGCCACCACTCGTCGCAGCTAATGCAAATGGCGAAGACTCT
TGGCAAACTTCCGGCGCCCACAAATCCTCCAGACTATGGCGGCTGGCTGGTCATCGATCGGGATAAGGATTACCCCGCCAGCTTGCTCACTCCGG
CCATCTATGCAGGTCTTCTCTTGGAAGTTTTCGAGCATAGTTCTGGCGAGATTCTGGTAGACAATTCCAAGAACAAGATCCGCAGCCAGCGTGTG
GAGTTACTCCAGGGAAAGAAATCCAAGATAGGCGTAAACTCAGCCAGCAAGCCGTGTTCCATTCGTCTTAACTCCACATCCGATGAGATCTACGG
CGATAATCGGTACAAACGATTTGCTCAGGTCAGCAGTTTGATTCACGCACAAGTAAAAGCCCTGGGCTTGGAACTGCAGAAACTCAATGACATGC
AGCTGGACGAGATGCATGACTATGTGGCCAGGAAGCTACCCAAACTAACCGAGCTTAAGAGCAAAGTCCTTAGGCATCTGAATGCCAGCGAGATT
GTGATCCAAATGATGGGTAACTTCAGGAAGCTCCAAACGCTGGAGGAGGACATACTAAACAATGATTCAAGAAAGCGATTGCTAAGCGAGATCGA
CGAGCTGTTGACCACAGATGGTCAGAGATTTAATACACTGCGACTGCTGTGCCTCTTGCATCATTGCGTTGGCGTGGCGCCCGAGGAGCTGCAGA
TATTTGCGCGGAACTACTGCAATCTGTTTGGACACCAGGAATTGGGCGTGTTCCAGCAGTTGTCGCAGGCGGGCTTGTTGCCACCACTTGTGGTG
GAGAAAAAGGCGCCAACGAAACTGCTCTCAAATCTACCTCTGCCCAAGTTCCAGCAAACGGAGTTTCAGGCCAATGCTAATCGGCTAAAGCTGTT
GACCTCCAGTGGAGATGGTCAGGATGGAGGTTCCTCCTCCAAGAGCCAATCCAGTGGCTTGCAGACCTGTCCCAGTTTTGTGTTCAATGGCACCT
ACATACCATTGGTGGCTCAGCTCTGCTCCATTTTGCTGAAAATCAATAGTGCTGAGGAGTTGTCCTCGAAGCTGGGCATGATTGAGGGGCTGCAT
CTACACCTGGACAGCGGAAAAATCACGCCCAAGGCCTATGCCAGCCAAGTGAAGCTAAACGGAGTTGCAGATCAGGATATGTTCCCCTTGCGTCT
CAGGAATCTCTTTGTATTCATTGTGGGTGGTGCCAGTTATGCGGAAATCGCCGCCTGCGATTTTGTGGCAAAGCTAACAGGCGCCCAAATAACCG
TGGCATCCGACTCTCTAATGGCGGGCAGTGATTTGATCGCCACCGCCTTCAACCGCTGACCATGAAGTAACTAAGAATCTGTGTATCAAATGTTT
TATATATTTTTATACAAAACAATGATGACAAAGCTTGTGATTAACAATTTTCGAAATTTACAATTTAAACAATGCTCTTTTCGAATAAATATTAC
CTAAAAGTGGCATTTGCTATTTATCACCACTGGCTCTGGTCATTCCAGGCACTCGGTAGAGCAGCTCTCCATCGTCATCGTAATAGGCATCCTCC ACCCGGTAAGTGGCTCCTTGGCGATGCAGTTTCCGGGGAATAACAATGCGTGTTTTCACCTGGGTTATTTCATACTTGCGCTGATCCGCGGCACT
GATCACAATCTCGCTGCTCGCAAACTTGGGCACGAAACTGGGCAGGAATCCGGTGCCACTGGGATTCTCGATGGGCCGCTTCATTTCCTCTGGAA
CTGCGGGCGCAGACTCAACGAGCTGCAATTCCTTAAGCTCCTGCAGCCGCATCTTCTTTTTATTACGGATTTTGTCCAACAAATAGGTTTCATCT
TCGGCAGCAGAGGGTGGAGCTTCATAGCCGGATGGGATTTGTGGTGTAGGCATCTCCTCTGTTGTTTTACTACTGCTGCCCAGCAGTTTGCGGAA
TTCGTTGCCTTGCGGAGTCGGTAGTTGTGATTTTGTGGGCCAATCCTGGATTTTAAGCTCCCGCAGATCCTGCCACCTTCGCTCGGCGAATTTCT
GCAGATGCTGGAGAAGAGACGGTGGGATACTGAAGTCACCCTTTCCCGTCCCTAAAAGCTGCCAGTTTTTAATGACGGTTTCATCGTGGGAGCGT
ATCCTTTGCACACTTCTCGGTCGCCACTTGGCCCGCAGAATTTTCTGCACAATGTCCGGAGTGGCGGGAAAACTTTCGGCCAATCGCTCAACGCT
CCATTCCTCGGGATCTCGCTCGTGCAGCAGGCGCATCTGCTCCTTTTCGGCATGAAGCAAGAGATTGGGCAACTTGGCGTCTCGGAAATACTTGT
GCTTTATCATAAAC
(SEQ ID NO: 559)

Exon: 1001..1057
Exon: 1113..1213
Exon: 1271..1589
Exon: 1654..3099
Start ATG: 1001

Transcript No. : CT16445
ATGGATTTGACGCTGGACAAAAAGCTGCAGGGATTCCAGTTGGTGGCACAAGAAAAGCTTTGTTCCATACTATGTAGCATACCTGGAAAGAAGGA
GTTAATTTTGGAGCCCGACTTGATAAAGCCACTGGAACATGTTGTCACTGCCTCCTGGCTGAAGTTGAAGGGCATACAACGGATCTACAAACATG
ATGCGGCACAATCTTTGCCCCGATCCGCCGATCAGGTGCACATCTACATGATCCGCAGTGTTTTGGGTACATTTCAGACACTTCTCAAGCAATTG
CAACCCGTGGCCTCAGAGGAAATGCCCGACATCTCCATGAAAATGTATCACATAGTCTGTGTGCCCAGTTGTTACTCCTATTTTCAAACCCTGCT
GGAACAGGCTGGTTTGTACGGACTGGTGCAACTTCATCACTTTAACTGGGACTTCATCTATTTTGATCAGGGAGTTCTCAGCTTGGAGCTGCCCA
ATCTTTACGAGTGTCTCTACCTGCAGAAGAACACATCTCCATTGCCTGCGGTGGCCCAGAGCCTGCGATTGCTTCAGATGATTTGCGGACAACCG
TCTTTGATTCTGAGCTTTGGCCACCACTCGTCGCAGCTAATGCAAATGGCGAAGACTCTTGGCAAACTTCCGGCGCCCACAAATCCTCCAGACTA
TGGCGGCTGGCTGGTCATCGATCGGGATAAGGATTACCCCGCCAGCTTGCTCACTCCGGCCATCTATGCAGGTCTTCTCTTGGAAGTTTTCGAGC
ATAGTTCTGGCGAGATTCTGGTAGACAATTCCAAGAACAAGATCCGCAGCCAGCGTGTGGAGTTACTCCAGGGAAAGAAATCCAAGATAGGCGTA
AACTCAGCCAGCAAGCCGTGTTCCATTCGTCTTAACTCCACATCCGATGAGATCTACGGCGATAATCGGTACAAACGATTTGCTCAGGTCAGCAG
TTTGATTCACGCACAAGTAAAAGCCCTGGGCTTGGAACTGCAGAAACTCAATGACATGCAGCTGGACGAGATGCATGACTATGTGGCCAGGAAGC
TACCCAAACTAACCGAGCTTAAGAGCAAAGTCCTTAGGCATCTGAATGCCAGCGAGATTGTGATCCAAATGATGGGTAACTTCAGGAAGCTCCAA
ACGCTGGAGGAGGACATACTAAACAATGATTCAAGAAAGCGATTGCTAAGCGAGATCGACGAGCTGTTGACCACAGATGGTCAGAGATTTAATAC
ACTGCGACTGCTGTGCCTCTTGCATCATTGCGTTGGCGTGGCGCCCGAGGAGCTGCAGATATTTGCGCGGAACTACTGCAATCTGTTTGGACACC
AGGAATTGGGCGTGTTCCAGCAGTTGTCGCAGGCGGGCTTGTTGCCACCACTTGTGGTGGAGAAAAAGGCGCCAACGAAACTGCTCTCAAATCTA
CCTCTGCCCAAGTTCCAGCAAACGGAGTTTCAGGCCAATGCTAATCGGCTAAAGCTGTTGACCTCCAGTGGAGATGGTCAGGATGGAGGTTCCTC
CTCCAAGAGCCAATCCAGTGGCTTGCAGACCTGTCCCAGTTTTGTGTTCAATGGCACCTACATACCATTGGTGGCTCAGCTCTGCTCCATTTTGC
TGAAAATCAATAGTGCTGAGGAGTTGTCCTCGAAGCTGGGCATGATTGAGGGGCTGCATCTACACCTGGACAGCGGAAAAATCACGCCCAAGGCC
TATGCCAGCCAAGTGAAGCTAAACGGAGTTGCAGATCAGGATATGTTCCCCTTGCGTCTCAGGAATCTCTTTGTATTCATTGTGGGTGGTGCCAG
TTATGCGGAAATCGCCGCCTGCGATTTTGTGGCAAAGCTAACAGGCGCCCAAATAACCGTGGCATCCGACTCTCTAATGGCGGGCAGTGATTTGA
TCGCCACCGCCTTCAACCGCTGA
(SEQ ID NO: 560)

Start ATG: 1

MDLTLDKKLQGFQLVAQEKLCSILCSIPGKKELILEPDLIKPLEHVVTASWLKLKGIQRIYKHDAAQSLPRSADQVHIYMIRSVLGTFQTLLKQL
QPVASEEMPDISMKMYHIVCVPSCYSYFQTLLEQAGLYGLVQLHHFNWDFIYFDQGVLSLELPNLYECLYLQKNTSPLPAVAQSLRLLQMICGQP
SLILSFGHHSSQLMQMAKTLGKLPAPTNPPDYGGWLVIDRDKDYPASLLTPAIYAGLLLEVFEHSSGEILVDNSKNKIRSQRVELLQGKKSKIGV
NSASKPCSIRLNSTSDEIYGDNRYKRFAQVSSLIHAQVKALGLELQKLNDMQLDEMHDYVARKLPKLTELKSKVLRHLNASEIVIQMMGNFRKLQ
TLEEDILNNDSRKRLLSEIDELLTTDGQRFNTLRLLCLLHHCVGVAPEELQIFARNYCNLFGHQELGVFQQLSQAGLLPPLVVEKKAPTKLLSNL
PLPKFQQTEFQANANRLKLLTSSGDGQDGGSSSKSQSSGLQTCPSFVFNGTYIPLVAQLCSILLKINSAEELSSKLGMIEGLHLHLDSGKITPKA
YASQVKLNGVADQDMFPLRLRNLFVFIVGGASYAEIAACDFVAKLTGAQITVASDSLMAGSDLIATAFNR*
(SEQ ID NO: 561)

Name: VACUOLAR PROTEIN SORTING HOMOLOG -like
Classification: transporter

Celera Sequence No. : 142000013384253
GGTCAACAAAACGGCACGGACCGGCGGACTGGACTCAGTGCCATATAGAATCAGGTTAGCCATTGTGGTTGCTTAACTAATTGCCTTCTAGCTGG
TTGAATTGAGATTCGTAGCAGACAGTGTGCCATCCACAACTGACTCAAGGCAGTCTAAATAATTTAAATTTCTTTCAAACGCGATAAGATTAGAT
ATTAAACTTAGTTTCTTGATAATTACCACAAAGACGTCATAATGCTGCAAGTTTAAGTTTGCCTGATTGTTTATTAATGTCCGGGATAAGTCGGT
CTGCTATCTATTAGCTGTGTCAATATTTGATCAATGTCCCCGTGATTTATTTGATCATAGTTGGAGCACCAAAGGGGCTACTTATATACACTGCT
AGAAACGTCCAAACGAAACCTAAAGTAACCAGACTCATTAGCAGTGTTTCTATGCAAACATTTTCATATAAATATAATTATAAAATTATGAGTTT
AATATTATTACTTCTGTGTATCAGATCATACAATTTATCCAAAATAACGATAAGCTTTATGCCAGCTTAACTTAAGCTTTAAGCTTTTAGAAAC
TTTCAAGCTTCGTTAGGAAGACTTGAATTGTAAATTTACATGGGTTCTACATGATTCAAATAGATGTATATTACAATAAATCATAAAACAAGTAA
CTGTATTAAATTAATTTCTTCTGACAACCAATGTTCCTGAGTTCACAGAGACCTACTTTGTTTTTGATGAGTATATGTTTTTTGTAGTTCACCAC
TGCATATGGTGTTTTAAAATTAGTATCATATAGATGATTCCAGAACTATCAGTTGGGGGTAATTAATGTTTGTTATGATGAAATAGGCATACATA
TTATATATATGGTTTTTTTTTAACTGTTTAACACATGGTTTCGAGCTTTTATCTTAGATTTACGAAATGCTCTCTCATTTAGCAAAAAGCTTGAG
GCAATAAGGTGTGTATATATGTACAGTAAATAGAGAGATCAGTCGAAAGAAAAACACTGACGGGTAAACAACACGTATCATGTCGAGCTCTGGAA
TTGTACTCTATGGGACAGATCTCAGTCCCTGTGTGAGGACCGTCAAACTTACCCTAAAGGTCCTGAATCTGGACTACGAGTACAAGGAGGTGAAT
CTTCAGGCGGGCGAGCACCTGAGCGAGGAATATGTGAAGAAGAATCCCCAACACACGGTACCGATGCTCGATGATAATGGCACTTTCATCTGGGA
CTCCCATGCCATTGCCGCCTACTTGGTGGACAAGTATGCCAAGTCGGATGAGCTGTATCCCAAGGATCTGGCCAAGCGTGCGATCGTCAATCAGC GTCTCTTCTTCGATGCCAGTGTAATCTATGCCAGTATAGCCAATGTCAGCCGCCCGTTTTGGATAAACGGTGTTACCGAAGTGCCCCAGGAAAAA
CTGGACGCCGTACACCAGGGTCTGAAGCTGCTGGAGACGTTCCTGGGCAACAGCCCCTACCTGGCCGGCGATTCGCTAACCCTAGCCGATCTGTC
CACCGGACCCACTGTAAGCGCCGTGCCCGCTGCCGTGGACATAGATCCTGCTACATATCCCAAGGTCACCGCCTGGTTGGATCGCCTCAATAAGC
TGCCCTACTACAAGGAGATCAACGAAGCTCCGGCCCAGAGCTACGTCGCCTTCCTGCGCAGCAAGTGGACCAAGCTGGGCGACAAGTGAAACTAA
ACTTATATTTAAATATGACATTTCACAAGTTTGAATTCCATCAATTAACAACATACACATCCATTTCTAAAACGTAAACTTCTTCAATAAAATAT
AACATATATATAAAATATTTAATTTATTTTTTTATTTAATTTATATTTATTTAAATATTTGAATTTATAATAAATACTGAAATTTATAAACTTTA
ATATGGGACTTGAGTCAGTAATTATTATCTCACAGTTGGGGAACCCGACCGTAATATTTTTATCGCTCATTTATGATATCGTCAGTGTACAATTA
CAAAAGTTTATTTAAGATACAAATGGGGCAAGCTCAGCGCACCCAATTGGGTTGTTTAGTTAAGCTCGTTTAGATTTCTGTGTGTGGCAAATTTA
GTGGAACTTGGGTCTCTCTGGTGATCGCATCATGTCGGATAAATTGGTTTTGTATGGCATGGATATTAGTCCTCCTGTTCGCGCTTGCAAGCTGA
CCTTGCGGGCCTTAAACTTGGACTACGAATACAAGGAAATGGATCTACTGGCAGGAGATCACTTTAAGGATGCGTTCCTCAAAAAGAACCCGCAG
CACACCGTACCACTCCTCGAAGATAATGGTGCCCTTATCTGGGATTCACATGCTATTGTCTGCTACCTGGTGGACAAGTATGCCAATTCGGATGA
GCTATATCCCAGGGATCTGGTGTTGCGCGCCCAGGTGGATCAGCGTTTGTTCTTTGATGCCAGCATTCTGTTTATGTCGCTGCGAAATGTCAGTA
TACCCTATTTTCTTCGCCAAGTAAGCCTGGTACCCAAGGAGAAGGTGGACAACATTAAAGATGCATATGGCCATTTGGAGAACTTTCTAGGGGAT
AATCCCTATTTGACCGGGTCGCAACTGACCATAGCTGATTTATGCTGCGGAGCTACTGCATCCTCGCTGGCCGCTGTTCTTGATCTGGATGAGTT
AAAGTATCCAAAGGTGGCTGCTTGGTTCGAACGACTCTCTAAGTTGCCCCACTATGAGGAAGACAATCTGCGGGGCTTGAAGAAGTATATCAATT
TATTGAAACCCGTATTAAATCTGGAGCAATAGTAATTTGTATTAAAAAAAAAATACCATCAAATGC
(SEQ ID NO: 562)

Exon: 1001..1821
Start ATG: 1030

Transcript No. : CT16545
AAAACACTGACGGGTAAACAACACGTATCATGTCGAGCTCTGGAATTGTACTCTATGGGACAGATCTCAGTCCCTGTGTGAGGACCGTCAAACTT
ACCCTAAAGGTCCTGAATCTGGACTACGAGTACAAGGAGGTGAATCTTCAGGCGGGCGAGCACCTGAGCGAGGAATATGTGAAGAAGAATCCCCA
ACACACGGTACCGATGCTCGATGATAATGGCACTTTCATCTGGGACTCCCATGCCATTGCCGCCTACTTGGTGGACAAGTATGCCAAGTCGGATG
AGCTGTATCCCAAGGATCTGGCCAAGCGTGCGATCGTCAATCAGCGTCTCTTCTTCGATGCCAGTGTAATCTATGCCAGTATAGCCAATGTCAGC
CGCCCGTTTTGGATAAACGGTGTTACCGAAGTGCCCCAGGAAAAACTGGACGCCGTACACCAGGGTCTGAAGCTGCTGGAGACGTTCCTGGGCAA
CAGCCCCTACCTGGCCGGCGATTCGCTAACCCTAGCCGATCTGTCCACCGGACCCACTGTAAGCGCCGTGCCCGCTGCCGTGGACATAGATCCTG
CTACATATCCCAAGGTCACCGCCTGGTTGGATCGCCTCAATAAGCTGCCCTACTACAAGGAGATCAACGAAGCTCCGGCCCAGAGCTACGTCGCC
TTCCTGCGCAGCAAGTGGACCAAGCTGGGCGACAAGTGAAACTAAACTTATATTTAAATATGACATTTCACAAGTTTGAATTCCATCAATTAACA
ACATACACATCCATTTCTAAAACGTAAACTTCTTCAATAAAATATAACATATATATAAAAT
(SEQ ID NO: 563)

Start ATG: 30

MSSSGIVLYGTDLSPCVRTVKLTLKVLNLDYEYKEVNLQAGEHLSEEYVKKNPQHTVPMLDDNGTFIWDSHAIAAYLVDKYAKSDELYPKDLAKR
AIVNQRLFFDASVIYASIANVSRPFWINGVTEVPQEKLDAVHQGLKLLETFLGNSPYLAGDSLTLADLSTGPTVSAVPAAVDIDPATYPKVTAWL
DRLNKLPYYKEINEAPAQSYVAFLRSKWTKLGDK*
(SEQ ID NO: 564)

Name: glutathione S-transferase (GST)
Classification: enzyme

Celera Sequence No. : 142000013384541
TTGGGCAAAACGAGAACAACAAATTATTTGAACACACACACGTATACATATGCGTACATATGTACGATTTCATGTGTGTTTGGCCCTACACGCA
CCTTTGTTTTTGTTAGCACAGATTCTTTTTTTTCGGCCTCCCTTTTCGCTCCTTCGGCCTTGGCAACAATAACAACAACACACAGCAGTGGTAGG
CGTTTCGCACTGATTTTCGATTCCAAAAACACAGGTGCTGTATTCTCTTTAACCGCGAGCTAATTCTTTGTCTTTATTTCGGATTTTTCTATTTG
TTAATGCACATTTCCGCGCGATTCTCGGACTCCGCCTGCGAAGCTCCAAAGAGCAATTGACAAAAACATCGAGAACTGCGCTCGGCGTTGCCAT
GCTGACTGCGCTGCCAGACGGCGTGGGTGGAGTCCACGCTGGAGGTAAGCCCAGACCGCAACCCTCTAACTGTGGCACAGTGGTGCAAATTAAGA
GAGGACTGCTGTCAAAAATTGTTTATAAAATTTGTTCCAGAGCCGTTATGTCATTGTTTCGTCATGTCAATTGTAAAAGAAAGCACCCTTTCAAA
ACGTTGTAAATAATTTCAACAAGTGCTACAGATATTTGTGTTATTCACTGGCATACAAGTTCGTTTAAACAAAATATTAAACATAAATAAACATT
AAAATATATTATTAAACAAAATATATTCTTGACTTGCAATAGATATGCCGTATCACTCATAAATGCAATACAAAGGGTAAATCATTATTTCCTGG
CTTAAAATTGTAATGAAACGGATAATGAATCACATAGCTATTCAGTTTTAGAGAATTTGTATGCACTTTGTCATATTTAACGTTAAAGTCGATCA
CTTTTTATTTAAGGGGCTAAAGTTGTTTTACTTTATTTGCCTAATTTAAATTTTTGCTCCTTATATTCAAAAATGCAGGCTCGATACCATCTCGA
CCGCGATGATTTGTTTGGGTTGGCAACGCCCCGACGTTTGTGGCGCAGCCAACTTCACGCGAGACGCAGCGAAAACAAAAAATACTAAGCTGAAG
TTAATTGAGAAAACCCCAAATAAAACGCGAGTGAAAGGGACCATGAACTTAGACCTGCGTTCGTACTCACGCCACTGGCTCACGGAGTTTATCGA
GCAGTACCAAGAGGAGGAGTGCCTCTGGCAGCCCAAGCACAACGACTACAGCAATCACACAGCCCGTAACAAGTCCTACGATCGCCTGGTGGAGA
AGCTAAAAGAAGTGGAGCCCAATCCGGACAGGGCGATGGTAGTAAGGTGAGAATTTCCATGTCAAATGTGCCACAGTTCAGTAAACACAATTCAC
GCTTTACAGGAAAATTAACTCACTGCGGTCCGCTTTTCGGCGGGAATTCCGCAAGACGAGTACCAAAGGCGACTACGCAACGCGTTTGTGGTACT
ACGACAAGCTGCTTTTCATCGCTGACCACAAGCCCAAGCGCCACGAACTCGGCTCCAAGCCCAAGAGAGAACTCCATATCAGCTTCGACGACGAG
GAGTCAATGGAGTTCGAGGACGACTCACATCACACGGGCACTCAGTCTCAGCACATGGAGTCCATAATACCCACGTCCCCGGACGATGTGGAAGA
AGTCGCGGCGACGGCCAACAATGTGGTCGTCAGCAGTCAGGGCGCCACTCTGAGCACCATTTCGGTGACGCCCGCGGAATGTGTGACCCTTGTCA
AGAGCGAGGAGCACCAGGCGGCCGAAGCAGCGGCAGCCGCAGCCCAAGCACACCAGCAAATGGTAGCCCATGCAGCAGCCCAGACCTCCATTGCG
GCGGCGGCGGCTCAGGGACATGCCGTGAAGGTCTTAGAGATCACCTCCCTAGACTCCAACTCCCAGCGCGAGATACAACAAGTGAGTAGCTCCAA
AGCAGTGAAGAGTTCCTTAGGGTCTTCAATCACCTCCTCTCCCCACGCAGGCGGTCAATCATCTGGAGCACCACCAGCAGCAGCTCCACCTGCAG
CAGACGAATGGCCAACATCAGGGCGTTCCCACCATCCAGATAGGCCGCGATCACTATCAGCCATTGTTTGGCAATGCCGGCACCACTGCCTATAC
CACCACAGCGGCTACGAGCACATCGCACCGGCAAGACGACGAGTACGATGCCATTGGCGTGAATGTGGCGAGCAAACTGCGCTCCATCAACCCGA
CGCAGCGGATCGTGGCCGAGAAACTGATCAGCGACGTTCTATTCAACGCACAGCTGGGCAACCTCACCGTTCACTCGGCCCTCACGCAGTAATCT
CTCTTGTCCCCCTAGACTAAGTATGTGTAGTCTCTGGCTTTATATCTCCATTTTGTCTGTGTCCCAACCTGCAGCCCGGCCAACATGTGTCGCCC
GGGCAGCAGCCGATTGTACCATACAGTTTGCATGTAGTTTTAATTATTCTATACAATAAATAGATTGTATGTCTTAAGCTCATCACCAGAGGGTT TGTCATTCCGTCGAACTTCCTGCGCCCGTTAGCTTGTTCCACACAAACCTGGCAAACTGGACAAAAAGAGGAGCTGCTGTCTTGAGGTGATCGCC
TTAAGAATTAGGACTAACATACCGTGACCGGCGGCATCTCGATCTGTTCCGCCTCCGTGACCAGTTTTCGGTTGCTCTGCATGTAGCTCCAGCCC
AGATGGATCCCCACCAGACTGGGGATCATCACGACGGCCACCAGGTTGCGCGACACGAACGAGGGCTGCTTGCTCATCTTTACAAAATTCGTAAA
ACGGAATTATTATTATTTAACAGCTATCACAAATCAACAATGACGATGTGACCGCATTGCGATGTTTGTTTAATCTTATCAACGAAAAATACCAA
CCTATAACGCTGCCCCAAAACGGGCGGCTAGTTTTGAATAAAGTTTCTATCTCCCCCAACTTGGTCCAAAGTCCAACGTTTTCGGGGATAATAAT
GGGAAACTAAACGTCTCGCAATTCTTTGTCTGGGACTTCGATTGCTTGGGCAGATAAGCATCTGTCATTAGTTTGTTGCGGTGGCTGGTTTTAAT
AACAAATGCGGTGGAGGTGGTTAGAGTAGATCAATGGCATTGTAAAGGGGAACTTCACTTCTCGTAGGGTATATTAGTTGCTGCGAAATTCTTTA
AAGACTTTTTGTGATTATAGAAGGCCTGAAGTAACTGGTAAGGTCCTTCGCTTTTATAACTAACATAAGATTATAATAGTTAAAAAACAAAAATG
TGTAATTATACTACTTTACGTACAAGTTAAAATTGTCTAAGCTTTGAATTCAAATAACAGAAAGATGAAAAATAATTTTAGGTGCTTAAAGTTCT
TAGTGGACAAACTAATTCGGAAAAATTAGAAAATATGTATGAAATAATTATAAGCTGAAATCTGAAATTTTAACTTAATCTGTTTTAAAAACCGT
AAAATAAGCTATAAATTTATCGTCACAATAAAACCA
(SEQ ID NO: 565)

Exon: 1001..1281
Exon: 1340..1886
Exon: 1951..2456
Start ATG: 1088

Transcript No. : CT16581
AACTTCACGCGAGACGCAGCGAAAACAAAAAATACTAAGCTGAAGTTAATTGAGAAAACCCCAAATAAAACGCGAGTGAAAGGGACCATGAACTT
AGACCTGCGTTCGTACTCACGCCACTGGCTCACGGAGTTTATCGAGCAGTACCAAGAGGAGGAGTGCCTCTGGCAGCCCAAGCACAACGACTACA
GCAATCACACAGCCCGTAACAAGTCCTACGATCGCCTGGTGGAGAAGCTAAAAGAAGTGGAGCCCAATCCGGACAGGGCGATGGTAGTAAGGAAA
ATTAACTCACTGCGGTCCGCTTTTCGGCGGGAATTCCGCAAGACGAGTACCAAAGGCGACTACGCAACGCGTTTGTGGTACTACGACAAGCTGCT
TTTCATCGCTGACCACAAGCCCAAGCGCCACGAACTCGGCTCCAAGCCCAAGAGAGAACTCCATATCAGCTTCGACGACGAGGAGTCAATGGAGT
TCGAGGACGACTCACATCACACGGGCACTCAGTCTCAGCACATGGAGTCCATAATACCCACGTCCCCGGACGATGTGGAAGAAGTCGCGGCGACG
GCCAACAATGTGGTCGTCAGCAGTCAGGGCGCCACTCTGAGCACCATTTCGGTGACGCCCGCGGAATGTGTGACCCTTGTCAAGAGCGAGGAGCA
CCAGGCGGCCGAAGCAGCGGCAGCCGCAGCCCAAGCACACCAGCAAATGGTAGCCCATGCAGCAGCCCAGACCTCCATTGCGGCGGCGGCGGCTC
AGGGACATGCCGTGAAGGTCTTAGAGATCACCTCCCTAGACTCCAACTCCCAGCGCGAGATACAACAAGCGGTCAATCATCTGGAGCACCACCAG
CAGCAGCTCCACCTGCAGCAGACGAATGGCCAACATCAGGGCGTTCCCACCATCCAGATAGGCCGCGATCACTATCAGCCATTGTTTGGCAATGC
CGGCACCACTGCCTATACCACCACAGCGGCTACGAGCACATCGCACCGGCAAGACGACGAGTACGATGCCATTGGCGTGAATGTGGCGAGCAAAC
TGCGCTCCATCAACCCGACGCAGCGGATCGTGGCCGAGAAACTGATCAGCGACGTTCTATTCAACGCACAGCTGGGCAACCTCACCGTTCACTCG
GCCCTCACGCAGTAATCTCTCTTGTCCCCCTAGACTAAGTATGTGTAGTCTCTGGCTTTATATCTCCATTTTGTCTGTGTCCCAACCTGCAGCCC
GGCCAACATGTGTCGCCCGGGCAGCAGCCGATTGTACCATACAGTTTGCATGTAGTTTTAATTATTCTATACAATAAATAGATTGTATGTCTTAA
GCTC
(SEQ ID NO: 566)

Start ATG: 88

MNLDLRSYSRHWLTEFIEQYQEEECLWQPKHNDYSNHTARNKSYDRLVEKLKEVEPNPDRAMVVRKINSLRSAFRREFRKTSTKGDYATRLWYYD
KLLFIADHKPKRHELGSKPKRELHISFDDEESMEFEDDSHHTGTQSQHMESIIPTSPDDVEEVAATANNVVVSSQGATLSTISVTPAECVTLVKS
EEHQAAEAAAAAQAHQQMVAHAAAQTSIAAAAAQGHAVKVLEITSLDSNSQREIQQAVNHLEHHQQQLHLQQTNGQHQGVPTIQIGRDHYQPLF
GNAGTTAYTTTAATSTSHRQDDEYDAIGVNVASKLRSINPTQRIVAEKLISDVLFNAQLGNLTVHSALTQ*
(SEQ ID NO: 567)

Celera Sequence No. : 142000013384633
CAGTTCGGTGGCTTGTTAGCCGTATATACATACATATTATATATGATATTATTGTGATAAATATTTATCATTGACTCATTTAAAGAATTTTGAGA
ATTCACGCGTTTGTAGCACATTCAAAATTTTTAAAAATTATTTTATTCATTTTAGACTGGGTTATTTGATATGGTTTTCTTATAATTAGTTCTTG
AAGAATTCTTTGTAGTATTTTAATATTTGTAGATACAAACAGTAATTTTTTTTAACCATAATATTTTTTTTTTATTTTACTTTGCTTTTATTTAT
TGAATCTTCTTGTATAAGAACTAACAATAAGTTTAAAAATCTTAACTATAACAAGTATTTTTTGAACAGTTGTATTATTTTTCCAACTGTTCTAT
GTTTAAACGGCCCTAATAATTTATTCGCTGGGTTGGTAGGTCCTTTCGCCGGAGACGGGAACGGCTGCTGAGCTGGATTAGACCTCGCGCTAGGT
GGTTGGGGTGCGTGTGAAGCGTGTGAACCATAATATGATATGAAAAGATATGATATTTACTATACCAATATTTTCGAAATATAAATAGAATAAAT
AAATAAATACATATATACTACAAAGGTATATATTAGGTATATTTGAAACAAAAATCATATTTTAACGATAACAGATGCAGAAATTGTATGAAAGA
CAAAAAATAATATTTGGTGAATATTATATTAGCCTGTGGTCAGGCTAAATATAAATGTAAATAAAATTCTTTATTGTTCTTACGGAAGTATTTCC
AACTGCCTACCAGCAGCATTTTTGGATTCAAATGGTCTCCAAGCAGGAATGAATGCAGTCACTAATTGGAATGTGTTCACCAGCATAGCGAGTCC
AATTTAAAATCCATTCTTCAAATCAGAATTGTACAGAGTAGCCGAATTTAACTATACTTACAATGGTCATTCAATTTGGGATTTTTCTTTTCCAA
CCTTATTCATATTATTTCATATCAGTTTTCAGAATAAAGAGACATTAGAATTTCCTTTTTTCGATTTATTTATTTCTTATATGATATTAGTGTTT
ATAGCTAAAGTTTTACATGGAAGACAATGATTCTTAGCCTAATTCTTATACGAAGACCCTAACAAACAAACATGGAAGACAATGATTCGGCTAAG
ACTAACTTAAGGCTAATAAGACACGATAAATCACAATGAGTTAACGATAGTAACGCTTGATTGTGATAATTGAATATCAATTAGAGTTGTGTTTC
CCTTGGGACGCGAGCCCAAAGAATCCAATCTATGCCTAATATCACCCTGAGATTACGAACATGCGAAGCTGAACCCGCATCCATCCGACGACCAA
TGGACGGAGACACTTGCACTTAAAGCTGCCAATTGGAGTTTTTCCCGGTGCATCGAGAAGTGGAACTGTGCATCCTGGCGATGTTTAGGCCTGAA
CCCAACGGTCGAACTGCTGGCGCAACTGCTGTTCGTGGTGCTGGCGAGCTCCCTCGGCTGAGGTCCAGAAGAAGGTGCCGCTGGTGGTGCGGGCG
AAGTGGACCGGGATGAAGGTCTGCTCCGGATGGACGGGCACGATGCTCTGTTGCTGACCCTGCTGCACGATCATGGCCACGTTGGTGGGGCACTG
GCGGAGATCGGTGTACAGTCGCTGCTCCAGCTCCTCGTTGGCCATGTTATCGCAACTGGCCGCCGGATCTTTGCGCATGTCCTCCAGCGAGGCGT
TGACTGCATTTTGGTTCTGGATCTCGGCCAGAGTCTTCCGGAGTAGCTGCTTCTTCTTCACCAGTCGCAGAAGGGGTTTGACCAGTTTCCTCAGA
CTCCGCATGGCCATCGTGTGCTGATCTGATTTCGGCTCCATCACCTTGCTGCTCTCAAACTTGTATTCCCGTGTGATGAACGACATTGTGTTGAG
GATTGTTGAGATTTATAATAAAACTTGGGATCTTAGTTGGTTGCACTCGGTTGAGAGTTGGTAGTATTCTGGTTTTCCTGCTGCACGACCGACTC
CTTATATACGATTTGCTCTCTTTGGTTTCTCTCGGCGGGGGAGAATTCTCGCACAGAGCGGCGGTTCTCTCGATCGATGGACCCAGCCAATGGGA
AGGCAGACTGCCTGCAGGTGGTTGCACAAACAGTGAGAGCGGGAGACAAAAGAGAGCCAAGAGAAAGCGGTCTCGGAATCAGGAGCATGTCCTTA
CCCTTGAGAAAGCAGGGTATGATGAATTTTTGAGTCTGTGCATAAAAAAATAGATTTACGAAAAATAAGGTTAATATGTTTTTATTGTGTGTATA TCTTTTAAGTGTATTTTTTCTAAAAAAAATTATTTATAATAGTAATATTGAAAGGGGCCATATAAGGTTGAATTTAATTGAATTGAATTCATTGA
ATTTATAATAACTATAGTAATAAGATCATAAACTTGATGAAAAATATCAATATTTAAGGACTCTATTAAAATTAAACTTAAAAGACTAGCAAGAA
TAAAATGTATCCTAAAATATTTGGTATACAACTAAATTAAAAACTATTTAAAATTAAATAATTAAGATCGGCACAGCCTTACAAAAAAAGTTTTC
CTTAACAGCACACTGCTAAATTAAGGTATGTAGGAAGTACATCGGTAAAATTACAATAAATACAAAGAGATCGTTGTATATTTAACAATTATTTA
GTATTTTACTAATGGTATTTATTTTTTGGAACATAGCATACCATACTAAGTCATTTACTTTAAAATTTCATATGTTTCCCACGTGATTCAAATGC
TGGGTATTACCCACTCGAGTTGCTCATTCACTGCAGGTTTTTAACGGATTTTTTGACAGTCGCATAGATCTCGGTCGGTTCTCGATCTTTCGCCC
CCTCTGAGAGTACCATGCCTCACAACCTCTCTTTACCTGCTCGACTCTGTCGCAAGAAAAGTAGAAGTCCCTAAATCCCAAACGTAAAATTCCAG
GAGAGTACCGA
(SEQ ID NO: 568)

Exon: 1956..1001
Start ATG: 1891 (Reverse strand: CAT)

Transcript No. : CT16583
TCTCAACCGAGTGCAACCAACTAAGATCCCAAGTTTTATTATAAATCTCAACAATCCTCAACACAATGTCGTTCATCACACGGGAATACAAGTTT
GAGAGCAGCAAGGTGATGGAGCCGAAATCAGATCAGCACACGATGGCCATGCGGAGTCTGAGGAAACTGGTCAAACCCCTTCTGCGACTGGTGAA
GAAGAAGCAGCTACTCCGGAAGACTCTGGCCGAGATCCAGAACCAAAATGCAGTCAACGCCTCGCTGGAGGACATGCGCAAAGATCCGGCGGCCA
GTTGCGATAACATGGCCAACGAGGAGCTGGAGCAGCGACTGTACACCGATCTCCGCCAGTGCCCCACCAACGTGGCCATGATCGTGCAGCAGGGT
CAGCAACAGAGCATCGTGCCCGTCCATCCGGAGCAGACCTTCATCCCGGTCCACTTCGCCCGCACCACCAGCGGCACCTTCTTCTGGACCTCAGC
CGAGGGAGCTCGCCAGCACCACGAACAGCAGTTGCGCCAGCAGTTCGACCGTTGGGTTCAGGCCTAAACATCGCCAGGATGCACAGTTCCACTTC
TCGATGCACCGGGAAAAACTCCAATTGGCAGCTTTAAGTGCAAGTGTCTCCGTCCATTGGTCGTCGGATGGATGCGGGTTCAGCTTCGCATGTTC
GTAATCTCAGGGTGATATTAGGCATAGATTGGATTCTTTGGGCTCGCGTCCCAAGGGAAACACAACTCTAATTGATATTCAATTATCACAATCAA
GCGTTACTATCGTTAACTCATTGTGATTTATCGTGTCTTATTAGCCTTAAGTTAGTCTTAGCCGAATCATTGTCTTCCATGTTTGTTTGTTAGGG
TCTTCGTATAAGAATTAGGCTAAGAATCATTGTCTTCCATGTAAAACTTTAGCTATAAACACTAATATCATATAAGAAATAAATAAATCGAAAAA
AGGAAA
(SEQ ID NO: 569)

Start ATG: 66 (Reverse strand: CAT)

MSFITREYKFESSKVMEPKSDQHTMAMRSLRKLVKPLLRLVKKKQLLRKTLAEIQNQNAVNASLEDMRKDPAASCDNMANEELEQRLYTDLRQCP
TNVAMIVQQGQQQSIVPVHPEQTFIPVHFARTTSGTFFWTSAEGARQHHEQQLRQQFDRWVQA*
(SEQ ID NO: 570)

Gene Symbol: Tom
FlyBase ID: FBgn0026320

Celera Sequence No. : 142000013384113
CCCCCCCCCGGCACAATTGTTTATAGAAATCAAATGATTAATATATTATTATAGAAGAAAAACCGTTTAATAGCACAAGCGTAAACACCAATTGG
AAGCAAATCAATAAATTTGAAGGAAAGCTAAAAAAATCCATAAATAAAATATCATTGAAATGGACAACTAATGTGTTTTTATCAGACTGCTTACT
AAACTAAATATCATCTTTTTCAAAACCCCCCCAAAAAAATAAGGTGTTTTAGTTTCGGTGTGTTCTGTGAAATGGTATTTTTTATTTATTATACT
CTCGGAAATTATATCAATTTAAAAAAATTTACTTTTGAATCAGCGAACATATTTATAGGAAAAGGTTTGAAGTGTTTGTATGTGATAAATACAAA
TTAAACTACAATTATTGTATATGTGTTTGCAATCTTAGACAGCTATCGTATTTTGACTCTTGTTTGCTAAAAAAAAGCATAGTTTTAAAGTATTT
GCAAGACGTTTGCAGTCGAGTAGAATTTTTTTCAGATACAAAACATGAATTTCAATAAAAAAAAATGAATTAAACAACATTGAATGATGGTGTAGA
TACAATTAAAAACGAAATAAAATTAAAATGCTCCACAACGGATTTTTACAACAAATATCTATCCGTTGCGTTACAGAAGTTTTGTGAAAATTGCT
GTTTTCTAATTTCAAATTTGTATTTGTGTGTTAAACTAATTCTTTCCGATCATCGGAACTTCGTTTATGTTTAAAAGTCAAAATGTATCACAATT
TTGATCATTTTGTTATAATAAATACGGCTGCACCTGTCACAATGCTAATTATTTAGTACACATTTATGCTGAATGTCTCGACTATATTTAATGGG
TCTTGCACAAATTTGATTCAATGAAACCCAAAAGGTAGTATAGTAAAATTTCATTAAACCGATATTTACAAATACCAGAAAATAAGCAGATACTT
AAGGATGCACATTTAAATGAGTATGCATGGATCGCGCATTAAATCGGTGCTTTTAAATTTTAAAACGTATTTATGATATTCCTTTTACAATCGTG
ATTACAAGATATAGGAGAGCCCAGTTGTTAATTCGATGACAAAAAAAAAAAAAAGAATAATTTGTGGGGTGAATTATTCTTTATAAATCTCTACAG
AAAATGCCGGAAAAGTACTCCTTATCGAATATAAAATGATATAAGTATGTACAATGAGCAAAACCTACCATTCGATATTATATTTATAAAACATG
ATTTCCTCTCTCTACCTTTCTTGTACAGTGCACACAATTTTGGATAAAAGAACGTTTCTAACAAACTATTATCAAAATTTATTGACAGTCGAGTA
CTTTCTCAATTTCAGTATGAGATTTTTATACCCTGTATCAATATTTTTGTGTAGTATGCGTAAATGTAAAAACGATCGTACATATGTAAGTTTTG
GATACATATTCTATACAAACATATGCGTAATTGAGTAAAGCAAAGTGAACTCGGCTATATAATTTCACAATTATTTGAAACGCTTCAATCAAGTT
AAATGAAAATCCGTCAAAGCAACCTAATCAATTTGATGCCTGGCTTCAGTTATTAATGCTAAGAGTGCATCCAGTTTAAGATCTTTAAACCGTTC
AAAGTGGTCCATAAGTGGCTGAATTGCATCCGACTCAATGGCTGCCGAGATGGTCTGGTTTTGAATAGTGCGATTGAGGCAGGATGCAACCTGTG
CCAGAAATTCTCGCCACTTTTGCCTGTTCTCCTCGCTAAGAGTTGCGTCAGTTCGCGAGACGTAGATTTCCTCGGCGCGAAGTATCAGGGCAACC
AGCGAAAGGATTCCAAACTGCCAATTTAATAATTAGTACGCGTATCTATTACTTAATACTGAGGATAACTTACGCGACTGCAAAAAATTCCAGCA
AGTTTCTTGTCATTCAGCGTAATAGCAGATGAAATGCTCACTAGGAGTTCGAAAGTAGCTTTGTTAACGTGTTTTTTAAACTCTGGGTAAAGAGC
GTACAAGACGCCTTCAACGTCGTCCTTGTCCTTTTTCACCACTGTTTGTAGGGAACAGAAGACGCCGCTCCACACGACCCAGCGAATGCTTTGAT
CCGCAATAAAGGGCATTATGCGTCTAATAAGTATCTGCAAAGGAAAGATTGATTTAAATAAAATAGTGAGTTTCATGCGTATAGCACTAGAACAT
AAATCGAATTCTATTTGGTTGCACTTGTTAAAATTAGTATAAGAAAAAGTACACACCTTTCCCTTGCGCACATTCATCATGGCGATAACCTTGTC
GAAGGCCAGACCTGCCTTTAATTTATTGACCAACGCAGCTTTCGTCTCTACCTCATAGTTGAACTTGTTCTTTAGTTGCGGATTCATGGTTTGCG
GATTGGCGGCTTCAGCAGCACGTTCTTCGGGCGTTTTATTGGCCATTTCCAGCTGCTCAAGGGCTGCGATCCGTTCGGCTTCCTTTTTCTTTTTC
AGCTCAATGGTGGCCATCACTTCTGGGCTTTCCAAATCCTCCAACTTCAGCAGATAGCGATACAGTGTTTCAATCAGAAGCAAAATGTGTCGCGA
CTTCCGCATGCTACTGGGATTTACATCATGGCTCGCGGAGGTGGGCAGCGGAGTCGAGCTTTTTGATGAAGAAGTTGCGTTGGCTTCAGCAGCGG
CATTTGATTCACCACTCATAATGTCAGCATCGATAATTTTTCGCGGAGCTGTCACACTTCCGTACTGTAGCTTTCCCAGTGAGTTCTCGAACTTC
AGTGGTGAGAATATATAGCCTGTCAGGTTGTTGTTGTTACCACCTGATCCATTGTTCGTGTTGCCTGACGTGCTGTTGGTGTTCTCCGAGTTGCG
TCGCTCACGTCCGTGTCCATTGCGAGTACCATTCTTGTTGCCCAACTGTACGAGAATAAGCTGCGCATGGCCGCGTGGCTGAGTAAGCGGATGAT
TCAACTGGTTGTCCTTGTGCGCCTGACTGTTGCGCATTTGCCCGTTCTGTTGGGCCTTGCGCTCCCTGAACACCGTGTAGTAATAGTCGTCGATA
TACGGCGTGTCCGTATTCAGCTGCGAAAGCTGGATTCCGATTAGCCAGTGCTTGTCGCGCGTGCTCATTAGGTTGGCATATTCATCGTACTCTTC CAGCGGGTAATTTCCTGTACCATCTGGACGTCGTCCTTGTTGCTGCTGTTGCGCCTGCGATCTCTGACGATCGCTGGCCACGGATCCTGCTCTGC
TCTGTTGCATTTGGCGTACAACAGCAGCCTGTTGAAGCAGCGGATGGTTTTGCTGGATCTCTTGCACTAGTCGCATGTTGAACATGTTATACATG
GAATTCGGTGGCTGCTGACCTAATAGACTTGTGGCAGCTTGCAGCGGGTGCGGCGGCATTCGCGGTGGCAGCATCTGGTGCGGATGGGGAGGTTG
CATAAAAGCCCCTGGATGGATTCCAGCGGCGCGCATCGCATTGAAGCTTGGATGCATCGCGAAATTGTTCAGGGCCGTGGGCAGAGCTTGTGGAT
TGGGTAGAGGTCGCTGGTTGCCGCCGGGCAGTGGAAAGTTGTGCGGCATGTGCTGCTGCATTAGAGGATGCTGGGGCAATTGCGGAATATTCCCG
GGCAGACCTTGCGGGTAAATAAATCCGGGCGGCACTCGGTTGCCACCAATACCGTTTAGTTGTTGCTGCGACGATGGCGTGGGCAGTAGCTCGGG
TCCGGGGAAACCCAAATTTGGCCTCGGTGGAGAGGTGTGCGGCGTGCCCAAGAAGCCAGGGGGTACTGCAATGAATTGTTAAATGGTGTTATTTT
CATATGTCGCAGAAATCTATCAGGGACTTGAAGTTTGTTCCTTAAATGGTTAAATCTGTCTTAAAAATTGTCCCCAAAAATAGATTCGTAAGAAA
TAAATATTTTTAGGAATTATACTTTTTGTTGGACATGTTTTCTTTTTAAATACTGAGGCCTGTTTTTGTATGCATCAATACTTTTTAGTTTTAAT
ATATAATTACCCTTGTGCTGCGCTTGTTGTGGCGGCTGCTGCTGCGACTGTTGTTTCTGATGATGCTGCTGCTGCAACATCTGTTGCTGCAACAT
GGTTGGTGTAGGCACCTGCTGCCTGTTACCCAGACTAAAATCATCAAACATTTTGCGTTCCGCCTGTTGCTGGCTCTGCTGCTGTTGTTTCGGAA
TGGCCTGCTGAATGATCATATTGCGCTCTATATCCTCGAGAGTTGTAATTTTTGGAAAAGGCTGTGGATTCAGTGCAAAGTTGGCATTCGCTTCC
TGCGGTGGCTTCATTTGTTGTGGTTGGTGCTGCTGATGTTGCTGCTGCTGTGGCTTGAAGGCGCTGCGCATAGGCTCGCGGAACAAATGTTGGTT
GTTGGGAAACGGCTGTGATCCCCAGACCCCGGAGTCCAGCTTAATGCGGTTGCTCAGCCCACCGGCTTCGCTATCAGTGGTGAAAGAGGACAGGT
CCATGTCGTCCAACTTCATGGAGGAAATGTTTAGCTCCAAGTCCGAGTCCCCTATGTGACGAGACTGTCGGAAGGGGGCATTCAAAGGGGCCGGA
GTGGAGCCGCTTGAAGAGGGCGCCGATGATAGCGGATTAGCGTGTCGCAGGAAGGCACCATTTCCCTGATCGGCAAAATCCGTATTTCCACTAGA
TTCCGCGGGTCGCTTCCGCACCCTTTCGCCATTCCCGCCCAGGCGTACCATCGTCTCATGGGCTTCCTCCCAGTCGCCATTTATAGCGGATCCAA
AGGTTTCGTCATTGAGGGCATCGTATTCCGCCTCGACGATGCGTCCATCGCCACCATCTTCGTCCTGGAGAAACAATTGAAGCAAGTAAATTAGA
CATTCCTACTTTTTCTGCCCCCGGTGGCCTTCGATGCCCCCTTATTTGCCGAGTGAAAAGTGTGCGTTGGGCATTTGCCGACCCCTGTGCGGCCC
GCTATCCCGGATATTGCAGCCGCAATGTCGGGACCGCTGCTTACCGGTAGATTCGTGTCAAAGCCGAAAAACGAGTCATCCATGGCGATAAATCT
ATTGCTTTACAAAAAATTATCATGACTTGTCAGTGACAAGTTGTCACCTCAGCAGTATAGCTGTCAAAATATCGATGGTACTATCGATAGTCTGA
CGTCGATGGTTTTCTGACTATCGCCACAATACATCAATTTCGCTCGCATATAAATATTATCATATTACAAATGTTGGAATTAACATGCAAATTTA
AAATATATATTTTTTTCATACGTTTTTTTTCAATAGGTGAACGACTGAAGATTTGTCTAAATTTATAAGTTTGCATTTTGCTACAGTGATGTTAG
AAAAAAATGATGATTTAACCACTGCCAAATTTCGTATGTTGCATATTTATTTATTCAGTTTGGGACTTACCACGACTGGTTAATAAGTCAACAAC
ATTAGATTTTACTGATCAATGAAAAATCTGCCCTAATTAAGGTGCATTTGCACTCCTTCAATGTATTCGATATTTTGAACTAGTTCGAAACTTGA
AATCAGCGCCCGCAAGCTCATCCCTAAATTACTAGTTCTTGAACTATTGCTTTGGACGGAACTACGAGCCTGTTTCCTTTTCCAAAACAACTTAG
TCGAAATGAAGCGGAAAACGAGCGAGATCTGGTGCTTTTTCCGGGCGGTGGACGACACGTTTGCGGTGTGTAATATCTGCAAGGCGAAGCTCTCT
TACAAGACGACCACCACGAATCTAAGCAAGCACATGAACAGGATGCACCCCACATCGGGACTCAACCGGAACTCCAAGTACAAATTCCAGCCGCA
GACCACCATCGCCATCGACCGGAACAAAGCCAAGCCGCGCAACTCAACGCAAGAGCTGATATTGTTAGAATTCGTGAAGAAACATCCGCGTCTGC
TTCAGAATCCGACGTGGGAAACACGGGGCAATCTGGAGTCGCTGTGGGAGGAACTGTCATCCGAACTTAATAGCCACGGTCCGCCGCGAAAAGAT
ATAGCCACCTGGAGAAGGGTATTCTAACTTACTTTTTTTCTAACCGCTTGCATTATAAGTTGATTTGTTTGTAGG
(SEQ ID NO: 571)

Exon: 5060..4985
Exon: 4814..4001
Exon: 3770..2242
Exon: 2124..1879
Exon: 1822..1001
Start ATG: 5023 (Reverse strand: CAT)

Transcript No. : CT16663
TCATGATAATTTTTTGTAAAGCAATAGATTTATCGCCATGGATGACTCGTTTTTCGGCTTTGACACGAATCTACCGGACGAAGATGGTGGCGATG
GACGCATCGTCGAGGCGGAATACGATGCCCTCAATGACGAAACCTTTGGATCCGCTATAAATGGCGACTGGGAGGAAGCCCATGAGACGATGGTA
CGCCTGGGCGGGAATGGCGAAAGGGTGCGGAAGCGACCCGCGGAATCTAGTGGAAATACGGATTTTGCCGATCAGGGAAATGGTGCCTTCCTGCG
ACACGCTAATCCGCTATCATCGGCGCCCTCTTCAAGCGGCTCCACTCCGGCCCCTTTGAATGCCCCCTTCCGACAGTCTCGTCACATAGGGGACT
CGGACTTGGAGCTAAACATTTCCTCCATGAAGTTGGACGACATGGACCTGTCCTCTTTCACCACTGATAGCGAAGCCGGTGGGCTGAGCAACCGC
ATTAAGCTGGACTCCGGGGTCTGGGGATCACAGCCGTTTCCCAACAACCAACATTTGTTCCGCGAGCCTATGCGCAGCGCCTTCAAGCCACAGCA
GCAGCAACATCAGCAGCACCAACCACAACAAATGAAGCCACCGCAGGAAGCGAATGCCAACTTTGCACTGAATCCACAGCCTTTTCCAAAAATTA
CAACTCTCGAGGATATAGAGCGCAATATGATCATTCAGCAGGCCATTCCGAAACAACAGCAGCAGAGCCAGCAACAGGCGGAACGCAAAATGTTT
GATGATTTTAGTCTGGGTAACAGGCAGCAGGTGCCTACACCAACCATGTTGCAGCAACAGATGTTGCAGCAGCAGCATCATCAGAAACAACAGTC
GCAGCAGCAGCCGCCACAACAAGCGCAGCACAAGGTACCCCCTGGCTTCTTGGGCACGCCGCACACCTCTCCACCGAGGCCAAATTTGGGTTTCC
CCGGACCCGAGCTACTGCCCACGCCATCGTCGCAGCAACAACTAAACGGTATTGGTGGCAACCGAGTGCCGCCCGGATTTATTTACCCGCAAGGT
CTGCCCGGGAATATTCCGCAATTGCCCCAGCATCCTCTAATGCAGCAGCACATGCCGCACAACTTTCCACTGCCCGGCGGCAACCAGCGACCTCT
ACCCAATCCACAAGCTCTGCCCACGGCCCTGAACAATTTCGCGATGCATCCAAGCTTCAATGCGATGCGCGCCCGCTGGAATCCATCCAGGGGCTT
TTATGCAACCTCCCCATCCGCACCAGATGCTGCCACCGCGAATGCCGCCGCACCCGCTGCAAGCTGCCACAAGTCTATTAGGTCAGCAGCCACCG
AATTCCATGTATAACATGTTCAACATGCGACTAGTGCAAGAGATCCAGCAAAACCATCCGCTGCTTCAACAGGCTGCTGTTGTACGCCAAATGCA
ACAGAGCAGAGCAGGATCCGTGGCCAGCGATCGTCAGAGATCGCAGGCGCAACAGCAGCAACAAGGACGACGTCCAGATGGTACAGGAAATTACC
CGCTGGAAGAGTACGATGAATATGCCAACCTAATGAGCACGCGCGACAAGCACTGGCTAATCGGAATCCAGCTTTCGCAGCTGAATACGGACACG
CCGTATATCGACGACTATTACTACACGGTGTTCAGGGAGCGCAAGGCCCAACAGAACGGGCAAATGCGCAACAGTCAGGCGCACAAGGACAACCA
GTTGAATCATCCGCTTACTCAGCCACGCGGCCATGCGCAGCTTATTCTCGTACAGTTGGGCAACAAGAATGGTACTCGCAATGGACACGGACGTG
AGCGACGCAACTCGGAGAACACCAACAGCACGTCAGGCAACACGAACAATGGATCAGGTGGTAACAACAACAACCTGACAGGCTATATATTCTCA
CCACTGAAGTTCGAGAACTCACTGGGAAAGCTACAGTACGGAAGTGTGACAGCTCCGCGAAAAATTATCGATGCTGACATTATGAGTGGTGAATC
AAATGCCGCTGCTGAAGCCAACGCAACTTCTTCATCAAAAAGCTCGACTCCGCTGCCCACCTCCGCGAGCCATGATGTAAATCCCAGTAGCATGC
GGAAGTCGCGACACATTTTGCTTCTGATTGAAACACTGTATCGCTATCTGCTGAAGTTGGAGGATTTGGAAAGCCCAGAAGTGATGGCCACCATT
GAGCTGAAAAAGAAAAAGGAAGCCGAACGGATCGCAGCCCTTGAGCAGCTGGAAATGGCCAATAAAACGCCCGAAGAACGTGCTGCTGAAGCCGC
CAATCCGCAAACCATGAATCCGCAACTAAAGAACAAGTTCAACTATGAGGTAGAGACGAAAGCTGCGTTGGTCAATAAATTAAAGGCAGGTCTGG
CCTTCGACAAGGTTATCGCCATGATGAATGTGCGCAAGGGAAAGATACTTATTAGACGCATAATGCCCTTTATTGCGGATCAAAGCATTCGCTGG
GTCGTGTGGAGCGGCGTCTTCTGTTCCCTACAAACAGTGGTGAAAAAGGACAAGGACGACGTTGAAGGCGTCTTGTACGCTCTTTACCCAGAGTT
TAAAAAACACGTTAACAAAGCTACTTTCGAACTCCTAGTGAGCATTTCATCTGCTATTACGCTGAATGACAAGAAACTTGCTGGAATTTTTTGCA
GTCGCTTTGGAATCCTTTCGCTGGTTGCCCTGATACTTCGCGCCGAGGAAATCTACGTCTCGCGAACTGACGCAACTCTTAGCGAGGAGAACAGG
CAAAAGTGGCGAGAATTTCTGGCACAGGTTGCATCCTGCCTCAATCGCACTATTCAAAACCAGACCATCTCGGCAGCCATTGAGTCGGATGCAAT TCAGCCACTTATGGACCACTTTGAACGGTTTAAAGATCTTAAACTGGATGCACTCTTAGCATTAATAACTGAAGCCAGGCATCAAATTGATTAGG
TTGCTTTGACGGATTTTCATTTAACTTGATTGAAGCGTTTCAAATAATTGTGAAATTATATAGCCGAGTTCACTTTGCTTTACTCAATTACGCAT
ATGTTTGTATAGAATATGTATCCAAAACTTACATATGTACGATCGTTTTTACATTTACGCATACTACACAAAAATATTGATACAGGGTATAAAAA
TCTCATACTGAAATTGAGAAAGTACTCGACTGTCAATAAATTTTGATAATAGTTTGTTAGAAACGTTCTTTTATCCAAAATTGTGTGCACTGTAC
AAGAAAGGTAGAGAGAGGAAATCATGTTTTATAAATATAATATCGAATGGTAGGTTTTGCTCATTGTACATACTTATATCATTTTATATTCGATA
AGGAGTACTTTTCCGGCATTTTCTGTAGAGATTTATAAAGAATAATTCACCCCACAAATTATTCTTTTTTTTTTTTTGTCATCGAATTAACAACT
GGGCTCTCCTATATCTTGTAATCACGATTGTAAAAGGAATATCATAAATACGTTTTAAAATTTAAAA
(SEQ ID NO: 572)

Start ATG: 38 (Reverse strand: CAT)

MDDSFFGFDTNLPDEDGGDGRIVEAEYDALNDETFGSAINGDWEEAHETMVRLGGNGERVRKRPAESSGNTDFADQGNGAFLRHANPLSSAPSSS
GSTPAPLNAPFRQSRHIGDSDLELNISSMKLDDMDLSSFTTDSEAGGLSNRIKLDSGVWGSQPFPNNQHLFREPMRSAFKPQQQQHQQHQPQQMK
PPQEANANFALNPQPFPKITTLEDIERNMIIQQAIPKQQQQSQQQAERKMFDDFSLGNRQQVPTPTMLQQQMLQQQHHQKQQSQQQPPQQAQHKV
PPGFLGTPHTSPPRPNLGFPGPELLPTPSSQQQLNGIGGNRVPPGFIYPQGLPGNIPQLPQHPLMQQHMPHNFPLPGGNQRPLPNPQALPTALNN
FAMHPSFNAMRAAGIHPGAFMQPPHPHQMLPPRMPPHPLQAATSLLGQQPPNSMYNMFNMRLVQEIQQNHPLLQQAAVVRQMQQSRAGSVASDRQ
RSQAQQQQQGRRPDGTGNYPLEEYDEYANLMSTRDKHWLIGIQLSQLNTDTPYIDDYYYTVFRERKAQQNGQMRNSQAHKDNQLNHPLTQPRGHA
QLILVQLGNKNGTRNGHGRERRNSENTNSTSGNTNNGSGGNNNNLTGYIFSPLKFENSLGKLQYGSVTAPRKIIDADIMSGESNAAAEANATSSS
KSSTPLPTSASHDVNPSSMRKSRHILLLIETLYRYLLKLEDLESPEVMATIELKKKKEAERIAALEQLEMANKTPEERAAEAANPQTMNPQLKNK
FNYEVETKAALVNKLKAGLAFDKVIAMMNVRKGKILIRRIMPFIADQSIRWVVWSGVFCSLQTVVKKDKDDVEGVLYALYPEFKKHVNKATFELL
VSISSAITLNDKKLAGIFCSRFGILSLVALILRAEEIYVSRTDATLSEENRQKWREFLAQVASCLNRTIQNQTISAAIESDAIQPLMDHFERFKD
LKLDALLALITEARHQID*
(SEQ ID NO: 573)

Name: BCDNA.LD27979
Classification: hypothetical
Gene Symbol: BcDNA:LD27979
FlyBase ID: FBgn0028470

Celera Sequence No. : 142000013384285
CTGAAAATTTCCGACCTTATTGCACAGCTTAAGTGCAAGGTTAATCCGGGCAGAGCCAGATCCCACAAGACCAACAAATCACCGTTTTTATAGTG
CGCGGATTTTAGTTTTTTCAAAGCAAAACGAAAGTTATCACCGATAGAACACACACACACACTTTTATACGTGTACACTACTGCGTATGCATATA
TAATATATATATATATATATATAGATATATAGATATTGAAGTATTTTGTTAGCCCTGGAAATCGAAACCCAAACGTTGCCTAGAATGGATCAACC
ATCCATGATACAATTGTATAACTAACTCAAGTCTCACAGCGCGTTATTTTATACCGATTAAATTGTAAACCGTAGACCTTAGGCGTACGCTCATG
TTATATCAGTCAGAGTTCTATATCAACAATTGTATAAAGATGATTGAATTGATGACAGTGACTTTTTTTAAATCACGCATATTTTTATAAAAATA
AGAGTAATAACAATGCATGCAACACATGTATTCACATGAATATATGGGGAGATTGCATAGCATGGGCTTGTACAGTGTACATAAAATAAGCCGTC
GCCGATTATATAGGACCCAAGAATATCATATTTTATATAGAAGCAAGCGCAAGCAAATAACCCAGGCAGCATGCCCTCAACTTTCAGTCGTAAAC
GGAGCGATTGGAAGTCGCTCCTAGTCTGTAAGATCCACGATTAACTAGCCGCTCTCTCCTTCGGTTAACTTCGTTCCGGTGTCACACATCTCTGC
AAGGAGGGCATTATTGGTGTAAGGCAAACTTTTGAAGAAGGCAACCTTAATGATAAAATATGTATTTAGATATCCCTAAGGTACCAGCTAATGTC
AAGATACTTTAATAAAACCGAATTCAAAATTGCAAGTATTGAAATATCGCCGACTAACTTTTATATGTGTTGGTTTTCTTTGGGTTTATATGTGC
TCTACAGTCAAAACTCATTTTCATTTCTGTTTTTTTTTTTTTTAGATTGGTTTATATTCTGGATATTAATACACTTTTAAGACATATAGACTAAA
TTCTTACTGCTATGTTTACACTGCGTTTGGTGGCTATATATTTATGCTAGGTTTCGAATAAACATTTCAAACACGCACACCAAATTTCCAACTCT
TATGAATATTTTGAAATCCATGCGCTGTTACATTTTGATGTGGGTGCGAGTGTATAAATGTTAAAAAATAGTTGCCATAACCGATAGAAATATAA
AATGGTAAGGAGATAACACAAAAAAGTAGAAAAAGAATCATGTACAATACAAATTAGGGGCGAGTGCTTATATACAGAGTGTTTGTGTCTAGTTT
TTAACTAAAACTAACGTATTTTTCCGTTTGCATTTGCATAGTTTTGAATATGTTACGCTTAGAACTAGATTTAAAGTTGAGGCGCTGCTTCTCTT
TGAATACAAAGAAATCCTGCTTTCTAAAGGATTTTCAACTTTCCGCTTATCTCTTTAGTTTGTCTAAAAAGGCCTCAATAACAACTTAATATAAT
AAAATACTAACATTTACAGCGTTTCGTTTTGAAAAAGAGAGATAATAAATAAACTAAGAGTTTTTCAAAAATATCAAAACGGGATTGGGCATAAG
GGGTTGGTGGTAAAGCAACGAGGGTCAGATCTCTAAAGCCTCGAATTGAGTAAACTAGTGGATCCGGTTTCATTTCTTGAAAACTTCGTGATACC
GGGAATTGAAGTGTTCTCATATTCTAAATAAATAACAAGTAAACGGTTTACCGTTTCCGATTCCAGTACCTTTCCGGGGAATGAAATTGGTAACA
TGGCCCTCGGCTACGATTTCGCAGCTTCTCTGTTTACAAGTTGGCTTGAATTGCATTTAAAATAAATACTACACTACTAGCAGGGGCTAAGATTA
CGTTTACACTGCTGCTAACTGTCCTGGAGGCGGACTCTCCTCAGATCTTTCTATTTGGGTCTGCTGCTTATTTTCCTCACTTGGTCGCCGCTTCT
TTAGTGGGGGAATTTCCGTTTCAATAGCGGGCGTTGGCTGCTGTTCTATAATGCAGGCGGTTCTTTTCTGGCCGGGACTGCTGTTGGGCAGCGGT
TCGTTGGATCCATTCACTATATCGGTGACTATGTGAGCCTCCAGTGAAGGCGGTAGCAATGGTGACAATGGAACGGCGTTCAGATCACATGCATC
CTCATCATCATCCTTATAATTGTGCCCCACATTGCCAAAGAGATCACTGTGTCTATTGTGTGATCTTTCCTCTTCTTCGTCATCATCATCGCTGT
AATCGTTGTCCCAGAATACCTGGGCTCCTGGAAACACATACGAATAGTTGTTGGTGTGCGAATAGAATGTTCCAGGCTGCAGACGCTCGGCTGCT
GTCTGTCGCTTTCCCCTCTGTTGTGGAATGGGCGTCAGGCTGGGCGCCACTGTCTTGGTCTCCTGAACAAGATTGCTGGGTCGCACGTAGCTAGG
CGTGGCTTCGTTGTCGCACTGCTCGATGCCGCTATCCTTGGAGGAATCAATGGAAAGATGGCGATAGCTCTCCACCGTTGTCTGAGGGCCTTCCA
GGCCCAGACGATCGCAACTTAGGGCTGTGGTCTCGTTCAGCTCAACCAGTATGTCTGTTTTAATACGTTCGATGGCTGCCGCTTCGGCGGCAGTG
GAACGCTTTCCACAGCTAAAAGTAGATGACTCAAATCCACTATCCGAGCAGGTGCCAGCTGATCCTAGTATGTAGTCCGCCGAACTATTTGATTT
AATAGACTGCGTATCCGTGTCCAGTTGCGACTGTCGCTCGCTCTCTGAACTGCAGTGGCGGTGGTGAAGTAGATGATGATGGAGGTGGTGATTAG
AGTGCTCCGGAGGCATTAGCTCCTTGCTTTCGGTAAGCACTGACTCATCGCAGCACAGCTGCCGCCAGCAATCATCGTTGTCCGACAACCGGTGG
CAAATCTGGTTGATGATCACATCGGAGTCGCCCAGCAGCTCCACATCGAACTTAAGGTGATGCAGCTGCTCGCGATTGATAAGAATCTGCGGCAC
CGTGGCCGGTATGCTGCTGGGAATGTGGGCCACAGGTCGGACCTTCAGCGAGGAGCCGATCACGATCAGTAGATCGCACACGTCCTTGTCGGTGG
CCATGACCGTGTGGTACTCATCCGGCAGTCCTGTTGGCAATATGAAAAGCAAACACAATATGATATATGGTAAATAGCGTTACTTTGTATTTTCA
ATAGTTTATCTCTTAAATAAACACTTCTTTTGATCGTCGAATTTGAAATTCTTGCATTTATTTTACCAAGGCTATTGATAATATATAATAAATCT
GTATAAAAATGGCACCTACCCTCGCCGAAAAAGACGATATCCGGCTTCATGATGCCGTTCTCGACCAGTTGGCGCAGCTCCTCCTCAGTAACGGC
CACCGAGGCATCCACGCTCTGCTCCTTATTGGCTGGCACTGCGGGCACACCGGAATTCGCTGGGCAAATATGTCCGCCCGCAGGGCGTCAGCGT
TGCACTTGAAACGACACTTGGTGCACGAGGCCGTTGAAAAGGAGCCGTGACACTCGATTACTCGCTGAATGCCTGCCACCCGCTCGAGGGTGTCG
ATGTTCTGTGTGTAGTTGCGCAACAGTTTGCCCTTGGTCTCCAGCATTTTGATGAAACGATGGCAGGGTGAGGGCTGAAACTCGCCGGGATATAT
CTCGCGGGCAAACTTGTAGAACGGTCGTGGATCCCTCTTGAAGTAGTTGATATCAAACATGGCCTGCGGATCGGGCAGATCGGGAAAATCATGGG CCAATCGCGCATATATGCCATTGGTGGACCGGAAGTCCGGAATGCCGCAGGAGACGGATACTCCGGCTCCCGTTAGCACAATGATCTTCTGTGAT
TTCTTGACCAAACTGATGACATCGTCGAAGGTGTTCACTGAGGCCAGCTTGTTGCGCCGCTTCGGCTCGTTCAACAGGTGGGCCAAATAGTCCCA
CAGCACGGAGTCGTCGGTGTCGCCCGCCAGGCCGGTGGCGAAATGCGGCATAATGCTGGCAATAACCTGGCGCGGCACACGACCTGTGTAAAATT
CTCGTTGCAACCAGCGCAGCTTCCAGTCGGGTTCCACGGATGAGGAGCAATTTGAGCTGGAGTCCTCATCCTCGTTGCTCGTTCCGGTGATTCCC
TCCTCGTCGTCCTCCTCCTCCTCCTCATCGTCCTCTTCCTCCTCCTCCTCGTCATCTTCATCCTCGCCCATTGACTTTGTGGGATTTTTGGTTTT
ATGCTCCAAATTGGCGCCAATCTCTTGTTCTTCCCTGGCAGCCAATGTTTTTGTTTTGATTTCACCATTTGCTTTGCCAGCAAGTTCGCTTGTTG
CTGGTTCTGTGGTTGTTGCTGTTGCTTCTGCCTCTGCCTCTGCCTCTGTTGACGTTGAGGCCAGAATTTCCGCGCCAAAATCAAACTTAGTTGGC
GGATAGAATTGCGTAGTGTCTGGCACCTGGTTGCCCAGATCTTTAGACCTAATGTGGCCCAGGCGAATTTCCTCGTAATTTTCCATCATTTTTTC
CGAACCCAAGCGCGCGCACACGCGCACACACACAGACTCACGGAGAGAAAACTCTCGTAGTTGGTGCTGTTGCTGGCTCTTCTTCTTCTTGCGCG
AGTGTTTCCTCGGTCTCTCCGCTTTGCGCTCTCGCCTCGTCCGTTTTCTCCGCTCTTTCGTTGGTACACACAAAAATTTTTACGTCGTCAGCTTC
GCACCCATTTGGCTTGATTGAAAAAATTCTCCAGCGATCGTTTGGCCGCGATTTTTTCAACCAACCCGACTTTATTTCACGTATATGCACGAAAC
TTAAATTTTAAAAAAATTTCGACACCATTTGGTTGCGATTTTTTCGTAATTTTCGAGCGTAGTTTCTGGAAAATTTTCCGATGAAAAAAGCAAGA
TGGCACACGTAGCTGCGCCTGTGTGTGTATGTGGGCTGGCAGACGTGATTCGGGTGGGACCCTGACACGTCGTGTGGAAAGTGCTAACGCGTTTC
TGCATGGAAAGTGCCGCCAGCATGACTCATCACGGTATGTTTTTAGTATTTTTTGGGATTTTTGAGGGTGATTACGTGTTGCTACAGTGGCCACT
GCCTTATGTCATATCTAATTTAATCCATTTCTTTAAAAACTGTTTAAAATATATCAATAATTTGTCAAAAAGTTAGTAAAATTAATTTTAAATTA
TGCTTCGAACTTTAATTTTAGCACTCTTTTACTTATCAAATTTACTCGATATTTAAACAATTAAGTAAAAATAATTTTTTTGTCCAATATTTACA
CATTTCATAGTAGTATTATAAATTGATGTATTGATAATATGCAGTTCATATGTCCAAAAACTTCCATCAAGCTGTTAAATACAAAAATGTGTAAA
CAGATTTCCAGAACGTTCCAGCAAGTGTCTACTGTTCCCCAAAAAAGCTGCGATTTTAAGTATTTATTTGGTACTTTCCCCAAAATTATAGGTTT
TTGGTAGAACTTGGGCATACTTGTTAGCCAATATGACTTGAAAATATTGTCATAAATACATTGTTAAATAATTTAATAAGTCGTACACTTACAAT
GTACAAAATATTTTAGTTTGTAGGGGGACTGGGGATGCAATAGGAAATGGACAACCTAAATTTATACGACGTTCTTAAAGTGGCTCCGGATGCAA
CTGATGAGGAAATAAAAAAGGTATGTAACAGTTCCAATTCGATATGTTGGTAAATAGTTTGTATTCACCTTTTCACCAATAGAACTACCGAAAAT
TGGCAAAAGAGTTCCATCCAGACAAGAATCCCGATGCGGGCGACAAGTTTAAAGAAATATCCTTCGCCTACGAAGTGCTGTCCGATCCCGAGAAG
CGGCGCATCTACGACCGATATGGATTGAAGGGCCTGCAAGAGGGCGCCGAGGGATTCTCTGATGCCTCCGAATTCTTCGCCCAGTGGTTCCCCTT
CGATCGAG
(SEQ ID NO: 574)

Exon: 4993..3345
Exon: 3165..1001
Start ATG: 4554 (Reverse strand: CAT)

Transcript No. : CT16687
CCGAATCACGTCTGCCAGCCCACATACACACACAGGCGCAGCTACGTGTGCCATCTTGCTTTTTTCATCGGAAAATTTTCCAGAAACTACGCTCG
AAAATTACGAAAAAATCGCAACCAAATGGTGTCGAAATTTTTTTAAAATTTAAGTTTCGTGCATATACGTGAAATAAAGTCGGGTTGGTTGAAAA
AATCGCGGCCAAACGATCGCTGGAGAATTTTTTCAATCAAGCCAAATGGGTGCGAAGCTGACGACGTAAAAATTTTTGTGTGTACCAACGAAAGA
GCGGAGAAAACGGACGAGGCGAGAGCGCAAAGCGGAGAGACCGAGGAAACACTCGCGCAAGAAGAAGAAGAGCCAGCAACAGCACCAACTACGAG
AGTTTTCTCTCCGTGAGTCTGTGTGTGTGCGCGTGTGCGCGCGCTTGGGTTCGGAAAAAATGATGGAAAATTACGAGGAAATTCGCCTGGGCCAC
ATTAGGTCTAAAGATCTGGGCAACCAGGTGCCAGACACTACGCAATTCTATCCGCCAACTAAGTTTGATTTTGGCGCGGAAATTCTGGCCTCAAC
GTCAACAGAGGCAGAGGCAGAGGCAGAAGCAACAGCAACAACCACAGAACCAGCAACAAGCGAACTTGCTGGCAAAGCAAATGGTGAAATCAAAA
CAAAAACATTGGCTGCCAGGGAAGAACAAGAGATTGGCGCCAATTTGGAGCATAAAACCAAAAATCCCACAAAGTCAATGGGCGAGGATGAAGAT
GACGAGGAGGAGGAGGAAGAGGACGATGAGGAGGAGGAGGAGGACGACGAGGAGGGAATCACCGGAACGAGCAACGAGGATGAGGACTCCAGCTC
AAATTGCTCCTCATCCGTGGAACCCGACTGGAAGCTGCGCTGGTTGCAACGAGAATTTTACACAGGTCGTGTGCCGCGCCAGGTTATTGCCAGCA
TTATGCCGCATTTCGCCACCGGCCTGGCGGGCGACACCGACGACTCCGTGCTGTGGGACTATTTGGCCCACCTGTTGAACGAGCCGAAGCGGCGC
AACAAGCTGGCCTCAGTGAACACCTTCGACGATGTCATCAGTTTGGTCAAGAAATCACAGAAGATCATTGTGCTAACGGGAGCCGGAGTATCCGT
CTCCTGCGGCATTCCGGACTTCCGGTCCACCAATGGCATATATGCGCGATTGGCCCATGATTTTCCCGATCTGCCCGATCCGCAGGCCATGTTTG
ATATCAACTACTTCAAGAGGGATCCACGACCGTTCTACAAGTTTGCCCGCGAGATATATCCCGGCGAGTTTCAGCCCTCACCCTGCCATCGTTTC
ATCAAAATGCTGGAGACCAAGGGCAAACTGTTGCGCAACTACACACAGAACATCGACACCCTCGAGCGGGTGGCAGGCATTCAGCGAGTAATCGA
GTGTCACGGCTCCTTTTCAACGGCCTCGTGCACCAAGTGTCGTTTCAAGTGCAACGCTGACGCCCTGCGGGCGGACATATTTGCCCAGCGAATTC
CGGTGTGCCCGCAGTGCCAGCCCAATAAGGAGCAGAGCGTGGATGCCTCGGTGGCCGTTACTGAGGAGGAGCTGCGCCAACTGGTCGAGAACGGC
ATCATGAAGCCGGATATCGTCTTTTTCGGCGAGGGACTGCCGGATGAGTACCACACGGTCATGGCCACCGACAAGGACGTGTGCGATCTACTGAT
CGTGATCGGCTCCTCGCTGAAGGTCCGACCTGTGGCCCACATTCCCAGCAGCATACCGGCCACGGTGCCGCAGATTCTTATCAATCGCGAGCAGC
TGCATCACCTTAAGTTCGATGTGGAGCTGCTGGGCGACTCCGATGTGATCATCAACCAGATTTGCCACCGGTTGTCGGACAACGATGATTGCTGG
CGGCAGCTGTGCTGCGATGAGTCAGTGCTTACCGAAAGCAAGGAGCTAATGCCTCCGGAGCACTCTAATCACCACCTCCATCATCATCTACTTCA
CCACCGCCACTGCAGTTCAGAGAGCGAGCGACAGTCGCAACTGGACACGGATACGCAGTCTATTAAATCAAATAGTTCGGCGGACTACATACTAG
GATCAGCTGGCACCTGCTCGGATAGTGGATTTGAGTCATCTACTTTTAGCTGTGGAAAGCGTTCCACTGCCGCCGAAGCGGCAGCCATCGAACGT
ATTAAAACAGACATACTGGTTGAGCTGAACGAGACCACAGCCCTAAGTTGCGATCGTCTGGGCCTGGAAGGCCCTCAGACAACGGTGGAGAGCTA
TCGCCATCTTTCCATTGATTCCTCCAAGGATAGCGGCATCGAGCAGTGCGACAACGAAGCCACGCCTAGCTACGTGCGACCCAGCAATCTTGTTC
AGGAGACCAAGACAGTGGCGCCCAGCCTGACGCCCATTCCACAACAGAGGGGAAAGCGACAGACAGCAGCCGAGCGTCTGCAGCCTGGAACATTC
TATTCGCACACCAACAACTATTCGTATGTGTTTCCAGGAGCCCAGGTATTCTGGGACAACGATTACAGCGATGATGATGACGAAGAAGAGGAAAG
ATCACACAATAGACACAGTGATCTCTTTGGCAATGTGGGGCACAATTATAAGGATGATGATGAGGATGCATGTGATCTGAACGCCGTTCCATTGT
CACCATTGCTACCGCCTTCACTGGAGGCTCACATAGTCACCGATATAGTGAATGGATCCAACGAACCGCTGCCCAACAGCAGTCCCGGCCAGAAA
AGAACCGCCTGCATTATAGAACAGCAGCCAACGCCCGCTATTGAAACGGAAATTCCCCCACTAAAGAAGCGGCGACCAAGTGAGGAAAATAAGCA
GCAGACCCAAATAGAAAGATCTGAGGAGAGTCCGCCTCCAGGACAGTTAGCAGCAGTGTAAACGTAATCTTAGCCCCTGCTAGTAGTGTAGTATT
TATTTTAAATGCAATTCAAGCCAACTTGTAAACAGAGAAGCTGCGAAATCGTAGCCGAGGGCCATGTTACCAATTTCATTCCCCGGAAAGGTACT
GGAATCGGAAACGGTAAACCGTTTACTTGTTATTTATTTAGAATATGAGAACACTTCAATTCCCGGTATCACGAAGTTTTCAAGAAATGAAACCG
GATCCACTAGTTTACTCAATTCGAGGCTTTAGAGATCTGACCCTCGTTGCTTTACCACCAACCCCTTATGCCCAATCCCGTTTTGATATTTTTGA
AAAACTCTTAGTTTATTTATTATCTCTCTTTTTCAAAACGAAACGCTGTAAATGTTAGTATTTTATTATATTAAGTTGTTATTGAGGCCTTTTTA
GACAAACTAAAGAGATAAGCGGAAAGTTGAAAATCCTTTAGAAAGCAGGATTTCTTTGTATTCAAAGAGAAGCAGCGCCTCAACTTTAAATCTAG
TTCTAAGCGTAACATATTCAAAACTATGCAAATGCAAACGGAAAAATACGTTAGTTTAGTTAAAAACTAGACACAAACACTCTGTATATAAGCA
CTCGCCCCTAATTTGTATTGTACATGATTCTTTTTCTACTTTTTTGTGTTATCTCCTTACCATTTTATATTTCTATCGGTTATGGCAACTATTTT
TTAACATTTATACACTCGCACCCACATCAAAATGTAACAGCGCATGGATTTCAAAATATTCATAAGAGTTGGAAATTTGGTGTGCGTGTTTGAAA TGTTTATTCGAAACCTAGCATAAATATATAGCCACCAAACGCAGTGTAAACATAGCAGTAAGAATTTAGTCTATATGTCTTAAAAGTGTATTAAT
ATCCAGAATATAAA
(SEQ ID NO: 575)

Start ATG: 440 (Reverse strand: CAT)

MMENYEEIRLGHIRSKDLGNQVPDTTQFYPPTKFDFGAEILASTSTEAEAEAEATATTTEPATSELAGKANGEIKTKTLAAREEQEIGANLEHKT
KNPTKSMGEDEDDEEEEEEDDEEEEEDDEEGITGTSNEDEDSSSNCSSSVEPDWKLRWLQREFYTGRVPRQVIASIMPHFATGLAGDTDDSVLWD
YLAHLLNEPKRRNKLASVNTFDDVISLVKKSQKIIVLTGAGVSVSCGIPDFRSTNGIYARLAHDFPDLPDPQAMFDINYFKRDPRPFYKFAREIY
PGEFQPSPCHRFIKMLETKGKLLRNYTQNIDTLERVAGIQRVIECHGSFSTASCTKCRFKCNADALRADIFAQRIPVCPQCQPNKEQSVDASVAV
TEEELRQLVENGIMKPDIVFFGEGLPDEYHTVMATDKDVCDLLIVIGSSLKVRPVAHIPSSIPATVPQILINREQLHHLKFDVELLGDSDVIINQ
ICHRLSDNDDCWRQLCCDESVLTESKELMPPEHSNHHLHHHLLHHRHCSSESERQSQLDTDTQSIKSNSSADYILGSAGTCSDSGFESSTFSCGK
RSTAAEAAAIERIKTDILVELNETTALSCDRLGLEGPQTTVESYRHLSIDSSKDSGIEQCDNEATPSYVRPSNLVQETKTVAPSLTPIPQQRGKR
QTAAERLQPGTFYSHTNNYSYVFPGAQVFWDNDYSDDDDEEEERSHNRHSDLFGNVGHNYKDDDEDACDLNAVPLSPLLPPSLEAHIVTDIVNGS
NEPLPNSSPGQKRTACIIEQQPTPAIETEIPPLKKRRPSEENKQQTQIERSEESPPPGQLAAV*
(SEQ ID NO: 576)

Name: silent information regulator 2
Classification: known_flybase_gene
Gene Symbol: Sir2
FlyBase ID: FBgn0024291

Celera Sequence No. : 142000013384004
AACGTATTGAACAATTATAATTAAATTATTTTTTAATAAAGATAAGCTTAATTCATTCACGTAACTGGAAATCTTAATTGGAGATAATCTAGCA
CTGATAATATTCTTCGCTTTATAAATAAGTTCTAATTGAAATTAATTCAAATATATATTTATATATATGATATATAATTTTTAAGGAATTACAAG
AAGTCGTTCCACTTAGAGCAAATTTTCTTAGTAACTGTTGGCATATTTTCAGCGGAACGTTTAGAGGATCGTGGCCCTGTGTTCCTGGTTTTCTT
AAAGTTCATAGAGATTTCGTCGGAAAGTTCATCGGTTTTCGTAGGTTTTGCTGCAGGCTTTTGAGTAGTTTCAATGGTATTATCCACATAGTTTG
CCCATTTATTTGTTTTCTTCTGAGGTGTGGTGTTTTCCTCTTTTTCTTGGCAGTCTTTCTCCTCTTCGAGCTGTTGCTTTGCCGTGAGGAATAAG
CCCGTGTTCAGACATTCCTCCTGCATTCCGCGCTCTAAGTTGAGATGCTGCACCTTAACCCGGCATTCCGCTGCCGATCCTCGAAAGAATTCCTT
GAGCAAACTTTGCTTTTGGCGGCAAATTTTACACTGCCATGTGCTTGCCTTTTTCACGAAGTCCACCTTGTTTAAATTAGGTATATATATATAAG
TAGTTATTGAGTTCTAAGATATATTTCAGTTTGTTTGCACTCACCTGGTACATTTTGCATTGAATGCATTGTACCACGCGAATTTGCTGGGACAT
TATTCAAATTTGCGAAAAACCAAATAAAGAGACCAGGGATGGAAACCAACAGCACTGCAACAAGTGGAGTGAAAAAAATGTGGTTGCACAAATGT
TAAAGCGTGATGACTACAGTTTAACAAGTAGTAAAACATTTACCAAAATTTGTAATTAACTAATTTGGTACCTATGGTTAATGATTTAGCCGGG
TGCTGATTCCGGTTCATAAGTGAACCAAATCGTTCCCCATCCCTGGTCCAAATATAAACAAACTTTGCATCGTCTAATCGGCACTGTCGGTTTAAT
AAAATGCGATTGGTAAGTCATCCTGAGAAGTAAATAACAACTTAATTAGCGGAAGTGACTATCCACTTTGCAGTATTGTCTCAGCGGGGACCTGG
CCAAGCCATGTTATATCATTACCTTCAAGGGCCTGCGGATTATGCTGGACTGCGGTCTCACGGAGCAGACAGTCCTGAATTTCCTTCCGCTGCCC
TTCGTTCAGTCACTGAAGTGGTCCAATCTGCCCAACTTCGTGCCCAGTCGGGATCATGATCCCCAAATGGATGGCGAGTTGAAGGACTGCTGTGG
CCGGGTTTTCGTGGACTCGACGCCCGAGTTTAATCTACCCATGGACAAAATGCTGGATTTCAGCGAAGTGGATGTGATACTTATCTCGAATTATC
TTAATATGCTGGCCTTGCCGTATATCACGGAAAACACGGGGTTCAAGGGCAAAGTCTATGCCACGGAGCCAACGCTGCAGATCGGCCGATTTTTC
CTGGAGGAGCTGGTGGACTATATCGAAGTGTCGCCCAAGGCGTGCACCGCGCGCTTGTGGAAGGAGAAGCTTCATCTGCTGCCCAGTCCCTTGAG
CGAAGCCTTTCGCGCCAAGAAGTGGCGCACTATCTTTAGTCTTAAGGATGTCCAAGGCAGTCTGTCCAAGGTGACCATCATGGGCTACGACGAGA
AGCTGGACATCCTCGGAGCTTTATCGCCACTCCTGTCAGCTCGGGCTACTGCCTGGGCTCGAGCAACTGGGTACTGAGCACGGCGCATGAAAAG
ATTTGCTATGTCAGTGGTTCCTCCACGTTGACCACACATCCGCGGCCCATCAATCAGTCGGCGCTGAAGCACGCCGATGTACTCATTATGACCGG
ACTGACGCAGGCGCCGACGGTAAATCCGGACACGAAGCTGGGCGAGCTCTGCATGAATGTGGCCTTGACGATCCGCAACAATGGGTCTGCCTTGA
TTCCCTGTTATCCTTCGGGCGTTGTCTATGACCTCTTTGAGTGCCTCACCCAGAATTTGGAAAACGCTGGCCTAAACAATGTTCCCATGTTCTTT
ATTTCCCCTGTGGCAGACAGCTCCTTGGCGTATTCTAATATCCTGGCCGAGTGGCTTAGTTCCGCCAAGCAGAACAAAGTGTATCTTCCAGACGA
TCCTTTCCCACATGCCTTTTACCTTCGCAACAACAAGCTGAAGCACTATAACCATGTGTTCTCCGAGGGCTTTAGCAAGGACTTCCGGCAGGTTT
GTCTAACATAATTGTGAAAACTTCATACTACAAATTCTCTGTCTTCCTTACAGCCCTGCGTGGTCTTTTGTGGCCATCCTAGCTTGCGTTTCGGC
GACGCTGTTCACTTTATCGAGATGTGGGGCAATAACCCTAACAACTCCATCATATTCACGGAGCCGGACTTTCCGTATCTGCAAGTACTGGCGCC
CTTCCAACCACTGGCCATGAAGGCTTTTTACTGTCCCATCGACACCTCTTTGAATTATCAGCAGGCAAATAAGCTGATCAAGGAGTTGAAACCAA
ATGTGCTTGTCATCCCAGAGGCATACACAAAACCACATCCCTCGGCCCCAAATTTGTTCATTGAACAGCCGGATAAGAAGATAATAACGTTCAAG
TGCGGCGAGATCATACGTCTGCCATTAAAACGGAAGCTGGATCGAATTTACATTACCTCGGAACTGGCCCAAAAGATATCGCCAAAGGAGGTGGC
GGCCGGCGTGACCTTCTCCACATTGACAGGAGTTTTGCAAGTTAAGGACAAGGTCCACTGCATCCAGCCATGTGCGGATAGCGTTAAAGACGAGA
CCATCTCGAGCAACAGCGCTCCGACAAAGGAGGATGTGCTGAAGAACGTCAAATACGAGTATGGCAGCATTGATGTAGATGCAGTGATGAAGAAG
CTGGCACAGGATGGCTTCTCCAACATCAAGCTAGACCGCACTGGCGGCGCTCTGACTCTGAACCTTGTCAATGAGGACACAGTCATTAAGTTCGA
GGACAACGAGACGCATATTATCTGCGGCGGAAAGCCAACAACCCGGCTCAAGCTGCGAGACACCATCATGAAATGCTTACAGAGTTTTTAAAAAC
ATAAATGTATTCCTTACACCTAAATAACAACACATCATTACGCTTAGTTCTTTGCCTCCATAACGTCAGAGCAACGTTGACACGTTTTCTGCTCA
TCCTCCAGACCATAGCGACGACAACGTGGGCACAGTGATATCTGAAGTTTACTTAAAGCAATATCCAAGTCGCTATTATGGGACTGTAAGAGCGT
AACTGACCCCACTTGCAATATCTCGCATAATTCAGAATTGCTCACAGACTCTCCAAGAGGGCTGTGAAGTTCTCGCAGCAAATCCAGCTGGCTTC
TTTCCTTTCCTTTGATGGTCACGGCCAAGTGCCAGGTGTTAACATCTCCAGCCTGTTGGTTAATAAGTCGTTTAACATCGAACGCTGCATTAATC
ACTTCAGTGGCTTTGGTGTCCTGCCATTCAGGATTAGTCTGAACAATTTGCTCGTGGAATGCACCACCTGTGGTGTCATAGTAGCTCCAGCTTTC
CTCCACCAGGAAGGGAACAATGGGCCATAAGCTCTTGCAGAGTTGTTGATAGCAGTGGGTAAGAGTTTGACGAATGGCCAGTAGCTCGTGATCAT
CACCACAATAAAGACGATCCTTGATGAGATGCACATAGACGGCGGACACCTGATTTGCAATGAAGTTTTGGACACAGGCGACAACACGATTGTAC
TCATAAGCTTGGTATAGCTTCTCCACCTTAAAAGCGATTGACATGATTAGTTGAAAAACTAAGATTAACAAAATTTCCTACCTCAGATTCAAATT
CAACCAGCTGGCTTAACAAATAACGATTAAGATAGCTCTTATCCGAAGTTCGTATAAGCTTCTCCCCCGATTGTTTCTCTCCAATTACGCCTTTT
AAATATCGCATAGTTCCGCGGATCTTGCATAGATTTTCTGCCGCTTGCTGCAGTAGCTTATCGCTCACTGTAATGGACATGTGCTGCGTTCCATG
GGAGGCAACCCACCAACGCGGCAGTGCATCCGTACCATATTTCTTGGTT
(SEQ ID NO: 577)

Exon: 1001..1057

FIGURE SHEET 317

Exon: 1182..2276
Exon: 2334..3131
Start ATG: 1182

Transcript No. : CT16697
AATATAAACAAACTTGCATCGTCTAATCGGCACTGTCGGTTTAATAAAATGCGATTGATGCTGGACTGCGGTCTCACGGAGCAGACAGTCCTGAA
TTTCCTTCCGCTGCCCTTCGTTCAGTCACTGAAGTGGTCCAATCTGCCCAACTTCGTGCCCAGTCGGGATCATGATCCCCAAATGGATGGCGAGT
TGAAGGACTGCTGTGGCCGGGTTTTCGTGGACTCGACGCCCGAGTTTAATCTACCCATGGACAAAATGCTGGATTTCAGCGAAGTGGATGTGATA
CTTATCTCGAATTATCTTAATATGCTGGCCTTGCCGTATATCACGGAAAACACGGGGTTCAAGGGCAAAGTCTATGCCACGGAGCCAACGCTGCA
GATCGGCCGATTTTTCCTGGAGGAGCTGGTGGACTATATCGAAGTGTCGCCCAAGGCGTGCACCGCGCGCTTGTGGAAGGAGAAGCTTCATCTGC
TGCCCAGTCCCTTGAGCGAAGCCTTTCGCGCCAAGAAGTGGCGCACTATCTTTAGTCTTAAGGATGTCCAAGGCAGTCTGTCCAAGGTGACCATC
ATGGGCTACGACGAGAAGCTGGACATCCTCGGAGCTTTTATCGCCACTCCTGTCAGCTCGGGCTACTGCCTGGGCTCGAGCAACTGGGTACTGAG
CACGGCGCATGAAAAGATTTGCTATGTCAGTGGTTCCTCCACGTTGACCACACATCCGCGGCCCATCAATCAGTCGGCGCTGAAGCACGCCGATG
TACTCATTATGACCGGACTGACGCAGGCGCCGACGGTAAATCCGGACACGAAGCTGGGCGAGCTCTGCATGAATGTGGCCTTGACGATCCGCAAC
AATGGGTCTGCCTTGATTCCCTGTTATCCTTCGGGCGTTGTCTATGACCTCTTTGAGTGCCTCACCCAGAATTTGGAAAACGCTGGCCTAAACAA
TGTTCCCATGTTCTTTATTTCCCCTGTGGCAGACAGCTCCTTGGCGTATTCTAATATCCTGGCCGAGTGGCTTAGTTCCGCCAAGCAGAACAAAG
TGTATCTTCCAGACGATCCTTTCCCACATGCCTTTTACCTTCGCAACAACAAGCTGAAGCACTATAACCATGTGTTCTCCGAGGGCTTTAGCAAG
GACTTCCGGCAGCCCTGCGTGGTCTTTTGTGGCCATCCTAGCTTGCGTTTCGGCGACGCTGTTCACTTTATCGAGATGTGGGGCAATAACCCTAA
CAACTCCATCATATTCACGGAGCCGGACTTTCCGTATCTGCAAGTACTGGCGCCCTTCCAACCACTGGCCATGAAGGCTTTTTACTGTCCCATCG
ACACCTCTTTGAATTATCAGCAGGCAAATAAGCTGATCAAGGAGTTGAAACCAAATGTGCTTGTCATCCCAGAGGCATACACAAAACCACATCCC
TCGGCCCCAAATTTGTTCATTGAACAGCCGGATAAGAAGATAATAACGTTCAAGTGCGGCGAGATCATACGTCTGCCATTAAAACGGAAGCTGGA
TCGAATTTACATTACCTCGGAACTGGCCCAAAAGATATCGCCAAAGGAGGTGGCGGCCGGCGTGACCTTCTCCACATTGACAGGAGTTTTGCAAG
TTAAGGACAAGGTCCACTGCATCCAGCCATGTGCGGATAGCGTTAAAGACGAGACCATCTCGAGCAACAGCGCTCCGACAAAGGAGGATGTGCTG
AAGAACGTCAAATACGAGTATGGCAGCATTGATGTAGATGCAGTGATGAAGAAGCTGGCACAGGATGGCTTCTCCAACATCAAGCTAGACCGCAC
TGGCGGCGCTCTGACTCTGAACCTTGTCAATGAGGACACAGTCATTAAGTTCGAGGACAACGAGACGCATATTATCTGCGGCGGAAAGCCAACAA
CCCGGCTCAAGCTGCGAGACACCATCATGAAATGCTTACAGAGTTTTTAA
(SEQ ID NO: 578)

Start ATG: 58

MLDCGLTEQTVLNFLPLPFVQSLKWSNLPNFVPSRDHDPQMDGELKDCCGRVFVDSTPEFNLPMDKMLDFSEVDVILISNYLNMLALPYITENTG
FKGKVYATEPTLQIGRFFLEELVDYIEVSPKACTARLWKEKLHLLPSPLSEAFRAKKWRTIFSLKDVQGSLSKVTIMGYDEKLDILGAFIATPVS
SGYCLGSSNWVLSTAHEKICYVSGSSTLTTHPRPINQSALKHADVLIMTGLTQAPTVNPDTKLGELCMNVALTIRNNGSALIPCYPSGVVYDLFE
CLTQNLENAGLNNVPMFFISPVADSSLAYSNILAEWLSSAKQNKVYLPDDPFPHAFYLRNNKLKHYNHVFSEGFSKDFRQPCVVFCGHPSLRFGD
AVHFIEMWGNNPNNSIIFTEPDFPYLQVLAPFQPLAMKAFYCPIDTSLNYQQANKLIKELKPNVLVIPEAYTKPHPSAPNLFIEQPDKKIITFKC
GEIIRLPLKRKLDRIYITSELAQKISPKEVAAGVTFSTLTGVLQVKDKVHCIQPCADSVKDETISSNSAPTKEDVLKNVKYEYGSIDVDAVMKKL
AQDGFSNIKLDRTGGALTLNLVNEDTVIKFEDNETHIICGGKPTTRLKLRDTIMKCLQSF*
(SEQ ID NO: 579)

Classification: hypothetical

Celera Sequence No. : 142000013384546
GCAGCGGGCACCAGTGGTTCTGTGACCATATCGCTGCATCCGCTGGTCATAATGAACATCTCCGAGCACTGGACACGCTTTCGTGCACAGCACGG
TGAGCCGCGACAGGTGTACGGAGCACTGATTGGCAAGCAGAAGGGCCGCAACATTGAGATTATGAACTCGTTCGAACTGAAGACGGACGTTATTG
GCGATGAAACAGTGATCAACAAGGACTACTACAACAAGAAGGAACAACAGTACAAGCAGGTGGGTGTCCAAGCCTCTACATACGCTGCTTTACCA
GCTGTTACTCTTTTTTCCCCAGGTGTTCAGTGATCTCGACTTCATAGGCTGGTACACAACCGGCGACAATCCCACTGCCGATGACATTAAGATCC
AAAGACAGATAGCCGCCATCAACGAGTGCCCCATCATGCTACAGCTGAATCCGCTCTCCCGCAGCGTCGACCACCTTCCCCTGAAGCTATTCGAG
TCCCTAATCGATCTGGTGGACGGCGAGGCCACCATGCTGTTCGTGCCCCTCACCTACACACTGGCCACCGAGGAGGCGGAGCGCATTGGTGTGGA
TCATGTGGCGCGCATGACCTCGAACGAGTCCGGCGAGAAGAGCGTGGTGGCGGAGCATTTGGTGGCCCAGGACAGTGCCATTAAGATGCTAAATA
CACGCATCAAGATCGTGCTGCAGTACATACGCGATGTGGAGGCCGGAAAGCTGCGGGCCAACCAAGAGATTCTGCGAGAAGCCTACGCTCTCTGC
CACCGACTGCCCGTCATGCAGGTGCCCGCCTTCCAGGAGGAATTCTACACGCAGTCGCAACGATGTGGGACTGATTAGCTACCTGGGCACGCTGAC
CAAGGGCTGCAATGATATGCACCACTTTGTGAACAAGTTTAATATGCTGTACGACCGCCAGGGATCCGCGCGCCGCATGCGAGGTCTCTACTATT
GATATATGCAAACAATCTATTAAAGCTTCGGAGATAAATACACATAATCGTACGATGGGTGAATGCGGTTTTATTTCAGCTGCCGCTGGGCAGGC
TACATACGTATACGGGTGGCATCAAGCGATATCACTTTCTTCCTGAGCTCCAGCTCCTCTTGCTTCGTAAATTCAATTCAGATGCACAGACAAC
ATTTCCTAGACACTAAATTAGGTAATTTCGCAGCGGAATTAGTGGTTGTAGTCGTCCAGCTTGATGCTGGGGGCATACTGCTGCAAGAACTCCAC
CTCCAGCGGATGCATCTCCTTGGCGGGAATGATGAGCGAGTGCAGCGGTCCGCCCAAATCGGTCGAGCGCATCTCAAGCAGCGTGCCAACGGCAA
TCTGCTGCGACTCCTGGCCAACACGGGCCAGTCCAACGCACAGTGACTGCTCGTTGAGCACTGTGTTCTTCTCCAGCGAGTCCTTCTTCTCCACA
ATGGACAGCAACTGATGAGCCGCCTCCGCCAGCGCGGTCATGAAACGCGGTGGCATGTACTCCTTGCGTTTGCGCATCAAGGACTCCGGCGTGGGCTC
CTTCACCTTGATGTCCAGCAGGCACAGCGTGTGCATGTTGTGCAGGCGATTCAGCTTGATCTTGTCGTAGAAGCTGTCCGGCTTCCATGTCTCGT
CCCAGTACGGAATCGAAACGGTCTCGCCGAATTTGTACAATTGCAGGCCGCAGCAGCCGACGGCGTTCATGATCGATGCATTGTGGATGACCTTG
TAGGGGATGTTCTTCTCCTTGGCGCGCAGTATGAAGTCTGTGTGGGTGGTGGCGCCAAAGGGGTCGCCCACCACGAGCAGCGCAACATCGGATTC
GCCCGCACCCGCCAGGATCTCATCCGCACCCTGCTCCACCAGATCGCGGTCGGCTAGCAGCAGTGGTCGTCCATAGAACTCTTGCTGCGAACAAA
GTGGAGATGCAATTAGCATTGGGGGTGCTCCCAGAACGAAGGCCATTCCAGATACCTACCATATCCTCAAGGCTGCAGCCCAGAATCGAGGTGTA
CATCTCCAGATAGACGCGACTGCATTGCTTCACTATCTCCAGACCCTTGACCGTGATGTCCTTCAGGTCGCCAAGGCCGAGGCCGATTAGGTAGA
ACATGCTGGGCGACTGGTGCGACTGCTCGGCCACTGCAACTCCTGCCAAATGTTATTAAAATCGCTTTTTAAATGCAGTCAACACGTGCCGTCGC
GCGTTGTGTGACCGCCGCCAGAGCGCCAAGAAATACTCACATTGCGACAATGGGCTAAAAAAGCCTGTGCAGCAATGGCGCGTATTTTGAATTTG
AAGGCCATTTCATTTAATTGGGAAATAAACACTAAAAACTTTGGTCCACTACTTAAGAAATGATATATTTGGTTTGCTTTTTTGATCTCAGCTGT
ATGATACCTATGTTACTCTTAGACTGTAATAATAAGTAAACTACTTAACATAACTACACTCCAGCAATTATTGGAACTCTGAATTTGTTTGCTCG
GAAATCTTGAAGCTGCAAAGTTGGGGTCTGTGGATGAAAAATATCATTTAATTAACGTACTTACGTACTTACAACAATATTACGCCATTTCAACT
TACGTTGTTGAGGCGCCCCGAACCACGCAATAAGCTATGAATCGTTCAATCTGCAAAGCAATCTTTATCTTTACCGATTCCCTTATTATAAATGC

FIGURE SHEET 318

ATAGGCACTCACCATCATTTCAAAGTCGCCATAGGCGGCGGAGTGATCCATGCGCACCTGCAGGAAGTACTTGTGTATCTCGGCACCCAGATTGT
CCTTCCAATCAGGACACTCCTCGCGTATACGTCTGCAATTGATGATCATGCTGAAAGTGCGGATGAGCATAAACAAATCTGCCTGGCGTCCACTG
TTTGCCAACTGGCGCCAGTTGACCGTTTTGGCCATTTCAAAAGCCTTGAGAGCCTGCATATATATGGGTTTAGATTTTAAAGTGCTGATGGAATC
AGTTTTAGGTTCATACATATTCCTTCTGGTCCAGTTCAACTGGTTCTCCCGTGTACCGTCCCATTATGGTGAGTAGCAGGGCCATAGCTACATCG
TTGCCAAGATGGCAGGATTCTACCATGGCGGGAATCGCGGCCTGCAGGTCCAGCACTCTTTCCAGGCGCTCCATACCCACGCCAGTGATAAGGTT
TTCGTACAACCCACTGGCCATGTAGAACATCTAAAGGGAATAAGATGTAATTGATCGGAAATGTTAGGATAGCAGAAAGGGGAACTACCTCCTCC
GAGTCCAGGGACTCTGCCAGGTGACACACCACATCCACCATCATGTAGCGCTCCTTCATCAGCAGAACGTTGTCCCTTTGGTACGTCATCATCAT
AATGGAGAGGGTAAACAGATCGAGCAGCTGCTGCAAATTGAGTTCCAGCTTCCCGGCTAAGGTAGCCATCATGCGATTCAGCAACTAAGTTAATA
TAAACAAATTAGTAATAGTTATTAGGAAATAAACAGAATAATAACCTGTTTGCCGTCTGTGGTTTCTGCAGCGTAAGGAAACAAATGCTTGATGG
ACGACTTCCGGAGAAAGGACATGATGGATTCGTGGTCATAGCCTAGGCGCATTTCATCCACTTCCACGAGGGAATTATTCAACGATGAATCAGAT
AGATTCATTTTGTATTGGCGGTAAAAAATGCGCAAAGCAAATAAATAGAAATAATAAACTGAAAGAGTGACCAGGCACCAAGGGGTGGGTCAAAT
AGCCTAACGCCTAGTTAAGCGCTGTATCGCATGAACGTAAACGGTCATACCATTATTGTTGCTCCACGTGCGGCGATTTTTATTCATTTACTACT
TTAATAATCAATTTTAGTGAATTGACACTAATTAAAATGCCGCCTGTTAAGAAGCCCAAGGCGCAGAAGATCGAGAAGCAAAGCACGCCCAAAAA
GCCCATCGATGCAGCCAAGAATGTGGTTTCCGGACAGGTGAGCGGCTACCAAAAACAAATGCTCCTCCGTTGGGTTGGATAACCGTAAACTGCGT
CCATTTTAGCTAAAGAAAAAGGTGACCAAGGCCAGGCCGCAGAAGCCAAAGGGTCCAGAACGCGGCGTGGTCATTGTGAAGCACCTGCCTCACGG
ATTCTTCGAGCAGCAGCTGCGCCAGTACTTCCGACAGTTCGGTCGGGTGCTGCGCGTCCGTTTGGCCCGTTCGCTGCGCACCGGTAACAGCAAGG
GCTACGCCTTCGTGGAGTTCGAGTACCCGGAGGTGGCCAAGGTGGCTGCCGACACCATGGACAACTACCTGATGTTCCAGAAGGTGGTGAAGGCC
ACCTACATTCCACCAGAGAAGCAGACACTCAACTTCTTCAGGACTTCCTTGAAGAAGGTTGTCAATAAGGTGCGTTCAAAGGGAAATACATCTAA
TGTCCGTTTGTTATTCATAGTTGTACTTCACTTGCAGGCCGGCAAGGAAATCTATGTCTCGGATTTAACCAAAGCCACACAGCGCAGCGTGAAAA
AGCAGAATAACTGGGATGAGTCCGCCTGCCAGAAGCGCACCGTGGCCAATCTCAACAAGATCAAGAAGCTGCAGGAGAAGTACAAGGATCTGGGC
ATCGACTTCTCCAACTTACTGGTGGAACCAGTAAAGAAAGCAGCAGGCTCCGCTGAGGCATCTACAAGCCAGGCAGCCGCCAAGAAAGCCGGTAA
GAAACAAAAAACGGCCGCGAAGAAAGAACCAACGCTGGAGGATTTGCTGGGCAACACCATCAACGAGGACTCCGATGATGAGGACTACGTTGATG
CATCCGATGATGAGTCCGATCTGGAGGCTGAGG
(SEQ ID NO: 580)

Exon: 3783..3466
Exon: 3397..3224
Exon: 3165..2962
Exon: 2903..2673
Exon: 2599..2569
Exon: 2132..1960
Exon: 1889..1001
Start ATG: 3618 (Reverse strand: CAT)

Transcript No. : CT16835
AATCGCCGCACGTGGAGCAACAATAATGGTATGACCGTTTACGTTCATGCGATACAGCGCTTAACTAGGCGTTAGGCTATTTGACCCACCCCTTG
GTGCCTGGTCACTCTTTCAGTTTATTATTTCTATTTATTTGCTTTGCGCATTTTTTACCGCCAATACAAAATGAATCTATCTGATTCATCGTTGA
ATAATTCCCTCGTGGAAGTGGATGAAATGCGCCTAGGCTATGACCACGAATCCATCATGTCCTTTCTCCGGAAGTCGTCCATCAAGCATTTGTTT
CCTTACGCTGCAGAAACCACAGACGGCAAACAGATGATGGCTACCTTAGCCGGGAAGCTGGAACTCAATTTGCAGCAGCTGCTCGATCTGTTTAC
CCTCTCCATTATGATGATGACGTACCAAAGGGACAACGTTCTGCTGATGAAGGAGCGCTACATGATGGTGGATGTGGTGTGTCACCTGGCAGAGT
CCCTGGACTCGGAGGAGATGTTCTACATGGCCAGTGGGTTGTACGAAAACCTTATCACTGGCGTGGGTATGGAGCGCCTGGAAAGAGTGCTGGAC
CTGCAGGCCGCGATTCCCGCCATGGTAGAATCCTGCCATCTTGGCAACGATGTAGCTATGGCCCTGCTACTCACCATAATGGGACGGTACACGGG
AGAACCAGTTGAACTGGACCAGAAGGAATATGCTCTCAAGGCTTTTGAAATGGCCAAAACGGTCAACTGGCGCCAGTTGGCAAACAGTGGACGCC
AGGCAGATTTGTTTATGCTCATCCGCACTTTCAGCATGATCATCAATTGCAGACGTATACGCGAGGAGTGTCCTGATTGGAAGGACAATCTGGGT
GCCGAGATACACAAGTACTTCCTGCAGGTGCGCATGGATCACTCCGCCGCCTATGGCGACTTTGAAATGATGCTTATTGCGTGGTTCGGGGCGCC
TCAACAACGAGTTGCAGTGGCCGAGCAGTCGCACCAGTCGCCCAGCATGTTCTACCTAATCGGCCTCGGCCTTGGCGACCTGAAGGACATCACGG
TCAAGGGTCTGGAGATAGTGAAGCAATGCAGTCGCGTCTATCTGGAGATGTACACCTCGATTCTGGGCTGCAGCCTTGAGGATATGCAAGAGTTC
TATGGACGACCACTGCTGCTAGCCGACCGCGATCTGGTGGAGCAGGGTGCGGATGAGATCCTGGCGGGTGCGGGCGAATCCGATGTTGCGCTGCT
CGTGGTGGGCGACCCCTTTGGCGCCACCACCCACACAGACTTCATACTGCGCGCCAAGGAGAAGAACATCCCCTACAAGGTCATCCACAATGCAT
CGATCATGAACGCCGTCGGCTGCTGCGGCCTGCAATTGTACAAATTCGGCGAGACCGTTTCGATTCCGTACTGGGACGAGACATGGAAGCCGGAC
AGCTTCTACGACAAGATCAAGCTGAATCGCCTGCACAACATGCACACGCTGTGCCTGCTGGACATCAAGGTGAAGGAGCCCACGCCGGAGTCCTT
GATGCGCAAACGCAAGGAGTACATGCCACCGCGTTTCATGACCGTGGCGGAGGCGGCTCATCAGTTGCTGTCCATTGTGGAGAAGAAGGACTCGC
TGGAGAAGAACACAGTGCTCAACGAGCAGTCACTGTGCGTTGGACTGGCCCGTGTTGGCCAGGAGTCGCAGCAGATTGCCGTTGGCACGCTGCTT
GAGATGCGCTCGACCGATTTGGGCGGACCGCTGCACTCGCTCATCATTCCCGCCAAGGAGATGCATCCGCTGGAGGTGGAGTTCTTGCAGCAGTA
TGCCCCCAGCATCAAGCTGGACGACTACAACCACTAATTCCGCTGCGAAATTACCTAATTTAGTGTCTAGGAAATGTTGTCTGTGCATCTGAATT
GAATTTACGAAGCAAGAGGAGCTGGAAGCTCAGGAAGAAAGTGATATCGCTTGATGCCACCCGTATACGTATGTAGCCTGCCCAGCGGCAGCTGA
AATAAAACCGCATTCACCCATCGTA
(SEQ ID NO: 581)

Start ATG: 166 (Reverse strand: CAT)

MNLSDSSLNNSLVEVDEMRLGYDHESIMSFLRKSSIKHLFPYAAETTDGKQMMATLAGKLELNLQQLLDLFTLSIMMMTYQRDNVLLMKERYMMV
DVVCHLAESLDSEEMFYMASGLYENLITGVGMERLERVLDLQAAIPAMVESCHLGNDVAMALLLTIMGRYTGEPVELDQKEYALKAFEMAKTVNW
RQLANSGRQADLFMLIRTFSMIINCRRIREECPDWKDNLGAEIHKYFLQVRMDHSAAYGDFEMMLIAWFGAPQQRVAVAEQSHQSPSMFYLIGLG
LGDLKDITVKGLEIVKQCSRVYLEMYTSILGCSLEDMQEFYGRPLLLADRDLVEQGADEILAGAGESDVALLVVGDPFGATTHTDFILRAKEKNI
PYKVIHNASIMNAVGCCGLQLYKFGETVSIPYWDETWKPDSFYDKIKLNRLHNMHTLCLLDIKVKEPTPESLMRKRKEYMPPRFMTVAEAAHQLL
SIVEKKDSLEKNTVLNEQSLCVGLARVGQESQQIAVGTLLEMRSTDLGGPLHSLIIPAKEMHPLEVEFLQQYAPSIKLDDYNH*
(SEQ ID NO: 582)

Classification: enzyme
Gene Symbol: Dph5

FIGURE SHEET 319

FlyBase ID: FBgn0024558

Celera Sequence No. : 142000013384285
TCGTTGCTGATCGCCTTCATGTTGTAACTGGCGGGCAGGAAATAGCCCAGCAGAAGGTATCGATTGTTGAAGCTAAACACGGCCGGTCCACTCGG
GTACAGGTTATCCCAAATTCCGTGAAGTATTGTGCACTTGTCCTCATTGCCGATATACAGCTCGAAGGGACCCGTTCGCATGTTGCTGTTCCAGG
TGGCCTTCATTCTGACGGACAGGCAGCAGCCATCCTTTCCGCTGTTAAAGTGATAGATGCCCACCCCATGACGTTGTCCCTTGAACCAGTCACCC
GAATAGTTGTCCCCATTCACATACTTGTACCGGCCCTTGCCGTGCTTCAAGTTCTTTCGCCAGTTGCCCTCGTACACGGATCCGTCCGGATAGAT
GAAGATGCCGCGCCCACAACGCTTCCCGCAGCGATACTGTCCGTAGTATCGTGAACCATCCTTGAACACGTACACCCCGATGCCGTGACGGCGAC
CCTTCCTGTAGTTCCCATCATACTGATCTCCGTTGGGCAGGATGGCCCAACCTCTACCTTGTCTCTGTCCGGCAGCATTTCGACCGCCTATGTAG
AGCTGGGATTGAGGATTATTATAGATATTTGTTTTAATTGAGCTCCTTGCTTACTAAAAACTGTTACTACTAGAGAATGTTCGTATTAAAGTTAC
TCCACTAAAAATTTATTTCTTTTGAGGAAGGAAGATGCACTACTAAGAAACTCATCCATTTTGGAACTTACGCCTATATTGGGTCCCAAATCCTC
CTCTTCCTCGGGCGCCGACAGATCCTCCTCGGACATTTCGGTCATGGCCATGGTGATGATTTTGAGTTAACTAACTCCTTTCGGTTCTTTTTATT
GCCGAGTGAAGTAGATTTTTACTTACGAATTACGTTCGGGAAATATTTTGTGTAGGCATTAAATAAATGTATTCTGTTTGTATAGTTAACTTAGC
AAAGGCTTACTACAATAAATATCAGAATCGAAGAATGATGAAATCGAGGGCTACGTTTTCGCATAGAAGTAGTTGGCCAGTGGATATCGTATGGT
CAGGGCAATCAGTGTACACAGCACCTGGAATCCCATCAGCATCTGGGTGACCACTCGCTCGTGGACAGGTCCGAAAACGACTAGGACAAAGTTAA
TGAGCGTAAAGTTGTTGGTCCTAACAACTCCGTCCGCTTTGGTATGCCAGCTTATTAGTCGCAAGTTCCGCAGTACTGTGACCATCAGGCGACCC
GGAGCGTTGAGATCCTCCAGGCGAAACTCCGTGGTGCTGATGTGGAGCAGATCCGTCTTGCTGTCGTACTTGGGCAGCCGGTGACGCGGACATGG
CACAAAGTGGAACAGCTGCGGCGTGGAGTACAGGAAATTCAGGATCTGCGGCAGGAAGAAGAGCAGCAGCGTCTTGCTGAAGTGGCCCAGGATTC
CAACCACGGCGAAAGTCATGCCGGCAAAGTAGCAGTAGGTGTCCCCAACAAACACCTGCGATGGATATCTGCGAAATAAGTAAGATAGAAAATAT
ATTACAAACGAAAAGTTAGTTAGAAGTAAAAAAAATATTAGGAATTAACAACAAAATTACGCATGACAGAAAAATTAACATTATTATCCGAACTT
TATTACATAAAAGTTTTATTTTTTGTGAATATGATAATTATTAAATTTAAGCTGACGAAAAGAGATTATAACGTATTTTTAAGTTTCAAATAACA
TCCTTAATAATTCGATAACAGTAACAACCAGTGTTGTAAGGCCCATCGATGCGAAACAGCCAGATTTACAACTGCAGCGGCGAACAGCTGACTGA
GGACATTTGCGTCAGCTGTGCGGGGGAGTTGAGGGGTGCCGTAAAATTTTTGGGCGTGTTTGCCAGCAGAAGAAAAGCGTGAAAAGTACGAAAAA
TCGAAACGGAATGAGCAGGATGAACTGCAGAAAGTGAACCAGTGACCATGGTGAGAAGCACATTCCTGGCCACCTACAACCAGACACCGGTAGCC
GGCGTTGGACGGCTGGCCATCACCAAGAAGCTGGTGCTCTGGTTGGTGCTGGTGCTGCAGGTGGGCTTCATCGGCTGCATATGGCTGCTGCAGAT
GAGCCGTGGCCAGGAGTCGCAGCAGCGCAGTGCAATGGACCAACTTGGCGGACGGGTCAACTTCGTGGCCAGCGGTGAAGCCCCTATGGAGAAGA
TGGCACTTGTGGGCGGAACCCACTGTCCGCATCTGCAGGAGAATGTCAACCGCTACGACAAGGACTTTTATCAAATGAAACCGGAACGACTGAAC
GAATCCCACCTGCCCGACTACAATGTGCCCGCCTATGTGGACGCGGAGATGGGTCTAACCCCAAACCTCTGGTGCTATCGCGAGGGGACCATCAA
CGAGAGCCAGCGGCTCAACGATGTGGACTATCTGATGGCGCCGCCTCAATGCAGATGTGAAAGTGGCTGGCACGGCAGAGATTGCGGCCAGCCGG
AGATCATATGGCGAGCCCTGATGACGTCCAATCGGGCCAGTAAACGAGGCGGTAGCACACCGCTTCAACTGGTCGAGGCCAGTTCTTCTTCACTG
CACCGCCTGTTCTATATGCTTGAATTGGGCGCCTGGGACCACCTAAGTCTGGAGCTCTTGGAGCTGCAAATTCGAGCGCTCATCGAGGTTGTGGA
CTACTTTCTCATATACTATGTGAGCAACGGCAGCAAGGAGCGGAGTCTGGAGAGCATGCTGGGCAGCCAAACGAGCTATACGCTACTACGCTGCT
CCTCCGAGAGCAACTGCACCAGCTCAATGGCCTACAGTCACTTTAGGCGGCAGCTGTGGCAGCAGTGTGGTGTCCAAATGCAGGCACAGGACCTG
CTGCTGCACGGGGACAGTGGAACGGTCTACGCGCCAGCAGCACTCAAGTTTCTGAAGTACTATGCCAAGGATGTGCTGCCGCTGAAATTTCGTTT
GAAGTACAATGTATATGGATTCTACTGGCAGCATCCGAAGAAGACCCTCCTAAATGGGGTGATAAGTTCCTTGGGGCACCTGCACAGTGCCCAAC
TGGATGCTCACCGCCTGCACCGGCTGGCGAGCAGCACACTGGGTGATCTCAACCACTACGGCGGCTGGAACTGCGAGCTGTGCCTGCCTCCCGAG
CAGATTGTGCTCCTGCTGCAGAGCTCCAGTCCCCGCAAGCTGCCAGTAAAACTACCCAACGATACCCGCAATGCCCACATCGATGCCAACTACAT
GCAGCAACTGATAGCCAATGGAGTTCACATCGATGGCACCACGCAGCTGCACCGCTTGCGGGAGCAGAGCGAGAAGTATTTCGCTCCGGAGGAGG
CGCTCCAGCACAGCAGCCAGTACGGCCAGCTGCTGGTGAACCTATACGATGTGGACGTCCTGGAAGATCTGCAGGACGAAGACTAACTACGCCTG
CCGAAGTTTGACTTGGGCATGGCAGCCTATCGAACCAGCATAAACCTACGAATATATATATTTATATGTGCCTGCTTTTGAATCCCCATCAAAGT
CTAACAATCTCATAATCATCATATCATACTCTGCCTAATCCACTCATGCGAATGCCCTTCTGTGTTTTTGGCCAGGTGAATTCCAAATTTAGTAT
CTCAGCAGACAGGACAGACAGACCCGCCATCTGTGATAAGAAAAACCAGAACTAAACAATGAATTTATGAGAGGAAGTCGATGCAACCAACTGAG
AGAAGTCTCAAATTTGCTGGAAAAAGTTGTGAAATGGGTTGATCGCAATTTAGCATTATTTTTAAGACATAACACACACGATCTGTATGAAAAAG
CTTTTTAGACTTACTTTAAATATTAATACCAATTATCAGAAGGCAAGCAAATTTAAGCTTAGTTTTGGTTACAATTTTGAAGCAATTTTGAATTT
GTGTTATTACTTTATTACTAACGTACCCTAATTATAATTAGACGAAAATTTGTTGACCTTCCAGATCAATTCAGTATTTATAAAAATAAAAATCA
ATTGGATTACTCACTTGTTGAACTTCCATAGCGCTAGGGTGGTGGCCAGGAAAGGCAGCATGAAGTAAATGGAGAATATATGCGAATCCACCTGG
TGACCGAGCAACAGTTCAATGGCATTGAAGACCAGAATGGAGCCTGCAATAATAAAGGATTGTCCCACCTCCAGGCCATTGATGCCCGCCAGGAT
GTTGATGGCATTTGTGCAGAATACCGCCAACATGCCCATGAAGACGTAGTACAAGGCACCTTGAAGAAATCAAAATAGGTTTCATCTCTTGATTT
TCATTTCTGGAAAACCTTAGCTACCTATATTCAAGGAGGTCCCAATCAGATTCCTTGCAAAGTTGGGCATAATGACCGTCGTGGAGTTATAGTTT
ACGTAGTACACCATTAGCAGCGGCAACGTGGCGATGGTGGGCAACAGGAGCTTGTGGCGCCATCGCAGGTCGAGAACGTCATCGGCGAAGCCCAA
GAAGATCATGCAGCAAATGGAAAGAAGGGCGGCAATCAATTCCACGAACTGTGTGGGGAATAACAGCCGATAAGGTGGAGCACAAAGACATCTAT
CAATTAGATAGCTACCTTATCATGTGGAAAGGTATCTGGTTTGCCTCCAGTAATCGCATCCGTGGCAGCTGCCTCGTCGAAGGCGAAGGGAATCG
GTATGAACAGAAACAAGGACACCAGGAACACACAGCCAATAAGCACACCAAAGGATTCAGGTCTAGAGTTTAGGAAGCGTTTTAGTTAGAAAACC
TACAAAACAAAGGAGAGCGAACTTACACCTGCGGCTTGTCCTTCTTGCACAGATCGTTGCCAAAGAGATTGGCCTTGATGAACATCTCGCGGAAG
CGGGGTATCATCCGGACTGTCATGCAGTAGGCGGCGCCCGAAATGGCCGCATTGATGGCTATGGCGACTCCCGACATGGTCGGCCTTGAAAATCC
ACCTTCCGCTGCACTAATTCAATTAGCTGGTGCAGCTCTGTGCGCAGCAAATTTGCCGGAGTCACGCGTACGGAGTGCGCTGTTTCAATTGGGAT
AGTGGGAGGCCGCGGAAAACCAGCCGATCACTCGATCATGGTGCAGAAATCAATTACGCCGACAAAAAAAAGTACACGCAATTGAAACTCAAATT
GCTGATAACAACAAACTCAGCTGTTCGGCGGCTAGTGTGCCCGTACTTTCGACTGTTAGACAAACCAAACAGCTGATTTTAGTTTACTAATTTAA
ATTATTCATATATAAAATACCACAAATGAATTTAATTTTATTTTGACCTACCTTAGTGAAAATAGTTTTTAATTTGTATAGTCGGCAATAATCTT
AATTTAATTTCGCTTACATATCAAAGTTAGAAAATGTTATAGTATTTCTAAAATCAAGAGATCGTTAAAAATTTAAAGACTGAAAGTAAAAACAC
TTTACTAGATGAAAAAGGCTTAACTTTATTTAATATCAATGATTACAACACTTGGACCAACTCCGTTATTACACATATAGATAAAGATATCTACA
ACGAAATAGATAAAATATGTTGCGAATACTTGTTCTTTTCGAGCTTCCTTTGTCAATTTGGATTCGGTAAAGATTGCTACCTATCCCTGAAGAAG
GGGAAGACCTTTTGCAGCTCCGCCTTCGACTTGCAGGCCTCCACCTGCGGCAGGGTCTCCACCAGATTGAGCAGATAAATCTGCAGCTGCTGGCG
GCGTTCCTCCACGAAGACCAGGTTCATGTTGCCGAAATGCTTCTTTGGTGGAAACTCCACGGCACTGACCACCGGATGGTCTTAAGCAGTGACT
TGTGCAGCTTGTAGAACTCGCTGTAGCGTCTGAAAAACGTCCAGTGCTCCAAACGCTGCCTCATCGTGATGTGAACTTCGTAAGTGTAGTGGGAA
CCAGATCGTTGTGTCTTTGCCAGCTTTACATGCGGAATGGTTATCAGGAAATTGGAGCACAGCGATGAGCTGGGGTCGATGCCGGTCTCTTCAAA
CTGTTTGGTTAGCCTTCGGATAAGCAGGCGATTTTGAAGACTAAGCTCCGCCACACGGGTTTCCAGCAGAGCGCATCTTTCGTTTAGCTGGTTGA
CATGCTCTTCCAGCGCAGCTTGCTGTTGGCTGTTAGCCAAGCAATTGGCAGAGGAGGAGGACTTGCTCCACTGCG
(SEQ ID NO: 583)

FIGURE SHEET 320

Exon: 5155..4777
Exon: 4717..4576
Exon: 4513..4300
Exon: 4239..4082
Exon: 1480..1001
Start ATG: 4922 (Reverse strand: CAT)

Transcript No. : CT16853
AACAGCTGAGTTTGTTGTTATCAGCAATTTGAGTTTCAATTGCGTGTACTTTTTTTTGTCGGCGTAATTGATTTCTGCACCATGATCGAGTGATC
GGCTGGTTTTCCGCGGCCTCCCACTATCCCAATTGAAACAGCGCACTCCGTACGCGTGACTCCGGCAAATTTGCTGCGCACAGAGCTGCACCAGC
TAATTGAATTAGTGCAGCGGAAGGTGGATTTTCAAGGCCGACCATGTCGGGAGTCGCCATAGCCATCAATGCGGCCATTTCGGGCGCCGCCTACT
GCATGACAGTCCGGATGATACCCCGCTTCCGCGAGATGTTCATCAAGGCCAATCTCTTTGGCAACGATCTGTGCAAGAAGGACAAGCCGCAGGTA
CCTGAATCCTTTGGTGTGCTTATTGGCTGTGTGTTCCTGGTGTCCTTGTTTCTGTTCATACCGATTCCCTTCGCCTTCGACGAGGCAGCTGCCAC
GGATGCGATTACTGGAGGCAAACCAGATACCTTTCCACATGATAAGTTCGTGGAATTGATTGCCGCCCTTCTTTCCATTTGCTGCATGATCTTCT
TGGGCTTCGCCGATGACGTTCTCGACCTGCGATGGCGCCACAAGCTCCTGTTGCCCACCATCGCCACGTTGCCGCTGCTAATGGTGTACTACGTA
AACTATAACTCCACGACGGTCATTATGCCCAACTTTGCAAGGAATCTGATTGGGACCTCCTTGAATATAGGTGCCTTGTACTACGTCTTCATGGG
CATGTTGGCGGTATTCTGCACAAATGCCATCAACATCCTGGCGGGCATCAATGGCCTGGAGGTGGGACAATCCTTTATTATTGCAGGCTCCATTC
TGGTCTTCAATGCCATTGAACTGTTGCTCGGTCACCAGGTGTTTGTTGGGGACACCTACTGCTACTTTGCCGGCATGACTTTCGCCGTGGTTGGA
ATCCTGGGCCACTTCAGCAAGACGCTGCTGCTCTTCTTCCTGCCGCAGATCCTGAATTTCCTGTACTCCACGCCGCAGCTGTTCCACTTTGTGCC
ATGTCCGCGTCACCGGCTGCCCAAGTACGACAGCAAGACGGATCTGCTCCACATCAGCACCACGGAGTTTCGCCTGGAGGATCTCAACGCTCCGG
GTCGCCTGATGGTCACAGTACTGCGGAACTTGCGACTAATAAGCTGGCATACCAAAGCGGACGGAGTTGTTAGGACCAACAACTTTACGCTCATT
AACTTTGTCCTAGTCGTTTTCGGACCTGTCCACGAGCGAGTGGTCACCCAGATGCTGATGGGATTCCAGGTGCTGTGTACACTGATTGCCCTGAC
CATACGATATCCACTGGCCAACTACTTCTATGCGAAAACGTAG
(SEQ ID NO: 584)

Start ATG: 234 (Reverse strand: CAT)

MSGVAIAINAAISGAAYCMTVRMIPRFREMFIKANLFGNDLCKKDKPQVPESFGVLIGCVFLVSLFLFIPIPFAFDEAAATDAITGGKPDTFPHD
KFVELIAALLSICCMIFLGFADDVLDLRWRHKLLLPTIATLPLLMVYYVNYNSTTVIMPNFARNLIGTSLNIGALYYVFMGMLAVFCTNAINILA
GINGLEVGQSFIIAGSILVFNAIELLLGHQVFVGDTYCYFAGMTFAVVGILGHFSKTLLLFFLPQILNFLYSTPQLFHFVPCPRHRLPKYDSKTD
LLHISTTEFRLEDLNAPGRLMVTVLRNLRLISWHTKADGVVRTNNFTLINFVLVVFGPVHERVVTQMLMGFQVLCTLIALTIRYPLANYFYAKT*
(SEQ ID NO: 585)

Name: N-acetylglucosaminephosphotransferase
Classification: enzyme

Celera Sequence No. : 142000013384548
CATACAAATATTATGTGGATAAATGGTCAGATGCTGATGAATCGGGAGAATCCAAGGATCAGGAGTCCTTTGCTCATTACCAACGCAACCAGCAG
CGCTCTAAGGCAAAGGCCACCAAGGAATCTATTAGTGACATGAGAGAGGTGAGGTTCCCCTTACATCCAGGACTTCTTTTGGTCTTTACTTGCCA
GTTCTCTCCTACAGATCATCCGACAAGCCTTCAGGAGCTCTGAAGTGAAGAGCCTGCGATTTCTTTTTGGCAACAATATGTTCATGCCCTCGGAG
GCCTATACTCTGCACATACCACATGATTCCATATCCAGAGATCACTATTGCGAGCACCATGCTCTGCCCGAAGGTCGCATCAACCAGGCGCTGCT
CCGCCTGCTCACCTGCGAGGAGCTGTACAGGCTATTCTCCACCGAACTAAAAGTCACCAACGTGTTTCTAGAAATGGAGCTCCTTACAGACTCCG
ATCGACCCCAAGGATCCCATTGTGACTCCTTTAATCTAATCCCAAAGCATATATTAAGCCAACTTCCGCGCAGCTGCAAGAACATACACCTGCAT
CTACTGCATTGCAGTGAAAACACACCGAATGAATTACGCTGCTGCAAGGAGATGGATATTTACCACGATCTTGGCGTGCGGAATCTGGATAAATC
TGGGGAAGACGTTAGCCAGACCAACGAAGAGCATGACGTTTTGAAAGCAGCAAATGAAACCAGCGGTTGGTGGCAGGCCGAGGTCATAGTTCGCG
GTTTCAGAGCTCCTGGCAACCAAAAATCGGGAGATTTGTGGTCTAGCTAACATTTTATAACTTGGATTCTTGCTATTCGGCGTGTTTGTGTCAAA
AATAAAGTTTCGAATCGTTTATATTTCAAGTATTAAGTTATTTTATTATGTATATAATTGTTTAATTTTATTTTTGGTTTCGATTTATTGAGAAT
GTTTTGAAAACCCAAGGCACTCAAAGATGATCCATCGTGGTATTGGTATTATCATCTTAGGTAGTGATAATCATGGAAACTGGTGCACTGCGCTC
TCGCTGCTTGGCCACAATCTTGTTGGCTATGCGATCCAAGTTACGTTGTCCTTGCGGAGTCAGCTTACGACCACCATCCGGGTGCCTCTCCACCA
TGTTAGCAGCTTCCAAGGCTTGAAGAGCCTGCTCATGTGTTAGATACATGCTAAGTAATATTAAATATAACCTTAAAGTACAACCATTTCCCACT
CACCTTGCGAATACAGCCATCCGATGAGCGACAGTGCTTGGACGGACGAACACCGTTGCGCTTGCGCCCGCTATAGACCTTGGTGAAGGCCCCAA
CGCCGGCGGGACTGCGCAGGTACAGGTGTCTCATAATAGAGGCGCAGCGAGTGTAGAACCAGTCGTCGTCGGTAGGAGCAGTCTCCTTGAACTTG
CCAGTCTTCATATAGACGGCCTGTTCGGGCACAAAAATTTTTCCGGATTTTTTGAGAAAAGCAGCCATGTTTTTGGTCAGAACGTGCTGATCGAT
TTCCTTTACTGTGACTCCAGGCATGTTGCTCTCTACGTTCTTGAAAGCACGTTTTTAAGGCTCATGGGTCCGATATATGTATGTATGTATTTAAA
AAAGTCTTACCTTTTGAGAAGAAAAAGGTTTGCTTCCGGTTAGTTTGCTGACTTTAGTCAAAATGGACGATTGGCAAGTGACGTTTGAAAGAGGG
ACCAGGTCATTGACCCCAAAGGATTACTTTCCGATAGTTTTGTCGTGCAGTATTGGTGAACTTGGCAATTCTTTTCGAAAACTTAACCTATAAAC
TTGGAAAGGAACGCAATGTAGCAAAACTACTGTTCTTGGTGACAGGGGGTTTAAGGTAGACTAACAAGGACAATTTTATGACACTGAAGCCCTAT
GGAGTAAGAATCAAAGAACTGCTGTATTTTGGTTTGTATAAATGAATAAAACGTTCTACGCTAATTGAAGAGCATTCGAAGAGGTTTGAATACAG
CGCCATAGGGTGACCAGCTTGTGGAGCATTGAAGGTATTTCTTGTTTTAAGAATGATCACGGGATGGTCACACTAGAAATACAGCCAAACAAAAC
AACAAAAAGCATTTCGAGCGCTAACAAATATATATCTTTCGACTTGACTCATTCGCATTCCGGTTGACCGTGTCGCGCCTGCAGCATGTCTGAAA
AGCCGACTGTTCTGATTTTGGGTGGTAAGTGGTCCCGCTGCATCCTCCTCATCGTCATCCTGCCCCCGCTCCCCACTCCACACTTCCGCTTATCA
GCATCGCTGACTGCATCGCTGCTCTTCCTCTTCCCGCAGGCTGCGGCTTCATTGGACGCAACTTGGCCACTTATCTGCTGGACAATGAACTGGCG
CAGGAAATACGACTGGCCGATAAGACCCCTCCGCAGATGGCATGGCTAAACGAGGAGCAGACGCGGGTCTTCGAGAGCGATCGGGTGGAGTTCTG
CAGCGCGAACCTAATAAACGCCGGTAGGTAATCACTACATTAGGGTGGCTCGTTCCACCAGGATGCGGATCACA
(SEQ ID NO: 586)

Exon: 1544..1239
Exon: 1168..1001
Start ATG: 1544 (Reverse strand: CAT)

Transcript No. : CT16966
ATGCCTGGAGTCACAGTAAAGGAAATCGATCAGCACGTTCTGACCAAAAACATGGCTGCTTTTCTCAAAAAATCCGGAAAAATTTTTGTGCCCGA
ACAGGCCGTCTATATGAAGACTGGCAAGTTCAAGGAGACTGCTCCTACCGACGACGACTGGTTCTACACTCGCTGCGCCTCTATTATGAGACACC
TGTACCTGCGCAGTCCCGCCGGCGTTGGGGCCTTCACCAAGGTCTATAGCGGGCGCAAGCGCAACGGTGTTCGTCCGTCCAAGCACTGTCGCTCA
TCGGATGGCTGTATTCGCAAGGCTCTTCAAGCCTTGGAAGCTGCTAACATGGTGGAGAGGCACCCGGATGGTGGTCGTAAGCTGACTCCGCAAGG
ACAACGTAACTTGGATCGCATAGCCAACAAGATTGTGGCCAAGCAGCGAGAGCGCAGTGCACCAGTTTCCATGATTATCACTACCTAAGATGAT
(SEQ ID NO: 587)

Start ATG: 1 (Reverse strand: CAT)

MPGVTVKEIDQHVLTKNMAAFLKKSGKIFVPEQAVYMKTGKFKETAPTDDDWFYTRCASIMRHLYLRSPAGVGAFTKVYSGRKRNGVRPSKHCRS
SDGCIRKALQALEAANMVERHPDGGRKLTPQGQRNLDRIANKIVAKQRERSAPVSMIITT*
(SEQ ID NO: 588)

Name: ribosomal protein S19 like
Classification: ribosomal_protein

Celera Sequence No. : 142000013384589
TCCACGAGATTCTCCACCTCGCTGACCTCTCCGTTCTTGATAATATCGAAGATGTCGTCCAAACTCACGGTGGTGGCACCATCGAGCCCCTCAAA
GAGGAGCACATTTTCGTGGTCCTCGACGCCGCTACTGCCGTGTCCACCGTCCGTGCCGCGACCCGTTAATGGCGGCGAATGCGGTCGATGATCCA
AATGGATGTCGTCGGCGTGGGCATGGCCATCCTCCTCCGCGACGACCATGTTGCAGGAGGAGGAGGCGGTTAGGGGCAACGCCCACACACTGCGC
GCCGCCCCCGGACTTGGATGCACCTTCGAGGCCATGTAGAACTCGAAGTCCACGCCCAGACGGTCCGCCGTTCCACCGTTGCCTTGATGCAGGGG
GTTTTCCAGTAGGTGTGCAATCTTGTCGCCTTTTTCCGTTACGCTCCGACCGAAATTTGTACTCTGTTTGGCCAATCTTAGGCGTGGAATGCTAG
GTAAACACGACTGCACTCGATGGCGAGGAAATTATGTCAGCACTGTGAGAAAATCAATATTTGTCCCGAATCGCAGGACTCGAATTGGGGCCACT
TTCGAACTCGACTTGGCGCCAAACAAATCAACAGCTGACCGTTATTTTCGCAGTTGGGCGCGCAGTGTTGCCAACACATACTGGTAATTAAGACT
TTTCTCAGCGAGGGGTGATTTAAGATTTAAGTCAAGAAGTATTAAAGAAAAAATATATATATTTAATTTGTTGGAAGGTCAATTGTTGAAACCGA
GGTATCATTTAGCTTAACTTAAATATACTAGAAATCTCGTGGCATAAGCAAACTAAAAAAAAAAGGTTTATCAACTGACTTTTATATTAGTTTTA
ACATTATTGGGAAACATTTGTTTTCCGCCGCTAGAAACCTTTAAAATGTATACTACTATATTGCTTGGTACGAATGTTGCATTTTGAACTGATGC
TAGCATTGCATTTTGTAAGGTTCCCATGTCTCTGTTATTTTGCCACCTGGTAACACTGTGCCCCTTTTTGATAAATTTGTTTCGTAAAAAATGGG
CGACAACGTGGTGACGGAACTAAATAACTTGGATTTGAACAATCAAAAGGCATGTTAAACTCTTTTCGAACTGCATTCGAGTGTATGAGAAGTGC
TAGTTAGCCGAATTATGTTGAAGTTGGCGCCGCAGGGCGGCAGATATTATAGCCAAATAAGCCGCATTTGCCAGTGGATTTTGCCGAAAATTCAG
ACGCAGTCGAAGCCACCAAAACAACAACAACAACAGCAACCACAATTGAAAGAACAACAACAACACAGCTACGCAACTTTGGTTGGTGTTTTAAG
CTAAAAAGAATTGACCTAAACTTCAATTTAAACGCCTGTTACTGCTGGCACGTGTAAATGTTATGCTTGTCTGTGTGAGTGTATGCGATTCTCCA
ATGAATCAGTGCCGCCGGCTGTGACGTCACTAACAACCAACCAACTTCATGAGTGTCTGTTTTTTTTTGCTACTCTATTGCATCAGCCATAAAAC
GACGAAGATACGCTCAAAGACGGCTCGATAAAACAGAGATAGGAGCACCGAAAACATAGCACCGAAAAGTGCTCATTGCCATGTCCCCAATTGTT
TAAACAATAAGAAAACATCAGTCGAAAGTAGATACCGAAAAAGAGCATTTGTCTAATTGCATACGTAGCACACTTGTGGCCACTTGAATATCTCC
GGTTTATATTGATTTTTAACCTATTTCCGATGGATTTGCAGGCTGCCAAGATGAAGAAGGAGAAAAAGGAGAAGCCATCCGGCGGTGGAGATACT
CGCAAGGGTAAGTAATTCTAACTAAGAATTAAAAACACAAAACGCACTTCCGTCTGTAAGATATGTAGCATATCTTTAAGATTAGCTGCCTTCTT
CTCTCTAATACCTGAAATTCCACTGATCTCTGCTATATTGATTTCAGAACTCAGTCCCTTGCCCAAGTACATCGAGGAGCGCAATGTCTTCTGGG
AGAAGTGCAAGGCGGAATACGAGGCCGAACTGGCGGCCAAGAAGCGTGAGCCCATCAAGGTGACACTGCCCGATGGCAAGCAGGTGGACGCCACC
TCCTGGGAGACCACTCCGTACGAAGTGGCCCGCGGCATTAGTCAGGGTCTCGCTGACAACACCGTCATCTCCAAGGTGAACGGCGAGGTGTGGGA
TTTGGACCGTGTGCTCGAGGGAAACTGCACCCTGCAGCTTCTCAAGTTCGACGACCCTGAGGCGCAGGCCGTCTTCTGGCACAGCTCTGCCCACA
TCATGGGTGAGGCCATGGAGCGCATCTATGGTGGACACCTGTGCTACGGTCCGCCCATTGAAAACGGCTTCTACTACGACATGCATCTGGAGGGC
GAGGGTGTAAGTAATTTGTGATGTTCAGTAAGAATTAAATTAAATTGAACGCCCAATTAGATCTCCACCAACGACTACGGCGCCATGGAGGGTCT
GGTTAAGCAAATTGTCAAGGAGAAGCAGAACTTCGAACGTCTGGAGATGAAGAAGTCCGACCTGCTGGAGATGTTCAAATACAATGAGTTCAAGG
TGCGCATTCTCAACGAGAAGGTGACCACCGACCGCACCACTGTCTACAAGTGCGGTTCTTTGATCGATCTCTGCCGCGGACCTCATGTTCGTCAC
ACCGGCAAGGTGAAGGCCCTGAAGATCACCAAGAACTCCTCTACCTACTGGGAGGGTAAGGCTGACGCTGAGACACTGCAACGCGTCTACGGCAT
CTCGTTCCCCGACCCGAAGCAGCTCAAGGAGTGGGAGAAACTTCAGGAGGAGGCGGCTAAGCGTGATCACCGCAAAATCGGTCGCGAGCAGGAGC
TGTTCTTCTTCCATGAACTTTCGCCTGGCTCATGCTTTTTCCAGCCGCGAGGAGCGCACATCTACAACACCCTGATGGGCTTCATCAAGGCGGAA
TATAGAAAGCGTGGTTTCCAAGAAGTCATTTCCCCCAACATCTACAACGCTAAGTTGTGGATGACCTCCGGCCACTGGCAGCACTATGCCGAGAA
CATGTTCTCCTTCGAGGCCGAGAAGGAGAAGTTCGCCCTCAAGCCCATGAATTGTCCAGGACATTGTCTCATCTTCGATAACCGCAATCGATCCT
GGCGAGAGCTGCCACTGCGAATGGCCGACTTCGGTGTGCTTCATCGCAACGAGCTCTCCGGTGCTTTAACCGGATTAACTCGCGTGCGTCGCTTC
CAGCAGGACGATGCGCACATCTTCTGTGCCCCCGAGCAGATTAAAAGCGAAATGAAGGGCTGCCTGGAGTTCCTGAAGTATGTGTATACCATTTT
CGGATTCTCCTTCCAGCTGGTGCTGTCCACACGCCCGGATAATTACCTTGGCGAGTTGGAACAGTGGAATGATGCGGAAAAGGCGCTGGCTGAAT
CACTCAACGAGTTTGGAATGCCGTGGAAGGAGAACCCCGGCGATGGCGCCTTCTACGGACCGAAGATTGATATTACCATTATGGATGCACTGAAG
CGTGCCCATCAGTGCGCCACCATCCAGTTGGACTTCCAGCTGCCAATTCGTTTTAATCTCAGCTACATCGCCGACGATGGCGAGAAGAAGAGGCC
GGTGATCATCCATCGCGCTATTCTTGGCTCAGTGGAGCGGATGATTGCCATTCTCACGGAGAACTTTGCTGGCAAGTGGCCCTTCTGGCTATCAC
CGCGCCAGGTGATGGTCGTTCCAGTGGGTCCTGCCTATGATCAGTACGCCCAGTCAGTGCGGGATCAGTTGCACGATGCTGGATTCATGAGCGAG
GCGGATTGCGATGCCGGCGACACGATGAACAAGAAGATACGCAATGCTCAGTTGGCCCAGTTCAACTTCATTCTGGTGGTGGGCGACAAGGAGCG
CTCCTCGAATACCGTTAACGTGCGCACTCGGGACAACAAGGTGCACGGCGAGGTCTCCGTGGCGGAACTCATCACAAAGCTGCAAAAGATTCGCG
ACGAATTCATCGCCAACGAGGACAGCTTCTAAGACTCTATTTCGAACTATTTATCAAAAGTATACTTAACATTTGCATAGCAAAGCAAGTACGCA
TTTTTGTTCTTTCTATGTATTTACGCTTACGAAACCGGAATTCACAAATAAAAAACCAAATCCAAACACATTTTAAGGTGTTTCAAATAGAAGAG
AAGAGCATGCAATCAAATAAAAGCAATTCGATTCAATATACGATTATTAAGCTTCCCCAACTAAAAATCGTATTTTTCTGATCCACCTTAAGCCG
CCTATTTCACTCCAGTTTCTTGACGAATCAGTGGAATTTGTCAGCAATTGAGGACTAGTCATGCCGACACAGAGGTGCGCTGTAGTCCATTCAGG
AACGATTTGGAATGATAAGATAAGTCGGCCCACATTTGGCGGAAAACTTTTTGGGAAAGGTGTGCGTGCACCCACAACGTATGAGTCATGTTTTG
AATTTATTTTTTTGTATTAATTTATTGCTAGTATCTTGTATACTTTTCATTTTCATAATTTGATTTATTAAAAATTGCATCAATAGTTTATGTTT
TTATTCAATTATCAATTTTGTAAGCTTTTGCTTTTCGCGTAAAAAATGCACAAAGTTCTCTCGCTAATCGAAGCAAAAATCGTTAATAATATTGT
TAAGTGTTTGCTCTGCTCGTGCTCTGCTTATCTGTTTCAGTTTTAGTCATAAAAATACATATTTTATATTTGTGTATATTTATTCATAAGATGCA
CGTGGCCAAGTCCTATGCCATCCACAGTTCCAGTTAGCAGTCGCGTTCGCTGTGCTAAAAAAAAAAACCGAAATCCTAACCAAAACTGGCGAAACA

FIGURE SHEET 322

AAAGCCGCAAACAGAACAGAACGGGGGCTAAAATTGGAAACAAAATGCCTGGCTGGTGGAATCATTGAACACAGACTGGCTGCGTGGTATCTACG
ACTGCTGGAGATGCCGAGAGCTGGAATGTCGGAGGATCCTGGGACCGCCTGGCCTGACATAAGTACATGGTCTTGGGTTTTT
(SEQ ID NO: 589)

Exon: 1001..1094
Exon: 1752..1812
Exon: 1948..2381
Exon: 2436..4022
Start ATG: 1761

Transcript No. : CT16980
TAACACTGTGCCCCTTTTTGATAAATTTGTTTCGTAAAAAATGGGCGACAACGTGGTGACGGAACTAAATAACTTGGATTTGAACAATCAAAAGG
CTGCCAAGATGAAGAAGGAGAAAAAGGAGAAGCCATCCGGCGGTGGAGATACTCGCAAGGAACTCAGTCCCTTGCCCAAGTACATCGAGGAGCGC
AATGTCTTCTGGGAGAAGTGCAAGGCGGAATACGAGGCCGAACTGGCGGCCAAGAAGCGTGAGCCCATCAAGGTGACACTGCCCGATGGCAAGCA
GGTGGACGCCACCTCCTGGGAGACCACTCCGTACGAAGTGGCCCGCGGCATTAGTCAGGGTCTCGCTGACAACACCGTCATCTCCAAGGTGAACG
GCGAGGTGTGGGATTTGGACCGTGTGCTCGAGGGAAACTGCACCCTGCAGCTTCTCAAGTTCGACGACCCTGAGGCGCAGGCCGTCTTCTGGCAC
AGCTCTGCCCACATCATGGGTGAGGCCATGGAGCGCATCTATGGTGGACACCTGTGCTACGGTCCGCCCATTGAAAACGGCTTCTACTACGACAT
GCATCTGGAGGGCGAGGGTATCTCCACCAACGACTACGGCGCCATGGAGGGTCTGGTTAAGCAAATTGTCAAGGAGAAGCAGAACTTCGAACGTC
TGGAGATGAAGAAGTCCGACCTGCTGGAGATGTTCAAATACAATGAGTTCAAGGTGCGCATTCTCAACGAGAAGGTGACCACCGACCGCACCACT
GTCTACAAGTGCGGTTCTTTGATCGATCTCTGCCGCGGACCTCATGTTCGTCACACCGGCAAGGTGAAGGCCCTGAAGATCACCAAGAACTCCTC
TACCTACTGGGAGGGTAAGGCTGACGCTGAGACACTGCAACGCGTCTACGGCATCTCGTTCCCCGACCCGAAGCAGCTCAAGGAGTGGGAGAAAC
TTCAGGAGGAGGCGGCTAAGCGTGATCACCGCAAAATCGGTCGCGAGCAGGAGCTGTTCTTCTTCCATGAACTTTCGCCTGGCTCATGCTTTTTC
CAGCCGCGAGGAGCGCACATCTACAACACCCTGATGGGCTTCATCAAGGCGGAATATAGAAAGCGTGGTTTCCAAGAAGTCATTTCCCCCAACAT
CTACAACGCTAAGTTGTGGATGACCTCCGGCCACTGGCAGCACTATGCCGAGAACATGTTCTCCTTCGAGGCCGAGAAGGAGAAGTTCGCCCTCA
AGCCCATGAATTGTCCAGGACATTGTCTCATCTTCGATAACCGCAATCGATCCTGGCGAGAGCTGCCACTGCGAATGGCCGACTTCGGTGTGCTT
CATCGCAACGAGCTCTCCGGTGCTTTAACCGGATTAACTCGCGTGCGTCGCTTCCAGCAGGACGATGCGCACATCTTCTGTGCCCCCGAGCAGAT
TAAAAGCGAAATGAAGGGCTGCCTGGAGTTCCTGAAGTATGTGTATACCATTTTCGGATTCTCCTTCCAGCTGGTGCTGTCCACACGCCCGGATA
ATTACCTTGGCGAGTTGGAACAGTGGAATGATGCGGAAAAGGCGCTGGCTGAATCACTCAACGAGTTTGGAATGCCGTGGAAGGAGAACCCCGGC
GATGGCGCCTTCTACGGACCGAAGATTGATATTACCATTATGGATGCACTGAAGCGTGCCCATCAGTGCGCCACCATCCAGTTGGACTTCCAGCT
GCCAATTCGTTTTAATCTCAGCTACATCGCCGACGATGGCGAGAAGAAGAGGCCGGTGATCATCCATCGCGCTATTCTTGGCTCAGTGGAGCGGA
TGATTGCCATTCTCACGGAGAACTTTGCTGGCAAGTGGCCCTTCTGGCTATCACCGCGCCAGGTGATGGTCGTTCCAGTGGGTCCTGCCTATGAT
CAGTACGCCCAGTCAGTGCGGGATCAGTTGCACGATGCTGGATTCATGAGCGAGGCGGATTGCGATGCCGGCGACACGATGAACAAGAAGATACG
CAATGCTCAGTTGGCCCAGTTCAACTTCATTCTGGTGGTGGGCGACAAGGAGCGCTCCTCGAATACCGTTAACGTGCGCACTCGGGACAACAAGG
TGCACGGCGAGGTCTCCGTGGCGGAACTCATCACAAAGCTGCAAAAGATTCGCGACGAATTCATCGCCAACGAGGACAGCTTCTAA
(SEQ ID NO: 590)

Start ATG: 104

MKKEKKEKPSGGGDTRKELSPLPKYIEERNVFWEKCKAEYEAELAAKKREPIKVTLPDGKQVDATSWETTPYEVARGISQGLADNTVISKVNGEV
WDLDRVLEGNCTLQLLKFDDPEAQAVFWHSSAHIMGEAMERIYGGHLCYGPPIENGFYYDMHLEGEGISTNDYGAMEGLVKQIVKEKQNFERLEM
KKSDLLEMFKYNEFKVRILNEKVTTDRTTVYKCGSLIDLCRGPHVRHTGKVKALKITKNSSTYWEGKADAETLQRVYGISFPDPKQLKEWEKLQE
EAAKRDHRKIGREQELFFFHELSPGSCFFQPRGAHIYNTLMGFIKAEYRKRGFQEVISPNIYNAKLWMTSGHWQHYAENMFSFEAEKEKFALKPM
NCPGHCLIFDNRNRSWRELPLRMADFGVLHRNELSGALTGLTRVRRFQQDDAHIFCAPEQIKSEMKGCLEFLKYVYTIFGFSFQLVLSTRPDNYL
GELEQWNDAEKALAESLNEFGMPWKENPGDGAFYGPKIDITIMDALKRAHQCATIQLDFQLPIRFNLSYIADDGEKKRPVIIHRAILGSVERMIA
ILTENFAGKWPFWLSPRQVMVVPVGPAYDQYAQSVRDQLHDAGFMSEADCDAGDTMNKKIRNAQLAQFNFILVVGDKERSSNTVNVRTRDNKVHG
EVSVAELITKLQKIRDEFIANEDSF*
(SEQ ID NO: 591)

Name: threonyl-tRNA synthetase
Classification: enzyme

Celera Sequence No. : 142000013384663
ATAGCAGTCGAATGGAGACGGCACAATGCCCACTGCGTTCTGCAGGAACTTCAAGCTTTTGTAGAGCTTCTCCGAGTTCATGGTGATGCCACCCA
TGACCACATCCGTATGACCGTTCATGTACTTGGTCAGGGAGTAGCAGACCAGATCAGCGCCCAGCTCCAAGGGTCGCTGGAAGTAGGAGGTCAGG
AAGGTGTTGTCGACGGCCAGGACGATATCCTCGCGTACTCCATGGACCAGCTGCGCAATAGCCTCGATGTCGGCTACCTTTACCAATGGATTAGT
TGGTGACTCGATCCACACCAACTTGGTCTCCGGCTTGATGGAACTTTTAATTAGATCCAACTTCGTGGGATCCACAAAGGTGGCTGAGATTCCCA
GACGGGTGGCAACCTGTCGGATCAAACGGTTGGTGCCTCCGTAAACATCGTCGCCCATGATGATGTGATCGCCGCTGCTCAGCATAGTTAGCACA
GCGGTGGTGGCTCCCAATCCCGATGAGAACGTGAGGCCGTATTTGGCATTATCCAAGGCGGCGAAGCACGTCTCCAGCACGTTCCTAGTGGGATT
TCCACTGCGGGAGTACTCATAGCCCCTGTGCTCGCCCGGTGCATCTTGCTTGAAGGTGGTGCTCAGCGATATCGGCGGAATCACGGCAGCACTCT
TCCACTGGTCGGGGCTCTGGCCCGAGTGGATGGACTTGGTGGCGAAGCCGCTCGGCTGGACTCTGTAGCTCATCTTGTCTGGGTAGGAGGATCGT
TGGGAACTGACTGACACGTGGAGAGAGACCGTCGCGAATATATATACTCCTGCCAGATGTTATCGCCTAGCCGGTAATTAAATATTTCGACCGTT
ACAACACTACATTCGCCGACAGTGATGGAGCTCTAGCTATTAAACGGCTAGAAAACGGAACCCTTCAAAAGTAACGATACATATATGCATTGAAA
CGATGGATATTCTTACTTTCCTTAGAACTTCTTCGATTATTTATACAATAATTTATTTGTTGATAAAGCACAATAATATTACAATCGCAGCTTAA
GAGTAAATACGATACTGAACAGAAAGGGACATGCGGAATGGGTTGGGAACTATACTCCAAGGTCTACCACAGTTTGTCGCTGAACACGATCTCCT
TGAAGATGCAATCCTGCTTGGCGATGCTGACCATTGCCTTCTTCGACTTCATGGCATCCTGCACCTTCTCGCGCACCTCGGCCGCCTTCACATCG
TTGCGAATGTAAAAGAGCCGTACCAGGTGGTCCTCGTTCAGAGACGGATAGCTGCCCAGCAAGGTGTGCAGGTCCAAGACGAGCAGTTCGATATC
CGAGCTAAGCAGTGCCGATAGCGTGGATATAAGATCCAATGGAGAGTCGCTGAGGGAAATCTTCGGCGCGATTTTCTCAAAGAAGAGCTTAAACC
GCTTGGCTTCGGTCTTGATTTTTCGCGTAATGGCATCGCACTCGGCCCGTGGCTTAGACAGTCGCTTGGATAGCAGTGCCCTAATGTAGCGCTTG
GCCAGCAGCTTCTGGGCCTCGTTGATGACCATCTCGAAGTTATTGGGTCGCAGGTGATTATAGTCCTGGAAGTAATCGTCCAGCGTTACACAAAT
GGTGTCCACGGCAATGTTACTGGCCAGCCACTTGGCAGTGAATAGGTCGTTAAAGTGACACTCCATGTCCAGGAAGGCTTCCTCCAGCAAGTAAC TTGCGGCATGAGCCCGGATCCGCTGGAATGTGGCAAGCAAACGTTCGAAATCCTCATAATGCTCAGTACGTGACTTGGGCCAGTAGAGTTGTTTC
ATCTGCTGCGCCAGTTCAACCATTTGCTGACTGTTATTCACGATGGTGATGATGTAGTGAGTGAAGTATTTGATCTGGTCCCGATTGCGAAAATG
GTGTTCCTTCAGCTCGATTACGTTCTTAAGATATGTCTGGCCAAAGATCTCCACCTGCTGAATGCTCATTACCAACGCCTTGAACGTCAGTTCCT
GATGAATTGTGTTGGTCACCTGCAGATGCTGGTCGATCATCTGGAATATGATGACAGGCGCTGAAGTGTGGTAGTACTCCTCATCCTGATCGGGC
ACCGTCTCAGTAAACCACTCCTGCTTCTCCGTTTCTGCGGCCTTGGTCATCCATTCCTGGAAGTTTCTCTGCATATTTTGCAGATATTCATCTTC
CAGCGCTTTGAGATGTTCCGGACGCAGCAGAGTACCTATCTGTCGGTGTACATCCACATTAAGATCCGGATGGGACATCAGCTCGACGCCAGGAT
AGGTGTGTGTAACCCAAGCCATCATTGATACATATTCATTGCCCTCCAAGCCCGAGCGCACAATGTTGTCAAGCTGGAATTAGTAAATATTAGTG
GTATAAAAACATTAATCAATTTAAATGATTGACGATTACTCACATAGCTAGAAAGTCCTTCGTGATAGAACTTGACATATTCGCCGAAAATGTCG
TAGTGCGGCGGGAAGCAGGGCACACAAAGGGACTTCACAACGCGCAGATCCTCGAGAATGATTTGACGCAATATCTCCAGGTCTCGTACTAACCA
CATCTTGTTATCGGCCCGCTCCTCTAGCTTGGATCCCTCTATGCGCGTTATCACCGACTGTTGTAGCACGTCCATGATCATGCGGCGCCAAGCCT
TTGGTCTTCCAGGCGGCAGGAATCCTGTGACCTTTTGCTGCTGCAACGCGAACTGGTCGTTTTTCTCTTCCCGCTCTATGATGCGTAGGGCGGTA
ACGATGATGGTGGGCTTCTTGCGCAGAGTGTTCAGCGTGCGGCTAAGAATGAGTCGCAGCTTTTTCTCCAGCTCTTGGGATACCGTGTCAACCTT
CTCGAAGTGACGCTTTAGGGTGATCTTGTCGGACGCATGCTGCTTGGGCTGCTTGTGCAGTTCGTAGAGAAGATCATCCCGCGAATTCTCCAGAT
CCGCCAGGCACTGATGGGCATTAAGCAGCTTATCATCCTCGATCAGCGCCATCGTCTTTTGTACGCTGGCATCTACGTTGAAGATGTGCTTCAGA
TTCTCCATGGCGGTGGCGTACTGGGAGTGCTTTGTGTTTTCCTCCCGCACAACTTCCAAAGCGTCGTAGACTTCGGGAACGCCCCTCAGCAGGCG
CTCCACCTCGTCCATTCGACGCCTTACCTCGCGCACGTCCTGCATGCAGGTCTCCAACTGCTTAAGTCCCACCCTGACCCCGTCCAGCTGTCCTT
GCATTCCGGTCTTAAGGAGCGCCTCAACGGATGCCTTCTTCCGGGCGATTCGGTGGCGATATTGTTCCACCTTCTCCAGTTGACCTGGTCGCTGC
AACATGTTCTGTATGTCCTTGAGCGCTGCCTGGCGAGCCTGCTCCTCCAGCTGCTGTAAATCCATCTTCAATTTATTTGGATCACTTTCAGTCTC
TGTTTTGGTCAATCTTCGTCAGCAGTGGAAGTGCTGGTGTGACCATATAGCAGTGCGGCTGACAATCTCACTTCCAAGAACTACAGTGTAACTTG
ACAATAAGCTATATTCTACTCTTAAAATTATTATAGTTTTATTGTGTCTTAAAATTTTTATTTTATTCTTCAAGCTTAAAAAATTATGAAGTTAA
AGTATATCTTTTAGTTTGCCAAAGCAACAGAGGATTCGACCTAAGTATGGAAAACTGTACTTATCGATAAGTTATCTTCTCATTGGTCTATCGCC
ATCGAGAGCTTTGTTTGTTTATAATTTGCAGCCAAACGTTTGAACGTAAACAACGCCCTAAGCAAAACATGAGCACGGAAAAAGAGATAATTTTG
CAATTTGCTCCGTGGGAATCTTTTGTGTCGCCCACTTTCTGGCACAAGCTAGCGGAGCTTAAGCTCGACCACGATCGCCTGTCCGACTCGAAACG
CTCCATTACTGGACACTACACAAATCGTAATGCAAGTGGATGCCTTTTGGAAGTAGACTACACGGCCTACAACAGGTGAGCTTGAAAACTACGAG
TTTGATGAAACCAGCGCTTGACCACCCACATTCCAGAATGGCAAAGCCTCCAAAATTCAGCCATTCCGCTATAGGCACCATCTACAATAAGAACA
CAATCGAAGAGTTCAAGGCCCTGGACAAATTACAACTGCTGGCCGATGAGGGCAAGGAACTGCTGGCTGATATGTGCAGTGGTGGCGCCTTGAGA
GATCCCAGTCTATTGACCCGGTTCTTTGTTCTCTCCTTTGCCGATTTAAAGTGTCACAGCTACTACTATTGGTTCGCCTTTCCGTGCCCGCTGAC
GCCCACCTTAAAGCTTCAGGGAGCCGTCCAAAAACTGCGGGACTTGCCCAATAGTAGTAGCTATATAATGGCTCTAAAGGCCTTACCCACTGAGT
CACAGAACTTCTTCATTCTGTATGCTAATGTGGAGAAGAACATTTTCGAAGCCCGTAGTTTAAGTTCCCTTGACGATAAAAATGT
(SEQ ID NO: 592)

Exon: 3455..3163
Exon: 3060..2692
Exon: 2622..2419
Exon: 2353..1001
Start ATG: 3390 (Reverse strand: CAT)

Transcript No. : CT16986
AGCACTTCCACTGCTGACGAAGATTGACCAAAACAGAGACTGAAAGTGATCCAAATAAATTGAAGATGGATTTACAGCAGCTGGAGGAGCAGGCT
CGCCAGGCAGCGCTCAAGGACATACAGAACATGTTGCAGCGACCAGGTCAACTGGAGAAGGTGGAACAATATCGCCACCGAATCGCCCGGAAGAA
GGCATCCGTTGAGGCGCTCCTTAAGACCGGAATGCAAGGACAGCTGGACGGGGTCAGGGTGGGACTTAAGCAGTTGGAGACCTGCATGCAGGACG
TGCGCGAGTACGCCACCGCCATGGAGAATCTGAAGCACATCTTCAACGTAGATGCCAGCGTACAAAAGACGATGGCGCTGATCGAGGATGATAAG
CTGCTTAATGCCCATCAGTGCCTGGCGGATCTGGAGAATTCGCGGGATGATCTTCTCTACGAACTGCACAAGCAGCCCAAGCAGCATGCGTCCGA
CAAGATCACCCTAAAGCGTCACTTCGAGAAGGTTGACACGGTATCCCAAGAGCTGGAGAAAAAGCTGCGACTCATTCTTAGCCGCACGCTGAACA
CTCTGCGCAAGAAGCCCACCATCATCGTTACCGCCCTACGCATCATAGAGCGGGAAGAGAAAAACGACCAGTTCGCGTTGCAGCAGCAAAAGTCG
GTGATAACGCGCATAGAGGGATCCAAGCTAGAGGAGCGGGCCGATAACAAGATGTGGTTAGTACGAGACCTGGAGATATTGCGTCAAATCATTCT
CGAGGATCTGCGCGTTGTGAAGTCCCTTTGTGTGCCCTGCTTCCCGCCGCACTACGACATTTTCGGCGAATATGTCAAGTTCTATCACGAAGGAC
TTTCTAGCTATCTTGACAACATTGTGCGCTCGGGCTTGGAGGGCAATGAATATGTATCAATGATGGCTTGGGTTACACACACCTATCCTGGCGTC
GAGCTGATGTCCCATCCGGATCTTAATGTGGATGTACACCGACAGATAGGTACTCTGCTGCGTCCGGAACATCTCAAAGCGCTGGAAGATGAATA
TCTGCAAAATATGCAGAGAAACTTCCAGGAATGGATGACCAAGGCCGCAGAAACGGAGAAGCAGGAGTGGTTTACTGAGACGGTGCCCGATCAGG
ATGAGGAGTACTACCACACTTCAGCGCCTGTCATCATATTCCAGATGATCGACCAGCATCTGCAGGTGACCAACACAATTCATCAGGAACTGACG
TTCAAGGCGTTGGTAATGAGCATTCAGCAGGTGGAGATCTTTGGCCAGACATATCTTAAGAACGTAATCGAGCTGAAGGAACACCATTTTCGCAA
TCGGGACCAGATCAAATACTTCACTCACTACATCATCACCATCGTGAATAACAGTCAGCAAATGGTTGAACTGGCGCAGCAGATGAAACAACTCT
ACTGGCCCAAGTCACGTACTGAGCATTATGAGGATTTCGAACGTTTGCTTGCCACATTCCAGCGGATCCGGGCTCATGCCGCAAGTTACTTGCTG
GAGGAAGCCTTCCTGGACATGGAGTGTCACTTTAACGACCTATTCACTGCCAAGTGGCTGGCCAGTAACATTGCCGTGGACACCATTTGTGTAAC
GCTGGACGATTACTTCCAGGACTATAATCACCTGCGACCCAATAACTTCGAGATGGTCATCAACGAGGCCCAGAAGCTGCTGGCCAAGCGCTACA
TTAGGGCACTGCTATCCAAGCGACTGTCTAAGCCACGGGCCGAGTGCGATGCCATTACGCGAAAAATCAAGACCGAAGCCAAGCGGTTTAAGCTC
TTCTTTGAGAAAATCGCGCCGAAGATTTCCCTCAGCGACTCTCCATTGGATCTTATATCCACGCTATCGGCACTGCTTAGCTCGGATATCGAACT
GCTCGTCTTGGACCTGCACACCTTGCTGGGCAGCTATCCGTCTCTGAACGAGGACCACCTGGTACGGCTCTTTTACATTCGCAACGATGTGAAGG
CGGCCGAGGTGCGCGAGAAGGTGCAGGATGCCATGAAGTCGAAGAAGGCAATGGTCAGCATCGCCAAGCAGGATTGCATCTTCAAGGAGATCGTG
TTCAGCGACAAACTGTGGTAGACCTTGGAGTATAGTTCCCAACCCATTCCGCATGTCCCTTTCTGTTCAGTATCGTATTTACTCTTAAGCTGCGA
TTGTAATATTATTGTGCTTTATCAACAAATAAAT
(SEQ ID NO: 593)

Start ATG: 66 (Reverse strand: CAT)

MDLQQLEEQARQAALKDIQNMLQRPGQLEKVEQYRHRIARKKASVEALLKTGMQGQLDGVRVGLKQLETCMQDVREYATAMENLKHIFNVDASVQ
KTMALIEDDKLLNAHQCLADLENSRDDLLYELHKQPKQHASDKITLKRHFEKVDTVSQELEKKLRLILSRTLNTLRKKPTIIVTALRIIEREEKN
DQFALQQQKSVITRIEGSKLEERADNKMWLVRDLEILRQIILEDLRVVKSLCVPCFPPHYDIFGEYVKFYHEGLSSYLDNIVRSGLEGNEYVSMM
AWVTHTYPGVELMSHPDLNVDVHRQIGTLLRPEHLKALEDEYLQNMQRNFQEWMTKAAETEKQEWFTETVPDQDEEYYHTSAPVIIFQMIDQHLQ
VTNTIHQELTFKALVMSIQQVEIFGQTYLKNVIELKEHHFRNRDQIKYFTHYIITIVNNSQQMVELAQQMKQLYWPKSRTEHYEDFERLLATFQR

IRAHAASYLLEEAFLDMECHFNDLFTAKWLASNIAVDTICVTLDDYFQDYNHLRPNNFEMVINEAQKLLAKRYIRALLSKRLSKPRAECDAITRK
IKTEAKRFKLFFEKIAPKISLSDSPLDLISTLSALLSSDIELLVLDLHTLLGSYPSLNEDHLVRLFYIRNDVKAAEVREKVQDAMKSKKAMVSIA
KQDCIFKEIVFSDKLW*
(SEQ ID NO: 594)

Name: sec6 -like
Classification: transporter

Celera Sequence No. : 142000013384663
TTAATTCTCATTTTGTCATTCAGCTGAAGCTGCTTGGCTATCTAATGGGTACGATATTAATTGGAGTGGCTGGCGTCGCTATTTATCGTTACAAG
TACTAAGGACAAGCATTGCACACGAACTACTGGTTATTTAAGCAATTGAAATGCATTTTTTAAGTATATATAGAAGGCAAAATTATGAATGTTG
GAAAGTCGCAGTTGCTTATTATGATGATATGGCTCTCGTTGTACATTTAATGCTATGCACACTTCACAATAGTATGTATCTTTCAAATAGTATGG
TTTTGGATATCGTACATATAATGTTAAAGCTTAAGTTTAATCAACTACATTCTGTCAGACAAGTAACGGGAATTGTTAAAATAAACACAATATTC
TCATCATTATGTTTTATACAATTTTCAAACGAAATAAAGCAACACAATCGAAATCAGACCATATTTATGAACTTGCAATAAGGTTCGAAAGAAAG
CATATGAAATACCATATGAATGTAATGATACTGATAAGAGCAGCACTGATAAGAACTCCTAACTTGATTTTTTTTGTTCGTTACTTAAATAATGC
ATGATTTAACTAAACTCTGCTCTAATCTAAAAGGCAAACGAACTTTTGTAAAAACAAATCGGAACATCCGTTCAAGAGATATAATTTTCTTCTAT
CGCGACTTAGAATGATTAAATGATGGTGCGAATTTAAACATGCTGATTCATTGTTTGCGTATGGTAATCGACATGACAATGGGTATATTTGGGTC
TCCCAAGGCTGTTTCTATGGGGGGTCGTGGAGGTAATGCAGCTGCGATCGTATATAAACCTATCAAGACATCAACAATTTTCAGTATCTGATCAC
TATATCAACAATAATTGTGAAAAAAAAACCAGCAATAACACAAAGCTTTATTTACCACATCTTATCAGTTCGCCACAATCTGTAATATCTATTCG
ATCTATCCAGAAAGTCTATATGTTTACAAACGTATGTTTATAAGCAAGTGTTTATAAATATCTTTCATTTGAGACAAAACACTTTTATTGGGGTG
ATTAATATACAAATTCATAAGCTTTCGGTTAAACAAATTCCTGCGAAAAATAAAAAAAATACATGTGATGCGAGTAACTTAGGCCTTCGATGCAA
TTTCAAGGGCCTGCTCCAGATCCTTGATCAAATCATCGGCATCCTCCAGTCCGACGGACAAGCGAACTAGACCGTCAGTGATGCCCAAAGTTTTC
CTATCCTCCGCTGGAACCGAGGCATGGGTCATTATTGATGGAAGCTCGGCCAGACTCTCGTAGCCACCCAGACTCTCTGCCAGGGTGAACACCTT
GAGGGCCTTGAGGAAAGCCGAGGAGTGCTTCAGCTCGCCCTTAATGTAGAAGGAGAACACGCCGCTGTATCCGTATGCCTGCTTCAGAGCGATCT
TGTGCTGCGGATGGAGGGCAAAGAGGGATGCAACACCTTCTCCACGAACGGATTCGTCTCCAGGTATTTGGCAACCTTCAGAGCATTCTTCTGG
TGCTGTTCCATGCGCAGCGAGAGCGTCTTAAGACTTCTGTTCACCTGATAGCAGTCGAATGGAGACGGCACAATGCCCACTGCGTTCTGCAGGAA
CTTCAAGCTTTTGTAGAGCTTCTCCGAGTTCATGGTGATGCCACCCATGACCACATCCGTATGACCGTTCATGTACTTGGTCAGGGAGTAGCAGA
CCAGATCAGCGCCCAGCTCCAAGGGTCGCTGGAAGTAGGAGGTCAGGAAGGTGTTGTCGACGGCCAGGACGATATCCTCGCGTACTCCATGGACC
AGCTGCGCAATAGCCTCGATGTCGGCTACCTTTACCAATGGATTAGTTGGTGACTCGATCCACACCAACTTGGTCTCCGGCTTGATGGAACTTTT
AATTAGATCCAACTTCGTGGGATCCACAAAGGTGGCTGAGATTCCCAGACGGGTGGCAACCTGTCGGATCAAACGGTTGGTGCCTCCGTAAACAT
CGTCGCCCATGATGATGTGATCGCCGCTGCTCAGCATAGTTAGCACAGCGGTGGTGGCTCCCAATCCCGATGAGAACGTGAGGCCGTATTTGGCA
TTATCCAAGGCGGCGAAGCACGTCTCCAGCACGTTCCTAGTGGGATTTCCACTGCGGGAGTACTCATAGCCCCTGTGCTCGCCCGGTGCATCTTG
CTTGAAGGTGGTGCTCAGCGATATCGGCGGAATCACGGCAGCACTCTTCCACTGGTCGGGGCTCTGGCCCGAGTGGATGGACTTGGTGGCGAAGC
CGCTCGGCTGGACTCTGTAGCTCATCTTGTCTGGGTAGGAGGATCGTTGGGAACTGACTGACACGTGGAGAGAGACCGTCGCGAATATATATACT
CCTGCCAGATGTTATCGCCTAGCCGGTAATTAAATATTTCGACCGTTACAACACTACATTCGCCGACAGTGATGGAGCTCTAGCTATTAAACGGC
TAGAAAACGGAACCCTTCAAAAGTAACGATACATATATGCATTGAAACGATGGATATTCTTACTTTCCTTAGAACTTCTTCGATTATTTATACAA
TAATTTATTTGTTGATAAAGCACAATAATATTACAATCGCAGCTTAAGAGTAAATACGATACTGAACAGAAAGGGACATGCGGAATGGGTTGGGA
ACTATACTCCAAGGTCTACCACAGTTTGTCGCTGAACACGATCTCCTTGAAGATGCAATCCTGCTTGGCGATGCTGACCATTGCCTTCTTCGACT
TCATGGCATCCTGCACCTTCTCGCGCACCTCGGCCGCCTTCACATCGTTGCGAATGTAAAAGAGCCGTACCAGGTGGTCCTCGTTCAGAGACGGA
TAGCTGCCCAGCAAGGTGTGCAGGTCCAAGACGAGCAGTTCGATATCCGAGCTAAGCAGTGCCGATAGCGTGGATATAAGATCCAATGGAGAGTC
GCTGAGGGAAATCTTCGGCGCGATTTTCTCAAAGAAGAGCTTAAACCGCTTGGCTTCGGTCTTGATTTTTCGCGTAATGGCATCGCACTCGGCCC
GTGGCTTAGACAGTCGCTTGGATAGCAGTGCCCTAATGTAGCGCTTGGCCAGCAGCTTCTGGGCCTCGTTGATGACCATCTCGAAGTTATTGGGT
CGCAGGTGATTATAGTCCTGGAAGTAATCGTCCAGCGTTACACAAATGGTGTCCACGGCAATGTTACTGGCCAGCCACTTGGCAGTGAATAGGTC
GTTAAAGTGACACTCCATGTCCAGGAAGGCTTCCTCCAGCAAGTAACTTGCGGCATGAGCCCGGATCCGCTGGAATGTGGCAAGCAAACGTTCGA
AATCCTCATAATGCTCAGTACGTGACTTG
(SEQ ID NO: 595)

Exon: 2354..1001
Start ATG: 2305 (Reverse strand: CAT)

Transcript No. : CT17004
CTCTCTCCACGTGTCAGTCAGTTCCCAACGATCCTCCTACCCAGACAAGATGAGCTACAGAGTCCAGCCGAGCGGCTTCGCCACCAAGTCCATCC
ACTCGGGCCAGAGCCCCGACCAGTGGAAGAGTGCTGCCGTGATTCCGCCGATATCGCTGAGCACCACCTTCAAGCAAGATGCACCGGGCGAGCAC
AGGGGCTATGAGTACTCCCGCAGTGGAAATCCCACTAGGAACGTGCTGGAGACGTGCTTCGCCGCCTTGGATAATGCCAAATACGGCCTCACGTT
CTCATCGGGATTGGGAGCCACCACCGCTGTGCTAACTATGCTGAGCAGCGGCGATCACATCATCATGGGCGACGATGTTTACGGAGGCACCAACC
GTTTGATCCGACAGGTTGCCACCCGTCTGGGAATCTCAGCCACCTTTGTGGATCCCACGAAGTTGGATCTAATTAAAAGTTCCATCAAGCCGGAG
ACCAAGTTGGTGTGGATCGAGTCACCAACTAATCCATTGGTAAAGGTAGCCGACATCGAGGCTATTGCGCAGCTGGTCCATGGAGTACGCGAGGA
TATCGTCCTGGCCGTCGACAACACCTTCCTGACCTCCTACTTCCAGCGACCCTTGGAGCTGGGCGCTGATCTGGTCTGCTACTCCCTGACCAAGT
ACATGAACGGTCATACGGATGTGGTCATGGGTGGCATCACCATGAACTCGGAGAAGCTCTACAAAAGCTTGAAGTTCCTGCAGAACGCAGTGGGC
ATTGTGCCGTCTCCATTCGACTGCTATCAGGTGAACAGAAGTCTTAAGACGCTCTCGCTGCGCATGGAACAGCACCAGAAGAATGCTCTGAAGGT
TGCCAAATACCTGGAGACGAATCCGTTCGTGGAGAAGGTGTTGCATCCCTCTTTGCCCTCCCATCCGCAGCACAAGATCGCTCTGAAGCAGGCAT
ACGGATACAGCGGCGTGTTCTCCTTCTACATTAAGGGCGAGCTGAAGCACTCCTCGGCTTTCCTCAAGGCCCTCAAGGTGTTCACCCTGGCAGAG
AGTCTGGGTGGCTACGAGAGTCTGGCCGAGCTTCCATCAATAATGACCCATGCCTCGGTTCCAGCGGAGGATAGGAAAACTTTGGGCATCACTGA
CGGTCTAGTTCGCTTGTCCGTCGGACTGGAGGATGCCGATGATTTGATCAAGGATCTGGAGCAGGCCCTTGAAATTGCATCGAAGGCCTAAGTTA
CTCGCATCACATGTATTTTTTTATTTTTCGCAGGAATTTGTTTAACCGAAAGCTTATGAATTTGTATATTAATCACCCCAATAAAAGTGTTTTG
TCTCAAATGAAAGATATTTATAAA
(SEQ ID NO: 596)

Start ATG: 50 (Reverse strand: CAT)

MSYRVQPSGFATKSIHSGQSPDQWKSAAVIPPISLSTTFKQDAPGEHRGYEYSRSGNPTRNVLETCFAALDNAKYGLTFSSGLGATTAVLTMLSS
GDHIIMGDDVYGGTNRLIRQVATRLGISATFVDPTKLDLIKSSIKPETKLVWIESPTNPLVKVADIEAIAQLVHGVREDIVLAVDNTFLTSYFQR
PLELGADLVCYSLTKYMNGHTDVVMGGITMNSEKLYKSLKFLQNAVGIVPSPFDCYQVNRSLKTLSLRMEQHQKNALKVAKYLETNPFVEKVLHP
SLPSHPQHKIALKQAYGYSGVFSFYIKGELKHSSAFLKALKVFTLAESLGGYESLAELPSIMTHASVPAEDRKTLGITDGLVRLSVGLEDADDLI
KDLEQALEIASKA*
(SEQ ID NO: 597)

Name: ECDYSTEROID-INDUCIBLE POLYPEPTIDE EIP40
Classification: enzyme
Gene Symbol: Eip55E
FlyBase ID: FBgn0000566

Celera Sequence No. : 142000013384546
CGCGCTTAGTACTCGATAACAAATCGTCGGCGGGACTGGACTACCGACTATTTCAACGAATCATTCGATTCCCGATTGCTTCCGTGAAATCGATA
TTTTCTGACCCAGCTTCATGACATCCCTGTTGAGTTGAATACGCAAAGGTGGCAACCTTATACGGCGACTGAATAAAATAAAAGTGGAATTGTAA
ATTATAAGTGTAAGCACTAGCAATGGCTGCCACCCCAAGCGCACCCGCCAAGTCCGAGATGATCGACCTGACCAAGTTGAGTCCGGAACAGCTGA
TTCAGATCAAGCAGGAGTTCGAGCAGGTGCGTTCCGCATGTGGGTGTGTGATGAGTCAAGTGTGCTCGCGGAGGGGGTTTCTGGAGGAGGGGCGC
CCCAATTGGCACATGCTTCTAAAATCGGTACATTTTTGTGATCCTTAGGAGATTACCAACGTACAGGACTCGCTGTCGACGCTTCACGGCTGTCA
AGCCAAGTACGCCGGATCCAAGGAGGCGCTGGGAACCTTTCAACCCAATTGGGAGAACCGTCAGATCCTGGTGCCCCTGACCAGCAGTATGTATG
TGCCAGGACGGGTCAAGGATCTCAACAGGTTCGTCATAGACATCGGCACCGGCTACTACATTGAAAAGGTGATTTACATTTCCAATCGAACCTAG
AATATTTATTGATTGCCATCTGTTTCTCAAACAGGATCTGGAAGGCTCCAAAGACTACTTCAAGCGACGCGTGGAGTACGTGCAGGAGCAGATCG
AGAAAATCGAAAAGATCCACCTGCAAAAGACGCGCTTCTATAACTCAGTGATGAGTGTGCTGGAGATGAAGCAGGCTGCTGCAGCGAAATTGCAG
TCGCAGCAGCAATCGCAGCCGGCGGTTACCCAGAGCTCCTAGACTACGGAGAACGACAGAGACACGAGACACGGAAAGCATTAAATTATTAAACT
TATTAACGAGATGTGTGCATTTAATTAACGTAGTTTATTAAATTGTTCAGCTATTTCTTGGCTTCTGCCAAAGCCTTGGTGAGAACCTTGACCTT
CTGCTCGTACGCGGACTTAAGATCCTGTAGGGAAAGAAGGTAATAGTATATCAAGTATATCATTGGACTCGAGTTATAAGGCACCTTGAATATCT
GTGACTGGGTGTCGTACTCCGAACGCAGCTTGTCATACACTCCTTTGGAGATGGCTAGTTTCTTCTCCGTGAGCACACACTTGTCTTGCTCCGCC
TTGATCCACTGCTGGCTCTTCTCCAGACGAGCCTGCGTGTGATCACATTCGGCGGTCTTTAGCTGCAACATGTCCTTGGTCACCTGCAGCACATC
CTTAATCGAGTCTACTTGTGTCCTAAGCACTGATATCTGCTGCTCCTGCTGTTTGTTCACCTTGGTCTTCTCGAACAGCAGGGTTTTGGCCTTTA
GAAGCAGCTCCTCCTGCTCTTGTCGTGATTTGGGAGCATCTGTGCCGCCCAGCATGACGGACTGCTTGAGCGACTGCTCCAACTGGACCACTCTC
CGCTTTAAACGCTCATTTTCCGCCTTGGCTTCCTGCAATCAGGGTCAGTAAGTGGGTGCAGCCCGTGGAGACGAGTAACTAACCTCAAAGTCTTT
GCGGAGCGCTCCGATCCGTTTGCGAGACTCCTCTAGTAGTGCCTGTTTTTCGCTTTCCAACGTGAAAACCATGTCCAGCAGTTCGTTCTGCGGCT
GCTCCGGCTGACGCACTTCCTCCTGCCCATTTGCTGTTATATTGTTGTTTAGGTCACCGCCAACAGCTTCATCTTCGTTATGATCGGCCATTTTA
TGAAGAATTCTTTTTAAATGATAAAAATTCGTAGAGCAATGTGCGTTTTCCGTGCTTTTTGGGATGTGTTTTCTTTTTGTATTAATAGACCAAAT
AGATGCACGCTCTATTTATAGGACATCCCACTCTCCGGATCGCTCTCTGCCTGCTCTTGGCCAGATCGCTCTCCCGAAATAACAAACTGTTTCCC
TCCAATTTAGTTTACGCCTCAGCATATTCTGAAGATCAGTTTATTATACATTGAAGCATGGATGAGAAAGGATTGCGGATGTGCGGTGTTAATAC
AGATCGCGAAGGGCAACACAATTAAATTGTTGTTACAATCAATGGGGCGACAATTGAAAGTGAGTGATTTGATTAAAATTAAATGCCTAAACAAG
ATAGAAGAAATGTGCTTCGCTCGCGGTGAAGAATGCTAACCGTCCAGCTCGCCGGCAGCGCATGCATCGGCGTAACTCTTGCCGCTCTTGTCCT
CCGGATTCAGCTTGATCATGTCGTCAATACGCAAAATGGTAATGGCGGCCTCCGTGGCGAACTTCAGCGACTTGATCTTGGACATGGCGGGCTCC
AAAACTCCAGCCTTCTTGTTGTCCCTTACCACTCCCTCGATCAGATCCAGACCGGTCCACTTAAGATCCGAACGCTCGGGCTTCGTCTGGCTGGA
GTTGTGGTAGGAGCGGAGCTTGGCCACTAGATCAGTGGCATCCTTGGCCGCGTTCACGGACAGAGTCTTGGGAATGACCAGCAGCGACTTTGCGA
ATTCGGCAATGGCCAGCTGTTCGCGGGAAGCCAGCGAGGTGGCAAAGTTCTCCAGGTAGATCGACAAAGCAGCCTCCACACAGCCGCCGCCGGCT
ACAACCTTCTTGCTCTCCAGCACACGCTTCACCACGCACAGAGCGTCGTGGACGGAGCGCTCCATCTCATCACAGTAGAAGTCATTGGGACCACG
CAAGATAATGGATGCGGCAGCACTAAAAAGGCATAGGGATACGATAAAGCAAACTATGTTACTGCATGATATAATCTGCACTTACCGTGCCTTAG
TGCCCTTGATGAGGATAAGTTCAT
(SEQ ID NO: 598)

Exon: 1874..1604
Exon: 1552..1130
Exon: 1069..1001
Start ATG: 1801 (Reverse strand: CAT)

Transcript No. : CT17018
ACACATCCCAAAAAGCACGGAAAACGCACATTGCTCTACGAATTTTTATCATTTAAAAAGAATTCTTCATAAAATGGCCGATCATAACGAAGATG
AAGCTGTTGGCGGTGACCTAAACAACAATATAACAGCAAATGGGCAGGAGGAAGTGCGTCAGCCGGAGCAGCCGCAGAACGAACTGCTGGACATG
GTTTTCACGTTGGAAAGCGAAAAACAGGCACTACTAGAGGAGTCTCGCAAACGGATCGGAGCGCTCCGCAAAGACTTTGAGGAAGCCAAGGCGGA
AAATGAGCGTTTAAAGCGGAGAGTGGTCCAGTTGGAGCAGTCGCTCAAGCAGTCCGTCATGCTGGGCGGCACAGATGCTCCCAAATCACGACAAG
AGCAGGAGGAGCTGCTTCTAAAGGCCAAAACCCTGCTGTTCGAGAAGACCAAGGTGAACAAACAGCAGGAGCAGCAGATATCAGTGCTTAGGACA
CAAGTAGACTCGATTAAGGATGTGCTGCAGGTGACCAAGGACATGTTGCAGCTAAAGACCGCCGAATGTGATCACACGCAGGCTCGTCTGGAGAA
GAGCCAGCAGTGGATCAAGGCGGAGCAAGACAAGTGTGTGCTCACGGAGAAGAAACTAGCCATCTCCAAAGGAGTGTATGACAAGCTGCGTTCGG
AGTACGACACCCAGTCACAGATATTCAAGGATCTTAAGTCCGCGTACGAGCAGAAGGTCAAGGTTCTCACCAAGGCTTTGGCAGAAGCCAAGAAA
TAG
(SEQ ID NO: 599)

Start ATG: 74 (Reverse strand: CAT)

MADHNEDEAVGGDLNNNITANGQEEVRQPEQPQNELLDMVFTLESEKQALLEESRKRIGALRKDFEEAKAENERLKRRVVQLEQSLKQSVMLGGT
DAPKSRQEQEELLLKAKTLLFEKTKVNKQQEQQISVLRTQVDSIKDVLQVTKDMLQLKTAECDHTQARLEKSQQWIKAEQDKCVLTEKKLAISKG
VYDKLRSEYDTQSQIFKDLKSAYEQKVKVLTKALAEAKK*
(SEQ ID NO: 600)

Celera Sequence No. : 142000013384832
ATGCAATATATTCAACTACTATCATTATTTTGCGGATCGGCGATTCTTAAGGTTGCGTTCCAGTTTGTGATGAGGCTTGCCTTCGTTCTTTCCTG
TCTTCTGAGTGATTCTTTGAGCATCCCGACTGCGAGTTTGGCGCACGGATTGCTGGGCATCCTTGGGAGGATTGGTTTTACGCTGCTTTGGAGGC
GGCGGCGTGAAGGATTCGTCGCTATCGTCTAGGTGGTCCTCATAGAGAGCATCGTCTTCTAAGTATTCCGTCACGAATTCTTCCTGCTTCACATT
GTCCATGTCTTCAAAATCGTCAAGATGTTCCTCCTTCTCATCGACGCCGCCTTCTCCTTCGCCGTCGTCTTCGAACTCGTTCTGGTACGGCTCCA
TTTCCACCACATGATCGTCCTCGATGTGGCGCTGCAGGCATTTCTGCGTCAAGAAGATGTGGTCACAGAACTCGCAGGCATGGCGCTCGCTCTGC
TTGTGCTGGTCCATGTGGCTCTCGACACTGTCGATATCTTCGATCTGCTTGCGACACATGGGACATTTCAGGCTGGCGGTGGCATGAATGAGCGC
ATGATCCAGTAGGTCGTTATAGTTGCTGTACGACACCTTGCACTCACTGCACACGAACGAGGCGTCGGAAGTCTGCGTGTGCGTGCGCAGGTGGC
GCGAGAGATGATGCGACAGCATGTAGGACTTGTGGCAGTACTTGCAGGGATAGGCTCTCTTCCCGGCGTGGGCAACCAGGTGGCGGGCCAGCTTG
GAAGCGGTGGAAAAGCTTCTCTCGCAATGCTGACAGGGGAAGGGAAGATTGGTGGAGTGGACTGTCTGAAAGTGGACATAATCGTTAGCCGGGGC
AATCCCAAATATGCTTGTCAACCCACCTCATGACGCTCCAATCCCTGCTTGAAGGCAAACGACTTGGTGCAGACACCGCATTGGAACGGACGCTT
CTTCTGATGTCGCTCGGCGTGCTTCTCCATCTCCTGGCGCGAAAGGAAGGGCTTCTCGCAGTACACGCAGATGAACTTGGGTACGTCCGTGTGGG
TGCGCTCGTGGCGATGGAGCAATGCCTTCCGTGTGAAGGCTTTCGAGCAGATGGCGCACTTGAATGGCCGCTCGCCGGTGTGCACAAAGTTGTGC
TTGGCCAGGTCGTACTTGGAGAAGAAGCTCTTCTCGCACAGGAGACACTGGAAGCTGCGCGAGCGAGTGTGATTCAGCCGATGGATCTCGAGCAG
CTGCTGCAGCGGAAAGGAGCGTTCGCAATCGGGACAGGGGAACACATCGGTGGCCACCTTCTCGGCGTTCTTGGTCGGATCATCTTGATCGTCCA
ATGGCAGATCCGAGTCCAGAACCTCTGTCACTATGGCCACATTGCCACTATCATCTCGCTTGACTTTGGGTGTGGCCAGGCGCGGTTCCACCGGA
GCGGCGGGTCCCTTGTTCAAGATCCTAATCGAGGACTTGTTCAGCACCTTCGGCTTGACGGGTGATGCCTTCTGGGGGATATCGGGGAACTCCTT
CTCTAGCTCACTGGCCATATCCTCCAGCATGCTCTGCACATCGTCCATGGACAGCTCCTGGTTGTTATCCACCTTCAGCTCATAGGCGTGCGAAC
GACGTGGCACTGGAGAGGAACCGGCTACCGTCCTGGGGGTCACCATGGCGCTCTCCAGCACCTGGACGTCCTCGATGATCACCTGACTACTGGAT
TTGGCCATTGTGTTCAGCAGCTTTTTGGGCGTTTCGCTTGGCTCGGCTGTCTTTGCTGGCACGACCAACAACTTCTTGGAAGCCACCATCGTCAT
GGGCGCACGGGGCTTCTCCAGCGGCGATGGCCAGTTACCCGTGAGCGGATACTGGCGCAGGAGGGTCTCCGCCCGCTTGCACATCTGCTTGAAGC
GGTAGCAGTGCTCGAAGAGGAGGCGGCACTCCAGACAGATGTGCCCCGGCATTCCGTCGCCGGCGTAGACCTGTTTTTAATGTTAGATTAGATAA
ATGTGTGAGTGACTAGGAAGCTACATTTATTCGGGGAAGTCCGTGCTTAAGCCAAATAATAAGGTAATATTCGTGGAACACCCCTATATGTTTTT
CGCTACATAATAAATTAAACGCCATAAATGTCTCTTTCCCTTAAAATGAACAATATAATGTTAGAGTTTAAATTTAAACAAAGGCGCCGAGGACC
AGAACACCCTCTACAAATTAATCGATGGCCACCAATCGATGATTAGTGCTATCGACGAGCGGCCATCGCCGCTTGGCGGCAAGTGCATACACACG
ACTACATGCAATCGCAGTTTGTTTTCGCCGCTCAGAGCACGCTTAACCTCCGTTAATTGATTGATTAAACACGTCCGACTGTGAGCCATAAAAGG
ACATTCGCTCGATCGAAAGCCGACAAAAGCTGGCTGAGAAGCGCAAAACAGCTGCGCTGCGCAAAGTTTGGCCAACGCAGAGCAATAGAAAACAG
AAGCAGTGTCAGAATAAAACAAGAATCAGACCAAAAAGGGCGCAACAACTGCGGAGAGAGAAAAGGAAGGAAAGAGCAGCGCGTGAGCGAGGGAG
GAGCAGGAGGGAGCGAACAAAAGGCAAGAGGAAACACAAGGAGAAACGCAAACAATCAAAACAAGAACTTAAGCAAGAAAAGGGGCGCAAGATGA
CCGACGAGTGCGTAACCAGAAACTACGGAGTAGGCATTCGCAGCCCAAATGGATCGGAAAATCGGGGCAGCTTTATAATGGCTGATAATACCGAT
GCCAAGGGCTGTACGCCGGAGTCTCTTGTTGTTGGTGGTGCAACTGCAGCGAGGTGAGTCCATGTGCCTCGCTCTCTCCCTCTCCCATCTCTCTC
TTTATGTTTCTGTGTTTTGTTATCAATGCAAGTACTGGCATAACTGCTATATCCTAGTTTCAAATGCAGCATATAAAGCTCTTTTTTTTTTATTT
ATTCCATTTTCATTCCACAATCTATTATTTTATATTATTTATACTGTCTATTGCCAACATTTAAAATCAATGTGTCAATCTGTCTTTATAATGT
TGTTAAAATGGCTGAAGTCACAAAGTTTGAAAGCACTTGACTTTAATTCTATTGTTCTATTTAGTCTTATTCACAAATATATTTGAAAATAATTA
CATAAATAAATACCCAATCATCGATTATTTCGCCGATTACCTTATCTTATCATGCTGCTTCCCAAATGGCTATTATAATTCTGATTTCTTTTTCC
CCAGCCCCTTGCCGGCCAACAAGTTTGTGGCTCGAATGCCCGTGGAACGATATGCAAGCGAATACAACATGAGTCACAAGCACCGCGGAGTTGCG
CTGATCTTCAACCACGAATTCTTCGACATACCCTCGCTGAAGAGCCGCACCGGAACAAATGTCGATGCCCAAGAGCTGAAAAAGGCCTTTGAAAA
CCTGGGATTCGCGGTGTCCGTGCACAAGGACTGCAAGTTGAGGGACATCCTGAAGCACGTGGGGAAGGCCGCCGAGTTGGACCACACGGACAACG
ACTGCCTTGCGGTGGCCATACTCTCGCACGGGGAGCACGGCTACCTGTACGCCAAGGATACGCAGTACAAGCTGGACAACATCTGGCACTACTTC
ACTGCCACCTTCTGCCCCTCGCTGGCGGGCAAGCCGAAGCTGTTCTTCATCCAAGCCTGCCAGGGCGATCGCTTGGACGGAGGCATCACTCTGGA
GAAGGGCGTTACCGAGACGGACGGGGAGTCCTCGACGAGCTACAAGATACCCATACACGCCGACTTTCTCTTCTCCTACTCGACCATTCCGGGTA
AGGAATATGATTAGGTAACTATTTAGTGAATTTCACTAGCAATCTCGTCCTGTTAGGCTACTTCTCCTGGCGCAACATCAACAATGGCTCCTGG
TACATGCAATCGCTGATCCGCGAGCTGAACGCCAATGGCAAAAAGTACGACCTGCTCACCCTGCTTACATTCGTTAACCAGCGCGTAGCCCTAGA
CTTTGAGTCGAACGTGCCCGCCACACCGATGATGGATCGCCAGAAGCAAATACCGTGCCTCACCTCCATGCTGACGCGCATACTGCGCTTCGGCG
ACAAGCCGAACGGCAATAAGGCTGGCTAGGAAGAGATCTCCCTTCGAAGAAGAACTTTCAACAGAGGTTGTACAACCATCGCCCGCAATCATTCA
CGTTGGATTCCAATTCACTTCAAGTTTAGTTTAGCTGACGCGTGCGATTATCCCGATGGATATTGAAGCACCCGACTCCCTTTCATTCATTCCC
CTGCCTTTCCCATGCCCATTTCGGCCTTATCATTGACGAAATTCGTTACCCATTTACCCACTAGATGACTTCCGTATGCATAAGCGAGACCTTGC
CAATAGAAAACCCACAAATTTGAGATAAGATAATACAATGAAGATTTATACATACATACATACTTTTATGTACACGCAAACATTTATATTTGATA
TGAATAAAAATGAATTAAAAACATAGCAAGGTATCTCCCCAATTGAACGTAGATGGGTAATTTCGATCTAAGCAACTTTGTTTGAAGACAGGAGC
TGTCTGGGCCAGATTGAGTACGTTGATATGGGAAATAAAAGATAACAATGAAGACTTGGTTGGCTGAATCAGTGAAATTGTACGAAACTTTAGTG
GAATTCAAATTAGCATTATTAAGAGTGATTAATTAAGATTTTTCTCACTCTAATTTTATTAATTTCCTAAATTTTATATTTATTTCCTAATTTTA
TAATTTAGGAAATTAATAAAATTAACCAAATGATGATTTTTGCGTAAATATAAGTATCGAAGGAACTATTAATGCATTTAAATATGATCTCGATT
TGAATTTAGCGCCAAAAACAACTGACAGCTGTCAGGGCGATCAGCTGTTGACGCACTAGTGTGCGTGTGGCGCAGTACAGTTGCCCCAAATCGCA
GAAATTTTCATTTTTCTTTGCACAAGAGGAAAAAGGGAAAGCCCAATGATTAGCCAACTAATTGGGCTGTAACCTGGTCGCACTTTTCAAGGACA
TTCGGCTGGGAAAGGGAAGCGGGGCAGTTTGGAGCGGGGAAACTTAGCCAAGACGCCTCGCAGTCGATGCGGAAACCCGCGATGCGGCTTCTTAG
CCAAGTTATGCGTGGCGCTGGTTAGTGCAAGCCAGAACCCATGGATGGAGCCGCTTACCTCGATCGCCGTGATGGCCATAATCTGCAGCGGCAGA
TTGGCGGTTGTTTTCACCCGCGGATTCTCCTCGAAAATCGAGGCCAGCTTCTGCTCGGTCAGACAGAAGCGGCAGACCCTCTTCTCGGTCAGCAT
GGCCTCGCGCACCTCCAGTTTCGCGGCCATCGGCAATTGGCGGTAATTCGTTCCGGGCGGCGGTAGAAACGCGGAATTTCACTTGCAAAGTGCGT
ACAGATTACAAATGAGAGGAAAACAATCGCTTGGCGTCGCTTAGAGATGTGCACTATGCAGATATCGATGTTTCTGTGT
(SEQ ID NO: 601)

Exon: 1001..2808
Exon: 3235..3797
Exon: 3858..4494
Start ATG: 2657

Transcript No. : CT17064
GCTTCTCGCAGTACACGCAGATGAACTTGGGTACGTCCGTGTGGGTGCGCTCGTGGCGATGGAGCAATGCCTTCCGTGTGAAGGCTTTCGAGCAG
ATGGCGCACTTGAATGGCCGCTCGCCGGTGTGCACAAAGTTGTGCTTGGCCAGGTCGTACTTGGAGAAGAAGCTCTTCTCGCACAGGAGACACTG GAAGCTGCGCGAGCGAGTGTGATTCAGCCGATGGATCTCGAGCAGCTGCTGCAGCGGAAAGGAGCGTTCGCAATCGGGACAGGGGAACACATCGG
TGGCCACCTTCTCGGCGTTCTTGGTCGGATCATCTTGATCGTCCAATGGCAGATCCGAGTCCAGAACCTCTGTCACTATGGCCACATTGCCACTA
TCATCTCGCTTGACTTTGGGTGTGGCCAGGCGCGGTTCCACCGGAGCGGCGGGTCCCTTGTTCAAGATCCTAATCGAGGACTTGTTCAGCACCTT
CGGCTTGACGGGTGATGCCTTCTGGGGGATATCGGGGAACTCCTTCTCTAGCTCACTGGCCATATCCTCCAGCATGCTCTGCACATCGTCCATGG
ACAGCTCCTGGTTGTTATCCACCTTCAGCTCATAGGCGTGCGAACGACGTGGCACTGGAGAGGAACCGGCTACCGTCCTGGGGTCACCATGGCG
CTCTCCAGCACCTGGACGTCCTCGATGATCACCTGACTACTGGATTTGGCCATTGTGTTCAGCAGCTTTTTGGGCGTTTCGCTTGGCTCGGCTGT
CTTTGCTGGCACGACCAACAACTTCTTGGAAGCCACCATCGTCATGGGCGCACGGGGCTTCTCCAGCGGCGATGGCCAGTTACCCGTGAGCGGAT
ACTGGCGCAGGAGGGTCTCCGCCCGCTTGCACATCTGCTTGAAGCGGTAGCAGTGCTCGAAGAGGAGGCGGCACTCCAGACAGATGTGCCCCGGC
ATTCCGTCGCCGGCGTAGACCTGTTTTTAATGTTAGATTAGATAAATGTGTGAGTGACTAGGAAGCTACATTTATTCGGGGAAGTCCGTGCTTAA
GCCAAATAATAAGGTAATATTCGTGGAACACCCCTATATGTTTTTCGCTACATAATAAATTAAACGCCATAAATGTCTCTTTCCCTTAAAATGAA
CAATATAATGTTAGAGTTTAAATTTAAACAAAGGCGCCGAGGACCAGAACACCCTCTACAAATTAATCGATGGCCACCAATCGATGATTAGTGCT
ATCGACGAGCGGCCATCGCCGCTTGGCGGCAAGTGCATACACACGACTACATGCAATCGCAGTTTGTTTTCGCCGCTCAGAGCACGCTTAACCTC
CGTTAATTGATTGATTAAACACGTCCGACTGTGAGCCATAAAAGGACATTCGCTCGATCGAAAGCCGACAAAAGCTGGCTGAGAAGCGCAAAACA
GCTGCGCTGCGCAAAGTTTGGCCAACGCAGAGCAATAGAAAACAGAAGCAGTGTCAGAATAAAACAAGAATCAGACCAAAAAGGGCGCAACAACT
GCGGAGAGAGAAAAGGAAGGAAAGAGCAGCGCGTGAGCGAGGGAGGAGCAGGAGGGAGCGAACAAAAGGCAAGAGGAAACACAAGGAGAAACGCA
AACAATCAAAACAAGAACTTAAGCAAGAAAAGGGGCGCAAGATGACCGACGAGTGCGTAACCAGAAACTACGGAGTAGGCATTCGCAGCCCAAAT
GGATCGGAAAATCGGGGCAGCTTTATAATGGCTGATAATACCGATGCCAAGGGCTGTACGCCGGAGTCTCTTGTTGTTGGTGGTGCAACTGCAGC
GAGCCCCTTGCCGGCCAACAAGTTTGTGGCTCGAATGCCCGTGGAACGATATGCAAGCGAATACAACATGAGTCACAAGCACCGCGGAGTTGCGC
TGATCTTCAACCACGAATTCTTCGACATACCCTCGCTGAAGAGCCGCACCGGAACAAATGTCGATGCCCAAGAGCTGAAAAAGGCCTTTGAAAAC
CTGGGATTCGCGGTGTCCGTGCACAAGGACTGCAAGTTGAGGGACATCCTGAAGCACGTGGGGAAGGCCGCCGAGTTGGACCACACGGACAACGA
CTGCCTTGCGGTGGCCATACTCTCGCACGGGGAGCACGGCTACCTGTACGCCAAGGATACGCAGTACAAGCTGGACAACATCTGGCACTACTTCA
CTGCCACCTTCTGCCCCTCGCTGGCGGGCAAGCCGAAGCTGTTCTTCATCCAAGCCTGCCAGGGCGATCGCTTGGACGGAGGCATCACTCTGGAG
AAGGGCGTTACCGAGACGGACGGGGAGTCCTCGACGAGCTACAAGATACCCATACACGCCGACTTTCTCTTCTCCTACTCGACCATTCCGGGCTA
CTTCTCCTGGCGCAACATCAACAATGGCTCCTGGTACATGCAATCGCTGATCCGCGAGCTGAACGCCAATGGCAAAAAGTACGACCTGCTCACCC
TGCTTACATTCGTTAACCAGCGCGTAGCCCTAGACTTTGAGTCGAACGTGCCCGCCACACCGATGATGGATCGCCAGAAGCAAATACCGTGCCTC
ACCTCCATGCTGACGCGCATACTGCGCTTCGGCGACAAGCCGAACGGCAATAAGGCTGGCTAGGAAGAGATCTCCCTTCGAAGAAGAACTTTCAA
CAGAGGTTGTACAACCATCGCCCGCAATCATTCACGTTGGATTCCAATTCACTTCAAGTTTAGTTTAGCTGACGCGTGCGATTATCCCGATGGA
TATTGAAGCACCCGACTCCCTTTCATTCATTCCCCTGCCTTTCCCATGCCCATTTCGGCCTTATCATTGACGAAATTCGTTACCCATTTACCCAC
TAGATGACTTCCGTATGCATAAGCGAGACCTTGCCAATAGAAAACCCACAAATTTGAGATAAGATAATACAATGAAGATTTATACATACATACAT
ACTTTTATGTACACGCAAACATTTATATTTGATATGAATAAAAATGAATTAAAAACATAGCAA
(SEQ ID NO: 602)

Start ATG: 1657

MTDECVTRNYGVGIRSPNGSENRGSFIMADNTDAKGCTPESLVVGGATAASPLPANKFVARMPVERYASEYNMSHKHRGVALIFNHEFFDIPSLK
SRTGTNVDAQELKKAFENLGFAVSVHKDCKLRDILKHVGKAAELDHTDNDCLAVAILSHGEHGYLYAKDTQYKLDNIWHYFTATFCPSLAGKPKL
FFIQACQGDRLDGGITLEKGVTETDGESSTSYKIPIHADFLFSYSTIPGYFSWRNINNGSWYMQSLIRELNANGKKYDLLTLLTFVNQRVALDFE
SNVPATPMMDRQKQIPCLTSMLTRILRFGDKPNGNKAG*
(SEQ ID NO: 603)

Name: caspase-1 precursor
Classification: endopeptidase
Gene Symbol: Dcp-1
FlyBase ID: FBgn0010501

Celera Sequence No. : 142000013384832
TGGGGGTGGGGTAGTTGAGGGGCACGGAAGGAACTGAACAAAATTGAAATAAAATAAAGCACCATAAAACGTACTTAAGATTGACGATTGTGTTT
TTTGGGGGAGCGATCAATGAAAGAGTTTCGATGAAGACAATATATGGCAAGTACAGTTGAGCTCTTTTTTGGATTTGGGCATTCGTGTTGTCTGC
AAAGGGTTATTGATAATTCTATGCTCTTCCCAATTTAGTTAATATTCTTTTATTACTAAATTATGAGGGAATTTTTGTGTCTGATTTCGAGACGG
GGGAACAATCGAAGGAGCCAGAAAGCGACCGAAGAACGCGTTGAGTAAATGCACATTCTGGAATATTTATATAGTACATTTGAATATATATGTAC
TTGATTAGATATAATTGGCTGTCAGTATGTCTCTTGATCGCTCCACTCAATCGCACCAATACTCGGATTCGGATACCGAGCAACCGCACAGATAC
ATTTTCGAAACAAACAAAATGTCGGCAGCTGCTTGTTGTGTTAGCTTATAAATTAAAACGCGTTTCATGGCATTATTATTTGATGGTTTTTTACT
TTTTTTTTTTTCGTCTTATGGCTGCTCAATTCATTCGATTGTTCGTATATTCACATTCTTTTTAGCCCATTCGTACCCATATACCCCCGATATCG
CTCACACCTCCTTCCCCCCCTTCTCCGCTCGGTTCATCTGTCCGCCTGTCTGCTAATTGAAAATCAATTAATGTGACTGCATCCTATAGCTGCTC
ATGTCAAAGTCAGATATCATCCAGGGTAGGGTAAATTCGATGGAATAAGGGAATGAAAACAAGAGAAGGAATTCAAGACTCAACGACTCAGATTC
AGAATCCGAATCAGAATCCTTTTGTTTTCACTGACCTTACTGTCTGAAAACAAAAACCCAATTGATGTGCCCCAAGTAACACTCTGATAATTACC
GAAAAACTCCAAATTTTTCGATTGCTTTCGACTTTGGCAGTATTCATCGCCAAGTTCATTGGGTTTTCGAGTGCGTCCCGCGAATCGCTTTCGTT
TGGTGCGGAATTTGGCACAAGTTTTGTATGCTCAACTACTGGGAAGGCCAATCTGGGGCTTCTAATTCCACTGTGCGGGTAATTTGGGGACTCTT
GCCAGTTACTAGTTACCTCCCAATACGAATCACTGATTTCTCACCTCCTGCCACTCGCTTCTTGCTTCCGTTGCAGGTCAACAAACAGTATTCGG
CCACCGATCTGGAGGCTTTTATGAAGATTGCCGCCAACTGGCAAAATTCCAATCACAACTTGCTGGAGGGCGTCGACATAAAGACGGGTAAGTTA
AACAAAACGAAGTGACCGTTGAAGGAACTTAATTCAATCATCGAATGCTTGCAGAAATGACACAGTACATGAACAGTCCTTCCATGAACATGTAC
AAGAAGAGGGAACGCACCCAGAACTGGAACCACCAGGAGAAGAAATACCTACTCGATCTGTGTCGCAAGGACATGCGCATTATCGAGAACAAGAG
ATTGGATGCCGGTCTGACCGCCGTGAAGAACAAGGCATGGAAGATTATCCACCAGAAGTTCTCCAATCAGTTTGGCACCGATCGCACCTGCAATC
GCCTGAAGGAACAGTGGCGTCGCATGAAGGGTAAGTCTTTATAAAATACATATATTTAATGGCAAAGCTAACCTTTTCGATCTCATCCTTTAGCA
TGTACTCGCAACGAGATCCTGGACTACAATAATCGCCTGGCCAGGTTTGGAGCAGAGGTGGCCGATCGCAAGAAGCCATCTCCGTTCACCTTCGA
GGTGTGGGATTTCATGCAGGAGGCGAAGAAGGCATGCAAATCGGAGGCCCTGGATGGCATTGATTACTCTAAGATTCCACTGGCCTTGGAGGAGG
GTTTTGAGTATCGTGAGGATTACAAATTCAATCCCGAAGACCACGACATGGATGAGTAAGTTGATCGCTATGTGGTAGTCTGAATAGATCTTTAT
TGAGCATTCTCTATTTGAGCAGCAGCCGCACACCGCCGCAGGAACTGTGCGATGTGGACATCAAGGAGGAGGAGAACAACGAGACCTTCAACGAG
ACCTTCAACCATCACCACCTCAACCAGAGCGACATCCTTGGCAGCGGCGAGCGTCTCAGTGTGTCGCCTAATCACAGCATCAGTCGCAACGGGAT
CCACGAGGCCGAGAGTCCCGCCACGATTTCCACATCTAATGTCCTGGACTCGAGCGGTGCCTATATGGCCGGAGGAGGTGACATGTCCGGCTTCC AGGCCAACTTCAACATGAACAACATATCCGCCACGCTGGAGGCACTGAATGCCCTCCGTTCTGGCCAATTTCCCAGTGCAGCAGCAGCGGCAGCG
GCCGCCATTCACCAGCACCAGGCACAGGCCCAGGTCGCCATGCATCACCAGCACAATAACAACAACAACAATAACAACAACAACGAGGACGACGA
GGACAGCATGAAGCCGCAGTCTAAGAGACAGCGCACCAGCAGTGGTAGCATGTTGGGCAGCGAGGATCAGGCACCAGTCCTGGCCCCATCAGTGC
CAGCATCCTCGGACTCGCAGGCCCTAGAGCGGTCCGGCAGCAGCAATGGATTGACCATGCCGGGAACGGCAGTCAGCACCAATGCCAACAGCAGC
AGCAGCAACAACAACAACTTTGAGCTGCGCATGTTCATGGAGATGCAGAGCAAGGAGCACATGATGCGCATGAAGATCCTGGAGGTGCAGTTGCA
GGCGGCAAAGCACAGTCGCGACCTAGTGGAGATCAACAAGACACTGGCGCTGCAGAAGCTGCAGTTGGAGCTGGCCAGCAAGCGACTGCCCAGTT
AGGAGGCAGTGCAGCAGCAAAAGGAGCAGCAGCAGCAACAGCAGCAGCAGCCCATCGCCGTTTCATGTTACATTAGTTTATAGAAATAAAGCCTG
TCAACTCGGTCACGTTCGCAGGCAGAGAGCGTGATTGGGAATCGACTAGAGTTAGCACTAGAGTTAGTCTTAAGTTGAAAGCAGGATCCACAGCT
ACACATCCAGACCCGACACACAGAGAGACATTCCTGGCATTGTTGATCAGTATTTGAAAGCTAGAAGCGAAACCCGACACACAGAACCGAACCCA
AGAACCCCAGCGAGGATCAGGAGGCGCTCGGAAGTATGCCATAATCTTATGATGATGATGACGATGATGATGATGAATCGCCTACCTCACAAGCA
CACACACACACACACACACAATATGCACACACTCAGCTAGCAGACACACACACACAGACACACTCTCTTCTGGCCTAACCAGCACTTGACCAAGT
CAAGTCAAGTTTAGTTAGTTTCTAGTTTTAGTTCGTATGGAACCACTCTCTCCAAGTTGCTCAACTACCACAAATGTATTGTACTTACGTTCTT
GACCTCTGCTACCCCACAACTAACGATTTGAACGAACATGAAATGCACACAAGATTATTTTTCATAGTCCTAAGAGAAGAACCTTATATATGTCA
ATGCATCATACACAATCGGCAGTTGTCTCTGATTTTGATTCTTACTTGAACTTGTATTTATTTGTATCTTTGTATAGACTATGTTGATATATATA
TGACCCTATATATGTTTGTTTCAATGCCATATTACATGAAAGTTCTTTTTAATTCATATTTTCCGTTTGCGCTGCAAAACAAATTGTTACCATAT
ATAATATATGATATGTATGTACCCTACGTATAAGCAGGCTTGAAGAAGGCCGCCAACTCGGCTTCAGTTGTCGTAGAAGACTTCTTTGTAAAGCG
TGTAAATGAGAGATACAAATTATTTTAAATAAAATACAAAACAAAACAAGCAAATGTTTCAGCTACACTTTATTAATTTTGTTCATGGTTCATCT
GTGAGCCTTCGGTCTTGGTTTTTTCCAACGATTGTATCTGCTTATCCACCTTGATGATCTTTGTTGTGACTTCGTTCTTCTGGCTGAGAATCTTT
TCTCGCAACGACTTCAGCTGTTCCCGTTGCTGGGTAAATTTGCAATTAAATTTAAATAGATTACTTTCGTTTTTTGAGATCACAAACCAACCAGT
TTAAGGAAATGTATGTTCTCCTCCGCCCTGGCTTTTTCGAACAAATGCTTGGATATGTTCCTGGATACAGAGATGCATCTAATAAGCGAAGCCAT
AAGTGCTCAGAACACGGAACTCACTTGTTGGATTGTGAAAACTGACACATCCTGGGTCGCAACAGTTGGAAAAGCTTTTCGACCAACTTCAGCAT
TGTATCCTTACGGAGGAAGATAATTTGGAATTTACTATAGTAACTGATGAGGTATTTCAAGGTGGAATATTGACAAACTTAAAAGTGATAGCCTA
CCGTTTGATAGGTCATTTTTCGAGACTCTTTTTGAATTGCTCCAACAAATCCTTCAGAGCTTTCAATTCCTTTAGCAGATTCTCCTTGTGTTTCC
TTGATTTGTGGCTAGTTTTGGATTCCAAAATCTTGATCTCCTCTTTCAATTTGACGATATCATTGGCGATTTCTTTAACCCTGTTCTTTTTTATC
TTCATAAATTGCTCTGAGGCCTATGGAATACCCAATTCTACAAGGTTATTCACAACATTAAATAGTTTCGATACATACAAGTTTGAGAACATAGT
TAAGTTCCTCGCCTCTGCCCTTCTCGGAAAATTTGTCAGTGAATTGACGTCTATCATATGTAAAAAAAAAATTATTTTTACGGGTCATTTGAATA
ATAAAATACTTACTTAGCAGGAAATTCGTTTAAATTATTATTCGACCTTGGGTGGAAAATGTTTCTACCGTGGTAAAAGTTTCTATGCCTTGGTA
AATTTCTGTGCAACTCATTGGAAGGCCAACTAATATTTAGAAGATTTACAAATAAAGTTTGGATAAATTTCCAGTACTACATACCAAACTCTTTC
TTGACATAGCACCTGAGGTTGAAATAGCCTGTTGCACGATGCCGAGCCTAAGATTCGTGCAACAGGAAACATGGCTTCTTAAGTT
(SEQ ID NO: 604)

Exon: 1001..1322
Exon: 1385..1645
Exon: 1709..1955
Exon: 2018..4025
Start ATG: 1073

Transcript No. : CT17108
CAAGTTCATTGGGTTTTCGAGTGCGTCCCGCGAATCGCTTTCGTTTGGTGCGGAATTTGGCACAAGTTTTGTATGCTCAACTACTGGGAAGGCCA
ATCTGGGGCTTCTAATTCCACTGTGCGGGTAATTTGGGGACTCTTGCCAGTTACTAGTTACCTCCCAATACGAATCACTGATTTCTCACCTCCTG
CCACTCGCTTCTTGCTTCCGTTGCAGGTCAACAAACAGTATTCGGCCACCGATCTGGAGGCTTTTATGAAGATTGCCGCCAACTGGCAAAATTCC
AATCACAACTTGCTGGAGGGCGTCGACATAAAGACGGAAATGACACAGTACATGAACAGTCCTTCCATGAACATGTACAAGAAGAGGGAACGCAC
CCAGAACTGGAACCACCAGGAGAAGAAATACCTACTCGATCTGTGTCGCAAGGACATGCGCATTATCGAGAACAAGAGATTGGATGCCGGTCTGA
CCGCCGTGAAGAACAAGGCATGGAAGATTATCCACCAGAAGTTCTCCAATCAGTTTGGCACCGATCGCACCTGCAATCGCCTGAAGGAACAGTGG
CGTCGCATGAAGGCATGTACTCGCAACGAGATCCTGGACTACAATAATCGCCTGGCCAGGTTTGGAGCAGAGGTGGCCGATCGCAAGAAGCCATC
TCCGTTCACCTTCGAGGTGTGGGATTTCATGCAGGAGGCGAAGAAGGCATGCAAATCGGAGGCCCTGGATGGCATTGATTACTCTAAGATTCCAC
TGGCCTTGGAGGAGGGTTTTGAGTATCGTGAGGATTACAAATTCAATCCCGAAGACCACGACATGGATGACAGCCGCACACCGCCGCAGGAACTG
TGCGATGTGGACATCAAGGAGGAGGAGAACAACGAGACCTTCAACGAGACCTTCAACCATCACCACCTCAACCAGAGCGACATCCTTGGCAGCGG
CGAGCGTCTCAGTGTGTCGCCTAATCACAGCATCAGTCGCAACGGGATCCACGAGGCCGAGAGTCCCGCCACGATTTCCACATCTAATGTCCTGG
ACTCGAGCGGTGCCTATATGGCCGGAGGAGGTGACATGTCCGGCTTCCAGGCCAACTTCAACATGAACAACATATCCGCCACGCTGGAGGCACTG
AATGCCCTCCGTTCTGGCCAATTTCCCAGTGCAGCAGCAGCGGCAGCGGCCGCCATTCACCAGCACCAGGCACAGGCCCAGGTCGCCATGCATCA
CCAGCACAATAACAACAACAACAATAACAACAACAACGAGGACGACGAGGACAGCATGAAGCCGCAGTCTAAGAGACAGCGCACCAGCAGTGGTA
GCATGTTGGGCAGCGAGGATCAGGCACCAGTCCTGGCCCCATCAGTGCCAGCATCCTCGGACTCGCAGGCCCTAGAGCGGTCCGGCAGCAGCAAT
GGATTGACCATGCCGGGAACGGCAGTCAGCACCAATGCCAACAGCAGCAGCAGCAACAACAACAACTTTGAGCTGCGCATGTTCATGGAGATGCA
GAGCAAGGAGCACATGATGCGCATGAAGATCCTGGAGGTGCAGTTGCAGGCGGCAAAGCACAGTCGCGACCTAGTGGAGATCAACAAGACACTGG
CGCTGCAGAAGCTGCAGTTGGAGCTGGCCAGCAAGCGACTGCCCAGTTAGGAGGCAGTGCAGCAGCAAAAGGAGCAGCAGCAGCAACAGCAGCAG
CAGCCCATCGCCGTTTCATGTTACATTAGTTTATAGAAATAAAGCCTGTCAACTCGGTCACGTTCGCAGGCAGAGAGCGTGATTGGGAATCGACT
AGAGTTAGCACTAGAGTTAGTCTTAAGTTGAAAGCAGGATCCACAGCTACACATCCAGACCCGACACACAGAGAGACATTCCTGGCATTGTTGAT
CAGTATTTGAAAGCTAGAAGCGAAACCCGACACACAGAACCGAACCCAAGAACCCCAGCGAGGATCAGGAGGCGCTCGGAAGTATGCCATAATCT
TATGATGATGATGACGATGATGATGATGAATCGCCTACCTCACAAGCACACACACACACACACACACAATATGCACACACTCAGCTAGCAGACAC
ACACACACAGACACACTCTCTTCTGGCCTAACCAGCACTTGACCAAGTCAAGTCAAGTTTAGTTAGTTTCTAGTTTTAGTTCGTATGGAACCAC
TCTCTCCAAGTTGCTCAACTACCACAAATGTATTGTACTTACGTTCTTGACCTCTGCTACCCCACAACTAACGATTTGAACGAACATGAAATGCA
CACAAGATTATTTTTCATAGTCCTAAGAGAAGAACCTTATATATGTCAATGCATCATACACAATCGGCAGTTGTCTCTGATTTTGATTCTTACTT
GAACTTGTATTTATTTGTATCTTTGTATAGACTATGTTGATATATATATGACCCTATATATGTTTGTTTCAATGCCATATTACATGAAAGTTCTT
TTTAATTCATATTTTCCGTTTGCGCTGCAAAACAAATTGTTACCATATATAATATATGATATGTATGTACCCTACGTATAAGCAGGCTTGAAGAA
GGCCGCCAACTCGGCTTCAGTTGTCGTAGAAGACTTCTTTGTAAAGCGTGTAAATGAGAGATACAAATTATTTTAAATAAAATACAAAACAAAAC
AAGCAAATGTTTCAGCTACACTTTATTAATTTTGTTCATGGTTCATCTGTGAGCCTTCGGTCTTGGTTTTTTCCAACGATTGTATCTGCTTATCC
ACCTTGATGATCTTTGTTGTGACTTCGTTCTTCTGGCTGAGAATCTTTTCTCGCAACGACTTCAGCTGTTCCCGTTGCTGGGT
(SEQ ID NO: 605)

Start ATG: 73

FIGURE SHEET 329

MLNYWEGQSGASNSTVRVIWGLLPVTSYLPIRITDFSPPATRFLLPLQVNKQYSATDLEAFMKIAANWQNSNHNLLEGVDIKTEMTQYMNSPSMN
MYKKRERTQNWNHQEKKYLLDLCRKDMRIIENKRLDAGLTAVKNKAWKIIHQKFSNQFGTDRTCNRLKEQWRRMKACTRNEILDYNNRLARFGAE
VADRKKPSPFTFEVWDFMQEAKKACKSEALDGIDYSKIPLALEEGFEYREDYKFNPEDHDMDDSRTPPQELCDVDIKEEENNETFNETFNHHHLN
QSDILGSGERLSVSPNHSISRNGIHEAESPATISTSNVLDSSGAYMAGGDMSGFQANFNMNNISATLEALNALRSGQFPSAAAAAAAAIHQHQA
QAQVAMHHQHNNNNNNNNNNEDDEDSMKPQSKRQRTSSGSMLGSEDQAPVLAPSVPASSDSQALERSGSSNGLTMPGTAVSTNANSSSSNNNNFE
LRMFMEMQSKEHMMRMKILEVQLQAAKHSRDLVEINKTLALQKLQLELASKRLPS*
(SEQ ID NO: 606)

Name: RNA binding protein
Classification: RNA_binding
Gene Symbol: apt
FlyBase ID: FBgn0015903

Celera Sequence No. : 142000013384541
ACCTGAATGTCAAGCCCAGCTGTGCCGGAGCCTGCGCCTTGGCCGTGGACACCGTCACGCCGTAGTCCTGCAACGTGCTGTCGTCCTCCATGACA
TCGTTGTCCTGATTGTATAACCGCTGGTCCACGGGCTGCACCTTTAGTATGCCTGCGATCGATGGGGTTGTATGATCAGTCATGGAGTTACCCAA
TAATGGCGCTGCTCTATAAATAGAAGCCAACACTTACCCTCAATCATTCGCTTCAGCTCGGCCACCGTTGTGTTCTCCTTGGCGTCCGTGAAGAT
GGTGGTCTTTTGCCGCCTGATCATAAGGAACACGTCCTGCAAAAGAGAGGGTTAGCCATTAGATTTGATTCGATGCGAAGTGATTCGTTTCGGTC
AAAGTTCAGTGGCGCTTTTTCAGTGTGTCATGCTTTCTGATCTTGCCATCACACAGGCGACATTTGTGCACATGCATTAAGAGCGCGACGGTGTC
TATGGCAGCAGCATCTGCGATGCACTGCATCCTTGCTAGGCTGCACGACACCGGCACGAGCACTCACCATATTGAGGAGTTTGTGGCGCTGGCTG
CGACTGAGGCTGCTACGCGGATGTGGGTTAACCAGGTGCGTGGGCTAGTGCGCTGTGTTCGGCAACTGACGGCGTGGGTGGCGCTTCCTTTGGCG
GTCGCGGGCGGACGTTTCGATCGGCTGGAATTTTCCTACTTCGCTTGCACCACCGCTGCTGGGCGCTTCTATTTTTTGCTCTGTGCCGCTCGACC
GGAGTTGGGGGCGGGCGCAGGTGGGCGTGGCGTGCGGTTCGCGGTACGATGAGCGTGCGTGAGTGTGTATGTTTGTGCAACAGCTTCCTCGGTTG
CCCCCCACTTGTAGGTTTTCGTAGTTTTACGATTTTTTCTAGCCTTTTGCTGCTGCTTTCTCAACTAATTAGAGCTGTCAAACCATCGATGGTCG
CATCGATAGTGAGCTATCGATAGTTCAGGGTCAGCGGCCTTCGTTGTCTAATGCCATCGCTAATCCGATATTATTGCAGGGCTTTTAGCAAGGGA
TTGTCTAAAGCCTTGGTGAATTCTATTAATGTGTATTAACAAATACTTCACAATTCCGTTTAATGTATATTTTCCATTAGTTTATAAATAAAATA
ATTCGCATAAGTAATGAGCTTTTGCAGCCCTGGTTATTGCCAAGAAAATGTACTAGAAAATACCGCCATAGCTGTCAGTGTCACTTTTCCCGTTT
CTCCTGTTTTATTTGCCACGAAATGGTTTTGCTAGACAATTCGAACGTAAATAAATGAAATACCTTTAAAAGAAGCCGATAAGTAACCGTATCTC
CTTACAGTTTATCCTGCGCCTGGAGAAGATCGCAAATGCGGCCAAGAAGGACTCCTCCTTCACGCTGACGTTCAAGCGATGTGAGTGTTCGACAC
CGAAAAACATGGTACACTAGGAACTAATTTACAATTTATTTAATGTGCCGCAGATGATGGCAACGATAAGCCCGTGCCGAGGGAAGGACGGCCAC
CGCTGCCCAAGCCGGAGACCTACATGTGCCTGATGCGCGCCCAGTCCAAGTCCCAAAAAGTAAGCCCGATTGAAAGCTCCACGTTTCGACTCCTT
ACCAAATAAACCTATTTTTCCGGCAGATTTCCACCGTTGTCCGGCAGGAGGATGTGCCCGCCATGATGAGCATGTACTCGCAGTTCATGAAGAGC
AAGATGGACGGGCTAAAGCGGGTTAAGAAAGTCAAAAGCAAGGCCAAGGCGACAAAGGGTTAATCGGGGCATAGTCTTAGTTAGATTTTATTTGA
CTGTTTACTGGTCGTTTGTTTTAAACCTTAAATGCATCATTTTGTACGGAAAGCACGCTATACTTCTTATTTCTATCATCAATCTGACGCAGATC
GAGCAGCCACTTCGGCAGTTCCCACTGCCGCAACCCGTATATGAACTTTGGTCTTATCAGGTCAACCAAACTGTAAAGATCCTCGTTTATTTGGT
TCTCAGCTAATAGCTCTTCGTCCACGTACAGTACATCGATTCCCTGACAGAGGCCCGTGTGAAGGGAGCCCGAAGCCTTTGGCAGAAAGTCCAGA
TACCCAGATAGGCAGTCCACAATTAAATATCGTGCATGGCCGTCTGCAAAGAGATAAGTGTTCTCAGACTACCAACAGGAACCAATGGCTCAGTA
CTCAGGTAGTACTCACTTTCTATGTAGAATAGGTTGCACTCCAAGCCGTTTTCCTTTCTTCCTGCTGGTATCAATGTGATTGTGATCTCGTTTTC
ATCGTACACTAGTCGGGTGGGCTTATTCGGCAGTAGTATTTCAAAAGTGCAGCTTTCTGAAACATCTGCATGTGATTGCAGCCGTGAGATGTCCA
GCTGCGAACCCACAGCTAACTGGCACCAATTTTGTGGTGCTATTAGATCTCCTAAGGCGGCTGACGTGAAGAGCAAGGGTCCACGGTGCTGGAGG
GCCAAATTGTATTGGAAGTGAATTTATATAAAACTAGGTGGTGTACGCACCTCCTCGTAGGAACTGTAGACTTTTCCTTTTTCCAGTATTAAGGG
CTGGCCTATATCGTTTAAAAACATTGTTAATTATGCGCCAATTCCTCAGGAAATTTGTTTTTCTATGTGTTACCAGATCGCATTGACAAGAAAAT
CCCAATTCTTCAAGGACTATTTTCTAAGTTCAAAACTACAGCGCCGAGATTTTAAAGTAGAATTCTGGATAATTTTGGAAATATTTGCAGAAAATC
CCCTCATTGAAAGAAACTTTTTAAGTATTTAAATATTACCATCTGCACTATGAAATCATCCAACCTTCCCTTTTGTAGCGCACTTCAATAAAAAA
CACAGATTGTAG
(SEQ ID NO: 607)

Exon: 1001..1060
Exon: 1219..1281
Exon: 1338..1410
Exon: 1479..1579
Exon: 1642..1862
Start ATG: 1001

Transcript No. : CT17184
ATGCCATCGCTAATCCGATATTATTGCAGGGCTTTTAGCAAGGGATTGTCTAAAGCCTTGTGTCACTTTTCCCGTTTCTCCTGTTTTATTTGCCA
CGAAATGGTTTTGCTAGACAATTCGAACTTTATCCTGCGCCTGGAGAAGATCGCAAATGCGGCCAAGAAGGACTCCTCCTTCACGCTGACGTTCA
AGCGATATGATGGCAACGATAAGCCCGTGCCGAGGGAAGGACGGCCACCGCTGCCCAAGCCGGAGACCTACATGTGCCTGATGCGCGCCCAGTCC
AAGTCCCAAAAAATTTCCACCGTTGTCCGGCAGGAGGATGTGCCCGCCATGATGAGCATGTACTCGCAGTTCATGAAGAGCAAGATGGACGGGCT
AAAGCGGGTTAAGAAAGTCAAAAGCAAGGCCAAGGCGACAAAGGGTTAATCGGGGCATAGTCTTAGTTAGATTTTATTTGACTGTTTACTGGTCG
TTTGTTTTAAACCTTAAATGCATCATTTTGTACGGAAAGCACG
(SEQ ID NO: 608)

Start ATG: 1

MPSLIRYYCRAFSKGLSKALCHFSRFSCFICHEMVLLDNSNFILRLEKIANAAKKDSSFTLTFKRYDGNDKPVPREGRPPLPKPETYMCLMRAQS
KSQKISTVVRQEDVPAMMSMYSQFMKSKMDGLKRVKKVKSKAKATKG*
(SEQ ID NO: 609)

FIGURE SHEET 330

Celera Sequence No. : 142000013384548
CACACTCACCGCGGGCGCAAATGCAGCACAAAGCAGACTAGAAATAACAATCGTTATCGAAAAGGTCGTCGAAATGGGCATAAATATTTTTATAA
ACAGTAAATATATAATTTCTTGTGGAGATCACGTTAAATGTGATGAGCTTTACAGTCGGATTGCGGAGAAAACAGTGAGTATGTTATGTATAATT
TTCATAAGATTTTGCAATGTGGCCCTTTTTTTTACAGAACCTGCAACCAGGGGAATACTACTTAGTCAGCAATGGCAAGCGCTTGGAGGGAGAAA
TTTCATCTGGAGATGTTCACTGCGTTCTCCGCCAGCTCGGTGGCAAAGGAGGATTTGGTTCCATGCTTCGAGCCATTGGTGCGCAAATTGAAAAG
ACAACCAATCGCGAGGCTTGCCGCGATCTAAGTGGTCGCCGTTTGCGGGATATCAACGAGGAGAAGCGGGTGCGCGCCTGGCTGGAGAAGCAGGG
CGAACGGGAACGGGAGGCCGAGGAGCGTAAAAAGCGAAAAATCGAGAAACTGCTGGCCGTGCCCAAGCACGACTTTAAGGACGATAAGTACGAGG
AAGCCAGGGCTAATCTGACCGAGAAGGTAAACGACGCCTTCGAGGAGGGACTCAAGCAGGCCGAGGAGAACAAGGAGAAAGGCGTCGAGGAAGCA
ACTTCCAGTGGCACAAAGAGGAAATCCCCCGCCGTAGACAAGACCAAGGCAAAAAAGAAGAAAAAGGGCACACTCTGGATAGACGATGACATCTC
TGGATCCGACTCTGACTCTGACGACAGCGAGGAGGAGCCAAAAACACAGAAAAAAGCTATACAAAACTAGATAAATAACTTTTGAATTAAGTATG
TACCAAAGACGTTCTTATTTCAAAATTTACCTGAAATAAACATAACAATATAAATACTTCTCATTTAAAATTTGAAAGATTTAGATTTAATACTA
TGGGGATAATTAAAGTAATTTATAAATATACATTTAAAAGAGAAAGAAAAATCACGGTGACACAAACTGTGAAGAAACCCAGGCCAATCCCCATTT
CAGGTTGGTTAGCATGAATTTCAGTGCCTTGGTCCACTGCTCCTCCGAGTTAAACTGGATTCTGTAAGGAAACCATCATTATTATAGGTAAAATC
TTTACCATTTCTAAACCTACTTAATAGAATAGGAATTTCCCGTGGAGGGATCGATGATCTTGCCCTTCTCCATCTTGTAGGGCAGCAGGAACTCG
GTGTCGCGCTTCTCGACCTCCTTCTGGAACTGGGTAAGACAGTCGAGAAAAGCTACCATGGCAGCATCAAACTTGGTGTCCCAGAAAAACTTAAA
TCCGCCGCTGCCATAAAGCGGGAGCTCTCGATTCTCGCCGAGCACCTCAACATACGAATGATTTCCAAAGGGTACTACACGATACCGCTCGAAGG
TGAGCCCTATCTTACGAGCAAGCGCAGAGAGCAGAAGCACCGTCTGGCCCCAAGCGGCGTTGATCTCTGACCAGTCCACGGATACAGAGGGCAAT
CGACCCAGCCTAAAGTTATTAATGGTACCGAAATGCCCGGCATGCCAGATGTGAAAGGTGATGTTGAATATGTTGGTGTCGCGCAGTTTGTCCAG
CTGCTGTTTCGAGTAGGCGATCTGACACTCCAGACTTCGTTTGTCATCCTCGGTGAGCATTAGCTCACGCCTGTGCTTGGTATACTCGCGCCAGT
AGCTTTCCTCCTGCTCGTGCAGCTCCTCTCGCTCCTGTTCCTCCTCGGCAATGGCATCATTTAGCGATTGTTCCTCCTTTTTGAGCTCTTTTAGC
TCCGACAGAAGCTGTTGCTCGCTGCGCTTTAGTTCGTCGAGCTCCTTGTCCAGGGCCTCAACGTTGGGTGCTACACGCTGTTGCTCTAGTTCATC
CAAATAAGCCTTGTACACATCCCACTCGTCCTCAGCGATGCGCAGTTCCCTGTCCATGATTTCCAGCATGGAGTCGGCACACTCTTCGCACAGCG
GATGGTCAATCTCAGAGTTGGAGGAGAGGCAGTCAAACAGCTCCGCTTTCAGCTTAAAAGCAGCACTCATTTTCTTGTTGTCCCTGCCATCGGAA
ACCAGCATAAAACCAGTGCCATTTATAGAGTCCGTAAGCCTGTAGGGCGGCACAAAGTGGTCGAAGCTGCTGGCGTCCTGCGGGTCCAATGTATT
GCCATTGTCTCCGTAGATGGGCACTGAAAAAGTGATTTATTAGACTAATTTCCAGAGTGTATCACCCATCATCACCTACAAGATAACTCCGCCAT
TGCGTGCACGCTAATCTTCTCCAGCTGCTCGTCCAGGACGATGGGCTGCAGGCAGCGCTGACAGGCGAAGGACACCGCCTGCTTTTCCGCCTCAC
TCATTGTCGTTCCTGTTTGTTGTCCTTCGATTTTTGCATACAATTAAATCTTTCACCGAGTGTAAAAACACAAATAATCCATCAGCTGTTTGCAA
CTGCTACCAGAGTTGCCACCCCCTCCGAAAAAGAGTGTGGAAAAATGGCGCAGTTAATCGGACAGTAAATCGTCAACCAACAACAACCTGAGACA
GTAAAAAAGAGAGAAATAACAGAAAACCAGTTTTAAACAATAACATTGCCTAATTGTGTCCGCCGGAGATGCTTAAGCGTGCCGCGAAGCTGCAG
GCCTTGACCACAATTCCCGCTGATAAGAGAGAACTCAAGGGGTTGGCTTTTGGTTTGTTTTGGTAAGCGACAGAACATTAGACGGAGTGCCGTCG
CCAGTGCTGCCAACCTATTTTAGCTATAGCAAATATTTCATAGTAGCAAAGAGGTAGAACCCAAATACAATTTTTATAAATAATAGTTTATAGTT
AGCGAACGGACTAAAAGAGAAACCTGATATCGAACGACTTATTATATTTTTTGTTAACTCAATTTTAAACTTACTCCAGCGTAAACCATACTTTA
TAAATAGTTTACCAAAAATGATAGCACAAGTGCCAGAAAGCTATTCACTTCATTTTTAATTTGATTAGGTAAATTGTGCGAAGGAAGTATTTAAA
AAAATGTGAAATGACGTACTAAGCACCCCACATATAGACTAAGAATTAAAGGTTAAGGACATTGACTTTCGCAATCTTTGTATTGTAGTTAAGCC
ACAAGCATTGATAAGCAAAGAAATTGTAAGAGTGAAATAAAATCATAATAAGATGAATTAATTAAAGTAGAGAAACTGATAAAGACTTGCACTTG
AAGCTGACACATGTGTTTAATAACTATATAATTGCTAAGGGAAATTTTGTTTTTGAAAAGTTTCCGTTATCAAGCTCGAAATTTCTAGCAATGGG
GCAGCACGAAATTTGCCGCTGTAAATCTAGCTTTCAAAACCTGGCAGCACTGTCGGTGGTCACATTGTAGCCTCTTCGCATTTGACGACCCATGG
AAAACTTTCAGTCTCTTGCAGGCAGCACAGCGATACGGAAGCAACAATTGAAACGTCCAGAACTCCTCCTCCCACGAGTATTTAAATTCTGACAC
AAGAGTGCCTGAACCAAAATCCCACTCACCGAATGCTGGTGCTTTGATTTGCAACTGTTCCTAGGTTCCGGCTGAATCCCTAGATTTGCGGATCT
ACGCAACTCATTCACTCAAAAGCCAGCCGAATTTATCGCGCCAGATTAAACAAACAGAAACAAAAAACAGAAGCCGAGACCAGTTCCACATCGTG
CCATTTTTATCTGGGCATATAGGCAGACGTGATTACGTGATTAGTGCGGC
(SEQ ID NO: 610)

Exon: 2755..2265
Exon: 2208..1161
Exon: 1106..1001
Start ATG: 2379 (Reverse strand: CAT)

Transcript No. : CT17226
CGACGGCACTCCGTCTAATGTTCTGTCGCTTACCAAAACAAACCAAAAGCCAACCCCTTGAGTTCTCTCTTATCAGCGGGAATTGTGGTCAAGGC
CTGCAGCTTCGCGGCACGCTTAAGCATCTCCGGCGGACACAATTAGGCAATGTTATTGTTTAAAACTGGTTTTCTGTTATTTCTCTCTTTTTTAC
TGTCTCAGGTTGTTGTTGGTTGACGATTTACTGTCCGATTAACTGCGCCATTTTTCCACACTCTTTTTCGGAGGGGGTGGCAACTCTGGTAGCAG
TTGCAAACAGCTGATGGATTATTTGTGTTTTTACACTCGGTGAAAGATTTAATTGTATGCAAAAATCGAAGGACAACAAACAGGAACGACAATGA
GTGAGGCGGAAAAGCAGGCGGTGTCCTTCGCCTGTCAGCGCTGCCTGCAGCCCATCGTCCTGGACGAGCAGCTGGAGAAGATTAGCGTGCACGCA
ATGGCGGAGTTATCTTTGCCCATCTACGGAGACAATGGCAATACATTGGACCCGCAGGACGCCAGCAGCTTCGACCACTTTGTGCCGCCCTACAG
GCTTACGGACTCTATAAATGGCACTGGTTTTATGCTGGTTTCCGATGGCAGGGACAACAAGAAAATGAGTGCTGCTTTTAAGCTGAAAGCGGAGC
TGTTTGACTGCCTCTCCTCCAACTCTGAGATTGACCATCCGCTGTGCGAAGAGTGTGCCGACTCCATGCTGGAAATCATGGACAGGGAACTGCGC
ATCGCTGAGGACGAGTGGGATGTGTACAAAGGCTTATTTGGATGAACTAGAGCAACAGCGTGTAGCACCCAACGTTGAGGCCCTGGACAAGGAGCT
CGACGAACTAAAGCGCAGCGAGCAACAGCTTCTGTCGGAGCTAAAAGAGCTCAAAAAGGAGGAACAATCGCTAAATGATGCCATTGCCGAGGAGG
AACAGGAGCGAGAGGAGCTGCACGAGCAGGAGGAAAGCTACTGGCGCGAGTATACCAAGCACAGGCGTGAGCTAATGCTCACCGAGGATGACAAA
CGAAGTCTGGAGTGTCAGATCGCCTACTCGAAACAGCAGCTGGACAAACTGCGCGACACCAACATATTCAACATCACCTTTCACATCTGGCATGC
CGGGCATTTCGGTACCATTAATAACTTTAGGCTGGGTCGATTGCCCTCTGTATCCGTGGACTGGTCAGAGATCAACGCCGCTTGGGGCCAGACGG
TGCTTCTGCTCTCTGCGCTTGCTCGTAAGATAGGGCTCACCTTCGAGCGGTATCGTGTAGTACCCTTTGGAAATCATTCGTATGTTGAGGTGCTC
GGCGAGAATCGAGAGCTCCCGCTTTATGGCAGCGGCGGATTTAAGTTTTTCTGGGACACCAAGTTTGATGCTGCCATGGTAGCTTTTCTCGACTG
TCTTACCCAGTTCCAGAAGGAGGTCGAGAAGCGCGACACCGAGTTCCTGCTGCCCTACAAGATGGAGAAGGGCAAGATCATCGATCCCTCCACGG
GAAATTCCTATTCTATTAAAATCCAGTTTAACTCGGAGGAGCAGTGGACCAAGGCACTGAAATTCATGCTAACCAACCTGAAATGGGGATTGGCC
TGGGTTTCTTCACAGTTTGTGTCACCGTGA
(SEQ ID NO: 611)

FIGURE SHEET 331

Start ATG: 377 (Reverse strand: CAT)

MSEAEKQAVSFACQRCLQPIVLDEQLEKISVHAMAELSLPIYGDNGNTLDPQDASSFDHFVPPYRLTDSINGTGFMLVSDGRDNKKMSAAFKLKA
ELFDCLSSNSEIDHPLCEECADSMLEIMDRELRIAEDEWDVYKAYLDELEQQRVAPNVEALDKELDELKRSEQQLLSELKELKKEEQSLNDAIAE
EEQEREELHEQEESYWREYTKHRRELMLTEDDKRSLECQIAYSKQQLDKLRDTNIFNITFHIWHAGHFGTINNFRLGRLPSVSVDWSEINAAWGQ
TVLLLSALARKIGLTFERYRVVPFGNHSYVEVLGENRELPLYGSGGFKFFWDTKFDAAMVAFLDCLTQFQKEVEKRDTEFLLPYKMEKGKIIDPS
TGNSYSIKIQFNSEEQWTKALKFMLTNLKWGLAWVSSQFVSP*
(SEQ ID NO: 612)

Classification: hypothetical

Celera Sequence No. : 142000013384004
AATAATTTGTTTGTAAATTTCTATTTTTACTTTGTGAAGTAATGATTTTATATTAATAATATAATTACCAAGACTAAACGGAATAATTATAAGGT
TGTGTATTAGTAGAGAACAAAAACAGAATGAAATACATTTGTAGGAATCACCTAATATTTAATTATATTTTATATTATATTAATTATAATTATAT
TTGTTCTTTATACAATTTTATACATTGTATTTTATAGTTTATTAAATATTCCCGCTTAAAAAATAAAATGTTGTTTCTATTTAAATTACCGCAG
CTGTTGGTGGTAATTTAGATGACCTGATTCGATTTGGTATTATGGGAACTTTTCCAGATTTGGTCACACTGCCCTTTACACTGTTTTGGTTTTCG
TGAAAATGTCCACATACTACTTTGTTATTGTGGGTCAAAATGATAATCCCATTTACGAGAAGGAATTCAGCACCGTGAACAAGGAACTAAGGGTA
TGTAGACCTGGGCAACGTCTCATAGAACTGTGTAAATACATTCTCCTTCTGCAGAAAGAGGACCACAGGCACCTCACCCAGTTTATTGCCCATGC
CGCCTTGGATTTGGTGGATGAGCACAAATGGAAGACGGCCAATATGCAGCTGAAATCCATTGATAGATTCAATCAGTGGTTTGTTTCGGCCTTCA
TCACAGCCAGCCAAATACGATTCATCATCGTTCATGACAACAAAAACGACGAGGGAATCAAGAACTTCTTTAACGAGATGTATGACACGTATATC
AAAAACTCCATGAATGCCTTCTATCGCATCAACACACCCATTAAATCTCCGATGTTTGAGAAGAAGTCGGAGATCTTTGGTCGGAAGTATTTGTT
ATCATAAATTTGTTAAAACCTGTAGCCATTAAGTAATTGTGTAATATAAAACTTGAAATAATTTAAAAGCATAACTTTACCCTTTCTTATACAGT
TGAGAAGACCCGAAACCAATGAATAATCTAGTTTATATTTTATTTAATTTATTTAGAAAAGCAGCCTAGGCTTAACATTGATGGACTTGTTTTAT
TCACTTTTTACTCAATGCGCCCTCGAATCAAATCTAAAACGATTTAACGCCCGTCTCCAGACGACAGTCCCAGACTGGAGTAAATTAGATGTGTG
GGTTGAATAGATGAACAACGCATGGAATCAATTTGAAACTAAAGCAACAAAATATACGGAATTTGTAATGGGTCTTTGCAAAGAAATCTCTTGGT
GGTGGCGAGGAAACCGTCCGTCCTGCAGCTTAGTGCTTCTTGTTCTTTCCAGAGCGCTCATATTTGCTCTTGGACTGGTGCCACAGAGCCAGAGG
AATGGCCAGGGAAGGCAGAGTCATCACGGCGAAGGCCACCCAGTCGAAGAAATGGGAGGAGAAGCGCTTGTTGTACTCGTTCAGGTTGACAATTC
CACCCTCACCGGGCTCAGAGCTGACCGCCAGTTGGAGCTGCAAGAATTGTTGGGTATTAAGTTCTTTGATCGATCTTTCAACAGGTAACGGGCAT
TTTTAAAAGACTGTTGTGTATAAATTCACTTAGTTGAGATTATTAAATTTAAAAGTGAATGATTTTGGTTTGCTTTGGCGGTGGCTTCTGTAACA
CTGAGATTAGATAAGATTTTTCAGGGCGGACACTGAGATTTGATGCCCCCACATTCAGCTATAACTTACCGTCTCCGACTCCTCGACAGCCTTGT
AGGACACCTCGGCGGCGGTGAAGTTGAAGTAGCCGAAGGCCTTGGGCCTCACCACCAGGACATGGGTGAAGTTGGTCTGGGGAGCGATCCTATCG
ACCACGGCGGTGGGCTGTCCTCCGACAACGTCGAAGGCCTCCGGGTGGAAGCCGGAGTCTACCAATCGCACCTTGGTGGCGGCACCGCTGCCCAC
GTTGAAGATGGTGTAGCGTACCAACAGGTCGCTCTTCTCCACCAGGTACTTGTTCAGGATCTGCTTAGAGACCAGGAGACGGGCACGGGTCTCGT
CTTCCGACAGGCAGGTGCTAAACACCGCGCACAGGGCGAACAAAGTCAGCAGGTGCTTGAACATTCTACAATCACAGATAATATGAAGTTTTATT
TTCACGTTTCACTTTTTTGTTGACGTGGAAGGGTCGCCGAAAAACGAGCGGCACATAAGGGCGACCGCTTTCCGGTGTGTTTTCTAGACATTCAC
GCATCATAGCTGCCCCGAGCACACGTTCAGCATAAACGTACACATTTTAATTCATAATTTAACTACTTACTTGTAATTTGGGTATTTCCTTATCG
AGTATTTCAGTACAACTAAGCAGCAGTCGTAGCAGGCAGCCGCTTTCTCGGTGGTTCGTGACGTGGAATGGATTCGCTGTCAAACTTCGTGCGTC
AGTGGTGCCAGGGCTGCGTCAACATATCGATGTATCTGCTGGCTGTCGGCAGTATATTAATACCAACACCATAGTATTTTCGTCGGTTATGAACA
CAACACAACTAAATTTTTTTGTGAAATTCATAAAGCTTAATTTGTTTTTTTATCACCAGTGAATATATTTAGTAATAATGAACGAAATAGTTTCA
AATTAAAACCGTTAGAAGCCGCTATGGTGTAGCTGTGTGCAGTGCTACATAAAAAGGAATTATGTTTATAATAACAAAAATTAAAAAAAAAAACG
TTTTAACGTAAACGTATACACTTAAATCTTTTCGAAATTAAATTATATTAAAATCGGTTTCAAATTGTTTTCTATAAAGTTTAATTTAGCTTTAA
ACAAAAAATTAAGTCGTTATTTTTAATTTGCATTCATATATTATTTAATAAAAATTTAAATTGCATGCAAAAGAAGTAAGGAAGCCTGAAATTTT
AATTATTTCTGAAATTTTAATTATTTCTGAATAGCGCACAACTACTCGTGGAGATTCGGCAACTCCGCTCCCCAGCGTCTGTTAAGCCGCTGTTA
ATAAGCAGCAGCTGTTGTTTGAAACACCATAAACAAATGTAAACAAAACTCTTTTTATGCCTTTTATGACTTTAACTAATGTTTTGCTACGCGGT
TTTAAAATAGTTAGGCATTTTATCTGCTTTTGTTCGTACATTTGGCATACATTTCAAATAGAACAGCTGTTAGCCGGCACCCGGGAATGCCCTTG
AATGACATTGCACCCTACATCAAGGTTCTCGGCCTCTCAGTTCACTAATGCATCATGATAAAATTACCTCAAATCACGATAAAGAAATGAAATTC
AAGGGGACAATAGTAGATAACTGGATTAATGGGTTCTTCAGCATTTTAACGACGCACCCCCAATACTAGATTAGGACTGACTAATAGCACGCACT
AATGATAGAGGTTATCTTGATCGCCATGACCGAACCGATTTGGCTTATCAGTGGGAGGCAAATTTCGCTGTGCACACTCAATTTTCATCGCACGC
AACCGCGGTTAAGTCGTCCAGTTGGAA
(SEQ ID NO: 613)

Exon: 2447..2439
Exon: 2336..2256
Exon: 2059..1685
Exon: 1462..1001
Start ATG: 2447 (Reverse strand: CAT)

Transcript No. : CT17318
ATGGTGTTGAACCACCGAGAAAGCGGCTGCCTGCTACGACTGCTGCTTAGTTGTACTGAAATACTCGATAAGGAAATACCCAAATTACAAATGTT
CAAGCACCTGCTGACTTTGTTCGCCCTGTGCGCGGTGTTTAGCACCTGCCTGTCGGAAGACGAGACCCGTGCCCGTCTCCTGGTCTCTAAGCAGA
TCCTGAACAAGTACCTGGTGGAGAAGAGCGACCTGTTGGTACGCTACACCATCTTCAACGTGGGCAGCGGTGCCGCCACCAAGGTGCGATTGGTA
GACTCCGGCTTCCACCCGGAGGCCTTCGACGTTGTCGGAGGACAGCCCACCGCCGTGGTCGATAGGATCGCTCCCCAGACCAACTTCACCCATGT
CCTGGTGGTGAGGCCCAAGGCCTTCGGCTACTTCAACTTCACCGCCGCCGAGGTGTCCTACAAGGCTGTCGAGGAGTCGGAGACGCTCCAACTGG
CGGTCAGCTCTGAGCCCGGTGAGGGTGGAATTGTCAACCTGAACGAGTACAACAAGCGCTTCTCCTCCCATTTCTTCGACTGGGTGGCCTTCGCC
GTGATGACTCTGCCTTCCCTGGCCATTCCTCTGGCTCTGTGGCACCAGTCCAAGAGCAAATATGAGCGCTCTGGAAAGAACAAGAAGCACTAAGC
TGCAGGACGGACGGTTTCCTCGCCACCACCAAGAGATTTCTTTGCAAAGACCCATTACAAATTCCGTATATTTTGTTGCTTTAGTTTCAAATTGA
TTCCATGCGTTGTTCATCTATTCAACCCACACATCTAATTTACTCCAGTCTGGGACTGTCGTCTGGAGACGGGCGTTAAATCGTTTTAGATTTGA
TTCGAGGGCGCATTGAGTAAAAAGTGAATAAAACAAGTCCATCAATGTTAAGCCTAGGCTGCTTTTCTAAAT
(SEQ ID NO: 614)

FIGURE SHEET 332

Start ATG: 1 (Reverse strand: CAT)

MVLNHRESGCLLRLLLSCTEILDKEIPKLQMFKHLLTLFALCAVFSTCLSEDETRARLLVSKQILNKYLVEKSDLLVRYTIFNVGSGAATKVRLV
DSGFHPEAFDVVGGQPTAVVDRIAPQTNFTHVLVVRPKAFGYFNFTAAEVSYKAVEESETLQLAVSSEPGEGGIVNLNEYNKRFSSHFFDWVAFA
VMTLPSLAIPLALWHQSKSKYERSGKNKKH*
(SEQ ID NO: 615)

Classification: hypothetical
Gene Symbol: SsRbeta
FlyBase ID: FBgn0011016

Celera Sequence No. : 142000013385214
AATTAGCGGAATAGCTTTTATTGGACGGGCTAAAAAAAAAAATCAAAGCCAATCAGTGGCGTGATCCGAAATCAACACCATCTTGGCCATCACCT
AGATGGGTGGTGGAAGATAGTGGGCTGGTGAACTCGATCCCTTTTGACATGTTTACACATTTAATTAACTTACACGCGCCGAAAGTTTCCGGACA
CGTTAGATAGTCCCCGTCTAATCACACCCAAGCGAAAACCCCACCCGCATGAACTTCCAAAATGGGGCTAAGAAAACAAAAGGATAAAGACCCTT
TCGCAACCCAACCCCTAAGTCTTCCCTTTTTGACAATTTGAAACCAGTTCAAGTGGTTTAATCATTTAACGCACATCATAAAAATCGCATCAAGT
GATTTTTATTTACACGCCCAGGACAAAAAGGATCCCCAAAACCTAAACGGAATACAATGATTGGGGCGGGGGTGCGAAATGGTTGGGGGTGAGCC
ATCCCTTTGAAACCCAAGGCGTTGGCTAAGAACAAGAAAAATGAACTCGCTCACTAGATAAGGTTTCGGTTAGTTGATAGACTTTTACGCTGTAA
TGAAATCTTAGAAATTCCATTTAAGAAGGAAATATATATGTATTACAAATAAGCTTAACCGCAAAAGGTATTAGCTTTTAATCTTAAGGAATATA
TAAGTCTTTATATAATGAGTACGAACTTCCTAAACATTTTTCCTTACTCCAATTTGTGATTAACTAATTTTATAGAACTATTTAACCTCAGAACA
AGAGCACATATCAGTAATTAAATTCAAGTTTTCATGTAGGTTGTGTTAGCGAAGTATTTAATCATATAGTTTTATTTTTTAAATACATGTTAAGC
TGGTGAGGCGTAGTGTATATGTGAATTTTATTCAAAATTTAATGCGCAACCGCATAATGGACATAAGATGTGAGACTTTAGATGAATTTGCGTGA
AGATTGATCTTGATCAGAGGCAGACGACCGAAGAATGCGGATTACACTGCTTAACTGAAGGTGTTGACCTGTGAATAAATAAAAACATTCATTTA
AATTTAAATCATTTCATTCATTTGTATAACACTTACAATATCGTCGATCTTCAAGATCGATCGAATCGTCTCCGTGGCCAGGGTGATCGACGAAA
TACTGACCAGCAGCGGCTGCACAACGTTCTCCGCGAAAATGTCTGTGATGGCGCCCTTGCGCACATTAATACCGGCGTTCTTCTCACCCTGAGCG
TGGCGGTTGCGTAGCTCCGTGACCGTGGCAATGGGATTCAAACCGGCGTTCTCAGCCAGAGTGGAGGGAATCACCTCCAAAGCATCGGCAAATGC
ACGGAAGCAATACGCATCCACACCCTCCACGGTTTGTGCCAATGCGGCTAGCTGCAGGGCCATCTCAATCTCGGGCGCACCACCGCCGACAATCT
GGGCGCGCAGCTTCACCAGGCAACGGACGACACAGAGGGCATCGTGCAGGGAGCGAGCAGCCTCCTCGAGCACCAGCTTGTTGGATCCGCGGCAG
ATGATCGAGACAGTGCGTCCCATGTTCTGAATGCCGGTGATCTTCACAAACTTGTTGGTACCACTGGCCACCTCCTCGACCAGATCGGCACTGGA
AAGGTTCTCGGCTGTGAAGTGATCCAGCGAAGCGATCGGTCGGCAGTGCAGGGTCTTGCACACGAACTCAATATCCTCGCGCTCCACATCCTTAA
CGACCATGCACTTGATCTTGTCCAGGAAATGCTGAGCCAGATCAGAGACAGCATCGCTAGATAAGTGGAGAACTATCAGCACAAAGTGGACAAAT
AACAAGTAAGCTAAACCTACCGCAAGATAGACTTCTGAACGAGAAGAACATTGCATCCTGACTTCTTGATCTGCTTGACAATGTTCAGGATGTAT
GAACGCTCCTCCTTGAGCACACGATCCATGGCAGCGTAATCCGATACAATCACATTGTGATCCATCTGTAATTTCGGCATAAATTATAAAAGACA
ATAAATTGTTAGGATCATAGCGATGTACTCACATCGGTCTTGGGGGCCGAAATGCAGAACTGGATAAGACCGATCTTGGCCTTCTCAATGCGCTT
GGGAGCGTTGGATCCGGCAGAGCGGCAGGTGAAGACCAATCCATCGACCAGCTCGGTGTCCTCAACAGTGCCACCCAGGCTGGAGATGACCTTGA
TGTTCTTGAGATCCACAGAGGTTTCCTTGCCGGGATCCGTAACCTTCAGCACGGCATCCACGGCAATGGGGGCCAGCAGGCTGCTCTGCTGCGAC
ACCACCTTGGAGTTCAACGAGGTGGAGGCGCTCTTGATCAGCGTCTCGCGGTCGTCCAGCTCGATGGGAGTGGACATCTGTTTAAGAATCTCGAC
GGCCTTGTTCGAGCAGCGCTGGAACGAGTCCGAAATGGCCGTGGGATGCAGACCCTTCTGCAGCAACTTCTCGCACGCCTCAAGCAGAGCTCCGG
CAATGACAACCACGGAGGTGGTGCCGTCACCAGCGGCCACATCCTGGGCACGCGACAGCTCCACCAGCATCTTGGCAGCCGGGTGCAGTACATTC
ATCTGCTTCAGGATGGTGGCGCCATCGTTGGTGATGGACACCTCGCCGTTGCCGGCCTGGATCATCTTGTCCATGCCGCGGGGGCCCAAACTGGT
GCGGATAGCATCGGAAACGGCTGGAAAACAGAATTATTTCAATAGGTTATAAATGTATTTTAATATTTCGTTAAAACTTAATGAGAAACTCAGAT
AAGTGGAATTCGTGTGGTTAGTTTTACACAGCAGCATGACTAATTTACATACATACATACAAAAAGACATATGGTGTTTTATGTGTTAATTCAAA
AAATCTACTGTAACTTATCTTAAGAGATAAACAATAAAATCCTTGTAGCGGATAAAAGGGTATTGGGAATAGAGTATTAAAAATCCTCAATTTTT
AGGTTGTTTCAATTCATCACATGAGTAATGCGCGCTCTTCTTCTTCTTCCGCCCAAGAAGTTTCCAGACAGCCGGCATCCAACTGCTTTTTCAAT
AGGCCATTTGGCCGGAATTCTGATGCACCACTGCTCGGAATTCAGTCACCTCGGTTCTTAGCTCAATAAATAGCACATACGCCAACATTTTGAT
ACAAAAATGTGTTTAATTTTGTTAATTCCTCGCTTTTTCTCACCTTTGGCCGCCTGGATGTTGGACAAACGCACATCGGTGGGCTTCGACTTGT
CCTTGAAGGCCTTGGCCGTTGGCTTGATGTTGACAGCTGCTGCCTTGGGCGCCATTGTAGGGTTAAGTTATAGTTTTTTAACAAAACACAGTTAT
TCTACAATAAATTCACAGCGATTTACACAGAACACGTTGCTGCGAAATGTTAAGGAAAGTGTGGCCGCACTCGCTGAGCTCAAATATACCGCCAA
CTTATCGGCATCGATAACATCATCCCTTGTGAATGGCAAATTGGTGTGACCGTATTTTGCGTTGTGACTCGGCTGCTTTATTTACATTGAATTTT
TGTTCGATTTTTGAATTTAAAATAAAAATAATGCCGCACGGACACTCTCACGATCACGGCGGCTGCAGCCACGAGGCCTCGGACGTGGACCACGC
CCTAGAAATGGGCATCGAGTACAGCTTGTACACCAAAATCGATCTGGACAATGTGGAGTGCCTGAACGAGGAGACGGATGGCCAGGGAAAAAGTG
TCTTTAAGCCGTACGAGAAGCGCCAGGATCTGTCCAAGTACGTGGAGAGCGATGCGGATGAAGAGCTCCTCTTCAACATTCCCTTCACCGGCAAC
ATCAAGCTCAAGGGCATCATCATAAGTGGGGCCAATGATGACTCCCATCCAAACATGGTCAAAATGTAAGGAACAAAAGTCAAGGCTGCTTTAAT
ATTACTATATTCATCATATATCTTATTTTTCAGCTTCAAGAACCGACCCAGGATGACCTTTGATGATGCCAGAGCAAAGCCCGACCAGGAGTTCC
AGCTGACCCGCGATGCCCGCGGAGAAATCGAGTACTCACCCAAAGTGGTCACCTTCTCCTCCGTGCACCATCTCTCCCTCTACTTCCCAGCAAT
TTTGGCGAAGACATAACACGCATTTACTATATAGGTAAGCTCACAACAATCTATGTTTTATCTGTGTTCCCAACTAAAACCAAGTCACTATTCAA
AGGTCTTCGAGGAGAGTTCACAGAAGCTCATTACCATGGCGTAACCATATGCAACTACGAATCCCGTGCCAATGCAGCGGATCACAAGGAAAAGG
CTTTCGATGGAGTCGGCAGAGCCATCCAATAGGGTTATAGAGATTAAAATTTACAATTTAATTGAGTATCTCTGTAGTGTATATATTTTGTGATC
(SEQ ID NO: 616)

Exon: 3370..3180
Exon: 2680..2028
Exon: 1965..1826
Exon: 1766..1082
Exon: 1018..1001
Start ATG: 3285 (Reverse strand: CAT)

Transcript No. : CT17430
TCGCAGCAACGTGTTCTGTGTAAATCGCTGTGAATTTATTGTAGAATAACTGTGTTTTGTTAAAAAACTATAACTTAACCCTACAATGGCGCCCA
AGGCAGCAGCTGTCAACATCAAGCCAACGGCCAAGGCCTTCAAGGACAAGTCGAAGCCCACCGATGTGCGTTTGTCCAACATCCAGGCGGCCAAA GCCGTTTCCGATGCTATCCGCACCAGTTTGGGCCCCCGCGGCATGGACAAGATGATCCAGGCCGGCAACGGCGAGGTGTCCATCACCAACGATGG
CGCCACCATCCTGAAGCAGATGAATGTACTGCACCCGGCTGCCAAGATGCTGGTGGAGCTGTCGCGTGCCCAGGATGTGGCCGCTGGTGACGGCA
CCACCTCCGTGGTTGTCATTGCCGGAGCTCTGCTTGAGGCGTGCGAGAAGTTGCTGCAGAAGGGTCTGCATCCCACGGCCATTTCGGACTCGTTC
CAGCGCTGCTCGAACAAGGCCGTCGAGATTCTTAAACAGATGTCCACTCCCATCGAGCTGGACGACCGCGAGACGCTGATCAAGAGCGCCTCCAC
CTCGTTGAACTCCAAGGTGGTGTCGCAGCAGAGCAGCCTGCTGGCCCCCATTGCCGTGGATGCCGTGCTGAAGGTTACGGATCCCGGCAAGGAAA
CCTCTGTGGATCTCAAGAACATCAAGGTCATCTCCAGCCTGGGTGGCACTGTTGAGGACACCGAGCTGGTCGATGGATTGGTCTTCACCTGCCGC
TCTGCCGGATCCAACGCTCCCAAGCGCATTGAGAAGGCCAAGATCGGTCTTATCCAGTTCTGCATTTCGGCCCCCAAGACCGATATGGATCACAA
TGTGATTGTATCGGATTACGCTGCCATGGATCGTGTGCTCAAGGAGGAGCGTTCATACATCCTGAACATTGTCAAGCAGATCAAGAAGTCAGGAT
GCAATGTTCTTCTCGTTCAGAAGTCTATCTTGCGCGATGCTGTCTCTGATCTGGCTCAGCATTTCCTGGACAAGATCAAGTGCATGGTCGTTAAG
GATGTGGAGCGCGAGGATATTGAGTTCGTGTGCAAGACCCTGCACTGCCGACCGATCGCTTCGCTGGATCACTTCACAGCCGAGAACCTTTCCAG
TGCCGATCTGGTCGAGGAGGTGGCCAGTGGTACCAACAAGTTTGTGAAGATCACCGGCATTCAGAACATGGGACGCACTGTCTCGATCATCTGCC
GCGGATCCAACAAGCTGGTGCTCGAGGAGGCTGCTCGCTCCCTGCACGATGCCCTCTGTGTCGTCCGTTGCCTGGTGAAGCTGCGCGCCCAGATT
GTCGGCGGTGGTGCGCCCGAGATTGAGATGGCCCTGCAGCTAGCCGCATTGGCACAAACCGTGGAGGGTGTGGATGCGTATTGCTTCCGTGCATT
TGCCGATGCTTTGGAGGTGATTCCCTCCACTCTGGCTGAGAACGCCGGTTTGAATCCCATTGCCACGGTCACGGAGCTACGCAACCGCCACGCTC
AGGGTGAGAAGAACGCCGGTATTAATGTGCGCAAGGGCGCCATCACAGACATTTTCGCGGAGAACGTTGTGCAGCCGCTGCTGGTCAGTATTTCG
TCGATCACCCTGGCCACGGAGACGATTCGATCGATCTTGAAGATCGACGATATTGTCAACACCTTCAGTTAA
(SEQ ID NO: 617)

Start ATG: 86 (Reverse strand: CAT)

MAPKAAAVNIKPTAKAFKDKSKPTDVRLSNIQAAKAVSDAIRTSLGPRGMDKMIQAGNGEVSITNDGATILKQMNVLHPAAKMLVELSRAQDVAA
GDGTTSVVVIAGALLEACEKLLQKGLHPTAISDSFQRCSNKAVEILKQMSTPIELDDRETLIKSASTSLNSKVVSQQSSLLAPIAVDAVLKVTDP
GKETSVDLKNIKVISSLGGTVEDTELVDGLVFTCRSAGSNAPKRIEKAKIGLIQFCISAPKTDMDHNVIVSDYAAMDRVLKEERSYILNIVKQIK
KSGCNVLLVQKSILRDAVSDLAQHFLDKIKCMVVKDVEREDIEFVCKTLHCRPIASLDHFTAENLSSADLVEEVASGTNKFVKITGIQNMGRTVS
IICRGSNKLVLEEAARSLHDALCVVRCLVKLRAQIVGGGAPEIEMALQLAALAQTVEGVDAYCFRAFADALEVIPSTLAENAGLNPIATVTELRN
RHAQGEKNAGINVRKGAITDIFAENVVQPLLVSISSITLATETIRSILKIDDIVNTFS*
(SEQ ID NO: 618)

Classification: chaperone

Celera Sequence No. : 142000013384254
AAGTTACGAAACCAAAGAAAAAAAATGAATGTTTCCTATTTCCCAACCGAAAACATATAATAATAAATATTGATTACAAAAACGAATCATCTTAA
TTTGAAAAATTCATTTGTTTATATACTTTAAATCGTCATATAGATGGCGCTACATTTGCCATTGTCACTCACAGCGCAACGCGCACACCTTATCA
GCTGAATTTGTTGCCATTCAGAATGCAGTGTTTGTGAAGGCGTAGTTCTGTTGTTTTTTATATTTTCCCTCTTTAAAAATACACAAAATGTTGAA
ACCCAAAGCTTTGACGCAGGTTCTCAGCCAGGCGAACACCGGCGGAGTGGAGAACACCCTGTAGGATAGTCCCTTACCATGCCATTCCTTCAAAT
ATCACTTATCCCTGCATCCACAGCCTGCTCAGCCAGGAGGGAGCTCTATTGGCCTACTCCGGTTATGGCGATAAGGATGCCAGGATAACGGCGGC
CATAGCCAGCAACATATGGGCGGCCTACGAGAAGCATGGACGCAACGCCTTTCGCGAAGGTCGCCTCACTTTCGTGCTCATCGATTGTGAAAACG
GTCATGTGGCCATCACACAGGTGGGTGATCCTCTTTTTTTTAGCAGGGATTCGTTCTATAAAATCTTAACTATATTCCTTTTTACAGGTTGCCAG
TGTCCTTTTGTGCCTGTACGCCAAGCAAACGGTGGGATTGGGTCTTCTGAAGCAAAAGGCCATGTCACTGGCCTCCTATTTGGAGCGACCGCTTA
AGCAGATCTCGGCCTCATAAGGATAAAACAATGATGTACCAAGTTCCGAAATGAATAAGTTAATAAGTGTATGCATCAAAAGTGAATCAAATGAA
TATGAATAGTCTGCGGAAAAGTTTAAACGATAATATATTAGTACTTGAAATTATGAATCTTTAAGGATTTTGTTAGTATTTAAGGAAAAACTTGT
CTGCTGGTTTCCAAAAGTAACCCAAAGATATTTCGTATTCTGAATTATTTGGATAGAGGGTCAGGTTTATTATTCTGCAAGATTTGTTCAAGAAA
ACACACAATCATTAGGGAATATTGTATAAGAAAATTTTGGACTTAATTACTAAGTGTGGACTTATTCGATGGCGTAGAGCTTCAGGGTGCGGTCC
ATGCTGGTGGATGCCAGATACTGGGCGTGCTTGCCGAATCTCACGCCCGTTGCCAGGGCCGTGTGGTCGTTGAATACCTTCAGTTCCTGCCACTG
CTTGCACAGGTAAACCCTGTAAATAAAACGAAGCAACCGTCAGAATTTGTATTTGTACCGTGGCAACCAAATAAACAAGTTAACTAAGGGAATCT
TCTTTGGCGAATTTAACTTAACAATGCGAAAGTTTAAAAGAAAAGTTTACCGCGAATATGAAAGTAAGTATTATATTCTAATATGCGAAGACTTA
AAAATGCATGCTGCTCTTCAAGATTTCGTGCGACCCAAGACCCATGTGGAACCGGAGCCTCCAAAGCCCATAAACTTATCGATTGAGGACTTCAA
TGCGGTGCGAAATAATTAATTTTTATATTTCCAAAGTTAAGTTTTATTAATATTCCTCAGCGCGGAGAGATCGCCAATCCCCGTGCTCCTTGTGT
GGTCACCACCATCGATCCCGATTATATTAAGGACGCCAGTGCGCAACGTTTGGCCAGAAAATTTCGCATGAAAACGTAAGGAATCAAATGAATTA
TGTGCTGGTGCAATTTCACAGCTTTTTCAGGGACATCCTACTCTTGAGGGAGATTACCCGCAATCGCTTTATGTACTATGCTACGCAAGAACTTT
TTTTGGACCGAAAACGCGAGAAGGAATACCAAGACAATGTATACGAAAAGGCCGAGGAGTTTCACAAGTTTGCAGAGGAGTCGCTCAAGAAAATG
GAAGCGGAGGAGTTTAAGAAAATGTTAGAGGCCCAAGAAAAGCTGAAGACACTGAAGGAAAGCAAACTGAGCGAAGAGCTGAACGAGGTGAAGCT
GGAGCATCAGCGAGTGCTGATGGAAGTGCAGGAGGTCTACGGTCGCTTTCAGTATTTACTCAAACTGATCAGCTACTTTGATGACACAGTTGAGG
AGGAGCAAACCGAGGGAGACGATGCCAGCAATAGGCTTAGCATGCCGCAGGAAATCGTAGCCATGGAGATCACCGAACGACATCCAGCGGGTCTC
GAGCAAGTGCGTCAAGTCCAAGACTACATGGAGAAGATAGTGCGTCCGTATTTGGCAAAGCGGAATCATCTCAATGCAGAGATTTGGATACGTGG
CTATGAGAGAAATCGCTTAAAGGTGTCCAACTACAACAGGCGCTTTTCTCAGTTGGCAATCTTGAACCACATCGTAGCCATCCTCCATGACAAGG
CCCAGAAGACGTACGAGCGTCAGGTGAAAGCCAATGTGTTCCTCAAGGATCCCGAGTTCCTGCAGCGACGGGTGGCAGGTCTTCAGGAGCGTGCC
AAGGGTCTATTAAATGACTTCGAGCAGAGATACTGCAAGGAGTGAGTTGGGATGCGTACATATTTGAATCAACTATTTTATATTCTTAATTTCCA
GCAAGCTGAATATCAAGCTAAATGCTATTGTACCAATTATTCTCAAGCAAATCCAAAACAAAGTTAAGCCGGAGCAAAAGCGAGAGGTTACGCAG
CCGCCATCCAAGCCAGCAGCCCAGAAGTCGTCCAAGCAATGGCGAACACTGGAAGACATGCAGCCTCCACCACCGCCACCCAAGTCTACATACGC
GGACGAACAGGACACGACTCTTGCCAAGGTGGAGAAAATCCAGGGCTACGTTTTGGAGCTCTTGGCTAAACTGGACCACATCGAACCGAGCAAGC
TGCGAAGTGTCGAGCAGCAGGTTCGACGTCGCATGGCAGCGGAGAAGGAAATGTCTCGCCGTGCGTTAGTCAAGCAGAACCGGCTACACAACTGG
ATGGCGCATTTCAAGAAGCATCATGATCAGCAGGTTGAGCAACGATGGAAAAATAAAGTCTAAGCTAGACAACAACACCATACTTAAAACATTAA
ATGAATACAATTTAAAACTTATTTTAACCTCATTCTGAATGATTTCAATAAGAAAAGTACAATTCACTTACCTGACATCGCTGCCGGCGATAGCC
AGATAGGTTCCGCTTTGGTCGAAGCACAGATCCTTGACCTCGTAGCCGTCATCAAGCTGGATTGTCTTAAAGTTCTTCAGCTTTCGCAGATCCCA
CAGCTTAACGCAGGCATCATCTGCAGCGGTGGCCAGGTAGTAACCGTTCTCCGAGAAGGAGATGGCCGAAATGGGACCGGTATGACCAGGGAAGT
TGGCCACATTGCTCTGCTCCTTCAAATCCCAGATCTTAACCTGCGAGTCCACGGTGCCCGTACCGAAGATCAGACCATCAGGATGGAATTGCGCT
GTCGTCAGCCCGACTTCGGCGGTATCGATTACCTTGGTGAGCAGGCGTCCTGTGCGGATATCGGAGAATGCCCAGTGTTTGTCGGATGATGTGGA
CAGCAAGTAGTCGCCAGTGGGGTGCAGCGAAAGGCCAGTAACAGGTCCTTCGTGGCAGCGCAGGAGAAGCTGCGTCTGCGAAGTGGGCACGTGCC
AGATGCGTATGTTCATGTCGGGCGAGCCGGTTATGACTGTATCCTCGTTAGGATGATATATGACTTTGGTGATCTTCTTGGTGTGTCCCTTCAGG ATGGCCACCATCTGCTCTGTGTCCTTGTTGAACACGGTGGCGTTTTTATCGTTGCCTCCGGTCAGAATCTTACTGTGATCAGCACTGTTGATGTC
CAAGGCCAGAATGCCGGGAACGGAGGCCGAGTGTAGGCCGGGATGGGATGCCACAGTAAGGAAGTTCTTAACCTGATCCGTTGTAACCAGATCCT
CGGGCACAGTGCGTCCGCGCTTCTTACGCTCCTGCGTCAGCACCGTGGCCTTGTCCTGCAGTTTCTGTATGACCTCGGCGCTCATGCCCGCCTGC
TCCATGGGATGGGCAGCAGCTCCGCCAGCCTCAGAGGCCAGGGCCGGTTGTGGTATTGCCGTGGGTGCGTTGGCAATGCCCGCCTGCGGTTTCAA
CGTGGCCAGAGCTTCGCGAGCGGCGGCCACCTCCTTATTGAGGCGGGCAATCACACGACAGGCGGCATCGTGCTGATACAGCGCATGGGACAACT
CCTGGCGCGTCGTTTGCAGCTGCTGGCGTTGTGTGAACGAGTGAATCATGAGGGCGTCCCACTCGTCCTGCATCGTTTTCAAAGTGGCCGGAATG
CTGGTGGCACTTGGCGGTTTCGGTTTCACCACAGCCGGCGTCTTGATCTCGATCAGCTCCTCCGGCTTCAGCTCCTTGCCGCTAATGGGATCGCA
GCCATTCTCTAACAGATACTTCTCAATCACCCGCTTTTCGAAAACGGCTCCCGAGTGCGGGGAAACCACGGGCGTCTCGGGGACTTCGTTTGTCA
CTTGGAATGGAAAGTGCGATTCATAATGGCCCAATTCAAATCAAAATCTAAATTATTCACTTACGTGCGCAAACCAAAGCCATTGCTGTTTGTGA
TTATGTCGCTTTTCGCGTAGTCTTGTTGGTAAATTAAATGTTTTACACGTTTTTCCCGAGCCAAGCGCAAAATTGTCGGCAAAGCCGCTTCTTCT
TATTATGCCAGTTACTCGGCGACGCGGGAGTTTCGAGCACAGGGCTGCCAGATCAAATGGATTTTGGCTAGAAATTTGCACAGAAAAAACTAGCT
AGAATTTAAACAATTTATTTTATTGATAACACAACACATTCAATAAGTATTTAATCCATAACAATAGTTTTTATAGATAAATGACATTTACTGAT
AGAGAAGTGAGTAACATATCTTAAATCAATCAGCTATCTCACCGTTTTGCCAATCACAGTTCCGCACGCACAATCCATAATTGCTGGCAACCCTA
GCACGTTGTTTCTGTTATTCAATTCACGATCTAGTTTTATAACATAGTTTACTGCCATTAAGGTATATTTTTAAAATGCTGAAGCATTTTGCACG
ATGGCGTCTGGGCAGCCAGTTGCTAAAGGGATGTGCCGCACCAGTGAGGCAAGCCTCCAAAACCTCCAGCGCAGAGAACCTGATAGCCGGCACAG
AGGAACCCCAAAAAAAGTTCGTCAATCCGTTTTCCAGCCCGCTCCTGCGTTAAGTAATGATACGATATCAGAGAACAAGGAGGAACGGGATAAG
CGACTCAAGGTGCTGCAGCTGGAGGCGGACATTGCCCACCAGGAGGGTCGGCGGGTGCCGTCACTGGAATTCTTTAAGGATCATCATTGGGAGCA
CGTGCTGACGCTACCCACAAAATCAGCTAGGATCAAGTACTTTGGCTATCTCTGGCAAATCGAGATGAAGAAGGAGGCGGATCAACGCAAGAAGG
CAGAGCGAGCGAAGGAAGCCGAGCGGCGGGTTGCGGAGATGCGAAAGGAGCGCGAGGAGAATACGCACATTATCTATGGCCTGGGACACACATCG
TTGTTTCTGCGTATCTATGATACCACTATTAATCACTGGCAGAACAACCGACTCACACGGGCCATGCAGTTTGCCCCCAAAATGGTTTTGGATTG
CTCCTACGATGAGCACATGAACAATCGGGAGGCTACCTATGCAGCAAAGCAATTGATGATGTGCTTTGCGGAGAACCGGATGAATGATGAGCCC
(SEQ ID NO: 619)

Exon: 4699..4530
Exon: 4465..3112
Exon: 1251..1001
Start ATG: 4548 (Reverse strand: CAT)

Transcript No. : CT17476
CCCTGTGCTCGAAACTCCCGCGTCGCCGAGTAACTGGCATAATAAGAAGAAGCGGCTTTGCCGACAATTTTGCGCTTGGCTCGGGAAAAAACGTGT
AAAACATTTAATTTACCAACAAGACTACGCGAAAAGCGACATAATCACAAACAGCAATGGCTTTGGTTTGCGCACTGACAAACGAAGTCCCCGAG
ACGCCCGTGGTTTCCCCGCACTCGGGAGCCGTTTTCGAAAAGCGGGTGATTGAGAAGTATCTGTTAGAGAATGGCTGCGATCCCATTAGCGGCAA
GGAGCTGAAGCCGGAGGAGCTGATCGAGATCAAGACGCCGGCTGTGGTGAAACCGAAACCGCCAAGTGCCACCAGCATTCCGGCCACTTTGAAAA
CGATGCAGGACGAGTGGGACGCCCTCATGATTCACTCGTTCACACAACGCCAGCAGCTGCAAACGACGCGCCAGGAGTTGTCCCATGCGCTGTAT
CAGCACGATGCCGCCTGTCGTGTGATTGCCCGCCTCAATAAGGAGGTGGCCGCCGCTCGCGAAGCTCTGGCCACGTTGAAACCGCAGGCGGGCAT
TGCCAACGCACCCACGGCAATACCACAACCGGCCCTGGCCTCTGAGGCTGGCGGAGCTGCTGCCCATCCCATGGAGCAGGCGGGCATGAGCGCCG
AGGTCATACAGAAACTGCAGGACAAGGCCACGGTGCTGACGCAGGAGCGTAAGAAGCGCGGACGCACTGTGCCCGAGGATCTGGTTACAACGGAT
CAGGTTAAGAACTTCCTTACTGTGGCATCCCATCCCGGCCTACACTCGGCCTCCGTTCCCGGCATTCTGGCCTTGGACATCAACAGTGCTGATCA
CAGTAAGATTCTGACCGGAGGCAACGATAAAAACGCCACCGTGTTCAACAAGGACACAGAGCAGATGGTGGCCATCCTGAAGGGACACACCAAGA
AGATCACCAAAGTCATATATCATCCTAACGAGGATACAGTCATAACCGGCTCGCCCGACATGAACATACGCATCTGGCACGTGCCCACTTCGCAG
ACGCAGCTTCTCCTGCGCTGCCACGAAGGACCTGTTACTGGCCTTTCGCTGCACCCCACTGGCGACTACTTGCTGTCCACATCATCCGACAAACA
CTGGGCATTCTCCGATATCCGCACAGGACGCCTGCTCACCAAGGTAATCGATACCGCCGAAGTCGGGCTGACGACAGCGCAATTCCATCCTGATG
GTCTGATCTTCGGTACGGGCACCGTGGACTCGCAGGTTAAGATCTGGGATTTGAAGGAGCAGAGCAATGTGGCCAACTTCCCTGGTCATACCGGT
CCCATTTCGGCCATCTCCTTCTCGGAGAACGGTTACTACCTGGCCACCGCTGCAGATGATGCCTGCGTTAAGCTGTGGGATCTGCGAAAGCTGAA
GAACTTTAAGACAATCCAGCTTGATGACGGCTACGAGGTCAAGGATCTGTGCTTCGACCAAAGCGGAACCTATCTGGCTATCGCCGGCAGCGATG
TCAGGGTTTACCTGTGCAAGCAGTGGCAGGAACTGAAGGTATTCAACGACCACACGGCCCTGGCAACGGGCGTGAGATTCGGCAAGCACGCCCAG
TATCTGGCATCCACCAGCATGGACCGCACCCTGAAGCTCTACGCCATCGAATAAGTCCACACTTAGTAATTAAGTCCAAAATTTTCTTATACAAT
ATTCCCTAATGATTGTGTGTTTTCTTGAACAAATCTTGCAGAATAATAAACCTGACCCTCTATCC
(SEQ ID NO: 620)

Start ATG: 152 (Reverse strand: CAT)

MALVCALTNEVPETPVVSPHSGAVFEKRVIEKYLLENGCDPISGKELKPEELIEIKTPAVVKPKPPSATSIPATLKTMQDEWDALMIHSFTQRQQ
LQTTRQELSHALYQHDAACRVIARLNKEVAAAREALATLKPQAGIANAPTAIPQPALASEAGGAAAHPMEQAGMSAEVIQKLQDKATVLTQERKK
RGRTVPEDLVTTDQVKNFLTVASHPGLHSASVPGILALDINSADHSKILTGGNDKNATVFNKDTEQMVAILKGHTKKITKVIYHPNEDTVITGSP
DMNIRIWHVPTSQTQLLLRCHEGPVTGLSLHPTGDYLLSTSSDKHWAFSDIRTGRLLTKVIDTAEVGLTTAQFHPDGLIFGTGTVDSQVKIWDLK
EQSNVANFPGHTGPISAISFSENGYYLATAADDACVKLWDLRKLKNFKTIQLDDGYEVKDLCFDQSGTYLAIAGSDVRVYLCKQWQELKVFNDHT
ALATGVRFGKHAQYLASTSMDRTLKLYAIE*
(SEQ ID NO: 621)

Name: GTP-binding-protein
Classification: signal_transduction
Gene Symbol: Gbp
FlyBase ID: FBgn0013969

Celera Sequence No. : 142000013384665
CAACCATCAGCAGTGTCATCCGCATCCGCGCCAGCTATCACAGCACCAGCCCAAGCCATCCGATCAGCTCATCCGCCGGCTGCACGTTCCTAGGC
ACTACTGGTAGTACTTTGGGCCGCCCGCGCAGTGCGGCCGCCCGATCGTTTGCGTCTGCATGGAGTCAATGAGACGTAACGAGGCGAACACTAGC
CACCACCCGAATAAGGTAAGCTAATTGTGGCACCTTAATCGGAAAACTATCCACGCATCATTTCTGAAGCATTTTAATCATATTCAGTATTGATT
TCTTATCAATAAATTGATTTAAATTGTAAATTTTTATGCTACAAAGCTAAACTTTTCAAATACCTAAGTGTATACATATCTTGTAAATGTCTGTA TGTATTTAAGCAAAGACGTCAGGCGAAGTAAACGTTTTTTTTTCTTTGAATACCATATAATTTTTTATTGCGAGTAATAACTTACTAGTGGGAAG
TACTTATAGCTTATAGCTTTGGATCTTTAATACTTGGTAACACTATTTACCTTCCTCCACTGTATTTAGTGGGTGATAAGAGCGTAATTATTTTA
TTGTCATCATTTTGGCCCACTCGAGTGGCGTTTTTTTCGTGCCAGTTTCTCAAGTAGCCACTACACTTTTGCAGTGTGCGATAAGCGAAAGGGGC
GATAATGAACTGACCGGCGAACTACATGCTTTACTCCTCCTTAGTTTGTTGGTTTATTGGGTCAGTCCAGGAAACTGATTTATTAGTTCAAAGGG
TGGAAAATGAAAAACAACAACAACGAAGATCAACGTGCACTTAAAGTTGTCAGTTGCCACTCGCGTTTTCCAACACTGAAAGCGTTTTGTTTTGT
TTGCCTTCGTCTCTCCGCCGCTTCTCTTCCGCTCACATAATCTCTTTCTCGCTCTCCCTCTCTTCACCCGTTTTCGGTGGTTGCTCTCCGGCTCT
TTCCTCTTCTTCTTCACTTTTTTTTTGGTTTTCCGTTCAGTCTCATCCGCCAAACGAAAAAGGACGCCGCGGAGAAGGCTCGCGCAAAATAATCG
AGAGTAATACGACGTTGCTTATTTATTTATTGTTTTTGTTTTTTGTTTTTCTTGTAAATTGAAGCGTTAAAAATACGCGCACGCACAAAACTATC
AACTAATTATGGTTATGGAATGGAAAAGAAGTTGGCAAAGGTAAAGAGCGAAAGCGGCGAAAGAAATAACAATTTTTGTTTGAGTTTTTTTTTTT
GAGTTTTCTTCACGTCATGCCCTACTCCTCACACTTACGCACTCACACCCATGCATATGTATGTAAGCTACAACTTATTTTGTTGGATTTCTTTC
TTTTTTTTGTGCAATCGCAGGTGGCCCTGAATAGCAGCAACGTAGCAACGGAAAGCAATATTAAGAATAATAAATTGTTAGCTAATTTAAGTGC
GGCAGGAGCAGCTACAGCTACAACGGCAACAACAGGAACAGCAACAACAACGACGGCGACAACAGCGAATCAAGCGCTGAATTTCAATAACAAAA
CGAAAGCAACAGCAAACGCGACTGCAGCATCGGCGAATAATCGGCACAATAACAACAACAATTCCAGTGCGATCAAGAAGCACACAAATACGAGT
AAGTAACTGCAAATCTCTCGCTGCCTCTCGCTTTTTTTTTATCAACAGTGGCGTAGACAGCATTGTTTTAAGGGGTTACAAATTAAATTACAGAA
AAAAGTGCTATTTCACACACACAGAAGTGTATAGAAATCGATAGCGTCCTTTCGATTAATGTGAATTCCCCCCTCCCCCATTTTTATTATTAATT
CATTAAAAGAATTGAAAATAAGTAATTAATATAATAAAAATTAAATGAATTAATCATAAATTTTACAAATTTGGAGGGACCGTTTAAAAAAATAT
TTAAACTAAATACAATTCAGCAACTCCCCATTTAGTACGCCACTGACCTCTAAGCTTTAATGCGACAACTCCAATCTAATCCATCTCTCCTTTTT
CGCAGAACAACTAGCTGGCAAGAGCCCCGCGTGCAACTCCTCCTCCTCGTCGCTCTCCTCGTCGAGCAGCTCCAACTCGAGCGAGTCGAAGGACA
CGAACTTTGAGTACGAGGACGAGTGGAATATTGGCGGCATACCAGAGCTGCTGGACGACTTGGACGCGGATATTGAGAAGTCCGCGCATTCTTCG
GGTGGTGGCAACCAGGCTACCGCGCTAAATGCCAAGCAGGCAAACAGCTCCTCCACATCCTCCTCATCATCCTCCAAGGGCGGCGCTTCATCCTC
GTCATCCTCAGCAGCAGCGACGGGATCATCATCGTCGCATAAATCGCACAAAACCACATTGCACAGCAATTTGTCGGCCACATCGCCAACCACAA
TTAAGTTCACACGCCAACCGGTGGCCATTGGCGGAGCTAACTCCTCCTCATCTTCATCAGCTGCAGCGCCCAGTGGTGGCAGCGCGAACGTG
GTGGCCAAGGGATCATCTTCTTCCTCGTCCTCCACATCTTCCTCATCTTCGGGGAAGCATCATCACCATCACCACCATCACTCAAACTCAAGCAG
CAGTGGAAGCAGTTCCAAGGGCTACAAGTCCGCTTTGGTGGCTCAACTGAACAGTCCGAGTCCACTGAACAGTAACTCCAAGTCCCTGAGTGGAT
CGGGGAGTGGAAGCGGGAACACAAACGGAGCAGCGGGAGCTGGAGCCGGCAGCACATTGTCATCCTCGACATTTGCCGGTTTCTCCAAAGGCGGC
AGCTTAGTGTCTTCGTCGGCAGGAGCAGCAGCGGCTTTAGCGGCTGGCAGTGGACAACAGGGCTCCAAATTCTCCGCTGGCGGCATGTCCTCGCA
AACGGGCAGCGGCAGCGGCGGCAACAACACTAGCAATAGCAACAACAGCAGCAGCGGAAGCGGAGGCAGCGGCTCAGGTAGCAGCACAGGGAACA
CCGCCAGCGGTAGCGGGAACAACAACAGCACAAGTGCCGGTGGGCCGCCGAGTTCGCAAGGCGGCAACAACGGAAACGGTAGCGGTAGCAGCTCC
AGCTCCTCCAGTGGTAAATCGAGCGCAAAGATGTCCATAGACCACCAAGCGACGCTCGACAAAGGACTCAAAATGAAGATCAAGCGCACCAAGCC
GGGCACCAAAAGCTCGGAGGCCAAACACGAGATTGTGAAGGCCACCGATCAGCAACAGAACGGAGCCCTGGGCGCCGGATCCAATAACTCGGCCA
ACGAGGATGGGAGTTCCGGTTCCAGTTCCACCAACGCGTCTTCCCTGGGGAGCACCAATTCATCGAGCAGCGCAAGCAGCGGCAGCTCCTCCAGC
AGCGGCAGTTCTTCGAGCAGCAGCAAGAAGCACCTAAACAATGCCAGTAGCGGTAGTGGCTCCTCCTCTTCCGGAGGAGGGAGCCAAAACAATGC
CAGTGGCCATGCCAGCGGAGGGGGATCCTCCGGTAGCAGTCAGTCTACGCCGCAGGGCACTAAGCGCGGTAGTTCGGGTCATCGGCGTGAGAAGA
CCAAGGACAAGAACGCACATTCCAATCGCATGTCCTGGACAAGTCAGCAGCTGCTGCCTCGGCGGCCGGCGAGAAGGATACACCTGAGAAGTGT
TCCGGTACGGGAGCTGGTGGATCTCCCTGCTCCTGCAACGGAGATGTGGGAGCTCCTTGCTCACATCATGCCTGCATTCGCCGTGCCGCACACAT
GTCCAACTCCGCAGGCAATGCGAATTCGAGTGCCGGCACTGGGCAATCCGGTGGTTCATCCTCCATGTCAGCAGTGCCACCGGGTGTGTTCACAC
CTTCAGCGGGCTCTCCTTCCACCGGTTCACCATCGACCGTGGTGCCTGCCGCTGCCTCACTTCTGGCAGCGACCGGAGCAGCCTCCTCCTCCGCC
TCTCAAATGGCCAGCAGTAGTGCCGGCGGCGTTGGCGGTTCGGGAGGAGGTGCCAATGCACCAGGACCGCCGGGTAAGGAGTCTGCCGGCAGCAT
CAAAATCTCCTCGCACATTGCCGCCCAACTGGCAGCAGCGGCCGCTTCCAATAGTTACAGCGGGAGTGGAGCCAACACGAATCAAGGCCAGAACA
GCAATGCTGGCGGCAACGGCGGTTCGGAGAGCAAAGCAGCAGCGGCTGCTCAGGCCAAGTTAATGGCACCCGGCATGATCTCAGCCACCATGCAC
CATACGATCTCGGTGCCGGCGGGCACAGGAACAGGCGACGACGATACCAAATCTCCGCCTGCCAAAAGGGTCAAGCATGAGGCTGGCGCTAGTGG
AGCAGGAGGCGGCAAGGAGATGGTGGACATCTGCATTGGCACCTCGGTGGGCACCATCACCGAACCGGACTGCCTGGGTCCCTGCGAACCTGGCA
CTTCCGTAACCCTCGAAGGGATTGTGTGGCACGAGACCGAAGGCGGCGTTCTCGTGGTCAATGTCACGTGGCGGGGCAAGACCTACGTGGGCACT
CTGCTAGACTGCACCCGACACGATTGGGCTCCTCCAAGGTGAGTTGGTGTGGCTTGGGAATTGAGTTGAGGCTTATGTTGACTTGCTTTTCAAAC
TGTTTCCAAAATTATTGTAGAGACTAGATAAATGAATAAAGATGCCTTTCAATATTATGTTGCAAGTTGATTTATTTTTATTATAAATTATCTTT
TCTATCTACCCATTGTTTTGGGGATCAGTTTGAAATATAGTCTATGGTTTATATACGAGAAACATAATTATCAAAACTCAGTGGCGTTTAAGTAA
ATTTGTCAGCACCTTATCTACTTGCCTAATATTTGCATCAAGCTGTTAAGTTATTTGTAAATTTAATCTAAATCTGATGCAACAGCAATCATTTG
CCGTTCGTTTACTGATGCGATTATTTATTAAGTGCTTAATGTGCCACTCAAGATTTCCACGAATGTACATATGTAGTTTGTTTTGATTGAAGATA
TGTGATATCTGTAGGGGGATTGCAAACATCACTAGTTTTAGATTTTACCGATTACTCATTCATTTTCGTTGCTTTCAGATTCTGTGATTCACCAA
CTGAAGAATTAGATTCTCGAACTCCAAAGGGACGCGGAAAGCGCGGACGCAGTGCAGGTCTCACTCCTGACCTGAGCAACTTCACCGAGACCAGA
AGTTCGGTAAGTAAAGCATACAGAATTCAGTTTTAGGCTTTTGAAAGCAGAAATAAATACGATGGTTAATAATATATATCTCTCATCAAATCGTT
ACAGATTTACTTCTCACACGCCCAGGTGCACTCCAAGCTGCGTAATGGTGCCACAAAGGGACGCGGTGCGACACGCAGTGCATCCGGTAATGCGG
CAGCGAACAGCAACAGCAGTTCATCGGGCAACGGAGGCGGGGCCACGCCCAGCACATCGCCGACGGCATTTTTGCCGCCACGGCCAGAGAAGCGC
AAGTCGAAGGATGAGGCGCCTTCACCGCTTAACGGCGACGCCTCGGATGGAGCGTCTGTTGGCGGTATTGGTGGAGCCGGTGGAGTGAACATGGT
GAACGCCAGTGGCATCCCCATATCGGCCAGCGGCGGTGGCCTGGCCACGCAGCCGCAGAGCCTGCTCAATCCGGTCACTGGTCTCAATGTGCAGA
TCAGCACCAAGAAATGTAAGACTGCTTCGCCCTGCGCGATCTCCCCAGTTCTGCTTGAGTGTCCCGAGCAGGACTGCAGCAAGAAGTACAAGCAC
GCAAATGGGCTGCGTTATCACCAGTCGCATGCCCATGGAGCGGGCGGTGGCGCAAGCTCCATGGATGAGGACTCCATGCAGGCGCCCGAGGATCC
GGCCACGCCGCCCTCGCCAGGAGTCGCAAGTGGAACGGGATCAGGAGCATCTGTAGCATCATCGGCAGTACCAGCGACAGCACCATCAGCGGGTC
AAGGAACTGTCGCAGTGTCCCCAAACACACCCCTCGCAAATTCAAGCAACCCCGTCACCAATGGCAATGTTGCACCATCGGCACCAGCTACTGGA
TCGGTAACTATCGCCGCTCCCAACACTACTCCCTCTGTGGTAGAGACGCAAGCGCCGCTTACTGGTCCTCCACCAGTCACGCCACCAGCTCCAAC
TCCCATCTGCGCAGTTGCAACACCCGGAGCGGAGCAATCTGTATCATCAGTATTGCCCCTGGGAAATCTTCCACTGACGGCAGGTCCAAATAGCG
CGACACAACAGCAACAGCCTCCTACACAGCAGCAACAACCACAGTTGCTCGTCCCAGGAGGCAGTGCGGCAAGCCTTCAGCAGCAGCAGCAGCAG
CAGCAACCAGTGGCCGGAGGCAGCATCACTGCTGGAATCTCCGGACAGGCTCTGTCACAGCATCAACAGCAACTAATGGGTGGATTGCCTGCCAT
GTTGTCAGACCAGCAGCAGCAGGCATTGTTGCAGCAGGGAGCACGTAAGTATTCGATTTTTCTACCTTTTGGAAAAGATGTGATTGAAATTATAT
TAATCGTACTAAATTCTTATCTATTTCTTTTTTAGTTAAAGCGGGTGTACTGCGTTTTGGCCCGCCAGATGGAAATCCCCTGCAGCAGCAGCCTG
GTCAAGCATCGGTTAATCCACAGACACAACAGTCTCCTCCAAGGCCTCCCAGTCATGTCCAGGATCAACAGACGCCATCGGCCTACGCCCAGCAG
GCAGGTTTAAAGACATCGCCTGGATTTGGCTCCGTTGGCGTGGGTGCCGCTAGCAGCAAACAAAAGAAGAACCGCAAGTCACCTGGACCCAGTGA
CTTTGAGGGCCGCGTATCGCGCGAGGATGTACAGAGTCCGGCATACAGTGATATCTCCGATGACTCCACGCCAGTTGCCGAACAGGAAATGCTGG
ACAAGTCAGTCGGCCAGGCGGTGACGGCAAAGCACATCGAATTGATGGGCAAGAAGCCGACGGAAGTGGGCGTTGGTGTTCCGCCACCACCAGCT
CCCAATATGTATGTGCCGGGAATGTATCAGTTCTATCCGGCGCAGCAGCAGTCAGCACCTCCACCACAGCAACAGCAACAACAGCCGCAATACAT
GGTGCAGACAGAGCCAGGCAAACCACCAGGATTGCCACCTGCTTTGACACAAGCTCAGCAGCAGCAACAATTGCAGCCGGGTGCTCCTCCGCCTA

FIGURE SHEET 336

CCTCACAGCCCCCGAGTCATTTGCTAGGTCCACCCGGTCAGCAGTCGGTGGCTGCCCACCTGGCAGACTACAGTGGCAAGAACAAGGATCCACCA
TTGGATCTGATGACCAAACCGCAGCCACAGCCGGGTCAGCCGCCTTCACAGCAGCAGCAGTCGGGCCAACTGTCGGGGCAGGAAAACAATGGCAA
GGATGTTGGACCGCCCACCTCTCAGCCAGGATCTCAGCCGCCGCCGGTTAACCTAAGTGCAGTGGCTGGGCCGCCGCCAGGAAGCCTGCCACCCG
GTTTGGGTGGTCTCTCGGCTTTGGGAGCAGCCGGTCTAGGTGGTCCTGGACCGGGCAAGGGCATGCCCCACTTCTATCCCTTCAAGTAAGTTGTT
GATCAATCGCTAAGGTCAGTTGCCATTGCATAACTAACCAATCGTTTACCTTTTAGTTTTATTCCGCCTGCGTATCCATACAATGTGGACCCCAA
CTTTGGGTCAGTTTCTATTGTTGCTTCAGAGGAGGCCGCCAAGCTGAGTGGGCATCCGGGTCTGCCACCCAGCTCACAAGCGCAGCAGTTATCCG
GCATAAGTATCAAGGAGGAGCGTCTGAAGGAAAGCCCCAGTCCGCACGACCAGCCGAAGCACATGCCATCTCAGCAACAGGTAAGTCCTTACCAA
CGTTATAATATTTTGGCAAAACTAATGCAATATGATTTCATATCCTCCGCAGATGATAGCCAGCAAGCTAATCAAGCAGGAGCCGATGACCAAGC
AGGAGATCAAGCAGGAGCCCAACTCAAATCCGGGCCAGCAGCATCCGCCTCCGCAACAGCAGCCAGCGCCTCAGCCGCAGCAACAACAGCCGCCA
CCCCCGCAGCCACAACAGCCGCATGCCCTGCATCCCAAGGATTTACAGGCACTGGGCGCCTATCCCGCCATCTACCAGCGCCATTCCATAAACCT
GGCCGTGCAGCAGGCTCGCGAGGAGGAGCTGAGACGGTAAGTGAAGTATAAGCATCATAAACGCGTCTTTGAGGAATACAAATCATAATAAATTT
AAAATTGTTTCTAACTTTTGGAAGTTGTAACTAACTTGTGCATCTTTTCACATCAGGTATTACATGTTCACTGGACGACAGAATTCGGCAGCCGC
AGCAGCAGCCGCAGCAGCTCAAAACGCTGCCAGTGGTGGTCTTCCACCGCATCCCGGCATGATGCACAAGGATGAGCCTGGCATGGGATCGGCGG
CGCAACAACAGCAGCAGCAACAACAGCAGCAGATGCAAATTGCACAGCAGCAGCAGCAGGCCATTCAGCAGCATCATCAGCACCTGCAGCAGCAG
CACCAGGCCCAGCAACAGCAGCAGCAGCAACAACACCAGCAGCAGCAGCAACAACAGCAGCAGCAGCAACAACAACAGCAGCAGCAGCAACAACA
GCAAAAGTTAAAGCAATCGCAGGCGGCTAGTGCGGGGGCAAATAATAAGGCCACCAACCTGACGAAGGATTCTCCCAAACAAAAGGGCGGCGATG
ACGATCAACCGCTGAAGGTGAAGCAGGAGGGCCAAAAGCCGACCATGGAGACGCAGGGTCCGCCACCACCACCCACGTCGCAGTACTTCCTTCAC
CCCTCATACATTTCCCCGACGCCCTTTGGGTTTGATCCCAATCATCCGATGTATCGCAACGTGTTGATGTCAGCCGCCGGACCGTATAATACGGC
ACCGTACCACCTGCCCATCCCTCGCCCGTACCATGCCCCAGAAGATCTCTCGCGTAACACCGGCACCAAGGCGTTGGATGCACTCCATCACGCGG
CCAGTCAGTACTACACCACCCACAAGATCCATGAGCTCAGCGAACGGGCCCTCAAGTCGCCCACCAGCGGCAGCGGCCCCGTCAAGGTGAGCGTC
AGCAGTCCCAGCATCGGGCCGCCTCAACCAGGCGGACCCACGAGCAGCGGCCCCGGATCCGGACCAGTTTCCGGTGTCCTCGGCCCCGGCAGCGG
TTCCAACCAGCAGCCCGGCTCGGCACCTGGGTCTGCGGGCGGTGTGCCGCTGAACCTACAGCCACCACCCGGAGGAATGGGCCCGTCACCCGGCA
GCAAGCCGGATCTGTCCGGCCCGAAAGGACATGGCGGAGTGACGCCCGGCTCGTCATTGGACGGCCACAAGCAGTCGATGCCCGGAGGTCCGCCA
CCGAACGGGCCATCGGGCAATGGAGCCGTTGGCGGTGTGGGAGGCGCTGCCGGCAATGGCGCAGCGGGAGGCGGCGGTGCAGGTGCCGCCGACTC
ACGCAGCCCACCACCGCAGCGCCATGTGCACACCCACCACCACACGCACGTCGGCCTCGGCTATCCCATGTACCCGGCGCCGTATGGAGGTGAGT
CCCCAACTGTGCTATTCAGTTCGGAAAGTTGAATGCTAATCATTTAAATGTTTACTCCCATAGCGGCTGTTTTGGCTAGCCAGCAGGCGGCTGCT
GTAGCTGTGATAAACCCGTTTCCGCCGGGTCCGTCGAAATGAGATCCACTGAACGGTAACAACGAGAAGAAGGCGTATAACGTAAAGAACAACTA
GTGTGGAGCGGAAAGTCATGGTGCCCGCCCCATAGTGCATTTGCTATTTTCTGAGATCCCCAGACAGACAGATAGAATGGGAGAAGGATAAGGCT
TTGTTCCCCGTTGGATTCCAACTTCTTCCCGTCGAAACCTGTCACAGTCTTGGCTGCCTCAACGAGTCCTTTCGATGCTGATGCATCGGCGGTCG
AGGAACCGAGAGGAACACAGAATCGACTATTTATATGCATAAGTATTTTTTGATGTTTCGTTCGATGTGGTTAACTATAACTAGCCTAAGGTATC
ACTACTATTACCACATACAACCTATACATATATAAATATATATAGCATAACTACATATAGCGACTTTTTCCTAAGTGTATTTGCATCTGCATATA
GATATCTATATTTATATTTATATCATACGAGAGAGGCGTAATCCGAACATGAACAAACACAACCAACAAACAGATTACATGAAACATGCAAAAAA
TGAAAGGGAAAAAAACGAATCAAACTCGATACTGTAGTGTGTTGATTTCTTTGTAAAAAAAAATAAAAACTAAACGTACGAGAAATGAAATTAAG
AAAAGATCGAAATGTATGAATATTGTTTAACTAAATGATTAAATTATGCAAGTAGAACGTACAAGATTAGCATTTAGCGTGTGTATTAATTATCC
TTATCTGTGTTGCGGATGGAGCTGCGCGGGATTTGCATCTAAAAGACAAATTGGGCGCGCCGCCCATTCAATTCTTATAAATATAAATATATATT
ATGTGTATCTAAATCTATATCTGTGTGTGTACTACTCGTATCCGTAGTTTCTACTTTATAAGTTCTCCGTGAATGACTACGATGAATTTTTCGGC
CAGCAGCCGCACATTAATTTTAATTGTTTCTAAGCATCAATTTGTACTTTAAATATTTATACGCATATGCTGCATATATGATATGATAACGA
(SEQ ID NO: 622)

Exon: 1001..1180
Exon: 1352..1613
Exon: 2001..4503
Exon: 5019..5136
Exon: 5230..5290
Exon: 5357..6409
Exon: 6496..7495
Exon: 7562..7775
Exon: 7843..8111
Exon: 8227..9494
Exon: 9564..9637
Start ATG: 1160

Transcript No. : CT17646
CAAACGAAAAAGGACGCCGCGGAGAAGGCTCGCGCAAAATAATCGAGAGTAATACGACGTTGCTTATTTATTTATTGTTTTTGTTTTTTGTTTTT
CTTGTAAATTGAAGCGTTAAAAATACGCGCACGCACAAAACTATCAACTAATTATGGTTATGGAATGGAAAAGAAGTTGGCAAAGGTGGCCCTGA
ATAGCAGCAACGTAGCAACGGAAAGCAATATTAAGAATAATAAATTGTTAGCTAATTTAAGTGCGGCAGGAGCAGCTACAGCTACAACGGCAACA
ACAGGAACAGCAACAACAACGACGGCGACAACAGCGAATCAAGCGCTGAATTTCAATAACAAAACGAAAGCAACAGCAAACGCGACTGCAGCATC
GGCGAATAATCGGCACAATAACAACAACAATTCCAGTGCGATCAAGAAGCACACAAATACGAAACAACTAGCTGGCAAGAGCCCCGCGTGCAACT
CCTCCTCCTCGTCGCTCTCCTCGTCGAGCAGCTCCAACTCGAGCGAGTCGAAGGACACGAACTTTGAGTACGAGGACGAGTGGAATATTGGCGGC
ATACCAGAGCTGCTGGACGACTTGGACGCGGATATTGAGAAGTCCGCGCATTCTTCGGGTGGTGGCAACCAGGCTACCGCGCTAAATGCCAAGCA
GGCAAACAGCTCCTCCACATCCTCCTCATCATCCTCCAAGGGCGGCGCTTCATCCTCGTCATCCTCAGCAGCAGCGACGGGATCATCATCGTCGC
ATAAATCGCACAAAACCACATTGCACAGCAATTTGTCGGCCACATCGCCAACCACAATTAAGTTCACACGCCAACCGGTGGCCATTGGCGGAGCT
AACTCCTCCTCATCTTCATCAGCAGCTGCAGCGCCCAGTGGTGGCAGCGCGAACGTGGTGGCCAAGGGATCATCTTCTTCCTCGTCCTCCACATC
TTCCTCATCTTCGGGGAAGCATCATCACCATCACCACCATCACTCAAACTCAAGCAGCAGTGGAAGCAGTTCCAAGGGCTACAAGTCCGCTTTGG
TGGCTCAACTGAACAGTCCGAGTCCACTGAACAGTAACTCCAAGTCCCTGAGTGGATCGGGGAGTGGAAGCGGGAACACAAACGGAGCAGCGGGA
GCTGGAGCCGGCAGCACATTGTCATCCTCGACATTTGCCGGTTTCTCCAAAGGCGGCAGCTTAGTGTCTTCGTCGGCAGGAGCAGCAGCGGCTTT
AGCGGCTGGCAGTGGACAACAGGGCTCCAAATTCTCCGCTGGCGGCATGTCCTCGCAAACGGGCAGCGGCAGCGGCGGCAACAACACTAGCAATA
GCAACAACAGCAGCAGCGGAAGCGGAGGCAGCGGCTCAGGTAGCAGCACAGGGAACACCGCCAGCGGTAGCGGGAACAACAACAGCACAAGTGCC
GGTGGGCCGCCGAGTTCGCAAGGCGGCAACAACGGAAACGGTAGCGGTAGCAGCTCCAGCTCCTCCAGTGGTAAATCGAGCGCAAAGATGTCCAT
AGACCACCAAGCGACGCTCGACAAAGGACTCAAAATGAAGATCAAGCGCACCAAGCCGGGCACCAAAAGCTCGGAGGCCAAACACGAGATTGTGA
AGGCCACCGATCAGCAACAGAACGGAGCCCTGGGCGCCGGATCCAATAACTCGGCCAACGAGGATGGGAGTTCCGGTTCCAGTTCCACCAACGCG TCTTCCCTGGGGAGCACCAATTCATCGAGCAGCGCAAGCAGCGGCAGCTCCTCCAGCAGCGGCAGTTCTTCGAGCAGCAGCAAGAAGCACCTAAA
CAATGCCAGTAGCGGTAGTGGCTCCTCCTCTTCCGGAGGAGGGAGCCAAAACAATGCCAGTGGCCATGCCAGCGGAGGGGGATCCTCCGGTAGCA
GTCAGTCTACGCCGCAGGGCACTAAGCGCGGTAGTTCGGGTCATCGGCGTGAGAAGACCAAGGACAAGAACGCACATTCCAATCGCATGTCCGTG
GACAAGTCAGCAGCTGCTGCCTCGGCGGCCGGCGAGAAGGATACACCTGAGAAGTGTTCCGGTACGGGAGCTGGTGGATCTCCCTGCTCCTGCAA
CGGAGATGTGGGAGCTCCTTGCTCACATCATGCCTGCATTCGCCGTGCCGCACACATGTCCAACTCCGCAGGCAATGCGAATTCGAGTGCCGGCA
CTGGGCAATCCGGTGGTTCATCCTCCATGTCAGCAGTGCCACCGGGTGTGTTCACACCTTCAGCGGGCTCTCCTTCCACCGGTTCACCATCGACC
GTGGTGCCTGCCGCTGCCTCACTTCTGGCAGCGACCGGAGCAGCCTCCTCCTCCGCCTCTCAAATGGCCAGCAGTAGTGCCGGCGGCGTTGGCGG
TTCGGGAGGAGGTGCCAATGCACCAGGACCGCCGGGTAAGGAGTCTGCCGGCAGCATCAAAATCTCCTCGCACATTGCCGCCCAACTGGCAGCAG
CGGCCGCTTCCAATAGTTACAGCGGGAGTGGAGCCAACACGAATCAAGGCCAGAACAGCAATGCTGGCGGCAACGGCGGTTCGGAGAGCAAAGCA
GCAGCGGCTGCTCAGGCCAAGTTAATGGCACCCGGCATGATCTCAGCCACCATGCACCATACGATCTCGGTGCCGGCGGGCACAGGAACAGGCGA
CGACGATACCAAATCTCCGCCTGCCAAAAGGGTCAAGCATGAGGCTGGCGCTAGTGGAGCAGGAGGCGGCAAGGAGATGGTGGACATCTGCATTG
GCACCTCGGTGGGCACCATCACCGAACCGGACTGCCTGGGTCCCTGCGAACCTGGCACTTCCGTAACCCTCGAAGGGATTGTGTGGCACGAGACC
GAAGGCGGCGTTCTCGTGGTCAATGTCACGTGGCGGGGCAAGACCTACGTGGGCACTCTGCTAGACTGCACCCGACACGATTGGGCTCCTCCAAG
ATTCTGTGATTCACCAACTGAAGAATTAGATTCTCGAACTCCAAAGGGACGCGGAAAGCGCGGACGCAGTGCAGGTCTCACTCCTGACCTGAGCA
ACTTCACCGAGACCAGAAGTTCGATTTACTTCTCACACGCCCAGGTGCACTCCAAGCTGCGTAATGGTGCCACAAAGGGACGCGGCGGGGCCACG
CCCAGCACATCGCCGACGGCATTTTTGCCGCCACGGCCAGAGAAGCGCAAGTCGAAGGATGAGGCGCCTTCACCGCTTAACGGCGACGCCTCGGA
TGGAGCGTCTGTTGGCGGTATTGGTGGAGCCGGTGGAGTGAACATGGTGAACGCCAGTGGCATCCCCATATCGGCCAGCGGCGGTGGCCTGGCCA
CGCAGCCGCAGAGCCTGCTCAATCCGGTCACTGGTCTCAATGTGCAGATCAGCACCAAGAAATGTAAGACTGCTTCGCCCTGCGCGATCTCCCCA
GTTCTGCTTGAGTGTCCCGAGCAGGACTGCAGCAAGAAGTACAAGCACGCAAATGGGCTGCGTTATCACCAGTCGCATGCCCATGGAGCGGGCGG
TGGCGCAAGCTCCATGGATGAGGACTCCATGCAGGCGCCCGAGGATCCGGCCACGCCGCCCTCGCCAGGAGTCGCAAGTGGAACGGGATCAGGAG
CATCTGTAGCATCATCGGCAGTACCAGCGACAGCACCATCAGCGGGTCAAGGAACTGTCGCAGTGTCCCCAAACACACCCCTCGCAAATTCAAGC
AACCCCGTCACCAATGGCAATGTTGCACCATCGGCACCAGCTACTGGATCGGTAACTATCGCCGCTCCCAACACTACTCCCTCTGTGGTAGAGAC
GCAAGCGCCGCTTACTGGTCCTCCACCAGTCACGCCACCAGCTCCAACTCCCATCTGCGCAGTTGCAACACCCGGAGCGGAGCAATCTGTATCAT
CAGTATTGCCCCTGGGAAATCTTCCACTGACGGCAGGTCCAAATAGCGCGACACAACAGCAACAGCCTCCTACACAGCAGCAACAACCACAGTTG
CTCGTCCCAGGAGGCAGTGCGGCAAGCCTTCAGCAGCAGCAGCAGCAGCAACCAGTGGCCGGAGGCAGCATCACTGCTGGAATCTCCGGACA
GGCTCTGTCACAGCATCAACAGCAACTAATGGGTGGATTGCCTGCCATGTTGTCAGACCAGCAGCAGCAGGCATTGTTGCAGCAGGGAGCACTTA
AAGCGGGTGTACTGCGTTTTGGCCCGCCAGATGGAAATCCCCTGCAGCAGCAGCCTGGTCAAGCATCGGTTAATCCACAGACACAACAGTCTCCT
CCAAGGCCTCCCAGTCATGTCCAGGATCAACAGACGCCATCGGCCTACGCCCAGCAGGCAGGTTTAAAGACATCGCCTGGATTTGGCTCCGTTGG
CGTGGGTGCCGCTAGCAGCAAACAAAAGAAGAACCGCAAGTCACCTGGACCCAGTGACTTTGAGGGCCGCGTATCGCGCGAGGATGTACAGAGTC
CGGCATACAGTGATATCTCCGATGACTCCACGCCAGTTGCCGAACAGGAAATGCTGGACAAGTCAGTCGGCCAGGCGGTGACGGCAAAGCACATC
GAATTGATGGGCAAGAAGCCGACGGAAGTGGGCGTTGGTGTTCCGCCACCACCAGCTCCCAATATGTATGTGCCGGGAATGTATCAGTTCTATCC
GGCGCAGCAGCAGTCAGCACCTCCACCACAGCAACAGCAACAACAGCCGCAATACATGGTGCAGACAGAGCCAGGCAAACCACCAGGATTGCCAC
CTGCTTTGACACAAGCTCAGCAGCAGCAACAATTGCAGCCGGGTGCTCCTCCGCCTACCTCACAGCCCCCGAGTCATTTGCTAGGTCCACCCGGT
CAGCAGTCGGTGGCTGCCCACCTGGCAGACTACAGTGGCAAGAACAAGGATCCACCATTGGATCTGATGACCAAACCGCAGCCACAGCCGGGTCA
GCCGCCTTCACAGCAGCAGCAGTCGGGCCAACTGTCGGGGCAGGAAAACAATGGCAAGGATGTTGGACCGCCCACCTCTCAGCCAGGATCTCAGC
CGCCGCCGGTTAACCTAAGTGCAGTGGCTGGGCCGCCGCCAGGAAGCCTGCCACCCGGTTTGGGTGGTCTCTCGGCTTTGGGAGCAGCCGGTCTA
GGTGGTCCTGGACCGGGCAAGGGCATGCCCCACTTCTATCCCTTCAATTTTATTCCGCCTGCGTATCCATACAATGTGGACCCCAACTTTGGGTC
AGTTTCTATTGTTGCTTCAGAGGAGGCCGCCAAGCTGAGTGGGCATCCGGGTCTGCCACCCAGCTCACAAGCGCAGCAGTTATCCGGCATAAGTA
TCAAGGAGGAGCGTCTGAAGGAAAGCCCCAGTCCGCACGACCAGCCGAAGCACATGCCATCTCAGCAACAGATGATAGCCAGCAAGCTAATCAAG
CAGGAGCCGATGACCAAGCAGGAGATCAAGCAGGAGCCCAACTCAAATCCGGGCCAGCAGCATCCGCCTCCGCAACAGCAGCCAGCGCCTCAGCC
GCAGCAACAACAGCCGCCACCCCCGCAGCCACAACAGCCGCATGCCCTGCATCCCAAGGATTTACAGGCACTGGGCGCCTATCCCGCCATCTACC
AGCGCCATTCCATAAACCTGGCCGTGCAGCAGGCTCGCGAGGAGGAGCTGAGACGGTATTACATGTTCACTGGACGACAGAATTCGGCAGCCGCA
GCAGCAGCCGCAGCAGCTCAAAACGCTGCCAGTGGTGGTCTTCCACCGCATCCCGGCATGATGCACAAGGATGAGCCTGGCATGGGATCGGCGGC
GCAACAACAGCAGCAGCAACAACAGCAGCAGATGCAAATTGCACAGCAGCAGCAGCAGGCCATTCAGCAGCATCATCAGCACCTGCAGCAGCAGC
ACCAGGCCCAGCAACAGCAGCAGCAGCAACAACACCAGCAGCAGCAGCAACAACAGCAGCAGCAGCAACAACAACAGCAGCAGCAGCAACAACAG
CAAAAGTTAAAGCAATCGCAGGCGGCTAGTGCGGGGGCAAATAATAAGGCCACCAACCTGACGAAGGATTCTCCCAAACAAAAGGGCGGCGATGA
CGATCAACCGCTGAAGGTGAAGCAGGAGGGCCAAAAGCCGACCATGGAGACGCAGGGTCCGCCACCACCACCCACGTCGCAGTACTTCCTTCACC
CCTCATACATTTCCCCGACGCCCTTTGGGTTTGATCCCAATCATCCGATGTATCGCAACGTGTTGATGTCAGCCGCCGGACCGTATAATACGGCA
CCGTACCACCTGCCCATCCCTCGCCCGTACCATGCCCCAGAAGATCTCTCGCGTAACACCGGCACCAAGGCGTTGGATGCACTCCATCACGCGGC
CAGTCAGTACTACACCACCCACAAGATCCATGAGCTCAGCGAACGGGCCCTCAAGTCGCCCACCAGCGGCAGCGGCCCCGTCAAGGTGAGCGTCA
GCAGTCCCAGCATCGGGCCGCCTCAACCAGGCGGACCCACGAGCAGCGGCCCCGGATCCGGACCAGTTTCCGGTGTCCTCGGCCCCGGCAGCGGT
TCCAACCAGCAGCCCGGCTCGGCACCTGGGTCTGCGGGCGGTGTGCCGCTGAACCTACAGCCACCACCCGGAGGAATGGGCCCGTCACCCGGCAG
CAAGCCGGATCTGTCCGGCCCGAAAGGACATGGCGGAGTGACGCCCGGCTCGTCATTGGACGGCCACAAGCAGTCGATGCCCGGAGGTCCGCCAC
CGAACGGGCCATCGGGCAATGGAGCCGTTGGCGGTGTGGGAGGCGCTGCCGGCAATGGCGCAGCGGGAGGCGGCGGTGCAGGTGCCGCCGACTCA
CGCAGCCCACCACCGCAGCGCCATGTGCACACCCACCACCACACGCACGTCGGCCTCGGCTATCCCATGTACCCGGCGCCGTATGGAGCGGCTGT
TTTGGCTAGCCAGCAGGCGGCTGCTGTAGCTGTGATAAACCCGTTTCCGCCGGGTCCGTCGAAATGA
(SEQ ID NO: 623)

Start ATG: 160

MEKKLAKVALNSSNVATESNIKNNKLLANLSAAGAATATTATTGTATTTTATTANQALNFNNKTKATANATAASANNRHNNNNNSSAIKKHTNTK
QLAGKSPACNSSSSSLSSSSSSNSSESKDTNFEYEDEWNIGGIPELLDDLDADIEKSAHSSGGGNQATALNAKQANSSSTSSSSSSKGGASSSSS
SAAATGSSSSHKSHKTTLHSNLSATSPTTIKFTRQPVAIGGANSSSSSSAAAAPSGGSANVVAKGSSSSSSSTSSSSSGKHHHHHHHHSNSSSSG
SSSKGYKSALVAQLNSPSPLNSNSKSLSGSGSGSGNTNGAAGAGAGSTLSSSTFAGFSKGGSLVSSSAGAAAALAAGSGQQGSKFSAGGMSSQTG
SGSGGNNTSNSNNSSSGSGGSGSGSSTGNTASGSGNNNSTSAGGPPSSQGGNNGNGSGSSSSSSSGKSSAKMSIDHQATLDKGLKMKIKRTKPGT
KSSEAKHEIVKATDQQQNGALGAGSNNSANEDGSSGSSSTNASSLGSTNSSSSASSGSSSSSGSSSSSSKKHLNNASSGSGSSSSGGGSQNNASG
HASGGGSSGSSQSTPQGTKRGSSGHRREKTKDKNAHSNRMSVDKSAAAASAAGEKDTPEKCSGTGAGGSPCSCNGDVGAPCSHHACIRRAAHMSN
SAGNANSSAGTGQSGGSSSMSAVPPGVFTPSAGSPSTGSPSTVVPAAASLLAATGAASSSASQMASSSAGGVGGSGGGANAPGPPGKESAGSIKI
SSHIAAQLAAAAASNSYSGSGANTNQGQNSNAGGNGGSESKAAAAAQAKLMAPGMISATMHHTISVPAGTGTGDDDTKSPPAKRVKHEAGASGAG
GGKEMVDICIGTSVGTITEPDCLGPCEPGTSVTLEGIVWHETEGGVLVVNVTWRGKTYVGTLLDCTRHDWAPPRFCDSPTEELDSRTPKGRGKRG
RSAGLTPDLSNFTETRSSIYFSHAQVHSKLRNGATKGRGGATPSTSPTAFLPPRPEKRKSKDEAPSPLNGDASDGASVGGIGGAGGVNMVNASGI

FIGURE SHEET 338

PISASGGGLATQPQSLLNPVTGLNVQISTKKCKTASPCAISPVLLECPEQDCSKKYKHANGLRYHQSHAHGAGGGASSMDEDSMQAPEDPATPPS
PGVASGTGSGASVASSAVPATAPSAGQGTVAVSPNTPLANSSNPVTNGNVAPSAPATGSVTIAAPNTTPSVVETQAPLTGPPPVTPPAPTPICAV
ATPGAEQSVSSVLPLGNLPLTAGPNSATQQQQPPTQQQQPQLLVPGGSAASLQQQQQQQPVAGGSITAGISGQALSQHQQQLMGGLPAMLSDQQ
QQALLQQGALKAGVLRFGPPDGNPLQQQPGQASVNPQTQQSPPRPPSHVQDQQTPSAYAQQAGLKTSPGFGSVGVGAASSKQKKNRKSPGPSDFE
GRVSREDVQSPAYSDISDDSTPVAEQEMLDKSVGQAVTAKHIELMGKKPTEVGVGVPPPPAPNMYVPGMYQFYPAQQQSAPPPQQQQQQPQYMVQ
TEPGKPPGLPPALTQAQQQQQLQPGAPPPTSQPPSHLLGPPGQQSVAAHLADYSGKNKDPPLDLMTKPQPQPGQPPSQQQQSGQLSGQENNGKDV
GPPTSQPGSQPPPVNLSAVAGPPPGSLPPGLGGLSALGAAGLGGPGPGKGMPHFYPFNFIPPAYPYNVDPNFGSVSIVASEEAAKLSGHPGLPPS
SQAQQLSGISIKEERLKESPSPHDQPKHMPSQQQMIASKLIKQEPMTKQEIKQEPNSNPGQQHPPPQQQPAPQPQQQQPPPPQPQQPHALHPKDL
QALGAYPAIYQRHSINLAVQQAREEELRRYYMFTGRQNSAAAAAAAAAQNAASGGLPPHPGMMHKDEPGMGSAAQQQQQQQQQQMQIAQQQQQAI
QQHHQHLQQQHQAQQQQQQQQHQQQQQQQQQQQQQQQQQQQQQQQKLKQSQAASAGANNKATNLTKDSPKQKGGDDDQPLKVKQEGQKPTMETQGPP
PPPTSQYFLHPSYISPTPFGFDPNHPMYRNVLMSAAGPYNTAPYHLPIPRPYHAPEDLSRNTGTKALDALHHAASQYYTTHKIHELSERALKSPT
SGSGPVKVSVSSPSIGPPQPGGPTSSGPGSGPVSGVLGPGSGSNQQPGSAPGSAGGVPLNLQPPPGGMGPSPGSKPDLSGPKGHGGVTPGSSLDG
HKQSMPGGPPPNGPSGNGAVGGVGGAAGNGAAGGGGAGAADSRSPPPQRHVHTHHHTHVGLGYPMYPAPYGAAVLASQQAAAVAVINPFPPGPSK
*
(SEQ ID NO: 624)

Celera Sequence No. : 142000013383837
CGCGCATCCAGCGGGCCACCACACTCACCTCGTCCATGTCCCTGCCGGCGGAGTGCCTGGTTCTCTCCGTATCCATGCCCTCGCTCAACTCGGAG
CCCAAGCGTCCCAAGAGCGCGGGACCCAAGAAGAAGCCCGGCCAGGCCGTCCACTCGAAGCCATTCCGCCTATATTGAGCCTGTCGAGGAAGGAG
CTGCTCCACAAGTCGCACGTGACGTCACCCAATCGAAGCACTCAGAGATTTGTGCACAAGTTGATATCGAGGCACGCACTTCTAAAACATGCATA
TGCAGAATACATTTTATCAAACCGTTGATTGTTTAGAACCGAAATGGAAACGAAACTTGGCATTTACAACATAACAATAAACGACTAAATGAGAG
GCAAAGTTAAGCACAAAATACAGCTGTGGTTTGTTTGTTTGTTTCTTTATATAATTACAGTATATATTTTCGTAAGTATTAAATCTGTTTCACGG
CTACTACATCGCTGGAGCCAAACGGCCTTCGTTTACATTTCATTTACATAAGACTTGCGTTTGATTTTCTATATATAATTAGTACAAAAATTGTC
CTGGGATTTCGTTACGTCTCATTGCGTCTTTATCATCGTGCTCATTGTGTGTTTGGAAAACTGTGTGCTTTTCTTGGTTTCTTTAGGTTTTGTAT
TCGTTTTTGATTCTTGTTCCTTTCGATTATTCGAGTCGCGTCACATTTAAATGCATTTAGTTGCCTTTTTCCATTTACATCATCCTTTTGCTCTA
CTTAAGCCATAAAAGTTGTTTATACAATTCGTTTTTAAAGTTAGGGTAATAAATAGGTCATTATAAAATAATAAACAACAGTTGTTACATTTTCA
AAAGACATCGTCAAATGAGCTTCAAGTGATTATGATTATGATTCGAGGGTCGAGTTAGAATTAAAAAAATGCGCATGCTTGAATATCATAAAAAG
TGGCTTCTCTAAGAGCTCGTCGTCAAGTGAATTGGCCTGGTTTCAGATTTGGTTAGCTGCGGATTGGCTGCCTTAGCTCATGGCTATATATAACT
ATAATACATTTAATGGGAAACTAGGAAATGCATAGATGCTCGTGATATGCGAAACCAATGTTTGCTGCGGTTGTTATAATTTTCTCTTTCTGCCA
GATACTATTCGTACAATACATTCGATTCAATTGACTAGATTTCTACATATGTAGTGCATTAGATTTATGATTTATCTGTGGTACCGATTTTGTTA
ACAATGTTTTTTTAGTTGTTGCGGGAGGGAATCGTGGTTTGCCAAATGTGTGACAGCAACGATCCGCAGAAAAAAACAGCCAAACAAAGAGAAA
TTTCATACGAATTTTGATGGCAGTACATTTCGATTCACAGAATTTCGTACAATATTTATCGTTTGTTTAGAGTTTCTTTCCGGGTTCGGTGCCTT
TTACGAGAGTACGGAGAATTTTATAAATAAATACATGTAATTGATTTGTCGATGAGGGCGCTGCGTGAGTGTCAATTTGTTGTGGCCATTGTGCC
GGTGTACGTGTCGCTTCCGAGGAATCTCTATACTTCGCCAAAGCCAATAACATTCTACCTTATTTACATTATTAAACACTTTCGCTGGCGTCGCT
TTAGCGGCTCTGGTCTGAGCACCGCGCGCACCGCTTCCTCGAACACCTGAATTTGCAATCGGAGTGGGAAGGGAAATTTAATGATGAATAAGGGG
TAGGTGGAGGGTGTGCCGGGCACCGATGACTTACCGGCTTGAGACCGCGCTGCGTCAAGGCGGAGCACTCCATGTATTTCACAGCGCGTATCTTG
TTTGCCAGCTTCTGGCCCTGCTCGCGCTTCAGCGGCGTCAGTCCCTGCTCTGCCAGGCCGCTGAGTGTCTCTCGATCTTCGCGCAAATCGATTTT
GGTGCCTGGAATACGCCCAAAGATATATGTATGATTCTCGTTTTCTGATTGCAGTTTTCATGTCGCTTGGCAACTTACCAACTAGAATGATGGGC
GCATCGGGACAGTGGTGCTTTATCTCCGGATACCATTTCGAGGTGACGTTCTCAAAGGACGAGGGACTCGCCACGCTGTAGCATATCAGGAAAAC
GTCTGTCTGCGGGTAGGATAGCGGTCTCAGGCGGTCGTAGTCCTCCTGACCCGCCGTATCCCACAGTCCCAGCGAGACCTGTATTGTGTCCACTT
GCATGGGCGCCGAGTAGTTGTCGAAGCTGTGAAAGATATCATAGTAAAAGTTAGATATCGATCTGCGGTTTGCGGCTATCGAGGCACAAACTTAC
ACTGTGGGCACATATTCGCCGGGAAAGCAGTCTGTCGTGTAGGAGATTAGCATGCAGGTCTTTCCGACGGTGCCGTCACCAACGACTACACACTT
TATGGGCCTTCCGGTTGACATCGTGAGTGTGCTGAGTGTGCCTGTGCCGATAGCTGTGTACTGTCTGTGTGCTGTGGGCAAAATAAGATGGAAGA
TGAATGTCTTCGCCAGCTTAATTCAATTAATTAAGTTCTATTCGAGGCAATAAACCCGCCAGTGCCAACTGACCGCAAATTATTTCACAGTCGTA
CTTCCTTAATAAAAATTCTTTAAAATAGAAACAAATGCTGTAGAAATACATATATGACACAATAAATTATCCTATTCGTTTTATTAGGTTTTTAT
AAATAAATTAACTACCACATCGTTTTTGGCGCGCAACTACATATATATAAGATAAACAATTGCTTAAATGGAATTTGGCAACTTTTAAAATTTGA
ATATCTAGACAAATTGAATCAGGATACTTGCTTCCTGAGTCGCAAACTATTTATATTGTATTAATGGAAGTTATACTTATTGGAGTATGCTACAT
CGTAAAGTGGGAATGTCCAAGCTGTGGAAGTACTACTGTACAGAGTATAATGGCGAAGGTCTACGGTATATCTCTGGGATGATCAAAGGCAGGGC
TCTCGAAAGGTGTGTCCCGGCCGCAAAAAGAAAGCAACCGCAGCGGCGGAGGCCCATAAAGCCTAATAAAACGAACGAGGGTCTCATTTCGGTTG
CGGTGGCACTTTGTTTTCGCAAATAAAATTTTCAAAAATAGATCATGATGGGCGACACAGACGGGGAAAAACAAAAAGCATAAATGGGAGCAGCG
GACCAAATGGCGACCGCCCCTCCAGTGGCGCCCCTTCGGCGGTGGGCGGGGTCGCCCGAGTGTTGTGGTGACGCGGAAGCCACCGGCAGACGCAC
CGCATCGAGAAAAAGAAACACAAAATGGGAAAATGAACCGCCCGAAAATAGACACAATTAAGTTCTCATAACCGATTCAATTAAAGTTCAACACA
CAGAGGCGGCACATATTGCGCCACATGCAACGGGGCTGGGCGTGGCCGCGGGGGCGGGTGCGGTAGCAATGAAAATCTTTTGTTGTGGCACAACA
CCGAATGGGAATACAATATTATTTTACCGTTTCACCACCACCTATCCTTTTCCTTTGTCTGTCGGCAGGCGGCGACTGTTTTGTACTTGGCTTA
TATCACTGTGCGTTTTCCGGCTACCGATATGCGTTCGAGGCGATGGTCCATGCGGCGCATTTAAATAATTGATTCGCACTATTTCGCAGCGGCTT
TTACTTATAAATATCTGTTTGAGGGACAAAACGCAGCGTCCCCGAATAATTTTCGTGTTTTTCCTTTTTGTTTCCACTCCACACAAACACACACC
CACCTTTTTGACAGCGCAGCGACGCTCTCTCTCGCCGTTGACAGTGGTGCCAACTTAGGGCCAGAAAATAGCTGACGGTAAATATAAAAAAAT
CACTTAAATGTATGGTACCAATAACTAAACTTAATAAGCATATCATCCAGTATAAAGTCGTTTTTCTTTTTCCAAAACTAAAATAAACTTTTTTT
TACAATTGGCACTTAAAAATCAGCTAGACTTGGCGTGAAAAAAGAGAGCGGGTAGTCCAGCTCCGCTCTCTCGAAACTGACAAGCAGTGCTGCAA
AAGGTGCAGGGCTCAGGCGGATTTGGCATTATACAATACTAATAGGCATGGTTGTGGGAGAGGGGTTGCAACCAATTTTCACATTGTAAACAAAA
TTATTTATTTAATTCTATTTCGAGCAGAATATTGTAATAATTACCTGTTAATTAAAAAATTATCATTTTAAAATTATCTTATGTAAGTTCAATAC
CCTTTAATTGCTATCGACTACGCCCATGCTGCCTATGTCCACTGTTGTTGTTTCGAGCGTCGTAATGAGCAGATTTGTTTATAAACTTTTACAGA
GTGCAAACCAAACTAGTTCGGGCTGCAGACGCATTTCTTTGGCTACTGTAAGAAATGCGGAAAGCGAATCTCAAGAGGGTGCCCCTGCCCGCACA
GTTCTGGTGGAGAAGGACTCGCACATAACACTTATTGGCCTAAATCGCGAGCA
(SEQ ID NO: 625)

Exon: 3423..3231
Exon: 2446..2281
Exon: 2211..1979

Exon: 1905..1745
Exon: 1661..1001
Start ATG: 2396 (Reverse strand: CAT)

Transcript No. : CT17672
CGGTGTTGTGCCACAACAAAAGATTTTCATTGCTACCGCACCCGCCCCCGCGGCCACGCCCAGCCCCGTTGCATGTGGCGCAATATGTGCCGCCT
CTGTGTGTTGAACTTTAATTGAATCGGTTATGAGAACTTAATTGTGTCTATTTTCGGGCGGTTCATTTTCCCATTTTGTGTTTCTTTTTCTCGAT
GCGCACACAGACAGTACACAGCTATCGGCACAGGCACACTCAGCACACTCACGATGTCAACCGGAAGGCCCATAAAGTGTGTAGTCGTTGGTGAC
GGCACCGTCGGAAAGACCTGCATGCTAATCTCCTACACGACAGACTGCTTTCCCGGCGAATATGTGCCCACAGTCTTCGACAACTACTCGGCGCC
CATGCAAGTGGACACAATACAGGTCTCGCTGGGACTGTGGGATACGGCGGGTCAGGAGGACTACGACCGCCTGAGACCGCTATCCTACCCGCAGA
CAGACGTTTTCCTGATATGCTACAGCGTGGCGAGTCCCTCGTCCTTTGAGAACGTCACCTCGAAATGGTATCCGGAGATAAAGCACCACTGTCCC
GATGCGCCCATCATTCTAGTTGGCACCAAAATCGATTTGCGCGAAGATCGAGAGACACTCAGCGGCCTGGCAGAGCAGGGACTGACGCCGCTGAA
GCGCGAGCAGGGCCAGAAGCTGGCAAACAAGATACGCGCTGTGAAATACATGGAGTGCTCCGCCTTGACGCAGCGCGGTCTCAAGCCGGTGTTCG
AGGAAGCGGTGCGCGCGGTGCTCAGACCAGAGCCGCTAAAGCGACGCCAGCGAAAGTGTTTAATAATGTAAATAAGGTAGAATGTTATTGGCTTT
GGCGAAGTATAGAGATTCCTCGGAAGCGACACGTACACCGGCACAATGGCCACAACAAATTGACACTCACGCAGCGCCCTCATCGACAAATCAAT
TACATGTATTTATTTATAAAATTCTCCGTACTCTCGTAAAAGGCACCGAACCCGGAAAGAAACTCTAAACAAACGATAAATATTGTACGAAATTC
TGTGAATCGAAATGTACTGCCATCAAAATTCGTATGAAATTTCTCTTTGTTTGGCTGTTTTTTTCTGCGGATCGTTGCTGTCACACATTTGGCAA
ACCACGATTCCCTCCCGCAACAACTAAAAAAAACATTGTTAACAAAATCGGTACCACAGATAAATCATAAATCTAATGCACTACATATGTAGAAA
TCTAGTCAATTGAATCGAATGTATTGTACGAATAGTATCTGGCAGAAAGAGAAAATTATAACAACCGCAGCAAACATTGGTTTCGCATATCACGA
GCATCTATGCATTTCCTAGTTTCCCATTAAATGTATTATAGTTATATATAGCCATGAGCTAAGGCAGCCAATCCGCAGCTAACC
(SEQ ID NO: 626)

Start ATG: 244 (Reverse strand: CAT)

MSTGRPIKCVVVGDGTVGKTCMLISYTTDCFPGEYVPTVFDNYSAPMQVDTIQVSLGLWDTAGQEDYDRLRPLSYPQTDVFLICYSVASPSSFEN
VTSKWYPEIKHHCPDAPIILVGTKIDLREDRETLSGLAEQGLTPLKREQGQKLANKIRAVKYMECSALTQRGLKPVFEEAVRAVLRPEPLKRRQR
KCLIM*
(SEQ ID NO: 627)

Classification: enzyme

Celera Sequence No. : 142000013384557
ACTGCGTGAGTTCTTTCTGTTGTTTTTTGTTTGTTTGCTGCTGCCAAGAGGAAACCTTACGATTAGTTTGTGATTTAATTGGAATTTTGTTGGTA
AATGTTGGATCTCTCATCTAGATTGCATGTACAATATAATCGTTTGATTTGTTTTGGGCGCGTTCTCATATCAAGAGCTATTTGTATTTGTATAT
GTATAACTACTATCTAAATAGCGTTAGTAATTTACGTATATTATTTACACTTGCATTGTTTTTCTATTTTTTTGTCGGTCTATGTCTTGATCCAC
TTATGTCTTGCGTTGTAAATATTTGCACGGATATTAAAAACAGAAATATTTCTATTATTGAACACAGTATTGCATTTCTCCGTCACCTCGCTCCT
TCTCCTTCTCCTTCTCCTTGTACATGTCTGCCTGTCCTCTGGTTTGGTTCATCACTTTTTTTTTTGCTAAGATCAATTGAATGTCTTTTGTTTTT
AACTCTGTTTCTGTCGCGGCATATGGTGCAACTGCTGCCGGGGCAGCTCACAAAATTTGCATAAATAAATTCTAACAACACGCTTAGGCTATGTG
GTTAAGTAAAAAAAATACATTAATAATTTGAATACAGCTGTTGTTGCCACCGGGCTTAGCGCACGCGGTACCCGGTATAAATAATAAATTAAACA
TTTATAACTATTGCAACGCTACTCGACCTATCAACTATATCAAATTGTATATAACCGTATATAAATATGTCCTTTTGCTAAAAATTATTATTATT
TGTTTGTTTCTTTCTTTCCTTCTTTCTTGCATTCTCGTTTCGTTACTAGTCTAATGCATTAAAGTAATAATAACTGCGGATTATCAACTTGCTAG
CTTGACTTTTGTGTGTGGTTAGTAGAAGAAAGTCGAGGCAAATATTCTATATACTCGTACCTATTCGCTAGTTACATATTATCATAATTATTATC
ATTATCGTTATCATTATTTCTTTATGTAGGTAAGCATAGTGTTACGGTTATTATGTACAACTGTCTGGGTGCTGGCTCTGCTTGCGCTTTGACTT
TGGCTCCTTCGGATGCTGATCGATCGACGGACGACGCGGATTGCCCAACGTGACTAAGGCGCTGGCCACAGCCAGACCAGCGGACTGGCCAGAAG
GCGCTTGCGAAAGGCCACCTGCGAGTAGAGTGATTCATAAGTAAGACACATACATTCTATAAGATGATTACTTCATCCTTACCCGTGGGCAGCCG
GACTAGAAGCGAGAGCACAGCGGCTCGGTTGCCACTGCAAGGCTCCAAAGCGATGGGACTAGGGCATTCCTGTGTACAAATAAGATACAAAATAT
TTCATAGTTTAATCTCAAACTTGTAATGTCCAAATTAGGCCTAGCTTTATATAATCTGTTCTGTATGGATTCCGTCCGCTAAAAAGTCGGCTCAT
AATTTTAAGCACTGAACGATTGATTCGCCTACCTTTTTGCGTTTTTTGGACAGGTGGCCAATGCCCTCCAGCGTCAGACTCAGATCAATACTTTC
GCGGTTCTCGATATCGACCAGCACCTGTGCAAAAATGTTTGCAGATTAGAGTCAACGCAATCAAGTTTCCTTTTTTAGATCTCACCTGGGAAAAC
GGTCGACTCGCCATCTGTTCCATTTCGACGAACAATCGCTGACGCCGCCGGAACATGTCGTACTTCTGCTTAATCTTCCACAGGACGGCGGCCAT
AAGCAGCAGCAGTAGGAAGCAGGAGGAGAATGTGATGAAGAATTGCTGCAGGTTGAGCTTGGGATACTGTGAGAAGGCAATTTGTATCCAGATTG
GGGGCTGGAAGTCGTGCACGAACACGTAGAACGTGGTCAGGGAGCTGTTGTCATCGGGCGAGTGCCCGAATTGGTAGTCCGTCTTGGGGAACCGA
TGACGGAACGTTGAGCAGTTAACGCCCACCAAGATCAGCATGTCCGGCGAGCCAGCCCTCTTGACCGAAATGTCCATTTTGGCCGGCACGCTGCA
CGTAATGGTGAAATCCGCATCGATCTCCGGCTTTCCCGGTGAGTTCCTGAAGTTAATTTGTGTAAAGTGGCGATCCTCCTTCTTTGAAAGATTAA
ACGTGAACTGGTAGTCGATGGTCAGCTCGTAGTAGCAGGAGCCCTTTAGCGGATCACCGTGGTAATGGTTCTGGGAGTCGCACTTCTCGCAGTGA
TCACCGACTATACCCTTGGTGGTGCAGAAACACTTCCCAGTGTCCGGATGACAGTAAACGCCTTGGCCGTTGCAATCGCATCGCTGGCATTTTCC
CCCGTTTATGGGATTACCCCAGTATCCAGTGCGACACTTCTCGCAGTGCGCTCCTGTCGTCAGATTATTGCATGGCTGTTCACAATGCTGTTGGT
CATTACAATACGAATGCCCGTTGCAATTGCACCGGGGGCAGGACGTAAAGAACCAGTGCTTTAGGGCGCACTCCGTGTCATCGTAGGGTGCCAGT
GCTCCGCCAACCACGCACCTGCCCAGACCGGTGTTAGAGCCATTGTCACACCAACCGCAAGCCGGATCGTCCAGGCACATCTGGCAGCTGTTGTA
GTAGCCACATTGAGCACTTGACAGTGCCGTAGTGCTGCCCACGGCCAGTGCCGTTGATTGGATGGGAGCCGACCGGCACTTGGCTGTGAAGGTGG
TCCACTCTCGGCACTGACCGTAAGGAAAGCTGGCCGTGTAGGCATTGCGGTCCACGCAGCGCTGTTCGTTTTGGCACCAGATGCACTCGTCCTCG
GTGCAATTCTGGCAGTTGGTCAATGAAGCGCAGGACGGCGAGCAGGCCACCTCATCCTGCGTCCGGTTGAGCGCCAAACCACCGTAGGAAGTGTA
GCTTTTGCAGCGGTTGTGCTCCGAGTCCCAGCGACACGCCAGGTTGGCAGAGCAGGCGCGACAATTGTGCAGCTGATCGCACACAGATGACACCA
GGTACTCCTCGGAGATGGGGCACGAATCCAGATGCTTGGCATTTAGCGGCGGACTAGCCGTGGACACTGCCATTTGTGTGGACGACTCGAAGAAG
ACCGAAGCCATTGAGGTGGTTTCACGACACCGCTCCTTGCTGCACACTCCGTTTCCGCAGTATGTGCAACCAAAGGCGGTGGACACGCACGATTG
ACAGCTGGCCAGTTCCTGGCAACGGTGCACATCGTGGAGTAACTCTGAAGTGAGGGTAAGACGGCTCTTCGACGGGCAAGCCACATAGTCGTATT
GCTCGCGTCCGTAGATCGCCGATCTTTGAACCTGGGTAATGGCGATGCAACGCATCTTTTGCACGTCCCAAATACACTTCACTCCAGGTCGCGCT
GCCGTGCACTTCTCCTGTTTGGTGTAGTAGCTGCAGTAGCCCGGCTGGTAGCGCAGCATATCGTTTAGCAGCTGGCCATTGAAGCCGCCATAAAT
GTACAGCGACTCCTCGAACACAACCGAACTGTGACCGAAGCGGGCCAGATCCGCCTGCAGGTGGCCCGGCATCGGATGGTAGTGCCACGAGTCGC
AGTACACGTCGTACACGAGCAGGTCCTGGCTATAGCATTTCGCGCCGTAGCTCTGCGATGTGTCGTTGTGCGTATTGCCACCGAAGACCATCATT AGTCCCTGGTTCACAAAGTTTGCCGTGTGAAGTAGACGCGCACTTGGCGCCGCAGACAGCAGACTCCAAACTCGCGTTGCCGGTTCATAGGCATA
CAACCTAGAGCTCAGCACCTGACTGGACTCACTCTCGGAGACTATTCCACCGTAGACGTACACCTTCTCCGTAAGAAAGTCGTACGCGGCACTGT
GTCCGTATCCGCCTTTCACCACATAGCCGGTGGTGGGGACGATGCGCCACTCTCGTGATGCAAAGTTGAACTCCTGCACTGTGTTGAGGTAGCCG
TAGTTTGGAGAGTGACCGAAGATAACAACCATGTACTGGTAGTTGTTTTTGTCCCCGTAACCGGGAACCAAGGTAGCTGTGTGACCCACCACATG
CAGGGGTCCGCACATAGCGGTGGTTCCTCCAGTGGCGTTGCACGAGGGATCCGCTCTTACCGAGATGTTCGCCCACGTTCGCGCCGAGACGTCGA
AGGCCCACAGTTCGTTGGAGATGCCGTGGCCCTTGACCACTCCACCGTACATGAAGATCTTGTCGCCGTACATCACTGTCGAGGCACCGTATCGC
TTGTCAGGAACCTCGCTACCATCCTCCGGGTGCACAGTCTCCCATACGTTGCCATTGAAGTCATAGGTGCTCATTAGTTTGCCTCGTCCGTACGA
TTCGCCGCCCACAATGTGCAACGTGTCTCGCCAGATGGTGGCGCCATGGGAGGCGCTTCCGGCTGGCGCCGGCGAGTGCTTCGGGTGGACCGTGG
ACCAGGCGCCGTGGGCGCTGATCTGACTGCAATCGTCGCCGGCGAAGCCCTCGTAACAGGAGCAGCTGTAAGAAAGTACGAGACTTAATGAGAAA
TTGCAAATTCGAAACGAGCCATTTGCGCCCTTTTTGCACATAGATTAGTTTCTGCTTGCATTTCCTCGCTTTTCTAGTTTAGTTTCTGGTTTACA
CTTAGTTAAGCTACTCAGGCACGTAATTGCATTCTAAATTTAGACAAGTGACAAACAACTAGTTATCTACAGATAACCGGTAAAGAGTTTGTTAT
ATAACACAAACAATAACAAATGTCTTAAAGGGCTTTTTGAATACTATAATAAAACTCAATACGATGCAAGCAAAATAATTAAGGGCTTCATATAT
AGAGCCAACTTACCGTTCCTGGTCAAGACGACAATGGCCCTGGTTCTTGGACTCGAAGCAGTTGTTGGGACAGGCGGCTATGTTGCAGGCTTCAC
CCCTGTACATGGGATCACAGATGCAGTCGCCATCGCGACACTTGCCATGGCCGGAACACTCCACCTCTGAAATGGTATAAGTAGTAACTATTTAG
AATCTTCTCTGTTTAAGGTAAGCTAAATGACAATCGTACCATCGCTATCCGAGGGACAACTGTTCATCTTGTAGGTGAGGTTGAAACCGGACATG
TTGTAGGCATCGTCACTGAAGAAGTGCACCAGCGCCGTGCCGGATGTCGCTATCACCTGTGGCACTCGACGAATGGAGAAGTTGCCGCGATACAT
GAGGCCACTGAACGATAATACGGAAAGGAAGGAAAGCCAATGGTTAGTCATGAAATAAACATGTTGTCCAAGCAAACTAAGCTCACCTGAACACC
GCCAGCAGGGGCGAGTCCACGCTGTCGCCATCGTATATGTACAGATGATCCCAGCCGCACTCCGTGGCGAACTCTCGCAGGTGGATCCGTATGTT
GGCGGTTCGCGACGGATTGGTATTGTGTCGGCGGTTCCAGTGCGGATGTCTGGCGTCGATTAGCCAGCTGCACTTGACACTCACCGAATAGTTGC
CCCATCCGTCGTGTATTGTGCCCATGGGGTGGTACATGCTGCAGATTGGAAAGATGGCAAGAGAGAGTGGATATGGCATCCATTAGCTTCGAGGT
GGCTAAATAAATCAATTCCTCTATCGATTTAGCGATATGGAGTGCACACGCAAATGGCAATAGCCCGATGCTGTGAGGAGATAATTGAATTTGCC
GGTCAGCCGGCCAGCGCAATTGCAATCTACAATTGATATGGGTACAGTGTATGTGAGATGGTATAGGTTGCTATAGGCTGCATCGTCCGTATTGC
ATAGACTATCTGTGTCCGAACTGAAGCCGTTCAACTGTTGACCGGCCAAGTCCGTTGTGCATTCTCCACTCTTTGGGCATTTGTTTCCCGTGGCT
TTTGTTCTTTGAATGCGGATTACGAGTGAAAATATGTCTGGAAGACAGTCTTCAACGAAATGTGACAAGTTAAGAGCTTGAAACTCGAGTAGGGT
ATCCGCCAGTCGCATGCCAGTGCCTTCCTTTGTCTGTCTTATTATTTTCTTAGTGTTTTGTTTGCACATCCGCTTATAAATAACTGCTTTCCCCT
GATTTAGTCGCACTGATTTCAATTTACAGCTGTGCGAGCACAAAACGCAGTGCTCAACATACTCATATGTACATATGTGATAATTAAATGCTACC
CTGTAGTTGCAGCAGCCGTCTTAATAGTTGATCTTTCGTTTCTTAAATTAAAAGGTCAAACGAACATTTGCTCGTTCTCTAACAACAAAAAGTTT
ATCGGAAAATAAAAATATTCATTAATTAAATCATGAAGCAGATTTTAACTATTATACGTTAATGGCATAGTAGTGAGTAAACACTCTTTATAAGC
CCTTTGAACCGTGTGCAGATAAAGAATGGCTTTTCACCAAGCAAAACTCCATATCTTACTAAGCTGGCAAAGATAAAACGCGACATAATGATTCT
ATATCATTATAAATGGATGGTACAGCTCGTAAAATTTACATATATTAATTATAATTTGCAATATGTATGCACAGCTTCAAGTACATTGTTTGCCA
TTTAAAGAAACTTTGCACACTCTTCTCGGTTATTTGTTTGTTCTAGTTTTAACAATTAACTCACATAGTCAGTGTACTCGGAGAAAGTGGAATCA
GCAGCCTTCCGCATTCTAAATGCGACTCACGTTACACCAAGCAAGTGCCGATAAGTACTGCGTATAGTACACTAACAATTGCGGCCACAACAATA
GTGCCGATGGGCATTTTTGATTATTAGAAAACACTTTCCGTGTGCCTACACTAATAATTGCTTATTTATCACAATGACTTATCTAGAGGGTACAA
TTTGGTTTGCTTGTTTAATCGTTTTATTTTTGTCATCGCTGGCCATCATATTTTTATTATTTTCGCTTGTCAAAAATATGAAATAGACCAGATCA
TTAAACGAGATTTTTTTAAGTTTATGGTATCTAGCTTTGTGGCATCATAAAGTCAGAAAGTCATAAAATATTATTTATGTGGATTGCAAGGCCA
TATCTTTCAGTAGTTCTAAAACCTCTTTGATATTGATTATATCTATGCTAAATTCATATAGATTCTTAGATTCTCCCCAAGAAACCTCATATTTT
TACGCCCGTAGCTGTAGGAGACTGCGTCGTGTGGGCGTTGTGTCTCGGTCAGTTCTAAACTTTGAGTAAACACTCCGTCCAGCCGGGATGCAGTC
GTGCCTGGGGGGGCATATCAAACGATAGCCACGAAAAATCAATGTCGGCCAAAGATATATTTACACACTCATTGGCAGCCAGCCGGTGAGTCACT
CTGTGCACTCGAGCACAGCTTAGCTTACGCACAGCTTTGGAGATGGTAGATGGAACCACATATATGTATAGCAATAGCTGGGGCATCGGCACCGT
GAGCTGGAGTAGGTGAATAGGCGCCCTCGTCATGTGGCCATTCGGCTGGAATGCATTTGGAGTGAGGGAAACCAGTTCGATTGCGCCCAGTTTTT
GCATAGAAAGCCGGCAAAGCAGTTGCCTTTCGAAGGCAACTTGAGCTGGTGAATCGTTGGCAGCGGTTAGATCCGAACTAGCAGCGAAAAGACTG
AAAACTCACAGGCGATAAGCGGACACACACCGCTGATAAGGCCATGCCCTTATCACTGCTCAATTTGAGCGGACAAGTGTGTGGCCCCGGAATTT
ATGGCCCGCTAAATGCTGCGATCCAACGATCTCAAACGCAGGCCGGGATCAGGGGTCTGTGTGGAGCCTGAAACTGGTTTCTGGATGGTTGGGGC
AGGTGAGGCGACGACCTCAATGCTCGAGTGCGCAAATTGCAGGTCCCATCATCAGCAGCACGGCAGGCAGGTGAATGGGTTTAATTATTGTCAAG
ATAGAACGCTCGCTTATCGGGCTTCGCGAGCAAATAGCCGCTGTTAAGAAACATAAACAAACTATTTCATGAGCTTTATGACGCCAGCCGTAAGC
GTGAGCAACCAAACTGGCCCAACGACTTCTCACATACATATCTATTAAATATAATGTATAGCATTCGTGCAACACTTTAAATACATCAGCCTATG
CCGGGCAAAAAGCTGTTATCTAATGTTTGGCAAAATAAACATTATTTACTGGGATAATATTTTGGGATTGATGTGAAAGAGTTCTTTTAGGTGT
ATATACACCTCATTATTTATTAGTATGTCATTTGACATTTCTTGAATTAGATATTTTTATAGCACTGTTCCTACTTGGTTCGTCTTAAAGAAGCT
TTACAGTAGATAAGCAAAGCGTTTTGTATCTGACTCAGGTAATATGACGAATATAACGTTTTCCAGAAATATATGTACATATATTTTCCCTGCTC
AATCAGCACATTAGATGGCAAAGAAGCTAATGTGGCCAAAAAGCAGTGGCCTCTGCCCCAAACAAGTTCAAAGTCAAAGCGAAATAATTGAATAA
TCCGCATTGGAAGCGTCAGGAGGCGTAGAAAGCGGCCAGCAGGTGAAAGAATGTCTAGAGGGAAATGGGAGAAAGAGAACGGGAATTGGGAGAAA
GTGGATGGTGGAGCGGTGAAGAGACGAGATAAACACGGCCAAGAACCCGTCCGACCAGATGAAACTGAACCGTTGGCTGACACAAATAGGCCGGA
CCGAAAAGGCAGAGGAGATCAGACCGAAAAGAATGGAAAATTGATAGGATATTGATGGCTTAACCACCACATCTTACTGGACTGGAGCTGATCTT
TGGGGTAGCTGATCTATGGTCAATTATGTGACCTAATATGGAGATCTTACTCTATCTATGTGGCATGCTGTGCATAACCAGCCACTTACCGCACT
TTTCCGCCACAGAACTGGCACTCCGGTCCCTGCCAGCCGTCGGCGCAGAGGCACTGGCCGTCCTCCTGGCACTGGCCGTCGTTCTGGCAGCGGCC
GCCGTGGGCGGTGCAGTTGAAGGCGGCCGCCCGATGGAGTCCGCTGAAGCAGCCGTGGAAGAGGAGCAGCGTGAGGAGGAGCAGGCATTTTCGCC
TGTACTTGGCGTTGAATGTGGGTGAGGTGCTGCTCCGGTTCGGTTGCTTCTGCGGTGGCTCCGCCGCCAGGCACATGATTTGCGTAGTTGATTCC
AATTCACCGCCCGCCCGCAGCTTCACATCGTCGTCGTCCTGCAGCGAGTCCTTCGATTTTCGCGACTATTGCACAATTTTCCTTTGGGCCTTTCT
CTCTGGCCGTTTTTCTTTTCTTTTCTATTTGCAATCTTTGCAATTCGGGGCAACCCAAGGCCCCGCACTTGAACGCACACACACACACACGCACA
CACTGGCACACTCACTCACACTCGCGAACGCGGCTGCACAACAAACAATATTGGCAAAAAGAAACAACAACCTGCATCCAGCGACTGGCAAAGTT
ATTGACAATTTATTTGTGAAACGAAACGAGAAATCTGCTGGGGGTCCAGTGCTGCACAGCGTTGCACTGCTTCGGCGTTGCAAGCACTGCTTAAC
AGGGTTGTCAAGTCACTGTCGGTATCGATAAGATATCTAGCAGGGATTACTTTAAAATTATTAAACAAGCTTAGTGTGGTACATTTACTTATCAC
ATACATAAAGGAGTGCCAAATTTATATGAATAATAATATTAAAAATAATATAAGAGAATATTTTTAAAAAGCTTAATTTTAAAGCGTTAACAGTG
CAAGTAATTTAACTGTGGCACACTTTTGTTGCTATAGTTTTTCGAAACGTTTTCAAAGTGGTAAAATTGGCAAAATTGTAATACCAATTTCATTA
CTTTAGAATATTCATAATGCGACATCGACATTTTTTATATATTTTCAGATATTTTTGTTATTTAAAAACAGCTCGTACAATCGATATCTTATCGC
TGCAAACATTTCAGCCCTCGCAGTCGTTACAACCGTAACAGCACAGTTACAGTTGCAGCTTTCTGTTAGTAGGACTGCTGTTTATTTGTTTATTC
AAAAATTAGAAATAAATGTTGAAACCAAAGTAATATTTATAAAAAAAGCACTTAAAATAGAGCAAGAATTGTAGTCTTAGAAAGAATACATAGAA
CTTAGCTTATGAACAAAGAATTAAACACAAATAAATAGAAATACAGTAACCAGAAAATCAATACCCGTTAACAACAACCGGAGCGCGTAAATTCC
GTCAGTTTGACAGTTGCGTTGATAAGAACGATGCGGACGGACTTTTGAGTGCGCAGGCGCGCTCCGAGCGCACCCGTCCCCCCTTTCGTCATCGT
GGCTGTTTGCCTGCCAACTACTTTCCGGAATCCGATTTCTCAGACAGTCCACGTTCGGGCGTCGTTGCAAGCAGTGTGTGCTAACGGTACTCCAA
CCGCGCTGCATGTGCGTTCCCCGTTTGCATCTGTGTGCGTGTGTGAGCGGAGAAG

FIGURE SHEET 341

(SEQ ID NO: 628)

Exon: 9315..8735
Exon: 5453..5217
Exon: 5137..4980
Exon: 4911..4764
Exon: 4396..3957
Exon: 3878..1606
Exon: 1544..1458
Exon: 1304..1223
Exon: 1158..1001
Start ATG: 9006 (Reverse strand: CAT)

Transcript No. : CT17798
TCAATAACTTTGCCAGTCGCTGGATGCAGGTTGTTGTTTCTTTTTGCCAATATTGTTTGTTGTGCAGCCGCGTTCGCGAGTGTGAGTGAGTGTGC
CAGTGTGTGCGTGTGTGTGTGTGCGTTCAAGTGCGGGGCCTTGGGTTGCCCCGAATTGCAAAGATTGCAAATAGAAAAGAAAAGAAAAACGGC
CAGAGAGAAAGGCCCAAAGGAAAATTGTGCAATAGTCGCGAAAATCGAAGGACTCGCTGCAGGACGACGACGATGTGAAGCTGCGGGCGGGCGGT
GAATTGGAATCAACTACGCAAATCATGTGCCTGGCGGCGGAGCCACCGCAGAAGCAACCGAACCGGAGCAGCACCTCACCCACATTCAACGCCAA
GTACAGGCGAAAATGCCTGCTCCTCCTCACGCTGCTCCTCTTCCACGGCTGCTTCAGCGGACTCCATCGGGCGGCCGCCTTCAACTGCACCGCCC
ACGGCGGCCGCTGCCAGAACGACGGCCAGTGCCAGGAGGACGGCCAGTGCCTCTGCGCCGACGGCTGGCAGGGACCGGAGTGCCAGTTCTGTGGC
GGAAAAGTGCGCATGTACCACCCCATGGGCACAATACACGACGGATGGGGCAACTATTCGGTGAGTGTCAAGTGCAGCTGGCTAATCGACGCCAG
ACATCCGCACTGGAACCGCCGACACAATACCAATCCGTCGCGAACCGCCAACATACGGATCCACCTGCGAGAGTTCGCCACGGAGTGCGGCTGGG
ATCATCTGTACATATACGATGGCGACAGCGTGGACTCGCCCCTGCTGGCGGTGTTCAGTGGCCTCATGTATCGCGGCAACTTCTCCATTCGTCGA
GTGCCACAGGTGATAGCGACATCCGGCACGGCGCTGGTGCACTTCTTCAGTGACGATGCCTACAACATGTCCGGTTTCAACCTCACCTACAAGAT
GAACAGTTGTCCCTCGGATAGCGATGAGGTGGAGTGTTCCGGCCATGGCAAGTGTCGCGATGGCGACTGCATCTGTGATCCCATGTACAGGGGTG
AAGCCTGCAACATAGCCGCCTGTCCCAACAACTGCTTCGAGTCCAAGAACCAGGGCCATTGTCGTCTTGACCAGGAACGTCAGATCAGCGCCCAC
GGCGCCTGGTCCACGGTCCACCCGAAGCACTCGCCGGCGCCAGCCGGAAGCGCCTCCCATGGCGCCACCATCTGGCGAGACACGTTGCACATTGT
GGGCGGCGAATCGTACGGACGAGGCAAACTAATGAGCACCTATGACTTCAATGGCAACGTATGGGAGACTGTGCACCCGGAGGATGGTAGCGAGG
TTCCTGACAAGCGATACGGTGCCTCGACAGTGATGTACGGCGACAAGATCTTCATGTACGGTGGAGTGGTCAAGGGCCACGGCATCTCCAACGAA
CTGTGGGCCTTCGACGTCTCGGCGCGAACGTGGGCGAACATCTCGGTAAGAGCGGATCCCTCGTGCAACGCCACTGGAGGAACCACCGCTATGTG
CGGACCCCTGCATGTGGTGGGTCACACAGCTACCTTGGTTCCCGTGCAGGAGTTCAACTTTGCATCACGAGAGTGGCGCATCGTCCCCACCACCG
GCTATGTGGTGAAAGGCGGATACGGACACAGTGCCGCGTACGACTTTCTTACGGAGAAGGTGTACGTCTACGGTGGAATAGTCTCCGAGAGTGAG
TCCAGTCAGGTGCTGAGCTCTAGGTTGTATGCCTATGAACCGGCAACGCGAGTTTGGAGTCTGCTGTCTGCGGCGCCAAGTGCGCGTCTACTTCA
CACGGCAAACTTTGTGAACCAGGGACTAATGATGGTCTTCGGTGGCAATACGCACAACGACACATCGCAGAGCTACGGCGCGAAATGCTATAGCC
AGGACCTGCTCGTGTACGACGTGTACTGCGACTCGTGGCACTACCATCCGATGCCGGGCCACCTGCAGGCGGATCTGGCCCGCTTCGGTCACAGT
TCGGTTGTGTTCGAGGAGTCGCTGTACATTTATGGCGGCTTCAATGGCCAGCTGCTAAACGATATGCTGCGCTACCAGCCGGGCTACTGCAGCTA
CTACACCAAACAGGAGAAGTGCACGGCAGCGCGACCTGGAGTGAAGTGTATTTGGGACGTGCAAAAGATGCGTTGCATCGCCATTACCCAGGTTC
AAAGATCGGCGATCTACGGACGCGAGCAATACGACTATGTGGCTTGCCCGTCGAAGAGCCGTCTTACCCTCACTTCAGAGTTACTCCACGATGTG
CACCGTTGCCAGGAACTGGCCAGCTGTCAATCGTGCGTGTCCACCGCCTTTGGTTGCACATACTGCGGAAACGGAGTGTGCAGCAAGGAGCGGTG
TCGTGAAACCACCTCAATGGCTTCGGTCTTCTTCGAGTCGTCCACACAAATGGCAGTGTCCACGGCTAGTCCGCCGCTAAATGCCAAGCATCTGG
ATTCGTGCCCCATCTCCGAGGAGTACCTGGTGTCATCTGTGTGCGATCAGCTGCACAATTGTCGCGCCTGCTCTGCCAACCTGGCGTGTCGCTGG
GACTCGGAGCACAACCGCTGCAAAAGCTACACTTCCTACGGTGGTTTGGCGCTCAACCGGACGCAGGATGAGGTGGCCTGCTCGCCGTCCTGCGC
TTCATTGACCAACTGCCAGAATTGCACCGAGGACGAGTGCATCTGGTGCCAAAACGAACAGCGCTGCGTGGACCGCAATGCCTACACGGCCAGCT
TTCCTTACGGTCAGTGCCGAGAGTGGACCACCTTCACAGCCAAGTGCCGGTCGGCTCCCATCCAATCAACGGCACTGGCCGTGGGCAGCACTACG
GCACTGTCAAGTGCTCAATGTGGCTACTACAACAGCTGCCAGATGTGCCTGGACGATCCGGCTTGCGGTTGGTGTGACAATGGCTCTAACACCGG
TCTGGGCAGGTGCGTGGTTGGCGGAGCACTGGCACCCTACGATGACACGGAGTGCGCCCTAAAGCACTGGTTCTTTACGTCCTGCCCCCGGTGCA
ATTGCAACGGGCATTCGTATTGTAATGACCAACAGCATTGTGAACAGCCATGCAATAATCTGACGACAGGAGCGCACTGCGAGAAGTGTCGCACT
GGATACTGGGGTAATCCCATAAACGGGGGAAAATGCCAGCGATGCGATTGCAACGGCCAAGGCGTTTACTGTCATCCGGACACTGGGAAGTGTTT
CTGCACCACCAAGGGTATAGTCGGTGATCACTGCGAGAAGTGCGACTCCCAGAACCATTACCACGGTGATCCGCTAAAGGGCTCCTGCTACTACG
AGCTGACCATCGACTACCAGTTCACGTTTAATCTTTCAAAGAAGGAGGATCGCCACTTTACACAAATTAACTTCAGGAACTCACCGGGAAAGCCG
GAGATCGATGCGGATTTCACCATTACGTGCAGCGTGCCGGCCAAAATGGACATTTCGGTCAAGAGGGCTGGCTCGCCGGACATGCTGATCTTGGT
GGGCGTTAACTGCTCAACGTTCCGTCATCGGTTCCCCAAGACGGACTACCAATTCGGGCACTCGCCCGATGACAACAGCTCCCTGACCACGTTCT
ACGTGTTCGTGCACGACTTCCAGCCCCCAATCTGGATACAAATTGCCTTCTCACAGTATCCCAAGCTCAACCTGCAGCAATTCTTCATCACATTC
TCCTCCTGCTTCCTACTGCTGCTGCTTATGGCCGCCGTCCTGTGGAAGATTAAGCAGAAGTACGACATGTTCCGGCGGCGTCAGCGATTGTTCGT
CGAAATGGAACAGATGGCGAGTCGACCGTTTTCCCAGGTGCTGGTCGATATCGAGAACCGCGAAAGTATTGATCTGAGTCTGACGCTGGAGGGCA
TTGGCCACCTGTCCAAAAAACGCAAAAAGGAATGCCCTAGTCCCATCGCTTTGGAGCCTTGCAGTGGCAACCGAGCCGCTGTGCTCTCGCTTCTA
GTCCGGCTGCCCACGGGTGGCCTTTCGCAAGCGCCTTCTGGCCAGTCCGCTGGTCTGGCTGTGGCCAGCGCCTTAGTCACGTTGGGCAATCCGCG
TCGTCCGTCGATCGATCAGCATCCGAAGGAGCCAAAGTCAAAGCGCAAGCAGAGCCAGCACCCAGACAGTTGTACATAA
(SEQ ID NO: 629)

Start ATG: 310 (Reverse strand: CAT)

MCLAAEPPQKQPNRSSTSPTFNAKYRRKCLLLLTLLLFHGCFSGLHRAAAFNCTAHGGRCQNDGQCQEDGQCLCADGWQGPECQFCGGKVRMYHP
MGTIHDGWGNYSVSVKCSWLIDARHPHWNRRHNTNPSRTANIRIHLREFATECGWDHLYIYDGDSVDSPLLAVFSGLMYRGNFSIRRVPQVIATS
GTALVHFFSDDAYNMSGFNLTYKMNSCPSDSDEVECSGHGKCRDGDCICDPMYRGEACNIAACPNNCFESKNQGHCRLDQERQISAHGAWSTVHP
KHSPAPAGSASHGATIWRDTLHIVGGESYGRGKLMSTYDFNGNVWETVHPEDGSEVPDKRYGASTVMYGDKIFMYGGVVKGHGISNELWAFDVSA
RTWANISVRADPSCNATGGTTAMCGPLHVVGHTATLVPVQEFNFASREWRIVPTTGYVVKGGYGHSAAYDFLTEKVYVYGGIVSESESSQVLSSR
LYAYEPATRVWSLLSAAPSARLLHTANFVNQGLMMVFGGNTHNDTSQSYGAKCYSQDLLVYDVYCDSWHYHPMPGHLQADLARFGHSSVVFEESL
YIYGGFNGQLLNDMLRYQPGYCSYYTKQEKCTAARPGVKCIWDVQKMRCIAITQVQRSAIYGREQYDYVACPSKSRLTLTSELLHDVHRCQELAS
CQSCVSTAFGCTYCGNGVCSKERCRETTSMASVFFESSTQMAVSTASPPLNAKHLDSCPISEEYLVSSVCDQLHNCRACSANLACRWDSEHNRCK
SYTSYGGLALNRTQDEVACSPSCASLTNCQNCTEDECIWCQNEQRCVDRNAYTASFPYGQCREWTTFTAKCRSAPIQSTALAVGSTTALSSAQCG

FIGURE SHEET 342

YYNSCQMCLDDPACGWCDNGSNTGLGRCVVGGALAPYDDTECALKHWFFTSCPRCNCNGHSYCNDQQHCEQPCNNLTTGAHCEKCRTGYWGNPIN
GGKCQRCDCNGQGVYCHPDTGKCFCTTKGIVGDHCEKCDSQNHYHGDPLKGSCYYELTIDYQFTFNLSKKEDRHFTQINFRNSPGKPEIDADFTI
TCSVPAKMDISVKRAGSPDMLILVGVNCSTFRHRFPKTDYQFGHSPDDNSSLTTFYVFVHDFQPPIWIQIAFSQYPKLNLQQFFITFSSCFLLLL
LMAAVLWKIKQKYDMFRRRQRLFVEMEQMASRPFSQVLVDIENRESIDLSLTLEGIGHLSKKRKKECPSPIALEPCSGNRAAVLSLLVRLPTGGL
SQAPSGQSAGLAVASALVTLGNPRRPSIDQHPKEPKSKRKQSQHPDSCT*
(SEQ ID NO: 630)

Name: LanB1-like
Classification: cell_adhesion

Celera Sequence No. : 142000013384557
CTCGCTCTCCTTTGTGTGGCTAATTTTTTCCTTTTAGTCCTTTTTTCGGTTGCCTTCGTGCAGAAATTCCCTGCTTTATGTAATTTAGAACACA
ATGTTTGCGTTGCACTGTTGGCCGACTGCAGCTGAAAACCGCACAAAAAAAGCGACGCACACACACACCTTCGAGCATCCGGACTTCCAATTTGC
ACTGCTTTTCTAACAGTCTATCGCGCACGCACTGCCACAATTTCACCCGCTTATCGCGCCGCAATATGGGACGTTCGCTTTTCAATCGATTTTGG
TAACCGGCAGGTGCGCTTTATGCGAGAATTACGAATTTTCTCCAGCGGCAACTAGAATCGTTCACACAGACACCGTAGAAGTGACGCCATCTTTG
AAGCGATTAGTGTTGCAAAGCGCGTCTGCAAAAGTGCTGGCTACCAACTACGGTTGATAGGATGAGGGCTATGGCTTGTTGACCGAAAATGATA
AATGTTAACTATGCCAATATATTTTAGATTTTACTAATACGTTACAAAAATAAGAAAAGACTATGATAAAATTGTGTTTTAGCTTGGCTCATAAG
TATTGATCCTTTATAAGCTATGGTCTTGCAGTGGCTAACATTTCTCAAATTAGGGCAACCATCTGATAAGATTTCTAATTCGAATTCTAATAAAT
GAATTTAAACTGCTTTTTCTTAAAGTTAAAAAAAAATTAGTTTTAAATCAAACGGCATGCATACATTAACCATCAAACAATGTAATTATATATAT
AATATTACCAATTGGGCTACTAAATATTGCTGATATGTAAGCTATGGTCATGAGGTAAAGGCATATTATTATTTATATAATTTTCATAGTATCTTTGT
TGTAGGGGAAAAATAACAAGTAATTTAAAATTGTTCAATTGACTTAAAACAAAATATAACAGATATTATTTTTAAATCCAACGACATACCATATA
AAGTTGGTATTTCTTTCTAATCTGCTTGGTATTCTCATCGACCCCAATCGGTCACACTGGTCGTGAATCAGAAACGCACTAATTAGTCAAAAAAA
CGGTACAAAAGATCGCTTAATTGCTGAAATTTCACCTGTCGCAGTTAAGTTTACCCACCAGCAGTTCAAAACCAGCCAGAGGCTAGCTAAAAACC
CCAAAGATCGACCCCAAAACATCGCCGCAAAGTGGACAACTCCCAGTTTTCAGAGCACCTGCCCCTCAAAAAGGAGCATCGCGACAAAAAGGCGA
GACTTCGCAGCAGAATGTCCTCGCTCTCTGCGTCCGCGGAGAATGTGTCCAGTTTGGGACTGGGATCGGGCGGAGGAGGAACTACTTCCCACGAC
GGCAACTCCCAGCAGGGTTCCGGATCCGACGGAGGATCCAGTATGTGCCTGGAACTGGCCCTCGAGGGTGAACGCCTCTGCAAGGCGGGTGACTG
CCGGGCGGGCGTGGCCTTCTTCCAGGCGGCCATTCAGGCCGGAACCGAGGATCTTCGCACTCTGTCCGCCATCTACTCCCAGCTGGGCAACGCCT
ACTTCTACCTAGGCGACTACAACAAGGCGATGCAGTACCACAAACACGATCTTACGCTGGCCAAGAGCATGAACGACCGACTGGGCGAGGCCAAG
TCCTCTGGCAATCTGGGCAACACCCTCAAGGTAATGGGTCGCTTCGACGAGGCGGCCATCTGTTGCGAGAGGCACCTAACGCTGGCCAGGCAGCT
GGGAGATCGTCTGTCCGAGGGACGCGCTCTTTACAACCTAGGAAATGTCTACCACGCCAAGGGCAAGCACTTGGGTCAGAGAAACCCTGGAAAGT
TCGGCGACGATGTCAAGGAGGCGCTCACCCGTGCCGTGGAGTTTTACCAGGAGAATCTGAAGCTCATGCGGGATCTGGGTGATCGTGGTGCTCAA
GGTCGAGCTTGTGGTAATCTGGGAAATACCTACTACCTACTAGGCGATTTCCAAGCGGCCATTGAGCATCATCAGGAGCGACTGCGCATTGCCAG
AGAGTTTGGTGATCGCGCGGCTGAGCGAAGGGCCAACAGTAATCTTGGCAACTCGCACATATTCCTGGGACAATTCGAGGACGCCGCCGAACACT
ACAAACGCACCTTGGCTTTGGCCGTTGAGTTGGGTGAACGCGAAGTGGAGGCCCAGAGTTGCTACAGCTTGGGCAACACCTACACGTTGCTGCAC
GAGTTCAACACTGCCATCGAGTATCACAATCGACACTTGGCCATTGCCCAGGAGTTGGGCGATCGAATTGGTGAGGCCAGGGCCTGCTGGTCACT
GGGCAATGCCCACTCTGCCATCGGTGGTCATGAGCGGGCCCTAAAGTATGCGGAACAGCATCTTCAACTGGCCAAGGAGCTGCACGACCCGGTGG
GTGAAAGCACAGCCAGGGTGAACATCTCCGATCTACGAAAGCTACTCGGAATGCCCGACTCCGAGCCTTCACCCACCGAGGAGGAGGCTCGATCC
ACCGCCTCCGATCACTCGGCCAGCGGAAATCAGTCGGATGGATCGGAGAACTCGCAAGGAAGAATGGTAAGAGAAACGAGCTGCAACAACATAAA
GCAATATGAATGATTCCTGAGATATTTTTAAACAATACTGGCAGTCCGTTTGTTCTATTTTTCGAAGTGGACACCTGCTGCTTGCAGTGTTTGCC
CCTTTATGTTAGCGTAAATATTTATACTTTGTACCAAAACACATCGTTAAACTTTCGATTCGAGCACATGCTGAGAAATTGAAACCCCTGAAAGA
TACATAGCTAAATTTATTACTTTAATTGCTTCCCGTCAGGTGCGCGTTCGTCGCCAGAGCATGGAGCAGTTGGACCTGATCAAGATCACTCCCGA
TGGAAAGCGCATGCAGGAGGAAAAGCTACGAGCACAGGCGACCAGGAAAGCCAAAGACGACGACTTTTTCGAGATGCTTTCGCGGTCGCAGTCGA
AGCGCATGGATGACCAGCGCTGTTCGATCAAGGTGAATCCCGCCGGAGCTCCGGCGGTGGCCACTGGCGCCACGCGTAAGCCGCTTGTGCAGCAG
AACTCGTTGTTCGTGGATCCCACCAACCTGCCTGGCCTCAAGTCACCGTCGTCGGCGAATCCATCAGCCATTGGACATGGGCCGCTCGCCAGGAG
CGCCACCACTACGCAGCAGCCCGATGATGACTTCCTAGACATGCTTATGCGCTGCCAAGGCTCGCGTCTGGAGGAGCAGCGGTCCGAGTTACCGC
GCCCCAATGTCACCATGGACGCAGAGGCGGAGGCACCACCGCGATCCGTCCCAGAGGCTGCTGTTCCAGGGGCACCACGCGGACAGACCGGACGT
GGAGCTACCGTCCCCGATGAGGACTTCTTCTCACTGATCATGAAGGTCCAGAGCGGTCGCATGGAGGATCAGCGCGCCTCGATTCCGTTCCGAAA
TGCCAACAATAACAACAATAGCCGCAGCAACAACAACGGTTCAGCCGGCGGAGCTGGAAAGTAGAGAGTTGTAGTCCAAAAAGCTGAAGTCCAAC
CAAACAATCCTATAAATCCATCCCTGGCCGCAGCTCCTGACTCATTTCGTTGTAAGCCCATCTTGCGGCCATTTATTCAGTCGTTTATTTTCGGA
AATTGGCTGCTAAACATTTTGTTCTTTTACAAGATTTATATATACACACGTACACGAAAAGCATTAATTTATGAATAGCAACTAACCACGTAACC
AAATATTAGGGGTGTATAGGGCCTCGTCTACACGAGCAGAGGGAGGAACCTCCAACGGATGCACACACTCATCCACTCATGACTCATTACATACT
CCACCATGAGCTGGCCATGATATTGAACGATATGCACTCGAGTCTTACGATATTAACGTTTTAATTGCATGTGCAAGTAGTTTAAGCCGGATAAT
ACTAATGTACTAATCCAATTTGCTCAATAGACGGAACCAAGTCTTCTCTACGATCAACGATCTTACATTCTCGTAGCCACATTCAGCTAAATATT
AAGTTTTAAGTCCATCGAACCCACTCTACATGTAAGCAATGCATTTTCCAAATCAAAATCTAACTACAGATATATCCAATTGTAACTATGAGTAT
TGCATTTTTCTATCAATCTATCGATCGATCTAAACTCTGAACATATTTTAAGCCACTTACAATTTTTGTTAGTATATTAACAAGACACAAAGAAT
AGCAGCTCGGAATTCCATTTGAGGACCGGCGCTTGTGCAAGCACTTAGCATACGATATACACAACCAATCATACTTACACATATACAAGAAACAT
ATGAACAATATATATATAGTTATACCAATGTCTAACGATTTGCCTCTTCGGGTATTGTTCTACACAATATATACAATACAAGTTATATATACACA
AAACAAAAACACAAAACTGAGTTCGAGTTGTACGAAATGAAGCCAAAATTTATTAATGTTATACTTTTTTGTAGCACGAGATCTACGGGATCTGC
GAATGAAAGATACCATACA
(SEQ ID NO: 631)

Exon: 1001..2536
Exon: 2795..3484
Start ATG: 1250

Transcript No. : CT17944
GTCACACTGGTCGTGAATCAGAAACGCACTAATTAGTCAAAAAAACGGTACAAAAGATCGCTTAATTGCTGAAATTTCACCTGTCGCAGTTAAGT
TTACCCACCAGCAGTTCAAAACCAGCCAGAGGCTAGCTAAAAACCCCAAAGATCGACCCCAAAACATCGCCGCAAAGTGGACAACTCCCAGTTTT
CAGAGCACCTGCCCCTCAAAAAGGAGCATCGCGACAAAAAGGCGAGACTTCGCAGCAGAATGTCCTCGCTCTCTGCGTCCGCGGAGAATGTGTCC
AGTTTGGGACTGGGATCGGGCGGAGGAGGAACTACTTCCCACGACGGCAACTCCCAGCAGGGTTCCGGATCCGACGGAGGATCCAGTATGTGCCT GGAACTGGCCCTCGAGGGTGAACGCCTCTGCAAGGCGGGTGACTGCCGGGCGGGCGTGGCCTTCTTCCAGGCGGCCATTCAGGCCGGAACCGAGG
ATCTTCGCACTCTGTCCGCCATCTACTCCCAGCTGGGCAACGCCTACTTCTACCTAGGCGACTACAACAAGGCGATGCAGTACCACAAACACGAT
CTTACGCTGGCCAAGAGCATGAACGACCGACTGGGCGAGGCCAAGTCCTCTGGCAATCTGGGCAACACCCTCAAGGTAATGGGTCGCTTCGACGA
GGCGGCCATCTGTTGCGAGAGGCACCTAACGCTGGCCAGGCAGCTGGGAGATCGTCTGTCCGAGGGACGCGCTCTTTACAACCTAGGAAATGTCT
ACCACGCCAAGGGCAAGCACTTGGGTCAGAGAAACCCTGGAAAGTTCGGCGACGATGTCAAGGAGGCGCTCACCCGTGCCGTGGAGTTTTACCAG
GAGAATCTGAAGCTCATGCGGGATCTGGGTGATCGTGGTGCTCAAGGTCGAGCTTGTGGTAATCTGGGAAATACCTACTACCTACTAGGCGATTT
CCAAGCGGCCATTGAGCATCATCAGGAGCGACTGCGCATTGCCAGAGAGTTTGGTGATCGCGCGGCTGAGCGAAGGGCCAACAGTAATCTTGGCA
ACTCGCACATATTCCTGGGACAATTCGAGGACGCCGCCGAACACTACAAACGCACCTTGGCTTTGGCCGTTGAGTTGGGTGAACGCGAAGTGGAG
GCCCAGAGTTGCTACAGCTTGGGCAACACCTACACGTTGCTGCACGAGTTCAACACTGCCATCGAGTATCACAATCGACACTTGGCCATTGCCCA
GGAGTTGGGCGATCGAATTGGTGAGGCCAGGGCCTGCTGGTCACTGGGCAATGCCCACTCTGCCATCGGTGGTCATGAGCGGGCCCTAAAGTATG
CGGAACAGCATCTTCAACTGGCCAAGGAGCTGCACGACCCGGTGGGTGAAAGCACAGCCAGGGTGAACATCTCCGATCTACGAAAGCTACTCGGA
ATGCCCGACTCCGAGCCTTCACCCACCGAGGAGGAGGCTCGATCCACCGCCTCCGATCACTCGGCCAGCGGAAATCAGTCGGATGGATCGGAGAA
CTCGCAAGGAAGAATGGTGCGCGTTCGTCGCCAGAGCATGGAGCAGTTGGACCTGATCAAGATCACTCCCGATGGAAAGCGCATGCAGGAGGAAA
AGCTACGAGCACAGGCGACCAGGAAAGCCAAAGACGACGACTTTTTCGAGATGCTTTCGCGGTCGCAGTCGAAGCGCATGGATGACCAGCGCTGT
TCGATCAAGGTGAATCCCGCCGGAGCTCCGGCGGTGGCCACTGGCGCCACGCGTAAGCCGCTTGTGCAGCAGAACTCGTTGTTCGTGGATCCCAC
CAACCTGCCTGGCCTCAAGTCACCGTCGTCGGCGAATCCATCAGCCATTGGACATGGGCCGCTCGCCAGGAGCGCCACCACTACGCAGCAGCCCG
ATGATGACTTCCTAGACATGCTTATGCGCTGCCAAGGCTCGCGTCTGGAGGAGCAGCGGTCCGAGTTACCGCGCCCCAATGTCACCATGGACGCA
GAGGCGGAGGCACCACCGCGATCCGTCCCAGAGGCTGCTGTTCCAGGGGCACCACGCGGACAGACCGGACGTGGAGCTACCGTCCCCGATGAGGA
CTTCTTCTCACTGATCATGAAGGTCCAGAGCGGTCGCATGGAGGATCAGCGCGCCTCGATTCCGTTCCGAAATGCCAACAATAACAACAATAGCC
GCAGCAACAACAACGGTTCAGCCGGCGGAGCTGGAAAGTAG
(SEQ ID NO: 632)

Start ATG: 250

MSSLSASAENVSSLGLGSGGGGTTSHDGNSQQGSGSDGGSSMCLELALEGERLCKAGDCRAGVAFFQAAIQAGTEDLRTLSAIYSQLGNAYFYLG
DYNKAMQYHKHDLTLAKSMNDRLGEAKSSGNLGNTLKVMGRFDEAAICCERHLTLARQLGDRLSEGRALYNLGNVYHAKGKHLGQRNPGKFGDDV
KEALTRAVEFYQENLKLMRDLGDRGAQGRACGNLGNTYYLLGDFQAAIEHHQERLRIAREFGDRAAERRANSNLGNSHIFLGQFEDAAEHYKRTL
ALAVELGEREVEAQSCYSLGNTYTLLHEFNTAIEYHNRHLAIAQELGDRIGEARACWSLGNAHSAIGGHERALKYAEQHLQLAKELHDPVGESTA
RVNISDLRKLLGMPDSEPSPTEEEARSTASDHSASGNQSDGSENSQGRMVRVRRQSMEQLDLIKITPDGKRMQEEKLRAQATRKAKDDDFFEMLS
RSQSKRMDDQRCSIKVNPAGAPAVATGATRKPLVQQNSLFVDPTNLPGLKSPSSANPSAIGHGPLARSATTTQQPDDDFLDMLMRCQGSRLEEQR
SELPRPNVTMDAEAEAPPRSVPEAAVPGAPRGQTGRGATVPDEDFFSLIMKVQSGRMEDQRASIPFRNANNNNNSRSNNNGSAGGAGK*
(SEQ ID NO: 633)

Classification: hypothetical

Celera Sequence No. : 142000013384669
TTCAATGCCCTTTTTCTTTGGCTACCGATCGAAATACCCACTTTATGGTCTACCTCCCGCCTTCCTCGCCCGCACACATGTCATGCATATATATT
TTCCTGCTCGATCGGCACACGCATAGCGACAGAAAACAGGCGAGATGTATAATTTTATATAATAGGGCAAAGTTATTTTTAAAGGCACTCGACAA
TATTATTATGCTAATAAAGAAATGAACTGCTTGCTACGCGGCGGCGGCGAAAAGACAAAACCGTTTTTCACACCAAATAACGGTCCATTCGAGT
ATGATTGTAAGTAAAAGTACCGTAACAGGGACTTACCGCGTTTTCGGCGCTTATCCTTGCGCTTACGCGGCTGCACATCGCCCGACATTTTGCTC
GCTAAAGGCACTAAAACCTATGCCAATATAATGGAGAGTGTTTGTTTTTCCTTTTCGAGCGGACCGGGCAAAACGGGCGATCTGGATCGACGAAC
AGCACGTTACTAAATGCAAATACCGCTCGCACCGTGGGAAAATTATTTATAAAGAGACAGTGGCGTTGCCAGATCCGGCGGGAATGATGAAAGCT
AGAGATGACAGCTGGGCAGTAAAGGCACCGCTATTTCAATTTTATTATTCTGGATGGAAAACTCATGACAGCTCTCAAAAACTATATTTACGCAT
AAATATTTATACATTTATTTAATTCTAATAATTATGTTTTATTTTAAATCGTGTTGTGTCGATAGATTGAATTTAATTTTAACAGTTCAGCAACG
CAAACGTTTAGAAAACCCAAATGTAATTTTTTCTGTTACTCGTGGATTTTTCATATTTTATGTCTATGCGCTATCCATACAACAGAACAAATTGA
TTTATTTGATTTAAAATGTAAAGTGCTCAAAGTATTAAATACAAGTAAATAATTTAAATTAAAAAAATTAGCTTTTTTTTAAATATCGCATGTCA
TTAAAATTCATGCGCACTGCAGTCTCCAGTATCGTCACGCGCCCATCTCGAAGGGAACCAACCCCGACCAAGAAAAAAAAAAACAAGAAAATAAT
ACACAATTGGCGACGGCGGTGCAGAGGTTCTCCGTGTGATCCGATCGAACGGGACTAGGACCGACACGGACCAGGTCTAAATCCGCGAGGTCAGC
GGTATTATGGCCGGCGACATGTCCATCGGCTGTGCGGCCCTGAAGCGATCCAGCAAGCTGAGGTCCTGCACCAGCGCCGCCGACACGGACTCGAT
GCGGGTGCCCAGCGACCACAGGGACAACGGGAGCCTGATCAAGCCGCCTCCGGTGCCGCCGCAGAATATGCGCGGCGGTCTGCGGGTCTATAAGA
TTGTCATCCTGGGCGACGGTGGCGTTGGCAAGTCAGGTGAGCTATTCTAGCCATGGATTAGACGAAAGAAAATGCCGAGTTATCACTGCGCACTT
TGATTGGGGCTGCGAAAAATCAATAAATTATCTCAATTTCTTTTACGCTTTGTTTTGACCCCCGTACCACCGACACCCACGAAACTCCACCAACC
ACCACTCCCAACGCCCTCTGAAAACGACGACGAAACCCGAACAGCTGTCACCCTTCAGTTCGTGAGCCACAGTTTCCTGGACTACCACGACCCCA
CAATTGGTGAGTAAGGCGCAGGGTGCGCAAGGCGTCTAAGGCACAAGCCCCCACAACCCCACTAAATGTATACCGGTTTTTTTTTTCTTTTTTGC
TGCTGCAGAGGACTCCTACCAGCAACAGGCGGTCATCGACAATGAGGCCGCCCTGCTCGACATCCTTGACACCGCCGGCCAGGTGGAGTTCACGG
CCATGCGGGACCAATACATGCGTTGCGGCGAAGGTTTCATCATATGCTACTCGGTCACCGACCGCCACAGCTTCCAGGAGGCCTCCGAGTACAGG
AAACTAATAACCCGTGTCCGCCTGTCCGAGGACATTCCGCTGGTTCTGATTGCCAACAAGGTGGACCTGGAGTCGCAGCGACGCGTGACCACCGA
GGAGGGCCGGAATCTCGCCAACCAGTTCGGCTGCCCGTTTTTGAGACATCGGCTGCACTGCGTCATTACATCGACGAGGCATTCTACACGTTGG
TCCGCGAGATTCGACGCAAGGAAATGCACAAGGCCCTGGGCACGGACTCCAATTCGGAAAAGATTCACACGGGGCGACGAAGTCGCTGGTGGCGC
ATCCGATCCATTTTCGCATTGGTTTCCGGCGCAGACGAAACCTTAACTAGACCAGGAGGCGGATTCCTTGAAATGAGTGCAATATTAACCACAA
AAACCAAGTAACTTTTGTTTGCTATATTTTGTATATAGCACATACCCATCAGATACAACATACAAAAGAGAAATTAACCGATCGAGGAGCAGATA
ACTAATTGTTATGGCCACAGTGGTTTATTTATTATTTGTTATGGAAACTATTTAAAGTACTTGTTGTTGGCCGGAAAGGATAGCGAGGCAGTAGA
TCAGCGATAGAGTATATCAATACGTTTAAGCACCGATCCAAAAGATACATATTAACAATGCACGTACATATGTTTATGTAGTAAATATTACTAAT
GTTGATTCCTAGACGAGAGCGATTAAGCAAGTGTGGCAATTGGCTAAAGCTCAAAAGCATTTAAATTCAGCAAGATCGAGGGGTCGAGTCTTCCC
CCACTAACAATCTGAACAACTCTGAATCCTAGCCAGGAGATTAACCCAAAAGCCAATTGCCAGGTGCGAAGGGCAGAGAATTGGAGGATTTTTAA
ACTTATGTATGTACGTATTTACCCAGAATACACGCACATGACATACGTTACACGAGCCACACATTTAACTAATCGAATAAATGTTGAATTTAATG
TATACTAATATTATAAATCGATCGATCGACCTAAGAAGTATGTAAAACGCGGGAACATTGCAAATTATGAAATATGAATGAGAATGTGCGTTCAT
TTCAGATCCAAGCCCAAATTGATAATTTAAGTCCACGACAGCCGATGCATTTGTTGTTTAAGTTTGAGAAAAGTCTATTGTTTATATTGTTAAGG
ACACACGTGTTACGCCTAAGTTTATTTATTATTAGTTTAACGAAATCTGTTGATTACTTTTACCACAAGAAACCACACATCACGTTCTCTAAGCA
ATCACCATGAGTTCCTCTCATCAATGTTAACTGCATCACCGGAAACAAAATACTAACACGGCTTTAATTACTCTGTTTGTTACATGATCCCAAAA AACAGTTGAATGGACTACCCATAATTACTAATAATTAATTGTTATTGCGAATCCTGCAACCGTTCGAACCAAACAGATCGACTGACGAAAAAAAG
AAAAACAACAGCTCCAACACGAAAACGAATCAAATGCGGGTAGAAATATAATAGAATTGCTTTCGCCGCGAAAGTTAAGCGATTAAAAAGTACGT
TTTAAGAGAAAAGGCTTGGGAACTAGATGTTCAAAGCAATGTGTCGTGTCCATGTTGTTTCGAAAACGACATACCTGTTCGGGAATAATATTGTG
AAACCTAATACCTAATCGATGAAAAACCAAAACATTTTGATTCATAATGTTATGTACATTTTAAATGTAAAAAAAAAAATTAAATACAAAAGCAC
AAAATAAACAAAAACAATACCCTCAATAAAGATTTTTTAACCCCGTTAAAGATAAGTGTTTTGACTTTAAAGGGCGGGTATTCCCCGGATTTAA
ATCCATTATCTTAGCCTAATAAAATTCGATGCCCGGCCAAATAAGAAAACAGTTAGTTAAACCAAGAGTAGATCAAATGTACTGTTTATTCATAA
GTATAATATAGTTTGGTTGTATCTGATGCATCTTCGAGTTTTTCAACTTCTGTGTGAGAATTACACGATTGACGGTACAAAATACAAAAAAAGAG
ACATACACATATGTACTGTATAGTATAATTATATGTATAATCGTATTTTATAAAATCATAAAATACTCTTCATATAGTTGTTTGGTTGTTTTGTA
GTATCTTTTTTTTTTTATGTTTTCCACTCGTTTTAATGCAAAGTACAAATATTAAAAACTCGCTTAATGCGCTCGAAATAGTTTTTCACTTCATC
AAAAATTTTCCCTCTTAGCATCTCCCACGCGAAAACTGAATGCATCTCATTTGTGGCTTACGTTTAGTTAAATAAACATTTATCGTTTTTGTTTT
GTTTTGTTTTGTGTTTAGTTCGGCTCTTGTAATGTAGTTTCGCTTCCAACTCCTATTGGCGGCCTGGTCTCTCTGTATTTGATAGATTTAATGGG
AACATAACTCTCATCTTGACGCCTACGACCTCCTTGGACCCCGGGATCCAACATCCGATTCCGTTTCCGATTCTGTTCCTAATTCCACTGATTCA
CCTGACTCACTCACCCTCGCATACGACACAATCTCGTCCAGCCACAGCCGACTCTACACTTGACAACACAGTTAACGAAATAATAACATACATCT
AGGAGGAGGGGGTGGACAGAAACGGACACAACTTGAATATGTTTACATATATCGATATATATTTTTTGCTTGCAGTGGCTGACTGATT
(SEQ ID NO: 634)

Exon: 1001..1366
Exon: 1565..1621
Exon: 1719..3553
Start ATG: 1147

Transcript No. : CT17993
AAGGGAACCAACCCCGACCAAGAAAAAAAAAAAACAAGAAAATAATACACAATTGGCGACGGCGGTGCAGAGGTTCTCCGTGTGATCCGATCGAAC
GGGACTAGGACCGACACGGACCAGGTCTAAATCCGCGAGGTCAGCGGTATTATGGCCGGCGACATGTCCATCGGCTGTGCGGCCCTGAAGCGATC
CAGCAAGCTGAGGTCCTGCACCAGCGCCGCCGACACGGACTCGATGCGGGTGCCCAGCGACCACAGGGACAACGGGAGCCTGATCAAGCCGCCTC
CGGTGCCGCCGCAGAATATGCGCGGCGGTCTGCGGGTCTATAAGATTGTCATCCTGGGCGACGGTGGCGTTGGCAAGTCAGCTGTCACCCTTCAG
TTCGTGAGCCACAGTTTCCTGGACTACCACGACCCCACAATTGAGGACTCCTACCAGCAACAGGCGGTCATCGACAATGAGGCCGCCCTGCTCGA
CATCCTTGACACCGCCGGCCAGGTGGAGTTCACGGCCATGCGGGACCAATACATGCGTTGCGGCGAAGGTTTCATCATATGCTACTCGGTCACCG
ACCGCCACAGCTTCCAGGAGGCCTCCGAGTACAGGAAACTAATAACCCGTGTCCGCCTGTCCGAGGACATTCCGCTGGTTCTGATTGCCAACAAG
GTGGACCTGGAGTCGCAGCGACGCGTGACCACCGAGGAGGGCCGGAATCTCGCCAACCAGTTCGGCTGCCCGTTTTTTGAGACATCGGCTGCACT
GCGTCATTACATCGACGAGGCATTCTACACGTTGGTCCGCGAGATTCGACGCAAGGAAATGCACAAGGCCCTGGGCACGGACTCCAATTCGGAAA
AGATTCACACGGGGCGACGAAGTCGCTGGTGGCGCATCCGATCCATTTTCGCATTGGTTTTCCGGCGCAGACGAAACCTTAACTAGACCAGGAGG
CGGATTCCTTGAAATGAGTGCAATATTAACCACAAAAACCAAGTAACTTTTGTTTGCTATATTTTGTATATAGCACATACCCATCAGATACAACA
TACAAAAGAGAAATTAACCGATCGAGGAGCAGATAACTAATTGTTATGGCCACAGTGGTTTATTTATTATTTGTTATGGAAACTATTTAAAGTAC
TTGTTGTTGGCCGGAAAGGATAGCGAGGCAGTAGATCAGCGATAGAGTATATCAATACGTTTAAGCACCGATCCAAAAGATACATATTAACAATG
CACGTACATATGTTTATGTAGTAAATATTACTAATGTTGATTCCTAGACGAGAGCGATTAAGCAAGTGTGGCAATTGGCTAAAGCTCAAAAGCAT
TTAAATTCAGCAAGATCGAGGGGTCGAGTCTTCCCCCACTAACAATCTGAACAACTCTGAATCCTAGCCAGGAGATTAACCCAAAAGCCAATTGC
CAGGTGCGAAGGGCAGAGAATTGGAGGATTTTTAAACTTATGTATGTACGTATTTACCCAGAATACACGCACATGACATACGTTACACGAGCCAC
ACATTTAACTAATCGAATAAATGTTGAATTTAATGTATACTAATATTATAAATCGATCGATCGACCTAAGAAGTATGTAAAACGCGGGAACATTG
CAAATTATGAAATATGAATGAGAATGTGCGTTCATTTCAGATCCAAGCCCAAATTGATAATTTAAGTCCACGACAGCCGATGCATTTGTTGTTTA
AGTTTGAGAAAAGTCTATTGTTTATATTGTTAAGGACACACGTGTTACGCCTAAGTTTATTTATTATTAGTTTAACGAAATCTGTTGATTACTTT
TACCACAAGAAACCACACATCACGTTCTCTAAGCAATCACCATGAGTTCCTCTCATCAATGTTAACTGCATCACCGGAAACAAAATACTAACACG
GCTTTAATTACTCTGTTTGTTACATGATCCCAAAAAACAGTTGAATGGACTACCCATAATTACTAATAATTAATTGTTATTGCGAATCCTGCAAC
CGTTCGAACCAAACAGATCGACTGACGAAAAAAAGAAAAACAACAGCTCCAACACGAAAACGAATCAAATGCGGGTAGAAATATAATAGAATTGC
TTTCGCCGCGAAAGTTAAGCGATTAAAAAGTACGTTTTAAGAGAAAAGGCTTGGGAACTAGATGTTCAAAGCAATGTGTCGTGTCCATGTTGTTT
CGAAAACGACATACCTGTTCGGGAATAATATTGTGAAACCTAATACCTAATCGATGAAAAACCAAAACATTTT
(SEQ ID NO: 635)

Start ATG: 147

MAGDMSIGCAALKRSSKLRSCTSAADTDSMRVPSDHRDNGSLIKPPPVPPQNMRGGLRVYKIVILGDGGVGKSAVTLQFVSHSFLDYHDPTIEDS
YQQQAVIDNEAALLDILDTAGQVEFTAMRDQYMRCGEGFIICYSVTDRHSFQEASEYRKLITRVRLSEDIPLVLIANKVDLESQRRVTTEEGRNL
ANQFGCPFFETSAALRHYIDEAFYTLVREIRRKEMHKALGTDSNSEKIHTGRRSRWWRIRSIFALVFRRRRNLN*
(SEQ ID NO: 636)

Classification: enzyme
Gene Symbol: Ric
FlyBase ID: FBgn0017549

Celera Sequence No. : 142000013383733
GTAATCCCGTTTCAGAGATCTATCGCATTGTGTCGCAGAAACAGATCAGAGATCCGCCGGAAGGCGACGTCATCCGCCCGTCGAACGTGGAGCCC
ATCGACGTAAAGCCGACTGTCACCGCCGATGTGCGCAAACAGTGCTGTCAGTGACCGCCCCAAGCAATTTTCGCTATTCCCCGCAACCGCCAGAA
CAGCAACATAAACAGAAGCAACAGCAATTACAACTACGACTACAAGAGGAGCAGCAGCGGCCAGAACTGCAACACCAAGATCAGGAGCAGCGTAC
ACCCGATGGACCGCACAAGATGTCTATGCGTTTGTCAGCCACAGTTTGTCATGTGCGCATAAATTGATAATTCAAATCTGAGCCGCCACTCTCCA
CCACCAACACCACCACCATCATCAGAAGCAGCAGCAGCAGCAAAAGAATCGAAAGCAACAACATCCGGCTGTAGTTAACTGCGGTTTAAACTGAA
GTTTTATATATATACAGATCCATGAGTATCGCATAAATCGACCGCCGCGGAAAGAAAGCAAGCAAAACTAAACACTCCAAATTCAGTTTAAGCTG
TAGAACTATAATTTATATAAATATACATATATGCTAATATTAAAATATTAATATTATTAATTTTTCGCAACATAAATATATAGTTGTAATTTCGC
GAGCAGAACAACAACAAACAACCGGAAATTCTTCGACTTAAACGCAAATTCATTACCACAGCACTGCAGCTCGGATTTTCTTCTTCGGTTTCTCG
CAACATTTTAAACGATTGGCCACTTGGTAAAACTAGCTGATAAAGAGAAATCAAACAAAAACAGTTGTAAAACTTTAAATGCATAAATGAAACGA
AATAACATCATTTGTGTTTGCTATGTTAAGTGTGATTAAATAAATATAATTTAAATAAAACAGAAGTGCTTTCAATTGGGCGGAAAATCGAAATT TAAAATGGGATTAGAGTGACCAAAGGCAGACGTCGGAGTGGGTGTTTGGTATTTTCCGCGCGAGCAGCCACACTGATCCATACACGTGCGGGAGA
AAAGTGAACAAAAACATTGAAACATGGGCGGTAAGAAGAAAGTGCATCCGAAGACGCGCACGGCGGCCTTCAAGGCCAGCGAGCCGAGCGAGATC
GTGGAGGCGCCGCACTCCTTCGTCATCCATCGCGGCCTCGCCTGTCCGTACATCACGGACCTCACCCTGGACTTCCGCCGCATTATGGAGCCCTT
TACGGCCAGCAATCTGCGCGAGAAGCGGATGAACCGCATCAAGGACTTTGTCAGCCTGAGCAGCTTCTTCCACGTCTCGCACATGGGCATCTTCA
ACAAGGCCTCCACGCAGCTGTCCTTCAAAGTGGTCCGCTTGCCGCGCGGTCCTTCCCTGACTTTCAAGGTTTGTTTGTTTCATCGCTTAGTTTAT
ACTGGATATTTTACCGCGAAGTTATTCTCTGTCAGGTTCACCAGTTCACCCTGGCCAGAGATGTGATCTCGCTAAGCAAAAAGCAGATGATTGAC
AACGATCACTTCAAGCACGCTCCGCTCGTCATCATGAACAACTTCAGTGGCGATGGCAAGCACCTTAAGCTGATGGCCACCACGTTCCAAAACAT
GTTCCCCTCAATTAACTTGGCCACGGTTAATATCGGCACCATTCGTCGCTGCGTCCTGTTCTCCTACAATCCGGACACGAAGCTGGTCGAGATGC
GGCACTACTCCGTGCAGGTGGTGCCGGTTGGCTTAAAGCGGGCGGTCCAGAAAATCGTCAAAGGAACGGTACCCAATCTGGGCAAGTGCAACGAA
GTCGTGGACTTTGTGACCAAGTAGGAAATGACCGTTTGTTCTCATTCCATCAAATAATCATAATATTGATTTTCAGGGACGGCTATGCCTCCGAA
TCAGAGGCCGAAGATGATGAGCAATCACATGTGGTGCTGGCACAGACTCTTAAAAGCAAGGGCAACTTGGAGGACAAAAAGAGCTCCATAAAGCT
ACACGAGATCGGACCTCGACTAACCATGCAGCTCATCAAAATAGAAGAGGGCCTTCTGACGGGCGAAGTACTGTATCACGACCATGTGGTCAAGA
CAGAGGACGAAAAGGAAACCCTGCGCAAGCTGGTCGAAAAGAAGCGAAAGCAGAAGGAGCAGCGCAAGAAGGAGCAGGCAGAGAACCGTGCCCGC
AACTTGAAGCTTAAGAAGGATGAAAAATGGGCTGCCAAGAGGGCGGCAGAGGGACGGACTGACAGCGATCCCGAGGATGATGCAGAGTACTACAA
GGAGGAAGTCGGCGAGGAACCAGACGAAGGTGAGTTGTGCTACATGCTGCGTAGAATATAAACTAATGTTTCCTTTGCAGAACTGTTCAAAATGG
AAGCGAAGTCCTCCCGAAAGCGGCCTAGTTTGGGCGGCGGAATGAAATACAAGAACAAGCGCGCTAAACTGGATACCAAGGACAAGAATGACAAA
TCTGAGCGCACGGACAAGTACGATCGTAAGGACAAGTTCGATCGCAAGGACAAGAAGGACAAATTCGACCCCAAGAACAGGAGAGCCAAGTTCGA
TCCCAAAAACAAGCGCGCCAAGTTTGACCACAGAAAGAGTAGAAAATCAAAGTAGTACATTTAACATAAGCTATTTTATAAAGACCATTGGTTAA
CACGACATCGCAATGTTATCAATGGGAACTAACTAAACATACGTTGCACCACCTCCTTGTAATGGGCCTTGCTATCCTTCCAGCTAACAGCGATG
TTGTCGCGCAGCTTGCTGAACTCTCGCTTCTCCTCGTAGTTGGGCATTCGCTCGATGGTGGCTTGCGCCTTGGCGAACTCCTTCAGGTGATAGTA
GGCGAGTGCACGCCGGTAGATGCTCTTCTCGCTGGGACTCTCCTCCGTCTCCACAAACTGCGTGTGGTAGATTACATGCTCATAGCGTTTCTCCT
GCAGCAAACAGGCGGCCAGGTTGGTCTGTATCTGAATAAAGAGCTCCTCCACCGCCTGGCCGTTGATGCCATTGGTCTTTTTGGTCAGTTTATCG
AAGGGTTTGTAGGTGATCAGCAACTTTGCGGCACGCACAAAGTAATCAAAGGCGAATTTCGGGAACGTCTTAAAGGTGGCCACGCCGCTTTCCTT
GAGACGTAGTGCCACCTCATAGATCTCTGCAGCGCTTAGCTTCTCCACCTGAGTGTTCTTCACAATTTTCTCCAGCTTCAGTTCAAATTCTATTC
GTTCGCCGGTTTTGGTCGTGATGCTACAGGCTGCCGTTTCACCCGGCACAAATTGCTGCAGCAGCAGCTCCAAGTAGCAGTCCACTGCGGTCAGG
CTGGTGCCCATTTCCAGGCTGTGCTTTTGAGGATACGTAGCGGACTCATCGCTGACCAAATATTTGCTAGGTCGTCCTCCCAAGTTGGTGGCTTT
CTTGTTGACACTGAATTCCACCGTACTGATTATCGTGGGCTTGTCCATTTCGGTGAATTGGAGGCCAATTACCTTCTTGGCCAGACCACGGTTCT
TGTCCTCCCACTCTGTGCCCACGTACCAGTCCATTTTGGAATATTTGCAAATTGGGAGCTTCGAAATTTAGCAGTAAGCAAAGTTTGCGATTTGG
CGATGTGACCAGAAAACCGTCAAAAATGTACCTATCGCGAATTTCACAAAAAAT
(SEQ ID NO: 637)

Exon: 1001..1398
Exon: 1461..1825
Exon: 1882..2309
Exon: 2361..2664
Start ATG: 1069

Transcript No. : CT18136
ATTTTCCGCGCGAGCAGCCACACTGATCCATACACGTGCGGGAGAAAAGTGAACAAAAACATTGAAACATGGGCGGTAAGAAGAAAGTGCATCCG
AAGACGCGCACGGCGGCCTTCAAGGCCAGCGAGCCGAGCGAGATCGTGGAGGCGCCGCACTCCTTCGTCATCCATCGCGGCCTCGCCTGTCCGTA
CATCACGGACCTCACCCTGGACTTCCGCCGCATTATGGAGCCCTTTACGGCCAGCAATCTGCGCGAGAAGCGGATGAACCGCATCAAGGACTTTG
TCAGCCTGAGCAGCTTCTTCCACGTCTCGCACATGGGCATCTTCAACAAGGCCTCCACGCAGCTGTCCTTCAAAGTGGTCCGCTTGCCGCGCGGT
CCTTCCCTGACTTTCAAGGTTCACCAGTTCACCCTGGCCAGAGATGTGATCTCGCTAAGCAAAAAGCAGATGATTGACAACGATCACTTCAAGCA
CGCTCCGCTCGTCATCATGAACAACTTCAGTGGCGATGGCAAGCACCTTAAGCTGATGGCCACCACGTTCCAAAACATGTTCCCCTCAATTAACT
TGGCCACGGTTAATATCGGCACCATTCGTCGCTGCGTCCTGTTCTCCTACAATCCGGACACGAAGCTGGTCGAGATGCGGCACTACTCCGTGCAG
GTGGTGCCGGTTGGCTTAAAGCGGGCGGTCCAGAAAATCGTCAAAGGAACGGTACCCAATCTGGGCAAGTGCAACGAAGTCGTGGACTTTGTGAC
CAAGGACGGCTATGCCTCCGAATCAGAGGCCGAAGATGATGAGCAATCACATGTGGTGCTGGCACAGACTCTTAAAAGCAAGGGCAACTTGGAGG
ACAAAAAGAGCTCCATAAAGCTACACGAGATCGGACCTCGACTAACCATGCAGCTCATCAAAATAGAAGAGGGCCTTCTGACGGGCGAAGTACTG
TATCACGACCATGTGGTCAAGACAGAGGACGAAAAGGAAACCCTGCGCAAGCTGGTCGAAAAGAAGCGAAAGCAGAAGGAGCAGCGCAAGAAGGA
GCAGGCAGAGAACCGTGCCCGCAACTTGAAGCTTAAGAAGGATGAAAAATGGGCTGCCAAGAGGGCGGCAGAGGGACGGACTGACAGCGATCCCG
AGGATGATGCAGAGTACTACAAGGAGGAAGTCGGCGAGGAACCAGACGAAGAACTGTTCAAAATGGAAGCGAAGTCCTCCCGAAAGCGGCCTAGT
TTGGGCGGCGGAATGAAATACAAGAACAAGCGCGCTAAACTGGATACCAAGGACAAGAATGACAAATCTGAGCGCACGGACAAGTACGATCGTAA
GGACAAGTTCGATCGCAAGGACAAGAAGGACAAATTCGACCCCAAGAACAGGAGAGCCAAGTTCGATCCCAAAAACAAGCGCGCCAAGTTTGACC
ACAGAAAGAGTAGAAAATCAAAGTAGTACATTTAACATAAGCTATTTTATAAAGACCATTGGTTAACACG
(SEQ ID NO: 638)

Start ATG: 69

MGGKKKVHPKTRTAAFKASEPSEIVEAPHSFVIHRGLACPYITDLTLDFRRIMEPFTASNLREKRMNRIKDFVSLSSFFHVSHMGIFNKASTQLS
FKVVRLPRGPSLTFKVHQFTLARDVISLSKKQMIDNDHFKHAPLVIMNNFSGDGKHLKLMATTFQNMFPSINLATVNIGTIRRCVLFSYNPDTKL
VEMRHYSVQVVPVGLKRAVQKIVKGTVPNLGKCNEVVDFVTKDGYASESEAEDDEQSHVVLAQTLKSKGNLEDKKSSIKLHEIGPRLTMQLIKIE
EGLLTGEVLYHDHVVKTEDEKETLRKLVEKKRKQKEQRKKEQAENRARNLKLKKDEKWAAKRAAEGRTDSDPEDDAEYYKEEVGEEPDEELFKME
AKSSRKRPSLGGGMKYKNKRAKLDTKDKNDKSERTDKYDRKDKFDRKDKKDKFDPKNRRAKFDPKNKRAKFDHRKSRKSK*
(SEQ ID NO: 639)

Classification: hypothetical
Gene Symbol: ppan
FlyBase ID: FBgn0010770

Celera Sequence No. : 142000013385214

FIGURE SHEET 346

TGAATGGCAAATTGGTGTGACCGTATTTTGCGTTGTGACTCGGCTGCTTTATTTACATTGAATTTTTGTTCGATTTTTGAATTTAAAATAAAAAT
AATGCCGCACGGACACTCTCACGATCACGGCGGCTGCAGCCACGAGGCCTCGGACGTGGACCACGCCCTAGAAATGGGCATCGAGTACAGCTTGT
ACACCAAAATCGATCTGGACAATGTGGAGTGCCTGAACGAGGAGACGGATGGCCAGGGAAAAAGTGTCTTTAAGCCGTACGAGAAGCGCCAGGAT
CTGTCCAAGTACGTGGAGAGCGATGCGGATGAAGAGCTCCTCTTCAACATTCCCTTCACCGGCAACATCAAGCTCAAGGGCATCATCATAAGTGG
GGCCAATGATGACTCCCATCCAAACATGGTCAAAATGTAAGGAACACAAAAGTCAAGGCTGCTTTAATATTACTATATTCATCATATATCTTATTTT
TCAGCTTCAAGAACCGACCCAGGATGACCTTTGATGATGCCAGAGCAAAGCCCGACCAGGAGTTCCAGCTGACCCGCGATGCCCGCGGAGAAATC
GAGTACTCACCCAAAGTGGTCACCTTCTCCTCCGTGCACCATCTCTCCCTCTACTTTCCCAGCAATTTTGGCGAAGACATAACACGCATTTACTA
TATAGGTAAGCTCACAACAATCTATGTTTTATCTGTGTTCCCAACTAAAACCAAGTCACTATTCAAAGGTCTTCGAGGAGAGTTCACAGAAGCTC
ATTACCATGGCGTAACCATATGCAACTACGAATCCCGTGCCAATGCAGCGGATCACAAGGAAAAAGGCTTTCGATGGAGTCGGCAGAGCCATCCAA
TAGGGTTATAGAGATTAAAATTTACAATTTAATTGAGTATCTCTGTAGTGTATATATTTTGTGATCATTTAAGGCAAGAAATGTTTTTGTATTCG
CTTAACTTATTGAGCATTTGTATTGCACAGATATTGTGGGCTAAATCATACTAAGTATATTGTGTGGGTGGAATCACATCGGGTCCTATTTTCAT
GCCCATATTGGGCACTTTATCCGAATGGATTTCAGCCGTGACCTCGGTGAACAGCTTGTCCCACTGCCAGAGATCGTCCTTCTCGTTGAGGCTCT
CCTGTGGAACCAGGCAATCGGTGAGGATTGAGAGATCAAAGCCATCCACAGCTGAAAAGGCGTACTGGGAAAGCAAATCGGAATTGGCCTCCTTC
AAAACAGCAGATCGTGAGGTGCCAATACTACAAATTACAACTTATTATCGTAGTGAAGAGAAATATAGCAGCTTCTGCTTACGTTGGCGGTTCTA
CAATCTCATTGAGCATGATTTCGTCCTTGACATCATCCATGTCTGGGATGACGGGAATGTCATCCGTTGGTATGGAATTTGTAGCCGACTTTGTT
TGTTTAAAGCGCTCACTAAAATGAATTTTATCATTATAACAGTCGGTGGAAAGTGAAGTTATTGTGATAAACTTGTACTCACTCATCAAAGGAGT
TTTTCTTGGACCTAAAAAGATATAGAGCAATCAGTAATGTGCCTAATTCGAGCCTAATCATACCCACTTTAATCCTTTGAGTCCAGAATCCGCCC
AGCCACCTGAAATGCGACGAATGGGTGGTCGATGTGACTCGAATTCATTGTTGTATGTGGACGAGGTGGCCGTGTCCGAGGTGGTCGGTGGGGTG
CCCGCCTGGACATTCAGCGTAATGTCGATGGAAATGTCCTTGGAGCCCCCAGCCGCCTGGACATCCTCCTCCTTCAGAACATCGCGACTCTTGGA
GCGCCGACCCTTCCTGGCCGTCGTCTAGGGTGGCAAATAAATCGAAACTTCAATTTGCATCCATTTAAACAGGGTTACTTACCTTTCTTATGGTC
ATCTTGAGTTCTTCGGCCCAGTCCATCATCTTTTGTTTACGTTTATCCTCAGCGTTTCCAAGGCAACAAGTGGTCATGGTTACTCCGTGGGAATG
TTCAAGTTTACTAATGGAGTTTGCCATTCGCAACGCGATGCGATAGTTTTCAAATCAGTTACCTATCGCCGATGACAGTTGGCGGAGCTTCAAGT
GGCCAAAATAAACAAATATTTATTTTCTAATAACGCAAAATGCTGACGGACACGGAAGATGACTTCTTTTTCGAAGAGGATAAGATGTAAGTGGC
CATTGAAAGCAATAAATTGCTGCAACACCTACGCCCAGCTCTATTTACGCACAACAATCTGTTGCGATGTGCCGAAAAGTGTCTGTTAAAAATCA
ATAATTGCCACCAAACTGAAACATATTGTTGGAATCAGGCCAGAACCGCTGCTCATCCAGTTGGATGGGGATGGTGCTCAGGCTGTCCGGCAGCC
CAAGGAACGCACGGAGCAGCGAGAGCATGCCTCCGGTTCCGTCGCTCCCAACGAGGCCACCGTTATGCTCTGCTCCCCGGCGGGATTCTCCTGCG
ATTCCGCATCCGGGGACAGGTTCGGCATCGAGTCCGCCAGTAGGCAGAAGTATGAGTTAGACCGTCTGTAAGTCAACTCCGTTGACCCGGAATCG
TTCCCATACTATTTCCTGTGGCAGCTCTGTTTTCTAAGTTCTGGTTTTTATAGTCTTTATCCTGTAGTTTCTACCAAATTAGCTTACTCTTGGTT
TTTTATTGATTTTATTCTTTTAAATTCATAAATTGGTGTATTTATATTAATAGTAGCATATACACTTCTTTATTTAACTATTAAAAATTTAATTT
TGATTCAGTTGCTGTTTTTTTTTTAATTATTTACTTTTTAAAGAGCGAACACAGTACTATATCCATTTTTTGTATAGTAAGAACTACAGAACTAG
AACTAACAAGATTGTTGTTTATTTAGTTTATTAATTCCACCGAAAAAGGACAAATGTGAATTTCCTTTGTAGAGCCTTAGATGCTTATACTTAGG
CTAGCTAGTATACAAACTATATTGAATTCGAGGTGTC
(SEQ ID NO: 640)

Exon: 1982..1888
Exon: 1829..1588
Exon: 1531..1508
Exon: 1440..1318
Exon: 1262..1001
Start ATG: 1977 (Reverse strand: CAT)

Transcript No. : CT18140
TAACCATGACCACTTGTTGCCTTGGAAACGCTGAGGATAAACGTAAACAAAAGATGATGGACTGGGCCGAAGAACTCAAGATGACCATAAGAAAG
ACGACGGCCAGGAAGGGTCGGCGCTCCAAGAGTCGCGATGTTCTGAAGGAGGAGGATGTCCAGGCGGCTGGGGGCTCCAAGGACATTTCCATCGA
CATTACGCTGAATGTCCAGGCGGGCACCCCACCGACCACCTCGGACACGGCCACCTCGTCCACATACAACAATGAATTCGAGTCACATCGACCAC
CCATTCGTCGCATTTCAGGTGGCTGGGCGGATTCTGGACTCAAAGGATTAAAGTCCAAGAAAAACTCCTTTGATGATGAGCGCTTTAAACAAACA
AAGTCGGCTACAAATTCCATACCAACGGATGACATTCCCGTCATCCCAGACATGGATGATGTCAAGGACGAAATCATGCTCAATGAGATTGTAGA
ACCGCCAACTATTGGCACCTCACGATCTGCTGTTTTGAAGGAGGCCAATTCCGATTTGCTTTCCCAGTACGCCTTTTCAGCTGTGGATGGCTTTG
ATCTCTCAATCCTCACCGATTGCCTGGTTCCACAGGAGAGCCTCAACGAGAAGGACGATCTCTGGCAGTGGGACAAGCTGTTCACCGAGGTCACG
GCTGAAATCCATTCGGATAAAGTGCCCAATATGGGCATGAAAATAGGACCCGATGTGATTCCACCCACACAATATACTTAG
(SEQ ID NO: 641)

Start ATG: 6 (Reverse strand: CAT)

MTTCCLGNAEDKRKQKMMDWAEELKMTIRKTTARKGRRSKSRDVLKEEDVQAAGGSKDISIDITLNVQAGTPPTTSDTATSSTYNNEFESHRPPI
RRISGGWADSGLKGLKSKKNSFDDERFKQTKSATNSIPTDDIPVIPDMDDVKDEIMLNEIVEPPTIGTSRSAVLKEANSDLLSQYAFSAVDGFDL
SILTDCLVPQESLNEKDDLWQWDKLFTEVTAEIHSDKVPNMGMKIGPDVIPPTQYT*
(SEQ ID NO: 642)

Celera Sequence No. : 142000013384550
ATGCGTCTGGCACGCGGCTCCTCCTCCGCCAATCCATTTGCCTCCATAATGCGCTGTCTCTGCGAATGAATGTGCTGCCACAGAGAGACTGCGTC
CTGGTGCTCGCTACTGCCCGGTATGTAGAAGGCCTTGGCATTGCCAATAAGCAGCTCCAGGTCGGCCATCAGATCATCCAAATCGTCGTAGGAAT
CGGTTTTCAGCTTCTGCTGAACCTTGAGCAGATCAATGGGATTGACCACCACGTCATAGTACGAGGGCTCTTGCCGGCGCTTCGGCACGCGGATG
AAGGTGTCGCACAGCATTGAACCGTCCTCCTTCTTTATGTTCCTTATGGAATCGTACAATTGCTGGCACAGTTCTGTGGGATCGAGACGGCGCTT
TTTTCGCGCCGATTGTGTCGTCGTCTGCTGCACCGGTGACTGCTCCGGCGTCGAGTCGTCCAGCTGCAGCGGATCCTCGTCCTGCCGGCTGGATA
TGCTGCTCGCCCGGCGCTTGCGGCTCAGCATCGTGTTATCCCTGTTCTTATTACAGTTAAAATCTAAATATCCGATAATAAGACGCCACACAAAA
TGCCACAAATTCTGGGAATGAGCGAAAAAGTAGTGGTGGGCGAAAGGTTCGATAGTGCGCGGTCGATATATAGTTCGATAGCCGGCCACTTGCGT
GGTGAGTTATCGTAATCGAAGCGCGCGGTGGTGAATATTATTTAAATGGTATGTTCCCACCAAAAATCATATTTCTTAACCAAATAAACAAGCT
GAACATCATTTTACTTAAGTTCTTTATTATAGCATCCCTAAAGCATCATTTAAAGTTTTAATTAAGTCATTGAATCACAGCAATATCGTAGGTAG TTTTCCTTAAATTAGCTCCTTCTCGAAAAAAGGCATTCAAGCCAATAGAAACAACGAAGTTAGGCTGAAAAAAAAGTTAAACAGAACAATATTTA
ATTTAAAAGTCAGCAAAACGCAAGCGCGCAATTAAAAAGCCATGATATTTCGATTAATTTAGTAAAATGCTTTGTTTATTATTATTTTTTATCAC
ATAAGTTTTAGACGCTTGTTAGTGTGTGATTGTGTGAATATTGGGTTACAGATTTGAGTATGCCGTAAAATGAAATGAACACGCCTCATCGTTTC
GCTGCTTAAGGAACATTGTTAAAATCTTATAAAAATAACTGAAATATACGTGGATAAATAGCGAAAAACATGTATGAAATGGAATTCACTCTGAA
CGACAAGAAACGAAATTCTAAACTACGCCTACTGCAAATTGACTGCGGCTTATGTTGCACAATTACATCTTCTATTTACATGCTAGTTATTGGCG
AGATTTCTGCGAATATCATGGTACACGAGTGCCATTGTTCTGTGTTTACTGGCACCACAGTGATATGCTGGTGCACTGTGAGGACTCTGTCTGTA
TAAAGTACAACAATTAAGCACAACAGTTAACATTGCAAAATTTAAATATTAGTATCAGTTCTGCACAACTATACGTGATCATATAACATATGTAA
AGGTATATTATATAGTTTCAGCTGCCCATCTCCCATGTTTTCTCGTGTCTTAACAGTTCATTTCGTTTGCCTTGCGACTAGCGGTGGTATTGCG
ACTGCTCTTACGACTAAGGTTACGATACTTGGTATAGAAACTTGTTAGGCTCTTTAGCGGCGACTCGACAAGGCGCCTCACCTCCTGTCGGTTTA
TACAAAACGCATTGTCGTGTCGCTTGCGCCAATATCAGTTGATGAAGCTAATGTAGTTAGTAAAGAGCACATAGTTCTCCACTAACCGGGCTCTT
AGCTCCCGGCGCACCGTAGCCGTGAATTTGTTTGCCAAGCACAGGGCAGTTGTGGTTCCAAAAACCAAATTGTAAAGCAATACAATCTGGAAGTT
TCCCAACCACTCGATGGCTCCAAAATCACCCAGCAGGTCAAAGTTTGTGATGCCTGTAAGAATCAATAATAGTCGCTTTTAAACACTGTATTATT
CATTAGTAATTTGCCACAGCCTACCTATGATCCTGCTGAGAAGCGGCAATGCCGACGACAAAACCAGCATGAAGCCACAGTTCAGCATTAGCTGT
GGCAGCGAAGTCTGGCGCCGCTTGGGACAAACCTTGCGCATGAACGGCATGCTGTAGAAGCCCACCACCGAGGTGGCGCCGAGATAGAAGATGAG
ACACACCTCCAGGCCGGCACCAAAGGGACCCAACTTCGAGAGCGAAGAGATGCCCAATGCGAATTGCTAAATAAGGGAAACAAACTCAATAAGCA
TTCGTCTTACGATCCCTGCAGTTAGACCTACCCTTGTGCTTAGTGGCAGCGCCTTAATGCCAATAAGGAGCTCTAGTGTATTCTGCACAACCAGC
AGAATGGTGACAGCTGTGCAGAAGAGCAGCAGCAGCATGGCCAGCGGATAGACGAATGTGCGTTGGAAGGTGCTCGATGTGCGCAGCTTGTCTAG
TTCCTTGCGCTCGGAGTCCAGTTCTCTTAGTCTATCGTTGAGCTCGTCCACGTCACTGGCCATCGCCTTGCGCTGGTATAGATGAGCCTGGGAGT
GTTGCAGCAGTGGCTGGGGATAGAAGGTGCGCCCACGTCCCAGACCAATCCGATTGCCAAGGCGACCTCCGTTGGCGGCATCCGCAATGCTCACG
TTGTGCAGCTCAATGTGCGCTAGCTTCCGCTTCACGCTCGCCTCCTCCATGTAGAAGGCGCTAAACTCCTCGTTGACGTCGCGCAGTAGCATAGG
TCGCACCAGCACCTGGTTAACAACGCCAAAGAGGCGCACAAAGCCATACGGGGTGCAAACTGTAAGAAAACAAAACGGTTGTCCTGGTTACCAAA
CTTGTACATGCCTTAATATTAGTATGTAAGATCTAGAACTTATTTCTCGTTGTGTACGAAACGTAAACAAAGGTCTCTTTGACATCCCACTCAAC
TTAAAAGACATTCTGTTCTGAGCAGTCGAACCAGTCGGTATCTTAACTAAATTTCTATTCCTTACATCTTTAAAATGGCAAACGAAGAGGTTAAA
GACAATGCCCAACTTAAGGCAACTATGTTAAACTGCAATTTGAACCCCAGTGTCGCGGATGATTTTGCTGAGTTCGAGGCAACCCTTGCGAAGAT
CGATTGTATACTGCAGAACAAGGCACCCTGTGACGATGAAGATTCAAAGGCAGGTGGCGATGCCAAGGAGAAGATCAACTTTGACAACTTGGATG
TGGATAAGGTGCGGCTTAAAGTGAAAGAAAATCGAACAGTCATCAACAGAAAGTCTCTAGAAGAAGACAATGAGAAGCAAGTCAAGGATATGAAC
CAGAAGAGTTTCATGGAGCAGGTGGAGAAGGATGCCAATGATCGTGCAGAGGCACGTGCCAAAGCCGAATACGAAGCAGAACTACAGAGAAGGTA
AACTTAATGGTCTCCCTAAAATTATAATATATTGTATATAAGGATAATTTTTTAGTCAGGGAAACGAAGCATTTCGCAGCCAGAAGTACGAGAAG
GCAATCCTACATTATGACAAGGCTATCATCAAAGTTAAGGACAGCGCTATTACATATTGCAATCGCGCCTTGTGCTACATCAAGTGAGTTACAAT
CTTCAAGCCTTATGAGCTATCCTAACAAGCCTTCTTCATCATTTTATTTCCATCTACCAGGCTACAGAACTATAAGCGCGCCCTCAAGGACTGCC
AGTACGTGTTGGAGAAGCTGCAGGAGAGTAATCTCCGCGCCTGGCTCTACCAGGCCCACGCCTACAAGGGTTTGAAACAAGACGACAAGTTCGAG
GAAAGCGTGGTCAAGGCACGTGAACACAATCCCAAGCAACTGGCGTACATTGACAAGTACATTAAGCAACTGGAAGCCGATCTTAAAGCACTAGA
AATATAACTTATTTAATTTTGCATTATATACTCACTCAGCATAAGCATGACACCCAAAAACGAGACACACGAATAAAGAAACGGCAGGTGAACAC
TGCCCAAATCTGTGAAGCATGAAAAGCGGAAATTAGAAATGCATTGTGCATCAGAATCCAATCCCAATTTGGGGATGGGCTTGTCAGGGGCGCGG
AAAGACAATTGACATTGGAATTGATCTCTTCCGCACCCGTGCATCATTACATTATATACTCACTTAGAAACCAGAAGAATTGAAGCTTTTCAATG
CCAAAGACTGCACTTAGGACGGCAGTTAGTACGAGGACAATAATGGCCATCAGCATAAATACTGTAAAGGTTTCGTAGACTCGCGGCAGGATGCC
CTTCTTGTTGCCGACGAATCCCGTGGATTCCGAGAACAAATAGACAAATGGCAGGAAGATGAACAGTGACAGATTGGAGAACAGAAATACATGGT
TCCACAAGCCTGAAATTGGCATATTAAACGGGTTAGTCAGTGTTCCTCGGTGGATAATGTAGTACTTACCCTGTATGAGTGAACTGTTTAGCCAT
TTCACATAGTAACTGTTGGGATAGAGGAGTAGCACCTCATTGCTGGCAATGGAAACGGGCAGCAGCATGGCAGCCCCTTCGGCAACGGCCAGTGT
GAATGTGCACAGCCAAAAGCTATGGGGTTGGTTGGGTGGAAAAGGCAAAAGCAAAGAAAACCATTCATTATTGCGAGTGCAAGTCAAGTGACGCG
GCAATTAGCGACACAGGTTGTTGACCACTGGATGCCTCACCTTATGCGATAGACCAGCACCTCGTCCTCGTCATTCGAATAGAGATCGTCACGGT
CGCGCCGCCTAAAACGTGAGACGACCACATAGGAGCTGGAGTACAGCAAGATTATCAGTAGCAAGAATATCTGAAAAGAACAATGCAACATGGCA
AGTTAGTAAGCTTTATGGTTTTATCAGCTAAGTAATATTTTACTATAATATAATCAAATTTATTTTCCCTTAGAAACTGCAACATTTCGATCGCC
CTCCTCAGGTTGGTTAATTACGTAAAACCCAAAGTAAATTTAGACTCGATTGTCTTTTTTGTTTTATTTTATTGAGGTTTTCATAGCACATTTCC
CCACATATTCTTGTGTTTAAACAAATGTCAAAAAGTAAACACATCACCCACGCATCTCCTTTGTTTTGTTTTTATAAATATTTGTCATTACCGCC
AACTGTGTGCACATTAGCCAAAAACATTTTCGATTCGTTAAGTTAGGGAAATCTGTATTAATCTAGCTCGGTGAATATATTACTTATTGATACTG
ATATGTGTACATGATTCAATTTAGTGTCAAAGTCTGGCATTTTAAGCGTTTCAGGGTCTAATCGTCAAAAACATTGCCAGAGTGATTTGAACTTT
TGTTTGCGGACATTTCAATTTTTCAATTTCCGGTATGTATGCTTAAAATAATATTATGTATGTATATAGAACAGGTACTCAGGTTTCTTTTGCCT
ACAACCCTATATCACCATAAACCACTTGGCAATCGATGAAATATTATGACCGTCAATTAGACCAATAAAGTTAATTTCGTCTGCGTTCAAAGGTC
ACAAAAGAAAGCTTATCTGTGGCCAACGACAAAACATGAAACATTTGATAAGAACTAAACCGATAGCGGTCATTTAAATCCCATTGAATGTCAGC
AACATTTGATTATCCGTACTCTTGACTATTAAATCCGAGTAGGTTGGCAATTTGAATCTTCATCAGCGATTTCCAAACATTGGACCCATCATTTG
CAGGGTAAATATATTTTTGGGACCGCGAAATATAGATGCCAATCACATGGCACACGTCATATTTTCGCTTTTTTTGTGTATGCGAAAAGCGAAAA
CAAAACAAAACGTAAATGGATACGAAAATACAATAGTCTAGGCGCACAAATAAATCATTAAGTGAAGATACTTTTCATGTTATAGCTAGCAAAAA
AAAACTTGGGGAAAAAATGCAGAGAGAGCAAAAAACATTAGTTTATACTCACGTCCCTGCTGTGTTTTGCTATTCTTTGTTTGCTATTCGAGATA
TTTTCAGTGGTATCTGTGAGATACTCTATTGCGTTATACAACGCGAGTTTTAATTAACTTATAACTTTATTCTTCTGCCTGCATTTGACCAGATC
AATTAAATGAAATTTTCTTTAATTGCTCGCAGCGTTTCGCATTTCGGGATTCCAACCTTTCATCTTGCCATTCGAAATGACCTTCTTTTCAGTCA
ACATTTAAACAGTTTTCTCTACACAGTAGACAAAAAATATGATCAAATATTAAAAATTAAATATAGAGACGTAAATCGCCTGCTATCAACAGCAG
AGTGCGTCGCTTTATTTATAGAACCCAAGTGTAGATCATGGAAAAATGTAGATACACTGAATGGCAAAACTATAAGGTTGCAGTATAATTAAACA
TCCAAAAGTACACATTTTGCGCATCTAGATAACGAGGCATTCGAATACTAATGTGATATGCACAGAGCATTTTTATAGAATCTAGGCCAGCTATG
CAGCTATGAAACGCAGTGTATTTTCTAGACTATGACGTGTTAAACTTGAAACACATAGGCGACGAATACCAACTGATATGAGAATCTTATAATAT
GTACGCCAGGCATTCCTGAATGGAAACAATTGAGCCAGCGATCTTCAAGCTTAGTTTAGTGCTTGTCAGTCGAGAAAACGTGCAACTGCAATGCG
CAGCCCCAAGTGGCATTTGTCACGCTCCAAGCGATTTGGATTTGGCCAAACTAAACGATCTGTGCCTCGGAATTAGCCGCACTTGCATCGTAGGC
GAACGACGAGTCAATGACTTGACATGAACTCGAGGGGGAACACAACACGCCCATTGAAATGTGGACGACGATTTGGCTAAAAATAGCAGCTACGC
CCAAAATGCAGCCAGAAGCCAGCGAAAACGACGACACTGTGGCCAGGCCAAAAGGAGAAGGGAAGAGGATCGCCGGTCGGACGGGTTTTGGCTTG
ATTTGTAGACAACTTTGCCGGTGAATGGGCTGCGAAATATTTATACTTTTCTATACCCAATAGTTGTGCCGAACAGGGGTATATATTGTATCCAT
ATGTGCTGCAAGGTGGGTTGGTCTACGCCTATTGATACCTCTTCATTTTATCATTTCAGATAATTTTTTAGAATGTAGCGTCTCTTCAGATTCTC
AAAGTGGAGAAGAGCTGTATGAGTCGTCCCAATTGTTTTAATGACTCCAAATAAAAATGTGTTTTCTAATGAGGGGAACTGCATTTGCAAGACTT
TTGGTCATGGTTTAAGTTACCCAATTCAGTTTCTTCATCAGACTTTTCCCTAATCACTACTTGGGAAATGACTAAGAACATAAGTGTGGTGTTAC
ACAATAAGTTTGTATGTATTTTCTCAGAATTTCCTGCTACTACACTTGGCATTAGTGGTTTTAATTCGGGTTTGGCTTTAGGTTCCTGAATTATT
TATGAGAGCTTTGCGTTGTTTGCATTTCATTATTGCATGGAGTCCCACACATCACGTATTCGGTATGTTGACCCACATTCTGACGAATTATTCAA
TTTTCGGCCATCCAATGCAATCAGAACCGCTGACTGAAACCAGTTTCCATTTCCTGTTCCTGTTCCAGTTCCACAGAATCATCCTCAATGAAAGA

FIGURE SHEET 348

AATGTGTATTTATAGACGTACAAATCATAATCGGTGGCATAAAAAGCAACCTGCAAGTGTATTGTATCTACGCCAGTCTATGCCAACCCTTTCAA
ATGTGTCCATTTAACGCCTCGTCTGCCATTGTTTAAACAGATCCAACAGCTGATCACGACAGCAGACACTTTCAGTGACCCAGACGGTACCAAAT
CGTGACCACTAGCCGTGCACTTGAAATCTGGCCTGCAAGTGTTTTGGCCATTTAACCGAATTTTCACAAAAGGAAATTAATGCCTTGCGCAATAT
AATAAACATGTGTTTTTATTCGATTCAGTCTGTTGTTTACATAAATCACTGGTTTCGTTTATTACACGCCCAACATTTCTATAAATAGTAGCTCG
AGTGAAACACTTTCACTTGTTGCTTTTGCTTATGTTGCCTTTCTTTGTTTTTGCCTGAATTGTTTAAAATTTGATTTCAATTGAAAGTTCTACGA
TATTGGTACCAATTAAGTGAAGTTTGTTGATTATCTTATCAATACCTTGGACTTCTAGTTACCTTCCATTTTTCAAATAGCAAAACCTAAGCATT
CTGATAGGGCTTATGAACTCACAAGAACCAATTAACTTAAGGGCAACATTACTGGGAACTATTAATGAAACTATTTAAGCCTGCCTTCCATTTGG
ATATTGGAATTTAAATATTCAACAAGAATGGAGAGTAATATTTTAATGAAATTTAAAACATATATTTTAAGAACCTATTGTTCTTAATTAATCTA
ATTGTAAACAAGAACATGTAAAAAAACATTTGTTTATAAAGTTCTAATAATAAAATAGAAACGAATAAAGCTTGGTAATGGTAGCAAGTATCTCG
CCGTCGAATCATCGATTGTGTCTAAACTCTTTGATTAACAACAGGTGTCCGTCCGTGTGGGCCACTTTTGGTGTGTCTGCGTGATAATTTTCGCA
GCTCAAATAGAAAGTGCAAGAAGAGAGTGGCTATCGCCGCCACTTCCTTCCCCGATTTTATATACAAAGCCCAAACGCAGGCGCCGAATGTGCTG
ACCACTGTAGTCCGAAACCGATAACAGAACCATAAACAAATACATTTCTGTAGACGACCAGCAACTGATTTCTCTGTTTATCAAAAGACCAGGCG
AAGTGTGTGTAATTTCCAGAAGTCGCACGCATTTTACACCCAGCCACATGTACAGTTAGAACAACAACAATAGGGACAGCTGCGCCCTGAGTTCT
TGTTGTTGTTTTATGCGTAGTGGGGTGGGAAATTGGGTGGAAAGGGGATGAATTCAATCCAGAAAAACACTTACAATGTGCTCGCGTACTGTATT
GTGGAACAATTGCAGCTTTAGATCCGTAACCTCCTCCTCCTCCTCTTCGTCCATGCCCACGAAATATTTGGACAATTTATCGCTGGTAGCCAGTT
TTCACAATTTTTCCTAGATCACGCCTCACTTAAAAATGTTACATACACATTTGACAGTCGCCAGAGTCTGTCAAATTCCTATGGGCAACAGTCCT
TCTTAGTAATGCGCTCCAGGTTACAAATTTTCTGAATTAAAGTCGCTGTGGCGCTGCACTGTCTGATTTCGCACGGTAATTGTGATTAATTTAGT
TAACTTTTTGATGCCGCATTGCCTTTCGACCCGTTTTGCGCTGGTCACTAATTTTCTACTAGCATTCGAGCCGATTTACGACCGAAACGTTAAAA
GATTTCTATAAACTGGCGTCAGATTGACCGCATCTGCTAGAGGTGGACAATTGACGATAGGTCGATAGCTTTCGATGTATGTGCTTACGTTTAGA
AAGGAAAATATTGAATCTCTAAAAAAAAAAAAAATTGAATTGGAAAGAAAATACTGAATTTAAAATTTTTATTGACCTCTATTATTAGAGAAAAAA
ATATTATACCAATGCAATATCTTCAAGTTAAGAAAACTGTAACCCTAAAAACTATCAATTGGTTCAGACATTCTGGCAACCTTACATCTGTCAGC
TGTTACCATACAAAAATGTCCAATTTGCGGCGCCAGGTAAATTAACTTAAAATCATAAATAATCGGTTAATATTGTTTGTATTCCAGGTTCTCAG
TGCTTTCAAGAAGCTCCACCGTACACGACAATACGTTTTTCAGGGGGATGCCAATGCTTTGGCGGCGGACGACTAAAAATCAACGAATCTTTCC
TGCAGAATCGTAATGAAAGCAGCGAGGATGAAATTCAAAAGGTTTAACCACTTTTTGTAAATTCTAACTAAGTACATATATGGCAATTTGGCAAA
TTACAGATGATCAAGCTGGCGCAGGACGTGGATTTGGAGCTGCGAACGAATGTCATCCAAGCCCAGAAAAAAGAGGATGGTGTTTATGGTCAGTG
GGGCATGGCGATTACATAAAAGAGCGCTCAAAATTAAAATTTGGCTATATTTACAGAACTAAGGATCACGCCAGAGACAACGCGACTCGACAATG
TGGTCTTTAATCCTGACGCAATTATCGAAAAACCGCGCAGGCAACGCGGCGACAAAAACACTGAAGGTTGCTGCGGTGGCGCTGCGATGGCGGCG
CTGGAAGCCGAAGTCCAGGCCCGCAACAAATAAAAATATATTCAATATTTAGCTGTAGTCAAGATGGTTTTGTTCTGATTAATTACGTCGTTTAT
CTTTAATTTCTATTATGTTTCTTCTTCGATTTGTGACTACTCTTTGACTTGGACTTCTTTTGCTTGGATTTTGTACTCTTTTTGCG
(SEQ ID NO: 643)

Exon: 9346..8910
Exon: 4820..4696
Exon: 4579..4440
Exon: 4379..4149
Exon: 3999..3931
Exon: 2814..2312
Exon: 2251..2020
Exon: 1953..1001
Start ATG: 8984 (Reverse strand: CAT)

Transcript No. : CT18210
CAGATGCGGTCAATCTGACGCCAGTTTATAGAAATCTTTTAACGTTTCGGTCGTAAATCGGCTCGAATGCTAGTAGAAAATTAGTGACCAGCGCA
AAACGGGTCGAAAGGCAATGCGGCATCAAAAAGTTAACTAAATTAATCACAATTACCGTGCGAAATCAGACAGTGCAGCGCCACAGCGACTTTAA
TTCAGAAAATTTGTAACCTGGAGCGCATTACTAAGAAGGACTGTTGCCCATAGGAATTTGACAGACTCTGGCGACTGTCAAATGTGTATGTAACA
TTTTTAAGTGAGGCGTGATCTAGGAAAAATTGTGAAAACTGGCTACCAGCGATAAATTGTCCAAATATTTCGTGGGCATGGACGAAGAGGAGGAG
GAGGAGGTTACGGATCTAAAGCTGCAATTGTTCCACAATACAGTACGCGAGCACATTATATTCTTGCTACTGATAATCTTGCTGTACTCCAGCTC
CTATGTGGTCGTCTCACGTTTTAGGCGGCGCGACCGTGACGATCTCTATTCGAATGACGAGGACGAGGTGCTGGTCTATCGCATAAGCTTTTGGC
TGTGCACATTCACACTGGCCGTTGCCGAAGGGGCTGCCATGCTGCTGCCCGTTTCCATTGCCAGCAATGAGGTGCTACTCCTCTATCCCAACAGT
TACTATGTGAAATGGCTAAACAGTTCACTCATACAGGGCTTGTGGAACCATGTATTTCTGTTCTCCAATCTGTCACTGTTCATCTTCCTGCCATT
TGTCTATTTGTTCTCGGAATCCACGGGATTCGTCGGCAACAAGAAGGGCATCCTGCCGCGAGTCTACGAAACCTTTACAGTATTTATGCTGATGG
CCATTATTGTCCTCGTACTAACTGCCGTCCTAAGTGCAGTCTTTGGCATTGAAAAGCTTCAATTCTTCTGGTTTCTAAATTTGGGCAGTGTTCAC
CTGCCGTTTCTTTATTCGTGTGTCTCGTTTTTGGGTGTCATGCTTATGCTGATTTGCACCCCGTATGGCTTTGTGCGCCTCTTTGGCGTTGTTAA
CCAGGTGCTGGTGCGACCTATGCTACTGCGCGACGTCAACGAGGAGTTTAGCGCCTTCTACATGGAGGAGGCGAGCGTGAAGCGGAAGCTAGCGC
ACATTGAGCTGCACAACGTGAGCATTGCGGATGCCGCCAACGGAGGTCGCCTTGGCAATCGGATTGGTCTGGGACGTGGGCGCACCTTCTATCCC
CAGCCACTGCTGCAACACTCCCAGGCTCATCTATACCAGCGCAAGGCGATGGCCAGTGACGTGGACGAGCTCAACGATAGACTAAGAGAACTGGA
CTCCGAGCGCAAGGAACTAGACAAGCTGCGCACATCGAGCACCTTCCAACGCACATTCGTCTATCCGCTGGCCATGCTGCTGCTGCTCTTCTGCA
CAGCTGTCACCATTCTGCTGGTTGTGCAGAATACACTAGAGCTCCTTATTGGCATTAAGGCGCTGCCACTAAGCACAAGGCAATTCGCATTGGGC
ATCTCTTCGCTCTCGAAGTTGGGTCCCTTTGGTGCCGGCCTGGAGGTGTGTCTCATCTTCTATCTCGGCGCCACCTCGGTGGTGGGCTTCTACAG
CATGCCGTTCATGCGCAAGGTTTGTCCCAAGCGGCGCCAGACTTCGCTGCCACAGCTAATGCTGAACTGTGGCTTCATGCTGGTTTTGTCGTCGG
CATTGCCGCTTCTCAGCAGGATCATAGGCATCACAAACTTTGACCTGCTGGGTGATTTTGGAGCCATCGAGTGGTTGGGAAACTTCCAGATTGTA
TTGCTTTACAATTTGGTTTTTGGAACCACAACTGCCCTGTGCTTGGCAAACAAATTCACGGCTACGGTGCGCCGGGAGCTAAGAGCCCGGTTAGT
GGAGAACTATGTGCTCTTTACTAACTACATTAGCTTCATCAACTGATATTGGCGCAAGCGACACGACAATGCGTTTTGTATAAACCGACAGGAGG
TGAGGCGCCTTGTCGAGTCGCCGCTAAAGAGCCTAACAAGTTTCTATACCAAGTATCGTAACCTTAGTCGTAAGAGCAGTCGCAATACCACCGCT
AGTCGCAAGGCAAACGAAATGAACTGTTAAGACACGAGAAAAACATGGGAGATGGGCAGCTGAAACTATATAATATACCTTTACATATGTTATAT
GATCACGTATAGTTGTGCAGAACTGATACTAATATTTAAATTTTGCAATGTTAACTGTTGTGCTTAATTGTTGTACTTTATACAGACAGAGTCCT
CACAGTGCACCAGCATATCACTGTGGTGCCAGTAAACACAGAACAATGGCACTCGTGTACCATGATATTCGCAGAAATCTCGCCAATAACTAGCA
TGTAAATAGAAGATGTAATTGTGCAACATAAGCCGCAGTCAATTTGCAGTAGGCGTAGTTTAGAATTTCGTTTCTTGTCGTTCAGAGTGAATTCC
ATTTCATACATGTTTTTCGCTATTTATCCACGTATATTTCAGTTATTTTTATAAGATTTTAACAATGTTCCTTAAGCAGCGAAACGATGAGGCGT
GTTCATTTCATTTTACGGCATACTCAAATCTGTAACCCAATATTCACACAATCACACACTAACAAGCGTCTAAAACTTATGTGATAAAAAATAAT
AATAAACAAAGCATTTTACTAAATTAATCG (SEQ ID NO: 644)

Start ATG: 363 (Reverse strand: CAT)

MDEEEEEEVTDLKLQLFHNTVREHIIFLLLIILLYSSSYVVVSRFRRRDRDDLYSNDEDEVLVYRISFWLCTFTLAVAEGAAMLLPVSIASNEVL
LLYPNSYYVKWLNSSLIQGLWNHVFLFSNLSLFIFLPFVYLFSESTGFVGNKKGILPRVYETFTVFMLMAIIVLVLTAVLSAVFGIEKLQFFWFL
NLGSVHLPFLYSCVSFLGVMLMLICTPYGFVRLFGVVNQVLVRPMLLRDVNEEFSAFYMEEASVKRKLAHIELHNVSIADAANGGRLGNRIGLGR
GRTFYPQPLLQHSQAHLYQRKAMASDVDELNDRLRELDSERKELDKLRTSSTFQRTFVYPLAMLLLLFCTAVTILLVVQNTLELLIGIKALPLST
RQFALGISSLSKLGPFGAGLEVCLIFYLGATSVVGFYSMPFMRKVCPKRRQTSLPQLMLNCGFMLVLSSALPLLSRIIGITNFDLLGDFGAIEWL
GNFQIVLLYNLVFGTTTALCLANKFTATVRRELRARLVENYVLFTNYISFIN*
(SEQ ID NO: 645)

Classification: known_flybase_gene
Gene Symbol: BcDNA:GH12663
FlyBase ID: FBgn0027539

Celera Sequence No. : 142000013384830
CTCCTCCTCCTTACCGTGGTCGCGCATCGAGTTGCGCCCCATAACCACCATTTTGCACATAGTCTCTTCCTGCAGCTGCCGCAGTGTGTTGCCCT
TGGGCCCCAGGATCTTGCCAACGAAATTGAACTTGGGGTACTCCTTGATGGGGAACAAGACTTTCTGGGCCACGCGGATGGGCTTTTCGCTGTAC
ACGTTGGCATATATCTCGGGCTTTGGTATGCGTCCGCTGACCAAGATCTTCTCCACCTCTGCGGGGCCATGAAAAATTGCAATTAGATCCACTAT
AGCTTACATGTCGCAGCGCCTAACTCACCGTCGTCAAGTAAGCGCTTGGTGATGATGTGCTTCTTCTCGAGCGTCTTCTTTTCCAGCAGGCACTC
CTGCAGATACGCGTTGGTCTTCTCATTCAGCTGGGGCGTGTCCCGCAGGGCGGCGTGGCTGGTGGTGTGTCCGCCGCCATCCGCCTCAGGGGTCT
CTGGAGCACCGGTAGCCGCTGGCTCCTCGTCGCGTCGCTTCCGCTTGTAGTCGGCGGCGTCCTCGTTGTAGTCTCTGTCGTAGTCGCGCGGCATT
GCGTTTTGTAGGATTTCTGGCCTGGAGGATTCGTGAATTTTAAAACTCCTACTCTTGAATACAAAATTCTACTATTGCAGAATTAGTTGGCTGAA
AAAATATGTATGTGGTAGGACATCGATAGGTAAATCGGCATCACCGATTCGATAGCGTATTATCGGTTACTGCCGATAACAACCCGCCATCATGT
GCATTAGTAGTTTATGACTTATCAATTTTATTAAAAACTTTCCCATAACAAAGAGAGCATTTAAATTATATTTGTAATTTAAAAATCACTAAGTG
CATATTATAAATTATTGCCATGCACCTGACGACGCATCTATGTTAATATATAGCGTTAGATAGTGTCTGCAAGCCGATAACAACTATGCGCCCTT
AACAGCACCGTCGATTGGCAGCGAACAGCACGCTGCAGAAGCACGAGAGACAGCCCGAGAGACCGGAGTTGCCGGACCGAGCCGCTGACATAGTA
AATGTCCGAATAAAATACACACTTGGAAAAAGAGAGAAAAATTAGGGCCATTGGGAAGGCTGAAGTGTGCTAAGTTAGCAATCATACCGAATCGA
CAGCAAAAGCGATCGCCCGCAATCTGCGCACGGAAAATCCGAGACTCGGCGACTTAGCAGGACGATAGAGCGACAGCGATCCCGAAGGCAGGACG
ACAAATGGCGGAGAACGGACTGCGCGTGCCAGGGTCATCCGCGGTGGCCTCTGCGGTGGCTTCCACTGCGACGGGAGTCGGCGGTGGATCAGCAG
CGGGAACTGCGGGGGCCGGGACAGGAGTGGTGCCCACCGGCGTCAGCGGCGGGACGAGCAACGGGGAGCATGAGAACGAACACAACGCCAACGCA
GACGGCGAGAAGGCCCAGCCGGCGCCGGCGGTCCAGAAGTACATGCAGGAGCTCATGACGGAGCGATCGCGCATGGAAAACCACTTCCCCCTGGC
GGTGAAGCTAATTGACGAAGGTAAATTGATTTGTCAGGGGCACTTCATGGTAATTACTTTGATTTCCCTCTGTTTTTGCAGCTCTGGAGCGTGTG
CAGCTAAACGGACGCATTCCCACGAGAGACCAGTACGCCGATGTCTACCAGCAGCGCACCATCAAGCTGTCCCAAAAAGTGCACGTGCCCATCAA
GGACAAGAAGTTCAACTATGTGGGCAAGCTACTGGGGCCCAAGGGCAACTCACTGCGTCGCCTGCAGGAGGAGACGCAGTGCAAGATCGTCATAC
TTGGTCGCTTCTCAATGAAGGATCGCGCACGTGAGGAGGAGCTGCGCAACTCCGCGGACGCGAAGTACGCCCACCTGAATCTTCCTCTGCACGTC
GAGGTGTCCACCATTGCTCCGCCCGCCGAGGCGTACGCTCGGGTGGCGTATGCCCTGGCCGAGATTCGGCGGTACCTCACGCCGGACAAGCACGA
TGACATCCGCCAAGAGCAGTACCGCGAACTCATGGAGGATCCGGAGGCGGCCAAGAAGCTGACGCTTCGCCAGCTGCAACAGCAGCAGTCGAATGCGG
CAGCTAGTGGTGCAGGAGGAGGAGGCGGTGGTGGAGGCGGAAACGGAAATGGCGGCGCAGCTGGATCCGGCAGCAATAATGGCAATGGGAACCAG
CGCTCCGGCGGCAACTACAGGTGGGTTGCAGTTCAATGTCCTCTACGAGCCTCGAGTCTAGCTAAACTCCCATGTTTCTTACAGACAAAAGTTTC
AGCAACAATCACACTATCGCCACAACGAGGAGACTGTCTATTTTCGCTCACACAACAATGCGTACCACCAGCCAAAACCCTATGTGCCAGGTAAG
TCTGGGCTCTCCTGGTCCATAGACCATAGATTCTATGTTCGCTTTTGCAGCCGCCCAACGGGGCAATGCCATGCACACCACCTTGCCACCGCAAG
CAATTGTGCGAGCCTCACCGCCCGGAATGGTCGTCAGTGCGGCCAGCTTCAATGGCCGAAATGCCGGACTGGGTAATGCCGGCGGTGGCGGAATC
ATGGCCAATAGCATCGTGGCCACCACTGGCGGTGGCATCGGTGGCGCTGTGCCGCCTAACATGCGTTACCGTCCCGCTGCCCCCTACCAGTTTGT
CAAGAAATAATACAGATGGGAGGATGCACCGCCCGCTGCCGTTCGCTGTTTGTTCAACTATTCCTCACCATCATTGATGCCTCATCCGGAAGTAT
TCACGCCCATCTGTCATACCCATCCAAACACCCACAACCACACACAGCTCCAAAGGTAGATGTAGTAACTATGAGAACATTGGAAACTTGTCATG
CATTGATTTCATCAAGATTTCGGCAGGGTGGAAACCAAAACGAAACGAATGAGTAAATCTATGTTTAAGAAAACTAGCCTAAGTAGACAAATGCT
CCGAGGAACAGACGAACACCTCAGCCACCCAACCAAAACCAAAACTAACCGACCAGACAAACACCCACCACCCCACACGCACGCAACCTCTTCTC
GAGGATTGGGTTCGAAGGATCACGAGGGTCTGCGATCTAAGACTTTGGAATCCGTGTGTTGGGCCCTGCGAGCATTTGGAAGAGAAGAATTGAAG
AAGAAGAACGAGGAGGAGGTGGAGAACGCCTCGATGTTGGATCGGGCCGAATCGAATGGACGCATTCAAGGTTGGTCCCAGTCGAGCCAAATGTC
CTTGTTTTGTTTTGTCGCATATTATTAACATTTTAATTTTACCACTGACGCGTGCGAAGATTTCATCACTTTGTAATTTATATAAATGAATATAT
ATATCTCCTTATGCTTACTATCATACGTATCCTTCTCGCAGTCGCTTTAACTCTATTGCTTTTCCAACTCTGCGTTTAAGTTTATCCCATTTTTT
GTTGTAATGCGTTTTGTATTATGTTTACGTTTAGAAGAGGAGGCTTCTTATTTTTATTTGTTACGTCGCCAGGACAGAAAAAGCAACTGCAAACG
ATCATGAATAATATATATAACAAGTATATACAAGCGGTATGATTTATAACACATAGTGCATATGCAACACCACACGATCATACGCGCGTACGCAT
ATTCAAAACATCAGCATATTCACCTAAAGCCGTAAAGTTTAAACCAAATGAACATTAGAA
(SEQ ID NO: 646)

Exon: 1001..1540
Exon: 1602..2205
Exon: 2270..2370
Exon: 2426..2670
Start ATG: 1240

Transcript No. : CT18271
CAGCCCGAGAGACCGGAGTTGCCGGACCGAGCCGCTGACATAGTAAATGTCCGAATAAAATACACACTTGGAAAAAGAGAGAAAAATTAGGGCCA
TTGGGAAGGCTGAAGTGTGCTAAGTTAGCAATCATACCGAATCGACAGCAAAAGCGATCGCCCGCAATCTGCGCACGGAAAATCCGAGACTCGGC
GACTTAGCAGGACGATAGAGCGACAGCGATCCCGAAGGCAGGACGACAAATGGCGGAGAACGGACTGCGCGTGCCAGGGTCATCCGCGGTGGCCT
CTGCGGTGGCTTCCACTGCGACGGGAGTCGGCGGTGGATCAGCAGCGGGAACTGCGGGGGCCGGGACAGGAGTGGTGCCCACCGGCGTCAGCGGC
GGGACGAGCAACGGGGAGCATGAGAACGAACACAACGCCAACGCAGACGGCGAGAAGGCCCAGCCGGCGCCGGCGGTCCAGAAGTACATGCAGGA GCTCATGACGGAGCGATCGCGCATGGAAAACCACTTCCCCCTGGCGGTGAAGCTAATTGACGAAGCTCTGGAGCGTGTGCAGCTAAACGGACGCA
TTCCCACGAGAGACCAGTACGCCGATGTCTACCAGCAGCGCACCATCAAGCTGTCCCAAAAAGTGCACGTGCCCATCAAGGACAAGAAGTTCAAC
TATGTGGGCAAGCTACTGGGGCCCAAGGGCAACTCACTGCGTCGCCTGCAGGAGGAGACGCAGTGCAAGATCGTCATACTTGGTCGCTTCTCAAT
GAAGGATCGCGCACGTGAGGAGGAGCTGCGCAACTCCGCGGACGCGAAGTACGCCCACCTGAATCTTCCTCTGCACGTCGAGGTGTCCACCATTG
CTCCGCCCGCCGAGGCGTACGCTCGGGTGGCGTATGCCCTGGCCGAGATTCGGCGGTACCTCACGCCGGACAAGCACGATGACATCCGCCAAGAG
CAGTACCGCGAACTCATGGAGGATCCGGAGGCGGCCAAGAAGCTGACGCTTCGCCAGCTGCAACAGCAGTCGAATGCGGCAGCTAGTGGTGCAGG
AGGAGGAGGCGGTGGTGGAGGCGGAAACGGAAATGGCGGCGCAGCTGGATCCGGCAGCAATAATGGCAATGGGAACCAGCGCTCCGGCGGCAACT
ACAGACAAAAGTTTCAGCAACAATCACACTATCGCCACAACGAGGAGACTGTCTATTTTCGCTCACACAACAATGCGTACCACCAGCCAAAACCC
TATGTGCCAGCCGCCCAACGGGGCAATGCCATGCACACCACCTTGCCACCGCAAGCAATTGTGCGAGCCTCACCGCCCGGAATGGTCGTCAGTGC
GGCCAGCTTCAATGGCCGAAATGCCGGACTGGGTAATGCCGGCGGTGGCGGAATCATGGCCAATAGCATCGTGGCCACCACTGGCGGTGGCATCG
GTGGCGCTGTGCCGCCTAACATGCGTTACCGTCCCGCTGCCCCCTACCAGTTTGTCAAGAAATAA
(SEQ ID NO: 647)

Start ATG: 240

MAENGLRVPGSSAVASAVASTATGVGGGSAAGTAGAGTGVVPTGVSGGTSNGEHENEHNANADGEKAQPAPAVQKYMQELMTERSRMENHFPLAV
KLIDEALERVQLNGRIPTRDQYADVYQQRTIKLSQKVHVPIKDKKFNYVGKLLGPKGNSLRRLQEETQCKIVILGRFSMKDRAREEELRNSADAK
YAHLNLPLHVEVSTIAPPAEAYARVAYALAEIRRYLTPDKHDDIRQEQYRELMEDPEAAKKLTLRQLQQQSNAAASGAGGGGGGGGNGNGGAAG
SGSNNGNGNQRSGGNYRQKFQQQSHYRHNEETVYFRSHNNAYHQPKPYVPAAQRGNAMHTTLPPQAIVRASPPGMVVSAASFNGRNAGLGNAGGG
GIMANSIVATTGGGIGGAVPPNMRYRPAAPYQFVKK*
(SEQ ID NO: 648)

Name: KH domain RNA-binding protein
Classification: RNA_binding
Gene Symbol: qrk58E-2
FlyBase ID: FBgn0022985

Celera Sequence No. : 142000013384530
TAATTAGATACAAAAGGATAGGACGTTAAGGATTTCATCATATAATCGCCAAATTTCCTAATTCATTTCCTAGGCCTGGCCAAACCCAATACCCT
GATAGCCAGCGTCCATCCGGCAGATAAGCTCTCCCTGCAGTCCTTTCAATCCCTGGGAGTGGAAACAGTGATCAAGAATGCACCCGTTGTGCAGC
AATCGGATGTGGTCTTCGTGTCCGTGAAACCCCAAGTGGTTCCCTCGGTTTTGTCGGAGATTCAGCCATTGAGCTCGGGCAAACTATTCCTTTCC
GTGGCCATGGGCATCACTTTGTCCACCATCGAGTCCAGTTTATCTCCACAAGCTCGCGTCATCCGTGTGATGCCCAATCTGCCGGCTGTCGTGTG
TTCCGGTTGTTCGGTTTTCGTTCGCGGATCCAAGGCCACAGATGCAGATGCGGATATTACCCAGAAGCTGCTGCAGTCCGTGGGCACTTGTGAGC
CGGTGGATGAGTCCCAGTTGGATGTGGTTACTGCTCTGAGCGGAAGTGGACCGGCCTATGTATTCGTGATGATTGAGGCCTTGGCGGATGGAGCC
GTTCACATGGGCATGCCCAGGGATCTGGCCTATCGTTTGGCATCGCAAACAGTCCTGGGCGCAGGTCACATGGTGCGGGACAGTGGTATGCATCC
CGGACAACTCAAGGATGGGGTCACAAGTCCGGCGGGATCGACAGCAGCGGCACTCAGACAACTCGAGCTGTCAGGTAAGTTGGGATGATGACGCC
GATGACGCACTCGCTTATCGCCGCCACTTCAACCTTTGATGTCGATTGCAGGTTTTCGGGCTGCGGTGTCTGGAGCGGTGGAACAGGCGACTCTG
CGATGCCGGCAAATCTCGGGAAAGACGAAGTAGGCACATAGGATTATCATATACATATACGTACATTGGGGTGGGTCAATTTTGTTATTAAAGTT
ATAGTAGTTAAAGGAAGTCGTTAAATTTTGTTGCTTCTTGAAGAAACATGTTTTAATTTGGAAATGTATGTTGGTGCTATAGTGCTTTCAAAGA
GCAATGATGAGATGTTTCATTTTAATCGACCCACCCTTGTGCTTAATCTGGGTTAGTAGCTTTGCATAACTATAAAAACTGTGAAGGCCGATTTC
GTGATACTAAAATATAAGCAACACTGCTATATTCTTTACTCTCAGCTTTGTTTATAGTCTAGCTAAAAATAACTAATTCAAAGTCGAGCCTAGAA
CTTCTTCTTCTTTTTGGCCCGGGACAGCTCATTGAGCTCGCCCTGTTGCACGGATGCCTCCTGGTAAATGCGCTTAACCTTCTCGTGGCGCTCCT
TGTCACTGTGGATATGAAATACAATAGATTAGAAAGGAACGGTTAAATTGTAAATGGAACACAAACCTTTGCAGGGTCTGTTTGAGCCTAAGCAT
CTGAACGAAGGACGTATCTCTGCGTATTTCTCGAATGGCACCCTTCTTCTCGCGCTTGATCTTGTGCAGCAGTTTGGCCCGCTCTTCCTTGGCCT
TGGACATCTTGGGACGACGTTTGTCATCGTAAACCGCCTCGAATCGAGGTTCCAGCAGCCTAAGAGCCTTGGGTTTCTTTTCCGCCGGAGCCAAG
GGTTTCATTTTCTGCGCAGCTAGCTTCTCCGCCAGTTCGGTGGCATCCTTGTGGTGCTGATGCACATGCTCGGGGTAAGACTCCAGTGGAAGGCG
GGAGAGTAGTGCCAAAAAGGGTTGGGCCAGGTAGCAGGCACCCACATGCTCTTCCACCAGTTGGAGAGCTTCCTTGATTAGCAGGAGGGAAGTGT
CCAGTGCTCGAACCTTGAAATCTGGAGTGATCGTCTGGGTGACCAAGTCAGTAGGCTGCAGCTGTTGGGGCTCCAACTTCGTGGATTCCGTGTTA
GCTGGAAGTGCTAGGAGCTTGCTCAATGGACCATCACGCTCAAAAGGCGGCGTGATCTCCAACTGTTCCACATCCCTCTTCGGTATGGACATGTG
TACAATGCCCTGCAGGAAGTTGAATACGGCTGGAACCAGTCTCTTGGATTGGGACACAAACTCCAAGACTACGGTGACCAGGAACAAACCCATAG
ATATTTCCTGACGCGTTCGCACTCGTGATCTGGACAGGACGTGTTGTATGAATATAAAGCAAGGAGTGACCACCGGATGGCGGAAATCGGAAGTC
GAGTACAAGTTGGCCACTAGTTTGAAGTACACCAAAGTGTCAAGTGAAGGATACATTTTGTGATTTTTCCTGAACTCTTCGTACTTCTCCTTGAT
CACCTCCAGTAATGTATTGGACATGCGCTCGGGATTCAGTTGCGTTAATTCATATAAGTAAGGCATGAGCTTTGAGAGCAACTGGAAATGTTCTC
GTATGTCCTGCTCGCTGGCATCTTCAAACAAATCCTTCAGATATTGCAGCAAAAATGAGTACAACTTAACCACGTTCTCGCGGTTAACACCTTCC
AGTTTGGGATGATTACATTTTATAATCCTTTCGATAATGATCGCCTTCTGGGCCGTAGCATGCTTGGAGAGCAGCTCCGTAAAGTCCTCGTAGGT
CTTGGGCATCTTGATGGTAAACGGAATACTGGTGTCCAAGGAGGCGGGAATTGTATCCGCAGACTTTTTCGCTTTCTTTTTGCTAGCCTTCGGAG
CTTCTTCTGGCTCTGACTCACTTTCAGATTCCTTGAGATCGCTCAGATTGTCGACCTCTGAATCACTCTCCTCATCCGAGTCCTCCTCTTCCTCT
TCTTCCCCCTCCTTGTCATCGTCATCCTCATTTCGTCTCCCTTCAACACGGCTTCCTTCTTTCCATTGAGATGTGTGCCCAGATTGCCGTCCAA
ATCGTAAGCGAGCGTATCATCTCCCTCGTCATCTTCGCCGGCCAAGAAATAGCCATCATCCAGGTCATCTGCGGATCGGTGCTTGGGTTTGGCAA
CGGAGGCCTCCTCATCCTCCTCGCCATCTGCTCGCATGCGACGAAGCCGTTCGTTCTCGAGCTTCTCCAATCGAGCGGCCTCCTGTTTGGCCAGC
TCGTCGGGATTGATTAGTTTATCCGCGACACTGCCACGCGGCTCGAAGATCATCTCCTTGAGCAGTTTATCGTAGGCATCTGGCGGTGGCTTGGC
ATCCTGCTCATCCTTCGTGACCTTGGCGACCAGCGGCAGCAGAAGCTTATAGTTGGCATCCAGTTTCTCTGTGAGATCATACACTTCGTCCTTCT
CCTTGGCGATTTCGTTCTTTCTTCGTTTTTGTTCAACGATCATCTCATCGATGGCCGCCTGTCTATCCTGGGCAGAGTCTCCCTCTCCGCCAAAA
TGAGCAGCAGCAGTAAAATCGGCTGAAAGAATATGAGAGTTAGTTGTGCGCTTCAAAGTACAATCATTTGGGTATACCATCTAATGCCTCGTCGT
CTAGCTCCTCGTCGTCGGAGCGCTCGTCCCTGTACTGCTCGATCTCCTCCAGAGTTTGTCCCCTGTGCGTCAGTAGTTCGTCGTCGTTGAGGTTG
AACTTCTCCGCTTTCTGGTTGGAGCGCACCTGGGACATCTTTTCGGCCAGGTAGCGGGCATTCATCACGGACTCGGTTAGCTGATCGCCACTCAA
GTGTTTTCCAATTCGGTTATCCTTGAAGCGATTGGTCTTGTGCTTCACGGCAAACTGTTGACCCAATGTCTGCGCTCGTTTCTGCAGAGCCTTGG
CCCGCGACACGCCCGGCATTCCCCTGTCATGCTTGCAGATCCTCCCCAGAATCTTGAACTTCTCCTTGTTCACGTGCACATCGAAGGGATTGCCC
CGCTTGCTGGACTGTGCCGTCGAGTTGTCGAAGGGATTGGCCGACCTGGTTGTCTTTTTGGCGTAAACCGCATCTGCGCTGGCCTTCTTTCCTTT
GGCCACCATTGTTTTATATCGCGTTCTACGGATAAATTAAACCGAGTTCATTTAGCAAAACAAAACACCTCACACGTGCAACCCAATAACGGACT AGCGCGTCTACGAAATGCCGAAATCAGTGTTGGCTAATCCTGCGAATAGTCACGTACAATGGTAATGGGATCAGTTTCAATTTCAACTGTAACTA
CAAATTAATCATAATTTACTGTATAACAATGTATTTTTCCTTGTTAATGTAATTGTAAATCTACAAGGGCATTTAAATATTACACAATTAAAAT
CTTTGTTTTGGTATCTACTTCGAAAAACTATTGTATATTACGAAACACCGGTACATACGCTGTATGATCTGAGTCATTTAACACAACAATTTTAA
GGGTAGACCAAGAAAACGATGCTTCAATTTGAAAATTTTGTAATCGAAGCAATCAAGTTGTACATTTTTGAATGGGTGACTGAATTAGTAGTTAT
ATTGTTATCACATTCTATTTATAATAGCTAAAATGTTAAATCGATAAATATTAGTTTTCGGGGAATTCCTTGGAACCTTATCCGCTGAAATGTAA
CAGTTACCGCTGCTCATCACTAATAGCATGACTTTTCCAGCACTGAACCACGTCGCCATTTTCGTTTCGTTCCTTGCCACAAAAATTTTCACACG
CAACGCCGGATACTGAAAAATTGGTTTTTAAAGCGTGTTAGGAGCTTTTATAACTTTGCGTGGCTACAGTCAGTCAGTTCTTGGTGTGAAGGTGC
TGGAAAAAGCATGAGCGCCACGCCGCCGGACCTACTTTCGTTGGCGGCGTCCCGAGAAGTCTCGGCCGCCGTCGCAGTCGCCGCCTCTGCCAACG
GAGGCAGCGGCAGAAGCGCTGATAAGGAGCGTTCACGTTCCAGAGATCGTGGGCGGGACAAGGATAAGGATCGGGACAAGGACAGGAAGAAGAGG
TGCGTGCGTTGCAGGGAGAATGATTTTGTACCCTTGCCCTTTTAGCTTCCCCTTTTTACTTCCTTTTCCGGTGTACACATTTTTCAACAATGTGC
TTTTATAAAAGCAGAACTTTTATTAACGCCATAGCATA
(SEQ ID NO: 649)

Exon: 3978..3403
Exon: 3347..2806
Exon: 2691..1397
Exon: 1335..1001
Start ATG: 3904 (Reverse strand: CAT)

Transcript No. : CT18277
GGTTGCACGTGTGAGGTGTTTTGTTTTGCTAAATGAACTCGGTTTAATTTATCCGTAGAACGCGATATAAAACAATGGTGGCCAAAGGAAAGAAG
GCCAGCGCAGATGCGGTTTACGCCAAAAAGACAACCAGGTCGGCCAATCCCTTCGACAACTCGACGGCACAGTCCAGCAAGCGGGGCAATCCCTT
CGATGTGCACGTGAACAAGGAGAAGTTCAAGATTCTGGGGAGGATCTGCAAGCATGACAGGGGAATGCCGGGCGTGTCGCGGGCCAAGGCTCTGC
AGAAACGAGCGCAGACATTGGGTCAACAGTTTGCCGTGAAGCACAAGACCAATCGCTTCAAGGATAACCGAATTGGAAAACACTTGAGTGGCGAT
CAGCTAACCGAGTCCGTGATGAATGCCCGCTACCTGGCCGAAAAGATGTCCCAGGTGCGCTCCAACCAGAAAGCGGAGAAGTTCAACCTCAACGA
CGACGAACTACTGACGCACAGGGGACAAACTCTGGAGGAGATCGAGCAGTACAGGGACGAGCGCTCCGACGACGAGGAGCTAGACGACGAGGCAT
TAGATGCCGATTTTACTGCTGCTGCTCATTTTGGCGGAGAGGGAGACTCTGCCCAGGATAGACAGGCGGCCATCGATGAGATGATCGTTGAACAA
AAACGAAGAAAGAACGAAATCGCCAAGGAGAAGGACGAAGTGTATGATCTCACAGAGAAACTGGATGCCAACTATAAGCTTCTGCTGCCGCTGGT
CGCCAAGGTCACGAAGGATGAGCAGGATGCCAAGCCACCGCCAGATGCCTACGATAAACTGCTCAAGGAGATGATCTTCGAGCCGCGTGGCAGTG
TCGCGGATAAACTAATCAATCCCGACGAGCTGGCCAAACAGGAGGCCGCTCGATTGGAGAAGCTCGAGAACGAACGGCTTCGTCGCATGCGAGCA
GATGGCGAGGAGGATGAGGAGGCCTCCGTTGCCAAACCCAAGCACCGATCCGCAGATGACCTGGATGATGGCTATTTCTTGGCCGGCGAAGATGA
CGAGGGAGATGATACGCTCGCTTACGATTTGGACGGCAATCTGGGCACACATCTCAATGGAAAGAAGGAAGCCGAATCTGAAAGTGAGTCAGAGC
CAGAAGAAGCTCCGAAGGCTAGCAAAAAGAAAGCGAAAAAGTCTGCGGATACAATTCCCGCCTCCTTGGACACCAGTATTCCGTTTACCATCAAG
ATGCCCAAGACCTACGAGGACTTTACGGAGCTGCTCTCCAAGCATGCTACGGCCCAGAAGGCGATCATTATCGAAAGGATTATAAAATGTAATCA
TCCCAAACTGGAAGGTGTTAACCGCGAGAACGTGGTTAAGTTGTACTCATTTTTGCTGCAATATCTGAAGGATTTGTTTGAAGATGCCAGCGAGC
AGGACATACGAGAACATTTCCAGTTGCTCTCAAAGCTCATGCCTTACTTATATGAATTAACGCAACTGAATCCCGAGCGCATGTCCAATACATTA
CTGGAGGTGATCAAGGAGAAGTACGAAGAGTTCAGGAAAAATCACAAAATGTATCCTTCACTTGACACTTTGGTGTACTTCAAACTAGTGGCCAA
CTTGTACTCGACTTCCGATTTCCGCCATCCGGTGGTCACTCCTTGCTTTATATTCATACAACACGTCCTGTCCAGATCACGAGTGCGAACGCGTC
AGGAAATATCTATGGGTTTGTTCCTGGTCACCGTAGTCTTGGAGTTTGTGTCCCAATCCAAGAGACTGGTTCCAGCCGTATTCAACTTCCTGCAG
GGCATTGTACACATGTCCATACCGAAGAGGGATGTGGAACAGTTGGAGATCACGCCGCCTTTTGAGCGTGATGGTCCATTGAGCAAGCTCCTAGC
ACTTCCAGCTAACACGGAATCCACGAAGTTGGAGCCCCAACAGCTGCAGCCTACTGACTTGGTCACCCAGACGATCACTCCAGATTTCAAGGTTC
GAGCACTGGACACTTCCCTCCTGCTAATCAAGGAAGCTCTCCAACTGGTGGAAGAGCATGTGGGTGCCTGCTACCTGGCCCAACCCTTTTTGGCA
CTACTCTCCCGCCTTCCACTGGAGTCTTACCCCGAGCATGTGCATCAGCACCACAAGGATGCCACCGAACTGGCGGAGAAGCTAGCTGCGCAGAA
AATGAAACCCTTGGCTCCGGCGGAAAAGAAACCCAAGGCTCTTAGGCTGCTGGAACCTCGATTCGAGGCGGTTTACGATGACAAACGTCGTCCCA
AGATGTCCAAGGCCAAGGAAGAGCGGGCCAAACTGCTGCACAAGATCAAGCGCGAGAAGAAGGGTGCCATTCGAGAAATACGCAGAGATACGTCC
TTCGTTCAGATGCTTAGGCTCAAACAGACCCTGCAAAGTGACAAGGAGCGCCACGAGAAGGTTAAGCGCATTTACCAGGAGGCATCCGTGCAACA
GGGCGAGCTCAATGAGCTGTCCCGGGCCAAAAAGAAGAAGAAGTTCTAGGCTCGACTTTGAATTAGTTATTTTTAGCTAGACTATAAACAAAGCT
GAGAGTAAAGAATATAGCAGTGTTGCTTATATTTTAGTATCACGAAATCGGCCTTCACAGTTTTTATAGTTATGCAAAGCTACTAACCCAGATTA
AGCACAAGGGTGGGTCGATTAAAATGAAACATCTCATCATTGCTCTTTGAAAGCACTATAGCACCAACATACATTTCCAAATTAAAAA
(SEQ ID NO: 650)

Start ATG: 75 (Reverse strand: CAT)

MVAKGKKASADAVYAKKTTRSANPFDNSTAQSSKRGNPFDVHVNKEKFKILGRICKHDRGMPGVSRAKALQKRAQTLGQQFAVKHKTNRFKDNRI
GKHLSGDQLTESVMNARYLAEKMSQVRSNQKAEKFNLNDDELLTHRGQTLEEIEQYRDERSDDEELDDEALDADFTAAAHFGGEGDSAQDRQAAI
DEMIVEQKRRKNEIAKEKDEVYDLTEKLDANYKLLLPLVAKVTKDEQDAKPPPDAYDKLLKEMIFEPRGSVADKLINPDELAKQEAARLEKLENE
RLRRMRADGEEDEEASVAKPKHRSADDLDDGYFLAGEDDEGDDTLAYDLDGNLGTHLNGKKEAESESESEPEEAPKASKKKAKKSADTIPASLDT
SIPFTIKMPKTYEDFTELLSKHATAQKAIIIERIIKCNHPKLEGVNRENVVKLYSFLLQYLKDLFEDASEQDIREHFQLLSKLMPYLYELTQLNP
ERMSNTLLEVIKEKYEEFRKNHKMYPSLDTLVYFKLVANLYSTSDFRHPVVTPCFIFIQHVLSRSRVRTRQEISMGLFLVTVVLEFVSQSKRLVP
AVFNFLQGIVHMSIPKRDVEQLEITPPFERDGPLSKLLALPANTESTKLEPQQLQPTDLVTQTITPDFKVRALDTSLLLIKEALQLVEEHVGACY
LAQPFLALLSRLPLESYPEHVHQHHKDATELAEKLAAQKMKPLAPAEKKPKALRLLEPRFEAVYDDKRRPKMSKAKEERAKLLHKIKREKKGAIR
EIRRDTSFVQMLRLKQTLQSDKERHEKVKRIYQEASVQQGELNELSRAKKKKKF*
(SEQ ID NO: 651)

Classification: hypothetical

Celera Sequence No. : 142000013384574
GTTAACAATGCGGCTATTGGCATTGTCACGAGTTTCTTCCTCAAGTACATGAACTCCATTCTAAAGACCTTCGCGAGCGCTCTGGAGTTGCTCTT
CACGGCAGTCCTATGCTACTTCCTCTTCTCCATACCCATTTACATGAACACCGCGCTGGCCATCGCGGTTGTATCCTACGCCATCTATCTCTACA
CCCAAAGCCCGGTGGTTAATTTGGGCAAGGTGCGTCCGCTGTCCAATTTAAGTGATGCCACGACCAAATCAACGGATAAACGAAAGCTGATCGAC GAGGAAGCGGCAGAATCGGACCTCGATATGGTGTAATGCTGTAGCTTGTCCTAGACGTAATCTTAGACTGTAAATAGTTGTGGAAAAGTGCCTGC
AAATGTTTTAAACGCCAGACGAATGTATTTGACCCCAGGCTTTGTGCAATGCAATAGCAACAGGCTTGTAAATACCAAAACTTTTGCTCCTCTAG
TTTAAGATTCTTATTTTAATCAGAACATAAATGCAATCAAACGAATATTGTGCATGCTTCTTCAAGAAGCTTTTTATTTTATGGTTCATATACTA
TCACATATGTACATGGTATATTTGGATGCCTGCTTGTCTTAGCCTAAAATGGTGTGTCCACATCATGTCCATCTTCCTGTTTGGGCGGTATGCGA
CTACGAAGCGCTATCTGCACCGCCTGGTTTTCGATGCTGCGGAGATAGTAGTCACACTCCTTCAGATGCTTCTCCATGTCCTGGACTCGGTGTGT
GGCGTTGTACTTGCAGGTCTGCAGCGGCGGTCCACAGTAGTTCTTCTCGCACTTAATTAAGTGCTTGGGCATCCGGAAGAGCAAGATGCGGTGCG
ATTTGTCGTAAGGGCAAATTCCGTACTCGAAATCGGACATTTTGAAAAAGTCAAGAGCCGTTTGTCAAAACAACAAATTCATAAAGCTTAAGGTA
CCGCTATGTTTTAAAGTTTTAGTTATCGGTTGTGTTATCGGAAGTAAGGAATTTTCGATTTATTTATTTTTCAAACCAGCTGTCAAGATATTGAC
CTTATACGGAATACCCCCGATGAATATAGGGTCACACTGAGCAGACGCGCGTAAACCACCCCGTCCCTCCCTTTTACTTTTCATTCAGCTTGAAA
ATTTCATAGAGTTCGGTCAATTGTCAAATCTGCTCAAAACCACTTAATTACCAGGTAAACGATGGCACGTACCAAGCAAACAGCCCGTAAATCGA
CCGGAGGCAAGGCGCCCCGCAAGCAGCTGGCCACCAAGGCGGCCCGTAAATCGGCGCCATCCACCGGCGGAGTGAAGAAGCCACATCGCTACCGT
CCTGGAACGGTGGCCCTGCGTGAGATTCGTCGCTACCAGAAGTCCACGGAGCTGCTCATCCGCAAGCTGCCGTTCCAGCGTCTGGTGCGCGAGAT
AGCCCAGGACTTCAAGACCGATCTGCGCTTCCAGTCGGCGGCCATTGGAGCCCTACAGGTATGGTGTACAGCACTCCCTGCACCGTGACTATTTC
ATACGGTCATGTAATAATGCGTCTCTCCCCCATTTCAAATGCGCAATTTGCAGGAGGCCAGCGAGGCGTACCTGGTCGGTCTGTTCGAGGACACC
AATCTGTGCGCCATTCACGCCAAGCGCGTCACCATTATGCCCAAGGACATCCAGCTGGCCAGACGCATCCGTGGCGAGCGGGCCTAAATGCCCAT
GACCGCCATCTTGGATTGGAAAAGCAGTGGCGGCAAAACTACCAACCCACAGCTGTCGCTTGGAGGGGGGAACTCGGAGCTAGAGGTGGAGGTGG
AGAAGCGGAAAACCAAACCCCCGGCCGCAGCTGCCGCCGCTTAGTACTTAGGTCTATCTATACTTACCGATAAGTAATCAATACACAATGTTCTA
ATAAAATCGAATTCATTTTTGTTTGTAAATGTTTAACCACAAAGGAAAGCGTTCATTCATATATTTTGTTCAGACTGTACATTATTAGTTGTGTC
TCTTAAATTGTAATTGTTGTCTTGCTGTCTCGGCAACAATTGAACATTAATTTGAATGGTTTCGTACAAAAATACATATATTCTATTGTATCATT
TTGTAAAATGAGGTAGACCATGTAGTAAATGCATTCATTTTTCGTTATTCTAGTACATATGTATATCTAGCATGTACTGGAATGAAAAGTATCTT
TAAACTATGTAGATTTCTGTGTGGTGGTGAGCTGCTCCCCTGGAGCCAAGCAGTTGAAGGTCCGGACAAAAACAGGCAGCCTTGTCAGGGAATTT
ATGGGTGAACCGCCCTCGACGAAATCGCTGCCGAAATACAGGGTTTGGCCGAAGGAACTCTGGCCAAATCTGAAGAAGAACAATTCCCTCAGAGA
CATGGTGGTGAAGTTGGGCTGCCTCTGGCTGAACTTGGAACCTTCTGCGAAGTAGGCTTCGTGGACCAAATGGAGCACGACGAGGTACTGGTCGC
GTTGGCTAAGCAAATTATCTTGGGTCCATGCGCTTACACACTCATCGCCGGCGGTAGTAATTTGGTTATCGTCGAACAATTGGAGCATATTGACC
TTATGATGTTTGCAATTAAAAAGATCGAAACTTTTTAACATCTCAAGGCCAAAGCGAATGCCCAAGGGTGTCACTTTGAAGATATCGTGGCTGTC
GGGATCAAATGAAGCATCTGCCAGAAAGTCGTATGCCACATAAATCGTATTTCCATTTTCCTCATACGCAGTTTCGAAGAAGAAATTCGAAATGG
GATATGAATGGAGCATGTATCGCCGGTCTTTGAAGTTCGGTTGGTCCAGTAAGCTTAGTTCGGCACGCGTTCGGTGCTCCAGAACCTTTAGGTGA
GCAGTCGCAAGTTCCTCGTCGTCCGCAAATTCAAGCTCCTTGTAGTATCGGGTTACGAAACGTCGATGGCCCGCCTTTCCCGGCAGATTGCCGAT
GCT
(SEQ ID NO: 652)

Exon: 1001..1483
Exon: 1574..1948
Start ATG: 1202

Transcript No. : CT18281
ATTTCGATTTATTTATTTTTCAAACCAGCTGTCAAGATATTGACCTTATACGGAATACCCCCGATGAATATAGGGTCACACTGAGCAGACGCGC
GTAAACCACCCCGTCCCTCCCTTTTACTTTTCATTCAGCTTGAAAATTTCATAGAGTTCGGTCAATTGTCAAATCTGCTCAAAACCACTTAATTA
CCAGGTAAACGATGGCACGTACCAAGCAAACAGCCCGTAAATCGACCGGAGGCAAGGCGCCCCGCAAGCAGCTGGCCACCAAGGCGGCCCGTAAA
TCGGCGCCATCCACCGGCGGAGTGAAGAAGCCACATCGCTACCGTCCTGGAACGGTGGCCCTGCGTGAGATTCGTCGCTACCAGAAGTCCACGGA
GCTGCTCATCCGCAAGCTGCCGTTCCAGCGTCTGGTGCGCGAGATAGCCCAGGACTTCAAGACCGATCTGCGCTTCCAGTCGGCGGCCATTGGAG
CCCTACAGGAGGCCAGCGAGGCGTACCTGGTCGGTCTGTTCGAGGACACCAATCTGTGCGCCATTCACGCCAAGCGCGTCACCATTATGCCCAAG
GACATCCAGCTGGCCAGACGCATCCGTGGCGAGCGGGCCTAAATGCCCATGACCGCCATCTTGGATTGGAAAAGCAGTGGCGGCAAAACTACCAA
CCCACAGCTGTCGCTTGGAGGGGGGAACTCGGAGCTAGAGGTGGAGGTGGAGAAGCGGAAAACCAAACCCCCGGCCGCAGCTGCCGCCGCTTAGT
ACTTAGGTCTATCTATACTTACCGATAAGTAATCAATACACAATGTTCTAATAAAATCGAATTCATTTTTGTTTGTAAATGTTTAACCACAAAGG
AAA
(SEQ ID NO: 653)

Start ATG: 202

MARTKQTARKSTGGKAPRKQLATKAARKSAPSTGGVKKPHRYRPGTVALREIRRYQKSTELLIRKLPFQRLVREIAQDFKTDLRFQSAAIGALQE
ASEAYLVGLFEDTNLCAIHAKRVTIMPKDIQLARRIRGERA*
(SEQ ID NO: 654)

Name: Histone H3.3A
Classification: DNA_binding
Gene Symbol: His3.3A
FlyBase ID: FBgn0014857

Celera Sequence No. : 142000013385213
ACAATGAGCAGCGGGACCACGATGATGGCGAAGATGACATAGGTGATAATGAGCAGCGGGCGTATCCAGATGCGCCACTCCTCGAAGAAGCGTCT
TACGTCCAAGCTGCACATCTTTGCCTCTGGTGCACTCCTTGGGAATGCTCCTTGAAATGTGCTGTTCACCGGAGTACCTAATATCCGGGTTGATA
TCGTTGATTCGTTGACGTCGACGCCGCCGCCCCGATTCTGTTTTCACTTGGGTTTCCGCTTTCTTCCGCTCCGATCCGCTCTTCTCCGCCAGAAA
TTCTCTCACAGCAGATTACAGGACACGGCGGTGGCACCCACGCTGGAGGCGCATTTTCAGAGATCTCCTGCTGGCAGAGCAAGTTCTTCGATCTA
TTGGTTTCAGTCCTATTGGCAGTAATATCGCGGCTTTCGTGCCCTTCTTTTGTGAGGAATCCAGTTCGTGGGTCGGGTGCCTACGTCTAATTGGT
GTGACCAGCCAATGCGAAATCCGAAATGACTAAAATACAGACTTCCTCCCGGTTTTATATTATTTAAAATTTTTACTATTTGTTTTATTTTAAAG
TTTAAAAGCTATCAGTAAAAAAATTAACTTAATTAAAAAACAAATGTCGAAGATTATTTAGATTTTGTTTGTCGCAGACGAAAAATATGAAAATT
TTCCGATGATTTAAAAAAGGGAAATTTCGAGGGCTGCAGAGTAAAAAAATAAAACATATTTTGAAAATTAAAGAAATATGTCAAATATATAAAGT
AGCTAACTCCAAACCGACTACTAATTGTTTCGTAGTTCAGAAATTTTTTTAATACTGAATTAATTGTAAAATATCTAATTTTAGTTAGTTCAATA
AAACAATTCACGAAAGTTAGATGCATTTTATTTATTTATAAGATTAAAATATCAATTATGTACAACTAAGTTAAGTATTTAATTAGTTCTCTTGA AATGGATATAAGGGGATTTACAAGTGAGCTTGATAAGCGTGATATTTTTTCGTTATGGATTTATTAAACAAATATTCTTAGATTATCTGTTTGAT
TTGAATATATGATGTCAAAATGTTCCCTTAACATTTATACGTCGATAACTTAAGATGTTCCGTGTACGTCCCAAGGCTGTCTTTTGGTTAAAAGT
ACTGCGGAATCGCTATTACTATTTGCCTCGCCCCTGGTAGTCATTTTCATATACACAAGATCGGATTACGTTAAAAGTAATTAAAAAGTATTTGC
ATTATAAGAAACAGTAGTCGCCAGTGCAGACTAATTGTTGTGATGATGAAGAAAGAGGATGGCGTCGATGTGACTACCGGTGAGCATGAATCGCT
TGTTGAAGTCGTATATTTGGTCTCTCAGCGCCTTCTTGAAGCTGAGCGTCACCACGCCGGGCACACTATGGTACAGGCTGGCCAAATCGCGGAGC
GTTCCATAAATGTGTCCCATCTTGAGCCACCACTCGATGGGCGACTCATCCAGCTGAACGACCACCTCGTTGCGATATCGCTTAAGATCGGACTC
CACGCTGCTGTCCGCATCTCGCTTCGGAGGATTTGGTATCTCGTTACTGTCAAACAGCAGTTTCAGACCTACGGGCATTTTCGTTTAGTCCATGG
TTTATGATAATCGATTTAGTTCGATGCACTTACCCAACTTCTTTGGTGCACTGCCGTCCACTACTCTTGGTTCTGACTTAATGGCCACCACGCTG
GAGGTAGCTGCCACTTCGTTGGATTCCCCTTCGCCCACTCCACCAAAGTTAATGTTATACTTATGGGTCAGCATACGAACGGTTCGCTCTAGGTT
GTCAATGGTGGTCAGGCGGTGGAAGCGTGGGTCCAACAATGCAGCAGCGGTCAGATTGTCATTGGATATAACGTGCGCCTGGAGGACACTGGAAA
TGGTCCGCTTCAAATTCATCATTAGGGGATCGTCCTGCTCGGCGATGCCCAACTTCTTGATAAGAATCTTTGAAGTGATTGGCGAAAGCATGCTA
CACAAGGGAATGTCTTCGCCACGCAGCGTGTCCAAAGCAATCTAAAAGATTTCACACAATAAGAAAACTGCTTAAACGTCTCATTTAGCTTGATG
GCTTACCACCAGAGCACTCAGGGCCTCCGTCACCGTCTTGGCTGATATAACCAGGTGATCCATGTCCTCGGACCAAGATATGGACTCGGCAAAGA
ACTTCAATGTTTCGTACAGTGTCCAGGGGAAGTGCTCGTTGTACGTGGGCATGGGCACCTCGGACACCTTGGAGGCAATCTCCGTTGAATGACGC
TGCATTAGGTCCTTCACCTGCTCCAATAAAGTGGCCACCTCTTCGATCTCAAACACACGACGCAAACATTTGTCAATTACCGAAACGTAGCACAG
CGAAATGGGTATATCTGCAATAAAAGATTCATATTCATTAGGAAGTCCAATATTTGATATATATTCTATATAAGGTAAATAATTCTGACTTGCTA
ATGCACTCACTTTTCTCTCGCAGATAGGTGTGCAAAAGGTCCTCTTCCTCGTCGTAGTTTATGATGGCCAGTGTGCAATTGGCCAAATAGAAGTC
GGTCAGCAGATCGTCAAAGACGATGTAGTCGTTGTACTCCACGGTGGCATACAGCATACCGCGAACTGAGTGCGTCTCCTCGTCCAGAAAGTGAT
GGAAGATGCTAAGGAAGCGCCGCTGTTCAACATTCACCCACATCTCAAAGGCGAGAGAGAAGGGCTTCTCGGAGGTGAAATCGCGCGTGATTTCG
CCAATCTCCAGAAACTTGGAGGCGTGCATCTCATTGATCAAAGAGTCGATCTTGTGTGGCTCGGGCATGGCTGCCGAATTGCCTAGGACTTGACG
CAGGAATTCACCAAAACCGGCATCGTACAGAGAATCCACATTGCGCAAATCCTTAATCACAATGTCCGTAAGGGCTTCGGCCAGATTGGCGATGT
TCGCCACGGCGGCATAGCCGCCTTCCTCGTGCTTGATGACACGCCCGTGCATCAGGGCACTCGATGGAGTGGCCACTTTGCGTTTGCGTCCGTAC
TTTGGTTCCATAACTAGGCGCTCCTCCTCCTCTACCAGATTTTCGGCCTCGTCGTAGGTGAAGGGCACCATGGTCTCGTACAGCATGGTTTGCGA
GGAGGCGTCCTCCTCCGCCTGCATGGCCGCAGTTGCCACGGCTGCTTCGTCCAGTTCATCATCGGAAGCGTTATCGTGGTTCCGGTTATTAATGA
ACTCCAGTTTGACCCGCCGCGAGGAAACATTCCGCTTGGACAGCGGTGGATGGGATACATTACGCGGCGTCTTGCGCGGCGGCACATGGATGTCG
TGCTCCTGGCACAGCTCCTTGAACAGATCCTTGTGTCGGTGCTGGAGATGCGCACGCAAATTGGTGGTGTTGCCATGGTTGGTCAGCACCTTGTG
ACACTTAATGCAGACCACATTCTGTTTGGTAATCACCTCATTATTGTCGTTCGAGGGGAATCCAAAGTAGCGCCAGTATACGCTTTTCATCTTGG
GCGAGTACAGTTTGGAAAAATTTAGCTGCGACACATCCTCGTACTTGAGTTCGCCAATGGCCACGGGCGACGCTGGTACCCCTTCGCTCATCTTG
TCTTCTGTGGGGGATTGGGATCTTCTTGTTTGTTTTGAATTAGATTCGACAACGATTGCTGTGCCCAATGCGTGTATTAGCGCGCAATTTCTCGA
TTATAGATAGACGGTTCAATAGTCAATAGTTTTTTATCTGTATCAGAAGTACAGTTCAGAGTTGCCACGCGACACGCCGTCAATCGATAAGGCAA
TAAAACGTTGCTAAATGCTTCAAATGCACTCTCATTTATTTGAGATTATTTTTACAGACTGCTCAAATATGAGAGTCACCGCTTTTTAATTTCAA
TACGTCTGACTGTCGTAAAAAATGCGATTTGTTGAGTATTCTCGCTAACACTGATTGCATCACCAATCGATAGCTGGGGAAATTTCTCGCTCGGC
CGGGGGAATTTCTCTAGGGAAATTTTCGCTTGGCCTACGACGTGAAGTTGGTTGCGATTTCCTTTTTAATTCGTTGTTGGGAAGAAAAGGTGTGT
AAATTTCGTGAGCGTCACGAAATTCAATGAAAATAAAAGATAAACGAAATGCAAATCGAGCCATCGAGTGTGCCAAGTGTGGAGGACACAAGTGG
GCATCATTGACACCCGTAGGCATGAAGAAGTGCTCGGAATTACGGCTTAAACAAATCGAAATTCGCCAGCCACGTGGGCCTGCAGCTTGGTTATC
CCATATATACGAGTTTACAAAGAGACATTGATGTTATTATTGTGTTTTTGCCCTCGTTGCAGCCAATCTAAACCGCCAAGATGGGTAAGGGTAAC
AATATGATTCCGAATCAGCACTACCACAAGTGGTGGCAGCGGCATGTGAAGACCTGGTTCAACCAGCCGGCCCGCAAGGTCCGCAGGCATGCGAA
CCGCGTCAAGAAGGCTAAGGCCGTCTTCCCCCGCCCAGCCAGCGGTGCCCTGCGCCCTGTGGTTCGCTGCCCCACCATCCGCTACCACACCAAGC
TGCGTGCCGGCCGTGGTTTCACCCTGGAGGAGCTGAAGGTAAGTGAAGCCGAAAACATTATCGGAATCCATTGGCCACTAACAAAATCTCTGTTT
ACAGGGTGCCGGCATTGGCGCCAACTTCGCCAAGACCATCGGCATTGCCGTCGACAGGAGGCGCAAGAACAAATCCCTGGAGTCCCGCCAGCGTA
ACATCCAGCGCCTCAAGGAGTACCGCAGCAAGTTGATCCTGTTCCCCATCAACGAGAAGAAGATCCGCGCCGGCGAGTCCTCTCTGGAGGAGTGC
AAGCTGGCTACCCAGCTTAAGGGACCCGTCCTGCCCATCAAAAATGAGCAGCCCGCCGTGGTCGAGTTCCGTGAGGTGACCAAGGATGAGAAGAA
GTTCAAGGCCTTCGCCACGCTGCGCAAG
(SEQ ID NO: 655)

Exon: 3968..2481
Exon: 2389..2097
Exon: 2036..1649
Exon: 1588..1001
Start ATG: 3606 (Reverse strand: CAT)

Transcript No. : CT18313
CTATCGATTGGTGATGCAATCAGTGTTAGCGAGAATACTCAACAAATCGCATTTTTTACGACAGTCAGACGTATTGAAATTAAAAAGCGGTGACT
CTCATATTTGAGCAGTCTGTAAAAATAATCTCAAATAAATGAGAGTGCATTTGAAGCATTTAGCAACGTTTTATTGCCTTATCGATTGACGGCGT
GTCGCGTGGCAACTCTGAACTGTACTTCTGATACAGATAAAAAACTATTGACTATTGAACCGTCTATCTATAATCGAGAAATTGCGCGCTAATAC
ACGCATTGGGCACAGCAATCGTTGTCGAATCTAATTCAAAACAAACAAGAAGATCCCAATCCCCCACAGAAGACAAGATGAGCGAAGGGGTACCA
GCGTCGCCCGTGGCCATTGGCGAACTCAAGTACGAGGATGTGTCGCAGCTAAATTTTTCCAAACTGTACTCGCCCAAGATGAAAAGCGTATACTG
GCGCTACTTTGGATTCCCCTCGAACGACAATAATGAGGTGATTACCAAACAGAATGTGGTCTGCATTAAGTGTCACAAGGTGCTGACCAACCATG
GCAACACCACCAATTTGCGTGCGCATCTCCAGCACCGACACAAGGATCTGTTCAAGGAGCTGTGCCAGGAGCACGACATCCATGTGCCGCCGCGC
AAGACGCCGCGTAATGTATCCCATCCACCGCTGTCCAAGCGGAATGTTTCCTCGCGGCGGGTCAAACTGGAGTTCATTAATAACCGGAACCACGA
TAACGCTTCCGATGATGAACTGGACGAAGCAGCCGTGGCAACTGCGGCCATGCAGGCGGAGGAGGACGCCTCCTCGCAAACCATGCTGTACGAGA
CCATGGTGCCCTTCACCTACGACGAGGCCGAAAATCTGGTAGAGGAGGAGGAGCGCCTAGTTATGGAACCAAAGTACGGACGCAAACGCAAAGTG
GCCACTCCATCGAGTGCCCTGATGCACGGGCGTGTCATCAAGCACGAGGAAGGCGGCTATGCCGCCGTGGCGAACATCGCCAATCTGGCCGAAGC
CCTTACGGACATTGTGATTAAGGATTTGCGCAATGTGGATTCTCTGTACGATGCCGGTTTTGGTGAATTCCTGCGTCAAGTCCTAGGCAATTCGG
CAGCCATGCCCGAGCCACACAAGATCGACTCTTTGATCAATGAGATGCACGCCTCCAAGTTTCTGGAGATTGGCGAAATCACGCGCGATTTCACC
TCCGAGAAGCCCTTCTCTCTCGCCTTTGAGATGTGGGTGAATGTTGAACAGCGGCGCTTCCTTAGCATCTTCCATCACTTTCTGGACGAGGAGAC
GCACTCAGTTCGCGGTATGCTGTATGCCACCGTGGAGTACAACGACTACATCGTCTTTGACGATCTGCTGACCGACTTCTATTTGGCCAATTGCA
CACTGGCCATCATAAACTACGACGAGGAAGAGGACCTTTTGCACACCTATCTGCGAGAGAAAAATATACCCATTTCGCTGTGCTACGTTTCGGTA
ATTGACAAATGTTTGCGTCGTGTGTTTGAGATCGAAGAGGTGGCCACTTTATTGGAGCAGGTGAAGGACCTAATGCAGCGTCATTCAACGGAGAT
TGCCTCCAAGGTGTCCGAGGTGCCCATGCCCACGTACAACGAGCACTTCCCCTGGACACTGTACGAAACATTGAAGTTCTTTGCCGAGTCCATAT
CTTGGTCCGAGGACATGGATCACCTGGTTATATCAGCCAAGACGGTGACGGAGGCCCTGAGTGCTCTGGTGATTGCTTTGGACACGCTGCGTGGC GAAGACATTCCCTTGTGTAGCATGCTTTCGCCAATCACTTCAAAGATTCTTATCAAGAAGTTGGGCATCGCCGAGCAGGACGATCCCCTAATGAT
GAATTTGAAGCGGACCATTTCCAGTGTCCTCCAGGCGCACGTTATATCCAATGACAATCTGACCGCTGCTGCATTGTTGGACCCACGCTTCCACC
GCCTGACCACCATTGACAACCTAGAGCGAACCGTTCGTATGCTGACCCATAAGTATAACATTAACTTTGGTGGAGTGGGCGAAGGGGAATCCAAC
GAAGTGGCAGCTACCTCCAGCGTGGTGGCCATTAAGTCAGAACCAAGAGTAGTGGACGGCAGTGCACCAAAGAAGTTGGGTCTGAAACTGCTGTT
TGACAGTAACGAGATACCAAATCCTCCGAAGCGAGATGCGGACAGCAGCGTGGAGTCCGATCTTAAGCGATATCGCAACGAGGTGGTCGTTCAGC
TGGATGAGTCGCCCATCGAGTGGTGGCTCAAGATGGGACACATTTATGGAACGCTCCGCGATTTGGCCAGCCTGTACCATAGTGTGCCCGGCGTG
GTGACGCTCAGCTTCAAGAAGGCGCTGAGAGACCAAATATACGACTTCAACAAGCGATTCATGCTCACCGGTAGTCACATCGACGCCATCCTCTT
TCTTCATCATCACAACAATTAGTCTGCACTGGCGACTACTGTTTCTTATAATGCAAATACTTTTTAATTACTTTTAACGTAATCCGATCTTGTGT
ATATGAAAATGACTACCAGGGGCGAGGCAAATAGTAATAGCGATTCCGCAGTACTTTTAACCAAAAGACAGCCTTGGGACGTACACGGAACATCT
TAAGTTATCGACGTATAAATGTTAAGGAACATTTTGACATCATATATTCAAATCAAACAGATAATCTAAGAATATTTGTTTAATAAATCCATAA
CG
(SEQ ID NO: 656)

Start ATG: 363 (Reverse strand: CAT)

MSEGVPASPVAIGELKYEDVSQLNFSKLYSPKMKSVYWRYFGFPSNDNNEVITKQNVVCIKCHKVLTNHGNTTNLRAHLQHRHKDLFKELCQEHD
IHVPPRKTPRNVSHPPLSKRNVSSRRVKLEFINNRNHDNASDDELDEAAVATAAMQAEEDASSQTMLYETMVPFTYDEAENLVEEEERLVMEPKY
GRKRKVATPSSALMHGRVIKHEEGGYAAVANIANLAEALTDIVIKDLRNVDSLYDAGFGEFLRQVLGNSAAMPEPHKIDSLINEMHASKFLEIGE
ITRDFTSEKPFSLAFEMWVNVEQRRFLSIFHHFLDEETHSVRGMLYATVEYNDYIVFDDLLTDFYLANCTLAIINYDEEEDLLHTYLREKNIPIS
LCYVSVIDKCLRRVFEIEEVATLLEQVKDLMQRHSTEIASKVSEVPMPTYNEHFPWTLYETLKFFAESISWSEDMDHLVISAKTVTEALSALVIA
LDTLRGEDIPLCSMLSPITSKILIKKLGIAEQDDPLMMNLKRTISSVLQAHVISNDNLTAAALLDPRFHRLTTIDNLERTVRMLTHKYNINFGGV
GEGESNEVAATSSVVAIKSEPRVVDGSAPKKLGLKLLFDSNEIPNPPKRDADSSVESDLKRYRNEVVVQLDESPIEWWLKMGHIYGTLRDLASLY
HSVPGVVTLSFKKALRDQIYDFNKRFMLTGSHIDAILFLHHHNN*
(SEQ ID NO: 657)

Classification: known_flybase_gene
Gene Symbol: Dref
FlyBase ID: FBgn0015664

Celera Sequence No. : 142000013384668
GCGGGAGATGATGCCGGTATCGAAAAGTTTAATCGCCGATTGGTCCGGGTAACGAAGGAGCACGCCAAAGAGGCCAAGGAACTGCTCACACTAAT
GGGTGTGCCCTATGTTGATGCACCGTGCGAAGCGGAGGCCCAGTGTGCCGCTCTGGTGAAAGCTGGAAAGGTTTATGCCACCGCCACGGAGGATA
TGGATGCCCTCACATTCGGATCTACAAAACTGTTGAGATACCTTACCTACAGCGAGGCACGAAAGATGCCCGTCAAGGAGTTCAGCTACGACAAG
CTGTTGGAAGGTCTGGCCATTAACAATCGAGAGTTCATTGATCTATGTATTCTGCTGGGTTGCGATTACTGTGAGAGCATCAAGGGTATTGGACC
CAAGCGAGCGATCGAACTGATCAACACCTATCGGGATATAGAGACTATTCTGGATAACCTGGACTCTAGCAAATACACCGTGCCCGAGAACTGGA
ACTACAAGGTGGCGCGGGAACTCTTCATCGAACCGGAGGTAGCTGATGCCGACTCCATAGATCTCAAATGGGTCGAGCCGGATGAGGAGGGCCTT
GTCAAGTTTCTCTGCGGCGACCGGCAGTTCAACGAAGAGCGCGTTCGCAACGGTGCCAAAAAGCTGATGAAATCCAAGCAGGCCCAGACTCAGGT
GAGACTCGATAGCTTCTTTAAGACACTGCCCAGCACTCCGAATGCCACAAACGCTGCAAAACGGAAGGCCGAGGAAGCAAAGAAGAGCGCCAATA
ACAAAAAGGCCAAGACCAGCGGCGGTGGACGAGGCCGGCGACCCAAGTAGTTCATTCGTGTGTTATCTGGAAAAACGTACAATTCTTTAATCTTA
ACTTAACCGTAAAGCCTATGCATACAATATAAACTACATCTTTGAGCTTAATGCTAGTTGGTCTGCTTGTGGGTGCGGGTGAGGTTGGGATGTTG
GATTATGGATATTGGATTTTGAATTAGAGTTTGGACTGTGGGGCTGCGACTACAGCAAATACTGCTTGGCCAGGGCACGCAGAAATCTCGATTT
CCGCACCATGGCAGATTCTCGTTTGATCTCCTCATTGTTGTTTGCATTCAGCTCCAGAGTGCCCATCATAGAAATCTGTTTTTAAAAATGTTAT
AAAGATAAATGATTACCCGCAAATGAGCACAGAGTAATAGATTCCTACCGCTTCAAGTTTCCGACTGTGTTCGCCTCGCTTAGCGTGCAGATTGA
CGATGAACTCCAGCAGAGTTGTATCCCAGATGCAGCTGTAATATGCATCCATGGCATCGGTGAAATTCGACGATTTCTCGCTGAGATTCTTGAAC
ACAATGCCGTAGTCGATCTCATCAAGGAACTGACACAGAACGGTGGCCTGCATGTGACAGCCCAGATTGGCGGCACATCGAATCATCTTGCGGAT
CACGTAGTCGTCGGCCACATTTCTCTGCAGCGGCATGGTGCAGTAGTCGGTGCCAGTAACCAGCGCATTTACATAGCAACGCATTGCGGACTCAT
TATTGCCGATGGCTAGATCTAGATCGCCTTTCATCTTCAGCCATGAAATGGTTTGCGGATAGTAGGACAAAGCCTCGGAAAGAAGCCATTGCAGG
GTCTCGCAAACGCTCCTCAAACTGTAGCTGACAGGGCTGAAATGAGGATTAAAAGTTATTATTTAAAAAAAAACTATATTACTGTCTGTCTACTC
ACTTGTTAATGCTGGTAGGCCACAGCTGCATGTACTCGCAGCTTAAATCATGATTGGGGTCATCCTTAAGTATGTTGTGGACTTTGCCTATCATG
GAGATGGCGAGTCCGAAAACGCTTTGGTGGCGGATTCGCTGTAGGAAGGCCTGCAGGGAACTGATACCGCCAACTCCTGAGGAGCCACGCTTCGG
AACGTTAAGGAACATGCTTAGCATCAGTTCCCAGGCATCGCGACATACCTTCTTGGGGCCCTTCATCTTCTCCATCTCGATGAAGGTGGCGGCGA
AGGCCAGGGGTAGTTCCAGGGGACCCGCCCGTTTATCCAGGTAAAGGAGAGGTGGAAATTCTGTGAGGTTAAGTAGCATGATAGCGCAACTCTCT
AGGATATCCGGACGTGGGACGATTGAATCTCCTGCCTGCAGGGCTCCCAAACATTGCTTGCATCTTCCTCCCAAGGATTGCAGATCGAGTGGCTT
CTGGTGCCACTCCTCCAGGCACTGTGTTATCTGAATGTGCAGGATTTCCCAGGTGATCAGCTTACACATCAGCTGCACATTGGCCGCCATCTCCT
GGCGCTGATTTTCCGACTTCAGTACACTCAGCATTGAAACGGCATCGATGTAGTTGCCCCTTGTGGCCAATTCTCGCGCCTTGCCGAGCAGAACA
TAGCTGAAGTCTTGCAAAAAGCTAACCGGCATGGCCATAATAAGAGTTTTCAGGGGCTGTGGTACGTCCCAACTGGGATTAATGGCCCACAGAGG
TTTTCCAGGAGCAGTTGCGCATAATTTCACTAGCAATATCCTCACTGTGTTGGCATTGGTGCAGCTTATCAGTTGTCGCTCCAGAGCGCCCACGT
CAACCCTGCTCACTAGAAGGGGTAAGTTAAAATATAATAAATGAATTTTGTTACAGGAATGGAGATGCATCTCTTACTCTTGGAGTGACACATCC
AGTCGGAAAGCGAGGCCAACGAGTTGGTGGGCACCGGCGGCGTCGCCTGCAGCATCTGTTCGTCAATATCCTGGAGTTCATCTGACGAGAACAGT
CCAAATCCTCGCACCGTTTGTAGCAACTGTCGTGACTGCCCACCCTGATGAAGCAAACAGTCGATGAGGAAGTGCTTGAGTGCCGCCTGTTCTTT
GAAAGTACAGTGGGGAAGCATTTCCTGCAAAGCCTCCACCAGCGGTGGCAGGCAGTCCAGTTCCCGGTACTTCTCAAAGTACTCAACGCTGCCAA
AGATGCTGCCCCACTCAAAGATGTTTCGCACCACATTCAATGCAGCCACCTGCAATTGCAGCTGAACTGTCTCCTTGAGTATGCCCGTGGAGATG
GAACCCTCAATGTCCAGTTCCACTTGCCGCCGGCTTATAAAGGGGATTTCTCGCCTTCTGTTGTCCATTCGCAGAATTGATACAATGTCTGTGTA
GTTGTTAAGTAGCGATTGCTGGAACTTCTCCAGCAGTGACTGCTCCTCGGCGCTAATTCCACAGGCCTGCAGTAGACCTTCCAGTTCTGACGGTC
GTATGTGGCAGTAATATAGAGTTGTCTGTGGCGGGATTGCCTGCAGATTAGTATTACACGCGGCGGCCGCTTCCCGGGCCAAAACATACTGTTTG
GTGTACAGGTAATATTGGGCGAGCTCGTAGTGCAGTTGGGCTCTCAATTCCTGGGGTGTTATTAGGTGCATAACATCGTAGTTTTGGCCATTGCC
GATATCATCACATCGCAGCGGAACAAAGCTGTCGTAGTGAAATATGTAGAAAGGTTTTGTCGAGGCGCAGAGTTGTTGCAAATACTCGATGGATG
GTTGAGTCGGTGTGTCCAGAAACTGCTGGAGCTGGTCCACAGTTTGGTACCTATAATTAAGCCTTATTTGAGCATTAGAGTATGGATAACTTAAC
CACATCTTACATTGTGTTTTGAGGACGTGGCGCTTTTAACGCCTGCTCCTTTATCAGTTGCATTCGCAGCAGCATGCGGTGGTATATGGTCAAGG
CGAATCTTGCTGCTCTTTCGTTTCCAGCAGCGGCTGAAAGGATTCACAGAGGATATAGAGAAGTATATGTGGAGGCTAGGAATTAACATACAAAT TCTCGCGTCAAAATCATTGGGCAGGGGAATACTTAAGGAGCAGCCGTAGCTTATGGTGCACAGATCGCGCAGCAAGGCCAGCTGCATAATCACAG
GCAGGTTCTTCTCCAATGCATCCAGATCCCACTTCAGCCAAGTGGCTACCTTCAGCTCGAGGATTTTCAGTGCCAACTGCTTGCGGTTCAATTGC
AGGCCCTTCTCCGCGGGCCTTTGTGGGCTATGGGGCATGCCCACTCCGCCGGAGGCAGTGGGCGTTGTCGGCGCAGGGGCACCACCAACCACGCC
GGGAATGGGTCCCGAATTCGATGGCGTCTGGTTTAGATTCTGCAAATCACTGCCAGGCGTCCCCACTGACTCCTGCGCCGTGTTCGGCGTCATGC
TGATGAACTGCACGATCAGCTCCATGGCGCTGGGCTCTATAAATGGTGGGCATGGATTGTAATCTCAATTTGTCGGCCGGATTCCACAAGTGAGT
CGAACATACCGGGATGCGGGCGCTGCAGATGCTGCGTAATCTTGTGCGGATCGAGCAGGAACTCGAACCACAGTACCGTTTCGGCAGCCAGTGGA
ACTGGCTTGGGCTTAAGAGGATCGTCCATGCTAATCCCTGCCAAAATTCACCAATCAAAACAAAAATTAAAGAATGGCGAAGGGAGACCAGCTGG
CTGTGGCTATACAATCGATGTATCTATCGATGGGCGATAGATTCTGTCCGCTTTTGATTTCGATAAATTTGCCAAATAATTTGATTTGTGTTATC
GATACATCCCTGCCAACTCGTTTTATGGACAATTGAAAGTTGGTTTTTGAAGATGCTGTTAAATTGAAATATTTAAATCTTTTTTTAAATAGACC
AGTAGCAGAATGTACTGTTATCTTCTTGAGATTCTTGTTGGCAATTAAAGTTCTCCTTATTCGTTTGGGACACAAAGAAGTATTTCCGCTTTTCT
AAAAAACAATTTTCCTCTTTTTGTTTAGGCATAATTTTACTGTTAATAATAATTATTTAGTTATCCATTTATATATGGGCAATTAACAGCCTTTA
CCTAAAATTTTACAATAATAAATACCCCTTAACCCAAATGAAGATTTCGAAATCCAGCTGTAATAATAAAATATAATACCGAATTTAATGTAGGT
CTAAAGTTTATGAAATAGTTTTTACTTCTTTCATTTAGTTTATATGTTTGTTTTATTTTATCCATACTTCATTAGTACCATAAAATGTTTAAC
TCCATCTCCTTTGCACATTGATCGGAAAAACACAAACAAAAACGACCAAAAGGGGAGTACCTAATCATTTCAATATGCCTAAGACTATTTTATTG
TTGTTCATTAAAAATGTAAAATAGCCTCAAAAACTTTTTGGTTAATTTATGCAAATATTCTGTTTGTTGTATATCGAGTCAGGTGCTCTAGAGTT
GGGTTATCTCTCTCTTTCAGTTTGATTTCGATGCAGACACTGAAAGAAATCTATTACAAAATTGTATAGTTTATAGTTGATGTTTTGCGGAATGT
TCATGGGTATTTTTTTCCACTGTAAGTTCCTCTAAGTTTATTGTACACCCTTTTTTTAGATGGTGATCTTTATGAGCATTTCTCGACTCCATAAT
CTGAATCTTAAATAAAATATTTAACGTTCAATCAGGTGATTTTATGCAAATTACAC
(SEQ ID NO: 658)

Exon: 4471..4285
Exon: 4216..3797
Exon: 3738..3621
Exon: 3565..2643
Exon: 2577..1713
Exon: 1651..1189
Exon: 1120..1001
Start ATG: 4399 (Reverse strand: CAT)

Transcript No. : CT18357
CCACAGCCAGCTGGTCTCCCTTCGCCATTCTTTAATTTTTGTTTTGATTGGTGAATTTTGGCAGGGATTAGCATGGACGATCCTCTTAAGCCCAA
GCCAGTTCCACTGGCTGCCGAAACGGTACTGTGGTTCGAGTTCCTGCTCGATCCGCACAAGATTACGCAGCATCTGCAGCGCCCGCATCCCGAGC
CCAGCGCCATGGAGCTGATCGTGCAGTTCATCAGCATGACGCCGAACACGGCGCAGGAGTCAGTGGGGACGCCTGGCAGTGATTTGCAGAATCTA
AACCAGACGCCATCGAATTCGGGACCCATTCCCGGCGTGGTTGGTGGTGCCCCTGCGCCGACAACGCCCACTGCCTCCGGCGGAGTGGGCATGCC
CCATAGCCCACAAAGGCCCGCGGAGAAGGGCCTGCAATTGAACCGCAAGCAGTTGGCACTGAAAATCCTCGAGCTGAAGGTAGCCACTTGGCTGA
AGTGGGATCTGGATGCATTGGAGAAGAACCTGCCTGTGATTATGCAGCTGGCCTTGCTGCGCGATCTGTGCACCATAAGCTACGGCTGCTCCTTA
AGTATTCCCCTGCCCAATGATTTTGACGCGAGAATTTCCGCTGCTGGAAACGAAAGAGCAGCAAGATTCGCCTTGACCATATACCACCGCATGCT
GCTGCGAATGCAACTGATAAAGGAGCAGGCGTTAAAAGCGCCACGTCCTCAAAACACAATGTACCAAACTGTGGACCAGCTCCAGCAGTTTCTGG
ACACACCGACTCAACCATCCATCGAGTATTTGCAACAACTCTGCGCCTCGACAAAACCTTTCTACATATTTCACTACGACAGCTTTGTTCCGCTG
CGATGTGATGATATCGGCAATGGCCAAAACTACGATGTTATGCACCTAATAACACCCCAGGAATTGAGAGCCCAACTGCACTACGAGCTCGCCCA
ATATTACCTGTACACCAAACAGTATGTTTTGGCCCGGGAAGCGGCCGCCGCGTGTAATACTAATCTGCAGGCAATCCCGCCACAGACAACTCTAT
ATTACTGCCACATACGACCGTCAGAACTGGAAGGTCTACTGCAGGCCTGTGGAATTAGCGCCGAGGAGCAGTCACTGCTGGAGAAGTTCCAGCAA
TCGCTACTTAACAACTACACAGACATTGTATCAATTCTGCGAATGGACAACAGAAGGCGAGAAATCCCCTTTATAAGCCGGCGGCAAGTGGAACT
GGACATTGAGGGTTCCATCTCCACGGGCATACTCAAGGAGACAGTTCAGCTGCAATTGCAGGTGGCTGCATTGAATGTGGTGCGAAACATCTTTG
AGTGGGGCAGCATCTTTGGCAGCGTTGAGTACTTTGAGAAGTACCGGGAACTGGACTGCCTGCCACCGCTGGTGGAGGCTTTGCAGGAAATGCTT
CCCCACTGTACTTTCAAAGAACAGGCGGCACTCAAGCACTTCCTCATCGACTGTTTGCTTCATCAGGGTGGGCAGTCACGACAGTTGCTACAAAC
GGTGCGAGGATTTGGACTGTTCTCGTCAGATGAACTCCAGGATATTGACGAACAGATGCTGCAGGCGACGCCGCCGGTGCCCACCAACTCGTTGG
CCTCGCTTTCCGACTGGATGTGTCACTCCAAGATGAGCAGGGTTGACGTGGGCGCTCTGGAGCGACAACTGATAAGCTGCACCAATGCCAACACA
GTGAGGATATTGCTAGTGAAATTATGCGCAACTGCTCCTGGAAAACCTCTGTGGGCCATTAATCCCAGTTGGGACGTACCACAGCCCCTGAAAAC
TCTTATTATGGCCATGCCGGTTAGCTTTTTGCAAGACTTCAGCTATGTTCTGCTCGGCAAGGCGCGAGAATTGGCCACAAGGGGCAACTACATCG
ATGCCGTTTCAATGCTGAGTGTACTGAAGTCGGAAAATCAGCGCCAGGAGATGGCGGCCAATGTGCAGCTGATGTGTAAGCTGATCACCTGGGAA
ATCCTGCACATTCAGATAACACAGTGCCTGGAGGAGTGGCACCAGAAGCCACTCGATCTGCAATCCTTGGGAGGAAGATGCAAGCAATGTTTGGG
AGCCCTGCAGGCAGGAGATTCAATCGTCCCACGTCCGGATATCCTAGAGAGTTGCGCTATCATGCTACTTAACCTCACAGAATTTCCACCTCTCC
TTTACCTGGATAAACGGGCGGGTCCCCTGGAACTACCCCTGGCCTTCGCCGCCACCTTCATCGAGATGGAGAAGATGAAGGGCCCCAAGAAGGTA
TGTCGCGATGCCTGGGAACTGATGCTAAGCATGTTCCTTAACGTTCCGAAGCGTGGCTCCTCAGGAGTTGGCGGTATCAGTTCCCTGCAGGCCTT
CCTACAGCGAATCCGCCACCAAAGCGTTTTCGGACTCGCCATCTCCATGATAGGCAAAGTCCACAACATACTTAAGGATGACCCCAATCATGATT
TAAGCTGCGAGTACATGCAGCTGTGGCCTACCAGCATTAACAACCCTGTCAGCTACAGTTTGAGGAGCGTTTGCGAGACCCTGCAATGGCTTCTT
TCCGAGGCTTTGTCCTACTATCCGCAAACCATTTCATGGCTGAAGATGAAAGGCGATCTAGATCTAGCCATCGGCAATAATGAGTCCGCAATGCG
TTGCTATGTAAATGCGCTGGTTACTGGCACCGACTACTGCACCATGCCGCTGCAGAGAAATGTGGCCGACGACTACGTGATCCGCAAGATGATTC
GATGTGCCGCCAATCTGGGCTGTCACATGCAGGCCACCGTTCTGTGTCAGTTCCTTGATGAGATCGACTACGGCATTGTGTTCAAGAATCTCAGC
GAGAAATCGTCGAATTTCACCGATGCCATGGATGCATATTACAGCTGCATCTGGGATACAACTCTGCTGGAGTTCATCGTCAATCTGCACGCTAA
GCGAGGCGAACACAGTCGGAAACTTGAAGCGATTTCTATGATGGGCACTCTGGAGCTGAATGCAAACAACAATGAGGAGATCAAACGAGAATCTG
CCATGGTGCGGAAATCGAGATTTCTGCGTGCCCTGGCCAAGCAGTATTTGCTGTAG
(SEQ ID NO: 659)

Start ATG: 73 (Reverse strand: CAT)

MDDPLKPKPVPLAAETVLWFEFLLDPHKITQHLQRPHPEPSAMELIVQFISMTPNTAQESVGTPGSDLQNLNQTPSNSGPIPGVVGGAPAPTTPT
ASGGVGMPHSPQRPAEKGLQLNRKQLALKILELKVATWLKWDLDALEKNLPVIMQLALLRDLCTISYGCSLSIPLPNDFDARISAAGNERAARFA
LTIYHRMLLRMQLIKEQALKAPRPQNTMYQTVDQLQQFLDTPTQPSIEYLQQLCASTKPFYIFHYDSFVPLRCDDIGNGQNYDVMHLITPQELRA
QLHYELAQYYLYTKQYVLAREAAAACNTNLQAIPPQTTLYYCHIRPSELEGLLQACGISAEEQSLLEKFQQSLLNNYTDIVSILRMDNRRREIPF

FIGURE SHEET 356

ISRRQVELDIEGSISTGILKETVQLQLQVAALNVVRNIFEWGSIFGSVEYFEKYRELDCLPPLVEALQEMLPHCTFKEQAALKHFLIDCLLHQGG
QSRQLLQTVRGFGLFSSDELQDIDEQMLQATPPVPTNSLASLSDWMCHSKMSRVDVGALERQLISCTNANTVRILLVKLCATAPGKPLWAINPSW
DVPQPLKTLIMAMPVSFLQDFSYVLLGKARELATRGNYIDAVSMLSVLKSENQRQEMAANVQLMCKLITWEILHIQITQCLEEWHQKPLDLQSLG
GRCKQCLGALQAGDSIVPRPDILESCAIMLLNLTEFPPLLYLDKRAGPLELPLAFAATFIEMEKMKGPKKVCRDAWELMLSMFLNVPKRGSSGVG
GISSLQAFLQRIRHQSVFGLAISMIGKVHNILKDDPNHDLSCEYMQLWPTSINNPVSYSLRSVCETLQWLLSEALSYYPQTISWLKMKGDLDLAI
GNNESAMRCYVNALVTGTDYCTMPLQRNVADDYVIRKMIRCAANLGCHMQATVLCQFLDEIDYGIVFKNLSEKSSNFTDAMDAYYSCIWDTTLLE
FIVNLHAKRGEHSRKLEAISMMGTLELNANNNEEIKRESAMVRKSRFLRALAKQYLL*
(SEQ ID NO: 660)

Classification: known_flybase_gene
Gene Symbol: EG:EG0003.5
FlyBase ID: FBgn0025830

Celera Sequence No. : 142000013384556
CACTTATTGTGAATTTTGTTTAAATGCCTTGGCCTCTTCGCACTTTGCTTTCCTGCCTTTTGTTGTTCTGCTCTATCTTCTTGCTTTTTCACTTT
TCGTGCTCCTCACACGCGTGACTCTGCGGTCGCATTAGGTGGAGCTGCATTTCCCTCGCGGAAACTGCGTCGGTTGTCCTGTGGCGGCCTGCAGA
GGCAGTGCGTCAAAGCGGAGGCTGACCACTCGAATGTCGGGCGACTCGGATTGCAAACTTTTCCATTAAACTCGCGCAGCACTCATCCGCCCTTC
GCGTTGCGATGCGATTTCCGTCGACAGCGGAGCGTCCGTGCGTTCGCAGCAAAGTTTTTTTTCGATTAATGTGACCAGTCGGCGGGGTCTGCGA
TTAGTACTGCCAAGAGTATGGCGCTCTTCGGTTCGGGGGAAAATGCTGAGGACGTGTAAAAACTATCCTACACCGTTCACACTAGCAATGCGATA
TTGTTGTACTGTTGGATTTTCAATGTTTGACATAAGCTTATAGCTAATTGTATATCTTATCACTAAAGTTGGTAAACTGTCGAATTCGAACTATT
AACATTCGTATTTGCCAAAATCAGCTTAGTATAAACACATTGAATAATTTTAATCAATAATTAATTAATGATAATAATAATAATAATAAATTAAT
AATAATAATAATAAAATAATAATATTAACAATGATAATAATTAATTATTACATAATATATAATGTTGTATTTCACATAGCTTAATGAATAAATTA
GAATGGGTACAAACATTTACGGCTTGAAACGCTTTAAATTTACTCAAAGTTCGAAAGTGAACTAAACTTTAGGCTAACAGGTTCGCTTCCCCACT
GCTTGTCCGTTCGAAAAGGTTCGAGTGCGCACTGTCCGCCAGTGGAGTACCGCACCCTGCATTCGCCTCGCACATCTGTCATTTTTTAGTGCCAT
TCAAGTTTCGCTGGCGCTTTCGCGTCGCTTGGTCACTAGTGTCGTTTTCGTAAGTTGTTGGGGTGGGTTAAAATCCGCGCGCAGAGCTATAATTT
TATTCCTGGAAAATCGTCGTTGTCGCTGACCGCGTCGCATTGCAAAGTTACCGTACGCCACCGAAAGTATTAGCCCTTTGTAGCCGGACAACTGT
CAAACGGATTTGACTGACACAAGAGCAGTGATATTAGCAGCGCAACGGAAAGCAATTATACGACATAAAAATGTTCTCACGACCCAGGTAAGCTT
TTCTTTTTCGTTTGGTTTTTTATGCAAGGACTCGCCTCGAAGGATTTGTGTGCGCGTGGGTGTGTGTGTGCCTCGGGCGCAAATTATGTAAGATT
TCACGATGCGGGAGGAGCAACTGCCCCAGCTGGTAGCCCAGTGACCTAGTCACTCGGATCAGACGAGCGGCCGCCAAGGCGTCCGTGTATATATA
CAATATATTCACATAGTATATCATCCCATTTCCCCTTCTCTTTTCCTCCTCCTTTTGCTGCGCAGCTTTCGTTTTCACTGGGAAGCGCTATGTGC
GAGCGAGAGGGATTCCGATTGGGAATCGCACATGGCCTGGCATTGACCCTTCGGCTTCCCTCCCTTTCTCGCACTTGCTGGTCCCGTTCGGTGAA
CAGCTGTTTTCAGAATTTTCACTTTTCCCTTGCAATTGCATAAGCGTTTTCGAACATGCATGTCTTCGTTTTTTGGCTGCCAAACAAGAAACAGC
TGAAAAAAATCAATGGGCTGCAGAGAGAGAAACGGGGTGCTACGTATCATAAGTATATGTGCTTTAATTTTGCTTTTCTTCGGTGGAGGAATATCG
CCGCACATAATTCGTATGAATTTTCTATGATTCACAGTTGGATAGGAAGTACAAATACGAATGTATTCCATTGTTTAGTAGTATTCTAAGAAAAA
AAAAGGAATGGAAAGTTTATCATCATACTTTTACAATCGAAAACATTTTGTTTCCTGTGTAGCGAAAACACAACACCTTCAATACCATGGACATG
GACATATATTCGAAAGATGGTCTGGCGGAATTCTAAATTTAGTGCATATACCGAAAAAATGTGTGCTTTGTTTCGCCGCTGTCAGCGTTTTTCGT
TGCCAAGTTCATCAAGAATGTTTTCAGCTGGTCTGCTATCTTGCCTCTCGTTCCCACGCAAACCGTTAGCCAGAAATTTGGCTAACAAAAAATGG
AAAGACGTAAAGAGTTTAATGAACTTGCCCAGCTTTTTCCTTCAGACTCCAGTTCTTAGGGCTTTTAAGACCCTAAAAATAATTATTGGTAGCAC
TCGGAGTATGGGGGTATCATTTACGACACGCACTTATTCCGTGTATTTGGCTCAGATATGCGAAATTGTTTAGCACTCGACGTGGTGGGGGCTCA
TGTGAGTGCCATTCAAATAAATGGAAAAAATTGACGAGTGATAGCGTTACCTAAACGATAATTATCAACCCAAAGTGCTCGCCTTTTGTCGGTGC
AAGGGATCTCGGGGTTTCCAGCCCGGCGCACGTCACTAACCGGTTTCAACTTGACCAAAATCCAGCAACGACACCGATACCGACCCTCTGCCAAT
CCCAATTCCACTCCCCGCGAGCATGATTCCATCAATGAACCGCAAACACAAATTAGTCACACGCCTCTGTCCCGCGATATTTGCCTCTCTCGTAA
TTAGCACCATCTATTCGAACTGCCAGCTAGCAAAAACCAAACAGCAGGGGTCAAAATTATAGGGTATCTTATAATATATGATCTTCGCTTGGCAC
TTCGATTACAGTAAGAGTGTTGCATAATCAGAACCTGTTTTTAATTAACTGATCTAGTCCGTTGGGGTCCATAATATTGTATATTTTTGTAAGCC
CTTCACTACGAGTTGTTAGTTTTGCAATCTTATCTGGGGGTATTTACGCTTCAAGAACAGAAAAACATTTTCAAGTTCAATGATCCAATTGGTTT
TGTAATTCATTAAATTGATACGATCACAAGTAAGTGCACAGAAAATTACCTACTTTAGTTGTCCCTAGAGAATAAATAATAATGCACTTCAATCC
AAGCTGTAGAACTGAACTTGTAGTTTTTAAATATTTTTTATTCTAAAGAATTTAGATAAGTTATTTATAAGAATTTATTACAAGTTATTAAGATT
CTGAGGATTAGATGCTAGATTTATGACCGCGGCTGTGCATAGATTTTTATCGTGATGTTGCCAGGCCATCCATCCCCCTTATCGCTGGCGCTTTG
GATTCCGGGGGACAGCTGTAAACAATGCGGCTTAGTTTCCTTCTTTTCTGCTTTTCATTTTATATTTTGGCGTGCCCAGCGCGGTGATAAACAAA
AAGCAGCTGATGTCGACCTTGGGCATGGCGTTTTTATTCCATAAATATATGCATATGTGTGTGTTTGTGGGTGGACAGAGGGGGCCCCCCCATTG
CCAGTGGCAATGTCAAGAATGACAGTGGGCCCACCTCAAAGTCAAGGGTTCCCAGGGGGTTCTCCAATTGCCGCGCTGATAAAGTGATTCACGTA
ATGCACTTTTGCAATTTGCAGCTTATGTGGAACTGTGGGCAAATTGTGTCGATGCGGCACTTCAGCAACAGGAAAGACTGCTGTGGCAGCAGCAA
CAGTTCCCACCGCTCGACACTATCATGAGGTGGTGGGCGATATCATCTGCCCGTCTCAGGTGCGCGGCATAGATCACATCCGTGATCCGCGACTC
AACAAGGTAAGGAGCACTAAATTAATTGTGTGACACTTTTGTTTTGTATAAACAAATGCTTTTGTTTCTAGGGCCTTGCCTTTACACTGGAGGAG
CGCCAGACTCTGGGCATCCATGGGCTGCAGCCAGCGCGCTTCAAGACGCAAGAGGAGCAGCTGCAGCTATGCAAGATCGCCGTAAACCGCTACAC
GGAGCCGCTGAACAAGTATCTCTATCTGAGCGATCTGTACGATCGCAATGAGCGTCTGTTCTTCCGCTTCCTATCGGAGAACATCGAGGATCTGA
TGCCCATTGTGTACACGCCGACGGTGGGCTTGGCCTGCCAGCGCTTGGCCTGATCTACCGACGTCCTCATGGTCTGTTCATCACCTACAACGAT
CGAGGACACATCTTTGATGTGATGAAGAACTGGCCGGAGCCGAATGTGCGTGCCATCTGTGTGACGGATGGTGAGCGCATCCTGGGACTGGGAGA
TTTGGGCGCCTGCGGCATGGGCATTCCCGTGGGCAAGCTGGCCTTGTACACGGCTCTGGCCGGAATCAAGCCCCATCAGTGCCTGCCCATTGTGG
TGGATGTGGGCACCAACAACATCGATCTGCTGGAGGATCCCCTGTACGTGGGTCTGCGTCAGAAGCGAGTGGTTGGTCGGGAGTACGACGAGTTC
ATTGACGAGTTTATGGAGGCCGTGGTGCAGCGCTATGGCCAGAACACTCTGATCCAGTTTGAGGACTTTGGCAACCACAATGCATTTAGGTTCCT
GGACAAATACCGCAACACCTATTGCACTTTCAACGACGACATCCAGGGAACCGCCTCCGTGGCCGTTGCTGGGCTCTATGCCTCCAAGCGTATTA
CGGGTAAGTCCTTCAAGGACTACACCTTCCTGTTTGCAGGAGCCGGTGAGGCCGCCATCGGCATCGCCGATCTCACGGTCAAGGCCATGGTGCAG
GATGGTGTGCCCATCGAGGAGGCCTACAACAGAATTTACATGGTCGATATCGATGGTCTGCTGACCAAGAGCCGCAAGGTGGGCAACTTGGATGG
CCACAAAATCCACTACGCCAAGGACATCAATCCGATGTCAGATCTCGCCGAGATTGTCTCCACCATCAAACCCAGTGTATGTTATAACAATTGTT
ATTTCTGATGGAACTTTTGGTAATCCTAAACTAATCAACAGGTGCTTATTGGTGCCTCGGCTGCTGCCGGCATTTTCACACCGGAAATCCTGCGC
ACCATGGCGGATAACAATGAGAGGCCCGTGGTGTTCGCCTTGTCCAATCCCACCAGCAAGGCAGAATGCACTGCCGAAGATGCTTACAAGCACAC
GGATGTAAGTTATTTCATTGGATATTGTAATGACCAACTAATGAGATGATTGAAATGCACAGGCTCGCGTGATCTTCTCGTCGGGCTCTCCCTT
CCCACCGGTCCAGATCGGTGACAAGACCTTCTACCCGGGCCAGGGCAACAATGCCTACATCTTCCCAGGCGTTGGCTTGGGCGTGATCTGCACGG
GTACTCACCACATACCCGACGAAATGTTCCTCATCGCCGCCCAGGAGTTGGCCAACTTCGTGGAGCCCAGCGATATTGAGCGCGGATCGCTGTAT CCTCCGCTGTCGAGCATCCGCAACGTGTCCATGAACATTGCCGTTGGCGTGACCAAATGTGCCTACGATAGAGGTAAGATACCAATAGCATACCA
ATCTTGGTGGAACAGAAAATATAACTAATTTGGATTATTTTTGTAGGCTTGGCATCTACCTACCCTGAGCCACAGGACAAGCGCAAGTGGCTGGA
GAATCAGCTGTACAACTTCAACTACGAGAGCTCGATGCCCGCTTCCTGGGTTTGGCCGCGGATGCCCTACATTAAGACTCGTGATTTAGTCCCCA
CAAAGCTCTATGGAAAACAAAGTGAAAATTAATTTCTTTCTTTATTTTATTCTAGGCGAAGAAAGCCCGCTCATTGCCGCCATCAAATAAAATAG
CATTAATGCGTTCAACTGGTTGATGGCACCGTTCTGTTTTGCATCTAACACACTCTACTACTTCCAAGCGTACACCATCAGCACCAAGCAACAAA
ACAACCAACCGACTACTAACTACCCTAGACTAGATAAATTTCCAGTGCTCACTCTTTTTAAATGTTTGTTAATCGATCCGTTGGCATCGACAGTC
AAACTCAGTCGCAACTAAAAAATGATTAAAATGTTTTTGATATTAAATAATTAGAACACCTAACAAGCTGCGAGGTCAAGGGATCGGTTCTTAAA
TGTATTTTCAAATTGTTTAATAGTATTATGTATGTATGCCATGTTTTTATATATGTAAAAATTATCATGTTATTAATTTTGTGATACCGAAACGT
ACGATACTAAATGACGACATTGACATGACGACTGTGACGGTGACTACGCCTTCGAAAAAGCAATTACGCAGTATTCTATTCTATCCTATCACTAT
CCTATCTGTATTTAATCTATGCTATGTTTATGGTTTGCTGTAACTTAAACACCCGATTGGCTTCGCAATTCCATTCCTCGCCGCTTGCCATAGCT
ATCCCGCATTATAAGTGTACCCCAGCTTCCGATATGATCTGCTGTGTCTACTACTACTACTAACTCTGACGGCGGCATCAAGCGAGCTCTGAAGC
TATACTTATTTATCAAATTCACGCTTAATCACAATCCACCCGAAATTCGACAATTGATTGATTTATCTATTGCTATATGCTCCTTTCGTTCACAC
ACAGAGAGCGAGGAAGTAATGTAAATTATCGATTACCCCCCTACAAACCGACCGCCTAGAACAATTGGCTAGACAGCAGAGCTAACTGGTGAGAA
CAACCCAAACAAGCAAACAACCAAACAACTAAACAGCCAACCATCCAACCGATTCCACATGTAAAACAACTTAACTCGCTGCCGTTAACCACCAC
CAACTATCTAAGTTAGAACATTATGCTTTCTATCGATTAGTTCACTTATATCTGTAGATATATTCGAGCGACGATTATGTTTGTTGTTTAGCCAT
ATCTGATATTTATTAACGCAATTAAGCAGCTTTGTTATAATTTATTGTTAAAAGGTCGAGCCTAATGTATCAGTAACTAGAAAACCTAACCCCTT
ATGATCGATCGGACCGATTCAGCCATTGTACCACTGACTAGATGATGATGATGTGCGATAAACAATAAAACGAAAACACAAGTTAAACACTCTCG
ATCCTTTATGCCAATTGCTTGCTGGAGATCTCTTGAGAT
(SEQ ID NO: 661)

Exon: 1001..1227
Exon: 3537..3711
Exon: 3777..4826
Exon: 4887..5039
Exon: 5099..5393
Exon: 5462..5590
Exon: 5661..5974
Start ATG: 1211

Transcript No. : CT18483
TAAGTTGTTGGGGTGGGTTAAAATCCGCGCGCAGAGCTATAATTTTATTCCTGGAAAATCGTCGTTGTCGCTGACCGCGTCGCATTGCAAAGTTA
CCGTACGCCACCGAAAGTATTAGCCCTTTGTAGCCGGACAACTGTCAAACGGATTTGACTGACACAAGAGCAGTGATATTAGCAGCGCAACGGAA
AGCAATTATACGACATAAAAATGTTCTCACGACCCAGCTTATGTGGAACTGTGGGCAAATTGTGTCGATGCGGCACTTCAGCAACAGGAAAGACT
GCTGTGGCAGCAGCAACAGTTCCCACCGCTCGACACTATCATGAGGTGGTGGGCGATATCATCTGCCCGTCTCAGGTGCGCGGCATAGATCACAT
CCGTGATCCGCGACTCAACAAGGGCCTTGCCTTTACACTGGAGGAGCGCCAGACTCTGGGCATCCATGGGCTGCAGCCAGCGCGCTTCAAGACGC
AAGAGGAGCAGCTGCAGCTATGCAAGATCGCCGTAAACCGCTACACGGAGCCGCTGAACAAGTATCTCTATCTGAGCGATCTGTACGATCGCAAT
GAGCGTCTGTTCTTCCGCTTCCTATCGGAGAACATCGAGGATCTGATGCCCATTGTGTACACGCCGACGGTGGGCTTGGCCTGCCAGCGCTTTGG
CCTGATCTACCGACGTCCTCATGGTCTGTTCATCACCTACAACGATCGAGGACACATCTTTGATGTGATGAAGAACTGGCCGGAGCCGAATGTGC
GTGCCATCTGTGTGACGGATGGTGAGCGCATCCTGGGACTGGGAGATTTGGGCGCCTGCGGCATGGGCATTCCCGTGGGCAAGCTGGCCTTGTAC
ACGGCTCTGGCCGGAATCAAGCCCCATCAGTGCCTGCCCATTGTGGTGGATGTGGGCACCAACAACATCGATCTGCTGGAGGATCCCCTGTACGT
GGGTCTGCGTCAGAAGCGAGTGGTTGGTCGGGAGTACGACGAGTTCATTGACGAGTTTATGGAGGCCGTGGTGCAGCGCTATGGCCAGAACACTC
TGATCCAGTTTGAGGACTTTGGCAACCACAATGCATTTAGGTTCCTGGACAAATACCGCAACACCTATTGCACTTTCAACGACGACATCCAGGGA
ACCGCCTCCGTGGCCGTTGCTGGGCTCTATGCCTCCAAGCGTATTACGGGTAAGTCCTTCAAGGACTACACCTTCCTGTTTGCAGGAGCCGGTGA
GGCCGCCATCGGCATCGCCGATCTCACGGTCAAGGCCATGGTGCAGGATGGTGTGCCCATCGAGGAGGCCTACAACAGAATTTACATGGTCGATA
TCGATGGTCTGCTGACCAAGAGCCGCAAGGTGGGCAACTTGGATGGCCACAAAATCCACTACGCCAAGGACATCAATCCGATGTCAGATCTCGCC
GAGATTGTCTCCACCATCAAACCCAGTGTGCTTATTGGTGCCTCGGCTGCTGCCGGCATTTTCACACCGGAAATCCTGCGCACCATGGCGGATAA
CAATGAGAGGCCCGTGGTGTTCGCCTTGTCCAATCCCACCAGCAAGGCAGAATGCACTGCCGAAGATGCTTACAAGCACACGGATGCTCGCGTGA
TCTTCTCGTCGGGCTCTCCCTTCCCACCGGTCCAGATCGGTGACAAGACCTTCTACCCGGGCCAGGGCAACAATGCCTACATCTTCCCAGGCGTT
GGCTTGGGCGTGATCTGCACGGGTACTCACCACATACCCGACGAAATGTTCCTCATCGCCGCCCAGGAGTTGGCCAACTTCGTGGAGCCCAGCGA
TATTGAGCGCGGATCGCTGTATCCTCCGCTGTCGAGCATCCGCAACGTGTCCATGAACATTGCCGTTGGCGTGACCAAATGTGCCTACGATAGAG
GCTTGGCATCTACCTACCCTGAGCCACAGGACAAGCGCAAGTGGCTGGAGAATCAGCTGTACAACTTCAACTACGAGAGCTCGATGCCCGCTTCC
TGGGTTTGGCCGCGGATGCCCTACATTAAGACTCGCGAAGAAAGCCCGCTCATTGCCGCCATCAAATAAAATAGCATTAATGCGTTCAACTGGTT
GATGGCACCGTTCTGTTTTGCATCTAACACACTCTACTACTTCCAAGCGTACACCATCAGCACCAAGCAACAAAACAACCAACCGACTACTAACT
ACCCTAGACTAGATAAATTTCCAGTGCTCACTCTTTTTAAATGTTTGTTAATCGATCCGTTGGCATCGACAGTCAAACTCAGTCGCAACTAAAAA
ATGATTAAAATGTTTTTGATATTAAATAATTAGAACACCTAACAAGCTGCGAGGTCAAGGGAT
(SEQ ID NO: 662)

Start ATG: 211

MFSRPSLCGTVGKLCRCGTSATGKTAVAAATVPTARHYHEVVGDIICPSQVRGIDHIRDPRLNKGLAFTLEERQTLGIHGLQPARFKTQEEQLQL
CKIAVNRYTEPLNKYLYLSDLYDRNERLFFRFLSENIEDLMPIVYTPTVGLACQRFGLIYRRPHGLFITYNDRGHIFDVMKNWPEPNVRAICVTD
GERILGLGDLGACGMGIPVGKLALYTALAGIKPHQCLPIVVDVGTNNIDLLEDPLYVGLRQKRVVGREYDEFIDEFMEAVVQRYGQNTLIQFEDF
GNHNAFRFLDKYRNTYCTFNDDIQGTASVAVAGLYASKRITGKSFKDYTFLFAGAGEAAIGIADLTVKAMVQDGVPIEEAYNRIYMVDIDGLLTK
SRKVGNLDGHKIHYAKDINPMSDLAEIVSTIKPSVLIGASAAAGIFTPEILRTMADNNERPVVFALSNPTSKAECTAEDAYKHTDARVIFSSGSP
FPPVQIGDKTFYPGQGNNAYIFPGVGLGVICTGTHHIPDEMFLIAAQELANFVEPSDIERGSLYPPLSSIRNVSMNIAVGVTKCAYDRGLASTYP
EPQDKRKWLENQLYNFNYESSMPASWVWPRMPYIKTREESPLIAAIK*
(SEQ ID NO: 663)

Name: MALATE OXIDOREDUCTASE
Classification: enzyme
Gene Symbol: Mdh

FIGURE SHEET 358

FlyBase ID: FBgn0029155

Celera Sequence No. : 142000013385213
CCGCTCGCAAACAGTTTGTCTATTTTTAAATAGAATTCAAGAAAGTATTCGGGGAGGAAACGTATGTACTTATGCATGAATCACATAATCCCGAT
TCGTAAGAGCAAAATATAAAGGATCGGGGATGTAATTGGATTTAAACACATTTAACTACGGGACAATGGAACCTTGGAATTTTGGTTTTACTTTA
GGTTTCCATGGGTTCGTTGCTGTCGATCGAGACACTATATCTGCGGGGTATATCTATTTATCGATGTACGCCGTATTATGTGAGCATGTATGTAT
ATTCGCACGTATGTATGTATATGGATGTGAGTAACGCTGCCGGCTGCTACACTGGGCGCAGGCTTTAACTTAAAAATTAAATCATCGGCGCGAGC
GATCAGTTGAAGACTAAAGACTTGATGAATCGCCGCGCCAGCCGAAAGCTCTTCATTACAGTTGTGCTCTCTGGAAAGCGATTCTCCGCTTCTCT
TTGCACCACACAACCAAAAGAATCTCGTGGGAAAATGCGAGAGCGATCCGTTTAGGGTTGTCGAGCGGCTCGAACTATAGAGCAAATATGTAGAA
ATAAATGAACATGATCGCATTCGTACACAAAATGATCTTTATCCTTATAACAATAGTTTCAATTCGATACATAAACAGAAATTACAGAAATGAAA
ACTAATCATGATGACAAATCAATAAAACAAGAATATTAACTTGTCTGCCTTGGTTTATCGTGGAAATGTTGCTGTTACTAATGAAGAAAAACTAA
TGTCGCCTCAACGGTGAAAAATTACTAACTCGATTTATGATCCACTTTTGGCATACCATACACCAAATCTCTCCTTGCATACAAGTTTAAAAAAT
ATACAAATACAATATTGTTAGAATAATTCAAACGATGTTAACAGGATTTGACAGCGGTAGGACGATTAGACCAAGTTGATCAAATGCTCGCGCAG
AATAAATACGGAGGTGGGGACAAGGACGAGAACGAGGACAACGAGAATGCCTATTTGGCGGGCGAGGCTATGGAGTTGTTTAGTGAATTGTTTAG
CTGCTCCTCCTGATCCTTGTCCAAGCCAAGGGCTGTGGTCAACAGCTTGACCACACATCGCTGCTCGTGCACCTCGCCCTTCTCGTTGGAAGTAA
TGTCCTTTTCTAGTTTTAGCTTCTCTTCGGCGGCCATCAGGATGCCCTCCTCGATGGTACTCTCGGAAATGAGACGGTAAATGGTCACCGGACGC
TGCTGTCCCATGCGATGACACCGATCCTCGGCCTGTTTATCGTTGTACGGGTTGAAGTCGATATCGTGAATGACACAGGTGTCGGCAGCCGTCAG
GTTGATGCCAACGCCACCGGCTTTGGTGGAGAGTAGGAACACAAAGATGCTATCGTCCCCATTGAAGTCGGTGATCAAATCCTGGCGGACATTTA
CGGCGGTCGCCCCGTCCAGGCGACAGAAACCAAACTTTCGTATTCGCAGATACTCCTCCACAATGTCCAGCATCATGGTGAACTGGCTGAAAAGC
AACACACGGTGTCCTTCTGCCTTCAGTTTTGGAAGCAACGTATCCAGGTAGAGGAATTTTCCAGAATCGCATATCAAATTATCGGGTATTTTCAC
GTCGTAAAACTCCTGAAAGATGCACAAATTTAGTCATTGTCATTGGACAACCTCTTTGATAGTCACTTACATGCTTGTTCATCATCTGATAGACC
TGAAAGTCTGACATAACGGCTAGCTCTTCAAAGATGTATTGCTCGTTGGTCTTTTTAAAGGAACTGGCATTAGCCAGGCGCTTAGAGAATCCACG
TAGATTGGCGTCGGTGAAGTAGTGACGCATCAGCAACGGATGGTTTGCAATGCGGCGCATCTCCATCATGATCGCTATGCCGGCCCTTTCGCTGC
TGCTGCACACCTCGCCCTTGTTATTGGAATAATAATCGACCAGCTCGTGATAGTATATTTTCTGTTGACTGCTCATGGGCACTTTTTCCTTTAAA
TAAAAAACAATTTAATTATTGTATAATATTTATTTTCGCCCGACGTACTTACCACCAGGCTTAGCTTCTTGGGCAGGTTCTTAAGGACATCTTTC
TTAAGCCGTCTGAGTACAAATGGCTTCATGATACGCTTTGCTCTCTGGATTTGTGTTTCCTGGAACTGTGAAACCTCATCCTGATCTCCATCGCT
TTTTCCCTTCTGCAAGGAACATGAAGTTTATATATTGTTTTGTGTGAAACCAATCTTTGTTTTACCTTAGCAAACAACGATTTTATGTCCTCAAT
GCTCTTGGCAAAGAATTTGGGCATCACGAAGCAGAGCAGAGAGATTAGCTCCAGCAGATTGTTCTGCAGCGGAGTTCCAGTGAGCAGGATTCGCA
TCCTAGCGTTTATGGTTATAAGGTTAGCATAGCGTTGCGTGGTCATGTTCTTCAGCATATGGGCTTCATCAAAAATGACGTAGTCCAACTTGCAA
ACCCGGAACATTTTCCTCTCCTCCGGCGTGGATCCCACAATGTGATATCTGTTCAAAATGTACAAGAAATTTAAGCTTAGATTCTTTTATGGCTT
TGTGGATATTTACGTGGTCAGAAGAACATCAAAGCCGGTAAATCCATCCTTGGCAAAGCGGCCTCGCATTCTCCTTCGCTCGTCCTGCGAGCCAT
GGTACTTCTCCACCACCAGTTCGGGACACCAGCGGCTAATCTCTGCCTCCCAATTATCCAGCGTGGACGAGGGCACCACAATTAAATGTGCAGCC
TGGCTAAGACCATTCTCCTTTAGATAGGCCAGAAATGCAATAACCTGAATTGTCTTGCCCAGACCCATTTCATCTGCCAAAATGCCATTCATTTC
TTGTTTGTGCATTACGGTGAGCCAATTAAGGCCAATTATCTGATAATCAGCCAGCTGTAGACTGCAAGAGGAACGAAAATAGAAACACAAATGGG
GACATGCATGCTGGTTAAGGCTCACCCGCTGCTAAGAAGCTTAGGTTGCTCCACAATGCCAGCACCATTGGAAATCGCCTTCTCCAGACGCGACA
CCATGTTATTGCACTTACTTAGAATAGCGGCCACCGTGTTCTGTTTGTTAATCAGCTCTTGAGCGTAATTCAAAAGATCACCCGACATCCTGATG
CTCTCCAGCTTTTGGCGCAAATCAGACCAATCACTAAATGGTCGCACATCAATGATGGCTAATGCCTTCTTCTCGGACAGCGTTTTAACTGACTG
GAGTTCAATTAGCGAAGCCTCGTTCATAAACTGGAAAACTTTTTTACGTTGCCCCGTCATCTTGGTGGACATCTCGCTATCGCTGTCATCGCTAT
CATACACCTGGTCCTTGGACTGCTTCACATCATCGTCGTCCGAATGGTCGTTATCCGAGAAGTTGCCTCCACTAATTCCGTTTGACCTGGGTTTC
AGCTTGGACTTGGCCAGTGGTCCATTGTGCCCCTTGGGCTTGCAGTTCTCCCTTAGGTATCGCACGGAAGCGGCCACATCCCAATTGGTGCGGGA
AAGAGACTCCTGGATGGCCTACGGAACATATTTGAAATTTATTTCAGTTAAAATCGAGATTTATGCAAAATATTGCATTAAAAATGAGCAATTTT
AAGCTATAAAATATTCTGATTAATTTTAAAATTCAAATAAGAACGGTGATAATGTCCGGAAATATTTTATATGAGGCACACCAAAGTAGTGGAAA
CAGTTACACGAGAGGGTTATTACTGCTCCCATCCCCGTCAGTGACGCCCCTGGCTAACGACAGCTGTTCGCAACGCCGGGCCGAACCGAATCGCC
ATGTTCCCCGAACTCAGATGCAGAGACGCGCGTTTCCCCGCGAATCGCCCCGTTTTACCTTGGTGGCATTTCGGCCGGAAACCTACCATTGTGTC
AAAGTGGGGCGAAATCTTGGCGGCTGCCATGTAGCGCTCCTCCTTTTCCTTAACGGTCAGCTCCAGTTTGGTCTTCTTGGGCGTCTGGAGTCGT
TGCCATCGCTGTCACTATCGGCCATCACCTGGATGCGCTTCTTTCCAGGCACACGCTCTGAAATCAGGCAGTTAGCTACCGTGTCAATCGCTTGG
AATTTAGCTCAGCAAGTACCAGTTCTCGAAGGACTAGCGACGACAGAGGAAGCATTCTTGTTGATGCGGAACTGACGCAGATCGCTGAGGCTCG
ACTTCGCGGACGATGAGGCGGAGGCCGACGCAGATGCGGCCACTGTGCTGTCCGACATCGTGGGACAAGGCGAAACGCTTCCTGGCAATCTGTCA
GTCCTTATTAACAAATTCTGTTTGCAACTCCTACAATCTTAAGTTGGTATTTGTGAATATTCGCATGCTAGTGCGGCCGTTTGATTATCCCGATA
AAACCTATTTCTATTTCTCCAACGGAATGCGGTCACACTGTGCGCCAATTTAAGTATTAGCTTAATGATTATTATTATTTTTCATTTATTTTTAT
CGAACTGTAACGCATTAGTGTAAGCTTCTATGAGATTATCTAACAATTTGCTTTTGTATATATCGTATATGATTTGATTTCGTCAACCTAACCGT
AAGTAATTAAAACCGATGCCAAAATGAAAGAAAGAAACTTAAAAAAATCCCAAACTGGCGGTAAATTAAGAAAGTTGCCAGAGTTGCCAGATGTT
ATCGGCTTACCGCAAGCAATCGGCCAACAATCGAAACATTGGGACGCGTTGCAACCCTCTCTTTTTTTCGCTTGCTCTTGTAGGTTAATTGAAAA
CACTTTTATTGCAAATAAACCGCTTGCCGAGCCAAGGGCAAACCGATAAACTGGCAAACATGGCTGGCGGCAACACCCCGCGTGTGATCCAGGTG
ACCAACATAGCGCCGCAGGCCACCAAGGACCAGATGCAGACGCTGTTCGGGAACATTGGCAAGATAGAGGAGATCCGCCTGTACCCGACAATCCG
TGATGTCTCCTGTCCGGTGCAGTCGCGCATCTGCTATGTGAAATACACGGACACGACCAGTGTGCCGGTGGCCCAGCACTTGACCAACACGGTGT
TCATCGATCGCGCCCTAATTGTCATACCCGTTCTGGCCATACCCGAGGAGTATCGGGCCCTGGAGATGCTCAAGAACGGAACCATTGTGCCGGGA
CTCCAGAAGCCGGACTCCAAGCTACCGCCCGAAGTCATTAACCGCATCGAGGGACAGCTGCCGCAGCAAGTGATCAAGACGTACGACCCCAAGTT
GGTGGAATTCAATCTGCCGGAGTACCCGGCCTTACCCTCGTTCTACGATGCGCGCAAAATCGAGGAGATTCGGCGCACCATTATCGTGTGCGATG
TTAAGA
(SEQ ID NO: 664)

Exon: 4326..4106
Exon: 4047..3887
Exon: 3533..2971
Exon: 2911..2579
Exon: 2518..2251
Exon: 2194..2048
Exon: 1988..1686
Exon: 1627..1001

FIGURE SHEET 359

Start ATG: 4238 (Reverse strand: CAT)

Transcript No. : CT18505
AATACCAACTTAAGATTGTAGGAGTTGCAAACAGAATTTGTTAATAAGGACTGACAGATTGCCAGGAAGCGTTTCGCCTTGTCCCACGATGTCGG
ACAGCACAGTGGCCGCATCTGCGTCGGCCTCCGCCTCATCGTCCGCGAAGTCGAGCCTCAGCGATCTGCGTCAGTTCCGCATCAACAAGAATGCT
TCCTCTGTCGTCGCTAGTCCTTCGAGAACTGAGCGTGTGCCTGGAAAGAAGCGCATCCAGGTGATGGCCGATAGTGACAGCGATGGCAACGACTC
CCAGACGCCCAAGAAGACCAAACTGGAGCTGACCGTTAAGGAAAAGGAGGAGCGCTACATGGCAGCCGCCAAGATTTCGCCCCACTTTGACACAA
TGGCCATCCAGGAGTCTCTTTCCCGCACCAATTGGGATGTGGCCGCTTCCGTGCGATACCTAAGGGAGAACTGCAAGCCCAAGGGGCACAATGGA
CCACTGGCCAAGTCCAAGCTGAAACCCAGGTCAAACGGAATTAGTGGAGGCAACTTCTCGGATAACGACCATTCGGACGACGATGATGTGAAGCA
GTCCAAGGACCAGGTGTATGATAGCGATGACAGCGATAGCGAGATGTCCACCAAGATGACGGGGCAACGTAAAAAAGTTTTCCAGTTTATGAACG
AGGCTTCGCTAATTGAACTCCAGTCAGTTAAAACGCTGTCCGAGAAGAAGGCATTAGCCATCATTGATGTGCGACCATTTAGTGATTGGTCTGAT
TTGCGCCAAAAGCTGGAGAGCATCAGGATGTCGGGTGATCTTTTGAATTACGCTCAAGAGCTGATTAACAAACAGAACACGGTGGCCGCTATTCT
AAGTAAGTGCAATAACATGGTGTCGCGTCTGGAGAAGGCGATTTCCAATGGTGCTGGCATTGTGGAGCAACCTAAGCTTCTTAGCAGCGGTCTAC
AGCTGGCTGATTATCAGATAATTGGCCTTAATTGGCTCACCGTAATGCACAAACAAGAAATGAATGGCATTTTGGCAGATGAAATGGGTCTGGGC
AAGACAATTCAGGTTATTGCATTTCTGGCCTATCTAAAGGAGAATGGTCTTAGCCAGGCTGCACATTTAATTGTGGTGCCCTCGTCCACGCTGGA
TAATTGGGAGGCAGAGATTAGCCGCTGGTGTCCCGAACTGGTGGTGGAGAAGTACCATGGCTCGCAGGACGAGCGAAGGAGAATGCGAGGCCGCT
TTGCCAAGGATGGATTTACCGGCTTTGATGTTCTTCTGACCACATATCACATTGTGGGATCCACGCCGGAGGAGAGGAAAATGTTCCGGGTTTGC
AAGTTGGACTACGTCATTTTTGATGAAGCCCATATGCTGAAGAACATGACCACGCAACGCTATGCTAACCTTATAACCATAAACGCTAGGATGCG
AATCCTGCTCACTGGAACTCCGCTGCAGAACAATCTGCTGGAGCTAATCTCTCTGCTCTGCTTCGTGATGCCCAAATTCTTTGCCAAGAGCATTG
AGGACATAAAATCGTTGTTTGCTAAGAAGGGAAAAAGCGATGGAGATCAGGATGAGGTTTCACAGTTCCAGGAAACACAAATCCAGAGAGCAAAG
CGTATCATGAAGCCATTTGTACTCAGACGGCTTAAGAAAGATGTCCTTAAGAACCTGCCCAAGAAGCTAAGCCTGGTGGAAAAAGTGCCCATGAG
CAGTCAACAGAAAATATACTATCACGAGCTGGTCGATTATTATTCCAATAACAAGGGCGAGGTGTGCAGCAGCAGCGAAAGGGCCGGCATAGCGA
TCATGATGGAGATGCGCCGCATTGCAAACCATCCGTTGCTGATGCGTCACTACTTCACCGACGCCAATCTACGTGGATTCTCTAAGCGCCTGGCT
AATGCCAGTTCCTTTAAAAAGACCAACGAGCAATACATCTTTGAAGAGCTAGCCGTTATGTCAGACTTTCAGGTCTATCAGATGATGAACAAGCA
TGAGTTTTACGACGTGAAAATACCCGATAATTTGATATGCGATTCTGGAAAATTCCTCTACCTGGATACGTTGCTTCCAAAACTGAAGGCAGAAG
GACACCGTGTGTTGCTTTTCAGCCAGTTCACCATGATGCTGGACATTGTGGAGGAGTATCTGCGAATACGAAAGTTTGGTTTCTGTCGCCTGGAC
GGGGCGACCGCCGTAAATGTCCGCCAGGATTTGATCACCGACTTCAATGGGGACGATAGCATCTTTGTGTTCCTACTCTCCACCAAAGCCGGTGG
CGTTGGCATCAACCTGACGGCTGCCGACACCTGTGTCATTCACGATATCGACTTCAACCCGTACAACGATAAACAGGCCGAGGATCGGTGTCATC
GCATGGGACAGCAGCGTCCGGTGACCATTTACCGTCTCATTTCCGAGAGTACCATCGAGGAGGGCATCCTGATGGCCGCCGAAGAGAAGCTAAAA
CTAGAAAAGGACATTACTTCCAACGAGAAGGGCGAGGTGCACGAGCAGCGATGTGTGGTCAAGCTGTTGACCACAGCCCTTGGCTTGGACAAGGA
TCAGGAGGAGCAGCTAAACAATTCACTAAACAACTCCATAGCCTCGCCCGCCAAATAG
(SEQ ID NO: 665)

Start ATG: 89 (Reverse strand: CAT)

MSDSTVAASASASASSSAKSSLSDLRQFRINKNASSVVASPSRTERVPGKKRIQVMADSDSDGNDSQTPKKTKLELTVKEKEERYMAAAKISPHF
DTMAIQESLSRTNWDVAASVRYLRENCKPKGHNGPLAKSKLKPRSNGISGGNFSDNDHSDDDDVKQSKDQVYDSDDSDSEMSTKMTGQRKKVFQF
MNEASLIELQSVKTLSEKKALAIIDVRPFSDWSDLRQKLESIRMSGDLLNYAQELINKQNTVAAILSKCNNMVSRLEKAISNGAGIVEQPKLLSS
GLQLADYQIIGLNWLTVMHKQEMNGILADEMGLGKTIQVIAFLAYLKENGLSQAAHLIVVPSSTLDNWEAEISRWCPELVVEKYHGSQDERRRMR
GRFAKDGFTGFDVLLTTYHIVGSTPEERKMFRVCKLDYVIFDEAHMLKNMTTQRYANLITINARMRILLTGTPLQNNLLELISLLCFVMPKFFAK
SIEDIKSLFAKKGKSDGDQDEVSQFQETQIQRAKRIMKPFVLRRLKKDVLKNLPKKLSLVEKVPMSSQQKIYYHELVDYYSNNKGEVCSSSERAG
IAIMMEMRRIANHPLLMRHYFTDANLRGFSKRLANASSFKKTNEQYIFEELAVMSDFQVYQMMNKHEFYDVKIPDNLICDSGKFLYLDTLLPKLK
AEGHRVLLFSQFTMMLDIVEEYLRIRKFGFCRLDGATAVNVRQDLITDFNGDDSIFVFLLSTKAGGVGINLTAADTCVIHDIDFNPYNDKQAEDR
CHRMGQQRPVTIYRLISESTIEEGILMAAEEKLKLEKDITSNEKGEVHEQRCVVKLLTTALGLDKDQEEQLNNSLNNSIASPAK*
(SEQ ID NO: 666)

Name: putative helicase
Classification: DNA_binding

Celera Sequence No. : 142000013384321
GTATTTTTAGAAAACATTGCTGTAATCCTAATTGGCTGTTAGCGAATAATTTAGAAGGCATATCATAGAAAATTTTGACACTTTTATGATTTTTC
TGCTTGTGTAAAAATGTTGTAATACCCCTGAGATCTGTATAGCATATATATTTGGGCTCTATATTTGGCTGGGGTTTCATGCTCTAGCCTCTTTT
CTTTTTGATAATAATATATGCTAAATCAATTTGAAATCAATCGATTCAAATATTTACATATATAGTCTCTAACGCTTAAATGTATTCAATATTCT
AGATGTTCTAATGTTCTAGAAACCGTTTCCAAAAGTCAAATCATTCTATTTAAGTTTGCTCCCAGAATTATATCTCAATCTTTATAGTCTAGGGA
CTACGTGCTGGAATACTGGTTTGGCACTACCTTTTAAATAATATCCGAGGCCCCTGAACCAAGAAAATGTGCCAATAAATATAAATTATGAACTT
TATGATCTGCAGAGGATGCCAAATATTTCAACATGACTTATATGTATGTACGTTCGAGAATTGGGAAAATTTATGTGTAGATACATTCTGGCCAG
ACGCTAGATACACAAAATGAAACGCACAAATGACACAGGCTAATTACAGGTAAGCAATAGAAAAGAAAAGACAAGAAAAGCAGGCGTACTTCGTG
TTTTTGAGTTTATTTTCGTAGGGGGCAAGCTCTCAGGCAAACTAGCGTGAAAATGCGTTCACACAAGCTTCGGCCCAAGTGAAATGAAAAATCAA
AGAATTTTCCACACAACTGAGCAATTAACACAACAACACGGCCGCGTGAAAAGTCACTCGAAAGTCCCACTCACATTCACATAGGTGGTGGTGGT
GGCTTATAGATATATCTCAGGGTATATCCCACTCGGATCCGATCGGCGGGGAGCCGATGGCGCCCGACGGCGACCGAAGGCTCCCGAAGGGAACC
GAATAAATCGTTGAAATAGACGAATTCAGCTGGCAGGCCAAACCAATTCAACGAAATACTCTTTATTCGAACGACAACGGGATCTCTTGTTCAGT
AGATCACCAGCCTTACTCCGACGTTTATTACGAATTTTCTCGGTGACTCGGTGACAACTACAAAACTGCGTGCGGTGCTGTATAGATTTTCGCTT
GAGAGGAACACACAAATCATAATACTAGATACGCGAACCGATCGCACATTAATTTATAGAACCAAAATCGAAAATCTGACCTAGCAAACATGTCG
TCATCGCAGGCTGTCCGCTCCTCGAAATACTCCTACCGTGCCACGTCCACCGGACCCGGTACCGCCGATGTGAACATCGAGTACATCCAGGACCT
GAGCTCGCTCTCCCGCTTGGAGGTAAGGATCCCGTCCCGCTCCGTCTCGGAATCTCGAATTCGAATTCGTAATTGGAAGCGGACCGGTATCGTTT
AAGAAATCGGCATCGTATTGGGCACCAAATCCCCAAAAGACGTTGGAATTCCGACCAGGGAATAGGAATACGAAATGCGTGTGCGCCAAATTTT
CTTCAAAATCTACGAGAATTTCTCTCTCTTGTTTCGGTGTCTGTGTAGAGACTGAAAAAGAATCGGAATATAATCAAGAAAAAATACGAAAAACA
AACTAAGAAACCCGAAAAATTCATCTACACTCTATATCAAATGCACATATATACCGTAGATATATATTCGTGTGTTAAGTTCTCGGCGCGTTCTT
GTGTGTGGAAATATAGAAAATTCGGTGAAGCAAAATTCTAGATTTGTATATGTATCTAAACGTGTCTGTATATACATATGCATTGCTAAAAAATT
ATGTAATGGCCACCTCTGGGCAATACATATACACGAGAAAACATCGAAGAAAAATTTGTGAAGAAATCAATCAACTGTGCTGTAAAGTGCTTTTT AATGAATGTTTTAATCAAATAATATGAAATAACGAGCCCATAAAAGATCAAACTCAATAAATGTATCCACCATTTTCTTGCAGGACAAGATCCGT
TTGCTCCAAGATGATCTTGAAGTTGAACGTGAGTTGCGCCAAAGGGTGAGTCATTCAATATGGAAATATTCATAATTTTAAATATTTTTAAGTTA
TTTTTGAACCGAGTATTTTTAAGGTATTACTATAGGTTTCTTTGGAATATTTTTGAACATTCTTAATTTATTGAGAGCATCGTTTTTAGTCAATA
AGATTATTTGCTGATGAAATCGGCGTCAGAGATATGACATATCCGAGGAAGTTAGAAAAGATCAGACCGCATTCTCCGAGACCCAATGGAAATCA
AAGCGCCAGGGAAAACCATTTTTACTTTTTTCACCTCGCAAATGTCACCCTAAAAACAGCAAAAATATGTGGAAAGCCAAAATAAAATCAAAATA
GACCAAAGTAGCAGTAGCGATAGAACCGATAGAAAAGTCAGCAAACAAATGCAAATCTAAGAATAAACTACCCTTCGTAGAGTTTCGAAAGTGTG
AAAGTAAATGATAATGATGTGCATTGAACTTCAATCGCTTTCGTTTTTGGCTTTTCCTTCCCTGCGGAGCATTGATAAATGATTTTTCCCCTGAC
TTTGCAAAGACAGCGGCCGCAAAGACAGCAAAGTCAGGAACAGCCAGAGAAAAGTGGAAAATTCGCAGGCCGAAAGTGCACTTCATTCAGCGCA
ATCCTCTTGGGCGTTACAAATTTAGAAAATGCGAAGAGCTCTTGCCGGAATGGAATGGGCTGGCCAGGAATGTTCTGAAAATTTTGTTAAAAAAT
CAAATTTAATTACTTTGTGCCTTATGGATTAGCACGCACTCGCACACAGATACAACGCCCCCCAACACACACTCACAATATATGGAACAAAATGG
CTAAAATTAGCGCACGACATTCAATACAGAGAAGCGAATGATTAACTTGAAAACAACCAAAATATGAGCAGAGAAGAAAAGAAAATAAAGTAGCC
AAAAAGTCATCATCATCACCATCTTCATGATCAGCGGCGGCAGAGAGGAAAATTCGCTCGCTCACTACGGGAAAATCTTCGCTTTTTGTCTGTGG
GCGTGTGTCTGTGGGAAAATTAAATAATTTTCATGCACATTAAAAGTCTTCACACCGCCTGGCATTCTTTCTACATATCCACATATGCATATATA
GGCGGCAAAAACATGTATCTACAAGATACATATGGCGCAAATGGATTTACGGCCCGTACTTACGTGGCCTTTGTGGCAATCGGCAACTTTTTGTT
ATGCCAAATGAACGGACAAACACATGTTCGCCTAGGTATTATCATAAACATAAATGTACAAACATATTCAGCGAGAGATTTAAAAGAGATTTATC
AGACCAATACGTTCTTTATTTAAGCTTGGGGCATTTCAGTTAGCTGAATTTTTTATGATTGCTTCGGACAGCTCCAAATACCAGAAATCCCAATG
GCCGCACATAGCTTTCATAAAATAGCATTTAATTGCAATTCGCAAAATTGACCAAACGAGGTCGTCGACAAAGGCGAAAAGCAAATGTTTAGATT
CCGAGGGAGCCAACAAAAAATGTTTCTGTTCAAGCGAAAAATGTTCGAATGCCTTTTTGGAAATGCAATCTAGGAAAGCGGTGTGCGGCCGCCCA
CAAAAGATATATACGCATATATAGACGCATATATCGTGGATGCAATCGGACTATGGCTACACCTCTGCGTGGAAGATTTCTTGGCAAGATGCCAT
TGTTATTTTAGGTGTTGCATGTGCATAATTATTTTTGACTGATTAATGTGATTTATAATTTTTATTATGGGCTGTTTGAGTAGCCACAGAGCATG
GCTAGCGCAGGGTATTTATAGATCCTTCACATTATACCAAGTCGCTAATGAAATCTCTTCTTAATCTCTGCTTATATTCTTCAAATTTCAGATCG
AGCGCGAGAAAGCCGATCTCAGCGTTCAGGTCATTCAGATGTCCGAGCGTCTCGAGGAGGCCGAGGGTGGTGCTGAACATCAAGTGAGTACCATG
TGGTAAACCAATATTGCAATCCAGCCATAACTGATGTATCTTCCAATCCCAGTTTGAAGCCAACCGCAAGCGCGACGCTGAGCTGCTGAAGCTGC
GCAAGCTGCTTGAGGATGTTCATCTTGAGTCGGAGGAGACCACTTTGCTTTTGAAGAAAAAGCACAACGAAATTATCACGGATTTCCAGGAACAG
GTTGAAATCCTAACGAAAAACAAGGCCAGGTAGGCATTGCAACAGGCTCTGGCCATCGCCACCCGACGTCCCCATTTCCATTCCATTGACCCAGA
AACCATACCATATCCAAAACATAAACATCTCCATCCCGAGCTGTCATGCATCCGCAGAACATATTTATTTGCCCCCAATGATGATGATCAAGTGG
CGTCAGCTGGCTCTTGCGGACATTTCAATGTCTCGAGATCTCGTGCAGTAACTAACCAATACAATGCCTAACCTTGCGCTGCCCCGTTGACCCAA
AAAAAAAAAAAAAAACAGAGAAAATCGAAGCAGATCATAAACCATTCATCAAAATGCCATGACATGCGAAATGCAAAGCGAAAAAAATCAGAAAA
CATAAACCTGCATGGCTTGCAAGTTCTATTGGCACAAATCGCGGCCGAAAGGCCAAACGAATGAGAAAAAAATTCGAGAAACTTTCGGTTGCTGG
CCGCCTCTCATATTTCCAAATCGATGCGAGCGATTTCCAAAAATAAATTCCTAGGAATTTTGAAATCGCAACAATTCAAGGCTATCAAAAGATAA
CGAGTCATTTAGATTAATATGCATTCGGATAAATCAAAATCAACTCATATCCTAAGATTTAAATCAAGTTCAAAGTTGAGTTTCTTTACCGTTCTT
TAAGATTTCCACCTTTAAGATAGGTGCGCCCGAGTTTGCGCACTTCCGTTCGTAGACAAGGACAGAAGGTCGGAAGATCAAGCAGCCGTCCCACT
CTATCGAAAAAGCTTTGGAAAGCTTTCGCACAGCGAAACTTTCTTCCATATGTTGTGCCCACCACCCCATACCATATTTCTTTCTGAGCGGAAA
TTTATTTATAGAAATTTTGAAATTTTCATCCACATTCTTGAACAGAGAGGCTCTTTGTTGCTGTTGCCATTCCGCTCCCACCGCCTCCCTGCATC
ACTCCCTCTCGCTCGCACCAACGCTCCAACCCAAATATGTCTTTGATTGAATCATATAGAAAATGTGTTTATTGTTTTTGTTGCTGTCCCGCTCC
GACCCATCGCGTATTATGGAAATCCGATACGTTTTTCGCTGGCTTTTCAGCTTGTGGGTGGAAAGGTCGGTTGCACCGATTCTAGCCCCCTGA
CAGGTGGAAAAGCTGGCAAATGCCACGAATTGCACACGGAAAATTCGATCGACAATCAAGGCGATACATAATGGGATATTACTTTGATCGATTCA
GAGCACACTGGACTTAATATATGACCACTATGATTAGAAAAGATTACAATGCGCCTTAGGTACAAAATTCACATATCTATAAGTAACATTCTCAA
ATTTACCAAACGTATCAAATTGATTTACACTGATCGGAGTAATTCATATTACATATCCTATCTATTCGTCCCAGCTTATGCATATTTATTTTACA
ATCAATTATCATAGCTTGCTTCCAGGCAGACCCAACATGATCTTAACCCTTGGCCTGCTGAGCCTTCGACCACCGTTCGATAATCCTACGATAAA
CTTTCGAACGGTGGCCGAAAGCTCGCAGTTCCACTCAAGCTTGCTAGCGACTCACAGCCTGGCCGATCTCACAAACCATGACTAAGTATCGGGAT
TGTGATCATAGACCCCAAAAACTAAAGTGGAGAACCCTCTTCTCCCTATTTTTAACCGAATGCTTGCAGAGCCGAAAAGGACAAGGCCAAATTCC
AGACCGAAGTCTACGAGCTGCTCTCCCAGATCGAGTCCTACAACAAGGAGAAGATCGTGTCGGAGAAGCACATCTCCAAACTGGAGGTCTCGATC
TCCGAGCTCAACGTGAAGATCGAGGAGCTTAACCGCACCGTTATCGACATTAGCTCCCACCGATCCCGCCTCTCGCAGGAGAACATTGAGCTGAC
CAAGGACGTCCAAGATCTGAAGGTTCAGCTGGACACGGTCTCGTTCTCCAAGAGCCAGGTCATTTCCCAGCTGGAGGACGCCCGCCGTCGCTTGG
AGGACGAGGACCGTCGTCGCTCGCTGCTCGAATCCTCTCTGCATCAGGTTGAGATCGAATTGGACTCGGTTCGTAATCAACTCGAGGAGGAGTCC
GAGGCCCGCATCGACTTGGAACGTCAGTTGGTCAAGGCCAATGCCGATGCCACCTCCTGGCAGAACAAGTGGAACTCCGAGGTGGCTGCCCGCGC
CGAGGAGGTCGAGGAGATCCGTCGCAAGTACCAGGTCCGCATCACCGAGCTGGAGGAGCACATCGAGTCCCTCATCGTCAAGGTCAACAATCTGG
AGAAGATGAAGACGCGCCTGGCCAGCGAAGTGGAGGTGCTCATCATCGATCTGGAGAAGTCGAACAACAGCTGCCGCGAGCTGACCAAGTCGGTC
AACACCCTCGAGAAGCACAACGTTGAGCTGAAGAGCCGTCTGGACGAGACCATCATCCTGTACGAGACCAGCCAGCGCGACCTGAAGAACAAGCA
CGCCGACCTCGTCCGCACTGTCCACGAACTGGACAAGGTCAAGGACAACAACAACCAGCTGACCCGCGAGAACAAGAAACTGGGAGGTGCGTTAC
CATACTAAAAGACTTTCACAATTGTATATTGTAGTTATCATGATATAATATTTAATAATAACCTATTATTAACCAGATGATCTTCATGAGGCCAA
GGGTGCCATCAACGAACTGAACCGTCGTCTGCACGAATTGGAACTGGAGCTGCGTCGTCTGGAGAACGAGCGTGATGAGCTGACCGCTGCCTACA
AGGAAGCCGAGGCTGTAAGTAATCACAAAAAAAAAAAAAAAACATACACATAACATTTTTAGTTATAATCCTAATAATTTGTGTAATATTATTTTA
TAGGGCCGCAAGGCTGAGGAGCAGCGCGGACAGCGCCTGGCCGCCGACTTCAACCAGTACCGCCACGACGCCGAGCGTCGTCTGGCCGAGAAGGA
TGAGGAGATCGAGGCCATTCGGTAAGTTACTGACCAGGGATTGGTAACTAGAGTTAACCCCCTTTTTGGAAGTAGCCCCACGCCACTGCACCACG
AGTGACAGCGAGAACAGACGAAGGTTTTCGTTTCCCCTGCCAAAGCGGAAGTCCCAAAAAAAATAAACACCCCTCAAGGCCCCAAGGGGGAAATT
ATTCGATTGATTCGCAATCGCTTTCGCAATTGCCAACACAATTGATAGTGAACTGACCCATTTAGCAATTAGCAATCAGTTTGAGTTCTTTAGTC
GCACAAAAAGCAACGGCATTAGTTTTCTATTCAGGAAGCCAGGCAAAAGATCCTGATCCCACTGAAGGTTCAAAGGCTGAGCTCAAGAAGTGGGT
TATATCCATCTGGTTTTCAAAACCATACCGATTTTTTAAAAATCCGTATCTAATTCTCTGCAGAAAATTGCGCAGTTGCTGTGATTACACAATCA
AAGTGGGTTCATAGTTGAAAATCGAAAGAACCCATTGAGAAAACTTTCGATTTGAAGAGTGGCTCTCCAGCAAGTGGTAGGTTTTTGGATCAATC
ATCAATCGAGTTGGTGGTCAGTGTTAGTCTGTGATTGAAATGATCTTATGTCTTAAGCAGAGATCAGTTCTAGCTTTCTTAAAAACAGATAAGTT
AGGTGTGCATAATGCTTGATCTTAATAGCTATTGTTGATTTTGTAAAATTTTTACACACGTTTCCGGTAATTAAATGATATTGTGAAATCGATAG
AAGTATCTATCTGAACTTGTACAAATTAAAATCGGTTGATTTGGAATGTTCAAATAACTTTACATAAATAGATACAATAACTGAATAGAAAATTG
ATTATATGCACTTTTAGACACTTTCCCTAGTTCCTTAGAGTCTTCCATGACTATTGCATAAAATGTCTTGCTATTATGACATTGTCTATGAGCAC
TTTGCCAAAATGAATCAATCATAGCCGCACACATTGACTGCCAACAAATGATGATAATAATGATGATGGTGATGATGATGTTATTGTCGTCATTA
TGCTCATACCTAGCCCGATGCCAACAGCTGAAAGAAACGAAATGCAATCTTTTTATAGATTTCGACAAATTTGAAAATTTATTTGCAAAGCAGCA
GCAACTGCCACTGCTGCCAACCGAGGAGAACCCAAGAAACCCGAAGCTACAGAGGCGACAAGGCGACACACAGAGGCGGCGACAATTGTAGCTTT
AATTAGAGTACTCTTAAGAAAACACATTAGGCCATTAGACCATTAGACCATCGCAACCCCCTTGAGAAATCCGCCCCCCCTTCACAAAGATCCCC
TTCCTAAACCATGGCCCTAGCCCTAAAACAAAGACCTTCTCGCTTCCGTCCGACGACGACAACGTATGAGGATAACTATGGGTACACCATGAACT
TCTACCAGCCCATGCTGGACTATCTGGACGCCAAGGCCAAGGGTCTGGAGGTCAAGAAGCCGCACCTGCCGTGGGTCAGCGAGAGGGGACTGAAG

FIGURE SHEET 361

CAGTACCGCCCCTCGAATGCGGTGCGACAATATAACGCCGACGAGATCGTCCGATTGTCGCGCACCTGCGCCGCTCGGGCCGACGAGATATTGCT
TAACTTTCGGGCCCAGAAACGCTCGCCGTTCAGTGTACAAAAGTTGGTCGACGCATCGCGAGTGACCAAGCACCTTGAACCGGACACAGTTGTCG
AAAGATCGCGCCAGCGCCGCCGTCGCCGTCAGGAGGAGCTCGAGGATTTGATCAAACGCGACACTCTTAAGATATTGCAGCGTATCCGTAAGATT
GAATTGGATAACGAACTCGACAAGATGTCCGACGATTTCAAGCGCTCGATTCGCGGCAAATCCGCCAGTGCCATCGCCCAGGCGCTGCTCTCCGA
ATCGGAGAAGAACATCAAGACGGCCAAGAAGGAGGAGGAGGACTATATCGCCCAAACTTTAGTGCGCTCGAGTCGTGCAGTTTCGCGTGCCCGTT
CGCGTTCCTCCTCCCCCCTCGATGGCCAGTATCGCGCCCATGCGCTCCACATCGAGCTCATGGACGACCGGCTGGTGGACAAGCTGGACCATCGC
GTCTCCTCGTCCCTTCACAATGTGAAGCGCCAATTGTCGACACTGAATCAGCGCACTGTGGAGTTCTACGCGGACAGCAGGTGCGGTATTGAGGA
TAAGTGCTGGATCTGTCGCAAGGTCTTGCGCACCCATCCCAAGCTCAAGGACTATAGCTACGTGTATTGGAAGCACTAGGTCCAGGTCGATGTCC
CTAATCCCAATTCCTTGCCCAATTCCAGACCCTCTTTTCGCTCATAGCTTCATTCGATATCTTAGATTTCAAGCACAAGGTAACTTAATCTTTTT
TGACCATCCGAAATGTATCTCAAATGTATACCAAAGGATATATTTGTGTTACTGCACACATCGAAGAGGAGAGAAAACCTTTTAAAAATCAAATA
TATGATTTTTAGAGGCCTCTATTTTGCTTACTGTTCACTACACGAAACGGTTCTTTACGAATACTAAAAGACATGGAGTGGTTAAATATATTTAT
CTCGAGATATTAAAAGATCCATCTTCAGAAAGCCAAAAAAATGTGTTAATATCAAGTGGATCGAACTGCGTTTCTCTGTGTACTTTCCCATCCGG
GCAATTTGAATAAATGCGAACATTTTTGAATTGCAGCTCAATTTTTTGTCTGAGCATCCTAGCATCCACCTCCCCCGACCCGGCAATTTGGCATC
TCTATTTGTCTGTTTGTCGTTTCTCGTCTGGCACAAAATGTATTTTTGTTTCAAGAGTTTTTGCAAATCGCGTTCTTGTTTTGTTCCTCTAGCAT
TGTGTCTGTTGTGCAGTCTTCTGAAAATTATTTATACAGAATTATGCGCAGCATATTTGACCACGGCTAATTGCAGAAAATCGCCAGCAATTTGG
TCATTAATTAGAAACTTTGTGGGTGTTTCTTATGCTTCTTGTGTTGGGCATCTAAACAAGCCTTTGAGTGGGAAATATCTTTGTTTTAATTGTGT
ATATAATCAACACTCTTATCTGCCGAATATGTCAAGTTAGTATAATCCCTAAATGCCAAGTTAATCAGAATGCACATATATTCATCACTTTCCCC
TGAAATAACGACTTCTTAGCCCAGTCCTATCATATTTCGCACCCGCACCTTAGAAATTTCGAGGCTGTCAGTCCGATTTGCGCGTAGATGGTCCG
ACCAACTATTTCTTTGGGTTTGTCCTTCAAATCGAGATTTATTTTATTTTCAACTGAAAAGAAAACTGAGGCGCATGACAGCAAAAACAATCACA
AGAAGAGGTGGCGACAAAAAAAAAAAAAACAGAACAACATTAGACACAGCAAATATTTTTGCGTAAACATTGAAACAATGGCGGTGAAAAATTAA
AATCTAAATGAGAATGCTTAAGCTTTCTACCTAAAACCAAATACCTTGGCAAAACGACAGCAATGGGCACACACACATGATTTTCAGATTAAGTA
ACCAACACAGGGGCTTTTATAAGAAAACTCAACTAAACAAGAATAATCATAGGAATTAGGAAATACTGACTGATGAGGGATTATAATATTGTTAT
ATAACCAGGGAAAAGGAAATGATTCTGCAAATTAAGCATCATTAAGATACTCCTTCCAAACTCAAAAATTGTTAGATACTGGAAATCCATTAGCT
TCCTATGTTTTCGATGGTAATATATTCTATCACCACCTTGTAAAACGACCTATCGCCACTGAAATAGAATTCAGTAGTCATGTTCACTTATCACT
AATTGCAACAGGTACACGACTTTGAATTAAATTAGAAAGTGAATCAGGTAGAGTATCAGAAGTGCAAGCATAACTCAAATTTAGTTGGCATCGCT
GCACCTTCGCCCAAGAATAGACGCATGATGCACTTACCCCAAAAACAAAAACAAAAATGCATTTTAGGGGGAGAAGGAACTAGTCGGCAAATAGC
TTGGCATGTATGTCCCAACTATTTGTGACAAGTTCGATGTCTTTATCATGCGTAAAAATACACCGAAATTCGCGAATGCAGCAGCCAGCGAAACA
ATGAAACATTTCTGACAATGCCAGTGCACCTGAGTTGAGTGGTTGAGTGCTTGGTGGTTGAGTGCCCAACTGCTGAGTGGTGCGAAAAATGTAAA
ATTGTGGGTCAGGCATTGGGGCCAAAAATAGAGCCAGCAATGCGAATCGACGGAGGGTCATTGTGTGGTAAACTGGGGCTACTTCTCGGTATCAA
TTCAATTGATAAATGGTGGAAAAATATGTCAAAGTTCTAATGAATGCATTCAATCCGTAGCAAGCAGACCTCGATCGAGATCGAGCAGCTCAATG
CCCGCGTCATCGAGGCGGAGACCCGGCTGAAGACCGAGGTGACCCGCATCAAGAAGAAGCTGCAGATCCAGATCACCGAGCTGGAGATGTCGCTG
GATGTGGCCAACAAGACCAACATCGATCTGCAGAAGGTGATCAAGAAGCAGTCGCTGCAGCTGACCGAACTGCAGGCCCACTACGAGGATGTCCA
GCGCCAGTTGCAGGCCACCTTGGACCAGTATGCCGTTGCCCAGCGCCGTCTGGCCGGTCTCAATGGCGAGCTGGAGGAGGTGCGCTCGCACCTGG
ACAGCGCCAACCGTGCCAAGCGCACCGTGGAGCTGCAGTACGAGGAGGCTGCCTCCCGCATCAACGAACTGACCACCGCCAATGTCAGCCTCGTC
TCCATCAAGTCCAAGCTGGAGCAGGAGCTCTCCGTGGTCGCCTCCGACTACGAGGAGGTGTCCAAGGAGCTGCGCATCAGCGACGAGCGCTACCA
GAAGGTCCAGGTGGAGCTCAAGCATGTCGTCGAGCAGGTGCATGAGGAGCAGGAGCGCATCGTTAAGCTGGAGACCATCAAGAAGTCCTTGGAAG
TCGAAGTCAAGGTGGGTGTTTGGGTTTTGGGACATCTATCTAACTAATATTTCATAGGGATAAAACTTACTACCTATCTGGTACTATATGACTCA
ACGAACCTTGCAATCTCTCCCGCAGAACTTGTCCATCCGCTTGGAGGAGGTCGAGCTGAACGCCGTCGCCGGCAGCAAGCGCATCATCAGCAAGC
TGGAAGCCCGCATCCGCGATCTGGAGCTGGAGCTGGAGGAGGAGAAGCGCCGCCACGCCGAGACCATCAAGATTCTGCGCAAGAAGGAGCGCACC
GTCAAGGAGGTGCTGGTGCAGTGCGAGGAGGACCAGAAGAACCTCATCCTGCTGCAGGACGCGCTGGACAAGTCCACTGCCAAGATCAACATCTA
CCGCCGCCAGCTGTCCGAGCAGGAGGGTGTCTCCCAGCAGACCACCACCCGTGTGCGCCGCTTCCAGCGCGAGCTGGAGGCTGCCGAGGATCGCG
CCGACACCGCCGAGTCCAGCCTGAACATCATCCGCGCCAAGCACCGCACATTCGTCACCACCTCGACGGTGCCCGGATCCCAGGTGTACATCCAG
GAGACCACAAGGACGATCACCGAATAGAGCCCCACGCTCCGCACCGAGATCATTTCATTATCAAACGCTAACCGAAGAACCGAACACAACCAATC
CCGAACCCATGAAGAAGACCATCTGGCGGAGGGCAGAGTTCAGAGTGCAGGACGAGAACGAGAATTGCGTGAGAAAGTTTTTATAATTTAAATTT
TTTTGTCAAACCCCCAAAACGCCGCGGCAGCGATTAGAACCCAGTGGACTTCGGCGGGGGCTCGTATAGGCTACACACTATAAATACATAACACT
ACACATCCTATCTATATAATAATAATACTATTTTGAAGTTCATGTAATTTAATTAAAATAATGAACCTGAAAAACCTAAAAACAAAATAAAAACA
AACCAACGAAAACTTGGCAGAGTTTTGCTAGCGCTAGAGATATGATATATACCATATACCATATACCACATACGATATATAATACTTGTACGTAG
AGAGATGAGAGAGATCAACCGAGTTGGCTGAACAATAACGTTTAATGGAAATGGAGCCCATTTGAACGAAAAGCACTAAAACTTAATAACTTGAA
ATGGAAATGATAATCGTCACCGAAATATCCCACTAAGCACGCCACCGCAGCATCGAGTTAACCGAGTTACAACCGCTTCTACTATTTGTTTTTAG
TTCACTTTATGTTTAGTAGGTAAATTTCTGTGTGCTCGTAACGAATTTGAATTTTACATTAAATCAGCATCAACAAAACTGAGCAATTTTCACAT
TTTTTACTTTGTATCTTGCAATAAAAACGAAATTCTATTCATAATAATAACAATAAGAAATTGTAAGTGAAATTCGGTTTTACTAATGGGGGGT
CTTCAAGATTTCAAGAAATGGTGTAGCTGCGAACCTTAGTGGACTTCAAGTAATGAAGTTTGGCATAGCCAACTCAAAGTTTTTGAAGTTTTTTT
TTTAGCCATCTAAAGTTTCATGGCATTCAAAAATAGGCAGAAGTTGTCGGAGTAAACAAACATTCTCATTTGCAAATAAAGATTCGCTCAAGTTT
GGTTTCCCAGCCCAATAAATGAATTTCCATTGATTTATATTGCTTTAAGCTATCACTATTTATTAACACTTTTGGAGCTATACAATCCAAGCTCT
TAGATGGCCACAACACCCAGTTTGGCGTCGGTCTTCAGGTACGCATTCTCGCCGTAAGATCCGCCGTATTGGCTCTTCTTGAAGACTGAAAGGTA
GAGAAGATACAAAAGAAGGTAAGTCTGGGTGGCAAAGCGGTGCTATGAAGTCAATCCAAAATCATAGGATAAACAATATTATCCAGTTAAGAACT
CCATGTTGTAGCTTAGTTTAGGAACCCACCTGGATCGACCTCAGCCACGAAGGAGCGTGGTGGCAGAGCAGCAGCGTATAGCGGGTCCAGAGGGC
CGTAGGGCTTGGCCAAAAGTGGGCGACCCTGCTCCCATCCATAACGGTTGAGGGAATTCCAGTCAGCACCGTCCAGCTTGGCGGCGGAGGCAGCT
GCTCCGGCAGCGTTGGTCAGGGCAGAAGCCTGAGCCTCGGCGGTCTCAGCGGCCTTAACCACATCGCCGTAGCTGGCTCCGTATCCGGATCCGCC
GTAGTTGGGGCGATTGGCCACAGCCAGGGCGACGCAGCAGGCCATCAGGCAGAGAAGACGTAGGGTGGCGGACATTTTTTTTGGTGGTGGTGCG
AGGAACGGACTGTTTCGAAAACTAATTAACCAGAGCGTGTGTCCAAATTGCTTTTATAGCAACACCATTTGAGCTGCTCCGCGATTTGTGAGCTC
ACCAGACGTGACCAAACC
(SEQ ID NO: 667)

Exon: 1001..1352
Exon: 1984..2040
Exon: 3892..3978
Exon: 4043..4209
Exon: 5865..6736
Exon: 6822..6949
Exon: 7034..7146

FIGURE SHEET 362

Exon: 11461..12076
Exon: 12186..13458
Start ATG: 1230

Transcript No. : CT18593
ACGAAATACTCTTTATTCGAACGACAACGGGATCTCTTGTTCAGTAGATCACCAGCCTTACTCCGACGTTTATTACGAATTTTCTCGGTGACTCG
GTGACAACTACAAAACTGCGTGCGGTGCTGTATAGATTTTCGCTTGAGAGGAACACACAAATCATAATACTAGATACGCGAACCGATCGCACATT
AATTTATAGAACCAAAATCGAAAATCTGACCTAGCAAACATGTCGTCATCGCAGGCTGTCCGCTCCTCGAAATACTCCTACCGTGCCACGTCCAC
CGGACCCGGTACCGCCGATGTGAACATCGAGTACATCCAGGACCTGAGCTCGCTCTCCCGCTTGGAGGACAAGATCCGTTTGCTCCAAGATGATC
TTGAAGTTGAACGTGAGTTGCGCCAAAGGATCGAGCGCGAGAAAGCCGATCTCAGCGTTCAGGTCATTCAGATGTCCGAGCGTCTCGAGGAGGCC
GAGGGTGGTGCTGAACATCAATTTGAAGCCAACCGCAAGCGCGACGCTGAGCTGCTGAAGCTGCGCAAGCTGCTTGAGGATGTTCATCTTGAGTC
GGAGGAGACCACTTTGCTTTTGAAGAAAAAGCACAACGAAATTATCACGGATTTCCAGGAACAGGTTGAAATCCTAACGAAAAACAAGGCCAGAG
CCGAAAAGGACAAGGCCAAATTCCAGACCGAAGTCTACGAGCTGCTCTCCCAGATCGAGTCCTACAACAAGGAGAAGATCGTGTCGGAGAAGCAC
ATCTCCAAACTGGAGGTCTCGATCTCCGAGCTCAACGTGAAGATCGAGGAGCTTAACCGCACCGTTATCGACATTAGCTCCCACCGATCCCGCCT
CTCGCAGGAGAACATTGAGCTGACCAAGGACGTCCAAGATCTGAAGGTTCAGCTGGACACGGTCTCGTTCTCCAAGAGCCAGGTCATTTCCCAGC
TGGAGGACGCCCGCCGTCGCTTGGAGGACGAGGACCGTCGTCGCTCGCTGCTCGAATCCTCTCTGCATCAGGTTGAGATCGAATTGGACTCGGTT
CGTAATCAACTCGAGGAGGAGTCCGAGGCCCGCATCGACTTGGAACGTCAGTTGGTCAAGGCCAATGCCGATGCCACCTCCTGGCAGAACAAGTG
GAACTCCGAGGTGGCTGCCCGCGCCGAGGAGGTCGAGGAGATCCGTCGCAAGTACCAGGTCCGCATCACCGAGCTGGAGGAGCACATCGAGTCCC
TCATCGTCAAGGTCAACAATCTGGAGAAGATGAAGACGCGCCTGGCCAGCGAAGTGGAGGTGCTCATCATCGATCTGGAGAAGTCGAACAACAGC
TGCCGCGAGCTGACCAAGTCGGTCAACACCCTCGAGAAGCACAACGTTGAGCTGAAGAGCCGTCTGGACGAGACCATCATCCTGTACGAGACCAG
CCAGCGCGACCTGAAGAACAAGCACGCCGACCTCGTCCGCACTGTCCACGAACTGGACAAGGTCAAGGACAACAACAACCAGCTGACCCGCGAGA
ACAAGAAACTGGGAGATGATCTTCATGAGGCCAAGGGTGCCATCAACGAACTGAACCGTCGTCTGCACGAATTGGAACTGGAGCTGCGTCGTCTG
GAGAACGAGCGTGATGAGCTGACCGCTGCCTACAAGGAAGCCGAGGCTGGCCGCAAGGCTGAGGAGCAGCGCGGACAGCGCCTGGCCGCCGACTT
CAACCAGTACCGCCACGACGCCGAGCGTCGTCTGGCCGAGAAGGATGAGGAGATCGAGGCCATTCGCAAGCAGACCTCGATCGAGATCGAGCAGC
TCAATGCCCGCGTCATCGAGGCGGAGACCCGGCTGAAGACCGAGGTGACCCGCATCAAGAAGAAGCTGCAGATCCAGATCACCGAGCTGGAGATG
TCGCTGGATGTGGCCAACAAGACCAACATCGATCTGCAGAAGGTGATCAAGAAGCAGTCGCTGCAGCTGACCGAACTGCAGGCCCACTACGAGGA
TGTCCAGCGCCAGTTGCAGGCCACCTTGGACCAGTATGCCGTTGCCCAGCGCCGTCTGGCCGGTCTCAATGGCGAGCTGGAGGAGGTGCGCTCGC
ACCTGGACAGCGCCAACCGTGCCAAGCGCACCGTGGAGCTGCAGTACGAGGAGGCTGCCTCCCGCATCAACGAACTGACCACCGCCAATGTCAGC
CTCGTCTCCATCAAGTCCAAGCTGGAGCAGGAGCTCTCCGTGGTCGCCTCCGACTACGAGGAGGTGTCCAAGGAGCTGCGCATCAGCGACGAGCG
CTACCAGAAGGTCCAGGTGGAGCTCAAGCATGTCGTCGAGCAGGTGCATGAGGAGCAGGAGCGCATCGTTAAGCTGGAGACCATCAAGAAGTCCT
TGGAAGTCGAAGTCAAGAACTTGTCCATCCGCTTGGAGGAGGTCGAGCTGAACGCCGTCGCCGGCAGCAAGCGCATCATCAGCAAGCTGGAAGCC
CGCATCCGCGATCTGGAGCTGGAGCTGGAGGAGGAGAAGCGCCGCCACGCCGAGACCATCAAGATTCTGCGCAAGAAGGAGCGCACCGTCAAGGA
GGTGCTGGTGCAGTGCGAGGAGGACCAGAAGAACCTCATCCTGCTGCAGGACGCGCTGGACAAGTCCACTGCCAAGATCAACATCTACCGCCGCC
AGCTGTCCGAGCAGGAGGGTGTCTCCCAGCAGACCACCACCCGTGTGCGCCGCTTCCAGCGCGAGCTGGAGGCTGCCGAGGATCGCGCCGACACC
GCCGAGTCCAGCCTGAACATCATCCGCGCCAAGCACCGCACATTCGTCACCACCTCGACGGTGCCCGGATCCCAGGTGTACATCCAGGAGACCAC
AAGGACGATCACCGAATAGAGCCCCACGCTCCGCACCGAGATCATTTCATTATCAAACGCTAACCGAAGAACCGAACACAACCAATCCCGAACCC
ATGAAGAAGACCATCTGGCGGAGGGCAGAGTTCAGAGTGCAGGACGAGAACGAGAATTGCGTGAGAAAGTTTTTATAATTTAAATTTTTTTGTCA
AACCCCCAAAACGCCGCGGCAGCGATTAGAACCCAGTGGACTTCGGCGGGGGCTCGTATAGGCTACACACTATAAATACATAACACTACACATCC
TATCTATATAATAATAATACTATTTTGAAGTTCATGTAATTTAATTAAAATAATGAACCTGAAAAACCTAAAAACAAAATAAAAACAAACCAACG
AAAACTTGGCAGAGTTTTGCTAGCGCTAGAGATATGATATATACCATATACCATATACCACATACGATATATAATACTTGTACGTAGAGAGATGA
GAGAGATCAACCGAGTTGGCTGAACAATAACGTTTAATGGAAATGGAGCCCATTTGAACGAAAAGCACTAAAACTTAATAACTTGAAATGGAAAT
GATAATCGTCACCGAAATATCCCACTAAGCACGCCACCGCAGCATCGAGTTAACCGAGTTACAACCGCTTCTACTATTTGTTTTAGTTCACTTT
ATGTTTAGTAGGTAAATTTCTGTGTGCTCGTAACGAATTTGAATTTTACATTAAATCAGCATCAACAAAACTGAGCAATTTTCACATTTTTTACT
TTGTATCTTGCAATAAAAACGAAATTCTATTCATAATAATAACAATAAGAAATTG
(SEQ ID NO: 668)

Start ATG: 230

MSSSQAVRSSKYSYRATSTGPGTADVNIEYIQDLSSLSRLEDKIRLLQDDLEVERELRQRIEREKADLSVQVIQMSERLEEAEGGAEHQFEANRK
RDAELLKLRKLLEDVHLESEETTLLLKKKHNEIITDFQEQVEILTKNKARAEKDKAKFQTEVYELLSQIESYNKEKIVSEKHISKLEVSISELNV
KIEELNRTVIDISSHRSRLSQENIELTKDVQDLKVQLDTVSFSKSQVISQLEDARRRLEDEDRRRSLLESSLHQVEIELDSVRNQLEEESEARID
LERQLVKANADATSWQNKWNSEVAARAEEVEEIRRKYQVRITELEEHIESLIVKVNNLEKMKTRLASEVEVLIIDLEKSNNSCRELTKSVNTLEK
HNVELKSRLDETIILYETSQRDLKNKHADLVRTVHELDKVKDNNNQLTRENKKLGDDLHEAKGAINELNRRLHELELELRRLENERDELTAAYKE
AEAGRKAEEQRGQRLAADFNQYRHDAERRLAEKDEEIEAIRKQTSIEIEQLNARVIEAETRLKTEVTRIKKKLQIQITELEMSLDVANKTNIDLQ
KVIKKQSLQLTELQAHYEDVQRQLQATLDQYAVAQRRLAGLNGELEEVRSHLDSANRAKRTVELQYEEAASRINELTTANVSLVSIKSKLEQELS
VVASDYEEVSKELRISDERYQKVQVELKHVVEQVHEEQERIVKLETIKKSLEVEVKNLSIRLEEVELNAVAGSKRIISKLEARIRDLELELEEEK
RRHAETIKILRKKERTVKEVLVQCEEDQKNLILLQDALDKSTAKINIYRRQLSEQEGVSQQTTTRVRRFQRELEAAEDRADTAESSLNIIRAKHR
TFVTTSTVPGSQVYIQETTRTITE*
(SEQ ID NO: 669)

Name: PARAMYOSIN, LONG FORM
Classification: motor_protein
Gene Symbol: Prm
FlyBase ID: FBgn0003149

Celera Sequence No. : 142000013384548
ACATAATTTCCTGCACCATCGAATTGGCTACTCTATTGTAATTGGCTGAGCTCCACAAAACTTCTTTATGCATAACATTCGAGCGTGAATTTGGT
TTAGTTATAACGTTACTCGATATATCCTATAACTATGAATAGTATTCCATGTAAAATTGCTCCTTGTTTTTGGTAATACATATATGTAAATTGTG
TATATTTCGAATTTATTTTTTTCCAAAGATTCATTTTATGAATTCTCATGCTCTTTGGTTTAATTTAAAGAATAAACTTGAACAATTTACAATAA
AAGTCAAATAAGCTTATTTTGATATTTTTATGTGGGCTTAATTTACTTTGTGCCCACTGTAGAACAGATGCAACCAGGTGAACACAGAATATCGC TTATCGATAACTCAGCCCTGTTAATATTTGTCTGCGAAAACAGCTGTGGCTATTGTCTGTTAACTCGCTTAGTCTATTTATTTAACTAAATACCA
TGTCGAATATTTCAAGTGTGGCACCACCTCCTCCCCCACCACCCATGATAGTCACTCCTAGCACACCTGCTACCACAAAGGAACGTCCAGTTGGG
GACAATATAACCACCGATGAGTGCACTTGGGCATGTGAGTATCCTGAGGTGCAGAAAGGATGCTATTTAAGTCGCGTCTGCCAATATACACCACC
GAAACACTGTCAATACTACTCCGTAAACAGCATAGTGCAGGTGAGTTAGAAAACAATAAAGATTTCTCAGTTTGTTATTCGATAACATATGTATG
TGCACCGAAGGTGGGACCTACTTGTGGCTTAGTGGCCCTCAGCATGTTGCTTGGTGGCAGTCCCACGGCAGATGATCTCCTCAAGGATGCAATCG
ACCAGGAGTATACCCTTAATGGTGAACTATTTAGTGCTCAGTATTTGTTTGAACTGACCCGGAAGCATATGCCAGGACCTGCTGCGTGTCAGTTG
CATGTAGGTCCTTTGGACTGCAAAAAAGTCAAGGAACTTTTAAAGGCCGGAGGCTGCCTACTAGTGCCGTATCCTTTTTCAAAAATATTGCCATT
TAAACCCGGGTTGAGTTTGGTATTCCCCTGCATTTAAAGCCGTTGGCGCCTAACAGCACTTGTAAACGGTGAACAGCACACTGTTGTCTGGCAGT
GTTGTAAAACTCGCGGTAGTTCAGTGGTGCAACTTATAAACAGCGTTTTGTGTTTCGCAAAATAATATACAATTTTCAGTCAGTAAGTAAACGAG
AAGTGCAAATACTTTTATTAAATGGCCGACGAAACAGAGCAGGTATGTGTAAGAATAAAAGCGAAAAGGATATTCTCTATATTCCGTACTTGCAG
CTCAGTCAGGTGATTTTGCCGGTAAAGGAGCCTTTGGATCTCATCCGATTGAGTTTAGATGAGAAGGTGTACGTAAAGATGCGCAACGAGCGGGA
ACTGCGAGGACGTCTTCACGTGAGTTGATGCCTCTTTTTACTGTTGCCCAGCAATCTTTCAATATACACCTTTATCTAGGCCTTTGATCAGCATT
TGAACATGGTGCTCGGCGATGCGGAGGAGACGGTGACCACTGTGGAGATCGACGAGGAGACCTATGAGGAGGTGTACAAGACCGCCAAGCGCACT
ATTCCCATGCTATTCGTTAGAGGCGATGGAGTCATCCTGGTTTCGCCACCCATGCGGGTGGGCTAGCGGGTCTTGTTTAGCTTTAAATCAATTAC
CTGCATTTATACAAGCTATATCTAAATAGGTTTATAAATGTCTTTTAAAAAAAATAATGTCTTGTTTAATTTTTGCTTACTATATAAATATATAA
AAATCTTTTCTATGGGTTGTCCTTAATCAATTGTAATTTCAAAAGCTACGATGCCGATGTAAACCATGCGCCATGCGTTAAAAATGGACACCGAG
CCCATTGGGCTTTGATTGTAGGTTATCTGGTGGACACGCAGGACCGGGTGAGTGGAAAAAGCTAGGCATATTAAGACCAATATTAATGTATAAGC
CCTTCCGCAGTTTTATGTCCTGGCTCGTCATGGTAAATCTCGTAACCTAGCCGTTTGGCCACTGGACACGCTCAGCCAAAGCAACGAAAATTTAA
AAGAGTTTGCCCAACCCAAGGGCTACCCAGATGATGAGTTTCTGCTGCCACCGGGTGGAATCGGTGGATCTCTGGGCCTCAACGAGCGCTGCATT
CTTGTCAACGGGCTGCCAAAGCAGGTGATTCATGTTCGCTGGTCCTAAATATATGTGCATCGAAATATTTTCAATAAAAAAAACCTTTTTAATT
ACGTAGTTAACTTTAATATATTTAATAGTACAGTTATAAATTACACGCCTTACAATATTTCACTTCGCAACGCAATCAACGCACCTCGAACTCCT
TTCCATCATTCAGTTCAAACGGGGAGAGAAACACGCAGAGTTTTCGTATTTAATCGGTTCGCAACTACTACGGGGACACGAATGCGATTTTAGGG
GGAATAGAATATAATATACAATAATGATATATCGAACTTTCATTTGGTTTAGAGCCAGCTGTGTATAAATTTATGTATACAAGTATAAATTTACG
CTTTTCCAACATCCGCTAATAAGACTGGGCTGCCTTGAAATTTCAAAAATCACAACAATAAGAGTAGTACACATGGTTTTGTATATATGGTAGAT
AAGATAGGTAACTATATATAGTATGTTTTGTATATAATTTCACACACAGATATTTTTCTGATTTAGGTAGTACATAGACGACGGGCTTGGGTATA
ATGTCAAATTTTTGTCAAGTAGATTTAGTATGCTGCTGTACTTTTAGGTTCATTTGATAGTTGGCCAAACGGGAGCGGCGATTTTGAGATCATGG
GGCCTAATGCTCCCGATTGCTTGGAAACTGTCGGTTAAAGAATATATATATATTTTATTATATATGCTAGTACATGCCAACAGGCAAGAGCAACG
TGTCCATAGAAATTTTTGAAACGGCAACTACAAAGTTTGGTTTTAGTTCTAGAACTTCTTGTACAGGATATTTTGATACGCGTTGTTCATCTCTG
ACGAGTTTATAATTACTTTGAGCATACCATTAAACTAGTTAGTGTCTGTTTGTCTGTATGTGTCTGGTTGCGGGTCGAAAGTATCTCTGATAAAT
TCACAAGTTGCGTGCGAAAATGAACTGAACTTAAATGAACGTTACAGGCTAACGGTTTATTAACTAAAAATTTACAAATACTAGTTATAAATAAA
TTA
(SEQ ID NO: 670)

Exon: 1001..1277
Exon: 1327..1444
Exon: 1505..1672
Exon: 2006..2233
Start ATG: 1409

Transcript No. : CT18597
AGGCTGCCTACTAGTGCCGTATCCTTTTTCAAAAATATTGCCATTTAAACCCGGGTTGAGTTTGGTATTCCCCTGCATTTAAAGCCGTTGGCGCC
TAACAGCACTTGTAAACGGTGAACAGCACACTGTTGTCTGGCAGTGTTGTAAAACTCGCGGTAGTTCAGTGGTGCAACTTATAAACAGCGTTTTG
TGTTTCGCAAAATAATATACAATTTTCAGTCAGTAAGTAAACGAGAAGTGCAAATACTTTTATTAAATGGCCGACGAAACAGAGCAGGCAGCTCA
GTCAGGTGATTTTGCCGGTAAAGGAGCCTTTGGATCTCATCCGATTGAGTTTAGATGAGAAGGTGTACGTAAAGATGCGCAACGAGCGGGAACTG
CGAGGACGTCTTCACGCCTTTGATCAGCATTTGAACATGGTGCTCGGCGATGCGGAGGAGACGGTGACCACTGTGGAGATCGACGAGGAGACCTA
TGAGGAGGTGTACAAGACCGCCAAGCGCACTATTCCCATGCTATTCGTTAGAGGCGATGGAGTCATCCTGGTTTCGCCACCCATGCGGTTTTATG
TCCTGGCTCGTCATGGTAAATCTCGTAACCTAGCCGTTTGGCCACTGGACACGCTCAGCCAAAGCAACGAAAATTTAAAAGAGTTTGCCCAACCC
AAGGGCTACCCAGATGATGAGTTTCTGCTGCCACCGGGTGGAATCGGTGGATCTCTGGGCCTCAACGAGCGCTGCATTCTTGTCAACGGGCTGCC
AAAGCAGGTGATTCATGTTCGCTGGTCCTAA
(SEQ ID NO: 671)

Start ATG: 360

MRNERELRGRLHAFDQHLNMVLGDAEETVTTVEIDEETYEEVYKTAKRTIPMLFVRGDGVILVSPPMRFYVLARHGKSRNLAVWPLDTLSQSNEN
LKEFAQPKGYPDDEFLLPPGGIGGSLGLNERCILVNGLPKQVIHVRWS*
(SEQ ID NO: 672)

Name: LSM3; U6 core snRNP protein
Classification: RNA_binding

Celera Sequence No. : 142000013384321
CTGTTTGCGGCTGGTTAACTGAGTGGGTGTATTGGCCACATCGTAGTCCAGCTCATCACCAGTTTGCTTAAGGCTGTGATACAGGAACTTGGACA
GCAAATTCTTTGTTTGCAGCGCCTCCCGGGACCGCTCCTTTAGGCAGTAGTTGTGCTGTGTATCTCCATAGGTCAGGACGTGCTCCAGAATAAAG
GATCTTAGCCACTTCCAGTCGTCATCCGCCTTTCGCAGCAGATACTTCTGGATGTCGAACTCATCCAGGAGCAACGTGTTGCCCCACCTTGTGCAC
AACCATGCTGATGGCGCTCTTCGCGCTGTAAGGCAACTTGAGTAGCTGCTTGATATTCTCCGCGTCGCTGACCACATCCACCTCTCCCACGCAGT
CCGGAAACATCTGGCCCAATCGAAAACTGGCAAAGCCAGCACTTTGGTAGAGGGCCTGGTGTAATCCATGACTGCTGTGCGACGTTGTCAGCCAG
TTGAGAGGCGGAAGATTCAAGTTGGTGTTGCACTCCAGCCGCTTGAAGTGGGCTGGCACTGGAACGGGAGACAACTTAATCACCGCCTGGCTTTT
TACGACGTCCAACTCATGTGGTCCAATACTCCTGCACGGTTCAATCTATCGAAAAACATGTGTTATTTATTTAAGCTTCTTTGCGCACATTCTTA
CTTCTTCGTTTCTATCTTCCATTATTGCGCTCGCTCATTGGTAACTCCCTGAAAATCCAATCCCGTGGAATATTCAAGAAACTTTCGAGCAGATG
TGTTTTTGTTTTGCCGGCTCAGCTGATAGCTGCCGCAGTTTTCCAACACCGGACCAGACCGGCGCTGCCAACTTAGTGCCAGCACAGTTGCATGG GATCAGGTAGACTTCAAAACCTCTACAATTTATAAGGGTTTAAACTAAGTTTCAAGACTAATTATATATGGCATACAATAAACCTCATATTTAGT
TATTCAATACTTCCAACACACTTTTGCTCTCTAGATGATCGAAATGAAACTTACAATGAAATTTCTTTCAGTGGTAGCTCAAAATTTAAGCATAA
TAATTATTTCAAAAACTATGTGAAAATATAACTGTGGGAAACCGTCCCCTCTCCTACGCCACTGGCCAATTCCAAGCTGATGACTTTCTGATGCT
CGTTATCCAGCACTGGTATATTATTTTGTTTTCCATTCAGTAACACGATTATCACAAACTGTCGCAAATTTTCCCGAATTGAATACAAATCTGAC
ACAAAAGCATGACACTGTTTGCCCTCATCGCCCTGCTCAGCCTGCTGAACACAATCCTGCCAGATTTCATAAGGAACTACGTGAGTACCATCCGC
AAGAGAAAACCCCAGTGTAGAACCTTATCCTGACCTGCAGCTCAAAGTGTCGCGGTTGTGGGGCGTAAGGAACTCCGCGGAAATTCGGCAGTTGC
AGACAGAACTGGACGATGCCCGGAAGCAAGTGGAGGTGGTCAGCAATGCGGAGCATTCCGGAGAGTACGCCAGGACCATCAAAATTATGCGCGCC
GAGCGTAAAGTATCAGAGGCGGAGGCGAAACTGAAATCTGCCCGGGGAATGGAGAACTTCATGCGGATAAGCATCGATACGGCCATGTTCTACGG
ATCTAAGGTGCTGCTCTCAGCAATAACCGTGTTTATCAGCATCCGGAATCGTGGAACGCCCGTCATGATCATCGATGAAGCGATCAGCCTGGCTC
CGTTCACAGGACTTCTTAGTTTTCCTACTGGCGTGGCCAATGCCATTTCGGTGCCCGCCTGGGCATTCTCCTGCAACCTGACATTTCGACTCATC
TACGGCTTTGTGAAAAATCGTGGGGCGTGATTCCATCCGAGCGAAATCCCTCCATTTCATTTAGCACTTAGAAGGCGCTCGAAACTATGTACTTT
GTTATGGTTTGCTAAGCTTCATCATGCATTGACTCTTGAATGTAAAGGCCCAATTTTATGTAAGCACCACATCAAATAAATGTATTTTCAGACAA
GATTCAGTTTGAATCACGCGCCTTGGTCTAAGGGTGTTTTCCATCACTGCTCGTAAACATAGTGTTGCGCTGTGCTCACTCTAGATGAGTGCGTG
TCATTTTCCCCATCCAATTTGTTTGGTGTTTTGTTAGCCGAAATGGACAAACTAAATGAAAATGCTCGACAGCGGAAGCAGATCAAGCTGGGAGA
GATCGACACGGGCCCCATTATAGTGGCCCTCCTGCTAGGCTTCATTGCAGTGGGTGAGTCCGCCACGTGGAGTTCGCCTTTTGCCCCAGGGAGTC
TCACCTGATGTCTATAATCCCGTTCACACGTTTTCTCTTTTAGCCATATTTGTGATCCTGCGAAGACGCTCTGCTGGTCGCAAGGACTTTCTGCT
TACTGGGCTCAGTGAATCCGGCAAAAGTGCCATCTTCATGCAGCTGATCCACGGCAAATTCCCGGCCACTTTTACTTCCATCAAGGAGAACGTGG
GAGATTACCGGACGGGCAGCGCGTCTGCCAGGTTAGTGGATATACCCGGACATTATAGGGTGCGCGACAAGTGCTTGGAGCTATATAAACACCGT
GCCAAGGGCATTGTCTTTGTGGTGGACTCGGTTACTGCCCACAAGGATATCCGGGATGTGGCAGAGTGAGTTTTCAATTAATGTACAACCTAGAT
GCGGTGCTAATCTTATTGGTTTTCCAGCTTTCTGTACACCATCCTATCAGACAGTGCCACACAACCCTGCTCTGTGCTAGTCCTTTGCAACAAGC
AGGATCAAACCACCGCCAAGAGTGCCCAGGTCATTAAAAGCTTATTGGAGTCGGAACTGCACACAGTGCGCGACACCAGAAGCCGCAAACTTCAA
TCCGTGGGCGACGAGGATGGCAGCAAATCCATCACATTGGGCAAGCCAGGCCGTGACTTCGAATTCTCACACATCGCACAGAATATCCAGTTTGC
GGAAGCCTCCGCCAAGGACACTGAACTTGATCCCCTCACCGATTGGCTCGCTCGGTTGCTGTGAATTGGGCACACAAGGCTCTCAGACTGATAAA
AAACTGGAGTCCTGAAGGAAAGAATGCGGAACAAAAAAACAACAGATTGATATTTATTTTAACGTTTAGCGCTCTGAATGTCGTATTTATTATGC
TAAGCCGATATACACCGCTGAGTATAAATCCGTGCATTGTTAAATATCCTCTTTTCCCATCCTTTGCCTTCCACCTATTTTCCCGTCTAATTTTA
GGTTATTGTGGAAATTTTATATACTTTTAGCATTAATTTGTCGGTAGATAAGTGATAAAGTCATTTATAAACCGATTAAAAAGAAAAAAACCCAA
ATAAGATTTACGAGTTTTTAAAAGCAGGTTGTGGGATCAGCAAAGGCTCCAAATAATAGCATGCTGGGGGGCTTAAATTTATGTCGTACATGTTT
TTCTTTATTTTTAAGAAATGCCGCCAAAACTGAGTTTAGTTCATTGACTATCGATAGCACAGATATGTTTAACTTTTTAGTTCAATTTTCAAACA
CAATTATCTGGTGGCGCCATTGTTTAGGCATGTAAAATTTTACGTAGCAGTCATGTAGAATTAGCACAACCTTATTTTTAAAATATAGCTTAGAA
TAATAAGCATTAAATAATTTAAAGCTCAGAAAAAAAATACATGTTTTGAAATTCTACATAAATTGGCTATAATAAAAATTTTTTTAATGTTATAAA
AAAATGGAAAAAGTACAATTAACATTGAGAGTATAAATATTTCTTCATTTGAGTAAGGCTTCTATGAAAAAGTTCGATTTATATATATGTTTATA
TCTACAGCAACAATTCGCTTCCTTTTATTTCAACAGCTGTATCTAATTTGATTATCACATGACCGAAATTCATGAAAAAGGGGTTTTGCTCAACT
AGCAGTTGGCAAAGCCATATTTTTGACCAACTGTCCCAGAAACGAGGATTATTGTTAGATCGCTGAGCAAACGTTTGGCGCATGCGCAAGCTTTC
AAACCTTTTTCGCGATTTG
(SEQ ID NO: 673)

Exon: 1001..1315
Exon: 1371..1824
Exon: 2080..2238
Exon: 2324..2630
Exon: 2688..3009
Start ATG: 1244

Transcript No. : CT18686
TTACAATGAAATTTCTTTCAGTGGTAGCTCAAAATTTAAGCATAATAATTATTTCAAAAACTATGTGAAAATATAACTGTGGGAAACCGTCCCCT
CTCCTACGCCACTGGCCAATTCCAAGCTGATGACTTTCTGATGCTCGTTATCCAGCACTGGTATATTATTTTGTTTTCCATTCAGTAACACGATT
ATCACAAACTGTCGCAAATTTTCCCGAATTGAATACAAATCTGACACAAAAGCATGACACTGTTTGCCCTCATCGCCCTGCTCAGCCTGCTGAAC
ACAATCCTGCCAGATTTCATAAGGAACTACCTCAAAGTGTCGCGGTTGTGGGGCGTAAGGAACTCCGCGGAAATTCGGCAGTTGCAGACAGAACT
GGACGATGCCCGGAAGCAAGTGGAGGTGGTCAGCAATGCGGAGCATTCCGGAGAGTACGCCAGGACCATCAAAATTATGCGCGCCGAGCGTAAAG
TATCAGAGGCGGAGGCGAAACTGAAATCTGCCCGGGGAATGGAGAACTTCATGCGGATAAGCATCGATACGGCCATGTTCTACGGATCTAAGGTG
CTGCTCTCAGCAATAACCGTGTTTATCAGCATCCGGAATCGTGGAACGCCCGTCATGATCATCGATGAAGCGATCAGCCTGGCTCCGTTCACAGG
ACTTCTTAGTTTTCCTACTGGCGTGGCCAATGCCATTTCGGTGCCCGCCTGGGCATTCTCCTGCAACCTGACATTTCGACTCATCTACGGCTTTG
TGAAAAATCATGAGTGCGTGTCATTTTCCCCATCCAATTTGTTTGGTGTTTTGTTAGCCGAAATGGACAAACTAAATGAAAATGCTCGACAGCGG
AAGCAGATCAAGCTGGGAGAGATCGACACGGGCCCCATTATAGTGGCCCTCCTGCTAGGCTTCATTGCAGTGGCCATATTTGTGATCCTGCGAAG
ACGCTCTGCTGGTCGCAAGGACTTTCTGCTTACTGGGCTCAGTGAATCCGGCAAAAGTGCCATCTTCATGCAGCTGATCCACGGCAAATTCCCGG
CCACTTTTACTTCCATCAAGGAGAACGTGGGAGATTACCGGACGGGCAGCGCGTCTGCCAGGTTAGTGGATATACCCGGACATTATAGGGTGCGC
GACAAGTGCTTGGAGCTATATAAACACCGTGCCAAGGGCATTGTCTTTGTGGTGGACTCGGTTACTGCCCACAAGGATATCCGGGATGTGGCAGA
CTTTCTGTACACCATCCTATCAGACAGTGCCACACAACCCTGCTCTGTGCTAGTCCTTTGCAACAAGCAGGATCAAACCACCGCCAAGAGTGCCC
AGGTCATTAAAAGCTTATTGGAGTCGGAACTGCACACAGTGCGCGACACCAGAAGCCGCAAACTTCAATCCGTGGGCGACGAGGATGGCAGCAAA
TCCATCACATTGGGCAAGCCAGGCCGTGACTTCGAATTCTCACACATCGCACAGAATATCCAGTTTGCGGAAGCCTCCGCCAAGGACACTGAACT
TGATCCCCTCACCGATTGGCTCGCTCGGTTGCTGTGA
(SEQ ID NO: 674)

Start ATG: 244

MTLFALIALLSLLNTILPDFIRNYLKVSRLWGVRNSAEIRQLQTELDDARKQVEVVSNAEHSGEYARTIKIMRAERKVSEAEAKLKSARGMENFM
RISIDTAMFYGSKVLLSAITVFISIRNRGTPVMIIDEAISLAPFTGLLSFPTGVANAISVPAWAFSCNLTFRLIYGFVKNHECVSFSPSNLFGVL
LAEMDKLNENARQRKQIKLGEIDTGPIIVALLLGFIAVAIFVILRRRSAGRKDFLLTGLSESGKSAIFMQLIHGKFPATFTSIKENVGDYRTGSA
SARLVDIPGHYRVRDKCLELYKHRAKGIVFVVDSVTAHKDIRDVADFLYTILSDSATQPCSVLVLCNKQDQTTAKSAQVIKSLLESELHTVRDTR
SRKLQSVGDEDGSKSITLGKPGRDFEFSHIAQNIQFAEASAKDTELDPLTDWLARLL*
(SEQ ID NO: 675)

FIGURE SHEET 365

Classification: enzyme
Gene Symbol: BcDNA:GM04779
FlyBase ID: FBgn0028478

Celera Sequence No. : 142000013384548
CTGGGTAAGACAGTCGAGAAAAGCTACCATGGCAGCATCAAACTTGGTGTCCCAGAAAAACTTAAATCCGCCGCTGCCATAAAGCGGGAGCTCTC
GATTCTCGCCGAGCACCTCAACATACGAATGATTTCCAAAGGGTACTACACGATACCGCTCGAAGGTGAGCCCTATCTTACGAGCAAGCGCAGAG
AGCAGAAGCACCGTCTGGCCCCAAGCGGCGTTGATCTCTGACCAGTCCACGGATACAGAGGGCAATCGACCCAGCCTAAAGTTATTAATGGTACC
GAAATGCCCGGCATGCCAGATGTGAAAGGTGATGTTGAATATGTTGGTGTCGCGCAGTTTGTCCAGCTGCTGTTTCGAGTAGGCGATCTGACACT
CCAGACTTCGTTTGTCATCCTCGGTGAGCATTAGCTCACGCCTGTGCTTGGTATACTCGCGCCAGTAGCTTTCCTCCTGCTCGTGCAGCTCCTCT
CGCTCCTGTTCCTCCTCGGCAATGGCATCATTTAGCGATTGTTCCTCCTTTTTGAGCTCTTTTAGCTCCGACAGAAGCTGTTGCTCGCTGCGCTT
TAGTTCGTCGAGCTCCTTGTCCAGGGCCTCAACGTTGGGTGCTACACGCTGTTGCTCTAGTTCATCCAAATAAGCCTTGTACACATCCCACTCGT
CCTCAGCGATGCGCAGTTCCCTGTCCATGATTTCCAGCATGGAGTCGGCACACTCTTCGCACAGCGGATGGTCAATCTCAGAGTTGGAGGAGAGG
CAGTCAAACAGCTCCGCTTTCAGCTTAAAAGCAGCACTCATTTTCTTGTTGTCCCTGCCATCGGAAACCAGCATAAAACCAGTGCCATTTATAGA
GTCCGTAAGCCTGTAGGGCGGCACAAAGTGGTCGAAGCTGCTGGCGTCCTGCGGGTCCAATGTATTGCCATTGTCTCCGTAGATGGGCACTGAAA
AAGTGATTTATTAGACTAATTTCCAGAGTGTATCACCCATCATCACCTACAAGATAACTCCGCCATTGCGTGCACGCTAATCTTCTCCAGCTGCT
CGTCCAGGACGATGGGCTGCAGGCAGCGCTGACAGGCGAAGGACACCGCCTGCTTTTCCGCCTCACTCATTGTCGTTCCTGTTTGTTGTCCTTCG
ATTTTTGCATACAATTAAATCTTTCACCGAGTGTAAAAACACAAATAATCCATCAGCTGTTTGCAACTGCTACCAGAGTTGCCACCCCCTCCGAA
AAAGAGTGTGGAAAAATGGCGCAGTTAATCGGACAGTAAATCGTCAACCAACAACAACCTGAGACAGTAAAAAAGAGAGAAATAACAGAAAACCA
GTTTTAAACAATAACATTGCCTAATTGTGTCCGCCGGAGATGCTTAAGCGTGCCGCGAAGCTGCAGGCCTTGACCACAATTCCCGCTGATAAGAG
AGAACTCAAGGGGTTGGCTTTTGGTTTGTTTTGGTAAGCGACAGAACATTAGACGGAGTGCCGTCGCCAGTGCTGCCAACCTATTTTAGCTATAG
CAAATATTTCATAGTAGCAAAGAGGTAGAACCCAAATACAATTTTTATAAATAATAGTTTATAGTTAGCGAACGGACTAAAAGAGAAACCTGATA
TCGAACGACTTATTATATTTTTTGTTAACTCAATTTTAAACTTACTCCAGCGTAAACCATACTTTATAAATAGTTTACCAAAAATGATAGCACAA
GTGCCAGAAAGCTATTCACTTCATTTTTAATTTGATTAGGTAAATTGTGCGAAGGAAGTATTTAAAAAAATGTGAAATGACGTACTAAGCACCCC
ACATATAGACTAAGAATTAAAGGTTAAGGACATTGACTTTCGCAATCTTTGTATTGTAGTTAAGCCACAAGCATTGATAAGCAAAGAAATTGTAA
GAGTGAAATAAAATCATAATAAGATGAATTAATTAAAGTAGAGAAACTGATAAAGACTTGCACTTGAAGCTGACACATGTGTTTAATAACTATAT
AATTGCTAAGGGAAATTTTGTTTTTGAAAAGTTTCCGTTATCAAGCTCGAAATTTCTAGCAATGGGGCAGCACGAAATTTGCCGCTGTAAATCTA
GCTTTCAAAACCTGGCAGCACTGTCGGTGGTCACATTGTAGCCTCTTCGCATTTGACGACCCATGGAAAACTTTCAGTCTCTTGCAGGCAGCACA
GCGATACGGAAGCAACAATTGAAACGTCCAGAACTCCTCCTCCCACGAGTATTTAAATTCTGACACAAGAGTGCCTGAACCAAAATCCCACTCAC
CGAATGCTGGTGCTTTGATTTGCAACTGTTCCTAGGTTCCGGCTGAATCCCTAGATTTGCGGATCTACGCAACTCATTCACTCAAAAGCCAGCCG
AATTTATCGCGCCAGATTAAACAAACAGAAACAAAAAACAGAAGCCGAGACCAGTTCCACATCGTGCCATTTTTATCTGGGCATATAGGCAGACG
TGATTACGTGATTAGTGCGGCTGGGGCTGCCGTTTATCAATAGCGAGAGCAACAATGGTTTCCTACTTCGTACCTCGTGGCCGCTTCCTGCTGAA
GGCCGGCAATCTCAGACAGGTGGTGCAGCAGCAGCATCAGCCGGCCCAGCTACAGCTGCAGCCCATTAAAGGACCACAGCCGCAGGCTCAGAATG
CCAGTCTGCCGGTGGCCCGTCACTTGCGCCAATTCTCCTCGAATCCAGCCTCCAAGGAGGCACCATTACACCACCGGCGCCCGCAACATAAACAA
CAACCGAATCCTAGTCAGGAGTTAGCTCAGATTCGGCGCAATATACTCTCACGGTGGACGGGCTTCCTGTTGCGTTGGGCTCCCATGGGCATCTG
TGTGTTTGGCGCCATCGAGTGGCAGTTGCAGAAGAACCGCTGCGAAAAGGAAGGAAAACCTCGGACAGCGTCCGAGCTCCAGTCGCGCATTTACT
GCTCCCTGCCACTGCGCATAATCAGCCGTTGCTGGGGCTGGCTGGCCGCTTGCTACTTGCCTCCCAGTCTGCGTCCCTACGTCTACGGATGGTAT
TCCAACACGTTTGATGTTAATTTGAGCGAGGCCATGTATCCGGAGTATGAGCACTACAATAGTCTGGCTGAGTTCTTTACCAGGCCACTTAAGGA
GGGCGTTCGTGTCATCGATCAGCAGGCTCCACTGGTCTCCCCCGCCGACGGTAAGGTTCTACATTTTGGCAGCGCCTCGGACTCGCTAATAGAGC
AGGTCAAGGGTGTTAGCTACAGTATCGAGGACTTCCTTGGCCCGCTGGAGACTGTGGAGCAGGCAAATTCCGGTGCCTCCTATGCCCAGGCCCTC
AAAAAGAAGAGCGATGGTTCTACGGAGCTGTACCAGTGCGTGATATATCTGGCTCCCGGAGATTACCATCGATTCCACTCTCCTACCGCTTGGAA
GCCCACCATTCGTCGTCACTTCTCCGGCGAACTGCTGTCCGTGAGCCCCAAAGTTGCCGGCTGGCTGCCTGGTCTGTTTTGCCTCAACGAACGTG
TGCTGTACATGGGCCAGTGGAAGCACGGATTCTTCTCCTACACCGCCGTGGGTGCCACAAACGTGGGATCCGTCGAAATCTACATGGATGCCGAT
CTGAAGACGAACCGTTGGACTGGATTCAATGTCGGCAAGCATCCGCCCAGCACCTACGAGTACGATGAACTGGTCTTGAACAAAGAACTAACAGA
AGCGCCCAAGGAATTCGGCAAGGGGGATCTGGTGGGCCAGTTCAATATGGGCAGCACCATAGTCCTGCTCTTCGAGGCGCCAAAGAATTTCAAAT
TTGATATTATCGCCGGTCAGAAGATCCGCGTTGGCGAGTCCCTCGGCCACATCGTCGGCTCCAAATGAAAATGGGAGCCACAATTATGTACCGAA
TCAGTGCAAAGTCCTGTCCCCCAACTGCTCAGATCACTTGTTGTATTAGCATTAGACGCTCGTGTCCTAGGCAAATGTATTTTGTGAACATCCTG
CGAAGCTAACTCTGTGTATTGTTGCCATTTCAGTAGTTTTAAGCTATATTTTATACAATAAACGTCGAAATTATATTTGAGAACAACAACAGCAC
CATCCATCAATTAACTCATTCAGGCACGCGCTTCTGAAGTAGAACACCGATTGTTGAGGTGGGGCGTTATCAGGGAACGTTTTGATAAGAGATAC
CAGGCTGAAACGCAGTCGTTGAACCCCTCGTTGCTGAGGATTCAGAAAGACTAAGTCTGTGTCTGTAGCCAGCTTATCGGGCCAAATAACGCTCC
GGGGGTCCACACTCACCTCCTTTTGCGGAGTCCACGCTATCAGTGAACCTGAAAATGAAGCAAAACCTTTTTGGGCTAGACAAGCGCGTGCCGCT
GCCGACGACAAGATGACAAGTCGTCTATGCCTTGCGCCACCCAGTGTTTACTTTAGCGCAGAATCCGGGATCGCAATCCATTCCGTTTAATTAAT
TCAATCAAGCCCGGACGCCGGGAATCTTGTTCGTTGAACTTATCAGGCGGTGACGGGTGATTTGGTTCCTGGCCTTGACACACACACTCCACGAA
GTCCGTGAGTGTTAATTATTCGCCATGGCAACCGATTTGATTGCAAATCGAGCATCGGCTTAAGGGCAATCACTAAGGGAACTTCGAATATGGCG
CCAACAGTGCTGTAAATGTTTAAATAAAAGTATAAGTCGTGGAATTGCCACTCTTTAAAGCTATTCGTTGTGAAAAAAAAACATAAGGAACTTTT
ATTTTGGCATATCACGCCATATTCTTATCAAATAATTTTTTTTCGGTTTAATTTTAAAAATTCGCGCCAACTCGATAAATGAACGTTCAGTTAAA
TTCACCTCATTGTACAAACGAGGTGAACTGTGTTAAACAGCTGACAGCCGGCATTCATTTGTTGTTCTCTGTGATTTTACGTAATATTGGTATTT
ATTCTGAATATAATTGTTTATAAAGCACATTAAAATGATGATGCGACACTGTATGATGGCCTTGAGGGTCGCTAGATCCCAGATCCCGTTCAGCA
CTGCCAGGAATACTCAGAGCAATCTCCTCCAACGTT
(SEQ ID NO: 676)

Exon: 1001..1458
Exon: 2121..4071
Start ATG: 2525

Transcript No. : CT18825
AAGATAACTCCGCCATTGCGTGCACGCTAATCTTCTCCAGCTGCTCGTCCAGGACGATGGGCTGCAGGCAGCGCTGACAGGCGAAGGACACCGCC
TGCTTTTCCGCCTCACTCATTGTCGTTCCTGTTTGTTGTCCTTCGATTTTTGCATACAATTAAATCTTTCACCGAGTGTAAAAACACAAATAATC
CATCAGCTGTTTGCAACTGCTACCAGAGTTGCCACCCCCTCCGAAAAAGAGTGTGGAAAAATGGCGCAGTTAATCGGACAGTAAATCGTCAACCA ACAACAACCTGAGACAGTAAAAAAGAGAGAAATAACAGAAAACCAGTTTTAAACAATAACATTGCCTAATTGTGTCCGCCGGAGATGCTTAAGCG
TGCCGCGAAGCTGCAGGCCTTGACCACAATTCCCGCTGATAAGAGAGAACTCAAGGGGTTGGCTTTTGGTTTGTTTTGTCACATTGTAGCCTCTT
CGCATTTGACGACCCATGGAAAACTTTCAGTCTCTTGCAGGCAGCACAGCGATACGGAAGCAACAATTGAAACGTCCAGAACTCCTCCTCCCACG
AGTATTTAAATTCTGACACAAGAGTGCCTGAACCAAAATCCCACTCACCGAATGCTGGTGCTTTGATTTGCAACTGTTCCTAGGTTCCGGCTGAA
TCCCTAGATTTGCGGATCTACGCAACTCATTCACTCAAAAGCCAGCCGAATTTATCGCGCCAGATTAAACAAACAGAAACAAAAAACAGAAGCCG
AGACCAGTTCCACATCGTGCCATTTTTATCTGGGCATATAGGCAGACGTGATTACGTGATTAGTGCGGCTGGGGCTGCCGTTTATCAATAGCGAG
AGCAACAATGGTTTCCTACTTCGTACCTCGTGGCCGCTTCCTGCTGAAGGCCGGCAATCTCAGACAGGTGGTGCAGCAGCAGCATCAGCCGGCCC
AGCTACAGCTGCAGCCCATTAAAGGACCACAGCCGCAGGCTCAGAATGCCAGTCTGCCGGTGGCCCGTCACTTGCGCCAATTCTCCTCGAATCCA
GCCTCCAAGGAGGCACCATTACACCACCGGCGCCCGCAACATAAACAACAACCGAATCCTAGTCAGGAGTTAGCTCAGATTCGGCGCAATATACT
CTCACGGTGGACGGGCTTCCTGTTGCGTTGGGCTCCCATGGGCATCTGTGTGTTTGGCGCCATCGAGTGGCAGTTGCAGAAGAACCGCTGCGAAA
AGGAAGGAAAACCTCGGACAGCGTCCGAGCTCCAGTCGCGCATTTACTGCTCCCTGCCACTGCGCATAATCAGCCGTTGCTGGGGCTGGCTGGCC
GCTTGCTACTTGCCTCCCAGTCTGCGTCCCTACGTCTACGGATGGTATTCCAACACGTTTGATGTTAATTTGAGCGAGGCCATGTATCCGGAGTA
TGAGCACTACAATAGTCTGGCTGAGTTCTTTACCAGGCCACTTAAGGAGGGCGTTCGTGTCATCGATCAGCAGGCTCCACTGGTCTCCCCCGCCG
ACGGTAAGGTTCTACATTTTGGCAGCGCCTCGGACTCGCTAATAGAGCAGGTCAAGGGTGTTAGCTACAGTATCGAGGACTTCCTTGGCCCGCTG
GAGACTGTGGAGCAGGCAAATTCCGGTGCCTCCTATGCCCAGGCCCTCAAAAAGAAGAGCGATGGTTCTACGGAGCTGTACCAGTGCGTGATATA
TCTGGCTCCCGGAGATTACCATCGATTCCACTCTCCTACCGCTTGGAAGCCCACCATTCGTCGTCACTTCTCCGGCGAACTGCTGTCCGTGAGCC
CCAAAGTTGCCGGCTGGCTGCCTGGTCTGTTTTGCCTCAACGAACGTGTGCTGTACATGGGCCAGTGGAAGCACGGATTCTTCTCCTACACCGCC
GTGGGTGCCACAAACGTGGGATCCGTCGAAATCTACATGGATGCCGATCTGAAGACGAACCGTTGGACTGGATTCAATGTCGGCAAGCATCCGCC
CAGCACCTACGAGTACGATGAACTGGTCTTGAACAAAGAACTAACAGAAGCGCCCAAGGAATTCGGCAAGGGGGATCTGGTGGGCCAGTTCAATA
TGGGCAGCACCATAGTCCTGCTCTTCGAGGCGCCAAAGAATTTCAAATTTGATATTATCGCCGGTCAGAAGATCCGCGTTGGCGAGTCCCTCGGC
CACATCGTCGGCTCCAAATGAAAATGGGAGCCACAATTATGTACCGAATCAGTGCAAAGTCCTGTCCCCCAACTGCTCAGATCACTTGTTGTATT
AGCATTAGACGCTCGTGTCCTAGGCAAATGTATTTTGTGAACATCCTGCGAAGCTAACTCTGTGTATTGTTGCCATTTCAGTAGTTTTAAGCTAT
ATTTTATACAATAAACGTCGAAATTATATTTGAG
(SEQ ID NO: 677)

Start ATG: 863

MVSYFVPRGRFLLKAGNLRQVVQQQHQPAQLQLQPIKGPQPQAQNASLPVARHLRQFSSNPASKEAPLHHRRPQHKQQPNPSQELAQIRRNILSR
WTGFLLRWAPMGICVFGAIEWQLQKNRCEKEGKPRTASELQSRIYCSLPLRIISRCWGWLAACYLPPSLRPYVYGWYSNTFDVNLSEAMYPEYEH
YNSLAEFFTRPLKEGVRVIDQQAPLVSPADGKVLHFGSASDSLIEQVKGVSYSIEDFLGPLETVEQANSGASYAQALKKKSDGSTELYQCVIYLA
PGDYHRFHSPTAWKPTIRRHFSGELLSVSPKVAGWLPGLFCLNERVLYMGQWKHGFFSYTAVGATNVGSVEIYMDADLKTNRWTGFNVGKHPPST
YEYDELVLNKELTEAPKEFGKGDLVGQFNMGSTIVLLFEAPKNFKFDIIAGQKIRVGESLGHIVGSK*
(SEQ ID NO: 678)

Name: PHOSPHATIDYLSERINE DECARBOXYLASE PROENZYME
Classification: enzyme

Celera Sequence No. : 142000013384303
AAATGGCGACCAGGGTCTGTGGGGCTCACCAGATTAATATCAGGGTGGTGACCACATTGAGGATCAGTCCCACGATGGTAATGAGATTGGGGGCC
AGCCAAAGGGGCGTCTGGGCGACCAGCCAGTTCCACCACGGCTGCAGCAGCGGATCGAGCAGGCTGACACTGAAGCAGGAGTACTTGTGTTCGCT
GAGCTTCCTCAGCTGCTGGGCACTCAGGATGTGCTTGTCCCGGTAGGCGAGCAGCGCCATTTTCCCCCACCTGGTTACGTCGTCCGATTCCTGCG
TCGTCGCGCTCTCCTCACGCTTTTCACTTTTCACTTTCCTCTGACCTAGCGCTTTTCCCTCGCGCGCATTTGTGTACGTGTACTTGACGTATGCG
CGCGTGTGCGTGTGTGTCCGTTTGTGTGTTCGCTTTTCCTGGCTATTTTCACACGTGGAGCGCGATGCTGGCGCAACTACGAAGCGCGTCTATGA
TTTGCGTTTATCAACTGCGGCGTGGTCAGTTTTACGATCGCTTGGATGCGCACGGAGTATCTGCACTTGTATGTTTACTTAGAAAAATTAACTTA
ATTGAACGACCGTGCCGTGGAGTTTTTTTTCTTATTGCCTATGACCAGTGTGACCGCGATTGTGACTGCAAAATAAACCATCTGCGCTTGCAAT
GAAATACCAGAAAAGAACGATGTCCATTTGCGATAACACATAGCCCAGACTCAACCCAATTTAACAGCAGTCTTGGTGTTCTCTGTTAGTTGCAT
TTTGCGCACAGCTATTTAATATCTTAGCGATATTGTTTGTGCAACTTAAAAAAAATAAATTTTCAATATTGAAGCAACTCAATTAATGACAATTT
TGTATAGACTAACAATGACACGATCATTTGCTCTGTTAATGTAACATCAACATTTGCAATTTCCTGTTAATAGCCCGTTATAAGTCTTTTACTAT
CGGTCGTCTATCGATATCGGCCTTTTAGCCGCCCATTCAAATTCAAATGTATATATCATAGTTTATTAGATAAATCAGTTTGTTGCTTAAACTAC
GTCCTCAACTTAACATACCGTATGCAATGTTTCATTTGTGTATTCGCTTGTTAGTTAATATCTAAACCTTGTCAATTGCCTGCTTTATTGTTACG
ATTAGAATTTATGTTTAAATATGCGGCTACTACTGGTTCTGGGCCGGGAAATGCTCGCCAACGCCTGCAAATATGCTCAAAAAGTACAAAACTGT
CGTGCGTCCAGCTGCTGGCCAATATAAATTGCGGCTTATGTAAACTATGGCCTATCAAAAGTTATTTTTGATGTGTTGTTTCCATGAGGCATCGT
CGTCGTGTTTCTTAGTTTGGTGGATATTAGGAAAATGTATAAATGTATTTGCTTCGATATATAATATTTATATATAGATAAAAAAATAGGCTTAA
AATGTTTCGTTTTAGCATTTTGTTGTTGTTTAAATTACTTTATATTGGCAACTCTCATTACATTTGTTAATGCATATAGTTATGTAGTTGAAAAA
CGCTCGAACGTGCAACTATTTCGCTTTGCTGATGACAAAAATGGTTACACACAGCACACTCAACCAATTATATAAATAGTAGTAGTAATAATTTA
TAGCACAATATGATATAGCAGCAGTTTGAAACTTTTTACACATGTCACAAATGTTTTCTTCCCGTTTGCAAGATTCATTTTTCGTTCATGGAGTT
TTTGTGGTCAGAAGACAGAGTGCAAATTATAATTACTGACAATTTTCAACTTTAAAGCGAAGGGACAAAATTTCACATAATCAATTTACAGTCGC
CGCAAAAGTTGCATGTGCAGCCGAGGCCTAATATCGTTCAATTTGCATTAAGAAGATACATATTTATTTATAGATGCGTGCATGTATGCATATAG
TAACCAGCGATGCAAAAATTAATTTAATTTATGTGGTAGGCATTTACGATAATATAATATAAATTTTGTTTTAATTGTCTTCAGCTTTGAGACAT
TTAGGCAAAAGTTTTCTTTTCATAGTGAATTTGTTTTGTTTTCTATAAAACGTGTTAAGCATTAGGTTGGTTGGTTGGTAATTCGTTATCATATA
ATCATAATAATATAAGTGTTCACTCGCTGCGAAACGCACTCCTTGAAAACATCAAAACATAAACTAAAGAGCACATGTAGGGCAAAATCCTCAAC
ACACGTTCAAAAGCACAGGACAGAACTTCTCTTTATCGAACTTAAATTATATATTTATATCAAAAATCCGCTTGTTTACAATAATAATAATAGTG
CCTGGTCTGGTATGTAGACATACTTGCATATGCCTATAGTTGCGGTCAAGATTGTAGCAAGTGAGTTTCGTCCTCTGTGCGGAAGGATTGCAAAG
GAAAACTCCGATCAAATGCCTTTTTCTTCGGCCGCAGCTATAAATACACAAATAAATTTACATATCTAGTTTAAAGTGTCACTCAGTTGCTATTA
AACGATTTCGTAATGTTATCGTAATGTAATTGTTTTATCAAAAAACGTCAAAACGTAAAAAATGCATTCGGCTTAAAGGCTTAAACTTGTGTTGT
TCTATACGTTGTCTACAGAATTTATGTCCACGTTTCTTGTATATAAATATTTAAAATTTGTGTTTTTTAGTTTCTTCTTGTTGTTATTCGCAATT
GCTGATAATGCTGCCTAATCGTTATGGGTGTGTGTTGTGTTTTTCGCGTTTCCCGGAGAGGATTGTGGCGTCCCTCCTTAGAAGTTATCTT
ATTATGAATGATATGGCGTCACATAAGTTGCTGGGAAGATGCCTTTCCTATTGCCGATCTCGCCGTTCCACCAGTTCTCATCGGAGCGATCTGTG
ACGGTGATGACATCGCCGCGTCTGAAGTCCAATTCCCCGGATTCCTGTGGCACAAAATCGTACAGCGCCTGCACGAGCATCTGCAATAAAAAAA
TCGTTCGGACATAATGAATCCAATCTAATACTCTTGGCATCGCTGTTTGTTTATAGTTCAAATGGGTGGGCGGTGGCGGCGGCATCGTACGCAAA CATGACCTCAATGTGTTATGCGAAATTTGTATTTTAAAATGAATCTGCATGTTTGCTGAGCAAACTCATCACATCAAAATGGAATGGAATGGAC
GGCACACCCACCTCTTCAGGTATCATATCACGCAATTTGACATCCTGCGACCGGGACACGCTCGCCGTCCGATGATATTCGACCAGTTCGTTGAG
GGAGTTGAACTTGACCACCCAGAGGAAGAATTTGCTTTGGGCATCGCGCAGAACCTTGAAATGCTGAACGCCATCGGGGCATCTGAAGGGGCAAA
GAATTTCGATTATATACGGTTTTCAATCATAAATATGAAAGCTGAAGCCATTCAAGCGCAACTCACTTGACTGATAAGGAGAAATCGCCGGGACT
GGATTCGCTGATGCGTATCAAGAAGGCGCCTTCGTGCTTATTTGACAGCAGCTTCTCAGCATCGGCGCGTGTGATGCGTCCGTAATACCAGCTAC
AATAGAAATGATCATTATTTGGGTCTCGATATTGGAAATTTCAGGCTCGACTTACTCGTGATTCTTCATTTCTATGTAATTACTAGGTATGAGGC
CTTCCTTTCCATCCAGCTCCGCGCGATACCAATTTGAATCGTCTTCCATATTTAATATCTGTGTAAAAAGAAGGGATGTAAGTTAATTTAAGCAA
TACAAATCAATGGGTTTGTAAATGTAATGAACCATATTTTTGATTAAATAACTAATAAAGAAAGCTTGATTTGTGGAAAAAAGGATCTTAATGGG
CATAAAATTACCTAAATCTTCTACCCCTGCCTAATAAAACAATCATATATTCAGCTTCATGAGGCTGAGTTAAATGTTAAATATGTTCTTTGGTT
TTTCCATGAAGTTATTAAAACCGGAGCATCTGATTTTAATTCCCATTTCTCACGAAACCAAAGTACCAGCTGCACAGTGAGTAATCCGATCCCCG
AAAATTTGTTGTAAGAACCTGCCTCCGTTGTTTCCATTTTGAGGGCCACTCCCCTTTAATCCCAACCCCCCCAGACAATGGCGATCAATCGAGAC
ATTCTTCCGCTTTGTTTATTGGCGACTGGCCCGATTCCCCAGTGGATTCGATGAACAGTTTTCAATTGTTTGTTGATTGAGCGTTGTCCCAAAAA
ACTGTGTCAGTGCGCAATCAGCGAAGATAGGCTTATGGTTTGGTATGAAACGTACATATTTATCTATTATCTCCACTATTCTCATATCTTTTTTT
TCTTGCGAAACGCTAAAAATAGGCAAGCATTATGGCCGCGACATGTGATAAGAATGTTAAGTGAAACGGAGCACTCACTCGAATGGACGAATTTC
ACTTTTGTCTATCTAATGAACTTTTTCCTAGCCCATTTCGCATGCCAATGACACAACAACAGGCTGCTGCCTACGTAATCATCGACTACTTTTAT
GATATCTTACGATTGACAGCCGAAATTGAAGATTGTCTATCTGCAAAGGTCTCGCCATTTGCTTGGCCACTGGGAATTCCCAGATTCGAAGGTGC
TGAGTTGAGCTTTTATGAATGAATCTCGTCGCTTATGACGGCGCCCAGCAGCCTTCAGTTTTCGGAATCTGTTTGCTTTTCTCAAGGAAATCGGT
TGCACAAATACCCAGGAAATGTGTTTATTGTGCAAAGGTCAGGATTTCGACTTTTAGTTAAGTCTTAAGTAAAGCATATTCCTATCTTTATGGAT
TTCTGCCATTTTTCCCTTGAGCAGTTCAGTGTTTATTTGGTAGCTTTGTTGTTTTCCAATATAGCTTGTTCGTCAAGTCGGAATAATGGAATGGC
ATTCAAATGAGTCACCCACAAAAAAAACCCCTGTTGATACTGTGTAGTTGAGGGTTGGTTACTTTTCTGAAGTTGCAACTTGTAATTACCCCATG
AATGTCTCATCGTTAATTATACACGCTACTAACATACGAGGTTAATAACAAACATAATACCTTAACCCACAGATCGATTTCTTGTTAATTAAAGA
TACAAATATATATATATAAATATGAGATATATCATATTCGATTCGTATAATGATGTTTCGAGTTTTTTGGTTACATTTTCGCACGTCGGAATGTG
GAGGGGATTTGGGTGATGTGGAGCTGGAGGTGGATGGGGTGTCAATGTCGTTTCCAGCTTATGTAAAACCCAATTATTGTGCTCACTGTTGGCTG
TGGCAGTGGGATTTTGCCCGCTCAGCTGGATCTGGCCGACTAATTGGCATAGCTCCATAGTTCTAATCCACCCCGCGATCACCGACCATCCCGCC
CGCATCTGTCACCCAGACATTGTTCATCGTATATTTATTTTATTTTAGATTGTTTCATTCATTGAAAACAGCCGCCGAGAAATTCATTTCCACG
GATTCGTCGTCTATTACAGAAAGTTTTCTCGCCGCTCAGCACTGGGAAAAACCAGAGGGTTTAGAAATAATATAAACTTAAATATGCTGAAATGC
TTCAAGAACATAAACTTTCCAAGTATTCCATGATCGCATATTTATTTTCCCAACTGCATAAGGAAGTGCACCATTTTTTTTTCAGTGCAGGCAAT
GTGCAATGTGCCTGTTGGATAATGCATAAATATTTAGCGGCGCTTTCGGAAGGCAGGCACGTAGTGGCCATGATTGTTATTATCAATTGTTTATA
CTCGTATGCTTATGTAATTACTAGAGAAAAAATTCTATTGTCGTTTCGGAAATCCGACGCTGAAAAAAGTGTCAAAGCAACACGAACGTTCACTT
TTCGCTGTTTTCGCGACAAGCGAAAGTTGAGCACAGAATCCCATTTCGTGTGTTTCACATTGTTATGATAAAACGTGGCCACTTTTGGTGCCCAC
ACAACAAGGCCGTTAGAATTGGAGGCATTTTTTTTTTTGGAAAATGGAGCTCCAAATATCCAAGAAATACGCTGACCTGTAAACCAGTTTTCTGG
AAAGAGAACGAACCCCAATGAAATGTTTGATGATTCACAGCGCTCCTCTCTCTATCGCCTTCTATGCCTGCTGTATGTTTGCTGGATTGGGGCAT
CTTTTCAGATAAGGCTATCGAGAAGTGACTAATCGCTGGCAAACAAACAAATGCGCTGGGAGTTCGAACAGATATGCGTAACATACATATCTCCA
ATGCGAGATAATCGTGTATTTCTATTTATCCCCCGCATCAATGGAGCCCAGAACTATGGGCTATTAAACGAACTATGACTATCAGTGCGGATTGT
TTACCCATTGATAAGACCGTGCAGCTGGACAGAGGGCTCATCTACGGCGTAGAAGCCCCTCTAATGGACGGGAGCAGCGCACACACTTGACCTTC
GGGCGGCGATAAAGAAGCCTCTTCGGCGAGTCATTGACACCATCAATCAGCAGCAGCGGCAGCAGCAGCAACAAATGCTGCAAATGCAGCGGCGG
CATATGGAAAAGAGGCGCAAAAAAAAGAGGCACAAAAAGGGAGAAAACCTGCCACGGGCCTGGGTTCCTGCTGTGACTAACCTACGACAAGGTAG
ACACACAGCAACGAAAATCAGCTTACATCGCGCCCTGGCAACAAGAAACCGGAAAATTCGCCAGCCAAAACAAAGGGTTTGGCCTAGGACAGCCA
GCCAGCCAGCCATCGAGCCAGTGAGCCAACACAAACACAAACACCTGGAAGGAAGCAAGGCGGCGAAAAAGATCGAATCGCAGCCTGCCAGCAGC
CTTTTTCTTGGCCAGAAAAGCCAGCGAATACAAGCAACACGGGTAAGCATCGGATGTCCCCCACAAAGTTCCGCAAAGTCAAAGGGGGCATCGAA
TATATCATCACTACAAACTGTTGGAATTGTTTTTCTAAGCATTCGGAAGAAAACGAATAAGGAAAGTTGAAATAGTATATATACTATAGGAATGC
TAACAATAAATAAGTTCATTCAAGGAAACACAGTGAAAAATGCTAGATTTGCAAAGTATAGTATATAGATTAAATCATATATGCATGTTTATAGC
TTTAGAAACCCCCTCCTCACATCATTTTTTAAACTTACTTTGTAATGCTAATCACAACTATATGCAGATTAAATGGGGTCAAAAATATGGTCTTG
ATAGATTTGAAGTGCAGTTGAGAAATGAAAAAATGTAGAGTAGAATGTACAATATTTCAGTATGTGATGCTTCACAAGGATTTTGTACTGATAGT
GGAATATATTTGACTGAATCTTTTCGTTCTAGTAAGAGTATTCGGGCTGCGGTGGCTAATGAGTCGTAATCCTTTCGTGTTGCCTTCTGCGAATG
CACCTTTTGAAACTCTTTAGCCAGCTTTTGCGACTGCTGTCTGTTTGGTCGCGATTTAGTAACAAAATCTGTCTGGGGATTGAACCTAGGATGTG
GGTTAAGGCAACGACCTGGACGGCGGCAGCTGCATCGCAGCGGATTATGCATGCAGGACCTGCCACGTCCCCCTGTGCACCCCCTTACACCCTTG
CGTGCCCCCATTCAGTGTGAAGTCTATGAATAAATGCAGATATTATGATTTGAGGTGGGAATTGATGATTTTGGAACAGCACTCACCTTTAGAAT
CTGAGTTTTGCGAAAACTCAGCTCGTCGTCAGCCGTCGCAGAGAAATCGTGTTTGGCAATCGCTTCCATTTTGCTGTGTTGTTTTGTGCGCAGTT
AGAAAACGCTTTCGGAGTTTGTTTTAAAATTTAGTTGCAATTGTAGTTTTGGATTTAGTTCTATCAGCCTTGATGCACCACACACACGCACACAC
AGAGGCACAGACACACACGCTCGTTCTCTGCTCTTTCTCTCTAACTCTCTTTGAATTTCTCTCTCACTCACTACTCAGTGCTGTGGAAATGAAAA
CGAAACGAGACGAATCCGCGATTAGTTAGCGCACATTATATAAACGATAAATCATGGATATTCGGCAGTGCGCTTTTCTCAGTTCGGTTAATAAT
AATATATCTTGTGCGAAGGCAAGGGAAGAAAGCGATTAAAAATACACCGACGACGACGACATTCCCAGGCGGAGCAGCAACAGAGAATGAACACA
GACACGAGCCGCTCTCTCCACGGCGGCCACTGTGTGGGTGTGTGTGCGTGAGCGTGGCAGCGTTGCCAGCAGCTTGCGATTTGGAATTTCGGGGA
AAAGCAGGTACCGCAAAAGCAATTAGACGATGTTTGGCTATTACTTGTTGTTATGCGAAGTAATTTGCCTTAAATAATATGAAATGTGTCGCTTA
GAACACAATTAACATTTGGCAATCTAGGGCGTGGGTGCTTGCTGTTGGCAATGCTGCCGCGGTGACGTTGTTGTTTGTTTTATTTTTTGTAACCC
CAATAAACACACACACACACACACACGCGGCGCTTATATTTCTATATGCGTAAGTTGCGGCTAACTATTTTCGAGTCTCTGGCACGTGCAAAGAG
GCCGCCGGGCTTACAATTTCAÅAGGGCTAGGGTGGCTGCAAGCTTAAGCGACACTAATTAGGCGCGGGAGCGGTTTGGCTAACATATTACTACTG
CTAAATTTGTAATTCACTTTTATTTTCATAGCAGCGTGACCGTGGCCGGGTCGCTTTATTATTCCAAGAAAATATACTGAACACAACACTGTGGG
AGAGGCATACCGCAGGGCTTTCGTAGTTTTCCTTCACCTGGTCACACCGCAAGACGCTTCGCCATTTTAAAAATCAAAACAGGAGACGCTTCGCC
GGAAAAGTCAGCATTACGTTTCATTCCCAACCGGACACTTCAGTTTGACTCGCCCATCCGTCACAGCAGTCGCCATGCAGCGCCACAAGGAACTG
TACAAGGAGCAATCGCTGGTGCTGAGTCCGCGCAATCACTGCCAGGAGAACAGGGATCGGTTGCAGGCGGCGCGCGCCAAAAAACGAGAGGATTG
TTTTTATCAGAACCGCATCATCAGCGTGAGCCCGACGCCCGTCAAAATAAAGCAATTGGCGGCGGCCCAAGCTGCTCTGACCCAGGAAAATGTGG
CACCCAAACTGGAGAGTCCGGAGCGGCTGGACACGAAGCCCGCAGAACTGCTGAAGGAATCCAACCCGAAGGTCTCCCGCCAGAAGCTCTACTTA
CAACGCTACATGGAGTGGAAGATAGCCAAGACCAAGGAGCATAAGCAGCAAGACCAGAAACGTCGAGGCGCAGCCATCAATGTGCCGACAGTAAA
ACAATCAAAGGCCTTGCCCAAATCACAAACATTTCGGGTTCCCGATAATCTGGCTTCTGCAAAGCAGAAGGAGGCGGCTCCCATGTTCCAGCCTC
CCAAGCGGTGTTCTCTCTACATGATTGCCAATCCGACGGGCAAGGGAAAAGCCGCAGAACCGATTAAACCTTCAATACCCAAGCCAACGTCAGCA
GCAGCTCCTCCGTCATCCAATACCGTGGCTGCATCTTCCGCCTTGGCCAGGCATAAATCAGCTGCTTCTGCAACAAAAATAGTGCCTGCAATTCG
TCAGAACAACAATCCAGTGGCCTTGGCCAGGCAAAAAGCAGCTGCACGACCCATTCCCAACACAACGAAGCAAACTACCAGTGTAAGGCAGCCT
(SEQ ID NO: 679)

FIGURE SHEET 368

Exon: 8594..8470
Exon: 7870..7592
Exon: 3668..3571
Exon: 3511..3392
Exon: 3312..3147
Exon: 2930..1001
Start ATG: 7669 (Reverse strand: CAT)

Transcript No. : CT18920
CACGGTCACGCTGCTATGAAAATAAAAGTGAATTACAAATTTAGCAGTAGTAATATGTTAGCCAAACCGCTCCCGCGCCTAATTAGTGTCGCTTA
AGCTTGCAGCCACCCTAGCCCTTTGAAATTCACTGAGTAGTGAGTGAGAGAGAAATTCAAAGAGAGTTAGAGAGAAAGAGCAGAGAACGAGCGTG
TGTGTCTGTGCCTCTGTGTGTGCGTGTGTGTGGTGCATCAAGGCTGATAGAACTAAATCCAAAACTACAATTGCAACTAAATTTTAAAACAAACT
CCGAAAGCGTTTTCTAACTGCGCACAAAACAACACAGCAAAATGGAAGCGATTGCCAAACACGATTTCTCTGCGACGGCTGACGACGAGCTGAGT
TTTCGCAAAACTCAGATTCTAAAGATATTAAATATGGAAGACGATTCAAATTGGTATCGCGCGGAGCTGGATGGAAAGGAAGGCCTCATACCTAG
TAATTACATAGAAATGAAGAATCACGACTGGTATTACGGACGCATCACACGCGCCGATGCTGAGAAGCTGCTGTCAAATAAGCACGAAGGCGCCT
TCTTGATACGCATCAGCGAATCCAGTCCCGGCGATTTCTCCTTATCAGTCAAATGCCCCGATGGCGTTCAGCATTTCAAGGTTCTGCGCGATGCC
CAAAGCAAATTCTTCCTCTGGGTGGTCAAGTTCAACTCCCTCAACGAACTGGTCGAATATCATCGGACGGCGAGCGTGTCCCGGTCGCAGGATGT
CAAATTGCGTGATATGATACCTGAAGAGATGCTCGTGCAGGCGCTGTACGATTTTGTGCCACAGGAATCCGGGGAATTGGACTTCAGACGCGGCG
ATGTCATCACCGTCACAGATCGCTCCGATGAGAACTGGTGGAACGGCGAGATCGGCAATAGGAAAGGCATCTTCCCAGCAACTTATGTGACGCCA
TATCATTCATAATAAGATAACTTCTAAGGAGGGACGCCACACACAATCCTCTCCGGGAAACGCGAAAAACACAACACACACCCATAACGATTAGG
CAGCATTATCAGCAATTGCGAATAACAACAAGAAGAAACTAAAAAACACAAATTTTAAATATTTATATACAAGAAACGTGGACATAAATTCTGTA
GACAACGTATAGAACAACACAAGTTTAAGCCTTTAAGCCGAATGCATTTTTTACGTTTTGACGTTTTTTGATAAAACAATTACATTACGATAACA
TTACGAAATCGTTTAATAGCAACTGAGTGACACTTTAAACTAGATATGTAAATTTATTTGTGTATTTATAGCTGCGGCCGAAGAAAAAGGCATTT
GATCGGAGTTTTCCTTTGCAATCCTTCCGCACAGAGGACGAAACTCACTTGCTACAATCTTGACCGCAACTATAGGCATATGCAAGTATGTCTAC
ATACCAGACCAGGCACTATTATTATTATTGTAAACAAGCGGATTTTTGATATAAATATATAATTTAAGTTCGATAAAGAGAAGTTCTGTCCTGTG
CTTTTGAACGTGTGTTGAGGATTTTGCCCTACATGTGCTCTTTAGTTTATGTTTTGATGTTTTCAAGGAGTGCGTTTCGCAGCGAGTGAACACTT
ATATTATTATGATTATATGATAACGAATTACCAACCAACCAACCAACCTAATGCTTAACACGTTTTATAGAAAACAAAACAAATTCACTATGAAAAGAA
AACTTTTGCCTAAATGTCTCAAAGCTGAAGACAATTAAAACAAAATTTATATTATATTATCGTAAATGCCTACCACATAAATTAAATTAATTTTT
GCATCGCTGGTTACTATATGCATACATGCACGCATCTATAAATAAATATGTATCTTCTTAATGCAAATTGAACGATATTAGGCCTCGGCTGCACA
TGCAACTTTTGCGGCGACTGTAAATTGATTATGTGAAATTTTGTCCCTTCGCTTTAAAGTTGAAAATTGTCAGTAATTATAATTTGCACTCTGTC
TTCTGACCACAAAAACTCCATGAACGAAAAATGAATCTTGCAAACGGGAAGAAAACATTTGTGACATGTGTAAAAAGTTTCAAACTGCTGCTATA
TCATATTGTGCTATAAATTATTACTACTACTATTTATATAATTGGTTGAGTGTGCTGTGTGTAACCATTTTTGTCATCAGCAAAGCGAAATAGTT
GCACGTTCGAGCGTTTTTCAACTACATAACTATATGCATTAACAAATGTAATGAGAGTTGCCAATATAAAGTAATTTAAACAACAACAAAATGCT
AAAACGAAACATTTTAAGCCTATTTTTTATCTATATATAAATATTATATATCGAAGCAAATACATTTATACATTTTCCTAATATCCACCAAACT
AAGAAACACGACGACGATGCCTCATGGAAACAACACATCAAAAATAACTTTTGATAGGCCATAGTTTACATAAGCCGCAATTTATATTGGCCAGC
AGCTGGACGCACGACAGTTTGTACTTTTTGAGCATATTTGCAGGCGTTGGCGAGCATTTCCCGGCCCAGAACCAGTAGTAGCCGCATATTTAAA
CATAAATTCTAATCGTAACAATAAAGCAGGCAATTGACAAGGTTTAGATATTAACTAACAAGCGAATACACAAATGAAACATTGCATACGGTATG
TTAAGTTGAGGACGTAGTTTAAGCAACAAACTGATTTATCTAATAAACTATGATATAT
(SEQ ID NO: 680)

Start ATG: 327 (Reverse strand: CAT)

MEAIAKHDFSATADDELSFRKTQILKILNMEDDSNWYRAELDGKEGLIPSNYIEMKNHDWYYGRITRADAEKLLSNKHEGAFLIRISESSPGDFS
LSVKCPDGVQHFKVLRDAQSKFFLWVVKFNSLNELVEYHRTASVSRSQDVKLRDMIPEEMLVQALYDFVPQESGELDFRRGDVITVTDRSDENWW
NGEIGNRKGIFPATYVTPYHS*
(SEQ ID NO: 681)

Name: downstream of receptor kinase
Classification: signal_transduction
Gene Symbol: drk
FlyBase ID: FBgn0004638

Celera Sequence No. : 142000013384288
TCCTGCGTGGGCATGTAGTCCTCCACGCGCACCTTCTTCTTTTTGCGCTTGCGGGCATCGTCCAACTCTTTGAGGCGTATTTTGGTAGCCTGTGT
CTTGATGGCCGTGGAAGTGCGTATGGATTTGCGGCCGGAATCGAGGACCGTGAAGCGTGGACGTGGCCGCCGTTTCGTTACCCCACCACCAGGTC
GTTTCTTGTGCAGGGCCGGCGTTGCCTTTGTTTCCTTTTTGACTGCAGGCTTGGTTTCCTGCGGAAATCATATGTACCATTTAAACACATTCAGT
AATCACAGGATTTTATCGCATTTTAAGAATGGTTCGCACCTTATAAGCCTTTGTGTTAACGACACCGCGTTTCCGCTTTTTCTCGGGCGCCTCTT
CCTGATCCGAAACGGGCTCGTCGTTCTCATCGATACTGAAGTCGGAGTCAACCACATCTTCCTCTTCGTCTTTTTGCCTGCAGAGTGAATTTTAT
ATGGCTTGAGCATTTAAATTTATTCAAATGATTAGTGCTCACTCGTATTCCTTATCCTCTTCGTCCTCCTGAAATCCACCATAGGACGTTTTGTA
AAAGTCGTCCTCCTCTTCCTCATTGAGCAAATGAGCTATTTTGTTGCCGGCATTGTTGCGCCGTGATCGCGAGGCAGCCATTTTTGTTATTTATA
TATAGAAACTATGATTTAAAGCAGCTATTAAATAATAATATTTTACAATTTGTAAATGTAAACAAGCAGAGCAGTGTGACCAATGTAGCAAACAT
AGTATATATCGCAGAGGCTTTACAACTTTGGTATGCGTTTCAGCCCTGGTAAAGAAAATGGTTTCTCCTGCATTGGCAGTTATTCAAACACATTT
AAAACATAGCTAAATTTATTTATTTATCTATTACATGTATCACAACAAAAAGCAGGCAGCTGCTTTAAAATCACATTAAAAAGCGGTCGGTAATT
CAACTACCGAAAGTAGACCACATTACTTTACACTTCGCGCTGGCCACACTCTTGGCTTGTTTGCTTTTTATTCTGCCGGCTGCCTGCATTTTCTGAT
TTAATTTAATACCATCGATAAAAAGACTGCTCGCAACATGTCGGAACAATGGGAGGTGGTCTCCAAGTCGCGCAAGCAAAAGAATCTGGACAAGA
AGGTGTCTGCACACAACGAGCAGAAGCGCATCGCGGCCCAGTTGCCCAAACTGGAGGAGCTGTGTAAGAATCTTTTAAAAGGTGCACCTTGCAAT
GCGATTACATGTTTGCCCCTGCCATTTTATTCACTTCGCAGTGCCAACTCAGCGGTATCGCAATTTGTTCGGCAGCAGCAACAACAACAACAGCA
AGTCCCATTCCCCTGCGAAATCTAGTTCAAGTGCCTCATCTTCCTCAAAAGCCAATAAGTCGCCAGTTAAAAAGCACACCGCAAAGAATGCCTCT
ACCCAAAAAAGGACCACGTCGGCAGCCGCATCGAAGCCAAAGACTCTGGAGCTGGCCTTGAGAAACATCACCCGGGATGATTTTGCTGCCCAACT
GGAGCAGGTGAAGCTCAGTTGTCCTGGCTCCGAGCTGCGCTGGTTAAGCCATGTATGTTTCTAAAGGAAATGTGCCTAAATATTTGCTCACCTAT CGTTGTCCCCCAGATTGCGCTATACTTCAATGAAGCCTTGTCCTATGACTGCGATCCCATCTTCTCCGGCCGCTCGGCTCAGTATCCCAGCAATT
TGGCCAGCGCCTCGCTCAAGTACTCAATTGTGGAGTTTCTGGGCAGTGTGGGCGAACAAAACCTGGAGTATTTCTTCTACTCCCTGCTGGATAGC
ATGTCAACGGATCTAAACAACAATCAGACAGTGGCAGGCTACAAGCTCATCCTACAGTTGATCGGTCAAAACTGGCCGAACATTTGTTCTAGGAA
CCTGGCCAAGACTGCGTTGCTAAGGAACTCCTATCAGAACCGTAGCAACATCTGCCTGAGCATCCTGTGGGCAATTGGACAAGGTGGCTATCAGT
CCCTAAACGAGGGCGTTCGCGTGTGGCAGAACCTGATGCTGCCCAACCTGGAGCTAAAGCAGTACACCAAGTTTGTGGTCGAGTATATGGAGCGG
GCTCTGAGTGCAGCAGCTGTCCGGAAGACAGCGGATCCTCTGCAGATCAACCAGCAGGAGTTCTTTGCCACTTACAATGCGCTCAATGCACCCTA
TAACCACCTGCCCAAGGAATGGCAGCAAAGTCTGAAGCGTAGTGCGCGTTTGTTGCTTGTAAGGACGAAAACAATTGATAGTTGTCCCATTGTTT
CACTGACCTTTCTTCCTCCTGTGTGTAGCAACACTATATCAACAGTCCTGTGAGGCATGCCAACATATTCCTTACGCTCTTCCGGGAAATAAGCG
CCGGATCCAAGCAGACTAATGAGATCGAAGGCTGTATTAGTTGTCTGCTCAGCAGCGGCAGAGATGATTGCCTCAGGGTGTGGCGCATGAACTAC
AAGAAGCAACAGTTGCCTAGTCTACTGCTTCTGAAAGCTATAAGTACGATCTACAGCTGTGAAAATTCATTTAATTGGATTTTTGTTTAAAAGTA
CCACCCACACTTAACGTTAATGTGTTATCTAATATTGAATTTCTATCTTTTCCTAGACGACAATTGGACCACGTCTACCCATGAGTTGGCTACGT
CGACTGTGTATCACTCTTTTCTGCAAGATGTGGCGAATCTGAACGAAGAACTGCAGGGAAGCAAGAGAAACGAAGGTCACCTAGATGATTTAAAG
GAGGTTTTGTTGGTGAGTGCGACTTAAGTATATCACTCGATTCCAAGCATAAGGCTCTGATCCCAGATCGATAAAAGGTGAATGTTGAATGTGTG
TTGTTTTATCTTTTATAGTTTATTGGAAAACTAGTATATAGGTAATATATTTATTTTGTTAGCTTTTTTAACCCAAACTTATTATTCAAACTTA
AATGAAATCAGAAACACTATAAATTTGAATTTTCTCACACCTCTGGTAACACTGTTTAAGTTAAGTGGTCTGGCTTAGTACATTACGTACTCTGG
TCACATTGCTTTAGTGAAAAGAAAAACGAAGGTATAAACTTGTAGAACTGCCGTCTAAAAGTGAATAATTTATTGCAATCGGTGCTAAAAAGAAT
GATATGAGCTTATTACACTGCAGCTAACTAATGTAAAACTCTTCACGTAGAAGTGGCCGAACTGTTAGCCGTTAATGAAGTTAGAGTTCTTTAGG
AGGACGCTGCCAACGCGACGTCGCTGCGGGAAAGAGATGGAAAGCGTTAGCCGGCGTTCGTCCGAAATTTCTCCGCTATTCAACTGGCTTTTGAA
GCCTGGAGTGAGCATAAATTAATGGTCCGCACCTTAATTATCGCGTTGTCGCAATTATTGTTGCTGTTGCAGTAGTGCAAAGTGCGTTTCGTGCA
TATGTGTGCGTGTCAGTATTAACGGTTGTGTATTCCGCCGTTCTGCACTGGTATTGGTGGCAGCTATAGCTGCACTTTTCCCATAGCGTTGCCAT
GCGGGTTCCAGTTGCCGCTAAATTTCTCCGAGCAGAGCAGACGTTTTGCTTTCGAAAAGAGAGTGGGCATGGCCATCGGGGATCATAAATTGCCG
CATTATCAGCCAACATTCTTATCAGTACACCCAATTTTCGGCTGATCTGAGGCTTATTTTTATTTTCCTATTGACTGATGTGTTCCAGCTGCGAT
TGGCCACTCGCCTCCTGCTCCCTCACCCACTCCCCTCTCACATCCCGCTTGTGCGCACTCTCCTCCTCTCTTCGCCT
(SEQ ID NO: 682)

Exon: 1001..1203
Exon: 1277..1572
Exon: 1629..2243
Exon: 2309..2513
Exon: 2622..2782
Start ATG: 1083

Transcript No. : CT19152
TTGGCTTGTTGCTTTTTATTCTGCCGGCTGCCTGCATTTTCTGATTTAATTTAATACCATCGATAAAAAGACTGCTCGCAACATGTCGGAACAAT
GGGAGGTGGTCTCCAAGTCGCGCAAGCAAAAGAATCTGGACAAGAAGGTGTCTGCACACAACGAGCAGAAGCGCATCGCGGCCCAGTTGCCCAAA
CTGGAGGAGCTGTTGCCAACTCAGCGGTATCGCAATTTGTTCGGCAGCAGCAACAACAACAACAGCAAGTCCCATTCCCCTGCGAAATCTAGTTC
AAGTGCCTCATCTTCCTCAAAAGCCAATAAGTCGCCAGTTAAAAAGCACACCGCAAAGAATGCCTCTACCCAAAAAAGGACCACGTCGGCAGCCG
CATCGAAGCCAAAGACTCTGGAGCTGGCCTTGAGAAACATCACCCGGGATGATTTTGCTGCCCAACTGGAGCAGGTGAAGCTCAGTTGTCCTGGC
TCCGAGCTGCGCTGGTTAAGCCATATTGCGCTATACTTCAATGAAGCCTTGTCCTATGACTGCGATCCCATCTTCTCCGGCCGCTCGGCTCAGTA
TCCCAGCAATTTGGCCAGCGCCTCGCTCAAGTACTCAATTGTGGAGTTTCTGGGCAGTGTGGGCGAACAAAACCTGGAGTATTTCTTCTACTCCC
TGCTGGATAGCATGTCAACGGATCTAAACAACAATCAGACAGTGGCAGGCTACAAGCTCATCCTACAGTTGATCGGTCAAAACTGGCCGAACATT
TGTTCTAGGAACCTGGCCAAGACTGCGTTGCTAAGGAACTCCTATCAGAACCGTAGCAACATCTGCCTGAGCATCCTGTGGGCAATTGGACAAGG
TGGCTATCAGTCCCTAAACGAGGGCGTTCGCGTGTGGCAGAACCTGATGCTGCCCAACCTGGAGCTAAAGCAGTACACCAAGTTTGTGGTCGAGT
ATATGGAGCGGGCTCTGAGTGCAGCAGCTGTCCGGAAGACAGCGGATCCTCTGCAGATCAACCAGCAGGAGTTCTTTGCCACTTACAATGCGCTC
AATGCACCCTATAACCACCTGCCCAAGGAATGGCAGCAAAGTCTGAAGCGTAGTGCGCGTTTGTTGCTTCAACACTATATCAACAGTCCTGTGAG
GCATGCCAACATATTCCTTACGCTCTTCCGGGAAATAAGCGCCGGATCCAAGCAGACTAATGAGATCGAAGGCTGTATTAGTTGTCTGCTCAGCA
GCGGCAGAGATGATTGCCTCAGGGTGTGGCGCATGAACTACAAGAAGCAACAGTTGCCTAGTCTACTGCTTCTGAAAGCTATAAACGACAATTGG
ACCACGTCTACCCATGAGTTGGCTACGTCGACTGTGTATCACTCTTTTCTGCAAGATGTGGCGAATCTGAACGAAGAACTGCAGGGAAGCAAGAG
AAACGAAGGTCACCTAGATGATTTAAAGGAGGTTTTGTTGGTGAGTGCGACTTAA
(SEQ ID NO: 683)

Start ATG: 83

MSEQWEVVSKSRKQKNLDKKVSAHNEQKRIAAQLPKLEELLPTQRYRNLFGSSNNNNSKSHSPAKSSSSASSSSKANKSPVKKHTAKNASTQKRT
TSAAASKPKTLELALRNITRDDFAAQLEQVKLSCPGSELRWLSHIALYFNEALSYDCDPIFSGRSAQYPSNLASASLKYSIVEFLGSVGEQNLEY
FFYSLLDSMSTDLNNNQTVAGYKLILQLIGQNWPNICSRNLAKTALLRNSYQNRSNICLSILWAIGQGGYQSLNEGVRVWQNLMLPNLELKQYTK
FVVEYMERALSAAAVRKTADPLQINQQEFFATYNALNAPYNHLPKEWQQSLKRSARLLLQHYINSPVRHANIFLTLFREISAGSKQTNEIEGCIS
CLLSSGRDDCLRVWRMNYKKQQLPSLLLLKAINDNWTTSTHELATSTVYHSFLQDVANLNEELQGSKRNEGHLDDLKEVLLVSAT*
(SEQ ID NO: 684)

Celera Sequence No. : 142000013384288
GCGGGCCACATGCACGGGTTCTATGGATCGTTTGGGCAGCGGCATGGTCGGGCGCGATTGACAATTATCTCCAAATTGGCAAACCCGTAAATTAG
TGCGTCCTCATCGACTGAAAACGGCATTAATAAGTAATAAATTGTTTTAATACGAATTAATGCATTTAAAATTAATTAAATATAAAACCCTTTAT
TTACTGATTTACTACATAATCTCATGCCAAATTGGGATCAATAATAAAAAGATTTCTTTTTATGCTGATTATCAATTGAAGACATTTCATTCCGA
TAAAATTGTACTTCCCAAATTGTCGTTTAACTTTGTTTATAAATTTTCCCGTAAAAGTAGACGTTTAAAAAGTTAATTGGATACTATCAAAATTG
GTTTAAAAGAAATTTTGTCATCACTATACTAAACCGTCTATGAACAAGACTCAGAATGGTATTGCAGAAGATTTCACGAGACGCTTATCCATGTA
TCCATGAGACGTGTTCATTACAATCACCAAAATGCCATTTGAATTGTTTTGTGATATGCGCGACTGACGAACTCGACGTCTGGACCACACCCCAC
GAAACGATACCCACAGCGAGGTGATAAGGGCGTAACGCCCAAGTCACCCCCGCAAGATGCACCTTGCAGTCCCGGCGAGATTAGTCGATAATGCC
CCCCTTTTCGGTGGCAGTTTCTGGGTGCTACGACCTGGGGCCTTTACGTGGGCACCTATTCCATACGTGCATATACGTATATCGTCGGCGGCCTC CCACCAACGCAAATTAGACCGTCACGCACTCACACACACGCATGAACCGCAGCAGCAGCAGCACCCAAGTAAATGTACATACATATGTGTGGGAC
GGAACGGCTGACTCTTTCAGATTTTCGCACTGAAACATTCGCACTAAATCGCAACAATGCACACACAAAGGTATCTCTCACACTTTCTAATCGTA
GTGGCTGCTGCGATTTTGATTTTGGTTTTGAACGGCGCAGCTTAGTTTTACACAGTCCACCTCACTTTACAGCATATCGTACACTCACCGCCCGT
CACACTTTTCGTTTGGCGGCTGGCACCACAACAAACATTAAGCAGCCACTTCCGTTTCGGGGGTTCGGTGGCAAATTCGATCCGATGCGAACTCT
AATTAGCCAATTTGGGGCTTGAAAACTGCAAATATTTGCTCGTTTTGTGGAAACTAAGATTTCCACACCTTTGCAGTGTGACCGAAGCTTTGTGG
TTCGAAAATACTGCAGGGATTCATCATTTCGGAAAATCAGACAAATATACTGCACGATGCGGTGGGGAAAAAGTTATTTTTATATTAAATGTAAT
ATGTATTTTAATTACTATATTTAAATAAATTTTGCAAGGGAATTTTCAGTAACTCATTTCATATTGTTTATTTACTGTATAGAATGAAATATTTT
AAATATAAATATATATTCAATTTATTTTATTTTATTTTAACTCTATATTATCCATAATAAGCTATTTTATTAACGTTATTTAAAATTACTGTTTG
CAGTTTCTTCCATTAACTTTAGAAATGTATATTTGGTATTTTTGGTATTTATCCGCCGATCGATAACTAGTGCTCCAGCCCTGGCCCCAATGCAT
AACATCTCTGTTTCGTCGCACACTGAATAGGTAAGTTTTCCGCACATTTCGTTGATTTCCTCTTGTATAATTCCAACTGCTTGCAGAACCAAATT
GAAAAGATGGCGAGTTTGGCTACCAAGGGATCAGGACTTGTGAACAGTGAGTGTCGTGAATCGAATGCAATCGAATGGATACACCACCATTGGCG
CCTGTCAATCGCAAAATTATGTAATGATCACTTTTTGCAGGGCTCCTCACACAGGCGAGGCCCCAACTGGACGTGTTCCTGAAGTACGCCAAGGT
GGAACTGACGCCCCCGACGCCCGCCGATATTCCGGCCATTCGCCAAGGACTGGGCAACATCATCAAGGGAGCCAAGACCGGCGCCTACAAGAACC
TCACGGTTCGCGAGGCCTGGCTTAACACCCTGGTGACCGCCGAGGTCATCTTCTGGTTCTACATCGGCGAGTGCATCGGCAAGCGTCACATTGTA
GGCTACAATGTCTAAGCTTACTATAGTCTCCGCTTGGCAGTCACTGGAATGGGCAACGTAATCCCTAACAGATGTGTATATTTATATGTCTGCGA
ACATTTCGACTCTGAATAAAGTGAAATAGTAATTTAAAATTCCGAAAATTTTCGAAAAATACATTGTTTTTTGAAAACCGTTAGAACGTTTGCGC
GGGATTTGTGTAAGCTAAAGATGAGGTGATGTAAAACCAAGTTTGGAATTAAAAGTTGACGATATTTAATGATAAAAATTAAAAAAATATATGTA
ATGTTATACATCAAATGTTTATGAAACGGTGTCGTAATCAAAGAGGCTAATGGTTCAGAAATACATAATATACTTAGAGCATTTAAAAGCACTCA
AGAATAATTTTATTTAAAAAAAAAAATAAATAAATCTAAATTTGCTTTTCATAGATAATTCATTTACACATTTTTTAAACAAAGTAAAGTAAGA
TGTATTGAATTATTTATTTATAAATAACGTTTTTATTTGAATCTTGAAAAGCATTAATATTATTATTATTATACTTATATTTTTTAACAACAA
AACTTTTGTAGACAGAGTAAATTTTTGTAATCTAACTGCGGTCACACTTTACTTTAGTTACCTTCCGATCGGAAGAAGAACCCGGCTGACATTAG
GAATAGGAACTTGGCAGAACTTTCCCAGGATCTGTCAGAATGGCCTACAAGAAGCGCCTACAATCGCAGAACCTCGTGCATCTGCTGCAGAACCG
CGAGTCCGGATACACCAACGTGGGCCAACAGCCGGGCAGGATGCCGCTGTTGGCCTACGAGCGTCTCTTCTACAAGTGCATCACGCCTTGCCTGA
CAATTGACTCGATTACCATTCCGCCGATCTACCTGCGCAAGTTTACGCCGGATGGCAGAAAACTGTTGGCCTTCTCGCAGGATCAGCGCAGTCTG
CTCATATACAGCTACGGGGGTTCTAGTTGTGCGGCGGTGGGTGAACTGATTCGCCAGGCGGATGTAGGCAGTGGCGAGTGCTTCAGTAGCCAGGA
CACCATACTCAAGAGCAGGATCTTTGAACGCCTGTTTCCCACAAAAGAGACGCTGAATCTATGCCAAGGCGACTTTGGCCTCTACTATCTGCACC
GGGAGTTCAGTGTGTTCCTGGAAGAGGGTCGTTATGCCATGCTGGCTGCCATGACCGTTGTGCGCGGCGCACTGCCGGTCGATGACTACGTACGG
TACCCAGATCTGTTCGACAAAGTGGACGCCTTCTCGTATGTGTTCTTTCTGGTGGATTTGAAGCTAGGCGTCGTCACAGATAGACTTATCCTGCC
TAACGACTCCATCGTCATTGCCCACAATCATGGAATTTCCGTGTTTGGCTCAAC
(SEQ ID NO: 685)

Exon: 1001..1296
Exon: 1524..1645
Exon: 1702..1756
Exon: 1846..2474
Start ATG: 1717

Transcript No. : CT19171
CACAGTCCACCTCACTTTACAGCATATCGTACACTCACCGCCCGTCACACTTTTCGTTTGGCGGCTGGCACCACAACAAACATTAAGCAGCCACT
TCCGTTTCGGGGGTTCGGTGGCAAATTCGATCCGATGCGAACTCTAATTAGCCAATTTGGGGCTTGAAAACTGCAAATATTTGCTCGTTTTGTGG
AAACTAAGATTTCCACACCTTTGCAGTGTGACCGAAGCTTTGTGGTTCGAAAATACTGCAGGGATTCATCATTTCGGAAAATCAGACAAATATAC
TGCACGATGCGTTTCTTCCATTAACTTTAGAAATGTATATTTGGTATTTTTGGTATTTATCCGCCGATCGATAACTAGTGCTCCAGCCCTGGCCC
CAATGCATAACATCTCTGTTTCGTCGCACACTGAATAGAACCAAATTGAAAAGATGGCGAGTTTGGCTACCAAGGGATCAGGACTTGTGAACAGG
CTCCTCACACAGGCGAGGCCCCAACTGGACGTGTTCCTGAAGTACGCCAAGGTGGAACTGACGCCCCCGACGCCCGCCGATATTCCGGCCATTCG
CCAAGGACTGGGCAACATCATCAAGGGAGCCAAGACCGGCGCCTACAAGAACCTCACGGTTCGCGAGGCCTGGCTTAACACCCTGGTGACCGCCG
AGGTCATCTTCTGGTTCTACATCGGCGAGTGCATCGGCAAGCGTCACATTGTAGGCTACAATGTCTAAGCTTACTATAGTCTCCGCTTGGCAGTC
ACTGGAATGGGCAACGTAATCCCTAACAGATGTGTATATTTATATGTCTGCGAACATTTCGACTCTGAATAAAGTGAAATAGTAATTTAAAATTC
CGAAAATTTTCGAAAAATACATTGTTTTTTGAAAACCGTTAGAACGTTTGCGCGGGATTTGTGTAAGCTAAAGATGAGGTGATGTAAAACCAAGT
TTGGAATTAAAAGTTGACGATATTTAATGATAAAAATTAAAAAAATATATGTAATGTTATACATCAAATGTTTATGAAACGGTGTCGTAATCAAA
GAGGCTAATGGTTCAGAAATACATAATATACTTAGAGCATTTAAAAGCACTCAAGAA
(SEQ ID NO: 686)

Start ATG: 434

MASLATKGSGLVNRLLTQARPQLDVFLKYAKVELTPPTPADIPAIRQGLGNIIKGAKTGAYKNLTVREAWLNTLVTAEVIFWFYIGECIGKRHIV
GYNV*
(SEQ ID NO: 687)

Name: ATP synthase g subunit
Classification: enzyme

Celera Sequence No. : 142000013384288
TTTCCGATAGAGTAGCCGGCATTCGGATATACCTGGAAGCTTTCGATGATAGGACAGATGCCACGCGCCTAGTTATTTTTGCCAAAGTGCGTAAA
CTAACGCCATGGGCCATTGCAGTTAATTTGGGGTGCTTAAATAAGAAAAAAATTTAGTAACAAATCTTAGTTTTCATTTTTGGCGGGCAATTTTG
AAAGCCAGTTCACACGGTTTTGATGTACATACAAATTCGCGAGTCTGGCATACAGAAATGTTTACTGTACCTCTGTGCCGCCCCCACAAGCGAATA
GCGGATAGAATCTGCAAATCTATTGGAACTTGCTCCCTCTTTAACGGCTCAAAATATTCAATTTCCAAGTCATCCCGTACAATTTCAATAATTCT
GCGAAGGTTTTCCTTAGTGTATCGGTACTTTAGTCGAAATTTATGCTCATTTAGATCGGTCAATGGATTAAATCTTGGGTTCCTTTTCTTTATAT
GCGTTGCCCGCGCTCGAGAATTGTGTTTGATATTCAGAAACATTGAAAGTCTTTGAAATAATCAAAGTCTTTTAGAGACCTTTGAAATCTTTGT
ATATCTTCCATTTTCACTTGTTTACTTGCATAGCAGGGTGGCTGTTTTGTATATATTAGAAAATACCTCATACGTACATGCGGTATTTAAGGCTC
TTGCAACGATTGAAATTTTATGATGAAACTTTACACTTTAAAAATAATCTTTTTAAATGTTGTTAATTAAAAAAATGTAAGTAAGTAAATTAATA CTTTTATTTTTTTTAAGCACGTTATGTACTTTTGGAGTTAAATAATTTTTTTTTATGTATTTCTATACTTTTAAAAAAACAGAACAGAAAGAAAT
CAAAGCTCGAAGTACCAAAAAATAAATACTAGGGAAATAGAACCTATTGCGAAGATTTGCAAAAGCGATTGTTTTCAGTTGTGAAGACTAATATC
TACACATTCCAAAAGCTTAACGATCTTTGAAATCTGGCCATTTGGTCACACTGAGTCCAAAGCGTCGTTTTCAAAGTACTCTTTCAGTTTCCATT
GTGAAGTTTTAAGTGATCGCGAGTGCCAAAAAGTAACAATGGCTGATGATCAGGGACGTGGACGCAGGCGTCCACTTAACGAAGATGATTCCTCT
ACTTCCCGAGGTAGTGGTGATGGGCCGGTATGTAAACTCTTATTCAAGCTAGGAAAAAAAATCATAGCGGTAAAGCAAATTCCTTATAATTCCGT
TATGTCGCAAACACAAACACAGCCATGTACATAGATTGTAAATGCGCGCATTTCTTCGGAATTCGACACCAAAAGGAAGCACTAAAACTAACAAA
CAAAAATCTGCTATGAATTTGAGCTTGACTGCATAAAATCTTCTTGAATTTCTGTTGACCAAGCACTTTTTTCAAAGGGAATTCATTAAACATAT
TTCCAAAAACGCTTCTTTCAATTTGAATTTCCAAGGAAATGTAAAGCATTATCTGTTTCGTTTCATTTATTTTTTTTTAATAAAAACTGCTAAAA
TAACCATCACCTGACAGGAAGGTGGCTGTGGCAAGCCGAATCTTATTTACCCTTGCAGTCTATGTCTTTGGAATCTGCATGCCCGACGTTGATAT
GGACGGACATGACCAAATGGACCCGGCTAGTGATACTCATCAAAAATCATGGTCGGAAACGCTTCCTTCTATCTGTCACATACATTTGATTCCTA
GAAACTCTACGAGTAACGGGTATTTCTCCGATATTCATCCCAATTCTATACAACTTTGAGATGGCTTTCAGCATTGATATACTCTGAAATTGCAG
GCAAAGCATACTACAAAAACTATTTTTTACCATTTTTTTTCTGCTTCATCTTTGATTATGAGTAACAATATTTTCGTAGCTTGACCGTTAGTTTT
ATGATTTAAAATCTGTCGTACTTTAGGTAGTTGTTTAAATGGCTCACATTTAGGAATCACAACTATTTGTTTAAACCCCTTAATATTTTTTCTTT
TAATAATAAATAATAAACAGGTAATACTTTTTGATTGTTCATCGCGATTGTTTTCAATGTACAAAGTTGAGTCTTTCTGGTGTTTATTGCTGTCT
CGTGTTTATTGCTGAATCTCGCACGATCTCTCTCTTTCTTCTATGTTATTTTTTCCATCGGCGTCAATTATTCATAACTGCCGCTAGGTGGAGCT
AGTGTGCAGTCATTCACTTCTATTAGGAGACAGCGTCCTCTATATCTAATATTATAATTTTTTTTAAATGAGTAACTTACATCATTTAATGCTTT
CATGCAGCGGGTGAAAGTATTCAGAGGATCTTCATCAGGTGACCCGAGAGCGGATCCTCGTATAGAGGCTTCAAGAGAGAGAAGAGCTCTCGAGG
AAGCTCCCAGGCGTGAAGGTGGCCCGACAGAGCGAAAGCCGTGGGGTGACCAATATGATTACCTGAATACCCGTCCGGCTGAGCTGGTATCCAAG
AAGGGAACCGATGGCGTCCCGGTCATGCTGCAGACGAACTTTTTCCGATTAAAAACCAAGCCGGAATGGCGGATCGTTCATTATCACGTGGAGTT
TGAGCCGAGCATCGAGAATCCTCGTGTCCGTATGGGAGTTTTGTCCAATCATGCTAACCTTCTGGGATCAGGCTATCTATTCGATGGACTGCAAC
TGTTCACCACCAGGAAATTCGAGCAGGAAATCACGGTGCTCAGCGGAAAGTCGAAGCTGGACATTGAATACAAGATATCCATAAAGTTCGTTGGA
TTCATATCGTGTGCTGAGCCCCGCTTTTTGCAAGTCTTAAATCTAATATTGCGCCGCTCCATGAAGGGCCTAAATTTGGAATTAGTTGGCCGTAA
TCTCTTTGATCCCCGAGCTAAGGTAATTTCTTTTGGTATCGTTTTAAGTGCTGTTTGGTCAAATATGATTTATTTTAGATCGAAATAAGGGAGTT
CAAAATGGAGCTATGGCCGGGCTATGAGACATCGATTCGTCAGCACGAAAAAGATATTTTATTGGGCACCGAAATAACTCACAAAGTTATGCGCA
CCGAGACGATCTACGACATAATGCGACGTTGCTCACACAATCCGGCTCGTCATCAGGACGAAGTACGGGTAAATGTTTTGGACTTGATTGTCCTT
ACGGATTACAATAACAGAACTTATCGTATCAATGATGTCGACTTTGGACAAACTCCGAAATCAACATTCAGTTGCAAGGGTAGAGATATCAGTTT
CGTGGAATACTATCTCACTGTAAGTCTAATATTTACCACGGATATACATCGGCGTCTTATTTCTCCCAACATTTGTTCTCTTTAGAAATATAATA
TACGCATTCGCGACCACAATCAGCCGCTGCTGATCTCCAAAAATAGGGACAAGGCTCTAAAAACTAACGCTAGCGAATTAGTGGTACTAATTCCT
GAGCTCTGCCGAGTGACTGGGCTCAATGCCGAGATGCGCTCAAACTTTCAGTAAGACTTTAAACTATATTTAAATTAACAAGCTCTTGTGTCGCA
AACTATCTATTTCTTAAGTTATATTCTGTGTATCCTTTCTTTACATGACTAAAACTATATTAATTTCGCTAGTCCGTCCGATTCTTGACCTGTTT
GGAGTCAACGAGTTCATGCCGATCGGTTCGAAAAAACTTCTTACTGTTTGCAAACCTGAGATTACCTCCTTATCCCAGTAGACTAATGTTATTAC
AATAGAACTAATAACTAATAAGACTAATATGAGATAGAATTATTCCCCGACTATCAGATACCCGTTACTCAGCTAGTGGAACGGTAATTTTCATC
ATTTTTCTGTGGTATCGATAGATATTGAGGAATAAAATGAGAACATTTTTTAAAAATTTAAAACTAAAATTTTAAAAGTCTGGTCGTGACCGTTT
TGGCCGTTTCGTATGTGAAATGAGAGGCGCGGCTAAAGTGTTTTAGCTATACAAATAAAAATAGGCAAGACAAACAATAAAACGAAGAAAAATCT
GAGCACTTTTCAAAAGTGTGGGCGTGGCAGTTTAGGGCGGTTTTATGGCCCATAAAAAATGTAATATTTAATTATTATAAACAGGCTTATGCGTG
CCATGAGCAGTTATACGCGAATGAACCCCAAACAACGCACTGATCGATTGCGCGCTTTTAACCACCGTTTACAAAACACTCCAGAAAGTGTGAAG
GTCTTGAGAGACTGGAACATGGAACTGGACAAGAACGTCACAGAAGTACAAGGCCGGATAATTGGACAGCAGAACATCGTGTTTCATAATGGAAA
GTGAGTTGAGCAAGTTAAGAGCACTGCAAGTTTATAGTTAATAATTTTTTCAGGGTTCCTGCTGGAGAAAACGCTGATTGGCAAAGGCACTTCAG
AGACCAAAGGATGCTTACCACTCCGAGCGATGGCCTCGATCGTTGGGCTGTCATCGCGCCGCAAAGGAATTCCCATGAACTCCGAACTCTACTTG
ACTCTTTGTATAGAGCAGCTAGTGGAATGGGTCTTAGAATTCGAAGCCCCCAGGAGTGAGTTTTTATAAAAAAACACGTATACCTCACATTACGT
CTTTACTTAATTCGTAAAGAGAGGTTTCGTGCTTCGTTTTCTGGGTATATATCCACTTTAACTATCGTTTTACAAACAGATTCATAATTTATGAT
GATCGCACTGGAACTTATGTGAGAGCAATGGATGATTGTGTGCGCTCAGATCCCAAACTTATATTATGCCTCGTACCCAATGATAACGCCGAAAG
GTATTTATTCCCTAATAAGTGTACAAATCTAAACTTAATGACTATATTTATCGAAGACATTGTTTAATTTTGGTACACTAAAGTTAATATAAATG
AAAGTACTGAAGTAAACCTTTTTATTTTAGATACTCATCAATCAAAAAGAGAGGATACGTTGACAGGGCGGTGCCAACTCAAGTTGTGACCCTTA
AAACGACCAAGAACCGTAGCCTTATGAGCATTGCCACCAAAATAGCAATCCAACTGAATTGCAAGTTGGGATATACACCCTGGATGATCGAACTA
CCCTTGTCCGGACTGATGACAATTGGCTTTGACATTGCGAAGAGCACACGAGATCGGAAGAGGGCCTACGGAGCATTGATTGCCTCAATGGATCT
ACAGCAAAACTCCACGTACTTCAGCACAGTCACGGAGTGCAGCGCCTTTGATGTGCTCGCTAACACCCTTTGGCCGATGATAGCAAAGGCCCTGC
GCCAATATCAACATGAGCATAGGAAGCTGCCATCTCGAATCGTATTTTATCGAGACGGTGTGAGCTCCGGCTCTCTAAAGCAGCTTTTTGAATTT
GAAGTCAAGGACATCATTGAGAAGTTGAAAACTGAATACGCCCGCGTCCAGCTAAGCCCACCGCAATTAGCTTATATTGTGGTAACCAGATCCAT
GAACACGCGCTTCTTCCTCAACGGACAAAATCCTCCGCCTGGTACTATAGTTGATGACGTTATAACTCTGCCCGAGAGATACGACTTTTATCTGG
TCTCGCAACAAGTTCGTCAGGGTACAGTGTCGCCGACCAGCTACAATGTTCTTTATAGCAGCATGGGTCTCTCACCGGAGAAAATGCAAAAACTT
ACGTACAAGATGTGCCACTTGTACTACAATTGGTCGGGCACCACACGAGTGCCAGCAGTTTGCCAGTACGCTAAGAAGCTAGCTACCCTCGTGGG
TACGAACTTGCACTCTATTCCGCAAAACGCGCTCGAAAAGAAGTTTTATTATCTATAATTGGATATAATTTAGAATGGAGTATTAATCCTTACTA
AGAGGCCATATATGAAACTAGCCCAGACATTTATACTTTTTCAATACTTTCTTACTTTTGCTAAGCACTTCAGCATTTATGACTAAATATTTTGT
ATTTGAAATGCATTACTGCTCTTTTTTCAAACAAAAGCAAAATTGAGGATTAAGATTCTGGTATTTAAGCATAAGACCAGAGGAAATTCCCAAAC
AAACATTTAAAGTTATCTATCAAGACATGTTCATTAATTTGGAATATAATTACTTTATTTTTTATTGTATATTTTAGTTTATGTAAAGAAAAATT
ACATACATCCATGTTTGCTTACTTAACCACACATTCATGGCTGCTTATATTCGTGAAACATATTTTATTAATTATACAGGTATTTAACTTTCACA
AGGATAATACAATTTCATAGCTTGTTGAGTATACTGAAATGCTACGGAGTTCGATATATTTTAATGTGTTTGTATTTACAAAATTCTAAATTTTC
ATTTTGGATAAATGTTTTATATTAATCGTATCGATTGCAAGTTGGGGTAGGATTGAGTTCAGTGATAATATCGATTATTTATAATTTAATATCCA
AACACCGACTACTATGATACAGAAGCCCATATCTACTCAGACCTTGACTCCAAAGAAGCGAACAAAATTAGCAAGTCTTTTAAATCGCTTTCCTT
GGATTGTCGTCTAGGCTTAAAATGCAAATGCGTTCGTTCACTATAGCGATTAATTTAACGATAATTACTCGTTGGTGTATATACAATTCAATGAA
ACTTTTGATTTTAGACATATTATTTAGGATTAGGTGTATATTGTATAAAGGGTGGTAGAAAAGCTTTGGTGCTTTTGTGTAATCCAATTTCATAC
CACGCTTGGTTTCGACCATCGTATGGATTAATTCTCTTTGGAATTACTTCTTCTTTTTGTTTTTTAGAATTATGTCAGGCTTTAACGAGTTAATC
AGGGATCAAGCCGATGTTTCGTTCGGTTCCATCCAGCCCTCGCTGTCGTCTTCGCTATCCGAATCCTCGGACTCGGATAATTCGATAGCCACACG
TCTGGCCAAGATTGAAGCCACATCCAATGGCGCCGCGTTTCGTTCAATTTCCTTTTGCTCTGACTTTTCAACTTTACGTAGAGTAATACCTGGAA
AGATTAATTTGATGATATTTTTGCATTCGAACCTTGAATGGCAATTACTTACCATCTCGAATGGCCTTCATCAAGTCGTTGCGTGGGTCATGGAA
TGGAGGCAGCATCTTCTTGGGTGCGACAATGTGAGGCACACCATTTTGTTGGCCGGGCTGCTGCATTTCGCCATTGGCCAGTGATTTGGGAAGAA
TTTGATGCGGGCGCAGCGTGTGTTGGTTGCCACTGCCCATGCCTTCCTCGACTGGAGGCGGTGGCGGCGGCGGTGGTGGCGCGGCATTAGGTGGC
GACATCTTAGGCGAGTGCTGTAAGGTTTTGCCACAAATTAAACCAAATTGTGATATATTAACACCCATCAGTGAACAACAAACCTGATCTGGAAC
CGGCGGCGGTGGCGGCAAGTCGCTAAGGGAGTTCAGTTGATTGCCCGTCATACCGATGCTGTGGAAAGTATTGCTCAGTTGCGTCATGACCATAT
CATTGGCATTCTGGACGCTGTTGGGAGATCCAGCTCCCGACGAACTGTTCGCCCGGCCAAGCAGTTTGGCCGCCATATGCCCGCTGTTGACTCCG

FIGURE SHEET 372

TTCATGCCAGACATTGGTGAAATGACGTCTGGAACTGGTGGAGGCGGTGGCAAGGCATCCCGACTGGTCGACATACTTCTGCCCCTTGTCGGAGT
GTTGGCATTGGAGGCTGTGGGCGTACCACCACCGCTGCCATTCGATGGCGGAGCCGGTGGCGGCTGC
(SEQ ID NO: 688)

Exon: 1001..1167
Exon: 2288..2872
Exon: 2929..3249
Exon: 3316..3470
Exon: 4075..4275
Exon: 4329..4520
Exon: 4640..4750
Exon: 4876..6667
Start ATG: 1084

Transcript No. : CT19209
CTGAGTCCAAAGCGTCGTTTTCAAAGTACTCTTTCAGTTTCCATTGTGAAGTTTTAAGTGATCGCGAGTGCCAAAAAGTAACAATGGCTGATGAT
CAGGGACGTGGACGCAGGCGTCCACTTAACGAAGATGATTCCTCTACTTCCCGAGGTAGTGGTGATGGGCCGCGGGTGAAAGTATTCAGAGGATC
TTCATCAGGTGACCCGAGAGCGGATCCTCGTATAGAGGCTTCAAGAGAGAGAAGAGCTCTCGAGGAAGCTCCCAGGCGTGAAGGTGGCCCGACAG
AGCGAAAGCCGTGGGGTGACCAATATGATTACCTGAATACCCGTCCGGCTGAGCTGGTATCCAAGAAGGGAACCGATGGCGTCCCGGTCATGCTG
CAGACGAACTTTTTCCGATTAAAAACCAAGCCGGAATGGCGGATCGTTCATTATCACGTGGAGTTTGAGCCGAGCATCGAGAATCCTCGTGTCCG
TATGGGAGTTTTGTCCAATCATGCTAACCTTCTGGGATCAGGCTATCTATTCGATGGACTGCAACTGTTCACCACCAGGAAATTCGAGCAGGAAA
TCACGGTGCTCAGCGGAAAGTCGAAGCTGGACATTGAATACAAGATATCCATAAAGTTCGTTGGATTCATATCGTGTGCTGAGCCCCGCTTTTTG
CAAGTCTTAAATCTAATATTGCGCCGCTCCATGAAGGGCCTAAATTTGGAATTAGTTGGCCGTAATCTCTTTGATCCCCGAGCTAAGATCGAAAT
AAGGGAGTTCAAAATGGAGCTATGGCCGGGCTATGAGACATCGATTCGTCAGCACGAAAAAGATATTTTATTGGGCACCGAAATAACTCACAAAG
TTATGCGCACCGAGACGATCTACGACATAATGCGACGTTGCTCACACAATCCGGCTCGTCATCAGGACGAAGTACGGGTAAATGTTTTGGACTTG
ATTGTCCTTACGGATTACAATAACAGAACTTATCGTATCAATGATGTCGACTTTGGACAAACTCCGAAATCAACATTCAGTTGCAAGGGTAGAGA
TATCAGTTTCGTGGAATACTATCTCACTAAATATAATATACGCATTCGCGACCACAATCAGCCGCTGCTGATCTCCAAAAATAGGGACAAGGCTC
TAAAAACTAACGCTAGCGAATTAGTGGTACTAATTCCTGAGCTCTGCCGAGTGACTGGGCTCAATGCCGAGATGCGCTCAAACTTTCAGCTTATG
CGTGCCATGAGCAGTTATACGCGAATGAACCCCAAACAACGCACTGATCGATTGCGCGCTTTTAACCACCGTTTACAAAACACTCCAGAAAGTGT
GAAGGTCTTGAGAGACTGGAACATGGAACTGGACAAGAACGTCACAGAAGTACAAGGCCGGATAATTGGACAGCAGAACATCGTGTTTCATAATG
GAAAGGTTCCTGCTGGAGAAAACGCTGATTGGCAAAGGCACTTCAGAGACCAAAGGATGCTTACCACTCCGAGCGATGGCCTCGATCGTTGGGCT
GTCATCGCGCCGCAAAGGAATTCCCATGAACTCCGAACTCTACTTGACTCTTTGTATAGAGCAGCTAGTGGAATGGGTCTTAGAATTCGAAGCCC
CCAGGAATTCATAATTTATGATGATCGCACTGGAACTTATGTGAGAGCAATGGATGATTGTGTGCGCTCAGATCCCAAACTTATATTATGCCTCG
TACCCAATGATAACGCCGAAAGATACTCATCAATCAAAAAGAGAGGATACGTTGACAGGGCGGTGCCAACTCAAGTTGTGACCCTTAAAACGACC
AAGAACCGTAGCCTTATGAGCATTGCCACCAAAATAGCAATCCAACTGAATTGCAAGTTGGGATATACACCCTGGATGATCGAACTACCCTTGTC
CGGACTGATGACAATTGGCTTTGACATTGCGAAGAGCACACGAGATCGGAAGAGGGCCTACGGAGCATTGATTGCCTCAATGGATCTACAGCAAA
ACTCCACGTACTTCAGCACAGTCACGGAGTGCAGCGCCTTTGATGTGCTCGCTAACACCCTTTGGCCGATGATAGCAAAGGCCCTGCGCCAATAT
CAACATGAGCATAGGAAGCTGCCATCTCGAATCGTATTTTATCGAGACGGTGTGAGCTCCGGCTCTCTAAAGCAGCTTTTTGAATTTGAAGTCAA
GGACATCATTGAGAAGTTGAAAACTGAATACGCCCGCGTCCAGCTAAGCCCACCGCAATTAGCTTATATTGTGGTAACCAGATCCATGAACACGC
GCTTCTTCCTCAACGGACAAAATCCTCCGCCTGGTACTATAGTTGATGACGTTATAACTCTGCCCGAGAGATACGACTTTTATCTGGTCTCGCAA
CAAGTTCGTCAGGGTACAGTGTCGCCGACCAGCTACAATGTTCTTTATAGCAGCATGGGTCTCTCACCGGAGAAAATGCAAAAACTTACGTACAA
GATGTGCCACTTGTACTACAATTGGTCGGGCACCACACGAGTGCCAGCAGTTTGCCAGTACGCTAAGAAGCTAGCTACCCTCGTGGGTACGAACT
TGCACTCTATTCCGCAAAACGCGCTCGAAAAGAAGTTTTATTATCTATAATTGGATATAATTTAGAATGGAGTATTAATCCTTACTAAGAGGCCA
TATATGAAACTAGCCCAGACATTTATACTTTTTCAATACTTTCTTACTTTTGCTAAGCACTTCAGCATTTATGACTAAATATTTTGTATTTGAAA
TGCATTACTGCTCTTTTTTCAAACAAAAGCAAAATTGAGGATTAAGATTCTGGTATTTAAGCATAAGACCAGAGGAAATTCCCAAACAAACATTT
AAAGTTATCTATCAAGACATGTTCATTAATTTGGAATATAATTACTTTATTTTTTATTGTATATTTTAGTTTATGTAAAGAAAAATTACATACAT
CCATGTTTGCTTACTTAACCACACATTCATGGCTGCTTATATTCGTGAAACATATTTTATTAATTATACAGGTATTTAACTTTCACAAGGATAAT
ACAATTTCATAGCTTGTTGAGTATACTGAAATGCTACGGAGTTCGATATATTTTAATGTGTTTGTATTTACAAAATTCTAAATTTTCATTTTGGA
TAAATGTTTTATATTAATCGTATCGATTGCAAGTTGGGGTAGGATTGAGTTCAGTGATAATATCGATTATTTATAATTTAATATCCAAACACCGA
CTACTATGATACAGAAGCCCATATCTACTCAGACCTTGACTCCAAAGAAGCGAACAAAATTAGCAAGTCTTTTAAATCGCTTTCCTTGGATTGTC
GTCTAGGCTTAAAATGCAAATGCGTTCGTTCACTATAGCGATTAATTTAACGATAATTACTCGTTGGTGTATATACAATTCAATGAAACTTTTGA
TTTTAGACATATTATTTAGGATTAGGTGTATATTGTATAAAGGGTGGTAGAAAAGCTTTGGTGCTTTTGTGTAATCCAATTTCATACCACGCTTG
GTTTCGACC
(SEQ ID NO: 689)

Start ATG: 84

MADDQGRGRRRPLNEDDSSTSRGSGDGPRVKVFRGSSSGDPRADPRIEASRERRALEEAPRREGGPTERKPWGDQYDYLNTRPAELVSKKGTDGV
PVMLQTNFFRLKTKPEWRIVHYHVEFEPSIENPRVRMGVLSNHANLLGSGYLFDGLQLFTTRKFEQEITVLSGKSKLDIEYKISIKFVGFISCAE
PRFLQVLNLILRRSMKGLNLELVGRNLFDPRAKIEIREFKMELWPGYETSIRQHEKDILLGTEITHKVMRTETIYDIMRRCSHNPARHQDEVRVN
VLDLIVLTDYNNRTYRINDVDFGQTPKSTFSCKGRDISFVEYYLTKYNIRIRDHNQPLLISKNRDKALKTNASELVVLIPELCRVTGLNAEMRSN
FQLMRAMSSYTRMNPKQRTDRLRAFNHRLQNTPESVKVLRDWNMELDKNVTEVQGRIIGQQNIVFHNGKVPAGENADWQRHFRDQRMLTTPSDGL
DRWAVIAPQRNSHELRTLLDSLYRAASGMGLRIRSPQEFIIYDDRTGTYVRAMDDCVRSDPKLILCLVPNDNAERYSSIKKRGYVDRAVPTQVVT
LKTTKNRSLMSIATKIAIQLNCKLGYTPWMIELPLSGLMTIGFDIAKSTRDRKRAYGALIASMDLQQNSTYFSTVTECSAFDVLANTLWPMIAKA
LRQYQHEHRKLPSRIVFYRDGVSSGSLKQLFEFEVKDIIEKLKTEYARVQLSPPQLAYIVVTRSMNTRFFLNGQNPPPGTIVDDVITLPERYDFY
LVSQQVRQGTVSPTSYNVLYSSMGLSPEKMQKLTYKMCHLYYNWSGTTRVPAVCQYAKKLATLVGTNLHSIPQNALEKKFYYL*
(SEQ ID NO: 690)

Classification: known_flybase_gene
Gene Symbol: piwi
FlyBase ID: FBgn0004872

FIGURE SHEET 373

Celera Sequence No. : 142000013384554
TAAGTTCTCGAATATTTTATTTAAAATTGTGTTGTACTTCAGTTTTAGTCTGATAATAAGACATACAATTTAATAAAACAACAAACCAGTTTTCA
TGCCACTTAAAATGAAAACCAAGAAAACACATTTAAAAACAAGCCCAACAAAAAAATTGGGTACAAAGTAAAAGAGATAAACAATTTTAATAAAA
ATAACACTTTAATTATGTATTTCGTCTTTTTATTAGGCGGGCTAAATATTAACTAAATAAAAACAAGATTGAACGCTACAGTCTGGATCCTCGAA
TTGCAGATAAACGATACTCTGGTAGTAGAAGTTCCCGCCAGAAATCACTATTTTTTACGAATACTCCAACCATAAATAAAATAAAACTAAAATTT
TGGATTTATTGTATGTTTATTTATTTGAAATATCAGTTTGTATGCTGCGGTTCTCTATAATTTATTTCAATTATCCATAATGATTTAGTATTATC
TGAACCTTCTTTGTTGGTATTATGGTGTTAAATACAGATCTTGAGCATCGTTAATATTGCTTAACTTTTCCGTTTTCATGTTAGATGCCTTGCTA
AATGTGCATTTTTATTTCATACAAACTACGTAATTTCCGTACGTTATGAAGATGCTGAGTTGATTGTATCTTTGTTTGAAGAGTAGATGCGTTTA
CTTATTTTGGTTTTGATTTTAGATGCTGATGTAGTTTTATGCTATAAATATTTAGCTACGTTCAATTCTGCTTAATATTTAGAGAACATTAAATT
TTGAAGATTTTATTTCCTAAATATTCCAATGATTTGCTACAAATCCAACAGATGAACGTATGAGGTTTAATTCTTAGCCTAAAACTTTATTATTA
ATGTATATGTGTTTCAACTCCATGAAATTCCGCTCGTAACTACTTACTAAGAAATGTTAAAATAAATATTTTACGTTAATGTGTAAATTTAAATA
CAATATATATTTATTGCAAATTGCTTTGTAAATTTAATATAATTTTGTCCTTATGTTGATTTTTGTAGATTTAATTTATTTAAACGTTGTGAAGG
GGTACAAAGTGTGACGTTCAGGCTACGCTTAACTAACAACAAAATTCACATATAACAACAATAAAATGAAAATGTTACAAAAAATATATATCCTT
CAATTAGTTTATGGTGTATGGTAAAAATACAATGTAAATATAGAGACTTTTTGTTTCGTTCGTGTGTACTATTCATTTAACATTTTGTGCTGCTT
CAACGGTTTCCCATATAAATAAGTTCCCCTGACACAAGGAGGGAAAAATCAAAAATTATTTCGATGCAGGTAAGTTGGATTCGACAAAATTCGTT
TCAAGTGTGGGTGATTTTAAAGGTTTCGAACTCACAGCATGGTCAACAATCACACGAACTTATCTATATATCCTTGCAGTTCTTACAATCAATAA
TTATATCTGCAAGGGTACACAAACATCTGTTTAAGATAGACGTACGATCATATTGACCATTATACTGTTTGGGGATCGTTTGAGGAGTAAATATA
CAGAATGCTGTTTGTCAACAGAATGGCCAACACTTACATATAATTTCCTAACGTTTTGCTTTTGCTCCTAGCTTATGCTCAAATAAATAGATCAT
AAATAAATTAAATTACAATTTTGTAAATACATAAAATATTTGGCATTTAATTTCGCGAAGCTCTACAAATTGAATGGTATTCGATTTTAGCACAA
CATTTTGCACAAGGTTCAGAAGTGATTTGAAAATATATTTTCGGCTGGGTCTTTGGATGGCAATGCGTTTTAACCAGAACAAAAATCTGTCAATC
ATTCTCATTCTTGTGGAATGCTATAATCATATGTTACATCATACGTCTATATGATTTCATATCTCTTTCTTTTGGCATTGTGTTAGCATACAAAA
ATGGCAACATCAAAAAAAAAAAGTAATCGATTCAAAAGTCTTATGGGAGGAAACAAATCGTAAGAGAAATGTACATGATTTCTTTTTTACATTTT
CCCATTTGTTTTTGGCATTTAACATTATACTTTTGTGCTTATGCTTTGATCTATATATTTAATATATAGTATGTATCTATGAATTCAAAATTGTT
TCGCTAGGCTAAGTATTATGGAGCTGCTTATGTTGTTCGTACATATATGAAGTTTACTGTCTGTGTTTTTTGTGGTAGAAATATTCTGTTAAAAA
AGAGTTTTATGTTTTTGCTCTCCTGGCATATCAAGTTCATATATAAAGTCGCTTCTGAGGCTCCTGTGGATTGTGCTTTAAAAACGTTTTACAAA
TTCCAAATGGTTGCCTCATCTCTAATACAATTGCTCATCTGTCTCGTGTTGTTTTCGCTTGTCTTGTTGTTAAAAGTACTACAAAAGTGTGTTGT
TTCTGTCGTCAGTAGTGTTGTTAAAGTATTGACCAGGGAACATCGTACATTATCTCGCTAGCCTTCGCTGCTAAATGCTTTTCCCCATTCGCACG
TCTTCAGTGATAACGCTCGCTATGCATCCGTTTCGATTTGGTTTGTTAGTACTTCTCATCGTCCGTAATTTCCCTATGGGAATTCTGTAATTCTC
AGGCCTTGTAGTGCTGATTCCTCACCGCGCAGCAGAGGCTCAGGGCGAAAGTCAGGGACAGCAGCTCCAGCAGAATGACAGCGGCGGTGACGGCG
AAAATGGTGACCCAGTTCTCGTAGATGATTTCAATCAGCTTGTCCACGCAGCCCTGCAAGAGACGTTTAATATGAAACTCATTAATCGGTTTGTG
TAAAAGTCAGCTCGATTTTCATTCAGTTTGTTTACAGCTCGCAATCTCTGGATCTACTACCCAACCAGACTGGCAGACAGAAGTTTGAGATGCGT
GTTGAATATCAATATTAATTAATACGTTTTTATCGTCTCAGCATTGGCGGGCGTGAATGTTTATTAACCCAATGCTTTCAGACCGCAGAAAAAAA
GGATTATTAGTTTTTATGGCCAGGCGGCGATAGCGATCGGTAGGCCAAGAAATTATGATTCGGGCACACCTATCAATTGAGTTTTGATGATTTTT
TGGAAATTCACTGAATCGAAAAACGATCTTTTCTGGTAAAATTCATATGACTCACGGAATCGAAAAACTCTTTGGTTGGTCATTGGCATTACCTG
CTGATAAATGGCGTTGTTCAATGGGCCACCAAATTTCAGGCGTCTGGACAGCTCACACTCATTATCCTTTAGATTATCCTTGCAGCAGGACTCGG
GTATGTTATAGAAGACATTCATGGAAGACACGGCGATCTCCACAATATTTGTGCGATCCACATTATTAAACCGACTCGTGGCCCAATCTCCAGGT
CCATCGGCGCCGCAGCATTTCAACTGAAACAGATCAGGAAAGTTCGCATAAATCGTTTTTCCGACGACGTGGTGGGTATGTCCAAGTACTTACAT
TCTTTTGCAGCGTATCAAAGGTGACGGTGCGCGAACTCATCGTGGACTGGCCGTACTCCTCCTGGACTGACGACTTGACAGCCGCCCGCACGATG
TCATCCAGCTTGTCTTTGTTGTGGAAGGCCCATGCTCCGGCTGCAATTTGTGCCACCATCACGATGAGTATGACACAGAAGAACTGCAAGAGAAT
TTCAGATTTATGAATGACGGAGTCCGGCCCGTGGGCGTTGAGTAAATAAACTGGTTGCGATTTAAGACAGATATGTTTGCACTCGCAATAAGGAA
CTCCAATTAAGTGCAACTTTTGTTTTCTTTACATCATTTATATGTATAAGATATACTTTCTGTTATATATATTTAATAAGTACTTTAAATGGCAA
TACTATTGGATAAATTTTCTGTATTCACAGTCCAATTTAGTTAGGTATAAAATTATTTTGGCAAGTGCATCGTTTTGCCAAACTGCCAAGACATT
GTGGGCGAACCTCCGTTGCAATCATATGAGCGGAACCGTGTGGGCCACACATTTGCATGCATTTTAATTGGAATTCCCAGACACTGGTTATGATA
TTACTTTTCACTTACCGAAACCAGCAGACATTGCGACTCACGACAGACTCCGCAACAGCCAAAGAATGCGCCCAATGTGATCAGTATGCCGATGG
CGAGGAAAACATACAGGGCTATGTGATAATGATTGTAGTTCTGTGTCATCGACAGCATAAATGTGGGATCCGTCAGCATCCAAACGGAGGTCACC
ACGATGGTCAGTCCGATGAGCTGCAAGCGAAAAGAATACAAAATATAGTAGAGCATTACCTATTTTTACACATTTTCGCTGTAATTCTCAAATTG
TTGCATCCATCTCACGCTGGGCACACGCGTCAATGACGCCATCTGGCGGCAAGGCGGCAATTAAAGTGGGAGACTGCCCCGCCCAGTTTCGCCTT
GCTTTAAACTTCTATAGTTTCATACATATGATGTCAGCTTAGTTGGACGCAGACTATATACATAGCAACTGCTGTTGCGCTTCTTTTAATTTAAT
TAAAGGCAGTAAACAGAAACCAAGTACAAATTACAATTTTCCCCATTCCATTCAATTTGTTAAAAAAAAAATCAGTAATTCTATCCAGTATACAG
ATTCAAAGGCAGCTTTTTGAGCTCCGAACTTTCAAAACCCGATAAGAAAAGGCCCATTAAGTTTGAAAATCAATGATGCGATAAAATTTGGTTTA
AAGTTAAATTTTGGCCTTCATCGCCAAGACATACTGTATGTATATACATATAGAAGTGGCAAGACATTGATCCCAAGCGAGAATATGAGAATTGC
GAGCTCGTGTTATCTCACTTCTCGGGTTATCAGCAAACGAAATATGAACTTTTCTTTGGATTTCCGCTAAAAGAATTCCGGTAATGTATTTCTTC
TTAAATTTTCCTACCCAGATATTAAACACTAAACTTGCTATTGCCAATCCATCCACCAGAAAAATGTTGTTCCGCTCGTGCAATGAGTAAGAGAA
TCTAATATAGAGGTAATGACTTAATGGGTTGGTCGAGGTGTCTATGCAAGTTCATTAATTATTCAGCAAAATTATTCATCGCAGGGAAATTGAGT
GTGCGATGAGAGCTAATCAAGAGATGTAAACAAGTGCACATATTACATGGGAAATATGTAAATTTAGAACCACTTAAGAACCGATGGCTAACTGA
GAAGCATTTCCAAATACAAAACACTTCTTATCTCGTATTTTTTCTCAGCCCGCAAGCTTTTGTAATTGCCAAGAGCATCAGTGCTTTCCGATAAG
ATTACGCAGTGGATCTCGCAATAAGCAAATATCTATTTAACTTAAAGATACAGCAAAATATAAGATACAGTTTTTGGCGCCCAGGAAAAACGGAT
GAAAAAGCATGAGGAAGTCTCGTAAATTTCATGAAAATCTTATGAAATATAAGAGAAGCGGAGACCGGCTTTTATGTGGGTGGTCCACGAAAGAG
AGAGCTGCCATAAAGTGAGCGAGACAAAAAGTGTGCCACAAAGTGCACGATATGCTGGCCCTAAAGTTCATGAATGTGCATGTGTGCAGCTAACG
GAAAAACTACTCATGGAAACGTAATACAATGTTGCCCCATTCGAGGGCAGTTTATTGAGTAAGTACATTGTAACCAGAAGCCCTTGTTTGCATAG
ATTTTACTTATTTTTCCAGGTCAGGTTTTCGGGTATGGATCAGTAACATAATCTTGAATTTGTTCATGTGTTGAATTAAAAAAAAAAATGTTTCT
GAAGAAGAGGTTTATTCCTAGAGCTCTTATAAAGTATGTGTATGTATATACTACTTTGGATAAACCTCAATTCCCTTATCCTTTTAGGGAACAAA
AGTTGACCTCGTTTTGAATCAGTCCCATTATCCCTGAACGAACTGAATCCACGCCTTGTTTGTAGCTCTGTTTGTTGGAATTTTTACGATTCCCC
GAACGTTTTCACACACATATATTTTTACACATCTGACACTATGTCGCGTGTCCAGGACAAACAAACAAAAATCCTGCCGAATGGGCCAATAAATG
TACAGAGTCCTTCGTTGACCCAGTTTTCAGAGCCGAGGCGTCGAAAGCGGAAAACGAGAGAGCATTTTACTGCTGCTAAATTGCAAAAAAAAAAA
TAAAATGGGGCCAAAAGGCAGCTGGGCTTGCATTGCATGTCCAGTCACAGTTTTGTCCCACAATTAACCGCATCGATGGCAAATCGCAGCCAACA
GCCATCATGCATCAGCCATAAGCTGAAAATACAAACTGAAAAATGAATGAAGCGCCACTCATGAATAATTGAGTGAAAAATAGCACAGCGAATTA
AGTATGTAGATGTGACATGTCACAGCGAATTGAAAATAGATACAGGCCAGCTTCGTTACTTGGAGAAATATTTTTAAATATTATTTTATTCACAG
CAAAAGATTACATTTTTTTCAGGAATTTAAGAATTCTGCACTATGGAAGTCTGACTGTGCTGAAATAAATGGTTTTTTTAGTGGGTGGACAGGAT AGGATTGTCAGATGGTCGACCGAATATTTGGAAATCTTTCAGTTTTGGTCACTGTCAACTTCAATGACGACAGCGCCGGCCGTTTAGCATTTTAG
ACGCTTATGGCATAGGCCTCCCCCAGCATCTTGGATGTGGGATATCGGCCCCATTGGAGCGTCAGCGTCCTCAGAGATCGTGGCGTTTGATCACG
ATGCCCCACGGCGACGATGAAAATGGAAATGTTTGGAAATCGATGCACAGTGGAGAGCGAGATTCAAAACTAATCGGACAGTGGTCATTTTTTGC
GAAGTTATATAAAAATACTATTATTAAATTTATTATGGCTTTGTGGGGTAATTGATAACATGCCCTGGCTAAGAATAGCCTCAAAACAATGTATA
AAAAGTCTTATATAAAATAATATCTGACGCACTTTCATCCATAAATCGCTCTAAAAATAGTTCAAACGATTAGTGAAACGAACTGCATCACAAAC
ACATCACAATTTCTATCGCTCATTGTTCCTCCACTGAAATCAAACACACCACTGTGCATCCAACAACAACAACGATGAATACTAAAACATCACAG
ATCAAGGAACATTACACAGAAACCAATTATTGGATATAATCTTATTGGGATCGGTTAATTTTAATTTTTTTTACATGACATATATACAATAAACG
AAAAATAATTGAAAGGTATTCGAAAGTTTCCAAACACGAAACTTGGCTAGGCATCAGTATTTTCTTTCTGTGTACAACAACGAAAAACTGAACGG
ACGCGTAAGTTTGTGTTGTTCCTCGCCCGTATTCGAAAATAGCTTTTGACTAATAAATACTATAGACAGAAATCGAAAAAAGGCAGCAACAATCA
ACAAACGAACGAAAAAAAAAATTAGAAATCAGCCCGCATAAGAATCAAAATTTTAAATTTGTTGCCCAAAGGAAAAGCGAAACTGATTTCGCAAGC
CGCGGAAGACAAGAGGAAACCCCAAGAAAAACTCAAGGAAACTCAAAACAAACGCAAACAATCGCTGTGGCAGATAGTAATTGAATGGAAACAAT
TGAAAGCCTAACGAGGCTATGTTGAAAGTCGAAAATTGCGTAAAACAACAAGCAGATAAGTTGGCCAAAGAAAGTAAAACCCTTTTTTTTGGGGT
GAGGAGAGGTCCTTTTTACCGAATTAAGCCAACCGAAGTTTGTAAAAATATCAACGGCACGTATACGTTATAAAAATAATAAAACAAAAAAAGA
GAGACAGGAAGAGACAGAAGCAAAAGAAAAACAACTGAACAAACATGTGGAGGGAAAAGAAAACAGTGGGAGGTGGGAATGGAGATGCTTAAATG
TTTATCTGTCTGTGTGTGTGTGTGTCCCCTCCCACAACGGAACTTCTATTGTTTTATGCGGGAGTACGAGCAGAGCGGTAGGGAGTGCGAGCGG
GAGATGGAGAGATACAGTGATGTCGCTTTTAAAAGCCAGTTGAAGTTTTGAAGTTATAAATGGTAGAAAATAATTTAAAGTCAAATAGTTCATAA
CAAACAAAACCGATTTGTTTAATTTCAAAAAGAAAAACCCTTCTATTAATGTTTTTAATTAACCGCGTACTTGAATATTTATATAATCTTGTCCA
TTTAATGTTTTTAAGCCCGCTCATTAAAAAAAAAATATTTAAGTTAATATATTATTATATTTATTTTATTATTTATTTATTTATATTTTTTACTT
CCTTTTCGATTAAATATTTCAAGCCGTACTTAAATAAGTTTCAACTTATGTTTTGGGCACCTCTGGGATCGAGAGAGTGGAAAGAGGGACTGAAA
GAGCGGTAGGACTCCAAAGAGCGTGCGCACGGCTCCTCCCTCCGCCCGCGCGCCAAGCGTGAGAAAGAGGGGCGTAGGGAATACACAACACACAC
ACATTCGCTCACGCAACACCCACACACACGCGCGCGAAAAGGAGGTCCGTGTGTTCCAGTTGTTGTTGTGATGGGAGAGAACCGAATCTCGCATT
GTTGTTGTTGCTGCTGCTGCTGGAATCTACATACCCAGAATAAAATGTTTATAAGGACCATCAGATATTTGACGCACGAACAGCAGCCGTTGAGA
CCCATGGCGCGGATTGATATTCTTAAATAGGTAACTCCTTAAAAAGTAGCTGCAATTTAACTGGTTTTTCAACCACTTGGAGATGCTCTTTTTCC
AAGGAACCCCGAACTGCAGTGTCGCCTGCACTTTTCGACCTTTTGCACTTTTCAAAACACCCGCTCGATTGTACTATATTTTTCAAATTTTTTT
AAAATTTCCCGTGCTAAAATCCACCGATTTGAGCCACTGTTTGCGCGATTGGCCGTTGCACCCGATTTGTTTTAAAAATTTTATTTGTGCATCGA
GGCGTCCGTCCAACGTAAAATTCTTGTATCAGTGCGACCATTAGCTCGGCCGTTCAAATATACCAGCGGGTATAGAAAGGCTAAAAACCGAAAAG
TGGTGACCCTTAGAAGATACCAAAGAAGTGGTTGAATAACTTTGATGAGGCTTAGCATGGCTTGCAACCTGCTTGGATTTGCAGCCTATACGCAA
ACCAAAGTGGCCTATCGATATTTTGGATAAGTTCTATTGCCAATTTTCCCAATAAAATAAAAACTTCACTTGAATGTTAAAAGTAATTTAGTTTC
AGTGTTTACATAATGTTCAAATAACCTTTTGATTGTTATTATGAAAGTTAAAAATTAAAAATTTAGATATTCTAACTAACTATTATCCCCAATGT
TTCAGCTATAATCACCATATTTAAAGTAGATTTCATTTTAAAGTATAAATTTGTGGTTGTTTACATTATTTTAACATGTCTATTTAATTATTACT
ATGAAAGTGGGTAATTGAAAATTAGGATATTCCAGGTTTTTGATTTACTTTGGCTATGATTTTCCCAAAATATTTAAATCTGTAAATGTAAACAG
TTTGAAATGTGACCTTAATAGTTCATGCTTTGTTCATTCTTCTGCGAAACGGTCACACTGTTCGCGCAGGCGAAAATGGCCTAAAGCGTGAAATG
TTTAATTCGTTGTTGTTTCTCCTCCGCAATAGTTACTAATAGAAACAAATGCAAAATGGCTGTCTAACGTTTAAGTGCAGCGACCGCCGAAGATC
GTGGAAATATGCATGAAAAGCGGCTCGCAGGCAAATGAAAGGCGCGTGAAAATGTAGCAGACACCTTTTTATCGCGAAAACGAACATCGGTGCAA
AGGGAAAAACAAAAACCAAGGAAAATACAGCCAAACGCGAATGTGAATGTGAAGGCAAAGTAAGCGAAAAGTCCCCCAACTTTTTTGGGGAGTAT
CGAGTGCACCACATACGTTTTTCAATATATATTTCGATTGCATTGAAATCAGAAACATGACAA
(SEQ ID NO: 691)

Exon: 8848..8490
Exon: 4200..4006
Exon: 3598..3419
Exon: 3348..3133
Exon: 2713..1001
Start ATG: 8555 (Reverse strand: CAT)

Transcript No. : CT19213
TTGGACGGACGCCTCGATGCACAAATAAAATTTTTAAAACAAATCGGGTGCAACGGCCAATCGCGCAAACAGTGGCTCAAATCGGTGGATTTTAG
CACGGGAAATTTTAAAAAAAATTTGAAAAATATAGTACAATCGAGCGGGTGTTTTGAAAAAGTGCAAAAGGTCGAAAAGTGCAGGCGACACTGCAG
TTCGGGGTTCCTTGGAAAAAGAGCATCTCCAAGTGGTTGAAAAACCAGTTAAATTGCAGCTACTTTTTAAGGAGTTACCTATTTAAGAATATCAA
TCCGCGCCATGGGTCTCAACGGCTGCTGTTCGTGCGTCAAATATCTGATGGTCCTTATAAACATTTTATTCTGGCTCATCGGACTGACCATCGTG
GTGACCTCCGTTTGGATGCTGACGGATCCCACATTTATGCTGTCGATGACACAGAACTACAATCATTATCACATAGCCCTGTATGTTTTCCTCGC
CATCGGCATACTGATCACATTGGGCGCATTCTTTGGCTGTTGCGGAGTCTGTCGTGAGTCGCAATGTCTGCTGGTTTCGTTCTTCTGTGTCATAC
TCATCGTGATGGTGGCACAAATTGCAGCCGGAGCATGGGCCTTCCACAACAAAGACAAGCTGGATGACATCGTGCGGGCGGCTGTCAAGTCGTCA
GTCCAGGAGGAGTACGGCCAGTCCACGATGAGTTCGCGCACCGTCACCTTTGATACGCTGCAAAAGAATTTGAAATGCTGCGGCGCCGATGGACC
TGGAGATTGGGCCACGAGTCGGTTTAATAATGTGGATCGCACAAATATTGTGGAGATCGCCGTGTCTTCCATGAATGTCTTCTATAACATACCCG
AGTCCTGCTGCAAGGATAATCTAAAGGATAATGAGTGTGAGCTGTCCAGACGCCTGAAATTTGGTGGCCCATTGAACAACGCCATTTATCAGCAG
GGCTGCGTGGACAAGCTGATTGAAATCATCTACGAGAACTGGGTCACCATTTTCGCCGTCACCGCCGCTGTCATTCTGCTGGAGCTGCTGTCCCT
GACTTTCGCCCTGAGCCTCTGCTGCGCGGTGAGGAATCAGCACTACAAGGCCTGAGAATTACAGAATTCCCATAGGGAAATTACGGACGATGAGA
AGTACTAACAAACCAAATCGAAACGGATGCATAGCGAGCGTTATCACTGAAGACGTGCGAATGGGGAAAAGCATTTAGCAGCGAAGGCTAGCGAG
ATAATGTACGATGTTCCCTGGTCAATACTTTAACAACACTACTGACGACAGAAACAACACACTTTTGTAGTACTTTTAACAACAAGACAAGCGAA
AACAACACGAGACAGATGAGCAATTGTATTAGAGATGAGGCAACCATTTGGAATTTGTAAAACGTTTTTAAAGCACAATCCACAGGAGCCTCAGA
AGCGACTTTATATATGAACTTGATATGCCAGGAGAGCAAAAACATAAAACTCTTTTTTAACAGAATATTTCTACCACAAAAAACACAGACAGTAA
ACTTCATATATGTACGAACAACATAAGCAGCTCCATAATACTTAGCCTAGCGAAACAATTTTGAATTCATAGATACATACTATATATTAAATATA
TAGATCAAAGCATAAGCACAAAAGTATAATGTTAAATGCCAAAAACAAATGGGAAAATGTAAAAAAGAAATCATGTACATTTCTCTTACGATTTG
TTTCCTCCCATAAGACTTTTGAATCGATTACTTTTTTTTTTTGATGTTGCCATTTTTGTATGCTAACACAATGCCAAAAGAAAGAGATATGAAAT
CATATAGACGTATGATGTAACATATGATTATAGCATTCCACAAGAATGAGAATGATTGACAGATTTTTGTTCTGGTTAAAACGCATTGCCATCCA
AAGACCCAGCCGAAAATATATTTTCAAATCACTTCTGAACCTTGTGCAAAATGTTGTGCTAAAATCGAATACCATTCAATTTGTAGAGCTTCGCG
AAATTAAATGCCAAATATTTTATGTATTTACAAAATTGTAATTTAATTTATTTATGATCTATTTATTTGAGCATAAGCTAGGAGCAAAAGCAAAA
CGTTAGGAAATTATATGTAAGTGTTGGCCATTCTGTTGACAAACAGCATTCTGTATATTTACTCCTCAAACGATCCCCAAACAGTATAATGGTCA
ATATGATCGTACGTCTATCTTAAACAGATGTTTGTGTACCCTTGCAGATATAATTATTGATTGTAAGAACTGCAAGGATATATAGATAAGTTCGT
GTGATTGTTGACCATGCTGTGAGTTCGAAACCTTTAAAATCACCCACACTTGAAACGAATTTTGTCGAATCCAACTTACCTGCATCGAAATAATT TTTGATTTTTCCCTCCTTGTGTCAGGGGAACTTATTTATATGGAAACCGTTGAAGCAGCACAAAATGTTAAATGAATAGTACACACGAACGAAA
CAAAAAGTCTCTATATTTACATTGTATTTTTACCATACACCATAAACTAATTGAAGGATATATATTTTTTGTAACATTTTCATTTTATTGTTGTT
ATATGTGAATTTTGTTGTTAGTTAAGCGTAGCCTGAACGTCACACTTTGTACCCCTTCACAACGTTTAAATAAATTAAATCTACAAAAATCAACA
TAA
(SEQ ID NO: 692)

Start ATG: 294 (Reverse strand: CAT)

MGLNGCCSCVKYLMVLINILFWLIGLTIVVTSVWMLTDPTFMLSMTQNYNHYHIALYVFLAIGILITLGAFFGCCGVCRESQCLLVSFFCVILIV
MVAQIAAGAWAFHNKDKLDDIVRAAVKSSVQEEYGQSTMSSRTVTFDTLQKNLKCCGADGPGDWATSRFNNVDRTNIVEIAVSSMNVFYNIPESC
CKDNLKDNECELSRRLKFGGPLNNAIYQQGCVDKLIEIIYENWVTIFAVTAAVILLELLSLTFALSLCCAVRNQHYKA*
(SEQ ID NO: 693)

Classification: known_flybase_gene
Gene Symbol: BcDNA:LD19727
FlyBase ID: FBgn0027865

Celera Sequence No. : 142000013385214
GTGGTGCCGTCACCAGCGGCCACATCCTGGGCACGCGACAGCTCCACCAGCATCTTGGCAGCCGGGTGCAGTACATTCATCTGCTTCAGGATGGT
GGCGCCATCGTTGGTGATGGACACCTCGCCGTTGCCGGCCTGGATCATCTTGTCCATGCCGCGGGGGCCCAAACTGGTGCGGATAGCATCGGAAA
CGGCTGGAAAACAGAATTATTTCAATAGGTTATAAATGTATTTTAATATTTCGTTAAAACTTAATGAGAAACTCAGATAAGTGGAATTCGTGTGG
TTAGTTTTACACAGCAGCATGACTAATTTACATACATACATACAAAAAGACATATGGTGTTTTATGTGTTAATTCAAAAAATCTACTGTAACTTA
TCTTAAGAGATAAACAATAAAATCCTTGTAGCGGATAAAAGGGTATTGGGAATAGAGTATTAAAAATCCTCAATTTTTAGGTTGTTTCAATTCAT
CACATGAGTAATGCGCGCTCTTCTTCTTCTTCCGCCCAAGAAGTTTCCAGACAGCCGGCATCCAACTGCTTTTTCAATAGGCCATTTGGCCGGAA
ATTCTGATGCACCACTGCTCGGAATTCAGTCACCTCGGTTCTTAGCTCAATAAATAGCACATACGCCAACATTTTGATACAAAAATGTGTTTAAT
TTTGTTAATTTCCTCGCTTTTTCTCACCTTTGGCCGCCTGGATGTTGGACAAACGCACATCGGTGGGCTTCGACTTGTCCTTGAAGGCCTTGGCC
GTTGGCTTGATGTTGACAGCTGCTGCCTTGGGCGCCATTGTAGGGTTAAGTTATAGTTTTTTAACAAAACACAGTTATTCTACAATAAATTCACA
GCGATTTACACAGAACACGTTGCTGCGAAATGTTAAGGAAAGTGTGGCCGCACTCGCTGAGCTCAAATATACCGCCAACTTATCGGCATCGATAA
CATCATCCCTTGTGAATGGCAAATTGGTGTGACCGTATTTTGCGTTGTGACTCGGCTGCTTTATTTACATTGAATTTTTGTTCGATTTTTGAATT
TAAAATAAAAATAATGCCGCACGGACACTCTCACGATCACGGCGGCTGCAGCCACGAGGCCTCGGACGTGGACCACGCCCTAGAAATGGGCATCG
AGTACAGCTTGTACACCAAAATCGATCTGGACAATGTGGAGTGCCTGAACGAGGAGACGGATGGCCAGGGAAAAAGTGTCTTTAAGCCGTACGAG
AAGCGCCAGGATCTGTCCAAGTACGTGGAGAGCGATGCGGATGAAGAGCTCCTCTTCAACATTCCCTTCACCGGCAACATCAAGCTCAAGGGCAT
CATCATAAGTGGGGCCAATGATGACTCCCATCCAAACATGGTCAAAATGTAAGGAACAAAAGTCAAGGCTGCTTTAATATTACTATATTCATCAT
ATATCTTATTTTTCAGCTTCAAGAACCGACCCAGGATGACCTTTGATGATGCCAGAGCAAAGCCCGACCAGGAGTTCCAGCTGACCCGCGATGCC
CGCGGAGAAATCGAGTACTCACCCAAAGTGGTCACCTTCTCCTCCGTGCACCATCTCTCCCTCTACTTTCCCAGCAATTTTGGCGAAGACATAAC
ACGCATTTACTATATAGGTAAGCTCACAACAATCTATGTTTTATCTGTGTTCCCAACTAAAACCAAGTCACTATTCAAAGGTCTTCGAGGAGAGT
TCACAGAAGCTCATTACCATGGCGTAACCATATGCAACTACGAATCCCGTGCCAATGCAGCGGATCACAAGGAAAAGGCTTTCGATGGAGTCGGC
AGAGCCATCCAATAGGGTTATAGAGATTAAAATTTACAATTTAATTGAGTATCTCTGTAGTGTATATATTTTGTGATCATTTAAGGCAAGAAATG
TTTTTGTATTCGCTTAACTTATTGAGCATTTGTATTGCACAGATATTGTGGGCTAAATCATACTAAGTATATTGTGTGGGTGGAATCACATCGGG
TCCTATTTTCATGCCCATATTGGGCACTTTATCCGAATGGATTTCAGCCGTGACCTCGGTGAACAGCTTGTCCCACTGCCAGAGATCGTCCTTCT
CGTTGAGGCTCTCCTGTGGAACCAGGCAATCGGTGAGGATTGAGAGATCAAAGCCATCCACAGCTGAAAAGGCGTACTGGGAAAGCAAATCGGAA
TTGGCCTCCTTCAAAACAGCAGATCGTGAGGTGCCAATACTACAAATTACAACTTATTATCGTAGTGAAGAGAAATATAGCAGCTTCTGCTTACG
TTGGCGGTTCTACAATCTCATTGAGCATGATTTCGTCCTTGACATCATCCATGTCTGGGATGACGGGAATGTCATCCGTTGGTATGGAATTTGTA
GCCGACTTTGTTTGTTTAAAGCGCTCACTAAAATGAATTTTATCATTATAACAGTCGGTGGAAAGTGAAGTTATTGTGATAAACTTGTACTCACT
CATCAAAGGAGTTTTTCTTGGACCTAAAAAGATATAGAGCAATCAGTAATGTGCCTAATTCGAGCCTAATCATACCCACTTTAATCCTTTGAGTC
CAGAATCCGCCCAGCCACCTGAAATGCGACGAATGGGTGGTCGATGTGACTCGAATTCATTGTTGTATGTGGACGAGGTGGCCGTGTCCGAGGTG
GTCGGTGGGGTGCCCGCCTGGACATTCAGCGTAATGTCGATGGAAATGTCCTTGGAGCCCCCAGCCGCCTGGACATCCTCCTCCTTCAGAACATC
GCGACTCTTGGAGCGCCGACCCTTCCTGGCCGTCGTCTAGGGTGGCAAATAAATCGAAACTTCAATTTGCATCCATTTAAACAGGGTTACTTACC
TTTCTTATGGTCATCTTG
(SEQ ID NO: 694)

Exon: 1001..1378
Exon: 1442..1632
Exon: 1696..1868
Start ATG: 1059

Transcript No. : CT19326
CTCGGCTGCTTTATTTACATTGAATTTTTGTTCGATTTTTGAATTTAAAATAAAAATAATGCCGCACGGACACTCTCACGATCACGGCGGCTGCA
GCCACGAGGCCTCGGACGTGGACCACGCCCTAGAAATGGGCATCGAGTACAGCTTGTACACCAAAATCGATCTGGACAATGTGGAGTGCCTGAAC
GAGGAGACGGATGGCCAGGGAAAAAGTGTCTTTAAGCCGTACGAGAAGCGCCAGGATCTGTCCAAGTACGTGGAGAGCGATGCGGATGAAGAGCT
CCTCTTCAACATTCCCTTCACCGGCAACATCAAGCTCAAGGGCATCATCATAAGTGGGGCCAATGATGACTCCCATCCAAACATGGTCAAAATCT
TCAAGAACCGACCCAGGATGACCTTTGATGATGCCAGAGCAAAGCCCGACCAGGAGTTCCAGCTGACCCGCGATGCCCGCGGAGAAATCGAGTAC
TCACCCAAAGTGGTCACCTTCTCCTCCGTGCACCATCTCTCCCTCTACTTTCCCAGCAATTTTGGCGAAGACATAACACGCATTTACTATATAGG
TCTTCGAGGAGAGTTCACAGAAGCTCATTACCATGGCGTAACCATATGCAACTACGAATCCCGTGCCAATGCAGCGGATCACAAGGAAAAGGCTT
TCGATGGAGTCGGCAGAGCCATCCAATAGGGTTATAGAGATTAAAATTTACAATTTAATTGAGTATCTCTGTAGTGT
(SEQ ID NO: 695)

Start ATG: 59

MPHGHSHDHGGCSHEASDVDHALEMGIEYSLYTKIDLDNVECLNEETDGQGKSVFKPYEKRQDLSKYVESDADEELLFNIPFTGNIKLKGIIISG
ANDDSHPNMVKIFKNRPRMTFDDARAKPDQEFQLTRDARGEIEYSPKVVTFSSVHHLSLYFPSNFGEDITRIYYIGLRGEFTEAHYHGVTICNYE
SRANAADHKEKAFDGVGRAIQ*
(SEQ ID NO: 696)

Classification: hypothetical

Celera Sequence No. : 142000013384548
GTAACCAAGTACACCTGTTGGAAGTTCTCCAGCGATCCATTAGCGGGATGTGGATGGAATATGTCCAGCAGACCGATTACGTTCTCATGATCCAT
ATGCTTTAAAAGTCGAAGCTCCCGGTACGTCCTCTTTGCATGGACAGCTGATTGAAAAGGCCTGGCAAGCTTTTTAATGGCCACATGCATATTGG
TGCCACGAACAACTGCCTTTGACACCTGTCCGTAAGCTCCCGATCCCACGGGCTGCAGATCCTGGTATATATCCGGGATCTCCCATTCCGTTCGA
TTTATATCCAACTTGTAAAACTTTTTTGTAATGGACACTGACATGGTATTGCTTGAGGAAGGGCGTCGTCACCTTAGTTAATGGTGCCTATAAGC
GAGATATGTATTGATTCTTAAAATGCCATGCGAACGATAATTCCATGCTGATTACGTTTATCTTGAGGCAGCTCTGCGTCAGTAGTACTTACCTC
TGTTCCACGCCCAAGAATATCAACAACTAAGTACTGGTCCCTGGCATTTTTCCTATATTTGCGCTATTACTCCATTCCGATGCGTGTTAGGCATT
CATGAATCAGATCGTCAGTGGATCAGATCGATCAGAAGCGACACACGAATGCGCTACATTTGATCAGAGTAAAGTTGTTAAAATCATTTTTGGCA
CGATATTAAAAAAAATCCTTAATATATAAGTAAATAAATAAAATAATATATTAACCATATCATTGCATTGTAACAAGTCTCTTTTTCCACTCTTA
TCGATGTCCTTAAATGTGAATAAAGGGATTAAAATTAAATAATTTTGTTAGTTTTAATAATATTCTAAAAATTAGGTAATATAATATATTTTTA
AAGCCCATATACCGTAAAATTTGGAGTGTAGAGCGTTTAAATGAAAATAAACACACGGCGTTGCCAGACCGTCAGCTGACAGTTCAATAAGAATT
TATCGAATAAGTATTTGAATCAGCTGTCTCTTGTTTTTCCTGCAAATTTGAGCAGCACCATCCCCTGACCCATTTTTTGTTGCACTTTTGGTGTA
CTTTGAATGAAAAATAGTCAGAGACACTACTCGCGCCTGCGCAGTTTCAACGCCGGGGTTATCAAATAAGCTAATCTAATCGTTCCGTAAACGCA
GCCTGACATTCCGCCCTACCATTCTCCGACGAACAGTTAGTTTCGCACGCAAGCCGCTCCCGCTCGCATCGTAACCTAGAAAACTTTAGCGTATG
TACATAAGTAAATTGACGAGTTTATCTGAATGATACTGAATATATTAGCGGTATAAAAGATAAACATTACATGGTTTAACGAGTGTTCGCTTGAA
AGCCTAAATGTTAGACCGCAGGGGAGCTGGAAGAAGCCACTTCAACCGCTGTGAACTGCGACCTTTGGAACCTGGACTGGCAAACATGCAGATTT
TCTGTAGTCCACTATCTCAGATAGCGGGAACATTGTTAACATCGATGGCATGTTCAGCACAAGTAAAAGATCTGCGAACCGAATGCGATTAGATA
GTCCGGGGGGTTCAAAGTATGGTTTGAAGGGTTGCTATAACTTCAACCCCTGAACCGTTTTTCTTTTAATATTTTCGAGGAAAACTTCACACTCC
CCAAAGGCGTGTATAATTTTTGGTAGATAACCCACAGTTCGTTATCTTCCATTATAGCTCATCATAAAATGCAAAACTATCATGTTTCTTTCTCT
TTGCAGACACAAAATGACTTCAAAGCTACTGCCCGGAAACATTGTGTACGGAGGTCCTGTGACTGAACGACAGGCCCAGGATAGCAGATCCTTGG
GTCAGTACATCCTCGACAAGTACAAGAGCTTTGGCGACCGGACGGTGCTGGTGGATGCCGTCAATGGAGTGGAGTACTCTGCCAGTTTCATGCAC
AAGTCCATTGTACGGCTGGCATACATCCTTCAAAAACTGGGAGTCAAACAGAATGACGTCGTTGGTTTGTCTAGCGAAAACAGCGTCAACTTCGC
CCTGGCCATGTTCGCTGGTCTAGCAGTTGGGGCTACGGTTGCTCCCCTTAACGTAACATATTCCGATCGTGAGGTGGACCACGCCATTAACTTGT
CCAAGCCAAAGATCATATTCGCCTCTAAGATTACCATTGATCGTGTTGCCAAAGTGGCCAGCAAGAATAAGTTCGTCAAGGGCATCATTGCGCTC
AGTGGAACTTCCAAGAAATTTAAGAACATCTATGATCTTAAGGAGCTGATGGAGGACGAGAAGTTCAAGACACAGCCTGACTTCACGAGCCCTGC
GGCCAATAAGGACGAGGACGTGTCTCTTATTGTGTGCTCTTCTGGAACCACCGGACTTCCTAAAGGAGTGCAGCTGACCCAAATGAACCTGCTGG
CCACTCTCGACTCACAAATGTAAGTTTAATAATATGCTATAAAGGCGTTTCTTTTAAATGATTTTTCTTTAATAGCCAACCCACTGTCATTCCAA
TGGAGGAGGTCACTCTACTCACTGTCATTCCCTGGTTCCACGCCTTCGGCTGTCTGACGCTTATCACCACCGCCTGCGTTGGCGCACGATTGGTA
TACCTGCCCAAGTTCGAGGAAAAGCTCTTCCTTTCTGCCATTGAAAAGTATCGCGTGATGATGGCCTTCATGGTGCCACCACTGATGGTCTTTTT
GGCTAAACACCCCATCGTGGATAAGTACGATTTGTCCTCTTTGATGGTCCTGCTGTGTGGAGCAGCTCCACTCAGTCGCGAAACTGAGGATCAGA
TCAAGGAGCGTATTGGAGTGCCATTCATCCGACAGGGATACGGCCTCAGCGAATCAACGCTGAGTGTTCTGGTGCAGAACGATGAGTTCTGCAAG
CCAGGCAGTGTGGGCGTTCTTAAGGTGGGAATCTATGCCAAGGTGATCGATCCCGACACCGGCAAGCTATTGGGGGCCAACGAGCGCGGCGAGCT
TTGTTTTAAAGGCGACGGCATCATGAAGGGCTACATCGGAGATACGAAGTCCACGCAGACCGCCATCAAGGACGGTTGGTTGCATACTGGCGATA
TTGGCTACTATGATGATGATTTTGAGTTCTTCATCGTGGACCGCATCAAGGAGCTGATCAAATACAAGGGATACCAGGTGCCGCCGGCAGAGATT
GAGGCTCTGCTGCTCACCAACGACAAGATTAAGGATGCGGCGGTCATTGGAAAGCCAGACGAGGAGGCTGGCGAGCTGCCGCTGGCATTTGTGGT
CAAACAGGCTAATGTTCAACTGACCGAGAACGAAGTCATTCAGTTTGTCAACGACAACGCCTCGCCCGCCAAGCGTCTAAGGGGTGGCGTGATCT
TTGTTGACGAAATTCCAAAGAACCCCAGTGGCAAGATTCTGCGTCGCATTCTGCGGGAAATGCTTAAGAAGCAAAAATCCAAGTTGTAAGGGATT
TCTCCCCTTAAGGGTGTGTGTACAAACAATTTACTATGTGTATGTTTTATTATTGCTAAACTTTGTTTTATAAACTACCAACTGGTTGGGTTTCG
ATTTACTCATATTTGGCTTTTCTTTCGAAGTATTCGCTTAAAACTTAAATACAAATAAAAACTGATGGATTTCCATGTCGCAGATAGCATGTGAC
ATCGCTGAAGCTCTAGAACTCAACTCCAGCTTTAATTACGTAGATGCCTGAACTATCAATAACAAGTTATATATAAACAACTACATACATTCGTT
CTCAACTTGTAACAAACATGTATTTTTTCCATATTGTTGTCGCTTTTATATAGACTCATTATTAATTTCGTATGGTGTATACATATATTTATATA
TTTATTTGAAATATTTAACTACTCATCTGCTCTGCTTTGTAAATAGTTGTTTAACATTTTTTGTTTTGCTTGGGAAAAGTTTCTATCTTGCTTTG
TCGCAGCAAATTGCATATATTGGGTTCATTTGTGTTTCCAGTATATAAAGAGGTTTATATGTCTGTCTCTAGCATTAGTTTACTAATTATTGTGT
ATGAAACCTTAAATGTAAGAGAAATGCCTTGGTTTCTATAACGGAAATATCATAGTTTGTGTAAAATCCTAAATACTGCTCATCCAGCACAGGCG
CACCCCCGTCAAAATCCTGCTTCCAATCTTTTCGAGCTGCGCTGCTACCAGTGCTTATTTGCAGTACATACTTATTGTTGCAATGCTAATCGACT
TGGTGCACGATTTACACTTAAACCTAGTTCGACAAATTAGATGAATAAATTCAGTTGTTCACTTCGTTAGTTTCTTTTCGTTTAACTTTACATAG
TTAAATAAAAACGGTGCATTTTAAAATTAGCTCGCTCTTTTTTCTTTTACCATTGGTACAATTCTAGTTTTCTGCTTTTGGCACAATCCTGACAA
CAAATTGGTTACTCTGATTGTCACTTGTGAACGAAACTAAATTG
(SEQ ID NO: 697)

Exon: 1001..1230
Exon: 1717..2394
Exon: 2451..3414
Start ATG: 1724

Transcript No. : CT19388
AGCAGCACCATCCCCTGACCCATTTTTTGTTGCACTTTTGGTGTACTTTGAATGAAAAATAGTCAGAGACACTACTCGCGCCTGCGCAGTTTCAA
CGCCGGGGTTATCAAATAAGCTAATCTAATCGTTCCGTAAACGCAGCCTGACATTCCGCCCTACCATTCTCCGACGAACAGTTAGTTTCGCACGC
AAGCCGCTCCCGCTCGCATCGTAACCTAGAAAACTTTAGCACACAAAATGACTTCAAAGCTACTGCCCGGAAACATTGTGTACGGAGGTCCTGTG
ACTGAACGACAGGCCCAGGATAGCAGATCCTTGGGTCAGTACATCCTCGACAAGTACAAGAGCTTTGGCGACCGGACGGTGCTGGTGGATGCCGT
CAATGGAGTGGAGTACTCTGCCAGTTTCATGCACAAGTCCATTGTACGGCTGGCATACATCCTTCAAAAACTGGGAGTCAAACAGAATGACGTCG
TTGGTTTGTCTAGCGAAAACAGCGTCAACTTCGCCCTGGCCATGTTCGCTGGTCTAGCAGTTGGGGCTACGGTTGCTCCCCTTAACGTAACATAT
TCCGATCGTGAGGTGGACCACGCCATTAACTTGTCCAAGCCAAAGATCATATTCGCCTCTAAGATTACCATTGATCGTGTTGCCAAAGTGGCCAG CAAGAATAAGTTCGTCAAGGGCATCATTGCGCTCAGTGGAACTTCCAAGAAATTTAAGAACATCTATGATCTTAAGGAGCTGATGGAGGACGAGA
AGTTCAAGACACAGCCTGACTTCACGAGCCCTGCGGCCAATAAGGACGAGGACGTGTCTCTTATTGTGTGCTCTTCTGGAACCACCGGACTTCCT
AAAGGAGTGCAGCTGACCCAAATGAACCTGCTGGCCACTCTCGACTCACAAATCCAACCCACTGTCATTCCAATGGAGGAGGTCACTCTACTCAC
TGTCATTCCCTGGTTCCACGCCTTCGGCTGTCTGACGCTTATCACCACCGCCTGCGTTGGCGCACGATTGGTATACCTGCCCAAGTTCGAGGAAA
AGCTCTTCCTTTCTGCCATTGAAAAGTATCGCGTGATGATGGCCTTCATGGTGCCACCACTGATGGTCTTTTTGGCTAAACACCCCATCGTGGAT
AAGTACGATTTGTCCTCTTTGATGGTCCTGCTGTGTGGAGCAGCTCCACTCAGTCGCGAAACTGAGGATCAGATCAAGGAGCGTATTGGAGTGCC
ATTCATCCGACAGGGATACGGCCTCAGCGAATCAACGCTGAGTGTTCTGGTGCAGAACGATGAGTTCTGCAAGCCAGGCAGTGTGGGCGTTCTTA
AGGTGGGAATCTATGCCAAGGTGATCGATCCCGACACCGGCAAGCTATTGGGGGCCAACGAGCGCGGCGAGCTTTGTTTTAAAGGCGACGGCATC
ATGAAGGGCTACATCGGAGATACGAAGTCCACGCAGACCGCCATCAAGGACGGTTGGTTGCATACTGGCGATATTGGCTACTATGATGATGATTT
TGAGTTCTTCATCGTGGACCGCATCAAGGAGCTGATCAAATACAAGGGATACCAGGTGCCGCCGGCAGAGATTGAGGCTCTGCTGCTCACCAACG
ACAAGATTAAGGATGCGGCGGTCATTGGAAAGCCAGACGAGGAGGCTGGCGAGCTGCCGCTGGCATTTGTGGTCAAACAGGCTAATGTTCAACTG
ACCGAGAACGAAGTCATTCAGTTTGTCAACGACAACGCCTCGCCCGCCAAGCGTCTAAGGGGTGGCGTGATCTTTGTTGACGAAATTCCAAAGAA
CCCCAGTGGCAAGATTCTGCGTCGCATTCTGCGGGAAATGCTTAAGAAGCAAAAATCCAAGTTGTAA
(SEQ ID NO: 698)

Start ATG: 238

MTSKLLPGNIVYGGPVTERQAQDSRSLGQYILDKYKSFGDRTVLVDAVNGVEYSASFMHKSIVRLAYILQKLGVKQNDVVGLSSENSVNFALAMF
AGLAVGATVAPLNVTYSDREVDHAINLSKPKIIFASKITIDRVAKVASKNKFVKGIIALSGTSKKFKNIYDLKELMEDEKFKTQPDFTSPAANKD
EDVSLIVCSSGTTGLPKGVQLTQMNLLATLDSQIQPTVIPMEEVTLLTVIPWFHAFGCLTLITTACVGARLVYLPKFEEKLFLSAIEKYRVMMAF
MVPPLMVFLAKHPIVDKYDLSSLMVLLCGAAPLSRETEDQIKERIGVPFIRQGYGLSESTLSVLVQNDEFCKPGSVGVLKVGIYAKVIDPDTGKL
LGANERGELCFKGDGIMKGYIGDTKSTQTAIKDGWLHTGDIGYYDDDFEFFIVDRIKELIKYKGYQVPPAEIEALLLTNDKIKDAAVIGKPDEEA
GELPLAFVVKQANVQLTENEVIQFVNDNASPAKRLRGGVIFVDEIPKNPSGKILRRILREMLKKQKSKL*
(SEQ ID NO: 699)

Name: luciferase-like
Classification: enzyme

Celera Sequence No. : 142000013384303
CCACTCCCCTCTCCAACACCACACTACCAATACCCTGCCAGCACGTTTGAGTTGCCCGTATTTTTGGGTTATCGCCCGGTCGTATTTGTTTATAG
AGAAAGAGAGAATTTTTTTTTTGTCTTTTTTGACCTGACCACCTGTTGCTGGGCGCTGAGCGCCTGTTGCGCTAGCAAATAATCGATCGTCAGT
TATTTATTGATTTCTGATTGATGGGCCAACCAAGTCCCATCCAATTTGAATCCAAACGACGTGGCTTAAGGGCGGGGGATTAGCGTCTGCTACGT
GGGATCTTCGTGTGTGCCGGGGCGGATTAGCTGGCTTTGGTCATGCGGCTAACAGAAAAACGGCAGCAGGCAGAGATCGCGTCGCCAGTGGAAAT
TTGAATAAAATTAACATTACAACTACAGTAGTCGGCGGCACAGAATGCTGATAAGCGCTTAACTTATCAAATGCATACATAAGTGGTTTTCGTTT
GGTTAACTTTAGTTTATTCATTTTTGAAATGTCTATAACAGAAACCCAAGAAAACATATTTAAACATAAACACTTAGGAGTCTAGGAATCAGGGA
CGAAGGTAATTTTGGGATATACTCGTATATGTAAATTGTTTTTTTTCTAAGTTTTTAATTTGTTTTGTTTTTTTTTTTGTAGTTTTGTGACTGT
TTTAGCAAAACTTATTTAGCTACGCCCTAAGCCTAGGCAATATTATCAATTTTTTTTTTTTTTTTTTTTTTTTTATTTACGATGATGTTT
TTATTATTTGATCAACGCACTGTTACCCATGCGGCAACTTAATTTGATCTGCTTAAATTATTTTATTTTACAATGTGTCTTGGTTACTTAAGACT
AACAGATTTTTAATCCTAAAAATGATAGGGAGAATTATAATAGTTGATATAACATAGTAATTATTATTTATTTGATTATTCTAATGAATTTTAAA
ACTAAGACTTTCTAGGTCAAAACCAGGTTAGGGAGGTCATGAGGGTGGTGAATATTATCAATACGATCGTTGAAAACCCAACACCCGAAAGTATG
CTATAAGTACGAACGCCTACTTGCGACTGCCCTTGCGACACAATTGCTGTACCGCCTGCGCTGCCGCCAGGAAACTCTTCTCGGCGCAGCGCTTG
GGCCAGTCCTAGGACTCGTAGAGCAGCCGCTGATAGTGTGGCAGGACCTCGTGCCGGTTTACATGCAGGCTAAACTCCAGAGCCACAAGCACAGC
GAACTCCGACGAGATCAGCTCCTTGCGATTCAACCGGAACACGCTCTCCGTCTTCTCGATGAGGCTCTTGAGTGCGTCACCCTTCACGTCATTCA
TCTTGGCGCTGAGCAGCAGACAGGCGCCGGCGCACAGCTTGCGGTTGCTCTTGTTAATCAGATTGGCCAGGATGAGCTTCTCGAAGTACACGTAC
GCCTGCGATATGGTCACCAGATCGATGCGCGAGTCCAACTTGTTGATTCGGCGCATTTCGCGCTTAATGCTGCAAGTGAAACGTAAATGGATAAG
TAGTGTTCCTTTAAATGGTTACTGAAAGAAGGTTATGGGTTCACTTTCTCAATATTACTTTCTATTGAGAGTAACTTTTTCCATTCCTTTTAAAA
GTGAAACCATAGTCCTTCAGATTCCTTGTCACTTACCTCCTCAGCTTACTCAGTGTGAGCTGGATGGTGGGGAACTTCTCGCGAAACTTATCGTT
CAGCTCCTTCTTAAGATCGGATGGACGCACATAGTCAATGACCGAGGTCATGTAAGAGGTGAAGGTAAGCAACGTGCGATGCTTTCCGGCAATCA
ACTCCGGATCGTCCAAAATGCTAGCGGAGTACTGCGGATTACGCAAGACATAACTCTAGTTAGTAAGGATATACATTCATAGAGATAACCATTCA
ACTTACCACCTGACCACGCGACGAGTCTCCGCCCAGGATAACACTCTCTATGTCCATATCCAGTTTCATGTCTGGCGTCGGACTGGTTGCACTAT
TGCGATTGTTGTTCTCATAAGTGAAGCACCTGCGAAGTCAATTTCGATTGATTAGGATGCACACTAAATACGAATTATATGCTAAGATAGCGCGT
GATAGAAGGCGGGATTGGGTTAGTCGAAGCATTGCTGTTCGTCGGATGTGTGCGAGAGTGGGTGGCTGGAGGTGTGTATGTGGGGATAGGTGAAC
TTGGTTAGTGGGCTAGAAGCTTTTGGCAGTCGACCAGGCTTTGAAACTACAGCAATTCAACTACTGAAGCTAGTAGTAACATAGCTAGGTTGGCT
GTTTTGTTTTTGTCATATTAGCTGTTTTTCAAAATTTACCATTTGCCTTGACGTTTGGTTATGGTTTTTGTGCTGAAACGAAGTAGTGCAAAGCG
TTAAATGAATTAGCAAAAGTTAATGGCACATAATGGTTTTATTTTTGTTTTGTTTTGTTTTTTTTTTTTGGGTCAACTATTACCGAACCAAAGCA
AAGAAAACAATTGAACATTGTAGCTTATCAAGCGATAAAAAATATCTTTCGATTTTGGGGATTATATAAATGCGAACAATGTGCTGAGCTTCAGTA
AATATATAATTATTGGTTTGGGTAACATTCGCGCTCAACTCTTGATGAGTCAGATTTTCAGGTCTTGCTGGGTCAGCTTTATGGCTGTTGACAAA
CACGAGCTAAACCAGTGTCTCCACTGGCAACCGAGTAATGCGAGAAGGTAACAAAGAAGCATTATGTTTACTTTTCGTTTTAAACGGAATGGCTA
CTTGCTCTTCGATCGGATAAAGGAATTATTAGTTTACAGTGGTCGTTCGGTATGGCTAACCATGCAATATGACGCTCAATGAATGTTTAGAATGG
TTCATGGGCATGACATGACATGAAATGGAGCTGATTGAATGTGTTCAACAAAAATGATACGAAAGATGATCCAAAATATGCTGGCAAACAGGAAG
CCGGCACCAACCTCGCAATGCCATGATTCTTAAGCGCCGCTGTGCTCGTGATCTCCATTTGGTTCTCAAAGATGGAAGGATTCGCCGATGCATTG
CCATGCTTCTTGCGCTCCTTTTCGTACTGACGTGAAGGTATCAGCAGGTGACCATATGATATGTCCTGTAAAAAACAAGTTGTAGTTAAGATCAG
TTACAGTTGAGCTAAACTTATTGACTTACCTGACCACTTTCGGCCTTCTGTATACCCAGCAAATCAAACGGATCGAATGGCGCATCGTTGATCGA
GCTCAAAGGACGCGAAGTGGATGGATTCCGACGACGACGATCCTCCTTGCGAAACTCAGCTCTGCAAATTGGAACATAATTATTATAATACTACA
CTAATAATTAGAATCTAGTTTTGCATGTCACCTTCCATTCTTGCCCTTGTAATAGGGAAGTGAAGAGAATATGAAGAACGGAATCTTGCGCGACA
CAAGCACCATTCGCTCATCCCGTGCCTGTCCAAGTCCCAATGGCTGGCCGGAGGTTCCACGCCGGCTATCGCTGATCTGGACCGACTTGCTGAGG
CTGTTCCGGAAACTGCCCGCATAGTTTCCCGCCGGAGTCAGGCTCTCCGTGCTGCTGTCGTCGGTGATGTGGCTAACGCTCGATCCACTCAAGAC
ATAGGTGCGCTTCAGACCGCCGCCCATGGCAATGCTCGAATTGGAGCCCACCCGCATACCCGGCGCCGTGTTCAAACGTGCCCTCCGCTCCGGCT
GCAAGTTCTGATCGCTTGCCCCATTGCTGAAGGTGCTGCAAGCGAGAAGCAGGAGATCGGTTAGAATCGTAGCGATCTAAGGAGCAACAGGCGCT
CAACAACTCAAGTAGCATGAAAAACGCGCAGAAAACGATACAAAAACGCGCTGGGCTGGACCTTGAAGGCCCCAAGTTGTTGCTGCTTTAAAATA CGATTTTTTTTTGGTATTTATAAATTCAATGACAAATGTTAGCGAAGAGACTAGTGATGTCACTTTAGCTATTAACCAAAAAAACATACTTTTAG
GATACTTTCTTTAAAGAAATTACTTTTAAATTTTTAAAATAAAAGCATTGATTATAATGTAACATTACTATTCATAGTTCTACTATACTTATTA
TAGCCTAACTAGCTATGCCTACGTTCTTAGCTCTAAATTGTTTAGCAATCTGTTTTAGTTTATAGCTAATTTTAGCCATTTTATGGGTATCTTGT
GGGAGCATCATCTCTGGAACTCTCTTCATCGCGGGGGCCCATTGTCACACCCCTCACGCAATGATCGATATTTTCACAGGCCCGCAGAAACGGAG
AGAAAAATCAGCGGAGGCAGAAAGATTTTCCCTTGTGCATTTAAAGGGCGATCAGGCCCGCTGCTTATCGCTTGTGTATTTTTGGAAATCAAACA
AACACATCAACACAAACACACACACGCATACACATTCACACGCTCGTTGGCACACACATGTGCAATGCCGAAGGGCAGCCGCAACGCAAGTCAAT
TAGCCAACTGAAGTCAACATCTTCACGGCATCTGTGCGCCTGGTTGATTACCTTGGGATAATTGGTCTAGGTCGAGGTTACAGTCAAAAAAAGTG
TGGTCTCTTGAAGCGGAAGGGGGCATGGGGCAGGGGGGTCTGTGCGCAAACTCCCCTCAAGTTCGTCGTGGTGACGATTCTGCGTTAATTAGCTG
GATGAAGTGCAAGGCAGCTCGCTTTTCATTAAAAAACCCCTTGCAAACCCAACCCCAAAAATATGATGGAAGTGGCGCCTAGGCTGTCATAACCC
GTTAATTAGTTGGAGCATTTTAACAGGCGCACAGAATTAGCAGCAGGAATTTAGTTTTACATGCTTACAACAGCAGTGAAGAAATGAAGAGGGTG
GGGATAGCTCCAAAATGTGTGTGTGTCTGCGTGTGTATGTTTGGCCGAAGAAGAAGAAGTAAAGGGCCGAGCAAACATTTATTTTTGTGCGTTTG
CTTTTGTGTTTTCTGTTCGTCTAACTATTGACTCGCTAATGAGTTTGTGTGCGTGTGTGTGTGTGTGCGTTGATAAGAGGTTGGGCAAAGTGCGT
GTGCGAGCGAAAGGGAGTCTATAGACCACCACTGCAACTCAAACAATAAAGCAAGTGAGCATGTATAGGTCCGGTATTTATAGTTTTTCTATTTC
AATTTCGTTTTTCGAAACTCCGTCTATGAAGTGCTGTGCCCCTGTGCCAAAAGCAAACAATATTTAAATTCTAACAATAGATTTGATGAATTGAA
AGAAAAATGATTCAGCATTTTTTGAACCGACAAAGAATTGGAAGAAAGTTCGACGAATTTTTTCAATTCTTCATGTTACATAACATTCGAATATG
TACAGTGCTATTTATAGATCGCCAGAAATGCGTTAGAAAATTCTCATAACAGAATCACAGTACTGTAATTTTAACAGAATGTTTTACAAAATTCT
TTACACATTCTGCTAATAGCATAATGTTTAAAACATGAACAATCCGACTTGACTTCTGTTGTTGACATAACCGATATGTTAAAAATATAAAACTC
AAATCACTTAGCAAATTTGCATGCCTTGTAGCATATAAAGAAAGAAATCCTATAGCTCTTATCTCCCAGCTGTGCAGATCTAAAGATATGTACAT
ATGTCTTTCTCCTAGAGACTATCTCTCTGATTTTATTTTGATTGCAAATATTGACCAAGAACTGCTACTAAAAGCTTTGGTAAATATACTTTTCA
CGTCTGCATGCGAGAGAGCGAGCAAATAAATCTGCCCAGAGTTTAATCGAAGAAAACACAATATTTTAATTGCAATATCTTTCCATTTTAATGGC
TTTTTCTTTGTGTGTATGTGTGTGTGAAGCAATCAAATCAACTGAGTCAATCGCGCTTTTATCAGCAATCGCTTTTGTTATTGTCATCGTGCCTT
GTTGTTTTTGCTGTTATCTGCTGGCTATGTGCAAACAGATGTTAATGGAAGTAAGTTTTATTATATAAGTTTCCGTTTGACCAGATCACGTGCCC
ATGAGCTTAAGCATGCAGCTCTGCTGATAAAAGCTTTCAGCCAGACATAAACAAAAACTAAAAAATAGACTAAATTAAATATGCAAATTTATTAA
AACATGTTTGACAACACCACAACTTTTAAAAAAAATTTCTAAAAACGCCCGCAAACCGCTTTCGAATCGCTAGAGAAACGCTAGCAAACCGCTAG
CAAATGCAACCAACTTCCATAAAAGTATGTACTCATTTCTTATGTTCATAATATTTTAACTGGAAATAACCACTACTCTACTATTATCTGAAACA
ACCCTAGTAGAAGATACACTGAAAGTAATAACTAGCAATTGCCACTTGAGGCTTTGTTTTGGCGGGCAATGACGCAAATTGATTCCAACATTATC
AATACTAGCTCCCTTTCACCTCGAAACAAAAGTGGATTTCGGAACGAAATGGTGTTCTAGATAAGGTGGAAACACATCCAGCGAAAACCGCCGAC
AAGCAACAATAACAATAATCGCGTTAGGAAAGGAAGGCGTAACCGAAGAATAAGCGTTTTGTAAACAAACAGTGGGAGCAAAACGGAATGCCAAA
AAACGCCAGCGATTTCGGGCGAGACGGGCAAAAACGTCGAACGAAATGTTTACACAAGCCGAAAGTAATTACATAAAGCAAATAGGCAAAAAAAA
AATAAAAAATTGCCTATTTACAAGTCCAATTGAAGGCTGTCGATAAAAAGCACAAACAAAGAAACACAATGATGTGTCGATATGAAACGAGTACA
TTTGTGTTCCATTATTTGATTTCAATACTTTGTGTGAATTAAAAAAATTGGATGTTATAACACGTTCCTACTGTTTTCCTCTTCTACTGACAGAT
CTTAACTTCAAGAGCAAAAACTTTGGCAAGAGCGAAAACCGAGAAATCAGTGAAACGGGAACCCATTTTATCCGCTTTTAACCGCTTTTACTACC
TTCAAATACAATGGAACAGATAAAACATAATAAAGCGACTTGAGAATGACGTGGAGTTCGGGCATGTGTCGATTAAATATATATTAAGTCGCAGT
TACTAGCAGAGAAGAGCATTAAGTTTAGTCGATACGAAGTGCATAGAGCTTTATTTATCGCAAGGGGTTCTTTGTTTTGTGTACTACATATGTGC
AATGAAGTCCACAAAGGCGGTGCAATAAGTATATTTACGAATCGGATTAGGTGTGTCTATGTCATCTTTGGGCTTATCGTTCATTTCTTCACCGA
CGAGAGAGACAATGGAGCTTTATGGCGGTCTGTGTTGACTTTAGCAGAGCTTACATATGCACAGAAAACAATTGGATAGCTTTTTCACAAATTTT
TAAAAAAAAAAGTTTAAGAACAAAGTTTTTTCCAGTGTTTATTAACTAATTGTTCTCCGTGTGTACTGAAAGCAAATCAAGTTCTAGGGGTTGGT
TGCATAAACTGGGATGCAGTGGCAAAATGCAGCATGCACTTCAAGCTTTTTGCACCACTGACACACATTTCGCAACCCGCCGGCACAAAGGAACC
CCTTTTTCGAAACGGCGTGTCCTTGAACACAAGGATTAGAACCCCTGAAACGCACAAGTAGTGCGAATAAAAATAACGAAAACAAACAAGAACAG
GGAAAACCGGTTCCTATTACGTCGTCGATTGCATAAAACTCTGCCTCAAGGTTACCCAGTTTGATGGAGTGAACGGGATGGGAGGGGGTACGCAG
AGGATTTTCTCGCTGTTTGGACAGGTTTGCTGGCTGGCTGGGGCGACATTGACATTGAAATTGGTACGAGGCAGGGAGCAGGATGAGGCCACAAA
AAAAGCTCAAGTTCAATGCTAAGCTTTGCCTTTTGCCGGCTGAAGGTCCTTGGTTGACTGTTGAATGAACAAAAAGGGCCGGGCCACTCCCCTAA
ATCAAGTTAATTGCCATGACGCAACCTTTGGCCAAAGGAAGTGAAAACTGAGAATGAAAAAGAAAAAAATGATAGATGGGGCAATAAAAAAAAAT
TGTTTACGTTTTCGGTAGAGTTGCGGATTTTTTTTCAGTTTTTTTTTTTCACTCTTCCATATTCCCATTCATTGGCCAACTCCACATAAAGCAGC
TCAGGTTTCAAAACAAAAACTGGACATAAGTAGTTTGTTTTGGTTTTGCCAATTGCGACGCAGTTTGTTTTTGCGCCTGCGCAGCTTTTTGTGGC
AAGATTCCCACACCGAAAAATGCGGACGATTCCGCATAGCACAATATTGTTGTTTGCAACAATGTGCCTCTTCAACAAATTCTGGCATCAACAAA
ATTGCTATCCCATTCCGGAGCGGAAATAGTAATGAAACCCTAGATTGGTGGGTAAAAAACAGAACTTGCTTTTTGGATTCAACGAAGAGCATAAT
ATTTTTTTTTCTTTTGCTGCGAAATGAGCGAAACTGGGAATACATATTTGAAATCGCTTAAAGACTTTGTAACTCGATGATGTGGCAAGAAATTC
ACATTTATTGTTCACGAACTGAGTCATGATAAAGGGTTAATATATAATTTTAAAATCAGCTGACACAAAAAATACCCCTTAATTAAAGTCTTTAA
CGTCACTGAGATATCTCATCGAGTGCTTTTATAATCTTCGAGGCTTCGATCATTTCCACATGCCAGATAAACCTGCTGAGTGTAAAAGATCTCAT
GATAGGACTATCCGTCATATATCAAGATCATTCTAACCAATCTTATCAGTTGATTGCTTTGTGTATATACATACATATGTACATATATGATCTAT
TGCTAGTTCATCGCTACGATAAGGTGCAAAAATATCAAAATTTCAAGCTTTCGACTTTATCAAAATCGATCAAAGAACTCATTGCAAGGAACCCT
GATAAAAATGTGTACATTTCACTATTTGCGAAGTATATATTTCTAGTTTTCCCTATGATATTCATTGACTATTTGCTATTCAGCGTGCTAAGTGT
TATGAATTTGCATTTTTATAGCTCGTTCGATAGTTTAGCTTTCATGGCGCAGTTAGATCGTATATGTATAAATGTATATGTATATTAATAAACGT
TTTATGGTATAATTAGAGTTATAGTAATAGCATCCTTCTCAAGCTTTTGCATAGTCATTGCCAAACTAAAACCAAATCCCCGGGAATTTGATTTG
CCACAGCAAATGGCAATGACAGGTCGCTGACAAGCCAATTGGCTGCAAGCCAAATGCATATCTACAAGTATGTAACCAACGGATGGATGACAATA
AGTCCCCTTCCCCACCCCTGCGGAATCCGAGGAAAAACGGGTTAGCCACCAGTTGAGTGGCGGCGGCATGCGAAAGAAACCGAAAACGAAAACGC
TAGGCAAAAATAGCGAAACGCCAGCGGAGCACGACTGCAAAGCTGCATGTGGCAAACAAGGTCAGTTAGCCAAAGCGCATCCAACGAGTTCAACG
AAACTTGTATCTGGCATTGGAAGTGAAAGCTCTGAGATGCACCTTAGCTTTGCCCAGCTTTATGCACGGAGAAAGACAAAGAAAGTCCCCCCGAG
TAGGGGGGGGGGGGGTAGAGTGGGGCGTAAGTTCAAGGCAGTTTGCGAGCGGTTTACGAGCGTTTCGCTAGCGATTTACGAGCGATTCGATGGCA
CACGCATTTGGACATTGCGTAATTACTTTGCGCTAATACAACCAGATATAATGCCCATGATTCAACGTTGACAGGCCGTTTAAGTGCGTGACAAA
ATGACTGGCGCCTCGGACAAAAGTTCCGAATTAAACGAACACCGCGACGCCCCTCGACATGCAATTCAATTCAACTTAATTCAAACAATTGTTTG
CACAGCTTTCGGCCGGGCACGCTCTCTAATTTACGTTAATTGAGCCGGCACACGTTGATGAATGAAGCCGATTCGATTACAGGCCCCACCCTCCC
ATCCAACGCCCAACCCCTTGCCCCTCATGAGATCAAAATATTTGATGTGTATTTTTGGGGTAGGCGATATTTTTAGCGCCAAGCGACCGGCAACA
GACAGACTCCTAATTATGCAGCATCAGGCGTTGAAAACGTGCAAATAGTCCCTCGCCATCTGCGAAAATACGTCACAATCGGAAAAGCGCTCTCT
CAATTTTCACAAGCTTATGTTTATAAATAATTTTCGATTTCAGAACGCCCAGCGAAGTGTTTTGCTTTCGCGGTACTTTCGATCAAGCTGAGCCT
TTTTCGTAAGCAAATTAGAGAACCAGTGTCAATTGGCTAACGTAAACTTAGCGGAAATTTCAATTAACAAATTTGGGGAGGGGAAAAATCGATGC
CAATTATGACGACAGCTTAATTGAACTCAACAAAAGTTCAGTGATCAAGCGGAATGATTCATTCATTCTCGTAGCGTAGAAATTATTTATAAATC
AACAAAGAGCAAAGGAATATTAAGCGAATTTCATTCGTACGTGTATGGTTGGAAAATATTGCGATTGGACTAAGGAAAACTGTCCACTTGACGTC
ACGTGTCAATCTATTTCTGAGTGTCTACAAGATAGAAGATCGTTTAATTGGAAAAACATAAATTTGAAGCTGCAATAACTTAACACATTTCCTGT
TTGAATATTTTGGTAGGTTCCCTTATAGTCGATCTAATATAACATTTATAATATTATATAAACTTATGGTAAGAATCTTTACAGTTGCCTCTTCA

FIGURE SHEET 379

TACAGCTAATTTGATTACAACTTCTAGCAACTGCTTAACAAAATGCTGATTAGAAACCATAATAAGCTAAGATAGTTCACTGATATGACAAACAT
GAATTGTGCATTGATTACTCACCGTTCCCTCAGCGGCAATAGCTTGCTGCCCGCTCCGCCGGCCACGCCACCGCCGCTGCCCAGATTGGACACCT
TGAGCGGTATCTTGACGCTGTCCGAATCGCTGCCACTCTCGGCACCCGATCCTCCGCTGCCGGCGGCGCAACTTCGTGCCTGCCGCTGTTGCTGC
TGCAACTTGTGCTGCTGCTGCTGCTGCTGTTGGAGCTTATTGCCCATATTGCCATTGCCCGGTGCCTGGTGGTTATGACGACCCGACGAGGTCGG
GCGCTTTATGTTGCGTCTCTCGGCCGGCACAATGCTGCTGCGATTGTGATCGGCGGCCGGCAGGACGTTCATCAGGTATTGACCCATATTTTCAG
TTTCACTAAAATGCCCGTCCCCATCGCTGGCACCGGTGGTGCAGTCCTCCAGTCCCAATCCCAGCCCGATGCCGCCATCGATGCCCATGTGGACA
TCGGCGCTGCAGAGGAGCGGCGAACAGAGGGCGCCATTCTGGTGTTGCTGCTGCTGCTGATGCTGCTGCTGATGTTGCTGCTGCTGCTGCTGCTG
TTGGGTGTGTTGCTGTTGTTGCTGTTGCTGCTGCTGCTGCGTGTGATGCCGCTTCTGGTGGTTGTGGTGCGTCGCCGAGTGGCTGCGCTGATGGT
GGTGCTGCTGATAGTGCGGATGAAAGCCCCCCGAGCCGAGTCCCAGCGAGGATGGGTTCTTATTCTGGTTGCAGAGCAGGCTGCTGCCGAATGTT
GCGCCGAATTTGGTGTCCCGATGGGTGCCATCTAACGAGATATTCGATAGGAACGAGATCGCAGCCAGTCTGCGCCTGTGTCTCGTCTTGTTGAG
CGAACTTGCCATTAGGCGATGAACCCTTAATTACCAAGCGAGATTAACCGAAGTGGGTGCTGTGGGTCGTTTCCCTGGATGCTCCGATGTTGCTA
TATATGTACCTATATGTATATATAGTGTGTTTGTGTGTGTGCATATACTGTGTGGGAATGTGATGTTGCACTTTTCTGGAACACTCTTCGCGA
TTCTTTACGAAAAAACTGGTTTCGAAAGTGATTATGCTGCTGTTGTGTATTTTCACTGCTGGTTGCTCACTTTTCTTGATCGAATCAATTAAGTT
TTTTAGTCTCTAACTTGGCAGCCGAATTAAAAAACAAACTACTTGAACGCGACATGGTGACGAATTTTTAGCACTTTAGATGACGGAAGATGGTT
GGAATACGAATAATTTTATGCACTTTTATTATTAACTAGCGTTTATGCGTCGATGCGTTGCTTTGGCTGCAAGTAGAAATAAGAACAGAAGAGAG
GAATGGAATCAATAAATGAGACTATAAAAAGCGGCAGGAAAGCTGCTTTTGGCCAAGAGAAGCTTTCTCCGAGCGTTTCTGGAATATTCGTTGAA
GTGCAGTGGGTGGCTTAGGGGAAATTGTGGTCAGCACATTCTCATTCTCAGTGGGCAAAATATTGAATATGATATAATATTGTTAGCAGAAGTCA
TCTCAATATGATATTTTATAATTAGCAATGTTTTTAAGCTATTTTTAAGTGAATATGCTATGGTTTTTTCAACTCTTTTAGATTATTTACAATTT
TTAGACATAATAATCATTTTAAAAAATCTCATTTGAAAACAACGGGCATTTTTAATTTTAAGAATTAAAAGTTTTCCTTGAAATAAACCCGAATC
TTTGCTGGGATTTTAGCCAACTGAATTGATAAAGCTTTTCCGCTGGCAGTTAAAAAAGCTGCATGCGGCTCAAAGCTGCAGTGGTTTTAGCCGCC
TTTGTTGTTGCTGTTGTTGCTGGCGGGCGGCTTAGTGTGTCAGTTTAGTGGGTGGCAACAGTGCGAAGAGAGGGGGTGGCAAAGAGAGAGATATT
GGGCCACAGCCGGCAAGGAAAATCTAAGCGCTTTTCCGCACTTTCGTGTGTGTTTTCTGTTTACATTCAATACGGGAGGCCCTAAAATGCCCAAA
ATTTCCCTCGGGCAACAAGAGCGAGTGGAAAATTTTTGAGAACCATCATAAACAGCTGTTCGGGAAGCGGGGAAATAGATTTTCCGGTGGTGGT
TTTTTTTTACCTAGGATCCAGTCTAATTGGATTTACCTGGACCAATTGGAGTGCGGCGGCACACACAAGTTTGAGCCTGTGCGAAAAATATAAAA
TCAATGCAGGAACAAGTGTGTGCGAAAATATTTATGACACCCACCCACTCACACGCTCGCACACACACACTTGCAAGCACACGCACACGTGTGAC
GTGTTTTTTCGTGTTTTCCCCTCGTCTTTTACTTACCACTGTGCTTGGTTTTTCCACGGTCGTTGGGTATTACTTAAAACTTAATTCGATTGATA
GTCGTTCTATGCTGAGAAATGTTTCAAGCGCGTCATTTTGATCTATTTTTATAGTGTTTTTTTCGATAGACTTTGATTTTTTGCCTTTGGCTGCC
AACTCGCCTGCGCTCCTCACTCTCTTTGGCTCTCTTTTGCACGGCTGTGTGTGTGTGTGTGTGTTGGTGCACTCACGCAGTTGCCTTCGTTGC
GTAAATTATGCAAAATGCAGGCCAATTGCAATGTGTTTACAAAAACAGAACAAACGATCGCGTTAAGTGTGTTTTTTGCGATTTTACGAGCGCGT
TAACTGGTCTCTGCGAAATACGCAAACGGTATGAACGTCAAAATATTGGCAGCAGCGACGAAAACATCTGCAGATGGGCTTACGAAAAATTCACA
AACTGAGGCCAGTGTTGGGCAGCGGACGAAGGGCGAAATACCAATTCAAAGGGAGGCAAAATATACCGCAATGGTACTCTAGAAAATTCACGATT
GTTTTGGTTTGTCCATAACTTCAACGTTTAAATAAGGTGCACTTAGAAAATTCTAGATGTTCACAATTTGTAAAAAAAATGTACACAAGCCAAAG
TTATCTTAGTTTTATGAACAATTTTTCTGTATTCTTAAAATATTGTTTACATGTTAATTAGGATTTAATTACTTTGGTATTAGCTGCGGTATCTT
AATACCACTACTTTTCAAACCTTCTGGCAACGCCATTTCGATCAGCTGTTTTCGTGGGACGCGCATGAGAAAATTATTGTTTGCGGCATTTCATG
AAAATCGCGAAAAATGGTGACAAAAACGATAAAATCTCTGAATTTAGAGATCAATTTCGTAAGTACCATGAAATATATGTAAATCACAACTAACC
TATCAAGTTTTTCACACACAGGAAGTGGAGGATGTGCCGTATGAGGAGGAAATCCTTCGAAACGCCTACTCCGTAAAACATTGGCTGCGCTACAT
TGATCACAAAGCGAAGGCGCCGAATAATGGTGTTAACATGGTCTATGAGCGTGCTCTGAAAGAGCTTCCTGGCAGCTATAAGATCTGGCACAATT
ACCTGAGAACTCGCAGGAAGCAGGTGCGCGGCAAGATACCCACGGATCCCATGTACGAGGAGGTCAACAGTGCCTTCGAACGTGCACTGGTGTTT
ATGCACAAAATGCCACGTATCTGGATGGACTACGGTGCCTTCATGACCTCGCAATGCAAGATTACCCGCACCCGGCACGTTTTCGATCGGGCTCT
AAGGGCTCTGCCCATCACGCAGCACGGCAGGATTTGGCCACTGTATTTGCAGTTTGTACGCCGCTTTGAAATGCCGGAAACAGCACTGCGAGTCT
ACCGTCGATATCTGAAACTCTTTC
(SEQ ID NO: 700)

Exon: 13464..13052
Exon: 12036..10758
Exon: 3740..3357
Exon: 3291..3165
Exon: 3105..2957
Exon: 2024..1907
Exon: 1836..1652
Exon: 1494..1001
Start ATG: 11602 (Reverse strand: CAT)

Transcript No. : CT19424
AGATGTTTTCGTCGCTGCTGCCAATATTTTGACGTTCATACCGTTTGCGTATTTCGCAGAGACCAGTTAACGCGCTCGTAAAATCGCAAAAAACA
CACTTAACGCGATCGTTTGTTCTGTTTTTGTAAACACATTGCAATTGGCCTGCATTTTGCATAATTTACGCAACGAAGGCAACTGCGTGAGTGCA
CCAACACACACACACACACACACACAGCCGTGCAAAAGAGAGCCAAAGAGAGTGAGGAGCGCAGGCGAGTTGGCAGCCAAAGGCAAAAAATCAAAGT
CTATCGAAAAAAACACTATAAAAATAGATCAAAATGACGCGCTTGAAACATTTCTCAGCATAGAACGACTATCAATCGAATTAAGTTTTAAGTAA
TACCCAACGACCGTGGAAAAACCAAGCACAGTGCCAAAGCAACGCATCGACGCATAAACGCTAGTTAATAATAAAAGTGCATAAAATTATTCGTA
TTCCAACCATCTTCCGTCATCTAAAGTGCTAAAAATTCGTCACCATGTCGCGTTCAAGTAGTTTGTTTTTTAATTCGGCTGCCAAGTTAGAGACT
AAAAAACTTAATTGATTCGATCAAGAAAAGTGAGCAACCAGCAGTGAAAATACACAACAGCAGCATAATCACTTTCGAAACCAGTTTTTTCGTAA
AGAATCGCGAAGAGTGTTCCAGAAAAGTGCAACATCACATTCCCACACAGTATATGCACACACACACAAACACACTATATATACATATAGGTACA
TATATAGCAACATCGGAGCATCCAGGGAAACGACCCACAGCACCCACTTCGGTTAATCTCGCTTGGTAATTAAGGGTTCATCGCCTAATGGCAAG
TTCGCTCAACAAGACGAGACACAGGCGCAGACTGGCTGCGATCTCGTTCCTATCGAATATCTCGTTAGATGGCACCCATCGGGACACCAAATTCG
GCGCAACATTCGGCAGCAGCCTGCTCTGCAACCAGAATAAGAACCCATCCTCGCTGGGACTCGGCTCGGGGGGCTTTCATCCGCACTATCAGCAG
CACCACCATCAGCGCAGCCACTCGGCGACGCACCACAACCACCAGAAGCGGCATCACACGCAGCAGCAGCAGCAACAGCAACAACAGCAACACAC
CCAACAGCAGCAGCAGCAGCAGCAACATCAGCAGCAGCATCAGCAGCAGCAGCAACACCAGAATGGCGCCCTCTGTTCGCCGCTCCTCTGCAGCG
CCGATGTCCACATGGGCATCGATGGCGGCATCGGGCTGGGATTGGGACTGGAGGACTGCACCACCGGTGCCAGCGATGGGGACGGGCATTTTAGT
GAAACTGAAAATATGGGTCAATACCTGATGAACGTCCTGCCGGCCGCCGATCACAATCGCAGCAGCATTGTGCCGGCCGAGAGACGCAACATAAA
GCGCCCGACCTCGTCGGGTCGTCATAACCACCAGGCACCGGGCAATGGCAATATGGGCAATAAGCTCCAACAGCAGCAGCAGCAGCAGCACAAGT
TGCAGCAGCAACAGCGGCAGGCACGAAGTTGCGCCGCCGGCAGCGGAGGATCGGGTGCCGAGAGTGGCAGCGATTCGGACAGCGTCAAGATACCG CTCAAGGTGTCCAATCTGGGCAGCGGCGGTGGCGTGGCCGGCGGAGCGGGCAGCAAGCTATTGCCGCTGAGGGAACGCACCTTCAGCAATGGGGC
AAGCGATCAGAACTTGCAGCCGGAGCGGAGGGCACGTTTGAACACGGCGCCGGGTATGCGGGTGGGCTCCAATTCGAGCATTGCCATGGGCGGCG
GTCTGAAGCGCACCTATGTCTTGAGTGGATCGAGCGTTAGCCACATCACCGACGACAGCAGCACGGAGAGCCTGACTCCGGCGGGAAACTATGCG
GGCAGTTTCCGGAACAGCCTCAGCAAGTCGGTCCAGATCAGCGATAGCCGGCGTGGAACCTCCGGCCAGCCATTGGGACTTGGACAGGCACGGGA
TGAGCGAATGGTGCTTGTGTCGCGCAAGATTCCGTTCTTCATATTCTCTTCACTTCCCTATTACAAGGGCAAGAATGGAAGAGCTGAGTTTCGCA
AGGAGGATCGTCGTCGTCGGAATCCATCCACTTCGCGTCCTTTGAGCTCGATCAACGATGCGCCATTCGATCCGTTTGATTTGCTGGGTATACAG
AAGGCCGAAAGTGGTCAGGACATATCATATGGTCACCTGCTGATACCTTCACGTCAGTACGAAAAGGAGCGCAAGAAGCATGGCAATGCATCGGC
GAATCCTTCCATCTTTGAGAACCAAATGGAGATCACGAGCACAGCGGCGCTTAAGAATCATGGCATTGCGAGGTGCTTCACTTATGAGAACAACA
ATCGCAATAGTGCAACCAGTCCGACGCCAGACATGAAACTGGATATGGACATAGAGAGTGTTATCCTGGGCGGAGACTCGTCGCGTGGTCAGGTG
TACTCCGCTAGCATTTTGGACGATCCGGAGTTGATTGCCGGAAAGCATCGCACGTTGCTTACCTTCACCTCTTACATGACCTCGGTCATTGACTA
TGTGCGTCCATCCGATCTTAAGAAGGAGCTGAACGATAAGTTTCGCGAGAAGTTCCCCACCATCCAGCTCACACTGAGTAAGCTGAGGAGCATTA
AGCGCGAAATGCGCCGAATCAACAAGTTGGACTCGCGCATCGATCTGGTGACCATATCGCAGGCGTACGTGTACTTCGAGAAGCTCATCCTGGCC
AATCTGATTAACAAGAGCAACCGCAAGCTGTGCGCCGGCGCCTGTCTGCTGCTCAGCGCCAAGATGAATGACGTGAAGGGTGACGCACTCAAGAG
CCTCATCGAGAAGACGGAGAGCGTGTTCCGGTTGAATCGCAAGGAGCTGATCTCGTCGGAGTTCGCTGTGCTTGTGGCTCTGGAGTTTAGCCTGC
ATGTAAACCGGCACGAGGTCCTGCCACACTATCAGCGGCTGCTCTACGAGTCCTAGGACTGGCCCAAGCGCTGCGCCGAGAAGAGTTTCCTGGCG
GCAGCGCAGGCGGTACAGCAATTGTGTCGCAAGGGCAGTCGCAAGTAGGCGTTCGTACTTATAGCATACTTTCGGGTGTTGGGTTTTCAACGATC
GTATTGATAATATT
(SEQ ID NO: 701)

Start ATG: 848 (Reverse strand: CAT)

MASSLNKTRHRRRLAAISFLSNISLDGTHRDTKFGATFGSSLLCNQNKNPSSLGLGSGGFHPHYQQHHHQRSHSATHHNHQKRHHTQQQQQQQQ
QHTQQQQQQQQHQQQHQQQQQHQNGALCSPLLCSADVHMGIDGGIGLGLGLEDCTTGASDGDGHFSETENMGQYLMNVLPAADHNRSSIVPAERR
NIKRPTSSGRHNHQAPGNGNMGNKLQQQQQQQHKLQQQQRQARSCAAGSGGSGAESGSDSDSVKIPLKVSNLGSGGGVAGGAGSKLLPLRERTFS
NGASDQNLQPERRARLNTAPGMRVGSNSSIAMGGGLKRTYVLSGSSVSHITDDSSTESLTPAGNYAGSFRNSLSKSVQISDSRRGTSGQPLGLGQ
ARDERMVLVSRKIPFFIFSSLPYYKGKNGRAEFRKEDRRRRNPSTSRPLSSINDAPFDPFDLLGIQKAESGQDISYGHLLIPSRQYEKERKKHGN
ASANPSIFENQMEITSTAALKNHGIARCFTYENNNRNSATSPTPDMKLDMDIESVILGGDSSRGQVYSASILDDPELIAGKHRTLLTFTSYMTSV
IDYVRPSDLKKELNDKFREKFPTIQLTLSKLRSIKREMRRINKLDSRIDLVTISQAYVYFEKLILANLINKSNRKLCAGACLLLSAKMNDVKGDA
LKSLIEKTESVFRLNRKELISSEFAVLVALEFSLHVNRHEVLPHYQRLLYES*
(SEQ ID NO: 702)

Classification: known_flybase_gene
Gene Symbol: BcDNA:GH06193
FlyBase ID: FBgn0027581

Celera Sequence No. : 142000013384674
TGTACAACAGCCCTAATATTAGATATTTAATGTTGTTCATATAACAAATATCCCGAACATCAACAATATTTCCTTATGATCTAATGACCCTTATG
ATCAGTTAAGCTTTCAGCCCTTTATGCAATTGGTTATTTCGGTCCAGAAGGCCTGAACTTCAGGATCCTGCATTAAACTACGTTTCTTAGCGTTC
AAAACTATGTTGAGGATGTCGGCATTTTTGCAGCAATCCCGTCTGGCGGATTTGCCATCCGGCGCCTCCGGGGAAAAGCCTTCCGTCTCCTGGTC
ATCCATTGGATCCACTTCACCCGCCGGACTGCCCAATTGTCCAACTGCAAAATAACAATGTATTTGGGGGAATCTATTGCTTAATCAACTTAAAT
ACCTTTCTTGCACTTGGTCGCCTCTGTTTTCGGTTTTTCTGTCCGTTTTTGGTAGGGTTTTCTTGGTTTTGAGACATCTTTCGTCTTGCTGCGCT
TGGCATTCGCATCGGTGGGCAGCAATTCGGGACTCTCGGCGGGATTATCCGCATCCTGCTGCAGGCGCCGCTTGACGTGCAGATTCAGGCGCTCC
TTGATGTTTTGCTGTTCCAGTTTTATTTGCACACCAGTGGTTTCTGCCATGTTTTTGCGTTTTGAATATAAAAACAATATCCAAAACAGTCCACC
AGTGTGACCCCTAAATAAATCTTACAAAAAAATAAACAGTAACGTAAGATACAACTTTCTCACTTGTATTTGATTGTTCCTAATTATTTCTAACT
ATGTAAATATCGTTAGTATTGGATGCAAAGCTATGGCGGTAGACGTAAGGAAGGAATTATCAGTGCAATTTAGAAGTTAAATAAATTTGTTATCT
AATAATTATTTGGCAAAATTTGTGGCAGTGTGAACGGAACTGGGTTGAGTCTCCGCTACCCCATATCCGAGCCACGCACCCCAGGTCTGCATTTG
TGTCGATGGCAAATCTGGTATTTTTCAGCGACGCCATGTTGGATTGCGAACAACAGTTAACAGCAGCAAACGAGAAATCAGCTCGCAGCGCAGAA
AAATTAAAAAATATCGCCGTAAAAGTGAGCCCAACCGACCCAAAACATATGAAAAGTGTGAATTAAAGGACAATAAAGATATAAATCATTAATTA
AGCTTTGAGCAAGCGCGAAAAGTACGCGAAATCAACGTTTTGCAAAACGTTCGCCATACGCGTCGCCATTGGTGTGAGCGATAGCTTGCCTGTGT
GTGCGTGTGGTATTGGAGGAGGTGAGAGCGCCTGTGTGTGTGTGTGTTTGCGTGCGTGTGTGAGAGCGAGCGAGCGGCCCCTATGAAAAGCAACA
GCAACAACGCCAGCAAAGGACCCGCAACAACAACAACAACAACAGCAAGAGTAACAAGCACAGCGTTTTAATATCCAAATAATGAGTGTCGCTGC
AATGACTATGGACGATCAAAGACCCTGTATGAACAGTTACGACAAAATGCCCCCGACCAAATACGAGCAAAACCTAAATATCCTAAACAGCAGCC
AAAACAGTGGGGCCACTGGCGGCCCCGCCTCCCCAACGCCCTCCGGCTTGGAGGACCACCATCATCATCACCATCCGCATCCGCACCATCATCAC
CATCAGGAGCAGCAGCAGCAGCAGCAGCAACAGCAACACTTGCAGCAGCAGCAACAACAGCAGCAGCAGCAACATGCAGCAGCTGTTGCAGAGGC
TGTTGCAGCCGCCGAACAGCGACAGCGCTTGCTCGAAGGTATTTTGCACATTTTGGTACACTGCTATATGATCAGAGATCTATCTGATCTATATA
ATACCCCCTATATACTACATACATACTCGTTTCGAATACCGACAAAAAAAAAAGAAAAGGAAAAAACCACGATCCAAAGTGTTGACTCTGTGTA
AATTGTATAAATAATGCAATATATAAACAACAAGTAAACGTAGTCTTTTAGTTTATTTCTGCCCCCACTCCACTTGGGTTTCTTGTGTCATTTGA
ATTTGTTTATGAAAAACACTCGGTAAAGAACTCAACGTATATATTATGTGAATCGAATCGAAGCGAACACTCTTTGCAACGAACATTCTTTCAGC
GGCGTTTTGGTTAACTTTATTTATTTATTTTTTTCAACACCACCTCGAGCAAACCGTCGAATGTAGTGAAAGTGCTTTCAAAAAGGACCATGCAT
ATAATAATCTATAATACCTAAATATGAACTAAGTTAAAAGGCAACTGACGCCTAAAGTTATCAAGTGATTACAAAGTGTTGTGCAACAGAACTAT
CTAAAATATAAAATATGAGTTAAATAATCATAAATAATATATGAGAATCGTAACCAATTATAACCAGTAAGCTGAGCTAAGCTTTAATATTGAAA
GCAATCGTACTTAAAATAAAAAATTATAAAATGAATCATAAGAAGATAAGGTTAACGAAGTAAAGTTTAAGATTTTATATAATCTTAATGAGAAA
ACCGGGCTGATAATAACATCAAATGAATAGAGCATATCAAGTAATAATAGTAGAGAATCCTAATCGGAGATTTTCCTCGTTTTCCGTCGTTTTTG
CGGTGTACAGTTTTCGTTTTGCGACCACTTTTCGTTTGCCTACGTGCCCGTTGAAGAAGAAGAAGAAGCACAGCAGCAGAGAAGTGGAGAGGAGA
AGAAGAGAGCCAACGTGTCTGCGTCCCCTGCCCCACCCCCTGGACCCATCTTATTCTCTCTCTTCGCGCCCCTCACGCTCTTTTCGTCGCGCCTA
AATATAAATAATAATATTAAATAATCAATTGAAAATGTGACAGTGCATAACCAAAGAGAAAATAAAGTTGAAATTCTTTTTCTGTTGAAATTGTG
TTAAAGAAGTGAACGTCAAATGAAAAAAACATTGCCTCGTGTGTTCAAACAAATACAAATGTTTAAATAAATGGCGCCAAAATACGGCGAACATG
TGTGCGTTTGTGTGTGAGTGTGTATATTCACAATTGTTAAGCTTACTTAATTGATTTTTAAACGCTTAATTGGCCGCCAATCAATCAATTAACAT
GCAATGTGGGACACACGCACATGCACACATTTGTTTGCCCCGATCAAATAGTATATATAAATATAAAATAATTGCTTGGCTAAGTAAATACAAAA
GCGAAGTTATATATGTACGTGTTTGCACAACAAATCCAACAAAAAAATGCAAAGTCAATAAACTTTTTGTATGACAAAAGAGTGTTCGAAAATGCC GCAAAAAAGAGAAGGGGAAAAGCTTTTGAAATCCATGCATACATACATCCATGCATAGGCATACGAAAAAGCTTCCGAAAGCCCATTGTGTGTGC
GTCGAGTTTTTTGCAAGTGTTTTTCAAAAATATTTTCAGTTTTGCCACAAAAAATATGTATACCAATCAGTCATCGTTGTTTTCCACAGTGTATG
CAAGTTCGAAAATGCCGCGAAGATTCAAATTCAATCGCCAATCAAGTTCGATGCAAATGCAAATGCATAAGCAAAAGCAAGAAATCAAAATGCAA
ATAATGGCAGGTGTTCAAGTTATTCAAGTGCCAATGATAATGCCAGAGATAACGAAGCAATCGAAATCGAAATCCAAACCGCAAGCGAATTCGAT
ACCGAAATCGATATCGTGTTGTCCAAGTTCAAGTGGTTCAAGTTGTGACACTCGCATCGAATCAAAATCTAAATCAATATCATTATCAGCCAGAG
ATTGACGACGGGATGCGGCCTTTTCCACCGACCATGTCACGAACTTACACGAATGATTGCAACGCATTGGTATGATTTCGTATTAAGTTCCACCT
AAAAAAACAAACACTTTGCCTTGCCCATTAAGAACTTGTAAAATATCTATGTATATATAGTACGATATTGTTATATCTCGTGTGCGAACCAAAAA
AAAAAAAAAAAGACAGTGGCTCTCTCAGCTTGGAACGCCCGTTATCTAGACCCCATTATTAGCTAATCCTTATCCTTCGATTGCGCAGATGAGATC
GAGAATCTCAAGCTGGAACAGGTCCGCATGGCTCAGCAATGCGCGGACGCCCAGCGACGCGAGAAGATCCTCATGCGACGGCTGGCCAACAAGGA
GCAAGAATTCCAGGACTATGTGGTGGGTACTCGCCTTAATATACACAAATTTCTCAAATACTAATGCACCCGTAATCCCCATTAGAGCCAAATTG
CCGAGTACAAGGCCCAACAGGCGCCAACTGCCCTCGCATTGCGCACTGCTCTGCTCGATCCTGCGGTCAATCTCCTGTTCGAGCGGCTCAAGAAG
GAACTTAAGGCCACCAAGGCCAAGCTGGAGGAGACCCAGAACGAGCTGTCCGCATGGAAGTTCACGCCGGACTCTAATACCGGCAAACGCCTAAT
GGCCAAGTGCCGACTGCTCTATCAGGAGAACGAGGAGCTGGGCAAGATGACCTCCAACGGCAGACTGGCCAAGCTGGAGACCGAACTGGCCATGC
AGAAGAGCTTCAGCGAAGAGGTCAAGAAATCGCAGTCGGGTAGGTTAAATCTGAACTAGGATTGGGATCGAAACTTATAGATATGTAAACTCCTT
TACCATTTAGAGTTGGACGACTTCCTGCAGGAGCTGGACGAGGATGTGGAGGGCATGCAGAGCACCATTCTGTTTTTGCAGCAAGAACTAAAGAC
CACACGCGATCGCATACAAACGCTTGAGAAGGAGAACGCCCAGTTGAAACAGGCCATCAAGGATGAGGTTGTGGCTCCAGCGGCTGCCACCAACG
GTGGCACCAACACGACGATAAATAAGCTAGAGACCATTCACGAGGACGCTTGCATGGCGAATAACCCAACGAATCCGGATTGTTACAATGGGAAT
ACCAACAACGAACAGATCGCGGCCGTGCCACAGATACCACTGTCGGATGATGGCAGCAATATGAACGGAAATGCAGCGCGATTAGCCCGCAAACG
AAACTACCAAGAGGAGGAAGCCCTTCCAACGGTAGTGGTGGTGCCGACTCCCACCCCAGTAGGAAATAACGTCCAGGAAGCGCCGCCCATCAGGG
AAGTTACCGCCCCACGTACTCTGCCGCCCAAAAAGTCCAAGCTGCGAGGCATTACCACGCGTCGCAACTCCCAGCTGGAGGAGGATCATCAGCCA
GTGACAACACCAGTGGCCGTCCCCATGATCGTGGACAACGCTGTGGCCGGAATGGCGAGCGAAGAGGCTGCTGCCGCCGCTGCGGCTGTTAATAA
CAGCAATACGGGAATAATCCCGGAAACGGGAGTGCAAGTGGGTGTCCCAGTTGAGGGCGGCGATCCAGGTGCTCCGGCGGCACCGGGCCGCATCC
TGACCCGTCGTCGGTCCGTCCGCATGCAGCAGAACGGCAGCGGAGCAGTCGACTACTCCACCTAAGCGCTGGCGAACCTTTTTCCAAAAAAGGGT
GCACTCCATATGAGTTCGTCAAATTGATCGTTAATTCCTGACGTTTACTTTTGTGAATTGAGATTTCAAAACAGAGAGAGACTTCATTTTATATT
TCTAACCTATCTTTTAGATTCTTTAATTTTTTTACACATTGTCTTGTAAAATACGTTTATTATTTCGTTTGCATGCGGCGTAGACATACATAAT
TCGCAAATTATTTAGAAGTCACTGCTTTACATACGAAATGCATTATGTAGAACAGTGTAAAACTTCAGCACATATATTTACAATAATACGATCGA
GCTAAATGATAATGCTAAAAACTGATACACTATTTATGTTTTTTAACCACGGCATCTACTGAAAAGCTGAAAAGAAAGCTTGGTCAAAACAAAAC
TTGTCATTTAGCAAAATTAGGTTTTAATTATCAACTTAAGGCATTTTTGTAATACTATGAAAGTTGTGTAAAATAATATAAACTTGTGTTAAAAT
AAATTGTTAAGCATAACAAATATTTCAAAAAACCAGTGTCCTTTAATTTCAATTGCCGCCCAGCAAAACAATCGTTTTGATTTTCGAAATTATCT
TGTGTTTATTATCAGTTTCTTCTTTTAGCACATTAGACAAATGGTTTTACTTGTATTTGATTGAATTCGAAATATGTTTATGTATGTAGTACAAT
TGTGGCTGCCAGCGAGTGTGTTTGTATCCTTTGTTTCGTTTGTGTCTGTGAGAAGAGTTTAAACTTGAGATCGGGCTAAAATGTTCTGGTAAAGA
GGCCTGCAAGCTTGGCATAGTTTGATATTTGCTTTACCCTACTTTCAATCGAAATGTACAAAATGAGTAGGGATGTGGTGAGACAACCTGCAAGG
GGGTTAAACGTACTTCCGATTCCATATTAAATAGTTAATAACAAATACTAGGCAGTTCGAATGGCACAAGTTGATTACACTACCATGGGGAAATG
TGGGGTGTCTAAAGCTTAGCGAGTTCTGTTCCGATCGGAGGAGATATCCTTTCGGCTGAGAGTTTGTTTGTCTAGATGTACGATAGTTTGTTATG
GTAAATTTCAACTAGTCAATGGTTTAAGTGTAGTATTATTAATAATTTAGTCGCTAGATGCTGCTGCGTTTACTCAATCGTCTCAGTTCTGTGGC
TCGTATCAAGTAGTTAGTAATAAAAAGTATTTCTCATATATGTATGTAGGTACTTGTGGGTAATGCTAGGTATCGTCATCATCAGTGTATATAAA
AACAATGCCTTTAAATCGGATCTCTTTTTGGTTTTGCTTGTTCTTGAGTGGCCTACAATGTCCTTTTTAACGAATGTCTATAAAAGTATGTAGTT
TTCCAAGGCTCCGAGGCTGAACTTTCGGTTAGTTTTTCTCTGGGCTAGGCTAAGCAAATATACAAAAGCTACTTAAATTAGTTAGCATGTACAGT
ACCGGGCGTACTCGTAGGTATATATCGTATTATCGTATGAGTGTGTGTATATATAATTAAATGGTTCCATTATTCG
(SEQ ID NO: 703)

Exon: 1001..1748
Exon: 3983..4107
Exon: 4171..4504
Exon: 4571..5916
Start ATG: 1412

Transcript No. : CT19764
CAACAGTTAACAGCAGCAAACGAGAAATCAGCTCGCAGCGCAGAAAAATTAAAAAATATCGCCGTAAAAGTGAGCCCAACCGACCCAAAACATAT
GAAAAGTGTGAATTAAAGGACAATAAAGATATAAATCATTAATTAAGCTTTGAGCAAGCGCGAAAAGTACGCGAAATCAACGTTTTGCAAAACGT
TCGCCATACGCGTCGCCATTGGTGTGAGCGATAGCTTGCCTGTGTGTGCGTGTGGTATTGGAGGAGGTGAGAGCGCCTGTGTGTGTGTGTGTTTG
CGTGCGTGTGTGAGAGCGAGCGAGCGGCCCCTATGAAAAGCAACAGCAACAACGCCAGCAAAGGACCCGCAACAACAACAACAACAACAGCAAGA
GTAACAAGCACAGCGTTTTAATATCCAAATAATGAGTGTCGCTGCAATGACTATGGACGATCAAAGACCCTGTATGAACAGTTACGACAAAATGC
CCCCGACCAAATACGAGCAAAACCTAAATATCCTAAACAGCAGCCAAAACAGTGGGGCCACTGGCGGCCCCGCCTCCCCAACGCCCTCCGGCTTG
GAGGACCACCATCATCATCACCATCCGCATCCGCACCATCATCACCATCAGGAGCAGCAGCAGCAGCAGCAGCAACAGCAACACTTGCAGCAGCA
GCAACAACAGCAGCAGCAGCAACATGCAGCAGCTGTTGCAGAGGCTGTTGCAGCCGCCGAACAGCGACAGCGCTTGCTCGAAGATGAGATCGAGA
ATCTCAAGCTGGAACAGGTCCGCATGGCTCAGCAATGCGCGGACGCCCAGCGACGCGAGAAGATCCTCATGCGACGGCTGGCCAACAAGGAGCAA
GAATTCCAGGACTATGTGAGCCAAATTGCCGAGTACAAGGCCCAACAGGCGCCAACTGCCCTCGCATTGCGCACTGCTCTGCTCGATCCTGCGGT
CAATCTCCTGTTCGAGCGGCTCAAGAAGGAACTTAAGGCCACCAAGGCCAAGCTGGAGGAGACCCAGAACGAGCTGTCCGCATGGAAGTTCACGC
CGGACTCTAATACCGGCAAACGCCTAATGGCCAAGTGCCGACTGCTCTATCAGGAGAACGAGGAGCTGGGCAAGATGACCTCCAACGGCAGACTG
GCCAAGCTGGAGACCGAACTGGCCATGCAGAAGAGCTTCAGCGAAGAGGTCAAGAAATCGCAGTCGGAGTTGGACGACTTCCTGCAGGAGCTGGA
CGAGGATGTGGAGGGCATGCAGAGCACCATTCTGTTTTTGCAGCAAGAACTAAAGACCACACGCGATCGCATACAAACGCTTGAGAAGGAGAACG
CCCAGTTGAAACAGGCCATCAAGGATGAGGTTGTGGCTCCAGCGGCTGCCACCAACGGTGGCACCAACACGACGATAAATAAGCTAGAGACCATT
CACGAGGACGCTTGCATGGCGAATAACCCAACGAATCCGGATTGTTACAATGGGAATACCAACAACGAACAGATCGCGGCCGTGCCACAGATACC
ACTGTCGGATGATGGCAGCAATATGAACGGAAATGCAGCGCGATTAGCCCGCAAACGAAACTACCAAGAGGAGGAAGCCCTTCCAACGGTAGTGG
TGGTGCCGACTCCCACCCCAGTAGGAAATAACGTCCAGGAAGCGCCGCCCATCAGGGAAGTTACCGCCCCACGTACTCTGCCGCCCAAAAAGTCC
AAGCTGCGAGGCATTACCACGCGTCGCAACTCCCAGCTGGAGGAGGATCATCAGCCAGTGACAACACCAGTGGCCGTCCCCATGATCGTGGACAA
CGCTGTGGCCGGAATGGCGAGCGAAGAGGCTGCTGCCGCCGCTGCGGCTGTTAATAACAGCAATACGGGAATAATCCCGGAAACGGGAGTGCAAG
TGGGTGTCCCAGTTGAGGGCGGCGATCCAGGTGCTCCGGCGGCACCGGGCCGCATCCTGACCCGTCGTCGGTCCGTCCGCATGCAGCAGAACGGC
AGCGGAGCAGTCGACTACTCCACCTAAGCGCTGGCGAACCTTTTTCCAAAAAAGGGTGCACTCCATATGAGTTCGTCAAATTGATCGTTAATTCC
TGACGTTTACTTTTGTGAATTGAGATTTCAAAACAGAGAGAGACTTCATTTTATATTTCTAACCTATCTTTTAGATTCTTTAATTTTTTTACAC ATTGTCTTGTAAAATACGTTTATTATTTCGTTTGCATGCGGCGTAGACATACATAATTCGCAAATTATTTAGAAGTCACTGCTTTACATACGAAA
TGCATTATGTAGAACAGTGTAAAACTTCAGCACATATATTTACAATAATACGATCGAGCTAAATGATAATGCTAAAAACTGATACACTATTTATG
TTTTTTAACCACGGCATCTACTGAAAAGCTGAAAAGAAAGCTTGGTCAAAACAAAACTTGTCATTTAGCAAAATTAGGTTTTAATTATCAACTTA
AGGCATTTTTGTAATACTATGAAAGTTGTGTAAAATAATATAAACTTGTGTTAAAATAAATTGTTAAGCATAACAAATATTTC
(SEQ ID NO: 704)

Start ATG: 412

MSVAAMTMDDQRPCMNSYDKMPPTKYEQNLNILNSSQNSGATGGPASPTPSGLEDHHHHHHPHPHHHHHQEQQQQQQQQHLQQQQQQQQQHAA
AVAEAVAAAEQRQRLLEDEIENLKLEQVRMAQQCADAQRREKILMRRLANKEQEFQDYVSQIAEYKAQQAPTALALRTALLDPAVNLLFERLKKE
LKATKAKLEETQNELSAWKFTPDSNTGKRLMAKCRLLYQENEELGKMTSNGRLAKLETELAMQKSFSEEVKKSQSELDDFLQELDEDVEGMQSTI
LFLQQELKTTRDRIQTLEKENAQLKQAIKDEVVAPAAATNGGTNTTINKLETIHEDACMANNPTNPDCYNGNTNNEQIAAVPQIPLSDDGSNMNG
NAARLARKRNYQEEEALPTVVVVPTPTPVGNNVQEAPPIREVTAPRTLPPKKSKLRGITTRRNSQLEEDHQPVTTPVAVPMIVDNAVAGMASEEA
AAAAAAVNNSNTGIIPETGVQVGVPVEGGDPGAPAAPGRILTRRRSVRMQQNGSGAVDYST*
(SEQ ID NO: 705)

Classification: known_flybase_gene
Gene Symbol: fl(2)d
FlyBase ID: FBgn0000662

Celera Sequence No. : 142000013384544
TTTTCTCGGATATAGGCAAAATGGAACAATTTAGCCATTTCTAGCCAATGACACGCCCCTTCACCTCGACGTTTCTACATCTGTGCAAAGTCATA
AAAGTTAAACGATTGCCAGAGCTATTAAATATTTCAGACACATTTTGTGGGCAAAAATTGTAACAGACTTCAAGCGAACGAAATAAACCGAAACC
CAACCCAAATTTAAGCAAAAACCTAAAATGTCTTTTGGAAATGTTAAGCGCGAAATTGGCAAACTTTATGTGCCTGAATTTTGGACTGCAATTTG
CGTTTAATTTGGGGTCACACACATTTCGGGCGAACCCCGGGCAATGTTAAGTTATGTAAAGGCAAATTTAACAATGTGCCAAGGGACGGAGCTGA
GGGTAATCAATGTGAAGCAGTTTTAGTCTCCGAAGGCATTTTAATTGCCACAGAGCAACTTGCAACATTGCAACCTGCCCCGCGGCCAAGTTAAA
TGACACATGTGTCTGCCCCGGCCATTTTTCTCTTTCTCCCCCAATATCTTATCTCTCTCTCTCTCTGTCTGTCTCTGTATATCTTGGCCTGTT
TGTTGCTGCTGCTGCCGATGCTGTTGAAAAGACTTTCACTCTGGCCGAGCGCTATAGATGAAATGGCATTTGACTTCATTTTTGGCCAAAAATAA
AACCGAACCATTAACTAATTAGCTTACATTTTGAACGATTTATTGAGCTCTAGACTTAAGCGAAGCTCGTCTAACTAAAAATACTACTTAAATGC
TATGGTTTGCTCTCTCTTCATGAGAGCAGGCAATGATTAATTTTAAAGGAAGGCACAAAAGTCGATGTTTCAGTTTTAACAAATATTGTGGAATA
TATTGAGCTCTAGTTAAGTTATATTTACTGAAATAACTCCTCCTTTTATTTTATGGATTTTGGTTTTTAATAAATATCTAGAAACACTCAGAAAA
CGTTCTCACTTGTCCTAATTATTTCTTTTATATTAACCATATCTGATCACTCACCTTCTGGCCTGCCTGGGAATGGACTGCGTCCAGCACACGGG
TGCCTTGTGTAGTTGATGCATATTTCGGGAGGACTTGTAGGTGAGATCGCCGCACTCCGTCTGCCACACCTGGAGATTCCCCTCCGCCGGATAGA
AGGTATACAGGCTGTGGGTGGCCGAGGCGATGACCGGCGAGGAGCCACCGCCCTCGACCACATCGACCACGCCCGCTGCCACCAGTGGAGATAGG
GTGGCACTAGAAATCGGTTGGACGAGTAGGGCCTGTCCGGCTGCCGGTGCTCCGGCTGCAGTGCCTCCGCCAGGCGACTTGTAGTTCAGCATGCG
GGTGGCGGTGGCACCGGCATTGCTGCTGCTTATATTGCCATTTCCGTCGTGCTTCAGGATCAGGCTACTTGGATCGTAGCCGTGGCGATTGTGCC
GCGAAATGGCGTCCACCGAATGGGATCTAATGCCGGTTCGAGGTGGATTCACGTGGAGCCGACGTCCGCGCCGGTAGTTAGCAGTGCCAGTTCCG
GTTCCCAGGCTACTATTGCCCAATCCCGAAGATCCCTGCTGCATCGACGCGGTCAACCGGTGATTGTGGACACTGGAGGCGGCACTTGGAACGAG
GGGCTGTCGTTGTTTTTGGTACTGGAGGCGTGGCTGTTGCGGGGGTGCCTGATGCCTTAGTTTCCCCTGATCCTTGGCAAAGAACTCCCGCCTCT
GCAGCTGGGGGGCGGCCAAAGTGAGTGCGCCCCTGACGGAGTTCACCATTGAGGGGCTGGATGCATTTGCTCCGGACGTCGTCTTAGTGGCGCCC
CCAGTAGCCGCCGAACTAAGCTGCGCGAGCTTACTGGCATTGTTGTTGCTGACCGTATTTGCTGCATTGCTGTTGTTGCAAGTGCTGGTGCTAGT
GGTTCCACTTGTCTGATGCTCCGAATCGGTGGAAACCCGATCCGGATCACTTTCGAAACCTTCGTCCAGGGATCGAGTTGGACTCAGAATGGGCT
TCGAGTGCTGCTGCTCCAGTTTCGTAGACATGGCTGCTGGCCACTAAGGGGTATTATTTGTTGTTGTTTCTTTTGTGTTTTTTTATTATTTTTTC
TACAGCTTTAGCCCGGGTATTGGGTATCGTTACACTTGCTGCACATATGCACCTTATTTCTCTCTTTCTCTGCCGCCTGCCATGCACACTTGTTT
TTCACATTTAATTTCGCTTGGCTTTCAGCTCGTTCACTTCGCGAAAAGTCGCGCCAAAGTTGCAGTTTGCAGTTGGTTTGGATTTTGGTTTTGGT
TCGAATAAAAAATAGCTACTGCGTTATACACGTCTGTCTCGCACGAAAGCTTTTTATCGACTGTGGAGTGCGAGTCGGAAACGGAATTAACTTGG
TTCGCTCTGTTATCGCCATGTTAAGTAACATTCGTTAACATTTACCAACGGAAAGAGCAAAAGCTTCGATCGACACTTGTTGCGGTGCACCTGTT
ACATTTAAAAAGTGCCTGAGAGAGAGAGAGAGTAACATCGCTCAGCTGTTTGCCAAATGTTATTCGCGAAACTTCCAAGTGAGAAAGATCATCAC
AGAATAACAAAGTAAAATGAAGAAAGACAGGAAAATATAAACACGGAAGTGTCGAGACATCATCCTAAAAATGCTTTTTCCTGTTCACATTTGCT
TTGCACGAAAATGTTATCAATTTACAATATTTTTTAAGTGTTTTATCAAAGCTGTTGTTTTAGTAAATACGATTGTGAAAATCTTTTAATTGACA
CTACACATTCAATATCTCCCAGATATATATCTATATTTTTCCGATATTCGGTAAAACTTTAAAACCACCATGCCATATATTTTAGAAGCGACTGT
GATTTTGTTTTCGGCTCCACTGGGATTTATCAATGAAAATACCAACTCCAAAGCAAGAGCAAAAACAACAACCGGCACAAGCCGAGAGAGGGAGC
GAAGCAAACAAAAACAAAACGAAGGCTTGAAAAGCTCGCTGTGCTGAGAGCAAAAGAGCAAGGAGCTTTCGACACCTGCTGCACCTGTACAACAA
CAGCATAAATATTTGTGGGAGGGTGGCGATAGGAAGTATTTTGCTTATTTTGTTGCTTAGATTCGATTGAATTTTGAGCAATGTCTTTTGTAATT
TCCTTTTTATATATTTTTTTAATTTTTGCAATATGCCTAACTGACTGTATGAACCATATGAATTAACTCCTATTGAATATATTTTAAAAACTTAC
GCCTATTGACTATATATTGTTCGAAAAATTATTGTAATAATCACTTGGCGGCACAGATCCTTCCGCAATCCTAATCCAATTCATGGA
(SEQ ID NO: 706)

Exon: 2317..1001
Start ATG: 2026 (Reverse strand: CAT)

Transcript No. : CT19790
ACAGACGTGTATAACGCAGTAGCTATTTTTTATTCGAACCAAAACCAAAATCCAAACCAACTGCAAACTGCAACTTTGGCGCGACTTTTCGCGAA
GTGAACGAGCTGAAAGCCAAGCGAAATTAAATGTGAAAAACAAGTGTGCATGGCAGGCGGCAGAGAAAGAGAGAAATAAGGTGCATATGTGCAGC
AAGTGTAACGATACCCAATACCCGGGCTAAAGCTGTAGAAAAAATAATAAAAAAACACAAAAGAAACAACAACAAATAATACCCCTTAGTGGCCA
GCAGCCATGTCTACGAAACTGGAGCAGCAGCACTCGAAGCCCATTCTGAGTCCAACTCGATCCCTGGACGAAGGTTTCGAAAGTGATCCGGATCG
GGTTTCCACCGATTCGGAGCATCAGACAAGTGGAACCACTAGCACCAGCACTTGCAACAACAGCAATGCAGCAAATACGGTCAGCAACAACAATG
CCAGTAAGCTCGCGCAGCTTAGTTCGGCGGCTACTGGGGGCGCCACTAAGACGACGTCCGGAGCAAATGCATCCAGCCCCTCAATGGTGAACTCC
GTCAGGGGCGCACTCACTTTGGCCGCCCCCCAGCTGCAGAGGCGGGAGTTCTTTGCCAAGGATCAGGGGAAACTAAGGCATCAGGCACCCCCGCA
ACAGCCACGCCTCCAGTACCAAAAACAACGACAGCCCCTCGTTCCAAGTGCCGCCTCCAGTGTCCACAATCACCGGTTGACCGCGTCGATGCAGC AGGGATCTTCGGGATTGGGCAATAGTAGCCTGGGAACCGGAACTGGCACTGCTAACTACCGGCGCGGACGTCGGCTCCACGTGAATCCACCTCGA
ACCGGCATTAGATCCCATTCGGTGGACGCCATTTCGCGGCACAATCGCCACGGCTACGATCCAAGTAGCCTGATCCTGAAGCACGACGGAAATGG
CAATATAAGCAGCAGCAATGCCGGTGCCACCGCCACCCGCATGCTGAACTACAAGTCGCCTGGCGGAGGCACTGCAGCCGGAGCACCGGCAGCCG
GACAGGCCCTACTCGTCCAACCGATTTCTAGTGCCACCCTATCTCCACTGGTGGCAGCGGGCGTGGTCGATGTGGTCGAGGGCGGTGGCTCCTCG
CCGGTCATCGCCTCGGCCACCCACAGCCTGTATACCTTCTATCCGGCGGAGGGGAATCTCCAGGTGTGGCAGACGGAGTGCGGCGATCTCACCTA
CAAGTCCTCCCGAAATATGCATCAACTACACAAGGCACCCGTGTGCTGGACGCAGTCCATTCCCAGGCAGGCCAGAAGGTGA
(SEQ ID NO: 707)

Start ATG: 292 (Reverse strand: CAT)

MSTKLEQQHSKPILSPTRSLDEGFESDPDRVSTDSEHQTSGTTSTSTCNNSNAANTVSNNNASKLAQLSSAATGGATKTTSGANASSPSMVNSVR
GALTLAAPQLQRREFFAKDQGKLRHQAPPQQPRLQYQKQRQPLVPSAASSVHNHRLTASMQQGSSGLGNSSLGTGTGTANYRRGRRLHVNPPRTG
IRSHSVDAISRHNRHGYDPSSLILKHDGNGNISSSNAGATATRMLNYKSPGGGTAAGAPAAGQALLVQPISSATLSPLVAAGVVDVVEGGGSSPV
IASATHSLYTFYPAEGNLQVWQTECGDLTYKSSRNMHQLHKAPVCWTQSIPRQARR*
(SEQ ID NO: 708)

Celera Sequence No. : 142000013384512
AATATGCATGTTCTTGAATCCCACAACGTGACTATTTGTTCATTGACCCCAGGGCGTATTTGTGGGTCAATTCGTTTGCGGAAGCCACCCGTGGC
CCCACCGCAACCCCTTAAGAGCCGATCCTATAACCGGCAAAACTGATGCCGGGTTCAGTGCGCCGGGTTTTAGAGCTGAACAAAGTGCAGTCATG
AAGAAACCCAGCAGCGGGCTTCAAAATTTTTGGTAATTCGGCATAAAAATGTCGAGCATGCCAGCAAAACAGAACGCCAATTGCCGGGATCAGCA
AATTTAGCCAATGGAAATTCGGATCAGAACCGATCGACCAGGAAACCTGATGCGCTGGCAGCGGCCATTGCACCGTGCTTATAAGAGCTGGATGG
CTAACTCTCAGGTTTTAGTTCTGGAATAGTACGTGTCGCGGTTGGTAAATCGAGGTACTTCGATACCCCGAGGAATCAGTTAAAATCATACATAA
TTGTTGACCACAATTGCCTCGGGAACTTCGATCGCGTCCTGAATTTATATCGAGTTATCTAAGGAAATAGTAGCCGTGATTTTACCCAAGAATTT
TTCACATATCACAGTTGCTGTTTCTTTTAGATAGCTCTTTTGTAAACAGCCTAGATCCGAATGCGAGTATCCGAGTGCCTTGCGTGAATCCTGGA
TGAAAAGGTCCTTCGGTTTCAGTTTATGGGATACACACAGTTCAGTTTTGTCACACTTCAAGCATCACTGGGCTTTGTTTATCTCATGAGAGCGA
AATTTATTCAACAGGAAACCTTAAATCATACCAATATATAAAAAAATCTGTATATAAAACATTTGAATTTCTTGGATCAAGTTTTTAAGCTTAAT
CAGAAAAGTAAGTACAAAAGTGAAATAAAGTAGGTTGGTGGATAAATATATTGTAAACTAAATTCTTTTGTCATAAAACGAAATAAGTTAAAATA
TTTTCATTGAAATCAATCTTTCATTTCCCAGAAAAACAAAGTACACCCAATTTAATTAGATACCAAGAATAAGGGCTTACTTTATTGGTTTGACC
AGGTTGGGGAAGCACCACCACAATTTAAAACTTAGGGAACTACAATTTACAGTGTAGAAATGCATGTGGAATATACATATATAAAAACAAAATAA
GATGAGTTGCTTAAGAGAGCATTTTGCGAATCATGTAGTTGAGGATTCCACCATTCTTGTAGTAGGTGATGTCCACCTCAGTGTCGAAGCGCAGA
ATAGTCTCAAAGACGGTGCCATCAGCCTTGAAAAAAGATAGTTCATTAATATAACCAAAATCGCTAGCACCAGGTTTCCAATAGCCTACCTCCAC
TTGGATCTTCTGGCCCGGCTTTAAACCGCTCTCTGGCAGGGCGATGTTGTACACCTCCCGGCCAGTCAGGTTCAATGTCTCGGCACTCTGTCCCG
GCAGGAATTGCAGCGGAATGATGCCCATGCCCACCAGGTTGGAACGATGAATGCGCTCGTAGGACTCCGCGATCACCGCCTTGACGCCCAGCAGG
AAGGGACCCTTGGCGGCCCAATCCCGAGAGCTTCCGCTGCCGTAGTCCTTGCCTACAACGAGGACCAGAGGAGTACCCTCCTCGCGGTACCGCTC
GGCGGCATCGAAGATATCCAGCTCTTCCTGGCTGGGAATGTGCACGGTGCGGGGTCCTGTCTTTTCGACCAGTTTGTTGACCAACCGAATGTTGG
CGAAGGTGCCGCGCGACATGATGGCATCGTTGCCACGACGCGATCCGTACGAGTTGAAGTCACGGGGTGTGATGTTCCGCTCGGACAAGAATCGG
GCAGCAGGCGAGGTTCTAGCAATAGATCCAGCCGGCGAGATGTGATCCGTGGTGACGGAATCGCCTAGGAAGAGCAGGCAACGTGCCTTCTGAAT
GCTCTGCAGCTTGGGAAGATCTCTGGTCATGCCCTCGAAGAAGGGTGGTCGCTTAATGTAGGTGGAATCGGCACTCCAGGAGAAGAGCTTGCCCT
CGGACACCTGCAGAGTCTGCCAATCCTGGGAGCCCAGCTCAATTTTGCCTGCAGATGGAAGTGAAATTAAACCAAACTCAAATAAAGATGGCGCA
CGAAGTACTCACTGTACACCTCCTGGAACATGGCGGGGATTACATGCTTGTTCTCCACTTCCTGTATCTCCGATCGCGTTGGCCAGATGTCCTGC
AAGAACACATTCTTGCCATTGGCATCCACTCCCAGAGGTTCCTTCTCGAAGTCGATGTCCACGCGTCCTGCGATGGCATATGCGATCACCAACAG
AGGACTGGCCAGATAGTTGGCCCTGGTGTTGGGATGGATGCGACCCTCGAAGTTTCGGTTTCCGGACAAAACTCCAGCACACACGAGGCCGTTCT
TCTCGATGGTGTTCACCACATTCTCCTCGAGAGGACCGGAGTTACCAATGCAGGTCATGCATCCATAGCCCACAATATCGAAGCCCAACTTCTCC
AGATAGGGAATGACTCCGGACTCTTTCAGGTAGTAGGTAACCACACCGGATCCAGGCGACAGCGAGGTCTTGATATAGGGCAGGATGCTCAGACC
CTTCTCAACGGCCTTTTTGGCCAGCAGACCGGCACCCAGCATCACCGAAGGATTCGATGTGTTCGTGCAGGATGTGATGGCCGCAATGACAACAG
ATCCATGATGCAGTTTGTAGGTCTTGCCATCATCCCACTGGAACTCCCCAAAAGCGGATTGAGCTTCCGGAGCAATGGCGAATCCCTTGAAACCC
ACCTAAGGTAATGGTGGAGCAAAACAATGTTTAATTTAATTCCCTTTTTCTCAATGAATTTGAAACTTACTGGGCTGGACAGGCACGACTTAAAA
TCCTCAGGCATGTCGGAGACAGAAACGCGATCGTGAGGACGCTTGGGTCCCGAAACGGAGGTGACCACCGTCGACAGATCCAAGGTGATACTCTG
TAGAAGGGATGTATGTTAGCTTAAGTTTTTAGTGGTATATGTAAGGCAATTTCAACCTGAGTAAACTTGGGATCTTGGGCCGCATCAGCATAGTT
GCGCAGCTGCTGAGTTGCCTTCAGATACTGGCGAATGATGTCGATCTTCTTTTCAGACCGATCTAAAAAGTTTGTTATGATATAGGTAAAATATT
GTTTTATGAAACAGTCTGGTTTTCCGTACTTGTCTGCTTCATGTAACCAAGAGTATTCTCATCGATGGGGAAGTATCCCACGGTGGCTCCGTATT
CGGGACACATATTGCTGATGGTGGCCCTGTCAGCAATGCTGAGTTCCGCAACTCCCGGGCCGTAAAACTCCACAAACTTTCCCACCACACCCAAC
TGGCGCAGGTGCTTGGTAATGGTCAGCACCAGATCGGTGGATGTGACCAGTGGGCTCAGTTTGCCCTCCAACTTGTAGCCAATTACCTCGGGCAA
CAACATGGAAATCGATTGGCCCAACATCACAGCTTCCGCTTCGATGCCTCCCACTCCCCAACCAAGTACGCCCAATCCATTTATCATCGTGGTAT
GGGAATCAGTGCCCACCACACTGTCGGGATACAGAATCTTGGAGCCATCGGTTGCGTCATTCTCGAACACCACGCGGGCCAAGTACTCCAGATTC
ACCTGGTGGACAATACCGGAGCCAGGTGGCACGATCAGCATGTTGTTGAAGGCCTTGGCTCCCCACTAATTAGGAAAAACAATATTATTAAAAAT
ACTATCTGGATAATAAGCTAAGGAAAAGTAACCTTCAGGAAGGTGAAGCGCTCCTTGTTGCGCTCAAATTCCAGTGACTGGTTCTTGGCCAAAGC
ATCAGGCGCACGGGCGAAGTCCACCTGGACCGAGTGATCGATGACCAAGTCGGCGGGGCAGATGGGATTGATTTTCTCCGGGTCGCCGCCCAGAT
CCAAAACAGCATCGCGCATAGCTGCAAAGTCCACCACAGCAGGAACTCCAGTAAAGTCCTAGTAGCAAGATATTATATAATTTAAATATTACTTT
GCTAGATTGCCGTATGAAACTCACCTGCAGGATGACACGGGCCGGCTTGAAGGACACCTCCACATCGTTGGATCCCTGCTTGAGGGCGGGCGACC
ATCCCAGGATGCTCTGCACGTCCTTCTCTAGGATATGGAAGTTGTCGCAGTTGCGAACCGCCGACTCCAAGAGCACTCGGATCGAGTAGGGCAGT
TGATCTACGCGTTGGAAATGTTAAGTGTTAATCAAAGTGTTTAGAATTTCATCACAGGTACAGTAAAGCCTCTTGGTGAGAGGACCTAAGACAAT
TTGCCGCACTAAACGTATGTATCTTTAAAAAACCTTTAAGTTGCACTTGTTGAATTAAAATTCACGAGTAGAGTAAAGAACCTCCCTTTTTCTAT
AACCGTCCACCTTAGTTAGTTTAAAGTGTGCTAGTCAGATAGCAGTCACTTCTTATCACAGGCACAATGATTACGTTTGTCCAGCACTTAATGCG
ATTCACAGGCGTCACTATATGGGAGGAGCCACCAAAGAAGCCCTCACCTCAGAACCCCGATTTCTGGACACGCGCGGTTCCAGTAAAAACATTCC
ACTGATCTTGAGATTTTTCGGAGTCATCGGACTACGACCCCAAATCAGCAGATCTGCGAAGTTTTAATTCGCTGATAAGTGAGCACGTAAAATTG
GGAAATGGAAATCAAATTTCGGAGGCACACGATTCGTTATCACCGCTAGACGAGCCCCATTATGAGGCAATCTGGCGGTGATAACTTTCGCTTTC
GGCGCAAGACAAGCCCGCCCATAGAAAACTATAGAAAATCCACTTAATGCTCCGGGAGCACCTTCTACTTGACATTGCCTGACTTGCAAATTGAG
CTGTTCTTCTACGCTTCTTTTTCAATTCAGGGGTCAAACTCCAACTTCAACAGGTGCTTAATTAATCCCATTTTTGATATGCATGTTTAGCCTAG TTTATTGCGACCACGTAGACAGACACGCCCACTTTTAAAGCCTTCTTAAGACCACATCCACTTACCATATTTACTATCGATGGAGGCGAGGTCAA
AGTACTTGTATGTTGTGCCGGCCTGGGAGAAAGTTTTCTCGAACTGGGCGAAGGGATTGGCGCCTGCGACGATACGAATGTGTTATATAAGCCAC
AGGATTCGGGGGACAGGGTATATGGTAGTCGAGGGAACTGCAAAGCTCCGGACTGGCAACCCACCTGACATCTTATTGGAACTCTTTACTGAACT
TATTCCGGACGAGCAAAGCAAGAAACTGATTGGAGAAGCAGTTCGGATAGGAGCTGGCCAGCCTTCGCTGTCTATCGATAGCCAGCGATAGTTGC
GTATATCGCCAGTCGGATCGACAGTGCATTTTATACATTATATATGGTGCATTATATTTTATAAAACGATAGCTTTATGTTCACTTCTCTTTTTC
TAAAATGAGATTATAGTGTTCTGCGCTTGGTATGTTATTATCATATGTATTAAATGCAGTAATAACTATTCGGATATTTATGTAATACACCATCT
TTTGAAAAGCCTGAAATTTGTGCAATTATCAGTAAACTAAATCGACGAAAATAATTGAAAGTTGTATAACATATGGTTCATTTTTAAAATGAAAA
CTCCACCCGCCAAACCTATCAGTAATCGACAGAGCTCGTGCAATCGCAACATCATATTGCACCGATATGTCGAGGGAAAATTGAAATCGTTATCG
AAAATACGAGGCGATAGCACGCGCACGTTGTTTTCTTTGAATATTAGGAAAATATAATATGAATTTACCAGCGAAAATGGACGTGGAAAAGGATA
AGCTTCGCCAGATGCACTGCGAATTCAATCCCTTGTCGCGTTGCGACGGATCCGTGATGTACAGCCAGGGTATAGCCGTGTTTTCAACTCTAGTA
CATGGCCAGAACCGGCTAACATGGTCTTGCCAATTTCAGGTGCTACAGGTCTCATAGGCGCAGTTCTCGGCCCCATCGAGGTGAAGACCCAAAAC
CTGAGCATAGATGGCAGCTACTTGGAGTGTAACTACCGACCAAAAGCGGGCCTGCCGCAGGTTACCGATCGGATTCGGGAGGCGGCCATTCGGGA
TGTGCTGGAACTGGCCCTCCTGTCGGAGGCTCATCCGCGCTCCAAGATGTCCGTGCAGATCCAGGAGCTGGAAGATCGTGGCAGTGTATGTTTTT
GAATCTCCTTCATCTGTAATCCTTCTAACAATATATATATTCTATCAGATTGATGCCTGCGCCGTAAATTGCGCCTGCCTAGCCATGCTCAT
(SEQ ID NO: 709)

Exon: 5267..5195
Exon: 5098..5006
Exon: 4184..4015
Exon: 3953..3738
Exon: 3675..3165
Exon: 3102..3002
Exon: 2942..2826
Exon: 2757..2103
Exon: 2043..1325
Exon: 1261..1001
Start ATG: 5201 (Reverse strand: CAT)

Transcript No. : CT19806
ACTGCTTCTCCAATCAGTTTCTTGCTTTGCTCGTCCGGAATAAGTTCAGTAAAGAGTTCCAATAAGATGTCAGGCGCCAATCCCTTCGCCCAGTT
CGAGAAAACTTTCTCCCAGGCCGGCACAACATACAAGTACTTTGACCTCGCCTCCATCGATAGTAAATATGATCAACTGCCCTACTCGATCCGAG
TGCTCTTGGAGTCGGCGGTTCGCAACTGCGACAACTTCCATATCCTAGAGAAGGACGTGCAGAGCATCCTGGGATGGTCGCCCGCCCTCAAGCAG
GGATCCAACGATGTGGAGGTGTCCTTCAAGCCGGCCCGTGTCATCCTGCAGGACTTTACTGGAGTTCCTGCTGTGGTGGACTTTGCAGCTATGCG
CGATGCTGTTTTGGATCTGGGCGGCGACCCGGAGAAAATCAATCCCATCTGCCCCGCCGACTTGGTCATCGATCACTCGGTCCAGGTGGACTTCG
CCCGTGCGCCTGATGCTTTGGCCAAGAACCAGTCACTGGAATTTGAGCGCAACAAGGAGCGCTTCACCTTCCTGAAGTGGGGAGCCAAGGCCTTC
AACAACATGCTGATCGTGCCACCTGGCTCCGGTATTGTCCACCAGGTGAATCTGGAGTACTTGGCCCGCGTGGTGTTCGAGAATGACGCAACCGA
TGGCTCCAAGATTCTGTATCCCGACAGTGTGGTGGGCACTGATTCCCATACCACGATGATAAATGGATTGGGCGTACTTGGTTGGGGAGTGGGAG
GCATCGAAGCGGAAGCTGTGATGTTGGGCCAATCGATTTCCATGTTGTTGCCCGAGGTAATTGGCTACAAGTTGGAGGGCAAACTGAGCCCACTG
GTCACATCCACCGATCTGGTGCTGACCATTACCAAGCACCTGCGCCAGTTGGGTGTGGTGGGAAAGTTTGTGGAGTTTTACGGCCCGGGAGTTGC
GGAACTCAGCATTGCTGACAGGGCCACCATCAGCAATATGTGTCCCGAATACGGAGCCACCGTGGGATACTTCCCCATCGATGAGAATACTCTTG
GTTACATGAAGCAGACAAATCGGTCTGAAAAGAAGATCGACATCATTCGCCAGTATCTGAAGGCAACTCAGCAGCTGCGCAACTATGCTGATGCG
GCCCAAGATCCCAAGTTTACTCAGAGTATCACCTTGGATCTGTCGACGGTGGTCACCTCCGTTTCGGGACCCAAGCGTCCTCACGATCGCGTTTC
TGTCTCCGACATGCCTGAGGATTTTAAGTCGTGCCTGTCCAGCCCAGTGGGTTTCAAGGGATTCGCCATTGCTCCGGAAGCTCAATCCGCTTTTG
GGGAGTTCCAGTGGGATGATGGCAAGACCTACAAACTGCATCATGGATCTGTTGTCATTGCGGCCATCACATCCTGCACGAACACATCGAATCCT
TCGGTGATGCTGGGTGCCGGTCTGCTGGCCAAAAAGGCCGTTGAGAAGGGTCTGAGCATCCTGCCCTATATCAAGACCTCGCTGTCGCCTGGATC
CGGTGTGGTTACCTACTACCTGAAAGAGTCCGGAGTCATTCCCTATCTGGAGAAGTTGGGCTTCGATATTGTGGGCTATGGATGCATGACCTGCA
TTGGTAACTCCGGTCCTCTCGAGGAGAATGTGGTGAACACCATCGAGAAGAACGGCCTCGTGTGTGCTGGAGTTTTGTCCGGAAACCGAAACTTC
GAGGGTCGCATCCATCCCAACACCAGGGCCAACTATCTGGCCAGTCCTCTGTTGGTGATCGCATATGCCATCGCAGGACGCGTGGACATCGACTT
CGAGAAGGAACCTCTGGGAGTGGATGCCAATGGCAAGAATGTGTTCTTGCAGGACATCTGGCCAACGCGATCGGAGATACAGGAAGTGGAGAACA
AGCATGTAATCCCCGCCATGTTCCAGGAGGTGTACAGCAAAATTGAGCTGGGCTCCCAGGATTGGCAGACTCTGCAGGTGTCCGAGGGCAAGCTC
TTCTCCTGGAGTGCCGATTCCACCTACATTAAGCGACCACCCTTCTTCGAGGGCATGACCAGAGATCTTCCCAAGCTGCAGAGCATTCAGAAGGC
ACGTTGCCTGCTCTTCCTAGGCGATTCCGTCACCACGGATCACATCTCGCCGGCTGGATCTATTGCTAGAACCTCGCCTGCTGCCCGATTCTTGT
CCGAGCGGAACATCACACCCCGTGACTTCAACTCGTACGGATCGCGTCGTGGCAACGATGCCATCATGTCGCGCGGCACCTTCGCCAACATTCGG
TTGGTCAACAAACTGGTCGAAAAGACAGGACCCCGCACCGTGCACATTCCCAGCCAGGAAGAGCTGGATATCTTCGATGCCGCCGAGCGGTACCG
CGAGGAGGGTACTCCTCTGGTCCTCGTTGTAGGCAAGGACTACGGCAGCGGAAGCTCTCGGGATTGGGCCGCCAAGGGTCCCTTCCTGCTGGGCG
TCAAGGCGGTGATCGCGGAGTCCTACGAGCGCATTCATCGTTCCAACCTGGTGGGCATGGGCATCATTCCGCTGCAATTCCTGCCGGGACAGAGT
GCCGAGACATTGAACCTGACTGGCCGGGAGGTGTACAACATCGCCCTGCCAGAGAGCGGTTTAAAGCCGGGCCAGAAGATCCAAGTGGAGGCTGA
TGGCACCGTCTTTGAGACTATTCTGCGCTTCGACACTGAGGTGGACATCACCTACTACAAGAATGGTGGAATCCTCAACTACATGATTCGCAAAA
TGCTCTCTTAAGCAACTCATCTTATTTTGTTTTTATATATGTATATTCCACATGCATTTCTACACTGTAAATTGTAGTTCCCTAAGTTTTAAATT
GTGGTGGTGCTTCCCCAACCTGGTCAAACCAATAAAGTAAGCCCTTATTCTTGGTATCTAATTAAA
(SEQ ID NO: 710)

Start ATG: 67 (Reverse strand: CAT)

MSGANPFAQFEKTFSQAGTTYKYFDLASIDSKYDQLPYSIRVLLESAVRNCDNFHILEKDVQSILGWSPALKQGSNDVEVSFKPARVILQDFTGV
PAVVDFAAMRDAVLDLGGDPEKINPICPADLVIDHSVQVDFARAPDALAKNQSLEFERNKERFTFLKWGAKAFNNMLIVPPGSGIVHQVNLEYLA
RVVFENDATDGSKILYPDSVVGTDSHTTMINGLGVLGWGVGGIEAEAVMLGQSISMLLPEVIGYKLEGKLSPLVTSTDLVLTITKHLRQLGVVGK
FVEFYGPGVAELSIADRATISNMCPEYGATVGYFPIDENTLGYMKQTNRSEKKIDIIRQYLKATQQLRNYADAAQDPKFTQSITLDLSTVVTSVS
GPKRPHDRVSVSDMPEDFKSCLSSPVGFKGFAIAPEAQSAFGEFQWDDGKTYKLHHGSVVIAAITSCTNTSNPSVMLGAGLLAKKAVEKGLSILP
YIKTSLSPGSGVVTYYLKESGVIPYLEKLGFDIVGYGCMTCIGNSGPLEENVVNTIEKNGLVCAGVLSGNRNFEGRIHPNTRANYLASPLLVIAY
AIAGRVDIDFEKEPLGVDANGKNVFLQDIWPTRSEIQEVENKHVIPAMFQEVYSKIELGSQDWQTLQVSEGKLFSWSADSTYIKRPPFFEGMTRD

FIGURE SHEET 385

LPKLQSIQKARCLLFLGDSVTTDHISPAGSIARTSPAARFLSERNITPRDFNSYGSRRGNDAIMSRGTFANIRLVNKLVEKTGPRTVHIPSQEEL
DIFDAAERYREEGTPLVLVVGKDYGSGSSRDWAAKGPFLLGVKAVIAESYERIHRSNLVGMGIIPLQFLPGQSAETLNLTGREVYNIALPESGLK
PGQKIQVEADGTVFETILRFDTEVDITYYKNGGILNYMIRKMLS*
(SEQ ID NO: 711)

Name: RNA-binding protein
Classification: RNA_binding
Gene Symbol: Irp-1B
FlyBase ID: FBgn0024957

Celera Sequence No. : 142000013384287
CTTTTCCATTACCTCGATGATCGTTAGTTGGTTCGGTTCATCCGGTCGCGTGGGCAACGTATTGGTCAACTATCGAGCCGTGGCCCACGAGGACA
AGTCCTTCGCCCAGGGGCTGGCGCTGATGATGATTAGCCTTCTGGCCCTCATACCGGGACCCATCATATTCGGCCGCCTCATCGACTCCACGTGC
CTGGTGTGGACAAAGACCTGCAATGGCAATGGCAACTGTCAGTTGTACGACCAGACCCGTTTCCGTTACTCCCTCAACTTTTTATCCTGCCGTAA
GTTTGATTCAAAATATGTAATAAGATAACATATTCTCTACCTTCTTGCTAACTTCCAGTGCTCACCTTTATGGGACTCCTCTTCGATTACCTCGT
TTGGTACTACGGACGCAACCTGGACATTTATGGCGACAAGGAGGCCAAGGAGGAGGAGCGTGCCAACAGAAAAGACCAGCCCATTACTCCGCTCC
TGGCCAAGAAATCCGAACAGGAGTAAAATCAACAAAAAAAAGAAAGTGCAACCCATCCGTGATACTCAATTATAAGGAGTAGATTCATATGAAAC
ACGCCAGTTCCGAGTATTTCATAACAATAATTCAAAGCACATTCCTAGAGTTAGTTTTTGAAATCAAAATAGAGAAAGATTGGGCAAAGCCTGTA
CTCCAACGCCATATGTACAAATCTTCCGCTTTTCGATAGGAATTTAGCTATTGAACTCGCGCTGTCAAATGTCTTCTTTCAGTGTACAATTGTTA
ATTACTTTTACTTTGTGCTAAGATCAATTAAATATACCATGCTTAGTTTAACAACAAAAATGAAAAGAATTTATGTGTACGTATGTATAAAAAAA
AATGTTTCAAATAAAAATGTATGTTTATTAAAATATTATGAGGAGTCTAAATCATAAATATTTATATTTTATATATATTAATTTTGCCAAAATAT
TCGATTGCAATCCATAAAACCAGAATATAATTTCTTAGGTTTCATTTTTTTTTTTTTTTGAAATTTTCTTTTCACTTTTATTGATAAAAAATGT
TCAAATTTATGCAGATCGTTTGTTTTTCATTCCATACGTATATGTATAATAATAATACACTTTAATTTCGATTTTTGTATAAATATTCATTCCCG
TTTGTCTATATAATTTCTATTATTACGATCGCTCTTATTCCTCAGTGGCGTAGTTTTCGACTTCCGTTCCGATTTCGCGAGTGATTTGTTGCTTG
AGTGTCAGTGTTGGGTGTCTGTGTGAAACATTTTGAATGAATTTCCGCGTTGTCAACAATTATATCGCACTCAGTATTATTACAATAATAATTAA
TTAATTAATTATCATTCGCGTTCGATTCGTAGGAGGCTGCGAGAAGCGTTAAAAGCTGGCTTAAGTCCTTCATTTACTAGGTCCGCAATGTAAGT
ATTAATCAGTTAATTAAATTAACTTAGACTTCAGGGGACTGCTCAACGTGCTTAATTGATATTATTTTATTTACTTGCGTCTGTTACGGCAACAA
CATTCAATTTAACAAAAACTGAATTTTCGACAATGGCAGAGGGGAAGACAGATTTTAAAAAATGGCTATGTGAATATTTTGAAACCGCCTTGGTC
CGGAATTTGAATGAGTGAATAGCGTATATAAACAATAAAGGGGTAAACTTAAATAAAAAGCTTTACTAGTTTGTGTTTTTGTTTCTGCTCGGTAG
CAAAAGGCATTTTATTTTTTCATATATGGGATTTCGTGTTCAACTCGCACGAATTCTTCAATTAACTAAATTATACAAAATCAAATGTGTTTTAA
GTAGCAAAATCAAATGGTTTTAAATGATTAACAATTAGGTGTTTCCGTAAATTTGAATTTTCTCCGTTCTGCTTTTACAGACTTTACTCCATGTT
CTTTAAGCTTAAACTTAAATTAAAGCATATAGATTATATCATTTAAAAAGAAGAGCAGAAATATCTTAATGCATTTTGCAGGGTATTTAACAAAT
TTGCAATTTAAAGGCGCATACAGGAAGATGGATGGGGAAAGGATTCTCGGGATCGTACTTTCGCTTACAAATACAAAAATTGGGTAGCTTGCAGC
TTTAGTTTTAGTATTTTAAAGAAATTCACGTATTGCGCGCGATTTAGGCATGTACGTGTAGGCTATTTAATGCTTACAGTTTATACAAAATAGTA
AACCAAAAGAAAACGACGACTGCGACAAGTGCTCAATATCCTTGCGAGATGGGCTCAACAAACAAAATCGTTATCAATGCAACTCCTCTTCTTCA
ACTCTTTCTCTCTCTTTGCATATATACGTGTGAGTTGTTTGTTTTGTATACATATATAAATAGTTCATCTTGTTTCGCATTCGCTGCCTCCGATT
TTGCTGCTTAGTTTACATAATATAGTTTATAATTCGTATATAATGCATTTCTGTTTCTATCTCCGAACTCGTCCTTGTTGTAAATTAACTTTTC
GCCTGCCTACATTGCCGTTCCGTTCCGTTTTGAATCGATCTGGATTCTATAATCGATTGCTATTGCTGGTTGAAAGTAATGTGAGTGAGAGCTCG
AGCGATGCTGAGTACTGTTTTTGTTGATTTGTCAAATGTGAAGAAAGCGTGGCGTGGCGTTGCTGTTGTTGTGGCTGTGGCTGTGTTCTCTCGTC
GGGCTTGCAATGCTATCTCAAAAATCGCAATGAAAGGCGGGCGCTCGAATTTAGCTAGGCTCAATTTATTCGACCACCTTCAGCACCTTGCCAAT
GGCAATGGTTTTGTCTGAAAGATAGAAATGATAATTAGACGGGGATCTCCCGAGTCACCAATCGACTTACTTTCATCTCTGAGCGTAAAACGGCC
CATTTGAGGGAATAGCTTAAATTGTTCAAGGCAAATCATTCCGGAGCACTCGATTCGCATAATTGCAACCTGATCCTGCTTAACGAACCGTGGAC
GTGTTTTTGATTTGTCACCAGACTTTTTGTCGACCAAACAGATGAGGGCCTATTGAAAAATAATACATATTCAGTATCTGGCTAATGTATGGGAA
TTATAGACCTAAAACTTACCTTAACTGTGACTTCTTCGGCTGCACAGTGTATGTGCATGACAGCCGAGTAACCCGCACAGATAATTGATTTGTGT
TCTAAAATTACGACCTGAGCATCAAAGATTTTTCCCGTCTTGATGGGATTGGCTGCATCGCAGAGAACAAAACCGGGCGAGACATCCTCCTCCTC
AATACCCTAAAAAAAAGTTTAAGAATCAATTAAAATAATCCAAGGGTATAACAAAAGAATCATGTACTCACTTTCAGCTTAATCTTGACGTTCTC
GCCGGGACCAACAGAAGTGACTTCAAAGTCGTCCGAGAACAACTGATCCACCGCCACTTGCGTCTATGTGAAAAACAAGCTTAGTTTCAAATATT
CAGCTGATTGCAAAGTGTATAAACTTACCCTATTTGGCATCACTAACAGGTTTTGACCCTTGCGCGCTGTTCCGGACTCAACCTTGCCCATCACC
ACGGTGCCCATATCCTTGTACTTGTCCACAATTGGCATGATGAAAGGCCCGTCCGACTTGCGGTTGAGCGAGGGCAGCTCGTCAATGAACGGAAT
GAAGGCGGGTCCCCGGTACCAGGGGCAGAGCGTCTCCGGGATTTGGTCTTTCAGCCCGTATCCGCTGAGGCCCGAGCAAGGCATAAAGGTAAGGT
CCTTGGCCGGGTTGAAGCCCAGCTTCTTGAGGTATGGTAGTATCTTGTCTTTGCATTCGTTGTAGCGCGTCTGATCCCAATTGACCGTTGGGTCA
TCCATTTTGTTGACCAGCACGACCAGATGCTTAACGCCGGCGGTCTTGGCCAACATGGCATGTTCTCGGGTCTGGCCGCCGCGATCGAAGCCCGT
CTCGAATTCACCCTTTCGCGCCGAGATGACCAGCACTGCGAGATCGGCCTGCGCCGCGCCACCGATCATGTTAGGCACGAAGCTCTTGTGACCGG
GTGCGTCGAGGATAGTGAAATGCTTTCGGTCCGTTTCGAAGAAGGCTCGTCCCACCTCGACGGTCTTGCCCTTGTCGCGTTCCTCCTGGTTGGTG
TCCAGCGCCCAGGACAAGTACCAACTCTCACGCGACTTCTCACGTGCCTCCCGCTCGTACTTCTCCAGTGTTCGCTTGTCCACCATGCCCGTGAG
CGACATGATCTGTCCGCCAATTGTTGATTTGCCAGCATCTACCCAAAGCAAAGTGCGAATGTTAATAATGGCTTTTGGTGGGACATATGTTTATA
AGTAATGATAACTCACCAACATGGCCAATGAACACAACATTCACGTGCTCACGCTTGCTCCTATTTTCCTCCACCTTAACCACCTTCTTCTTGGA
CACCTTCGGCGTGGCCTCGCCCTCCGTGAACTCAGCATCTTCCACCTCCTCATCCTCGGGCGTGATCACTGCATCGTCCACATCCCAGCTGTCAG
CAGGATCGGTTTCTAAGCAAATAAAAAAAAACCAAATAAAAGGTCATTAGTCGAGACATTTACAAGGCGATTCTACTGTGCTTGGTGGTGAAAAT
AATATGGCTTGTTGAGGAATATATAATTGTTTGTTGTTTATTTTCTATCGATTACTAAAATTGTTATCGCGCAAATATATAATTTATTTACATTA
GACAATCTTGGGAAAACTAGTAATTTTAAAAATTGTTCAAAATAGTGTCGGTTTGTCCAGATCAATCCAGTTAAAAACCGAATAAAGCAATGAAT
TTTTTTTATTTTTGGAATTGTCCACATCATCGTAATAGTTTAAAGAAACTTTAGTGATGGGAGTAAAATTCACTTTAACTTTCTCTATTTCACAA
TATCGAAACCTTTGTATTTTGAGCGACATTTAGTAAATGCAAACATGTCTCTTTTTATGCACAAAAATAAAAATGCAAATGTCATGCCTTTTATT
TTTGCACATGAAACAACTGTGTAAATAGTTTCTTTTTAATTTAGGTCGGTTTGTTAGAAACTTATAGCACTTCAGATGATTTAAACTCAGGGAAG
TTGAGCTATCACTTCACCAATTATATACTTCGTACTACCACTCATGCACTCGCCGTGTTTGACCTGGCGGCCACATGCTAATTGCTAATCGCTGA
CTCTAGCCACCCGGGCGGATGAGTCATGTGCGGGATTGGATTGGTGGAGTGCTGTTCTGTGCTGGTGTCAACGTGCTTGGTTAATAGTAGTTCCC
GAACCTTTGACGTAAATGTCGGAGGATCATTTGACCGTCTGGAGATGGGCTGTAACGAATGGTATCCCAACTCCACGATTACTAACTTTTTCTCC
ACTGCGAAAACGAGTAAATGTAGCGAGATCCGGCGCCCTTACTCATGATTCCGATGCATACAACTCAATTCTAATCGGATTTCGGAACTAGGAGC
GGATGTAGATATAGCCGGAGAAACGAGCTTCGATCGCGCCAAAGTGTAAGAGCCAACAGCAAATGCTATTTTTTTTCGGCGCTTTGGCAAGCGCG
CCGCACAGCCAAACGCCATGTAATCAAGTTCGAAGCGGTTTCAACCGCCGGCGAGCTGCACTAAGCGCTTCCATTCGGCCAAGCAACTACAAAA GTCGCCACATTGGAGTCGCTGCGATAACGACGAGTGAGCCATTCCCATTCCCATGCCCATTCCATTCCAGTCCACACCGCCAGTCGAAGCTGGGC
GCAGCGTAGGCTCCAATGAATGGCTGACAAAAGAGTAAACGTGTCCAAAACACAAGAATTGGGGGGCAAGCATTTGCGAGTGTGGGTGCGGAAGA
AGGGGACAAGGCAATGGCCAAATAAACGACACCACAAAGCGAAGCGGCAGTAAAATGGCAGCACAAACAGCTGCTTGTCAACGTCGCCCGGCGAA
TGGCAAGTAGGTGAGTGGCCACCAGAGATGCGCCGTGATTGTTAACAGTTTAACAAGTGACAGTGATAAGTCGTTACATCGAGAAATCAACAAAG
CTAAACAAGAAAGTGTTTTCTAACTATGAAATTTTCAGAATATTAAAATTATGAACAAGTTTATAGAATTGAAAAATACACAAGGCTAGAATATT
TATATTAGCATATTCGTGTAAAATTTTCATGGCTTAACTCTTAAATATCCCAATTCTTGAAACTCAAAATACTGAACGACGATTAAGAATATAAG
AATACTATTCGGACGAAAGTTTTCACAAATCCCAAATCCCAAGATCACAGCGAGGCGTGGATTGTTTGATGTTCATGTACATATAGATTCAACAA
GTATTTTTAAATGTATGTACCTACATTTGTTTAAAGCAAAAATGTCAAAGTGCATGATTAATTCCCAACCATTAGCTGGTTTCTAGAAAACAACT
AGACCTGATTTGCGGTTATTTCACCATTTGGTGACACCTCTGTAGTGATTCTGGTCGTGATTCCTGGGCATCTCTGCGCTGAGCCACTGCTGGCG
ACACGACGACGAGAAAAGCGGCCAAAGAAAGGGCCCTGGCCGGACGAACTGTTTTGCGCGCAGGCCGAAAGCGATTAGCCATTTGTTTAGCGGC
ACAATAATGCCCGCAATTCGAATAGAAGTCAAGCAACACATGCGACGCCGACGTCGGCAGTGCTGACGCAGATTGAGGTTATGTACTAGGGCCAG
CGATAATAACCTAAACGGAACCTGGTGAATGCAACCTATCTTTGGGGTTTTCCCTATCCCATTCCCCATTGTTGTGTCTCTGCCAACGGTCTTGC
GACCAGCAGGTAGCAACAATAACACGCTTCTTTGTTGACGTCACAGAAGAAGCGAGTTCAATGGACGTGGGGCATGTGTATTTGGCAGGGGGTAT
TTAGGTAGCTAGCAAGCTCTATTTACCATTGTTTGCGATTTTGTCCGAGGGGTTGAGACCATCGATGGGCGTTGGATCCGCCGCCGCTGCTCCTG
CTGAAGGCGTGGTGGCTGGCGAACCCGGCGCTGGCGATGCGGAATTGGAGGATGATGTGGGCGGCTGTGCTGAGGGTGCTGCTGCCCCCGCCCCC
TGTGCAGTTGGAGGCGGTGGAGCTGCTCCCGCTGTGGATCCCCCGCTGCCGACGGAATCGGGTGTGGTGGCTGGCGTGGCTGAACCGGAGGCGGG
ACCCGGATCCGCCGTCTCCTCGGCCGCAGCCGCTGCAACCACTACTGCCGCCGCCTCCTCAGCTACATTCACAACGCTGTTGTAACTGAAACTGG
GCACAAATTCTACCGCGTTCACGTTCAGCGTTGAGAACTTTGTGCTGATCTCCGTGTTTTCCTGGGCGGCCATCGTTGCAGTGCGTCCGTAATCC
TCCGCAGTGGTTTCCTCCGATGAAAATCTCTCTCTCGCTTTTTTCACGCGACGACACACTTTCGCCCTCCTTCTACAAACTGCTTCAGCTGCTTC
TTCTTGCTGCTCCCGCACTCACACAGAACACACGCGGTCGTTCGGAATTCTTGGGATTGCCTATGGTAATGGAAATTGGGAATGGCAAAAGCAAT
GCCACCAACACACGCACGCCTTGATGGTTGTTGGCCGGGGGGGTGGCTTGTGGGGGGTTAGGCCAGACTTTCGGCTCAATGTGGTCTACACTTT
TGTTGTGACTCGGTGTTGTGTTTGTTGTTTGTGCTTTGCTAGCCTGGCCAACTCGGGTTGAACTCGAATTCCCTTTAATTTGATCGACTATCGCC
TGTTTGGGGCAGTGGTGACCACCTGGTGATCTGCAGGTATGATTCGACTACCTGAACACTAAATGCAGTGCTCGGAACTAGCAATCTTCTATTAT
TTTACACGTTTTAAGCCACGCATCAAGTCAGGGTTGCCACTTGTATGCGGTGTTATCGGTGCATCGATATGTGCTGGCTGTCACAGTGGCCTATA
ATTGATTTGGGGCAAAGTATTAAGATATTTTTAAATTTTTTTAGTAAGATTTTTAATACTTTTAAAATTATTCAACATAAATAATTATATTGCTT
TTGTACTTTGTTCTGATTAATATAATTTTTTAAGGCTAAATATAACGTAGTCCACATGTACATATATAAATACAAACTGTATTTGTTTTATGTGT
GACTAGACATTAATAATTTTTTATTCACTTTCAGTGAGTTTTTATAATTATTAATTTAGTTATTTTGTATAATAGAAGTGTAATGCGAGTTTTGT
AAATATTGATAAGTGTGTAGTGAGCCTTGGGGTTTCAATACATTTCTAAGCTCATCATCAATGGTATCGAATTACAATCGATGTTGTTCCAGCTC
TAACGTCGTGCCAGACGCCATTTTAACAGTAGTGAAAAAAATCGTCTGGAGTTTGGCTCGTTTTCAGCATTCGCATTAGCATTTTAGCGGTAAAAC
AAATATCCAAATAGACAATGAGCAACGGTGGTGGTGCCGGGGGATTGGGCGCAGCGCGTCCACCTCCACGGATCGATGGAATGGTCTCGCTTAAG
GCAAGTATCTGCTAAGTAAAATGCGACTAAATCGCCCACAAAATGGCGGCCGGCTGGCAACGTTGTGTGGTTAGGTAACCTCTCCAAAAGCATGT
AAATTAATCCGCGTGTAATTATGCCTACAGGTCGACAATCTCACATATCGCACCACGCCGGAGGATCTGCGTCGGGTCTTCGAGCGGTGCGGCGA
GGTGGGGGACATCTACATACCCAGGGATCGCTACACACGTGAGAGCCGCGGATTCGCATTTGTTCGGTAAGCATTCACTTCTCTTCCGGGAAAAT
TGTGAAAGTCTTAGGTCTTTTTTGTTTTGTTACTTTCACTTGCCGGCGGTGGATTTTAATTATCATGGGACCTAAAATGTA
(SEQ ID NO: 712)

Exon: 7821..6867
Exon: 4477..4292
Exon: 4218..3449
Exon: 3388..3302
Exon: 3236..3060
Exon: 2994..2826
Exon: 2769..1697
Exon: 1007..1001
Start ATG: 7293 (Reverse strand: CAT)

Transcript No. : CT19890
CTGACTTGATGCGTGGCTTAAAACGTGTAAAATAATAGAAGATTGCTAGTTCCGAGCACTGCATTTAGTGTTCAGGTAGTCGAATCATACCTGCA
GATCACCAGGTGGTCACCACTGCCCCAAACAGGCGATAGTCGATCAAATTAAAGGGAATTCGAGTTCAACCCGAGTTGGCCAGGCTAGCAAAGCA
CAAACAACAAACACAACACCGAGTCACAACAAAAGTGTAGACCACATTGAGCCGAAAGTCTGGCCTAACCCCCCACAAGCCACCCCCCCGGCCA
ACAACCATCAAGGCGTGCGTGTGTTGGTGGCATTGCTTTTGCCATTCCCAATTTCCATTACCATAGGCAATCCCAAGAATTCCGAACGACCGCGT
GTGTTCTGTGTGAGTGCGGGAGCAGCAAGAAGAAGCAGCTGAAGCAGTTTGTAGAAGGAGGGCGAAAGTGTGTCGTCGCGTGAAAAAAGCGAGAG
AGAGATTTTCATCGGAGGAAACCACTGCGGAGGATTACGGACGCACTGCAACGATGGCCGCCCAGGAAAACACGGAGATCAGCACAAAGTTCTCA
ACGCTGAACGTGAACGCGGTAGAATTTGTGCCCAGTTTCAGTTACAACAGCGTTGTGAATGTAGCTGAGGAGGCGGCGGCAGTAGTGGTTGCAGC
GGCTGCGGCCGAGGAGACGGCGGATCCGGGTCCCGCCTCCGGTTCAGCCACGCCAGCCACCACACCCGATTCCGTCGGCAGCGGGGGATCCACAG
CGGGAGCAGCTCCACCGCCTCCAACTGCACAGGGGGCGGGGGCAGCAGCACCCTCAGCACAGCCGCCCACATCATCCTCCAATTCCGCATCGCCA
GCGCCGGGTTCGCCAGCCACCACGCCTTCAGCAGGAGCAGCGGCGGCGGATCCAACGCCCATCGATGGTCTCAACCCCTCGGACAAAATCGCAAA
CAATGAAACCGATCCTGCTGACAGCTGGGATGTGGACGATGCAGTGATCACGCCCGAGGATGAGGAGGTGGAAGATGCTGAGTTCACGGAGGGCG
AGGCCACGCCGAAGGTGTCCAAGAAGAAGGTGGTTAAGGTGGAGGAAAATAGGAGCAAGCGTGAGCACGTGAATGTTGTGTGTTCATTGGCCATGTT
GATGCTGGCAAATCAACAATTGGCGGACAGATCATGTCGCTCACGGGCATGGTGGACAAGCGAACACTGGAGAAGTACGAGCGGGAGGCACGTGA
GAAGTCGCGTGAGAGTTGGTACTTGTCCTGGGCGCTGGACACCAACCAGGAGGAACGCGACAAGGGCAAGACCGTCGAGGTGGGACGAGCCTTCT
TCGAAACGGACCGAAAGCATTTCACTATCCTCGACGCACCCGGTCACAAGAGCTTCGTGCCTAACATGATCGGTGGCGCGGCGCAGGCCGATCTC
GCAGTGCTGGTCATCTCGGCGCGAAAGGGTGAATTCGAGACGGGCTTCGATCGCGGCGGCCAGACCCGAGAACATGCCCATGTTGGCCAAGACCGC
CGGCGTTAAGCATCTGGTCGTGCTGGTCAACAAAATGGATGACCCAACGGTCAATTGGGATCAGACGCGCTACAACGAATGCAAAGACAAGATAC
TACCATACCTCAAGAAGCTGGGCTTCAACCCGGCCAAGGACCTTACCTTTATGCCTTGCTCGGGCCTCAGCGGATACGGGCTGAAAGACCAAATC
CCGGAGACGCTCTGCCCCTGGTACCGGGGACCCGCCTTCATTCCGTTCATTGACGAGCTGCCCTCGCTCAACCGCAAGTCGGACGGGCCTTTCAT
CATGCCAATTGTGGACAAGTACAAGGATATGGGCACCGTGGTGATGGGCAAGGTTGAGTCCGGAACAGCGCGCAAGGGTCAAAACCTGTTAGTGA
TGCCAAATAGGACGCAAGTGGCGGTGGATCAGTTGTTCTCGGACGACTTTGAAGTCACTTCTGTTGGTCCCGGCGAGAACGTCAAGATTAAGCTG
AAAGGTATTGAGGAGGAGGATGTCTCGCCCGGTTTTGTTCTCTGCGATGCAGCCAATCCCATCAAGACGGAAAAATCTTTGATGCTCAGGTCGT
AATTTTAGAACACAAATCAATTATCTGTGCGGGTTACTCGGCTGTCATGCACATACACTGTGCAGCCGAAGAAGTCACAGTTAAGGCCCTCATCT
GTTTGGTCGACAAAAAGTCTGGTGACAAATCAAAAACACGTCCACGGTTCGTTAAGCAGGATCAGGTTGCAATTATGCGAATCGAGTGCTCCGGA ATGATTTGCCTTGAACAATTTAAGCTATTCCCTCAAATGGGCCGTTTTACGCTCAGAGATGAAAACAAAACCATTGCCATTGGCAAGGTGCTGAA
GGTGGTCGAATAAATTGAGCCTAGCTAAATTCGAGCGCCCGCCTTTCATTGCGATTTTTGAGATAGCATTGCAAGCCCGACGAGAGAACACAGCC
ACAGCCACAACAACAGCAACGCCACGCCACGCTTTCTTCACATTTGACAAATCAACAAAAACAGTACTCAGCATCGCTCGAGCTCTCACTCACAT
TACTTTCAACCAGCAATAGCAATCGATTATAGAATCCAGATCGATTCAAAACGGAACGGAACGGCAATGTAGGCAGGCGAAAAGTTAATTTACAA
CAAGGACGAGTTCGGAGATAGAAACAGAAATGCATTATATACGAATTATAAACTATATTATGTAAAACTAAGCAGCAAAATCGGAGGCAGCGAAT
GCGAAACAAGATGAACTATTTATATATGTATACAAAACAAACAACTCACACGTATATATGCAAAGAGAGAGAAAGAGTTGAAGAAGAGGAGTTGC
ATTGATAACGATTTTGTTGTTGAGCCCATCTCGCAAGGATATTGAGCACTTGTCGCAGTCGTCGTTTTCTTTTGGTTTACTATTTTGTATAAAC
TGTAAGCATTAAATAGCCTACACGTACATGCCTAAATCGCGCGCAATACGTGAATTTCTTTAAAATACTAAAACTAAAGCTGCAAGCTACCCAAT
TTTTGTATTTGTAAGCGAAAGTACGATCCCGAGAATCCTTTCCCCATCCATCTTCCTGTATGCGCCTTTAAATTGCAAATTTGTTAAATACCCTG
CAAAATGCATTAAGATATTTCTGCTCTTCTTTTTAAATGATATAATCTATATGCTTTAATTTAAGTTTAAGCTTAAAGAACATGGAGTAAAGTCT
GTAAAAGCAGAACGGAGAAAATTCAAATTTACGGAAACACCTAATTGTTAATCATTTAAAACCATTTGATTTTGCTACTTAAAACACATTTGATT
TTGTATAATTTAGTTAATTGAAGAATTCGTGCGAGTTGAACACGAAATCCCATATATGAAAAAATAAAATGCCTTTTGCTACCGAGCAGAAAAAA
AAAA
(SEQ ID NO: 713)

Start ATG: 529 (Reverse strand: CAT)

MAAQENTEISTKFSTLNVNAVEFVPSFSYNSVVNVAEEAAAVVVAAAAAEETADPGPASGSATPATTPDSVGSGGSTAGAAPPPPTAQGAGAAAP
SAQPPTSSSNSASPAPGSPATTPSAGAAAADPTPIDGLNPSDKIANNETDPADSWDVDDAVITPEDEEVEDAEFTEGEATPKVSKKKVVKVEENR
SKREHVNVVFIGHVDAGKSTIGGQIMSLTGMVDKRTLEKYEREAREKSRESWYLSWALDTNQEERDKGKTVEVGRAFFETDRKHFTILDAPGHKS
FVPNMIGGAAQADLAVLVISARKGEFETGFDRGGQTREHAMLAKTAGVKHLVVLVNKMDDPTVNWDQTRYNECKDKILPYLKKLGFNPAKDLTFM
PCSGLSGYGLKDQIPETLCPWYRGPAFIPFIDELPSLNRKSDGPFIMPIVDKYKDMGTVVMGKVESGTARKGQNLLVMPNRTQVAVDQLFSDDFE
VTSVGPGENVKIKLKGIEEEDVSPGFVLCDAANPIKTGKIFDAQVVILEHKSIICAGYSAVMHIHCAAEEVTVKALICLVDKKSGDKSKTRPRFV
KQDQVAIMRIECSGMICLEQFKLFPQMGRFTLRDENKTIAIGKVLKVVE*
(SEQ ID NO: 714)

Name: eRF-3
Classification: translation_factor
Gene Symbol: Elf
FlyBase ID: FBgn0020443

Celera Sequence No. : 142000013384669
AGCTAGCTCCGTTGGGCTCCATGCTGCAGTACATACTGGATCATGGTCATGAGATCACGGCCAATGCGGAGCTGAAAGTTTGGGCGTCACAGATT
GCGTGTGGTAAGTCAAATTCAAGACAATTTGATTCAATTCAATTAATTAATTAATGTTTGTACCAGGCATGCATTATCTGGAATCACAGCATTTT
GTACACCGCGATCTGGCCGCCAGAAATATATTGCTGACCGCACGCCACCAGGCGAAGATCAGTGACTTCGGCATGTCGCGATCACTGAGACCCGG
TAGCACGGAATACCAATTCACCCAGGGCGGACGTTGGCCCATCCGCTGGTACGCACCGGAAAGCTTCAACCTGGGCATCTTCTCGCACGCCAGTG
ATGTGTGGTCCTTTGGCGTGACCATCTGGGAGATGTTTTCCCTCGGCGCACCGCCATATGGGGAAATATCTAATGTCGATGCCATCAAGTTGGTG
GACAGTGGCGAACGCCTGCCGCAGCCCAATCTCTGTCCAGCTTACATCTATGCCGTGATGCAGAGCTGCTGGAAGGAACGACCCAAAGATCGGCC
AACCTTTGTCTATCTCACCGAGTTTTTCGCCCGCGATCCTGATTACCAAAACCTGCCGGAATTGGTGCAAACGGTTCACATTTAAGCCAGTTTCC
ATTTTCCATTTTTTCCGTTCTGAGTGCAATTTTCTGTAGCTATTTATGCAATGTCTTCTATTTCGTTTTCAACGTATTAACGATCTGGAACCCAC
AGATCACTATTGTTGTTCCGTATCCTAGTATTCATGTTTATAGCTTGTAATATATTTTTTAATCATATGTACAACCAATTTGTGTCAAAAGAAAG
CGAACAAGTGCCTTAAAGATTTAGCATATAAGCTTTGTATTCATTTTTACAAATCCATTTTGTTTCATTGGTTATACAAAATAAAAACTATTTTT
ATACATACTGCGCTTTTTGATTTAGTATTAAATAATACAGCAGTATGCTTTAATAATCAATGTTTAAACATTTAATGCAGTTCTTTTATATAAAA
CGTGGTAACAAAAGTAAATAGTTTGTTGGTAAACCGCTTAAATACTAGGTTAGTAATATGGTTTCTTGGAAAGATTATAACTACGTTAGCGTGGT
TAGTGCTCTAGAAATGGATTATATATTTTTTTGTTAATTTTTTCGAGCTAGCACAACAGTAATCAAGCTGATCCGTTTATTGCCTGCTTCACATT
CGATGCGCTGACGAGCTTAAGGGCGCCAAGTATTCCGTTCAGGTTCTCCTCGTTGTAGGGCTTGCCCTGGAGCGGAGTCACCACCGGGACGAGCT
GATCGCTCTGCGGCAGCTGGATGCCGATCTCCTTCATTAATCCCTACAAATTTAGTAAAATCATAAGTGATAATTCTCTAAAACAGGGCAAAACA
AATCTTACCGCTTCCACTTCCACGCTTAGTTTCAGTTTCATGTCCTGCTCATCGCCCTTCACCTCCAGTTCCTTCTGCACGGTGAACTTGGGAGT
CTTGCCGATGACCCAGTCCCAAGAGCTGTAGTTGGAGCGCAATTCCTCAATGCCGGGGAACCATTTCTCTGTGGGATTGACCAGCTGAAAGCCGC
GCTGCTGCATCGTCTGTGTGCTGCCGCCGTCTTCAAGCGTAGTTGCAGCCGTTCTCAAATACTCGTAACCCACGGCGGAACGCAGCTGAGCAACG
TTCACCGTGCGATTGACATCAACCAGGTTGCGAATGGGCGACGGCACCGAAGCCGTGGCCTTGCTAATATAATTGGCCGGCTCCCGCACCAGAGA
TTCGCCCAAGTGCAATTTGTTGGCGCTGGCCAAAATGGTGCAGTGATGGTACGAGTTCGGGTGTCCCAGCTTGGCCGCAGTGCCGGAAATCTGTA
ATTGAACAAGGGCATACTCGTTGAGTGGGCAAATAAAGACCAGATGCACAGCCCCAGCTGTTGGTTAAGTGAGCTGATGCCAATGTGAGGGATCA
GCCGGGGTCGCATCATTCCTTGATAAGAGCCACCGCTCCTCCTCACCTTCTTATTCATCACTACAATGTCGTCGCGCTCATTTATCTCTGCCTTG
ATGGCCCATTCGCGGAACAAGGCCCTGGTCACGATGTTCAGGTTGTACTTGCGATCGTAGCGCTCTCTGGGCGAGAAAAAGGTGCAGTTGAGGTT
CCCAAGATCATGGTACACCGCTCCACCGCCACTATTGCGGCGTGCAAGTGTTATGCCGCGTTCCACCAGCTGCGAAACATTAGCCTCGGTGAAGG
GATTCTGGTGGCGACCAATGACTACGCACGGGTCGTTGGCCCACAGCAGCAGCACATGGTGGCGGCTGAAATCAAAGTTTTTGTACAGCCAATCC
TCTAGAGCGAGGTTGGTGAACACATCGCTGGACTGCGAGATGAACACGGACTTCTTGATCTCCGAATCGGGAACCACGGGCGGTGGCTGGCGCCT
CTGCTTTTTAATCTCCTGCTGTCCAGCAGATGGTGGCTCCACTCCGCTGGATGCCAGGCGCGTGGCCTGAGCGGCGGAGGAGAGAAGTAGCCGCA
GCTGGCTGGAATTGCGTCGCAACAGCATGCTCATGGCTTACACAAGGAAGTGGGGCGTACGGGTGTGTGTGATTTCTGTTGCCAGGTGATCTGGG
ACACAATGCACTTGCAAGCGAAACAAGGTCAATGGTGTCGAAAAAAGCTTTTGGCTGGTTGATTGGTTGGTTGGTTGGTTGGTTTCTACGGTTGT
CGTCTGCCTGGTTCTGTGTGGTCCGTGTGTGCTCTTCTTTAGGTTATGTATGGTCTACTATCTACGCTATTCGTTTTGGTCTTTAAATGGCTTTG
GTCGCTCTGGACTTTAGACTGTGGCGTTCTTAGTGGCTCGGGATGTGTTTGCAGCCACGGAGCTGGCCGAGATGAGGTATTCGTGCAGGGCGGGC
GTCTGATGCAGCCACTTCCACGTTTGATGCAGACCACAGACACGCTTACGGAGACCCAGGCAGTCCTTGTTGGCACAGTTCACTGGCATACTACG
CCTCACACCCATCCAGGTGGGGATACAACGAATCCGGTGTTTACGGGGGGCCGCAACGTTACGGGGCCCAAATAAGATGGCTAAAGGGTTTCCT
TTTTAGCTGACACCAAAATTTTCCACTCTTTGTTCGCGGCGCACGGGAACTGCGGGGGGCGGGGGCAAGGCGGATGATCGCAGTGGGCGGGGGTA
GCAGTTATAGCACAAACAAACGAACGAACACAGAGCCGATCGAAAAGCAGCTGCGCGTGTGGAAATATCACGACCGATTGGCTTTCGTTTCAGAT
GAGCAGTGGTGCTCGCTGCTCTTGTTCTTCCTCGACGGTCCCCAAATGCCATTCGCAGCGAACGACGAAAGCTCCGGTCATTAAAAAAAAAAAAA
AACAACGGCACTCTGGCGCCGCACTTAATTTATTTTCATCTTTTTAATTCGAACTTGTATAATTTACGCTAAACATGTGTGATAATCCGAGACGT
CTACAACAGATGTGACATTAATATGTGTTATATTTTATAAGCAGCATACTTTGAGAGCCCCTTCAGTTTGGAATACCCCCATTATTAATGTAAGC CGCCTCTTCGGGATCAATTGGCTTGCGGGCAAATCGTGCCGGCAGCTCGTAGTCCTCAATTGCTGGTCCACCGGCCAACTAAATGTAGAAGGGAC
AATTACGAAGATTAGTTATGATGCACAGAAGAAGCCGTGGTATTGTGTATAAATGAAATGGGCTGGGTTAACCTTTTGCCTCCTGCGGCCTGGG
AACTTGCCTTCTGGTTTGCTGTCTGGGCGCCCGGCACTCCTGCACCACCCTTGCGGAAGTGTATGAGCGGTACGCGCTTAGCCAGCGCAACTAGT
GTTGGTCGAACCATAGCAACAGCAATTGAATTTCTACCAAAAAGCCAAGGCAAAAGTAAAAGTTACGTGAATAACAGCTGACTGTAAACTCATAC
AAGCGCTGCCAGATCGTTAAAATTGCATGCCATTCGCCGCGCAATGGATTATTATCGTTATTGAAATTTACGTGATCCTGTGAATGGCTAAGGCA
GATAAGAGGAAGCGCAAAAAACTATTTTGGTCCAAATCGGTAATATTTTTATATTTAAAATGAATTGGGGACAGAAGATAACCGGCAGCCGACGG
CCCTAACTTCTGGACGGACATCGCCAGTATATGGATTGCTCCTAAAACTAGCAAACCAACGTACTTATGCTCTATGCAACAATAAATGTCATATG
AAAACAAACTATTGAAGACGTTTTTATGAGTATAACCGGTAACTATTTCATTTGTTTATTATATTAATGACAAATAAAC
(SEQ ID NO: 715)

Exon: 3354..2042
Exon: 1895..1434
Exon: 1373..1001
Start ATG: 2593 (Reverse strand: CAT)

Transcript No. : CT19977
AAGAACAAGAGCAGCGAGCACCACTGCTCATCTGAAACGAAAGCCAATCGGTCGTGATATTTCCACACGCGCAGCTGCTTTTCGATCGGCTCTGT
GTTCGTTCGTTTGTTTGTGCTATAACTGCTACCCCCGCCCACTGCGATCATCCGCCTTGCCCCCGCCCCCCGCAGTTCCCGTGCGCCGCGAACAA
AGAGTGGAAAATTTTGGTGTCAGCTAAAAAGGAAACCCTTTAGCCATCTTATTTGGGCCCCGTAACGTTGCGGCCCCCCGTAAACACCGGATTCG
TTGTATCCCCCACCTGGATGGGTGTGAGGCGTAGTATGCCAGTGAACTGTGCCAACAAGGACTGCCTGGGTCTCCGTAAGCGTGTCTGTGGTCTG
CATCAAACGTGGAAGTGGCTGCATCAGACGCCCGCCCTGCACGAATACCTCATCTCGGCCAGCTCCGTGGCTGCAAACACATCCCGAGCCACTAA
GAACGCCACAGTCTAAAGTCCAGAGCGACCAAAGCCATTTAAAGACCAAAACGAATAGCGTAGATAGTAGACCATACATAACCTAAAGAAGAGCA
CACACGGACCACACAGAACCAGGCAGACGACAACCGTAGAAACCAACCAACCAACCAACCAATCAACCAGCCAAAAGCTTTTTTCGACACCATTG
ACCTTGTTTCGCTTGCAAGTGCATTGTGTCCCAGATCACCTGGCAACAGAAATCACACACACCCGTACGCCCCACTTCCTTGTGTAAGCCATGAG
CATGCTGTTGCGACGCAATTCCAGCCAGCTGCGGCTACTTCTCTCCTCCGCCGCTCAGGCCACGCGCCTGGCATCCAGCGGAGTGGAGCCACCAT
CTGCTGGACAGCAGGAGATTAAAAAGCAGAGGCGCCAGCCACCGCCCGTGGTTCCCGATTCGGAGATCAAGAAGTCCGTGTTCATCTCGCAGTCC
AGCGATGTGTTCACCAACCTCGCTCTAGAGGATTGGCTGTACAAAAACTTTGATTTCAGCCGCCACCATGTGCTGCTGCTGTGGGCCAACGACCC
GTGCGTAGTCATTGGTCGCCACCAGAATCCCTTCACCGAGGCTAATGTTTCGCAGCTGGTGGAACGCGGCATAACACTTGCACGCCGCAATAGTG
GCGGTGGAGCGGTGTACCATGATCTTGGGAACCTCAACTGCACCTTTTTCTCGCCCAGAGAGCGCTACGATCGCAAGTACAACCTGAACATCGTG
ACCAGGGCCTTGTTCCGCGAATGGGCCATCAAGGCAGAGATAAATGAGCGCGACGACATTGTAGTGATGAATAAGAAGATTTCCGGCACTGCGGC
CAAGCTGGGACACCCGAACTCGTACCATCACTGCACCATTTTGGCCAGCGCCAACAAATTGCACTTGGGCGAATCTCTGGTGCGGGAGCCGGCCA
ATTATATTAGCAAGGCCACGGCTTCGGTGCCGTCGCCCATTCGCAACCTGGTTGATGTCAATCGCACGGTGAACGTTGCTCAGCTGCGTTCCGCC
GTGGGTTACGAGTATTTGAGAACGGCTGCAACTACGCTTGAAGACGGCGGCAGCACACAGACGATGCAGCAGCGCGGCTTTCAGCTGGTCAATCC
CACAGAGAAATGGTTCCCCGGCATTGAGGAATTGCGCTCCAACTACAGCTCTTGGGACTGGGTCATCGGCAAGACTCCCAAGTTCACCGTGCAGA
AGGAACTGGAGGTGAAGGGCGATGAGCAGGACATGAAACTGAAACTAAGCGTGGAAGTGGAAGCGGGATTAATGAAGGAGATCGGCATCCAGCTG
CCGCAGAGCGATCAGCTCGTCCCGGTGGTGACTCCGCTCCAGGGCAAGCCCTACAACGAGGAGAACCTGAACGGAATACTTGGCGCCCTTAAGCT
CGTCAGCGCATCGAATGTGAAGCAGGCAATAAACGGATCAGCTTGATTACTGTTGTGCTAGCTCGAAAAAATTAACAAAAAAATATATAATCCAT
TTCTAGAGCACTAACCACGCTAACGTAGTTATAATCTTTCCAAGAAACCATATTACTAACCTAGTATTTAAGCGGTTTACCAACAAACTATTTAC
TTTTGTTACCACGTTTTATATAAAAGAACTGCATTAAATGTTTAAACATTGATTATTA
(SEQ ID NO: 716)

Start ATG: 762 (Reverse strand: CAT)

MLLRRNSSQLRLLLSSAAQATRLASSGVEPPSAGQQEIKKQRRQPPPVVPDSEIKKSVFISQSSDVFTNLALEDWLYKNFDFSRHHVLLLWANDP
CVVIGRHQNPFTEANVSQLVERGITLARRNSGGGAVYHDLGNLNCTFFSPRERYDRKYNLNIVTRALFREWAIKAEINERDDIVVMNKKISGTAA
KLGHPNSYHHCTILASANKLHLGESLVREPANYISKATASVPSPIRNLVDVNRTVNVAQLRSAVGYEYLRTAATTLEDGGSTQTMQQRGFQLVNP
TEKWFPGIEELRSNYSSWDWVIGKTPKFTVQKELEVKGDEQDMKLKLSVEVEAGLMKEIGIQLPQSDQLVPVVTPLQGKPYNEENLNGILGALKL
VSASNVKQAINGSA*
(SEQ ID NO: 717)

Classification: hypothetical

Celera Sequence No. : 142000013384513
TTAATCCCGAGGACGACGTGGGCAACATAAATGCTGCCCAGAGCAAATCGACGCCGAGAAGTAAACAGCTAAATGATTCAGCTCACAAGCCACGA
ACAAGCACGACGGCATCTGCACCAACAAAACGAAAGTCTGCGGAAAATTCTTTATCCGAGGTGTTTGCTAAAACTGTGCGATTGATACAGCCCAT
CCCAAAGATGTGGCCTACTCCTTCTGATGCCGACTCGGGGATATCTTCGATGGGCTCATCATTGGCATCGACAGCCCGCCTGAAGTAGTAGCCGT
GTTTCGTCTTAAATGTGCTTAGTAGTTCTTTGTAGATAAGATTCCTTGCGTCCTGACCCAGTAGTAGAGTCTAGTTTGTGTGCCCCCTTATTCGA
ATTCAATTTTTATGTATATTATTTTCAGGCCGAGAGATCAATGCGCTTTCCCATGCGGTACAACAAGATCAAGAGGCTGCATTAGATATATGTTC
TTGCCAGATTATTTACCCGCAATCGTGTACAAATGTAAGTTTTAGTTACGTATTATTAGGAAGCTTGCAATAGAAAGAATGCTTTAGCTTAAGCT
TATCGATGTATGAATCAATATTTCTTTAGAGTAGTAAACCAGTATTATCTAAGCTCGATTTTCCTAAGCATGAAGCCGTTTTTTAGTTTTTCTTT
CACTTCACTTTTTTAACTTTTTACGACGCTTTTAGTTGCTTATGAAATTTTCACATTTTTATTAATTTCTATTTCTTTTGAACATTTTTGATTTA
TTTTACTTTACCTACGAATAGATTTATTTCGTATTCTTATTATTTCTATGATTTCCTAAAAATTTAACACTATACCTCCTTTGATTTAGAACAAA
AATAGACAAATGACTTTTTGATTGACGAAGCGCGTGTTTTGGAAATCCTCATGAGCTGATAGTACTAAATTCAAGTACCTGATCTCGTCTGTACA
AAAGTATAAACATAAGAACTCTTCGGACATAAGACAAAGTTCAAGATAAATTAAGGATAAAGTGTATATATACGTATGTATTTACCAGAGTGCAA
GCTAGTGTCTATTTACAATCATTTTAAGATATAATGTTTTTTTCGTAAGTATAACGTGTAGTTCTTAAGGAATAAAACGGAACCATGCAATTACT
TAATGTGTTTTAATGAAAGTAAGTCGGCGATTCTCCCAATGCTACTCCGAGTCGCTGCTGCCTGACTTGTGCTCCTCCTCTTTCTTCTCTTCAGT
CTTGTAGTGGCGATATTCTTTCTTGAGCTCCCACATGTTCTTGTGCGGGTTCTTCATATTGTAATCGCAGACATCCTTGAGAATCTCCTTCAGGT
AGCTAATCGGCTGGTTGGTGATCTTGACCAGATCCTTGATGTTATAGTATTGATGCTTCTCGAATGCGTGGAAGAGCATATCCATCACGGCATTC
TTGTCGTCGCGCGCCTTCTTGCCCTCGGCCTTCTTTCGCTCCCGATATTCAATCTGCAGGAATGGAGGAGTTATATATACATATATATTACCAAA
ACAGAGTGTATTATTGTTCTCACGTTGTGTGCGTGGTCTTTTACAGGCTTAAAGTTCTGCACGATTTTGTCGATAGGCTGCACACGTCGCTGTGG TTCCGATGCCTTGCGTATGGACTCCAGCTTTAGTTTCATGTAGCAGTTGTCGGCGATGGGTCGGCACTCTAGCTTTTGCACAATCCTGCCCTCCA
TATACAACTTTTCGTTATCCGGCTGTGCCGCCGAGGTAGTCGAGTTCTCCTTGCCATCGGACGGTGCCATGTGCGAGAATACGCCGAGCGTCTGC
TTGGTGACCTGCGACACGTCCAGGATGTGCTCGGTGGGTATTTTCTCCTCGGGATCTAGAGCCAAAACGGCGGGCGTGAGGGAAAGCGAGACCTG
GGCCTTTTGGCCAGGTGTCTTGTTTATCCGGAGCTTGCCCACGTCCATGTTCGTCGGCGCCTTCTCCCATTTCTGGGCAATGTACTTGGGCACCT
TCACCAGCCATACGCCTCGCCCAGCATTGGACAGGTCCAGGTCCTTGTCGATGATCTGTGTCTTTTCCTTATCCTCCTTCGACATTCTGTTTGCT
TTAAATTATTAAAAACGAATTTGCAAAGCCACTTGTACCGTTTTCGGCTTTGCTTGTTGTTGTTGTTTTGCCGTAAATTTAGTGCGGTCGAATAA
ACAGTTTCGAAAAAATGCTAGTTTAGTATATCACGGTATTTTTCTTTCGGTATTTATTCGTTATGTTATTATTAGGCGCCAAGTTTGAAAAAGTC
CGAAGTGCAGATAACGAAATAGAACTATTTACATATCTGAATTTTATATAGTTAGCAAGAACTTTAGAACATAAGAAATAACTTTTATAATGAAA
TGTCTTAGAAAGAATATGATATCTTAATTTTGATTTATTCAGCAAATTTTATGACTAAATTTAGAACACAACATTGTATTGATTTAAGATGAATT
TATGAATTGATGTGACACCTTATCCAGCATTATCCACCCCATTGCCCTATTAAATTGTTTTTCTAATATTTTATTGTTTTTTCATTCTTTTTAA
ATTAGGTTGACAGCATGGTGATTGTGTAGAATCTATTCCTCCTCCTCTTCCTCGTCCTCCTCCTCCTCCGCATCGAGATCCTCCTCGTAGCTATT
ACCACCAGTGGGGGTAACATTAGAGCCGAGCTCGATGATCGGTTCCTGTTCCTCAACGGGCGTGACGGGCTCTTCGACCACAGGCTCGCTGGTCT
CGTTCTCGTTCTTCTGGATGGCCTGCAGTTCCTGGGCGGCAAGCTCGGATTCCTGGCGGGCGATCTCGGCCAGCTCGGCGGCCTGGCGAGCAAGT
TCTCCCTCACTCTCCTTCTCGATCTCCGCCAGGCGCTCCAGCTCCTGCTCACGGACACGCTGCTCCTCCTCCAGGCGAGCCTCTTCAGCGACACG
AGCCTCTTCGGCGGCCTTTTGGGCAGCTTCTTCGGCGGCACGAGCCTCCTCTACAGCCTTCAGTGCGGCTTCTTCGGCGGCCTTTTGGGCAGCTT
CTTCAGCCAGACGAGCCTCTTCGGCTGCCTTTAAAGCGGCTTCTTCGGCAGCCTTTTGGGCAGCTTCCTCGGCGGCCTTTTGGGCGGCTGCCTCC
TCTGCTAGGCGAGCTTCCTCAGCAGCTTTTTGGGCAGCTTCCTCGGCGACCTTTTGGGCGGCAGCCTCCTCCGCTAGACGCGCTTCTTCGGCAGC
TTTCTGGGCAGCATCTTCAGCGGCTTTTAGGGCTTTAGCTTCTTCGGCTGCTTTTTGGGCGGCAGCTTCAGCCAGGAGAGCCTCTTCGGCAGCGA
TT
(SEQ ID NO: 718)

Exon: 2327..1544
Exon: 1478..1001
Start ATG: 2080 (Reverse strand: CAT)

Transcript No. : CT20349
ATAAAATTCAGATATGTAAATAGTTCTATTTCGTTATCTGCACTTCGGACTTTTTCAAACTTGGCGCCTAATAATAACATAACGAATAAATACCG
AAAGAAAAAATACCGTGATATACTAAACTAGCATTTTTTCGAAACTGTTTATTCGACCGCACTAAATTTACGGCAAAACAACAACAACAAGCAAAG
CCGAAAACGGTACAAGTGGCTTTGCAAATTCGTTTTTAATAATTTAAAGCAAACAGAATGTCGAAGGAGGATAAGGAAAAGACACAGATCATCGA
CAAGGACCTGGACCTGTCCAATGCTGGGCGAGGCGTATGGCTGGTGAAGGTGCCCAAGTACATTGCCCAGAAATGGGAGAAGGCGCCGACGAACA
TGGACGTGGGCAAGCTCCGGATAAACAAGACACCTGGCCAAAAGGCCCAGGTCTCGCTTTCCCTCACGCCCGCCGTTTTGGCTCTAGATCCCGAG
GAGAAAATACCCACCGAGCACATCCTGGACGTGTCGCAGGTCACCAAGCAGACGCTCGGCGTATTCTCGCACATGGCACCGTCCGATGGCAAGGA
GAACTCGACTACCTCGGCGGCACAGCCGGATAACGAAAAGTTGTATATGGAGGGCAGGATTGTGCAAAAGCTAGAGTGCCGACCCATCGCCGACA
ACTGCTACATGAAACTAAAGCTGGAGTCCATACGCAAGGCATCGGAACCACAGCGACGTGTGCAGCCTATCGACAAAATCGTGCAGAACTTTAAG
CCTGTAAAAGACCACGCACACAACATTGAATATCGGGAGCGAAAGAAGGCCGAGGGCAAGAAGGCGCGCGACGACAAGAATGCCGTGATGGATAT
GCTCTTCCACGCATTCGAGAAGCATCAATACTATAACATCAAGGATCTGGTCAAGATCACCAACCAGCCGATTAGCTACCTGAAGGAGATTCTCA
AGGATGTCTGCGATTACAATATGAAGAACCCGCACAAGAACATGTGGGAGCTCAAGAAAGAATATCGCCACTACAAGACTGAAGAGAAGAAAGAG
GAGGAGCACAAGTCAGGCAGCAGCAGCTCCGAGTAGCATTGGGAGAATCGCCGACTTACTTTCATTAAAACACATTAAGTAATTGCATGGTTCCG
TTTTATTCCTTAAGAACTACACGTTATACTTACGAAAAAAACATTATATCTTAAAATGATTGTAAATAGACACTAGCTTGCACTCTGGTAAATAC
ATACGTATATATACACTTTATCCTTAA
(SEQ ID NO: 719)

Start ATG: 248 (Reverse strand: CAT)

MSKEDKEKTQIIDKDLDLSNAGRGVWLVKVPKYIAQKWEKAPTNMDVGKLRINKTPGQKAQVSLSLTPAVLALDPEEKIPTEHILDVSQVTKQTL
GVFSHMAPSDGKENSTTSAAQPDNEKLYMEGRIVQKLECRPIADNCYMKLKLESIRKASEPQRRVQPIDKIVQNFKPVKDHAHNIEYRERKKAEG
KKARDDKNAVMDMLFHAFEKHQYYNIKDLVKITNQPISYLKEILKDVCDYNMKNPHKNMWELKKEYRHYKTEEKKEEEHKSGSSDSE*
(SEQ ID NO: 720)

Name: TRANSCRIPTION INITIATION FACTOR II
Classification: transcription_factor
Gene Symbol: TfIIFbeta
FlyBase ID: FBgn0010421

Celera Sequence No. : 142000013384643
ACCAGCATCCAGTGATTGTATTTATAGCCCAATTGAAGCGTTAGATTACGATTCACGGAGGGATAGACCGTTTTTAGATTGGCATTCGCCTCGAT
GACCGGCTGAAGATTTGAGCCCAAGTGCAGGGATGTCAGCAGCGCAAAGTAACCAATGTCTCGTATTTTGGGTATGAACATGGTTCTCGAATTTG
GAGTTCAAAATGAAAAAATTTTAAGTCGTTTTTTAAATTTTGTATCTAATTTTGTGTGACCTCAATGTGCTCTGACATTCCCAGTCTGATTGCTT
AAAAAACGTTATATTATAAACATTTTTTGATTTTTATTTTAAATTATACGTAATTAAAATTACGTAATTAAACAATTAGGTAAATAATAAAAGAT
TTTATCGTTGTTTGTTATAAATTAATTTATTAAATTGAAAGGCAGCGTGCTGAAACTACTTAACTGCATCAACTTATTTTAGCGACATAAATTAT
TTGAAATTCCCGCCAGCTGGTACAGTTTGAGAGCAACTATTAGCTGTGCTAAAACCCCTGCATTTAAGTGCTTGACAATCTTGCCTTATTCCAAC
CTATTGGAAATATAAATTTCATATTAAAACAATCAACGGTACGATGTACATATTTTTTTATTGTAAAACAATATATTGTTAAGATTTCAAAAGGA
ATTAATTTTTTATTTTTAGTTCAATTGGTTGGAGTGCTTGGTAAATAGTTAGCACAGATAGCAACCTTGGTGTGAGCCTTCGCTAATATTTCGAC
ATAAGATTTAAATACAGAAAATAATATTTAATTCTAACAATTATACCTTATTTCTGTGTGAAATTATGAAAAATGTAAACATTTCTCTGAATACA
AATGACATTTCGTTACTGTAGGTTTTGTTCTGTGTAAATAGGTTTAATATTCACGGATAATTCGTTTGTAGTATATTTTAGTATATAATTATTCG
CGTATGATGGATTTTTTGGCCGGCAATAAAAAAGTGTAAATTGTAGCAAGGCAACCGAATCGTTTCAAAATTTTGTCCAAAAAGTGGAAATTTAC
GCGAAATGGAGCGCGAAATAGCGCACAGTTTAGCTGGCGGCGAGGAACGAAGTAGCGATGTGGCACCTGGACAGGTTAAGACCTTCGAGGAACTG
CGTCTATACCGAAATCTGTTGAACGGATTGAAGCGCAACAATTTCGTGACGCCAACGAAGATTCAGGCAGCTGCCATACCCATGGCACTGGCCAA
AATGGGTAAATATCTTGCATGCAACAGAAGATTATCAATAATAGTTGCTATATTAATCTGCAGATCTAATAATACAATCGAAGAGTGGAACTGGC
AAAACTCTAATCTATGTTATAGCCGTCGTTCAGAGCTTTAATCCCAACATAAACCAACCGCATGCCATGATCGTGGTCCCAACTCGAGAGCTGGC CATTCAGGTGCAGGACACATTTTTCCATCTCTGCAAATCGTTTCGGGACTTTAAATGCTCTGCTTTCATCGGTGGCACCGATGTGGCCAAGGATC
GCAAGCGAATGAATGAAAGTCGAGTCATTATCGGTACACCGGGACGTTTGCTGCATCTGTATGAGAATAGAGTATTCGATGTGTCCAAACTGCGA
CTGCTGGTGCTCGACGAGGCCGATCAACTTTATCAGACAAAGAGCCTGCAGCATACGGTCAGTAAACTCATTGAGGCAATGCCCAAGAATCGGCA
AATAATTGCCTGCAGTGCCACATACGATCAGAATTTGGATGAGCGTCTGGCCAAGGTCATGGACAAACCCATGCTTATATCGAATTCCGAAAGGG
CTACCGTTCTACTGGGCATTCGGCAGTTTGTCTACGAATTGCCACAGCAGAATAACAGTGTGGAGGAGATGCGTCTTAAACTGCAGATTCTTGGC
CAGATCTTTAATCAGCTGCCTTACGAACAGGCCATCATCTTTGCTAGCTCACAAATGCGAGCGGATTCTTACAAGAACTATCTTACAGCCAGTGG
TATCGATTGTCATTTAATTTCGGGAGCCATGGAACAATCGGAGCGTTTGCATGTTTTCGAGGGCTATAGAAACTTTACTATGCGCATCCTGGTGG
CCACTGATTTGATGGCACGCGGAGTGGACTCCCCGCATGCCAACCTGGTTATCAACATTGATCCACCACAGGATCATGTCACCTATTTGCACCGC
ATTGGACGAGCTGGTCGGTTTGGCTCCAAAGGCATAGCCATCACGTTTATTGCCTCCAAGAAGGAGAGCCAGAGATTTAGGGAAATGTCAAAAAA
AATCGCTACGGCTTGGTCGGTTCTGGAGTTTCCCAAGGAGCCAATGCCCAATGAATTCAATTTTTGGGATTTCGAAAAGTACAACTTTGATTATT
ACATTAAGGAAGAGAATCCGCTACAGGAAATGCCTATGCCTATTAAAGAAAATAGAAGTAAAGAAAATGTTGATGCTTCTTCAGTTGACTTGGAA
AATCTTCAAAAGGATCAGGATGGCAAAAGGAGAGATCCAGACAAACTACCAGTGGCCTTAGAAAATGTTGAAACCCAAAAAGAGTTGGAGCTCGA
AAACTTACCAGAAAGTTCACATAATAATAAGAATCTTAGGGTCAAAGAGAAAGAAATTGTAAGGCAAGGAAAGCTTAAAGAAACTAATTCCAAAG
CTGGAGGTTCTAAAACGAACAAGACGGAGAGAAGGAAAAAATCTAACACTCCATCAAAGTTACAGAAACAAATAACTGAAGTGCAGCAAACACCA
GAGATCACCGTAAATAAATACTATATGCAAGAAGACATACAACGAACAGCAGACGGCAAAGAGTATCATCCTGTTAATGGAGCGGGAAACCACCA
GGTTCCGTCAAAATCTAATCAAAAACCGGTGGAGTTTATATCTCCCGAATTGACACCAACCCTAACACCATTGGAACTGACCCAGGAGCCGTCTC
CAACCACAGTGACACCACCTGCACCGCCAGCCAACTCGATTAACAACAAAACCTATTGCCTAGCTGCTCCAACGCAAACCAGTTCGATGACCATA
CAGAACATGGTAATATCGAACACGGTGGACGATGCCAGTAGCATCAGTTCGGATAGCATGGTGGTATGTGGCTATCATAGCGATAGGTCCTACGA
CACATACTATGCAACCAGTGATGAGGAGGAGATCTGGAATAGATTAATGTCGAAACAAAGGCGTCAGCTGAAGAGCAAGAGAGGCCATGGAAAAC
GGCGTGTGATACTATACAAGAAAGTATTTCCTAAACTAAAGGCGAATGTTAAACGCAAGCTTAAAAAACGGATGAGCTCGTCATGCAGATCCAAA
AAAGCACACCATTTGCGAAAACGTCATGTATACAAAAATATATCACTTTTGCCACACATGAATTTGTGTCATCTGCTTCAAAAATTTACAAATCA
AGAGAGATTTTTGAAACGGCTCCACAAATATGCAAAGAATCAATTCATTGACAATGCGAGGGTTGGCTTTTTGCTGGATAAGCTCTATAAATCCA
TCCTGGAAATGTACTATAACAGTGCTAAGGAGAGGAAGAAGCATTTTAAGGAAGCTATGAAGGAGTCCCTAAAATCCATTGATAACTACGAGAGC
CAAGAGTCTTCGGAATCAGAGGAGGAGGAGGAGGAGGAGAAGGATCTAAAGAACAAGTTAAGTGTTCATGTGACGAATCAGATGGACATACCACC
AATGCCACAGGCCGCTGTTGAAATTGGTTCAGGAAGTGAATCGGATACGGAGGACTCGCAGGAATACGGCGAAGGCGAAGAGATCATTGTGGACG
ATGAGGACGATGGCAGCGATGGCGGGCCAAATTCATCGAGTGGTTTTGTAGAGAGTCAGGAGAGTGTTTCGTCTGGAATAGACACTTCCGTTTAC
GAAACGGAATCTACGGGCGCATCTGGAAATAATTCAAGTGCATTCTTTATTTCGGATGATGAATCAGATACTGAATCCTTAACAGATTCGGAAGC
TGGAAGCAATGTCAGCGCGACAGGATCAAGCTCACAGCGATCTTCAGTAGCGAGCAGCACCTATGAATCTTCGGATGATGATTCTGTAACTGTAA
CCAATGTCAGTTCAATGCAGAACGCTCAATCATTGTGGTTGCAGACTTTCAACATGCAGTACCAATTCATTGCATCCCATGTGGCCAAGAATCTA
CAGAACTATTACTAAGTGGTTATGAATGAAAAACTAGTGAAAACTCAGGCATTAAAATTAAACTCAACTAATCACTTCATTCGGAAACAAAACGG
ATCAGTTCCAAGAGAGGCTGTATCAGTCTCTTTCCTTACAATTGTATATCGTAGCCAGTTAAACCGTTTTCTTAATTAGAATACTCAATGTCGAA
ATAGTTGATAGCATGTTGGATACCATGAATGTTTTTTATGCAAGCAATAAATTGCAGAATTTGTTACCAAAAAAATAAATGAATTAAAGCAGGA
AACTAACTATTTTGAATTTATTAAACAATAAGTTCATTGCTCAACTTCTTTGATTTCAAAATTGATTGTTTTTCATGTTTATTCGCTACATAATC
GCATCAAACAAATTAATCCACAATGTGAAAGTTAAATCCCTTTAATCACTCGCAATGATTTATCTAAGAGATGGAAAACAAACATTTTTCTTGG
TTTCGGCAAGCCGGATGGATGAAGGTAAAGAAGCGGCGCCAACCGACTGCCGGGACATAAATCATATAGTCAGTGGGATCGGGATCGGCATCGAC
CATCGACCATCGGGCAACGGGCATCAGCTGTGTGGCAGACAACATTGTTGCACGGGCGCCGCTCACTTTGCAACTGACTGCAGAGGTGTTAACCC
ATTAATTAGCTGTTGTCAAAAGTCGTTCACTCGATTTTGAAAGCCACTCGAAAATCAGAATGGATTGTACAAAAATATGACATATATTTATGTTT
TATTTATTTATTTAATGCATTTTGTGAATTATTTGTGCAACGAATGCCATGTTTGTCAGCAAATAAATGAGTTCTACTATTTTCTTTTTATACTC
CACTGCTGTATTTAATTTTTAAAATACTTCGATTCATAAATAATTTATTTTTAAATTGATTAAATGCAGTTAAAATTTTTAAGTTTCCTTTTACG
AGTTTTGTGTCCCCATTTGCGAGTGCTTCGCAATGGGTTAAGCGAATGAGACGGTCCACAGGCGGCATGCCGCGTCGGTGGCATAGTCAAAACAT
TCGCCCTGCGGTCGAGCACGCAAAAAGCCGGCATCTGGATGGTACTGCTCATTGGTCGTCGATCTGCAGTGCCCCAAGTGCCCCTCTTTTGGAGT
GCAACACCCCTCCCCCCCCTGCGTTGCAAGTCCAATAAGGAGCGTGAGAAAACGCAAATTCAAAGCGAGCTGGAAGCGACAACATTTTATAGATC
CTAGAGACATGGATAGCGTTGCATTTTGTCGCTGCCGCAGTGGCAGCAAACT
(SEQ ID NO: 721)

Exon: 1001..1240
Exon: 1299..4467
Start ATG: 1051

Transcript No. : CT20361
GCAACCGAATCGTTTCAAAATTTTGTCCAAAAAGTGGAAATTTACGCGAAATGGAGCGCGAAATAGCGCACAGTTTAGCTGGCGGCGAGGAACGA
AGTAGCGATGTGGCACCTGGACAGGTTAAGACCTTCGAGGAACTGCGTCTATACCGAAATCTGTTGAACGGATTGAAGCGCAACAATTTCGTGAC
GCCAACGAAGATTCAGGCAGCTGCCATACCCATGGCACTGGCCAAAATGGATCTAATAATACAATCGAAGAGTGGAACTGGCAAAACTCTAATCT
ATGTTATAGCCGTCGTTCAGAGCTTTAATCCCAACATAAACCAACCGCATGCCATGATCGTGGTCCCAACTCGAGAGCTGGCCATTCAGGTGCAG
GACACATTTTTCCATCTCTGCAAATCGTTTCGGGACTTTAAATGCTCTGCTTTCATCGGTGGCACCGATGTGGCCAAGGATCGCAAGCGAATGAA
TGAAAGTCGAGTCATTATCGGTACACCGGGACGTTTGCTGCATCTGTATGAGAATAGAGTATTCGATGTGTCCAAACTGCGACTGCTGGTGCTCG
ACGAGGCCGATCAACTTTATCAGACAAAGAGCCTGCAGCATACGGTCAGTAAACTCATTGAGGCAATGCCCAAGAATCGGCAAATAATTGCCTGC
AGTGCCACATACGATCAGAATTTGGATGAGCGTCTGGCCAAGGTCATGGACAAACCCATGCTTATATCGAATTCCGAAAGGGCTACCGTTCTACT
GGGCATTCGGCAGTTTGTCTACGAATTGCCACAGCAGAATAACAGTGTGGAGGAGATGCGTCTTAAACTGCAGATTCTTGGCCAGATCTTTAATC
AGCTGCCTTACGAACAGGCCATCATCTTTGCTAGCTCACAAATGCGAGCGGATTCTTACAAGAACTATCTTACAGCCAGTGGTATCGATTGTCAT
TTAATTTCGGGAGCCATGGAACAATCGGAGCGTTTGCATGTTTTCGAGGGCTATAGAAACTTTACTATGCGCATCCTGGTGGCCACTGATTTGAT
GGCACGCGGAGTGGACTCCCCGCATGCCAACCTGGTTATCAACATTGATCCACCACAGGATCATGTCACCTATTTGCACCGCATTGGACGAGCTG
GTCGGTTTGGCTCCAAAGGCATAGCCATCACGTTTATTGCCTCCAAGAAGGAGAGCCAGAGATTTAGGGAAATGTCAAAAAAAATCGCTACGGCT
TGGTCGGTTCTGGAGTTTCCCAAGGAGCCAATGCCCAATGAATTCAATTTTTGGGATTTCGAAAAGTACAACTTTGATTATTACATTAAGGAAGA
GAATCCGCTACAGGAAATGCCTATGCCTATTAAAGAAAATAGAAGTAAAGAAAATGTTGATGCTTCTTCAGTTGACTTGGAAAATCTTCAAAAGG
ATCAGGATGGCAAAAGGAGAGATCCAGACAAACTACCAGTGGCCTTAGAAAATGTTGAAACCCAAAAAGAGTTGGAGCTCGAAAACTTACCAGAA
AGTTCACATAATAATAAGAATCTTAGGGTCAAAGAGAAAGAAATTGTAAGGCAAGGAAAGCTTAAAGAAACTAATTCCAAAGCTGGAGGTTCTAA
AACGAACAAGACGGAGAGAAGGAAAAAATCTAACACTCCATCAAAGTTACAGAAACAAATAACTGAAGTGCAGCAAACACCAGAGATCACCGTAA
ATAAATACTATATGCAAGAAGACATACAACGAACAGCAGACGGCAAAGAGTATCATCCTGTTAATGGAGCGGGAAACCACCAGGTTCCGTCAAAA
TCTAATCAAAAACCGGTGGAGTTTATATCTCCCGAATTGACACCAACCCTAACACCATTGGAACTGACCCAGGAGCCGTCTCCAACCACAGTGAC
ACCACCTGCACCGCCAGCCAACTCGATTAACAACAAAACCTATTGCCTAGCTGCTCCAACGCAAACCAGTTCGATGACCATACAGAACATGGTAA TATCGAACACGGTGGACGATGCCAGTAGCATCAGTTCGGATAGCATGGTGGTATGTGGCTATCATAGCGATAGGTCCTACGACACATACTATGCA
ACCAGTGATGAGGAGGAGATCTGGAATAGATTAATGTCGAAACAAAGGCGTCAGCTGAAGAGCAAGAGAGGCCATGGAAAACGGCGTGTGATACT
ATACAAGAAAGTATTTCCTAAACTAAAGGCGAATGTTAAACGCAAGCTTAAAAAACGGATGAGCTCGTCATGCAGATCCAAAAAAGCACACCATT
TGCGAAAACGTCATGTATACAAAAATATATCACTTTTGCCACACATGAATTTGTGTCATCTGCTTCAAAAATTTACAAATCAAGAGAGATTTTTG
AAACGGCTCCACAAATATGCAAAGAATCAATTCATTGACAATGCGAGGGTTGGCTTTTTGCTGGATAAGCTCTATAAATCCATCCTGGAAATGTA
CTATAACAGTGCTAAGGAGAGGAAGAAGCATTTTAAGGAAGCTATGAAGGAGTCCCTAAAATCCATTGATAACTACGAGAGCCAAGAGTCTTCGG
AATCAGAGGAGGAGGAGGAGGAGGAGAAGGATCTAAAGAACAAGTTAAGTGTTCATGTGACGAATCAGATGGACATACCACCAATGCCACAGGCC
GCTGTTGAAATTGGTTCAGGAAGTGAATCGGATACGGAGGACTCGCAGGAATACGGCGAAGGCGAAGAGATCATTGTGGACGATGAGGACGATGG
CAGCGATGGCGGGCCAAATTCATCGAGTGGTTTGTAGAGAGTCAGGAGAGTGTTTCGTCTGGAATAGACACTTCCGTTTACGAAACGGAATCTA
CGGGCGCATCTGGAAATAATTCAAGTGCATTCTTTATTTCGGATGATGAATCAGATACTGAATCCTTAACAGATTCGGAAGCTGGAAGCAATGTC
AGCGCGACAGGATCAAGCTCACAGCGATCTTCAGTAGCGAGCAGCACCTATGAATCTTCGGATGATGATTCTGTAACTGTAACCAATGTCAGTTC
AATGCAGAACGCTCAATCATTGTGGTTGCAGACTTTCAACATGCAGTACCAATTCATTGCATCCCATGTGGCCAAGAATCTACAGAACTATTACT
AAGTGGTTATGAATGAAAAACTAGTGAAAACTCAGGCATTAAAATTAAACTCAACTAATCACTTCATTCGGAAACAAAACGGATCAGTTCCAAGA
GAGGCTGTATCAGTCTCTTTCCTTACAATTGTATATCGTAGCCAGTTAAACCGTTTTCTTAATTAGAATACTCAATGTCGAAATAGTTGATAGCA
TGTTGGATACCATGAATGTTTTTTTATGCAAGCAATAAATTGCAGAATTTGTTACCAAAAAAATAAATGAATTAAAGCAGGAAA
(SEQ ID NO: 722)

Start ATG: 51

MEREIAHSLAGGEERSSDVAPGQVKTFEELRLYRNLLNGLKRNNFVTPTKIQAAAIPMALAKMDLIIQSKSGTGKTLIYVIAVVQSFNPNINQPH
AMIVVPTRELAIQVQDTFFHLCKSFRDFKCSAFIGGTDVAKDRKRMNESRVIIGTPGRLLHLYENRVFDVSKLRLLVLDEADQLYQTKSLQHTVS
KLIEAMPKNRQIIACSATYDQNLDERLAKVMDKPMLISNSERATVLLGIRQFVYELPQQNNSVEEMRLKLQILGQIFNQLPYEQAIIFASSQMRA
DSYKNYLTASGIDCHLISGAMEQSERLHVFEGYRNFTMRILVATDLMARGVDSPHANLVINIDPPQDHVTYLHRIGRAGRFGSKGIAITFIASKK
ESQRFREMSKKIATAWSVLEFPKEPMPNEFNFWDFEKYNFDYYIKEENPLQEMPMPIKENRSKENVDASSVDLENLQKDQDGKRRDPDKLPVALE
NVETQKELELENLPESSHNNKNLRVKEKEIVRQGKLKETNSKAGGSKTNKTERRKKSNTPSKLQKQITEVQQTPEITVNKYYMQEDIQRTADGKE
YHPVNGAGNHQVPSKSNQKPVEFISPELTPTLTPLELTQEPSPTTVTPPAPPANSINNKTYCLAAPTQTSSMTIQNMVISNTVDDASSISSDSMV
VCGYHSDRSYDTYYATSDEEEIWNRLMSKQRRQLKSKRGHGKRRVILYKKVFPKLKANVKRKLKKRMSSSCRSKKAHHLRKRHVYKNISLLPHMN
LCHLLQKFTNQERFLKRLHKYAKNQFIDNARVGFLLDKLYKSILEMYYNSAKERKKHFKEAMKESLKSIDNYESQESSESEEEEEEEKDLKNKLS
VHVTNQMDIPPMPQAAVEIGSGSESDTEDSQEYGEGEEIIVDDEDDGSDGGPNSSSGFVESQESVSSGIDTSVYETESTGASGNNSSAFFISDDE
SDTESLTDSEAGSNVSATGSSSQRSSVASSTYESSDDDSVTVTNVSSMQNAQSLWLQTFNMQYQFIASHVAKNLQNYY*
(SEQ ID NO: 723)

Name: DEAD-box helicase
Classification: RNA_binding
Gene Symbol: Dhh1
FlyBase ID: FBgn0011802

Celera Sequence No. : 142000013384666
GCGATATGACTGTCATGATCTACTTCTATGGCCCGATGCTGTTGCTAATCGCTTTCAACATAATAATGTTTGTCCTTTCGGCGATTTACATATAT
AACATAAAGAAAAATGTGAAAGGCCTTGTCCACAAGCAACAAACAAACCAACAGATAAATGACCAACAAATGTAATTATATTATATTATAAGATA
ATAACTATAATGTCAAATGGCACTTTTTGTAATCTTTTATAGGTTTGCTATATTCCTGCGACTTTTCATCTTAATGGGTTTGTCGTGGAGCTTTG
AGATATTATCCTTTTTGTTAACCAAACAGCAAGCTTGGGCTAGGGCTTTAATGGTGGCTGACTACTTTAATTGGTCCCAGGGTACCATCATATTC
GTGCTTTTTATTTTAAAGCCTAGCATTCTAAAACTTATAATAGCAGGGTAAGTAAAGTATTACAAATAACCTTGAAATTTGACCGTCTCATACGT
ATGAACAATCTTTTGATTTAGGGGACGTCAAAACCTCCCAGGAAGTCACCATAATTCGAGATCAAAAGCAGCTCGATATAATTCAACTCATACGG
CTTGTGAAGGATCAATTGCGGATCCAAACGCTTACTGCTAAAAAAATGGAATTCAATAAGATGCAACGTCTCTGTTATTGATCACATTATTTTAA
TTTTCTATGGAGCAAAAGTTTAAAAAAAATATTTGTTATCAAGACAATAAATAATGTCTTGGAACATATAAAGCAAAATATATTAAAGGGTACAA
AAAACAGGAAAAGTATGGGGCAATACAGCAAAATATTTTTCGGATCATCAACTTTTTTGTAAGACAAAATGTAGAAATATTTCTGGCACCGTTGT
TTCAAACCAGGGTTTGAGTCAACAATGCTGGCCCACCACTGGCAAGTACCAAACGATTACAGAAAACTTTTTCTAATCGATTAAGCATCGGGGGT
CATCGATGTTTCTCCACCACTACAATTTCATGTTGTTTTTTTAGTCGCGGCTGTTTGACGTTTGTCGCTTTCCTCCGTTGCGAATATAATATATT
ACGTAGCTCATTTTTATACAAACGGAATTACGAGCGCAACGACGACAGCAACACTAGTAGCACTAATCGTAAGCGCAGGGGCCAAAAATTAAATT
GCGTTTGCGGCCGCAAAGATTTGATGACGTCGCATACGCCGTCTTCTAGGGCGTAAAAAGCAAAGCAAAGCAAACAAACGCGAAAGCGAAACGTG
TAAACGGCGTAGAAGCGATAAACGCGACTCAAATACGCAGCAGATAAAATACAATACGCGAGAAGAGAAAAGTCACGGGAAATATTGTTCATATT
CGGCGTCTTTCTGCGAGCGTAAACGTGTGTGCGTGGGCTTGTGCTTTTGCCAGTGTCGTGTGTGTTAAGTGCCTGTGTGTGTGTGTGATTAAGAA
GATATAAAGGAATATAACGGTAAATGCAGCGCCGCAAAAATGTGCAGCCTGACGCCAAACCACATGGTAAACGTAACGCAGCAGCACCTACACGA
TCTATTGGAAACTTTCGAAAAAAAGTCCTTCGAGGCGGCGGCCTTTGAGGAAGGGACGGCGGTAAGTTAACGGTACCAGTGTGTGCTTGTGTCTG
TGACTGTGTGTGTGACATACATTTAGGCGCACGTGCACGTGCTGCCGCCGCAAAAACACGCAGACACACACACACCCATGCATGATATGCCTGTT
GTGCTAGTGTGCGTGGCGCTTACACCGAGGACACGTCATAATGTCCTGTCCTCCTATTGCTCTTATTCTCTTCCCTTTCTTGCGCTCCTCTCCCT
CGCCGTCTTCCTTCTGCCGCGCCCCGAAAATACTGAGCCACTCAAAATGGCTGCCATTAAGCTTCCTGCGAGGAAAATCGCATTTTCATGGCAAT
CAATAGGCGGTAAAACATGTCGTTTGAAGGACTTAATGGTTCGTTTTCTCAAAGAGCAGAATTAATCACGGGATAGCTTTTCCAATTTGGTAGTC
AATCAAGGTTGTTACCTATAAGAGCACTAATCACTAATTAAAATATCTTTTTTAAATAAGATGAGCAATAAACGGTATTTTTGTATAATTTCTAT
TAACATACATTTTATGGTCCTAATATTATTTAATTTAATTGATTTTTCTATTCCGTTTCTTAGCAAATTTTTAATTAATTGATAAGAATTAAATA
TTAAGTTTCAGCTTTCAGAGTTCCTTATCGAGTTGCATTCATTTTGATTATTAAATCAATTTCAACTAGGAAATCCCGAGTAAGCAGGTTTTCCG
AAACCGGAAACTTCCTAATGGCTTTTGTTCTCGAATTGCCATTGAAACTCAATATCCCACTAAGCTGTGCTAAGCGATAATTAAAAGCCTAACAA
CGGCCTTTTTAGGCCCGCCCCTGACCCACGCATAAATGTGCATTTTCTTTCCACGACACGCACTCGAATTCAACTTTTGTCTTTTGCCTTCAGCT
CATCCCCTTGCACCCGTTCATCCATTTTACCCCCCTCGAATGTCACGCACGCCTTTTAAATAGTCCAGTGTGTAATGCCATCTTATCGCCCGCTT
AACCGGCAATAACACAGAATAACAATTGTAATGGCAACTTGGCAACAGCCGCTGCTCATTTGCATGCCAGTGCTGGTGAATATATTTAAGCCAAA
TCCCCGAGCCAGGCTGCCTGGAAACAGAGCGAGGAAAGCCAAGTGGGAACTTGGCACGTAACTCACGTTTCCGCGACGATCTTACATCGGTTTGT
TCAGCTGCAATCGGCACATAAATATGTACATACATACATACATATGTGCATACTTACTTGTGAATGTTTAACCGCTACCGCAAACTTTGTTGCAA
ACGTATGTTTTTATCAAACAATGGCTAGGTCTTATCACCAACCAGGGCGCCAACCTTCGATTTGATTTTCCACAAGTATTTTCCTATTCCTTATC
TATCTGCCAGCTATTCGAAGGCACAAACAAAACGCTGCTACTGCCCCTTGATACAAAGCATTGCATTTTTGATGGGGTGCAAAGGGTGAATTATG TGTGCGCTTCTCTCTCACTTGTTTATTTCCCAGTCTCCTCGGGGTTCAGGGTTAAGTTTAGCCACACCGATTAGATTAGGCGTTCGCCCAGCCAA
AGTCACAATACCTAAGCAAATGACGTAGGCAGGCGATGAGGTTTATAGCTTACAGAGAACGTATGTAAGAACCATTAAATGGGTTAAATATACGA
GCTAATAAGGTCAAAATGGCATTTAAATTGCAGCTAAAGATAATATTGCTACCTGAAATATATTTGGAAATCTTTAAATTGAAATTGAAGAGCTT
TCCAAATTCATAAGTTTTACTCCTCGTCTTATCGCAGCAACCAAAAACAAGCAATCCTCTTAAAAGGACTCAGAAAAAAAATCGAGTGAATAATAA
GATTGAGTTTGCTCCAATTTACATCAAGACATGGAAATATTTAATATTCAACATCCATCAAAAAAAATTACACTTATTTATGTTGGTTCACCACA
AAAAAAAATACATTTATATATGTAGATTTGCTAAAAAAAAAAAATCAACGTACATTTAAAAAGTTTCGCAGTAGACGCCGACCGACAATCGTTGG
ACAATTATTGTATGCTTATGGACTTAGAAACCCTGGAAACTCCGGCGGAACTCTTCCTCGAAATCCGCGTGGCCAAGATCAAGCTTGTGGTAGTC
GGTGAATCCCTCGCGATCCAGCTTGGCCTGGGCCCAAAGGATTAGCTTGATGAGGAACATCATTCTTGGCTCCATGGGCTCCTCTTTGCTCTTAC
TCTCATCCTCGTGGCAGCGTAACATGGCTGCATTCATTTCACCGGCCACCTTTTGGCGATATGAGTAGTACATCAGCTCCCCGTAGGGACTGTAT
TCCGGCCGATCGAAGGCCAGCAGACCCATGGTCCGCTCCACTTCGTGGTAGTGACTTGGATCGACCTTGGAAAAGCCCGCTGCCTTGCTCTGGGC
AAACTTCAAGGCCTTCTCCATCTTCTGATCCCTGATCATCTCGATCAGGCGCAACTGTTGCATGTGAAAAAATACATAGTTGTCGGTCTCGAAGA
GCCGTGGATAGATCCGTGTGGCCAGGTCCATGGCGTACTTGACCTGACCCACACGCACGGCATCCTGAATCCTTAAACGATCCCCGATGGTGTCC
ATGTGTGGACCCGGCTTCACAGACGCCTCGGTCATGAAACGCTTGGCGGCCTCTTGATATCCCTCTAAATTTGAAGTTATGTACTTCAGTTAGGG
GGGAAGCATACTAGTGAGGCTCACCTGTAACCAGATAGTTCATCACCAGGCGATTCAGGTCCGCCTGCCGGCACTGGAAGCTCATCATCCGATGG
GGCCACGAAGTGGATGGTCTATACTCGGCCATTCTCAATTTTTATAGTTTGATTTAGGTACTGAAAATTGAAACATAGGTAAACATGCAAATTGA
CATTAGTCCTGCTTTACTTCCTTAGTTCTTTAATTATTTCTCGTTTTTATCTATCTACTAATTGTAAACATGTTCTTTCCATTTATGTGAAGACA
TTAGAAAGCTGTCGAGTTTTGTCTTCTTTGTTTTATTGATTCCCACACATTTTGTTGCCATATAGGAAAGTTCCGCTGATGATCATCTATTAACA
ATGTGCTGATCATTATATCACTTTTGTTTTCAGCGAGTGAGTTACACATCATTTTTGCGCATTGGTTGTACGTACTATCGCCAACTGATTTATTT
TTATGGCCTGGCATTGAAAACTGTTGCAGTTGCGAGTGTGTATTGGGATTTGCATTTGTATTAAGTATCTGCGCGGGTGGGGTGGACCATCTGTC
TGCTCGTGTGGGCGCCAAAAAGTCAATCCCTGGCCAAGCAGAGAAATGCCAGAAATAGCAGGGAAGGCTTTTTCTTCATAAATATCTCACTTTCG
TAAACATTTTTTGTCCGCGCGTCTTGCCGTGTGTTTGCCGTTTTTTGTTGTTTTTATTTTTATATATTTTATTTGTTTATTTGCACAGTGTTAAA
ACCCACCTGTTGTTGTTTTTGTTGCTGCTTTCGTTGTCAATCAAAGATTGTTGCAAAAATTTCACCTGCTGAAAACGAAGAAAAGGCTGAAATGA
TTTTGCAATACAATGGAATATGGAAAACGTACTCTGTTGTATGTATTGTTTTGGATGGCTAGCGATGGCTAGCTGCAGTTTTTCTTCTATTTTCT
TTTTGGCAACAATCGGCTTAATCCAAACCAATTGGACCAAAAATGGCCGCGTTGCGAGCGCTGCCTTTGGCGCCTGCTGGAACACTACTCTGGTC
CCAGGAGCTGCAGGACCTGGACTGCAGCTACTCCTCCGCATTAATGTGTATCCCGCCTGGAGCCTTCCAGTCTGCAGCTCGCTTCCAGTTCGGAG
ATTGCACTCGTTTTGGGGGTTGCAACCAGTTCCAGGAACAGTGGAGACACCGTATGACAAACGCCGGTGTACGGAGCATTGAGTGTTGGACCCTT
CTGGTCGGTCCTGCTCGCCTGCTGTTGTTGGCAGCAGTCTGTGCCGTGGCCACGCCCCCGTCAAACGGCAGCTTCCCACCACCGCCCCCGGAAAC
GGATGCAGCTGCGCTGCAAGCCGTGCGGCGTCATTTGTGTGGGCGCTTTGGAAAATGCGGCACAGGCGCGCAGGAATCGCCGGAAGAGCGGAAGT
GCGACGCCTTCCAGCGCAACAATTGCAACCAAAGTTGGGTACTGTGGGATAAGTTCGAACAAAATGGGTCAAATATGAGGAATCTATGAGCAATA
GAGTTTATGTTGCGCCTTATCAGTCGAAGATTTCAGGATCAATAAGCTTTTAAAAGCTATTTATTGTTTCCTAAAATTATTATTATATCTAAACG
TTGAAAAATATATAAAAAGTACATTGAAATTGACAAGGCTAACGCGTTTTTGGTGATTGATTTTTAATGTATACATTATGGTAGCTCGTCAAGCA
TGCCAAAAATAATTATTTGATGACCTCAGTGTGTAGAGTTGGGAAATGAGAACTGCCATGAATTGTGGGTCAATGATTGTTTATTTATATCAATT
ATAAAGAAATATAGAAATATAAAATTGTTCAAACTTTTTGTTCCATTTGTTCCACTTTTCTAAAGAGCGCCTGTTAAGATACTCCCACTGTGCGA
CTTGGCACGACTTGGCACCCTGCACCCTTTTATGACAGCCTGTTGCACGTTGAACTTTGCTCCCACGCGTTTGGATGCTCCTCCCCGCGCCGCCC
CCTTTGTAGGCAGTGTGTGTGTGTGTGTGTGCAAAGTGTGTTCGATGATGGCCAGCTGTTTGCTGCAAGGTGCGTGGGTCGCACCACAGACACTT
GTGCCAGGAACGCAGGAGTGGAAGTAATCGCCCCCTTGAAGGGAATGGCCAGACGGGAGGAGTGTCTAGCGGAGTGGAGGGGAAGATGCATCTCC
GCATACCCGCATCTGTAGCAGTGCGAGCAGCTGCGTTTCCAACATTTATCGGGGATGCAGCAGCAGCTTTTCGGGCGCATGTCCACAATGAAGAG
AGCCGGCGAGTTCGATTTGATTAAGGGCCACTCCGATAAAGGGGTTCCAATGCTTCCAGTTACATGCTCATATATATGAACATATGTGTGAATGG
ATATGGCTCCGCCAGTCGAAGTGCAGTAAGTCGAATCACCCTGGTGCGGAACTCCTTGCGCATTCCGGACTAACTGCCTAGCATCCGGACCCACC
ATGCAAGCATGATTAGAAGAAGGGCACAACTCGGCATCGCCGTGTTCGCTACTACTCCTTCGATTTTCCAGCTACGCGTGGTTTCGGATGCTGCC
GATTTTTAGCCACCAACTTGACATTCATGCTCGCCTGTTCGCTAACAGATAAAATCGATAATGTGCGAAATGGCAATGCCGCTTTACTCAAATAT
TTGGTGAGAGTTCGGATTCAGATTCGGATTCGTTACGTTGGTTGGGGGATCGGACTTCGTTTGGTTATGACCTAAGCATAAAATATAGGGGATGT
TGGCTGAAGGCAAAACGAATTATTTAGTTGTGTGCTTGATTTACAAAGCGCCAACAGGAGCGCAGAAATTTTATTCTACTTATTGATTTTAATTT
GTGGTAGTGCTGGATTAAAGCACTGGGAAAAATGTAACCCACATTAAACCCAAGTGTTGCCTTATTTGTATGAGTTAATATATGATTAGTGTAAT
ATTTTCGGATGTAATAGAACTTCATATCGTTTCTGCTAGCCCATGCTGGCATTGCCAAACTGAATCGATTATTCAGATGACCTTCTTTTCGCATC
ACAGTGAATTGTCTGATGGGAAGCCAGAAAGCGTGAAAAGCGATCGGCGCCTGGCGGAACTCAGTTCTGTTTGTGGCAACTAGTGTGGGCGGGGA
AAATCTCTTCCTGGCTGGCTGGCGAATAAATTAAGCAAATGATAAATAGATTTCTGAAACAACCCTGCCTCGTACTCATTATTCGTAACGCCCAC
TTACTGCGCTCAATTATTGTCATTGCGAAGTGTTTGAAGTGCTTTCAGGCGTTTGTTTGGCAAGCAAAAATCATTTAGCTCTTCAGGGCGGCAAA
AAACTCCTCCATTGGATACATCTTCTTCGCATATTATCCACAAAGCGGTTTCAATGCCTTTCGAAAGTTGCCCCACACACTGTCAAGTGTTTTTC
TATACCCGTGGTGATAATTATGTACATCTTAAAGAAATAAATGCAAGTTAACTGCACCGGCAATTTGCATACTAAAAGTTCATTAATATCCACAA
TCGATGTGGATGATGTTGCATAAATTAAAAGAAATGCTAGTCGTTAACGTAAAGATTAGTTGAAATTATAAAAGTTGTGGTTAAAAGTTTTAGCA
TATTATTTTCAATTCAGTCATTTACATACATATGCGTCGTAATAAACCTTAAAATATTTATTTTACAATGCACAATGTAAACAATGCCTTGTTTT
TGGTTGCTTTATGTTGGAAAAGAAAGGCATTGTTTATACTTATATAGATAAATATGTTTATTTATTTAACTTATAATAAACCCAACCGAACTGTA
CTGCTTATGGCAGTTCCTTGATTTGGAACCTGATCCCAACGCCAACTCAGAGTTTGAAACGTGGGCGCAACTTGTTTTCATATCGGGGGGGTCTT
TGAACGCCGACGAAAACAACACGCTGCACATTTTAAAGCGCAAGCATAAATCATGTAAACAAGAACAACGAGAATCAAAGGCGGAACTCCCCTCT
CTGTCGCAGTCATTTTGGGTGTGGTCAGTGGCCCCAGTTTAATGCCACTGAATAATTCATTCAAGAAAAGCCATTTCCCTGTCGCCGGCGGATTG
ATGAATATGCATCGTGTGGCCAGCACCGAGGCCTCCTTCAGTTTTTCAGGTTATTTGGCAAAAAAAAAACCACACAAGACAAGAGTCAGAGCAGG
AGCTCAAGAGTCAGCTTATACAGTAAACATAACTTAAGGCGGAATATGACATGAAAATACGTATTAAAAATAAGTGGTAGCTTGGTTGAAGTAGT
TGTTGGTCTGAATAGTTTTATTCATTTATACAATGTTGCAACTCAATGGTGTTTACTTGACTACTTTCCATTACGTTCCCCTGAGGAAAGTGCAG
CTCCGTTAATGTCACAGTTAAAGAAGTCGTACTGTACTTAATGGGCGACCTCTCCACCCTTTTCTTTTGCTGATTCCCTGTGCTTGGTCGAGTTG
GTTCGGTTCGGTTGGTGGTTTTCTCGGTTCGATTGCACACGAGTGCGACTACGATTATTTTCAGCTGTGCGGTTTCTTACCGCTGTTGTTCAGTT
TTTTCTTTCTTTCTTCTCTCTTTTTTTTAATTTTTGTAAGCTTTTCTGCTTTATTTTCTGTTCGGTTCCATTTTTCAAGAGAGAGCGAAGAAAAG
TGTGTCGCACTCTGCAGCTTCTGCTGCATTTCTGGTGGCCCAGCATCGGCAGAGTCTTTAAAATCCGGGTTTGTGAGGCGAGCTTGGGTTCCGAG
CCAGCCTTTCGGTTTGAGTTTCACTATTTGGGTCAGCGATGATGAAAGCGCCAGCGCCGTTCGTGATGTTGATGATGACGATGGGGCTTAATGAT
CACCACGCTCGCAAACTATTTTCCGCGCTGTAACTAAACGAGCGCGCGTCTGTTTGTTGTTTTTAAGTTTTACAGCGCCTTTGGAACAGGCGCTC
AGTTTTTCAAGCAGCGCTGCTGCACTTACAGTTGCACTTGCTCGCTTACAATGAAAAAACGACAGCGGCAGCAAAAGCAACGAAACAACGGCAAC
AGAAGCAGTGGGCAAGCAGTTCAATGCACACAACAACAGTAGCCACCCGTACATGTGTGCATGTGTGACTTGACTGCTTTGTAACGGCAGCTTCT
CCGACTTGGAGCGCACTCACACTCAAACACTCACTCGCGCATCGGCCATCGATGGGGCTTATATTTTCTTTCCGACAGTCCCATCTCTCTCACAC
TCATCACCTCGCCTGCTCCCGCTCGCATCATCTGTCAAACAGTGCTGCCGAAAGTAGCTGCATGGAACCTCAAAAGTAGCTAAACTCTTTTAAGA
CTAGCTTTGGCATTTCGAGCTTTGATATTTGCTATTTTTATTTATTATTATTATTATTTTGATCCGTAGATCCATTTTTCACCTTCGTATTAATA
GTTCAACCGCTAAAACAGTGAACGCATTTATCATTAAATTAATTTCCAACACTGTAAGCCAAATACTCGATTAAATTGTAATCAATAAGTATTTA

FIGURE SHEET 393

ATAAATAGTAAAGCAATAGTAGTTTTGTACTGATGTGTTTTATCTTAAACCTATCGTTATGCAATTCAAAAATGCTAAAAATACAATAAAAGCAC
CATAAAAAGCGATTGGCTTTTGCGTGTTTCCGTCGGCGTTTTTCTTGGTAATTGTAATTGCGTTTTAGTTGTTTTGCTCGTTCGCTTCGCACTGC
GCACTTGTGTGCAGTAGTTTTGAGTCCCCACACACAGACACACATGCGCCCCACTAAGTTTTCATCGGGTTTGTTTTGCTCGCTGCTTCGCTTTT
GTTGTTGCCAATTTTTGCGCAGCTACGGCGGTCTTCGTCTTTTTATAGTTTTTGTTTTTCTCTCCTCCATTTGTTTTGCACATTTCTCTCTGTGA
GCTAGAAACCTGTTTTCCCAAGGTGTTTGTTTTTGCACGAGTCGTTTTATTTTGAGGCTATATTATTATTGTGCTTTTATCTAGTCGCAGTTGTT
TGTCTGGGACAGCTGGCTGGGGGCCACGCCCCCATTCGCCGCCACCGCCCCCTTGCTCGCCTTTCCTTCTATTTTTAGCCAGTCGCCTAAACAAC
CTTTAGAATTCTTTTTGATTAGCACACAAAATACGTATTATTTTGTTTCTTATGAATTGGTTATACTTGTTGTGAATTTATTACTGTATCTCGAT
GGTTAATTGGCGTTGTAACTTGGCCATTACCCCCCTTAGCTTATCTGTTTTAACCCTTGAGCGGCAGATAGCAACCAGTCGAAGCCGAACGATCC
AGATTCCAGTTCTCCTACCCTGGTAGCGTCCAAGTTCCATTGAACTCGGGTTAGGAATGTCTATATAGTATATGTATACACACATTGCGAATGCA
TGAAAACCAGTTGCACTCCGCGTTCTAATCTCGCTGTCCATTAAGAAGCGTCTCCGGCATCGCTGATTTATGCAAACCATTGACTTTACACACTG
CCCGTCAAATACTTAATGTTTACCCGAAGTGAATGGGTACTAAGGTCATTCGTAAATGGATCCCATTTGTGGCAAGAAAAGTTGCACAACTTTAT
TCAAACGATTATTTTACCACATAATCCTTACCTATTACATCTACTTTTAGCATATATGTATTATATTAACTCCCTATTCATGGTATCCTGATCTT
TTTCCTTTCCTTTTAGGAGTACGACATCTCCAAAAAATGCGAATACCTGTTTAAGCTCGACTACAGCCTAATTGAGCTGGATAATACGAACGGAT
TGCTCAGTCCGCGATATCCTGGCCGAATACTCATCCCGGAATATGAGCACGGGCACATGGCCAAGACGCTGGTACCGGGAAATGGACTCTTCGGG
CAAGTTGGTGGGGGAGTGGGAGGTGGAGGCTCCTCGGGAACAACCGCCACTGCCACGCCTCTGAACAGCAGTGCAGGAAGCACCGGAAGTGAGGG
TGTGGGCATCCAAGCCTTTGTGACCTTTGCCAATCCCCTGCAGACGCAACAACAGCATCCGCTCCAGCAACAATATCCCTCGCAGCAGATGCATC
CCCTCCACGCGCAATATCCCTCCCAGCAGCCACATCCACTCCAGCAGCAGCAGCAGCAGCCATCGCAACAGCAACCACAAAATACGATATACGAG
GATCAGTATGATATCCAGCGAATGCGGGAATTGGTAACGATGGCCAAATATGCGAGATGCCGTCAAAGATTCGCCGTGCCTGTGATTATGTATCG
CGGAAAGTACATATGCCGCTCTGCCACGCTATCCGTCATGCCAGAAACCTACGGCCGAAAAGTGGTGGACTATGCCTACGACTGCCTGAGTGGCG
GCAATTACACCGCGCCAAACGGAGAAGAGAACGATGCTGACTCCACGGACGAGTCGCTGATCACCCACATGCACGACCAGGCGCAGTCGCAGTTC
AGCTACGACGAAGTCATCAAGAGTGACATCCAGCTGCTGCATACGCTCAATGTCTCAACCATTGTGGACCTCATGGTCGAAAACCGCAAAATCAA
ATACTTCATGGCGTGAGTACACTTTAAGATACCGAGTACAAAACAAAAACTGACCACCTGTTTTTTTGTTCTTTTAGCGTTTCCTCGTCAGAGA
AAGCGGATCCCAACAAGCACTATAAGAGCTTTAACCTTCTATCCCTGCCGTATCCGGGCTGTGAGTTCTTCAAAAAGTTCCGGGACAATAATTAC
ATGGCTCGCAACCTGCACTACAACTGGAAGCAAACGTTCAACGATGCGAATATCAACATTCCCAACATGGGACCCGCTGCGGATATCGATGTGGC
GTGGTCGGAGTACCGGGATTGGGATCTGGTGGCAATCACCCAAAACTATTTGAGAGCTACACTGAAATACGTGCAAGAGGAAAACTCCGGCCTGC
TGATTCACTGCATCAGCGGTTGGGATCGCACGCCACTGTTTGTCTCCTTGGTCAGGCTGTCTCTGTGGGCAGATGGACTCATCCATCAGTCGCTG
AACGCCATGCAAATGGCCTATTTCACACTGGCCTACGACTGGTACCTGTTTGGCCATCAACTTCCCGATCGCCTGAAACGAGGCGAAGACATCAT
GTTCTTCTGCTTCCACGTGCTGAAGTTTATCACGGACGAGGAGTTCAGCATTGTGGAGCACCGCAAGCGCACCAAGACATCCAGCAGCAGCGGCA
GTAGTGTAATAGTAATCAAATCCGATTGCTGCGACGATGAACCGCTCAAGGAGTGAGTATAGCCAAAGACACTAGAATTATAGCCAAGTATTGTA
AATGAACAGTACCATTATCAGTCCATTTACTTTGAATTGCAGAGACTACATCCTTTCGTTCGATCAAGATAGCAACGACAGCTACTCAAACTGTT
CCAACTGTGATATGTCCATAACAGATAACTTCTATGCCACGACGCCGGCGCAAGTCAATCCGTTGACCAGCAGGTCGCCAAATCCGAAGAGGTTG
AACAGCTGAATACTAAAATTAGAAACCTGACTAACTGTGAACTCAACTTGTTTTAGATCTAGAACCAGCCCCATTTCAGTGCCCGGATCAAATGC
GCGGCAAAGACAGGAGTCTACATCGTCCAATGGTAGCTGGCAGGTGGTTACCGACACGGGTTCAATTGACTCCATGATGAACGGCAGCTACATGA
TGCGCTTTGTGGCGCAACAGGCAGCCGATGGTGGCGGCTCCTCAAACATTCCTTTATGCAATGGCGGCAATGGTTACCACTGCAGCATCAATGCA
GCATCGAGTGGCAGTGGGAGCGGAAGTGGTAGCAGTATCAGTAACGGCAGCTCGACGCACGGTTTCGCAAACGGTTCCTCCAAAGACGTAGGCGG
CAGCACTATGGCCAGCAAGCAATGCATCAACTTGTAAGTTGTAGTCTGATTATTCGACAGCAAATACATAATGACATAATTTTGTTTTACAATTG
GAGACGAAAGCAACGCCTGAATGCAGTGCGCGCCATTTTTATACAAGCCTACGGCAAGACGATTGGACTGAAATTCAAGGAGGGCTCATCCATGA
ACCTGGCCACGTTCATTGGGAACCTGGCGGACCAACTGTTTTGAGAAAGGATTAGCAGCTATGACCGTTTGTTAGATTTCATCAACATTGTTTGT
TTCTTGTTAAGTGCTACGCTTTCAACCAACGACTGTATTTATAGACCTGTTAAATTGCGTTCTTTAGTATCTGTTGACGATTGTGTAGTGTAACG
GATTACTGATTACCGATAAGCATCGAAAGAACCAGGCGATCGTAGGCAACGAGCAAACAAAATCCTGTCGTCCTTCTGCCCCGGCTAAACCGCTC
TCCTGTTCTCTAGGTTCTCCCGCTCCTTGTTTGTTTAGTTATTAGTTCTTCGAGAATGCAAAGCAAGTGAAATATAAAATGCTATTTGGATTATA
CAATAGTTTTAAGTTGTAATTTATAGTAATGTATTTTTTAATAAACTTATGTGCATTTTATACGAAAGAAAGTCATGTTCTCAGCGTAGGCCGCC
TTGAGCGCCGTATTCTAGCTAAGGGTAAATAATCATCAATTTCCACTCGCTTCAGCCGGATGCGACACCTTTTAATGTAGTATTTCGCGCTTTTA
AGAGGAACGAAGCGTGGTGTTTCTATCGGTCGTTCGTCACATTTTGTTGTATCTTTAATTTTAGGTTCAATAGCTGTTTCTATTTTGATTTTGAC
ATCATTTGATCCTTTGCAAGCATTATTATATCTGATTCTTTTATTGGCACTTGCGACATTGGGTCTTATTTTGTGTGGGCTAATGCCGAATCTGT
CCATGGCCGGACTGAGTAAATTGTCTGCTGGGAGCTCTTTCACCCGTATCGCTTTAAGAAATTCGTCGTATTCGCTCTGAACCGTCTCCAGGTCC
TTAGGACCCAGCTTTCGAGTAGCTTTCTCTTGGCGCTCTTGCTCCAGGATGAGGGCGAGGACCTCCACTTCTAAATGCCGGCGTTCCGCTTGCGC
CATAGATTTCACGAAAGGCAACTGACTGAGAAGAAACTCCTGACACTTGGTTTTCGGCACATCCGCCGGATTCGGGGCTTGCATGCGAATGTGCA
CATCGTGCATCACCCGCCACAGAGGTTCAGGGATTTGCCCTTTGGAACCGGCCAAGGCTCTGACCAGCGGGCGCAGCTTCACCCAACGCAGCTTC
AGTTCACTTACGGAGAACGGAGTACTCAGCTCAACGTGCTCGTAGCTTTGGTTAAAGGACTTGGCCAGCTGATCCCAACCCCAGGAGTCGTAGTC
AACGTCCATTTTGGGCTCCACCTGCGGGATGATAAGGAAGGGATACCGGGCGAGCATCTCCATGAGCAGCAAGTCGTTTAAAACAATCTGGCCGC
TGATGTTGGTGTTTGATATGTTAATCTCCAAATGGGGAACAGTGGAATGGATCACCGTTTCCTCGGCGCTGTCGGTACTCATTTTAATATTTTTC
GCACTGTGTTTCTCCAACG
(SEQ ID NO: 724)

Exon: 1001..1581
Exon: 10942..11792
Exon: 11859..12497
Exon: 12583..12726
Exon: 12787..13143
Exon: 13209..13744
Start ATG: 1465

Transcript No. : CT20377
CTGTTTGACGTTTGTCGCTTTCCTCCGTTGCGAATATAATATATTACGTAGCTCATTTTTATACAAACGGAATTACGAGCGCAACGACGACAGCA
ACACTAGTAGCACTAATCGTAAGCGCAGGGGCCAAAAATTAAATTGCGTTTGCGGCCGCAAAGATTTGATGACGTCGCATACGCCGTCTTCTAGG
GCGTAAAAAGCAAAGCAAAGCAAACAAACGCGAAAGCGAAACGTGTAAACGGCGTAGAAGCGATAAACGCGACTCAAATACGCAGCAGATAAAAT
ACAATACGCGAGAAGAGAAAAGTCACGGGAAATATTGTTCATATTCGGCGTCTTTCTGCGAGCGTAAACGTGTGTGCGTGGGCTTGTGCTTTTGC
CAGTGTCGTGTGTGTTAAGTGCCTGTGTGTGTGTGTGATTAAGAAGATATAAAGGAATATAACGGTAAATGCAGCGCCGCAAAAATGTGCAGCCT
GACGCCAAACCACATGGTAAACGTAACGCAGCAGCACCTACACGATCTATTGGAAACTTTCGAAAAAAAGTCCTTCGAGGCGGCGGCCTTTGAGG
AAGGGACGGCGGAGTACGACATCTCCAAAAAATGCGAATACCTGTTTAAGCTCGACTACAGCCTAATTGAGCTGGATAATACGAACGGATTGCTC AGTCCGCGATATCCTGGCCGAATACTCATCCCGGAATATGAGCACGGGCACATGGCCAAGACGCTGGTACCGGGAAATGGACTCTTCGGGCAAGT
TGGTGGGGGAGTGGGAGGTGGAGGCTCCTCGGGAACAACCGCCACTGCCACGCCTCTGAACAGCAGTGCAGGAAGCACCGGAAGTGAGGGTGTGG
GCATCCAAGCCTTTGTGACCTTTGCCAATCCCCTGCAGACGCAACAACAGCATCCGCTCCAGCAACAATATCCCTCGCAGCAGATGCATCCCCTC
CACGCGCAATATCCCTCCCAGCAGCCACATCCACTCCAGCAGCAGCAGCAGCAGCCATCGCAACAGCAACCACAAAATACGATATACGAGGATCA
GTATGATATCCAGCGAATGCGGGAATTGGTAACGATGGCCAAATATGCGAGATGCCGTCAAAGATTCGCCGTGCCTGTGATTATGTATCGCGGAA
AGTACATATGCCGCTCTGCCACGCTATCCGTCATGCCAGAAACCTACGGCCGAAAAGTGGTGGACTATGCCTACGACTGCCTGAGTGGCGGCAAT
TACACCGCGCCAAACGGAGAAGAGAACGATGCTGACTCCACGGACGAGTCGCTGATCACCCACATGCACGACCAGGCGCAGTCGCAGTTCAGCTA
CGACGAAGTCATCAAGAGTGACATCCAGCTGCTGCATACGCTCAATGTCTCAACCATTGTGGACCTCATGGTCGAAAACCGCAAAATCAAATACT
TCATGGCCGTTTCCTCGTCAGAGAAAGCGGATCCCAACAAGCACTATAAGAGCTTTAACCTTCTATCCCTGCCGTATCCGGGCTGTGAGTTCTTC
AAAAAGTTCCGGGACAATAATTACATGGCTCGCAACCTGCACTACAACTGGAAGCAAACGTTCAACGATGCGAATATCAACATTCCCAACATGGG
ACCCGCTGCGGATATCGATGTGGCGTGGTCGGAGTACCGGGATTGGGATCTGGTGGCAATCACCCAAAACTATTTGAGAGCTACACTGAAATACG
TGCAAGAGGAAAACTCCGGCCTGCTGATTCACTGCATCAGCGGTTGGGATCGCACGCCACTGTTTGTCTCCTTGGTCAGGCTGTCTCTGTGGGCA
GATGGACTCATCCATCAGTCGCTGAACGCCATGCAAATGGCCTATTTCACACTGGCCTACGACTGGTACCTGTTTGGCCATCAACTTCCCGATCG
CCTGAAACGAGGCGAAGACATCATGTTCTTCTGCTTCCACGTGCTGAAGTTTATCACGGACGAGGAGTTCAGCATTGTGGAGCACCGCAAGCGCA
CCAAGACATCCAGCAGCAGCGGCAGTAGTGTAATAGTAATCAAATCCGATTGCTGCGACGATGAACCGCTCAAGGAAGACTACATCCTTTCGTTC
GATCAAGATAGCAACGACAGCTACTCAAACTGTTCCAACTGTGATATGTCCATAACAGATAACTTCTATGCCACGACGCCGGCGCAAGTCAATCC
GTTGACCAGCAGGTCGCCAAATCCGAAGAGATCTAGAACCAGCCCCATTTCAGTGCCCGGATCAAATGCGCGGCAAAGACAGGAGTCTACATCGT
CCAATGGTAGCTGGCAGGTGGTTACCGACACGGGTTCAATTGACTCCATGATGAACGGCAGCTACATGATGCGCTTTGTGGCGCAACAGGCAGCC
GATGGTGGCGGCTCCTCAAACATTCCTTTATGCAATGGCGGCAATGGTTACCACTGCAGCATCAATGCAGCATCGAGTGGCAGTGGGAGCGGAAG
TGGTAGCAGTATCAGTAACGGCAGCTCGACGCACGGTTTCGCAAACGGTTCCTCCAAAGACGTAGGCGGCAGCACTATGGCCAGCAAGCAATGCA
TCAACTTACGAAAGCAACGCCTGAATGCAGTGCGCGCCATTTTTATACAAGCCTACGGCAAGACGATTGGACTGAAATTCAAGGAGGGCTCATCC
ATGAACCTGGCCACGTTCATTGGGAACCTGGCGGACCAACTGTTTTGAGAAAGGATTAGCAGCTATGACCGTTTGTTAGATTTCATCAACATTGT
TTGTTTCTTGTTAAGTGCTACGCTTTCAACCAACGACTGTATTTATAGACCTGTTAAATTGCGTTCTTTAGTATCTGTTGACGATTGTGTAGTGT
AACGGATTACTGATTACCGATAAGCATCGAAAGAACCAGGCGATCGTAGGCAACGAGCAAACAAAATCCTGTCGTCCTTCTGCCCCGGCTAAACC
GCTCTCCTGTTCTCTAGGTTCTCCCGCTCCTTGTTTGTTTAGTTATTAGTTCTTCGAGAATGCAAAGCAAGTGAAATATAAAATGCTATTTGGAT
TATACAATAGTTTTAAGTTGTAATTTATAGTAATGTATTTTTTAATAAACTTATGTGCATTTTATACG
(SEQ ID NO: 725)

Start ATG: 465

MCSLTPNHMVNVTQQHLHDLLETFEKKSFEAAAFEEGTAEYDISKKCEYLFKLDYSLIELDNTNGLLSPRYPGRILIPEYEHGHMAKTLVPGNGL
FGQVGGGVGGGGSSGTTATATPLNSSAGSTGSEGVGIQAFVTFANPLQTQQQHPLQQQYPSQQMHPLHAQYPSQQPHPLQQQQQQPSQQQPQNTI
YEDQYDIQRMRELVTMAKYARCRQRFAVPVIMYRGKYICRSATLSVMPETYGRKVVDYAYDCLSGGNYTAPNGEENDADSTDESLITHMHDQAQS
QFSYDEVIKSDIQLLHTLNVSTIVDLMVENRKIKYFMAVSSSEKADPNKHYKSFNLLSLPYPGCEFFKKFRDNNYMARNLHYNWKQTFNDANINI
PNMGPAADIDVAWSEYRDWDLVAITQNYLRATLKYVQEENSGLLIHCISGWDRTPLFVSLVRLSLWADGLIHQSLNAMQMAYFTLAYDWYLFGHQ
LPDRLKRGEDIMFFCFHVLKFITDEEFSIVEHRKRTKTSSSSGSSVIVIKSDCCDDEPLKEDYILSFDQDSNDSYSNCSNCDMSITDNFYATTPA
QVNPLTSRSPNPKRSRTSPISVPGSNARQRQESTSSNGSWQVVTDTGSIDSMMNGSYMMRFVAQQAADGGGSSNIPLCNGGNGYHCSINAASSGS
GSGSGSSISNGSSTHGFANGSSKDVGGSTMASKQCINLRKQRLNAVRAIFIQAYGKTIGLKFKEGSSMNLATFIGNLADQLF*
(SEQ ID NO: 726)

Classification: protein_phosphatase
Gene Symbol: BcDNA:LD23181
FlyBase ID: FBgn0027506

Celera Sequence No. : 142000013384666
TGCGGCATTAAAAAGTCGTTCGTTACCTGTCGGAGCTAGCGGAACTCGATGGGTTGTAGAACTTGATTTGTTTCGTCTGGGTCACAGACATTTCG
ACAAGAGAATAGTGATTGCAGCAGCCAGTTGCAGCGATTAGAAAAAAACACGCGGTGATTTACTTCGTCGTGCCTCTCCCTCTCCGAGCAAGTGA
CTGATTCGTTTCTGAAGGCATTGCGTTGGAAAAACGTGCGCCGCCTTCGTATACATACATATGTATACATCTACCCGAGCTTGAATGGTCAAGTA
AAGTGCTAATTGTCAGCTGGGGAAAGGCACTGGAGCGGAGGGACGCTCATTGCCTTGTTTATCTCCATTTGATGCTGTCATTGAGGCATTTATTT
ATATGTTTTGGGGCAATTCAATTCCATTCGCAAGGCGCTCAGCTGTTTGATTGGGGCGGCGACAGTGTTGCGAAGCGCTGTTGGCTGTTGGGTTG
CAGTAAATTCGAATGTGAATGGCTAAATCCGAAGCGGGGTTTTTAAATGTTTGATAATTATTACTTCGAGCTTGTGTCAATATAAGTGAATATTT
TACATAAAACTTTGTGGTTTCTAAAAGATTAGCTTACAACATGATCTTTAGGTACTAACAAATAAAAGGTTGTAAATAGCGGTAGTGCTCGGAAA
ATATATCAACATGAGACAATTACCAATTCGATTATTTTTTGTTGGTCCTCTATCGATAACTGTTACTCTTACTCTCTTGCACTGCAAGCCAAATT
CATATTAATTAAGACTATAAAAATAAACACATACAGAAACATGTGGCTGTTTCCTGGCTATCTTGGATGGAGAAAGTAGTATGTAGTAGTATCAT
AATTTATAGTTTTCTTTCCTCTTGTTCTGTCCCTTAAAGAAACTTTGAATAAATTGCATTTTGTTCAGTTTTAAAATGCATTAAATAATCGATTG
CCACGCTAGTTCGATAGTATTTAACGAGCACCGAGTATTGTTCGAGCTCTAAAAGATGGTCACTCCGGACCAGAGAGACGCAACAATATAGCAAT
TCTGAACTTGGTTCGAGTGTTTTTGCAGCACGAATTGATAATATGCCGTAGGTGCGGCCCAGCGCGGATCATCAGCAGCAGCAGCGATGGCCTAC
ATCAACATCGCCGAGTGGACGCCCGACCAGGTCACCGACTGGATAAAAGGTAATGCTCGAGGTCAAGGAAAGCGCAGCTGAGAAAAAAAAAACTG
CATCTCGCAGCCACTGCCCCAAAAAGCAGCAGCAACAACAAGTGCAACAAGAATTTCCGCTTTGTTCAAGGTTTCAACAGGCACATCATAATAAT
TATGTTTTCCTGATTCTCGCAGGTCTGGATGAGTCTATGAAGGGGTATTTGTACGAGTTCTCCAAGCAGGAGATCGGCGGACGGGCGTTGCTCAA
CATACGGCCATACGAGCTGGAGAATCTGGGCATGCTGCGCATTGGCCATCAGGAGATCGTGCTGGAGGCGGTGGAGAACTTAAGAAACTTCGTGA
GACCCCAAACAAATATTGTGACATACAAACCCGTTAATTGAGCTTGATATTCCAGCATTATCACCTGAAAAACGACAATCTGCAGTTCATGGCCT
TGCATGTGGCCACGGCAGCTAAGAATCTGCATCGCGAACTGGCCAGGAATCATGCGGAGAGCACTAAGATCGATACCCGGATACTGCACGATATT
ACCAGGACGATAGCTACTCTAAAGCCATTGGTGGGCAGCCTGGAGCGAACACCGTTCCGTAAGCAGGAGATGTACCGCGAGTATTGTGGCAATGT
GCTCAAATGCGGCCTGGAGCTGGCCACAATTGCCCACCGTGATCGTTTTGCCCTGCAGCCGGTGCCAGCGATTCGACAGTCAGCGGAACGGCTCG
AGAATCTTGCCAACTTTGTAATCCAGGACATATCTGATCCCATGGTACTGCAGCCAGCCTCTCTGAACCTTGTCACCCTTAAAAAACGCGAATCC
GAGTTGGGTTTCAACATAGAGTCCAGTTATAATGGCATTCACCGTGTCACGGATATCAAGTACAACTCGCCAGCTCACAATTCCGGAAAAATCGA
AGATGGCGACGAGATTGTGCAGATCAACTACCAGACCGTTGTGGGCTGGCAGCATCGCACAGTACTGGAGCATCTGAGGGAAGCACTTCCAGATG
TGGTGCTGACGGTGAAGAAACGGCCGAAGCACACAAAGATGTTTGGACAGATCTATATGCAGCCGTACAGGTTGCCCAGCAAGAAGAGGAATATG
GCCGCCCGCTGGGCGGCACAGATGCCAAGTCCCCGTGCTGCATTTTTAACCCTGGACACGGAGCAACTGGCAACAGGAGGAACAGGAAGCGCGGT GCCAGATCCCAGTAAATCCCTAAGCAGTGAGAAGAGGGAGGTACTTACCAAGGCCAATCCAGTGTCCTCTGCCTCCGACTCTGATTCCAGTTGCA
GTGATATTCCAACACCAACGGATCCCAAGCTAGCCGCACGGGAGATCCGTTTGTATTACCCAAAGCCAAGAGCTTTGCTCCAACGAAGAAACACT
ATTTGTGGATGCGAGTATCTTAGCCTGAAAAACTCGGATCTAGTCGTTCCATCGTGGCACGAAAGAAAGCCAGGAATTGGTTCGCCCACCAATTG
CGACCCTGGCTCGCCCAGTATACGGGATAAGTCGATATCCTTCGGTTATGGCCTAGAGATGGCAGCAAGGCCGACCACTTGCATTGGGATTGCGG
GCGATACCTCCACGGACAAGGCCAGGCGAATGTTTCATGAGGCGCGAAAACTAAAGCAGCTGACGGAGGACTCGCAGCGCGAATTCCTCGTGGAT
CGTTACAAGCCGGGTGTCAGCAAAGTAGTTCGGTTCGACGCCAAGGAAGATTATGTGATGAAGAATGAAAAATTTATCTGTAACGTTGAGAACAC
CATACTGGAGACCTTTGAACCGATTCCCTTTGCGGATGAGGGAGACGAGGACGCCTTGGAAACGCTGCGCAACTGCAAAACAGAAAACGCAGAGG
AGCTCCTAGAGGCAATTAATCTGGCTACAAAAGGTCAGGACTTGCCCCTGGCCGAGGCCATTAACATGCCTTTGTTGCAGCAAGGTCGAAGGGGC
CGATTAGACAAGAGTCATAGTACTCCGGCATACGATAATTCGGGTGAAGAATCGGATACGCCGCCAGCGATTGAGCCAAGAAAGGAGTTCCTGCT
TGTCACACCGCCAGCACCGCCACCGCGACCCCGCAAGCAAAGGGAAATGACGCCACCGGCGGTGCCTCCACCTCCACCAAAACCAGCCAGCATGC
AGCCGGCTAGTAGTATCACCAGTATCTCCATTCCCGTGCCAGTACCTGTACCAGCCGCAGTTGATCCATCGGAGATCAGTGAGCTTCATACGCCC
AGCAAATCCCGGACACTGACCCTTAAAAAGAAGCACAGCTTAATGGCCAAGCGGCGGAACACAAATCTCAAGCTGTTGGGGACTGGGGATATCCA
AGGTCATCTGTACAGGCGCAAGAAAAATCATCGCGGAGTGACTTACTGGGCGAGAATCTATTTCGTGATGCTGGATACGATACTGTACGGATTTC
GCAGTAAGCAGAGTACCAGCGCCAGCTTGGTAATATTTTTACCGGGCTTTACGGTTTCATTGGCAAAAGAAGTGCACTCCAAACCGCATGCCTTT
AAAGTTTACCACACGGCCAAGAGCTTCTACTTTGCGGCCGAGTCGCTGGACGCACTTAACCAATGGGTGGACTTCTTGCGCCAGGCTTCGCTCAA
AGTGCCGCCTAGTACGGGTTCAAAAGGCGGTGGTGACGCAAAGGATTTGTATTCGGAGAACGATAGCTCAGGCGAGGAATGCGATGCCCTTGTGA
TCCAGAATTTAAGCACGCCCTCGCCGCAAGGCAACAAGGAGTCAATGTCCATGTCGATGACACTATCTGGCGGAACACCACCTTCCTCTGCACCC
ATTAAGCATGAACGCGGCTACTTGGACTCGTTTCGCAAATTTACGAATACATTCAAGAGCAGTGCAGCGAAACCGTCGAGCGACATCCCTGTGCC
AACGGAGCAATACCGCAGCTATAGGAAGGTGCCAGGCGGAAGTTTTGGCATTCAGATTGGTGCCAATACACCGGGCTACCATGATCCCGCAATGC
CGCCGACACAGATTCCACCTTTGGTGGGTCCTAAACTGTCGCGTAGCTCAAGTAGGAGTTCGGTGGTCAGTGGAACCGAGTCTGCCGTATCATTA
TCTGCTTCGATTCTGGGTCCGCCCGCGTCGCCAGCGCCAACGCCCACGCCTACAGCCACTCCCACATCGCTGCAGCATCAGAGCTCCGAGGAGAG
TCCAAGTCAGAGCCAGAGCCAGAGTCCCAGTAGCAAGTCGAGTTTGAAGAAGGCACCATTCAACTTCTTGCACGCCTCAAATCCGAATTTGGTGG
AATTCGATTTCCATACCTCGAAAACACTACTCCCCAAGATGAGTGTGGGTAATACACTCGACCATGGCCATAATATACAGGGCTTTGTGACGCTT
AAGGATCTGATGCTGCGCAAACAGGAGGAGGAGGCCCAGGAAATGTACAACAATCGAGTGCACTTGGGTGTGGAGAAGCACAAGCACGCACGGAC
GGAATCCACGGCCAGTCAGCAGAGCGCCATGAGCAGCAGCGTGACAAAGCCGCTGGAAAAGTTGCCCAAGATCCAGAGCGTGAGTCTGCCCAAAA
CACCCGACTACGAGATCAGTTTTAAGCCTGACGACGAGAGTATTAAGAGAACCAGAACTAAGGAAGGTCAGAAGTTGCGCGACTTTGGTTACGAG
CTGATATGTGGGGATGAGCCGAGCACTAGCTCCATCAGCCGGCAAGAGCACCACCATCATCATCATCATCACCAGCACCACCTGCAGCATGTGCA
ACAGCAGCAGCAGCTACAACATCAGCAGACGCAGCAGCAACATAGCAGCAAGGCCAAGCACTTCTTGCGCTCACAGCAGTTACAGCTCTCCAGTT
TCCTGCACAAGAACAGCAGCGGCGGCAGCGGCAAGAGTTCCGGATCCGGTGCGGATCAAAAGAAGTCCAAAGGAAAGTCTAGCGGCGATCGTCGG
TTTCCCTTTTCCAAGCACTCAACTGGCTCCGCGGGCAGTGGCTGTGGGCCGGGTCATGCGATGACTATGACGCTGCCGCTGAACAAGAAGTCCAA
ATCGAATCACGCCTTGGATGGAGCCGTAGGCAATGGAGTCACCATAATCGGCAGCGGCAGCAGCATCAAGAAAAGCCAGACGTACAATCAGGATC
TGCGAGACAAGATAGTGGGCACCAAGTACGATGCGCATCGCAAGAACTCGGCCCCGATACCAATCTTTTCGAAACTCTCCATATCGGGTGGCACG
CCGGCGAAGCCCTCCAAGGAGAATCGTTTCCTGGGCTCACCGCTGCTGCATCGCACGCTGTTCGGGCACCATCACCATCAGCAGCAGGCAGTAAC
GCCACCAAGCAGTGCGGATCCCGATTGCGATCAGGAGATCTTCTCCCAAATCACCCTGCCCACGCACAATCAGGCGGGATATCGAAGTTACCGTG
GACCTGGCATACTAACCACCTCGACCACTAATTTGTGCTCGTCGGAGGGCTTGCAGCCGCCGTTGCCCCCAGCGCCACCGCCTCCCGTCAACACC
AGCAGGCAGAGAGAGGAGGAGCAAGCGGAGGCAACGATATCAGAGTGTGCGGCCACCCCAAAAGTGTCCAGTTCGGGATCTGTGGATTCGAAGGC
GGCAACGCCGGACTATCCAAATATGGAGTGTCCGCCTGTCTTTGAGCCGGAAATCTACTCGCTCAGCGATACCAGCTTGTCCCGCATCGTGATGC
GGACGCCCAGCAGCAGTGGTGCCACCAGTGCCACCGCCAGCACCACCACCACCAACAACAACAACAACAATAATAACACCAATAACAACACCAAC
ACCAACAGCAGTCCCAGTGGCGGCGAACACCATCAGACCTAGATGTGTGATGAAAACTATTGTGAATGCTCGCGGGGATTAGCCCCCGTTTACTT
ATGTATTTATACACACGCATATAGATATATATATATATATTATATATAGCGATATTCTCGTACGATTTAGGTATACAACTTGTTCATTTTGATCG
TCTTCCCTGTCTGTCCACCAGAAACAAACACACGCATACCTGCAATCCCTTCGATTCGAAACCCACTTAGATGTAAATGTTTAATCTGCCTTATT
TGCATTGTATTTCGGTTCTAGGCAAAATGTTTTACACATGTAGTCACGCAAGCAAAACAATGAATTATAGCGAAAATGGAGAATAACTTTAGAAG
TCTGTGCATCGAACAAAGACGGTTCTTTATGATTTGCCTTTGTACGCGATTAACCAAGTTAATCCGAGCTGTTTGATTTGCTCAACAGTTTGTGT
CTAGATTGCGTGTAATATACATATATTATTATGCGAAATGAGATATTATTGTAATGGCATCCAGCGACGCCAATGGAGCCAGAAATGTTGTAGCG
GAATGCAAGAAATATATATATACACAATTACACGAAATATACATGCATACGAATAAAGTCAACTGTACATAATAGAATAACGATCTTTTTATTTT
GGGATTTTTCAAGAAACAGGTTGTTTCATTAGAGGAGGATTGAAAATCTTTTTATGCACGCAACTTATTCAAAGACCTAAGAAATGAGAATCTCT
GGACAGAAGTGCTGAACCCTGCTTCTTTTTACTAATGTAACCAAATCAACTTGATCAAAACGAGTATTACCTTCTATTATTAGTTCGATTTAGAA
TCCCTTTCTTTATTCACATTACATTTGAAATTAGATCAATTTAAAACCACTGCCGCTTACGCAATGTTCTTAATGTGCTGCTCCACCTCCTCCTT
GGTGAACATGTAGAACTCTCTTTCTTTCGTCATGGTCATCACCTCCACATTGGTGGAGTTTAGTTTCTCCTCCATAACCTGTTTAAGTGTGTTGA
GCGAAATGTCGATAGCCTCATCGAGAGTCAAATCGGGTCTAAATAAGTCCTGCAGATTCTGCTGAGCACCTTCGCTGCCCGAGCCAATGGCCTTG
GCTCCGTGGCGCACGAATGTGCCGGAGGGATCCATGTGCCACAACTGGGGTTGTCCCGCCTCGATGCCGGCAAATAGAATGGCCACACCAAAGGG
ACGACTCATGGCGGCGGCACCATCGCTGTCGCCACTATCACCGAACTGGATGGCCAAAGTGGACACAGCCTGGGCGCAGGACTCGATGGACATGC
GCTCGTTGTAGACGAACCAGTGGTTCTGGCACTCCACGCGTGCCCTCTCGATCAGAGTCCTGGCATCGGCCATCAAGCCGGAGGTGGCGCAACCA
ATGTGCTTGTCCACCTCCACAATCTTCTCCACAGTACTGGGTACCATTAGCGGCGAAGTGATGCGCTTCTCCACCGCCAAAACCACTCCTGGAAT
GCAATTTTACCATTAGATCTCCGCGTGTACTTATGGCAGCAAAGAACATACCTTCTGGCGTGCAAATTCCAATTGCTGTGGAGCCCAATTTGATG
GCCTCAATGGCATATTCCACTTGGAAGAGGCGGCC
(SEQ ID NO: 727)

Exon: 1001..1189
Exon: 1353..1516
Exon: 1576..6635
Start ATG: 1132

Transcript No. : CT20428
AAAAGATGGTCACTCCGGACCAGAGAGACGCAACAATATAGCAATTCTGAACTTGGTTCGAGTGTTTTTGCAGCACGAATTGATAATATGCCGTA
GGTGCGGCCCAGCGCGGATCATCAGCAGCAGCAGCGATGGCCTACATCAACATCGCCGAGTGGACGCCCGACCAGGTCACCGACTGGATAAAAGG
TCTGGATGAGTCTATGAAGGGGTATTTGTACGAGTTCTCCAAGCAGGAGATCGGCGGACGGGCGTTGCTCAACATACGGCCATACGAGCTGGAGA
ATCTGGGCATGCTGCGCATTGGCCATCAGGAGATCGTGCTGGAGGCGGTGGAGAACTTAAGAAACTTCCATTATCACCTGAAAAACGACAATCTG
CAGTTCATGGCCTTGCATGTGGCCACGGCAGCTAAGAATCTGCATCGCGAACTGGCCAGGAATCATGCGGAGAGCACTAAGATCGATACCCGGAT
ACTGCACGATATTACCAGGACGATAGCTACTCTAAAGCCATTGGTGGGCAGCCTGGAGCGAACACCGTTCCGTAAGCAGGAGATGTACCGCGAGT
ATTGTGGCAATGTGCTCAAATGCGGCCTGGAGCTGGCCACAATTGCCCACCGTGATCGTTTTGCCCTGCAGCCGGTGCCAGCGATTCGACAGTCA GCGGAACGGCTCGAGAATCTTGCCAACTTTGTAATCCAGGACATATCTGATCCCATGGTACTGCAGCCAGCCTCTCTGAACCTTGTCACCCTTAA
AAAACGCGAATCCGAGTTGGGTTTCAACATAGAGTCCAGTTATAATGGCATTCACCGTGTCACGGATATCAAGTACAACTCGCCAGCTCACAATT
CCGGAAAAATCGAAGATGGCGACGAGATTGTGCAGATCAACTACCAGACCGTTGTGGGCTGGCAGCATCGCACAGTACTGGAGCATCTGAGGGAA
GCACTTCCAGATGTGGTGCTGACGGTGAAGAAACGGCCGAAGCACACAAAGATGTTTGGACAGATCTATATGCAGCCGTACAGGTTGCCCAGCAA
GAAGAGGAATATGGCCGCCCGCTGGGCGGCACAGATGCCAAGTCCCCGTGCTGCATTTTTAACCCTGGACACGGAGCAACTGGCAACAGGAGGAA
CAGGAAGCGCGGTGCCAGATCCCAGTAAATCCCTAAGCAGTGAGAAGAGGGAGGTACTTACCAAGGCCAATCCAGTGTCCTCTGCCTCCGACTCT
GATTCCAGTTGCAGTGATATTCCAACACCAACGGATCCCAAGCTAGCCGCACGGGAGATCCGTTTGTATTACCCAAAGCCAAGAGCTTTGCTCCA
ACGAAGAAACACTATTTGTGGATGCGAGTATCTTAGCCTGAAAAACTCGGATCTAGTCGTTCCATCGTGGCACGAAAGAAAGCCAGGAATTGGTT
CGCCCACCAATTGCGACCCTGGCTCGCCCAGTATACGGGATAAGTCGATATCCTTCGGTTATGGCCTAGAGATGGCAGCAAGGCCGACCACTTGC
ATTGGGATTGCGGGCGATACCTCCACGGACAAGGCCAGGCGAATGTTTCATGAGGCGCGAAAACTAAAGCAGCTGACGGAGGACTCGCAGCGCGA
ATTCCTCGTGGATCGTTACAAGCCGGGTGTCAGCAAAGTAGTTCGGTTCGACGCCAAGGAAGATTATGTGATGAAGAATGAAAAATTTATCTGTA
ACGTTGAGAACACCATACTGGAGACCTTTGAACCGATTCCCTTTGCGGATGAGGGAGACGAGGACGCCTTGGAAACGCTGCGCAACTGCAAAACA
GAAAACGCAGAGGAGCTCCTAGAGGCAATTAATCTGGCTACAAAAGGTCAGGACTTGCCCCTGGCCGAGGCCATTAACATGCCTTTGTTGCAGCA
AGGTCGAAGGGGCCGATTAGACAAGAGTCATAGTACTCCGGCATACGATAATTCGGGTGAAGAATCGGATACGCCGCCAGCGATTGAGCCAAGAA
AGGAGTTCCTGCTTGTCACACCGCCAGCACCGCCACCGCGACCCCGCAAGCAAAGGGAAATGACGCCACCGGCGGTGCCTCCACCTCCACCAAAA
CCAGCCAGCATGCAGCCGGCTAGTAGTATCACCAGTATCTCCATTCCCGTGCCAGTACCTGTACCAGCCGCAGTTGATCCATCGGAGATCAGTGA
GCTTCATACGCCCAGCAAATCCCGGACACTGACCCTTAAAAAGAAGCACAGCTTAATGGCCAAGCGGCGGAACACAAATCTCAAGCTGTTGGGGA
CTGGGGATATCCAAGGTCATCTGTACAGGCGCAAGAAAAATCATCGCGGAGTGACTTACTGGGCGAGAATCTATTTCGTGATGCTGGATACGATA
CTGTACGGATTTCGCAGTAAGCAGAGTACCAGCGCCAGCTTGGTAATATTTTTACCGGGCTTTACGGTTTCATTGGCAAAAGAAGTGCACTCCAA
ACCGCATGCCTTTAAAGTTTACCACACGGCCAAGAGCTTCTACTTTGCGGCCGAGTCGCTGGACGCACTTAACCAATGGGTGGACTTCTTGCGCC
AGGCTTCGCTCAAAGTGCCGCCTAGTACGGGTTCAAAAGGCGGTGGTGACGCAAAGGATTTGTATTCGGAGAACGATAGCTCAGGCGAGGAATGC
GATGCCCTTGTGATCCAGAATTTAAGCACGCCCTCGCCGCAAGGCAACAAGGAGTCAATGTCCATGTCGATGACACTATCTGGCGGAACACCACC
TTCCTCTGCACCCATTAAGCATGAACGCGGCTACTTGGACTCGTTTCGCAAATTTACGAATACATTCAAGAGCAGTGCAGCGAAACCGTCGAGCG
ACATCCCTGTGCCAACGGAGCAATACCGCAGCTATAGGAAGGTGCCAGGCGGAAGTTTTGGCATTCAGATTGGTGCCAATACACCGGGCTACCAT
GATCCCGCAATGCCGCCGACACAGATTCCACCTTTGGTGGGTCCTAAACTGTCGCGTAGCTCAAGTAGGAGTTCGGTGGTCAGTGGAACCGAGTC
TGCCGTATCATTATCTGCTTCGATTCTGGGTCCGCCCGCGTCGCCAGCGCCAACGCCCACGCCTACAGCCACTCCCACATCGCTGCAGCATCAGA
GCTCCGAGGAGAGTCCAAGTCAGAGCCAGAGCCAGAGTCCCAGTAGCAAGTCGAGTTTGAAGAAGGCACCATTCAACTTCTTGCACGCCTCAAAT
CCGAATTTGGTGGAATTCGATTTCCATACCTCGAAAACACTACTCCCCAAGATGAGTGTGGGTAATACACTCGACCATGGCCATAATATACAGGG
CTTTGTGACGCTTAAGGATCTGATGCTGCGCAAACAGGAGGAGGAGGCCCAGGAAATGTACAACAATCGAGTGCACTTGGGTGTGGAGAAGCACA
AGCACGCACGGACGGAATCCACGGCCAGTCAGCAGAGCGCCATGAGCAGCAGCGTGACAAAGCCGCTGGAAAAGTTGCCCAAGATCCAGAGCGTG
AGTCTGCCCAAAACACCCGACTACGAGATCAGTTTTAAGCCTGACGACGAGAGTATTAAGAGAACCAGAACTAAGGAAGGTCAGAAGTTGCGCGA
CTTTGGTTACGAGCTGATATGTGGGGATGAGCCGAGCACTAGCTCCATCAGCCGGCAAGAGCACCACCATCATCATCATCATCACCAGCACCACC
TGCAGCATGTGCAACAGCAGCAGCAGCTACAACATCAGCAGACGCAGCAGCAACATAGCAGCAAGGCCAAGCACTTCTTGCGCTCACAGCAGTTA
CAGCTCTCCAGTTTCCTGCACAAGAACAGCAGCGGCGGCAGCGGCAAGAGTTCCGGATCCGGTGCGGATCAAAAGAAGTCCAAAGGAAAGTCTAG
CGGCGATCGTCGGTTTCCCTTTTCCAAGCACTCAACTGGCTCCGCGGGCAGTGGCTGTGGGCCGGGTCATGCGATGACTATGACGCTGCCGCTGA
ACAAGAAGTCCAAATCGAATCACGCCTTGGATGGAGCCGTAGGCAATGGAGTCACCATAATCGGCAGCGGCAGCAGCATCAAGAAAAGCCAGACG
TACAATCAGGATCTGCGAGACAAGATAGTGGGCACCAAGTACGATGCGCATCGCAAGAACTCGGCCCCGATACCAATCTTTTCGAAACTCTCCAT
ATCGGGTGGCACGCCGGCGAAGCCCTCCAAGGAGAATCGTTTCCTGGGCTCACCGCTGCTGCATCGCACGCTGTTCGGGCACCATCACCATCAGC
AGCAGGCAGTAACGCCACCAAGCAGTGCGGATCCCGATTGCGATCAGGAGATCTTCTCCCAAATCACCCTGCCCACGCACAATCAGGCGGGATAT
CGAAGTTACCGTGGACCTGGCATACTAACCACCTCGACCACTAATTTGTGCTCGTCGGAGGGCTTGCAGCCGCCGTTGCCCCCAGCGCCACCGCC
TCCCGTCAACACCAGCAGGCAGAGAGAGGAGGAGCAAGCGGAGGCAACGATATCAGAGTGTGCGGCCACCCCAAAAGTGTCCAGTTCGGGATCTG
TGGATTCGAAGGCGGCAACGCCGGACTATCCAAATATGGAGTGTCCGCCTGTCTTTGAGCCGGAAATCTACTCGCTCAGCGATACCAGCTTGTCC
CGCATCGTGATGCGGACGCCCAGCAGCAGTGGTGCCACCAGTGCCACCGCCAGCACCACCACCACCAACAACAACAACAACAATAATAACACCAA
TAACAACACCAACACCAACAGCAGTCCCAGTGGCGGCGAACACCATCAGACCTAGATGTGTGATGAAAACTATTGTGAATGCTCGCGGGGATTAG
CCCCCGTTTACTTATGTATTTATACACACGCATATAGATATATATATATATATTATATATAGCGATATTCTCGTACGATTTAGGTATACAACTTG
TTCATTTTGATCGTCTTCCCTGTCTGTCCACCAGAAACAAACACACGCATACCTGCAATCCCTTCGATTCGAAACCCACTTAGATGTAAATGTTT
AATCTGCCTTATTTGCATTGTATTTCGGTTCTAGGCAAAATGTTTTACACATGTAGTCACGCAAGCAAAACAATGAATTATAGCGAAAATGGAGA
ATAACTTTAGAAGTCTGTGCATCGAACAAAGACGGTTCTTTATGATTTGCCTTTGTACGCGATTAACCAAGTTAATCCGAGCTGTTTGATTTGCT
CAACAGTTTGTGTCTAGATTGCGTGTAATATACATATATTATTATGCGAAATGAGATATTATTGTAATGGCATCCAGCGACGCCAATGGAGCCAG
AAATGTTGTAGCGGAATGCAAGAAATATATATATACACAATTACACGAAATATACATGCATACGAATAAAGTCAACTGTACATAATAGAATAA
(SEQ ID NO: 728)

Start ATG: 132

MAYINIAEWTPDQVTDWIKGLDESMKGYLYEFSKQEIGGRALLNIRPYELENLGMLRIGHQEIVLEAVENLRNFHYHLKNDNLQFMALHVATAAK
NLHRELARNHAESTKIDTRILHDITRTIATLKPLVGSLERTPFRKQEMYREYCGNVLKCGLELATIAHRDRFALQPVPAIRQSAERLENLANFVI
QDISDPMVLQPASLNLVTLKKRESELGFNIESSYNGIHRVTDIKYNSPAHNSGKIEDGDEIVQINYQTVVGWQHRTVLEHLREALPDVVLTVKKR
PKHTKMFGQIYMQPYRLPSKKRNMAARWAAQMPSPRAAFLTLDTEQLATGGTGSAVPDPSKSLSSEKREVLTKANPVSSASDSDSSCSDIPTPTD
PKLAAREIRLYYPKPRALLQRRNTICGCEYLSLKNSDLVVPSWHERKPGIGSPTNCDPGSPSIRDKSISFGYGLEMAARPTTCIGIAGDTSTDKA
RRMFHEARKLKQLTEDSQREFLVDRYKPGVSKVVRFDAKEDYVMKNEKFICNVENTILETFEPIPFADEGDEDALETLRNCKTENAEELLEAINL
ATKGQDLPLAEAINMPLLQQGRRGRLDKSHSTPAYDNSGEESDTPPAIEPRKEFLLVTPPAPPPRPRKQREMTPPAVPPPPPKPASMQPASSITS
ISIPVPVPVPAAVDPSEISELHTPSKSRTLTLKKKHSLMAKRRNTNLKLLGTGDIQGHLYRRKKNHRGVTYWARIYFVMLDTILYGFRSKQSTSA
SLVIFLPGFTVSLAKEVHSKPHAFKVYHTAKSFYFAAESLDALNQWVDFLRQASLKVPPSTGSKGGGDAKDLYSENDSSGEECDALVIQNLSTPS
PQGNKESMSMSMTLSGGTPPSSAPIKHERGYLDSFRKFTNTFKSSAAKPSSDIPVPTEQYRSYRKVPGGSFGIQIGANTPGYHDPAMPPTQIPPL
VGPKLSRSSSRSSVVSGTESAVSLSASILGPPASPAPTPTPTATPTSLQHQSSEESPSQSQSQSPSSKSSLKKAPFNFLHASNPNLVEFDFHTSK
TLLPKMSVGNTLDHGHNIQGFVTLKDLMLRKQEEEAQEMYNNRVHLGVEKHKHARTESTASQQSAMSSSVTKPLEKLPKIQSVSLPKTPDYEISF
KPDDESIKRTRTKEGQKLRDFGYELICGDEPSTSSISRQEHHHHHHHHQHHLQHVQQQQQLQHQQTQQQHSSKAKHFLRSQQLQLSSFLHKNSSG
GSGKSSGSGADQKKSKGKSSGDRRFPFSKHSTGSAGSGCGPGHAMTMTLPLNKKSKSNHALDGAVGNGVTIIGSGSSIKKSQTYNQDLRDKIVGT
KYDAHRKNSAPIPIFSKLSISGGTPAKPSKENRFLGSPLLHRTLFGHHHHQQQAVTPPSSADPDCDQEIFSQITLPTHNQAGYRSYRGPGILTTS
TTNLCSSEGLQPPLPPAPPPPVNTSRQREEEQAEATISECAATPKVSSSGSVDSKAATPDYPNMECPPVFEPEIYSLSDTSLSRIVMRTPSSSGA
TSATASTTTTNNNNNNNNTNNNTNTNSSPSGGEHHQT*

FIGURE SHEET 397

(SEQ ID NO: 729)

Name: connector enhancer of ksr
Classification: signal_transduction
Gene Symbol: cnk
FlyBase ID: FBgn0021818

Celera Sequence No. : 142000013384589
ATAAAAGCAATTCGATTCAATATACGATTATTAAGCTTCCCCAACTAAAAATCGTATTTTTCTGATCCACCTTAAGCCGCCTATTTCACTCCAGT
TTCTTGACGAATCAGTGGAATTTGTCAGCAATTGAGGACTAGTCATGCCGACACAGAGGTGCGCTGTAGTCCATTCAGGAACGATTTGGAATGAT
AAGATAAGTCGGCCCACATTTGGCGGAAAACTTTTTGGGAAAGGTGTGCGTGCACCCACAACGTATGAGTCATGTTTTGAATTTATTTTTTTGTA
TTAATTTATTGCTAGTATCTTGTATACTTTTCATTTTCATAATTTGATTTATTAAAAATTGCATCAATAGTTTATGTTTTTATTCAATTATCAAT
TTTGTAAGCTTTTGCTTTTCGCGTAAAAAATGCACAAAGTTCTCTCGCTAATCGAAGCAAAAATCGTTAATAATATTGTTAAGTGTTTGCTCTGC
TCGTGCTCTGCTTATCTGTTTCAGTTTTAGTCATAAAAATACATATTTTATATTTGTGTATATTTATTCATAAGATGCACGTGGCCAAGTCCTAT
GCCATCCACAGTTCCAGTTAGCAGTCGCGTTCGCTGTGCTAAAAAAAAAACCGAAATCCTAACCAAAACTGGCGAAACAAAAGCCGCAAACAGAA
CAGAACGGGGGCTAAAATTGGAAACAAAATGCCTGGCTGGTGGAATCATTGAACACAGACTGGCTGCGTGGTATCTACGACTGCTGGAGATGCCG
AGAGCTGGAATGTCGGAGGATCCTGGGACCGCCTGGCCTGACATAAGTACATGGTCTTGGGTTTTTTTCGTTTAGAGGGTTTAGGGGGTATCGG
AAATGCACTACACTATATTCTTGTCTGGTAGCTAACTCGCAAATATTACTCTGATCTTGATCCCTGATCTCGTGTCAATGAGTTAGCATTCGCAC
TCGCCTGCGCTCGGGATTAGCTCGTCAATTAACAGTAATTAGTTAGCCGATTTCGTTAATTGTTGTTTAGTCTATTTGCCTTTGCTATCATTTGT
TACTTTATAAATAAACTTAAACGTAAAGTGTGTATGTGTGTATAGATGTTGAGGAATCCGCCGCAGATCCGGCCAGTACATACACCTGACACCTG
TGTACACCAGTGCTGCTGGCCGATCTCCTGCATCTGCATCTGCTCCTGCTGTTGAAAAAGGGGGAGAGGATGGTTGGATCGTCGGCTCAACCGGT
TCTAGCAGGCGCAGCCGCCCTCGGGATCCTTTGTCTCGTTGGGTGAGTCCTTTAGCACAACCTCCTGCATGTCCTCGGAGGGCTTGTTCTCCGTG
GAATCCATGCCGGGCAGTGCCGCGGCCACCCGTCGGAACAATTGCTTCACATTGTAGCCGGCCTTGGCGCTTGTCTCGATGAACATCACGTTAAG
CTCCTTCGCCTTGCGCTCACCCTCCTCGGTGGACACCTGACGCTTGTCGGAGAGATCCGTCTTGTTGCCCACCAGCATGATGATGACGTCGCTAC
CCCGCTCCGTGCGCACGTCATCGATCCACTTGGAGGTCTGGTGGAACGAGTTGGTGTTGGTGATATCGTAAACGACCACTGCCACCGTGGAGTCG
CGTATGTACGAGGGTATCAGCGAGCGGAATCGCTCCTGTCCCGCCGTATCCCACAGCTGCAGGCGCACAGTGCGATCCTCCAGGTACATGGTCTT
CGATAGGAAATCAATTCCGATCGTCGCCTGGTACGTGTTGTCGAAGCTGTCGTACATGAAGCGCGTAATCAGCGAGGTCTTGCCCACACTCTGCT
CGCCGAGGAAGACGAGCTTGAACTTCCGCAGCGGATTGCCAAAATCTCCGGATGACATCTTCCTCAACGTACGTGTCTACTTTTTCTTAATTACG
GGTTTGCTGAACTCTCTTCTCGCTCCGCTCCGCTCTCACCAATCTCCACCCCTCCTCACTGTTTATAATGGGGCTGGGCCAGCGGTTTTCGGGGC
CCTTTCGCACTGCGATTTCTCGGGATGCACCGCTTTCAAGTTGCCGCACTCTATTACACACGCTCTAAATGCTTTCCGTCTGGCTAAAGACTCAA
TTGCGGCTCGAATGGCTTGGTAAATCGCTAGGTTGAGTCGTGGAAAAATTACGGTCTCTGCTTCTTCTTCTTTAACTTCTGAGTCAGTTGCTGTG
TGACCAGAGTGGCAATCAAAAGCAATTTCTCTGCCACGCTATCGATAAACGCATATTTGTACTAAATCGATGTTTTATGATTTAAAAAAAAATCG
ATTGATATTCGTTACCGTTATTAAATAATTTTAACTAAAATTTACCTGCTTAAAATGTTTAAATACTGATGAAGTACAAGGTAATTGCTTAACTT
TTTATTTCATATTAAAAAGTGAATACTAAGTGTAAGAAATACTAACAGGTGATAACGCGATTTTCAAATATAAAGCTCTCTAAAGTGATTTGCTT
GTTTTTAGATAAACGAGCGTAGGTATTTGCCCATCCTATCGGTGGAACTTGACGTACTTCTGTCAAAGAGTCACTGTTCGGGCGTCGCTTAATCT
CAAATTATAATAAGTGGTTATCTGAAGAACACACGGTCCTTAATTGAAAGCCTTATCTGCTGGCGCTGGCAAAATTTTGGAATGGCGAATTAATT
TAAACGTGCCGCGATAAAGGTCGATGTAAACAGTTCCGCGAAAACTATGTTAGCGAACGGACAGCAAACAAAGTCGTTGGCCAGTGGGCTTCTTC
TCCTACTGGGCATATGCCGAATATCCGGAGTGGCTATCGGCGCACCCGAGGGGCGTGTCGTGGGTGGATCTCCGGCAGCGGTGAATAGTGCTCCC
TATGCGGTGTCCATGCAGTACGGTGGCACCCATTACTGTGCCGCCAGCATTCTGAATGCCAACTGGCTAGTCACCGCTGCCCACTGCCTGACCAA
TAGTAACCAGGTGCTGGGCAGCACCTTGGTGGCCGGAAGCATCGCGGTGGACGGAACTGCAAGCACTACGCAGACGCGGAGCATCACGTACTTCG
TGATCAATGACTTGTACACCGGCGGAACTGTGCCCTATGACATCGGAATGATCTACACGCCCACCGCCTTCGTTTGGAGCGCCGCCGTTGCCCCA
GTGACGCTACCATCCTCGGGAGTGGTGCCCACTGGCACCGCCAATCTGTACGG
(SEQ ID NO: 730)

Exon: 2188..1001
Start ATG: 1863 (Reverse strand: CAT)

Transcript No. : CT20524
TCACACAGCAACTGACTCAGAAGTTAAAGAAGAAGAAGCAGAGACCGTAATTTTTCCACGACTCAACCTAGCGATTTACCAAGCCATTCGAGCCG
CAATTGAGTCTTTAGCCAGACGGAAAGCATTTAGAGCGTGTGTAATAGAGTGCGGCAACTTGAAAGCGGTGCATCCCGAGAAATCGCAGTGCGAA
AGGGCCCCGAAAACCGCTGGCCCAGCCCCATTATAAACAGTGAGGAGGGGTGGAGATTGGTGAGAGCGGAGCGGAGCGAGAAGAGAGTTCAGCAA
ACCCGTAATTAAGAAAAAGTAGACACGTACGTTGAGGAAGATGTCATCCGGAGATTTTGGCAATCCGCTGCGGAAGTTCAAGCTCGTCTTCCTCG
GCGAGCAGAGTGTGGGCAAGACCTCGCTGATTACGCGCTTCATGTACGACAGCTTCGACAACACGTACCAGGCGACGATCGGAATTGATTTCCTA
TCGAAGACCATGTACCTGGAGGATCGCACTGTGCGCCTGCAGCTGTGGGATACGGCGGGACAGGAGCGATTCCGCTCGCTGATACCCTCGTACAT
ACGCGACTCCACGGTGGCAGTGGTCGTTTACGATATCACCAACACCAACTCGTTCCACCAGACCTCCAAGTGGATCGATGACGTGCGCACGGAGC
GGGGTAGCGACGTCATCATCATGCTGGTGGGCAACAAGACGGATCTCTCCGACAAGCGTCAGGTGTCCACCGAGGAGGGTGAGCGCAAGGCGAAG
GAGCTTAACGTGATGTTCATCGAGACAAGCGCCAAGGCCGGCTACAATGTGAAGCAATTGTTCCGACGGGTGGCCGCGGCACTGCCCGGCATGGA
TTCCACGGAGAACAAGCCCTCCGAGGACATGCAGGAGGTTGTGCTAAAGGACTCACCCAACGAGACAAAGGATCCCGAGGGCGGCTGCGCCTGCT
AGAACCGGTTGAGCCGACGATCCAACCATCCTCTCCCCCTTTTTCAACAGCAGGAGCAGATGCAGATGCAGGAGATCGGCCAGCAGCACTGGTGT
ACACAGGTGTCAGGTGTATGTACTGGCCGGATCTGCGGCGGATTCCTCAACATCTATACACACATACACACTTTACGTTTAAGTTTATTTATAAA
GTAACAAATGATAGCAAAGGCAAATAGACTAAACAACAATTAACGAAA
(SEQ ID NO: 731)

Start ATG: 326 (Reverse strand: CAT)

MSSGDFGNPLRKFKLVFLGEQSVGKTSLITRFMYDSFDNTYQATIGIDFLSKTMYLEDRTVRLQLWDTAGQERFRSLIPSYIRDSTVAVVVYDIT
NTNSFHQTSKWIDDVRTERGSDVIIMLVGNKTDLSDKRQVSTEEGERKAKELNVMFIETSAKAGYNVKQLFRRVAAALPGMDSTENKPSEDMQEV
VLKDSPNETKDPEGGCAC*
(SEQ ID NO: 732)

Name: RAB6
Classification: signal_transduction
Gene Symbol: Rab6
FlyBase ID: FBgn0015797

Celera Sequence No. : 142000012790778
ATTCTTTATTGGAAATCTTCACACTACAACTATCTGCTGAAACTTAAAAACCTTCATACATTTACACATCATATCTTCACAAAAGGCTCCACCCT
CGATCACGGACTTAACTCGCGCACAACAAAATATAAATAAAACTCCAATGTCACCGAGTCGAGTTGATAAAAAGCATCGCTAAAGGCCTTTTAAT
TGCCGCTGCAGTCGATAAATCATCAAACGGGAATATGAAAGCATCTCAGGAATTCAGTGCGTAAAATTAGAATGCAACAACAACAGCAGTAGCAG
CAGCAACAACAACAACACGCGGGCGGAGGCAGGAAAGATACAAAATAGCCAAGGAGCCAATATACATACATATACATGTACATATACATCCACGT
CGTAAAGTGCGTCTCTCTCTTGCACTCTCTCTCTCTCTGTGTTAGAGCTCCATCTCCCTCTCCCCACAGCCACCTACTTCCTGCACATATGCT
GCGAGCAACAACAACACAACGTGCTCCTCTTGGGGATGCTGTGTGCGAGCGAGAAAGAGAGAAAGCCAGAGAGAACGGCAGAGTAACTTCGAATC
AAAGAGCGCAACTACACTCGTAAAAATTATTACAGCTGCCAAGTTAAAAGCTATTACATCGTAATAATGTTGTTGTGGAATTTTTTTAAAACAAA
TATAACTTTTTATAAATACGTTACATTTGAATAAGATATAATTACGAGAAGGTTAGGGAATATATTGTTATTTAATGTTTTTACAATAGATTTGC
GTTTTACTCTATTACTATTACTCTAACCAAACTAAAAAAAAAGTTATAGGAATCTTTAATGAAATTCCTTTATTCCTTTTGTTTGAGTTGACTGAT
AACTGAATTTCCACCCTAAATTTTTGCGTTATCGTTTTCCCGTTTAGGGCATCCATTTCTCTGAGTGCAGGGCTCAGTCATCGCAGCCTTTTCGC
CTTGGCCACGAACACACGTCTCATTTGAACGCGAAACGCCGAGTCAAACGGACGCAGTCGCTCGTCGCAGTGGTTGTTAAACTCGAGTTTCGTAC
TTTCGAGCGCGCGTATTGAAACATAAGTGAGCGATCGTGTGAACAGTGATATAAAGTGCACCGTGTATGCGGGATAGAGATACCTAACCTAGTGC
CACACGAAAGTTGAAGTAATACCAGCAGGATATCTACTCAGTTGGCAGTGAAAAGCGTGGTGAAGTGTTCGGTCATAATGAGTGTGTGAGCGGGG
ACAAGCTGACAAACTGAATGCGATAAGGTTACAGATGTCCTAAACACACAGGCACTGGCACACAAGGATTCCCGGGGTCCTGGTGACATGTAACT
GGATCCGGATCTGGATACATGTTGGCTCCTAAGACAACAGCCCGCTCCTTTGCCTATCGTCTGGCCGCACTGCAGAAACGGGAGCAACAAAAGCG
AGACACCGGGTAAGTAGCGATGCTTAACTATAATAAGAAACCTGTCCCCTCGGACAGGATAAAAACAAGCCGCACACACAGTAGCACATGCGGAC
AAAGGGGCGCACTGCAGTGGTCGTCCGATGCTTCCTGCGCCGCTAAGTATGCCACTGCAATGCTATTTTAAGGTGCAAAGTGCATTGAGTAGGAG
GAGGCAAAGTGCCAGCCAGCTAGCCCTAACCCACACACACACTTCGCATAGACACACATGGGCAGTGGACTACGGCGACAACACACAAAACGTAT
TCAAGTGTAACTAAAGACGACCAATTCACAAACAAACAAGCGCGCCAGGAGCAGTTGGCGGATGTGTGGGAGGGAGGGAGTTGGGGGAAACGGAA
CCGACTGAAGCGGAGCGGAGCGGTCGACCCTCGAACCGTGTGACCGCGGGGCAGGAGGGGGCGGGGTTCTGAAGGGACGACAGGGGCCGCTCGCT
AATGTTTATTATGAAAAGCGTGCCCTTTTGAACGCCATCGTGTATTTTTATTTTTATTTGTATTTTATGATTGCGCTTAGCCATGTGTATTTGCT
GTGAGTGGAACTGTGGTGAGCGCTAGTGCACAGGAAGAAAAAGATATAGACTTGGTTTTTTATTTGAGGTTAAAGGGAGATCCCATTTCAAAGCA
AAGGAAAACAATTCTATTGAAGGTTTCGATTAGGAGACGTTTCGTTTTTTGAAATCTGAACTCTACACTGTGGAATTATTGAAGTTCATACCATG
TTTGGTTTACGATCAATTAAAATGGGATACATTATACATCATGAATACTATGTTTGGTTTACGATCAATTAAAATGGGATAGATTATACATCGTC
AAATGATAAGACAGTTTAAAACAATGATTAGTGAATCATATAATGTGTATTGAAACCTTTTCGATTGGAATACGATTATAAAATCCATCTAAAGG
CCTGGGAATAATCCCCCGAGAGCTCTTACAAACCATTCTCGATCGATTCCGAGTACTACATTTTCTCTCAGTATGTTTATTTATGTTTTTCTTGT
CACGGAGCTGGATCAGAGGGGGTGAAGGGGCGGCTGTCGAGAGGCCCTCATGTGAGTGCAGCACTCAATTCATTGATAAAAGATGCAGCTACAAT
TATAATAATAATAATAAGAACTCCGGCCAACGGGATGCCGCCGCGATCAACATGCCGCAATTACAGTTATAATTTGGGCCCGTAAGCGTTGTTCA
AATGTAAATTCAAATGTGGATGAATTGCAATTACCAACCCTCCGCGGCGACAAACGTTGGCTGCTTCGCTGAGTGGGGGTAACAAACAATCGCCA
ATTGGCATATAATGATCCCCTTTGGACGTCGAAACGTCCTAACTGACTGACTGACGTACCAACTGGCTGACTGACTGACTGACAGTCGGACGATA
TACATACGAGTATATGCGCCATGAGGTGGGTATGGTAAAAAGTGGCATGGGACTCAGACAACCAGCAGCGACATTCGGAACAATTCTCAGGCCTT
GACAAATGCACGTAATGATTGGACTCACACTTTGGTTTCTGCTTTTTTAACAATTTACGCGCAGCTCTTACTCTTACCCCTTCTTCGCTGGTTCT
CACACTCACTCGGCCTAGTCATAATTTTAGGGGTTGTGCAACCCGGCACAGTAATCGAAACTCAAACCCAAAAACTCGTAGATACAGATACAGCT
GTTCGCCTTGATGGGCAAACAAGGGCTTGGAGGTAGACCTCCGCCCTTCGACTTTCGATTTTTCGGGACATGGGAACGGAACGTTGCATGAACAT
CTTAGACTCCTGCGGTGATTAATTGTCATTCCAGGGCCCTACAGCATATGTAGAGGCCACTCGGGCTCCTATGTATATGCGTTATGTAGGATCCA
GGGTTCAGGGTCTTAACACTGGATTAGATGTCGATCGAAGTGAAAGAATAGGCTCTTTTCAGTTTCTTTCGGCAACTGGCTTTGTTCCGAGCCTA
GGTAGCTGATGTTGGTAAGGGCTTAGCGTCGTAAATCGTTGGATTGAACCATTCCGATCGATGGCGGAGAGAATCGGTAGGGCATTAACATGCCT
AGGTAGTAGAACTTTCTATACGCCAGACTCTTATCATTGCATCTTCGACATGCGTAGGCAATACGTTTGCTTTCCATTTTTCTCTGGCTATCATC
AGCTGGCATCATGTGGCAGTAGTTTTGGCAACATAAATTAGGCCACGGGCATCATTTGTTACAACCGGACACATTAGAACTTTGCTAATACGATA
CAAATGATAAGGGCCTTTCATCAGTTGTTCAGTTTGTGCTACTTATGCCGCTGATGGGATAGAATCATAAATAATTTGTTTATTGCATGCAGAGG
GGGTCACAAGTATGCTGGCTACGATTGTATCTTGTGTATGCTGTGTATCTTGTAGTAACATGAGCCTGTGTAGCTTGGCCCATAACTCATGCTTG
AAACTTTTGTTTCTACTTCTATTTAATTCCTCGACAATTACGCTTAATTAATTTAAAGATGTTTGTTGCCGTTGTCGTGCTCGCATCCCCCGTCG
AGTTGTTCGATCAATTTTGAGCAGTTATGACGGCGGCTCGGCCATGGGGGAGGATTTTTTAAATAGATTAATTAAAATCATCTTTAATTGTTTGA
TTACAAGGCAAGCGCGGCCCGAAAAAAATGCGAAGCGAACGCAGATAGCTCACAATAGCTGCTTTCATACGTTCTCAAGTTGCGGAGTGTGTGGG
CAAAATGCGCAACATGTGAAATACAGATGCCTCAGAGTTACCAGCACGGTCCCTTGGGCATTAAAGATTTCATTTGTGCTACAGATGTTCCGGCG
ATTGTACAACATAACTACAAGGAGGAGTCTCACGCAATTGAGGCAACGGCATCTGCCACAACCACACCAACACTCACAGCCACATCCACATCCAC
ATCCATGGATCCATGGTTCCACTTCAGCGCAGTCACCAAGCGACTGGCGCAGCGTTTCGAGTGGCATTTGATTTAGTGCTCGAGAGTGTGTGTG
CGAGTGCTTCAGAAGTATAAAAATTATTGCTGCCAAGCAACTGAGTCAGTCAGTCATCAATTATTTTATAGAATGCTCACTTGTTTTGTGTGTTC
TGGCATTGTTCCCCGACCAGACCCAATCTCCATCTCCCCGACCCATTTCGGCATCCCCATGCCCCGAAATGCCAAAACCGAATCTGTGTTCTTGG
AGTTCACTTGGAAGTTCTCGTTCGGTACAGGAAGGGCTTCTCCGCCCTCTACACTTCACTTCACTGGGACTCCGGCAATAGTTGTGAAATTAAAT
TGAATACGACGCCGATTATCCCACGCAGTCTTCCATTCGCATTTCCCATTCATTCAGGCAGGCATCCACGGGCTGCCTAGGAAGCAAGTGCTGGC
GACACAATCTCATCCTCATACTCCTCCGCGGAATCCGAGAGCTTGGGAAATCATCAAAGTTCAGCGGGACTTCGGTGGCGTCTCCTGCTCACAAT
ATAAGATGATTACATGCACACGCAACTTGCCGTATCTGGCCATAAATCTCAAAGAGTGCACAGGGAAAAAAGGATATTAATATATACAAATTATG
AAACGGTATAGTGTTTCTACTGCGCAAGGCTTTAATATTAATAGACATGAAATCAATTGAAAAATGTATAAAATTCTTATCTGAAATACACGTTC
CTTGACGCAGTATTCCGTTCTATGTAAAGAACAAGAAATATCACCAATTTGGCAGAAGTTCTAATATTTATTTTAATATTTTGTTTAAAATTCTC
CTTTTCTTTGATTTTTTCGCTCAGTGCATGTGCGTGTGTGTCCCACAGTTTGTCACTCAGTCATTCCATTCAGAGGATGAGGAAGTGGATGTAGA
GGGGGTTTTCGCCGGATGCTTGCGTGCCAAAATCAATGCAGGTTTTTTTATTTGTCAACGACAAGTTTGCATTCAATAAATAAAACCCATTCGAT
TATAAAGTACACCCGCAGACAATGAAATGTCGCTGATAAGCGCCTCTTACAATCCATTTGGCCTACTTCAGTTCATTAAAAATCTATTAAAATGT
AATGTACAATACCCCACCTCCCCTATGCATGAAGCTTTCGGTCCGATAAGGCAGACAGCCATCCAATCGATCGAATCGGGGCTATTTAATGTGCG
AGACTTTGATTAATCTCGCCATCAGTTCGGTTGTTCCCTTGTCATGCGGAATATATGTACATATGTACAGCTATCTGTATCTGTCTGCAATTCAG
CATTATTCTTGAGAGTAGCTGCAGTAATAAATAAGCCATGTTTGTAAGAGCTGAAAATTTGTTCGATTTTCGCTGATGGCGATATCGATTTAGTT
TAGCCGAAATGTAATTTGGCTAAGCAGCCCGGCAAACAATGTGGCCCAATATCGGCCTCGTCAAACAAAGGTCTAGACAAATCGAAAACAAAACG
AACTTCAATATCCCATCTATAATTGAATGCACACACAAAACAAAGCGGATAGAGTTGGAAGACTATTATAATCTGGTCAGTTACATGAGCACCGC
CCGCCCACACACTCCATATCCACAAATATAGCAGATATGAGATAGCACATAGTATATATGGCATATATGGCATTTACCATTACTATTACCCCAAC

FIGURE SHEET 399

CCATCCACACACAAAGGAGAATATTGACAGACACTCAAGTGTCCACAAGCACCCTGTAAATCCAATTGAATTACGCATAAAGGCGCTTAAGCCGA
ACGAAACGAGTCTCTCGATGATGACGACCCATCAAATGTATGATTTCCCTTTAACTTCTGATTACCCGATATTTTATTACGTTTCGTGGTCACGC
CGGCTACTGGGTACCACTGATTTGGTGTAGCTATGGAGCTGTGGCGCATGGATCCCCCAATAATAATCACTTATCGCATATCAGCGTTTCCGCAA
AATTTACATATCGACTTTTACTTGATGCGCCTTTTAATGGCCCACGTCGACGGCAATAAAATATTGAGAGACTGAGCGTGCGGGGGCCTTTGAGT
TTTAACTTATGCATGATTAATACATAATTACAAAGACAAACGCATAAACTCCAACTCAAACTCCAGCTCTAAGTGAGGCCCAAAGAGGGGGGCCG
GACTTATCGCGGTATTCGTGCAGGTATGCCTCCTCCATATAACCATTTGCCACTCCAACGTCCACCACACCACCACTTAATAACTCTAAAAGACA
AAAGGCACTTTTCCCACAGCCAAAGGCAAAGGCAAAGGCAAAGCCCGTGGAGGAGACCACGTCCTGAACCGAGCCAAGCTGCCTAGGTGCCCGGA
GAACTGCAGTGTGGCGGAGCATACTTATACCTGTTATTAATATTTCGATTAGGTACCAACGATTCGTAGAACCTGACGCATGACTTGCATGGCTA
ATGGGAAATTTTGTAACTTGTGACCACGCTGCCCTACAATTTGTGGGTCGTCGGACGGGGTCGTCGGATTGGTCCCCTGATTGATGGAGACAACT
CATCGATTGTGCGGCGAGGACAGGAAGTGTCCCTAAGTGCAGCCGATACATCCTCATTTTCCCATAGATCCTGACAGTAGATTGGAATCTGGGCC
TACCTTCGCCAGGAAATGATATCTAAACTCATGCGTACAACTCGAGATAGTTTCATTCGTGAAAGGAGCATATTTTTTGACCTTTTGGAAGGGTT
TGTTGCGTGATCATTTCATCTTCTCTTCGCAGACACCACCCTTAAAATATTGTTGATTCTGGGAAATGTGATTGTAAGCAGACACCTTTTTCTTC
CTTACTCATAAAGAGGATTTGCGTCATAAAAAAGCAGGTGTACATCTGAGGGTTCCATTAAATGTTTGAATAACACTGTAATAGGATATGCAGCC
TAAATACAGATACAGGTTAGCAATATCTACAACAAAATGTAACATGATGTTTAGGTTAGGTTCTATAATGAATGAATTCAATATAAATTCACTGA
ACAGCAGATTTCTTAGGCAATAGAGTGTGTACTAGTCGTCTCAGATAGCAAAATCCAAGTGCAAGACCATAAGTTTGTTAATGCTGAGCGTGTGC
GTCAAAGATATGAACAGTTTAGTCAAACCGTGGACACTTTCGTGGCTTGACAGACCGCTTTGTAAATAATCGCCTTATGGCCAAGTGCGCAAATT
GCCTGGTCGAAGGAGCAAAAGTAAATGTAGCTAACTGGCGTTTCTTATCTGACTTTCCAGATCGTATTCACCACGTGAACAAAGCGAGTGTGCGG
CTAATGCTAATGCCAGCTCCTTCAGCTAGCTCGCCACATCGCCAGCAGCAGCAACAACAATTGCAGGTGCCCCTGCAGGTGCATCAGTTGCACAG
GAAGCGCCGGACAAAGGGACACCTACACCACCTTCACCATCTCAACCACGAAACGACAGGTCAACTGACAGCGAAGCATGGCGGTGATTAATAAA
GCCGGAAATGTGATTGCCCTCCTGCTGGTTAAGCTTCAGCTAATCCTGCTGTTCACGCTGTCAGTTTCCGGAGAGTTGCCGCAGCTGGACTACGG
CAGCTTGTCCGCATCCCTGGAGGAGGATGCTATTGACCCACTCACGGCGATGGCACCCTTCGCCAACTCCCTGGTCACCGAAGAATCGGCGCAGC
ACAAGAACAACGCCGAGCTGCTTGGCAATAGCAGTGAGGATGAGAATGTGAGACCGCAGCAAGGGTCCTCTTCCTCGGGACTAGGATCATCGGGA
GCAGCAGGTGGATCAGGCATACTGCTCGAGGAGTTTAACAGCGGCAAACTGAGTCCCGGAGAGGCGAGTAATACGCTGCCCATATTCCTCATCGA
GCCGGAGAGCGTGTTCGTGGTCAAGAACCGGCCGGCGGTGCTTAAGTGCAAGGCCTCCCACTCGCTGCAGGTGATCTTCAAGTGTAGCGGCAGTT
CGCAACCACCGCCGTCCACGCACGAAACTCACGTGGATCCGCACACGGGGGTCAACATGGAGGAGGTCACCGCCACCATCCACCGCGACCTGGTC
GACGAGTTCTTCGGCGACGGACCCTTCAAGTGCGAGTGCCACGCGTGGTCGTCGCGTGGCGTGGTCAAGAGTCAGGCGGCCACCGTGCACATTGC
TTGTGAGTACACTGTTCAAAAAGTTGTAGTTTACAAATTTATTATGAGCGAAACCTTATCCTAGGATTTTCGTATCGGAAAAAAAGTTAAAATAA
ATATTTATTCTACAATAGTTAATTTTCCTTACGAATTTTTGTTTCAGTATAATGGCATGCAGTTGAAAATGTAATTTTTGTAGTTAACTTTGCAC
CTTTGTTCGGGGGTGGCTTCCTGTCAACAACTGACCCTCGCTTAGCTTACCCCTATCTGTATCTGAATCTACATCGGTAACCTGCATCTGTCCGT
TTAACCCCCACAGATATTCGCAAGTCCTTCAACCAGTCGCCCACCTCGCTGCGCCTGGAGCTGGGCAGTCGGGCGGAACTGCGCTGCGAACCACC
CGGCGGTTTCCCCGAACCGAAGCTCACCTGGCACAAAAACAACGCGGTCATCACGGCGGACAGCGAGCCGGGGATCACCGTTTCGGCCGGCACAC
TCATCTTCCGCCAGGTGGCCCTGCAGCATATGGCCAACTATAGCTGCAGTGCGGAGAATATCGCTGGCAGACGCGTCTCCGATTCCGCCGTGCTC
ATCGTTTATGGTCAGTACAGATGGGCTTTGGGGCAAATTAAAAATTTATAGGTTTCATGCTGTAAATTCCAGAAAGAAACCCCATTTACTGGGGG
TTCTCGGTTTTAATCATTTTCCATGAAATTTTTATTAAATTTATTGCTAATAGAACTGAGGAACTATAATCATTTTACACTAATATACTCTTAAAT
TATATGGCCAAAAATCGCATAGCACCTTAAATGGAGTAGCGAAAAATCATTTGGTATTGCAGGTCGATAAAGCTCTTAATTGTTTTATTTTCCGT
TTTCATCCCACAGTCAACGGTGGCTGGAGCACCTGGAGTCCATGGCGCGAATGCAAGTGTGCGGGCAAGCCCAGCCAGGGAAGGAAGCGTTCGCG
CACCTGCAACAATCCGATGCCATTGAATGGGGGCGCCCAGTGTCCGGGCCCCCAGATCCAGAAGTCCGCCGACTGCGCCGCATGTCCAGGTACGT
TCCTGCGGTCATCCGCAAAATTGTGGGCGCATCGAATTGCGGCCAACACGCCCATTATACGGGCCCATTATATGTGCTGCTGTGGGGTTTTTGGG
GGGAAAATGGGAATGGGAAAATGCTTAAAGGCAGATGTTAAGCAGAAGCCAAAATTGTCAATTTAAATGGTATTTTGCGGCCGGGATTCCAGCTT
GGGCGCCACCTGAAAATCCCCATCTGGTTGCCCCGCTGCTTCTGTCGATACATCTCCCGGAGCGTCGAGAACAACGCGTATTTTTCACACCAGGG
CGGACATGAGGATACCAGGATGGTGTGGAGTGGCAAGGACTGCCCAAAATACAAAGCACTGCACAACGCAAAAGTTCAGGGGGCGTTTCACAAAA
AAAAAAGATGAGAAATAAAAGACAAGATAAGCTTTTGAGGGTCAATGCGAACTAGACATACTCTAAGGACCTCAGTGAATTATCATAATCCGAAA
GGGAGCGGATTTACCTGAATGATGGGAGTGGCATTGGGATTAATTTACAAAGTACAACAGCTGAACGAAATATTTTAATATTAAATTTATTTAAG
ACTAATCCGCATGGTTCTTACAAATTTCTACAGATTTTTATCAGCAATCAAAGTTACTAGATGTCAAAATATTTTCCCGGTTTAAAGTTAGTCTC
ATTATAACTTTTTGACACACCTTATTTCAACAATTAGCGATAACTATTTCTTACAATAATGAGTACATCAAAAAATGCCTATTTCAAGATTAATA
ACTTAATACCCACTAGAACTAAATATAGACCAACCCCAGTACATAGTCAACATGCCCCGACCGAACAATGGTATAATACACTTTTGAGTGAGTGC
TGAGTATTTCATTTTAAACACGCATTCGGTTCCTCGGACCGACGACAGATATCTCCACATGCGAGATGCGTATATAGATGGATAGATTGGCCGC
CGCCTTTGGCAGTGGGGAACGCCTGCCGCCGGCGTGCCACCGACTAAATGGTGACAAAGGAATGAATCCGGGGGAAGGCAGTCCAGAGACTTGGT
GCGACTCAGCATTGAGGACTGGAGATGTGAGGATGAAATCTGGAGTGGAGTGGCATGGAATGGGTCGGACGGTGGTAGCTGGGGCGCTCTTTTTG
ACAGACGCACGGGCGGCATGTGTTTGAGACTCTTCACTTTTATTCATGTAAATTTATTGTATTGCATTGTATTGTATTGTAGTGCTCGCACAGAT
ACTCACCCACACGGAGATTTCGTAGGATACTTGGCCAGGCGCACAGCGGGCACAGCAATGAGCAATTGTTGACAGACAAGCGGGCCAAATGGGTG
ATGGGAAATGGGTGGGTGGACTACGAGTATATACTGTGCTCCAGAAGGGGGCCTTTCGGTCGTCAAGAGGGGGACGCCATTGTGGGCTCGGGTAT
TTCTTTTCTATGAAAAGTGTGTCATAAAATTAATTTTAAATTTCGCTTGGCTTTCGTTTTTCTTCCTTTTTTTTTTTTTGTCCCCGGACGACTTTT
CATCCCCATGGAACCGTGTCAACCTTATGGTCCTGCCGCTGCCACGCCCACCAACGCCCCGTGATTACGCTGTCGCTCTGACGTCCCGTCGTCCT
GACGTCCCGTCGCCATCGTCGCCATCGTCGCCCGCCAACAACAGAGGACACTCAAATCGTGAGCCCTGATGGATTTGACATTTCGTCGAGTAAGC
GCAGTAAGTTGAACCGAAAGCCCGACAATATGCATTTCCCTCAAAGGCTTCCGAGCCGTTTCAGGATCCAATGGGATGGGGCTACTCGAATGGGT
GGATGGGGGTTCCAAAGGATTCAATACATCGACATTGTGTTCGAGCAGTTAAACTTGAATGTTTAACGAGCCGACGACAGTTAAATTTTTTAGTT
GGGGTCGCCTCGCTATCCACTGGGTCCTTAACAATCCAATAAACAATCGTGTTAACCCGAACCGGAGGCATCAGCATCCAACCAACCGTGGCGTC
ATTCGTTTCGGGACTTCCCCCAAAAAAAAATCCTCCGCACTTTAACTGACTTTAACTGAAGTGACTTACTTTGCGACGGGGTAGTTGTTGGTGAC
GTCACTGCGGCAGATAGCAACTTAAAAATCACTTACCACGACTCACGCTCTCTGATTCATGCAACAGTCTGAGTCTGGGTCTGGGTCTAGTTCTG
GGTCTCGGTTTTTGGCTGGGGTCGAAAAGGATACGTCCTGGATGGGTATTGACAGGCGGGATGGGTTGGGGATCAGGATGCGCACGGCGTGGCA
GCGGGGAAAACTAAATGCCTGGCAATGTGATGATGGCTGGCGACAAGTCCGGAATTTTGTGCGCCCTTTCTGAGGGTGGTTTTATGTTTCCAAAA
CAGGAAGTGCCAAATGCCGATGTATTTATACCAGGATGTGCGCACACTTAGCGAAAAACTAGCCCAGGAACTAAATACATAATTAAAATAAACCA
TCGCAGACATGTGGAAATATGAATATTATTGCAAAAGAAGTAACTTAATGAAAACATTTTGAATTCGATTAAATCAAACCAGAGAAAAGAGTGTA
CACATATGTATTATGTTTATAAAGTAGGCTTGTTAATTGTATCTGTTTTCATTAAGAATAACTTGAATAACTTGAATCGCTTTGAATAGATTCAA
GTCAACTTCTTTTTCTCAGTGCATAGCTGTCGAACATATATTTCAGCTGCCATTGGCATGCATCACACCATGGACATTTTTGGCTTTTTGTTTAG
CTTTCGGACTTTCCGCTTTCTCCCCCTCATTTAGTGGAAATTGAAATAGCAAAGAAAATGCGAAAATAGAAAAGCATTAAAATGACAATCACTTT
TACTCACCCACCCACGCAGAAACCAGCCCAAACCAAACCCCACAAATCAACAGAGGCGTCGTCAGTGGAGTTTTGGGGGTTAAGAAAAAAACGGG
AAATGGGAATCAGGAGTGGAGGAAGACCCACTAATTTTATGGTGGGAACAAACTTTCGATTTCTCCCCATGGACCATCTATTAGACCGTAATTGT
GCAGCCGGAGAAGCTGTGAACAAAGGGGGGGGGGGGGGTTGGAATGCCACGTCCATGGTTGTGGCCCCGATGGTCTTGATATATGACCCGGGGA
GTGCCGCTGTCGGGAATGTGTGCTAAATCATGTTAATATGACTTTTGATTTCTAAACTGCCTGTGCTTTTGCCTCTGCTCTTCCATTTACAGTGG

FIGURE SHEET 400

CCCGCTGGTCGGCGTGGAGTGACTGGAGCATCTGCTCCGCGGAGTGCATTCAAGTGCGTCGCCGGAAGTGCCTGACTCAGGGCCAGACTCAGATT
TCCTCCGAGGCGGAGGAAGCCGGTGATCTGCTCCTGGGAGCTCCCGGAGTGGGCATGGCCGCCCTCATCGCCGCTGCAGGAGTGGGCGCAGTAGG
AAGCCCCAGCGAAGCGACTGGCTCCAGTTCCGACATTATCCCGGGATATGGCAAATCATTGTGCGCCGGAAAAGACATACAAACGGCCGAATGCC
GCGGCGAACAGTGCCAGATTGGCAAGGATGGTAAGTCTGTGCTCATGACTAGGATGAATGCCTGGCAGGATCAACAAAGTAGACAGTTAGACAAC
AATAACAGCAAAGCCGGAGTGCAGCATCCACAAAACCAGAATCCCAGAATCCCTCGCACAAAAGATGAGCACTCAACGCTGATTGTCACAATGGG
AAATTAACCAAGTGCATTTGTTTGTGCACGACCACGGGCTTATTTATATATATATAATGGAAGTATAGATGGTATAGAAAGCATGGCCAGGACAT
TTCACTTTTCACCCCAAAGGACCCCCAGCTGTAAGCTCTCAACTTGCGACTTTCAATCGCCCCAAATGAATCCCGGACCCAATCGAAGAAGGGTC
GCAAATCAATCGCAGCAGCACCACTTGGAATTGAGATTTAAGTGGGGGTCCCACACAAGTCTTCCGAGGGTTTATGTGCTTTGCCAGATAATTAG
GCGTGCGGCAAAGACAGCAGCATCAGCATCAGCATCCACACACCCATTTGCCACCCCAATCCGGGGCTTTTCCCGTGTCATTGTTGCTGTTTGCG
ATTCGATTTTCATCGGCAGGGCGGCTAGAGGGGAAAATTGTGCGATTGACCCAACTCAAACATAGTTTTGTGCGGTCCATGGGGATCAATTAGAT
GGCTGTCACAGTGTGTAATTGAAAGGATCAGGATACACAGGGAGTACCAGGAGTTGTTCGGCTTTTTTGGCAGGTTTGTCCTTTATTTGATTGCC
TGCTGAAAAGTTTTCGAAGAGCTGTGACACTCTGCAGCTTATTTTCGATTTTATTACGATTCGCTAAAGCTCGAGCAATCCGGGCAAATCCCTGG
GGCCACCGATACCTGCGGCTTCATCATGGCCCATTGTCAGCATCTCGTACTCAACCATCTGATATTAAAAGCGTATTTGTCAGACCAAGGAGACG
AATCCCCTTTTGATGTCCCTTGCAGGAGGCA
(SEQ ID NO: 733)

Exon: 1001..1434
Exon: 7661..7873
Exon: 7950..8335
Exon: 8423..8552
Exon: 8849..9130
Exon: 9419..9589
Exon: 11255..11308
Exon: 12823..13307
Start ATG: 7705

Transcript No. : CT20824
GACGCAGTCGCTCGTCGCAGTGGTTGTTAAACTCGAGTTTCGTACTTTCGAGCGCGCGTATTGAAACATAAGTGAGCGATCGTGTGAACAGTGAT
ATAAAGTGCACCGTGTATGCGGGATAGAGATACCTAACCTAGTGCCACACGAAAGTTGAAGTAATACCAGCAGGATATCTACTCAGTTGGCAGTG
AAAAGCGTGGTGAAGTGTTCGGTCATAATGAGTGTGTGAGCGGGGACAAGCTGACAAACTGAATGCGATAAGGTTACAGATGTCCTAAACACACA
GGCACTGGCACACAAGGATTCCCGGGGTCCTGGTGACATGTAACTGGATCCGGATCTGGATACATGTTGGCTCCTAAGACAACAGCCCGCTCCTT
TGCCTATCGTCTGGCCGCACTGCAGAAACGGGAGCAACAAAAGCGAGACACCGGATCGTATTCACCACGTGAACAAAGCGAGTGTGCGGCTAATG
CTAATGCCAGCTCCTTCAGCTAGCTCGCCACATCGCCAGCAGCAGCAACAACAATTGCAGGTGCCCCTGCAGGTGCATCAGTTGCACAGGAAGCG
CCGGACAAAGGGACACCTACACCACCTTCACCATCTCAACCACGAAACGACAGGTCAACTGACAGCGAAGCATGGCGTTTCCGGAGAGTTGCCGC
AGCTGGACTACGGCAGCTTGTCCGCATCCCTGGAGGAGGATGCTATTGACCCACTCACGGCGATGGCACCCTTCGCCAACTCCCTGGTCACCGAA
GAATCGGCGCAGCACAAGAACAACGCCGAGCTGCTTGGCAATAGCAGTGAGGATGAGAATGTGAGACCGCAGCAAGGGTCCTCTTCCTCGGGACT
AGGATCATCGGGAGCAGCAGGTGGATCAGGCATACTGCTCGAGGAGTTTAACAGCGGCAAACTGAGTCCCGGAGAGGCGAGTAATACGCTGCCCA
TATTCCTCATCGAGCCGGAGAGCGTGTTCGTGGTCAAGAACCGGCCGGCGGTGCTTAAGTGCAAGGCCTCCCACTCGCTGCAGGAGGTCACCGCC
ACCATCCACCGCGACCTGGTCGACGAGTTCTTCGGCGACGGACCCTTCAAGTGCGAGTGCCACGCGTGGTCGTCGCGTGGCGTGGTCAAGAGTCA
GGCGGCCACCGTGCACATTGCTTATATTCGCAAGTCCTTCAACCAGTCGCCCACCTCGCTGCGCCTGGAGCTGGGCAGTCGGGCGGAACTGCGCT
GCGAACCACCCGGCGGTTTCCCCGAACCGAAGCTCACCTGGCACAAAAACAACGCGGTCATCACGGCGGACAGCGAGCCGGGGATCACCGTTTCG
GCCGGCACACTCATCTTCCGCCAGGTGGCCCTGCAGCATATGGCCAACTATAGCTGCAGTGCGGAGAATATCGCTGGCAGACGCGTCTCCGATTC
CGCCGTGCTCATCGTTTATGTCAACGGTGGCTGGAGCACCTGGAGTCCATGGCGCGAATGCAAGTGTGCGGGCAAGCCCAGCCAGGGAAGGAAGC
GTTCGCGCACCTGCAACAATCCGATGCCATTGAATGGGGGCGCCCAGTGTCCGGGCCCCCAGATCCAGAAGTCCGCCGACTGCGCCGCATGTCCA
GAGGACACTCAAATCGTGAGCCCTGATGGATTTGACATTTCGTCGAGTAAGCGCATGGCCCGCTGGTCGGCGTGGAGTGACTGGAGCATCTGCTC
CGCGGAGTGCATTCAAGTGCGTCGCCGGAAGTGCCTGACTCAGGGCCAGACTCAGATTTCCTCCGAGGCGGAGGAAGCCGGTGATCTGCTCCTGG
GAGCTCCCGGAGTGGGCATGGCCGCCCTCATCGCCGCTGCAGGAGTGGGCGCAGTAGGAAGCCCCAGCGAAGCGACTGGCTCCAGTTCCGACATT
ATCCCGGGATATGGCAAATCATTGTGCGCCGGAAAAGACATACAAACGGCCGAATGCCGCGGCGAACAGTGCCAGATTGGCAAGGATGGTAAGTC
TGTGCTCATGACTAGGATGAATGCCTGGCAGGATCAACAAAGTAGACAGTTAGACAACAATAACAGCAAAGCCGGAGTGCAGCATCCACAAAACC
AGAATCCCAGAATCCCTCGCACAAAAGATGAGCACTCAACGCTGATTGTCACAATGGGAAATTAA
(SEQ ID NO: 734)

Start ATG: 479

MPAPSASSPHRQQQQQQLQVPLQVHQLHRKRRTKGHLHHLHHLNHETTGQLTAKHGVSGELPQLDYGSLSASLEEDAIDPLTAMAPFANSLVTEE
SAQHKNNAELLGNSSEDENVRPQQGSSSSGLGSSGAAGGSGILLEEFNSGKLSPGEASNTLPIFLIEPESVFVVKNRPAVLKCKASHSLQEVTAT
IHRDLVDEFFGDGPFKCECHAWSSRGVVKSQAATVHIAYIRKSFNQSPTSLRLELGSRAELRCEPPGGFPEPKLTWHKNNAVITADSEPGITVSA
GTLIFRQVALQHMANYSCSAENIAGRRVSDSAVLIVYVNGGWSTWSPWRECKCAGKPSQGRKRSRTCNNPMPLNGGAQCPGPQIQKSADCAACPE
DTQIVSPDGFDISSSKRMARWSAWSDWSICSAECIQVRRRKCLTQGQTQISSEAEEAGDLLLGAPGVGMAALIAAAGVGAVGSPSEATGSSSDII
PGYGKSLCAGKDIQTAECRGEQCQIGKDGKSVLMTRMNAWQDQQSRQLDNNNSKAGVQHPQNQNPRIPRTKDEHSTLIVTMGN*
(SEQ ID NO: 735)

Name: UNC-5 like protein
Classification: cell_adhesion

Celera Sequence No. : 142000013384585
TATATATTTACGATTAATTGTGTAATGAAAAACGTATTTTATATAAACAAAGATATATCAAATAAAACTAAAACTTAAACATAGCGATCGCCTTA
CCTGTGGACCGATTAATGAGTCGAAAAGTAATTTTATAATATTTTTTATTTAAGTTCCTTTCCATTTGCGATTTCAGTTTTGTTTTGGTTACGAA
AAAAACTTACAATTACTTTGTTACGAAATCTTGTTCTCAGTTTTTTTTCAATGAAGTGACGACGATGACTGGTTTAGTCATTAAAACTACAAAA
TAGTAGGAAGTTGGTTTTTATTTATATTCTTTTTTTCTTTTCTTTTCCTTTATATATCAGCACTATACTCGTAATTGCCTTTCTTTAAAATAACA AATTTCGCTGTGGTGGAGCCTTTTTAATGTTCAAGTCTAAAATCATTATTAGTGAAAGGTAGTATTTGACCAAAAAAACAAATTTCGAACGCTTA
AAAATATCACATTAAAAAATCAAACCGAATCCGATTTCATATATAAATAACACAAATTTATTTAATTTTGTTTTGGAATTTGGAATAGGTTGTCT
TAAGTTTTGTATACATAGATTTATTTCGTTTTCGTTTACCACTTCATTTTTAGTCTTTTGTTGTTGAGAATTTTCCTTGCTGTGGCCAGTTTTT
TTTTTTTTTTTTGAATGAAAATCATCTTTTACGAAGTTTACTGCCCTGACATTGGTTGCATTAATATTACGCATTACGCATTAAAATAGGCTTTT
CTCTTTACTCGTTTAGCTCCATTTTCACTTAACACTGTACACATATAATGTAAACTAATTGTATTTATATTTATTATGCAGTTGAATAGTTTATA
GTTTAATATGTCAATGTGCAATTCATGATGCAGTTTTTCATCGAATGTGACTCGTTACAATGTTTTCGGTTGCTAAGCGAATTAAAAACAAAACT
AGTTTCCGAAAAATACAACTCAAGAAATCTCCAAATGTTTTTTTTTTTTTACAACTTCTGTATTAACGTGATATAAATATAGACTGAATTTAGAT
TGGATTGGATCGACTGGCTGTTGGCGGTTGCTTTTCGTGTTACGGTAGTTGTTACTGTTAATTTAGTAGTTATCGTACTTTAATATATATTTATA
AAATAGACTTTCTCCGTTGCAAGATGCGAATTTTCGTTTCTGTTGTTGCAGTTTTCGGTTTGTGGTACATGCACGTTGCCAAAACTTACGCATCA
TGTTGCGTACCTAAAAGACAAGCACACAGATTACTAAGTTTGTTTACTCGCTTTTCCAGCGACAACTCACCTTTTTGTCCAGAGACGCGCAATTC
GATCGTGCTCCTCACGATTCTGCAAATATTGCGTGGCAATGCTGCCCACCAGCGGATCGGCTGTAAAGACACATGATATAAACATGAGATCATAT
TTACTACAGTCCTAGGAAAAGTTAAATCAAAGTGGAGAACACGACACTGTATATCAAAGTCTAAAAAAAATAAGTCTCACCTGGATTACAGTCTG
TGAGCAGGGAGCAAATTGACAGCAAGACCTTTGATATGGTCAGCGCCGGCGACCAGTTGTCCTTGAGTATGTCCAGGCAAATGACGCCCTGGCTG
TTGATGTTGCAGTGATAGATGCGCGTGCGGAACGTGACTTTGGGTGGCTTGAAGGGATACTCCGGCGAGAAGTGTATGTCGAGGAAGAAGACGCC
GCCCTCGTAGACGGATCCGGGTGGTCCCAGTATGGTGGATACCCACTCGTACAGGTTGTCGCCCTTGGGCCCGGCACTGCAGTTGGGCGGTGGGT
CCAGTGTGATCTCAGCCAGCTCCTTCTGTATGCGCTTGGCCGAGGTGCCCAGCGCCCTGGATATCCTGGGCGTTGTTTTGGCTTCCTTTCGCGGC
TCATCTCCGCCACCGGCATTGCTCCCGGAGGCACCACCGTTGGCGTTGCTGCCCCTGCCGCCACGTGCCTGCGGAGTTCCGGCAGTCGTCGGCTG
GCTGGTATTGCTCACGTTGCTGGCCGTTGTGCTGGGTGCACTGGGCGCATTTGAGGTGGCACTGGAGGTGGCCACCTCGGCGGCACTGCCCGCTG
CTGGGGTTGAAGACATTTTTGGTCTCGTTTCTTCGAACTGAAATGAGTATTTTGATGTTTGGTTAGATAATGGTTTATGTAAACGATCCACTATG
TTCAGCAGGGAATTTCCATAGAAAACTGGTGAAATATGAAGCCAAAGCCTACTTGGGATTCACATTTATTTTTAAAGGGAAATCCCTTCTTGCCT
GCACTTTGTGCGTACGAATGTAGTTGATGTGAAAAGTATGGCCAGTGGAGTCGGCAATTATACGCGAATCTTGGACGGGGCTTCCCCAGGGTCCT
TGACCTGGTTTTCCACCCAGTTTGTGCCCCTTTATGATGACAGGGGTTTGCTTTTTTTCGCACAAACGCACGCATTTCTATTGAGCAGCGGCCAT
TTTGGCAAACCCCCGACAGTAAAAAGTGGGTTTTGCATGGGATTCGTTGTCAGGCCAGTGGATGCTGGACAGGATTAGGTGATAGCTGGACAAGC
ATTTGCCCCCAAAGTTTCGAGAGCATGTGCTGGATGCCGCAAAAAATCAATCAGCAGACATTTGCAAAATGCCGCCGCCGACGGCGGAGGATGAT
GATGACGGTGCTGACTCCGCCGCCTGCAGCTCGATTGCACAATTTCGCGGAATTTGGACGCTGATTAGGTGGGGTCTATCTTGGGACCAGCCCGT
GAAGCACTATACACACCTCACTATTGCAGTTTCTTTCACTTTTTTCTATCACAACACTTGCGAAAATGATTCTCCCTGTGTCGCCTGCTGCCCTC
TCGCTCGCACTCTCGCGCACACGGCCTTCGCAGTGGATGCACGGCTGTTCCGCTGGCGTCCTTGGTGGGTGGCAGTGTCGGCGCTCCAAACTCCT
CGGCGGCTCACGGTCGCGATCGTTGTTATTTCGCTAAATTACAGTTGGCAAATTACGAGGCGACGCAGAGCCGACTTTATCTTTGTTAGAAACTC
GATAATTTGTATGTTTGTAGCCAGCTATCGGTCCGGGTCCGTCTCTAGGTGCTCGCGCTGTCCGCTCATCCTTAGCGAACTATCGATGTTCGGCT
TCTGGCAACCGTTTTTTGCCTTTTCTAGCACTGTGGCAACTCGGAAGCGGATACCATAAAAATAATATTCAAGTATTGAAATCTAACTATTTCGT
AAATGAAATAAAAAACAAGAATATTTACACCATGTATAATACACTTTGAATACCTCTCTGCTTCACCCACTTCGATAATTTAAGTGTAACACCCC
AGATGTAAAATCTTTCAATATTTACTTTAAAGTTTAAACTAGTTTTGTATTTATAAAAAGTTTACAAGTTTTGGGATTACTTCGTCTCCGCTTCT
TCCGCTAGCGCCTTGCGAGATTTGAATACGCGCACCGTGTTGTCGACACCACCAGATACAATGTACTTGGGATTGGACCAGTCGATGTCCAGGAC
CTTTTCACCGTGACCCAGAAGATCGTACAGTGGGGCCTTGGGACTCCTGCAGTCCCACAGCTTGTTCTGGTTGTCATAAGCGCCGGAGACAAATA
GGAACTCCTCCGTGGTGGACCACATGACGGTCTGCACCCAGGCATTGTGTCCCAGATAGGTATTCCTTACCACTGATCCCTCTGAAAGATCCGAA
TTATATTGGTTAGGTGGAAGTTCCATTGTTGATATTGGCAGTATTAGATCTTACGGTTTGTCCTAGGATCATAGAGCCGCAGATTCTTGTCCGCCG
AAGCAGTCAGTATCAGCCGATTCAGCTTTGAGTAGCTCGCATCGAATATGGACTTGTTGGTGGATATTTCGGTCTTGATGCCCTCAAGACTCAGA
TCCCACACCTTGAGTGTGTGATCCCAGCTGCCAGTTAGCAGAGTGGTAGCATCCATCCACTGCACGGCTGATACGCTCTCACGATGTCCCTGCAG
CGTAATTTTGGGGGTCTGAAAGGAATTGTAAAGCTGATTACAAGTCTAATTATAAATGGCAAGACTACT
(SEQ ID NO: 736)

Exon: 3059..2772
Exon: 2127..1506
Exon: 1390..1306
Exon: 1245..1001
Start ATG: 2106 (Reverse strand: CAT)

Transcript No. : CT20873
TACAAACATACAAATTATCGAGTTTCTAACAAAGATAAAGTCGGCTCTGCGTCGCCTCGTAATTTGCCAACTGTAATTTAGCGAAATAACAACGA
TCGCGACCGTGAGCCGCCGAGGAGTTTGGAGCGCCGACACTGCCACCCACCAAGGACGCCAGCGGAACAGCCGTGCATCCACTGCGAAGGCCGTG
TGCGCGAGAGTGCGAGCGAGAGGGCAGCAGGCGACACAGGGAGAATCATTTTCGCAAGTGTTGTGATAGAAAAAAGTGAAAGAAACTGCAATAGT
GAGTTCGAAGAAACGAGACCAAAAATGTCTTCAACCCCAGCAGCGGGCAGTGCCGCCGAGGTGGCCACCTCCAGTGCCACCTCAAATGCGCCCAG
TGCACCCAGCACAACGGCCAGCAACGTGAGCAATACCAGCCAGCCGACGACTGCCGGAACTCCGCAGGCACGTGGCGGCAGGGGCAGCAACGCCA
ACGGTGGTGCCTCCGGGAGCAATGCCGGTGGCGGAGATGAGCCGCGAAAGGAAGCCAAAACAACGCCCAGGATATCCAGGGCGCTGGGCACCTCG
GCCAAGCGCATACAGAAGGAGCTGGCTGAGATCACACTGGACCCACCGCCCAACTGCAGTGCCGGGCCCAAGGGCGACAACCTGTACGAGTGGGT
ATCCACCATACTGGGACCACCCGGATCCGTCTACGAGGGCGGCGTCTTCTTCCTCGACATACACTTCTCGCCGGAGTATCCCTTCAAGCCACCCA
AAGTCACGTTCCGCACGCGCATCTATCACTGCAACATCAACAGCCAGGGCGTCATTTGCCTGGACATACTCAAGGACAACTGGTCGCCGGCGCTG
ACCATATCAAAGGTCTTGCTGTCAATTTGCTCCCTGCTCACAGACTGTAATCCAGCCGATCCGCTGGTGGGCAGCATTGCCACGCAATATTTGCA
GAATCGTGAGGAGCACGATCGAATTGCGCGTCTCTGGACAAAAAGGTACGCAACATGATGCGTAAGTTTTGGCAACGTGCATGTACCACAAACCG
AAAACTGCAACAACAGAAACGAAAATTCGCATCTTGCAACGGAGAAAGTCTATTTTATAAATATATATTAAAGTACGATAACTACTAAATTAACA
GTAACAACTACCGTAACACGAAAAGCAACCGCCAACAGCCAGTCGATCCAATCCAATCTAAATTCAGTCTATATTTATATCACGTTAATACAGAA
GTTGT
(SEQ ID NO: 737)

Start ATG: 310 (Reverse strand: CAT)

MSSTPAAGSAAEVATSSATSNAPSAPSTTASNVSNTSQPTTAGTPQARGGRGSNANGGASGSNAGGGDEPRKEAKTTPRISRALGTSAKRIQKEL
AEITLDPPPNCSAGPKGDNLYEWVSTILGPPGSVYEGGVFFLDIHFSPEYPFKPPKVTFRTRIYHCNINSQGVICLDILKDNWSPALTISKVLLS
ICSLLTDCNPADPLVGSIATQYLQNREEHDRIARLWTKRYAT*
(SEQ ID NO: 738)

FIGURE SHEET 402

Name: Ubiquitin conjugating enzyme 2
Classification: enzyme
Gene Symbol: UbcD2
FlyBase ID: FBgn0015320

Celera Sequence No. : 142000013384588
AGCGACACGTGATCACCACCCAGACGGAGCACAAGTGCGTGCTGGACTCTTGTCGTGCTTTAGAGAACGAGGGCTTTAAAGTCACGTACCTGCCA
GTGCTGGCCAACGGACTCATCGACCTCCAGCAACTGGAGGAAACCATCACATCGGAGACCTCGCTGGTGTCCATTATGACGGTGAATAACGAAAT
CGGCGTACGGCAACCCGTCGATGAGATTGGCAAACTGTGCCGGTCTCGCCGAGTATTCTTTCACACGGATGCCGCTCAGGCGGTGGGAAAGGTCC
CGCTGGACGTTAACGCCATGAACATTGACCTGATGTCTATATCCGGCCACAAAATCTACGGCCCAAAGGGTGTAGGCGCCCTGTATGTCCGACGA
AGGCCGAGGGTTCGCCTCGAGCCCATCCAAAGTGGCGGCGGCCAGGAGCGTGGCCTAAGGAGCGGAACGGTTCCAGCCCCGCTCGCCGTGGGATT
GGGAGCTGCTGCGGAACTTTCTTTGCGTGAGATGGACTACGACAAGAAATGGGTGGACTTTCTATCCAATCGCCTGCTGGACAGGATTTCAAGTG
CCTTGCCGCATGTCATCAGGAATGGTGATGCCAAAGCCACATACAATGGTTGCCTGAATTTGTCGTTTGCCTATGTCGAGGGCGAGTCACTACTG
ATGGCTCTTAAGGACGTGGCCCTGAGCAGTGGGTCCGCCTGCACCTCCGCCTCCCTGGAGCCCTCCTATGTTCTGCGTGCCATCGGCACCGACGA
GGATCTTGCCCACAGCTCCATACGCTTTGGCATCGGGCGCTTTACCACCGTCGAGGAGGTGGACTACACCGCCGATAAGTGCATCAAGCATGTGG
AGCGACTGCGCGAGATGTCGCCGCTGTGGGAGATGGTCCAAGAGGGCATCGACCTAAAGACCATCCAATGGTCGCAGCATTAATGTACTAATATT
TAAGCCGTTACTGTTACACCACACTTTGAAAGCGAAGGGAAAATAAATTTGTTGGAAGAGTATCTAGGTTTATTTGTACACAAAACCACTTATAA
CTAAGCTTAGTCCGAACGAATGTGCTTGTGTAAGAGGTGAGGCAAGAGAGACCCCAAAAAGCGAAAACGGCTCAAAGTGCGACGGCCAATGATAT
GCAAATGATGCAATAATTTGCATTCGCCGCTGGTCAAGGTTCAGTTGGCCTTCTTCTGGGGTGAGCCGCTGGATCCACCGCCCAGGATCTTACGG
CGCTGGGCGAACATGTGCAAGTACAACTGCGGGAAGATGGGGATGTAGCCGAGCATGACGATCCACAGGAATCCAAAATACGAGAAGGTGGCGTT
CCACTTGTTGGGCATCACCACACTCCACACGCTGTTCTCACGGGCATAGCTCTGGGCCCACCAGAAGCACAGCAGCTCCCCAGTCACGCCGATGG
GATACAGGACAATGAATGTGGTGTAGCGCAGGAACACCACAAAATGCGGCACCACCTTGACGATGTTCAGAGCGTAATATCCATATCGGATGATC
TCAGTGATGGCCCAGGCCAGCAGGGCGATGGCAGACCGGGTGAAACCTTTCCAGTAGGCGTGGCCATCACCACGCCGACGACCACCATCATGCG
GCTGAACACCTGGAAGCCAGTGACCACCGGGTTCGACTTGACCAATCCAAAAGAAGCATTGAGTATCTCCACGAACGCGGCATTCTGGAAGATGA
TCACGGCCAGCCGAGTATACTCCCACAACGTCACCTGGGCACGGAACTCCGGACCCTGCAATATGTAGTAGTTGACCAGCTGCCACAGGATGTAG
CTCCATCCGACCACCTGGCCGGCGTTGTACGCAAACAGGTACAATTTAGTGACCGCCGACGGCTCCTTGGAAGCGCCTGGTTTGCTGGACTTGGA
CACTGCCTTTGCTGACATGTTGGAGCGGAGATGTGTGAACTTTCACCTTGCCGATCGCCGCTGGTTAACTAATCAGTCGTCACAGTCTTATCGCC
CTGTAGCGCGATAATTCCGAAGTCGCTTTCACCTGATTGGGTCAGTATGACCGCACGGCGACCACACAAAAAATACCAAAAAAAAGGGCTAAGAA
ATATATATAACTATTAAATACCCTTCCATATAATATCTTTTATAAATAAAAACGCTTTGATATCGAAAATTGTTCATTTAATCATTTGTAAATTA
ATAATCATTTAATTAAAATTTCTTGATATAAAATTTCATTCGCCTTTATTTTCTCTGAATTTTGTTTTTTGCTATTCACAATTTTTCCAACGAGT
ATAAATAAAAGATGAACTTCATTCTTTCAAAGTCAACGGGTACAAAGTGCATAGCCTTATAACCTTTCCTCTATTCACAGATCGCAAATCTAAGT
TAACAATGCCACAACCATTAGGCATGCTTAGCAATTAAGTCGTTTTTATGTGCAAAGTTATTTCACTTAAGTTAAGTTAAGTCTCAAAACGTTAA
AATTCTTTGAAAACTATGATTTTAAATCCTATCAACTTACTTTAAAGCTGAATTACCGTTTCTTATGTTAGTACAAATTAAAGTAAATAAACTAA
ATAATAACACAATTTATATTTCTTCGAAAATATTCTTAGTATCATTAGTAAAACTATAATAATTTTTAATTATAGTAAAAATTAATACCTATCAT
ATATATTCTTTCTTTAATGTATAGTAAAGCATGGTTAAGAACAATGGATAATGGGTGGTTATGAGCCGACATATAAAAATTTATCGCTAACGACA
AGGTGGAGAAATCAATTTTTTTGATAAGAACTAGCCCATTGTACGCTTTGCATTTCTAACCACATTTCGCTTAAAGCAGCCCACTGTAGGCGGCA
GCTGACGTTTCCCAGCGAACGACGGCTGGTTTGCGCGATGAGCCAGCAAGGCAGCTAAACTTTCTGGTCGCCTGGTGGAAACCGAACCGAAAACC
GAACGTGTCTGAAAAAGTCCGCCACCACCACGGACCGGTGCACGTCCCCACCTGCCAAGTCGCGTGTGTGTGGTGTTGCCTGTGGACCGACCCCA
G
(SEQ ID NO: 739)

Exon: 2041..1001
Start ATG: 1918 (Reverse strand: CAT)

Transcript No. : CT20927
ACTGACCCAATCAGGTGAAAGCGACTTCGGAATTATCGCGCTACAGGGCGATAAGACTGTGACGACTGATTAGTTAACCAGCGGCGATCGGCAAG
GTGAAAGTTCACACATCTCCGCTCCAACATGTCAGCAAAGGCAGTGTCCAAGTCCAGCAAACCAGGCGCTTCCAAGGAGCCGTCGGCGGTCACTA
AATTGTACCTGTTTGCGTACAACGCCGGCCAGGTGGTCGGATGGAGCTACATCCTGTGGCAGCTGGTCAACTACTACATATTGCAGGGTCCGGAG
TTCCGTGCCCAGGTGACGTTGTGGGAGTATACTCGGCTGGCCGTGATCATCTTCCAGAATGCCGCGTTCGTGGAGATACTCAATGCTTCTTTTGG
ATTGGTCAAGTCGAACCCGGTGGTCACTGGCTTCCAGGTGTTCAGCCGCATGATGGTGGTCGTCGGCGTGGTGATGGCCACGCCTACTGGAAAGG
TTTCACCCGGTCTGCCCATCGCCCTGCTGGCCTGGGCCATCACTGAGATCATCCGATATGGATATTACGCTCTGAACATCGTCAAGGTGGTGCCG
CATTTTGTGGTGTTCCTGCGCTACACCACATTCATTGTCCTGTATCCCATCGGCGTGACTGGGGAGCTGCTGTGCTTCTGGTGGGCCCAGAGCTA
TGCCCGTGAGAACAGCGTGTGGAGTGTGGTGATGCCCAACAAGTGGAACGCCACCTTCTCGTATTTTGGATTCCTGTGGATCGTCATGCTCGGCT
ACATCCCCATCTTCCCGCAGTTGTACTTGCACATGTTCGCCCAGCGCCGTAAGATCCTGGGCGGTGGATCCAGCGGCTCACCCCAGAAGAAGGCC
AACTGAACCTTGACCAGCGGCGAATGCAAATTATTGCATCATTTGCATATCATTGGCCGTCGCACTTTGAGCCGTTTTCGCTTTTTGGGGTCTCT
CTTGCCTCACCTCTTACACAAGCACATTCGTTCGGACTAAGCTTAGTTATAAGTGGTTTTGTGTACAAATAAACCTAGATACTCTTCCAAC
(SEQ ID NO: 740)

Start ATG: 124 (Reverse strand: CAT)

MSAKAVSKSSKPGASKEPSAVTKLYLFAYNAGQVVGWSYILWQLVNYYILQGPEFRAQVTLWEYTRLAVIIFQNAAFVEILNASFGLVKSNPVVT
GFQVFSRMMVVVGVVMATPTGKVSPGLPIALLAWAITEIIRYGYYALNIVKVVPHFVVFLRYTTFIVLYPIGVTGELLCFWWAQSYARENSVWSV
VMPNKWNATFSYFGFLWIVMLGYIPIFPQLYLHMFAQRRKILGGGSSGSPQKKAN*
(SEQ ID NO: 741)

Classification: hypothetical

Celera Sequence No. : 142000013384588

GCGTACTCAGTGGCGGTGAGATCGGCATCACGATGGTCCAGTTGGTCAGCGGGTTGCTTATTGCGGAGCAGGATTGGCCCGTGTTCTTCTATCTG
GTTGGTGGAGGAGCCGTGGCCTGGTTCTTGGGATTTGTAAGTCTATACGAAGTCTAAAGTCATGATAATCATAGTTTAAACCAATTTGTTCCCAA
GACCTTAGTTTGCTATAGCACTCCGGATCATTGTCCGTTTATTCAGAGCGAAGAAAGGGAATACATAAGGTGCAATACTAGCAACTCCTTTTTGT
TGACCACTGGCAGAGAAAGAGAGGAGATGGACGGGGAAGATGGATATGAAGGTGAGGATAGGGAGCACCGCAGAGAAGTGGAAGCAACGTGCAAC
ACTGCACCTTGGCGGAGCATGCTTAACAGCACGCCACTCTGGGCCCTGGTTTCCACCTCCATGCAGCAGGAATTCCAACAGAAATTGCCCCAGGA
GCTGCAAATTGCGCTAGAGGAAGTAAGAGCCCGTGGCACCAGTTTCTCAGAACTAACCACCATCATCGAAACGATAGCACCGTCCGTTGGAAACT
GGATAGCTTCACTGACAACAGGGCGGCTGAGCGACGTGCTAATCGAGCAGCAGATTCTCACGCGCACTCAGACACGCCGCCTCATGTCCTGGTTG
GTCTTCCTATGCGGATCCATGTACATGCTACAGATCAAGATGAGCGGAGCACGAATCTGGAGCGTTCTTGGCATGGGAGCCTACTATGCGAGCAT
TAAGCTGCTACCGCTGGATATGAGTCCCAACTATGCTGGCACTTTGATGGGCATTTCGGGCGGCATGGGCGCGCTTCCAGCACTTCTGATGCCCT
ATCTGGAACAACTGGAGACCGACTACAAGCTGGTGAGCAGTGTGAGGGCCGCCATGTGGGTAATCGGCGCCAGCTACATATCCGGCGATGTCCAG
GCGTTTAACCAACCGGAACGGGAGCCACAATGAGGAGACTTGCTTGTTTTAAGTTTAATCTTACGCTTAAACATAAGCTACTGGATTTGTCTTAG
TGGATTCCTTAGGCAACAGATTCTAGTTTACATATGTACCATAATACATGACAATTTCTATGCTAAAGCTAGGAGCATAAACGTAAACAAGCTTT
ATATATATATATATAAATAACAGGTATGGTCGATATTAACTTAATTAGAGTAGGACTGCTGGCTAAATGCTCCGCGCTGGCTCTTATTTTCTCGG
GATATCAATCCCAACACACACCGGTTTCATACTCTATGCAACGCCCTGGGCCATCAATCCGGATTGGGCCATTGCCGACACTGAGTTCATGTCGA
TACCCAGCTTTTTGGTGACGTTGATTTGGGCCACTGCCGCGTTGCGCAGCGAGTAAACGTGCACCAACTCCGCCTGACTCTTGGCATAAAGCAGT
GCCTTTTCAAAAAGCTCGACGGCCCGTGTGAGTTGCGCCCGCTGAACTTCGACTGTTCCGAGTGTCTCGTAGGCCAGCTCGCATTTGGGATCTAC
TTCGATCGCCTTGTTGAGCAGCTGGACAGCCAAATTAATGTCTCCGCGCCACTGAAGCACCATGATGGCCTGGTGAACGATAAGTGCAGGATTTG
TTGGCGCCAATACCATGGCCTTTTTGTAGTATTCCTCCGCCTGGGTAAACTGTTGCTGGTCGGCCAACACCTGAGCCGTTAGACTATAGCACTCA
ACGCAGCTCGGGAAACGCTCGATGGCATTTTGGAAGGTGTGCATTACGCTCTCCAAGCGCCGCTGGTCGCCGGCCAGGAGGGATAGTCGGTACTC
GGCATAGCACTTCTGGACGAAGGCGATGGCGTGGTTGGGTGCAATGCTCACCGCCTTTTCGAACTCGGCCAAGGCGGGCTCTATCTGCTCCAGCA
GCAGAAGTATCTGGGCGCGCTGGTGGTACACATCTGGGTTCTCTGGGTTCAGGCGTTCCGCCTCAGCAAAATCGGCTATACCCTTTTCGCGCTGA
TCCAGCTGGATGTAGAGAGCTGCCCGCTTTATGTAGGCATACGCACGCAAGTTGGGATCAGCATAGTCTGTAGTGAAATAAAGTTAATAGAATAG
AAATCAAAAAACAACTGAAGAAAACCGACTAATTAATGAATTAAACTTAAACAAATTCTTACCATTAGCTATAATAGCATCAAAGTCCTGCTGGC
TTTCTACATAGGAGCCGCACAGCAGATGGAAAGTTCCCCGCATAAGCAGAGCCTCCACTTTGTACTGTGCTTCGGCCTCGGAGGATTCGATCTCT
TCGGTGCAGGCGGGAATAATTTCCTCGTACTTCTCCTCGAGGAAAGCGAGGTGGGCGCGCAGGAAACCCTTTGGGGGTGCATCGGATTTAGGGGC
TGGGACTTTCATGGTCTGCAGCGGATCCGCGATGAAGGAACGCGTGTAGGTGTTTACGAAGCAAGCCGACGGCACGACTGGCACCCGATTGCGCA
TACCCTTCTCGGCGTCCAGTCGGCCGGTCTCCTTGAGCACACGGTCAGCGAACATGATAGTTTGATTATTTTGGAACATCTCCAGGATACAGGTG
GCTGTGACATCGTCCAAGCACTCGTTCATATCCTTGGTGGCTTCGTGAGCACGGGCACGACGATAATATGCCTTGGCGTAACGAGGATTGAACTC
CAGCGAGGCTGTGCAGTCCTCCTTGACGTTGGACCACTTCTTGAGCATCTCGTAAGAGGCGGCGCGGTTCTGGTAGAAGATGGCCATGTCAGTGC
GGTGCTCCTTGGGACACTTGTCGATGGCCTTGTCATAGAATTTAATGGCCTCATCGTACTTCCCATTCCTGTAGCAGTTGTTACCCTCCGTCTTG
TAGTTGTTGGCCTCCTTAAGAGGCGACAGCTTCTCGCCCAGCTCAGCGGACTTTTGATTGCGCTCTAGCTCCTGGTCCGGTGCGGTGCCGTCCAG
GGAGATGGCCTGCTTCTCGATCTTGGCCTTTGGTCTCTTCTTCTCCCCGTCCAACTCCTTGGACGCAGCCGTCCAGCTCTTCACCGCATAGGTGC
CCAGTCCAATGGCCAGGGGAGTTCCAAGGATGAGCGCCAGCTGCCACTTTGTCAGCTTCATCGAGCCAATGTTCAGAGTCATCGCCATTGAGCCG
GTCTTTTTATGGATGTGTGTTATGTGTGATGAACTGCAAGAAAAGAGCTGAATCAGTTTGGGTGCCGCCACAAATTGTGTAATACTCCGCTGGCT
TATCGCTCAGCGCCTTTTGAGCTTGCTAAATGCCGGGCGGGGGGCACGTTTCTGCAGTACCTAACCCCCAACCCAATTGATTTTTCACACCCCCA
ACTGGCCGGGATGTGAATCAGTGCAGTCAGCGAACGGAACTTACACTTTTTTAAAACTTTACACTGCTGTGAATTTGGCAATTGTTAAACGTCGA
TTGTTCTATTTTCAGTTAGAACTCGGGAAACTTAGATTCTATTGTATATCAGCCTGCTGAGCACACGACATCGAAAAACGATAGACATCGATAGG
TATGGAGTAATAACGGCACTGCGAATGCTTATTATGGAAGAAGAAGATCAGTGAGAGAATAAATTGTGTGAATAGTTTAAAAAAAAACTAAGGAG
TTCGAATATGATGTATTTGTAATAAAGCCTGAATTTATACTTTACGAATACTGTACGAATAAATATTTTAGATCTCTATATTACATTCTATCAGA
CCGAAACAGAGTTCTTAAATTTTAAAATCGGTTTCATCCACTTTACAAATTGAAATACAAATGCATTGTAATATTACAATCAATGTATTTATAGG
AATTCACTAGAATACACGGACAGCCTATGGGTGATTCTCCTCATCTGTGCTGGAAGTTGGAGCTGGAGCAGGAGCAGAAGCGGAACTGGTAGTCG
ACTTATCGGTTTCCGTAACCAAGATCTTGTCCAGATTCTCCAGTTTAACTAGGCCCTGGGAATCGGCGTTGTGGATGAGATCACATATTGTGGC
GACTCCACGACCAGGATATACTGGCACGTCTTCGGCTCAAGCAGGTACATGGATACAGCGGTGCCGCTGTTCGTTACAGGTGTGCAGGTTAACTT
CACGTCCACTTCGCGGGGCACTCCAATCTGTTCGCAGTGGGTTCCCTTGCCATAATGGTGCCAGATGGATGTCGTGAAGCCGGAACGGCGTGCAC
CCTTGTCCGGGTTGGCGTTGGACCAAGCACGATGCGCTTCCTCTGAGAAGTAGCCAAGAAAGAGCTCCACTTCGCTGGTCTTATCTTTGTGGAAC
TGACGCACATGTCGGCCATAGCAGAACTCGTACTTCCACCAGCCATTGCCCTAAAAAAAAGAGTATTATTGAAGCAAATGCATGGGTCAGCTGCA
TGTTATTCCTACCCCAGTTAGGCAGTTCTTGCCCGATATAAAGTCCTTAAGGGGCGTCAGATCAGTGATGGGTGTTGGTCCAGTTTCAGAGGCTG
CTATAGACAGCAGGA
(SEQ ID NO: 742)

Exon: 3480..3370
Exon: 3122..2153
Exon: 2062..1001
Start ATG: 3122 (Reverse strand: CAT)

Transcript No. : CT20965
TCAGCAGGCTGATATACAATAGAATCTAAGTTTCCCGAGTTCTAACTGAAAATAGAACAATCGACGTTTAACAATTGCCAAATTCACAGCAGTGT
AAAGTTTTAAAAAAGTATGACTCTGAACATTGGCTCGATGAAGCTGACAAAGTGGCAGCTGGCGCTCATCCTTGGAACTCCCCTGGCCATTGGAC
TGGGCACCTATGCGGTGAAGAGCTGGACGGCTGCGTCCAAGGAGTTGGACGGGGAGAAGAAGAGACCAAAGGCCAAGATCGAGAAGCAGGCCATC
TCCCTGGACGGCACCGCACCGGACCAGGAGCTAGAGCGCAATCAAAAGTCCGCTGAGCTGGGCGAGAAGCTGTCGCCTCTTAAGGAGGCCAACAA
CTACAAGACGGAGGGTAACAACTGCTACAGGAATGGGAAGTACGATGAGGCCATTAAATTCTATGACAAGGCCATCGACAAGTGTCCCAAGGAGC
ACCGCACTGACATGGCCATCTTCTACCAGAACCGCGCCGCCTCTTACGAGATGCTCAAGAAGTGGTCCAACGTCAAGGAGGACTGCACAGCCTCG
CTGGAGTTCAATCCTCGTTACGCCAAGGCATATTATCGTCGTGCCCGTGCTCACGAAGCCACCAAGGATATGAACGAGTGCTTGGACGATGTCAC
AGCCACCTGTATCCTGGAGATGTTCCAAAATAATCAAACTATCATGTTCGCTGACCGTGTGCTCAAGGAGACCGGCCGACTGGACGCCGAGAAGG
GTATGCGCAATCGGGTGCCAGTCGTGCCGTCGGCTTGCTTCGTAAACACCTACACGCGTTCCTTCATCGCGGATCCGCTGCAGACCATGAAAGTC
CCAGCCCCTAAATCCGATGCACCCCCAAAGGGTTTCCTGCGCGCCCACCTCGCTTTCCTCGAGGAGAAGTACGAGGAAATTATTCCCGCCTGCAC
CGAAGAGATCGAATCCTCCGAGGCCGAAGCACAGTACAAAGTGGAGGCTCTGCTTATGCGGGGAACTTTCCATCTGCTGTGCGGCTCCTATGTAG
AAAGCCAGCAGGACTTTGATGCTATTATAGCTAATGACTATGCTGATCCCAACTTGCGTGCGTATGCCTACATAAAGCGGGCAGCTCTCTACATC
CAGCTGGATCAGCGCGAAAAGGGTATAGCCGATTTTGCTGAGGCGGAACGCCTGAACCCAGAGAACCCAGATGTGTACCACCAGCGCGCCCAGAT
ACTTCTGCTGCTGGAGCAGATAGAGCCCGCCTTGGCCGAGTTCGAAAAGGCGGTGAGCATTGCACCCAACCACGCCATCGCCTTCGTCCAGAAGT
GCTATGCCGAGTACCGACTATCCCTCCTGGCCGGCGACCAGCGGCGCTTGGAGAGCGTAATGCACACCTTCCAAAATGCCATCGAGCGTTTCCCG AGCTGCGTTGAGTGCTATAGTCTAACGGCTCAGGTGTTGGCCGACCAGCAACAGTTTACCCAGGCGGAGGAATACTACAAAAAGGCCATGGTATT
GGCGCCAACAAATCCTGCACTTATCGTTCACCAGGCCATCATGGTGCTTCAGTGGCGCGGAGACATTAATTTGGCTGTCCAGCTGCTCAACAAGG
CGATCGAAGTAGATCCCAAATGCGAGCTGGCCTACGAGACACTCGGAACAGTCGAAGTTCAGCGGGCGCAACTCACACGGGCCGTCGAGCTTTTT
GAAAAGGCACTGCTTTATGCCAAGAGTCAGGCGGAGTTGGTGCACGTTTACTCGCTGCGCAACGCGGCAGTGGCCCAAATCAACGTCACCAAAAA
GCTGGGTATCGACATGAACTCAGTGTCGGCAATGGCCCAATCCGGATTGATGGCCCAGGGCGTTGCATAGAGTATGAAACCGGTGTGTGTTGGGA
TTGATATCCCGAGAAAATAAGAGCCAGCGCGGAGCATTTAGCCAGCAGTCCTACTCTAATTAAGTTAATATCGACCATACCTGTTATTTATATAT
ATATATATAAAGCTTGTTTACGTTTATGCTCCTAGCTTTAGCATAGAAATTGTCATGTATTATGGTACATATGTAAACTAGAATCTGTTGCCTAA
GGAATCCACTAAGACAAATCCAGTAGCTTATGTTTAAGCGTAAGATTAAACTT
(SEQ ID NO: 743)

Start ATG: 112 (Reverse strand: CAT)

MTLNIGSMKLTKWQLALILGTPLAIGLGTYAVKSWTAASKELDGEKKRPKAKIEKQAISLDGTAPDQELERNQKSAELGEKLSPLKEANNYKTEG
NNCYRNGKYDEAIKFYDKAIDKCPKEHRTDMAIFYQNRAASYEMLKKWSNVKEDCTASLEFNPRYAKAYYRRARAHEATKDMNECLDDVTATCIL
EMFQNNQTIMFADRVLKETGRLDAEKGMRNRVPVVPSACFVNTYTRSFIADPLQTMKVPAPKSDAPPKGFLRAHLAFLEEKYEEIIPACTEEIES
SEAEAQYKVEALLMRGTFHLLCGSYVESQQDFDAIIANDYADPNLRAYAYIKRAALYIQLDQREKGIADFAEAERLNPENPDVYHQRAQILLLLE
QIEPALAEFEKAVSIAPNHAIAFVQKCYAEYRLSLLAGDQRRLESVMHTFQNAIERFPSCVECYSLTAQVLADQQQFTQAEEYYKKAMVLAPTNP
ALIVHQAIMVLQWRGDINLAVQLLNKAIEVDPKCELAYETLGTVEVQRAQLTRAVELFEKALLYAKSQAELVHVYSLRNAAVAQINVTKKLGIDM
NSVSAMAQSGLMAQGVA*
(SEQ ID NO: 744)

Classification: hypothetical

Celera Sequence No. : 142000013384588
ACTTTTGTAATGCGAGTTTAACGAATCTTTAATTTAGAAATACATTTAATAAAAATAAAAAACCGATTCTAAGGCACTTTTAACACGCAATATAT
TGCAATGTTTAATTTTATAAAAAAACAGGTTTTTCATCACCTTCTATTTGTTTGAAGTTTGGAACACCACATTTTTAGATAGATCAATGATTCAG
ACGAAATGCTATTTAATGAAGATAAGGAATATTTATGACTAACCAAAATGCGAATTTAAACATACATAAGAGTCTTGGAATTTTAATTGTCAATA
TGTTCGAACAATTTCATTAATATGCATTATAGCAAAACCACCTGATCGAGAGTCTGTTTTATTGTTTACCAAATATCAACAACGCAATTCAAAAA
GCCGGCAAATGGCGTTTATAGAGAGAGAGAGAGCGAGAGAGAGGAGAGAATTCCATTAGAGTGGACCTTTCTGGAAAAGTTTGTTCGGTTTATTT
TTGTACGTGTGCTTGTTTGTTTGTGAGTGGAAAATAACATAGCTTTTGTAATTTTGGACACCTAATGTAAAAATATCGTTTAGTATTGAAAGTCA
ATAAAAGCGGCGCAATATTCATAAATGCAACCTTACACGCAAATTTAAACCGGAAGAAATGATGCAGGAATATGTGTGTGCAAGTTTAATTACCT
GTGTAACTGGTGAACTTTCAATGGAAGGTCTCGGGAATATTTCCGTTTGCAAACTAACATACATACATTACATACACAAATAAATATGTTCATAC
ATGTTCTCTTTTTGGTCGATCGCTGTAAACAAAGAAAAAAGTCGACTGCAACTGCTTTTGCGATAATCGAGGAGCTGAGTGCAAATGAGTTCAAC
TAAAAGGCTATAAATATGCACAACAGCACACCAACGGCATTCAAAAAGCTCTCTCGCTTGGAAAGGTGCGCTGCAAATGCAAATGAAAATAAGAC
GACCAGGCTATTCAGTTTTGGTTTTCTCTTTATTTTATATGTATTACCTAAGTCAAACTTCATTATTTGAAACGCTCTAAGGCTTAGCAACTAAA
ACTTGCAAGTCTGAATTAGTTTAGGAATATATTAGAAGCTAAGAGTAGTATGTGCCTTTCTTTTTTTGTGTTTGTGAAATTATAAGCGAAATAAA
ATTATTATAATGTTCACAAAGTTTAGCGCCGCATGAAAAGCCAATGCACAATACAAATGCAATGTGTATTTCCAGCTGGCTTTTGTTTTTCTTTC
TTTCCTTCCAGCAAAACTGCTGCTTGTTCTTCTTTTTCTTCTCTCCTTTGCTTTTGCTTTCCTTTTAAATTCGAAGATTTCTTTTCTCCTTTCAG
CGCGGCCCCGTTACTTCTTTCTCTCCTGTTCCACCGCCTCCGTCGATGCCCTGCATCAGTTCTTGCAGGCGGCGGCTTTCTTGTTGTTGTTGTTG
GTGTTCATCAGCTTGGTCAGAATCTTGCGGGAATGACCGGAGGGATCGAAGTGGTTGGTGTGCTCATTGGCCTCCCTCTTGTTGCGCTGCTTGCC
GCTGTGTCCAGAGAAGATGTGCTTGTCATGGTCGAAGTTGTAGTGCTCGTACTCATCGAAGTGGGCCTCGGACATAATGGCGATTTAAGGTTGCA
AAACTAACTGCGTTCTTGGTTGGTGTCTGCTTTTTGTTTCTCTGCAAACTTGCAGGCTGCTTTCCAAATTTCTCTTCTGCTTTTTTTTGTTCACT
TTTCGCTGAGCTGCGAACGGAATTGAATTTTTTCGGTCGAGCAGCGGCTTTTATAGGCGCGCAAGCTTTCTGTTCCGTAACCAAAGCTCTCTCTC
CGTCAGAGTTGCCGGATTTAGCTAAAGAAACTACTAGAAGGGCATTTAATTGTTGCTTACGTGTAGTTACTAAAAATATTTAATTTTTCTATAAC
TTTCTACTGAACTTTTACAAAATATATTTGCTCTTTTTTATGTAAAAGAATTTTTAGTTATTAAAATTCATAGTTATTGGGCCTGACAACCCTTT
TGCGCTCAAGAGAGTGCCTCCTTGACAATTTTTGCTGCGCAATTTAATTTTTTGCTGTTTACAAAGTGCGCGGTAAACAAAAAAACTGAAATCGC
CAAACATATTATTTCGCCTTGTTCATTTATTTTAATAATTTAAGAACTTTTAAGCATACACACGTTCCTGAGTGGTTACATAACACACACCCACC
TTGGCCCTCCGCAAACGACCATCAAAGTGCATTTACCCTGCATTTGTTTCTCCACCCAATAAATATAGAATTAAATGCATCATATGTTCTGGATA
CACTGCTCAAAATTTGTTTATTTTTTTACACTCAACAATATTTGAATGTTAGGGCACAAGAAACAATTTAGCAATAATTATAATTCGAATAACAT
TTTTGATTTACAAAAGATATACTCATAATGGATATTTATTTTGGTGCATTAGAACCTGATCGGTTGACCCACTTCCCTCCCACCAGGCAACGCAT
TTGTTTATTTCTGAATAGCGAAAAGCTTTCAGTTTGTTTTGGTTTAATGGATTTTATATAAACAAATGTTACGTACATACATATATACATAGCCT
TCTGGCGTTGATAAGGTGCTAACTATCGCTCTAGTTAGTCATTTGGCAGGTATTCGTTCTGAAAGTTCGTCTTCAAACGACGCAATAGATCGTAG
TCACCATCTTAGATAAGATAGAACGGCCTCAACAATGTTGTTTCAAGAACCTGCCACAAT
(SEQ ID NO: 745)

Exon: 1720..1001
Start ATG: 1595 (Reverse strand: CAT)

Transcript No. : CT21019
CTCAGCGAAAAGTGAACAAAAAAAAGCAGAAGAGAAATTTGGAAAGCAGCCTGCAAGTTTGCAGAGAAACAAAAAGCAGACACCAACCAAGAACG
CAGTTAGTTTTGCAACCTTAAATCGCCATTATGTCCGAGGCCCACTTCGATGAGTACGAGCACTACAACTTCGACCATGACAAGCACATCTTCTC
TGGACACAGCGGCAAGCAGCGCAACAAGAGGGAGGCCAATGAGCACACCAACCACTTCGATCCCTCCGGTCATTCCCGCAAGATTCTGACCAAGC
TGATGAACACCAACAACAACAACAAGAAAGCCGCCGCCTGCAAGAACTGATGCAGGGCATCGACGGAGGCGGTGGAACAGGAGAGAAAGAAGTAA
CGGGGCCGCGCTGAAAGGAGAAAAGAAATCTTCGAATTTAAAAGGAAAGCAAAAGCAAAGGAGAGAAGAAAAAGAAGAACAAGCAGCAGTTTTGC
TGGAAGGAAAGAAAGAAAAACAAAAGCCAGCTGGAAATACACATTGCATTTGTATTGTGCATTGGCTTTTCATGCGGCGCTAAACTTTGTGAACA
TTATAATAATTTATTTCGCTTATAATTTCACAAACACAAAAAAAGAAAGGCACATACTACTCTTAGCTTCTAATATATTCCTAAACTAATTCAG
ACTTGCAAGTTTTAGTTGCTAAGCCTTAGAGCGTTTCAAATAATGAAGTTTGACT
(SEQ ID NO: 746)

Start ATG: 126 (Reverse strand: CAT)

MSEAHFDEYEHYNFDHDKHIFSGHSGKQRNKREANEHTNHFDPSGHSRKILTKLMNTNNNNKKAAACKN*
(SEQ ID NO: 747)

Name: p8-like

Celera Sequence No. : 142000013384588
TGGTGGCCATGGCAGATTTCGTACGACCAGTAGGCCTCGATGCGGTACGTGCAAGTCAGGGCGGAGAAAATGGGCTGCAGCAGAGTAATTGGAGC
TGCGGAATTCGGAAATTATGTATAATCCAATGGGATGTTAGTTGCAATGCCAATTTCTTACACAACTCTGGCTTGTCGGACTTTTCCTCCTCTTT
TTGGTGTTCCAAAGTGGGAATCAGGCAGTCGTACTTCTCCTTATCCGGCGTGTAGAATGTTCGCAGCTGATTGCCCAAGCTCTAAACAGCATTAC
TTAAGGAAATTTGTTATGTCTGCATTAATAAATTTGTACTCACTGGCTGCACATCTAAATCCGGCACTTCGAAATCAATTTTATACAAAATTGA
ATCGTCAAAATCTTTGGCTTCGTGGGAAACCGCTGCAATTATTAAATTCAGCAGCAATGCTATTCTCGCAATTATCACGTAGGACTTGCCCATTT
TCGTGTTTAAGGCAGCGATTTCTTTACATGAGTATTTTCGTGACAATATACAAATAGTTGCAAATGCTACGTGTTGTTTTTCTCAAAAAAATAAG
GAACATATGTTGATTGTGTGTGCGGCACTGTGAATGGTTACTGCGAAAGAAGAAGAAAATCTGCTGGCCTGCATGGGCATTTTAGCTTGGAAATA
GCTAAATATCAAAAAATAACAGTCGCAGTCGACGGCACATACAAATTTTTTGAATTCAAATTCTTTAAAATCTAAGTTTTGCATTTAAATCTAGT
CATTGAATATTTCTCATTAACAAAATACAAAATTTTATCTCTTAAACTTAACTGAATGTTTTCGTATTTATTGCAGATTTAATGGTCATTCATCA
TAAAATCTTTTAAGAATCTGTATGAAAATCCAAAATAAGTCGAGAAACTAAAGCCACGTCCTCCAACAAATTAAACTCAGTTCCCAGTTTATCTT
CAACATAATTATATTTCCTTAACAAATATCGCATATGGTAGTCAGTTCCCTATCTCATTCCCAGCGCCGGCGTGTCCTTTTGCGCCGTGGACCA
GCCGAGCTCCTTGTCCTTATCATGATCCACTGGCACCTTGTCGATGGCATCCAGTATAAACTGGATGGAATGCGCCGTCCGTGGCAGCCACTCCA
TGATACGAGAGGTGGTCGAGACGGGCGGTGTCGCTGCATCGCCGTCATCCACGAAATCCGCATCTCCGCCGGACAACGAACGAACTCCACCCAGG
TAATCCGTGTAGTCGTAATCACTGGTCAGCGGATTCACCTTGGAGTAGTAAATGGCAGCGAACGTCGAGTAGATAATCAGCAGTGCTGTGCCCAC
CTATAAGTTTTATATACATATTTAAAACGATTATATTACACATTGCACTCATATACTTTATGTATTTTCACTCACCTGAAAGACGGCCCAGAACT
TGTAGGAGCCCTCCGTGATGACGAAATCGTAGTATCCTTTGAGAGGATCACCCTTGATATAGCGACCCTCGCCCACATCCGTGTCGGCCTTGTCC
TCCGCCTCGGCATCGCGTCTTTGGCGCAGTCCACGCACCGATCTCAGATTTCCCTTTTCCCCCTTTAGTGCCGAGACTTTGGTGGCGGGTGCCGA
TGGTGTGACTGTCTCAACTTTCTCCACTGTCTTCTGCGACTGTTCCTCCTCCTCCGCTTCCTCCTCCTCCTCATCAGAGACATCTGGAGCAGCTG
TCGTCGTCGTCGTCGTGGTTGCCTTAGTTGTCGTTGTAGCCGGCCTCTTGTTCTGGTTCTTTTTGTTTCCCTCGATGCGCGGCGGTTTTTTGGAG
TTTATCCTGTTCTTCTGCTGCTGCTGCTGACGCAGTTGCTCCTTCTCGGCTTTCTTCGCCGCCTGCTCTTGGCGGAACTTCTCAGTGCTCTGCTG
ATGGCGTTCGCTGACCGCGTTCCAGGCACTCATCAGTGCCTGATACAGATCCCAGATCTGCTTGAGGCTCTTCAGCACGGTGACCAGTGTGGATT
CACTTTGGATTTGGACTACTGCATTGTCGGACGTGGGCTGAGATTGTTTGGCCATCGCTGTTTCCGGATGTGGGCGCGGCTGGAAGCCCATGGGA
TAGTCGTACATCTCATCGTAGGCGGGATAAGGCGATCTGTAGAAAAATACATACGTTTCGTTTATGTTGTTGTAATAATTTCATCCAACACCCAT
GACCCAGATCTAGTTGGATTAAGCATTTCTCACCTGCTAGGAGCTAAAGACGCCTGAAGCTTTCTATTATTGCCCTCGGCAGCGGGATGAGTAGC
GACTGGAGCTGGCTGCTGTTTATATGACCACGGAGCGTAGAAGGAATCGTAGGGACGTGCCTGCTGTGACCTGCCCTCACCGGTGTATTCCTTAT
CATAGAAACGCTCATCCTCTTCCGACTCCTGCTTGGACTCTGCACTGGGATATCGTTCAGGTCCGTAGTCATCGGCCACATCGTAGTACGGATCC
TGCTCGTAGGAATCCTCGCGACTCTGCGGCGGACCGTAGGCATCCTGGCGTTGTCCCAACACGGGAGAATCCATGCTCTCTGCATTCACCACCAC
CGCCTGCTGCTCCTCGTAGAAGTTTCTGCCCTGCTGCGATGCGGATGCACTCGGATTGCTTGCATTTCCGGCATCCCTAGCAATTCGCTCCACCG
TGGCAATTTCTGTATCATTATCGGCACCGGACTTGAAATGATTCCACATGCGCGTAAGGATTAGGAGATCGCTTTCTCCGCCCGCGTTGCTCTGT
GCCCGTCCAGCTTCGATCACGGCCAGCGCCGTTAAGGTGGTGGCAAAGAGAAGAAACGTGACCACCAGAAACCATATGGGTGAGAGGCGTCGTGG
CGCCTTCGCCGGCATTTTCTCGTAGGCAGACATTATCCGTTTGTCACTATTGATTCTATTGTTTCGAATCCTGGTTCAGCACACACCGCACGGCC
AGTTGGCTCGGAGTTAAGTCGACAACTAACCGAAGATGTCCCAATGCTGAGCCAGAAAAACTCCGCCCGGCAATGGTGCTAATGGCGGGTTTTTG
GGTATCTAGAACATCCATCCGTAGTGGCTCGTTGAAAGGTGCTAATCCGCGGGCCGCGTGCATCATCGTTATTGGGCCAGTGCTCCAGTTTCGAT
TTAACGGTTCATCCAAGCCACCAAGTGCCGCGGCAATTAGCACCATCCATATCACCAATGTAGCCAGTACTACGATCCCATCCCATCCGATGCTA
ACTTCCATTCTCCATTCAGTTATGCATAATTCCCGATTTTGTTGTTCGCCACAAATTCGTTTTTTTTTTCGCGGTGAAAGTGTGCAATATGATT
CTCTTTCCAGAAGATGGACTATGGAATTTAGGAAATCGTAATTGGAATGGCTTTGTGCCGTTGGAGCACAAAGATCCACGCCTGTGGAGTGGCCG
CCATCGAGGTCCGTCGTCGGTCGTGTGCCAGGCGAAGATCACGATCTAGGAAGCTGCATACATGCCCATATTTAGACACAAATCGTGGCAAGCGT
GCGACTTTCATTAATGGGGTTGAAAAGAAATCTATTTCTACAATTAAGATACGTTAAGTCAACATCAATGGGGTGTTTGTACATTGGTGAGATCG
CCTTAACGATTCGAAATTTGAAGACAACACCATTTTAAAAATGCTAATACACAGTTTTTTTGGGAAATTGGTATACTACACAAAGTAACCAAAA
AGAAAGGATATCGTATTAGAATATTGTATACACATATGAGCTTATCATAGTTTATTATATAGATACATATAGGTAGCCACCTATTAAAACTCATA
TCTTAGAAAAGAAAGCGATGTTAACAATTTTATTCTTTAATGCGAATTGAAATGAAATGAAAATTGCTCATGTTATGAAGTTA
(SEQ ID NO: 748)

Exon: 2883..2219
Exon: 2126..1406
Exon: 1330..1001
Start ATG: 2883 (Reverse strand: CAT)

Transcript No. : CT21031
ATGTCTGCCTACGAGAAAATGCCGGCGAAGGCGCCACGACGCCTCTCACCCATATGGTTTCTGGTGGTCACGTTTCTTCTCTTTGCCACCACCTT
AACGGCGCTGGCCGTGATCGAAGCTGGACGGGCACAGAGCAACGCGGGCGGAGAAAGCGATCTCCTAATCCTTACGCGCATGTGGAATCATTTCA
AGTCCGGTGCCGATAATGATACAGAAATTGCCACGGTGGAGCGAATTGCTAGGGATGCCGGAAATGCAAGCAATCCGAGTGCATCCGCATCGCAG
CAGGGCAGAAACTTCTACGAGGAGCAGCAGGCGGTGGTGGTGAATGCAGAGAGCATGGATTCTCCCGTGTTGGGACAACGCCAGGATGCCTACGG
TCCGCCGCAGAGTCGCGAGGATTCCTACGAGCAGGATCCGTACTACGATGTGGCCGATGACTACGGACCTGAACGATATCCCAGTGCAGAGTCCA
AGCAGGAGTCGGAAGAGGATGAGCGTTTCTATGATAAGGAATACACCGGTGAGGGCAGGTCACAGCAGGCACGTCCCTACGATTCCTTCTACGCT
CCGTGGTCATATAAACAGCAGCCAGCTCCAGTCGCTACTCATCCCGCTGCCGAGGGCAATAATAGAAAGCTTCAGGCGTCTTTAGCTCCTAGCAG
ATCGCCTTATCCCGCCTACGATGAGATGTACGACTATCCCATGGGCTTCCAGCCGCGCCCACATCCGGAAACAGCGATGGCCAAACAATCTCAGC
CCACGTCCGACAATGCAGTAGTCCAAATCCAAAGTGAATCCACACTGGTCACCGTGCTGAAGAGCCTCAAGCAGATCTGGGATCTGTATCAGGCA
CTGATGAGTGCCTGGAACGCGGTCAGCGAACGCCATCAGCAGAGCACTGAGAAGTTCCGCCAAGAGCAGGCGGCGAAGAAAGCCGAGAAGGAGCA
ACTGCGTCAGCAGCAGCAGCAGAAGAACAGGATAAACTCCAAAAAACCGCCGCGCATCGAGGGAAACAAAAAGAACCAGAACAAGAGGCCGGCTA
CAACGACAACTAAGGCAACCACGACGACGACGACGACAGCTGCTCCAGATGTCTCTGATGAGGAGGAGGAGGAAGCGGAGGAGGAGGAACAGTCG
CAGAAGACAGTGGAGAAAGTTGAGACAGTCACACCATCGGCACCCGCCACCAAAGTCTCGGCACTAAAGGGGGAAAAGGGAAATCTGAGATCGGT
GCGTGGACTGCGCCAAAGACGCGATGCCGAGGCGGAGGACAAGGCCGACACGGATGTGGGCGAGGGTCGCTATATCAAGGGTGATCCTCTCAAAG GATACTACGATTTCGTCATCACGGAGGGCTCCTACAAGTTCTGGGCCGTCTTTCAGGTGGGCACAGCACTGCTGATTATCTACTCGACGTTCGCT
GCCATTTACTACTCCAAGGTGAATCCGCTGACCAGTGATTACGACTACACGGATTACCTGGGTGGAGTTCGTTCGTTGTCCGGCGGAGATGCGGA
TTTCGTGGATGACGGCGATGCAGCGACACCGCCCGTCTCGACCACCTCTCGTATCATGGAGTGGCTGCCACGGACGGCGCATTCCATCCAGTTTA
TACTGGATGCCATCGACAAGGTGCCAGTGGATCATGATAAGGACAAGGAGCTCGGCTGGTCCACGGCGCAAAAGGACACGCCGGCGCTGGGAATG
AGATAG
(SEQ ID NO: 749)

Start ATG: 1 (Reverse strand: CAT)

MSAYEKMPAKAPRRLSPIWFLVVTFLLFATTLTALAVIEAGRAQSNAGGESDLLILTRMWNHFKSGADNDTEIATVERIARDAGNASNPSASASQ
QGRNFYEEQQAVVVNAESMDSPVLGQRQDAYGPPQSREDSYEQDPYYDVADDYGPERYPSAESKQESEEDERFYDKEYTGEGRSQQARPYDSFYA
PWSYKQQPAPVATHPAAEGNNRKLQASLAPSRSPYPAYDEMYDYPMGFQPRPHPETAMAKQSQPTSDNAVVQIQSESTLVTVLKSLKQIWDLYQA
LMSAWNAVSERHQQSTEKFRQEQAAKKAEKEQLRQQQQQKNRINSKKPPRIEGNKKNQNKRPATTTTKATTTTTTTAAPDVSDEEEEEAEEEEQS
QKTVEKVETVTPSAPATKVSALKGEKGNLRSVRGLRQRRDAEAEDKADTDVGEGRYIKGDPLKGYYDFVITEGSYKFWAVFQVGTALLIIYSTFA
AIYYSKVNPLTSDYDYTDYLGGVRSLSGGDADFVDDGDAATPPVSTTSRIMEWLPRTAHSIQFILDAIDKVPVDHDKDKELGWSTAQKDTPALGM
R*
(SEQ ID NO: 750)

Celera Sequence No. : 142000013384638
CTTCATCTCGCCCGTCATTTTCCAGATAACCTGGACCCGCTTGCGTGAGTCTCGCAAATCGACGCAGTGCCTTGCCCAAAGCTCGAGCAGCAGTT
CGACCGCGTGGAATGACCACTCGGACGGCTGAAAGGAGTTCCAGCTCAGGCGGCGCTCCAACGAATCCTGCAAGTGAGACATGGTAATTTGGACT
ACTATTGACTTCTAATGGCGTCGTTGTACGTACGTCTAGTTTAGGGGGATGGATTTCCGCGATCCCCTCCTCGCACAGTTCCTCGGTACGCAGGT
AGTCCACATGGCACTTGTGGGTGCGCAGATTGGACGTGTTGAAGGATCGCATGACGCGCTTGCAGCCCGTGCAGAAGTAGAGTCCATTGATTATG
GCACCATCGGTGCGCACGATTTCCCGATACACCTTCCACACGGAGCCGCGCTGCTTGCGTCGTAGTAGCCGGTACTCGCCGCGGAGCACCTTCGC
CGAGATCACCTGGTTGGATTCGAATTTTGATACGTCCTGCATCGTGCGGGCCTCAATCATGTCGTCCTTACGCTCGAAAAGTATAAACAAAATGT
GCCTAGAGATGGGCAGCAGCTCGATATCGATTTTTCTAGAAATGGTCGGTATTGGCTTCATATATCTATCGATAGTTCTATGATATCGATTTAAA
TTATATCTAAAATACAAATAAAAAAACATTTTACGAATTGAGAAACTAAATGTAACAAATACGATTTAAAACAAATTTATAATATTAAAGTAAAG
TAAGTAATTAAAGTTTTGCTAAAAAAAGTAAAATATAATTTCATTGCATTTATTTTTACTTAAGAAACTAATTTGTAAGATCATAACAATGCAAA
ATCTAGCTTTTTACAATATATATATATATATTTAGATTAATTTGAAGTTGAAGCAATATTACATTAAATATTCACTGTTTTAGTTGTATATTTTG
CTGAAAAAGTAACACCACGCTACTTCTACGTATAACACTTAATATTTACACTACTGATTGTTATGCTTAAGCAAATAAACAATATCTTTGTGAAA
TGCGTTTAGCTCCAGCAGTGCATCCTTCATAACCTGCAGCTTTTCTCGCTCGATCGCCAGTTTTTCCTCCTCTATTTCAAGGAGTCTGTCCGAAT
GGTTGTTCGATGCTTTCCGTTTTGTCTGACATTTTGAAATTGGCGATGGGGAGAGATCCTTCATGTGGTCATCATCCTCCTCCTCCTCCTCCTCC
TCCTCGTCTTCTTCCGGGATTTCCGGAATACTGGGAGAGGGAGTTCGCGTTCTTTTCATGGCTTTGCTAGCAACCATATCACTTTCGAATACGTT
CCCATCGTCCCCGGCCATAGGCTCGTCTTTTAATGAAGACAATTCCTCAGGCTCATAATCCTCATCGCTGAACAAAGCTTGAGCTGTAAAATTAG
CGTATTTTTAAGACATAATGACATAACTAGCATTTATTGCACTACGACTTTACCTGGATTTTCGGCGGTAATATCTTCGAAGACATCAACTGATT
TCGTGCCAATCAGAAGTGCTTGAAGCTTATGAAAGTGCTCCCACTTGGATGGCACTCCAGTTTCCCGAACTCTCTCAGCTTCTATTCTGTAAATA
CCAATATAAAAGTTAATATACTATAAAAATAAAAACTTTTGGTATGCAAAATATAAGAGCGCACCTATACTTTCGCGACAAATTGTCCATTTTGG
TTTTAAGCTCCGTGTGGCTGGGCCCAAACTGACTCATCTCCCTAGCCATTTGCCGGTAGATGATCACATTCTTGGACTCTCCACGAAAATCCTTC
AAATGCTGTGCCCACAGTTGCAGCAACATCTTCTCCGCATCCTTTTTCCAAACGTGTCGCTCCGTTTTCGTATAGTAGTCCTCAAACTTTTCCTC
CTTGCCAACATTCTTGGGCAATGGCGAGATGCCATTGGCTCGGATCGCTGGCTCAACGACCATTTTCTGTGCAACGTTTATCTTGGCGGTTCGCT
GTGGTCCCGTCGGTGATCCTTCATCGCTCAACAGGGCTTGGAGTGAGCTCTTCATGCGCGGTCCTGGCTTACGACGTTCTGGTGTTATATTCTAG
AAGAGTTAGTTGGTTTAGAAGCATGGTTACTGAGTGATTAATTAGAATTTTAGTATGTTCGCTAGTGGTCCATGTTGGACTATGTAACTGAAGTG
GACTTTCATACAGAAATTAGGTCAAATTTGATATCCTATCACATGTTTTAACGAATCTCGCTTTGTAGTGCCAAAACACATTATGAAAAGGTAAA
CAGGTCTATTGCCACCCATGTGGGATAGGTAAACAAGATATTTGGTGTGTGGCTGTACTCGGTAAAACCGGGTAAGTACCCCAACAACCCATGTG
GGGCGATGGACTCACTTCCTCCGGCTGCAAATCCTCCGCCAGGAAGACGGTCTCGTAGAACTTCTCGTACTCCGATTTTGGCGGGAATGACAGCT
GCGACTGAGTTTTCTTTTCGGCGGCAGCAAGACTGCGATTGCGACTGTTTAGGGCGATTCGCTTGCTCTTCGGGCCGATCAGTGAATTCCTTGTA
CTTCGGTGAACCTCCTTGGCGCCGGCGGCATCGTCAATATTTCTGGACGGCATTACGTTGCGGTCTTTTGTGTCCAGCGCTAGATAGCGTGAATT
GTTGTGTTTTTATTTTGATAATTGGTGGAAAAATATCTTTTGTAATTCCTGTTCCTGTTGTCCTAGAGATGCAACAAGAGTCGATAGATGTGCAG
TAATATCGATTGTTGCAGTTAGTGAAGTTTTTGAACACTGTTTATTGGTTTGGCTTATCGATAATTTAACATTAATACGCAGCCCTGGTTAAAAT
GGCGGGCAATTTAAAAGTTTTTATTAGTTAAGACTTCAAATGTTCGTAATTTGGATATTGTTAAAGTAAACGTTATCAGTAAATCAAACGCGATT
TAAGTTAAATGTATCAAAGTCCTCTTGTTTGGCTTATAGCTCAATAATAAAACTAAGTGTTCCAACAAAAATATCTCTCTTCAATACATATTTTC
TTGCATCAATTATTTTATTTACTTTACCAATTCAAATGAAGTGCATTTCATTTGCTTTAGCATTTATATTTGTTAGGCACTGCCTCCTAATACAA
TAAAGATCATTTAATTGAAATGAATTGATGTAAGGACAATTACCACAGATGTCATTCTATGTGGATTTCGCACGCACTTTTAGCTAATCAAGATG
GGTCAGCAGGCATTTGCCGCAGCAAATGTATCTGCATCTGCGAACAGCATCTGCATCTGCATCTGTATCTGGAAAAAGCACAAGGCACAACGGAC
GACGGCAATCAGCGACAATTGCCCAAAGATTGCGACTAATGGTTATAGTTGGACCGACGCACGTCGTCGCATCAGACAGAAGGTGCCTGTGGGAG
ACTTGCAACCGGTTTCGAATGATTCTCTTGTCTTCCGACTCTTGCCGTTCTCACATGGAGAAAAAGTGAACAAATCCGGCCAACAATAGGGTTAC
AATATCAGTCTGTCCATATATTAATATGTTACATTCTTTAAAACAATACAATTCATTTGGGAAAAAATTCAGACATTGTTTCACAGATTAATACA
TTGAAAACTGCTCCATTTAATTTGTAATTCTCAGTGTAGTCTCCTGGCTCCTGCATTTCGGCCGGCTGCAAAAGTTTGTGGCTCGTGCTCGGTGA
TTGCCAGCT
(SEQ ID NO: 751)

Exon: 2714..2391
Exon: 2086..1680
Exon: 1606..1479
Exon: 1413..1001
Start ATG: 2618 (Reverse strand: CAT)

Transcript No. : CT21095

GAACAGGAATTACAAAAGATATTTTTCCACCAATTATCAAAATAAAAACACAACAATTCACGCTATCTAGCGCTGGACACAAAAGACCGCAACGT
AATGCCGTCCAGAAATATTGACGATGCCGCCGGCGCCAAGGAGGTTCACCGAAGTACAAGGAATTCACTGATCGGCCCGAAGAGCAAGCGAATCG
CCCTAAACAGTCGCAATCGCAGTCTTGCTGCCGCCGAAAAGAAAACTCAGTCGCAGCTGTCATTCCCGCCAAAATCGGAGTACGAGAAGTTCTAC
GAGACCGTCTTCCTGGCGGAGGATTTGCAGCCGGAGGAAAATATAACACCAGAACGTCGTAAGCCAGGACCGCGCATGAAGAGCTCACTCCAAGC
CCTGTTGAGCGATGAAGGATCACCGACGGGACCACAGCGAACCGCCAAGATAAACGTTGCACAGAAAATGGTCGTTGAGCCAGCGATCCGAGCCA
ATGGCATCTCGCCATTGCCCAAGAATGTTGGCAAGGAGGAAAAGTTTGAGGACTACTATACGAAAACGGAGCGACACGTTTGGAAAAAGGATGCG
GAGAAGATGTTGCTGCAACTGTGGGCACAGCATTTGAAGGATTTTCGTGGAGAGTCCAAGAATGTGATCATCTACCGGCAAATGGCTAGGGAGAT
GAGTCAGTTTGGGCCCAGCCACACGGAGCTTAAAACCAAAATGGACAATTTGTCGCGAAAGTATAGAATAGAAGCTGAGAGAGTTCGGGAAACTG
GAGTGCCATCCAAGTGGGAGCACTTTCATAAGCTTCAAGCACTTCTGATTGGCACGAAATCAGTTGATGTCTTCGAAGATATTACCGCCGAAAAT
CCAGCTCAAGCTTTGTTCAGCGATGAGGATTATGAGCCTGAGGAATTGTCTTCATTAAAAGACGAGCCTATGGCCGGGGACGATGGGAACGTATT
CGAAAGTGATATGGTTGCTAGCAAAGCCATGAAAAGAACGCGAACTCCCTCTCCCAGTATTCCGGAAATCCCGGAAGAAGACGAGGAGGAGGAGG
AGGAGGAGGAGGATGATGACCACATGAAGGATCTCTCCCCATCGCCAATTTCAAAATGTCAGACAAAACGGAAAGCATCGAACAACCATTCGGAC
AGACTCCTTGAAATAGAGGAGGAAAAACTGGCGATCGAGCGAGAAAAGCTGCAGGTTATGAAGGATGCACTGCTGGAGCTAAACGCATTTCACAA
AGATATTGTTTATTTGCTTAAGCATAACAATCAGTAG
(SEQ ID NO: 752)

Start ATG: 97 (Reverse strand: CAT)

MPSRNIDDAAGAKEVHRSTRNSLIGPKSKRIALNSRNRSLAAAEKKTQSQLSFPPKSEYEKFYETVFLAEDLQPEENITPERRKPGPRMKSSLQA
LLSDEGSPTGPQRTAKINVAQKMVVEPAIRANGISPLPKNVGKEEKFEDYYTKTERHVWKKDAEKMLLQLWAQHLKDFRGESKNVIIYRQMAREM
SQFGPSHTELKTKMDNLSRKYRIEAERVRETGVPSKWEHFHKLQALLIGTKSVDVFEDITAENPAQALFSDEDYEPEELSSLKDEPMAGDDGNVF
ESDMVASKAMKRTRTPSPSIPEIPEEDEEEEEEEDDDHMKDLSPSPISKCQTKRKASNNHSDRLLEIEEEKLAIEREKLQVMKDALLELNAFHK
DIVYLLKHNNQ*
(SEQ ID NO: 753)

Celera Sequence No. : 142000013384638
GTGTTGATGCTGTGCCTGGTGTCGCTGCTCTTTGTCATCTGCACGGTTTTGTGAGAAAGGATCATGCTGGAGGTGTACGAGGAACGATACGGAAA
GGTAGTGCCCATGCAGGATGCGGCTGTTCAGCTGCTGAATCGCTACCGGATGCTGGCCAGTGGAAATGTGCACAATTGAAGGTGATTGCTTTTTG
GCACTGAACGGATTGTGGGTGGACAATAGCGGCACTTGCCACAGCAGTAAGTGTGGAATATCCTGTATTCCTGTAGAATTTCGTATTTTCATTTA
ACGTTTGTGATAGTTTTTATATTCTGTTGAAACAAAGTGAGCGGACGACGACCATATCGATAAGCTTAATTATCAACCTACGATGGTACATAATC
AATACAACAAACTGTAATCTTCCATTTAGAACCGTTGACCGATACCGATGTTAAGTGCATTATCATTATTAATCCCATAGTTGAACTTAGGTATG
ATGTAGTGAAATCCATTCCTGGAAATACCGGGAACTTACGAGTAGAAGGGTATAGCCCCCATAGTCACAACGATATACAATTATTACAAGGCATG
AACACATGTGTAGATTAGTTATGGAACAACGATGCGGATACTTAATATTGATAATGGATTGTGGAAGAGGAAGCCCACCCAGTGTTATTCTACCT
TAACAAGTTACATGTGACTTAGACTGTTGTTAGATAATAACAATATTATACATGTTCATCATGACAAACCAAAATATTCCAGTACATCTAGTAGA
TAAACCACAAACGAATAACAAATAACACAAAACCAAAATCGTAGTAATCAAAATTAGCGTTATACTATATTGTTACGATTGACTTGACACCAAGT
AAATCAAAAACATGCAGATATTAATATTTGGAATAGCCTATACTTATACACATATATATATATATTTTAGTATACAAAATTATATTGAATAAACT
TTAAGAGACTGAATATCCAGTAGTTTCCTTAGAGTGTCAAAAACGGTGAGTCCAACACAACCAATTTCATTTATTTGTAGTTCTCTTTTATTGAA
AGATAAAAATTTTAATTTTTTCATTGTCTCTTTTTTGTAATTATATATATTTTTTTATTGCTATATATATCTATATACACATGCTAATGTATATT
TGAAAATTTCAAGTCAAGACGTTCAAAATGCATTTTCCAAAAATACAATTTGTTTTTAATGCTTTGTGTTACTAAAGTAGCCGATTTTGTTTAGC
CACAAAATGATTTTCATGTTCTTTTGTGTGTAAAGTAGAAGACATTTTTAAATTAAACGTAAAGCGAGAAAACATATTAAAAATAATGGAATGTT
CGTTCTTACATACTCGCGCAATAGAAATACATAAAATAGGTGGCTTTTGTTGAGCTACTCGGGCAGCTCCCTTAAATAAGTTTTTAACTCAATTT
TGCAAACAAAAAGTTCATAAAATTAACTAAAAATGGACGGTATTCTGTGATAGAAGAAATTTCAATAATGCCGTCAGACAGAACCAAAGACTAAA
AAAAAAAACATAAGTGCAAAATGTAGCCAACCAATTATAAATCAAATCTTAGCATTTACTTGCGCAAAACAATTGGCAGTGCATGGAAAAGTATT
TTCTGTCTGTTATGCGTGGTGAGCCTTTTCCGTGTCTATTTGATTTTCACTTCGTTCTCATCTATTTTTTTTTATCTTTTGGTGTGTCTGAGTG
GTCGCTGTTGCGTGCCTAAGGCGATTTAAAAACGATTTATGTGCATATTCTTGCGACCGGTTTAGATAAAGATCTCTGTTCGCTTCCTGACTTGA
TGGCCAGTAGTTGAGTGCAGGACAGCATCGTCTGGATCGTCAGCTCCATCGGCACCCTGATCCTCGTGCGTCAGGTAGTCGCCTTTGTGTCGGTG
CAAATAGCGACCGATAAGGAAGAACATAAGGATCAGCAGCAGGAAGAGAATCACAAGCAGACCTGAAAGAAAGTTTTGTATCACTAATATGTTTC
AGTGCCAGAAAATGATTTTACTTACATGCCAACAGCACAGAGTCAACTTCATTGTATGCCTTGCGCAACTTCTCCTCATCCACCAAGGGTGGTGG
CCTAGTCTCGATTTCAATGGGCGGATGCGTAACTGGCTCCACTCCGCAGAAATCTTCAGTCAATTGAGCTATAACAACATACGATTAGGTTTAGA
TTGTACTACTAACTATTCTGTAATTGAAAATACTTACTGCCCAATGATTTGACATTCTTGGGAGGATTCTGCTGGAACATCAGCTTCAGTGGATA
GATATCATCGAATTGAACTCGCGACACACAACCCACAAAGCCATCTGTCATAGATTCATTTTTGCCAATGTACATGTACTGGATATTGTTGAATT
GAGCATCCGCTGAGGCCTTAATATCAAAATTATACTCGACCGGCTCGTAGTTGTCAACCTTCAAAACCACTGTGGATCCACCATTCTTGCGCATA
AAGTGCATATCGTGGTACTGACCCAGGCCAAAATGTTTTTGGGGAATATGATTTCCTGCCTCTCGAAACCGAAATCAAATACACAACGCAAATG
ACCTGAAAGAAAACGATTTGAATATGAAGTGGTTCTCACTAAAAAATGTATGCCAATCAATTTACCAGAATTCGATATTTGAATAGTTAAATATT
CGCCAGTTAGGTTGGAAGAGAAGCCAAGCAGGAATCCCTTCGGAATGGTGGTGGTGAAACCGACGCGAATGTTCTCGGCAATTGTGGAGCGGAAG
GAACCCTCGAACTCGTAGCGAATAATCGAACTGGAGCGTAGGTTGACACCAATCTCTGCAATAAGTAAATAGAAATTGAATAAGATGCAATTACT
GCACTATCCAATTACCCACCATCTGCGCAAATAGGTCCTTTGAATGCGCTCCAACGGCAATCGCAGCTGTAGCCATCGTATCGCTCGATACAAGT
ACCATTGTTTAGGCATGGATTTGATTCACAGCGACCCACGCAACCGGTGCTGATGCCGTATAATCCACGCTTGGAGTATTCCTTCAAGTCAACCA
TCTTTCCGTTCAGCAGCAGTGCACGAATGCATCCTACGTAACCATCGCGGTACTCAGTAGTGGCGCCAATCACCAGATCCGATGTTAAGTGAAGT
GCACGCACTGGACCCGGCGGCTCTCGAACCTCAGCCTTGATAGAACCATCAACCACCAGACGAGCCTCCTTCCTGTTGCGCTCGACACTAACCGT
GTGCCAGTTGTTGTCGTTCAGGTGATAGCTTGTGCCCACATTAACGCCCAGTGGACCACTTCCCGCCTGATACTGGAATTGCAATTTGTTGCCGC
CATTGAGACTTAGCTTAATGTAATCTGTAGGTCCGGTAGCATGGAAGATCACAGAGTTCTCTTGTGTGGTACGGAATTCCAGATAAATATCTCCA
GAGTGACCCATATCGAATGGTGGTAAGTTAATAGAAGCATCGGCAATGCGGAAGGTCACCACATTACTGAACAGATCATCGCCCTCACAGCGCAG
CGGTCCCAGAGTATAGCGACCCATTTTCTCGTCCAACGGAGTTCCAGTGTCGCCAAACTTCACAGCTCGCACGGGAAGGTATTCCTTCTCCCGGA
TATCACCACCATCCTCCATCCATTCCAGACTGTTCGAATCGCAGTTGCACCACTTTGTGGGATCGTGACACTTGCCCAGAATTCCACATTCGCAC
TTACGAGAGCCAGGTAGAGCTCCAGCCCAATAGTCCATCGGTTGATTGTGGCGAGATATCCACCAAGAGAAGGGACGGAAATTTCCGGCCTCAGC
TGGATACAAAATTCTATTATAACTCTGAATCAATTCAAGGAATCGCATTACTACTCACATGGCGAGTTGAAGAGTCGGGAGGAGCGGCAGGAGTA
GCTCAGGCGCTGCCAGCAGCTATGAGACCGATTCAACAGAGCTTCAATTTGCAGTTGGTTGGCATCGTACATGATGGACTGCTCAAAGGAGCCAG
GCTCCTGAAAACCATCTACTGTTGTGGTGTGCTCTTGACTGTGACTGAGGGTGGTAATCACGCGTCCATCCGCTGCAAAAACATCAATCAATGTC ATAAGTTTTATAAAATTACACAATTTAGGGTGTATCTACACATGTTTTAAACCATATAATATGTATGACATATTACAGAGGATATAATAATTTGA
TTGATGGTAATTTTTCCATTTTCAATTTAAGGAGTAAACAAAGAAATGTAGGAGTTCTATACAATTCAAGTGATATCCACTTACAGTAGAACTCG
CAGGTCACTGGGAAAGGTTCTAGGGGACCACTGCCATCCACATCGAGATTCAAGTTCACACGCTGCTGCACATGCTGGACATTCTTGAGAGCCAA
GCAGGACAATGGATTGTTTGCTAAATAAGAAAAAACAAATAATATGTAAAAACAAGATCGAGTTGAAAACATGTGAGAACTCACATGTATGGCAA
ACAGCTCCGGCGTAGCCAGTATGTCCGCAATCACAGAAGAACTCCCTGGAGTTTTGGTGACAAAGTCCCTTATGCTGGCAAGGATTCGGGTTGCA
GCGATCAATCATCTGGCAGGCATCGACGACGACATCATCGCCACAGCAAACCTCCTCGCCCTTCACCCAGTCCTGCGGTAATTTGTAATTTCCAT
CCACCGAAATTAAGCGCATGCAACCGACAAATCCATTTTTGTCCTTTCCACCAGCAATATAGTACTGTGCTCCAGTGGCAACCTGCATGCTCTTT
GTTGTGGTCATCGGTCTCTGATCAATATTTAAAATCAAGCGATTCTTTTCGATGGATATAACGAACGAATGCCATTTGCCATCATTGAACTGATC
ATCGTAGTTGTCCAGAATGATTCGCGCTTTGTCCTTGACTTTAAGATCAATTTTCACTTTGCCAAACTCCAAAAAGACCTTTAGATAACCACCCG
AATAGAAGTCGTGATGCAGCATTACTCCAGTTTCCTCGTAAGTACGGAAATAGAAGGAGACGTTAAGACGCTGCGAATTTTCATAACCCTTCAAA
CGGACGAACGACGAACGGGTAGTGAAGGTCACCGGATAAATCGGAGGCGAAGGACACGCGTAGATCGTGTTTACCCTAGTGAAGAGATATCCCTC
TCCCAGTTCAGTGCTGTCTTTCATCACTCGAATAAAGTTGGTCGAATTAAAGTAGATGTTTTCTAAGCAGCCGGAGAAATTTTGTTGGACAATCA
AGCCCTCTTGTACGTTGGGCACACCACCTAGATACAGCTCCCTATTAAGATTCAGTCGTGTGAACTCGCCTTGGATGCGTCCTCTTACGATGACA
CGATCCACTGAGAAGATTATGTCCCTTTGATTCCTTGAGATCACAACGTCATGCCACACATTATCATCCAGCAGGCTGCCCACCGATAAGGAGGT
CATCACCCGCGATCCCAAATCCAAATTCAGCACCATTTTGTTGTCCTTAAGCTGCAGGGCATAGTAATCCCCTTGTGTGCCACGCGAATACATCA
TCACTCCGTTGGCAAAGGCCGTCTTGAAGCGGAAGCGGATGGACTCTTTGGTGGAGGTAATGGGTTCCCGCCTCAGATCATAGCGCACCAAGCCA
GTGCCATTAAAGTATAGGTTTTCAGAGACTGAAAGAAAAGGTTTGGGATTAGAAACAACACAATATCAATGAATCCATTCAAAATTTACTGTAAT
CGCAGCCGTAGAGCTCCACACGCATGGAAATACGATCGTGCCACCTGGTGGGATTGATCCTCACCCATTGGGCAATAATGGGCACCTCGAAGACG
TTGTAATGGATAGAGTTGCCATCGGAGTTGCCCTTGAACATCTGTGATGGATATCATACATATACATTAATATTAAAACAATTAATAAACAAAAA
AGGGTAGTTCAAAGCCAGATTCTAAAGCATTAATCCATCGCCATCCTTTAAGCCGGGATTAGTTGTGTTTTAAGTGTAGTCTTAGTTCTAGGATT
AGTCACAGTACCTGCGGCTCGCTCGTAGGATTCACGTAGGAGCGCCAGAACTCGCCATCATCCGAATATTGGACAATGTACTCCGTCACGAACTC
ATCCGTATGCATGCGTCCCATGGTGGCGATCTTGCGCACCATGCGCGGATCTCCCAGGTCGAGTGTTAGAAAGTGGTTATAGGTATTCTCGACCG
GTGTCCAAGCAGCGTTACCTGCACAAGGTGCATTTACCAATCTAGTTAGTCGCAGTGTCAGAGTGTGGAGAAGGGTGTGGTTTTTTTGTAACAG
AAGTAATCTACAGAACCATTAGCCAAATGAGTAACAAACGCATGCGGGACGAATTAAATCATAAAATAAAAACCAAGCACAAAAGCAAGCAAAAG
TGTTAATGAATTTATGTAAGGATAATCCGCTTTCGCAGATTCAGGGTTCACCCAACCACCATTGGTTTTCACAGAGAAAAAAATTAATATGTATC
CTCATCGAAATGAAATATGAACGGGAATGCTTAATGGAAACATACTAGTTTCTTTTCTGTGCAATAAACCACCACCAAAAGCGATCCATTTTCTC
TAGGATTAGCGATACACATTTCCAATTGTATGTGGTGATCAATTGTTTACCTTGACATTGCCGCCCGGCTCTTTATAGTCGGCAAACTCTAGATC
GGTTATGCCATAGCTAATGGTGTACTCGGTGACGTACTCATTGCTATGTGGTCGTCCTTGCAGGGCGATGTGCGTCACGTTCCGCACCACGCCCA
GGTCAATAATCAGACGCTGGTCGAAATCCGAGTTCTTCGCGGACCACGAGGTGCCAGCTGGGGTTCGCAAATGGTCATGGGATGATGGGCAATAA
AATAAAAATGATACAATTTAAACCAAAACAAAGGCAACATAAAATAAACCTAAAGTGGGGGGGGGGGGGGGCAAACAAACAGCAAATGGGAGTTC
TACGCTCTATAATTGCCTAAAACTAAGGGGTTTAAAATTACGCTAAATCTGCAGCAGGGGGTGTTTTCAATTAATAAACCATAATTTAGGGGCGA
TCGCGATTGACAGCTGCAAGTGGTCGAAGTCCTTCAGCACAAGGATCAACCCCTGCCCAAAAAGTGAAAAAGGATTTGGGTAGCCCGAGGGTTGA
GTTGATGGTGTCAACACAAAATGGGAGAGTTCGCAAATGGTTAGGCATAAACAATTGCAGTCGTGTGCTTTTGTTTTAATTGCTCAGCGCGCCAA
ATTGCAAGCCGGTGTGACAAAATAGTGTGAGAAAGTCCAAACTGCACAGATTTCTGAGCGCACAATCCATTCCCCAATATTTTTATAAGCCGCAT
TCAAGTTGTCTTTGTCCGACGTTGGCAACGTGGCATATCAGCCAGCCATCGTGTTCCCATCGATAAAACTTTCGGCAATTCCAAAAATAATTCAA
ATAAACGAGCCATTCAGTGCTACCCTTGCGGATGGTTATCCTGTTGGCGCATAAATTCAACCAAAACCAATGTCTGGCCCCTGTCTGAGTTCCTT
CCCGTTTACGGGTTCCTAAATTTTGGTTTATGGCCTTTTAAGCATATTTCCGGCTTCGTTTCGTAGCGTTTGTTTATCCAGTGCCAGGCAAACAA
ACGATTTTTTGTTGGGGTGTGAGCGCTGCGCAACATGACAACACAAGGATTACAAACTATTCCAAATTTGGCACACAACCATTGAGAAAATATAA
ATGCATGTTTATTCTAGGGATAACGCTATTTTTAGGAGCTACGTTTGCTTGGCTTAGATTCCTTATAGTTCCTATACATCATGATCGCTTGTAGG
GCTTAAGAAGAGCCTTTTGGCAGTAGCTGATCACTTCCTCAAGTTCCGAATCTTCACTCTTCACGAGAAGTTCCTCAACTTGCAGAAACTTGAAC
TTTCCACGCTCCTGTGGCAAGCAATTCCGGAATGCAATGGCCGCACAGTAGTCCTCCTGCAGTAAATGCTCCTCGAAATGCCAATTGTCCATGGG
TTGGTCGTGGCAACGCAGACTAGTACCGATCAGAGGGGAAACATCTGTCTCCAAACTGCGAGTAGTGTCCACTGAGAAGCTGATCTTTTGCAGAT
CTACAGTGATGCCAACACCCAGCTCCTTGACGTACGCCTCCTTGAGACACCAGTGACGCATAAAGGCCTTCACCTGCTCCCGTTCATCATGATGC
GGTCTTCCAATATAACTCCATTCCTCCGCCGAAAATTTGCTCTTCATCAGGCCAAAGAATTCCGACAGAGGCTTGCCACCATTGTACTCGATCTT
CATGACATCTGTGCCGATTCCAAAGTCGGGATCACTGCTCTCTCCTGCAATGCCCGCTAGAAGTACCAGGCTTCCCTGATGGGAGACATTGAAGC
TGAGAGGTGGCCCATCGTAGTCCTCCCCTTTCACCCAGTAAGGTTTACCCCTCACATCCCGGGCGAACTTCACTTCGGCCGACGGCAATCCGCTG
CACGTGCTCACATATTTTCGCATGAAAAGACGACCAATTAGCGAGGACAGAAAGTCATCGATAAAGTGGAACTTCATAAGCCGAGCTCGTTCCTC
CGGTTGAATTGAGGCCACCGCCTGGCTCAGTTGAGGTAGTGTGGGCCTCCAGCTGCCCAGGTCAAAGGCCCAGCGGGTGCAGATGTGTTTGCTCA
TTTCAATGCGTTTTGTAACTATCTAATTGCTTTTATAATCATTGTTTTCAGGGCGTTTTCGCTTTGCAATGTTGTTTTTAATTCGCTATTGTGAT
GCAGTATGGCCAGAACTGGAGAGGGTAAAAATCCCCCAGCGATTACGCCTTATAAATATACTGCAAATATACTGCTCCACCAAATGCGGGGTGTA
CCCATTTTCATTTTAAAAAATTAAGAAATAATGACTATCTTTAATTTAAAAAAAAAAAATGGGATAGCTATATGTAGCATTTAAAAAAAGCAATCT
AATAACCTGTATATATATAAAAATGTGTACTTAAAAAGGTTCTATTAAAATAAAAACATATTATCCTATGAATTTTTGGCGCAGCATTTCGAAAT
AATAATTGCTAATAAAACAACTGAAAGGCAACTAAACTTTCGAACGAATAACTTTCAACAAAAAATCAATATTACTCACCGTTTAGTCGTGCTTT
GTCGGGTCCTCTTTCCGTCAAGGATGATGTGGCCGTGAGGACGGCTCTTTCCATCAGCGGCTGGTTGCAATCGTAGTCGGAGAAATAGTCCGTGA
AGGCGTCTGAAAGAGTGCAATATCGATTTATAAATATCCGGAATTCCATGACCCATATATGTACGAGTGTACATTGTTGGGCGAAAAAATGAAAC
GCAAACTGTCACGGACGCAATTAAAATTGAGATATGAAGAATCTGTTTGGATGGCGGCCAATAAGCTGAAGTACTCCAGCCGGGACATAATCATT
GGCCTCCTTTTTATGGGCCCATAAAGAAAGCCACATCTATAAGGCAGCAAGAAGTAAACAAATTGACTGAGGAGTAAATATTTGCTATTTATTTT
AAGAGTTCTTAGTTCTCTGTTTTCCGGGTAATTTAAGTCGTACAAGATATATTGAATTTGCTTGTAATGAATAAATATCATATAAATAGAATCTA
TACAATTGAATCTTTAAATTTCACATGAAGTCCAAGGAAAATTCCTATGAATTAAGACAATCAGCATTAAATTGGACATAAACTGATGTAATTAG
TTGCTTTATTTAGAATATTTTACTCTTAAACATGTATTAAGAGTACTAGGTACTAGTTAGAAATATTTCTTATTAAGATGGTTCCACTGTTTTAA
GAGGCAGATTCTTGTCTCATATTTGCACCATAATATTTTCCGTTGACGAGAGTCTTTTAGCCCCTAGGATCCGTGACAAAAGCATGCGGATGTGG
GGGCCAGGTCGTGTCGGAAATCCAGACAGTTGCCCCTGTCTGCCGCAACCCCCAAGAAATTGTTTACAATGGGTGCAGCAGTAGCTCCTCCTAGG
CAAACAGCACACTGGCATTTTCTTAGCGGAGTGGGGAAAACAACCCTTGCGAGGTCATTCGGAGTTCGTGGGCACTTTAAGCTGACTTTGAGTC
TTGGGTGGAGTGGTACAAATCAACCTGATAAGCTCGAAAGGAAACCGAGGAAACACGCATGACAATCTTCTGGTAAATAACACAGGAACATATGT
ACATACATATATAGCCAGTTTGAACTACTTTTTGCTACATAATTGCCCAATGGTGATTAGAAAGAAAACGAAATACATAGAATTTGGCTAATGTT
CTAAATGAAACAAATATGACGAGGTCTGAAAGGCCATTTCCGTCCATCTGGGGGAAACTCGAAGTGCGAATGATGCTATTTTCGAGGCAATAAGA
ACCGAAATAAATTATGGAAATCGACCAAAGTCTGGGAGGATATATGTCGGCTGTCTGCTTTCGACGCTTCAAGGCAAATTAATTGCGCGGCATTG
TTTATTTTTAGTCATAAAAATGTTTGCATATCATCGATAGATTGTTTATTTTTCAAGATATGTGGAAATTTGTGGGGAAAAGCGCTTAAGTCTGT
TGACATATGGAAGGATAATGATAAAATCACCTGTTTCACACAGCATCATCAATCAGCAGATGCTTCTTATTTGCCGCATGCGCATTTGAAAAGCC
GGAAAAGAAGGCAAGCACAACTGGGGATGCAACCGGCAAAATTTTCGAATTGCTCCCCCGGGAAGCTTCATAAAAGTCCGGAAATCAAGAATCTA
AAACCCCAATGCCTTTGCTCAAAACGAACGAGTAAAAACGGGCGTTGTTAAGCGGCATTTTTGTTTTGCCACCGCTATTCGTAAGCAACCGTTTG

FIGURE SHEET 409

ATCGCTCTCCCGTTCTCACCAAAACTCTCGCGATCGCTAAGAGCGAGTTAAAAAGCGAACAACGGGCCAAAGGAAAATGGAAGAGCGAGTCTTCA
GCTTTGGGGAACACGCCCAAAAAGTTGGCTTACAAACAATCGACGTTTTATGTCACATATTGCTGGGAAAATCGAGCCGAAAGGATCTGAATTCC
TGGGTTAGTCAATGGGTATCACTGGTTTTTACCTGCTTGCACCGATTTAATGCCATTATTGACCAGCAATAGGAGGCATAACAATCCAAACTGAA
GCGAGGAAAATGCTGCTTTCGTATTGCTCCTGGCGGCCTCATCTTGGAGGCTGTTAATTAAACACTATCGCTTGGTAGATTTATAAACACATCT
ATATTCGATTTCCGAAGAAGTTTAACACCAAAATGCACTTTTCCGCTGGAAAAACCACCGTGAAAAGCTGATGATTTGTGGCAACGCGTCCGCGG
TGTTAAAAACGTTGGACTGCACTTTACGCTCCGCTTTAAATCGATTTTGAATTTATGTAATTTATCCACTGGGTGTACGGCTCCAGCAGATCACG
CCCACTTCGGAAGAGTTTCGTTTGAATTAAGAAAATAATTATCGCAACGCGGATGACACACGAACAGAATGTCTCGCTGCCAGTGTGACCGTGAC
TCAAACGTGGCAAGATACCGAGGGAGTCACCAACTGGGTGCTTGTCGCGTGAGCTAAGCTATCGTGTGATTAAGTATATGAAGTATTTACAAATT
ATTTCAACTGCTACTATGAAATTAAATTTGGTCACTAATAATAGCTTTCCGTTAACATTTATATTAATTCGTGATAGAAATTTTTTTGCATAGTT
TTAAAGCCATGTAATATCATTGCAAAATGAATGATATAAGCAAAGTATACAAATGTAATGGCAAATAAGTCAAATCCCCTCTAAAATATTTTTA
AAAATCTAGTTTTCTTATCTATCCAGAAATTTGAAATAAAATACATATTTTACAAAAAATTATTTCGAATACCAAATCGATAGGGGCGTAAAACA
TCGATAGTCGTAGTAGTATCATTATCGATAGTTGGTCACACTGTTTATCCCTCTTTTCGCCAAAAATTTGTTGGCGTGTTGTCAATTTCCTAAGC
ATTTGATCGGTTTTTTCGTTTTGTGTGTAACCCGGAGAGGATAAAACAGCGACAATGTACGGTGGAGACGAATACGCAACCAACTCGGTGAGTGC
AGCCAGCGAGGAATGATTCATTCTCGGGAAACCAATCCCCGGACTCCGCCGACAACATAACCCATCTTTTGTTGCCCTCGCACAAATACAAAACT
CACTGGGATGATTTTAAAGCCGTTTTACGACTTGGCATAGTTGGTGTTTAGATCATCATAGGTCATTAAGCACTGATAATCCGTGGGCCACTCCT
TTGACACGTTCCTTTGCTATTTGGAAACGAATCCTCTGTAGTCCGGGGGACACCCCGGCGCCATGTGGTATATTATTGGTATCGGTGTACATTATTA
ATAAGTCATAATACCTTCTACATTTTTGATTTGCGTGCAATTTTAGATGGTGTGTACACACCTTTAAAGAACACATGAATATATTCTA
(SEQ ID NO: 754)

Exon: 11438..11053
Exon: 9221..9105
Exon: 6193..5997
Exon: 5836..5695
Exon: 5633..4455
Exon: 4390..4265
Exon: 4062..3859
Exon: 3799..2870
Exon: 2810..2631
Exon: 2567..2223
Exon: 2158..2021
Exon: 1962..1001
Start ATG: 11158 (Reverse strand: CAT)

Transcript No. : CT21123
TTATTTTCTTAATTCAAACGAAACTCTTCCGAAGTGGGCGTGATCTGCTGGAGCCGTACACCCAGTGGATAAATTACATAAATTCAAAATCGATT
TAAAGCGGAGCGTAAAGTGCAGTCCAACGTTTTTAACACCGCGGACGCGTTGCCACAAATCATCAGCTTTTCACGGTGGTTTTTCCAGCGGAAAA
GTGCATTTTGGTGTTAAACTTCTTCGGAAATCGAATATAGATGTGTTTATAAATCTACCAAGCGATAGTGTTTAATTAACAGCCTCCAAGATGAG
GCCGCCCAGGAGCAATACGAAAGCAGCATTTTCCTCGCTTCAGTTTGGATTGTTATGCCTCCTATTGCTGGTCAATAATGGCATTAAATCGGTGC
AAGCAGACGCCTTCACGGACTATTTCTCCGACTACGATTGCAACCAGCCGCTGATGGAAAGAGCCGTCCTCACGGCCACATCATCCTTGACGGAA
AGAGGACCCGACAAAGCACGACTAAACGGTAACGCTGCTTGGACACCGGTCGAGAATACCTATAACCACTTTCTAACACTCGACCTGGGAGATCC
GCGCATGGTGCGCAAGATCGCCACCATGGGACGCATGCATACGGATGAGTTCGTGACGGAGTACATTGTCCAATATTCGGATGATGGCGAGTTCT
GGCGCTCCTACGTGAATCCTACGAGCGAGCCGCAGATGTTCAAGGGCAACTCCGATGGCAACTCTATCCATTACAACGTCTTCGAGGTGCCCATT
ATTGCCCAATGGGTGAGGATCAATCCCACCAGGTGGCACGATCGTATTTCCATGCGTGTGGAGCTCTACGGCTGCGATTACATCTCTGAAAACCT
ATACTTTAATGGCACTGGCTTGGTGCGCTATGATCTGAGGCGGGAACCCATTACCTCCACCAAAGATCCATCCGCTTCCGCTTCAAGACGGCCT
TTGCCAACGGAGTGATGATGTATTCGCGTGGCACACAAGGGGATTACTATGCCCTGCAGCTTAAGGACAACAAAATGGTGCTGAATTTGGATTTG
GGATCGCGGGTGATGACCTCCTTATCGGTGGGCAGCCTGCTGGATGATAATGTGTGGCATGACGTTGTGATCTCAAGGAATCAAAGGGACATAAT
CTTCTCAGTGGATCGTGTCATCGTAAGAGGACGCATCCAAGGCGAGTTCACACGACTGAATCTTAATAGGGAGCTGTATCTAGGTGGTGTGCCCA
ACGTACAAGAGGGCTTGATTGTCCAACAAAATTTCTCCGGCTGCTTAGAAAACATCTACTTTAATTCGACCAACTTTAATTCGAGTGATGAAAGAC
AGCACTGAACTGGGAGAGGGATATCTCTTCACTAGGGTAAACACGATCTACGCGTGTCCTTCGCCTCCGATTTATCCGGTGACCTTCACTACCCG
TTCGTCGTTCGTCCGTTTGAAGGGTTATGAAAATTCGCAGCGTCTTAACGTCTCCTTCTATTTCCGTACTTACGAGGAAACTGGAGTAATGCTGC
ATCACGACTTCTATTCGGGTGGTTATCTAAAGGTCTTTTTGGAGTTTGGCAAAGTGAAAATTGATCTTAAAGTCAAGGACAAAGCGCGAATCATT
CTGGACAACTACGATGATCAGTTCAATGATGGCAAATGGCATTCGTTCGTTATATCCATCGAAAAGAATCGCTTGATTTTAAATATTGATCAGAG
ACCGATGACCACAACAAAGAGCATGCAGGTTGCCACTGGAGCACAGTACTATATTGCTGGTGGAAAGGACAAAAATGGATTTGTCGGTTGCATGC
GCTTAATTTCGGTGGATGGAAATTACAAATTACCGCAGGACTGGGTGAAGGGCGAGGAGGTTTGCTGTGGCGATGATGTCGTCGTCGATGCCTGC
CAGATGATTGATCGCTGCAACCCGAATCCTTGCCAGCATAAGGGACTTTGTCACCAAAACTCCAGGGAGTTCTTCTGTGATTGCGGACATACTGG
CTACGCCGGAGCTGTTTGCCATACATCAAACAATCCATTGTCCTGCTTGGCTCTCAAGAATGTCCAGCATGTGCAGCAGCGTGTGAACTTGAATC
TCGATGTGGATGGCAGTGGTCCCCTAGAACCTTTCCCAGTGACCTGCGAGTTCTACTCGGATGGACGCGTGATTACCACCCTCAGTCACAGTCAA
GAGCACACCACAACAGTAGATGGTTTTCAGGAGCCTGGCTCCTTTGAGCAGTCCATCATGTACGATGCCAACCAACTGCAAATTGAAGCTCTGTT
GAATCGGTCTCATAGCTGCTGGCAGCGCCTGAGCTACTCCTGCCGCTCCTCCCGACTCTTCAACTCGCCATCTGAGGCCGGAAATTTCCGTCCCT
TCTCTTGGTGGATATCTCGCCACAATCAACCGATGGACTATTGGGCTGGAGCTCTACCTGGCTCTCGTAAGTGCGAATGTGGAATTCTGGGCAAG
TGTCACGATCCCACAAAGTGGTGCAACTGCGATTCGAACAGTCTGGAATGGATGGAGGATGGTGGTGATATCCGGGAGAAGGAATACCTTCCCGT
GCGAGCTGTGAAGTTTGGCGACACTGGAACTCCGTTGGACGAGAAAATGGGTCGCTATACTCTGGGACCGCTGCGCTGTGAGGGCGATGATCTGT
TCAGTAATGTGGTGACCTTCCGCATTGCCGATGCTTCTATTAACTTACCACCATTCGATATGGGTCACTCTGGAGATATTTATCTGGAATTCCGT
ACCACACAAGAGAACTCTGTGATCTTCCATGCTACCGGACCTACAGATTACATTAAGCTAAGTCTCAATGGCGGCAACAAATTGCAATTCCAGTA
TCAGGCGGGAAGTGGTCCACTGGGCGTTAATGTGGGCACAGCTATCACCTGAACGACAACAACTGGCACACGGTTAGTGTCGAGCGCAACAGGA
AGGAGGCTCGTCTGGTGGTTGATGGTTCTATCAAGGCTGAGGTTCGAGAGCCGCCGGGTCCAGTGCGTGCACTTCACTTAACATCGGATCTGGTG
ATTGGCGCCACTACTGAGTACCGCGATGGTTACGTAGGATGCATTCGTGCACTGCTGCTGAACGGAAAGATGGTTGACTTGAAGGAATACTCCAA
GCGTGGATTATACGGCATCAGCACCGGTTGCGTGGGTCGCTGTGAATCAAATCCATGCCTAAACAATGGTACTTGTATCGAGCGATACGATGGCT
ACAGCTGCGATTGCCGTTGGAGCGCATTCAAAGGACCTATTTGCGCAGATGAGATTGGTGTCAACCTACGCTCCAGTTCGATTATCGCTACGAG
TTCGAGGGTTCCTTCCGCTCCACAATTGCCGAGAACATTCGCGTCGGTTTCACCACCACCATTCCGAAGGGATTCCTGCTTGGCTTCTCTTCCAA
CCTAACTGGCGAATATTTAACTATTCAAATATCGAATTCTGGTCATTTGCGTTGTGTATTTGATTTCGGTTTCGAGAGGCAGGAAATCATATTCC CCAAAAAACATTTTGGCCTGGGTCAGTACCACGATATGCACTTTATGCGCAAGAATGGTGGATCCACAGTGGTTTTGAAGGTTGACAACTACGAG
CCGGTCGAGTATAATTTTGATATTAAGGCCTCAGCGGATGCTCAATTCAACAATATCCAGTACATGTACATTGGCAAAAATGAATCTATGACAGA
TGGCTTTGTGGGTTGTGTGTCGCGAGTTCAATTCGATGATATCTATCCACTGAAGCTGATGTTCCAGCAGAATCCTCCCAAGAATGTCAAATCAT
TGGGCACTCAATTGACTGAAGATTTCTGCGGAGTGGAGCCAGTTACGCATCCGCCCATTGAAATCGAGACTAGGCCACCACCCTTGGTGGATGAG
GAGAAGTTGCGCAAGGCATACAATGAAGTTGACTCTGTGCTGTTGGCATGTCTGCTTGTGATTCTCTTCCTGCTGCTGATCCTTATGTTCTTCCT
TATCGGTCGCTATTTGCACCGACACAAAGGCGACTACCTGACGCACGAGGATCAGGGTGCCGATGGAGCTGACGATCCAGACGATGCTGTCCTGC
ACTCAACTACTGGCCATCAAGTCAGGAAGCGAACAGAGATCTTTATCTAAACCGGTCGCAAGAATATGCACATAAATCGTTTTAAATCGCCTTA
GGCACGCAACAGCGACCACTCAGACACACCAAAAGATAAAAAAAAAATAGATGAGAACGAAGTGAAAATCAAATAGACACGGAAAAGGCTCACCA
CGCATAACAGACAGAAAATACTTTTCCATGCACTGCCAATTGTTTTGCGCAAGTAAATGCTAAGATTTGATTTATAATTGGTTGGCTACATTTTG
CACTTATGTTTTTTTTTTAGTCTTTGGTTCTGTCTGACGGCATTATTGAAATTTCTTCTATCACAGAATACCGTCCATTTTTAGTTAATTTTAT
GAACTTTTTGTTTGCAAAATTGAGTTAAAAACTTATTTAAGGGAGCTGCCCGAGTAGCTCAACAAAAGCCACCTATTTTATGTATTTCTATTGCG
CGAGTATGTAAGAACGAACATTCCATTATTTTTAATATGTTTTCTCGCTTTACGTTTAATTTAAAAATGTCTTCTACTTTACACACAAAAGAACA
TGAAAATCATTTTGTGGCTAAACAAAATCGGCTACTTTAGTAACACAAAGCATTAAAAACAAATTGTATTTTTGGAAAATGCATTTTGAACGTCT
TGACTTGAAATTTTCAAATATACATTAGCATGTGTATATAGATATATATAGCAATAAAAAAATATATATAATTACAAAAAAGAGACAATGAAAAA
ATTAAAATTTTTATCTTTCAATAAAAGAGAACTACAAATAAATGAAATTGGTTGTGTTGGA
(SEQ ID NO: 755)

Start ATG: 281 (Reverse strand: CAT)

MRPPRSNTKAAFSSLQFGLLCLLLLVNNGIKSVQADAFTDYFSDYDCNQPLMERAVLTATSSLTERGPDKARLNGNAAWTPVENTYNHFLTLDLG
DPRMVRKIATMGRMHTDEFVTEYIVQYSDDGEFWRSYVNPTSEPQMFKGNSDGNSIHYNVFEVPIIAQWVRINPTRWHDRISMRVELYGCDYISE
NLYFNGTGLVRYDLRREPITSTKESIRFRFKTAFANGVMMYSRGTQGDYYALQLKDNKMVLNLDLGSRVMTSLSVGSLLDDNVWHDVVISRNQRD
IIFSVDRVIVRGRIQGEFTRLNLNRELYLGGVPNVQEGLIVQQNFSGCLENIYFNSTNFIRVMKDSTELGEGYLFTRVNTIYACPSPPIYPVTFT
TRSSFVRLKGYENSQRLNVSFYFRTYEETGVMLHHDFYSGGYLKVFLEFGKVKIDLKVKDKARIILDNYDDQFNDGKWHSFVISIEKNRLILNID
QRPMTTTKSMQVATGAQYYIAGGKDKNGFVGCMRLISVDGNYKLPQDWVKGEEVCCGDDVVVDACQMIDRCNPNPCQHKGLCHQNSREFFCDCGH
TGYAGAVCHTSNNPLSCLALKNVQHVQQRVNLNLDVDGSGPLEPFPVTCEFYSDGRVITTLSHSQEHTTTVDGFQEPGSFEQSIMYDANQLQIEA
LLNRSHSCWQRLSYSCRSSRLFNSPSEAGNFRPFSWWISRHNQPMDYWAGALPGSRKCECGILGKCHDPTKWCNCDSNSLEWMEDGGDIREKEYL
PVRAVKFGDTGTPLDEKMGRYTLGPLRCEGDDLFSNVVTFRIADASINLPPFDMGHSGDIYLEFRTTQENSVIFHATGPTDYIKLSLNGGNKLQF
QYQAGSGPLGVNVGTSYHLNDNNWHTVSVERNRKEARLVVDGSIKAEVREPPGPVRALHLTSDLVIGATTEYRDGYVGCIRALLLNGKMVDLKEY
SKRGLYGISTGCVGRCESNPCLNNGTCIERYDGYSCDCRWSAFKGPICADEIGVNLRSSSIIRYEFEGSFRSTIAENIRVGFTTTIPKGFLLGFS
SNLTGEYLTIQISNSGHLRCVFDFGFERQEIIFPKKHFGLGQYHDMHFMRKNGGSTVVLKVDNYEPVEYNFDIKASADAQFNNIQYMYIGKNESM
TDGFVGCVSRVQFDDIYPLKLMFQQNPPKNVKSLGTQLTEDFCGVEPVTHPPIEIETRPPPLVDEEKLRKAYNEVDSVLLACLLVILFLLLILMF
FLIGRYLHRHKGDYLTHEDQGADGADDPDDAVLHSTTGHQVRKRTEIFI*
(SEQ ID NO: 756)

Name: Neurexin IV
Classification: cell_adhesion
Gene Symbol: Nrx
FlyBase ID: FBgn0013997

Celera Sequence No. : 142000013384650
TGGCTGTTATAAAAAGTTAATAGCCGTTCAAGTCCCCCTTCCAAACCACTTGGAAACTGGTCCTGCTCCTGCGCAGTGAAAGTATATAGGAAACG
GAGCACATAGGCGAAGCTACCATCCAACCGCACACCAGAACTGTGTAACCCATTCCCCGATCCCGTAGAGAATTTATTGCATGGGCCGCGACTGC
CGTTGGCTTCTGTCCATCTATCTTTGGCTGTGCTTTTCCTGGGATTTTCCCCAATGCGATGGAATGGGTACTCAGACCACAGAGGACCTGCCCAC
AATGCCACCATTGGCAGTTACATTTTATGGCCAAAGTTCACCAGAACCCAACTCGTTCCCCAGCCCCACGCATTCTGGCGACCAAGTGGCGCCAT
TTTTGCCGCATTGTCATCGATGGGAGGATGAAGATGGGGATGGGCAACTGACAGGGATTCTAGTTTATGCTTGCGAGGACTTTTCAAGAAATAAA
CTTTTTCCTCTGTCGACATCAGCGAAAATAATATCGCATTCGGAAAAGTATAAAAATAAAATGAGGACGCAGATTAAAACTATCAAGTTGAACAG
TTGGAGATAGATTTTTCTATAAATTGATTTTTATTTTCACTTTAAACATTTCTATCGAGACTGGAATGGACAACATATATAAAAACACACTTCAC
TTCAATTGTTTTATAATTTATCAGTATGTATATTAAGATTATTCAGTAGAAAACTTCCTTACATCGCACCAGTGACGATGCGAACCGAACAAAAA
CTTAGTGAGACAGTTCATCATAATTATTAAATTAATTCACTTTCTGGCGTAATAACAAAAATGCTGGCTAACTAGCTTTGTTGACCATTTGGCGC
ATGAAAATGGGAAAAAAGATTTATGTTGCCAATTCAGTTTCAAGAGCCGAGCCTGATGGATTCATCTCAACTCTAAAGTATACAAGATATTACAA
AAATTTGCTACGTTTACGGAATTTTCGTACTTATATAGATTTTGCCATTTTTATTTTTATTTTTTTTAGATAGATTTTCTTGTGCTTCTTATAA
ATGCCTGCACACATGATATGCAGAGTTGAGAATGGAGTGAAACTTTCGACTTGACTTGCTAAAACAAATATGAAACATCTTCTGTTGGCTATTAC
TAAGGGAAGTTTGTCTTGTGGCTTCTTCGACGGTTTCTTCGTTTTGTATTGCGTGGCATTGTCATGAGGCATACATCATTGATCAAATTTCTTGT
TCTTGCTTTGATTAAGTAACGACTTGAGTTTGTATTCGTGACCTGACTTCTTAAACAGACTTCTATTTAAAAAACAAACAGTTACACATAATGGT
AGAGCATGCTACGCTGAAGTCTTAAATCTTTCATTTTAACTAAATTTAGTTGCTGCCTAGTCAGGTGTGCGAATCTGTTTCCTCGTGATTTCTGT
GGGTGTATGCTTGTGTGTTTGTTATTCGTTACGATCCCAATAAGTCGCGAATTCGCCTAATAGAACTTTTTCGCCTGTGCTTCGCTGCGGTTTCT
GCAAGGAATAATAAGTTAGATTGTTTAGTTTCGAATCCACGCTTAAAGATTCCATGAACTCACTTGAAGACGTTGTAGATGAAGACTAGCAGCAG
TTGCACAACAGTTACGCTTAGGAACAATGTGACTCCAACGCAATTGCCCGTGGGACAATTGGCCACCTGCGCTGCTCCCTGTGGCGCTGCCAATC
TGCAAGGTAAGGGAATGCATATTGAGTATCAAGGAGGTACTTAAAAGATGACAATAAAGTATAATAGTCTAAAACTCATAAACATGTTCCTCTGA
ATCAAACTTGTTAAAACTCTAATTTCATAATGTGGAATACGAAAAATTAGTATAAATATGGCTGAAAAGGTTAAAATTAATTCGAGCTCAGAATA
ACTTCGATGACAACAGCTTTAGGAAACTTAAAATAGACTTTGAGCGTATTCCTCACCTTTGGCCCACGTGGGTGATGCCCTGCTTGACCTGATTC
ATGCCATCGCGCATCTCGGCGATGAGCGTTTGTACATCATAGCCGGTGGATTGGATTTGTGCTGTGGGCGCATGCTTCTGATTCGTTTGAATGTT
ATCAGTGCGCACATTGATATCGCCAACCAGTTGACGAATCTCGCGGATGGAACTGAGCAGCATGTTCTGATTAGTGAGCAGAAGATCTACATCGC
TCCTGCTGACTGCGCCAACGGGCAGCTGTTGCTGTGGCACTCCGCCGGCGGCGGGCGGAGGCAGAGCCTGTCCAGCATTACGTGAGACCAGCGAC
AGCGTGGTCTCCTGGCGGCCAATAATCTCATCCACTTTGCGGGAAAGTTCGCGTAGGTGATCGGCAATTTGGCTCTGACCCTGCCAGATCTGACG
CAGCTCACGCTGGTTCTCCGACTCGTAGAACTCCTCCCAGTCCTCCTCGTCTTTGTGCTGTGGGATTATACGAAAGTTGATTATCAAAACTAGCG
ATAAGACATCTTTATCAGCTGGCTGCGTGGCAATTACCTCGTCGGGATGGTCCTTCTTGTACTCCTGCTTCTGTTTCTCCAGTTTATCTTGGTAT
TCCTTGTACTCTTGCGTAAGCTTCTCCTGGTTTTCCACCTTGGGCTGCTCCTGAACTTGTCCAGCGGCATGCAACGACGTGGTCAGGAAATGGAA
CACATCGTGGTCATCGGCCAGACCGCCCGTGGCGGCGGAAATGCCAAAGTAGCCGTTCTTGGGCAGATTGACGCCATCCGCTCTCAGACACAGCT CGTAGTCATCGTTGTTGTTGGACATTCCGTTGTGGATCATGACGGTAAGCACGTTGTTGTAGTACTCGATTCGCGCCCGTGTAGGGAAGGGCTTG
TTACGGAAATCCCTGAGGCAACCGCTCAGGAGCTGAGTGGTTCCATCTTCGGCATGGTCATACAGCTTGGTGCCATCATTGAGCACGGCACTGAT
GTAAGGATTGTTGTGCTTGTTGTCATTATCGAAGGAATCGAACATGATGGCCAGACCATTCCAGCGGTCCGAGGATCCGAACACAGGCCCATTGT
AGTCACCCTTTTCCGTGGTGTACCAGAAGGCCAATCCATCGGCTCCGATCCTGCCACGTCCCGTCACCCGGAACACGATCTCCACGTCCCACCAG
TCGAAGTTCGTCTGTGACTTTGTCCAGATGGCACCCTTCTGTGAGCGCAGCGATGGCGCCACGCGCACACTTTCCGAACTGGCGATGGCATCTGA
AATGAGGAGCAACAAGTTGTGGCTATAGAAACACCCGAAACCGTGGTCAAAACGACATCCAAACAAAGTGCCTGCGTGTACACTTGGCCGCCTCG
CGCCATCTCGCTCGCACCCATGGCCGCAGACCAGCAGCGAGTGGGCCAAAACAACTGACGTGGAGCTGCGTCTTCCACTCGTACTCACTTCCCCC
GTACTCCCAAAACGGCACGGTGCCGTCTTTCTGTGCCAAATACGGCGGCTTGAACGAGTACTTGTACTCGAAGCGACGGTGCACGCCCACGGCTC
CAGGACTCAGATTGCCGGTCGCCTCGGAGCTGGGATTCCACGCCAGGAAGCACAAAATGGCCAGGAATGTGGGCCGCATCTTTGCAATTATATGT
TGACAACTAGTGGTGGGTGGGCGACGATGGTGCAAACTGATGATATCGATAACCAGCCGGCACCGATAGGCGGTGGTATCGCACTGGATGTTCTA
AAAGCATTGTATAATTTAAAATCAAATATTATTTTATGTATTGTCTACCATTAACAATTAAGGTAATATAATATAAATTGATTAGAACATTTATT
TAGGCCATCCTTCGTATATAAATGTTGAACTTAAATAAAACCAGCCATCCTATAACAATTAACTTCAGCTTAGATCACAATTTAAAATTCTATAA
GATAAAAGTTTTTCCATGCATTCTAAGAAACAAGAACCAAGTGATCTAAAAAATATTCAGGCAGCGACAATACAATCGCTATCGATTTCGGTAGA
TTTTATATCGATATCGCAAATGCCCACCAAATTCAAAAGATCTTGTTATCACTTTATGATGTTGAGGTGGAAAAACATTTATTTTGAAAATTTAA
AGTGTTTACGTCCCGTTAGAAAATAAACATAAATATAGCAAAATACGCGCCATTCGCATGTGCTTACATAGATACATGTTTATCAATACGTTATT
GTAAAATTATTTCGTTAGTTGTTTCAATTGCCTTTTGCGTGATATCACCAAAGTAGTATTACATCCATATCTCCAAAATTCCTTTAGCACAGTTA
GCACAGTGTGTGTATATATGTTTACATCTTTATTCTTTGTTTCTGATTTCCTACCGTTTGTAGTTTTCGTAGAGCTTACAGCTAGAATTATTATA
GGTTTTAATGCCTCGGTAGCACATAGTGTGGGCTTCATAAAATATTGTTAGTTGCTCAGTTTACACAAGTGATAGCTTTGTGTGCAGATCGGTGT
GTGGGGGATAGTCATTAGGGGCGATCGTGCCGCAAGTTTCGCCATTTTACAAATGTTAGTTACTTATTTTGAATCACAATCACTTTCGTGTTAGT
TCTGTGCGCGATCAAAAGAAAAACTCAAATCGATTAAAACAAAATCAAAGTCT
(SEQ ID NO: 757)

Exon: 3613..3414
Exon: 3226..2508
Exon: 2432..1957
Exon: 1709..1584
Exon: 1518..1001
Start ATG: 3594 (Reverse strand: CAT)

Transcript No. : CT21141
TCAACATATAATTGCAAAGATGCGGCCCACATTCCTGGCCATTTTGTGCTTCCTGGCGTGGAATCCCAGCTCCGAGGCGACCGGCAATCTGAGTC
CTGGAGCCGTGGGCGTGCACCGTCGCTTCGAGTACAAGTACTCGTTCAAGCCGCCGTATTTGGCACAGAAAGACGGCACCGTGCCGTTTTGGGAG
TACGGGGGAAATGCCATCGCCAGTTCGGAAAGTGTGCGCGTGGCGCCATCGCTGCGCTCACAGAAGGGTGCCATCTGGACAAAGTCACAGACGAA
CTTCGACTGGTGGGACGTGGAGATCGTGTTCCGGGTGACGGGACGTGGCAGGATCGGAGCCGATGGATTGGCCTTCTGGTACACCACGGAAAAGG
GTGACTACAATGGGCCTGTGTTCGGATCCTCGGACCGCTGGAATGGTCTGGCCATCATGTTCGATTCCTTCGATAATGACAACAAGCACAACAAT
CCTTACATCAGTGCCGTGCTCAATGATGGCACCAAGCTGTATGACCATGCCGAAGATGGAACCACTCAGCTCCTGAGCGGTTGCCTCAGGGATTT
CCGTAACAAGCCCTTCCCTACACGGGCGCGAATCGAGTACTACAACAACGTGCTTACCGTCATGATCCACAACGGAATGTCCAACAACAACGATG
ACTACGAGCTGTGTCTGAGAGCGGATGGCGTCAATCTGCCCAAGAACGGCTACTTTGGCATTTCCGCCGCCACGGGCGGTCTGGCCGATGACCAC
GATGTGTTCCATTTCCTGACCACGTCGTTGCATGCCGCTGGACAAGTTCAGGAGCAGCCCAAGGTGGAAAACCAGGAGAAGCTTACGCAAGAGTA
CAAGGAATACCAAGATAAACTGGAGAAACAGAAGCAGGAGTACAAGAAGGACCATCCCGACGAGCACAAAGACGAGGAGGACTGGGAGGAGTTCT
ACGAGTCGGAGAACCAGCGTGAGCTGCGTCAGATCTGGCAGGGTCAGAGCCAAATTGCCGATCACCTACGCGAACTTTCCCGCAAAGTGGATGAG
ATTATTGGCCGCCAGGAGACCACGCTGTCGCTGGTCTCACGTAATGCTGGACAGGCTCTGCCTCCGCCCGCCGCCGGCGGAGTGCCACAGCAACA
GCTGCCCGTTGGCGCAGTCAGCAGGAGCGATGTAGATCTTCTGCTCACTAATCAGAACATGCTGCTCAGTTCCATCCGCGAGATTCGTCAACTGG
TTGGCGATATCAATGTGCGCACTGATAACATTCAAACGAATCAGAAGCATGCGCCCACAGCACAAATCCAATCCACCGGCTATGATGTACAAACG
CTCATCGCCGAGATGCGCGATGGCATGAATCAGGTCAAGCAGGGCATCACCCACGTGGGCCAAAGATTGGCAGCGCCACAGGGAGCAGCGCAGGT
GGCCAATTGTCCCACGGGCAATTGCGTTGGAGTCACATTGTTCCTAAGCGTAACTGTTGTGCAACTGCTGCTAGTCTTCATCTACAACGTCTTCA
AAAACCGCAGCGAAGCACAGGCGAAAAAGTTCTATTAGGCGAATTCGCGACTTATTGGGATCGTAACGAATAACAAACACACAAGCATACACCCA
CAGAAATCACGAGGAAACAGATTCGCACACCTGACTAGGCAGCAACTAAATTTAGTTAAAATGAAAGATTTAAGACTTCAGCGTAGCATGCTCTA
CCATTATGTGTAACTGTTTGTTTTTAAATAGAAGTCTGTTTAAGAAGTCAGGTCACGAATACAAACTCAAGTCGTTACTTAATCAAAGCAAGAA
CAAGAAATTTGATCAATGATGTATGCCTCATGACAATGCCACGCAATACAAAACGAAGAAACCGTCGAAGAAGCCACAAGACAAACTTCCCTTAG
TAATAGCCAACAGAAGATGTTTCATATTTGTTTTAGCAAGTCAAGTCGAAAGTTTCACTCCATTCTCAACTCTGCATATCATGTGTGCAGGCATT
TATAAGAAGCACAAGAAAATCTATCTAAAAAAAAAATAAAAATAA
(SEQ ID NO: 758)

Start ATG: 20 (Reverse strand: CAT)

MRPTFLAILCFLAWNPSSEATGNLSPGAVGVHRRFEYKYSFKPPYLAQKDGTVPFWEYGGNAIASSESVRVAPSLRSQKGAIWTKSQTNFDWWDV
EIVFRVTGRGRIGADGLAFWYTTEKGDYNGPVFGSSDRWNGLAIMFDSFDNDNKHNNPYISAVLNDGTKLYDHAEDGTTQLLSGCLRDFRNKPFP
TRARIEYYNNVLTVMIHNGMSNNNDDYELCLRADGVNLPKNGYFGISAATGGLADDHDVFHFLTTSLHAAGQVQEQPKVENQEKLTQEYKEYQDK
LEKQKQEYKKDHPDEHKDEEDWEEFYESENQRELRQIWQGQSQIADHLRELSRKVDEIIGRQETTLSLVSRNAGQALPPPAAGGVPQQQLPVGAV
SRSDVDLLLTNQNMLLSSIREIRQLVGDINVRTDNIQTNQKHAPTAQIQSTGYDVQTLIAEMRDGMNQVKQGITHVGQRLAAPQGAAQVANCPTG
NCVGVTLFLSVTVVQLLLVFIYNVFKNRSEAQAKKFY*
(SEQ ID NO: 759)

Name: mannose-specific lectin
Classification: chaperone

Celera Sequence No. : 142000013384670
GAGACCACGGATCCTGGAGATAACTCGCAAACGAAGGAAAGAACAAACACGCATCTTGAGGAGACGCAAAACCAAGGAAATACTACACTCTGGGA
TTCTGCACACAGAAAAGATTGACTCGGCTATTGATCCTGACTAATAATATATATATTAACAATATATACACTTTATTAAGTCGGAATCGTTTAAT TCTACATACAAATTTCATAGGATGTGTCACTTCATGTGAGAATATTAACAAGATTATCTTGGCAATAAGCGCTTCGTCACTTCGTGGATCGCTAG
ATGACGTTTATTTGGGAACTCGTCATCTTCATCACAACCTTTTCATCTGTAAAACGTGACTCTACTAATTATTATATATTTTTATTATTATAATA
CAATAATAATACAAAAACATATTTACAGAAAATAACTTTGAAACCTATGATTTGTTTCATAACTTAAAATTTATAATTATAATTCAGCAACAAAA
ATCTTAGATACTGAGATATTACGGGGTATTATGAATAGGTTGGTTTTGATAAAAACGGTAAAGGTATAAAACAAGACATACACCCACAAAAAATA
AATTATATTATTCATGCAAGGATGTACCAAGGAGTTTTTCGGACAATTCGGGGATGATTGCAAAACAAAGGTAAATTATTGAACGCCGTGTTGAA
CAAATCATGCTCAGGTATACCCAGGCTCATTTACCCTGCAAATTATGGCACTGAATGTGGCATGTTTACCTTTCAAATTGAGCGCACAATACAAA
CCAAATGCGTTTGACACTGAAGTCAGAATATGCCTTTCTCGCAAATCCAGGGACCTTCTTCGTCTCGAAGGATATCAGATTGAGAAAATTAGCTG
TTGGAGTGGGGAAAATAATGAGGGATCATAGACACACATTGAGGAAGGCACAGTTACTATTTCATTATATTTTGAAGACTCAGTTTTAATCTAAA
TAGCAATCTATAGGTTTGTTCAATTGTTTGTTCGGTGTTTTCTTTTATTTCGTTTGTTGTTGTATATGGGCTTTAATTTGAATATTTATTTACAA
TTTATTTAAGACTCGTTACACCCTTGCTCAAGTCAAATATAGTAACAGTTGCAATAAACAAGCTTTCAACTTATTGCTTACGTGTCTCATCAATA
TAATTTACAAGAAAAACTTACTTAAGGCTAATCTCCGTTGATGTTTTGCTTTATGTCTCTGTGCTTCACGCATAATTTACTTTACGGATATTTAC
CGGCTGCTTATTTTGATGCTTCTTTTATTTTGTAGGTATGTGTATTTTTACTAGTGAGAATATTGGTTGGTTAATTGAGAGTATATATAATTACT
ATATATATCTGACTTCTATATACCATTTTTAACATTTGTAATTTATGTACGTTCGTTTTTACGAATTGAGTTTTTACTATGCGCTTGCGGTTGGT
TTTCTTTGTATAAATAAAATAGAATATTTTCGCTTTTGCTTCGCTTCGAATAATACATGCCATATACATACATATAAGAAAATGCTCGATTACGA
TTCTCATAACTTATGGTTCGACGTTAACCAAATGAGGCCCTCGGACAGGCCATCGCCGGATGTGGCACATGATGGTTGTACATACCAATTGCGAT
CTCTTATTCTAGTTAAACCTAGTTTTTCCTGGATTTCATGGGGTTTCATTGCTGCAAGAGAGAACAATAAGCGGATGGAAACAATTGGCTGAGCA
CTATACTAACCATCAGGCAGATCCTGCTTGTTAGCAAATATCAGTATGATGGCGTCGCGCATCTCCCTATCGTTAATTATCCTATGCAGCTCCGT
GCGCGCCTCGTCTATCCGATCCCGATCCGCACAATCCACGACGAAGATCAGACCCTGTGTACCCGTGTAATAGTGTCGCCATAGCGGTCGAATCT
TATCCTGCCCACCGACGTCCCACACATTGAACTTGACATTCTTATAGGTGACGGTTTCCACATTAAAGCCCACAGTGGGTATCGTTGTAACAGAT
TGGCCAAGTTTCAGTTTGTACAGAATCGCTGTGGGTGGACAAAAACAATATTACTTTAGACACGCAAAGGATGTATAAACAAAATAGCTCGAATT
CGATTAGTGATAGTACTGGTGTACGTATTGAAAGGTCTTTATATTGTACATTTTTTCAAAGTACAATAAGAATAAAAACAAAACAATAATTGCCT
CGCCTCAAGAGTATTTTTTAAATGGGATTGGTTTCCACTTAGGAAACTGATGAAACTAATGGGTACTAATCAGGCCCACAATCGAATTCGAGAAC
CCTTTATTGTTTATGTGCTTACTTGTTTTTCCAGCCGCGTCCAGTCCGAGCATGAGAATTCGCATTTCCTTGTTGCCGAAAATTTTTGATAGTAA
CTTTCCCATGGTGCTGATGTGTCATCCATTAAACCTTAGCCAATCTGAAAAACAGTTCGAGTAGAGTTGGCGAGGTCTTCCAAATAAGCATATCG
ATAAGAATAGCTGGGCGAGATTCAGGGCAGGGTCAGTGAATTTCCAGATAATAGGGCCATTGTAATACAGTTTGCAGTTAACATATCAATTTATG
ATATAAGAACGCCGTCGCGCGAAGGCGCGTAAGTGATATATGAACATACAAATGTAGCTACATATGTACACATACGGCGGGCACAGGCAATTTGG
TGGCCATATAGAGCTTGTACGACGGCGGAAGCTAAGACCATTATTTTGCATAATAATTTCACTTACATTGTCATCAGCTCGTTGCTAAAAAGCGA
GAAAAAAGTGGAGAGGCAGAATTTATCAGTGAAGAGCTTGCAGCACACAGTCGCACACACAAACACACGCACACATGCTTACACATAGGAAGTAC
AATTGGACAGATAAACACACTATAGTGTCTCGCAAATTGAGGCAGAGTTATCTCAATTGCGGGCTTATCGCTGGCTCCACTGAATGGGCGGGTGG
ATCCGACCGCTCCACCCCCGCCCCCTGAACAGCCACCGCACCCCTCGACGACCCAGTAAAGCCGGCTTGGGAGCAACGATATCGGATGGTTTTCG
GATTCTACGGAATTTCGCTCGCTCTCTCGCTGCTGCTTGCCTACGTCACAAACACGCCCGTAACACACATACACATGTATACACACCCAAGTCTC
CGACGACCGCCGTTACGCACCGCTTTCCAGCCCAATTCGTTCCACGCCAGCCTGAAATCCGTTAACATGTAGTGCCAAAGTGCGCGGGCCGGGGC
ATAAAATGCATTTGCTAGCACACGGCGGCCAAAAAACTATAACTAACAACAACAATTTTGCACTAATCTTCTTGTATTTATATACACATACACGA
AGCAATGTGCCCGTTAGCGCAGAGCGGAACAAGATCTTCGGGAATTCCAGAAAATACGCTAAAAAATGCAAAGAATGCGGAGGATAAATACCAAA
AATACTGAATTTATCAGATGAAAAACGGTGACTGGCGGGGATATCGTGATTTTTTGGCCAATAAGTTATTACTTTTGCAATTCAAAATTGAAAAA
GATTTATTTTCTTATATTCATTTATTATTCATATTAATTTAGCAAACAATGTAGCTGATATATTCTCCTCGTACGTTCAACAATTTGTTAATTTT
TTTTAATTTTAAAAATTTTTGTTTTGTGTATTTAGTGATTTGGTATTTTAATGTAGCCCTGGTGAACTTACAAAGCCCTAGGGCGGCCACACTGA
AACCGATGATTGAAATCAAGTCGATTGATTTCAGTTTCCTTCTTTTGTATTGTTTTATATTTGAGCAATACTTACGATACTGACATCGCTCAGAG
GTACAATGGAACTTAGTTAGTCGTCGACCAGAACAGACTCGGAAAACATGGCTGGCATTTGCCCCCGGGAGGCGGTTCGGGTGAAAGTGAAGGCA
AGTGAAAGGTGGCCAGAAGGCGAGACAACAAAAGGGCTGCTTAGTTTGTGTTCCTCAATCTAATTTTTTTGAAATCGCCCACAGAAATGCGAACC
CACTGCTCGGCCGGAGTGGCGAAAGTTTTCAGTGGACCCGCAGATCACCACGCTGGAGGTGTTGTACTCCCTGCTGGCCAAGGCCTTCGATGTCA
AGTCGGACTTCTCCATTAAGTACAAGGCCTTTGATCCGGCGGGCAACGAGATCTACCTGGCCGTGCGCTCCGACTGGGATCTGGATGCCGCCTTT
CTGAGGATTCACAACATTTCCATTCAGACGGCCTCAGAACCCTGCCTCACCCTGCAGATCGATGTGAAGCCATTTACGGTGGTCAGGGAGTGTGA
GACCGAGGCCTCCCCGGGTAGATCCATAACGGGAGCGCCTGCTCCCGCAACTCCTGCACCT
(SEQ ID NO: 760)

Exon: 3336..3127
Exon: 2419..2303
Exon: 2023..1721
Exon: 1666..1001
Start ATG: 2384 (Reverse strand: CAT)

Transcript No. : CT21197
GGCACATTGCTTCGTGTATGTGTATATAAATACAAGAAGATTAGTGCAAAATTGTTGTTGTTAGTTATAGTTTTTTGGCCGCCGTGTGCTAGCAA
ATGCATTTTATGCCCCGGCCCGCGCACTTTGGCACTACATGTTAACGGATTTCAGGCTGGCGTGGAACGAATTGGGCTGGAAAGCGGTGCGTAAC
GGCGGTCGTCGGAGACTTGGATTGGCTAAGGTTTAATGGATGACACATCAGCACCATGGGAAAGTTACTATCAAAAATTTTCGGCAACAAGGAAA
TGCGAATTCTCATGCTCGGACTGGACGCGGCTGGAAAAACAACGATTCTGTACAAACTGAAACTTGGCCAATCTGTTACAACGATACCCACTGTG
GGCTTTAATGTGGAAACCGTCACCTATAAGAATGTCAAGTTCAATGTGTGGGACGTCGGTGGGCAGGATAAGATTCGACCGCTATGGCGACACTA
TTACACGGGTACACAGGGTCTGATCTTCGTCGTGGATTGTGCGGATCGGGATCGGATAGACGAGGCGCGCACGGAGCTGCATAGGATAATTAACG
ATAGGGAGATGCGCGACGCCATCATACTGATATTTGCTAACAAGCAGGATCTGCCTGATGCAATGAAACCCCATGAAATCCAGGAAAAACTAGGT
TTAACTAGAATAAGAGATCGCAATTGGTATGTACAACCATCATGTGCCACATCCGGCGATGGCCTGTCCGAGGGCCTCATTTGGTTAACGTCGAA
CCATAAGTTATGAGAATCGTAATCGAGCATTTTCTTATATGTATGTATATGGCATGTATTATTCGAAGCGAAGCAAAAGCGAAAATATTCTATTT
TATTTATACAAAGAAAACCAACCGCAAGCGCATAGTAAAAACTCAATTCGTAAAAACGAACGTACATAAATTACAAATGTTAAAAATGGTATATA
GAAGTCAGATATATATAGTAATTATATATACTCTCAATTAACCAACCAATATTCTCACTAGTAAAAATACACATACCTACAAAATAAAAGAAGCA
TCAAAATAAGCAGCCGGTAAATATCCGTAAAGTAAATTATGCGTGAAGCACAGAGACATAAAGCAAAACATCAACGGAGATTAGCCTTAAGTAAG
TTTTTCTTGTAAATTATATTGATGAGACACGTAAGCAATAAGTTGAAAGCTTGTTTATTGCAACTGTTACTATATTTGACTTGAGCAAGGGTGTA
ACGAGTCTTAAATAAATTGTAAATAAATATTCAAATTAAAGCCCATATACAACAACAAACG
(SEQ ID NO: 761)

Start ATG: 246 (Reverse strand: CAT)

MGKLLSKIFGNKEMRILMLGLDAAGKTTILYKLKLGQSVTTIPTVGFNVETVTYKNVKFNVWDVGGQDKIRPLWRHYYTGTQGLIFVVDCADRDR
IDEARTELHRIINDREMRDAIILIFANKQDLPDAMKPHEIQEKLGLTRIRDRNWYVQPSCATSGDGLSEGLIWLTSNHKL*
(SEQ ID NO: 762)

Name: ADP ribosylation factor 51F
Classification: ligand_binding_or_carrier
Gene Symbol: Arf51F
FlyBase ID: FBgn0013750

Celera Sequence No. : 142000013384809
GGACCATACAAAAGAAGTGCAAGAAAGGTGCGCGCGGTAACTTCTATATGTATCATAATCCTACACAGCGCCTCCCCAAAAGGGGAACGTAGTAG
AATCGGGCATTCCCATAAAAGAGCAAGGCGGTGTCATTGCCGGCTTAATGGGTCCAAAGGTCACAAAATGCAAAAATCACTCTTGTTGACCCATA
TACAAGAATGCTTCCTTCTGGGGAGGATTGTGCTCTCTTCGACCCACTTCGAGGTTCTCCCCGCCACAGCTTCGTTTCGTTTCCTAGGAAATACT
GCAGTTCCTGTTCCTAACAATGCAGCGAGTGCATCCTTCATAATAGCAAATACTTTCCAAAATTAATTTGAAATTTTGCGTACTTCCTTCGGTAG
GCTGCCGCTATGAAAAGGGTGAATGGTCTCAATGCGTCGGAGGACAAATAACCAGAGAGGATAAGTTGGAACCAGAGGCAACTGGCGGTAGTGAT
CAAAACTGCAATCCTGTGCGTACCGTCAGCAAGAAGTGTAAAGCAAATGGCAATTCCAGTGGAGGAAAACAACACGGCCAGAGTCGTCGAACAAA
AGAGCAAAAGCAAAAGGATAAGGGTAAAAGTGGTGAATTTGACCCCTTTGTGAAAAGTTTGATCCAAATTCTCTGTTTACAGGAGCCAGTCACAT
TTCGTCTTGATAATGAAAATTATTTATTTTATACGTATACGGAAGCAACATTTTTAATATTAAATAAGCGATTTTTAAATGCTAGCCCGTACGGA
CTACTTGAACAACAATAAAGAATTGGCCTTCTTAGGGCTAAATGAAAGCACTCTTTTAGAAATTCTTGAAACAAGGCTTTCACAAACCCCAATAC
CGCGAAAACCTGCACAAAATGAGACCTGTTATTGAGTAATCAAAGAGCATTGATAGAACTGTTAGTTGGCTCTGAGTTTTTATTTAATATTAGAC
GCGACAGTAAAATAACCGTCTGCGACAAAATTTAATTAACATTACACAAAAGAAAACGTTACCTCTAACTCGGCTTGGTAATATAAAGATGTTAA
ATTTAATAGTGTTTCTTTACTTAACTGCAAGCCCCCTTTAAATTGATCGATCTTTCGAGGCAAATCTTCAAGTTACCAATGTCTTTAATAGCCAT
TGAAAGGGTGTTATGTGGCTGGCCCAAGATTTGCCGCAAACTTATTGTAACGTCGCGGTCGCTGACCTCCGGCTTGCGGCGGGCACTGGTCAAGC
AGCCCCGTAAAGGCGGAGATGTTGGAAAACCCGGAATGGAGCTTGGGCGCTGTTCGTGCTTTGGACTCCGTGTGAACCTCAGCAATGCATCCGTC
GTATACGTTGGCCACCGACGCTACTCGACGTACGAGAAGACGTCTACGCAAATTTTAACGAAGCTCTTTCCACAAACCTCTGAGGAGTCCAACGA
CGAGGAAAGTCGTGAGCGGCGGAAACTTGAGGAGGAGGAGGAGCAGAAGGAATTGGAGCGGGCATTTAGGCGGATGAAACTGGGCTTTGGGCTTT
TCGGCATAGGTAGCATGTTGTTCTCGTTTTGGGCTATATATTTCTATGGAAGGCCGTCCTTGGATGAGCACGGAAATGAAGTAATCGACGAATTT
AGTTGTCTGCCACAGATGCAGCAGCTTATGTGGCGGACATGGAAGTCGGTGAACCGCTTTCAACGGTTTTTCAAAGAGCCGTCGAGAAAAAAGCT
GCTTCCTGATCCCCTTCAGCCCCCCTACGTGCAGCCGCCGTATACTTTGGTACTTGAGATTAAGGATGTGCTGGTACATCCCGATTGGACCTACG
AAACAGGATGGCGCTTCAAGAAGCGCCCTGGCGTTGACGTGTTTTTGAAAGAATGTGCCAAGTATTTTGAGATTGTTGTTTACACGGCGGAGCAA
GGAGTTACTGTGTTCCCGCTGGTCGACGCGCTTGATCCGAACGGCTGTATTATGTATCGCCTGGTTCGCGACTCTACGCACTTTGATGGAGGGCA
CCACGTGAAGAACCTTGACAACCTCAACCGAGACCTAAAGCGAGTGGTTGTCGTGGACTGGGATAGAAATTCCACCAAGTTTCACCCTTCGAATT
CATTCTCGATCCCGCGGTGGTCTGGAAACGACAATGACACTACCCTCTTTGAACTCACGTCGTTTCTTAGTGTTCTAGGAACGAGTGAGATCGAC
GATGTCCGAGAAGTGCTGCAATACTACAATCAGTTTAGTGACTCGTTATCCCAGTTCAGAGAAAACCAGCGAAAGCTGGGTGAGCTAATGCACGC
CGAGGAGGTAGAAAAAACTAGCAAGTCTAGGCCCGTTGTCAAGAACTGGACCCGTGGCTTCATAAATCATTAAAAAGATTGTGCGTTTGATGTGT
CCCTTAAATACTGTTAATTCACCCAAAAAATTACATTAAAACTTTCCTAGCATTCTTCAATGTCTACCTACTAACAGCAGTTACTTTTGCAGTTT
TTTGCGTATTCTGATTGAAAAAGTCTGAAAACATATGATTTCTGATTTGGCATTTAAAGCAGACTGCCCTGCGGAACGTCAATGCTTCCTTGAAG
GTAACAGTGCAGCCACTAGGCGGATACATAGCCGTAATGTTGTGAAAAATGTTGTGTTACGGTTTTATATGAATGCAGGCTTCCAGAAATCCTCA
GTCCAGCACGAGCACGCAAGCTCAGCAACATGTTGCTGCCATGTGATGGTGTGCGTGAGCACGTGCCAAAATAACTACGACACATGTGTACTCTT
GAGGGAATGTTTCCACAATCAACAACTACGCACTTCACACCACTAGGTGAGTCATGCGCAGTATCGTCCCTGCGAACATTCATCCGAATGTTGGC
ATAAGTAAGTAAAGGGATCAGGTGTACTGTAAGCCTTCCGTCTAGTTACTTTCGATGCAGATTTTGATTCTGGCTGAGGGTTCGTGGCTGGCTGG
GCCTCTTCTCCTTATGTTGAAAACACACAACAATTCGGTGGTGGAAGTATACTGCGGACGTCAAACTGGCGAGCCAGGGCGCAGGCGTTGGTTCA
TTTGGCACTTTGTCTGGTACTCTCCCACATCGGCATCCTGCAATCTCTTTGGCTCAGCATCCTTGTAAGCTGTTGTCGGAGCAATCTGGGCATGG
GGCAACTGAAAGGAAAGCAACTTTCCCATTCAGGAGCGCACAAGCCGCAGGAATCGCGAGCGCAGACAATTCAGTTCGGCTTTAACGTAATGGAC
GGAAGGTTTGAATATCGCTTCTCGCCCCAGTTGTACAGATAAAGTCCCACTGCACGCAATAGGGCACTTGGAAGATACAATAGAACGCCGAGCAG
TGTGTGTATATAGGTTTGAATGCTTACG
(SEQ ID NO: 763)

Exon: 1001..2353
Start ATG: 1124

Transcript No. : CT21286
AGAAAACGTTACCTCTAACTCGGCTTGGTAATATAAAGATGTTAAATTTAATAGTGTTTCTTTACTTAACTGCAAGCCCCCTTTAAATTGATCGA
TCTTTCGAGGCAAATCTTCAAGTTACCAATGTCTTTAATAGCCATTGAAAGGGTGTTATGTGGCTGGCCCAAGATTTGCCGCAAACTTATTGTAA
CGTCGCGGTCGCTGACCTCCGGCTTGCGGCGGGCACTGGTCAAGCAGCCCCGTAAAGGCGGAGATGTTGGAAAACCCGGAATGGAGCTTGGGCGC
TGTTCGTGCTTTGGACTCCGTGTGAACCTCAGCAATGCATCCGTCGTATACGTTGGCCACCGACGCTACTCGACGTACGAGAAGACGTCTACGCA
AATTTTAACGAAGCTCTTTCCACAAACCTCTGAGGAGTCCAACGACGAGGAAAGTCGTGAGCGGCGGAAACTTGAGGAGGAGGAGGAGCAGAAGG
AATTGGAGCGGGCATTTAGGCGGATGAAACTGGGCTTTGGGCTTTTCGGCATAGGTAGCATGTTGTTCTCGTTTTGGGCTATATATTTCTATGGA
AGGCCGTCCTTGGATGAGCACGGAAATGAAGTAATCGACGAATTTAGTTGTCTGCCACAGATGCAGCAGCTTATGTGGCGGACATGGAAGTCGGT
GAACCGCTTTCAACGGTTTTTCAAAGAGCCGTCGAGAAAAAAGCTGCTTCCTGATCCCCTTCAGCCCCCCTACGTGCAGCCGCCGTATACTTTGG
TACTTGAGATTAAGGATGTGCTGGTACATCCCGATTGGACCTACGAAACAGGATGGCGCTTCAAGAAGCGCCCTGGCGTTGACGTGTTTTTGAAA
GAATGTGCCAAGTATTTTGAGATTGTTGTTTACACGGCGGAGCAAGGAGTTACTGTGTTCCCGCTGGTCGACGCGCTTGATCCGAACGGCTGTAT
TATGTATCGCCTGGTTCGCGACTCTACGCACTTTGATGGAGGGCACCACGTGAAGAACCTTGACAACCTCAACCGAGACCTAAAGCGAGTGGTTG
TCGTGGACTGGGATAGAAATTCCACCAAGTTTCACCCTTCGAATTCATTCTCGATCCCGCGGTGGTCTGGAAACGACAATGACACTACCCTCTTT
GAACTCACGTCGTTTCTTAGTGTTCTAGGAACGAGTGAGATCGACGATGTCCGAGAAGTGCTGCAATACTACAATCAGTTTAGTGACTCGTTATC
CCAGTTCAGAGAAAACCAGCGAAAGCTGGGTGAGCTAATGCACGCCGAGGAGGTAGAAAAAACTAGCAAGTCTAGGCCCGTTGTCAAGAACTGGA
CCCGTGGCTTCATAAATCATTAA
(SEQ ID NO: 764)

Start ATG: 124

FIGURE SHEET 414

MSLIAIERVLCGWPKICRKLIVTSRSLTSGLRRALVKQPRKGGDVGKPGMELGRCSCFGLRVNLSNASVVYVGHRRYSTYEKTSTQILTKLFPQT
SEESNDEESRERRKLEEEEEQKELERAFRRMKLGFGLFGIGSMLFSFWAIYFYGRPSLDEHGNEVIDEFSCLPQMQQLMWRTWKSVNRFQRFFKE
PSRKKLLPDPLQPPYVQPPYTLVLEIKDVLVHPDWTYETGWRFKKRPGVDVFLKECAKYFEIVVYTAEQGVTVFPLVDALDPNGCIMYRLVRDST
HFDGGHHVKNLDNLNRDLKRVVVVDWDRNSTKFHPSNSFSIPRWSGNDNDTTLFELTSFLSVLGTSEIDDVREVLQYYNQFSDSLSQFRENQRKL
GELMHAEEVEKTSKSRPVVKNWTRGFINH*
(SEQ ID NO: 765)

Classification: hypothetical

Celera Sequence No. : 142000013384615
CATTTCGTACAATGCTTCTCCCTTCTCTTTTTGTCTTTTTTGCCTTTCTTGTTTTCTTATTTTCCTGCCGGCACACACACGCACACACATGCAGT
TGCGCTCTCTCGCGCTCGCACACCAACACACTCACCGTTTGGGAGTTTTTGTAGTCAATCAACTGATTGGAAGCCGCATCGCGTCCAGCCATTTT
GCTTAAAATTTAGGATATTTGCTCAACGGGATAACCAGAATTTAGAAACACTCGAACTGGAAAGTTGTTGATTTCTAGCCGCCTTCGGTTTTTG
CTGTGACTGCGTCGAGAATTCTGTCAACTAAAGCAACTGCAGCGCAGTTCCATTTGTTTTTATAGCCCAGCACCACGTACTTGTTGTTGCTCAGG
GTTGTCGAGTGGGCCGAAGATATCGATATTTCGATTATAGTTGGAAATATATCGCTTAAATATTACATAATATCCATTATTATTCATATTTGTAT
TTAAATAGTATGAAATTCATTTTCAAAGTTTTTTTTTTGCACTGTCCATTTAAAAACGTGTCCCAACACCATTAAGATTTATTATTGATAATTTA
TAGTACCTTCGCTCCATTTGCTGCCCAGAAAGGTGAATAAATTTAAACTGTTTGTTAAGTTATTTATTTTTTTAATTTCATGAAAATGTCGGCAT
CATTAAGTTATAAACTAAGTCGGCTATCTATTGGTGCTCCTGCCAAATAAATATCTATGGCCTCTTTTTTTCTTAAGTTGTGAACCTCTTCCAGT
GGTGCCTTTAAAATAAATGTACTTCATTCATATAATATATGTAAATATCATTAAACATGTTAAAATTATAAACTTCAAGGAAATCTCCAAATGGC
GGCTATCTTTCTGTGGCTCCTGCCAAGCTAACATCTCTGTCTTTCTTTATTTTAGCGTACAAAAATATCTAATTAAATGAAACTTAGAAACTAGC
ATCAACTAGCATATGTATCTTGTTCTCTAGTCACAACTTAAAAAAATCACCTAACCACCTGTGGTTCCCATCAAGTAAATATCCATGGACTGCTT
GTCCAGGACGGTCGGGCGCCTCTTTGGAATCGGCTGAATGTGCGGCAGTCGCGTGCCATTCACGGCGTTCAAACTGAGATTCGAGTTGGGGTCGT
AGTCGTCGCAATCCGGAGTAGTCTGGGCCAAGCTCAGCCTCTGCGATGGTTTCACCATTAGGTTTGCCCTCGCAAGCTGGCGTTTTTGGATCGCT
GCAGCGCTGGTAGTGGGCACATTGTCTGAATCTTGACTTAAGCTTCTGTGGGAGCACAGCTCTTCATCGGGAGTCACAATGCCCCCCTCACTGTA
TGAGGCACCGAATTCGGAACTTTGGCCAGAGACATGCAAAGAGGGCGCACTTTGGTGCGACGATGACTGACTGCCGCTGACGTCCGTAATGCTCG
CGGCAGTCTCCCTGGCCATCTTGTGCCGTTTGGCATTGTCGTTCTTCTTCCGGTAGAGTCGCACCAGGTCCGTGTAGCACTTGCAGCAGATGAGG
TTGCCCGCCCGAATTTCGCTGTTCAGCAAACAGGCGAAGCGCACCAAATATTTGTTGTTCAGTTGGCGATACGGCTTCCGCAGCGTGTGGTTGCC
GACTGCGCAGAATCTCCGCTCAACGCGCGAGCCCTCGTCAATGGAGGCCATCTGGAATAGATCATGCACCTAGTTCTCCACAACTCGGGCTTACA
AAACAATGCTTACACTGGCATTTTAACTTCCAAACGCAACAAAACGAAACATGAAGCCAATTGTCCCGCCACTTTGGAAACATATAGTGTGACCA
CATATGGATTGCTGAAATATACCAAAATTAGGCGTAAAATAAAATGCATTTAACTAATAAACAAATTCAATTTTTTTAAATGTTATAAAATCTAA
AAACATACTGACATGGTCACAGTTTCTCACAATTTAAATGTGGCTTATTGTAATGCCAGTTAAGTAATTAATATGAAGAAACTATTCGTTTAAAA
TTGACAATAATCTAATTATTGGCGTGTTCGATGTTCATGAAATACTTATGTTATATCAGTTAGTTTGAAAATTGACTGTATTTCTTCTGTTGGTT
GTATCAATTAAAATGAGTTTAAAAACACATTTTTTAAAACCCTAAAACCACATTCAAATCAAACTGTAATTATACCAACTAATACTGAAAATACC
GAAAACTGCAAAATCAGCTGCTCGCCGAACAGCACTCAGCGTGCTGTTGGACGCGAAATGTTAGCCCATTAAACCCAGGTTATTTTTTGTCATTC
ATTGTTCATACGTTCGTCTCGTCTGATTTTCTTTTTATAAAAACACAATTAAAATTTCAAACGAATACACATAATTTTTATAAATATAATGTAGT
GCAACACGTATATGTATAATATAGCTTAATACCAAGTGCAATCCCTCGAAAGATAACTTCAAATGGCAATCTAATTTACGTAAAGAGAAGAGACA
AAAAAAGAAACGGCGCGTGTGAAATTTTTTCAAGCAAAGCAAAGGAGAGAAGTTGGAGCAACAAAAAAAAGAGGAGAGAAAAAAATACAGCAACAA
CACACAAAGTAGGCCAACAACAACAGCAAGAAAAAAGCAAGCAAGCGGCAACAACCACAGCAACAACAATAACAACGTCGAGCGAAAGAAGCAAA
AACCTTGTAATTGTGTCAATAAATGTTTTAAATAATATTTCCTTTGG
(SEQ ID NO: 766)

Exon: 1707..1001
Start ATG: 1666 (Reverse strand: CAT)

Transcript No. : CT21292
AAGCCCGAGTTGTGGAGAACTAGGTGCATGATCTATTCCAGATGGCCTCCATTGACGAGGGCTCGCGCGTTGAGCGGAGATTCTGCGCAGTCGGC
AACCACACGCTGCGGAAGCCGTATCGCCAACTGAACAACAAATATTTGGTGCGCTTCGCCTGTTTGCTGAACAGCGAAATTCGGGCGGGCAACCT
CATCTGCTGCAAGTGCTACACGGACCTGGTGCGACTCTACCGGAAGAAGAACGACAATGCCAAACGGCACAAGATGGCCAGGGAGACTGCCGCGA
GCATTACGGACGTCAGCGGCAGTCAGTCATCGTCGCACCAAAGTGCGCCCTCTTTGCATGTCTCTGGCCAAAGTTCCGAATTCGGTGCCTCATAC
AGTGAGGGGGGCATTGTGACTCCCGATGAAGAGCTGTGCTCCCACAGAAGCTTAAGTCAAGATTCAGACAATGTGCCCACTACCAGCGCTGCAGC
GATCCAAAAACGCCAGCTTGCGAGGGCAAACCTAATGGTGAAACCATCGCAGAGGCTGAGCTTGGCCCAGACTACTCCGGATTGCGACGACTACG
ACCCCAACTCGAATCTCAGTTTGAACGCCGTGAATGGCACGCGACTGCCGCACATTCAGCCGATTCCAAAGAGGCGCCCGACCGTCCTGGACAAG
CAGTCCATGGATATTTACTTGATGGGAACCACAGGTGGTTAG
(SEQ ID NO: 767)

Start ATG: 42 (Reverse strand: CAT)

MASIDEGSRVERRFCAVGNHTLRKPYRQLNNKYLVRFACLLNSEIRAGNLICCKCYTDLVRLYRKKNDNAKRHKMARETAASITDVSGSQSSSHQ
SAPSLHVSGQSSEFGASYSEGGIVTPDEELCSHRSLSQDSDNVPTTSAAAIQKRQLARANLMVKPSQRLSLAQTTPDCDDYDPNSNLSLNAVNGT
RLPHIQPIPKRRPTVLDKQSMDIYLMGTTGG*
(SEQ ID NO: 768)

Celera Sequence No. : 142000013384546
ACAACATTTGACAACAGCGTGCTTGGCCATCGGATTCCGGAAGTGCCGGTGCCCTTATTCAGCGTTTATCCGGCCACGAAGCATGCAATTACGGC
CCTCTGCCAAACGGTGCGCCAGGAAATACATTTTCTCAAATTAAATATTAAATTAACGGTAAGTTAAATGCAGTGCATACATGGCGCGCCTCATC
CTCCATCTTAATCCTCGGGAAATGCGGCAAACATGACGCGTCTGCTCATTGGTTACCCTCTCCATTTTTATCCCTCCATTGCAGAGCATTTGCCC
GGGCATGGTAGACACGGATTTCCTTAGTGTTTACTCGCAGGCGGTAGCCGAGCTGCCCAAACTGCAGGCAAGGGATGTGGCCAAGGCCGTGTTGT ATGCGCTGAACACTCCCGATGGCGTCCAGGTGGAGGACATCATCCTGCAGCAGATGCGGAAGGTCGATTGAATTTTAGTTTGAATTTCAAGAGAA
TTACATTTTACCCAAAACGATATTATTTGTACATTTTGTATATGTTCTTCTATGTAATAAGAGAACAAATGTACATATTTTTAAATATAAAAAAT
TACATTATTGCATTTCAAGCAACTGTTTCGACACTTTATATTCTTTAAGATGTTATCTGTAGATAACATCTGTATTAACATCTTATTACAAATAA
CATAAAAATGCAATAAAACGATAATTAAACATTTATAATATTTTGCATATTCTCTAATCGATATAACATTAAATGCGTGTAAATAGTTTGGCAAC
ATTATGAATGCATTTATACATTCATTCATTTGAATTGGAATTGCCCGCGCATGTAGTGGAGTTGCCACCTTGCGGTAGGGCTGCCAGATTGAGTC
AAAAGACCAGGGCTGTACAGCTATCGCTAGCGAGTACAACAACCACTCTTGATTTGGCTCGCTTCGCTCTAGCAGAGTTATCCACCAAAACATCG
ATTACTCGTGCTACCCCCAAAATCGATGGTACGAAACAAACATCGATATTTCACAGCTTTCGCTTATTGGTCACACTGGGGCTTATGATTAAAAA
AAACTGAACTGACTCCAATAAAAACGTGAGGTAGAAAAAGCGAATTAGGTTGACAATTAATACACACAGCAGACGCACGGTAACCAGCCGCCAAT
ACCGATACGAACGCGCGGCGGCAACAGCAAGTGCGCAAGTAAAAGTCCATATCAAACGCAAGCTACCCGCAGCCGCGGGCAGTTAAATTCCGAAA
TGCGTCCACGTAGTGCAAAATCCGAATCTCAATTCGAATTCGAATCGGAAGTCCGGATGTCTGCGCCCTTTTTATGCTTTTTTCGAGGGTGCGGC
TTAGATCGGCGTGCACCTGCCGTCCAAAGTGTGATTACGAAATGTGCTCCAACGTGAAATGATATTATAAAGTATAATATAATGCATGTTACCAC
GTAGTTGCACACAGACAGGCAGCACACGCACACACACGCGCACACCCAGTGCCACTCACACACACACACAGACAGTGAGCGAGCGAGAGGGCAGG
AGGCAGAGAAAGAATGAAATAAAGAAAGTGCTGCCCAGTTGACAAAGAACAGGTTTTAACCTAATTAACTAAATAATGGGCCCAAGTGAATGTTT
CGCCGCCAGGAGGAATTTGCTTCCTTATATCCGCAAGGTCCCCGCCGCTCGAGTGTGCGTGTTGTTGTATGTGTGTCAAGGTTCCGGAAGTTGAG
CCGCCGTAAAATTGATTTCCTATACACCAAGCCGCTGTTGCTGCCGCTGCTGTTGTTCTTATTGTGTTTCTGTGGCTGGACATTGAACTTGAGTC
GAAATGCGCACTAACCCATTATCCATGCCATATCTCTTTTCGATCCGGCAGCCGTCTAGCCCAGCAGCTCTCTTCCCCCCACAATAAACACACAC
AAGCTGCTCTTGGAGCCAATCACCCGCAACCGATAGCCACACGAAACCATCAGGATGTTCATCTGGGACTGGTTCACCGGAGTGCTGGGATACCT
GGGTAAGCAACGTCGCCATTGCCGACCTTGTGCCTTGGGGCGGCGTTTCTTGAACGAGTGCCAACAAGGCAGCCGCACAAAAGAAACCCAAATTC
GACGGCTGTACAGCGGAGGTCGTGGTGATAGCTCTAAACGTGCGATTATCTCGAAATCTAGAGGTTAAACTGTGTCTATAAGGTGTCGAAAGCTT
ATAACTTTCCATTAGGTCTCTCTATCACAACAAATGCGCGTTGAATATGCATTACTCTAGGGTGCATATACAATATACACTTCTGTAAAAGGTAT
TTTGATTGCATAGCCATGTACTCTTCAGCCACAATTATTTAAGCAGACATTTTTGATAGGGTTTTCCTCGCTTCCAGATGGCTGCTACACTTTTA
TTTGCTTTGTAATGCTAAAAGTTAAAATTATTCCATACGAAAAGTACTGTTCTACAGTGCAGGCCAAACTGATAGCAGTTGTTATAAGCGCATTT
TTGTTATAGCTTGATCTTTAATCAGGTTAATGATAGCCGAACATTTTGGGTAGCAAAGGTAATAATTAGCCCGAAGTCCAAGAGCTATTGTCTCG
ACCTCAAATGTATATTCGGCTGTCTGTGGCTGGGCAAACACAAGTGAGCCGCCACTAGTGTTAGTTTAGCTGCGTATATTAATTGATGACGCGTA
AGTCAAAAGGCTATTCAACACACTTTCTCGTTTTCAGGTCTGTGGAAAAAGTCTGGCAAATTATTGTTCCTGGGCCTGGATAATGCTGGCAAAAC
CACACTCTTGCATATGCTCAAAGATGATAAGCTGGCGCAGCATGTGCCCACACTGCATCCAAGTGAGTTTCCTTCATGGACTAAATAGTGGTTAT
GTGTGTGACTTTAATTAACTAATATGATTGACTTGCAGCATCCGAGGAGCTGTCCATCGGCAACATGCGCTTCACTACATTCGACTTGGGTGGCC
ACACTCAGGGTAAGTGCCTAATCTTGACCAGAGCTCAGGGGAATGTGAATGTGCATCCAAATCGTTGCTATTTTCCGTACGTGCCCACGACTAAA
TATAGACCAGTATGCAAATATCGCAGGGCTAAGCAAGCGCAGCCGCCAGATCCACGACAATCAGCATGAAATATAGCGCATCAGGTCACCCATAC
AGCCAGTGCGTCTTACACTCGTAGCATTTGTTGCGATCAATCAGCGCCACACACTCGAAGCAATGCCACCACAGTGGTCACAAGCAGCTCATCCA
GAGATCTCAATTATCATCTTATCTCAACTGTGATTATGAAGACCTCAGAATACTAGAATATTTAACCCATTGCATACAATCAATATGTTCATTTA
TGTTTAGAAAGCAATTAGTGTCTTGTTGATTTTCGCAAATACTATCTTCCTTACCACTGTGCACATATAGGCGACGTATTTATTATTAATATTAT
GAAGGCAAACATTCTCTATGTAGATAACAAACAGAAACGAAAAACTCGCATACATGCAGTTGATATATGTATATAAATATGAACATTATGAAAAG
TGATCAAACATCGTGAAATCCAGTTGTTTTGATAACGAAGCTCTAGCACTCATTTTAAGGCAGCTCGTCATCGTGACGATCGTTTTCGCTTCGGA
ACTACTAGGTACACTAAAGTAGAAAGGTTCTTAGCGGCGGAAAGATATCAGATTTGTGCCTGATATCAGTGACTTGCGCTTTGTTATTCTAGCGA
TGTTATATAAATTACAGATTGTTGGTCAACAGCAGCGACTACTAAGGTGCCCTTGCAAATCTTGATTCAAAAATCGGAAGACTAACCCATCTAAA
GACTAACTGCTGCTTTTGTATTTATGAGACATATCTACTTATTTCTGCAGCACGACGCGTCTGGAAGGACTACTTCCCTGCTGTGGACGCCATCG
TTTTCTTAATAGACGCCTGGGACCGTGGCCGCTTCCAGGAGAGCAAAAACGAGCTGGATTCGCTGCTCACGGATGAGGCGCTGTCCAACTGCCCC
GTGCTCATATTGGGCAACAAAATCGATAAGCCCGGCGCGGCTAGCGAGGATGAGCTGAGAAACGTGTTCGGACTGTATCAGCTAACAACCGGCAA
GGTGAGCACCAAAACCACCTCCCTCCCTCCCTCCCTCCTTACTCCTGCTACATAATTGATATCCATTTGACTTGCAGGGCAAAGTTGCACGCGCC
GATTTGCCCGGCCGTCCTCTGGAATTGTTCATGTGCTCCGTGCTGAAGCGACAGGGCTACGGCGAGGGTTTCCGTTGGCTGGCGCAGTATATCGA
TTAAGTCAGCATTAGCAACCACCACCAGCACCATATTTCAAGAACACCACTCAACACTCAAAACCGAAAACTTGGCTACAAAATTTCCAAAAAT
GATTAGAGACCGCAGAAAGAACAGAACCCAAGGGATGTGAACCCAGCCCAATTCAAACCGTCAGACCTTAAGCAAAACGAAGCTGCGTGCGCAAT
TTCTAATTTATACAAAACAATTACAAATATTTCATAATAATAAAAAAAAAAAAACAGAAAACCATACAATGTACATCTGTAACACACAAGAAATC
GCGGGAAAAACAGAACACAACATCAAAGTGAAGACAACTTTTCTATCTGGAACATCGGGATACATTGTAAGGAGCTGAAGGATGCGCGGAGTGCG
CAAGGGAAACTTTTAATAATAATTATGAGTAACAAATTATAGCAAATTAAAGGTGATTTATTTAAGAGCATGTGCTTTCAACGAACGCTGTTTCG
CCAATAAAATGTAGCCACCTACCTTTATTTCAAGTTTATGAATTGTAAATGTCGCTATTGATTTCCTAAATAGTTTACTTTGGCCGCAAAACATT
ATGTACATCCCTATAAGGATTCGACCTCCGATAAATGGTACACCTTAGTTTAGCTAAAAATTTTAAGTTGCATGTCATCGATGTACTTTGTTTCT
TTTATACAATACGAAAGGGAAAGCAATTTATATAAAAAAGCATTTTTGTTTGCAGACAGAATTCTAAATAAAACGGAGAAAAGTAATTTTGTAAA
ATACATAAATTGGTGACTATTGTTGTTTTGCATTGGATTTATGTGCCGAGCTTGAATGAAACCCAGCGATGTACAAACATATTGGATTCATTTAT
TTATTTGCATTTAGGGTTTACGCTAATGAGTCACGTCCGGAGCATCTATTGAAATCAGGGAGCAGGCATTCGATGAGGGCGAGCACGGGATCCAG
GAGCTGCAAACATGCTGGTCCAAGTAGAAAAATACACAAAACTCTGCAGAGTATGATCGCGACCTCAGTGCTAACTGAGCCGGCAGCGGCGGGGC
AGTCCTCTCAGCAGCATCAGTTGGCGTTGAAAGAGGCGCATGAGCAAGCCCTTGCGCTTGGCCCGCTCCCTGGATCAGGAACGCGATGATCCGCC
CATGGAGCCGGACCCGGAGCCGCCGCCAGCCATGCGCCGCTTCTTTTTCTTCTTGGCCGTCAGACTCTCCTGGCCGCTGTCCGTGTTGGAATCGC
CGCCAT
(SEQ ID NO: 769)

Exon: 1001..1075
Exon: 1857..1997
Exon: 2698..2817
Exon: 2889..2954
Exon: 3851..4086
Exon: 4163..4516
Start ATG: 1955

Transcript No. : CT21873
TCACAGCTTTCGCTTATTGGTCACACTGGGGCTTATGATTAAAAAAAACTGAACTGACTCCAATAAAAACGTGAGCCGTCTAGCCCAGCAGCTCT
CTTCCCCCCACAATAAACACACACAAGCTGCTCTTGGAGCCAATCACCCGCAACCGATAGCCACACGAAACCATCAGGATGTTCATCTGGGACTG
GTTCACCGGAGTGCTGGGATACCTGGGTCTGTGGAAAAAGTCTGGCAAATTATTGTTCCTGGGCCTGGATAATGCTGGCAAAACCACACTCTTGC
ATATGCTCAAAGATGATAAGCTGGCGCAGCATGTGCCCACACTGCATCCAACATCCGAGGAGCTGTCCATCGGCAACATGCGCTTCACTACATTC
GACTTGGGTGGCCACACTCAGGCACGACGCGTCTGGAAGGACTACTTCCCTGCTGTGGACGCCATCGTTTTCTTAATAGACGCCTGGGACCGTGG CCGCTTCCAGGAGAGCAAAAACGAGCTGGATTCGCTGCTCACGGATGAGGCGCTGTCCAACTGCCCCGTGCTCATATTGGGCAACAAAATCGATA
AGCCCGGCGCGGCTAGCGAGGATGAGCTGAGAAACGTGTTCGGACTGTATCAGCTAACAACCGGCAAGGGCAAAGTTGCACGCGCCGATTTGCCC
GGCCGTCCTCTGGAATTGTTCATGTGCTCCGTGCTGAAGCGACAGGGCTACGGCGAGGGTTTCCGTTGGCTGGCGCAGTATATCGATTAAGTCAG
CATTAGCAACCACCACCAGCACCATATTTTCAAGAACACCACTCAACACTCAAAACCGAAAACTTGGCTACAAAATTTCCAAAAATGATTAGAGA
CCGCAGAAAGAACAGAACCCAAGGGATGTGAACCCAGCCCAATTCAAACCGTCAGACCTTAAGCAAAACGAAGCTGCGTGCGCAATTTCTAATTT
ATACAAAACAATTACAAATATTTCATAATAATAAAAAAAAAA
(SEQ ID NO: 770)

Start ATG: 174

MFIWDWFTGVLGYLGLWKKSGKLLFLGLDNAGKTTLLHMLKDDKLAQHVPTLHPTSEELSIGNMRFTTFDLGGHTQARRVWKDYFPAVDAIVFLI
DAWDRGRFQESKNELDSLLTDEALSNCPVLILGNKIDKPGAASEDELRNVFGLYQLTTGKGKVARADLPGRPLELFMCSVLKRQGYGEGFRWLAQ
YID*
(SEQ ID NO: 771)

Name: GTP-BINDING RELATED PROTEIN SARA
Classification: ligand_binding_or_carrier Celera Sequence No. : 142000013384669
AATGGCCAAAACGCGGCGGTTGACGTCAGCCTTGTTCATTTCGCTGCTGCTGGTCGCTTCTATTTTCCTATATTACCCTTTATTTCCGCCAGGTG
TAACAGCTGTTGTGTGTGGCAAATGGGAAGAGAAGAGGAGAGAAGACGAGTGGTTACGGGAGGGTTGATAAAAAAGGAAGTAACGCGACAGAGAA
GTAGAGAACTGACAACGTGCACAAATCTCAATAAGGCAATGTTCGAGGTTCGGTTCACGCTTCTCGTTTTTTTTTTTCCTGCTTTTGTTGTTTTC
TCTGCCCTGTTTTTTGGCATTCACTTCTATGGTCTGTTATTTTGTAGTACAAAAAGCAACACTGAGCTGCTGGAACATCTAGAAATTTCAGATAA
TAATCTACTTGCCTCGGGCTCCCACTTGTTCCCAATTAACACGGCTGCTGTGTCGATTTCTGCACAAAATTAGCACAAAAAATCTTCGCTAAACG
GCAATCCCAAAAACTCGATTCCAGTGTGACCACAGCGATAAAGTCACAAAATACCATCGGGCTCTGGCAAAGAATGGGGAAAAAAAAATGAAATT
AGTGATGGAATTATATTTATACGATACAAAAAACAATAGGTGTATGACATTTGTATACTAGCTTAATTATTTGTAGGTTTGTAGGGAACAGCCT
ACCTTGATAATACATACATTTTCTTATTACATTTTTTTTTATCAAATCCAAAGCAAAACCCATACTTTTAGAAAAAAAATTTTTTTTAACATTTT
TTGGAAACATAAAATATGTATCGTACACATTAAAGACCAGCTTCACTTTATTATTTATATAATAAATAAAACTTCTGCTACAAGCCAGAAAAAGC
TAAAATGTAGCCAAATATAGCATGGACCCAAACCAGCGGGAGCACTAACAACTCGTAACGTAAGCGCAGCACGTAACATTTCCGCTATCTCACTC
GCACGTTCAGCTACATAGTGCGGACTCACTTGCACCTAGTAGTATTCGATCCGCTTGGAAATTTTGCTCGCCGTTTGCTTTCTCAAAGGCTCAAA
AAAATGCAGCTACCACCGACTTACCTGGCTTCGCAAGTGAACGCGAACTAAGCCAATAGCATCTCGATTCGCCGGCGTTGCGCAGCGTTCGCAAA
TGCAGCTGAAACGAGCAAAAAACACGCGCACAACGAAAAATCCGCAAGTGGAAAAAACTGCTACGGAAAAATCAACTCTGCCAGCAAACAGTGTT
GCAAATCGATGGAGTTAAACAGCTGAGTGGTTAGTGTTGACTGACAGCCGAGTACGGCAACTTACAACACTGTAGGCGTTTTGGCGCGATTTTAG
GTTTTGGAGGGAAACTGCATCTAGTGAAAAATCGTGGCCAGTTGTAATTCGAGCAGTGCGCTGGCACGACGTGGTGATAAAAAAGGAAAACTAAT
AGAATTATACTGACTAGTGATAATTAACCGGACGTGCCCATCTGTTAATTCAGCCAAGTGGTATCTTTACAACCGTTTAGCCAACAACCAAATTG
CTATCAGAAATATATATTATACACACTTACTATGGCCCAGCCATCGGTAGCTGCATTTTTCACAAACCGCAAACGCGCCGCCTTGGATGATGCTA
TCAGTATCAAGAACAGGGTAAGACTTCCGTCCCAGCAACGTGACTCCAGATACAAAAGTATCTGCAAGGACGTTCTGCCAATACAGGCATTTTAA
AAATGGATTTGTTTTGCAGCGTTTGGTGGAACCCGCTGAAACCGTCTCTCCTGCCTCCGCCCCTTCCCAGTTGCCAGCCGGCGACCAGGATGCGG
ATCTAGACACCCTGAAGGCGGCGGCCACGGGCATGCGTACCCGATCCGGACGCACTGCCCGACTAATTGTCACCGCCGCTCAAGAGAGCAAAAAG
AAGACACCGGCTGCCGCCAAGATGGAGCCACACATCAAGCAGCCCAAGCTGGTGCAATTCATTAAAAAGGGCACTCTGTCGCCCAGGAAACAGGC
TCAGTCCAGTAAGCTGGACGAGGAGGAGCTGCAGCAGTCGTCGGCCATAAGCGAGCACACGCCCAAGGTTAACTTCACCATCACAAGCCAGCAGA
ATGCGGACAATGTGCAGCGTGGCCTGCGCACACCCACCAAGCAGATCCTCAAGGATGCCTCGCCGATCAAGGCGGATCTCCGCCGTCAGCTCACT
TTCGACGAGGTAAAAACGAAGGTATCGCGGAGTGCCAAGCTGCAGGAACTCAAGGCAGTGCTGGCCCTTAAGGCGGCGCTCGAGCAGAAGCGCAA
GGAGCAGGAGGAGCGCAACAGGAAACTCCGCGACGCTGGCCCCTCCCCATCGAAGTCCAAGATGAGCGTGCAGCTCAAGGAATTCGACACAATCG
AACTGGAGGTGCTTATAAGGTGAGCTTTATGCTTATATAAGAAGTTTTATGGGTACTGAACCAAATTCGGCTTCAAATACTTAAAAGAGATTGAA
GCTATATTGAACATCATGTTGTGTCCTATAGTTTCAAGTCCTCTCGAATCAACAATTTCTTTTTAAATTTCTTTGAGGTTGTTTGATACTCGCTT
TATCATTCGAAGAGGCATCCTTAGGGTATTAAACCTTGATTGAATGATATAATTTGACATGCCTTTCGCATCCTCTTCAAATCGAGTAATCATGG
GTGTCGAAGAAAATCAGCCATGTAAGAAGCTCAAGATATGTGCCTGCCGCAACAATTTTGATTGAGCTGGCTGGTGGCCTAGAATCGGCATAAAC
AAACCACGGACTGTGGAGTGTGGTCTATGAAAAAACCGGGTAACATCATTTAGCGAAAGGCCAGCAGTTGCTGCCGTGCAGTTCTGCTGCAATCG
AGGTCGTTCTCCGGGTCTCCAGCTTATTCAAGCTCTCGACTGCTGAAGTTGCATATTTTCCGCCCAAGAGTCGTCAAGTCACCGATGGCTTGGCT
TTGGTTCGGCAATATGGCTATTTTTGTACGAGCAATTGCTGCTGATTCGTGACGTCTGTACAACATGCATAAATACCCAACTGGCTGACTGACCC
TCCCCATGCGGCGACGCTGTGTGTGTGTATCGCTATGCGCAGCATGTTTACCCTTCGCAGACGTTACAATCTAGCCTGACCTTCCCTTTGAAAAT
GCTTATTTTCCGCCCGCATTCGGTGGTTGCTTTCCCTTCGGCACTCGGAAAACAAGGATCTTAACTGCTGTACTGCATGGGAATGTGCATGTGTA
TATCTGTGTATATGTATTTTGGGTCTGACGCTCAGGTAGCAACCTTTTTTTGTAACGGTCGTCTTGAAGAAAAGTCCCAAGCAGCAAGCAGGATA
AATTTTCAAATAGGACATGCCTGTTTGTATTTCGTATTAATTTCATGAAATAAATAAGTGCATTAGCAACCCTAATGTTTAGAAGATTTTTTTTC
TTCTATTTTTATATAATGAAATTATTGTTTCGCGCAAACTTAAGCACCGAATTTTAAAATGTTGATATAGATAACTTATAATTTTCGTTTTTTTT
TTTTTCACAATCAGCCCTTTGAAGACCTTCAAGACTCCCACAAAAATACCGCCACCCACCCCGGACAAACATGAGCTTATGTCGCCGCGTCACAC
TGACGTCTCCAAGCGCCTTCTCTTCAGTCCGGCCAAAAATGGATCTCCTGTCAAATTGGTGGAGGTGCCGGCTTATAAGCGCTACGCCAGTCTGG
TGGAAAGCAGCCGCGCCGGCCAACTTCCATTGCCTTATAAGTACCGACACCTGTTGGACGTGTTCAAGGGTCTCGATTCCGTGGTGGCCATGTTT
CACAACCGCAAGGAGACCATCACATTCAAGAAGCTTAAGCCGGCAGTGCAGCGCATGCTCCGGAAGAACTTCACTGAGACCCATTTGGCCCAGAT
CAAGCACATCTATCCAGACGCATTTATCTTCAGTCAGGTGAAGACGCGCAATTTCGGTTCTGTCTCCAAAGCGGACTATTTCCAGCTGATCATCG
CTCCCAATGTGGAGCCACTGCCCGAGCAACAGCAATCGGAGAAGCCACAACATTTCACCAAGATCAACGAAGACGATGTGCTCGCGTCGGCCCAG
TCGACGTCCATGAATCCACACGTTATGACGGCGCGCATGCAGCGCTTTCAGAGCCTTCTGCTCGATCGGGCAATGCGGGCGCACGACCAGTTCCT
TCGCTCCCAGGATCCGCCGATCATCATCGAAAAGGCGCTGACTCGCTGGCATCCGCAGTTTGATTTGGAGAGTTGTCCGGAAGTGGAGCTGTCCC
CTTTGCCGCAGCCGCCCAATGTCGAGAAATACTCGTCAGCTAAGGATATTCTGTCTACCGCTCGAAATCTCTTCAATTGCGCCACGCCCATGGAG
AGAGCAATGGATCGCTATGAGGCCAAGTTGGAGTCGGAAAAACAGCAAGCAGCTGAAAGCAATAAAAAGACGGAGGAACAGCAGGCAGGAGAAGT
TACCAGGACAAGTACAGCGATTCAAACCAGTCAGGAGGTGCCTGGAATATCTGGATCATCGAAAAACCCAACTGTCCCTGAAACAACAAACCAAA
CAGAAACTGCCAAGCCCACCGTGAAGGATTGCACAGTGCCAGATGCCAGCTCCAATCTACTGAAGGGACTGCCAAAATCACTGATCGAGAAAATT
CGAGCCAAACAGGCAGCAAAGGCTTTGGAGGCGATGACTCGACGTCCTTCGCAGGACCAGGAGGCCACGAAGTACTCACGTTTGCCCGAATTGGC
CAGACACCTGCGCAATGTCTTCGTTACCGAGCGTAAAGGAGTGCTCACCCTGGAAGTAATCATCAAGAAGATCCAGAACAGCTTCCGGGCGAACC TCACACCGCAGGAAATTGAGGCGCATCTGAAACTACTTGCCAAGGAGCTACCCAGCTGGGCTTCCTTTCATGAAGTGCGCAAGACCATGTACCTC
AAGGTTGCCAAGGACATGGACATGAACAAGATCATCGAGAAGCTGGAGAGCGTGGCTAACGCCAAGAGCAATTAGACCGGAAACACGGAAACGCA
ACCAGGACGCGGGACTCCGTCGAGCAATGACCCTGTGGCTATATCCAGATATATGTTTAAGTACTTGTCAAACTCGCTGGCCATTACTTGATTAA
ACAACCGGATTAGGCTAACCATCTTGACATTTCCACATTCAACAAGCACCTTGACAACCAGGATTGGATTCATCACATTTACCCAAGCAATCATT
ATCATTATATGTGTAATTTTTGGACCAAACGTTTATACATTCATATTTATTAGTTTTAAGACCATTTTCATGTTGTACCACGTTGAATAAATAAA
TATTTTTCCTGGAAATAATAAACGTACTCATTCAATTGTGTAGACAGGAAATATAAAATTTATAGCCTGGCTCACAAGCATTAAATTCATCTCTT
ATCTTCCAAGTCTATCTATGTATATATAAGCTATTTAAATCAAAATCATTTTCAGTTCCAAAATGCAGCTCATCGTGAAATTACTGGTGAGTAAG
CTAATCAGTGAAAAGGTATCTTTCGCTAACATTCCATCTCCCTCAGATTGTCCTTTTGGCATTATTTGAATTGCTGTCTGGCAATTCAAATAATC
GACAAGAGACCTGGGGCCACCCTCCATGGGGGTAAATTAAATGGCGTGAAAATTAGATACAAAAGATTCAACTGTAGTTGTTCTTGATGTCTTAT
TAAAAAGTGAAATACTTTTGACTTGTGCATTGGCTTTTATTTATAAAAATTAATGGTGATGCGTCTAAAAAACTCGAACTTAATAGTTTTTTTGC
GCAATATAATACTTATATACAAAGGCGACAGCGCCCTCTAGCGCTTTTTATTTTACAATAATGCGGGACTATAGCTAATCCCATTGTCCCAGCTG
CCAAGTACCATATTCAAAAGATCTGGAAATTCGGGACCCGGCTGAGAGTGGAAACTTTTGGATGCCGTGGAGAGGCCCTGATACGGAATGTGTCA
TCCAAGTCTACTGACGTGGCGTATTTATTC
(SEQ ID NO: 772)

Exon: 1001..1632
Exon: 1730..2394
Exon: 3530..4106
Exon: 4191..5015
Start ATG: 1552

Transcript No. : CT21945
CCGCTTGGAAATTTTGCTCGCCGTTTGCTTTCTCAAAGGCTCAAAAAAATGCAGCTACCACCGACTTACCTGGCTTCGCAAGTGAACGCGAACTA
AGCCAATAGCATCTCGATTCGCCGGCGTTGCGCAGCGTTCGCAAATGCAGCTGAAACGAGCAAAAAACACGCGCACAACGAAAAATCCGCAAGTG
GAAAAAACTGCTACGGAAAAATCAACTCTGCCAGCAAACAGTGTTGCAAATCGATGGAGTTAAACAGCTGAGTGGTTAGTGTTGACTGACAGCCG
AGTACGGCAACTTACAACACTGTAGGCGTTTTGGCGCGATTTTAGGTTTTGGAGGGAAACTGCATCTAGTGAAAAATCGTGGCCAGTTGTAATTC
GAGCAGTGCGCTGGCACGACGTGGTGATAAAAAAGGAAAACTAATAGAATTATACTGACTAGTGATAATTAACCGGACGTGCCCATCTGTTAATT
CAGCCAAGTGGTATCTTTACAACCGTTTAGCCAACAACCAAATTGCTATCAGAAATATATATTATACACACTTACTATGGCCCAGCCATCGGTAG
CTGCATTTTTCACAAACCGCAAACGCGCCGCCTTGGATGATGCTATCAGTATCAAGAACAGGCGTTTGGTGGAACCCGCTGAAACCGTCTCTCCT
GCCTCCGCCCCTTCCCAGTTGCCAGCCGGCGACCAGGATGCGGATCTAGACACCCTGAAGGCGGCGGCCACGGGCATGCGTACCCGATCCGGACG
CACTGCCCGACTAATTGTCACCGCCGCTCAAGAGAGCAAAAAGAAGACACCGGCTGCCGCCAAGATGGAGCCACACATCAAGCAGCCCAAGCTGG
TGCAATTCATTAAAAAGGGCACTCTGTCGCCCAGGAAACAGGCTCAGTCCAGTAAGCTGGACGAGGAGGAGCTGCAGCAGTCGTCGGCCATAAGC
GAGCACACGCCCAAGGTTAACTTCACCATCACAAGCCAGCAGAATGCGGACAATGTGCAGCGTGGCCTGCGCACACCCACCAAGCAGATCCTCAA
GGATGCCTCGCCGATCAAGGCGGATCTCCGCCGTCAGCTCACTTTCGACGAGGTAAAAACGAAGGTATCGCGGAGTGCCAAGCTGCAGGAACTCA
AGGCAGTGCTGGCCCTTAAGGCGGCGCTCGAGCAGAAGCGCAAGGAGCAGGAGGAGCGCAACAGGAAACTCCGCGACGCTGGCCCCTCCCCATCG
AAGTCCAAGATGAGCGTGCAGCTCAAGGAATTCGACACAATCGAACTGGAGGTGCTTATAAGCCCTTTGAAGACCTTCAAGACTCCCACAAAAAT
ACCGCCACCCACCCCGGACAAACATGAGCTTATGTCGCCGCGTCACACTGACGTCTCCAAGCGCCTTCTCTTCAGTCCGGCCAAAAATGGATCTC
CTGTCAAATTGGTGGAGGTGCCGGCTTATAAGCGCTACGCCAGTCTGGTGGAAAGCAGCCGCGCCGGCCAACTTCCATTGCCTTATAAGTACCGA
CACCTGTTGGACGTGTTCAAGGGTCTCGATTCCGTGGTGGCCATGTTTCACAACCGCAAGGAGACCATCACATTCAAGAAGCTTAAGCCGGCAGT
GCAGCGCATGCTCCGGAAGAACTTCACTGAGACCCATTTGGCCCAGATCAAGCACATCTATCCAGACGCATTTATCTTCAGTCAGGTGAAGACGC
GCAATTTCGGTTCTGTCTCCAAAGCGGACTATTTCCAGCTGATCATCGCTCCCAATGTGGAGCCACTGCCCGAGCAACAGCAATCGGAGAAGCCA
CAACATTTCACCAAGATCAACGAAGACGATGTGCTCGCGTCGGCCCAGTCGACGTCCATGAATCCACACGATCCGCCGATCATCATCGAAAAGGC
GCTGACTCGCTGGCATCCGCAGTTTGATTTGGAGAGTTGTCCGGAAGTGGAGCTGTCCCCTTTGCCGCAGCCGCCCAATGTCGAGAAATACTCGT
CAGCTAAGGATATTCTGTCTACCGCTCGAAATCTCTTCAATTGCGCCACGCCCATGGAGAGAGCAATGGATCGCTATGAGGCCAAGTTGGAGTCG
GAAAAACAGCAAGCAGCTGAAAGCAATAAAAAGACGGAGGAACAGCAGGCAGGAGAAGTTACCAGGACAAGTACAGCGATTCAAACCAGTCAGGA
GGTGCCTGGAATATCTGGATCATCGAAAAACCCAACTGTCCCTGAAACAACAAACCAAACAGAAACTGCCAAGCCCACCGTGAAGGATTGCACAG
TGCCAGATGCCAGCTCCAATCTACTGAAGGGACTGCCAAAATCACTGATCGAGAAAATTCGAGCCAAACAGGCAGCAAAGGCTTTGGAGGCGATG
ACTCGACGTCCTTCGCAGGACCAGGAGGCCACGAAGTACTCACGTTTGCCCGAATTGGCCAGACACCTGCGCAATGTCTTCGTTACCGAGCGTAA
AGGAGTGCTCACCCTGGAAGTAATCATCAAGAAGATCCAGAACAGCTTCCGGGCGAACCTCACACCGCAGGAAATTGAGGCGCATCTGAAACTAC
TTGCCAAGGAGCTACCCAGCTGGGCTTCCTTTCATGAAGTGCGCAAGACCATGTACCTCAAGGTTGCCAAGGACATGGACATGAACAAGATCATC
GAGAAGCTGGAGAGCGTGGCTAACGCCAAGAGCAATTAG
(SEQ ID NO: 773)

Start ATG: 552

MAQPSVAAFFTNRKRAALDDAISIKNRRLVEPAETVSPASAPSQLPAGDQDADLDTLKAAATGMRTRSGRTARLIVTAAQESKKKTPAAAKMEPH
IKQPKLVQFIKKGTLSPRKQAQSSKLDEEELQQSSAISEHTPKVNFTITSQQNADNVQRGLRTPTKQILKDASPIKADLRRQLTFDEVKTKVSRS
AKLQELKAVLALKAALEQKRKEQEERNRKLRDAGPSPSKSKMSVQLKEFDTIELEVLISPLKTFKTPTKIPPPTPDKHELMSPRHTDVSKRLLFS
PAKNGSPVKLVEVPAYKRYASLVESSRAGQLPLPYKYRHLLDVFKGLDSVVAMFHNRKETITFKKLKPAVQRMLRKNFTETHLAQIKHIYPDAFI
FSQVKTRNFGSVSKADYFQLIIAPNVEPLPEQQQSEKPQHFTKINEDDVLASAQSTSMNPHDPPIIIEKALTRWHPQFDLESCPEVELSPLPQPP
NVEKYSSAKDILSTARNLFNCATPMERAMDRYEAKLESEKQQAAESNKKTEEQQAGEVTRTSTAIQTSQEVPGISGSSKNPTVPETTNQTETAKP
TVKDCTVPDASSNLLKGLPKSLIEKIRAKQAAKALEAMTRRPSQDQEATKYSRLPELARHLRNVFVTERKGVLTLEVIIKKIQNSFRANLTPQEI
EAHLKLLAKELPSWASFHEVRKTMYLKVAKDMDMNKIIEKLESVANAKSN*
(SEQ ID NO: 774)

Celera Sequence No. : 142000013384581
AAGCGAGCTTTTTGCACTTGTCTTGGATTTAAATATTGTAACGAAAAACGTATAAACACAATCAGGCAGCGAAGAAAAGCTCTCTTCTGAGATAG
TTAAAAAAATAACATTATAATTGCACTAATTTTTCACACCAAACTATGATCGCATTTTCCCCGGCGATTTATGTATTTTTGGATATTTCGAGTGC
GAATGGGGAGCCCAGCGACCCGAGCAGTTGGAGATTCCGGAAAGTTGTGAGTTAATTGTTCATCTCGGTTCATTTTGCTAGACCAGGGCTTGAGA AACACACGAAAGTATCGATTAAATGCTCGATATTTTTTTTGAAATGCGTTCCGTTACTTTTACATTCACCTGGAGTGGAAAATGTATACATTTT
TTGGACCAGAAACAAACTGGTAATTTTTATGACAAGCGAATTTTAAGCATTAAAAAGGAATTTAATCGCATTACTATTTTTATTTCAAACAGCTA
TGATAGTAAGTGTAATAGTAATTTAAATTAATATAATTTGTTTTAGCTTGATATCTTAAGAACAATCAGAGTGCAATTCCAAAATGTAAATAAAA
TTTTTGCTTTATTTGAAAAAATATTATAATTCTTATTTTTAACGGTACAAAAATACACAGCTTAGCGGTGACACGAACCGCGATGTATTTGAAT
ATAAAAGTAAATTGGATTCATAGTCTTTTTCTCTAAAATTTCTTAAAATCTTTTATCTGAGACAAATAAATCATTTCGGAAGTCCAATTGGTTT
CGTTATTACTAGCTTCTATTTCTGTATTGCATTTTCGTAAGAAAAGGAAATTTCGAAACAAATTTAAAGAAAGAGCTCTATTAAATTGTAATATG
TTTTTGAAATGTGTTCTCTTTACATTCGATTTAAAAGTCTTCGTCTTTCGACGACTATCGATCCTCTGTTATCGAAGCATCGCAAAGTATCGAG
TACGGATTCCCCACTGAAGTTTGAAATCATTCTCGCGAGTGGATCTCTCGAGAGCGGACGTTTTTCGAGTCGGAGCCGGGTCGAGTCGAGGGCCC
CAACTTGGAATTTTCTTTCCGATTGACTTGGAAAATAGCTTCTTCGTCGCGTGCGAGTGTGTGTGTGTGTATGTGTGTGCGCGCGGTGTGGAGTT
TATAAAAAGAAGTCGAAAAGTGTTTGCCGCATCAACGAAAATAAAAACACCCAAGAAGAGTGTTTGTTGTTTTGTCTGTATAACAGAAAACTGAT
TTTCTCAACTTCACCTCTGCACATCGATCAAGGACTAGATATAGATGCATCATATGTAGCCGAATTAAAGTATCTGGTAAAGTAGCTGTTGATGA
ATCTTAAGAAACCGATTTACAGTTAGTTTTGGATCCACGCGTAGTTTTTACGCAGGTTTCAACAGCTGCAGTCCCCCCGTCTCGCTCACTCCTT
CTCCCTGCCTATTCTGTTTCTGTCTTGAGGTTTATCTTGTGGCCTGTTTTTGTTGTTACTTCACTTGCGTACTTCTATTTCCACTCCTTCGCATC
CGCTGCCGTTGTTGTTTTTGTTGTGGCACACTGCCTCTTTTTATCGCCTCTCTGTTACGAACAGAAAACTCAAGATAACTCCAAAAAACTCGAAG
GGGGCAAGGGCTTCAAATGCCTTTTAAGATCCCCAAATCATTTAAGGGATTTCGGGATAATTCTAAAAAATGAATATATTATTATCTATTAAAAA
TTAATATTTTATATTAAGGTAACCTCTTTTTTAGTTTTGAAAAAATAAATAATTTTTACAGTTCTTTTTAGAGATTTTCCGGTTAGATTTTTTTC
AAATGTTAAAAGTTTTTTGGTCGTACTATTTTAAAATGTAGAGGGGTTACTATTGTTAGATAGTTTTAATACTTAAGTTATATTTCATTTTCGTT
ATCTTTCTATAATTCATTTGTTATAGAAAGCGTGCAAGTGAGCATCGATGTCGATCTCTAGATTTTAGCAATATATTTCTGTTTCTTCTAGATAT
TCTTATTTCAGTATCTCATAAATATCTCATGTACTGTGGGACTTTTGTTAAGTTCCTGATAAGCTTGTTTAAAATATTTTCCATCTTGTGTCTCC
ATTTTCTAATCTTTTCAAAAGTTACTCTACTATGTCACAGAGCAGTGCTAAGAAGCATTTGAATGCACATCTACTTTGGCTAGGGAATTTTTGTA
GATTAAGCATACAAACCCGAACATATAGAAACATGATGCCATAACGGCAAGCCAAGTGAATGACTGCATGTGGACTAAAAAAGTGCATTGCCAAG
CTGATTTTCTTTATTTCAGCGACCATGGAGAACGGGCTAATTAAAATGTGAGCCGGGCCTGTCGCCTTGATGCAGATGTGCAGCCGACGAATTAA
TTTATCTAGATTGGATTGCGGACTGTGGGCAGAAAGGATTTAGTATTTAGTCGGTGTCTTCTAATTATAGCCGCTCTATCGCGGTCTGATCTCAT
ATTTAGACGGTAGACTTCCACAACATGTGTGCTCCAGACCGAGAATTGAAATTCGGTGCTGGGGTTGGAATGGTGCATATGTGTACAGTGTAAAC
ATACAGTGGTCAGTCGCGAGGAAAGTTTTACTATGCGAAGATATTAGCTTTTGAACATCAAAGTTTCAGAACATTTCTAGTGCCGGATACACATA
TCATTTAAGGGTTTTGGATTGATTAAAGTCATGTACTAACAGAGCCATGTGATTTTTTTTTCTAAATAAAAGCATATGTTTGAATTAAATCATTG
GCATCAGTGATGACAATTGAATTTGAATTCCCACTGTCCACTGAGTGACTGCATGAAATCATATTTTTTATTTGTATGGTCAAATAAGCTCTGTG
CCTTGATGAAATTGGAAATATAAACAACGTCGCCCGGCAAAACTAAGAAAACATGAGCCACGGCAATTGTTCGCGCAAATTTTTATGAACTGGCT
ATACACAGATATGCACGAATATAAAATGTATATACAGACCGACCCCTACACTTAGATACAGATATGTACACATCCAGCGAAGTCGAGAATCGTGG
AGCGCTCCAGTGCTCCATTATTTACCCACATACACATATGTACATTGTATGAACCCATATTCTTATAGTGTATTTGGCTTGTATGTCTGGTAAAT
TTACGTTTTGTTTCTTTACTTATTTGTTTATTTGCCAGTTTTCTCGGCGGCAAAACGAACGAAAATGAAATTAACCAACGCACAAATAGCAAACA
AAAAAAATTTAAACACACTCCAAGTAATTAAGTTTGGAGCGGAGTCAAAAACTTCCCATGTGCCACAGAGCTCCATGGAAAAAGTGTATCTGTGA
ATGAACTCTTATCGGGGCAGTTGAAATTATGAAATATGTATTATTAGACTAGGGAGAGCAGCTAGCTCCATGTTTGGGTCTAGAAAATGTGTTAG
TCTTAAAAACTTGGGTTCTTATCTCACCGGCTCGTAGCTCAATATTTGATTCTCGATTTTGGTGGCCGATTTTTCCCTGCCCCGTCGAAATCTTC
ATGATAAGAACATAAAGGTCATCGAAACATTGTGTCTAATTTCTAATATTTAATCCTTACATATAGTTAAAAAATATTTATTTATATAGATATTT
ATATAGGTCTTAAGTCTGATTCTGCTCATCTTTTTTGGTAGAGAGATTCTGATTCCATTTCTACAGCTTAAAAACGAAATTATACACAAATCACA
ATTCTTCAATTGTATTCTGTGCGAGAATCCCTCGTACTACAAATGAATACTGATAAAAACAGCGATCCAACGCACCAGGCAACAACGGATTATGA
TTATGCTATACCATTATCGGGACCTTATATTGAGAGTAGTCGGATTGATAATAGGATCCATTCAGTTTCAGTTCAAGATTCGGTTTGCGTCTCAG
TTTGTGCGTAAGATTCGTTGGACGCGGATGCCTTTTTTTTAATGGTACGAGACGAAAATAAATCGGTTTTTTTTATTCTGATTTTGCTGTGTAGA
AAATTAGAGCATCTCTGTTGATAAGCGGTTTACAGTGATGATAGAAGCGTGAAGTTTGTTTAGAGAGTAAAATTGAAATCAAAGGAATATTATTA
ATTAATAAGGCAATCTGTTAATTTTTCAGCTACAGGACTAGTTGGAAAATGCCACAATGAATAAATAAATATTTTGATCAAAATAAGGAAGAGAG
CCGTGGTTAAGTAAGTAGCAAAGCACTGTTTTTAATTCATGATCTAATAATAGTTGGTGGAATTCACAAATGTTAATCACTGTTAATTTGGAGAA
GTGATGAAAACTGATACTTGAATCACCAACCTTTTTTTTGATAACTTTTACAAACTAAAATGAATTTTTTTTAGATTTTCATACTGAGGATCACG
TGGACAAGTGTAAGAGATCCCCTTAAAAAACGAACGAAAAGAAAAGCAACTGATTAAAGTCCCGGCCGGAAGTGCCCCAGTGGAACGCGACCCCA
ACAACTGAGAGCCACATCGAGATGTTGGAGCTGCGGCTTATCGTGGTCATTGTGCTCGCCCTGCTCAGCTGGCAGTGGGACCCAGTGGACTCCCA
AAGACCGCCCCAGCATGGCCGACGTGATCGTCCGAAATATCCACCGAACAAGTTTATCAAGACTCATCCATGCGAGAGATCCTCCTGCTACCCGG
CAACGGGTAATCTTCTGATCGGCCGAGAAAACCGCCTGACTGCCAGTTCCACGTGTGGTCTGCACTCGCCGGAGAGATTCTGCATCCTGTCCCAT
TTGCAGGATAAGAAGTGTTTCCTCTGCGACACGCGTGAGGAGACCAAGCATGATCCGTACAAAAATCATCGCATCGGACAGATTATATATAAAAC
TAAGCCAGGCACCAACATACCCACCTGGTGGCAGTCCGAGAATGGCAAGGAAAATGCTACCATTCAACTGGATCTGGAGGCGGAGTTTCACTTTA
CCCATTTGATCATAACCTTCACCACCTTCCGACCAGCGGCCATGTACATCGAGAGATCCTTTGATTTCGGACAGACGTGGCACATCTACAGATAT
TTCGCCTACGACTGCAAGGAATCCTTTCCGGGAGTGCCCACTGTCTTGGAAAACATCACCGATGTCATGTGCACCTCGAGGTATTCCAACGTGGA
GCCCTCGAGGAATGGTGAAGTGATATTTAGGGTGCTGCCACCGAACATCAACGTTACCGATCCCTATGCGGAGCACGTGCAGAATCAGCTGAAGA
TGACCAATCTGAGGATCCAGATGACGAAGCTGCACAAGCTGGGAGACAATCTTTTGGATAGCAGGCTGGAGAACGAGGAGAAGTACTATTATGGC
ATCTCCAACATGGTGGTTCGCGGATCCTGCTCCTGCTATGGCCACGCCTCTCAGTGTCTACCGTTGGATCCCGCATTTTCCCAGGCGGACAACGA
AGATGGCATGGTGCATGGCCGATGTGAGTGTACCCACAACACCAAGGGAATGAATTGTGAAGAGTGCGAGGATTTCTTCAACGATCTCCCATGGA
AACCCGCTTTTGGAAAGAAAACGAATGCCTGTAAGAAATGTGAGTGCAACGATCACGCCGTTAGTTGTCACTTCGATGAGGCTGTCTTCACTGCA
TCCGGTTTCGTTTCCGGCGGAGTGTGCGACAATTGCTTGCACAATACTCGGGGTCAGCATTGCGAGGAGTGCATGCCGTACTTCTACCGCGATCC
AGAGCAGGATATAACGTCCGAAAGGGTTTGCCAGCCCTGTGACTGCGATCCTCAAGGTTCGTCGGACGACGGCATCTGTGACTCCCTAAATGAAC
TGGAGGAGGGAGCAGTAGCAGGTGCCTGCCATTGCAAGGCCTTTGTCACGGGACGTCGTTGTAATCAGTGCAAGGATGGTTACTGGAATCTGCAG
TCGGATAACCCCGAGGGCTGCGAGCCGTGCACCTGCAACCCCCTGGGTACACTGAACAACTCCGGATGCGTTATGCGCACCGGCGAGTGCAAGTG
TAAGAAATATGTGACGGGCAAGGACTGTAACCAGTGTATGCCGGAGACCTATGGTCTTTCGGAATCTCCGGAGGGTTGCTCTCTGTGTAACTGCG
ATGCTGGTGGATCCTACGATAATTACTGCGATGTCATAAGTGGTCAGTGTCGCTGCAGGCCCCACATGACGGGTAGGTCATGTTCGCAGCCGAAG
CAGAATTACTTCATTCCCCTGCTGCCCGAGGTTCATGAAGCAGAGGTGGTGGACGAGTGCATCTCGTATGGCGCCAACGGTAACTGCAGCCTGGT
GGCCGAAACTCCTGATGGCAGTTTCACGGGCATTGGTTTTACCAGGGTTCCTGAGAACTCGGAACTGGTTTTCACTGTCGGAGATATTCCTCGAT
CCATGCCATACGATGCGGTTATACGTTACCAGAGCACTTCACGAGGAGATTGGGAGAACGCCTTTATCACTCTTGTCAGACCCGATCAAGTGGAT
CCTGAAGGAGGATGCGGTGAACTAGCTGCAGCAACTTCTTCGGAAACCAGGATTCCGTTCTCCCTTCCTGATCGCAGCCGTCAGGTGGTTGCTTT
GAATGAAGTATGCTTGGAAGCTGGAAAGGTTTATAAATTCCGGATTTACTTTGAGCGAAAGCGACACGATGTGGACAGTCCCACAGCGACGATCT
TGGTGGATTCTCTTACGCTCATTCCCCGCATCGATGTAACGCCCATCTTCCAAGGATCCGTTCTGGCTGATATTCGCAAAAAGGATTACGAAAAA
TACAATTGCAAATCCTCTTTGTACGATATGAACTACAAGTCGGATCCTAAATGTCAAAATCTGGACAATATCCTCAGTGTGTTTGTCCACGATGG
AGCCAGTATGTGTAATTGCAATCCAACCGGATCGCTGAGCAAGGTGTGCGAATCCAATGGAGGTTACTGCCAATGTAAGCCCAATGTGGTGGGCA
GGCAGTGCGATCAGTGTGCTCCGGGCACCTATGGTTTTGGTCCCGAAGGTTGCAAGGCTTGCGATTGCAACAGCATCGGATCGAAGGATAAATAC

FIGURE SHEET 419

TGCGACCTGATAACCGGCCAGTGCCAGTGTGTGCCGAATACATACGGCAGGGAGTGTAATCAGTGCCAGCCGGGCTATTGGAATTTCCCCGAGTG
CAGAGTGTGCCAGTGCAATGGTCATGCGGCCACGTGTGATCCCATTCAAGGAACCTGTATAGATTGTCAGGTATGATGATATATAATATAGACAA
TATCTTGCTTGTACTTAATGAACTTTTTAAACTTGCTTCTCTTATCACCAGGACTCGACCACGGGCTATAGCTGTGACAGCTGTTTAGATGGATA
TTATGGAAACCCACTTTTCGGCAGTGAGATCGGATGCCGACCATGCCGCTGCCCGGAGACGGTAGCCAGTGGCCTGGCGCACGCAGATGGCTGCT
CCCTGGACACACGGAACAATAACATGTTGTGCCACTGCCAGGAGGGATATTCCGGCTCCCGTTGCGAGATCTGTGCGGACAACTTCTTTGGCAAT
CCGGACAACGGTGGTACCTGCTCCAAGTGCGAGTGCAGCAACAATGTCGATCTTTATGACACTGGAAACTGTGATCGGCAGACGGGAGCTTGTCT
AAAGTGCTTGTATCAGACGACTGGCGATCACTGCGAGCTCTGCAAGGATGGATTCTTTGGGGATGCACTGCAGCAGAATTGCCAGCAGTGCGAAT
GCGATTTCCTCGGAACGAATAATACCATAGCTCATTGCGATCGTTTTACGGGTCAGTGCCCCTGCTTGCCGAATGTCCAGGGTGTGCGTTGTGAT
CAGTGTGCCGAGAACCACTGGAAGATTGCCTCTGGCGAGGGTTGTGAAAGCTGCAACTGCGATCCAATTGGAGCACTCCATGAACAGTGTAATTC
CTACACGGGGCAATGCCAATGCAAGCCAGGATTTGGCGGCAGAGCGTGTAATCAGTGCCAGGCTCATTACTGGGGCAATCCCAACGAGAAGTGCC
AGCCGTGCGAGTGCGATCAGTTTGGAGCTGCTGACTTCCAGTGCGACCGGGAGACGGGTAATTGCGTCTGTCACGAGGGAATTGGGGGCTACAAG
TGCAACGAGTGCGCCAGGGGCTATATTGGGCAGTTTCCACACTGCTCACCTTGTGGCGAATGCTTCAACAACTGGGATTTGATTTTGAGTGCTCT
GGAGGATGCCACAACTGCCACTATCCTACGAGCCAAGGAAATCAAGCAAGTGGGAGCGACAGGAGCCTACACGTCCGAGTTCAGTGAACTGGATA
AGAAATTGCAGCACATTAGGAATCTGCTGCAGAACACCTCGGTCAGTCTGGTTGATATAGAGAAACTGGACTATGAAACCCAATCACTTAGGGAC
CAACTTCAGGCGTCCCATGGCCGATTAAGTGAAACCGAGCAAAACCTGGATGACATTTACAATTCGCTAAGTTTGTCGGGCGTTGAGCTAGAGAG
CCTACAAAATCACTCCAGATTGGTGCAACAACTGTCCAAGGAACTGAAGGAAAACGGCATACAACTGCAGGAGTCAAATATCGAGGGAGCTTTGA
ACCTCACACGTCACGCCTACGAAAGAGTCAGCAATTTGTCGACCCTTAAAGACGAGGCCAATGAACTTGCATCGAACACCGATAGGAATTGCAAG
AGAGTGGAAAATCTGTCTAATAAGATTCAGGCCGAAGCCGATGACCTGGCAAACAATAACAAGCTCATTGAAGACTACCGAGCAGAGTTGACTTC
GCTAACCTCCCAAATTCCCGAGCTGAACAATCAGGTTTGCGGCAAGCCAGGTGATCCCTGTGATAGTTTGTGCGGAGGTGCTGGCTGCGGTCATT
GTGGCGGTTTCCTGTCCTGCGAACATGGCGCCAAAACCCATTCGGAGGAAGCCCTTAAGGTGGCCAAGGATGCTGAGACGGCCATTACCAGCAAG
AAGGATCAGGCGGACCAAACCATCAGGGCTCTGACCCAGGCCAAACTGAATGCCTCCGAGGCATATGAGAAGGCCAAGAGGGGTTTCGAACAATC
CGAGCGTTATCTGAACCAAACCAATGCCAATATCAAGCTGGCCGAAAACCTATTCATAGCCCTCAACAATTTCCAGGAGAACAAGACAGCTTCTC
CTTCGGAGAGCAAAGAACTGGCACAGAAAACTCTCGACTTGGACCTGAAACTGGAACCCGAAGAGATTGAGACCCTCGGCGACCAAATCAACAGG
GCTGTCTCATCGCTAAAGAATGTTGAAGCCATAATCTACAGGACCAAACCCGATTTGGACAGGGTCAATAATCTGCAGAGCATTGCCAATGCCAC
CAAGGAGAAGGCCGATAAGATCCTGGACTCTGCCAATTCGGTCGTGGAGAGCCTGGCGGCGGCAGATGAATCCCAGGGTAAAGCCAAGGATGCCA
TTCAGCAGGCGAACAGTAACATTGAGTTGGCCGGTCAGGATCTGGAGAAGATCGATGAGGAAACGTATTCCGCCGAAGCTCCGGCCAATAACACA
GCACAGCAGGTTGAGAAATTGGCCAAGAAAGTGCAGAAACTGCAGAATAACATAATGAAGAACGATCGGGATGCCAAGGAGATAACCAAGGAAGC
GGGTAGCGTCAAACTGGAGGCCATGAGGGCTCGCGGAGAGGCCAATAATCTTCAGTCTGCCACAAGTGCCACCAATCAGACCCTCACCGATCGCG
CCAGTCGCTCCGAAAATGCCAGGGAAAGGGCCAAGCAGCTGCTCCAGAGGGCCTCCAAACTAACAGTCGATACGAACGCCAAGCTAAAGGATCTG
AACGATCTGCAGACCGTCTATCTGAACAAGAACCAACAACTACTGCGATTGCAGGCCGAGATCGGCCCCTTGAACAAGGAGCTCAACGAGCACCT
GATTCACATCAAGGAGCGGGGGTCGCACTACAGGCAGTGCTATACGTAGATTGGGAAACGTAAGTAATGCAGTTTTAATACTATTACAAGCAAAT
AACTAAAATCAGTAATATTTTTAGATCCATTTGCGTGGCCATCTAAATTGCCATATTCATGAACAAATAAGCAAATTGCGAAATACGAGAATCA
AGTAAAGAACTACAAGAACAACTAGGAAGGCGACAGTTATTATGTAACCACTGTTAAGTTACCGTTACGTTTTGTACTCTAAGCGAAAACCAACA
CTGCAATGTTAATTTTAAAAATTGAGCGAAAGAAATCGATGCCTTCACTTTTAATGTGTACACACTGAGCTAAGTTTTTCTTATACTATCCCTAT
ACCATTTTGTAATGCAATTAATGTAATTAAATAAAACTACTTAAATGTGGAAATGTCTAGCATTTGTTTGGGCTCGATCGGGAGAGGAATGAGAT
AATGGTCATTTAAATGGAGAGCGACAGGTGAGAGTATTTTTGCAACACAGTTCTATTTCCCAACAATAAATCTTTTTCGCTGAACAAATGCAACT
ACTTTTAAGTATAATAACAGAAATATATTATTTACAAACGTTGAATAAAACAATATTAATAACGTTGGAAATGAAGCCTAAAAGCTTAATATAGA
TAAAAAGTATTTAAACAGAAGTTTGTTGGAGTTCAAATATATACAAAAATTCGGCTTATGCTATTTTCACTGTACTTCGATTTCTATACTATTGT
ATACTTATGCTGCCATAAACATTGCCAATTTATTCCATTTTCCGTTTTGTTTTAGTTCTTCTGCGCGTCGCGTGCGGCTTGTTTTTGTTTTTAAT
TTTCGTCCAAATAATTTTCCACATTTTTTTTTCGGGGGCCAGAGGTTCTTTTAAAACCGGAAGTTGTTACGAATGGATCACCGTTACAGAAGATC
GTTAAGGAGCTCAGCAGGTATTTAATAACAATTAAAAAATTAATAATGCAGTTGGCACAGTTGCAGAGAAGCCCACTTCAAGCACAAAGGTCAAG
GTAATGCAAAAAATGCAAAAGTGCTTGAAATCATGCAATTTCTAGTTATCCCTGCCTGCTCGAAAATCACTAAAGTTTTGCATGAAAAGAGTACC
CCTGCTGGCTATCGATAAGAGTTATCGCTTCGGCCCCTATCGATATTTCAAAAGTTCATCAATTTCAGCTGAAATCTCAACAAGTGCAAGTTTCG
AGCTCTGTTTTAATTAAACACAGACGTGTCGCCGAACAAGTCGGCATTGTTTGGATCGGTTTTCAGGTTGCAGTGCGTGAAAATATATATATATT
TTTTATTTATTTATTGCGACATCCGTGCGGCCACTCACACACACAGGCGCGATTGACAGATGTGCGACGTGCATACGTATAAAGAGCACACACTC
GCACACAC
(SEQ ID NO: 775)

Exon: 1001..1311
Exon: 4115..4190
Exon: 4350..7195
Exon: 7272..9939
Exon: 10001..10313
Start ATG: 4487

Transcript No. : CT22015
AGAGCGGACGTTTTTCGAGTCGGAGCCGGGTCGAGTCGAGGGCCCCAACTTGGAATTTTCTTTCCGATTGACTTGGAAAATAGCTTCTTCGTCGC
GTGCGAGTGTGTGTGTGTGTATGTGTGTGCGCGCGGTGTGGAGTTTATAAAAAGAAGTCGAAAAGTGTTTGCCGCATCAACGAAAATAAAAACAC
CCAAGAAGAGTGTTTGTTGTTTTGTCTGTATAACAGAAAACTGATTTTCTCAACTTCACCTCTGCACATCGATCAAGGACTAGATATAGATGCAT
CATATGTAGCCGAATTAAAGTATCTGCTACAGGACTAGTTGGAAAATGCCACAATGAATAAATAAATATTTTGATCAAAATAAGGAAGAGAGCCG
TGGTTAAATTTTCATACTGAGGATCACGTGGACAAGTGTAAGAGATCCCCTTAAAAAACGAACGAAAAGAAAAGCAACTGATTAAAGTCCCGGCC
GGAAGTGCCCCAGTGGAACGCGACCCCAACAACTGAGAGCCACATCGAGATGTTGGAGCTGCGGCTTATCGTGGTCATTGTGCTCGCCCTGCTCA
GCTGGCAGTGGGACCCAGTGGACTCCCAAAGACCGCCCCAGCATGGCCGACGTGATCGTCCGAAATATCCACCGAACAAGTTTATCAAGACTCAT
CCATGCGAGAGATCCTCCTGCTACCCGGCAACGGGTAATCTTCTGATCGGCCGAGAAAACCGCCTGACTGCCAGTTCCACGTGTGGTCTGCACTC
GCCGGAGAGATTCTGCATCCTGTCCCATTTGCAGGATAAGAAGTGTTTCCTCTGCGACACGCGTGAGGAGACCAAGCATGATCCGTACAAAAATC
ATCGCATCGGACAGATTATATATAAAACTAAGCCAGGCACCAACATACCCACCTGGTGGCAGTCCGAGAATGGCAAGGAAAATGCTACCATTCAA
CTGGATCTGGAGGCGGAGTTTCACTTTACCCATTTGATCATAACCTTCACCACCTTCCGACCAGCGGCCATGTACATCGAGAGATCCTTTGATTT
CGGACAGACGTGGCACATCTACAGATATTTCGCCTACGACTGCAAGGAATCCTTTCCGGGAGTGCCCACTGTCTTGGAAAACATCACCGATGTCA
TGTGCACCTCGAGGTATTCCAACGTGGAGCCCTCGAGGAATGGTGAAGTGATATTTAGGGTGCTGCCACCGAACATCAACGTTACCGATCCCTAT
GCGGAGCACGTGCAGAATCAGCTGAAGATGACCAATCTGAGGATCCAGATGACGAAGCTGCACAAGCTGGGAGACAATCTTTTGGATAGCAGGCT
GGAGAACGAGGAGAAGTACTATTATGGCATCTCCAACATGGTGGTTCGCGGATCCTGCTCCTGCTATGGCCACGCCTCTCAGTGTCTACCGTTGG

FIGURE SHEET 420

ATCCCGCATTTTCCCAGGCGGACAACGAAGATGGCATGGTGCATGGCCGATGTGAGTGTACCCACAACACCAAGGGAATGAATTGTGAAGAGTGC
GAGGATTTCTTCAACGATCTCCCATGGAAACCCGCTTTTGGAAAGAAAACGAATGCCTGTAAGAAATGTGAGTGCAACGATCACGCCGTTAGTTG
TCACTTCGATGAGGCTGTCTTCACTGCATCCGGTTTCGTTTCCGGCGGAGTGTGCGACAATTGCTTGCACAATACTCGGGGTCAGCATTGCGAGG
AGTGCATGCCGTACTTCTACCGCGATCCAGAGCAGGATATAACGTCCGAAAGGGTTTGCCAGCCCTGTGACTGCGATCCTCAAGGTTCGTCGGAC
GACGGCATCTGTGACTCCCTAAATGAACTGGAGGAGGGAGCAGTAGCAGGTGCCTGCCATTGCAAGGCCTTTGTCACGGGACGTCGTTGTAATCA
GTGCAAGGATGGTTACTGGAATCTGCAGTCGGATAACCCCGAGGGCTGCGAGCCGTGCACCTGCAACCCCCTGGGTACACTGAACAACTCCGGAT
GCGTTATGCGCACCGGCGAGTGCAAGTGTAAGAAATATGTGACGGGCAAGGACTGTAACCAGTGTATGCCGGAGACCTATGGTCTTTCGGAATCT
CCGGAGGGTTGCTCTCTGTGTAACTGCGATGCTGGTGGATCCTACGATAATTACTGCGATGTCATAAGTGGTCAGTGTCGCTGCAGGCCCCACAT
GACGGGTAGGTCATGTTCGCAGCCGAAGCAGAATTACTTCATTCCCCTGCTGCCCGAGGTTCATGAAGCAGAGGTGGTGGACGAGTGCATCTCGT
ATGGCGCCAACGGTAACTGCAGCCTGGTGGCCGAAACTCCTGATGGCAGTTTCACGGGCATTGGTTTACCAGGGTTCCTGAGAACTCGGAACTG
GTTTTCACTGTCGGAGATATTCCTCGATCCATGCCATACGATGCGGTTATACGTTACCAGAGCACTTCACGAGGAGATTGGGAGAACGCCTTTAT
CACTCTTGTCAGACCCGATCAAGTGGATCCTGAAGGAGGATGCGGTGAACTAGCTGCAGCAACTTCTTCGGAAACCAGGATTCCGTTCTCCCTTC
CTGATCGCAGCCGTCAGGTGGTTGCTTTGAATGAAGTATGCTTGGAAGCTGGAAAGGTTTATAAATTCCGGATTTACTTTGAGCGAAAGCGACAC
GATGTGGACAGTCCCACAGCGACGATCTTGGTGGATTCTCTTACGCTCATTCCCCGCATCGATGTAACGCCCATCTTCCAAGGATCCGTTCTGGC
TGATATTCGCAAAAAGGATTACGAAAAATACAATTGCAAATCCTCTTTGTACGATATGAACTACAAGTCGGATCCTAAATGTCAAAATCTGGACA
ATATCCTCAGTGTGTTTGTCCACGATGGAGCCAGTATGTGTAATTGCAATCCAACCGGATCGCTGAGCAAGGTGTGCGAATCCAATGGAGGTTAC
TGCCAATGTAAGCCCAATGTGGTGGGCAGGCAGTGCGATCAGTGTGCTCCGGGCACCTATGGTTTTGGTCCCGAAGGTTGCAAGGCTTGCGATTG
CAACAGCATCGGATCGAAGGATAAATACTGCGACCTGATAACCGGCCAGTGCCAGTGTGTGCCGAATACATACGGCAGGGAGTGTAATCAGTGCC
AGCCGGGCTATTGGAATTTCCCCGAGTGCAGAGTGTGCCAGTGCAATGGTCATGCGGCCACGTGTGATCCCATTCAAGGAACCTGTATAGATTGT
CAGGACTCGACCACGGGCTATAGCTGTGACAGCTGTTTAGATGGATATTATGGAAACCCACTTTTCGGCAGTGAGATCGGATGCCGACCATGCCG
CTGCCCGGAGACGGTAGCCAGTGGCCTGGCGCACGCAGATGGCTGCTCCCTGGACACACGGAACAATAACATGTTGTGCCACTGCCAGGAGGGAT
ATTCCGGCTCCCGTTGCGAGATCTGTGCGGACAACTTCTTTGGCAATCCGGACAACGGTGGTACCTGCTCCAAGTGCGAGTGCAGCAACAATGTC
GATCTTTATGACACTGGAAACTGTGATCGGCAGACGGGAGCTTGTCTAAAGTGCTTGTATCAGACGACTGGCGATCACTGCGAGCTCTGCAAGGA
TGGATTCTTTGGGGATGCACTGCAGCAGAATTGCCAGCAGTGCGAATGCGATTTCCTCGGAACGAATAATACCATAGCTCATTGCGATCGTTTTA
CGGGTCAGTGCCCCTGCTTGCCGAATGTCCAGGGTGTGCGTTGTGATCAGTGTGCCGAGAACCACTGGAAGATTGCCTCTGGCGAGGGTTGTGAA
AGCTGCAACTGCGATCCAATTGGAGCACTCCATGAACAGTGTAATTCCTACACGGGGCAATGCCAATGCAAGCCAGGATTTGGCGGCAGAGCGTG
TAATCAGTGCCAGGCTCATTACTGGGGCAATCCCAACGAGAAGTGCCAGCCGTGCGAGTGCGATCAGTTTGGAGCTGCTGACTTCCAGTGCGACC
GGGAGACGGGTAATTGCGTCTGTCACGAGGGAATTGGGGGCTACAAGTGCAACGAGTGCGCCAGGGGCTATATTGGGCAGTTTCCACACTGCTCA
CCTTGTGGCGAATGCTTCAACAACTGGGATTTGATTTTGAGTGCTCTGGAGGATGCCACAACTGCCACTATCCTACGAGCCAAGGAAATCAAGCA
AGTGGGAGCGACAGGAGCCTACACGTCCGAGTTCAGTGAACTGGATAAGAAATTGCAGCACATTAGGAATCTGCTGCAGAACACCTCGGTCAGTC
TGGTTGATATAGAGAAACTGGACTATGAAACCCAATCACTTAGGGACCAACTTCAGGCGTCCCATGGCCGATTAAGTGAAACCGAGCAAAACCTG
GATGACATTTACAATTCGCTAAGTTTGTCGGGCGTTGAGCTAGAGAGCCTACAAAATCACTCCAGATTGGTGCAACAACTGTCCAAGGAACTGAA
GGAAAACGGCATACAACTGCAGGAGTCAAATATCGAGGGAGCTTTGAACCTCACACGTCACGCCTACGAAAGAGTCAGCAATTTGTCGACCCTTA
AAGACGAGGCCAATGAACTTGCATCGAACACCGATAGGAATTGCAAGAGAGTGGAAAATCTGTCTAATAAGATTCAGGCCGAAGCCGATGACCTG
GCAAACAATAACAAGCTCATTGAAGACTACCGAGCAGAGTTGACTTCGCTAACCTCCCAAATTCCCGAGCTGAACAATCAGGTTTGCGGCAAGCC
AGGTGATCCCTGTGATAGTTTGTGCGGAGGTGCTGGCTGCGGTCATTGTGGCGGTTTCCTGTCCTGCGAACATGGCGCCAAAACCCATTCGGAGG
AAGCCCTTAAGGTGGCCAAGGATGCTGAGACGGCCATTACCAGCAAGAAGGATCAGGCGGACCAAACCATCAGGGCTCTGACCCAGGCCAAACTG
AATGCCTCCGAGGCATATGAGAAGGCCAAGAGGGGTTTCGAACAATCCGAGCGTTATCTGAACCAAACCAATGCCAATATCAAGCTGGCCGAAAA
CCTATTCATAGCCCTCAACAATTTCCAGGAGAACAAGACAGCTTCTCCTTCGGAGAGCAAAGAACTGGCACAGAAAACTCTCGACTTGGACCTGA
AACTGGAACCCGAAGAGATTGAGACCCTCGGCGACCAAATCAACAGGGCTGTCTCATCGCTAAAGAATGTTGAAGCCATAATCTACAGGACCAAA
CCCGATTTGGACAGGGTCAATAATCTGCAGAGCATTGCCAATGCCACCAAGGAGAAGGCCGATAAGATCCTGGACTCTGCCAATTCGGTCGTGGA
GAGCCTGGCGGCGGCAGATGAATCCCAGGGTAAAGCCAAGGATGCCATTCAGCAGGCGAACAGTAACATTGAGTTGGCCGGTCAGGATCTGGAGA
AGATCGATGAGGAAACGTATTCCGCCGAAGCTCCGGCCAATAACACAGCACAGCAGGTTGAGAAATTGGCCAAGAAAGTGCAGAAACTGCAGAAT
AACATAATGAAGAACGATCGGGATGCCAAGGAGATAACCAAGGAAGCGGGTAGCGTCAAACTGGAGGCCATGAGGGCTCGCGGAGAGGCCAATAA
TCTTCAGTCTGCCACAAGTGCCACCAATCAGACCCTCACCGATCGCGCCAGTCGCTCCGAAAATGCCAGGGAAAGGGCCAAGCAGCTGCTCCAGA
GGGCCTCCAAACTAACAGTCGATACGAACGCCAAGCTAAAGGATCTGAACGATCTGCAGACCGTCTATCTGAACAAGAACCAACAACTACTGCGA
TTGCAGGCCGAGATCGGCCCCTTGAACAAGGAGCTCAACGAGCACCTGATTCACATCAAGGAGCGGGGGTCGCACTACAGGCAGTGCTATACGTA
GATTGGGAAACATCCATTTGCGTGGCCATCTAAATTGCCATATTCATGAACAAATAAGCAAATTGCGAAATACGAGAATCAAGTAAAGAACTACA
AGAACAACTAGGAAGGCGACAGTTATTATGTAACCACTGTTAAGTTACCGTTACGTTTTGTACTCTAAGCGAAAACCAACACTGCAATGTTAATT
TTAAAAATTGAGCGAAAGAAATCGATGCCTTCACTTTTAATGTGTACACACTGAGCTAAGTTTTTCTTATACTATCCCTATACCATTTTGTAATG
CAATTAATGTAATTAAATAAAACTACTTAAATGTGGAAA
(SEQ ID NO: 776)

Start ATG: 525

MLELRLIVVIVLALLSWQWDPVDSQRPPQHGRRDRPKYPPNKFIKTHPCERSSCYPATGNLLIGRENRLTASSTCGLHSPERFCILSHLQDKKCF
LCDTREETKHDPYKNHRIGQIIYKTKPGTNIPTWWQSENGKENATIQLDLEAEFHFTHLIITFTTFRPAAMYIERSFDFGQTWHIYRYFAYDCKE
SFPGVPTVLENITDVMCTSRYSNVEPSRNGEVIFRVLPPNINVTDPYAEHVQNQLKMTNLRIQMTKLHKLGDNLLDSRLENEEKYYYGISNMVVR
GSCSCYGHASQCLPLDPAFSQADNEDGMVHGRCECTHNTKGMNCEECEDFFNDLPWKPAFGKKTNACKKCECNDHAVSCHFDEAVFTASGFVSGG
VCDNCLHNTRGQHCEECMPYFYRDPEQDITSERVCQPCDCDPQGSSDDGICDSLNELEEGAVAGACHCKAFVTGRRCNQCKDGYWNLQSDNPEGC
EPCTCNPLGTLNNSGCVMRTGECKCKKYVTGKDCNQCMPETYGLSESPEGCSLCNCDAGGSYDNYCDVISGQCRCRPHMTGRSCSQPKQNYFIPL
LPEVHEAEVVDECISYGANGNCSLVAETPDGSFTGIGFTRVPENSELVFTVGDIPRSMPYDAVIRYQSTSRGDWENAFITLVRPDQVDPEGGCGE
LAAATSSETRIPFSLPDRSRQVVALNEVCLEAGKVYKFRIYFERKRHDVDSPTATILVDSLTLIPRIDVTPIFQGSVLADIRKKDYEKYNCKSSL
YDMNYKSDPKCQNLDNILSVFVHDGASMCNCNPTGSLSKVCESNGGYCQCKPNVVGRQCDQCAPGTYGFGPEGCKACDCNSIGSKDKYCDLITGQ
CQCVPNTYGRECNQCQPGYWNFPECRVCQCNGHAATCDPIQGTCIDCQDSTTGYSCDSCLDGYYGNPLFGSEIGCRPCRCPETVASGLAHADGCS
LDTRNNNMLCHCQEGYSGSRCEICADNFFGNPDNGGTCSKCECSNNVDLYDTGNCDRQTGACLKCLYQTTGDHCELCKDGFFGDALQQNCQQCEC
DFLGTNNTIAHCDRFTGQCPCLPNVQGVRCDQCAENHWKIASGEGCESCNCDPIGALHEQCNSYTGQCQCKPGFGGRACNQCQAHYWGNPNEKCQ
PCECDQFGAADFQCDRETGNCVCHEGIGGYKCNECARGYIGQFPHCSPCGECFNNWDLILSALEDATTATILRAKEIKQVGATGAYTSEFSELDK
KLQHIRNLLQNTSVSLVDIEKLDYETQSLRDQLQASHGRLSETEQNLDDIYNSLSLSGVELESLQNHSRLVQQLSKELKENGIQLQESNIEGALN
LTRHAYERVSNLSTLKDEANELASNTDRNCKRVENLSNKIQAEADDLANNNKLIEDYRAELTSLTSQIPELNNQVCGKPGDPCDSLCGGAGCGHC
GGFLSCEHGAKTHSEEALKVAKDAETAITSKKDQADQTIRALTQAKLNASEAYEKAKRGFEQSERYLNQTNANIKLAENLFIALNNFQENKTASP

SESKELAQKTLDLDLKLEPEEIETLGDQINRAVSSLKNVEAIIYRTKPDLDRVNNLQSIANATKEKADKILDSANSVVESLAAADESQGKAKDAI
QQANSNIELAGQDLEKIDEETYSAEAPANNTAQQVEKLAKKVQKLQNNIMKNDRDAKEITKEAGSVKLEAMRARGEANNLQSATSATNQTLTDRA
SRSENARERAKQLLQRASKLTVDTNAKLKDLNDLQTVYLNKNQQLLRLQAEIGPLNKELNEHLIHIKERGSHYRQCYT*
(SEQ ID NO: 777)

Name: lamininB1
Classification: cell_adhesion
Gene Symbol: LanB1
FlyBase ID: FBgn0002527

Celera Sequence No. : 142000013384840
AGCCGCCGAAAAGCATCCTTAATCTCACTGTCGGTGGCATTTCTCGGTAAGCCCAGAACCTGGTAGTGATCTTCGTAGACATCGCTCATTTTGGC
CAATTGGTCTATTTGATGGGAGAATAATTAGATGATTTTATCGATAGTAGCACGATGGTCAGTGGTTTTTGGTGCAGAAGTCGGTATTTATTGAT
GTTTATGTTGCGGGATGTAAGGCACTGGGAAAACCTGAGAAAACACTAAAGCTGATTCTTTCATTACAAATAGAGATGCACATCTGAAATGTGTG
TTATCTTTGTATGGAAACAACATCGATAAATACATCGTGTCATTTGTCGTGTCATCGTGTCAGCGAAATAATATTCGCGACAAGAACATATTGTT
TAAGGAAAATAAATGCGTCTTTCGTTTCTTCATTTGCCATCATATTTTATTGAGAATACGAGTCATTAGGTGGCCAACAGAAACAAAATCTAGAA
AAATATGTCTTTTTTTTCAGAACAAACCATTATATTTCCGTCTTATCTGGTACATACCAAAGACACTAGAATATTCTAGTGTTATTCTATTCTAT
TCTATTATTATTATTCTAGTGTCTTTGTACATACTATATGTAGTAGCAGACTGGCTCTGCTTAGCAACAATTTGTAATAAGCAAGTGCATTTAAT
TTTCTCTACTATGGCATTGTTATATTTTTTACTATTTGTATCGCATAAACGTTTTTTAAATTAAAAAAAAAACAAAACTATTAGTTCGTCTTACAG
TATTTATCCGTTTTATCATTCGATTTGGCTAAAGGTATTAGCTATTTTCGAGCAACAGTCGGACGAATTCCATAATTTTTATTTATCTTACTAAA
TAAATAAATAAATTAATCAATAAGTAACGCAGGATTCATTAGATAAACAGTCAATAATTAAGTTCCTATAAATTAATCTTAAAGACTATTCAGCG
AAGAACGCTAGGTACCCGAGATTGCTTCATCAAGCCCTTGGATCCTTAGCTCAGTCCGAGGAGGATCCATCGCCGTGGGTAGCCTCTTTTTTCCG
GTTGAAGAACTGGAATGTCTTGTAGGCGGCGAACGCAAAGAGCACGGTTCCTCCGACGGCGCACATGAAGGGGAGCATGTCTGGCGTGGGCTGGG
CGAAGGTCGCAGCAGGCTCGTCATCACATTTGAGACCCTCCTCGCCGTGCTGGTCGTATATCTCGCGCTTTTCCTTATCAAAGAGCACTTCGAAG
GCGGCCACCACCTCCCTAAACTGCTCCTCGGCCTGCGGATGGTCGTTCTTGTCCGGATGGTAGCGGAGAGCCATCCGGCGGTATCCCTTCTTGAC
GTCTTCGCTGGACGCATTCCTCTCGATGCCCAGAATCTTGTAGTAATCCTTACCCATTGTGGTGAAATGGTATTCTCCTTGTTCTGGCTGAGATG
GTCGTCTAGCGGTGTTGCGCCGTGTATGGAATGTGAGGCAGCGTCTCGACTTGTTGGTGCTTATGTGGTAATGCGAGTATATATTGCTGATTCGA
TTCGCTGATTTAAAACATTATTACAAATAAACAGTCAATCGATAAATTATCGGCCGCCAGTGGCCAGAGTGACCCTACCTTACCACCAGAAGCAC
TGTTAGTTAACAGAAGAGATTCTGACGATCGTAGCAGCTGTATAGGAGCACTATTAGCCTATTAGTAATTAATGATCTGTTAAATCTATCTTTTT
TGAGTACTTTAAAAGGAATTACACATTTCGAAAATAGAAAATATTCATATCGCTTACCGGTTTTGGTATTTTTTCAGACCGTGCGGTATCTTATT
CGCCATCGAAGCGGTCACACTGGGTGCCGCCGCCAACTTCACTCTTTCCGTTCTGTGAGCGAAAACCGAAAAGTCTGTGCTTTGGTAAGTGTTGC
TAAAAGTTCGGAATAATGTTGCATCCCGAGCATTTTCGGGTACATAACTGTTCCACGGCGGTGGTCCAGCAAAGACTAATCGTTATCACGCCTTT
CGCAGTTCTTAAATTCACCCGACGAGTCCCTAATACACAATTAAAATGGTTAGGGAGAACAAGGCAGCGTGGAAGGCTCAGTACTTCATCAAGGT
TGTGGTAAGTATAGAACCTTATAGAATTCGCTCACTAGCTGGCGCCTGGCTTATGCTGTTAACTGATCCCTCCTCCAGGAACTGTTCGATGAGTT
CCCAAAGTGCTTCATCGTGGGCGCCGACAACGTGGGCTCCAAGCAGATGCAGAACATCCGTACCAGCCTGCGTGGACTGGCCGTCGTGCTTATGG
GCAAGAACACCATGATGCGCAAGGCCATCCGCGGTCATCTGGAGAACAACCCGCAGCTGGAGAAGCTGCTACCCCACATCAAGGGCAACGTGGGA
TTCGTGTTCACCAAGGGCGATCTCGCCGAGGTGCGCGACAAGCTGCTGGAGTCCAAGGTGCGCGCCCCCGCCCGT
(SEQ ID NO: 778)

Exon: 1450..1001
Start ATG: 1387 (Reverse strand: CAT)

Transcript No. : CT22047
ACACGGCGCAACACCGCTAGACGACCATCTCAGCCAGAACAAGGAGAATACCATTTCACCACAATGGGTAAGGATTACTACAAGATTCTGGGCAT
CGAGAGGAATGCGTCCAGCGAAGACGTCAAGAAGGGATACCGCCGGATGGCTCTCCGCTACCATCCGGACAAGAACGACCATCCGCAGGCCGAGG
AGCAGTTTAGGGAGGTGGTGGCCGCCTTCGAAGTGCTCTTTGATAAGGAAAAGCGCGAGATATACGACCAGCACGGCGAGGAGGGTCTCAAATGT
GATGACGAGCCTGCTGCGACCTTCGCCCAGCCCACGCCAGACATGCTCCCCTTCATGTGCGCCGTCGGAGGAACCGTGCTCTTTGCGTTCGCCGC
CTACAAGACATTCCAGTTCTTCAACCGGAAAAAAGAGGCTACCCACGGCGATGGATCCTCCTCGGACTGA
(SEQ ID NO: 779)

Start ATG: 64 (Reverse strand: CAT)

MGKDYYKILGIERNASSEDVKKGYRRMALRYHPDKNDHPQAEEQFREVVAAFEVLFDKEKREIYDQHGEEGLKCDDEPAATFAQPTPDMLPFMCA
VGGTVLFAFAAYKTFQFFNRKKEATHGDGSSSD*
(SEQ ID NO: 780)

Classification: chaperone

Celera Sequence No. : 142000013384534
AACAACAAGTGCTACACGAGCAACCCCAACAACAACAACAACAACAACAATAACGGCGGCAGCAACAGTGGCAACAACAACAGCAGCCCGAGTGT
AAACAACTTCAATTGTGATAGTGTCGCCGGTAATGGACGTTACCTGCACGGCGGACACCAGCATCCGCATCCGCACCAGGCGGGATTTGCAGCGG
TTGCCGCCGCCGTCGGAGCAGCTCCCTCCGCCCTGCAGAGCCTGCAGCAGCTCCACCAGCAACACCACGCTCAGCAGCAGGCCACCCTGAGCTTT
CAGCGGGAAAAACTCAAGTCGGGTAAGCAGGTGTTTCAGTCGATGAATAACCCATGATTTGATCATAAGTGGGTATTAAGTAAACATAGTGTGTG
CACATCTAATACCTCCATTTGATCATCATTTTGTGATTCGGCAGATTCTCACAAGAAGAGCGCACTGAAGAACAAGCGCGTCCGGACAATCTTCA
CGCCGGAGCAGTTGGAGTGCCTGGAGGCGGAGTTCGAGCGCCAGCAGTACATGGTCGGCCCGGAGCGGCTCTACTTGGCACACACCCTAAAGTTA
ACGGAGGCTCAGGTGAAGGTGTGGTTCCAGAATAGGCGGATCAAGTGGCGCAAGCACCACTTGGAACTGACACAACAACGGCTGGCATTGATAAG
GCAAACTCAACTGCCAGGTACATCGTTATTGGGCAATCAAGTATCCGTGTCGGCCAATGCGGCCCATTCTGTGTCCACGGAACGCACAAACGGAT
GCAGTGCAGCCTCGCCCAGCCTGCAGGAGGAGGACAACGAGGATAGCAAGCACTCGCTGTCGCTTTCGGGCGCATTACCGCCGTTGAGTCGAGCG
CAGTCCGAGTCGGATTTGTCCATCTGTAACGATTCCCTGGACGGCGACAGCCTCATGGACGGCAGCGAGGAGGCCTAAAAACCACGCCAGTGCAA AGCAAGTTTCCTGTAAATATAGTCAAATAAATATGTACAATATCGGTTTTCTATACTTCTGCTTGTCTTTAATTGTTGATGATTAGCTGCAAGTT
GATTGTTACAATCAATCAATGCAAACTATATTATATTGTATAAGCATTGCAGTATATCCATTACATACGAGTACTGAAAAAGCTTATTTAAAAAC
AGAATAATACAGACATTTACACTCAATTCGCACTTTATACCTTGATCAGTTATCACATTGGAGTATTTCACTTATTGCTGAGCAGCCGCCCTGGC
GAGCCGATCGTGGCAGGATAGGTGCACGATGTGCCCATTTGGATAGCGCACGAAGGCGGACTGGGTTTGAAAACGCTTCTTGCACTCGGAACACA
CACTAGACTCGTTTAACTCGAAGCTAATGTTTCGCTGCTCCTCCAAGGCATTCTCCAGGCGCGTGGACTCTGCCTCCAGGAAGCCGCACATCATC
TGCATCTCGTGCTTGTCGGCCATCATTTACGTATAGATTTCTCCAAGTATTTCTCCAGCTGGGGCATGGGCATGTCATCGGGAAGGTGCTGCAA
AATCCAAAATGGTTGAGAAATATTTCTAATAAGTCATGCATTCAATGCATTCTTCACCTCGAAGATCTCGAATGGATCGATTCTGGTGGCGTGGG
TGTTAAGTATTTCCAGGGCCACCTCTCGATTCACTTGCGAGAAATCCGGATGCAAGGGCACACCATCATAGAGCGGTTGAGTTGGTGGTATTAAT
ATGCACTTAATGAGCGTGTGAAATATGTGCTTGTCCTCTTTGTAATGGGCTTCCGCATAGGCCGTTGCCTTGGCCACATCTCCGAGAACATGAAT
ATAGATGGACAGGACGTTGTCGTGCTTTTTGAGCCTGCCCAGGATTAGGGCACGCTCCTCCAAGAGTATATTGGTTGGAAATTCCTCTAGGAGGC
GATCCGGCGAATAGTCGTTGGACTCCTCCAACATCTTGTAGAGCTTGGCTCGCATCGGAATGAGTTCGGGAACTTCCTCTCTAGAAAACAGGTGA
GTATAAGCATTTTGATCCAGTACAATGACAGACTCTCACCCTTTTTCCTGCTGAGCAAGAAGCCGTTGCACCTTTTCGCGATACTGCTTGAGGAG
CACATTGTGGAGCAGGGTGTTGCCGTCCTTCCATTCAGTGATTACGTGCTCCAAATAGGGAATGACAAGTGCTTTGTGCTTGCTAATAAAAAAAT
CAAGAACTTTGGCGCGCGGCAGGGATTCCACTTCAATAAGTTCGTCGGTGAAAATGGTTAGGCCTTCCTCGGGATTATCGTTTAAGACCCAGTCA
GCGAACTCAAAGATCAGCGGCAGATGATCACCACCCAGCTCCTGAAGATAGCGTATGGTACGCTTGCGACCCTGCAGCACAGATCCTTCGATGCT
CGCCTGCTCTCGAAGCAGTTTAAGGGCCTCCTTGTGCTTGCCCTTCATCTGGTAGAGGATGATAAGTTCAGAGATCTTGTTGTGCTTCTTCAACG
TCTTTTCCGACTCCTCTAAGTGGCACTGGTTTAGGCGTAGCAGTGGTGCCACCAGAGAGTCGTTTGTCTGCAGGTAACACTTCAGCAACGTTGTA
TCGATGATCTCCAGCAGGGACTTTGAACTACTTTTAGTGTCGCGCAGCTTGACCACCTCCCGCTGTCGGGCCCATGCCAGATACTCGATCAGTGC
CAAGTAGGCGTTCTCCAGGTCGCTATCCTCAAGCGCCGGAGTACTGGACGTAGGCACGGTGACATCTTCGGTGCCGGGCTTTGGTTCTGGCACCA
AGTTTGGGAACAGTCTTATCACATCGTAGGGATCTATAGCCGCCTTTTCAAACTCCTTCATGGCCGCCGAGAACTCCTTATTGGTAAACAGCTCT
TTCGCATAGAGCATGTGTATCTGGCGAATGGTTTGGGCTCGGTCCGCGGCAGGTTCATCGGAGATTTGCTGAACATAAAGTTTGTTGTAGTCGTC
GTATTTTGATTTCGTTTATCGGACTCACCGTCAGCTCAATAGCCAGTTGGAATTTCTTTTGCTGTAGCAACTGCTGACGCTGGATAGGGATTTCC
ACCATTCGAATGCACCAAAGCTCGGAGGTGGCGGCGGCAAAGATGGTTCCCTTGTCGGCGTGAACCAGGAATTTCGTCTTCTGTAGCTCGGGAAT
GGTCTGGACCAGGGTGTCCTTGCCCACTAGGCTGCGCACCTCGATGGCGTTGTTGACACGACCCACAGCGAATGGCTCATCCCAGACTGTAATGA
AGATAATGTGATTTAGAAATTGGCTTGAAGTGAATAGTGAGTATCGTACCCAGATCTAAAAGCGGACTTGACCAGAGCAGAGGAGTTAGGGAACT
ATTGCTGTCCATGGCAGCTGGCCGGACATCTGTTGAGTTATTGATTCCATCCGATTCTTTGTACTGACTCGGATCTACTACGACGAGGTAGCTGT
CCTTAGAGATGCCCAACATGTTGTTCCGGATAAGGCAAATGCAGGGATCTCTGCTGATACTAGAGGAGGTAAGGAAGAGGTTGTGCTTCTTTGGT
GCTTTTCCTGATATCTAGAATTGGATATGCAGACCTTTAAAATACGAAGTAAATCGACTTTAAAGCATTTCTCACATCGTAAACAACATATTCGT
CTTTGAAGCCCACGCAGACAGCATGGCCCACCCAGCACAGTGTCCTGGGCACATCGCTGAGCTCGATGATCAATTCCAGGGAATTAAGCTTGTCC
TCCTTCCAAAAGAAGAACACAAGACGCCGCCGGATAGCGCAGCACACCCGTATGACGGTGGCCACACGTCCGGTTGTGGACTTCGGCGTGTCCAC
GTCCATGGTGAACAGGGTGCATCCCTTCGTGTCGGGCGCACTGTGCATGAAAGCGAAGTTGCTCTCAATCCGCCGAATGTCGCACACCTGCACCT
GTAAGTCGGTGAGTACGAAGAGCAGGTTCTCCGAGGCAATCACTTCCATTTGGGTGATCGGTTTCCGGCTGAAGTTCTTGTTGAACATCCGCATG
TCCACGCCCGTCTCCTCGTCCACAGAGTACATGATCAGCTGTCCGCTGCGGGTGCCCAAGATGACATGGTTGCCTGAAAAAATGCGTCCGGTGAG
TAATAGCTGTGCACCGAAAATTCCACTCACCATATGCCGCAATTGACTCTATCTGCACGCCCTGTTTCAGGATCGAGTGAACACTGTAGGCCTGG
TGCATCTTGGCCAAGTGGAAAAACTTCGGTCTCCTCCGCCTCAATTTATTTTCGTAAAAAAGCTTATAAACAAACCAGATGGGAGTACCACTAAT
GATAGCTGATGATGATAGATATCGATAGCTTTAGCGGTGGTAAATCGATTTCTTCCTCTTATGGTGATAGCGAAATAACTTAAATATACAAAGTA
GAAAATAAAATTTGTACATGTTATAATTTAAGATTCAATCGCTAATGACTAAAAAGTTGAGTGAAATTTTAAATTACGATACTTTAAACGAATGC
TGCCAGACTCTGCATTGCTGTCGATAGCACCAGTTCGATATACTGGTTCCCCGCGAAACCGTCCACCTCTAGTCCTTTTCACTTTAGCGAGGCGA
AATTGTCACATTTACATTTGACAAAATTGTAAGTTTTGAAACAACTCTGTCGCTTTATTTCGGGTTGAATGTTTTCATTGCATTACTACCCACCC
AGTGAAGTCGTTGAGTAACAGTTTTACCCCGTTCCCGCTCCAGGGTCGCCAACAAGCCCGCAGACAGCAACAACATCGAAAGTAGCTGCACAGCA
ACAACAGCAAACAGCCAAAATGCCCAAGAATAAAGGAAAAGGAGGCAAGAATCGTCGTCGTGGTAAGAACGAGAACGAGTTCGAGAAGCGTGAGC
TGATCTTCAAGGAGGACCAACAGGAGTACGCGCAGGTGACCAAGATGCTGGGCAACGGTCGTCTGGAGGCAATGTGCTTTGATGGCGTCAAACGC
CTGTGTCACATTCGGGGGAAACTTCGCAAGAAGGTGAGTGCTGCTCTGACTACGCTCTTTGTTTCGCCTGTGCTCTCTTCGCTTGCGTTGAGTGG
GTGCCCCTCTCTAAGGTGGCTCTCTTAAGCCATTTTGGCATTGATTGCCAGCGAATGCTACGTATTTACGTTATTGTTTTTGTTGAAATGCAGGC
AGTTTTTGTGATTTTGGGGGATTTTGCATTACCCTGCTAACTTTCGACCTTTCTATACCTAATTTTCAACTCTCTTTTTCTGCAATTCTCTTTTA
CTGGTCCATTATTGAGTGGGTGTCATCGTCCTTGTGC
(SEQ ID NO: 781)

Exon: 4262..4116
Exon: 4063..3591
Exon: 3529..3280
Exon: 3221..2974
Exon: 2918..2035
Exon: 1980..1578
Exon: 1514..1001
Start ATG: 4185 (Reverse strand: CAT)

Transcript No. : CT22081
CCATCTGGTTTGTTTATAAGCTTTTTTACGAAAATAAATTGAGGCGGAGGAGACCGAAGTTTTTCCACTTGGCCAAGATGCACCAGGCCTACAGT
GTTCACTCGATCCTGAAACAGGGCGTGCAGATAGAGTCAATTGCGGCATATGGCAACCATGTCATCTTGGGCACCCGCAGCGGACAGCTGATCAT
GTACTCTGTGGACGAGGAGACGGGCGTGGACATGCGGATGTTCAACAAGAACTTCAGCCGGAAACCGATCACCCAAATGGAAGTGATTGCCTCGG
AGAACCTGCTCTTCGTACTCACCGACTTACAGGTGCAGGTGTGCGACATTCGGCGGATTGAGAGCAACTTCGCTTTCATGCACAGTGCGCCCGAC
ACGAAGGGATGCACCCTGTTCACCATGGACGTGGACACGCCGAAGTCCACAACCGGACGTGTGGCCACCGTCATACGGGTGTGCTGCGCTATCCG
GCGGCGTCTTGTGTTCTTCTTTTGGAAGGAGGACAAGCTTAATTCCCTGGAATTGATCATCGAGCTCAGCGATGTGCCCAGGACACTGTGCTGGG
TGGGCCATGCTGTCTGCGTGGGCTTCAAAGACGAATATGTTGTTTACGATATATCAGGAAAAGCACCAAAGAAGCACAACCTCTTCCTTACCTCC
TCTAGTATCAGCAGAGATCCCTGCATTTGCCTTATCCGGAACAACATGTTGGGCATCTCTAAGGACAGCTACCTCGTCGTAGTAGATCCGAGTCA
GTACAAAGAATCGGATGGAATCAATAACTCAACAGATGTCCGGCCAGCTGCCATGGACAGCAATAGTTCCCTAACTCCTCTGCTCTGGTCAAGTC
CGCTTTTAGATCTGGTCTGGGATGAGCCATTCGCTGTGGGTCGTGTCAACAACGCCATCGAGGTGCGCAGCCTAGTGGGCAAGGACACCCTGGTC
CAGACCATTCCCGAGCTACAGAAGACGAAATTCCTGGTTCACGCCGACAAGGGAACCATCTTTGCCGCCGCCACCTCCGAGCTTTGGTGCATTCG
AATGGTGGAAATCCCTATCCAGCGTCAGCAGTTGCTACAGCAAAAGAAATTCCAACTGGCTATTGAGCTGACGCAAATCTCCGATGAACCTGCCG
CGGACCGAGCCCAAACCATTCGCCAGATACACATGCTCTATGCGAAAGAGCTGTTTACCAATAAGGAGTTCTCGGCGGCCATGAAGGAGTTTGAA AAGGCGGCTATAGATCCCTACGATGTGATAAGACTGTTCCCAAACTTGGTGCCAGAACCAAAGCCCGGCACCGAAGATGTCACCGTGCCTACGTC
CAGTACTCCGGCGCTTGAGGATAGCGACCTGGAGAACGCCTACTTGGCACTGATCGAGTATCTGGCATGGGCCCGACAGCGGGAGGTGGTCAAGC
TGCGCGACACTAAAAGTAGTTCAAAGTCCCTGCTGGAGATCATCGATACAACGTTGCTGAAGTGTTACCTGCAGACAAACGACTCTCTGGTGGCA
CCACTGCTACGCCTAAACCAGTGCCACTTAGAGGAGTCGGAAAAGACGTTGAAGAAGCACAACAAGATCTCTGAACTTATCATCCTCTACCAGAT
GAAGGGCAAGCACAAGGAGGCCCTTAAACTGCTTCGAGAGCAGGCGAGCATCGAAGGATCTGTGCTGCAGGGTCGCAAGCGTACCATACGCTATC
TTCAGGAGCTGGGTGGTGATCATCTGCCGCTGATCTTTGAGTTCGCTGACTGGGTCTTAAACGATAATCCCGAGGAAGGCCTAACCATTTTCACC
GACGAACTTATTGAAGTGGAATCCCTGCCGCGCGCCAAAGTTCTTGATTTTTTATTAGCAAGCACAAAGCACTTGTCATTCCCTATTTGGAGCA
CGTAATCACTGAATGGAAGGACGGCAACACCCTGCTCCACAATGTGCTCCTCAAGCAGTATCGCGAAAAGGTGCAACGGCTTCTTGCTCAGCAGG
AAAAAGGAGAGGAAGTTCCCGAACTCATTCCGATGCGAGCCAAGCTCTACAAGATGTTGGAGGAGTCCAACGACTATTCGCCGGATCGCCTCCTA
GAGGAATTTCCAACCAATATACTCTTGGAGGAGCGTGCCCTAATCCTGGGCAGGCTCAAAAAGCACGACAACGTCCTGTCCATCTATATTCATGT
TCTCGGAGATGTGGCCAAGGCAACGGCCTATGCGGAAGCCCATTACAAAGAGGACAAGCACATATTTCACACGCTCATTAAGTGCATATTAATAC
CACCAACTCAACCGCTCTATGATGGTGTGCCCTTGCATCCGGATTTCTCGCAAGTGAATCGAGAGGTGGCCCTGGAAATACTTAACACCCACGCC
ACCAGAATCGATCCATTCGAGATCTTCGAGCACCTTCCCGATGACATGCCCATGCCCCAGCTGGAGAAATACTTGGAGAAATCTATACGTAAAAT
GATGGCCGACAAGCACGAGATGCAGATGATGTGCGGCTTCCTGGAGGCAGAGTCCACGCGCCTGGAGAATGCCTTGGAGGAGCAGCGAAACATTA
GCTTCGAGTTAAACGAGTCTAGTGTGTGTTCCGAGTGCAAGAAGCGTTTTCAAACCCAGTCCGCCTTCGTGCGCTATCCAAATGGGCACATCGTG
CACCTATCCTGCCACGATCGGCTCGCCAGGGCGGCTGCTCAGCAATAAGTGAAATACTCCAATGTGATAACTGATCAAGGTATAAAGTGCGAATT
GAGTGTAAATGTCTGTATTATTCTGTTTTAAATAAGCTTTTCAGTACTCGTATGTAATGGATATACTGCAATGCTTATACAATATAATATAGT
TTGCATTGATTGATTGTAACAATCAACTTGCAGCTAATCATCAACAATTAAAGACAAGCAGAAGTATAG
(SEQ ID NO: 782)

Start ATG: 78 (Reverse strand: CAT)

MHQAYSVHSILKQGVQIESIAAYGNHVILGTRSGQLIMYSVDEETGVDMRMFNKNFSRKPITQMEVIASENLLFVLTDLQVQVCDIRRIESNFAF
MHSAPDTKGCTLFTMDVDTPKSTTGRVATVIRVCCAIRRRLVFFFWKEDKLNSLELIIELSDVPRTLCWVGHAVCVGFKDEYVVYDISGKAPKKH
NLFLTSSSISRDPCICLIRNNMLGISKDSYLVVVDPSQYKESDGINNSTDVRPAAMDSNSSLTPLLWSSPLLDLVWDEPFAVGRVNNAIEVRSLV
GKDTLVQTIPELQKTKFLVHADKGTIFAAATSELWCIRMVEIPIQRQQLLQQKKFQLAIELTQISDEPAADRAQTIRQIHMLYAKELFTNKEFSA
AMKEFEKAAIDPYDVIRLFPNLVPEPKPGTEDVTVPTSSTPALEDSDLENAYLALIEYLAWARQREVVKLRDTKSSSKSLLEIIDTTLLKCYLQT
NDSLVAPLLRLNQCHLEESEKTLKKHNKISELIILYQMKGKHKEALKLLREQASIEGSVLQGRKRTIRYLQELGGDHLPLIFEFADWVLNDNPEE
GLTIFTDELIEVESLPRAKVLDFFISKHKALVIPYLEHVITEWKDGNTLLHNVLLKQYREKVQRLLAQQEKGEEVPELIPMRAKLYKMLEESNDY
SPDRLLEEFPTNILLEERALILGRLKKHDNVLSIYIHVLGDVAKATAYAEAHYKEDKHIFHTLIKCILIPPTQPLYDGVPLHPDFSQVNREVALE
ILNTHATRIDPFEIFEHLPDDMPMPQLEKYLEKSIRKMMADKHEMQMMCGFLEAESTRLENALEEQRNISFELNESSVCSECKKRFQTQSAFVRY
PNGHIVHLSCHDRLARAAAQQ*
(SEQ ID NO: 783)

Classification: hypothetical

Celera Sequence No. : 142000013384235
CATGTTGTTGGTTCGGTTTGCTCCTGGTCGCCATTTTCCTGCAGCCATCCGCGAGCCAATACTACGGTTATCCCTATTACGGCGGCGCTAATGCG
GGAGCGGGATCGGGATACGGGAACATATACGGCAGCGGCATGTACGGATACCCCTACAGCTACGGCGGATATCCGTACTACTCGTATCCCGGCTA
CAACCCGTACTCGATGTACGGTGGATACGGGCAGTACGGATACCCCTATGGAGGATATCCCTACGGCGGCAATGGCATGAGTGAGTTTCCCGACT
GATAGCACCTCGGTGCCTAGCACACAAGTAATCTACAAGTGTTTTGGACCTGTTTCTTCCTCTAGACGTGGCCTACGCCAGCAGCAGTGGAGGAT
TCGCAACAGCCAGTGCGGGTGGAAGCGGATACTACGGCTAGGAAGCGCGAAACCTGATATAGTTTAGTGATAGGTATACGGTTAAGTCATCCTAC
CCCATAAGTGTGTTAGTGCTAATAAATATGATATTTATGTTCTATAAGTCAAGACTTATTCTTATGACGTGTCCAAAACTAGTGTACCTGGTAAA
AAATTGTACACCTAACTAGTGCCTTCATGTATACCACCATAATTTATTAGCTCCCGGAACTGATGTGATAATTTGTATGTCTTTTAGCACATTT
GACCCTATGTATGTTCCGCCAAGTTTATGCTGCCATGACTCTTTGTGGGATCATTAGATCCTTTTCTCAGCTTTTAGCTTTGAGTCAATAACTAC
GTACGCATATCTGGTCGTTTTAATAGTTATAAAAAAGCCTTGAGGCTGTGATCCCATATATAACCATATACCGAAAAATATTTTTTGCTTCGTGA
TAACAAATCGACAAAGTTTGATCCATGTGCATTCTTGGCGCCTTATCGATAGCTATGGACAGTGTTGTAAGGTGCACGATAGTAAGGGGGGCAAA
ATTGTATCGGTCTGCCGATAGTTCCCGGCCGTTAGCCAAGTCCAAATTCGACCGACCGACCAATAGTCTCGCAAAACACAAAACAAAGGCACACC
ACACTTCGTGCTCTCGCCGAATTCCGCCGCCGTCGCCTGAAACTCACACAAAGTAAGCCCGAAATCAGTGGAAAAGCGCCGAATAGTCGAATTGC
AGGTTCAAATGGGATGGACGGCGACTTAAAAGGCGGAGGCCAATAGGCGGCATAAAAACATTGTATTGCGTAATTGGGGCCAATAAGAAAAGCAA
AAAAACAAAGCCAACCGACTGCATTCTATTGCGCCTGTGTGTGTGCTTGTGTATCTACAGCTGAGCAGTAAATAAATTTGTTTTACATTTGGCCT
CCAAAGGCAATTTCTCGGTGTTCCCGCTCCCTGCGTTTCCATAAACTTCCTCTCCTTTCGCATTAATATCAATGTCTTTAGTTCATCGTTACATA
TTATTAAGCACTTAACAAGCAGTGAGTGGAAAGAGGAAGACAAATAGCCAAAGTATGCTTACGTTAAAAGAGCTTGTTCCACATATTCGCCACCT
TTCTCCCGCACTCTTCCTCTCCCACTCTATCAGCCATCTCTATCCCTCTCACAGGGGCTGCTCACGCGCACCGTGGGGTGTTTTTTCGATTCTCT
ACCATTTTCGCTGCTATTGCACCCCTTCCCCAGCATTTGTGCCGCTTAATTTCATAAATCAAGGCAGCGTCAGTTAAAAAACACAAGAACTACAT
ACGTATGTACTTCTGCCCACATCCCCTTCAGCCACCTTCTCTTCATCTTTCTGGTTTCGGCAATGGGAAATTTCCGTAGCCACCGCACAGTGGAA
AGAGACAACAGCACGCAATTTAAATTACAAGATTGCAATCTCGCTTTTTGGCAGTTGGTTAAATTTTCATCGAGACACAAGCTGAGCCAAATAA
ACATTCACTTTTTAAACGAACAGTGCACACGAATTGGGTAGCAATGCCTTGTTCTAAACATAGTGTAAAATGTTTTTAAGATAATTTTTATTTTT
TAGTCCAGCGTTCAAGGCACTCGACAAATAAAACAGCATTCATAAATTTACTAATTTGCGATTAACTAGATTGTGCCAGCTTTGACACGCTCTCA
TCCCACTGTGCGCTTCGTAGACAGAACAGCTGATGCTCGTCAAATTTTAGCTTCTGCTTGTGCAAAAAGCGCTCTGAGTGCGCTTGTGTGTGAGT
GCGTGTGTGAGCATGGGAAAGGGAACGTGGTTATCGATAATAAAGTAAACTGAAAATAAATCAGTCATCCGCTCGGTTGACCAACTGCCCAAGTT
AGTGCACCTTCTAGAATTTCTTGCAAGTGCACATTCTTTTGGTTCGCAGTGTTTCTGTTTTGCGCCTTATCTGGGGGGTGTGTCGTCGTCGGGAG
CTTCACGTTTGGCTGGTTATCAAAATCACGCGACTTGACGCGGACCCCCAGTGAATTGCCAAGGTTGCTGATAAATGAATACTAATCAAACGTTT
GCTCTTTTCGCGGGCCTATCGCTCAGATAGCAAAATTCTAGGTGGTACGAGCCGACGACGACGAAGAATCTGAGAGACCGCTTATATAATCCGGC
AGCGAACGAGACAGGCCCCAAATCCCGACAAGATGTTGCGAATGATGCGAAGTTCCTCCTCCAGATGCTCTAGTCTTCAGCAGAGCTTGTTGAAA
AGGTATGCCTGAGGTTATATCCTTATATTTCATAATTTACAACTGACACAATATGTATAAGTAACCATATTATGCATACACTAGCTAGTAGTTTA
TTAGTTTTATTACATTGAACGCGCTTCATTTTTATCAGTTCGACACGCTGTCTGGGTTCCGTTATACCGGACCTTAAACTGAAGGACTTCCCGAT
CGCCAATGAGCCAATCCTGGGATATCTCAAGGACTCTAAGGAGCGTAAGGCCCTCGAGCAGGCTCTAAAGGGCACGGCCTCGAGTTGCGAAGACA
TCCCCATCGTGATCGGCGGCAAGGAGTACAAGACGCCGGAGGTTCGATACCAGGTCATGCCCCATGACCACCAACACAAGCTGGCCAGCTTCTAC
TACGCCGACAAGAAGCTTATCGAGAAGGCCATCAAAACGGCGGTGGAAACACAGCCCAAGTGGGACCGTGTGTCGATTGCAGACCGTCTGAAGAT CTGGGAGAAGGCAGCGGACCTAATGGCAACGACGTACCGCCAGGATCTCAACGCCGCCACCATGCTGGGTCAGTCAAAGACGGCGATTCAGGCGG
AAATCGATTCAGCAGCGGAGCTTATCGACTTTATACGGTGAGTGTCCCCATAATTTATTACAAGGAACATGCAGAACCAGAACACAATCTGTTCC
AATCGATTTTTTTAAAGGATTTTCCCAATGGAAGAAGCAATCATTTCCTCATTATGATATTCAATATAAATACAAATTCTATTTCGCAGAATGA
ATGCCTATTTTCTGAAGGAGGTCACTAAATACCAGCCCATCAGCGAGAACATAAAGGTCACGAAGAACTCCTTGCGCTATCGTGGCATTGATGGC
TTCATCGCCGCTGTCAGCCCCTTTAACTTTACGGCCATCGGCGGCAACTTGTCCTACACGCCAGCTCTGATGGTAAGACTAGCCAATGGCTGGAA
ATACCAATTAACTAAGCAACCGCCTTCGATTTTCGCAGGGAAACGGCGTGCTGTGGAAGCCCTCGGACACTGCCATGCTGTCCAACTGGATTATT
TTCAAGATTATGCGCGAAGCGGGAGTGCCCGATGGAGTCGTTAACTTTGTGCCCGCCGATGGCCCGTGTTTGGAGACACGATTACGGCCAGTCC
CCACCTGGCAGGCATCAATTTCACCGGCTCTGTGCCGTAAGTAATTGTCGGTCTATTGATTTTCCCGTTCAATACCATTTCCTCCGACGACAGAA
CCTTTAACCGCCTGTGGAAGCAGGTGGGCAACAACATTGACAACTACGTGAACTTTCCTCGCTTGACTGGTGAGTGTGGCGGCAAGAATTTCCAC
TTTATACATGCATCAGCCGACGTTGAGTCAGTGGTGACCTCCACGATACGCTCAGCATTTGAGTACTGCGGCCAGAAGTGTTCCGCCTGCTCGCG
AATGTATGTGCCGGAATCCCTTTGGCCACAGGTAAGTTTAAAAAGCATCAGATTGCGATGTTTTCGCAACGCTGACCTGTTTAACCCCTAACCCG
CAGATCAAGGAGGGCCTGGTATGCGAGGCAGCAAAGCTGAAGATCGGTGACGTTCAAGACTTCAGCAGCTTCACGTCGGCTGTGATTGATGACAA
AGCATTTAAACGCATTACGGGCTACATTGAGCATGCCAAAAAATCCCCGAACCTCGAGATTCTCGCCGGAGGCACTTACTCAGACAGCAAGGGCT
ACTTCGTTAATCCGACCATTGTACTCAGCAAGGATCCCAAGGACCGGATCATGACCGAAGAGATTTTCGGTCCCGTGCTATCTATTTATGTGTAC
AAGGAGTCGGACCTCCTTGAGACCATGAAACTGGTGCACACCTCTACCAAGTTTGCTTTAACCGGAGCAGTATTCGGGCAGGACGAGTAAGAGAC
TTCTATACAAAGGGTTATCTTTAGTTCATAACGTATGCTTCCAGGGATTTCGTCAAGTGCGCTCTGCAGGAGTTTAAAATGGCCGCTGGAAACTT
CTACATCAACGACAAGTCCACTGGATCCGTGGTGGGCCAGCAGCCATTCGGAGGCGGCCGGATGTCCGGCACCAATGACAAGGCCGGAGGACCAC
ATTATATTCTGCGCTGGACCTCTCCGCAGTCCATCAAGGAGACCTTTGTGCCGCTGCGGGACGTCAACTATCCATACATGTGCGAGTAAGCTGGC
CGACAGAAGATGCGCAAGGGGAATGGATGAGCAAAAGTAGTGAAAACCAGACAGGAATCTCATATAACTACTAACTATATAAACATACTTAAAT
GTATTTTGTTGAAATACTTTTAAACATCTCCAACACCCAAAGACCTGCCCCGTAACCCTACATACCTAGTTCAGATAGCTTCGATTTGTATACAC
ACACACTCTAAGAATCTCAAAACAACCCATGAGAATGCCTCGAAAGTTTGTAAATTGATATGCTGATACCTTCGAACTACAAACACACCATGACA
TGGATATTTTAAATGAATACTATGTAATATCATTATTTTACGATTTAAACGCAATGTGATTATTTAATTATATATGATTTATAATTAAATGGCCC
GCCTTATGTTTTATTCGTTATCGAAATTGCTTGAATTGGTTGAACCGTTTTCAATTATAAAATACTTAATGTACACACCTATGTATGTGAAATCA
AACGACAATACATTCTGAATACTAAATGTGAAAGATCATGAAGAGATAAAGTGAAACCTAGTTACATGTAACGTAAGCATCAAATTCATATTAAT
AAATATAACAAAGAATTAAAAAGAATTATTTGGGTTCCGTTTTCAACATTTCGTTTAACCCAAAATGCTATCCGCATCGATTGGGGCAGTTCCTT
TACCCGAAATAAGATGAGTTCTTAGAGATTAGAAACCCGTAGAATTTAAACTTCAAAACTTGATGGTCTGAAGAGAACATGCAAAGGTTTAGTTT
CATTTGATTCAAATTTGTAATCAAACTACAAACAATTCTGTTATTAAAAAATACATGTATTTCTTTCCGTGTTTTCTTAGTTCAATTAAATACAT
TGTCCAATGTGACAAAACAAATTAATCTTTTACATATTGAAGTTGTCATAAGCATTCATAAACCGGCTATCACCACAAGTTAGCGGAAAATTCAA
CCCTTCATTTAACCCAAGCGTCTGAAAAATACCTTGGCTTACTC
(SEQ ID NO: 784)

Exon: 1001..1097
Exon: 2497..2662
Exon: 2794..3267
Exon: 3416..3587
Exon: 3649..3836
Exon: 3894..4116
Exon: 4184..4551
Exon: 4605..4839
Start ATG: 2598

Transcript No. : CT22083
ACCGACCGACCAATAGTCTCGCAAAACACAAAACAAAGGCACACCACACTTCGTGCTCTCGCCGAATTCCGCCGCCGTCGCCTGAAACTCACACA
AAATAGCAAAATTCTAGGTGGTACGAGCCGACGACGACGAAGAATCTGAGAGACCGCTTATATAATCCGGCAGCGAACGAGACAGGCCCCAAATC
CCGACAAGATGTTGCGAATGATGCGAAGTTCCTCCTCCAGATGCTCTAGTCTTCAGCAGAGCTTGTTGAAAAGTTCGACACGCTGTCTGGGTTCC
GTTATACCGGACCTTAAACTGAAGGACTTCCCGATCGCCAATGAGCCAATCCTGGGATATCTCAAGGACTCTAAGGAGCGTAAGGCCCTCGAGCA
GGCTCTAAAGGGCACGGCCTCGAGTTGCGAAGACATCCCCATCGTGATCGGCGGCAAGGAGTACAAGACGCCGGAGGTTCGATACCAGGTCATGC
CCCATGACCACCAACACAAGCTGGCCAGCTTCTACTACGCCGACAAGAAGCTTATCGAGAAGGCCATCAAAACGGCGGTGGAAACACAGCCCAAG
TGGGACCGTGTGTCGATTGCAGACCGTCTGAAGATCTGGGAGAAGGCAGCGGACCTAATGGCAACGACGTACCGCCAGGATCTCAACGCCGCCAC
CATGCTGGGTCAGTCAAAGACGGCGATTCAGGCGGAAATCGATTCAGCAGCGGAGCTTATCGACTTTATACGAATGAATGCCTATTTTCTGAAGG
AGGTCACTAAATACCAGCCCATCAGCGAGAACATAAAGGTCACGAAGAACTCCTTGCGCTATCGTGGCATTGATGGCTTCATCGCCGCTGTCAGC
CCCTTTAACTTTACGGCCATCGGCGGCAACTTGTCCTACACGCCAGCTCTGATGGGAAACGGCGTGCTGTGGAAGCCCTCGGACACTGCCATGCT
GTCCAACTGGATTATTTTCAAGATTATGCGCGAAGCGGGAGTGCCCGATGGAGTCGTTAACTTTGTGCCCGCCGATGGCCCGTGTTTGGAGACA
CGATTACGGCCAGTCCCCACCTGGCAGGCATCAATTTCACCGGCTCTGTGCCAACCTTTAACCGCCTGTGGAAGCAGGTGGGCAACAACATTGAC
AACTACGTGAACTTTCCTCGCTTGACTGGTGAGTGTGGCGGCAAGAATTTCCACTTTATACATGCATCAGCCGACGTTGAGTCAGTGGTGACCTC
CACGATACGCTCAGCATTTGAGTACTGCGGCCAGAAGTGTTCCGCCTGCTCGCGAATGTATGTGCCGGAATCCCTTTGGCCACAGATCAAGGAGG
GCCTGGTATGCGAGGCAGCAAAGCTGAAGATCGGTGACGTTCAAGACTTCAGCAGCTTCACGTCGGCTGTGATTGATGACAAAGCATTTAAACGC
ATTACGGGCTACATTGAGCATGCCAAAAAATCCCCGAACCTCGAGATTCTCGCCGGAGGCACTTACTCAGACAGCAAGGGCTACTTCGTTAATCC
GACCATTGTACTCAGCAAGGATCCCAAGGACCGGATCATGACCGAAGAGATTTTCGGTCCCGTGCTATCTATTTATGTGTACAAGGAGTCGGACC
TCCTTGAGACCATGAAACTGGTGCACACCTCTACCAAGTTTGCTTTAACCGGAGCAGTATTCGGGCAGGACGAGGATTTCGTCAAGTGCGCTCTG
CAGGAGTTTAAAATGGCCGCTGGAAACTTCTACATCAACGACAAGTCCACTGGATCCGTGGTGGGCCAGCAGCCATTCGGAGGCGGCCGGATGTC
CGGCACCAATGACAAGGCCGGAGGACCACATTATATTCTGCGCTGGACCTCTCCGCAGTCCATCAAGGAGACCTTTGTGCCGCTGCGGGACGTCA
ACTATCCATACATGTGCGAGTAA
(SEQ ID NO: 785)

Start ATG: 199

MLRMMRSSSSRCSSLQQSLLKSSTRCLGSVIPDLKLKDFPIANEPILGYLKDSKERKALEQALKGTASSCEDIPIVIGGKEYKTPEVRYQVMPHD
HQHKLASFYYADKKLIEKAIKTAVETQPKWDRVSIADRLKIWEKAADLMATTYRQDLNAATMLGQSKTAIQAEIDSAAELIDFIRMNAYFLKEVT
KYQPISENIKVTKNSLRYRGIDGFIAAVSPFNFTAIGGNLSYTPALMGNGVLWKPSDTAMLSNWIIFKIMREAGVPDGVVNFVPADGPVFGDTIT
ASPHLAGINFTGSVPTFNRLWKQVGNNIDNYVNFPRLTGECGGKNFHFIHASADVESVVTSTIRSAFEYCGQKCSACSRMYVPESLWPQIKEGLV

FIGURE SHEET 425

CEAAKLKIGDVQDFSSFTSAVIDDKAFKRITGYIEHAKKSPNLEILAGGTYSDSKGYFVNPTIVLSKDPKDRIMTEEIFGPVLSIYVYKESDLLE
TMKLVHTSTKFALTGAVFGQDEDFVKCALQEFKMAAGNFYINDKSTGSVVGQQPFGGGRMSGTNDKAGGPHYILRWTSPQSIKETFVPLRDVNYP
YMCE*
(SEQ ID NO: 786)

Name: DELTA-1-PYRROLINE-5-CARBOXYLATE DEHYDROGENASE-LIKE
Classification: enzyme

Celera Sequence No. : 142000013384663
CCAAAACTCTGCCTTCGACACGATTTCTTTTCTATTTCAACAGCGAGCTGACATTTTTTTGCATGTTGTTGTGGCTGCGAATTAAAAATTGCATA
CAAAAAATGGCAGCAAAAAACTAGTCGATCTTTACTCGACTTTGGAATACCAACTAATCGGTTTTCACTATATTTGCTTGATCAAAATAAAGCAA
GTTAGTTATTTATATATATTTATAATATATAGATCATTTCCAATGCAAATGTGAGAAAAACGATTATAATATTGGTAATTTTTAATGTAGTGATT
GCTTTGATCCTTTTGAATTATTTTAATAAGAATCGCAAAACTTGCTTTCAAGTTAATTAATTCAAAACTTCAAATCGCTAGCAGTAAACTTACTT
CAATAATTAAAGAAATTCGATATTGTTTTAACATACCCCTGTCCTTTAGAAACACAGGGTGCAAATAGCGAAATGAAATTCCTGGCACAGAACGT
AATATTATTAGCGGGGAAGCCTTGTCGACCGCCTCCACTTGACTGCGAGCAACTCGGGGCCATAAATATTGCATTACAATCGCTTTACCCCCTTT
TTTTTGGGTTGGCGAGTTGTCGTGCAGTCGGTGGTTCCACCTCCACGTGGTGGGTGGTGACCCCTCCAACCCCATCCCGTCGGGATATGCAATTG
CGAATTGGATTTCATGTTAATGCAGGGTCCTTATCGCCGGTCATGTGCTTGGACGGTCAGCAATGGGTTCATTTGTGTTCTATTTGGCCGGTAAT
TTCACTTAATTGCGATGACGTTGTGTGCAAAAAGCCATGGCAAGTGGGGGCGTTTTGGGGCGGGGGATGGAGACCCAGTGGATTGCTGATTTATA
TCGCCATCGAGCGAGGTAGCACGGTCCATCAAATATTCAGCGGTCCGTGGCTTATTGAAAAGCACAAATGGCAATTTCAGCAAGTGCGAATGCCC
AGGGAGCCGCCAGTTTGCCTTCCAGAAAAGCACTTAATCGGTGTTTTTTTGTGTGTGTACATTTAGGTTTTATTCTTGTATTTGAATGCAATCGT
GGTTTACAATATATAGAGTTTTCATTTCAACGTTGCCTTGCACATTCAATATATAATATACGTAATAAAAGTAATTATAAACAACAGTTGTAAT
AAAAATAATAAACATGTAGATGCATTTTCTCGTAGACGGTTGCGGTAACGGATAATTGGGAATTTATCTTTTTATGTTTCTTAGTGTTATGTCAT
GTGGGTCATCAGCTCGAGCTCAAATATACACTCGTGTGTATATATATATATATTTGTTTAAATTATATTTAGATATAGGTTGTATAAAAGGTGTA
CTGCAAGTGCTGCGTATGCGTGGGCTGGTGTTCATGTGTGTGAGTGTGTGTGCGGGTTTACTTAGAAAATCATCCGAATGGTTTAAAAATAATTA
TAAAATCTACTGCGTTTGCTGCTGAATTTCAATCTTCTCGACTGTCATGTCCGGATTCATGGCCGTCGCTTCCTGTAATCGCGTAAAAAACAATT
GGTATCAGTTAATGTATCTACTAACGTTGAAGTTAATCCATTAGATACTCACTTGTATTGCCTCGGCCAAGGCTTTGTCATGATCGATCGGATCT
CCATCGGACTGAATGGTTATCTTCTGTTCCACTCGGGTCTCCACAATGCCATCGCGTTCGGTTTTGTACTGTTCATTTAGAGTAGAGTATTAATT
AATGTTATTTTATAAATGTGGTACAACCTGAACCCATTCGAACAAGGACTATGCATGGAATATACAGTGTGGTGCATACGTTCACAGGAAATATC
TTTTGGATAGATAGATAGAAAGCCTACCTCTGGCTACTTACGCAACCTAATCGAACGGGATCAGTTGGATTAGTTCCGGTTACTTACGGTAATGG
TTTCCACAGTGCGGGTTTTGCTGCTCACGGTTTGGGTGGAGATGATTTCGCCATGTCCGGAGAATCCGGGTGTGTCCTCACCGAGAACCACTCGG
GTGCTTTCCACATGGGGTCCAGTGGTGGCGGAGGTCGTAAACAGCGGAGATTTCTGTGCAAGATTCGAGATTATTAAGCTTTGAATGTAACTTTT
TTTTTTTGGAAGCGCAACTAATTTTAGAGGGCCTAATTATCGATTGCTTATTGGAAAGTAGCCATGCATGACCCACCTGGTTATCTGTGCGCACC
ACACTGGCACCATCGTAGGGTCCGTCGATGGGCGTGCCCGAATCGCCGGAACTGGTCGAGGAAACGCTATCCCTCCTCTGATACTACACAACACA
TAATATAACATAACATATCGAAATCATAATGACAACAATCAACTCATGCAATTGGGATGCAGCCATGCGATCTTACCTGATCCCCACTGGTGACC
GTCGCCGTCGTCTTCACCTCCTGGGTAACGACGCGCTGCTGCTGCTTGTTGGGATCGTGGGTGCGGGTGGTGGCCACCGTCTTCTCCTCCAGCTG
CTCCGTCTTGGCGTTCTTGCCCAGATCCTCGTGCGTGGTGGCGGTGCGGGTGGTGACTGCGGTGGCCGTGACATAGGCGCCACTCAGGTCGGTGG
GTGTAGCATCAGCCTAGGTGGATTGAGTGGCAAGTGGGTGGTTCAGTGGGTTAGTGCGTACGGCATAAAAATACAACAGCAATAATACAACAATT
TAAGCAACAACATCAAATACAGGCGGAGTTAGGCAAAGGCAGAGATTAAGATTAATATAACTTTGGAAAGCGAAGCGCAAAGAGACAGAAAGAT
AGACGTTTCCGGTTTTCAGAGCCCTAGGTTTTGATCCAATTCGATTGCGATTTAATTAAGATTTTCTAAATATTATATTGTTTGCGATGATTGGA
AAAACCTCAATTGAATACCAATATCTTTTATGCCCCATTAATTAAAATCGAATTCGATCAAAGCCCTTAAGAAGTGAATTCCAGTTTATCCATAA
GGGACGCAGTCCCTCGCTAACCTTGTGTTCCTGCGTAGAGTAGGTGACCTCGCCGGTGCCCAGATTGCGCACCTCCTCTTCCACATTGTGGGTCA
CGCCATCGATGTTCTTGGTCAGCACCTGTTGGTGGTCTTCACCACCGTGGGCGTGCTCACTGGCTTGCCCAGCTTGCCACCCGCCTGTCCC
GCCGGACTGCCGATCAAGATCTCATTGACCTGGTCGGCGCCATACTGTGCGGTCATGTCGTCATCGGAGCTGCCCTCGGAATCCCGCCGCAGAGC
ACCCTTGCTTATGTGCTTGACTCCGTCGAAGAACTGCTGGCGGGTGATGGGTACCGTTTCCGTGGTGGTTTGCACCTGCGCCTGTTTGCCGAAGT
GGGAGGGATCGATCTGGGCATAGTTCAGGATCAGTTTTCCGGTCACGGGATCCGTGACAGCCGTGGCGGGATCAATATCTCCCGTGTTCGGATCA
ATGTCGCCCATACTCGCTCTTAATCCTGCCGGTCACGGGATCAATCTCTCCTGTCAGCGTCATCGTGTGGGTGACCGTGGTGCGGGCGCCAGCGAA
ACGCGGGTCATTGGGGTCCACCTGAACAATTTCACCGGTCACAGGATCAATCATATTGTAAACATAAACGGTCTTATTGAAGAACTTAAGAACGC
GGCCGGAGACGGGATCGATTTCGCATGTGGAGGGATCGATCTCCTCCGGTCGACCACGTTCGTCGGTCTTCGAGATAAGCAGGATGCGCACGATC
ACGATCTTGCCCGTCTTGGGATCGACGCGGGCCAGCTTGGTGTAGACCTCGCCGGATTCGGGATCCACCTGGGTGGCCGCATACAACGGCTCCCC
GGTGGCCTGATCCACCTCCCCGGTGGCAGTGTATATCTTTCCGGACGTGGGTTCGATTTTGATTGTGTTGGGGTCGAGCTTGGTCTGTTTCTTGA
TCTCGTTGGTCTTGGGGTCCAGGTAGCCATAGATGGTGATGACGTATCCCGTCTTGGGGTCCACGCTGCTGGAGATGTACTGCTGCTCCTTGGTG
GCAGGATCGGTGGCTCCAGTGGGCACCCAAATCTGGTTGGACTTGGGATCCACCACGATGTCCTTGTCCTTGGAGGCACTTACTTCAGTGATGGG
CGCCTTAGTGGCCGGATCCACGCGCTGTTGCACGATCCTCAAAGAGATAATCCTGGCATAATCCTTGTCGGGCTTGTTGTTCTTCGGATTGACCT
GGTTCTTCAGCACAATCTGTCCGGTGGTTGGTTCAATCTTAATGTCCCTAGTAACCGTCTTACCTGATTTCGGGTCATTGAACGTGATCGTATGC
TTAACCAGATCAATCTGTCCATATTTGGTATCAATCTTGCCGGCCTTCGGATCGAACTGACCTCCAGAGGTCTCCACCTGCGCCGTCTTGGGATC
GATGATGTTCCTCTTGGAATCGAACTTGCCTGCCAAGGAAGTGACCTCCACAATTGGGTCAATCTGTTGGCCCACCTCAATGAGGCGACCTTGGT
TCGGATCGATCTTGTTCGTTTTGGGATCCACAATGCCCAGGATAGTGATCTGGCCAGTACCCGGATCCACTTTCACGTTCTTGCTGACTACAATC
TTGCCAGACTTGGGATCAATGGCCTTAAGTTCGCCGGTGCGTGTGTTAATCTCTCCATACTTGGTATCCAGCAGGCCGGTATCCAAGTTCAGGAC
GCCCAAGGAACGCTCAACATCTCCGTTAACTGTGTCAATCTTTCCGGTTGCAGGATCAATGCGACTGGTGATCACTGTTAGCTCCACCACAGGAT
TATCCTGGGGTGTGATGCAAACGATCTGACCAAGGGTGTCGTCAAGGCGTCCGGTCTTTGGATCCGCCACACCGGATACCAAATGAAGATTGCCG
GTCTTGCCATCAACATCGCCCTGGAACACTTCCTTCTTTCCGGTCTTGGTATTCAGAGCCTCCAATGTTCCCTTCTTGGGATCAATCACGCCATA
TTTGGTGTCAATGAGTCCGGTGGCGGGGTCTAGAATGCCGGTGGAGTGCTCAATACTTCCGTTCTCCGCATCAATGCGTTTGGTGGAAGGATCGA
ATTTGGAGGTGATGACCATGATCTTGACTCGCCTCTTTTTCGGCTTGGCCGCTGCTGCTGCAGCTCCTGCGGCTCCAGCTGCTGCCGCAGCAGCA
GCTCCTGGAGCTCCCTTTCCTGTCTTGGTGGGAGAACCAGGCTTCTTAGAGCCAGCAGCACCTGCAAGACCAGCAGCAACATCAGCTTTGGAGGG
ACCAACGTAACCGGGCTCTTTGTTGTAGCGCTGTGATTCCAGGAAATCAGCCGTGGGATCTGAGATGGGCTTGTAGCTTCCTGGAGCTCCAGAGG
AGTAGCCTTGGGGTCCCTTGGTGGGCGAGTAGGATCGCTTCTGGGAATCGCTCAGAGGAACAGCAGCCGCATCCACAGCGCTGCCCTGGAGCTTA
GCACGAGTGGTGGGCGAGAGGAGTGGATCCTGGAGTAGCTTAGCCCGCGACTTGGGCGACAATTGACCGCGGTTCAGCTTATCTTGGGTGCGTGG
AGACAGCTGTCCTGCCTTCAGCTTCTCAGCCGTTTCCTTCAAGGCGTTCTCGTTACCAGGAGCATAGTTAAAGGCCAAACCAATCTTTTTTTGCT
GCGAGGTAGGAGACAGCTGCTCCTGGCCATCGGCACCGGATTTCCTAGAGTTAGGATCCTGATCGTAACGGAAGCCACCAGGGGTGTATGATTTC
CTTGTGGGACTGGTATTGCCATCATTATCCACGGCATACTCATACTGCCTAGTGACACCGGGAGTGGTGGATCCTCGGTTCTTAGCCGCATTCCT AGCCGCCTCGTCCAGGTTTTGATCCTGCTGATTATCGCCCAGACCAGACGTAACGACCAGACCAAGTCGACCCACCTCCTTGTCCTTATCCTTTC
CGGACTTATCCTTGCCATCCTTGGATGGGGAACCGCTCTTGCTCTTGCGACCCGAGGAGAATATGCCAACGCCCTGTGGATCGTCGTTGGATCGT
TTTTTTTTCGAGGATCAAATGAAAAGGTCAAACATAAAACGAAAAGAAATGGAGGTAAAAATTAACAAAAGGAAACCATAATAATTATTACACA
ACCAATGAGTTCAACTTAAGATCAATTTTCGGGTTTCACTACAAACTATCATAACTTACGGGTGAAACTTAAGTGATTTGGTATGTGGATTTGGG
TGGGTTTTGGGTCGGGGGGGTTAAGAGTATTTACACGAGGGCGGGCGCATTCGGTGCGGGGATATCGCTTAGCTCAGTACACCTAGTCTTGTGTG
TTCCTATGATCTAGCTTAAGTTGGGGATAGTCAGATAGGATACTTACACGTCTGCCTGAGGACTTGTCAGACTTGTTGGAATCATTCAGCTCGTC
ATTGCCTAGATAATATTTTCAGGGAGGTTAGTAAGATTGCTTCTTTAGATACTTTATCCTGGGGATACTTACCATTAACAGCCGCTCCTGCAGCG
GCACCAGCGGCAAGTGCTGCCTTGGCAGCCTTTTCGGCCTTCTTCTTCTCCTCCAACTCCCGCTTCTCCCGCTCCTTTCGCTCCTTCTCCTCCTT
CTCCTTTTGTTTCTTCTCACGCAACTTAGCCTCCTTATCAGCATCCTGAGAAAACATCGATCATTAGTTAGTTATAGTTTTTAGCGTATAATTCA
GAGGAAACAGATATTTGGGGCGAAAAGGCGACATGCTACAAAATGGCTGAGATGTACAATATATATTTACAATACAAGCAACAAAATTATAATAT
TTCGTTAATTAGGCATTACAGATGAAACTTTTTTAATACAACTGCATGTTTTGTGTGGACTGTACTGGTGTGGCCCTAAATGGTATTTACAGCTC
GAGAAAGGACTCTTACAGACGTCACAAAATAATCAAATCAAAGTTAAATAAAACACGTAAAAAAAGTCAGATAGTTATGATGTAATGCACATTTA
ACAGACAATTGACGGCACTGATTTCTTTTTTTTTACAAAAATTACCATCAGATCAAGGTACAGCTCGTTCGGGTTCTATCACATTGGTTAGAGGA
TAGTCGGTTATGAAAACAAAAAATATAAATTAATAGGTTCAGAACATTCATAAATTACTGGGGTAAAGTAGCCCTAAGCTGAACAAATAAACGAA
TAACTGAGGGAGACTTCAAATCAAATCGTTTCATACGTAAGCTCACAACATTCGAAAAGCAGAGTTCAAAGCCGATAAAAAAGTTAGGAAGGATA
CATTGTAGAAGATTCGATTCGGAGGATACTTTTTTTTTGGTTTTTTTTTTTTTCGATTTTTTTTTGAGTTGTAGGTAGTAAAGTGTTAACCTGAA
CGGGGGGCTCAGCCTCGATGGCCTCAATCTCTAGGTTGGTCTCGTAGTCACCCTCGAGGGAACTTTGCGAGGAGGCCGAAGCCGTGCCGGTGCTC
GACTGTCGCATCAACTGGTTAGTGTAATGGGGGGTTAAGGTGTGTTTTTTTTTTTTTTAGGGGACGAAGGGTTAACATTACGAGCACATCATTT
CATATTCAGAATCACAGAGTGGATGTGTGTGTGGTTGTTTGGTTTGTGAGTGGTTGTGAGTTAGTAACAAACCGAGAAGAAAGTACAAAAAACTC
TGGTTAACTCCGAAATCATCGTTAAACATGTTCATCTCAATAGCTATGTTTCGTCAGGCATTAGTTGGTTAAAAACTGGATGGGTTACCTTCTCC
TTCTTGTTCTTGATGGGACTGCGGCTGTGGGCATCGCCATCGGCATTGCGATCTCCCCGATGATCCAGGGTGCTGCTCTTCCTAGCCACCTTTTC
CTTTTCGGCCAAGGCCAGAGCTGAAAGGATCAGGTAATTAGAAACAATTCAAACCACATAGATTCAAAACTATCAGGTTATATATAAGCAAGCTC
TACTCAAGACTAGGTGTAATTACCATCCATGCTCCTGGAAGTGAGACGAGCTCCGGACAGAGTCCTATTGAACTTCGGAGGAGTACGATCCACGG
GTGTGTTCGTGCTCTCGGCCTGAGTGCGACCCTTGTAGCGATAGGTGGACCCGAAGACTGGGAACATCTTGGACTTGCTGACCGGTTCGGGGGTC
ATCAGGCGGAAGAAGGTGTGGTGCTCCACGCAGGATTTCCACAGTTTCTTGGCGGCACGATGGTTGGCCAGCTTAAAGCCAATGGTGGATTCGTA
CTGCTCGAATTCACCCGGTCGGATCTTGATGTAGAAATGGTGGCGCTTGTAGGAGATCTTCAGAATCTTGGGCCAGGCAAAGCGGTTGATGCGCA
ATCTAGTTGGATAGTGGTTTAAATATATTAGCAATTGTTTAATTTAAATATAGTAAGAGCTGCTCACTTATCGCGGTAGACGAGCAAACCGGAGG
CACAAACGCCCAGCATGATGTCCACGCCCTCAGAATCCTTAGCGGGATGCAAGTCCACGCCGTACATGGCCAGCTTCTTGGCATTCTCCAGGTAG
TGTAGCTCAGCCTCGGCGGGCGATTGTCCCCTAGAATACAAAATATTAAAGTGAGTATAAATCCTTGATATAATAGTCCAAAACTTACTTGTGGG
TCTTGTGAAGATCCATGACCTTATCCTCCAACTCAGCCGTCTGATTTGGAGCGATCTTGAAGTCCTTCAGGTAGGCCCTGGTGGGCATTTCCTCT
GCATCGTAGTCGCCCATCTCCGACTGCACCAAGTAGGATCCGAGCAGAGCGTGGGTGACGAATGTGCAGGGCAGTCGACCCTCCAGGATGTCATT
GCGCACCTGCAGGCACAAATGGTAGCGCGTGATGTCCTCCTTCAGCTGCGATGGCTCCGGCGGATAGAACTTGACGGCGAAGGTGAGAGGCCAAG
TGTCCGTGCGGAAGAACTTGGATACCGGCTTCTCCAGATCCAGCCAAGTGCGCGGATCTGTGGGCGTCTCATAGGTCAGACCAAAGTAGTCCTTT
TCGATGAGGTTCAGACCGGCGCAGATTGAGTTGATCACATCACGGCCAATGGCTTTGCGCTGTGGAAATCAAATTGAACAATTCATCATTGTAAA
TGTTTTTAATCATAACCTTAAAGGGTTTGACTTGTTTAACACATCATCATCCCTGCTTACTCACATCAATGGACACGTCCAGAAGGGAGCCATCC
AGCAGGGTGACTCGTGCTAGGGCAGGCTTTCCGTGCGAGGATGAGCTGGACTTGGGTTTGCTCTTGGTCGGCGTTTCCGGCTCAGCGGGCGCGGA
TGGTTTAATTTCCGCCGGCATCTTGGATTGGGGGACTTGGCTACGCCAGCGACAGCTTGGAGTTGGCTGCAAGAATGTAAAGACTTTAGTAAATT
GCACTGGATCCCAGTTAAATGGCCGGAAGTGTCCACTCCGCGGGGTCATGTGTCCCAGTGTGTGTGTGTGTGTGTGTGGGCGCCTTTCGCTCA
TTAGAAGTCTGCAGTCTGGACATAAAACACGACATAAACTTTCTCAATTTGCCTGGCGCCACTGCGCAAATAAACTCAGCACACACACATTTAAG
CACAGGACCCTCAGCCAGGATGTGTACAACTCCTCCTTCTCCACTCGCTGATGACTATGATGTCACCAGTTGCAATTGCGTACTCACTTCCAAAG
AGCTCTAGAATTTCTCCGGCAATGATTTCCAGCGAGCTGTAAGAGAAATTTCGCCATTAAAAGCTGAACTGCAAATTGAATTACCATTTTACTAG
CGAAAGCAGATAGTAAAAAAAACTTTCAGGTCTGAGACCATTACAATGAGTTGACCATAAACCGCACAACAGTCAGATTTCGCAGATCTATTATT
AAGCAGAGTGAATACAGATAATGCCCCAGTAATTAAAGTCATTAAATATACAAAAGTACATGGGAATAAAAGTTGGGAACGTCCTTTGAGTAAGC
CGAAAAGTCAAGTGATCGGCGACAGCTCACGTTCCAGATCTGGATTCAAGTTCAGCAGTGACATAAGTCTTCCATATATACATATATATAAATAT
GTATATGTATGCTCCATATCGGTGTGGGTTATATAAGCCGGCAAGTCGAGGCAGCGTCATGTTCTCGCTTTTATCCCCTTCCGTTTCCATTTGAT
TCCGTTTGCGGTCGGAATTTAGCGGGACTGCAAATTGCGCAAAATAATGTTGTTTTCTTCTGAAAAGAGACGATATCGGCATTTTGCCACGGATG
TGGACACACTGCCCCACCCAGAAAAGAGCCTTCAATCAACGCTGATTGGGAATGTACTTGGGTGTAGCCATAGTTATGGGTATGGTTAACGTGCG
AGGATCGAGAGTCAATTGAGCCCAGATGCGCTGACCGATTGCACAGTGAGTTCAATTTACAATCGGAGTGTTTAATTGGCTGGGAGTCATGAGCC
AAGAGATGTGTCCATCGATCCCGCAGAGGAAACTAGCTGAACCAGTTTGCCACAGACTTCGTGATAGAGGTCTTCTATGGCGCTATAATACTGTT
TCAGTTTCGGACACGACCCCCAAAGCGAATTAACTCTGGTGGCGTCATCGTGCGTTCAAAATTAAACAAAAACACACACATGAAATATGTATGCT
GAGAACCAGAACCCGAAAACCAAAAAAAAAAAAAGCAGACAAACATCTAATTTATATTATTTTATTTATTCTCGCGTCTTTGTAGCGCGCAGACC
ATGTGTATATGGACTCCATATAGCATTACTTTTGGCAGCGTGCTTGTTCTCATAGTTGAAGGTTGCGCATACGCAATGTTGACATCATCGACGGG
CGGTTGCAACCACCTCGTTATTTTCACTTGGCCAAATGCAGGGCCCCATGAGTAGTGGGAATGGGTATGGGAATACTTGACTAAGATCGGCGGTG
AATCAGCGGCATTATCTTGCCGTGCCGACTTACAAATTCGTTTGGCTGGCAAACCAAAACAAAGTAAATCGCTCGAATTGTCGATAGCGCATAGC
GATTTTACAATGCGGGGGCATTCGTACATGATTTATTTTCGATGACATCATCAGCTAAGCGATCAGCACCAGCTAAGGCATAATATCAAGAGCTA
TTTCTAGAGTTTATACAAATATATTTGCAGAAGATGCCGACACCCAAAAACATTTTCAGCACTTGGCGCATTCGCCTCAATTGAAGGAGGTCGAG
GTGAAATTCATCAAGTGGCGCGCGTCTAATCTTTAGGTTACAATATTGCTGGCCAGGCGAGAATAAATACGTCCAAATTGAGCAGAGAAGAAGCA
GCCTAACCAAGTGAGTAGAATATATACATATATATGTATATATATATCTGGTATTATTGTGAAAGTAACGAAGTTCTTGTGGCGGACAGAAGGCA
GAAGCACAAAAGATGGCAATCGCGTCGTTTCAATTGAGATTCGGAATGAGAACATGGGCACTCGTACTTTGGGTGCAGCCGGCTCCCCTTTAATT
AAGTTTCATTTAATACAACTTAAATCAAATTCAATTGGCGACGGGTCTGCGCCAGGTTTTTCATATCCGCGGGGATGGCTCATACATGTGTCATC
GAGTTATTACTCTGACATCAACATGGGTCACCTGGTGGGCGGTGGCGTCACTTCCCCGGGAACGGCGTGCCCCCCACACATTGAATTTCTCCCTT
GTATGTACATAATACATATATAGTACATTCCCTCTAGTCATTGTGACTAAACTTTCGCTTTTATGCCCATTAACATTAAAATTTCCCCCGGGGCT
GTGAAGTGCACAAAACTTTTCAAACTTGCCATTTTCTGAGCTCAACGAAGCGTTGCCAATAAATCGCATTTAAAATGTATTATATACTGACTTCA
CATCCGTTTATAAACATGGCCGCATTTCCGCAAGGGAAGCTGTTACATTTTCCGTTGTGGTGCATAAATTGAAATATGTACATTAATTTGACAGA
CATCTGAGTGTCATTTTAGCTAATTAGAGTTATATTATTATATCAATTTAAGCTTTTAAGAATACTTTCATTCTCTTTATCACTTTACCCCTTTG
AACCAATCATTCACTCGAATGAACAATGGATTTCATGCCTGGTGCGTCAGGTCTTCCAAGTTATTTTGTATATTTTTCGAGGAAATATGGAGTGG
GAAATACGTAAACATTCGCGCATTCTGGACTGTGTGCTAAAGTGGGAAAGTGGGTCAATCAATACAGAACGATTAGAGGAGGGTGTGTTTCGCTC
TTGCGAATCCATAGACTTATCGACGGAGTGGAACCGCCTGGCAGTCGAGGATGGCGACTCTATGGAACCCGTCAGTCGATAAGCCAGATCCGTTC
CCATTTCCCATCGCACTGGCAGCCCTGAGACAGAGATGACCACTAGCTAGTAACTCAGAAGTGGATCAGCCACTTGAGGGGAACTGGTTTCTGGT
CACCAGATGCCACTTTTCGACAGCTCAAGTGACGGCTCTGTGGAGCAGTGTGTCGCTTGACTAATTACCGCTATGATCGACGTTCGGATGACAAG
GCGACATAACCGCACTGGATCACACCCACACATAGCCATCTGCACCACCATCGCTCCACCACCCGGCACCATCAGTTCTCCACTGTCAATGGCTA

FIGURE SHEET 427

TTTAAAGCATTTGACTTCGCCTGGCCAACGAACTCTGAAATGCATCCACAGTTGCTGCTATTTCAACACCATAAAATATAAGCTGAACCAAAATC
ATTTTAGATGTTGTATCCGTATGCAAGTCTTTTTAAAATAATATATATAATATAGAAAAGGGTTGAAACAATTTTTTGGTTTAAGGAACATAACT
ATTTTATTTAGTAGAACAGAATAAGTGGTTTTAGGTTAATATTTTTCACTGTGTTGGTATGCCGCACCCACATGCACATCGCGTTTTGATTTCTG
CCCAGAAGGTGAGGGAAAAAGTGTCGCGAAGGGCGGAGAAAGTAAACAAACGAACCGCCCTCGAGGAGAATTTTGTCCACTTCAGCGCTTTGCAC
ATTAATCATAGACCTATAGACGCCCCATCCGCACAAGTAAAAATCGATGCGACAAGGAATAAAAATAGAAAACGGAAAATCGAATGGGCATTTAG
GAGGAGCGCAAGAGGGAAACTGATTGGCTAAAAAGGGGGCTGGAAAAGCTGCCTTCCATCCGATTAAGTTTGTTGAAAGATTAGATTGGTTTTTC
ACCTCGCTGAAGGAGGGTGGAAATCTTCCGGTGAACTAAGAATAGCTAGCGATTCTAAAGAGGATTCATAAAGATGAAGATATTAAGTGCTACAC
ATAGTAGGTGAGATCCCCAATCTTAACAACGATCTGGCCACGCTGGAAAATCGCTGGTTGGGGCTTAGTCTCCGTTTTCCGACGAGAGAATCCGA
GAGAATACGGAGAGACGCGCTCTGGGAGCTTCTAACGCTGGAAGACACACCTAGTTGGTAACGCTCGAATTCGGAGTCGTGTTCGAATTCAGGTT
TTCGAGGGGGCTCTGATTCCGACTCATTTTGTTTTTTTTTTAGCCATGTTCATTCGCGTGCTGCCAAGTCGTTAGCCCTCCGAAACTCTCTCACT
CTCCAGATTTTTGTAGTATAGTTTTCCACTCGCTGGTTGTACAGTTATTGGCATTCAGTTGGCTGGCACTCCTCGTTTGCTTTGCTCGGCTGCTT
TATCTGTTTGTCTGCTGTGCAGCCAACTTCTTGGCCAGCAACAACCGGTTTTTTTATTTCTTTCTTTTCTAATGCAAGCTCAACCTCATGTTAG
CCAGTTCGTTTCCATTCCCACTTTGCATGGCCTGGCCAAGAAGACGAAGTCTACATGTTAATGTTTCTTACTATTTGGGTCAAAGCCCACACCTC
CCGGAAAAGGTGGAAGAAAAAAGACTTCACGTAAACAGCGGTTTTCGAAGAACGGTTTTTTGGTTGCCAAGTCAACGCCCCAGGTTTTCCGGGGA
TGGTGAAAATCGTGCCGTGACTCAGTGGATGGGGGATGAGGGGACACCTAAAATATCGCCACCAGTCACCTGCCATTCATAACTGGCCTTTGTTG
TGGTGGCCTTATCTTATCTTAGCCATGTTTCCTAGTGGCTGGGATAAAGACCGACGTTGTTTACCCCAGCCGATATCAAACATATGAAAAATGCC
AATGCAAAAAGCGCTCAATGTTGTGATAAGAAATGTGGAAACCTGCTCGCAAACCCAATGGATTCTATTTTGGGAACAGTGACGTCTTGATGCTT
GGGGAATTTAGCCGCCATATGAAACTATTATATATGCCATATGAATGCGACGAAATTCCAAAATTATATTTAAGCGAGAGAAGGAAATGAAAGGA
ATCGGTTTCATAAAGTGCGCAGTTCTAGGAATTTTGATTTTTCGGTTGGTAGTTGGCCTTCTTTAAAATATAAATTCAAAGTATAAATTCTACTC
AATTGATATTTACACTTAAGAAGTTTTCTATTCATAATCATCATTATGAATAACCTTTTCAATTTGCGTAGAATTCAAAAGTGATTGTATGCCTT
TCCACATGCGTATCTTTGAGATACATATACATACATACGTTGTAGTTTTACCGATACTGAGTAGGTTTTATAAAGATATAAAGTATTTGCCCCCT
TTTTTAAAGTTCACTGCTAAACGAAACTACCTTTGAGATACATTTGTATCCGATCGGTGTTGTGGAACGTTTCCTTGACTACCGCGGGCCCAATA
AGAATTTCCCACCCTGCGCCCCGAAATGCGAAGCAAACGAGGAAAACACAGAAGAAGGAAAATTGGAGTAAGGCAAAGACAGAGGCAAAATCAAA
AGAGAGCTGGCGACAACAACAATGTGGGCCGAGTTGACAAAAACAAGAAGTCGAAAGAATAAGAATATCGTGCCAAAAGATACACTCGAAAAGCT
TGACAGCTCACAGATACAGATACGCAGATACAAATGCCGCGTGAGTGAGTCGAGCTCTCTTTTCGCTCCCGCTCGCAAAGCTGCTCTCAATTAAC
TCTGCTTTCGGGTGTGTGTGTGTGTGTGTGGTGTGTGCTATGAAGTCATACTGCCCAAGTCATTCTGCGCTTGTGTTGGTATCGAAAACATAAGC
CACCAAAAACTCCCGACCACAGCCCAAAAGAAAAAAACTTGAATAAAAATGTAATTAACCTATGTCGCAATCCCCAAATTGTACTCACCCTTTTA
AGACGCCTCTAGAATCCTTTTTAATCCACAGCAAGGACACGCAGTTACCGTTAGTTTGGCGGTTGGCTGATTTTTACTCCTGTATTTGTGTTGTT
TTCACTTTTCTCCCGTGGGCACTGCACTCACTCGCTTTCACACTAGTAAACAAATTCTTTGCCACTTTTTTCTATTCGTTCGCGAAAAAAGACAA
TTTGTTGTTGTCGTCGTCGTCGTCGTTGAATACCTGTTGAAAATTTGACGTTGAGTTTCTTTGAGTGAGTAATAGAGAACGCAAGAGTGGGAGTT
GAAGGGGTGTGTGTGCTGTGAGGGGGGTTGGGCTCAGGGGTATAATAGAGAGCGGGGTGGGCGTGGGCGGAAAATGCGCGAATAGTGGTTGCTAA
TAAATTAATTTCCCATTTTATTTATAAACACACTGCTGCCGAATTGCGCGCTTTTCTTTTCTATCCGCTCGTCGCCGTTTTGCAATTACTTTGCT
GCTGGCCAAACAACAAATCTTCTCACAATTCTGGCAGCGCGATCACACAAAACGTACCGTCTTCACAAATATTCGATGTGCTGTGCACGAAGAGC
AAACTGGTACTGAAACCGAAAACTGAAACTGAGAGCCATCCGCTTGCCGCTGCTCGATTTGGATTTGAGTCGATTTCAGTTGAGACCACTGAGTT
TTGCTGAGAAACCACCACCGAGTGGTTGCAGTGCTGGCAAATGCCGTTGGTTCATCTGAGTGCTTCGGTTTGCTTTTCAAATGTTTATAGCAATA
GCGCTGTTTGATATCGCTACAAAATGTATATAAATCTATGTTTTCTTAATAAATGTATGGTCCGATTTCAATCGTTAAATTTTTTAAAAATTATA
TGACCTCTAATGGAAATTCGAGTGATTTTTTATCTTTTATACATTTTTGTCGCATATATCAAGGCGCTATGTATTCGACATACATTTTTAATCTG
TGCCCTTTTTTGTTGCTAAATTATCGCGCCTTATTATCAATTTGTATATTTTCGACCGAATAATAAGAGATCAAAACACATTTGTAAGAATTCCA
AATTTATTGCGGTTTCTCCTACATAAAATTAATGTAACTATCTATAATTGCATTCGCTGTCTTGGTTTCTTTAACAGTTCGCAAAGTCGGAAATC
TACTAATCTGAATAGGATAACATCCTATCGCTTGCGATATAAGCAAGGTTTGAGAGAGAAAGCTTTCATCTTGGTGTTCTTGGGCACATGACGCA
TCTTCTTGAATTGGAAGAAGTAGAAATAGTTAACAGCCACATCCTTCTTGTTAAGATCGAATCCACATGCATTGAGGCAACGCACAAACTCCCGC
ACATCCTGGAATCGCGACTGAATCTCCGCGATATAGACAGTGCCGTGCAGCTTGAGCACTCGATTGGCCTCCAGGAAGAACTCGTTCAGATCCGT
GCCCATTAGTGAGAGGCAGTATACGGCCACGTCCAGAGTTCGAGCTTGGAGTGGAGTATCCGTGATGTTGCAGGCAATGATGTCGCTACGAGCAG
CGACCAAGTCCATGGAGTACACCTTGTTGGGCACGGATTGTGCCAATTTGCCCTCGCCGCAA
(SEQ ID NO: 787)

Exon: 15687..15634
Exon: 15328..15099
Exon: 9631..9588
Exon: 9281..9090
Exon: 8989..8544
Exon: 8485..8333
Exon: 8267..7909
Exon: 7810..7689
Exon: 7424..7311
Exon: 6600..6438
Exon: 6370..6318
Exon: 2578..2357
Exon: 2048..1893
Exon: 1683..1573
Exon: 1497..1001
Start ATG: 9236 (Reverse strand: CAT)

Transcript No. : CT22161
CAGTACCAGTTTGCTCTTCGTGCACAGCACATCGAATATTTGTGAAGACGGTACGTATTCAACGACGACGACGACGACAACAACAAATTGTCTTT
TTTCGCGAACGAATAGAAAAAAGTGGCAAAGAATTTGTTTACTAGTGTGAAAGCGAGTGAGTGCAGTGCCCACGGGAGAAAAGTGAAAACAACAC
AAATACAGGAGTAAAAATCAGCCAACCGCCAAACTAACGGTAACTGCGTGTCCTTGCTGTGGATTAAAAAGGATTCTAGAGGCGTCTTAAAAGGC
TCGCTGGAAATCATTGCCGGAGAAATTCTAGAGCTCTTTGGAACCAACTCCAAGCTGTCGCTGGCGTAGCCAAGTCCCCCAATCCAAGATGCCGG
CGGAAATTAAACCATCCGCGCCCGCTGAGCCGGAAACGCCGACCAAGAGCAAACCCAAGTCCAGCTCATCCTCGCACGGAAAGCCTGCCCTAGCA
CGAGTCACCCTGCTGGATGGCTCCCTTCTGGACGTGTCCATTGATCGCAAAGCCATTGGCCGTGATGTGATCAACTCAATCTGCGCCGGTCTGAA
CCTCATCGAAAAGGACTACTTTGGTCTGACCTATGAGACGCCCACAGATCCGCGCACTTGGCTGGATCTGGAGAAGCCGGTATCCAAGTTCTTCC GCACGGACACTTGGCCTCTCACCTTCGCCGTCAAGTTCTATCCGCCGGAGCCATCGCAGCTGAAGGAGGACATCACGCGCTACCATTTGTGCCTG
CAGGTGCGCAATGACATCCTGGAGGGTCGACTGCCCTGCACATTCGTCACCCACGCTCTGCTCGGATCCTACTTGGTGCAGTCGGAGATGGGCGA
CTACGATGCAGAGGAAATGCCCACCAGGGCCTACCTGAAGGACTTCAAGATCGCTCCAAATCAGACGGCTGAGTTGGAGGATAAGGTCATGGATC
TTCACAAGACCCACAAGGGACAATCGCCCGCCGAGGCTGAGCTACACTACCTGGAGAATGCCAAGAAGCTGGCCATGTACGGCGTGGACTTGCAT
CCCGCTAAGGATTCTGAGGGCGTGGACATCATGCTGGGCGTTTGTGCCTCCGGTTTGCTCGTCTACCGCGATAAATTGCGCATCAACCGCTTTGC
CTGGCCCAAGATTCTGAAGATCTCCTACAAGCGCCACCATTTCTACATCAAGATCCGACCGGGTGAATTCGAGCAGTACGAATCCACCATTGGCT
TTAAGCTGGCCAACCATCGTGCCGCCAAGAAACTGTGGAAATCCTGCGTGGAGCACCACACCTTCTTCCGCCTGATGACCCCCGAACCGGTCAGC
AAGTCCAAGATGTTCCCAGTCTTCGGGTCCACCTATCGCTACAAGGGTCGCACTCAGGCCGAGAGCACGAACACACCCGTGGATCGTACTCCTCC
GAAGTTCAATAGGACTCTGTCCGGAGCTCGTCTCACTTCCAGGAGCATGGATGCTCTGGCCTTGGCCGAAAAGGAAAAGGTGGCTAGGAAGAGCA
GCACCCTGGATCATCGGGGAGATCGCAATGCCGATGGCGATGCCCACAGCCGCAGTCCCATCAAGAACAAGAAGGAGAAGTTGATGCGACAGTCG
AGCACCGGCACGGCTTCGGCCTCCTCGCAAAGTTCCCTCGAGGGTGACTACGAGACCAACCTAGAGATTGAGGCCATCGAGGCTGAGCCCCCCGT
TCAGGATGCTGATAAGGAGGCTAAGTTGCGTGAGAAGAAACAAAAGGAGAAGGAGGAGAAGGAGCGAAAGGAGCGGGAGAAGCGGGAGTTGGAGG
AGAAGAAGAAGGCCGAAAAGGCTGCCAAGGCAGCACTTGCCGCTGGTGCCGCTGCAGGAGCGGCTGTTAATGGCAATGACGAGCTGAATGATTCC
AACAAGTCTGACAAGTCCTCAGGCAGACGTGCTGATGCTACACCCACCGACCTGAGTGGCGCCTATGTCACGGCCACCGCAGTCACCACCCGCAC
CGCCACCACGCACGAGGATCTGGGCAAGAACGCCAAGACGGAGCAGCTGGAGGAGAAGACGGTGGCCACCACCCGCACCCACGATCCCAACAAGC
AGCAGCAGCGCGTCGTTACCCAGGAGGTGAAGACGACGGCGACGGTCACCAGTGGGGATCAGAAATCTCCGCTGTTTACGACCTCCGCCACCACT
GGACCCCATGTGGAAAGCACCCGAGTGGTTCTCGGTGAGGACACACCCGGATTCTCCGGACATGGCGAAATCATCTCCACCCAAACCGTGAGCAG
CAAAACCCGCACTGTGGAAACCATTACCTACAAAACCGAACGCGATGGCATTGTGGAGACCCGAGTGGAACAGAAGATAACCATTCAGTCCGATG
GAGATCCGATCGATCATGACAAAGCCTTGGCCGAGGCAATACAAGAAGCGACGGCCATGAATCCGGACATGACAGTCGAGAAGATTGAAATTCAG
CAGCAAACGCAGTAGATTTTATAATTATTTTTAAACCATTCGGATGATTTTCTAAGTAAACCCGCACACACACTCACACACATGAACACCAGCCC
ACGCATACGCAGCACTTGCAGTACACCTTTTATACAACCTATATCTAAATATAATTTAAACAAATATATATATATATACACACGAGTGTATATTT
GAGCTCGAGCTGATGACCCACATGACATAACACTAAGAAACATAAAAAGATAAATTCCCAATTATCCGTTACCGCAACCGTCTACGAGAAAATGC
ATCTACATGTTTATTATTTTTATTACAACTGTTGTTTATAATTACTTTTTATTACGTATATTATATATTGAATGTGCAAGGCAACGTTGAAATGA
AAACTCTATATATTGTAAACCACGATTGCATTCAAATACAAGAATAAAACCTAAATGTACACACAC
(SEQ ID NO: 788)

Start ATG: 374 (Reverse strand: CAT)

MPAEIKPSAPAEPETPTKSKPKSSSSSHGKPALARVTLLDGSLLDVSIDRKAIGRDVINSICAGLNLIEKDYFGLTYETPTDPRTWLDLEKPVSK
FFRTDTWPLTFAVKFYPPEPSQLKEDITRYHLCLQVRNDILEGRLPCTFVTHALLGSYLVQSEMGDYDAEEMPTRAYLKDFKIAPNQTAELEDKV
MDLHKTHKGQSPAEAELHYLENAKKLAMYGVDLHPAKDSEGVDIMLGVCASGLLVYRDKLRINRFAWPKILKISYKRHHFYIKIRPGEFEQYEST
IGFKLANHRAAKKLWKSCVEHHTFFRLMTPEPVSKSKMFPVFGSTYRYKGRTQAESTNTPVDRTPPKFNRTLSGARLTSRSMDALALAEKEKVAR
KSSTLDHRGDRNADGDAHSRSPIKNKKEKLMRQSSTGTASASSQSSLEGDYETNLEIEAIEAEPPVQDADKEAKLREKKQKEKEEKERKEREKRE
LEEKKKAEKAAKAALAAGAAAGAAVNGNDELNDSNKSDKSSGRRADATPTDLSGAYVTATAVTTRTATTHEDLGKNAKTEQLEEKTVATTRTHDP
NKQQQRVVTQEVKTTATVTSGDQKSPLFTTSATTGPHVESTRVVLGEDTPGFSGHGEIISTQTVSSKTRTVETITYKTERDGIVETRVEQKITIQ
SDGDPIDHDKALAEAIQEATAMNPDMTVEKIEIQQQTQ*
(SEQ ID NO: 789)

Name: coracle
Classification: actin_binding
Gene Symbol: cora
FlyBase ID: FBgn0010434

Celera Sequence No. : 142000013384322
TCTGAATACAATTAATTACTATAATTAGATTATCGTAAACTTATATTTGATAAGGATAGATGGACTCTTTTATTAACTTGTCAGTCGAAAAATTA
AAACCATAATTTTATTAGGTTTTCTTTTTTATTTCTAGCGAATTTTGTATTAACAGTTTCATAAAGTTCAAGGGTCAAAAGTCATCATGCAATCT
TTTTATTTCAACAATAAATATTTCTGGGACTAGAAAAACACCAGATGAGAAAATATCAGATTAGATCTAGATAATTTATTCGCCCCGTCATTACC
AGCTTATTTACCAATCGCAAGTCTTATCAATATCGTACTATGTTCGAATTCTCCCAGTTGGACTAGAAAAAAAAACGCTTGTGAAATTCGTTTGG
TGAAAGCATAAATATTGTTATTATATATAATTGTGGGCGTGGCCTCAGCTTATGGCGTGTTCGGCGATCGCGCCACCTCAATATGTTAATTAGGT
ACACATGTACCTATAAAGACTTAGAGATATTTATATTAAAGTCAGACAATGGATCTATTAAATATGAGAAGAAAAATCCAAAAAAACATCACGCA
ATTGCTATTTTAATTTGGAAGTAAATGGCATTGACTGAGTAGATAAGAATGGTAGACGTTTCAAGATAATCAGAGCGAGCCTCCTTCGCAACAAA
AAAAAAAAAAGATTGGCGCCCAAGTTCAAATATTATCTAAGCTTTAACATGTCAGTTCGACTATCGTTATCGATAGTACCGCACGTACCAGCTGA
TTTTGAATTCGGGTGAAGTTGAATAAATAAGCTTAATGCCACGCGCTTTTCTAATTTGTATTCCTTATCAAAACAAGTCGGCCGTGAACTTTAAA
TAAAAGTGGCTAGCCCGCAATAGTGGAAAAGTTTTTCGCCAGCTGATAAACGCAACAGTTGTCATTCGGAAGAGAGGGACAATGCCACCCGCAAT
GCGAAAGCGATTGACAAGTCAGCCGGCGATAACGATTACATGTTTACGCGTTCGCCGAGTGCTTATTGTTTTTATACTCTCGTTACATTATTAA
TTAAAACACTTGCTTTAAGTGTGCCGAGTGTTGTGAGAGCAGCTTATCAAAGTCCGAGGTTCTAAATCTTATCTGACTGGGCATTTAGAACGTT
GTGATTACGCCGATTGCGCAACAATTTGACGATTGTACGCCACCCAAGAGAGTCGGAAACTGTAGCGCTTAACGGCACTTTACAGTTATCAGTTA
CGGTTAGAGCGCGTCTGACGCCCACAGCATTTAATTTTGCTTTGTCCGAAAATTGTTCTCTTTCCCGGGACTCCAGTGTCATATTGTCTCGTATT
GTTTCACATTGGTGACAAACACTATCGTCTCTCGTTTCCAGTCGTCGGTCGGTTCATTCATAATAATAATACCCACATCCACACCAATCCGGTTG
TAAAATGTTCGCCCTGCGCCGCACAGCCGCAATGATGACGTCGGTCCACCGGCAGCCGCATCTCAGCCAGGCCGTTTTTCGGGCCAATTTCGCCA
TCAGCGCCGCGGTAGGTCCTCCTTGTATCCTCGCCCTCTGTCGCTCTAAATCTCTTTGCTTACTAAATTTCGGAATAGGGTGGGTCGATGAGCAG
GAGAAAAAGATATTTTGAATTTTTTGAAGTCGGTCTCAATATTAAGATTATAAACAATCACGTAGTCACCTGTGCTGCTAGCATCCGATAAATAG
GATTACTATATTTACTGTTTATACAAAAAAATTGAACAATTTTTTCTTAAATTTATAACCTATGAATGCAAAGTAGAGATATTAACTTTTAGGCA
AGTACCTTAATAATTACGTCGTCACGACGAAATATTAAATATTACAAAGTAAAGATAAGGGATTACTTTTGAAACACGGTGTATTTTAATTTCCA
TCCATCAATATCGACCCACCCTATCCCAGGCTGATCAAAGTTTACTTTGCTTTGACCAGTTGTCAGTTTATTATCGTCATACATATAAGTTTCGC
CTGTATCGCCTGTGCTTAGGACCCCAAAACCCATAAGATATCCATGGATAATGAAAGGATGTCCGCCGTGAGCGAGGTGAATACCCCAATACCGC
AGCATTCAGACACAAATCCATTTTTCATGTAGCTAATAAGATTCCCATCCTGCCCTTCAAGCACTCAAGTGTGGTATGCTCTCCCGAACAGATGG
CCCAGAAGATCAAAGCCGGTCCCGTTGTGGATGTCCTCGGTGACGAGATGACCCGCATCATTTGGGACTCCATTAAGAGCCAACTGATTCTGCCC
TTCCTGGACATTGAGCTGCATACCTACGATCTTGGTATTGAGAACCGCGATAAAACCGAGGACCAGGTCACCATTGACTGTGCTGAGGCCATCAA
GAAGTACAACGTGGGCATCAAGTGCGCCACAATCACTCCCGACGAGAAGCGCGTAGAGGAGTTCAACCTGAAGAAGATGTGGAAGTCGCCCAACG GTACCATCCGTAACATCTTGGGAGGAACCGTCTTCCGTGAGGCAATCATCTGCAAGAACGTGCCCCGTCTGGTGACTGGCTGGCAGAAGCCTATT
GTGATCGGTCGCCATGCCCACGCCGATCAGTACAAGGCCGTCGACTACGTGGTTCCCGGACCCGGCAAGCTGACCCTCACCTGGAAGGGAACCGA
CGGTCAGGTGATCGATGAGGTCATTAATGACTTCAAGGGCCCCGGTATTGCCCTGGGAATGTTCAACACGGACGATTCCATTGTGGACTTTGCCC
ACGCCTCTTTCAAATATGCTCTGGACCGCAAGCTGCCGCTGTACATGAGCACCAAGAACACCATTCTGAAGAAGTACGATGGACGCTTCAAGGAC
ATATTCGAGGACCTGTACAACAAGCAGTACAAGAAGGAGTACGAGGCGGCGGGCATCTGGTATGAACACCGTCTCATCGACGATATGGTTGCTTA
TGCCATGAAGTCGGAGGGTGGCTTCGTGTGGGCCTGCAAGAACTACGACGGTGATGTGCAGTCGGACTCCGTTGCCCAGGGCTACGGATCTCTGG
GTCTGATGACCTCCGTGCTGCTATGCCCCGATGGCAAGACCGTGGAGGCTGAAGCCGCTCACGGAACGGTGACGCGTCACTTCCGCTTCTACCAG
CAGGGCAAGGAGACCTCCACCAACCCCATTGCCTCGATATTCGCCTGGACCCGTGGCCTGCTGCATCGTGCCAAGCTGGACAACAATGAGCCACT
GAAGCAGTTCGCCGACACCCTTGAGCAGGTGTGCATCGACACAATTGAGAGCGGCGCCATGACCAAGGATCTGGCCATCTGCATTAAAGGCAACA
TCAACGCCGTTACTCGCAGGGACTACCAGGAGACTTTTGAGTTCATTAACACGCTGGCCAAGAACCTGGAGGGTGCCCTGGCCAAGAATGCCGTT
GCTGCCAAATGACTATCCGGCACTCAGTCCGAGCAGCAGGCCTCGCATCTCTAGAAAACTACTCAGCGATGCCTTGTCCTCGTCACCATATTCAC
AATATTTCCATTCGTTTTTGTAGATGTGCATGTCCTAGGCTAAAAATCCGTGTCCTCGATGCATGTTTCCCACTGTTTCATTGTCTCTGCGAGAC
GCAAAAAAAAAACCCTGATTTCCCTTTAACGTCTAACGGAAAAGAAATTTCAAATAAATGTATTTTTATACCGGACTCGAGAGGTCTTTAACCCAG
TCGAGGGTGGGCTCGTTACGAGGCCCGGTCCACTTGTGCGGCTTCTGATGGCTCTGGGTTTATTGGATTTGCCAGCGAAATGGCCACAGTTGTGT
TCTAACACTTGGCGGCACCAGACCGAGACGGTTCAAGCGGAAGGGGCTCAGGATCCTGTTAGAAGGACGAAACTATCGATGCTAGCCGAAGCATT
GGGCTATGGCTACCTGCTGGCCTACGTGATCTGCCTGCTCTGCTGGCCAGGAGAGGCGTATCCCGCCAGCAGTAGCTACCGGGATCTGGATATAT
GCAATCATTGGGACGGAAGACGTCACTTCCTGGAACTGGGAAGTCCAGCTGGAGAGGTGCACGCCAGGAATGTGACTACTACTGCCTATAGAGTA
AGTGTATTTACAAGCTTCTCCAGACGGGATTTGGTCAGCAATTATGAACTTAAAAACAGAGCTCGCCGCTGGTTTTTAAGAACGATGCAGTGGCC
GGGGATGTGTGGTACCAGTGCAGCCTGGAGCTGGTCACCTGTGCCGAGTGCGTCATCCGAGTGGCCTTCACCTATGCCAACTTCTCCAAAAGTTG
CGGCAATACGGGTGGCAAGTCCAGCATGTGTCCCTGCGAGCATATCCAGTTCTCGGAGCCGCCCTATGATTCCACCATTTCCGGCCAAGAGTTCT
GTGGAGATGGCAAGGTGTTTCGGAGCAAAACCAGGACACTGCAGTTGAAATTCTTCTACAGA
(SEQ ID NO: 790)

Exon: 1001..1531
Exon: 2182..3432
Start ATG: 1430

Transcript No. : CT22171
TTCGCCGAGTGCTTATTGTTTTTTATACTCTCGTTACATTATTAATTAAAACACTTGCTTTTAAGTGTGCCGAGTGTTGTGAGAGCAGCTTATCA
AAGTCCGAGGTTCTAAATCTTATCTGACTGGGCATTTAGAACGTTGTGATTACGCCGATTGCGCAACAATTTGACGATTGTACGCCACCCAAGAG
AGTCGGAAACTGTAGCGCTTAACGGCACTTTACAGTTATCAGTTACGGTTAGAGCGCGTCTGACGCCCACAGCATTTAATTTTGCTTTGTCCGAA
AATTGTTCTCTTTCCCGGGACTCCAGTGTCATATTGTCTCGTATTGTTTCACATTGGTGACAAACACTATCGTCTCTCGTTTCCAGTCGTCGGTC
GGTTCATTCATAATAATAATACCCACATCCACACCAATCCGGTTGTAAAATGTTCGCCCTGCGCCGCACAGCCGCAATGATGACGTCGGTCCACC
GGCAGCCGCATCTCAGCCAGGCCGTTTTTCGGGCCAATTTCGCCATCAGCGCCGCGATGGCCCAGAAGATCAAAGCCGGTCCCGTTGTGGATGTC
CTCGGTGACGAGATGACCCGCATCATTTGGGACTCCATTAAGAGCCAACTGATTCTGCCCTTCCTGGACATTGAGCTGCATACCTACGATCTTGG
TATTGAGAACCGCGATAAAACCGAGGACCAGGTCACCATTGACTGTGCTGAGGCCATCAAGAAGTACAACGTGGGCATCAAGTGCGCCACAATCA
CTCCCGACGAGAAGCGCGTAGAGGAGTTCAACCTGAAGAAGATGTGGAAGTCGCCCAACGGTACCATCCGTAACATCTTGGGAGGAACCGTCTTC
CGTGAGGCAATCATCTGCAAGAACGTGCCCCGTCTGGTGACTGGCTGGCAGAAGCCTATTGTGATCGGTCGCCATGCCCACGCCGATCAGTACAA
GGCCGTCGACTACGTGGTTCCCGGACCCGGCAAGCTGACCCTCACCTGGAAGGGAACCGACGGTCAGGTGATCGATGAGGTCATTAATGACTTCA
AGGGCCCCGGTATTGCCCTGGGAATGTTCAACACGGACGATTCCATTGTGGACTTTGCCCACGCCTCTTTCAAATATGCTCTGGACCGCAAGCTG
CCGCTGTACATGAGCACCAAGAACACCATTCTGAAGAAGTACGATGGACGCTTCAAGGACATATTCGAGGACCTGTACAACAAGCAGTACAAGAA
GGAGTACGAGGCGGCGGGCATCTGGTATGAACACCGTCTCATCGACGATATGGTTGCTTATGCCATGAAGTCGGAGGGTGGCTTCGTGTGGGCCT
GCAAGAACTACGACGGTGATGTGCAGTCGGACTCCGTTGCCCAGGGCTACGGATCTCTGGGTCTGATGACCTCCGTGCTGCTATGCCCCGATGGC
AAGACCGTGGAGGCTGAAGCCGCTCACGGAACGGTGACGCGTCACTTCCGCTTCTACCAGCAGGGCAAGGAGACCTCCACCAACCCCATTGCCTC
GATATTCGCCTGGACCCGTGGCCTGCTGCATCGTGCCAAGCTGGACAACAATGAGCCACTGAAGCAGTTCGCCGACACCCTTGAGCAGGTGTGCA
TCGACACAATTGAGAGCGGCGCCATGACCAAGGATCTGGCCATCTGCATTAAAGGCAACATCAACGCCGTTACTCGCAGGGACTACCAGGAGACT
TTTGAGTTCATTAACACGCTGGCCAAGAACCTGGAGGGTGCCCTGGCCAAGAATGCCGTTGCTGCCAAATGA
(SEQ ID NO: 791)

Start ATG: 430

MFALRRTAAMMTSVHRQPHLSQAVFRANFAISAAMAQKIKAGPVVDVLGDEMTRIIWDSIKSQLILPFLDIELHTYDLGIENRDKTEDQVTIDCA
EAIKKYNVGIKCATITPDEKRVEEFNLKKMWKSPNGTIRNILGGTVFREAIICKNVPRLVTGWQKPIVIGRHAHADQYKAVDYVVPGPGKLTLTW
KGTDGQVIDEVINDFKGPGIALGMFNTDDSIVDFAHASFKYALDRKLPLYMSTKNTILKKYDGRFKDIFEDLYNKQYKKEYEAAGIWYEHRLIDD
MVAYAMKSEGGFVWACKNYDGDVQSDSVAQGYGSLGLMTSVLLCPDGKTVEAEAAHGTVTRHFRFYQQGKETSTNPIASIFAWTRGLLHRAKLDN
NEPLKQFADTLEQVCIDTIESGAMTKDLAICIKGNINAVTRRDYQETFEFINTLAKNLEGALAKNAVAAK*
(SEQ ID NO: 792)

Name: NADP dependent isocitrate dehydrogenase
Classification: enzyme

Celera Sequence No. : 142000013384534
TTTAATTATACCATTCATATGCTTGCTTTCGTTTTGCTGCCTTGCTAAGATAAAAAAAAAAAACAAAAACAATTGAACTGCGATTATGTGGTATG
GTCTGATTTCTACATGAGCAAGTGAATTGAATCGGTATTATTGGGATCTTGGGAGTTTGCAGTGAGGTGAGTGCTTGCAACAACTAAACTAAACA
CAAGGCTCACTAAACTTGTTGCATACATGTTTAACATTACTTTAAGCAAACAGTCGAATGTCCGCAAGGCGAACTATATTCGTTACATAGATCTA
GTCCGACTTACGAATATTCGACCGCATTTGTTTGTTCATTACGATTACAGTTTTTGTTGCTTGGTTTTGTTTTCATTACATTTCAGTATTATCTC
AAGTTTTGCCGGAAAACACTTCCATTCTGATCACTGGCCACTGCCCAGCTGTGGCCTTCTCCTGAGTTCCACTGCCATTTTTTACGAGTTAAAAT
TTCCAAACAAAAACTAAAGTTAAGCATAGAATACAAGAACGAAACGAACTAATCTAAAATCTATAGCGTGAAATCCAGGACTAAGGACAGTGGCA
GTGGCAACAGAACACTTCTGCGCCCGTTTGATCCTTTCACAATTTTACATTTGCTGCTTTTAGTCTATTATATTTAAGGGCTTTGCTTTTTCGCT
TATTTTTCTTTTTTTTTTTGCTTCGCTTTTTCTATTTCTCATACATGCGTTAAATGTTAATTACTTTATGCTTATGTATCAAGGATTTCTACTAC CGCGTTCTTATTTGCTGCGTGTTGTGGTGTTGCGTGTGGTCATCGCCTTCAGAAATTGTTGTTGCCATTACTGAGCAGATTGGAGGCGGCGGCCC
CAAGAGCAGCAGCCGCAATGGAAGCGGCCGAGGAGCTGCCCGCCGCCGATCCGTTGGACGCCGCAGCCGCCACCACAGCTGCCACAGCGGCTGCC
ACCGTGTTGAGATGCTGCTGATGCTGCTGCTGCTGTTGCTGGTGATGTTGTTATGGCATAAAGTAGTCCGGATGATCTGTGTCTTTCTCGAACCG
CTTGGCCTCCTCGTGCATGCTCTCCTTGATCTTCAGAATGGCCGCCGATTCCGTTTGATCGTTCTCGCCGGGTCCGCCGAATCCGCCCAGATTGT
AGTCACCCATGCCGCTGCCAGAGTCTTCGCGCGGCGTCCCAGGTCCTCCGTTGGCCGGCGAGTTTTTCATGCCATCCAAACCGGATCCGTCCGGA
CCGCCGCCGCCATTAAGTACGGGGCCCATTGAATTTGGCCCGCCGCCCATCGGTCCCATTCCGCCGGGACCACCTCCGCCACCGCCGCCATCCGG
CCCTCCGCCCATCGGGAACTCGGGTTTCATCAGGGCGTACATGCTGTCGCCCGGTCCGCCCACTGGTCCACCTTGCGTGTTATCCTGCGGCGACG
GCATTATTGGCGTTCCCGGTCCCGGCGGTCCATTCGAGCCGGGTCCATAGTTTCCTGGCGATGATGACGAGTACGCATTTAGTGGCGCCGAGGCG
TTTGGCTGCCATTGCGGCGGTCTTCCGCCCGCTCCGCCCATGCCCATGGGCGGCATTCCGCCGGGTCCCGGTGCTGGGCCGCGCATTCCTCCTGG
TCCACCATAGCCCATCGGTCCCATGCCACCAGGACCGCGTGGCGGATTCATGCGCGGATTCATCGGTCCCATCCCTCCGCCTGGCCGTGTCGGAT
CCATACTGTTGGGCATCATGGGCTGGCCGGGGGGTCCATTGAATTCATTGCCCATGCCCTGCATACGCACGCCGGGCCGCGGTCCGCCCGGGTAT
CGGGGTCCGCCCATGAACGGCGGCTGGCCTGGCATCATTTGCGACGGCGGCGGTTGCGGACTGGAGGCGTGCGTCGGCGGCGACGGTCGCATCGT
CGAGTTAGGGAAGAAATTCGGTCCCATTGGTCCGCCGGGACCCATTGGACCGCCATCGCCGCCGGGCGGCATTTGCCCGAGGGGACTGGGCGCTG
GTCCGCCAGCATTGTGGGGTCCACCCGGTCCAATTCCATTCACTCCGTAGCCGGAGCTAACAAAGCCGTAGTCGTGGAAGGCCTTGGCCTCCGAG
CTGTGATCGCACTGATCTCGGCGCTCTGGCGCCGCACAGTACAGGTCCCAGAAGACGCACCACCAGGTGTGCAGGAATCCCGGCGGCTCGCCCAG
CGTTATGTTCTTCTCCCATCGGATCTCCGAGAGGAATGTCTGTGCCGCCTTCTGGGCGCCAACGTGCAGCAGATATTCGTACACGTACAGGGCCA
ACTTTTCGCGGGCCTGGGCGTCCGATGGAACCGCCGATGTCTTTGATTTGCCGTACATTTTGTTTGTGTGATGTTGGTTGTTGGCTGTAGTTGCG
TTTTGTTTCTGCTGTTGTTGTTGTTGATGATGATGTTGCTGTTGTTGCTATTGGTGCGCTGGGTAAGGTGGTTTTAAGATTTCGGAGTTTGGGTT
TTCTCGCCTCTCTTTCGTCGCTAGTTCGCTTTTTGTCTACCGACTTCGAGCGTATTTAAATTTTTATACTTTTTTTATGTACTTTTCGAGGCTCT
TGCTGTCTTGCTGCCTCCTCTTCGGTTGTTTCAGCTTCAGCTTCTTCGTCGTCGACGTCTTCTTCTTCTTCTTCCCTTTAGCGGCTGCTACTGCT
GTGCTGTTGTTGTTTTTTAATTGGCCGCGCTTTGGCTCACGCAGCCGTTCTCCGCCGCTCTATTACTTCCACCATTTTTAATAAAATATATATTT
TTGCGAATGGAGAATGAAACGCACCGTGGTCTTTACTTTTGCCTTTACTTTTCAGATTTTACTTAATAAACTTTTTAGCGCGCTCTCGCCGTACG
TGTGTGCGTGTGTGTGTTGCCACTTCTTCGTTTTACCGTTTATTTTTTTCAGGTATTTTTTTGCCTGATTGTTGCTGCTTCTTCTTGCACAACCA
CTAAAAACAGAAAAAGAAGAGCAGAGGGAGAGAGAGAAAAAGAGAGCATGAGTGAGAGCGAGCGACAGTTCGTGTGTATGTGTGTTGCAAATTTT
CGTGAGCCTGTGTGAAGTGCGGTGTGTCGTGTATTTGTGTCAGTGTGTGCGACCGTACTTGCGTGAGTGCGAGAGAGGGAGCGCGCGCATTGTCG
ACAAAACGGCACAAGTGCCACACTAACCGTCAAAACTTTTGTACCACCTTGAACATTTTGCTAAACAGTTTAAATAAAATCAGGAGTAAAGAAGT
GGCGAAAAATTTATTTCTAATTTAACACTTTAAACTCAATTTAATGACGTAATTTTTGTATTTTTTCTTAAAATTCTTAAAATTTCTTTTCGTGA
CACATAAATTAAATTGGAAATTAAAAGTGTCTCGCTTTTACTTTGATTAAGTAATTGGATTATTTTGATTTATTTTAATTAAAAGTATAACTTGC
TAGTGCATTTCTTAAGGGGAAGACGACCTTGTCACAAACTATTTTGATAACCATTTAGAATTAGAACATTAATCTTTTACAACTTTTTACTGGGT
TTTTGTAAAACAAAAATTAGACTAACAGAGGTTTAAGTACTTAACGTGTTCGCTTTCACTAAGAGTTTGTTAGAGCTGTATTAAAGGTAAAAACT
TTATTATTTGGTGGAATACTTTTAGAATCCACTTTGTTGGATTCCCTTCTCCCTCGTTCCACTCAGGTGAGTGAGGAGCAGACAGTGATGCTCTT
GGCCTCTCGGCTTAGTACACATTGTACACAGGTAGGTTGCTACCTAAAAGCCTAAAGGCCAGCGGGCAGCATAGTCCGCCTGTCAGTCAAACAGA
CATTCAAATCAGAACTCGTCTCCGGGGTCCCAAAATATTGGTGGCACTGTGCGGGGGCGAGCGGGTGCAATTGGGGTTGGGTGGGTGGTTGGTTT
GGCAGAGTGACAGCTCGGAGAGACAGGGCGCGTAGCGATAAGGTCAATTGGCTCTGCGGACAGGTGCATCAGTTACTAGGCACTATCGGCTATAT
ATCCAATGGCTGGGAAAACTGTACGACCGATTTGAATGCGGTCGAAGGCGAACTCAACTCAAACTAGCGAATGTACACAGAGAGCGAAAACTATG
GGCTGTCAGCTGTTATCATTTAAAACAGAAGGTGTTATCGGAATCTATTATGAAACCAGGTGGCGAAACTATTCGAGTGCCCAAAACCTGTGATC
AACGACGAAGCCCAAGGGCTGAGTACCTAAACTTGCAGTGTGGCTGCTACAAAAAATACCGGTCCATCTCTCACTCTTTCTTGCTGCCGCTGCCC
GCGAGCTCTGCTGGCGTCGCTGTCAGCATGTACAACAATAACAAAAAATATGAGTAAAATCTACATTAGTGCCGATATTGCTGCATTGTTGTTGT
CTATTTGAAGACGTCATCAAATTGGGTACGCGGGTTTTCTCTCGCACGTTCTACTTTTTGCCACACACTCTCGCACACACCACACGCACGCACAC
TCGAACGCACAGCTTCACAGATGGCCGTTTGTTGATATTGTTGCTGCTGTTGCATACGCACCTTTGTTGTTTATTGTTGGCTTTGGCTATCTGTC
GTTTTGTGAACGCCCTAATACTTTGAATACTTTTATTTTGGCGAGTGTCGTGTGCTGCTGATTGCAATTTTATCACAAAATCAACAAGAAACACA
AACACACAATTCGAGAGGCTGCTGCTGCTGCGCTCGCGAAAGAGAGTAGAAGAGAGGCAGAGAGAGCGGGAGCGAGTGCGAGAGCGGCAGGGCGA
GAGGGAGGAGCGATAGCGAGAATACGGAATTTTATTACAATCATTGATTTTTCGTATTCGTATTTGTATTAGCGGCTCCCCGGCTCTTCACATGT
TTTGCGCGCATACATATAATTATTTATTATTAAACCGCGCGCTATTTTACTTCGTTTTTTTATTATTAGCTTTTTGCACCAATTCTCTTGTATTT
ATGTGACGGTGTGTGTGTGTATGTTTATTCGTTTTGCATGGATGTGTGTATGTATATGTTCGAGTGTTTTTAATTTCTTTTCTAAACACACTTTT
TTGCCTGCCGCCGCTGTGTTGTTGCTGCTGCTGTAATTTTTGCAAGTTTCTCTTCACACGCCTTTCATTCGCCGTGCGCTTTGTCCGTGTATTC
GACGATTGCTTTTACTGCCTGTTCGGCTGCTGCTGCTTCTTCTTCCACTAAAAATCGGCTCTTTTTTGCCTGTACGAAATTTTCACAGAGAGCTA
TTGCGTTGAAATGCATTTTAAATTGATGTCATTTCGAAAGCAAACACAACGTTCACATTTTCACTTTGATTGCAAATAACTATTAGTTTGGTTTA
ATCGTTTAAACACGGCAAAATCGTATAAATATTTTTACTGCTACAAGTTGCGTCGTCGTCGTCTTCGTCTCGTTCGAGTGTGACCGTTTGCCGAG
CATTTAAATAATCCGCTGCGAGCTGAGAAACGCACTAAAATTTACTAAAAGCACGCCATTTTCAGTGCTTTTAATAAATGAATATTTATTATTTA
GGTGTGGTAAAGGTTAAGCAGTACGCTTTATATGAAATAAATGGGAGGTTGTGATTAAATGAGCTAAATTCTATTAAGGTTTAATTATATTATCG
ATTAATTATGACAGGGCTGCCAGCGTGCTGGAAAAAGCTCATTTGGCGTTGCCACGGTCGCCTAAGGGTGTCTGGCAGCGTAGTTGGCAATTCAC
CAAGGAGGACCGTACAGAAGTTCGCGGATAAAATATATCTTAAATGCTAAAATAGTACGCCTTAATGATAAAGAGTTCACGATTACCTAAGTTGC
CAATGGGTAAGTTGTTTGCTTGCATTATAGACTGCGGTCTGCACCTAAACTGCTGGGCGGGGACTTACAAAAGCCGGCGAATTTCCATGTATATG
CATTTACATTGTTGTTGGCCCGCAACTGCAGTGCTGTTAGGTTAACAGCGGCAGTGTGACCAGACGCCCGTTTGTTTATGTTTGGGGCTCGAAAA
ATAACAGTGTCTGTTCAAAACGCATTCAGTGCGCAAGAACCTCCGCTTGCCGCCAAATGGAAACCCCCCAAGCGAAGCAATATTGAAGAGATCCG
AGGCATAAACAGTGCTGAGGTTTAGTGCAACTGCAACTGCTCGCGATTGCGCTACGTGCGCTGCGGTTTCCTGCTGTAATTCAAAGTTCTGCAAT
TCGCGCGATTTCCACGCCATGCAGTTGAAGCAAATGGACTGTTGATTGACTGGCCCTCAAGAGAGGAAAGCGGATTAAACGGCTTTAACAGTTAA
GTTCGAAAATGGTTGAAAAACCAATGAAACGTATTTTTTTCTTTGCACTTACAAAACGAGCACGTGATGACCGAATTTTAATGGTACCCCCCCCC
CCCCCCCACAAGGCACTTTAAACCATTCAAGTT
(SEQ ID NO: 793)

Exon: 5398..4527
Exon: 2945..1001
Start ATG: 2338 (Reverse strand: CAT)

Transcript No. : CT22195
CTCGAACGAGACGAAGACGACGACGACGCAACTTGTAGCAGTAAAAATATTTATACGATTTTGCCGTGTTTAAACGATTAAACCAAACTAATAGT
TATTTGCAATCAAAGTGAAAATGTGAACGTTGTGTTTGCTTTCGAAATGACATCAATTTAAAATGCATTTCAACGCAATAGCTCTCTGTGAAAAT
TTCGTACAGGCAAAAAAGAGCCGATTTTTAGTGGAAGAAGAAGCAGCAGCAGCCGAACAGGCAGTAAAAGCAATCGTCGAATACACGGACAAAGC
GCACGGCGAATGAAAGGCGTGTGAAGAGAAAACTTGCAAAAATTACAGCAGCAGCAACAACACAGCGGCGGCAGGCAAAAAAGTGTGTTTAGAAA AGAAATTAAAAACACTCGAACATATACATACACACATCCATGCAAAACGAATAAACATACACACACACACCGTCACATAAATACAAGAGAATTGG
TGCAAAAAGCTAATAATAAAAAAACGAAGTAAAATAGCGCGCGGTTTAATAATAAATAATTATATGTATGCGCGCAAAACATGTGAAGAGCCGGG
GAGCCGCTAATACAAATACGAATACGAAAAATCAATGATTGTAATAAAATTCCGTATTCTCGCTATCGCTCCTCCCTCTCGCCCTGCCGCTCTCG
CACTCGCTCCCGCTCTCTCTGCCTCTCTTCTACTCTCTTTCGCGAGCGCAGCAGCAGCAGCCTCTCGAATTGTGTGTTTGTGTTTCTTGTTGATT
TTGTGATAAAATTGCAATCAGCAGCACACGACACTCGCCAAAATAAAAGTATTCAAAGTATTAGGGCGTTCACAAAACGACAGATAGCCAAAGCC
AACAATAAACAACAAAGTGGTTGTGCAAGAAGAAGCAGCAACAATCAGGCAAAAAAATACCTGAAAAAAATAAACGGTAAAACGAAGAAGTGGCA
ACACACACACGCACACACGTACGGCGAGAGCGCGCTAAAAAGTTTATTAAGTAAAATCTGAAAAGTAAAGGCAAAAGTAAAGACCACGGTGCGTT
TCATTCTCCATTCGCAAAAATATATATTTTATTAAAAATGGTGGAAGTAATAGAGCGGCGGAGAACGGCTGCGTGAGCCAAAGCGCGGCCAATTA
AAAAACAACAACAGCACAGCAGTAGCAGCCGCTAAAGGGAAGAAGAAGAAGAAGACGTCGACGACGAAGAAGCTGAAGCTGAAACAACCGAAGAG
GAGGCAGCAAGACAGCAAGAGCCTCGAAAAGTACATAAAAAAAGTATAAAAATTTAAATACGCTCGAAGTCGGTAGACAAAAAGCGAACTAGCGA
CGAAAGAGAGGCGAGAAAACCCAAACTCCGAAATCTTAAAACCACCTTACCCAGCGCACCAATAGCAACAACAGCAACATCATCATCAACAACAA
CAACAGCAGAAACAAAACGCAACTACAGCCAACAACCAACATCACACAAACAAAATGTACGGCAAATCAAAGACATCGGCGGTTCCATCGGACGC
CCAGGCCCGCGAAAAGTTGGCCCTGTACGTGTACGAATATCTGCTGCACGTTGGCGCCCAGAAGGCGGCACAGACATTCCTCTCGGAGATCCGAT
GGGAGAAGAACATAACGCTGGGCGAGCCGCCGGGATTCCTGCACACCTGGTGGTGCGTCTTCTGGGACCTGTACTGTGCGGCGCCAGAGCGCCGA
GATCAGTGCGATCACAGCTCGGAGGCCAAGGCCTTCCACGACTACGGCTTTGTTAGCTCCGGCTACGGAGTGAATGGAATTGGACCGGGTGGACC
CCACAATGCTGGCGGACCAGCGCCCAGTCCCCTCGGGCAAATGCCGCCCGGCGGCGATGGCGGTCCAATGGGTCCCGGCGGACCAATGGGACCGA
ATTTCTTCCCTAACTCGACGATGCGACCGTCGCCGCCGACGCACGCCTCCAGTCCGCAACCGCCGCCGTCGCAAATGATGCCAGGCCAGCCGCCG
TTCATGGGCGGACCCCGATACCCGGGCGGACCGCGGCCCGGCGTGCGTATGCAGGGCATGGGCAATGAATTCAATGGACCCCCCGGCCAGCCCAT
GATGCCCAACAGTATGGATCCGACACGGCCAGGCGGAGGGATGGGACCGATGAATCCGCGCATGAATCCGCCACGCGGTCCTGGTGGCATGGGAC
CGATGGGCTATGGTGGACCAGGAGGAATGCGCGGCCCAGCACCGGGACCCGGCGGAATGCCGCCCATGGGCATGGGCGGAGCGGGCGGAAGACCG
CCGCAATGGCAGCCAAACGCCTCGGCGCCACTAAATGCGTACTCGTCATCATCGCCAGGAAACTATGGACCCGGCTCGAATGGACCGCCGGGACC
GGGAACGCCAATAATGCCGTCGCCGCAGGATAACACGCAAGGTGGACCAGTGGGCGGACCGGGCGACAGCATGTACGCCCTGATGAAACCCGAGT
TCCCGATGGGCGGAGGGCCGGATGGCGGCGGTGGCGGAGGTGGTCCCGGCGGAATGGGACCGATGGGCGGCGGGCCAAATTCAATGGGCCCCGTA
CTTAATGGCGGCGGCGGTCCGGACGGATCCGGTTTGGATGGCATGAAAAACTCGCCGGCCAACGGAGGACCTGGGACGCCGCGCGAAGACTCTGG
CAGCGGCATGGGTGACTACAATCTGGGCGGATTCGGCGGACCCGGCGAGAACGATCAAACGGAATCGGCGGCCATTCTGAAGATCAAGGAGAGCA
TGCACGAGGAGGCCAAGCGGTTCGAGAAAGACACAGATCATCCGGACTACTTTATGCCATAA
(SEQ ID NO: 794)

Start ATG: 1480 (Reverse strand: CAT)

MYGKSKTSAVPSDAQAREKLALYVYEYLLHVGAQKAAQTFLSEIRWEKNITLGEPPGFLHTWWCVFWDLYCAAPERRDQCDHSSEAKAFHDYGFV
SSGYGVNGIGPGGPHNAGGPAPSPLGQMPPGGDGGPMGPGGPMGPNFFPNSTMRPSPPTHASSPQPPPSQMMPGQPPFMGGPRYPGGPRPGVRMQ
GMGNEFNGPPGQPMMPNSMDPTRPGGGMGPMNPRMNPPRGPGGMGPMGYGGPGGMRGPAPGPGGMPPMGMGGAGGRPPQWQPNASAPLNAYSSSS
PGNYGPGSNGPPGPGTPIMPSPQDNTQGGPVGGPGDSMYALMKPEFPMGGGPDGGGGGGPGGMGPMGGGPNSMGPVLNGGGGPDGSGLDGMKNS
PANGGPGTPREDSGSGMGDYNLGGFGGPGENDQTESAAILKIKESMHEEAKRFEKDTDHPDYFMP*
(SEQ ID NO: 795)

Name: SSDP-like
Classification: DNA_binding

Celera Sequence No. : 142000013384839
ATAATAAAACATTCGCGTGTACTTATGTGAAGCAGACGATGTTAAATTATGCCTCCAGTACAAGGACACTTCGTGCCATTTAGACTTACAATCCG
ATCTAGATCGATTTCAAATATGGTGCCGTGATAACGTGTTAGACTTAAATGGCTCCAAGTTGTTGTGCCAACCCAATACGCACGACTTACACTCT
AAGTGGGTGCTCCTTGGACAGAATAACACGAGTTGATGATCTTGGATGATCTCTGGACCCAAAACTAAAATTTTCTGACCATATTTCGTCTATTG
TCAATAAGGCCAGGGTTGTTCTTGGTTTTATAAAAAGGTGGTCTAAGGAATTTGATGATCCTTACTTGACTAAAACCTTATTTATTTCGTTAGTC
CGTCCGATTCTCGAGTACGGATCACCTGTTTGGAGTCCACAATACGCAGTCCACTCGGACCGCATTGAATTGGTCCAAAAAAAAATTCTTACTTT
TTGCCTTGCGGCGCCTAAATTGGGATGCAAACCGTATATTACCTCCTTATATTAGTAGACTTCCTTTAATTAATTTACCGTCCCTAGCTAACCGT
AGAACTATGCTTGGAACAGTCTTTATTTGTAAGCTTATTCGTGGGGATGTTGAGAGTCCCGACTTTATTAGTCGGCTTAACTTTTCGGTTCCAAG
TAGATTCACTAGAAACTATATACCCCTTATCTTAAATCATTGTAGATCTAACTATGAGTTGCATGACCCTTACAGAGTTTTATGTTCTGACTATA
ATAGACTTAACTCTCTGCCGCTCTTAAAGCAATCGATTTTAACTTTTTTATTACATAATTAGATCCTACTAACAGTAATATTTAATATAGTTATT
TTACATTATATTCATTTCCTCGTTCCTGTTCTCTTTTTTATATCGCGTCTATATCTTCTCGCGAATCGAGCCGTACGATACACGGCAGCGCCCCT
CGGTCGGTTGGGCGGGAGGTGTGGACGTAGGACCCGTGCGAACAAAAAAAAAAAAAGAATCGAATTCTTTTAGCCTTCTCAAACGGTTCTTTCTT
CTACATGCGATTTGTGCCCAGTTTTCCTGTGTGGGTTTGCAAGTGTGTTAGCAGTGCGGATTTCCGCGAAAAAGTCCTTGGGCAGCTGGAACACT
TAAACGGTTTTCTTTGTGCGTTACTATGTGCCGGCTTAGATCCTGAAGATTTGCAAGGACCTTCGAGCAATGGCTTATTTTTGGTGTGTGATTTC
AAGTGAGTGGACAGAGCCGAACGGTCAGTGAAAGTTTTTGGGCACTTACCACACTTAAGTGCCTTTGAGTGGCCTAGTGTTTTGTGAGCAGATGC
TTTTGAGCTTTGAGAGCATCTCGCGTTCCTTGACAGGTGTCGCTTGAGATACGCATGTAGCGCAAAGTCCTTTGAGCAATGGCCACAAGTAAAGA
GGCGTTCTTGGTGCACTCGCATGTGCATCCAAAGTTCATGTTCGACTTGAAAGGACTTCGAGCACTGGGAACACTTGAACTGCGTTTCATCAGTG
TGCGTGGCCAAATGCTGCTTGAGAATTAAAGAAGTTAGAAAGCACTTTTGGCAGTATGGGCACCTTAACGATCCTCTTCTTTCGTGCATCTGTAT
GTGGGCCTTGAGGTGGTGCCCAGCTGTAAAGGACCTTGGGCAATGCGAGCACTGGAAGGGTCGTTCTCCTGTGTGGGTTCGCATGTGATTCTGAA
GACCAGAGCTATAGCCAAAGGACTTGGGGCAGAGGGAACACGTGAAGGGACGTTCTCCTGTGTGTGAACGCATGTGTACCTTCAGATTTGATTTT
ACTTGAAAAGATTTAGGGCAGTGAGAACAGCTAAAGCCTGGTTTCTCCTTGGCCTTGATATCACATTCGTTAATATCAGGTTCATTGCCGGAATC
GACGTCGTCGGCACCATCCTGGAGATCCCTCTCAGCTGCCTCCACTTCTTCTGAGCATCCGGATCCATCATTTTCACTCTCCTCCTCCCGTACAT
CCTTGAGGAAGCGGTAAAACTGGTGACTTCTCTCGTACGTTTCTATGATATCGAATGCATTCTGCGCATCCTCCAGACAGGACTTGCATATGGTG
TTGGACAGTGGATCGTGCTTCTCAACTTGCCAGCCGGTGCACTTGTATATTATGTACGCAATGGATAGGCCCGGTTCATGAGACTCATCGAAAAC
ACTGGCCATATTTTCGTAACTGACCAGGCAAACTCGGCATATTGACGATTCCATCGATCTGAAATGACACGAACTGTGTGAATATAAAATTGCGA
ATATACAAAATCGTGCACTTAAACGGTTTCAAAAAAGTATAATGGTTATTCCCAGATCTTTGAGTATTAGCGTTTCTGGAATCTACATCCTGAAT
GCTAAATACACTGAGATCTCAACTTTCAAACAAACGGACAGAATAGGTACGACTAGATCGTAGTCATGGATGACACATACACTTTATAAGGTCAG
TGACAAACGTCATCTTTTAGTTGCATAGCATCAAAAAGAACCCTCTGCACTCTTTCTTATATTTAATAATCAATGAAATTTAATACTTGTGTAGA
GCTTTAAACATAAATTGCACTAATTTCCAAATACATCTTGGTTTATTTATGACTTTGCTAACTCGGCACGAATTGACCCACAATGGCAATCCTTA
CCTTAAACTTACCTTATTTTCGTGTTTGTTCACGGCGAATGCGTATTTAAAATGTGGCAATAAGCACAGGAATTGGCAATCTGTAAAGATGTTGC

FIGURE SHEET 432

TATGACAAGGGTTGTACTCCTTCTGAAGTGAATAGGTAAGTCGTAAGGCTTATATACAAACATGTCCCAAGGTCGTTTGGTTCTGTAAAATGGGC
AACATAGCATATTTAACAATGTTACCTGGGTCAGGTGTCATCAAAGAAGGGCTTTCCAGCAGCTGCACTCATCTTTTTACGGTGCGTCCCAACTA
ATCTTACGATTTTCTGTAGATCCAAGCAGGTCAATGCATAATGTGATACATGCAGGTAAAAGTAACTATGGTTAAAGAAAAAATCTTTCCTTGGT
CGACCCCAAAGTGCTAAATCATTATTGCTGAACTCTAAAACCATGTGTTTGTAACGAAATATACTTATTGGGGTGGTGGAAAACAGGGGAAAACC
ATTTACCCAATGACCAATAAAGCTAGCCATACCCTTCTATTCCCAATATACCCCATGGCGGAATCATTCTAGTAGCAAATTATTCAATAAAAAAC
(SEQ ID NO: 796)

Exon: 2230..1001
Start ATG: 2194 (Reverse strand: CAT)

Transcript No. : CT22233
TCAATATGCCGAGTTTGCCTGGTCAGTTACGAAAATATGGCCAGTGTTTTCGATGAGTCTCATGAACCGGGCCTATCCATTGCGTACATAATATA
CAAGTGCACCGGCTGGCAAGTTGAGAAGCACGATCCACTGTCCAACACCATATGCAAGTCCTGTCTGGAGGATGCGCAGAATGCATTCGATATCA
TAGAAACGTACGAGAGAAGTCACCAGTTTTACCGCTTCCTCAAGGATGTACGGGAGGAGGAGAGTGAAAATGATGGATCCGGATGCTCAGAAGAA
GTGGAGGCAGCTGAGAGGGATCTCCAGGATGGTGCCGACGACGTCGATTCCGGCAATGAACCTGATATTAACGAATGTGATATCAAGGCCAAGGA
GAAACCAGGCTTTAGCTGTTCTCACTGCCCTAAATCTTTTCAAGTAAAATCAAATCTGAAGGTACACATGCGTTCACACACAGGAGAACGTCCCT
TCACGTGTTCCCTCTGCCCCAAGTCCTTTGGCTATAGCTCTGGTCTTCAGAATCACATGCGAACCCACACAGGAGAACGACCCTTCCAGTGCTCG
CATTGCCCAAGGTCCTTTACAGCTGGGCACCACCTCAAGGCCCACATACAGATGCACGAAAGAAGAGGATCGTTAAGGTGCCCATACTGCCAAAA
GTGCTTTCTAACTTCTTTAATTCTCAAGCAGCATTTGGCCACGCACACTGATGAAACGCAGTTCAAGTGTTCCCAGTGCTCGAAGTCCTTTCAAG
TCGAACATGAACTTTGGATGCACATGCGAGTGCACCAAGAACGCCTCTTTACTTGTGGCCATTGCTCAAAGGACTTTGCGCTACATGCGTATCTC
AAGCGACACCTGTCAAGGAACGCGAGATGCTCTCAAAGCTCAAAAGCATCTGCTCACAAAACACTAGGCCACTCAAAGGCACTTAAGTGTGGTAA
GTGCCCAAAAACTTTCACTGACCGTTCGGCTCTGTCCACTCACTTGAAATCACACACCAAAAATAAGCCATTGCTCGAAGGTCCTTGCAAATCTT
CAGGATCTAAGCCGGCACATAGTAACGCACAAAGAAAACCGTTTAAGTGTTCCAGCTGCCCAAGGACTTTTTCGCGGAAATCCGCACTGCTAACA
CACTTGCAAACCCACACAGGAAAACTGGGCACAAATCGCATGTAGAAGAAAGAACCGTTTGAGAAGGCTAAAAGAATTCGATTCTTTTTT
(SEQ ID NO: 797)

Start ATG: 37 (Reverse strand: CAT)

MASVFDESHEPGLSIAYIIYKCTGWQVEKHDPLSNTICKSCLEDAQNAFDIIETYERSHQFYRFLKDVREEESENDGSGCSEEVEAAERDLQDGA
DDVDSGNEPDINECDIKAKEKPGFSCSHCPKSFQVKSNLKVHMRSHTGERPFTCSLCPKSFGYSSGLQNHMRTHTGERPFQCSHCPRSFTAGHHL
KAHIQMHERRGSLRCPYCQKCFLTSLILKQHLATHTDETQFKCSQCSKSFQVEHELWMHMRVHQERLFTCGHCSKDFALHAYLKRHLSRNARCSQ
SSKASAHKTLGHSKALKCGKCPKTFTDRSALSTHLKSHTKNKPLLEGPCKSSGSKPAHSNAQRKPFKCSSCPRTFSRKSALLTHLQTHTGKLGTN
RM*
(SEQ ID NO: 798)

Name: zinc finger protein
Classification: transcription_factor

Celera Sequence No. : 142000013384534
ATGCATACATAGATAGCTATATGACATCCAGACATTCATGCCACATGCCACTATTATACACACATACTATATAAAACATGTTTACTACTCCACGA
CTCAAATTTGCAAATATTGTACGCTATTTAGCCTAGCAGTTAGAGCAGCATACCCATAATATATTTATATGAAACAAATCGCCCAGCAGGACACA
TAAATTGTGGTATGTATGTGCGTGAGTGTATTTTTGTATGTACTACCTATTAAATATAGAAATATATATATATATATATATGTGCGGAGAACCGTGT
TCCTGAACACCGATCAAAAGGAATTAGGCATTTTTGTTTGTCCTGGACTGGCCGTGGATGATCCTGCGGACCGCCAAGGAATAGAGATGTGCCAA
TTTCTGGTCCACCAAGCACAGTTGATAACCTATAAGCATCCTTACAACGTCACCACAACAGACTGGGACAAATTGCTGGTCGTAGCGTCTACTTC
TATACGTTAATCTATATCTATATGTTAAACTGTAATTTTGGATCCGTGTCAACCAGTCGTTTAGTTCCATAGTCAAGTCATTACCGGGTCCGTTA
GACAAGGATTTATGCAGATACTCTCAACTAATCTAGAATCTAGACAAAGGCGACGAAGCAGATCAAAAGAGTTTTGCTACCACTACCAAGTGCTG
TACACGCCAAAAACGAAAGGCTTCAGTTTAGCTATAGACACAAATATATATATATATATATATATTATATAAAGAGATGTATTTACATATTTTTG
GCATTATAGATACATACACAATGTGGAAAATTGCAAAACAATAATATGGGTGGAGAGGTAAAGGGAAAGTAATTCTTAGAAAGGCAGATTTTTTC
ATACAGGAAACGGTGAAAATCAAACTTTTCAACATAAGAATTAAACATATATATATATATGGGAAAACCAAAACCTATAAAACATTTACTAAAAG
TGAAACCAATAAATGAAAAATGAGTTATACACCCTTAAAACAATATATATGTGCAAATTGTAAATGGAGCATGTAATTTTGTAAAAATTATAAAT
AAAAGTTTATCAAGTCGAGAACTTTTGAACTTAAGTTAAAATTGGAGACAATTTACAGAGCTGACGGCCTATTTAAATACAAACTAAATACAATT
ATAGAAACTAGATCAAAATCCGGATGGATAAAGATGTCATTTGGCCACTTATTGCATACACTCATTTCACTGGAACTTTTCTGTAAGTCCTCGGG
TCTTCATTGCCATTTCCGACAAATGTTGTTGCAATAACCTCTTGTTGACCTTTTCCCTGTGAAAAAATTTATAAAATTAATACAATCTTTAAGGA
TCTATATATAAGTAACGCCTCTCACTTGATTATTAGAGCAGTGTAGCGCGTTTTATCCGCGTCGGTTATGAGCTGTGTGGGGAAATTGGGAGTGG
ACATTAGGGACTTCATCCAGACGGCCATCTCGGCGGCATATTTTCTGTTCATGGCAAGAAGGATGTCTGCAAACTTATCCACCTGCGACCGCGGC
GTTAGGTAGCCCACGCACATCATCGCCGTGTACAGCGTCTGCTCGCCGGTGGCCAGGACAACTTCTGTGACATGAGCATGGTTACGCGACTGCAT
CACAAAGTGGGTAAGAAACTGTATGCTATTTCGGATGGCACCACTCTCCGGCAAAGTCATTCCACGCTGGGCGTAAAAGACCAGACGATCGTAGG
CCAGTGTCTTGTCCTCCAAAACTTGAGGGATTTCTTAATGATCTGCGTCAGACAGCCGAAGAAGGTTTCCATGGTGTCCGAAATGTTGGAGAAG
TTCTGCTCGGGAGTGCTCTCAAATAGCTTAAAGCTGTGTTGGATGAACTCCCTCAGAAGTTGCTGCATCAGCGGCTTGCAGCCTTCGTCCTTAAA
GAACATAACAATGGCCTGAAACAAAGGATTCTATTAGATCACTCAGTCATTTGCAATATATTGGTAAGGCTCACCGTTTTGGATATTTCTAGAGT
AGGAGCGCAGCATCGGGTCTGAAAGCTGGCAACAATGAAGAGACAAAGATCCTGCAGCATTGGCTGGAAGCTGCTCCTTAAATTCGTTATCGCAT
GCTTCATCGCACTGCAAGCGGCCTATATGAATACGATAACATTTTATTAAAAATATGCAAAATTTTGTGTTTATTGCCTTACCTCTAGGACATCG
ATCTCCTCCACCCACATCTCGGCGATTCTCTTGAAGATGGGCATCGTGCGCTGCATGACGAGCAGAACTGGCTGCACAATCGGTTGGTCCGTCGC
CTGCTCGTCCACATCCGTGTTTAGCGAGGAGAAGAGAGTGGAGATCATATTGAGCCGGAAGATTGTGCGAATTCGAGCAGCGGGAGTTTTCTAGT
GCAACAAAAGAAATGGTTAGCAACTGATCTCTTTATATATTTTATATTTATATTTACTCACCGAATCTGCCTGGCAAATGGCCTGTAGCTCCTCG
AAGCAGGGACTGACGATAATATCCAAGTATTTGGGTATTTCCTCTGGCCGCAGCAGGCTCATTAGCTTACCGATGCTGAACATAAGCCTCACCGA
ATCGGAGTTCTTCATGCGGCCCGTGTTTAGGGAAGCGTGGCATGCGTTTAGGAGCGGATCCGCATACGGCTTCAGCTGCAGCTGACAATCGCGAC
ACAGCTCCTTCAGGCCGAGCGTCGCCTGTGCTGACATTGAGGAGTTGAGGCCGCGCACCAGTAGGTTAATGGCTGGCGGAATGTACGCCGGATTC
TCCATCAGCCAATTGCAATAGGAGCCCATTGTCTCTAGCGCAGTGCCCAGTAGCTTGACATTGAGCTTCTCGTAGGGAATCTCGGCCAGCACGCG
CATCAGCCGTGGTATTTGCCGCTTCTCCTCGCCACCAAAGTGCTCGGCCACCGACTGAAAGGAATAGATGCACGCCTCCAGCTTTGTCCAGTGTG TGGGATGTCTTTGCAGATCGGCAATGGCCTCGTCCAACATGGCAGCCAGAATCTCCAAGATATAGTCATTCAACACATCATAGCAATACATCTAA
AATAAATAAAATAAATGCTATATTATGCCTGTTTGTTAATAGTTGAAAACGGTAGCCAATCCTTTCGATTTGGAGACACTCCAACTGTTGCAACC
ACTCACAAAGGTATCGGATATATCCTGTCTGTAGCACCTAAAGCATTCCAAATCATCGGAGCTCCACTTGGCGAGCGACTTTTCGTCTGGCTGCT
CTGACTTTCTTACTAAAATCCTGGTTAGATGGGCGTACAATGGTTTGATGTACTCCCAGCACTTGTGTTTCTGCTCATCGTTAGACATGGCGAAC
ACTTCGTCTTGCAGCATATACCAAAACGCCAAGGCCATTGTGCTGCAGGACTCCTCCACCGGGTAAATGCCCGGCTTGTCCGTGCAGTGGAGAAT
CTCCTGCACGATGCGATGCACTAGGATAGACAATTCCGGATCCGCGGACGTGATGCCGCTGAGCAACAGCGTCGAATGTCGCTCCACCGAAGAGA
CGAACAGCATGTAGATATGTACGATAATGTCCTCGTTGTCGTTCTCCCTCTTCCATTCCGTCTTTGTGATTTCGGATAGCGAGTCCAGGAACATT
TTTATAAGCACAAATGCCGTCTTTGGATAGTTGTGGCAGTCTGGCTGGATGATAATGTTCACCATGGTCTTCAGACAGGACTCGGCCAGTTCGTT
CTCATCGGCGGTCATGCAGCCGTCGCCGGCGTGTATGCAGGGCCAATAGCACTTGTGCACCACTTCCAGGAGCACGGCGGTGATGGTGACGCAGC
CCTCAATGGTGTAGCCGATGTTTCTGTCCAAGTTGGAAACTCACTTAGAACGTGTAAAGAATAATTTTGTAAATTGAATACTCACTTGATCCAGG
TGCCGACGCACTTAACGGCCCTGTTCATGTTACTGTACGCCTCGGCATCCCACACGCGGTTCATTTGCAGCTTCAGATATCGCTCAACGGTGTGA
ATGACCAACTGCACTCGCTTGGCGATCTCGGCGCGCAGAACAACCCGCTTGACAGACGTATGTATGACCTGCGCTTCCTCGGGAATGGCGGTCAG
CACCTCCAGCATGATCCACAATTGCACATCGGCGCTGACATTTGGCATCCGTTGATTCTGAAACGTGTTGATCACCTCCTCGATGGCGCCGGGCC
ATTCGCCCAGCATGTGAACGATGTAAGCGCCCAGCGAGATGCACAACCGATTGAGGACGATCTTCGGTCCGCCAGCGAAGCGAACGATGGATTCG
AGTATCTTTTGCTTTAACTCCTCGCGATTCTCTGGCGGCACTTCGTGCCAGTGCTTCATAAGCTTGGAGTGCAGCGTGATGGCGCCGAAGAACTG
CACCTCCTGACTCTGTGTGGGCGGTGGGGTGATTGGGTGGGCGGTAGGTGCATGAGTATACATATCCGGGTAATTGATGCATTGATGCGCAGGTC
CTGCGTGGTACTCACCTTGCCGAGCTGCATTAGCTGCCAGGAAAACTGCCAGGCCTGTGGACTGGCCTCCGCATCGGTAAGCCATTCATGGTGA
TCGCCTGGTTCTGCGAGTTCGAGCGGTAGAACGACACGACCGCCTCCTCCAGACGCGCAATGTCAATGGGCTCCATGTGGAATGGCTGCTGCTGC
TGCTAATGCTGCTGCTGCCGAGAGGCAGTCTCCTGTCCGCTAATCCTCGGGTGGTGGTTTTCTTTGCTTCTGCCTGTGGGCACTGGATTCGCGAG
TGTGACCAACGCGCGAAGTCACCAATTCGCGGACGGGCCGAGTGTGCGGTCACTCCATTTTCGACTTTGCCGCGCTTTTTTTCCTCCTGTATTTT
TTATAAAAAGTGTTGAAATGTACGTATTTAATAATAAATAAATATGTAATATAGTATAAATTGCTTGTGGCCTATATGCTCGATATATGCAGGAA
AAATTCAATTTATAACAACATTTATTCATTCGTACACTTCATAAAATTTTACTATTTCTATTTAGTAAATACTCTCTGCAATTGAGGAGTATCTT
AACAAGTTAACAGTGAATTTGGAAAGCCCAAAAAGTCCTATATAAAATCGAATTTAAGTTGCCAGAAACAGTATCGCAATTTGGAACACCGGTCG
GCGATGAAATCCCTGCTATCCTCATCGATATACACCTCAATAAGGACGTTGTCGCAGAATTGAGCGACCTGCCTCTCCACGTCTTGGCAGTCCAA
AGTGGAGCGATTAACGACGGCCCATCTGTCGGTATTCAAGCCCGGGTTCTGTGACTCCAGTAATGCGAAGATCACACAGAGCGACTTATTCGGAC
TGACCAAGGGCAGGACAAAGGTCGTCCTCACTAGATCGAAGAACTTAATGAAGGGCTGGCAGGAGTGGGGCGGCTCCACACCTTCGACTGCTTCG
ATGACCCATTGGGCCGTTTCGTTATCCTCGCAGACCACCAGCATGTTGCAGTCGAATGTCTGCGTTGAGGCACACTCACTAAAATTGAGATCGCT
GACGCTCGATCCACTGTCCTCGAATATTGAATGAAAGTGCTCCATTAGGGCGATAGTGTCCACACCATCCGAGCACGAACTCTGGTTAGTTATCA
CCAAGGCGTAACGTCGGTTCTCGGGCATTGTGTTCGCATACGGCGGCCGAGTATCCCTCTTGCGACAATTCTTTGGCGTGCAGCAGTCCTTCTTC
CTCTCCTTGCACTCCTCGGCCTGCTCCACTGAGCAGCTTGT
(SEQ ID NO: 799)

Exon: 4741..4481
Exon: 4382..3886
Exon: 3823..3142
Exon: 3036..2437
Exon: 2370..2173
Exon: 2112..1975
Exon: 1915..1356
Exon: 1291..1001
Start ATG: 4636 (Reverse strand: CAT)

Transcript No. : CT22245
CCAGTGCCCACAGGCAGAAGCAAAGAAAACCACCACCCGAGGATTAGCGGACAGGAGACTGCCTCTCGGCAGCAGCAGCATTAGCAGCAGCAGCA
GCCATTCCACATGGAGCCCATTGACATTGCGCGTCTGGAGGAGGCGGTCGTGTCGTTCTACCGCTCGAACTCGCAGAACCAGGCGATCACCCATG
AATGGCTTACCGATGCGGAGGCCAGTCCACAGGCCTGGCAGTTTTCCTGGCAGCTAATGCAGCTCGGCAAGAGTCAGGAGGTGCAGTTCTTCGGC
GCCATCACGCTGCACTCCAAGCTTATGAAGCACTGGCACGAAGTGCCGCCAGAGAATCGCGAGGAGTTAAAGCAAAAGATACTCGAATCCATCGT
TCGCTTCGCTGGCGGACCGAAGATCGTCCTCAATCGGTTGTGCATCTCGCTGGGCGCTTACATCGTTCACATGCTGGGCGAATGGCCCGGCGCCA
TCGAGGAGGTGATCAACACGTTTCAGAATCAACGGATGCCAAATGTCAGCGCCGATGTGCAATTGTGGATCATGCTGGAGGTGCTGACCGCCATT
CCCGAGGAAGCGCAGGTCATACATACGTCTGTCAAGCGGGTTGTTCTGCGCGCCGAGATCGCCAAGCGAGTGCAGTTGGTCATTCACACCGTTGA
GCGATATCTGAAGCTGCAAATGAACCGCGTGTGGGATGCCGAGGCGTACAGTAACATGAACAGGGCCGTTAAGTGCGTCGGCACCTGGATCAAAA
ACATCGGCTACACCATTGAGGGCTGCGTCACCATCACCGCCGTGCTCCTGGAAGTGGTGCACAAGTGCTATTGGCCCTGCATACACGCCGGCGAC
GGCTGCATGACCGCCGATGAGAACGAACTGGCCGAGTCCTGTCTGAAGACCATGGTGAACATTATCATCCAGCCAGACTGCCACAACTATCCAAA
GACGGCATTTGTGCTTATAAAAATGTTCCTGGACTCGCTATCCGAAATCACAAAGACGGAATGGAAGAGGGAGAACGACAACGAGGACATTATCG
TACATATCTACATGCTGTTCGTCTCTTCGGTGGAGCGACATTCGACGCTGTTGCTCAGCGGCATCACGTCCGCGGATCCGGAATTGTCTATCCTA
GTGCATCGCATCGTGCAGGAGATTCTCCACTGCACGGACAAGCCGGGCATTTACCCGGTGGAGGAGTCCTGCAGCACAATGGCCTTGGCGTTTTG
GTATATGCTGCAAGACGAAGTGTTCGCCATGTCTAACGATGAGCAGAAACACAAGTGCTGGGAGTACATCAAACCATTGTACGCCCATCTAACCA
GGATTTTAGTAAGAAAGTCAGAGCAGCCAGACGAAAAGTCGCTCGCCAAGTGGAGCTCCGATGATTTGGAATGCTTTAGGTGCTACAGACAGGAT
ATATCCGATACCTTTATGTATTGCTATGATGTGTTGAATGACTATATCTTGGAGATTCTGGCTGCCATGTTGGACGAGGCCATTGCCGATCTGCA
AAGACATCCCACACACTGGACAAAGCTGGAGGCGTGCATCTATTCCTTTCAGTCGGTGGCCGAGCACTTTGGTGGCGAGGAGAAGCGGCAAATAC
CACGGCTGATGCGCGTGCTGGCCGAGATTCCCTACGAGAAGCTCAATGTCAAGCTACTGGGCACTGCGCTAGAGACAATGGGCTCCTATTGCAAT
TGGCTGATGGAGAATCCGGCGTACATTCCGCCAGCCATTAACCTACTGGTGCGCGGCCTCAACTCCTCAATGTCAGCACAGGCGACGCTCGGCCT
GAAGGAGCTGTGTCGCGATTGTCAGCTGCAGCTGAAGCCGTATGCGGATCCGCTCCTAAACGCATGCCACGCTTCCCTAAACACGGGCCGCATGA
AGAACTCCGATTCGGTGAGGCTTATGTTCAGCATCGGTAAGCTAATGAGCCTGCTGCGGCCAGAGGAAATACCCAAATACTTGGATATTATCGTC
AGTCCCTGCTTCGAGGAGCTACAGGCCATTTGCCAGGCAGATTCGAAAACTCCCGCTGCTCGAATTCGCACAATCTTCCGGCTCAATATGATCTC
CACTCTCTTCTCCTCGCTAAACACGGATGTGGACGAGCAGGCGACGGACCAACCGATTGTGCAGCCAGTTCTGCTCGTCATGCAGCGCACGATGC
CCATCTTCAAGAGAATCGCCGAGATGTGGGTGGAGGAGATCGATGTCCTAGAGGCCGCTTGCAGTGCGATGAAGCATGCGATAACGAATTTAAGG
AGCAGCTTCCAGCCAATGCTGCAGGATCTTTGTCTCTTCATTGTTGCCAGCTTTCAGACCCGATGCTGCGCTCCTACTCTAGAAATATCCAAAAC
GGCCATTGTTATGTTCTTTAAGGACGAAGGCTGCAAGCCGCTGATGCAGCAACTTCTGAGGGAGTTCATCCAACACAGCTTTAAGCTATTTGAGA
GCACTCCCGAGCAGAACTTCTCCAACATTTCGGACACCATGGAAACCTTCTTCGGCTGTCTGACGCAGATCATTAAGAAAATCCCTCAAGTTTTG
GAGGACAAGACACTGGCCTACGATCGTCTGGTCTTTTACGCCCAGCGTGGAATGACTTTGCCGGAGAGTGGTGCCATCCGAAATAGCATACAGTT TCTTACCCACTTTGTGATGCAGTCGCGTAACCATGCTCATGTCACAGAAGTTGTCCTGGCCACCGGCGAGCAGACGCTGTACACGGCGATGATGT
GCGTGGGCTACCTAACGCCGCGGTCGCAGGTGGATAAGTTTGCAGACATCCTTCTTGCCATGAACAGAAAATATGCCGCCGAGATGGCCGTCTGG
ATGAAGTCCCTAATGTCCACTCCCAATTTCCCCACACAGCTCATAACCGACGCGGATAAAACGCGCTACACTGCTCTAATAATCAAGGAAAAGGT
CAACAAGAGGTTATTGCAACAACATTTGTCGGAAATGGCAATGAAGACCCGAGGACTTACAGAAAAGTTCCAGTGAAATGAGTGTATGCAATAAG
TGGCCAAATGACATCTTTATCCATCCGGATTTTGATCTAGTTTCTATAATTGTATTTAGTTTGTATTTAAATAGGCCGTCAGCTCTGTAAATTGT
CTCCAATTTTAACTTAAGTTCAAAAGTTCTCGACTTGATAAACTTTTATTTATAATTTTTACAAAATTACATGCTCCATTTACAATTTGCAC
(SEQ ID NO: 800)

Start ATG: 106 (Reverse strand: CAT)

MEPIDIARLEEAVVSFYRSNSQNQAITHEWLTDAEASPQAWQFSWQLMQLGKSQEVQFFGAITLHSKLMKHWHEVPPENREELKQKILESIVRFA
GGPKIVLNRLCISLGAYIVHMLGEWPGAIEEVINTFQNQRMPNVSADVQLWIMLEVLTAIPEEAQVIHTSVKRVVLRAEIAKRVQLVIHTVERYL
KLQMNRVWDAEAYSNMNRAVKCVGTWIKNIGYTIEGCVTITAVLLEVVHKCYWPCIHAGDGCMTADENELAESCLKTMVNIIIQPDCHNYPKTAF
VLIKMFLDSLSEITKTEWKRENDNEDIIVHIYMLFVSSVERHSTLLLSGITSADPELSILVHRIVQEILHCTDKPGIYPVEESCSTMALAFWYML
QDEVFAMSNDEQKHKCWEYIKPLYAHLTRILVRKSEQPDEKSLAKWSSDDLECFRCYRQDISDTFMYCYDVLNDYILEILAAMLDEAIADLQRHP
THWTKLEACIYSFQSVAEHFGGEEKRQIPRLMRVLAEIPYEKLNVKLLGTALETMGSYCNWLMENPAYIPPAINLLVRGLNSSMSAQATLGLKEL
CRDCQLQLKPYADPLLNACHASLNTGRMKNSDSVRLMFSIGKLMSLLRPEEIPKYLDIIVSPCFEELQAICQADSKTPAARIRTIFRLNMISTLF
SSLNTDVDEQATDQPIVQPVLLVMQRTMPIFKRIAEMWVEEIDVLEAACSAMKHAITNLRSSFQPMLQDLCLFIVASFQTRCCAPTLEISKTAIV
MFFKDEGCKPLMQQLLREFIQHSFKLFESTPEQNFSNISDTMETFFGCLTQIIKKIPQVLEDKTLAYDRLVFYAQRGMTLPESGAIRNSIQFLTH
FVMQSRNHAHVTEVVLATGEQTLYTAMMCVGYLTPRSQVDKFADILLAMNRKYAAEMAVWMKSLMSTPNFPTQLITDADKTRYTALIIKEKVNKR
LLQQHLSEMAMKTRGLTEKFQ*
(SEQ ID NO: 801)

Name: nuclear transport receptor
Classification: receptor

Celera Sequence No. : 142000013384139
AGGCCACCACGGCGGCGCAGGTGTGAATGAATATGGAGGAGAACAGGGCCCACAGAAAGACGTGGTACCACATTTCGCGAAACGTATTGAGACGC
GCCTGTGACCGGAGTCCCATCACATCGGCGATGGTGTCCAACTCATCGGTGTCGTCCGAGAACATGGCTAAAACGTAGTCGATGGATGTTGACGT
GGTATCCCTAGTTACTAGTTGCTAGTTATTGCTTTTCCGTTGGTCAGTTGAGTGTCCAGCCGCATGTCTGGTGGGGATTCCCTTTCTATAGCATG
TATCCAGCCAATATTCATGGACCTGCAAACAATAACTCCCTTTAGACTTGACCTTCTGGCATTTAATTATACTCACGCCAACACATGTGTGTGCT
AATGGCCACACCCATACCACATTTGTCGTATTCTATAGCCGGATTTGGATTGCAGTCTTTTTCAGTTGCTTGATCCTATTTAGCATGGCCTTAAC
TTCCGGTTAGCACTGTAGTTTAGCAAATGTTTGGCTTATTTTTAATTCGGTCAACAATCGATTGAACTTTCGTCACGGCACTCAATTAGCGCTCG
GCTGGCGGCAGTGAATGCTAAATCGGGCCTAATTACCAGGCTACTGGTGTGCGGCAGCCCTAACTCCACATTTTGAGCAACACCAAACACTTTTA
GTTGGTTTAATTTAATTTTATATTGTTCTTGTCTGCGATTTACTATGGCAATGGGAATGGAACGTTTGGGATTGGGCCAGTTCTGATAAGCAAAC
AGCTGTGACTCAGTTGCGAACTGGTTCGGGGCTTGCAGCGCAGCTCTAAATTATTATACTCAAGATATCCATATGTAAGGCAGATATCGTAGTGA
AAAGTCACAGGGTTTTTAAGGTATATTCTTTTGTAAGCTGTGTTCAAATGCACTGCTTTCAGCACAAGCATGCTTATCGTTATCGAGCAGCGATA
ATCGGCGAACTAGTTCAACATAAACCTTCTTGGCACAAGTGACAACTCTGAAACCAATCCATAAACAAAAAATTTGTGTAAACTAAAAACAAAA
AGCGGAAGTTGAAAAACAACACCTTAGCGTATAATTTGGCCCCTTATGATTTGTTAAGTTTCTGTTTTGGAAAATGGGATGCTGAGATAGCCCTG
AACAGGTGTAAGTCGTCCTCCTACACTATGACACATTTCTTCCGAGACGAACTTACATACATACGCACATATGTACACATATGTATGCATGTTTG
TAACTGCATCCATATACGATATATGTATCTTACGCACTCGCGGCTATATACATATATATGCGGAATATATATGTATGTAAGCCGTCAATATGAGA
ATCGGTTGAAGTTAAGTCTTCATTTAAAGTGGCTATAGTACATATGTATATACACACTTTTAACCAGCATATGCTTGTGAATCGAGATTAATCAA
AGGCCCTGCATTGCAGACTTCATATACTTCAAGCCCCACAAAACCAACGACGCATTTAATCAATGTTCTCCAACGGATTGCCGTGCAATCTGTCG
TTTCCGAGCTGTCTCAGTGTACCAAAAGACGAGATCGGTAATGAAGAGCTACTGCCATCCAATATGGGTACTCGCGAGCCTGTTATACTCAATGT
CTACGATATGGTAAGCTTACTTACTCCTGTTGCCCATGCGGACATCGCACAACGATAAATGTAACCTTGCATTTGCAGTACTGGATCAACGAGTA
CACCACCTCAATCGGCCTGGGCGTATTTCACTCCGGCGTAGAAGCCTTTGGCACCGAATTCGCATACGGCGGACATCCATTTCCGTTTACGGGGG
TATTCGAGATCTCACCGAGGGATCACGACGAGTTGGGCGATCAGTTCCAGTTCCGGCAGAGCATCCAAATCGGCTGCACCGACTTTACGTACGAG
GAGGTGCGACGTATCGTCGAGGAGCTGGGTAATCAGTTCCGTGGCGACCGATATCATCTCATGAACAACAATTGCAACCACTTCTCGGGCTCATT
AACTCAGGTGAGACATAAATCGAGGAAACTTTCCACTGGGTGGATCCAATATCAAGCAATATTTTGGGTGTGCTTATGCATGATTCACCGATTGT
CAGATACCGCCTGTTACAATCAGAAGTTCTTATTGTGAATCACCTCAAAAAGTAGGACAGATTACCATCCTAAACACGTCCAATACAATTAGATG
CTTCCAAACGATTCGAGTTTAGGAGCAAGAAAATGCAAGCTTAAAAGCCCAAATGAATATTCATTTGACTATATCTGCAATTCCAATTACTCGTT
CTAGATACTTTGCGGCCAAGAAATACCCAGCTGGGTCAATCGTCTAGCGCATTTCAGCTCCTGTGTGCCATTTCTACAAAGATGTTTGCCAAAGT
AAGCCTTTCTAAGTGAAACAAAAGCCAAGTTCATGATTATTAACTACTCTATGTTGTTTTTAGAGAATGGCTGACACCGAATGCCTTGCAGCAA
AGCATTACCACAATCCAAGAGCGCGAAGACTCCGACAACAGTCCCCTTTGAGACGTTACCTGACCGAAAATATGTCACTTGGCGACACACAAGCG
ATCATAGTTCACATAAAACAACAGTCCTGAGACCAACATTGTTAAGTTACGCAGAGCAAAAAGCCGGGTTACTCATGTCACATCAATTTCCAAGC
CAACAACGCCCCCTAAATAGAAAGCAACAACTATTATTAATAGACTTAAATTAGGCGATATACATATACATACTTACATAGAACAAACCTACATT
GAGACATACTTATACATACATGCGAAGTGACTAAATTATTGGCTATTGTAATTTGTATTTGTAATATGACTATTCAGAATTAAGATATTATTAAG
TGGCCGATAAATTTAAGTAGCAGGCGCCGTTCAGCAGCAGTGTCATTTATAGAATTTTAAATTAACTACGAAGACATCGAGAAATCATCATTAGG
CACTTGCTAAAATTGTACTAACAATACCGCAGACATATTGGTGAACGATATCAAAATGTTGCCCAATTTACTTGTTTACTTTTGTCAGCGGTGGG
GATTTGGTTTTTTTGAATTCCCACCAAACATCGGAGCTCGATTATTGAGATGATTTCCTGGTTGATTTCGTTTACACAATTATACAGAGTTCATA
AGCCGCATGTCTATCAAAACACCAAAATGATCTGTTATCAATAAATATATGTACTTGACATTCTGATATTTACACATGCATAAATACTATTATTA
AACATTTTTAAAGAAAAATATATTTTGATCGAAAACATTCGGTTGCGTTTGATTTACAAGCGAGCAGGTTGGAACGTTTTTAATATTTTGGGTAT
TTTTGGGGTCAAAAGTGGAATAACCAAATAATTAAGTACACGATATTCTCATAAATTACGCAGAATATGAAAACACTCAGACCCAAAACTCCTCA
ACAAAAAACAACAAAATTATTGTACATATATCTTTGTATTATATTTATATATTTTAGACCCTCCAGATTAGATGCATCAGTTGAAAATAAGTTAA
CTTTTC
(SEQ ID NO: 802)

Exon: 1001..1147
Exon: 1442..1625
Exon: 1694..2002

FIGURE SHEET 435

Exon: 2285..2373
Exon: 2440..2521
Start ATG: 1488

Transcript No. : CT22269
AAACCAATCCATAAACAAAAAATTTTGTGTAAACTAAAAACAAAAAGCGGAAGTTGAAAAACAACACCTTAGCGTATAATTTGGCCCCTTATGAT
TTGTTAAGTTTCTGTTTTGGAAAATGGGATGCTGAGATAGCCCTGAACAGGTACTTCATATACTTCAAGCCCCACAAAACCAACGACGCATTTAA
TCAATGTTCTCCAACGGATTGCCGTGCAATCTGTCGTTTCCGAGCTGTCTCAGTGTACCAAAAGACGAGATCGGTAATGAAGAGCTACTGCCATC
CAATATGGGTACTCGCGAGCCTGTTATACTCAATGTCTACGATATGTACTGGATCAACGAGTACACCACCTCAATCGGCCTGGGCGTATTTCACT
CCGGCGTAGAAGCCTTTGGCACCGAATTCGCATACGGCGGACATCCATTTCCGTTTACGGGGGTATTCGAGATCTCACCGAGGGATCACGACGAG
TTGGGCGATCAGTTCCAGTTCCGGCAGAGCATCCAAATCGGCTGCACCGACTTTACGTACGAGGAGGTGCGACGTATCGTCGAGGAGCTGGGTAA
TCAGTTCCGTGGCGACCGATATCATCTCATGAACAACAATTGCAACCACTTCTCGGGCTCATTAACTCAGATACTTTGCGGCCAAGAAATACCCA
GCTGGGTCAATCGTCTAGCGCATTTCAGCTCCTGTGTGCCATTTCTACAAAGATGTTTGCCAAAAGAATGGCTGACACCGAATGCCTTGCAGCAA
AGCATTACCACAATCCAAGAGCGCGAAGACTCCGACAACAGTCCCCTTTGA
(SEQ ID NO: 803)

Start ATG: 194

MFSNGLPCNLSFPSCLSVPKDEIGNEELLPSNMGTREPVILNVYDMYWINEYTTSIGLGVFHSGVEAFGTEFAYGGHPFPFTGVFEISPRDHDEL
GDQFQFRQSIQIGCTDFTYEEVRRIVEELGNQFRGDRYHLMNNNCNHFSGSLTQILCGQEIPSWVNRLAHFSSCVPFLQRCLPKEWLTPNALQQS
ITTIQEREDSDNSPL*
(SEQ ID NO: 804)

Celera Sequence No. : 142000013384094
TCACGTCACATACCACCACATTACCTACCACGCATGCCCCAATCGCATTAGGAGTTCCCTCAACACATCTGCACGCTTTGCGGACAGCGAGAGAG
ATTTATAAGATTATTTATTTTAGTGCCAAATAACAGCAGAAAACGCAAGCAAAAAGTCATTAACTATTTTAGTAGGATAAACTAAATTGTATATA
GAGCGACTCGCTTAGAGCGCCCCATTACTCATTTTCCTTAATTCTTGAAGTTTAAACTGCGCATGCCCAAAGTATTTATATTTATATAATAATGC
ATAACATTTGTAGAGCGATATTTAAGATTTTAATGCAGATTGATCTGAAGTTATATAGAAATAATATTGAACAGAGAACATAGGTAGCGAGAATT
GTTGCTCATTTACATAGGTAGGCCGAAAAACTAAAAATTATAGTTGTTGTTTTAAGTCTTGTACAAATAACGCTAGCACTGCAAAGATTACGCAT
ATCCTATGTACAAATGTCGATCAGTGTAAGATCTAAATACCTAGATTATAAAGCACAGCTGTGAACCCCGGAAATATTTCCAAAAATTCCTTAAG
ATAAATGAATAGAAAAAATTATTAAAATCAAGTGATCAAAGAGGGACTTTCTGAAAATGGCAGTAGTTACTAAAACTACGTATGGAGACCCTGAA
AAAAAAATATCCAAACATATCTTCATATAAATTTTAAATTCGAAATCCAATCAATTTATACATTTGTTACTATTAAACTTTACATTTGTCTTTGC
CTTGAGAAACATATTCCCTTAAATAAGTTTCTTTAAATCCACACAATACACTTGAATAATTAAATGTGTTTTAAAATTCATCTTTTTTATATAAG
ATGACTCGTCATCCAAGGCGATTTCCAACAATTCCACCTAAACGAAAATAAAACTGTCAACACATAAAAGTATAAGTTTTAATTATGTTTTCTGG
AAGTTGTATAAAAATTGCTCTGATTACCGTACTTATATTAATTACGTATATTATAACCGCTGCATCCAGCTGGACAGAGCCCAAAAACAAAGGCT
CATGAAACTGAAGCCAAACAGGGATTTGAAGGTGCTGGCTCCGTTGCCGGGATTGTCCAGGTTCAATTGTGAGGCCAGCTCCTCCGGCACATCCA
GATAGACTCTATCCAAGCCGAAGCTGAAGATCAGTTTGCGCAACTTATCCACATCCACATAGTCACCGGCAGACGACCAGATGGTCAGGGTGCTC
TCGTTTGTCTCGTTCACCGCGGCCACCAGTCGATGCAGTTGCTCCTCGCTGTTGGCGGCAATGCCAGCGCGCACGGGAAAGGTTATGGCCTGGCC
AGTGGATAGGACATTGTTCTCGCTCAGCGTTTCCAGCATGTCATCACACTGCTGCTGCGTGTACTCGCCATCCCGGAAGTCGGCTCCCCAGTTAG
TTGTCCAGCCAATGGAGAGCACTGCCTGTTTGTAGCGCATACAGCCGGCGAAGAATCGGTCCGCATCAACGGGTACGGTTCTATTCTGTTCCACG
GGACCACTTAGAATATCGGCGTTTATCCACACAGGATACGTGGTAGGCTGCACAACACAGAGATATTGTTTAATTTGTTCTGATATCTGAGATTC
GATGACCAAACTTACGTTCGGAATATTCACGTCCAGAATGTCCAGGGAACCCTCGAATACCTCGATCGACTTGAAGTCGAGCTTAACGCCCTTTT
TTTGGTCCTCATGATCACGGTTGAAATTAATGATCTGGTTGAGAAATTCCGACAGCGTAAGATCAGAGACATTGGCCGGCGGATGGGCCATTATG
GGCATGTCCTCGCCATCGCCATTCAGTTTGCCCAGCACAATGTCCGCTTCGATGAAGTCAATGCCACCTTGGGCAGGGAAATGATACTATTGATA
AGTTGGTTACACGCGCATATTTGGCCAATGATCTTACTGGTTTCGGTTAGGACCTCGTCCAGCAATTGCTGGCTGTTGACGGCATGGGCCCAGGT
AATGGCAGTGAGATTTGTGCCCCATACCTTCATCATATCCGACTGTTTGAGGAATATATATTCGATCTGGGAATCGTCTGGCGCTGTCTGCTCGA
CCACCACTTGGTACTGATAATTGCTGGCGTTCAGAGCAGACCCATTGATTTTGGCCACGAGCACTGCGAGTGGACGTGAAATAGACGGCATTAAT
ATTCCACAATTGGACAATGGGACGCACAGAGGGCATAATATGGCAGATACGCGTAGATAAGCCCATTTGCCTTCCTTACCACCCTACCAGCGAGA
ATTGATACGCAAACACATGCAATCCAATCCAATGTGAATTTGTTTACTTCGCAATGAGCGTGTACATATGTATGTGTGCGCGAATGGACTCTAAT
TAACTCCCTTTGTTATGCGATTTTTATGGAATGCAAAGCGCGTTGTGCCCTTCTTCCGCTTTCACCGAATGCTGCAATGCAACTGCACATCAATA
ATTCTCTTCAATCTGTCAGCTGTGCAATGGCGCAAGCGTAGAGAGCAGACGTGAAGTGAGAATGGCGAGAAATGTGCTTAACTTCAAGAGACCGA
CGCTCATATACCCTAGCTCTAAGAGTTTACATGACAACTTATTGACAAAAAATAACAAAATGTTGCTATTTTACGTTTTACCCCCTTTTTGCGAT
TGTGTAAATGTATTATCAAGTAATGTTACCCAACACACTCGTCAGATTTAAATGTTTTAATTGAGTACAGGAGCATCGACTATCAGATACCTGTT
AGTTTTTTTAAGTTATGTCAAAACTAAACTGTCTGGATCCTAATGTTTCCAAGCGACCCAGGGGTCGTATGTACATGAGTTAAAAACATTAAAAA
ATGATGATATGTAATGATTTTGAAAAGTGCAAAAATACGAATTACCAAATAGTAGCGTTGTAAGTAGAAAGGTAATTTTTGAGTCCATTTTTTCT
ATAGGTCTAAGGGCACTTGATCATGAACTTGGGACCGCCACGGTTAGAAACGAACTAAATGGCAATTTTTCAGTTTGGCTTATCGATAGCATTTG
CTGATTTAATTAAACATTGATTAAGTATTGTAAATTGGTAGTGACAATCTATCCGCATATCCCAAAATCTAATCTTTTAAGTGGTCACGTTATCC
GATGAACTCGCGGACTAGTTAAACTAGTTACTACATTATAAAGAAGAAAGAACAAACAAACGTTTTTATGGAAATTATTACCACACATCTTGTAA
AATCATATATTTCATTAAGTACGATTTACATTTATTTGCTTATTAAAAGATAAAATGTTATTTAAATAAGTTTAGACCGCGGTCTCTGTTAGAAA
AGCGTTGCATTTTAACATTTCTGTTAAATGAGCAGCAGTAATAGAAGAGAAAACGTAAGAGAGCGGTTCAAAGAGCGGCACTAGAGTGACCATGC
GGCGGTACACAAGAAATGCGGCCAATAAGCGAGAGCACAAACTTTACCGAAACGAGCGCTAGAAGAACTGGCCACACTACACCCCCGACACTCAG
TTTTAGTTCGAAAATTTAACGGCTCTGGAACCGTTCGGACGTGTCGCTCTCGGTGCGCGTGTGTGTGAGTGGCGAATATAAATATCGGGGGAAAA
GCTCGCACGTGCGACGCTTGCGAAAAAAAAAATTGAAAATATATAGTAAAATTGTTGTTTTATTTATGAGTCGAACTAATGTCCCGTCAGTTGAC
TAAGGACAACGCCAAGAAATAAAAAATAGTTTTAGGAGAAATAGTTTCACGACTTTATTCTTTGGATCTCAGCTTAAGACTAAAAATCAAATGCA
AATTGGATTGAGGAGAAGCCTCAGTATTTGAACAATATTTGTATTTCGGGAGAGCCTCGCTCTTGGGTTCTTAAGATTAGGTAGCGTTGAAAGAG
GGCAGTCAAATCTGCTTAGGTCAGGCTTTAGGATGTTTACAAGAACGGCTGCGCTGCCAAAGATAAACGAAT
(SEQ ID NO: 805)

Exon: 3715..3468

Exon: 3165..2896
Exon: 2153..1938
Exon: 1872..1001
Start ATG: 2031 (Reverse strand: CAT)

Transcript No. : CT22297
GTTGTCCTTAGTCAACTGACGGGACATTAGTTCGACTCATAAATAAAACAACAATTTTACTATATATTTTCAATTTTTTTTTCGCAAGCGTCGC
ACGTGCGAGCTTTTCCCCCGATATTTATATTCGCCACTCACACACACGCGCACCGAGAGCGACACGTCCGAACGGTTCCAGAGCCGTTAAATTTT
CGAACTAAAACTGAGTGTCGGGGGTGTAGTGTGGCCAGTTCTTCTAGCGCTCGTTTCGTAACTAGTTTAACTAGTCCGCGAGTTCATCGGATAAC
GTGACCACTTAAAAGATTAGATTTTGGGATATGCGGATAGATTGTCACTACCAATTTACAATACTTAATCAATGTTTAATTAAATCAGCAAATGC
TATCGATAAGCCAAACTGAAAAATTGCCATTTAGTTCGTTTCTAACCGTGGCGGTCCCAAGTTCATGATCAAGTGCCCTTAGACCTATAGAAAAA
ATGGACTCAAAAATTACCTTTCTACTTACAACGCTACTATTTGTGCTCGTGGCCAAAATCAATGGGTCTGCTCTGAACGCCAGCAATTATCAGTA
CCAAGTGGTGGTCGAGCAGACAGCGCCAGACGATTCCCAGATCGAATATATATTCCTCAAACAGTCGGATATGATGAAGGTATGGGGCACAAATC
TCACTGCCATTACCTGGGCCCATGCCGTCAACAGCCAGCAATTGCTGGACGAGGTCCTAACCGAAACCAGTGGCATTGACTTCATCGAAGCGGAC
ATTGTGCTGGGCAAACTGAATGGCGATGGCGAGGACATGCCCATAATGGCCCATCCGCCGGCCAATGTCTCTGATCTTACGCTGTCGGAATTTCT
CAACCAGATCATTAATTTCAACCGTGATCATGAGGACCAAAAAAAGGGCGTTAAGCTCGACTTCAAGTCGATCGAGGTATTCGAGGGTTCCCTGG
ACATTCTGGACGTGAATATTCCGAACGTAAGTTTGGTCATCGAATCTCAGATATCAGAACAAATTAAACAATATCTCTGTGTTGTGCAGCCTACC
ACGTATCCTGTGTGGATAAACGCCGATATTCTAAGTGGTCCCGTGGAACAGAATAGAACCGTACCCGTTGATGCGGACCGATTCTTCGCCGGCTG
TATGCGCTACAAACAGGCAGTGCTCTCCATTGGCTGGACAACTAACTGGGGAGCCGACTTCCGGGATGGCGAGTACACGCAGCAGCAGTGTGATG
ACATGCTGGAAACGCTGAGCGAGAACAATGTCCTATCCACTGGCCAGGCCATAACCTTTCCCGTGCGCGCTGGCATTGCCGCCAACAGCGAGGAG
CAACTGCATCGACTGGTGGCCGCGGTGAACGAGACAAACGAGAGCACCCTGACCATCTGGTCGTCTGCCGGTGACTATGTGGATGTGGATAAGTT
GCGCAAACTGATCTTCAGCTTCGGCTTGGATAGAGTCTATCTGGATGTGCCGGAGGAGCTGGCCTCACAATTGAACCTGGACAATCCCGGCAACG
GAGCCAGCACCTTCAAATCCCTGTTTGGCTTCAGTTTCATGAGCCTTTGTTTTTGGGCTCTGTCCAGCTGGATGCAGCGGTTATAA
(SEQ ID NO: 806)

Start ATG: 641 (Reverse strand: CAT)

MMKVWGTNLTAITWAHAVNSQQLLDEVLTETSGIDFIEADIVLGKLNGDGEDMPIMAHPPANVSDLTLSEFLNQIINFNRDHEDQKKGVKLDFKS
IEVFEGSLDILDVNIPNVSLVIESQISEQIKQYLCVVQPTTYPVWINADILSGPVEQNRTVPVDADRFFAGCMRYKQAVLSIGWTTNWGADFRDG
EYTQQQCDDMLETLSENNVLSTGQAITFPVRAGIAANSEEQLHRLVAAVNETNESTLTIWSSAGDYVDVDKLRKLIFSFGLDRVYLDVPEELASQ
LNLDNPGNGASTFKSLFGFSFMSLCFWALSSWMQRL*
(SEQ ID NO: 807)

Classification: hypothetical

Celera Sequence No. : 142000013384094
TCACGTCACATACCACCACATTACCTACCACGCATGCCCCAATCGCATTAGGAGTTCCCTCAACACATCTGCACGCTTTGCGGACAGCGAGAGAG
ATTTATAAGATTATTTATTTTAGTGCCAAATAACAGCAGAAAACGCAAGCAAAAAGTCATTAACTATTTTAGTAGGATAAACTAAATTGTATATA
GAGCGACTCGCTTAGAGCGCCCCATTACTCATTTTCCTTAATTCTTGAAGTTTAAACTGCGCATGCCCAAAGTATTTATATTTATATAATAATGC
ATAACATTTGTAGAGCGATATTTAAGATTTTAATGCAGATTGATCTGAAGTTATATAGAAATAATATTGAACAGAGAACATAGGTAGCGAGAATT
GTTGCTCATTTACATAGGTAGGCCGAAAAACTAAAAATTATAGTTGTTGTTTTAAGTCTTGTACAAATAACGCTAGCACTGCAAAGATTACGCAT
ATCCTATGTACAAATGTCGATCAGTGTAAGATCTAAATACCTAGATTATAAAGCACAGCTGTGAACCCCGGAAATATTTCCAAAAATTCCTTAAG
ATAAATGAATAGAAAAAATTATTAAAATCAAGTGATCAAAGAGGGACTTTCTGAAAATGGCAGTAGTTACTAAAACTACGTATGGAGACCCTGAA
AAAAAAATATCCAAACATATCTTCATATAAATTTTAAATTCGAAATCCAATCAATTTATACATTTGTTACTATTAAACTTTACATTTGTCTTTGC
CTTGAGAAACATATTCCCTTAAATAAGTTTCTTTAAATCCACACAATACACTTGAATAATTAAATGTGTTTTAAAATTCATCTTTTTTATATAAG
ATGACTCGTCATCCAAGGCGATTTCCAACAATTCCACCTAAACGAAAATAAAACTGTCAACACATAAAAGTATAAGTTTTAATTATGTTTTCTGG
AAGTTGTATAAAAATTGCTCTGATTACCGTACTTATATTAATTACGTATATTATAACCGCTGCATCCAGCTGGACAGAGCCCAAAAACAAAGGCT
CATGAAACTGAAGCCAAACAGGGATTTGAAGGTGCTGGCTCCGTTGCCGGGATTGTCCAGGTTCAATTGTGAGGCCAGCTCCTCCGGCACATCCA
GATAGACTCTATCCAAGCCGAAGCTGAAGATCAGTTTGCGCAACTTATCCACATCCACATAGTCACCGGCAGACGACCAGATGGTCAGGGTGCTC
TCGTTTGTCTCGTTCACCGCGGCCACCAGTCGATGCAGTTGCTCCTCGCTGTTGGCGGCAATGCCAGCGCGCACGGGAAAGGTTATGGCCTGGCC
AGTGGATAGGACATTGTTCTCGCTCAGCGTTTCCAGCATGTCATCACACTGCTGCTGCGTGTACTCGCCATCCCGGAAGTCGGCTCCCCAGTTAG
TTGTCCAGCCAATGGAGAGCACTGCCTGTTTGTAGCGCATACAGCCGGCGAAGAATCGGTCCGCATCAACGGGTACGGTTCTATTCTGTTCCACG
GGACCACTTAGAATATCGGCGTTTATCCACACAGGATACGTGGTAGGCTGCACAACACAGAGATATTGTTTAATTTGTTCTGATATCTGAGATTC
GATGACCAAACTTACGTTCGGAATATTCACGTCCAGAATGTCCAGGGAACCCTCGAATACCTCGATCGACTTGAAGTCGAGCTTAACGCCCTTTT
TTTGGTCCTCATGATCACGGTTGAAATTAATGATCTGGTTGAGAAATTCCGACAGCGTAAGATCAGAGACATTGGCCGGCGGATGGGCCATTATG
GGCATGTCCTCGCCATCGCCATTCAGTTTGCCCAGCACAATGTCCGCTTCGATGAAGTCAATGCCACCTTGGGCAGGGAAATGATACTATTGATA
AGTTGGTTACACGCGCATATTTGGCCAATGATCTTACTGGTTTCGGTTAGGACCTCGTCCAGCAATTGCTGGCTGTTGACGGCATGGGCCCAGGT
AATGGCAGTGAGATTTGTGCCCCATACCTTCATCATATCCGACTGTTTGAGGAATATATATTCGATCTGGGAATCGTCTGGCGCTGTCTGCTCGA
CCACCACTTGGTACTGATAATTGCTGGCGTTCAGAGCAGACCCATTGATTTTGGCCACGAGCACTGCGAGTGGACGTGAAATAGACGGCATTAAT
ATTCCACAATTGGACAATGGACGCACAGAGGGCATAATATGGCAGATACGCGTAGATAAGCCCATTTGCCTTCCTTACCACCCTACCAGCGAGA
ATTGATACGCAAACACATGCAATCCAATCCAATGTGAATTTGTTTACTTCGCAATGAGCGTGTACATATGTATGTGTGCGCGAATGGACTCTAAT
TAACTCCCTTTGTTATGCGATTTTTATGGAATGCAAAGCGCGTTGTGCCCTTCTTCCGCTTTCACCGAATGCTGCAATGCAACTGCACATCAATA
ATTCTCTTCAATCTGTCAGCTGTGCAATGGCGCAAGCGTAGAGAGCAGACGTGAAGTGAGAATGGCGAGAAATGTGCTTAACTTCAAGAGACCGA
CGCTCATATACCCTAGCTCTAAGAGTTTACATGACAACTTATTGACAAAAAATAACAAAATGTTGCTATTTTACGTTTACCCCCTTTTTGCGAT
TGTGTAAATGTATTATCAAGTAATGTTACCCAACACACTCGTCAGATTTAAATGTTTTAATTGAGTACAGGAGCATCGACTATCAGATACCTGTT
AGTTTTTTTAAGTTATGTCAAAACTAAACTGTCTGGATCCTAATGTTTCCAAGCGACCCAGGGGTCGTATGTACATGAGTTAAAAACATTAAAAA
ATGATGATATGTAATGATTTTGAAAAGTGCAAAAATACGAATTACCAAATAGTAGCGTTGTAAGTAGAAAGGTAATTTTTGAGTCCATTTTTTCT
ATAGGTCTAAGGGCACTTGATCATGAACTTGGGACCGCCACGGTTAGAAACGAACTAAATGGCAATTTTTCAGTTTGGCTTATCGATAGCATTTG
CTGATTTAATTAAACATTGATTAAGTATTGTAAATTGGTAGTGACAATCTATCCGCATATCCCAAAATCTAATCTTTTAAGTGGTCACGTTATCC
GATGAACTCGCGGACTAGTTAAACTAGTTACTACATTATAAAGAAGAAAGAACAAACAAACGTTTTTATGGAAATTATTACCACACATCTTGTAA

FIGURE SHEET 437

AATCATATATTTCATTAAGTACGATTTACATTTATTTGCTTATTAAAAGATAAAATGTTATTTAAATAAGTTTAGACCGCGGTCTCTGTTAGAAA
AGCGTTGCATTTTAACATTTCTGTTAAATGAGCAGCAGTAATAGAAGAGAAAACGTAAGAGAGCGGTTCAAAGAGCGGCACTAGAGTGACCATGC
GGC
(SEQ ID NO: 808)

Exon: 2423..2273
Exon: 2153..1938
Exon: 1872..1001
Start ATG: 2031 (Reverse strand: CAT)

Transcript No. : CT22299
GCACAACGCGCTTTGCATTCCATAAAAATCGCATAACAAAGGGAGTTAATTAGAGTCCATTCGCGCACACATACATATGTACACGCTCATTGCGA
AGTAAACAAATTCACATTGGATTGGATTGCATGTGTTTGCGTATCAATTCTCGCTGTGCTCGTGGCCAAAATCAATGGGTCTGCTCTGAACGCCA
GCAATTATCAGTACCAAGTGGTGGTCGAGCAGACAGCGCCAGACGATTCCCAGATCGAATATATATTCCTCAAACAGTCGGATATGATGAAGGTA
TGGGGCACAAATCTCACTGCCATTACCTGGGCCCATGCCGTCAACAGCCAGCAATTGCTGGACGAGGTCCTAACCGAAACCAGTGGCATTGACTT
CATCGAAGCGGACATTGTGCTGGGCAAACTGAATGGCGATGGCGAGGACATGCCCATAATGGCCCATCCGCCGGCCAATGTCTCTGATCTTACGC
TGTCGGAATTTCTCAACCAGATCATTAATTTCAACCGTGATCATGAGGACCAAAAAAAGGGCGTTAAGCTCGACTTCAAGTCGATCGAGGTATTC
GAGGGTTCCCTGGACATTCTGGACGTGAATATTCCGAACGTAAGTTTGGTCATCGAATCTCAGATATCAGAACAAATTAAACAATATCTCTGTGT
TGTGCAGCCTACCACGTATCCTGTGTGGATAAACGCCGATATTCTAAGTGGTCCCGTGGAACAGAATAGAACCGTACCCGTTGATGCGGACCGAT
TCTTCGCCGGCTGTATGCGCTACAAACAGGCAGTGCTCTCCATTGGCTGGACAACTAACTGGGGAGCCGACTTCCGGGATGGCGAGTACACGCAG
CAGCAGTGTGATGACATGCTGGAAACGCTGAGCGAGAACAATGTCCTATCCACTGGCCAGGCCATAACCTTTCCCGTGCGCGCTGGCATTGCCGC
CAACAGCGAGGAGCAACTGCATCGACTGGTGGCCGCGGTGAACGAGACAAACGAGAGCACCCTGACCATCTGGTCGTCTGCCGGTGACTATGTGG
ATGTGGATAAGTTGCGCAAACTGATCTTCAGCTTCGGCTTGGATAGAGTCTATCTGGATGTGCCGGAGGAGCTGGCCTCACAATTGAACCTGGAC
AATCCCGGCAACGGAGCCAGCACCTTCAAATCCCTGTTTGGCTTCAGTTTCATGAGCCTTTGTTTTTGGGCTCTGTCCAGCTGGATGCAGCGGTT
ATAA
(SEQ ID NO: 809)

Start ATG: 274 (Reverse strand: CAT)

MMKVWGTNLTAITWAHAVNSQQLLDEVLTETSGIDFIEADIVLGKLNGDGEDMPIMAHPPANVSDLTLSEFLNQIINFNRDHEDQKKGVKLDFKS
IEVFEGSLDILDVNIPNVSLVIESQISEQIKQYLCVVQPTTYPVWINADILSGPVEQNRTVPVDADRFFAGCMRYKQAVLSIGWTTNWGADFRDG
EYTQQQCDDMLETLSENNVLSTGQAITFPVRAGIAANSEEQLHRLVAAVNETNESTLTIWSSAGDYVDVDKLRKLIFSFGLDRVYLDVPEELASQ
LNLDNPGNGASTFKSLFGFSFMSLCFWALSSWMQRL*
(SEQ ID NO: 810)

Classification: hypothetical

Celera Sequence No. : 142000013384576
ACTGGGCTTGTACAGACCCAGTGCCGGATAGAAGGCGGTGTTTAGGATTCGCACTGGTCGCGGCGTGGTCAGTGGCACATCGTTTGGGTGCTCCG
CTGGCGGCGGAGGCGGCTTCTTCGACTTGTACCACGGCACCGGGGCAGTGTAGAATATGTGCACTGCACTGATCACCACATCCAAAGTGGTACGC
GACTGAACAAAGTGTACATTTTTAAGATTTAAGGACTAAGATTGGCCACCTTCTTGGACTGAACTGGAAACTTACAGACTGCTCCGCCTCGTGGT
CCCGCTGCTGCTGCTGCTTCATCAGATCGATTTTGCTCTGAATGATGCGCTCCTTGATCTTCTGCTCGTCATACTTCTCGGGCACAATCACTCCG
TTCTCCCGCTGCGGCTGGAGCAGCGCGACGGCCACCGGCGGCGGCTTCTCCGCCACTTGGGGCTGATCCCCGGGCCTGTAGGCGCGTGCGATGAA
TCGCTCGTCCAGCAGCAGTTCGATGGCCGCATTGCGTCCGCTGGAGCCCAGCACTATGATGGTGATGACCAGCAGGGCGACGATGGCCAGCAGGA
GTAGAATCTTCAGCTTACGCCGCGTTTTCACATACTTTTTAGCAGCATTTTCGCAAGCGTGCATTTTCTCTCATTGTTTGGACGTCCTCGTTGT
TTTTCGTCCCCAGTTTTTCGTACCTCCACCCCACAACCCCTTCTCTTCCTGTCGCAATGCAGCTGCCGGAAGTTCCTGGCCATTGCGCATGTCCT
GAAACGGACACACTAAACTATGCCCAGCGAGTTCCCAATTACCATTTCACCATTAAAGCATATGCGAGTTTGTTATTTTTTTGGACATTTTATT
GTGAGTTGATTTATAATATTGTACACATTAATATTGCTAAGTTATTTAAGGGAATATGCCCCAGAAATTTTCACAAATAAAATAGTTTAAACGGA
AATGTGAAACAAGTGGGTTTTAGAATCCATTCCCAAAATAAATACATTACTTATAATTCCGTTTTTGTTTGTCAACACATTGTCTGAATAGTTTT
TATTTAGTTATAAAGTAGAGTTTTAAAAAAGGTTTTAGGTTTGTATCTATTCGAAGTGCATAGTCTTGTTCCGATTAACATGCACCTTCGAGCTC
TAGCGTCCCTCAACTGGAAAAGAAAATCAAGTTAGCACTGCTGGTGGCTGGGGATTACTCATCATTGCAACTTACTGTATGTAGAGAGATCGATT
TCCTCGGGCAGCTCACTGATGTTCACATCGAAACGATCCTGTACTTCGTTAAGTATCTTGGCGTCGTTCTCGTCCGAAACGAATGTGATTGCCAG
TCCCTTGGTGCCGAAGCGACCGGCACGGGCCACGCGATGCAAGTAGGTGTCGGAATCCTCGGGCATGTCGTAGTTGAACACGATGTTCACACGCT
CGATGTCCATGCCGCGGCCAAAGAGATTGGTGGCCACCAGAATGCGCTTCTGGAAGTCCTTGAACTGCTGGTAGCGATTCAGACGCTCCTCCTGG
GTCATCCCACGATGGATGCCGATGGCGGGGAAGTTCTGCTCCGTCAGCAGCTGCGACAGAGCCACGCAACGTTGCACAGACTTCACAAAGATGAC
CACCTATGACAGGGATAATCAAGTAAGTGGTAAATATAAGTTAAGACCACCGAATGACCTACCTGATTGAACTCGAGCACGTCGAGCAGTTCGAA
CAGTTTCTTGTTCTTCTCGTTCTCCTTCAGATTGACGTAGTGCTGCTGCAGTCCGTGCAGCGTCAGCTTGGCCTCATCGTCGACGTAGACCTCCA
TGGGCTGGATTTGGGAAATAGAATGTGGCGCATTTTAAAGGACACAATTAGGAGGGGTACAGAGAAATCGAACTTAGACTAGGCTCGCCTCGGAA
CATACAACAATATGCATAGAATATTCTACATACGGCCACGCTACCACCACATCTCATCAACTAGTCTCTGAACTGCTCCCGAGGATCGATGATCG
CTCTGAGAAGTGTGCGGATTACAGATGAGCGGGCCTATCGCATCGCATTCGCTCTGGATTGATTCAACTCGTCTCATCGGCCAGTCGGCGGGATC
TTTGCTGTTTGCTTGTAGTTTTATTTAGGTATTGGTTTTTGCTAGCGTTGGTATTGTTAAATCTTTTGCGATTTCAATTGATTCATTCAGCGGTT
ACTGCTTGTTTATGCTTTTGCAACGGTTGCCAATTTCCACGATTAACCATTTAGAAAATGGTGTCCGATAGTCATTAACTAAGTTTTTCGATACG
AGTTATGCTCACAGAGCGCTGGACGTTTGGTTGTACGCGTTTAACCATTTGCAAGATGGTGGTTGGCTTATACGGAGGGGATCAAGATCGAATGT
TCGATATCGCGTGGCATTAACAAAATAATAACTAATTGTCGTGATAGCGGTGGATGCGAGGTGGAGAAGTACGAGCATTTTGGTTATGAACACGT
TGATATTTACATCTTGCATGAACTTTTTGCAAACGGGACGAATGTCCTTGCTCAATGTGGCAGAGAACATCATCACTTGTTTGCCGTGCGGCGTG
CTACGGAAAATCTCTTGAACGTCACGACGCATATCTAAAAGAATGGTTTGGTTATTAGTAAAACGTCCGTCATTTGGTGATTATTAGTCAACTTA
CCCAGCTGCTCCAGCATCTTGTCGCACTCGTCGAGCACAAAGTGCTTCAAAAGCTTCAGATTAAGTTTCTTGTTGCGAATGAGGGCGAGAATTCG
GCCAGGGGTGCCCACCACAATATGCGGGGTGCCGCTCTTGAGGGTCTCCTCGTCCTTTTGAATAGCCATTCCGCCAAAGAAGACAGCCACCTAAA
TAGAAAACATATCGAATTAATATATAGTAACTATATAGTCGAACCAAACTTTTTGTTGAATTATATACAATGGATTAAAACGTAGACTCACCTTG
ACTGTGGGCATGTACTTGGAGAATCGCTCATACTCCTTGCTGATCTGGAAGGCCAGCTCGCGGGTGTGGCACATGACCAGGACGTGGCAGGTGTT GTTGTCCGACGGCTCCAGCTGCTGCAGCGTGGCCAGAACGAAGACGGCGGTCTTACCCATGCCGGACTTGGCCTGACAGAGGATGTCCATGCCCA
GTACGGCCTGCGGAATGCACTCGTGCTGAACTGCAAGCGGAGAGCATCGTTAGTGACTGTACCTTTCGTCACTCCAGGTGGAGTGCAAGTACTCA
CCCTCCGAGGGATGCTCGAAGCCGCAGTCCACGATGGCGCGCAGGATCTCCGGTTTCAGGAGGAAATCGCGGAAGCCGGAACTGTGAATGGACAC
ATAGGTGCCCTTGACATCCTTCTTGGGGGCCTCCTGGTTTTCGACCGCAGTGGTCTCGGTCTGCTCCTCATCCTCGTAGTCCAAAAGATCGTCAT
TGTCGGCCATTTCTGCGGCTTTCTTACCTTTAACTAGTTATCGGCTATAAATTCGCAACTAAATGCTGGGAAATAAAATGGGTGCGACTAGATAA
GTTACATGTGTTTGTTAAAGAAAATGCCGCTTTTTTTTGCGGAACCGGTGCCGGCGTTCCCTCCGCCATTTTGTTTTTTCACCGCACCGCATTAC
ATGTATTTCGAAATAAAACGAAATACCCATTACAAGCGACGATTTTATTTAGTGCAGTGTGATTTTCAGTGTCAAACTCACCTTTTGTGCACGTT
TATCACTTTAAAATACAGCTTTTAAAGTGAAATTAACTATTTTAAAATCTTTAACGTGATGCGGAGGAAAAAACAGCGCAGAGCAGTGTGACCGA
AGTACGTTTAAGAACTCATGCGAGCTGAGCCGGGTGATATCGTTAAGTTATCGATAGTTGTGCACAACAAATCCATTTGTAAGCTTCAACTAAAA
AGTTTTTATAAAATATATGCCTTCTAACGCTTTAAATTAAAATGGCTTGTTGAGCTTAAATTTAATTTTTTTTTTATCATTTTGGGGTCAAGCGG
TTCTTAGTCTTTTATCTAGCGCGGCGTTTGGTCACACCAGGCATGCCGGAAAGTTATCGATTAGTCTCTGAAACCATCGCAACAAATTCGATTAC
ACGTTCCAGCGTCGGCCGCGTTTTCCTGCTGCAAGATACTTCATTTTCAAATTTGTGCATTTTCCGTTCGTTATAAAAAGTCAGGTGAGTTGCGC
TGCTATCTACGAGCATTAGGAAAACTTGTAGAAAAAGTTGAAATAACTGATTAAGTGCCGAACAATAGAGGCGGCACTGTTTCACTCAAAATCGA
AATAACCCCCCTGCCTGTATTAGTGTAAAGTCGCTGTAAATATTGAATTAAAATCGCCATATTGTGCAATTTTTGGCTCCTTATCAAATCGTTTA
AAGTGCGTCGACTGGATTAGCTAAGCGTTGCGATTGATTAAACTAGTATTAGCCGCGCCATTTGCCTCCACGCCCATAAACAAACGCCGACAAAC
TCACTTCGTTTTCCTCGTCCGCTTTAGTACAGTCGCTTGAGTGGAAAGCGATGTGCGTGTGTGTGAGTGAGACGTAGAGGAGACTGCGAGAGAGA
GAGAGAGCGCGTTAGAGAAACTCGTTTAGCTTCTGTTTTTGAGCGTTTTGTGCGTTTCCCCTCTTTCGTGTTCGGTTCTGTTTGGAATTTTATCA
GGGCGCAAAAATAACATACCCTACACCGAACGAAAAAGTTCAAATATAAGTATTGCATATAAAACGCGTTTAGAAGGCACGCAATTGTGTTATTC
AACTTTTCTTCAAGTGTTGTGTCCTAAAGAGGTCAGTCACAAAA
(SEQ ID NO: 811)

Exon: 3794..3692
Exon: 3485..3232
Exon: 3165..2942
Exon: 2845..2662
Exon: 2599..2481
Exon: 1809..1678
Exon: 1618..1216
Exon: 1153..1001
Start ATG: 3430 (Reverse strand: CAT)

Transcript No. : CT22389
ACACTGCTCTGCGCTGTTTTTCCTCCGCATCACGTTAAAGATTTTAAAATAGTTAATTTCACTTTAAAAGCTGTATTTTAAAGTGATAAACGTG
CACAAAAGCATTTAGTTGCGAATTTATAGCCGATAACTAGTTAAAGGTAAGAAAGCCGCAGAAATGGCCGACAATGACGATCTTTTGGACTACGA
GGATGAGGAGCAGACCGAGACCACTGCGGTCGAAAACCAGGAGGCCCCCAAGAAGGATGTCAAGGGCACCTATGTGTCCATTCACAGTTCCGGCT
TCCGCGATTTCCTCCTGAAACCGGAGATCCTGCGCGCCATCGTGGACTGCGGCTTCGAGCATCCCTCGGAGGTTCAGCACGAGTGCATTCCGCAG
GCCGTACTGGGCATGGACATCCTCTGTCAGGCCAAGTCCGGCATGGGTAAGACCGCCGTCTTCGTTCTGGCCACGCTGCAGCAGCTGGAGCCGTC
GGACAACAACACCTGCCACGTCCTGGTCATGTGCCACACCCGCGAGCTGGCCTTCCAGATCAGCAAGGAGTATGAGCGATTCTCCAAGTACATGC
CCACAGTCAAGGTGGCTGTCTTCTTTGGCGGAATGGCTATTCAAAAGGACGAGGAGACCCTCAAGAGCGGCACCCCGCATATTGTGGTGGGCACC
CCTGGCCGAATTCTCGCCCTCATTCGCAACAAGAAACTTAATCTGAAGCTTTTGAAGCACTTTGTGCTCGACGAGTGCGACAAGATGCTGGAGCA
GCTGGATATGCGTCGTGACGTTCAAGAGATTTTCCGTAGCACGCCGCACGGCAAACAAGTGATGATGTTCTCTGCCACATTGAGCAAGGACATTC
GTCCCGTTTGCAAAAAGTTCATGCAAGATCCCATGGAGGTCTACGTCGACGATGAGGCCAAGCTGACGCTGCACGGACTGCAGCAGCACTACGTC
AATCTGAAGGAGAACGAGAAGAACAAGAAACTGTTCGAACTGCTCGACGTGCTCGAGTTCAATCAGGTGGTCATCTTTGTGAAGTCTGTGCAACG
TTGCGTGGCTCTGTCGCAGCTGCTGACGGAGCAGAACTTCCCCGCCATCGGCATCCATCGTGGGATGACCCAGGAGGAGCGTCTGAATCGCTACC
AGCAGTTCAAGGACTTCCAGAAGCGCATTCTGGTGGCCACCAATCTCTTTGGCCGCGGCATGGACATCGAGCGTGTGAACATCGTGTTCAACTAC
GACATGCCCGAGGATTCCGACACCTACTTGCATCGCGTGGCCCGTGCCGGTCGCTTCGGCACCAAGGGACTGGCAATCACATTCGTTTCGGACGA
GAACGACGCCAAGATACTTAACGAAGTACAGGATCGTTTCGATGTGAACATCAGTGAGCTGCCCGAGGAAATCGATCTCTCTACATACATTGAGG
GACGCTAGAGCTCGAAGGTGCATGTTAATCGGAACAAGACTATGCACTTCGAATAGATACAAACCTAAAACCTTTTTAAAACTCTACTTTATAA
CTAAATAAAAACTATTCAGACAATGTGTTGACAAACAAAAACGGAATTATAA
(SEQ ID NO: 812)

Start ATG: 159 (Reverse strand: CAT)

MADNDDLLDYEDEEQTETTAVENQEAPKKDVKGTYVSIHSSGFRDFLLKPEILRAIVDCGFEHPSEVQHECIPQAVLGMDILCQAKSGMGKTAVF
VLATLQQLEPSDNNTCHVLVMCHTRELAFQISKEYERFSKYMPTVKVAVFFGGMAIQKDEETLKSGTPHIVVGTPGRILALIRNKKLNLKLLKHF
VLDECDKMLEQLDMRRDVQEIFRSTPHGKQVMMFSATLSKDIRPVCKKFMQDPMEVYVDDEAKLTLHGLQQHYVNLKENEKNKKLFELLDVLEFN
QVVIFVKSVQRCVALSQLLTEQNFPAIGIHRGMTQEERLNRYQQFKDFQKRILVATNLFGRGMDIERVNIVFNYDMPEDSDTYLHRVARAGRFGT
KGLAITFVSDENDAKILNEVQDRFDVNISELPEEIDLSTYIEGR*
(SEQ ID NO: 813)

Name: DEAD box helicase
Classification: RNA_binding
Gene Symbol: Hel25E
FlyBase ID: FBgn0014189

Celera Sequence No. : 142000013383821
TTGTTGTTGCATGTGAACTTTTTCGTATCCCCCAACGAACGAGAGAGCGAGATGGGGCTATGCTATGCGACTGCCGAAATAAGAGGGCCAATTTG
TAGTTGTAGTTCTTGTTGTTGATGTTCTTGCTTCTGTTATTATTGTTGATGTGGTTCTTGCTGTTGTTGTTGATTTTGCAGGGGACCCCCAGTCG
TTGTTATTGTTGTTAACGCTCCTCTTTTATCCGCTCTGCGCTTTGCAGTCCGCTTTGCCGTTAATTATTTTTTCACTCCTTCGCTTTGTGGCTCA
TCTTCGCTTTATCCTGCGCGCACCGCACTCACTCTTTCTCGCTCGCCCTCACTCACTCACACAGCAGTAGCAGCAGCAACAACAACGTTGCACAC AACATCAATATATTGGATATATATCAACACTTTTTCGCCTGCGTGCTTGTCAGTGTGTGTGTGCATGCGTGCGCTTGTCGATTTTCACTGCCTTC
TTTTCTTTGTGTGTGTATATGCGCTGCGCGTTGTGTTTGTCTGCGTCTGTGCGTGTGTTAGGTTTACGTGTGTGTGTGAGTGAACGAACGAAATG
CGTTTAGCGAACGTTTTTTTAAAAAAATCCTTAAATTTTTTGTGGATTTTGGCGATTACCGACACTTAAAACGGCACTGCACACGCGTCCCCGAAA
ACAACGGCACCTAGATTCGCTGGCCGAGTTACGATTTGTTTGATGCTACGCACGGTTTTCGGACACTTTTACACGGGGCTTTGTTTTTACCCATC
GCATCGTCGACTCTTTTGCTCCTAAACGTTGTTGGTGTTAGTGGTCAGCGATAGTGCTCACACACTCGATATGGGTTTTCGATCATTTTCGGCTG
AATATTCGATAAGGTCAATAGTATCGGTTTTCCGCGTACGATTTCCCAGTTTTCAAATGACGGTCACACTGACATTCATTCTTGACAATCGATAG
TTTTTGTCGAGTGACGCTCTTAATATCGAAAAACCATAAGTAACGATAGGCCCATTTTGTTGGTGGTGTTCACAATCTTCTCGCGCTTTCCCAGG
AACTGGTCAAGATGCCCATCGCCGGGCTGTGCATCGAACTGCGCCCGAACCTACGCAGCGGCGTGGTCTTCCTGCGATTCGACCAACAGGTTTCG
CAGAGCCAGAAGACTCGCGTCGTCGTCCGCGACTACAATGTTTATATCAGCGAGAAACCTAAGAATCAGGCAATCGACTTGGATTCCAGCTCCGA
AAGCGACAGCGAGGACTCCGACAAGCTGATGCTCATCCGGCACGCGCAGTATGGTATGGACATTGTCTGCCTGTCCACGTTCTTGGTCAGTGGCA
GGAACATCAGTTTCCGCTTCAACTACAACCAGATTGATCTGGCCAGCGTGGATGGAAGCGCTGTGGACGTGCCTCTGGCGCCACTACTCCTCTCC
TGCCAGGAGAACGAGCCCATCACTATCAACTGTCGTGATTGCCGAGCGGAATTGGTGGCAGGCCGAAGCTATCGCAGGTTGAGGGAGTTTCCCAG
CCTCTTGGTGGATCCCACTGAGTTCTTTTGCCACAATCATGGACCAGCGGGCAAGACCCAACCAATTAGCTTAGTGCCCGCCGAAACGGATCTTT
TCTATGGCCTCAACTATGTGGTCATCAACTTTAACGAAGAAAGTTCGTGCATGCTCAATCGCGACGATCACTTGTACTGCCAGCGCTGCATGCGT
TATTTGGGGCTGACCATGTTCGATGGCGCCGCCGCTCGCATCTGGGCTGATGCAGTACGTTGGCGTCCCGCAGGAGCGGCGACAAATGCCCCCGA
TCGCCACTTCTTCCAAAACTCCACGCTAACGCAGCTTTTCAAGCGTCTGCTGCACTCGCTGTGGCCTCAACCGTTGCCTCAGCTCTGTTTGAACA
CCAGTCGTGCGGTGCTGGTCACCTCGCTGCCCAACCGAAATCAGCAATACATGTTTTTGCACGTGGTGGAGTCACAGCTGCGTGTGCTGCGTCGC
ATTCGCCCAAATTCGAACCGACTACGCTGCTTTCGCGCCTGCAAGCTGTACTACGGCGTTTTTGGAGCCAATCCGCCGCTGCTGGAGAAGTGGCA
GGCGCAGCAGACGCTGCCCCAAATGGATGTATCACCGAACATGTTCCTAAAGATTCAGAAGCGCCTCGAGACGAATGGCCACTTGATTCCGGACG
CCTTGAGCACGAACTGTGCGGAGGAGCACCTGCAGTTGTCGTACTTCTTTTATGAGAACGAGGATCAACACGACGGCGGGGTCGTCGCTTCGGAT
GTGTTTACGGATCAAATGAGCAACGTGTATCAGAAGGAGGTGGATCCGTACGAGACGGATGCAGGACATGCCAGCGAGAGCGATGACGAGTACTC
GGATACGGACACCGCTTCGGGGGACACGGCGGCTTACTCGCTCGGCATGCGTACCCTGCAGAAACGCAGCCCCACTCCGCCGCGGTCTTTCGCCA
AAATGGCCACCTCCGCCTCGCCGGAGGACAAGTAGTGACCCAATCCGATTCAAAAATCAAGCATAGCTTGTATGTCGGAAACTATGTTACTTGTT
TTCACTATACAAAGACGGACTTGGCCCAATAATTTGTCAAAGATATTTTTTTTTTAAAGTTAGCCCTTGATTGATAATCAATTCCATCCAAAATA
CTTTACTATGCCTTTGATTCAAATCCTCACATCCTTTGCTTTTGTTTATCGTTATACATTCGCTTAGAATGAATTAACAGTACGCGGAATTGATA
ACGCCAAAGACTATTTATTGTTTTGTGAAGAAAATTTTGATTTTATTGCTTGACTCGATCGTTATATATATATATATGTATATTATATATATAGTTTAA
CAAACGTTTTGCAACAAGTATTAGCTGGATAAACGACTTCTATATATATGTATGTACTAGCACAAATGCAGTGCGTTCCGTGACTGTAAGTGCCA
ATGTCTTGGCCTTACAGCTGCGAAACGCACTGCACATGTTTTGAAGAAAAGTAAGAAGATTGTTTGCTTTTGCTTACACTTTGACGTTCCCTATT
AATTCACTTAAGTTAACGAGAAAAAAATGAGAGTAGAGTAATAGTTTAAAAGTAAAATTGAAATATTGAAAATATTCAATTTTAATATATTTTCA
AAGAACTGAATTAACAAGTTTTCCAAAATGTGACTTACCAAAACAAAAAAAAAACAAAAAATGGACTAAACGAAAAAAGAAAAGTTATTGCTTA
CGAAAAACATATATTATAAATATATACTAATATACTTCAATATGTTTCCAGAAACAAGATTAAAACAGAATATGTATGAACTATGATTTAGCTGC
GTAAACATTTACACACAACTATTATTGTCCAACATTTGTAATTCTGTTCGCAACTACGCATGTCAACGAATAGCCGAGAAAAATTGTAATTTCAA
AACTCTGATGTAAAGTATATGGAAAACAACTATTTATATGTATATATTTAAAGTCAAAATGGGATGAATGTAAGGCGGAGCAGTG
(SEQ ID NO: 814)

Exon: 1001..2505
Start ATG: 1057

Transcript No. : CT22601
CCCATTTTGTTGGTGGTGTTCACAATCTTCTCGCGCTTTCCCAGGAACTGGTCAAGATGCCCATCGCCGGGCTGTGCATCGAACTGCGCCCGAAC
CTACGCAGCGGCGTGGTCTTCCTGCGATTCGACCAACAGGTTTCGCAGAGCCAGAAGACTCGCGTCGTCGTCCGCGACTACAATGTTTATATCAG
CGAGAAACCTAAGAATCAGGCAATCGACTTGGATTCCAGCTCCGAAAGCGACAGCGAGGACTCCGACAAGCTGATGCTCATCCGGCACGCGCAGT
ATGGTATGGACATTGTCTGCCTGTCCACGTTCTTGGTCAGTGGCAGGAACATCAGTTTCCGCTTCAACTACAACCAGATTGATCTGGCCAGCGTG
GATGGAAGCGCTGTGGACGTGCCTCTGGCGCCACTACTCCTCTCCTGCCAGGAGAACGAGCCCATCACTATCAACTGTCGTGATTGCCGAGCGGA
ATTGGTGGCAGGCCGAAGCTATCGCAGGTTGAGGGAGTTTCCCAGCCTCTTGGTGGATCCCACTGAGTTCTTTTGCCACAATCATGGACCAGCGG
GCAAGACCCAACCAATTAGCTTAGTGCCCGCCGAAACGGATCTTTTCTATGGCCTCAACTATGTGGTCATCAACTTTAACGAAGAAAGTTCGTGC
ATGCTCAATCGCGACGATCACTTGTACTGCCAGCGCTGCATGCGTTATTTGGGGCTGACCATGTTCGATGGCGCCGCCGCTCGCATCTGGGCTGA
TGCAGTACGTTGGCGTCCCGCAGGAGCGGCGACAAATGCCCCCGATCGCCACTTCTTCCAAAACTCCACGCTAACGCAGCTTTTCAAGCGTCTGC
TGCACTCGCTGTGGCCTCAACCGTTGCCTCAGCTCTGTTTGAACACCAGTCGTGCGGTGCTGGTCACCTCGCTGCCCAACCGAAATCAGCAATAC
ATGTTTTTGCACGTGGTGGAGTCACAGCTGCGTGTGCTGCGTCGCATTCGCCCAAATTCGAACCGACTACGCTGCTTTCGCGCCTGCAAGCTGTA
CTACGGCGTTTTTGGAGCCAATCCGCCGCTGCTGGAGAAGTGGCAGGCGCAGCAGACGCTGCCCCAAATGGATGTATCACCGAACATGTTCCTAA
AGATTCAGAAGCGCCTCGAGACGAATGGCCACTTGATTCCGGACGCCTTGAGCACGAACTGTGCGGAGGAGCACCTGCAGTTGTCGTACTTCTTT
TATGAGAACGAGGATCAACACGACGGCGGGGTCGTCGCTTCGGATGTGTTTACGGATCAAATGAGCAACGTGTATCAGAAGGAGGTGGATCCGTA
CGAGACGGATGCAGGACATGCCAGCGAGAGCGATGACGAGTACTCGGATACGGACACCGCTTCGGGGGACACGGCGGCTTACTCGCTCGGCATGC
GTACCCTGCAGAAACGCAGCCCCACTCCGCCGCGGTCTTTCGCCAAAATGGCCACCTCCGCCTCGCCGGAGGACAAGTAG
(SEQ ID NO: 815)

Start ATG: 57

MPIAGLCIELRPNLRSGVVFLRFDQQVSQSQKTRVVVRDYNVYISEKPKNQAIDLDSSSESDSEDSDKLMLIRHAQYGMDIVCLSTFLVSGRNIS
FRFNYNQIDLASVDGSAVDVPLAPLLLSCQENEPITINCRDCRAELVAGRSYRRLREFPSLLVDPTEFFCHNHGPAGKTQPISLVPAETDLFYGL
NYVVINFNEESSCMLNRDDHLYCQRCMRYLGLTMFDGAAARIWADAVRWRPAGAATNAPDRHFFQNSTLTQLFKRLLHSLWPQPLPQLCLNTSRA
VLVTSLPNRNQQYMFLHVVESQLRVLRRIRPNSNRLRCFRACKLYYGVFGANPPLLEKWQAQQTLPQMDVSPNMFLKIQKRLETNGHLIPDALST
NCAEEHLQLSYFFYENEDQHDGGVVASDVFTDQMSNVYQKEVDPYETDAGHASESDDEYSDTDTASGDTAAYSLGMRTLQKRSPTPPRSFAKMAT
SASPEDK*
(SEQ ID NO: 816)

Celera Sequence No. : 142000013384221

FIGURE SHEET 440

GGTTCCAGCCCAGCAATTAATTTGTGGCCTGGAGCGTTTTAATTACTCAGCATCAGTGTGCGCGCGAATCTCGGTCAGGTGAGACAAAGCCACAT
ATGTATATCCGTTTCCCCGTAACTCCCAACTCACCCATCCAACAACTAAGGGCCAGGCCACAAAGCCAGCAAAGCGCTAACATCTCTGTACCAAA
GTCGACGTCACTGTGCCACGGGAATCGGGTGTGTGGATTTTATAGCGTACGATAAGCTAGACGAGGGCCAGGTGTCAATCAAGACTGGAGTTTTG
GACGGACTGCTGGCCAGGTTGAAGCCTCGGTCGGAAGGGTCTCGGCGTTATCATTCCAACTCAGTTGGGCGTCCCAAGCGCGGCGCTGTTAAATT
GGGTTAAGCCCAGTTCATCGGTGCATACTAATCTAAGGTGCGTTGCCCCGGTATTGAAAAGTGGAACAATATAAATATTTGAAAATATGTTCGGT
AATTTAGTTAAATAAGTTACAATAACAATTACATTTTTATAAGTGTTTTTATGAAAAATGCTACATCTTATGTACACATAGATTAAATATTATTT
AGATTTTCAGCGATGGCTATGTAAATTTTTCACAAATGCAATACTTTAATGCACTAACATTATAACAAATTTCAAATTTATAGAAAACTTTAAGT
ATTCAAAATCTAAAACGGTCATGTAAAATACCATACATCAAACCATGTAAGCATACATCTTACATGTAAAATATTGCTGGCATTTGACCTAAGTA
GATTAAGTAGATTACAAAAATATGTAATCCGCAATTTCAAAGAAACATTTTTGAGTGCATCTTATAAAACTCTATTTTTTGCCAATGCTATGTAA
AAGAATAATTAAACTTTGTTAATTGTTGGGTGCGCAAATGAGTAAAGCCAGAATTACGTGGCCTATTACATTGCCTAATTTTGTTTAGTATATCT
AGATGTGTTGTTGCATTTTCGAAAATATCACTTGCTGCCACACTGGCTGTGCGTCATTTTCAGAAACGCCGCGAATATTTTGCCATTGAAATCTA
GCTAAGCATTGGAATTTCGCAACGTGCAGCAGCAAAGCAAACTACAAACATGTCGGGCACATCGCAGAAACACAGGAACTTCGTTGCGGAGCCAA
TGGGCAACAAGTCGGTGACGGAACTGGCCGGAATTGGGGAAACCCTCGGTGGACGCTTGAAGGACGCTGGATTCGATATGGTGCGTGTGTAAATA
CGATGACGCCATGTGCGCAAATAAACAATGCCAGTCAAGTGCTAACGATCATTTCCATTCGTTTTAGGCCTACACCGTTTTGGGACAGTATCTGG
TGCTGAAAAAGGACGAGGAGCTGTTCAAGGACTGGATGAAGGAGGTGTGCCACGCCAGCTCCAAACAGGCATCCGATTGCTACAACTGTCTCAAC
GATTGGTGCGAGGAGTTCTTGTAAGAGGTGGACACACAAGCCATCCGAGTAATTCGATCAAAAGGAATCTGCTAAAGGCATCGGCCAATCATTTT
TATTCGCAGTCAACGAAAGTGGCCCAATGCTAGCTAAGCATTTGCCGTGTTCACTGTTAGTATGTATAGCTGTAGGGTGTAATTTAATGTCTAAT
CCGAATAAATGTACAGTCATGGAAACGATCCTGCATTTGGATCTCTGTTCTGCGAAAAGTACAGTAGGTGTAAAACATTTGTTGCTGGCCGGCGA
AGCAGCCTAATGCAGATTTTTATTAATTTGATTAGGGGACAACAATAAGCAACACTATAGAAGGCAGATCGGTTGGCGACTATATCTTCTCTATG
TTTTCGATTGTTGGCGAGTAGGAGTCTCTGACTCGCTGAAATAAGCCTCTGTCTTTTTGATGTTTCTTTATCAGCGGGCTGATGTCGCCTAATTT
TGAAATCTATTTCTTTTTGTTTTTCGGAAATGATCTTTTATAATGATGGACTTAGAACCTTTTAAATCCCAATCGCTGTTTTGTTTGGGGATTAT
GTGTAAGCGGTTAATATATATTTTATAATGAAACCCCTTTTGTCAAAATTAATTGTCCTCGAGTAATTAATTAGTACCGAGTATTTGATTATAAA
TACAACTTTTTTTAAATAAAAATATATATTTTTAAAAACTTATTTTTAAAGTGAGTGGTATTAAATAGGATTTCTTTTCCCTGAAGTGGTATCAT
ATGGTATTTATTTTTGGTCCCGTGGTATTTTTTATCGTTATCGGCGCGGTCACGCTGCTAAGAATTACATTACGCGTGAATACCAATGAAAATTA
AGAGAGAAATTGCAAAACACAGCCAAGCGGTGCAATAAATCGCAAAGTAAGAGGCGCAAAACGCGCAAATACCGTTTGCGCGGTTAAAAAATGCA
AAAACACCAAACGATAGATTAAACAAAGTGAAATTAACTCGGCTTTGGCATATGCGAACACCAGTGTGCCAGTGTGTGTGTGTTTTTCTTTGTAT
ATAGACTCGCAGAGCGAGACGGCCATACACGACGGCAGACGGGACGGTGCAGGTGCGCGAGTGCGAGCGGGAAAAAGGCTGTGCGGTCACTGCTA
CTCTGTGTGTTATTTCAGAGTTACAGGCCAAACATTCTGATGTGCGGCCGAATCAAATCGACTTTTTGTGTGCATCGCCCCAGCGTTCGTCTTAA
TTAA
(SEQ ID NO: 817)

Exon: 1001..1220
Exon: 1303..1664
Start ATG: 1095

Transcript No. : CT22713
GCGTCATTTTCAGAAACGCCGCGAATATTTTGCCATTGAAATCTAGCTAAGCATTGGAATTTCGCAACGTGCAGCAGCAAAGCAAACTACAAACA
TGTCGGGCACATCGCAGAAACACAGGAACTTCGTTGCGGAGCCAATGGGCAACAAGTCGGTGACGGAACTGGCCGGAATTGGGGAAACCCTCGGT
GGACGCTTGAAGGACGCTGGATTCGATATGGCCTACACCGTTTTGGGACAGTATCTGGTGCTGAAAAAGGACGAGGAGCTGTTCAAGGACTGGAT
GAAGGAGGTGTGCCACGCCAGCTCCAAACAGGCATCCGATTGCTACAACTGTCTCAACGATTGGTGCGAGGAGTTCTTGTAAGAGGTGGACACAC
AAGCCATCCGAGTAATTCGATCAAAAGGAATCTGCTAAAGGCATCGGCCAATCATTTTTATTCGCAGTCAACGAAAGTGGCCCAATGCTAGCTAA
GCATTTGCCGTGTTCACTGTTAGTATGTATAGCTGTAGGGTGTAATTTAATGTCTAATCCGAATAAATGTACAGTCATGGAAACGATCCTGCATT
TGGATCTCTGTT
(SEQ ID NO: 818)

Start ATG: 95

MSGTSQKHRNFVAEPMGNKSVTELAGIGETLGGRLKDAGFDMAYTVLGQYLVLKKDEELFKDWMKEVCHASSKQASDCYNCLNDWCEEFL*
(SEQ ID NO: 819)

Classification: hypothetical

Celera Sequence No. : 142000013383755
TTGCCCGACAGATCCAGCTCGCCGAGCGACTGACAGAGCTTAGTGCCCCGCAGCCAGCACCAGTCATTCTGAGTACCCAGTAAGTTGTTGCCCAG
GTGCAGCGAGGTGAGCGGAAGACGACCCAGCTCCGAGGGAATCTAAAAGGCAGAATTAAGCTTAACTCAGTGGTCTAAAATGATAACTAATTAGT
CAATCCACCTTGGTCAGCTTGTTACCGCTGACATCCAGCTTTGTGAGGTTGCGCAGGGTGCATATCTCGAAGCTCAGCTTCACTAGCTGGCTGTT
GTTGATGGTCAGCGATTTGAGGGTGCGCGGAAATCCCTTGATGGGATACTCGCTCCGCTTGCTGATTACCATGCGCACCTGGGGCTGTGCCTTCT
GCGGAATTGCCGTAGCGGCGTTTATGTTCAGTCTCAAATTGATGGCGTCCTTGCCATCCATGCCCAGCTTGAGGGTCTGCAGGAATCCTTTCAGC
TGGATAGGATCGCACTTAATAAGCAGGTTATCTGGCGGCTGTATGAAACCAATGGTGGTCTTCCCATCCAGCACAAACTTGGTGTGCACGACATG
AATGTTATCCTTGACCTTGTAGCGATTTCCAGTCTTGTTTTGTCCACTAAAGAGCACCATTTCCAGCTCCTTCTTGGTGTTTCCATTCGCATCCC
TGGCGCTTTGCTTGTAGCCAATGGCCAGTGTGGATTTCACGGGACGTGGCGTTTTGTTCGTCTGGGTGGCGCGATTCACCACCTGAACTTCGCAC
AAAATCTTCATGGCGAGGCAGTGATTAGACAATAAACAAAAAAAAAACCCGCTAAATAAAACTAAACATTTGTTTTGGCCTCAAGAGTTGCCACC
TGATGGTTGGGACAGCTGATGATATCGAGCAGCCATTCGATAGTTAGTGGTGGACCACATACCGATGTTTTGGATTTTAGGAACTAGTTTCTAAG
AGCAGCATCAAAAGCTCTCGAAAAAAAAACAATTGGCGCAGGACAAGTTACAAAACCAAAACAAGCAACGGCAATTGTTTAAAAACTGCAAAGTT
ACTCCCATTTAAATACCGGAAAATGTTATTTCGCAAGGCTCGCCGACACTTTCTGCCGTTCTACATGTTCAATGGATTCTTGTGACAGCGCAACG
AACGATATCAGCGTTTGCGTTACAATAGCTCAAATATTGGTCATCCGAGGCATGAGCTTACAGTAAGTAATGTGTGCAACATATGGAGCAAGACA
GTGGTCATGCAATACAAAGAACACTCAAATTTTAAAAACTGAAATAAAATGCAAAAATGTTTCTGCAGCACAACAGCCTGTTGGACAACTATGCG
AACAGCAATGTGATAATAAACATTGACAACTGCGCGCTCTACAGCACCAATGTAAGAATTTAAATCTCAAAACCCATTTCGAATACTAACGATCT
TATTTTCTTTTCGCTGATCTGGCAACGCCAAGCGGCCAGCTGATCGAAAGTCGATAACCGACGGCTCGCACGATCGACAGCGACGTCGCCGCCAG
CGGTTTTTAGTCATTTTTCGGTTTTTCTGCGCAACGGTCGCTTTCGGTTTGGCAATCGCCTGCGTCATCTACACGCTCCACACAATGGCTGGAT TTTTGCTGTGCTCGTCGCACTGGTGGCTCTGCTACTGACGAAACCCGGCTGGCGCTGGTTCTACATAGCGGGTGCGACCGCTAGTCGCGATCTAA
CGTGAGTGCTGCTCTTGTACAGGGAGGGCATACTGTACCCAAGACCAAGTCCAGTGATAAGTTTACAATACCGCCCCCGTGCGGTTTGCATTTCA
ATACACAACAACATCTTGGGGGCTTTTCTTTTGTGAATCGATTGAGAACATAAGCGAACTGAAAAATCAGCCGAGTGCGAGGTTCACTTCGTAGC
CGAAAGTCAGAAACCACAGTGGAAAAAACTCGTTTTCCATCTATTTGGGTCGCCAACAGCAGCATTCATTTCCAGTTGGGAAAACCATAAAAGAG
AAAACTTAACTGGCGAAATGATCCATGCGACATTGTGACGAATAGTCAACGCAAATTATTAGTTTTTGCCACTCGATTACGAGCAGTTTATTGAC
TTCTTCAGGTTCAAGGTCGCACAGCCCAAAAAAAAAAAAAAACCTACGAGAAACCAAAACAAAACTCGCTTTTATTTACCATTGACTTCATACGA
TCGTCGCCCAGCGAAACCCTCCGCGCATACTAATCGATCCGAATGCGATCGAGTGCGTCAGGCGGAAGACCACTGGCACACTAACCGATCTGTTC
TTGAAAACGTACGCCAAAGAGCCAAAGCTTGGGTCATTATGATGGCGGAAGTGTCGCCTGCGTCTTGGAATTTTCGTTTTTCCAGGGTTGCCAGG
GCTACTTACATTTTGAAATTTTGCAGAAAGGTTATTAAGTATTCAGAATTTTTAAGCAGCTCTTTACTTTTAAAATTGTTATAGTTAAGAATGTC
TAGGACTTGGATATCAAAGTAAGTTTGCTAACCTCATAAATAGTATAAATTTAAAGAAATTACAATAATATTATAAACCACATAGATTTTTAATT
TTTAAGTGATTCACTTTTTTATGGCTACAGTGGAAGTGTTAAGATTCCAGGGTTGCCACGGCAAGCCAAACTATACCAATTGTAGACCAAGCAAT
AAGCGAACGAAAAGCTTGTCAAAATTATGTATGTCTCATCAATATACTTTGTGTCGTCTGTCGTTACGATAATTAAAAAAGCGGAAGTGTCGCCT
TTTGACTTGTGTATGTATTTTGAAGACGGCTATAGATATTGCTTTTTAGCACAGGTATTGTTAGTAATATACATTTTTACAACCAAAACCATCTA
ACCAAACACCTTAACTAATAGGAGCAAAATCTTTACACTTCATTTTAACTAAGTATTTTAAGATTCAATTAAGTTTGAATTGAGCTATAGCCTTC
GCAAATATTCACACATTGCAACGCATTTTACAAAATTATGTTTGACCATAAATAAGGTTAAATACGTAAAGTTATAGCTATTAAAATAGCAAGTA
TTCTCAGCAGCATTTAATTTGCTCGGCAGTTTTCGCTTAATGAGTCAAACTCGGCAGATCAAGTTCCATGCCAAGGCCAACACTGGTTTCCCATT
TACCCAGCTCGTCTATATGGCCATTCGTATATTTCGCGCTCACAACAGATTCTTAAGATCAACTTCAAGTCTGGCCGGTCAACCTTGGCCACGTA
TCGAAGTTTTTTGCTCGGCCACCAAGTAGACGAATCCAATCTGCGGGCAAACATGTGCAGCAACTCCAAAAGGAGCCAAGCAAACAAAGCACTCG
ATGGGGGTCATAAGGCCTGATTAAAAACCCTATAAATACGCGGCTAATGTGCGTTAAGCGCTAAGCTAAGTTAACTAGCTGTTACCGGCAATCTT
ATCGACACTTCACTGCCCCGTTGACGGTGCAAAGTACGCACGGGTGCAAAGCGAATTCAAATTGAGATCGTCGTTGTGGTCGAGTCCCAAGTCGA
GTGTAGGTTTTTTTCCCCCTTTTCTAATACAGTTCCCATCGAACTATTGTATTTGCGATTTGGATTAGTTCTACCTCACACTCTTTCCTATCGT
ATCAAATCTCTGTGGATCTTAAGTGCTTGCAAATGCCTTTCAGACCGTAGCATCAGCTCTTCTAGAACTTGTAGAGGAAACTATTAGTATTACAG
AGGCAGCTCTTTATAGTTTATACAAATTAATACCGTGTAACAACTTGAAGGCATCTATCTTTATAAGAAATACACATGATTACAAAAAAATCAAA
TTTCTAAACTCACATTTGTCAATACAAGTGCAATTTATTTCAACCGCTAGTCAATGATAAACATTATCTGCCTTCGTTCAGTGTGCAGGTTTATT
TATTTTGCCGATAGCTTCTTCAATATTGATAAACATGGGCCAAACAACAGTTACAGTTTAAGTATAAAACTCTTAATCCTCATAAGTGATAAGAT
ACTAAGATGTGTAAGAGTTCTGTTCCAATGATTATACGATTGCAAATGAAAATATAAACGTCAGATTTAGATATCTGTAGCTATTGGTTAAGCTT
TCTCCCGGAAAATTCAAAAGCCCTTGAAACTGGCTAAACAAATACGATTTTATCTCAACCTTCCCGTGAACTTTGCATTACTCAGCTCGAAATTA
GCAGCGTCATTAAGTTGTGGCTCGCATGGTCGGACTAGGTTACCACGTTCGGATTGAATTGCAACCACTTCGAGCGGGTTTATCTCTGGGTTTAT
CGCATCACGGCTGTTGCGCTTGTCGAGCTTCGATTTCTGTTGGCTATTTATACAGACCCCAACCACTAACCATAAAACACACGCGATTGATGGCA
AAGATAATGCCGGTACGGCTACTATCCTCGACTAGCCGCTAATCAAACACTTTCCCTCCAAAACTGAGTAACATATCAATATCCGTTGGTTATAC
ACGTTATTTGTGGATTTTCCATTGCAAAGAAGATACGCTATCTTCAAAAATATTGTCTAGTCAACACACTTTTATATAGCACTAACTAATTTAGC
ATTGTTCGTTTGAAGATTCCTCGATTTATCAGGTTTGATATTTAATTTACTAATCAAATTTCCCCTTAACAGAGCTCTCTGGGCCTATATCAAGC
TGCTGAGGTACACGAAGCGCCATGAGCGGCTCAACTACACGGTGGCGGACGTCTTCGAACGAAATGTTCAGGCCCATCCGGACAAGGTGGCTGTG
GTCAGTGAGACGCAACGCTGGACCTTCCGTCAGGTGAACGAGCATGCGAACAAGGTGGCCAATGTGCTGCAGGCTCAGGGCTACAAAAAGGGCGA
TGTGGTGGCCCTGTTGCTGGAGAACCGCGCCGAGTACGTGGCCACCTGGCTGGGTCTCTCCAAGATCGGTGTGATCACACCGCTGATCAACACGA
ATCTGCGCGGTCCCTCCCTGCTGCACAGCATCACGGTGGCCCATTGCTCGGCTCTCATTTACGGCGAGGACTTCCTGGAAGCTGTCACCGACGTG
GCCAAGGATCTGCCAGCGAACCTCACACTCTTCCAGTTCAACAACGAGAACAACAACAGCGAGACGGAAAAGAACATACCGCAGGCCAAGAATCT
GAACGCGCTGCTGACCACGGCCAGCTATGAGAAGCCTAACAAGACGCAGGTTAACCACCACGACAAGCTGGTCTACATCTACACCTCCGGCACCA
CAGGATTGCCAAAGGCTGCGGTTATCTCTCACTCCCGGTGAGTGCAATAGCTTTTCTGAACTAAGTTTAAATGGAAAGGTTCTAAACAAATTTGT
ACTTTAGTTATCTGTTTATCGCTGCTGGCATCCACTACACCATGGGTTTCCAGGAGGAGGACATCTTCTACACGCCCTTGCCTTTGTACCACACC
GCTGGTGGCATTATGTGCATGGGTCAGTCGGTGCTCTTTGGCTCCACGGTCTCCATTCGCAAGAAGTTCTCGGCATCCAACTATTTCGCCGACTG
CGCCAAGTATAATGCAACTGTAAGTGAGATTTATGGCCTAACTAAATCACTCTCTAATTTGGCTTTTGTGATTTCCAGATTGGTCAGTATATCGG
TGAGATGGCTCGCTACATTCTAGCTACGAAACCCTCGGAATACGACCAGAAACACCGAGTGCGTCTGGTCTTTGGAAACGGACTGCGACCGCAGA
TTTGGCCACAGTTTGTGCAGCGCTTCAACATTGCCAAGGTTGGCGAGTTCTACGGCGCCACCGAGGGTAATGCGAACATCATGAATCATGACAAC
ACGGTGGGCGCCATCGGCTTTGTGTCGCGCATCCTGCCCAAGATCTACCCAATCTCGATCATTCGCGCCGATCCGGACACCGGAGAGCCCATTAG
AGATAGGAATGGCCTATGCCAACTGTGCGCTCCCAACGAGCCAGGCGTATTCATCGGCAAGATCGTCAAAGGAAATCCTTCTCGCGAATTCCTCG
GATACGTCGATGAAAAGGCCTCCGCGAAGAAGATTGTTAAGGATGTGTTCAAGCATGGCGATATGGCTTTCATCTCCGGAGATCTGCTGGTTGCC
GACGAGAAGGGTTATCTGTACTTCAAGGATCGCACCGGTGACACCTTCCGCTGGAAGGGCGAGAATGTTTCCACCAGCGAGGTGGAGGCGCAAGT
CAGCAATGTGGCCGGTTACAAGGATACCGTCGTTTACGGCGTAACCATTCCGCACACCGAGGGAAGGGCCGGCATGGCCGCCATCTATGATCCGG
AGCGAGAATTGGACCTCGACGTCTTCGCCGCTAGCTTGGCCAAGGTGCTGCCCGCGTACGCTCGTCCCCAGATCATTCGATTGCTCACCAAGGTG
GACCTGACTGGAACCTTTAAGCTGCGCAAGGTAGACCTGCAGAAGGAGGGCTACGATCCGAACGCGATCAAGGACGCGCTGTACTACCAGACTTC
CAAGGGTCGGTACGAGCTGCTCACGCCCCAGGTTTACGACCAGGTGCAGCGCAACGAAATCCGCTTCTAAGAGCTGCAATAGAGTTGTGTCTGAA
CCTTGCCTTTTGCCCAATATGCTGTTAATTAGTTTGTAAGGCTAAGTGTAGTAGAGGAAAATCGGGGGAAATCGGCAGCAAAGATCATTCAGCCT
AGGAGAGATGCATCCGAAGCACATTTCCATGTCAACAATGCACTTTTGTATATCGTAAGCATATATATATCGTATATCGTAAACGTAGTTGTATC
TGCATTTGTGTAGATGATAGCCTCCTATACGCATTTCAATTGTTTTTAGCGTGCTAAAGAACCTTGTTAAATGCAATTTCAGCTATTGTTTAGTC
AGTTTTAGTGGCATTTACACTTCCATTCTCGTTGCGTTTCGTTTTTGCCTGTACATATGAGAAGCTCTGATGTTTTTGTATCAAATAAAGTTTAT
TCCTTCACCACGGACCACGTATTTAAATTCGCAGTCTATCGTGCGGCAGAATGACACCATTCCACCTGCATACAAATGATTATGTGCGATTCGCT
CCTCGACTCTCCGATCTATAGAAATGCATAGAGATATACTTACACTCATACCCATGCTGTGAGTATTCAATTAACCAAACTTGAACCTTGTCGAC
GTTCAAGTGCATGAAATTAACGAGAATTTTTAATAGCATTATATAATAATCTGTGAATCAGCTAACGACAATAACGTTTAATAGAAGATGCGCCC
TTAATTTAATTATGGTTCTACTCCGCTTTCTGTGATTTTTGAAAAGTTGAGAATATAACTACTCACTGCTTGCTTACTCTTTCATTATCGCACTA
TTAGAGATACCCATTTAATGGACAGCAATTAAGGGGTAATTATATTCTAGCAGTTAGCTTGTTTAAGCCAGTGCTAGTATTGGTAGCATCATTCA
ATCAGAAAACGTTTCAAATCTTTTTGATATTTTAGAAGAATAATGTAACACAATGAGTCTTTCTTTCAAAGAAAAACCAAATAAAGTACTTACAC
ATCCACTTTTAAGAGAACTTAAAGAATATCTCAATTTCTTTGGAACATGCTTACTATATCTGGATATTAGGATGATAGTTCCTAATAGTTCAGAG
CTATTCCATTTGATATTAAACTTTGCAATGGAAAATTCAAATCAGTTGGAGGGCGGCGAAAGAAAAAGCTCTTTCCCTCGCAGATCCTAAATAT
GACCAAGTGGGTGAGTCTTCCGGGTGACTGGCAGATCGGTAGGAAGCAGCAGCTAGTCGAGAACCGTTATCAGTGGCGGCAATAACAAGCGAGGC
TTCAATTCGCTTCCAGTGCAAAGAAGATTATTGCAGTTGCATTGCCGGGTGCGATCCGCCCAGTTGTCCACGTGTGAGTACGGATGATTGTCGAT
CGCTCGATCGATTTCATACAAAGTGTGTGAGGTGTTTACCTCGAGTCCAGAAAGTCAAGACC
(SEQ ID NO: 820)

Exon: 1001..1202
Exon: 1312..1381

FIGURE SHEET 442

Exon: 1458..1711
Exon: 4633..5262
Exon: 5328..5533
Exon: 5629..6947
Start ATG: 1192

Transcript No. : CT22721
CAAAACCAAAACAAGCAACGGCAATTGTTTAAAAACTGCAAAGTTACTCCCATTTAAATACCGGAAAATGTTATTTCGCAAGGCTCGCCGACACT
TTCTGCCGTTCTACATGTTCAATGGATTCTTGTGACAGCGCAACGAACGATATCAGCGTTTGCGTTACAATAGCTCAAATATTGGTCATCCGAGG
CATGAGCTTACACCTGTTGGACAACTATGCGAACAGCAATGTGATAATAAACATTGACAACTGCGCGCTCTACAGCACCAATCGGCCAGCTGATC
GAAAGTCGATAACCGACGGCTCGCACGATCGACAGCGACGTCGCCGCCAGCGGTTTTTAGTCATTTTTCGGTTTTTCTGCGCAACGGTCGCTTTC
GGTTTGGCAATCGCCTGCGTCATCTACACGCTCCACACAATGGGCTGGATTTTTGCTGTGCTCGTCGCACTGGTGGCTCTGCTACTGACGAAACC
CGGCTGGCGCTGGTTCTACATAGCGGGTGCGACCGCTAGTCGCGATCTAACAGCTCTCTGGGCCTATATCAAGCTGCTGAGGTACACGAAGCGCC
ATGAGCGGCTCAACTACACGGTGGCGGACGTCTTCGAACGAAATGTTCAGGCCCATCCGGACAAGGTGGCTGTGGTCAGTGAGACGCAACGCTGG
ACCTTCCGTCAGGTGAACGAGCATGCGAACAAGGTGGCCAATGTGCTGCAGGCTCAGGGCTACAAAAAGGGCGATGTGGTGGCCCTGTTGCTGGA
GAACCGCGCCGAGTACGTGGCCACCTGGCTGGGTCTCTCCAAGATCGGTGTGATCACACCGCTGATCAACACGAATCTGCGCGGTCCCTCCCTGC
TGCACAGCATCACGGTGGCCCATTGCTCGGCTCTCATTTACGGCGAGGACTTCCTGGAAGCTGTCACCGACGTGGCCAAGGATCTGCCAGCGAAC
CTCACACTCTTCCAGTTCAACAACGAGAACAACAACAGCGAGACGGAAAAGAACATACCGCAGGCCAAGAATCTGAACGCGCTGCTGACCACGGC
CAGCTATGAGAAGCCTAACAAGACGCAGGTTAACCACCACGACAAGCTGGTCTACATCTACACCTCCGGCACCACAGGATTGCCAAAGGCTGCGG
TTATCTCTCACTCCCGTTATCTGTTTATCGCTGCTGGCATCCACTACACCATGGGTTTCCAGGAGGAGGACATCTTCTACACGCCCTTGCCTTTG
TACCACACCGCTGGTGGCATTATGTGCATGGGTCAGTCGGTGCTCTTTGGCTCCACGGTCTCCATTCGCAAGAAGTTCTCGGCATCCAACTATTT
CGCCGACTGCGCCAAGTATAATGCAACTGTAACTACGAAACCCTCGGAATACGACCAGAAACACCGAGTGCGTCTGGTCTTTGGAAACGGACTGC
GACCGCAGATTTGGCCACAGTTTGTGCAGCGCTTCAACATTGCCAAGGTTGGCGAGTTCTACGGCGCCACCGAGGGTAATGCGAACATCATGAAT
CATGACAACACGGTGGGCGCCATCGGCTTTGTGTCGCGCATCCTGCCCAAGATCTACCCAATCTCGATCATTCGCGCCGATCCGGACACCGGAGA
GCCCATTAGAGATAGGAATGGCCTATGCCAACTGTGCGCTCCCAACGAGCCAGGCGTATTCATCGGCAAGATCGTCAAAGGAAATCCTTCTCGCG
AATTCCTCGGATACGTCGATGAAAAGGCCTCCGCGAAGAAGATTGTTAAGGATGTGTTCAAGCATGGCGATATGGCTTTCATCTCCGGAGATCTG
CTGGTTGCCGACGAGAAGGGTTATCTGTACTTCAAGGATCGCACCGGTGACACCTTCCGCTGGAAGGGCGAGAATGTTTCCACCAGCGAGGTGGA
GGCGCAAGTCAGCAATGTGGCCGGTTACAAGGATACCGTCGTTTACGGCGTAACCATTCCGCACACCGAGGGAAGGGCCGGCATGGCCGCCATCT
ATGATCCGGAGCGAGAATTGGACCTCGACGTCTTCGCCGCTAGCTTGGCCAAGGTGCTGCCCGCGTACGCTCGTCCCCAGATCATTCGATTGCTC
ACCAAGGTGGACCTGACTGGAACCTTTAAGCTGCGCAAGGTAGACCTGCAGAAGGAGGGCTACGATCCGAACGCGATCAAGGACGCGCTGTACTA
CCAGACTTCCAAGGGTCGGTACGAGCTGCTCACGCCCCAGGTTTACGACCAGGTGCAGCGCAACGAAATCCGCTTCTAAGAGCTGCAATAGAGTT
GTGTCTGAACCTTGCCTTTTGCCCAATATGCTGTTAATTAGTTTGTAAGGCTAAGTGTAGTAGAGGAAAATCGGGGGAAATCGGCAGCAAAGATC
ATTCAGCCTAGGAGAGATGCATCCGAAGCACATTTCCATGTCAACAATGCACTTTTGTATATCGTAAGCATATATATATCGTATATCGTAAACGT
AGTTGTATCTGCATTTGTGTAGATGATAGCCTCCTATACGCATTTCAATTGTTTTTAGCGTGCTAAAGAACCTTGTTAAATGCAATTTCAGCTAT
TGTTTAGTCAGTTTTAGTGGCATTTACACTTCCATTCTCGTTGCGTTTCGTTTTTGCCTGTACATATGAGAAGCTCTGATGTTTTTGTATCAAAT
AAAGTTTATTCCTTCACCACG
(SEQ ID NO: 821)

Start ATG: 192

MSLHLLDNYANSNVIINIDNCALYSTNRPADRKSITDGSHDRQRRRRQRFLVIFRFFCATVAFGLAIACVIYTLHTMGWIFAVLVALVALLLTKP
GWRWFYIAGATASRDLTALWAYIKLLRYTKRHERLNYTVADVFERNVQAHPDKVAVVSETQRWTFRQVNEHANKVANVLQAQGYKKGDVVALLE
NRAEYVATWLGLSKIGVITPLINTNLRGPSLLHSITVAHCSALIYGEDFLEAVTDVAKDLPANLTLFQFNNENNNSETEKNIPQAKNLNALLTTA
SYEKPNKTQVNHHDKLVYIYTSGTTGLPKAAVISHSRYLFIAAGIHYTMGFQEEDIFYTPLPLYHTAGGIMCMGQSVLFGSTVSIRKKFSASNYF
ADCAKYNATVTTKPSEYDQKHRVRLVFGNGLRPQIWPQFVQRFNIAKVGEFYGATEGNANIMNHDNTVGAIGFVSRILPKIYPISIIRADPDTGE
PIRDRNGLCQLCAPNEPGVFIGKIVKGNPSREFLGYVDEKASAKKIVKDVFKHGDMAFISGDLLVADEKGYLYFKDRTGDTFRWKGENVSTSEVE
AQVSNVAGYKDTVVYGVTIPHTEGRAGMAAIYDPERELDLDVFAASLAKVLPAYARPQIIRLLTKVDLTGTFKLRKVDLQKEGYDPNAIKDALYY
QTSKGRYELLTPQVYDQVQRNEIRF*
(SEQ ID NO: 822)

Name: fatty acid transporter-like
Classification: transporter

Celera Sequence No. : 142000013384839
CTTTATATGGTCACGAATGTCTCTGTTGCACACTACAGACTAAAATCAAAATATTCTCTGAAAGGTATTCCCAACAAAAAACGCTATATCCTGGG
ATAACCATTGTATTCTTACGATTAATTTCACAAAATGAATTAAGAAACTATAATTGTACAGAAACGATTATTTAAAGGATTATTGCCGTTCAAAA
ACGAAAGAGTAATTCCCGCTACTGTTCCGCTGTTTTCACGTCCGCAGATTTAAGTGACCCAATTGCAAAAACAAAAGCAAAACAATATTAATTCA
ACTCTGAGCCGACTGATGCTGCAGGCACCTCAAAGTTAAAAAATGCGTAGCACGTGCGTTCAGAAATTCGGCCAAGAAAAAAGGAAACTGTTAAC
TGGGTCCATAAATTCAACTTTGTTGTATATACATACATACATACTGTATGTTCATATAAGTACGTCACTTTAAACATCTGCCTTCGTTTCCTTTA
ACTCTTTAATTTATTTTTGATCCAGCTTTAATAACTATTAATTTATTATTCCTATAACTTGTACGTTGAATGGGCATAGGTAATTTTCTTGAAAT
ATGAAATATTTAAAATGGAATGCATTCTGTATGAAATGTATTCGGGCCTAAAAAGATGATTGTAGTTATTTAAATTTGAAACTAGATTTTTAATA
CAAGAAGATTGATAAAAAGTTATTTTTGATTTATATTTAATAAATATTTTAGAACTAAAACCAAAATAAATGATGTTTTCCCTACTAAAATTATA
CTCGAACTTGTAGCTGTATTAAAACGTGTTCACTTATTGATTAAATCATAGCCCATACAGTTAGTTATACGTTCTCAATTTTTGCCAATCTTGCG
CTTCTGATTTCCAATGAAATAAAAGTGACTATTGTACGAATCACCCTAATATTTTTTCACAACTGGTATTTTTCTCCGTCCCGCAATCGGTAACA
CCATGCAGGGTGTCTGAGTTTCGAATCGGCATAAATTCGCCGGCAGCTGAGCAAGATGTATCCTGTGAGCTCGCAAAAGAGGTCCTGGACATTCG
CCAATGAGGGCCAGCTCATGGAGTTCCGCGTGGAGCAGAACAGCAAGTACATCGAGTCGCACGAGGAGGAGGCGCAGGGTCGCGACCTCAATGAG
CACTTTCTCACGTCGGCGGAGGAGCGCCTGTTGCTGAAGCAGTACGAGATCTACCTGTTCGATTTCTGCCGCCGCTTCGAACCGACGATGCCCAA
GTGCGTTGTGGGCACGGCCTTCCACTACTTCAAGCGGTTCTATCTGAACAACTCCCCCATGGACTATCACCCCAAGGAGATTCTGTAGGAACGCT
CACCTGAGAGCAGCAAACACCCAGCTGAAAAGCAAAACATTCTAAAAATGTATAAACCTTTTCAGAGCCACATGCGTGTTCGTTGCCTGCAAAGT
TGAGGAGTTCAACGTGTCCATCAACCAGTTCGTAAACAACATCAAGGGCGACAGGAACAAGGCCACCGACATAGTGTTGTCCAATGAATTACTGC TGATTGGACAGCTCAACTACTACCTCACCATACACAATCCGTTCAGACCCATCGAGGGTTTCCTGATAGATATAAAAGTGCGATATATATTCACA
TTTGCTCTCCAGATTGTTTCGTTCATATTGGTTTGTTTCAGACTCGCAGCAATATGCAGAATCCAGATCGTCTGCGGCCACATATTGATAGTTTC
ATTGATTCCACGTACTACTCGGATGCCTGTCTTCTGCATACGCCTTCGCAAATTGCATTGGCTGCCGTCCTCCACGCGGCCAGCAGAGAGCAAGA
GAATCTCGATAGCTATGTGACGGATCTTCTGTTTGTCTCCGCCAGGGAGAAGCTACCCGGACTCATAGATGCCGTGCGAAGTAAGTTTGTGCTGT
GAGATGGTGCGCCCAGCCCTACATGCCTTTTTCCCGACAGAAATTCGCATAATGGTGAAGCAATATCAGCAGCCCGATCGGGAGAAGGTCAAGGC
CATCGAGAAAAAGTTGGACAAGTGCCGAAATCAAGCCAATAATCCTGATAGCGAACTGTAAGACGCCCTAATTTGTTCATGCATTCCGAATTTAA
TAACCCTTATACTTTAAAAGCTATAAGGAGCGCCTACGCCGATTGTACACCGATGAGGATGACATGCCCGCCGAAGATGCCTCATTCCACATTGC
AGATGTGAGCTCGGACACATCTGCTATGAACATCAGCCAATAGACTTAAGAATATTTATTTAAATGATGTGATGATCTACTACTGCGTGGATTTC
ATCGATATTAAAGCATTTTGTAATTTACCATTTCTTGATTGTTAAAATGTATGCGTTTAGTGTTAGTTTACTAAACAAAGTTGGATTAGGTACTT
CACTTTTCCAATATATAAAATATTAAAAAAAAAACCTTTTGAAAATCCGCTTAGCGCTGCTTGGCAATATTTCGTTCGCAGCTAACGGCCACACT
GCGCCCCAAGAAAAACAAGAATAGTGAACTCAGTCACAACAAATAGCAAAAAGAGTTCGAAATGCAGGATTTTCTGCCTTCGCTGGATGTTCTCT
TTCTTGGACTACCAGGCCACTACTCGGTAGCGCTGGTCACCCTTCTGCTGTGCGTTTGGTCGCCTTCTACTTCGCCAACATCTTCAAGGACAAA
GGCGTGGGTGTTTTTGCCGGAAGAAGTAGACGTCTCCTGGAATATTTCCTTACATTATCTTGCAGGAACTGAGGACGAGGGCCTGGGGGCCGAC
GAGCCGCGCGATGAGGAGGATTCCGAGTCACGGACTCCGCAAGGGGAGGAAACCGACGATGACGAGGCCTACGAAGAGAACTCCACCGAAAGCGA
AGTTGAGCTAATCGAGGAACAGCTGCCCGAGCACAGCTACAACCACCTGATGGGCCAGCTCAAGGCCAAGAGGCTCCAGCATAAGATGGAGAAGA
CCCTGACTCCCAGCCAAATCGAGGAGGAGCGCCGAATAGAGCGCGAGCAGCTGGCGGCCATCTTTGAGCTCCTGCGCAAACAGGAGGCGGAATTG
AACCTCCAGGACCGAATAAGCGACCAGGATCTCAAGCAGGTGCGGCTCTATCGCTGAAGTGGCGCCGAGCCTGGGCTCACCCTACCTGAATG
TACAGACTTGTGTGATCTATTAGTTTAATGTTTAAAATTCCAAGATTTGGTGTTGCCTCATACGGTCCACTAAGTGCGGGCAAGTCTTTAGTCAG
AGAGCTATCTCATCAGTCGATGATGTCGGAATATAATATCTTAGTTGTATGTAAATTATATGTATTCCACTTCGATCTATGTATTTTGTGAGTTC
CTGGTGTTATTAATATCTGATTTAGATTTGTAGTAAATGGCTGTTCGGCTCTTAGTCTCTTAAATCAGCTTTCGAATTAAGAAT
(SEQ ID NO: 823)

Exon: 1001..1319
Exon: 1396..1597
Exon: 1657..1885
Exon: 1941..2052
Exon: 2111..2409
Start ATG: 1006

Transcript No. : CT22750
GCAAGATGTATCCTGTGAGCTCGCAAAAGAGGTCCTGGACATTCGCCAATGAGGGCCAGCTCATGGAGTTCCGCGTGGAGCAGAACAGCAAGTAC
ATCGAGTCGCACGAGGAGGAGGCGCAGGGTCGCGACCTCAATGAGCACTTTCTCACGTCGGCGGAGGAGCGCCTGTTGCTGAAGCAGTACGAGAT
CTACCTGTTCGATTTCTGCCGCCGCTTCGAACCGACGATGCCCAAGTGCGTTGTGGGCACGGCCTTCCACTACTTCAAGCGGTTCTATCTGAACA
ACTCCCCCATGGACTATCACCCCAAGGAGATTCTAGCCACATGCGTGTTCGTTGCCTGCAAAGTTGAGGAGTTCAACGTGTCCATCAACCAGTTC
GTAAACAACATCAAGGGCGACAGGAACAAGGCCACCGACATAGTGTTGTCCAATGAATTACTGCTGATTGGACAGCTCAACTACTACCTCACCAT
ACACAATCCGTTCAGACCCATCGAGGGTTTCCTGATAGATATAAAAACTCGCAGCAATATGCAGAATCCAGATCGTCTGCGGCCACATATTGATA
GTTTCATTGATTCCACGTACTACTCGGATGCCTGTCTTCTGCATACGCCTTCGCAAATTGCATTGGCTGCCGTCCTCCACGCGGCCAGCAGAGAG
CAAGAGAATCTCGATAGCTATGTGACGGATCTTCTGTTTGTCTCCGCCAGGGAGAAGCTACCCGGACTCATAGATGCCGTGCGAAAAATTCGCAT
AATGGTGAAGCAATATCAGCAGCCCGATCGGGAGAAGGTCAAGGCCATCGAGAAAAAGTTGGACAAGTGCCGAAATCAAGCCAATAATCCTGATA
GCGAACTCTATAAGGAGCGCCTACGCCGATTGTACACCGATGAGGATGACATGCCCGCCGAAGATGCCTCATTCCACATTGCAGATGTGAGCTCG
GACACATCTGCTATGAACATCAGCCAATAGACTTAAGAATATTTATTTAAATGATGTGATGATCTACTACTGCGTGGATTTCATCGATATTAAAG
CATTTTGTAATTTACCATTTCTTGATTGTTAAAATGTATGCGTTTAGTGTTAGTTTACTAAACAAAGTTGGATTAGGTACTTCACTTTTCCAATA
TATAAAATATTAAAAAAAAAA
(SEQ ID NO: 824)

Start ATG: 6

MYPVSSQKRSWTFANEGQLMEFRVEQNSKYIESHEEEAQGRDLNEHFLTSAEERLLLKQYEIYLFDFCRRFEPTMPKCVVGTAFHYFKRFYLNNS
PMDYHPKEILATCVFVACKVEEFNVSINQFVNNIKGDRNKATDIVLSNELLLIGQLNYYLTIHNPFRPIEGFLIDIKTRSNMQNPDRLRPHIDSF
IDSTYYSDACLLHTPSQIALAAVLHAASREQENLDSYVTDLLFVSAREKLPGLIDAVRKIRIMVKQYQQPDREKVKAIEKKLDKCRNQANNPDSE
LYKERLRRLYTDEDDMPAEDASFHIADVSSDTSAMNISQ*
(SEQ ID NO: 825)

Name: Cyclin H
Classification: cell_cycle_regulator
Gene Symbol: CycH
FlyBase ID: FBgn0022936

Celera Sequence No. : 142000013384658
TGCTTGCTTTTCGCTTTCACAATGCGTAAAAAAACACCTAATTTTGTATAGCATATGAATATCATTAAGTGTATCAGTAAATTTGTATCAGTAAC
AGTTGCAATATTATCGTTATCCTTGTATTATATCCTTTTTTCCTTTTTCTTTTGTTTTACCCGACGAGATACCACGAACGACGATTACGATTACG
AACGAGCGACGAAAATACGCGAACGCGAAACCGTTAGAACCCGAAACGCGACGATTTTTTTCGATTCCATTTTTTGTTTGTTATATAAATGACGA
AAGTGTTGGATACTTCTGGGAAATTGGAATCCGCTGTTGATGAATGCTTTCTATGGTTTTTGAACGGAGTTGAACATCAGTCTTTGTTTGATTTG
TAACAATTTTGTGTGCACCTGCCATTGAATCCATTTTTCCATTTCTGATCTTAGGATTTCACAGGAGACCCAACACTTTCATCCTTTAAAGATTT
TATTTAGTTATTTAGTTTTTAATTACCGCGACGAGGACCCGCAATATCATTTAGTTTCGACGATTTTTCATTTAGCTTTTCTATTACTATATGAG
AAACACCCGTGTGTTTAACATATTCAACTCTATTTTCGGTTTGGGTTTTGGGGCAGAGTGTATTGGAGAATGGGGCATATCTGCTATAGCACTGA
CTCCGGTTAAGTACGGCCGGAACACATAATTTTCTAGTGGTTCCTACTAAGTTTTCTGCACAAGAAAGGCATTTTATATGCTGTAAGCGGACAGT
CGTGTGCCTAAAGAGGTTCTACAGATCAAAGATCCTCTAGCTTGAATTCAAATATATACGATTCTTCTCTATTCGATTTTTCGATATATGTTTGT
GGATTTAAATCTAGTTATGTAGTTTCTTTTATGTGGATTTGCTGTTTTTTTCGATTTCTATAAGCTTAGATTTTCAATGTTAACTTAACATTCGA
ACTGCATCGAATAACTTAAGGAGGCTAAAGATAAAGACGACACGCTTATTACGCATACTTGTACATAATTGTCTAGTTAAAAAGTTGCTGCTTGG CTCGCTAATGGGTGAAGGTGGGTGTTTTATGGCATGGCTAGCCTTAGATGTTATACATTGTGGTCAGGCGCTCGGCCAAGGTTGGCGGGAATTGC
TCCACAAATCGACGCCAGTTCTCCTCGCCCACTTGGGTCTTAAAACCGTGCAGAATCTTGAAAGAAACATGTGTGAAATAAAGAAAATAGTTACT
ACCTGTAGGGTACAAACCTTCTGTATCATCTGATGCAGATCCTCTGGTGGGTTAACCCAGGAAGCGATGGCATCGCAGAAGAATATAAAGTCTGC
TACCACGCCAGCTGGATTCACCGTGATCATATGACACATTCCACGGAAGGCTGAGTCCTTCTCATCATTGTCTCGTATGTGCCGCAACGATGTGC
ACCTGCATTTTTCAAAGAAAATGTTTAAATGTCGTTTTCAGGAAAAGTAAACTAAATTAGCAGGCTTTGGCAAACACGAAAGTTCAAAAGCAAAT
TTAAATTCCAGTTAAATGATGTGGATTGTTAGTGAGTTGTGGAACAAAGGAATAGATCGATGTGCTTATAGGTTTCAGTGTTCAAGCGTAATTTA
AGAGTAATGGGAAGAACGGGAAGGATAGATAAGAGAATAGAAGGAAAGAATAAGCATTTTAAATATAAAACGTGTTACACACCACTGTCGTACAA
ATTCGGGCAAATAAGGAGCCACTTCAACTGGGCACACATAACCTAGACGACCGATTGTTATTGCTAAAAGAACAGAAGAAATAAGTATAAATAAA
TCAACTGAATAAATCAATATCATACGTAGTTCGCTGCGATTGATTGCTAAATTCGAATTGAATATCAATTGCGATTCTGGTCTATCTATATCTAT
GCATGTTGTATGGGAATGAGGTTCGATTTCGTTTCGTTGCTGCTCATGCAACAAGTAACACAAATTAAAACAGAAACAAATTTCCGGACATCCAC
ATACACGCATACATTCAGAGTAATATATATACAAACAGATCGCATATAAGTTCTTAGATAGCTCGGGAAATTCGAAAGATTTCTATCAGCTCAAA
CGAATTACCTGTGTTCTCCAGCAGTGTCTTGGGCGTGTTCGGGCGGTTGATAATGATGAAAAGGTCGCTGAGTACAAGGCGTATGTACTGCTTGG
TCTCCTCACCTTTGAATCAAAATATATATTAAAACGATCCTAATACTCCTAAGAAGCTCCTCCCACTTACCCAATTTCATGCAGATTTCGCCTAT
GGCCCAAGTAGCATTATTGCAGACCGAAATGAAGTCTGGGTTAAGGTTTTGACCCAAGATGGGGAAGAAATCGGCCATGAAGGGATGCACGTGGG
GGAAACAGGCCTTAGTCAAATCACCCAGCAGGGCAAACGAAGATTGGCGAACCTGGAATACAACAACATTATAGAAATTCAAAGGTTAATTTCGA
AAAGATTGGTTTTAAGGGAGACATACCTCAGGCAAAACGTCCTGCATACACTGGTAGAGTAGATGCATAATGTTGCTGTTGGCCACCAATGTCTC
GATGTGGCGATCCAAACCCTCGGCTAGGCCAGACAGCAGATCTAGGGCGACAATCATGCGCTCTTTGTCGGGATGGTCGTACGTTTGGTTTTGTT
TACACAGCTGTTGGCGATTTAGATTGATGAAAAAGATTCCTTAGAAAATTGACAAGTAGATTACCATTTCCTGGTTGATAGTCTGCTCAATAAGA
GAGATGCACCTTCGATACACCGGGTCGCAGTAGGGCAGAAAGCCGGACTGCAAGGCAGTGGCGATGCTCGACAGGCACTCCAACAATGGGAACAG
ATCCTTATCGTCATCCTTCAGCAGGTTCCACTTATCAATTAGCGGAGGCATTAGGATGTCAATATATTGCGGCTTATTCAGATGATGACCTACGG
AGTCCGCCAAAGTACCCACGGCATCGTACAGTATCAATAAGTTCTTGTGCTGGTACTTGGAGAAGGCAAAGACGAGCGTCTTTAGAATATACTCC
AGGTAGGGCACCAGTTCCGTGCAGGCCTCCTCCTCCAGAGTAGCAAAGGCAGAGCACGCAGCTTCCTGAACGCGCTTATTGGAGTCTAGAATGCG
CTTCAGCAGTTCTTCCATTAGAGGCTTCAAGTACTGGTCGTGCGGCTGGTTGACAACCCAATTGGCGTATCGCGAGAGCGTCCAGCATGTGATGG
AGCGCACCAGTGCCTTCTTGTCGGAAAGGCAGCTAATTAGGTAGGGAATCAGCTCTGGCAAGTGTTGGATCATGCCCTGCATGCAGCCCTCCGCA
ATAGCTCCCAAGGCCAGCACACCACTCTCTTTGATCACCCATTCTTGATGGAACAGAGTCTCTTTCAGGATGGGCAGCACAACGGGCAGACAATC
CTCTCGGAAAACATTCGCCAATACATCGAGAGCAGCTGCGCTGCACTTGCGCAAGTTCCATTCCGATAGCGAGCTATCGTCGTCCATTCCATCTT
CAAATTCGTCGTCGTCATCATCGCCTGTCGCTCCAGCTCCTCCCTCTTGTGTACTCCTGATTGTGTGTGCACGGGACTTGTGGAAACGCGGGCGG
ATATCCTCTTCTCGATCGGGCACCATGTCATCCTCCTCAACGTTTCCCTTGAGGAGAATTATGTCGACCTCTGAGTACCGCATGCCTCGTACAAG
AACTGGCGCTAATTGAGCAAGATAAGGGGCAAGCACGTCCTTGCAGATGCTTTGCTCGGCCAGTGAAAGCCAGAACTCGGATGCTTCCAGGGCCA
CACCCTCATCGGTGTCCTGGGTGCGCAACAGCATGTACTAAAATTCGTTAAATAAGATATTTAAACAAAAATTTATCAGAATAATTATTATTAAT
TATATATTTTATTTTAAAGTTATACCTCAATAATCTGCGACATGTGCGGCATCAGACGGTCCATTCGCACCTCCAGCAGCATGACCAATCCGTGG
CACACGTTTTTGCGCACCTCGTGGTCCTCATCTGATGACAGGTGAAAGAGGTTCTCAATGAAGCTGTCTATGTTTAGCATCAGAGCCTGTGATCT
GTTGATGATGAACTGGTTGATGCAGGCAATGGCGTGGGAGCGGATCTTTGGACTGCTGTGCTTGAAGTACTCCAGGAACTTTGGAATCATTATGT
TTAATGGCCTGTTGAGCGCTGCGGAATCCAAAATCTCGGCAGAGTCCTCGCAAATTTTCTGCAGGGCACTGAATGCGCCTTCGCACACATTATAG
TCCTGGTTGTCGAGCATTTCGCAGAGAGATGGAAGCAGCTGCGGCCAGTTGTGCAGACCGCCATTGCTGGCGATGGTGGTAATCAGGATGCCCAC
GGTGGCACGGATCAGGGGCGAAGCGTCGCCCACTGCCTGCAGGCACTCGTGTTTGATATACTCCACGATCTCCGGCTGCAGAGTGGTGCCGTGCA
TGCGGATGTTGTTCTTGAGGATTAGGCCGCTGAGTGATCTCGTGGGCTCGTCCTCTGTCTTCAGTTTCGTCAGCACATAGATAAGATAGTTGTTG
AAGTCGGGGTAGCGATTGAATTCCTCCAGTTTCTGTTGAGAAGGACACAATATGTGCATGCAGTTCGAGGAACCGTACCTGGTAGAAGTTATTAC
TCACCATCTGTACGGCCATTTGAGTGGCTGTGTCCGGTGACTGCGACTCCTTGAGGATCGCTATGATCTGCTGCAGACCTTCTCCCTGTGGTTCC
CACGTCATTTTGCTGCTGCAAGGGAAGATCGCAAGGGTTTTAGGTTTGATTAGTGAATTCGGAATTAGAAATTAGGGTTAATGGCCTCGCAAAGG
GTAGCAAATGGGGGAGAAAGAGAGAGCACGAGAGACACTCTGTTCGAGGCCACTCACGCACACCAGGGCATTTTGCACCCACACCCGCAAACAGA
CATCTGCTGTTGTGAAATTTACGTTTTCCGTTCGATGTTTCCTTGGCACTTAATGGTTTTACGGCGGAAGGCGGGAGTTGAAAGCCCTGCCCCGA
GAGTAACGTGCGATTTTCTGCCCACAACCCCAGACAAAAAAAAACACACGAATAGAACTCGCCTGCCTCCGCCATATTTCGTGACATCGGGCGTG
CGGTTGAAAACGCTTTTCCGAGATAAGTTCTGCGTTGTCCGCATACCCCCTACTTACCTTTGGGTGTTGGCTGTGCTTTAAAACTATTTTAGTTG
GAATTTTCTTAAGATTTTGCGTAAATTGTCTCTTTTTTCACCTTTTCTTTGCACAATTAGCGAGATGTATACAGTGTGACCGTGCAAGAGAGAGG
GAGTATGCTATTTTTTATTAGAGATGGCAACGTGTCGTCACGGGTTTTAAAATTATATTTAATGTAGTTGATTTTTTAATTTATTGTGCTTAATT
TAATATTTTTAAGCAGCTTAAAATGTTTGAATCACTCTGATATATAATTTCCGAACAACAAATTATTTTATTGCCAAAATGAAAAAAAATGAATA
TTAAATCAAATTTTGCAGTCCAAAGCTGCTCCGATGTAACGAACTTCCTCTCACATATGTATCTAAGTGCTGCTGCACGGTCACACTCGATACGG
CTCTCGAAATGCGTCCACACTCTCGCCATTTAGAGTGCCCACATTCGCCACCCTGTTCAATTTTGTTTGGGTTTGAGGCCAGACAGAGGAGTCAT
TAATTTTAAACAAAGGACCACGCTTCAGGACATTCATCCCGGGTCAGACAAAGCCGCCACACACTTTCCTCGAGGCCGAGTGAAAGTTTCTCGCC
TTGTCGCCGCTTAACATCCGAAGCGACCGGACATGAACAAGCGCAACCATGTGAGCAGAAAACCTACGGCTCCACACACAAAGCAAATGTATTGA
GTGAAAAGTGCTATTTCTTTTGCAGATCCGCCTGCCGCCAGAGGTGAATCGGCTATTGTACGTGCGGAACCTGCCGTACAAAATCACCTCGGACG
AGATGTACGACATATTCGGCAAATTTGGAGCCATTCGACAGATACGCGTGTAAGATTGAAGATGATAATGCTATTCGCCGTGAATCCTCTCAATC
AATTTGTGTATCTTTTGCAGAGGCAACACTCCGGAAACGCGTGGCACCGCCTTTGTCGTCTACGAGGACATTTTCGATGCCAAGAACGCCTGTGA
CCATTTATCGGGTTTTAATGTGTGCAATCGCTATCTGGTGGTGCTCTACTACCAATCCAACAAGGCCTTCAAGCGCGTGGACATGGACAAGAAAC
AGGAGGAACTGAACAACATTAAGGCCAAGTACAA
(SEQ ID NO: 826)

Exon: 5304..5188
Exon: 4765..4660
Exon: 4592..3921
Exon: 3837..2725
Exon: 2667..2497
Exon: 2427..2256
Exon: 2194..2099
Exon: 1773..1698
Exon: 1427..1253
Exon: 1196..1001
Start ATG: 4758 (Reverse strand: CAT)

Transcript No. : CT22759

FIGURE SHEET 445

TCACACTGTATACATCTCGCTAATTGTGCAAAGAAAAGGTGAAAAAAGAGACAATTTACGCAAAATCTTAAGAAAATTCCAACTAAAATAGTTTT
AAAGCACAGCCAACACCCAAAGCAGCAAAATGACGTGGGAACCACAGGGAGAAGGTCTGCAGCAGATCATAGCGATCCTCAAGGAGTCGCAGTCA
CCGGACACAGCCACTCAAATGGCCGTACAGATGAAACTGGAGGAATTCAATCGCTACCCCGACTTCAACAACTATCTTATCTATGTGCTGACGAA
ACTGAAGACAGAGGACGAGCCCACGAGATCACTCAGCGGCCTAATCCTCAAGAACAACATCCGCATGCACGGCACCACTCTGCAGCCGGAGATCG
TGGAGTATATCAAACACGAGTGCCTGCAGGCAGTGGGCGACGCTTCGCCCCTGATCCGTGCCACCGTGGGCATCCTGATTACCACCATCGCCAGC
AATGGCGGTCTGCACAACTGGCCGCAGCTGCTTCCATCTCTCTGCGAAATGCTCGACAACCAGGACTATAATGTGTGCGAAGGCGCATTCAGTGC
CCTGCAGAAAATTTGCGAGGACTCTGCCGAGATTTTGGATTCCGCAGCGCTCAACAGGCCATTAAACATAATGATTCCAAAGTTCCTGGAGTACT
TCAAGCACAGCAGTCCAAAGATCCGCTCCCACGCCATTGCCTGCATCAACCAGTTCATCATCAACAGATCACAGGCTCTGATGCTAAACATAGAC
AGCTTCATTGAGAACCTCTTTCACCTGTCATCAGATGAGGACCACGAGGTGCGCAAAAACGTGTGCCACGGATTGGTCATGCTGCTGGAGGTGCG
AATGGACCGTCTGATGCCGCACATGTCGCAGATTATTGAGTACATGCTGTTGCGCACCCAGGACACCGATGAGGGTGTGGCCCTGGAAGCATCCG
AGTTCTGGCTTTCACTGGCCGAGCAAAGCATCTGCAAGGACGTGCTTGCCCCTTATCTTGCTCAATTAGCGCCAGTTCTTGTACGAGGCATGCGG
TACTCAGAGGTCGACATAATTCTCCTCAAGGGAAACGTTGAGGAGGATGACATGGTGCCCGATCGAGAAGAGGATATCCGCCCGCGTTTCCACAA
GTCCCGTGCACACACAATCAGGAGTACACAAGAGGGAGGAGCTGGAGCGACAGGCGATGATGACGACGACGAATTTGAAGATGGAATGGACGACG
ATAGCTCGCTATCGGAATGGAACTTGCGCAAGTGCAGCGCAGCTGCTCTCGATGTATTGGCGAATGTTTTCGAGAGGATTGTCTGCCCGTTGTG
CTGCCCATCCTGAAAGAGACTCTGTTCCATCAAGAATGGGTGATCAAAGAGAGTGGTGTGCTGGCCTTGGGAGCTATTGCGGAGGGCTGCATGCA
GGGCATGATCCAACACTTGCCAGAGCTGATTCCCTACCTAATTAGCTGCCTTTCCGACAAGAAGGCACTGGTGCGCTCCATCACATGCTGGACGC
TCTCGCGATACGCCAATTGGGTTGTCAACCAGCCGCACGACCAGTACTTGAAGCCTCTAATGGAAGAACTGCTGAAGCGCATTCTAGACTCCAAT
AAGCGCGTTCAGGAAGCTGCGTGCTCTGCCTTTGCTACTCTGGAGGAGGAGGCCTGCACGGAACTGGTGCCCTACCTGGAGTATATTCTAAAGAC
GCTCGTCTTTGCCTTCTCCAAGTACCAGCACAAGAACTTATTGATACTGTACGATGCCGTGGGTACTTTGGCGGACTCCGTAGGTCATCATCTGA
ATAAGCCGCAATATATTGACATCCTAATGCCTCCGCTAATTGATAAGTGGAACCTGCTGAAGGATGACGATAAGGATCTGTTCCCATTGTTGGAG
TGCCTGTCGAGCATCGCCACTGCCTTGCAGTCCGGCTTTCTGCCCTACTGCGACCCGGTGTATCGAAGGTGCATCTCTCTTATTGAGCAGACTAT
CAACCAGGAAATGCTGTGTAAACAAAACCAAACGTACGACCATCCCGACAAAGAGCGCATGATTGTCGCCCTAGATCTGCTGTCTGGCCTAGCCG
AGGGTTTGGATCGCCACATCGAGACATTGGTGGCCAACAGCAACATTATGCATCTACTCTACCAGTGTATGCAGGACGTTTTGCCTGAGGTTCGC
CAATCTTCGTTTGCCCTGCTGGGTGATTTGACTAAGGCCTGTTTCCCCCACGTGCATCCCTTCATGGCCGATTTCTTCCCCATCTTGGGTCAAAA
CCTTAACCCAGACTTCATTTCGGTCTGCAATAATGCTACTTGGGCCATAGGCGAAATCTGCATGAAATTGGGTGAGGAGACCAAGCAGTACATAC
GCCTTGTACTCAGCGACCTTTTCATCATTATCAACCGCCCGAACACGCCCAAGACACTGCTGGAGAACACAGCAATAACAATCGGTCGTCTAGGT
TATGTGTGCCCAGTTGAAGTGGCTCCTTATTTGCCCGAATTTGTACGACAGTGGTGCACATCGTTGCGGCACATACGAGACAATGATGAGAAGGA
CTCAGCCTTCCGTGGAATGTGTCATATGATCACGGTGAATCCAGCTGGCGTGGTAGCAGACTTTATATTCTTCTGCGATGCCATCGCTTCCTGGG
TTAACCCACCAGAGGATCTGCATCAGATGATACAGAAGATTCTGCACGGTTTTAAGACCCAAGTGGGCGAGGAGAACTGGCGTCGATTTGTGGAG
CAATTCCCGCCAACCTTGGCCGAGCGCCTGACCACAATGTATAACATCTAAGGCTAGCCATGCCATAAAACACCCACCTTCACCCATTAGCGAGC
CAAGCAGCAACTTTTTAACTAGACAATTATGTACAAGTATGCGT
(SEQ ID NO: 827)

Start ATG: 125 (Reverse strand: CAT)

MTWEPQGEGLQQIIAILKESQSPDTATQMAVQMKLEEFNRYPDFNNYLIYVLTKLKTEDEPTRSLSGLILKNNIRMHGTTLQPEIVEYIKHECLQ
AVGDASPLIRATVGILITTIASNGGLHNWPQLLPSLCEMLDNQDYNVCEGAFSALQKICEDSAEILDSAALNRPLNIMIPKFLEYFKHSSPKIRS
HAIACINQFIINRSQALMLNIDSFIENLFHLSSDEDHEVRKNVCHGLVMLLEVRMDRLMPHMSQIIEYMLLRTQDTDEGVALEASEFWLSLAEQS
ICKDVLAPYLAQLAPVLVRGMRYSEVDIILLKGNVEEDDMVPDREEDIRPRFHKSRAHTIRSTQEGGAGATGDDDDDEFEDGMDDDSSLSEWNLR
KCSAAALDVLANVFREDCLPVVLPILKETLFHQEWVIKESGVLALGAIAEGCMQGMIQHLPELIPYLISCLSDKKALVRSITCWTLSRYANWVVN
QPHDQYLKPLMEELLKRILDSNKRVQEAACSAFATLEEEACTELVPYLEYILKTLVFAFSKYQHKNLLILYDAVGTLADSVGHHLNKPQYIDILM
PPLIDKWNLLKDDDKDLFPLLECLSSIATALQSGFLPYCDPVYRRCISLIEQTINQEMLCKQNQTYDHPDKERMIVALDLLSGLAEGLDRHIETL
VANSNIMHLLYQCMQDVLPEVRQSSFALLGDLTKACFPHVHPFMADFFPILGQNLNPDFISVCNNATWAIGEICMKLGEETKQYIRLVLSDLFII
INRPNTPKTLLENTAITIGRLGYVCPVEVAPYLPEFVRQWCTSLRHIRDNDEKDSAFRGMCHMITVNPAGVVADFIFFCDAIASWVNPPEDLHQM
IQKILHGFKTQVGEENWRRFVEQFPPTLAERLTTMYNI*
(SEQ ID NO: 828)

Classification: known_flybase_gene
Gene Symbol: Trn
FlyBase ID: FBgn0024921

Celera Sequence No. : 142000013384640
TAACTGTAGAGGGGAAAATGGGCTTAATTCAAGGACTAATAAATTAATAATTCCATAATATATTTTAAAATGAAACGTGTAAGTACAACATTAAT
TTTTTATGTATATAAAATTTAATACTTTTCAGTAAAATATGGACATTTAAAACAGTTTCGGTGTAAGCATTTCAAATTAAAAACTCCAGAGGACG
AGAGCTGCAGTTACAAATAAAATTCGTGTTAAAAATGTTTAACTTGCATTCGTCTCGATTTTCTTACGTCGCTTTAGTGTGTTTAATTCCCTAGA
ACTTCATAAAAGCCGTAAATTGCACCTGAAACTGGGTAGAACTTCATAACTAAATCGGGTTTCTAAAAATCCAATTAAGCGTATTCAGTTTATGG
TTGGAAGCAGACACAATCACTTGCTGAAATCTAAAGAAACCAACCACATGGAGCCGTTCCCAAAATTCGTTATAATATTTCTAGCTGCCTTTATC
AATGTGGCATATGGCATGCATAATCCAATGATGCGTGATAGTGAGCTATTCTAAGACATATCTATATAAAATATGAACTAAAATTTATTTTCATA
TATTTTAGATTGTAATTTGGGAGAGCATCTAACTTGTAGGCTTAAGTTTATTCACTGTTGGCTGTACGCGTGCGTTTGTCTTCCGAATCACTCTT
ACTTGGGACTTGGAAATGGATGCCTTCACATCAGATACGCTTAAATATAAGTTATGAAATCTATATTCGTTTCTTCATTCATCTTGAATCATGTG
GATATGATTTTCCTATTTTATTGTCAAAAGGAAAATGGTCTTGCCACAACACATATGCATGAACATCCTCAACTGTTAATAAACATTGAAAACTA
TCCTGTTTTTTGAAGTAACAACTCCTTGGTCACAATTCTCAAATATATAATTTACAACCGTCGTAATAAAACGCATAAGACTTTCAGCTTACATG
CTAATCACGAACTACTACTTTATTTGCACTGAACGGCGGGGAGAGGATGACTACTTCGCTTTGTCCAGAAAGTCTTTGGCCTCGTTGATCTTGGC
CGCCAAATAGGGAGATCCTCCTCGATCCGGATGGTTCAACAGCATGATCTTCTTGTGCGCGTCCTTAATCTGTAAACAAATATAGGAATAAGAAT
ATTTGTATTTAAGCCAAAGGAGTATTTGATTTAAGCCAATACCATAAATATTATATAAACAAATTTGACAATCACAGGAACTACTTAGTTTCGGC
TTTTTCATTGCTTGGAATGCCTTTATAGAAGTATACAGCTCGGACTTCTGAGAGATCCTAAGCAAGAGAACTCCACATTACCTTTATCTTGGACG
CACTGGGGCTGACACCTAGGATTAGGGACGCCTCCCGCTTGTTCATCTTGGGATCGAAGCCGCCCTTGTAGTATTTGGAGGCGGCCATGCTCTCC
GCATCGTATTTGGGCAGGTTCTTGAGGGCCTCGTTGAATTTGGTGGTCATCTGGGGCATGCGGCGCATCAGGTGCTTTCCGGCGAATCCCACGGC
GGCCACGCTAAGACCCGCCAGAATTACGGAGCTCGCCTTCGGAATGGAATAATTCGTATTGGTCGACATCGCACGGACAATTTAATATTATGAAA
CGAAAGAGATTCGCAATATTTTACATTTGTTTTTGATTAAAACAATGTGATTTAACACAGTACCATTTTTATGTAATTTTAACAGCTGTAAGTC AGTGGAACTGCATAGCCTGCTGTCAGCTGTTGGATTATCGATAGACTCAGGGTTGTCGCTCTATTGAAAAAAATATTGCTAATTTAATTAGTATT
TTCATTTAATACTGTTGAAATTATAGTTAAATACTAATTAAAAGGATAATTTGTATGCACTATGCTTTTATATTATTTGCTTTAATATCTACATT
TTAAATCCCCATTTACTACGACACTGCAACCAAGCTGCTGATTGTCAACAACCAGGGCTGCAGGCTCACAACAGCAGTTGTTAAAACGATATTAA
GGTGATCTATCACCAACAGTTTGCAGCTGCAAATACATTAAGTGCTTAAACCAAACAGGTATTTCTAGAAATTCAGTGAATTTTATATCATGCTC
ACAAAATCGGCGCATCTGCTATCGAATGTGTGCGCAGACGTTGCCTATCGATAACAATCAGGTCGCATCGATAACGGGACTCAACAAAGTGCACA
AACAAGTGAAGAAGAAGCAGGAAAAAATTTTGATGTGCAAAGTTTGGAAACCAAATAATATTGATTGACGAAAGTAAGAGTTACGAAATTGGTGA
TCTCCACATCCTGGGTGGCGTGGTGGTGTGCGTGAATGATCGTCAGCGTACCGCTAATCGTGAGCGTGCGTGCGTGTGTGCGTGCGTGCCGTGTG
TCTGTGTCCGTCGGTCGCCGAGAGTGTGTGCGTTAGCTCCTCAGCTGGGAAAAACTTTTGGAAAATTAGCAGTTCTCCGAGATAAACAGCCGTC
AAACTGGAGCGAATTCCGGAATATCTGCGCGACACTGTCGATTGGCTTATGGGGTGAGTACCGTTACACCACTAAAGACAATGTAATCTATGGCT
CGAAAGTGTTAGTCCCGAAAAAAA
(SEQ ID NO: 829)

Exon: 1589..1317
Exon: 1114..1001
Start ATG: 1589 (Reverse strand: CAT)

Transcript No. : CT22766
ATGTCGACCAATACGAATTATTCCATTCCGAAGGCGAGCTCCGTAATTCTGGCGGGTCTTAGCGTGGCCGCCGTGGGATTCGCCGGAAAGCACCT
GATGCGCCGCATGCCCCAGATGACCACCAAATTCAACGAGGCCCTCAAGAACCTGCCCAAATACGATGCGGAGAGCATGGCCGCCTCCAAATACT
ACAAGGGCGGCTTCGATCCCAAGATGAACAAGCGGGAGGCGTCCCTAATCCTAGGTGTCAGCCCCAGTGCGTCCAAGATAAAGATTAAGGACGCG
CACAAGAAGATCATGCTGTTGAACCATCCGGATCGAGGAGGATCTCCCTATTTGGCGGCCAAGATCAACGAGGCCAAAGACTTTCTGGACAAAGC
GAAGTAG
(SEQ ID NO: 830)

Start ATG: 1 (Reverse strand: CAT)

MSTNTNYSIPKASSVILAGLSVAAVGFAGKHLMRRMPQMTTKFNEALKNLPKYDAESMAASKYYKGGFDPKMNKREASLILGVSPSASKIKIKDA
HKKIMLLNHPDRGGSPYLAAKINEAKDFLDKAK*
(SEQ ID NO: 831)

Classification: hypothetical

Celera Sequence No. : 142000013384523
TGCTCTAACTAGGCCACACACGGAACAGGGATTGGAAATTTCACTTTGAGCTGCAAAGTTCTGGCGATCACCTCCACCTCTCGCAACGCGGCAAA
ATATCAACTGAATATTTTCAGACCTCGAGTGTGTTATTTGCGTTAAAAGAAAGAGTCGCGAATCGCTGCGAAGAGAAGAAAGAGAAAAGAAATAC
TAAAAGCTCGCTCCGAAGCTTTGGCGACGCGAGCATGATTCTTCTCATATACAGTATATAGCATTTGAATTGATTAAATGCTAATTTAGCATGCT
GTGGTCGTTGCCGCCATCGGAGATCTTACACTGAAACTTGAAAAGCGGATTCTGAATATCAATTCTTCTTGAAAAAAGGCTTTTATATGTATACA
TAGATCTATAGCTTCCTAAAAATCATTGCAGCTCATTATCAAACATGCTTTAATGCTGATTCGTCTGTATAAATATTTAATTATTGTCTACCAAG
TCATTGGAAAATTTTCACCACTATGCTTATTCGCCAACACTCTCGGAATATTTTATTTTTTCCATGGTCTATTTGTATAATTTCTTACCTTAATG
CCAAGACCATTTGAATATTTATACCCTGTCCTTTGCTGTTTTGTTCTCTTATCAATGCCCTTCGCATTGACCGAGTTTTCAGATTTCCTTGCCTT
TGGCATCATTAATCCCTTTCAACATGGCCAAAAGCCATTCAAAACTGAATTGTTGAGAGCTGTCACTTGGCATTTTATTGCCATCAGATAGCTGT
ACTCACAACAAAATTCTACGACAACCCAACCGACAAAGCCCACACGATGATAGTTAATTAAAAAGTTGTTGGCACACTCAGAATATCATGCAAAA
TTAGCCTGGCTAACTGGCCTTATCATAATTATCAGCAATCCCCAAACAAAACTTTACAACATGATAATTATTAAATAAAAAGCAAATAACCACTA
ACAGTAGAACCGAATTAACATTTGTGAGCTCAGAAAACAAAAGCAAAATACAGGTGAAACAAAATGCAGCAGCATCCGTTTACTAATTTATACGC
AATCTCAAATAATTTACAAAACAAATGGTTAACCGAAAGAAATATTTTAACAAGCTTTCTTGAGGCATTACAAAAATTAAAATAATATATTTCAG
ACAGAGCAAGATATCTATTTAAATATTATTTTATACAAAATGAAGCAATTGTTAAACAATTTGGACAACGCATGCAATCGACCCTATTTGTAATT
TAATTGATCAAAAGCGAATGTGTCTTAAAGCAGTACCTCTCTACTACACGCTTGATGTTAAATTGAATTTTTGCAATTTTTATTTTTCCGGTTCT
TTAAATATAATATAATAATAATAATAATAATTTTTCCAGCTGATTTTTATTTGTAGTTTTGTTTTTCTTTGTATTTAAACTTATTATGTTGATGC
TGTTGTTGGTAGCTGTCTAGCTTTTAATGTTTAATGCTTACATCATTTTTTCAGTAATTATTATTAAATTATTTCCGTTTATGCTGTTCTGTTTC
TGTTCGGTCAAACACACAATTAATCGCATGTTCGCCACCAATCCGCCAGTTGCTGCTCCAATTGCCACTGCCACAGCTGCAGCGGCTGTTGCTGC
TGATGTTGCTGCAGCTGCTGATGTTGCTGCGGCCCCAAGGACGCCTTTGCCGCTGCCGTTGCTCTTGGTACCGCCGCCAAATTTGCTGCTCCTAA
TGCTAATGCCGCTGCGAAGGCGGTAGCAGCGGCTGCTGCGGCGAAAATGACTGCGGCAGTTGATGATCTTGCTGTTGTTGCTGCTGCAGCTGCTG
CTGATGATGTTGCTGCTGTGGCGAGTGTTGGTGTTGTGTTTGTTGCTGCTATGGTGGTGACCGCAGTTCCTGCTGATATTGTGGCTATTGTTGTG
GACAACAGCACGGCGGCCATTGCCACTTACAATGACGCTGCTGCAGCTCCTCCTCTTCTGAATCTGACTATTGTAAACTGTTGATGTTATCTTTG
TTGCTTTTACTGTTGTTGTTGCATCTGCTTTTACTTCTGCTATTGTTGATGTTGAATTTGCTGATTCTGTTGGACTGCTGCAATCTGGAACGCAT
CACATAGCATACTTTCTAGTCCACTCTCGTGCCAGCTCATTGTATTTTTCCCGATCGGTTTTATATATTCTGGCAATCTCTGGAACAAGAGGATC
GTCTGGATTGGGATCACAGAGTAGAGAGCAAATTGATAATAAAACTGAAAGAGAATATGGAAACACATGTTAGTATCATTTTCGATGTAAGAACT
TTAGATGAACTCACCTTTTGAAATAGTTAATGCTGGCGACCACTGAGATCTTAATATATCGAGACAAATCGATCCATTGCTGTTGATGTTTGGAT
GGTATATGCGCGTTGTAAAAGCCACTTTGGGTGGTTTAAAGGGATAGTCTGTTGGAAAATGTATAGTTAAGAAGAATACACCTCCTTGATAAGGG
CTGTCCGGCTGTAAGAAAATTGATAACAAATACTATTAGTACAAGAACACTAGTTTACTACACACCTAGTTTATTTTATTTTGGTTTATTTGGAG
GTCAAATCATAGATTGCGTTCACTTGAAAAATTTGGTTAAAAGAATGCTTTGAAATAATAAGAAGTTCTGAAGTAAATTATCGCGAGCTTCAGAC
GCATGCCACAATGTTTACACGTTTAATGGATTGTTCTACACATGTACTGGATTTCTATTTAAACACACGATTACAAATGTACTTGGCTATTATAT
ATTATCTATCATTTCAAAGCATCTAATCAACTGACGTAGCTTATTTATAAATACAAATAGAGTATTGTTTTATTATTGCATTCTAATTTACATTA
ATGATTTATTAATCTGCTATTTTTAACTGTATACGGCAATCCCTGATCAGACCAAAAATAAACCAATATAAAATATTTCAGGCTACAAATTAAGA
TAGAATCGATTCGATCTTTCGGTGAAGTCCTCTTACCGGGCCCATTATTGTAGCTTGCCAGTGAAATACTGTAAGAAAACAAGAGATACATTAAT
CAAAACTGTTAAAAACGTAGTTGTGATATAATCCTAAAGAGCAAACATAAACTGCGCTGCAGTTAAACGTTTTCTGTTTGCTTTGATATGAGTCC
TATATCTACCTATATCTGCCCTAGATGGGAAATTACTGTGTGTACGTAAAGCATCTTGGATATTTACATTTGATAATGAGATGATGACAGAGTAT
ATTAAAATTTTCCCTTCGCTCAAAACTAAAACGTATTTTTCCTTGCCCAAGTTATATTCAAGTAATGAGTTTAGATACAGGAACTGATTTGCTAA
ATAACTAGGTAAATAAAATTAAGCTTCCAACAAGCCACAGAAATGTAATCTTCTTGTAGTACAATACCACTTTCCCCTAGTTCGCCACGTCTAGG
CCCCACTGTATATGCATCCAATGCAGCAAACTCGCTCTCGTCTAAATAAATGCACCACTCTCTCAGCGCCGCCCACCACCCCACTTCACCACTTC CATTCTCATGGCCACGCTCTTTAGCGATTCCCCCCCACAAAAGAACAAACACAAACAATGCCAGCCAAAGAGCCTTGGCACCGACAATTGGCAGC
AGCGTCAGCAGCAGAAAAAGCACCAAATGCTCTCCCCCTTGAAACAAAAACAAAGTTTTTAAAGTAAGGAATATACCTATACCGAGATACCCTGT
AACCAACCAGGCTTTAAAGCACACATACGAAAAATTCATTTCTATATAAAACTGAGATATTTTTATAAAATCATGTTTTCTTAATGGTGGAACGC
AATATATTCGATTTTTCAACCGATTTCATGCTAAACAAACCTTGACTATTATTGGCATACATTTCCATGAGTTCTATATATCCTTTCACACTGCA
GAACATCACATATGTATATATATATACCCTTGTACCCTGTGAGAGAGCACAAAACGTGTGGCAGTTGGCTCAGAATCATGGCCAAAACAGAGCTACT
GGCTATGCCGTCAATGTCATTCTGGTGAACGAATCGAATGCGACTGGGAAACTCTCTCTGTTGTGGCAGAGCACTGAGAACTGAACTGGGAACTG
GGCCCTCGGTAACCAGCTGCTGCCTTGACCATAATTACACGAAATGTTCATTTGTCCATCTGCAGTAGGGAGTTTGGGTCTGGAAAATGCGTCGG
CATTGTTTTTGTCATAGCTCAGACGAAAGTAATCTCATAGCTGCAGCCATTTTGATTAATACCACTTAGACAACAATCAATAATTTCTGAGCATT
GCTAAGGCAACAAAAACCCTGCAACCAGATGATATTAATAAAAGCAATGCATATTTAGATAAAAACATCCTTAGTGCATTTAAAGAATTGATTAA
TCCGACCATGGTAGCTTAGCTCAAAAGCATTCAATCAATGTTGAGTTTAAATGTTTAAATACATGATTAAATCATAAGGTTTCCTTTGCCATACT
ACAATTACAATGGATTAATTTCACACACATACACACACACACACACACACACACAGCGCCACACTGAGCTGAAAATGGATGGGAGTTTCCATTGC
ACTCGAGTGAAAATTCGCCACCCACCCAACCAACACCTAAAAAACCAAAGTAAGCCCCGCCCTGAGCTGCAATTCCTTTCTTTTACCCCAGTTGC
TGGGAATTCGAAGGCAAGGGTTCGGAACAGCCAAATTGATAATAAAAGCAAAGTGATAAGAACTGCGGAAATTATTGAGCTGACTCCTCAATAAT
CATAGAAATATTCACGCTTATATACAAACATACTTTTAATTGTATATAATAGCGACGTTTAAACGCTGTTAATAGAAATCGAGTGAAATCGCCAC
ACTGGTCGTTCATTATCAGCAAACGATGACAATTATTAATATTATTATTTACTCTGCCTCGCGGGAACTTGAATGAGTTTGATTTCCTTACGACC
AGAGAAACTGGGAAATGAAACACAAAGAAATGAGCTAACGAAAGTGCTGGGATATATATAAAATATTTCAATATTTTGCCGTTCTGTATAATATT
TTCATTTCCACAAAAGTGCGTTCACTAAATTATAATATATATATAATACTGCAAAGCATTACGAACAAAATTTCTATAAGTTCCTATAGTTAAAA
CAATAGTTTATATAGCTTTTTGCAGAATAATTTCAGTTCCTAGCCATTTTCCCTAAAACTAAGTATTTAGTTTGCCATTTTCTTTTTAAAATTTT
ATCGCTTACAAAGTATGCCGGTGTTTTTTTTTTTTAACCGAAATCGTCGTCAGCAAGACTATATAATTTACGATTTCACTTTTTGTGACGTCATT
GGAGAGTGACCCCCATATGGCTGGCACCTCTTCCTCTTCCCGCTTGAGTGGTGAAGGGGTGAAGGGAGGGGGGGGGGGTGCTTTTCAGTAACGGT
TGTCTGTATGCAGTACAGCTCTACGTGCTATAACGTAACCGAATCCGATCCACAATCAGCGTGAATTTGTTGGCTAATTGCATGACGGCTTCGTG
AGTTTTTTAAATCGAGTTTAAGACAGCGAAGAAAAAAGAACCAAGTCATGGCGATCAGCTGTTTGGAGGCCGTCGCTATCACAAAATAAAAAGAA
CCGAATCCAAACTTGGCGCAAAAGAATTCCAAATTAGCAAAGTCCAAACTAAAAGTAACAGCCAATAGGAAAACAAACGATGTACAAATTTAGTG
TGTTATATGCCTAGTCACGATCGAAATCTATGACGTGGTGATGGTCGATCGACAATATTTGCATTTTTTATTAACAATTCCGAGATAGTGGTATT
GTGAATTTTGCCTAATATATATATAGTTCCTATTCCTTGCATCAGACTATATACTATACTGACTCAGACTTGGCAACTCAGAAATATTTCACATA
ATTTCATGTCTTGGAGCTCCCACACGATATGGTGAAATCGAAACTTGGGTTAAAGCCCCCCCAACATAATACAACTGACTCACGGCAAATCAACG
AGTTGTTGAATAACATTAGCAATACTTACAATCATCTCCAACTGGACCGGCTGAACATTGTGCAGGTGGATCTCTGCCCAGATCTTGCAGTTCCT
GTTGAACAAAGACATTTTCAAATTAGTCATTGAAATAAAAGTTAAATATAGGTATGTAAGCTCAGTCAATTTCTGATTGTTTTTAACAGTTATGT
CAAGTCCTACAAAAAGAACTGGTTTTTAAAGAGTATATCTAATTTCTAGTCAAACCTTATATACTACCTACTTTCTGAAAGCATAGGTAACAAAC
CTAGCAATTGCAATACAGGAAACCCCAAAAAGAATTCTCGAAATGGGAAATGGTCAAAAGTGCATTTCATGGATATCTGCTTATGTTTTCCGGTA
GTCGGTTCTTTTGTTTTGCTCTATGATCCAGCTATATGTACATACATATGTATGTATGTACCACGGTTTTCCGGGTGTGCGTACATTTTATGCTG
TGTGGTTGGTATGCAAATGATGTAAATTTTAAATGCAGAATTTAAAAACAGATATGTGGGGATACAAAATAAACATTTTTATGCGAGAGCTTCGT
TCGAAGCGAGTGCGAGCGAGAGGGAGAGACGTGAAAAATCAAGTTCGTTGGCCCGGACCACAAATGGCGCTGTCTCCTTCTGCCCCACCCCCCGA
CCAGTCGCTCCATCCCTGTTGCACTCGCACGCACACAGCTGAGCGGCTCCCCTCCCTCTCTCTTACACTCCGACTCTTCTTCACTTATCACAGCT
GCCCCACACACACACACTCCAAACGGGGAGAGAGAATGAGGTGTAAGGTAAACCGGCAAAAAAAAAGAATATATATATAAAAAGAATAATGAAGA
TGAGCTGCGAAAGAGTAGCGCGACTCAGTGGAGAAGTAAGAGGAGGAGCAGCAGGAGGAGGAAGAATGAAGGAGAGTGAGAAGACTGAGCTTCAG
TGTATGCGTGTGTTTGTAACGGCACCACAAAATCAGAGTGGAGCACAACAAAAATAGCCGTCGCGAAAAACACCGTGTTTCTTTGCCCCATCTCA
CTTACTCATTTTGGGAATTGTACCTGTTGAGCAAAAATAAATTACAAGAAATTGTTACATTTCTTTTTTCGTTGGGAGTCGGAGCGGTTATGACT
CATATCAGACGAACAAATGAAGTAAAAACAAACACGCACACTTGTGCACAGCAAGAAAATTCGATAATATTATCAATATTAGACCAGGTGCACTA
CCAATACAAACTTCTATTTAATTCTTATTCGAATAATTAATATTGTGAACTTTAAGAATTGGTTCAGTAAGACTAAATGCCATATGCATTGGTTC
TAAAGCCCATTTCGTTCAGTGTACGGTTCAAGTGAGCTCCGATCGGCGTTTAAGCCGTTCTCTCTCGCTCTTTAACTCTCTTTTTTGGCAAATGA
GGCCATCTAGAGAAAAAAGGCTTTTGAAGAATTGACCACAAAAAGGGGGCGTGAGTGATTTTAAGAGTTTACTACAATGTATACTTTTATTTCCG
GTTTGCCGCTTGCCATTTCGTTTTCATTTAGGCAGGCATTAAAATGTTATAATGGATAGAAAACTACGAAAAACGAGGAAAACTCAATGGCCATG
ACGCCGACGCAGGCAGCGCTGCTTTTGTCGAGACAGTCAGCAGACCCCCGCCCCACACATTCAAACACAAATACACACCACGCTCACACATACGC
ATAGATATGAACAAATTCCGCATTCGCTGCTCATTTTGTATGTAAATTATGCTTAATTATAATTTATAACTAATTATTTGGGGCCCCCTTTTGG
CTGACGGTGTTTTGCAACACTAAGCCCCGCTAGCACTCACACACTTGCGCTCTCTTTGGCTCTGCCCCATTGCGCGAGCGGGACCGAATGAGGCC
TCAGCTGTCGCGGGCAAAGGGAATGCGCCAGGGCCAGAGCGAGATGGCATGCAATGGCCATAGCCAAGTGATGGCGAGACTTTGTATTTGCGAGC
GTTTTAATGTGTGTGTGTGTGGGGTATGACTATGATAACCGGCTTCAAACGTAAAAAAAGATCCCAATTTGCCAAGTAACATTTCCACAACTTCG
AGATATTACTAATGCTTTTGAGGAAGGCTGGGATGACTTTGAAAAAATATCGGGTTGTCAGGGCCTTGAACATTGGGGTGTAAAAAAGCATTTAC
TGGACAAGGACAAACGACGCGCAGGCACTTTAAAAATAATTATCGAAGCACGCACGCTAGAACCACTCTACCTAAATACATATATAAATATATAT
GCTTGGGGGCAGCACTATTTCTGAATTATCAGCGCAAAAAGTAGGGTTAGGTTAATTTTATACGCTTCTTGCTTTTGCTCTGTTTTATTTTTTGC
TGGATCTTTCTGCGGCGCTGGCAGTGTGTGCGTTTATGTGTGACTGTTGCGAGGCTGAGAGTGTGTGCGAGTGCCGTGTACAGCGTGTATTGGGT
AACAGCGCCCGTAGAGCTGCGAAAACTCCGCCGTATAGTTGCATTAATGTAAATGCATCCAGGTGCCCGGCACACACGCACACAAACAATGCACA
TTTGCATTGCACTTTCACGCACACGCATCGCACACACACTTATCCCACACTCTCGCAAAAGTAACGGAAGCGATGACTGCACTACACGTTGCCTT
GCCCACCACACACACACATCCTTATACCTTTTTCACCACCCTCAAAATTTCTAATCTGCTCCTAATTACTAACTTATTAATTAAATGGTAACTCC
ACAGCTCATTTTCTCCCTTCCCTCTTGCACGCTTCTTTCCCCCCGCTTCTTCTTTCTTCTCCTCGGTTACTACCTACGTTTCACATTTCTTGCAT
AAAATTTTTCTCCCGTTGAAAACTGATGTCTGTTCGCTTTTTTTTTAGACTATCATTTTGGTGTATCGCAAAGGGTTCTGTTCTTTCTTTTTTTA
GTCCGTTTCGCAAAGTTTTTTGAGATATTCCTTTTTTCACATACCTTATTGATTCTTTTTAACGCCATTTTCTGATTGAAATTTGATTTTCTGGG
TTGTGTGTGTGTTTGGTTGGTTGTGTGTGTGTTTGGTTGGTTGTGTGCTGGTGTTGGTGTCTCGCGTATTTCTTTTGTTCTTCGCACAGAATTGG
GTTTTATTCAATATATAATCCTCCTGCTTAGAATTGAACGAAAAACGAAACACAAAGCTGCGTTGCGCCTCTAGAACTTTGATGCTTAAATATGG
CTCTTTCGGTTGAGTGTCCCTTGTCACGAAATAAAGCAGCACCAGCGCACTGCAAGTAAAAACGGCGACCCGACGAAGACTACGGCGACGATTAT
TTTTTCACAATCAATGCGGGGCCTTTCGACCGTTTGTGCGATAGAGACGACCGTTAGTGAGCTGAGAACGCAACGAAGCACAATCGTTACACCGA
AGTGTAAGCCCGAGCGAGAGGAATGGTGTGTCTGTGTCGTGTGGTAGTGTTGTGAAGCGGAAGTCCAGCAGAGCAGTCCAGCTATATGACCTTTT
CGCTAGGGGTGGCCAGATCGATTGGGTGGCAACGCCTTTTAGGTGAGGGATGAATCAGTTAATTACAATTTGATTGCCAATGCAAGACTCTTCAT
ACTCACTTTAGTTCGGGAACAGCCAGAAGAAATAGTTTTACCGGCAGCGAGGAGGTGTTATATTTTATTCGAACTACCTTCTTATCGATGGTGCG
TGCGCCCAAAAGCTTGCAACTTGTATGTAAATTTGTTAACACCCAACGTGTTGCAGGCTGCCGGAATGTTTTTACTGAGCAATTTTGAGATGTTG
GTAATCCGAGTTCTTGAAAACTTTCCGACTAGCTACTGAGTTCTACAACTGAATTGACAGGGCGTTATTTTAAAATTTAAATTCACTCCAGAGCG
CTGGTCTGGCAAGGCCGACGTGCCAATTCAGGATACTTGTCGATATTTTCCGTTGTGCTATCGATAGTTTTTGGGAATAACAGGCGTTAGTAGAT
TTTTAGTATTTAGATTTTATTATCATAAGGATGAAAATATTTTTAACAAAATAAACTGGTTCATTTAATTTAACTTTTTATTTTCTCACTACTCC
AAATGGCGCTTCCGCTGTCTGAAACTGCCGTTATAATAGTATGAACAGTTAAAACAATCGACGGTAGCTGAATTTAATCAATGCAGCCCTCTTAC
CCTATACATCGATAGTATCGCATAAACATCGATTTTGGTTCCAGCTCTAACTTTAACTGTCTGCAAAATATTTCAAACAAAAGTGTTTGTTAATT

FIGURE SHEET 448

AAGTAATATACTTAATATTAGTGGCTGTTTTGCTTCGACATTGATCGAATTGCGGTTGTGCAAGTGTTTTGTTTGATTTGTTGGCGTGTTTTTCC
TAGTTTGGCGGCCCTTTGAACTCGTTCGTGTATCGCCATCTCTCTCCCACCCCCGCAATCGGCTTCGTGCGTATTTTTTTGTGAATTTTTACACA
GAACTCACACTTTTGTATGGCCCAAGAATTTGTACAATATTTTTGCACTTGAAAAACAAGAAATAATGAAGAAAGCCAAGATAAACGCGACGATG
TGCAAGTGCTAATCATTCAGTTTTGGCAAGCGCTGAACTTCGCTGACTTCTTGAACAGCAAAAAAGATGGAGGAGGATAATGCCAAGGTCCTAAG
TAATAACAACAAGAACAACAGAAACAACAATAAGGGACGCCAGCAGCTGCAGGGACACGCCCACAGCTCCGCCACCGCCCACGCCTCCGTCGATA
TATTTATATTCGATTTATAGTAGCTGTAGTTGTAGTCATGCCAACAACAAAAACGCAAACACAGACAACAAC
(SEQ ID NO: 832)

Exon: 9807..9602
Exon: 9535..8975
Exon: 6078..6015
Exon: 3013..2982
Exon: 2478..2295
Exon: 2229..1001
Start ATG: 8998 (Reverse strand: CAT)

Transcript No. : CT22777
AGTTTTCAAGAACTCGGATTACCAACATCTCAAAATTGCTCAGTAAAAACATTCCGGCAGCCTGCAACACGTTGGGTGTTAACAAATTTACATAC
AAGTTGCAAGCTTTTGGGCGCACGCACCATCGATAAGAAGGTAGTTCGAATAAAATATAACACCTCCTCGCTGCCGGTAAAACTATTTCTTCTGG
CTGTTCCCGAACTAAAGCGTTGCCACCCAATCGATCTGGCCACCCCTAGCGAAAAGGTCATATAGCTGGACTGCTCTGCTGGACTTCCGCTTCAC
AACACTACCACACGACACAGACACACCATTCCTCTCGCTCGGGCTTACACTTCGGTGTAACGATTGTGCTTCGTTGCGTTCTCAGCTCACTAACG
GTCGTCTCTATCGCACAAACGGTCGAAAGGCCCCGCATTGATTGTGAAAAAATAATCGTCGCCGTAGTCTTCGTCGGGTCGCCGTTTTTACTTGC
AGTGCGCTGGTGCTGCTTTATTTCGTGACAAGGGACACTCAACCGAAAGAGCCATATTTAAGCATCAAAGTTCTAGAGGCGCAACGCAGCTTTGT
GTTTCGTTTTTCGTTCAATTCTAAGCAGGAGGATTATATATTGAATAAAACCCAATTCTGTGCGAAGAACAAAAGAAATACGCGAGACACCAACA
CCAGCACACAACCAACCAAACACACACACAACCAACCAAACACACACACAACCCAGAAAATCAAATTTCAATCAGAAAATGGCGTTAAAAAGAAT
CAATAAGGAACTGCAAGATCTGGGCAGAGATCCACCTGCACAATGTTCAGCCGGTCCAGTTGGAGATGATTTATTTCACTGGCAAGCTACAATAA
TGGGCCCGCCGGACAGCCCTTATCAAGGAGGTGTATTCTTCTTAACTATACATTTTCCAACAGACTATCCCTTTAAACCACCCAAAGTGGCTTTT
ACAACGCGCATATACCATCCAAACATCAACAGCAATGGATCGATTTGTCTCGATATATTAAGATCTCAGTGGTCGCCAGCATTAACTATTTCAAA
AGTTTTATTATCAATTTGCTCTCTACTCTGTGATCCCAATCCAGACGATCCTCTTGTTCCAGAGATTGCCAGAATATATAAAACCGATCGGGAAA
AATACAATGAGCTGGCACGAGAGTGGACTAGAAAGTATGCTATGTGATGCGTTCCAGATTGCAGCAGTCCAACAGAATCAGCAAATTCAACATCA
ACAATAGCAGAAGTAAAAGCAGATGCAACAACAACAGTAAAAGCAACAAAGATAACATCAACAGTTTACAATAGTCAGATTCAGAAGAGGAGGAG
CTGCAGCAGCGTCATTGTAAGTGGCAATGGCCGCCGTGCTGTTGTCCACAACAATAGCCACAATATCAGCAGGAACTGCGGTCACCACCATAGCA
GCAACAAACACAACACCAACACTCGCCACAGCAGCAACATCATCAGCAGCAGCTGCAGCAGCAACAACAGCAAGATCATCAACTGCCGCAGTCAT
TTTCGCCGCAGCAGCCGCTGCTACCGCCTTCGCAGCGGCATTAGCATTAGGAGCAGCAAATTTGGCGGCGGTACCAAGAGCAACGGCAGCGGCAA
AGGCGTCCTTGGGGCCGCAGCAACATCAGCAGCTGCAGCAACATCAGCAGCAACAGCCGCTGCAGCTGTGGCAGTGGCAATTGGAGCAGCAACTG
GCGGATTGGTGGCGAACATGCGATTAATTGTGTGTTTGACCGAACAGAAACAGAACAGCATAAACGGAAATAATTTAATAATAATTACTGAAAAA
ATGATGTAAGCATTAAACATTAAAAGCTAGACAGCTACCAACAACAGCATCAACATAATAAGTTTAAATACAAAGAAAAACAAAACTACAAATAA
AAATCAGCTGGAAAAATTATTATTATTATTATTATATTATATTTAAAGAACCGGAAAAATAAAAATTGCAAAAATTCAATTTAACATCAAGCGTG
TAGTAGAGAGGTACTGCTTTAAGACACATTCGCTTTTGATCAATTAAATTACAAATAGGGTCGATTGCATGCGTTGTCCAAATTGTTTAACAATT
GCTTCATTTTGTATAAAATAATATTTAAATAGATATCTTGCTCTGTCTGAAATATATTATTTTAATTTTTGTAATGCCTCAAGAAAGCTTGTTAA
AATATTTCTTTCGGTTAACCATTTGTTTTGTAAATTATTTGAGATTGCGTATAAATTAGTAAACGGATGCTGCTGCATTTTGTTTCACCTG
(SEQ ID NO: 833)

Start ATG: 744 (Reverse strand: CAT)

MALKRINKELQDLGRDPPAQCSAGPVGDDLFHWQATIMGPPDSPYQGGVFFLTIHFPTDYPFKPPKVAFTTRIYHPNINSNGSICLDILRSQWSP
ALTISKVLLSICSLLCDPNPDDPLVPEIARIYKTDREKYNELAREWTRKYAM*
(SEQ ID NO: 834)

Name: effete
Classification: enzyme
Gene Symbol: eff
FlyBase ID: FBgn0011217

Celera Sequence No. : 142000013384523
TGCTCTAACTAGGCCACACACGGAACAGGGATTGGAAATTTCACTTTGAGCTGCAAAGTTCTGGCGATCACCTCCACCTCTCGCAACGCGGCAAA
ATATCAACTGAATATTTTCAGACCTCGAGTGTGTTATTTGCGTTAAAAGAAAGAGTCGCGAATCGCTGCGAAGAGAAGAAAGAGAAAAGAAATAC
TAAAAGCTCGCTCCGAAGCTTTGGCGACGCGAGCATGATTCTTCTCATATACAGTATATAGCATTTGAATTGATTAAATGCTAATTTAGCATGCT
GTGGTCGTTGCCGCCATCGGAGATCTTACACTGAAACTTGAAAAGCGGATTCTGAATATCAATTCTTCTTGAAAAAAGGCTTTTATATGTATACA
TAGATCTATAGCTTCCTAAAAATCATTGCAGCTCATTATCAAACATGCTTTAATGCTGATTCGTCTGTATAAATATTTAATTATTGTCTACCAAG
TCATTGGAAAATTTTCACCACTATGCTTATTCGCCAACACTCTCGGAATATTTTATTTTTTCCATGGTCTATTTGTATAATTTCTTACCTTAATG
CCAAGACCATTTGAATATTTATACCCTGTCCTTTGCTGTTTTGTTCTCTTATCAATGCCCTTCGCATTGACCGAGTTTTCAGATTTCCTTGCCTT
TGGCATCATTAATCCCTTTCAACATGGCCAAAAGCCATTCAAAACTGAATTGTTGAGAGCTGTCACTTGGCATTTTATTGCCATCAGATAGCTGT
ACTCACAACAAAATTCTACGACAACCCAACCGACAAAGCCCACACGATGATAGTTAATTAAAAAGTTGTTGGCACACTCAGAATATCATGCAAAA
TTAGCCTGGCTAACTGGCCTTATCATAATTATCAGCAATCCCCAAACAAAACTTTACAACATGATAATTATTAAATAAAAAGCAAATAACCACTA
ACAGTAGAACCGAATTAACATTTGTGAGCTCAGAAAACAAAAGCAAAATACAGGTGAAACAAAATGCAGCAGCATCCGTTTACTAATTTATACGC
AATCTCAAATAATTTACAAAACAAATGGTTAACCGAAAGAAATATTTTAACAAGCTTTCTTGAGGCATTACAAAAATTAAAATAATATATTTCAG
ACAGAGCAAGATATCTATTTAAATATTATTTTATACAAAATGAAGCAATTGTTAAACAATTTGGACAACGCATGCAATCGACCCTATTTGTAATT
TAATTGATCAAAAGCGAATGTGTCTTAAAGCAGTACCTCTCTACTACACGCTTGATGTTAAATTGAATTTTTGCAATTTTTATTTTTCCGGTTCT
TTAAATATAATATAATAATAATAATAATAATTTTTCCAGCTGATTTTTATTTGTAGTTTTGTTTTTCTTTGTATTTAAACTTATTATGTTGATGC TGTTGTTGGTAGCTGTCTAGCTTTTAATGTTTAATGCTTACATCATTTTTCAGTAATTATTATTAAATTATTTCCGTTTATGCTGTTCTGTTTC
TGTTCGGTCAAACACACAATTAATCGCATGTTCGCCACCAATCCGCCAGTTGCTGCTCCAATTGCCACTGCCACAGCTGCAGCGGCTGTTGCTGC
TGATGTTGCTGCAGCTGCTGATGTTGCTGCGGCCCCAAGGACGCCTTTGCCGCTGCCGTTGCTCTTGGTACCGCCGCCAAATTTGCTGCTCCTAA
TGCTAATGCCGCTGCGAAGGCGGTAGCAGCGGCTGCTGCGGCGAAAATGACTGCGGCAGTTGATGATCTTGCTGTTGTTGCTGCTGCAGCTGCTG
CTGATGATGTTGCTGCTGTGGCGAGTGTTGGTGTTGTGTTTGTTGCTGCTATGGTGGTGACCGCAGTTCCTGCTGATATTGTGGCTATTGTTGTG
GACAACAGCACGGCGGCCATTGCCACTTACAATGACGCTGCTGCAGCTCCTCCTCTTCTGAATCTGACTATTGTAAACTGTTGATGTTATCTTTG
TTGCTTTTACTGTTGTTGTTGCATCTGCTTTTACTTCTGCTATTGTTGATGTTGAATTTGCTGATTCTGTTGGACTGCTGCAATCTGGAACGCAT
CACATAGCATACTTTCTAGTCCACTCTCGTGCCAGCTCATTGTATTTTTCCCGATCGGTTTTATATATTCTGGCAATCTCTGGAACAAGAGGATC
GTCTGGATTGGGATCACAGAGTAGAGAGCAAATTGATAATAAAACTGAAAGAGAATATGGAAACACATGTTAGTATCATTTTCGATGTAAGAACT
TTAGATGAACTCACCTTTTGAAATAGTTAATGCTGGCGACCACTGAGATCTTAATATATCGAGACAAATCGATCCATTGCTGTTGATGTTTGGAT
GGTATATGCGCGTTGTAAAAGCCACTTTGGGTGGTTTAAAGGGATAGTCTGTTGGAAAATGTATAGTTAAGAAGAATACACCTCCTTGATAAGGG
CTGTCCGGCTGTAAGAAAATTGATAACAAATACTATTAGTACAAGAACACTAGTTTACTACACACCTAGTTTATTTTATTTTGGTTTATTTGGAG
GTCAAATCATAGATTGCGTTCACTTGAAAAATTTGGTTAAAAGAATGCTTTGAAATAATAAGAAGTTCTGAAGTAAATTATCGCGAGCTTCAGAC
GCATGCCACAATGTTTACACGTTTAATGGATTGTTCTACACATGTACTGGATTTCTATTTAAACACACGATTACAAATGTACTTGGCTATTATAT
ATTATCTATCATTTCAAAGCATCTAATCAACTGACGTAGCTTATTTATAAATACAAATAGAGTATTGTTTTATTATTGCATTCTAATTTACATTA
ATGATTTATTAATCTGCTATTTTTAACTGTATACGGCAATCCCTGATCAGACCAAAAATAAACCAATATAAAATATTTCAGGCTACAAATTAAGA
TAGAATCGATTCGATCTTTCGGTGAAGTCCTCTTACCGGGCCCATTATTGTAGCTTGCCAGTGAAATACTGTAAGAAAACAAGAGATACATTAAT
CAAAACTGTTAAAAACGTAGTTGTGATATAATCCTAAAGAGCAAACATAAACTGCGCTGCAGTTAAACGTTTTCTGTTTGCTTTGATATGAGTCC
TATATCTACCTATATCTGCCCTAGATGGGAAATTACTGTGTGTACGTAAAGCATCTTGGATATTTACATTTGATAATGAGATGATGACAGAGTAT
ATTAAAATTTTCCCTTCGCTCAAAACTAAAACGTATTTTTCCTTGCCCAAGTTATATTCAAGTAATGAGTTTAGATACAGGAACTGATTTGCTAA
ATAACTAGGTAAATAAAATTAAGCTTCCAACAAGCCACAGAAATGTAATCTTCTTGTAGTACAATACCACTTTCCCCTAGTTCGCCACGTCTAGG
CCCCACTGTATATGCATCCAATGCAGCAAACTCGCTCTCGTCTAAATAAATGCACCACTCTCTCAGCGCCGCCCACCACCCCACTTCACCACTTC
CATTCTCATGGCCACGCTCTTTAGCGATTCCCCCCCACAAAAGAACAAACACAAACAATGCCAGCCAAAGAGCCTTGGCACCGACAATTGGCAGC
AGCGTCAGCAGCAGAAAAAGCACCAAATGCTCTCCCCCTTGAAACAAAAACAAAGTTTTTAAAGTAAGGAATATACCTATACCGAGATACCCTGT
AACCAACCAGGCTTTAAAGCACACATACGAAAAATTCATTTCTATATAAAACTGAGATATTTTTATAAAATCATGTTTTCTTAATGGTGGAACGC
AATATATTCGATTTTTCAACCGATTTCATGCTAAACAAACCTTGACTATTATTGGCATACATTTCCATGAGTTCTATATATCCTTTCACACTGCA
GAACATCACATATGTATATATATACCCTTGTACCCTGTGAGAGAGCACAAAACGTGTGGCAGTTGGCTCAGAATCATGGCCAAAACAGAGCTACT
GGCTATGCCGTCAATGTCATTCTGGTGAACGAATCGAATGCGACTGGGAAACTCTCTCTGTTGTGGCAGAGCACTGAGAACTGAACTGGGAACTG
GGCCCTCGGTAACCAGCTGCTGCCTTGACCATAATTACACGAAATGTTCATTTGTCCATCTGCAGTAGGGAGTTTGGGTCTGGAAAATGCGTCGG
CATTGTTTTTGTCATAGCTCAGACGAAAGTAATCTCATAGCTGCAGCCATTTTGATTAATACCACTTAGACAACAATCAATAATTTCTGAGCATT
GCTAAGGCAACAAAAACCCTGCAACCAGATGATATTAATAAAAGCAATGCATATTTAGATAAAAACATCCTTAGTGCATTTAAAGAATTGATTAA
TCCGACCATGGTAGCTTAGCTCAAAAGCATTCAATCAATGTTGAGTTTAAATGTTTAAATACATGATTAAATCATAAGGTTTCCTTTGCCATACT
ACAATTACAATGGATTAATTTCACACACATACACACACACACACACACACACACAGCGCCACACTGAGCTGAAAATGGATGGGAGTTTCCATTGC
ACTCGAGTGAAAATTCGCCACCCACCCAACCAACACCTAAAAAACCAAAGTAAGCCCCGCCCTGAGCTGCAATTCCTTTCTTTTACCCCAGTTGC
TGGGAATTCGAAGGCAAGGGTTCGGAACAGCCAAATTGATAATAAAAGCAAAGTGATAAGAACTGCGGAAATTATTGAGCTGACTCCTCAATAAT
CATAGAAATATTCACGCTTATATACAAACATACTTTTAATTGTATATAATAGCGACGTTTAAACGCTGTTAATAGAAATCGAGTGAAATCGCCAC
ACTGGTCGTTCATTATCAGCAAACGATGACAATTATTAATATTATTATTTACTCTGCCTCGCGGGAACTTGAATGAGTTTGATTTCCTTACGACC
AGAGAAACTGGGAAATGAAACACAAAGAAATGAGCTAACGAAAGTGCTGGGATATATATAAAATATTTCAATATTTTGCCGTTCTGTATAATATT
TTCATTTCCACAAAAGTGCGTTCACTAAATTATAATATATATATAATACTGCAAAGCATTACGAACAAAATTTCTATAAGTTCCTATAGTTAAAA
CAATAGTTTATATAGCTTTTTGCAGAATAATTTCAGTTCCTAGCCATTTTCCCTAAAACTAAGTATTTAGTTTGCCATTTTCTTTTTAAAATTTT
ATCGCTTACAAAGTATGCCGGTGTTTTTTTTTTTTAACCGAAATCGTCGTCAGCAAGACTATATAATTTACGATTTCACTTTTTGTGACGTCATT
GGAGAGTGACCCCCATATGGCTGGCACCTCTTCCTCTTCCCGCTTGAGTGGTGAAGGGGTGAAGGGAGGGGGGGGGGTGCTTTTCAGTAACGGT
TGTCTGTATGCAGTACAGCTCTACGTGCTATAACGTAACCGAATCCGATCCACAATCAGCGTGAATTTGTTGGCTAATTGCATGACGGCTTCGTG
AGTTTTTTAAATCGAGTTTAAGACAGCGAAGAAAAAAGAACCAAGTCATGGCGATCAGCTGTTTGGAGGCCGTCGCTATCACAAAATAAAAAGAA
CCGAATCCAAACTTGGCGCAAAAGAATTCCAAATTAGCAAAGTCCAAACTAAAAGTAACAGCCAATAGGAAAACAAACGATGTACAAATTTAGTG
TGTTATATGCCTAGTCACGATCGAAATCTATGACGTGGTGATGGTCGATCGACAATATTTGCATTTTTTATTAACAATTCCGAGATAGTGGTATT
GTGAATTTTGCCTAATATATATATATAGTTCCTATTCCTTGCATCAGACTATATACTATACTGACTCAGACTTGGCAACTCAGAAATATTTCACATA
ATTTCATGTCTTGGAGCTCCCACACGATATGGTGAAATCGAAACTTGGGTTAAAGCCCCCCCAACATAATACAACTGACTCACGGCAAATCAACG
AGTTGTTGAATAACATTAGCAATACTTACAATCATCTCCAACTGGACCGGCTGAACATTGTGCAGGTGGATCTCTGCCCAGATCTTGCAGTTCCT
GTTGAACAAAGACATTTTCAAATTAGTCATTGAAATAAAAGTTAAATATAGGTATGTAAGCTCAGTCAATTTCTGATTGTTTTTAACAGTTATGT
CAAGTCCTACAAAAAGAACTGGTTTTTAAAGAGTATATCTAATTTCTAGTCAAACCTTATATACTACCTACTTTCTGAAAGCATAGGTAACAAAC
CTAGCAATTGCAATACAGGAAACCCCAAAAAGAATTCTCGAAATGGGAAATGGTCAAAAGTGCATTTCATGGATATCTGCTTATGTTTTCCGGTA
GTCGGTTCTTTTGTTTTGCTCTATGATCCAGCTATATGTACATACATATGTATGTATGTACCACGGTTTTCCGGGTGTGCGTACATTTTATGCTG
TGTGGTTGGTATGCAAATGATGTAAATTTTAAATGCAGAATTTAAAAACAGATATGTGGGGATACAAAATAAACATTTTTATGCGAGAGCTTCGT
TCGAAGCGAGTGCGAGCGAGAGGGAGAGACGTGAAAAATCAAGTTCGTTGGCCCGGACCACAAATGGCGCTGTCTCCTTCTGCCCCACCCCCCGA
CCAGTCGCTCCATCCCTGTTGCACTCGCACGCACACAGCTGAGCGGCTCCCCTCCCTCTCTCTTACACTCCGACTCTTCTTCACTTATCACAGCT
GCCCCACACACACACACTCCAAACGGGGAGAGAGAATGAGGTGTAAGGTAAACCGGCAAAAAAAAAGAATATATATATAAAAAGAATAATGAAGA
TGAGCTGCGAAAGAGTAGCGCGACTCAGTGGAGAAGTAAGAGGAGGAGCAGCAGGAGGAGGAAGAATGAAGGAGAGTGAGAAGACTGAGCTTCAG
TGTATGCGTGTGTTTGTAACGGCACCACAAAATCAGAGTGGAGCACAACAAAAATAGCCGTCGCGAAAAACACCGTGTTTCTTTGCCCCATCTCA
CTTACTCATTTTGGGAATTGTACCTGTTGAGCAAAAATAAATTACAAGAAATTGTTACATTTCTTTTTTCGTTGGGAGTCGGAGCGGTTATGACT
CATATCAGACGAACAAATGAAGTAAAAACAAACACGCACACTTGTGCACAGCAAGAAAATTCGATAATATTATCAATATTAGACCAGGTGCACTA
CCAATACAAACTTCTATTTAATTCTTATTCGAATAATTAATATTGTGAACTTTAAGAATTGGTTCAGTAAGACTAAATGCCATATGCATTGGTTC
TAAAGCCCATTTCGTTCAGTGTACGGTTCAAGTGAGCTCCGATCGGCGTTTAAGCCGTTCTCTCTCGCTCTTTAACTCTCTTTTTTGGCAAATGA
GGCCATCTAGAGAAAAAGGCTTTTGAAGAATTGACCACAAAAAGGGGGCGTGAGTGATTTTAAGAGTTTACTACAATGTATACTTTTATTTCCG
GTTTGCCGCTTGCCATTTCGTTTTCATTTAGGCAGGCATTAAAATGTTATAATGGATAGAAAACTACGAAAAACGAGGAAAACTCAATGGCCATG
ACGCCGACGCAGGCAGCGCTGCTTTTGTCGAGACAGTCAGCAGACCCCCGCCCCACACATTCAAACACAAATACACACCACGCTCACACATACGC
ATAGATATGAACAAATTCCGCATTCGCTGCTCATTTTGTATGTAAATTATGCTTAATTATAATTTATAACTAATTATTTGGGGGCCCCCTTTTGG
CTGACGGTGTTTTGCAACACTAAGCCCCGCTAGCACTCACACACTTGCGCTCTCTTTGGCTCTGCCCCATTGCGCGAGCGGGACCGAATGAGGCC
TCAGCTGTCGCGGGCAAAGGGAATGCGCCAGGGCCAGAGCGAGATGGCATGCAATGGCCATAGCCAAGTGATGGCGAGACTTTGTATTTGCGAGC
GTTTTAATGTGTGTGTGTGTGGGGTATGACTATGATAACCGGCTTCAAACGTAAAAAAAGATCCCAATTTGCCAAGTAACATTTCCACAACTTCG
AGATATTACTAATGCTTTTGAGGAAGGCTGGGATGACTTTGAAAAAATATCGGGTTGTCAGGGCCTTGAACATTGGGGTGTAAAAAAGCATTTAC

FIGURE SHEET 450

TGGACAAGGACAAACGACGCGCAGGCACTTTAAAAATAATTATCGAAGCACGCACGCTAGAACCACTCTACCTAAATACATATATAAATATATAT
GCTTGGGGGCAGCACTATTTCTGAATTATCAGCGCAAAAAGTAGGGTTAGGTTAATTTTATACGCTTCTTGCTTTTGCTCTGTTTTATTTTTTGC
TGGATCTTTCTGCGGCGCTGGCAGTGTGTGCGTTTATGTGTGACTGTTGCGAGGCTGAGAGTGTGTGCGAGTGCCGTGTACAGCGTGTATTGGGT
AACAGCGCCCGTAGAGCTGCGAAAACTCCGCCGTATAGTTGCATTAATGTAAATGCATCCAGGTGCCCGGCACACACGCACACAAACAATGCACA
TTTGCATTGCACTTTCACGCACACGCATCGCACACACACTTATCCCACACTCTCGCAAAAGTAACGGAAGCGATGACTGCACTACACGTTGCCTT
GCCCACCACACACACACATCCTTATACCTTTTTCACCACCCTCAAAATTTCTAATCTGCTCCTAATTACTAACTTATTAATTAAATGGTAACTCC
ACAGCTCATTTTCTCCCTTCCCTCTTGCACGCTTCTTTCCCCCCGCTTCTTCTTTCTTCTCCTCGGTTACTACCTACGTTTCACATTTCTTGCAT
AAAATTTTTCTCCCGTTGAAAACTGATGTCTGTTCGCTTTTTTTTTAGACTATCATTTTGGTGTATCGCAAAGGGTTCTGTTCTTTCTTTTTTTA
GTCCGTTTCGCAAAGTTTTTTGAGATATTCCTTTTTTCACATACCTTATTGATTCTTTTTAACGCCATTTTCTGATTGAAATTTGATTTTCTGGG
TTGTGTGTGTGTTTGGTTGGTTGTGTGTGTGTTTGGTTGGTTGTGTGCTGGTGTTGGTGTCTCGCGTATTTCTTTTGTTCTTCGCACAGAATTGG
GTTTTATTCAATATATAATCCTCCTGCTTAGAATTGAACGAAAAACGAAACACAAAGCTGCGTTGCGCCTCTAGAACTTTGATGCTTAAATATGG
CTCTTTCGGTTGAGTGTCCCTTGTCACGAAATAAAGCAGCACCAGCGCACTGCAAGTAAAAACGGCGACCCGACGAAGACTACGGCGACGATTAT
TTTTTCACAATCAATGCGGGGCCTTTCGACCGTTTGTGCGATAGAGACGACCGTTAGTGAGCTGAGAACGCAACGAAGCACAATCGTTACACCGA
AGTGTAAGCCCGAGCGAGAGGAATGGTGTGTCTGTGTCGTGTGGTAGTGTTGTGAAGCGGAAGTCCAGCAGAGCAGTCCAGCTATATGACCTTTT
CGCTAGGGGTGGCCAGATCGATTGGGTGGCAACGCCTTTTAGGTGAGGGATGAATCAGTTAATTACAATTTGATTGCCAATGCAAGACTCTTCAT
ACTCACTTTAGTTCGGGAACAGCCAGAAGAAATAGTTTTACCGGCAGCGAGGAGGTGTTATATTTTATTCGAACTACCTTCTTATCGATGGTGCG
TGCGCCCAAAAGCTTGCAACTTGTATGTAAATTTGTTAACACCCAACGTGTTGCAGGCTGCCGGAATGTTTTTACTGAGCAATTTTGAGATGTTG
GTAATCCGAGTTCTTGAAAACTTTCCGACTAGCTACTGAGTTCTACAACTGAATTGACAGGGCGTTATTTTAAAATTTAAATTCACTCCAGAGCG
CTGGTCTGGCAAGGCCGACGTGCCAATTCAGGATACTTGTCGATATTTTCCGTTGTGCTATCGATAGTTTTTGGGAATAACAGGCGTTAGTAGAT
TTTTAGTATTTAGATTTTATTATCATAAGGATGAAAATATTTTTAACAAAATAAACTGGTTCATTTAATTTAACTTTTTATTTTCTCACTACTCC
AAATGGCGCTTCCGCTGTCTGAAACTGCCGTTATAATAGTATGAACAGTTAAAACAATCGACGGTAGCTGAATTTAATCAATGCAGCCCTCTTAC
CCTATACATCGATAGTATCGCATAAACATCGATTTTGGTTCCAGCTCTAACTTTAACTGTCTGCAAAATATTTCAAACAAAAGTGTTTGTTAATT
AAGTAATATACTTAATATTAGTGGCTGTTTTGCTTCGACATTGATCGAATTGCGGTTGTGCAAGTGTTTTGTTTGATTTGTTGGCGTGTTTTTCC
TAGTTTGGCGGCCCTTTGAACTCGTTCGTG
(SEQ ID NO: 835)

Exon: 9385..8975
Exon: 6078..6015
Exon: 3013..2982
Exon: 2478..2295
Exon: 2229..1001
Start ATG: 8998 (Reverse strand: CAT)

Transcript No. : CT22799
CGTTGCGTTCTCAGCTCACTAACGGTCGTCTCTATCGCACAAACGGTCGAAAGGCCCCGCATTGATTGTGAAAAAATAATCGTCGCCGTAGTCTT
CGTCGGGTCGCCGTTTTTACTTGCAGTGCGCTGGTGCTGCTTTATTTCGTGACAAGGGACACTCAACCGAAAGAGCCATATTTAAGCATCAAAGT
TCTAGAGGCGCAACGCAGCTTTGTGTTTCGTTTTTCGTTCAATTCTAAGCAGGAGGATTATATATTGAATAAAACCCAATTCTGTGCGAAGAACA
AAAGAAATACGCGAGACACCAACACCAGCACACAACCAACCAAACACACACACAACCAACCAAACACACACACAACCCAGAAAATCAAATTTCAA
TCAGAAAATGGCGTTAAAAAGAATCAATAAGGAACTGCAAGATCTGGGCAGAGATCCACCTGCACAATGTTCAGCCGGTCCAGTTGGAGATGATT
TATTTCACTGGCAAGCTACAATAATGGGCCCGCCGGACAGCCCTTATCAAGGAGGTGTATTCTTCTTAACTATACATTTTCCAACAGACTATCCC
TTTAAACCACCCAAAGTGGCTTTTACAACGCGCATATACCATCCAAACATCAACAGCAATGGATCGATTTGTCTCGATATATTAAGATCTCAGTG
GTCGCCAGCATTAACTATTTCAAAAGTTTTATTATCAATTTGCTCTCTACTCTGTGATCCCAATCCAGACGATCCTCTTGTTCCAGAGATTGCCA
GAATATATAAAACCGATCGGGAAAAATACAATGAGCTGGCACGAGAGTGGACTAGAAAGTATGCTATGTGATGCGTTCCAGATTGCAGCAGTCCA
ACAGAATCAGCAAATTCAACATCAACAATAGCAGAAGTAAAAGCAGATGCAACAACAACAGTAAAAGCAACAAAGATAACATCAACAGTTTACAA
TAGTCAGATTCAGAAGAGGAGGAGCTGCAGCAGCGTCATTGTAAGTGGCAATGGCCGCCGTGCTGTTGTCCACAACAATAGCCACAATATCAGCA
GGAACTGCGGTCACCACCATAGCAGCAACAAACACAACACCAACACTCGCCACAGCAGCAACATCATCAGCAGCAGCTGCAGCAGCAACAACAGC
AAGATCATCAACTGCCGCAGTCATTTTCGCCGCAGCAGCCGCTGCTACCGCCTTCGCAGCGGCATTAGCATTAGGAGCAGCAAATTTGGCGGCGG
TACCAAGAGCAACGGCAGCGGCAAAGGCGTCCTTGGGGCCGCAGCAACATCAGCAGCTGCAGCAACATCAGCAGCAACAGCCGCTGCAGCTGTGG
CAGTGGCAATTGGAGCAGCAACTGGCGGATTGGTGGCGAACATGCGATTAATTGTGTGTTTGACCGAACAGAAACAGAACAGCATAAACGGAAAT
AATTTAATAATAATTACTGAAAAAATGATGTAAGCATTAAACATTAAAAGCTAGACAGCTACCAACAACAGCATCAACATAATAAGTTTAAATAC
AAAGAAAAACAAAACTACAAATAAAAATCAGCTGGAAAAATTATTATTATTATTATTATATTATATTTAAAGAACCGGAAAAATAAAAATTGCAA
AAATTCAATTTAACATCAAGCGTGTAGTAGAGAGGTACTGCTTTAAGACACATTCGCTTTTGATCAATTAAATTACAAATAGGGTCGATTGCATG
CGTTGTCCAAATTGTTTAACAATTGCTTCATTTTGTATAAAATAATATTTAAATAGATATCTTGCTCTGTCTGAAATATATTATTTTAATTTTTG
TAATGCCTCAAGAAAGCTTGTTAAAATATTTCTTTCGGTTAACCATTTGTTTTGTAAATTATTTGAGATTGCGTATAAATTAGTAAACGGATGCT
GCTGCATTTTGTTTCACCTG
(SEQ ID NO: 836)

Start ATG: 388 (Reverse strand: CAT)

MALKRINKELQDLGRDPPAQCSAGPVGDDLFHWQATIMGPPDSPYQGGVFFLTIHFPTDYPFKPPKVAFTTRIYHPNINSNGSICLDILRSQWSP
ALTISKVLLSICSLLCDPNPDDPLVPEIARIYKTDREKYNELAREWTRKYAM*
(SEQ ID NO: 837)

Name: effete
Classification: enzyme
Gene Symbol: eff
FlyBase ID: FBgn0011217

Celera Sequence No. : 142000013384651

FIGURE SHEET 451

CTTTTTCCGGATGGCTTCCAACCTCTGGCTCTCCGTCATCAGCTACCATACGTGGAAAGTCTTGACGTCGCTCAATCGAGTCGACCCTAACTATC
GGTTCCTGCGGTACAACGCCTTCGTCTGGAGCACAGCCGCAATCATGACGGGAAGTATTTATATAGTTAATCAGATTTGGGAAAACGATCCCAGT
AAATGGAACTGGTTGCCTCTGGTCGGTTTTATTCGGTGCTCGGTCAAAGGTAAACTTTCAATGCGATTGCTTTTAAATCGTTACCATGGTTACGT
ATTGCTTTTCCATATCAGATTGGCACCCATCCGTCTGGATCTATATAAGTGGACCGTCGCTGGCCCTGAGCACTTTCAATGTCGCCATGTTCGCC
CTGACAGCCATTTACATTAGGAAAGTGAAGGGGGGTATAAATAAGTTCACAAATGAGGAGGAGGGAAGGATTAACTGCATAAACTTTGACAGCCA
GACGTAAGATATGATAAAACCTTGGACCTTGGTAAACTAGTTATCCTTGCCGTATTATCCACATAGTTACCTACAGTTCCTGCGGCTCTCCATCG
TGATGGGCCTTACTTGGATATTCAATGTCATTCCGTATTCTGCACGGCTCCACATTTTCTGGGAATGGGTCGGGATAATATCCGAGTATTTTCAC
AGCGCGTTTGGAATTGTTTTGTTCGTTCTGCTCGTCCTGAAGCGCAGCACATGGACTCTAATGATGGATTCTTAAGCTTGTTTCTATATAATTCT
AATAATTGTTTACAATTAAAGCTTTAAACAATTAAAGCCCCTCATTTTATTAATATCCTTTGCTGAACGAAGGAATTGAATTGAATTTTATTGAA
CTCAATAAATAAATATAGTTTTAGAAAACGATGTACTTTAAACTGCCAAGAGGTCACCGCGACAAGCTTTTCACTTCGCCACCCTCTGGTAACAC
TGATTCTCCAGCCACTTTCGATTCTTTAAAAAACATCGATAGGTATCGCCAAAAAAATCAGCTGCTCTGCTTGTAGTTTTGCGATTTCATTGCAA
TTTTAATTTGCTTTACTGTTCAAAAAGAAATACAGTGCAAAATATGCCGAACGAAAACGCAGAGGACCTCTCGGGTCAAGAGCTAAAGCAGAAGG
CCAAGGAGGTGGCCGACGCATCGGAGGCAATGCTCGAAAAGGTTGTTGCCGGCTTAAATATCCAGGACACGGCATCGACGAATGCAGCAGGAAAC
GAGGATGCGGAGCAGCCTGATGGTGCCAAGAATGAGGCTTCAGTGTCTGCGAATGCAAGTAAGTTTTCAATATGCCTGTGAAAAGTCATTTAGAG
GCTCCTCCTGCGGCTGAAAAAATGAGGTTAGGTTTTGTCGGGAACTACAGTCCAACCTCTCTAACTTGAACTGCTGTGCTATTCATTTCAATTCA
ATTTTCAATTTTCATTTTCTGTGCAATTACTCCAAAGATTAGCCCTAACGGAAAAATAAACAACTCATAAATCATAAATACATATTTGATTTTGA
TGAAATATGAATATACTTACATAGATACAATTGAGTTTTTTATTACGAATAAAATATGTGTAATATAAGATTTCTACCTTGTTGATTCCATTGAT
TGATGCTTCATTGAAACCCCAAAATTGGGCAAATTTGTTGTCATGGGAAACTAGTCCACTGTCGTGATGCCTTAAGCTTTTTTTGGGGCAGATTA
GTCATTCCAGTTTAAACTAATCGAAAAATGTTATAATACTATTCAACGCATCATCGTTTCTTTCAGGCAAACAGGCCTTGCTACAAGCCGTTTCC
GATGCTATGGCCAGCACCCGTCAGATGGCCAAGAAGTTTGCATTTTGGTCCACACAGCCAGTCACCAAGCTGGACGAGCAGGTGACCACCAACGA
ATGCATTGAACCGAACAAGGAAATTAGTGAGATTAGAGCATTGCCATACACTCTGCCAGGCGGCTTCAAATGGGTGACACTAGACCTGAACGACG
CCAATGATCTCAAGGAGCTGTACACGCTGCTCAATGAGAACTATGTGGAGGACGATGATGCCATGTTCCGTTTCGATTACCAACCCGAGTTTCTA
AAGTGGTCGCTGCAGCCACCTGGCTGGAAACGCGATTGGCATGTTGGCGTTCGTGTGGAGAAGTCCGGCAAACTGGTTGGCTTCATCTCAGCCAT
TCCCAGCAAGCTGAAGTCGTACGACAAGGTGCTAAAGGTTGTGGACATCAACTTCCTATGCGTCCACAAGAAGTTGCGCAGCAAACGGGTGGCTC
CAGTCCTGATTCGGGAGATAACGCGTCGCGTCAATCTGACGGGGATTTTCCAGGCGGCCTATACAGCTGGAGTTGTGTTGCCCACGCCAGTGGCC
ACCTGTCGCTATTGGCATCGATCGCTCAATCCCAAGAAGCTGGTAGACGTGCGTTTCTCTCATCTCGCACGTAACATGACCATGCAGCGGACAAT
GAAGCTGTACAAGCTACCCGATCAGCCCAAGACGAAGGGCTATCGCCGAATCACAGCGAAGGACATGGACAAGGCCCACAAGCTGCTGGAGGACT
ACCTAAAGCGCTTTCAGCTGAGCCCGGTGTTCAGCAAGGAAGAGTTTCGTCATTGGTTTACCCCCAAAGAAGGTATTATCGATTGCTTCGTGGTT
GCCGACGAAAAGGGCAACATCACTGATCTGACTAGCTACTACTGCCTGCCATCGTCCGTGATGCACCATCCGGTGCATAAGACGGTTCGTGCCGC
ATATTCGTTCTATAATGTGTCTACAAAGACCCCGTGGCTGGACCTGATGAACGATGCACTGATCTCGGCCCGCAATGTCCAGATGGACGTGTACA
ATGCCCTCGACCTCATGGAGAACAAGAAGTACTTTGCACCGCTAAAATTCGGCGCCGGGGATGGAAACCTGCAGTACTACCTCTACAATTGGCGC
TGTCCATCGATGCAGCCGGAGGAGATTGCTCTGATACTCATGTAGTCACCTTGTCACCTAAGCTCACATTCTCGCCCTGCCTTTCACAGCTCCCC
TCCTCCGCTTTCTTCACCCTGCTGGAAGTGCCGTGCGGCTGCTTTGCTTTGCTCCTATTTACGTAGCTATTACCTGTAATCTTCAGTTATTCCAG
CGAGGAAAGCCCTTTGCGAGCATACACCTAAATAGCATCATTGTGAAAATTGCATTTTGCAACGGCCAAGCTTCGATATTTTTACTACAAGAAC
GAACACAAATTGTATAAAATGCGCAGCAATATCAATAAAAATGTAACGTTTACTTGGACCTTTATTGCCTATAATTGACAATAAATTATTTTGCT
GCTCTTTTAAAGATGACAAGTTTTATTTTTTTAAGCAGATTATTGTATTTTTGCCCACTGTCCCAGCATGTGATAGTCTGGCCACTCTGTCAC
ATGGCCATTGGTCTGGCAAGGTCGGTGAAAAAGCGCGCGCTAAGCAAAACAGCTGCACTTGTGTTGGTTTATTAGTTAACGAAATCTGATTCCAA
TGTTGGTTTCCTCATAATATTGACAATTAAAGACAGCCGCCGACATGGACGATTCGGTGTTCAAGCTAAAATACCAAAAGTACAAGTTGCGCGTC
AAGGTGTGGGAGAAGGACTTCAAGAAGAAGAATGGCCGTGTTCCATCGAAGGTGAGATTGGGATGCGGATATGACAAGTATGCTAACTGGTTGAC
CTGTTGCAGTATGATATAAGGGACGCCAGTCAGGAGATTCGGGACTCATACAAAATGTACTACAAACTGAAGACATCCTTCCTGGAAGAGACGCT
GAACGATGTTCTCAGCGAAGATGGATACGATATTCTGGAGATGTCGCAGGCCAGTGATTTCGGTGTGAGCATGCTGGACCAGGACGTCAGTCTTA
ATGAAGGTCCTCAGCTACCGTTGGATATATCTGCACTGGTGGGGCCGCAGAGCTCTGGTAATCTTGAGGAAATTCCACAATCGGTGGAGGGCTCA
TTCTCAAATCTCATCGACCTGCCCAATCGTCAAGTACTCACCAATCTGGTCAATCGCGATGAAAACCATGTCATTCGCAAATTCGAGGCGGTGGA
GGAGCTGCCAATCAACCAAAATGCCTGGGGCTTGAATGTGAGTAAGAAGCCACCAGCTCCACCACAGCCTGTAGAGGCCTCCAAATCCGCTCCGG
GGCACGGAAAGCAACCCAAAGCGGGCGCTAGTCTTAAGCCCAGCTTGAGTGCCAAGTTATTCCAATCCTCACGCGGTTTTGCTAAACGAAATCCC
CGAAAGC
(SEQ ID NO: 838)

Exon: 1001..1293
Exon: 1777..3282
Start ATG: 1089

Transcript No. : CT22825
AAAAAAATCAGCTGCTCTGCTTGTAGTTTTGCGATTTCATTGCAATTTTAATTTGCTTTACTGTTCAAAAAGAAATACAGTGCAAAATATGCCGA
ACGAAAACGCAGAGGACCTCTCGGGTCAAGAGCTAAAGCAGAAGGCCAAGGAGGTGGCCGACGCATCGGAGGCAATGCTCGAAAAGGTTGTTGCC
GGCTTAAATATCCAGGACACGGCATCGACGAATGCAGCAGGAAACGAGGATGCGGAGCAGCCTGATGGTGCCAAGAATGAGGCTTCAGTGTCTGC
GAATGCAAGCAAACAGGCCTTGCTACAAGCCGTTTCCGATGCTATGGCCAGCACCCGTCAGATGGCCAAGAAGTTTGCATTTTGGTCCACACAGC
CAGTCACCAAGCTGGACGAGCAGGTGACCACCAACGAATGCATTGAACCGAACAAGGAAATTAGTGAGATTAGAGCATTGCCATACACTCTGCCA
GGCGGCTTCAAATGGGTGACACTAGACCTGAACGACGCCAATGATCTCAAGGAGCTGTACACGCTGCTCAATGAGAACTATGTGGAGGACGATGA
TGCCATGTTCCGTTTCGATTACCAACCCGAGTTTCTAAAGTGGTCGCTGCAGCCACCTGGCTGGAAACGCGATTGGCATGTTGGCGTTCGTGTGG
AGAAGTCCGGCAAACTGGTTGGCTTCATCTCAGCCATTCCCAGCAAGCTGAAGTCGTACGACAAGGTGCTAAAGGTTGTGGACATCAACTTCCTA
TGCGTCCACAAGAAGTTGCGCAGCAAACGGGTGGCTCCAGTCCTGATTCGGGAGATAACGCGTCGCGTCAATCTGACGGGGATTTTCCAGGCGGC
CTATACAGCTGGAGTTGTGTTGCCCACGCCAGTGGCCACCTGTCGCTATTGGCATCGATCGCTCAATCCCAAGAAGCTGGTAGACGTGCGTTTCT
CTCATCTCGCACGTAACATGACCATGCAGCGGACAATGAAGCTGTACAAGCTACCCGATCAGCCCAAGACGAAGGGCTATCGCCGAATCACAGCG
AAGGACATGGACAAGGCCCACAAGCTGCTGGAGGACTACCTAAAGCGCTTTCAGCTGAGCCCGGTGTTCAGCAAGGAAGAGTTTCGTCATTGGTT
TACCCCCAAAGAAGGTATTATCGATTGCTTCGTGGTTGCCGACGAAAAGGGCAACATCACTGATCTGACTAGCTACTACTGCCTGCCATCGTCCG
TGATGCACCATCCGGTGCATAAGACGGTTCGTGCCGCATATTCGTTCTATAATGTGTCTACAAAGACCCCGTGGCTGGACCTGATGAACGATGCA
CTGATCTCGGCCCGCAATGTCCAGATGGACGTGTACAATGCCCTCGACCTCATGGAGAACAAGAAGTACTTTGCACCGCTAAAATTCGGCGCCGG
GGATGGAAACCTGCAGTACTACCTCTACAATTGGCGCTGTCCATCGATGCAGCCGGAGGAGATTGCTCTGATACTCATGTAGTCACCTTGTCACC
TAAGCTCACATTCTCGCCCTGCCTTTCACAGCTCCCCTCCTCCGCTTTCTTCACCCTGCTGGAAGTGCCGTGCGGCTGCTTTGCTTTGCTCCTAT TTACGTAGCTATTACCTGTAATCTTCAGTTATTCCAGCGAGGAAAGCCCTTTGCGAGCATACACCTAAATAGCATCATTGTGAAAATTGCATTTT
GCAACGGCCAAGCTTCGATATTTTTACTACAAGAACGAACACAAATTGTATAAAATGCGCAGCAATATCAATAAAAATGTAACGTTTA
(SEQ ID NO: 839)

Start ATG: 89

MPNENAEDLSGQELKQKAKEVADASEAMLEKVVAGLNIQDTASTNAAGNEDAEQPDGAKNEASVSANASKQALLQAVSDAMASTRQMAKKFAFWS
TQPVTKLDEQVTTNECIEPNKEISEIRALPYTLPGGFKWVTLDLNDANDLKELYTLLNENYVEDDDAMFRFDYQPEFLKWSLQPPGWKRDWHVGV
RVEKSGKLVGFISAIPSKLKSYDKVLKVVDINFLCVHKKLRSKRVAPVLIREITRRVNLTGIFQAAYTAGVVLPTPVATCRYWHRSLNPKKLVDV
RFSHLARNMTMQRTMKLYKLPDQPKTKGYRRITAKDMDKAHKLLEDYLKRFQLSPVFSKEEFRHWFTPKEGIIDCFVVADEKGNITDLTSYYCLP
SSVMHHPVHKTVRAAYSFYNVSTKTPWLDLMNDALISARNVQMDVYNALDLMENKKYFAPLKFGAGDGNLQYYLYNWRCPSMQPEEIALILM*
(SEQ ID NO: 840)

Classification: enzyme
Gene Symbol: Nmt
FlyBase ID: FBgn0020392

Celera Sequence No. : 142000013384620
ACATGCCAACAACGTGGCGGCCATGGTGAAGATGTTCTCTCGCAGAAGCGGCGGATTGTGGGGCATGGTAATAGAGTGCAAATCCACAATACACA
CGGTGACATCGTCACGAGCATTCTGCAGCTGCACCCATTTGCGCACGGCGCCGAGATAATTACCCAGATGCAGGGAACCCGTCGGCTGGATGCCA
CTAAAGACTTTCCTCGGCCAGCGGGTGTTATGCTGGGTTGGGGTAATATATTAGAGTCTTGTGTTATGTAAACTATTTCTACGAATGCACTTACT
TCTTCGTGGCCACTGTTAACGGAATTACCATGGGGGTGTACGTGCTGCTTGTTTCCACCGGTTACCTGGGCCGTCGCAGAGGGCGTTCCAGCCGT
CCTACTAGCCAATCCCGGCAAGAAACTCCTCGCCTGAATGCAACGGCGCTGGGAATACACAGCTGTCTGTCCCTTTTTGGCCACCTTAGACAGAC
TGCGATGGAGCTTGCCAAATCGGAACATTGCAATGAGCTATGAATTTTGTACCCCAAAACTTTTGAGTAAAAAATATTGGGAATAATGCGGTGCT
AAATGTGTGAACAAAGCCCAAAAATAAATTATTTGTTCGAAACGGCCGAAATTTTGACACTGAGCGTTCGCGAGCGTTGCCAGATGGCTTTTGAA
AAGCCGGTACGACAGCTGTGAACAGTGATACTCAGCTTGGCGAGTTTTCCGCTAAATCGTGGATTAATATTAATATTCAAATTTAATAAAGAATG
TTATTTATTATCATTTTTTTTATAACTCTCTATTTAAGGGTATTACCTATTTACATCTTACTTGTGAACGTATGGCTTGAAATTTAATGTAATTG
TTTGATGGTAAATAAATTGTAGAGACCAATTGAACAATTTTTTTTTTTAACAGGACTCCTATTATTTTTATGCTTATAGCTTTATTAGTGGTAC
ACCAGAAAATCTAACGACATTGAAAAAGAATTAATCTGCAGAACTGCAGTTTCGAGTTTTCAAACAGTGTTGTATTTATTCTAGCTTAATACACA
TATTACATTGCAATTAACGCCTGGCGCCATTACCATTATTTATATTTCCACTTTTCTGTTCCTACATTGAGAGTTACAAATATGCGGAGACTGT
CGTTTCGGCCGTCAGGATAATTTTTCGAATAGGGGTTATTCAAAGATTTCAAACGCGGTGCAAAATTCTTCACTATCTGGCAGAGATTGGGAAGT
GCTTAGAAGTTGATGGGTTTGCCAAAGGCAGCTGCCACATTGGCCTCACGCAGGGCCTCGGAACATGTCTGAAAGAAGGAATTGTGCGCATTAGG
TTCGAAAGGTTCAAATCAGATTAGGTAATCACTTACTGGATGCGCATGGCAAACGCGGGCAACGTCCTCGGCAGCGGCTCCGTACTCCATGGCCA
GCACAGCCTCGTTAATGAGCTCGCCGGCACCAGGTCCGATAATATGGGTTCCCAGGATCTTATCGGTGGCCTGGTCGGCCAGAACCTTGACGAAA
CCGTCGGTGTCGTTGTTGGTCTTGGCACGAGAGTTGGCCAGGAAGGGGAACTTGCCCACCTTGTAGGCAACACCCTCCTGCTTCAGTTGCTCCTC
GCTCTTGCCAACCCACGCGACCTCGGGATGCGTGTAGACTACACTGGGCACGCAGTTGTAGTCGATGTGCACGTGGCCGCCGTTGATGCCCTCAA
TGGTGATGAGGCCCTCATCTTCAGCCTTGTGCGCCAACATGGGTCCGTGGATGCAGTCGCCGATGGCGTAAATATTGGGCACCACAGTTTGGAAA
GTGGCGTTGACGGGGATCCTGCCGCGGTCATCCTTAACAATGCCCACGGCCTCCAGACCCAAACCTTCGGTGTAGGGACGACGTCCAACACTGAC
CAGCAGGGCGTCGCACTGGATCTCCTCTTTCTCGCCAGACTTGGCGTTCTCCACGGACACGGTGACGTTGTCGCCGCTGCGAGAGGCAGCCGTCA
CCTTGGTGCCCAGCTTGAACTTAAGACCCTGCTTGGTGAGCACCTTTTGGAACGTCTTGGAGACTTCGTTATCGATGCCCACGCCGCCGATCGTA
TCCATGAACTCAATGGCAGTGACCTCAGCGCCCAGACGCGACCATACCGAACCCAGCTCCAGGCCAATGACACCGGCGCCGATGACAACCAGATG
CTTGGGCACCTTGGCCAGCTTCAGGGCGCCAGTGCTGCTCACAATAACTTCCTCGTCGATCTGTGAAGGTTTTTGAATGGCATGCATTAGTAATC
AAGCGCGCTGTAGAGGTTTTGCACTTACTTCAATGCCAGGGAAGGGGGTAACCTCCGAGCCGGTGGCGATGAGGATGTTCTTGGTCTTGACAGTC
TCCGTGGAGCCGTCGGATTTCTTAACCTCCACCTCGTTGGGATTGACGATGGTGCCGAAGCCCGTCAGCTGTGTGACCTTGTTCTTCTTGAAAAG
CATGGCAATGCCACCGGTCAAAGCCTTCACGGCGTTGGACTTTTGACCCATAAGCTTCTCCAGATCCAGGCTAACGCTGCCGCAGCTAATACCAC
GTTTCTCCAGATCACCGGAGTGGGCCATGTGGTAGTAGTGGGAGTTGTTCAGCAGCGCCTTTGAGGGAATGCAGCCAACATTCAGGCAGGTGCCG
CCCAGAGTTGCCTCCTTCTCCACGCTGACCGTCTTCATGCCCATCTGGGCGGCCTTGATGGCGGCGACATAGCCACCGGGTCCGGAGCCAATCAC
CACGATGTCCGCCTCGTGGGTGCTGGAGTAGCAGCGGGCGTTGAGGGCACCCAGAATGGCGGCATTGGTGCGCAGAGGAGTCTGTAAAGACGGCA
GATTACTACATGTTGTGGCACCTTATCATTTATCACGCCAGTCGCACGCATTTCGCACTAATCTTCGGCCGACTATCAGCTGATAATTGGCCTAA
TTAGCGACCTTGAAAACGGGGCCAAACAAATCCCCAAACGCCAGTGAATCACCCACCGGGATCATATGAGCACTGCAGGTGATCCAAGTGCATTT
TCCAGCCTTTTCCTGCCCATTTCTCGACCCCCTCGGTGAGGTTAGATTGCATAACTTGAGGGGCGATGGCGTTTGGGGAATCGGTTATGTCGCCC
GATCCTTACCTTGGCTACTGCCGAAACAACATGACGGAGCGTGAATTGCATGGCTGGTGCGGGCGAGTTATGAGGATAATCGTTATTTAACTACA
AACACAACACTAGTTTGATGTGTGTTTTTCCGACTGTTTTTCGTGTTGTGGGGCTCGGAGCGGTCGCAGGGCTGGCGATGTGCATTCGATAGTGG
TCATATGATGGCCGCGATGCTATCGATTGTTTTGGTGATTTTCCACTCTGTTGGAATTTGAAATTCTAAAACATTTTCGTATGAAAAAGATGTGT
ATAAAAATATTAGCTTGATGATCGTTCAAAATACGATATGTCCGTCACTCAATTGCTAGTTTATACAATATTCACTTTATGGGTCATTTGTTGTA
GCAAAAGCTACCTAAAAACAAGCCAACTATACGTGTAAGCCGGCTTTTATAGTTTTGGCACCCATTAATTAATGTTTTTGTACGTATAAAATAAA
CTGTAATAAATAAACTGTAAAATAACTGTTTTAAAAATATATAACTCAACGTACATACGATACATATATAATAAGAGTTCCAAAGTAATATTAAC
TTTATTATATCTATAGGTAATTAAAAATGTATTATACGATGAATATTCGATAGTTTGCCCTACAGTACAACCCTGTGTGGTATTCCCCATCTGGG
ATATTTCCCACAACACTTTTGGTATTTTCACGTCGCGTTCATCTCGCGTTTTCGTTGAAGCCTCAGTATTTCGCTAGCTGTCGCAATGCGGTCAC
ACTGGTTCGCGGACACAACAAGATGGCGAGACTTGCCCCCGAAATCTGTTAGAAAACGCCACAAGAGCAAATAATTAGTTCAGTTTTCGACCAGA
AAAGAGTCAGCCGAAGTGCCGGGCAGACGCGGCGCATTTTGCAGAGTGTGAGCTTGGCCAGCGTTGCCCGAGAGCCGCGACAGGCGACACCTTCT
GCTGGCCTTGCCTTGTTGCTGTGCCCCTGTGTGCGTGAGCGTGTGCGGTGCGGTGCGATTGTGTGCGTGGGTTGCCAAGAGTGAAGAGAATCGCT
GAGTTTCCAAGATGATGAGCAACTACGGCAACATGATGGACTCACCGAAGTCATCGCCCCACGGCGGCGGCCGATCACCCGTGGTGGCCCGTCAA
GACTCATCCGGCACCCTGAAAACGACCATTTCGCTGGGCAAGACGCCAACGATCATTCACACGGGGCCATTTTACTCCATGAAGGAACCACCCGC
CAAGGCAGAACTTACCGGCGACAAGGATCTCATGACCGAGTACGGACTGCACCACACACTCACCAAGTTCAAGGAGAAGAAGTTCAAGGAGTCGC
TG
(SEQ ID NO: 841)

Exon: 3467..3145
Exon: 2836..2309

FIGURE SHEET 453

Exon: 2245..1367
Exon: 1303..1001
Start ATG: 3186 (Reverse strand: CAT)

Transcript No. : CT22859
TGACGGACATATCGTATTTTGAACGATCATCAAGCTAATATTTTTATACACATCTTTTTCATACGAAAATGTTTTAGAATTTCAAATTCCAACAG
AGTGGAAAATCACCAAAACAATCGATAGCATCGCGGCCATCATATGACCACTATCGAATGCACATCGCCAGCCCTGCGACCGCTCCGAGCCCCAC
AACACGAAAAACAGTCGGAAAAACACACATCAAACTAGTGTTGTGTTTGTAGTTAAATAACGATTATCCTCATAACTCGCCCGCACCAGCCATGC
AATTCACGCTCCGTCATGTTGTTTCGGCAGTAGCCAAGACTCCTCTGCGCACCAATGCCGCCATTCTGGGTGCCCTCAACGCCCGCTGCTACTCC
AGCACCCACGAGGCGGACATCGTGGTGATTGGCTCCGGACCCGGTGGCTATGTCGCCGCCATCAAGGCCGCCCAGATGGGCATGAAGACGGTCAG
CGTGGAGAAGGAGGCAACTCTGGGCGGCACCTGCCTGAATGTTGGCTGCATTCCCTCAAAGGCGCTGCTGAACAACTCCCACTACTACCACATGG
CCCACTCCGGTGATCTGGAGAAACGTGGTATTAGCTGCGGCAGCGTTAGCCTGGATCTGGAGAAGCTTATGGGTCAAAAGTCCAACGCCGTGAAG
GCTTTGACCGGTGGCATTGCCATGCTTTTCAAGAAGAACAAGGTCACACAGCTGACGGGCTTCGGCACCATCGTCAATCCCAACGAGGTGGAGGT
TAAGAAATCCGACGGCTCCACGGAGACTGTCAAGACCAAGAACATCCTCATCGCCACCGGCTCGGAGGTTACCCCCTTCCCTGGCATTGAAATCG
ACGAGGAAGTTATTGTGAGCAGCACTGGCGCCCTGAAGCTGGCCAAGGTGCCCAAGCATCTGGTTGTCATCGGCGCCGGTGTCATTGGCCTGGAG
CTGGGTTCGGTATGGTCGCGTCTGGGCGCTGAGGTCACTGCCATTGAGTTCATGGATACGATCGGCGGCGTGGGCATCGATAACGAAGTCTCCAA
GACGTTCCAAAAGGTGCTCACCAAGCAGGGTCTTAAGTTCAAGCTGGGCACCAAGGTGACGGCTGCCTCTCGCAGCGGCGACAACGTCACCGTGT
CCGTGGAGAACGCCAAGTCTGGCGAGAAAGAGGAGATCCAGTGCGACGCCCTGCTGGTCAGTGTTGGACGTCGTCCCTACACCGAAGGTTTGGGT
CTGGAGGCCGTGGGCATTGTTAAGGATGACCGCGGCAGGATCCCCGTCAACGCCACTTTCCAAACTGTGGTGCCCAATATTTACGCCATCGGCGA
CTGCATCCACGGACCCATGTTGGCGCACAAGGCTGAAGATGAGGGCCTCATCACCATTGAGGGCATCAACGGCGGCCACGTGCACATCGACTACA
ACTGCGTGCCCAGTGTAGTCTACACGCATCCCGAGGTCGCGTGGGTTGGCAAGAGCGAGGAGCAACTGAAGCAGGAGGGTGTTGCCTACAAGGTG
GGCAAGTTCCCCTTCCTGGCCAACTCTCGTGCCAAGACCAACAACGACACCGACGGTTTCGTCAAGGTTCTGGCCGACCAGGCCACCGATAAGAT
CCTGGGAACCCATATTATCGGACCTGGTGCCGGCGAGCTCATTAACGAGGCTGTGCTGGCCATGGAGTACGGAGCCGCTGCCGAGGACGTTGCCC
GCGTTTGCCATGCGCATCCAACATGTTCCGAGGCCCTGCGTGAGGCCAATGTGGCAGCTGCCTTTGGCAAACCCATCAACTTCTAAGCACTTCCC
AATCTCTGCCAGATAGTGAAGAATTTTGCACCGCGTTTGAAATCTTTGAATAACCCCTATTCGAAAAATTATCCTGACGGCCGAAACGACAGTCT
CCGCATATTTGTAACTCTCAATGTAGGAACAGAAAAGTGGAAAATATAAATAATGGTAATGGCGCCAGGCGTTAATTGCAATGTAATATGTGTAT
TAAGCTAGAATAAATACAACACTGTTTGAAAACTCGAA
(SEQ ID NO: 842)

Start ATG: 282 (Reverse strand: CAT)

MQFTLRHVVSAVAKTPLRTNAAILGALNARCYSSTHEADIVVIGSGPGGYVAAIKAAQMGMKTVSVEKEATLGGTCLNVGCIPSKALLNNSHYYH
MAHSGDLEKRGISCGSVSLDLEKLMGQKSNAVKALTGGIAMLFKKNKVTQLTGFGTIVNPNEVEVKKSDGSTETVKTKNILIATGSEVTPFPGIE
IDEEVIVSSTGALKLAKVPKHLVVIGAGVIGLELGSVWSRLGAEVTAIEFMDTIGGVGIDNEVSKTFQKVLTKQGLKFKLGTKVTAASRSGDNVT
VSVENAKSGEKEEIQCDALLVSVGRRPYTEGLGLEAVGIVKDDRGRIPVNATFQTVVPNIYAIGDCIHGPMLAHKAEDEGLITIEGINGGHVHID
YNCVPSVVYTHPEVAWVGKSEEQLKQEGVAYKVGKFPFLANSRAKTNNDTDGFVKVLADQATDKILGTHIIGPGAGELINEAVLAMEYGAAAEDV
ARVCHAHPTCSEALREANVAAAFGKPINF*
(SEQ ID NO: 843)

Name: Didydrolipoamide dehydrogenase, DLD
Classification: enzyme

Celera Sequence No. : 142000013384523
CTCCGGCGATAATGGAGACCGACCCGCACACACACACACACAACACGGCCACACGGTGACGGGCGTAGAGGCACACACCGAGCCAACTCGAATAC
ACACGCGCGCAGGGGAGAGAGAGCGGGAGAGCGCGGGCGCTCTCAATTATTTATTTACTTTTTTCGTAACTGCATTCCATTCCAGCTCAAACA
CACGCACACATATGGGGGACGAACACAAGCGCACACGATCACTGCTCACAGTTGGTGCTGCTTCTTTTCATTTCTTGTTGTTGCAAGCGTTTGAA
CTCCTTTACTTATTTTCTTATTTTCGCCTAATTGAAACTAATTAACGACGATAATCCAACCATCCACTTGGTGTTCACAAAAAAATATGTACTTC
AGTTTAGTGAGTTCGCGCCGTCGCCGATCTCTTCGGTTCCGGAATTCCTTGGGGGAGCAGCAAAAAACACGAGTAGCGCGCTTGATGACCGTCCG
ATTCGGATTCGGAATTTGTTTTGGTAACATTCGCTGCTAGTGGTGTAGCAGAAAACATCGCATTGCATATCGATACACTCGCGGCGATGTTATTC
GATGTATTGGTTGATATCGATATTATAGGCTGTATTGACGCGGTTGCAGAGATGCGATATTTAACAATCATGCACGAAAAGTATTTATTGTTATT
TGGCTTGTGTAGTCCCCAAGCATAGGTGTAATTGTTGAGGGAAGAAAATAGGAGTTGTACGTTCAAAGATCGGCTTGGTAACAGGAACTAGTTCG
GTTCTTCAAGCGATGTTAATCAAAGCCAGTTCCGATAGATCATGTTAACTCGCTCTGTTAACAATTACTGTTATCTTAATCCTAACATTTCCGTT
ACATTTTAAAAACAGAAAAAGAAAAAATTTAAAAAAAAAGACTGTAAACTGAGTTACGCATTTCGAAATCAATATGTATCCCAACCATAGATAGA
AAAATAAATTATGTTTCCGAAACATAACTTCAATAAAACCACAATTTCGCTTGCTTTGTACGTTTGATATTGTATTTGCATTTTATGAATTGTAA
AAATTGAGTCAACAAGACTAACACAGCTTCAGCTCAAGACACATGCAATTTCATTGACATTGTTTAATTGTATATATTAAAGGAAATCAATTAGG
ATATAAAGAGAGAAACCTTTTTGCCGCTTATGCGATGCCAACTATCTGGATCTGGATTGTCTAACACGAAACCCTAACTAATTGGTAAATTAAAC
ATAAATTAATCATATCGGTCAACAACTACAACTAAATATTAGTTATTAGCGGATAAAGAGCGCCCCATAAACTATTTACACTAAGCTTTAGTCTA
CTAGAGTCCCGGATTCCATCTCCGCTCCTCGGATCTTCGGATCTTAACTCAGATGTTCGGATCTTCAAGTTCTAGGAGAGAACTGGTGCAGTGCA
TCCGTTATTCAGGCGATACTCGGCATAGACCAGTCCGGTGTTGTGCCAGTGATAGAAGGCGGCCACGATGATCAGGTGCCACCAGTTGTGCGAAT
GCCCAACGAAGTCCACCTTGCCGGTGAACCAGCGCTCCGGAATCTTGGCCGCATAGAAAACGAAGGCGACGAGGCAGAGCAAGTACATGAGCACG
ATGCGGGGCACCATCAGCTGCAAATGGTAATGATTGATGGATTAGCAAATGACAAGATTCCATAAATTTCCAACTGATGCCTACCCTGACTAGCT
CGTTCTCCAGACCGCCCATGGCCACCGCCCAGTGGCCCAGAGGTATGATTCCATAGGCAGACCAGAGTAGCAGCACCGCCACCTTGCCGTTCATG
GACACATTCAAACGGGGTATCTGCACGGCAATGGCCAGTGCGAACATGCCCAGTGCAATCGTGGAGTACAGGGTGCGCAGGAAGGTGTGGCACCA
GAAGGCATAGTACATGCCACTGATATAGATGGCCACCAGCGACAGCGAAATGCCCAGGAAGTCAACGGACAGAAAGAGCTCGTAGTGCTCCTCCG
ATTTGCAGGAGAAGATGTGGTATATGGCGGACATCAGCATGCACAGACAGAAGCAGACCAGCAGGCAGACCACCAGCACCTGGTCGCTCAGGGAG
GCGTGGAGGCGCAGGAACTGCAGATCGAAGATGGTCAGTCCAATGAACAGGATGCAACCGGCCAGATGGCTCCAGATGTTGATCTATGAAAAATA
TAGCAATAATAATGTTATAATAATAGGGAATAGAGTTTAAGGAAAACTATTGTAGCTCCAATTGGAATGGAGTATCATTCTAGTGTGGCAATCTT
ACCGTCTCATTGGTCCACCAGAAAATGCTCTGCAGGCACATTTTTGTGGAAGGTAGAAAGGTGCGGTATCCGCGACGAATGTACGGGTTGAACTT
CAGGTGACTGGGGGCCTGTATCGAAAGCACAAGTGAATAAACATTCCAAATAAATACAAAATTTTCCAAGCCGATAAGACATGCAAATCGCATGC
GTGTAGCATTGAAAATAAAATAAAAACCAAATAGACAAAATGACAAAATAAAATAGAAACAAACGGAATAATTCGAGGATCTGGCACCCCGCCGA ATGTAAAAAAAAAAAACCAAAAAGCTTTCCATTTGCTTCAATTGAAAGAAAATAAAACTAATTAATCCAATTTGTGTTGTTAGCAATCTTGTATG
GGAATTGATTAAATGCCAAATACTGTGTATATTATTTACTTTCTTTGAATTTAACTAGCTAAGTTTTATATATTATAAAAAATCCATTTAATTAG
TTAAACAAGTGCTAAGCTAGTTTTGCACTGCATTTATGTATTATTACCTTAATTAATGCCTTTCAATCGGAAACAGTAATTATTTCAAGCCCGTT
TTAAGCCCAGTTCGAAGTCGAATATTTAACTTGGTCAAAACTAAGCATGGTCCGAAAAACCCAAGAAATTCGATTCGGGAGTTACCTTGAGGATT
TTCACAAACATATATGTATGTAACTTGCATACCACCCAAAGAAAACAACAGTAGCTTCTTTTTATTTGCCACCGCTATTTAAATATTTAATGCCC
GCGAAGCACAGAGCTTTTTATTTGTTGCTAGTCGCGACCTTGATTCAGTTGGCATTTGGTGGGTTTGTTCGTTGTCTAATTGTATTATTTGGCAA
TTGCTGCCAACTCGACCGCCATGGCGGATTTCACATATTTAAGCGTTTTGGCCATTTTACAACGGTCGCTTAATAATGCTTTTCTGGCCATACAT
ACATACGTATGACGATAACAATTGGCCAAAATCAGTGTTAAAGCCATGTAAAATGCAATGAGTGAATATTTTCTGCGATTTGTCCCTGATTCTGA
CGTATTTTTTCAATTCGCCAAACAAAATTTGCGATCAATTAGAATTCAGTGCGCGACAATTGGCGACAAATTGACCCTACCAAAGTTCGCGCGTG
GGGTTAACTCACATCATCGAAATTGCACAGCCATTTGAATTTGGACAGCTTGTCGTCGTAGTTGGGTCCATGCCCCAGAATATTGGGCTCCTCAT
TGGACGGAAATTGATGCGCTGCGTCCACCGAATCCGCAACCAGTTGGCCATCAAGCTGCGAAAAGAGATTTAAGATGGAATTAGTTAAAATGGAG
GAAACCCTATCGATTAGCGGCAATTCGAAACTTAATTTGAATTGAGGACAAGAACGATGCTCAAGATCTATACTCATATTCTTCCGCCTTAGAAA
ACTGACGTTGGCAACTGGCGGGTTTGTTTCTCTGCACATTTGTGTATATTTTTAGCCAATAGAGCAACTGCAGTCGAAAAATTGATTTGTTTGCT
TTTATTTTATTATTATCTTTTCTGCGGTTTCTGCTATTTTATACGTTGTTGTTGTTGTTGTTTTCGTCTGGGGGTTTTCGGTTTCGTGTGTA
AACAACCAACCAACCAACCAACCGACTAACCAGCATTGCAAAAATGCAATCAAAACATCGCTACTATTAGTGCCTCCAGCAAACTGCAGCAAAAA
TTGAGAAAGGGGGCTTGACTCTAATTTGTTTATACAGCTTCTAAATCTAATGCATAACAACAAACAACAACAACAACAACAAGTGTGGGAGGGCA
AGTGCAAGTGCCTAAGCAAAAGTATCTTATCCAACGTGATGACGTTTTGTTTACAATTTGCATTGTTTTTTTGCATTCCGCTTTAAAGGAAAAT
CATGTGCAGTAAGCGTCGTGCCCATAAATGCAGCAGTAAGTATAAAAATATATGCATTTTTCAATACAAATTAAATATAACCGCTCATTAAAACG
AAATACAGGAACAATTGAATTCCCAATCCTAATTCTTTTGTACAAGCAACAATTTCGTAGTTACTTAAATGCTAATTAAAAATCCATGATGTCAA
AACTTAGCTACATTTATCAATTTTTAAAATTTACTCATGATCTAATAGTCACTAAAAGGCTAAATAGCTTTCGCTACCTATTTGTAAACAATGTT
ACTAGTAAGTGCTTTGTGGTTTACTCTGTCGTCATTATTAAATATTTATTTGACACTCAGGAACGTGTGGATTTATAGTAAATTTAGGCAAAAAA
TATATAGAAATTTTTCAATAATTTAGAAACATAAAAATATGTTTATGAAATGAAAATGAACCGCTATTTAACTTAAAGACATTCGTTAAGACAAG
AAATGTACTATTATAATATTGATTGTTTTAATTTTAATAATTAAGGAACTAAAAGTTATTTGTGTAAAATGATTTTGAACAAAACTAAAATAAAA
TATAGAACAAATAATTTTACATAAAAATTATTATACACGAGCACGTCAACTTGACATTGCGGCTTGTTAAATATTTTCCAGCAAATGCACTTCAC
GAAAATGTTGTAGATTCCAAAAGATAAACACGGTAATTGTTGGCAAATAGAAAATAAAATGGAATGCCATCGATAAACAGGATGTGAAATTCATT
AATTGGCCATTGACGTAGTTTAGCCAATTGTTTGTTCTACTGAATTGAAAACGTCAGATTTTTAGAGTTTGGAACGCAGCTTACATCTTTCTTTT
TACTGCCGCGCATAGTGCATTTAAACTCAGTAGTAGTTGTTGTAGTAACAATTGTAGTTTCCATTTTACACAGGCACTTTTAACTAGTTGTTGAA
ACGTTTTGAAAGTATTTAGTTTTAATATTTTATTCGCAGATAACTATTATTTTATTTCAACACACAAAAGCCAGCCAAGTGGACATTCCAAAAC
AATGTTTTCAAAGTTTTTTTTTCGCAACTCCTTGGAGAGATTTTCAACTGAGCGCGGAAATTTTAGGGTGAACCGTTGCGATCGCCAACTTGCT
GGCAACTAAAAAACCCCCCGATATCCAATGTGGCCAATGGTGTGAATCGAAAAAGCTCGCCGAAAAGCTTTCTATAATTTCGCAGCAGCCGAGAG
ACGACGAATGCACTATCAGTTTTGTTTTATCAAGTCGCAAATGCTGAGCAATCATTTTGCCAGAGGGACGGTTTTCAGATTTTTCAACGGACAGT
TATGCTGAAATTATGCGAAATTTCGTGGCCAATGAGCTTTCGCTTCTTGTGCAAGCAGCCTGTTTTGGTCAAGTCGGTTTGATTATCGAATACAC
TGAAAAACATCGGCCTGCATTTTCATCCAAGTAAGCTTATAGCTTCGATCTAACATAAGAAAAATGAATAAATAATTTTAAAATAAATAAAAAAT
AAAATGCATCTACACATATTTTACTTTTTTAGAAGCTAGTAAAATACATTATTATACATTCGACATTTTTTTATATGAATTATTTGTTAAGTGT
ATATTTTCCAAAAAAAAAGTTGTTTGTGCCTTTCTCAACACTTTTTTTTGTCGCAGTCAAGCCCCCGTATTATATAACCAATCGAGCTGATTATC
GATCCAGCATTGAGAACCCTTTTGTAAACACCAGTTGCACAACATGAAAAGCTGATGCCAATTCGCAATAATTGTTTACACGATCCCAATACACA
CGGATGGGTTTTTATCGCTGGACGGGAGACGTAAATAAAAGACGAAAAACAAATCTGAAAATCGAGCCCAAAAACCAGTTTCAATTTTCGACGAA
GTTCAGGAATTCCGCGTGCGGACTTTCGCAATTCCCATGTTTATACCCTTACATACCTACGCACATACATATGTACATATGTGTAAACATAATGC
ATAACAAGATATCGGTGTGGCAAGCTCTAATCGGTTACAAATAACGCCGACTCGTCATGACCTTGGCTCCATTCGTGGCGATCTGCTGGGCTTTT
TGACCTTGTGCTGTGGGGAAAATCGCGCACTCTGACACTTTGTGTAAGGTTATCTCCAAACTGCTGGCTCGTCTTTTCGGATGACAAATCATTTT
TTTTTTGAACTGATTGCATGTGCTGCGATGCACGTGCCGTTTTCAAGTCGCCGAGAACAGGACCGGATCTGGTATGATCAGTTTCCGGGTCCATT
CGATGCATCATAACATTGATAAAATTTTCGAAATATTTAAAATAGCTCATAATTTCCACATTTTAAAGCTTATGGTGGAAAAAAAGTATACAAAT
AAGTACTTATATATTATACTTTTGCTACATTATATTACATATATATTTGCTATTATATATTACACTTTTGATCAAATGAAATATTTATATAGTAT
GTATGTAAACCCCCGATAAGATTGAACTGCCCCCGTCTGAGCTTAATCCATTCAAAAAAATCTTTGTTGAGGAATGCATTGTAAACAGGAATATT
CCACTCACCAGGCAGCTGTCGTCACAATCCTGTCCAGATTTTCGCAAGTAGCAGGAGGACGAGTCCAGCGACAGTTCTGGTTCCTCGAGGATCTC
ACGGGGACGGGGACTCATGGCCACTCGGTAGCCTGATGGGGGTATTCACAGAAATACAGCTCGTTTAGAGATCGAGTGTCCGGGTAAAAATGTAA
ACATATACATAAGCTGCGATCGCCAGTTGGTGACCGGCTGTTATCAACAACCCCCCCCCCCCCCACCGTCACCGCTACCATTTCGCAGAAGAGTG
CGAAAATCGAGTCGAGCTGCCTAACAAAAGACAACTTGAGTGGTGCCAAGTGGGGAGCGCAGCCATGTTGCCATGTTGGAGCCAACAAAGACAGC
GAGCTTCGCTCTCTGCGTAGCCTCTCTTTTCTCACTTGGACTTTCTTCGGAGCTTAATCGATTAGAGGCCGAAGAAGCCTGCTCTACAAGGGTCT
TGAAAATAGTATATTTTTGTGATTGAGTTCTTTTTAATTAACACTATATAAGATATATTGACCTTATCGATAGTATTCTTAAGAAAAAGAAAATC
AAAAGTTTTATTTTTCAGATAAAAATAGTTTTCAAATAAGATTGCTCTGCAATGAAGGTGGTGCGTTGAGCACATGAAATACATATATGCATATA
ATGAATACAAAATATATAGTTTGCTTTGTTTCCACGACTGCAGTTTCGAGTTTATTTCTTTTACAGCACAGCACAGCCACACGAATTTCTCTCAC
AAAACCGTTTGCATAACCAAAATTTCTAAAAGTTTTCCAGGTCACTTGTTTCGCAGGCAGCTTTCGCAGCACGTGTCTCGACGAATGCAGTTGTA
TTGACATTCCCAAGGGTCCAGATAACCTTCAATTGATTTTGATGTACTTGCTCTAACTAGGCCACACACGGAACAGGGATTGGAAATTTCACTTT
GAGCTGCAAAGTTCTGGCGATCACCTCCACCTCTCGCAACGCGGCAAAATATCAACTGAATATTTTCAGACCTCGAGTGTGTTATTTGCGTTAAA
AGAAAGAGTCGCGAATCGCTGCGAAGAGAAGAAAGAGAAAAGAAATACTAAAAGCTCGCTCCGAAGCTTTGGCGACGCGAGCATGATTCTTCTCA
TATACAGTATATAGCATTTGAATTGATTAAATGCTAATTTAGCATGCTGTGGTCGTTGCCGCCATCGGAGATCTTACACTGAAACTTGAAAAGCG
GATTCTGAATATCAATTCTTCTTGAAAAAAGGCTTTTATATGTATACATAGATCTATAGCTTCCTAAAAATCATTGCAGCTCATTATCAAACATG
CTTTAATGCTGATTCGTCTGTATAAATATTTAATTATTGTCTACCAAGTCATTGGAAAATTTTCACCACTATGCTTATTCGCCAACACTCTCGGA
ATATTTTATTTTTTCCATGGTCTATTTGTATAATTTCTTACCTTAATGCCAAGACCATTTGAATATTTATACCCTGTCCTTTGCTGTTTTGTTCT
CTTATCAATGCCCTTCGCATTGACCGAGTTTTCAGATTTCCTTGCCTTTGGCATCATTAATCCCTTTCAACATGGCCAAAAGCCATTCAAAACTG
AATTGTTGAGAGCTGTCACTTGGCATTTTATTGCCATCAGATAGCTGTACTCACAACAAAATTCTACGACAACCCAACCGACAAAGCCCACACGA
TGATAGTTAATTAAAAAGTTGTTGGCACACTCAGAATATCATGCAAAATTAGCCTGGCTAACTGGCCTTATCATAATTATCAGCAATCCCCAAAC
AAAACTTTACAACATGATAATTATTAAATAAAAAGCAAATAACCACTAACAGTAGAACCGAATTAACATTTGTGAGCTCAGAAAACAAAAGCAAA
ATACAGGTGAAACAAAATGCAGCAGCATCCGTTTACTAATTTATACGCAATCTCAAATAATTTACAAAACAAATGGTTAACCGAAAGAAAT
(SEQ ID NO: 844)

Exon: 7736..7648
Exon: 6872..6754
Exon: 3570..3433
Exon: 2390..2283

FIGURE SHEET 455

Exon: 2173..1700
Exon: 1632..1001
Start ATG: 6858 (Reverse strand: CAT)

Transcript No. : CT22875
CGTTGCGAGAGGTGGAGGTGATCGCCAGAACTTTGCAGCTCAAAGTGAAATTTCCAATCCCTGTTCCGTGTGTGGCCTAGTTAGAGCAAGCTACC
GAGTGGCCATGAGTCCCCGTCCCCGTGAGATCCTCGAGGAACCAGAACTGTCGCTGGACTCGTCCTCCTGCTACTTGCGAAAATCTGGACAGGAT
TGTGACGACAGCTGCCTGCTTGATGGCCAACTGGTTGCGGATTCGGTGGACGCAGCGCATCAATTTCCGTCCAATGAGGAGCCCAATATTCTGGG
GCATGGACCCAACTACGACGACAAGCTGTCCAAATTCAAATGGCTGTGCAATTTCGATGATGCCCCCAGTCACCTGAAGTTCAACCCGTACATTC
GTCGCGGATACCGCACCTTTCTACCTTCCACAAAAATGTGCCTGCAGAGCATTTTCTGGTGGACCAATGAGACGATCAACATCTGGAGCCATCTG
GCCGGTTGCATCCTGTTCATTGGACTGACCATCTTCGATCTGCAGTTCCTGCGCCTCCACGCCTCCCTGAGCGACCAGGTGCTGGTGGTCTGCCT
GCTGGTCTGCTTCTGTCTGTGCATGCTGATGTCCGCCATATACCACATCTTCTCCTGCAAATCGGAGGAGCACTACGAGCTCTTTCTGTCCGTTG
ACTTCCTGGGCATTTCGCTGTCGCTGGTGGCCATCTATATCAGTGGCATGTACTATGCCTTCTGGTGCCACACCTTCCTGCGCACCCTGTACTCC
ACGATTGCACTGGGCATGTTCGCACTGGCCATTGCCGTGCAGATACCCCGTTTGAATGTGTCCATGAACGGCAAGGTGGCGGTGCTGCTACTCTG
GTCTGCCTATGGAATCATACCTCTGGGCCACTGGGCGGTGGCCATGGGCGGTCTGGAGAACGAGCTAGTCAGGCTGATGGTGCCCCGCATCGTGC
TCATGTACTTGCTCTGCCTCGTCGCCTTCGTTTTCTATGCGGCCAAGATTCCGGAGCGCTGGTTCACCGGCAAGGTGGACTTCGTTGGGCATTCG
CACAACTGGTGGCACCTGATCATCGTGGCCGCCTTCTATCACTGGCACAACACCGGACTGGTCTATGCCGAGTATCGCCTGAATAACGGATGCAC
TGCACCAGTTCTCTCCTAGAACTTGAAGATCCGAACATCTGAGTTAAGATCCGAAGATCCGAGGAGCGGAGATGGAATCCGGGACTCTAGTAGAC
TAAAGCTTAGTGTAAATAGTTTATGGGGCGCTCTTTATCCGCTAATAACTAATATTTAGTTGTAGTTGTTGACCGATATGATTAATTTATGTTTA
ATTTACCAATTAGTTAGGGTTTCGTGTTAGACAATCCAGATCCAGATAGTTGGCATCGCATAAGCGGCAAAAAGGTTTCTCTCTTTATATCCTAA
TTGATTTCCTTTAATATATACAATTAAACAATGTCAATGAAATTGCATGTGTCTTGAGCTGAAGCTGTGTTAGTCTTGTTGACTCAATTTTTACA
ATTCATAAAATGCAAATACAATATCAAACGTACAAAGCAA
(SEQ ID NO: 845)

Start ATG: 104 (Reverse strand: CAT)

MSPRPREILEEPELSLDSSSCYLRKSGQDCDDSCLLDGQLVADSVDAAHQFPSNEEPNILGHGPNYDDKLSKFKWLCNFDDAPSHLKFNPYIRRG
YRTFLPSTKMCLQSIFWWTNETINIWSHLAGCILFIGLTIFDLQFLRLHASLSDQVLVVCLLVCFCLCMLMSAIYHIFSCKSEEHYELFLSVDFL
GISLSLVAIYISGMYYAFWCHTFLRTLYSTIALGMFALAIAVQIPRLNVSMNGKVAVLLLWSAYGIIPLGHWAVAMGGLENELVRLMVPRIVLMY
LLCLVAFVFYAAKIPERWFTGKVDFVGHSHNWWHLIIVAAFYHWHNTGLVYAEYRLNNGCTAPVLS*
(SEQ ID NO: 846)

Classification: hypothetical

Celera Sequence No. : 142000013384523
CTCCGGCGATAATGGAGACCGACCCGCACACACACACACACAACACGGCCACACGGTGACGGGCGTAGAGGCACACACCGAGCCAACTCGAATAC
ACACGCGCGCAGGGGAGAGAGAGCGGGAGAGCGCGGGCGCGCTCTCAATTATTTATTTACTTTTTCGTAACTGCATTCCATTCCAGCTCAAACA
CACGCACACATATGGGGGACGAACACAAGCGCACACGATCACTGCTCACAGTTGGTGCTGCTTCTTTTCATTTCTTGTTGTTGCAAGCGTTTGAA
CTCCTTTACTTATTTTCTTATTTTCGCCTAATTGAAACTAATTAACGACGATAATCCAACCATCCACTTGGTGTTCACAAAAAAATATGTACTTC
AGTTTAGTGAGTTCGCGCCGTCGCCGATCTCTTCGGTTCCGGAATTCCTTGGGGGAGCAGCAAAAAACACGAGTAGCGCGCTTGATGACCGTCCG
ATTCGGATTCGGAATTTGTTTTGGTAACATTCGCTGCTAGTGGTGTAGCAGAAAACATCGCATTGCATATCGATACACTCGCGGCGATGTTATTC
GATGTATTGGTTGATATCGATATTATAGGCTGTATTGACGCGGTTGCAGAGATGCGATATTTAACAATCATGCACGAAAAGTATTTATTGTTATT
TGGCTTGTGTAGTCCCCAAGCATAGGTGTAATTGTTGAGGGAAGAAAATAGGAGTTGTACGTTCAAAGATCGGCTTGGTAACAGGAACTAGTTCG
GTTCTTCAAGCGATGTTAATCAAAGCCAGTTCCGATAGATCATGTTAACTCGCTCTGTTAACAATTACTGTTATCTTAATCCTAACATTTCCGTT
ACATTTTAAAAACAGAAAAAGAAAAAATTTAAAAAAAAAGACTGTAAACTGAGTTACGCATTTCGAAATCAATATGTATCCCAACCATAGATAGA
AAAATAAATTATGTTTCCGAAACATAACTTCAATAAAACCACAATTTCGCTTGCTTTGTACGTTTGATATTGTATTTGCATTTTATGAATTGTAA
AAATTGAGTCAACAAGACTAACACAGCTTCAGCTCAAGACACATGCAATTTCATTGACATTGTTTAATTGTATATATTAAAGGAAATCAATTAGG
ATATAAAGAGAGAAACCTTTTTGCCGCTTATGCGATGCCAACTATCTGGATCTGGATTGTCTAACACGAAACCCTAACTAATTGGTAAATTAAAC
ATAAATTAATCATATCGGTCAACAACTACAACTAAATATTAGTTATTAGCGGATAAAGAGCGCCCCATAAACTATTTACACTAAGCTTTAGTCTA
CTAGAGTCCCGGATTCCATCTCCGCTCCTCGGATCTTCGGATCTTAACTCAGATGTTCGGATCTTCAAGTTCTAGGAGAGAACTGGTGCAGTGCA
TCCGTTATTCAGGCGATACTCGGCATAGACCAGTCCGGTGTTGTGCCAGTGATAGAAGGCGGCCACGATGATCAGGTGCCACCAGTTGTGCGAAT
GCCCAACGAAGTCCACCTTGCCGGTGAACCAGCGCTCCGGAATCTTGGCCGCATAGAAAACGAAGGCGACGAGGCAGAGCAAGTACATGAGCACG
ATGCGGGGCACCATCAGCTGCAAATGGTAATGATTGATGGATTAGCAAATGACAAGATTCCATAAATTTCCAACTGATGCCTACCCTGACTAGCT
CGTTCTCCAGACCGCCCATGGCCACCGCCCAGTGGCCCAGAGGTATGATTCCATAGGCAGACCAGAGTAGCAGCACCGCCACCTTGCCGTTCATG
GACACATTCAAACGGGGTATCTGCACGGCAATGGCCAGTGCGAACATGCCCAGTGCAATCGTGGAGTACAGGGTGCGCAGGAAGGTGTGGCACCA
GAAGGCATAGTACATGCCACTGATATAGATGGCCACCAGCGACAGCGAAATGCCCAGGAAGTCAACGGACAGAAAGAGCTCGTAGTGCTCCTCCG
ATTTGCAGGAGAAGATGTGGTATATGGCGGACATCAGCATGCACAGACAGAAGCAGACCAGCAGGCAGACCACCAGCACCTGGTCGCTCAGGGAG
GCGTGGAGGCGCAGGAACTGCAGATCGAAGATGGTCAGTCCAATGAACAGGATGCAACCGGCCAGATGGCTCCAGATGTTGATCTATGAAAAATA
TAGCAATAATAATGTTATAATAATAGGGAATAGAGTTTAAGGAAAACTATTGTAGCTCCAATTGGAATGGAGTATCATTCTAGTGTGGCAATCTT
ACCGTCTCATTGGTCCACCAGAAAATGCTCTGCAGGCACATTTTTGTGGAAGGTAGAAAGGTGCGGTATCCGCGACGAATGTACGGGTTGAACTT
CAGGTGACTGGGGGCCTGTATCGAAAGCACAAGTGAATAAACATTCCAAATAAATACAAAATTTTCCAAGCCGATAAGACATGCAAATCGCATGC
GTGTAGCATTGAAAATAAAATAAAAACCAAATAGACAAAATGACAAAATAAAATAGAAACAAACGGAATAATTCGAGGATCTGGCACCCCGCCGA
ATGTAAAAAAAAAAAACCAAAAAGCTTTCCATTTGCTTCAATTGAAAGAAAATAAAACTAATTAATCCAATTTGTGTTGTTAGCAATCTTGTATG
GGAATTGATTAAATGCCAAATACTGTGTATATTATTTACTTTCTTTGAATTTAACTAGCTAAGTTTTATATATTATAAAAAATCCATTTAATTAG
TTAAACAAGTGCTAAGCTAGTTTTGCACTGCATTTATGTATTATTACCTTAATTAATGCCTTTCAATCGGAAACAGTAATTATTTCAAGCCCGTT
TTAAGCCCAGTTCGAAGTCGAATATTTAACTTGGTCAAAACTAAGCATGGTCCGAAAAACCCAAGAAATTCGATTCGGGAGTTACCTTGAGGATT
TTCACAAACATATATGTATGTAACTTGCATACCACCCAAAGAAAACAACAGTAGCTTCTTTTTATTTGCCACCGCTATTTAAATATTTAATGCCC
GCGAAGCACAGAGCTTTTTATTTGTTGCTAGTCGCGACCTTGATTCAGTTGGCATTTGGTGGGTTTGTTCGTTGTCTAATTGTATTATTTGGCAA
TTGCTGCCAACTCGACCGCCATGGCGGATTTCACATATTTAAGCGTTTTGGCCATTTTACAACGGTCGCTTAATAATGCTTTTCTGGCCATACAT
ACATACGTATGACGATAACAATTGGCCAAAATCAGTGTTAAAGCCATGTAAAATGCAATGAGTGAATATTTTCTGCGATTTGTCCCTGATTCTGA CGTATTTTTTCAATTCGCCAAACAAAATTTGCGATCAATTAGAATTCAGTGCGCGACAATTGGCGACAAATTGACCCTACCAAAGTTCGCGCGTG
GGGTTAACTCACATCATCGAAATTGCACAGCCATTTGAATTTGGACAGCTTGTCGTCGTAGTTGGGTCCATGCCCCAGAATATTGGGCTCCTCAT
TGGACGGAAATTGATGCGCTGCGTCCACCGAATCCGCAACCAGTTGGCCATCAAGCTGCGAAAAGAGATTTAAGATGGAATTAGTTAAAATGGAG
GAAACCCTATCGATTAGCGGCAATTCGAAACTTAATTTGAATTGAGGACAAGAACGATGCTCAAGATCTATACTCATATTCTTCCGCCTTAGAAA
ACTGACGTTGGCAACTGGCGGGTTTGTTTCTCTGCACATTTGTGTATATTTTTAGCCAATAGAGCAACTGCAGTCGAAAAATTGATTTGTTTGCT
TTTATTTTATTATTATCTTTTCTGCGGTTTCTGCTATTTTATACGTTGTTGTTGTTGTTGTTGTTTTCGTCTGGGGGTTTTCGGTTTCGTGTGTA
AACAACCAACCAACCAACCAACCGACTAACCAGCATTGCAAAAATGCAATCAAAACATCGCTACTATTAGTGCCTCCAGCAAACTGCAGCAAAAA
TTGAGAAAGGGGGCTTGACTCTAATTTGTTTATACAGCTTCTAAATCTAATGCATAACAACAAACAACAACAACAACAACAAGTGTGGGAGGGCA
AGTGCAAGTGCCTAAGCAAAAGTATCTTATCCAACGTGATGACGTTTTGTTTACAATTTGCATTGTTTTTTTTGCATTCCGCTTTAAAGGAAAAT
CATGTGCAGTAAGCGTCGTGCCCATAAATGCAGCAGTAAGTATAAAAATATATGCATTTTTCAATACAAATTAAATATAACCGCTCATTAAAACG
AAATACAGGAACAATTGAATTCCCAATCCTAATTCTTTTGTACAAGCAACAATTTCGTAGTTACTTAAATGCTAATTAAAAATCCATGATGTCAA
AACTTAGCTACATTTATCAATTTTTAAAATTTACTCATGATCTAATAGTCACTAAAAGGCTAAATAGCTTTCGCTACCTATTTGTAAACAATGTT
ACTAGTAAGTGCTTTGTGGTTTACTCTGTCGTCATTATTAAATATTTATTTGACACTCAGGAACGTGTGGATTTATAGTAAATTTAGGCAAAAAA
TATATAGAAATTTTTCAATAATTTAGAAACATAAAAATATGTTTATGAAATGAAAATGAACCGCTATTTAACTTAAAGACATTCGTTAAGACAAG
AAATGTACTATTATAATATTGATTGTTTTAATTTTAATAATTAAGGAACTAAAAGTTATTTGTGTAAAATGATTTTGAACAAAACTAAAATAAAA
TATAGAACAAATAATTTTACATAAAAATTATTATACACGAGCACGTCAACTTGACATTGCGGCTTGTTAAATATTTTCCAGCAAATGCACTTCAC
GAAAATGTTGTAGATTCCAAAAGATAAACACGGTAATTGTTGGCAAATAGAAAATAAAATGGAATGCCATCGATAAACAGGATGTGAAATTCATT
AATTGGCCATTGACGTAGTTTAGCCAATTGTTTGTTCTACTGAATTGAAAACGTCAGATTTTTAGAGTTTGGAACGCAGCTTACATCTTTCTTTT
TACTGCCGCGCATAGTGCATTTAAACTCAGTAGTAGTTGTTGTAGTAACAATTGTAGTTTCCATTTTACACAGGCACTTTTAACTAGTTGTTGAA
ACGTTTTGAAAGTATTTAGTTTTTAATATTTTATTCGCAGATAACTATTATTTTATTTCAACACACAAAAGCCAGCCAAGTGGACATTCCAAAAC
AATGTTTTCAAAGTTTTTTTTTCGCAACTCCTTGGAGAGATTTTCAACTGAGCGCGGAAATTTTAGGGTGAACCGTTGCGATCGCCAACTTGCT
GGCAACTAAAAAACCCCCCGATATCCAATGTGGCCAATGGTGTGAATCGAAAAAGCTCGCCGAAAAGCTTTCTATAATTTCGCAGCAGCCGAGAG
ACGACGAATGCACTATCAGTTTTGTTTTATCAAGTCGCAAATGCTGAGCAATCATTTTGCCAGAGGGACGGTTTTCAGATTTTTCAACGGACAGT
TATGCTGAAATTATGCGAAATTTCGTGGCCAATGAGCTTTCGCTTCTTGTGCAAGCAGCCTGTTTTGGTCAAGTCGGTTTGATTATCGAATACAC
TGAAAAACATCGGCCTGCATTTTCATCCAAGTAAGCTTATAGCTTCGATCTAACATAAGAAAAATGAATAAATAATTTTAAAATAAATAAAAAAT
AAAATGCATCTACACATATTTTACTTTTTTTAGAAGCTAGTAAAATACATTATTATACATTCGACATTTTTTTATATGAATTATTTGTTAAGTGT
ATATTTTCCAAAAAAAAAGTTGTTTGTGCCTTTCTCAACACTTTTTTTTGTCGCAGTCAAGCCCCCGTATTATATAACCAATCGAGCTGATTATC
GATCCAGCATTGAGAACCCTTTTGTAAACACCAGTTGCACAACATGAAAAGCTGATGCCAATTCGCAATAATTGTTTACACGATCCCAATACACA
CGGATGGGTTTTTATCGCTGGACGGGAGACGTAAATAAAAGACGAAAAACAAATCTGAAAATCGAGCCCAAAAACCAGTTTCAATTTTCGACGAA
GTTCAGGAATTCCGCGTGCGGACTTTCGCAATTCCCATGTTTATACCCTTACATACCTACGCACATACATATGTACATATGTGTAAACATAATGC
ATAACAAGATATCGGTGTGGCAAGCTCTAATCGGTTACAAATAACGCCGACTCGTCATGACCTTGGCTCCATTCGTGGCGATCTGCTGGGCTTTT
TGACCTTGTGCTGTGGGAAAATCGCGCACTCTGACACTTTGTGTAAGGTTATCTCCAAACTGCTGGCTCGTCTTTTCGGATGACAAATCATTTT
TTTTTTGAACTGATTGCATGTGCTGCGATGCACGTGCCGTTTTCAAGTCGCCGAGAACAGGACCGGATCTGGTATGATCAGTTTCCGGGTCCATT
CGATGCATCATAACATTGATAAAATTTTCGAAATATTTAAAATAGCTCATAATTTCCACATTTTAAAGCTTATGGTGGAAAAAAAGTATACAAAT
AAGTACTTATATATTATACTTTTGCTACATTATATTACATATATATTTGCTATTATATATTACACTTTTGATCAAATGAAATATTTATATAGTAT
GTATGTAAACCCCCGATAAGATTGAACTGCCCCCGTCTGAGCTTAATCCATTCAAAAAAATCTTTGTTGAGGAATGCATTGTAAACAGGAATATT
CCACTCACCAGGCAGCTGTCGTCACAATCCTGTCCAGATTTTCGCAAGTAGCAGGAGGACGAGTCCAGCGACAGTTCTGGTTCCTCGAGGATCTC
ACGGGGACGGGGACTCATGGCCACTCGGTAGCCTGATGGGGGTATTCACAGAAATACAGCTCGTTTAGAGATCGAGTGTCCGGGTAAAAATGTAA
ACATATACATAAGCTGCGATCGCCAGTTGGTGACCGGCTGTTATCAACAACCCCCCCCCCCCCCACCGTCACCGCTACCATTTCGCAGAAGAGTG
CGAAAATCGAGTCGAGCTGCCTAACAAAAGACAACTTGAGTGGTGCCAAGTGGGGAGCGCAGCCATGTTGCCATGTTGGAGCCAACAAAGACAGC
GAGCTTCGCTCTCTGCGTAGCCTCTCTTTTCTCACTTGGACTTTCTTCGGAGCTTAATCGATTAGAGGCCGAAGAAGCCTGCTCTACAAGGGTCT
TGAAAATAGTATATTTTTGTGATTGAGTTCTTTTTAATTAACACTATATAAGATATATTGACCTTATCGATAGTATTCTTAAGAAAAAGAAAATC
AAAAGTTTTATTTTTCAGATAAAAATAGTTTTCAAATAAGATTGCTCTGCAATGAAGGTGGTGCGTTGAGCACATGAAATACATATATGCATATA
ATGAATACAAAATATATAGTTTGCTTTGTTTCCACGACTGCAGTTTCGAGTTTATTTCTTTTACAGCACAGCACAGCCACACGAATTTCTCTCAC
AAAACCGTTTGCATAACCAAAATTTCTAAAAGTTTTCCAGGTCACTTGTTTCGCAGGCAGCTTTCGCAGCACGTGTCTCGACGAATGCAGTTGTA
TTGACATTCCCAAGGGTCCAGATAACCTTCAATTGATTTTGATGTACTTGCTCTAACTAGGCCACACACGGAACAGGGATTGGAAATTTCACTTT
GAGCTGCAAAGTTCTGGCGATCACCTCCACCTCTCGCAACGCGGCAAAATATCAACTGAATATTTTCAGACCTCGAGTGTGTTATTTGCGTTAAA
AGAAAGAGTCGCGAATCGCTGCGAAGAGAAGAAAGAGAAAAGAAATACTAAAAGCTCGCTCCGAAGCTTTGGCGACGCGAGCATGATTCTTCTCA
TATACAGTATATAGCATTTGAATTGATTAAATGCTAATTTAGCATGCTGTGGTCGTTGCCGCCATCGGAGATCTTACACTGAAACTTGAAAAGCG
GATTCTGAATATCAATTCTTCTTG
(SEQ ID NO: 847)

Exon: 7004..6754
Exon: 3570..3433
Exon: 2390..2283
Exon: 2173..1700
Exon: 1632..1001
Start ATG: 6858 (Reverse strand: CAT)

Transcript No. : CT22885
ACGGTGGGGGGGGGGGGTTGTTGATAACAGCCGGTCACCAACTGGCGATCGCAGCTTATGTATATGTTTACATTTTTACCCGGACACTCGATC
TCTAAACGAGCTGTATTTCTGTGAATACCCCCATCAGGCTACCGAGTGGCCATGAGTCCCCGTCCCCGTGAGATCCTCGAGGAACCAGAACTGTC
GCTGGACTCGTCCTCCTGCTACTTGCGAAAATCTGGACAGGATTGTGACGACAGCTGCCTGCTTGATGGCCAACTGGTTGCGGATTCGGTGGACG
CAGCGCATCAATTTCCGTCCAATGAGGAGCCCAATATTCTGGGGCATGGACCCAACTACGACGACAAGCTGTCCAAATTCAAATGGCTGTGCAAT
TTCGATGATGCCCCCAGTCACCTGAAGTTCAACCCGTACATTCGTCGCGGATACCGCACCTTTCTACCTTCCACAAAAATGTGCCTGCAGAGCAT
TTTCTGGTGGACCAATGAGACGATCAACATCTGGAGCCATCTGGCCGGTTGCATCCTGTTCATTGGACTGACCATCTTCGATCTGCAGTTCCTGC
GCCTCCACGCCTCCCTGAGCGACCAGGTGCTGGTGGTCTGCCTGCTGGTCTGCTTCTGTCTGTGCATGCTGATGTCCGCCATATACCACATCTTC
TCCTGCAAATCGGAGGAGCACTACGAGCTCTTTCTGTCCGTTGACTTCCTGGGCATTTCGCTGTCGCTGGTGGCCATCTATATCAGTGGCATGTA
CTATGCCTTCTGGTGCCACACCTTCCTGCGCACCCTGTACTCCACGATTGCACTGGGCATGTTCGCACTGGCCATTGCCGTGCAGATACCCCGTT
TGAATGTGTCCATGAACGGCAAGGTGGCGGTGCTGCTACTCTGGTCTGCCTATGGAATCATACCTCTGGGCCACTGGGCGGTGGCCATGGGCGGT
CTGGAGAACGAGCTAGTCAGGCTGATGGTGCCCCGCATCGTGCTCATGTACTTGCTCTGCCTCGTCGCCTTCGTTTTCTATGCGGCCAAGATTCC GGAGCGCTGGTTCACCGGCAAGGTGGACTTCGTTGGGCATTCGCACAACTGGTGGCACCTGATCATCGTGGCCGCCTTCTATCACTGGCACAACA
CCGGACTGGTCTATGCCGAGTATCGCCTGAATAACGGATGCACTGCACCAGTTCTCTCCTAGAACTTGAAGATCCGAACATCTGAGTTAAGATCC
GAAGATCCGAGGAGCGGAGATGGAATCCGGGACTCTAGTAGACTAAAGCTTAGTGTAAATAGTTTATGGGGCGCTCTTTATCCGCTAATAACTAA
TATTTAGTTGTAGTTGTTGACCGATATGATTAATTTATGTTTAATTTACCAATTAGTTAGGGTTTCGTGTTAGACAATCCAGATCCAGATAGTTG
GCATCGCATAAGCGGCAAAAAGGTTTCTCTCTTTATATCCTAATTGATTTCCTTTAATATATACAATTAAACAATGTCAATGAAATTGCATGTGT
CTTGAGCTGAAGCTGTGTTAGTCTTGTTGACTCAATTTTTACAATTCATAAAATGCAAATACAATATCAAACGTACAAAGCAA
(SEQ ID NO: 848)

Start ATG: 147 (Reverse strand: CAT)

MSPRPREILEEPELSLDSSSCYLRKSGQDCDDSCLLDGQLVADSVDAAHQFPSNEEPNILGHGPNYDDKLSKFKWLCNFDDAPSHLKFNPYIRRG
YRTFLPSTKMCLQSIFWWTNETINIWSHLAGCILFIGLTIFDLQFLRLHASLSDQVLVVCLLVCFCLCMLMSAIYHIFSCKSEEHYELFLSVDFL
GISLSLVAIYISGMYYAFWCHTFLRTLYSTIALGMFALAIAVQIPRLNVSMNGKVAVLLLWSAYGIIPLGHWAVAMGGLENELVRLMVPRIVLMY
LLCLVAFVFYAAKIPERWFTGKVDFVGHSHNWWHLIIVAAFYHWHNTGLVYAEYRLNNGCTAPVLS*
(SEQ ID NO: 849)

Classification: hypothetical

Celera Sequence No. : 142000013384703
GTCGCGCAAAGCCCAGGAGAAGGAGCGTCCCACCAAATCGGAACGCATTGATAGCACCAACCTGCTGCACTTCCGCATTCGTGCCTTGGATTTGT
TGGAGCTCTTCATAACCAAGAAACCAACTCAATCGGTAATCCTGGACGTGCTACATTGCGTGTTCCAGGTGTACAGCCATTGCGCCGCAGACAGC
AAACTACAATCCTTGCGAGAAGCCAGTTTGAAGTTGCTCAAAAAGATACTCGCTAGGAATATCGAACTCAAGGAAAATCAGAGCACCGCACCCAT
TCTGGAAGCCATTGAGCAGCTGATGTCGTCTGGCGAGGAGCATTCAGAAGAGGACCAAGAGAACGGCAAGCAGCCCGCCAGCCGACAGGCCAAAA
GAGACATCATTATTTGGCGGGACAGGTGCTTCGCTTACCTGGTCAGCCAGGCATCAGCAGATGGCGAGCCCAAGAAAAGTGCCGTCTGGCCCCTT
CTAGTCGAATTCCTGGAGCTGTGGGTAGCCAAGCGACGTAGTCGCCTCTCTCTGGCCAGTTTCGAAGCCCTCTTTCAGTCTGGCCAATGGCAGGG
AGTTGCTCCGCTGGCCGTTGTCCTGGCCTCTCACTTGGACGTACAGAAAACACGCAGTTTTCGGCGGGCACAGATACTGAAGCTGCTCAGCGAGC
AAGGTCGCCGGCTCGAAGTCGCTTTCAAGGACAACAACTCGTCTTCCAAGAAATTTGAGAAGCAGATAGCCAGATATGTAAATCAGCTAGAAACG
AAGGCTAGCAGTTCCAAGGAACTCAATCTGCTGCTTAAGATCCTCGCCCAAGGAGGCGAGAAGTGGCAGAAACTGCGTGAACAAATTCAGCTCGT
CGCCAAGGATCTTCAACCCAACAAGAAGGTGGCGAAGCAGAAGAAGCAGGCAGCCGCCAAACCTATGGTCGTGGAAGATGAAGAGTCCACATAAC
GTAAAAGAAGGAAACACCCCAATAAGAAACCTTACAATTAGATGTATAAATATCTTGCATAATATAGGATACTATTAATTTTTTTGTTCTTTAAA
AAATTCTGACGAAAAGTACTAAATTAGTATTGAAGTCATTGAAAAAATAGCAAAAGTACACTAAACTTTATAAAAATGTATTTTTACCTTTATAG
AGCAATTTGAGTGGACGTACAACTGCGCTAACGTTAAAAACCAAAATCACAGACGAGGTGGAAAGTACACGTGCTGGCGAAATGTGCTTTTAACA
TTCGGCACCATGGACTCGTCATTACTGCCTCGCTTTTTAGACACTTCGTTGGTGACAATCGTCAGGATATCGGCGATGTGTTCACTAAAGTAACA
AAGAACAACTTATGCATTAATTCGGGGCTAGCTTGCTTTGGCAGCTTTTTACCTGGCGGAACGGCGATCGATGGCATCGCACAGGCTCCCGATAA
ACCAGCTACCTGTTTGGGTGTGGCGCAGAGCAGCATATCCATTTACCGTGGACATGGCCCGCAGCATGTCGATGTGCTGGTCCGGCGACACGGTG
GTCACGTCTATCCTAAACTGAAAGAGGAATACGAAAATGTATAGGCTTTCCCATTCGACGACTTCATGCTTATAAATCTCCTTACGAGCTCATTT
GGCTTCTTTTTATGGACAAGCTTCTCCTGGCAGGCTTGTATGATTAGCAACTTCGGTTTGTAGTACAGGGTGTCGTAGCTGCAGAGCAAGTCCTC
GATATCCGTGATCTTCATGGCGATGCTGTTGGATGCGTAGACGGCCTCCTCGAAGCCGTGGCTCAGGATGAAGACCACTAGGGAATCGCGCACGA
GCGATCTATCGCACGCACTGCGAATGCGCTCTATGATGCCCATGTGATCCACGTTGTCGTACGCCTCCACATTGTATCCCATCGAGGAAAACACC
TCGATTAGTCGTTCTTTATCCACATCCGTGCCATCCCGTCTACGCAGTGGGTCGGGCGACAGAAATTTCTGTGGAGAAGGGCAATGTTGTACTTC
TTTTTGTTACTCAATATTGCAGAGATGAAACCATATTATCCCTGCTAACATTCCGGTGAAACTTCTGCTGGTTGATAATCAAGGCGATTCCTGCG
TTCTCCCGGGTCAACTTAAGAGCATCTATTTGTGTGGAACAGTACGACTGCTGGTTATCCGATTCAATCTCTTGCTTGACTGCCATCGCAGCAGT
GCCAGCCGCATCTGGCTCCGGAGCGTTACTAATGATGGTGTCTTTGAGCAAATTTGCTTGCGCCTGCAGACCGTTGGACTTCAAATGGCCGACCA
GCAGCTGAACATCGCTGCCTGCGGCATTTATGTCCCCTAACTTTATGCTCCTTCTGGTCAGCCAGTCCAGCAAAAAGATCTCCAGGTACGCGGGA
TCGTAGAAGCGAAGTGGATCTCCTGCCTGCTGGCTCTCCACCTTTTCGCGAACATCTAGGAGCAAGCGGCCACTCTGCACCAACGACAACTCCTC
ACACATCCTGTAGAGGCTCTTCAACAGAGGATGGACATGCAGCGTGATCCCAGCGATATGCGGCAAGTAGTGCATTCGCAGCTCCTGCCAGCAGA
AACCCAGTCTCCGGAGCACCTTGCGGGCCCCAATAATGCACAGGGCCTCCACGAGATGTCTTCTCCAGGTTTCTGGCCGGGACTTGGCGAACTTT
ATGAGTAGATCACTTTGCGGGAAGTCTGATCGTGTCATGGCCAAAAGTTTCTGCAGAATGTAGGTGGCATCCGAGTGGTCGTCGCCATAAAGCAG
AAAGCAGAGGCCCACCTAGAAGAAAACGAAGGTTCTACTGTTTAATTAACACTTTGGTCTAGCGGATGTGTAAAACATTTGAGTCATATTCGAAA
AGTCCTCCCAGGGAGGTGCCATACCTTTTGGGCAAAGTTCATGTCACGTTCCACGTAGATCAGATCGTTCTGATCGATGGTGTCTAGATGAATCA
ACAGGTTTGATCCGGCCATGGCGATCGGGAATATACAAAAATGTTTCACTTTAGGAAATGGCCGATAAATTGCACTCGCTGACATCCGATAGCCG
TGGCCTGAAGAGCTTCCACCGATCGATATCGATAAATGGATATGTTTTCTGCAATAGCGAAAGATCGGGGTGCTACCTATTAATTATACTTAAGA
AACAGATGATGTAGTTTTTTGATATAGAAGTTTAACAACCGGTTCAACAATCGGTTAATATTTAAAAATGTCGCAGCCAGCGAGCCTTTAGCTTT
AAAAGTAAGCTTGCGTTCACGGTTTTTGGGGAAATACCAAATATACTAGGTAAAAACATCGATTAACTAATATCATCCAACACGACGATATGTTC
TTTGCGAAAAATATCGATGTACTGGTATTTTTATGTTTCCACACCTCTAGTTCGTTTAAGTCGATCTGTTGAACTGTTAACAACACAACTCCTGA
ATATTATGTTTTGGACGAAAAGTTTTATTAATTTAATGTTTTTGTATATTGTATTCTGTCCATGAGCGTAACAGAGACAGACAGAGAGAAAGGGA
CAGATACTGAGATACGGGGCCCTCAGGCAGAGAAAGAGGGCGAAAGCAAGCTACAAGCGGGTGCGAGCGAGAGCGCGCGCTTGCCTCACGCACAT
ATATATAAATCTGTACATACATATAGTATCAGAAGAAAAAACTAAAGCCGCTATTCGATTTACGAAAACTGGCGAAAAATTCGACGATTTGTCTC
GTACCTATCTATGTACCTCACAACCACTTCGTCATCAAATACGTATAAGTCAGATGTATGTCAAACATATATATACATATGCATGTATATACACA
TCTATGTGAGGCCACTGCTATATCCCATACATGTATGCCTCTATATATATGTATATATTTATCCACCTACTGTACCACTTCCACATTATGTAAGC
AGCGACGCAAACAAAACACTAAAGCAGAAAATCCGAAAAGCAAAATGCGAAATGCAAAACAACGAACCAACAAAATCCCATCTATAAACCGAAAA
CCGAACAGCAATGTTATAACAAATACCGAAAAGTTGTTAATGTTCCACAAAAAAGCATAAAGCAGTCACGCTAAGAGAGTAAGATCGAACAAATG
AAATGTTTGTATGGCATAAGTAGTTCCCAGATTTTTGTATGTACTTCAATGCATATGCATGTGTGCGTATGCATGTATGTATGTATGTTTCTCGG
GGCCATGTCTCCCCACGCCCACGTACGT
(SEQ ID NO: 850)

Exon: 3208..2875
Exon: 2770..2027
Exon: 1968..1606
Exon: 1537..1383

Exon: 1319..1001
Start ATG: 2964 (Reverse strand: CAT)

Transcript No. : CT22949
CGACATTTTTAAATATTAACCGATTGTTGAACCGGTTGTTAAACTTCTATATCAAAAAACTACATCATCTGTTTCTTAAGTATAATTAATAGGTA
GCACCCCGATCTTTCGCTATTGCAGAAAACATATCCATTTATCGATATCGATCGGTGGAAGCTCTTCAGGCCACGGCTATCGGATGTCAGCGAGT
GCAATTTATCGGCCATTTCCTAAAGTGAAACATTTTTGTATATTCCCGATCGCCATGGCCGGATCAAACCTGTTGATTCATCTAGACACCATCGA
TCAGAACGATCTGATCTACGTGGAACGTGACATGAACTTTGCCCAAAAGGTGGGCCTCTGCTTTCTGCTTTATGGCGACGACCACTCGGATGCCA
CCTACATTCTGCAGAAACTTTTGGCCATGACACGATCAGACTTCCCGCAAAGTGATCTACTCATAAAGTTCGCCAAGTCCCGGCCAGAAACCTGG
AGAAGACATCTCGTGGAGGCCCTGTGCATTATTGGGGCCCGCAAGGTGCTCCGGAGACTGGGTTTCTGCTGGCAGGAGCTGCGAATGCACTACTT
GCCGCATATCGCTGGGATCACGCTGCATGTCCATCCTCTGTTGAAGAGCCTCTACAGGATGTGTGAGGAGTTGTCGTTGGTGCAGAGTGGCCGCT
TGCTCCTAGATGTTCGCGAAAAGGTGGAGAGCCAGCAGGCAGGAGATCCACTTCGCTTCTACGATCCCGCGTACCTGGAGATCTTTTTGCTGGAC
TGGCTGACCAGAAGGAGCATAAAGTTAGGGGACATAAATGCCGCAGGCAGCGATGTTCAGCTGCTGGTCGGCCATTTGAAGTCCAACGGTCTGCA
GGCGCAAGCAAATTTGCTCAAAGACACCATCATTAGTAACGCTCCGGAGCCAGATGCGGCTGGCACTGCTGCGATGGCAGTCAAGCAAGAGATTG
AATCGGATAACCAGCAGTCGTACTGTTCCACACAAATAGATGCTCTTAAGTTGACCCGGGAGAACGCAGGAATCGCCTTGATTATCAACCAGCAG
AAGTTTCACCGGAATGTTAGCAGGGATAATATGAAATTTCTGTCGCCCGACCCACTGCGTAGACGGGATGGCACGGATGTGGATAAAGAACGACT
AATCGAGGTGTTTTCCTCGATGGGATACAATGTGGAGGCGTACGACAACGTGGATCACATGGGCATCATAGAGCGCATTCGCAGTGCGTGCGATA
GATCGCTCGTGCGCGATTCCCTAGTGGTCTTCATCCTGAGCCACGGCTTCGAGGAGGCCGTCTACGCATCCAACAGCATCGCCATGAAGATCACG
GATATCGAGGACTTGCTCTGCAGCTACGACACCCTGTACTACAAACCGAAGTTGCTAATCATACAAGCCTGCCAGGAGAAGCTTGTCCATAAAAA
GAAGCCAAATGAGCTCTTTAGGATAGACGTGACCACCGTGTCGCCGGACCAGCACATCGACATGCTGCGGGCCATGTCCACGGTAAATGGATATG
CTGCTCTGCGCCACACCCAAACAGGTAGCTGGTTTATCGGGAGCCTGTGCGATGCCATCGATCGCCGTTCCGCCAGTGAACACATCGCCGATATC
CTGACGATTGTCACCAACGAAGTGTCTAAAAAGCGAGGCAGTAATGACGAGTCCATGGTGCCGAATGTTAAAAGCACATTTCGCCAGCACGTGTA
CTTTCCACCTCGTCTGTGATTTTGGTTTTAACGTTAGCGCAGTTGTACGTCCACTCAAATTGCTCTATAAAGGTAAAAATACATTTTTATAAAG
TTTAGTGTACTTTTGCTATTTTTTCAATGACTTCAATACTAATTTAGTACTTTTCGTCAGAATTTTTTAAAGAACAAAAAAATTAATAGTATCCT
ATATTATGCAAGATA
(SEQ ID NO: 851)

Start ATG: 245 (Reverse strand: CAT)

MAGSNLLIHLDTIDQNDLIYVERDMNFAQKVGLCFLLYGDDHSDATYILQKLLAMTRSDFPQSDLLIKFAKSRPETWRRHLVEALCIIGARKVLR
RLGFCWQELRMHYLPHIAGITLHVHPLLKSLYRMCEELSLVQSGRLLLDVREKVESQQAGDPLRFYDPAYLEIFLLDWLTRRSIKLGDINAAGSD
VQLLVGHLKSNGLQAQANLLKDTIISNAPEPDAAGTAAMAVKQEIESDNQQSYCSTQIDALKLTRENAGIALIINQQKFHRNVSRDNMKFLSPDP
LRRRDGTDVDKERLIEVFSSMGYNVEAYDNVDHMGIIERIRSACDRSLVRDSLVVFILSHGFEEAVYASNSIAMKITDIEDLLCSYDTLYYKPKL
LIIQACQEKLVHKKKPNELFRIDVTTVSPDQHIDMLRAMSTVNGYAALRHTQTGSWFIGSLCDAIDRRSASEHIADILTIVTNEVSKKRGSNDES
MVPNVKSTFRQHVYFPPRL*
(SEQ ID NO: 852)

Name: DreD protein
Classification: endopeptidase
Gene Symbol: Dredd
FlyBase ID: FBgn0020381

Celera Sequence No. : 142000013384651
GTGCTCGACATTTCGCTTGCGTCCCGTAAAGAAATTGTCCACCACGATGACCTCGTGCCCCTGGACCATCAGATCGTCGACCAAGTGGGAGCCCA
CGAAGCCAGCTCCTCCGGTAATTAGTATGCGTTTGCGATTCTTATAGTTCAGGTATTTAACCTTCGGATACTTGCGCGGTGTGCTGGTCTGGAGG
CTACGAACTTGTTCCTCCAATCTGGCCAAATTCTCCCTTGTGCGCTGGAGTTCGGCCTTTTGTTCTCGAATAAGAGAGCTCTGCTCCTCGTACGC
CATCTGAAGGCTCCTTTGTAGCGGACTTTCCGTGGGCGGCCATTTGGCCTGAACCTCCTCGACGCCGGGAACGGAAACGGCGACCTTTCCGCTTG
GGCAGAAGCTGGCCATTCGGTAAAGGTAGACCAGGAGCAGGAGGAGCAGCGAGATGGCTGCAACGATCTTCAGACGCTTTTTGGTGGCAGTCATC
GTCGGTTATGGGTTGTGTACTGCAGGGTTCCAGTGCTTATCAGCAACTGATATCGCCACATTGCATTCTCGTTCGGCTTTAGAAACTATATAAAC
AATACAATTGCGTTATCAGGAGGTGCCAGAGTGGCCAGATGGCTCAAACGGAATTTCTAAATGGATTAATAATCTAACGCCAGGGAAAAGCTCCC
GCCTAATTTTAAAATTTACATCAAAAGTATCGACAGGCGAACATTTTGATTTTGGATTATAAATTATAATGAATTGATAATGAATTAGACATTTT
TGTTGGTGATCTTCCCCAGGGACGAATATTTTTCGTTTTAACGATAAAAGGTCGGAAATTGCCAAAAAATGAGTTTGAAAACTAAATTTGTTTGA
GGGCTTTCTTAGGCTGGTCAGCAGGGACTACTTTCCGAATAAAGTGTTTGCCCAAACGGCTATTGAAGGCTATTTAAACTGCCAACGATGAGCAT
CGATCGCCAGTCGGGCAAAGTTCTTAGTGCCAAGTGTTGTAGTGCTCAGCATGAGGCTTCCTTGGGTGATTTTCTGTACAGTTCTGCTTTTAATT
TTTACGAACAACTCAAATGCAGATATTCCCGGGTGCAACTACTACGACACGGTTGATATCTCATACATTGAAAGGCAAAACGATTCGTATTTATA
TGATGACATCGAAATTCCTGCTAGCTTAACTGGATACTACGAGTTCAGGCAGTTTGGGGACGGTTCGATTACGCCGATTGAAAAGCATTTAAGGG
CCTGTGTTTGCAGCGTGCGGCCCTGTATTCGAATCTGCTGCCCAGCCAAGAACTTTTTGGCCAACGGAAAATGCGATGATGGTCTCAAAGAGGAG
CTCGCCCGGTTCAAACCCTATATATACTTCACATACATGGACCTACAGGCACGAGTACCACTCACCGATATGGCTATTATCAGAGATGAGTTCTT
TGATTGTGATGAAATGATTTACATCAGCGACTTTAACTATTTCTTAGAAGAGGTTAGCATTCAAATCTTCAATAAATGTGGACTTATAGTTTGGT
TCCAGGATGGAAAATTTTGGGTTACCGTTGACCTCTTCATGGAAAAACAGGACTACTGCTTGTACCGGCACAACTTTGATTCGGATTTTCCAAAG
TCCATGTGGATAATACGACACCGCTGCACAAGCCACATATCTCCTGGATCCTTAGAGAGTAATTCAATTATTATTTATAACAAAAGTCATCAATA
TCGTTTTCATAGCTATATAGAAAGAAACGAAAATAACTCCTTATTGGTGTGCAAACTGCTGACTGCATTCTGTGTGCCCTTTGCAAGTTTTTTAA
TTACAATAAGCTGGTTTTTATTTCTTATATTTTCTTTTTCAGTTCTAATTATAACAATGATATGCTTTGTCCTAACAATCGCAGTATATCTATA
CATTAAGAAGCTGCGAAATGTTACTGGCAAGTGCATTGTATGCTGTATAGTTTCGAGGTTTATCCAGTGCTTGATCATGATACTAGATCATTTAA
ATCTATTGAATGGCATTTGCTCTCCAGCTGGTTAGTTCGAATTGGAGATATCTCTGGAAGCTTTAAATGTTATATCGTTGACTTCTTGCAGGTTA
CAGCTCGCACTTTTTCCGGATGGCTTCCAACCTCTGGCTCTCCGTCATCAGCTACCATACGTGGAAAGTCTTGACGTCGCTCAATCGAGTCGACC
CTAACTATCGGTTCCTGCGGTACAACGCCTTCGTCTGGAGCACAGCCGCAATCATGACGGGAAGTATTTATATAGTTAATCAGATTTGGGAAAAC
GATCCCAGTAAATGGAACTGGTTGCCTCTGGTCGGTTTATTCGGTGCTCGGTCAAAGGTAAACTTTCAATGCGATTGCTTTTAAATCGTTACCA
TGGTTACGTATTGCTTTTCCATATCAGATTGGCACCCATCCGTCTGGATCTATATAAGTGGACCGTCGCTGGCCCCTGAGCACTTTCAATGTCGCC
ATGTTCGCCCTGACAGCCATTTACATTAGGAAAGTGAAGGGGGGTATAAATAAGTTCACAAATGAGGAGGAGGGAAGGATTAACTGCATAAACTT TGACAGCCAGACGTAAGATATGATAAAACCTTGGACCTTGGTAAACTAGTTATCCTTGCCGTATTATCCACATAGTTACCTACAGTTCCTGCGGC
TCTCCATCGTGATGGGCCTTACTTGGATATTCAATGTCATTCCGTATTCTGCACGGCTCCACATTTTCTGGGAATGGGTCGGGATAATATCCGAG
TATTTTCACAGCGCGTTTGGAATTGTTTTGTTCGTTCTGCTCGTCCTGAAGCGCAGCACATGGACTCTAATGATGGATTCTTAAGCTTGTTTCTA
TATAATTCTAATAATTGTTTACAATTAAAGCTTTAAACAATTAAAGCCCCTCATTTTATTAATATCCTTTGCTGAACGAAGGAATTGAATTGAAT
TTTATTGAACTCAATAAATAAATATAGTTTTAGAAAACGATGTACTTTAAACTGCCAAGAGGTCACCGCGACAAGCTTTTCACTTCGCCACCCTC
TGGTAACACTGATTCTCCAGCCACTTTCGATTCTTTAAAAAACATCGATAGGTATCGCCAAAAAAATCAGCTGCTCTGCTTGTAGTTTTGCGATT
TCATTGCAATTTTAATTTGCTTTACTGTTCAAAAAGAAATACAGTGCAAAATATGCCGAACGAAAACGCAGAGGACCTCTCGGGTCAAGAGCTAA
AGCAGAAGGCCAAGGAGGTGGCCGACGCATCGGAGGCAATGCTCGAAAAGGTTGTTGCCGGCTTAAATATCCAGGACACGGCATCGACGAATGCA
GCAGGAAACGAGGATGCGGAGCAGCCTGATGGTGCCAAGAATGAGGCTTCAGTGTCTGCGAATGCAAGTAAGTTTTCAATATGCCTGTGAAAAGT
CATTTAGAGGCTCCTCCTGCGGCTGAAAAAATGAGGTTAGGTTTTGTCGGGAACTACAGTCCAACCTCTCTAACTTGAACTGCTGTGCTATTCAT
TTCAATTCAATTTTCAATTTTCATTTTCTGTGCAATTACTCCAAAGATTAGCCCTAACGGAAAAATAAACAACTCATAAATCATAAATACATATT
TGATTTTGATGAAATATGAATATACTTACATAGATACAATTGAGTTTTTTATTACGAATAAAATATGTGTAATATAAGATTTCTACCTTGTTGAT
TCCATTGATTGATGCTTCATTGAAACCCCAAAATTGGGCAAATTTGTTGTCATGGGAAACTAGTCCACTGTCGTGATGCCTTAAGCTTTTTTTGG
GGCAGATTAGTCATTCCAGTTTAAACTAATCGAAAA
(SEQ ID NO: 853)

Exon: 1001..1673
Exon: 1849..2025
Exon: 2087..2338
Exon: 2403..2836
Start ATG: 1001

Transcript No. : CT22963
ATGAGGCTTCCTTGGGTGATTTTCTGTACAGTTCTGCTTTTAATTTTTACGAACAACTCAAATGCAGATATTCCCGGGTGCAACTACTACGACAC
GGTTGATATCTCATACATTGAAAGGCAAAACGATTCGTATTTATATGATGACATCGAAATTCCTGCTAGCTTAACTGGATACTACGAGTTCAGGC
AGTTTGGGGACGGTTCGATTACGCCGATTGAAAAGCATTTAAGGGCCTGTGTTTGCAGCGTGCGGCCCTGTATTCGAATCTGCTGCCCAGCCAAG
AACTTTTTGGCCAACGGAAAATGCGATGATGGTCTCAAAGAGGAGCTCGCCCGGTTCAAACCCTATATATACTTCACATACATGGACCTACAGGC
ACGAGTACCACTCACCGATATGGCTATTATCAGAGATGAGTTCTTTGATTGTGATGAAATGATTTACATCAGCGACTTTAACTATTTCTTAGAAG
AGGTTAGCATTCAAATCTTCAATAAATGTGGACTTATAGTTTGGTTCCAGGATGGAAAATTTTGGGTTACCGTTGACCTCTTCATGGAAAAACAG
GACTACTGCTTGTACCGGCACAACTTTGATTCGGATTTTCCAAAGTCCATGTGGATAATACGACACCGCTGCACAAGCCACATATCTCCTGGATC
CTTAGAGATTCTAATTATAACAATGATATGCTTTGTCCTAACAATCGCAGTATATCTATACATTAAGAAGCTGCGAAATGTTACTGGCAAGTGCA
TTGTATGCTGTATAGTTTCGAGGTTTATCCAGTGCTTGATCATGATACTAGATCATTTAAATCTATTGAATGGCATTTGCTCTCCAGCTGGTTAC
AGCTCGCACTTTTTCCGGATGGCTTCCAACCTCTGGCTCTCCGTCATCAGCTACCATACGTGGAAAGTCTTGACGTCGCTCAATCGAGTCGACCC
TAACTATCGGTTCCTGCGGTACAACGCCTTCGTCTGGAGCACAGCCGCAATCATGACGGGAAGTATTTATATAGTTAATCAGATTTGGGAAAACG
ATCCCAGTAAATGGAACTGGTTGCCTCTGGTCGGTTTTATTCGGTGCTCGGTCAAAGATTGGCACCCATCCGTCTGGATCTATATAAGTGGACCG
TCGCTGGCCCTGAGCACTTTCAATGTCGCCATGTTCGCCCTGACAGCCATTTACATTAGGAAAGTGAAGGGGGGTATAAATAAGTTCACAAATGA
GGAGGAGGGAAGGATTAACTGCATAAACTTTGACAGCCAGACGTAAGATATGATAAAACCTTGGACCTTGGTAAACTAGTTATCCTTGCCGTATT
ATCCACATAGTTACCTACAGTTCCTGCGGCTCTCCATCGTGATGGGCCTTACTTGGATATTCAATGTCATTCCGTATTCTGCACGGCTCCACATT
TTCTGGGAATGGGTCGGGATAATATCCGAGTATTTTCACAGCGCGTTTGGAATTGTTTTGTTCGTTCTGCTCGTCCTGAAGCGCAGCACATGGAC
TCTAATGATGGATTCT
(SEQ ID NO: 854)

Start ATG: 1

MRLPWVIFCTVLLLIFTNNSNADIPGCNYYDTVDISYIERQNDSYLYDDIEIPASLTGYYEFRQFGDGSITPIEKHLRACVCSVRPCIRICCPAK
NFLANGKCDDGLKEELARFKPYIYFTYMDLQARVPLTDMAIIRDEFFDCDEMIYISDFNYFLEEVSIQIFNKCGLIVWFQDGKFWVTVDLFMEKQ
DYCLYRHNFDSDFPKSMWIIRHRCTSHISPGSLEILIITMICFVLTIAVYLYIKKLRNVTGKCIVCCIVSRFIQCLIMILDHLNLLNGICSPAGY
SSHFFRMASNLWLSVISYHTWKVLTSLNRVDPNYRFLRYNAFVWSTAAIMTGSIYIVNQIWENDPSKWNWLPLVGFIRCSVKDWHPSVWIYISGP
SLALSTFNVAMFALTAIYIRKVKGGINKFTNEEEGRINCINFDSQT*
(SEQ ID NO: 855)

Name: mth-like 7
Classification: G_protein_linked_receptor

Celera Sequence No. : 142000013384804
GAACTCTCCCTGCGAATTTCTATGGAATTTCACATGCAGCGGCAACTGCAGCAAACAGAAAACAACAAACGTGAGAGGCAAATAAATAAAAACAC
ATTATGCAGAAAGCAGCACACGTCCCTATCTACAGATGTACAAATGTACATACATACATATGTACATATGTATGTACACACCTACAGCCGTATGC
GTTATAAACAAATTGCAATCAAAAGCCAAGTTTGGGAAACCAAAAGATACACTTTCGGTCGACTCAAAAATGCCCTAGAGAAACCGAAGTTGCGA
CACAAAAAAAAAAAATAGATAGATCCCTTGACAAAATGTATCTTTATCTTTGTATCACAGGTTACGCTTCTTCTCGAATTATTTATATATGTATA
TACATATATACAACACTTGGATATGAATTCATAAAGTCAAATCAAATCATGCTAATTTGTTAATGCGACAAAAGTTCAGTCGCAATATGCGATTG
ATTCGTGACCAGAGAATATATGAATCGATTCAGTAACATAAGCATATTAGTATCATTCCCAAATCGACTCATAGTCATGACCTCCCAGTGTGACT
CCCAGGGTACTTCAGCACAACTTTTGGCTCCCCAAACGGAAGGTTGAGTAACTTTTTTAGCCCTCGGAGAAGGGGTTCACCGACTACAGATCCAG
CCCAAAACAATCGCATGAGCCGTGGATACGGAGATACCTAGATAACTAAGCTACAGATACATTTGCTGACTTTAATTGATGTGACAAGTAACAAG
TGGCGAAACAATGGCCAACCCGAAGACGAAGAGACTGAGAGAACGTATTGTACATGGCAAATTGCAAGTGACAGTGGGGTACCCACTCGAAAAAC
CAACTAAAGTCATTTGCTTGCTTAAAATAATATGAACAAAGAAATCAATCTTTCTCATTCTCTTAATTAAGCTTCATGAAATATAAGTCACGACT
TTAAGCTTGATTCAACGTTGATACGAAATGACTTTCCCACTATTTATAGATTATTTAAAGATCGTTGGCCGGAAATTCCAAAATCGGAATTTGGA
TGTATGAATAATGCCTAGACTAATATATATGTTTTTCAATTCATCTTTCAAGACATTTCCCCACCCACTCACCATGTCCTCCTCGTCCTCGCAGC
AGTTTACATCCTGCAGCGTTTCCCGCCACGCCAGCACGGAGTCCGTGAGCAGCAGCCTCGCATTGGAGCGAACGCGCAGTTTGCGTCCCGTCCTC
GGAGCCACGCCCCTCTTACCGGCCACCGCCCCCGCGGCGAGCACGGCCCGCTCCCACTCCTCCTTCAAGGGCTTCGGAATGGCCGGCGTGGGGTT
GTGCTGGTGGTTATACGAATCCTCCGCCTCGCAACTGCAGCCACTATCATCGCTGCGTGGTGCCAGACTCGTGGTGTTTGAGGTGGCCAGTTGGG CGGGTGGCGGTGGTGCTGGTCGGCGGATCCGGGTCATGAACCGCTGGTGGACCAGCGAAAGATGGTAGTCGTAGAATATAGCGCTGTACTTCTTC
GGATCTTTTTGGCTGTAGAAAATGCAAATGTTCCTTAGGATCGGATGCACCACGACTGATGGCTGCTGATCCGCTGGCAGATCCTTTGGCGTATC
CTTTGGCTGCCCGGTGACGCTGCTGCCAGTGCTGCTGATGGAGCCCAGGGTCGCTGTGCTGTTCGTCACCGTACTGCCCAGGCTTAGCGTTTCAT
CCGCCTCCTCCTTACTCTCCCGCGAGTACATGAACTCCATATCCGTCTCCCACGCTCCATGGTCCATGGAGGCGGTGGGCGAGGGCAGGGGCGTC
GGCATCATCATCTTGGAACGCTTGGTCAGCGTCGATGTGGACAACTTATGGCGCACTCCGGCGGCAAAGACCGCCGCCGCTTGGAGAGCCATCAC
ATCCGGATCAGCATCGGATGGCAGCGACTCGTCGTAGTCCCCCAGATCCTCCTCCTCATCATCCACGTCGTCGTCTTCCTCGTCTTCGTCCTCCT
CATCTTCGCCCTCGACGGGAAGGGCTTCGATTATCTCCTGATCTACGGGTTCGATTGTCTTGAACTGCCAAATGGGTTGGTAAATGGACTCCTCC
TCCTGCTCCTCTGGGCTGGAATTCTCCGCGGCAAAGGAGTTGCCTCTCAGGTTATCCTTTTTCCCTCCGTTCGGCTTCGTCTGCTCCTCTTCAAT
CTGGCGGGGATTGCTCAAAGATGTGTTGGGATTTCGAACGGGTACCTTTGGCGCCGGTCGTCGAACTTTAATAACGCAATTCTAAAAGTTGAGGT
GGAAACATACTATATTGTCAAAACAAAAAATAATATCCTGTTTCGACTGTTGTGTTTTACTCGCTGCAATAATTGACGAACGGTGGGATATCGTT
TTGATTTCATTTCGTTTCAATTATAATAAAAACATTTAAGGAAACCCCATCTTTGAATAAAGTTACGAATTTAGGGTTACTTCTCACAAACTGAT
AAACATAGTTAATTAGTTAGGTAATTACGTAAAATAACAAAAGTGGAGGCGGATTTCCCGATCAGCTTTTAATGGAAATTATCATTAATATGCCG
CCTGCGAAAACAATGAATTACTCCATTAATAACTTCTTTGCTAGGAATCACAATATTGAACTTTTTTGTGCAGTTGTGATGGCAACTTTACTGCT
TTTTACGCAAATTTTGCAATCAGTAAAAAAAAAATATTCAAAAAAATAGTGTGAAAAATGACGTTAATTAAACGCTGATTATTTTATAGTTATCT
TGTGCTTTCATTGCAAACTTGTTTGTTTTACTTCACATTTTTTTCATTGTTCAATGGTTGTTTTTAATTAGATAAGTTTGTTTATTTATTTATTT
TTTTTTTTCGTTTCGCTGGCCAATCGAATGTTGGCATCCCTTTCGCACGTGAACCGTTAGTCAATTTTGAACTGCAGTGAAACGTAACAGAATCA
AGTACACAGAGAGAAAAGTATAATTGCATCACAATATTAACGTATTGCCCTCAAACTGTTTTTCATATATAAGAACAGAAAAAAAAGTAGGGATC
AATTTTAATCGTTCCTGATTGATGTTGAACTGATTTGACGGATCGCAATTGGGAATTATAAATTTTATATTTATTTACATGCACTATTTGTATTA
CTTTGATTTACGGAAATCAAACCAATTATAGTTAATAAAAAAATTGGTAAAATTCAACCGTGTCAATTGAATTTTTAAATAATATATTTTTTTTT
TGTGGCGCTCGTTGATACCGCCCAAACTTTTTCTCTCTGTGCATTTTAATTTTGCCTTTGATTGATGCGGCTTTTGTTTTTGCTTTTTATTAATG
AGTGTTGACCTGTGTGATTGGCTGCTGTTGTTGTTGTTGCTGTTGTTCATTGACATTGCAATTGGCGTTGCCGTCGTTATTCTTGTTGTTGTTGA
TACCGCTTTCATTGTCAACGGTGTGATGGTTGTTGTTGTTATTGCTGATGTTGTCATTGTTGTTGTTGCTGCTGCAGTTGATGGTGTTGTTGTTG
CTGTTTGTTGAGGGGCGCTCTGCCTCGCCATTTGGCTTAGGCGCTGCCATCAAAGCTCCGCTGTTGTTGTTACTGTTATTATTATTGTTTTTCTT
GCTGTTGTTACTGCTAGTGGAGCTCTCGCCCCCGCACACACCCTCTTCCCTGACTATCGCTGTCCCTCTTCGCCTCGTACTTCGATTCGCGCGGC
GTCGCGACGCAGCAGCAGCACACACGTCTACGCTCTCTGAAATCGCTGGCGAAACTGAAACCGAAGCCGAGGCCACCGAACGATCGTTGCCGCCG
GCGAAGGAGAAGGCGAAGAGAGGCAGGCGCCGTCGCCAATCCCCCACAACGCCAACAACTGAGTCACGCGCTCTCCTTCGCCGATAACCGTTGAT
CGGTGGTTGTTGTCGCTGTTGTTGTTGCTGGTGCCACAGCCACAAGCTGAACGATTTGTCATAGGCGGTGAGAAAGCCACGCACACTCACGTGCA
AGCTGGCCGAAAGAGCGAGACTCTGCATCAAGCGCAAGAGAGATACAGAGACTTGAGGCTGAATTGCGATTGCGACGACTGCGACGTGCTCTTCG
ATTGCGGCCACCTGTTGATGTTGCACTGCCTCTTTCTCTTCGCCCAGTGCGCTCAGATAGTCATTCACAAAGTTGGCCGTGATGGCGCAGCGCCG
TTGCTCTCTTTCCGGCTCCACGTTGTGCGCTCTCTTCTGCTGCAGCTTTCGTTTAAAGTCCTTGACCAACTTCGCCTGCTCGTCCGCACACTTTG
CACTCTCCTCCGTGCTTCTCCGCAGTGTGACCGTGCTCTCCTCGGCGGAGGATGAAGGATCGCGCGCTGGTACGCTCTTTGGCTGCTGCCACGGC
CCCTCGTCGTAGTGGTGCACCTGCCGCCTCAGGGAGGTCATCCACTGGCAGATGCTCTCGTTGAGATACAATGATGAGGATCCTGATGTGCTTTC
GTCCTGCAGCAGGCGAATGCGAGAGACGCGCGGCCTCTTGCGCTCTCTCTTGTGGCTCTGGCTCTCTTCGGGCTCTCTTACGCGGCCGTAGATGT
GCTGATCGCTTTGGCTGCCCTTCAGTTGCTGCTGCTCTAGCTTGAGTTCGCAAATGCGCTGGAGGTCAAAGGTCTCCTGGGTGCGGAACACCTCG
TCCACGTTGTGGATGATCTCCAGGGAGCCAGCGCTGCTACTGCCAGTCGTGGGTGTCCTCGGGAATATCCTGCGCTGCAGCGACGACGAACGGTT
CAGCTGCTTAAGAGAGCCAAAGAGACGGGTCAAGGTCGCCGCACTGGACTTGGAGTAGCCCAAGAGCGACCGCGACTTGACCTTGGTGGGTGGTG
TGGGCGGTGTGGTTGGTGTGGACGGTGCGGGCGCTTTGGCTGGCGTCTCTGACCTTTGACACCGGCACCGCTCGTTGTCGCTATAAATGCCGCGG
CACAAATCGCAGATGTTCTCATAGATGTTGCTGCTCTCGCCGGAAATCGTCGAAAGGGGCGGTGGCGGTGGGGGAGGCGGTGTACTCACCACGCC
CCCGCTCACGATGCACTGGCAGAAATGGCAGTAGCGTCCTTGGGCGGCAAACACGCCGTAGCCGCAACCCCGACAAAGATTCTCGTAGATCGCCT
CGCGCGGAAAATACTTGCGCAGCTCCGCATTCAGGTGACCTTTGGGGGTGGAGGTCAGGCCCGGCAGATTCTCGTAGATGTGCGCCTCCATGCCG
ACGTTATCGTTAATGTCCTTCGCCTGCTGTGGCATCTCTCTTCTTTATTTCTTCTTCTGCCTCCCTACTTTCTCTTATCGCCGCTGCGTCACATC
GTAATTCATTATTAAGTGAGAAAATAATCGCCGAGCGGGGCAATTGGAGAGATAGTAAGTGAGAGCACTGTCATCGAGAGAATTTCGTGCACCGC
AAAAGAAATGTCGCGAAGGTATTTAATTAACATAAATTCGATTTGGAAATGCTCGAATGGCTCTTCTTAAATTTCTCACTCGAGTGAATTGAATA
ACTTGTAATCTTCGATTACTCACTATTATTTTTTGAGAAACACCCCAAAAACGACCTTAGTTCTCGCAGTGTAATCACTGAGAAAAGTCAATGGG
CTTGAACTCTTTAAGTGATGCCACTACCCTCATTTTCTTTCTTTCTGTCTCTTTCCCTCCCGCTTCCGACTGCAATCAGCGATATTCATTATCTC
AGCCAAAGTCGCTGCACTCTGCACTCAGTTTTCCTCCAAACCATCGGCTTTGCCTTCAAAACACAATTCTTTGGCTTGACTTTTTTTAAATCTGG
GAATTTAAAGGATGAATTTTTCGAATCTAATTGCAAACAGCTTTTAATAATATGACCCTGTTATCGTGAATTTCTTTACCATTTCTTCTAATATT
TACATATATTAGCTATTTTGATAAAATATTATTGGAACCCATTGCTGTATTCAATATATGTGTAACTAGACCCAATATCTCTGTATATTTCACGC
CCAAAAAGATCCAGAGCACTTATCACTAATCAGTTTAGAGCTCTAAAATGAATTGTTTGTTTGCCCTAAAACATTTGATGCTTAAATGCAAATAA
TGTTTAAAGTAAAAAAAACCCCAATGCATTTCATCTGACTAGAATTCCACAGTGCTGCTTCTGCTTTTGAGCTTTGTTTTTCGTTGATATACGGA
GATGAGTCACTAACCGATCCACCAAACCATGTCGGTCCTCTCGTAACCCCCGTCCTTATCCCTCGGACTCAAAATGATGGCCATG
(SEQ ID NO: 856)

Exon: 5260..3335
Exon: 2266..1001
Start ATG: 5260 (Reverse strand: CAT)

Transcript No. : CT23013
ATGCCACAGCAGGCGAAGGACATTAACGATAACGTCGGCATGGAGGCGCACATCTACGAGAATCTGCCGGGCCTGACCTCCACCCCCAAAGGTCA
CCTGAATGCGGAGCTGCGCAAGTATTTTCCGCGCGAGGCGATCTACGAGAATCTTTGTCGGGGTTGCGGCTACGGCGTGTTTGCCGCCCAAGGAC
GCTACTGCCATTTCTGCCAGTGCATCGTGAGCGGGGGCGTGGTGAGTACACCGCCTCCCCCACCGCCACCGCCCCTTTCGACGATTTCCGGCGAG
AGCAGCAACATCTATGAGAACATCTGCGATTTGTGCCGCGGCATTTATAGCGACAACGAGCGGTGCCGGTGTCAAAGGTCAGAGACGCCAGCCAA
AGCGCCCGCACCGTCCACACCAACCACACCGCCCACACCACCCACCAAGGTCAAGTCGCGGTCGCTCTTGGGCTACTCCAAGTCCAGTGCGGCGA
CCTTGACCCGTCTCTTTGGCTCTCTTAAGCAGCTGAACCGTTCGTCGTCGCTGCAGCGCAGGATATTCCCGAGGACACCCACGACTGGCAGTAGC
AGCGCTGGCTCCCTGGAGATCATCCACAACGTGGACGAGGTGTTCCGCACCCAGGAGACCTTTGACCTCCAGCGCATTTGCGAACTCAAGCTAGA
GCAGCAGCAACTGAAGGGCAGCCAAAGCGATCAGCACATCTACGGCCGCGTAAGAGAGCCCGAAGAGAGCCAGAGCCACAAGAGAGAGCGCAAGA
GGCCGCGCGTCTCTCGCATTCGCCTGCTGCAGGACGAAAGCACATCAGGATCCTCATCATTGTATCTCAACGAGAGCATCTGCCAGTGGATGACC
TCCCTGAGGCGGCAGGTGCACCACTACGACGAGGGGCCGTGGCAGCAGCCAAAGAGCGTACCAGCGCGCGATCCTTCATCCTCCGCCGAGGAGAG
CACGGTCACACTGCGGAGAAGCACGGAGGAGAGTGCAAAGTGTGCGGACGAGCAGGCGAAGTTGGTCAAGGACTTTAAACGAAAGCTGCAGCAGA
AGAGAGCGCACAACGTGGAGCCGGAAAGAGAGCAACGGCGCTGCGCCATCACGGCCAACTTTGTGAATGACTATCTGAGCGCACTGGGCGAAGAG
AAAGAGGCAGTGCAACATCAACAGGTGGCCGCAATCGAAGAGCACGTCGCAGTCGTCGCAATCGCAATTCAGCCTCAAGTCTCTGTATCTCTCTT GCGCTTGATGCAGAGTCTCGCTCTTTCGGCCAGCTTGCACGTGAGTGTGCGTGGCTTTCTCACCGCCTATGACAAATCGTTCAGCTTGTGGCTGT
GGCACCAGCAACAACAACAGCGACAACAACCACCGATCAACGGTTATCGGCGAAGGAGAGCGCGTGACTCAGTTGTTGGCGTTGTGGGGATTGG
CGACGGCGCCTGCCTCTCTTCGCCTTCTCCTTCGCCGGCGGCAACGATCGTTCGGTGGCCTCGGCTTCGGTTTCAGTTTCGCCAGCGATTTCAGA
GAGCGTAGACGTGTGTGCTGCTGCTGCGTCGCGACGCCGCGCGAATCGAAGTACGAGGCGAAGAGGGACAGCGATAGTCAGGGAAGAGGGTGTGT
GCGGGGGCGAGAGCTCCACTAGCAGTAACAACAGCAAGAAAAACAATAATAATAACAGTAACAACAACAGCGGAGCTTTGATGGCAGCGCCTAAG
CCAAATGGCGAGGCAGAGCGCCCCTCAACAAACAGCAACAACAACACCATCAACTGCAGCAGCAACAACAACAATGACAACATCAGCAATAACAA
CAACAACCATCACACCGTTGACAATGAAAGCGGTATCAACAACAACAAGAATAACGACGGCAACGCCAATTGCAATGTCAATGAACAACAGCAAC
AACAACAACAGCAGCCAATCACACAGAATTGCGTTATTAAAGTTCGACGACCGGCGCCAAAGGTACCCGTTCGAAATCCCAACACATCTTTGAGC
AATCCCCGCCAGATTGAAGAGGAGCAGACGAAGCCGAACGGAGGGAAAAAGGATAACCTGAGAGGCAACTCCTTTGCCGCGGAGAATTCCAGCCC
AGAGGAGCAGGAGGAGGAGTCCATTTACCAACCCATTTGGCAGTTCAAGACAATCGAACCCGTAGATCAGGAGATAATCGAAGCCCTTCCCGTCG
AGGGCGAAGATGAGGAGGACGAAGACGAGGAAGACGACGACGTGGATGATGAGGAGGAGGATCTGGGGGACTACGACGAGTCGCTGCCATCCGAT
GCTGATCCGGATGTGATGGCTCTCCAAGCGGCGGCGGTCTTTGCCGCCGGAGTGCGCCATAAGTTGTCCACATCGACGCTGACCAAGCGTTCCAA
GATGATGATGCCGACGCCCCTGCCCTCGCCCACCGCCTCCATGGACCATGGAGCGTGGGAGACGGATATGGAGTTCATGTACTCGCGGGAGAGTA
AGGAGGAGGCGGATGAAACGCTAAGCCTGGGCAGTACGGTGACGAACAGCACAGCGACCCTGGGCTCCATCAGCAGCACTGGCAGCAGCGTCACC
GGGCAGCCAAAGGATACGCCAAAGGATCTGCCAGCGGATCAGCAGCCATCAGTCGTGGTGCATCCGATCCTAAGGAACATTTGCATTTTCTACAG
CCAAAAAGATCCGAAGAAGTACAGCGCTATATTCTACGACTACCATCTTTCGCTGGTCCACCAGCGGTTCATGACCCGGATCCGCCGACCAGCAC
CACCGCCACCCGCCCAACTGGCCACCTCAAACACCACGAGTCTGGCACCACGCAGCGATGATAGTGGCTGCAGTTGCGAGGCGGAGGATTCGTAT
AACCACCAGCACAACCCCACGCCGGCCATTCCGAAGCCCTTGAAGGAGGAGTGGGAGCGGGCCGTGCTCGCCGCGGGGGCGGTGGCCGGTAAGAG
GGGCGTGGCTCCGAGGACGGGACGCAAACTGCGCGTTCGCTCCAATGCGAGGCTGCTGCTCACGGACTCCGTGCTGGCGTGGCGGGAAACGCTGC
AGGATGTAAACTGCTGCGAGGACGAGGAGGACATGGTGAGTGGGTGGGGAAATGTCTTGAAAGATGAATTGAAAAACATATATATTAGTCTAGGC
ATTATTCATACATCCAAATTCCGATTTTGGAATTTCCGGCCAACGATCTTTAAATAA
(SEQ ID NO: 857)

Start ATG: 1 (Reverse strand: CAT)

MPQQAKDINDNVGMEAHIYENLPGLTSTPKGHLNAELRKYFPREAIYENLCRGCGYGVFAAQGRYCHFCQCIVSGGVVSTPPPPPPPPLSTISGE
SSNIYENICDLCRGIYSDNERCRCQRSETPAKAPAPSTPTTPPTPPTKVKSRSLLGYSKSSAATLTRLFGSLKQLNRSSSLQRRIFPRTPTTGSS
SAGSLEIIHNVDEVFRTQETFDLQRICELKLEQQQLKGSQSDQHIYGRVREPEESQSHKRERKRPRVSRIRLLQDESTSGSSSLYLNESICQWMT
SLRRQVHHYDEGPWQQPKSVPARDPSSSAEESTVTLRRSTEESAKCADEQAKLVKDFKRKLQQKRAHNVEPEREQRRCAITANFVNDYLSALGEE
KEAVQHQQVAAIEEHVAVVAIAIQPQVSVSLLRLMQSLALSASLHVSVRGFLTAYDKSFSLWLWHQQQQQRQQPPINGYRRRRARDSVVGVVGDW
RRRLPLFAFSFAGGNDRSVASASVSVSPAISESVDVCAAAASRRRANRSTRRRGTAIVREEGVCGGESSTSSNNSKKNNNNNSNNNSGALMAAPK
PNGEAERPSTNSNNNTINCSSNNNNDNISNNNNNHHTVDNESGINNNKNNDGNANCNVNEQQQQQQQQPITQNCVIKVRRPAPKVPVRNPNTSLS
NPRQIEEEQTKPNGGKKDNLRGNSFAAENSSPEEQEEESIYQPIWQFKTIEPVDQEIIEALPVEGEDEEDEDEEDDDVDDEEEDLGDYDESLPSD
ADPDVMALQAAAVFAAGVRHKLSTSTLTKRSKMMMPTPLPSPTASMDHGAWETDMEFMYSRESKEEADETLSLGSTVTNSTATLGSISSTGSSVT
GQPKDTPKDLPADQQPSVVVHPILRNICIFYSQKDPKKYSAIFYDYHLSLVHQRFMTRIRRPAPPPPAQLATSNTTSLAPRSDDSGCSCEAEDSY
NHQHNPTPAIPKPLKEEWERAVLAAGAVAGKRGVAPRTGRKLRVRSNARLLLTDSVLAWRETLQDVNCCEDEEDMVSGWGNVLKDELKNIYISLG
IIHTSKFRFWNFRPTIFK*
(SEQ ID NO: 858)

Celera Sequence No. : 142000013384502
GCTCCGTCCTTGCCTACCAGTGAGGTCACATATTTATCTAGCTGGACAATGGTGAACTCCTCTAATTCTCCATTGTGCTGCATCACGTTCAGCTG
ACTGGCCAGCATCGCATAGCTGTTAAAGTACTTGCCGTCGGAGATTAGGATGCGATAGCGCTCTGAGTCCGCTGCGCTGTTAATCTTCTTGATTG
CCAGGATCTGGAGAACCGGGGCATCCACAACCTCGCCATGCATAATGCGCTGTGGCCGGTAGTACGATGTGTTACTATACCAATCCATTATTTTA
AGCTGGCATACTTACAGCAATCACACCAGTGGACAAAGATGCCAGGACCATTTTGATTATAAAAATAAGTTGGGCAATTTCACAAGCAAATATAA
TTCATGCGTCGAGGGCTGGGTACAAAGTGAAGCTAGAAGAGGCGGGAAGGGCTTCTGTGTAATTTTGAATCAGTTGTTGCGGAACTAGTTCAATT
TGCTTTCCAGTTAGAGCTGTATTTCAGGGCAGTAAAGTTTTGGTTGCTTAAGAGAAAACATTTATTTTACTTTATTATTACTATTTCCTACAGCA
ACATATTGAGAATAATTGTCTATTATTTTGACACATAGCTTTAAGCTTGACTTACATTGTTTGTGTTAATGCTCACAACTAGTTATTGTAAGCAT
TTCTATTTCAATGGAATTATAAATATTTAATAACTGTGTGATATTTTATTGACACATTCTTTGTATTAAAGCCTACATTCAGTGCCTTGTAAACT
TTTTAAATTGAATGGTGTAATATATATATTTAAAATTTTTTGTAAGCTCTTTAAACTCGGTGATATTTTATTGACACAAGGAAAGTTGTTACAGT
CGGGTGTTCTTATAAACATGTATGCAGAAGCGGGTGTCCACTGTATGACCCAGACGTTAACAGCACTGCTTATCGGAACTAGACCGCAGCCCTGA
GTTGGCTCGATTAGCAAACATTTTCCCGCGCATTTTCGCACGCGTCGTCACAACAAGATCGGCGGTACAAAACAAAACATATTACAGATAAACGC
TAAGCACAACAGACGCACGTAATGGACAATCCCAGTTCACCACCGCCAAATACGCCCAGCGATGCCGCCGAACGCCGCGATCTGCGGGCAGCAAT
GACGTCGCCGGTTGGCGACTTTGAGCCGTTCGAGAACGAGGACGAGATCCTGGGAGATCAGACCGTTCGCGATGAGGCCGAGGAGGAGGATGGCG
AGGAGCTGTTCGGGGACAACATGGAGAACGATTACCGGCCCATGCCTGAGCTGGATCACTACGATCCGGCGCTGCTGGACGACGAGGATGACTTC
TCGGAGATGTCCCAGGGCGATCGCTTTGCCGCCGAGTCGGAGATGCGTCGACGCGACCGGGCCGCCGGAATCCACCGCGACGATCGTGATCTGGG
TTTCGGTCAGTCCGATGATGAGGACGACGTTGGACCCCGGGCCAAGAGACGAGCTGGCGAGAAGGCAGCTGTTGGCGAGGTAGAGGACACCGAGA
TGGTGGAGTCTATTGAAAACCTGGAGGATACCAAGGGACACTCAACTAAAGAGTGGGTCAGTATGCTAGGACCACGCACGGAAATCGCCAATCGC
TTTCAATCCTTTTTGAGAACTTTTGTGGATGAAAGGGGCGCATACACCTATCGTGATCGCATACGTCGGATGTGCGAGCAGAACATGTCTTCGTT
CGTCGTCTCCTACACTGATCTGGCCAACAAGGAACACGTATTGGCCTATTTCCTGCCCGAGGCTCCCTTTCAAATGCTCGAGATTTTCGATAAAG
TGGCTAAGGACATGGTGCTCTCCATTTTCCCCACTTACGAACGTGTCACCACAGAGATTCACGTGCGCATCTCGGAGCTGCCGCTGATCGAGGAG
CTGCGCACATTCAGAAAACTGCATCTGAACCAGTTGGTTCGCACTTTGGGCGTGGTAACTGCCACCACCGGAGTTCTTCCCCAGCTATCCGTGAT
CAAGTACGACTGCGTTAAGTGCGGCTATGTGCTGGGTCCCTTCGTTCAGTCGCAAAATACGGAGATAAAGCCCGGTTCCTGCCCAGAGTGCCAGA
GCACTGGACCCTTCTCAATCAACATGGAGCAGACGTTGTATCGAAATTATCAAAAGATCACGTTGCAGGAGTCGCCAGGCAGGATTCCAGCCGGA
CGCATTCCTCGCAGCAAGGATGTCATTTTGCTCGCTGATTTGTGTGATCAATGCAAGCCTGGAGATGAACTTGAGGTCACAGGTATATATACCAA
TAACTACGATGGCTCCTTGAACACCGACCAAGGATTTCCCGTGTTTGCCACCGTGATTATTGCCAATCATGTGGTTGTAAAGGACTCCAAGCAGG
TAGTGCAGTCGCTTACGGACGAGGACATTGCCACCATTCAGAAGTTGAGCAAGGATCCGCGTATCGTAGAGCGTGTAGTAGCATCCATGGCGCCT
TCTATATACGGACATGATTATATCAAGAGGGCGCTGGCCTTAGCTCTCTTTGGGGGTGAGTCAAAGAATCCCGGTGAGAAACACAAGGTTAGAGG
TGATATAAACCTACTCATCTGTGGAGATCCCGGAACGGCAAAGTCGCAGTTCCTCAAGTACACCGAAAAGGTTGCGCCACGTGCGGTTTTCACGA
CTGGGCAGGGAGCCAGTGCCGTGGGTCTCACGGCTTATGTGCGCCGCAATCCAGTATCTCGGGAGTGGACATTGGAAGCGGGTGCTCTGGTTCTG GCTGATCAGGGAGTTTGTCTAATCGACGAGTTCGACAAAATGAACGACCAGGATCGTACCTCTATTCACGAAGCCATGGAGCAGCAGTCTATTTC
GATTTCCAAGGCTGGTATTGTCACCTCTCTTCAAGCTCGTTGCACCGTGATTGCTGCTGCCAATCCCATTGGCGGTCGCTATGATCCGTCGATGA
CCTTCTCGGAGAACGTGAATCTCTCGGAGCCCATCCTGTCCCGTTTCGATGTGCTGTGCGTGGTGAAGGACGAATTTGACCCCATGCAGGATCAG
CAGCTCGCCAAATTCGTGGTACACTCGCATATGAAGCATCACCCGAGTGAGGAGGAGCAGCCGGAGTTGGAGGAACCACAGCTGAAGACCGTTGA
TGAGATCCCGCAGGACTTGTTGCGACAATACATTGTATACGCTAAGGAGAACATTCGGCCCAAGCTAACGGTAAGCGAACTTATTGAAATCACAG
GAAAAGTGTAACAACATTTCCGTTTCATACAGAACATCGACGAGGACAAGATCGCCAAGATGTACGCCCAGCTGCGACAGGAGTCTTTTGCCACG
GGCTCACTGCCCATTACGGTGCGTCACATTGAGAGTGTCATCCGAATGTCCGAAGCGCACGCGCGGATGCATCTGCGCGAAAACGTAATGGAGGC
AGATGTCAGCATGGCCATCCGCATGATGTTGGAGAGCTTTATCGAGGCGCAGAAGTTCAGCGTTATGAAGAAGATGCGCAGCACATTCCAGAAGT
ACCTGTCCTTCCAAAAGGACCATTCCGAGCTGCTGTTCTTTATTCTGCGACAGCTGACGCTCGACCAGCTCGCCTACATTCGCTGCAAGGACGGG
CCTGGCGCCACACATGTGGAGATTATGGAGCGGGATTTGATCGAACGGGCTAAGCAGCTGGATATTGTAAACCTGAAGCCGTTCTACGAATCAGA
TCTGTTTCGCACAAATGGCTTCTCTTACGATCCCAAGCGACGCATCATCCTTCAAATTGTGGTCGACGGCAACACAGCTTAAGTTTCAGCCATTT
ACTTCATCTCATTTAGTTATAGTATTCATGTTTTGTTACCCCCATTTTCGGTCTAATAAAGTTTGATATACTTATGTATGTATTTATACTAAAAT
AGGTATTTGAATTGAAATTTATACTTCCGTAAATATTTTTTATTGTGCATACAAATCAGCCCCAGAGTATGTCAATCGTTGTTCCCTTCGATGCC
CATGGCTTTGTCGAAATCTTCCTCGCTAATCTTGTTCTTTTTCAGCCGCTTGAAGAGCCGAATATCGCTGGCCAGTTCATCGAGGTCCTCCTGGC
TGAACTGCTGCCTCTTTTTTCCCTTCCCGGACCTGCTCGCCTCCGCCTCTGCCGCTTTCTTTCGCTGCTTCTTCGCCTTGCGCAGCTCCTTCTTA
GACTTGGCATCCAGTTTTGCCTTCTTTGTCTGATCCCAGGACTCAACACGCTTTTTGTGCTGCTTTTGGCCCGGCCAGCTTCCCGTTTGCTCGTA
AGTTTCCATTTTCTTTTGCCGGACTTGTTCTTTCTGGGCGTTTTTGTAGGTAAGTTTGGATAAATCCACTTCAAAAGCAGGCGCCACATAGCCGC
CGCCCTGGTAGTTCTTTAGCTCCGGCATGCGTGGCAGTTGCAGGAGACCGTAAGCAGTGGCCATCTTGCCCAGGTCCAGATCCTTTAGTCGCAGA
ATAGCGCTGCATTCGTGTTTGGTGTATGCTCTAACATGGGAAACAAAAGCGCGCATGCCTTTGTCATAGACGCCCTTGTCGGCCGCCTGCAGCCG
ATGGAGTTGATCTAAGACGGCTGGTAGCTTCTTTTTTTCACGATCTGCATCCTCAGCCTCCTCGGTTAGCAGTTTAGTTAGCTCCACTTTCTGGT
TGATCTTCAGGAAGTGCACATAGGCATCCTCGCTGGGCAGGAGAAACACCAGAGCGTTGCCCTCGTTTCCCTGCCGAGCCGTGCGACCTACACGG
TGTACAAAGCTGGAGGCAGTTGATGGTGGATCCCACTGCACTACCCACTCGATCTCAGGTACATCCAAACCACGTGCGAGGACATCTGTGCAGAG
G
(SEQ ID NO: 859)

Exon: 1001..3205
Exon: 3263..3846
Start ATG: 1067

Transcript No. : CT23073
CAACAAGATCGGCGGTACAAAACAAAACATATTACAGATAAACGCTAAGCACAACAGACGCACGTAATGGACAATCCCAGTTCACCACCGCCAAA
TACGCCCAGCGATGCCGCCGAACGCCGCGATCTGCGGGCAGCAATGACGTCGCCGGTTGGCGACTTTGAGCCGTTCGAGAACGAGGACGAGATCC
TGGGAGATCAGACCGTTCGCGATGAGGCCGAGGAGGAGGATGGCGAGGAGCTGTTCGGGGACAACATGGAGAACGATTACCGGCCCATGCCTGAG
CTGGATCACTACGATCCGGCGCTGCTGGACGACGAGGATGACTTCTCGGAGATGTCCCAGGGCGATCGCTTTGCCGCCGAGTCGGAGATGCGTCG
ACGCGACCGGGCCGCCGGAATCCACCGCGACGATCGTGATCTGGGTTTCGGTCAGTCCGATGATGAGGACGACGTTGGACCCCGGGCCAAGAGAC
GAGCTGGCGAGAAGGCAGCTGTTGGCGAGGTAGAGGACACCGAGATGGTGGAGTCTATTGAAAACCTGGAGGATACCAAGGGACACTCAACTAAA
GAGTGGGTCAGTATGCTAGGACCACGCACGGAAATCGCCAATCGCTTTCAATCCTTTTTGAGAACTTTTGTGGATGAAAGGGGCGCATACACCTA
TCGTGATCGCATACGTCGGATGTGCGAGCAGAACATGTCTTCGTTCGTCGTCTCCTACACTGATCTGGCCAACAAGGAACACGTATTGGCCTATT
TCCTGCCCGAGGCTCCCTTTCAAATGCTCGAGATTTTCGATAAAGTGGCTAAGGACATGGTGCTCTCCATTTTCCCCACTTACGAACGTGTCACC
ACAGAGATTCACGTGCGCATCTCGGAGCTGCCGCTGATCGAGGAGCTGCGCACATTCAGAAAACTGCATCTGAACCAGTTGGTTCGCACTTTGGG
CGTGGTAACTGCCACCACCGGAGTTCTTCCCCAGCTATCCGTGATCAAGTACGACTGCGTTAAGTGCGGCTATGTGCTGGGTCCCTTCGTTCAGT
CGCAAAATACGGAGATAAAGCCCGGTTCCTGCCCAGAGTGCCAGAGCACTGGACCCTTCTCAATCAACATGGAGCAGACGTTGTATCGAAATTAT
CAAAAGATCACGTTGCAGGAGTCGCCAGGCAGGATTCCAGCCGGACGCATTCCTCGCAGCAAGGATGTCATTTTGCTCGCTGATTTGTGTGATCA
ATGCAAGCCTGGAGATGAACTTGAGGTCACAGGTATATATACCAATAACTACGATGGCTCCTTGAACACCGACCAAGGATTTCCCGTGTTTGCCA
CCGTGATTATTGCCAATCATGTGGTTGTAAAGGACTCCAAGCAGGTAGTGCAGTCGCTTACGGACGAGGACATTGCCACCATTCAGAAGTTGAGC
AAGGATCCGCGTATCGTAGAGCGTGTAGTAGCATCCATGGCGCCTTCTATATACGGACATGATTATATCAAGAGGGCGCTGGCCTTAGCTCTCTT
TGGGGGTGAGTCAAAGAATCCCGGTGAGAAACACAAGGTTAGAGGTGATATAAACCTACTCATCTGTGGAGATCCCGGAACGGCAAAGTCGCAGT
TCCTCAAGTACACCGAAAAGGTTGCGCCACGTGCGGTTTTCACGACTGGGCAGGGAGCCAGTGCCGTGGGTCTCACGGCTTATGTGCGCCGCAAT
CCAGTATCTCGGGAGTGGACATTGGAAGCGGGTGCTCTGGTTCTGGCTGATCAGGGAGTTTGTCTAATCGACGAGTTCGACAAAATGAACGACCA
GGATCGTACCTCTATTCACGAAGCCATGGAGCAGCAGTCTATTTCGATTTCCAAGGCTGGTATTGTCACCTCTCTTCAAGCTCGTTGCACCGTGA
TTGCTGCTGCCAATCCCATTGGCGGTCGCTATGATCCGTCGATGACCTTCTCGGAGAACGTGAATCTCTCGGAGCCCATCCTGTCCCGTTTCGAT
GTGCTGTGCGTGGTGAAGGACGAATTTGACCCCATGCAGGATCAGCAGCTCGCCAAATTCGTGGTACACTCGCATATGAAGCATCACCCGAGTGA
GGAGGAGCAGCCGGAGTTGGAGGAACCACAGCTGAAGACCGTTGATGAGATCCCGCAGGACTTGTTGCGACAATACATTGTATACGCTAAGGAGA
ACATTCGGCCCAAGCTAACGAACATCGACGAGGACAAGATCGCCAAGATGTACGCCCAGCTGCGACAGGAGTCTTTTGCCACGGGCTCACTGCCC
ATTACGGTGCGTCACATTGAGAGTGTCATCCGAATGTCCGAAGCGCACGCGCGGATGCATCTGCGCGAAAACGTAATGGAGGCAGATGTCAGCAT
GGCCATCCGCATGATGTTGGAGAGCTTTATCGAGGCGCAGAAGTTCAGCGTTATGAAGAAGATGCGCAGCACATTCCAGAAGTACCTGTCCTTCC
AAAAGGACCATTCCGAGCTGCTGTTCTTTATTCTGCGACAGCTGACGCTCGACCAGCTCGCCTACATTCGCTGCAAGGACGGGCCTGGCGCCACA
CATGTGGAGATTATGGAGCGGGATTTGATCGAACGGGCTAAGCAGCTGGATATTGTAAACCTGAAGCCGTTCTACGAATCAGATCTGTTTCGCAC
AAATGGCTTCTCTTACGATCCCAAGCGACGCATCATCCTTCAAATTGTGGTCGACGGCAACACAGCTTAAGTTTCAGCCATTTACTTCATCTCAT
TTAGTTATAGTATTCATGTTTTGTTACCCCCATT
(SEQ ID NO: 860)

Start ATG: 67

MDNPSSPPPNTPSDAAERRDLRAAMTSPVGDFEPFENEDEILGDQTVRDEAEEEDGEELFGDNMENDYRPMPELDHYDPALLDDEDDFSEMSQGD
RFAAESEMRRRDRAAGIHRDDRDLGFGQSDDEDDVGPRAKRRAGEKAAVGEVEDTEMVESIENLEDTKGHSTKEWVSMLGPRTEIANRFQSFLRT
FVDERGAYTYRDRIRRMCEQNMSSFVVSYTDLANKEHVLAYFLPEAPFQMLEIFDKVAKDMVLSIFPTYERVTTEIHVRISELPLIEELRTFRKL
HLNQLVRTLGVVTATTGVLPQLSVIKYDCVKCGYVLGPFVQSQNTEIKPGSCPECQSTGPFSINMEQTLYRNYQKITLQESPGRIPAGRIPRSKD
VILLADLCDQCKPGDELEVTGIYTNNYDGSLNTDQGFPVFATVIIANHVVVKDSKQVVQSLTDEDIATIQKLSKDPRIVERVVASMAPSIYGHDY
IKRALALALFGGESKNPGEKHKVRGDINLLICGDPGTAKSQFLKYTEKVAPRAVFTTGQGASAVGLTAYVRRNPVSREWTLEAGALVLADQGVCL
IDEFDKMNDQDRTSIHEAMEQQSISISKAGIVTSLQARCTVIAAANPIGGRYDPSMTFSENVNLSEPILSRFDVLCVVKDEFDPMQDQQLAKFVV

HSHMKHHPSEEEQPELEEPQLKTVDEIPQDLLRQYIVYAKENIRPKLTNIDEDKIAKMYAQLRQESFATGSLPITVRHIESVIRMSEAHARMHLR
ENVMEADVSMAIRMMLESFIEAQKFSVMKKMRSTFQKYLSFQKDHSELLFFILRQLTLDQLAYIRCKDGPGATHVEIMERDLIERAKQLDIVNLK
PFYESDLFRTNGFSYDPKRRIILQIVVDGNTA*
(SEQ ID NO: 861)

Name: Minichromosome maintenance 2
Classification: DNA_replication_factor
Gene Symbol: Mcm2
FlyBase ID: FBgn0014861

Celera Sequence No. : 142000013384523
TTTGCAATTGTTTATGGGCAAAGCAACAGACAGAGATGGCGAGTGGGGCGGCAGCGAGGGGCGCGAGCGAGATGGAAGACAAAAAATGTGAGCGA
ACGGCAAACTAAAATGTATCTATGAGATACATGGCCTGATCGCCAGCGCTCTCGCTCGCTCTCCTTTGGCTCTCTCGCACTCATTACGTATGAGT
TTGTTGGTTTTGTTTTCCTTTTATTTTACAGATCATTCGCCGAGCTTTATTTAACTTTTGCTCTCTCTCACTCGAATTTTTGTTGTTGTATTTCC
CTGGCTTTACAATCCATTTTTTGTTTGTTGCCACTCTCTGTTCAGTTCAGTTATATTCGGAGTCTTAATCATCGCATCGGAATGTTTACTCCAAG
TTTTTCCCCCGTTCCGTTGCGTTTTGTTTTGCCTGCTGCCGCTGCTGTCTTGTTTAAAATATGTAATTTATTTTGCTGCTGCCTCTTTATTTTAT
TTTCCTTTTATTTTTCTTTTTTTTTTTTGCTTCATTTCGCCTCCACCGATCGCATTCCTTTACACACACAGCTGCAGCACGCACCTTTTCTTTCC
GGTTCAAGAGCGCTTCGGAATCGGAATTTATATGGGTTTTTTTTTTAGCTCGTTTGCCGGAGCTTCCTGAATGAGTGAACTGCTGATCTCTCACC
TGCGTTTTATGCCTTCTTAAGCCACTAACAACTTGCCAAGAATTTTATTCTATTTTAATTTGATTCTCAATGAGTTATCTGCTTCACTTATTAGC
CATTAAGCAGCAATTGGGGTTTATAAGCACTCTTGATAGTTTGCGATGTTAAAGCATCTATAACTTATTTAAAACACAACCTGTTGGTTTGGTCA
TTCGTTATGTATGCCTCATTTCTGATAATTGTTCTAGTAGTTTTAATAAGTTTAAACTAACTTTCCAAATGCAAATATCTTATAATTATATTTCA
GATCGCCCTTGTTTCAATTTCGTTTCTTTAATTGACCCTTTCCGGAACACTTACCAATCTCTGGGATCCAGCCAGGTGGTCTTCTTGTTGATATG
ATCTATGTAATAGGTCTTGCCATCGAAATCCTTGGCGATATCCCAGCCATCGGGAAGTGGGAAGTCGCTGTGGTGTTGTTGCTGCTGCTGATGAT
GCGTGTGTTGTTGTTGTTGCTGTTGTTGATGATGATGATGATGTTGCTGTTGCTGCTGTTGGGGTCGCAGGTGGTGGGGATGCAGATGATGCTGC
GATTGCGATGCGGTTTGTTGCAGATTCGGCATTTTAACTTTGTTTCTCGCCGTGTACTTTGGTTAGTCTGAGAAAACGTCGTTGTTGCTGGATTT
TTCACCCGACGCGCGCCTTTTCTTTCTTTTCGCTATTGCTATCTACGTTTGCTTCTTTTTTCGGGGGGTTTCTCTTTGCGCTGTTTACATTAGCA
AAGACATTTCAATTCCGTTTCTTTTGCTCCGGCGATAATGGAGACCGACCCGCACACACACACACACACAACACGGCCACACGGTGACGGGCGTAGA
GGCACACACCGAGCCAACTCGAATACACACGCGCGCAGGGGAGAGAGAGCGGGAGAGCGCGGGCGCGCTCTCAATTATTTATTTACTTTTTTCGT
AACTGCATTCCATTCCAGCTCAAACACACGCACACATATGGGGGACGAACACAAGCGCACACGATCACTGCTCACAGTTGGTGCTGCTTCTTTTC
ATTTCTTGTTGTTGCAAGCGTTTGAACTCCTTTACTTATTTTCTTATTTTCGCCTAATTGAAACTAATTAACGACGATAATCCAACCATCCACTT
GGTGTTCACAAAAAAATATGTACTTCAGTTTAGTGAGTTCGCGCCGTCGCCGATCTCTTCGGTTCCGGAATTCCTTGGGGGAGCAGCAAAAAACA
CGAGTAGCGCGCTTGATGACCGTCCGATTCGGATTCGGAATTTGTTTTGGTAACATTCGCTGCTAGTGGTGTAGCAGAAAACATCGCATTGCATA
TCGATACACTCGCGGCGATGTTATTCGATGTATTGGTTGATATCGATATTATAGGCTGTATTGACGCGGTTGCAGAGATGCGATATTTAACAATC
ATGCACGAAAAGTATTTATTGTTATTTGGCTTGTGTAGTCCCCAAGCATAGGTGTAATTGTTGAGGGAAGAAAATAGGAGTTGTACGTTCAAAGA
TCGGCTTGGTAACAGGAACTAGTTCGGTTCTTCAAGCGATGTTAATCAAAGCCAGTTCCGATAGATCATGTTAACTCGCTCTGTTAACAATTACT
GTTATCTTAATCCTAACATTTCCGTTACATTTTAAAAACAGAAAAAGAAAAAATTTAAAAAAAAAGACTGTAAACTGAGTTACGCATTTCGAAAT
CAATATGTATCCCAACCATAGATAGAAAAATAAATTATGTTTCCGAAACATAACTTCAATAAAACCACAATTTCGCTTGCTTTGTACGTTTGATA
TTGTATTTGCATTTTATGAATTGTAAAAATTGAGTCAACAAGACTAACACAGCTTCAGCTCAAGACACATGCAATTTCATTGACATTGTTTAATT
GTATATATTAAAGGAAATCAATTAGGATATAAAGAGAGAAACCTTTTTGCCGCTTATGCGATGCCAACTATCTGGATCTGGATTGTCTAACACGA
AACCCTAACTAATTGGTAAATTAAACATAAATTAATCATATCGGTCAACAACTACAACTAAATATTAGTTATTAGCGGATAAAGAGCGCCCCATA
AACTATTTACACTAAGCTTTAGTCTACTAGAGTCCCGGATTCCATCTCCGCTCCTCGGATCTTCGGATCTTAACTCAGATGTTCGGATCTTCAAG
TTCTAGGAGAGAACTGGTGCAGTGCATCCGTTATTCAGGCGATACTCGGCATAGACCAGTCCGGTGTTGTGCCAGTGATAGA
(SEQ ID NO: 862)

Exon: 1932..1880
Exon: 1462..1001
Start ATG: 1267 (Reverse strand: CAT)

Transcript No. : CT23083
CCGAATCGGACGGTCATCAAGCGCGCTACTCGTGTTTTTTGCTGCTCCCCCAATATCGCCGGAGCAAAAGAAACGGAATTGAAATGTCTTTGCTA
ATGTAAACAGCGCAAAGAGAAACCCCCCGAAAAAAGAAGCAAACGTAGATAGCAATAGCGAAAAGAAAGAAAAGGCGCGCGTCGGGTGAAAAATC
CAGCAACAACGACGTTTTCTCAGACTAACCAAAGTACACGGCGAGAAACAAAGTTAAAATGCCGAATCTGCAACAAACCGCATCGCAATCGCAGC
ATCATCTGCATCCCCACCACCTGCGACCCCAACAGCAGCAACAGCAACATCATCATCATCATCAACAACAGCAACAACAACAACACACGCATCAT
CAGCAGCAGCAACAACACCACAGCGACTTCCCACTTCCCGATGGCTGGGATATCGCCAAGGATTTCGATGGCAAGACCTATTACATAGATCATAT
CAACAAGAAGACCACCTGGCTGGATCCCAGAGATTGGTAA
(SEQ ID NO: 863)

Start ATG: 249 (Reverse strand: CAT)

MPNLQQTASQSQHHLHPHHLRPQQQQQQHHHHHQQQQQQQHTHHQQQQQHHSDFPLPDGWDIAKDFDGKTYYIDHINKKTTWLDPRDW*
(SEQ ID NO: 864)

Celera Sequence No. : 142000013384651
CAATTCAGTGGATTTCCGAAGAATCACACGAAACTCGCAATAAATATGTACACATATAGAAATATATATAGCATACATACATATGTAGGTGCCCC
AAAGATATCGACTTGTTGCCTCTGGGGCAACAACATAGAAGTCGGGATAATGGTAAACACATAAAGGGCAAACTTTTTGACCGATATCGGATTAC
ACTATCCACACCCACACACTTGTACAACGACCAGAGTGATGAAGTGCGGGAGCGAGGGAGGTTAAAAGCGAACAATTAAAAAAGCACATGGTTTT
CAGGCGATGGCGCCACCTCCAAAGACCTTTCGAATTCAAGTGCAGGCGTTTATTTTTGGGAGCAAACTCACCTGGGCCAGTTGATCCTCGGCCGC
CTTGCGCTGTTCCGGATTCGGATCAATAGTTGCGCGCAACAGTTCCGTGAGTTTTTGTGCCTCCATTTTTGCTACTTTTGCTTGATTCTATGTTT CGCCGGTCTTTCTGCTGCACTTCGTCGTTTGGCGGTCACCTTGTGCCCACTGTGCACCCGCTGTTCTTGCCTTTATATAGACCTTGGTTTATGCT
AGCCGAACCAGTGGCTCCAATGTGTGGGCCAAATTGCAAATCTCTTTTTCCGGAGGAAAAAACGTGGAAAAGACTCCACACACGCACACACACAC
CGCCGAAATTCGCGAGACGAACGAAGCTTAGAAGAAGAAGAAACAGCGCCTGTGTGTGTTGACTAACGCCGCAGTGTATGGGGCCCTACAGGGCT
GCATTATGTTCGCCGGTAACAGTTTAGCCAAAAATTCGAGCAATATTGAAAAGCCTTCGCTGCGGAAAATCTAGGCACCATTTATATATAGACCA
CTTGCTTCATAAGGTAACTATATTTAAAGGCTTAAAAAACAGCGACTTTTCACAATTCCCGATAAATTGCCATTCAAGTTGCATGGCCAATCGAT
TGTTGCAGCCCTGGCAGCTGCTCGTACGTGAACACGCGAATGTGTGTGTGACGAAGAGCAAAGTGACACATAGTTGGAGGTGTGGTTGAAAATAT
ATAGAAATCTGGGTTTATCTGCAACTGAAACGAAGGGAAATTTGTGTTAAAGGCGAGCGAAGATCGCAACTGAAGAGCTTTAACTGGCAGCAAGG
CAAAAGGACGAGCAGCGACCATGGCAGGCAGGCTACCGGCATGCGTAATCGATGTGGGCACCGGGTGAGTTTTTAGTTTCGATTGCCCGTGGGGG
TCTCCAATTGGACGGAAAGGAGGTCGACTGACTAACACTCTGCTTGTCTGCACATCCATCAGCTACTCCAAACTGGGATTTGCCGGGAATAAAGA
GCCGCAGTTCATTATTCCCTCGGCGATTGCCATCAAGGAGTCGGCACGAGTGGGAGACACCAACACACGGCGCATCACAAAGGGCATCGAGGACC
TGGACTTCTTCATCGGCGATGAGGCCTTCGATGCCACCGGCTACTCCATCAAGGTATGCTCTTGTATCTATGGTCATTAAGCAACCGACATCACA
TTTATCATTGCATTCCAATAGTATCCGGTGCGTCATGGTCTGGTGGAGGACTGGGACTTGATGGAGCGCTTTCTGGAGCAGTGCGTCTTTAAGTA
TCTGCGCGCCGAGCCTGAGGATCACTACTTCCTGCTGACTGAGCCGCCGCTAAATACGCCCGAAAATCGGGAGTACACCGCGGAGATAATGTTTG
AGACGTTCAACGTTCCTGGTCTGTATATCGCCGTCCAGGCGGTGCTTGCCCTAGCCGCCAGTTGGGCCTCCCGGTCCGCAGAGGAGCGTACCCTT
ACAGGCATCGTGGTGGACAGCGGCGATGGAGTGACGCACGTCATACCCGTGGTAAGTAGCACAGATCTTATCTTATCAGCAGAGTTGGGTTGGCA
CTGGATTCGGTAAAAACTGTTTGAAAAGAGAACCCAAAACCGAAACAGTCGACGGATTTATTTAATAAATAAATAGCACATTCTGAGGCTATTAT
TAATACTACAGAATGTTATATTAAGAGGGAATTATTAAGATAAAATAGCGTATTAGTTATAACCATATAAATATATTAAGCTGTTTTTCATTTCT
AGGCCGAGGGCTATGTGATCGGCTCCTGCATCAAGCACATTCCCATCGCGGGCCGCAATATCACCTCGTTCATCCAGAGCCTGCTACGCGAACGG
GAGGTGGGCATTCCGCCGGAACAGAGCCTCGAGACTGCTAAAGCGATCAAGGAGAAGCACTGCTACATCTGTCCCGATATCGCCAAAGAATTTGC
CAAGTACGACACGGAGCCGGGCAAGTGGATACGCAACTTTAGCGGCGTTAACACGGTAACCAAGGCGCCGTTCAATGTGGACGTGGGCTACGAGC
GATTCCTGGGACCCGAGATCTTCTTCCATCCCGAGTTCTCAAACCCCGACTTTACCATTCCACTGTCGGAAATAGTGGATAATGTCATCCAAAAC
TGCCCAATCGATGTGCGGCGTCCTCTATACAATAACATTGTTCTGAGCGGTGGATCAACGATGTTCAAGGACTTCGGCAGGAGGTTGCAGCGAGA
TATCAAGCGATCGGTGGACACACGTCTCCGGATCAGCGAGAATTTGTCCGAGGGACGCATTAAGGTGGGTGATATCACAGCTGCTAATGAGTCAT
ACTTCTTACTTTGATTATTTTTGTTACAGCCAAAACCCATTGATGTTCAGGTGATTACGCACCACATGCAGAGGTACGCCGTGTGGTTTGGAGGC
AGCATGTTGGCTTCAACGGTAAGTTATAGTGGCCTAAGATCCGTAAAATCCTTTATCTCAATATTCTTCCCATTTCTAGCCCGAGTTCTATCAGG
TGTGTCACACGAAGGCTGCCTACGAGGAGTATGGCCCCAGCATTTGCCGTCACAATCCCGTCTTTGGCACCATGACATAATTGATCCGATCCAAT
CGGCTTGCAGCAGTTATTTTTGATTTATTTTTCCATTTAAAATTGATTTATTGATTTATTCTCCAACTATATATATATATATATATACATTGCGATT
CGGTATTCCACGCTAAAGTATTAGTAATTATTCTTTTCTATATGTGTTTAGCTATTAACTCTGTGTAAATCAGTTTCGTTCTGTTTAATTTCGTG
TGATTTTGTTAGGCTAACTATAAAGCAACAACTCCGATGTCTGCCAGTTCAACCCCCTATCTAAGGTGCATTATTTCTAGAAGTCGACTTTTATA
CCATACTCAAACACGATCACACACAGTCACACCGATCTAAGCTCTTGGAGAAATCCCGGCTCTATACACAATTAAATACGAAAACGCTCTACTTG
TCATAGAAATATTTATAATTGCAATAACTGCAACCAATTCAAACACTGAATGAACAAAAAAGGAAAAACGAAAAGAAATATTGATGAGAAATCTG
TTTGTTATATTGATAAGCGTAATTAAAAAGGCATTAAATAAATCAATAAAACATTCTTTAAGCTCAAACACTTTCGTCGCTTTCGATCTAAAGCT
TTTACTGGAAAATTTTATTCAATGCATAAGTTACATATATATATTTTTTGTGTTCAAATTGCTCTATGTATTGTATATATAAATTTTTGTGACGG
TGTCGCTAAGCTGAGAAAATAGCAAAAGGTGGTTTCCAAAAAACATGTCCCGAGCTAGAAATCCGAAACAACTTCGTTACGCCTCGCGTAATTGA
CAAACTGACTAGTCAATGTAGTCACTGGAGCCCTCCTCCTCGTCGTTGCTGCTCGTGGATTGTGCCGCCGCCGTTTCCGGCGAACGCAAGTGCTC
TGCAATCCGGAAGTTTTGCAGGAAGTCTCGCATCGCGTCCATCATTAGCGTTAATGACTGCTGCAAACCAGCTTCTGCAATAATGTTGGAGGAGA
AGTGTAACTACGATATCCGCTAGCGATTCTTTTGG
(SEQ ID NO: 865)

Exon: 1001..1204
Exon: 1298..1478
Exon: 1542..1856
Exon: 2093..2629
Exon: 2690..2773
Exon: 2835..2930
Start ATG: 1161

Transcript No. : CT23123
ACGAAGAGCAAAGTGACACATAGTTGGAGGTGTGGTTGAAAATATATAGAAATCTGGGTTTATCTGCAACTGAAACGAAGGGAAATTTGTGTTAA
AGGCGAGCGAAGATCGCAACTGAAGAGCTTTAACTGGCAGCAAGGCAAAAGGACGAGCAGCGACCATGGCAGGCAGGCTACCGGCATGCGTAATC
GATGTGGGCACCGGCTACTCCAAACTGGGATTTGCCGGGAATAAAGAGCCGCAGTTCATTATTCCCTCGGCGATTGCCATCAAGGAGTCGGCACG
AGTGGGAGACACCAACACACGGCGCATCACAAAGGGCATCGAGGACCTGGACTTCTTCATCGGCGATGAGGCCTTCGATGCCACCGGCTACTCCA
TCAAGTATCCGGTGCGTCATGGTCTGGTGGAGGACTGGGACTTGATGGAGCGCTTTCTGGAGCAGTGCGTCTTTAAGTATCTGCGCGCCGAGCCT
GAGGATCACTACTTCCTGCTGACTGAGCCGCCGCTAAATACGCCCGAAAATCGGGAGTACACCGCGGAGATAATGTTTGAGACGTTCAACGTTCC
TGGTCTGTATATCGCCGTCCAGGCGGTGCTTGCCCTAGCCGCCAGTTGGGCCTCCCGGTCCGCAGAGGAGCGTACCCTTACAGGCATCGTGGTGG
ACAGCGGCGATGGAGTGACGCACGTCATACCCGTGGCCGAGGGCTATGTGATCGGCTCCTGCATCAAGCACATTCCCATCGCGGGCCGCAATATC
ACCTCGTTCATCCAGAGCCTGCTACGCGAACGGGAGGTGGGCATTCCGCCGGAACAGAGCCTCGAGACTGCTAAAGCGATCAAGGAGAAGCACTG
CTACATCTGTCCCGATATCGCCAAAGAATTTGCCAAGTACGACACGGAGCCGGGCAAGTGGATACGCAACTTTAGCGGCGTTAACACGGTAACCA
AGGCGCCGTTCAATGTGGACGTGGGCTACGAGCGATTCCTGGGACCCGAGATCTTCTTCCATCCCGAGTTCTCAAACCCCGACTTTACCATTCCA
CTGTCGGAAATAGTGGATAATGTCATCCAAAACTGCCCAATCGATGTGCGGCGTCCTCTATACAATAACATTGTTCTGAGCGGTGGATCAACGAT
GTTCAAGGACTTCGGCAGGAGGTTGCAGCGAGATATCAAGCGATCGGTGGACACACGTCTCCGGATCAGCGAGAATTTGTCCGAGGGACGCATTA
AGCCAAAACCCATTGATGTTCAGGTGATTACGCACCACATGCAGAGGTACGCCGTGTGGTTTGGAGGCAGCATGTTGGCTTCAACGCCCGAGTTC
TATCAGGTGTGTCACACGAAGGCTGCCTACGAGGAGTATGGCCCCAGCATTTGCCGTCACAATCCCGTCTTTGGCACCATGACATAA
(SEQ ID NO: 866)

Start ATG: 161

MAGRLPACVIDVGTGYSKLGFAGNKEPQFIIPSAIAIKESARVGDTNTRRITKGIEDLDFFIGDEAFDATGYSIKYPVRHGLVEDWDLMERFLEQ
CVFKYLRAEPEDHYFLLTEPPLNTPENREYTAEIMFETFNVPGLYIAVQAVLALAASWASRSAEERTLTGIVVDSGDGVTHVIPVAEGYVIGSCI
KHIPIAGRNITSFIQSLLREREVGIPPEQSLETAKAIKEKHCYICPDIAKEFAKYDTEPGKWIRNFSGVNTVTKAPFNVDVGYERFLGPEIFFHP

FIGURE SHEET 465

EFSNPDFTIPLSEIVDNVIQNCPIDVRRPLYNNIVLSGGSTMFKDFGRRLQRDIKRSVDTRLRISENLSEGRIKPKPIDVQVITHHMQRYAVWFG
GSMLASTPEFYQVCHTKAAYEEYGPSICRHNPVFGTMT*
(SEQ ID NO: 867)

Name: ACTIN-RELATED PROTEIN
Classification: cytoskeletal_structural_protein
Gene Symbol: Arp66B
FlyBase ID: FBgn0011744

Celera Sequence No. : 142000013384139
TGTGCCTCGTCGACGACGCTGCTTAATGTCAAGGTTTTTGGCTGCTGTTGCAAGTGCAGCAGCAGCAGGAAAAACAGGAAAACCAGAAACGGCC
GAATGAGAACGGCACGTGGCCAGCCCCCGCAACGAAAAGGGGCCAGAAAGGGGGTCGATTATGCCATTACCAGGGCAAAGCTGCACCTTCCGCCC
CCGGAACCCCCAACCCCCTGCCAGTGCGCCGCGCATGAATGCCGCGACAGACCCGATTCGAAAGCCAATGTCAAGTGCACGCGGCACAAGGATAT
GGAGGCAGGAGTATATTACAGGCCGCCATCTGCCCCACTGTCAGTTCCCCTTCCTCAGTGCCCACAGCAGCTACAGTGGAGCTTCTATAAATTGA
CATTGGGCTTTCATCAATATTGAACTCTTCGATATGGACTGGCTTATGAAGACTCGTTTATAATAACACATAAATCCTATTTTCATATACGGCTT
AAGTTTGACATACACAGGCTCGACTGTACCTCATCATCGAGCATTAGGACGGTCGTTGTTGTGACCTCCAAATTGGTTGGCACACTCACCTAAAT
GGGAGTTTATCTATATTTTATGTGCACGACTTATACCTCAGGCCCATTTCACTTGATCACCAATTAGTGACTATATGCTCAATATTTGCCAATAT
CAAACATCAGGTGCTTCGTCAATTAACTTGTTAATTAGATAGGAAATAGATTCTGTGGTTATAATTGTTTTTGTACCGTATTATAATTGTTACTA
CTTATTGTAGACGAATTTACATTAATCGATATCCATCCAAATTAGTCTGCGAATTCATTAGTTCAACAAACTACTCAAGGATGATGAACTTTTAC
TAAAACTAATTCCGTTCATCGGCTTTAAATAAAATAAATCAACTGTTTCATAATAGTAATTAATAAGTCATATTAGTCATATAAATAATAAGGGT
CCACACACAAAATTGAATACAAGATAAAACGCTCTTCTCATTTGATATTTATTCAAATTATTATTTAATGTAAGTTTTGAACTTATTTATGTTAA
ATAACCTAGTGAGAATGAAATACAATGTTTTGTTTGTTTCTTCTTTACTGACTGCAGTGGATTGACTGCTTGGCATAACTTGTTTATTACTTCTT
AAAAATTCTTCAATAATCTCTTTATAACTTAGGCGTATAAACTCATAATTCCGGCTAGTTTCGAGAACGGATTACCAAGGACAAAAGTAAATTAC
ATATCTTCTACTAAAACTAGAATCTAAGGAAGAGAACAGACCAATCCGTCTACGACCAGGTCTTGGGAACACTGAACGGCCCGAATCGTTCGTGA
CTATCAACGCCCCGCACAGCGAAGTAATACCTCTGGTTCTCCTGGAACTGATTTAAAGTCACTGCCATTGGCAGCAACATAGCGCTGACATCGCC
CACATGCCGCCAGCTATCCGTGCTGGGCTCGTTAATCGTCTCCTGGTATGCATAGATCTGGTACATTACGCACTCTGCGAACCGCGGGCTCGAAT
CCTCCAGAGTCCAGGATATAACGATACCAGTATCAAGGAGACTAATCCGGATAACGGGTCGCGAAGGAGGCACCTTCCAGGATGGATTGAAGGGC
TGGGGAGGAGACGTGGGCAGTGGTGCAGGATGTGAGTATCTTAGACGAGACGCTGGAGGCGGGGTGTTTTCCGAACGTATCTGCATAGTTACGTT
TGAGCCCAAGGGACTTTGCTGACCTTTGAATACGTTTGAAAATAAGTACGCCGAATATTTTGAATATAATGATTTTCCAACTCACCTCCTCCATT
ATTATGGACTATCTGTCGAGCATTTACGCGAGGCAATTGCATTGGAGAAGCTCGCACCACATTTCCGCCTCCTCGTCCTCCTCTCGTCGCTGCTG
CAGTCTGAGCATTCCGCTTAAGCATCTCCATACGCAAACGAGCGTTTTGTGCTTGGGCAGCCCTAGCCGCCGCCGCAGCCGCTGCATCATCCTCA
TCTGTGAGGTCAATGACTGCCTTCTCCTTGGGCTTGGCCGGCGCCAAGCTGGACTCCTGCTGCTGTCCATAGCTGCCCAATTCCGATCCACTGCT
GCTAGATGAGATGGGCACCGAGACCGTGGCCCCCGAAAGCGGTGGCTGCTTGGCGCGCACTTTAGTTGTGCACTTCGGCACTTGCTTGGCGGGAC
TCGAACCTGGCGTGGGACCGGGACTAGGTCGAGGTCTGCAATATGAAACAATTGTAAGTTAGTAATGTGAATATGACATGTTTCTTTTGACGAAG
AATTTGAGATCTCGGCGATTATACGGACGGACAAATGGACGGACGGACATAAACATATTGATTCGACAAGTATATTTTTATATTGGTAACGCTTT
TATTTACCCATTTGGGTTTATTACCCCAACTATAAAGATTTTCAATAGCAATAAAATATACTTGAATGTTAAGAAAACAAAATTTTTTCTGGCAT
ATCAATACAAATTGGGAAATAGAATAATAAAATTTAAAAAAAAATCTATGTATGCTTTTATAGCCACTGAGTTCGAGGCGTTCATATGGACACAC
GGACGGACATGGCCTGATTGATCCAGATAAAAAAAATATATACGGAAACTCTGCCTTCTACCAGTTATATACTCTGTAACGAATCTAGTATACCG
TATTACTCTACAAGTAAAAATATGAATCTATTTAGCTAATTGGGTCTGAAACGATTCCCAATAAATTGCTAATTGTAAACTTCTGCACAAGCGTG
GAATTCGCTTTTAATCGAAGATCACGATTAGGATTATACTCACAGTAGGAACTGTTGCTGCGCCTGTTGTTGCTTTTGTTGTTGTTGCAGGTGTT
GTTGCTGTTGTTGCTGCTGTTGCTGGTGCTGTTTCTGCTGTTGTTTTTGCGCCAAGAAAGCGGCTTCTGAGTTCCGGGCACGCATGACGGTTTTA
TTAATCGCATTGGCCACCGATGAAGGCGTGGAGCCAGGCGTTCCGGTGTGCTTGGAGGCGTGCATTGTCCTTTGAGCTATAGGCGGTGAGGACTG
CAGACGTTGAACGCTGGACTGATTCATAAGCATTGGCGCGGGCTGTAAGTTAGTAGGTACCGGCCGATGGGGCGTGACCTTCTGCAAGCAGCCCC
GGCGCACAGGTGGCGTGACACTAGCCGTTGTTAAGGATTGAGATGACCGTGCTGCTGGCTGCTGTTGCTGGTGATTGGAATTCGGAGTGACACTG
ACGCCCGCACCCGTTTCCGATGAGGATGTGGATGGTCCAAAGGTAGGCGGAGGAGGTCTTGGTCGCACGGTCGCACGCGTCGGGGAGGTGCTGGC
CTTGGGTGGTGTTCCGCTGGGCGGCGCCAACACGCTGCCAGCAGCATGAGTTGACTCTGGTGCGGCGACGGTGGGCTTTATAGCCTTGAACGGAA
TGCCCACCTGAAGACCAACAGCTCGTGTTATACGCACAGGAGCGGTGAAATGAGAGTTCTTAGCCTCCAAGTCCTTAAGCACACGCTTGTGCACC
GTCTCCAAATCCAGGAATTGCTTCGACACCTCGGCAATCTTGCGGCGATAATTGGCGAGAGTGCTCTCGCATTTGTCCAGCTGCATACGTATTTC
TGCGAAATCACTTTTAACCATCATCGCCTCGACGACTTTCTGCAGCACCAGCTCCTCCAGGTCGTCACGGGTCATTGTGTCGAAACTACGTCGGA
AGGTCTTAAAGAATTCCAAGCGCAGGGGCTTAACATTCTGTTTAATTTCTGGAACGGGGTTAAGGTCGAAGTCCAGTTTCTTTTGGGTATCTTTT
TTGGGGGATTCTTCTTTGTCTTCCTGACCACCCATATCAATTTGTAGCGTGCCTTCGTGGAGCTATTTGAGTCAGAGTCTTCAGTCTTAGCTTT
CTTATTAGGTATTTCCTCCTGAGGGCTGCTGTCCAGATGTTCATGGCTCCGCTTGGTTACATCCTTCAAACCACCCTCTGCTCTGCTGAGTATTG
GTAATGATTCTTGATTCGTCTCCGCTTCGAATTCATTTTTTTCATCGGTACTAAGACGCAGCCGTTTTGGAACCGACTCTTCCGCGTACTCGGCG
GGTCGCAATAGATTGCTGGAATTACTGTTCCCATCCTCTGTGGTAGTTTGCTTCACCATATCATGGGTCTTCAGTTTCTCGAACTGATCGCATGC
ATTGTCGGAATTGTCTATTTGGAGATTCTTTGCTTCAACTGATTCTGTAGTTGACTCATTGGGAAGTCCTTTTAAAGCTGTTTCCTTTTGGATAG
TTTGAACTTCCTTTTCCGATATCCCATTCTGCGGTGTTTCATCCTCATCCTCGGAGACGAGAACAACTTCGTCATCCTTAGCTTGTGGTTTCACA
GAATTTTCGTTCGTTGGATTGGCTGTGGTGCCCACATTTTCGGTCTTATCTAGGGGTTCAAAGAATATAACTTCGTCATCGGACTCCGTCTCTTT
GGTCTCCTCTTCAACAACCGTTGATTCATTGCTTTCCAAATCCTTTAAATTTCCATCAGTAGAAATTTCGCATGCTCCATTTGTCGTGGGTTCCT
TATCGCCTTTTGGTATCACCCCGAGTTCGTCCTCTGCAGCCTTCTTTTCTTCTATCTCTACAACATCCTTGACCGCTTCATCAAGCTTATCATCT
ATGGTTGTGTAGTTCATTTCGTGGTCTGCAGTTCGAACATCAAATTCTTTTTGGACTTTCTTTTGGGGATCTTCTGTTTCTTCACCTTCGATCAC
CACAGGTTCCTCAAGCTCTTCAGTGTCTTCTATTTCCTTTTTATTTCTGGCTCTTCTGTTTCCTTAACGTCTTCCACTTCCTGGGTTGGGCTTG
GATCTTCCTCTTCCTTGGTGTCTCCCAGTATCTGTGCTACTTTCGAAGCTTTGATGATTTTGATCTCCGACTTTTCTTTTTCAGTCGCCTCTTCT
GAATCTTTTGTTTCCTTGCAGTAATCAGGCTCTTCTTTTTCCTTGTGCTCTTCAAGTTCCTCGGATTCCTTGGATTCTTCTGGTTCATCCACTTG
TATTGACTCTTCGCTCTGGATTGGGATAGACTCTTTCGACTTTTCGGTTACTTCGTCTCCAACTAACATGGGTTCTTTACCTTCTGTCAAATGTT
GATCAGCTTTGACAGACTCATATTCGGCCGCACTCGCTGACTTTTCTGAGATATTATTTTGCAAATTCAATGATTTCTTCGTAGAAACCTTACCG
TGAGTAAGGACTTCGGTATCTTCTGTGTTAGCTTCAGTTTCCTCGACCTCTGATTCCGCTTCGCAAGGCACACATTCACTCGACGAGTCTAAATC
TATAACCTCAGTGTTGGGTTTTTCCGTTTCCTTAATTATATCATCGTCATCAGATGAAATGTCTTCTAAATCATTGACAGATGAGTTGTTTTCCG
TGTTTAGTTTTTTGCTTGGCTTCGCCTTCTTGGAGTCCTGAGAGGCAAAGGCATCAAACTCGTCGGCACTCGATATACAGTCTAAAGCATACATA
AACACATCATCTGTTGATGTATTTTTCCGGTCTTTTTCAATGTTATCCGCAGTATTGGCTGGGACTTCATCCTCTTCCTTTGACTTTAATATTTC
ATCTGAATCAGCTAAATCTTCGGTTTTCTGTGTGGATTCTTTAGCTGAAGCGTGTTCTTCAGTTTCATCTAATTTCTCCTCAGTCTTTAATTCAG AATCAGGATCGATGCACTCTTCTCCTTCTAGAGAACTAAGCACCTCTTCGCCTTCTTCTTCTTCTTCTGGTTTTTCTCTTTGCTCTTTTAGATTT
TCGTCCGTATCAGCAGCTGTTCTCTTCTTCGCCGACGCAGAGTCGCATTCCTCGTCTCTATCGAGTGAATCGATATCGTCGGAATTCCTGGGACT
ACAATCCACAATAGAGCTAATCTTGTCCAGAAGAGCGTCCAAATCACTACCTGGATTACGCTCTCGGTCCGATATCTTTTTTGGTTTGTCAATAA
CTTTGACGTTATCGGAGCTATCGACGCCATTGGTTAGCTCACAAAGATCCACTTCATCCACAGAAGTTTGACTGGATTCGTTGAGAATGGCTGTA
ATTCAGATATCGATATATCCCAAACGGATTTATCCAAATAACTAAGTCGCACTTACCGGGGGTGGAGAGAGGTTCCACTTCATTGCCGAGCTCTG
TGGATAGGGTTCGCATCAAAGCTTCCTCTGTAGAGAGTTCCTTCAGTTCCATGGTCTGGTTTACTCCCATCATTTTGAATGTTTTTATCGATTTA
CTTAATCGTCATTGAATTGCTAAAAGTAAAACCATATTATAGTTCACGACGTATGTTGACAACTCTGGGATATAACAAACATGTCACAACCCTGC
TACCGCCATATTTTTTTAAAAATTAAATTCAATCTCATTCAAAAATTTCTTGTAAATAGCTTTTAAAAGAAAGCTCGCTAAAAGCTTATTCCCA
GTTCTCGCCAGTCAAAATGCTAATGCAATAACTTGGGAATTATACCTTTAAGTGAGTCTGAAGCCAGCGATATTTTATTAAGACTCCGCCAAAAC
TCATAAACCGCTTTCCCGAATTCATTTTGAAGTCCTTTCTAACTCTAAAGTATACGAAGCCATTAAAGCAATGTTATCTTTGAGTATGGATGTTC
CATAGTCAAAGGATGATAGGAACATCATAACTCAAGACCAACATTTTTGTTTTTTTTTTTTACTTTTTTTTGTGTTCGGTTTGGTGTGTATCTAC
TCCGTTGTTATTGTTCTTGTTGTTGGTAGTATTAAGCGTTCGTCGCTTTCCGAACGCAACAATAACTACACGATTGTAGCGAAAAGACAAAGCAA
AGCGACGATAAATATTCGTGCAAGGGAAAAAAGTGCGTGACGAAAAATGCGAATATGGGGAGAAAGAGAAAATTAACTGCTACCTATTAATTTAT
GCTCATAACTTTATAGTTATAGTTTTTACTATCGAAAGTGGGGTTATGTTGAGTTTGTTGCGTTTTTACGTGATAGCGTAACTGCACATTGTTAT
ATTGAGTTTAGTAACTTACATGCTTAAACTTCCTGATACCCTGTTAACGATTTATTTTGATTTGGCTACACTCGAAGAAATCAAAATGACTTCAA
CATCTTGCCGCGTTTAGTGCAAAAATGAACGAGGTGAACGCCAAACCAGCTCTCGACGAACGAAAATGAGAGCGAGAGAGCAAACAGCTGAGAGC
GGTAAAAGCGGCAGGGGCGTACGGGTAAGAGGAAGATAGTCGGCGGGAGGGCGTGTCTCGGGATGATATGATAAGATTCGATAATGTAATTCCAC
CTGGAGTTTAAGGAAACTACATTCACATCTTGAACTTTAACCTTTCGCGAAAAATAGGGCAAAGCTACAGTCCTCATTGTTATTGTGCTCTATGG
CAAGTTGGCAGTCTCTTTTGGTATGGCAGTTTCTCCATAAAATTATAAAAATAAAAGCAATAGGGGATGGTATAAAAATCGAAATGAAGTGAGCA
GGGATCCTCATTGAATCAAAAAACATTGTTTGATAACAACGAGTAAAAAGCAAAGCGTTTAATAATAACGCAAATAGAACGCGTTTTGTTGGTCG
CGAGCGGCAGGGTGAGATGAGGAAACAGGCAGCTAGAGCGGGACGACTATACGTTTACAAATTAATAGGGGAGCAATATAAGTAAAGAACATTAT
GGAATATCCATTTCTTAGTGCAACTACACACAGCTCCAACCAGTGTTAATAAATAGATGATTTGTAGATGGAGGCCGAACGCAAAGATTATGTGG
AATCAGAGAAGGCTGAAGCAAAAATGTAACAGAATGTAACCCTGTCAAAAAAAGAAACTTTCCAAACTTTCCAAACTTTCAAAACTTAGAACCTA
TAGTCCGTCCGTCCTTCTGGTCTTTTCGAAACGAACTTAGGACCTTGCCAGGATACCGGTTTTGTAGAAAGTTGCGGAGTGAGCGGGACGGACAG
AGAGAGCGGCCGGAGAGTAATTGCAAGAGAGAGCAAGAGGCCAAATTTATATATGCACGTGGCTATATATATTTGCCTGTATGTAGGAATTGAAT
AAAGTTCGCGTAGCGCCAAACACAGCACGACAAAGATACAGCAGCAAGCCGAAAGCAACAACTACAACACCGGGCAAACAAAAATAGAGGCGTAA
AGTCGTTGTTTTTGTAGATGAAATGCTAAAACCTTCGATATCAGCTCTATTAAAGAAATTGATCCTAGAAGCTAGTGACATTGGATCATTAAATT
TCGACTTGCTCTGATGGCAATACTTTTTTCAAGATGCTTAGGTCCATTAAAACCGTTGCTTATACACACAAATGTAGATAACAAACATGTTTAGG
TGTCGTATTTTTGCAACTTAAAGTATATATGGCCAATTTATCGTCTTTAAAGTTCGGTCTTGTATTTAAGCCAATTTTGGGCTATATGTCTATTA
TAGCTGTCCCGCTCTAACACGCGCACACACACCAGTTAAGTTCGTTGTAGCAACGGCACATCGGTGTGAGCGTGTATGTATATCAGAACGTGTAT
TTGTGCGATTTTGCAACGCATTTACATTCTTTTTAGGTTACGTATCGATTTTGATGCAGAGTGAGGTTAGATCGAAAAACATCCAAGTTTTTGCA
TGCTTTACGAAAGCAAGGACATTTTTGAAATCCCCTCGGCGCCCTCTGCATGTTTCTGGTATCAGACGTTCGATAAAGACTAAACCCCGAAAAAC
CTAAAACGAGCAGGTTGCAAGCAGAAGCAAAAGCAAAACGGGCGGCGTTTTTATTCACCTATTGTACAATTTTATGTTTTTAGGGTTGCCAGGTA
TGCATTATGTTTATCATGAATATAATATAAAACCTCGATGTGTCCGATTAGACGCAAATCAAATGTCTTTAAATGTATAATTGAGACCATGATGT
CGCGCAGGGTTGCCACCGGCAGGTCATTTTTTGTCCTATTGCAATGGCATTGCGGTATATAGTCTTGCCTACACGTCGGTAGTCTAGTCTAAAAT
ATAGCATAGTAACAAATCCAGATATATATCAGATTTCGCCTGATTTGCAAATCGCGGTCACTTGACAACCCTGAAAACACAAATGTCTTTAAAGA
GACTCGTACCATATCTGGCGTATGGTACCCGTACCCAGTCCAAATAAAAAAAAACTTCAAAACCCAGTAAAAAAAATGCAAATCCCAAATGTACC
ATTCGATTGGACCATTATATTACAGGGTATTTTTATAAAGAAAATTATAAATATAACATAAAATGGATAAAAAAAACTACACTTACCTTTCTACG
ACACGACAAACTCGTTTATTAACTTATATATTACCGAAAACTATTGAAATATGACTTGTGGTCTAACGGCAACTATCAAATGTCAATGATTTGAA
TGAATTTAACAGCTTCTCCGTGATTTGTTTACAATTCGCAGGCAACTCCACTTCCGATGCCCTTAAACGACGAAGACTGAAACACAGACTAAAAT
CGCACAACAACAGAAGGTGCCGAAAAGAACCAGTCTATGCACAACTGGTTCCGAAGAGCAGCGCCCAGATTGCAAGCTAGCGGCACTTGGAATAG
AGATTGGCGCGTGATTCCGGATGCCGATTTCTGATACGCATCGAGAAGACATTTTTTATGGACGTTTCTAACAATACTTATTATTTTTGTATTTA
TTTAGGTTGGATTTTGGCAAAACTTATTTTATCTTATATTCAACTTTGCATTTTTACGCAATTTGTATTATTATTATTATTATTATTATTAACAT
GATGACCAGATATAACTTAAACTGGTTACCTTCTCATTACGATAGTAATATTATAAAAGGATGTATATTTAATAGCTGAGGAGAAGCAGCATTTC
TATAGTATTTATATACAAAAATAAAAAACGTTATGCAGTTCATGCACGTGTACATCCCTAGTTTGGAACCAAACAAAATCATATGTTGTTACTAG
GGCTGTATAGCTAAACGTTTTATTTATGGGAGCAGAACTATTAAGTGCCAGTTGGAACTAAGACGTGATCTCCCCTGTCCCTTCTTTTGCTTAAA
ACTGAATCATATTGACAAATGTTTTCGGCCCGTTTAAGTAATGTGACGTTCTCATGAAATACAACGGTGAACATTGCAAAAATCGTGTTATTTTC
GTTAATTGTTCCAATGGGTGAACTAGTGAACGGAGTCAGCATGTGCCAGCCCTGATGGCTGCTTTGTTGAACTAGTTCCAGTTCCGGAGCTAGTG
AACCAATAGCAAACGGAACAAAACAAAAACATCTGTAGATTATAGGTTAATTTGTTTTATAATAACAAATGCGGGAATTATTCAATTAAGATGAG
CAATCTGCTGAATTTTGCCCTGCGGCAGGGCGTCAACTCCATCAAGCGCCTTAGCCTCCAGAGTTTCAGACTGGCAGCTCCGGCCATTGTAACAA
AAACGCCGGTTACTTCCACGATAAAGAGATTCTCCTC
(SEQ ID NO: 868)

Exon: 9487..9302
Exon: 6289..6137
Exon: 6075..2799
Exon: 2220..1796
Exon: 1733..1001
Start ATG: 6248 (Reverse strand: CAT)

Transcript No. : CT23297
TTTCAGTCTTCGTCGTTTAAGGGCATCGGAAGTGGAGTTGCCTGCGAATTGTAAACAAATCACGGAGAAGCTGTTAAATTCATTCAAATCATTGA
CATTTGATAGTTGCCGTTAGACCACAAGTCATATTTCAATAGTTTTCGGTAATATATAAGTTAATAAACGAGTTTGTCGTGTCGTAGAAAGCAAT
TCAATGACGATTAAGTAAATCGATAAAAACATTCAAAATGATGGGAGTAAACCAGACCATGGAACTGAAGGAACTCTCTACAGAGGAAGCTTTGA
TGCGAACCCTATCCACAGAGCTCGGCAATGAAGTGGAACCTCTCTCCACCCCCGCCATTCTCAACGAATCCAGTCAAACTTCTGTGGATGAAGTG
GATCTTTGTGAGCTAACCAATGGCGTCGATAGCTCCGATAACGTCAAAGTTATTGACAAACCAAAAAAGATATCGGACCGAGAGCGTAATCCAGG
TAGTGATTTGGACGCTCTTCTGGACAAGATTAGCTCTATTGTGGATTGTAGTCCCAGGAATTCCGACGATATCGATTCACTCGATAGAGACGAGG
AATGCGACTCTGCGTCGGCGAAGAAGAGAACAGCTGCTGATACGGACGAAAATCTAAAAGAGCAAAGAGAAAAACCAGAAGAAGAAGAAGAAGGC
GAAGAGGTGCTTAGTTCTCTAGAAGGAGAAGAGTGCATCGATCCTGATTCTGAATTAAAGACTGAGGAGAAATTAGATGAAACTGAAGAACACGC
TTCAGCTAAAGAATCCACACAGAAAACCGAAGATTTAGCTGATTCAGATGAAATATTAAAGTCAAAGGAAGAGGATGAAGTCCCAGCCAATACTG
CGGATAACATTGAAAAAGACCGGAAAAATACATCAACAGATGATGTGTTTATGTATGCTTTAGACTGTATATCGAGTGCCGACGAGTTTGATGCC TTTGCCTCTCAGGACTCCAAGAAGGCGAAGCCAAGCAAAAAACTAAACACGGAAAACAACTCATCTGTCAATGATTTAGAAGACATTTCATCTGA
TGACGATGATATAATTAAGGAAACGGAAAAACCCAACACTGAGGTTATAGATTTAGACTCGTCGAGTGAATGTGTGCCTTGCGAAGCGGAATCAG
AGGTCGAGGAAACTGAAGCTAACACAGAAGATACCGAAGTCCTTACTCACGGTAAGGTTTCTACGAAGAAATCATTGAATTTGCAAAATAATATC
TCAGAAAAGTCAGCGAGTGCGGCCGAATATGAGTCTGTCAAAGCTGATCAACATTTGACAGAAGGTAAAGAACCCATGTTAGTTGGAGACGAAGT
AACCGAAAAGTCGAAAGAGTCTATCCCAATCCAGAGCGAAGAGTCAATACAAGTGGATGAACCAGAAGAATCCAAGGAATCCGAGGAACTTGAAG
AGCACAAGGAAAAAGAAGAGCCTGATTACTGCAAGGAAACAAAAGATTCAGAAGAGGCGACTGAAAAAGAAAAGTCGGAGATCAAAATCATCAAA
GCTTCGAAAGTAGCACAGATACTGGGAGACACCAAGGAAGAGGAAGATCCAAGCCCAACCCAGGAAGTGGAAGACGTTAAGGAAACAGAAGAGCC
AGAAAATAAAAAGGAAATAGAAGACACTGAAGAGCTTGAGGAACCTGTGGTGATCGAAGGTGAAGAAACAGAAGATCCCCAAAAGAAAGTCCAAA
AAGAATTTGATGTTCGAACTGCAGACCACGAAATGAACTACACAACCATAGATGATAAGCTTGATGAAGCGGTCAAGGATGTTGTAGAGATAGAA
GAAAAGAAGGCTGCAGAGGACGAACTCGGGGTGATACCAAAAGGCGATAAGGAACCCACGACAAATGGAGCATGCGAAATTTCTACTGATGGAAA
TTTAAAGGATTTGGAAAGCAATGAATCAACGGTTGTTGAAGAGGAGACCAAAGAGACGGAGTCCGATGACGAAGTTATATTCTTTGAACCCCTAG
ATAAGACCGAAAATGTGGGCACCACAGCCAATCCAACGAACGAAAATTCTGTGAAACCACAAGCTAAGGATGACGAAGTTGTTCTCGTCTCCGAG
GATGAGGATGAAACACCGCAGAATGGGATATCGGAAAAGGAAGTTCAAACTATCCAAAAGGAAACAGCTTTAAAAGGACTTCCCAATGAGTCAAC
TACAGAATCAGTTGAAGCAAAGAATCTCCAAATAGACAATTCCGACAATGCATGCGATCAGTTCGAGAAACTGAAGACCCATGATATGGTGAAGC
AAACTACCACAGAGGATGGGAACAGTAATTCCAGCAATCTATTGCGACCCGCCGAGTACGCGGAAGAGTCGGTTCCAAAACGGCTGCGTCTTAGT
ACCGATGAAAAAAATGAATTCGAAGCGGAGACGAATCAAGAATCATTACCAATACTCAGCAGAGCAGAGGGTGGTTTGAAGGATGTAACCAAGCG
GAGCCATGAACATCTGGACAGCAGCCCTCAGGAGGAAATACCTAATAAGAAAGCTAAGACTGAAGACTCTGACTCAAATAGCTCCCACGAAGGCA
CGCTACAAATTGATATGGGTGGTCAGGAAGACAAAGAAGAATCCCCCAAAAAAGATACCCAAAAGAAACTGGACTTCGACCTTAACCCCGTTCCA
GAAATTAAACAGAATGTTAAGCCCCTGCGCTTGGAATTCTTTAAGACCTTCCGACGTAGTTTCGACACAATGACCCGTGACGACCTGGAGGAGCT
GGTGCTGCAGAAAGTCGTCGAGGCGATGATGGTTAAAAGTGATTTCGCAGAAATACGTATGCAGCTGGACAAATGCGAGAGCACTCTCGCCAATT
ATCGCCGCAAGATTGCCGAGGTGTCGAAGCAATTCCTGGATTTGGAGACGGTGCACAAGCGTGTGCTTAAGGACTTGGAGGCTAAGAACTCTCAT
TTCACCGCTCCTGTGCGTATAACACGAGCTGTTGGTCTTCAGGTGGGCATTCCGTTCAAGGCTATAAAGCCCACCGTCGCCGCACCAGAGTCAAC
TCATGCTGCTGGCAGCGTGTTGGCGCCGCCCAGCGGAACACCACCCAAGGCCAGCACCTCCCCGACGCGTGCGACCGTGCGACCAAGACCTCCTC
CGCCTACCTTTGGACCATCCACATCCTCATCGGAAACGGGTGCGGGCGTCAGTGTCACTCCGAATTCCAATCACCAGCAACAGCAGCCAGCAGCA
CGGTCATCTCAATCCTTAACAACGGCTAGTGTCACGCCACCTGTGCGCCGGGGCTGCTTGCAGAAGGTCACGCCCCATCGGCCGGTACCTACTAA
CTTACAGCCCGCGCCAATGCTTATGAATCAGTCCAGCGTTCAACGTCTGCAGTCCTCACCGCCTATAGCTCAAAGGACAATGCACGCCTCCAAGC
ACACCGGAACGCCTGGCTCCACGCCTTCATCGGTGGCCAATGCGATTAATAAAACCGTCATGCGTGCCCGGAACTCAGAAGCCGCTTTCTTGGCG
CAAAAACAACAGCAGAAACAGCACCAGCAACAGCAGCAACAACAGCAACAACACCTGCAACAACAACAAAAGCAACAACAGGCGCAGCAACAGTT
CCTACTACCTCGACCTAGTCCCGGTCCCACGCCAGGTTCGAGTCCCGCCAAGCAAGTGCCGAAGTGCACAACTAAAGTGCGCGCCAAGCAGCCAC
CGCTTTCGGGGGCCACGGTCTCGGTGCCCATCTCATCTAGCAGCAGTGGATCGGAATTGGGCAGCTATGGACAGCAGCAGGAGTCCAGCTTGGCG
CCGGCCAAGCCCAAGGAGAAGGCAGTCATTGACCTCACAGATGAGGATGATGCAGCGGCTGCGGCGGCGGCTAGGGCTGCCCAAGCACAAAACGC
TCGTTTGCGTATGGAGATGCTTAAGCGGAATGCTCAGACTGCAGCAGCGACGAGAGGAGGACGAGGAGGCGGAAATGTGGTGCGAGCTTCTCCAA
TGCAATTGCCTCGCGTAAATGCTCGACAGATAGTCCATAATAATGGAGGAGGTCAGCAAAGTCCCTTGGGCTCAAACGTAACTATGCAGATACGT
TCGGAAAACACCCCGCCTCCAGCGTCTCGTCTAAGATACTCACATCCTGCACCACTGCCCACGTCTCCTCCCCAGCCCTTCAATCCATCCTGGAA
GGTGCCTCCTTCGCGACCCGTTATCCGGATTAGTCTCCTTGATACTGGTATCGTTATATCCTGGACTCTGGAGGATTCGAGCCCGCGGTTCGCAG
AGTGCGTAATGTACCAGATCTATGCATACCAGGAGACGATTAACGAGCCCAGCACGGATAGCTGGCGGCATGTGGGCGATGTCAGCGCTATGTTG
CTGCCAATGGCAGTGACTTTAAATCAGTTCCAGGAGAACCAGAGGTATTACTTCGCTGTGCGGGGCGTTGATAGTCACGAACGATTCGGGCCGTT
CAGTGTTCCCAAGACCTGGTCGTAGACGGATTGGTCTGTTCTCTTCCTTAGATTCTAGTTTTAGTAGAAGATATGTAATTTACTTTTGTCCTTGG
TAATCCGTTCTCGAAACTAGCCGGAATTATGAGTTTATACGCCTAAGTTATAAAGAGATTATTGAAGAATTTTTAAGAAGTAATAAACAAGTTAT
GCCAAGCAGTCAATCCACTGCAGTCAGTAAAGAAGAAACAAACAAAACATTGTATTTCATTCTCACTAGGTTATTTAACATAAATAAGTTCAAAA
CTTACATTAAATAATAATTTGAAT
(SEQ ID NO: 869)

Start ATG: 228 (Reverse strand: CAT)

MMGVNQTMELKELSTEEALMRTLSTELGNEVEPLSTPAILNESSQTSVDEVDLCELTNGVDSSDNVKVIDKPKKISDRERNPGSDLDALLDKISS
IVDCSPRNSDDIDSLDRDEECDSASAKKRTAADTDENLKEQREKPEEEEEGEEVLSSLEGEECIDPDSELKTEEKLDETEEHASAKESTQKTEDL
ADSDEILKSKEEDEVPANTADNIEKDRKNTSTDDVFMYALDCISSADEFDAFASQDSKKAKPSKKLNTENNSSVNDLEDISSDDDDIIKETEKPN
TEVIDLDSSSECVPCEAESEVEETEANTEDTEVLTHGKVSTKKSLNLQNNISEKSASAAEYESVKADQHLTEGKEPMLVGDEVTEKSKESIPIQS
EESIQVDEPEESKESEELEEHKEKEEPDYCKETKDSEEATEKEKSEIKIIKASKVAQILGDTKEEEDPSPTQEVEDVKETEEPENKKEIEDTEEL
EEPVVIEGEETEDPQKKVQKEFDVRTADHEMNYTTIDDKLDEAVKDVVEIEEKKAAEDELGVIPKGDKEPTTNGACEISTDGNLKDLESNESTVV
EEETKETESDDEVIFFEPLDKTENVGTTANPTNENSVKPQAKDDEVVLVSEDEDETPQNGISEKEVQTIQKETALKGLPNESTTESVEAKNLQID
NSDNACDQFEKLKTHDMVKQTTTEDGNSNSSNLLRPAEYAEESVPKRLRLSTDEKNEFEAETNQESLPILSRAEGGLKDVTKRSHEHLDSSPQEE
IPNKKAKTEDSDSNSSHEGTLQIDMGGQEDKEESPKKDTQKKLDFDLNPVPEIKQNVKPLRLEFFKTFRRSFDTMTRDDLEELVLQKVVEAMMVK
SDFAEIRMQLDKCESTLANYRRKIAEVSKQFLDLETVHKRVLKDLEAKNSHFTAPVRITRAVGLQVGIPFKAIKPTVAAPESTHAAGSVLAPPSG
TPPKASTSPTRATVRPRPPPPTFGPSTSSSETGAGVSVTPNSNHQQQQPAARSSQSLTTASVTPPVRRGCLQKVTPHRPVPTNLQPAPMLMNQSS
VQRLQSSPPIAQRTMHASKHTGTPGSTPSSVANAINKTVMRARNSEAAFLAQKQQQKQHQQQQQQQQHLQQQQKQQQAQQQFLLPRPSPGPTPG
SSPAKQVPKCTTKVRAKQPPLSGATVSVPISSSSSGSELGSYGQQQESSLAPAKPKEKAVIDLTDEDDAAAAAAARAAQAQNARLRMEMLKRNAQ
TAAATRGGRGGGNVVRASPMQLPRVNARQIVHNNGGGQQSPLGSNVTMQIRSENTPPPASRLRYSHPAPLPTSPPQPFNPSWKVPPSRPVIRISL
LDTGIVISWTLEDSSPRFAECVMYQIYAYQETINEPSTDSWRHVGDVSAMLLPMAVTLNQFQENQRYYFAVRGVDSHERFGPFSVPKTWS*
(SEQ ID NO: 870)

Classification: known_flybase_gene
Gene Symbol: BcDNA:LD26050
FlyBase ID: FBgn0027499

Celera Sequence No. : 142000013384139
TTAAGTTACGCAGAGCAAAAAGCCGGGTTACTCATGTCACATCAATTTCCAAGCCAACAACGCCCCCTAAATAGAAAGCAACAACTATTATTAAT
AGACTTAAATTAGGCGATATACATATACATACTTACATAGAACAAACCTACATTGAGACATACTTATACATACATGCGAAGTGACTAAATTATTG
GCTATTGTAATTTGTATTTGTAATATGACTATTCAGAATTAAGATATTATTAAGTGGCCGATAAATTTAAGTAGCAGGCGCCGTTCAGCAGCAGT GTCATTTATAGAATTTTAAATTAACTACGAAGACATCGAGAAATCATCATTAGGCACTTGCTAAAATTGTACTAACAATACCGCAGACATATTGG
TGAACGATATCAAAATGTTGCCCAATTTACTTGTTTACTTTTGTCAGCGGTGGGGATTTGGTTTTTTTGAATTCCCACCAAACATCGGAGCTCGA
TTATTGAGATGATTTCCTGGTTGATTTCGTTTACACAATTATACAGAGTTCATAAGCCGCATGTCTATCAAAACACCAAAATGATCTGTTATCAA
TAAATATATGTACTTGACATTCTGATATTTACACATGCATAAATACTATTATTAAACATTTTTAAAGAAAAATATATTTTGATCGAAAACATTCG
GTTGCGTTTGATTTACAAGCGAGCAGGTTGGAACGTTTTTAATATTTTGGGTATTTTTGGGGTCAAAAGTGGAATAACCAAATAATTAAGTACAC
GATATTCTCATAAATTACGCAGAATATGAAAACACTCAGACCCAAAACTCCTCAACAAAAAACAACAAAATTATTGTACATATATCTTTGTATTA
TATTTATATATTTTAGACCCTCCAGATTAGATGCATCAGTTGAAAATAAGTTAACTTTTCTTTGTAGTTTAAAACTTGATTACAATTAAGATAAA
TATGTAGGGATTAGCTATGTACAATGGGAACAGCTGTGGGATTACCGAACTCAAACTAGACTCGAGACATTGTTGTAGAGGCCAACGGCAGACAG
CTCGTCCAGATCGATTTCATTGGATGGAAGATTGGGATGAGGCCAGTTCCTTGGCCTTTGATTAACATGGGGCGGCACAATGGCCTGAAAGGTGG
GGGACTGCAGAGGCCTATAGGCTACCGCATCCACGTAGTCCACTTGTCTTGGTGGAGCATTTGGATGTGGAATCCTTCCCACGTAAAGATCTTCA
CTGCGATAGAGACTCGCATTTGGTACGTAGCCGGAGTGCAGCCTTCTCTGCGGAGTTTGCGGAATCGGTGGACGGTGGGGCAGTTCATGGAAGTA
AGCATCTTTGGGTATGTGTCTCTCGGGCAGCCCAAACTGGGCGCTACTCCGGTGGGGAATACTATACGTGGGCGAAGGGTTCGAAGAGGTGCCCT
CCAAGTGATGGAAGTTATTGTTCAAGCGGGAGTGTGATCTTGCGGCGATCACATGTGCCGTCTGGGAGTCCTGTCGATTGGAGTCAATGGTGTTT
TGCAGTTGGGCCACCATATCCCTCACCTGACCAGCGTTCGGCTTTTAGGCACTTGATTTCACTGTTCCGAATCTCCACCTTACTCATACTTTC
ATTGCCATTTTGACGCACTTCTGTTTCCTCGGCGTACTCCATGATGGGATTGGAGTAAAATAAATTCGACATGACGGGATAGTTGTCTTCCAAGC
AAAGAGGCTGCCGTTTCATCAGATTGGAGATACCTGCCGCCTCGCTCGCTTGCTCCTTGTAGAGCAGCTTGTCGCCTCCCATTCCCTCGGCAGTT
TCATTGACAGCCGTCTCCTCTTTGCCCAGATCCGCGAAGGAGGCATCTTTTCGAAGCGCCTTGATCACCGAGTTCAGCATGTTCTCTCCTCTCCC
AATGCGCTGGTAGTACTTATTGTAATCCGGGTGGGGATTGCTGCCCGTGGGTGATGCCTCCCAGTCCCAGCTGTTGGAGTTCTGGGAGGGATTTG
AGGTCTCACTGGAGTTCGGATAGCGTCGTATCACGTTGGCGTACTCGTCGAAATTGGGACTATTAACACTCTCTTTATCTTCTCGAAGTTGGGCA
GACTCCGCCCTTGGATGGGGATTATAAGGTGGCGATAAGGAAGAAAGCTGGCGCTTGCTCTCCTGTTCGCTGTCCCTTTCCATGATCAGGGTGGT
TTTCTCTAAAAGCACTCCCAGTCTTTCGGAGACTTTTAGGAAATCTAGCTTAAGTTCATCTAGCTTCGAGTGCTCCTCTGGTTCCGCCTCTTCTT
GCACCTGGTCCTTGTCACCCACTTCTGCCTCTTCTTCATCCCGAGCTTCATTGGAATCGTCATCGCTGTCGCTATCCACCTGGACCTCCGCTGAT
CGGTGTACTATAGCCTCCACTGCCTGATCTTCCAGGACATCTACACTCCGTGAGTTGGTGAGCCTACCACCTTCGTGGTTGTTTTCCAAGAGCTC
TAGACTGCGGCACCTGGACATTGTTCTTTCGATCCTTGAGCTCTTGTTCTGCTGATCGAAGGTGGACCGCATAGGTTCACCTCGTCGCAGGAACT
CACTGAGGTGCTGCCTCTTGCTCTCGCATCGCAATCTGTCCTCGATCATCGTTCTTGTGAGCTGTTCAATCTGATCGTTCGTCTTGATTGCCAAT
GCCTGAACTTTGTGACCTAGACGTTCCTTGGTTTTGTGAACGTATTTCTTCAAACTCTTTCGATTGCAATTTAGTTTGTTTTCAATGTGACGGAA
GAAGGGACCGCAATAGCATGTGTTGCCCACGCTGACCGGACCCTTGTGAATATGACCAGCCAAATCCAGGAAGTATTGCTCCCCCGACTTAAGTG
GCTCCTTGGGCAGTGTCTCCAGTTTTGGTGAAGGAAAGGCACGCGGATCGGGAAAGTAGTGACAGCCATAGGGTGACCAGTTGATACCCTTGTCC
ACCACATCCCTTTCACGATCTCTGTCCTTGTCCGATCTGCTGCCGCCCCTCCTTGGGTTTCTCCTTGCGATTCCGTATCTTCTTCGGCGTGTTCAG
GATCTCGATGATTTCACGGTAGTTCTTCCTGATCGCTATGTGCATGGGGCAGTCGCCTTGTGCGTTTTTAATGCCCAGCCGAGCATCTGCCTCTA
GGAGAATCCTTGTCAGCTTCCTGCGACCCATGGCACAGGTGATGTGCAAAGCGGTGTCGCCGTTCAGATTTGTTTTATTCGGATCGCAAAGGGCG
GAGAGCAGGATCCGGGAGACTCCTGCATGTCCATATCTGCAGGCGGTGTGCAGCGGAGTATCTCCATACTGAAATTGTTAAACATGTTAAACATG
GTTATCACTGATATGATCCAACACTTACATTATTCCGGACATCGGGATCGGCGCCGGCCAGCAGTAGCTCCCTAGAGCTCTGATTGTGACCATTT
TGAGCGGCCAAGTGCAGGGCGGACAACCCTTCGTTGTTGGCAATACCCAGGGCGCTATTGTGTAGGGCTTCGATGGTCTGGTGGGCCACCTTCAC
TCTGCCCTTGTTCTTATCCTTGTCTTTGTCCTTCTGTCCCTTTGCTGCTTTTCCCACCCCCGAGGAAGCGGGTGGCGTGGGGGGCGTGCAGATCA
ATTTCACGCAGCGACTGAACCCCCGACTGGCGGCCTCATGGAGCGGGGTATTCCCCTGCACGGATTCCCTGGCCAGTCGATCAGCATTGCTGAAC
AGGAGACCCTCCACCCGGCGATCATCTCCGGCGGCTACCGCCTCGTGCAGCGAAGTCCAATTGCTGGAGTCGGGCTTAAATCAGAAAAAGAAGTT
ACATCGGTGTAAGATTTGTTGGTTCAGGCAAGTGCCCTTACTTACCCCGGATATCGCATTCGGGAGAGCTTCCTGTTTCGGAATGCGGGAGGATC
CATGCTGCATTGTCTGCGAAAATATTCATTATTTATCAAATTTGTTAAATTATAATTTCATTCATTTATCATGATGTGTTGCAATTATAACTTTT
TAAGTAACACTTTATCAAAACCAGATAAAATTAAAAAAATTATTTATATTAGAACTACATTTTGTCTTTAATAAATGAAAAATCTTACTTAAAGT
ACCGTAATTACCGTTAGAATCGTTTATATGTCGAAAATCATATGAAAGATGGTATTCTTTGATATAACCTTGTTGACGACGAAAGAGCTTAACTT
GACCTGGGATCAAATGAATCTGATCTTCGATCGCACATTTTCTAGCCGTGTATGCGCATGTATGTGTGCCTCACGTAATGGCGTACCACGTAGTA
ATTGTCATTACAAATAGAAGTGGGAGTTACCAAAAGCGATCAAATAAAGGACTCGTAATTTGAAATACAACCTTTTTGAGGGTAGATTAAATGTC
TTTCATTATAACACATTGATAAAACATGTATGGTTTCTTAAATGTTCAACACTATTACAGTAAATTTCTAGACCTGAAAACCAGGTTTAAAGTGC
GCCTAGGTTTTCTCGATTCCCGACTTACTTTTCACTAATTTTAAATCCCGTCTTTGGACCGCAATTTACGCATTGCAATTCGCCACTCTCACGTA
TTTACACATGTTTACTTTCGACTATTGTTCAGTACCCGACTTTGCAGTATTTGGCCATTGATGGATTGATGGAACGCCCAGAGTTAATTTGGCTT
CAAGCCAGGCCTAAAAAGAGACTAAAAGAAAGCCAATCACAGGCAAAATTGGCAACAGGTTTCGAGCTGGGTTGCCGTACCTGCGACAGCTAACG
GTGAAGCCGATAGTCTGCATTATTGCTCCAACAGAAGTACGGTCACTCTACAAGTAGGCAACGAATTTTGTTTGTCATCGGCATTTCGCATTCAA
CGTTTCCAATTGTTTTTTAAGGAGCTTTAAGAATGGCTTTAGCTGAAATCTGCAAGATATCGAATGCTCCGTACATGCGGCCCAATGCCTGGTCA
TCGGCGGATGTGGAGGAAGAGCAAAAAGGGCTTATGTGCAATCTGGCCAATCCCTACACACTGGCTGCTCCGCCATTCGAGAACGTATGTAGTTA
ATTAGCTGATCTTCTTGGGAAATTTACTAAAAAATTTGACAATTTCCTCAGCCCCTGCACAACCTTAATCAGATCCAGGCCAATGGCGACAAGAC
CGGCGTCAAAATCAACTTCGATCACGGCACCACAACGTTGGGCTTCAAGTTCAAGGGCGGCGTTCTCCTGGCAGTCGATTCCCGTGCCACGGGTG
GATCGTACATTGGCTCCCAGTCGATGAAGAAGATCGTGGAGATCAATCAGTTCATGCTGGGCACCTTGGCCGGTGGCGCAGCCGATTGCGTTTAC
TGGGACAGGGTCCTTTCGAAGGAATGCCGCCTTCACGAGCTTCGAAACAAGGAACGCATCTCGGTGGCCGCCGCCAGCAAGATAATGGCCAACAT
TGCCCACGAATACAAGGGAATGGGTCTGAGCATGGGCATGATGCTGGCCGGTTACGATAAGCGTGGTCCAGGCCTCTACTATGTGGACTCCGAGG
GATCTCGCACGCCTGGCAATTTGTTCTCTGTTGGTAGTGGATCGCTGTACGCCTACGGTGTCCTGGACTCTGGCTATCATTGGGACCTGGAGGAC
AAGGAGGCCCAGGAGCTGGGACGTCGCGCCATCTACCATGCCACCTT
(SEQ ID NO: 871)

Exon: 4652..4494
Exon: 3908..3846
Exon: 3768..3354
Exon: 3298..1001
Start ATG: 3898 (Reverse strand: CAT)

Transcript No. : CT23371
CCAAATTAACTCTGGGCGTTCCATCAATCCATCAATGGCCAAATACTGCAAAGTCGGGTACTGAACAATAGTCGAAAGTAAACATGTGTAAATAC
GTGAGAGTGGCGAATTGCAATGCGTAAATTGCGGTCCAAAGACGGGATTTAAAATTAGTGAAAAACAATGCAGCATGGATCCTCCCGCATTCCGA
AACAGGAAGCTCTCCCGAATGCGATATCCGGGCAATTGGACTTCGCTGCACGAGGCGGTAGCCGCCGGAGATGATCGCCGGGTGGAGGGTCTCCT
GTTCAGCAATGCTGATCGACTGGCCAGGGAATCCGTGCAGGGGAATACCCCGCTCCATGAGGCCGCCAGTCGGGGGTTCAGTCGCTGCGTGAAAT
TGATCTGCACGCCCCCCACGCCACCCGCTTCCTCGGGGGTGGGAAAAGCAGCAAAGGGACAGAAGGACAAAGACAAGGATAAGAACAAGGGCAGA GTGAAGGTGGCCCACCAGACCATCGAAGCCCTACACAATAGCGCCCTGGGTATTGCCAACAACGAAGGGTTGTCCGCCCTGCACTTGGCCGCTCA
AAATGGTCACAATCAGAGCTCTAGGGAGCTACTGCTGGCCGGCGCCGATCCCGATGTCCGGAATAATTATGGAGATACTCCGCTGCACACCGCCT
GCAGATATGGACATGCAGGAGTCTCCCGGATCCTGCTCTCCGCCCTTTGCGATCCGAATAAAACAAATCTGAACGGCGACACCGCTTTGCACATC
ACCTGTGCCATGGGTCGCAGGAAGCTGACAAGGATTCTCCTAGAGGCAGATGCTCGGCTGGGCATTAAAAACGCACAAGGCGACTGCCCCATGCA
CATAGCGATCAGGAAGAACTACCGTGAAATCATCGAGATCCTGAACACGCCGAAGAAGATACGGAATCGCAAGGAGAAACCCAAGGAGGGCGGCA
GCAGATCGGACAAGGACAGAGATCGTGAAAGGGATGTGGTGGACAAGGGTATCAACTGGTCACCCTATGGCTGTCACTACTTTCCCGATCCGCGT
GCCTTTCCTTCACCAAAACTGGAGACACTGCCCAAGGAGCCACTTAAGTCGGGGGAGCAATACTTCCTGGATTTGGCTGGTCATATTCACAAGGG
TCCGGTCAGCGTGGGCAACACATGCTATTGCGGTCCCTTCTTCCGTCACATTGAAAACAAACTAAATTGCAATCGAAAGAGTTTGAAGAAATACG
TTCACAAAACCAAGGAACGTCTAGGTCACAAAGTTCAGGCATTGGCAATCAAGACGAACGATCAGATTGAACAGCTCACAAGAACGATGATCGAG
GACAGATTGCGATGCGAGAGCAAGAGGCAGCACCTCAGTGAGTTCCTGCGACGAGGTGAACCTATGCGGTCCACCTTCGATCAGCAGAACAAGAG
CTCAAGGATCGAAAGAACAATGTCCAGGTGCCGCAGTCTAGAGCTCTTGGAAAACAACCACGAAGGTGGTAGGCTCACCAACTCACGGAGTGTAG
ATGTCCTGGAAGATCAGGCAGTGGAGGCTATAGTACACCGATCAGCGGAGGTCCAGGTGGATAGCGACAGCGATGACGATTCCAATGAAGCTCGG
GATGAAGAAGAGGCAGAAGTGGGTGACAAGGACCAGGTGCAAGAAGAGGCGGAACCAGAGGAGCACTCGAAGCTAGATGAACTTAAGCTAGATTT
CCTAAAAGTCTCCGAAAGACTGGGAGTGCTTTTAGAGAAAACCACCCTGATCATGGAAAGGGACAGCGAACAGGAGAGCAAGCGCCAGCTTTCTT
CCTTATCGCCACCTTATAATCCCCATCCAAGGGCGGAGTCTGCCCAACTTCGAGAAGATAAAGAGAGTGTTAATAGTCCCAATTTCGACGAGTAC
GCCAACGTGATACGACGCTATCCGAACTCCAGTGAGACCTCAAATCCCTCCCAGAACTCCAACAGCTGGGACTGGGAGGCATCACCCACGGGCAG
CAATCCCCACCCGGATTACAATAAGTACTACCAGCGCATTGGGAGAGGAGAGAACATGCTGAACTCGGTGATCAAGGCGCTTCGAAAAGATGCCT
CCTTCGCGGATCTGGGCAAAGAGGAGACGGCTGTCAATGAAACTGCCGAGGGAATGGGAGGCGACAAGCTGCTCTACAAGGAGCAAGCGAGCGAG
GCGGCAGGTATCTCCAATCTGATGAAACGGCAGCCTCTTTGCTTGGAAGACAACTATCCCGTCATGTCGAATTTATTTTACTCCAATCCCATCAT
GGAGTACGCCGAGGAAACAGAAGTGCGTCAAAATGGCAATGAAAGTATGAGTAAGGTGGAGATTCGGAACAGTGAAATCAAGTGCCTAAAGAAGC
CGAACGCTGGTCAGGTGAGGGATATGGTGGCCCAACTGCAAAACACCATTGACTCCAATCGACAGGACTCCCAGACGGCACATGTGATCGCCGCA
AGATCACACTCCCGCTTGAACAATAACTTCCATCACTTGGAGGGCACCTCTTCGAACCCTTCGCCCACGTATAGTATTCCCCACCGGAGTAGCGC
CCAGTTTGGGCTGCCCGAGAGACACATACCCAAAGATGCTTACTTCCATGAACTGCCCCACCGTCCACCGATTCCGCAAACTCCGCAGAGAAGGC
TGCACTCCGGCTACGTACCAAATGCGAGTCTCTATCGCAGTGAAGATCTTTACGTGGGAAGGATTCCACATCCAAATGCTCCACCAAGACAAGTG
GACTACGTGGATGCGGTAGCCTATAGGCCTCTGCAGTCCCCCACCTTTCAGGCCATTGTGCCGCCCCATGTTAATCAAAGGCCAAGGAACTGGCC
TCATCCCAATCTTCCATCCAATGAAATCGATCTGGACGAGCTGTCTGCCGTTGGCCTCTACAACAATGTCTCGAGTCTAGTTTGA
(SEQ ID NO: 872)

Start ATG: 170 (Reverse strand: CAT)

MDPPAFRNRKLSRMRYPGNWTSLHEAVAAGDDRRVEGLLFSNADRLARESVQGNTPLHEAASRGFSRCVKLICTPPTPPASSGVGKAAKGQKDKD
KDKNKGRVKVAHQTIEALHNSALGIANNEGLSALHLAAQNGHNQSSRELLLAGADPDVRNNYGDTPLHTACRYGHAGVSRILLSALCDPNKTNLN
GDTALHITCAMGRRKLTRILLEADARLGIKNAQGDCPMHIAIRKNYREIIEILNTPKKIRNRKEKPKEGGSRSDKDRDRERDVVDKGINWSPYGC
HYFPDPRAFPSPKLETLPKEPLKSGEQYFLDLAGHIHKGPVSVGNTCYCGPFFRHIENKLNCNRKSLKKYVHKTKERLGHKVQALAIKTNDQIEQ
LTRTMIEDRLRCESKRQHLSEFLRRGEPMRSTFDQQNKSSRIERTMSRCRSLELLENNHEGGRLTNSRSVDVLEDQAVEAIVHRSAEVQVDSDSD
DDSNEARDEEEAEVGDKDQVQEEAEPEEHSKLDELKLDFLKVSERLGVLLEKTTLIMERDSEQESKRQLSSLSPPYNPHPRAESAQLREDKESVN
SPNFDEYANVIRRYPNSSETSNPSQNSNSWDWEASPTGSNPHPDYNKYYQRIGRGENMLNSVIKALRKDASFADLGKEETAVNETAEGMGGDKLL
YKEQASEAAGISNLMKRQPLCLEDNYPVMSNLFYSNPIMEYAEETEVRQNGNESMSKVEIRNSEIKCLKKPNAGQVRDMVAQLQNTIDSNRQDSQ
TAHVIAARSHSRLNNNFHHLEGTSSNPSPTYSIPHRSSAQFGLPERHIPKDAYFHELPHRPPIPQTPQRRLHSGYVPNASLYRSEDLYVGRIPHP
NAPPRQVDYVDAVAYRPLQSPTFQAIVPPHVNQRPRNWPHPNLPSNEIDLDELSAVGLYNNVSSLV*
(SEQ ID NO: 873)

Name: Ankyrin-repeats containing protein
Classification: cytoskeletal_structural_protein Celera Sequence No. : 142000013384684
ACCCAGGCCGGAGGCTCCACGCATCCCGCTGCCAGTGCCAATTGCCACGGTTACGGGAAGCCGGACGCTTATCCCACTTTCCGGATACGATTGCC
TAGCAGATCTGCCGTCCGTACATATTGAACAGACCTTTGAGCTTAACGATGGTAAGTACAAGCCCAAAAATTAGCTAAAATCGCTTCTAATAGTT
CGTCTTCCCTTTGCAGCCCTAACAGGCGTCTCCTCGGAGAATCGATATGTGGTGCGATCTCCACTGGGTGATGCCATTTTCGCGGCCAACGAGAG
TTCCACAGAAAAAAATCGACTACTTTGGGGAGCTGGTCGACCCTTTCAGATGCACCTGCTGGATAAAACGCACCAGGAAGCTCTGGTTTTTCGCA
AAAAACTAGCGATGGGATCCATGTGCTGCCAGGCAAAAAGTCTAGAAATTTGGATACCACCTGGTAATTTGCTGGGTAAAGTGGTGCAGTCGCCC
ACCTTCATGCAGCCGGAGTTCTTTATCGAAGACGAAAGCACAGGACAACTAACATTCTGTGTAGAGGGTCCTGTCGGTTTAGGATTCTGCTGCTT
CAGTTTGCCCAAAGATTGTTATTTTAAGGTTGGTAGTAGCTTTAACATTCGGAACAGAATATTCAATTATAGTGTTTTTGTTCCCTTACAGATCC
ATTCGGGAGGCAATATGAGGGCTTCCATAGACCACAAATGGCTCGCCAGCAAGTCTCAGTACACCACAAATATATACTTTAGTGACGCCAAGCTA
ACCGCCAAGGAGCGGGCTTTGATACTGGGATCAGCCTTTCTACTGGTACTGTGCTCCTAGTTTATATACATATATCATTTGCCACAATAATGTTT
TGTATTCGTTTTTCAGGAATATCTATTCTTCCAAACCCGCTTTTGACGTGATTAATCAATAAAAAAAAAACATTGTATATTCACATTGATTTCTTT
ATTTTTTGTCATTTTTTTGTATAAGATTTTATGTTTGTTTGTGTTTTGTTTTTTTTTTTTCTCAGTTTTTTGATATATTTTACAATAATGTAATA
GATCACTTCATTTTCTTGTTGTTTAACCACATACACACATTCAAATATATAGATATATATCTATGTGTATATATAGATTTTGCTGCAGCGCTTGC
CATAGCAGTTTGTACAATATTTCATTTATATCTATCAACTTTGTGTAGTTTGTTTATCTAACCTACCGCTTAATGCATATATGACAACATATTGA
TTATTTACAGTTAGCGTTTTTTTTCATCATTTCGTTTCTCTTCTGTCAAATACAAAATTAAAAGAAACAATTAAATGAGTCTCGTGGTCTCGTTG
TTTAAAGAATTAAAACAAAACTAGGGGCGCAAGTCATTTCTCATTCACCGTTAATAGTTGCGCTTCAAAACTTGGTGTGATAACAATTTGAAATA
AGGAAGAACTACGTGATTTTCAAAGGGCAAAACTTGGATTTGGACATAGAAAACCAATATACTTAGTGTGCGGGTGTGTTCTGGTTCGGTTTGGA
GGTTCATTTTCGGGGCTAGGCCTTAAAAATAACACACTTCTCTCGCTCTCGGATCTTTACATTTGTAGATAGACTCACAGCACTTCAGGAGTTTT
TGCATTTATGCATTTCGAAAACAAATTATGGTTAAGTGTATACAATATAGATAGATTTATAAGTGTGCTCGTTGGTTGGCTTATAACTAGGGCTA
GCTGATGACGATTCCTTAACCTAAATACTTAAGAGGCAGATCGAAACGATCTGTGTGGGGTGACTGCCTTTTAAAACCGTAAAAGGCTTTGTATA
TGATTATTTTAGCGCAATTCGCCTAGAGTGTTTACACTGGAATAGCTGACTCGCTTATCTGGCTCCCCTATCGTTTGATTACTACTCGCGATTAG
CCCAATACTAGTTGGGCCCATCATCGAAGAGAGGTGGGTCTTATAGGCTAGCTCTAGAGTAAGTTGTGTGTGCCCATATGCGATATGCTTAGA
CATTTGATATGCGCTCGTTGGAGGTGGTTTGGTCATGGCGGCCCTCGATCCTGGAATTGTAGATGCCGTACTGACTGCTGTCCAGGTGGTAGACC
GCGGGATACTGATAACCTCAGCTGGGCTGCAGCATGTACATGTACTGTCAGTTGCTTGCCGCTGCTGAAGCAGCCACGGGAACGGCCACGGGAAC
AGGCAGCTCCTGGCCAGAACGAGCCCGCTTCTCGCCACTGCTTTCCGGTGGATTATCGCTCTCCTCGCCCGTACTGCTGAAACTGCCCGGCAAAC GACGCTTCAGGCTATGGTTTAGGCCATTGGCCACCGTTTCATCCTCGGACATCGAGCTGGCTCGCTTGGGTGTGTTGCCAGCACTGTCGTTGTCC
AGCGAAGCTATAGCCGAGGCAATTGCGGCACTAAAGCCATCCTCGGACGCACTATCCTGCGAGACGGGACCTGCTGCATCCTGGGCCAGCTGCAT
CATGCCAGAAGGTGTGGTATAGCTACTGAGCTTACCAGGATCCTTCTCCTGCAGTTTCTGGGCCAGCAACTTGAGTGATATCAGCGAATTTTCAC
AGTCGCTTGTATCGATTTCAGTGAGACTAATTCCGGCACGTTCAATTTCAGCATAGGTCCCGAAGGGCAACTTCTGCAGACACTCTAGCTTCTGA
ACATGCGTCTTGGAGCGCAAATGCTTGGCCAAATGCCCATGGATGCGGAAGGCGATCTTGCAGTCGGTGCACTCGAAGGGTCGCGGATTTGAGGT
GGTTGGAACACCAAAAGTCGACGTCATCATAACCTTGTTTTGTGCGCTTCCGATCGCTCGTGCTTCTGCAGATGTCCTTGCGTGCGGAAGGATA
TGCTGCATGGCTCGCACTTAAACTTTCGCTCCATGTAATGAATATTCATGTGCAGGGTCAGCTGATGTTGCCGCTGAAACGTCTTGGAGCACATG
GTGCAGGTGGGACGTGCATCACCTGCAATGGGAGCTGGCGGCACTCCTCTGCCATACGATACATGCTGGAGATCGCCGCTCTTGCTAGTGGGAGT
AGAGCTTTTGAAGCCATCTTCACCCACAATCACAGTACGCTGCGCGGGCTGAGTTGAGTTGGCAGTGGATGAGGGTGCCACAGGTGCAGCTGTTG
TTGTGCTTACTGAAGTAGCAGTAACAGACGATGTTGGTGGTGCAGTCGGATTTCCAAGTACTCCAGTAAATTCATTGACATCCGGTTGCTGCACT
GCAGCAGGCAGATTGGCATTGTGTGGCTCTGCGATATTAGGCTCCTCGTTTTCTTCCTGGGCAATCTGAGCAAGAATAACCGGGGCCTGTTCAGG
TGCACTCCGAGGTGACTCAATGGCCTCTGGGGTCTTTACTTCGTGCACTTCGATGCTAGGTACCTCATTTACGCTCATAACGGGCCTGCTGTTGG
CGGTAAAGAGAGTGCTACTACTGCTCATTACAGGAGACGCCGCTGTGTATAATGTGTTGATCAGATAGCTGCGGCTAAACTGACTCTGCTTTATC
TTGGCTTGATGCAGCGCATGCTCCTTAATGTAGGTCTGTAGTTGAACATCCTCGCCCTCGGCCTCGTGCTTGGCCTGCTCTTCCATTTCGGCAGA
TATTCGCACTTTGTCCGAAACCGAGATTAGAGTCTTCATGAAACCGCTTTCGTTGCCGGAGGTTCCAAAGATAACATCGTGCATCTGTTGGGCCT
GCGATTTGGGAAGATCATGAGCGGGCACCGAAACAGGCGAGGGGGATATTAATAAGATGGAGCCGCGTGGCTTAGTGAGATCCATGGGAGCACTC
TCCTCGTTGGCCACACTCCGTTTCGGTTTGGACTCCTCCGGATTGGAGTAATACTGTTCCTGCTTTTGGTAGTCGAAAGGCGGCTTCGGCGATGT
AAAGGAGCACACTAATCTTTTAGGTTGCGAACCCGAAGAGCCAATGCTGTTTGCAGGACTGGCCGCTGGTAGGGGTGTATCCTGCAACTGCGGAT
AGGGCGATACGCTCTGCGGTATGGGCGGCGTCATTGATAACGAGAGTAGGCCTCTGGCTGCTTCGTGCTCTTTCTGTCGCGACTTGGACTCATCC
GTATCTGTGAAGAGATTATAATGAATCAGCTATTTGAACATATAAGTGTATATGATTGCTTTCTTACCACTACTTTCAGATTCATTATCACTGTA
GTCATCGGAATCCGATTCCCCAGCCATCGATGATGTGCGTCCTCCTGCCGAAGTGGATGACTGCTGGTCAAAGTCCATATCTACATCCAAGAACT
CGCTGTCTGGCGGCATTGGTCCCGGATTTATTCCCAGTTCAATGCACTTCTTAAAGTGAGTTTTCGATTGCATATGCTTGGTCAGATTTCCCTTG
GTCTTAAAACTGTGGAATGGAACAAAGTTTATAATAAGTTATCTCTTAAGTACGGAAAAAATGCAATGACTCACCTGAAGTTGCAATGGCTGCAT
GTGAATGGCCTCACGTCCGTGTGAGTGCGAATGTGCTTCTTGAGCATCGACGGCTTCTTGCAACGAATTCCGCACTCGGAGCAAACATATCTTCC
CCTTCCGCGGCCACGGATGTACGTGTAATCCTCATGAGACTCGTAGCCACCCACCAGGGGCTGCCCGGATGGACTTGTCTCCAACTTTTGGCCT
GTGCCTCCTCATTCGCCTTGGCCGCCACATTTGCCTCACTGAGAGCGGCAATCGTGACAGTGGGTGGGGTCTTTAGGGGTCCTTGATAGAAAGCA
CTGCTAGTGGAGGACGTCGAGGGGGAGGATACGATTTGCTGGGAAGCGACTAAGTTGTAGCTAAGTTTTCCCGATCCAGCCATGGCGGTTGAGCT
GCCATTTCCTAACATCCTTTGACGTGAGTCGTAGAGTGCCATAACTTGCTTTAGTTTGAATCCAAGTGGATGTGGCTGGTTCTCCTCGCAAACCT
GCCACACACTATACATCGATAGTTTGTGCATTCCTGCCACATACGAAGGCTGTGGACAGTTCACCGTACAGTAAAACATCTTTGTGCTGCATTTG
AGGCCCAGATATGTGTAGGCGTGTCCATTGAGATACAGTTGCACACAGGATTTGGACGGCCTGGGGGTCTCCGGCGAGATCAGCGGCAATGTATT
GGCTGTCGGTGTAATGCCATGATGGCGTTTAGGAGTAAAAGTACCGGGTTTAAGTGGCAAACTAGTAGGCCGCAGAAACTTGGACTTCGCCGATG
CTGAGGCACTGGCTACGGGACTGGTCTCTTCTGGAGCGTTTCCGTTGGGAGTATCAACATGTAGCGGTGTTAGGGGCAACTCTTGCTGTTTCCCA
GAAATCACATTTTCCAAATTAAAGTGTCGAACTTCAGGTTCAGTGGTCTTCACATTATCAGCCATGCGTAGAAAGTTAAATGGTGCTTTCTTCGG
TGCCTCCTTGCTGTTCCACTGCAGCGCTTGCCGCTGGGCAGGAGTTGGTGGCTGTCGACTGAACTCGCTTGGCACATTCTGAACTCCACCGAATG
GCGATAGGGCCTTCAGTTCACCGGATCCTCCTCCCAACAGCAGCGGACTGGGTTGCTTTCGATTTGGACTGCGACCTCGACTAGAGGGAATGGGT
AGCTGCAGCTGTTGTGGCGGAGGCGGCAGTAGCGGCATTTGTGGTGTCAGACTACCGGGTCCTGGCATTCCAGGCACATGAGGTATTGGTGTTAC
TGGAGTGGTTTATCTCCACCGCTCATCGGTGGCAGCGTTAGCGGATTGAAGGCAGTTATTGAGTTAATGGGCGGAAATTGAAAGTGCTGCGGAC
CTGAGCTAACGCCGAGAAGTCCACTGCCACTGACCAGTGCCATCAGCTTGCGCTCCTTACTGGATGATCCTGTTTCGTTGTTGACTTTGACCGAA
ACATCCTGGAAGCTTCCGCCGGACAGCAACGGTGTTCTAATCATCTTGGGGCTGTTGTCCAAGTCTGGGCACTCCGAAATGGGAATCATGCTGCC
TCCCGAAGAGGTGAATCTGCGCAGTCGCTCCTCCTTGGAGGACTGCAATTCCGGCACACTATTACTGCTATTCTGATTATTAAAGGAAAAGTTGA
AACTTGTCGGTTGCTGAGAGGAGGATGCTACAACCAAATCGCTAGTCTTGATGCGTTTGGCAGGCTGAGCTTCAATCACAAATTGCCGATCCTCG
TGCATTTTGGTTATGACCACAGAATCCTGGGCCTTGCGTGGTGTACTTTGCTGAGCATAGTCCACTAAGGGAGTTTTTCCCAACAATGGACCAGG
CGATGGTAGAGGCGCATCCACAAAGCGCAGTGCTTCAATCTGGGGGGCAGGTGCTGATGATGGAGCAGTGACCGTAGCAACAGCAGGAGCTGGGG
CAGAAGCGGTTACAGTGGGAGCTGTTACAGTTGATGTCCTTGCTGGCGTCTGTGCTGCACTTAGGCGACTTAATACCAAACTGCTCCTTTTGGTC
TTCAACTGCGACCAGGCCAACTTGGCCAGAGATAAGGGATTCTTCGAGTTGGCCATGTGGCTCTTCAGCTCCGGTAGACTCAGCGAGATCGAGTT
GGAGCGGAATGGCGAAGATGCTGGACTCATTGGGGCACTTGAGCTCGCATCCTGACAGTAAGTGCTGTTGTGCAGCTTCAAATCGTCCGCACTGC
GGAATTCGCTTGCACAGATAGGACACGAATAAACAGCATCATCGCCTTCGCCAATCGGCACGGCCAATCCTCGAGCATTAAGCAGTAGGTTCTTA
ATTATCGAGTTATTAACCTGAGCAGGTGGTGGAGCAGTTTTGGAGCTACTAGTCGGATTGGTAGAAGTCGTTGGAGTCGGTGCCAGAGAACTGGT
GGACAAGGAACTGACGGGCACAGTGACCAGAGTTGGTTTAGGCTTCGCTGATAGATTCAGAGGCATAACAGGCACTGCCGTCGTCGGTTGCTCAA
TTTTCGTCACTGGTGTTGCAGGATCCTGGCGATATTGCATTGTTTGCATGGGCAACGGGGACGGCGGTGGAGGAAGTTGCTGCTGTTGCTTCACC
GGCGTAGTCATCACTACTCCAGGCTTATAGGCATTCCTTTTAACCACCCCATTTGGTGGTTCGAGCTGTTGCTGTTGGCATTCCTGTTGCTGTTG
GATGTACGTATAGTAGTTCTGTTGCTCGAGCTGCTGCTGCTGCTGGGTTATCTGCTGCTGTTGCTGTTGCTGAAGCTGATGTTGCTGTTTCT
GGAAGATGGCCTGTGCCAAATTCACTTTAGTCTCGCGCTCCGGCATCTGTGCGTTGGTGTTGTTTTGACTATTGTTTGCATGCAATGCCGACGCG
TTGCTCCCGTGCTGCGAAGCATTATTGCTGTTGGCATTGTTGAAACTGCGGGAACGACTAAGCTGTTTGGGGTACTTCTTCTGCAACAATATCTC
CTTGTTTTCAACTATGGCTTCATTTTGAGAGATCAACTTGGAAATGTGTTCCTGCACTTTCGCCACATTCTGAAAAGGATAACACAAATTTTAGT
TTAGTTTTTCTGTAAAAATAAACTTTTAGTGCAACACTCACTACTTGCTTGCCACCACTTGAGCTGGCAAAAGTGCTGAGATTGGCGGCGGGCGT
GGGAGTGGCTGGTGCTGTTGCTACACTGGAAATCTGGCTATTGGCACGCACCAACTGTAAACAATAAAGGTATATAGATTATAATTAATCTCCTC
GTTCAAAAACAATCGTTCTTAACCAACCTGTTGCGGCGGGAGACTCGGAGGTTGTTGCATTGGTGGTGTCGCCTTGACCAACGGTGGGTGTTGCT
GCTGCTGTTGTTGCTGCTGCTGTGCCAGGTGGATTTGGAATTGCTGAATGGCTAACGCATGCTGGTGAATGGCAGCCGCTGTATCTTGGTTGTAG
TATGAAGGTTGCCCCAGGTAATACACCCCGCCAGGTGGCATGGCAGCTAGCAATGATTGCTGGGCCAAAAGGGATTGCTGCTGCTGCAATTGCAA
CTGGATCTGATGCGAGTTAATGTGGTGCTTCATCTTCATTTGCGTGCTTGGCGAAAGCGTGGGATGCGCCAGTGACGGCTGCTGAACCAGAGGAA
GCTGAATGGACAGCTTTTGCTGCGCCAATTGGTGTTGCTGTTGCTGTTGCTGTATCTGCAGTTGCTGCTGCTGCTGTTGCAGCTCCTTACTGCTA
CATGAGTACAACGAGGCATTGTGGAACTTGGGCTTATATGGCTTATAGTCGATCGACTGGCGATGCTGGGCAGTGGCCGAGTGGTGATTGTCCGC
TGTGGTGGGTGGCAATGTTCCTGCTGCCGGCGAGCCCAGAGGCAATTGCTGCATGTAAGTGGGCAGCGGAGGCTGTTGAATGTATGCGCTCTTGG
CCGCAGACAGTGTGGAAGGTGAGGGTGTGGGCGAATTGATTGGCTCCTCGTAAGGCGAACCAGCGCGACTCGGCTGCAAAAACGTAAGGAGTTAC
ACATGTTTGCGATAACAATCACAGTTATATTTGACTTACCAACTCTGAACTACTGTTGCTCAGCTCTGCATCCTGATCGGATAAACCATCGTCCG
CATCGGCTGGCACTTCCAGGCCCCGCGCTCTTGCCGCATGCGATCTCGAGCGGCAATGTTTGTACAAATTACTCTTCGTCTTAAACGCAATGCCG
CACGTGTCGCACGGATACGGCCGTTCGTTCGTGTGGGCCCGTATGTGCTTCTCCAGCACCGAGGGCTTGGCACAGATCAAGTTACAGTACTGACA
AACGTATCGTCCGGACTTCTCGCATGCAGGATTTGGCGCTGCTGCTCCGCCTGGAATACCAGGACTCACTGTTGTTGGCTGCGTCAATTGCTGAT
GCTGGGCAAATGAAGCCGGTGACAGTGTGGCATTTGCTGCATGGTTACTGTTGCTGTTGCTGGTGCTGTTCGTGTTACTGTTGCTGTTGGCTAGA
GGCGTTCGCGTTCTTCCCGCCGCTTTGTAGCCACTATTGCTGATGATGCTCTCCTCATGACCAATGGCATTGACATGATTGCTATTTACAAAATT

FIGURE SHEET 471

GGCACTGAATTCATGTATTGCTACTGAAGGCGGCGGCGTCTGTTGCTGCTGCTGCTGCTGCTGCACTTGCTGGTGGCTTTGTTGTTGGGTCATCA
GATGGTGACCGTTGGCCAGCGGCGTTGTTGGTGGCGGTGAAAGCGAACTGTTTGAGGAGAGCGATGTGGTGCGAACGGCATCGCCACTTGCTTGC
AGTGCTCCGCCGCCATTCGTCGCACTCCAGCTGTCCACCTCGGTGGTGCTGGCCAAACGTTTGAACTTCTTGTGCAGATAGCGTGAAATATTTGA
CCGATCCCCCAACGGAGCCTCATCGGTGGCGGGTGTGGCATTTACGGTGGTCTGCTGGCTGTTGATGATGCTCGAGTTGCTCATCGTGTTGGCCA
CATTGGGAGCCACTGGCTCCTGGTTGCTGCTGACTGCTGCCATCTGTTGTAGCGTCATTTTGCTATCACTTAGACTTGCTTTATCTCTACTCTTA
AATTCATAATTATTCTCACTAATACTATTATCACTGTGGTGGTTGTTGTTGTTATTATTACTTGTGTTGTTATTGTTATTATTATTATTGTTGTT
GCTGATGATGTGGTTGCTGTCAACAGTCGGCAGCGGCACCTCGCCTAGCTTATCTCGTGTGCTTGTGCTGGGTTTGCTGCTGCTGTTGCTGTTGC
CACTAGCAGCATCTGTTGTTGCTGCTGCTGTTGCTGCCGCTTTAGAAGCTGTTAATGTTGCATCTGTTGCTGTTGCTGTTGCAGATGCTGATGCT
GATGCTGTTGCCTCTGTTGCTGCTGCCAATGCAATTGCTGCAGCGATGTTGGCCTTGTTGGTTGATCTCTGAGTGACTATGGTTGCTGTTGCAGT
TTCCCGATATGTCCGCTTCTTGGTTGGCGTTGCTGCTGTTGTTACTGTTGTGGTTGCTGCTGCTGCTGCTGCTGCTGCCGCTGCTGCTGTGGCAC
GTCGCGTATTGTTCACTTTATTGGTCTTGTACTGTTTGCCTGCGGTTTTGTAATGCTTGGCCGTTGTGGTGGTTGCATTTTCCATATTATTATCG
AATTTATTATCCTGTGACGTATTTGCAGTGGGCTCATCTATACCGAAACGAGAAGATAGAGGGAGAGGGAGAGAGAAAACCGAAATTAATTCAAT
GTGTTTCGCATAATTTAATTTAAATAGCAATGCTAATTGATACATTCATGATAAGCCCATTTATATACACTGATATCCCTGCTAGGTAATCCAGT
AGAAATCAACCACATCTGACTTTGTGGATTTGCAAATCTTCGGACGATTAAATATTTAATATTAGTTTCTAATACACCCTTGTCCCCTATAAGTC
CTCACATGATTAGTGAGAGGTTTGGTTTTATCTTTTATATGTTAATTGCGCTGTTATGTTACTGTTACTGCATTGTATTGATTCATCGCTTCTAA
ATAAATAAATATATAAAAAAAAAAAACCCTTGTCCCCTGGCCAATAAACATCTGCGGTTTGCATTTGGGTTTCCCAAGACGAGTTCCCTGCCCAT
ATAGTACACTTTTATTTCGAGCCCCATTATCAGCACTAATTCGGGCTCAATCTTATCAACGCGTAGCCGAGAATGCCAGATACGGAGCACGCTAA
TTCTCTCCATGGCGATCAATCCGTCAGGTGAATCACAAGCTGGCGAATTCCCGTGCTCTATTGAAAATCAATTTCCCACTCTGTGAACGTGTCAA
CATCGATAAAGCACAGTGGCGAAAATATACGAACACACACAAATGTATATTCGCCTTGTTTCTTTTTATCAACTTTCTATTTTGAATTCCCAACT
TAGCTGGGGTTCAGGCCCCACCTGCCGAAAACCAGACATGCGACCAAAAGATACAAAAATCCAAGAAAAGTGACAAGTGAAGTGTAATGACTGGT
GTCGCTGGCATTTCGTTTGTTGTTGGGGGCTTCCTTATCACCGCTCGTGCACACATGTGTGACAACAGTGCGTATCAGTACTGTAAAGCTGCTGG
CAGGTGTGTGATTAGCAATGGGATTATAAAGCGTTGCCAAATATGAAGAGTGAGTATTTGAGAACTCCATTTGCTCGCATTAATTAAGGCTTCAG
TTTGAAAAACAATTTAGGCAGTCTTTGGTAAATTCTTTGTTTTGTGCATGCCAAACGAAACGAAAAGCTGCAAAAATCTTTTAAAAATTTTTCAC
TTTTGCTGCTATTTATGTGAGCCCCACTGTCTGCATAGATGGTATTATATGACTCTTGGCCGGCTGGGCTGTCGGGCGATTAGTAAGCCGGGGCA
GTTCTCAAATCACAATCGCACACAGACTGAACACAAAAAACGCTCACTGGCAACCGAGCTGGGTCGCGTTAATTGACTCGACTGCGGCGACTGTT
TAGCATTCAGCGTTATTATTATACACATTATACGGCATTATGCGATCGCAGCGACTCTCGTCGCGTACCAATGTTTACTCAATTTGTTATCAGCA
CGGCTGGCTAATAAGGCTTTCAAACCGTGCGACCGCAAAAAAAAAAATAAATAAATAAAAAAAAAAATGAAAAAAATTGCCCAAAAGTTCCATTGA
TAATGCCAAGCTCTACATGCACAGGCGGTAAGGTAAGTATTTTCGGTACGTGTGTTTGCCAGATTCATTATCAGTTATCAGTGGGGACTATCGTG
CGCGCCTGAGTCAGAAACAGAGCACCCGATAAGCGAGCCCCGTTGTAAGCCACCAAGTGATTGCCAATTTGCCGGAGTTCAGACGCGTTGACGTC
AGTTATCCGATACGTAGTACTATTCGTTCGCAATCGTAAGGGGCTATATCAGATTGTCAACTCATTGGGCAATTAAGTGGCATTCGCTGGCGATT
AGCTGTTCGAGGATACAAATCCTAATTACATAATCATGTGTAGTAAATATGTGTATGCACTCGACTTATTAATAAAACGAGTGAGTGGGTCAATT
ACAAGGCGCCAACTGCGCCACAATTGAAATGCATACATATGTGTGGCGATTACACGGAATGTGTTGTTTCTTGCTAGTGAAAACAAAAGCGGAGC
AGACAGTGTGTGTGAGCATTTTGACTAAATAAGTAGAATAAAGTTTAATAACACAACGCCCAGAATCTGTCTTTCGAAATAATATTTACATTTGT
GTTCATTCGCTGTGCGAGAAACTATTGAAGTTCAACTGTACATAATGACAAAGTGGGCTATACATTCATTATACAGCAGAAACTGGCGAAACTAA
TGCCATCATCTACAGTCACGACAGTATAATAAAGTCAAGCGGGAATAAAGAAGATAAGCTAATCAGAAGTAGGCGCTTATAAAAACGCCAGCAAT
TAAAACCAGAATACTCATATGCAAGATACCCCGCCACCCAATGTGCAAACAATTAGCGCAAAGTGCACAGTGACGTTTAAAGATCCCAAGTTCGT
TTATCCACCATTTAGTTTATTGTTAGCCACGTAAATCCAATTGTCAGAGTCATCAATATCAATACGACGTTTTCATTATCACGAACTTTTGTTTA
ACGATCGGGGGTCTTCTAATTACGCCTGTTTGCCAGCATTTTGAGGCGTGAAAACGGCAAGTGAACGCGAAACACATGGGAACGTATTTCAATAT
ATGTGAACAAACTGGAACTGCATTTGCATTGGCATTTTCATTTGCATGCACATTTTTATTGAGCCAAGCGAAATACAATTGCCCCTGTTCAAAGT
GCACATAAATAAAGCGCCACGGCAAATAATCGAATAGGGTTCGGTACACTCTTACAAATATCTAAAAATTGGTTGCAATTAGTAGTTCTTCTAAC
CAGTAAATAAACACACAATCTTAGATTTAAACACCAACTTCCGCGCCAAACTTCATGAATATCTAAGATACATAAATAAATCACTTCTTATTAA
ATCATATTTACATTTGTTCAGAGAGTTTGTTTTTCGAAGCATATGGAAATGCTGGCATTGTTTCTGTGTAGAAAAGCTTGATAAGTTTGCAGCTC
ATATTGAGCACACGCTATCTCGCCTACGTCACAAGTGCATTTCGCGTTTGACTGAGTGACTGCCTGAATTCGAAATTATAATAAAACCAAAAAAA
AAACGAGAATACATATAAAAACACCCACACCAGCGCAGCGAAATAATGAAAAATAAATAACAAAATCAACGAGGTGCGGCGGCAACGGCGCCACA
AAGTCCACACATCTGTCTGACGGTCAGTCTGTCAGTCCGTCACTCTGTCAATCGGTCATTCGCTCAATCCGCGCGATGACGACTACGTCATCGCA
GAGCAAAAAGCACTAAGCACTCGCCCACTTGGCAATTGTTTATAATTTATTAGTAAGAAGCGTTTTACAGCGGTTGAGCAGAACGAACGAAAAAT
GCATATGTAATAGTATAATACGTCAAAAAAAATTCGCGGAAAAGATTCCGAAATTCCAGCGAACGGCCAAAATGCGAAATGCCCGACAAAAATGA
CGAAAACGGCACAAACGGTAAAGAGAAACATACCCAAGTTTAATTGTGACCACACGCATTTTTCCGCCTGTACCGCTCATTTGCATAGTTGGTGT
TGTTGTTCGTTTGGTTTGAAGCGCAACAATTGGAAGTGCACGGCGAGAAAAATCTGGCGGCGCGAATAGCAAGAAATCGAAAAGGCGACAATCGA
CAATCGACGACAACCGACGCGCCTGAAACATTTAAGGCAACTAGACGAGGCGACCAGCGAAATTCATTCAGAGTGTGCTCAGCGTGTGTGCTTGT
GTGTGCATGTGTGTGGTGTGTGCGAAAAGAAAACGAAGAAGCGACCGAACGAAGCAAAAACAACAAGTAAGAAGCCCAAAGTCGCACTAGTCGAC
TACAATGTACCCTTGAGTGGCAGTAAAAGTTATTCTTACTACAAATTACGTATAATTAGTAGGAATAGGCTAAACGTTTTGGCATTCTGCGATTT
TGAGTTGAGCATAACGAAAATATCAGTTCAGAAAATAAGTATATATTAGGAAAGTTGAAGTCTTCATGCCCGAAAAGGTTTTATAGGGCAGTCTA
TATCCCAGAATATTCGGTAGTAGCTCCAATAGATCATAAGCTTATTAATTTTTCTCATATTGAAAATACATCTGTATTCAAATAAAGATAGGTGG
AAAGATTTCTTGCTATAGCGTTTTTTGGTAAATCTATTAATTGGTATAATATTAAGAAGTTGTTTTGTAATATCTTTACTTATTTTAAAAATGCC
ATATACCCATGTTTTCATTCAGTTACTGAGTGTTAAAGAGGCGCGACGTCAGCGCAGGCAGCAAAAAAAGTACAATAATCAAATAATTGCGGCAG
CTTCGTCGTCGCCCCCCGCACACTCACACACAAACACACACATGTGCTCTCAATCTCCTCTCCACTCATTCGCAATTGTCAATCAAATGTAAGCA
CAGGGTCGCCACTTCTTTTTGTTCAGCTTTTGATTTTGCGGCAGCCACTGAGAAATGATCAAATCAAGCAAAAATTAAGACTCAAAAAAAAGTAT
AAAAATTAAACAACAACAGGTGACGCGAAGTACGAAGCGAAATGAAACGAAACGATTCGAAATGAAAGACTGTCGCCAGCCAGTCAGACGTTGCT
GTTGTTGCTGCAGTTGTTGTTATTTCCCCCTATTGTTGATTACGTACCCCATACACACACACTCACACACAAGTGCGC
(SEQ ID NO: 874)

Exon: 13708..13524
Exon: 10107..8495
Exon: 8433..7723
Exon: 7654..7547
Exon: 7479..4445
Exon: 4379..4153
Exon: 4089..1001
Start ATG: 10060 (Reverse strand: CAT)

FIGURE SHEET 472

Transcript No. : CT23537
TTTCAGGCGCGTCGGTTGTCGTCGATTGTCGATTGTCGCCTTTTCGATTTCTTGCTATTCGCGCCGCCAGATTTTTCTCGCCGTGCACTTCCAAT
TGTTGCGCTTCAAACCAAACGAACAACAACACCAACTATGCAAATGAGCGGTACAGGCGGAAAAATGCGTGTGGTCACAATTAAACTTGGATGAG
CCCACTGCAAATACGTCACAGGATAATAAATTCGATAATAATATGGAAAATGCAACCACCACAACGGCCAAGCATTACAAAACCGCAGGCAAACA
GTACAAGACCAATAAAGTGAACAATACGCGACGTGCCACAGCAGCAGCGGCAGCAGCAGCAGCAGCAGCAACCACAACAGTAACAACAGCAG
CAACGCCAACCAAGAAGCGGACATATCGGGAAACTGCAACAGCAACCATAGTCACTCAGAGATCAACCAACAAGGCCAACATCGCTGCAGCAATT
GCATTGGCAGCAGCAACAGAGGCAACAGCATCAGCATCAGCATCTGCAACAGCAACAGCAACAGATGCAACATTAACAGCTTCTAAAGCGGCAGC
AACAGCAGCAGCAACAACAGATGCTGCTAGTGGCAACAGCAACAGCAGCAGCAAACCCAGCACAAGCACACGAGATAAGCTAGGCGAGGTGCCGC
TGCCGACTGTTGACAGCAACCACATCATCAGCAACAACAATAATAATAATAACAATAACAACACAAGTAATAATAACAACAACAACCACCACAGT
GATAATAGTATTAGTGAGAATAATTATGAATTTAAGAGTAGAGATAAAGCAAGTCTAAGTGATAGCAAAATGACGCTACAACAGATGGCAGCAGT
CAGCAGCAACCAGGAGCCAGTGGCTCCCAATGTGGCCAACACGATGAGCAACTCGAGCATCATCAACAGCCAGCAGACCACCGTAAATGCCACAC
CCGCCACCGATGAGGCTCCGTTGGGGATCGGTCAAATATTTCACGCTATCTGCACAAGAAGTTCAAACGTTTGGCCAGCACCACCGAGGTGGAC
AGCTGGAGTGCGACGAATGGCGGCGGAGCACTGCAAGCAAGTGGCGATGCCGTTCGCACCACATCGCTCTCCTCAAACAGTTCGCTTTCACCGCC
ACCAACAACGCCGCTGGCCAACGGTCACCATCTGATGACCCAACAACAAAGCCACCAGCAAGTGCAGCAGCAGCAGCAGCAGCAACAGACGCCGC
CGCCTTCAGTAGCAATACATGAATTCAGTGCCAATTTTGTAAATAGCAATCATGTCAATGCCATTGGTCATGAGGAGAGCATCATCAGCAATAGT
GGCTACAAAGCGGCGGGAAGAACGCGAACGCCTCTAGCCAACAGCAACAGTAACACGAACAGCACCAGCAACAGCAACAGTAACCATGCAGCAAA
TGCCACACTGTCACCGGCTTCATTTGCCCAGCATCAGCAATTGACGCAGCCAACAACAGTGAGTCCTGGTATTCCAGGCGGAGCAGCAGCGCCAA
ATCCTGCATGCGAGAAGTCCGGACGATACGTTTGTCAGTACTGTAACTTGATCTGTGCCAAGCCCTCGGTGCTGGAGAAGCACATACGGGCCCAC
ACGAACGAACGGCCGTATCCGTGCGACACGTGCGGCATTGCGTTTAAGACGAAGAGTAATTTGTACAAACATTGCCGCTCGAGATCGCATGCGGC
AAGAGCGCGGGGCCTGGAAGTGCCAGCCGATGCGGACGATGGTTTATCCGATCAGGATGCAGAGCTGAGCAACAGTAGTTCAGAGTTGCCGAGTC
GCGCTGGTTCGCCTTACGAGGAGCCAATCAATTCGCCCACACCCTCACCTTCCACACTGTCTGCGGCCAAGAGCGCATACATTCAACAGCCTCCG
CTGCCCACTTACATGCAGCAATTGCCTCTGGGCTCGCCGGCAGCAGGAACATTGCCACCCACCACAGCGGACAATCACCACTCGGCCACTGCCCA
GCATCGCCAGTCGATCGACTATAAGCCATATAAGCCCAAGTTCCACAATGCCTCGTTGTACTCATGTAGCAGTAAGGAGCTGCAACAGCAGCAGC
AGCAACTGCAGATACAGCAACAGCAACAGCAACACCAATTGGCGCAGCAAAAGCTGTCCATTCAGCTTCCTCTGGTTCAGCAGCCGTCACTGGCG
CATCCCACGCTTTCGCCAAGCACGCAAATGAAGATGAAGCACCACATTAACTCGCATCAGATCCAGTTGCAATTGCAGCAGCAGCAATCCCTTTT
GGCCCAGCAATCATTGCTAGCTGCCATGCCACCTGGCGGGGTGTATTACCTGGGGCAACCTTCATACTACAACCAAGATACAGCGGCTGCCATTC
ACCAGCATGCGTTAGCCATTCAGCAATTCCAAATCCACCTGGCACAGCAGCAGCAACAACAGCAGCAGCAACACCCACCGTTGGTCAAGGCGACA
CCACCAATGCAACAACCTCCGAGTCTCCCGCCGCAACAGTTGGTGCGTGCCAATAGCCAGATTTCCAGTGTAGCAACAGCACCAGCCACTCCCAC
GCCCGCCGCCAATCTCAGCACTTTTGCCAGCTCAAGTGGTGGCAAGCAAGTAAATGTGGCGAAAGTGCAGGAACACATTTCCAAGTTGATCTCTC
AAAATGAAGCCATAGTTGAAAACAAGGAGATATTGTTGCAGAAGAAGTACCCCAAACAGCTTAGTCGTTCCCGCAGTTTCAACAATGCCAACAGC
AATAATGCTTCGCAGCACGGGAGCAACGCGTCGGCATTGCATGCAAACAATAGTCAAAACAACACCAACGCACAGATGCCGGAGCGCGAGACTAA
AGTGAATTTGGCACAGGCCATCTTCCAGAAACAGCAACATCAGCTTCAGCAACAGCAACAGCAGCAGATAACCCAGCAGCAGCAGCAGCAGCTCG
AGCAACAGAACTACTATACGTACATCCAACAGCAACAGGAATGCCAACAGCAACAGCTCGAACCACCAAATGGGGTGGTTAAAAGGAATGCCTAT
AAGCCTGGAGTAGTGATGACTACGCCGGTGAAGCAACAGCAGCAACTTCCTCCACCGCCGTCCCCGTTGCCCATGCAAACAATGCAATATCGCCA
GGATCCTGCAACACCAGTGACGAAAATTGAGCAACCGACGACGGCAGTGCCTGTTATGCCTCTGAATCTATCAGCGAAGCCTAAACCAACTCTGG
TCACTGTGCCCGTCAGTTCCTTGTCCACCAGTTCTCTGGCACCGACTCCAACGACTTCTACCAATCCGACTAGTAGCTCCAAAACTGCTCCACCA
CCTGCTCAGGTTAATAACTCGATAATTAAGAACCTACTGCTTAATGCTCGAGGATTGGCCGTGCCGATTGGCGAAGGCGATGATGCTGTTTATTC
GTGTCCTATCTGTGCAAGCGAATTCCGCAGTGCGGACGATTTGAAGCTGCACAACAGCACTTACTGTCAGGATGCGAGCTCAAGTGCCCCAATGA
GTCCAGCATCTTCGCCATTCCGCTCCAACTCGATCTCGCTGAGTCTACCGGAGCTGAAGAGCCACATGGCCAACTCGAAGAATCCCTTATCTCTG
GCCAAGTTGGCCTGGTCGCAGTTGAAGACCAAAAGGAGCAGTTTGGTATTAAGTCGCCTAAGTGCAGCACAGACGCCAGCAAGGACATCAACTGT
AACAGCTCCCACTGTAACCGCTTCTGCCCCAGCTCCTGCTGTTGCTACGGTCACTGCTCCATCATCAGCACCTGCCCCCCAGATTGAAGCACTGC
GCTTTGTGGATGCGCCTCTACCATCGCCTGGTCCATTGTTGGGAAAAACTCCCTTAGTGGACTATGCTCAGCAAAGTACACCACGCAAGGCCCAG
GATTCTGTGGTCATAACCAAAATGCACGAGGATCGGCAATTTGTGATTGAAGCTCAGCCTGCCAAACGCATCAAGACTAGCGATTTGGTTGTAGC
ATCCTCCTCTCAGCAACCGACAAGTTTCAACTTTTCCTTTAATAATCAGAATAGCAGTAATAGTGTGCCGGAATTGCAGTCCTCCAAGGAGGAGC
GACTGCGCAGATTCACCTCTTCGGGAGGCAGCATGATTCCCATTTCGGAGTGCCCAGACTTGGACAACAGCCCCAAGATGATTAGAACACCGTTG
CTGTCCGGCGGAAGCTTCCAGGATGTTTCGGTCAAAGTCAACAACGAAACAGGATCATCCAGTAAGGAGCGCAAGCTGATGGCACTGGTCAGTGG
CAGTGGACTTCTCGGCGTTAGCTCAGGTCCGCAGCACTTTCAATTTCCGCCCATTAACTCAATAACTGCCTTCAATCCGCTAACGCTGCCACCGA
TGAGCGGTGGAGATAAAACCACTCCAGTAACACCAATACCTCATGTGCCTGGAATGCCAGGACCCGGTAGTCTGACACCACAAATGCCGCTACTG
CCGCCTCCGCCACAACAGCTGCAGCTACCCATTCCCTCTAGTCGAGGTCGCAGTCCAAATCGAAAGCAACCCAGTCCGCTGCTGTTGGGAGGAGG
ATCCGGTGAACTGAAGGCCCTATCGCCATTCGGTGGAGTTCAGAATGTGCCAAGCGAGTTCAGTCGACAGCCACCAACTCCTGCCCAGCGGCAAG
CGCTGCAGTGGAACAGCAAGGAGGCACCGAAGAAAGCACCATTTAACTTTCTACGCATGGCTGATAATGTGAAGACCACTGAACCTGAAGTTCGA
CACTTTAATTTGGAAAATGTGATTTCTGGGAAACAGCAAGAGTTGCCCCTAACACCGCTACATGTTGATACTCCCAACGGAAACGCTCCAGAAGA
GACCAGTCCCGTAGCCAGTGCCTCAGCATCGGCGAAGTCCAAGTTTCTGCGGCCTACTAGTTTGCCACTTAAACCCGGTACTTTTACTCCTAAAC
GCCATCATGGCATTACACCGACAGCCAATACATTGCCGCTGATCTCGCCGGAGACCCCCAGGCCGTCCAAATCCTGTGTGCAACTGTATCTCAAT
GGACACGCCTACACATATCTGGGCCTCAAATGCAGCACAAAGATGTTTTACTGTACGGTGAACTGTCCACAGCCTTCGTATGTGGCAGGAATGCA
CAAACTATCGATGTATAGTGTGTGGCAGGTTTGCGAGGAGAACCAGCCACATCCACTTGGATTCAAACTAAAGCAAGTTATGGCACTCTACGACT
CACGTCAAAGGATGTTAGGAAATGGCAGCTCAACCGCCATGGCTGGATCGGGAAAACTTAGCTACAACTTAGTCGCTTCCCAGCAAATCGTATCC
TCCCCCTCGACGTCCTCCACTAGCAGTGCTTTCTATCAAGGACCCCTAAAGACCCCACCCACTGTCACGATTGCCGCTCTCAGTGAGGCAAATGT
GGCGGCCAAGGCGAATGAGGAGGCACAGGCCAAAAAGTTGGAGACAAGTCCATCCGGGCAGCCCCTGGTGGGTGGCTACGAGTCTCATGAGGATT
ACACGTACATCCGTGGCCGCGGAAGGGGAAGATATGTTTGCTCCGAGTGCGGAATTCGTTGCAAGAAGCCGTCGATGCTCAAGAAGCACATTCGC
ACTCACACGGACGTGAGGCCATTCACATGCAGCCATTGCAACTTCAGTTTTAAGACCAAGGGAAATCTGACCAAGCATATGCAATCGAAAACTCA
CTTTAAGAAGTGCATTGAACTGGGAATAAATCCGGGACCAATGCCGCCAGACAGCGAGTTCTTGGATGTAGATATGGACTTTGACCAGCAGTCAT
CCACTTCGGCAGGAGGACGCACATCATCGATGGCTGGGGAATCGGATTCCGATGACTACAGTGATAATGAATCTGAAAGTAGTGATACGGATGAG
TCCAAGTCGCGACAGAAAGAGCACGAAGCAGCCAGAGGCCTACTCTCGTTATCAATGACGCCGCCCATACCGCAGAGCGTATCGCCCTATCCGCA
GTTGCAGGATACACCCCTACCAGCGGCCAGTCCTGCAAACAGCATTGGCTCTTCGGGTTCGCAACCTAAAAGATTAGTGTGCTCCTTTACATCGC
CGAAGCCGCCTTTCGACTACCAAAAGCAGGAACAGTATTACTCCAATCCGGAGGAGTCCAAACCGAAACGGAGTGTGGCCAACGAGGAGAGTGCT
CCCATGGATCTCACTAAGCCACGCGGCTCCATCTTATTAATATCCCCCTCGCCTGTTTCGGTGCCCGCTCATGATCTTCCCAAATCGCAGGCCCA
ACAGATGCACGATGTTATCTTTGGAACCTCCGGCAACGAAAGCGGTTTCATGAAGACTCTAATCTCGGTTTCGGACAAAGTGCGAATATCTGCCG
AAATGGAAGAGCAGGCCAAGCACGAGGCCGAGGGCGAGGATGTTCAACTACAGACCTACATTAAGGAGCATGCGCTGCATCAAGCCAAGATAAAG
CAGAGTCAGTTTAGCCGCAGCTATCTGATCAACACATTATACACAGCGGCGTCTCCTGTAATGAGCAGTAGTAGCACTCTCTTTACCGCCAACAG
CAGGCCCGTTATGAGCGTAAATGAGGTACCTAGCATCGAAGTGCACGAAGTAAAGACCCCAGAGGCCATTGAGTCACCTCGGAGTGCACCTGAAC AGGCCCCGGTTATTCTTGCTCAGATTGCCCAGGAAGAAAACGAGGAGCCTAATATCGCAGAGCCACACAATGCCAATCTGCCTGCTGCAGTGCAG
CAACCGGATGTCAATGAATTTACTGGAGTACTTGGAAATCCGACTGCACCACCAACATCGTCTGTTACTGCTACTTCAGTAAGCACAACAACAGC
TGCACCTGTGGCACCCTCATCCACTGCCAACTCAACTCAGCCCGCGCAGCGTACTGTGATTGTGGGTGAAGATGGCTTCAAAAGCTCTACTCCCA
CTAGCAAGAGCGGCGATCTCCAGCATGTATCGTATGGCAGAGGAGTGCCGCCAGCTCCCATTGCAGGTGATGCACGTCCCACCTGCACCATGTGC
TCCAAGACGTTTCAGCGGCAACATCAGCTGACCCTGCACATGAATATTCATTACATGGAGCGAAAGTTTAAGTGCGAGCCATGCAGCATATCCTT
CCGCACGCAAGGACATCTGCAGAAGCACGAGCGATCGGAAGCGCACAAAAACAAGGTTATGATGACGTCGACTTTTGGTGTTCCAACCACCTCAA
ATCCGCGACCCTTCGAGTGCACCGACTGCAAGATCGCCTTCCGCATCCATGGGCATTTGGCCAAGCATTTGCGCTCCAAGACGCATGTTCAGAAG
CTAGAGTGTCTGCAGAAGTTGCCCTTCGGGACCTATGCTGAAATTGAACGTGCCGGAATTAGTCTCACTGAAATCGATACAAGCGACTGTGAAAA
TTCGCTGATATCACTCAAGTTGCTGGCCCAGAAACTGCAGGAGAAGGATCCTGGTAAGCTCAGTAGCTATACCACACCTTCTGGCATGATGCAGC
TGGCCCAGGATGCAGCAGGTCCCGTCTCGCAGGATAGTGCGTCCGAGGATGGCTTTAGTGCCGCAATTGCCTCGGCTATAGCTTCGCTGGACAAC
GACAGTGCTGGCAACACACCCAAGCGAGCCAGCTCGATGTCCGAGGATGAAACGGTGGCCAATGGCCTAAACCATAGCCTGAAGCGTCGTTTGCC
GGGCAGTTTCAGCAGTACGGGCGAGGAGAGCGATAATCCACCGGAAAGCAGTGGCGAGAAGCGGGCTCGTTCTGGCCAGGAGCTGCCTGTTCCCG
TGGCCGTTCCCGTGGCTGCTTCAGCAGCGGCAAGCAACTGACAGTACATGTACATGCTGCAGCCCAGCTGAGGTTATCAGTATCCCGCGGTCTAC
CACCTGGACAGCAGTCAGTACGGCATCTACAATTCCAGGATCGAGGGCCGCCATGACCAAACCACCTCCAACGAGCGCATATCAAATGTCTAAGC
ATATCGCATATGGGCACACACACAACTTACTCTAGAGCTAGCCTATAAGACCCACCTCTCTTCGATGATGGGCCCAACTAGTATTGGGCTAATCG
CGAGTAGTAATCAAACGATAGGGGAGCCAGATAAGCGAGTCAGCTATTCCAGTGTAAACACTCTAGGCGAATTGCGCTAAAATAATCATATACAA
AGCCTTTTACGGTTTTAAAAGGCAGTCACCCCACACAGATCGTTTCGATCTGCCTCTTAAGTATTTAGGTTAAGGAATCGTCATCAGCTAGCCCT
AGTTATAAGCCAACCAACGAGCACACTTATAAATCTATCTATATTGTATACACTTAACCATAATTTGTTTTCGAAATGCATAAATGCAAAAACTC
CTGAAGTGCTGTGAGTCTATCTACAAATGTAAAGATCCGAGAGCGAGAGAAGTGTGTTATTTTTAAGGCCTAGCCCCGAAAATGAACCTCCAAAC
CGAACCAGAACACACCCGCACACTAAGTATATTGGTTTTCTATGTCCAAATCCAAGTTTTGCCCTTTGAAAATCACGTAGTTCTTCCTTATTTCA
AATTGTTATCACACCAAGTTTTGAAGCGCAACTATTAACGGTGAATGAGAAATGACTTGCGCCCCTAGTTTTGTTTTAATTCTTTAAACAACGAG
ACCACGAGACTCATTTAATTGTTTCTTTTAATTTTGTATTTGACAGAAGAGAAACGAAATGATGAAAAAAAACGCTAACTGTAAATAATCAATAT
GTTGTCATATATGCATTAAGCGGTAGGTTAGATAAACAAACTACACAAAGTTGATAGATATAAATGAAATATTGTACAAACTGCTATGGCAAGCG
CTGCAGCAAAATCTATATATACACATAGATATATATCTATATATTTGAATGTGTGTATGTGGTTAAACAACAAGAAAATGAAGTGATCTATTACA
TTATTGTAAAATATATCAAAAAACTGAGAAAAAAAAAA
(SEQ ID NO: 875)

Start ATG: 233 (Reverse strand: CAT)

MENATTTTAKHYKTAGKQYKTNKVNNTRRATAAAAAAAAAAAATTTVTTAATPTKKRTYRETATATIVTQRSTNKANIAAAIALAAATEATASASA
SATATATDATLTASKAAATAAATTDAASGNSNSSSKPSTSTRDKLGEVPLPTVDSNHIISNNNNNNNNNNTSNNNNNNHHSDNSISENNYEFKSR
DKASLSDSKMTLQQMAAVSSNQEPVAPNVANTMSNSSIINSQQTTVNATPATDEAPLGDRSNISRYLHKKFKRLASTTEVDSWSATNGGGALQAS
GDAVRTTSLSSNSSLSPPPTTPLANGHHLMTQQQSHQQVQQQQQQQQTPPPSVAIHEFSANFVNSNHVNAIGHEESIISNSGYKAAGRTRTPLAN
SNSNTNSTSNSNSNHAANATLSPASFAQHQQLTQPTTVSPGIPGGAAAPNPACEKSGRYVCQYCNLICAKPSVLEKHIRAHTNERPYPCDTCGIA
FKTKSNLYKHCRSRSHAARARGLEVPADADDGLSDQDAELSNSSSELPSRAGSPYEEPINSPTPSPSTLSAAKSAYIQQPPLPTYMQQLPLGSPA
AGTLPPTTADNHHSATAQHRQSIDYKPYKPKFHNASLYSCSSKELQQQQQLQIQQQQQQHQLAQQKLSIQLPLVQQPSLAHPTLSPSTQMKMKH
HINSHQIQLQLQQQQSLLAQQSLLAAMPPGGVYYLGQPSYYNQDTAAAIHQHALAIQQFQIHLAQQQQQQQQQHPPLVKATPPMQQPPSLPPQQL
VRANSQISSVATAPATPTPAANLSTFASSSGGKQVNVAKVQEHISKLISQNEAIVENKEILLQKKYPKQLSRSRSFNNANSNNASQHGSNASALH
ANNSQNNTNAQMPERETKVNLAQAIFQKQQHQLQQQQQQQITQQQQQQLEQQNYYTYIQQQQECQQQQLEPPNGVVKRNAYKPGVVMTTPVKQQQ
QLPPPPSPLPMQTMQYRQDPATPVTKIEQPTTAVPVMPLNLSAKPKPTLVTVPVSSLSTSSLAPTPTTSTNPTSSSKTAPPPAQVNNSIIKNLLL
NARGLAVPIGEGDDAVYSCPICASEFRSADDLKLHNSTYCQDASSSAPMSPASSPFRSNSISLSLPELKSHMANSKNPLSLAKLAWSQLKTKRSS
LVLSRLSAAQTPARTSTVTAPTVTASAPAPAVATVTAPSSAPAPQIEALRFVDAPLPSPGPLLGKTPLVDYAQQSTPRKAQDSVVITKMHEDRQF
VIEAQPAKRIKTSDLVVASSSQQPTSFNFSFNNQNSSNSVPELQSSKEERLRRFTSSGGSMIPISECPDLDNSPKMIRTPLLSGGSFQDVSVKVN
NETGSSSKERKLMALVSGSGLLGVSSGPQHFQFPPINSITAFNPLTLPPMSGGDKTTPVTPIPHVPGMPGPGSLTPQMPLLPPPPQQLQLPIPSS
RGRSPNRKQPSPLLLGGGSGELKALSPFGGVQNVPSEFSRQPPTPAQRQALQWNSKEAPKKAPFNFLRMADNVKTTEPEVRHFNLENVISGKQQE
LPLTPLHVDTPNGNAPEETSPVASASASAKSKFLRPTSLPLKPGTFTPKRHHGITPTANTLPLISPETPRPSKSCVQLYLNGHAYTYLGLKCSTK
MFYCTVNCPQPSYVAGMHKLSMYSVWQVCEENQPHPLGFKLKQVMALYDSRQRMLGNGSSTAMAGSGKLSYNLVASQQIVSSPSTSSTSSAFYQG
PLKTPPTVTIAALSEANVAAKANEEAQAKKLETSPSGQPLVGGYESHEDYTYIRGRGRGRYVCSECGIRCKKPSMLKKHIRTHTDVRPFTCSHCN
FSFKTKGNLTKHMQSKTHFKKCIELGINPGPMPPDSEFLDVDMDFDQQSSTSAGGRTSSMAGESDSDDYSDNESESSDTDESKSRQKEHEAARGL
LSLSMTPPIPQSVSPYPQLQDTPLPAASPANSIGSSGSQPKRLVCSFTSPKPPFDYQKQEQYYSNPEESKPKRSVANEESAPMDLTKPRGSILLI
SPSPVSVPAHDLPKSQAQQMHDVIFGTSGNESGFMKTLISVSDKVRISAEMEEQAKHEAEGEDVQLQTYIKEHALHQAKIKQSQFSRSYLINTLY
TAASPVMSSSSTLFTANSRPVMSVNEVPSIEVHEVKTPEAIESPRSAPEQAPVILAQIAQEENEEPNIAEPHNANLPAAVQQPDVNEFTGVLGNP
TAPPTSSVTATSVSTTTAAPVAPSSTANSTQPAQRTVIVGEDGFKSSTPTSKSGDLQHVSYGRGVPPAPIAGDARPTCTMCSKTFQRQHQLTLHM
NIHYMERKFKCEPCSISFRTQGHLQKHERSEAHKNKVMMTSTFGVPTTSNPRPFECTDCKIAFRIHGHLAKHLRSKTHVQKLECLQKLPFGTYAE
IERAGISLTEIDTSDCENSLISLKLLAQKLQEKDPGKLSSYTTPSGMMQLAQDAAGPVSQDSASEDGFSAAIASAIASLDNDSAGNTPKRASSMS
EDETVANGLNHSLKRRLPGSFSSTGEESDNPPESSGEKRARSGQELPVPVAVPVAASAAASN*
(SEQ ID NO: 876)

Name: schnurri
Classification: transcription_factor
Gene Symbol: shn
FlyBase ID: FBgn0003396

Celera Sequence No. : 142000013384684
CACATACGCTAGCCAAATGCGTGGGACCCTCGAATATTCGGTGGTCCATTAAGTAGCCTAAGAATTGCACCACTGACCAGTATCCAAATATTATG
ATCTTATTTATCTAAGCCTAACAACAGAAAACACAAGCAAGTAATTATTCTCTCTACCAGCTAAGATATGAAACGCAATAAAGCCTAAACATATT
CATATCACCACAGACTTTCGTTCTGCCCAGAGGAATGCAAAGCTGATCGGTCATTAATCAACGTACAGGATTGCAATTGCAGTGGCACTTTGAAT
GGCCGCTTGGCCAGTCGAGGGTTAACGAGCTAGGCCAATTGCCAGTTGCAGTGGCAGTTTCCGTTGCAGACAGTAGCCAGCGGGTCTTAGTAGTT
GCAATTGCATCCCGCTTTGTGGGTAATCGGAGGGTTGGTCAAAGGCCACTCATAAATCAAGCAGCAGGACGGCTACTGAACATAACTGAAATTGG
ACCTCAGTGGGTCACGAAGCTTTACATATCATTAGGAACTACTTTCTTTATGATGACTACACTACTTTCGCATATGCGGTTGTAAACTTTCGTGC CGAAAATTCCACTATCAGCATGCGAAAATGGATCACATCCAGAGAAAACTTACCACAAAGCATCGTAGCATCCATTCCTGACCCCTTTTAACAAA
AATGCCCAAATACACATAAATTGCAAATTTTCACATTGGAAAGACACTTTTCCATTGAGTACACTTTAATAAGAATTTAAATAAATTAAAACCGA
TCATTATATTCTTAAACATATATAAAAAAACATAAATTAATGCAGATATGGAATCCCAATTGCTGGTCTTGACTAGCACATTTGAAAAGTGTTCG
GTAGAACGTAGAGCTTTGCAAATGACTCATTGGTGGGAAATTTGACCAAAGCGATGCAATTACTATTATCTGACAACCGTCTAACGAATAACATA
AGTTAAGGATAATAGATTACATTATTTACAAATACCTAGTAGCTAGCCCTTTAATCGTCGAAGAATAGTATTTCTAGGATCCGTTTCTGTGCACT
TTTCTTCCGTTCCTTGTTCATTTTCAGCAGTTCCGTGGTGACTAATTCTCCCAGCAAATGCTCAGACAACCGCTGCACACCCGGATGATTGGGCG
GCGCCTGGAATTTCCCGAAGTTTGCGGGATGCGAACTGCTGGCCTGATGTGGGAACTGCTGGTATAACTGGAAAAGGAAGTCCGTGTTTGACGGA
AACATGTTCTGGTGCTGTTGCTGCTGCTGGTTGTTGTGGCTATTATTGCCGCTGGGATTGTTGCTCCCGCTATTGCTGCTACTGTTATTCCCATT
TCCATTGCCCCGCTGCATGGGCATCGAATTGCTGTAGTGATTCTCCTGCTGCATCATAGCCTGCGGCTCCATCAGATCATGGCTGTTCTCATCGG
ATTCGTCGTCCGAGTCATTGCCAAAGTGACTACCATTGCTGGTCATCTGGTTATGGGCATTGCCATTTAGTTGAATACGGGGTTTCTTCATATGG
AAATGGCTCGATGACGAAGAGTCTAGACCATCGCCCTTGGGGTTATAGACATGTGACTGTTGCATCTGCAGAGTGGAACTGTTGCCGATGGAAGC
GCCCGTGGCGCTGGAAGAGGAATGTACCACCGGAAGCTGCTGTTCAGATGCCGGCGACTGTTGCTGCGCTTGTTGCTGCTGCTGCTGCTGTTGTT
GTTGCGTCTGCTGCTGAGGATGATGGGATCCTGCCCCAATTCCTTGCAGCGGCGACGACAGCGGTGATTTCATCGAGGATGATGTTGAGGTCAGA
CTGCCAGCGCTGTTCTGGGCCCCGTTCATGCCCACGGAGCCATCCTTGTATTGATCCTGATAACCTTGCGAGGAATCAGCCATTACAGCTGCAAC
GGCCGCCGCCTGTTGCTGCATTTGTGACTGTGATATGTGCTGGAGCTGCTGTGAGGCCACGGCAGCCGCAAAATCCCTGAACACCTGGTCCGCCT
CGATCTTCACCTGGCCATTGACGTTTTCCAGCGCAGATGCAGCAACGTTACTCAGAGCACTCATTGCGTGTTGCTGATCCGGCTGGTGGTAAAGA
TGACTTTGCCCTGAGCTGCCAAACTGAGACACATTCTTCATGGAGCCATTGGACTTATCAACCTGGTATTCGTTGTAGCCGGAGCTGTTGGCGGA
CTGTGGAGATGTTAGGAAGTTCGGCACATGGCGGTAGGACTTGCGCGGCTGGATGTGCTGGTCCAAGAACTTCATTTTCTCCAGGTATGGACGCG
ACAGGTGTTCGTAGACAGGTGGATCGCCCTGCTTCCGCTGCGACACGTAGCGTTCGCGTAGGTACTTCCACCGCTTCTTGCACGTGTCCACTGGA
AAGGAGGGCAACATTTATATAGAGGATCTGCCGGAGGAGCGCGTCTTCCTCACCATCCGTGCGCAGCTTCATCGCAATCAGCTGCCAGGCCTCGT
CCTTCGTCTCGTACTTGCCACCATTGGCGCCGCCGTTGAGGTAGTACTTCTGCCGGTTGTAGATCACTCCGTGCTGCGCTACCTCGTCAATTAGC
TGCTCATCCATCATTTAGTTTAATTCGTGTTTTCAGCTGCCAATTTGCCTTTGGTGTATGTCAGGCCATTTCAACACTGTTCATGGGACATCG
AAACAGTGTGACCGAAAATGTAGCAGCAGAGTGTCAAATATAATTTGAAGATATTGATATCGAAATATATTCGACAATTTGCATCATGTTTAAAT
TCGTCAGCATTTTGATTTATATATAGTAATGCATTTAATTAATTAACACGCAATAAAATTAATAATTTCAGCAAAAGTAAATCATTTGCTGTTCC
TGAATTTACTAAATAAAAATGTTTAAAAATTTAACTTATAAGTTACCTTCACAAAATTCTCGAAAAATAAAAGTCAGCTATAAAATAGTTGCTAT
AAACGTATTATGGTTATTTGAAATTTTAAGGTGGGTTCTTTTGCGAACCGAGATTCAGTCACACTGGCAATTTGGTACCCGAAGTTGAATTGCCG
TTTTGTGAAGCGGATAGTTACCTGCCGATAATCTTAAATAAAAATGTTTAAACTGGCCCGTATGCTCCTGCCGCAGCAGCGGATCCTGGCCAGCC
CGCTGCGCCTGCAACGCCTGATCTCTACCAGCGACGAGGTCAACGCAGAGCCCATCATCAAGTCCATGGACACCATTGGCGGCCTCCCCACCGAA
CTGGTCAACGAACAGAAGCTGAAGAAGACTAGCAGGTAATCAATCTACCGGTTTTCGCACTTGACCTTTGCCTTGCCTGTTTGTTTTGTTTACAT
TTCGACCGGTATGGGCATGGGCATGGTATGCATGTATCGGAGGCCTGTTTTGGGCGTGATTTTCGAAAAGGAGTTTCGGGGTCTTTTTTTCTTGA
TTTCAAGTGGGGGAGAAAGTTTGTATCGAGCCGCTTATGCAGTCACGTAGACCATAGATGCGTGCATGTGTGTGTGTATGTATTTGTGCCTGCCT
GGTGGTGTCAGTTATGGGCTCTATTGTTCTTGACTTTTGTTTTGTCCACAGAACCTTATCGACGCTCCAAAATCACTCGGTTCCCATTGCCGCTC
GCGTCACGGTGTCGAAAGATG
(SEQ ID NO: 877)

Exon: 2631..2429
Exon: 2370..1001
Start ATG: 2579 (Reverse strand: CAT)

Transcript No. : CT23567
CCTGACATACACCAAAGGCAAATTGGCAGCTGAAAACACGAATTAAACTAAAATGATGGATGAGCAGCTAATTGACGAGGTAGCGCAGCACGGAG
TGATCTACAACCGGCAGAAGTACTACCTCAACGGCGGCGCCAATGGTGGCAAGTACGAGACGAAGGACGAGGCCTGGCAGCTGATTGCGATGAAG
CTGCGCACGGATGTGGACACGTGCAAGAAGCGGTGGAAGTACCTACGCGAACGCTACGTGTCGCAGCGGAAGCAGGGCGATCCACCTGTCTACGA
ACACCTGTCGCGTCCATACCTGGAGAAAATGAAGTTCTTGGACCAGCACATCCAGCCGCGCAAGTCCTACCGCCATGTGCCGAACTTCCTAACAT
CTCCACAGTCCGCCAACAGCTCCGGCTACAACGAATACCAGGTTGATAAGTCCAATGGCTCCATGAAGAATGTGTCTCAGTTTGGCAGCTCAGGG
CAAAGTCATCTTTACCACCAGCCGGATCAGCAACACGCAATGAGTGCTCTGAGTAACGTTGCTGCATCTGCGCTGGAAAACGTCAATGGCCAGGT
GAAGATCGAGGCGGACCAGGTGTTCAGGGATTTTGCGGCTGCCGTGGCCTCACAGCAGCTCCAGCACATATCACAGTCACAAATGCAGCAACAGG
CGGCGGCCGTTGCAGCTGTAATGGCTGATTCCTCGCAAGGTTATCAGGATCAATACAAGGATGGCTCCGTGGGCATGAACGGGGCCCAGAACAGC
GCTGGCAGTCTGACCTCAACATCATCCTCGATGAAATCACCGCTGTCGTCGCCGCTGCAAGGAATTGGGGCAGGATCCCATCATCCTCAGCAGCA
GACGCAACAACAACAGCAGCAGCAGCAGCAGCAACAAGCGCAGCAACAGTCGCCGGCATCTGAACAGCAGCTTCCGGTGGTACATTCCTCTTCCAGCG
CCACGGGCGCTTCCATCGGCAACAGTTCCACTCTGCAGATGCAACAGTCACATGTCTATAACCCCAAGGGCGATGGTCTAGACTCTTCGTCATCG
AGCCATTTCCATATGAAGAAACCCCGTATTCAACTAAATGGCAATGCCCATAACCAGATGACCAGCAATGGTAGTCACTTTGGCAATGACTCGGA
CGACGAATCCGATGAGAACAGCCATGATCTGATGGAGCCGCAGGCTATGATGCAGCAGGAGAATCACTACAGCAATTCGATGCCCATGCAGCGGG
GCAATGGAAATGGGAATAACAGTAGCAGCAATAGCGGGAGCAACAATCCCAGCGGCAATAATAGCCACAACAACCAGCAGCAGCAACAGCACCAG
AACATGTTTCCGTCAAACACGGACTTCCTTTTCCAGTTATACCAGCAGTTCCCACATCAGGCCAGCAGTTCGCATCCCGCAAACTTCGGGAAATT
CCAGGCGCCGCCCAATCATCCGGGTGTGCAGCGGTTGTCTGAGCATTTGCTGGGAGAATTAGTCACCACGGAACTGCTGAAAATGAACAAGGAAC
GGAAGAAAAGTGCACAGAAACGGATCCTAGAAATACTATTCTTCGACGATTAA
(SEQ ID NO: 878)

Start ATG: 53 (Reverse strand: CAT)

MMDEQLIDEVAQHGVIYNRQKYYLNGGANGGKYETKDEAWQLIAMKLRTDVDTCKKRWKYLRERYVSQRKQGDPPVYEHLSRPYLEKMKFLDQHI
QPRKSYRHVPNFLTSPQSANSSGYNEYQVDKSNGSMKNVSQFGSSGQSHLYHQPDQQHAMSALSNVAASALENVNGQVKIEADQVFRDFAAAVAS
QQLQHISQSQMQQQAAAVAAVMADSSQGYQDQYKDGSVGMNGAQNSAGSLTSTSSSMKSPLSSPLQGIGAGSHHPQQQTQQQQQQQQQQAQQQSP
ASEQQLPVVHSSSSATGASIGNSSTLQMQQSHVYNPKGDGLDSSSSSHFHMKKPRIQLNGNAHNQMTSNGSHFGNDSDDESDENSHDLMEPQAMM
QQENHYSNSMPMQRGNGNGNNSSSNSGSNNPSGNNSHNNQQQQQHQNMFPSNTDFLFQLYQQFPHQASSSHPANFGKFQAPPNHPGVQRLSEHLL
GELVTTELLKMNKERKKSAQKRILEILFFDD*
(SEQ ID NO: 879)

Celera Sequence No. : 142000013384668
CGCACGCTTCACAAGGATCTTCGTCTTCCTCTGGCTTGCAACGAACACAGTACGCAGTGGGATACCACCGATCATTGCCGGACGTAGATCTTTCA
TGGTGCACACCTAAGAACTCTTCATTTGGTGGCTCAGGCTCTAGAATCATCTTGTAGAAGGTGTACCCGCACCTGGTTTCACTGCAGCTGGGACT
TAAAAAAGCTAGAGGCGATATGAATGTGTCCTCCGAAAAATTGGGTGGGAAATGTCCTTCCTTAATGGGACAGTTAGCTTCCTCCTGTGTAAAAA
TAGAAGATAATGGTTCACTATTCAATATCCAGTGCAAAAACCATCCACTCACCTCCAAGTTTCCCAAGAAATGCAAGTCCTCGAAGTAGGAGTAC
CTTGGACTATAACTATAACCCTCAATTTGACTATTTCGGATGGCGGCCAATTCCTTGGAGTAGTAGTGCCGCAGACCGAGCACCTGCAGCTCCAC
CTGGTCAGGAGTCAGGCCGCAGTTCATCCGCCGGGTGATTTGTCGCCAGGCGTCATCCTTCGCAGAACCACTATGGAAACCAGGTGACTTTGGAT
TCCAGAGGCACTCGTTCGATCGATAAAGTCGGATGAGCTTCTGCGTCTTCTTCAATCGCTCCAAATTCAAATACGACGTAATATCCTTCTGTGCC
ATCGTGCCCCTCTGTTCTCCACAATCCTTTCCAGCGACTCGGTGATCAATCTTCCATAGCGTTTTCCTATTGAACCTACAGAGGTTGTATGCCTA
GTTTGGAGCTATATATTGCGCCCAAGCCGAAATATTTGGACAGGAAAAACAAAAGTGACAATAAACAAGCAATTTTGAATAATTTTTGAATGATT
TTTAAACGGTATCGCTTAATTAGGAATATTATATGCCGTTACCATTTTCAAGATCTGCAGGGTGTCTCATACATTCGAAGCTTTTGAGAGTATTA
ATTCAGTATTATTGTGCAATTAAATGGCGATTGGTATTTAGCTGGGCGAGCAGAACGGTCACACTGGCGCACAGTAGCGAAAATAATAGTCGAAT
AATAAAATAGTTTTGAGTGCAACTAATTCCGACCTACTAACGTATGCGAGTGCATTTAGCGGCTGCACTTAATCATTCCGGGCAAAAAAGTGCAA
AACAGTACGACGCGGAGCAGTCAGAATCGAGGTTGCGCTCCAGCGTTATCGCCATTTGACCAATTCAACTTTTGTGTCTGGTATAACCACAAAAT
TTTCACTGCATCTTCTTATTTGAGCCGCCCCCAACCCAATTTTCGCGAGTGTGTCGGAATCAGCAGAGAATCGGAACAAAAGGGGCCAAACGGAG
TACCAGAATCGGCACAAGCAAACAGTGAACAGCAGATAGTGCGGACGATAGCGAGTCCGTTGATTATCCACGTAAACAGTGAGCTGCATGCGCAG
AGGTCGCGCCCAGAGCTGCAGAAATCCAACAATCTCCGCCAGAAAGATCTATCTCCGCCCTGTAAGCAATGTCCGCGGAACGAGAGATTCCCGCC
GAGGACAGCATCAAAGTGGTCTGCCGATTCCGACCGCTGAACGACAGCGAAGAGAAGGCCGGCTCCAAGTTCGTGGTCAAGTTCCCCAACAATGT
GGAGGAGAACTGCATATCCATAGCGGTATGTGTTCCAGATCTATAGTTTTCGCCAGCCCCCAGTGCCTTTTCCCTATGTGTTATGCATTAATCTC
GGCGTGCCGCGCCATGACGTCATGCCTATTAGCGTACATTACCCTTCCCCAAAATTGCCGACCAATTGGAATGCCAGGCGATAAAAAGAGAGAGG
CACTAAAGTTACCCATGAATAATTGCACAAAACAAAACTAGATGTACATATACATGTATATGATGAAACCAACTAACTTTACTCCAAATCAATAT
TGCTTTGCACCAAATTGATTTTCCCCCAGTCGAAAAAGAATAGGGTGTGTAAATCGAAAGAAGCGCGATGACGGGGTGGAGAAATGCCACCCACT
AGACGGTTTTCTGCTAAAAGCGGGTGTTCCATTCTTTTGGGCCGCATAAATATGCGCTTTTCTAGTTTCCAGTCCGCCTTCAGTGCTTACCTCAC
TTACATTTCCACACAAACACATACACACATTGACGGTAGCCCCCGCTCCACTTCCACTCCCCTGTCCGCGCGCCAATGAGTCATGCACGCAAAGC
ATACAAAAAAAAAAAATATGAGGAAAAACAATAAGAGCAACTTTGGAGGCAATGGAATTTGGCTGTATTGCTTTTATGCCACATGAAATGTTATT
GCTTTGTATGCTATGCTGAATTTCCCGCTTTTCCGCCAGGTGTAATCCGTCATATTCCTGGTAAAGCTTGGGCAATTGAACCAGTTCCAAAAAAG
TCAGCACTAATATAGTGCCTCCATACACAGACATTATCATTACGCTCTCTCTCTCTCTCTGACTAACTCTATCTATCTCTCTTTCGCTGTGGCTT
TCTTCTGGCGCTCGTTATTCACTATTCTTCCCCCTTCCACTTAACATGTCTTAATGCTCATAATTACAATCTGCTTCGCGGCCATGCGTTGAAAA
TGATTCAAAGGCAGTCAGCGGGAAAAGATCGGGGACAGGGGGAATGAATCTCCGAAAGAAATTTCACCGCAACTGACACCAGTTTATAGCTAATG
TAACTGGCTGCTATGTACTAAAGAAAAAAACACATTATACTAAACCTAATCTCCATCGTCTGCAGGGCAAGGTGTATTTGTTCGACAAGGTCTTC
AAACCGAATGCATCCCAGGAGAAGGTCTACAATGAGGCGGCCAAGTCCATTGTTACGGATGTCCTGGCCGGGTACAATGGAACGATATTCGCATA
TGGTCAGACGTCCTCCGGAAAAACGCATACGATGGAGGGCGTGATCGGGGACTCCGTAAAACAGGGTATCATACCACGTATCGTCAACGACATTT
TCAATCACATCTACGCGATGGAGGTGAACCTGGAGTTTCACATCAAGGTCTCCTACTACGAGATCTACATGGACAAGATTCGAGATCTGTTGGAC
GTCTCCAAGGTGAACTTAAGCGTGCACGAGGACAAGAACCGGGTGCCGTACGTCAAGGGCGCTACGGAACGGTTCGTCTCGTCGCCGGAGGATGT
TTTCGAGGTGATCGAGGAGGGCAAATCCAATCGTCACATCGCTGTGACAAGTGAGTACTAATTAAAATCGATGGTCAGGACCATTTCAGCCAAAC
AAGTCTAGGAGTTATTCCAGCATTCGCTCTGACCTCGATTGTAGTGTTTCATGTACCAGATCATCTTTTATAACGATTTATCCATCCTTTCAGAC
ATGAACGAGCATTCTTCGCGATCCCACTCAGTATTCCTTATCAATGTGAAGCAGGAGAACCTGGAGAACCAGAAGAAACTATCCGGCAAACTCTA
CCTGGTGGATTTGGCCGGTTCCGAGAAGGTTTCCAAGACTGGAGCGGAGGGAACCGTTCTTGATGAAGCCAAGAACATCAACAAGTCGCTGTCGG
CCTTGGGCAACGTAATTTCAGCCCTGGCGGACGGAAACAAAACGCACATCCCCTACCGTGATTCCAAGCTCACGCGCATCCTGCAGGAGTCGCTG
GGAGGCAATGCACGCACAACCATCGTCATCTGCTGCTCTCCAGCCAGTTTCAACGAATCTGAAACGAAGTCAACGCTGGACTTCGGTCGTAGAGC
CAAGACAGTGAAGAACGTGGTCTGCGTTAACGAGGAGCTTACTGCCGAGGAATGGAAGCGACGCTATGAAAAGGAGAAGGAAAAGAACGCCCGAC
TAAAGGGTAAGGTGGAGAAGCTGGAGATCGAGCTTGCGCGCTGGAGAGCGGGTGAAACTGTTAAGGCGGAGGAGCAAATCAACATGGAGGATCTC
ATGGAGGCAAGCACGCCCAACCTGGAAGTGGAGGCAGCACAGACGGCGGCGGCCGAGGCCGCTTTGGCCGCCCAGCGAACGGCTCTCGCCAATAT
GTCCGCATCGGTTGCCGTGAACGAGCAGGCCAGGCTGGCTACAGAGTGCGAGCGTCTCTACCAGCAGCTGGACGACAAGGATGAGGAGATCAATC
AGCAGAGCCAGTACGCCGAGCAGCTCAAGGAGCAGGTGATGGAGCAGGAGGAACTCATCGCTAACGCTCGGCGTGAGTATGAGACTTTGCAGTCG
GAGATGGCGCGAATCCAACAGGAGAACGAGTCCGCCAAGGAAGAGGTTAAGGAGGTGCTCCAAGCTCTCGAAGAGCTGGCTGTAAACTACGACCA
GAAATCCCAGGAGATCGATAACAAGAACAAGGATATCGATGCCCTCAACGAGGAGCTGCAGCAGAAGCAGTCTGTGTTCAACGCCGCCTCCACAG
AGCTACAGCAGCTCAAGGACATGTCCTCACACCAGAAGAAGCGCATCACGGAAATGCTAACCAACCTACTGCGCGACCTTGGCGAAGTGGGCCAG
GCCATTGCCCCCGGCGAGTCCAGCATTGACCTCAAGATGAGTGCTCTGGCTGGCACGGATGCCAGCAAGGTGGAGGAAGATTTCACCATGGCGCG
TTTGTTTATCAGCAAGATGAAGAGGGAGGCCAAGAACATTGCCCAGCGATGCTCCAACATGGAAACACAGCAGGCTGACTCCAACAAGAAGATCT
CCGAATATGAGAAAGATCTGGGCGAGTACCGGCTACTCATTTCGCAGCACGAGGCACGCATGAAGTCGCTGCAGGAGTCGATGCGGGAGGCAGAG
AACAAGAAGCGCACGCTCGAGGAACAAATCGATTCGCTGCGCGAGGAATGCGCCAAGCTCAAGGCCGCCGAGCACGTTTCCGCCGTTAACGCCGA
GGAGAAACAGCGGGCTGAGGAGCTGCGCTCCATGTTCGATTCTCAGATGGACGAGCTACGCGAAGCCCACACCCGGCAGGTGTCCGAGCTCCGGG
ATGAGATTGCCGCCAAGCAGCACGAAATGGACGAGATGAAGGATGTCCATCAAAAGCTGCTCTTGGCGCACCAACAGATGACGGCCGACTACGAG
AAGGTGCGCCAGGAGGATGCCGAGAAGTCCAGCGAGCTTCAGAACATCATCCTCACCAACGAGCGTCGGGAGCAAGCGCGCAAAGACCTCAAGGG
CCTGGAGGACACGGTGGCCAAGGAGTTGCAGACGCTACACAACCTGCGAAAACTTTTCGTTCAGGATCTACAGGTAAAGTTTAAGCAATCCTATC
TATTATTGCTACGTACAGATCTTAAAATGTATTTCCCTTGTGCCAACAGCAACGAATCCGAAAGAATGTCGTAAACGAGGAGAGCGAGGAGGACG
GTGGATCACTCGCGCAGAAACAGAAGATTTCCTTCTTGGAGAACAACCTCGACCAGCTGACCAAGGTGCACAAGCAATTGGTGCGGGACAACGCC
GATCTGCGGTGCGAGCTGCCCAAGCTGGAGAAGCGTCTACGCTGTACCATGGAGCGGGTGAAAGCTCTGGAGACAGCGCTCAAGGAGGCGAAGGA
GGGCGCAATGCGGGATCGCAAGCGCTACCAATACGAGGTGGACCGCATCAAGGAGGCGGTGCGACAGAAGCATCTGGGCAGACGTGGCCCACAGG
CACAGATCGCCAAGCCGATCCGGTCCGGCCAGGGTGCAATCGCCATTCGTGGTGGTGGCGCCGTTGGAGGACCATCCCCGCTGGCCCAGGTTAAT
CCTGTCAACTCGTAGATCCAATCACCACCTGTCGCCGCCCAGTTCAGCTCCGCTTTAAACTAAACTAAATGGATTACGTTATACATACTTAACAT
AACTGATAATTGCCTTCGCTTAGATGAGATGTGTCGCGATCATGTGCAGCGCTTTAAATATACATACATATAATTTAATTAAATAAATGAAAGGA
AACCGGAAATTAACTAAATTTTACAAACCGAAAATAATAAAACCCACAGATATGTAAGGACATCTATATACGTTAAGAGTATTTATAAACTTTTC
AAACATAAACCTAAATAAAAGTCGCAGACAAATTAAGGTCTCTTTAGTTTGATTCTTATTGCAGTTCAAAAAAATTATGCCGATTATTTGGCTAT
TGGTTGTTATTACATCGTCTGCTGTTACAATCGCATGTTGTAACCTGTCCCGCGTGTGTTATGGTGCTCCCAATCGTCTGGAGAATTGACCACCT
GCCATTCGTACCACACTTTGGTTGCATCCACGCATCGCCAAAACTGGATGGATATAGTCTGTCCCTCCCTCAGAGTTCTTGGACGCTGAGTAGTA
AAAATATATATTAATGTAGCAGTTATCAAAGGCTAACTAATCACATCACACGTACCGTTGCGAAGAACATGGGGAACCAGGAGAACATGCCAGGC
GTATGGGTCAGAGGATTGATGCTTAGGCAGATGTCCTTGTACAAATGGGTATCAAAGTATCCGCCGATTCCGTGCAGCACGCAATCTTTATTGAC
TTTAAATGAAACCGTCTTGCAGCGAGTATTGTCAATATTTTCCGCTCGATTAGGATGTACGAATTCAAACAGAGCCTGCGGCTCGTCAATATGGT
AAATATTCTTTAGCAGCGACACATAGCCGTAGTCGAAGGCAGGATAGGTTGGTAACAATTGGCAGACATTTTGGTGCAGCACTGCTGACATCAGT

FIGURE SHEET 476

GGATTAATGTAGGAGGTGGATTTGTAGGGTATACTGATTCCATCCGGTTTGAGCAGCTTCAGTGCTCCATCAAGGCACTCGGGCGAAAGTTCATT
ATCGCCAAAGGAACCAAGTAACTCCGAAACCATGATGTCAGCCAGCTCTGGAGGGGAAAAGTCCCGCATGTCCTTTGAAAAAATGTGAACATCTG
AAAGATTTGTTGCGGATTAAGACTGGATTAAAGCAAGGTGTTTTTTTTTTTCTTATTCTTACCCTTATCGGCCCAAAGCGTTTTAACCATGTTGG
AGAGGGTGCGGATGGCATTGGGATTCTTTTCTATGATGTAGAGGCGAACTTTGCGCTTCGTTAACTCGGCAGCATTGAA
(SEQ ID NO: 880)

Exon: 1001..1640
Exon: 2726..3185
Exon: 3324..5203
Exon: 5275..6014
Start ATG: 1494

Transcript No. : CT23616
CAGAACGGTCACACTGGCGCACAGTAGCGAAAATAATAGTCGAATAATAAAATAGTTTTGAGTGCAACTAATTCCGACCTACTAACGTATGCGAG
TGCATTTAGCGGCTGCACTTAATCATTCCGGGCAAAAAAGTGCAAAACAGTACGACGCGGAGCAGTCAGAATCGAGGTTGCGCTCCAGCGTTATC
GCCATTTGACCAATTCAACTTTTGTGTCTGGTATAACCACAAAATTTTCACTGCATCTTCTTATTTGAGCCGCCCCCAACCCAATTTTCGCGAGT
GTGTCGGAATCAGCAGAGAATCGGAACAAAAGGGGCCAAACGGAGTACCAGAATCGGCACAAGCAAACAGTGAACAGCAGATAGTGCGGACGATA
GCGAGTCCGTTGATTATCCACGTAAACAGTGAGCTGCATGCGCAGAGGTCGCGCCCAGAGCTGCAGAAATCCAACAATCTCCGCCAGAAAGATCT
ATCTCCGCCCTGTAAGCAATGTCCGCGGAACGAGAGATTCCCGCCGAGGACAGCATCAAAGTGGTCTGCCGATTCCGACCGCTGAACGACAGCGA
AGAGAAGGCCGGCTCCAAGTTCGTGGTCAAGTTCCCCAACAATGTGGAGGAGAACTGCATATCCATAGCGGGCAAGGTGTATTTGTTCGACAAGG
TCTTCAAACCGAATGCATCCCAGGAGAAGGTCTACAATGAGGCGGCCAAGTCCATTGTTACGGATGTCCTGGCCGGGTACAATGGAACGATATTC
GCATATGGTCAGACGTCCTCCGGAAAAACGCATACGATGGAGGGCGTGATCGGGGACTCCGTAAAACAGGGTATCATACCACGTATCGTCAACGA
CATTTTCAATCACATCTACGCGATGGAGGTGAACCTGGAGTTTCACATCAAGGTCTCCTACTACGAGATCTACATGGACAAGATTCGAGATCTGT
TGGACGTCTCCAAGGTGAACTTAAGCGTGCACGAGGACAAGAACCGGGTGCCGTACGTCAAGGGCGCTACGGAACGGTTCGTCTCGTCGCCGGAG
GATGTTTTCGAGGTGATCGAGGAGGGCAAATCCAATCGTCACATCGCTGTGACAAACATGAACGAGCATTCTTCGCGATCCCACTCAGTATTCCT
TATCAATGTGAAGCAGGAGAACCTGGAGAACCAGAAGAAACTATCCGGCAAACTCTACCTGGTGGATTTGGCCGGTTCCGAGAAGGTTTCCAAGA
CTGGAGCGGAGGGAACCGTTCTTGATGAAGCCAAGAACATCAACAAGTCGCTGTCGGCCTTGGGCAACGTAATTTCAGCCCTGGCGGACGGAAAC
AAAACGCACATCCCCTACCGTGATTCCAAGCTCACGCGCATCCTGCAGGAGTCGCTGGGAGGCAATGCACGCACAACCATCGTCATCTGCTGCTC
TCCAGCCAGTTTCAACGAATCTGAAACGAAGTCAACGCTGGACTTCGGTCGTAGAGCCAAGACAGTGAAGAACGTGGTCTGCGTTAACGAGGAGC
TTACTGCCGAGGAATGGAAGCGACGCTATGAAAAGGAGAAGGAAAAGAACGCCCGACTAAAGGGTAAGGTGGAGAAGCTGGAGATCGAGCTTGCG
CGCTGGAGAGCGGGTGAAACTGTTAAGGCGGAGGAGCAAATCAACATGGAGGATCTCATGGAGGCAAGCACGCCCAACCTGGAAGTGGAGGCAGC
ACAGACGGCGGCGGCCGAGGCCGCTTTGGCCGCCCAGCGAACGGCTCTCGCCAATATGTCCGCATCGGTTGCCGTGAACGAGCAGGCCAGGCTGG
CTACAGAGTGCGAGCGTCTCTACCAGCAGCTGGACGACAAGGATGAGGAGATCAATCAGCAGAGCCAGTACGCCGAGCAGCTCAAGGAGCAGGTG
ATGGAGCAGGAGGAACTCATCGCTAACGCTCGGCGTGAGTATGAGACTTTGCAGTCGGAGATGGCGCGAATCCAACAGGAGAACGAGTCCGCCAA
GGAAGAGGTTAAGGAGGTGCTCCAAGCTCTCGAAGAGCTGGCTGTAAACTACGACCAGAAATCCCAGGAGATCGATAACAAGAACAAGGATATCG
ATGCCCTCAACGAGGAGCTGCAGCAGAAGCAGTCTGTGTTCAACGCCGCCTCCACAGAGCTACAGCAGCTCAAGGACATGTCCTCACACCAGAAG
AAGCGCATCACGGAAATGCTAACCAACCTACTGCGCGACCTTGGCGAAGTGGGCCAGGCCATTGCCCCCGGCGAGTCCAGCATTGACCTCAAGAT
GAGTGCTCTGGCTGGCACGGATGCCAGCAAGGTGGAGGAAGATTTCACCATGGCGCGTTTGTTTATCAGCAAGATGAAGACGGAGGCCAAGAACA
TTGCCCAGCGATGCTCCAACATGGAAACACAGCAGGCTGACTCCAACAAGAAGATCTCCGAATATGAGAAAGATCTGGGCGAGTACCGGCTACTC
ATTTCGCAGCACGAGGCACGCATGAAGTCGCTGCAGGAGTCGATGCGGGAGGCAGAGAACAAGAAGCGCACGCTCGAGGAACAAATCGATTCGCT
GCGCGAGGAATGCGCCAAGCTCAAGGCCGCCGAGCACGTTTCCGCCGTTAACGCCGAGGAGAAACAGCGGGCTGAGGAGCTGCGCTCCATGTTCG
ATTCTCAGATGGACGAGCTACGCGAAGCCCACACCCGGCAGGTGTCCGAGCTCCGGGATGAGATTGCCGCCAAGCAGCACGAAATGGACGAGATG
AAGGATGTCCATCAAAAGCTGCTCTTGGCGCACCAACAGATGACGGCCGACTACGAGAAGGTGCGCCAGGAGGATGCCGAGAAGTCCAGCGAGCT
TCAGAACATCATCCTCACCAACGAGCGTCGGGAGCAAGCGCGCAAAGACCTCAAGGGCCTGGAGGACACGGTGGCCAAGGAGTTGCAGACGCTAC
ACAACCTGCGAAAACTTTTCGTTCAGGATCTACAGCAACGAATCCGAAAGAATGTCGTAAACGAGGAGAGCGAGGAGGACGGTGGATCACTCGCG
CAGAAACAGAAGATTTCCTTCTTGGAGAACAACCTCGACCAGCTGACCAAGGTGCACAAGCAATTGGTGCGGGACAACGCCGATCTGCGGTGCGA
GCTGCCCAAGCTGGAGAAGCGTCTACGCTGTACCATGGAGCGGGTGAAAGCTCTGGAGACAGCGCTCAAGGAGGCGAAGGAGGGCGCAATGCGGG
ATCGCAAGCGCTACCAATACGAGGTGGACCGCATCAAGGAGGCGGTGCGACAGAAGCATCTGGGCAGACGTGGCCCACAGGCACAGATCGCCAAG
CCGATCCGGTCCGGCCAGGGTGCAATCGCCATTCGTGGTGGTGGCGCCGTTGGAGGACCATCCCCGCTGGCCCAGGTTAATCCTGTCAACTCGTA
GATCCAATCACCACCTGTCGCCGCCCAGTTCAGCTCCGCTTTAAACTAAACTAAATGGATTACGTTATACATACTTAACATAACTGATAATTGCC
TTCGCTTAGATGAGATGTGTCGCGATCATGTGCAGCGCTTTAAATATACATACATATAATTTAATTAAATAAATGAAAGGAAACCGGAAATTAAC
TAAATTTTACAAACCGAAAATAATAAAACCCACAGATATGTAAGGACATCTATATACGTTAAGAGTATTTATAAACTTTTCAAACATAAACCTAA
ATAAAAGTCGCAGAC
(SEQ ID NO: 881)

Start ATG: 494

MSAEREIPAEDSIKVVCRFRPLNDSEEKAGSKFVVKFPNNVEENCISIAGKVYLFDKVFKPNASQEKVYNEAAKSIVTDVLAGYNGTIFAYGQTS
SGKTHTMEGVIGDSVKQGIIPRIVNDIFNHIYAMEVNLEFHIKVSYYEIYMDKIRDLLDVSKVNLSVHEDKNRVPYVKGATERFVSSPEDVFEVI
EEGKSNRHIAVTNMNEHSSRSHSVFLINVKQENLENQKKLSGKLYLVDLAGSEKVSKTGAEGTVLDEAKNINKSLSALGNVISALADGNKTHIPY
RDSKLTRILQESLGGNARTTIVICCSPASFNESETKSTLDFGRRAKTVKNVVCVNEELTAEEWKRRYEKEKEKNARLKGKVEKLEIELARWRAGE
TVKAEEQINMEDLMEASTPNLEVEAAQTAAAEAALAAQRTALANMSASVAVNEQARLATECERLYQQLDDKDEEINQQSQYAEQLKEQVMEQEEL
IANARREYETLQSEMARIQQENESAKEEVKEVLQALEELAVNYDQKSQEIDNKNKDIDALNEELQQKQSVFNAASTELQQLKDMSSHQKKRITEM
LTNLLRDLGEVGQAIAPGESSIDLKMSALAGTDASKVEEDFTMARLFISKMKTEAKNIAQRCSNMETQQADSNKKISEYEKDLGEYRLLISQHEA
RMKSLQESMREAENKKRTLEEQIDSLREECAKLKAAEHVSAVNAEEKQRAEELRSMFDSQMDELREAHTRQVSELRDEIAAKQHEMDEMKDVHQK
LLLAHQQMTADYEKVRQEDAEKSSELQNIILTNERREQARKDLKGLEDTVAKELQTLHNLRKLFVQDLQQRIRKNVVNEESEEDGGSLAQKQKIS
FLENNLDQLTKVHKQLVRDNADLRCELPKLEKRLRCTMERVKALETALKEAKEGAMRDRKRYQYEVDRIKEAVRQKHLGRRGPQAQIAKPIRSGQ
GAIAIRGGGAVGGPSPLAQVNPVNS*
(SEQ ID NO: 882)

Name: KINESIN HEAVY CHAIN

FIGURE SHEET 477

Classification: motor_protein
Gene Symbol: Khc
FlyBase ID: FBgn0001308

Celera Sequence No. : 142000013383872
ATAAGGTGAAGAATGCGGCGCGAAAGCAAAAAGAAGAGGAAATCAAGGACGGCATTCGAGAAAAGTCGCGGTCGCCAAGTCCGATTGTGCTCGAG
AAACCCCTACCCAAAAAGAGCAACAAGCGAGTTTATCGGTGAGTGTTGGTTTTCCATCAAAAATTTTCACACAAAAACTAGAAATATTTGCACTT
ATTTTCTTGCGCAGATCCAAGAGTCGCAGTCGCTCCCGCTCAAAAACGCCGCCCCATCGAGATAGATCGTTGTCTCGCTCCCGATCCCGCTCGCG
ATCCATGGAGCGCTCTTTAACGCCGCCACCGATGAATCGGAGCAGGTTGGGCGGTGGTAACAACCGCAAGGGTCGCAATCGATCTCCTCGCCACG
AACGGGACAACAACAGCGGCAGCACAAATACCAGAGAGGGCCGTGGTGATCGTGGCAATTCCAATAGCCGAGACAATGGCAACAGCACCAACCTA
AGACGAGTGGACCGCGACAGATCTCTAACACCTCCGAGCTTTCTGTAAATCATGGCTATAGTACAATTTCATGACAGTCGGACCAATGAGCTATC
TTTGTTTTTCCAGGGGAAGCACATTTGCCAAGCCAGCGGATTTCATCGAGGAATCGAACAAGGGCCACCAAATGCTCATGAAAATGGGTTGGGCG
GGCACGGGAACTGGACTGGGCTCAAAGAATCAAGGCATCGACACGCCCATTTCGGGAGGCGAGGTGCGCGATCGTCGAGAGATGTACAAGGTGAA
GTGGCAAGAGTGCGCAAGAAAGGACAACTTATAATTTTCTATCCACAGGGAGTGGGCGCTAATATGCACGATCCCTTCGAGAGCTTTCGGAAGAA
CAAAGGAGCTGCCTTCGCGCACCGGATGCGATCGCGAGACGACAAGAGTTAGGATCTGCCAACGGTCATAACTTCCCAGTTTTTTGTTTCCTTTA
GCCCAGAAAATATACATTTTTATAAAAGCGAACTGAATTTTTATACAAGATTAGGCTATAACATTAAAGCTGGATTGAGCGGCCTTGGCATTTAC
TTTTTCCAGGACCTGGACCAGGCCCTTGCCAGGACCGCATTCGAAGGTGCGTGGAAAGTCGACGCCCTGCTTGCGCTCGTACATCTCGTGGAGAG
TCTGCTCCCACTTGACGGGCCTCACGATTTGCTTGGGCAGCTGCGTTAGGATGTGCTTGGCATGGCGATAGGGTTTGCCATCCACATTGGAGTAC
ACTCTAATGACGGGGTCCTGAAGTCGCACCGTTTTCAGGGCTTTGGTAAATGGCTCCACGGCGCTTTGCATTAGAGGAGTGTGAAAGGCGCCACT
GACAGCCAATCTCTTCATCCGCCGGATTTTGAAGGACTTGGCATTTTGTTCCAGGAACTCCAGGGCCTCTACGTTGCCGGCCACTACCTTGCAGT
GCGGATACATGTAGTTGGCGATGCCACAGTAGGGCGACTCCACTCCTTTGTCCAGACACCATTGCTGCGCACGAGCGCAGGCCTCTCCCAGATTG
GTATCCGGTCCGTAGAGAGTCATCGCCATGGCTCCGGCTGCCTGGTCACATGCCGCCTGCATGGCGGTGGCCCGCACCTGCACCAATCGCAATGC
CTTGTCGAAAGGCAGGGCATCCGCGTACACCAATGCGGTAATCTCGCCCAAACTAAAGCCTGCGGCAGCTACACACGTTTCAATGGCCTTGGGTC
GCTCCTCACGCAACTGCTCCAGTGCTGCCAGCGAGGATACCATCACAGCCAGCTGAGCGTGCTCCGTGCGATTCAGTTTCTCACGTGGTCCCTCC
AGGCAGATCTTGAGCAGATCGTATTTCAGCACCTCGTTGGCCAGCTCGAAGATGCGACGGGCGCCCGGGAACCGGAGCAGGTCTTTGGCCATGCC
CACGTACTGGGTGCCCTGACCGGGAAAGAGCATCACACTTGTTTCCTTGGGATCGATGGCGGGCCGGCCTTTCTGTTCCAGCGGCTCAGAAAGCT
CGTTGAGCAGTTGCTGCCGCTTCTCCGCGTTCTGCAAAAGGGCGGAGGTTTCTGTTGTGGCCTTCGCGGCATCGCTGCTCCAGCGGGACCAGCTT
AGGGCACCGGTAATCCGCGGTGATCGTAGTAATCTGCGGGCGGCCAACATTTTTGTTGAAGGAGTTCGCGGCATAACATAACAGCTGATTGGAGC
AGAGAAAAGTAGATCATATCGATAACTGTAATGCGGCCATCGATAGCTTTAGTACTTCGATGATTTTAGTACAATTGTATTTTGAATTTTGGCGG
CTTATGCTCAAAAACAATATGATCTTAAGAAATGGAAAACATTCAGTGCATTGTGATAATCGACACTTTATTGTAAATCTTAATTATTAAAGTCA
ACATGCTATATACGCTATTAAGTGGTTCAAGTATTTACTATTAACTTTAAATAAATCCAATGGCCAATTGGAATTGGTAAAAAGATCAAAATTCC
CAGGTATTTTATTTCCCCAGACATCTTAGTCATGGTCTGCGGTCTTTTTCCACTATTTATAGCCAAACTTGATTTATGTTGCTAGGCTCTTATTT
AGTCGTTGATGGTCATGACGAAATAATGTTGGTTGTTTATTCATGAGTCACTGACTACATAGAAACTGAGCCAAGTTTTTAGTTGAGTACAGAGT
AACAAAGTTACTGTGCTTAGTAACATTTCATTTAAGATACTATTTTAAAATATTAATAATTTTTTTTTTTTTTTGGTGTAGCCTTTTATTTATTAT
TTAAAATCTGTCCTAGTGGACAATAATTAAATTTTATGGAGGGAAACATTAACGTAAGGGGAGTACATCGAGTGTACTTGGGTAGGGGAATATTA
ATAATGACAATATTTTTCTGAAGAAAATTTGGAAGCTAAGTTACGACTTTTCGTTTCATTTGCATTGTATTCTATAATTTACGTTTTCTAAAGTC
AGACCTTAAATATCTATGAAAATTTAAAGAAATAATAGCTCTTTATATGTTTAAATTCAAAGACATAAGATTAAAACCCTGCCAAGACAAAAGAG
TATTTTTTGGCCATGTGCTATTCGGAACCCCCGAAATAAGAGTTTCTAATTTGAAATGCGATCCCAGCAAGGCAATCGCAGAGTTTTTTGAACCC
AGGGCAAAAGAATAACC
(SEQ ID NO: 883)

Exon: 2152..1001
Start ATG: 2140 (Reverse strand: CAT)

Transcript No. : CT23794
CCTTCAACAAAAATGTTGGCCGCCCGCAGATTACTACGATCACCGCGGATTACCGGTGCCCTAAGCTGGTCCCGCTGGAGCAGCGATGCCGCGAA
GGCCACAACAGAAACCTCCGCCCTTTTGCAGAACGCGGAGAAGCGGCAGCAACTGCTCAACGAGCTTTCTGAGCCGCTGGAACAGAAAGGCCGGC
CCGCCATCGATCCCAAGGAAACAAGTGTGATGCTCTTTCCCGGTCAGGGCACCCAGTACGTGGGCATGGCCAAAGACCTGCTCCGGTTCCCGGGC
GCCCGTCGCATCTTCGAGCTGGCCAACGAGGTGCTGAAATACGATCTGCTCAAGATCTGCCTGGAGGGACCACGTGAGAAACTGAATCGCACGGA
GCACGCTCAGCTGGCTGTGATGGTATCCTCGCTGGCAGCACTGGAGCAGTTGCGTGAGGAGCGACCCAAGGCCATTGAAACGTGTGTAGCTGCCG
CAGGCTTTAGTTTGGGCGAGATTACCGCATTGGTGTACGCGGATGCCCTGCCTTTCGACAAGGCATTGCGATTGGTGCAGGTGCGGGCCACCGCC
ATGCAGGCGGCATGTGACCAGGCAGCCGGAGCCATGGCGATGACTCTCTACGGACCGGATACCAATCTGGGAGAGGCCTGCGCTCGTGCGCAGCA
ATGGTGTCTGGACAAAGGAGTGGAGTCGCCCTACTGTGGCATCGCCAACTACATGTATCCGCACTGCAAGGTAGTGGCCGGCAACGTAGAGGCCC
TGGAGTTCCTGGAACAAAATGCCAAGTCCTTCAAAATCCGGCGGATGAAGAGATTGGCTGTCAGTGGCGCCTTTCACACTCCTCTAATGCAAAGC
GCCGTGGAGCCATTTACCAAAGCCCTGAAAACGGTGCGACTTCAGGACCCCGTCATTAGAGTGTACTCCAATGTGGATGGCAAACCCTATCGCCA
TGCCAAGCACATCCTAACGCAGCTGCCCAAGCAAATCGTGAGGCCCGTCAAGTGGGAGCAGACTCTCCACGAGATGTACGAGCGCAAGCAGGGCG
TCGACTTTCCACGCACCTTCGAATGCGGTCCTGGCAAGGGCCTGGTCCAGGTCCTGGAAAAAGTAAATGCCAAGGCCGCTCAATCCAGCTTTAAT
GTTATAGCCTAA
(SEQ ID NO: 884)

Start ATG: 13 (Reverse strand: CAT)

MLAARRLLRSPRITGALSWSRWSSDAAKATTETSALLQNAEKRQQLLNELSEPLEQKGRPAIDPKETSVMLFPGQGTQYVGMAKDLLRFPGARRI
FELANEVLKYDLLKICLEGPREKLNRTEHAQLAVMVSSLAALEQLREERPKAIETCVAAAGFSLGEITALVYADALPFDKALRLVQVRATAMQAA
CDQAAGAMAMTLYGPDTNLGEACARAQQWCLDKGVESPYCGIANYMYPHCKVVAGNVEALEFLEQNAKSFKIRRMKRLAVSGAFHTPLMQSAVEP
FTKALKTVRLQDPVIRVYSNVDGKPYRHAKHILTQLPKQIVRPVKWEQTLHEMYERKQGVDFPRTFECGPGKGLVQVLEKVNAKAAQSSFNVIA*
(SEQ ID NO: 885)

Name: malonyl coenzyme A-acyl carrier protein transacylase-like
Classification: enzyme

FIGURE SHEET 478

Celera Sequence No. : 142000013384534
GTTTGTGCAGGTTTCGGCGGTTCCTGCAAAAACAAAAGAAAAATGAATGATAAGTATGAATCAAATATAAAGTATATGCATAGATTCTAATGATT
TAAGTAAAATAGATAACGATTGATTACAAATCATTGATTATACATCCTTATCCTTAGTTAAAACAACTTCAAAAATTGCAAATTATGATATATTA
GGTTTTTAAGAGCTTTATCTGGAATTTAAGTTAATTAAAAATCTCTCTAGAACTTTAAATATAGCATCAAATCTAAGGCAAATGTGTATGTTATG
ATCAAAAGTAAAGTTGCTATGAAATAGCGCGAAACCCAATTAAAATTAGTTAACGTAAATGTCATCCTAAGAACTAAATAATAATAATTCAAAAG
AATGTTTTTCCAATCAGTAAATCCGTGTTTACCGCTCTGCAGTCGCTGCTGCGCTGAGCCCGCTGCCGGCGTCGCAGTCGGCGTCGCTGCAACGT
CATCCTGGGCGAGCGGCGCCTTTTGCTTCTGCTCCTCCTGCTGCTGATGATGCAGTTCCTCCACTCGGCTGCCGGTGACGTCGCCGCGAAAGCGC
AGCTGACGCTTGCCGCCCGCGGAATTGAGTGTGGCGTTCATTAAGTACGGTGTGCGGAGTCCATAAAATTAACAATAACAACGAGCTACAAAATT
TCGGGGTGAAACAGCAGTTATATGAAAATGTACTAACGCGTGCCGAAAATACCCAAACGTAAACAGTGTGTGTATCGAATGTACAGAACTATCGC
CTAAAGTAACAGCTTAGTTTATATTATATTAACATGGTTAATATTTGCAATGATTTTTATTCTAAGCTTAAAGAATAAGTTCCCGTTAGGGCCAT
GAGAGAAATTGATATATAAGTATACAACGAATTTTAAAATAATATATTTTTGCTACCCAGTAAACTTTTTATGCACTAGCTCACCGATTCATATT
TCAAAGTGCTATCGAAGTATCAGTCAATAGAGTGCCGTCACTAAATAAAAGCAGAGAAAATATTTCAATAGTTTGTAGCTGAAAAATATGTTCGC
ATCTGTGGAATTAAGCTCATATCGCGATCAGCACTTCAAGGTGAGTACATCCGAAGGCGCCACAGCAGATCTCCGACTCAATAAACCAATTGCAG
GGCTCGCGCTCCGAGCAAGAGCGATCGCTCCGCGACTCGTGTACACTTTACGTGGGAAACTTGAGCTTCTACACCACCGAGGAGCAGATCCACGA
GCTCTTCTCCCGCTGCGGCGATGTTCGTGTGATTGTGATGGGCCTGGACAAGTATAAGAAGACGCCCTGCGGCTTCTGCTTCGTGGAGTACTATG
TCCGATCGGAGGCGGAGGCGGCCATGAGGTGAGCCATATCCATCTCTCCACGCTAGAAAAAGCCGCCTTTTTTCCGGCATTTGTAGAAGTAATCA
GATGGGGTATCATTATCTCTTAACTAACTTCAACACTCTTTTCTTCTCCCACAAAAGATTTGTGAATGGCACTCGCTTGGACGACCGTCTGATTC
GTGTGGACTGGGACGCCGGCTTCGTGGAGGGCAGGCAGTATGGACGCGGCAAAACCGGCGGACAGGTGCGAGATGAATACCGCACGGATTACGAT
GCCGGCCGCGGGGGTTATGGCAAACTGTTGTCACAGAAGATTGCACCCAACACGGACAATCGCTAGTTATTAGATAAAATGACTGTAAAGACTAT
AAGCCCCCCAATTAGATATTAAAGCATACCCCTTAGACATAACATCTCTAATCGCATATATATTGTACGTTTTACATAGTTCTTTTGAAGACGTA
ATTGATATCATTGCGGCCTAGCATTAGCATGTATGAGTTTCTAGTGTTTTCGGGCTGACTGGATTCCATTTACTTCTTGCCAATGTTGTTGGCCA
GCGAGCAGCTGAGTCCGGTGCCATCGGGCTCGACATTCAGCTCGGTCACCTTGCCGTTCTCCACCACCAGCGAGTAGCGCTTTGAGCGCACGCCG
CCAAGTGGTGGCAGATCGATGGTCACATCCAGGGCCTTGGTGAAACCGCCGGCGGGATCAGCTAGGAGGCGCACCTTGCCCGCGGCTCCGTGCTC
CTTGCCCCAGGCGGACATCACAAAGGGATCGTTGACCGAAACGCAGACAATCTCGTCCACGCCCTGCTTGGACTTCAGCTCATCGGCGGAGCTCA
CATAGCCGGGCAAGTGGGTCTGTGGGTGTGGGGAAATGCATTATTCAGTTGGAATACATAAGCTGCATAAATTACACTATACTGCTGGAAGTTTC
TACAATATTCGGAAACTCAAAGCAGATGACTTTGCAACTATGCTACCTACGCACCTTTGAGCAGCCTGGAGTGAAGGCGCCGGGAACGCCGAAGA
TGATCACCTTCTTGCCATTGACGAGATCGCCGGTGTTGATTTTGTTGGCTGGCGAGTCCTCGAACAGATCCACCGATGGCAGGGAGTCTCCTACC
TGGAAATAAAGTGGGAGGCAGACAGGCGTACTTAGAGAAAAGAGGCAGCAAGATGGAGGCGATAACCTTGAAACGCTGTAATTTCTGGGTGCCGC
CGCAATCAATATTTATGCAGCTCGGCACCGGCTTATGTAATGGAATCCGGACTGCCGCACAGCCGGAAATCCGCGTTTGCCGGTCAACCTGCACT
TACTTTCACCATAGCTGCACTGGTTTTGGACAGGGATCGCAGTGAAATGATTTGTTGGGGCAGCGCGGAGTTAACAACTCGGCCAA
(SEQ ID NO: 886)

Exon: 1001..1085
Exon: 1141..1358
Exon: 1483..1746
Start ATG: 1038

Transcript No. : CT23846
GCAGAGAAAATATTTCAATAGTTTGTAGCTGAAAAATATGTTCGCATCTGTGGAATTAAGCTCATATCGCGATCAGCACTTCAAGGGCTCGCGCT
CCGAGCAAGAGCGATCGCTCCGCGACTCGTGTACACTTTACGTGGGAAACTTGAGCTTCTACACCACCGAGGAGCAGATCCACGAGCTCTTCTCC
CGCTGCGGCGATGTTCGTGTGATTGTGATGGGCCTGGACAAGTATAAGAAGACGCCCTGCGGCTTCTGCTTCGTGGAGTACTATGTCCGATCGGA
GGCGGAGGCGGCCATGAGATTTGTGAATGGCACTCGCTTGGACGACCGTCTGATTCGTGTGGACTGGGACGCCGGCTTCGTGGAGGGCAGGCAGT
ATGGACGCGGCAAAACCGGCGGACAGGTGCGAGATGAATACCGCACGGATTACGATGCCGGCCGCGGGGGTTATGGCAAACTGTTGTCACAGAAG
ATTGCACCCAACACGGACAATCGCTAGTTATTAGATAAAATGACTGTAAAGACTATAAGCCCCCCAATTAGATATTAAAGCATACCCCTTAG
(SEQ ID NO: 887)

Start ATG: 38

MFASVELSSYRDQHFKGSRSEQERSLRDSCTLYVGNLSFYTTEEQIHELFSRCGDVRVIVMGLDKYKKTPCGFCFVEYYVRSEAEAAMRFVNGTR
LDDRLIRVDWDAGFVEGRQYGRGKTGGQVRDEYRTDYDAGRGGYGKLLSQKIAPNTDNR*
(SEQ ID NO: 888)

Name: RRM-type RNA binding protein
Classification: RNA_binding
Gene Symbol: Cbp20
FlyBase ID: FBgn0022943

Celera Sequence No. : 142000013384534
ATGTGGCCGCTCTGTTGACTATGCTGTCCGCCAGTCTCTCCAGGTCGTCCAGGCTCTGCTCGTTGATTTTCCGCTCGAAGTCGGCCATAAACTCA
TTGGTCATACGCTCAGCTAGGGGCTCCGAATAGTGCTTGCGGAATCCCCGCAGGATGCTGTCCCTTAAACAGGGCTTTATCACCACCAGATTGAG
TTTGGTGCCCTCCTTGATGTTGGGATATGACGCAATTGTCTGTTCATTGTTAAGCGGTCGCCCCAACAGCAGTAGCTTTTGATTTGTAGCCGATA
TCTGCAGTTCCGCCTCGATCTGGTGTTTCACCTCCAGAATCGTCGATGTCGGCGCCACCTGTGTGAAATATTACCATATTAGCGACCTCACTTGA
TTTTGGCAAGGTTCATTCTTACCTCGATGGTGCAGTCCTTGCCCTTCAGCACCTTGATTGTTATCTGCATAGCAATTGCCGTAAAATTTATTAAA
AAATTAAAAGTCAAACTCGAGAAGTCGAGCGATATAAACAATCTGTCTTTGGCGTTGCCACCTGTATTGCCACCAAGTGTCATTAGGCCAAGCGG
CCCTGGTTTGTAAAACAAGTGCCGCAATATTTGCTAATATATAATTTACAAAAATATTTCCTTATATTAATATATAGTACATATATATGATTCTT
GTAAATTGCCAAATGTTATTTAAAATTATTAATATTTTAATGCAGCTAGCACAAATTATGTACAAGCTATCGAAAACCACTCGAAGTTATTATTT
TACAAAATTAAAGAATAATGTGAGATCAACAATTAAATAACAGTTTGTAAACATTCGGTTTATTATAATTAATAATGATCTTTAAGTCTTTCGCA
TTTGGCAATAAGACAGTAGAGGAGAGTAAGGTATAAAGATAGTAAATATAAATAAGTAAATAGCATAAGCAAAAGCTCGTTTTAGCTTTTAAACG GAGTCGGTAAAATCTTCCTAAAAGTAACTATCGAGGGTCGGCTGGGTCAGGCAACGCCGCCGCACGCCTGCAGCCCTGGTAACTCTATTTTCTAT
TGAGCACCGACAACGTTGCGTGTATAAGACAGTTTACATAAATTATTATTTACAATTGCACAGAGCGTTGATGTTGTGCGTTCTAAGCGAAAAGG
TGAACTTGACCCCGGTGCCGATAGACCGCCGAGCTATTGGGTGTGAAATTCGCGAGCGAGCCTTGTGGAATTCGCACGCGAAAATCGAAGCGAAT
CGCAGCGATCGAAGAAATTGCAGCGCAAATAATTCGTGTAGCCTCGACGACTGAATTTTAACGCGAGAGCGGGGTGTGCGTGTGTGTGTGTGCGC
TGTGCTGTGATTCTGTGTGCGTGTGCAAGCGTTTTTGTTAGAATTCGCATTTTACGCAAAGAACTAGCTTTTATCAGCAGTGAACTTGATGTTGG
CGAACCTATATCGCAGCAGGGCCAAATTGAACAAGTTCTTGCAGCTTCTGGCGGTAAATTGGCGAAATAAGACCCATTAAAAACCCCCCTCTGAA
AATATAACCCACAAATTAACCTCGCCCCTTGACATTCAAAGTTATATTTGTTTCCCCACTTATATATGTGCACATATATATATATAAATATATAT
ATATTTAATAATAATTGTGTGTTTGAGTCTTGGAAGTGCAACTACAACTATTAATCGTGCCTAGTACACATTTTACTTTTACGCTCTCGACTGTC
TCCGTCTCTCTCCCTCTCTGTTTCACCCCTTCCTTGCAACAACAAAACTTATGAGTACTTGCTGGGTGCCCCAACAATACTTGTGTTGATGATTG
CCCATCCTTGCACCTCCAAAAAGAAATGAAAAAAAAATTTGAAAAACACCAACACCACCCAAAAGCGCTCTTCCTTCCCCATTTCTATTGGCATG
TCTGGCAACCCTGGCAATTGGTCGACGGCCATTGCTTCTCAACTTGTTGCTCGTCTCGCTTGCTCTCCTCTCTCTCTCTACTCTCTTTTCAAGTA
CGCTCTCTCTGCGCCAGTGTTTTGGCATTTTTGTTACTTATTTTCGTTTCGAGTATAGTTTTATGCGAAATGAACAATGCCAAACAATGAAACGC
CTGAAGACCTGCATAAAGTGTTGATGCTAACATTTAAATGGGAATCCGAAATTCCACATCACCGACAACACCTGTCCACTTGGAAGTTACAGCAC
TAATCGGAGGAACGCTGCATGAACGTGTTTTCGGTACCGTTTAGAACCGGATTTTCTATGCTAGAGAATGAGAATATGATCGCGGTTCTGTGGGG
ACATCTTGTGACAACTTAGGAACTCCGATACGAAGCGGTTTTCCGCCATTAAGGCATTTCCAATTGGAAAGCGCGCAGCGAGAGATTCTTAAAGG
TTGCTCCGTTTCCCATTGGTAATGTGTTGTTTACAGTTATGGTTAAGTTAATAGCAGCGTGTTTATGTAATATATAGATAATTCGAGTTATGCAC
GTTCCACTGTACAGTGATCAAAGGGAAAAGAAACAGTATTGGAATTTCCATGAAGTTGCATAACAAATGAGGAATAGTAGTGATGAGAAGATTCG
TGGTAGATTTCAGTAAACCCTTAATTTACGTTGAGCGCCCCTCGAATGCGAATGTTAATGCGTGTGTGTGTGTGTGTGTCTGCTTGAGTGTGT
TGTTTTGTGGCTTAATTGCACGGTGTGTTGTGATGCTATTGTTATTTTTCCTTTAGTTATTGCTACGTTAATTTTTTTCTTTCGACCCTCCACAG
TGCAAATATAATTTTCAGATAGCAATCAACTGAGAGCGGTCCAGCCCGGCCTGTTGTATTTGTTTGTTTGTCCGGTTGTTTACGTTTTTTTCTCT
CGTTCTCGCTGCTTTTCATACGTATTTTATATTTGTAAAAATAAAAAATCGTTATAAAAAACCAAAAACACACATAGAGGAGAGCACATCCAAA
GAGCCAAAAAGAGTCAGAACCGATTGCGTATTATGGATAACGAGGCGTTAGATCCAACAATAAAAAGCAGTACGTCGGCAGCGACGCCAACAGCA
GCAGCATCAGAAACGACAACAACAGCAGCATCTTCAGTTGTGGAAACCACAACAACAATCGCGGCGGCCACAGCCTCAGCGGCAGAATCAAAAAA
CGAAACAACGGCCACAAACAACAATAGCAACACAAGCGGCAGCATCAGCAGTAGTAGCAGCAACAATATAGTCATACCGGCATCGGCCACTAACG
GTATCAAAGAGAGTAACAGTAACTTAAGTACAACAACAACAGCAGCAGCAGTAGCGGCAGCAACAACTGTAGAAGGAGTAGCTCCAGCAATAACG
TCCACAATCGTGGTGACCGGCGGCACTCCTCCATTGAGCAGTTTGGTGAGTAGCTCTCCCCCAAAACACTAGCCCTCCCCACCACACTCCCTCAC
TCACTCTCTTTCTCTTGCTGTCTTTAAGCCACAGTCTCTCTCTGTTTCTGTTACGATCTCTCCCTGTCTTTCACTTGTCGCCCTATTTGCATGCC
TACCGTTATTTTGGCGTAACGTAAACCTCACTCGTAATGCTTACACGCACACTGTGCATTTGTGTGTGTGCCTAAGCCTTATCTTATCTAATCAG
TGCTAATGATGTGTGTTATTGTATCGCTGCTTCACCTTACCCCGCACGATTCAAGTTAGATTGACCAACACCAATTAGATTCACAATGTTGCCAA
TTGTTAAATGAGTGTATGTCGTTCGGATAACAAATCGAATCGTAATTGTATCGCAAGTGCTTGACAAACCGATATTCACTTTCCCCCTTTTCCTC
ATCTCCAATTTGACCAATTCGTTAGTCCTTAGAGAGATAAACTTATTAGATTTTAATTTTTTTAATTTTAAAAAATGATTTTTTAATTAATTTCA
TAAGTTTTTTTATACGAAATATGATGCATTTAATTATTTCTTTAAATAGAGGAAATACTCTTTATTTAACAAACGATATAAATAGCATTTAATGA
CCTTGTAAGTGGTAACAGTAATCTAGCAATCTTTATTGCTTTTCAATTTTGGTTTACAAATCGTTATCGTTTCAATTATATTACCTTGGGTTCTA
CTTTCTGATAAGACTTTTGCGATTGAATGAATAGATTGCCCTAAATCCTAGATTTTATACGATTTCCCGAAAGTTTTGTGTCAACAAAAGACGGA
GTTGATTATACAAATCTTTATACTCACATGCCTGTTATTAACTAGAAGAACTTTTAATGAAAATTTTTTACATTTTTGTCTCTCCAACGACAAAA
ATATTGAACATTTGCAATAAAACATAAAGTATAAGGCGAGCACTTTGCTTTTTGAAACTGCCAAAAAATTGCCCAATGAAATGCTTTAAAAAATA
CATAAATGTTAGTGCCTGGAAAATATATACATATATGCCACCACCTGATTCCCTGGTAGATGCCAGCAATATAATCCTATACGTGTATGGAGAGC
CTACGGAACTCCAGCTTCCTGATCCCAGAGCACATTTCAATGTTCGGCATTACTAAACTCAGACTAAAACACACCCACAGGCAGCTCAACTTAGG
CGTCAAGGATTCGCACAGTCCAAGGTAAAAGCGATGGCCGGCCAAAATGGCAGCGAGGGACCATCCCGAACTGAACTGCTTTGCTCTGATTTTGC
AAGTGCTACGTTTTGAGTATGCTTTTTATTTGACCGCATATTGCTTTGCATTCGTTGTTAAAATTATTTTCATTTACTAAGCATAAGCCAAACCG
TTGACATGGGAAAAGATAATCAGATAAGTGTCATTTATGCCCCTTTGCAGGCTAACAAACTCAAGGACAACACACCACCGTACGATGCACCGCCG
CCCACGCCGATCAGCAAGGTCCTGAACATCACCGGCACCCCGATCGTTCGCAAGGAGAAGCGCCAGACCAGCGCCCGGTACAATGCCTCCAAGAA
CTGCGAACTGACGGCCCTCATTCCGCTAAACGAGAGTGAGTAGCCTTGGAGTAGATCCTACTACTTAGTATATTACTTTATAATACATGTACTGC
CAGCTGTTCAGATCGATATCTCTTAAGCCTGCAGATCGGTTGCATGGGGTAGAACTTGGTCGTAGCCATGTCGTAGCATACATTTTAGGGCAGGG
TTCCGTTTAGGCGATATAAAATTACCTTTCTTACTGTCTACCAACATCGTCAATTAAGTTTTTATGCAACTATACACTCAAAACAGATTGTATAA
ATCGTAGTAATTCCCATTAACGATGCATAATTACATATATTATGTCAATTAACTCCGGTAAATTTCCATGATTATAAGTTCAGCTTTAACTTACA
AGAGGCATTCTCTGTAAAGTGTACCTACGACCTGCAAGCTTGTTGGGAATATTGATTGGCCGGCGCTTGATTAATTTCGCTCAGCTGTTGTAATT
TGTTTATTATTTGTTAAAGTTAAAGGTCAAGGGAGTGTCGTCTGATTAGGTGGGTGGCAACACTGACGCACGGCCACTCACACATGTGAACCAAG
CAGCCGCATCAATTCACACCTCTCTCCACCTCTCTCACTCACCGGAATTTCAACACATGCGCTCTCTCCGCAGCCTCTCATTACACTGGGAGAAA
GCATCGTTAGAGGATTTCTCAGACCGTCTTAAATTTCATATATACACCGGCATTTCTTTATGACACAAATGTATTCGATTGATTTAAACTTGTGT
ATACAAATAATTAGAAAAACTGTATCCTGCAGGGAATTAATTTAAAAAAAAGCAAATTCAATATTTTTGAAAATCATATATGTACATATCTGCGC
GTAATGATTATGAAATTGCTACACTTTTTTTTCTGTGCAGCATGAATGTCATCGCATTGCGTTATTCACATACCTTTCTGCTAATTGCTTGGGC
GGTTTCGACTCACAAATCGAATAAACAAATTTCGCTTGTTCAATACTATTTTATTTTATTAGGTTTTATTGTTATTGTGGCTCGCTCGCCCAC
(SEQ ID NO: 889)

Exon: 1001..1139
Exon: 2929..3370
Exon: 4801..4983
Start ATG: 2978

Transcript No. : CT23882
GCAACGCCGCCGCACGCCTGCAGCCCTGGTAACTCTATTTTCTATTGAGCACCGACAACGTTGCGTGTATAAGACAGTTTACATAAATTATTATT
TACAATTGCACAGAGCGTTGATGTTGTGCGTTCTAAGCGAAAAGAGGAGAGCACATCCAAAGAGCCAAAAAGAGTCAGAACCGATTGCGTATTAT
GGATAACGAGGCGTTAGATCCAACAATAAAAAGCAGTACGTCGGCAGCGACGCCAACAGCAGCAGCATCAGAAACGACAACAACAGCAGCATCTT
CAGTTGTGGAAACCACAACAACAATCGCGGCGGCCACAGCCTCAGCGGCAGAATCAAAAAACGAAACAACGGCCACAAACAACAATAGCAACACA
AGCGGCAGCATCAGCAGTAGTAGCAGCAACAATATAGTCATACCGGCATCGGCCACTAACGGTATCAAAGAGAGTAACAGTAACTTAAGTACAAC
AACAACAGCAGCAGCAGTAGCGGCAGCAACAACTGTAGAAGGAGTAGCTCCAGCAATAACGTCCACAATCGTGGTGACCGGCGGCACTCCTCCAT
TGAGCAGTTTGGCTAACAAACTCAAGGACAACACACCACCGTACGATGCACCGCCGCCCACGCCGATCAGCAAGGTCCTGAACATCACCGGCACC
CCGATCGTTCGCAAGGAGAAGCGCCAGACCAGCGCCCGGTACAATGCCTCCAAGAACTGCGAACTGACGGCCCTCATTCCGCTAAACGAGAGTGA
GTAG
(SEQ ID NO: 890)

FIGURE SHEET 480

Start ATG: 189

MDNEALDPTIKSSTSAATPTAAASETTTTAASSVVETTTTIAAATASAAESKNETTATNNNSNTSGSISSSSSNNIVIPASATNGIKESNSNLST
TTTAAAVAAATTVEGVAPAITSTIVVTGGTPPLSSLANKLKDNTPPYDAPPPTPISKVLNITGTPIVRKEKRQTSARYNASKNCELTALIPLNES
E*
(SEQ ID NO: 891)

Celera Sequence No. : 142000013384543
GCTATTTCCAATTGTGCTATTAATCTGCCACATTTGCACTTCCGCGGAAAAGAGTCGGCGGGCGGATGTGATCTCTTTCGCTCGTCAGTTGGCTG
ACTCGCTCTGCAGGGGTGATTTGCGGGCGAGCGAGTGAGACAGAGCGAGGCAGAGTGGTAACGCTTGGCTAACCTGAAAATAGAAACAATCGAAA
TAAAAATACATTCTCTTCATGCTCTCGTCTAATAAAAAACCCCAAAAGCAAAACGTTTTCCATTTAAAATGTCGTCGCAACTGCCAGCGGGAAGT
GGACGTCGAGAGTGGCAAGTGTGTGGGGCAAACTCCGGCCAGCGGCCAATGGCGGTTGGCCGAGGCCACGCCCCGTGGCTCAATTACCGACCAGT
GCTGCCCATCGGCGGGCAGAGCGAAACCTGTTTCCACGAGCGAGAGGCAGTCAGGCGCATGTGCGATCAGAGCGGGATGGATGGCTCAAGGGTGG
ACCAACCAGAAGAGGCAGGTTGCTGGTATTATGGTAGGTTAGGTTCAAACAAGGTGGCAAACTGGCTCTTAACCGAAATAGGAAGGAAGTCGGCA
GCGGCGTCGACGTCGGGCAACTGGTTTGACTTGTTTCCGGCTCACTCCAACAGCCCAAACCCACCAGCAATCGGCAGAGGCAGCCAAGTCGGCAG
AGGGCAGGCAGAGCAGCGGCCGTCGGCACAATTTGATTGCATTTATGAAAAGCGTTTTCGCCCGCTAGCACGCGTCCGCTCCCAGCTCGCAATTC
GCCATCCGTAATCCGTAAACTTTAATCCGTAGACCGTAATCCGTGAATCCAAAGCAGTTCTCAGTTGGAATTTCCCGCAACGGGTAGTGCTTAAG
CGCGGAAACTGAATTGAAATCAATCGGACGATTAGTGTGTGCTTCGCGGTTGAAACACTCTACATCTAACTATTAAGAGAAAAGAGTGCCCAATA
AGATTCGAAAAGTGCAGTGAGCGAGCTCCAAATTGGCGCCACTAATTGCCAAAATGTCCAGCCACGAGGAGGATGACCATGAGCACGAGAACGAG
CACGGCGAAGAGGTGGAGGAACAGGAGATCCACGTGGATGTGGACTCGGACTCGCGGATGTCATGTGGCAGCGGATCCGATGTGGATATGGACGG
CGGCAGCTGCTACGACGAGTCCGAAACGCCATTGAGGTGAGAAGGAGAGCTTTTAAATAGAACCAGGAAGTAGGAAAAATGTCCCAAAAATATAG
ATATTATCAGTATAGATATACCATAAATAAGCAGATCTTCCAATTACAATAAGACTTCTACATATACATACATATATTATTTTTTTAACTAGATT
GTGATAAAATGCTTTGGCTTCCGTACTACTTACTTAAAACTGAAGAGGCCTTTTTTTTTAAAATTCATTTTGGTAAATATTTTTCAAATATGAAT
AACGTCTGAATTTATGTACGTTGCAAAATCGAACAATAAAAAATATTTTTGGTTTAATTGTATCGTAAATAATCTGCTACACTAAACTTGAAAAG
AGATTGCATCTCTATTAATAATAATAATGGCTTTACTTTCCCAAATTATACGATGTACAAACATAATAATTGGTCTGAAACAATTCATTACGGAAAA
TCCCCAAAAAAAAATATATTAAAGAAAAAGCTCAGTTTTTCGTTTACTCTTGATGGTTATGATCATCATGCAAATTAATAAATATTTTTTTGTAAG
TACTGGGCTTGATTTAGTTGGCCACATTATTCGTTAATTACTCATAAGTCAAAATTTAGATCGACAGCAATTTGATCGACTAACTGAGAGAAAAA
GATCTATAAGCTATAGTTATAATAGTTGGCATACAGTCTTATTTTATTGCCCTATAAAAGTCAAACAAGTATTGTGGCGGAGAAAAGCTATTTGC
ATTTGTTATTACGAGCTCATAACTCCCACTGTTTTACGATCTTTAACATTGTCACTCATAATGCTCACAAATCCTATTTTTCGAATCGTGGCTCA
ACGCCATTGAAATGCGTTGATGTTTAAGCCCCATTGTCCGCTCTTACAAATGGTCCCATTTTCCAGCGACAAAAGGGGATAACAAGATGCCAGAG
CATCCAGCAGACCGTGTTAACTGATCCCATTCAAGCGTTTGTGCGCTTAGAAGAACAGTGTGAACAAACCTCTTAAACGCTAATGAATTGACCAC
AAAGCCACCAAAAGAATCAAGTCGAAATGTCCCATAAAGTGCCAAAGAAACTCCCTGAATTTACATAGTTCACGGATGGCCAGGGTTTCCAATAG
ACGACGACGATAAAACGCACATTAGTAAGGCGCCAAAAACGGGCTGTGATAAGACATTGGGGTCCATTTGGGGCTCAATCTGGAGTTGGATCTTC
GGCTTGAATGCCGGACAAAGACGAAATCGTTTGCGGATTAACATTTTAATAGAGATCGTCATAAAAATGCCATAAAACCCGCGTTCCAGCGAAT
GTAGATCACCAGATAGCAGCAAGTTTTGGCCAGTGAAATAATATGTGTTTGCTCATAACTTTTGATATTGGAAAGTGTCTGTGTGTCGGTGGTTG
GCGATTTGAGATCATTGTTCCGATACAATTCCATTCCTGTTCCAAATGGGTTTTTACTTTTTGGATTTATAAATTAAATGCCGTGCGTGACTTGT
TTTCGGTGCGTCAGTTGATGGCATTTGATGATTTATGGGCGCGTATTAAATGCCTCTAACGGCCGTCAGCATTTGCATAATTACTTCATTTCCAG
CCGCATTGCGTATACGCAGCGGTGGCCACACGGGTTCTGCATGTCATGTCGTCAACTCGGCTTATCCGCTCGCGTGGGCTTTTGGTTAGTGGTTC
CGAGACTGGTACGCACTGCAACAGACTTAATTATAGTCAATGTTCTCAGGCTTTCCCGCTTATCGGGCGACACATTTTAATGAGCCCGCACCTCC
AGAGGGCTTCTTTCCCTTCGATTCTGATGTCTTTTCTCCGGTTTTTATTCCCAGCGAGTCCCTGCAGTCGGAGCAGACGCGCTCCTCGTCCAGTG
AGAATCTGCCCTTCAGCATATCACGCCTGCTATCCAAGCCCTTCGAGACGAGTCACCACCACCACAACAACAACAACCACCTGCTCAGCAGCAGT
CCGGGCTCCAGCAGCAACAACAACAACAGCAGCGGCGAAAAGGGCGAGGAGAAGGAGCTACTGCAGCAGGAGGACCACGACCTGGCCTATAAGCTGGC
CACCAGCATCGCCAACTCGACATACGGAAGCGCCGCAGCACTATACTCGTATCCGCATCTCTATCCCTCAGCGGCCGGCGGTCATGTGCTACGTG
TACCGCCCCAGAGAACGCCGCTCACCTGGGCACTACCGCCACTGCATCACGCGGCGCTGGCACATCAGGCGGTCAAGGATCGGTTGGCAGGTGAG
TGAATAGCAGCGAAGTCAAGAGGGTTTGCCAAATCCAACCCATTCGGGGCCCCCATGTCGGGATGGCCCATGTTCGCCGAGATCTTTCGGGGGAG
CGATCCTCCAATGACCCGCGGTGGCAATTGCTACTGATCCCAAATAAGCACGATCAGAGAAGACTTTTAAGGCAACATGCCTATCGGCATGTCA
TTGTTGGCCAACACATTCGTGCACCAAGAGAAAATGTGGCATTTGAAATAAAAGAATTGGTAACATTAAGAATAAAAATGTTATATATGTGCCTA
CATAACGCGTAGTTGGATGCATTCAATTGTGCAATAGGGTGTAGGAACATAATTTTAAACTTCTTGATAAAACATATTTTTGTATATTCATTGTT
GAAAATAAGGTGCGAAGAACGTTGTCTAATGGTCTAAAAGGGCTTACTTACATATTTCCTTATAATATAATTACGATGGTCTATTAGATGGTATT
TTCTGTGGGTAAGAAACAGCTTAAGGCTAGAACACAGGTCTCATAATACGAATTTTCGCTCAGTGTACACTCACTCTGGTGAGCTTGGGATGCTA
AAGTATAAAAACATGTTTGCCTTCAAATGCGCAATCGCAGCTTAAGTTAAAAACTTAACGCTGAGCCGCCGCCCCAGAAGCGACTCAGGAATGAGA
TGCGCCTTCTTATTTGCATGCGCATGCGCAGTTGAATTTGTATCTGTATCTGTCGCTGGTCCTCTGAATCCGTATCCGAATCTGTATCTGTATTC
CATCTGAATCTGCAACTTCACGTGCAGCTGGGTCTTCTGGCTCCCTTTTTGTTAATTTGTTTACATTATGAGCTTCACTTGTAGCTACAAGCGAT
GGGCACAGCGCGAGCCCTTTGAAATAATGAGACGGCGTTGATTTTATTACGCCTCGGCAGCCGAGGGATCTTCAATGGTGTGGAAGGGGGATCCC
GATAGGGTTCGGATCCTATAACTCATAATATTCGGGCCTTTTTCGGCCTTGTGATGTGGAAAAGCTGCTTAGGAGCAGCGCAGCCCGGCAATCTG
ACGGGCTTTTATGGCCGACATCCGCCCAGTGGTTCTGGTTAGCTGTTTGGCCTTTTTCTTCATTTTAGTTATTTTAATGAGCTGGTTTACATGAC
TTTTTAATTTCGCGCTGCGCTCGAAAAGGAATTAATTACGCATTGGGCGGTCGCTGGGCTCAGCGAGTGAGTTTTCTGTCCTCGCCGGCTTATTT
ATCGCCGCATACCGCACTTCACATTTGAGTCCAACTGACATGGTCAGCTTTTAATTAGCCAGTCGAATGCTGGCGATCCGAGGGCTGCATATCCA
TATCCATACTTGTGTGTATATCCGCCGAGGAGGGGCATTCGATCGAGTGGATCGTATAGAATGGAATGGGATCGGATCAGTCACTTCGAGTCGAC
TATTCCACCTGAGGGGCACACTTATGAGCCCGCCGGGTGATCCAAGCTTCTGCCGCTCGGTTTCGTTTTGTCAACATCTTCGTTTTCGTCTTGGT
CTTGGTCTCGGCCAACGTCTGTGTCTTTTTGTGTTTATTGTGTCGCTTGCCTTGTGGCTGATAAGCTGGCGCCTTGGCTTTTTTCATTAACAAGA
CAAACGAGCGTCCAGGGTGCGGATCCGATCCGATCCGATCCGATCCCTTCCCGCGACCAAAGTGCTCCTCTCTCTTCCGCCGGGGCCCTTAGCGC
CATATGATTAATAACCATCGCATGTTAATTCTCGTTATTTTTTGGGAAACTACGTCGCAGCAGGCGCCAATTACTTTTCGGCCATGCACGCCCTA
ATGCAGTTTCATAACAGCCATAATAGCCTGATTGGAAGGGAGTTGGGCTTTTGTCACGACACTTGCCCACACGAATGTTACCAATCAATGGCGGA
GTAGGATCTATAGGCTAGTGTATAGAAATTCCCTTTACTAGGGAGCTCCTTTAGTAATTTAGTATTTAATATTAAAAAATGATGTAAACTCCGTG
AGACTGTATACTAATTTGCCATTTAACAGTTCCCATTTGCATGCGCTTTGATTGGTTACGTGCTAGTCTTGAGGTAACTAGTATATAACTAATCC
AAATCACTAGCAAAGGTCAGAGTGCAGCACTTTTGAAAAGAGACCAAAATAGCGGAGTGGGAGGAAACCAGTCCCAGCCACAGGCCGTCATCAAT
AATGCATGCTAAAAGCTTTTTGCATTATTTTAGGTATTTCTGGTGAGACTTCTCGGCCGCAGCCACACACTCACCGCCATCTGTATCTTAAAGAT ACTTGTGTTAGCTTGTGCGAAACATCATAAATAAGCTCGGTGGAGCACGGTGGAGTGCCGGAAAGCTATAAAATTATGCTTATGCGCCTTAACCT
CCCTCTAAGCGGATATGTTACATCCTTGAAGGATACACACATCTGAGCTGCGGCAGAGGGGAAAATCCCGAGGCTGCTGCTTATGTGGTGCGATA
AATGGCTTTTTATTGAAATTGATATTGCCTGAAATATTCAAATGATCGGCAAGCCACAAGACCTCCGACCCGAAAACCTTTGAAAAATTTATGCA
CCCAGCCTCGAAAGTTTATCCCCTGGGCGGGAAAAGCCCGAAAAAAGGGTTACCGAGAAAAGTCGCAATAAGATGCATGATTTGTCAGCTTAACA
CCCGCCATTCGTTCGCCGGCATTTGATGGCTTTTGACAGCCCAACGCCATTTTCCTACGCCAACTTGGACACCCATAAACACAACTCAGTTTCAA
TGGGAGCTGGTCGGGTTTAAAACGAAAAGTTATATGCACATTGAAAAGGTTTTCATACTTTAGAAAGTATTCCAAGGGATTGGGAAAATCCGACT
TACGCTGCAAATCATTGAACATTTACGCTCCAGTTAACGAGTTGCGCGTGTATTTTCAAAATCATGTTGAATGTATCGCTAAAGTTTTTAGGTTC
CTTAAATAAGTTAAGAACTGAGAAAGCAGTACATTCTGCTTTATGCAATGCTAATGAGCACACTTGAAATTAGATCATTTAAACATTTGCCACCT
TTACTGAAACTACACGTATTTTTCTCTACCAGGAATGATATAAACAAATTGCTTTTTGCATAAATGTATTAAGATTTCTTTCAATCATGTTTTTT
CGTTGTCTGCGATTAAAATGGCATTCAAAGAATTGAGTGACAGTTGATTAATTTGAATAGTTTTGTGGCATTATCAGTATGGTTTTAAATTAATC
ATTGCTAAATTGTGTTAAAAATCTTTATTAATAATGAAATAGTTGCTATTTTCCCGGCGGCGTTTGGCCATTAAATTGCACAAATGCTGACCAGC
TAATTTCCCTCCAATTTTTCACTTGACCTCATCTGCGGATCAGTCAGTCGGTAATCCGGTTTCCTAATTGTCTCTCGTGTTGCGTTGTTGTGAGC
GAGTGGCCGAACGCCTTACAGTTTCGGCGCGCACTGTGCCCGCCTTATCGCGCCCAATAAACAACAAAACACACACAACGGCGACTGGCAGGAAT
TTTAAAAGGTTCAGCGCCAGCACAGGCTCAGCCACCGTTCCGCGCCCGAATCCACAAATCGAGAAATCCACAAACCAAAAACCCAGAGATCCAGA
CTCGGACACTGGGTCACTTATGCGTCCTCCGAGCGCGACTTTATGACTCAACCTCAATCCGAATGGAAATGGATGTCGCGTGCTTTGTCTACAAG
AGGCGGCGATAAGGGCTCCTGCTAGACCGCCGCCCGAAACCTCAATCCTTGGCCATTAGGCAGCAAGGCAGCGAGCCAGCGCGTCAGCGGCCTCC
AAATTGATTTCCCAGCGGGAGGGGTCGTATTTAGCCACTTAGCCATTTAGGCAGCCAGGTAACAGCTATGAGCTAACAGGTATCGAGTAGCCAGC
AGCGCTAAGTACTCGCAGGCGCACAGGTGCCGCCGCGCAACTCCGGAAGCGGCGCTCGGAAATGGCCAGTTATCTAGGAATTTATTGTTTGCTAA
TTGCCCGCCAGGACACTTACCGCACGCAGGGGAGACGGATACAGATGCAATCGCAGGACTCGCATCTAAAATTCGAGAGGGTTTCCTTGCTGAAA
ATTGTATAACAAGCCCCTTGTTTAAAAGCGTTTCAAGTCTAAGAAATGATAAACATTCCCATTTTGTGAGTGCACTCAATTGCTTATCGGTTCTT
AATGAACATAGTTACTTAACAAATTGAAGCTTTTCGAATAAGCAAGAGCATAAATCTTTTACTATTGCCGGTATTATCTTTGGATATGGAAAGTT
TCATTAAAACTTAAATAAGAAACACCTTATAGAAAATGCTTCTATACTACTCTAGATGCACATATTATTAATTTTTTGGAGATCATCCCTTCAGT
TTATTATATGACTACAGGTGTATGTAGAGAGAATAAAGAGAATCTGAGCGAGCGTTATTAAGTACTTAACATCCCTCTCGTTACAGCTGCCTTTC
CGATCGCCCGACGGATCGGACATCCCTACCAGAATCGCACGCCGCCGAAGAGGAAAAAGCCACGCACATCCTTCACGCGCATCCAGGTGGCCGAG
TTGGAGAAGCGCTTCCACAAGCAAAAGTATCTGGCATCCGCGGAGCGAGCGGCACTGGCCCGCGGACTGAAGATGACCGATGCCCAGGTGAAGAC
GTGGTTCCAGAACCGACGCACCAAGTGGAGGTGAGTGTCCAGATTTCCAATTTTCCCTTTCGCAGCGCATCCCGCTGGGCTAGAGGCAAAAATCA
ATACCCATACCCTTGAGCAGCTACTGTTTTTCCGTGCTTGGAAGTGCTGACAGCTTGACACTTACCCTCTTCTATACCCCCCACCCCCCCGCTTT
TTCGTTTTTTACGTGCCGTTTTAAACTACAATATGCACAAAAGGCTTTTGTTAAACAGACCGAGGGCAGAAAATAGCCGACGTGAAAATGCCCTA
GAAATGCGTGCTTAGTAATTATTATTATTTTATAGTAATTTAATGATGCTCGTTCAAACATTTCATGTAATTTTATTTCTCTTTCTTTTTATTTC
AAATAACAATCCGCCAAATAGAAACATTACTGTAGATTAAGTTCGTTCATACTAAATTTAGATAATTATTCTTTGTATAATTCAGAAACTTTCTT
CTTACACGGCTAATGCCCAGTACGGTGTAACTCAACTAGATTATAGGGCATCAAAGCCCGACGCGCATAAACGGGGAGCAAATGGCTTATACAAT
ATGCATGAGCACATTAAATGAACAGCACCCAGCCCCAAGAAAAAGGGGAGCATATTTACGAGGCTTACGGAGAGGGGTAGGTAGCTGCATTTTGT
AGCCACAAAGAGCGCTCTTGTTAAACAAGCTAATTGCCAAGTTTTTTATGGCAGTTGCAATGCCTGGCTAACTATATGGCTTAGAGTCGCATTAA
GGCAGACATAGCACTCGTATTAAAAAATTCCATTCAAAATCATAGTTATACGTTTTGTAGTTGCAATAATTACTTGGGCAGTTAATTCGATTAAC
ATTTTGATACACCAATAAAGTGTTATTACGTACTCTTGCGAGCATACTCTACATAAATATGACAATTTTCTAATTATTTACATTTTCCGAATTGG
TTACTTACATTGTATTGTATCAACATTATTTCTTTTAGTTTCCTTTTAAATAATTGGGTGTACCAAAGCTAGGTGTCAGATGACAAAGGAATTTC
TGATTTATGTGGCCCCTATTAGTAAAACTCTTGTACTCACTTTCACATGCAAATGACTATTTATTTGAAACCGAAATTAGTCAGACAAAACATGT
GCCCAATTTGGCGGGGTATTGATGCGTGATATTGCGTGCGCCTAATTGGTTTCTTTTTTATTACCGTCAACTAAAAGTATTTGAATATGAAATTA
TTTGAGCGGATGAGTTCGGATAGTCTTGCACTCATATGCGATTAGTGGCCGTCATAAAGACGATGGCAAATGGCGGCTAAATGGCCGAAGTTTCC
CACTTTCCCAGGAAAGGGAGCAGGGAAAGCGGCAAGTCGGGAAAGCAGCAAGGCGGGAAAGCTGGCGGGACGGCGCTTAAGTCGCGTTAATTGCC
GCTTAGCAGGCGGCGTTTTCAGGCATTTCAGACATTTTTAGAGCCCAGTCCTCCTGGCTTATCAGCCATTTTGGGCCTATTCCAGCTCGTAAAAA
TTAATGATGTAAAACGCAATTTTGTTAACGGCAGCGTCACCGGCAACCGCCTCGGCCACGGCTCGTTTGCGGTTAAGTGAAATGGCAATGGCACA
TTATAGTTGCCATGATTACGAGGCGGCACTACTCGTAAATATCCAGGGTATATGTAATGTGCTCACATAATTGCCTTAATGCACACTGCGCTGCA
TTTGCCAGTAATTTGAATAATTAGCCCTGTCCAACGTGGCGTATGTGCTATGTGCCAGTTGCCCATTAGACAGCAAATAAAGATTGCGAAACTGT
TGTCTCTTGCCCAATTCTTAATAAATAGCAACTCGTTTGCGACAAGGTGAGTGCCTCATTACGAGAATTGTCTGTATATTGAGTGATTCGATTCG
ATTGGATTCAACAAGAACAGCAACACTTGCCATCAATTATTAATAACAAATTGTGCGGCCAAATGAATGAACTCCTGTTGCCCGTCACTGTCTGA
CAATGTGTTTAGCAAAAAGGCAAGAAAAAAAGACGAGGAGCAATCTGCCAAAGCAGATACATACACAACGCAGATACAGATACAAATACGGATAC
AAAAAAGTGTAGCACACTTCCGGGCGTTTTATCCATGTGGCTCCGAAACAAATGGCAGAGTCGGACTTCTGTCTGGGTCCTTTTCCCTCATTCTC
CGGGTCTATAACTCAATTAGTTTTACACCCATAAATCAAGCTGCCGCTAAACCCTTTTTAATTACACGCTCGTTCATCATCCGAAACATTTCCAT
CCCACTCAAAAATATTCTTGCAAAATCTTAGTTTAGCTTAGCTTAGCTGGTACTTCATGGTAATTGCCTGGCATGTGCGAAAGTTTTCCTGCTGA
AAGCTGGCTAATTAAAAATTTACACACATGCCAGAAAGCAACTTTGACCGCAGAACAAAAATCAATTTGACTGAAAGCAAAGTTTTTGCGGCCGG
AGCCGAAAAATCAAATAAAATTAATTACAATGGCGAGGGCCATTTGTAAATTAACTCGCAATCTTGTTTCGCCCGTCGGCACGTGTCCTGCGAAG
AATCTTCAAGTTGGTGGTGGGCCGTTCCCTTGGGATCTTGGCCTGAAAGCTCCTTGGACGCCTTGGCCAGTCAATTGATGGTCTGGCTAAATTGT
TATGTCTTTGGGGATAATTACCACAGGACCTTTTTGGGGACCGCTATCTTCATCTCGACTTGCCGACATCGTTCGCGTGCAATGTGTGAAATGAT
TTTAATTACCAGGACATGACCGGAAAAGTCTTAAACAGCAGCTGCCTCCGTTGGCGACAATTGGTACCCTGGGGCGGGGGAGCTAAGGAGATTTA
TGCGCCGGGTTTTAATAAACATTTTAGGCTAATGTCGGGCCATTACTTATCGCGGATGGCAACAGAAACTTTCCACATCAACGCGATGGCGCCTA
GAGACTAACATTTAACATTTGTAAAGCGTTTGTTACATTTCCCAGCATCGTGCCCGAAGATAAATTACAATCGTGTCTCTGTCTCAACCCCAAAC
AGCGAATTAAGCCCGCACACATCCCAAGCTCACAGAGCCGGCTTCGTTAGCCTGGCCTTTTTGGAGTTTTAATCAATTTTCGTTGAATTTTTCA
TGCGGTAGCTGGTAAAAATGCTGCCCGATAAAGCCAGCTTGAAGGCGAAAAGGTGAAAAAGTAAAAGCGAAGTGCTTGCTGCATAATAACTCACT
TCCAACGCGAAAACGACAATTGAATTGTTTTGCCAGCAATTGGAAATCGGGGTGTTAGTTGTGTTAGTTGTGAGTAAGAAAGCAATTTGCAGTTA
AAAAAAAAAACACTTTTCAGAATTACCTAAAATAAATGTATAATTGATTAACTAAAGATGTTATAGATCATATTAAATGAAATCATTTTGCTAAC
TAGCCATATATCCACTTCTCATTTAAGTTGGCTGCTAGTCAGCCGTAAAGACACAAGCTAGTTATCCAATTTGTGGCCCAAAAGTTTGCACTAA
ACGCCCAGGCTAATGTATTTTTAATGAAGCCCACTTGCGAGTTACGAAAGCGTAGTTTGAACGATGACAATGCTGATGAAAACCTGAAAACCGTA
ATGAAAGCATATTAAACAATAATTATGATATATGTTTGCCATGTGCTAGCCTCGCCTAGTTGTGGTTATAATTCGGGCAACCCCTTCCTCCGCCT
CTTTAGTCGAAACATAAGAACTTCATTAGCTCATGAAATATTCAAGATGGCGCAGAACAACCCCTAGCTCTGCGGGGGTGGATATACCACTGGAT
GGAGCATCGCTTGTGAAGTGGAGGTGGAGGGTCTCTCCGGTGCTCGGGCGGTGGTGGTGATGGTGGTGCGGGTCCATGGCCACAATTAGAGCAAC
ATGCTGCGCAAACGCGGGCCGGAGTTGCTGCATCTGCAGTGCAATTCAGCCCTGAATTATTTATCAGCTGGCAGGGCACAAGTTGGAAGTTGGGG
GAGTTGGCCAAATCCCTTTAAGCTGGGGGCATTCAAAATGCAATTTACGTACACAGCTCCAGCTCGGCACAAAATTAATTTTCCATTTTCCGCAG
AAACAAGCACAATCGATGGAGCACTGTGCCTGTACAGCAGTCAGCATATTTGATTTGATTAGTTTTAAATGGTCTTTGTAGGCCGCCCACATAAT
GACTTGATGAGCCCCTGATTAGGCCCCAATTGGACAGGTGTGAGCCACTGAAATGGGTTTGCGGCAAATTGGTTTTCCATAATGAATATGTACAT
TAGGCGATACTATTTGCCAGATAAGATTCACGGTCATCCAATGTATCGATTGAGCCGGGGCAGATGTTGCAACTTTGAAATTCGTTAAATAAATT

FIGURE SHEET 482

CAATCCGAACCCTATATCCTATACTTCCCATAAGCAATTTCGTAGTAATTAGGGGGAATATGTCAGAATTTAAATGTTAATCAAGGAAATGAATT
AAGAGTGGATCAAACTATCACAATTTTTAATGTATTCTAGCAAACGTCACCACTTTCATTTTCTTTGAACAACTTAAGTTTCATAAAAAGCGTAT
AGTACAGAACTTCCAAAGAGAACTTGAGCCTTACGAAACACAAGTTATCCTTATTAAGCCTTAAACCATATTTCAATAATATTTAAATAGATTCT
TAATGAAAGTTTTATCCATGACCTGGCCAGTTACTTACCATTACCTTCTTTTTCTCCATTTCAGACGACAGACGGCCGAGGAGCGCGAGGCGGAG
CGGCAGGCGGCGAACAGACTGATGCTGTCCCTCCAGGCGGAGGCCATCAGCAAGGGATTCGCGCCTCCTTCGGCACCCCTGGGTTCCCAGGGGGG
CGTGAACGGGGCACCGCTGGCTGCGTTGCACGGACTACAGCCGTGGGCAGAGGCGTCGCATGCGGCGGGCTGCTAATCGGGGCGCCATCGGCGGA
CGGAGCCTGAAGTTTGGCGGGAGCTGGTTTATTTGTGATACACTTCGCTTTGTACATAGTTCGGATGAACGGACAGTTTGCACTGTACTGTACAT
AGGAAAGAGGGGCGTCGCCTCGAGCGCCCACTGTAAATACCTAGCTTTACTCTGTAGTGACGCTTACCTAACCGATGCCGGGATGACGAGGATTT
GCGATGGTGACCCCGAAACAGCGCTTTAAGTTTGTGTAGAATCTGGAATTTCCGTTTTGCGTTTCGTAGCGGTGCATTTAGGATCTTAGTTATTG
TTCGACAGTTTCGACAGTTCGGCAGAAGCAAACCGCATCTCAAAACGTCGCAGTGAGCTTGGAAGCCACATTTAGTAATAATATATTTAATATAC
AAAATTATATACGGATTGTAATTGTAATGTATTGTAATTGTAACATCTGTCTGTAGGCTTAAGCGAATGGCATTACCTAGTATTATAAATTATGA
ACCCTAAAAACATGTACGATTATTGAAAAGTAGAGAGGATGAGCAATGAAAATAAACATATTATTGAATCAAAGAACAGAGGTATTTGGTTTTGG
CTTTTTTACAATAGTATAGAACTGGATCTTTCAGTTCTGGAGAATAAGTTTCTTTTGGTTATTTGACCACATCAATTCTTGTTTGGATACCAAAT
AGGTAGCAATTGATAAAAAACTCCCCCAAAACAAACGAAATCAAAAGTCAGGGGATGTTTCCCTGCCTTTTCAGTTGAGTTCCGCATTTAATCGG
CTCTGTCTCAACCCTTAACTAGTACAAATACCCCATTGAAGATGATTTATAGACGCTTATTGACAGGACTGGGTGTTTCGATCAATAGACCAATT
TTGATAGAAACCTGCTCCTCAACCGGATACCATTCGACGTGCTAATGACTGGGATGCTCATAAAAAAATCAGCCATATGCTCGACCCCGAAAAAC
CAACAACAATTAGCGGCGAATATCCGAGGCCGTTCATTATAAGTGTATTACGTGTTTTTGCGCTGAAAGCAAAACAAACAGGCGCCGCCGGACAG
GTAGCCCTATACTTAGAG
(SEQ ID NO: 892)

Exon: 1001..1176
Exon: 3000..3415
Exon: 7877..8105
Exon: 12795..13078
Start ATG: 1103

Transcript No. : CT23946
AAAATGTCCAGCCACGAGGAGGATGACCATGAGCACGAGAACGAGCACGGCGAAGAGGTGGAGGAACAGGAGATCCACGTGGATGTGGACTCGGA
CTCGCGGATGTCATGTGGCAGCGGATCCGATGTGGATATGGACGGCGGCAGCTGCTACGACGAGTCCGAAACGCCATTGAGCGAGTCCCTGCAGT
CGGAGCAGACGCGCTCCTCGTCCAGTGAGAATCTGCCCTTCAGCATATCACGCCTGCTATCCAAGCCCTTCGAGACGAGTCACCACCACCACAAC
AACAACAACCACCTGCTCAGCAGCAGTCCGGGCTCCAGCAGCAACAACAACAACAGCGGCGAAAAGGGCGAGGAGAAGGAGCTACTGCAGCAGGA
GGACCACGACCTGGCCTATAAGCTGGCCACCAGCATCGCCAACTCGACATACGGAAGCGCCGCAGCACTATACTCGTATCCGCATCTCTATCCCT
CAGCGGCCGGCGGTCATGTGCTACGTGTACCGCCCCAGAGAACGCCGCTCACCTGGGCACTACCGCCACTGCATCACGCGGCGCTGGCACATCAG
GCGGTCAAGGATCGGTTGGCAGCTGCCTTTCCGATCGCCCGACGGATCGGACATCCCTACCAGAATCGCACGCCGCCGAAGAGGAAAAAGCCACG
CACATCCTTCACGCGCATCCAGGTGGCCGAGTTGGAGAAGCGCTTCCACAAGCAAAAGTATCTGGCATCCGCGGAGCGAGCGGCACTGGCCCGCG
GACTGAAGATGACCGATGCCCAGGTGAAGACGTGGTTCCAGAACCGACGCACCAAGTGGAGACGACAGACGGCCGAGGAGCGCGAGGCGGAGCGG
CAGGCGGCGAACAGACTGATGCTGTCCCTCCAGGCGGAGGCCATCAGCAAGGGATTCGCGCCTCCTTCGGCACCCCTGGGTTCCCAGGGGGGCGT
GAACGGGGCACCGCTGGCTGCGTTGCACGGACTACAGCCGTGGGCAGAGGCGTCGCATGCGGCGGGCTGCTAATCGGGGCGCCATCGGCGGACGG
AGCCTGAAGTTTGGCGGGAGCTGGTTTATTTGTGATACACTTCGCTTTGTACATAGTTCG
(SEQ ID NO: 893)

Start ATG: 103

MSCGSGSDVDMDGGSCYDESETPLSESLQSEQTRSSSSENLPFSISRLLSKPFETSHHHHNNNNHLLSSSPGSSSNNNNSGEKGEEKELLQQEDH
DLAYKLATSIANSTYGSAAALYSYPHLYPSAAGGHVLRVPPQRTPLTWALPPLHHAALAHQAVKDRLAAAFPIARRIGHPYQNRTPPKRKKPRTS
FTRIQVAELEKRFHKQKYLASAERAALARGLKMTDAQVKTWFQNRRTKWRRQTAEEREAERQAANRLMLSLQAEAISKGFAPPSAPLGSQGGVNG
APLAALHGLQPWAEASHAAGC*
(SEQ ID NO: 894)

Name: C15
Classification: transcription_factor
Gene Symbol: C15
FlyBase ID: FBgn0004863

Celera Sequence No. : 142000013384668
AGGATTATGACAAGTGCTGGCAACTGGATTTCCGAGGAGCTGGAACCAGCTACTCTACTGTCGATTCAGGAGGATAATGGTATTGTTACCAAGGT
GTACGTGGCGCCCTGTTTGCAGCCGATAAAAGAGGAGAAAGTTTTCCTGGAGGACAACACGCAACGCTTCCACTGTCCGCTTTGCTCTAATGTGA
TTCGCACGGCCGGTGCCTACAAGGTCCATCTGATGGCCTGCCAAAGACGCTTGGCACGCATGATGAAGGATGTGCCGGACGTGTCCCAGCATCAG
TGCAACATTTGCAAGAAAATCTTCTCCTCGGTGGATGCCCTGATCGGCCACAGGCTCCTGCATGGAAGCCCATCAATGAATCGCACCTGTGCATC
CTGCCATGTCAAGTTCGGGACGGATCTGGAGTATCGCACCCATTTGGAGAGCCATCTGATACCGTGCGAGTCCACGGATGAATCCTACGAAGGGG
CGTACACCATCACCAAGACCTTCAATTGCGTCTTTTGTCGCACGGAGTTCAAGGCCTGCTTTAAGCCTGGCCAAGTGACCCGTCGATACGCGTGC
GACGCATGTATCGTAAGGCTGAAGGCCCAGGAGGAGGAGAAAAAGATCTTAGGGAAGAGAAGGCCCGAATTAATCTGTGATCGTTGTGGGAAAAA
GTACAAATATGAGGGTTTCCTTCACCGTCATCTGAAAACTTGCCAGATGCCGGATAAATGCAAAAGAAAGCGTGAGATTGAAATCACCGAGGTCA
GCGAGGTAACATTTACAGAAGTTGTGCAAAGTTTTAATAATTGATTATACAAATTCGCACATTTTAATTTTAAATTAAATAAATATATTTTTTAA
TTGTAATATTTTTTATAATTTCAAATTATGGCGCCCATCCCACCGATATCTATTTCGATCTGCTATCGATGTGGTCACACTTATCGATAAATCC
ACCGTGGCGTGGTATTTTTGATTTAAAGCGTTAGTCGATTTCCCGCCCAGCTGCACGTGTATATTTTTTTGCGGTCCAAAGAAAAGTTCGTAAAT
AAACGAATTTGCGTGCATTTCCAGCGAACACGATGAGTTCAGACGAGTCCAGCGACGGTTTGGAGGAGCTGCAGAGTCTGAAGGCCCTCTACGGC
CAGCAGGAGCAAGAGAAACCGGCAAAGATCAAAAGGGAACGTTATATTCCAAAGGCCTCGCAGGCCAAGGAGCTCAACTATGTGGAGGTGCCCAT
GGAAAAGGTGCTCTTCGGCGACAGGCAGCGACTGCTCACCAATCTAGCCAAGTCCGTGGGACAAAAGTTGCCGAACGATGACGAAGACGAGCAGG
AGGAAAATCCCGGCCAGGCAAAGCCAGGCGACAAGCGGAAAGCCGCCTGGTCGGATTCCGATGACGAGGACCTGCAGGTGGGCGATGTCAAGAAG GCCACAAAGCACACGGGTCCACTGAACCACCTGCGCAAGGATAAATCGTACAAGGAGTATCTTACGGCGCGATTCCAGCGCACGCTTAACCAACC
CAAGTGGGCGGAAAAGAAGGTCAAAAATGAGGACGACGAGGACGTATCCTCCGACGAAGAACTGCTGCGGACGGTTGGCTTTATCGATCGTAAAG
CCCGGAACAGTGATCTGCCCCAGAAGACTCTGAATTTTAAACGGGTCAAAGACCTGAACAGGGCCACATATGCCGAGGGTAATGCCACCAGCATT
CAGTTTCATCCAACCAGTACTGCTGCTCTAGTGGCGGGCATGAATGGCCTAGCCACCATCTACGCCGTGGATGGGCAAAAGAACGAAAGGTTGCA
CAACATGCGCTTCAAGAAGTTCCCGCTGGCGTGCTCCAGAATTGCTCCATGCGGCACAAGGGCGTTCTTTGGTTCTGTGAAACCATTCTACTACT
CCTACGACTTGCTGGAAGCCAAGGAATCGAAGCTAAAGCTGCCGGGCGCAATGGAATTTATGCACCGCTTTGAGGTGTCTCCATGTGGCAAATTT
ATCGTCACTGCTGGCAAGTTTGGAGCCATTCACCTGCTCACGGCCAAAACAAATGAGCTGCTGCACAGCTTCAAGCAGGAGGGCAAAGTGAAGGG
ATTCACATGGTCTAGTGACTCCAAGAGGATCCTCGTCTGCGGTTCCACTTCCAATGTCAGCGTGCTGAACCTGCGCCAGAACCTCATCGAGCACA
TCTTCATGGACGACGGCTGTATACATGGAGAGTCCATTCAACTGTCTCCCAACCAACGCCTACTGGCCACCGGCAGTCAAGAGGGCGTGGTCAAC
ATCTACGACTACGAGAGCATTTTCGCATCCAAGGCCCCACAACCCGAGAAGCGCTTCATGAACCTACGGACTGCCATCACGGATCTCCAGTTCAA
TCACTCATCTGAGCTACTGGCGATGTGCTCCAGTGAGGCGCCGAATGCTTTTAAGCTGGCCCATTTCCCCAGCGCCACTGTGTACTCCAATTTCC
CGGCACAGAACGAGAAGGTTGGCTTTGTGACCTCCATGGCCTTTTCGCCGCACAGCAGCTTCCTGGCCTTTGCCACTAAGGGCAAACAGGTGCCG
CTCTTTAGGCTTAAGTACTTCAAGGGTTATTAATTGAAGGCAGTATGATGTTTACAATAAATTCTTAAATAAAATCATTACTCTTTCTGTGGTTA
CAATGGAACCATCTTTATTTAAGTTAACAAATTAAGGGGACTTATCTTTAGAAAGGAGCTCGGAAAATATCGCGTTTCTGGGAGTCTTGAATCTT
GCCAATGTCTTCCAGCTTCTTGCTGATGTTCGTCGACTGCGATTCGATCCACTGCAACGAATTCATATGGGCATTAAGGATTTTTCCGATCTGTA
TGATGGGATCAGTGGTGTCCTGGCCCTTGTTGGCCTCGTTCAAGTTGTCTATTATCTCCTTTAGATCCTCGGACATCTGCTTCAGTTGTGTGTCC
AGATTCTCCACCATCAGGTAGGTTTGGCTGCGTTCCATGTCCACCCTCGGGAGATTAACGAATTCCTTCTCAAGCGGTCCCAGGCTGTCCTCAAG
CTCTTTTTGCTGCGTGGCTATAAACTCCAGCTCCTGGTCCAGCACTTGCTGATCGGTTTCACTTTTTTCACGGCATCGTTGAGCTCGACGATCT
TCCCGTTGTTGCTGATGAGCAGTTTGTCCCATGCGTTGATCTGAGTGGCCTGTTCGGTGAATACCTTTTCCTGTTCCTCGAACTCGAGAGTCCAC
TTGTTGATATGCTCCTCAAGTTGGTGGTAGGACAATTGGGATGCCGTGGAAACGGCCGATGAGTCTGTGGTCTTGGTTTCGGTAGTGAGATTGGC
AAAAGCACCACCAGTACTTAAAGTTGGGGCCGGTGCAGCTCCCTGCGTGGAGGCTATGGCCGACGGAGCTGCAGTCAGAGTTGTGGACGCAGCGG
CCGTGGTCTTGGGAGCTCCCAATCCAGACCCGCCCAGCAATCCAGTTGTGGTAGCTGCGGTGTTGGGTGCACTGGTTGCTATAGTTGGCACCACA
GATGCCGCTGGTTGAGCCGTAAAGCCTCCGAAGGCGGGAGGAGCAGCAGAGGTTCCAGTCGCGGTCGCAGAAGTGGTGGACGC
(SEQ ID NO: 895)

Exon: 1001..2598
Start ATG: 1078

Transcript No. : CT24010
CTGCACGTGTATATTTTTTTGCGGTCCAAAGAAAAGTTCGTAAATAAACGAATTTGCGTGCATTTCCAGCGAACACGATGAGTTCAGACGAGTCC
AGCGACGGTTTGGAGGAGCTGCAGAGTCTGAAGGCCCTCTACGGCCAGCAGGAGCAAGAGAAACCGGCAAAGATCAAAAGGGAACGTTATATTCC
AAAGGCCTCGCAGGCCAAGGAGCTCAACTATGTGGAGGTGCCCATGGAAAAGGTGCTCTTCGGCGACAGGCAGCGACTGCTCACCAATCTAGCCA
AGTCCGTGGGACAAAAGTTGCCGAACGATGACGAAGACGAGCAGGAGGAAAATCCCGGCCAGGCAAAGCCAGGCGACAAGCGGAAAGCCGCCTGG
TCGGATTCCGATGACGAGGACCTGCAGGTGGGCGATGTCAAGAAGGCCACAAAGCACACGGGTCCACTGAACCACCTGCGCAAGGATAAATCGTA
CAAGGAGTATCTTACGGCGCGATTCCAGCGCACGCTTAACCAACCCAAGTGGGCGGAAAAGAAGGTCAAAAATGAGGACGACGAGGACGTATCCT
CCGACGAAGAACTGCTGCGGACGGTTGGCTTTATCGATCGTAAAGCCCGGAACAGTGATCTGCCCCAGAAGACTCTGAATTTTAAACGGGTCAAA
GACCTGAACAGGGCCACATATGCCGAGGGTAATGCCACCAGCATTCAGTTTCATCCAACCAGTACTGCTGCTCTAGTGGCGGGCATGAATGGCCT
AGCCACCATCTACGCCGTGGATGGGCAAAAGAACGAAAGGTTGCACAACATGCGCTTCAAGAAGTTCCCGCTGGCGTGCTCCAGAATTGCTCCAT
GCGGCACAAGGGCGTTCTTTGGTTCTGTGAAACCATTCTACTACTCCTACGACTTGCTGGAAGCCAAGGAATCGAAGCTAAAGCTGCCGGGCGCA
ATGGAATTTATGCACCGCTTTGAGGTGTCTCCATGTGGCAAATTTATCGTCACTGCTGGCAAGTTTGGAGCCATTCACCTGCTCACGGCCAAAAC
AAATGAGCTGCTGCACAGCTTCAAGCAGGAGGGCAAAGTGAAGGGATTCACATGGTCTAGTGACTCCAAGAGGATCCTCGTCTGCGGTTCCACTT
CCAATGTCAGCGTGCTGAACCTGCGCCAGAACCTCATCGAGCACATCTTCATGGACGACGGCTGTATACATGGAGAGTCCATTCAACTGTCTCCC
AACCAACGCCTACTGGCCACCGGCAGTCAAGAGGGCGTGGTCAACATCTACGACTACGAGAGCATTTTCGCATCCAAGGCCCCACAACCCGAGAA
GCGCTTCATGAACCTACGGACTGCCATCACGGATCTCCAGTTCAATCACTCATCTGAGCTACTGGCGATGTGCTCCAGTGAGGCGCCGAATGCTT
TTAAGCTGGCCCATTTCCCCAGCGCCACTGTGTACTCCAATTTCCCGGCACAGAACGAGAAGGTTGGCTTTGTGACCTCCATGGCCTTTTCGCCG
CACAGCAGCTTCCTGGCCTTTGCCACTAAGGGCAAACAGGTGCCGCTCTTTAGGCTTAAGTACTTCAAGGGTTATTAA
(SEQ ID NO: 896)

Start ATG: 78

MSSDESSDGLEELQSLKALYGQQEQEKPAKIKRERYIPKASQAKELNYVEVPMEKVLFGDRQRLLTNLAKSVGQKLPNDDEDEQEENPGQAKPGD
KRKAAWSDSDDEDLQVGDVKKATKHTGPLNHLRKDKSYKEYLTARFQRTLNQPKWAEKKVKNEDDEDVSSDEELLRTVGFIDRKARNSDLPQKTL
NFKRVKDLNRATYAEGNATSIQFHPTSTAALVAGMNGLATIYAVDGQKNERLHNMRFKKFPLACSRIAPCGTRAFFGSVKPFYYSYDLLEAKESK
LKLPGAMEFMHRFEVSPCGKFIVTAGKFGAIHLLTAKTNELLHSFKQEGKVKGFTWSSDSKRILVCGSTSNVSVLNLRQNLIEHIFMDDGCIHGE
SIQLSPNQRLLATGSQEGVVNIYDYESIFASKAPQPEKRFMNLRTAITDLQFNHSSELLAMCSSEAPNAFKLAHFPSATVYSNFPAQNEKVGFVT
SMAFSPHSSFLAFATKGKQVPLFRLKYFKGY*
(SEQ ID NO: 897)

Classification: hypothetical

Celera Sequence No. : 142000013384534
TTGCAGGATGTACTCCTTACGCCGTTGGATGACTGCCGCATCGAATCTCTTGAAATATGTGCTATCTGTGGGCACTGGCAACTTGCCGGGTAGTT
GGAGACTCTTGTGGCGCCGGCTAAGCTCGCGATGCAGCCGCTTGACATCGTGGAACCGTTTCCACACCACCAGGCAGGTCAGAGCTTGAGGTACC
GACCTTGGGAAGACCTAAAAGTGGGTGAGGTTTACTATTTGGAACAGTTCATCTGCCCCAAAAAAAAACGACTTACAATCGAGGTGATTTGTAT
ATTGTGTACCCGCCCTTGTGCTCCTGGGTGTCCGTCACTGTGAAGCTGTGGATCCAGCCGCCCAGGTTGAGAGTCATTCTGGTTTCTGCTGCAAG
ACCTGGTGGTTTAGTTTCTAAACATATTTCCCATATCAAATGTCGTTGTTCCCCAACTTTTTTGCAACATTAAAGCTAGTGTGACCAAAGGACGC
CAAAATAACCACTTCCGGACTTCGAAATTAAATAAGAGCATTTAGTAGCTTATTTTTTTAACTTAGAAGGATTAAATTAAACCATAAAAATATTA
ACTGTTTTTTAAACACTTTTATTTAAAATAAAAAACGGTCACATTTTAAAATTTAAAATTTATACTCTAATCGAAAGTATCATAAGTATCGATAG
TCTGCAGTGCATGTGGGTTATGTCATGACTAATGACAAATTGAATTGCACAGAAAAGGTGGAAGTCCCTGCTAACGACATTGCTTCATGTGTTCA
TTTAATACAACATATTTATAGCTATAGCTTTTTTAAATGTGTCAATTTACTATAACATTTTAAAACTTCCGAATAAAAGCTTCACACAAACGGAT TTTCACAAGTAATATCCAGATAGAAATACCATTTTAAAAAGAAATTTTTCCGATTTTACCACCATCGCTTGCGCATGCGCACGGAACGCGTGATG
CGTTTTTAAGTCCGTCATTAGGCCATCGCCCATCAATTTTAGTGTTTCAACCGCCGCCCGATACGGTCACACCGCTCGAGAAGTAGAGAAAAAAG
AAGGCGACGAACCACAGGCAGCAAGCAAAATCGACGCCGCACGTACCGGGAGCATTTAAATAATTTTTTCTGTGGATTAATTTTACCGAAAAGGC
TTCAACACAATGACTGAGCGCGAGAACAATGTGTACAAGGCAAAGCTGGCCGAACAGGCCGAGCGCTACGACGGTGAGTAGTGATTCCGAAAAAA
AATGGTAGCAAAAATGGTAGAAAACGGTAGACAAATGCTAGTAGAGTAGGGAAAAAATTTTCTCGACTGAGGAGCGCCAACGTTTTTGGGGAGGG
GTCGCCTGGGATTTTTTTTTGTCTTCCCGATCCATTGCGTCGTCGCGTGGTCGTTGAAAAAGTCTAGAGCTCCGCTTTTCGTCCGAATGTGCCAA
TTAAAAGGTTTTCTTCCAGAGAAAACGATGGAAATTTTCAATTTTCATCGCTGTAGCTGCATTCGAAGCGACGCAGCGTCGCGATGAGTAGTATT
TCTTGCGAAAAGAACGGGAGATGGAGGAAACAGTAAGAAGAGGAAGAAGCCGAAGAAGAAGCAGAGCGTCGGAAGAACGAAAAGAGATGAATAGA
GTGTAAAACCTGATTTTTACCGGCAAAAATTCGCGTGGTTTTGCACAAAAAGAGAAAGAAACGGAATTGCGTATTATAATTTACAGCAAATAGTT
TGCTCCGCTCTTTCTTTTTTGGAACTATATAGTATTAGTTTAGAAGGGGAAAATTTTGTGTATTTGGCGTTGCGAGCAAGGGCTGCGCGGCAGCT
AGCATTTTATTTTCTTCCTTGGTTGCTAAGGGCTGTTTGCAGTTGATTCCAGTTCGCGTTCTTTTTTTTTCTTTCTTAGTAGTTGTCAAGGCGTA
ACTTTCTAGAAACGACACATTTTTTGGGGATTCTAGTTTCTTAAATACACTTATTCCACACCCAAAATCAATGATTGTGGGGCAGGGGTAGGTGC
AGTCCTCTCTTTCAGACCCCCTCCCCCTTTTTTTCCACGAAATGTGCTTTTCATGCGCAGCAGCGGCGTCGTCACCATGCCGTTGCTGCGAAAAA
TCGATGAATGAATCGATTGTGTCGCCGGCTGTCTCCCTCTCTCACTTTCTGCCTATTGCTTAATTCTTTATTTATGCAAATTAGTTGCGGCTAGT
TGCAAGCAGTTATGCGGCCACTTGGCAACCCTATCTGATAATGCGAAAAAAGGAAATATAAAATTTTTCTGTGCTTCTTCTGTTACTCTCGCATT
ACTCATGCTTATGCGCATGTATGCATGCGTGTGTGTGTGTGTTTGTACGGAGGTGTGCGTGTGCCGATGAGTGTCCGCCGGGCGGTTTTTATTGT
TGCTTCTTCTGTAGCCTTTGCTTATATTTAATTAAAAATACTCCAATTAATTAAAAAGCCAGCTCAAAATGCAAAGAAAGTCGCAGTGGGAGGGG
GACGGCAAATTCGGCATTTGCAAAAAGCGCGCGCTTAACCAATTGCCATAAACGCTGCGTGCGCCAAAACGAGATGGCTAGTGTGTCGAAGTGTC
GGCGACGCTGCACAGTGGCTGTAAAAAGTTAACAAACATTTGGCGATTCCTCTGTCTGCCGTTCCTTCCTGCTGCTGTACTTGGGCAGCGACTAT
AGCAACAATAATTGCAAACGGTACTCTGCACCTAATTGCCTGCAAAACTGACAACATTAACGGGCGGTGGCGGCGGCAAAGAAGTCAATCAACTA
TTAGCACACACAAACAGGGCATACATGCATACATACACCACTGGTGGGGATATTTGTGTCTGTATCACATGTTTGTCTTCTTATTTTCGCCCATC
GGTGTGCGTTGGTGTGCAGCACTTGGCGTTGGCCTTGTCACACTCGGACATTTTGCGGTGGAGCTCATGCTGGAGCACCAATACCATTGCGCGCG
AAGAGAGAGAAAGAGCGCGGCGGAGAGCGAAGCGGAGCGGCAAAGCCGCCAGCCGGCAATGTCTGCGCCCCCAATCTGAACTTGCCTCGCCCTCT
CCGCCCCTGATCTCATCTCCTCTTCAAACCCCTGCTCCCCTTTTCTGCACACATTAACGTCAGCCTTTAAGTGTGCTTTCTCAGGTGCTGCCCCC
TGCGCCCACCATCCCCCGCTCCATGCTCTTTCCATCTTGCGCTCTCTGCGTTCTATCTACATTTTTTTCGAGGTCGCGCGCTGCTTTTTCCGTTG
ATGTTCGTTCTCGTCAATGTCGTCAATATGCGCAAAAGGCAGACAAAAAAAAAAATGAGTGGAAAAAGTAGCATACATACGGTTGATTGATGGGCG
GTGGGTGGCGGTGGTGTTAGGTGTGTTTTGTTTGTTGCTCGCTTTTTGCTCAAATTGCACCATTTTAGGGGCTGTTGTTGCTGCTTCCTTTGTCT
AATTACACATTCTCTGCCCGCTGTAACGGTATGTGCGCATGTTTTTTCAGCTGCTGCGCCCTTATGCGACTCACACACACACACATACACACACA
CACAAAACCACGCGCACTCATACCCACACGAGCGCAAGACACACCCACAGGCGTCTCATAAGGGAGGGGTGGATCTCTGGGGGCGTGTTGGTAGG
AGGGGGTGGAAAATCCTGCCCATTCCTTTTGCTCCCTATTTCGTCCCAATATTTCATTCCAGCTCGCGTGACTTCTTTTTACTTTTGGGTGGTGG
TGGATTGCCTTTGCAGGGTTGTCGCTAGTTTATCAAATTCCAATACTTATTTCTTGGAAAAACAACACAATTGAGATGACCACGCTCATCTTTGC
AATCAACTTGTTTATGAAAAAGATTAATCATTTTTTATAATAAAAAAGATGAATACTTTTCAAATGTAGTTCAACTACTCACGAATCTACTTAGA
ATCTATTCCATACTATTTTCGCCAAATTTGCTAGACTTTCGTGAACTTTGCACTTTCTACTGAAAGTTCATATGATTCGAGAAGTTTCCATACAT
TTCTTTTTACCACTTCGTGGTTCCGCAAATGATTTATCATGCCCGCGGACTTGGCTCTTTATTTTTGGGACGCGTTTATTGATTTTCGCCTTGC
TATATGTACATGATTTAGTGACTGGTCTGACGCGCATGTCTCATAATTGGTTGTGGATTACTTACTACTAAGCAACATGTGCTGTATACTTTTAA
AGTTGCAAGGATCCCAGCCACCCTTCACCACCCAACTGCGCTCCCCCTCCCCTTCCCCCTCCCTACCCACTCTCAAGTTCATTTTTTATGCGTAA
CTCAGCATAGCTTGCAAGCGTTGTAAAATGCGTGTGCACATCATCATCCACATTGGTTTCAAACAGCCCGCCAATGCGAACAACAATGTTTGAAG
TTCAATCACAGCCACAAATATTCGTGAATCATGCAACTTTATTGGCAATTTTTCACAAATACGTGCTACAACAAAAATCGCACTAATAAGCAGAC
AGTCGGCAAATGTCCCGATGTCTTTGTGTGTGAGTGCTAGTGTGTGTGTATGTATGGGGGTGTTGGTGTGCGAAATACGTCAGCAGCTGACGGGC
AGCGGGTGCGAGCGAGAGAGGGCAGACAGTGCAAGTCAGCAAACGCGCTACAATTACAATATTTTGAATAGTAGTGTAGTCTAGCTCTGTATTGT
TATCAGCCACCAGATATGCCCGAGATAGTTAGCCTGCAACTGGCTTTACCCAGACAGGCAGCACTGCAATGATAATTTAGATGATTTGGTTCGGA
AATATCTTACATTTCCTTTGGTCAGATATCAAAAACTAATCTTGCATAATTCCAAATACTAATCATATGCCCGAAAAGCATTTAAATGAACTTCG
AAATATATTTAGACTTCAATTGACTGACTCGAAAAAGGAAATGAAATGGCCAAATGATATCAGCTCTTAACCTACTCACTTTAATTTGATAAACG
AGCTCCTTGTTTGCTTCCGTGTTGAGTTCCGAACATGTGATTCATGACGCAGTTTTAGATGGTGATGCAGACGCAGATAGAGATGCCCCCGATGG
GGACGATAGGATTGGGTGCAACAATGTGGCGGAAGCCCTTATCACCGGCTGATTGGATGGCCCCGTATTGGTATTGGTATTGGTATTGGTATGAC
AGAACCAGCTAAATCAGGCGTAGACGCAACGCCACCTTATGCATAAATATATCTGCATAACTTATATATCATCGCGGATTGGGCGTGTCGGCGAT
AAGAAATGGAAAATAGGTAGTCTAGGCTGTCGCGAGGGGACAAGGACAAGCGGAGGAAAGTCCAGATAACAAGCCTTCCATACCTTGGATAAAT
TTATCTACGCAAAATGTATATAATGTATGTATCTTGTTGGCTTTCCAATTGAAATGTTTGGTTTTTATTTTTAATCTTAACATGAAATATATGAA
AGCAATTCAAAAATTATATGAACAATCAAACAAACATTTGTATTCTACGAAATTGTTGATAAAATAGCGTCCGATAGCATTGTTTAAACTACATC
ATAAACATTACTTCTTACTCACTCAAATGAAGTATTTGTTTAATGATGTATATTTTCCTTAGGCATTGCAGAATGAATATACATATATGCGAACT
AATGATTAAACTAATCGTTAGTTAATGGGCAATCCCTTAAATTTGGTTTGAGATGTTACACTTGATTATTGTAAACATTTACTCTTATATACTAA
AGACCACACCTTTCATTTGTTATGTCCTCTTTACAGAAATGGTGGAGGCCATGAAGAAGGTCGCCTCCATGGACGTAGAGCTGACCGTCGAGGAG
CGAAATCTGCTGTCGGTGGCGTACAAGAATGTGATTGGAGCACGCCGTGCCTCGTGGCGCATCATCACCTCGATCGAACAGAAGGAGGAGAACAA
GGGGGCCGAGGAGAAATTGGAGATGATCAAAACCTACCGCGGACAGGTGGAGAAGGAGCTGCGCGACATCTGCTCGGATATACTGAACGTGCTCG
AGAAGCATCTCATTCCATGCGCCACATCCGGCGAAAGCAAAGTATTCTACTATAAGATGAAGGGCGACTACCATCGCTACCTGGCCGAATTCGCC
ACCGGCTCCGACCGCAAGGATGCGGCAGAGAACTCGCTGATTGCCTACAAGGCGGCCAGCGATATTGCCATGAACGATCTGCCACCAACACACCC
CATCCGTTTGGGCTTGGCATTGAACTTCTCGGTGAGTGATTGTGAAGAGACACGATGTCGTCATATGTTTTCTATATATATATTTTAAAATCCTT
GCAGGTGTTCTACTATGAGATTCTCAACTCGCCGGACCGCGCTTGCCGCTTGGCGAAAGCCGCTTTCGATGATGCCATTGCCGAGTTGGATACAC
TGAGCGAAGAGAGCTACAAAGACTCGACACTCATCATGCAGCTGCTGCGCGACAACCTCACATTATGGACGTCCGATATGCAGGCAGAAGGTAAG
TTGTAATATCACATCCACTTGTTCGGCTCCGTTATTAAGTTCTAAATATTATACTAAGAAGTAGACCCCAACGCAGGTGATGGCGAGCCCAAAGA
GCAAATCCAGGATGTTGAGGATCAGGACGTGTCGTAATTTAAGTAAACCCCCGCCCTTCCATTTAAAACACATTATATACCTTCTAAAGTAAATA
TAATACCATATAATATATATGCATACAACAACAACAACAAAATCAACAACAACACGACAACAACTTCAAGAACAACAACATGGAACCAATGCGGC
AACAACAACCATAGCAGTCGATCACCACAACAGCAGCACCCGTATGTGTATCAACATATTTGCAACATGATAACAGCAAGCAAAGCAGCAGGAAC
ACAAATTGTCATCCACAATAAACAGCATGGAAAACAACAGCACAAAAACAGAAAAAAAAAACAACTATCCAAGCAAAATGTTTGAAAATTGGGCG
GCCTGGTGGGCGTGGCGCGGCTGTTGCTGCGGCCCAGAATCGAATCGCAACATAAAAAATTCGCGGTACTATTAAGTTGGCGTCGCTTCGCAATT
TGGCTCCTTAACGTTAGAAAACTGCAACATCAAGTCTACTACATTTGAATTTTTTGCATTCGAGAAACCAAGCATTTTATTATATTTGAATAAAT
ATTATATTTAATTATGAGAAGCAAAAACGAAACAAATAAAATTCATTTAAACCACAAAACACATTAAAGCACAAGCAGAAAAAGAACGAAAGTCG
AAACACTAAACGAAAATTGAGAAACAATCACACGAGAGTAAATCACAAAGCAAATTTCATCGAGTTGGCATGCATTAATTTTTAAAACAAACTTT
AAATACGACAGCAACACGTAAAATACAACTTTAATTTTAAGCCAATAATAAACGTGAGAACGAGGTAATAAAAATGAAAAACGATTTAATAAGCG
CAAACGTAAAAGTAAAACATAAAGTCGAAAATGTAAGGAAAAAATACAGCAATTAATTTAAATTTAATACATGAATAAAACGTAAATGGAGTAAA
CGAAACGAAATGAGCAAACAGAATGAAAGACGCAAAAAGCTAAAAACTATATTAAATGAGAAAAAGGAATGTTAGTTAAGCGAAATTCAAAACGA

FIGURE SHEET 485

ATTCTTAAGCTTAAATTTGTATGTATGTAAGTGTACTGTTCAATAACACCGACACACCCTCACAGACACACACACACACGCGCAGACTAACACAC
ACCCACCACCCACACAGACACCCATATTACGCATACGAGCCGTTTGTTTTCTCTTAGCGTTTCCTTGCTCTCTCACACTCGCACTCATATTCACA
CTCACACACCCATGCATGGTCAAATCACATGAAACGAAACCGAACAATCGAACGGGAATTTGGTGGATTTCTGTTTTTCGCCTTTCGTTTTGAGT
TCTCCATCGCAATCGCAAACAATTTTCTTCATCATCTCTTACCTTGCGCAACAAAGAAACATATTAATAATATAGAAAAGTATTTGTAGTTGCTA
AATACAAGAAACAAAAAGAATACAAAACAAAACAACGGTACATATATATACGTATATATATATATATATATTGTATACATATATACTTGTATATT
TTCTATGCCTACCACTTATGTAATTTGTAGAGATTTCGAACTTTTCGCCCCACCACCCAACTAACCATCTCTCCAGAGATTCCGATTCCAAAACT
CCC
(SEQ ID NO: 898)

Exon: 1001..1213
Exon: 5737..6206
Exon: 6275..6455
Exon: 6525..7173
Start ATG: 1150

Transcript No. : CT24092
CCGCCGCCCGATACGGTCACACCGCTCGAGAAGTAGAGAAAAAAGAAGGCGACGAACCACAGGCAGCAAGCAAAATCGACGCCGCACGTACCGGG
AGCATTTAAATAATTTTTTCTGTGGATTAATTTTACCGAAAAGGCTTCAACACAATGACTGAGCGCGAGAACAATGTGTACAAGGCAAAGCTGGC
CGAACAGGCCGAGCGCTACGACGAAATGGTGGAGGCCATGAAGAAGGTCGCCTCCATGGACGTAGAGCTGACCGTCGAGGAGCGAAATCTGCTGT
CGGTGGCGTACAAGAATGTGATTGGAGCACGCCGTGCCTCGTGGCGCATCATCACCTCGATCGAACAGAAGGAGGAGAACAAGGGGGCCGAGGAG
AAATTGGAGATGATCAAAACCTACCGCGGACAGGTGGAGAAGGAGCTGCGCGACATCTGCTCGGATATACTGAACGTGCTCGAGAAGCATCTCAT
TCCATGCGCCACATCCGGCGAAAGCAAAGTATTCTACTATAAGATGAAGGGCGACTACCATCGCTACCTGGCCGAATTCGCCACCGGCTCCGACC
GCAAGGATGCGGCAGAGAACTCGCTGATTGCCTACAAGGCGGCCAGCGATATTGCCATGAACGATCTGCCACCAACACACCCCATCCGTTTGGGC
TTGGCATTGAACTTCTCGGTGTTCTACTATGAGATTCTCAACTCGCCGGACCGCGCTTGCCGCTTGGCGAAAGCCGCTTTCGATGATGCCATTGC
CGAGTTGGATACACTGAGCGAAGAGAGCTACAAAGACTCGACACTCATCATGCAGCTGCTGCGCGACAACCTCACATTATGGACGTCCGATATGC
AGGCAGAAGACCCCAACGCAGGTGATGGCGAGCCCAAAGAGCAAATCCAGGATGTTGAGGATCAGGACGTGTCGTAATTTAAGTAAACCCCCGCC
CTTCCATTTAAAACACATTATATACCTTCTAAAGTAAATATAATACCATATAATATATATGCATACAACAACAACAACAAAATCAACAACAACAC
GACAACAACTTCAAGAACAACAACATGGAACCAATGCGGCAACAACAACCATAGCAGTCGATCACCACAACAGCAGCACCCGTATGTGTATCAAC
ATATTTGCAACATGATAACAGCAAGCAAAGCAGCAGGAACACAAATTGTCATCCACAATAAACAGCATGGAAAACAACAGCACAAAAACAGAAAA
AAAAAACAACTATCCAAGCAAAATGTTTGAAAATTGGGCGGCCTGGTGGGCGTGGCGCGGCTGTTGCTGCGGCCCAGAATCGAATCGCAACATAA
AAAATTCGCGGTACTATTAAGTTGGCGTCGCTTCGCAATTTGGCTCCTTAACGTTAGAAAACTGCAACATCAAGTCTACTACATTTGAATTTTTT
GCATTCGAGAAACCAAGCATTTTATTATATTTGAATAAATATTATATTTAATTATGAGAAGCAAAAACGAAACAAATAAAATTCATTT
(SEQ ID NO: 899)

Start ATG: 150

MTERENNVYKAKLAEQAERYDEMVEAMKKVASMDVELTVEERNLLSVAYKNVIGARRASWRIITSIEQKEENKGAEEKLEMIKTYRGQVEKELRD
ICSDILNVLEKHLIPCATSGESKVFYYKMKGDYHRYLAEFATGSDRKDAAENSLIAYKAASDIAMNDLPPTHPIRLGLALNFSVFYYEILNSPDR
ACRLAKAAFDDAIAELDTLSEESYKDSTLIMQLLRDNLTLWTSDMQAEDPNAGDGEPKEQIQDVEDQDVS*
(SEQ ID NO: 900)

Name: diacylglycerol-activated/phosholipid dependent protein kinase C inhibitor
Classification: enzyme_inhibitor
Gene Symbol: 14-3-3epsilon
FlyBase ID: FBgn0020238

Celera Sequence No. : 142000013384504
CCAGCGACCTATGGATTTCTATTGCATAATTTTCCAACTACAGTCCACCGCTCTACCAACTGAGCTATCGAAGGTTGAGTTCAAACTTGGCCGTT
GTTCGTTTTATGCATGCGCACAAACGAAATGCACCGTATTTGGTTATTTATTTTTGATTTTTACTTATTTAGGTCAAACAAAATTGATCAACTTT
CTCTATTCAGTCCATTGCAGTAAGCCTATAGTTTCCAAGCCTAATAGCCTAGGCGCTTTTCACAAACTATATCAATTTAGTTACGGTTTATTTCT
TCCAAATAAAATCCTTCTTATATTATTTAGTTTAAACAGCTCAGTTATATTCTGAATGTCTGTAGATGAATTAAATTGATTTAAATTGTGCACTA
CAAAATATATAAAAAAAAAGGTATGTGCACTACAAAATATATAAAAAAAAGGTATTTATATCTTTTCGATCCTTCGAGCCGGATTTGAACCAGCG
ACCTATGGATTTCTATTGCATGTTTTTCCAACTACAGTCCACCGCTCTACCAACTGAGCTATCGAAGGTTAAATTCGCTTGCGGCTAATTCACCT
TTTGTTCAGGAGCGAGGTGGGGAAAGTGACAAAAAGAGAGGGCACTTCTCTTAAACACCGCTGCTCTTTAATACTCGCGGCCAGAAAAATAGGAC
CTTAAATTCTTGTAAACTTATATTAAATACTAAAGCATTGTAAATCTTAATGAGAAAATATTCAGGTACAACTGTTCATGGCTTAATTTTAGACC
AAAATTGTGCATGAATTTAGAAAGGCAGCAATGCACTATTTGAAACTAACTAGTTACCCACCCACAGCTGTGCACCGATAAAGGGGTGGTGTGCG
AGCAAAGATGCCATATTTATACATATATCCATCTCGTTCCAGCGCCGACGATAGACGATACCGATACTTTGCGAGTCCGCTCCCAAGATTGAGCC
CCCACAGCGTAAAAGCGACCGAAGTGCCGGCGACGAGAGCAGTTCGTTCCCAGAAGCCGGCAGCAGTGGTCCGTTGATAACTCCGACTCGAGCTA
CTTATCCACCACGTCGATACTCTTGTCTGTCTATTGCAAACATAGAGGAGTCACCCTTTGGCTAACGAATCCGAAACTCCCGAGTTTTGTTGTGC
AACATATCAAAAACCGCATTTGTTCGGATCCAATTTACATTCGCATTTCAAAGATGTCGTACCACAAGCCCGAAGCTAAGACCGTCCAGGATCTG
AAAGATCTGGCCCAGAAACTGCGAATTCACTCTATCAACGCCACCCAGGCCTCCAAATCGGGGTAAGTTTATCAATAACTGAAAGTCCATAGGCA
TATTAAAGTGTGCGTATTTAGATTTGTTTGTGTAGATGTGAATTTTAAAAGTTGTGCACCTTGCACTTGTTGCTTCAAAGGTGACCCCCTCCATT
TCCAGGGTGGGTGCGAAAAAGTTTTTGAGGGGGCTGCTAAATACATACATACATATGTATGTGTTTTGAAACATTACAAAAGAAAATAAAACAAA
AATAGTTACGCATATACATAGTTATGCATCTATGTTTGTATGAATGTGAGAAGTAAAATATGGGAAGACCGGTTCCTTTAGTGACCCCTCCTGGG
ATTCAGTTGCCAACCCACGTGTTGTCCAGTAGCTTTAGTGAATTTGCGAATTTGTTGCCCTGCCTGCGTGCTCAGTGATAAGCCGCGTTCACCTA
CCTTAAATTGTGAGCTAATATTTTTTGACCTTAGACAACCTTGAAACGTTAGGTTTTTCTTACTGCCTTTTAATTTCTTTTGCTTTTGTTTTGTG
CGTGGCGTTCAAAACGCCGAAAGCACATACATATGTACATGGGGTAAAAACAAACATACTTACATATCAAACAGAGGCATTTAATATACGTATGT
ACATATGTACATACAAGTGTTGGAAAGCACAGCTTGTGACGGGAGTGGAATTGGAAAGAGAGGGATGAGAATAGTAATGGAATGATCCCCTACAC
TTGAGATTTACGACTGTATGGCTTTTAATGTAATTATATCTCGGATAGACGCGATCAAATTATTACTGCAACAGTAAATAAAAAAGTTACTATGC
TGATAAGGAAAACACTTTTATCGCCTCCATTAGTTTTTCCATTCTGTTTCGTTTTTTTTTTTTTTTGTGACGGTTCAAGATAAGATCTGCTCTGT TTGCTCTAAATGTGACCTCTGCCGACGAGATAAGCCCGGTTTGGTTACTCATTGACCACGATATGACCGATTAGAGGTGACCAGCTCAAGTGTGT
TCCCCGCATGATAATCGAAAATCACTGAAAACTGATAAAAAAAAAAAAAGCGCGCCGGGTCACTGCTAACACTCCGTATCACCTTCAATAGTTCT
TGATATGGCTGCAGGAAACGGGGACGCACTTCGGAACTATCTAGAAGCACGTGCGTTCACAAAGATCGCCATGCAACACAATCGTGGAAGCCAAG
AATTTGGTTTTTAAGGCTATTATTTAGGTTTTTTGGTGATCAGAAAAGTTCAAGGTCCCAGAAACCGGTGAGGAATTGCGATGGACTCACGTCGC
GACAAACACACATATCACACCATATAACGCCAATAAATACATATGCATGTACTCGTTATAGTTTATTTATATGTCTGGGGTAAGACGAGCCCCCC
ATTTTGTCTGGGGTTGCGTGTTTTCTTTGCGGTTGGAGTTGTGCCAGATCTGCGATTCAAAGCAATTTTTTTTGGAACACGATCGCATGGGAACA
TTGAATTCCAAGAATGGATCTTATCTTATTTATATGTACATTGCAATTGGATACTCGAGAAATCTTCATTTGAAATATGAACAGAGGGGGGGGGG
GGGGTTTAAATAAAAGCTTCAATAGACAAATGGATTTCTTTTATTAAACAACGTTTTTAACAAGTATGCACAGTGTTCAGTTCCACTTTTCCTTT
GTTGATCGGCCTTCACTTACCCACCGTGAGGTCGACTTCTATAATTCATTAGGCACTTACCTTAACCTAGAACTACATGCAAACGAAATGCCTTG
TCACAATCTAATATTTTGCCTACTTTTCCCTCTTTATAGCCATCCCACATCATGTGCCTCGATCGCTGAGATCATGTCCGTGCTGTTCTTCCAGC
AGCTGCGCCTGAACCTGAAGCACCCACGCGATCCCTCCAGCGATCGCTTCATCCTGTCCAAAGGACACGCTGCTCCCATTCTGTATGCCGCCTGG
GCTGAGGCTGGTCTCTTCCCCATCGCGGATCTGAACAACCTGCGCAAGATCGACAGCGATCTGGAGGGTCACCCGACGCCTCGTCTGAACTTCAT
CGATGTGGGCACTGGATCCCTGGGACAGGGTGTCGCCGTCGGCGCTGGCATGGCCTATGTGGGCAAGAACTTCGACAAGGCCGACTACCGCACCT
ACGTGGTGGTGGGTGATGGTGAGTCCGCCGAGGGTTCCATCTGGGAGTCGCTGCACTTTGCCGGCCACTATAAACTGGACAACCTTTGCGTGATC
TTTGATGTGAACCGCTTGGGCCAGTCGGAGGCCACCTCCCTGCAGCATAAGCTGGATGTTTACCGTGATCGTCTGGAGGCCTTCGGCTTTAATGC
CGTCGTTGTCGATGGTCATGATGTCGAGGAATTGAGCAAGGCTTTCCATTGTGCTGCAATCACCAAGAACAAGCCCACCGCCATCATTGCAAAGA
CGTTCAAGGGCAGGGACTTCCCCAACATCGAGGATTTGGACAACTGGCACGGCAAGCCACTGGGCGACAAGGCCGCCGAAGTGGTGAAGCATCTG
GAGGGACTGATTGTCAACAAGAACGTCAAGCTGACCCCTAAGCCGGTGCCCAAGACTGGTGCTGCTCCCGACGTGGACATCAACAACATTAAGTT
GAGCTCGCCACCCGCCTACAAGCTGGGTGATTCCATTGCCACCCGTTTGGCCTATGGAACAGCTCTGGCCAAGATTGGCCAGAACAACCTGCGTG
TTGTTGCCCTAGACGGAGACACCAAGAACTCAACTTTCTCCGACAAGCTGAAGAACCTCGACCCGCAGCGCTACATTGAGTGCTTCATCGCTGAG
CAGAATCTTGTGGGAGTGGCCGTTGGAGCCGCCTGCCGTCGCCGCACTGTGGCCTTTGTGTCCACCTTTGCCACCTTCTTCACCCGTGCCTTCGA
TCAGATCCGTATGGGCGCCATCTCGCAGACGAACGTTAACTTTGTGGGCTCCCACTGCGGCTGCAGTATCGGTGAGGATGGTCCTTCGCAGATGG
GTCTGGAGGACATTGCCATGTTCCGCACCATTCCGGGCAGCACCATCTTCTATCCCTCCGATGCAGTGAGCACGGAGCGTGCCGTCGAACTGGCC
GCCAACACCAAGGGTGTCTGCTTCATCCGTACGTCCCGTCCCAACACCTGTGTGATCTACGACAACGAGGAACCCTTCACCATTGGCCGCGGCAA
GGTGGTGCGCCAAAAGAGCTCCGACGAGGTGCTTCTGATCGGAGCTGGAATCACTTTGTACGAGTGCCTGGCTGCCGCCGATCAGCTGGAGAAGA
ACTGCATCACCGTCCGTGTGATCGATCCGTTCACCGTGAAGCCATTGGACGCCGAGCTGATCATCGAGCACGGCAAGCAGTGCGGAGGACGCGTA
GTCGTCGTGGAGGATCACTACCAGTAAGTGTTCTTTGTAGTCTTTTTATTTGCCTCCTTTGCTAACTTGAAATTTACTTAATTTCTTATAGGCAA
GGAGGCCTGGGTGAAGCTGTGCTGAGTGCCCTGGCTGGCGAGCGCAACTTCGTTGTCAAGCACTTGTACGTGCCCACCGTGCCACGTTCGGGTCC
TCCGTCGGTACTCATCGATATGTTCGGCATCTCCGCACGTCACGTCGTCAACGCCGTTAACGAGATCCTCAAGGATTAGGGGACCAGTCGTGATC
TGGCTACATTCATTTACCGCCTACAGGAATTCCCCCAGTTACTACTTACTTCCAATATTACCATTCCCTCTAAGATTGTTAATTGCTTCATTGAT
TTGAACCTTACATCATGGAAATAAAATATCTTTAATAAAAATAGTTAAGCCGAACTATATACCTTATTTACATATTATATTACTTATTTACTATA
TTACTTATTACATGTTAAGCATGCCTTTAAAATGGCTGGACGATTTCATTGCGTTTGCCTTTGGTTTGCTTTAGACTTGCTTTGGTTTGTTTTTA
GTTTGCTGTGGTTTTGCTTTGGTTTATCTCTGGATTTGCTATGCGCTTGATGTTGATTTGACATAGATACTGAAATAAAGATAAGATGAGAAAAT
GAATAAAATTATAAATTTTTTAAATTTAAGCATACTGCATACTTTTTTAATTTACAAATTTTTAATATTTTTCTAAAAAAAATCGGAGCTTAAAA
CTAACAAGTTGGCAGTACCCTTCCAATTATAAAGGGTTATCGATAACTCTGCTGTAGCTATCGGTGCTGCCAGCTGATTATAGTGCGGCATGATT
ATCTAAACATCAATTTGTTTCAGCCGATCCCGAAAACTATTCAAAATGAACTTAAGCACAAGAGTTATGCTGAATAGGTTGACACAGCAGTGTGT
CTACAAGCGGATTGGTAAGGAGAGACGTTTTATCTTGTGCCACACATTCAGGAAACGTATTTTCAGTGACCTTCTCCACCAAAACTGCGGAACAT
GTAATTGAAAATCAGGAGGAACAGAAGAAAGAGGCTCCGCCAACCACGCCGACTTCACCGGTGAACCGGAAGACAATCATTCCGGCCAATTATCG
GTTTGTTTACCCAGAATTCCTGCCCGATCCGAAGGTGGAGTGGCGCAACCTCGTGCGCGAGAAGCTGGAGCGACTGGACATGCTGGATCGCCGCA
AACAGATCGACCTGCCCGAGTTCTACGTTGGATCTGTGCTTGCGGTGACAAGTTCGGATCCCCATGCCGCTGGCAAAACCAGTCGATTTGTGGGT
ATCTGTATCAATAGGGATCGCTGTGGACTGCGCGCCCGTTTCATTCTTCGCAACGTGATTGATCACCAGGGAATGGAGGTGGTCTACGAGCTGTA
TGATCCTACCATCCTAAAGA
(SEQ ID NO: 901)

Exon: 1001..1297
Exon: 3080..4678
Exon: 4747..5100
Start ATG: 1194

Transcript No. : CT24118
CAGAAGCCGGCAGCAGTGGTCCGTTGATAACTCCGACTCGAGCTACTTATCCACCACGTCGATACTCTTGTCTGTCTATTGCAAACATAGAGGAG
TCACCCTTTGGCTAACGAATCCGAAACTCCCGAGTTTTGTTGTGCAACATATCAAAAACCGCATTTGTTCGGATCCAATTTACATTCGCATTTCA
AAGATGTCGTACCACAAGCCCGAAGCTAAGACCGTCCAGGATCTGAAAGATCTGGCCCAGAAACTGCGAATTCACTCTATCAACGCCACCCAGGC
CTCCAAATCGGGCCATCCCACATCATGTGCCTCGATCGCTGAGATCATGTCCGTGCTGTTCTTCCAGCAGCTGCGCCTGAACCTGAAGCACCCAC
GCGATCCCTCCAGCGATCGCTTCATCCTGTCCAAAGGACACGCTGCTCCCATTCTGTATGCCGCCTGGGCTGAGGCTGGTCTCTTCCCCATCGCG
GATCTGAACAACCTGCGCAAGATCGACAGCGATCTGGAGGGTCACCCGACGCCTCGTCTGAACTTCATCGATGTGGGCACTGGATCCCTGGGACA
GGGTGTCGCCGTCGGCGCTGGCATGGCCTATGTGGGCAAGAACTTCGACAAGGCCGACTACCGCACCTACGTGGTGGTGGGTGATGGTGAGTCCG
CCGAGGGTTCCATCTGGGAGTCGCTGCACTTTGCCGGCCACTATAAACTGGACAACCTTTGCGTGATCTTTGATGTGAACCGCTTGGGCCAGTCG
GAGGCCACCTCCCTGCAGCATAAGCTGGATGTTTACCGTGATCGTCTGGAGGCCTTCGGCTTTAATGCCGTCGTTGTCGATGGTCATGATGTCGA
GGAATTGAGCAAGGCTTTCCATTGTGCTGCAATCACCAAGAACAAGCCCACCGCCATCATTGCAAAGACGTTCAAGGGCAGGGACTTCCCCAACA
TCGAGGATTTGGACAACTGGCACGGCAAGCCACTGGGCGACAAGGCCGCCGAAGTGGTGAAGCATCTGGAGGGACTGATTGTCAACAAGAACGTC
AAGCTGACCCCTAAGCCGGTGCCCAAGACTGGTGCTGCTCCCGACGTGGACATCAACAACATTAAGTTGAGCTCGCCACCCGCCTACAAGCTGGG
TGATTCCATTGCCACCCGTTTGGCCTATGGAACAGCTCTGGCCAAGATTGGCCAGAACAACCTGCGTGTTGTTGCCCTAGACGGAGACACCAAGA
ACTCAACTTTCTCCGACAAGCTGAAGAACCTCGACCCGCAGCGCTACATTGAGTGCTTCATCGCTGAGCAGAATCTTGTGGGAGTGGCCGTTGGA
GCCGCCTGCCGTCGCCGCACTGTGGCCTTTGTGTCCACCTTTGCCACCTTCTTCACCCGTGCCTTCGATCAGATCCGTATGGGCGCCATCTCGCA
GACGAACGTTAACTTTGTGGGCTCCCACTGCGGCTGCAGTATCGGTGAGGATGGTCCTTCGCAGATGGGTCTGGAGGACATTGCCATGTTCCGCA
CCATTCCGGGCAGCACCATCTTCTATCCCTCCGATGCAGTGAGCACGGAGCGTGCCGTCGAACTGGCCGCCAACACCAAGGGTGTCTGCTTCATC
CGTACGTCCCGTCCCAACACCTGTGTGATCTACGACAACGAGGAACCCTTCACCATTGGCCGCGGCAAGGTGGTGCGCCAAAAGAGCTCCGACGA
GGTGCTTCTGATCGGAGCTGGAATCACTTTGTACGAGTGCCTGGCTGCCGCCGATCAGCTGGAGAAGAACTGCATCACCGTCCGTGTGATCGATC
CGTTCACCGTGAAGCCATTGGACGCCGAGCTGATCATCGAGCACGGCAAGCAGTGCGGAGGACGCGTAGTCGTCGTGGAGGATCACTACCAGCAA
GGAGGCCTGGGTGAAGCTGTGCTGAGTGCCCTGGCTGGCGAGCGCAACTTCGTTGTCAAGCACTTGTACGTGCCCACCGTGCCACGTTCGGGTCC TCCGTCGGTACTCATCGATATGTTCGGCATCTCCGCACGTCACGTCGTCAACGCCGTTAACGAGATCCTCAAGGATTAGGGGACCAGTCGTGATC
TGGCTACATTCATTTACCGCCTACAGGAATTCCCCCAGTTACTACTTACTTCCAATATTACCATTCCCTCTAAGATTGTTAATTGCTTCATTGAT
TTGAACCTTACATCATGGAAATAAAATATCTTTAATAAAAATAGTTAAGCCGAACTATATACCTT
(SEQ ID NO: 902)

Start ATG: 194

MSYHKPEAKTVQDLKDLAQKLRIHSINATQASKSGHPTSCASIAEIMSVLFFQQLRLNLKHPRDPSSDRFILSKGHAAPILYAAWAEAGLFPIAD
LNNLRKIDSDLEGHPTPRLNFIDVGTGSLGQGVAVGAGMAYVGKNFDKADYRTYVVVGDGESAEGSIWESLHFAGHYKLDNLCVIFDVNRLGQSE
ATSLQHKLDVYRDRLEAFGFNAVVVDGHDVEELSKAFHCAAITKNKPTAIIAKTFKGRDFPNIEDLDNWHGKPLGDKAAEVVKHLEGLIVNKNVK
LTPKPVPKTGAAPDVDINNIKLSSPPAYKLGDSIATRLAYGTALAKIGQNNLRVVALDGDTKNSTFSDKLKNLDPQRYIECFIAEQNLVGVAVGA
ACRRRTVAFVSTFATFFTRAFDQIRMGAISQTNVNFVGSHCGCSIGEDGPSQMGLEDIAMFRTIPGSTIFYPSDAVSTERAVELAANTKGVCFIR
TSRPNTCVIYDNEEPFTIGRGKVVRQKSSDEVLLIGAGITLYECLAAADQLEKNCITVRVIDPFTVKPLDAELIIEHGKQCGGRVVVVEDHYQQG
GLGEAVLSALAGERNFVVKHLYVPTVPRSGPPSVLIDMFGISARHVVNAVNEILKD*
(SEQ ID NO: 903)

Classification: enzyme

Celera Sequence No. : 142000013383969
GTGCTGGAATTATATCCTGTTCCATATTTCGTGATATTCAAAACATTCATCTCATATCTCTGCCGAAAGTTTGACTTGAAAAGAAGGAGCATTA
TGTATGTACATACATAAGTAACGAGTGGGATGAGCTTAGGAAATTTTTATTAATTTGGCCTAGAGCTAAATGTTTTTTTTTTTTCGAAACCAAG
GCTAGAAAACATATGTAGTAGCAGTAGTTCAAGATCGTAATCGTATTAAAAACGCCATTCTAATTGGCCTAGAAACCGTATTCATAGACCAACGC
CAAACGTTTCAGGTTTTAGGGAATTCCACCATCGTTTGCTCGCTTTAAATTAAAATGGCTAGTTCGGCGGCTGATACTCGTGAATATTGTGTTTT
CCAATTAATCAAATCACACTTTGCCCCACGGTGGCGTTGTCGGTCGATGGCAAAATCAAATTCTAATCGTCGACGCTATCATAATGTATTTATGA
GTTGTGTTATTTGTTTTTGGTTTTCGCGTACCGTGCGTATACGTAATGCGCTCAGTACGGAGTTATCTGTGTGTGCGCCGATGTCCGTGGGTGTG
TGTGGTGCATATGTATGTATATACATACATATGCCCATATTTGCCGCTGATAATCGGGTCTGCGACGACAAAACTAATTACAACAACAGTAAAGC
AAATACAGTGGTAACACGGAATAATGCCCTTATCAAAAAACGCGGCAAGGCGGCGCAACAACAAATGCAAACACAGGCGAAAAAGAAAGAAAAAC
AAAAAAAAAAAAATTGGGAAGATGAGGCGGAGCGAGCAGGAGCAACGGTAAAGGTGAAGCTACAGCCGAAGCTAAAGACCAAAATAACACGCACA
CAACGACAAACGGGAGAAGTGGAAACAAACGGCGAGCGGGCCATTGCATTGATGTGTGCCAGTGTGTGCGTTGTGTTTGGCTGTTTAATACTATA
ATTCACAAAATTGTTCAGTTCAGTTCGCGCTGGTGAACGTAACGGAAAAGTCGTCGCCTGTTGAATATTTACATTAGTTCTATATATGTTTTTAT
ACAAATATATATATTCTATTTACTTGAATTGTTTTTGTCGCCGCCGCCGCTCGTTTCGTTTTGAATTCTTCATCTTCTTCTTTTAATTTTTTTTT
TTTGGTGCTTTTGTTTTTGTTATTGTTTTGTATCTCAACTTTACTGCAGCATAACAACCACAACAACAACAGACGACGAAGGAGAGGGGAAATCA
TTTACAAAAATAAAACGTACGGCCCAAATACATAAATATATGTACATATATTTATATGTATATATATATAGTGTGTGTGTGAGCGTTAGCATTTG
TATTTAAGTTTAGTAGCAATTAGCACTAGAGCAGCAAACTAAATGATATATTTTTTTTTACCCGAAGCGCGCGCTTTTCGCGAGACACGTGCGCC
ATACTGAATAATATGTGGGGCGTATGTAACGCAAGTATCTGAAAGATACTTTCTCGAAATGGATGTGAACTTCAAAAGACGTTTTTCGAACACCT
TCGCCATGTGATTACAACTCACCAAAATCACTTCTAATGGTGAAATTACCGGTAAAAACAATTTGATATCAGATAGTCAAATATTCTTGGAATTC
CCAGTGTACATATTTTACGTGTGTCTTATCAAAGTTTGCGAGTTTCAAGTTTATGATTAACAAAAAATCAGATACCTATGGTGCAATACATCATT
TGTAATGAAGGTCTTTTGGAAATCTAGTTATTGCAAGCAATTTCACCACTTCATTATTATATATTCAGATATATTTTATAAAAATAGTCGGTTTA
TTGTGAAATGTCGACGACGACATGGGATGAAATAATTTTGAGCGTTACGTATCATTTCGATAGCGGTGCATACGTGCTGTGCTATTCTCCCGCCA
ATCAATCAATCAATCGAATATCAATCAAAGTGGCTACTCCTCTCAAACGGAGCGATTTCGCCTCATAGATACAAATGTATGTACGTATGTATGTA
GAGCCACAAACCGTGGCAAACAGTGGCTACCAAAAGGCAGTCTACCGGCCGTAAATGTTTTTACGGCATCATCTCCATTCCCGACATCTTTGTTA
GGCCAATGCAAATACTCCTTTATGGTGTGTGAATATAATCATCATACCCCTTGCCTGATGGGTCGGAACGGAAAGTGAATGGTGGGAGGGGGGGG
GGAGGGGGGGTAGTCATATAATGCGGAAAGCTCTAATTATACAAATGTTTGTGTTTGGCTTTAGACGGCTCTTGATCGCCTTAAACGACGCGTGT
TAATCAAGCACTTGAGGCACCTGGAGTACTTAGATGGCTTTTCCGAAACGCTAATCTTAAATCTTGAATTTTGATACTAATGAATGTACATACAT
ACATATGTGCGAATAAACCAAGTAAAAAACAAACATTTAGGAATGTTAATTATCCTCAAGTTTCTTTGTGGAAAGTGATAAAATCAGGAAACGAC
AGTTAATCAGCGGTCAAAGTTTACACATCGAATCGATTCACAATTAGCTGATTATAAAAATTGTATGATTTCATTACGCAAAAGCACTACAGTGG
TTTAAAGTATTATTATTTGATTATTTATTGTTTGAAAAACAATGAGTAGCAGCTGTTCATTCGATTATATTTGATGTGTGTCAACTAAATATGTA
TATCTGTTTCATCTCTGTAGCCTTTCCAGTCATTGTGCAACAAATGTAATTATTCACATGAAGATAGACTTAATTGAATTACGTGGGTACAACAA
AAAAGATACAATTGAAATAATCTGATTGGTTAATCTGATAAACGAATTTCACTGGATTTCCAAACAAATCTCGCAACAAGAACTAGTTTCGAATC
ATGATAATTCAATTATCCCATTCAGTTATGCATGCTCATAACTCACACCACAAGATGGCAATTAAATATGCATCTTAAAGTGCGTTCTTTTCTCT
GCGTACTTTTTCCTTCTTAGGTGCAAAACCTTATCACTTATCACGTGTGTCTTGTCTTGCCGTTATGACCAATTTCTGCCATGTGCCTGCTGATG
GATGGATGGATGATTGGCATTGAAATATTCCACAGTTGTGGTCATAATCATATCCACTCTTGCTTCGATAACGCAACGAGCTGATTTACTTGGAC
TGAAAAAACTGAAAGCTGAGGTCAATTAGGCCTATTATATGCGGTTATATCGAGTACCGAAACACACTTCGATTGATAAGCACTCGTCGCAGAGT
CAAAAGTCTGATCCTACCCACTGTGTGTTTGTTTGGCATGCATAGAAATGTGTATGTTGCTGATTGCCTGGCAATTAAAAAGCACTGTAAAATTG
CTATATGAACAGCGTTTTACTGGCCAACTAACTTGTTCCGTGTGGCGCGACCTTTAGTACAAGCCGCATACCGCTTTCTTAGTGTATCCGCCTAC
GAGTATAAGGCGAACTTTGCCAGCGAGTCTTATCACTTGCCCCCATATATTTTTGCAGTGGTCATTCGCGGATCGGGTTCGTTTGGGTTCGGTTC
GGCTGGGTTCGGTTCGGTTCAGCTGCTGGAGCAGCTGTCGCCAGACCACTGGTGGCCATTCGGAGTGCGATAGAGCAGTGAGTAAGTGGGACAGT
GGGTGCTACGAGAAAAACTCGAACACAATTCCATAAACATTGTTTGTTGCAATGATGTGCGGAGTGGAATTAAATATATAGTTTAGTTTAAAAGG
AGCAATGAAGCGACATTGCAGTTGTAGTACAGTGATTCCGGCAATTGATTGTGGTTGTGTAAACCCTTGTGTGGCGGATATAACCGAGGTGCTAC
AATCTAATTAGACGATATCGGCGCGGGCAAAGGAGTGCGCCTTATCACATGGTACCCCCACCCCCACCGCCACCGCCATATGATCTCATTTAAAG
CCCCACATGCCGACAGGCCCTGATACATGTCATACATTCATACATATACATATGTATCTCGATGATTCGGTGCCTTTGTCGCCCAAGTTGGCTCA
AGTATTTACGATGGACACTTCTGACTTCTGGTCAGCAAACTCTCGGATACGGGTTCCGAATTCGAGAAAAAAGCAAATAAAGTTCGTAACTTTTG
CTCTCCGAAATGAAATCGCTGGCGGTCGCGATAAGGCGGCGCTCTCCCGACCAACCAACCAACCAAACAAACTGACTAACTAACCAACCAAACGA
TCATCATCATAATCATCGCAAACGACAATCGAACCCATTGACGTTTTGATGAGACGTTGTTGGTTGGTGTTACCGTTTTTATATAATGGGTGCTA
AATCGATACTATTTACATACCTGTCGCTTTTAGGCAGTCACGTTTCCAGGCCTCCAAAAATTTCACCCGCCCGCCCTCGAAAAAACTCAAAAATA
TCAAATCGTTTAGCACACGATGAGTGAGAGTTGCCAAAAATATTACGCAGCCCGATTGATCAGTCAGTCGAGGTTGTGGCTTTCGTCCCGCCGCC
TCGCAACATCTTGTTCCGATCTAAACAAAAAAAAGAAAAAAAAAATTAATAAAAGTCCAATCAATTGAGGCTGTAAACGGCTGTCTGGCTGCCTG
TGTAAAAAGTTCAATTATTGCTTAGTTTTATTTCCTTTATTCTCTAGTTAATATAAAATTACATTTGAAATATTTTCATGAGAGCGAACACTTTA
AATGAATAAGCAATGAATGTGCAAAATGAAACTGAACTCAGCATGCCGAAATAAATAAAGTGATGTTTAATACAAAACTAATTTAGATTCTAACG
ATTCCACTAACGAAGTTTGCAATCTTCCCGCTTTTCAATGCACAGAATTGCAATCACTGGTTCCAGCATTTGATCGCACCCATCAATCCGATTCG AGCAGTAATGCAACAACCGGTCAAGAGCCCGCAGCGCTAAACCAATCCAAGCCCCACGCTCCAAGTTCCAAGCCCACCTAATCCTAGTCCAGGAC
GCCTAGCCGTATACACAGTTCCAAGATGACCGATAATGGGAACAATCATAACAACAACAACAACAACAACAACGATGAGGCACTCAGACTGAGGC
TACCGGAAGAGCAGGCAGAGCAGCTGCTGCCCAAGAATGGATCAGCCGGCCAGACCAAGATAGCGCCACCTACGCATACTCATTCCATAGCCGCC
GCTTCGGTGCCACAGAAGGTACCAGCGAAAAAAAAGCGAGACAAGAGCGATCTGGGTGAAGATTTTGTGGCGCCCGACGGCGGATGGGGCTGGCT
GGTGTCCGTCGCCAGTGGCGTTAACATTGTGAGTGACCATCGCATTTACTCGCCTGTCTGCACATAGATATTCACTCATGCCTCTTTTTCTTCAT
TCCCATTCCCATATCCATTCTCCACGCCAGCTAGTGACGTTCGCATTGGCCCAGCAGTTTGGCATCCTTTTCCGCGATCGCATGGCTGGTCTAGG
AATCTCCAGCTCCGAACTGACCACCATTATCAACACACAGATTGCTGTATCCGCATTTACAGGTGAGACGATGAAAACCATATATACGAGATTAT
AGAGTGATAGATACAGAGAGATATTCAAAGCCATGAGCAGCCGTAACTCACATTTGTATGTAGTCCACGTAGTGACGAATCGCAACGAGGGTGTG
ACTATAAGATTTATAATATCGCACTATATCACAATTTTTTTACGATTCTCTGATGAAAAAAATCGATAGTATTTTAAATTGAGTAAGTTTTGAAT
ATTAAATATAAATAGTTCACATTATGAAGCCAAAATACTACTTCTTCACAAATTTAAACTACGTGACAACAATTAAATATTAATTTCTTAATCAA
AGGTCTGCTGAACGGTCCGCTTTTCCGACGCTACACATATCGAGTGGTGGCCCTGGTGGGATCCGTGCTGACCTTTCTGGGTCTCTTCTGGATGG
TGTTCGCCGACACCTTCGCCGTCTACATAATGAGCTTCTCGATCTTGTACGGATTCGGACGAGGACTGACGGTATCCGCATCCTCGCTGGCGGTC
AATACATACTTCAAGGTGAAGCGACGCACTGCCACAGCTTTTCAGTTCGGAGTAGCCGGCCTGGGACCAATTGTGTGTCCCTACTTTGCCACCTA
CATGCTGTACGAGTTTGGTGTCCAGGGGACGACACTACTCTTTGCCGGCGCCTCACTGCACACCATCGCCTGCTCGCTGATCTACCAGCCAGTCA
AATGGCACGTGGTGAAGCGAGATCGCGATGCGGAGGCACTGCAGCAGGTCCAGCCACTGGCAGAGCGTGAGGATCAGGACGAGGATATTATCAAG
AATGTTGTAGAGCCGGAAACCCCGGTGCTGCCACGTGCCAATGACGGTTGGTTTGGCTCGCGGGCCTCGTTGAACAGCGTGGGCACTCGGAATCG
ACTGAACACCTGGGAGAAATCGGACAGCAATGGCCACGTGGAGCTGAAGAGGCTAAGCAGTAAGGACTCAAATCCGGGACGCCAGCTGCGCAGCA
TATCCGTGAGTCACAGCATTAAGGAGGAGGAGGCCACTGGCTACAATTCTGACCACGAAGTGCAACACACCGAGCTAACGGAGAAGGAGAAGCAA
GAGCTGGAGGATGAGAAGGAGCGCCAGCGCCGCAAGAAGCTGCCATTCTACATGAAAGTGGTGATATTCTTTGATATGGATCTGCTGAGGGATAT
CACGTATGTCAACCTGGCTGTGGGCATCACACTGATCAACTTTGTGGAGATCAACTTTGCCATCCTGACACCCTTCATCCTAAGCGATTTGGGTT
TCAATAAGGATCAGATTGCCCTGGCCATGTCCACGCTGGGATTCTTCGATCTGGTTGTTCGATTCCTTATACCCCTGATCACGGCCAAAATCAAT
CTAAGCAACCGTACCTTCTTCGTTGTGGGCATTTTGGGCATGTGCATTGGCCGCATGTTCCTCTCGATGACCTCCAATTTCTACGTCATGATGGC
CATCTTCCTGTGGCTGGGCCTTAACAAGGCCTTCCGCACGGTCTTCTGGTCCCTGATCATACCCAGTTATGTGCCCCTGAAGAGATTGCCGGCGG
CAGCTGGGCTGCAGCTGCTGATGTCCGGCACCTTTTCGATGATCTTCGGACCGCTGATTGGTGAGCAATAGATATACATAGACCAATATAATTGC
AATTTCTAATCTTCTAATTGTGTAACCCAACGATCATCCAGGCTTAATCCGGGATCACACCAGCTATGCGGTGACCCTCAACCTGCTGAATGCCC
TTTGCGTGATGGCCTTTGCCGGCTGGTATCTGGAAGATTTCATCCGCGCGCGCAGCCGGAAATCGCCACCGGTCAAGTCAATCAACTGATCAACA
TACGATGGCGTAGTTTACTCAGTGCCAGCGAATTCCAGGACCAACACCGTTCCCCCATCCATCCTAACTTTAGCAAAATGTTATTCTTGTTATC
GCATTTGCCCAGTGCTTTTTTTTTTATCTGTATGTTTATGTAAACTATATTCAGCGTGTACATTGTGTATATACTTTTCGAGTGTAGCAAATTGT
ATTAGATATTGATAATTGTTAAATAATATGCGTAAGCTGCCAATACTTAAACCTTAAAACAAGCGTTTCATTGAATGTTATCTTCGAATGTTATA
CCTAAAGTTATCTAAGATCTATGCGACAATTTATAGCGTTTGAAATATTCTAAACCATCGGACAACCACAGACTGTCAATTTTTCTTGTGGTGCG
ATTCGTTACTACGTGGCCCTGGTAAACGATCAGTCTCAACATTATATGATCCAATCTCTTGTGGCGCAGCAATAAAGTCGAATTAAAATCTGTTT
GTCCATCCGTCTGACAGCATCCAAAGTTCAACATCTAACAAAAATCTTATGACACAACGGAAGAAAGTCCAACTGAATTGGAAGGAGCACGTGAA
TATCACGAGTCTACTCATCATAACATCCAAATCAATGATCAATGACACTGAGAATTGATGCGGAAAAAAAAATTGAACAAACACTGGTGGCAAGT
TGACTTCTGAGAATTTATATTTATACCCGTTACTTGTAGAGTAAAAGGGTATACTAGATTAGTTGTAAAGTATGTAACAGGCAGAAGGAAGCGTT
TCCGACCATATAAAGTATATATATTCTTGATCTGGATCAAATTCTAGAAGGTTGAGATTCAACATACTGATTCTAGAAACAAAGACGCAGCGCAA
GTTTGTTGACAAACCGTACAAAACTGCCGCGCCCACACTTTTGAAAAATGAGTTGATATCATTTCACATTTTTATAAGTCTCGTAAATTTCTATC
GATTTGCCAAATAAAACTTTTTGCCACGCCCACTCTAACGCCCTAGGCCGTTGAACCGTTCACGTCCACACTTTGAAACAATTTGTATATTTTTT
CTCATTCTATCTCATTATACTGAGTAGGCTGAGCACTTGACTAATGAACATCGGAAGCTCGGAAATAAATAAATAAATAAATACCTAGATATAGA
TATCCAGATATAACGGCGTGAAAGGTTAAATCAAACCTTTAAAACATATTAGATTTGATTGAAACTGTTATCAATGCAAAACACCCACACTGAAT
GGATTTGTAAAATTATTTGACCAAACAATTAAATTTGCAAAATTTGACGCGTGCTAAAGAATAAACCAGTTTTGGTCGATGACAACAAAACATAC
AACAATGAATGGGTTAAGAACCGGGAATCAAAATGATATGTAACTCCGCGCCAGCGGAAAGTTACAGGCTCAAAAAAAAGTGTTTAAAAACAATC
TCATAACGAGGCGATCAGGTTGAATGCACCGCGGTGCTTATCAAATAGATCGAGAGGAAACATACTGAAAACATATGCAAAAATCGGGCAGGAAA
CTCGGGCCAAGTTCACTGTCTCTACCAAGTCAATGGCAAATAAATTTGTCGCAGTCGGTTTTTGTAACCACGAGTATTGCTGTCGCCATCAGCGG
AACTAAATGGAAAAAAAATCTGAGTGAATCAAACCAAATCGACCAGCTTGGGCATACCGAACACTCTTTTCATTTCAAAAAAGAAAAAAAACCAAT
TAAATCCAAATTAACTTATTATATATTGTATGTATCTAAACATATAGTGTAAGTACTAACAATTTTTTAAGGTGTTTCGTGTGGGTCAGTGATCC
ATTGCGCGCATAGTGGGTGGTAATCCATCTTTCGCACAACTGAACCTTCGCCCTACTAAATCCTCTTTTCATCAGAGATAAACGAAGGCACACAT
ATAAAGCCACCCACTTGTGGGCATCCCACCCACAGAGAGTAGGTGGCGTAATCAACTGAGCAACAAGTGGAAACAGGAAACAGGACTCAGCAGCT
GTGCTGCCCATCTAGCCTTTTTATAGCTACAATTTCAATACCATATATGTTGGTGTACGATTTGTTATTATTTAAAATAAAAATTTTTTTTTAA
ATATAAGCTCAATAATTCATTTTGGTAATGTCAAGTTTGACCCTAAAATTGTGCGAAATTAGATTTTACACATATTTTTTTGCCAATTATAGAAA
ACGGGCCTGTTTTCTAGAAACGTTTAAAAAAATTCGAGTTTATTTTGCAAGTCCTAACAAAATAACTCACTGCACGGATGTGTGGCGCCAGGACT
GCCTAGTTTGTTCGAGATCGGGTCAATAGACTGTTAGCAGGTGTGTAACCAATAGGGGTGGTTTAGTGGCAACATCGTACAGCAAATCAACAATC
TGTTGCCGGCAGTTTCAGCTTCAGGTACTCGCATGCAAATGCCACGTGGTTGTGTGCGGTGTCATTGCCCCACTTCTCAACTATCCCCACAGGAA
CTCCAGCAATTATCGATTATTTGTCAATCTTTTGGGACACCGCCGTGACCTTAGATATACAGTTTAATATCCTTAATTAAAAATAAATACCAATG
TTGGATAAAAATGTACACATGACATACATGATTTGCAAACAAAAAGAACTAACAAACAAAATCCAGATACAATATTTAAAATCTCCTGATCTCAT
TTACGAGGGCGCACTGTTATCACTCTTTAACAAAGACGCAACAAGTTAACAGAAGAGAAAAGAGTGAGCGAGAGTAAAGAGCGAAGAGCTGAAGA
GAGAGCTGGCTCATTTGCGCAACTGCAGCAGCGTCAAAAGGCCAAGTGAAGAACGTAAAGAGGAGAACGAGAGGAGAGGAAGAGCCTGCGAATGC
AGCGCAACAACTGCAGACAAAGAACGAATGTAAACAAAGAAGGAAGGCGCATTGTTTGTAGATTTTGGCAAGCGAAGTAAGCGACTTCTCTCACT
CCACGTTTTATTTCTCTTTCGATCGGCATTAGAACGCGATCTTGAAATACTGCAACACCGACACACACACACACACACACACACACACACACACA
CACACACACACACACATGGACATGGGGACTCTCTCTGAATGAAACGACACTGTGGCACAGTGGGCCCAAATGTAACCACTCTACTCCAATTTCAT
TTGAACCAGTTCCGATTTTCATTGTTTAGTAAGAGATCGGCAGGCTAAATATATCTAGTATCAAAAAAACCGATAGTAATTCATAAGTTAATAATA
ATTAGTAATTCCCACCTTGCAGCCTTCTAATTTTTCGCGTTCTTTACAAAAGTGTGATCAAAAGTTCTAGAAATCTGGATCACCAATACCCATTG
CTAGCTAGTTAACCAATTAATTTGGCCCACTGTGCGACGACGGTAACGGCGACTGAGACAGCGGCAGCGACGGGACGGCAAACGGCGACGGCAGT
CAGTGTTCAGTATTCAGTATCGATTGAACAGCCGCGCGTAGCTCATCGAAATCGAGGAAGGAAGAGACGCGACGAGAGAGCGAGCAAGACGGACA
GGCGACCAGACAGAGACAGCGACAGCAGGGAAAGGGAGACCAAGACGGAGACCGAGAAGGAGACATTGAGCGCCTGCCGCCCCCTCTTTTGTAAT
AAATAGCGCTGTGCGAAGCGACCACACTACCAAACGGCAAAAGTCCGCTGAGAGCGACGCAACGCAGGCCACAAAGGCCCGCCCCCCTCCCCCCT
GCGATAGACACAACAGAACAGGAACAACTATTGCAACAACACTATCACACACACACACACACACACACACACCCGCAGTCAACAACACCCCCCTG
AACGAAAGGGAGAACAGTGAAACAGCTGGAACAAGAAACCAGAAAACAAAACAGGCTGACAAAACAAATGTCAAAATTAGCGACTGACCAAAGGG
AATTTTAATCAAAAGTTAATACGAAAAAACCAACAAACCACCACGCGTTTCTCCACCAAGTGCCTTAAAAGAAAAAAAAAAAACAGAAAGAACAT
AACAAACAAACACCGATTCAAATGAATTTAAATAACAAATTCCAATGTGATAAAGCTGAAATAATCGTAAAAACCTAACAAACAAGAGTTCACGT
CTGTTCTTTTTTTTCGAATTTTTTTCGTAAGTGTGTTGTCTAAAAATCAAAGAAATGGAAAAATATAATTAGAACATCAGAAACAACAAACCCCA
CGGAGACGGCGGGCATAAATTAAGAAAATCGAAAAACACAAAGCCACAACGTAAAAAAAGTATCCATAAATCTATATGTGTGCTACACCTCATAT

FIGURE SHEET 489

ATAGAGACCTAAAATAAAACCAAAACAAAAACAAAGCAAATCCAGGAAAAGCAGACAACCGAGGAGAACTCAGCACAGCACAGCACAGCACAACA
AAGCAGAAATGGCAAGCAAACAACCCAGAAAAGTGGCGCCCGACGGTGGATGGGGATGGGTCGCTTGCTTTGGCGTTAGTTTGGTCAACGTAAGT
TCAAATTTCCAGTTCTTAGTTGCCAGTTCACTGATTAATACTAAATAGATTCACCCAACGACACAACATTCCAATGCCAATTAGCTAATACGTAT
TGGCCAAGCTTTTATCAAGCAATTCCCTTCGGCCATCTCACTTACTTTCCCCATTTGCACTTAGGATAGGTTAGTTCCAAAAGCCCATGGCATTT
CATAGTTGTATATTTTTATATGGCTCGTGGTAAACGTGTTTTCACATCGACGATAAGATTCAAATGAAATATGACGAAACTCAATATGCTTCTGG
TCCTACCCGCATTCTCACATGTTTGTACACGGATTTATGATGGCTACCTGTAATATTCGTATGTTTGGTGTAGGGGCGGCATTTAGACCATTTTC
ATTAATAATAAATCGTCAAATGGACGTGTTTTGGTCAGCAAAAAGGGGAAGAGGTTATTGGAAGGGCGATGTTGGTGTTTATCAAATTTCAAACG
CCCTTAAAATCACTGCATATC
(SEQ ID NO: 904)

Exon: 1001..1251
Exon: 4796..5253
Exon: 5351..5477
Exon: 5798..7090
Exon: 10702..11276
Start ATG: 4966

Transcript No. : CT24124
TCGTCGCCTGTTGAATATTTACATTAGTTCTATATATGTTTTTATACAAATATATATATTCTATTTACTTGAATTGTTTTTGTCGCCGCCGCCGC
TCGTTTCGTTTTGAATTCTTCATCTTCTTCTTTTAATTTTTTTTTTTTGGTGCTTTTGTTTTTGTTATTGTTTTGTATCTCAACTTTACTGCAGC
ATAACAACCACAACAACAACAGACGACGAAGGAGAGGGGAAATCATTTACAAAAATAAAACAATTGCAATCACTGGTTCCAGCATTTGATCGCAC
CCATCAATCCGATTCGAGCAGTAATGCAACAACCGGTCAAGAGCCCGCAGCGCTAAACCAATCCAAGCCCCACGCTCCAAGTTCCAAGCCCACCT
AATCCTAGTCCAGGACGCCTAGCCGTATACACAGTTCCAAGATGACCGATAATGGGAACAATCATAACAACAACAACAACAACAACAACGATGAG
GCACTCAGACTGAGGCTACCGGAAGAGCAGGCAGAGCAGCTGCTGCCCAAGAATGGATCAGCCGGCCAGACCAAGATAGCGCCACCTACGCATAC
TCATTCCATAGCCGCCGCTTCGGTGCCACAGAAGGTACCAGCGAAAAAAAAGCGAGACAAGAGCGATCTGGGTGAAGATTTTGTGGCGCCCGACG
GCGGATGGGGCTGGCTGGTGTCCGTCGCCAGTGGCGTTAACATTCTAGTGACGTTCGCATTGGCCCAGCAGTTTGGCATCCTTTTCCGCGATCGC
ATGGCTGGTCTAGGAATCTCCAGCTCCGAACTGACCACCATTATCAACACACAGATTGCTGTATCCGCATTTACAGGTCTGCTGAACGGTCCGCT
TTTCCGACGCTACACATATCGAGTGGTGGCCCTGGTGGGATCCGTGCTGACCTTTCTGGGTCTCTTCTGGATGGTGTTCGCCGACACCTTCGCCG
TCTACATAATGAGCTTCTCGATCTTGTACGGATTCGGACGAGGACTGACGGTATCCGCATCCTCGCTGGCGGTCAATACATACTTCAAGGTGAAG
CGACGCACTGCCACAGCTTTTCAGTTCGGAGTAGCCGGCCTGGGACCAATTGTGTGTCCCTACTTTGCCACCTACATGCTGTACGAGTTTGGTGT
CCAGGGGACGACACTACTCTTTGCCGGCGCCTCACTGCACACCATCGCCTGCTCGCTGATCTACCAGCCAGTCAAATGGCACGTGGTGAAGCGAG
ATCGCGATGCGGAGGCACTGCAGCAGGTCCAGCCACTGGCAGAGCGTGAGGATCAGGACGAGGATATTATCAAGAATGTTGTAGAGCCGGAAACC
CCGGTGCTGCCACGTGCCAATGACGGTTGGTTTGGCTCGCGGGCCTCGTTGAACAGCGTGGGCACTCGGAATCGACTGAACACCTGGGAGAAATC
GGACAGCAATGGCCACGTGGAGCTGAAGAGGCTAAGCAGTAAGGACTCAAATCCGGGACGCCAGCTGCGCAGCATATCCGTGAGTCACAGCATTA
AGGAGGAGGAGGCCACTGGCTACAATTCTGACCACGAAGTGCAACACACCGAGCTAACGGAGAAGGAGAAGCAAGAGCTGGAGGATGAGAAGGAG
CGCCAGCGCCGCAAGAAGCTGCCATTCTACATGAAAGTGGTGATATTCTTTGATATGGATCTGCTGAGGGATATCACGTATGTCAACCTGGCTGT
GGGCATCACACTGATCAACTTTGTGGAGATCAACTTTGCCATCCTGACACCCTTCATCCTAAGCGATTTGGGTTTCAATAAGGATCAGATTGCCC
TGGCCATGTCCACGCTGGGATTCTTCGATCTGGTTGTTCGATTCCTTATACCCCTGATCACGGCCAAAATCAATCTAAGCAACCGTACCTTCTTC
GTTGTGGGCATTTTGGGCATGTGCATTGGCCGCATGTTCCTCTCGATGACCTCCAATTTCTACGTCATGATGGCCATCTTCCTGTGGCTGGGCCT
TAACAAGGCCTTCCGCACGGTCTTCTGGTCCCTGATCATACCCAGTTATGTGCCCCTGAAGAGATTGCCGGCGGCAGCTGGGCTGCAGCTGCTGA
TGTCCGGCACCTTTTCGATGATCTTCGGACCGCTGATTGCGGCAGCGACGGGACGGCAAACGGCGACGGCAGTCAGTGTTCAGTATTCAGTATCG
ATTGAACAGCCGCGCGTAGCTCATCGAAATCGAGGAAGGAAGAGACGCGACGAGAGAGCGAGCAAGACGGACAGGCGACCAGACAGAGACAGCGA
CAGCAGGGAAAGGGAGACCAAGACGGAGACCGAGAAGGAGACATTGAGCGCCTGCCGCCCCCTCTTTTGTAATAAATAGCGCTGTGCGAAGCGAC
CACACTACCAAACGGCAAAAGTCCGCTGAGAGCGACGCAACGCAGGCCACAAAGGCCCGCCCCCCTCCCCCCTGCGATAGACACAACAGAACAGG
AACAACTATTGCAACAACACTATCACACACACACACACACACACACACCCGCAGTCAACAACACCCCCCTGAACGAAAGGAGAACAGTGAAA
CAGCTGGAACAAGAAACCAGAAAACAAAACAGGCTGACAAAACAAATGTCAAAATTAGCGACTGACCAAAGGGAATTTTAATCAAAAGTTAATAC
GAAAAAACCAACAAACCACCACGCGTTTCTCCACCAAGTGCCTT
(SEQ ID NO: 905)

Start ATG: 422

MTDNGNNHNNNNNNNNDEALRLRLPEEQAEQLLPKNGSAGQTKIAPPTHTHSIAAASVPQKVPAKKKRDKSDLGEDFVAPDGGWGWLVSVASGVN
ILVTFALAQQFGILFRDRMAGLGISSSELTTIINTQIAVSAFTGLLNGPLFRRYTYRVVALVGSVLTFLGLFWMVFADTFAVYIMSFSILYGFGR
GLTVSASSLAVNTYFKVKRRTATAFQFGVAGLGPIVCPYFATYMLYEFGVQGTTLLFAGASLHTIACSLIYQPVKWHVVKRDRDAEALQQVQPLA
EREDQDEDIIKNVVEPETPVLPRANDGWFGSRASLNSVGTRNRLNTWEKSDSNGHVELKRLSSKDSNPGRQLRSISVSHSIKEEEATGYNSDHEV
QHTELTEKEKQELEDEKERQRRKKLPFYMKVVIFFDMDLLRDITYVNLAVGITLINFVEINFAILTPFILSDLGFNKDQIALAMSTLGFFDLVVR
FLIPLITAKINLSNRTFFVVGILGMCIGRMFLSMTSNFYVMMAIFLWLGLNKAFRTVFWSLIIPSYVPLKRLPAAAGLQLLMSGTFSMIFGPLIA
AATGRQTATAVSVQYSVSIEQPRVAHRNRGRKRRDERASKTDRRPDRDSDSRERETKTETEKETLSACRPLFCNK*
(SEQ ID NO: 906)

Name: monocarboxylate transporter-like
Classification: transporter

Celera Sequence No. : 142000013384832
GACTGATAACACACAAAAAGAACACGCGTCTATTGTACAAAAAAGAGAAATCGATACGAAGAAACAATTTATTTACCTATTAGTGAGAGATTATT
AATGGAAACTATCAGCGGAAACAATTCCCAGCCCCAAAAACTACTAAAGGAAACTGTAGCGAACATTTTACTGTATTGCTGTAAATAATCATGAA
ACATTGGGCAAAGGACAGAGTTAGAAACCATTGCGGCCGAAACAATACACTGAATACAACCGAATTGAAGAACTTGCGAGTTCAAAAACTAGCTA
AAGAAAACACAACACGAATATTATATTTCTATTAACTAGGCGAATGCAAAGCATCTTGGAGCATTGAACATTGAATTTGAATTCCAAATCGAAAC
TGACTTAGCCACAATAAAATGCGCATAGCATATGAATGTACGTTGAGCGTAATGTTGAGTTTGAAATATATATTTTATGGTGTTTGGCCAAAAAC
ACGAAAATAATTAGAACTCAAGGCGAGGACTCGAAATGCAAAATTGCAACTTGAAAGCGGAGGTGCAAAGAACACACTTTGTAAATGAAGAGCAT AATTTAATTTATATTTATTCATGTATGATAACCGTAAAACACACAAATTATACAATATGCATACAGAATAAACTAAACTAACCAAAATCCCGCGT
CTTCTTCTTTTAATCAACACGTATCTGGACCTAACTTCCCGGGGATTTCCCTTCTGGACGTGTCCTTTGGAAAGATAAAAGAGGAAAGCTTAAA
GATCGCTGTAAGGTGCTTGCACCGATTGAGAAGGCTCAATGCAACCGTTTTTATAGATGATGCATCCTATGGCCTGCGAAAATATTTAAGTTGTG
CATTTTATTGTTTGATTATAGTAAATGACTTTTTAAAAAGTAACGTTAAATACCATTTCCAATGATTGGTATTTCTACAAACTGAAATGGTATAT
AACGCCATTTTCTGCCAGGTCCGAAGGAATTCTTATCGTTTGTAGCACGGTCACACTGCTCAGTTATTTCAATTGTTTGTCCCGTTTGCTCGAGC
ACTTGTTCCCAACGTAAGTCTAAAAAGACTTATTTTCCGAGATAATAAATCGCCGTGGCTGCGCATTATGTAAAGTGGAGTGGTTCCGTGCCGAT
TTCGCTGCGTTGGGGCCGTTCCAAACATATGGAATCTAAACGCAGCGTATTTCACTCCTGCTCGTGTGTGTCTGTGTGTGTTTATGGTTGTAGTG
GGGCTTCCGTGTCGCAAGTGGAAAACAAATGAAATTGAGTTCTCGCTTTGAGTCATATTCGAGTGACAAATAAAGCGCGTCATGCGTTGTCCATT
GAATTACAGTTTAATTTGATTACAGTTTAATTTGGTACCGCCAAGACATGTACGTCCAACCACCGATCGATCTGTGAGGGCCTCAAATATAGACA
TGGTGTACCCGCACAGGAATGAAGATGCGGGAGCATCTCTGGCGTGTTTGTGTGCTAATTAATTAATTGCTCATACTTGACCTGGACACTAAGCA
GACGCTGTTGAAATCGACAATACATATAACACTTTGTGCTCGCGTAGATGAAATGGGCGAAAATAGTGCGTGCTTGGTTCAAGTTACGTGAGCCC
CTCGCTTCGTGTGTGTTGGTAGGGAGCATTCAATGCGCGCGAGTGTGTGTGAGCAGCGGTGTGGGGATGGGCACCTCCTCTTTGCTTGTACCTAG
GTGGAATAGTTTGGTACCCGTGACTTTCCCAGGAAAAGAGCATTTTATAAAGTTTCCCTATTCTTTTGTTTTGTAAATTACTGTGAACATTGGGT
GATTTATTCAAAGTTGATTCAAAATAAATTACTAAGTACTAAGGAAACTTACAGAATAAAATATTTCTGAAACATCTCCTCGCGTTCGGAAATGT
AGGAAGCATGACTCAATTTGTATTCGTGAAATCATGAACCCACAATGCAGTACCCGAGGTTCAAAGAACTAGTACCCTCCACAGCAGTGTTTAAG
CAGGGTTTCTCTCAGTAGCGCAGTTCATTTGGCTTAATTTCTCTTTATTTACACTCGGTTCGCACAGATCAGGTTTTGTTCGCTGCTCGACGGGG
CAGCTGCATTCTTTCTCGCTCCCACCCTGCCCCTGGATTCCCCTGCACCTGTTCGTTCTCGAGGTGCGAGCGAGAGGCCAAGAGGCAGAGGTAGA
GCGGCACTTGCCACGCTTGACTTGCAGCAGGTCTGCAGGCGACGCGGAAATGCCACTAGAAGGTCCAGCTACAGCCGCCGATAGACACCAGTTCC
AGTCCCGATAAGGAAGCGATAGACTGAAGTAGACAGCTAGCTGGAAAGACAGATAGCGACGGGGAGAGTGGATTTATTTATTATTCAAATTCTGA
ATGGAATGACGATGTGATGGGCTCGTGCTCGTGTACGCGGCGACACTTTTTGCTGTCAATATGCTTCCTGCAAGTGGTGAGTAGACCGCGATCCG
AATGATTACAATTCGAAATCTACAGCCGTTCCCCATAGATAACGATTATCGAGCGCCAGGTATTCGACTTCCTCGGCTACATGTGGGCGCCTATC
CTAGTGAACTTTTTCCACATTTTGTTCATCATATTCGGGTTTTACGGCGCCTACCACTTTCGCGTTAAATACATCATCACCGTAAGTGCCCTGAT
TACCATATCTCTGCGATAACCCCATTTTATTTTGTGTGCCCGCCTGCAGTATCTAATATGGAACTTCCTGTGGATCGGGTGGAATACCTTCCTCA
TTTGCTTCTACTTAAATGTGGGGCAGTTGAACAGGGTGAGTTTCGTGGCTCCACAATAGACATATCTCTTCTTAACTAGAAGGAAATCTCTTCAC
AGGACAGTGACCTGCTCAACCTGGGCACTGGCAGCGTCTCCTGGTTCGAGGCGAATGGGTACGGTTGCAAGCCCACCTATAACATGGCCGCGGAC
GATACGTTCCGTCCCCAGCGGCCGGAGCGCGTGGAAGGCTGCCTGCTGGACTACCCGCTGGTGGAGATCACCCACTCGGGGGTACAGTGCGCTCT
GGCGGTGAGTGATCTACTAGCTTAAGTTCCCTGAATTGTGTAAATTGTCTCGCCCACTCCCACAGCTGCTCGGCATACTCGGTGCGATTCTGATT
AGTTGCATATTTCTTGACGAGGACGACAGATGTAAGTGGCGCTCTCTGAATGCGAATAAGAAACATGCTCGCCTGTCATAAACACCACTAACCGG
GAACGGTCATTGCTAACCCCTCTCATCCCCATAAGATCTTTCACTTTCGGGTCTGTGCACTGAGGTGTATGTTTTCTTTTCTCACAAAACCTAAA
ATAATACCCTATGTGTAAGCAATGTTTGTAAAGTTATCATCGAGAATTTGGCCAATGGCTTTATATTATTCTCGATTGTATAAGGCTCTCGATAA
GAAGTCTCTTGCCTCCCTACCAAAAAACCCGCAACCTGGAATGCGACTGTACCCCCAGAAAATTATGGTTTCGATTTAAACATAAATTGTGTCCT
ATATTAACCATTATGACTTGTCCATTTGAATTGTGTGCATCTATACACATGCCCTTTAAAACATTTTACTCACATACCACATAATCGTATTGTTA
TTCATGTTATGTATATGTCATTTACTCATAATCAAGAAATCAGAAACATTGTATTTGCATATGGGCAGCGACACTGTGCAGCTCTAAACCATGTA
AGACGACATTGAGATAGGTGCTCCGAAATGAATATAATTAATTGATATGAAAGTATGTAAATGTAAAAATGTAGACAAAATGAGCAAACAATATA
AAAACATATTTATTTACACAAATAAGAAGCTAAATCAATTACTCTTGACTAGTTCTATAATTAGTAAAAAGCTTGTGGGTGCTGCACGGTGTCCT
GCTGCCTCCGATGTTTTCCTCTGTTTATTGTTAAAGCATCTTAATCAATTTCTGGTTTTCAGTCGATTTCATGAACGGCGACGCGAAGAGTCCAC
AGCATACCGTGGTGCACCCAATGTACGTGAGCTATACAAGTATACCCACAACATCCGCAAGCGCCACCATGCAATCAAATAAGCATCTGCAACTG
CAGCACCAGCAGCCGCAGCAGAACTCACTGAAACTCTATCATCATCAGCAACAACAGCAACCCAAACTACACCACTTCAATAAGAACTACCAGTT
GAGCGGCAGCAACAATAATACACTGAATAATAATCTCCACCAGCGTGCGCCTGCGCTGCTGCCGCCAAACACAACAAATAACCGCAGCGCATCAT
TCCAAACTCAAAGTCACCCTTCAAACAACCATGTAACTCAACGCACAGGCGGAGAGGGGAGCAACTGCAGTAGTCTACGCCGCCATCGACAACAC
CATTCCAAGGCACTCGTCAGCCCCAGTCCCATGTCACCTCAGACCACGCCGTCGCTTTCGTACGCTTCCCTGCAAAACTCGAGTCCCTACCTAGC
CGGAAACTCCCTTAGCAACAGCAACTACAGCATATTCCAGAGCCCCGACTCGCTCCAGGGCAGTTCTCATTTCGCCCGTATTCATCACAAGCCCA
AGCCGCCCAAATCTGATTATCCTGTTTCTGGAGAATTCAATCCGGGCGGAATATATCCTCGCCTGTCCGTCCGCTCGATCGCCTGTCGCGCAGT
CTCGAGGACGACGAAGACAACTTTTCGCTGCAGAAGTTCGCTCCCGGCGAACACGGTGTCACCTACGTCCCTTTTCAAAGTCCTACTCCAAACAG
CCTTTTTCTGGGCGAGAACAACAACTCCCAGCCCCACCTCGTCTTTCACACCAACTCTCGGTCTAGTCCCAACAACAATGCTTATCCCTACGACC
AGAGCGGTTTGCCCTCTTCCCTCCGTATGGGGTCAAACTCCAATGCCCGACGGCCGACTCACATTCCTCTGCCCACGGTTCCCATGCACAACTGC
CAGGAGGTAGAAAATGATGAGGACGCAGATGGCGAATCCGAGCAAGATCACGATCAGATGCTGACGCCTCCGCCTCCGCCGTTAGTGCGGCCTCA
CATCCATCAACGCTTGGGTCAGGCGCCCTACCTCGATCTCTCTCCGGAAGTGGCAGAGCGCTATGCGATTCCCAGCAAGCTTGGACCCAGCCTTC
CCATTCAAGTGCCACTCCCCGTCCCACATGGTTCGCCCATGGTACGTCGCAGTAATCGTCGACCTAGGCCATCCAATCCCGTGAACTTTTGCGAC
CAGATTCGCGCTACACCTCCTGGTTATGTGGTACGCGCCCAGAGCGACGACCGTCTAATGGAGCAGGTCGAGGCTGATGCAGCACCGCACGTGAA
TCGTCGGAGCGGTCGCGGCGGTAGCGGTCAAAAGACCCGTCCTCGGTCGTTCTGCAACTCGATAGTGGGCGTGCAGGGTTAGACTTAAGTACGTC
CCGCTGCACTTGCTCCTCTCCTCTCTCTTACTCACGCTTTCTGCCTAGGCAGGATGGCTGTTACTAACTCTACCAGGATCACTCGATCCCTAAAC
ACATACAAAAAATTTCATATACATAGGTGTTGCTGTTTCTTTGTTGTGCCTAACCAGCCGGCTAACCTGGCTAAGAACAGGTCCTAACCATAGCT
TCCCATGCAAGCGTTTATCGATTTTAATGATACCTTGCAGAGCTGACTTTAATTGTGTAAATCTAATTAATAATTCAGATACGTGCGATCAGTAG
AGACTTTCCTCGAATTGTGATAGAAGGCGTGGAAAGTCGTGACAGAATGCAAGCCTAACAATTTTATGTTGATCTGTGATAACTGAAAACAAATA
TGAACGACAAACGATAATTTGAAAAACGAAAATGTCACAAAATCATTATCAAGAAAAGGATATGACAATTTGTTGAGAATACGAGCGATAAATGA
AATTTTGAGCCAATTGCAACCAGATGCCTTGGATGTATGACGGAATAGAGATTAGAATATACAACATACATATATATACCGATGTTATGGGCGGG
AGAGCCCAGCCTCCCCAAGAGTTGCCTTTGTTGTTTAACTAATAATACATATGAATGTATATTTGCCCTTAATAACGAAATGTACTACGATGCAA
ACTTTAGTTGTCGAACACAAACAAGAAGTTGCCTATTCCGTTAAGTGAGAGATTCGTTATACAAGCGCAAGCAAACGTAAAAACGTTTAGAATTA
CGTATAGAAATGTTAAGCCTAGTATTAAGCTTGAGGCCACAAAACGCAAGAGCAGAGCAGATCTAAATCCATTTAGCGTAGACACTATTTACTGT
TTTAGATAGATCCCTCATATTTAGCCATGCGAATTGTGCGTAGACTGGTGCCAATTCTCGAAGAGATTGAACGCGTTTCCAATAAAAATGTTCAT
TTACACCATAGTACGGGTAATCTTTCTCTGTCTCGGAAGCTTTTTTCGTAGCCGATCCTTCTATCTTCCTAAGTTGCTCTCTTACTGGTAGTTGG
CTTTTTGTAGCAATTGTGCCTCTAACCAACCGCTAACTATTGATTCTCTCCGAACGTAGCTAATCCAACTTGATTAACAGCTCCAATCACAAAAG
CACACTCAAAAGCAAGCCAAGGTAACTTTGAGCATTGTATCCGCGGCTTAACGGTCTAAACAATCTTCCACTGATCCTATATTGTTCTCTCCGGC
GCAGTGAAGCATATTAGGAAGCAGTCTAAACACCGCCAGTCGCTGTACTCCATCGAATTCGGCAGCAGTACCGACACCATCCGGCATGGCGGCCA
CTCCTTGGGACTGGGCGATCCTCGGGGCGACCAAGATGGCGGCGAACTGAGTCCTAAGCCGATGACACCACGACGCGTCAAGCGGCGATCGGTCA
TGGCGCGCGGCACACAAGGAAGGCAGTCAAATGGAGGAGGCTCTAGCAGGCGCTCATACCACGGATCAAGCGGCACCCTGAGATCCAAGCACGGA
CATAGTGGACGTGGAGGCGGAGCAGACAGCAGTAGCGGAAGCTATGTGAGGAGCAGCACTCGAAGCTCTCGCCGGAAGTATCATCAGAATCCAGT
GACTAAAATCATCGATCAGCAGCTTCAGCAGGAGCAACCTCACCTGGGTTCCTTCCACCGACAGGATAAACTCTCGCTGACTGCCTCCAACCTGC
AATCACTCAACAATGACTTTGTGAACAACACCAATGCTTCCGGCAGTCAATTGGGAAGTCTCGGCAAACCCAATGAGCACTACTACCACAGCTAC
CGCAAAAACATTCCGCTGGATCCCATTTACTACAATACCAACGGTCTAGGAGCGCTGGAGGAACCACCGAGCCTTCCACCGCCACCACCTCTGCC

FIGURE SHEET 491

ATCTGCAGCTGGAGCCTCAATCCTGCACGCGGGCGGTGGAGGCCACTACAACCCCAGTTACCAACACTCCACGACGCACCTAAACGACGTTGGTC
ACGCTCCCGATGAAGTATACAACAATCGACCGCCCTCGGTGCGCTCCAGTTACTCGAATTTTCATGGCTCACGGCCACTCTCCACCGCTTACGGG
AATGCCACTGGTGAGAATGTATTCGCTGGACTGAACGGAGCCAGCGCCAGCCCACCGCAGGCTCCTTGTACGCCACCCCTCTACCAACAGCATCC
CATGCAACTACAGCAGCACCAACAGCAGCAGTATCCTCCACCGCCGCCAATGGATCCGGCGCCTGCTTACGTCAGCACCATGTCGTTCTCCAAAA
GAACTGCCTCTCGGGAAAGCATTCGCTCAATGGCCTTTCTCAACAACGGCCCGCCCGCCTACAATCTGAATTACCACACGCCGCCCGACTCGGAG
ACGACCATGTAATTTGGTTCGCCCTTTGTCTTTACCGTCGCACATGGATCTTGAACTATAACACAATCATCATCAAGCCATCAGCCCATGCCCAA
CACATATTATATCTTGTGCAACAAGCCAAGGCTACCACTTGGTGCTTTAACCACATGGATAGCATATACTTGATCAGTAAAATAACGATATCTGT
AGTGCTTAATTTATACGTAAGTTTCTGTCGTTTTACCAAAGTGCCTTTGTAAATAAATACTTAAAATAATGGATCGGTTATTTAAATATCAGAAA
ATATTGTTAATACTTGATTGTTTATGTTCATTTATATTTCTTCTTAGGTAATTGGCTTATAGTTTTATACCTGTAGATAAGTACGTGCTGTACTT
GGTATCTTAGTCCCTTCGACACACTGTAAGATGTACGAAAACTTAGGAAACTGCAAAAGTTGGATATTTGCTCCAATACTTACATTCATCTGCAT
CCCAGCCCGGCTCGATGTCCAGTTGCTTGTTGCGCTCCTTCAGCCACGTGAAAAGTGGGGCAAAGTACTCAAGGATACCGCGTCCGCTCAACTTT
CGTTCACCGGTGGCTATCTCCATGACATCCCGCCAATGTCGAGTGGCTCCCAGCTGCATCATGTCGCGAATCTTTTTTCCTGCTTCTTTGCTGTC
GTAGAAATCGCAATTGTGAAGTGGGAAATTGGGATCACCGGGCTTGTACTGGCCACTTGCCAGGCAAAAGGAACGGTAGAACTGGAATCCCAGGA
TCTCGGCCAGGAATTTTCTGTGGGTCCCGGGGAATATGAAATTCATGATTATCAAAAACAAATTATGGAAACTGACTTGGTATTGGAGGTTTCCG
GATTTAGTCCTCGATAGAACTTGAAATCCACATCAAAGTCCTTGTTAAGACGTTGTAATGGCGGCTGAACTCCGGCGAATTTGTCCTGGAGGCCC
CAGTAAGCGCAGTTATAGTCCTTTACTCCGATTCGCCCGTCCATTACGTCCACGAGGAATTT
(SEQ ID NO: 907)

Exon: 1001..1058
Exon: 2063..2451
Exon: 2509..2646
Exon: 2710..2790
Exon: 2853..3044
Exon: 3106..3166
Exon: 3958..5397
Exon: 6655..7802
Start ATG: 2392

Transcript No. : CT24170
TCACACTGCTCAGTTATTTCAATTGTTTGTCCCGTTTGCTCGAGCACTTGTTCCCAACATCAGGTTTTGTTCGCTGCTCGACGGGGCAGCTGCAT
TCTTTCTCGCTCCCACCCTGCCCCTGGATTCCCCTGCACCTGTTCGTTCTCGAGGTGCGAGCGAGAGGCCAAGAGGCAGAGGTAGAGCGGCACTT
GCCACGCTTGACTTGCAGCAGGTCTGCAGGCGACGCGGAAATGCCACTAGAAGGTCCAGCTACAGCCGCCGATAGACACCAGTTCCAGTCCCGAT
AAGGAAGCGATAGACTGAAGTAGACAGCTAGCTGGAAAGACAGATAGCGACGGGGAGAGTGGATTTATTTATTATTCAAATTCTGAATGGAATGA
CGATGTGATGGGCTCGTGCTCGTGTACGCGGCGACACTTTTTGCTGTCAATATGCTTCCTGCAAGTGATAACGATTATCGAGCGCCAGGTATTCG
ACTTCCTCGGCTACATGTGGGCGCCTATCCTAGTGAACTTTTTCCACATTTTGTTCATCATATTCGGGTTTTACGGCGCCTACCACTTTCGCGTT
AAATACATCATCACCTATCTAATATGGAACTTCCTGTGGATCGGGTGGAATACCTTCCTCATTTGCTTCTACTTAAATGTGGGGCAGTTGAACAG
GGACAGTGACCTGCTCAACCTGGGCACTGGCAGCGTCTCCTGGTTCGAGGCGAATGGGTACGGTTGCAAGCCCACCTATAACATGGCCGCGGACG
ATACGTTCCGTCCCCAGCGGCCGGAGCGCGTGGAAGGCTGCCTGCTGGACTACCCGCTGGTGGAGATCACCCACTCGGGGGTACAGTGCGCTCTG
GCGCTGCTCGGCATACTCGGTGCGATTCTGATTAGTTGCATATTTCTTGACGAGGACGACAGATTCGATTTCATGAACGGCGACGCGAAGAGTCC
ACAGCATACCGTGGTGCACCCAATGTACGTGAGCTATACAAGTATACCCACAACATCCGCAAGCGCCACCATGCAATCAAATAAGCATCTGCAAC
TGCAGCACCAGCAGCCGCAGCAGAACTCACTGAAACTCTATCATCATCAGCAACAACAGCAACCCAAACTACACCACTTCAATAAGAACTACCAG
TTGAGCGGCAGCAACAATAATACACTGAATAATAATCTCCACCAGCGTGCGCCTGCGCTGCTGCCGCCAAACACAACAAATAACCGCAGCGCATC
ATTCCAAACTCAAAGTCACCCTTCAAACAACCATGTAACTCAACGCACAGGCGGAGAGGGGAGCAACTGCAGTAGTCTACGCCGCCATCGACAAC
ACCATTCCAAGGCACTCGTCAGCCCCAGTCCCATGTCACCTCAGACCACGCCGTCGCTTTCGTACGCTTCCCTGCAAAACTCGAGTCCCTACCTA
GCCGGAAACTCCCTTAGCAACAGCAACTACAGCATATTCCAGAGCCCCGACTCGCTCCAGGGCAGTTCTCATTTCGCCCGTATTCATCACAAGCC
CAAGCCGCCCAAATCTGATTATCCTGTTTCTGGAGAATTCAATCCGGGCGGGAATATATCCTCGCCTGTCCGTCCGCTCGATCGCCTGTCGCGCA
GTCTCGAGGACGACGAAGACAACTTTTCGCTGCAGAAGTTCGCTCCCGGCGAACACGGTGTCACCTACGTCCCTTTTCAAAGTCCTACTCCAAAC
AGCCTTTTTCTGGGCGAGAACAACAACTCCCAGCCCCACCTCGTCTTTCACACCAACTCTCGGTCTAGTCCCAACAACAATGCTTATCCCTACGA
CCAGAGCGGTTTGCCCTCTTCCCTCCGTATGGGGTCAAACTCCAATGCCCGACGGCCGACTCACATTCCTCTGCCCACGGTTCCCATGCACAACT
GCCAGGAGGTAGAAAATGATGAGGACGCAGATGGCGAATCCGAGCAAGATCACGATCAGATGCTGACGCCTCCGCCTCCGCCGTTAGTGCGGCCT
CACATCCATCAACGCTTGGGTCAGGCGCCCTACCTCGATCTCTCTCCGGAAGTGGCAGAGCGCTATGCGATTCCCAGCAAGCTTGGACCCAGCCT
TCCCATTCAAGTGCCACTCCCCGTCCCACATGGTTCGCCCATGGTACGTCGCAGTAATCGTCGACCTAGGCCATCCAATCCCGTGAACTTTTGCG
ACCAGATTCGCGCTACACCTCCTGGTTATGTGGTACGCGCCCAGAGCGACGACCGTCTAATGGAGCAGGTCGAGGCTGATGCAGCACCGCACGTG
AATCGTCGGAGCGGTCGCGGCGGTAGCGGTCAAAAGACCCGTCCTCGGTCGTTCTGCAACTCGATAGTGGGCGTGCAGGTGAAGCATATTAGGAA
GCAGTCTAAACACCGCCAGTCGCTGTACTCCATCGAATTCGGCAGCAGTACCGACACCATCCGGCATGGCGGCCACTCCTTGGGACTGGGCGATC
CTCGGGGCGACCAAGATGGCGGCGAACTGAGTCCTAAGCCGATGACACCACGACGCGTCAAGCGGCGATCGGTCATGGCGCGCGGCACACAAGGA
AGGCAGTCAAATGGAGGAGGCTCTAGCAGGCGCTCATACCACGGATCAAGCGGCACCCTGAGATCCAAGCACGGACATAGTGGACGTGGAGGCGG
AGCAGACAGCAGTAGCGGAAGCTATGTGAGGAGCAGCACTCGAAGCTCTCGCCGGAAGTATCATCAGAATCCAGTGACTAAAATCATCGATCAGC
AGCTTCAGCAGGAGCAACCTCACCTGGGTTCCTTCCACCGACAGGATAAACTCTCGCTGACTGCCTCCAACCTGCAATCACTCAACAATGACTTT
GTGAACAACACCAATGCTTCCGGCAGTCAATTGGGAAGTCTCGGCAAACCCAATGAGCACTACTACCACAGCTACCGCAAAAACATTCCGCTGGA
TCCCATTTACTACAATACCAACGGTCTAGGAGCGCTGGAGGAACCACCGAGCCTTCCACCGCCACCACCTCTGCCATCTGCAGCTGGAGCCTCAA
TCCTGCACGCGGGCGGTGGAGGCCACTACAACCCCAGTTACCAACACTCCACGACGCACCTAAACGACGTTGGTCACGCTCCCGATGAAGTATAC
AACAATCGACCGCCCTCGGTGCGCTCCAGTTACTCGAATTTTCATGGCTCACGGCCACTCTCCACCGCTTACGGGAATGCCACTGGTGAGAATGT
ATTCGCTGGACTGAACGGAGCCAGCGCCAGCCCACCGCAGGCTCCTTGTACGCCACCCCTCTACCAACAGCATCCCATGCAACTACAGCAGCACC
AACAGCAGCAGTATCCTCCACCGCCGCCAATGGATCCGGCGCCTGCTTACGTCAGCACCATGTCGTTCTCCAAAAGAACTGCCTCTCGGGAAAGC
ATTCGCTCAATGGCCTTTCTCAACAACGGCCCGCCCGCCTACAATCTGAATTACCACACGCCGCCCGACTCGGAGACGACCATGTAA
(SEQ ID NO: 908)

Start ATG: 388

MGSCSCTRRHFLLSICFLQVITIIERQVFDFLGYMWAPILVNFFHILFIIFGFYGAYHFRVKYIITYLIWNFLWIGWNTFLICFYLNVGQLNRDS
DLLNLGTGSVSWFEANGYGCKPTYNMAADDTFRPQRPERVEGCLLDYPLVEITHSGVQCALALLGILGAILISCIFLDEDDRFDFMNGDAKSPQH
TVVHPMYVSYTSIPTTSASATMQSNKHLQLQHQQPQQNSLKLYHHQQQQPKLHHFNKNYQLSGSNNNTLNNNLHQRAPALLPPNTTNNRSASFQ
TQSHPSNNHVTQRTGGEGSNCSSLRRHRQHHSKALVSPSPMSPQTTPSLSYASLQNSSPYLAGNSLSNSNYSIFQSPDSLQGSSHFARIHHKPKP
PKSDYPVSGEFNPGGNISSPVRPLDRLSRSLEDDEDNFSLQKFAPGEHGVTYVPFQSPTPNSLFLGENNNSQPHLVFHTNSRSSPNNNAYPYDQS
GLPSSLRMGSNSNARRPTHIPLPTVPMHNCQEVENDEDADGESEQDHDQMLTPPPPPLVRPHIHQRLGQAPYLDLSPEVAERYAIPSKLGPSLPI
QVPLPVPHGSPMVRRSNRRPRPSNPVNFCDQIRATPPGYVVRAQSDDRLMEQVEADAAPHVNRRSGRGGSGQKTRPRSFCNSIVGVQVKHIRKQS
KHRQSLYSIEFGSSTDTIRHGGHSLGLGDPRGDQDGGELSPKPMTPRRVKRRSVMARGTQGRQSNGGGSSRRSYHGSSGTLRSKHGHSGRGGGAD
SSSGSYVRSSTRSSRRKYHQNPVTKIIDQQLQQEQPHLGSFHRQDKLSLTASNLQSLNNDFVNNTNASGSQLGSLGKPNEHYYHSYRKNIPLDPI
YYNTNGLGALEEPPSLPPPPPLPSAAGASILHAGGGGHYNPSYQHSTTHLNDVGHAPDEVYNNRPPSVRSSYSNFHGSRPLSTAYGNATGENVFA
GLNGASASPPQAPCTPPLYQQHPMQLQQHQQQQYPPPPPMDPAPAYVSTMSFSKRTASRESIRSMAFLNNGPPAYNLNYHTPPDSETTM*
(SEQ ID NO: 909)

Celera Sequence No. : 142000013383969
CATAGAGCGGCTCTATAAAGATCTATTTTCCCCTTACTCTCTGTCTCTCTCTCTCTCTGTCTGTTTGTAGCTCTCTCTTTTTTCCCATAAGAT
GATTTCTGAACGCAGATAATTATTCTTATTCTTATTATATTTTTGTATTAATTTGAGCCAATAATTTTGCCTTTTTCCAAAATTAGTTAAGCATA
ATAATTTCTATTATATTTCTTATTAATTTAGAAACGTGTTCAGCTCAAAGCTAAACAAAAACATGTCAAAAGAAACGGAATTTTTGTTCAGTGCA
ATAAGATCTCTGAGCGGATCTATTCAACAGTCCAAGTTCTACGTCGTCATCATGATGGTGTAAACACATTTGCCAAATCACATCACAGCCCACTG
TTGAGCCGGTCTTGTGAGAGTGCGATAGAGAGGGGTCGCCCAGGCCAAGACAGAGAGACAGAGAAAGAGACAGGTGGAGAGAGAGGGAAGGCTAT
TGCCCGGCAACTGCTAATTGGGATGGCTAAATGCTGCATTGCATCCTCTGCCGCGATTCCTGCTGCACTTACGGTGCATCGTCGTCTATCCTGGC
GCTGCCCACGCACGAAGAGAGAAGTTCACACTCTTCCCGCCTTCCGCCGGCGGTACAGAGCAAAAAAAAATTTTATTAATTTCGGTTAATTACAA
ATTTGTACCAGGGACTTAAGCTAACGAATTTCAGAACCGAAACATTCATAAGCTTATGCTTAACAACGTAATTATATAAAATAAATAAAATTGGG
AATTTGCTAGCATGCCAAGCATGTGATGTGTAATGTGATCCTTGGTCAAGAGATTTACATTCTCTCTTGCTTGCCCAATGCAAATTTCTCTCAGT
GTACGGGCCAGCTCTCTCCGACCATCTCGCTCTCGTTCCGCCGTTTTGCTTTGCCAGTGACTTTGCTTTGCTTTGGCGTAGAGAATGCTATAAAG
CAGACCGCAGCAGTGGAATAGCAGCAAGTCGACTGCTGGCCGCGTAACAGTAAACACACCAACGAGCGGACGTACACGGAGCGAAAGAAGAAGTT
GGCTACCACGAAAGAGTTATTGTTTGTTAGAAACACCAAGCGCAGCAGCAGCAGCAGCAGTACAAATATTATTGTGTGCCGTCCGAAGAGAACAG
CTGAGCCACACGCTGTTTTTTAACGCTGTTCCGTTCTGCGGCACTTGCTGTTTGTTATCCGTATCCGTCGTGTTTCGTCGTCGTATTTGAACTCT
CTTTTTGTTACTGTGCATATATTTTTGAAATCTCTGTGCTGCACACAGCGCAGGGGGAAAAGTGCTAGAATTAGCAGATCATCAAGACATCTGGC
TAACCTGTGATTTCCAACACACCCGAAGGCAAATTGGCAACAAGTTACCACCGTAAGTCTCGTGTCGATCAACAAGTGAAGATGTTAGTTAAGTG
TGGCAAAAGAACTGAACAAGAATTTATTGCATTTGCAAATATACATATGTACTATACCGATAGGAACGCGTTTTAAGAAAGTAATCATGCTTTTA
ATTTACGTGATGTGTGACTGTTATTTGTGATTCAATATAAGAAGATTAAGAAGATTAATAAGATTTTGTGAAATTTTCAAACTATGCCCAAGACA
AATGTAGCCCACTGTTTTGGGGGTAGGGGATTTTCAGAAGCTTTGCTTTTGAGCATAAACCGTAATTAGAAGGCATTAAAAACGTGTGATTTGGA
AATTCGTGAATTAAACCTTATAGGATTTCTCTCTCTCTCTCTCTGTGAGAGAGTGTGAGAACCCAAATTGAGTTTAAGAATTAGCTGAAGTTT
CCATAATAACCACTGGCCAAGTGATTAGTTCACATGGTGGGTGGAATCCGTCTAGTCCAAACCATAATCCCCTGCCCAGTCTGATCTGATCCCGG
AACCAAATTGAGTTTTGCCAAAGGTTTCAGCATTTTTCATGTGCATTTTTTTTTCATCTAACCATCGACGGGGAGCAGAAAATGTTTACCAAATT
GAATTACACATTTTTATGATGTGCTGGTGCCTTGCTCTTCCCCCTTCCTCAAAGCCACCGCCACCCCGCCGCCTGACAGGCCTCAGGTGCTGTCC
TGAATCTGGAAATCCGTGTGTCCGGGTGCCGAAGCCGGAATGGAAGGAGTCCACGTTTTCGAGAGCGGGAATGCATTTATGGCGCCGCCATTAGG
GTGGACCAGTAAATTAGGTTAATTGTAGAAAGTAATCGAAAGCTTTAACAGCACCAAATTGCATATTCTGAATCAAGGAGACTGTATTTTTCCCA
CACTGCAAGTCACATTTCAATATGTAAGTGCTGCATTGAATATGTACATGTTCAACTTATAAATGTGTATTCTATATATATATATATATAGGCAC
ATAATCTATAATCTGTTTTGTAATCACTACTGCTTTTTGCAACTTTATGGTAAAAAATACTTTGTAAATCCTTTGGTGTGCACCAAAATGAGCAT
GAATGCATAAGCAAACATAAGCGCTTAATTATGAAAACATACCGATTTAACTAGAGTCCTGGATTATAATTGACCGATTATTTGATTAAAAGGCA
TCCGAGGCATTCAAGAGCAACCAAATATTGTTGGCCGTTGATAACCATTGCTGGTTGCCAAGGTTTCCATAGTATTTGCAATCGGCTCAGAAGTG
AAATGCTCTGTCTGAAATTCCGACTTAACTCCCCACCAGATAACCTGTTGCATTTCGCAATGGGGTAAACAATGGAATCACCTGTGCGCCCCCAC
ATTTTGGCCTTCATATGGAAGCACATTCGTGCGCATTCATCTGGAAAATTGATGGTAAATTTCGCATTTAGTTTGATTCTCAATTGAATCAACAG
TTCTAAGCCTACTGCTTACGTGTTTGTGCGATGATGATGATGATGTATAATGGTCTATCCACCTTTCGCAAATTTGCAATGGACAAGGAGGCGGT
GCAAAGGTCTGTACATAAGTCCAGAATCTCAAGGGGTGATAAGCCTAAAAAAAAGGCAGACTGTTATATGTCAGATACTCGTAGATAGTTAGAGG
GGTTTTTCAATGAAAAACTTAGAAGTGTTATTTTGCCTTCTGACACTTCACAATGAATATTCAGAAAAAAAAAAAATGGGGAATTAACAAAGCAAT
ATGATTATGATATGATATTATATCAATAGTTTTATTTATCAACATTCAGGTGTGCACTAATTTCTTGCCGCCAAAAACAAAGCCAATCAATAATT
TATGTAGATAAGCATTTTGCTTATAACCATGCATTTTCATTATTGAATTGTCATTTTTTATCTTAGTTGAACCCAACTCCGCCTCCTCCGCGTAG
ATCGTGTGTCAGCCACTTGTCTTGTTTGACAGCACACCCAAGTGGCATTAGCATTTGGGGACTGAAACTGGAACCATTGGCCAGTTTGCCCAAGA
GAATTTCTGGGATTGGTTTTGGGTTTCTCCAGTGCACCGCAGTGCACTCCTCTCGGGCCACCACTTCAGTTCACGGAAGGCACCACTTGGTGGGA
GTCGGCTTGAAGTACGTGAGTTTATTTGGCTGAGCACAAAAATCAGAGACTCGAACAACACACAAGATCGAAAACAAAAAACAAAATTAAACAAA
AAATATAATAAAATAAAAGAAGTGAAGTGAAGAGCAGGGTCGAGAGGAGAGGAGGGGAGAAGTGCCTAGAAATGGTCTGAAATGTGCATTAAACG
CTTTGCATAGGAAAGCGACATGGACATGGTATGGGGATTGCGCCGGAGATTGACATTCCCATTCCCATTCCCGTTCGTATTCCTATTCCATTGGG
CTACCCACTCCTATTTCCATTTCCCATTCCCTAACCCAAATCCCTACTATACCATTTTCACTTCGAGAATCGCAGAGAACACACAAAACACACAT
GTGAGAATGTGCCGGGTGTTGGGATTATTTTGTGGCCGGGTGAGGGGCCTTCAGGCCTTCAGGCCTTCGGGCAATAACAATCATTCGAAATGCGC
CTTAAAATAGCAAACACCAAACACGTTGCTCATAATCTCCGATGCAATTGAGTGCTGGCAGCCAGCACATGAATGATAACTTTGTCCAGGCCCGC
TGGAGTATTAATAGCCATTTCTAGTCCCTATTGAAAGCGAGCATGACGCCCGCTGCCATGCCAACCAGCATCCCCATTGAGCTCCTAACCATGGC
CGACCAACCAACATCGTCCGAACCTGCAGAACAAAGCCGAAAAAACGTCTCTAAGCCACAGTCCAACTTCAGTTTTGGTTGTCGCCACCAGGTGT
CAATGCTTTAAATTATGTTTTACATTTCCACCAAAAAACACATCATCAGCCAACCAACAACACCATCATTTGCACTTGTTGTTGGCTAATTAGCG
GCGAGAAGTTTTTTCTAACACAGCAAAGCCCATCCATTCACCCAACCGTTTGTTCGAGTTAGCGAAGTTCAACTGTATGGCTTGGTGCCCGAAAT
TTTTGCCCACTCCTGGGATTTGGTCTTATGCATTTTGCAATTTGTTTTCCACCACGAAAGTAGCAGGCGCCAAAAACTCTGGGTTCGGAATAAAG
GCCATAGATTCCGTGAAACCAAGGGGGTCTTCTTTATTAGAGTTTACGATTCGATGCGTTTATATTACCGAAATAAACCCTAATTGGACACATTG
ATGCTGCAAAACGCAACACACATTTGTGCTTTTGACTTTCCTCCTCCCATCGACGTTGATCTCTAAAAACCGGTTTTCCAGCCTTATATGCATAC
AAATCACTTCCTCTAAACAACGATTCAACGATTTCAGCGTCATTATACCGTCAATTAAAGAGTACGCCCCTAAAAACGAGAGTTTGACATATTTG
TACATATGTAAACCCGTTTTGAACGAGGAACTATTTTAGTTAATAATAGGTATGTATATAACTACAGATTTCTAGCCAACAAAATGACTTCCGAA
ACAAATAATTAAGTAAAAAGTATTCTATAGAACTCTATTGTTTTGATAGCTAGATTAGTGCGCAGGTATAAAAAACTGAATATTTCCTCTAACAC
ATTTTCTAGACACTCAACTTGAAAGCATTGTGGCATTATTTGTTTTCGCCTTCCTCGAATACTAAATCATTTAATAATGTTCCTCAATCAGATCA
AAGCGGAATCCGTTCTTATTGTAATCTTCTGAAAAAGAGGTAAGCTCTTCGGGCAAATATGTATCTCATTGATAGATGGATGATATCTCCCATAT AGTATAGCCATCCATACCAGTGGGTGATTATAATAATTATATTTACAACGAAGCGTTCAGTTCACAAGTCCGATGTTGCCCTTTTCCCTTCTCAA
ACTTTAAGTACACCTCCAACCAGATTGTACATATGTACATACATATATGTACATACATATATGTTTGTTCTCTTATTTGATCAGCTGAATGTTGG
GCGTTCTCTTACTTTTCTCATTAGCAGCGAATCAATTACGCGCGTATCGCTGGGTGTTTAATCAATTCTCATTGACACAATTTAATTGAAGCGTT
TGCTTGTGAAATAAAACGATCTGAGCGCCAATTCGTTGACGCCTCTCGTTGCGCATACCCATGTATTCACTATATGTTGTGAATGAATATACTCA
TATACTCATATGTTGTATATATACGATTCGATTCCGTTTATTACACACAAAGCAAACCGATTAATCTCAATTAGGGGCCAATTGGCTGAGCGAAA
ATGCTGGAGAAAACTTCCGTTGCGTGTGTAAACACTGGGAGAAAATCTTGTACGTTAGAACTGAAGAAGTGATCGTAATAATATAATATAATATA
ATAATAATAATAATAATAATAGCATAATATGATAACGTATTTATATTATTATTGTATATAATTAAATTATTTTATGTGTGAATAATTGTTAACAC
AATTGATATGTCTTTCTCTGAGTGTATCAATGGGAAGCTTGTTTGATAGTTGTTCGCCCATTAGCTGCACCTGTTCTACACGCTTGCTCCTTGTA
TTCTTTTTTTGTCATCTGTGTGCCTGAGTGGGCATGTCGTGAACTCGAGAAAGTACAAGTGTTTCCAGCACTTTGTTCTCTGGCTCCACTTCGTC
CCGCCCAGAGATAACCGGCGATCGGCCTAATCAATAGTGCCGCGCCATCGGGGCCCTCTATCTATATATTTATCTTTCTATCTTTCCGAGCGTAT
GACTCATCACAGGCCCGACCGTTTGCCATTCCGGGTGCGATAAGGCCTAGAATTTGGTAGACCCGTTAATTGGTGCACAGAGAAAAAAAAATGAT
GTCATTGGTAAGCCGCATTCCTTGATACACAGTATCAAGCTGCTCTTCACTCCGAAGCCTTGCTCATTTTGAGATTGGCTTTTCAAGAGCAATTC
TTTGAAGATTCATCTTTGATTCCACATTACATCATGGCGGAATCGAAATCTTCGAAAAACACCATTTACCGATGCGGACTTGAAAAGAAGATAAT
TTGGGATTTGGAACTGCGTTTTTTTTTTTGGCTTTAGTCTTCCAATTTTTGCGTTATCTTATCTCATAAGTGACATGATCGTATAACCACCAAT
ATTCCAGTTTGCATGCAAGTTTCTAGACAGACAGATTCGCGATATATATGTACATATATAGCACGTGCTTTTTGGCTGTATTCGATTCTATTATC
TGGCCATTGCGAAAAGAATTTGCCAATCCTTGGGCGCATTCGGTTCCTTTGTCCGATCGCTTGGGGAACACTCCGGCTTTCCATTCGTGGTGGCC
CGTCTTATCGTTTATAAAAGATAACACCATTCGACGGCAATAAGCCCAGCGAATCCCTTGTTTATTGACTTCTTATTCACCGGGCCCCGGTCATT
AAAATGCAAAATTATAGGCGGCACACAAGCGTCTTATCGATGAACGGGTTATCCAAAAATAGGTTTCAACCATCCAGACAAATTGCGATTTGTAT
TTTATTGCATGTTGGCAAATCGAAATGTGCGCGAATTAAAAAGAAAAAAATTAAATAATAAAAAAAAACATAATTGTGAAATAACCAATTGTCAC
CAACTAACCCAACCAAACAACAGCCAGCACTTACCAACATTATCTCAGCAGCTATTTGTATTTGTTTTTTTTTTTTCACAAAAAATTGTTGCCCA
TGCGGCATGACGGCGCAAAATACATTGTCATTTATAAGAAAACATCAACGACAAATTGCGGAAACCACTCGGCAAATGCCCCACCGTAACCCGAA
GCCCCAAAGACCGGAATATGGTGGATCGATCGATGGAGATTGGGCGATCTCTCGAACGCTCCAACTTGCTCGATATTCCGACGACTCAGAGAGAA
AGTATCGCCACTTAATGCTCTCACGATAGCGTAGAGCCATATTGAATATGTGGAATGTCATGCGATGAGTTTGCAAGTACAGTGTAGCAAACTAG
TCGAGTGTGTTTGTTTTAATCACTTCTAGTCGATAATGTTAATAATGTAGTGGCATAATTTTAATGTTATCGCATTGGAAGTGTTGTAGTTCAT
GGAAAAGACTTCAGTTTTATCGAAAAGGTGTCTAAAAGTAGGCTACAACATCTTACAATAGGCGTACTACTTAACCAAGTAAAAATGTTAGAAGT
TAGAAGAATACTTATGCCACCACATGGTAACCAAATTATTTGTTTAAATACATAATTCCTTTAAACTTTCTTTAGAAACTGCATTGCTAATACAT
TAACTTCCGTAGAAATGTTAACACAATCAATTCCTCTTAACTTTTGTATATTCATTAACTCATCCTGTGCAGATGGCCAGACTCTCATCCAGCTT
TTCTCAGTTGATCGATGGCTTGGAACTTAGAGTCTACTAAGTGCCATCGTCGGGGGTTTTGTACTTCTGGTTCTACCCCTTCTGCCCTCGATCCC
AGACTGACTGCGTCAGCGGGCGGGCGTCAATTTATGGCACGCTTCGATGAAGTTCCATGGATGATGATGATGATGATGATGATGGGATGGAGCGT
TGATGATGGGACGGGGCTTCCGGGGAAGCACTGTCTGAATGAAGACATATCCCCAGTGCACCAGCTGTACTCGTTCCCGCATTATCGATGCATAA
ATAAACGAGATGCCGAGGTTGTGCGATGCCACACGATCCACGATACGCGATCCGCGATCCGTCGAGCTATGCTTTTATTTTTAAAACTTGTCCTT
TGATTATCGCAAGAACCGAACGATGACAACACGTTGGTGTCTCGCATTGCCGCATTTTGATGGTCCGGTCTGGCGGCTTTCGCACTCTGCTCCAA
TCTCCCAATCAAAGCACACACACCCGCTAAGTGATTTCCCTTCAAGATCACCAAATTGCATCAGTTTTTTTTAGCGGTACAGGCAGAGCGTGCC
TTGCATAACCAAGCTCCGTGCGCTGTGTGTCGCACCCATGATAAAGGCAAATCAAAAAAAAAAAAAACAAAAAAAAGAAAAAATAGAACTATCTAT
ACGATGGAGCCACTCGATCGAGTGGTCTATCGACCCCACCCCGTTCATAAATGCCTATGACTGTCATATAAAAATGACTCCAGCAATTCCAGCTA
TCTGCTGCGATCCCAATTAGCAATTAGAGCATTATCTCCCCCGTCACCACCCTTTACCACGTTACCACTGCAAAGAGTCGTTAAAGGTGTGTCGC
CGATTTATATGATATTGCCGATGGAGTCTGATACCTTGTAATTTGGAAAATCGCCGGATGGGCATATGTTGTCCCAAGTGATGTGCATTTGTAGA
TTCGTTAGATCGCTGGCATTGGTATGGGTTGAGCATTTAACGCCTGCTTTAGAACTTATAACGCATTGTGAGAGAGGTCTCAGGAAAAATAGGTG
TTACCTAATGAAAAGTGTGGATGCCTTTTAATTTACACGATTTACTCAGCAATTTGCACTTTAAAGTGGTGGGAAATCGAAGTCAAGCACTAAGA
TTCTTGAAGTACCACAAATTAGGTACATAAATAAAGCGCTTAATAGTTGTAAGTAGTTAAACCCTTTACAAGTTGGTATATGGGCTCACCTGCAA
AGTTGCTAATTTCTGCTGTTTCGACGAGAGCACCAACTAATTTCTTCGAAAAATGTGACATTTGCTTATCATTTAGCCTTGTATGTACATACAAG
TATTTATTCAATTAGCACACTATCGAGTAGATCATTAGTCGCATTATAGGATGGTTTCAACAGCGCAAAATTCCTACTCCTTAAATATTAAATCA
GTGAATACTACTATAGTAGGCCCAGTGTGTTCTGCCTTCAGCGACAAATTAAGGCCTGAACTAAAAAAAGAAACGACCCAGGCAGTGCCATTAAT
CAACGTCTTTGCCCTTTTCAGGATCAAATCTCGCCACAATGGAAAAATCCAGCTTAACGGAGAAGAATCACACCCAAGTGTACAATGACACAACG
AAGCCAAAGAAGCCCAAGCGTCGCGACAAGAGCGATCTGGGTCCGGATTTTGTGGCGCCCGACGGGGGATGGGGCTGGGTGGTCTGTCTGGCAGC
CGGTTTGAATAACGTAAGTGATATATAGCGTGGCCGAATTGCAGCAGTCTGGATGGTGCATAATAATCTCCCTATCCTCATCCTCACATTCCCGC
ACAGTTCTTCCTTTTCCCGGCTCTGCAGCAGTATGGCCTGATCTACAGGGTGCGGATGCAATCGCTGGGCTTCGATGCCAAGCAAACCACGACCA
TTGTGAACGTGGTGATGGCAATCTCCTCGCTAGTGGGTGAGTTTCACCTGGCCAACGTTCAATCGATTATGCATTTACTGATATATATATATATA
TACATTAAATTCTCCGTGCATAGGCATTGTCAATGGCGCCATGTTCCGGCGGTTCACATTCCGTCAGGTGGCCCTGACCGGCACCAGTCTGGCCT
TCCTGGGCGTCTTCTTGTCGGCCTTTTGCACCACCTTCTGGCAGTATATCATCTGTCTGTCGGCGATATTTGGTATCGGTTTGGGTCTTGCCATG
GCCGCCACCTCACTGGCGGTCAATACGTACTTCAAGCTGAAGAGGCGTCGTGCCACGGGTTTCTCGTGGACGATCACTGGCCTGGGACCCATATT
CTTTCCGCAGGTGTCTACCGTCCTGTTGGGCTACTATGGTGCCCAGGGCACCATTCTGATCTATGCTGGAATCGCCATGAATGCCATTCTCTGCG
CTTTGACCCTGCAACCCGTACTTTGGCATGTGAAGAAGCCCGAAAAACCAGTTCACAATACAATCGAGGGAATTGCCGAGACGGAGAAGCTGCAA
CCAGAACTTTTGGAGGCCAATGGCAATCTGTTGTCGCCCAGCAATGATCCGTGGAAGGATTACGAGTGCAAGTACTGTCAGTATCAGAAACGTTC
TAAGCGAGGCCTTTTCTCGTCCCAATACCTCTTCAATGTCGATGATCCCGAGAGGCCGGGGTACGAGATCACCGAGCCAGGAACTCCCATGTTGG
CTCGCGCCAATGACGGTTGGTTCGGGTCGAAGCTCTCCCTGACCTCGGAGAGCGCGGGAGGAGCTCGCTCTCGCACTCGTCAAGCTCTGATGCGT
CAGGTTTCATCCAGAAGTCGTGAGAATCTCGATAGACTGGAACAGAATCGTCATGACCAGGGTCCAGACACTCCATCCGCTGCGGCCTTGTACAA
GCCAAACTACTTCAATCGGGAGCGCGAGGATCTCGATCGCTATGCCAGCAAGACGAGCGTGTATTCTCGGCCTGGTCAGGATGAGCTGCTGCGCT
GCACCTGTGCAGAGGACAAGGCACTGTTGCAAAAGACAGCCGAATCGCTTCAGGTGAACCTGTTCAATAATTCGGCCGACAACACGGAGGCCGAG
GAGGAGGCCAAAAGGCGCATGACCTTCTTCCAGAAGGTGAGCAAGTTCTTTGATTTGGATCTACTGCGGGACTTTACATTTGTCAACCTGGCCGT
TGGCATGAGCATCATGATGTTTGGCGAGATGAACTTCTCGGTGCTGACACCATTCATTCTGAACAGCTTTGGGTACACGGATACACAGATCTCGC
TGGTGATGTCGCTGCTGGCCTGCATGGATATATCGGTGAGATTTCTCGCTCCGCTCGCCTTGGAGAAGGTGAAGCTGGATAACCGTGTGCTGTTT
GCCTTCGGCATCCTATGCATCGCCGTGGGCCGCGTGGTTGTGGCCTTTACCGACTCCTACGAGATCATGATCGGCGTCTTCCTGCTGATCGGCTT
TGGCAAGGCATTCCGCACCATCTTCTCACCGCTGATAATACCCAGTTACGTTCCGCTCAACCGCTTGCCAGCTGCATCTGGTCTGCAGCTCATCT
TCAACACAATATTCTCGTTCGCCATGGGCCCAATTCTTGGTGAGTTTAATGTTAATTAGATTGTGTCTGAAACGTAAATGACCTTTACTATTTTC
CTTAAAGGTATCTTGACGGAGGCCTACGGTTATGCAGCCACCATTCATACCATCAATGCACTCACCCTTTTGGCTTTACTCCTTTGGTTAGCTGA
GTCCGTGGTGCGCCGCATTTTGGGTATACCCTCCAAAGGATTGGGCCAATAGAAGAGGCATTCATACTAATCCGATTTGAAATTGCGACGAGTGT
GAGCTGAAAACCTTCGTCGGAACTGAACTACTTGCTATATGTCCATCCCAGTGTGCGAGATCATGGCTAACTTGGAGCTGTAGACATAACCTAGT
CCATACTTCCCGATTGATGTGTGCGAATAGTATTAATTGAGCGTAAAGATACCTAAGAAACATATCTCTTAACTAGCTCATAATCACCCATCGCT
ACATAAAATTTACGGTCCATTTTTTTTTTTAGCTTTTGATACTCGTACTAGAATAATTGAATGTACTTAGTGATACGTTATAAGTGTAATAATAT
TGTTCTGCAGTTGATAAAGAAATATATATATGTATATTAGTTAGAAAAAAGTTAATGCACTATTGGTAAGGTGACTTAATTGAAATACACCATAT

FIGURE SHEET 494

GGTTTGAACATGTGAGTCAGCATATTTATAAAATGGGAAATTGAACTACTTTTGTGTGCTTCGTTTATACATAAATGTAGTGATTAGAGGGTAGG
TTTAAAGGAAATGTTAAAGCATATCTCAATGTTTGGGGATGATTTCATGATGAGTTCATACTACATTTAGTATGCACTTTACTCAAAGATTACGT
AGAAGAAATAAATATTTACCAGAAATTCGAGGGCTTGTTCAATATTTGTCAAGGTTCTAATTAAGATATCGGCCAGTTAAAAATAAATACAATCT
CAAGTTTGTTTTGTTCTACAATATATGTGCAAATGCAGCTTGTTGAACTAGCTTATTAAGATTACTTACAATCTTTGTGTATGTAAAGTTAAAAA
CTGTGAGAAACTATTTTCAATAGCTATAGTCGGTGTTTTCCATTTGAGAACGATTTAATAAAGTTCATATAATAAATTTGCCCGTTGGTAGAATA
TGTGTAAACATTTTTATTTGCATATAAAGCTTAACAATAAACCAATAAATAGATAAGTAAATGTTGTGTACGTTTCTGGTTCGATATTGAATATT
TAAAATG
(SEQ ID NO: 910)

Exon: 1001..1382
Exon: 9332..9513
Exon: 9600..9726
Exon: 9809..11344
Exon: 11408..11547
Start ATG: 9349

Transcript No. : CT24172
TAAACACACCAACGAGCGGACGTACACGGAGCGAAAGAAGAAGTTGGCTACCACGAAAGAGTTATTGTTTGTTAGAAACACCAAGCGCAGCAGCA
GCAGCAGCAGTACAAATATTATTGTGTGCCGTCCGAAGAGAACAGCTGAGCCACACGCTGTTTTTAACGCTGTTCCGTTCTGCGGCACTTGCTG
TTTGTTATCCGTATCCGTCGTGTTTCGTCGTCGTATTTGAACTCTCTTTTTGTTACTGTGCATATATTTTTGAAATCTCTGTGCTGCACACAGCG
CAGGGGGAAAAGTGCTAGAATTAGCAGATCATCAAGACATCTGGCTAACCTGTGATTTCCAACACACCCGAAGGCAAATTGGCAACAAGTTACCA
CCGATCAAATCTCGCCACAATGGAAAAATCCAGCTTAACGGAGAAGAATCACACCCAAGTGTACAATGACACAACGAAGCCAAAGAAGCCCAAGC
GTCGCGACAAGAGCGATCTGGGTCCGGATTTTGTGGCGCCCGACGGGGGATGGGGCTGGGTGGTCTGTCTGGCAGCCGGTTTGAATAACTTCTTC
CTTTTCCCGGCTCTGCAGCAGTATGGCCTGATCTACAGGGTGCGGATGCAATCGCTGGGCTTCGATGCCAAGCAAACCACGACCATTGTGAACGT
GGTGATGGCAATCTCCTCGCTAGTGGGCATTGTCAATGGCGCCATGTTCCGGCGGTTCACATTCCGTCAGGTGGCCCTGACCGGCACCAGTCTGG
CCTTCCTGGGCGTCTTCTTGTCGGCCTTTTGCACCACCTTCTGGCAGTATATCATCTGTCTGTCGGCGATATTTGGTATCGGTTTGGGTCTTGCC
ATGGCCGCCACCTCACTGGCGGTCAATACGTACTTCAAGCTGAAGAGGCGTCGTGCCACGGGTTTCTCGTGGACGATCACTGGCCTGGGACCCAT
ATTCTTTCCGCAGGTGTCTACCGTCCTGTTGGGCTACTATGGTGCCCAGGGCACCATTCTGATCTATGCTGGAATCGCCATGAATGCCATTCTCT
GCGCTTTGACCCTGCAACCCGTACTTTGGCATGTGAAGAAGCCCGAAAAACCAGTTCACAATACAATCGAGGGAATTGCCGAGACGGAGAAGCTG
CAACCAGAACTTTTGGAGGCCAATGGCAATCTGTTGTCGCCCAGCAATGATCCGTGGAAGGATTACGAGTGCAAGTACTGTCAGTATCAGAAACG
TTCTAAGCGAGGCCTTTTCTCGTCCCAATACCTCTTCAATGTCGATGATCCCGAGAGGCCGGGGTACGAGATCACCGAGCCAGGAACTCCCATGT
TGGCTCGCGCCAATGACGGTTGGTTCGGGTCGAAGCTCTCCCTGACCTCGGAGAGCGCGGGAGGAGCTCGCTCTCGCACTCGTCAAGCTCTGATG
CGTCAGGTTTCATCCAGAAGTCGTGAGAATCTCGATAGACTGGAACAGAATCGTCATGACCAGGGTCCAGACACTCCATCCGCTGCGGCCTTGTA
CAAGCCAAACTACTTCAATCGGGAGCGCGAGGATCTCGATCGCTATGCCAGCAAGACGAGCGTGTATTCTCGGCCTGGTCAGGATGAGCTGCTGC
GCTGCACCTGTGCAGAGGACAAGGCACTGTTGCAAAAGACAGCCGAATCGCTTCAGGTGAACCTGTTCAATAATTCGGCCGACAACACGGAGGCC
GAGGAGGAGGCCAAAAGGCGCATGACCTTCTTCCAGAAGGTGAGCAAGTTCTTTGATTTGGATCTACTGCGGGACTTTACATTTGTCAACCTGGC
CGTTGGCATGAGCATCATGATGTTTGGCGAGATGAACTTCTCGGTGCTGACACCATTCATTCTGAACAGCTTTGGGTACACGGATACACAGATCT
CGCTGGTGATGTCGCTGCTGGCCTGCATGGATATATCGGTGAGATTTCTCGCTCCGCTCGCCTTGGAGAAGGTGAAGCTGGATAACCGTGTGCTG
TTTGCCTTCGGCATCCTATGCATCGCCGTGGGCCGCGTGGTTGTGGCCTTTACCGACTCCTACGAGATCATGATCGGCGTCTTCCTGCTGATCGG
CTTTGGCAAGGCATTCCGCACCATCTTCTCACCGCTGATAATACCCAGTTACGTTCCGCTCAACCGCTTGCCAGCTGCATCTGGTCTGCAGCTCA
TCTTCAACACAATATTCTCGTTCGCCATGGGCCCAATTCTTGGTATCTTGACGGAGGCCTACGGTTATGCAGCCACCATTCATACCATCAATGCA
CTCACCCTTTTGGCTTTACTCCTTTGGTTAGCTGAGTCCGTGGTGCGCCGCATTTTGGGTATACCCTCCAAAGGATTGGGCCAATAG
(SEQ ID NO: 911)

Start ATG: 400

MEKSSLTEKNHTQVYNDTTKPKKPKRRDKSDLGPDFVAPDGGWGWVVCLAAGLNNFFLFPALQQYGLIYRVRMQSLGFDAKQTTTIVNVVMAISS
LVGIVNGAMFRRFTFRQVALTGTSLAFLGVFLSAFCTTFWQYIICLSAIFGIGLGLAMAATSLAVNTYFKLKRRRATGFSWTITGLGPIFFPQVS
TVLLGYYGAQGTILIYAGIAMNAILCALTLQPVLWHVKKPEKPVHNTIEGIAETEKLQPELLEANGNLLSPSNDPWKDYECKYCQYQKRSKRGLF
SSQYLFNVDDPERPGYEITEPGTPMLARANDGWFGSKLSLTSESAGGARSRTRQALMRQVSSRSRENLDRLEQNRHDQGPDTPSAAALYKPNYFN
REREDLDRYASKTSVYSRPGQDELLRCTCAEDKALLQKTAESLQVNLFNNSADNTEAEEEAKRRMTFFQKVSKFFDLDLLRDFTFVNLAVGMSIM
MFGEMNFSVLTPFILNSFGYTDTQISLVMSLLACMDISVRFLAPLALEKVKLDNRVLFAFGILCIAVGRVVVAFTDSYEIMIGVFLLIGFGKAFR
TIFSPLIIPSYVPLNRLPAASGLQLIFNTIFSFAMGPILGILTEAYGYAATIHTINALTLLALLLWLAESVVRRILGIPSKGLGQ*
(SEQ ID NO: 912)

Name: monocarboxylic acid transporter; putative
Classification: transporter
Gene Symbol: BcDNA:LD28120
FlyBase ID: FBgn0028469

Celera Sequence No. : 142000013384504
TCTTCAGTTCGTTTCGTGTCTTTGAACTTCCCAGCTGAACCCTAAAGCTATGGTTTCTTATTTTACATCAGGCTGCCTGATGCTAACTTATGAAA
TACTACGTGAGCATTGACGAGTGCGTCCTTGGAAGAGCATTCCTCGGCGGCATGGCATCCTCCGCCTAACCGCAGAGATTCGCGATGGCCTGAGC
CGCATTAGCGGCTGCCACCTGTGGAGCGTCCTCTGCCGGAATGCGTTTGCGTCGGAATAGAATCACATGCGGCTCCGGCGCGTGGACCATGTAGT
GCACCCAGCCGGGGCTCTGCTGCACGCCCAGGTTGCGCCACTCCGTCTCGGTCATCAGATGAGCCTTCGGCACATGTTTGGCCAAATCCGGTGGC
AAGATAACATGCCTGCAGGGAGGGAAAGTGGTTTGTGTGTAAACAAACAGTTCACGGATGCTGAAACGCAAGTTGAACGTACCTGTATTCAAAGT
TGTCGTCGAAGTACTTCTCTGAGTATTGAATTTGATCGGCCGGCATTGCGAAAAGCCAGAAAACCTGAGGTAAATTAAGCAATTTTACCAAAATA
GGTCAATAAATTCAGATAGATATGCCACAACTGATTCGATTCTAAATACTATTGTTATCGCTGCACGTATCGAACATAAAGTTATCGATTTGGTT
ATCAGCTGTCCAGTTAACAGCACCTTTGGCGGTAAACTCAAATGTACTGTTTTTAATGGCACGATCTTAGCGGGCTTTAATATATTGAACATAAA
CTTTTTTCTGTATAACAATATTTTTGCAATGTTTAAAGCCATTTTAAAGCCATTTTGTTAAAAAAACGAGTACTTTGTAAAAAGATGCTGTTAGA AAATGTTAACATATTTAGCGAATGAAAAACTCAATTGGATAATATGTGATTTCCAGTGTGACCGGAACTCGCAGGCTCGCACATTTTCCAAATGC
AATCGGCAATTTCTCCGTTACTCGCCCATGGCCACATTTGTGCATGTGCGTTTGAGGTTCCTTTCCTTTTTATATAAGCCCCTCGTCTCTTGCCA
ACAAACCAACAACAACAACAACCAGCCAGGCCAGCGGGCAACAACAACGCACAACAACGCGTATAAATAAACGTGAACGCATGTACTTAATATTA
GCATAGAGTTGTCGCCTGCGTGCATTTCATATACATAACATAACATCCACTTACTCCCATGACAACGGGACTTTAGACAGTAACGGTGGAGCAGC
TAGAAGAAGAGGAAAGGCGAAGTAGAACGGGAACAAGAAGAAAAAGCAGTGGAAGAGGTGAGGACGATACGTAAATACAGTCAAACTTCCATAAG
TAGATACGACTTTACTACTACAATAAAAAGTGTCCTTTAGTGATGAAGAAAATGGGTTCTAAGAACCTAAAACCTTTATGTATATGTACTCCCTA
TTGTCGCTTAATGAATTTACCGTTACGGTATGCTAGTAAATAAATGCATACAATGTACATATGTAGATACATAGGCACAGCAAAACCACCTATAA
ATTCGATTGATTTTATGAAGTTCTAGTTGAGGAAGTTTGACTGTATGTATGCGCGCATTGGTAAATACGAGCAGACCGCAATTAGCAAATATTTT
TCAGTCCAGCAGGTATCACTCACCACGTACCGCCCAAAGGTCCCAATGCTGGCGTAGAGAAGCCGAAACACCTGCTGCTGCCAGTGGAAAAGCGG
GAGGAGCTGCTCCAAACTGCCCAGGTGACATCCAATCATTTAGAGGCGACGCACCTGCCGCCTTGAGGAACTGGTCGCCACGCAGGAGGACACGG
ATACGGCAACGGTTACGGACTCGTTTCCGCAGTAGCGGGCACCATGAACGCCAGCCTCATCTATGAGATACTTATGTATCTGAACTCGTTCTACT
TTGGCATGTACGCCGCCTTCGAAGTGGGCGTGGGCGTTCTTAAGGCGATTAATCTAAACTACGGCGAGAACGCGTTGTCCCGGGAGGCCAGCATC
CTGCTCTCACTGTGCATCATCGAGACCGTGCGCATTGTCTTCGGGCGGAAGAGCAGTCTAAGCGATCGTGGTGAGTAATCCCCATGATCCCCATG
TTACTGCAAGGGTGGGAAAAGTCCACCGGCAGCGATGATGACATGGCGAAATTATTTGTTTGCCCGGTCACAATGCCCATTTCATGCCATCCCCC
TACCTCCGGGGCCATAACCCATAAACGTTTGGACGGGCATACATACATATATGTATGATGTAGCCCACTCGGCGTATGCGTAATTATGGTCATCA
CCCCGGATGAAAACACGCGTTTTATGGTGGCAGGGGAAAGGCGCCCTTCTGGCACATTAAGCAATATGCAAAGGAAATCTATCAAAGCGAATCAT
CGAAATGAGTTATTGGAAAAGCAATTGGAGCTGTTAATATTAATTATCGCAATGTGTAAACATGAAATTATTAGTATAATACTTTAAAACACTGA
ATCACTTTCAATCGAATACACTTAATTATAAACAAGTAGACGAACTATACGATTTTCCGTGCATCTGTAGCTAACATTTTCCTTGTTTTTCTCTC
TTTGCAGGCTGGCAAGCAACCGCATCCGTAATATTAACACTGCCCAGTCTTGCTATTGTTATCTACTTGTGTTGTTTTCAAACCTTTGTTCTCAA
ACTCGAAATTATTCTGAGTGCCTTAATGATCACCCTACAAGGTGCTGAACTAGTCTACGCCAGCATATTCATTTGTACAATGTGTCGCCCCGTCA
CATACACCTAGCAGTTGATAAGCCGCGTTGCCGCCGCCACGTCAACGACCAAGATCGAGATCAAGACCAAGCCAGCACTAACACTCCCACCTGGA
GGAGAAGGAGTAGAAGCATCCACAGCCGAGCGACGACTACGACGAAGACGAAACACTTTCCTCTGGCAATTTCACATCAAACGATTCGCCAAGGC
CTCAAAACTAAGCCACTTAAATGCACACTAAGCCACCGCACATAAAAACAAAACAAAAAATCTAGATCCTACTAGACCTCCTAGGAATCCGTGCC
AAGACAACCCGATAACATACCCAATGGCTGGCAGTTGAGGAGGACTTTCAACAAGGTACGTGAACCTTTATAAACTTATATAATCCGCACAGATC
ATTCGCGCCCGCGGAAATCACATCGCAGCGAAACACGACGCGTCCGATTCTATCAAAAGCAAAGCTGCATTTAATTTGCATTTCTTGGTTGCATT
CTTTTGCCCGGCCTTTGTGGCGTTGCCTCCCTGCTGGCGCAGTTGCTCCTCGGACCCGCTCGGTTCTGGTATTTTTATACGGCTCTGATGGTCTA
AAATTATATGCGAACTGCACGGCTCGTGCAACACCGCTGCTGTCCCCTAGGTGCAATGTACACTTCTAATTTGAATGTAATATACACGGCCCACT
GCGGGCAAGTTAGCCTGACTGTAATGGCCAAGATGAGAGGGCTCTCCGTTTGGTCTTTGGTCTAGTGAACATGCCCTGTACGATTCACAGGAGAG
AGATTCACGGGACTTTAGCGAGGCATAACGCTTTGAGTTTTTAAAAATAATTAAAATTCCAACAATGGTTTTCATATATTCACCCTAAACCTATC
CTGAATTTCAAGGTAACCATTTAATGGCCCTGGGCCCTGTAGAGCATAACGCCCAGGGAGTTTTTAGTAGTTTTTTCCCCCCAACTAGCCGCCAG
TGAAATCATTCTCCCCCACATTTCTAGGCAGGCGATCTGCCGGCCAATGCTGACCCAAACAGCGAGCAGAGAAAACAAA
(SEQ ID NO: 913)

Exon: 1001..1292
Exon: 1620..2065
Exon: 2573..2784
Start ATG: 1849

Transcript No. : CT24260
TTTGAGGTTCCTTTCCTTTTTATATAAGCCCCTCGTCTCTTGCCAACAAACCAACAACAACAACAACCAGCCAGGCCAGCGGGCAACAACAACGC
ACAACAACGCGTATAAATAAACGTGAACGCATGTACTTAATATTAGCATAGAGTTGTCGCCTGCGTGCATTTCATATACATAACATAACATCCAC
TTACTCCCATGACAACGGGACTTTAGACAGTAACGGTGGAGCAGCTAGAAGAAGAGGAAAGGCGAAGTAGAACGGGAACAAGAAGAAAAAGCAGT
GGAAGAGTCCAGCAGGTATCACTCACCACGTACCGCCCAAAGGTCCCAATGCTGGCGTAGAGAAGCCGAAACACCTGCTGCTGCCAGTGGAAAAG
CGGGAGGAGCTGCTCCAAACTGCCCAGGTGACATCCAATCATTTAGAGGCGACGCACCTGCCGCCTTGAGGAACTGGTCGCCACGCAGGAGGACA
CGGATACGGCAACGGTTACGGACTCGTTTCCGCAGTAGCGGGCACCATGAACGCCAGCCTCATCTATGAGATACTTATGTATCTGAACTCGTTCT
ACTTTGGCATGTACGCCGCCTTCGAAGTGGGCGTGGGCGTTCTTAAGGCGATTAATCTAAACTACGGCGAGAACGCGTTGTCCCGGGAGGCCAGC
ATCCTGCTCTCACTGTGCATCATCGAGACCGTGCGCATTGTCTTCGGGCGGAAGAGCAGTCTAAGCGATCGTGGCTGGCAAGCAACCGCATCCGT
AATATTAACACTGCCCAGTCTTGCTATTGTTATCTACTTGTGTTGTTTTCAAACCTTTGTTCTCAAACTCGAAATTATTCTGAGTGCCTTAATGA
TCACCCTACAAGGTGCTGAACTAGTCTACGCCAGCATATTCATTTGTACAATGTGTCGCCCCGTCACATACACCTAGCAGTTGATAAGCCGCGTT
(SEQ ID NO: 914)

Start ATG: 522

MNASLIYEILMYLNSFYFGMYAAFEVGVGVLKAINLNYGENALSREASILLSLCIIETVRIVFGRKSSLSDRGWQATASVILTLPSLAIVIYLCC
FQTFVLKLEIILSALMITLQGAELVYASIFICTMCRPVTYT*
(SEQ ID NO: 915)

Celera Sequence No. : 142000013384474
GCACATACAGACAAACAGGCGACATTTGAAGAAATAAAAAGTGAATAATAACCAATGCGTGGCCGTTTAGAGCATTTTACATTTAAATCTACGAT
TCGGCTTGTTCATTTTGCGGCCCCTCCGCCCCTTGTTGTCCTTGTCCTTGCGGATTTCGCGCACCAGTGTGTAAAATGCATCGTCCACGCCCATG
CGCGTCTTGGCGGATGTCTCAATGTATGGAATGCCGTACTGTTTGGCCACCTGAGAACAACCATAATTAACGGAATGTTCGCTCGGAACTCTGAA
GGCCGGTACTCACCTCTCTTGCCTGCTCGTTGTTAACGTTCCACGAGGCCAGATCACATTTGTTGCCCACCAGCACCATGGGCACCTCTTCGGCA
TCCTTTACGCGCTTGATCTGCTCACGGTAGGTGCCGATATCCTCGAAGGACTTCGCACTGTTGACGGCAAAGACCAGCAGGAATCCCTCGCCAGT
CCGCATATACTGATCCCGCATGGCCGAGTACTCCTCTTGGCCGGCGGTGTCCAGGATGTCCAGCAGGCAGGTCTCTCCATCTGCAGGGGAATATA
AAATGCATTTGAATATCGCAACTTCTTAAGGTCTCTTCTAGTATAAACGGGAAACCAAACCAGCGAAAGGGTGCAGAAATCTCTAGAGTATTTGG
ACCTGTGCAGCCCTAGCTTTGCCAGATCTAAGTACATATAACTCACCGATAACCACTTGCTTTCGGTAAGAGTCCTCGATTGTGGGGTCGTACTC
GTCCACGAAATGGTTCTGGATTAGCTGGATGGTGAGCGCGGACTTGCCCACGCCTCCGGCTCCAACGACGACCAGTTTGTATTCCGTCATTTGGC
TGTGGCGTCCGTTTTCGATTTGCCGTAGTCAAATGTCACAGTAACAGTCTCTTTCTCGCGATCGATGCTTACTCTCTTGTGAAGCGCCCGCAGAT
GCAGTCTCTCTCTCCGTACGCTTGTTGCGTGTGTTTGTGTGGGTGACTGTGCGTGTATGGGCTGCAAGTGGAGTAAATTATTAATTAAGATTGAT TAAAATAAATTAAACGCATAATTAGGCAGGAATTAATGCACGTCACTGAGTCACTGTGACTAGGCGCTTACTCGCACAAACACACACGCACCACT
GCATGCACACAGCCAGACGGGCAACACAAAAAAAAATGGGAAAAAGAGATCAATGACTCAAACTAAAATTAAAACCCATTCGCTCAATGCAAATT
AGTTAGTCTCCCCCATAGCCGAGTTGTTAACTAGGTGAATTTGCTAATTCGGCGGCGTTGTTTTTAGCCCTTTTCTTTATTATTTTTCTTTTGCC
TGCCGGGGCTGCGGACCTTCTTTGTTGCTGCCTCTTCAGCTAGCTCCTCCTTGTTTTTCCGCTCCGCTCCTCTCTATCAATACTCTGCCTCTCTC
TTCTCGCGCGCGGCGCAGTTGCTGGGCACGTTTCACGTCACTTTCGCGGCTAACGGTGCGACAGGCGGTACTCCTCGATGGCACCAATTTAATTG
CCGTGCGGTAATTGCAATTAACAGCGCAGGAAAACAATAAATCCGTATGTGAAATGAAGATGAAATCTAGGCTGTACGTAGCTGTGAAGATACTA
GAGCTGGCACCAAGCCGATGGCACTATCGATAGCGATGGCTGCATTCTGGCCGGCACCATCGATGGACTTGCAATAGCGATTGCTATATGAAAAC
TAATCTAAAGAGGTGGATGCACTTCAGTCGACTCTCTATAATTTGCTTAAACTAATAAATGATTTGATCAATACAGCTTTCTGTAAAAACTGGCA
GACGCTTTCTGCTTTTAATAATTGTTAATTTAAGTTCAACGGGCTGGCATCACCGTTTCTTAGCACGGACTCAAGCCTGAGTCTATTATTTCAAC
CACCACTGTAACGAAAACAGCATGGACAGATTGAAATTCAATAATTTGGTAAATAAACGATTTTATTTAAAATTATAGAGTTTTAATTAAAAAGA
ACTTTTACAGGTGATATCCAACAAGAAGGTCATTCAAAAGGCACGCGCCCAGACCATCGCCAAAATCGTACAAAAGCTGCGAAAGACAAAAGAGG
CTCTGGCCAAAAATCCAGACAGTGAAAAGGAAAAGATTCGTTTACGCAAGAACACAGAATGCCTGGCCCAGTTGAAGGCTCTAAAATATATGGAT
ATGGTACGCCAGTCGCTCCTGCAGGAGGGCACAAATCCCAATGCGGTGATTGCTAACGAGCGCTCCACGCCGGATGAACTGGGCATTGCCATGCT
GCGGCTAAACAAATTGATGCACGGACTGGTGGACAAGTTTGTGGAAACCTTGAAGCTGAGCACCACCGATAAGGAGGCCAAGTGGCGTGAGGAGA
TCCTAGAGACGAGCAAGCGAAGGGCCAAAATAGAACGCACTGAGGAGCGGAAGAGGAAGCGCAAGGAGCTGAAGGAGCAGAAGGCCCAAACCAAA
AACCGACTGGAGTGGTTAGAGCAGAACAAAGTGGTGGATGCAGATGTTAATGGAGCAACTGCGGAAACGCCCACTCTTCAAGTCAGCAAAGTAAA
TGATCAGGAAATACCACAGTCTTTTGCAAAAACTGAAAATTCTCCAGTTCTCAAAGTCAAAAAGGAAAAGACACCTAAAACACCAGCCAAAAAAG
AAAGAAACCTTCAGAAAAAACAAGCTTTTGATGAGCAGATCAACCCGGAGATAACTAAGCTCAGTTCCAAAAAGCAGAATTTAAATACAATCAAG
GAGAATAATGCAGAGCCACAACTAGAAGGCAGACCGAAAGAATCTAAGCCAAAACCCTTCGAGAAAAAACCAGCCAGAGAGCAGAAGCCTAAGCC
ACGATTAGAAAGGCAGCCAAGTATCGATGAAGAAGAACCACAACTTGACAATAATCGTCCCACACATGTCGTTGATCCCTTCTTCATTACGGAAT
CAGGCCAGCCCTACTTGTCCAGCGCCGTGGTTCTTTCCGGGGACAATGACAGCGAAGCTGATGAGGAACAGGCACCGCCGCCAGTCAAAAGGTTC
CGCAATGAGGATCGACGGTCGAACACATATCGGGAGAAACCGGAAAGACAGCCAGAGTTCAAAGCGAGAAAGCCAACTGATGATCGTCATCCCTC
CTGGCTGGCTAAGCAACAGCAGAAACCAATCATTGGTGATTTTAGAGGCAAGAAGATTACATTCGGCGACGACGGCCAGGCGGCGGAAATTATTG
CTCCAAGTATCAATCAATTAACCGCTACTGCTGCTCCTTTGCCCACCGATGGCATGCACCCGTCTTGGGTGGCCAAACAGAAGTTTAAGCCGAAA
ATTGCCGCGTTTCAGGGCACAAAGATTAAGTTTGACGAAGATTAAAGATGATGTCAATGGTATTTTGTTGTTTTAATAACTAAATAACTGCAGCT
TTGCTGCTCACACGCCAACTTTGGGCACATAGTGACCACGAATCTTGTCCTCGTTGCGCAGCTTGTCCACGTTGACATCGGGGAACTGGCGACGC
AGCACATCCAGATCGAAATTGGGGTTGCGACGCAGGATCATCATGACTTCGTTGCGGGAGCGGCTGCAAAATAACAATTTTTATTGAGATATCCC
ATTTAACTAAGGGCAACATACTTCTTGGCCTTGCGCTTGGCATTGTAGAGTTTCTCCCTGTACTTTAAGAGGAATCTGTTCACAGCTCTGCCGCC
GTAGCCAATGTTGCGGGATTTAATCCATTTGAGGTTCATGAAGGGCGGCAGGGCGTGTTCGCATGCTTTGTATGAGACCTGCAGGCCAAATGCGT
TCTTCACCGCCTTCTGGGGCCGTTCACCCGTTTCACCTGTTTCCAGCAGGTGATACGCCTTGTTCCGCTCCCTCACTACTGTCTCCAGGTTTTCC
ATGGAGATTTTCACCTGCAATTCTAAAGTTTTAGAAAAGGATCTCCACCATCAAATATCGCCCACCTTATCGATGCGCTCCGGACTAGGGAAGAC
TTCCATTTTGTCATTGCACTCGTGCTCCATGGTCAGCAGCATGTTGCGCTCCTTGAGGAGCACGAACCACAGCTGGTGCAGCTCCTTGTTGGACT
TGATACGCAGCTCCTCCGTCCGCCAGGCGCGGCCCACCTTCACCTCATTCTCGCTCCAGTTCTTCTTGTCGTCGAAGAACTCCATAAGATCCCGG
CGAACAGCGGAAGTGTGCATTTGCATCGGCATTTGAACATGCGGCGTTTGCAGGGCAGCCGCACTACATATTACATAAAAACAAAGGCGCGTTTA
TATCGGTTACTCTGTGTAAAAGTCGGATTTGTGAAAGAGAACGGACCTGCACGACTGCCATGGCTGCTTGGGAGCTGCCAAAAAGCTCCTGACTG
TCGCATTTCCCACAGTT
(SEQ ID NO: 916)

Exon: 1001..1722
Exon: 1787..1948
Exon: 2006..3387
Start ATG: 1922

Transcript No. : CT24354
GCGTGTATGGGCTGCAAGTGGAGTAAATTATTAATTAAGATTGATTAAAATAAATTAAACGCATAATTAGGCAGGAATTAATGCACGTCACTGAG
TCACTGTGACTAGGCGCTTACTCGCACAAACACACACGCACCACTGCATGCACACAGCCAGACGGGCAACACAAAAAAAAATGGGAAAAAGAGAT
CAATGACTCAAACTAAAATTAAAACCCATTCGCTCAATGCAAATTAGTTAGTCTCCCCCATAGCCGAGTTGTTAACTAGGTGAATTTGCTAATTC
GGCGGCGTTGTTTTTAGCCCTTTTCTTTATTATTTTTCTTTTGCCTGCCGGGGCTGCGGACCTTCTTTGTTGCTGCCTCTTCAGCTAGCTCCTCC
TTGTTTTTCCGCTCCGCTCCTCTCTATCAATACTCTGCCTCTCTCTTCTCGCGCGCGGCGCAGTTGCTGGGCACGTTTCACGTCACTTTCGCGGC
TAACGGTGCGACAGGCGGTACTCCTCGATGGCACCAATTTAATTGCCGTGCGGTAATTGCAATTAACAGCGCAGGAAAACAATAAATCCGTATGT
GAAATGAAGATGAAATCTAGGCTGTACGTAGCTGTGAAGATACTAGAGCTGGCACCAAGCCGATGGCACTATCGATAGCGATGGCTGCATTCTGG
CCGGCACCATCGATGGACTTGCAATAGCGATTGCTATATGAAAACTAATCTAAAGAGCTTTCTGTAAAAACTGGCAGACGCTTTCTGCTTTTAAT
AATTGTTAATTTAAGTTCAACGGGCTGGCATCACCGTTTCTTAGCACGGACTCAAGCCTGAGTCTATTATTTCAACCACCACTGTAACGAAAACA
GCATGGACAGATTGAAATTCAATAATTTGGTGATATCCAACAAGAAGGTCATTCAAAAGGCACGCGCCCAGACCATCGCCAAAATCGTACAAAAG
CTGCGAAAGACAAAAGAGGCTCTGGCCAAAAATCCAGACAGTGAAAAGGAAAAGATTCGTTTACGCAAGAACACAGAATGCCTGGCCCAGTTGAA
GGCTCTAAAATATATGGATATGGTACGCCAGTCGCTCCTGCAGGAGGGCACAAATCCCAATGCGGTGATTGCTAACGAGCGCTCCACGCCGGATG
AACTGGGCATTGCCATGCTGCGGCTAAACAAATTGATGCACGGACTGGTGGACAAGTTTGTGGAAACCTTGAAGCTGAGCACCACCGATAAGGAG
GCCAAGTGGCGTGAGGAGATCCTAGAGACGAGCAAGCGAAGGGCCAAAATAGAACGCACTGAGGAGCGGAAGAGGAAGCGCAAGGAGCTGAAGGA
GCAGAAGGCCCAAACCAAAAACCGACTGGAGTGGTTAGAGCAGAACAAAGTGGTGGATGCAGATGTTAATGGAGCAACTGCGGAAACGCCCACTC
TTCAAGTCAGCAAAGTAAATGATCAGGAAATACCACAGTCTTTTGCAAAAACTGAAAATTCTCCAGTTCTCAAAGTCAAAAAGGAAAAGACACCT
AAAACACCAGCCAAAAAAGAAAGAAACCTTCAGAAAAAACAAGCTTTTGATGAGCAGATCAACCCGGAGATAACTAAGCTCAGTTCCAAAAAGCA
GAATTTAAATACAATCAAGGAGAATAATGCAGAGCCACAACTAGAAGGCAGACCGAAAGAATCTAAGCCAAAACCCTTCGAGAAAAAACCAGCCA
GAGAGCAGAAGCCTAAGCCACGATTAGAAAGGCAGCCAAGTATCGATGAAGAAGAACCACAACTTGACAATAATCGTCCCACACATGTCGTTGAT
CCCTTCTTCATTACGGAATCAGGCCAGCCCTACTTGTCCAGCGCCGTGGTTCTTTCCGGGGACAATGACAGCGAAGCTGATGAGGAACAGGCACC
GCCGCCAGTCAAAAGGTTCCGCAATGAGGATCGACGGTCGAACACATATCGGGAGAAACCGGAAAGACAGCCAGAGTTCAAAGCGAGAAAGCCAA
CTGATGATCGTCATCCCTCCTGGCTGGCTAAGCAACAGCAGAAACCAATCATTGGTGATTTTAGAGGCAAGAAGATTACATTCGGCGACGACGGC
CAGGCGGCGGAAATTATTGCTCCAAGTATCAATCAATTAACCGCTACTGCTGCTCCTTTGCCCACCGATGGCATGCACCCGTCTTGGGTGGCCAA
ACAGAAGTTTAAGCCGAAAATTGCCGCGTTTCAGGGCACAAAGATTAAGTTTGACGAAGATTAAAGATGATGTCAATGGTA
(SEQ ID NO: 917)

Start ATG: 858

FIGURE SHEET 497

MDRLKFNNLVISNKKVIQKARAQTIAKIVQKLRKTKEALAKNPDSEKEKIRLRKNTECLAQLKALKYMDMVRQSLLQEGTNPNAVIANERSTPDE
LGIAMLRLNKLMHGLVDKFVETLKLSTTDKEAKWREEILETSKRRAKIERTEERKRKRKELKEQKAQTKNRLEWLEQNKVVDADVNGATAETPTL
QVSKVNDQEIPQSFAKTENSPVLKVKKEKTPKTPAKKERNLQKKQAFDEQINPEITKLSSKKQNLNTIKENNAEPQLEGRPKESKPKPFEKKPAR
EQKPKPRLERQPSIDEEEPQLDNNRPTHVVDPFFITESGQPYLSSAVVLSGDNDSEADEEQAPPPVKRFRNEDRRSNTYREKPERQPEFKARKPT
DDRHPSWLAKQQQKPIIGDFRGKKITFGDDGQAAEIIAPSINQLTATAAPLPTDGMHPSWVAKQKFKPKIAAFQGTKIKFDED*
(SEQ ID NO: 918)

Classification: known_flybase_gene
Gene Symbol: Rlb1
FlyBase ID: FBgn0014022

Celera Sequence No. : 142000013384474
TTTATTGAGATATCCCATTTAACTAAGGGCAACATACTTCTTGGCCTTGCGCTTGGCATTGTAGAGTTTCTCCCTGTACTTTAAGAGGAATCTGT
TCACAGCTCTGCCGCCGTAGCCAATGTTGCGGGATTTAATCCATTTGAGGTTCATGAAGGGCGGCAGGGCGTGTTCGCATGCTTTGTATGAGACC
TGCAGGCCAAATGCGTTCTTCACCGCCTTCTGGGGCCGTTCACCCGTTTCACCTGTTTCCAGCAGGTGATACGCCTTGTTCCGCTCCCTCACTAC
TGTCTCCAGGTTTTCCATGGAGATTTTCACCTGCAATTCTAAAGTTTTAGAAAAGGATCTCCACCATCAAATATCGCCCACCTTATCGATGCGCT
CCGGACTAGGGAAGACTTCCATTTTGTCATTGCACTCGTGCTCCATGGTCAGCAGCATGTTGCGCTCCTTGAGGAGCACGAACCACAGCTGGTGC
AGCTCCTTGTTGGACTTGATACGCAGCTCCTCCGTCCGCCAGGCGCGGCCCACCTTCACCTCATTCTCGCTCCAGTTCTTCTTGTCGTCGAAGAA
CTCCATAAGATCCCGGCGAACAGCGGAAGTGTGCATTTGCATCGGCATTTGAACATGCGGCGTTTGCAGGGCAGCCGCACTACATATTACATAAA
AACAAAGGCGCGTTTATATCGGTTACTCTGTGTAAAAGTCGGATTTGTGAAAGAGAACGGACCTGCACGACTGCCATGGCTGCTTGGGAGCTGCC
AAAAAGCTCCTGACTGTCGCATTTCCCACAGTTTTTGCCAAATTTAAACATTTATTAACGCCGAAGACATTTTTTCGACCGAACAAAACAGCTG
AAGCAATAACAATCGATACTTTTTTGTATCGATTTATTGGATTGCGTGCGTACTACATTTTTAGCCGGGCTTTACTCCATTTCAGGGCTGCCATG
CATTTCAACTGAAATTAGTCGATAGTATAATTTCAGCATCGACTTGTTGGCCAGCTCTAGTTGCGCTTCGCTCAGTGCTAATGAAAAATCGAATT
TTTCGCTTCAAATCGACTGAAGTTTACACGGGCTAAAGTATTACAGAAGTTTGGCTCAAGCCATTACACAACATGCAATAAGTAAATGTAAGTGA
AGTGGCCACTCCCCGAAAAAAACAACGCGCTGCACTGTCATCTTCTCTGTTCCATCCAATCCAATTTGTATGCCAAGGAACGCCAACTTAATGTT
TGGCTGTGTGCATGCATGTGTGATTGTGTGCTGGTGTTTGTGGGTTTCAGTACACAAATTTAAATTGATAAAACTCGACAAAGGCAGCGGTTCTG
AATTGCAGCGAGTGCAGGGAATGCACTGCCAAGTGCCTGTTAATTGTGCATTTATCACAGCGAATTCAAGCAATTTGCACCTCGAAATGGGCATT
CAAAAACAAATTCATTGAAGAGTAACGCCAGGATGAAAAAAAAAAAAACAAATGTAGAACGGTATAGTAACAGGACAGTGTTGCCGAGCTGCTCC
AAGTTCCCCGGTACTATTGCCGTGCAGCGCAGTGTAGCGTACATAAATATTTATCTCACTGCCTTATCAGGCAGCATTATTGTTGAAGCGACTGT
GTATCTGTGGGCATATTAATTGTTTGTTTGTCTGCTCTTAGCAAGTGTTATATAAAGTGCAGAACATCATTGAGTTAAAAGGTCAGCGAGTGAAT
TGATTGATCAATTTGGCAAGGGGAAGGCGCAATGTGGGGGCTACGGAGTAACTTGTAGGGTTTTCTTCGCTCGGCTTTCGTGCTTTTATCATTTC
CCCTTTCCCACTTTTCGAACAACTTTTCTGCTCACGGTGAACGCCCAAATAAAAAAAAACACAAACAAGTCTTCTTGTTTGTACTGTCGCCATGC
GCGCGTGTGTGTGAGTGCTTCGGCTTTTTGTGACCAGGGGTTAATTTAACGGTGTCGCCTTAATTATCCGGGTTCTGCATATTCCTCCGGTGTTT
GCTTTCTCCGGACTTGTGCTGCCACTTGTTGCCCCTGTTAACGGCGCTGTTAGCTGCAATCCGAATCCCCCGGTTTCGTCGCCATATCGTGCGAT
AACCTTTCATTTGCCAATCGGTTGATTATCATGTTCTTAATGAAAGTAGCAACAAATAGCTGAATTTTCGCTTGCCCAAACTTACTCAGCGATGT
TTTAGAGGGGACCCTCATCACTACTCCTACAGTTTTTAGTTTGCGACGCCCATTGGTGATAAATACTTGTGTACATACATACAACATGTGATTAT
TTTTATGGAATGTGTTTATCTGGAACCCTCTCTATATGCGTCAACACATAATTGCACATGTTTAAATTTCCCGAAAATAAAATGTATATACAATG
CCTGCAGCTATAGCTGCTGTCATTGACTTTACTTTCATTTTAGCAGTGTAAGTTTTAAATTTTGTTTCCTCCCATCCAAGATATGAAACTGTAAC
TATGAAAACTCACTCCTGAGCTGCTCCGAAAATATCATGAATACGACAATTATGTGCACATCATTTAGTATACGTGATATTTTAGGAGCAGCTAA
ATTATATTTAAAGTTCCGTAATTTATTGCTTTCTCGTGATATACTAGGCAAATACATTCACATACACTGATAAAGAAACTCAGTTATCGTTTATT
TACAAACACAACCAGTGTTGACCTCAAGTTAAAGTTAAAGAATCGGTAAATGGCTTGCCAATGCTCGATTGCTTCATCAAACTCACCATTGCTTA
TAACAGTGCCAATTTTAATGCTGAAATCTTATCTACGAATATTAACTACAACCATTTCTCAGTTCTTTAGTCTAATGTAAACCAACTTAATGTAA
GCTACTTCTGTGTGTCTGGTAATGTGGAGGCAGTGAGTAGTTGTGCTGTATTCTCTTAAAGCTCTGCTCTATTCATTAAGATGTGCGTGTGCATT
GAGGAAGAAAGCCAACGAAAGTTGTTCGCCACATTACCGGCAATGTTGCAACATCGGGCGCGTTGTAATCGTGTGCAAGATGCGCGAAATCCAGT
CAAACGCGAACAGAAGAACGCGCCTCGAGGCGCAATGTTATTAAATAACAATGCAGAAAGAGCAGGGAGCACGGAGCAGCAGCCACCTCCTCATG
GGAAACATTACCAGGGTGCCAGTTGAAGAGTCTACAATGAACCACCTCAAACCACGATCCTTCTTTTTCCTCTTTTCTCGTTTCCAAAGACAGA
GGAGCTAAAATGTCGCAAAAAGAATTGGCGGCTCTGGTTGCCACGAGAACGAGTCGCAAACGCACCATATCCTCGACCTCATTCTCTATTTCCAC
TCGCACTGATCCAAAATCCATCATAGAGATACACATATTCAATGACTCCTTGCCCATAAAAAGAGCTTGCTGCGAAGTGGAGAATCCAACTTTAA
AAGCGGAACAGCGAGTGCAGCAGGAAGAAGAGAGCCTGGGCCAAGTGCCGCCGCTGACCGAGGAAGAGCAGCAGCGGCACGATGAGTTCCGAAAT
AGTGGTTCGATATTCCTGCAGGATTTGCCCTGCTTTAAGCTGCAGCAGGCACAGCCGATAGCAGGATCATCACCCATTCCCAAGTGTCGGGAGTG
CAGAAGAAGAAATTTGGCTACAACAGAGGGCGAACCCAGTTCAGTTAGCGACGTTTACTGCCGGTTCTACGAGTTCCGACGCCTTCAGTTCAATG
AGAATGGAGAGCTGTGCGTGGTTGGCTTCCCAAATCCCTACAGCGAGCCCTCACCAGAGGACATCGCCATTTGGCAGCCGGATAAAAATACACCG
CCGACCAGCGGTTACATGGATATACAGGTTTGCAGGTACATCCTACTCCATGCCGGCGACCAGTTCTGCTATATTTGGCACCAGGAAGCAGAGGC
TTTAAGTTTGCATCAGAATACGGACGGAACCATTGCCTGGAAGAAGGCCGTAAAAGGAACACGAGAGATTTGCGACGTGTGTGACACCACATTGT
TCAACTACCATTGGACTTGCCGCAAGTGCGGCTTTGGAGTGTGTCTGGACTGCGTTAAAGATCGCAAGGAGGGATTGCGACTGCGGCGAGCGGAG
AACGCTGCCCAAAAGGGATGCGATGAGTACCACTGGCTGCTCTGCAGCGACCCCAGTGGCCCACAGGAGCACGTCCTTACCGAGCTGATGCTAAC
ACAGATCATAGCCGGAGATGCCCTCAACGTCTTGGGCAGGCTGCTGCACGAGGTTCGTACTTTGTGGCAGGTGCCACAGGTCTGCGGCTGCCTTC
TGAGCAAGCAAGCGATTGAAGATGCACAATCAAAGGAAGTGATCCAGGATATGATTAAGGAGTCTCAGCTGAAGCAGCACACCAGCTACTCGTCG
CTGGCCTCCGAGCAGAAGGTGCACCAGCAACAGCGCCTCGATCAACTGCACGCCACGAAGTTGGAGTTTGCCAGAGAGCTAGGTGTAGATTATGT
TCCAGGTCGAGTGTGGACCAAGGAAACCTTGGGAAAGGATCCAATAACAACGGCGTTTGATAATTTGAAGCACATTAATTTTCTGAGAAAGGGAT
TGGCCGGCTTGAGAAGGTTTCTTCCACCAAGGACCATGACTTTTGCTTACTCCACTCAGTTGGCTCCAGGAGTTCCTCACGAGTTTCTGTGCGAT
GGCAGACTGCTTAGACTCACCGATGCCATGCATCCGGATAATCGAGTTCTTTTCCAGGAGGTTTGGAAATGCGGCCAGCCAGTTATGATTTCGGA
GGTGGCTCGCTCTTTGAACTTAGACTTATGGCATCCACAAGCCTTTTGCCGGGACTTTGGCGACAAGCCCAATGATCTTATTAATTGCCTGAATG
GCAATCTGGTGCCCAATCAGCCAATGCGACACTTTTGGGAGGGTTTTCAGTGCATGACCAAGCGTCTGCCAGATGCATATGGCAAGCCAATGCTC
TTAAAGCTTAAGGATTGGCCGCCGGGTGATGATTTTGCCGAAATACTGCCCACCAGGTTTGCTGATTTGATGAAGGGACTGCCCATGCCGGAGTA
CACACTTCGCACGGGAAACCTTAACATAGCTAGCTGCTTACCCAAGATGTTTGTGCCACCAGACTTAGGACCCAAAATGTACAACGCATATGGCT
CAGCATTGCACCCCGACAAGGGTACAACCAATCTTCACTTGGACATTTCGGATGCAGTGAACATAATGGTTTATGTGGGAATACCCCAGGATGGG
GACACGAGACCTCAGATGGCGGCCACGCAGAAAGCCATAGAAATTGGCGGATGCGATTACATCACTAGAGCTCGTTGCCAATCGCCAGATGTATT
ACCCGGAGCACTTTGGCACATCTTTCCAGCTCGCGATGCAGACAAAATAAGAGATTTACTTAACCGCGTGACCCTGGAGAAGGGTTTCCGTCTGG AGCCGGATCACGATCCAATTCACGATCAGAATTGGTACTTGGACGACAAGTTGCGAGCTCGTTTATTCAAAGAGTATGGCGTGGAGGGGCATCCG
ATTGTCCAGTGCTTGGGCGACGCAGTCTTTATACCAGCTGGCGCCCCACATCAGGTTCAAAATCTCCACAACTGTATTAAGGTGGCCGAGGATTT
TGTATCGCCGGAAAATATCACGCACTGCTATCATCTAACTCACGAGTTTAGAAGGCTTTCGCACTCGCACACAAATCACGAGGACAAGCTTCAGA
TCAAGAATATTATCTACCATGCCATCAAGGACTGTTGCACCATCCTGACCAGAGCTGTGGATGAGAGACTTAATGCGGAATTAACCAAGCTAAAT
GCAGATTAGAATTTTCTTACCTTTTAGTTTTTTCAACTATTTAACATTTATTATTATTTTTTAAGATCAAAAATTGTCAAATATTCAATAAATA
CTTACTTAGAACTAAATAAAAGGTACATTTATTTATTTGTCATCCAGTGCATAATTAAGTAAATTTTCTATTTTAAAAACCTAAATAAATATCAA
TTCAAATTAATTGATTTAATTGAAATTTCTAGTATTTACATAGACAACACTAAGCCTAAGCAAGATACTCTCCAGCAACAAATGCCCATGCATGC
TGAGGACGGAGCTGAATCTGATGATGAGGAGTCCAGCCCAGGCAGACATTAGCATCGTAAGGATCATACTACTAATTTGGCGCCCATATAGAAGT
CAAGTCAATTACAACGCCAGAAAGCCTTTTATGTTAATCGAGAGTGGAAAGGGAAAATAATTTTTTTGCTAAACTAGCCTAGAGATCGAAATATT
AAGAATACAACTAAAATGACGGTGGATTTCAACGATTATTTTTGGGTGAGTTAAATAAGGTGCATATGGACGGATCATTGCTTAAATATATTCTT
CCATTTAATATCCAGGGGGAGAAGAACAATGGCTACGATGTTCTGTACCACAACATGAAGTTCGGCCTGATTGCCAGCAAGGAGTTATCCGAGTT
TCTGCGCGAGAAGTCTAACATTGAGGAGCAGAACTCAAAGATGATGTCCAAGCTGGCCCACAAGGCTGGTACACTAAATAGCACATTCGCTCCTG
TTTGGACCATACTGCGAACATCGGCAGAGAAGCTCTCCACGCTCCACCTGCAGATGGTGCAAAAGCTGACTGAGCTGGTCAAGGATGTTGCCAAG
TATGCCGACGAGCTGCACAAAAAGCACAAATCCGTCAAGGAGGAGGAATCGCAGACTCTTGAGTGTGTCCAAGCCATCCAGACGTCGACGGTGGC
AGTGCAAAAGTTGCGCGATCTGTACGCCAGCAAGGTCCAGGAGCTGGAGAAGCTGCGCA
(SEQ ID NO: 919)

Exon: 1001..1132
Exon: 3226..5804
Start ATG: 3240

Transcript No. : CT24376
CCAGCTCTAGTTGCGCTTCGCTCAGTGCTAATGAAAAATCGAATTTTTCGCTTCAAATCGACTGAAGTTTACACGGGCTAAAGTATTACAGAAGT
TTGGCTCAAGCCATTACACAACATGCAATAAGTAAATACAGAGGAGCTAAAATGTCGCAAAAAGAATTGGCGGCTCTGGTTGCCACGAGAACGAG
TCGCAAACGCACCATATCCTCGACCTCATTCTCTATTTCCACTCGCACTGATCCAAAATCCATCATAGAGATACACATATTCAATGACTCCTTGC
CCATAAAAAGAGCTTGCTGCGAAGTGGAGAATCCAACTTTAAAAGCGGAACAGCGAGTGCAGCAGGAAGAAGAGAGCCTGGGCCAAGTGCCGCCG
CTGACCGAGGAAGAGCAGCAGCGGCACGATGAGTTCCGAAATAGTGGTTCGATATTCCTGCAGGATTTGCCCTGCTTTAAGCTGCAGCAGGCACA
GCCGATAGCAGGATCATCACCCATTCCCAAGTGTCGGGAGTGCAGAAGAAGAAATTTGGCTACAACAGAGGGCGAACCCAGTTCAGTTAGCGACG
TTTACTGCCGGTTCTACGAGTTCCGACGCCTTCAGTTCAATGAGAATGGAGAGCTGTGCGTGGTTGGCTTCCCAAATCCCTACAGCGAGCCCTCA
CCAGAGGACATCGCCATTTGGCAGCCGGATAAAAATACACCGCCGACCAGCGGTTACATGGATATACAGGTTTGCAGGTACATCCTACTCCATGC
CGGCGACCAGTTCTGCTATATTTGGCACCAGGAAGCAGAGGCTTTAAGTTTGCATCAGAATACGGACGGAACCATTGCCTGGAAGAAGGCCGTAA
AAGGAACACGAGAGATTTGCGACGTGTGTGACACCACATTGTTCAACTACCATTGGACTTGCCGCAAGTGCGGCTTTGGAGTGTGTCTGGACTGC
GTTAAAGATCGCAAGGAGGGATTGCGACTGCGGCGAGCGGAGAACGCTGCCCAAAAGGGATGCGATGAGTACCACTGGCTGCTCTGCAGCGACCC
CAGTGGCCCACAGGAGCACGTCCTTACCGAGCTGATGCTAACACAGATCATAGCCGGAGATGCCCTCAACGTCTTGGGCAGGCTGCTGCACGAGG
TTCGTACTTTGTGGCAGGTGCCACAGGTCTGCGGCTGCCTTCTGAGCAAGCAAGCGATTGAAGATGCACAATCAAAGGAAGTGATCCAGGATATG
ATTAAGGAGTCTCAGCTGAAGCAGCACACCAGCTACTCGTCGCTGGCCTCCGAGCAGAAGGTGCACCAGCAACAGCGCCTCGATCAACTGCACGC
CACGAAGTTGGAGTTTGCCAGAGAGCTAGGTGTAGATTATGTTCCAGGTCGAGTGTGGACCAAGGAAACCTTGGGAAAGGATCCAATAACAACGG
CGTTTGATAATTTGAAGCACATTAATTTTCTGAGAAAGGGATTGGCCGGCTTGAGAAGGTTTCTTCCACCAAGGACCATGACTTTTGCTTACTCC
ACTCAGTTGGCTCCAGGAGTTCCTCACGAGTTTCTGTGCGATGGCAGACTGCTTAGACTCACCGATGCCATGCATCCGGATAATCGAGTTCTTTT
CCAGGAGGTTTGGAAATGCGGCCAGCCAGTTATGATTTCGGAGGTGGCTCGCTCTTTGAACTTAGACTTATGGCATCCACAAGCCTTTTGCCGGG
ACTTTGGCGACAAGCCCAATGATCTTATTAATTGCCTGAATGGCAATCTGGTGCCCAATCAGCCAATGCGACACTTTTGGGAGGGTTTTCAGTGC
ATGACCAAGCGTCTGCCAGATGCATATGGCAAGCCAATGCTCTTAAAGCTTAAGGATTGGCCGCCGGGTGATGATTTTGCCGAAATACTGCCCAC
CAGGTTTGCTGATTTGATGAAGGGACTGCCCATGCCGGAGTACACACTTCGCACGGGAAACCTTAACATAGCTAGCTGCTTACCCAAGATGTTTG
TGCCACCAGACTTAGGACCCAAAATGTACAACGCATATGGCTCAGCATTGCACCCCGACAAGGGTACAACCAATCTTCACTTGGACATTTCGGAT
GCAGTGAACATAATGGTTTATGTGGGAATACCCCAGGATGGGGACACGAGACCTCAGATGGCGGCCACGCAGAAAGCCATAGAAATTGGCGGATG
CGATTACATCACTAGAGCTCGTTGCCAATCGCCAGATGTATTACCCGGAGCACTTTGGCACATCTTTCCAGCTCGCGATGCAGACAAAATAAGAG
ATTTACTTAACCGCGTGACCCTGGAGAAGGGTTTCCGTCTGGAGCCGGATCACGATCCAATTCACGATCAGAATTGGTACTTGGACGACAAGTTG
CGAGCTCGTTTATTCAAAGAGTATGGCGTGGAGGGGCATCCGATTGTCCAGTGCTTGGGCGACGCAGTCTTTATACCAGCTGGCGCCCCACATCA
GGTTCAAAATCTCCACAACTGTATTAAGGTGGCCGAGGATTTTGTATCGCCGGAAAATATCACGCACTGCTATCATCTAACTCACGAGTTTAGAA
GGCTTTCGCACTCGCACACAAATCACGAGGACAAGCTTCAGATCAAGAATATTATCTACCATGCCATCAAGGACTGTTGCACCATCCTGACCAGA
GCTGTGGATGAGAGACTTAATGCGGAATTAACCAAGCTAAATGCAGATTAG
(SEQ ID NO: 920)

Start ATG: 147

MSQKELAALVATRTSRKRTISSTSFSISTRTDPKSIIEIHIFNDSLPIKRACCEVENPTLKAEQRVQQEEESLGQVPPLTEEEQQRHDEFRNSGS
IFLQDLPCFKLQQAQPIAGSSPIPKCRECRRRNLATTEGEPSSVSDVYCRFYEFRRLQFNENGELCVVGFPNPYSEPSPEDIAIWQPDKNTPPTS
GYMDIQVCRYILLHAGDQFCYIWHQEAEALSLHQNTDGTIAWKKAVKGTREICDVCDTTLFNYHWTCRKCGFGVCLDCVKDRKEGLRLRRAENAA
QKGCDEYHWLLCSDPSGPQEHVLTELMLTQIIAGDALNVLGRLLHEVRTLWQVPQVCGCLLSKQAIEDAQSKEVIQDMIKESQLKQHTSYSSLAS
EQKVHQQQRLDQLHATKLEFARELGVDYVPGRVWTKETLGKDPITTAFDNLKHINFLRKGLAGLRRFLPPRTMTFAYSTQLAPGVPHEFLCDGRL
LRLTDAMHPDNRVLFQEVWKCGQPVMISEVARSLNLDLWHPQAFCRDFGDKPNDLINCLNGNLVPNQPMRHFWEGFQCMTKRLPDAYGKPMLLKL
KDWPPGDDFAEILPTRFADLMKGLPMPEYTLRTGNLNIASCLPKMFVPPDLGPKMYNAYGSALHPDKGTTNLHLDISDAVNIMVYVGIPQDGDTR
PQMAATQKAIEIGGCDYITRARCQSPDVLPGALWHIFPARDADKIRDLLNRVTLEKGFRLEPDHDPIHDQNWYLDDKLRARLFKEYGVEGHPIVQ
CLGDAVFIPAGAPHQVQNLHNCIKVAEDFVSPENITHCYHLTHEFRRLSHSHTNHEDKLQIKNIIYHAIKDCCTILTRAVDERLNAELTKLNAD*
(SEQ ID NO: 921)

Name: TESTIS SPECIFIC PROTEIN A LIKE

Celera Sequence No. : 142000013384474

FIGURE SHEET 499

TGCGGGGCTGTAGCTCCAGCTTATGACCCTCCTGCGTAATGTATTCCTGTAGAATTTTCGAGTCGGTGGTCTGCGGGTAGCCAAAGTCGAGCAAT
TCATCCAGCAGCTCGTAGATGATCACGAAATTGTCCCGAATGGACTCCTCCTCCAGCTCCTTGAAGTATTCCACAAAGACCTGCGCGATCTTGTG
CAGAAAGACGAAGACCAGAGCGATATTAACGTTCTTATTGCGCGGCGTCGTGGATACGATATAAAGATTGTTCGTTTTGATGTAGGCAAATGTAG
TCTCCGCCGTCTGAAGGATCGGAGTGATTAGGCCCTCCTCCTCGCGCTCCATCAGCAATGGCATGAATTTGTCGATCACGGCCATGTCGATGTTG
TCACCGCGGTAGTTCCGCGATATCAGCACCTTGCCCTTCACGTCCAGAACGAAAATGGCCGACGAAGACATGTCTCTTGGTTCCCAGCAGCTGCC
ACTTGTCCCAGGTGTAAAATTCCCAATTGGATCGAGTGGGAGGTCGCTTCGATGGTTCTACTGCTCGCGGCAGGCGTTGCGCGTGGAAGTTGGCA
ACTGTCGCGAGGTGGCGATGAGTGGGCTAGGTCTATCAATGGCTGGATTTACATATTCCGTTTCGTAGACTGGAAAATGCGAATGAAAACTCCG
GAATTTCTTACGTCGCCTTTTCTGCTGCTTCTTTTTCTTATTAGTTGGCCCACCAGTGCTGTGAAATGTTCACATCAGGTGTTGGGCAGTGTGGC
CAGGTGAGATTGGTCTACTGCTGATTAACTAGCGAATTAAGCTTAAAGGAAATGAAAAATGTGCAAGGTGTAACATCTTAAGGTTTCTGTTTTTA
AATAAATACCTTTTAAATTATTTTCATTTTCCCATTGGTACCTTTAAATTCAAATCATAAATATATTGGAGAATGTAATCTAGCATCACTATTGT
GCCATCCGGCATTTGTGGCCATCCGCAGTACGGCCACACTGCTAGCCCAGACGCTGCTTTTGTGGAATTGTTAATTATTTATTTCGGCGAGCATG
CAAATGAACCCGAGCGTCACAATCGAGCGCAAACGCGTCGACTGCAGTGTCCTGCCAAAGGGATGGCAGCGCGACGAGGTCCGAAAGTCCGGCAG
CAGCGCCAATAACAACGCCAGCAGCAACAACAACAGCAGTGCCACAGCCAGCAGCAACAACAACAATAACAAGGTGGATGTTTTCTACTACAGGT
AAAGAAGAAGAGCAGAATTACTATATAGACTACTATATACCTAAAATCGGAACACTGCACGCTGTTTAATCGGATAAACGTTTATAATCACTTTC
ACTACCTTTCTGTTATTACATCCGCATAACCACACACACACACACCATATACACCACACACACGCATACGCCTATGTATACACACGCACACGAAC
TACCACCTAACCCACCAAAAATATCCATCCACCGCCGTGTCTGTTCAGCAGTCCCACAGGAAAAAGGGCGGAGGGAAAGCCACAGGACATTGCAA
TCCCTGATTTCCAGCCTGGCAAAATGCCGCACTGCGCCCTGCCCTCGCCCTCCATTTCGCTGTACCGCTGCAGCGCCATGCCGCTGCCTATAGCA
AGCGGGGGCGGTAATGGGGCCACCAGCGGATCGGCGGCCAATGCCCTCAAGCGCAAGTTCGCCCGGAGTCAAGGAGGCAATGCTGCAGGAGCAGC
AGGAGCTGCTCCTCCGGCAGCGACCGCCTCGTCAGCAGCAACAGCGACAGCAGCATCTGCTTCACCATCAACGGCCAATCGCCAGCAGCAACAGA
TCGAACTCAGGTAGAGCCAAGTGGATGAGCACTTGACTCTTGCATGTCAGCGTGTCATGTCTTGTTTGCCAGGACGCAAGGTCTACAGCCTGCGG
CAATTAAAAAGCATCAAATGAAAAAATACCCAAAGAAACACACAATTGGCAAAACAATTCGTAGTTGTCTTCAAAAACGCTGTAGCTCTGTGCCA
CCTGAGATTTATGTTCCACCATCTCTGCATGCTAAAGCTTTACTTTACGCTTTGTCTAATGTGCTGTTCGGTGTTTTAGCTTTTTGAAGGCGTTT
CTCTAATACATTTCCAATCTTTAATCCCTTACAGCCGAGCCCTGCGCACTGATGTCTCCCTGGTGCCTCCCATTCGACAGACTGCCTCGATCTTC
AAGCAACCGGTGACGGTGATTCGCAACCATAAACAGGATCCCGCCAAAGCGAAGAATGAACCCAAGCATGGCACTCGGGAGAAGCCGAAACAGCT
GTTCTGGGAGAAGCGACTGGAACGACTACGCGCCTGCCACGACAGTGGCGAGGAGCTAGACGACATCTCACTGCCCAAGACCATACGCACCGTTG
GCCCCAATGTCAACGAACAGACCGTCCTCCAGTCGGTGGCCACGGCCCTGCATATGCTCAACGCCGGCGTACACGGCCAGAGTTCTACGAAGGCT
GATTTGACCAAGAATGCCATGGCGTTTATGAATCCTGAACAACCGCTAATGCACGCGGTGATCATTTCGGAGGACGACATACGCAAACAGGAGGA
TCGGGTCGGAGTTGCGCGGCGAAAGCTGCAGGATGCACTCAAGACATGAGTTCAATGGTTAACCCCCATGCATCTACCAATTCCATTGTAGGCTC
TAACATCTCTATCGTATTGACCCCTATTCGAAATCTACATTTAAGACTAGTGTGTAATAAACCAAATCCAACTCCAATCGAGGAATTCTGGTTTC
TTATTGGACATCGAGAAAGCTTCGCTTGTCTTTTCCATGACAACAGGGCTCTGTTATCCAATTTTATTACGCTCAGATGACTTTAAAATGCTATT
TTATACAAGACAGTTTAAAAACGAATTCGAACTATAATACATAAACCGAATTTTCATACTTAGTCGATTTGTTTGGCAAATCCTTGGAACGAAGC
GTTATCTACGACGAGGGGATCATTACCTGACGAAATTTTCGGTCCAAAGATTTATGGCCAAGTAAATCGATCTCCTTCAGTGTTTAGGTAAACCT
TTAAAGCTGGACAGTTTTTGTGCTTCATCCCCACATTGTATTTTAAAATATATATACTATACACATAGATATCGTTGCAGAGATGCGATTAGTCT
AGGCCCTCCTCCATCTCGTCATCCTCGTAATCTATGCCATCGTAGTCCGTCGAAGAGCGTGTCGTTAGCTGCAAGGATGAATCAATCGGAATTTG
CAATTAACTGAGAATTTTGCACGTGCTCAAGCTGAGGCTGTCTACAAGAGTGTCTGGAGCCAACAGAAGACATTGAACCAGAACTATCGAATAAG
CTCCATCAAGTCAAGAGTAAAGAACTACAAATTTCAGCCAAAAATACCCACCTGGTTGTAAATCCCACGCCATGCCGCAAACGCTCCCATGGCCA
AGACGGCTCCCACGCCGGCTACTATTTTGGTGTTCAGCTCGGAGTCTAGGAACTTGCGCTCCGAGGCCGTCAGACTGGCCTCCGTGCCACTGGGT
GTCTTTGTGAGCTTGACGGAACTGTATCCCTCGATGCGGAATATGTCCTTCGTGATGCGGTTGATAAAGTTCACTAGGTTTTGGCAGCCCTTAAT
GTGATTCTGCAGTGGATTGTTAGGCAGTGCGATCTTAAAGATGATGGCAAGATAGCTGTAGACAATGGCATCAAACTCGCTGTAGGTGTCGCCAA
AGAACCACACCTTGCGACCCAATTTCCG
(SEQ ID NO: 922)

Exon: 1001..1233
Exon: 2125..2733
Start ATG: 1043

Transcript No. : CT24429
ACGCTGCTTTTGTGGAATTGTTAATTATTTATTTCGGCGAGCATGCAAATGAACCCGAGCGTCACAATCGAGCGCAAACGCGTCGACTGCAGTGT
CCTGCCAAAGGGATGGCAGCGCGACGAGGTCCGAAAGTCCGGCAGCAGCGCCAATAACAACGCCAGCAGCAACAACAACAGCAGTGCCACAGCCA
GCAGCAACAACAACAATAACAAGGTGGATGTTTTCTACTACAGCCGAGCCCTGCGCACTGATGTCTCCCTGGTGCCTCCCATTCGACAGACTGCC
TCGATCTTCAAGCAACCGGTGACGGTGATTCGCAACCATAAACAGGATCCCGCCAAAGCGAAGAATGAACCCAAGCATGGCACTCGGGAGAAGCC
GAAACAGCTGTTCTGGGAGAAGCGACTGGAACGACTACGCGCCTGCCACGACAGTGGCGAGGAGCTAGACGACATCTCACTGCCCAAGACCATAC
GCACCGTTGGCCCCAATGTCAACGAACAGACCGTCCTCCAGTCGGTGGCCACGGCCCTGCATATGCTCAACGCCGGCGTACACGGCCAGAGTTCT
ACGAAGGCTGATTTGACCAAGAATGCCATGGCGTTTATGAATCCTGAACAACCGCTAATGCACGCGGTGATCATTTCGGAGGACGACATACGCAA
ACAGGAGGATCGGGTCGGAGTTGCGCGGCGAAAGCTGCAGGATGCACTCAAGACATGAGTTCAATGGTTAACCCCCATGCATCTACCAATTCCAT
TGTAGGCTCTAACATCTCTATCGTATTGACCCCTATTCGAAATCTACATTTAAGACTAGTGTGTAATAAACCAAATCCAACT
(SEQ ID NO: 923)

Start ATG: 43

MQMNPSVTIERKRVDCSVLPKGWQRDEVRKSGSSANNNASSNNNSSATASSNNNNNKVDVFYYSRALRTDVSLVPPIRQTASIFKQPVTVIRNHK
QDPAKAKNEPKHGTREKPKQLFWEKRLERLRACHDSGEELDDISLPKTIRTVGPNVNEQTVLQSVATALHMLNAGVHGQSSTKADLTKNAMAFMN
PEQPLMHAVIISEDDIRKQEDRVGVARRKLQDALKT*
(SEQ ID NO: 924)

Classification: known_flybase_gene
Gene Symbol: methyl-CpG-binding-domain-like-protein
FlyBase ID: FBgn0027950

Celera Sequence No. : 142000013384654

FIGURE SHEET 500

TGATGATGAGGACTGTGCAAGCATGCGAAGCAGTTCGCCGTCAACACAATCCGAGATGCTAGTGGTACCGCCACTTTCGGTGCAACCCACGCGGA
AAAACAAGGCCGTTGTGGGCCGCATTTAGAGCTGATGATGATGATGACTCCACAGTCAAATTGTGTATTCCATTTTGGAAGTCTCTTTTTGGAGA
GACTCGCTTGCAGTGCTATTCCTTGAGCATTGGTCGCCCATGTCCGAGTGCATATACAAGCTTCGAATTCGTAATCTCACAACACAACCAGAAAC
AAATTATCGAGCGTCCAATATTGTTTAGATTGTAAAATGTATTGTTAAGTTGCACCTGTCGATAGGAAGGCTCGCAAATGTTGAAGCGTTTGCCC
GAGCTGTCGATTGATCATGATTAACTTGTAAATAGTTCTCCATATGTGTACTCCCGTGCCCGTATAATTGTGTCGCGTCGCTAAATGTAATCAAC
TACTCATTGCAGTGACTAGGGATCGAATTCACGCACGCACCGAACGATCGATTCGGATGGTTTTCGGTCGGATGATCGCCACACCGCAACAAGCT
GTGAATGTTTACTGAGTAAATTTTTTAAAAACCCTATCTTACCATATTGATTATAACTCAACGATTTTGCTTGAGTAGGCAATTACGACCCTAAG
TCGTAAGGCGTTCAAAGCATGAAGATGTTTAAGTTAATATATGAACAATGATTAAAGGAAAACATTTTTAAATCAAAGCATTTTTTATTCTTAGC
TTTGAAGCTGCAAAGTAGGCAACGAATTACACAAACTTCGACAGTTACCACAATCTCACCCGAAAAGATGCAATTGTTGCGCATAGAAAATTAGG
TTTTTAATTTAGTCTATAGAACAATTTTGTAGGGGCAATTCCAAGTAAATATTCATATACACCAAGCCAATCATATCTTCCACACTTACGAATCT
GGTGTACAAAAATAAAAATATACTAACGTAGAGGACCTAAACAATCGCTTTCAGAGTGTATAAACCGATTTGACGCCCGAATTGAATTTGGACAT
TGCATCGGAATGAAGTTGATACTGCAAACTATGCGATTGCAAATGAAGGAGTATCTTCAGCTTCTGGCCGATCTCCAGAATGGCCATTTCGTTAC
TCCCGTTGGCAGTCCAAACCGCTGTAATAGATACAGTTTTTTATCAATGTGCAGAACACATTTGATAAACTTACAGATTTTGTTGCTCTTGTTAC
GTATATTGATGACAGCTCCGCAGATCTCGTCGGAGTATTCAAAATTTTGGCCCACCATCAGCAGTAGAATGTCCAGCCAAATTTGATCCAATTCC
GCTTTGGCACTCTTACTCACGGTGACCAGCCAGCGACCACCCTTGATGTTGGCTTCATCCTCCCACATGGGTCTTTGGGAGTAGAGGATTTAAGT
TAGCATCTCTCAATGAACAATGATTTATTCGTACTTTATGCCCTTCTTGAACACGGAGTAATCGCATCCAATCTTCAGCTCCGCTGGGGTCTTGA
TGGTATGGTACAAGCTCCAGAAGGTCTCCACACTGTCAATCTCGGTAATCTCGTTTAGCATGTCCTTCCAGTGCTTGGTGCGATCGTTTTCCAAA
TACCACAAAGTCCACACATGCTCCAAAGGATGCTTGTACTCGACTTGGTATATCTCTTCATCGATAGGTTCTGGGCTATTGCTCTCCAGTGGAAC
ACCTTCGTGGTGATGATGATGCTTATGGATACTATTCAGCTGATGTTGCTGATCCTGCTGCTTCATAATATCAAAACTTTGCACTTGTGCACTGG
CCATGTTGTTGGTTGACTTGTTTTTTTTTTTCGATACGAACAGGTAACCTTAATTTATTTGCTGACGGCTGTGTTCTCAACGAATTTTGTCGCG
ATTCGAGTGGGAATTGCTTACTAATAACCAAAAATACTTTAGCACATTTTTCTAGACCTAAACGAAACCTGTCGAAAAGAAGGAAATGAAATGAC
AATGACACCTGGGTGTAAGCATACTATGCTGGTTTTTTCTTTTAATATAAATTATTTTTATTCATTTATAAATACTGCAAAACTTAAGACAAATC
AATTTACATATTGTTAACATAGAAATGCGCGCTTGGTCCTTAAAAAAAAAAAATAATAACATACAAAATGAAAATGTATGCACTCTATTCCAATGG
TCAATTAAACACTAAGCGGAGGCACTAGAGAAAACAAATCGAAACAGCTACGGGGTGTTCAAAATAAAAAAAAACACGGTTTTCGTAACCATATT
TGAAAAGATTCTCAATTCTTTTAGAAATACGTTAATAAATTATCTCAAGGCTGGTTTTGAATCATCCACCCGTCTAGACCCATAAAACAGCGGCT
GCATCCTCGTTGGACAAAGTGGAGAAGCGCTGGTAGCGATTCGCATTGCGATAGGTTTTCGAGGGCGATGGAGCGGTTGATATCTGAGCTTGAAC
CTGTACTTGAACTTGAGTCTGATTTTGCATGGGCAGCCCCACCATATTTAATCCGGACTTTAGTGTGGAGTTCCTGCTGTCCGAGGACATGGACA
GGCGTCGCTGGTTTCCATTCATCAAGGTGGAACTCAGGGGCAAGCCGACATCGTGAAAGGAGCTAATCGAACTGAAGCCACTCTCATCCTCGGTA
CTGGAACCGCTCTGCTTATTGCTGGTGGTTTTGTTATTGCTATTGCTGATGGCTGTGTTGCTGGCGGTGGTCTGTGTCTGCGTCTCCTCATCCGT
TTCCACTTTCGAGGAGGAGGATGCCGTCGACGAGATGGTGGAATGCACGGAACTGTCGGTGGAGCTGCGCAACGATAGCCTCGAGTCGCGCATGT
TGTTGGCCCGCAGAAAGATGAGTTCCGCATTTGATTTCCCGCCCGGTGATGGAGTCTCCAGTGTGGCACTCATGATACTGGTGGAATTGTGCAAT
GGTGGCGTCAGTA
(SEQ ID NO: 925)

Exon: 1958..1460
Exon: 1402..1215
Exon: 1161..1001
Start ATG: 1776 (Reverse strand: CAT)

Transcript No. : CT24507
GGTCTAGAAAAATGTGCTAAAGTATTTTTGGTTATTAGTAAGCAATTCCCACTCGAATCGCGACAAAATTCGTTGAGAACACAGCCGTCAGCAAA
TAAATTAAGGTTACCTGTTCGTATCGAAAAAAAAAAAACAAGTCAACCAACAACATGGCCAGTGCACAAGTGCAAAGTTTTGATATTATGAAGCA
GCAGGATCAGCAACATCAGCTGAATAGTATCCATAAGCATCATCATCACCACGAAGGTGTTCCACTGGAGAGCAATAGCCCAGAACCTATCGATG
AAGAGATATACCAAGTCGAGTACAAGCATCCTTTGGAGCATGTGTGGACTTTGTGGTATTTGGAAAACGATCGCACCAAGCACTGGAAGGACATG
CTAAACGAGATTACCGAGATTGACAGTGTGGAGACCTTCTGGAGCTTGTACCATACCATCAAGACCCCAGCGGAGCTGAAGATTGGATGCGATTA
CTCCGTGTTCAAGAAGGGCATAAAACCCATGTGGGAGGATGAAGCCAACATCAAGGGTGGTCGCTGGCTGGTCACCGTGAGTAAGAGTGCCAAAG
CGGAATTGGATCAAATTTGGCTGGACATTCTACTGCTGATGGTGGGCCAAAATTTTGAATACTCCGACGAGATCTGCGGAGCTGTCATCAATATA
CGTAACAAGAGCAACAAAATCTCGGTTTGGACTGCCAACGGGAGTAACGAAATGGCCATTCTGGAGATCGGCCAGAAGCTGAAGATACTCCTTCA
TTTGCAATCGCATAGTTTGCAGTATCAACTTCATTCCGATGCAATGTCCAAATTCAATTCGGGCGTCAAATCGGTTTATACACTCTGA
(SEQ ID NO: 926)

Start ATG: 183 (Reverse strand: CAT)

MKQQDQQHQLNSIHKHHHHHEGVPLESNSPEPIDEEIYQVEYKHPLEHVWTLWYLENDRTKHWKDMLNEITEIDSVETFWSLYHTIKTPAELKIG
CDYSVFKKGIKPMWEDEANIKGGRWLVTVSKSAKAELDQIWLDILLLMVGQNFEYSDEICGAVINIRNKSNKISVWTANGSNEMAILEIGQKLKI
LLHLQSHSLQYQLHSDAMSKFNSGVKSVYTL*
(SEQ ID NO: 927)

Classification: translation_factor

Celera Sequence No. : 142000013384654
TATATTGCTCATTTAATTGAAAGAATTTATTTATAAATTATAAATTTATTTATAAATTTATTTATATTTATTTATAAATTTATATTTTCAATAAA
TCGAATGAATTATTAGCATTTATTGAAGTTCCCGCAATATTTAAATTACGCTCCATTAATTTATGATGTGTAAGCCACTGTAAATCCTATTATTA
CATTTTTGTTAGCTTAATTGAGAACTAAATTTGATGAAAATTTTCAAGAACATTTTTATTTACAGCTTACTACCCATTTTTTTTTTTTGTGCTAA
GTTACCCCGATGCAACTTTCAATTCCACTTGATGTTTGCTGGCAAATTCATTGAGACACTTAATAAATGTTACATATACGCCTTTCAACCACTTT
AGACCCCCAACTATGCCCCCTTATCACCCTTATCAATGCCAAGTGAAGTTTACTCTCCAATTTCGACCCACACACGACACTTTTCGCACATAAAT
CAAGTTGACCTTAAAAAAATCAGTGAAACAAAAACTTTGTCATATCATGGCCAGCAACAACAACAATAATAACAACAACAACTGCAAGACGCCAA
AGGAGGCGAGGATTTTTGTGGGCAGAAGAGGGGGTAGTGGGGTTGTTAAGGGGAGGCTGTCAAGGCTACGTGACAAACAACAAGGTGACATAAAT
ATCCAGTTGCTCCAAAAAGGAAACTGAACTTTTTTCTTTAATGCCAAGGCAACATAGCAAAGTTTAAGGGAGCCGGGGGATGTGGGGCAGAGTGA
GAGGGGAGACGGAGACGCGTTCCAAGCAAAGAAAGCATAAAGTGATACAGTGGGCACTCGCGTAACAGAACTTCAGGGAATTCCAAGTCAAAGAA AAGTGAACTTGAATTCAGAAAAAGTTGTTAATTAAATATGTACATAGTATTAACTGTTTTTAATATTGTTTGTAAATAATTTTAACAAAATATTT
GAAAATCACGTTGTTTCTATAAATTTCCCTTAACGCATATACATATGTACTTAATTTTTTTTGTAGCCCAAGCATTTCCTCATAACGTTAAATGT
TGGCATTACTGCGGAATTTAAATTCCGAGAATTCTCGTTTGGCGCAAAGATTACTGTACTAACCTGCTGCTGTGTTGGCTGATGTGTCGGTTGCA
TTGGCCAGACGAGATTGAGATTCCTGGCGGATTGTGCCGGTGGTTGTGGATGCTGAGGGGGATGGGGCGGCTGGGCGGTGAGCAGCTGATTAGAG
GCGCCAAAGTGTATCATGTTGGCGGTGTGACGTCGTGCTGGCAGAGCGGGGGGCGGGGTGGCGCAGGGGGAATCCTGTTCGTTGTCTCTCTCTAG
CGATTCCTGATTCTCCAGCTGCTGCTGTTGTTGTTGTTGTTGTAGTTTGGCCTCGTTTGTTGGCGGCTTCTTGGGCAATGTCAAGGCATTGTTGT
TGTTGTTGTTGTTGTTGTTGTTGTTGTTGTTGTTGTTGAGCGAAAGCGAACGCGCAAAAGAACTTTTGAAATAGCGACACGGCATCTGGAAATCA
AAGTCAAGATCCGTTGTCTGCTGCATGTTTGTTGTGGTTTTGTGCATTTCTATTGGCTAAAACGGGATTTCTTTATTTATATATTTGAATTTTCC
CTTGTGCTGCCTCTTTCTCTGCTATTTTTTTTTGTTGGTCTCTTTTAAATTGGCATTGTTGATGTTTTCCTCTTTAGCGGTATTTCCCTTTGGAT
TATTGCATTTTTTCACGCACCCATAAGTTCACTTTCACACACTCACGCACAAATCAATTAGTTTTTGACACTCGAAGGATTTTTTTCAATACAAT
TTAATAGAAATTCAATGGAAATCAATTTCTGGGATTTATTCGCGCGCGCATAACACAAACAAAATTCATAAAGCCGCAGCTAGTTTTCGTTTGCG
CCCGAATTGATGAGTTTTACTGTACTAAAATCCAGAAAAATTGGGAAATATTGATTCGTTGAAATGTTGTTGGGTTTGAATTTTAGTGCGAACTG
TTGTTATTAAATGTTCAAGAATAATGTTCTACTAATAAATAGCTTGTTTTTCAACTTTACAACAGTTTGCTGCTTCTCGTAATTCACGCGACTTT
TCCCGGCCGAGGTGGAAACCTAACTGGAAGACCAACTGTATGTTACCGCCAAATTCGCAGACAGTTTGTGCTTGGGTCACCCTGCTTGGGTTATT
ATTTCGATCTCCAATGTTAATGTTAATGTTATTAACAGTAAGCTCGTTCTCTCTGAAATAAATGAATGAAGAAGTTACCAAGGCAACCGAATAAA
ACAGAGTCTGCAAAGAATGTCTTAACAGCTAGCTATTCTCTTAATAACAGTGCAACAACAGTAAAAAAAAATATGCTTAAAAGTATGCTAAGCATT
TTGTTAAACAATCGTTTTTATGTCATAAGATCAGATCGTGAAACCTAAATTTAACAAATTAAATGAAAGAAACGTCTTGAACGTATACATTTAAG
TGATTTTATAGAGACTTTTTTTTTAGCTTATAGCATTTAGTCAATAGCTTAGTTAACTGCACAAGAGTCTATAATAATAAAAGTCTATAAATACA
TTAAATTCGTTAACATGTTTTCAAATGTAGAAATGTTAATGATTTGGCGCGCCAAGAAATTTGAAAAATGTAGATTGTATTTTACAAGAAAATAT
GAAAAAGTATATTAAAAAGATAAAGTTTATTTTTGTTCTTCTTTTAGTTAAATAGATTGCATCTTAGTATTCATTATAAATATTATTCCAAATGT
CTTAAAATTAATTAGTTTTTATATTTTATCATGAGTAAGAAAAGGGTTTTTTTCCAGTGCAAATTTTGTTCAACGAAACTAATAATATCGGTTGA
GAAATGGAAATTGTTTTACCATTCCCCCTTCTAAGGAGGCATTAGCATTCGTTCCTCCGCTGACTAATCCCCGGCCTAATTCCCATACCTTATGT
GGTATCTATATTGGGGAGACAGCTTGCCAATCAATTTGATTGCGCTGCGCTGATGTTTGCCCCTGTTTATCTAGCTTAGGGGAAGGATTTTCAAG
CTTTTATCATAACAGAAGTGCTTTAATTCCCTTTGATGAACATTTGTACATAACCCCCTTTTGA
(SEQ ID NO: 928)

Exon: 2104..1001
Start ATG: 1546 (Reverse strand: CAT)

Transcript No. : CT24537
CACCTCGGCCGGGAAAAGTCGCGTGAATTACGAGAAGCAGCAAACTGTTGTAAAGTTGAAAAACAAGCTATTTATTAGTAGAACATTATTCTTGA
ACATTTAATAACAACAGTTCGCACTAAAATTCAAACCCAACAACATTTCAACGAATCAATATTTCCCAATTTTTCTGGATTTTAGTACAGTAAAA
CTCATCAATTCGGGCGCAAACGAAAACTAGCTGCGGCTTTATGAATTTTGTTTGTGTTATGCGCGCGCGAATAAATCCCAGAAATTGATTTCCAT
TGAATTTCTATTAAATTGTATTGAAAAAAATCCTTCGAGTGTCAAAAACTAATTGATTTGTGCGTGAGTGTGTGAAAGTGAACTTATGGGTGCGT
GAAAAAATGCAATAATCCAAAGGGAAATACCGCTAAAGAGGAAAACATCAACAATGCCAATTTAAAAGAGACCAACAAAAAAAAATAGCAGAGAA
AGAGGCAGCACAAGGGAAAATTCAAATATATAAATAAAGAAATCCCGTTTTAGCCAATAGAAATGCACAAAACCACAACAAACATGCAGCAGACA
ACGGATCTTGACTTTGATTTCCAGATGCCGTGTCGCTATTTCAAAAGTTCTTTTGCGCGTTCGCTTTCGCTCAACAACAACAACAACAACAACAA
CAACAACAACAACAACAACAATGCCTTGACATTGCCCAAGAAGCCGCCAACAAACGAGGCCAAACTACAACAACAACAACAACAGCAGCAGCTGG
AGAATCAGGAATCGCTAGAGAGAGACAACGAACAGGATTCCCCCTGCGCCACCCCGCCCCCCGCTCTGCCAGCACGACGTCACACCGCCAACATG
ATACACTTTGGCGCCTCTAATCAGCTGCTCACCGCCCAGCCGCCCCCATCCCCCTCAGCATCCACAACCACCGGCACAATCCGCCAGGAATCTCAA
TCTCGTCTGGCCAATGCAACCGACACATCAGCCAACACAGCAGCAGGTTAGTACAGTAATCTTTGCGCCAAACGAGAATTCTCGGAATTTAAATT
CCGCAGTAATGCCAACATTTAACGTTATGAGGAAATGCTTGGGCTACAAAAAAAATTAA
(SEQ ID NO: 929)

Start ATG: 559 (Reverse strand: CAT)

MQQTTDLDFDFQMPCRYFKSSFARSLSLNNNNNNNNNNNNNNNALTLPKKPPTNEAKLQQQQQQQLENQESLERDNEQDSPCATPPPALPARRH
TANMIHFGASNQLLTAQPPHPPQHPQPPAQSARNLNLVWPMQPTHQPTQQQVSTVIFAPNENSRNLNSAVMPTFNVMRKCLGYKKN*
(SEQ ID NO: 930)

Celera Sequence No. : 142000013384474
AATGAAGGCTTCTGTGTCCGCAGCGAATGCCAAGCCCAAGCTAACGCGACCGTCGGACTCGATTTTAGTTGAGCAACTGAGCGCCGCCGTTTTGT
CACATTCGGTGCTTAATTTTGGCTAGCAGCGAACTGGGAACGGGCAGAGCTGTTTTACCACCTCTCATCGACGTTCTCGCAGGCAAGCCGGTTTC
TTGACTCAGCCTGATTTCGATTTAAAAAGCTTAACTAAGCATTCATACATTTAACGGATTCGCAATACGATAATTAACACTTTTGGCTTAGTGCA
AATATTGGGAAGAAGTTACTATGAAGGCTAATAAACTTTTTATTACTTGTCAATAACTATGCTATTATATTTATTGTATTATATTTATGTACTTC
TTTGTTAGATAAGCATAATTTAAAGATACAGTATCTCACCTGTTTCATATTCAACTTAAGCTGCTCCTTGATTTCCTGGCATATATTTTCAAGTA
CCGAGTAATATGTGAAAGTCTGCCATATCAGAAGAGACAGCATAAAGGATAGTATTATATTCACACTTAGTCTGTTCATGTCTGCAATAAATATA
CCAACTAGTAACTACGTTTTCCATATCAAACTAATTTGCATGGCCAATTTCACGGAAGCGTTTAAAATACAATTATTTGCTTTATTTGAGTCTAA
ACGGTGTAGCGCGAACTATTTAAATGCAATCGATTGGCGACTGTGGCTACAGTTATCGATAGATTTTACTTTTAAAAACCGTGACTCAATGAATC
TAAATTATCAACTATGAATTATAATGAATTACTATTTTCAATTTCTTGTTATTTTATTAACAACATAACTTTGCTTACCTTTCATTTATAAATAC
CGTGATCGAAAATTGGAGTCACTAAAGTCACGGCAGAAAAGTTCATCTCTATTAAGCCAAAGCCAAACAAAGAAGCACACAAAAGTTTATACCAT
AGTTTATTGTTTACCAAAAATATGACCTGTAGTTAAACAGCAGTTAAGCAATGGAGGACCTGTGTCGAATTTGTGGCGGGGCCTCGGAAAACATG
CTGGGCATTTTCGACGATCAGGTGGAAGAATATGTTGATGGAGCCAAGCTCGCTGAGATGGTGAAGACATGTGCCGACGTGCAGTTGGATCCCGA
CGACGCTATGCCCCAAAAAATGTGCATTTCCTGTGTCCACGATGCACGAACTGCTTACGGATTCAAGCGAAGATGCGAAGAGAACTACAAGAAGT
TCTATTTGGCGATATTAAATGGGCAGGTCATCAAGGACGAGCCCAACGAGGAGGATTTCCTATTCATTGAGAACCCAGACAAAGGCAATCTGGAA
GCAAAGAAGAAACTCAACAAGGAAATTAAAAAGACACATCAAACAGCTTCCAGAACAACCAAGTCTTCCATAACAACCAGTAGAGCTGGCAGACA
GCTAAGGAGTATAAAGAATCAGACTTTCAAATGCGAACTATGCATCAAACAGTTCAAGCGCCAAATAAACCTCCTGGACCACATGAAGTAATTAC
AATCAATACATATGATTTCACCTGTTCTTAAAATTGTATATCTCATTCCACAGGGTTCACAGCAATTCACACGTATGCCAAAACTGCGAAGAGCG
TTTTCTGTTCAAGGCCGATCTGGATAACCACCAATGTTATCGCAATAGCAATTCCACCGTCGAGTGCCCGGAATGCTTAAAGGTCTTTTCAAGCA CCCAGAGCCTGGACAGCCACAAATGCAAGGATATGCAGGAGCGTTCGCCCTTTCAGTGCCCCCACTGTCAGCAGGCCTTTACTCGCGAACAAAAC
CTCAAGGCGCACCTGTTGATCCACGCGGAATCGAAACAGGGAAACGGACCCCACAAATGTTCATACTGCCAAACGGGATTCTTCAACAAGTCGGC
CCTCAAGGTGCACATCCATGCGCACATGGGCGAACGGCCGCATGCCTGTCCCTTCTGCGTGTCCAACTTCCGTTCCAAGCAGGCCCTTAAGGTCC
ACATCCGCATACACACGGGCGAGAAGCCCTACCAATGCCCCCACTGCCCCAAGACTTTTTCGGACAACAATAACCTGGCGAAGCACCGACGACGC
CACTCGGATGAACGGCCCTACAAGTGTTCCATCTGCCTGCAGGACTTCCGGGAGAAACATCATCTGAAGCGGCACTTTCTGGGCAAGCATCGGGA
TGGAGATCAAAAGCTAAAGCTAAAGTGATACCTTAAATTCTTGACCAAATACCACGGCTTACTCGAATAAATAAATTAGGATTCGGTTATGTTTA
TATCTCATTGTTTCTATAGTTCATATTGGGATTTAATTGAATTTAGGATTTATATTTTCGTAGAATTCGAACAGCACTTTGAAAACCATTTGGAG
TGGCAACACCGTTTTTCTGTAAATCAAAATTCGATGTAGACACGACGATATAGACAGCGTTGCCATTCGGCCGTGATTTGTTCACGTGGCACCAC
CATTTTGATAAACAAGCTAAACAACCCTTAAATCGCTCGAAAAGAGCAATGGAAAAAAACAACAAGTTGTATGTTTATAAATTATAAGTCTTACA
AATTGTAATTGTGGTTTCCGTTTGCTTAGAACATCAAAGCAGCTACCAACACACAAAAAATACCGAATATTTCTCGACGTAATTTTCCCTAGACG
TCCTTACAATTCGTCGTGTTCGCTTTGATCTTTGTCTTGCTTAGATTCATCATCCTTCTCCTCATCGTCATCATCCTCGTCCTCATCGTCCTTGT
CGGAAGCCTTTTTCGCCTCCTCCTCGTCCTTCTTGCGCTGCACCTCATCCTGGGCCTCCTTCATTTTCTTCTCGCCCGCCTGGGTGTTCTTGACT
TCGGCAGCAGCCTTAGCGGCCAGCTCCACGTCGTCCGTGATCAGGACGTTGTCGAAGATAGTGCCGGACTTGACCTGCCAGAGATCGAAGCCCAG
GGTGCAGATCTCCTTGCGCAGATACAGCTTGTCGTCGGGCACATACTCGGGATTGGCGATCTCGGGATGCTCCCAGGCGCCCTTGTAGTTGGGGT
TGTCCAGCTGCTTTGGCTGCCACTCGCCCTTGAACTCAGGGTTGTCGATCATCGGTGGCTCCCACTCGCCGTCCATCTCATCGTCCCAATCCTCA
GGCTTTGTGGCATCTGGGTCGGGAATGTGCTCTGGTTTGTCCCAGTCCTCGGGCTTCTTGTCATCGGGATCGGGAATG
(SEQ ID NO: 931)

Exon: 1001..1512
Exon: 1574..2213
Start ATG: 1001

Transcript No. : CT24575
ATGGAGGACCTGTGTCGAATTTGTGGCGGGGCCTCGGAAAACATGCTGGGCATTTTCGACGATCAGGTGGAAGAATATGTTGATGGAGCCAAGCT
CGCTGAGATGGTGAAGACATGTGCCGACGTGCAGTTGGATCCCGACGACGCTATGCCCCAAAAAATGTGCATTTCCTGTGTCCACGATGCACGAA
CTGCTTACGGATTCAAGCGAAGATGCGAAGAGAACTACAAGAAGTTCTATTTGGCGATATTAAATGGGCAGGTCATCAAGGACGAGCCCAACGAG
GAGGATTTCCTATTCATTGAGAACCCAGACAAAGGCAATCTGGAAGCAAAGAAGAAACTCAACAAGGAAATTAAAAAGACACATCAAACAGCTTC
CAGAACAACCAAGTCTTCCATAACAACCAGTAGAGCTGGCAGACAGCTAAGGAGTATAAAGAATCAGACTTTCAAATGCGAACTATGCATCAAAC
AGTTCAAGCGCCAAATAAACCTCCTGGACCACATGAAGGTTCACAGCAATTCACACGTATGCCAAAACTGCGAAGAGCGTTTTCTGTTCAAGGCC
GATCTGGATAACCACCAATGTTATCGCAATAGCAATTCCACCGTCGAGTGCCCGGAATGCTTAAAGGTCTTTTCAAGCACCCAGAGCCTGGACAG
CCACAAATGCAAGGATATGCAGGAGCGTTCGCCCTTTCAGTGCCCCCACTGTCAGCAGGCCTTTACTCGCGAACAAAACCTCAAGGCGCACCTGT
TGATCCACGCGGAATCGAAACAGGGAAACGGACCCCACAAATGTTCATACTGCCAAACGGGATTCTTCAACAAGTCGGCCCTCAAGGTGCACATC
CATGCGCACATGGGCGAACGGCCGCATGCCTGTCCCTTCTGCGTGTCCAACTTCCGTTCCAAGCAGGCCCTTAAGGTCCACATCCGCATACACAC
GGGCGAGAAGCCCTACCAATGCCCCCACTGCCCCAAGACTTTTTCGGACAACAATAACCTGGCGAAGCACCGACGACGCCACTCGGATGAACGGC
CCTACAAGTGTTCCATCTGCCTGCAGGACTTCCGGGAGAAACATCATCTGAAGCGGCACTTTCTGGGCAAGCATCGGGATGGAGATCAAAAGCTA
AAGCTAAAGTGA
(SEQ ID NO: 932)

Start ATG: 1

MEDLCRICGGASENMLGIFDDQVEEYVDGAKLAEMVKTCADVQLDPDDAMPQKMCISCVHDARTAYGFKRRCEENYKKFYLAILNGQVIKDEPNE
EDFLFIENPDKGNLEAKKKLNKEIKKTHQTASRTTKSSITTSRAGRQLRSIKNQTFKCELCIKQFKRQINLLDHMKVHSNSHVCQNCEERFLFKA
DLDNHQCYRNSNSTVECPECLKVFSSTQSLDSHKCKDMQERSPFQCPHCQQAFTREQNLKAHLLIHAESKQGNGPHKCSYCQTGFFNKSALKVHI
HAHMGERPHACPFCVSNFRSKQALKVHIRIHTGEKPYQCPHCPKTFSDNNNLAKHRRRHSDERPYKCSICLQDFREKHHLKRHFLGKHRDGDQKL
KLK*
(SEQ ID NO: 933)

Name: zinc finger protein
Classification: transcription_factor

Celera Sequence No. : 142000013384474
CGCGATGACTACCACTTACCGTTGTCGAAATTCTCCTTCAGATAAACCTCGGCACTAATAAAGCCGACTGTCGCCAGCAACACTATCACTGTTTT
GCACCACATCATGTGAACGATCCCGCACCACTTTTTGGACTGACTCTTCCAACTCCGATGGTTGTCCGAACTCGGTTAAAGTTAAGTACTAAATG
CCGGCAAGAAAGTGCTATTTATTTATTGCATCTAAATCGTGCGTGTCGGAGCGGGACGGCTTGTTACTGAAATTGGTTTGCTGGAACGTTTTCAT
TGGCCCAAATCAGGCCAATCAGGGATGTCTACGTATTCTTTTTCACCGGCCAGGGCTGATTTCGATAAGCAATCGCATGCTGCCCTGTCGCTATC
GATTGCTTGAGCTGGAATTAGAAACACTAAAGTGACCGTTTGCTAATTAAATTAAATTATAAAATATATAAAATTAATATATTCTGGCATACAAT
TAATCACTTGCAGCAGGCTAAGCTAAGAAAACATAAAATTACTCCAATAACAATTCTTCTACTACTTAACAATTGTAGTAGTTACAGGAAGAACA
GTTGTGCTTCCAGAACATTCCTAAGCTTTTTAACGGCTTAAGGGTTTTGAAAATTTTAACTCACACTTACATCACATGTTAACAATTAAGTTTTC
ACCCGATAAAGTTCATAGTATTTAAAAAGTTAGAATGTTAATTATACATTATAATACAAATCAAAAACAAATAAAGGAATTCCAAAACTTTGCAC
CTGTATTTCGTTAATTTTAGGAACTTTTTTATCTATAAGTGCTAACTTTTACATTTGACTTTATTACATTAAAAAATTACAATTTTCGCTGGAAA
TGTATTATATTAATAAAAAAGATAAATAGCCAGAAATAGAAAAGTGAAATTAAATTAATTAAAACAAAAAAGCTTTGGTATTTATACCAATAGAC
CTTCTAAGGTATTTTTTAAGACCTAGCTTTGTGGCAGATACGGTAAGTTCGTGTCGAGCCCACGTGTTGAGCCAATCTTATCAAACGCCGATTCG
AATGCGGCATTAAACAAATGGATTCCCTTAACAACGGATGGTTCAGCGAACTGCAGGCCGATCTCTGGCCCGGTCAGTCATTCTCCCTGAAAGTC
AAGGAGGTCATCCACAAGGAGAAGTCCCGGTTCCAAGACATCCAGATCGTTGAAACGTAAGATAAATAATAGATAAACAAATACTTGGACACACA
ACCCCATTTGTTTACATCCGAAATTCCTCAGTCTAGACTGAAGTTTGAAGATAGATGTCAAAATAAATTAGCTTAGATTGAGATTAAAAAACTAA
ATTAAAATCATTATAAACACGCAAGTCACACAAATCCGAAATTTTTAACAGCTTAAGCTGTTGAGATTTTAAGGACTAACCTACAATAGCCTAAT
CCCATATGTATCCTACATTGAAGGTCCCTAAATCATAGATTGTAGAAATCGAAAATTTTCCACTGGTTGTTCAAACACAAATTGCCCAGCCAGCA
TTTTCGGACCCCTTTGGTTTTCGTGTGTTTATTCTTGATCTGCACCAACAGCCTTATCGATGGAGTCATCTAGGGCCAAAAACGACAGACAGAATA
CTGATAGCAAGTCAGCTCGTCTTTCAGGTTTGAGTTCCTCCAGTCGAACATTGGGTACACTTGCGCCGCTGAAAAAATCAATAATTCGATAATTC
TATTACAGCGAAACCTATGGACGGTGCCTAATTCTGGACGGAATCATTCAGTGCACGGCCAGGGATGAGTTCTCGTACCAGGAGATGATATCTTT CCTGCCGCTCTGCGCCCATCCCAATCCCAAAAAGGTCCTGATCGTGGGCGGTGGCGATGGCGGCGTTGCTCGCGAGGTGGTAAAGCATCCACTGG
TCGAGGAAGTGCATCAGGTGGAAATCGACGACCGTGTCGTCGAGCTGTCCAAGCAATATCTCCCAGCGATGGCCTGTGGTTTCGCCAACGAGAAG
TTGAAGCTTACCATTGGCGATGGATTCGACTATATGAAGAAACACAAGAACGAATTTGATGTCATCATCACCGACAGCTCGGATCCCATTGGTCC
GGCAGTGAGCCTGTTTCAGGAAAGCTACTACGAGCTAATGAAACACGCGCTGAAGGATGACGGAATCGTGTGCTCCCAGGGCGGTAGCTTCTGGC
TGGACCTGGACTACATCAAGAAGACCATGTCCGGCTGCAAGGAGCACTTTGCTAAGGTGGCCTATGCCGTCACCTCCGTTCCGTCCTATCCCTGC
GGCCACATTGGCTTCGTCATGGGCTCCCTGAACAAAAACCAGGACTTCGCTACTCCCAAGCTTGGAAAGTCCGAAATCGATTCTATAGACCTAAG
GTACTACTCCTCCGAGGTTCACTCCGCCGCCTTTGCCTTGCCTCGATGGGTGCAGAAGCACTTTTACGAATGACCAGGTTGCGGAAAGATTCGTG
TGTATCTGTTTGTTAAAAATAAATATGATAATAATATGACTTGTTTATCATCGCTTCTTAAATTCTTGGATATTTTCAACAAATGCTGACTCTTG
CAATGATTCATTTTTAGTCGAATTTTTGTAGCCTGAGTATTTTCCTTCCAATCCGACTACCATCTTTCAGTTATTTTACTGTTGAAAATAGAACA
AATTGTAATGTTTATTACGTAATGATATATACAGTTGGCTCTATTTAATTTTTGTATTTGTAAGTGGATGCTGGGTTAACATAATGAGACTTATT
GCAATATTTTACACGACCGAATGTTACTCTCATTTATATATCGCATATATTGCAAAACTTTGAAAGGAAGCGTTTCTTATATGCAAAAATGACCT
TAACTGCATGTGAATAATTAACTAAAAACTGATATTCAATTTCAATAACTTAATAGAAATTAAATCTTCAACCTGTTTAATGACTAATTAAATAT
TGTTATAGTTAGGAAACGCAATTGATACATAATTACAAAATTAGATGTAAAATATGTACAATCATTTAATATTGGTTTTTATTTTCTCGCCTATT
CTAAAGTTAATTATCATTTCTTTTGTGTCGGATAGATTTTGGTGTCTAATGTGCGTGTTTTATGTGTAATAAATATAATGTATGTGCATTGCGA
TTTTGGTAGCCGAGCTCCAGTTTTCGAAAAAGTCGAATCATTTTGTGTCCAATTGAGAACTATTTCACATTTTTCGAAATAGATGGATAAACTAA
TTATTGTGTGTGTACGAATACTCCACTCCTTTGACTGGGTAAATTTGAATAAACCTATAAAAATTCCTAATTCAAGTATAATAATTTTGTCTAAA
TAAATCAATTTGTAAATGTGTATTCCAAAAAAAGAATCACGAGCAGTTGGAAAAAAATTAATAATAATGGTTTTGAAAACCGGAGCTTGACTGTG
TATAATTTGTTATGCGATTGATTTTGTATAGGGAATTTCATGTCTTCGCGATTACATTTGTTATAGCGTGTTTTATATTATCAAT
(SEQ ID NO: 934)

Exon: 1001..1196
Exon: 1719..2505
Start ATG: 1063

Transcript No. : CT24589
GTGTCGAGCCCACGTGTTGAGCCAATCTTATCAAACGCCGATTCGAATGCGGCATTAAACAAATGGATTCCCTTAACAACGGATGGTTCAGCGAA
CTGCAGGCCGATCTCTGGCCCGGTCAGTCATTCTCCCTGAAAGTCAAGGAGGTCATCCACAAGGAGAAGTCCCGGTTCCAAGACATCCAGATCGT
TGAAACCGAAACCTATGGACGGTGCCTAATTCTGGACGGAATCATTCAGTGCACGGCCAGGGATGAGTTCTCGTACCAGGAGATGATATCTTTCC
TGCCGCTCTGCGCCCATCCCAATCCCAAAAAGGTCCTGATCGTGGGCGGTGGCGATGGCGGCGTTGCTCGCGAGGTGGTAAAGCATCCACTGGTC
GAGGAAGTGCATCAGGTGGAAATCGACGACCGTGTCGTCGAGCTGTCCAAGCAATATCTCCCAGCGATGGCCTGTGGTTTCGCCAACGAGAAGTT
GAAGCTTACCATTGGCGATGGATTCGACTATATGAAGAAACACAAGAACGAATTTGATGTCATCATCACCGACAGCTCGGATCCCATTGGTCCGG
CAGTGAGCCTGTTTCAGGAAAGCTACTACGAGCTAATGAAACACGCGCTGAAGGATGACGGAATCGTGTGCTCCCAGGGCGGTAGCTTCTGGCTG
GACCTGGACTACATCAAGAAGACCATGTCCGGCTGCAAGGAGCACTTTGCTAAGGTGGCCTATGCCGTCACCTCCGTTCCGTCCTATCCCTGCGG
CCACATTGGCTTCGTCATGGGCTCCCTGAACAAAAACCAGGACTTCGCTACTCCCAAGCTTGGAAAGTCCGAAATCGATTCTATAGACCTAAGGT
ACTACTCCTCCGAGGTTCACTCCGCCGCCTTTGCCTTGCCTCGATGGGTGCAGAAGCACTTTTACGAATGACCAGGTTGCGGAAAGATTCGTGTG
TATCTGTTTGTTAAAAATAAATATGATAATAAT
(SEQ ID NO: 935)

Start ATG: 63

MDSLNNGWFSELQADLWPGQSFSLKVKEVIHKEKSRFQDIQIVETETYGRCLILDGIIQCTARDEFSYQEMISFLPLCAHPNPKKVLIVGGGDGG
VAREVVKHPLVEEVHQVEIDDRVVELSKQYLPAMACGFANEKLKLTIGDGFDYMKKHKNEFDVIITDSSDPIGPAVSLFQESYYELMKHALKDDG
IVCSQGGSFWLDLDYIKKTMSGCKEHFAKVAYAVTSVPSYPCGHIGFVMGSLNKNQDFATPKLGKSEIDSIDLRYYSSEVHSAAFALPRWVQKHF
YE*
(SEQ ID NO: 936)

Name: spermidine synthase
Classification: enzyme

Celera Sequence No. : 142000013383927
GCCCTGGTCGACTTTGAGAAAGTCAGCGTCCCAGGATGAGATGTCATCAGTGCGCTTCTCCTTGTTCTCAACCTCTTCGGTAACCACAGGATCGT
CCTTGTGATAGGTGGCCCAGTGGAGCACTTTCTTCAGGATCAGCGAGTTGACATTCGGCAACGGCAGCACACTGTTGTCGCTCTCATCGCCCAAA
TCCTCTATTGCAATGCGAATCGTTTCCGAGCACTTGGCGATCTCCTGATCCGTGTCAAAGATCTCCTTGTCCGCAGACTCCAGCCGAATGATGGG
CATCTCTGCGTAAAAATTTTTATTTTTGCTTATATCTATATTTTCAATTTTATTCGTACACACCTCCTGCTGATTTGGATCCCAAGATTTGATAC
GAAATCGGTTTGATTTATTTGCAGACGCAGCCAAACAAAATTTTTAGACACAACACGATGTCACTTAGCTGTGGCCTACTGGCTAAAAATAATAT
TCCCTTGCCTTCAACTTGAACCGGACTGGTGCGGCGGCCGCCGCCTGAGAACAGAGCGTTTGTTAAATAAAGAACTTGGCTGCCAATAATTCCCCGGA
TTCTTAGAAAACTAGAACGTCGTACGATTTGAAGAGGAAATTTGTTAGTGAAACGGCCGCCAGTGTGCACATACTCGGAATGGCTTTAAAAGATG
GCGCCTATTACAGTTAATGGTGTGGAGACACTGTGACAGCTAGCGGTAAACAAAAGCTCAGTTATATTTTTTTATAATGTATATATATATATTTT
TTTTAAACATATATATTTGGCACAATTCAAGCGTGCTGGGCGTTGTATTATTTAAACAGAAACCTACAAAATTCTGCCTTTATAGTTAGTTTTT
ATCCTGTTTTTATTTAATGAATTTCAAATTTCAAATATTTTTGTAAACAATTTTAAGCTAGGCCAAGGGTTTGTGTCGCGGCTAGTGCAAGCAGT
CAACTTGCGGCATTTTTTAGTACATTTCCCTCTGTGCTGGGTTATATATTCGCAGGCTATACTCCACACTGCTTCCAGCGGAATCGTCAAAAAAA
TAACATTAAAATCGCCGTGTGCATAATTAGAATATTTCCGAATAGTAATCGCCCGTGAAATCGCTAATTAGCGGTCAGCACTTGCGCCAGTTAAA
GAAATCGCGGCACCGGCAGTGGGCCAAAAGAACATTTTTTCCGGCTGAAAAAAACAGGCGGCGGCGTCGACACGCGGACCGAACCAAAGGATCCG
AAGCCATCCGATCAGATCTAATCCGATCCGGAGAAAATTCCAGGACACTAAGGACTTCCGAAACTACCCCGCACAAGAGATGGACGTGTACGACG
TGAGCGATGATCTGATAAAGAAGCTGCAGGACTGGAAACTAATCGGCATCATATCCGGCAAGTTCAACGAGCTGAAGGAGAACCATCGCAAGGTT
GACTTCGTGATGCGCGCTCTTATTGACTTCAAGTACATTGAAAAGATATTCCTGAATGTAACGCTTCGAGAGGACAAGTGCAACAAGCGGAGCGT
GGAGTTCCGTATGCTGGGCAACGAGCAGTTTTCGCTCAAGAACAGGAATTACTTCCAGGTAATCATTGCCCCCTCAATCGGCAAACTTAAGCTAA
TCCCTGCGACTCGTTTCAGGCTCTAGAGCTGTACAACAAAAGCATCTGTTATGCCGAACCGAATTCGGAGCACCTGTCCATCGGCTATGCTAATC
GGTCGGCGGTACTATTCGAGTGGAAGCGCTATCGGCAATGCCTGGACAATATCAAGCTGGCAAGGCAGGCCAACTATCCGGCGAGACTGAGCCAC
AAACTAGACAAGCGAGAAAGGGACTGCCAACAGCTACTCGATCAGCAACCGCCGGATGTGGTGCCCTATGAGTTCAAGCTCAGTTTCGAACCGCA TGCCCAGGTGCCCTTCATCGCCGACTGTTTGGAGTTGCGCGAAACCGCCGCCGAGGGTCGCTTTGTGGTGACCAATCGGGATTTGGCCGTTGGGG
ATCTTGTGTCCGTGGAGGAGCCCTTCTGCTCCACACTGCTGACGCCGATGCGATACATTCGGTGTGCCACCTGCAAGCGGGAGAACTATCTGACC
CTCATACCCTGCGACAGCTGCTGTTCCACGATGTTCTGCTCCGAGGAGTGCAAGTCGATTGCCATGCAAACCTATCACCGCTACGAGTGCCCCAT
CATTGACTTTCTGAACCGCATGTTCAACAAGATCCACTGTATCGCACTGCGCACCACACTGGTCGCGCTGAATATCTTTCCCAGCATCGAGGAGC
TAATTGACTTCTGTGAGCAGGAGCAGAACCAGGACAAGTGCGCCTTTGACCTCAACTACAACGAGCTGACGCCGGAGGAGCACTACCGGGCCATC
CATGGACTGGTGACAAACCAGCACCTGCGCTCCGTCTCCGATCTCTTCCAGCGCTCCGTGGTCTGTGCTGTGCTCAAGCACTTCATAATCGAATA
CACACCCGTCAAGGAATATTTGGGCGGCGAAGAAGGCGTGAACTTCTTCACGGACCTCCTGTTCCGACATCTGCAGACATCTCCCTCGAATATGC
ACGGCATCGACCTGGTCGAGCAGGTTAACGAGACCAAGGACGACCAGACGCACTCGTCTGGGGCGTACGCCTTCCTCTCGCTCATAAATCACTCT
TGTGCGCCGAATACTGTAAGGATATACGAGGGCACCAAGGCGTACATGTTCGTCCTGCGGCCTATTAAGGCGGGAAATGTGCTCTACGACAATTA
CGGGTAAGTAGTAACCAAAGCATTCTGACCACACCACTTTAGTTCAAGCTAATAGGGGTCCAAGTCACTGCAGCTCTCTTCAAATACTAAAACTA
ATAGATATCCAACTTTTTAGTGCTCACTTCGCCATCTGCAGCAAGGAGCAGCGTTTGAAAAGGCTGTCCCTGCAGTACCGCTTCGACTGCAAATG
CGAGGGCTGCGAGCTGAACTATCCTATGTTCGGAATGATGCCGCACAAGGCGACGGTGCCATCGGTTACCGATGACACGGAATTGGCACTGAGCT
CCTACAACTATGATTTCGCGGTGAGCAACTATCGAAAGTACTGCGACTTCCTCACGCAATACGGTGACGACTATCCGTGCGAGCAGATTAGCTCC
GCGGAGGAGTGCCTAAAGATGGCCCTGCATATCATGGCGGACGCAGTGCCGCTCAAGGCGAAGATGTAATCGGATCCTGCCGCTGAACCAACCCA
CACAACCAACACGGACGAACTTTTCCTTTGCTAACTTTAACTGGAGACAGCGTATTACAAGCGAGACACAAATCAAGGAGAGTAATTGATTATAC
ATACATGTTGTTGCCATAAGTCTGTAGCGCAGGCAGCAGCGCGATGGGGAGGGAGCATGCCCTTAACTTTTATATTTGTAATTGTACATTTTCGA
CCTTTGATTATGTTTTACCCCGCACCAAGCCCGCACACCACACCCACACAACGCCCAGCACACCCACACAACGCCCAGCACACCCACACAACGCC
CAGCACACCCACCACACATTTCACAACAATTCGAAAGTTCAAAATTCTAAAGTTTATTTATTTTTTGATCACAACAATGTCTTCGATGAAAACAA
ACAAACAAAGGATTATTATGCAACCTACGTCGTTTTTATAATTATTTTACAAAAACCAACTGAAGCAGAAATAAAATATTTTCAAAACGAAGTGA
CTTTGGCCTCAAGGCATTTTGCTGTACAGGTCCAGCAGGTTCTGGTTCAGCAAGGATCCTCCCCGGGACATGGACGTCGCCACCTTTTCCGAGGA
CGATGCCGATGTCGTGGGCTGCAGCTGTACAAACTCGCAGCCAGAGGAGCTGGCCGCTGTGTCATTGAAAAGCACATTGCCGAAGGCCTGCTCGA
ACTGCTGCTGGAACTGGCGGGCGTTGATGGGCTGCAGATCCTCACTTTGCGCCGGATTTATGTTCAGCTGAGCGGCCAGCTGATCCATGCTGTTG
GGCTCCCGTTGTTGGCGCTCCCGCTGGTCGGCACTCTTCGCATAGATATTATCGCCGGCTGACTCAACGTATTCCGCGTAGTAATCTTGATCCAC
GTCCCTGATGAAACTACCGTCCATGGCCTGAAAGCCCATGCGAATCAAAAGCGATATCTTTGTGTTAAAGCACTGCAGCCAGGCCCGATTCGTCT
GGTAGATGGACAGCTGCGCATCCTCACCGCTGGCATTCCAAAAGTCCAGCAGCGTGTTTTTCGTGAAGTCAATCAGCATATGCCGTTTGGCATCC
GGATACAACCTGTTGATCGCCTCCAAGTGCCGAAATGTAATCTCCAGCAGATGGTGCTGATGGCGGGAAACGAAAAGCTGCCACTTGTAGACCAT
AGTCATCAGATTCCACAGCTTGGACATCGACTGCTCGTCGAGTCGCATCAAGGAGCAGGTGGCAATGTCGTTCAGCATAAACTTGCAATGCTCGG
CGGTCAAAAGCTGCGCACTATTGTGTTTCGATCCGTTTAGGAGCGAGTCTATAAACTTTGGTTCGAGCAGCACAGAAGTCACATCGTGGATAACT
GGTGGAAGATATATATATAGTGTCTTTTAAATTTGAATTTGAATTTGAATTGAAGCATATAGCTATGCAGAAGACTC
(SEQ ID NO: 937)

Exon: 1001..1578
Exon: 1635..2758
Exon: 2871..3637
Start ATG: 1315

Transcript No. : CT24669
CGCAGGCTATACTCCACACTGCTTCCAGCGGAATCGTCAAAAAAATAACATTAAAATCGCCGTGTGCATAATTAGAATATTTCCGAATAGTAATC
GCCCGTGAAATCGCTAATTAGCGGTCAGCACTTGCGCCAGTTAAAGAAATCGCGGCACCGGCAGTGGGCCAAAAGAACATTTTTTCCGGCTGAAA
AAAACAGGCGGCGGCGTCGACACGCGGACCGAACCAAAGGATCCGAAGCCATCCGATCAGATCTAATCCGATCCGGAGAAAATTCCAGGACACTA
AGGACTTCCGAAACTACCCCGCACAAGAGATGGACGTGTACGACGTGAGCGATGATCTGATAAAGAAGCTGCAGGACTGGAAACTAATCGGCATC
ATATCCGGCAAGTTCAACGAGCTGAAGGAGAACCATCGCAAGGTTGACTTCGTGATGCGCGCTCTTATTGACTTCAAGTACATTGAAAAGATATT
CCTGAATGTAACGCTTCGAGAGGACAAGTGCAACAAGCGGAGCGTGGAGTTCCGTATGCTGGGCAACGAGCAGTTTTCGCTCAAGAACAGGAATT
ACTTCCAGGCTCTAGAGCTGTACAACAAAAGCATCTGTTATGCCGAACCGAATTCGGAGCACCTGTCCATCGGCTATGCTAATCGGTCGGCGGTA
CTATTCGAGTGGAAGCGCTATCGGCAATGCCTGGACAATATCAAGCTGGCAAGGCAGGCCAACTATCCGGCGAGACTGAGCCACAAACTAGACAA
GCGAGAAAGGGACTGCCAACAGCTACTCGATCAGCAACCGCCGGATGTGGTGCCCTATGAGTTCAAGCTCAGTTTCGAACCGCATGCCCAGGTGC
CCTTCATCGCCGACTGTTTGGAGTTGCGCGAAACCGCCGCCGAGGGTCGCTTTGTGGTGACCAATCGGGATTTGGCCGTTGGGGATCTTGTGTCC
GTGGAGGAGCCCTTCTGCTCCACACTGCTGACGCCGATGCGATACATTCGGTGTGCCACCTGCAAGCGGGAGAACTATCTGACCCTCATACCCTG
CGACAGCTGCTGTTCCACGATGTTCTGCTCCGAGGAGTGCAAGTCGATTGCCATGCAAACCTATCACCGCTACGAGTGCCCCATCATTGACTTTC
TGAACCGCATGTTCAACAAGATCCACTGTATCGCACTGCGCACCACACTGGTCGCGCTGAATATCTTTCCCAGCATCGAGGAGCTAATTGACTTC
TGTGAGCAGGAGCAGAACCAGGACAAGTGCGCCTTTGACCTCAACTACAACGAGCTGACGCCGGAGGAGCACTACCGGGCCATCCATGGACTGGT
GACAAACCAGCACCTGCGCTCCGTCTCCGATCTCTTCCAGCGCTCCGTGGTCTGTGCTGTGCTCAAGCACTTCATAATCGAATACACACCCGTCA
AGGAATATTTGGGCGGCGAAGAAGGCGTGAACTTCTTCACGGACCTCCTGTTCCGACATCTGCAGACATCTCCCTCGAATATGCACGGCATCGAC
CTGGTCGAGCAGGTTAACGAGACCAAGGACGACCAGACGCACTCGTCTGGGGCGTACGCCTTCCTCTCGCTCATAAATCACTCTTGTGCGCCGAA
TACTGTAAGGATATACGAGGGCACCAAGGCGTACATGTTCGTCCTGCGGCCTATTAAGGCGGGAAATGTGCTCTACGACAATTACGGTGCTCACT
TCGCCATCTGCAGCAAGGAGCAGCGTTTGAAAAGGCTGTCCCTGCAGTACCGCTTCGACTGCAAATGCGAGGGCTGCGAGCTGAACTATCCTATG
TTCGGAATGATGCCGCACAAGGCGACGGTGCCATCGGTTACCGATGACACGGAATTGGCACTGAGCTCCTACAACTATGATTTCGCGGTGAGCAA
CTATCGAAAGTACTGCGACTTCCTCACGCAATACGGTGACGACTATCCGTGCGAGCAGATTAGCTCCGCGGAGGAGTGCCTAAAGATGGCCCTGC
ATATCATGGCGGACGCAGTGCCGCTCAAGGCGAAGATGTAATCGGATCCTGCCGCTGAACCAACCCCACACAACCAACACGGACGAACTTTTCCTT
TGCTAACTTTAACTGGAGACAGCGTATTACAAGCGAGACACAAATCAAGGAGAGTAATTGATTATACATACATGTTGTTGCCATAAGTCTGTAGC
GCAGGCAGCAGCGCGATGGGGAGGGAGCATGCCCTTAACTTTTATATTTGTAATTGTACATTTTCGACCTTTGATTATGTTTTACCCCGCACCAA
GCCCGCACACCACACCCACACAACGCCCAGCACACCCACACAACGCCCAGCACACCCACACAACGCCCAGCACACCCACCACACATTTCACAACA
ATTCGAAAGTTCAAAATTCTAAAGTTTATTTATTTTTTGATCACAACAATGTCTTCGATGAAAACAAACAAACAAAGGATTATTATGCAACCTA
(SEQ ID NO: 938)

Start ATG: 315

MDVYDVSDDLIKKLQDWKLIGIISGKFNELKENHRKVDFVMRALIDFKYIEKIFLNVTLREDKCNKRSVEFRMLGNEQFSLKNRNYFQALELYNK
SICYAEPNSEHLSIGYANRSAVLFEWKRYRQCLDNIKLARQANYPARLSHKLDKRERDCQQLLDQQPPDVVPYEFKLSFEPHAQVPFIADCLELR
ETAAEGRFVVTNRDLAVGDLVSVEEPFCSTLLTPMRYIRCATCKRENYLTLIPCDSCCSTMFCSEECKSIAMQTYHRYECPIIDFLNRMFNKIHC
IALRTTLVALNIFPSIEELIDFCEQEQNQDKCAFDLNYNELTPEEHYRAIHGLVTNQHLRSVSDLFQRSVVCAVLKHFIIEYTPVKEYLGGEEGV

FIGURE SHEET 505

NFFTDLLFRHLQTSPSNMHGIDLVEQVNETKDDQTHSSGAYAFLSLINHSCAPNTVRIYEGTKAYMFVLRPIKAGNVLYDNYGAHFAICSKEQRL
KRLSLQYRFDCKCEGCELNYPMFGMMPHKATVPSVTDDTELALSSYNYDFAVSNYRKYCDFLTQYGDDYPCEQISSAEECLKMALHIMADAVPLK
AKM*
(SEQ ID NO: 939)

Classification: known_flybase_gene
Gene Symbol: BcDNA:LD29892
FlyBase ID: FBgn0027495

Celera Sequence No. : 142000013384673
CGAGACCCCCAATTCCACACTATGGAGTAGCGACGGATGCATTTGGAGCGATGAAAGCAGCAAGAGCAGCCGGCATCGTTCGCAACTCTCTGTCA
AAATGGCCCGAGAACACTGTGTCGTATACGCAATGCCGCGCAGCCACTAGTTGCTGGTGTTGTGATGATGATGATGATGAAGGTGCTATTTGGTA
TGGATGTGACTGTTGACTTTGCCTCCGTTTCGATTTGAGTTTTTGGGTGTGTTTGCTGTGGCGGTTCTCTTTCGTTTTTTTTTTTTTGGGACTTT
TTCCGGAGAAGAAACAACACATATACTCACTTGTATATCGTGTTCCTGAACAACAATATCAATAGTTTTGGTTAGCTCGTGTATTTGCCCTCGTG
CTGTGGCCATTTCTATTGTGGTGTGTGTGCGTGGAGGGTTTTTGGCTTTTTCCACCAGCAAAGAGATAAACTCAAAAATGTGAATGGGAGCTCAT
TCACCGGGTTTTCGGGGAGTTCGGGACCTATGTATGTATGTATGTTTGCTCATCAGCAGGTTGCCAGCTTTCTGCTTGCTAATGGCCCAACAACA
AACAGTCGGACATTTCGAAATTGTTTCTAGAAATTATGAAATCGGAGCAGCGTCGAAAAAAGAAGATAGATAAACCCAATACGGTTGTAATTAGT
AGTACAAAAATAAAAAAAAAAAACGAAAGTCAGGCACTGCTTCGCATTCATTTGAAGGGCCATGAACTGTGAGCACTTGAAGAGTGCTAATTGAT
TAAGGCAAAAGCAAAAGCAAGTGAACCGCGATTTGTAGACCCATCGGGATTACGCCTTTATCAGTCTGGCGTTTATCCGGTTGCGGTGGCATTAT
CTTCCGGGCGACTCTCGAACTTTGTTCCCTTTACTTCCTGGGAAACTTTATTAATGAATTAATTCAAGTACAGTTGCGGTTAAAATAATAACACT
ACTGCAGTTGCAAAGTTGATTTCCTAAAAAAAATTATTAAATATTTATTTAAGTCAGATTGCATGAATAATAAGTACCATATGTAGTCTCTTTAA
GTAGTAAATGTTAACTCTCTCAATGTAACGGTTCTTTTTGTTTTTGGTCACTTGCTGCAAAAGTGCGCGAAATTAGGCGGTAACAAAAATAGTAC
TGATTACGTATTTGCTGAATAAAATTAATAAAAAATACAAAAATAAATTTGATTAAAACAAAATCAAACAAAATGATCCGCAAAGCACTGCTGTT
TGTCGAAAAGAACGAAACACGGCGAAGAAAGCCCTCAATGTCCAACGTGGAGATCAGGCGCTTGGTTCGGCAAAGCAAGAAGGATCAAGATGAGA
GCAAAATTGTGTTGTTTGGTGGGAAAGGCTCTTGGTCTTATGTTCGGCGTCCACCACGAACTGAATATAATCATCGCTTCACCTTTAAGGCGGTA
AGCACATCATGGATCAGCACATTTACACAGATATCCTGGAAAATCTGATGCTGCCATATGCCGAGGATGAAATGCCGTTGGTTTGGACATTTCAA
CAGGATAACGACTCAAAACACACGAGCAAATCACTGTAGTATTTAAGTTTAGTCAGCAATATGATGAAAAAGTGTTAGAAAATACAGAAACGGTG
GGCCAAACACGAAATGTGCTTATGGTGCTATTATTGTTACCGCAACTGTACAATACGACCATGGATATTCGATATCGTTTCGGGTCAATTCCGCT
TTTAGTTTCGTTTCTATCGCATCGACCAATCGGGCCGTGCGACAAATTTGCGTTTTTTATTGATAAGGCGCTCCGCCGTACCCTCGAAAACCCCT
TGTGCAGTGATAAGCGCCGAAATTTATATGACCATGGGTGGCACGTCATAAACATATATTAGATTAGAGAAATTAAATTCTTCTTTCAGCGCCAA
CGGCCAGCCAAACATCTTACCTAACTTGGCCGGATTTAGTGTTTAATCTAATCGCAGTATTACGGCGCACATAAATATGTACTTCGGTCTCGACT
GGGTGCAATAAAAAAAACAAACGTGTAATATATTTTAAGTCCGGATCTTACATAACAGTCTCGCAAAGAATGCCGGGTGCATTCACAGCCAGAAA
TTATTATGTTTTATTTTATGCGGCATCTCTGAATGTTAACTAAATGTTGCACATCGCCTTTATTACTATTGTTTCAACGATTAATGTTTGATTAG
GAATTTCTGTCATGTCAGCATATATAGCGAAAATATGCCCCAACTAAATATCATGGAATAAAGTAGCATCATCACTCCCCGAAGCGAGTTCCAAA
ATGATGATTCATTTGCCTCCAAATTCGGTTATCACAAAGGGGTACAAGCCCCAAAAATGTTGACGCATCTTTGGGTACATTTGGCTTTTGTTAAT
AATATGGGATTCACCTTGAAGGTACGCAAATGTGCCAAAATTACTGCACAGCATTAGTTATTTTTATATAGAATAAGCAAATAGGTTTTATTTTT
AGAATTTCAAAAAATCAGTTATCTTCTTTACAAAAAAACCAGGGCTGCGCCTTTTGTTGGTTTGAGTCCAGGGTGGATGAACGTATTTGTCAGCA
CTTTGTGACCATATGTTTGCGATAAGCATATATGCGTAAGCATATGTTAAATATTTGAATGTGCGTCAAATTAGCGTCGTTGAGTTAGCCGCGAT
GGCTGAACATTGGAAAATTTTTTTATTTATTAATTTTTTGTTATATAGAGGTGAATTCAAAGAAATAAAAATTCAAAAATGTGTCGCGCGTGCTT
GTCCCGCCGTATCTCGCCAACGTTATCTAGTGGCTAATTTACTTTCTTTAGTTAAATCTTTCTTTTCGTAACATTATTGCATATCTGTTTTTTGA
AATGCACCGCGAAATAACTATATATTCAATAAAACAATACCTAATAGTTATTGCAACTAAACCAATTAAATTTTTATTTAGTTGTATAAAATATT
TGTACGATATATCGTGGTTAAATCTTGCAAACTATCGTCGCTGGTGTTCCGGGTGAACCACGCGGCGGTCACACTGAAAACATCGCTGGTATTTC
GTAACGCTCAGCAACGGTCACTCTGCCATCCTTCTTTTTATTTCCGCCGTTTGCCGAGAAAGTTGGAAAATTATGGGTGAGTTGCTGAAAAGCGT
AGTTTTTGTGCGAATTAAGCGAACAGCGCTGACAAACAGTGAACAAACGGAGCTTACAATGCGGCGCGGCTGAAAGAGTAAGTGAATTTGCGCCG
AAAGTGCGAAAATATTGGCAAATGCAAGTCGCGGAAACTTGCGATTTCAGCTGTCCGAAAATCGCACAAAATCCAGTGAATCTTTGGTTCCAGCG
AACAAATATTTCGTTTCACATGCAAAAGCAATCGATGTGCACAAGGCACTAAAGTTATTTGTGTGAAAAATGCATTTGGCAGTATTTCCGAGCCT
GGACTCTGTCTAACCTCAAAACCGAAGCCGCACAAGCTGCCATTTGTTTACATTGTGTTGTTGCATCGCAGACGCATATTAACTATAGCTAATGT
ATACGTTTAATCTACAACAGGCAAGCCAAGAGGTCTGCGCACTGCCAGGAAGCATGTGAACCACCGTCGCGACCAGCGTTGGGCCGACAAGGACT
ACAAGAAGGCTCATTTGGGCACCAGATGGAAGGCTAATCCCTTCGGAGGTGCTTCCCACGCCAAGGGAATCGTCCTGGAGAAGGTGTAAGTACAC
GGTGGTTGACCCCACCATTGAAGTGCTATGCCCGCCATCCGGATGAGATGGCGGGGTTAATAACACGTCTCGACGCCTCGCAGTATATTTTTGTG
TTTTGTTTCGTTTTGCAATCCAAATCACAGGATTATACTGTGAGATGACCAGCGTGCCAGCAGCGAAAAGCGACTGATATGATATCAATTATATT
AATCTCTTAGTAGTATATCAAAACTAATCGGTTTCCTCTACTCCACAGCGGCGTCGAGGCCAAGCAGCCTAACTCTGCCATCCGCAAGTGCGTGA
GGGTGCAGCTCATCAAGAACGGCAAGAAGATCACCGCCTTCGTGCCCCGTGACGGTAGCTTGAACTACATTGAGGAGAACGACGAGGTCCTGGTT
GCCGGTTTCGGTCGTAAGGGTCATGCCGTCGGTGATATTCCCGGTGTGCGCTTCAAGGTTGTCAAGGTCGCCAACGTCTCCCTGTTGGCCCTCTA
CAAGGAGAAGAAGGAACGCCCAAGATCTTAGATGAACATGCATCTAATCTTTTTCCAGACAAGCAGAGTTAGGGTTTTACAAATCTAAATAAACA
AAAAACAGAAACAAACTTGTTAAATGTTTCAATTAAATGTGATTTCCTTGAATATATTTGTGGCTCGCATGTTTGTGTTTACTGATGGTAGAATA
TAGTGATTCCAATCGATTCTGTTTTATAAGGCCGATGTACTTAATGAGTTACATACTTGCATATTTAAACTATAACAGTTTACAGTTTTCGTTGT
TTTCAAGTATTTTCTGTAAAATTTAAAAATGATTATTGCCCTATATTCACATCTATGCGAAATATATTTCCCAAATTTTCGAATTTCAAAAAATA
TATAGGTATTTTTGAATCCTCTTATTGGAAAAACAATAAATATGAACATATATATTTTAAAAAGAATATATGTTTATCTTATTATTAATCAAGTT
TTTAGACTACCTGGCAACCATGGTAGTGATGCAAAGCGAAGATGCTCGAGTGCTTTCCAGCACTATTAGCCGCGTAAATTCGAATTTTTTAAATT
TGCCTAAGCGAACTCAGGACTTGCTCTTAGTTTCAGTTTCGAAAACTATGCATTCCACTAATAACTTAATTGTCAACCACACATTGGCCACCAAA
TTGTGCGATGCCGGAACACTCCTTCGATGCGGCGAACTGTGCGATCTGCAGGCGGTCGTACCTACCGCAGTTGCTATTGCCAAGTATTTCTTACA
TAACAGAACGGCAAGAGCCGCGGAAACAGACAGCCATCATCAAAGCATGAGGCCCGGACCTGGACCACAGCAACGTGTGCCGGGCTCCATCAGCG
ATAAGGAGTCACAAACTGCACCTCCTACCTGGCGGTGCACAGCGAGAAATCGGAGCACTTCGAATCGGGCTCGATTTGGAGTGGAGCTGTCTGAT
TTCTTGCAGTGCCTCGGTTCGATCTGCTTATCAATAATTTGTTTTTTTTTCTCCTCTTTGCCGCATTTAGGCAGAGATTCGCTGGCGATAGCCGC
TCAAGTGTCACACGCCCACATTTTTGGAGCAGTCGATGTCGATGGAGCGGCTATTTGCACATACGCCACGCCAATAAACTTGTACCCA
(SEQ ID NO: 940)

Exon: 1001..1348
Exon: 1420..1501

FIGURE SHEET 506

Exon: 3052..3116
Exon: 3536..3695
Exon: 3944..4313
Start ATG: 1273

Transcript No. : CT24703
AAGTCAGATTGCATGAATAATAAGTACCATATGTAGTCTCTTTAAGTAGTAAATGTTAACTCTCTCAATGTAACGGTTCTTTTTGTTTTTGGTCA
CTTGCTGCAAAAGTGCGCGAAATTAGGCGGTAACAAAAATAGTACTGATTACGTATTTGCTGAATAAAATTAATAAAAAATACAAAAATAAATTT
GATTAAAACAAAATCAAACAAAATGATCCGCAAAGCACTGCTGTTTGTCGAAAAGAACGAAACACGGCGAAGAAAGCCCTCAATGTCCAACGTGG
AGATCAGGCGCTTGGTTCGGCAAAGCAAGAAGGATCAAGATGAGAGCAAAATTGTGTTGTTTGGCGGTAAGCACATCATGGATCAGCACATTTAC
ACAGATATCCTGGAAAATCTGATGCTGCCATATGCCGAGGATGAAATGCCCAACGGTCACTCTGCCATCCTTCTTTTTATTTCCGCCGTTTGCCG
AGAAAGTTGGAAAATTATGGGCAAGCCAAGAGGTCTGCGCACTGCCAGGAAGCATGTGAACCACCGTCGCGACCAGCGTTGGGCCGACAAGGACT
ACAAGAAGGCTCATTTGGGCACCAGATGGAAGGCTAATCCCTTCGGAGGTGCTTCCCACGCCAAGGGAATCGTCCTGGAGAAGGTCGGCGTCGAG
GCCAAGCAGCCTAACTCTGCCATCCGCAAGTGCGTGAGGGTGCAGCTCATCAAGAACGGCAAGAAGATCACCGCCTTCGTGCCCCGTGACGGTAG
CTTGAACTACATTGAGGAGAACGACGAGGTCCTGGTTGCCGGTTTCGGTCGTAAGGGTCATGCCGTCGGTGATATTCCCGGTGTGCGCTTCAAGG
TTGTCAAGGTCGCCAACGTCTCCCTGTTGGCCCTCTACAAGGAGAAGAAGGAACGCCCAAGATCTTAGATGAACATGCATCTAATCTTTTTCCAG
ACAAGCAGAGTTAGGGTTTTACAAATCTAAATAAACAAAAAACAGAAACAAACTTGTTAAATGTTTCAATTAAAT
(SEQ ID NO: 941)

Start ATG: 273

MSNVEIRRLVRQSKKDQDESKIVLFGGKHIMDQHIYTDILENLMLPYAEDEMPNGHSAILLFISAVCRESWKIMGKPRGLRTARKHVNHRRDQRW
ADKDYKKAHLGTRWKANPFGGASHAKGIVLEKVGVEAKQPNSAIRKCVRVQLIKNGKKITAFVPRDGSLNYIEENDEVLVAGFGRKGHAVGDIPG
VRFKVVKVANVSLLALYKEKKERPRS*
(SEQ ID NO: 942)

Name: ribosomal protein S23-like
Classification: ribosomal_protein

Celera Sequence No. : 142000013384673
CGAGGAGGCAGACGCCACAAATGCCACGGACCAAATCATGAATACTTTGAATGCAGCCAAAGCAACGCTTCAACAAGAGCAATATTTTAATAACA
ATACCAATCTTAGTAGGAACTTCAATCACAATCACAACCAGAGCATCATCCACATCAGTAGCCAGAAAGCCAACGGCAAGAAGTCCAACGAAACA
CCAAAAGATATTTATAATCTGAACTCAATCGAGCATATCGACTTGATTTTGGAGGATAAAAGCCTTACCAAAGCAATACACGTTACCGGCTCTAA
ATGCTTTGTCACCATGAAGAAAATCCGACGGCTGGGAAAATATTTTCCCGTGATGAACTTCTCTTAATAGACACAGTTACTTCTTTGCAAAGTGC
ATTCTAAATATTAAAAAGAAACTCGGTTAAGCGAACTACATAGAAAATATGCATGTATTAATTAAAACGTATAAACGTCAACGTTATCCCCCGTA
TATAGGAAAGAGCGCGAGAATATTTAAATTTAGTGGTAGCGTAATTGTTTTGTCTGTCGTCGTCATTACGCTTAAATTATTCTAAATATATTAAT
TTATGTTAATTATAAGTCTAATCACTCAATGCAATATTTAGTGAAAATACATTAATGCCCATATGACAATTGACTAAAAAGGTTATTTGTTTTCT
TTTTAACAAATTGTGACGAATTAAAATGGAATGAAACTCGCAACTCGCACAATCTAAAATTGGCAATTCAAATGTTTGCGCCCAACTACAGTGTG
TACACACCACAAATGTTGTAGAGTAGGTAAAGGAAATAAAGCAATAAACATTTAACTACTTAAAGCTCTTAAGATGTAGTTAAGCAATGATGGAT
GTCACCAAGCAATTTTTTTTTATTGTAAGAAAAATATACAATATACAAAAATATATTCTTTTATTTTACAAAATGATGCGTGTAAAATACATTGT
ACCTAATGCAGGTACCCCAAACGAGTACAAGCCACCCTTTTCAACTCTGGTCACACAGAGCACATCCCGTAAAGTTTTTCAGAGATGAGTTTGCG
GCAGGAAAATTGAATTATTCACGGAAATAAACAAAGTAAACTAAGTGGAAACTGTAATCCTGACCAGCAATTATGTTGCGCATCTATCAAAATAC
TTACCGGTGAGAGACCACGCCCGAAACGCGAAAGCCTTACGTGCAGATTTTCTGCACGATTTCGTCATCGGCGAATCTCATCATTCAATGTGTTT
TGCCCACAGGCGCACCGCGAGAAAAGCTGTTGTCTACTCCACCAAGGTCGCCTGCTGCAATCATTCCACGCTCTGTGGCATCACCAGCCATCCAC
GTCGGGCGCAGGATAGCGGGAGCTCCAGTTCGAATGGCAGGCACCGTGGCCACGAGGAGTTCCTACTTGCCGGCAATCCGGCGCGGGGCTGGCAA
ATGCCTCCGCCGTCGCGTGGTTACGGAATGCTGGTGGTGCGCATACTGCGGGGAGCCCTCAAGCTGCGATACATCGTCCTGGGCGGCGCCATCGG
CGGGGGCGTGTCGCTGAGCAAAGTGAGTTTCGCAAGTTATATAACTTGTATAGAACTTAGGAGACATGATTTGTTTTCCGCAGAAATACGAGGAA
TGGAAGGATGGACTGCCGAATTTTAAGTGGCTGGAGGATGCCATGCCGCAGGGCGAACGGTGGAGCCAGTTCTCGCGGAATCTCATTGAGGTGGG
CTCGCTGGTGAAGAACGCCATCGAAGTTGGTGAGTGTCCATGTAGACCTACCATCGCCCTTTCAATCTCTCACTTTAAATGGTCATATACCTTGG
TCAGATTCGCATTGAACTCTTCGTTTTGATTGATTGATACTGATGTTATTGGGGCGTTTGCTTGTAGATCCAAAGCTCAAGCAGCTGGGCGAGGA
TAAGTTGTCGGAATGGCGCAACTGGTTTGACAGTCGTCTGGACGATGCCATCGAGGCGGCCGATTATCAAGGAGTTCAGATTGTCGAAAGTAGGT
TACACAAATTACACAGACTCCCAACGTTGGGACCATTTAAAGTGAGAGATCCCTATCTACCGCATTCGAGACTTATTCCTAACATCTGTTGCAGC
CAAAGATGACTTAAAGGCCAAAACAACGGTGGCCGCTTTAGGCATAACATCCGATGAGAGTCGTAAGAAGTATGGTAGGTTTTTTGCACACCTGC
CGAAAGATATACTATATCTAATCCTTCTGTGATTCCGCAGAGAAACTCCAGAGCCAGGTGGAGACGCTGCAGACGGAGATCATGAACGTCCAGAT
TAAGTACCAAAAGGAGCTGGAGAAGATGGAGAAGGAGAACCGTGAACTACGCCAGCAATACCTCATCCTGAAAACAAACAAAAAGACCACGGCAA
AAAAAATCAAAAAATCCCTGATCGACATGTACTCTGAGGTCCTTGATGAGCTATCCGGCTACGATACGGGCTACACCATGGCCGATCACCTACCC
CGTGTTGTGGTAGTGGGAGATCAGAGCAGCGGCAAGACCTCTGTCCTGGAATCCATTGCTAAGGCTCGCATCTTTCCCCGTGGCAGTGGAGAGAT
GATGACGCGAGCCCCAGTCAAAGTTACTCTGGCTGAAGGACCATACCATGTGGCTCAGTTCCGTGACTCTGACCGGGAATACGATCTCACCAAGG
AGTCTGATCTGCAGGACCTCCGTCGGGATGTGGAGTTCCGAATGAAGGCGTCGGTGAGAGGTGGTAAAACCGTCAGCAATGAAGTCATTGCCATG
ACGGTCAAGGGTCCCGGTCTGCAACGCATGGTTCTAGTCGATTTGCCAGGAATAATTTCGGTGAGCAAGTCAATACAAGTAAAACTGCGCACATC
TAATGCTAATATCATTTTAGACCATGACTGTCGACATGGCCTCAGACACAAAAGATTCCATTCACCAGATGACCAAGCATTATATGAGCAATCCG
AACGCCATCATTCTCTGCATTCAGGATGGATCTGTGGACGCTGAGCGCAGTAATGTGACAGACTTGGTCATGCAGTGCGATCCCTTGGGTCGACG
CACTATTTTTGTGCTCACAAAGGTGGATCTGGCCGAGGAGCTCGCCGATCCTGATAGAATAAGGAAAATCCTTTCGGGCAAACTCTTCCCCATGA
AGGCTTTGGGCTACTATGCCGTCGTTACCGGTCGTGGACGAAAGGATGACAGCATAGATGCTATTCGGCAGTATGAGGAAGACTTCTTTAAGAAC
TCCAAGCTTTTCCAGTAAGTATAGAGAGGATGTGATTGGTAAATTCCAAAGTTCACCTCTCTCCATACTTAGTCGTCGAGGGGTTATCATGCCCC
ATCAGGTGACCAGCCGCAATCTGAGCTTGGCGGTGTCAGATCGTTTCTGGAAGATGGTGAGGGAAACCATTGAGCAGCAGGCGGATGCATTTAAG
GCGACTAGATTTAACTCTGGAAACCGAATGGAAAAATAACTTCCCCAGGTTTGTAAAAATGTTTTAAAAAATATAAGAGATCTATAACATTTGAGG
TATACTCTTTTAGATTGCGCGAGTCTGGTCGAGATGAGCTGTTCGACAAGGCAAAGGGCGAGATACTGGACGAGGTGGTAACGCTCTCGCAAATC
TCCGCTAAAAAGTGGGACGACGCTCTGAGCACCAAGCTATGGGAAAAGCTCTCCAATTATGTGTTTGAAAGCATCTATCTGCCCGCTGCACAGTC
AGGTTCTCAAAGTAATATTTTGTAGTACTAAGTGTAGGTTGTAAGCAGATTTCGCCGACGTCATCGATGGGGGCACGTCCATCCAATCGCCCGCC TTGTGTGCTCCGTCATTGTGTGTGTTTCTTGCAAGAAGATATGGCTTGGCCTCGAACCTCACGTGTCTCTGCAAAACGTTGTGTCGTTTAAATGT
TTTGTTTAATTTTGTATTTATCATGGCCCGCATTCAGCGTCGAATTCCCGTGCAAGGGAATCACATGCGTTAAATAATTTCAAACCGGTTTGACT
GATATTCCTGCAACATTTCTTGAATCACAAGTGTAAATTTAATGTGTACTCCCCGGCGGACGATTTCGAATCCCATTAACACCGTTTGCCTTTGC
CCCAAAATAGTGACCCGGGATTGTCACAGGTTCTGCGTTGCGATCATGTGCCGGAAAGTCGCTTATAACGAAGATTTACGAGCACCTGTACCGAA
ACCAGATTTTGGTTTATGTTCACATTATAAAAACGTATGCGATATTAGCGATTTATGACCGAAAAACCCGTTTAAGCCATCGCTCAGCTTGTGTT
TATTTAGCATTTTATGACAGACCTGTTAATTTGCTCAATGAATTCATCCAAATCAATGTCTAATTGAATTAAATTGCAGTTATCGAGTTAGGAAT
CTGAATGTTTCGTCGCTTTGTTTATCATTCCCCCCGTAGTTGTGTGTCTAGTTAATTTGGCTCAACTAATTTCATACGATTACTATGCTCTTTAT
AGATTCCTTCAACACGATGGTAGACATCAAGTTGCGCCAGTGGGCCGAGCAGGCACTGCCCGCTAAGTCGGTGGAAGCTGGCTGGGAAGCGTTGC
AGCAGGAATTCATATCGCTGATGGAGCGTTCGAAGAAGGCGCAGGATCACGACGGCATCTTCGATCAGTTGAAGTCTGCGGTGGTGGATGAGGCT
ATACGTCGGCACAGCTGGGAGGACAAGGCCATCGACATGCTTCGCGTTATCCAGCTGAATACGCTGGAGGATCGGTTCGTGCACGACAAGCAGGA
GTGGGATTCGGCGGTTAAGTTCCTGGAGAGTTCGGTGAATGCCAAGCTCGTGCAGACGGAGGAGACTTTAGCACAAATGTTTGGTCCCGGCCAAA
TGCGACGAATTACCCACTGGCAGTACCTGACGCAGGATCAGCAGAAGAGGCGAAGCGTTAAGAACGAACTCGACAAAATACTCAAAAACGATACG
GTATGGGTAGTATACATTATATAGTTAGTTATTCCTCATTTACACGCATTACATTATGTTGGTAGAAACATTTGCCCACCCTGACCCATGATGAA
CTGACTACGGTTCGCAAGAACCTTCAGCGTGATAACGTGGATGTGGACACGGACTACATAAGGCAAACGTGGTTCCCGGTCTACAGAAAGTAAGT
TGTAATGCTAAACCATTTAGACTGCTTATCAGTTAGCACATATGTCTCTTTTTTCAGACACTTTCTGCAGCAGGCGTTACAGAGGGCAAAGGATT
GCCGCAAAGCATATTACCTCTACACGCAGCAGGGAGCCGAGTGTGAGGTAAGTGTTAAGGTTTTCCCTCTTATCTGAACCAATTTACTTAACTTA
TTGCTTTCTCAGATATCCTGCAGCGACGTCGTGCTCTTCTGGCGCATCCAGCAGGTGATCAAGATAACAGGCAACGCACTGAGACAGCAAGTAAT
CAATCGGGAGGCGCGGCGGCTGGACAAGGAGATCAAAGCGGTGCTGGACGAGTTCAGCGATGACGAGGAGAAGAAGGGTTACCTGCTCACCGGCA
AGCGCGTGCTACTAGCCGAGGAGCTAAGTGAGTGCTTTGCTTAATTGAATTTGGCGCCAATTTAATTGCTTTCAATTCAACAGTCAAAGTGCGGC
AGATCCAAGAGAAGCTGGAGGAGTTCATCAATTCACTTAATCAGGAAAAGTAGTGTGCCATGACCAAAGACACAACACCCGAGGCGTTACTTATT
TAACTTGATAGTTTAAGACCACATTTGAAATGTTTGTTCATAGTCACGCTTGAGCCCCTTAGTTAAGCATACTTTGTGCTCCGAAAGTAATAAAC
AAATAGATCGTTAGTTCGTATTATTGAAATCGTCTTTATTGTTTATGAAGTGTAACCTTATGTCGCATGCAATGCAATGTAAACTCATTAATTTA
AATGTAATATAAATCATTCATTCTGTTTTAATGTAATTGTAGTTGATAAACGTTAACGCGAAACGCACTCATCGTGCTGAGTATGTAGCGGTCCG
TGTGTGTTTCTGAATCTGTATCGTGTAATATATATATATACATATATATTTAAATCGGTTTGCATAAGAGCACAGCACTTTTACCAGATGCCTCA
TCGTGCGGTTGATTGTTTGTTTCGTTTTGTCCACGATCGGCTAATCCCGCGATGCGCCGGCATCTGTATCGGTATCGAGATCGGTGGTGGGTGCA
TTAACCCCGACCGATCGTCTGGCCGCGTCTCTAATTGATTGATTGTTTGATTGATAAACGTATATCTAGCTAACTATGTATGTAGCTAGCTATGT
AACATAACAAGTCCGTGATTGCGGTGCAGTACCATATCTCTTACAAGGTAAACAAATGCTCGTTCCCTATCATGTTAAATAACTCAACAAACGAT
TCTTAACTTGGCAGTCGACTTGTGGCCCAGCCATAGCCATGTGCTCAGCTGCTTAAGGCTATCGTAATAATATTAATAATGTGTTCGGTTCTCCT
CCACTCCGATCCTCCGCTTAGTCTAGCTGCTAAATTCTAGTCCACATATGGGCTCCTCCACTAAAGCTTATAGAAACATAATTTACACTCGCGCT
CCACTCTGCTCGTATGCGTGTGATTTGGGATAGGGTTGGTTGTGTGGTATTAGGGGTGTGTGTGGTAGGCACTCGATATCGCTGAAGGCACAACA
TTACGATTAGTCTTATCTTAATTGTATTAAGTACTCGGAACACGCTTTCGCACTCGCTTCCCTCCGAAATCGGGAGTTCCTTCGACAGGATGAGT
G
(SEQ ID NO: 943)

Exon: 1001..1146
Exon: 1245..1542
Exon: 1604..1739
Exon: 1873..1989
Exon: 2090..2164
Exon: 2226..2815
Exon: 2871..3244
Exon: 3303..3467
Exon: 3529..3707
Exon: 4468..4535
Exon: 4725..4940
Exon: 5006..5124
Exon: 5188..5272
Exon: 5333..5537
Exon: 5594..5746
Start ATG: 1118

Transcript No. : CT24795
TCACACAGAGCACATCCCGTAAAGTTTTTCAGAGATGAGTTTGCGGCAGGAAAATTGAATTATTCACGGAAATAAACAAAGTAAACTAAGTGGAA
ACTGTAATCCTGACCAGCAATTATGTTGCGCATCTATCAAAATACTTACCGGCGCACCGCGAGAAAAGCTGTTGTCTACTCCACCAAGGTCGCCT
GCTGCAATCATTCCACGCTCTGTGGCATCACCAGCCATCCACGTCGGGCGCAGGATAGCGGGAGCTCCAGTTCGAATGGCAGGCACCGTGGCCAC
GAGGAGTTCCTACTTGCCGGCAATCCGGCGCGGGGCTGGCAAATGCCTCCGCCGTCGCGTGGTTACGGAATGCTGGTGGTGCGCATACTGCGGGG
AGCCCTCAAGCTGCGATACATCGTCCTGGGCGGCGCCATCGGCGGGGGCGTGTCGCTGAGCAAAAAATACGAGGAATGGAAGGATGGACTGCCGA
ATTTTAAGTGGCTGGAGGATGCCATGCCGCAGGGCGAACGGTGGAGCCAGTTCTCGCGGAATCTCATTGAGGTGGGCTCGCTGGTGAAGAACGCC
ATCGAAGTTGATCCAAAGCTCAAGCAGCTGGGCGAGGATAAGTTGTCGGAATGGCGCAACTGGTTTGACAGTCGTCTGGACGATGCCATCGAGGC
GGCCGATTATCAAGGAGTTCAGATTGTCGAAACCAAAGATGACTTAAAGGCCAAAACAACGGTGGCCGCTTTAGGCATAACATCCGATGAGAGTC
GTAAGAAGTATGAGAAACTCCAGAGCCAGGTGGAGACGCTGCAGACGGAGGATCATGAACGTCCAGATTAAGTACCAAAAGGAGCTGGAGAAGATG
GAGAAGGAGAACCGTGAACTACGCCAGCAATACCTCATCCTGAAAACAAACAAAAAGACCACGGCAAAAAAAATCAAAAAATCCCTGATCGACAT
GTACTCTGAGGTCCTTGATGAGCTATCCGGCTACGATACGGGCTACACCATGGCCGATCACCTACCCCGTGTTGTGGTAGTGGGAGATCAGAGCA
GCGGCAAGACCTCTGTCCTGGAATCCATTGCTAAGGCTCGCATCTTTCCCCGTGGCAGTGGAGAGATGATGACGCGAGCCCCAGTCAAAGTTACT
CTGGCTGAAGGACCATACCATGTGGCTCAGTTCCGTGACTCTGACCGGGAATACGATCTCACCAAGGAGTCTGATCTGCAGGACCTCCGTCGGGA
TGTGGAGTTCCGAATGAAGGCGTCGGTGAGAGGTGGTAAAACCGTCAGCAATGAAGTCATTGCCATGACGGTCAAGGGTCCCGGTCTGCAACGCA
TGGTTCTAGTCGATTTGCCAGGAATAATTTCGACCATGACTGTCGACATGGCCTCAGACACAAAAGATTCCATTCACCAGATGACCAAGCATTAT
ATGAGCAATCCGAACGCCATCATTCTCTGCATTCAGGATGGATCTGTGGACGCTGAGCGCAGTAATGTGACAGACTTGGTCATGCAGTGCGATCC
CTTGGGTCGACGCACTATTTTTGTGCTCACAAAGGTGGATCTGGCCGAGGAGCTCGCCGATCCTGATAGAATAAGGAAAATCCTTTCGGGCAAAC
TCTTCCCCATGAAGGCTTTGGGCTACTATGCCGTCGTTACCGGTCGTGGACGAAAGGATGACAGCATAGATGCTATTCGGCAGTATGAGGAAGAC
TTCTTTAAGAACTCCAAGCTTTTCCATCGTCGAGGGGTTATCATGCCCCATCAGGTGACCAGCCGCAATCTGAGCTTGGCGGTGTCAGATCGTTT CTGGAAGATGGTGAGGGAAACCATTGAGCAGCAGGCGGATGCATTTAAGGCGACTAGATTTAATCTGGAAACCGAATGGAAAAATAACTTCCCCA
GATTGCGCGAGTCTGGTCGAGATGAGCTGTTCGACAAGGCAAAGGGCGAGATACTGGACGAGGTGGTAACGCTCTCGCAAATCTCCGCTAAAAAG
TGGGACGACGCTCTGAGCACCAAGCTATGGGAAAAGCTCTCCAATTATGTGTTTGAAAGCATCTATCTGCCCGCTGCACAGTCAGATTCCTTCAA
CACGATGGTAGACATCAAGTTGCGCCAGTGGGCCGAGCAGGCACTGCCCGCTAAGTCGGATCGGTTCGTGCACGACAAGCAGGAGTGGGATTCGG
CGGTTAAGTTCCTGGAGAGTTCGGTGAATGCCAAGCTCGTGCAGACGGAGGAGACTTTAGCACAAATGTTTGGTCCCGGCCAAATGCGACGAATT
ACCCACTGGCAGTACCTGACGCAGGATCAGCAGAAGAGGCGAAGCGTTAAGAACGAACTCGACAAAATACTCAAAAACGATACGAAACATTTGCC
CACCCTGACCCATGATGAACTGACTACGGTTCGCAAGAACCTTCAGCGTGATAACGTGGATGTGGACACGGACTACATAAGGCAAACGTGGTTCC
CGGTCTACAGAAAACACTTTCTGCAGCAGGCGTTACAGAGGGCAAAGGATTGCCGCAAAGCATATTACCTCTACACGCAGCAGGGAGCCGAGTGT
GAGATATCCTGCAGCGACGTCGTGCTCTTCTGGCGCATCCAGCAGGTGATCAAGATAACAGGCAACGCACTGAGACAGCAAGTAATCAATCGGGA
GGCGCGGCGGCTGGACAAGGAGATCAAAGCGGTGCTGGACGAGTTCAGCGATGACGAGGAGAAGAAGGGTTACCTGCTCACCGGCAAGCGCGTGC
TACTAGCCGAGGAGCTAATCAAAGTGCGGCAGATCCAAGAGAAGCTGGAGGAGTTCATCAATTCACTTAATCAGGAAAAGTAGTGTGCCATGACC
AAAGACACAACACCCGAGGCGTTACTTATTTAACTTGATAGTTTAAGACCACATTTGAAATGTTTGTTCATAGTCA
(SEQ ID NO: 944)

Start ATG: 118

MLRIYQNTYRRTARKAVVYSTKVACCNHSTLCGITSHPRRAQDSGSSSSNGRHRGHEEFLLAGNPARGWQMPPPSRGYGMLVVRILRGALKLRYI
VLGGAIGGGVSLSKKYEEWKDGLPNFKWLEDAMPQGERWSQFSRNLIEVGSLVKNAIEVDPKLKQLGEDKLSEWRNWFDSRLDDAIEAADYQGVQ
IVETKDDLKAKTTVAALGITSDESRKKYEKLQSQVETLQTEIMNVQIKYQKELEKMEKENRELRQQYLILKTNKKTTAKKIKKSLIDMYSEVLDE
LSGYDTGYTMADHLPRVVVVGDQSSGKTSVLESIAKARIFPRGSGEMMTRAPVKVTLAEGPYHVAQFRDSDREYDLTKESDLQDLRRDVEFRMKA
SVRGGKTVSNEVIAMTVKGPGLQRMVLVDLPGIISTMTVDMASDTKDSIHQMTKHYMSNPNAIILCIQDGSVDAERSNVTDLVMQCDPLGRRTIF
VLTKVDLAEELADPDRIRKILSGKLFPMKALGYYAVVTGRGRKDDSIDAIRQYEEDFFKNSKLFHRRGVIMPHQVTSRNLSLAVSDRFWKMVRET
IEQQADAFKATRFNLETEWKNNFPRLRESGRDELFDKAKGEILDEVVTLSQISAKKWDDALSTKLWEKLSNYVFESIYLPAAQSDSFNTMVDIKL
RQWAEQALPAKSDRFVHDKQEWDSAVKFLESSVNAKLVQTEETLAQMFGPGQMRRITHWQYLTQDQQKRRSVKNELDKILKNDTKHLPTLTHDEL
TTVRKNLQRDNVDVDTDYIRQTWFPVYRKHFLQQALQRAKDCRKAYYLYTQQGAECEISCSDVVLFWRIQQVIKITGNALRQQVINREARRLDKE
IKAVLDEFSDDEEKKGYLLTGKRVLLAEELIKVRQIQEKLEEFINSLNQEK*
(SEQ ID NO: 945)

Classification: enzyme

Celera Sequence No. : 142000013384522
TCATCCATGTGGTGGTGGTGGCCCGCAATCGCATTGGAGTATTTGTTATGGATATACAAAAGGGGAAGTTCGCCGCTAGTGGAATGCATTTGTAG
GCTTTGCCGCAGGGATTAACTGATGATATTCCTCAGATAGGCGGAGTTTTCCGATTTAGGGTTCTAACTTTGGGGTTGATTAAAGCTAAAATCAT
CATGGAACTAATAGTTTTACATTTTTAAAAGTAATGCCGATTTTTTCCTTACTTGGGATACTTCCGAAATCCTTGTTATTAATTTGTATCTTTTC
TTTTTTGGTCATCTATGATAAATCTTATGTTGTTATATTGATATGACCGCATAGAGATATTGCATGCTATCGGATGCATAAGCTTAAACCTTAAA
ATCTCGCAGGATTTCAGAAATATCCCTTAAATTACATAATTTCACTGGTGTGCGGTATTCTTTTTCGTTTTACTTTACAATTCTTCTAGAGTTTT
TTGACTTATTTACCCAATAATTCGAATTCTAAAAGTATATCCGATCATTTAAATAATATTAGATAAAAACAAAGAATTTTTCAAGCATACTAACA
GTTTTTTCGCTCTACAAAATATTATTTTTCAAAAGTATAATTTTTTTCGTCAAATTAAGTAAAACATAAATTTAGAATCAAACTATAGCACAAAA
TGGTTACTTGTTTGTTTCGTTCTAAATCCTGATTTTTACGCCTAAGACTACAACATGCATGCACAACAACAACAACAATTATGCCAACGACAAGG
TTAACAACAACGACAACAACATGGAACACAGCTTGCCTCAAAACTACAATGTGTGACGGTTCGGATTATGGTGAATATCAGACGGATTCATAATA
CTGACTGGCTACCCGGGTGCGCGATCGATCCTTTCGCCTATGTGAGGATGGTGGCCTCGCCGCCACCCAGTGGGCGAGGAGCGCCCACATGCGGA
CGCTGCTGCTGCTGCTGGAGCCGCCCACCGCCCACCCTCAGCTTCTTGTGTCATTTCTTGCCACCGAAAGTGGGTTTCGGTAGCGCACCCATGAA
CGCACCAGCATTTGTGGGCAAGGCCGGTGCAACGAAGCTGAGATCGGGGATCAGGGAGATGCGTGGAGCCACCTTGGCGTTGCCGATTTGGAACT
GCTGCCGCTGATGCTGCTGCTGGTAGGTGGCACCCACACCCAATCCTCCAGACACGGGTGCAGTCGAGAAGTCGTGCATGATGTGTATTTGCTGT
GGAATGGCTGGCACATTGTTGTTATTGCTGCTGCTGGTGCTGCCCTTGGGCACTAGATTGCTATGAGGCTGTTGCTGCAGCTGCTGCTGCGCCTG
GTACAAACTCAAGGGATTGTTGTAGAAATTAGCGCTCTGCCACGCACCGGAATTGAATTGTGGAGCCGGTCGTGCTGGCGGAGTACTGCTCACAA
AATCCGACCAATCATCTTCTTTGGGAGCAGCTGGTTTCCTAGCGTTGCTGTTGACTATATTATTGTTGTTAGCAATTGCGTTTTGCTGATGATGC
GGTTGCTGTTGGGTGACTGGAACAGAGACAAAGTCCGACCATTCATCGTCTTCTTGAGGCTGAGACTGAGCTGGCGTGGAAGGAGCTGGTTTCTT
GGCCACCGAAGCGCTTATGGTGAGCGGTTTGGCCTGCGAGGAGAACAACTCCTCTATCCTGGCCATTTCCTCGGCATTTATGCTAGACAGAGCAT
TGTCGCCCCATTCAATAGTTGCAGCTGGCTTCTTTGCCAGCGGAATGGCTTGGGGCAGCAGAATAGCCGGACTAAGGATCATCTGTTCGCCAAAA
GTGGGTGTATCAATTCGAGACCTTGGCGCCGGCATAGATTGAAAATCACTAAAGTCGTCATCTTCCGTCGTCTGTGGTGGCAACTGAAAGCTGCT
GGCAGCTCCATTGCCACTCAGTTTGCTGGGCGAATCCAGACCAAATGGGGGTTTGTACTCCACGTCGCGATACTCCTTCTTCACCACCGTCTCAT
CGATGATAATGCCCGTCGCAGCCATCTCGTAGTCGAAATCAATGGGCGCTAGTGTGGTGGTCTTGGCCACCGCCGTATCCGATTTGGAGGGCGTA
TAGATATGGGTCTCCTTCAGCGGCACCGAATAGCTGGCCATCGAGCTGCCCACGATCTCCTCCTGAGCTGGCGCTGCGGCCGGAGGAGTGGTCCT
CAAATCAAACTGCTCCGGCTCCGACCGCTGCTGATGCAGCTGCTCACCGCCGTTGAGTTTGTGGGCAGGGCTGTCTGCTGATAGAGTAGTCGGTA
GCGTCGCTGCTGCTGCAGCAACAGCTGCTGCTGATGCCGCTGCTGTGGATTCAATATGGTTCGATTCGGGGCTGGGGACTGCAGTTGGCTGGTGG
CTATGACTCGGTCGCTCTTCGCCGTCGGAATTGCTGGCGGAACAGGAGCCGGTGGAGCCTTCCCCATGAGACGGGCCAGTCCGCGTTTCAGTTTG
GCTCGCCGTTGTTGCGGCGGCGTTTTCCAATCCTGTGCGAAGGAAAGAAAACAATTACTTGGCTGTCATGAATGAAAACTATGAGATAAACAAAG
ATAATTAATTAGTTATTCGGCTATAATCATCTGTTATGTTGCAGATAACTAAAAAAACACTGTGCTTATGAAAGATATGGAATGGATATGGATAC
TAATCTTGCATTAATCATTTTATTTTACTAGATACATTGTATCTTTTATAGAATCAAAGAAATCAGAAAATGGTTACATTTCAAGCATTACTTTT
AGTTACCAGATTTAGCAACACATCAGATGATGGCTTAGTTTAGAGACAATATTTAGGTATTAGTATGATCAACTGTATCTAGCTAAGTAAAATGT
GAAAATGAAGGGAACTCTTGGGCGGGCTTCAACTACTTGTGCTAGAACTGAGCTGGCTGAGATTGGATGCGTTGTGCCAAAGTAACAAGAACTGG
GGGAACTGTGGATCGGTAGGACGGTACGGGTAGATAGAGAGATAGAGCTGAGAAGTATATAGAGAATCGAAACTGAACTGAACGAACCAAAAAAG
AGTGGAGATTCAACTACAACACACGCACAGAGCCAACGAAACTTACTAAAATCCAGCAAGGCGTCGTGAGCAGTGAGGTTTGTGTTAATTGTTAT
TGTCATTGTTGCAGTATTTTTTGCATGATTGTTGTTAAGATTGTTGGGATTGTTATTATCGTTATTATTGTTGTTGCAGATGGTGGCAAAATGTG
TGAGTGATGGAGAGTGGTGCAAATCGATTGTCAAATTGTGATCGTTATGGGTCATCAAATCCATCACAGGTGGCATACAATCCAGTTGATCAACG
GGTGCAGCAACGTCGTTATCACCATTATCGTTGTTGTTATTGGTGTGGGAGTTAGAGGTAACAAGATTTATTTTATCAGCATTAGCCACCACCGT
TAGTTGGTCTAGTTGTTCCAATTGTAATGTCTGTACATGTGATTCTAAATACAATTTATCGTAAGGATAAACTTTTTGATTGTTTGTTGAGATAG
TTAGAAGTAATGTGGTCACAAGGAAAAACAAGGCAAACGAAAATCAATAAGAATATATAGAAAGGAGCAGCCAATCGAACGGCAGGCCAATCCGG
GAAGCGTGTGTCAATAGGATCGGGAAATAGGCAACGAAAAGCGTTTGAAAGTAAAGCGAGCGTTAGGCGATAGGGTGGCAATTTCTCGATTTACG AAACTTGTGTAGCGGTTAATTTGCGGCAACTAAGTGGAGCAATCTCGCAGAGACTCTAAGGACACTCACCCTGGTAGCTGGTGGAATTGGAAATG
GGCTCCAGGCTGCTTGCGGCGCCGGTTGATTGAGGTTTCAGCGGCTTCAGCGGATCAAAGCTCAGGTTGGCAGCAAAACGTGGCATCGATGAGTT
CCACTTGTCGCCGAAGAGCTGGAAGTTTATGAATTTCAGTTATTTGAAATACATTTTGAAGCCCTATCTAACTTACTATATTCCTTGAATCGATG
CCCAGCGATCGAACAAGGGCGTGTCTCATTTCCGAGCTGCTCCATTGGTAATCAAGGGCTTGGGCATGCTCTATGGCACCAAAATTGAATCGCTG
GCACTGAGCCAAAGGCCTGCGATTGTCCATACTTTTGCTGTCCAGTTCCGTTGGTTGTGGAAACATCATATCAAGGACTGGCTTAACCCTTTCAT
CTATGCTCAGATGGACAGCAGCTGGCGGCGGTGGCGGAGGTACAGAAACAGGAGTCACTACGGGCGCGGCGAAGTCGCCAAAATCATCGTCGTCT
TCGCTTTGACCGTGGTTTCCATTCGCAGGAGTGGCAAACTCCTGAAAATCATCGAAGCCATCATCGGTCTCTGCAGGAGGTAACTTAGAGGATTC
TTCTGTGCTAGGAGCCGTCTTAACCTCTAGAGGTTGAGATTCCGTTCGGGAATTGATTGCTAAGGAAGGTGTCTCAAAGGCAGACGTTGAATTCT
CCGTGATTTCTAGTTGGGGTTCTGCTGCTGAGAAATCCGCAAAGTCACCGAAGTCATCATCATCTTCTTGCTCTTGCATTTCGGGAACAATTTCT
TTGTGTACTAAGTCTTTTGGCGTCGCATCAAGATTTGTAAATGAATATGTATCACTATTTGCTGGTTCACCCCATTGGTGAGGGGATTCCTCCTG
ATTTGGAGGATTTGATAAGCCACGGCTTTGATTTTCCATAGGCTTTTCTAAGGTATTTGAACTTTCCTCCTGGGCTTCCAAACTTCTAAAGCTTT
CTTCTGGCTGGGAGGTATTCTCTACGTATTCTCCTTTCCCTGTATCCACATTCTCCTCCGAAAAGCCTTCTCCATATGGTAGGGTTGGAGTGGCC
AATACCTCTATGGCAAAGAAATCCACAGCTCCCTCGCGTATAAATAGTTCTTTGGGCTTCTTTGGCGAGCACTCCTCGTCGCTGTCATCGGACAC
ATCCTCCAGCGTGACTTGGTGGCTGAGGATATGGGCTTTGGTTGTTTGCATAGCCGGCGGAGCAACTGCACTAGTCTCCGCAACCGGTGAGAGTG
TGGAGGCGGCAGAAACGCTTTCCGTGGAATAGAGACTTAGACTGTCCAACTTAAGGGAGGGCACATGCTCCTCCAGTTCCTCATCATCCAGTTCC
AAGCTCAACGGAGGCGGCGTCGGCGGTGCTGTTTCCTCGAAAACATCGTAATCCATCTTCTGTTTCACCTGGTAATTAAATGCCTCGACGGTTTG
TTTGTCTTCCAGCAAATCAGGTGGCTTTTCTCGAAATTCCTCCACGGGATCTGGTGGTGGAGGGGGTTCTAAAAAGCGAGAATTAACTGAGTATC
ACTTTGAGATTCGATAAATATCTAAGCTTGCCTTTCGAGCTGCTGACTAAGCCAAAATCTGAGTATTCGTCACCCTCGTCCAAATGGATGGTGGA
TTGTAAACCGGAATCGTCGTCTTCCTCACCAAAATCGATGGGCGGGGGGGTGCTGCAGAGCAGCGGTGGTACATTCACCATAATGCCAGCTGCAA
AATTCAGTAAAAGGATCCCCTAAAATTCACTTCCTGCTTCAAGAAGAACAACAAAAACGCTGGGAACGGTTCGATCTTCTATCTCTCTCGCTCCA
CTTTATCACTGTGTGTGTGGTGTGTATGTGTGACGCAGGTGTGGAGGGCCTGCAAGTGTGTGTGTGTGTGTTAGCCACTCAAGGTCTGTGTTGGA
ATTTCTTGTTTGCATTTAACACGCGTCAATTTTGTTGTGTCTCTGTATTATGTCTAATTGTCGCCTTATTGGTGGCTCTAAAAACAGATTTGCC
GAATTTGCAAGTCGCGTTTTATCTGCAATTAGCCATGTTTTCCAGAAAACAATACTTTTTCCTCTGCCCACAGTGTGAACGTTTAACTTTTGGCC
AACCGACAGTGCTGAAAAACGTTGCGCAACATTGATAACATACAAAATTTGAATCTTATCTTTTTCAATTCCCATTTTCGATTTAAATCATTATC
CATAGTTCAGATAGAATAGTTATATTAGTTATATTTCTATAATAGATTTTTATTCTTTCCAATTCTTTTACCGTTAAAATTGTATTTGAAAATTA
TTAGTAACAAGAGTAAAATATACATGAAAGTCTAGGCTGCAGTATGTAATACGTCAAATTTTGTTGGGACACTAAACAACAAATAGTCGTCATAA
AGGCTTCTTTTAAATTGTTATGATATTTTCCACAATTTCTGCATACTTTTTTAAGCTTGCTGGCAACGCCGCCACCGTACCAATACAACTATCGA
TAGCCGCCTGTCAGTTTTGACAGCTGTTTTAAGGTTATACTGCGCTGCCGTTGCAATCGCTCCACCAATTTGGTAATTTTGCTTATTTAACATCA
AATATTGCATAAAACTAGGAAAACCAGGAATCTGTAAAGTGGAGCGAGACGGGGAACGCTATTAAGGAAGTCGGATAACTAAAGTACATCCTTTT
CTTGCAGTTCACGGTCGGACAATTACATAACTTGAAGAAGAAACCATGTCGCAGGCTCCCGTTCGCGTTTCCCCGCTGATCAAGTTCGGCAGATG
GTCCCTGCTCCTGGTGGGCATTGCCTACGGCGCCGCCCACCAGAGCCGCCTGTCCAAGAAGGAGGAGAAGTTGCGCGAGATCGAGGCACAGCAGA
AGGCCGTCCGTGATGCCAAGCTCGCCGAGGAGAAGAAGCGCAGCGCAGAGGCTGAGGCCCGTGCCTTGGCTGAGCTTTCGAAGCCCACTCCCAAG
CACTAGGATCCTTCAGGATGCAACATCCGCAGTTCCCTTAGCTTAAAAACATTGAAAAACCACAACATTTACACACGAAGTTCGCCCAAAAGGAG
GAGCATCATCGATAGTGGAGCCACC
(SEQ ID NO: 946)

Exon: 5865..5352
Exon: 5293..3972
Exon: 3913..3775
Exon: 2502..1001
Start ATG: 5496 (Reverse strand: CAT)

Transcript No. : CT24913
TGGGCAGAGGAAAAAGTATTGTTTTCTGGAAAACATGGCTAATTGCAGATAAAACGCGACTTGCAAATTCGGCAAATCTGTTTTTAGAGCCACCA
ATAAGGCGACAATTAGACATAATACAGAGACACAACAAAATTGACGCGTGTTAAATGCAAACAAGAAAATTCCAACACAGACCTTGAGTGGCTAA
CACACACACACACACTTGCAGGCCCTCCACACCTGCGTCACACATACACACCACACACACAGTGATAAAGTGGAGCGAGAGAGATAGAAGATCGA
ACCGTTCCCAGCGTTTTTGTTGTTCTTCTTGAAGCAGGAAGTGAATTTTAGGGGATCCTTTTACTGAATTTTGCAGCTGGCATTATGGTGAATGT
ACCACCGCTGCTCTGCAGCACCCCCCCGCCCATCGATTTTGGTGAGGAAGACGACGATTCCGGTTTACAATCCACCATCCATTTGGACGAGGGTG
ACGAATACTCAGATTTTGGCTTAGTCAGCAGCTCGAAAGAACCCCCTCCACCACCAGATCCCGTGGAGGAATTTCGAGAAAAGCCACCTGATTTG
CTGGAAGACAAACAAACCGTCGAGGCATTTAATTACCAGGTGAAACAGAAGATGGATTACGATGTTTTCGAGGAAACAGCACCGCCGACGCCGCC
TCCGTTGAGCTTGGAACTGGATGATGAGGAACTGGAGGAGCATGTGCCCTCCCTTAAGTTGGACAGTCTAAGTCTCTATTCCACGGAAAGCGTTT
CTGCCGCCTCCACACTCTCACCGGTTGCGGAGACTAGTGCAGTTGCTCCGCCGGCTATGCAAACAACCAAAGCCCATATCCTCAGCCACCAAGTC
ACGCTGGAGGATGTGTCCGATGACAGCGACGAGGAGTGCTCGCCAAAGAAGCCCAAAGAACTATTTATACGCGAGGGAGCTGTGGATTTCTTTGC
CATAGAGGTATTGGCCACTCCAACCCTACCATATGGAGAAGGCTTTTCGGAGGAGAATGTGGATACAGGGAAAGGAGAATACGTAGAGAATACCT
CCCAGCCAGAAGAAAGCTTTAGAAGTTTGGAAGCCCAGGAGGAAAGTTCAAATACCTTAGAAAAGCCTATGGAAAATCAAAGCCGTGGCTTATCA
AATCCTCCAAATCAGGAGGAATCCCCTCACCAATGGGGTGAACCAGCAAATAGTGATACATATTCATTTACAAATCTTGATGCGACGCCAAAAGA
CTTAGTACACAAAGAAATTGTTCCCGAAATGCAAGAGCAAGAAGATGATGATGACTTCGGTGACTTTGCGGATTTCTCAGCAGCAGAACCCCAAC
TAGAAATCACGGAGAATTCAACGTCTGCCTTTGAGACACCTTCCTTAGCAATCAATTCCCGAACGGAATCTCAACCTCTAGAGGTTAAGACGGCT
CCTAGCACAGAAGAATCCTCTAAGTTACCTCCTGCAGAGACCGATGATGGCTTCGATGATTTTCAGGAGTTTGCCACTCCTGCGAATGGAAACCA
CGGTCAAAGCGAAGACGACGATGATTTTGGCGACTTCGCCGCGCCCGTAGTGACTCCTGTTTCTGTACCTCCGCCACCGCCGCCAGCTGCTGTCC
ATCTGAGCATAGATGAAAGGGTTAAGCCAGTCCTTGATATGATGTTTCCACAACCAACGGAACTGGACAGCAAAAGTATGGACAATCGCAGGCCT
TTGGCTCAGTGCCAGCGATTCAATTTTGGTGCCATAGAGCATGCCCAAGCCCTTGATTACCAATGGAGCAGCTCGGAAATGAGACACGCCCTTGT
TCGATCGCTGGGCATCGATTCAAGGAATATACTCTTCGGCGACAAGTGGAACTCATCGATGCCACGTTTTGCTGCCAACCTGAGCTTTGATCCGC
TGAAGCCGCTGAAACCTCAATCAACCGGCGCCGCAAGCAGCCTGGAGCCCATTTCCAATTCCACCAGCTACCAGGGATTGGAAAACGCCGCCGCA
ACAACGGCGAGCCAAACTGAAACGCGGACTGGCCCGTCTCATGGGGAAGGCTCCACCGGCTCCTGTTCCGCCAGCAATTCCGACGGCGAAGAGCG
ACCGAGTCATAGCCACCAGCCAACTGCAGTCCCCAGCCCCGAATCGAACCATATTGAATCCACAGCAGCGGCATCAGCAGCAGCTGTTGCTGCAG
CAGCAGCGACGCTACCGACTACTCTATCAGCAGACAGCCCTGCCCACAAACTCAACGGCGGTGAGCAGCTGCATCAGCAGCGGTCGGAGCCGGAG
CAGTTTGATTTGAGGACCACTCCTCCGGCCGCAGCGCCAGCTCAGGAGGAGATCGTGGGCAGCTCGATGGCCAGCTATTCGGTGCCGCTGAAGGA
GACCCATATCTATACGCCCTCCAAATCGGATACGGCGGTGGCCAAGACCACCACACTAGCGCCCATTGATTTCGACTACGAGATGGCTGCGACGG
GCATTATCATCGATGAGACGGTGGTGAAGAAGGAGTATCGCGACGTGGAGTACAAACCCCCATTTGGTCTGGATTCGCCCAGCAAACTGAGTGGC
AATGGAGCTGCCAGCAGCTTTCAGTTGCCACCACAGACGACGGAAGATGACGACTTTAGTGATTTTCAATCTATGCCGGCGCCAAGGTCTCGAAT

FIGURE SHEET 510

TGATACACCCACTTTTGGCGAACAGATGATCCTTAGTCCGGCTATTCTGCTGCCCCAAGCCATTCCGCTGGCAAAGAAGCCAGCTGCAACTATTG
AATGGGGCGACAATGCTCTGTCTAGCATAAATGCCGAGGAAATGGCCAGGATAGAGGAGTTGTTCTCCTCGCAGGCCAAACCGCTCACCATAAGC
GCTTCGGTGGCCAAGAAACCAGCTCCTTCCACGCCAGCTCAGTCTCAGCCTCAAGAAGACGATGAATGGTCGGACTTTGTCTCTGTTCCAGTCAC
CCAACAGCAACCGCATCATCAGCAAAACGCAATTGCTAACAACAATAATATAGTCAACAGCAACGCTAGGAAACCAGCTGCTCCCAAAGAAGATG
ATTGGTCGGATTTTGTGAGCAGTACTCCGCCAGCACGACCGGCTCCACAATTCAATTCCGGTGCGTGGCAGAGCGCTAATTTCTACAACAATCCC
TTGAGTTTGTACCAGGCGCAGCAGCAGCTGCAGCAACAGCCTCATAGCAATCTAGTGCCCAAGGGCAGCACCAGCAGCAGCAATAACAACAATGT
GCCAGCCATTCCACAGCAAATACACATCATGCACGACTTCTCGACTGCACCCGTGTCTGGAGGATTGGGTGTGGGTGCCACCTACCAGCAGCAGC
ATCAGCGGCAGCAGTTCCAAATCGGCAACGCCAAGGTGGCTCCACGCATCTCCCTGATCCCCGATCTCAGCTTCGTTGCACCGGCCTTGCCCACA
AATGCTGGTGCGTTCATGGGTGCGCTACCGAAACCCACTTTCGGTGGCAAGAAATGA
(SEQ ID NO: 947)

Start ATG: 370 (Reverse strand: CAT)

MVNVPPLLCSTPPPIDFGEEDDDSGLQSTIHLDEGDEYSDFGLVSSSKEPPPPPDPVEEFREKPPDLLEDKQTVEAFNYQVKQKMDYDVFEETAP
PTPPPLSLELDDEELEEHVPSLKLDSLSLYSTESVSAASTLSPVAETSAVAPPAMQTTKAHILSHQVTLEDVSDDSDEECSPKKPKELFIREGAV
DFFAIEVLATPTLPYGEGFSEENVDTGKGEYVENTSQPEESFRSLEAQEESSNTLEKPMENQSRGLSNPPNQEESPHQWGEPANSDTYSFTNLDA
TPKDLVHKEIVPEMQEQEDDDDFGDFADFSAAEPQLEITENSTSAFETPSLAINSRTESQPLEVKTAPSTEESSKLPPAETDDGFDDFQEFATPA
NGNHGQSEDDDDFGDFAAPVVTPVSVPPPPPPAAVHLSIDERVKPVLDMMFPQPTELDSKSMDNRRPLAQCQRFNFGAIEHAQALDYQWSSSEMR
HALVRSLGIDSRNILFGDKWNSSMPRFAANLSFDPLKPLKPQSTGAASSLEPISNSTSYQGLENAAATTASQTETRTGPSHGEGSTGSCSASNSD
GEERPSHSHQPTAVPSPESNHIESTAAASAAAVAAAAATLPTTLSADSPAHKLNGGEQLHQQRSEPEQFDLRTTPPAAAPAQEEIVGSSMASYSV
PLKETHIYTPSKSDTAVAKTTTLAPIDFDYEMAATGIIIDETVVKKEYRDVEYKPPFGLDSPSKLSGNGAASSFQLPPQTTEDDDFSDFQSMPAP
RSRIDTPTFGEQMILSPAILLPQAIPLAKKPAATIEWGDNALSSINAEEMARIEELFSSQAKPLTISASVAKKPAPSTPAQSQPQEDDEWSDFVS
VPVTQQQPHHQQNAIANNNNIVNSNARKPAAPKEDDWSDFVSSTPPARPAPQFNSGAWQSANFYNNPLSLYQAQQQLQQQPHSNLVPKGSTSSSN
NNNVPAIPQQIHIMHDFSTAPVSGGLGVGATYQQQHQRQQFQIGNAKVAPRISLIPDLSFVAPALPTNAGAFMGALPKPTFGGKK*
(SEQ ID NO: 948)

Celera Sequence No. : 142000013384673
TCGCGTGGACATTGAGACTCCAGTGCGCAAGCGTGAAATCGAGACGGCGGTTGCCTCGCCCAACCAACAGCATGTGCCATCGGTGAACAAGGCGG
GAAAAGAGGTGTACTATCCACCCGGACACGACACCATCGTCATGAAGCGCGAGGAGATGCATGCTGGATCTGCCTCAGGCGTGAGTATTGGATAC
TTACCAAGGTGGAATATGCCCAACTGATAATCCTACATCCACAGGGTCGCTGGGCCAAGGGATCCGGAATGTACGAGTACGAGTCCGGCTCGAAG
TCAAAGACGAAAACCAAGTCCGGTGGCGCCGTTGTGCCCGTGTGCCTGCCCCTCTGCTGTGCCATGCCCTGCTCCATTATGTAGTGGGCGGACAT
CGCCGGAAGACCGTATCTTGTACATAGGTTTCTAATATTTGCCGTTAATAGTTCTAACGCTAAATCCTGCCCCGCGTTTTTGATTGCTCTCTACT
AGGTCGTCTAACTTCTATCGGGCTTGCTGCTTGTCAATTGGTTGTACGCGTAATTTGTTTGCCAAATTGTATGTCTATATATCTATACGTTATTG
TCTATGTATATAATTTGTGAAGCGTCATCTACGGATGGGCCGGTTGTTATACCATTTTATTTTGGATTTAGTAGTTCACCCCAAACTAGTTTGCT
CAAAATTGTTGCTCAAGCATTTAAATTCGCCAGTGGGATGCCCAAAAAGTTTACTCGATGCCAATTGTTTTAACTTAAATTTGCATACCGCATAC
CAAACACTAATAAATGAGCCGTGGAATCCAATTCCCTCTATTATTCGTTTCGCCAGCGCCCCCAAATACCCACTAATCATAAACCATAATCGTAA
CAGCGACTTAAAAGGTAACTCAGTCGTTACAGAGCCATAAATACTATTTCTAATACACGTAGTAACCATAATAAAAAACGAGATCTAACAAACGA
AGCGATGAACTGTTTGAATGCCTCTTTTGAATGGATCGATTTGCGTGGGGTTTTGGTATAGTAAAAGTTTTTATAAGTTTATTTTGGTATAAATC
GTTCTGATCGAATAACAATTTGCATATCACAAAAGTAATATCTACATTTCACCTTGTAGGAATAGGTGTAGCTTTCTTTTGAGAAGTTATTAAAA
AACACTATAGTGAAACAACAAAAAACTAAAAACAACATAAAACAATACAAAAATCAACAGAGGTATATTATTTAGATAAGTATCATTGAGCACTT
TGAGTAGTGAAACGGGAGGATTATTGCTACAGAGACGAGTTCTTATTGTTGTTCTTGGATTACGAATTGAAGCTAAATGATGGATTAAAAGTATA
CTACATCGTAATATGAGTATAGTTACTGGACTTACTACCATACACACAATATGTGCCTAATATTCTAACCATGCCGCCATGATCTGTCATTCTAT
TAAAAGAGACTACCGTTTGTGAAAGTAATGTTGTCCTTTGTACATACGCATATTTGAGAGTTGGAAAGGTCACGTATTGTAACGCTGTCTTTTAT
GCAGGCTAACTTTTGCGCTCGGAGTTCTTTAGCTCTGCTAAGTACCAAGTGAAAGTTGGAAATTGTTTGATGCTGTAGATAGAATACTTTATCGA
GTTGATTCCATCCTGTTCTATTTTGCTCATGCCATTCTGTAAGTTTTCATAGCTGTCAAAAAAAGAAGGGTAAAAATTCCATATTTGTTAGTCTA
AATTATGGATAATAGTATGGTCTACTGACCGCTTAGGATTGGCCTTTTCCTTCTGATGCTTCAGCATCTTGTAGCGAGCTATGTTGACCGGATAC
CTTGATATGAATAGGTTTGCGTGCTTCAACCTGTTGGACATGTCGTCATCCTCGCCGCCCCAGCCAAAGAACGAGTTTGAGAACCCATTTACGGC
CTGAAAGTGCTCACGCGTCATTGCGGAAACACCTCCAAATATTGATCGATAAGGCAACCTATAAAGAATTGAATCAATTTACCATTGATAGTTGT
TATCTCTTTGCTCTACTTGCCTGAAGTTCAGCGTGTCTATAGCCACTGACATGTGTCGCGGCTGACGTGGACAGTTGTAAAGATTGCGGTCGTCC
AAAGGCAGAAGATCGACATCGTGGAATATAAAACAATCCCACTGGTACAGCTTTAAGGCCTCCAAATAACCAATGTTCATCATGGCAGCCCGATT
AAAGGGCTTCCCGTTGGTCTGCTCTACAATGAAAATGCGATAGGCGATGCGCTGCTTCATCAGAAATGGGTGGATGTTGCGCAGGAAAAGTAATA
GATGGGCGTATCGATCGCGGAAGGGCACAACAATAGCCACGTGATGCTGGGCATTGCAGTTTTCAGGCTCGAAGGCGCCACCAGGGCGCAAAAGA
GGTCCAAGCTCCGCCTCAATAACGTCCAGTGACTCCAGTGTCGTGTTGGGCGTGATGGGTCCACCTAAACAAGGTGGACGTATTTTAAATCGTGC
TAAAGAAAGAGCCAAGCCGAGCTTACCATCACGGGGATCGGGATCAGTGCAGTTGGCAAGGAGGGCGGATGTGGATTTCTGTCGCGGGGGCAAAA
ATTTCTTTGTGCCCAGCAGGAAGCGCGTTAAGTCTTGTGGAATGGAAGTAAAGTTTGCCGTGGCAATCACAGTTCTTATGGTAGAGTTGGGTCCG
CCATTGAGCTCCTGGTCCCGCTCTCTGTCTTTTGATAAGGCGAGCGGGGAAGCGGGCAGCCTGGATGCTTCACTGCCTCCGGCTCCATCGCTGCT
AGCGTTCCCGTAGATATGAGCATACTTGTGCACGCGCCGAATGCTAATATCCGTTCCCAAAAATAATTGATAAGATAACCTCTGCCAAGGCAATA
TGATAGATTTAGTTACCTGAGCTTGCTGAGGGAGGTGGCGCTACCTCCGTCGGAACGGAAGCCCACAAAGTTAAGCACCAGCAACAAGCATATCG
CGCCGGCTAGGAAGCGTATGAGATTCGCCTTGGTGAAGAGGTACATGGTCCGAGGATTGCATCATACCTTGCTCGACGCCCAGGCGCTGCGAACT
GGCATTTTCAAGCGCAAAACGTTCGACAACCGAACAAAAACGTTAAAATTCGCAACTCCAGGGTTCAATCAGAAAAGTCAGCTGAGAGTCCCCCT
CGACCAGGGTTGCCAGAGTTGCGCAATTGCTGCAGCCATAAATCGCCGACTGCCGATAGTTTGCAGGCGCCAAATTCAAAAAACAAACTTCACAG
CATATTTTTATGATCTATTATTACTAAAAATATTAAATGCATTTTAAAATTGAACGAAAATCTAAATGTTTTATCTACAAAACAATGAATACATA
TAATATAAGGCAAATTAATTTGTTATTCTAAAGTCCGAAGTTCTCTTGGTTTTGTGATTTATTGCGCTGTTCGGATCTCGTAAGTATCCCAAAAA
TAGCGAGTTACAGAGTGGTATTGTAAACTGGGGAAATATACGATCTGACATTTGCCCCCAAGTCCTGGGAATGGGTCTTTTCTATCAAGAATATA
AACAAGTTACAAACACAACTGAAGATTTAAACTAATTGTCGTGCAGAGCAGTAAGGCCCCACTATCCTGACAGCGGTTGTCGCAGCGGCAGTCGC
AGCGCCTCGTTGTCCTTGATGTGAATCACTTCGAACTGGTTTTGATAGGTGTACTCTATCCGCAGAATCTTGTCTTCGCCGATGCCCGGATCATA
GAAGCCGGGCAGGTCGCTCTACAAAGACGTAAGGAATGGTATTATATCAACCCAGAACACAATCAGTGAAAGTGTCTCACCTTTGATGAATCATG
CAGCTGCAGGGTCCCGTTCTTGACCATGCATTGAATGGCTACGGTGACGTCGAGCGATTGCTCTGGCTTGAACTGTCTGCCGCCCGCCAAGGTAC
AGCCGTAGACAGCTCGTGTGACAATCAGCCCATTCCTCGCCAGCTCCTCCGTCATGATCCTATTGTACGTGGCCTGCATTAGATGAACGGCAGCA CTCGCCTCGTGCCTCTTGGCGGACAGTCTCTGCTCATTCTGACGCTTCGTCCTTTCCACCTCGATGTTCTTTCGCTCCGCCTCCATTGGGTCCAT
CACAGTCC
(SEQ ID NO: 949)

Exon: 3093..2867
Exon: 2798..2497
Exon: 2439..2016
Exon: 1958..1740
Exon: 1667..1001
Start ATG: 2991 (Reverse strand: CAT)

Transcript No. : CT24923
GCGAATTTTAACGTTTTTGTTCGGTTGTCGAACGTTTTGCGCTTGAAAATGCCAGTTCGCAGCGCCTGGGCGTCGAGCAAGGTATGATGCAATCC
TCGGACCATGTACCTCTTCACCAAGGCGAATCTCATACGCTTCCTAGCCGGCGCGATATGCTTGTTGCTGGTGCTTAACTTTGTGGGCTTCCGTT
CCGACGGAGGTAGCGCCACCTCCCTCAGCAAGCTCAGCATTCGGCGCGTGCACAAGTATGCTCATATCTACGGGAACGCTAGCAGCGATGGAGCC
GGAGGCAGTGAAGCATCCAGGCTGCCCGCTTCCCCGCTCGCCTTATCAAAAGACAGAGAGCGGGACCAGGAGCTCAATGGCGGACCCAACTCTAC
CATAAGAACTGTGATTGCCACGGCAAACTTTACTTCCATTCCACAAGACTTAACGCGCTTCCTGCTGGGCACAAAGAAATTTTTGCCCCCGCGAC
AGAAATCCACATCCGCCCTCCTTGCCAACTGCACTGATCCCGATCCCCGTGATGGTGGACCCATCACGCCCAACACGACACTGGAGTCACTGGAC
GTTATTGAGGCGGAGCTTGGACCTCTTTTGCGCCCTGGTGGCGCCTTCGAGCCTGAAAACTGCAATGCCCAGCATCACGTGGCTATTGTTGTGCC
CTTCCGCGATCGATACGCCCATCTATTACTTTTCCTGCGCAACATCCACCCATTTCTGATGAAGCAGCGCATCGCCTATCGCATTTTCATTGTAG
AGCAGACCAACGGGAAGCCCTTTAATCGGGCTGCCATGATGAACATTGGTTATTTGGAGGCCTTAAAGCTGTACCAGTGGGATTGTTTTATATTC
CACGATGTCGATCTTCTGCCTTTGGACGACCGCAATCTTTACAACTGTCCACGTCAGCCGCGACACATGTCAGTGGCTATAGACACGCTGAACTT
CAGGTTGCCTTATCGATCAATATTTGGAGGTGTTTCCGCAATGACGCGTGAGCACTTTCAGGCCGTAAATGGGTTCTCAAACTCGTTCTTTGGCT
GGGGCGGCGAGGATGACGACATGTCCAACAGGTTGAAGCACGCAAACCTATTCATATCAAGGTATCCGGTCAACATAGCTCGCTACAAGATGCTG
AAGCATCAGAAGGAAAAGGCCAATCCTAAGCGCTATGAAAACTTACAGAATGGCATGAGCAAAATAGAACAGGATGGAATCAACTCGATAAAGTA
TTCTATCTACAGCATCAAACAATTTCCAACTTTCACTTGGTACTTAGCAGAGCTAAAGAACTCCGAGCGCAAAAGTTAGCCTGCATAAAAGACAG
CGTTACAATACGTGACCTTTCCAACTCTCAAATATGCGTATGTACAAAGGACAACATTACTTTCACAAACGGTAGTCTCTTTTAATAGAATGACA
GATCATGGCGGCATGGTTAGAATATTAGGCACATATTGTGTGTATGGTAGTAAGTCCAGTAACTATACTCATATTACGATGTAGTATACTTTTAA
TCCATCATTTAGCTTCAATTCGTAATCCAAGAACAACAATAAGAACTCGTCTCTGTAGCAATAATCCTCCCGTTTCACTACTCAAAGTGCTCAAT
GATACTTATCTAAATAATATACCTCTGTTGATTTTTGTATTGTTTTATGTTGTTTTTAGTTTTTTGTTGTTTCACTATAGTGTTTTTTAATAACT
TCTCAAAAGAAAGCTACACCTATTCCTACAAGGTGAAATGTAGATATTACTTTTGTGATATGCAAATTGTTATTCGATCAGAACGATTTATACCA
AAATAAACTTATAAAAACTTTTACTATACCAAAA
(SEQ ID NO: 950)

Start ATG: 103 (Reverse strand: CAT)

MYLFTKANLIRFLAGAICLLLVLNFVGFRSDGGSATSLSKLSIRRVHKYAHIYGNASSDGAGGSEASRLPASPLALSKDRERDQELNGGPNSTIR
TVIATANFTSIPQDLTRFLLGTKKFLPPRQKSTSALLANCTDPDPRDGGPITPNTTLESLDVIEAELGPLLRPGGAFEPENCNAQHHVAIVVPFR
DRYAHLLLFLRNIHPFLMKQRIAYRIFIVEQTNGKPFNRAAMMNIGYLEALKLYQWDCFIFHDVDLLPLDDRNLYNCPRQPRHMSVAIDTLNFRL
PYRSIFGGVSAMTREHFQAVNGFSNSFFGWGGEDDMSNRLKHANLFISRYPVNIARYKMLKHQKEKANPKRYENLQNGMSKIEQDGINSIKYSI
YSIKQFPTFTWYLAELKNSERKS*
(SEQ ID NO: 951)

Name: beta-1,4-galactosyltransferase
Classification: enzyme
Gene Symbol: BcDNA:GH13356
FlyBase ID: FBgn0027538

Celera Sequence No. : 142000013385198
ATGTATATACAACAGGATATTCTGCACGATACTTATCCTGCAGCTGATGCATTTTCTCCACCAGTTTAACCACTCCCATCGAGTACCACGCTTCT
TCGTAAAGGCGCATGAGCTGCAAGACACGGCGGTCACTATATCTATCAGCCGGGTCAGGCATCCTTAACTGAATAACCCAACGCATGGAATCATT
GGCGGCCACATCAACTCGCTCATCAATGAATACACCATTCAAGCCGTATACGAGAAATTTTTTAGGATGCAAAATCCACTGATTGACCAGTTCTT
CGGGACGAGGATTCCCGTGAAGCTTTCGCGTATCCTCCTTGCAGGCCTTGTAGTATTGTCGCATTTGCTTTATCAGTCGGGGTGCCAGTGTATCG
TTTTCACCCAAGTGGCTCTCCATGAATTCCACCATGGCAGTGGCGAACTGATCCTCGACTCGCTCAAAGTTGTCCACATATTTAGAGGCACTGGA
GAAGCGACCGCAGGCAAAATTCCAGAAATTCGTGCACGGTGATGTTGTTCTATTGAGATTATTGTGAATATCGTTCGACGTTGCCACGTTGATGT
CCACTATTGCCTGGATGGGAATGAATAATGCCACCAGGCAAGAGCACAGTAAAAGTAAACATCCCATTAAGCTCGCTCGATTCACAATGAAACAA
CAGATTATCGCAACGCTCTGCTGAGCTCGGCCACCTTCGAACTACCTATAGAGCTTTGGGGCTGATAGTGACAGCTTGGTCAATACTAGAATTCA
CATTTGAAATGTAGAGCAATTACCTCTAATGAAATGTGCCTGCCACCTATATAAACCCGCTTGGTGAGTACATTAAACCGATCTTAACGTTTATT
GAATCTTAATTACACCGCTGTTGTAGTTCAATCTTCAATCGTTCGCTAAGACAGTTCGCAATATAAAATTGGTAATCGCGTCGGGACTACCCCAA
CTATATGTCACACGCTTATAGTCTACTTAACAAAACTGGATCTAAGGTGTTCACTTCTTGAACTTTTGCTTCTTTCCCGCATTCGCACCCGCCGT
GGACTTTTTCAGCTGGCCGATCTGTTTGGATTTTTGCTTCAGCTTGTTCTGCTTCTTGATGGGTTTTCCCTCGAGAATGGGCACATCGTCGATAT
CCACTCGCGGCGCCTTGGCCAGTTTGGCGTTTCCCTTGGGCGACTGTTTTCCTTTCGGCTGTGGCTTCGTTTTCGTTTCCTTAATTGCTGATTTG
CTAGGGGAGTTTGTGCCATTGGTTGTTGGCTTATTGTCATCTGGTTTAGCTGGTGATCCGGCTCCATTTTCCTTGGGTTGCGATCCTTTGTTCTT
TTTATTGAATGATTTCGCATCTGAATTGGAAACAGTGGTTTTCCCATTGGTTTGTTTTTGTTTAGGTGCAGACTTGGAAGGTGACTCGCTTGAAT
TTGTTTGCTTGTCCGGTGCCTGGGATTTCTCATTTTTCTTCTCTGCTGGCTTTTCTGGCTTTGGCTTTTTGACAGGCTGCTCAAACACCTTGGCC
ACATACTTGGTCTTGCTCTCTTCCCGCTTCTTTTTCTTCAGTTCCTGTTCGATTTCGGTGAAACTGGGTTTTCCGGCGCGCTTTCCAAGCAGTTT
TCGGGGACCCTTCTCCTTTGACGCTACCTCCTCCTCCACCTCCTCAGACTCCGCAGCCGCTTCTGTAGTGGCGTCCGCTTCGATGGCCTCATCCA
GCTGCTTTTCATCCTCCTCCTGCTGCTCCTTAGTTATGGGTATGGTGTTGGAGAATTTCTTGAGCTTGGCCACGTAGAACCCGTCCATGTTGTGG
GTGTGCGGATAGTAGCGCTTGGTAAGGTTTAAGCTAGGATGGAACCGATGCTGACGGAATTTGGTAAAGCCCTCCACGCCGAAGTCCAGACCAGT
GGGCACAAGTTTGACATTTCGCTTCTTCAGTGCATAGTCGATGACCCATTCGTTCTCCTCGGGCAACACCGAACAAGTTGAGTATACAATGTAGC CGCCAGTTGATGACTTCGCATCCGTACAATCTATGGCAGTCAGCAGAAGCTTCCTCTGCAGGTTGTAGCACCTTTGTACATCTACTTCCGACTTG
GTGGTCTTCACACTGGGATCCTTAGAGACGACGCCAGTTCCAGTGCACGGAGCATCCAGCAGGACACGGTCAAAGCCAGTCATAATATTCCGGAA
CTTAGTGCCATCCTCGCAGCTGACCACTGCATTTACAATTCCCAGGCGATGGAAATTGGCAACAATGGCCTTGATGCGATCCCTGTTAGAATCGT
TGGCGAAGAGCACACCAGTGTTCTTCATGATGCTTGCGATGTGGGATCCCTTTCCACCTGGGGCGGAGCACATGTCCAGGATGCGTTCGTTCTCT
TGCGGGGCGAGTGCCATTACAGGCAACAGCGAAGAGGCGCCCTGGATCATGTAGTGGCCAGCCAGATACTCTGGAGTTGCACCCAGTGGCACCTG
TGAGTTAAAGACAACCAATCCAACTTTCGTCCATTTACCAAGGGGATCCAAGTTGACGCCACGATTGATCAGAGCTCCGGCCAAATCCCTACGAC
GTGTTTTTAGAGTATTGGTGCGTATGGTTAGGGGACGAGCAATCTAAAGGGGTTAATTTTTAATGATTAATCTTGTAACTATATTTTTTATGAAA
TATACTAACCTCTGAGGCCTCCAGATATTCCATTAGCTCTGTCAGCGGCAACATATCCATCAGCTTCTCCATCAAAAATTCGTTGTAGCTGTAAT
ACAAACACAGATCCCTGCGCAGCAAATCGATGTACTCCCCGCGAGACCTATCCGCTTGACGATACCTTTTGAAGTCGGAAAGAACCAGACTGACG
TCCTTTATGCGCTGTTGCACTTCCTGCAGGGTTAGGTCCTTCTCGGTTTCTTCGCCTTCGACGGGTAGCTGGAAAACATCCTGCTTGTCAACGGT
TTCCAACATTTCGTCGTCGGCCAGTTGGGCTTCCTCTGCCTCGCGCTTTTTCAACTTCTTGTTAGCCCGCTCGATGGGCAGCTTGTCATCATCAT
CATCATCATCATCATCGTCGTCGTCCTCATCCTCCTCTTCATCACTGTCTGCCTGAGCACCATCTTCCTCGCCAGATATGTCAAAGTCATCGTCG
GAGTTGGCATCATCATCGTCGGATAGATCGGCCAGCTTGCCAACCTGAGCGGTATCATCATCAGATTCCAATCCTTCCTCATCGTCTCCCTCCTC
TTCCTCTTCACATTCTTCTCCCAACTCATCTTCGGAGTCCTCCTCCGACTCCTCATCCTCCTCCTCCTCCTCGGACTCCGTTTCTGGCTGCT
TCTGTTGCTTCTTGGGCTTCAGCCAGGCATCATTATCATCTGTAAAACCCTTGGGAGCTGTAGCTTTCTGGCCCTTCGGAGCCGGCACCAGTTGA
GGCACCTCCTCATCGGAGGATGCAACCTGTGGTTCCTCTTCATTATCCTCAGGATCGCTGTCGCTGTTGTAGGCCGTCTTCCGCTTAGCCGGTTG
TGGTAACTTTCCCTTGGCCCTCTTCTCCTGTAGTTTGGCCTTCTGGACTACTTTCTTTTGCTCTCGCTTAACGAACCTCTGCTTCTGTCGGTGGG
AAAGCTTCTTGTCCTCCTCTTCCATGGGAGCTGTGAAGTAAAACATTTGAATTGAACACCCATTGAATAGGGTAATATTCAGGAGCTCTCACCAA
ACGATTGTTTGCGAAAAACAGGCGGTCCTTGCTTGCGCGCCTTGCGCCCAGGTCCCTTTTTCGGTTTCTCACTGTATTCAGCCTTCCGACCCATA
TTTTTAACTTAGTTTATCCAGTTTCTTGGAGCAGAACTTAAAAAAAAACGTGAGCACTTCGATTTTGCTCCACGTGCGCCGCTCAAAAGACAGCG
AGTGTTTTCCAGCACTGGTCAGAGGGAATTGCTTGAGCCAGTGCTGTCAACTTTTCAGCTTTTAACTAGCTATGAACAATGTTTTTTTTTCAACA
TATATTAATAACTAATAAAATTATATATTACTTTAAATTTTATTTTGTCGGACTTTGCTTGATTCTTACACAGTTTATTTATACAGATTACGTTA
GTATATATATTTGGAAAACACGTGGAACTTTTTAATTAAGATATTTTAGCTACTTGCTCTCCCAGCTGTTTAGCAGCAAACGTATTTCTCAGCAC
TATAAAAACGAGTTGGTAAACTAATTGGTAAATCCAAAAATATCATAAATAAAAAAAATCTGGAATATATCTAATTAACAGAATTCTTGCTTATA
AGTAAGTATTATATCCATTCAATAATTAGATATGATCTTTAGTTGTAATTTAAAATGAAAAATTAATTTAAATAACCGTTATAGTTGCTGCCAAC
TTGATGCGAATAGTAGTTTGTTGACAACCCTGCCATATTTGATTGTGTTGGTGAATGGCTGGTTCAAACGACTGCGCCTTTTTGCGAAAAATTTA
ATTAGTTGCAAATCATGGCATACCAGGAGAAAATAACAGAATTTAAGAACTGGGCCACTAATCTTGGCTGCCCGCCCACTGCCCTGCCCACCGAT
GATGCACTCCGAAGGTAAGTTACAGCTGTGTTAGGCAAATCGGCAACTATCCGTACTTAAAACCCGCTTTTTGCTTCACAGAATTTTTAAGTCCG
GCTCCAGTTTACTTTTGAACCAGCTGCAATCCCGCATCCAGCCGGTGGATTACGTGCGGGAGGTGCGCGAGAACCTGCTGATTGCCCAAGTGGCT
CGCTACAAGGACAAAATGGTGCCGCTGGCCTCTAGGAGTTTCCAGCCACCGGAGCTCCAGAGGTACCAAAAAATACAGGAGCTAAAGAAGCACAA
GGAGAAGGCGAACCAACAGCTTACGGAGGCCCGAAAAGAGTACCAAAAGCTATCTGCCGGCATC
(SEQ ID NO: 952)

Exon: 3909..3703
Exon: 3635..2670
Exon: 2608..1001
Start ATG: 3635 (Reverse strand: CAT)

Transcript No. : CT24929
TGCTGGAAAACACTCGCTGTCTTTTGAGCGGCGCACGTGGAGCAAAATCGAAGTGCTCACGTTTTTTTTTAAGTTCTGCTCCAAGAAACTGGATA
AACTAAGTTAAAAATATGGGTCGGAAGGCTGAATACAGTGAGAAACCGAAAAAGGGACCTGGGCGCAAGGCGCGCAAGCAAGGACCGCCTGTTTT
TCGCAAACAATCGTTTGATGGAAGAGGAGGACAAGAAGCTTTCCCACCGACAGAAGCAGAGGTTCGTTAAGCGAGAGCAAAAGAAAGTAGTCCAG
AAGGCCAAACTACAGGAGAAGAGGGCCAAGGGAAAGTTACCACAACCGGCTAAGCGGAAGACGGCCTACAACAGCGACAGCGATCCTGAGGATAA
TGAAGAGGAACCACAGGTTGCATCCTCCGATGAGGAGGTGCCTCAACTGGTGCCGGCTCCGAAGGGCCAGAAAGCTACAGCTCCCAAGGGTTTA
CAGATGATAATGATGCCTGGCTGAAGCCCAAGAAGCAACAGAAGCAGCCAGAAACGGAGTCCGAGGAGGAGGAGGAGGAGGATGAGGAGTCGGAG
GAGGACTCCGAAGATGAGTTGGGAGAAGAATGTGAAGAGGAAGAGGAGGGAGACGATGAGGAAGGATTGGAATCTGATGATGATACCGCTCAGGT
TGGCAAGCTGGCCGATCTATCCGACGATGATGATGCCAACTCCGACGATGACTTTGACATATCTGGCGAGGAAGATGGTGCTCAGGCAGACAGTG
ATGAAGAGGAGGATGAGGACGACGACGATGATGATGATGATGATGATGATGACAAGCTGCCCATCGAGCGGGCTAACAAGAAGTTGAAAAAGCGC
GAGGCAGAGGAAGCCCAACTGGCCGACGACGAAATGTTGGAAACCGTTGACAAGCAGGATGTTTTCCAGCTACCCGTCGAAGGCGAAGAAACCGA
GAAGGACCTAACCCTGCAGGAAGTGCAACAGCGCATAAAGGACGTCAGTCTGGTTCTTTCCGACTTCAAAAGGTATCGTCAAGCGGATAGGTCTC
GCGGGGAGTACATCGATTTGCTGCGCAGGGATCTGTGTTTGTATTACAGCTACAACGAATTTTTGATGGAGAAGCTGATGGATATGTTGCCGCTG
ACAGAGCTAATGGAATATCTGGAGGCCTCAGAGATTGCTCGTCCCCTAACCATACGCACCAATACTCTAAAAACACGTCGTAGGGATTTGGCCGG
AGCTCTGATCAATCGTGGCGTCAACTTGGATCCCCTTGGTAAATGGACGAAAGTTGGATTGGTTGTCTTTAACTCACAGGTGCCACTGGGTGCAA
CTCCAGAGTATCTGGCTGGCCACTACATGATCCAGGGCGCCTCTTCGCTGTTGCCTGTAATGGCACTCGCCCCGCAAGAGAACGAACGCATCCTG
GACATGTGCTCCGCCCCAGGTGGAAAGGGATCCCACATCGCAAGCATCATGAAGAACACTGGTGTGCTCTTCGCCAACGATTCTAACAGGGATCG
CATCAAGGCCATTGTTGCCAATTTCCATCGCCTGGGAATTGTAAATGCAGTGGTCAGCTGCGAGGATGGCACTAAGTTCCGGAATATTATGACTG
GCTTTGACCGTGTCCTGCTGGATGCTCCGTGCACTGGAACTGGCGTCGTCTCTAAGGATCCCAGTGTGAAGACCACCAAGTCGGAAGTAGATGTA
CAAAGGTGCTACAACCTGCAGAGGAAGCTTCTGCTGACTGCCATAGATTGTACGGATGCGAAGTCATCAACTGGCGGCTACATTGTATACTCAAC
TTGTTCGGTGTTGCCCGAGGAGAACGAATGGGTCATCGACTATGCACTGAAGAAGCGAAATGTCAAACTTGTGCCCACTGGTCTGGACTTCGGCG
TGGAGGGCTTTACCAAATTCCGTCAGCATCGGTTCCATCCTAGCTTAAACCTTACCAAGCGCTACTATCCGCACACCCACAACATGGACGGGTTC
TACGTGGCCAAGCTCAAGAAATTCTCCAACACCATACCCATAACTAAGGAGCAGCAGGAGGAGGATGAAAAGCAGCTGGATGAGGCCATCGAAGC
GGACGCCACTACAGAAGCGGCTGCGGAGTCTGAGGAGGTGGAGGAGGAGGTAGCGTCAAAGGAGAAGGGTCCCCGAAAACTGCTTGGAAAGCGCG
CCGGAAAACCCAGTTTCACCGAAATCGAACAGGAACTGAAGAAAAAGAAGCGGGAAGAGAGCAAGACCAAGTATGTGGCCAAGGTGTTTGAGCAG
CCTGTCAAAAAGCCAAAGCCAGAAAAGCCAGCAGAGAAGAAAAATGAGAAATCCCAGGCACCGGACAAGCAAACAAATTCAAGCGAGTCACCTTC
CAAGTCTGCACCTAAACAAAAACAAACCAATGGAAAACCACTGTTTCCAATTCAGATGCGAAATCATTCAATAAAAAGAACAAAGGATCGCAAC
CCAAGGAAAATGGAGCCGGATCACCAGCTAAACCAGATGACAATAAGCCAACAACCAATGGCACAAACTCCCCTAGCAAATCAGCAATTAAGGAA
ACGAAAACGAAGCCACAGCCGAAAGGAAAACAGTCGCCCAAGGGAAACGCCAAACTGGCCAAGGCGCCGCGAGTGGATATCGACGATGTGCCCAT
TCTCGAGGGAAAACCCATCAAGAAGCAGAACAAGCTGAAGCAAAAATCCAAACAGATCGGCCAGCTGAAAAAGTCCACGGCGGGTGCGAATGCGG
GAAAGAAGCAAAAGTTCAAGAAGTGA
(SEQ ID NO: 953)

Start ATG: 208 (Reverse strand: CAT)

MEEEDKKLSHRQKQRFVKREQKKVVQKAKLQEKRAKGKLPQPAKRKTAYNSDSDPEDNEEEPQVASSDEEVPQLVPAPKGQKATAPKGFTDDNDA
WLKPKKQQKQPETESEEEEEEDEESEEDSEDELGEECEEEEEGDDEEGLESDDDTAQVGKLADLSDDDDANSDDDFDISGEEDGAQADSDEEEDE
DDDDDDDDDDDDKLPIERANKKLKKREAEEAQLADDEMLETVDKQDVFQLPVEGEETEKDLTLQEVQQRIKDVSLVLSDFKRYRQADRSRGEYID
LLRRDLCLYYSYNEFLMEKLMDMLPLTELMEYLEASEIARPLTIRTNTLKTRRRDLAGALINRGVNLDPLGKWTKVGLVVFNSQVPLGATPEYLA
GHYMIQGASSLLPVMALAPQENERILDMCSAPGGKGSHIASIMKNTGVLFANDSNRDRIKAIVANFHRLGIVNAVVSCEDGTKFRNIMTGFDRVL
LDAPCTGTGVVSKDPSVKTTKSEVDVQRCYNLQRKLLLTAIDCTDAKSSTGGYIVYSTCSVLPEENEWVIDYALKKRNVKLVPTGLDFGVEGFTK
FRQHRFHPSLNLTKRYYPHTHNMDGFYVAKLKKFSNTIPITKEQQEEDEKQLDEAIEADATTEAAAESEEVEEEVASKEKGPRKLLGKRAGKPSF
TEIEQELKKKKREESKTKYVAKVFEQPVKKPKPEKPAEKKNEKSQAPDKQTNSSESPSKSAPKQKQTNGKTTVSNSDAKSFNKKNKGSQPKENGA
GSPAKPDDNKPTTNGTNSPSKSAIKETKTKPQPKGKQSPKGNAKLAKAPRVDIDDVPILEGKPIKKQNKLKQKSKQIGQLKKSTAGANAGKKQKF
KK*
(SEQ ID NO: 954)

Classification: hypothetical

Celera Sequence No. : 142000013384681
CAACGTCTAGGGGTCTCTGGACACTTGTGGCCGTTCTCCGCTTACGCATCTGTTCATTGATATGGCGAAGTAAAGACCGCAGCATTTCATCATCG
AAGAGCAGCATCCATGCTTCCACTGCATTGGACACTGTTCGGGCGGGTCCCTTGCCACAGGCCTGTTGCCCCAAAAGGGGTAGATCCTCTGCAGA
AATATCTGGGCTCCTGGTCACGCTCCATAGCTGCCCACAAGGAGATGTGTAGTTTCCGTTATTATTTGGTGGACGACCACGTCCTCGCTTCGGGG
CAGCTGGCCTGGCGGAATCCTCCTTCTTCAGCACCACGTCAGCCAGTTGGTCCTCGTTCATCAGCATGTCGCTGTCCTCGAAAATCCAGGGAAAA
TTGCATACTGCTTCCTGTAGCGGATCGGAGTCATCTCCGTTAAAGGAGGCACTTTGGACTGTGGAATCGACCGGCGGCAGCCGCTCCTCCACCTC
CATCTTTTCACCATCCTCGTCTTCTTCCTCCTGGTCGCTACATTTAATATTGGCCAGCAGCTCCTCGTCCAGCACGCATTCCATTGTTTGTTTAT
AAACTTGCAACAAAACAAACCTTTTCAGTCGTCGATAGGTTAGGACAGTAACGTCTATACATATCGATAATTTATATAGTTATCGAAAAAGACAT
TTAAAACATAAATCTTAAGCTTGAAAGGTTGAAAACTTATAAAAAAAATAGTTTGTTCTATTTAGAAAAAATTATGTACATTCTAAATATAACTT
ATTTATTTTAAATGTAGATTTAATTTCCAGCGTAGAGATAACTAGTGTATGTTTATAATTCTTAAACAAATTATACTTAACAAAACTTGTATTTA
TTCTTGGCGCCACTGTTCAAATTTCAAATGAACCTGCCAACTGAACTAACTCCCCAGTGGACCCCCATCCATGATTTATCGCACATAAGCGGCTA
TCGGATTTCTTTCGCCACTAATTTGTTGTTTGGCACGCAGCAAGGAAAAGGAATAAAACGCTTTAAAACCAGTGCCAAAATAGCTTTCCCCAACG
TTCGTTACTATATTTACGTTGTCTGCAAAAAGAGTTTGTCTAATTGGCCTCGATACTACGGTTGTGACGACTGCCCCGTCACTACAGTTTGCTGA
GTGCAGTAACCGGGGCCTGGCTGAAACACTGGGAAAACCAGTGTTTAGTGTAAATAAATGATAGTGGCACCCATTCGGACATCGCAGGTGAATCC
CCGGGAGCTCAAGACGCCCGTTATTTGGGCGCGCAGTGAATTTGTCAAAATATTTTGGTTAAAGTGTCAATTTGACATGTTATATGTCATGGTCT
CTCGTGTGCCAGTGCGATAGTTATCGATAGATAGCCCCAACTTAATTTGTTTTAAATATTTTTAAATTTCTTCTTTACTTAATTCACTACTGTAA
TACGTTCGTTTAATGTATAGTTCCTTGGAAATTAATCGATTTAGCAAGTAGACCGATTGGAAAGAAATCAAAAATCGATTTGAAATGCGTATTTG
AACCTTAGTTGGCCATGACTTTGGTGTCTGAATGACGCCTGCCCTCAGAAAAAGTTAGTTGAATCTCAAAGTCTGTGGTGACAACACCTAAAGAA
ACTAAAAAGTGACAGGTTTCTCTGTTTGTAAAAAAAAAAAAAATTGTAATTAAAGTTCTGTTCTTTTCCTTTCAATATTTGCATACCGTTTCTGGT
TGTGTTTTAATGAATTTTCTGTTTTCTGAAGCTTAAGTCTGAGCTGCAATGATCTCGCCGGAACAAGAAGAGGTCAACATGGTCCTGGATCGCCA
TGTACGGCAGAATATCCAGGACATGATGCACGAGGCTCATGTCCAGGCGAGCCTGCTGGAGAACGAAGGTGAGTTTGCTATATTTCGGTCGAGTT
CGGTCTTGTTCATGCCCGTTTTTTTTGCATGTCATCTGCAGGACGCGGCCGTTTCCACTCGGACTCAAGTTTGGACCAGGATTCTCTTCACGCTG
ACGTCATCGTGGAGGAGGATCAGAGCACCGAACACGGCGCCAACCAGGTGCAAAACTACCACGACATGATGGTGGACAGTGAACACCACATCGAC
ATAAATGGGTCGCTGCGCAAACGTCGTGGAAATCTTCCCAAGACCTCTGTAAAGATTTTAAAGCGTTGGCTTTATGAGCACCGCTATAACGCCTA
TCCGAGCGATGCGGAGAAGTTCACCCTGTCCCAGGAGGCCAATCTGACGGTGCTCCAAGTGTGCAACTGGTTCATCAATGCCCGTCGCCGCATTC
TACCGGAGATGATCAGGCGCGAGGGCAACGATCCTCTGCACTTCACCATATCGCGACGTGGCAAAAAGGTTAGCCCCAACTGTTCGAGATCAAGT
GCGTTGGGCGCAAACTTGACTGGGCCGAATCCCGCACACGGAAGTCCTGCTTCCGAAGTGGTGTGTTATCTTCTGGTCAATCATTATACCACTGA
AGTTACTAAATTGCTTGACTCCAGGTCGTTGGCGCTACAGAGGAGGTGGATGGCGCCGGTGAGATTCACGAGGGCATCGCCAATGTGCTGACCAA
CTTTGAACAGTATGTGCAGGGCCCCAACGGACAAATGGTCAAGATGGAGCCGGAGTACGAGGACAGTGTCATCTACAGGTAACTGGTAACCGGTC
TTTATGACCTGCTTCCCTAGCGTTAGTCACTTCTATCTCCTATCCCATCCCACCTATGTCCAAACTCCTTTTCCTCTTCCAAGCTGGCAGCAGGC
CATTGCAAACAACCCGATGGGCTTTCAAAGTCTTCACTCCTCGCTTCAAGCAACCATGATCGATAAAATTAAAAACTATCAGATGCGCAAGGCTG
CCGCCATTGGGGGTTCGGCGGTTGGCTCTGGTGGTGCTGGTGGGTCGAGCTCCAACTCCAGTCCTGCCACATCAATACTGCCATACAGCCTTTTT
GGCCAGCTGCCGCCAGAGTTCGATGACGAAGAAAAGCCAAGACCTCCGAAGCGCGTAAGAACGCGGACGGTTGCTGCAAAGAGTCCTAGGGAGAA
TGCCAAGCAAGCAAAGCAGAAGACTGGGAATAAGCAAGAAACCATGTACTGCTATAAGGATTCATACGGCGGAATCGTGGTGTCTCCTAGGTACA
GCTTCTGCTCCCATTGACTGATCCAGAGCCTTAAATCTTACTCAAGTGCGAGTGGCGGTGCTAAGATTTTACTTTTACCCCCAGGTCCGAAGGCG
AAGAGAGTGCACAGGGATACGAGTCCTGTGGGCCGAACAGCGAGGAGGAAGTACGCTTCGAGACCTCCCATGATTGGCAGAGCGTTATAAAGTAA
GTAGCTATGTGGATGTATTAAGAAAATATTGTAATCTCGGCCTCTGCAATTCCAGAACTGTATTTGGTACTGAGGAAGTCAGCACTTCGGCTGGC
AATAATCCAGGTACCTCTGGTTCTAAGGGATCTGTTCAGAATACCGCCAT
(SEQ ID NO: 955)

Exon: 1001..1227
Exon: 1759..1873
Exon: 1942..2377
Exon: 2434..2470
Start ATG: 1759

Transcript No. : CT25384
GAATAAAACGCTTTAAAACCAGTGCCAAAATAGCTTTCCCCAACGTTCGTTACTATATTTACGTTGTCTGCAAAAAGAGTTTGTCTAATTGGCCT
CGATACTACGGTTGTGACGACTGCCCCGTCACTACAGTTTGCTGAGTGCAGTAACCGGGGCCTGGCTGAAACACTGGGAAAACCAGTGTTTAGTG
TAAATAAATGATAGTGGCACCCATTCGGACATCGCAGATGATCTCGCCGGAACAAGAAGAGGTCAACATGGTCCTGGATCGCCATGTACGGCAGA
ATATCCAGGACATGATGCACGAGGCTCATGTCCAGGCGAGCCTGCTGGAGAACGAAGGACGCGGCCGTTTCCACTCGGACTCAAGTTTGGACCAG
GATTCTCTTCACGCTGACGTCATCGTGGAGGAGGATCAGAGCACCGAACACGGCGCCAACCAGGTGCAAAACTACCACGACATGATGGTGGACAG
TGAACACCACATCGACATAAATGGGTCGCTGCGCAAACGTCGTGGAAATCTTCCCAAGACCTCTGTAAAGATTTTAAAGCGTTGGCTTTATGAGC
ACCGCTATAACGCCTATCCGAGCGATGCGGAGAAGTTCACCCTGTCCCAGGAGGCCAATCTGACGGTGCTCCAAGTGTGCAACTGGTTCATCAAT GCCCGTCGCCGCATTCTACCGGAGATGATCAGGCGCGAGGGCAACGATCCTCTGCACTTCACCATATCGCGACGTGGCAAAAAGGTTAGCCCCAA
CTGTTCGAGATCAAGTGCTGGTGTGTTATCTTCTGGTCAATCATTATACCACTGA
(SEQ ID NO: 956)

Start ATG: 228

MISPEQEEVNMVLDRHVRQNIQDMMHEAHVQASLLENEGRGRFHSDSSLDQDSLHADVIVEEDQSTEHGANQVQNYHDMMVDSEHHIDINGSLRK
RRGNLPKTSVKILKRWLYEHRYNAYPSDAEKFTLSQEANLTVLQVCNWFINARRRILPEMIRREGNDPLHFTISRRGKKVSPNCSRSSAGVLSSG
QSLYH*
(SEQ ID NO: 957)

Name: Homebox Protein
Classification: transcription_factor

Celera Sequence No. : 142000013384574
TCAAAATCGTCAGGTAAATCTCAATAGAAATTAGAATCTTACGAGTCGATTAACAATTGGTGTTCACTTCTAGAAACGACGAAGACGGCCTGGAG
TTCGATCTGATTGGCGTGTATCCCGCCATTGCAAATGCCTTCCGTCGCCTGATGCTCAGCGATGTGCCCAGCATGGCCATCGAAAAGGTGTACAT
ATACAACAACACCTCGATCATCCAGGACGAGGTACTTGCCCATCGAATGGGTCTACTTCCGTTGCGGGCTGATCCCCGTCTATTCGCATACCGCA
CCGAGGAAAGCACTGAGGCGGGGACCGAGCAGGATACGCTTGAATTTGAGCTGAAGGTGAAGTGCTCGCGGCGACGGGATGCTGGAAAAGATCAG
TCCAACTTCGATGACATTTACAAAAACCACAAAGTGTACTCGGGTCATCTGAAGTGGCTGCCCAAAGGAAAGCAGGCGCAGATATACAGCGAGAG
TGCTGTGAACTGCATTCACGATGACATACTGATTGCCCAATTGCGTCCGGGTCACGAGTTGGATCTGCGCCTGGTGGCGGTTAAGGGACTTGGAC
GGGATCACGCGAAATTCTCGCCGGTGGCCACGGCCACCTACCGACTGCTGCCCATGATTAAGCTGAACCGCGAGGTGACCGGTAAGGATGCGTAC
CTATTACAGAACTGTTTCTCACCAGGAGTAATTGGCATTGACGAGAATGAAACTGCCTATGTAAAGGATGCACGCTACGACACGTGCAGCCGAAA
TGTGTATCGCTATCCCCAGCTAAACGACGCTGTGACTTTGGCCCGTATCCGAGATCACTACATTTTCTCCGTGGAATCAGTCGGCGCACTGAAGC
CCGATGTCATCTTCCTGGAGGCGGTCAAGGTATTGAAGAGAAAGTGCCGGGCGCTAATTGACGAAATTGAGGCAGAATAGTTATTTATTTAGTTG
TTAAAGAAATTATATTATGTACATAAGACAGCTTGATATAAATTGTAAGCCTACGAAGATCGTGCTTGCTCTCTCTTGCGCTTGAGCACCTTCAG
GCGAAATTCCGTTAGGACCACCTGCAGACGCTCCTGGCACATTAGTGCGTCCTCCAGGTCCATGTTGTTCAGCTGCAGAGCCAAACTCTTGCCAA
ACAAGTCAAATTCACTAATAATGGTGTCTTCCGTCATCGCGTCGACTTGGTATTCGTTATTAATCTCCGTATCTTCCGGCTTGAGCTGTATCATC
TCTTCCTCGTAGACCACCTCTTGGTCCTGGAGATCTGTTTCATTCTGTTGTACTTCGAGGAACTCGTTCTCAACCTCAAATTCTTGCTCTTGATA
GGGCTGATCTGTTCTGAGTAAATCATCCAGGATTGAGTCGTTCGAGGCGATTTCGTCCTCCTCCGTCTCCTCCTCCATGCTCTCCACCTTCGTGT
CGTTCTTGATCTTTGGCTGCATTTTGCTCCTTGGCTTTTGCCTTGGATAGGTCTTTGATTTGGCTTTGGGCTTTGCTTTGGGTGAAATTATGGAG
GCCTCCAAGTCTGGGTCATGCTCATCTTTGACAAGTTCACCCTTAATCATATTCTGTAGGTATAAATACGGAGTTGTTAATTTTATGTAAATTAG
TAATGAGATGAGAATTTTTTTTTTGGAGCGATAAGTTGTGCATCGCATAGAGGGAGCTACTGGTTTGGTTAACCATTGCACAAGAAGTAGTCAAT
GGAATAGTTAACGAAAAGTATGGCGAAAACTCACACAAAAATCGTGTTTGAAATTTAGTTTGGATCGCAAAATATTTGAATCAATAATGGACACG
GGTCATTCCTATTGCTTATGCACAAACCCAATCCCACCTTGGCAAGAATGTTGTGGTACTTGAAACTTTCCTGGTGTTTCCGCGTTGCGAGGTGC
TGCTTGATGGACGCTAGTCTGGCGAGGACATTGATGTCGCAGATCTTGCAGTGCGCCGAGTAACCGTCATTACTAGACGCCAGCCAGCTGGAGAG
CTCCGGATATTTCTCCCACTCTGTGCGATAGCGTTGGTGGTACAGTCGCTTCACCTTCTTGTCCTCATCCGTCTTGTAACCCTTCAGCATTGTGC
CCGCTTTCGGATGAAGCTTGTCTGATTTGTGGAAAAGTATTCTTTGAAAGATGAGCGCCAAAAGCAGTCTTTAATAGCTGATGGTGGTAAATATT
TTGGTATATTCCAAAAATTTGCGACGCGAAAAAAATCTGAAAGTCGATGCGGTGTGACTGTAATCGAATACGTTATAATACCAGCAATTAATTCC
AGGGTTGCGACATAGAGGTTGCTGCGCAACGGTCACACTAAGCTGTTTTGTTTATATAAACATTTTATGCCTTCAAGTTTATATTAGAGGCGTTT
ATGGTTGTGTTATGTACTTTTTGAAAATACCTTACTTGTACATAGTTCAAATTAATTTAGTTTGAGATTTTAAATAAAATATTCTTTCATGGTTT
GGGTCTCAGGTAAAGTTTAAGCAGTCACAATACGGCCACACTACACACTCATAGAGAAAAAATATAGTAAATAAAAAGGCTTTGCCGAATTCAGG
ATAGCTTTTGCCTGCACCGTGGGTGCTCAGCCAACATGGTCATTCCAAAGGAGATCCTAAGCGACTTCAAGGAGCTATACGAGAAGGCCAACCGT
CTGGTGGAGGAGGAGAGCCGCAATGATCCGCCCACGGATCCATTCCGCTCCCATTATAAAGCGCGCGATGTGCTAATTGTCTTGAAGAAGCAGCT
GGACGACCAACTGGTATCTGTGCAGGCCAGCGAGGAGGACGGTGGTCAGGACGATCGCTGCTATCACTCTCTGTTGGCCTTCGTTTGCCGGGATC
TAGGCAGGATCTACATCTACACAGAGGAGCAGGCAGAGGGCGAAAAGATGCTCAATCGTTGTCTGGAACTAGTCACGCCGTTTAAGGAGTGCCCT
GAGGGCATCATTCCATTCATTGGGGCAATCAACGAGCTTAGCATTGTGCTGGCCTCCAAGGAAGAGTACAATAAGGGACTGGAAATTCTCCTGGA
GGCAGAAAAAATCTACGAGGACTTCAAAGCCAGTGGTCTGAAGCCCCTGGCCATTCAAGATGTGTTCAATCCTCCGGAGGAGGGACAACAATCTC
ACGAAGCTGGTCCCAAGGAACTGGAATCCCTGTACACGCTAGTCTCATTTTACATGGCGCAAATGTACGGGCATTTGGGTGAGCCGGAAAAGTCG
GCCAAGTGCTGC
(SEQ ID NO: 958)

Exon: 2242..1876
Exon: 1573..1001
Start ATG: 2085 (Reverse strand: CAT)

Transcript No. : CT25498
TCACACCGCATCGACTTTCAGATTTTTTTCGCGTCGCAAATTTTTGGAATATACCAAAATATTTACCACCATCAGCTATTAAAGACTGCTTTTGG
CGCTCATCTTTCAAAGAATACTTTTCCACAAATCAGACAAGCTTCATCCGAAAGCGGGCACAATGCTGAAGGGTTACAAGACGGATGAGGACAAG
AAGGTGAAGCGACTGTACCACCAACGCTATCGCACAGAGTGGGAGAAATATCCGGAGCTCTCCAGCTGGCTGGCGTCTAGTAATGACGGTTACTC
GGCGCACTGCAAGATCTGCGACATCAATGTCCTCGCCAGACTAGCGTCCATCAAGCAGCACCTCGCAACGCGGAAACACCAGAATATGATTAAGG
GTGAACTTGTCAAAGATGAGCATGACCCAGACTTGGAGGCCTCCATAATTTCACCCAAAGCAAAGCCCAAAGCCAAATCAAAGACCTATCCAAGG
CAAAAGCCAAGGAGCAAAATGCAGCCAAAGATCAAGAACGACACGAAGGTGGAGAGCATGGAGGAGGAGACGGAGGAGGACGAAATCGCCTCGAA
CGACTCAATCCTGGATGATTTACTCAGAACAGATCAGCCCTATCAAGAGCAAGAATTTGAGGTTGAGAACGAGTTCCTCGAAGTACAACAGAATG
AAACAGATCTCCAGGACCAAGAGGTGGTCTACGAGGAAGAGATGATACAGCTCAAGCCGGAAGATACGGAGATTAATAACGAATACCAAGTCGAC
GCGATGACGGAAGACACCATTATTAGTGAATTTGACTTGTTTGGCAAGAGTTTGGCTCTGCAGCTGAACAACATGGACCTGGAGGACGCACTAAT
GTGCCAGGAGCGTCTGCAGGTGGTCCTAACGGAATTTCGCCTGAAGGTGCTCAAGCGCAAGAGAGAGCAAGCACGATCTTCGTAG
(SEQ ID NO: 959)

Start ATG: 158 (Reverse strand: CAT)

FIGURE SHEET 515

MLKGYKTDEDKKVKRLYHQRYRTEWEKYPELSSWLASSNDGYSAHCKICDINVLARLASIKQHLATRKHQNMIKGELVKDEHDPDLEASIISPKA
KPKAKSKTYPRQKPRSKMQPKIKNDTKVESMEEETEEDEIASNDSILDDLLRTDQPYQEQEFEVENEFLEVQQNETDLQDQEVVYEEEMIQLKPE
DTEINNEYQVDAMTEDTIISEFDLFGKSLALQLNNMDLEDALMCQERLQVVLTEFRLKVLKRKREQARSS*
(SEQ ID NO: 960)

Celera Sequence No. : 142000013384574
CTTTTGGGTACCAAATCTTAGGCGTTCGGTGGTCCATAGTCATGTGCTGGACTGCTACATGTCCGTGGTGGTGACGGAACGCACGCTGGAGCAGA
TCCATGAATGTCATGGCTTTGATCACTACCTCCTCAAGAATCGTGCCTGCGATCTTCGCTCCGCTTTGGCTCTGAAACTCAAGCGAGAGGTGCTT
CAGGCCCTGCAGAACGGTGTTCCAGCCCTCGCCGACGAGCCCGAACGCCAACAGGAAGTGCTTAAGGAATACCGCCGCTATCTGGAACCATATAC
GCCCGAGGAAATCGATTGGTACGGCCATACCTATTTGGAGGCCATACGCAAGCTGCAAAAGCAGCTGCGCGAAGCGGAAAAGGTGGTGCCGCATA
AGTTGGAGTTCCGCGGAAAGCTTATCGAGCAGCTGCGCCAGGCGGGGATCAGCGAAGCGGGAAAGCTGGAGAAGCCGGATGCATTAGCAGCAGAA
TCGTCGGTCGAACACAAGGATTCGGATATCGAAGCGCTTACAAAGCTGTAAGTCACAAATACTTCTGTAATGAATTTCCTAACCAATGATTTATT
CCAGGGAATCCTCCCCCTCTTCCAGTTGGCTGTCTAAAATCAATCCTTTCGGCAAGAAAGAAACCTAGAAAAGCTGTCCGCGTTTGTTTTTGATT
TATGTGTTTAGCCTCGAACGAATAAACATAACTTCGGAAACATTTCGTTACAATTTGAAGGTATTAAAACGTTGTTACTCGAACGTCTTTATTTC
AAATATTCGTTACATCTGGTACTGTATAAAAACAAGTAGAATCACACACTGAACATGAACGTACGCGGCAAAGTAGAAAAAGGAATGATTGCAAA
TCCCCACGAGAATACAGAAATACATTGACAAATCAACTACGCTGATCACTTTACGCTTAGACTATGGTTAGTGTATAGCTCCGCAAGCGGGCAGA
GAGCTTTGTGCCGTAAATGATCCCAGTCCGAGCTGGAAGCCAGGTAGGCCTTAAGCGATTGGATTTTTCCTCATTAATTCGATGTCAGCCTTCAT
CATGTCGCTAACCAATTCCACGAAGGTAACTTTAGGCGTCCAGTTTAGCTCTCGATTGGCTTTGGACGCGTCGCCTTGCAGCAGATCGACCTCCG
TCGGCCGAAAATACTTTGGATTTATGCGGACGCGCACAATACCCGTGCCGTTCTCCACTCCCACCTCGTCCACACCCTTGCCCTTCCACGTTATC
TCTCGATCAATATGCTTGAACGCGGCTTCCACGAATTCGCGCACACTGTGCGTTTCGCCTGTAGCTATGACGTAGTCGGAAGGAGACTCCCGCTG
CAGCATCATCCACATGGCCTCCACGTAGTCGCTGGCATGTCCCCAGTCGCGCTTTGAGTCGAGATTGCCCAGTTCAAAATACTCCATTTGCTTGT
GATAAATCTTGGCCACGCTACGGGTGATTTTTCTAGTCACAAAGTTCTCGCCACGTCGTGGACTTTCATGGTTGAAGAGGATTCCATTACAGGCG
TACATGTTGTAGGCTTCCCGGTAGTTGATGACGATCCAAAAGCCGTACATCTTAGCGCAGGCTAAAGTTAGGTGGGATTAAGTATTACTTTTAGC
ATACATTATCGAAGCTGCTGCCTTACCATATGGCGACCTGGGATAGAAGGGCGTCTGTTCGTTCTGTGGCGTCTCCACCACTTTACCATATAGCT
CCGAAGTGGAGGCTTGGTAAAACCTCACGTTCTTTTCCATGCCACAAGTGCGGATGGCGTCCAGAATGCGCAACGTGCCCACGGCGTCCACCTCG
GCCGTGTACTCACTGAGATCGAAGGAGACCTTGACATGGGATTGTGCTGCCAAATTGTAAATCTCCGTGGGCTTCACCATATTGATGATCTTCAC
CAGGCTGCTGCTGTCCGTCATGTCGCCATAGTGGAGCTTCATACGCCCACCTTTGTGCGCCTTTGGATCGGCATATAGATGCTCAATGCGGGTGG
TGTTGAAGGTGCTGGCCCGCCGAATAATGCCGTGCACCTCGTAGTCCTTCTTGAGCAGAAACTCTGCCAAATAGGAGCCATCCTGGGCGATAGGG
AACAAGTAAGAATCGAGCACTTTGAACACGTAAGCACGGAATGAAGGAGATGCCCCTGAAACAGCCGTGACTAATTCATCAATTACACACCTGGC
CCGTTATGCCTGTTATCAGCGCCACTTTATCACGGGAGTCGCCTTCGGCGCCGGCTTCCGTTCCGTTTTGGTCCTTGCTGCCGTTGCTGCTGCTT
TCAGGACGTTGCTTCTTGGTTTCCGGGGCCCCATCGGAAGTCGACATAGCAATTAGCCGGGTATTTAGCATTTACTGACGCTAGTTTTAATTTTC
ACGCCGACGCAGCCCGGATAATAAACAAACTTTTGTCTACAGCACTCAGGTAGAGGTGAATAAATAATCGATTGGTTATCGATACATCGCAATCG
AAGCACTTGTACGGGACAGTGGGGCAATCTATTTAAGACAGCCTAAATTATTTTCAATAAGCAAAAAGTAAATATTTTATCACAAAAAACAAATT
ATGTATGGAATAACATTTTAAATAAGAATTCAGCGCAAATTTAAAATTAAAACCAAATCTGGTTGAATAACACTTTATTTACTTTACTGCCAATG
TTGCACTTTTTTTCGATTTTGTTCCACTTTGTGGCAGTGTTGAGTAGCAGGAAAACCCACGTAGCGATTTTTAGCGCATACCTTTCAGCGAAAGC
CGGACGAAAATAACATAACGTTGGCACAACCACCTATCTTATCATTCCTCCTCCACTCCCAAGCCGATTCGCCACCGGGCATCAATATCTTCTTC
GGCGGAACCCGCATTACGTGTGCGTAAACGGCGGCTTTCAATTTCATTCTCGGAGCGACCGGCCGGCCAGCTTGATAACACCGGTGCATAGTGAA
ACCAGCGCCGCTTACTAATTAAGTACGACCACGACCTCCGAGATAAACAGAAGTCAATTGTTCGCAGCACAAAAATGACGGATCTTATCAGGCAG
GGTGCTCTGTTCCTTATGAGCGAGAAGTGCTATGATAACTACTTCCTCTATCACAACTTTTTAGATGGTGAGTGGCTGCTAATTCAAAAAGGTAT
GTGCCTATTAAGTATCAATTAACATTTCTCGTAGTTCCGTGCTTCAAGGCTTTGCTGAGCAAGGGCTTGGGATTGGCAATTATCGCAGGTTCCGT
GCTGGTCAAAGTACCACAAGTGCTGAAGATCCTTAACAGCAAGTCTGGCGAGGGCATCAACATTGTGGGCGTAGTGTTGGACTTGCTGGCCATCT
CCTTCCACCTGTCGTACAACTTTATGCATGGCTATCCGTTTAGTGCCTGGGGCGACAGTACCTTCCTGGCCATCCAGACCGTCACA
(SEQ ID NO: 961)

Exon: 2411..2181
Exon: 2077..1642
Exon: 1581..1001
Start ATG: 2327 (Reverse strand: CAT)

Transcript No. : CT25524
ACAAAAGTTTGTTTATTATCCGGGCTGCGTCGGCGTGAAAATTAAAACTAGCGTCAGTAAATGCTAAATACCCGGCTAATTGCTATGTCGACTTC
CGATGGGGCCCCGGAAACCAAGAAGCAACGTCCTGAAAGCAGCAGCAACGGCAGCAAGGACCAAAACGGAACGGAAGCCGGCGCCGAAGGCGACT
CCCGTGATAAAGTGGCGCTGATAACAGGCATAACGGGCCAGGATGGCTCCTATTTGGCAGAGTTTCTGCTCAAGAAGGACTACGAGGTGCACGGC
ATTATTCGGCGGGCCAGCACCTTCAACACCACCCGCATTGAGCATCTATATGCCGATCCAAAGGCGCACAAAGGTGGGCGTATGAAGCTCCACTA
TGGCGACATGACGGACAGCAGCAGCCTGGTGAAGATCATCAATATGGTGAAGCCCACGGAGATTTACAATTTGGCAGCACAATCCCATGTCAAGG
TCTCCTTCGATCTCAGTGAGTACACGGCCGAGGTGGACGCCGTGGGCACGTTGCGCATTCTGGACGCCATCCGCACTTGTGGCATGGAAAAGAAC
GTGAGGTTTTACCAAGCCTCCACTTCGGAGCTATATGGTAAAGTGGTGGAGACGCCACAGAACGAACAGACGCCCTTCTATCCCAGGTCGCCATA
TGCCTGCGCTAAGATGTACGGCTTTTGGATCGTCATCAACTACCGGGAAGCCTACAACATGTACGCCTGTAATGGAATCCTCTTCAACCATGAAA
GTCCACGACGTGGCGAGAACTTTGTGACTAGAAAAATCACCCGTAGCGTGGCCAAGATTTATCACAAGCAAATGGAGTATTTTGAACTGGGCAAT
CTCGACTCAAAGCGCGACTGGGGACATGCCAGCGACTACGTGGAGGCCATGTGGATGATGCTGCAGCGGGAGTCTCCTTCCGACTACGTCATAGC
TACAGGCGAAACGCACAGTGTGCGCGAATTCGTGGAAGCCGCGTTCAAGCATATTGATCGAGAGATAACGTGGAAGGGCAAGGGTGTGGACGAGG
TGGGAGTGGAGAACGGCACGGGTATTGTGCGCGTCCGCATAAATCCAAAGTATTTTCGGCCGACGGAGGTCGATCTGCTGCAAGGCGACGCGTCC
AAAGCCAATCGAGAGCTAAACTGGACGCCTAAAGTTACCTTCGTGGAATTGGTTAGCGACATGATGAAGGCTGACATCGAATTAATGAGGAAAAA
TCCAATCGCTTAA
(SEQ ID NO: 962)

Start ATG: 85 (Reverse strand: CAT)

MSTSDGAPETKKQRPESSSNGSKDQNGTEAGAEGDSRDKVALITGITGQDGSYLAEFLLKKDYEVHGIIRRASTFNTTRIEHLYADPKAHKGGRM
KLHYGDMTDSSSLVKIINMVKPTEIYNLAAQSHVKVSFDLSEYTAEVDAVGTLRILDAIRTCGMEKNVRFYQASTSELYGKVVETPQNEQTPFYP
RSPYACAKMYGFWIVINYREAYNMYACNGILFNHESPRRGENFVTRKITRSVAKIYHKQMEYFELGNLDSKRDWGHASDYVEAMWMMLQRESPSD
YVIATGETHSVREFVEAAFKHIDREITWKGKGVDEVGVENGTGIVRVRINPKYFRPTEVDLLQGDASKANRELNWTPKVTFVELVSDMMKADIEL
MRKNPIA*
(SEQ ID NO: 963)

Name: GDP-mannose 4,6-dehydratase like
Classification: enzyme

Celera Sequence No. : 142000013384668
AAAAGATATGAAAGAGCCCCCGTTAAGCTATTCAAAAACAAAACAATGTGCAACATGTTTTAAATGCTTAAATAATTTTAATTTGATATAATTCA
CAAGCGTTATACATTTTTTCCCTTAGACAACCCTATGAAGTGAACCTGATGCTTCCCACATAAGTAAACATCTTGGATGCACTCGAATTTCGTCG
CCAGGCACCGCCAGTCTGGATCGAACTAAGCAAAGTCCAGAGCACCGCGATTGAGTATTGGGCGTTTCAAATTTCCTGGCTAATTTCTCACAATC
AGTTAATGCTAACAAAAGTACTTATGCGGCGGATAGTTCCTAAGAATGTGGGAGTATGACTTTAAGATACGATAAACTTACTTAATGCAAATAGG
AGTAAGATTGAAAGTTAATAATTAGTTTTAGGTACCCATAAGATGTTTTTTTCTTCGGCTCTCAAAATCTGCTTTATTTAGTTTTCGTTCTTTAA
ACTATGTATCTTTTAAGTGGGCAGTAAACAAGCTTCATCCACTAAAAGCCCAAACAAATATTTACTGCCTTTTTTTGCTACTATAATTGGTTTAT
TACTGAGCTGAGAACCTCTCCCAAAGAGATCTATTTAAATGCCGACTGAGAGATTTTAAGAACAGAGAGAGAGTTCCATTTTGTTTATGAAAAGC
TAATTGCCAAATTGGGAAGCCAAAGCCTGCTGGAATATTGCATTCCATTTAAGAAAAGAGGGTAGGAAGAAGAAGAACTGGAAACGTGGCTAAAT
ATGTTAACTAATTCATTAACTTCGTTTCCTTTTCAACGCCCACTGGAACTAGAATCAGAGAGAGAGAGAGAGAGAGAGAGAGAGAGAGAGAGAGA
GAGCCAAACTTAAAATTAAAACACTACCTTTTTCCAGTTAACCGGCCGGCTTACACACACAGTCAAACGCCTGAAGCTTGAAAGAGAGTGTTTGC
TTGATGAGAGCGGCAAGCGTATAAAAGCAGCGTCGCCGGCAGAAGAAAGTCAGTTGCAGTGCAGTCGTCGTGACGATCGGTTCAGTGATAGCTTC
CCAGTGGCTGGAGAGAGTGAGAGTAGAGAGTAACGGAAAGAGAGTGCGAATCGAACCGAACGCTATTCCTTCGCCCACGATTTAAGTGAACGCTT
ATTAGCGAATTGAAGACCCGAGAGCCCCAGTGCCCAGCTGATTTCGTATTCTTTGTTGAGGTAAGCCAAGGAATCCCTGGAACCACCTCATTTCG
TAGCACCTTAGTGATGTAATTACGCACCAAGATTTACCCTTGCCAAAAAGTGGAAAACGCTTTTGCGAACTTCGATGCCGAATGGTGTTCGTCTC
GAATCGGTTCTAAAATTACACACAATGGTTTTTTGGCTTCGATTGATTTGATTTGATTTTTGGGTCAATCGATTCGAAATCGAAAAGTTTTGAAC
TCGTTTCGCAGAATCGCAGTTCGCGCGGATCTCTCGCCTCGCTCGCAAGCAAATATGTGAAGGACAACGACGTTAACCGATCAACTAGAAGCCCT
CTTCTTCTGCCTCTTCAGAACCGATCAGATCGGAATAGAAATATAGAAACGACCATAGCACCTCCGTCGACTGTGGAGTGCGTGAACGTATTTCG
AAGCGTGAGGTACTCGAACCGGAACCAACTTGAGTGTAGTGCATATTCGGGATCTTATCCAAACGCAGGCTTACATAACCCCTATTTTAATACCT
TTTCAAAAAGGAATAATTGAAATTCAAAACAAAATTATTTAGCAACAAACAAACAATCAGTTATATTTTTGAACTGATATGCCTCGGGGCTAGGG
GTCCCAGACTTTCAAATTCTAGTGATAACCCCCCCGATCGGCGAGTTCATCTGGAAATGTTGCCCATATGGGCCGGGTGCACGTGAATCTCTTCA
GTGCCCATTGACGCACTTTGTGTGCCTCCACTGGGTCCTTGACCCGCTGTGATCCCTGCCCTTTCCCATGGATTGGATAATCTAGGTGTCATTAT
CTTCCCTAACCTTTTCCCACGATTAAAGTGAAACCATTTGCCACGATTTTAGTGCCGTAGTGCCAGATCAAAGAGCCAAAATAGATCAGAGAATC
GAAATTTAATTAAATCATGACACCGAAACACCGAGACAGACCAAATTAAATTCAATTGAAGCTGTCATGGCAACAAGTGCCAGCAAAAAAAAGGA
AGAGCACTACGGCGAAACCAGAAGATAACACCGAAAAGTCAAATCGATTGTTGCAATTTGAGACTCTCCGAAAGCGAAAATTGCAGCGGAAGAGG
CGGCCAATCGGCCATTACTAAACGGTGATGGGGTTGGGGAGGGGATCCGAAGTCTTGGTGACTGACTGGGCGCCCTGCCAAAATGATGGCAAAGG
CAGAGACACCATGATTCCTCAGCCAAATCGAACGAAAACGGGTTTACGCTCTACATGGACCCCATTGCACACTGAATCCGTTTATCCAGCGAGGC
AAAAAGTGCCGACGACAATGGAAACAGGGGCGTAGTATCCGTACCTCCTCCGTCCTACGATTCTTCCAGCAGCGCCAACGCCCCAAAAGATATTG
ATTCCGACTTTTGCGCGATTCAGCGAAAAACATAAGGGGACCAAAAGTGGGCAGACGGGCGGAGGAGTGGTGTCTGTTTCTTTGATATGCGTGGG
TGTGTTGTCTGTGCGGCAATCGATGCACTTCCGGTGGGTTCTATGGGGAAATACTCTTGCGTTTCAGTATATATCTACTATATATATTGCAATTT
TATGGTAATTATATTTTCTGTCAACTTTTGCCTTGACTCCGCTTGATTTATTGCATTGTTCTTGAAGAATAGCCTCATAAGGCATGCAAGCAAAC
ATGGCTTTCGAACTAGCGCAAAATTAGCTAGTAGCTTATAGAGTATATGTAGCTTACCCCCAACGGTTTTTATATCATTTGTTTAAACCACTTAA
GAATATTCGTAGCCTTGTGGACACACTTTATCGTGGATCGTGGAAGTTATACGACACCGTAATATATCCTTATCACTCACGCATATTCTGGCCCA
CTTCAGCTAGAAACGTTTGGCGCGTTCGCCTTATCATAAAAATCAGGCTATCGACTGATTAACTGAGTTTAATAAGCCAGCAAACGTAAACAAAA
ACTACGAAAGTTCTGGAAAACTAACCAAGGCTATTTCAAAACGGCGTGAAATGGCTAGCACTCTAAATTATTGAAGTTTTCAACATATGTATATC
TAATCTGATAGCCAAGAAAACATAATGGTTACCAACTTTCCATATACACCGTAATTTATTATTGATGAATATCAAATTATCGATAGTACTTCCCC
GATAAGATTCTGTTAACACACATTGCTCTACTTTTCTATCAGGGAATTGCATTGAGAAAGCGCAGAGATGGCCGATGAAGCACAAGCACCACCAG
CTGAGGGAGCACCACCAGCCGAGGGAGAGGCGCCACCACCCGCCGAGGGAGCCGAGGGTGCCGTCGAGGGCGGAGAGGCCGCTCCACCAGCAGAG
CCCGCCGAGCCCATCAAGCACAGCTACACGCTCTTCTACTTCAACGTGAAGGCGTTGGCCGAGCCCCTGCGCTACCTGTTCGCCTACGGCAACCA
GGAGTACGAGGATGTGCGCGTCACCCGCGACGAGTGGCCAGCCCTGAAGCCCAGTGAGTGCCATAGTCCATCATTGAGTGGTCAGTGGACTAACC
ATAATCTACTCTGTCTCATCCAATAGCCATGCCCATGGGACAGATGCCCGTGCTGGAGGTGGACGGCAAGCGTGTGCACCAGAGCATTTCGATGG
CTCGATTCCTGGCCAAGACTGTCGGCCTGTGCGGCGCTACTCCGTGGGAGGATCTGCAGATCGACATTGTCGTTGACACCATCAATGACTTCCGT
CTAAGTAGCGAACAATGTGTGCCTCAGTTTCATGTTCAGTGTCCTTGATTAACTCTGGAATTTTTAATGTATAGAAATTGCAGTCGTCTCGTACG
AGCCGGAGGACGAGATTAAAGAGAAGAAGTTGGTCACCCTGAATGCGGAGGTCATTCCATTCTACCTGGAGAAGCTCGAGCAGACCGTCAAGGAC
AACGATGGTCACCTGGCTCTGGGCAAGGTGCGTGCTCAAATGAGAACTTGAAACCATACACTCGTTAATTTTGAATGAACAATACTAAGAACCAT
CGATTCCTTTCACCCACAGCTGACCTGGGCCGACGTCTACTTCGCAGGCATCACCGACTACATGAACTACATGGTCAAGCGCGATCTGTTGGAAC
CCTACCCAGCTCTGCGCGGAGTCGTGGATGCCGTCAACGCTTTGGAACCGATCAAGGCCTGGATCGAGAAGCGCCCCGTCACCGAGGTCTAAGTT
CACCGAACAGGACTTGGAGGATGGGAAAGCATTGCACAACCACTCAGACACAACCGCACCGCAGAAATGCACACCACCCACATCTGCACACATT
TTGTTCCTTTTTGCGGAGGATCCGAGAGGACGGCGGATTTTCGCACGGGGTCATAAACGCGTAGGAGTTTAGCACGTATCACTATGGATAAATCG
TATTTGTTCTTAATTTCTTGGTTATAATTCTCTTTGCATGGCGCTATATACATATTTCTATTGGGGTCCGGCAGCGGATCGCCGTTCGTTAGCTT
CTTCTGAAATGATGAAAGATAATACTTATTGCACAGTTTATAATATTTTGGCTTACTTTTAGAACATACATTTAGCGCACCTATGCAGACATTTG
CTGTACCTATATATATATATATATGCATAAAATACAAAAGCTACGAGTGGTTCATCTTATAGGCGTATTCTATTGCAATTTATTCAATGCGGAGG
GCTCAATAAATATTTAAAACAACACCAGCTAAGGCTGAGAAACAATTACAAATTCTTATTTTGTTTTTTATACAACACGCCATCGCGGCCCCAGG
AATTTTCTTCGTCTCATCCAGTTCCCTTTTAAGTAGCCATTAAAAAAAGACTCACATCAATAGAACCGGTTTCTCCAAAAAAAAAAAAAAACAGAC
TCTTACTGCCAAATTTCAAATGCACATAATCACATTATTATATACATATTATTTATTCAAATTTGTAATTGTATTTTTTGAATATTTTCACAAAA
CACTTTTTAATAAACATAACACCTAAAAAGGAATGAGCACTTTTTAAAAGCACGACAACTGGTTTTATTTAATTTTTGTACGATGTATTGGAATA
ATTTATTAATTGTTGACATATTTAAGAAATTTAAAGAAAGTGTTTATTTACATTATTAATTTTTATTTTTATTATCCTTTCAATTTGCATTTCCA
AAGCCGACCCGACAGACATAAATAAATGCATGGAGTTGTGTTCAACATTGTTTATAAACGTTTAAAAAAATAACATTTCAAATTAACATTCTTT
TAAGTCACTTTGGACAATTCAAGCTTAAAAGTATAAATGCACAATTGGTCAGTTTTGATTCATTATTTCATATTGTATGTTGCGGTTACTGGTGC
TTCCAGTTGGGTGGGCGCTTCTCGAAGAAGCTAGCAATGCCCTCTTTGGTGTCGCCCAGCTGGAAATTTTCGCACATCTTCTCCTGCGCAGCCGA AAAGGCTTCCGCTTGGGACATGGCCAGTTGCTTGTAGTAGAACTCTTTTCCCAGAGAGATGACGGCACGACTTTTTGCCTTTATGGCATTGGTGA
TTTCCTCGATCTCCTTATCTAGTTCCTCTGCAGGAACAGCTTTGGTGACCATTCCCGATATGTAGGCTTCTTCACCAGTAACGGGAAGACCGGTC
ATTAGCATATAGGCGGACTTTGGACGCGACATAATCCGGGCAACTGCGACTCCGGGTGTTGAGCAAAAAACTCCGACTCCAGCCCTAAAAATATA
AATTATAACATGATTAACTGGTTTCATAGAGGGTTTTCATCCTTACCCTGGAGTAGAGAACTTG
(SEQ ID NO: 964)

Exon: 1001..1200
Exon: 3368..3663
Exon: 3732..3899
Exon: 3970..4112
Exon: 4200..4954
Start ATG: 3393

Transcript No. : CT25660
CAGTTGCAGTGCAGTCGTCGTGACGATCGGTTCAGTGATAGCTTCCCAGTGGCTGGAGAGAGTGAGAGTAGAGAGTAACGGAAAGAGAGTGCGAA
TCGAACCGAACGCTATTCCTTCGCCCACGATTTAAGTGAACGCTTATTAGCGAATTGAAGACCCGAGAGCCCCAGTGCCCAGCTGATTTCGTATT
CTTTGTTGAGGGAATTGCATTGAGAAAGCGCAGAGATGGCCGATGAAGCACAAGCACCACCAGCTGAGGGAGCACCACCAGCCGAGGGAGAGGCG
CCACCACCCGCCGAGGGAGCCGAGGGTGCCGTCGAGGGCGGAGAGGCCGCTCCACCAGCAGAGCCCGCCGAGCCCATCAAGCACAGCTACACGCT
CTTCTACTTCAACGTGAAGGCGTTGGCCGAGCCCCTGCGCTACCTGTTCGCCTACGGCAACCAGGAGTACGAGGATGTGCGCGTCACCCGCGACG
AGTGGCCAGCCCTGAAGCCCACCATGCCCATGGGACAGATGCCCGTGCTGGAGGTGGACGGCAAGCGTGTGCACCAGAGCATTTCGATGGCTCGA
TTCCTGGCCAAGACTGTCGGCCTGTGCGGCGCTACTCCGTGGGAGGATCTGCAGATCGACATTGTCGTTGACACCATCAATGACTTCCGTCTAAA
AATTGCAGTCGTCTCGTACGAGCCGGAGGACGAGATTAAAGAGAAGAAGTTGGTCACCCTGAATGCGGAGGTCATTCCATTCTACCTGGAGAAGC
TCGAGCAGACCGTCAAGGACAACGATGGTCACCTGGCTCTGGGCAAGCTGACCTGGGCCGACGTCTACTTCGCAGGCATCACCGACTACATGAAC
TACATGGTCAAGCGCGATCTGTTGGAACCCTACCCAGCTCTGCGCGGAGTCGTGGATGCCGTCAACGCTTTGGAACCGATCAAGGCCTGGATCGA
GAAGCGCCCCGTCACCGAGGTCTAAGTTCACCGAACAGGACTTGGGAGGATGGGAAAGCATTGCACAACCACTCAGACACAACCGCACCGCAGAA
ATGCACACCACCCACATCTGCACACATTTTGTTCCTTTTTGCGGAGGATCCGAGAGGACGGCGGATTTTCGCACGGGGTCATAAACGCGTAGGAG
TTTAGCACGTATCACTATGGATAAATCGTATTTGTTCTTAATTTCTTGGTTATAATTCTCTTTGCATGGCGCTATATACATATTTCTATTGGGGT
CCGGCAGCGGATCGCCGTTCGTTAGCTTCTTCTGAAATGATGAAAGATAATACTTATTGCACAGTTTATAATATTTTGGCTTACTTTTAGAACAT
ACATTTAGCGCACCTATGCAGACATTTGCTGTACCTATATATATATATATATGCATAAAATACAAAAGCTACGAGTGGTTCATCTTATAGGCGTA
TTCTATTGCAATTTATTCAATGCGGAGGGCTCAATAAATATTTAAAACAACACCAGCTAAGGCTGAGAAACAATTACAAATTCTTATTTTGTTTT
TTATACAACACGCCATCGCGGCCCCAGGAATTTTCTTCGTCT
(SEQ ID NO: 965)

Start ATG: 226

MADEAQAPPAEGAPPAEGEAPPPAEGAEGAVEGGEAAPPAEPAEPIKHSYTLFYFNVKALAEPLRYLFAYGNQEYEDVRVTRDEWPALKPTMPMG
QMPVLEVDGKRVHQSISMARFLAKTVGLCGATPWEDLQIDIVVDTINDFRLKIAVVSYEPEDEIKEKKLVTLNAEVIPFYLEKLEQTVKDNDGHL
ALGKLTWADVYFAGITDYMNYMVKRDLLEPYPALRGVVDAVNALEPIKAWIEKRPVTEV*
(SEQ ID NO: 966)

Name: glutathione S transferase 2
Classification: enzyme
Gene Symbol: Gst2
FlyBase ID: FBgn0010226

Celera Sequence No. : 142000013384668
GCTTTATTTAGTTTTCGTTCTTTAAACTATGTATCTTTTAAGTGGGCAGTAAACAAGCTTCATCCACTAAAAGCCCAAACAAATATTTACTGCCT
TTTTTTGCTACTATAATTGGTTTATTACTGAGCTGAGAACCTCTCCCAAAGAGATCTATTTAAATGCCGACTGAGAGATTTTAAGAACAGAGAGA
GAGTTCCATTTTGTTTATGAAAAGCTAATTGCCAAATTGGGAAGCCAAAGCCTGCTGGAATATTGCATTCCATTTAAGAAAAGAGGGTAGGAAGA
AGAAGAACTGGAAACGTGGCTAAATATGTTAACTAATTCATTAACTTCGTTTCCTTTTCAACGCCCACTGGAACTAGAATCAGAGAGAGAGAGAG
AGAGAGAGAGAGAGAGAGAGAGAGAGAGAGAGCCAAACTTAAAATTAAAACACTACCTTTTTCCAGTTAACCGGCCGGCTTACACACACAGTCAAACGC
CTGAAGCTTGAAAGAGAGTGTTTGCTTGATGAGAGCGGCAAGCGTATAAAAGCAGCGTCGCCGGCAGAAGAAAGTCAGTTGCAGTGCAGTCGTCG
TGACGATCGGTTCAGTGATAGCTTCCCAGTGGCTGGAGAGAGTGAGAGTAGAGAGTAACGGAAAGAGAGTGCGAATCGAACCGAACGCTATTCCT
TCGCCCACGATTTAAGTGAACGCTTATTAGCGAATTGAAGACCCGAGAGCCCCAGTGCCCAGCTGATTTCGTATTCTTTGTTGAGGTAAGCCAAG
GAATCCCTGGAACCACCTCATTTCGTAGCACCTTAGTGATGTAATTACGCACCAAGATTTACCCTTGCCAAAAAGTGGAAAACGCTTTTGCGAAC
TTCGATGCCGAATGGTGTTCGTCTCGAATCGGTTCTAAAATTACACACAATGGTTTTTTGGCTTCGATTGATTTGATTTGATTTTTGGGTCAATC
GATTCGAAATCGAAAAGTTTGAACTCGTTTCGCAGAATCGCAGTTCGCGCGGATCTCTCGCCTCGCTCGCAAGCAAATATGTGAAGGACAACGA
CGTTAACCGATCAACTAGAAGCCCTCTTCTTCTGCCTCTTCAGAACCGATCAGATCGGAATAGAAATATAGAAACGACCATAGCACCTCCGTCGA
CTGTGGAGTGCGTGAACGTATTTCGAAGCGTGAGGTACTCGAACCGGAACCAACTTGAGTGTAGTGCATATTCGGGATCTTATCCAAACGCAGGC
TTACATAACCCCTATTTTAATACCTTTCAAAAAGGAATAATTGAAATTCAAAACAAAATTATTTAGCAACAAACAAACAATCAGTTATATTTTT
GAACTGATATGCCTCGGGGCTAGGGGTCCCAGACTTTCAAATTCTAGTGATAACCCCCCCGATCGGCGAGTTCATCTGGAAATGTTGCCCATATG
GGCCGGGTGCACGTGAATCTCTTCAGTGCCCATTGACGCACTTTGTGTGCCTCCACTGGGTCCTTGACCCGCTGTGATCCCTGCCCTTTCCCATG
GATTGGATAATCTAGGTGTCATTATCTTCCCTAACCTTTTCCCACGATTAAAGTGAAACCATTTGCCACGATTTTAGTGCCGTAGTGCCAGATCA
AAGAGCCAAAATAGATCAGAGAATCGAAATTTAATTAAATCATGACACCGAAACACCGAGACAGACCAAATTAAATTCAATTGAAGCTGTCATGG
CAACAAGTGCCAGCAAAAAAAAGGAAGAGCACTACGGCGAAACCAGAAGATAACACCGAAAAGTCAAATCGATTGTTGCAATTTGAGACTCTCCG
AAAGCGAAAATTGCAGCGGAAGAGGCGGCCAATCGGCCATTACTAAACGGTGATGGGGTTGGGGAGGGGATCCGAAGTCTTGGTGACTGACTGGG
CGCCCTGCCAAAATGATGGCAAAGGCAGAGACACCATGATTCCTCAGCCAAATCGAACGAAAACGGGTTTACGCTCTACATGGACCCCATTGCAC
ACTGAATCCGTTTATCCAGCGAGGCAAAAAGTGCCGACGACAATGGAAACAGGGGCGTAGTATCCGTACCTCCTCCGTCCTACGATTCTTCCAGC
AGCGCCAACGCCCCAAAAGATATTGATTCCGACTTTTGCGCGATTCAGCGAAAAACATAAGGGGACCAAAAGTGGGCAGACGGGCGGAGGAGTGG
TGTCTGTTTCTTTGATATGCGTGGGTGTGTTGTCTGTGCGGCAATCGATGCACTTCCGGTGGGTTCTATGGGGAAATACTCTTGCGTTTCAGTAT ATATCTACTATATATATTGCAATTTTATGGTAATTATATTTTCTGTCAACTTTTGCCTTGACTCCGCTTGATTTATTGCATTGTTCTTGAAGAAT
AGCCTCATAAGGCATGCAAGCAAACATGGCTTTCGAACTAGCGCAAAATTAGCTAGTAGCTTATAGAGTATATGTAGCTTACCCCCAACGGTTTT
TATATCATTTGTTTAAACCACTTAAGAATATTCGTAGCCTTGTGGACACACTTTATCGTGGATCGTGGAAGTTATACGACACCGTAATATATCCT
TATCACTCACGCATATTCTGGCCCACTTCAGCTAGAAACGTTTGGCGCGTTCGCCTTATCATAAAAATCAGGCTATCGACTGATTAACTGAGTTT
AATAAGCCAGCAAACGTAAACAAAAACTACGAAAGTTCTGGAAAACTAACCAAGGCTATTTCAAAACGGCGTGAAATGGCTAGCACTCTAAATTA
TTGAAGTTTTCAACATATGTATATCTAATCTGATAGCCAAGAAAACATAATGGTTACCAACTTTCCATATACACCGTAATTTATTATTGATGAAT
ATCAAATTATCGATAGTACTTCCCCGATAAGATTCTGTTAACACACATTGCTCTACTTTTCTATCAGGGAATTGCATTGAGAAAGCGCAGAGATG
GCCGATGAAGCACAAGCACCACCAGCTGAGGGAGCACCACCAGCCGAGGGAGAGGCGCCACCACCCGCCGAGGGAGCCGAGGGTGCCGTCGAGGG
CGGAGAGGCCGCTCCACCAGCAGAGCCCGCCGAGCCCATCAAGCACAGCTACACGCTCTTCTACTTCAACGTGAAGGCGTTGGCCGAGCCCCTGC
GCTACCTGTTCGCCTACGGCAACCAGGAGTACGAGGATGTGCGCGTCACCCGCGACGAGTGGCCAGCCCTGAAGCCCAGTGAGTGCCATAGTCCA
TCATTGAGTGGTCAGTGGACTAACCATAATCTACTCTGTCTCATCCAATAGCCATGCCCATGGGACAGATGCCCGTGCTGGAGGTGGACGGCAAG
CGTGTGCACCAGAGCATTTCGATGGCTCGATTCCTGGCCAAGACTGTCGGCCTGTGCGGCGCTACTCCGTGGGAGGATCTGCAGATCGACATTGT
CGTTGACACCATCAATGACTTCCGTCTAAGTAGCGAACAATGTGTGCCTCAGTTTCATGTTCAGTGTCCTTGATTAACTCTGGAATTTTTAATGT
ATAGAAATTGCAGTCGTCTCGTACGAGCCGGAGGACGAGATTAAAGAGAAGAAGTTGGTCACCCTGAATGCGGAGGTCATTCCATTCTACCTGGA
GAAGCTCGAGCAGACCGTCAAGGACAACGATGGTCACCTGGCTCTGGGCAAGGTGCGTGCTCAAATGAGAACTTGAAACCATACACTCGTTAATT
TTGAATGAACAATACTAAGAACCATCGATTCCTTTCACCCACAGCTGACCTGGGCCGACGTCTACTTCGCAGGCATCACCGACTACATGAACTAC
ATGGTCAAGCGCGATCTGTTGGAACCCTACCCAGCTCTGCGCGGAGTCGTGGATGCCGTCAACGCTTTGGAACCGATCAAGGCCTGGATCGAGAA
GCGCCCCGTCACCGAGGTCTAAGTTCACCGAACAGGACTTGGGAGGATGGGAAAGCATTGCACAACCACTCAGACACAACCGCACCGCAGAAATG
CACACCACCCACATCTGCACACATTTTGTTCCTTTTTGCGGAGGATCCGAGAGGACGGCGGATTTTCGCACGGGGTCATAAACGCGTAGGAGTTT
AGCACGTATCACTATGGATAAATCGTATTTGTTCTTAATTTCTTGGTTATAATTCTCTTTGCATGGCGCTATATACATATTTCTATTGGGGTCCG
GCAGCGGATCGCCGTTCGTTAGCTTCTTCTGAAATGATGAAAGATAATACTTATTGCACAGTTTATAATATTTTGGCTTACTTTTAGAACATACA
TTTAGCGCACCTATGCAGACATTTGCTGTACCTATATATATATATATATGCATAAAATACAAAAGCTACGAGTGGTTCATCTTATAGGCGTATTC
TATTGCAATTTATTCAATGCGGAGGGCTCAATAAATATTTAAAACAACACCAGCTAAGGCTGAGAAACAATTACAAATTCTTATTTTGTTTTTA
TACAACACGCCATCGCGGCCCCAGGAATTTTCTTCGTCTCATCCAGTTCCCTTTTAAGTAGCCATTAAAAAAAGACTCACATCAATAGAACCGGT
TTCTCCAAAAAAAAAAAAAACAGACTCTTACTGCCAAATTTCAAATGCACATAATCACATTATTATATACATATTATTTATTCAAATTTGTAATT
GTATTTTTTGAATATTTTCACAAAACACTTTTTAATAAACATAACACCTAAAAAGGAATGAGCACTTTTTAAAAGCACGACAACTGGTTTTATTT
AATTTTTGTACGATGTATTGGAATAATTTATTAATTGTTGACATATTTAAGAAATTTAAAGAAAGTGTTTATTTACATTATTAATTTTTATTTTT
ATTATCCTTTCAATTTGCATTTCCAAAGCCGACCCGACAGACATAAATAAATGCATGGAGTTGTGTTCAACATTGTTTTATAAACGTTTAAAAAA
ATAACATTTCAAATTAACATTCTTTTAAGTCACTTTGGACAATTCAAGCTTAAAAGTATAAATGCACAATTGGTCAGTTTTGATTCATTATTTCA
TATTGTATGTTGCGGTTACTGGTGCTTCCAGTTGGGTGGGCGCTTCTCGAAGAAGCTAGCAATGCCCTCTTTGGTGTCGCCCAGCTGGAAATTTT
CGCACATCTTCTCCTGCGCAGCCGAAAAGGCTTCCGCTTGGGACATGGCCAGTTGCTTGTAGTAGAACTCTTTTCCCAGAGAGATGACGGCACGA
CTTTTTGCCTTTATGGCATTGGTGATTTCCTCGATCTCCTTATCTAGTTCCTCTGCAGGAACAGCTTTGGTGACCATTCCCGATATGTAGGCTTC
TTCACCAGTAACGGGAAGACCGGTCATTAGCATATAGGCGGACTTTGGACGCGACATAATCCGGGCAACTGCGACTCCGGGTGTTGAGCAAAAAA
CTCCGACTCCAGCCCTAAAAATATAAATTATAACATGATTAACTGGTTTCATAGAGGGTTTTCATCCTTACCCTGGAGTAGAGAACTTG
(SEQ ID NO: 967)

Exon: 1001..1174
Exon: 2918..3213
Exon: 3282..3449
Exon: 3520..3662
Exon: 3750..4504
Start ATG: 2943

Transcript No. : CT25674
CGGATCTCTCGCCTCGCTCGCAAGCAAATATGTGAAGGACAACGACGTTAACCGATCAACTAGAAGCCCTCTTCTTCTGCCTCTTCAGAACCGAT
CAGATCGGAATAGAAATATAGAAACGACCATAGCACCTCCGTCGACTGTGGAGTGCGTGAACGTATTTCGAAGCGTGAGGGAATTGCATTGAGAA
AGCGCAGAGATGGCCGATGAAGCACAAGCACCACCAGCTGAGGGAGCACCACCAGCCGAGGGAGAGGCGCCACCACCCGCCGAGGGAGCCGAGGG
TGCCGTCGAGGGCGGAGAGGCCGCTCCACCAGCAGAGCCCGCCGAGCCCATCAAGCACAGCTACACGCTCTTCTACTTCAACGTGAAGGCGTTGG
CCGAGCCCCTGCGCTACCTGTTCGCCTACGGCAACCAGGAGTACGAGGATGTGCGCGTCACCCGCGACGAGTGGCCAGCCCTGAAGCCCACCATG
CCCATGGGACAGATGCCCGTGCTGGAGGTGGACGGCAAGCGTGTGCACCAGAGCATTTCGATGGCTCGATTCCTGGCCAAGACTGTCGGCCTGTG
CGGCGCTACTCCGTGGGAGGATCTGCAGATCGACATTGTCGTTGACACCATCAATGACTTCCGTCTAAAAATTGCAGTCGTCTCGTACGAGCCGG
AGGACGAGATTAAAGAGAAGAAGTTGGTCACCCTGAATGCGGAGGTCATTCCATTCTACCTGGAGAAGCTCGAGCAGACCGTCAAGGACAACGAT
GGTCACCTGGCTCTGGGCAAGCTGACCTGGGCCGACGTCTACTTCGCAGGCATCACCGACTACATGAACTACATGGTCAAGCGCGATCTGTTGGA
ACCCTACCCAGCTCTGCGCGGAGTCGTGGATGCCGTCAACGCTTTGGAACCGATCAAGGCCTGGATCGAGAAGCGCCCCGTCACCGAGGTCTAAG
TTCACCGAACAGGACTTGGGAGGATGGGAAAGCATTGCACAACCACTCAGACACAACCGCACCGCAGAAATGCACACCACCCACATCTGCACACA
TTTTGTTCCTTTTTGCGGAGGATCCGAGAGGACGGCGGATTTTCGCACGGGGTCATAAACGCGTAGGAGTTTAGCACGTATCACTATGGATAAAT
CGTATTTGTTCTTAATTTCTTGGTTATAATTCTCTTTGCATGGCGCTATATACATATTTCTATTGGGGTCCGGCAGCGGATCGCCGTTCGTTAGC
TTCTTCTGAAATGATGAAAGATAATACTTATTGCACAGTTTATAATATTTTGGCTTACTTTTAGAACATACATTTAGCGCACCTATGCAGACATT
TGCTGTACCTATATATATATATATATATGCATAAAATACAAAAGCTACGAGTGGTTCATCTTATAGGCGTATTCTATTGCAATTTATTCAATGCGGA
GGGCTCAATAAATATTTAAAACAACACCAGCTAAGGCTGAGAAACAATTACAAATTCTTATTTTGTTTTTATACAACACGCCATCGCGGCCCCA
GGAATTTTCTTCGTCT
(SEQ ID NO: 968)

Start ATG: 200

MADEAQAPPAEGAPPAEGEAPPPAEGAEGAVEGGEAAPPAEPAEPIKHSYTLFYFNVKALAEPLRYLFAYGNQEYEDVRVTRDEWPALKPTMPMG
QMPVLEVDGKRVHQSISMARFLAKTVGLCGATPWEDLQIDIVVDTINDFRLKIAVVSYEPEDEIKEKKLVTLNAEVIPFYLEKLEQTVKDNDGHL
ALGKLTWADVYFAGITDYMNYMVKRDLLEPYPALRGVVDAVNALEPIKAWIEKRPVTEV*
(SEQ ID NO: 969)

Name: Glutathione S transferase 2

FIGURE SHEET 519

Classification: enzyme
Gene Symbol: Gst2
FlyBase ID: FBgn0010226

Celera Sequence No. : 142000013384668
TCACCAGTAACGGGAAGACCGGTCATTAGCATATAGGCGGACTTTGGACGCGACATAATCCGGGCAACTGCGACTCCGGGTGTTGAGCAAAAAAC
TCCGACTCCAGCCCTAAAAATATAAATTATAACATGATTAACTGGTTTCATAGAGGGTTTTCATCCTTACCCTGGAGTAGAGAACTTGCTGTTCT
TGGTGCAGACTACCATGTCACATGACACCACCAGTTGGCAGCCTGCAGCAGCCGCATAGCCATTGACTTTTCCTAGTACGGGCACCGGCAGTCTT
TGGATGTCGTTTATAACATCGGTTAGCTTCTGGAACACACAAGCCTGTATCTTGGGGTCATTGTGCAACTCCTTGAGATTGTGACCTGCCGACCA
GATCTTTCCTTGGGCCGTCAGGACCACGCATCTCAGATCCAAGTTGTCTTTATCTTTTAGCAGGGCGTCCTGAAGGGCACACATCATGTCCAGTG
ATAGGGAATTCAGAGTTTTTGGATGATTCAGCGTTATCTCTCGCACTCCGTTATGCTCCTTGACCAGGACCAAATCACTGGGTCCATTGCTGGTA
AAGCGAATGACCTGTTGCACGCAACCTGTTGCATATTTTGATATTTTTAAGGAGTTGTTTAAAATACGCAACATTTTTATTTTGATTTGGCAGCA
AGTGTTGGTAAATTCGCCGCCCAAACAGCTGGTTATCTATCGAAACAGCTGCAAGTCGATAGCAAGGCGCAACAGTTGTCAAACGGTCACTCTAA
GCCGCAATGAGTTTGTACGATTAAAAGTTTATGTCTATTCGCGTTTTTCGAAGCTTTCCCGATTCCCGTAGCTGTCCCACTGTACAGGTGAGTAA
CCGCTCAGGTGCGTCAACAACCGCTGCCGTTCTTTGTCCATCAGCTGAGCGGTCAGACAGAACAACAACAAAGCCAGAAGCTCGCGCGCCAGCCT
GTGTACGTAGTAAATCTATGTGACTACTACAAAAGCAGAACTTTATCAGCCACCAAAGCCATTTGTTATTTGTCGCCCCACATTCGCGGCCCCGC
CAATCAGTTAACAAATCGAACCACGCGAGTGCGGATCCCCCGACTTGAGCTCCACTAAAACGTACACCATTAAATTACCACATTCCAGCTTGCCA
CACGATGCGTCCGTTCTCCGGCAGCGATTGCCTTAAGCCCGTCACCGAGGGCATCAACCGGGCGTTCGGCGCCAAGGAGCCCTGGCAGGTGGCCA
CCATCACGGCCACCACGGTGCTGGGAGGCGTCTGGCTCTGGACTGTGATCTGCCAGGATGAAAGTGAGTTGGTGGTGTCTATGTGTGTGATAGAT
CTCCTGGAATTAGTTCTAAACAACAATGCCTTTGCTGGATTTTCTTCTTGCACAGTTTATATGCAATCTGCAAGAAAATATGACAAAATTCGACT
TAAACGAAAGTTGGACTTATATAAAACAGTGTCAAGTCATCACAGTCAGCCGATTTCATTTATTTCGTGCTTGCAGGGCAGGGCACGTCAATTAC
CTAAATCCATCAAACTATCTTATCTGATGGGTGCGTTGCTTATAAACATAGCTAGACTTCTTCTCTTACAATTTTCCTAAAAAACGCTAATATAA
AACGTATCGTACAAAGAGAATTCACCTAAGAATTCACCACTTTTATAATATTGTATTAAAATAAGCACGCTTTACTGTGTACTTTGTGCCCATAG
CTTATATAAGCCATGCACTCGTCTGGTGCCCTCCCCGAACTTCTGAATTTAATCTAGTCACAGATTACGATAGATTAGAGTTTAAATGTTTGCTA
AAGCGTGTAGCAACTTAAAATCAATCAAATATGCAAAGTTCAACAGCGCGAAGAAAATTGATAAGATTGAGATATCCTGCCCTTGCTAGCACATA
GTAATAGTTTAGGGGCTTAGTACCAAAACTAATGAGATTAGGTAGGTAGTTTCCCCGATACCATGACTAATGCTTTAAATTAGGAATGATGAAAA
AATAATGTTTCTAGCATAGCTTCTCGATAAAGTGCCATAAAGCCTGTCCAAAGTTTCGTCCACAGCAAGGCATGTCATGTCCGATAAGATCGAGC
GGGTATCATACACACTTCGTTTATCAGGCTGCAATTTTTTTCAATGATTCTTTGTTTTGGGTCTGTTAACCTCATGAATATAAAACTTTTAACGA
CTTCAGTCTGATGAAAACAAAGGACAGTGAAAGGTTTATCTATAGTAATATAATAATAACTGTACGCAAACTTATTCCATAATTTTCTCTCCCAA
GATCTTTACATTCGTGGCAAGCGTCAGTTCTTTAAGTTTGCCAAGAAGATTCCAGCCGTGCGTCGTCAGGTGGAGACTGAATTGGCCAAGGCCAA
AAACGACTTCGAGACGGAAATCAAAAAGAGCAACGCCCACCTTACCTACTCGGAAACTCTGCCCGAGAAGGGACTCAGCAAGGAGGAGATCCTCC
GACTGGTGGATGAGCACCTGAAGACTGGTCACTACAACTGGCGTGATGGTCGTGTATCTGGCGCGGTCTACGGCTACAAGCCTGATCTGGTGGAG
CTCGTCACTGAAGTGTACGGCAAGGCCTCCTACACCAATCCCTTGCACGCAGATCTTTTCCCGGGAGTTTGCAAAATGGAGGCGGAGGTAGTGCG
CATGGCATGCAACCTGTTCCATGGAAACTCAGCCAGCTGTGGAACCATGACCACCGGCGGCACCGAATCCATTGTAATGGCCATGAAGGCGTACA
GGGATTTCGCTAGAGAGTACAAGGGAATCACCAGGCCAAACATCGTGGTGCCTAAGACGGTCCACGCGGCCTTCGACAAGGGCGGTCAGTACTTT
AATATCCACGTGCGATCCGTGGATGTAGATCCGGAGACCTACGAAGTGGACATTAAGAAGTTCAAACGTGCCATTAACAGGAACACGATTCTGGT
ATGGGTTTACATAGCAAAATGTATTCTAAAACTAATCTTGAAACTTTAATCAGCTGGTTGGGTCTGCTCCGAACTTCCCCTATGGAACCATCGAT
GACATCGAAGCTATCGCCGCTTTGGGCGTTAAGTACGACATTCCCGTGCACGTGGACGCCTGCCTGGGCAGCTTTGTGGTGGCCTTGGTCCGCAA
CGCCGGCTATAAGCTGCGTCCCTTCGACTTTGAGGTCAAGGGAGTGACCAGTATCTCCGCTGATACCCACAAGTATGGTTTCGCGCCCAAGGGAT
CATCGGTGATCCTTTACTCGGACAAGAAGTACAAGGACCATCAGTTCACTGTGACTACTGACTGGCCTGGCGGCGTGTATGGTTCTCCCACAGTC
AACGGTTCCCGTGCCGGAGGTATTATCGCCGCCTGCTGGGCTACCATGATGAGCTTTGGCTATGATGGTTATCTGGAAGCCACTAAGCGCATTGT
GGATACGGCGCGCTATATCGAGAGGGGGTAAGTTTGTATCAAAGTTCGTTGTGACAATAATATAATTTTAAATCTATATTACCAGCGTTCGCGAC
ATCGATGGCATCTTTATCTTTGGCAAGCCAGCTACTTCAGTGATTGCCCTGGGTTCCAATGTGTTTGACATTTTCCGGCTATCGGATTCGCTGTG
CAAACTGGGCTGGAACCTGAATGCGCTGCAGTTTCCATCTGGGTAGGTGACTCAACTTTTAAATTAGCGGAACCATTCTTATAAGTGAAATTCCC
TCTAAGTATCCACCTGTGCGTGACGGACATGCACACACAGCCCGGAGTCGCGGATAAATTCATTGCCGATGTGCGCAGCTGTACGGCGGAGATCA
TGAAGGATCCCGGCCAGCCCGTCGTTGGAAAGATGGCTCTCTACGGCATGGCACAGAGCATACCCGACCGTTCGGTGATCGGAGAAGTGACTCGC
CTATTCCTGCACTCCATGTACTACACTCCCAGCCAGAAATAGACACCTGGAGCAATCCCCGTTCTCTTCGCCCACCCCACGGAGCTAATGCATTT
CCTGTGCTGTATTTAAACCACCAAAACACCCCGTCGTTAAACCTTCCTCAAGCAATTTATATTAGGATGCAATTAGTGCTGTAATCGAGGGTACA
AAACGTCGTTCTACGCGAAAATCTATCTACCTATGTTCATCCCATTTGTCAACATTCGTCGCTCTAAGAGCCATGTTATTAAAGTGTTTTTCTGT
GTAACTTGCTAGTGAAATAATAATATAATATTAATCAATTTTTGTGTACTATACATTTGTGAATGCTGTTAATGCTCGTTAATCTTGAAACTTCC
ATTTCCTCTGCAAAATAGAATGAAAACATATACATTTAGCTTAATTGGATTGTGGCCTCACAAATTTTTAGCATGGATCTATTTGTTACCATTTA
ATTTATATTTGTTTACATTGTTTACCACTTCAGCAATTAACAATAATTACTGCTGCGTGGGTATATGCAATCCGGTCCGATCTGATCTGGATTGG
TGTTTTTATTTCTTTTCGAACATTTTGCCACGCGTCGGCGTTTTTTAATTTAGTTGATCTTGGATGCCCAGCTGACACGCCCATTTCCTCTTTTG
TAATTTATGGAAGTCTCGAATGGCGTGCACAAAAATTATTTCAAATACATTTCTATGGCGGAAACATTTATTTCAAAGGCAAGCGCACATTTTAA
CAAGGCACACGTTCGTTGTCATTTTTCAAAGAAAAAATAAATATAAATAGCCAAAGCGAAGCAACAAGTGTCGCACAAAGGTGACGATCGATTTG
TGGCATCCATATCAAAACCTGTCACCCTAACACACCTAATGCGCCCACGCAACTCTGCACTTCCTGCCCCTGTCCACCAGAAATCCGGGTGCACT
AGCAACTCCAGACAGCCGGGCAGCCCAGAAAAAATTCGGCTCAAACTGGGTTGCCAAAAAAGTGTGCATGAAATAAATTCACTTTTTTCCCCA
(SEQ ID NO: 970)

Exon: 1001..1298
Exon: 2282..2943
Exon: 2999..3447
Exon: 3506..3652
Exon: 3712..3937
Start ATG: 1145

Transcript No. : CT25678
CACCAAAGCCATTTGTTATTTGTCGCCCCACATTCGCGGCCCCGCCAATCAGTTAACAAATCGAACCACGCGAGTGCGGATCCCCCGACTTGAGC
TCCACTAAAACGTACACCATTAAATTACCACATTCCAGCTTGCCACACGATGCGTCCGTTCTCCGGCAGCGATTGCCTTAAGCCCGTCACCGAGG
GCATCAACCGGGCGTTCGGCGCCAAGGAGCCCTGGCAGGTGGCCACCATCACGGCCACCACGGTGCTGGGAGGCGTCTGGCTCTGGACTGTGATC TGCCAGGATGAAAATCTTTACATTCGTGGCAAGCGTCAGTTCTTTAAGTTTGCCAAGAAGATTCCAGCCGTGCGTCGTCAGGTGGAGACTGAATT
GGCCAAGGCCAAAAACGACTTCGAGACGGAAATCAAAAAGAGCAACGCCCACCTTACCTACTCGGAAACTCTGCCCGAGAAGGGACTCAGCAAGG
AGGAGATCCTCCGACTGGTGGATGAGCACCTGAAGACTGGTCACTACAACTGGCGTGATGGTCGTGTATCTGGCGCGGTCTACGGCTACAAGCCT
GATCTGGTGGAGCTCGTCACTGAAGTGTACGGCAAGGCCTCCTACACCAATCCCTTGCACGCAGATCTTTTCCCGGGAGTTTGCAAAATGGAGGC
GGAGGTAGTGCGCATGGCATGCAACCTGTTCCATGGAAACTCAGCCAGCTGTGGAACCATGACCACCGGCGGCACCGAATCCATTGTAATGGCCA
TGAAGGCGTACAGGGATTTCGCTAGAGAGTACAAGGGAATCACCAGGCCAAACATCGTGGTGCCTAAGACGGTCCACGCGGCCTTCGACAAGGGC
GGTCAGTACTTTAATATCCACGTGCGATCCGTGGATGTAGATCCGGAGACCTACGAAGTGGACATTAAGAAGTTCAAACGTGCCATTAACAGGAA
CACGATTCTGCTGGTTGGGTCTGCTCCGAACTTCCCCTATGGAACCATCGATGACATCGAAGCTATCGCCGCTTTGGGCGTTAAGTACGACATTC
CCGTGCACGTGGACGCCTGCCTGGGCAGCTTTGTGGTGGCCTTGGTCCGCAACGCCGGCTATAAGCTGCGTCCCTTCGACTTTGAGGTCAAGGGA
GTGACCAGTATCTCCGCTGATACCCACAAGTATGGTTTCGCGCCCAAGGGATCATCGGTGATCCTTTACTCGGACAAGAAGTACAAGGACCATCA
GTTCACTGTGACTACTGACTGGCCTGGCGGCGTGTATGGTTCTCCCACAGTCAACGGTTCCCGTGCCGGAGGTATTATCGCCGCCTGCTGGGCTA
CCATGATGAGCTTTGGCTATGATGGTTATCTGGAAGCCACTAAGCGCATTGTGGATACGGCGCGCTATATCGAGAGGGGCGTTCGCGACATCGAT
GGCATCTTTATCTTTGGCAAGCCAGCTACTTCAGTGATTGCCCTGGGTTCCAATGTGTTTGACATTTTCCGGCTATCGGATTCGCTGTGCAAACT
GGGCTGGAACCTGAATGCGCTGCAGTTTCCATCTGGTATCCACCTGTGCGTGACGGACATGCACACACAGCCCGGAGTCGCGGATAAATTCATTG
CCGATGTGCGCAGCTGTACGGCGGAGATCATGAAGGATCCCGGCCAGCCCGTCGTTGGAAAGATGGCTCTCTACGGCATGGCACAGAGCATACCC
GACCGTTCGGTGATCGGAGAAGTGACTCGCCTATTCCTGCACTCCATGTACTACACTCCCAGCCAGAAATAG
(SEQ ID NO: 971)

Start ATG: 145

MRPFSGSDCLKPVTEGINRAFGAKEPWQVATIITATTVLGGVWLWTVICQDENLYIRGKRQFFKFAKKIPAVRRQVETELAKAKNDFETEIKKSNA
HLTYSETLPEKGLSKEEILRLVDEHLKTGHYNWRDGRVSGAVYGYKPDLVELVTEVYGKASYTNPLHADLFPGVCKMEAEVVRMACNLFHGNSAS
CGTMTTGGTESIVMAMKAYRDFAREYKGITRPNIVVPKTVHAAFDKGGQYFNIHVRSVDVDPETYEVDIKKFKRAINRNTILLVGSAPNFPYGTI
DDIEAIAALGVKYDIPVHVDACLGSFVVALVRNAGYKLRPFDFEVKGVTSISADTHKYGFAPKGSSVILYSDKKYKDHQFTVTTDWPGGVYGSPT
VNGSRAGGIIAACWATMMSFGYDGYLEATKRIVDTARYIERGVRDIDGIFIFGKPATSVIALGSNVFDIFRLSDSLCKLGWNLNALQFPSGIHLC
VTDMHTQPGVADKFIADVRSCTAEIMKDPGQPVVGKMALYGMAQSIPDRSVIGEVTRLFLHSMYYTPSQK*
(SEQ ID NO: 972)

Name: sphingosine phosphate lyase-like
Classification: enzyme

Celera Sequence No. : 142000013384668
TGGGCGCTTCTCGAAGAAGCTAGCAATGCCCTCTTTGGTGTCGCCCAGCTGGAAATTTTCGCACATCTTCTCCTGCGCAGCCGAAAAGGCTTCCG
CTTGGGACATGGCCAGTTGCTTGTAGTAGAACTCTTTTCCCAGAGAGATGACGGCACGACTTTTTGCCTTTATGGCATTGGTGATTTCCTCGATC
TCCTTATCTAGTTCCTCTGCAGGAACAGCTTTGGTGACCATTCCCGATATGTAGGCTTCTTCACCAGTAACGGGAAGACCGGTCATTAGCATATA
GGCGGACTTTGGACGCGACATAATCCGGGCAACTGCGACTCCGGGTGTTGAGCAAAAAACTCCGACTCCAGCCCTAAAAATATAAATTATAACAT
GATTAACTGGTTTCATAGAGGGTTTTCATCCTTACCCTGGAGTAGAGAACTTGCTGTTCTTGGTGCAGACTACCATGTCACATGACACCACCAGT
TGGCAGCCTGCAGCAGCCGCATAGCCATTGACTTTTCCTAGTACGGGCACCGGCAGTCTTTGGATGTCGTTTATAACATCGGTTAGCTTCTGGAA
CACACAAGCCTGTATCTTGGGGTCATTGTGCAACTCCTTGAGATTGTGACCTGCCGACCAGATCTTTCCTTGGGCCGTCAGGACCACGCATCTCA
GATCCAAGTTGTCTTTATCTTTTAGCAGGGCGTCCTGAAGGGCACACATCATGTCCAGTGATAGGGAATTCAGAGTTTTTGGATGATTCAGCGTT
ATCTCTCGCACTCCGTTATGCTCCTTGACCAGGACCAAATCACTGGGTCCATTGCTGGTAAAGCGAATGACCTGTTGCACGCAACCTGTTGCATA
TTTTGATATTTTTAAGGAGTTGTTTAAAATACGCAACATTTTTATTTTGATTTGGCAGCAAGTGTTGGTAAATTCGCCGCCCAAACAGCTGGTTA
TCTATCGAAACAGCTGCAAGTCGATAGCAAGGCGCAACAGTTGTCAAACGGTCACTCTAAGCCGCAATGAGTTTGTACGATTAAAAGTTTATGTC
TATTCGCGTTTTTCGAAGCTTTCCCGATTCCCGTAGCTGTCCCACTGTACAGGTGAGTAACCGCTCAGGTGCGTCAACAACCGCTGCCGTTCTTT
GTCCATCAGCTGAGCGGTCAGACAGAACAACAACAAAGCCAGAAGCTCGCGCGCCAGCCTGTGTACGTAGTAAATCTATGTGACTACTACAAAAG
CAGAACTTTATCAGCCACCAAAGCCATTTGTTATTTGTCGCCCCACATTCGCGGCCCCGCCAATCAGTTAACAAATCGAACCACGCGAGTGCGGA
TCCCCCGACTTGAGCTCCACTAAAACGTACACCATTAAATTACCACATTCCAGCTTGCCACACGATGCGTCCGTTCTCCGGCAGCGATTGCCTTA
AGCCCGTCACCGAGGGCATCAACCGGGCGTTCGGCGCCAAGGAGCCCTGGCAGGTGGCCACCATCACGGCCACCACGGTGCTGGGAGGCGTCTGG
CTCTGGACTGTGATCTGCCAGGATGAAAGTGAGTTGGTGGTGTCTATGTGTGTGATAGATCTCCTGGAATTAGTTCTAAACAACAATGCCTTTGC
TGGATTTTCTTCTTGCACAGTTTATATGCAATCTGCAAGAAAATATGACAAAATTCGACTTAAACGAAAGTTGGACTTATATAAAACAGTGTCAA
GTCATCACAGTCAGCCGATTTCATTTATTTCGTGCTTGCAGGGCAGGGCACGTCAATTACCTAAATCCATCAAACTATCTTATCTGATGGGTGCG
TTGCTTATAAACATAGCTAGACTTCTTCTCTTACAATTTTCCTAAAAAACGCTAATATAAAACGTATCGTACAAAGAGAATTCACCTAAGAATTC
ACCACTTTTATAATATTGTATTAAAATAAGCACGCTTTACTGTGTACTTTGTGCCCATAGCTTATATAAGCCATGCACTCGTCTGGTGCCCTCCC
CGAACTTCTGAATTTAATCTAGTCACAGATTACGATAGATTAGAGTTTAAATGTTTGCTAAAGCGTGTAGCAACTTAAAATCAATCAAATATGCA
AAGTTCAACAGCGCGAAGAAAATTGATAAGATTGAGATATCCTGCCCTTGCTAGCACATAGTAATAGTTTAGGGGCTTAGTACCAAAACTAATGA
GATTAGGTAGGTAGTTTCCCCGATACCATGACTAATGCTTTAAATTAGGAATGATGAAAAAATAATGTTTCTAGCATAGCTTCTCGATAAAGTGC
CATAAAGCCTGTCCAAAGTTTCGTCCACAGCAAGGCATGTCATGTCCGATAAGATCGAGCGGGTATCATACACACTTCGTTTATCAGGCTGCAAT
TTTTTCAATGATTCTTTGTTTTGGGTCTGTTAACCTCATGAATATAAAACTTTTAACGACTTCAGTCTGATGAAAACAAAGGACAGTGAAAGGT
TTATCTATAGTAATATAATAATAACTGTACGCAAACTTATTCCATAATTTTCTCTCCCAAGATCTTTACATTCGTGGCAAGCGTCAGTTCTTTAA
GTTTGCCAAGAAGATTCCAGCCGTGCGTCGTCAGGTGGAGACTGAATTGGCCAAGGCCAAAAACGACTTCGAGACGGAAATCAAAAAGAGCAACG
CCCACCTTACCTACTCGGAAACTCTGCCCGAGAAGGGACTCAGCAAGGAGGAGATCCTCCGACTGGTGGATGAGCACCTGAAGACTGGTCACTAC
AACTGGCGTGATGGTCGTGTATCTGGCGCGGTCTACGGCTACAAGCCTGATCTGGTGGAGCTCGTCACTGAAGTGTACGGCAAGGCCTCCTACAC
CAATCCCTTGCACGCAGATCTTTTCCCGGGAGTTTGCAAAATGGAGGCGGAGGTAGTGCGCATGGCATGCAACCTGTTCCATGGAAACTCAGCCA
GCTGTGGAACCATGACCACCGGCGGCACCGAATCCATTGTAATGGCCATGAAGGCGTACAGGGATTTCGCTAGAGAGTACAAGGGAATCACCAGG
CCAAACATCGTGGTGCCTAAGACGGTCCACGCGGCCTTCGACAAGGGCGGTCAGTACTTTAATATCCACGTGCGATCCGTGGATGTAGATCCGGA
GACCTACGAAGTGGACATTAAGAAGTTCAAACGTGCCATTAACAGGAACACGATTCTGGTATGGGTTTACATAGCAAAATGTATTCTAAAACTAA
TCTTGAAACTTTAATCAGCTGGTTGGGTCTGCTCCGAACTTCCCCTATGGAACCATCGATGACATCGAAGCTATCGCCGCTTTGGGCGTTAAGTA
CGACATTCCCGTGCACGTGGACGCCTGCCTGGGCAGCTTTGTGGTGGCCTTGGTCCGCAACGCCGGCTATAAGCTGCGTCCCTTCGACTTTGAGG
TCAAGGGAGTGACCAGTATCTCCGCTGATACCCACAAGTATGGTTTCGCGCCCAAGGGATCATCGGTGATCCTTTACTCGGACAAGAAGTACAAG
GACCATCAGTTCACTGTGACTACTGACTGGCCTGGCGGCGTGTATGGTTCTCCCACAGTCAACGGTTCCCGTGCCGGAGGTATTATCGCCGCCTG CTGGGCTACCATGATGAGCTTTGGCTATGATGGTTATCTGGAAGCCACTAAGCGCATTGTGGATACGGCGCGCTATATCGAGAGGGGGTAAGTTT
GTATCAAAGTTCGTTGTGACAATAATATAATTTTAAATCTATATTACCAGCGTTCGCGACATCGATGGCATCTTTATCTTTGGCAAGCCAGCTAC
TTCAGTGATTGCCCTGGGTTCCAATGTGTTTGACATTTTCCGGCTATCGGATTCGCTGTGCAAACTGGGCTGGAACCTGAATGCGCTGCAGTTTC
CATCTGGGTAGGTGACTCAACTTTTAAATTAGCGGAACCATTCTTATAAGTGAAATTCCCTCTAAGTATCCACCTGTGCGTGACGGACATGCACA
CACAGCCCGGAGTCGCGGATAAATTCATTGCCGATGTGCGCAGCTGTACGGCGGAGATCATGAAGGATCCCGGCCAGCCCGTCGTTGGAAAGATG
GCTCTCTACGGCATGGCACAGAGCATACCCGACCGTTCGGTGATCGGAGAAGTGACTCGCCTATTCCTGCACTCCATGTACTACACTCCCAGCCA
GAAATAGACACCTGGAGCAATCCCCGTTCTCTTCGCCCACCCCACGGAGCTAATGCATTTCCTGTGCTGTATTTAAACCACCAAAACACCCCGTC
GTTAAACCTTCCTCAAGCAATTTATATTAGGATGCAATTAGTGCTGTAATCGAGGGTACAAAACGTCGTTCTACGCGAAAATCTATCTACCTATG
TTCATCCCATTTGTCAACATTCGTCGCTCTAAGAGCCATGTTATTAAAGTGTTTTTCTGTGTAACTTGCTAGTGAAATAATAATATAATATTAAT
CAATTTTTGTGTACTATACATTTGTGAATGCTGTTAATGCTCGTTAATCTTGAAACTTCCATTTCCTCTGCAAAATAGAATGAAAACATATACAT
TTAGCTTAATTGGATTGTGGCCTCACAAATTTTTAGCATGGATCTATTTGTTACCATTTAATTTATATTTGTTTACATTGTTTACCACTTCAGCA
ATTAACAATAATTACTGCTGCGTGGGTATATGCAATCCGGTCCGATCTGATCTGGATTGGTGTTTTTATTTCTTTTCGAACATTTTGCCACGCGT
CGGCGTTTTTTAATTTAGTTGATCTTGGATGCCCAGCTGACACGCCCATTTCCTCTTTTGTAATTTATGGAAGTCTCGAATGGCGTGCACAAAAA
TTATTTCAAATACATTTCTATGGCGGAAACATTTATTTCAAAGGCAAGCGCACATTTAACAAGGCACACGTTCGTTGTCATTTTTTCAAAGAAAA
AATAAATATAAATAGCCAAAGCGAAGCAACAAGTGTCGCACAAAGGTGACGATCGATTTGTGGCATCCATATCAAAACCTGTCACCCTAACACAC
CTAATGCGCCCACGCAACTCTGCACTTCCTGCCCCTGTCCACCAGAAATCCGGGTGCACTAGCAACTCCAGACAGCCGGCAGCCCAGAAAAATT
CGGCTCAAACTGGGTTGCCAAAAAAGTGTGCATGAAATAAATTCACTTTTTTCCCCA
(SEQ ID NO: 973)

Exon: 1001..1097
Exon: 1384..1548
Exon: 2532..3193
Exon: 3249..3697
Exon: 3756..3902
Exon: 3962..4187
Start ATG: 1395

Transcript No. : CT25696
GTCACTCTAAGCCGCAATGAGTTTGTACGATTAAAAGTTTATGTCTATTCGCGTTTTTCGAAGCTTTCCCGATTCCCGTAGCTGTCCCACTGTAC
AGCTTGCCACACGATGCGTCCGTTCTCCGGCAGCGATTGCCTTAAGCCCGTCACCGAGGGCATCAACCGGGCGTTCGGCGCCAAGGAGCCCTGGC
AGGTGGCCACCATCACGGCCACCACGGTGCTGGGAGGCGTCTGGCTCTGGACTGTGATCTGCCAGGATGAAAATCTTTACATTCGTGGCAAGCGT
CAGTTCTTTAAGTTTGCCAAGAAGATTCCAGCCGTGCGTCGTCAGGTGGAGACTGAATTGGCCAAGGCCAAAAACGACTTCGAGACGGAAATCAA
AAAGAGCAACGCCCACCTTACCTACTCGGAAACTCTGCCCGAGAAGGGACTCAGCAAGGAGGAGATCCTCCGACTGGTGGATGAGCACCTGAAGA
CTGGTCACTACAACTGGCGTGATGGTCGTGTATCTGGCGCGGTCTACGGCTACAAGCCTGATCTGGTGGAGCTCGTCACTGAAGTGTACGGCAAG
GCCTCCTACACCAATCCCTTGCACGCAGATCTTTTCCCGGGAGTTTGCAAAATGGAGGCGGAGGTAGTGCGCATGGCATGCAACCTGTTCCATGG
AAACTCAGCCAGCTGTGGAACCATGACCACCGGCGGCACCGAATCCATTGTAATGGCCATGAAGGCGTACAGGGATTTCGCTAGAGAGTACAAGG
GAATCACCAGGCCAAACATCGTGGTGCCTAAGACGGTCCACGCGGCCTTCGACAAGGGCGGTCAGTACTTTAATATCCACGTGCGATCCGTGGAT
GTAGATCCGGAGACCTACGAAGTGGACATTAAGAAGTTCAAACGTGCCATTAACAGGAACACGATTCTGCTGGTTGGGTCTGCTCCGAACTTCCC
CTATGGAACCATCGATGACATCGAAGCTATCGCCGCTTTGGGCGTTAAGTACGACATTCCCGTGCACGTGGACGCCTGCCTGGGCAGCTTTGTGG
TGGCCTTGGTCCGCAACGCCGGCTATAAGCTGCGTCCCTTCGACTTTGAGGTCAAGGGAGTGACCAGTATCTCCGCTGATACCCACAAGTATGGT
TTCGCGCCCAAGGGATCATCGGTGATCCTTTACTCGGACAAGAAGTACAAGGACCATCAGTTCACTGTGACTACTGACTGGCCTGGCGGCGTGTA
TGGTTCTCCCACAGTCAACGGTTCCCGTGCCGGAGGTATTATCGCCGCCTGCTGGGCTACCATGATGAGCTTTGGCTATGATGGTTATCTGGAAG
CCACTAAGCGCATTGTGGATACGGCGCGCTATATCGAGAGGGGCGTTCGCGACATCGATGGCATCTTTATCTTTGGCAAGCCAGCTACTTCAGTG
ATTGCCCTGGGTTCCAATGTGTTTGACATTTTCCGGCTATCGGATTCGCTGTGCAAACTGGGCTGGAACCTGAATGCGCTGCAGTTTCCATCTGG
TATCCACCTGTGCGTGACGGACATGCACACACAGCCCGGAGTCGCGGATAAATTCATTGCCGATGTGCGCAGCTGTACGGCGGAGATCATGAAGG
ATCCCGGCCAGCCCGTCGTTGGAAAGATGGCTCTCTACGGCATGGCACAGAGCATACCCGACCGTTCGGTGATCGGAGAAGTGACTCGCCTATTC
CTGCACTCCATGTACTACACTCCCAGCCAGAAATAG
(SEQ ID NO: 974)

Start ATG: 109

MRPFSGSDCLKPVTEGINRAFGAKEPWQVATITATTVLGGVWLWTVICQDENLYIRGKRQFFKFAKKIPAVRRQVETELAKAKNDFETEIKKSNA
HLTYSETLPEKGLSKEEILRLVDEHLKTGHYNWRDGRVSGAVYGYKPDLVELVTEVYGKASYTNPLHADLFPGVCKMEAEVVRMACNLFHGNSAS
CGTMTTGGTESIVMAMKAYRDFAREYKGITRPNIVVPKTVHAAFDKGGQYFNIHVRSVDVDPETYEVDIKKFKRAINRNTILLVGSAPNFPYGTI
DDIEAIAALGVKYDIPVHVDACLGSFVVALVRNAGYKLRPFDFEVKGVTSISADTHKYGFAPKGSSVILYSDKKYKDHQFTVTTDWPGGVYGSPT
VNGSRAGGIIAACWATMMSFGYDGYLEATKRIVDTARYIERGVRDIDGIFIFGKPATSVIALGSNVFDIFRLSDSLCKLGWNLNALQFPSGIHLC
VTDMHTQPGVADKFIADVRSCTAEIMKDPGQPVVGKMALYGMAQSIPDRSVIGEVTRLFLHSMYYTPSQK*
(SEQ ID NO: 975)

Name: sphingosine phosphate lyase-like
Classification: enzyme

Celera Sequence No. : 142000013383850
ATCATTATTAAACTGTTTGCTTTATTTTTGTTTCGAATCTGCGCAATTCGCAGATCCATTCCTTTTGTTTGTTGGTTTGTCAAGTTAAGATTTAA
AAAAAAAAAACTCAAAATTACAATTGTTAGTTCTTCTTTCCCCGCCCTTCTCCCTCGTGTCTGCTTTCGCTTCGCTACGCTTATGTAACAATAAA
ATTGTAGCTTTTGCCAAATAAATAATATATGCATATATAATAAAATATATATATATATATACGATCATATATCATAAAGACATTAATGTAGTGCA
TACAAAAAAAAACTAAACTAAAACAAATCTATCTGCAATTTGAATCGGAGGTTAAAGAATATGGTGTGTTGTAAATATAAATTTTTATGCTTATA
GTTTTAAAATAAAAAACATGAATTGTAATCGGTAAATAACTACAAAACAAGATATAAATTCTGCACCAATTAGCAGGATACCAAGCCGATGATCA
GCAGATTAAACAAACATTTCGATCGCACTGTAAAAATAAATGTGGGAAGTGTGGTGGCTGCCAAACCTATAAATAATATATATACAAATAAATAT
ATATATATAAAATTGTCGATTTCCTCGTCCCGAGAAGCGTGCATTCGGTTCGACTTGACTCGCATTTTGGTTGTCATCGTAATCATTTTATCATC ATGATTTATCCTCCGTATTTATGTTAGGTGGATGTAAATATACACTCTTTCATATACTCTATTTATATATATTTGTTTATATATAATTTGTATAT
AGTTTAATTAGCTTTTTATTGCAGTTGAGTATACTATGTTGACTTGTTTTTTGTTGGTGTTGTTGCTTTGCTGGTGTTGTTGATCCTATTTCGTT
TGTTTATCCTTTTGTTTTGTTTTGTTTCTTTCGATTCGATTCGATACGAGGCTTTATCCATATTGCTTCTTGATCTTGATAGGTCGGCTGTTGGC
TGTATTCTTCTTTTGTAGTTATCTTGAATGGTGTTGTATTTTATTTGTGGCTATTTCTCTGGCTTTTCCTCCGTCTTGCTTAATGCAATGCTTAT
TTTAGTTTATTTTTGCTTTTAATTTACGCTTTGCTAATTATAAATTATGTTTTAGTTTTTGTGTTTCTTGTTGAAGTTCTTGTTGCAGCTGTTGG
TTGATTTATCCTGATTTGTCCTGTGCCAAGTCCATGCAGTCCGCTCAGCCAGTTACATACTGCCACTATATAGTCGGTTGGGGACTGGAACTCGA
TCCGAACACAAGTGAATCGCGGGCTGGTTGTGGTGGTGGGGAGAGATGCGTCGCCCAGAGGAGAGAAGTAAGAGGATGGAGCAGGATGCACGCGG
TTTCTCAGTCATTGTCGTGGGCCACCGCCAGTCGTCGTCATCATCTAAGCCATTTCCAGATGCCCTCAATAAATAGGGTTGGATCCGGGCCTGCT
AAACGAGGACAAGCTGCTGACGGCGGCCACAATCGACCAATCATCATCGCAATCATCATCAGCTGCGCCAGAAGAAGCTCTTTTTGAGCCTAACA
GACAGCTTGCGATGTACGCGCAGCCTAACCTGCTCCTGATCCTAAGTATCGTCTGACATGAACGCGTTCTGAGTCTTCGACTCCTCGATACGGCG
GATCTGGTGGCGTAAATACATAATTCTGCGAAAGGCAATACATAAAATGCATTGGTTAGAACAACTACCATTTAGATGTCATTGCAACACTCACT
TTTGTTCCTGCAGGGTGGCATTGATTTCGGTGCTTCGCACCAGGCTGCGGGCGCACTTCAATTCCGCGCATATCCTCGTGCACGTTATGTCGCCA
AACAGGTGCGTATCCTCACAGCACTTCTGCGCCTTCGAGAAACAATGGAAAACATTTACAATCAGTTCGAGTCCATGGATATATGTATACGTATG
TACAGAGGTCGGGTTAGTGCCTTATTCGCAGGCAAATCCTACCTCACAGCTTACCTGACGCTCCAGCACCTCCGCGTGCCAATTGGTCACATGCG
CGATCAGATCGGCGCGGAAGTATTTGGCCAGCTTTGGCGAAATCTCGGGACCACGTAGGTTTGCCGCCTGTCCTGAGGAACTCACGCAGCTCTGC
AGTGAGCTCAGCGTGGCCGACGACGTCCCATCCACTGGAATAACAAATGGGCAAACATTGTCATATATTTTAAACTCGGAACACACTAGAATTTT
GAATACATACATTTCCGCTGCTGCTGGGCCTGTTGCGCCGCCTGTAGCTGGAGGCTTGACGCTGTCGCGGCTGCCGCTGCGGCGGCCAACTGTTG
CTGCTCCAACGCCGAGCCGCTCAAATCCAGCTCCTGGGTGGGCGTAGGCGGTCCTTCGCATAGCGTGCCGCTGTTGCTGCCCATCGAGGTGATCA
CACTGATTCCGCAGACGGGGCCCATGCCGGGCACGATGCTTTGGCTGCTATTCGCTCCACTGGAGCCGGAGGAGGCGTTGCCACCGGGCGTGGCC
GGTGAGGCATTCGCCACCATCACTCCGCCATCGAGGGTAGCCTTGAGGCCAAAGGGTGGATTGCAGGTGTAGGCGATGCTCATGTTGTTCGTGTG
GCCCACAATCGTCGGTATGGGACTCTTGGTGAAGTTCAACGAGGGCGACATGCTGTGGTGCATATACAACGGCGAGTTTACGCTGTTGTCCCTGC
AATATTGATATCCATGAAGTTTAGTTGATGATCTTGCAACATGCCTTCAATAGCTTACCGTAAGCTGCCGGAGACCGAGTTATTGACCGAATTGT
AGGCGTGATTGGTCCCATCTGACACCGAACCAACCGAGTTAACGCCGTGATGTGATTGTACATCGAGGACGCCCAGGCCCAGGTGCATCTTCTGG
CGCATCAGCAGCGCCTGATCCTTGCCCTTGGCACCCGGTGGCAGTGGAGCATTCGAGTTCAGATGATGCTGGTGCGGATCCTGACTTCCCAGTGT
GGGCACAGTCGTCTGCAATGCATAATGCATATAAATAAGAATAAAGCCAAAGCTTAAGGCTATCAAACAAGCCAAACTTACGCCAGATGTGGAGC
CAATGTGACCGACAACGGAGTTCCTCAGACTGCTGCTGCTGGCATTGCTGCTGCTGCCGCCGGCACTGTTGCTGCTGTTGCTGTTCAGCATTCCC
GACATGGTGGGCAGCATTGTGGCGCCCGTCACCGGGCCACCGCCCGTTCCGCTGCCGTAGTGCAGTCCCCCCGTCGCACCTGTGCCCGTCGCCAC
GGATGCGGAGGAGTTGGCAGTTGGGTGGGAGGACAAACGAGGCAGGGCATTGCCCATTGGCTGATCGCTGTTGCTACCGCCGCCGCCTCCGGGAC
CGCCTCCGCCCGGACCGCCGCCGTGTGTGGTGGGCGTGCCGCTTAGCGAGTAACTGGCTTCCGAGGTAGGCGTCGAGTCGCCGCTTATATCCATG
TCAGCATTGTCGTTGTGTCGACCTGTCGGTAGGATTTTAAAATCAATTAACTAGATCCTACGCAACCTGCTTTATGCTCACCATCCAAACGCCTT
CGATGACTGGGCGGACCGCCATCGTTGTCGTAATTCCATCTCAGTCGTGAATTGTCCCGCGAAGAATTGGAATGTTTGTATGCTGCAAAGAAAAA
CACATGTTTTGAATATCATATTTGAAATTTCTGAAGCAGGTTCTTAACTCACTTGATCTGGAGAAACGATCATCGCGGTCGCGATCGCGATCCTT
GTCACGATAATCCTTCTCACGATGCTGATCGCGCGGCAAATTTCTGTAACCATATAACACATTAATGACTATTTAACCAAGGACTAGGGTGCTCT
TATTACAGATTCTTCCCAAGATCTTTGCTGGTCATATTATAATGCCATTGCCTTTACCTTTCTCTGTCCACCCATTCCTTTGGCTTCTCCCACTG
AGAGATTTCCGTCTTGCAGTTGTAATAATACATTTTGCCTGAAAGCAATCCAATATTATAGTTTGGAGCCTGGAGAAGAATAAGCTGTCATGGGG
GGACTCACCTGATGAGCTGACATGCTCGCTCCAGTCGCCATAACGCGCCGTCCGTTCGCCGCGATCGCTGCGCTCTCGTTTGTCTAACAAAAAAA
AAAACAAAAGCCACAGAGTATGTTTAGTAAATAAGGGGAGATGTGGGGTAAATGGGCGCTTGGACCTACCTGCGTACTTGTCCTTCTTGTACATG
TCCCTGTCGCGATCGGAACCGCGGTCCCGCTTGTCGCGCAAGTCGCGCAGATCTCGATCCCGATCTCGATCGCGATCGTCGGACCCGGATCGTTT
GTCGTTCTCCCGCGAGGAGCAGAGCTTGCCGCTGCCGCCTCCGCTGCCTCCTCCGCCACGACGATCCCTATCATGGTTGGTGCGATACGACGACT
CCGAATCGCGATCGTTGCCACGCCGATCACGTTTATCTATGAAGAATAGAATAATGTATTGTTATGGTATACAACTCCAACTTGCAGCTGCGCTA
ACTCACCTGAATATTTATCCTTCTTGTAGACATCCCGATCTCGATCTCGCATCTTCTGCATAAAGCTGTACCGCTCGCCACTGCCGCCACGCCCA
TTGCCGCCACCTCCGCCCCGATGATCGCTGCGGTCGCGCAGATCGTGCGAACGGGACGACGGCGAATCAATGTCCGGCGACTGGGAGCGGTAGCT
GTTGCCATTGTTCAATGGTCCGCCGCCATTTCCGCTACCGCCGCCACCTCCTCCAGCGGATCCGCCGCCTCCTCCACCGCCAGCGCCTGGCGACA
GGTCACGATCGCGATAATTGGAGGAACGATCGCGTTCGTAGTCGCGCTTTGAACTGCTGTACTTTGAGCTCTGCACGGGTAAATAAAAGCGCACA
CAGTTTTTAGTCGATTTACATTCCCAAAATCAATTGCACAGTGCTACAAAATACAATGTTTGTCGAGTACTCTCTAAGAAATCGCAGTAAGGATT
CAAGATGTGGTCAATATAATCAGTACATCAAGTAATGTAGCCAATATATGAGTTTTTCGTGTTCCAACAAATGGGATTAATTTAGGAAATCCTTA
CTGAATCTCTTGGATAGTACCAACCCACTGGTATATTTAGTATTGCATTCTTAATAGCGGTTGATTTAAGTCTCGGTTTAGTTGTAACTTTTGAA
GTTGGGTGGTTGGTTAGTTGAACTAAATCTACTCAATAGGAAAATCATAAGTTAATGCATAATGCCAGCTACTTTTGCCAATTTTCTCGCTTGTG
ATTATTGCCAATGGAAACGAAAGGATACAAAAAGAAAGTTGGGTGAAATGAAACTCCCGATGGTTTGAGAAATCAAATGTGTAATCGAGAAGAAT
TTTGAAATGTGTCGTGTGTTTGGTGTGTGTTTTGGTTTATCGTCTCCTGAGTAAATTATATATTAATTGAAACTAATTATTTAGGATTTTTTTAA
GTGATACTTTCGTTTTTGGTTCATATTGGTCGTTGTCTTCAGGTTATCCAAACTGAAAATCTAATTGTCCAGTTTAATATTAATCAAAATTAAAA
TCCTTGTTTGTTGTCCATCGTAAATTTTGGGATCATCCATAAAATTCCAATCTTGTGTTTATCAAAAAATTTTATAATAATTAATAAAGAATCCT
TCATAATTGAGTGGTGTTTCATTGTTTAAGAGATATAGAATAATAACTCTTTGGGTGTTTGGTATGTAAATCATAATTTGTTGATGTTTTTTATT
AGCGGCGATTTGTGTGTCGTTTTAGTCAGATTTTTGTTTAAAATATACGAGTTTGGATGGAAGATTTATTCCTGCTGCATGTTTCATGTTCTGTT
GCCTTCTTTTGATTTTTATTATTCATTATTAAGTAATTTTATTTGTTCCTTAATTTGAATGTTTTTTGTTTATTCCTTATCAGGATTGCTTTTCC
TGCGCACAGCACGATGTTCGTGGCACTTTATTGGTTTTTGATCACTTTATTTGCGTTTTTATATTTTACTATTGTTTTTAACCATTATTTTCTGG
GATCTTTGGGTTACTTACTTCTAGGCGACAGAGACCCACTGCTGAAGGCGTTGAATTCGCTGCCAGCGTCGCTGCTGATGCGCTGTTTTTGTTAT
TGTTGTTATTGTGGTTGCTAATGTTGCTGTTGCAATTGGCAATTGTTGTTGTCGAAAGGGAGAGATCAACAGCCATGTTGTTGCTGTTGTTGTTG
CTGCTGCCGTAGGAGTTTTTGTTGCTCCTCATAGATAATTAATTGAAGTGTATTTGGTTTTAATTTGAATTAAAAGTCCAATTGGTCGCTTGTTT
TCGAGGGCACACTTTATTTGGCTTTGGTTTATTTCCTATTTGTTTTGCATTAGTTATTTGTTGGTGTCTTAATTGATTGTTGTTGCTTTATGTAT
GAGGCACATTTGTGTTTTTGTTGTTGTCGTTGATTATTTCGTTAGACAATTTGGAAATTGGTTTGTTCTTCCGTTCCGCACATTCATGTTATTTT
TAATATTGGTGTATAATTGTTTACTACGTCGTTTTTAAGGCTATTTTAATTTGATTAGGTTCCTATTCCTTAGGCAGAGTTTAGAAATTGGTTAT
GCATTCGATTTCTAATTAATATAGTTTGATAAATTTGTATACTTTTAACCATATATATCATTCGATTTAAAACATTTGTTGGTGCTGTTCGGTTA
GATGTTGTAATTGATTAAATGATCGAATTCGGATTGGGTTTGTTTTTTGTTTGTTTTTTTTTTTTAGCAGTGATGCGTACAGATTCGTTTCTCAA
GTTAAGATCAGTTCAGGCTGCAATGCCGCGTTTTTGAATGGGTTAAAATGAAACACGATTCGGTCAGTTCAAAAATGGATGAGGTTACGGGAACG
TAAGATCTGGGATGCACAACAAAGACAGCGATTGACAAAGAAGGAGAAATATGAACCAAAAATAATCCAAAATCCAGGCTATACAATTTGCAAAT
TTTGTTAATTTTTCTCTTTACCAAAATATCAGCAAATGACACTAGGGAAATCGACGGTTCGATAAAAAATACGATTTACATTGGCTTTTACATTCT
TTTTTTTGTGGCTTTGGGTGCACTACGGGCTAATGAGCTAAACTACAAAATTAAAAATGTCCACTAAAAGCTGGCATGTAAATGTGATTAATTGC
GGTGTTCGAGGAGAATTTTCGGATCGGTCTGCTTACCTGGTATGATGTGTGACTGGTATGCTTCTCAAAGTACCTGGAAAAC
(SEQ ID NO: 976)

FIGURE SHEET 523

Exon: 6207..6004
Exon: 4820..4472
Exon: 4406..4155
Exon: 4073..3999
Exon: 3933..3858
Exon: 3748..3663
Exon: 3597..3502
Exon: 3442..3027
Exon: 2957..2719
Exon: 2656..2196
Exon: 2124..1955
Exon: 1837..1710
Exon: 1640..1001
Start ATG: 6207 (Reverse strand: CAT)

Transcript No. : CT25711
ATGAGGAGCAACAAAAACTCCTACGGCAGCAGCAACAACAACAGCAACAACATGGCTGTTGATCTCTCCCTTTCGACAACAACAATTGCCAATTG
CAACAGCAACATTAGCAACCACAATAACAACAATAACAAAAACAGCGCATCAGCAGCGACGCTGGCAGCGAATTCAACGCCTTCAGCAGTGGGTC
TCTGTCGCCTAGAAAGCTCAAAGTACAGCAGTTCAAAGCGCGACTACGAACGCGATCGTTCCTCCAATTATCGCGATCGTGACCTGTCGCCAGGC
GCTGGCGGTGGAGGAGGCGGCGGATCCGCTGGAGGAGGTGGCGGCGGTAGCGGAAATGGCGGCGGACCATTGAACAATGGCAACAGCTACCGCTC
CCAGTCGCCGGACATTGATTCGCCGTCGTCCCGTTCGCACGATCTGCGCGACCGCAGCGATCATCGGGGCGGAGGTGGCGGCAATGGGCGTGGCG
GCAGTGGCGAGCGGTACAGCTTTATGCAGAAGATGCGAGATCGAGATCGGGATGTCTACAAGAAGGATAAATATTCAGATAAACGTGATCGGCGT
GGCAACGATCGCGATTCGGAGTCGTCGTATCGCACCAACCATGATAGGGATCGTCGTGGCGGAGGAGGCAGCGGAGGCGGCAGCGGCAAGCTCTG
CTCCTCGCGGGAGAACGACAAACGATCCGGGTCCGACGATCGCGATCGAGATCGGGATCGAGATCTGCGCGACTTGCGCGACAAGCGGGACCGCG
GTTCCGATCGCGACAGGGACATGTACAAGAAGGACAAGTACGCAGACAAACGAGAGCGCAGCGATCGCGGCGAACGGACGGCGCGTTATGGCGAC
TGGAGCGAGCATGTCAGCTCATCAGGCAAAATGTATTATTACAACTGCAAGACGGAAATCTCTCAGTGGGAGAAGCCAAAGGAATGGGTGGACAG
AGAAAGAAATTTGCCGCGCGATCAGCATCGTGAGAAGGATTATCGTGACAAGGATCGCGATCGCGACCGCGATGATCGTTTCTCCAGATCAACAT
ACAAACATTCCAATTCTTCGCGGGACAATTCACGACTGAGATGGAATTACGACAACGATGGCGGTCCGCCCAGTCATCGAAGGCGTTTGGATGGT
CGACACAACGACAATGCTGACATGGATATAAGCGGCGACTCGACGCCTACCTCGGAAGCCAGTTACTCGCTAAGCGGCACGCCCACCACACACGG
CGGCGGTCCGGGCGGAGGCGGTCCCGGAGGCGGCGGCGGTAGCAACAGCGATCAGCCAATGGGCAATGCCCTGCCTCGTTTGTCCTCCCACCCAA
CTGCCAACTCCTCCGCATCCGTGGCGACGGGCACAGGTGCGACGGGGGGACTGCACTACGGCAGCGGAACGGGCGGTGGCCCGGTGACGGGCGCC
ACAATGCTGCCCACCATGTCGGGAATGCTGAACAGCAACAGCAGCAACAGTGCCGGCGGCAGCAGCAGCAATGCCAGCAGCAGCAGTCTGAGGAA
CTCCGTTGTCGGTCACATTGGCTCCACATCTGGCACGACTGTGCCCACACTGGGAAGTCAGGATCCGCACCAGCATCATCTGAACTCGAATGCTC
CACTGCCACCGGGTGCCAAGGGCAAGGATCAGGCGCTGCTGATGCGCCAGAAGATGCACCTGGGCCTGGGCGTCCTCGATGTACAATCACATCAC
GGCGTTAACTCGGTTGGTTCGGTGTCAGATGGGACCAATCACGCCTACAATTCGGTCAATAACTCGGTCTCCGGCAGCTTACGGGACAACAGCGT
AAACTCGCCGTTGTATATGCACCACAGCATGTCGCCCTCGTTGAACTTCACCAAGAGTCCCATACCGACGATTGTGGGCCACACGAACAACATGA
GCATCGCCTACACCTGCAATCCACCCTTTGGCCTCAAGGCTACCCTCGATGGCGGAGTGATGGTGGCGAATGCCTCACCGGCCACGCCCGGTGGC
AACGCCTCCTCCGGCTCCAGTGGAGCGAATAGCAGCCAAAGCATCGTGCCCGGCATGGGCCCCGTCTGCGGAATCAGTGTGATCACCTCGATGGG
CAGCAACAGCGGCACGCTATGCGAAGGACCGCCTACGCCCACCCAGGAGCTGGATTTGAGCGGCTCGGCGTTGGAGCAGCAACAGTTGGCCGCCG
CAGCGGCAGCCGCGACAGCGTCAAGCCTCCAGCTACAGGCGGCGCAACAGGCCCAGCAGCAGCGGAAATTGGATGGGACGTCGTCGGCCACGCTG
AGCTCACTGCAGAGCTGCGTGAGTTCCTCAGGACAGGCGGCAAACCTACGTGGTCCCGAGATTTCGCCAAAGCTGGCCAAATACTTCCGCGCCGA
TCTGATCGCGCATGTGACCAATTGGCACGCGGAGGTGCTGGAGCGTCAGGCGCAGAAGTGCTGTGAGGATACGCACCTGTTTGGCGACATAACGT
GCACGAGGATATGCGCGGAATTGAAGTGCGCCCGCAGCCTGGTGCGAAGCACCGAAATCAATGCCACCCTGCAGGAACAAAAAATTATGTATTTA
CGCCACCAGATCCGCCGTATCGAGGAGTCGAAGACTCAGAACGCGTTCATGTCAGACGATACTTAGGATCAGGAGCAGGTTAGGCTGCGCGTACA
TCGCAAGCTGTCTGTTAGGCTCAAAAAGAGCTTCTTCTGGCGCAGCTGATGATGATTGCGATGATGATTGGTCGATTGTGGCCGCCGTCAGCAGC
TTGTCCTCGTTTAGCAGGCCCGGATCCAACCCTATTTATTGAGGGCATCTGGAAATGGCTTAGATGATGACGACGACTGGCGGTGGCCCACGACA
ATGACTGAGAAACCGCGTGCATCCTGCTCCATCCTCTTACTTCTCTCCTCTGGGCGACGCATCTCTCCCCACCACCACAACCAGCCCGCGATTCA
CTTGTGTTCGGATCGAGTTCCAGTCCCCAACCGACTATATAGTGGCAGTATGTAACTGGCTGAGCGGACTGCATGGACTTGGCACAGGACAAATC
AGGATAAATCAACCAACAGCTGCAACAAGAACTTCAACAAGAAACACAAAAACTAAAACATAATTTATAATTAGCAAAGCGTAAATTAAAAGCAA
AAATAAACTAAAATAAGCATTGCATTAAGCAAGACGGAGGAAAAGCCAGAGAAATAG
(SEQ ID NO: 977)

Start ATG: 1 (Reverse strand: CAT)

MRSNKNSYGSSNNNSNNMAVDLSLSTTTIANCNSNISNHNNNNNKNSASAATLAANSTPSAVGLCRLESSKYSSSKRDYERDRSSNYRDRDLSPG
AGGGGGGGSAGGGGGGSGNGGGPLNNGNSYRSQSPDIDSPSSRSHDLRDRSDHRGGGGGNGRGGSGERYSFMQKMRDRDRDVYKKDKYSDKRDRR
GNDRDSESSYRTNHDRDRRGGGGSGGGSGKLCSSRENDKRSGSDDRDRDRDRDLRDLRDKRDRGSDRDRDMYKKDKYADKRERSDRGERTARYGD
WSEHVSSSGKMYYYNCKTEISQWEKPKEWVDRERNLPRDQHREKDYRDKDRDRDRDDRFSRSTYKHSNSSRDNSRLRWNYDNDGGPPSHRRRLDG
RHNDNADMDISGDSTPTSEASYSLSGTPTTHGGGPGGGGPGGGGGSNSDQPMGNALPRLSSHPTANSSASVATGTGATGGLHYGSGTGGGPVTGA
TMLPTMSGMLNSNSSNSAGGSSSNASSSSLRNSVVGHIGSTSGTTVPTLGSQDPHQHHLNSNAPLPPGAKGKDQALLMRQKMHLGLGVLDVQSHH
GVNSVGSVSDGTNHAYNSVNNSVSGSLRDNSVNSPLYMHHSMSPSLNFTKSPIPTIVGHTNNMSIAYTCNPPFGLKATLDGGVMVANASPATPGG
NASSGSSGANSSQSIVPGMGPVCGISVITSMGSNSGTLCEGPPTPTQELDLSGSALEQQQLAAAAAAATASSLQLQAAQQAQQQRKLDGTSSATL
SSLQSCVSSSGQAANLRGPEISPKLAKYFRADLIAHVTNWHAEVLERQAQKCCEDTHLFGDITCTRICAELKCARSLVRSTEINATLQEQKIMYL
RHQIRRIEESKTQNAFMSDDT*
(SEQ ID NO: 978)

Celera Sequence No. : 142000013384682
TGATCTATTAGAATTTGTTTAAAAAGTTTAGAAACTATAATTTTATACCAATCAACCATTTTACCTATCCAACAATTTCATAGAAAACTTCTACA
GTTTTATAAACATTATATGATTAAGAGCCGAACCTTTCAATCAAAAGATTCAATTGGATTTAAATTTATATGTCATTGTTTTTAAATTGGTTTTG CTGTATTATCAAAATTTTCCTTCGTTGCTCTTAGATAACATTTTCTCTCATAGAACATTTTAAAATTTTCTTTATTTCTTCGAGTGTGGAAAATT
GGTAGTGGAAGTATCTTGCAGTTTCGTCGTATATCTGCTCGTAAAAGCAGCAAGCCACCAATGGATTTCCTCCCACTGCCGACCGGCCACCCCAT
TTTAGCTGATTCTTGCTTTGGTCATTAAGACGCATTATTGTTTGGACTCAAAAAAAAAAAAACAGGGGGAAACGGTTGGATGATGAGACAGCGGG
CGGTTTGCATAGTGACTCTCTGATCTGATTGCAGACAACTGATAGCTTTATTTCATCAAATGAAATTAGGAAGAGTGTCGGGTTCAGCTAGGGGG
AATAATCGCAAATTAAATACTCATGTTTGATATAAACTCATAAAACAATTCTTAGTTTTTTAATCACAATAAACCATTTTTACCACATCTCACGA
TGATCATCTTAAGTTGGTTGCTCTTTATAAATATTATATATTTATATATATTATATAAATTAATTTTAGGTTTTGGTGTATTTTAAATTAAATGA
AACTTGTGAGTTAAGTCTTTAAAATTCCACTTCAAACTTGCCGCGCCACAAACGACTGCTGCAGCTCGGCAGCACTGGCAGAAATACAGGGCATG
CAAGAAATACTGGTCACGAGTAGGTATATTCCACCGGAGAGAGCGCTAACTGAACCCAGTATTTTCCGCTGAGAGAGCAGCAAAAGCCGGTTCCC
ACCAACAACTTCGAACAGCCGGCGGAGTTCAGTAATAAACAGACTTCGAACGCGTGCAGTTCAGATTGAGTTTGAGGTTCGATTGGATTCGAGAT
ATCCAAGTTCCTTTTGCGCTACGTTTTGTTTAGCCGAGTTTGCCCCGAACTAAAATCACCCACCAAAGCCGGTTCGGGATGCGATGATGCCAAGG
ATGCAGCTGATGCAGCCGGGCTCTTGTATCTTTAAGATACAAATTAAGTTGATTTGTTGCGCTCGCGTTCTCTTGGGTAATTGAACCCCACAGTT
GGGCTCCTTGCGCCCTCTGCCGCGCGGTCTTCGGTCTTCGGTCTTCGAGCATTTCGTTGCATTTTGTGTATCTAGATACCTTTGTCGGTATCCGT
ATCCGTCGCTTGTCAATCTGGTCGCTGATAAAAAAGCAAACGCGAACGCAGCCACGAAACATAAACCAGCCGTCAACGGAAAATAAAAGTAAAAA
GCAACAAACAGCAAGTGGCGTATCAGTTCGTGTGTTCTCGGTGATAAATGCATTTCATGCGTTCCAACTATGTAAATAGCAATTTAATTTGAGTG
TCCACAGTAAACATCAAAAAACCGCCCTGGACTCCAGTCACCACCACCAACAACACCATCCCCGGTGGAGCCCAGTGATCCCATTGAAACCCCGG
TAAACCCCTGAAAAGGGCAGTCGTTGTCATCGTCGTCATCGTCGTCGTCGTCGTACGTCTGTGCCATCCAAATATTGAATATTTACAAATGCGTT
GAGTGCATTTTCGAGTGGCCGGCACTTACAGTGACTATCTGGTGGATGTGCGAGTGTATTCATCGGATTGCCAGCAGCATAAAACTTCGTTTTCG
ATACTGATCCAATACGCGAGTGCTTATATATTTTTTGTGTCGCTAATTGAGACCAAAGGTGTCGAAGTGCGGCGGTTATACATATACGCAGATGA
CTGCTAGGATGATCTCAATATGCGGCCTGGTCATGGCTTTGATGATGGGTAAGTGGTCTGCTACGATTGGATTTTGTGGACTAAGTGAGGGATTG
CCTTATTCTCGGGGGGTTCTTTGCAATCAAATTCATTTCATTTGCTTAAGGGGGTTCTCAATTCCCATTTATTTGCTTATTTCGATGTCGGCATT
TGGCGATTGCCTTTGCAACTGAATCGCTGGGAACTTCAAAGGAATCACAACATTTGTGTTGCGCAGAATATTGGCCATTCCATCTTGGGTGAGAC
CACCCATAATATGGACTCTATTAACCTCGAGGGCTCTGCCGTCCACACAGAACTACTCCTATTTCCTTATTCTCCAAGGGCGATTTTGTTTTGCG
AAGAAAAACCGAAAACCCAGAGAGCCTTTGTCTCTGGCTATTCAATTTGAAAGGCAAGCGGCGTGCAAAATGACTCAATTAAAAGTCAGCCAGGA
GCCACCAAGCTGGCATTACTAATTTGGAATAGGAGAAGGAAAGCAGCGGGAGAGGAAGCCGTTTGGAAAATTATGAGTCTCAGGTCTCAGTTCAA
AATGAAGTCATTTTGGGCAAACATCAACATCGAAAATGTGACGAGCTCACTAACACAGGCAACAATTGAGGTCCTTGTGGCCAGGTTATCCTTTT
CAATGACAGATGTTGCTCATTAAATACTTTTCTTTAGATAAAGTAGTTAATTTATAGGCAGATCAGCTAAAATACTCGCTCGGAATAAGAAAATA
TTGTTATAAAACTAATAAATATTTCATTTCTATACCTTTTAGATCCGTTCTGTTTTAATAGATTCACTAATTAGAAACACTATATAGGCATGTTT
CCGAATGTTTTTTCCCAGTGCTAGCACACACACACACTTGAAATATAAGGACCATCCTGCCAAGGATCACGATACCCACTTGAAGTGAGACAAGC
GACGCCGAAATTTCGGCTAATCAAATATAGTTTACAGCGGGGATTACGAGTGGGATAAGGATCGTGCCCGAAGGAGGGGGATCTCGGGTCTCAAG
AGGGACACGATTATGCAAACGAAGGTCCTTAACAACGCATGTGTGTGCGTGCGTTCGAGTGTGTGTGTGAGACAGGACAGAGCTGAAAACTGC
TGACTGTTAAGTAGCACAAAGGCAAACAGCCGCTAACAAAAGCCAGCCGGCAGACAGCGAGGATAGGGGGATTTGGATTCGCATATTTCAAAATC
TGTGCAACGCTACTACAGAGGTCCATTATTTGTATGGCAAATAATGTGGCTGTCAGTGTGTGTGTGTGTGTGTGTGCTTGTTTGTGTGAGTTCCT
TTTGTGTGGCAGTCATAATTTGTTATTCAAGCATGCAAAATGCTGCATGCAACATGCCAGGCCAAAAGCAAAAGCATCGTACATCCCACATTAAG
GGCAGCTGTGGCAACTACAAAACTCCCCTTCACCAACCTTTGCCACTGCCACTGCCACACCCCCCGCCCCTGGTCCTTCCGCCTGTCTGCATCCT
TCGGCAACCTTAAAGACTGCCAGTCGAAAGTTCTCCAGAGGGTTCTCTCTCGAAAATTGTATGAACTAGTCATGCATTTGCTTAGAAAGCCGGGG
TATAAAGGGAATTTCAGGATTTAATGCTGCCTTATAATGAATCCAATTTATTAGGCTGTGTTCTATGAACAACTGGTCTCCGTTTGAAATACTTT
GAATTGAATACAGCATCCTTGAGGTTTTCTACTACACTGGATTGGCTGGATAAGGGTATTTTACCTATATGTAATAGACATAAAACCATAATTTT
GTAAGCTAGTTATTTCCTACAAAGTAGCGTTCAAAGAAATCATATCCAAAATGGTATTTATTTTACACATAAGAAGTAAGAGACTACATAATAAC
TTTTCATAAATAATGCTTGGCAGGCAGTACGATTCCCATTTTCATGTTGTTAAATCAATTTTGTTTGAAACACAAAGGAAATGATCCCGAGAAGC
TCGATTGTAGTTGAAGGGAAAATCCCTGAATAAAGCCCTGATGACTGTTTATTAGCCATGCTGTAACCTTTAAATTGAATTCCAACTCTATCAAA
GACCATCCAGTCCTTTTTCTGGCCATTTTTACCCCTGAAAAAACCCTAGATCAAACGTTTGACGCGTAATTGTCAGACACAATTCCACTTTTCAT
TCAGTGCCTGTCTGTCTGTTGACTTGCAGTTTTCCAGCACCGCTTTTCCCAGACAAATGCCTCGCATTCCACAGTGACAGTTCAGTTCTAGCCCC
CCATTCCCCATTCCCATTGCCACCCCCCGCACACAGACACACGCACACAAAATCAAATCAAAACGCCACCCATGGGGCAAGTTCAAGTGGCTGCC
ACAGTGGGTTGCCTGATTATTACTACAATATTTCGCATTCATTGTGCTTAATCGACGAATGTTGCCGCACCATTTGTGGCAGTCGAAGTTGGATC
TGTATCCGCATCTGCATCAGAATCTGAATCTGAATCTCAAAGATGCTGATGAGCATGAGGCCACAGCAGTGGGCACTCGTAATACTGCCTGCTGC
TGACTTGCTGATTTCGGTTATTCGAGCCAAACAAACGAACTAATTATCACACACGCACACACACCCGCGACGAGGGTAAGTGGAAGAATGGAACG
ATGCACTGAGAAAGATTTCTTTGGGTTTAAAAAAAGAATCTTTAGAGTTCCAAGTACACACCTTAAAGTATATAAATCACAAACGTATTACTTGT
GAAACGGTTGTTATAGAGAAGATTGTTATACCTATAATGTCAAAAGATAAAAAAAGATAAAAACATCTACCAATTCCTATCATAAACTCTGTCAT
ATCTCATTACATGCTCATAATTTGCGAAACTGCTTACCAAAAGTTATAAATAAACATTACTTAGTTTAATAAATCAATTGAAAGACACAGTGTTG
AAAATTCGTTTGTATTGTTTTTAAATTTAGAAAATCAAAAATTCCCACTTGGCTACCCTTCTTTTTCGCCAGTGTATGTCCACAGACAGATCGAG
ATGGGCAGTTGGAACCGGGACTGCCCGCTGCTCCGTGGCTCTGTCGCTGATGTTTGCAGCATCAACACTTTTTCAGTTTGCTGCTCGGCTTCTGC
GGCATCAGTGCTCCTCCACAGAGCTCCACCTCCTGCCCCACTCCTCGTCGCTTTCCGCACCCTCTCACGCATTTTTGTGCCCACATCAGCGCAAT
CAACGGACTGCGGAGCGGGACGCATATTTCTTTAATCGACGCCCAGTAACTGACATTGTTCCCTCGTCTCGTATCGAATCGACTCAACTCGACTC
GACTTGACTGGAACTCGAACTCGTTTTCCGCACGGCAAATTAAATCGATTCAGGGGAGGATCGAGTCGAGCAGGGCAGGGAGTTAAGCCCAGCCA
AGAGGAGGAGGTGGAGGGCATCCCGGTGCCTGCCCAACTGCCTTTTCGGTTGGGCCGTGTATCATAACACGTCTGTCGGCGATGTGACTGGCATA
TGAATCGCATGGAGTTCCTCCTTCGAACGTCGAAAGGCCAGTAATGATGTTGTGGCTGTTGTTGTTGGCCCGCTTATTGATTCCTCGGTGCGGTC
GTGCTCTTGGCCAAAAAGGAACTGCGCCCGGGACCCACAATCTGAGGTGTTGTCTCAAATTGCTCCAATTAGTGGCCAAATATAATGGTTGCCGT
TTTGTAGTTCTTGTTCATGTTCCTTGCTCCTGCTACCCAAGTCGTATAATCAAAAGTAATTGCGTTTGAATTGCTTTTCGTTTCGAGTTGCGGTT
GGGAGTTATGTATCTTCTGGCCATATCTACTCACTTGACTTTGTAGCCTCGAATGGCGCCACTTGTGGTCTGGATTTAAACAGCTTCGATATGAA
AAGGTTCTTCGCTCATTTGGTAATCGCCATTGAAATGCATTCATATGGGCCACACCTGACCAGTGAATTGCATTTTAAATGCAGCAAATTGCATT
TGCGGCTGTTGATTTAATATAACAACCGATTTGCATTCACAAATAAATGAGAAACACACAAATTAAATGTATAAAAACATTTTTCCTCTCGAAAT
GCGTTTATTTTTCGCATGGTTTTATGGGCGCCTTTTTCTTCTGGCTTTTAATTATGTTGGTACAAAACTCTGAATACGTTTTTGTTTGTTTTTT
TTTTTCACCATACACATATTGTAATTTTGTTTGAGGACACGCAACTTTGGACAGCAATGGCGTAGGTTTTTCTCCATGCCTCTCTCTGATACTC
TATAAAGGGTATTTTTTTAAATTTTAATGGCAAAGATCATTTCATTTAAGCTTTGAACTTATGTAATTATTTAGTTTGTAACAAATTGTCCAATA
ATTCAATAATAATAATATGCTACTTAATAAGCACTTTAATCATTGCAGCTAAAGAGTATTCAAAAAGGGTTTTTAGATTTAAAAAAAAAGCCTCT
GTTTTTTGTGCTTCCGCCCTTTTTTGAGTATTTTGTTGCTGGTGTTTCTGCCTTTGCTCCTGCCCTTGCAGAGCGCTTTACAAAATTACATTTGC
GTTAAACACTGTAATTTAAGCAGCTTAAGCGCATTTAATTTGTTTAAACCACTTTAATTAAACAAAATTATGGTTAATGCACTTTTTTTTTTTAG
TTAATTAAGCCAAATTGTTCGATGTTCAATTTAAATTTAAAGGGACTTTTGTAAGAGCTGCAAAACTCTGCCCTTTAATCGGGATAATGGCTGAC
TGTAATGAGATCCAGTTTACTAATTTCCCTCGCTTATTTCTATAATTACAGCTTCCGTTTTGGCCAGCTCATCGCGTTTCCAGCGAGTGCCCCAA
AGTCAGTCCGTGGTGGAAAATGAATCCGTGAAATTCGAGTGCGAATCGACCGACTCCTACAGTGAACTGCACTACGACTGGTTGCATAATGGTGA
GCAGTGCGATTTACATATCCCATGGTTGTGCATTAAGCATTCGCCTTCCTTGCACTCCATTCCAGGTCATCGGATTGCGTATGACAAGCGTGTCC

FIGURE SHEET 525

ATCAAATCGGTTCCAATTTGCATATCGAGGCGGTGCGGCGCACGGAGGATGTTGGCAACTATGTTTGCATCGCGACAAATTTGGCCAGCGGCGCC
AGGGAGGCGTCTCCGCCCGCCAAACTGAGCGTGATATGTGAGTAGTTATATTCCCAGTTTCAGTCCCCATCTCCATCCCAATCCCAGTGCCCATG
TCATTCCAACTCCAAGACCCACAATTGTTCGCAATAAGCAAATTGACTGATGGTTAAGGGCGACAGCAAATCTGTCTTTGCTTGTGCAAATTAAC
AAAGCGAAATTGAATTGTAAGCGGGTAGTTGAGAGCACTGCAAAAAACTTCACTTGATATTGTTACATTTTTATATCTAAAAACTGAAGTTAGTT
CTTGAGCCATAAACTTTCAGTGGAATATTACATAGAACTTACCTAGATTGATAGTAACTGCTGCACTCTGTAAATGCTCACCGGTTTCTTTGCGT
GTAGGGCAAATTCATTTGATTAATGCTGCATTTAATGGTATTCCAACCCCAACCCCACCTCTCCCTGGCCCAAACCCCCCTTTTCAGATACGGGC
AAACCACAAGACAACAAGAAAAGGTAAAGAGGCATAAAAACGCAACCGAAGCGAACGGAACGCAGCCCAACAAACCGATGAAAGATAAAAACCGA
AAGTTTTGATGTACATGCGTCAGATCCCATGCTAACCCAGTCCCTTTTGCCAACTCCCCCTTCCAAAGACCCCCCCCACCCCTTCACCAATTAA
CCCCTTCGCGCAGAGCTACAGGAAGTGCAGTGCAGTGCACAGAATGCATCCCATGCATCGGACCGTGAAGAAGAAGACCCTGGTCGAAGAAGAAC
CACACAGAGAAAGATCACTTGGTTCTAAAATGCAGCTATGCATTCGAAAAGTAAACTTCTTTGAGAAAACCATCTTCAAGATACATCCTCAAGAT
ACATCTTCTTCTTTGCAATTATGATAAATTGTAGAGTTCGTTTCAAATCTACCTTTTCAATTCTTAATAGCGGATAAAGAAACATATCTATGAGT
CTTGAGTTAAAACAATACGATTAGATAAAATATCTCTCAGTGCATCGCTGATTTCCTTCAAGTAGCAAGTGCAGTTGCAGTTCTTGGCCTCGTGT
TGAGGCAGCGGCGTCACGTGATTGATGTTCATTTAGTTGCGTTTGCCTTTAAGCAGAAAAATGCATAAATTTACCAAATAGCTCCCCCCACTTCC
CCTACTCCACCGTCTTCCTTTTTCATGTAAACAAAACGCGAGTTTTATGCACAATCTGGAGTGCATGTGTTTGGGGGCCCTCCAATATACGAGAT
ACATATATCTGGTATCTGGTATCTGCTATCTGCATCTGCATCTGCATTTGTATCTGTATCTGTAGCTGGGCTGTCAGCGCGGCCACGGCATCCGA
GCTGTGATCAAAGCCACCCAACAGCAGGGGCATCTTTCCTCCGCCGTCGCTATTTATACACCAGCCTCATCTCAAGTGTTTTTAGCTAATTAATT
AACTAATTAATTTGTAGTTTCGGGAGTTGATTTTAATTGCCACAGCTCCCTTCCCCCCCCAAAAAAAAAAAACAGCTGCTGCTGAAAAGCGTGGAG
AGTGTATATATATATACGTATTTGTATCTTGGAGGGGATGCAGGGAAAGTATCTTGGCGCCAGCTGAAGCTAAGTGGGTTATGTGATTACCACCTAC
TCCTGCCCAGCTTGCATCAATCTCATAATTCTTGAGCAGCAGACAAAAACTATTAAAATATGCATGGGGCAGTATGGATGGAGATGGTGTCGTTG
CTCCTCAGTTTTAGGATTCGGTAAATATTTTATTCAGGACTCGTCGCCATTGTGTCCCCTGGCTGCATTGTCTTAGCCCGGATTATCCTTCCCCG
TCTGCACTTTTCTCGCAAATAAGTGTTCAATTAAGCGCGAGAAAAGTGTCATTTTCCTATGCGACATTTAACAAATTTGCAATGGAGACTGGAAA
ACAAGAAAATTGTGTGGATGGGAAAGGCAATCTGGTAAAAGCTCATTAGATAGTGGAATATATACTTCTGCATCAATATAAAATAGCAGATAGAT
AGAGCATTAACATTTTAAATGGTAAATAGGTACTAAAAGTTCGGAAATAAACATATTTTTAAAGAAATATTATGAGTTTGTAAATATATTTTAGT
CTTACAAAAGATACACACACATAGTTGAGTTTTAGTACTAAAGTTAATCTGAATTTATGAAGTTATTGTGAGTAAGCGCTTCTTTAATGAAAGGC
TAATGGAAATCCCAAGGATAGTTCCAATCTTAGCGGGCAAATCAAGTAAACCTCTTTTTCGGTATTCATAAAAGCGGGAAGACAAATGCTGACAG
TGCCCGGCGACTAACCGATGACTACAAGGAATTAAGCAGACAGCGAAGAAATTAAACAGACAGCAATAAAGGCAAAAGCGAGTCAGAGCCAAAAA
CAAGGACCAAGAAGAAAGCAGCCGCGTCAGACCAAAACCAGACGACTGGCTCCTCTGTGAGGACGATGAGTTTGGGGCGAAAGGACATTCCAAAC
ATTTGCTCAGCGAAAGGGGTTGTTGGACTCACAGGACTGGCAGCTCCGGTACTCAGCCAGGATACACAGACTAACCATTGAACAGCTGAGCGAAG
CTGGTGGCTAAAACCGGAGGGAAATGTGTGTTGTGCGCTGAAATGTATGGGGGGGAAATGAAATGCAACATTAACACGAAACATAAACATAAAAT
GAGAAATGGCAGCAGCAACAATGGCAACCGAACCGAGCCAGCAAAGTCATAAAAACCAAACAAAATGCAAAGACACAGCAAGGACGGGATTTGCA
GGGGAATGTCAGGACGAAAAGCAACCCCTTAAATCGACCGCCCAGGCACCCGGGCACCCGAACACCCCCATCACATATATATATAGACTGTTGTA
TCTGTGCTCTAGACACAAGTTCAAGTTGACTGCAGTTGGTAAGTTGGGTTTTTATTTTACGGATACAGCGGGGGTGGAACGCGATGCCCGGGGAG
TCGCGCGGTCGGGTGGCGGTAGCGGTGGGGGGAACCGGATAATTTTCATTTTGTGAATGCCGGAAAAACGCATAAAATTTTACGAGCCAAGCTCG
GAGAACATTAAAGGGAGACGACGACAGACAGACCGAAAAACAGAAAAACAGACAAGAGCTTGCAAACGGAAAATGTAGCCAACTTTTTGGCGCGC
TAACCTGCGTCCTCTCTTCATTTCTAGTACTCTTCACACAGCAAGGATAATACCAGTTTTCATTTGAAGCTATGATTAAGAAAAACAGCAACTAG
ATTGACTTTGATAAGCAACGAAATTAGACATTGTGAAACTACACATTTTCCTTTAATTAAAGGTTCTTAAAAATTCATATTGGATATACTATACA
GTATATATGTGCATTGAAAATAAAAATATTGTAATAAAACATACTTGGCTAAAGATTTGAAATCAGTAGATATTTAATTTAAATAAAAACATAAA
AATGCCCTAGCACAGACCAATTGTTTTGCTCTGTGCATCTCTTTCAACCACTCTTTTCCTAACTCTAGGATTTTCTTTATATTCCTTTTTGGCAT
TTATTTTACTTTTAGCTTTTCTGTGCTGCTACACGAGTTGATCATTAGCAACTTTTGGGGAAAGCATTACGGGGGGGGGCAACGGCAGCAGGGG
CGTAGTTCAGGGAATCCCCCCTTTAAAACGGGGGCTAACTGCCCTCGCCAGAGGGCAAAGGTCACTGCAACGGAAGTCCCCTTTTTTCGCAAGCC
ACTGGAAAACCAGAGGGCAGACAATGTGCGATAATCGAATGTTTAACGTTTTAATTTGAAAAACGTTTGGGGTGCTGAGACAGCGACTGGCCAAC
TTTAATTAAAGATCCAACGATAACGCTATGGAGCAGGACACATCGAATGTTCTTCGGTCAGTTGTTGCAATAAATTTTCCATAAATATAAATGGC
TGGCCACTGAAAACGGAGAGCTGGGGAAAATGGATGGTAAAATTTGGAAATTCATTGATATCGAAATCCGCTGATGAAAGCCACTCATCGATTTG
TATCTGTGGCAAACGATCTGCGAAATAGTTAATTCGTTGAGTAAGATATCTGCAAACAATTTTGATGCATTTCCCTCTTGCATCTGCGTTAATTT
GCGAAATGGGTCAATAACTTGTAAGCCGCTTTGTGCACCGCACACACACAAGAATGCCCAGCCAATTGAAGTGAAATGGAGTGGAGTGGCCACTA
GCCGCTAGCCACTGGCCAGTGTCCAGTTTTCCAGTTGGACAACTGGATAGATGGAAGCGCAGAAGGGCTGCATAAGTCCATTAACGTTCACAATT
ACCGCCGGCCACTTCAGAAACACAGCCACTTCTATGGGCTCCCATTTCCATTCCTCCATCTTTCGGTGGACACGGGCCACTTGGGTTTATGACAG
CGCTGAAAACCCTTCCACTCGAGTTCGATTCCCAACTCTGCCCGTCCGAAAATAATCTATTTTTGATTATCAATTAATTATATTTTCATAAAAGC
GGGCGATAACAAGAAGTGCAGCACTGCAGCTCAAGGAAAAAAAAAAAAAAAACAAAAACTAGTTATCTTATCGGGAGGAGCGGACTCATAGTTGAC
GAAATAAGACTCAGTCGGCACACTTATTCTGGGGTCTTTGGAGCTCCAGAGGTGGTGATGGGGAGTGAGTTCCCAAGACCCAACCGATAAGAACG
ATCCGCTCGGGGGAACTGTCAATTTCGATATCTATAATTCTGCTTGCCTTTCGACGTTTACTTCCACTTTGTTTACCCAAGGCGTCTCTATTTTT
TTATGGGTCCTACCCACACCCACACTCCACGGCATTCCGGCAATTGTTTACAGCGATTGTGGTTTATGCTCCATCCTCGGCCAGCGAAAAGTTTA
ACAAATTTATTTTGTTTTGGAGTCGTGTTGGTTTACATCGTCTTATTTCCCTCGTTCCCAGTGTTTAGTGTTTACCTCGACTTGCACGTTCAACG
TGTGAATGACGACCGCCTTCCGACCGACCCCTACTACAACTTAGAGTTACCCCTCCTCCCCCCACTCCCCGCACGCCATCCCTCGCCCACAGGTA
CATGTAGATACAACCCATGGGTGTCAAAAGATCTGCTGTCTCTGGCGATGCATGCATCAGCCTAATGAGAAGCTCGTTAATTAGCGACTCGCGAC
TTGCTAGTAATTAAAGTTACAGTTAGTCATACCTATTAGTCAGATTCATATAATACTTTCTAGGATCGCAGAGGTATCTCAACATGAAGCCAAAA
AGAGGTAGCACCAAACAAGCTATATATTATAAAGATACTTACAAGGGATGCAAGTTGAGGATGTTAATCTCTGGTTCTTGTACTAGCACTTATAA
TGTTAGATACTAATCGTACCTTACAATACTTTAGAATCTTTTACTTACGAACCATAGTAAATGCCGAACCTCTTTAACGAAAATACGAATATCAT
TAAGCAACATTTCCCCACTTCTATGTTAAGATGCTCAACCATCAGATACTTGTGTGCTTACCTGTCCAGTGGCGAGTTGAATCCGTTCCCGTTCC
CGTTCCACACTTTACCCGCTGCTCACTTCCCCCTAGATGTTTGGCCATCCATTAGATACTTTTGCTCCTCGGCTGTCTAAGTGCCAATTAGTTCA
CTCTACTGTCATTTTAGTCGTAACATATACCAAAAACTTTGTGCCACAAGCCCACAGAGTATAGCCATTGGTACGTACTACGTACCACCATACAA
AGTCGTCGTCGAGCTGACGGACGTGCCCCAAGAAGAGCAAATATACAAACACATTTCAAACTTTTGACACTTACCCAACGGAGACGAAAGACAGG
GCACTGTTTATTGAGTTGTTGCTGTCGGTTCAGTTTGGTTCGGTTCGGTTTGGTTCTGTTTTTCCACTGCCTGCCACCAAATAAGTGTCTACAAA
TATTTAGAGGCATTTTTTGTTCACTGACTGAGTCTGCGAGAGGCAAACAAAGTCGGTCCCAAACAAGATTTATGTGCATATGTAAATTTTCTCT
AACGCGGCCAGCAAACCGCAGCCATCCAGACCTGGCAAACATTCAGATAGGCAAAGAGGAGAAATATCCATAAAACATACATCATCCATTTTGCC
TAGATCTCGGCTCGCTCCTTTGGGCCGCAGATAAAAAAATGTTTTATGAAAATTATGGCACCATCTCCGAAGGCTGTAGCAATCACACATAACATA
CATACATATATATGGAATACCAAACGCGGGCAAATAGAGAATGTAGGAAAACAATTTGAATAAATTATTTGGGGGGATACCAAATTAGAACTTTA
AGGAGCAGCATCGCTCGGCATCCGACAATTATCGCTCGGAATACAAAAGTATCTCATTCACATCGCCACAATGGGCTGCAGATACACGATTGCAG
CTACAAGATATTATGGAAGTCCGGTCATACAAAAGCCACACACAGAGAAATTTTTATAATTACTACAAAATCGGAACTTGAAAAACTTCAACTGT
CGTTGATAACAATAAAACATTAAATGAACACTAAATAAGCTGATGAAATGTATTTCAAATTTAAGGAATATGCAGTGGATATTCTTATTTTGACT
AGTATTTCAATCTTAATCATATTAATATGCATTTGCCCAACTTAGCATACCAGAGAACACTTTTAAGTTTTCTCTCTGTGCAGCGATTGTGTATG

FIGURE SHEET 526

CTAGCGTGTCTGCAACATGACTGGCCACGCCCCTTGCGCCTCCGGCTGCCACTAAAACATAAATTAAACCCTATGCCACGGCAGAGAGTTTAGAG
AGCAGCGCATTCTTCTTTTGGACTGCAGTTTTTTCCCCCCATTTTTATGCGCTTTTCTTTTGCGCCATAGAAACTCTTTTCTCATGCGGCAA
TTGTTGGCAAGTACCGTTCCATACCGTTCCGTCTGGCCAAGAAGTGGAGAAAGAAGCCGGCGGGCAGGAAAATGGAGAGGGCCATGTGAGCATTT
ACATATGGGCAGCAAGGTGGGATCGAGGTCGGGAGCGAGAGGTGGAGCCTTCTCCCGACTGACTGACAGTTCAATTTATGCTTCCTCGCCACCTT
AAATGGGCTGCCAGGCTGTGCCGATAAAGACAAAGATTGCAGCGTCGTGTTCGGCGCTGAACTGACGATAAAATGCACTTAATGCCGCGCGAAAT
ACCCCTGCTTTCCAGGGCGAAATATGTATTGTATGTAGTTATAACCAAAGGGCCACGGAAAGCGGAAAGCAGAAAATCTGAAATCAGAAGAGGGA
GAGCAAGCGCAGCGAATTCGCATAGCCAAGAAAACGCATTAAGGCTAAATGTATCTTCCGGATATATTATGCATATTTATGGAATGCCAGCCTAT
TCGCATTTTACAGGGGCTGATCAATAACTTTTGCTGGCAACGAGCCTTCCGTTGGCCGAACTGTTGTGGCAACCCTCGGCCTGCGTCTTGCATTA
ATTCAATTAGTTTATAGCCCACACTCATTCCGCAGCCTCAATCTCCGCATCTGCTACTTCTTTTACACGGTCAGAAAATATATGAATTTACTTAG
TTTTTTATAAATAATGTAAAATTTAAAATGTTATTCCCTGTCATCTCTTCTTTAATATATTGTGGTTCTTAGCATCACTTACTTTTATATATGTA
TCTTTTATGAGGCATTAGATGATAAAAAATATACATACTTGGCTCGAACGTATGTTTATATAAAAACTATAATCGACTTATAATAACACCATTCT
ACCCATTCATTCCTACCTTCAGATCTTGAATCGGCCAGTGTTCAGCTGCTGGGCAGCAATCGCAACGAGCTGCTGCTCAAGTGCCACGTGGAGGG
CGCCTCAGGAGATTTGGAACCGCTAGAGATCGAATGGTATCGCAACAGCGAGAAACTTAGCACCTGGAAGAACGTCCAGCTGGATCAGCATCGCC
TGATAATCCGACAGCCGGGAAGCGAGGACGATGGCCTGTACCGCTGCACCGCCTCCAATGCGGCGGGTCGAGTGATGAGCAAGCAGGGCTATGTC
TACCAGTCCAGTGTGAAGTGCCTGCCCCGACTTCCTAGGCGCAAGAACGAAAAGATGATGGAGTCCTGGGACAAACAGACCTTCCTGTGCCGCGG
TAAGCGCGGTGGAGCTGCTGGACTAGAGGCACTACCCGCCGCTCCCGAGGATCTGCGCATTGTGCAAGGACCCATTGGTCAGTCGATTATCAAGG
AGGGTGAGCCCACGGCTTTGACCTGTCTGTATGAACTGCCCGACGAGCTGAAGAACCAGCGCATTCAACTCCGTTGGCGCAAAGATGGCAAACTT
TTGCGTCAAGTGGAACTGGGTGGCTCGGCGCCCATTCCAGGTCACTCCTTCGATTCCGGCAAGGATGCTCTGTTGCGTGAGGACGCCCGTCTAGT
GCTGCACAAGCAGAATGGCACCCTAAGCTTTGCCAGCATTATTGCCAGTGATGCGGGTCAGTACCAGTGTCAGTTGCAGCTAGAAGCTCATGCTC
CGATTAACTCATCTCCTGGCATCTTGGAGGTCATCGAGCAGCTAAAGTTTGTTCCTCAGCCCACGTCCAAGAATTTGGAGCTGGATGCAGTGGTG
GCCAAGGTTCACTGCAAGGCGCAGGGCACTCCAACGCCGCAGGTGCAATGGGTTAGGGTAAGTAATTCAATCCAATTAGATTCAAATAAATACTT
ATTTTAAGGTACGAACTAAAATGGCATAGCATTCCCTTCGATATATTTACACATGGTTTCAAACAAGTACTAGCTTTCATTTATATATTTGTTAC
ACTTACTTTTGATAAGTAATAGATTGTTCTTGCAAAATTTTAGTACACCCTATCCGGTTGACATCTGCCTCCTATTCAGTAATTGCCCAGGCACT
TCGGTCTTCATTTCGACCGCTTCCAAATGGGAATGTTTCTGGACATTTCTGGCTCACTTTTTCGCCCACTCCACCACGGCAATGATGGCCACATG
TCACTGACAAATTGAAAAAACGCGCATTGCGCCGCTGGGCAAACTTTTGCTCCAAACAAACCGTTTCATATGCAAAACTCTATCGTGTCTATGTG
GCCTAAGCACCCTTCTTCTATCGCCCGAACATCCGAAAAACGAACCCACTCCATTTGGTGGCCATTGAGCGTTTTGTGTTGCCAGCTGTTTGCCA
TGGCCAACCAATTTCGACAACTGTTTGTCTATTTGGGAACGGAGCGAAAAAAGAGGATCGAACCCTTTCAAAGAAAGTTTTTCATTTGGCCGAAA
AACAAACCTGACTCAAACCTGTTCAAAGTGTATTGCGTCCTTTTTGTCTGCTTTTCTGCATTTTTGATGAAAACGCATGGCACACGTTGGCAAAT
TGGTTGGTAATGGTCAGCTGTCTGTTTCTATTTCTCACTGATGTTTCACATTCAACTTTGATATTAACAGATTGGAAGTGCATAATAAATGTGCA
TGTGTCTTTGATATTCAAATTAAGAAATGTGGGGGTGCATAAACCAGTGCACCACTGCAGTGGTTTGATATCAAAAGTAATAACCAGAAAGAAAA
TCTATCCTTAGATTGCTATTGATATATGATAGATCCTCATAAAATCTACTAACACAACAAAAAATTATTTCTCTACAGGATGGGGAAAATACCAC
TTTACCCGACCATGTAGAAGTGGATGCCAATGGAACACTGATTTTCAGAAACGTTAACTCGGAACATCGCGGCAACTACACTTGCTTGGCCACCA
ACAGCCAAGGACAGATAAATGCCACTGTGGCTATAAATGTGGTGGTCACTCCCAAATTTAGTGTGCCCCCAGTGGGACCCATCGAGACTTCGGAG
CAGGGCACCGTGGTGATGCATTGCCAGGCGATTGGGGACCCCAAGCCGACAATTCAGTGGGACAAGGATCTAAAGTATCTGAGTGAGAACAATAC
GGACCGCGAAAGATTTAGGTTCCTGGAGAACGGCACTCTGGAGATACGGAATGTCCAGGTGGAGGACGAGGGTAGCTACGGCTGCACAATTGGAA
ATAGTGCAGGACTCAAGCGAGAGGATGTCCAGTTGGTAGTGAAGACAACCGGTGACGGTTTCGCTCCAGAGGAATCCGGAGGTGATGGCTTCCTG
GTCACCCGAGCTGTACTGATCACCATGACGGTGGCCCTGGCCTACATAGTGCTCGTGGTGGGCCTGATGCTGTGGTGTCGCTATCGCCGTCAAGC
CAGAAAAGCCCGTTTAAACGATCTGAGCACAAAGGAAGCTGGCGGGGATCAGCCGGATGTTGCTGGCAATGGCAAAGGCTCCGAGCAGGAGCCCT
GCCTGTCTAAGCAGCACAATGGCCACAGCAAATCCAGATCCAAGTCCAGTGGAGATGCCCAGAAATCCGATGACACAGCCTGCAGCCAGCAGTCG
AGGGCCTCAAAGAAATCGGCACATATTTACGAGCAACTGGCTCTGCCAAGATCCGGGCTCAGTGAACTCATACAAATTGGACGCGGCGAGTTTGG
GGATGTGTTTGTGGGCAAACTTAAGGCTACCTTAGTCACCTCGCCCTCGGACAAGGATGCGGATACGGAAAAGCAGCACAGCAACAGTGAAAATG
GCAGTGGAGGCAGCGGAAGTGGAAGCACCACGCTAAGTACTCTAAATGAGAAGCGTCGCTCCAAGACCTCCATGGACGACATTGAGGAGATCAAG
GAGGAGGAGCAGGATCAGCACAATCAATCGGGTCTCGAGCAGCTCGTTCTGGTCAAAGCCCTGAATAAAGTGAAGGATGAACAGGCCTGCCAGGA
GTTTCGACGACAGTTAGATCTGCTGCGCGCCATCTCGCACAAGGGAGTAGTACGTCTGTTTGGCCTGTGTCGCGAAAAGGATCCGCACTACATGG
TGCTGGAGTACACGGATTGGGGCGATCTCAAGCAGTTCCTGCTGGCCACCGCCGGAAAAGTGAACACTGCCACCGCGGGCAGCTCCTCACCGCCG
CCACTCACCACCAGTCAGGTTTTGGCCGTCGCCTATCAAATTGCCCGAGGAATGGACGCCATCTACAGAGCTCGCTTCACCCATAGGTAAGTGAT
TTGAGAAGGCCAGCATTTTCATAGATCCAATTGGCAATACTTTACCTTACAGGGATCTGGCCACTCGCAACTGCGTAATTTCCAGTGAGTTTATA
GTGAAGGTATCCTATCCGGCTCTCTGCAAGGACAAGTATAGCCGCGAGTACCACAAACACCGCAACACGCTGCTCCCGATCCGCTGGCTGGCGCC
CGAGTGCATCCAGGAAGACGAGTACACCACCAAGAGCGACATCTTTGCCTACGGTGTGGTGGTGTGGGAGCTCTTCAACCAGGCCACCAAGCTGC
CCCACGAGGAGCTGACCAACGAGCAGGTGGTGCAGCGTTCCCAGGCGGGCTCCTTGGAGTGGTCAGTGGCCGAGGCGACGCCCGATAGCCTGCGA
GAGATATTGGTAAGCATCCTTATAACTTAACAATTATATTCGTACCTATTAACAAATTTCAATTAAATTAATTATATTAGTCAATGATTCGATGG
ATCCTCGCTTGGCTTAGCTATGAAATGAATGCTTAAGTCGCTGACAAACTACTGATATAATCCTTTTCTGCGTCCACTTTCAGCTGTCCTGTTGG
GTGTCCAATCCGAAGGAGCGACCTTCGTTCAGCCAACTGGGAGCTGCTCTCAGCAAGGCGATGCAGAGTGCCGAGAAGTGAGGCCAGACTGATGG
CTCGATCATGCCAAAAAGTAATTCGTAGTATTGTCTTAGTGTCTGCACGCCCGAGTTTTGCTATGCGCTCAGAAACCTAGTCTTAAGGATCGAAG
GATAACTGCGCCTGTTTAACATGCGCATTGCGCACTTGGTGGCACACAGAATGAAGTTAAGCAGCTACTGTACAAACACAATGTATGGAAATGGG
GATATCTTCGTGAATAGTATTGCGTGGTGCTGCATATTTTTAGGTATGCAGCTAAAATGTACATAATAACTGCCACAAATATGCATTTAAACCAG
TTGAAGCATTTCTAGGATTAGATCATTTCAACCTTCGTCAGCATTTAATAATCGACTTCTAAGCTAAATTAGTAAATAAAATAAAATATAAATAC
ACAAGCATATGCATCACACAAAACAACGAGCGATTTCATTGTTTTCAAACATTGAGAAACTAAGCCAAATTTTAAGTTTAGCATTAAATATAAAT
AACACACACCACCCACATATTTTATCACAAGCCTAGTTATACACTTTTTAATGCGTAAGAAACAAACAGCCGAAACAATTTTATGACTAGCCATT
TAAGCTTTGATGCATGTTTACAAAACATTTAAATAAACTCGAATAAAATAAATTTAATCAGAAGGCACAAATTTAAAGAATCAGCTTTATTTCGA
AAGTAGAAGACCAAGGGGAGAGACGAAACCTTTCGTGGGCTACTACTTTTTATGGGCCTTTCATTTGGCATGGCAAATTTGTTGAGGGTCCTTTG
GGCCTAAGCGGACTTGGCTCATTCACACTTCACTTGATTTGAAAAATGAGCGCCTATTGAATGTCGGGGTTAGGCCGTCTTGCCTCCACGTCTTT
TCCCAAAACGATTGACAAACAAACATGGCAATAAACCGTAAAGTTGCCTCGGCTTATTGGGGCTTAAAGTCGCCGCACTCTCCGATTTTTTTTC
CCGGAATTTGCTGCTCCGGAAGTTCCAGCGCCTATGTAGCCAACAAAGTTTCGTCGTGCGAAAACTTTGGCCAGGACCAAATCCAAGCAATATTT
GCATTTGAATCAGCAGCAAAAACAACACCGTTACACAATGAATTGCCATTTTCCTAGCCTAGTGGATAGGCTGCTTAGCTTTTCCTGGCACGTAC
AAATATCTGCCTGTCATGAATATCAAATGCCTTCGGAAAAAGGTTGATTGAACCAGTTGGTAGCAGGAAGTGTGGCAGAAAAAAAGAAAGAGCAC
AAATGATATGTCGAAACGGGATGGCAGAGAATTTGATACTCTATTTCACATGTAAAGGAAACCTAAAAGGATTCAAAACGTATTTACTTCCACAT
AGGCCACTTTTTAAAATTAAAACTCCTTGATAACTTTTAGAAGCATTAGCGAACGAAATAAATGGGATACCCCTAACTCAAAGGCTCGAAAGGCA
AACTGCATTCGCAATTGGTAAAGCTGCCTAAAATAAAATCCATGCCCTGCCGCACATGGCGTATGCGCAATATTTGCAATGTTTGTAATGGAACG
ACAGATGTGCAACAACAAAAGCCTAAGCTCGACACAGAACGAAAACATAAAAATGCCATTTCGCATGGCTTTCAATTTATTAATATTTTATACGG
GCCACTGGCAGAAAGGGA

FIGURE SHEET 527

(SEQ ID NO: 979)

Exon: 1001..1948
Exon: 6702..6836
Exon: 6906..7067
Exon: 14748..15637
Exon: 16609..18041
Exon: 18103..18439
Exon: 18609..19348
Start ATG: 1897

Transcript No. : CT25769
CGCGTGCAGTTCAGATTGAGTTTGAGGTTCGATTGGATTCGAGATATCCAAGTTCCTTTTGCGCTACGTTTTGTTTAGCCGAGTTTGCCCCGAAC
TAAAATCACCCACCAAAGCCGGTTCGGGATGCGATGATGCCAAGGATGCAGCTGATGCAGCCGGGCTCTTGTATCTTTAAGATACAAATTAAGTT
GATTTGTTGCGCTCGCGTTCTCTTGGGTAATTGAACCCCACAGTTGGGCTCCTTGCGCCCTCTGCCGCGCGGTCTTCGGTCTTCGGTCTTCGAGC
ATTTCGTTGCATTTTGTGTATCTAGATACCTTTGTCGGTATCCGTATCCGTCGCTTGTCAATCTGGTCGCTGATAAAAAAGCAAACGCGAACGCA
GCCACGAAACATAAACCAGCCGTCAACGGAAAATAAAAGTAAAAAGCAACAAACAGCAAGTGGCGTATCAGTTCGTGTGTTCTCGGTGATAAATG
CATTTCATGCGTTCCAACTATGTAAATAGCAATTTAATTTGAGTGTCCACAGTAAACATCAAAAAACCGCCCTGGACTCCAGTCACCACCACCAA
CAACACCATCCCCGGTGGAGCCCAGTGATCCCATTGAAACCCCGGTAAACCCCTGAAAAGGGCAGTCGTTGTCATCGTCGTCATCGTCGTCGTCG
TCGTACGTCTGTGCCATCCAAATATTGAATATTTACAAATGCGTTGAGTGCATTTTCGAGTGGCCGGCACTTACAGTGACTATCTGGTGGATGTG
CGAGTGTATTCATCGGATTGCCAGCAGCATAAAACTTCGTTTTCGATACTGATCCAATACGCGAGTGCTTATATATTTTTTGTGTCGCTAATTGA
GACCAAAGGTGTCGAAGTGCGGCGGTTATACATATACGCAGATGACTGCTAGGATGATCTCAATATGCGGCCTGGTCATGGCTTTGATGATGGCT
TCCGTTTTGGCCAGCTCATCGCGTTTCCAGCGAGTGCCCCAAAGTCAGTCCGTGGTGGAAAATGAATCCGTGAAATTCGAGTGCGAATCGACCGA
CTCCTACAGTGAACTGCACTACGACTGGTTGCATAATGGTCATCGGATTGCGTATGACAAGCGTGTCCATCAAATCGGTTCCAATTTGCATATCG
AGGCGGTGCGGCGCACGGAGGATGTTGGCAACTATGTTTGCATCGCGACAAATTTGGCCAGCGGCGCCAGGGAGGCGTCTCCGCCCGCCAAACTG
AGCGTGATATATCTTGAATCGGCCAGTGTTCAGCTGCTGGGCAGCAATCGCAACGAGCTGCTGCTCAAGTGCCACGTGGAGGGCGCCTCAGGAGA
TTTGGAACCGCTAGAGATCGAATGGTATCGCAACAGCGAGAAACTTAGCACCTGGAAGAACGTCCAGCTGGATCAGCATCGCCTGATAATCCGAC
AGCCGGGAAGCGAGGACGATGGCCTGTACCGCTGCACCGCCTCCAATGCGGCGGGTCGAGTGATGAGCAAGCAGGGCTATGTCTACCAGTCCAGT
GTGAAGTGCCTGCCCCGACTTCCTAGGCGCAAGAACGAAAAGATGATGGAGTCCTGGGACAAACAGACCTTCCTGTGCCGCGGTAAGCGCGGTGG
AGCTGCTGGACTAGAGGCACTACCCGCCGCTCCCGAGGATCTGCGCATTGTGCAAGGACCCATTGGTCAGTCGATTATCAAGGAGGGTGAGCCCA
CGGCTTTGACCTGTCTGTATGAACTGCCCGACGAGCTGAAGAACCAGCGCATTCAACTCCGTTGGCGCAAAGATGGCAAACTTTTGCGTCAAGTG
GAACTGGGTGGCTCGGCGCCCATTCCAGGTCACTCCTTCGATTCCGGCAAGGATGCTCTGTTGCGTGAGGACGCCCGTCTAGTGCTGCACAAGCA
GAATGGCACCCTAAGCTTTGCCAGCATTATTGCCAGTGATGCGGGTCAGTACCAGTGTCAGTTGCAGCTAGAAGCTCATGCTCCGATTAACTCAT
CTCCTGGCATCTTGGAGGTCATCGAGCAGCTAAAGTTTGTTCCTCAGCCCACGTCCAAGAATTTGGAGCTGGATGCAGTGGTGGCCAAGGTTCAC
TGCAAGGCGCAGGGCACTCCAACGCCGCAGGTGCAATGGGTTAGGGATGGGGAAAATACCACTTTACCCGACCATGTAGAAGTGGATGCCAATGG
AACACTGATTTTCAGAAACGTTAACTCGGAACATCGCGGCAACTACACTTGCTTGGCCACCAACAGCCAAGGACAGATAAATGCCACTGTGGCTA
TAAATGTGGTGGTCACTCCCAAATTTAGTGTGCCCCCAGTGGGACCCATCGAGACTTCGGAGCAGGGCACCGTGGTGATGCATTGCCAGGCGATT
GGGGACCCCAAGCCGACAATTCAGTGGGACAAGGATCTAAAGTATCTGAGTGAGAACAATACGGACCGCGAAAGATTTAGGTTCCTGGAGAACGG
CACTCTGGAGATACGGAATGTCCAGGTGGAGGACGAGGGTAGCTACGGCTGCACAATTGGAAATAGTGCAGGACTCAAGCGAGAGGATGTCCAGT
TGGTAGTGAAGACAACCGGTGACGGTTTCGCTCCAGAGGAATCCGGAGGTGATGGCTTCCTGGTCACCCGAGCTGTACTGATCACCATGACGGTG
GCCCTGGCCTACATAGTGCTCGTGGTGGGCCTGATGCTGTGGTGTCGCTATCGCCGTCAAGCCAGAAAAGCCCGTTTAAACGATCTGAGCACAAA
GGAAGCTGGCGGGGATCAGCCGGATGTTGCTGGCAATGGCAAAGGCTCCGAGCAGGAGCCCTGCCTGTCTAAGCAGCACAATGGCCACAGCAAAT
CCAGATCCAAGTCCAGTGGAGATGCCCAGAAATCCGATGACACAGCCTGCAGCCAGCAGTCGAGGGCCTCAAAGAAATCGGCACATATTTACGAG
CAACTGGCTCTGCCAAGATCCGGGCTCAGTGAACTCATACAAATTGGACGCGGCGAGTTTGGGGATGTGTTTGTGGGCAAACTTAAGGCTACCTT
AGTCACCTCGCCCTCGGACAAGGATGCGGATACGGAAAAGCAGCACAGCAACAGTGAAAATGGCAGTGGAGGCAGCGGAAGTGGAAGCACCACGC
TAAGTACTCTAAATGAGAAGCGTCGCTCCAAGACCTCCATGGACGACATTGAGGAGATCAAGGAGGAGGAGCAGGATCAGCACAATCAATCGGGT
CTCGAGCAGCTCGTTCTGGTCAAAGCCCTGAATAAAGTGAAGGATGAACAGGCCTGCCAGGAGTTCGACGACAGTTAGATCTGCTGCGCGCCCAT
CTCGCACAAGGGAGTAGTACGTCTGTTTGGCCTGTGTCGCGAAAAGGATCCGCACTACATGGTGCTGGAGTACACGGATTGGGGCGATCTCAAGC
AGTTCCTGCTGGCCACCGCCGGAAAAGTGAACACTGCCACCGCGGGCAGCTCCTCACCGCCGCCACTCACCACCAGTCAGGTTTTGGCCGTCGCC
TATCAAATTGCCCGAGGAATGGACGCCATCTACAGAGCTCGCTTCACCCATAGGGATCTGGCCACTCGCAACTGCGTAATTTCCAGTGAGTTTAT
AGTGAAGGTATCCTATCCGGCTCTCTGCAAGGACAAGTATAGCCGCGAGTACCACAAACACCGCAACACGCTGCTCCCGATCCGCTGGCTGGCGC
CCGAGTGCATCCAGGAAGACGAGTACACCACCAAGAGCGACATCTTTGCCTACGGTGTGGTGGTGTGGGAGCTCTTCAACCAGGCCACCAAGCTG
CCCCACGAGGAGCTGACCAACGAGCAGGTGGTGCAGCGTTCCCAGGCGGGCTCCTTGGAGTGGTCAGTGGCCGAGGCGACGCCCGATAGCCTGCG
AGAGATATTGCTGTCCTGTTGGGTGTCCAATCCGAAGGAGCGACCTTCGTTCAGCCAACTGGGAGCTGCTCTCAGCAAGGCGATGCAGAGTGCCG
AGAAGTGAGGCCAGACTGATGGCTCGATCATGCCAAAAAGTAATTCGTAGTATTGTCTTAGTGTCTGCACGCCCGAGTTTTGCTATGCGCTCAGA
AACCTAGTCTTAAGGATCGAAGGATAACTGCGCCTGTTTAACATGCGCATTGCGCACTTGGTGGCACACAGAATGAAGTTAAGCAGCTACTGTAC
AAACACAATGTATGGAAATGGGGATATCTTCGTGAATAGTATTGCGTGGTGCTGCATATTTTTAGGTATGCAGCTAAAATGTACATAATAACTGC
CACAAATATGCATTTAAACCAGTTGAAGCATTTCTAGGATTAGATCATTTCAACCTTCGTCAGCATTTAATAATCGACTTCTAAGCTAAATTAGT
AAATAAAATAAAATATAAATACACAAGCATATGCATCACACAAAACAACGAGCGATTTCATTGTTTTCAAACATTGAGAAACTAAGCCAAATTTT
AAGTTTAGCATTAAATATAAATAACACACACCACCCACATATTTTATCACAAGCCTAGTTATACACTTTTTAATGCGTAAGAAACAAACAGCCGA
AACAATTTTATGACTAGCCATTTAAGCTTTGATGCATGTTTACAAAACATTTAAATAAACTCGAATAAAATAAATTTAATCAGAA
(SEQ ID NO: 980)

Start ATG: 897

MTARMISICGLVMALMMASVLASSSRFQRVPQSQSVVENESVKFECESTDSYSELHYDWLHNGHRIAYDKRVHQIGSNLHIEAVRRTEDVGNYVC
IATNLASGAREASPPAKLSVIYLESASVQLLGSNRNELLLKCHVEGASGDLEPLEIEWYRNSEKLSTWKNVQLDQHRLIIRQPGSEDDGLYRCTA
SNAAGRVMSKQGYVYQSSVKCLPRLPRRKNEKMMESWDKQTFLCRGKRGGAAGLEALPAAPEDLRIVQGPIGQSIIKEGEPTALTCLYELPDELK
NQRIQLRWRKDGKLLRQVELGGSAPIPGHSFDSGKDALLREDARLVLHKQNGTLSFASIIASDAGQYQCQLQLEAHAPINSSPGILEVIEQLKFV
PQPTSKNLELDAVVAKVHCKAQGTPTPQVQWVRDGENTTLPDHVEVDANGTLIFRNVNSEHRGNYTCLATNSQGQINATVAINVVVTPKFSVPPV
GPIETSEQGTVVMHCQAIGDPKPTIQWDKDLKYLSENNTDRERFRFLENGTLEIRNVQVEDEGSYGCTIGNSAGLKREDVQLVVKTTGDGFAPEE

FIGURE SHEET 528

SGGDGFLVTRAVLITMTVALAYIVLVVGLMLWCRYRRQARKARLNDLSTKEAGGDQPDVAGNGKGSEQEPCLSKQHNGHSKSRSKSSGDAQKSDD
TACSQQSRASKKSAHIYEQLALPRSGLSELIQIGRGEFGDVFVGKLKATLVTSPSDKDADTEKQHSNSENGSGGSGSGSTTLSTLNEKRRSKTSM
DDIEEIKEEEQDQHNQSGLEQLVLVKALNKVKDEQACQEFRRQLDLLRAISHKGVVRLFGLCREKDPHYMVLEYTDWGDLKQFLLATAGKVNTAT
AGSSSPPPLTTSQVLAVAYQIARGMDAIYRARFTHRDLATRNCVISSEFIVKVSYPALCKDKYSREYHKHRNTLLPIRWLAPECIQEDEYTTKSD
IFAYGVVVWELFNQATKLPHEELTNEQVVQRSQAGSLEWSVAEATPDSLREILLSCWVSNPKERPSFSQLGAALSKAMQSAEK*
(SEQ ID NO: 981)

Name: off-track
Classification: protein_kinase
Gene Symbol: otk
FlyBase ID: FBgn0004839

Celera Sequence No. : 142000013384084
TTTGCATGTGTTTCAAACTACATATAAATATTGGGAAATATTCAATGCTCTGCTCGGCGCTTTTGCTTTTATTTTGTATTGTTATGTGATTTCTG
TCTTGGTTATTTTTATTCGATGCTCTTCCAAATCTATAGATGTGTAAGTTAATCTGATTGCTGAATCATCTTTATATCTTTTTTTCATCTCCCGA
AGAAGAATCATCTTCTATCGTCCGCCTAAACGTATAAAATGCATGTAAATCTAAAATCTTATTTAATCAACTAACTCTGTCACGCCCATCCCTTC
GTTATGTGTATATATATATATATAACTTCTATATATATATATATATAATGCTCTGATTATGATTTGCAGTAACGAAAAGTGACCAGAAGAAAGAG
TATTAATATCTAGTTCTTTTTCCTTCCGCATAGGTTTATATTTATATTTATATATATATATATATTTATATATATATGTATTTATGTATATATAT
GCATATACGTAAGTGTAAAGTTAAGTGTACTCGATTCGGTCTTCGGTGTTATATATGGATATTATCTTCATAAAAGCCGCGTGCCGTCAGTGGCA
TCGCCAGACGGCCATGCCCTCGCCGCCCATCCAGAGATCCGGGAATCACCGCCAGGCGGTCCGCAACCGTCTGTCCGCCTTGCCACGTCCAGCCG
ACGTTAGATTGGCCCCGATCTCCAGGCTCCGCACATCCCGGCAGCCAGATGGTGAACCTCTCCTCGATCGAAGCGATAAAGGCGAGGCAGGCGCC
TTAAAGATCACGGATTACCTGGAAACCGAAGCCCGCCAGCTGGACAGTTGTTGGAGTGGTTGGTGGCGGATGTTGCAGGCGGACAGGCGACAACG
GCCGCCCGGTGGTATTCCCTCCTTCCAAAACGAAGAGGTGGACCCGGATTTGGAGAAGAAGGAGCACGGCGCAACGTACACGGTGACACCGACGA
CGCACAGGCGAGAAAAAAAAACTTAAAAACTAATTGATAATAGTAATAATAAGAGTTATAAAATAATTTTTAAGCATTACAGTAATGTTGTGTGTT
GTTTTGTGTGTGGTGTTTTTCTTATCGACAACGTCATGCTGACGATTCGATTGAACAACAAAAGGATGATAAATGTATACATGTAAATATGAATG
ATAGATTGGATCAATGTGTCGCTGGTATAGCTCCTTGGCGTGCACCTCTCCTACAACGGTACGTGAATGGTCTACTGTTCGGGAATGGACGACAG
TGATCGAATCTGGCGTTCCTGCTGATCCACCTTAAGCACGCTCGCCACGGATGCGGCGCGCCAACTGGATGTCCTTAGGCATGATTGTCACGCGC
TTGGCGTGGATAGCGCACAAGTTGGTGTCCTCGAAGAGACCCACCAGGTACGCCTCAGATGCTTCCTGTAAGTCAAGAGAAATTCATATGAGTTG
GATAACCAAGTTCCTTTTAGATATTAGTAGCCCCCCCTTCATAATCCCATGAATCCTGTCATTTTTAGTTAAGTTAAGCCACTCTGATTCTTTGG
AGCATAATTCTCACCTGCAAGGCACCGATGGCAGCCGACTGGAAACGCAGATCGGTCTTGAAATCCTGAGCGATTTCACGAACCAGACGCTGGAA
GGGCAGCTTGCGGATGAGCAACTCGGTCGACTTCTGGTAACGACGGATCTCACGAAGAGCCACAGTTCCGGGACGATAACGATGGGGCTTCTTCA
CTCCGCCGGTGGATGGCGCCGATTTACGGGCAGCCTTGGTGGCTAGCTGCTTACGAGGAGCCTTTCCTCCGGTCGACTTACGGGCAGTCTGCTTA
GTACGAGCCATGTTTTCTTAGCTTTTTTTTTAAACTGCAATTAAGAGAATGGGAAATGCAAATGTTAGATTTTGCGCGTTCCAGATTGACACAG
ATTAAATAAACACTTCTACAATCATTGTTTGGTTGGTACCCAAAATAAACACGCTGATCCTCGCCAGATGAGAAAGACAACTCGATGAACTGGGC
ACAAACTCTAAACTATTCGTCCAGCACAGGCGCAGTGCACGATGCAATTGGCCAGGATACGATTGTGCTGTGTCGTGGACTCTTGACGGATATAC
ACGGATGGATATCGCTGGGAGCCAAAGTTTGGACCGATGCACAGCGCCGAAGCGCTGGCGGCCAACTGACGAGGAACTTTGGTTCGTGGTCATAA
CGATAACGAGGGTTGAAGGTGAAATTTTTTTGAGGCAGCTGCCTGCTTTTCCTTCTTGCCCCCCATTTCAAATATTTTCCCATCTTCTGGGAACG
AGGCACTCGAGAAACTTCCACTTCAGTGGCAAAGGAATAAATCGTGCCTCGGCAGCAAAACACTCAGAAAAATAATAGTGTGATCCATATTTATA
TTGGTGTGCAAATGAAGCTTAGCTAAGATGATTCTAAAGTTTTCACATTACTTATAATTAAAAAAACTTAAGAAACATTTCTGATAATTCATAAA
GGTGGTCCATAAAAAAACCCTAATTTATCCGTTCTAAATAGCAATAGGAATACCATCTAATTCTCAATTGGTGGTATAGATATATTACATCTGCT
TTTCTCGCTGTGTAGTTGTTCCACGATGGAGGACCACTTGAAAATCTCATTTCTTTTCTTCGCGGGCAAACATCGTGAGTCGCCGTTTTTTGTGT
TCCCCTTCTTTTTATGTACAGCCTCTTGAGTTTTTTTCGCGCTTTATGCGGAATCAATCACGCTGAAGTAATGAGTTGTAGTTTTCAATTTATAA
TTACTTGTGCAGGCAAGAGGAAAATATCAAATAAAAGGAAGCCAAAGAAAACGAAAAAAATTCTTCGACTGGTAGCGCCAAAAGAGTAAACATAA
ACAAAAGGAAGGAAAATCAAGCGGTAAAAACTTGGCGCGCATTGAAAGGCGGCAAGTCGAAGGGAGATGCCTATAGGGGCACGTTCGCGTTAGAA
AGAGAAGAAAGGTGTGCCAGCAGTTAATTGCGTCGTTTCTCCGCTAAACAGCATGTGTGTGCGTGTAGATGTGACAGCTGCACATCCTCACAAAA
GAGAATGCCAAAGGAAAAAGAAAATAAAAAGCAATTATGCAATAACATACGGGAAAAGCTGGCGGTGGGAAAGAGAGATGGCACACACTGCGCAT
GACAAGCGCAGCCATGCACATTTGCATTTGTTAACCAATGTGCGTGTTTAGTATACACACACATCAACGCGCGTGCCACTTAAGAAATAAATAAA
TAACTTTTATATGTTTATGCCAACCAGCATAAATACGATTACTCATACTTTTTGGCGCCAGTTTTCGCACATTGGCAAATCGTTTTTATTTATTT
TTTTAATTTCTTTTTGCCAATTTCATCAACGACTGCAACTTTTTTATTTCTTGCTATTCTCCTGCTTGGCGGCCATTTTGGAAAAAAAAAAAAAA
GCAGCGCACCTCACCATTACAACTAAAACAACAATGCAACCAACAGTCGTGCGAATACGAGACCTCTCACATCTTCGTGTATTTGTGTATGTATC
CACCAGCGAGAATGCGCCTGTGTGTGTGCGGTGAAAAATAGGGCTCCGCTGGACGGCCGGCGGAGCCCCAAAAACGGCAAAACATAAACTCAGGC
GATTCACAACGAAAAAAAAATTTGGAAAACAGTGCACACACGCACATATTCAGCGGCCACAAGCACGTGCGTTTTAAGAACCACACTTAGTATTA
TAAGTATTTAGCAATAAAAAAAAACTCACCGTTAAACACGGAATAAAGTTATTCTTCACAATTTGTCACTTTCAACACGAGACGAACAAATTCGG
ACGAGAGAAATTTTCACAATGATTTCGTTTCGTTGAGATCTAGAGATGGTAGCCTAGTAGGCGAAGGCCTACTTCGATTGTATTCGATTACACTC
GATTGTCTGACAAGACCATGCCCGCCAAATAGTTTGGTTCTGTTCTTTGCTAATTACATTTTTATAACTTTTTAAAATTTTTTTAACTCCAACCT
AAGATTAAAAATGAATATGTTTTAATGGGTTGGACTCTGCTAATTTTAATGAAATATAAGCTTCATTAAGCAAAAAAAAAGCCAAGTTCTTTTAT
GGATTGTGGGTTTCTCTCTGCAGAGAACTTTATTTTAGTGCATTGTGTGTTACATTTGAGTTGAACGAACGTGCATACTACTGCGACTTCTTGTC
CTCCTTGGCGGCCCTGCCCACGGGCTCATCCTTGAAGTGAAGGAACACGAATGAGAAGACAAACACGCCGATCATCATTGAGAAGGCGCTGGTGT
AGTAGGGGAATGCGCTCGGGATAAAGCGCTCGTACTGTGTGTGCTCCAGCGGACGCACCGACACCTGGGTGGTGCTGTACAGATGCGTGTAGCCC
ACGCGATTGTAGTCCACCTTGAACTGATAAACGCCGTAGACGTCGGGTATCTTGAATTTGGCCTGGTAGGCGCCCGTGTTCGTTTGCTTCAGATA
GGTGCGGACGAAGGGATCGATGCGCACGAACTCCAGTTGAATGTCGCTGGCCTTAAAGGCGCGCCACTCGCCCTGCACCAGCTCCTCGATGCCGA
TGGTGTAGACGACCGGATCGGTGATGGTGTACGCCTGATCCGGTGGCAGCAGCTCGCCCTCCTTGTGATGTTGCACGGATGCCACGCGCAAGCGG
CCAGTCTCTCCAAATACCCACTTGCTAATGGACTCGGCCACGTCGCGATTACCGGCCAGCTTGTGGAACACACCGCTCTGTGCGTACTGCACGGC
CGTTGTGAAGCTCTCGTCAGAGAAGAAGAGCAGCGAGCCGGAGAACACTACGCGGGCATTGTTCCTCGCCTGCAGGGCGGCGATTAGCA
(SEQ ID NO: 982)

Exon: 3839..3735
Exon: 1840..1535
Exon: 1395..1001
Start ATG: 1816 (Reverse strand: CAT)

FIGURE SHEET 529

Transcript No. : CT25818
ATCTCAACGAAACGAAATCATTGTGAAAATTTCTCTCGTCCGAATTTGTTCGTCTCGTGTTGAAAGTGACAAATTGTGAAGAATAACTTTATTCC
GTGTTTAACGTTTAAAAAAAAAAGCTAAGAAAACATGGCTCGTACTAAGCAGACTGCCCGTAAGTCGACCGGAGGAAAGGCTCCTCGTAAGCAGC
TAGCCACCAAGGCTGCCCGTAAATCGGCGCCATCCACCGGCGGAGTGAAGAAGCCCCATCGTTATCGTCCCGGAACTGTGGCTCTTCGTGAGATC
CGTCGTTACCAGAAGTCGACCGAGTTGCTCATCCGCAAGCTGCCCTTCCAGCGTCTGGTTCGTGAAATCGCTCAGGATTTCAAGACCGATCTGCG
TTTCCAGTCGGCTGCCATCGGTGCCTTGCAGGAAGCATCTGAGGCGTACCTGGTGGGTCTCTTCGAGGACACCAACTTGTGCGCTATCCACGCCA
AGCGCGTGACAATCATGCCTAAGGACATCCAGTTGGCGCGCCGCATCCGTGGCGAGCGTGCTTAAGGTGGATCAGCAGGAACGCCAGATTCGATC
ACTGTCGTCCATTCCCGAACAGTAGACCATTCACGTACCGTTGTAGGAGAGGTGCACGCCAAGGAGCTATACCAGCGACACATTGATCCAATCTA
TCATTCATATTTACATGTATACATTTATCATCCTTTTGTTGTTCAATCGAATCGTCAGCATGACGTTGTCGATAAGAAAAACACCACACACAAAA
CAACACACAACATTACTGTAATGCTTAAAAATTATTTTATAACTCT
(SEQ ID NO: 983)

Start ATG: 130 (Reverse strand: CAT)

MARTKQTARKSTGGKAPRKQLATKAARKSAPSTGGVKKPHRYRPGTVALREIRRYQKSTELLIRKLPFQRLVREIAQDFKTDLRFQSAAIGALQE
ASEAYLVGLFEDTNLCAIHAKRVTIMPKDIQLARRIRGERA*
(SEQ ID NO: 984)

Name: Histone H3.3B
Classification: DNA_binding
Gene Symbol: His3.3B
FlyBase ID: FBgn0004828

Celera Sequence No. : 142000013385192
TTTCCGCTGCCATCTGCAGCTGTAGCTGCCTAACAAATGCAATTAAAATCTTTGCGCAAGAAAATTGTTGCAGCAGGCACGCAGAGATACTCGTA
CTGTATGTGCTGCAATAGTTTGGTGGCAGCAACGGGGCGGCAGATAACATATTGCCCACGTCCGGCTGAAATTGTACGGACAAGGCGAACTCAAA
AAAAAAAAAAAAAAAAAGGAATCCCTCAAAAGGAGAACCAAGAAAAATGGGATTTATCTCTGGCCAAGCTCCAGCCATACAAATCTAATTTAGAC
CACACGACGGCTTCAGATATTTTATATTCCCCACTCAGTTGCGGTCCATCCTGATCTCCTCCAGCTTGCTTGATGAGCCCAGCCGTTGGCCAAAT
GAAATTATTTATGGGCAGTCCTAGGTCAGTGAGAATTTGGTTTTTAAGGGTTTGAACTTTGCGGCTCAACAATGCCTGTGATTTTTTTTTTTTT
TATTATTTTTTTGCATTGCATCCATTAGAGAAAGCACTCCTTTGGCATTCTACTCAGCTACTTGCCACATAAATATCTACGGAGGGTAGCTAACT
AGTCCTTATCTCAACTTCCCCATTTATCCTCGCCGCAAGTGCACTTTTCCTGCTGCTAATTAAGTTGCAAGGCAGCTTTCTCAGCAGGCGTTGCA
CGAAGTAGATAAAAGGAAAAGCCCCCGATTTGCAGACACTATGCTGGGAAAGATATATATATATATATATATTTTGCCAGCATTCGCTAATCGGCTT
AGGGCAGCCACCATGCGACCACAACAACAACAACAACAGCAGCAGCAGTGTGCTCCATGCAATATTTAATCACATTAGTTGATGGGGTAACGGCC
ATGTACGCAACAATTTACAACTTGCATTAATTATACGTCTAGTTGGACAATGGCGCCTCTAACTATCCCACTCTAAATGTATCTCTATCTCTATC
CTTATTTGCAGGGGACACCCGTTGATAATAAATTATTAATGCATCTGCTGGGAAGGCGGCACTGCACGGCTGTCCTTGGCAGCAAATCCAGTTGC
AACATCGGTGAGTGACGGGCGGCAATCACAAAGGACTTGCAACAGTTGCCGTTGCTTCTGCTATTGCTGTTGCTGTTGCTGTTGCAACAATGGCC
AGTGGCAACAATGAAACTGAGCCGCTCTACTGCGGCAGCGGCATGGATAATTTTCATACAAGGTAAGCGACTTTCACCAATGTCACGATCAAGGC
CAAGGGGCTTTTCCACCAGACATGGCGACAACAATACCATAAGCCAACAGTTGGGGGCGTGGTCGGGGGCGGAGGCGATGGTGGCAACATCATAG
CCATTAGCTGCTGGCGCAAGGGAACCGTTCAAAAATCGATTATCGCCCCATTTCGGGGGAGCTTCTATTTTGATTTGCCGTACAATTTTCTCGGG
CGATTAAACGACGAAGCAGAACGAAAACAAAAAACAGATTTGTCAACAGCAAGGTCAACAATTGATGGCTGAAATCAATTTAATTGACCATATCC
TACGGGCCCTCCAAGTGGCCATCTGCTGCACCTATAAAAAAGTGAATCCGGTCTGCGATTATTTATATATTCGTTGCATGGCAGGCGGTCGTAAA
ACCTCGAGATGATGATTAAAAGCGGCCCTAAAAACTTAATGGCGGTTTAGGAAATTCAATTCCTGTAATTTAAGCCGAGTCACCATTCTTCGAAG
TTCTTACATGTAAGCGATAATAAATAGTTAAGTCAATTGGCCAATAAACCTATTAATATTGTGCATTTACCACGATTAGACTTTGATTAAAGTGA
CAATGCTGATTTCTGTAGAGGAAATCTAGTTCTAGTCTTCCCACAAAGCTATTTAGTTACTCTTGAATAAATATGTTACTTTTCTTTTGCCAAAA
CCAACAGAATTTTAAATTTAATAATTTGGATTTTTTGCAATAAACTGTACTGATTAATGGGCCACACAAAAATGTCTAGTTTATTATGGAGCTCT
TGGTTTCATAAATTAAGAACATAATCCAATCGGCATATAAATCATTGATAGCAATTTATTTTCCGTGATGAAACTGTGCTCCGTGTGAACTGCGA
ATTACTCATTCTACGGTTGCAAAAAAAGCCACCAACGGTCAACATTTAGACCAGGACTTTTAGTTTTAATTAGAGCCAGCCTGGCCAACAGCAGT
GTTAATGACCACAAAGTGGCTGGCCACAGGATCAGCATCCCAGAATGCGATGCCGCATTTGCTTTAATTAAAGGTAGTAGCTGGAGTTTGAAAGA
TGACTGTATGGCAATTAGATGTGTAGCCAGAACACTTGGCCATTTACTTTTGTGTCAAAGTCGTGCCAAATTGCCAGCGGAGGCGACACTTGACG
CTGTCACGCCCCAGACAGACGCAGACCGGCCCAAAAGCACCCACTCAGCCGTCTCCAGGCGCCACTCAAGCGGCAAAGGAACGCCAAAACACTAG
GACACAGAACGCCAGAAGACTCGAAAAAAAAGTATAAAATTCAAACGCGTATACAATTCAATGTGTCACATCGAAGAAGAACCCTTTCTCTGGCG
GCAACGTGACGTATACGCAATATTAATGGCAAAGCGAAAAGGGCCTCAAAAGCTAACGAAAAACCGCAGCATAACACGCACAAAACAAGCAATTA
ACATAAATAATAAAGAACGCACAAAGGCGTTCGGCTCTCCGTTGCCAAAGAGAAAAGCCAACGAAAGGAATAAAAAACGCCAAAAAGCCCGAAAA
AAAAACCGAAGACCCAAAAAATGTGTAAAATTGATTTCGGAAAATATTTAATTTACCAAATGCATGCTCGCTTTTTGCGGCCGTGTACGCCCCGA
ACAAATAAAACAAATAGGCACACATCGTCTGGCATTTCATGTTAAAGGCTTCTCATGCTGATGGACAGGATACAGAAAATATATATACGAAGTGA
GGTGTGTGTCTACGTGCCACAAAAACAGCGAAATTGAAACGCTTTCCGAATGCCGGCGACACTTTTTGGCGGCACAACCCTCGTCTTGTCGACCA
ACTCCTGGGGAATTTACAACTCCATTCATCAAACTCACAAAAACTTTGCCTGGTGTACGGTCTTGGGTTCGTCGTCGCAGGATTTCACCTGGCTA
AAAATCCAGACTCCCAGCCATCCCTGAGTCTAATTTATGGCCTTTGATAATCCATGTTGATGAATGGCGGCAACGACAACAACGTCGACGACATG
AATGAAGTCCTGGAATTGTTTTGCACCAGGATGGCATCGGGGCTCCAGGTGGGACGTACTGGCTCAAAGTTATTGGCCCAGAAATCAGGCATAGT
TAGCTGCCGAAATGAAACCCAAATACCGAGAAAACTAGGCAAAACAAACAGTAGTACACCGGAAATGCATATCATTGTAAAAACTACATCAGTTT
ACCTAAAAGGCTTGGCTTTTAAGCTTTCACATTTATAAAATATTGAAAATGCATATAAAAGTATGAAATTAATTCCCTTTTGTCAATAAACTTTC
TTTCTTTCTTTCTGTGTAATATGGGGGATACCGGTTTTTTTTTTTTTCAATGAAATCCCTTCGAAAGGTATAAGTTCAGAATCGAGAGTTTTAT
GCCAAGTTGGGCACAGTTTTTTTTTTTCCCCAGCTACCTAAAATAATAGAGACATTTTCCTCCCACTACAACTGATTGCATTGCCGGTGCAGAAAG
TTTTTTCAGTTGGTTCGGAAAAATTTGGTTCGCAAACAAATTAATATGAACTGGCAAGCATTTTTCGGGCAAAAAGCTCTCATCTATGTAGATTG
GAATGGAAATTCCGGCTAGAATTGCATAAGACCACCTGCAGTGTGGGCTAACATGACTAAAAAGTTGTCCACAAATTTGGCTTAGATTCTCCAAT
AAAACTGTCGTTCGGCCAGGAATCCCCTTTTTTGTTTCGAGTGAATGGGGAATTTCGCACGACAGACAGCAATAAAGAATTTAACTAAAGTCCTG
ACACCGACAGCACCAGCAGGACGCACACGTGTCACTCCATTTGGAGAGCTTGGAGTATATTAAACATTTTTTCCCCACCAGTCAGCCGCAGGACT
TGCATCGGTCTCGCCTCGCATTTTCCTATATAAATTTTATGCTAAGTCTAATTTGTTGGCTGCAACTTGCACAAAGGCAAAAAATAAACAAGGGC
GAAATGCCGAAAGCCAAAACCCAACCGAAACCGTTGAGGGCTGCCTCGCTTTTTTCCTGTGCCGAATTCCCTAAAACTTTGCACATAAATTTGAG TCCTGCGCCTGGGCTTTTCCTCTTCCACCTTTTTTTTAGCCTCAAAGCGCTCGACGAAAACTAAACAAAAGCTGGTAAAATGTTTATCCCAGAA
GGGGGCGGTGTGGGCGTGGCTTGCTTAAGCCCTAGACACCCGAGAGTTTATTGCCTCAGTGTTGCAAACGCTGCTGCTTGGCAAGTCAACGGAAA
TGGCTTTCGGATGGTTTATTGCCTACTTTTGCTGCGAGAAAGCGGACTAGACATGGAAGTAACAAATTGGTTAAGGCTAACTAGAGCATAATAA
CAGAAACATCAGAAACATAATTTGGGAAATGCCTGCCACTCACCGACAACATTTCGATTTGTGTCTTTATTACACTTCTCTGCCGTGATGGGTTA
TAACTTTTGGATCCTTGCAGAGAGTTGGGAAATTGCTTAAAAATAAAATTTGTTTAATTTAATTTGAGGTGGTTTTTCAAACAATTTTAATGGAT
TAATAAGTTTAGGAAGTTAAGTATATACATCTATCTATTATACCATCTTCAAATATTGTTGAATTGAAGAGATAACTCGGAGCTAATCCCATATT
TTTCATTTTTTTCAGCTACAAGAACATGCATGGCTATGTTTCGCTGGTGGTCTGCATCCTGGGCACCATCGCGAATACCTTGAATATCATTGTGC
TAACCCGACGGGAGATGCGCTCCCCCACGAATGCCATACTCACGGGTCTGGCCGTGGCCGACCTGGCAGTTATGCTGGAGTATATACCCTACACC
ATACACGACTACATCCTGACGGACAGTTTGCCGCGGGAGGAGAAGCTCAGCTACAGCTGGGCCTGCTTCATCAAGTTCCATTCGATTTTCGCCCA
GGTTCTGCACACCATTTCCATTTGGCTGACGGTGACCCTGGCTGTTTGGCGTTATATAGCGGTGGGTTATCCGCAAAAGAATCGCGTATGGTGCG
GTATGAGAACCACCATAATAACGATAACCACCGCTTATGTGGTGTGTGTTCTGGTGGTGTCGCCGTCGCTCTATTTGATCACGGCTATAACCGAA
TATGTCGATCAGTTGGATATGAATGGCAAAGTGATAAACTCCATTCCCATGACCCAGTACGTAATCGATTATCGTAATGAGTTACTGAGTGCCAG
GACGGCTGCCCTGAATGCCACGCCCACCAGTGCACCACTGAACGAAACTGTGTGGTTAAATGCGAGCACCTTGCTGACATCGACAACCACCGCTG
CACCACCCACGCCATCGCCAGTGGTGCGAAATGTTACTGTCTATAGGCTATACCACAGCGATTTGGCGTTGCACAATGCCTCGCTGCAAAATGCC
ACATTTCTCATATACAGTGTAGTGATTAAGCTGATACCATGCATAGCACTCACCATTCTGTCGGTTCGATTGATCCTGGCCTTACTGGAGGCCAA
GCGGCGGCGGAAGAAGCTCACCAGCAAGCCCGCCACTCCGGGTGCCAGTAATGGAACCAAATCACCGGCCAATGGTAAAGCAGCGGATAGGCCCC
GGAAAAATAGCAAAACTCTGGAAAAGGAAAAGCAGACGGATCGCACCACGAGAATGCTGCTGGCGGTGCTACTCCTCTTTCTCATCACTGAATTT
CCACAAGGGATTATGGGTCTGCTGAATGCTGTGCTCGGAGATGTCTTCTATCTGCAGTGCTACCTAAGACTGAGTAAGTAAATATGTACTATGCA
TAACGCCACAGTAAATTCCACAGATTCCCATTTCACTTTAAGATGTAATAACCCAATGCCTTTTGCCTTTTGCCACCAGGTGACCTGATGGATAT
CTTGGCCCTGATCAACTCCAGCATCAACTTCATTTTGTACTGCTCCATGAGCAAGCAATTCCGCACCACGTTCACGCTGCTCTTTCGTCCAAAAT
TCCTGGACAAGTGGCTGCCGGTGGCGCAGGACGAAATGGCAGCTGCTCGAGCTGAACGCTCTGCGGTGGCACCGGTCCTGGAAAAGGGACGACAG
CAGCCGCAGGTGGTGATGGCCAGCACGACCACCAACATCACGCAGGTGACAAATCTGTAGCACAGGAGGAGTCGTGGTCGCCGAACTTTGCTCAG
TCGCCTGCTGAGTGTCCTGAAACGCGGCAGAAGGCGCTCCTCCGGCGAAGGAGGAGGCGTGGAGGAGGTGGTGCGCCGTTGGCCGGCAACGATG
CGGTGGAACCAGCGTTCCAGGCCATCGTGGTGGTGGTGGACAAGGTGAGCGGTGCCACGGAGAATCAGCTGTACACCGCCGAGCAAGCTCGTATT
GTGACGTAGTAACCCTGATAGTAGTACATATTATATGCCTAGTTATCCTTGTAAAAAGTAAACTAGTTGTGTAAGAATCGCAGATAACCACAAGT
TATGTGCATACTTTGGTGGGAAATCGTAAAACCCGTACAGTCATAATAATAAAATGCTGGTTCATCACTCATACGCACCGTTTGACTTCACTCTA
TTCCACATTCACAGTCAAGTAGGAGCTGTAAAAATGCTGTGCATAAACGAGCTCGTATACGCTACAGCTGGCGTCACAATAATAGTTACCATTGG
GTTGGCTTCACAACATAGATCAAAGTCAAAAAATATATAGTTTTGTAAAATGTTTCATAAATCTATCTTCATATTTAACTAACACAATTCAGAAA
CTTTCGCTTGCATGGAAAATGTTTTATTTTCCCCACTTGACCCAATTGTGCGCAACTGTTCAGCTTTTCGGCATGAATCAAATCAAATATAGTAA
ACTTTTGCATCTTTTCCACTTTGATCCCATGCGTTTTCATGTTGATTTCATTCGCATAAAGTATGCAGCACACGTACTCACTCAAAACTACGAAT
TTTCGGCAACGATTTGAGCAGAATATTTGCCATTTGTTGTACAGATTATATATACACACACACACACTTATGTCCGTATCTTTAATAATGGCAAT
TAAGTCCTAGAAATTTTGACCTGATATTGATGCAGGCATTGGAAAAATAAGTGGCAGTTGCAGTGCGGTGCGTTGATAAATGAAATACTTTGCGA
ATTCTATTATTGGAAATCGCAATTTGGGCTGTGAATGAAATTATAGTTTTCTTGAACGCAATTGAGAATTCAGTTCCGTTTCGTGGGTTACTGAA
TTTATGGGAAATAATTTAAGGCAGTCACTGCAGCTGACCGAATAATCCAATGAAACATTGCATAAACAGTTTGCAGTTTTTCCACACTTGCGAAA
ATTGTAATTGCAAATCGCTTAAGCCCCACGACGAATGACAAATGGCCAGCGAACGCATA
(SEQ ID NO: 985)

Exon: 1001..1202
Exon: 4861..5963
Exon: 6065..6282
Exon: 6331..6564
Start ATG: 1135

Transcript No. : CT25824
GGAAGGCGGCACTGCACGGCTGTCCTTGGCAGCAAATCCAGTTGCAACATCGGTGAGTGACGGGCGGCAATCACAAAGGACTTGCAACAGTTGCC
GTTGCTTCTGCTATTGCTGTTGCTGTTGCTGTTGCAACAATGGCCAGTGGCAACAATGAAACTGAGCCGCTCTACTGCGGCAGCGGCATGGATAA
TTTTCATACAAGCTACAAGAACATGCATGGCTATGTTTCGCTGGTGGTCTGCATCCTGGGCACCATCGCGAATACCTTGAATATCATTGTGCTAA
CCCGACGGGAGATGCGCTCCCCCACGAATGCCATACTCACGGGTCTGGCCGTGGCCGACCTGGCAGTTATGCTGGAGTATATACCCTACACCATA
CACGACTACATCCTGACGGACAGTTTGCCGCGGGAGGAGAAGCTCAGCTACAGCTGGGCCTGCTTCATCAAGTTCCATTCGATTTTCGCCCAGGT
TCTGCACACCATTTCCATTTGGCTGACGGTGACCCTGGCTGTTTGGCGTTATATAGCGGTGGGTTATCCGCAAAAGAATCGCGTATGGTGCGGTA
TGAGAACCACCATAATAACGATAACCACCGCTTATGTGGTGTGTGTTCTGGTGGTGTCGCCGTCGCTCTATTTGATCACGGCTATAACCGAATAT
GTCGATCAGTTGGATATGAATGGCAAAGTGATAAACTCCATTCCCATGACCCAGTACGTAATCGATTATCGTAATGAGTTACTGAGTGCCAGGAC
GGCTGCCCTGAATGCCACGCCCACCAGTGCACCACTGAACGAAACTGTGTGGTTAAATGCGAGCACCTTGCTGACATCGACAACCACCGCTGCAC
CACCCACGCCATCGCCAGTGGTGCGAAATGTTACTGTCTATAGGCTATACCACAGCGATTTGGCGTTGCACAATGCCTCGCTGCAAAATGCCACA
TTTCTCATATACAGTGTAGTGATTAAGCTGATACCATGCATAGCACTCACCATTCTGTCGGTTCGATTGATCCTGGCCTTACTGGAGGCCAAGCG
GCGGCGGAAGAAGCTCACCAGCAAGCCCGCCACTCCGGGTGCCAGTAATGGAACCAAATCACCGGCCAATGGTAAAGCAGCGGATAGGCCCCGGA
AAAATAGCAAAACTCTGGAAAAGGAAAAGCAGACGGATCGCACCACGAGAATGCTGCTGGCGGTGCTACTCCTCTTTCTCATCACTGAATTTCCA
CAAGGGATTATGGGTCTGCTGAATGCTGTGCTCGGAGATGTCTTCTATCTGCAGTGCTACCTAAGACTGAGTGACCTGATGGATATCTTGGCCCT
GATCAACTCCAGCATCAACTTCATTTTGTACTGCTCCATGAGCAAGCAATTCCGCACCACGTTCACGCTGCTCTTTCGTCCAAAATTCCTGGACA
AGTGGCTGCCGGTGGCGCAGGACGAAATGGCAGCTGCTCGAGCTGAACGCTCTGCGGTGGCACCGGTCCTGGAAAAGGGACGACAGCAGCCGCAG
GTGCACAGGAGGAGTCGTGGTCGCCGAACTTTGCTCAGTCGCCTGCTGAGTGTCCTGAAACGCGGCAGAAGGCGCTCCTCCGGCGAAGGAGGAGG
CGTGGAGGAGGTGGTGCGCCGTTGGCCGGCAACGATGCGGTGGAACCAGCGTTCCAGGCCATCGTGGTGGTGGTGGACAAGGTGAGCGGTGCCA
CGGAGAATCAGCTGTACACCGCCGAGCAAGCTCGTATTGTGACGTAG
(SEQ ID NO: 986)

Start ATG: 135

MASGNNETEPLYCGSGMDNFHTSYKNMHGYVSLVVCILGTIANTLNIIVLTRREMRSPTNAILTGLAVADLAVMLEYIPYTIHDYILTDSLPREE
KLSYSWACFIKFHSIFAQVLHTISIWLTVTLAVWRYIAVGYPQKNRVWCGMRTTIITITTAYVVCVLVVSPSLYLITAITEYVDQLDMNGKVINS
IPMTQYVIDYRNELLSARTAALNATPTSAPLNETVWLNASTLLTSTTTAAPPTPSPVVRNVTVYRLYHSDLALHNASLQNATFLIYSVVIKLIPC
IALTILSVRLILALLEAKRRRKKLTSKPATPGASNGTKSPANGKAADRPRKNSKTLEKEKQTDRTTRMLLAVLLLFLITEFPQGIMGLLNAVLGD

VFYLQCYLRLSDLMDILALINSSINFILYCSMSKQFRTTFTLLFRPKFLDKWLPVAQDEMAAARAERSAVAPVLEKGRQQPQVHRRSRGRRTLLS
RLLSVLKRGRRRSSGEGGGVGGGGAPLAGNDAVEPAFQAIVVVVDKVSGATENQLYTAEQARIVT*
(SEQ ID NO: 987)

Name: G-protein coupled receptor-like
Classification: G_protein_linked_receptor

Celera Sequence No. : 142000013384084
ATGCAATAACATACGGGAAAAGCTGGCGGTGGGAAAGAGAGATGGCACACACTGCGCATGACAAGCGCAGCCATGCACATTTGCATTTGTTAACC
AATGTGCGTGTTTAGTATACACACACATCAACGCGCGTGCCACTTAAGAAATAAATAAATAACTTTTATATGTTTATGCCAACCAGCATAAATAC
GATTACTCATACTTTTTGGCGCCAGTTTTCGCACATTGGCAAATCGTTTTTATTTATTTTTTTAATTTTCTTTTTGCCAATTTCATCAACGACTG
CAACTTTTTTATTTCTTGCTATTCTCCTGCTTGGCGGCCATTTTGGAAAAAAAAAAAAAAGCAGCGCACCTCACCATTACAACTAAAACAACAATG
CAACCAACAGTCGTGCGAATACGAGACCTCTCACATCTTCGTGTATTTGTGTATGTATCCACCAGCGAGAATGCGCCTGTGTGTGTGCGGTGAAA
AATAGGGCTCCGCTGGACGGCCGGCGGAGCCCCAAAAACGGCAAAACATAAACTCAGGCGATTCACAACGAAAAAAAAATTTGGAAAACAGTGCA
CACACGCACATATTCAGCGGCCACAAGCACGTGCGTTTTAAGAACCACACTTAGTATTATAAGTATTTAGCAATAAAAAAAAACTCACCGTTAAA
CACGGAATAAAGTTATTCTTCACAATTTGTCACTTTCAACACGAGACGAACAAATTCGGACGAGAGAAATTTTCACAATGATTTCGTTTCGTTGA
GATCTAGAGATGGTAGCCTAGTAGGCGAAGGCCTACTTCGATTGTATTCGATTACACTCGATTGTCTGACAAGACCATGCCCGCCAAATAGTTTG
GTTCTGTTCTTTGCTAATTACATTTTTATAACTTTTTAAAATTTTTTTAACTCCAACCTAAGATTAAAAATGAATATGTTTTAATGGGTTGGACT
CTGCTAATTTTAATGAAATATAAGCTTCATTAAGCAAAAAAAAAGCCAAGTTCTTTTATGGATTGTGGGTTTCTCTCTGCAGAGAACTTTATTTT
AGTGCATTGTGTGTTACATTTGAGTTGAACGAACGTGCATACTACTGCGACTTCTTGTCCTCCTTGGCGGCCCTGCCCACGGGCTCATCCTTGAA
GTGAAGGAACACGAATGAGAAGACAAACACGCCGATCATCATTGAGAAGGCGCTGGTGTAGTAGGGGAATGCGCTCGGGATAAAGCGCTCGTACT
GTGTGTGCTCCAGCGGACGCACCGACACCTGGGTGGTGCTGTACAGATGCGTGTAGCCCACGCGATTGTAGTCCACCTTGAACTGATAAACGCCG
TAGACGTCGGGTATCTTGAATTTGGCCTGGTAGGCGCCCGTGTTCGTTTGCTTCAGATAGGTGCGGACGAAGGGATCGATGCGCACGAACTCCAG
TTGAATGTCGCTGGCCTTAAAGGCGCGCCACTCGCCCTGCACCAGCTCCTCGATGCCGATGGTGTAGACGACCGGATCGGTGATGGTGTACGCCT
GATCCGGTGGCAGCAGCTCGCCCTCCTTGTGATGTTGCACGGATGCCACGCGCAAGCGGCCAGTCTCTCCAAATACCCACTTGCTAATGGACTCG
GCCACGTCGCGATTACCGGCCAGCTTGTGGAACACACCGCTCTGTGCGTACTGCACGGCCGTTGTGAAGCTCTCGTCAGAGAAGAAGAGCAGCGA
GCCGGAGAACACTACGCGGGCATTGTTCCTCGCCTGCAGGGCGGCGATTAGCAGCGTGCCTCGGCCAACGGCATGCGGATAGTCGGAGACACTTG
CCTCGGGATTGTAGCTATAGGCGGTGCTCTCGGCGGTCAGCAGCTTGAGTACCAGCGGGTTCTCCTTGTCGGCAATCAGTCCTGTACCGCGATAG
AGCAGCGGTGCGGCATCCGCCTGCCTGTTGGCCTTGCCCACAATGGTGTCGGCCTGTATAAGATTCTTGGCGGAGGTCAGGATGGTTGTGTGCTC
GCCAGCATCGCTAACATCGTAGTGCAGATGGTCAATGACCGCCGCATTCTCCTCGTCCAGCTCGAAGCCGCACTCGGAGGCGAATTCCCTTAGCG
CGTCGCCGGATTTCTCGCTGCCCGCCACCAGAACATTGCCGCCATCGTCGACGAACTGGGCCAAACGCTCCACGCTCACATCGCCGCCGAATTCC
TCGACACTTGGTGCGAATATGATGACGTTCTTGTACAGATATTCACCGTATTTGGACAGCAGCAGGCTGGAGTCATCCGCCAGTTTGTAGGTGAG
CTTAAATCCGCGATCTGTAGCCCAAAGTTAAACAATTATCAACACATTTCATTGTCCACGTCAGAGGTTAACCGGCATTTTCACTCACCCTGCAG
CGATTTGAAGAAGATCGAGTGGGTTTCCCGGATGGCCAGGTTGTCCAGCAGAACCAAGGTGTTGGCGTCCGTTTCCAGTACCGCCTGGCAGTGGG
CAATCGCCAAAACGGCGATCAGGAGAGCCTTCCACATCATTTTATCCAACTAAAACACAAAATTCTCTCCGGCTTTTCTTGAAAAAAAAAAATGA
CTGGCTGTCAGTGTGGCCGAATACTGGTAGGGTGTGCCAAAATATATACAAATATACCAGAAGGAATTCAAGAAATTATAAAAAATCGATGATTT
GATTAATAATCGATTACATTTACTAGCCAATTTATAAACAAAACATTTTAATTCAAATTTTAGATTGTGAATAACATTCCTTAGCAACAACCATA
ATGGACATATTCGAGAGCTTCTGTCGCACGTGCGGAAACGAATGCCTGGAATCGCTGTCCATTTACAATGAGTGTGCCCAAGTGCTTGACCAGAT
GGTGCCCATTGCGGATATGCTAGCGTCCTGCCTGCCCGCCTCCTTGCCGCCACTGGACCCAGAGGACGACTATCCCAAACAGATCTGCCGCATCT
GCGTGAAGAAGCTGTCGATGGCCTACGAGTTCAGCCACCAGTGGCTGGGCGCCCACGGCGAGTTCAACGTGGCCCTAAAGTTCGAGCAGCGCCGA
AGGCGCAGCCAGGCCAGCAAATCCCAGTCGCACACGCAAACCCAAACTCATCCGGTGGAACCGAAGAATGAGCAACTGCCCACGGTGCTGGCGGA
AGCAGTGTCGACCAAAAGAGGTGGGTGTACAATTTTCTTATCTAGGCTAGGTAGATTTCAAACTTCTCAATCTTCCCCAGCAGCTGCTACTCCCA
CCAACGAGTTCAGCAGCGACTCCGGACCGGCCTTCAAGTGCGGCTTCTGCGGCGAATGTTTTTACACGGAGAAGGCCTGCAAATTTCACTTAAAG
TTCTCGCACAAGGATCTTTAGAGAACTGTCTGTTTTTTCCCTTACTTGTAATTTGGTTTTAAGTGTATAAATCTTTTGTGAAATTAATTTTAAAT
TAGGAATATATATATATATATTCCTTCTCTTTATACAAGTGCCTTCTTTGAGTTTTTAAACCCAAAACGTTGCAATTGTAGGGATATAGAGTGCATT
TGTGTAAGTATGAAACACAAAAAAAAACCTGGAAAACTACTACCCGCTATAGTTGAACCACTGAA
(SEQ ID NO: 988)

Exon: 2579..2369
Exon: 2294..1001
Start ATG: 2510 (Reverse strand: CAT)

Transcript No. : CT25930
ACACTGACAGCCAGTCATTTTTTTTTTTCAAGAAAAGCCGGAGAGAATTTTGTGTTTTAGTTGGATAAAATGATGTGGAAGGCTCTCCTGATCGC
CGTTTTGGCGATTGCCCACTGCCAGGCGGTACTGGAAACGGACGCCAACACCTTGGTTCTGCTGGACAACCTGGCCATCCGGGAAACCCACTCGA
TCTTCTTCAAATCGCTGCAGGATCGCGGATTTAAGCTCACCTACAAACTGGCGGATGACTCCAGCCTGCTGCTGTCCAAATACGGTGAATATCTG
TACAAGAACGTCATCATATTCGCACCAAGTGTCGAGGAATTCGGCGGCGATGTGAGCGTGGAGCGTTTGGCCCAGTTCGTCGACGATGGCGGCAA
TGTTCTGGTGGCGGGCAGCGAGAAATCCGGCGACGCGCTAAGGGAATTCGCCTCCGAGTGCGGCTTCGAGCTGGACGAGGAGAATGCGGCGGTCA
TTGACCATCTGCACTACGATGTTAGCGATGCTGGCGAGCACACAACCATCCTGACCTCCGCCAAGAATCTTATACAGGCCGACACCATTGTGGGC
AAGGCCAACAGGCAGGCGGATGCCGCACCGCTGCTCTATCGCGGTACAGGACTGATTGCCGACAAGGAGAACCCGCTGGTACTCAAGCTGCTGAC
CGCCGAGAGCACCGCCTATAGCTACAATCCCGAGGCAAGTGTCTCCGACTATCCGCATGCCGTTGGCCGAGGCACGCTGCTAATCGCCGCCCTGC
AGGCGAGGAACAATGCCCGCGTAGTGTTCTCCGGCTCGCTGCTCTTCTTCTCTGACGAGAGCTTCACAACGGCCGTGCAGTACGCACAGAGCGGT
GTGTTCCACAAGCTGGCCGGTAATCGCGACGTGGCCGAGTCCATTAGCAAGTGGGTATTTGGAGAGACTGGCCGCTTGCGCGTGGCATCCGTGCA
ACATCACAAGGAGGGCGAGCTGCTGCCACCGGATCAGGCGTACACCATCACCGATCCGGTCGTCTACACCATCGGCATCGAGGAGCTGGTGCAGG
GCGAGTGGCGCGCCTTTAAGGCCAGCGACATTCAACTGGAGTTCGTGCGCATCGATCCCTTCGTCCGCACCTATCTGAAGCAAACGAACACGGGC
GCCTACCAGGCCAAATTCAAGATACCCGACGTCTACGGCGTTTATCAGTTCAAGGTGGACTACAATCGCGTGGGCTACACGCATCTGTACAGCAC
CACCCAGGTGTCGGTGCGTCCGCTGGAGCACACACAGTACGAGCGCTTTATCCCGAGCGCATTCCCCTACTACACCAGCGCCTTCTCAATGATGA
TCGGCGTGTTTGTCTTCTCATTCGTGTTCCTTCACTTCAAGGATGAGCCCGTGGGCAGGGCCGCCAAGGAGGACAAGAAGTCGCAGTAGTATGCA
CGTTCGTTCAACTCAAATGTAACACACAATGCACTAAAATAAAGTTCTCTGCAGAGAGAAACCCACAATCCATAAAAGAA
(SEQ ID NO: 989)

FIGURE SHEET 532

Start ATG: 70 (Reverse strand: CAT)

MMWKALLIAVLAIAHCQAVLETDANTLVLLDNLAIRETHSIFFKSLQDRGFKLTYKLADDSSLLLSKYGEYLYKNVIIFAPSVEEFGGDVSVERL
AQFVDDGGNVLVAGSEKSGDALREFASECGFELDEENAAVIDHLHYDVSDAGEHTTILTSAKNLIQADTIVGKANRQADAAPLLYRGTGLIADKE
NPLVLKLLTAESTAYSYNPEASVSDYPHAVGRGTLLIAALQARNNARVVFSGSLLFFSDESFTTAVQYAQSGVFHKLAGNRDVAESISKWVFGET
GRLRVASVQHHKEGELLPPDQAYTITDPVVYTIGIEELVQGEWRAFKASDIQLEFVRIDPFVRTYLKQTNTGAYQAKFKIPDVYGVYQFKVDYNR
VGYTHLYSTTQVSVRPLEHTQYERFIPSAFPYYTSAFSMMIGVFVFSFVFLHFKDEPVGRAAKEDKKSQ*
(SEQ ID NO: 990)

Classification: enzyme
Gene Symbol: Ost48
FlyBase ID: FBgn0014868

Celera Sequence No. : 142000013384683
GAAATGCAGTCGGTACGAAATTACTGTGACTGGAACGGCCTGGACTTTATCTATTGACTTTAAATTAAATAGATACTTACATACATATTTTAAAT
GAAGTCAGCCCAACGTAAATGTATTGCAAAAGGAATCCCCTCAAAGACGTTTTAGACAAGGAACTTTGGGTATTTGCCTAAGTACAAATTAAGCC
ACCAATTTGATCAAAGTTCACTTTGATGTTTTTAATATCAGCGCAATAGCGATCTAAAGCAGAATCCTCCAAAGTGATGGATTGCATTCGGTACT
CGATCATAGCTGAGCAATTTTTCCTTAAAACATTACAATTTTGTATAAATATAATTTAATAAGAATTTTAGTCTTTTAATCAAAGTAAGACTACA
AAAATTTAACCTGTTGGTGAAGAATTCTATTTGTCATTATATTTTTATTTATAAATTTAATTTAATTTATTAATATTTAACTTTAATATAATTGT
TTTTTATTTAAAATTCGATATTTTCAAATTATATATTTGAAATTGAAATCGCTAGAAATTGAATTGATATGGGAGGAAATTAAGTCTACATATCT
CAATGCCCCTATAATTAGGAAAGATTTATTTTGACAGGACTGACATCATTAGTAATAACTTTATTCCAAATAAAATGAATCCCATATTTTTATAT
TTTTTATGTATACGCACTTATTTTTAATACTTGTATATACAAATTTTATATGAATTTTATAACATTTACGTATACGTACTAATTGCTATCATATT
CGAACGACAAACATTCCCGGAGAAATCTTAACATATAGATGTCATTAGGAACTACAAAAAACCGCTTTCTAAAACTGTATTTTTAGATATAACA
AGTAAAAAATCGGAAAAATTTACCACGGGCTACTAGCTATTTTGTAGCTATTCTCGACTGAGCGTTGCCATCCCTGGTCACGACCAGTGTGACCA
TCGAACTGGTACGACTTCGGCAATTTTCGTAGCTGTCAAGTGACGTGACGTATGTATGGTGCTGTCGTGGCGTTCGCTTCCAGAGAGAAAGAAAG
TCGCAGGTCGCCGAGTTGGATAGCCGTAGAGTTCCGCCTATTCCATTGATTACTAAATAAAAACCACCTCATAACTTGATCAAGATGTCCCGTCA
ACTGTTCGCCATTTGCCTGATTGCCGCCGTTTGTGCGTCCGGCGTCTACGGTAGCTGCAAGGCCACCGTGAGCTCTTTCAGCACCCAGGATGCCA
CGATTCTGACCCAGCTGGCCCATGTGGGCGAGTTCACGCTGCAGTGCAGCGGAGCCGCTCCCGCCAGCCTGTTCGCCGAGTTCCCCTGCGGCAAG
GTGGTGCCGGTGGCCAAGGTGGGCGACAACAAGTACCAGGTGAGCCAGTAGTAGCCCCGTCAAGTTTTGTGCAAAGGCTAATCTCTGTTCTGCAC
TAGGTGAGCTGGGTGGAGGATATCAAGCAGGGCAGCAGCGGCAATGTTCAGGTGCGTCTCTTCGACGAGGATGGCTATGCCAATGTGCGCAAGGC
CCAGCGGGATGGCGACAAGGTTTCATCGGTGAAGTCGCTGCTCGACATTTCCGTGCCCACCAAGGGTGCCTACAAGGGTCCCTGGATCAAGGCTG
AGCTTTTGGCCGCCTTCTTGGTCGGCGGATTCGCATACTTCGCCTTCACCACCAAGGGCAAGGTGCAGTCCTAAGTAGAGGATGCCTTCGTCATC
GAGATTTTGAATGAAATTCATTCGCACTAAAGTCATGTACCATCAAATTGCCGGGTCCCGGAGATTTTTCCACATTTTGTACACCTAAGCATCGG
ATCACCCGCCGCTCCAAAATAAACTGATTGAAAGACCAACCGAAGGAACCTAGTTGAGATTAATTTAATTTTAATTTAGAGATAACTTGTACGAA
TACGCTTAAACCTGGCCCGTGGAGGGCGCTCCATTCATGGTCGCCTCCTCGTCGGAGGAGATGTCTATCATGCTCTCCACACGCGACGGCGACAT
CACATACACAAAGTGCTCCGTGGAGCCCTCGGGGCCGACTGGCGGCGGGGGTATGACCACGGAGCCGTCCTGCGGCGGCGGTGGCGGAGTATCTA
TGCTGCAGTACTTGAGATTCCCAGCTCCTCCTCCGCCTGAATCATCCGGCGGTGGCGCTCCACCGTTGCAATCAAAGTTCTCCAGCTCTAGCTCC
AAATCACTGACGATTCGCATGCAACGCATCTTGGCGAGCGACTGGAATTTCATGGCGATAGCTCGCACCTGCCGCGCCAGACTCAAGAAGAAAAG
AGTGTTTGCGTCAAGTTCTCTGTTGGCCTGTAGCACGGCAGAGACGTCCCAATCGCTCGGAAAACGCGGATCGCAAATCTTACGCGTTTTGGCGG
GCGACGGCTGTTGTTGCTGTTGAATTTGTGGCATTTGCATTGACTGCTGCTGCTGCGTTTGTACGGAATTCCCTCCGGAGCAACTTAGGTTGATG
GCCGTGGTTTGCGGCGAAGGTTGTACCCTTCGCACCTTGGAGGCTGGTGGCGCTGGCGGCGGCGGCGGAGGAGTGGGATTACCCATGGGTAAGCT
CGGGCAGCTGCCGTTCAAACGATTGGCGTTCTGCACTTGGTTGGCCAGGTTCTGGAACAATCCCAAAGGTGCTCCAGCTGCCGCAGCCGCTGTCA
GTTCCTTCTTGAAGTTGTCCGCCGCCGCAAAGAGATGCGGCTCGATGATCAGACAACCGACATTGCTGTTGGTTGCGCTGCCGGTGCTGCAACCA
GGCGGCGTGATCGTAGGTGGCAGGGGAAGACCAGCAGCCACTGCCGCCGCCTTGAGCGTGGCTAGCGGGAACATCTGCTGGGCCAGTCCGCTCA
(SEQ ID NO: 991)

Exon: 1001..1369
Exon: 1429..1849
Start ATG: 1130

Transcript No. : CT25954
TATGTATGGTGCTGTCGTGGCGTTCGCTTCCAGAGAGAAAGAAAGTCGCAGGTCGCCGAGTTGGATAGCCGTAGAGTTCCGCCTATTCCATTGAT
TACTAAATAAAAACCACCTCATAACTTGATCAAGATGTCCCGTCAACTGTTCGCCATTTGCCTGATTGCCGCCGTTTGTGCGTCCGGCGTCTACG
GTAGCTGCAAGGCCACCGTGAGCTCTTTCAGCACCCAGGATGCCACGATTCTGACCCAGCTGGCCCATGTGGGCGAGTTCACGCTGCAGTGCAGC
GGAGCCGCTCCCGCCAGCCTGTTCGCCGAGTTCCCCTGCGGCAAGGTGGTGCCGGTGGCCAAGGTGGGCGACAACAAGTACCAGGTGAGCTGGGT
GGAGGATATCAAGCAGGGCAGCAGCGGCAATGTTCAGGTGCGTCTCTTCGACGAGGATGGCTATGCCAATGTGCGCAAGGCCCAGCGGGATGGCG
ACAAGGTTTCATCGGTGAAGTCGCTGCTCGACATTTCCGTGCCCACCAAGGGTGCCTACAAGGGTCCCTGGATCAAGGCTGAGCTTTTGGCCGCC
TTCTTGGTCGGCGGATTCGCATACTTCGCCTTCACCACCAAGGGCAAGGTGCAGTCCTAAGTAGAGGATGCCTTCGTCATCGAGATTTTGAATGA
AATTCATTCGCACTAAAGTCATGTACCATCAAATTGCCGGGTCCCGGAGATTTTTCCACATTTTGTACACCTAAGCATCGGATCACCCGCCGCTC
CAAAATAAACTGATTGAAAGACCAACCGAA
(SEQ ID NO: 992)

Start ATG: 130

MSRQLFAICLIAAVCASGVYGSCKATVSSFSTQDATILTQLAHVGEFTLQCSGAAPASLFAEFPCGKVVPVAKVGDNKYQVSWVEDIKQGSSGNV
QVRLFDEDGYANVRKAQRDGDKVSSVKSLLDISVPTKGAYKGPWIKAELLAAFLVGGFAYFAFTTKGKVQS*
(SEQ ID NO: 993)

Classification: known_flybase_gene

Gene Symbol: BcDNA:GM12291
FlyBase ID: FBgn0027912

Celera Sequence No. : 142000013383806
AATCCAGCCGTATATCCCACTTCGATCCCTGATCACGGATGAGTGCCGCGAGCGCAGCTACATGGCCTTTATTATCTCGGGTAGTGTTCTTCTGG
GACTACTGCTGCTCCTCCTGATCCTTTTGCTGTGGTGGCGAGTAGTCCAAAAGCGACGACGTCGTAAGCTGGACGTAGTGCAGCCGGAACCGCGC
ACTTACAAGGAAACCCAGATCGTATACCAAATCGAGAACGCTGGCCTGCTAAAGACTGATTTGTAGACGGCAAGGAAAGACACATAGATCACAGA
TGCCTGTTTTGGACTGTTTTTCAGTACCATAGCAGATCATCTACCCACAAGAGACACACAGCTGAATGAAGCTAAAAGGAGCGGTGGGCGGTGGA
ATGGTTGGAGCACCATTGCCACCATTACCACCACCGATCATACAGAACCACCAATGCGTGACCTTTCGCTGTACCAAAACCATAGCCTACAGTTA
GTCGTAATATATCTTAATCTAATTATTCATAACTCGCAATGTTCGTCAGTTGTAAGTGGCCCATGTATATAGTCGCATGTAGGCTGGGATCTTGC
CCAAAAATATCCAGGTGGATTAGCCATATCCCACCAAATACGTATGTATATGGAATAAATCAATTTAAAGCCAAAATGTGGTGCTCTTAAATGTA
TATGCTACATATGTACATATATGTTAATACTATTTGGAAGCGTAATTTAAAATAACAAAATTTGGAGGACAAAGTCAGCTAATAAAATATTGTAT
ACAAATTGCGGATGACAGACGAGATGTACGTGTAAACAAAAGTTTTATTGATCCCTATAGCTTTCGAAAATATTTTTAGAAACTTGACACATGTT
TACAAGATAATCATAAACTTTCAAAGGGAAATAGTGTTGGAAGGAAGCCCATTTTTGTTTACGATATTTAAATATTTATAAATAATATTATATTT
CCCATTTCCCAAATACATTACGATTTAAATAATGATAGTACTTAAAGAACTCACCCGATGGGTAAATATGATTCCAAAGCCTGGTGAACGGTCAA
CTGCGGTTCAGATAGGGCAAATCCTTTAGAGAGCAGGGTATGATGAGTGTTGATGGTCTCCTCAATGCCGCTCATGTCCTCCACGTCTTTGTCAT
CTGATGTGATACATATTTGGTTTAATATAATCCAAAGTAAAAGTAATACTCGCATAAATTACCTGGCAGATTGAGCTCCTTCTTCATCAGATTG
GCACTGCACATGCCACCCAAATAGGCCAACTCCTGTTCAAGTCGTATCAGACACGAGTTGCTGGCATTAATCTGAGCGAGATGGAAGAACACGGT
TTAGAAAGAGATAGTATTACACACGGAATCCACTCACCGATGTGGGATTGTCATAGCCAACCACTAGACACTTGAAGCCATAGCGATTGTTGTGC
GGATCCTGGGCGTAAAGTGAGGCTGTTTCCAAGGAGAACTCCACACAGTTGCCGGGCAGAATGAGGACATTGTGGAGCCAGGTGGAAGCACTATA
ATAATAAGAGCCATCTAGGATCATGACTCCTCATTGGAATATGTTGCTACTTACGTATTAAACTTCTTGACCACAATCCACTCCCTGTCATTGGG
ATCCTGGCTGCGCAGAGGCATTGAACTGGGTGCGGCAGCAGATCCCGGAGCATTTCCACAACCTGGACTCCGGCAGCAACTGGCCATGGTCAACT
GGACACTGGCGGAGCGTTGATGGGTGTTCGGTGCTGCGCCACTACCGGCGATGCCACCGCCCGTGTTGCGCCTCCTGTCCCCCGCTCCATTCACA
TTGTTATCCGCCTGCTCCAAATAGTCATCCACATGCGGCACTGGCGGCGCCTGCGATGCTGGACGCATGGGAATCGACAGGAGCAGGTAATCTTC
CAGTTGAGCAGTGCCACACTGCGGGTCAAACTCGATGGTGAGCCACTGTACGCAAGGTGGAAACTCCACGCGATAGCTACTAATGCTAGCACTCT
TATACGGATGGTCACTCTCCACTACACAATAATGGTTACTGGTGGTGCTGCTCGAATTGGAATTGCCAGAACCAGAGGTCTGTGTAGCAAAAATA
GCCGGCTCCGGCTGTCGCTGATCCTTGGACACGTGCAACTGATTTAGGGCCGCGATATGCGGCAGAATCTCCTTGATTAAGCCCAGAATCTGGAC
GGAACTCTTTGGATCACTGCAAGCCAAATTGGCAATATGTGCATAGACCAGTGGCAGTAACGTGTGGAACATATTGGAGGCGGCCAGATTAAAGA
CCTCGAGCAGCTGCACTGCAGCTGCTTGACTGCCCACTCCTGCCACTCCACCAGATCCATCTGCCACACTTACTCCGCCACCGGCAGCCATGCCG
GCAACCTCCAGCGGAGCCTCCTCCGAATCGGAGTGCAGATGCTGGGGCATTGACTGTTGAGCCGATTGCTCTGCGAACTCAAAGTCAGCGGTTCG
TTCATTGCCATTTATCGGAACACTTTGACTTTGACTCTGACTTTGGCTTACACTTTGGCTTTGGCCATTTCTCAAGTCTGCCGATTCCTCGACTT
CGGTGGCTCCGATTTCAATTTCCATCTCGAAGGGATTCGTGGATCGCTTGTCGAACTTTAGGGTCTCCATGAGACCCTTGCTAAACGACTCAATA
CGTTTGCCCAAATCCCTGGCTGTGGACAGCTGCGGATCTATGGCTGTTGGCAGGGCAGCTGTTCTGGAATTGTTTGCCCAATTGATGTCCATGTG
CTCCTCGATGGGTGTGATATTGTGCTCGGAATCGATGGTCTGTGTGTGATTGGAACTATTATCTGACGGCGAACAAGATGCAGCCATCGCATTGC
GTGCCAAAATCAGCAGTTCAGTACACTTTTTGGTTATATCAGCGGCGATCTGCAGGGCTGTATCGCGGGTGGAGACCTCGTGGGGACCAAGAAGC
ATAATGCGATCCTCCAAATGAGTTGCTACATTGGATCCATCGCCCGTTCGTCCACTCGCCGAGTGTCCATCCTGTTTCATAGGCGTGCTGTAGTA
CAGGATGCAAGGCAATTGACCTCTAGCTGGAGTGGTTCCATTGAAGCTAAGATCGCATGCATAGAAGTGGAACTGGGCGCCACAAGGCCCTCGAA
CCGCCGGCATTCCCGCGTCGCCAGAACAAGTCCTTGCTCCTTGGGAGCATAGACGAAGGGCGTAGCGGGCATTCTCCTTGATATGCACCGGATGG
TCAAATTTGATCTCCGCCAGATCGTTGTGAACTGCATCCTGATCGTAACTGCCGGATACCGATTCCAGGGTCTCCCACTTGTGCTGCGGCTGCAG
ATCCGCCGTATTATCGTACAGCAACTCCAATTGGTAGTCATAGCTCCCGGATCCCGAGTAAACCATTGCGCCAGCTATGGCCACACCAGGTCGAT
CCACGGCGAAGGCAATAGCATCGGGTCCAAAGTTTCCGGTATTCCAGGTCCTACTCACATCGCAGCGGGCAAAGCGAGCTCCCGTCGAATGAAGG
GTTCTGGGTGGCATGAACAGCTTGTCATATTCACCCATCGCCGTTTGATAGACAATCTCGGCCAGAACTCTGGCCAGCAGATGACAACAGTTGTC
AATCAAGCCTTGATTAACACAATCTTTACCTCCGGGATAGCCAAGACTTCCTAAGCTCCGGCTGTATATCGCCTCGATGCGAGAACGTATGGGAC
TGGCAATAATGTCTAGCAAACGCACGAGTACATCCTTAAATGTCCAGGAATTGCTCAGAAAATCACTCTTCTCCTGCTGTGTGCGATATATCATT
TGCTCCACCAGCACGGGATACGGATGGGCATCCGTGGAGGAGAGCATGGGCAAGCCGGAATTGTCGCTGGGACTGATAATTGACTGGCGTTCGTT
TCCAGCCGCACTAAGGAGTGAGAAAGTGGCTCTGAGTTTAACCGATGGCGAGCATAATCCAGCAAGGATCGCGCTTAGCAGGCGGGAATGCAAGG
CTCCACGATCCATCTGAGCAAGCAGATCGCACAAGCAGTTCCACTTCAACGAGGACGTCGGATAGAATGCATCGAAACAGGCCACAAAGCTCAGA
TGACACTCGTCGAGAATCTCCAGCGATAGTTCATAGCCTACAAAGTAAGAGATATCATAGAATAGAATAGGTAAACTATAATTTCCAGACTTAAA
CTAACCCTCATCCGTGGCTATATCCTTGAATATGTCATCGCAAAAGATGCCAATGAGCAGAGCTCTAACATTGCCAATGCACTCCGCCAGCTGGA
TGTTTTCCATGTTGGTCTTCCGGGTGACGGGAGTTCCGCTCCCAGGTGCCACAGCTGCCGAGGCCGATGTAGATGGAGCTCCTCCGCTGCTGGCA
CTGCTAATCATGGCTGGGGCCACCGATGTGGAGGGATCACCAAAATACTTAGCCATTACTCCTGCGTTGCCCACCACACGAGGGGTATTCTTGTC
TATAAATGAATATTATTGAATATTACATTAAAATGAAAGCAAAGGTGTTCACCTTTGTTTGGCTTAGACTGAACAGACTTGGCAGTGGTTACTAC
GCCACTACCATGGGCTGCATTGGAGCCACCGCCCGTGGCCACCGATGTGGAAGAGTTCCTCTGCGGGTAAATCTCGATTGTGTACTTGCGCAACA
GGCGGAGACATGACTTAATGACATAGCCGAGGTACTGCAGCGACTGTTGCAGCTGCAATGGACGGGAGCGATCGCGCTCCTCGCGCAGCTGCAAC
TTAAAGCAATCCCACGACCAGCTTAGCAGGACCACCAGACTCTCGAAGCACTCACGACTCACACTGTTGGCAAAAGCCCGGGAAATACGCTGCAC
AGGATCGGCGTCCATTTGGGCCGGCGTCTGTTTGCAATCCTGGGTGACCAATCGGTACAAAATCGCCGGTATCTGGCCAGAGTTGACATCGGTGC
CGTTGTTTGCCTTTTTGCTGGATTTGAAGGAGAAAACCACCTGATCCTCGGTGGTCACGGACGCCTGACCGCAGGATCCGCAATCGGAGGAGGGA
CCTGCAATCCGGGCCCACACCAAATACCATCTGCCAGCTACCGCACTGACCGGTTTGGGCAGAAGGATATGATGTTTACTCCTGGCGCCGCACTC
GTAGGGCACCTCTTTGGTCTCGCTGATCAGGATGCCTTCCTTCTCGTAGCCACCACCGTCGCCGCCCAAATCGAAGAGCTTCAGTTTGCAACTGT
ACTCCCCGCGGCCACCGAACATCCCGAAGCCACAGATCACAATATCGGTGTCCGCCGAGAAGCGTATGGCCTCCACACTGTGGCCGGAGTAGCCC
CATCCGCCGCCAAAGTTATCGAACCGATTGACTACCTGGAATTCACCGGCCTGCGTTTCTGCCGTCTGTTGGGTTTGCTTCAATAGAGGCTGCTC
AAAGCACCCGGGTATGTTGTCCTGCGCCGAAGTGAGGATGTCGAGACAGGCGAGTAAGTTCAGGGAGGCCTGCGAGCGGGCCACACGCGAATCCA
CCCGATCCGGCAAAGATAACTCCGGCGAGAGCAACGATCGATAAGTGGCCGCGTTCTGGAAGATAGTTTAAGATAAGAGGAACAAGGAAAACTGA
TTTCATCTATTAGCTTACCGCATCGCTGTCGTTGATGTCACTGGCCACCACATTGTGGCAGCGTAGTTTCCGTGCAGCTCCATCGAAAACCCAGA
GAACATTGTATGTGGGATCCATGGTGAAGGCTAGTTGTGGTGGCGATGGAATGGGTTCCGGTGAACTCGTACCCTGTTTGCCACCACGACGACTC
CTTGGCACAGACCCCGCCGATACCGGTGTCCCAGGTGCTGCTACTGCTGCTGCTGCAGCAGATGATCCCACCTCCGGTAGCTGTTCCTCAAAGAT
CTGATTCCTGGCCTCGTGCATGCTTCGGGACATCTGCTCGTTGATGGGCACTCCAGCCGTAGCTGTGCCCGTCAGAGCCGCAAGAAGGGACGAAG
TGGAGGCATGTGCCGGCGAATCCGCAACCGGAGTAACGGCCACATCCAAATTGGAGTTGATCTCCGGTTGCTGTTGCTCCGGCTGTGCTTGCATC
AGTTTCACAAAGTTGGTTTGTCCACGATAATGGGCAGTACAACTACCATCCCGTCGATTTATAGAGAGCGTATGGAAGGACAGCGGAATGCTGGG
AATGAGCACTATATCGGGGATGAGTCAAATATTAGTATTTGATTTTTTTTAAATCTTGTGAGAAACTTACATATCGTCTTTTTATTGGCCACCA

FIGURE SHEET 534

CATGCATCTTGGGCAGCATTTGTGCCGTGATCAGGGATTCGTCTATCTTGATAAAGGTCTGATCTCCATTGGCTCCAATCCAGGTTACCTTCTTG
CCATAACAGGGACCCAAACCACTGCAAAGGATAATAGATAATCATTAGCAATCCTTATTCTACTAATGTGGTTTTTTCCATACAAGACGGCTCCA
GGTGAACAATTCCACAGAAACTTCTGACGCTGGGTGAGCACCGGCAACAGTGGAGGCATCTCCTTGGAGCCACTGGGCTGCACATTGGCCGGCGA
TTGGGATCGTTCCGGGCCCGGCATTCCCACCGGCGCAACCGTTGGCGATCCTCCTGCTCCTCCATCAGATCCAGCTCCCACCGGAGAGTCATCAT
CCTGGGGCGGAGGCTTCAGTCCATAATCACTGGGCAGTCGGCCCAGTTGACCCTTCTGGTAATTGCCAAACGTGTAGACCATTCCTTTCGATGTC
AGCAGTACGGTGTGATTGCTCCCAGCGGCCACTTGGCTGATGGCACCCGGTACCTGAACACGAACTGGTCCGCTCACTGGCTGCAGATCTCCACT
GCCCAATTGACCATACTGATTGCTTCCGAAAGTGTAGACTTCACCGGCCAAGGTGAGCACCACCGTATGGTGCAATCCACAAGCCACCTGCACTA
CAGGCGATGAGCTGGTGAGCTGTAGCAGCTGCGGCGCCAGTGGAGCCACTCGAGGCGGATCCTTGTCCAGATCAGTGGGCGTTGCAGCTCCTCCT
CCGGCGGCTCCTGTTTCCAGTTCGCCCTTGCGCTCCTTGCGGCGCATGATAAGGGTTTTGGAACGCTGCTGGCGCTGTTGTACATCACTGGGTGG
AGGTTTTAGTTCCGTTTTGGCCTCTGCAAGTGGAGATCGGCATTAAGCATGCAACTAGGAATTTTTCGATCAGTAGATATACTCACCATCGCTAT
CCTGGAGGGCAATGCAGGCGGCGCACAGGCCACACTTGGCACAGCCCGCATCTCCGTGACCACAGGGACATATACTGCCCGCCAAACGCTGATCC
AGTGGTACATTTAGAGCGGAGACACAGCTAACATTGTATCCCGTGCATTCGCGACAAATGACGCACACGCGGCACTGACCCTGCACCAGATTATG
GTCATCGTAGTCGCACAGCGTGGAGAAGTCCAATTTGAGGCGCTTGTCCAGTGGCAGCAGGGATGCAAAACAGGCGGCGGCCGTTGAGGATGAGG
CAAATGGCGGCACATCCTTCACCGGCTGCAACTTGTTGAATATCCTGCCGCACTGACCCTTATTGTTCAGTCCGAACGAGAAGAGCTGCCCCCTTG
GCATTGAGAGCCACACAATGGGCCTTGCCCAGCGCCACCTTGGTCACATGCTGTTCCAGCAGCTCACTGACGAAGCCCATGGCATCACAGTGGGC
CGTATCCTTGCCATACATGATCAGCTTTCCAGTTTTGGTTACAAATGCAGAGGTGCCATTGTTGCAGGCGGCATGCACCACCACATGGCCATCGA
TTTTGGTCATCTTCTTCGGTTTAACCGCCTTCGGTTGCCTCCGGTTCTTGCTGCTATCACCATCTTCACCGCGACGAGCTGTGCCCGCAAAGAAA
ACGGTACCATCATCATTGACCAACAGTGCATGAATGCCATCGTGTCCCACGGCCACATGGACTATATTGGCCGCCTTCGAGATGACCAATTCGGT
GAGCTTGAGTGTCGGGGTCCGACCCACACACTTCAATCCGAGCGCAGCGGATTTCCCATAATAGTAGACGCGACCATTACTGGCACGCACCAAGC
CAAACTCCTTGCCGCAGGCCATGCCCATAACATCAACATCCGCATCTCTGCAGGGAGCGGGTAGCTTTGGTTCGAAGCTATTGTGGGCCGACTGG
ATGCGTTGAATCTGATACTGATTGAGCAGCTCATCCTCGAAGGCCGCATACCCCAAGGTCCGGAACTTCTTGCGGGCCAACTGGAGCGGCAGTTC
AAAGGGCGGCGGATCAATGTTGTAGCTATTGTGGTACAGATTTAGTTTCTTAACCACCAGTGTATCCTATTAAAAAAAAAACAATACTCATTACA
AAATAATCTTATATAGTTATACATCAATTTCTAAATGTTAAGGGTATCCTGTCATATTTTATATGAAATATAAAATATACAAAAATCGTTATTTT
CTATGATTATACTGAGATTTTAAATAAAATGCAGTTACTTACATCGCGATTGCTGCAGATGGCGTGCAGTGAGTCGTCGTCCGTAAAGAGCACGT
AGTTGAGTCCTTCGCGCATATGCAGCATACTCAGGGGACTCATTGCCTTAATGGCTAGCGTGTCCAGGCCCACCATTTGCAGTTGATCACCAGCA
CTGCGGCGACAGGTGCGCCGAAAGTAGAGCTGCCCGCCACTGTAGCCCAGCCAGGCGCTCCTCTCGTGGCTGAAGTCCTCATTCTGGGCATAGAT
GTGACCCTTGTAGGATCCCCCAAAGCCAGTGCCAATTTTTAGCAGCGTTCCTCCATAGAGTAAATAGACAAACACTCCATCGCAGGCCATTGCTG
GCGAGGTGATGGGAGCACCTGTGCTCAAGGGCGGCAACTTCACGGGAAACTATTAAAAAAAAGGGGGAACATTTTTGTTTAACCACGCATACAAT
AACAATAATAAAAAAAAACACCGATCACTACACAGCTCACGCACGCAATCTACTACAAAAATAGTAAATATATTATACAAATATTGTATAAAACA
TTAGCTCTTTATAAAATAAACAAAAAAAAAACACTAACCAAGTCCATAACTCACCTCATCGATCAGGGAATTGTGCGGCACCCCGTGGCTGTGAA
AATCCGGTCTGGTCGGCTTATTCAACGCCGCACTGATCACCGTGTGCTGCAAGGTGGCCAGCACCACCGGCAGCTGGACAATCTGGGCGGAGAGC
TGACGCGGCGTCATCAGCATGGCGGCAATAGCCTTGAGCATCTTGCCCGTATCACCGCGTGCGATGCACAGTCCCAGGAGGGCGGCACAGGCCAT
GGCCGACCAATTGGCCTCCGCACCGGTGGCCGAATTGAGTGCGGCCGGCATGGTGGCCAAATCGAGAAGAAGATCGTACAGCGGATTGATCAGCT
CCTCCGGTTCTAGCTTAAAACTTTCCGGCTGCTGGCCCTGGATGACATCCAGCAGGGCCTTCAGCGCCTTGGTGCACAGCAGCGGATGTACATGC
CGGGCATCAGCGATCAGCTCGAAGAGACTGCGCAAGCCGGCGCCCACAATTAGCGGCACAGTGGCGTAGACGGGCTCCCTTTCGGTGGGCTCCTC
TGTGTCCGAATCCGCATCGCTGTTGGCGCTATCCCGACGTGGTCGCTTCTCTGCTGGCAAACCGGGTCCGCCGACGACCACCGGCACTGGTGCCG
GTATCCGGCCATCGACAAGGACTCCAACTGGTCCGCCAGGACCTGCATTCCCAGGTCCAACGGCGCCGTGCATAGCCATATGCGCGTGGCAAGAG
CAATCGAGTAGATTGCTTATCATACAGCTGTGGGCACACATCATGCAGCAGGCTGAGTTCACGTTATTGCTCCACTTCTTCTGGTTTGATCCGCT
TTGGCCACTGGGTGCTCCGCCCTCCTGGAACAGGGAGTAGCGCGTCTCTGCCTCCAGAACCGTGGATCTAATTGCCGAGAAGACCGCAAACTTGG
ACGCATTCGGATCCAGTTCAATGTGCGCCACCGGAAACGAGGGCAAGATCATCAGTTGCTCCTTGACCAGCGGTGGATCTAGCGGATTCACCAGT
CCCCCGGCACCCGCATTCCCTTCCAGAACAGCGGCAGCAGCTGCCGCTGCCATTGCTGCGGCCGATTTGTCCTTTCGACTTTTGCGTTTCGTTAA
CACCTTGCGATCGTGTTGCATTTTTCTGTAATAGAAAAGAATAAATAGGTTTAAAAATATTATACAAAATGTATGATGAACTTGAATAAAAAATC
AATAAGTGCCCACCATGAAAATAACATTAAGCTAGAAAAAATACAAGAGCTTGAGGAAAAGAAAATTCTAAAATCCATTAAACAAGAAATCATAA
AATAATAGTTTGCGAAAAAAAAAAATTTTAGACTAAAATCCTTTTATAATGTAAGTAGCAATTTATATCCTTGCACAAATGATAATCTTTTCATT
TTTTTAAATTGTGTATCTATTCGACAGGTGGAACATATGTATATTTTGTATTTTGAACTATGATAAACTTGAAAACTTTGATTTCGTGTGATATT
TGTTATTGGTTTATACACTATGTAATAGTTGCTAATTAAAACGCACGAATTTTCTTTAAACGGACTCACTTAAAAGAAAAACTTTTGAAAATATT
TAGGGACACTAATCAACATCTAAGTCATAAATCAAAAACGCATTCCAACTAACTGAAAAAGGGGAACAAGCTTAATTTGCGAGGTCCTGGCGAAG
GACTGGCATTTGTTTTTGTTTGCCTACAGGAAGCTTTTAGCTCTTATTGGCTCTTATCAGCCTGCAAGCTTTTATCCTGGATGGCGGTCGTTATT
TTTGGACGACAGATGCACATGCATATGTACACATATCGGACACCAAGGTGCAAGCTTTGGGATGCACATATATATGCATATACCCACATGACCAT
CTTTGCTACTGAGTGCATCCGGAACTTTCGATCCTGCAGCTGACAGGTGGTTTTCAATACTGTTTAACACATCGCAAAGTGAGCTCAAAGTCCGC
GAAAGAAGCAATTACTGCCTCCAAAGTGTGTAAATTTCGTCACAATTTATTTGCATCAATTGAATGTCATGCTTTAAAAGAAATTTTTAAAAGGG
GTTTATAATATAAATGGTTGAAAAGTGGCGGTATAAAATTTGTTATGATTTAAAAAAAGTATATATTCAATGTGAAATAATGTGTTTGCGAAAAT
CAAGTTCTTATTGACAAACTGAAGTTTAGTGTACTAAATCCATGAAATCCGAAAACCCAAAACCTTGGCGCAAACGTTTAATTATTCTAAAGCAA
TTTGCAGGCAATCAATAAAAGCAAGACAATAAGAAACTTTTTACACGCCTTCTGACAAATCGATTTTCTTGAGCTGATTCGACATTTTGCCAACT
AACTGTTGTCTAGGTATTCAATTAAATAATCTTAAGCCCAAGGTCCCGAAACGGTAACCAGCATATATACATACCCTGTTAGAGTATTTAAGACT
CAACTCATTAAAGCTACTTAAGCAATGTTTCCTTTTCGTAAATTTAAAACTCAATTGATCTTTGAACACTTCTAGTTTTGTTTTAAACTACAAAT
CTGTCGTAGCATATATAATCCTGCTTTAAACCTATTTAAAGACATTAAAGTTAACATTTTTCTTCGGCAGATATTGGGATTTCGATTATATAAAT
AATATATATTGAAATATATATGATCCCCAATCGTGTGATGTGAATAATATATATTGAAATATATATAATCCCCAATCGTTTGATGTGGTCTCCCA
AAGATAGTGTTTTTTGGCGGTCTTAACGGGGAGCGACATTCTAAACGCCGCACCATCGCCTCGTGGGCCATCAGTGGATTAATGCAGGTCGCTAG
GCTCATGGCAGTCAGCTGATTGAGAGCAGCGCTCAGCTGTTCGGCGCAGGACTGTCCACTTCCGCCCGTTGCAACCCCCAAAAATCGGGGGGTGC
TGCGACAGCGCGGAGAGCGAATGTGAATTGTGTAGGGGTTGAAGACCCAGATTGGAAGCCGAAAGCCGAGTGCAGCAGATCGATTTTTCAACCCC
AAGTCGGATGGGCTGTACGGGACGCAGGGGATGTAGGGGTTAGGGGGTGGCAACTGAATGGGACTCCGGGACATCTACTTATCCAGATGCTGGCG
GGGATTACCTGCGCGTGCTGTTCGTGTACAGCTCGTAGAAGTGGTCGCCATACTTGAGCGGATTGAGCAGGCCAACCATTTTGGCCCGATTTTCC
GTTAGATCCAGTGCTCCAATCGATATTTTCTATATATTCTAATGCTCCGTTACCGTAGCCGTTACTGTTGCCGTCTACCGTTACAACGTTATGCT
CGCTCTCTCCCGTGAATCTCCTCTCTTCTTTGGCTAATGATTTATATTGCACAGCGGTTATTAAACAAAATATGAATTAACAACTAGAATTTAAC
TAATTTGCCGAGCATCGTCTGGCAATTTGAGTGCCCTTTGTTTTCGCCATTTGCCTTTTGTCACTTTCACCCAAAAAAAAGGAAACACACACCGA
GCGACAACGCAACGGTACAATGGGAACGAGGGAACTAAACTTTCGTCCCGCTTGCTCTTGTGCGCTTCCTGCGAGAGAGGACGCTCAGCTGTGTG
GGAGACAGTGACAGTGTTGGTAACAGAGCGGCATGTCCTATTCTGTGCTTAAAATCTTAAATTTTTCGGAGCTTTCCGATTTAATTTCTGCCTAA
ATTAAAGGTACTTTAAATCGCACGAGTATTTTCTTCAATTTTTTATTTATATATCTTAAATCAACAATTTTGGTTTCCACCTTTCATCCATAGC
TAAGGCTTTTCAGTTTTATTTTATGGCACAACGCAAAAGTATCGATCACGAAATATCACATTTATTGTTCAACTTTTAATATCTGTGTGCCTTTT
CCCTAAAAGTTCCGTTATAAAAGTTAACATTTAAAAATATTTCACATACATTGCAATACACCAGCTGTTCGAGCAGTGCTGAAAAACGCCGACGC

FIGURE SHEET 535

ATCGCGAACTGGCAACGCTGTCAGCAGCTGTCACTTGCAACAAAAACAACAGGGGCAGGAAGAAGAAGAACTTTGACAGCTGCGGCGCAACCGAA
ATCTAAGAAAAACAATTTACGTAATTTAATTGAGCGAATTTCAATGGTTTGCGAGTGTACTAAAACGTTTTTTCCCCACCCGCAGGATGGGCAAC
GCGCTGACGCACTACATGAAACCGGACGTGATGC
(SEQ ID NO: 994)

Exon: 12239..12169
Exon: 12077..11808
Exon: 10190..9080
Exon: 8884..8498
Exon: 8331..7212
Exon: 7148..6449
Exon: 6386..6247
Exon: 6183..5624
Exon: 5565..4569
Exon: 4464..4186
Exon: 4122..1575
Exon: 1515..1368
Exon: 1306..1204
Exon: 1140..1001
Start ATG: 12239 (Reverse strand: CAT)

Transcript No. : CT25974
ATGGTTGGCCTGCTCAATCCGCTCAAGTATGGCGACCACTTCTACGAGCTGTACACGAACAGCACGCGCAGCCCATCCGACTTGGGGTTGAAAAA
TCGATCTGCTGCACTCGGCTTTCGGCTTCCAATCTGGGTCTTCAACCCCTACACAATTCACATTCGCTCTCCGCGCTGTCGCAGCACCCCCCGAT
TTTTGGGGGTTGCAACGGGCGGAAGTGGACAGTCCTGCGCCGAACAGCTGAGCGCTGCTCTCAATCAGCTGACTGCCATGAGCCTAGCGACCTGC
ATTAATCCACTGATGGCCCACGAGGCGATGGTGCGGCGTTTAGAATGTCGCTCCCCAAAAATGCAACACGATCGCAAGGTGTTAACGAAACGCAA
AAGTCGAAAGGACAAATCGGCCGCAGCAATGGCAGCGGCAGCTGCTGCCGCTGTTCTGGAAGGGAATGCGGGTGCCGGGGGACTGGTGAATCCGC
TAGATCCACCGCTGGTCAAGGAGCAACTGATGATCTTGCCCTCGTTTCCGGTGGCGCACATTGAACTGGATCCGAATGCGTCCAAGTTTGCGGTC
TTCTCGGCAATTAGATCCACGGTTCTGGAGGCAGAGACGCGCTACTCCCTGTTCCAGGAGGGCGGAGCACCCAGTGGCCAAAGCGGATCAAACCA
GAAGAAGTGGAGCAATAACGTGAACTCAGCCTGCTGCATGATGTGTGCCCACAGCTGTATGATAAGCAATCTACTCGATTGCTCTTGCCACGCGC
ATATGGCTATGCACGGCGCCGTTGGACCTGGGAATGCAGGTCCTGGCGGACCAGTTGGAGTCCTTGTCGATGGCCGGATACCGGCACCAGTGCCG
GTGGTCGTCGGCGGACCCGGTTTGCCAGCAGAGAAGCGACCACGTCGGGATAGCGCCAACAGCGATGCGGATTCGGACACAGAGGAGCCCACCGA
AAGGGAGCCCGTCTACGCCACTGTGCCGCTAATTGTGGGCGCCGGCTTGCGCAGTCTCTTCGAGCTGATCGCTGATGCCCGGCATGTACATCCGC
TGCTGTGCACCAAGGCGCTGAAGGCCCTGCTGGATGTCATCCAGGGCCAGCAGCCGGAAAGTTTTAAGCTAGAACCGGAGGAGCTGATCAATCCG
CTGTACGATCTTCTTCTCGATTTGGCCACCATGCCGGCCGCACTCAATTCGGCCACCGGTGCGGAGGCCAATTGGTCGGCCATGGCCTGTGCCGC
CCTCCTGGGACTGTGCATCGCACGCGGTGATACGGGCAAGATGCTCAAGGCTATTGCCGCCATGCTGATGACGCCGCGTCAGCTCTCCGCCCAGA
TTGTCCAGCTGCCGGTGGTGCTGGCCACCTTGCAGCACACGGTGATCAGTGCGGCGTTGAATAAGCCGACCAGACCGGATTTTCACAGCCACGGG
GTGCCGCACAATTCCCTGATCGATGAGTTTCCCGTGAAGTTGCCGCCCTTGAGCACAGGTGCTCCCATCACCTCGCCAGCAATGGCCTGCGATGG
AGTGTTTGTCTATTTACTCTATGGAGGAACGCTGCTAAAAATTGGCACTGGCTTTGGGGATCCTACAAGGGTCACATCTATGCCCAGAATGAGG
ACTTCAGCCACGAGAGGAGCGCCTGGCTGGGCTACAGTGGCGGGCAGCTCTACTTTCGGCGCACCTGTCGCCGCAGTGCTGGTGATCAACTGCAA
ATGGTGGGCCTGGACACGCTAGCCATTAAGGCAATGAGTCCCCTGAGTATGCTGCATATGCGCGAAGGACTCAACTACGTGCTCTTTACGGACGA
CGACTCACTGCACGCCATCTGCAGCAATCGCGATGATACACTGGTGGTTAAGAAACTAAATCTGTACCACAATAGCTACAACATTGATCCGCCGC
CCTTTGAACTGCCGCTCCAGTTGGCCCGCAAGAAGTTCCGGACCTTGGGGTATGCGGCCTTCGAGGATGAGCTGCTCAATCAGTATCAGATTCAA
CGCATCCAGTCGGCCCACAATAGCTTCGAACCAAAGCTACCCGCTCCCTGCAGAGATGCGGATGTTGATGTTATGGGCATGGCCTGCGGCAAGGA
GTTTGGCTTGGTGCGTGCCAGTAATGGTCGCGTCTACTATTATGGGAAATCCGCTGCGCTCGGATTGAAGTGTGTGGGTCGGACCCCGACACTCA
AGCTCACCGAATTGGTCATCTCGAAGGCGGCCAATATAGTCCATGTGGCCGTGGGACACGATGGCATTCATGCACTGTTGGTCAATGATGATGGT
ACCGTTTTCTTTGCGGGCACAGCTCGTCGCGGTGAAGATGGTGATAGCAGCAAGAACCGGAGGCAACCGAAGGCGGTTAAACCGAAGAAGATGAC
CAAAATCGATGGCCATGTGGTGGTGCATGCCGCCTGCAACAATGGCACCTCTGCATTTGTAACCAAAACTGGAAAGCTGATCATGTATGGCAAGG
ATACGGCCCACTGTGATGCCATGGGCTTCGTCAGTGAGCTGCTGGAACAGCATGTGACCAAGGTGGCGCTGGGCAAGGCCCATTGTGTGGCTCTC
AATGCCAAGGGGCAGCTCTTCTCGTTCGGACTGAACAATAAGGGTCAGTGCGGCAGGATATTCAACAAGTTGCAGCCGGTGAAGGATGTGCCGCC
ATTTGCCTCATCCTCAACGGCCGCCGCCTGTTTTGCATCCCTGCTGCCACTGGACAAGCGCCTCAAATTGGACTTCTCCACGCTGTGCGACTACG
ATGACCATAATCTGGTGCAGGGTCAGTGCCGCGTGTGCGTCATTTGTCGCGAATGCACGGGATACAATGTTAGCTGTGTCTCCGCTCTAAATGTA
CCACTGGATCAGCGTTTGGCGGGCAGTATATGTCCCTGTGGTCACGGAGATGCGGGCTGTGCCAAGTGTGGCCTGTGCGCCGCCTGCATTGCCCT
CCAGGATAGCGATGAGGCCAAAACGGAACTAAAACCTCCACCCAGTGATGTACAACAGCGCCAGCAGCGTTCCAAAACCCTTATCATGCGCCGCA
AGGAGCGCAAGGGCGAACTGGAAACAGGAGCCGCCGGAGGAGGAGCTGCAACGCCCACTGATCTGGACAAGGATCCGCCTCGAGTGGCTCCACTG
GCGCCGCAGCTGCTACAGCTCACCAGCTCATCGCCTGTAGTGCAGGTGGCTTGTGGATTGCACCATACGGTGGTGCTCACCTTGGCCGGTGAAGT
CTACACTTTCGGAAGCAATCAGTATGGTCAATTGGGCAGTGGAGATCTGCAGCCAGTGAGCGGACCAGTTCGTGTTCAGGTACCGGGTGCCATCA
GCCAAGTGGCCGCTGGGAGCAATCACACCGTACTGCTGACATCGAAAGGAATGGTCTACACGTTTGGCAATTACCAGAAGGGTCAACTGGGCCGA
CTGCCCAGTGATTATGGACTGAAGCCTCCGCCCCAGGATGATGACTCTCCGGTGGGAGCTGGATCTGATGGAGGAGCAGGAGGATCGCCAACGGT
TGCGCCGGTGGGAATGCCGGGCCCGGAACGATCCCAATCGCCGGCCAATGTGCAGCCCAGTGGCTCCAAGGAGATGCCTCCACTGTTGCCGGTGC
TCACCCAGCGTCAGAAGTTTCTGTGGAATTGTTCACCTGGAGCCGTCTTTGGTTTGGGTCCCTGTTATGGCAAGAAGGTAACCTGGATTGGAGCC
AATGGAGATCAGACCTTTATCAAGATAGACGAATCCCTGATCACGGCACAAATGCTGCCCAAGATGCATGTGGTGGCCAATAAAAAGACGATATT
GCTCATTCCCAGCATTCCGCTGTCCTTCCATACGCTCTCTATAAATCGACGGGATGGTAGTTGTACTGCCCATTATCGTGGACAAACCAACTTTG
TGAAACTGATGCAAGCACAGCCGGAGCAACAGCAACCGGAGATCAACTCCAATTTGGATGTGGCCGTTACTCCGGTTGCGGATTCGCCGGCACAT
GCCTCCACTTCGTCCCTTCTTGCGGCTCTGACGGGCACAGCTACGGCTGGAGTGCCCATCAACGAGCAGATGTCCCGAAGCATGCACGAGGCCAG
GAATCAGATCTTTGAGGAACAGCTACCGGAGGTGGGATCATCTGCTGCAGCAGCAGCAGTAGCAGCACCTGGGACACCGGTATCGGCGGGGTCTG
TGCCAAGGAGTCGTCGTGGTGGCAAACAGGGTACGAGTTCACCGGAACCCATTCCATCGCCACCACAACTAGCCTTCACCATGGATCCCACATAC
AATGTTCTCTGGGTTTTCGATGGAGCTGCACGGAAACTACGCTGCCACAATGTGGTGGCCAGTGACATCAACGACAGCGATGCGAACGCGGCCAC
TTATCGATCGTTGCTCTCGCCGGAGTTATCTTTGCCGGATCGGGTGGATTCGCGTGTGGCCCGCTCGCAGGCCTCCCTGAACTTACTCGCCTGTC
TCGACATCCTCACTTCGGCGCAGGACAACATACCCGGGTGCTTTGAGCAGCCTCTATTGAAGCAAACCCAACAGACGGCAGAAACGCAGGCCGGT
GAATTCCAGGTAGTCAATCGGTTCGATAACTTTGGCGGCGGATGGGGCTACTCCGGCCACAGTGTGGAGGCCATACGCTTCTCGGCGGACACCGA TATTGTGATCTGTGGCTTCGGGATGTTCGGTGGCCGCGGGGAGTACAGTTGCAAACTGAAGCTCTTCGATTTGGGCGGCGACGGTGGTGGCTACG
AGAAGGAAGGCATCCTGATCAGCGAGACCAAAGAGGTGCCCTACGAGTGCGGCGCCAGGAGTAAACATCATATCCTTCTGCCCAAACCGGTCAGT
GCGGTAGCTGGCAGATGGTATTTGGTGTGGGCCCGGATTGCAGGTCCCTCCTCCGATTGCGGATCCTGCGGTCAGGCGTCCGTGACCACCGAGGA
TCAGGTGGTTTTCTCCTTCAAATCCAGCAAAAAGGCAAACAACGGCACCGATGTCAACTCTGGCCAGATACCGGCGATTTTGTACCGATTGGTCA
CCCAGGATTGCAAACAGACGCCGGCCCAAATGGACGCCGATCCTGTGCAGCGTATTTCCCGGGCTTTTGCCAACAGTGTGAGTCGTGAGTGCTTC
GAGAGTCTGGTGGTCCTGCTAAGCTGGTCGTGGGATTGCTTTAAGTTGCAGCTGCGCGAGGAGCGCGATCGCTCCCGTCCATTGCAGCTGCAACA
GTCGCTGCAGTACCTCGGCTATGTCATTAAGTCATGTCTCCGCCTGTTGCGCAAGTACACAATCGAGATTTACCCGCAGAGGAACTCTTCCACAT
CGGTGGCCACGGGCGGTGGCTCCAATGCAGCCCATGACAAGAATACCCCTCGTGTGGTGGGCAACGCAGGAGTAATGGCTAAGTATTTTGGTGAT
CCCTCCACATCGGTGGCCCCAGCCATGATTAGCAGTGCCAGCAGCGGAGGAGCTCCATCTACATCGGCCTCGGCAGCTGTGGCACCTGGGAGCGG
AACTCCCGTCACCCGGAAGACCAACATGGAAAACATCCAGCTGGCGGAGTGCATTGGCAATGTTAGAGCTCTGCTCATTGGCATCTTTTGCGATG
ACATATTCAAGGATATAGCCACGGATGAGGGCTATGAACTATCGCTGGAGATTCTCGACGAGTGTCATCTGAGCTTTGTGGCCTGTTTCGATGCA
TTCTATCCGACGTCCTCGTTGAAGTGGAACTGCTTGTGCGATCTGCTTGCTCAGATGGATCGTGGAGCCTTGCATTCCCGCCTGCTAAGCGCGAT
CCTTGCTGGATTATGCTCGCCATCGGTTAAACTCAGAGCCACTTTCTCACTCCTTAGTGCGGCTGGAAACGAACGCCAGTCAATTATCAGTCCCA
GCGACAATTCCGGCTTGCCCATGCTCTCCTCCACGGATGCCCATCCGTATCCCGTGCTGGTGGAGCAAATGATATATCGCACACAGCAGGAGAAG
AGTGATTTTCTGAGCAATTCCTGGACATTTAAGGATGTACTCGTGCGTTTGCTAGACATTATTGCCAGTCCCATACGTTCTCGCATCGAGGCGAT
ATACAGCCGGAGCTTAGGAAGTCTTGGCTATCCCGGAGGTAAAGATTGTGTTAATCAAGGCTTGATTGACAACTGTTGTCATCTGCTGGCCAGAG
TTCTGGCCGAGATTGTCTATCAAACGGCGATGGGTGAATATGACAAGCTGTTCATGCCACCCAGAACCCTTCATTCGACGGGAGCTCGCTTTGCC
CGCTGCGATGTGAGTAGGACCTGGAATACCGGAAACTTTGGACCCGATGCTATTGCCTTCGCCGTGGATCGACCTGGTGTGGCCATAGCTGGCGC
AATGGTTTACTCGGGATCCGGGAGCTATGACTACCAATTGGAGTTGCTGTACGATAATACGGCGGATCTGCAGCCGCAGCACAAGTGGGAGACCC
TGGAATCGGTATCCGGCAGTTACGATCAGGATGCAGTTCACAACGATCTGGCGGAGATCAAATTTGACCATCCGGTGCATATCAAGGAGAATGCC
CGCTACGCCCTTCGTCTATGCTCCCAAGGAGCAAGGACTTGTTCTGGCGACGCGGGAATGCCGGCGGTTCGAGGGCCTTGTGGCGCCCAGTTCCA
CTTCTATGCATGCGATCTTAGCTTCAATGGAACCACTCCAGCTAGAGGTCAATTGCCTTGCATCCTGTACTACAGCACGCCTATGAAACAGGATG
GACACTCGGCGAGTGGACGAACGGGCGATGGATCCAATGTAGCAACTCATTTGGAGGATCGCATTATGCTTCTTGGTCCCCACGAGGTCTCCACC
CGCGATACAGCCCTGCAGATCGCCGCTGATATAACCAAAAAGTGTACTGAACTGCTGATTTTGGCACGCAATGCGATGGCTGCATCTTGTTCGCC
GTCAGATAATAGTTCCAATCACACACAGACCATCGATTCCGAGCACAATATCACACCCATCGAGGAGCACATGGACATCAATTGGGCAAACAATT
CCAGAACAGCTGCCCTGCCAACAGCCATAGATCCGCAGCTGTCCACAGCCAGGGATTTGGGCAAACGTATTGAGTCGTTTAGCAAGGGTCTCATG
GAGACCCTAAAGTTCGACAAGCGATCCACGAATCCCTTCGAGATGGAAATTGAAATCGGAGCCACCGAAGTCGAGGAATCGGCAGACTTGAGAAA
TGGCCAAAGCCAAAGTGTAAGCCAAAGTCAGAGTCAAAGTCAAAGTGTTCCGATAAATGGCAATGAACGAACCGCTGACTTTGAGTTCGCAGAGC
AATCGGCTCAACAGTCAATGCCCCAGCATCTGCACTCCGATTCGGAGGAGGCTCCGCTGGAGGTTGCCGGCATGGCTGCCGGTGGCGGAGTAAGT
GTGGCAGATGGATCTGGTGGAGTGGCAGGAGTGGGCAGTCAAGCAGCTGCAGTGCAGCTGCTCGAGGTCTTTAATCTGGCCGCCTCCAATATGTT
CCACACGTTACTGCCACTGGTCTATGCACATATTGCCAATTTGGCTTGCAGTGATCCAAAGAGTTCCGTCCAGATTCTGGGCTTAATCAAGGAGA
TTCTGCCGCATATCGCGGCCCTAAATCAGTTGCACGTGTCCAAGGATCAGCGACAGCCGGAGCCGGCTATTTTTGCTACACAGACCTCTGGTTCT
GGCAATTCCAATTCGAGCAGCACCACCAGTAACCATTATTGTGTAGTGGAGAGTGACCATCCGTATAAGAGTGCTAGCATTAGTAGCTATCGCGT
GGAGTTTCCACCTTGCGTACAGTGGCTCACCATCGAGTTTGACCCGCAGTGTGGCACTGCTCAACTGGAAGATTACCTGCTCCTGTCGATTCCCA
TGCGTCCAGCATCGCAGGCGCCGCCAGTGCCGCATGTGGATGACTATTTGGAGCAGGCGGATAACAATGTGAATGGAGCGGGGACAGGAGGCGC
AACACGGGCGGTGGCATCGCCGGTAGTGGCGCAGCACCGAACACCCATCAACGCTCCGCCAGTGTCCAGTTGACCATGGCCAGTTGCTGCCGGAG
TCCAGGTTGTGGAAATGCTCCGGGATCTGCTGCCGCACCCAGTTCAATGCCTCTGCGCAGCCAGGATCCCAATGACAGGGAGTGGATTGTGGTCA
AGAAGTTTAATACTGCTTCCACCTGGCTCCACAATGTCCTCATTCTGCCCGGCAACTGTGTGGAGTTCTCCTTGGAAACAGCCTCACTTTACGCC
CAGGATCCGCACAACAATCGCTATGGCTTCAAGTGTCTAGTGGTTGGCTATGACAATCCCACATCGATTAATGCCAGCAACTCGTGTCTGATACG
ACTTGAACAGGAGTTGGCCTATTTGGGTGGCATGTGCAGTGCCAATCTGATGAAGAAGGAGCTCAATCTGCCAGATGACAAAGACGTGGAGGACA
TGAGCGGCATTGAGGAGACCATCAACACTCATCATACCCTGCTCTCTAAAGGATTTGCCCTATCTGAACCGCAGTTGACCGTTCACCAGGCTTTG
GAATCATATTTACCCATCGGGTGA
(SEQ ID NO: 995)

Start ATG: 1 (Reverse strand: CAT)

MVGLLNPLKYGDHFYELYTNSTRSPSDLGLKNRSAALGFRLPIWVFNPYTIHIRSPRCRSTPRFLGVATGGSGQSCAEQLSAALNQLTAMSLATC
INPLMAHEAMVRRLECRSPKMQHDRKVLTKRKSRKDKSAAAMAAAAAAAVLEGNAGAGGLVNPLDPPLVKEQLMILPSFPVAHIELDPNASKFAV
FSAIRSTVLEAETRYSLFQEGGAPSGQSGSNQKKWSNNVNSACCMMCAHSCMISNLLDCSCHAHMAMHGAVGPGNAGPGGPVGVLVDGRIPAPVP
VVVGGPGLPAEKRPRRDSANSDADSDTEEPTEREPVYATVPLIVGAGLRSLFELIADARHVHPLLCTKALKALLDVIQGQQPESFKLEPEELINP
LYDLLLDLATMPAALNSATGAEANWSAMACAALLGLCIARGDTGKMLKAIAAMLMTPRQLSAQIVQLPVVLATLQHTVISAALNKPTRPDFHSHG
VPHNSLIDEFPVKLPPLSTGAPITSPAMACDGVFVYLLYGGTLLKIGTGFGGSYKGHIYAQNEDFSHERSAWLGYSGGQLYFRRTCRRSAGDQLQ
MVGLDTLAIKAMSPLSMLHMREGLNYVLFTDDDSLHAICSNRDDTLVVKKLNLYHNSYNIDPPPFELPLQLARKKFRTLGYAAFEDELLNQYQIQ
RIQSAHNSFEPKLPAPCRDADVDVMGMACGKEFGLVRASNGRVYYYGKSAALGLKCVGRTPTLKLTELVISKAANIVHVAVGHDGIHALLVNDDG
TVFFAGTARRGEDGDSSKNRRQPKAVKPKKMTKIDGHVVVHAACNNGTSAFVTKTGKLIMYGKDTAHCDAMGFVSELLEQHVTKVALGKAHCVAL
NAKGQLFSFGLNNKGQCGRIFNKLQPVKDVPPFASSSTAAACFASLLPLDKRLKLDFSTLCDYDDHNLVQGQCRVCVICRECTGYNVSCVSALNV
PLDQRLAGSICPCGHGDAGCAKCGLCAACIALQDSDEAKTELKPPPSDVQQRQQRSKTLIMRRKERKGELETGAAGGAATPTDLDKDPPRVAPL
APQLLQLTSSSPVVQVACGLHHTVVLTLAGEVYTFGSNQYGQLGSGDLQPVSGPVRVQVPGAISQVAAGSNHTVLLTSKGMVYTFGNYQKGQLGR
LPSDYGLKPPPQDDDSPVGAGSDGGAGGSPTVAPVGMPGPERSQSPANVQPSGSKEMPPLLPVLTQRQKFLWNCSPGAVFGLGPCYGKKVTWIGA
NGDQTFIKIDESLITAQMLPKMHVVANKKTILLIPSIPLSFHTLSINRRDGSCTAHYRGQTNFVKLMQAQPEQQQPEINSNLDVAVTPVADSPAH
ASTSSLLAALTGTATAGVPINEQMSRSMHEARNQIFEEQLPEVGSSAAAAAVAAPGTPVSAGSVPRSRRGGKQGTSSPEPIPSPPQLAFTMDPTY
NVLWVFDGAARKLRCHNVVASDINDSDANAATYRSLLSPELSLPDRVDSRVARSQASLNLLACLDILTSAQDNIPGCFEQPLLKQTQQTAETQAG
EFQVVNRFDNFGGGWGYSGHSVEAIRFSADTDIVICGFGMFGGRGEYSCKLKLFDLGGDGGGYEKEGILISETKEVPYECGARSKHHILLPKPVS
AVAGRWYLVWARIAGPSSDCGSCGQASVTTEDQVVFSFKSSKKANNGTDVNSGQIPAILYRLVTQDCKQTPAQMDADPVQRISRAFANSVSRECF
ESLVVLLSWSWDCFKLQLREERDRSRPLQLQQSLQYLGYVIKSCLRLLRKYTIEIYPQRNSSTSVATGGGSNAAHDKNTPRVVGNAGVMAKYFGD
PSTSVAPAMISSASSGGAPSTSASAAVAPGSGTPVTRKTNMENIQLAECIGNVRALLIGIFCDDIFKDIATDEGYELSLEILDECHLSFVACFDA
FYPTSSLKWNCLCDLLAQMDRGALHSRLLSAILAGLCSPSVKLRATFSLLSAAGNERQSIISPSDNSGLPMLSSTDAHPYPVLVEQMIYRTQQEK
SDFLSNSWTFKDVLVRLLDIIASPIRSRIEAIYSRSLGSLGYPGGKDCVNQGLIDNCCHLLARVLAEIVYQTAMGEYDKLFMPPRTLHSTGARFA
RCDVSRTWNTGNFGPDAIAFAVDRPGVAIAGAMVYSGSGSYDYQLELLYDNTADLQPQHKWETLESVSGSYDQDAVHNDLAEIKFDHPVHIKENA
RYALRLCSQGARTCSGDAGMPAVRGPCGAQFHFYACDLSFNGTTPARGQLPCILYYSTPMKQDGHSASGRTGDGSNVATHLEDRIMLLGPHEVST
RDTALQIAADITKKCTELLILARNAMAASCSPSDNSSNHTQTIDSEHNITPIEEHMDINWANNSRTAALPTAIDPQLSTARDLGKRIESFSKGLM

FIGURE SHEET 537

ETLKFDKRSTNPFEMEIEIGATEVEESADLRNGQSQSVSQSQSQSQSVPINGNERTADFEFAEQSAQQSMPQHLHSDSEEAPLEVAGMAAGGGVS
VADGSGGVAGVGSQAAAVQLLEVFNLAASNMFHTLLPLVYAHIANLACSDPKSSVQILGLIKEILPHIAALNQLHVSKDQRQPEPAIFATQTSGS
GNSNSSSTTSNHYCVVESDHPYKSASISSYRVEFPPCVQWLTIEFDPQCGTAQLEDYLLLSIPMRPASQAPPVPHVDDYLEQADNNVNGAGDRRR
NTGGGIAGSGAAPNTHQRSASVQLTMASCCRSPGCGNAPGSAAAPSSMPLRSQDPNDREWIVVKKFNTASTWLHNVLILPGNCVEFSLETASLYA
QDPHNNRYGFKCLVVGYDNPTSINASNSCLIRLEQELAYLGGMCSANLMKKELNLPDDKDVEDMSGIEETINTHHTLLSKGFALSEPQLTVHQAL
ESYLPIG*
(SEQ ID NO: 996)

Name: RCC1 (regulator of chromosome condensation) protein homolog
Classification: DNA_binding Celera Sequence No. : 142000013384684
TCTTCACCTGGCCATTGACGTTTTCCAGCGCAGATGCAGCAACGTTACTCAGAGCACTCATTGCGTGTTGCTGATCCGGCTGGTGGTAAAGATGA
CTTTGCCCTGAGCTGCCAAACTGAGACACATTCTTCATGGAGCCATTGGACTTATCAACCTGGTATTCGTTGTAGCCGGAGCTGTTGGCGGACTG
TGGAGATGTTAGGAAGTTCGGCACATGGCGGTAGGACTTGCGCGGCTGGATGTGCTGGTCCAAGAACTTCATTTTCTCCAGGTATGGACGCGACA
GGTGTTCGTAGACAGGTGGATCGCCCTGCTTCCGCTGCGACACGTAGCGTTCGCGTAGGTACTTCCACCGCTTCTTGCACGTGTCCACTGGAAAG
GAGGGCAACATTTATATAGAGGATCTGCCGGAGGAGCGCGTCTTCCTCACCATCCGTGCGCAGCTTCATCGCAATCAGCTGCCAGGCCTCGTCCT
TCGTCTCGTACTTGCCACCATTGGCGCCGCCGTTGAGGTAGTACTTCTGCCGGTTGTAGATCACTCCGTGCTGCGCTACCTCGTCAATTAGCTGC
TCATCCATCATTTAGTTTAATTCGTGTTTTCAGCTGCCAATTTGCCTTTGGTGTATGTCAGGCCATTTCCAACACTGTTCATGGGACATCGAAA
CAGTGTGACCGAAAATGTAGCAGCAGAGTGTCAAATATAATTTGAAGATATTGATATCGAAATATATTCGACAATTTGCATCATGTTTAAATTCG
TCAGCATTTTGATTTATATATAGTAATGCATTTAATTAATTAACACGCAATAAAATTAATAATTTCAGCAAAAGTAAATCATTTGCTGTTCCTGA
ATTTACTAAATAAAAATGTTTAAAAATTTAACTTATAAGTTACCTTCACAAAATTCTCGAAAAATAAAAGTCAGCTATAAAATAGTTGCTATAAA
CGTATTATGGTTATTTGAAATTTTAAGGTGGGTTCTTTTGCGAACCGAGATTCAGTCACACTGGCAATTTGGTACCCGAAGTTGAATTGCCGTTT
TGTGAAGCGGATAGTTACCTGCCGATAATCTTAAATAAAAATGTTTAAACTGGCCCGTATGCTCCTGCCGCAGCAGCGGATCCTGGCCAGCCCGC
TGCGCCTGCAACGCCTGATCTCTACCAGCGACGAGGTCAACGCAGAGCCCATCATCAAGTCCATGGACACCATTGGCGGCCTCCCCACCGAACTG
GTCAACGAACAGAAGCTGAAGAAGACTAGCAGGTAATCAATCTACCGGTTTTCGCACTTGACCTTTGCCTTGCCTGTTTGTTTTGTTTACATTTC
GACCGGTATGGGCATGGGCATGGTATGCATGTATCGGAGGCCTGTTTTGGGCGTGATTTTCGAAAAGGAGTTTCGGGGTCTTTTTTTCTTGATTT
CAAGTGGGGGAGAAAGTTTGTATCGAGCCGCTTATGCAGTCACGTAGACCATAGATGCGTGCATGTGTGTGTATGTATTTGTGCCTGCCTGGT
GGTGTCAGTTATGGGCTCTATTGTTCTTGACTTTTGTTTTGTCCACAGAACCTTATCGACGCTCCAAAATCACTCGGTTCCCATTGCCGCTCGCG
TCACGGTGTCGAAAGATGAGAGTCGCGACTTTATGGCCGTGTTCCCAGGTGAGATTTGTTTATTTATGCCCAGTAACAATTATCATGCAAATACT
AATGCTAATTATATTTCGATGTGCAGATCTTGTGCGTGACATCACCACCGTGACGAAGGCATACAATTGCAGCGACGCAGCCAAATGGTTCGCCC
AAGTCCTCCAGTACAATGTGCCCAGGGGCAAGAAGAACCGCGGCATCCTCACCGTGCTCACGTATAAGAATCTAGTGCCCACCCAGGATCTTACG
CCGGAGAACATAAAGCTCGCCCAGTATCTGGGCTGGTGTGTGGAAATGGTAGGAGTTTTATGCATTAAATAGTTTTCCTAATACAAAGTTATCGA
TCATCTTTTCAGCTCCAAAGTTTTTTCATCATCTCAGACGATGTGATGGACAACAGCACCACCAGACGCGGCCAACCCTGCTGGCACAAGGTGGA
GAACGTGGGCCTGACTGCCATTAACGATGCTCTTATGATTGAAAACGCCATGTATGCCATTCTCAAGAAGCACTTCAGCCACTTGGACTGCTATG
TCGCCCTAATGGAGCTCTTCCACGAAATCACATACATCACTACCTGCGGACAATCGTTGGACCAACTGAACTCGAACCGCTGTGTCTCGGAATTC
ACAATGGAAAACTACAAAGCAATTGTCGAAAATAAGACTGCCTATTACTCCTTCTACCTTCCATTCGCACTTGCTTTGCACTTGGCTGGGTAAGT
AATGGCCATACATATATAAGATTCCGCTTATTAATCTTCCGCTCTATTGTTTAGCTATAAAGACGCAGAGGCCTTCCGTCAATCGAAGACCATTC
TCCTAGAAATGGGCAACTTTTTCCAGGTTCAAGATGATTTCCTCGACTGCTTCGGTAATCCGGAAGTGACTGGTAAAATTGGAACCGACATTCAG
GACAACAAGTGCTCGTGGCTGGCAGTGGTGGCAATGCAGCGAGCCAATGTCGAGCAAAAGCAAATCATGGTCGATTGCTATGGCAAAGAAGGTAA
AACTAGCTTAGCAAACCCGCACAATTAGACATTGACTTTTGAATATTAACCTGCAGAACCAGCTAAAGTGGAGCGAGTGAAAGAACTGTACAAGG
AACTTGGACTGCCATCCACCTATGCCATTTTCGAGGAGGAATCCTACAACATGATTAAAACGCACATACAACAAACCTCACGCGGGGTGCCTCAC
CAGACCTTCCTGCAAATACTCAACAAAATCTACCAACGTGACTCCTAAATTACTCAAGCGCAACGACTTTACGGATACGTTTTTAATTAAATTGT
AGTTTTAGCATTTACATGGATGAACTGTTAGCAAGGGCTCAGCAATTACAACCGATATGAACTTTTTACTATACATACAATGTTCTTTGCTTAAT
CGTCTGTAAAATCAAAGGGCGCAAAAGCCTTTCGGAAATCTTCCACATACGCCACTTCTTCGTCCTTATCGAGAAGGCAATCCTTCCAGTTCACT
TTTTCATCGCAGTTAAGAAGATTCTCCGAACAGAACACGTCCCTGAAAAAATGAGTTTAGTCAAGAGTTGGTAGCTTAAATCGAGAAGTTAACGC
ACCTTGCGAAATGAATGGGAAAGTGTTTCATTTGCCGCGTTATAAGTGTGCTATCGTCGGGTAACTCGGCCAGGAAATAAGGTCCCATTTCAGGC
AGCATTTTCTCAGAATCCAATGCGGGAAGTGTCTCAAATTCCAGATTAAATTCCTCCGCCTTATCCTGCAATGTTGTGGGATATACATCATATGT
TATAAAAGGTTGAATGTCGTGAGCATACCTCAAAACTATGTTTTATCTTCCAGGCATAGCCTTCTTCAAAGGCAAGCGCGTTGATTTGTAGGTGA
ACCGATTTATAGTGCCGTTCAGTAAAACACACCACTTGGCCTAACGTTTTGAAGAACTTTCGCAAAGCTGCCTTGAACTTGTTGAGCTCCTTCCA
ATCATCTGGACTTAGTTGAGCAGCGCAGGGCACATGCTTGGTGGACAATATCATGACATGGTGTTTGTTAATCGGTCCTTTGGCCAGAGCAAGAT
AAAAATGTTCGCCCACAGTGATAATGAGATGCTTCTCCACATCAGGTGAGGATAAACAGAACCAGCATTTATCTACAAATATAGGAATAGTATTA
AGGATGCAGCTTGTAAAATTAAGTACTAGACAAACCTTGCTCAATCTGCGGTATTCTAGGACGTTTATCTCTTTTGTTATTATCACCGCCTTGTC
GCTTGCGTCTGCCACCATCCATGTCGTAGAAGTATTGTCGGTTTTCTGACTGAAAGAATATATAATTAGTCACTTGGAGTACTTATAGATATGTA
AAGGTTACCCACCGAATCATTCTTGCCAATAGCTC
(SEQ ID NO: 997)

Exon: 1001..1267
Exon: 1569..1663
Exon: 1737..1948
Exon: 2008..2369
Exon: 2430..2656
Exon: 2717..3025
Start ATG: 1086

Transcript No. : CT26006
TTCAGTCACACTGGCAATTTGGTACCCGAAGTTGAATTGCCGTTTTGTGAAGCGGATAGTTACCTGCCGATAATCTTAAATAAAAATGTTTAAAC
TGGCCCGTATGCTCCTGCCGCAGCAGCGGATCCTGGCCAGCCCGCTGCGCCTGCAACGCCTGATCTCTACCAGCGACGAGGTCAACGCAGAGCCC
ATCATCAAGTCCATGGACACCATTGGCGGCCTCCCCACCGAACTGGTCAACGAACAGAAGCTGAAGAAGACTAGCAGAACCTTATCGACGCTCCA
AAATCACTCGGTTCCCATTGCCGCTCGCGTCACGGTGTCGAAAGATGAGAGTCGCGACTTTATGGCCGTGTTCCCAGATCTTGTGCGTGACATCA CCACCGTGACGAAGGCATACAATTGCAGCGACGCAGCCAAATGGTTCGCCCAAGTCCTCCAGTACAATGTGCCCAGGGGCAAGAAGAACCGCGGC
ATCCTCACCGTGCTCACGTATAAGAATCTAGTGCCCACCCAGGATCTTACGCCGGAGAACATAAAGCTCGCCCAGTATCTGGGCTGGTGTGTGGA
AATGCTCCAAAGTTTTTCATCATCTCAGACGATGTGATGGACAACAGCACCACCAGACGCGGCCAACCCTGCTGGCACAAGGTGGAGAACGTGG
GCCTGACTGCCATTAACGATGCTCTTATGATTGAAAACGCCATGTATGCCATTCTCAAGAAGCACTTCAGCCACTTGGACTGCTATGTCGCCCTA
ATGGAGCTCTTCCACGAAATCACATACATCACTACCTGCGGACAATCGTTGGACCAACTGAACTCGAACCGCTGTGTCTCGGAATTCACAATGGA
AAACTACAAAGCAATTGTCGAAAATAAGACTGCCTATTACTCCTTCTACCTTCCATTCGCACTTGCTTTGCACTTGGCTGGCTATAAAGACGCAG
AGGCCTTCCGTCAATCGAAGACCATTCTCCTAGAAATGGGCAACTTTTTCCAGGTTCAAGATGATTTCCTCGACTGCTTCGGTAATCCGGAAGTG
ACTGGTAAAATTGGAACCGACATTCAGGACAACAAGTGCTCGTGGCTGGCAGTGGTGGCAATGCAGCGAGCCAATGTCGAGCAAAAGCAAATCAT
GGTCGATTGCTATGGCAAAGAAGAACCAGCTAAAGTGGAGCGAGTGAAAGAACTGTACAAGGAACTTGGACTGCCATCCACCTATGCCATTTTCG
AGGAGGAATCCTACAACATGATTAAAACGCACATACAACAAACCTCACGCGGGGTGCCTCACCAGACCTTCCTGCAAATACTCAACAAAATCTAC
CAACGTGACTCCTAAATTACTCAAGCGCAACGACTTTACGGATACGTTTTTAATTAAATTGTAGTTTTAGCATTTACATGGATGAACTGTTAGCA
AGGGCTCAGCAATTACAACCGATATGAACTTTTTACTATACATACAA
(SEQ ID NO: 998)

Start ATG: 86

MFKLARMLLPQQRILASPLRLQRLISTSDEVNAEPIIKSMDTIGGLPTELVNEQKLKKTSRTLSTLQNHSVPIAARVTVSKDESRDFMAVFPDLV
RDITTVTKAYNCSDAAKWFAQVLQYNVPRGKKNRGILTVLTYKNLVPTQDLTPENIKLAQYLGWCVEMLQSFFIISDDVMDNSTTRRGQPCWHKV
ENVGLTAINDALMIENAMYAILKKHFSHLDCYVALMELFHEITYITTCGQSLDQLNSNRCVSEFTMENYKAIVENKTAYYSFYLPFALALHLAGY
KDAEAFRQSKTILLEMGNFFQVQDDFLDCFGNPEVTGKIGTDIQDNKCSWLAVVAMQRANVEQKQIMVDCYGKEEPAKVERVKELYKELGLPSTY
AIFEEESYNMIKTHIQQTSRGVPHQTFLQILNKIYQRDS*
(SEQ ID NO: 999)

Classification: enzyme
Gene Symbol: Fpps
FlyBase ID: FBgn0025373

Celera Sequence No. : 142000013384577
GTTGGCCAAGTAGCGCGTACATGTGTGGGTTTTCGCCATTTAAGGCGTGCACCCAGCACGAAAGTCGCTTTGTACGCAATTTACCCAAAGTGTTG
GTCGGTTTTCGATTTTTGTCGAACCACCCCACGTTCAGTAAGTCTAGAGAAATCTCTTTCTAAACGGATTTCCAGGAAACCCACGGCACTCACAC
TGTTCACACGCTGCGGTAAAAATTCAGAGTGACCGTCGACAAGCGGTAGTACTGGAACACAAGTCGCTGTTCGCTCGAAACAATCGATGTGTGCC
AAAATTCGATCACGATATTCCTCGCAATCGATTGTATTCGCTATTTGCCTTCGTAAGTCCCGGTTAGACCAGCGGCATGAAAAGTTTAAATTCAC
TTCCACATTCGAGTACTATGAGATAAGATTACTGTACTTAAACTCAAAAAGATTCAAAACAACACTGATCGTTAAGCTACTAAGACAAATAGCTG
GCCGGTTCCAGTCCCACGATTTAAAAACAGTTCACTGAATAGCAGCATATGTAAAATTCCATACTTTCATATATTTGTATAATATGATTCACATA
AGGTTGTTGTTCAAATGGTTGAATACTACAATTAAGTCTTTACAACAAGAGAATGTAATCTGTTGGAAAACAATATTACAATCAAATTTATTAAA
CAAATATAAGATTCGGGTTTAAATATTTATACTGGTGGAAAACTTTGATGGGCGTAATATCGATAGCAAATAAAATAGCGAAGTCAGGCACCCCA
GCTCTGGGTCTGCAGCCCTGAACTTCAAGTGGCACCTCCAAAATAACGTAAAAAAGTGCAAAATAATACAAATTGAATTCAAAATATTTGCATTA
TTTTATGCTTTGTTTTTCTTTACCATACACACTGCGAAGCCGCAGCGAAATTGCCGGATATCCGCTAACATCTGGCGATAGTTGGCGATCGATCT
ATCGATAGTCGCTAATGTTTTCTTACATCACTAAAACTTTTGCAAGATGGAGCCTCTTTTGCTTGGTTTTAACAAATCAGTAGCAGCACGTGTAT
AAAAAGTGCCAAATAATTTTCAGAAAATGTTAGTATATACCCTAGATTAAGCGTTTGAAATGTAAAAAGCCGCAAGGCGATCTTGTGCCGCATCG
ATTCCGCAACTGCTTAGCATAATTTCCGCGTGTTTTAATGCAAAAAACGCGATTTTAAATTTCTGACGGTCAAAATGAGTGGAAAAAAATTACAC
GCCCGTATGACAGTGCAGGGAGTGGGAGTGAGAGGCAGCCACCATGCGAGCGAGAGAGAGCGAGCGCAGTGGTTGCTCCAAGAGAGTTTTGTTGC
TGGACTCGGTCTTTGCACCCCTCCCCCTTCGCCTTGGCGAAACCTAGAACTCCGAACTGGGGACTTTTGTTGAAGTCCGGTGACGTCGGTGTCGC
CACTTGACTGGATTTTATGCACTCTCGTCCGTCCGTTCGCTTGACTCATGACTGGACAATGACGCAGACCGCTGATTCTATCTTTAGTGGACGAC
GGCATTCGTGGCTGATTTAGCCTTGCTCCAACTCAATTTTCGATTTGCTTTGGAATATTTGCCTGTCAGTCGGTTTTTTTTTCTATCCCCACC
CCGCCGTACTGTCAAAACTACTGCTATTTTCGATCAACTACTACCATTCGCAACTGGTGTTAGGCAACACTGGCGCCACTGTTACGTGCTAATAT
CGCTCGGCTGCTCTCGCCCGTTGACATTGACACGAACGACACTAGGGTCGTCCCGCTCGCACACGCTCAGGGGCGGACTCTCGCCGCTTGTCGCT
CAAAAAGGCTGCCTAGCTATCGCTTTCGGTCTCATACGTAAAGTCACCGCTTCGCAGAGCGCATCGCAGCACAAACGTAACGGACTAAAAGCAAA
GCGCTCGATAGCTCGAGAAAACAACACAGTCGGCGTTCGGCCCGAATTCTCCGTTATTCGTTCTAGACAAATAGGCAAACAGTTGATTGAGTGAA
CCGGGCCCAAGCCGTCGAAATTCAGGATATAAGTTTACCTAGTCAATTCTTTATTGTTGATAATGTGAGTGGTTGCCAAGCGGCGCTCGCGGTTT
TCGATTCTCCCTCCACCAGCCTTACTTACTTTTCGCTTTTCTGCCATTCGCCATAACCAACAATTGTGGCTGGAAAATTTTTTACCCCCGTCCCG
CTACTGCTTTTGTTGTTGTTTCCACTGTTCCGCCCCACTAACGCATTCTCGCTTTCTTGCAGGGATGACCGAAATGAGATACCTCAGGATGGCCC
CGCCAGCATGGAACCCGAGGGCGTCATCGAGTCCACCTGGCACGAGGTGTACGACAACTTCGATGACATGAACTTGCGCGAGGAGTTGCTGCGCG
GCATCTACGGTTATGGTTTCGAGAAGCCGTCGGCCATCCAGCAGCGCGCCATCATTCCCTGTGTGAGGGGTCGCGATGTCATTGCCCAGGCCCAG
TCGGGTGAGTAAATGGCTCCGAGTCCCCCATCATCATCTTCACCATCATCCCCCTCGATCAGTCACAAAGAAAAACTTTCGAGAATGTGCAAAAT
CGGCGAAAAAACAGCACGATGACTCAGCCGCTGCGCCTGTATTTCTTTGTTGAAATTCCGCTTTGCAGCACTCTCTTTCTTCTCCTTATACTCTC
TCTCTTCCGTCCGCTCTCTTCGATTGTCGGCGTCGTTGCGCTTGCGCGCCACTTTTCGCTGACCAGCTGCGTTTCGGTTTCTCGGCCGCCAGGCC
AGAAGAAAGTTCCCAGAAAGAAGGTCGCTCTTCGAGCGCTCTTGGCGAATTCCAGCTGCTATGCGTTTTTAAGGTCATCTGTTCCAAATGCGATC
TACCTACATTGCTCATTCGGCACTAATCCATTTTGCAGGCTCTGCAAAAGAGGCTCTATATACATATTAATATAGTTCATTCTCAACTCCTGTTT
TGTGTTCTGGCACTTGCACCTGCCTATCGATGTATAGGCAGGGATTAGTGGCCAGCTCGACCCTGAAATGGCACATCAGCTACCTGATGAAACGA
TGGACAACTGTCTTTATTCCATTGATCTTTCCGTCATTCAAGTTTACGCCTAACAGAATTGCATAACAAATGGCGTACTGGTTAGTCGAAAATTG
GAATTTTGCTGAATTTCCATAAGAATATCACATAGTTAGAAAAGTAATTGTGTATAGTCCGTAGCACACACTATTCTGCATACTAACCATTTTAC
CTTTAATCTCCTCCGTAGGAACTGGCAAGACTGCCACCTTCTCGATTGCTATCCTTCAGCAAATCGACACGAGCATTCGCGAGTGCCAGGCGCTG
ATCCTGGCCCCCACTCGCGAGTTGGCCACGCAGATCCAGCGCGTGGTGATGGCGCTCGGCGAGTACATGAAGGTGCACTCGCACGCCTGCATTGG
CGGCACTAACGTGCGCGAAGACGCCCGCATCTTGGAATCCGGTTGCCATGTGGTGGTGGGCACTCCTGGCCGCGTCTACGACATGATCAACCGCA
AGGTGCTGCGCACCCAGTACATCAAGCTGTTCGTGCTGGATGAGGCCGATGAGATGTTGTCCCGCGGTTTCAAGGATCAGATCCAGGATGTCTTC
AAGATGCTGCCCCCAGATGTGCAGGTCATCCTGCTGTCCGCCACCATGCCGCCGGATGTGCTCGAAGTGAGCCGTTGCTTCATGCGTGATCCCGT
CAGCATCCTGGTTAAGAAGGAGGAACTGACCCTTGAGGGTATCAAGCAGTTTTACGTCAACGTGAAGCAGGAGAACTGGAAACTGGGCACCCTTT
GCGATCTGTACGATACGCTGTCCATCACCCAGTCGGTAATCTTCTGCAACACCCGTCGCAAGGTAAATTCACTCATTCTTATAATTGTGTGAAGC
TGGATTAGTTTCAATCGCAAAGCCGATAAGTTGCTAACAAAAATGTCTACCCATTCTTCAGGTGGACCAACTGACCCAGGAGATGTCTATCCACA ACTTCACCGTCTCGGCCATGCACGGCGACATGGAGCAGCGTGATCGCGAGGTCATCATGAAACAATTCCGTTCGGGCTCGTCTCGTGTTCTGATT
ACCACTGATTTACTGGCGCGCGGTATTGATGTGCAGCAGGTGTCGTTGGTCATCAACTATGATCTGCCCTCGAACCGCGAGAACTACATTCATAG
GTAAGTGCTCACCACCTCGCCCCTGAATCTACTCAGCTATGTGCTATACTAAACATGATACCATCACTTTCAATCTATTTCAGAATTGGTCGCGG
TGGTCGTTTCGGTCGCAAGGGTGTTGCGATCAACTTTATTACAGATGATGATCGACGAATCCTTAAGGATATTGAACAGTTCTACCACACAACAA
TTGAGGAAATGCCTGCTAATATTGCCGATTTGATTTAAATTTTTTCTGCTGAGCCGCAAAACAACTAAGAAAGAATTCTAAACAAAAAGTGAGTG
AGCAAAACAGCAAACAAGAACTGCGAAATCGATAACCGAGCGCAACTATAAATTATTCAAAGATCAACAAGTCAAGTTAAATATTTATTATTCAA
ATATTAATTCGAAAAGGCAGCCGACCGACCACCCAAAAAAAGGACTAAACCAGGACAGAGCAGCAACATCTTCAGCAGCGGCGCAGCAGCAGTAA
CATCAGCAGCAGCGGAAGCGGCAGCAACACCACCACCAATTGCCGATTAGCCGGAACCCCTCTGTATCCATTTAGTTCTCTGTGTATCATCAATT
TTAAAACTGCGTTGTCAACCAGCAACAACAAATATATACAAATATATAAAAAAAAAAAAAACAAAACTTAAAACAACATTTGCATCTATCTAAAAA
AAGTAATATCTGAAACCAGGTACAAGATACCACTTGCTAAGAAGAGCGAGGAACTAAACGCAAAAGCCACAATATCAGAACACCTTTTTGCCGCA
CCTTTGTTTTAGCTTTTTCTAGAACTATTGATAAAAATATATTAAAACAAAACAAAATACATATGTACACATTATGTTTAAATATACCACTCCTA
AAAAACAGCTGACAACCGAAGCAACATTTTACGCTAAACACGAACACACAGCGAATCCACCCAGATCTATAAATGTATTAACATATAGCTATATA
TCTTTCGGGGTATGGCCAAAAAATATATGGTTGCCGCTATTGGGTGTATAGCATGAGTTGATATAGCTGTGGATATATACAATTGGGTGGTATTG
TAGATTATGTTTAACAAAGCGGAAGTAAATTCCTTATCTCAAAACAGTAGAACGAAAATGGCTGTTTTTGAAAAGTTTTTATGTATCTGTTACGT
ACGGGTTGGGTTAACCTCATATTAACCCAAACCTTTTTAGCCAATTTCATAAGCTTTCGCTTTAAAACCAGCTCTCTAAGCAAGATGAGTTCCAA
AAGTTAAACTAATTTTTTAAAACTTTCAACACCACTCCACTGCATATACTTTTAAAACGAAAGCGCAGTGGGTAAGTTGCATTTCGTTAAGCCTT
CACATCAACTTATCGGTTGAAATTCTGATAACAAGCTATCGATAATCTATCGATTCGACTCGCAGCCCTATCACGTCAGGTCATATTAATTTTTC
AATCCGCCCAGTTGGATGTTTGGACAGTTTCCTTCCTCGCGCCGGTCGATAATGTTGGCCAACTAACACCGACCTGTAGCACGTCACCCGTAATA
ACCCATAACCGCAACCAGTCCAAGCATCCAAGATGGGACAGAAAGTTTCGCGCACCGACTTCGAGTGGGTGTACACGGAGGAGCCGCAC
(SEQ ID NO: 1000)

Exon: 1001..1073
Exon: 2248..2474
Exon: 3249..3862
Exon: 3957..4180
Exon: 4264..4789
Start ATG: 2288

Transcript No. : CT26044
AGCCTCTTTTGCTTGGTTTTAACAAATCAGTAGCAGCACGTGTATAAAAAGTGCCAAATAATTTTCAGAAAATGGATGACCGAAATGAGATACCT
CAGGATGGCCCCGCCAGCATGGAACCCGAGGGCGTCATCGAGTCCACCTGGCACGAGGTGTACGACAACTTCGATGACATGAACTTGCGCGAGGA
GTTGCTGCGCGGCATCTACGGTTATGGTTTCGAGAAGCCGTCGGCCATCCAGCAGCGCGCCATCATTCCCTGTGTGAGGGGTCGCGATGTCATTG
CCCAGGCCCAGTCGGGAACTGGCAAGACTGCCACCTTCTCGATTGCTATCCTTCAGCAAATCGACACGAGCATTCGCGAGTGCCAGGCGCTGATC
CTGGCCCCCACTCGCGAGTTGGCCACGCAGATCCAGCGCGTGGTGATGGCGCTCGGCGAGTACATGAAGGTGCACTCGCACGCCTGCATTGGCGG
CACTAACGTGCGCGAAGACGCCCGCATCTTGGAATCCGGTTGCCATGTGGTGGTGGGCACTCCTGGCCGCGTCTACGACATGATCAACCGCAAGG
TGCTGCGCACCCAGTACATCAAGCTGTTCGTGCTGGATGAGGCCGATGAGATGTTGTCCCGCGGTTTCAAGGATCAGATCCAGGATGTCTTCAAG
ATGCTGCCCCCAGATGTGCAGGTCATCCTGCTGTCCGCCACCATGCCGCCGGATGTGCTCGAAGTGAGCCGTTGCTTCATGCGTGATCCCGTCAG
CATCCTGGTTAAGAAGGAGGAACTGACCCTTGAGGGTATCAAGCAGTTTTACGTCAACGTGAAGCAGGAGAACTGGAAACTGGGCACCCTTTGCG
ATCTGTACGATACGCTGTCCATCACCCAGTCGGTAATCTTCTGCAACACCCGTCGCAAGGTGGACCAACTGACCCAGGAGATGTCTATCCACAAC
TTCACCGTCTCGGCCATGCACGGCGACATGGAGCAGCGTGATCGCGAGGTCATCATGAAACAATTCCGTTCGGGCTCGTCTCGTGTTCTGATTAC
CACTGATTTACTGGCGCGCGGTATTGATGTGCAGCAGGTGTCGTTGGTCATCAACTATGATCTGCCCTCGAACCGCGAGAACTACATTCATAGAA
TTGGTCGCGGTGGTCGTTTCGGTCGCAAGGGTGTTGCGATCAACTTTATTACAGATGATGATCGACGAATCCTTAAGGATATTGAACAGTTCTAC
CACACAACAATTGAGGAAATGCCTGCTAATATTGCCGATTTGATTTAAATTTTTTCTGCTGAGCCGCAAAACAACTAAGAAAGAATTCTAAACAA
AAAGTGAGTGAGCAAAACAGCAAACAAGAACTGCGAAATCGATAACCGAGCGCAACTATAAATTATTCAAAGATCAACAAGTCAAGTTAAATATT
TATTATTCAAATATTAATTCGAAAAGGCAGCCGACCGACCACCCAAAAAAAGGACTAAACCAGGACAGAGCAGCAACATCTTCAGCAGCGGCGCA
GCAGCAGTAACATCAGCAGCAGCGGAAGCGGCAGCAACACCACCACCAATTGCCGATTAGCCGGAACCCCTCTGTATCCATTTAGTTCTCTGTGT
ATCATCAATTTTAAAACTGCGTTGTCAACCAGCAACAACAAATATATAC
(SEQ ID NO: 1001)

Start ATG: 114

MEPEGVIESTWHEVYDNFDDMNLREELLRGIYGYGFEKPSAIQQRAIIPCVRGRDVIAQAQSGTGKTATFSIAILQQIDTSIRECQALILAPTRE
LATQIQRVVMALGEYMKVHSHACIGGTNVREDARILESGCHVVVGTPGRVYDMINRKVLRTQYIKLFVLDEADEMLSRGFKDQIQDVFKMLPPDV
QVILLSATMPPDVLEVSRCFMRDPVSILVKKEELTLEGIKQFYVNVKQENWKLGTLCDLYDTLSITQSVIFCNTRRKVDQLTQEMSIHNFTVSAM
HGDMEQRDREVIMKQFRSGSSRVLITTDLLARGIDVQQVSLVINYDLPSNRENYIHRIGRGGRFGRKGVAINFITDDDRRILKDIEQFYHTTIEE
MPANIADLI*
(SEQ ID NO: 1002)

Name: eIF4A
Classification: translation_factor
Gene Symbol: eIF-4a
FlyBase ID: FBgn0001942

Celera Sequence No. : 142000013384577
CAGAGCAGCAACATCTTCAGCAGCGGCGCAGCAGCAGTAACATCAGCAGCAGCGGAAGCGGCAGCAACACCACCACCAATTGCCGATTAGCCGGA
ACCCCTCTGTATCCATTTAGTTCTCTGTGTATCATCAATTTTAAAACTGCGTTGTCAACCAGCAACAACAAATATATACAAATATATAAAAAAAA
AAAAACAAAACTTAAAACAACATTTGCATCTATCTAAAAAAAGTAATATCTGAAACCAGGTACAAGATACCACTTGCTAAGAAGAGCGAGGAACT
AAACGCAAAAGCCACAATATCAGAACACCTTTTTGCCGCACCTTTGTTTTAGCTTTTTCTAGAACTATTGATAAAAATATATTAAAACAAAACAA
AATACATATGTACACATTATGTTTAAATATACCACTCCTAAAAAACAGCTGACAACCGAAGCAACATTTTACGCTAAACACGAACACACAGCGAA
TCCACCCAGATCTATAAATGTATTAACATATAGCTATATATCTTTCGGGGTATGGCCAAAAAATATATGGTTGCCGCTATTGGGTGTATAGCATG AGTTGATATAGCTGTGGATATATACAATTGGGTGGTATTGTAGATTATGTTTAACAAAGCGGAAGTAAATTCCTTATCTCAAAACAGTAGAACGA
AAATGGCTGTTTTTGAAAAGTTTTATGTATCTGTTACGTACGGGTTGGGTTAACCTCATATTAACCCAAACCTTTTTAGCCAATTTCATAAGCT
TTCGCTTTAAAACCAGCTCTCTAAGCAAGATGAGTTCCAAAAGTTAAACTAATTTTTTAAAACTTTCAACACCACTCCACTGCATATACTTTTAA
AACGAAAGCGCAGTGGGTAAGTTGCATTTCGTTAAGCCTTCACATCAACTTATCGGTTGAAATTCTGATAACAAGCTATCGATAATCTATCGATT
CGACTCGCAGCCCTATCACGTCAGGTCATATTAATTTTTCAATCCGCCCAGTTGGATGTTTGGACAGTTTCCTTCCTCGCGCCGGTCGATAATGT
TGGCCAACTAACACCGACCTGTAGCACGTCACCCGTAATAACCCATAACCGCAACCAGTCCAAGCATCCAAGATGGGACAGAAAGTTTCGCGCAC
CGACTTCGAGTGGGTGTACACGGAGGAGCCGCACGCCTCGCGGCGCAAGATCATACTGGAGAAGTACCCGCAGATCAAGAAGCTCTTTGGCCACG
ACCCGAATTTCAAGTGGGTGGCCGGCGCAATGGTGCTCACACAGATCCTGGCGCTGTTCGTCGTGAAGGACCTGTCGTGGTCGTGGCTCATCGTG
GCCGCCTATTGCTTCGGCGGCATCATCAACCACTCGTTGATGCTGGCCGTTCACGAGATCTCGCACAACCTGGCCTTTGGACACAGCAGACCTAT
GCACAACCGGATCTTGGGCTTCATCTGCAACCTGCCCATCGGGTTGCCCATGAGCATTTCCTTCAAAAAGTACCATCTGGAACATCACCGGTACG
TGCCAATCGGTTCGAATTCATACCCTAAACCGCACCCTCACGCACACATGGGCATTAACACTTTTCTCTGGGCAATAGGGCGTAGTCACACAGTA
AACAGCGAAAACATCATCCCATTCCGCATTTATCCATTTAAAAGCCGGCTTGTGTTGTTCAACACTGATTGCTCTCCATTGGGTTTCATGTGAAT
TTTCACCCCGCAAACTTGTGAATCAGTTTTCATGTTGTTCCCTTTTGCCGGGCATCGAGTGCGTCTTAATTGCGCCGATTAGATAAGGTTGTAGT
TATATGTGTATCCGAATAGGCGCTCAATTGGTCACGTAGCTCAGTGATTTGCCACTCGACTTCTCGGCTGCAAGTCGCGTTCAGTTGAGTCACTG
CTTCGCCTTCCGCAAAAAGTTCCCGAAATATTATTCAAACTAATTTTATGAGTGTTGTTTATGTTTACAGTTACAGTCATTCACTATGTTTCTAG
TCGTAGATAGTGTTTATCTTATCGCCCAGGTGCACCATTGGGCGGATCATTGATTGTCGTTCAACAACGTCCCAATCCCAAATGTTCGCTTCTCA
GTCCCAACTAAGTCTAAAATAAGTCATGTACGTAAATCATCACAAACTATCTGCATTCTAAAAAAATTATATTGCTAACTACATGCTATGCATAC
ATTGTTCACCGTTCACCAGCTCAATAAACTGTAACGTTTATTTGTCCTTTCAGTTACCAAGGTGATGAGGCAATTGACACTGACATACCCACACT
GCTGGAGGCGCGCCTGTTTGACACCACATTTGGAAAATTTCTGTGGGTGTGCCTGCAGCCTTTTTTTACATTTTCCGTCCACTGATTATTAACC
CGAAGCCACCTACACGCCTGGAGATTATTAACACCGTGGTGCAGCTAACTTTCAACGCCCTGATCGTTTACTTTCTGGGCTGGAAGCCACTGGCC
TATCTGTTGATCGGCAGTATTCTAGCAATGGGACTGCACCCGGTGGCCGGACACTTTATCTCGGAGCACTACATGTTCGCCAAGGGCTTTGAGAC
GTACTCCTACTACGGTCCGCTCAACTGGATCACCTTCAATGTGGGCTACCACAACGAGCATCACGACTTTCCGGCGGTGCCCGGCTCCAGGCTGC
CAGAGGTTAAGCGCATCGCTAAGGAATTCTACGACACAATGCCACAGCACACCAGCTGGACCCGGGTTCTGTACGACTTCATCATGGACCCAGCA
GTGGGACCTTACGCACGCGTGAAGCGACGCCAGCGCGGCCTGGCCTCCTAAGCCATCGATGCTATTCAAGGTTTCCTGCCATGAATGTAATCTCA
GCGTTAGACCTAAAACGGCTTTTTATGTATATATACACCGTAGAGACATTTACAGCGGATGCAGAAGAAATAAGGGGAACAACCACACACATAG
CACCAGCTAATCTCTGTGATTAGATAAGGGGCATTCGGACACTTGCAGCGGCTGATATGAACAATTACGTGGATATAGTTTTTGGTATTATTGCT
AGAGTGTGAGCTTAGTTAGGTTCGTTGGCCTAACTGAGAGGCACTTTCGAGCGCTTTAATTAATTGTTACCTCATAAATTGGAAAGCCTGTTAAA
TCTAGTGTGTAATACTTGTCCTATTATACTATTGTCTTAGTATTTTCGATACATATTTATATTGCTTTCAGATCATTTATGTGCAGACACGATTT
GGTGTGATCAATCTTAATCCTTATCGCCGCCACCCTGGCCGATAGCAAGCCACTAATCAAGCAACCAACTACTATTTTTGATAGACTCTTGAAAC
TGTTACCTAAGAATAAAGTCTAAATAATTTGACCGGGGTGGCTGCATGTACAGAATACACTATAAAATTTGTAAGCAAACTAATGAAATAAATAA
CAACATCGTATTGTAACGACTCTGTGACCAATTAAACTTTTTGAAGCTTGCAAAGTTATTGCTTACGCCGATTGCATGTCGCACGTCAGTCATGT
GGGCACAGTGCTATCAACTGATAATGATAATTTCGATAAGCACCTGTGGAACGACAAGGTAGGCAATGCGGTTATATGAATTGCTTGCCAGATAA
CTCACACCTTGGAGAATGTGCACCTAGGAGATCGAGGATGTTTTTCTGCTTTGCAGCCAACTGGATTGGATTAATCATGGCTTAGTTACTTAATC
TATATGTCTATTGTATTGTCGTATTGTATTCTACGCCATCTGGAATGCGATGTATTATCAACATGTTCCTCTTTTAAGGTGCTCTTTAAAAGAGC
TTTGAT
(SEQ ID NO: 1003)

Exon: 1001..1515
Exon: 2239..2806
Start ATG: 1118

Transcript No. : CT26064
GTTGGATGTTTGGACAGTTTCCTTCCTCGCGCCGGTCGATAATGTTGGCCAACTAACACCGACCTGTAGCACGTCACCCGTAATAACCCATAACC
GCAACCAGTCCAAGCATCCAAGATGGGACAGAAAGTTTCGCGCACCGACTTCGAGTGGGTGTACACGGAGGAGCCGCACGCCTCGCGGCGCAAGA
TCATACTGGAGAAGTACCCGCAGATCAAGAAGCTCTTTGGCCACGACCCGAATTTCAAGTGGGTGGCCGGCGCAATGGTGCTCACACAGATCCTG
GCGCTGTTCGTCGTGAAGGACCTGTCGTGGTCGTGGCTCATCGTGGCCGCCTATTGCTTCGGCGGCATCATCAACCACTCGTTGATGCTGGCCGT
TCACGAGATCTCGCACAACCTGGCCTTTGGACACAGCAGACCTATGCACAACCGGATCTTGGGCTTCATCTGCAACCTGCCCATCGGGTTGCCCA
TGAGCATTTCCTTCAAAAAGTACCATCTGGAACATCACCGTTACCAAGGTGATGAGGCAATTGACACTGACATACCCACACTGCTGGAGGCGCGC
CTGTTTGACACCACATTTGGAAAATTTCTGTGGGTGTGCCTGCAGCCTTTTTTTACATTTTCCGTCCACTGATTATTAACCCGAAGCCACCTAC
ACGCCTGGAGATTATTAACACCGTGGTGCAGCTAACTTTCAACGCCCTGATCGTTTACTTTCTGGGCTGGAAGCCACTGGCCTATCTGTTGATCG
GCAGTATTCTAGCAATGGGACTGCACCCGGTGGCCGGACACTTTATCTCGGAGCACTACATGTTCGCCAAGGGCTTTGAGACGTACTCCTACTAC
GGTCCGCTCAACTGGATCACCTTCAATGTGGGCTACCACAACGAGCATCACGACTTTCCGGCGGTGCCCGGCTCCAGGCTGCCAGAGGTTAAGCG
CATCGCTAAGGAATTCTACGACACAATGCCACAGCACACCAGCTGGACCCGGGTTCTGTACGACTTCATCATGGACCCAGCAGTGGGACCTTACG
CACGCGTGAAGCGACGCCAGCGCGGCCTGGCCTCCTAA
(SEQ ID NO: 1004)

Start ATG: 118

MGQKVSRTDFEWVYTEEPHASRRKIILEKYPQIKKLFGHDPNFKWVAGAMVLTQILALFVVKDLSWSWLIVAAYCFGGIINHSLMLAVHEISHNL
AFGHSRPMHNRILGFICNLPIGLPMSISFKKYHLEHHRYQGDEAIDTDIPTLLEARLFDTTFGKFLWVCLQPFFYIFRPLIINPKPPTRLEIINT
VVQLTFNALIVYFLGWKPLAYLLIGSILAMGLHPVAGHFISEHYMFAKGFETYSYYGPLNWITFNVGYHNEHHDFPAVPGSRLPEVKRIAKEFYD
TMPQHTSWTRVLYDFIMDPAVGPYARVKRRQRGLAS*
(SEQ ID NO: 1005)

Classification: known_flybase_gene
Gene Symbol: ifc
FlyBase ID: FBgn0001941

Celera Sequence No. : 142000013383842

TCACGCCTGCCAACCACATCCTGCCCGAGGCAGAGGATGCGCCATATGGAGGCCACACCAACGGTGGCCAGACGGACGCCGAACGTTCGGCGAGC
AAAAGGAGACGAGGGCGACGTAGTATACTGCCGCACTCGGGCAAGATCACAATGGCAATAGTGGAGGCGCTGCGCAAGGAGAACAGTTTGCTCGA
GCAGCAGAACGACGCCTGTCTGCAGTCGCTCGTGCGCAAGGAGAAGCAGTTCCTGGACATGAAACATAACTTTCTGGCGTATATGGAGCGGCAGG
AGGCAGTGCTGGCGTTAATAAAGCAAACGACCATCAAGCTGGAACCATGATCCCGACTACTAGCACCACGTGGTAAGGACATTGTATGACAGCTT
TAGCTTTAAGTTGGGAATAGAGTCGCGGCGCTCGACCCTGTGTATGTTTTTCAATTCGTTCCTTTCTCAGACACAGATGTCTAATTCACTCGACG
TACAAAGCAGCAGCATAGCGAACCGAAGATATTATAATTTCTCAAACGTTCTTTTTCTAGCGTCATAAGTGTAATGTGTATGAACAATCGTCTGT
GCAAAAGATCAATCTATACGGTCTTTAGTCTTAAATTAAAAACATTGTCTTGAGGCGAACTTGTATGGTAGCTACATTTTTAAAAAAAAAACTAA
AACTAAACAACTGGCTAAAAAATAAATTAGATGAAAGACTATTATACTATATATATATACTATACTATATAGACTATACTATTATTTCTATTGTT
ACAGAATATCTTGTTGATATAATAGTAACGAAATCAAACATAAATTCAAATGAAATCAGTGTGAATAGCCTATTAAGTTTTGCATTTCGATCAAC
TTAGCGTGTGCAACAACCGCCGGTTATTTGTTCATCAACCCCTGCTGCAGCAGTGTGGCCGTAGCCGGAATGTGAAAATATCCGCAAACACCGCA
TGCGGACCTCTCTTAGTCGCTCTCTTAGCGCACAATGCGCTCTCTGCCAACCGAAATGCCACAGACTTTTTGTAGGCTTTTCCACTTTTTCGATT
TCGAGACTTCGAGCGAAACGGTCGTGTTTTTCGCGTGTGTGCGGGTGGCGGACGCGCGTGCCAATCGGAAAAGGCCTTTAAATCAAATGAGTGGC
TCGCCAAAGGAGCGCATCAAGGTGTGTGCGATTGTATCGAGTGTGTGTGCTTGTGCGGTGCGGAGAAAGCCAGCCAGCCGCCAGTCTGGGATAAA
AATAAAGATTAAGATTGGGATAAAACAAACGAACGGCAGCGAAGTGCACAAATTGCCGTGGAATCGGGGCTAAAGAAGGAAAAACAAGTGTGCAG
CACACACGGATTGAAATGTTTGCCAATGTGTGCGAGCGTCACCTAAATAAACAACAAAAAATTCGATTTGCAGCAAAGAGAGCGAGCGAGTGAGA
GAGCGCGAGAGTGGGAGGCTGTTATTGTTGTTGCTGCTGTTGCCGCCGCTGCATGTGGCATGCCCGAAAATCCCAATCACAATCAGCTGAGCCCT
GCCGCGCCTCTCCCTACCTCACCCCCCGCACCCATACGCCTTCTCACACTGTTTGTTGGCCAGTGTAAAAGTTTCTCGTTCTGTTTTGCGTGTCT
CCTCCGTTTCTCTTTCTCCAGGGCCACAACACTGGGCTACAAACTATGTGAAAACCCGTTTCGTTACATTTCCGCTTTGCCCCGCCTAACCCCCC
CCCCCCCCTCCCATCATTAATTCGGTTTTTTCTCTGCTGTCGCGTCACGCCTCTCACGTCTTTTTTTTACTGTTTTGTTGCAGTTGTTGCTTTT
GCCCAGCGCCTCTTTCATTCATAGAAAACGGTCAGCAAAGCAAAGCATAGCGAGGCGACAGCAACAACAAACAGCAGGTAGAGCAGAAATATTAG
CGCGATTTCTTTTCGTTTCGCCCAAAAGAGCAGCCAAAAAATCAACAAAATACGAAACACAAAGCCAAATCAAAAGAAATCAAATTTCAAATTCG
TGCGGCCACCAGCAAATATCGAAATAAAGAAATTATCTAAATCATCATCAGCAGCAGCACAAAAAATCGAAAATCTCCTCGCTGTGTGTGTGATGT
AAGTGCGATAATAATATTTAACAATTGTAAAAGTTTATTTTATACATCATGCCTAACTGGCGCTATTGTTCGCCCCTTTTTTTTTCGTCTTCCGC
CTTTTTTTTTATGAAATTTGCTACTCATATCAGACCAACTTCGTAACTACATCAAGTACAATTTTTAAGGTTTATAATGTTACCATAATTTGTTT
AAAATTTCCCATGATTGTCGTCATTTATGGGGTTTTCCTTGAGCGCTAATCATGCGGTTCTATACCACTTGAATGATAAGATTGATAACATTCTT
GGCAATCATTATCGAATCTATGGGAAAATCATAACAAGTTCCATTTTATTCGCAGGCAGAGAACTGAAATTAATCGTTTTGGTTAATTGCCAATT
TGATGAGTTCCATTTTCCAATCGCGATTTAATTTTCACATTAACAACACATTTGTTAGCCCATTAAAAATTTGTTTGGCATTTGTTTTCTTTAAA
AACAGCTCATTAAATCGCCGGAGTCCACATAAATCTTCTCGTCGTTTGTGGCTAAATATTGTCACTTAGCAAACACTCGAAAATATATAACTTAA
TTTATGCGCACGACTATTAAAAAAGAACTTGGAGGTGTCGAAAAAAGCTAAATATAGGAGGAAGTGTATTAGGTAATTGTGTATTCCACATTGTT
ATAAGCACTACTGTCTTTTTATTGTTATCTGACAATTCTATGCAATTTATTAAGTACATGGATCTTAAGTTGTATAAAAATAGACATGAGCTGTA
CATAAAAAATCAACATTTCGCTGCGAAGTGGTTCGAACGGGCAATTTAACACGATCTACTTAACTTGTTGTGTTGCTGTTTATTAATAAAATATT
TGCCAATTATACGACAGTTTGCGCGTTTAGTTCCATGTGTTTCGCCCTATTATTAAATATTTATACTTGATAAACACGTGCTTATTTACACCATT
AGTATGATTCGATCATTTTCTGGGTAATCAAACGATAACTGAACTAAACAAATGTTTTTCTCAATAATTGCGAATATTTGTATAGTAAAACAAGC
AGAGCAGTTTTCTGCATCACAGAGCTCAGTATCTGGTATCTGATGTCGCATATTGTAGATAAGAAACTATAGTAAGGGACTTGGTAAATTTAAGG
CGATACCAACGCATTGCGGTGTTGGGATTACGTAGAACATAGGACCTTGGATGCGATTAGCTCGGAAAGATGTCTGGTTTTTAGATAAATAGCGA
GAGAAACAATCTAATACACAAGATTCAAGCGGAAGTTTATAATCGTTGCCAAGAAAATTCCAGAAGGCTGATTTCTGCCTATGCACTTCAAAGCT
TTTCGATAAATAAACAGTGTAAAATAGTTTTTCCCAGATTAAAAATGCTTTTTAGGATGAATAAGTTCTGGTGAATTTCTCTTTGCTAGAAATAC
CCTCTTGTGCATTTTAAGTTTTTTAACATAAATTGAAATTATTATTTCTTTAATTTTTCCTCTGCCCCTTTTGACCTGAAAAATCCATACGTCGC
TTGGTGACTTCTGAAATACAAATGACACCCCCAGGGGGTCACCCACCTACAAGTGACGTAACTTCAAAGCTCACATATGCATTTACACAAATTTT
GTTTGTCATGGAGACAACTGAATCATCTTGAGCAACAGCATTTATTACACTGGTTGACAAGAAACCCGTTTTTAAACGTGTAACCAAATCTACGC
TATATACACTTTTAGTTTCTTTATTTACTTTAACATATATAAATTCCAATATTTAAATATTTTTATATAAATAAGTAATTTAGTTTCTATCAAAT
TTATATAAGAAAAGGCGTGAGGTTTTGTAGTCCACTTGGGTTAGCAAGTTCGTAAGCCTTTTCCTGGATTCCTTATCGGTATTGAATTGCCGTGT
TGTGGTTAACCGCAAATAAGCAGTTTTGTTCATTTGGTTTTGGTTTACGTTTTACACTTTCCAAGACCCAGACCTTAGAAATCAGTCAGTTGTAA
CGTACATCTTATGTTAAGAGAAAAAGATATCTATCATGATATCTAAAAAAGTTTGGTTTAAGAACAAAACTTAAATTAAAATTTTAGGATTTTTT
TTTTCGTTCCTTAACTGAACTTTCTCTGTCACGCATTGAAGTTCAAAGTTATTCAAAACTTCCACTAATTGGCATTAATATCTTTTGCTTTCCTA
TTTTACTACATTTTGTTAATGTGCTCATCATGCGCTGTGTTGTGTTGCCAGTTTCTCTTGTTTAGGCCAAATATGAAATGGGGCAGTCAGCTTTG
TCATGACAACTGTAGGGCAACAAAATGTTTATCCAACTTCCTTTAACAATTGGGCACGCAAAACCGTCAGTTCCGTCAGTCATGGCCAGGGGTAT
GCCGTCGGGCAGGGGAAGGGCGGTGAATAGGGATTGGGTTCGGAATTGGGATTGGAAGCGGGAGCTGGACAGGTGCGCCCCGTGTGCGGTGTTCT
GACACCTTTCTCCACGGCCAGGGGCCATGTCATCGTCAGCATGACAAGCGCTGGGTTGCCCGGTCGGTTGCTTAATGGTTGATTGAATTGAAACG
AGGGAAACTGGGTTGTTTAAAGGGCTGTAGTTGAGCTTGTGGGTCCTAACCCCTAGATGAGGGTTCAACGAAAGTCAGTTTACTGGGGAAAAGCG
TTAAAACGGAGGTTAGGCAACTCTGGTTCCTTGCTTTTTATGTTGCGCTTATAAACGAACTTTGGGATAATATTAACCAGATATATTTGTTTATA
TAAACAACTTGTGAATAGATCCATTAGTTTGATCTTTTAGTGCATTTCATTTTAGCAGGCTAATGCAATTTCTTACACCTAGTTAACAAATTTGT
TTTGGTCTAACGCCAAATGTGTTCTGAAATGAGTTTTACTAAAAAGATGCATTACTTTTTTGCTTTTATGGATATTTAACTTTCAAGGGTATCTA
AATTTATTCATTTTCTTAAAAATTGCAGATGCATCTAGAGTTGCTGACAAATAAGGATACTAGATGACACAATTAGAATGGCATAATTTCATTAG
GACGAATTGCCTGAATTCAAGCGCCTGGCAATATTTATGCAGTACTTTCCTCACAAGCGTCGCTTTTCATGCACGAGCAGCAAAAGTTTAGTTGT
AATTATTATGCAAATGTATACAGTTCAAGCGACGAGAGAAAATGTTTGTCGGCTAAAAAAGTGAAGAACTTGAAGGCGACGTCAAAGGCATTTGC
ACAAATCATTGGTTGGCTCTGCCAGTGTTGCCTAATTGTTATGCAAAAGGGTTGCTCACTAAAGACAGACTGTTGCTATTGTTGTTTATTGCTTT
ATTATTGTTTGTTTTGACTGGGATTCTTCTAAACTCGATTGAGCCTTTAAAACAGTCCATAGTTCACTTCAAAACATAATACATAACAGCATAGA
TATCAAATTGAAATGCAAGCTTAGTATTGGATTTTAATATTTATATGCCAACAATGGTAAGCGACTAAGAGGTGGCACTTCAGTGGGGAAAAGAA
CGAAATTTAATTAAAATTCGTTTGCCTTTACCCCCATCACTTATGCTCTTCGTCTTTGCAGCTTGTGTGTAGTTTTTGGCAGGCTGCCAAGTGGA
AAAGCCGCCTGTGTTGTCAGTTTCCTTATACGTGGAGAAAAATTGTGGCAAATTTCGGTATTTCAAGCCGCAGATGTTAAACATTTTCTTAAAAA
CTTACAGTTACTAGAGTAGATTCGTGTTGGCCCAGGAAAGTTCTTTCTCGATATTGTCAAATGCTCAAAAGGTGTTTAATGGATCGTTTTTCTAA
GTGCAGGCGGTTGAGACGACTTAGAGATAAGACTAGGAGGATGGACCATGGGTGATGGAGTGTGGCAGCCACTCAAACTTGACATAGACTTGGGC
CACGGGCTTTTGTTCGTGAATGTGCTTCTGAGGTTGTGTGTGCCTGAGTGTACAAGGACGTGAGCACTATGTGACCACTGTGGCACCCAGGCCAT
GGACGGGAAGTCCTTAGTGGAAACCAATTTCATCACTTATTGTCCCCAGCTAAGCTGGCAAAGAATCCGACTCGTGAGCGCCCGGCACCACCTTT
GATGGGATTTGAACACTGTGCCTTAACTCGGCTTGGATTCCTGTTAAGTGAATTAGTGAAAAACACATTTTAGTTTTGAACTGCATTCTTCTTGG
GTTCTTGATTACTTAAAAGCTTTTCCTCACGCACAGACTGGCACAGGCAAAGAACAAGGGCGCTTGTGGCTTTTAAATCAATAGTGTGGCAGAGT
GGTAAAGGAGGCTGAATGGATAGGCATAGAATGGACCTTCGGCTGGCGATCTGTTCATTTGATTGAACTGAGTGGTCGGAAACCTATTCAATTTA
ATAAGCGCCATTGAAAATTGAATGAGCGGTAAGGACATAACGATTAGTATGGCAAAATGTTCGGAACGCTATAAACGGATTTGCAACAATGCAGA
CTGAACCACTGTGTAATTTATTAAAAGTAAAATTCTTTTATAATTACCTTTTTCTTAACGCGTTTGAAATGGCTGGTTTGCTTTTCGTTTGCAGA
GGGAGTTTACAAAGTATGTTGGGGTTTTTAAATAATTGCGTACTCAACGTGCACGAAATATTTTCCTTTGTTTCATTGCCTTTTCAGTTGTCTCT

FIGURE SHEET 542

CTTTTTTTGCCTGTGAAAAATATGGCAACGTACTTAAGTTTCTTGATGCGCATACAAAAACTGACAAATTGCCTTCATGAACTACCCACCCACTT
TATTTTTGCCTTTGAGTACTCATTAAAACCGGGTAAGAATAAATCTTTACAAATTTCAACGTTCGCTGCGGGAAGTCTGTTTAAAAATGGGACAA
TGTGCATATTCTCTAAGTAATTTAGTGAGCCAAAATCACATTTTCCTTGTTACCAAAACATACGGGTTCGAAAAAAGATACCAGAATAGAGTTTG
TGTAAAACTCTGGCGAAAAACTGATTATTTGTTGGTGCATTTTTACTGTCAGTCATTTAAAGATTCATATTTTCCCCTACTAGTTTTAGTGGTAC
TTGTTTAATTATTTTCTTTTGGTCACTTGCTGTTGTAGTGGCCTTTTTAATGTGTTTCCCTGAGAGCTTTATTTTAACTGGTTAGCATGGGAGAA
CTGCGAGCTGGTTAAAAGGATAAGCGTTGCATGAAATATGAAAATGTCCTTGACCAAAATGCTGCCTGTTTTGAAAATCCTAATTAAACAAGCTT
ATTTGTACAAAAAATAATTCACTATTCTTGTGATAAGATTTAACTATCATTTCCACTTTAACTTAAATAAATGGTAAACTGCTCATTCAAAATGCT
TATCGAATGCCTTTTAAATAGTAGTTTATCATAAGCTTGCTGAGTTTACCCCTCGATAGCTACACTCCTTTATTGGCCCACTGAAGCATCCATCC
AGCCGGTAAATCAATATGCCACCTCGAGAGGAGTCATCCATAACGACCTGCTTGCCAAATATTCGTGCGCAGTTAAGAGGCGAAAAAATCATGAC
AGCAGCTGGGTGTCGACAATGGATCCTTGTGCAGGCACCAGGATCGCGGCCCCAAAGGCGGGTAATGTCATTAACAACAAATTGAGCACATTAAT
AAATATGAATTATGATTGTTAATAAAAAACGTATGGCCAAAAGCGACGGAAGTGGAAGTGTGGCGTAGTTTCGGCGAATTTGCACGCCCAGTGGC
AGGAAGCTGACACCTATCCAGTGCCACGCCCACTTAGAAGGGGCGCAATAAACGGAGTTGCGGGTAAACCAAATGGTAATTCACCCTGTGGGCCA
CAAGCTGATGTTGCATAACTTTCAGCGCTCCATGGAATGCGAGTGTGTGGCAGACATCATAAATCAATTTTGGTCACGGGAAGAGGCAGCCGAGT
TTCCGTAGTTGAATAAAAATAGTCTATTTTATTTCGGCCAGATTCAATGGGGAGTCAAAGCTCCAAATGGTCAGCATATAGATAGAAGGAATGAA
AAGCCACTGCCAGTTCATCGAAAATTCCCATCGAAACAAGTTTAAGTATCGACTGGAAAGTTTATTTAGTCGTAACCTATTCCCTACTTTTAAGT
ACACTAAGCTAGCTGCTGTCAAACGTGGCCATACTTTTACCTTAAAATGCACTTTAAAAGCCATTTACAACCTAAATCCTCGTAAACCGCGCCCG
AGCCCGCAAACGATTCATCATAATGGTGGCCACAGCCATTTTAGCCAAGTTACAGCTCATCCGCAGAACGGTTGCCATTTTGTTCTTTATTATTC
AAGATACGGGTCGGAGGCGCTTAACTGGGGCCACAAATTGGGTACTACCTAGATATTTGTTGGCATTAAAAATGCCTTTGGTATATTCGATTTTA
TATTGAACTCAAGTGCGCTTTCAGTGTGTTTTATTGATAACGTCAGCTTGTCACGTTTTTTTTTCTTCGTCCCGCTCGACGCGAAAAGTGACAGC
CGTGAATTAGGAAAACGAAAAGTTTTCCCTCAAAAAATGTGTTCCTGTGTATTTGTAATGCTATCTGTGTAATTTGGACCCAACATTTGCCCAAA
CATAAGGGGCGTCCTGTTTTTGCTTCTTTCACGACTGACACTTGTATTCGAACTTTTTCCGTACACGAGTTTTCGGTTTGTTATTTACAGCATGC
CACATCACTTTCGTCATGATGATAATGATGATTCCTTTATCTTTGCAGCACCTTGCACATTCATCGCATTTCCTTTTGCCAGTGAAGTTTCTTGG
CTCTAATGTAATGTGAAATGCTACAATTAAGTGCTAGACGAGATTATCTACTAGGTTGCGTGTCAAAGACCATCTTTTGTCATCACAGCCTCCTC
CATTTTGAAACGTAACTGAAACTTCACACACAATGGACTTGAAAATTAGATGATGCCTTGCAAGATTGATTGCGATAGTGCTTAATTAAACAAAA
CCTGCCCAGTTCACCGTGTAATGTGATTTGGTTAATTGGAAAATATTTGGTCTTAACCATCATGATTAGGCGGCCATTGAGAAAGTTTCACAATC
CACTTGGTTTCGGTGTGAAACCGTAGCTTGACTAACAAATAACAAAAATAACTTCATTTAAAAATCGTTTATTTCCGTAATCGAAAGCTTACAAA
AAGGGCAATCATCTCTTTAGGGCGAATATTCGTTTTTAAAATGCTCGAAATTAACAGGCAGATGTGTCATATGGAAAGAGAAATATATGCAAATC
GAATCAGAATCTTAAATGTTTGTGGGGTTTTTTGTGTTTTTTTTATTTTTTATTATTTGCCTTGGGCTGTGCATGCGTTTGTCATATGTATTTT
TAAGGCCCCACTGCTTTTGGCCATCTTTAAGGTTGGCTGGTTGTTGTTGTTTTTTTTTTTTGACTGATTGCCGCCTTGGGCACGAGTGCGTGTGTA
ATACTTATCAGTCCATTCAATTTACATACAAAGTGCTAAGTATAATTGAAATTCGCAGTAATTTCCTACTGAGCTCCGTAAACTGTCAGTGAATT
ATTTACTTTCATTTCATGAGTTTTTTATATTGCAAGGAAATATTTGTAAAATTCATGCACTGTAATTTTCTTTCTCAGGATGACTAATCTATATT
CTTCTTCACTTTTCAACGCCTTTGTTTAATGATTTGATAAGCACTATTATAATTAAATTTCTAGCTATGTAGGTAACGCCTTTTTAATCTAATCT
TTTGGCCTACGACAACCTTCAAATCACTTGATATCAATTCTATTAAATTTCCAGGCACCCGCCCTAATGAGCGATAAAATGGGTCTTTTAAACTT
TTTATACTCTATTCAATCATTAATTTGTTTGTATTTATAAGCAAACCCCTTTGTTATTAAATGCAATAATCCGTTTATACTCTATGCAGCCTATA
AAAGAACCAATAAATAATTTTGCAAAACAGTTTACGCGGATTTTTTTTTAAAGTGCAATTAATTCTGAAGAGCTCTTGACTGGCTTTAGGAATTA
AAAGCAATTTGCTGTTAGAAGTTTAATGCACTCTTTAATTGGTCTTTTATCGTGCCACTTAAAAATCGTCTGTTTTTGGTACAATGTCAAAGCAC
GATTCTGATTTGTTCGAATTCCAAGATAGCTTATCTAACAAATTGGTAGCCAAATTCAATTGCTGCAGAAACCAAATGTACGACATGGTTTGTTT
TACAAGTGATTGGAAAATGCCGTCTTATCAACGAAAGGGTAACCAACTCAGTTACTAATAACTCTTGTTGTATACACGCATGTATACCAGCAAAA
AATATCGTTTTCAATTAGCTATAGAATGTTCAACCCATTTTCAGGATAGTTATCTTTTATTGAAGACCAATTATTTGGCAGAGTGTTGGCTGTTG
GGAACTCAACCCTTTGCCAAAATGAAGCTGATTATGTCTGCAGACTGCGCTGCTGGAAATTCAATTAATTTTGAATGCAATTTTAAGTGCACTTG
TGTAAAGCATTCTACTTAGCAGACGCTTTACCTTCTGCCTGCAACTAAATTCACTCGGACATTTTCGTTTTAAGTTTTGCTAGGGGTTGTGGTAC
TTTTTCGGTGTTTTCTGTTAAAAAAAGAGTTTATGAAATACGCTAATTTAAATTAGCTTCCGACCAGAGACTCAGTTTCACCACCCAGAGCTATT
CGACAAATCCAATTTCGCTTTTATTTCTCTACCCCGCCCATCAGATCGGGTAAACAATTTTGTTTTGGGTCTGGTTGGCGGTATCTTTATGTGAG
TCCCTAGTTTATATATTTATATAGTATATATATTGCCTGTCGTCCCAATGTATTCCATTAGCCAAGCGAATGCTTCCCCGGGGAAACGCACAGTT
TATTTGCTTTGTTAATTAAAATTACGAGCGTCAGACAAATTTGTCTGCAATGTACATGCAATGGGATCATTAGAGGTGGTTTGATTTGTTGGTCT
ATGGTTCATTTGCAGCTAATTTAATTAACAGTTTGAGCAGCACTTTGGGGCTATGCTACTCTTTTAGTATATTTTTTTAAGAGCATTGTCCAATT
TGATCGGAATCGCCGAGAAAGCCTTTTTTATGCCACGGTGTGCCAGGCACACTTGCTTAATCTTCGGCTATTCAAGTACAAACCTGGGCCGTTTG
GTTTTTATTATTGGTTCAAACCATGCAAGGACCTATTCATAGTCCTCACCACAGATGCAGCGGAAAATACAGAGTTCCCAAAAGTGTGTAAAATG
CCGCGGAAATCGACTTGCCTGCAGTTGTTGCTTTTCCTGGCTCCAAATACCAAACCATTTCTGAACACACTTACTAAAATGTAAATATTAACAAA
ATCGGGTTTGCTTGTGCATTTGTAGTTCTGTTCCAGCTTTTAATTAAGATAGCAGTAAAAACGAAAATATTAATCATATTCCAGTTCCGAATATT
GATTGGTTATTTTTGTAATCTTCATTTGCAGTAGCATAGCTGGATTTCTTTTCCAATTCTAGGGCATCTCTCTTTCTCTCTCTGAGTTTCCAC
TTTGCTATCCTTCGGTTTTCCCTTGCCAAACCTAATAAATTTTGCATTGTGCGCGGCGTTTGGTTGAGCGTCGCAGTTACCTGAATTCAGATATT
GCCTTCCGGACATACAAGTTGGCAGAAGCTGAGGCTGTGGTCCTTTTTGCCCAACCCGCTATTCGAATCCTTAATATTCCCTTGTTGGCTGACCC
TGCGAAAGTGCCATATGGCATGCTAAATATTTTAAAACACGAAGTGCATGCTGTGCAGCTTGTTTTGTGTTTTAAAGTGATATCATAAGCCAACT
ACATGATGTTTGGATTTTGGAAAGTGTGAGCGACTGTTAAAATTTGTAGCTAGGTACTGAAACTTGGTCCTTTGTCCTTTAAGATGTTTGGAAAG
AGTTATGTGCACATTTGTGCGGCCCTCCTTCACAAATTTTCCGAGTTACTGGCTGTAAGTTATTTGCAACAGTTAACATGCAATATAACTGTGGA
AATTGTAAAGAAAATATTACTTTTGCTTATGTCTACCCAGAATTTAGAATTCGAGTGAGTTTTGGGAAGACAATTTTATAGCCTAATCTAAAAGT
CCCAACATCATTTGATTTCTATTAATATTGTAGTGTATTTCCCTAACTTCAGTATTATAAGAGCACTTTTAAAGTTTCCACTCCAAGGAACTTTA
GAAAAATCTTATTATTCAACTACAGTGCTCTTGACCTATGGCTTCCACTCGGCCTCGGTGCATCTAACTCCTCCATGTCTCAAGACAAAACAGAT
AAATGACTTTATTTGTTGAGTTTGCTCTGGCTGCAACATCCCCAACCGTAATCCTATCACCACTCGAGAAGTCAAGTGGCGAGGACCAACTGCTG
AGCTGGGATGAGCCCTTCTATGGATTCAATGGGTGAGCAAGGAGGTTCAGTCAAGCGGCTTTTAAGAAAACCATCTTACATCATAAAAGTATAAA
ATTGCTGCACAATGTGTGACCACGAATTACTTATTTCAAATAACATGAAACGGAACAAATTTGCATTTGTTTTTTTAAGCTATCATCTTTGCAAA
AATGGGTGAAAAGCATTTGCAAACTTACAACCTAAACCTCTTAGGTACAAAAAAGCGTTGAATTGCTTTGTTTTCCTTTCAGCCAGCTCCGGCTA
CTCCTCTCAAGAAGTCCGAAGTACACACCTGCTAACACGGGCAACAATCTTGGGGCAGGGAGTCCTGGCTGCACTGCATCCCCAGGGCACCGTTT
ATTCAGCAGACGATGACGGGGAAAATGTGCTGTGCAGAAAGGCAGTTTGCTTTACTCTACAGCGTCTTTGTGTTCCTTGGCGCATCAATTTTTAA
ACAGACCAAATGCAGCTGAATTGCATTTTAAAGCAGACCTTAACGGTTCGTCTGCAATGCGTAGAAATTGGCCGGAGGCCTATTTTAGATACATT
GTGTAGCTAACCCAAAATCCATTGTTTGCATTGCATTCTAGCTTGCTTTAGGCTAAAATACGAAATTGAAAATCTATTTAAAAACTAGTTACCTA
ACTTAAATGTGAGTTTAAGATTGCACAACATATGAAATACATAGAATATGACCAATTGACTAATTACATCTATTACATATGACTAATTTTTCATA
TTCTCTGTCTTTTCAGTAACTAGCAAAATAAATTAGGTAAGTGTTTGCCATTTTCTCTTACTCAACTTGAAGTTCAGTTTTCTGCCACAATCGCT
TAGGTTTTGAATTGGCTAAAATGAATCTACTGTAAACATCTGTTTCAAGTAAAAAACTAATATTTTACTGAGATTAGGGTCTGTTTTGAGATGTA
GGTTGATGGTAAGGGGGGCCTAATTTATGTTGAACAGAAGTACGTGCCAAATTTCAAAAAACTAAAGTCGAAAACTTTTTACGCCGACACCAGAG

FIGURE SHEET 543

AAACAAAAAGGTCTATGCTAATTTCGCTGGTTCGGGCAAGGTAATACCAATATTTGGATTATCCGGCAGTAAACATAAAGACTTCCAATTTAGTT
AGCTGTGTCCTCGTTAATCACCGCCGTCTGTTTGTTGTCATGCTTTATTTTGTTGAGCCCGGCTTGTCGTTTTCATTAACCTTAATTAGCGTGTG
CCGTTGACATTCGTCACTATCCACATAAATGCAATTGCCTTACTACACCCGTCACTATTCCCCGCCGCACAGCCATGATTATCAGCAGCAACATC
ATCGCCAAATGAGAGTGATATTTTGTGTCACACGTTTTCCACGTCGCTCCTCCGCATTATATGTATGTATGTGCTTGCCAGCTTTTCTGGACTGG
CCCGAAGACCTCTTCGTTGGCGTCTGATATTGACCATGGCTGGCATTTGTGGCCAACCACCCATCTCCGCCAGCCAGCCAGTTGCTCATTGCAAC
TGACTTGGATGACTGCCATCGCCGTTTGTGTCAGCTGCAAATGAGTTTCTGGGCCATAAACGTGAAGTGGAATAGTGGCAATGTGGATGCCTGGG
CCACCGAGTTTTGAATGGTCTAGGTTCAGAGGTCTTGAATATTTAGGATATCATTTTAGTATAGTGTAGTATAGTAATCTTAGAAACTATACGTT
TATACTATACGTTTCATATGCCAATTAGAGTGTTAAATAATATACCAACCAGCACTAATTACGACGCCCATGCCTTAAGTCGTTTTCCTCCCCAA
CTTGGCTTATAAGCCCCCAGTTGCGATGTCGCTTTTGCTCCATTTACTTGCCAATGACAGTGAGTTCGAAAAGTATGTCGACCTATCGCTTACTT
CATTCACTGCCCCCACATGGGGAACTAGTTTTTTTGTATTGGAATCGCATTGCACGCGGCCGGATCGTGTGACTTTGAACTCAATAAGTGTGGAT
TGGTCCGGTCGATTTTTATGACAAGTAGCGAAACCGAACAATATTAAACTGGATTAAAAAATGAACCAAAATGAGCCCGCCAGTTGTAAAAACTT
TCACGTACTTCATTTGCCAGATGAAAAAAAAAAAAAACAAGCTATTTGTGCCTTTTTCCATCTGACTGTTTGTCACGTTTGAAGTTTGTTTGGCG
TTTTGTTCGCAGTTTTTGCTTCCTACACACGGGTTTCTTGGGATCTTGAGATCTTTGGGTCGCGGTCTGGGTTTTTTTTATGATGGTTCTTCG
AATGCCTGGCAGCTTGAGGACTGCTTGTCAATAAAGTTCTTGACACCTTTTCTTCATTTGCACAGATTTCTCTCGCAATGACTTTCGGTTTGCTT
TCGAATGTATTGTTTTATACTCATTCGCACACATTCCATGTAAATTCAATTGCTTTTTTCGCTTAGCAAAATAAAGATACTCGAACGGAAGCTAA
TGAATATAAGATAAGCACGAATACATTAAAAGTTTATGGTAGAGAGTTCGTTAAACTTGCCAACAGCTCTTTATGACCTAGATAATTGAGCTTTA
AAACAACAAATGAATAGTTGGAAATGGGATGCTAAAAAATCCTGAACTATAAAGTAGTAATTGTACCAAAAAAAAAAGTAATTGTTCTGCTCTGG
ATTTTCATCTATTTACTTTGCTTGCCTACAAATGCTTTATCATTCATAATTTGTATACTGCCGAATGAGAATGGCATAACGAAAACAATAGCTAA
CCCACTAAATCGCAATAAATGGCATTTGCATTCAATTTGTTGCATCAAATGCTTAATGACCGAGTGAACAAAGGCGGCAGCGACCTTTGGCAAAT
ACACGCACAAAGATATGAATATTTCTCCTTCCCGAATTTAATTGTCCAAACAAAAGCTACCCATCTCCACCTCCAAACTCAGTGCCCCGGACTAC
TACTGGTCACCTGCCTGACCTCGGAGTTAAGTTTGTGTGTGGCTTAATTGCTTGTGACTTGTTGTTGCTTCCTTGTCTTGGCTTGTTGAACTCTC
AAGGTAACAAGAAGTAGCAAGCTGGCCCCTTCCGCGGCTGCTATTTAATTTCCACGAAATGAAGAGGGAAGAAGCGGCAAATAAAATGTCTAAGA
TTGCGATTATCTTTTTAATAACATCTCGAGGAAGGCGAACATTACCACAAAAAAAGGCGGGAAACTGGCAATGAAAAGAAACTACAAAAATCACG
AATTTAATTACCACGCACCCCAGATAGCGCCTCAAATGAAGCAATAAAATCCCAGTTGCCTGGGAGTATTGGACATTGCAAAAGTATCTAAGTAG
AAACATTGACCGAATAGTAAATACAATATATTCAGTTTTTCCTACATGATTTGTTTAGTTTTTTTCCGCATGCCTGCATCTCAAAAAGCATAGCT
GACACAGGTCTTTCATATCAAAAGCGCCCCCTTAATCGTTTCAGAGTTTTGCTCTAAATGTTTTCAGGGTCCCCCCAAAAAATATGTGGCAGTTA
TTTATTTTAAATCTCATTCGTTTGTAAACGCCGCTTCACAAGAAAGCCAACAGACTGCTAAGAATAGCCAACAAATATCTACATAAAATCAAATT
TATCTCATTTTACACAACCCTTGCCAGGCCAACAAATGAATAAAATGTCATTGCTGAAATTCTGTGAGTGGCATTCATGCGCAAAAATCATTTCA
AGTAAATTATAACTTTTCCTCTTCACTGGTTCTAAAACACAGACATTGTTATTTATGCGATTTCCTTGTAAAAATAAACATTCATTACAAGTGGT
CAATTTGACTTGGTTATTTGAAGTATCGAAATATTTTGTTCGAAGTTCAATACCAAATGCGCCAAGTAACTATAAAGCAATATACTTTAATGAAT
AATCAGGTGGATAAACTGAAAGCACTGAGTAATTGAACTATAATATAGATATTTAAGGCCAAATTGAAAAGCTCTTCCTGAGAGTTGCCCCGATT
TCATCAGCCCTCCGCCGTATGAACGTGAGGCACTGGCTCCTGACCCTGCTGCTGATGCAGTTGTTGCGGAGGATTGTTCTGAATACTGGGGTGCT
GATGGACTGTCGGCTCCTGCTCCTTATCTTCCATTTCCATCTGCTCCTGTGGCTCGAGCGGCGTCTGCGGCTGCTGGGTTTCCTCGGAGGACTCG
GCATTAGGGGGATCCGGATCACCATCACTGCTGACCAGCGAGTAGTTCGGGGGCTTCTTAAGCAGGTAGCGTGTGTTCGGGTTCTGTCTCGTTTC
GAGCTCCAGGCGATCGATCAGCCAGCCCTGTTTCTGGTTGTTTGAGGCCCAGAAATAGACGGTCCCCCTGTCCTTGGGACCCTGGACATGGAACT
GCAGCTGGGCCTTGTCCTCGTCACAGCGATTCTTCTCGTTGGACAGATTAAAGCCCGACTCCTTGATGGGCTCGCCCAGCAGACCGACCGCTCCA
CTGTGCTGGCGTAGCTGCTGGATGGCCAACTGATAGAACTCCGTCTGGCGTACACGGTCCTCAAGTCGCCAGCGCATGTAGGCCAGGCCCGAGAT
GGAGGCGAGTGCTCCGCAGATGCATATGCTGCCCATCGTTCGCTTCGAGGGCAGACCGATACGCAACTTTAAGGTTGGCATGGCGGCCTCTTAGT
CGGCAAGAAATCACTTTTAGAATTTTGTGTGTGTGTGTGTGGAGGTGTCAGAGGCCTACAAATACTTGAAATGCGAAACAACTCGATGACAATGA
TCTCAAAGATTTCGAACTCGTAGCGCCGTTCCCACAAGCACCGATGTATCACTAGATGGCACTTACCACCGAGCCTTGAAATCACTGCCGCTGCC
TGGGATCGGCGGGCGTTGCCTCCGCATAATTGCGCTGCAACTTCCTCCTTGGCCTGGCCAACTTAATGCTGCCTGCTGGCGAGCAGAGAGAACCG
GCGGCCTGGCTCAATTTCATAGTCACCACCCAAAAGGCGGGGACCGCAAAACGACGTAGAAGAATCCACAGATAGAACACAGAACTCGTTTTGTT
TCTCTGGCTAGCTGTACATACTAGTTTTTTTTTTTGGTTTGTAGGCCAAATGAGCGGCGCCATTAATGACAGCCCGAAAAGTGAGCCGTCCAGTG
GAGATGGTTCACTACCTTGCATCCTTGTGGCCCTTGATCGTGGGAGGGTATCCAACAAGTAGAATAACGAACCCGAGAGCACGCGAATTCTTCAG
ACTGGGAGTTCTCTGAATTTTACATAATAACTTATAAAGCGAGATGTTTTTTTAATATTTGGTTCTGATAGGTATTTCATAGTCAGCTCAACCGC
GTCCATCGATATTTTTTTGTTTATCTCATTACAGCAGTTATATTTTTACTGGTCAGGGCCAGTGGAGTCGCGAATAGAAGCAGACGAGAGACCAA
TGAGTATCCAATTAGGGAGCACATAGTTATTTAAAAATAGTTTTCCAAGAACGCAGGGTATGCGATGAGAAATGCCCCCATAGCGCGTCGGTAAT
CGATACTCTTGCAACGCCTGTCACGGATGGGAACGGAATATTGCATCTGATACTGGCCAGAGTGCGGTTAATCTATCAATGCATCTTCAAGTTTG
AATTTCTGCTGCGGCGAGCCTGATGTTACATTTCTGGCCTAAGTGGCCTCTGGTGTGGCGGTCCTCCTTATCGAGGGGGGGGGGGGGGTTGGAG
GATCATGAGTTACTCAGTTAGTTACTCTGTCTGTCTGCGTGCCCGTCCTTCTGCCCCCCACTCCGCTGGCCGGGAAATGTGACAATTTCTGTGTT
CGTTTTTTAGCCTCATTAAGACCTCTCTAAACACTGCCACTTAAAGACCATTTTGGTGTGCTTATCTTTATGGCCAAGACATCTAGTGCCTGCCC
CCTCCACCATCCACCGAGACATGTATGTATCTTCGACGGCAAGTACGCCTCATACATATGCTTAACATGACTTTGATGTACTCAGCGTGGTGGTC
AGAGTAAGATCTTTAATAAATCAAATTGCCTTGGTATTCGGGAAGGGGGTATGGGGTACTTAAAGCTTAATCTCTCTGCTTAAGTATTTCCCAGA
AAGTAATTCTATGAGTTTTATAGTCGTTCGGGAAGCCACGGGTTTTGCAGGTGTTCATCGTACGTATACTGAAATCTGGGTATTAACTCTTTAGC
GCGATTGGCCATAAAAGCTAAGTTGAATGCAAAAATTGGTTAATAAGTGAGTCATTTCCGATCAAAAATTACAACCAATTGTAATGTACAGGAGG
AACTTGTTATCAGAAATTACAAACAGTTTCGAATGATTATCTTTACATAGTAAGCTTTTTCAAGCCGTTTTAGCAGTGAGTAATTTTAGCATTTG
ATGATTTCATATTCTTTACAACATAAGTTACAAGTTAAGCTGTAAAGATTAATTAATCCCCCGTATCAAATTTAACATTTTCTCTGGTAGACACT
GACGCACAATCCGAGAAAAGGCAATTTATCAACTTTTTAATGACATATGTGCTTTTTGTTAAGTTTTTATAAGCAAGCGTCAAGGCTTTTTAATT
AGTTTATGCTGAAAACGAGTAAATGATGCTCAGCATAAATTAATTGTGAGTAGGGTCGGATCCGAGTTGAATCATAAAACTGGTTGCTTGTCTT
CCCAAAGATGAAATATGCAATTGAGCACAACAGTGCCGCAAATAAGTAATTGCCGACTAGTCTGCCTACGATGTTCTTCGTTGTTGATTATGTAT
TTTGTTTATTTAAATGATTTAGTCAATCCTAGTCGCTGCCCATCGATTCCTATACCTTCATTAGCTCAAATGGCCTTCAAGGCTCACCGGCAAAA
TTATCCATTTGCTTAAAATCTTAAAAGACCATAAATTATGAAAGACTACTGAAGATGCCAAGCAGAAGAGGACAGCGCAGTTGTTCGTTCAATCA
GGCACTTCTTCAGTCAGCCATTTGAGCGTTCACTCACTCAGCTATTATTTTCAATAAAAACAAAATAAATATGGCAAATTGTTGGGACCAGCCCG
CCTCGGCAGCCAGCGGCAAAAAGTAAAAATCAAACTACAAGTCCAAGCAAAACTACAGAAAACGCTGTGCGCCTGCGCAGCACGCAACGCCAAAA
GAAAAGCCGCTGGCCAAGTCAAAGGCAGAGGCAAAGGCAAAAGCTGCTTCTCGGATGCGGCTTAGTTGGAGCCAAAGTCGTAGCCAAAGCCAAAG
CCAAGGTTTCTGCCTTTGTAATTGCTTGTCTCCGCTCGGCTTCAAGTACGGGCAGCAGAAAAAAAAAAAACAAATATCCAGCGACATGCGTCTGAG
TAATGTTAGCGCCATAAATAGGCAAGACAGACAGAAAGAGACGAGTTCGCCATAATGGAGTGCCTCGACTACCACATACCTGTTACTCAACTAAG
AGAAGTGCGAGATTTATGTTGGATTCATGGGCGCAGCATACTTGTCAAAGCGTCCAGCATACCCTTTGCTCGTAGGGTAACCAACATGCTGATCG
AACCTCGACGGTCAAACCTTGGTCCCAACTTGTGTGTTTAATTGCCAGTTGTAAAAATCTTTTAGGGTGGAGCTAATCACCAAGCTACAAATGCA
AAAATAAAACTTCCCTATAAGTGAGTTGAAGGCCAACTCGGCTTTATTCTTAACTGAAAGTTCAGTAAGATTAAATTCCTTATCCTTTAATTTGT
TCAATAAATTAAACATCTTAAATGCAAGCCGAATGGTAATTCTTTGCCCATTTTTAAGCCCTACTTAAATTTTTTATCTTGCTGTGGAAGCTTGG

FIGURE SHEET 544

CCACTCCCTTTTTTTAAGCAAATGGAAGCCGCATTGATTAGAGCAGCACATGGCACACATATGTTTGGACATGCCACCATGTGGACCATGGAACT
GGATACAGCAAAATCAGACCTCGAACTACTCTTCCGCCTGAACTATGGGATATTATCTTATATGCCTGCTGCTGGTTATATGCCGCTGTTTCGGT
TGCTGATACTTTTGCTGCTGTGTAGGAGCTCGGTTTCCATCTGGGAAATGGGTGAACAATGGTCACTGATAAAGTCCAGCGAAAGAGAGCTATTT
CGAAGCACTCGTCTGTAAAGTAAAGTAGCCGACACAAAACACCAGCGAAGCTAGCAGCTCGATGTGGGATCTGTGCCTGGGGATTTCTTTCTTTT
ATCATCGGCTGTCAGGCAATCGAAACTACATTCAAGAATTTTCTATTAAGAAAATGTAACCATAACATTTCCTGCAAAGGGAGCGGTCGGCTTTT
GTTTTGTTGTGCAACTTATGGCAACAAGTTAATTGTTTCTTTTATGTTCGTGTAATTGCCGGCGAAAGCCAGCGCTCACTTTACACTTTTTTCTA
CTTCAAGAACAAACTAGAATAGCTCTTTTAGTTTTGCAATATAATATATCAAACGAGCTTCAAGGGGTCCCAAGAAAAAATTTTTTTTTTTAAGT
GCTATAAATAAAATGGGTGTAGGGTCTTTTAATCTCTCTATATACATTTCGCTACCCATTTCTTGCCTTCTTTCAGCAATTTGAACTTATACATT
TTGGATAGATAACATTTCAATTTAAAAACACACTACACTGGCAAAATAAATAAGGCAAATAGCTCTTTGTTCGGCTTGGTCTTTTCTGAAAGTGC
ACTGCGGTGGAGGTAGGAGTGGGAAGTCTTGGCACAGCCTCCTCGAGCTCTCCAAGATGCAGTCGCGGATTAGATGACAGATTAGTTAAATGCGC
ATGAAATGAGGATCCGTTCGCGCCGTTGCCTGCTGGTCGGTAGAATCCCAGAACCCGTGGCTGCCTTCAGAACGCTTCCTACTTGGCCTTATGAC
CATGCGGTGCCTCCTTCGCCCCCGGCACACGTTCCTCTAATGTCTTCATTCGTTAATCAGGCGTCGGGCCAAGCACGCGTAAATCGCCTCTATTA
ACAGGCGTTGTAATTGCCGGTTGCATGCAGGTGATTAGCTGAAGTCCGCTCCATAGCGGAATTAGCACCGAAAGATGCGTAGTTGAGATACTTTT
CGATTCCCACAGGAACTCTTACATTTATTAGTCGCCGGCGCATTTAATTTAAACGCGTCTGCTTGTGACATCACTGCCATTAATGAGCTCATGAT
GTAACGCACTTAAGGGTCGTAAAAGTTGAACATTATAACTAAGCCCACAGGCTTTTTTTATTCCTCTAGGGCTCGAATAAACAATAATTTAAATT
TAGCTAATGAACCTAATGACCTCAGGCTGCCCTTGAACGAGTTGACCGTAATTTATATAAGTGGAACAGCCATATACCGCCGCACAATCAGGCAA
TCATTCCCACAAAATAATTTCCTAATCGACTTCCTTCTGGTGGTAGTTCATATTTTTAACCGCAAGTATCCGAGAAACCATTGGTAGTCCGCTGA
AATAGCCACCATTTTTACAGCCCACGTGGCTATGCGATTGTATTTCCAATTGCATTTTAGCAGATCCGATTTGAGGCAATCAGCGATTTATGCCC
CATTACGTCTCGTTTACTAATAACCCATAAATGTGCATTCTATCACATTTGCCAGCATTTCACACTAAGATCTATTGCTATAAACTATGCGAGTG
GGTTCTCATATTTGTTTGGTTTCCACTTCATTGAGTTTTCCTTTGCTATCGGTTGGCCATCCTGTCTAATGTGCTTTGTTGGCTAAAATCGCTTC
TGATAGGATTAATAACACACCATTCGCATAACAAAGCATCGGTATTGCACATCAACAAAGCTTGTAAGAAAATAAGAGGAAACAATAAATAATGC
TGAGTCGACTGGAACGAATATTTAGATACACTGAATTGCTTGGTGAAGGATTGCTGATTACAATGAATATTAATTGTTCTGTTAAATATTTAGCT
AAAAGTTACAAAGGTTGTGAATGGGTTTACATAAATCCTATACATTTTTTGTAAACACGAACTGAAAGTATCATTCACTTTAAAACTTTGGCTTT
TAAACGAGGTACTTATATTTAATTTTAAAGCAGTACTATGTATTTTAAGATCGATTTAAAGCCTCAACAAAAATCGCTGTTGCAATAACCATCC
TCAAATGCTCCTGCCTGTAGCTGTTTTGTTGTAATGACAAGGGTACAAAAGAACCTGCCACACCCGAAAACTTTTCCCTCGCTCCTTGCAACTCG
ATGTGGAAGAAATGTGCGCAAAAACCAACAAGTGATATTAAATGTTGCTGTAAAAGGGGGGAAGCTGCTCAGCCCTCTCAATATATTAATACCGG
CTACTTGTAGATTAAAGGGGTATACAAGACTACTTCACAAATATGCAAATGTGCTTCACAAATATGCAGTAGTATTACAATCTTTTTAAGGACTA
ACAATATTCATCTACAATCCAAACATTTTTTAAAAATTTGGTGTCCAATTAAGGTATACTCCTCTAGTGGAACTGTTGCTCAAAGTGCGAGCAAT
GAGTATCTGATAGTCGAGCCACTAGTCTCATATCTTGCTCGTTCGCATTTTTCGTGCGGTTCAGCGAGAAGAAGAAGACGGCTGGCATACGGAAA
AGCTGTATACGTATACGGCGAAAATGTTGAACGCAATTGTGCTCGCACTGCTGTCACTTTTCCATTTGGTTGCCGTCCGCATAAATAAATAAAAG
TCTGCGAGTGTGTCCGCATCCTGGTTGCCGGCTTTTAGCGCCGTTGTAGCTTGTTGCCAGCTTTAAGGCGCTTTAGGGTCCTTACACTTTCCGCG
ACTCACGATGATTCACCTCACCATTCACGTCCTGCGTTCGTTGTCATCATGACTTTGTTCTGCAAACGCACTCACCTTCTACTCGTACCGTATTC
ATGGCGCGTGTGATGAAAATTCGTTTTCACTCCTTGCGACGGCTGGGCGAAGTAATGAACCCGTGCTCACGTAAAACGCTTTCAGTTCGCTAGAA
GAATATTCTGTTTTTTCTTCTGCTCCACAAAGTACCTGCTAATTAGCTCTCACCGAGTGGTAATCATGTAAGTCAACAATTGAACGAGAAATTTC
ATTAGGGCAGCCAACAATAACAGCGCGAGTATCTCAAGTACCTGGTCCGCTGTTTGGCTCCTAACTCTCCGACCTCACGATTGCGTCACTTTCCG
CACACCGCGTCCTCTCTGACCAATCCATTAGTCGGGGAAAATCACATAATGCATGTAAACGATAATGAAAATGACATTAGTCCAGGCCGCACGAG
AAGCGGCAAAGCCAACAACAGCAGATTGAACATCAAATTCAGATGTTTTCGCATTCCCAAGGGGAGGCAACAAAATATTTGCACAGAGATGAACT
TGTGAATGCCCTTTGAAATACTTTTTTTAAAAATTAAGCAATTAGCAACATTTTAACTTTGCCAAACCGAATGCAATATGCCCTTAGATGCACA
TTGTAGCATAATAATGTAATCACAATCAAATGAGTTAACCAATTGAGAACAGGGTCTTGCTTAATCTGCAATACCCTGTAGAAATGCACAACCCA
GCGAACGGGAAAGCGAAATTAATGAAATTAAGCTAACAAACTGGGACCAAACCTCTGAGTGTGTGTGTGTGGGAAAATGTATCTATGTGGATT
GGTTTACGTGGTTCGCCCACGCGTATAGCATTAAGTTTTCCAGCTCCTTTTTTTGTCGAAGCTACAATCTTCGCCCCTCCTCGTCCCCGCCCCAC
GGAAGTGATAATCGATTCGCACCTGTCCTGATGTGGGCGTGTGCTCTCCTGTTGCCAACTTTTCCCTTACCGCCAACTGTCGCTCATTATACGAA
TTAATGTCATGCATTCGCGTTCGATATTTTCCATCTTATATTTAGCATTTGTCCAGGGGAAAACAAAACCGTTGACATCAGCCAGTGGACATTGG
GTGCAATTGACTACGACATAATGGCATGCAATGACATATTATTGGCAGTTAAGAGACTGTTGACCTTTAGCTCTGCTGCAATCAATAATCCCCGG
GACGGAATTCGTGTTAAACAATAAATATTTACCTAATAATATCTTTGTGATCAGCAAGTCAGTCGATATAGAGGATAATGTCCCAAAAATGTATC
TGAAATTCTTACTTTATATGGATATTATTCCCTTTAGCCATATTCCCTTATCTTCACGGATTTCAACACAATTTCCTTTGCATTTTCTTCTCTCT
GTTAACATTTGTACTATAGAAACTTTGTTTGCTCGTTTGCTACTTACTTACTATCTGGGTGTTGCGGCAATTTATTGGGTTTTTGCTTCATAACT
TCAGTTTTTGTACATTTTGATCGCGTGATAGTTGGCGTCGCTAAATAGGCAAAAACTGGCTGGCGATATACATAAACCCGTACAAGGTTCTGTCT
CGACCGAAATCGGTGGTCCGTGGCAGCACCTACCCTCTAATTCGTGGCTTGTTTGTTTGCCTTTCGCTTTCGCCGCGTCTTTCCTTGGACGCTCT
CTTTTGGCCAAAAGCTTCATTAGTGCCAATGCACCCATCATCGCAGTATTTGTCGCTGCCAGTTGGCAGCAAAAAGGGAGCTCCGAATTGTGTTA
CGCGTCCATGAGGTCAAAACCAATCGATTTTCTCGACTTTTTCGGTCGCCTTTTTTTTATATGTGATACTCCTGTTTTGTTCTTTGCATTTGAGA
ATTTTGTTTTCTATGGCACACGCTGCGTATGAGCAATGTATTTGGATAGGTTTGAACTTATAACTTCCACGAAACTTTATACACAGCAAAGATAT
CAAGTGAATTTTTTGAATGGGCTAAACAAGGTAATATTAAACTAACTACGGGTGAAACAATCTATTCCATATAAAAATAAAAAAGATGGCTTGAT
TTGATATTTCCGTGACGGTTGTAATTATTGTTGAGTATGGACACAATAATTTGTTGTATTCCTTTGTGTGAGTAACATTGCACGGCTATGACAAA
TAATTGTAGCATTAGGTGAAACGACATTATTTTTAGTGAATTAGTGGGGTCCCGCCAACCAATAGGCTAAGTAATGTGAATCCAATATCGATCGG
TGCGAAAGTGTTTTTACGACATGCATCTAGACTTTATGTCTAATTTTCTCAAATTAGTTATATGAAATCATCCCTGGCTATCACATAAACCAATT
TTATAGTTGTTAGACCTGAAGTATAATGTGACTAATCAAGATTCAAGAAAACGTTAGTTTTTTATATGTATTTTTTTATATTCGAGATCTCTTTAT
TTCTAGCCATCGATTGGCAATGCTAATGAAGTTAGTACGCAAGTGCCATTGGTTGGCTTGGGATCTCCTAGAATTTTACGAGGTGGCGTAAATCT
TCTTCCGCATGGAACCATTGGAATCGCCCGACGAACTGCGTGGCCACACCCTCAGCGAAATGGTTATAACTCAATTCTGTCGTTTCCGATGTCAA
AACAAATGAACTAATATAAATTGAAGACTTTATGAGTGTTTCTATGAGCGCGTCCTGTCCCAAGCCATAGTGTTCCTTTCTTTCCGAGTATAAAT
ATGCCAATGGCAAACATGGTGCGACAGGTATTTGGGCATTCATCAACTTGTGTATGACAGCATGTTGTTGGAACTGCTCGTACCATAGGTTCCAC
TCCCTCTCTGGTGTAGAGAATTCGATATTGACCATCAGGCCATCATTAAGTGGCCATAAAACTCTTTGTTAATTTATTAATGCGTAATTATCGAT
AATTACAGCCATATCTATTGACTATGGGTTGGCAGTTTTTTGTTTGTGTTGCCTGCCCGGCAATTATGTCATGCATTGTGTTGAATTTCCTGGCA
AATTGCTAATTTAATTAAACTTTATTGAACACTATCACTATTGATTTTCAGCCAAGCAGGCGAAGCGAACATGAACTGATTAATAAATAAATTCG
CCACTATTTTTACTTATCTAATAGTTTGAACTGTGCGGAAAATGAACCATAGATTTCTACCCCCGATCAAGTGGGTTTCTTCGATCAGCTCTACG
ATCCTCCCCCCATTGACCCCCGCGCCCAATCACTTTATAAGCTAGCTATCCAAAAATAATCAGCATAGGCAGAAACACAGAGGCGAAGCAAACAA
TGTTTTCATAAACGATTTTCGCCTGTGACCGCGTCGCAGAAATTTCTGAGAGAGGCGCAAAAGGCGAAAACGAGAAATAATGAGGCATTCCATTC
GGCAGAGCCTCCCAACCATCTGGAAATGCCCAACAAGGGGCCAGCGCAATCTAATTAGACATAATAAGGCAGGCAGGCAGGCAGTTGGAGGGGGA
GGGGAGGCACCATCGGGTTGAGGGCACCACTGGTCATATACCAAAGAGTTTGTCAGCTCGCAGCGGATCGACTGTTGCCAGGCGAAGGTTAGTTT
CGCTATAGCCAACCAGCCACCTCCATCCACTCCAGCCGCTCCGACAACTCTTGGAACTGACCAAACGACCCAGCCGGCGAGGCCCCAAACAGCCT
CACGAGAATTGGCGATCGCAGTGCGGAGTTTTTCCGGCCATGCTCTGTGCTATTAAAATATATTACAGCAGCAATTTCAGTCGACTTTATTTTTG

FIGURE SHEET 545

CGCTCAGTTGCGGCTGTGGATGTCCGCAGTCCGCAGTCTGTGGTCCGTAGTCCGCGAACCGCTGTTCGCCGCTTATAACTTCATTTTTTATGGTC
ATGAAAGTCAATTGCAGTTTGGCATTTCTTCGATGGATTTTCCCTCGTTCGCCCGTGGAAATGCCAGCATCATCGCTTGGCTGCGACTTGGGATC
TGTATTGCGGAGAAGAAGTCGTAACTTGGCGTAGAAAACTATTATTCACTTTGCAATGGAAAACATAAACCTATTTTAATTGCACTGCCCACTAG
GCAAATGTGTAAATTTTTTTTGGCAATATATATTTTCTAACCTTTGTACCTATCTTAAAGAATTTTGGTTCTTGATGTTCATCTTGAGATAACCG
GTTTAATCAATATGAGAAGTTTATTAACCTTCAGTCTTATCGATGACTAATGAAGTATGCAAATCTATATATTATAACAAACCAAGGATACAAAA
AATGGAGATTTTTCTATACAGAACAGATTGAGCACAACATACCCTTGAACTCTAGGGTGCTTTTTTTTTTTTTGTAGCAACCCACATTCATTGTTG
CAAAACAAACGTGTGTCGCACTTCACGTTGCCGTTTTTGGGGGCACAACTTCAGTTGGCAAATTGAAAACTCATAATAATTCTCACGTTTCGCTC
CAAATTTTTTAAGTCATACAACTTTGGGGTTTTGCATAATCACCATATATCACAACGAGTCACACACGCCGCAGCCAAAACAAAGTGACGAAGAA
CAGCCGCAAAGTGTGTGTACGTGTGAAAAGGAACCTGAAAAATCATATAAACATATAAATAGTTTGGGTATCGAATGATTATAATGCCAAATGTG
ATCGTTAGGGTGGCAACTAAAGCTCCAGACGTGTTGCCAAGCCGACTTCCTCTGGTTCTGGGATTAAGTTTCTCTCTTCAATCAAACTTTTATCG
GAACTCAAATTGTTTGTGTACTTGGCTCGGTTTCCTGTGAAGTGAAGTGCGGATTGACCGACTCCTACTATGCAAATTCATCATCCGACAATGCC
CCAGAAACACACAAAACCGGTGGCACTTTAAGTGCCCTCCAGGAGGCCCACGCGTCCGCCTACCAACCAAATTAACGATGGAGCAATGAACTCAA
AACACGACGGTCCATACGGTCTAATAGTTTTGAATTTCGGAACTCGTGTGGACCTCTGATGGACCCCCAAGGCAAGTCCGCTAATGAATGTTTTT
GTCTTCTCCAGAAGCCGCGATTGATTTGTATTCATCTGGCCAACACACCTTGCCAATTGTTGTTTTTTTTTTTTTGGCAAAGAAAATATACTTTG
TGCCTGGAAAATAATATTTTTATATGCGATATTCAGGTGTAAGGTCAGGTGTTTCTTATGGCAGTTCGCACAGAACAAAGGGCAGTAGATGAGCA
AGGTTTCAATAGTGTGCTCTAGGCAATCCCATACAAACCAGTTGTTTTTCTAAGCATTTACTGGGTACTTTTTTGCTTATAAAGAATTATCCAGC
CTAAAAAAACTTAGCGAGTTTGGATAAGAACTATCTGAACTCGAAGCGGAAGTTAAGGGCACGCTTAAATGACGTAAAATGTTTAACAATTGAAT
GCAGCTTTTATATTGTATATTGTATTTTAAATATGTATACTATTTAGCCAAAGTCGTTGCACCCGTGAATGAATATTTAATTTCGGTGGCATCCC
TCAGATTTATTGTGAATCACAAAGTTGCCGTGCGCACATTTTGTATGCACAAGACCTGAACTGCTTTCAAAGTGGCATTGAGATCTTTAAACAAG
TCGACACCCGCATCTTGGAGCAGAGAAGAGTGCTTGGCAAACGGAGACCCACGTAAGCACTTCCTGTGCGACATTTTGTTTGGTTAACCACGCTG
AATGATAAGCAATCATTCAGTTAATTGATAACGAGCTCAAACAATACGCTAGCTGAAAAGGGAAGCATGTACGATACGTGGGTTGGAGAAAACTG
TGCCAATTAGACAGGAATGCAGCAGTTTCATTTCAAGAGTCTGCGGCTTCAGTCTATTTGCTACCAAATGGAGCCCAATAAAAGGCAAGCAAAAC
TACATATATTCAGTTTCAACCGAATGTTTTTAATATTTATCAATTACCGGTCTAAGAAATAGCAGCAGTTGACTTATCACATTTTCTAATAGAAA
TATTTTGAAATTCCGTATAAAAGCTTACATTTGAAAATGTACAAGGAAATTAAAAAGCAATTCTACTGCTTTTTATTATTTAATTAAAAATAAAT
TCGAGTGAACATTAACAATTGATTTAAAGAGTGTACAAATTTTTAATGCAATAACCTACCTATTTCAAGTGAACAAAAAACATATAAAAAGTAAA
ACAACTTATGAGTTAAGTTTATAGATTTCTTTCTGTGCTGGTATCATTATTTAATTAAGATTGACATTTTAAAGCTGTTGAGATTTCCAAGAGTA
ATACGCGTTAAAATATGACGTCTTCTCTATCAAACTTAATCTTGTGATTACTCGTTTATTGTGTATTTTATAATTAAAATGCTATCAATGAAGAC
GTCTGATCAATAAAAAAAAAAAACATGTTACACTCAATTGTTAAACACAGCCTGCAATTTTCAATTAAAACTACACGCTTCGGATAAGCGTTGCTT
ATATAAGAAATAAACTTTTATATTTTTTACTTTTCTAAGTACACAATAAATCTGTGCGAGTTTATTCATAAAAAATATAAATAGTTTAATTTAAA
TTCTGTTATCACGGCTCAATTTTCTAGCATAAGGCCAGCAATGACTTTCAAACTTATGAATTCTCAAACCTTTGAATAACGCCATCTACCGTAAA
GGGTGTTTCTTTTAAATCTGTGAGAGGGCGCTGCTGTAGAACTACATGTTTTCTACATGGATATCTACATGCTAGCATGGACATGATTTTAGTTT
CGCGCATCTGTTGTTTTTCAAATCATGTTTTACAAATGAACATATATTTTAATGTTAATTTTTTTTTGCAGCTACAACATGCGTTTTGAGCCTCT
GGGCCAGAAAATGTTCACCCGCCGCAATTGGTTGTTGCGCTGCAGCATCCTTATCAATGTGGCGGTGATCCTGTACATTGGCAGTCAATTGATGA
TCGGCGGCGGCAACAACTTCTCGAACGGCGGTGGCTTCCTGCTGCAGGAGCAGCAACAGGTGTCAATGATGCAAGTGGGCTCCGCCTCATCAGCG
GCCCAGGTGCAGCAGCAACAGCAGCCCACTCCCAAGAACCAGAACGTAAGATACATCTAGATAATGCTCAAGCGAACTTTGGAACTAACGCCTCG
TTTCCTCTTTAGCAGGTGGCCGAGATCTTCGAGTCCGAGGAAAAGCAGCTGGTCAATGCCAACGCAGATCCTCCAGCAGCAGCGGCTCAGGTGGC
TGATGGCGGTGCTGGAGCCCCGCAGTTGGCGAACGATAGTGGTGCCGGGGCGGCTGCTCTGGGCGATCCCTCCCAGGTGATAGGAAACATTGGGC
CCGGCGGTGTCGCCGAGGTGAACAATAGCCAGTCTGACGGCGGCTACATAGTCACAGGCGATGAGAAGGAGCTGGAGGAGCGTGTGCGATCGTTG
ATCAACTGCTTCGACCACGACTACCACCAACAGACCTTGCAGCGTGGCGACTTCTGGGTGCTGCAGAACTACGTGCGGGCGGAGCATGGCGACAT
CAAGTGCCATGAGTCGATCACCTACACCACGCACGCGGACTACACGTTCCTGGACAACCTGGTGCCGCTGTTGGAGCGCTGGAACGCCCCGGTGA
GCATTGCCATGCACGCGCCCGGCACGGACTTCCAGCCCACTCTGGACTCGATCCGGTATCTGCGAGAGTGTCTGCCCGGCAGTCACCTGGTGCGC
GCCTATACCACCTTCCACATCTACTTCGGAACCAAGCACATTCCTAAGTCTGTGCCCAAGCCTCACGAAGTCTTCAAGACGGGATACAACTGCAC
ACTTCCACCTCCGTACTTCAACGTCAGCTCCGGGCACCTGTACAAGGCGCAAAAGAAGTTGCTGTATCCGGTGAACGTTGGTCGTAACATTGCCC
GCGACTCGGCACTCACCCACTTTATTCTGGCTTCAGACATCGAGCTGTATCCGAACCCGGGTCTGGTCAAGAAGTTTCTCGAGATGATTGCTCGC
AACGAACAGTACTTGAGACGCAAGGCACCCAGGTGAGTTGCCTTCAGTTCCTTGACAGAAAGACCTTGTGATTGAGATCTAACATCTATTGCACA
TTACAGAGTATTTCCATTGGCCATCTTCGAGGTGGAAGAGAACTCCCCAGTGCCACACGACAAGACAGAGCTACAGGAGTTCCTTCGCACGGGCA
AAGCCATACCATTCCACAAACGAGTGTGCGCCAGCTGCCACGGGGTGCCCAAGTCCAAGGAGTGGATGTCCGCCAACGAGACAGATGAACTAAGT
GTGTTTCACATAGGTAATGAATTATAATTATATCTTTGTTGCATTTAGATTAATTTCTTATGTTGCCATTGCAGGAAAACGAACGGGTTACTATG
TGCACTGGGAGCCCATATATATTGGAACTCATGCCGATCCCCATTACGATGAACGGCTCAGCTGGGAGGGTAAAAGCGACAAGATGCCTCAGGTG
AGTCATTCCGCATTATTGCAAAGCAGCAGTAAACTTAATAATATTATTTATTCACAGGGCTATGCGCTTTGCGTAATGGACTACGAGTTCCACAT
ATTGGACAACGCATTCCTGGTGCACAAGCCGGGCATCAAGGTGCTGAAAAAGGACAACCGACGAGCGATGTTGTCCGGCAAGACAAACCAGCTGA
TACGGAAGATCATCTATCCAGAACTCAAAATAATGTATGGCATGCGCAAGGGATGTGCGATATAGTAACTAATACTGAAGCCAAGCTGAGGTCAG
TCCCGATTGAACGGGAAGGAGGAAAAGGCGAAAAGACTACAACCAACTTCACTATTACTATTTGCAATGCTATAGATCGGTTGTGTTGACTACCG
GTTCCCATTCCCTCTATAGCATTGAATGCGCACTTCAAGTGCGTGTTTTACAATTAGCTAGAGACTTAGCCCTAGAACTATAGAGCATTATGTAG
TTAGGCTTAGCTATAGGTCAGGACGTGTAACGCCATGGGGGCCTATTGGGTTTTACCGCGTTCTGGGTTATCTTTTTCTACTCTGCAAAGCCTTG
AGAGCATGGCTTACATAGACTTAACGTAGTTAAATGTGGCTTTTAGGTATCATGGTGTATTCCATTTAGCTGGCCATTCTTAAGTTGGAACTAGA
CGTCAAGTAAGCAGTCGGCCCTTTTGATAGAGCGTGCTTAAGAATACACGCCCAAAATTGATTCACTTCCAAGAAATTTCTGTAAATAATAACAC
ACTAGGACCTTTCATTTCTTCTGTTCTCTGGACATAAGCGGCCAGAGACCTGGGTTATGCGGTGTCCACCACTCATAGGCAGTCATTATCAGTTA
CTTTTAGTCTAGGCCATAAACTTAAGTTGAACGTTATTTAGTTGAATTTTCCATATACATTCATTAACGAGTTAAAAATAGTTTTTATTGGATAT
TCTTTTCAAAATACTCAAAAAGAGAAATTGAGAGCAACATTATTTTCGTATACCGGGGCGAGTTTCCTAGACATCAGCAAAACAAACAGTCTTAC
CACTTTTTTGTGTTTTATATATTTCCGCATTAAAGGCATAGATTAAACAATGTTTTTTGGGCAATGTAGACTTACTGCAAAGACCAAAATTTAGA
TTAGACCGATACCGGGCCAAAACAATTCCAACGTTAAATATTTGACTTGATTAGCAGAGTAGGAATCATTGAATTGAAACGTATTAAATAGACTT
TGAGAGTTAAAGCGTAATAGTAATAATGATAAAGACAAGTTTCAAACAAAAAAAAACACAATTACTATTAAAATTTATACAAGAAACACACACAT
TGAGAATTGATTTGTTTACTTACCGCACTGAATGGTAGGCAGAGCAATTAATGCGATTGAAGATTACATTTCAATAAGCATAAATGCGAACCGTG
ATATTTGTACTAGTAAAGCGATTTGGAGATGTTAAACCTATTTGATAAGAAATGAGTGGGCGACGATCAAAAGGAAAGATCAGAGACCCATATGC
ATTAAACTTAATCTAAATTTAGTTTTGTATATGTTTTTAATTAGTGTTGAACATTAAGTCAAACTTGTGCACATATAAATGTTAAAAAACAACAT
TGCGAAATCGAGTCCGCGATTAGATTTCGAGTGAAATGCTGAAGGTTTTTGTTGCGTAGGCCTTAACACAATAAAGAAATGTAATTGTAACTAAG
CTATCGGTTTTAGAGAGTTTAAAAAAGATTAGTACTTAGCTGAAAAACAGCAAATTTTACGTATGTTGTTGGAAATTGAATGATGTACGTTTTCG
ATGTGACTTGGGAACAACATACAACAATTGGTGTTTGTATAATTACATAAGCCTTGATTCCGCTGATATCATGTTTGCAAATCAAGTCTTCGCTC
AAAAATTGATTTAATTGCATATTTTCCATTCGTAAGACTAAAATATCACTAAACATAATAAAAATGTTGAAAATGTAGCTAAGAGCAGAATTAAA
ATATAATTAGAATACAACAATTTGAATTAAAGAATATATTTGTATGATGTAAAGAAAAGTGTAAAAGTGCCTTAGACAAAACGATAAACATAAAT

FIGURE SHEET 546

TATTTGTAAGTCCATTAATCAAGCAGCTGAATACTATTTAGTTTGCAATTAAATTGGCAACGCTGTGTGTTCATGCATACAGCATATTTTTGTAT
GTATATAAATAAAACCGAAGGGCAATGTATTAAACTATAATGTTTACTATATATCGAAATAGATTATTTTTTATAACTTGAGTCTATGTCACAAT
TCCTATTGAATGAGTCTTCTTGATGATTCACAGCCTGCCAATTATT
(SEQ ID NO: 1006)

Exon: 1001..1161
Exon: 1929..2083
Exon: 29997..30255
Exon: 30318..31192
Exon: 31262..31458
Exon: 31520..31632
Exon: 31693..31890
Exon: 32136..32961
Start ATG: 1132

Transcript No. : CT26212
CCGAAATGCCACAGACTTTTTGTAGGCTTTTCCACTTTTTCGATTTCGAGACTTCGAGCGAAACGGTCGTGTTTTTCGCGTGTGTGCGGGTGGCG
GACGCGCGTGCCAATCGGAAAAGGCCTTTAAATCAAATGAGTGGCTCGCCAAAGGAGCGCATCAAGAGCAGCCAAAAAATCAACAAAATACGAAA
CACAAAGCCAAATCAAAAGAAATCAAATTTCAAATTCGTGCGGCCACCAGCAAATATCGAAATAAAGAAATTATCTAAATCATCATCAGCAGCAG
CACAAAAATCGAAAATCTCCTCGCTGTGTGTCTACAACATGCGTTTTGAGCCTCTGGGCCAGAAAATGTTCACCCGCCGCAATTGGTTGTTGCGC
TGCAGCATCCTTATCAATGTGGCGGTGATCCTGTACATTGGCAGTCAATTGATGATCGGCGGCGGCAACAACTTCTCGAACGGCGGTGGCTTCCT
GCTGCAGGAGCAGCAACAGGTGTCAATGATGCAAGTGGGCTCCGCCTCATCAGCGGCCCAGGTGCAGCAGCAACAGCAGCCCACTCCCAAGAACC
AGAACCAGGTGGCCGAGATCTTCGAGTCCGAGGAAAAGCAGCTGGTCAATGCCAACGCAGATCCTCCAGCAGCAGCGGCTCAGGTGGCTGATGGC
GGTGCTGGAGCCCCGCAGTTGGCGAACGATAGTGGTGCCGGGGCGGCTGCTCTGGGCGATCCCTCCCAGGTGATAGGAAACATTGGGCCCGGCGG
TGTCGCCGAGGTGAACAATAGCCAGTCTGACGGCGGCTACATAGTCACAGGCGATGAGAAGGAGCTGGAGGAGCGTGTGCGATCGTTGATCAACT
GCTTCGACCACGACTACCACCAACAGACCTTGCAGCGTGGCGACTTCTGGGTGCTGCAGAACTACGTGCGGGCGGAGCATGGCGACATCAAGTGC
CATGAGTCGATCACCTACACCACGCACGCGGACTACACGTTCCTGGACAACCTGGTGCCGCTGTTGGAGCGCTGGAACGCCCCGGTGAGCATTGC
CATGCACGCGCCCGGCACGGACTTCCAGCCCACTCTGGACTCGATCCGGTATCTGCGAGAGTGTCTGCCCGGCAGTCACCTGGTGCGCGCCTATA
CCACCTTCCACATCTACTTCGGAACCAAGCACATTCCTAAGTCTGTGCCCAAGCCTCACGAAGTCTTCAAGACGGGATACAACTGCACACTTCCA
CCTCCGTACTTCAACGTCAGCTCCGGGCACCTGTACAAGGCGCAAAAGAAGTTGCTGTATCCGGTGAACGTTGGTCGTAACATTGCCCGCGACTC
GGCACTCACCCACTTTATTCTGGCTTCAGACATCGAGCTGTATCCGAACCCGGGTCTGGTCAAGAAGTTTCTCGAGATGATTGCTCGCAACGAAC
AGTACTTGAGACGCAAGGCACCCAGAGTATTTCCATTGGCCATCTTCGAGGTGGAAGAGAACTCCCCAGTGCCACACGACAAGACAGAGCTACAG
GAGTTCCTTCGCACGGGCAAAGCCATACCATTCCACAAACGAGTGTGCGCCAGCTGCCACGGGGTGCCCAAGTCCAAGGAGTGGATGTCCGCCAA
CGAGACAGATGAACTAAGTGTGTTTCACATAGGAAAACGAACGGGTTACTATGTGCACTGGGAGCCCATATATATTGGAACTCATGCCGATCCCC
ATTACGATGAACGGCTCAGCTGGGAGGGTAAAAGCGACAAGATGCCTCAGGGCTATGCGCTTTGCGTAATGGACTACGAGTTCCACATATTGGAC
AACGCATTCCTGGTGCACAAGCCGGGCATCAAGGTGCTGAAAAAGGACAACCGACGAGCGATGTTGTCCGGCAAGACAAACCAGCTGATACGGAA
GATCATCTATCCAGAACTCAAAATAATGTATGGCATGCGCAAGGGATGTGCGATATAGTGTAACGCCATGGGGGCCTATTGGGTTTTACCGCGTT
CTGGGTTATCTTTTTCTACTCTGCAAAGCCTTGAGAGCATGGCTTACATAGACTTAACGTAGTTAAATGTGGCTTTTAGGTATCATGGTGTATTC
CATTTAGCTGGCCATTCTTAAGTTGGAACTAGACGTCAAGTAAGCAGTCGGCCCTTTTGATAGAGCGTGCTTAAGAATACACGCCCAAAATTGAT
TCACTTCCAAGAAATTTCTGTAAATAATAACACACTAGGACCTTTCATTTCTTCTGTTCTCTGGACATAAGCGGCCAGAGACCTGGGTTATGCGG
TGTCCACCACTCATAGGCAGTCATTATCAGTTACTTTTAGTCTAGGCCATAAACTTAAGTTGAACGTTATTTAGTTGAATTTTCCATATACATTC
ATTAACGAGTTAAAAATAGTTTTTATTGGATATTCTTTTCAAAATACTCAAAAAGAGAAATTGAGAGCAACATTATTTTCGTATACCGGGGCGAG
TTTCCTAGACATCAGCAAAACAAACAGTCTTACCACTTTTTTGTGTTTTATATATTTCCGCATTAAAGGCATAGATTAAACAATGTTTTTTGGGC
AATGTAGACTTACTGCAAAGACCAAAATTTAGATTAGACCGATACCGGGCCAAAACAATTCCAACGTTAAATATTTGACTTGATTAGCAGAGTAG
GAATCATTGAATTGAAACGTATTAAATAGACTTTGAGAGTTAAAGCGTAATAGTAATAATGATAAAGACAAGTTTCAAACAAAAAAAAACACAAT
TACTATTAAAATTTATACAAGAAACACAC
(SEQ ID NO: 1007)

Start ATG: 132

MSGSPKERIKSSQKINKIRNTKPNQKKSNFKFVRPPANIEIKKLSKSSSAAAQKSKISSLCVYNMRFEPLGQKMFTRRNWLLRCSILINVAVILY
IGSQLMIGGGNNFSNGGGFLLQEQQQVSMMQVGSASSAAQVQQQQPTPKNQNQVAEIFESEEKQLVNANADPPAAAAQVADGGAGAPQLANDSG
AGAAALGDPSQVIGNIGPGGVAEVNNSQSDGGYIVTGDEKELEERVRSLINCFDHDYHQQTLQRGDFWVLQNYVRAEHGDIKCHESITYTTHADY
TFLDNLVPLLERWNAPVSIAMHAPGTDFQPTLDSIRYLRECLPGSHLVRAYTTFHIYFGTKHIPKSVPKPHEVFKTGYNCTLPPPYFNVSSGHLY
KAQKKLLYPVNVGRNIARDSALTHFILASDIELYPNPGLVKKFLEMIARNEQYLRRKAPRVFPLAIFEVEENSPVPHDKTELQEFLRTGKAIPFH
KRVCASCHGVPKSKEWMSANETDELSVFHIGKRTGYYVHWEPIYIGTHADPHYDERLSWEGKSDKMPQGYALCVMDYEFHILDNAFLVHKPGIKV
LKKDNRRAMLSGKTNQLIRKIIYPELKIMYGMRKGCAI*
(SEQ ID NO: 1008)

Classification: enzyme

Celera Sequence No. : 142000013384661
GGGAGCGGATCTTCTTCAGACGCTCCAGATCGTCACGCAGCTTCGAGTCCAAGTTGGAGGAGGTCAGCTGCCAGTACTTGCCATCGATGATGTCC
TTCTGCCTGTTGAGGAACCAGTTGGGCACCTTGTACTGCAGAGGGTTCGAGATGATGGTCACCACCTTGTCGACCTGCAAACATGGCATTTAGGT
TGGTGTGCGTCTCGAACGGATTGGGCGTGCTCAACTTACCTCCTCCTCGGTGCACTCACCGGCGCGCTTGGTAAGATCGACATCGGCCTTCTTCA
GCACAATGTTGGAGTAGCGGCGACCCACTCCCTTGATGGCGGTCATGGCGATGCCAACCTTGCGCTTGCCGTCGATGTTCGTATTCATGATACGC
AGGATGTGCTGGAACTTCTCTGGGATGACGAGCGACTGCAAGAATGCAAAGAAAAAACATTAGTATAATGCATATAAACCACGCCATTTTTGCCA
ACAGCTAACGGCATTTGCAATTCACTATAAATTTGTCGTTTGGCGCTCAGAATCGCACATATTTGAGGTAACTCACCATTTTGCCGTTTGTATTC
TCGTATTTACTCCTCACTGTAAAGAATTAAGAGGTATTTTGTTTTAGAATTTTGGAAAAATCAAATGGGCAGCACACCACTCACCGGAAACGGGA
AAAGAAAAGAAGGCCGAATTAATGTGGCTGCCTGAGGCGGAGTAAAAAACCTAAAATTGCCTGCCACGTTCGGGACGCGTGCTGTTAATAGTTCG CCGTGTGCTGTTAGGCGCACTCTGGTCCATCACTAATGCAAATTTAAAAATTCAAAAGGCGCCGAACTTTTGTTCAATGAAAATGCTTAAAGTGC
CATTTAGATATGCTCTGTGTGCACATTTAAAAAATTAAACTTCATATTTTATGTTTCTTTATATTTTATATTTTATTCCCCACATTTCGTAATAC
GTTTTATCGTACTGCATCCCTAGAGCACCGTTATATGAAAGCTTTTCAGAATGGGTGAAATAAATGGTAAATTATATTAGCTATGCGAATTTCCA
ATATTGATAAAAATGCATTGCATTTAAGCACTCAGCTGCGTTGGACAGGACGATGTCGTTTCCCTGCGCATCGTGTGCACCATGGCTCGCGACGG
CAAGCAGCACAACCTCGAGGATGTGGACATGTACGGGAATACCGCCCTATTGAAGGCCTGCTATTTGGGTCGATTTGAGTGCGCTCGTACGCTGC
TGGAATTCGGTGCAAATATCTTTGCTATGAACTATTTTGGTCAAAATGCCCTGACACTGGCCACTTATGCTGGGCATTTGACTTTAGTAAAGGAA
CTGTTGAGGCGAAGATCCTACAAGGATTTCAATCTGTCCTCGATGATCCCGGCCCTCTGTGTGGCTACACTGCAAAAACACTCCGCTTTGGTGGC
CTATTTTACTCAATTGGATTCGAGGGGCGTGCAAGAAACTCAAACAGTGCATGGTTAGTAAAAATCAAGTGTATTTATATAGTAACATTAAAGTA
AATTTATTTCAGGTCTGGGAGTTGCAGAGCTGCGAGGAATGATTAAAGCTGCAGGCCGCTTAGATAAGCGCAATGTGCGCTCTCCTCCCACTTTT
ATTAGCAATCGTCTGCGTTAATGTATTGTCATTTTGTAATAATTTATTAATTTTAATGTTTGAAATAAATATACTCTGTAAAAAGTGTGAACATA
ATATGTTAATCAAACCAGTTGGCAGGCCGCTCGCTGGCTGCTATCGATAGATTCAGTCGATATCGCCCGTGGCTTTTCACATCCCTATCCCGCTC
ATTTAGCCCGCCTGAAAGTAAAAAAAAAAAACAGCCCACGTTAATCATTCATCCCAAAGTCACAGCCGCGGTAACATTACTGCTGTTAAATTCTT
AAGCCCGTCATCAGTATTTAAATAATAAAACACATTCAATATGTTCGAGGCACGCCTGGGTCAAGCCACCATCCTGAAGAAGATCTTGGATGCCA
TCAAGGATCTGCTCAATGAGGCAACCTTCGATTGCAGCGACTCCGGCATTCAGGTAAAAATTGCACAAAAAAGATTTTAAATGCATATCCCTAAC
ACCTTGTTCAACTTACAGCTACAGGCCATGGACAACTCCCATGTGTCGCTTGTCTCGCTGACCCTGCGTTCCGATGGCTTCGACAAGTTTCGCTG
CGACCGCAATCTCTCCATGGGCATGAATCTGGGCAGCATGGCCAAGATTCTGAAATGCGCCAACAACGAGGACAATGTGACGATGAAGGCGCAGG
ATAACGCCGACACTGTCACCATCATGTTCGAATCGGCTAACCAGGAGAAGGTATCGGACTACGAGATGAAACTGATGAACCTCGACCAGGAGCAC
CTGGGCATACCGGAGACAGACTTCTCTGCGTGGTCCGCATGCCGGCCATGGAGTTCGCTCGCATCTGCCGCGATCTGGCGCAGTTCAGCGAATC
CGTTGTGATCTGCTGCACCAAGGAGGGCGTCAAGTTCTCGGCCAGCGGCGATGTGGGCACCGCCAACATTAAGCTAGCCCAAACCGGCTCTGTCG
ACAAGGAGGAGGAGGCGGTGATCATCGAGATGCAGGAGCCGGTGACGCTGACATTTGCCTGTCGCTACCTG
(SEQ ID NO: 1009)

Exon: 1001..1016
Exon: 1074..1478
Exon: 1533..1636
Start ATG: 1001

Transcript No. : CT26230
ATGGGTGAAATAAATGCACTCAGCTGCGTTGGACAGGACGATGTCGTTTCCCTGCGCATCGTGTGCACCATGGCTCGCGACGGCAAGCAGCACAA
CCTCGAGGATGTGGACATGTACGGGAATACCGCCCTATTGAAGGCCTGCTATTTGGGTCGATTTGAGTGCGCTCGTACGCTGCTGGAATTCGGTG
CAAATATCTTTGCTATGAACTATTTTGGTCAAAATGCCCTGACACTGGCCACTTATGCTGGGCATTTGACTTTAGTAAAGGAACTGTTGAGGCGA
AGATCCTACAAGGATTTCAATCTGTCCTCGATGATCCCGGCCCTCTGTGTGGCTACACTGCAAAAACACTCCGCTTTGGTGGCCTATTTTACTCA
ATTGGATTCGAGGGGCGTGCAAGAAACTCAAACAGTGCATGGTCTGGGAGTTGCAGAGCTGCGAGGAATGATTAAAGCTGCAGGCCGCTTAGATA
AGCGCAATGTGCGCTCTCCTCCCACTTTTATTAGCAATCGTCTGCGTTAA
(SEQ ID NO: 1010)

Start ATG: 1

MGEINALSCVGQDDVVSLRIVCTMARDGKQHNLEDVDMYGNTALLKACYLGRFECARTLLEFGANIFAMNYFGQNALTLATYAGHLTLVKELLRR
RSYKDFNLSSMIPALCVATLQKHSALVAYFTQLDSRGVQETQTVHGLGVAELRGMIKAAGRLDKRNVRSPPTFISNRLR*
(SEQ ID NO: 1011)

Name: plutonium
Classification: DNA_replication_factor
Gene Symbol: plu

Celera Sequence No. : 142000013384591
TCACTATAAGCTGCAATAAAGTATATCAAAGGCCTGTTCGGGCGGCATTCTGGGGGCTCGAGTTCCCTCCCCTTTCAGTGCAATCTTTCGTTTGT
TCATCCATTTCATAAAAATTCCTGATAATGCTTGATTTCCACAACATGCACAAGTGCGTGTATGTATCCGTTTTAGTACTGACTATATTCTACTC
TGTTTAAAATAAATATTACACGAGACACTCGTTATGTTATTGCCCCTTGATTAAAACATCTGAATTTCTAAAATGTAATTTTTGCATATCCGATA
GATATTTTGTCTGTGCTGCTTCCAAAAAAAAAAAACGTTAAAACTCTAAATATAATTCACAATATTTTGTTTGTATAAATTATTATGCTGGCGGG
TGGTTACTCGTTATGTTATTGCTATATCTTTATCAATTATCTGCAAGCACAGATGATATACATATGTATGTACCTATTTATAACACAAAGCTGAT
CTTGAAGAGGGCAAAAATAGATTGAGTGCGTTGTCAACGCTCACTTTCAACATTTTATCACCCTTGCGCTTCAGCGAAGCCTGTCTTACGTGTCT
ACCAACTATGAAATGCAAAGTAACCGCCACTGAGTACTCTTAGTACACTTAACGCATAATATGCCTGGGGCTGGGTTACGCCTCGTTTCTATTTA
TGTACAAAACATCGATATCCAGATAGCAAGTACCCTCGTTACTTAGCTACTATCACACACACTGACTGAACCTGTTGCTGTCGCATTGTTGCTTT
GTCAGAGAGGTTTTACAACTAGTATCATAGCTATTTTGTGAGTATTGCTTCATTTTTATACAGGGTTTTTTCTTTTGGTAACACTAGGCTTTTCT
TACACTATTTATTGAATCGTTTTCCACCTTGATATTTTGCCGTCTTTGAGGGAGATAAGAACTAAGCTTTCAGTCGAATCTGAAATAGGTTGTAT
TACTGATTGTGGTTGCAAATGAAATAAAATAAAAATTCATAACTTATGTTCTTGCTAAATATTTATTTATGTAGTACCCAATTGAAAGTGTATAT
ATTGAAGGATCCTTCGGGCCATGCCGAAGTCATTCATTACACAAGTAAAAGTTTGGCATGTCTCCATTTCGAAACGGCTTCATATTTGTTTTCAA
ATTAAGACTAGAAACTGGACCTTAGTGTCTAAACTCTACTTTGAGACTGCACATCTATATGGCGCGATAAAGTCACTTAATAACTTAAATGTTAA
ATACGTGTGTTGTATGCAAAGTTATGTGAGGTCATCGAACGAAGCGGACAATTAGACAGATTCAAATATGGTTTGTGGACATGCTCGCACTTTGA
TGTAATCGATTCGTTTGATTAACGTTGAGTTGTTGGGTGTAAAACAAGTAAACCCAACAAAACCAAGTTAATGGGTTTCCAAAAAAGAACGACAA
AATACGAGAGATCGTGTAAAAGTTTGGCATTTTGCCCTAAAAGTTTATGCTATTTTACAAATATACAATGTATGCATATATAGATGTATATCGCT
TATGATTTGATTTGACTTGTTGATTGCCTACGAGCTAATAATACCTTAGGTTTGAACTAAGATTTCCATATCGTATGTACGTTAGTATATGTGTA
TAAGTATATATATATCTATATATAAGTTATGTATACAATTGTATAATATTGCAATTTCCAAATGTTCAGTTTCAATATGATGTATTTTTTTTTGT
ATGGGTTAGGGATCTGGCCGTTTAATGGATTGAAAGTCGTGGACCGGCGGCACCCATCTGTATGTTACAATACAAAATTGCTTGTCTTCTCTTGG
TTAATAATAATATTACAATTTCTGCTGTCATTTCAAGGGGGTTTTTCGTCGTCCACAGCGACGTCTCATTTACAAATTTGATCCCTATACTAATA
CTACTTTCTACAAATATATGTATGTGTAATTATATGTTACGATCGAGATTTTTCATTACTTTCGTTTGGGTGTTTGTTGACCCAGATTCAAATTC
TGTTTGAATTCACCATACATCATTCGCTTTGAGTTTTGTATTATTGCAAAATAAGATATTTTCTCTACTATTGTTGTTTTTTGTGCATCAGCGCC
ATATTGAATGATTAAATATAAGTTCTCACACCGCCTTTTCAAAGGGCAGACAGGGAAAAGTATTTTTCCTAAAATTGAGAGCTCCTCTCACTTAT ATGACAATGATCTTACATTGGTATTCTGCTGTAACCATTTCTTAAAATTGTAAGCAAGATAAAATATAAATTCATTTGATTTTGTGGCTGATTGC
TCCAAAAGCCTATTCAAAACATTTTACCGATCTTAAGCAAGGCCTCGCAGCAAATAAATTGTGTCATTCAATTGTTCTCTGATTTAAAATTATTC
TTATCTTTGTCTTGTACTCGAACATTCTCACATTACTAAGATTCTTTAAATATTTAAAGGAGACAAAATTTACAATGCGGTAAACGTTTGTTGTC
CATTGCTTATCAATGTTAATATACATGTGCTATAAAATGAAACTGAGAAATACACAATAAAACCAAAACATAAATTAAATACTCTTTCTCTATTA
AAATGTATGTTTATATTAAAGTAATCCAATGGCATGAAAATAAAGTCCTGTCAAAACAGTGGGTAATAAGTAGGGTAAGGTATGTTTTCAATGAG
TTAATTAACAAATTAGTCTTCATTGGAGAATACTTCAATTTCTTTCGAGTACAAGACTATAAGATGGCCTTGGTAGGATCATGGGTAACATGAAT
TCCCTTTTGCTTGCCCTTTTGTCCATCGGCGTTTTAAAACAGGCCTTTGGCGCCGGCCAACTTACGTCGCCGGAATCACATGAGTCATCATTTG
AGCGTATTGTAAATGTTATCCTCTCCGGCCAATTCAACGGTGGTGATGTGGCAGCGTGCCTCTCGCCCAGCGGTTCCTCGCCCAGGTACACAGT
ATGGTAGCTGATTGCGCTGCTCTTCACCGCCGCCGTAGCTCCATTCACCTCAATCCGACTGACCGACTGTGGTCCATTGACCGAATACTTGAGCG
ATGCATAATCTCCATCATCGTCGGGCACATGAGTGAACTGAGTGGCGCCCGAAAAGGTGTCCACTGTGTGCGAGGGACAGATTTCGGCGTATATA
TTCTCCTTGGTATAGTCCACAGCGGGAACTGGTCTACTGGCGGACTCCGATCGCAGGCAGTCCCCGCCGGAAATCACAAGCGAATCGCGCACACT
GGAGTAGGGCAAGTCGTCTTCCACCAGCGATGCGGGCGATATCGCCAGTTGGTTGAGTCCTCCTCCCAACAGAGAAACTCCACCGGCTGCCCTTC
TTCCAGTGACCGGTTCCTTGGTCAGCGCCTGTTGCTGCGCCTTTAGCAACATCAGATGTCGCTTCTCCTTTTCAGCCTCGTGAAGTTGCAACTTT
TGCGGCAAGCTAAACAGAGGTAACTGGTGCAAACTGGACGATGACTTGCTATACTGCCTGGTCTTCACGTGAAACTCGTTGTACAGCTTCTCCGT
GATGAAGGACTGTGGAGGTGGGGTCTGATTCTCCACATCTTCCAGCTCGGTACCTGCCTCACTGATGGCGTCATTGTGATTGTGGCTGGCCAGCA
AATCAGGTCGTTGCTTGCATTGACCATTGAGAAGCTCAATATCCTGCAGGGACATGGACTTTTGCATCATTGTGTCCAGAGACCTCGGCTCCATG
GTAGTCAGCATCGTTGTTTCGGTGTCGGACGCTGCTGTGCTGTTTAGGGAGATAGCATCTTGCTCTGGCTGTTCGGGATTCGAGCCAAAACGCTC
CTGCAGAAGCTTAGACATATCCGTATAGCGCTCCATGCTCATTCGCTTGGCCTGCTCATCGAGATCTAAGTCAGATTGATGTTTCTCTATTTGTG
GTTGCTGTTGCTGCGGATGATGCTTTCCGAACCACTTCTTCTTGGTAGACTGGAATACACGCATGCGCTCAGAGATGCGATTCAAACTGGATTCC
GAGTGAGCTGCAGCAGAAGCTGCCGCTTCCTTGGCTTCCAGATTCTCCAGATCCGATTTGCTGAGGAAAATAATGGAATCCTCCTTTTCGTGCGC
TGCTGCCATGGAGCTCTTCTCGCGTCTCAGGATCTTTGGAAAATGCAGTGGCTTCAAGATTCGTAGCCCCTCTCGATTCTTGCTTCCCGAACGTT
CCGAGCGCTGAATTAACTCAATCTCCACGAGCTTCAGGAATGGATCGCAATTAAATTGACAAAACTTTAGCATATTCTGCACATTCGTGTTAGCG
AGCATCCGTTGTTCGGAGTCAAATCCTAAATAACTTTTTACCAGCTGAATATCTCGACTGGGATAGAACTTCCTCAGCTGCAAGGGCGTCTGGGT
ATCGACGTCCTCAATGGAACAGCCAACAACCACATCCTCCTTGCTCACTTGACTAATACATAGCTGCTCGGGAATGTCGGGTCCGCCTGGACCGG
AGATATAGCGCAGTGTTAGCGGTAACTGCTTGGCCGCCGTCACCAAAGCACTCAAACGATGCACGCACTCCGGATTCAGCTTGCGCTGCGCATCG
CCCAGTTTCTGAAGCAGCTGAGGAATTCCCGGTTCAATCTCGTAGAACTTGCCCTTGGTGGACAGTGGGACGTACAACACCTGCCGGTTTTCATT
AAGCAGCTGGGCATACCGGTTCTTTTCCTTCTCCCTTCCCATGTACCCACTGCCATGGGACCTGGTCGCATTGCCGTTGCCATGTTGCGACATAT
TGACCTGATCCTGTTTGCCATCCTCGAAGACGGCCAACAGACGGAATACCTGCCCGCCCCTTGCCGTCGTTTTCACGTACTGTGGTCGTCCCTTG
TTTATGGGCAGGCATCCCTCGTGCGTTGGACTGCTCGTACTGTTGGGCGAGGATTCCGTAAACGCCGGCATGTTGTCCACTGAGACAAACTTGTA
AACCCGTTCCCGAACCAGCTGTATCAGAGATCCGTATTGTGTGGCCGTGGGGAGACCCTTCTCGCTTAGCATCGAAAAGTAACCTGCGGAAAAA
GAAAAAATACAAATGTTAAAATTGTCCTTGTATCTTATGTTGTATGCGTATCTCTTCTATTAAAGTGGGTTCATCTAACCATTATACATTTCATA
AATAAATTAATTACAATTGGGTCAAAATAAATGTTCACAGAAGCTTCGCCTTCTCAAGGTCATAAAAGCATTTAAAAAAAATAGCACAAATCAAT
AATTAAAAACTAATTTTGAAATCTCTTTGAACAAGACAGATATTTTGGTTCAGTCGCTGAACAAATCTGTTTACTGTCTAAAATCTGAAAACCAT
TTTTCCGACAGCTGACAGCTTCGAACAGAATATAGTACACAATTTGCAATCCAAAAATGAGTACAAAAAATAAAACAAATAACGTGACGTGCGAC
TGGGCATCTCTTAGTATTGAGATATATGTATTTAATTTTCTTAAAATAAAAGCATTTTTTGTCAATTAAATGCAAAACCGACAAGTTTGATTGGA
GGGTTTGTAAAAAATAAAATTCGAATGTAAAAAGAGTTTCAGTTAGCGCAGGTGGATTTTACAGAAAAAAATGCAATGCAATTAAACATTACATG
TATCGATGAGTCCATTAATCATTTCATTTGGTTCAATTCGCGCCACTGAGCTTAAATTATAATGATACAATAAAAAAAATTGATGATAAAGAGAG
ACTAATGCAATCAGCGTCGAGACCAATTGAATCAACACAAGAAAAATCCAATATGCTCGTGCAAATTGAATCACTCCAATTTGCCATCCATTTTT
TCCGGACATTGCAAGCCTAATGAATAAAATGATAATACCCAGCGTCAGTAAGTCTATAAATGGGCAGATTGCATAATATTTGCACCCATTGGTTT
ACATTGCGCCTCGCCAAACGGCTGTGAAAAGTCACATGGCGTTGCGATTTGAAACAATGGCTGACCGCACAGTACGGCGAAGAAGCAGCAGTGGG
TGGTTGGTTGGGTACTGCAGGTGGTATCGGTGGTGTCGGTGGTGCCGGTGGTGTTGCTGGTGTCGGTGGTGGGCCACCGAAGAAGTCACCGCTGC
CAGACAGACTGGGCCAACAACCAAAACCACCGGCACTGGAACCCCGAATAGAGCTCATTGCATAACGCCTGATGAGCAATAGTTGCGATTACTTT
CCATTGTTGAACTGTGACTGTGTCACGCAAAAAAAAAAAAAAAACATCAAAGTGCTGGATACATATGTCTGTATGTTTAGGGAATTGTGTACTTAG
TAACCTCGCACTGGGAGATCAGAGTTCGCTTGGCTGACTCACTAAGCGAGTTGAGTTGGTTACGAGTGGACCGTGTAATCAGGCAAAAGTAGTAA
GTATCTAAATGCATTCGTCATGAGAACACTAAATTGTGCCTTCAAATGTTCCCGTCTGGATTATGTAAATGGGCATGCGACTACAATCAGCCGTG
TTCGTGCCGAATCAGTCACAGGTTTTCCTCCCATTTTTTTTTTTTTAATCATTCGGTTATGCCCTTAGCTACTGCCAATCGGCGCATCAATCGG
TGGGTCATTGAAGTTAATTTACTGTGAGCGATAAATTAACTTCCCTCAATGGAATGACAACTTGTTTGAAGCCGCCCTCGTCGGGGCCAACGTGT
AATTACAATTAGCCGCAGCACTTAAGTTCTAGCTGTTCTGTGAAAAATGTATCTTTCGCTTTTACAATTGTAATAATCAATAAATAGCAGGTAAT
TAGAACGCAAACGTACTATAAACCTGAGATAGCATACATGTAATAATATGACTACTTAACTATTGTAACAATCAATTTTAATAGTTAATAAACAA
TATGTTTGCTAATTGATTTTAGTTTATTACAGATACATACTGTTAAGCAATATGACAAATTGTTATTTATGATTTAAATAAACCCAGAACTCGAT
GCAATCATCCAATTCAGAAACTCACCCGGAAACTCCTGTGGAATGAGCAGAGTCTTCTTGCGCTGCGATGCCTGAGTCTTGGCGTTGTGTCCGTG
GTAGATGTTGCGCTGTCGCACCAGCCTGTAGAGCAGAAAAAGCTCATCGTGGCCGGGTGGAGTGCCACCGTTGCTGCTGTGGCGACCGTTGTTGT
TCTGGTGACCAGAACCAGAACCAGAACCCGAGCCCGAACTAAGACCAGGACCAGAGCCAGTTCCGTTTCCGGTGGCGCTGCCTCCGCTGGACGAT
GAATGGGTGCCGGTGTCAATGTTGCCACTGGAAATGTTTCCACCACCACTGCCACCAGAACCAAACGGATTCGCTCCCGTCGAGGAGCTGCTCGA
TGCCGCCGTGGAGGAGCCATGCGATGAGCTGGACTGCAGCGTTTCGTTTGAGCTCTTGCTCGCATGCAGAATGCGGACGACTCGTGGCAGGGAAT
TCCGCTCAAGGAACTCAATGGCTGTCAGCGCACCCTGTAAGATGCATTGTTTATTAGTTGAAGTTAGAGTTTATTTAAATAATTTCGAATGTGGT
TAGGAAACTTACAAATCGACAACGAATAATTAACCAACATTTTTGCGCGATTAGAAAACTTATTGACGTCATGTACACGAGAAAATTTAATATAA
AAAAATGTATATTCTATATTTTATTTTAATCCTAATCTACGTTAATCTGCTTTTATGATATATTGTATTTGTAGAACAAACTTTGGGGGATTTTA
AAAACCCGTTTCTATCGTTATTCGAATTTTTTGCCATCAGATTATGTTACTATTTGAAATTGGTTTGACGTAGATTTGTGTATATATAGGTATAG
TGTAATTCAATCTTACTTCGCTGCTGCCCTTGGAGGCCTTGCTGTCCCCGGTGGAGTAATCGCCGCTGCCATTGAGTGCGTCACAGTATCCAGAA
TGGGCACCTCCCAGCAATCCTGAGCCCGATCCCAGGCCGTAGGTGCTGTTGTTGGCACTGCCGCGCACGCGTCGTGCCCTCCGCTGGTTCAGCTC
GATCTCGTTGCGGCGAGCTAGGCGGGCGTTCTCGAAATCGGCCACCGAGAACATATTCGAACTGGTGTCGTGGGAGTTGAAGCGCCGCAGTTTGG
GCTTGCGCGCCCCAGCCGCCGAATGGTGGCCGTGATGGGCGCCAACGGCTGCTCCACCTGCAGTGGCAAGAGCAAAAGGTACGAAAAAAATTAAA
ATAAAGAATAAAGAAACGCAACGCAACGCGGAGGAGTCGTGAGTGAGTGAGGTAGCACATTGTGCATCGGTGAGGTAATCGCATAAATATAAATG
CACATGTGAGTGTCTAATTGCCACCCCGTTGTCTGCAGTGGGAAAAACCCACACACCGTCGTATCAACTTCCACATCTACGAGTACAGTGGCAGA
GCTTCGTCTATAATGAGTGTATATTCCCCAAGCGAATTTCAGTTGGCGTGACGCAACAACAAAAAAAAAAATATAAAAAAAATAAGGCAAGTGGTT
CAAAACTGTTGCTAAGCGCAGCTAATTTTCAGTCAACGGTCAACGAGACGATGACACACAGTGGGCAAATATCGCCCCAAAGCGTAACCGCAAAA
TTAACAAGAATTTTCGAAATAGACAGGAAGGAATGTCGAAAGATCTTGCACTGAATTTAAAGTGGGGAAAATCGAACTTTTATTGTTCAAGACGG
CCATTTTTAGACCACAATAAATTTAATGCACTGAATAGCTGCACCTGTACACAACATTCTTGCCTGCTCGGCTTTGTTAAACATCGTTTCAAGGC
TAAATATAAATGAAAATCTTTTAGCCAAAGTTTTGTATATGATTTGGAATCTACGAACTTCAAGTTCAACTGGCCAGAAAGGCAATCTATCTCTA
TCTAATAATAACATGCAAATACTAAAAACGTAGGTATACACAAAACTCAAACTGCTCTATTTGCACTCGATTCTATAATTCAAAGTTTACTAATC

FIGURE SHEET 549

AGTGCTTATTTTTGCGTTTTAACAACGTTTACGCAAACAAATTTGTCACTAACAAGACTTTATTTGCAATACAAATATATTGACTATCAGCTAAT
TGATACTAAATTTTGCTATTGACGTTTGCCATGGGTCATTAAAAATACCTGCTTGGTTTATGAAATGCTTGAAAATTGCTTAAAAACTTGTGAAA
ACATTTTTGATTTATTTCCAAGCATAAAAATTCGTTATCAGGTCAATGATCTATGTGTAAGCTATTAATCAACGTATTTTATTATCGATTAGGTC
ACTTCGATTCGCATTTCCGGGTTATTGATTACTTGTTTAAAAAGTTTTGAGAACTTTTTGTTAGATTCGAATGCACTTGAGTTAATATCGAGGAA
GAACTGCGGGGGTCTATGACTTGACAATTTTAAGGTCGAATTGTATTTTTGGTTGAAAGATCCAATCGGATCGGATATCGAGGCACTAATAAAAG
AGTCAACAACTGGAGGCGATTAACGGCACACAAGTACGTAGACAACACATAAAGATAACACCTCCCTCATGGGCAACATATATTGTATTATATCG
TTATCGGGCCGACATCCAAAAAAGCAATTGTCTGTCGCCCCAAACAATACCGCATGAAATCACTTAGCCATATTCGTTTTTTTCCCCGATTTTTT
GTGTTGCTTTAGAAATATATAGGTATGTATGTAGTTGTGTAAATAAGCGAACTTCGAGCGTTGCAATTAAAAAGAGATATCGCGATTTTTGATTG
CTCATTGTTCGAATGCGGCCCATGGTGCGATTTGGATCCGCTGATTGGTGGTCGACGGCGCATTACTCACTTTAATTGCGCACATTTGGCTTAAT
TTTTTGCCCCACACACAACACACATTTAATAAATGCAGGCGAGGGCAGAAATCACAGCATAACACCGGGAAGGGGCTAAAACGTTTTGTGAAATT
GCTCTTATCTTTCGTGAAATATCAATTGCAGAGTAGACTTTCAGCCAGCGAGCGAGAGAGTAAGCCATATACATACATACATATATATATACATA
TAAATAGAGAGAGAAAGCGATAGAATGGATGAAGGGGGGTGGGTGTGAGATTGTCACGTTTCGTGTGAAATTATGCGAATCGACGCGCGCGCCTT
TTGCGAAAAGAAATCCCCATACAGACAACACAACCACCAGTTAGACAAAAAAAAAACTACTTCTGGTAACGAAACTGTTGTACCCTTTCAATCCA
ATCTAAAAACCCTTCTTCTGATCTTACCCTTTCCGGAATTTACCGCAGATACACATACTTATCAACAATATGACTTAATCTACACATCTTAGTCT
TTAATGGTCGAGATTTCTTTAGAACCATTCATATTTTTGAATGGGTAGACAAAAATAAGTCTTTCTAGGTCATCTTATCAACCATATATTTTAAA
ATTTAAGTGAGTAATGTTAATCACTTCATCTCTTTATTGTTCAGAGTGTTGATTGGTATTCCATCCAAACTAGCTGGCCATAAAAATAGCACATG
TTTCGGTTTTCACTTTTAAACGTTCTGCTCGAATTCGATTTGCACAAAAATAAATATTTATACGATTTGGATTCGCTTATCCCAAAGACCAGTAC
AGTTGGCTATCAAATTAATTAATTTAGATGCAAATTCGATAATCAAGAACTTTAAATCATACTGCAATCTCTTTTGAACTTTTTTCGTATAACAC
CACCATTGAAATTGATTACAACTTCGTTAATATATTGCACAAATCCATTTTCAAATCATTAGTTTCACTTACTGAAGTTTACCTGTAGTTGTAAA
CTTGGATCTTTTATTACGTGCTGTAAAATCTTGTAACGGCGCACCTTTTACGGAAAATGACGTAGAAAATACACTCATTTTTAAATAATTGGGTG
CTTGTTGTAAAAAATTAAATTCATTATTTTACAGCAGCAACCAATTGCTCGTAATTACCATACTGTATTGTGTGAAAATAGTTAGTGCCACTACT
GTTTCAGTCTCATAAAGTTGTATTTATCAAACTTCCTAAAGGAATCAACGCAAAAACATTTTCATTTTCGAAATGGTGTAAATTAAGTCTTCAGT
TTAATCATTTTTTGAGTGTATTAGGTCTTATCTTTTTAGTACATTCAATTCCCTTCGCAGGATTATTAAGTGTATATAAGGATGATCTGAATTAC
CATACCCTAAATGCAGAGCATTTACAAAATAAAAGCAAAGGCGACGTCATTGAGCAAACAATTACCCATTGCGCTCTCCCGCTCTCTCCTCTCTC
TCTCTCACGCTCGCTTGAAGCGCGTGCCTTGTCAACCTTCCCCACCACCCCTCCTCCGCACCCACTTCCACTCTTCGCGCTAAGCTTACCGTTAC
ATGCAGCTGCTGCTGCAGCTGCGACGCTGTTGCTGGGTGCGCCCGCTGCTGCTGCTGTTGCGACCCCGTTGCCGCCCACTGGGCCAGCGCCTGCT
CCACCCACTGTGGAGCCAGGATTTGTAGTTGTAGCTGTTGTTGTTGTTGCGCCCTTTGTGGCTGATGCAGTGGGTGTTGTTGCTGCTGCCGCTGA
TGTTGTTGTTGCTGCTGCTGGTCCGCCGGGCATGTGCGGTCTACTGTTCATCAGCCAGTTGGCCAGGTGCCTCTGCCGCTCGAGCTCGATATTGG
TGCGCTGCATTCCGAGTCCGGACAGCTTTAAGGTCTCGTTCATAATCGCAATCAATCAAACCGAAAAAAAAAAATGAATGCGCCACTGCAACGAG
CGGACGCGTCGCCGCCGTCGAAACGAATGTATTCCAACTCGGTACGTCTCGCGATGCCGATTTTCAGCGACCAACTGAGCAGACTTGTCCGACTG
CAGCGGCGCCCTCCTCGATCGTTGCTGCTGCTGCTGTAACGAGAGAGCCACAGAGAGAGAGGAAGAGAGAGAGAGAGAGAAAAGCGTGAGAGAAAAA
CAACGGAGAGCACAAAATGCGCGCACAGTGGGCAGCGTTTACATAAGTGGCGTCGCGGCCAGCGCAACTCGAATTCGCACAGTGGCCTCAATCTG
ACAGCTGCACACTCTCACAATTATCGGCAAAATAATATTTGCCGAGCTGCTCAATTTTGTTTGGCAAATATTTTTGCCTTATTATTAGACTACCT
ACTTATTTATTGAGTGTGGTTTGGGCATAGTAGAGTACCTTATATCGGGGAGTTGTGTCACCCCCAGTTTTAGTTTATGCATTTCTGAATCATCC
GTATTTCAGAAGAATGAACATTACCGTGAACAATTTCTTATTTCACAAAAGGCTACTGGATGACAAATTAAAATAAGATATAGTGCTTCCTAGAA
AGCTATTTTTCAAAGATATTCACTTTAATTGATTTGTATAAATTTACTTTAGTTTTAGTTTCACGAATTTTGTAGTTAATCTTTTCTATTCTAAT
ATTTATGCGTTTAAGTTTCTTTTTATTGTTGCCCTAATCAAATGATCAACTAAATTAGCAGCTGTGCAAACCTTTTCGCAGAGTTCATATACCCC
AAATCCAAGCGTAACAACAACAATTGCAAAATGTGTAAAAAGATGTTGAGCTTTAGCAAAAAAAAAAAATCTCCATCGTAATTGAGATGGTTGCT
GTGTGCCTGTGTGTGTGAGATGGATGTGCGTGTGTTGTGCATAAATTAAAATTGCGATGACGATGACGACGTTATCAGAAACTTGGCTCTCTCGC
TCCCTCGCTCGCTCACTCGCCCGTTCGTTCCTTGGCTTGTTCAATGTCGCCGCACCTTTTCGATTGTCGACCGCCCGCCGCCCACTTCGCCGCCC
CCCAGCCACCACCCACTACTCGTGCAACAGCGTAGAAAGCAGAGCCAGTTCGTCTGGCGTTGGCAGCAAAAACAACAACCGCGCGTCATCTTCAA
ACGTTATGCGACAGCGTAATCGGTGCGATTGTTAGAAGAGCGAGC
(SEQ ID NO: 1012)

Exon: 11870..11300
Exon: 8132..7807
Exon: 7444..6961
Exon: 5023..1001
Start ATG: 11633 (Reverse strand: CAT)

Transcript No. : CT26270
CTCTCACGCTTTCTCTCTCTCTCTCTTCCTCTCTCTCTGTGGCTCTCTCGTTACAGCAGCAGCAGCAACGATCGAGGAGGGCGCCGCTGCAGTC
GGACAAGTCTGCTCAGTTGGTCGCTGAAAATCGGCATCGCGAGACGTACCGAGTTGGAATACATTCGTTTCGACGGCGGCGACGCGTCCGCTCGT
TGCAGTGGCGCATTCATTTTTTTTTTTCGGTTTGATTGATTGCGATTATGAACGAGACCTTAAAGCTGTCCGGACTCGGAATGCAGCGCACCAAT
ATCGAGCTCGAGCGGCAGAGGCACCTGGCCAACTGGCTGATGAACAGTAGACCGCACATGCCCGGCGGACCAGCAGCAGCAACAACAACATCAGC
GGCAGCAGCAACAACACCCACTGCATCAGCCACAAAGGGCGCAACAACAACAACAGCTACAACTACAAATCCTGGCTCCACAGTGGGTGGAGCAG
GCGCTGGCCCAGTGGGCGGCAACGGGGTCGCAACAGCAGCAGCAGCGGGCGCACCCAGCAACAGCGTCGCAGCTGCAGCAGCAGCTGCATGTAAC
GGTGGAGCAGCCGTTGGCGCCCATCACGGCCACCATTCGGCGGCTGGGGCGCGCAAGCCCAAACTGCGGCGCTTCAACTCCCACGACACCAGTTC
GAATATGTTCTCGGTGGCCGATTTCGAGAACGCCCGCCTAGCTCGCCGCAACGAGATCGAGCTGAACCAGCGGAGGGCACGACGCGTGCGCGGCA
GTGCCAACAACAGCACCTACGGCCTGGGATCGGGCTCAGGATTGCTGGGAGGTGCCCATTCTGGATACTGTGACGCACTCAATGGCAGCGGCGAT
TACTCCACCGGGGACAGCAAGGCCTCCAAGGGCAGCAGCGAAGGTGCGCTGACAGCCATTGAGTTCCTTGAGCGGAATTCCCTGCCACGAGTCGT
CCGCATTCTGCATGCGAGCAAGAGCTCAAACGAAACGCTGCAGTCCAGCTCATCGCATGGCTCCTCCACGGCGGCATCGAGCAGCTCCTCGACGG
GAGCGAATCCGTTTGGTTCTGGTGGCAGTGGTGGTGGAAACATTTCCAGTGGCAACATTGACACCGGCACCCATTCATCGTCCAGCGGAGGCAGC
GCCACCGGAAACGGAACTGGCTCTGGTCCTGGTCTTAGTTCGGGCTCGGGTTCTGGTTCTGGTTCTGGTCACCAGAACAACAACGGTCGCCACAG
CAGCAACGGTGGCACTCCACCCGGCCACGATGAGCTTTTTCTGCTCTACAGGCTGGTGCGACAGCGCAACATCTACCACGGACACAACGCCAAGA
CTCAGGCATCGCAGCGCAAGAAGACTCTGCTCATTCCACAGGAGTTTCCGGGTTACTTTTCGATGCTAAGCGAGAAGGGTCTCCCCACGGCCACA
CAATACGGATCTCTGATACAGCTGGTTCGGGAACGGGTTTACAAGTTTGTCTCAGTGGACAACATGCCGGCGTTTACGGAATCCTCGCCCAACAG
TACGAGCAGTCCAACGCACGAGGGATGCCTGCCCATAAACAAGGGACGACCACAGTACGTGAAAACGACGGCAAGGGGCGGGCAGGTATTCCGTC
TGTTGGCCGTCTTCGAGGATGGCAAACAGGATCAGGTCAATATGTCGCAACATGGCAACGGCAATGCGACCAGGTCCCATGGCAGTGGGTACATG
GGAAGGGAGAAGGAAAAGAACCGGTATGCCCAGCTGCTTAATGAAAACCGGCAGGTGTTGTACGTCCCACTGTCCACCAAGGGCAAGTTCTACGA
GATTGAACCGGGAATTCCTCAGCTGCTTCAGAAACTGGGCGATGCGCAGCGCAAGCTGAATCCGGAGTGCGTGCATCGTTTGAGTGCTTTGGTGA CGGCGGCCAAGCAGTTACCGCTAACACTGCGCTATATCTCCGGTCCAGGCGGACCCGACATTCCCGAGCAGCTATGTATTAGTCAAGTGAGCAAG
GAGGATGTGGTTGTTGGCTGTTCCATTGAGGACGTCGATACCCAGACGCCCTTGCAGCTGAGGAAGTTCTATCCCAGTCGAGATATTCAGCTGGT
AAAAAGTTATTTAGGATTTGACTCCGAACAACGGATGCTCGCTAACACGAATGTGCAGAATATGCTAAAGTTTTGTCAATTTAATTGCGATCCAT
TCCTGAAGCTCGTGGAGATTGAGTTAATTCAGCGCTCGGAACGTTCGGGAAGCAAGAATCGAGAGGGGCTACGAATCTTGAAGCCACTGCATTTT
CCAAAGATCCTGAGACGCGAGAAGAGCTCCATGGCAGCAGCGCACGAAAAGGAGGATTCCATTATTTTCCTCAGCAAATCGGATCTGGAGAATCT
GGAAGCCAAGGAAGCGGCAGCTTCTGCTGCAGCTCACTCGGAATCCAGTTTGAATCGCATCTCTGAGCGCATGCGTGTATTCCAGTCTACCAAGA
AGAAGTGGTTCGGAAAGCATCATCCGCAGCAACAGCAACCACAAATAGAGAAACATCAATCTGACTTAGATCTCGATGAGCAGGCCAAGCGAATG
AGCATGGAGCGCTATACGGATATGTCTAAGCTTCTGCAGGAGCGTTTTGGCTCGAATCCCGAACAGCCAGAGCAAGATGCTATCTCCCTAAACAG
CACAGCAGCGTCCGACACCGAAACAACGATGCTGACTACCATGGAGCCGAGGTCTCTGGACACAATGATGCAAAAGTCCATGTCCCTGCAGGATA
TTGAGCTTCTCAATGGTCAATGCAAGCAACGACCTGATTTGCTGGCCAGCCACAATCACAATGACGCCATCAGTGAGGCAGGTACCGAGCTGGAA
GATGTGGAGAATCAGACCCCACCTCCACAGTCCTTCATCACGGAGAAGCTGTACAACGAGTTTCACGTGAAGACCAGGCAGTATAGCAAGTCATC
GTCCAGTTTGCACCAGTTACCTCTGTTTAGCTTGCCGCAAAAGTTGCAACTTCACGAGGCTGAAAAGGAGAAGCGACATCTGATGTTGCTAAAGG
CGCAGCAACAGGCGCTGACCAAGGAACCGGTCACTGGAAGAAGGGCAGCCGGTGGAGTTTCTCTGTTGGGAGGAGGACTCAACCAACTGGCGATA
TCGCCCGCATCGCTGGTGGAAGACGACTTGCCCTACTCCAGTGTGCGCGATTCGCTTGTGATTTCCGGCGGGGACTGCCTGCGATCGGAGTCCGC
CAGTAGACCAGTTCCCGCTGTGGACTATACCAAGGAGAATATATACGCCGAAATCTGTCCCTCGCACACAGTGGACACCTTTTCGGGCGCCACTC
AGTTCACTCATGTGCCCGACGATGATGGAGATTATGCATCGCTCAAGTATTCGGTCAATGGACCACAGTCGGTCAGTCGGATTGAGGTGAATGGA
GCTACGGCGGCGGTGAAGAGCAGCGCAATCAGCTACCATACTGTGTACCTGGGCGAGGAACCGCTGGGCGAGAGGCACGCTGCCCACATCACCAC
CGTTGAATTGGCCGGAGAGGATAACATTTACAATACGCTCAAATGATGACTCATGTGATTCCGGCGACGTAAGTTGGCCGGCGCCAAAGGCCTGT
TTTAAAAACGCCGATGGACAAAAGGGCAAGCAAAAGGGAATTCATGTTACCCATGATCCTACCAAGGCCATCTTATAGTCTTGTACTCGAAAGAA
ATTGAAGTATTCTCCAATGAAGACTAATTTGTTAATTAACTCATTGAAAACATACCTTACCCTACTTATTACCCACTGTTTTGACAGGACTTTAT
TTTCATGCCATTGGATTACTTTAATATAAACATACATTTTAATAGAGAAAGAGTATTTAATTTATGTTTTGGTTTTATTGTGTATTTCTCAGTTT
CATTTTATAGCACATGTATATTAACATTGATAAGCAATGGACAACAAACGTTTACCGCATTGTAAATTTTGTCTCCTTTAAATATTTAAAGAATC
TTAGTAATGTGAGAATGTTCGAGTACAAGACAAAGATAAGAATAATTTTAAATCAGAGAACAATTGAATGACACAATTTATTTGCTGCGAGGCCT
TGCTTAAGATCGGTAAAATGTTTTGAATAGGCTTTTGGAGCAATCAGCCACAAAATCAAATGAATTTATATTTTATCTTGCTTACAATTTTAAGA
AATGGTTACAGCAGAATACCAATGTAAGATCATTGTCATATAAGTGAGAGGAGCTCTCAATTTTAGGAAAAATACTTTTCCCTGTCTGCCCTTTG
AAAAGGCGGTGTGAGAACTTATATTTAATCATTCAATATGGCGCTGATGCACAAAAAACAACAATAGTAGAGAAAATATCTTATTTTGCAATAAT
ACAAAACTCAAAGCGAATGATGTATGGTGAATTCAAACAGAATTTGAATCTGGGTCAACAAACACCCAAACGAAAGTAATGAAAAATCTCGATCG
TAACATATAATTACACATACATATATTTGTAGAAAGTAGTATTAGTATAGGGATCAAATTTGTAAATGAGACGTCGCTGTGGACGACGAAAAACC
CCCTTGAAATGACAGCAGAAATTGTAATATTATTATTAACCAAGAGAAGACAAGCAATTTTGTATTGTAACATACAGATGGGTGCCGCCGGTCCA
CGACTTTCAATCCATTAAACGGCCAGATCCCTAACCCATACAAAAAAAAAATACATCATATTGAAACTGAACATTTGGAAATTGCAATATTATACA
ATTGTATACATAACTTATATATAGATATATATATACTTATACACATATACTAACGTACATACGATATGGAAATCTTAGTTCAAACCTAAGGTATT
ATTAGCTCGTAGGCAATCAACAAGTCAAATCAAATCATAAGCGATATACATCTATATATGCATACATTGTATATTTGTAAAATAGCATAAACTTT
TAGGGCAAAATGCCAAACTTTTACACGATCTCTCGTATTTTGTCGTTCTTTTTTGGAAACCCATTAACTTGGTTTTGTTGGGTTTACTTGTTTTA
CACCCAACAACTCAACGTTAATCAAACGAATCGATTACATCAAAGTGCGAGCATGTCCACAAACCATATTTGAATCTGTCTAATTGTCCGCTTCG
TTCGATGACCTCACATAACTTTGCATACAACACACGTATTTAACATTTAAGTTATTAAGTGACTTTATCGCGCCATATAGATGTGCAGTCTCAAA
GTAGAGTTTAGACACTAAGGTCCAGTTTCTAGTCTTAATTTGAAAACAAATATGAAGCCGTTTCGAAATGGAGACATGCCAAACTTTTACTTGTG
TAATGAATGACTTCGGCATGGCCCGAAGGATCCTTCAATATATACACTTTCAATTGGGTACTACATAAATAAATATTTAGCAAG
(SEQ ID NO: 1013)

Start ATG: 238 (Reverse strand: CAT)

MNETLKLSGLGMQRTNIELERQRHLANWLMNSRPHMPGGPAAATTSAAAATTPTASATKGATTTTATTTNPGSTVGGAGAGPVGGNGVATAAAA
GAPSNSVAAAAAAACNGGAAVGAHHGHHSAAGARKPKLRRFNSHDTSSNMFSVADFENARLARRNEIELNQRRARRVRGSANNSTYGLGSGSGLL
GGAHSGYCDALNGSGDYSTGDSKASKGSSEGALTAIEFLERNSLPRVVRILHASKSSNETLQSSSSHGSSTAASSSSSTGANPFGSGGSGGGNIS
SGNIDTGTHSSSSGGSATGNGTGSGPGLSSGSGSGSGSGHQNNNGRHSSNGGTPPGHDELFLLYRLVRQRNIYHGHNAKTQASQRKKTLLIPQEF
PGYFSMLSEKGLPTATQYGSLIQLVRERVYKFVSVDNMPAFTESSPNSTSSPTHEGCLPINKGRPQYVKTTARGGQVFRLLAVFEDGKQDQVNMS
QHGNGNATRSHGSGYMGREKEKNRYAQLLNENRQVLYVPLSTKGKFYEIEPGIPQLLQKLGDAQRKLNPECVHRLSALVTAAKQLPLTLRYISGP
GGPDIPEQLCISQVSKEDVVVGCSIEDVDTQTPLQLRKFYPSRDIQLVKSYLGFDSEQRMLANTNVQNMLKFCQFNCDPFLKLVEIELIQRSERS
GSKNREGLRILKPLHFPKILRREKSSMAAAHEKEDSIIFLSKSDLENLEAKEAAASAAAHSESSLNRISERMRVFQSTKKKWFGKHHPQQQQPQI
EKHQSDLDLDEQAKRMSMERYTDMSKLLQERFGSNPEQPEQDAISLNSTAASDTETTMLTTMEPRSLDTMMQKSMSLQDIELLNGQCKQRPDLLA
SHNHNDAISEAGTELEDVENQTPPPQSFITEKLYNEFHVKTRQYSKSSSSLHQLPLFSLPQKLQLHEAEKEKRHLMLLKAQQQALTKEPVTGRRA
AGGVSLLGGGLNQLAISPASLVEDDLPYSSVRDSLVISGGDCLRSESASRPVPAVDYTKENIYAEICPSHTVDTFSGATQFTHVPDDDGDYASLK
YSVNGPQSVSRIEVNGATAAVKSSAISYHTVYLGEEPLGERHAAHITTVELAGEDNIYNTLK*
(SEQ ID NO: 1014)

Classification: known_flybase_gene
Gene Symbol: B4
FlyBase ID: FBgn0023407

Celera Sequence No. : 142000013384789
CAAATTATGCATTTGAATTCTCTAGAAATGAGTACCAAACAACCCATAAATTCAAAATCAATGCTTATTGTACATCTATAAGTATTTTATATTTA
TTTTGGAATTTATCATAAATTTTGCTTGAATTTTAAATACACATCCATAGATCGTCATTAGCTATTCTCAATTCAGTTTTAAATAGGTCGTAACA
TAATAAGTTTGACTTGCAAGCAAAACAGAAACGAACAAAATGTATCTAAAAAATGTGAATACTTAAGTGAATCAATATATTTTATATGCTGTCTT
CATGTACATAGATAATAGATAATATATAACAATTACGATTACAAAAAAACACGACATTTTATGTGAGTGCAGGACAGTGACGGCGGAAAAAGGGG
GTCGGGACATGGAACAGGGGGGAGGGAGGAGAGGGGGACAGTGGAGCAGTGGGCGTAGGAGCACAGCTTGGATGAAAAATGAATTTCGCTTTCTT
GTTGTCTCTCTGGTCGAGGCGACGAGAGATAAAGTTCTATAATGTAAGCGTTAAATATATTATTTATATTATGTTTGTTATATATATAAGATCGT
ATATATGTGAGTGTGTGTGTGTGTGTGTGTTGCGTGTGCGAGGGAGTGGGGTTATTCCTATATCGTTTAATGACTTAAAGAACTAGAAAACATC
ATCATCAGCAGCAGCAGCAGCAGCATCATCGTCATCAGTGTCATCCCTTTCGCCTGATTAATCTGGGTTAGTATCAGAATCGAATTATTCCACAG
GACAGAGACAGACACACAATAATTTAGTCTAGATACTTGTATTTGGAGGCATATATCGTGCGATTAAGATGTCCTGTCTACTTGATCCGCTGCAG
CTGCGTGTCGAAGGCATCGTGGGCCGCTTTAGTTTCCTTTTGTTTTTTGTTTTCTCCTTTTTGTTTGGTTTTTTTTCACTTTCAGTTTAGTT CCAAGTTCGGTTTTGTTCCGTTTATAAATATTGTTTATGCATTGTGTGTTGTTTCTGTGTTATCATTACAGTAATTATTTGTAATAAAGACGACG
GCATTCTAGGAATTGTTTATGCACAAAAGCAAATAGTTATTAGTTCCATGCTCCAATGCTAGCTTTAGTTTCATGTTTTTCTTTACTTTCATTTC
GTGTTAAGCTATTTCAATGTTTATTAAGTGTTCTTTCTCCATCTCCCTCTCTCTGGCGCGGCTATCATCATCTTTTTCTGTCCCAGTTAAGCAGG
ATGAGTGCTGCTTGAGTTCGTGGTTGATTGATTGATTCTCCTTTTGATTTGATTAGATCCCCGGAAAGCAGAGTGTCACTTAGTACCTGCTGTTG
TTAAACTGCGAATTGATGGCCGTATTAACGGCCGAGGAGGCTGCTTCCTGGACGTGCTGGTTGCGCAGAAACTCGGTGGTGAACTCCGCCTGGGC
CTTGGCCATACTGGCCCCTGTGCTGCGGTAGATCGAGTGAATCTTTGTGATCATCAGCACATTGGCCACGGCCACCGCTGTGAAACAGAATGCCA
CGTTCAACAGCAGAATGCCGACGATAATACCCGACGCTTGCCCATCGAACTGCCCGATGGCCGTAATAAAGCCACAGTAGCCCATCTTGTTGAAG
CCCACCGCCTGCACAATCGAGTACAGCGTTTGAAAGAAGTAGATGAAGAAGAAGACCATGAAGTTGAAGCTCGAATCGTTGCGGAATGCCTTGTA
CGCCGGTCGGAACCTGAAAATTAATCACACATCATCACATTATTCATGTTTTAAGAATCTTCCAGGTATAAACTCACCAGCAGACATAGGAGGCG
GGCGAGAAGAGCATCGTGTAGAAGATGGCCAGGAAGAAGGTCTCGAATTCGCCAGCGTGGAACAGCAAAATTAGACCGCCTATCACGTTGGCCAA
CAACGTCATGGTGTAAACTGTCGGAGAAAGTATTCAAAATAGACACATACAATCAGCATAATGCTATAATCTGTAGGGGAAAGCATTATTATATA
CTATATACTATGCATGCAGTAAATAATGCTAGAAATGCATTTAAAAACTATCTTAATACTGATAACATGTAAATCAAACAAATTTCATGCTCCCC
TCTTTGCAAGCATATTCTGCACAAAGGCACGCACACATCCAAGACCATTAGCCATTCAGCTATATCTGATTAATAATGGCATCGGCCTGTAGACG
ACACGCGATGACTAATTCCACAACCTATGGCACCGCTTATCAGCGAAAACATGTAGAAAACACAGCCATAAAGAACCAATACTCACAAATCCAAA
TGTAATACAATCGCTTGACCAGTTTCTGGAACTCGGGCGGTATCTCCACCTCGAAGTCCTGGTAGAAGCACGGCTTTACACAAAAGTTATCCGGC
AGCGGTGGCCAGTTGTTCAGCTGCGGCACATTGCCCTGTAGCTGCTGCTCGCGGCGGTCCAGTTCGGCGGCCTTGCGGTCCAACTCCTCCTGCCG
GCGCTGGATACAATGAAAATCATATGATTATCGACTGTTTTATATATACATTTTGTATGACTTAATAAATTGGCCGTATATGGTAAATACTTTAA
ATCTTATTCATTTACATATTTGGGAAAACAAAGGCGAAATTCAATGATAGGAATTCACATCCAAATCTTGAGTTTGTTAAACTTCTATCTTAACC
TCAGGCATTTGGCCTATCTATAGGAAATATTCTGTACAAGAATAAAGTGCAAACTTAAGCCTCCAAATCATATGTATTTAGATCTACTAACTAGT
ATTTCTTGAATTATTGTGTAGGGCCGAAGAAGCCAAGTAAATCAAGAGAAACCGCAGTTTGCACAGTGAAGACTCGGCGCGGCAGCCGCTTCTAG
TCTCAACCAGATAAATGCTCCAAAGCGGATATATCGTTGGCAGATCGAGATAAGCCCGCTTATCTTTCTGACTCTTGATGGAGAGTAAAATGTGA
TATGCCTGCCCTAATCCCGGCACTCTAGCAAAGTGATTACTGTACAGACTTTTAGGGCAAACTTTTAGTGTAACTGTGTGGTGTGGTCCATTTCG
ATTGTTTCCGAGTATTTGGATGTACATATGCGGTTTTTGGAGTATTGCGGATGTGGCCATGCCGGCACAGCACACCGCAGAGTGCTCACTGTTGT
GTGGGCGGTAACGCGAGACGACCGGCCAAGTGGGTTACCTGCAGCTCCTCCGAGGTGATCTGTATGCTGGTGCTAGGCGCCGAGGCGCCCAGGGA
ACTGGTCTGCGGGGGCGGAATGTTCTGCGATAGCGGCTGGACCACCGCCGCCGTGTTCGTTGAGTTGATCTGCAGCTGCGGCTTGGCCTGCTCCT
CGAATGGATTGTAATCCTCAAGAGAGACAAGGGCGGCGCCGCTCTGGAGTCGTCGTGCCTGCTGGATGGCGGGGTCCTGCGGGGGAAAACCGGGA
AATCCCAATCAGAAACCAATTCATTCAACATATGTGACGAATGCACCCAACACACACACACACTACACTCACAGGCACGCACACCAACACCCCAC
CTTTGCGTACGTGTGCGTGTGTGTGCGATGGGTTTTTCTTCGGCTTCCGCGCTCTCTCTCCTAGCTCTTCTATCGCCTCACCGCAAACGGATTG
TCCAGATTGGGCTCCCCGAAGGGATTCTCGTCGAGACCGGAGCCGGACATGGGAATTCTACTTTGGATACGGCTGTTCAATGACCAGAAAAACGC
ACTGACTCGCACTTTGCTTTTCGCTGTGTATATTTTCCCTAAGACTCTGCTCAGTTATCGATGTCGGTTTTAGTGATGGTTCAGCATCGATAAGC
TTTCGTTGGGAATCAAAGTGTAGGCCTCAAATATCGAAAGAATTACTTTAAAGAATTAATGTTATTTGAATTACATATTAAATTCATTTTGGCAG
AAAAACTTATTATTTAACACATTTAACATTAATCTAGAATTCTGAAAAATGTGAATAACTGGTATACAATGGTCTGATTTTTTAGGACCTATTAA
TACATTTTATTAAAATGATAGCAAAAAGAAAAGATTCTATATACAATTGGATGTAAACCAGCAGTTATCATATGAATTTTAAATTTAAATGGCAA
CAATCGTGCCAATCGGAACTGCTCCAGCTGAACCAGCTGCGTGGAACCAGTTCCCATCCCTGGGGCCGCCATTCCGCAATTGGAATTCTAGTGTC
TTGGGTTGCGATTCGATTCATTTACCGCTGCCCGCGTCTCCAATTCGGTTGTGTGCGATTCTGTCTGCTCCGCATCCAAGTCAAACATCCAATCC
TTGCAAGAATGTCGAAGCCCAGCTACAAAGTCGGTGAGTTGCGTTATAAATAAACCCAAACGGATGGCAAACTCTCGAATCGAATCTCCGGCCGG
CAACAGGCGACATGTGCGGGTGAATTGCATCTATTCATGAGCACATGTTTCTGAGGTTAAAAGAGAGACAAAACAGAGGAGAGCACGTTGTTGCT
GGGGCAAAAAACGTAGAAATTCAGACCGTATGGTGTATAAATCAACAGTGCCTGCTTATCTGACCCTATCTCCCTTTTATATCCCACTCGACAGC
CGATATCAGTCTGGCGGAATGGGGACGCAAGGCGATCATTATTGCGGAGAACGAGATGCCCGGTCTGATGGCCTGCAGGAAGAAGTACGGCCCAT
CTAAGCCCCTCAAGGGCGCCCGCATCACCGGCTGCCTGCACATGACCGTCCAGACCGCCGTGCTCATCGAGACCCTCGTCGAACTGGGCGCTCAG
GTGGGTTCAGT
(SEQ ID NO: 1015)

Exon: 3761..3598
Exon: 3401..3174
Exon: 2473..2272
Exon: 1917..1788
Exon: 1723..1001
Start ATG: 3660 (Reverse strand: CAT)

Transcript No. : CT26276
AACTGAGCAGAGTCTTAGGGAAAATATACACAGCGAAAAGCAAAGTGCGAGTCAGTGCGTTTTTCTGGTCATTGAACAGCCGTATCCAAAGTAGA
ATTCCCATGTCCGGCTCCGGTCTCGACGAGAATCCCTTCGGGGAGCCCAATCTGGACAATCCGTTTGCGGACCCCGCCATCCAGCAGGCACGACG
ACTCCAGAGCGGCGCCGCCCTTGTCTCTCTTGAGGATTACAATCCATTCGAGGAGCAGGCCAAGCCGCAGCTGCAGATCAACTCAACGAACACGG
CGGCGGTGGTCCAGCCGCTATCGCAGAACATTCCGCCCCCGCAGACCAGTTCCCTGGGCGCCTCGGCGCCTAGCACCAGCATACAGATCACCTCG
GAGGAGCTGCAGCGCCGGCAGGAGGAGTTGGACCGCAAGGCCGCCGAACTGGACCGCCGCGAGCAGCAGCTACAGGGCAATGTGCCGCAGCTGAA
CAACTGGCCACCGCTGCCGGATAACTTTTGTGTAAAGCCGTGCTTCTACCAGGACTTCGAGGTGGAGATACCGCCCGAGTTCCAGAAACTGGTCA
AGCGATTGTATTACATTTGGATTTTTACACCATGACGTTGTTGGCCAACGTGATAGGCGGTCTAATTTTGCTGTTCCACGCTGGCGAATTCGAG
ACCTTCTTCCTGGCCATCTTCTACACGATGCTCTTCTCGCCCGCCTCCTATGTCTGCTGGTTCCGACCGGCGTACAAGGCATTCCGCAACGATTC
GAGCTTCAACTTCATGGTCTTCTTCTTCATCTACTTCTTTCAAACGCTGTACTCGATTGTGCAGGCGGTGGGCTTCAACAAGATGGGCTACTGTG
GCTTTATTACGGCCATCGGGCAGTTCGATGGGCAAGCGTCGGGTATTATCGTCGGCATTCTGCTGTTGAACGTGGCATTCTGTTTCACAGCGGTG
GCCGTGGCCAATGTGCTGATGATCACAAAGATTCACTCGATCTACCGCAGCACAGGGGCCAGTATGGCCAAGGCCCAGGCGGAGTTCACCACCGA
GTTTCTGCGCAACCAGCACGTCCAGGAAGCAGCCTCCTCGGCCGTTAATACGGCCATCAATTCGCAGTTTAACAACAGCAGGTACTAAGTGACAC
TCTGCTTTCCGGGGATCTAATCAAATCAAAAGGAGAATCAATCAATCAACCACGAACTCAAGCAGCACTCATCCTGCTTAACTGGGACAGAAAAA
GATGATGATAGCCGCGCCAGAGAGAGGGAGATGGAGAAAGAACACTTAATAAACATTGAAATAGCTTAACACGAAATGAAAGTAAAGAAAAACAT
GAAACTAAAGCTAGCATTGGAGCATGGAACTAATAACTATTTGCTTTTGTGCATAAACAATTCCTAGAATGCCGTCGTCTTTATTACAAATAATT
ACTGTAATGATAACACAGAAAC
(SEQ ID NO: 1016)

Start ATG: 102 (Reverse strand: CAT)

MSGSGLDENPFGEPNLDNPFADPAIQQARRLQSGAALVSLEDYNPFEEQAKPQLQINSTNTAAVVQPLSQNIPPPQTSSLGASAPSTSIQITSEE
LQRRQEELDRKAAELDRREQQLQGNVPQLNNWPPLPDNFCVKPCFYQDFEVEIPPEFQKLVKRLYYIWIFYTMTLLANVIGGLILLFHAGEFETF
FLAIFYTMLFSPASYVCWFRPAYKAFRNDSSFNFMVFFFIYFFQTLYSIVQAVGFNKMGYCGFITAIGQFDGQASGIIVGILLLNVAFCFTAVAV
ANVLMITKIHSIYRSTGASMAKAQAEFTTEFLRNQHVQEAASSAVNTAINSQFNNSRY*
(SEQ ID NO: 1017)

Name: SCAMPs
Classification: transporter

Celera Sequence No. : 142000013384663
TGTTTTTATTTAAAGCAAATATACCGGAATTTTGGCTGTGTGTAGTTTTTCTTTTCCAGAATTTTTCCTCTTTTCATTCCATTGCCTCTAGCAAT
TTCCTCTCCAAGTCGGCACATTTTATGCCTTTAATTACGCGCAGAACTAAAAAATTGCTAGTGGGTGTAATTGTAAAAAATCGGGTCAGCAATAA
TGCACATTAATTATGGTTTATTGTTGCTGCAAGTGTGTCATCGTGTAGGAATCGAATGAAGTAGTCGGTTCGTTTTTAGTTGGTTCGGGTTGCAT
TTTTTTGGCTGAGCCAAGAAATTGTTTTTCGATTTATCTTAGTCGTGTTGACATTATTTATTTATCTTTAGCATTTTTATTCGCACGGGGAATGT
TACAACAATTTGAAGGTTAAAATTTGTGGTATTTGTACGCACCACGCCTAAAGATTTAAAGAGCAACACACAATTTGGTTTGTTTATTTTGGTTT
CTCGCTCTTTCGTTTCGTGATCGAGATAGCTAGTAGTTCCTTCTTTTCGTTTTGATTTTCGTGGCATTAATTTTGGGTTTTCTAAAAAGCCAAAT
GGATCTAAAAATAGTTTCACCGATTCTCGTTTATGCTGCCGCTGCTTCAGCACGTGTATATGGGAAAAATACGGATGTACATATGCGTTTTTCC
CCTAAAATCTAGAACTTATTTTGGCCAAAATTAGAAATTAACTAAAGTGGAAATATGCGGCAGTCCATTCTGTCGCCCCGCCACTTTCTCTGCTT
TCCCCAAAAATACTTTTTGACATTCACAGGGAAACCTGTCAGTTTTCCGCTCTCTGAGAGTCATTCCATATCTCTCTCTATTGGTTGCATTGCAT
TCTCTTCGTTTTCCACTCTCTCTTGTTTGCCACCCCCTTTTTGGTGCTACTGCCCTGCAGTTTTTAAGGTCAGTCGAAAATTTTCCAGCTGAGCG
TCAAGTTGAAGAAGAACTTATTCTAAATTCGGGAAAAACCCTTTTTCTCCATTTAATTGCAGCATTTTAACTGAAATCATGACTGAAGTTGAGCA
ACCGCCACAGAATGGCATAGATCCCACTGCCGGCGAAGATGATGACAATAGCAAAGCACGTCCCGCGGATATTGAACAGGTAAGTGCAGGCCGTC
GAAGTCCCAACTGGATAACAACCCCTCCACCAAACACTCACCACCACCACTTTACTTTCTCCTCCTCCAGGATATGCGCGAAATGGAGCGTCGCA
AGCGAGTCGAGGCTATAATGGGCTCGAAACTGTTCCGCGAGGAGCTGGAGCGTATCGTGGACTCGGCGCGCGATGGAGGTGCTGGCGCTAGTGGA
ATCCTGCAGCAGCTGTCGGACATTGTGGGCGTACCAGTGTCCAGGGTGGGCAGCGTCTTCAAGAGCAGCAACTGCATGGTGCCAATCAACGATAT
ACGCGGCGTCGAGTCCATGGGCTATGCCAAGGGCGAGAAGATACTCCGGTGCAAGCTGGCCGCCACATTCCGTCTGCTCGATCTGTACGGCTGGA
CCCAGGGTCTGGGGGCACAGATCACCGCCCGACTCAAGGTCGATCAGGAGTACTTCCTGGTTAACCCATACGGCCTGCTTTACCACGAGATCACT
GCCTCAGCGCTGAACAAGGTGGATATGCAAGGACAGATTGTGGAGCAGGGCACCACCAACTTTGGCGGCAACAAGAGTCGTAAGTGGCTGACAAT
TGAACCTATAATTGAATATATCAAATATATATTTATCTGTTTTTAACTGCCTTGCAGACTTTGTCCTCCATTCGGTGGTACATGCTGCCCGTCCA
GATATTCGATGCGCCATCTATATCGGCTGCAGTCCAGTCGTGGCTATTTCCTCACTAAAGACGGGTCTATTGCCCTTGACCAAGGATGCCTGTGT
GCTGGGCGAGATCACCACTCACGCTTATACTGGTCTATTCGACGAGGAGGAGCGCAATCGATTGGTCCGCAGCCTTGGTCCCAACTCCAAGGTGA
TTCTGTTAACTAATCACGGTGCTTTGTGCTGCGGAGAGACCATCGAGGAAGCCTTCTTCGCCGCCTGTCACATTGTACAGGCGTGTGAGACGCAA
CTGAAGCTGTTGCCCGTCGGTTTGGATAACTTGGTGCTGATTCCAGAGGAGTCGCGCAAGGCCATTTACGAGCAGTCGCGCCGGCCGCCGGAGGA
TCTGGAGAAGAAGTTTGCCGCCGTCGCCGCTGCCGAAGATGGTGCTGCTACTGCTGAAAAGGATGCAGCCGAAGCAGTACCCAAGGTTGGCAGTC
CGCCCAAGTGGCGTGTGGGTGGTGCTGAATTTGAGGCCTTGATGCGCATGCTGGACAATGCTGGCTATCGCACTGGCTATATCTACCGTCATCCA
CTGATCAAATCGGATCCTCCCAAGCCTAAGAACGATGTCGAACTACCGCCAGCTGTTTCATCACTGGGCTATCTTCTTGAGGAGGAGGAACTCTT
CCGTCAAGGGTAAGCGAATGCACTTAAATTGTACCTAAACAATTCCCTAATAAAATCTATTTACTTTTAGGATCTGGAAGAAGGGAGATATTCGC
AAAGGCGGCGATCGCAGTCGGTGGCTCAACTCGCCAAACGTTTACCAAAAGGTCGAGGTTCTGGAGACCGGCACTCCGGATCCCAAGAAGATTAC
AAAGGTAGAAATCATTACTTTCGAAGATATGAAGCAAACCAAAACCACCAACCTTAAGGAGATTGAGGGAAAATAGTTGAAATTGTTGGACACCG
AATCCTTCAACTCTTTACAGACATTCCACTTGCTATCCCCATATATAATTTCCATTTCGTTAGCACTCAGTTTTAGTTTCAACTTTGCCACTAAG
CTGCAACTATATTCACGCATAAAATTTTTAGAGTTTAAGTAAATGAAAGTAATCAATATACAAATTCTATATATTTATATACTTTGGAAATAGAA
TTAAAACTCGGGCTAAACCAAAATTATTTTACGTGCTTTGCTAGCAAGCAAACAAATATTGTGTAATGTGCATTAATCAAATAAATAAAATAAAC
AAGAAATAAAAATTTGCATAGATGATTTTGTGCCTCATTTAGGGATTTCGCTGCCTCAAAAACAAGACAATAGCGCTAAAACAATGCAAAGAAAG
AGAAAGAAATTTGCTATGAATACTAATCACTATGTAATAAATAAAACATTTTTTAATTTACCGAATCAATGATTTCATATTTAACCGCATTATTT
TTCATTCATAAAATTTTTCTTTGCATGTTTTATGGTATCTTTCTTTTATTCTCTTTGTGATTGGTTTTCATTGTTATTCAAGGCACAAAATCATT
TATGCTTGTTATTTTAGTTAATTTATGTTTATTTGATCATTGAAAAGTTTGATATCTAGGAACATATTCTTATGTATGTTAAAAATAAACATTTC
GAAAAACACTTGCATTGGAATGCCTACGATGTAACATTAATTTTAAGACTGGTGTAAACGAATTCACATAAGATCACACGTGTAAAAATCTATCG
AACAGTTGAATGGGAATGTTTGTTTATAATTAAGAATCTTCCCATATTGATATGAATCTTAGTATTCACTCCACATTAAAATCAAATTTCTTTCT
CTTTCTTTTCTATTTGCATTGATCCCACCCCACCCTCAACACACAACACATAATTTACAATATAAAACAAAATATGACAGTGGGTGGCTGAGGGT
TCCCCCACCCACTCAACGCCAGTGAGGATAGAAGATCCACTCCAGTTTGTGCCTGCAGGAACCAATCCAAGGGAATTTAAGCGTGTCCAGCAACT
AGTCAGTATTATAATACTCTTAGTCCCAATGAACTTTGTTAACAAGTGGAAGCTTTTTCAAACAGATTAAGGACAACCGCCGGGCAGATAAGATT
TCAGCCGGACCACAGTCGCATATTCTGGAGGGCGTGACATGGACGAGGCGAGCCGACTCAAGGATGCAACGGTCTCGCAGGCCGGCGATCATGT
CGTCATGATGGGTGCCGCCTCCAAGGGAATCATTCAGCGTGGCTTCCAGCACAATGCCACTGTCTACAAGGCACCGTATGCTAAGAACCCATTCG
ATAACGTCACAGACGATGAACTCAATGAATACAAACGCACGGTGGAGCGCAAAAAGAAATCGGTGCATGGTGAATGTAAGTTAGCAATCATACAA
AACCAATAACCAAATAGTTACTTATAATGCATACAACAACTTTTGCAGATACCGACACAGACTTTTCGGAATCCGAAGCGGTCCTGCAGGCGGGG
ACAAAGAAATACCCACAAAGCGAACCCGAGACCGGTATGTTAACTATTTAGAAACTATACTGATTACTGGAAACTAATATTATGTGGATATTCTA
GAGCACCAGGTCATTGAGATCCAAACACAGCAAGCGCCAGTGCCAAGGCAGGCGGAAGTCGTGCTGAGCGATGGTAAGTCCAGTTTTGTACTAAA
AAATGTGATCTACTTGTTTTTAATTTTTATATATGATTAAAATTACTTCAATCATGCACACTATAAAACATTTCAAGTACACTTGTCCAAGAGTT
TTGTCTTACAAGTCATTATGTGATCGAAATTTTATAGTTCTATTTTTTATGTTCCGTTATTTTGTTTATCTCATTTTTATTTCTTTTGTTTTACT
TTTGTTTTTTGTTAACTATTTGTTTAATAATTTATTAATAATTTAGGTCTTTAAGATGCTGCTATATTTAAAACGTATTTTGCGTAGTTTTTAAA
TAATAATAATTTCCTTGTAGTATTATTTTCCTAGTTTTTTTTTTTTGGTATTCTTATTTTATTTGATTCCTAACATTTATTAACATTTTTATGCC
ATTTCCCTCTTTTCGTTTTTTTGCTGTATTTTCGCATTATAAATTTACCAACCACACACAAACGCCTAAAACTACACACATTTCAATGGAAACCA
ACACTTTCAAATTACTTAATGAAGTCAACAAAAAAATTCTTGTAGCAATTGATACTATCACAACTTCCTTTCTGTAAAATCCTCAAAATTATTTG
CTGTTTTGTTAAAAATCTTAAGCTTCTAATTAGTTATGTTTTATTAGTTAAATATTGTGCAATATAATTCACATTTACACAATACTTCCAAGGAA
CCAACTGTTGTACGGCGTTCATAAAATGATTTATAATTCAACGTTCAACAATACGACAGCACATCAATCCCAAATGTTACAACAAAAAGAAACT
TTTTATAGTAGAAAAGCTGCAGTTTTAGTTAATCCTTTGTTTTACAAAATTTTTCGTTTAATTTTCCGAATTTGGCAATTTGTAAATCAAAATTTG
ACCTTTCCATTATTTTTACATAGGAAAAAGAACAAAACCAAATAAATTGGCAAATTGAACAGGAAAAATGCGAATTAAAAGCACTAGTTAGTAT
TGATATGAAAGCGAAGTGTGTGTAGGCTAAAAATAAAATAAACCAAAAATTTATAACAAAACGAAAGACCAGCAACCAACAACAAGAAGCAACCG
AAGTTCTCAACAGAACACAAAAATTCTACTACTACACTACCACAACTACTACATACTACCTTTTCTACTACTACTTCTGCGGCTGCTGCGCTCTA
TAACACAAAATAAAAATAACTAAATAATATGCAGTTTAAAAAGAAAAACCCTTTTGAGTTGGAGGTGAGTGCAGCCCCAAAGGTTTAGTGTGTAG TCAAAAAAATAAAAAAAAATAAATAAAAAATCAAGAAAATAGTTTATAGAAAAAATGTTCAGCATAACAAAAACATAAGCCACCTGCACACTAAA
CCACATTCAACATGTCATATCAACTTTTGCTGAATGCTCTTAGTTGAATCACAATATGCGCTGTTAGCCAAGAAATTAAATTGCAGCTTGCTGTT
TTGTTGGGTTTTCTCCGTGTTAACCGCAATTTTCCATAAATTTTTGTTTTAAACTGCAGCTGTTTTCTGTTGATTGCTTCTTTAGTTGCCCAGCA
GCCATTTCGTACATTAGTGAACACAACTAATCCGTATACCATAAGTTTAAGGCATGCTTGATCGATACTAAACTCTAAAACTCATGCAACACTAC
GTATTTATAGTTTAAGGCAACTGATTACGTCTGTCTCACAATTGTTTAGCGATTTACTTGCGATCGTCTGTCGCTGAATATGATTTTATAATTTT
ATTTCTCAATACTATTTTAGCCACACTTAGTTTTATAAACGGCGAACGCTCTCACACAGCCACAAATCGCAAGCCGCCAACTGGCCGAGGTAACG
AACAAGACCCATTTGAAAGATACTCCACAGTACTTACATCCTTCAATGTACTCAGGCTAAACGCCCATTGTATATAATATCGTTGAAACATTATA
ATACCCCATATAATCCACTAGCAGTTCGTTGTTAATGGTGTATACTCAATATAACCCTTATATAATCCACAAGCCCATGGCAAATTATTGATGCA
CCACAACTAAACACTAGCTATAGTTTGAGGTTGATATTTACCATTGAAATAATTTATTGCGGTTTTCTTAGTTCATTACATTGGTTTTGGGTGAA
ACGATACATCGTCAACTCTTTTGCACAGGAAACTCGTTGTTTTAATTCAAATGCCCTTAAAAACTGCTCGTTTTTCCAAGCTCGAGATATTTTTA
ATAGGTCAGACTTAAGTACAACCAAAAAATGGGATATGTTTTTCAGATTTATGGATCTGTAATCCAGTACGTATTGGCATTATGTATGTATTTCGA
GAGCCGCACTTATCTAAGATGCTGGCTCCGGACTTTTTATAGATTGTCACATATACTTACAATTTTTCGGCTTTTCTTACCTCCCACACCTGCAT
TTAATGTCGCTTTAACTAGACGATAGTAAGAATAATGAGTATGGAGACGACATGGAGAACCAATTATATGAGCGGAACAGGAACGTACACAATAA
CAGCAAGTGTCGACGTGATCTGTTTGCAACAAAGCGCAGGGATCCCCATCCATCACCGGAGCGTCTGTATACCTATGTCTATGCTACAGCTGCCT
CTGTGGGCCAGTGCGTCCAACCGGAGGTGTGTTCCGCTTTGTTGCGGGCTCTGCATAGCGAGCAGTTGGGCTACCTGGCGAGTAGCTATCGCGGA
GGAGCTGGGAACTCAAATGCCACCACCGCCAGCACATGCACTATAACCAGCGTCACGGGCTCCTCTACCGCATCGCGCAGACCATTGCAAAATGT
GAATATTATGTATCCGCAGCCGTATCGCACGGGCTCCCATTTTGGATTCAATTCACCACGCCAGCAGCCACGCACTGAGCATAAGCATGTGCCCA
GGGAGCGAGACTATAATGCCTTGGGCTACCGACCGATGCAACGAGGGATCAGTTACGAGGAGATCTTCGCCACACCTCGCTATGAACAGTTGTGC
CAGGTGTGTTTCGACAAACTACTGCGCCTTAAGCCCGAGCTGCAAAGGATTGGCAGTGGCACGGCTACTAGTAGTTGTGCGGAGGAGCAGGCAAG
TACAGGGAGCACTCCCTTGCAACGCCGCCAATTGCCGACTTTGCCTGAGTTATGCGATCATCGTAGGGAAATGGAAAAGTTGCCAGAACCTCCGA
GGGTCCAACGTAATGCGTACACACAGACACAGAAGTGTTCTCCATCCTCTTCCACCTATAATTTCCTTAGTCAAATCGAAAAGTTTAACTTCTCG
GAAGAATCGACGGACATAGATTATACTCCACGCCCCATTAACAGTGAAAGTAGCCTGTTGGGACTGATTGTGGAACAGGCAACCTCGAGTGCTGG
AGCGAGTGCCACAAGTGCTCCACCTCAAAGAATTTACTGTGCAGAACAAGTGGACATTACAGAAGTGTGGAGTTTTGGGCGTTGGTTGGAACCCC
AGGACCATATGATAGCGAGTAATGCAGATGAGTTTTCCCAACAGCCGCTGACCGAGCATTGCATCACATTGGAGTTTAATCAACAATATTCGACT
GGCGACAATCAGGTCGATCGCCAATTGATGACACGCGAAGAGCGTCAGCGTCGAAAGTCTGAGTTCCAGGAGCTTTGGCAAGATCATGTCGAGTA
CTTTGAATCCAAAGAACAGATGCATACCCATGAAAATATCCAGGAAGTCGCGACTCTTAGTGCTTATGATTGCTTAGACCAGGATATAGGCGAGA
TTGAAGACGGATTCAATGATGGAACAATCGCTGATGCAAGTGATGAGTTACCGAACATTCTGCAGATGTTCGAGGATAGTCTTACATTAGCCGGC
GAAAACCTAGAAAAGCTGGTGGAAAGTACCAAAAAACTACAAGCAATTCACAGTGAAACATCACCAGCCTCTTCCAATAGTTCCCTAGCCGAAGT
TTGTAATCTCTTTCGGTCGAGAAGTTTCGAGAGCATTCCTGCTATCGATGATACTGTGTCTGTACAGGAACCACTTTACGATTTGCCCATAAATT
CAAGTATCGAAGAAGATGACGGACTGCAACATAATTTTGTACAGGAGGAAAAGCGTGACGACGAAAAACCTCTTACTCCCATTTCAACGGAGCCA
GAGGAACCTTCGGATAAGGAGAAGGATCTTGTCGACGAGAAAGACATAGACGAAAATGAAAATCACGTGGAGGCTGAGTTCCAAAAGGCTCTTGG
CGAAACAATGCAAGTAACCGTCCTTATGCCAATGGAACACAAAACCCCCCTGAAAGATACAGATGAAAATGATCGTTTGGTTGAGACTGAGATCC
GAGATCCTCAAGAAGTTAGCTCCTTAGAGACAGATAACCAGTTTTTCACACCGCTGGAACGCGAGGTTCTGCATCGGATCGAGAAAGAAAGACTT
GACGAGGCGGAGCCTATATTTGGAAAGATTGACCATAGTATTCGCAACAAGATGACGCCAAAGAAGCTGCAAGACTTGGTCAGCGAAGAGATATT
TCGCACACAAACGCATGTATACACGAATCTAAGGACACCGATATCGAAGAATATACAGCATGACACCACTTTGACTCCCAGTGGCTCATCCCTGT
CAGCTCATAATATCAGTGCACCGTGCAGCTCAATGGCGCACACTCATCTAGTCACCCGACCAACACCCCGAATGTCGCGATCCTGGTCCGAAGAT
CAGCAAAGTGAGGATGACGATCAAAAGAAGAACGAAGCGGGAGAACGGGGATACATTGACAATGACACTCCCATAGATCGAGTCATCTCGTCTAC
AACATTTGTGTGCAGAAGAAGTCCAACCAGAAAGCGCAACTTTATTCAGGAGAATATTCGCAATGCCAGCAGACCACGAATTGCAGCCGGTTCGA
TTAGAAAACATAAAAGCAACATCGTAACTTCCCCTAGAGCCAAATCAAGCCCATCCTCGGTGTATACTTTTCAGTGTGGCCAACGGGATAGCGGA
GCACGCCTATGGGTTGCCTTGCCAACGTCTCCACGTGGTCAAAACGATGAGAAATCGTCTACTGCAGCTCGGGCTTTGTACACCGTTCGGGGTAA
TCCCCCATCACCATTTGCCAAACGTCGTAGACCCTTGGTTATCCTTCCACCAATGCGTAATAAAAATAAAGCCCATAATCGCGAGATGAGCTCAT
CTAATGAATCTCTGCACAGAACTCTTTCCAGTAGCACGTTCAATGTGGACGATGATGAAGATCCTGCAAATTCGGATAACATTTCAATGAGTACC
TTTCAGTTGGAGGAAGGTCAAGAAGTATCATCTCCTGCAACTCAGGATAATAGGAATGGGACTAACAGTTCTGTGTACTACAGCGCAAACGATAC
CACGCGAGAAGAGAGAGAATCTTCACAGCCAAGCAGGGACGAAGCAGAAGAGAATCTTGGAGTCATGGAATTTATGCCCGAATCAATTCCACTTT
TGGAAATACCAGATATCTGTAACCAACTCGATGAAGACGGATCATCGTTAGAACTCGCACGCTTAGCAGGCGGATTTGAAGTGGGTACAACAGAA
GACGACCAAGTCGAAGAAGTGGAACAACAGAAGAAGAGCATAGATAACGAATCCAAAAATGTTCTGCCTATGGGAATAGAAGAAATTAATGGCGT
TCAGGACAGCATTTGTTCCATGCAGGCGGATATTGATAAGGATGATATTGTTAATACCGATGATCAACCCTCGACTTCAAAAGCGGCAATGAAAA
AAATTCGCATATATGGTGGTGCGGAGCCCGAAGAGACTCCTCATTGCGAAGATGAGGATGTGGTGACGCTGGAAACGGTTTGCATTGTGCGTGGT
CTGGAGATGTTTGTGCGAGAGGTGGAGCCCATAAAGCAAGAGACTTCAGAGGAACTATCAGAGCTTGGGGGACTTTTTGAAAATGGGTTAATTGA
TGAAGGTGGCGAGGAGGCCATGTCCCAGTAGCAGTGAAACCAGAAGTTGATGAAGAATTTATGAAAAAATATTGAGGAACGAAAGGATAACACTA
ACTTTGAACACTTTTTTTTTTGAACATTTTATATTCGTTTATGATTTTAACATTGCTTGTCATTACCATTTTTTGTACTATTTTTCATATATTTA
ACATTGTAACATTGAAAACTTTCTTCTTTTGTAATGTAATTTATAGAACCATTAAAAATGTGTGAATTATTGGTTTTGTACTCAGCAAATTTATG
TTAAGTTATAAAGGGTATGGTGTTTATCTTTACAATTATGGGTTAAAAAAAATCGAACATTATGGGTTTATATTAATAATAAGACATTGTTTAAA
TTTAATTATTAGTAGTAAATATTCCATCATAATGTCTTAGAATATGTCATCCAGTGTTTCACGTCCCTTGTCCTGCGTCCAGTGTGTAAATTATG
TTGGTCGTGATAATTTTTGGAGGTTCAGGTGCTCAGAATCATACTTACATTACTTTCTATATCCACATCACCCGCCATTTGATATATATCGATTC
TAGCACTTGTCTCTCAACTGGCTCAAAAGTATGCGTTCCTTTATTCGCCTGGCCAATACATGTATGCCTGCATGAAAATGGCTCCATTAATGCAT
AAGGTTTATGTTATACACAAGGTCGAGCCCGTCAGCAAGCACAACTATCCGCCAGTTAACGATGGCAATATGAGTATTCATCACAACGAAAGTGG
AGCCGGATTCATGGCCCAAGAGTCCAGCGTTATTAGTAGCACCCCCGTACGCAATGCCTTGGCATCTGTATCATTGCCGGAAGAGAGGAATCATT
CTATTTTGGGCTTATCATCGACTCCGTATCGCACCATCTCGCATTTCGGGTTCAATTGTCCGCTTATTACGTCACCAACCATTCTCCTGCATCCC
GAACATCGATCCATTTGGCAACGGGTGGCCGAGCAGCGCGAGAAGGTTGTGTCCTTCATAGATCTCACAACATTGAGCTTGGACAACCGCAAGCT
GCTCAATGTGGTGACATCAACGCATCCAACCCAGTGCCAATCGCAATCGCAATCCTTTATCTCTGAGAAGCACATTCAGCTGGAAGTTACGCCAC
CGAAGCGAAAGCAGCGTGTCTACAGCGCCACCATCAGCAGTGGTCTAGACGACAGCCTCGATGAGCTGGACTCCCTGATGAGTGGCCTAGCCATC
AATATGCCGCGCAGTCGGGAGCAGGACAGCGGTCTGTACCGCAGCTACACCTTTCTACCCAGTAATCATGCTCTGCCCAAGGATACAGATGCCAA
TAATAGGGATCAAACGGATCGGGAGCGACCAGAAGCGGAGCAGGAGGAAAGTTTTCACTGCGCAGGCGACAGTGGTATTGGCGATTCCACCGGCA
GGCGTCCGCGTCTGGCCACCACCAGCAATGATTCGTCTATTCAAGAGGCCGAAGCCTATACCCAGGGCAAGCACGTCAAGTTGACCTTGAGCAGC
TCACCCACGCCGACGGCCACACAGTCACCTGCAACCATCGAAATTCTTATCAACGTATCGCTGCGCAATGCCGAGTGCGTCCAAACGGTCCAGAC
CCATGAGCAGGAGTTTCGCGCCAAGTTGGAGCGAGTAATCGACGAGGAGATCCACTATATTTCGCAGCAACTCGCATTTAAACAGCGACAGGCAG
AGTTGCATGAACAACAGACTACATCGCGGGCTCCAATCGCTACGCCTTCTTTCACAACTATGCATCCGCCGGCACCGGCTTCTTCATCATCCATG
GTTCACCGCAGCAACTCGGCACCAGAACTGTGCCACACCTATAGCTATGTGGCCGTGGGCGATTTGTCGACCAAACAGGATCAAGCCTCTCCCCA
ACTGCCAGCGGAGGGTGAGCCGTTGAATGATATACTCAGTAGTTTGGAGAAGGAACTGGAGCGTCTGCTGAATAGCGTGGTGACAGCCCACATGC
TGCACAACAAGGCCATCATACACGAGTGCCGGGCTCGCTTCTCGCAGCTGGCCGATGGAATTGTCAGCTCGTAGATACATATTATGATTTTGATG

FIGURE SHEET 554

GAAAATTTACATCTTCGCTTTTGTTGTGATATTTGAAAATCGACAACAGTGAAATGATTGTATAAAGCAACTAGATTAAGTTTAATGATGATAAT
TTGGAAATCTTCAAATCGAACTAATGCATTTTTTACTTCTTTGTTCTCTTAATTTAAATGTTAAGACTGTAACTTAAGCACAATATGAAAATGCA
AAGTTAAAACTGAATCTGAGCCAACCATTGTACATTTAAACATCTGTGAAATTGTTAAGTTTAATTTTTGTCGAATCTTGATTTTCGTTTCATAT
TTTTATAATTAAAATATAATAAATATAGTTTTCATTATGTTTAATGTTTTTAAGAAAGTTTTAGGTTAAGTGTTCATACTTACGAAACATTAATT
TCAATCAGTTAACTTTAATCAGCGCCCAGGTAAAATAATTTCATTTATTATTTATGTTTGTGTTTTGTACTGCATGTCTGCTTGCTTTTTAACAT
ATATTGCTGATCCTGCTGCATGTCCTCGTGTTTGAATAGCGAATCCTAAACTCCATCTATGTACTTATACATCCACACCAATCAAAACATTTAAT
ACATGTACATGTTTTAGTTAGATTATTATTCGTGCGTGTCTCATATGGTGAAAGTAATTACGAAATTAATATCAAATATTTTGTGTGCGTCCACT
GAGTTACATTTGTAGGAGACCCATGCCAAATTACACTGCTATACAAATTACTAACGACATTTTCGACCCTTTTGCAACAGGTGAAAACGTACAAA
ATGGCGATCATTCGGAGGCACACTTGAGCACCTTCTCGCAGAGCAGTAAAGAGGTAAGTACATCCGAACTGATCCTGCGATCCAAGATCTACGGA
TCTCTTCTTCAACTCGAACACTCACAAGCAGTAAGCTGGGTGGTAAGCGATTAGCAAGTAGAGTTGCTACATCGACAAGACAACCAGTTTTAAAC
AACATCATCATGCATTGAGCTAACCTCATTTGATTTACTAACCGAAGCGCAACCGATATTCTCACTGCAAATTTCTATTACGGTTCCAGGATGTC
TCCACGGACGGATCCCCCAAGAAAGACAAGAAGAAGAAGAAGGGTCTGCGCACACCATCGTTTTTGAAAAAGAAGAAGGAGAAGAAGAAGGCCGA
GGCCTAAGCTGACCATCAGCGTGATCCGTAGGAGTAGCAATCTTGACCAACCTCCCACCATCAGCGGGAACCGAGAAAAATAACGACAATGATAC
CACGAGAAAATGGAAACTTTAGCCAGATCAGCAAAAGAAGCATTATATAAAAAAAAGAGAGAGGCCTAAACAAGCAACGGATGAGCA
(SEQ ID NO: 1018)

Exon: 1001..1124
Exon: 1211..1694
Exon: 1768..2479
Exon: 2541..2664
Exon: 3691..3801
Exon: 3866..4160
Exon: 4229..4309
Exon: 4372..4443
Exon: 10929..12767
Start ATG: 1029

Transcript No. : CT26485
ATTTAATTGCAGCATTTTAACTGAAATCATGACTGAAGTTGAGCAACCGCCACAGAATGGCATAGATCCCACTGCCGGCGAAGATGATGACAATA
GCAAAGCACGTCCCGCGGATATTGAACAGGATATGCGCGAAATGGAGCGTCGCAAGCGAGTCGAGGCTATAATGGGCTCGAAACTGTTCCGCGAG
GAGCTGGAGCGTATCGTGGACTCGGCGCGCGATGGAGGTGCTGGCGCTAGTGGAATCCTGCAGCAGCTGTCGGACATTGTGGGCGTACCAGTGTC
CAGGGTGGGCAGCGTCTTCAAGAGCAGCAACTGCATGGTGCCAATCAACGATATACGCGGCGTCGAGTCCATGGGCTATGCCAAGGGCGAGAAGA
TACTCCGGTGCAAGCTGGCCGCCACATTCCGTCTGCTCGATCTGTACGGCTGGACCCAGGGTCTGGGGGCACAGATCACCGCCCGACTCAAGGTC
GATCAGGAGTACTTCCTGGTTAACCCATACGGCCTGCTTTACCACGAGATCACTGCCTCAGCGCTGAACAAGGTGGATATGCAAGGACAGATTGT
GGAGCAGGGCACCACCAACTTTGGCGGCAACAAGAGTCACTTTGTCCTCCATTCGGTGGTACATGCTGCCCGTCCAGATATTCGATGCGCCATCT
ATATCGGCTGCAGTCCAGTCGTGGCTATTTCCTCACTAAAGACGGGTCTATTGCCCTTGACCAAGGATGCCTGTGTGCTGGGCGAGATCACCACT
CACGCTTATACTGGTCTATTCGACGAGGAGGAGCGCAATCGATTGGTCCGCAGCCTTGGTCCCAACTCCAAGGTGATTCTGTTAACTAATCACGG
TGCTTTGTGCTGCGGAGAGACCATCGAGGAAGCCTTCTTCGCCGCCTGTCACATTGTACAGGCGTGTGAGACGCAACTGAAGCTGTTGCCCGTCG
GTTTGGATAACTTGGTGCTGATTCCAGAGGAGTCGCGCAAGGCCATTTACGAGCAGTCGCGCCGGCCGCCGGAGGATCTGGAGAAGAAGTTTGCC
GCCGTCGCCGCTGCCGAAGATGGTGCTGCTACTGCTGAAAAGGATGCAGCCGAAGCAGTACCCAAGGTTGGCAGTCCGCCCAAGTGGCGTGTGGG
TGGTGCTGAATTTGAGGCCTTGATGCGCATGCTGGACAATGCTGGCTATCGCACTGGCTATATCTACCGTCATCCACTGATCAAATCGGATCCTC
CCAAGCCTAAGAACGATGTCGAACTACCGCCAGCTGTTTCATCACTGGGCTATCTTCTTGAGGAGGAGGAACTCTTCCGTCAAGGGATCTGGAAG
AAGGGAGATATTCGCAAAGGCGGCGATCGCAGTCGGTGGCTCAACTCGCCAAACGTTTACCAAAAGGTCGAGGTTCTGGAGACCGGCACTCCGGA
TCCCAAGAAGATTACAAAGTGGGTGGCTGAGGGTTCCCCCACCCACTCAACGCCAGTGAGGATAGAAGATCCACTCCAGTTTGTGCCTGCAGGAA
CCAATCCAAGGGAATTTAAGCGTGTCCAGCAACTAATTAAGGACAACCGCCGGGCAGATAAGATTTCAGCCGGACCACAGTCGCATATTCTGGAG
GGCGTGACATGGGACGAGGCGAGCCGACTCAAGGATGCAACGGTCTCGCAGGCCGGCGATCATGTCGTCATGATGGGTGCCGCCTCCAAGGGAAT
CATTCAGCGTGGCTTCCAGCACAATGCCACTGTCTACAAGGCACCGTATGCTAAGAACCCATTCGATAACGTCACAGACGATGAACTCAATGAAT
ACAAACGCACGGTGGAGCGCAAAAAGAAATCGGTGCATGGTGAATATACCGACACAGACTTTTCGGAATCCGAAGCGGTCCTGCAGGCGGGGACA
AAGAAATACCCACAAAGCGAACCCGAGACCGAGCACCAGGTCATTGAGATCCAAACACAGCAAGCGCCAGTGCCAAGGCAGGCGGAAGTCGTGCT
GAGCGATGCACTTGTCTCTCAACTGGCTCAAAAGTATGCGTTCCTTTATTCGCCTGGCCAATACATGTATGCCTGCATGAAAATGGCTCCATTAA
TGCATAAGGTTTATGTTATACACAAGGTCGAGCCCGTCAGCAAGCACAACTATCCGCCAGTTAACGATGGCAATATGAGTATTCATCACAACGAA
AGTGGAGCCGGATTCATGGCCCAAGAGTCCAGCGTTATTAGTAGCACCCCCGTACGCAATGCCTTGGCATCTGTATCATTGCCGGAAGAGAGGAA
TCATTCTATTTTGGGCTTATCATCGACTCCGTATCGCACCATCTCGCATTTCGGGTTCAATTGTCCGCTTATTACGTCACCAACCATTCTCCTGC
ATCCCGAACATCGATCCATTTGGCAACGGGTGGCCGAGCAGCGCGAGAAGGTTGTGTCCTTCATAGATCTCACAACATTGAGCTTGGACAACCGC
AAGCTGCTCAATGTGGTGACATCAACGCATCCAACCCAGTGCCAATCGCAATCGCAATCCTTTATCTCTGAGAAGCACATTCAGCTGGAAGTTAC
GCCACCGAAGCGAAAGCAGCGTGTCTACAGCGCCACCATCAGCAGTGGTCTAGACGACAGCCTCGATGAGCTGGACTCCCTGATGAGTGGCCTAG
CCATCAATATGCCGCGCAGTCGGGAGCAGGACAGCGGTCTGTACCGCAGCTACACCTTTCTACCCAGTAATCATGCTCTGCCCAAGGATACAGAT
GCCAATAATAGGGATCAAACGGATCGGGAGCGACCAGAAGCGGAGCAGGAGGAAAGTTTTCACTGCGCAGGCGACAGTGGTATTGGCGATTCCAC
CGGCAGGCGTCCGCGTCTGGCCACCACCAGCAATGATTCGTCTATTCAAGAGGCCGAAGCCTATACCCAGGGCAAGCACGTCAAGTTGACCTTGA
GCAGCTCACCCACGCCGACGGCCACACAGTCACCTGCAACCATCGAAATTCTTATCAACGTATCGCTGCGCAATGCCGAGTGCGTCCAAACGGTC
CAGACCCATGAGCAGGAGTTTCGCGCCAAGTTGGAGCGAGTAATCGACGAGGAGATCCACTATATTTCGCAGCAACTCGCATTTAAACAGCGACA
GGCAGAGTTGCATGAACAACAGACTACATCGCGGGCTCCAATCGCTACGCCTTCTTTCACAACTATGCATCCGCCGGCACCGGCTTCTTCATCAT
CCATGGTTCACCGCAGCAACTCGGCACCAGAACTGTGCCACACCTATAGCTATGTGGCCGTGGGCGATTTGTCGACCAAACAGGATCAAGCCTCT
CCCCAACTGCCAGCGGAGGGTGAGCCGTTGAATGATATACTCAGTAGTTTGGAGAAGGAACTGGAGCGTCTGCTGAATAGCGTGGTGACAGCCCA
CATGCTGCACAACAAGGCCATCATACACGAGTGCCGGGCTCGCTTCTCGCAGCTGGCCGATGGAATTGTCAGCTCGTAGATACATATTATGATTT
TGATGGAAAATTTACATCTTCGCTTTTGTTGTGATATTTGAAAATCGACAACAGTGAAATGATTGTATAAAGCAACTAGATTAAGTTTAATGATG
ATAATTTGGAAATCTTCAAATCGAACTAATGCATTTTTTACTTCTTTGTTCTCTTAATTTAAATGTTAAGACTGTAACTTAAGCACAATATGAAA
ATGCAAAGTTAAAACTGAATCTGAGCCAACCATTGTACATTTAAACATCTGTGAAATTGTTAAGTTTAATTTTTGTCGAATCTTGATTTTCGTTT
CATATTTTTATAATTAAAATATAATAAATATAGTTTTCATTA
(SEQ ID NO: 1019)

FIGURE SHEET 555

Start ATG: 29

MTEVEQPPQNGIDPTAGEDDDNSKARPADIEQDMREMERRKRVEAIMGSKLFREELERIVDSARDGGAGASGILQQLSDIVGVPVSRVGSVFKSS
NCMVPINDIRGVESMGYAKGEKILRCKLAATFRLLDLYGWTQGLGAQITARLKVDQEYFLVNPYGLLYHEITASALNKVDMQGQIVEQGTTNFGG
NKSHFVLHSVVHAARPDIRCAIYIGCSPVVAISSLKTGLLPLTKDACVLGEITTHAYTGLFDEEERNRLVRSLGPNSKVILLTNHGALCCGETIE
EAFFAACHIVQACETQLKLLPVGLDNLVLIPEESRKAIYEQSRRPPEDLEKKFAAVAAAEDGAATAEKDAAEAVPKVGSPPKWRVGGAEFEALMR
MLDNAGYRTGYIYRHPLIKSDPPKPKNDVELPPAVSSLGYLLEEEELFRQGIWKKGDIRKGGDRSRWLNSPNVYQKVEVLETGTPDPKKITKWVA
EGSPTHSTPVRIEDPLQFVPAGTNPREFKRVQQLIKDNRRADKISAGPQSHILEGVTWDEASRLKDATVSQAGDHVVMMGAASKGIIQRGFQHNA
TVYKAPYAKNPFDNVTDDELNEYKRTVERKKKSVHGEYTDTDFSESEAVLQAGTKKYPQSEPETEHQVIEIQTQQAPVPRQAEVVLSDALVSQLA
QKYAFLYSPGQYMYACMKMAPLMHKVYVIHKVEPVSKHNYPPVNDGNMSIHHNESGAGFMAQESSVISSTPVRNALASVSLPEERNHSILGLSST
PYRTISHFGFNCPLITSPTILLHPEHRSIWQRVAEQREKVVSFIDLTTLSLDNRKLLNVVTSTHPTQCQSQSQSFISEKHIQLEVTPPKRKQRVY
SATISSGLDDSLDELDSLMSGLAINMPRSREQDSGLYRSYTFLPSNHALPKDTDANNRDQTDRERPEAEQEESFHCAGDSGIGDSTGRRPRLATT
SNDSSIQEAEAYTQGKHVKLTLSSSPTPTATQSPATIEILINVSLRNAECVQTVQTHEQEFRAKLERVIDEEIHYISQQLAFKQRQAELHEQQTT
SRAPIATPSFTTMHPPAPASSSSMVHRSNSAPELCHTYSYVAVGDLSTKQDQASPQLPAEGEPLNDILSSLEKELERLLNSVVTAHMLHNKAIIH
ECRARFSQLADGIVSS*
(SEQ ID NO: 1020)

Name: ADDUCIN
Classification: actin_binding
Gene Symbol: hts
FlyBase ID: FBgn0004873

Celera Sequence No. : 142000013383756
CGGATTGGGTCTGCGCAATCCTGCCGATATTACGCTCAACGAGTACAACCGGAGCGAGGGTAGCAGTGCCGAGGAGCTGCTGCGACGAACTCCAC
TGAAGATCCGGGCTCCCGAGATGCTAACCGCACCCGCTGGTTATGGAACGGGTGCGTAGTAGATTGATTCGAAGCAAGAAGACATTTCAATAATA
TATTTTATATACTATTTCAGAACCCTGTCGCATGACACTTAAACAGGAGCCAGAGACTGGTTACTAGAAGAATAACGAACGGTGCAATATGCAGT
TTGCAATAGGACACCCCTTAAGCACACAACCCATACACATACAGGCCCTCTCTTGCTGTACTCCCCACCAAGTGCTATATAGAGATGAAATTGAA
ATGAAGAACTTACTTAATTGTTATGCCTTGAACCATTTTGATACTTTTTATTAGTCCTAAGTAGGTATTTTGGAAATTGTTGCTTAATTTTTAAT
GTTTAACGCAGTTGCAATATATTTTTGGAGTCATATTTTGCTCAAGAAGTTTATTATATACAATTATACTATATATATATACACCATTTAGCATGTA
CTGAGTTTGTTGGTTATTTGGTTATCTTATACTTGTGCGTGGATCACAAAACATTCATATAAGGCCATGCAATATATTGTTTTAGGTTAGGGTGT
TGTCTAGATTATGCTGAAAGTGTAATATATATATTTAATTTTAAACAAAGAACTATTTTTATATGAATATGTATAATATACAAACTATTTCTAAGAT
GGCTGAATGAATAAACAAAATCAAAATAAACACTGGAGAATATGAATGTAAATCGTTTACTGCGGCATTTTTACTAGTAATAAATATTACTATAA
TTTATAATTTATGCCATCTCTTTCAGCAACAACTTTAAATATCCAAACTGATAAAGCGATATATGTTCCTATGCTCCCACTTAGAACGTAACCCT
GATCCTGCATAGAAAAAATTCAATAACGTATTACAAAGACTAACTAACGTTTATTTATCGATATTGCTAATGCCCGTCTTCTCGACCTGGGCGAG
GAGCTCTTGGAGCTTGTTGTCGAAGAGCTCGCATCGAATGGGCATCTCCAGGGAGTAGAAGGGGTTCTTGAGCACGTAGTCTGAGTACAGCTCGT
AAACCTTTCGCAGCAGCAGATCAATGCCATTGAGACCCGTTTCCGAGATTATAATGAACTTGATTCCGGTCAGCGTTTGGAAGCAGTGCAGCGTG
AAAGTGTCCGCCTCTAGGATCTCGATGCCGGAACTCTTGGGCTCCGGACTCAGTTGGCTGGCGATGGCGAACAGCGGGTAGAACATGCTGGCCAG
AAAGATTTTCTCGTTGGTGGTCATCTTTGGCCGGCTGAACTTCAGGTTAATGGGATAGTTCTCCGGTGCATCCAGTGTCGTCCTCACATCGCGTC
CATCATCCAGGGTGACTCCATTGACGGGCATACCGTTGACCGCCACCAGGACATGGCCCACTGTTCGTAAGCATATATTAAGGTGGTTATGTTTC
TAAAATTCACAGACACACCCACCATTTATTCCATCCTTTCTGTTGAACGAGACCGATACCTTCTTGGAATCGTAGTCCAGCACCAAGTCCAGAGG
GTATGTAAAGGTCTTCTCGTGCTCAATGCGTGGCACATTGTTGTCCAGGTTGAATATAAGGCCACCCGATTTACTAACTATATAGACGCCATATA
TAATCATTTCTTACTATTACTAATTCTAAGTTTCCTAGGAATGTTTTTATATTTTATGCGAATTAGCGATGGTAGTGCCAGCCAGCTGTTTGCCG
CGGAACCAGTTCCAGTTCCGGCTTAGTTGCCATTAACAGTACATTAACATTGCGCCTTAACAGTTGGGTCCATCGAAGAAATTATAATTATTAGG
ATAAATAAACCATTAAATTATTATAAGAAGCATTATTTAAAATTTAGGAATAAAATGGGAAGTAAACTCTTTAGCCAGAATACTAAGAATACTTA
AAAAATATTTACAAGTTCAACCAAAAATCTAGTTCTACCAGGGCGGAGTAGCTCTTTAAACTGATTCCATCTTGCCTATCGCGTTCATTTAACTA
GTTCACGGCCGAACAGCTGTCTCGGCATTAGAATTAAAAATAAACATAATTGATTTTCTGCCCGAAAGTATACGTAAACGCGTAGGCGCTCCCAC
CTGGCAGTGCACCCGATTGACCGACTTGCAACCTCCACGGCCACCGATGGGCTCCGACGACCAGAGTGCCGGGGACAGGATCCAGAAGGGATTCC
AGATCAACTATATGATTCTGCGGGATGCCGACAGCGGAAAAATAATCTGGCAGGAGAACAAGGACTTCTCGGCACCGGACCAGGAGCATGAGGCC
CGAGTGCCGGTGAAAATACTCGACATGCGTGCCGTTTCCCGGGAGATCAACTTCAGCACCATCGAGTCGATGGAGAACTTTCGCCTGGACCAGAA
GGTGCTCTTCAAGGGCCGCATCATGGAGGAGTGGTTCTTTGAGATGGGATTCGTGGGTGCCAACACCACCAACACCTGGCAGTCGACAATCGAGG
CGGCACCCGAATCCCAGATGATGCCTGCCAAGGTCTTGAACGGCAATGTGACTATCCAAACCAGTTTCTACGACAACGAGACACTCATCACCAAA
TCGGTTGTGCGCCTGTACTACATTTAGGCAAATGTGAGTCACCTGCCGTTCTGCTGA
(SEQ ID NO: 1021)

Exon: 1717..1543
Exon: 1485..1001
Start ATG: 1717 (Reverse strand: CAT)

Transcript No. : CT26491
ATGATTATATATGGCGTCTATATAGTTAGTAAATCGGGTGGCCTTATATTCAACCTGGACAACAATGTGCCACGCATTGAGCACGAGAAGACCTT
TACATACCCTCTGGACTTGGTGCTGGACTACGATTCCAAGAAGGTATCGGTCTCGTTCAACAGAAAGGATGGAATAAATGTGGGCCATGTCCTGG
TGGCGGTCAACGGTATGCCCGTCAATGGAGTCACCCTGGATGATGGACGCGATGTGAGGACGACACTGGATGCACCGGAGAACTATCCCATTAAC
CTGAAGTTCAGCCGGCCAAAGATGACCACCAACGAGAAAATCTTTCTGGCCAGCATGTTCTACCCGCTGTTCGCCATCGCCAGCCAACTGAGTCC
GGAGCCCAAGAGTTCCGGCATCGAGATCCTAGAGGCGGACACTTTCACGCTGCACTGCTTCCAAACGCTGACCGGAATCAAGTTCATTATAATCT
CGGAAACGGGTCTCAATGGCATTGATCTGCTGCTGCGAAAGGTTTACGAGCTGTACTCAGACTACGTGCTCAAGAACCCCTTCTACTCCCTGGAG
ATGCCCATTCGATGCGAGCTCTTCGACAACAAGCTCCAAGAGCTCCTCGCCCAGGTCGAGAAGACGGGCATTAGCAATATCGATAAATAA
(SEQ ID NO: 1022)

Start ATG: 1 (Reverse strand: CAT)

MIIYGVYIVSKSGGLIFNLDNNVPRIEHEKTFTYPLDLVLDYDSKKVSVSFNRKDGINVGHVLVAVNGMPVNGVTLDDGRDVRTTLDAPENYPIN
LKFSRPKMTTNEKIFLASMFYPLFAIASQLSPEPKSSGIEILEADTFTLHCFQTLTGIKFIIISETGLNGIDLLLRKVYELYSDYVLKNPFYSLE
MPIRCELFDNKLQELLAQVEKTGISNIDK*
(SEQ ID NO: 1023)

Classification: hypothetical

Celera Sequence No. : 142000013384591
TTTAACATTTGAGTATTATTTCTGCAACTTTTTAAACTCATTCTCAGTTTTTTGTCTCAATTGAGTGTTTTGATTGAGTGGGTGTTTTTAACTCT
CTTAGCTGCATATTCCTCCCTTAAATGCAGTTTTTTTAGCTCAACTACCAATTGAGTGAATGTTAACGGAATGTTAACTGCAATCTCAAGACTC
AAGCGCAGTTCTGAGTGAGTCAAATATGTGGCTTTGAGTGGAACAGACTAAGCTCATAAGAGTCATGAGCAGTATTTTGACGATTCTTTTGCCCA
ACCATGATATAAAATAATAATGACATATTTATTTTCAAAATGTTGGTATAATAATAAGCTATTAACTATCAAATAGCTATTGATATACATTCGTT
TTCCCCATTCTCTGCTCGAAAAAATATAGTTTTGAAATTTGAAAGCTGGAATTGTTAGCCCATCAAAATGCTAAATTACTTAGTTCTTTCTGTAC
CTGGTAATTAAATAAACTTTGTGATTCGTATTTGATTTTACATATACTACGTTTGCTTTTATTTCAACTCAGATCAGAGGATAGCTTGAACATAA
AATGGCCTACAAGCAATAGTATTTTAAGTCGTAATTGTAACTACTAAAAGATTAGGGGATTACATTTAGTACATGTCTTATACGGATTTTATTTG
AGTAGAAATTAGTCAAGGCAACACGGAACTATCGTAAATTTCAACTATTCTAGAAAATTGAAATATTTAAGCATAGTAACGGTGCTCTCGAAACT
AAACAAAAGGGCTTTAACATTGTAAAATAGAAAAATATAGCATGGAAACTTTCGTGTGTATAGACGTATTATAAAACCAGCATAAGACATGCCTA
TTGTGGATGTGTTATCTTATACTGCCTTATAAGGAAGTAGTATGATGCGAAGCGCTCCCCCTTCTTCATCGTCCCTCAGAGCACTAAGTCCAAAT
TAATCTTCCTCATCCTGTCCCAATCCCAGTCGCTGCCACTAGACGCTTTGTCACAGAGTGTCGTTGAACAAGCGCTTGGCCTTGTAGCTCGGATG
AATCGGTCCCGGTATCCAGTGTGGCTTAAGGGCACTCTTACCGGGCAACCGATTCGCGTCGTAGGGCACCTGCGGAGACAGCTTCAGCTGGCGGT
AGTAATCGCTCTTGGGGTAGATGCAGTTGCTCTTAGTCACGATCCGCACATGCTTGCCACTGCCCGTTTGTGGAGTCGCAAACTCTGCGCGCGCA
GGCTGTTTGGGTGTGGACTGCGGCAGCTTACTGTTGGCCTGCTTCACTTGCAGTTTTCGAGAGGGAACAAAGATGTCCTGCTCACCGTCCTCTAA
AGGGGCATCCCATCCGTTGGTCGGAGCATCATCATCAACACCGGCAGCCTTCGTTTTGGGAGTCGGCTTGGCCTTGGACTGTCCCTCCACCTTAG
GTGTGGGCTTGGGCTGCTCGTCTGTCTTCGGCTTCGACTGCTCCTCCTTCGTCTTGGAGTGGTCCAATTTCTTGCGCTTCGCAGGCTCTTCTTTT
TCTGCCTTCAAGGTCGGTTGATCCTCTATCTTGGGCTTGGACTGGTCATTCTTCGGCTTAAGCTGGCTTTTCTTCTTCACCTTCGTCTGGTCATC
TTTGTTCTGCTGTGGCGGTTCTTCCTTTTTTGCTTTCTTCGACTTGGGCTCGGCCTCCTTGACCTCCTCTACTACCCATGCGTTGTTTATGCTAG
AACGCACCTTTGCATTGTAATTCACCTTCTTCTGCAGCTCAGGAGGCAGAGCCTTGCTAATAACCTCATCGTAGTTGTGCTCGTCCACCTCCTCA
AAGTTAATGGACTGCAGTAGGCGTTTGCGTTTGGATTTGTTGAGCTTCTTCAGTTTTCTTCCGGTTGCAAAGACCTCGTCCTCCATCTTATCTAA
GGCAGCCACTTTTTGCTCCACCATTTCGGACAGAGTTTGTCCCTCCACCTTTGGCATTGTCCTCACGCCAAGTGGAAACTCTCCTCTCTGGTAAG
TCTCAAAGATCTGGATAAGTTTGCGCAATCCCTTGCGTCTCTTGCTGTTAAAATCGTTGGTGCGTAGCTGCGTCTGCAGCTCATCTAGTACGCAA
TCAGCGTTGAGCGGCAGCTCCGGCATGTGAACGTCCACGTTGCCCGCTCGGGGATCCAAGGATGTGGCCCGCGGCTGCTCCTCCTCGGCGTTGAC
CTCGTCATCCTCCTCGTCAAATCCAGAATCTAGTTTCTCAATGTCATCAATGGAGGCGGTGGGAAACCCATCTGCTTCCAGGCATTGTACTTTT
CGCTGTACTGTCGTCCTAAGTCGCTCTGGTACATCAGATGATAGAGTACCCTTGTGCGGCACTGTGCCACTAGCTTAGCATCGCGTTGTGTAGCA
ATGTAGGTGACAAACGGACGCAAGAACATATTAACCTGAGCAGCAGTGATCTCACCATTGGCCGCCTTGGCCAGCTCCTCAAAGAAAACATCTAG
GTAGTGCATGGTCATGCCGCGAGACTTAGGCTGCTCCGACATCACAGAAAGCTGCATGCTGCTGTTGAATGCGGCTATCAGGTCCGCATTCCAGT
TGTTCTGTTTGAGGAATCTCAGTAGATAACGCACCATGCGGCGGGTGAGCATCAGGAATTTGTCCATGCGCCACTGATCTATGCCAAAGTACTCC
TGGCACATTGTGCGCATAAACGCACTAAAGTAGGCCAGACTGCAGGCCGTATTACCGCCGAAGCTGTCCACCATTTGAGCCAACTTCTCGGCCAG
CTCCTCCTGCACCAGCGGCTTATCCGACATCCACATGGTGTAGTACAATCCCTTCCAGATGCGCATGAAGTCGTCCTCGTTGAAGGGAAAGGAGC
TACCGGCACGCGCCTTGAACCACTTGCGCAAAATGCGGATCTGGCGATTACGCTCCACCACATCGTTGCAGGCAAGAGCACGTATAATTTTCACC
TCCTGGGCGACCACCATCAGCTCCTTGGCCACCTTCGGCTGTGAAGCGTCCTCCTCCTGCTCGACCTGGATTTCGGCCGCCTCGGCGTTGCGCTT
AACTGGCTTCTTGCGCGTCACCATTATCCGGCTAATTCAACTTTTAGTTGCGAAAAATAAGTGAGCTGTGTATATTGAATACGGTACGGCACGAC
CGCACGTGTTGCCGTTCGATGTTGCCAGATGTTGAAACGACATTTTCTCCAAATTTCGTCCAACAGCTCTAAATGCATGAGCTGTACTGAAAATG
ACAACAAAAACTCAAGCTAATGAAATAATTTTCAAAGAATAAAATAAAGAAAAAAAGAATAATAAAAAGAATATTTAAATTGCTAGTTTTGATAC
TTCATGAAACGCTTGCTTTATACATTTTAATACAATTTTATATATTTTTAGCCATTTATAGGTTGTTATTTTATAGCTACCAGCGCTGACTTCTT
TACGGAAAGTGGCAACTCTCTTCCACAGCTGATAATTCGGTCTGCTTTTTGTAAATTTTGCTTGTCCAGCAAATTTAGTTAAATAATTCAAAGAA
ATCATGCCCGTGGTGAACGTGTCGGCTGCCGAGGAGTACCAGAAGTACATTAATGCGGATAAGACGACCGTAGCTCTATTCGCCGCCGAATGGGC
AGAGCAATGCGGTCAGGTGAAAGACGCGCTGGAGGAGCTGGCCAAGATTACTGGCGAAAAACTGCAGTTCATCAGCCTAAACGCTGAACAATTTC
CCGAGATTTCCATGAAACATCAGGTACGCTCGTATTTATTTTATGAAAATATAACAGTAGTTCCTCATTCATTTGCGATGCCACCAGATCGAGGC
CGTGCCCACAGTCATATTCTTCGCCAAGGGCTCCGCCGTTGACCGTGTCGATGGTGTAGACATCGCCGCCATAAGCGCCAAATCCAAAAAGTTGG
CCGAAAACGCAAGCAGCGCGGCGGCAACAGGACAAACGTTGGAGGAACGCCTAAAGGCCCTAATCAATACAGCTCCGCTGATGATATTCATGAAG
GGCGACCGAAATGGACCGCGTTGCGGATTCTCCAAGCAGCTCATCGGCATTGTGAACGAAACCAAGTATGCAAA
(SEQ ID NO: 1024)

Exon: 3064..1001
Start ATG: 3064 (Reverse strand: CAT)

Transcript No. : CT26519
ATGGTGACGCGCAAGAAGCCAGTTAAGCGCAACGCCGAGGCGGCCGAAATCCAGGTCGAGCAGGAGGAGGACGCTTCACAGCCGAAGGTGGCCAA
GGAGCTGATGGTGGTCGCCCAGGAGGTGAAAATTATACGTGCTCTTGCCTGCAACGATGTGGTGGAGCGTAATCGCCAGATCCGCATTTTGCGCA
AGTGGTTCAAGGCGCGTGCCGGTAGCTCCTTTCCCTTCAACGAGGACGACTTCATGCGCATCTGGAAGGGATTGTACTACACCATGTGGATGTCG
GATAAGCCGCTGGTGCAGGAGGAGCTGGCCGAGAAGTTGGCTCAAATGGTGGACAGCTTCGGCGGTAATACGGCCTGCAGTCTGGCCTACTTTAG
TGCGTTTATGCGCACAATGTGCCAGGAGTACTTTGGCATAGATCAGTGGCGCATGGACAAATTCCTGATGCTCACCCGCCGCATGGTGCGTTATC
TACTGAGATTCCTCAAACAGAACAACTGGAATGCGGACCTGATAGCCGCATTCAACAGCAGCATGCAGCTTTCTGTGATGTCGGAGCAGCCTAAG
TCTCGCGGCATGACCATGCACTACCTAGATGTTTTCTTTGAGGAGCTGGCCAAGGCGGCCAATGGTGAGATCACTGCTGCTCAGGTTAATATGTT
CTTGCGTCCGTTTGTCACCTACATTGCTACACAACGCGATGCTAAGCTAGTGGCACAGTGCCGCACAAGGGTACTCTATCATCTGATGTACCAGA
GCGACTTAGGACGACAGTACAGCGAAAAGTACAATGCCTGGAAGCAGATGGGTTTCCCCACCGCCTCCATTGATGACATTGAGAAACTAGATTCT
GGATTTGACGAGGAGGATGACGAGGTCAACGCCGAGGAGGAGCAGCCGCGGGCCACATCCTTGGATCCCCGAGCGGGCAACGTGGACGTTCACAT
GCCGGAGCTGCCGCTCAACGCTGATTGCGTACTAGATGAGCTGCAGACGCAGCTACGCACCAACGATTTTAACAGCAAGAGACGCAAGGGATTGC
GCAAACTTATCCAGATCTTTGAGACTTACCAGAGAGGAGAGTTTCCACTTGGCGTGAGGACAATGCCAAAGGTGGAGGGACAAACTCTGTCCGAA
ATGGTGGAGCAAAAAGTGGCTGCCTTAGATAAGATGGAGGACGAGGTCTTTGCAACCGGAAGAAAACTGAAGAAGCTCAACAAATCCAAACGCAA ACGCCTACTGCAGTCCATTAACTTTGAGGAGGTGGACGAGCACAACTACGATGAGGTTATTAGCAAGGCTCTGCCTCCTGAGCTGCAGAAGAAGG
TGAATTACAATGCAAAGGTGCGTTCTAGCATAAACAACGCATGGGTAGTAGAGGAGGTCAAGGAGGCCGAGCCCAAGTCGAAGAAAGCAAAAAAG
GAAGAACCGCCACAGCAGAACAAAGATGACCAGACGAAGGTGAAGAAGAAAAGCCAGCTTAAGCCGAAGAATGACCAGTCCAAGCCCAAGATAGA
GGATCAACCGACCTTGAAGGCAGAAAAAGAAGAGCCTGCGAAGCGCAAGAAATTGGACCACTCCAAGACGAAGGAGGAGCAGTCGAAGCCGAAGA
CAGACGAGCAGCCCAAGCCCACACCTAAGGTGGAGGGACAGTCCAAGGCCAAGCCGACTCCCAAAACGAAGGCTGCCGGTGTTGATGATGATGCT
CCGACCAACGGATGGGATGCCCCTTTAGAGGACGGTGAGCAGGACATCTTTGTTCCCTCTCGAAAACTGCAAGTGAAGCAGGCCAACAGTAAGCT
GCCGCAGTCCACACCCAAACAGCCTGCGCGCGCAGAGTTTGCGACTCCACAAACGGGCAGTGGCAAGCATGTGCGGATCGTGACTAAGAGCAACT
GCATCTACCCCAAGAGCGATTACTACCGCCAGCTGAAGCTGTCTCCGCAGGTGCCCTACGACGCGAATCGGTTGCCCGGTAAGAGTGCCCTTAAG
CCACACTGGATACCGGGACCGATTCATCCGAGCTACAAGGCCAAGCGCTTGTTCAACGACACTCTGTGA
(SEQ ID NO: 1025)

Start ATG: 1 (Reverse strand: CAT)

MVTRKKPVKRNAEAAEIQVEQEEDASQPKVAKELMVVAQEVKIIRALACNDVVERNRQIRILRKWFKARAGSSFPFNEDDFMRIWKGLYYTMWMS
DKPLVQEELAEKLAQMVDSFGGNTACSLAYFSAFMRTMCQEYFGIDQWRMDKFLMLTRRMVRYLLRFLKQNNWNADLIAAFNSSMQLSVMSEQPK
SRGMTMHYLDVFFEELAKAANGEITAAQVNMFLRPFVTYIATQRDAKLVAQCRTRVLYHLMYQSDLGRQYSEKYNAWKQMGFPTASIDDIEKLDS
GFDEEDDEVNAEEEQPRATSLDPRAGNVDVHMPELPLNADCVLDELQTQLRTNDFNSKRRKGLRKLIQIFETYQRGEFPLGVRTMPKVEGQTLSE
MVEQKVAALDKMEDEVFATGRKLKKLNKSKRKRLLQSINFEEVDEHNYDEVISKALPPELQKKVNYNAKVRSSINNAWVVEEVKEAEPKSKKAKK
EEPPQQNKDDQTKVKKKSQLKPKNDQSKPKIEDQPTLKAEKEEPAKRKKLDHSKTKEEQSKPKTDEQPKPTPKVEGQSKAKPTPKTKAAGVDDDA
PTNGWDAPLEDGEQDIFVPSRKLQVKQANSKLPQSTPKQPARAEFATPQTGSGKHVRIVTKSNCIYPKSDYYRQLKLSPQVPYDANRLPGKSALK
PHWIPGPIHPSYKAKRLFNDTL*
(SEQ ID NO: 1026)

Classification: hypothetical

Celera Sequence No. : 142000013384832
CGTTGCCAAGCCCCAAAAAGGGGGCTCACCAGAACGAGCACAGTAAAAGAGCAAGCTGAATATATTTCTAAGTAAAATTTATTTATTATGTATA
AATAATTCTCTTTTAGCTCTCGCACAAGCGCTATTAACGTTAGTAATTTACAGTTCGCTCTGCAGTCCTCGTTGCCGAACCAGGGACTCACAGTC
GGGTATCCAGGTCACCTTTGGTGGGATTTAGGAGATCCCCCCTGCTGTAACCACTGGGTGTCCCTGGTCGGCTGCGAAGTGGAAATCAAACGAAA
CATAACGGCACAAATAGTTGGCTTAAACAATTACAATAACAATTGTGGAATATATAAATTTGCATACAGGCTAAAAGTGAAGTGGTCCCGTCTCC
ACAAGCATAGCTCCCACTTCACTTACGTTCGTATTCGTAATTTAGTTAGAAATTAGATTTCTTGTACTTGTTGAACATCGTTTGCTTTAGTGTTG
TTTTGCAGTTCCCATAGCTATCTATCCAATATATAAATACGAAAATCAATTGTAAAGAAGAGGGATATTCGGGCCGGTGCCACCGCTGCGCCATG
GTGGTTATTTGTTGACTTGGGCGCAATGGAGCCCCAACGGGTACAGAAGGAATGATTGGGATAGATGCGACTCGCTTCTGTGATTTTTGACTTTG
GCTACCCTTAAACCCATAAGAGAGATGCAACGCAGAGGTTACAATTTTTACAATAGAACGTTTGTTAATTTGTTGCTTAGGCGCTGCTTTATCCA
CTACTATATCTACCAGTTATTTATCATCCTCAGTTATACATTTATACAATCCTATTGCACACATACGATTCTCATATGTCTTGCTTAGCACCCCC
TCAAGATACATATACATAATCATATACATACATAGATATAGATATTTTGATACAGTTATAGTTAAAGTTAAAAAAATACCTCACACTTGATAATA
ATGAGTGTAAAGACCCGCCCGCGACTATGGTATGAAGTTAACCCCGACCAGCTCGAAAGAAAGTGATAGTGTAGGAGGCATAGGAAATAGAGGGT
CGAGAAGGCCTTGAGTTGGCGGTCCTAGACGGGCCCAATATCACTTTGGTATCTGGCGGTCAGGTAGTTGGCCGCCTCTGTCATTTGTTCCAGGC
ACTGGTACAGACCGTTAAGATGCCTCCGGCAGCGCTTGGCCAGCTCCGTGGCCTTGTCCCCCGAGCCCGGCTTCGATTTGGCGACGTCTACAATG
TCGCTGCCGTCGCTGCTTTGGGCGTTGTCGCTCTTGTTGCCATCGGACTCTAGCCCCGAGTCGTTTTCCTGCGATATGTCCGAGTCAGAGTCACT
CATGTTGCTCACCGAGTTGGTGGACATCATGGATGCGGTAGAGGTACGGCGCACATGACCCTTGACACTTCCGGATGCGGTTGTGCTTGGACTGC
CGCTGTTGAATTCAGTCTTGCTCTCGCTGGGATTGCAGCTCGAAGTGGAACTGGTACTGGCGTTGAGCTGCTGTTCGGAGTGCTGCTGGTCGTCG
TCCTCCTGGTTGGCGGTCCAAAGCAGATCTTTTTTCAGGGAGTTCAGCATGTTGTACAGATTGAACAGCTCGGAGGCGCTGAGAAAGTCTTGGAC
ATTTTTTGAATGCGCCGCTCCCCGCTTGCCGTGGGCACTGGAGGTCTGTGTCAGCTGGTTGGCGGTCGAGTCCTTGCCGGTTGCTGGGATGATGT
CAGTGCTGTCGCCGATCTGGGGATAAATTATGTAAAGTGGGAGCCATAAGTTGTTGGTTCCGGATCCGGATGGCTGGTCAAATGGGGGGCTGGGG
TTCTTGGGTTATGCGGTACCAACCTGCCGATCCATGAGCCTGCATGGCACCAGTATGGTGTCGTCCATAATGTTGACAGTCTTTACAAACTTTTC
CATCACATTGACAATGCTGTCTTTGGAGAACTGCTGCTCATCGTGACGGGCGATGCGGCGCAGGCAGTTTCTGAAAAACAGAACAATCGAAAGAT
GAGCTTGGGCCAGAGCACAATAAACCAGTAGAGCGTGTGCAGGGGAACCAGTTTGGATTGGACAATAGTCTGCGTGATTAGTGACTATGCCACAT
CACGCCAGACTGGACCAAGCGCTGGCCGTTCTAAAGCGTCGTTAAGTCTGCGGCGATCAGACTTCCGCCACTCGAAGCCATCTTTCTTTGATGCT
TTCGACTGGAGATGGGTGCGCCTCCTGCTGACCAACGTGGCATATGATATATATGAATTGGTTTCTATGCAAATCAGCGACTCGCTGGCGTTGTC
GCAAATTCAATTTGTATAAAATAGAAAACCAGTTGGTGCTTTATACCTGACATTGCTCGTGTGGCTCTTAAAACAAAGCACAGACGGACGGACAG
AAAGATTTCTATTTTGGTTTCCAAAGCCAATTTAACGCGTCCACGTGCTGTCGGTGGCGGGGTGCGAGGGTAAAGCCCGACTTTGCTCGCAAGCT
TCAATGTAATGGTTATACAATCCTGGCTGGTCGCATTAACTTTAATTTCACGAAAAGATCGCGTAACATCTCCAGGTCAAGCCCCATAAACTTGC
CTGAGCTCCCTCCATTAACCCGCCGGGAATATATGTTAGTTGCTGATATCTGGAGCTGGAGCGGCCAAAGTCTAGAGGCGGCTTGGCTTATCGTC
GCTAGACAGTTCCCAGACAGAGCTGAAGTTGCGTATCTCCCGCACCTCCTATTTAATGCGGCCAGATTGCTCGGGGCGGATCGGCATGTGGGCAG
CCAGTTCGGGGCCGCGTGATCGCAGCTAGTTGACAGAGCGAGCGCCGAGCGCACTGATAAATTTAGTTTCAGTGACTGCGCCATTTAAAGACCTC
TACCCTACAGTTCTATCCCTGGCCAGCGCCCGCCCCGATGCCATGGCAATCCAACTTAGAAAATCTAGATATCGATGACTGAAGTGTAACGCGCG
GCAGGCCGGGGTGGGGTGGCCACGCGAGTACTGCGTGCTCCGAACTCTGCTGACCGACATCGTCTCACTGTGGTCTAGAACCACAATAAGATCTA
GATCTAGAGAAGGCTGGCGCGGGTGTCAATGTTCTTTCCACTGGCACGGCCAGATGTCGTGGACGTCGACGGAGGATTCCCAGCCACTGAACAGA
GTGACTAATTAAGCTAATTGCAGCGGGTTCCAATCATGGAAATCCGCGTAGGAATGCGAAAACAATTACCATCTTATCAACGCTTTTCGCTTAGA
CACTCGACCATAATTGACTGCCATCTCGTGGAAACCTGAGTAATCGCCTCTATTTATTTTAAATTATAGATATTTTCTAGCCCTGACCACGACCC
TTGCTTCGCTTAGTCACTTAAGCTGGCCACACGATAGTTCAACTTATCACTGCATTTTGAATCCTTTCCTTGCGAATCCTCTGAACAGATCCCGA
AAGCCCAAAAACGCCGGCTTGGGCAACACGCCAGATGCTACCAGCCAATTGACCAGGCAATAGGTACACCTGAAGTGTTATGGAAATTTGGCTAA
GCCCCACAAGCGTCACGCGACATGCTCGCCAAGAAGGGCGGGGTAAGCAGCGGGAGAGGGAGGGTACCGCATACAACGCCGAAATCAGGCGACTT
TTTCGCTCAGCGGTAGCTAAGGGCGGTGAAGGAGTGCTGAAGGGGTGGTGGTTTGGTGGGTGGCTGATGACGAGCTGGCTTTATGTGGCAAGCGA
ATCAAACGCTTCTCTTCGCACTCTCTCTTCGGTCCGTTTCGCCGTTTTCTCTTTGCCGCCGAGTGGCGTGATGTTGCCCAGAAACTGTACAGCGG
CCAGAGTCGCCTCCATCAGCTGAGCAAGATGAATGAATCTCTAGCGATGCTCTGCCTTCCCCTCACCTTCCTACCATCGCTCATGCAACCATGTT
TAGTGGTATTTCTCGTATTTGCAATGTTGAGCAATGGCATATACATAGCCATACGAACAGAGTTGACCAATATTTGGTTTACTTTGGCTTTGGCT
GCGCCTCGACCTCCAGCATAATCGATTTTTGATACGCCCGCAAATTAGATATTCTACCTACTCGGTGGCCGGGTTGGCCGGATTGGCTCGGCCAT
CGGGCATAGAGCATTGACGACCGTAAGTTGGCGCTCAAGGCGACACCTGCCTCAAAAAGTGACACACTGCCAGCGCAACGAGGTGAATCAGAGAA TTTTCTGCGATTTAAGCGCCCCAAGGAGGCGGGCAGCACCAGAAGCGATGAGTAATGGCTATGGCCGATAGCTGGGCTGGCGGACTGGTGTCAGT
GGACCGGAGGTGCGCACAGATAAGGCATCTTATCGCTTATCCCAAAGCTGTGATTTGCCTCCGCTGGCTCACTCGAAACATTTGGGCAAACAAAC
GGCAAAAAAAACACCAACATACTTCTGTATAGGTGTACAATATATAGCCGATTGTGTCATATTAGCGCTGGCTTGATTTTTTTATTTTATTTTAT
TTTTTTTGTATTTGTTGTTG
(SEQ ID NO: 1027)

Exon: 3485..3376
Exon: 1970..1829
Exon: 1726..1001
Start ATG: 3380 (Reverse strand: CAT)

Transcript No. : CT26531
ACCTATTGCCTGGTCAATTGGCTGGTAGCATCTGGCGTGTTGCCCAAGCCGGCGTTTTTGGGCTTTCGGGATCTGTTCAGAGGATTCGCAAGGAA
AGGATTCAAAATGCAAAACTGCCTGCGCCGCATCGCCCGTCACGATGAGCAGCAGTTCTCCAAAGACAGCATTGTCAATGTGATGGAAAAGTTTG
TAAAGACTGTCAACATTATGGACGACACCATACTGGTGCCATGCAGGCTCATGGATCGGCAGATCGGCGACAGCACTGACATCATCCCAGCAACC
GGCAAGGACTCGACCGCCAACCAGCTGACACAGACCTCCAGTGCCCACGGCAAGCGGGGAGCGGCGCATTCAAAAAATGTCCAAGACTTTCTCAG
CGCCTCCGAGCTGTTCAATCTGTACAACATGCTGAACTCCCTGAAAAAAGATCTGCTTTGGACCGCCAACCAGGAGGACGACGACCAGCAGCACT
CCGAACAGCAGCTCAACGCCAGTACCAGTTCCACTTCGAGCTGCAATCCCAGCGAGAGCAAGACTGAATTCAACAGCGGCAGTCCAAGCACAACC
GCATCCGGAAGTGTCAAGGGTCATGTGCGCCGTACCTCTACCGCATCCATGATGTCCACCAACTCGGTGAGCAACATGAGTGACTCTGACTCGGA
CATATCGCAGGAAAACGACTCGGGGCTAGAGTCCGATGGCAACAAGAGCGACAACGCCCAAAGCAGCGACGGCAGCGACATTGTAGACGTCGCCA
AATCGAAGCCGGGCTCGGGGGACAAGGCCACGGAGCTGGCCAAGCGCTGCCGGAGGCATCTTAACGGTCTGTACCAGTGCCTGGAACAAATGACA
GAGGCGGCCAACTACCTGACCGCCAGATACCAAAGTGATATTGGGCCCGTCTAGGACCGCCAACTCAAGGCCTTCTCGACCCTCTATTTCCTATG
CCTCCTACACTATCACTTTCTTTCGAGC
(SEQ ID NO: 1028)

Start ATG: 106 (Reverse strand: CAT)

MQNCLRRIARHDEQQFSKDSIVNVMEKFVKTVNIMDDTILVPCRLMDRQIGDSTDIIPATGKDSTANQLTQTSSAHGKRGAAHSKNVQDFLSASE
LFNLYNMLNSLKKDLLWTANQEDDDQQHSEQQLNASTSSTSSCNPSESKTEFNSGSPSTTASGSVKGHVRRTSTASMMSTNSVSNMSDSDSDISQ
ENDSGLESDGNKSDNAQSSDGSDIVDVAKSKPGSGDKATELAKRCRRHLNGLYQCLEQMTEAANYLTARYQSDIGPV*
(SEQ ID NO: 1029)

Celera Sequence No. : 142000013384828
TCGTCCGGATGCTTGTCCTTGAAGTGCTCGCGGATGCCGTCGAAGTCCTCGGCCAAGAATATGCACAGCTCGCAGCCCATGACTATGTAGCGCTT
GATCAGTTCCTCGTCCTCTTTGCAAAACGGCGGCAGGCGTTCCATCTTGAATATCCTCTTGGGCGGTCCCCGCTTGACCACCATCTTCTCCTTCC
CCTTTCTGCCCACCGACACCGTTCCTCTTTTCGTTTTAGCCGGCTTGGCCACGTCCCGTTTACGTTTGCGTCCACTCCGGGTCACGATCAGGTCG
TCGGTGTCATCATCCTCGTCGTCCTCGTAGTCCTCATCCTGTTCATTGTTGGCATCCTCAAAGAGGAGTTCCATGTCGGGTGACTGTCGCTCTGT
TTTGATGCCCACCTTGCTGTCTTCCGGGGACATGGGTTGGCTAAGGTCTAACTCGTCCAGGGGATTCACATTTATCTGCGCACCGACATCGTTGT
CGACGGCAAGGACGTCGGCCGGCATGAGCACCTCCTCCGGCCAGGAGGTGTTCACCATCTCCGGATCCTGCTTGAACTTGGAGGTGGTGGCGTAT
ATCACCTGGGCCTCCTGTATGGACACGTAGAACTGATGGAACTCGGACACCTGCGTCCAGCAGACGTTGCAAATAACCTTGGATATCTCGTCGTT
GGGCAGTACCTGTACGCGTTCCGGAGACGAGATGGTGGTAAAAAAAGATTCCCAGGCACAAAAGTGGGTGGAGGGCAGCAGCTTACCTCGAACCA
GAAATGTTGGCGCAGCACCTCCGCCACCTTGCTCTCGCCCGAGTCCACATCGAAGATCTGTAGACACATCTGGGCGCCGCTCACTCCGCGTAAAC
AGAGGCGGCAGATATCCATTTCGCATTTATTTGATAAAACTATAATAAAAAGTAGTCATTTACATAGCTCTGTCGATAACTCCCATCGCAACTAT
CGGCTGCATCGTGATTTGTTCGCTGTTCATTCTGTGCACTGGTTGTACGACGTCGGTCACACTGGCAAATTGTTGGTTTTCCTATTTTCGTATTT
GCTGATAATGTGCATATTGTGTGGAAAAGATGAGTAAACAAGGGAATAAAAGCAAGGATTCGGCTGCCGCATCCGCCACTTTAAAAGTAAAGGTG
TCCTGTGTAGCCGGAAAAACGAGCCTAACATTTTTCGGTCTTGTTTTCAGCGGATAAGCGAAAAGAAGTTGGAGGCCTTCACGGTGGGCACCTTC
TCCAAACGACAATTGTCCAAAAAAGAGCTCGAGGACCAGAAAAAAAAGGAGGATGCAGCTGCTGCGGCACATGTAGGCGCCTCTAGCAAATCCCT
CCTCCACGCATTATAATCCAATACGATTTTTAGGCCTTCAAAGAGTTCGTAGAGACTTTCCAAGATGCACCCACCCCCTCCTCGAAAGTTTGGGT
CAAAGCCGGCACCTATGATGCAGGATCCCGGCGGGAGGACAAGTCGGAGAAGGGCAAGCTATACAAGCCGGTCTCCAAGCTGATGGAAAAGAGCT
CCTCGGACAAGGTCGAGGATTACGCCAAGACCCTGGCCTCGGATCTCAAAAAGGACTCGGGTCCATTGAAGAAGAAAAACCAGGAGAAGAAAAAG
AGCAACTTGGAGCTGTTCAAGGAGGAATTGAGACAGTAGGCCCACTTGGTTGTGCATGTGTGTATTCCATACTAATTGTTTCATGCCCACAGGAT
TCAAGAGGAGCGTGAGGAGCGCCACAAGTACAAGCACATGGCCTCAAGCCATTCCGCACCAGCACAGCAACCGGCTGCATCAGCTGCTCCTGTGC
CCAGCAGCAGTGTCTCCACCACCTCCCAGAACTCAAGCAGCTCAAAGGAGTCTGGTTCGTTTGACACGGGCGATCCAAATACCACAAACCTGTAC
CTGGGCAACCTGAACCCCAAGATATCCGAGCAGCAGCTTATGGAAATCTTTGGGCGATACGGTCCCTTGGCCAGTATCAAGATCATGTGGCCCCG
CTCCGAAGAGGAGAAGCAAAGGGGACGCAATTGCGGCTTTGTGGCCTACATGAGCCGCAAGGATGCGGAAAGGGCCCTAAAGACACTGAACGGGC
GCTACATCATGGGCTACGAGATGCGTCTAGGATGGGGTAATCTATAGATCTTATATTGAAGTTCTTATTCCTCATACATCTTACTTAATATTTCA
GGAAAGACTGTGCCCATAATGAATACGCCCATTTTTACACCGCAAGCATTGCTTGAGATGACCCTGCCTCCGCCTCCTTCAGGATTGCCCTTCAA
TGCCCAACCTCCACCCAGTGAAGCTGATGTGCTGCCCAAGAAAAACTACAAGGAGTTCAACCAAGAGGACAAAGAGAATATGGAGCGGGTAAGTG
AATAATCACCTGCTAGCGTCTAAAGAAATAAAAATGAAAATGTTCAATTTTGTAGATACTTGCCAAATGCGTCGTTAAAGTCCATATACCCACAG
AGAAGTATGAATTGCACCAAGGACATTCACTTAACAAGAACTCACGTTACTGTGCTTTTCTTTTTTTCCAGGGCTGTTCTTAATGTTATCCATCG
GATGATCGAGTTTGTAATACGCGAGGGACCGATGTTTGAGGCTTTGATCATGATTCGGGAAATGGAGAATCCGCTCTTTGCGTTCCTCTTCGACA
ACGAGAGTCCTGCCCACATCTACTACCGATGGAAGCTGTTCTCTTTGCTACAGGGCGATACGCCCAATGAATGGCGGGAGGAGGAATTCCGTATG
TTTAAAAACGGACCGGTTTGGAAGCCCCCGATTGCCAACTTCTACACTCAAGGCATGCCAGATGAGCTGGTTGTTGATCCCGATGCTCCTGTGGT
GCACAAAGGAGCCTTGTCCAATGCGTACGTTTAGCATAGATAATCCTCGAAACATAAATGTTTACTGTACTGTAAATGTATACTGAAATAGGCAA
CGCAACCGACTCGAGGATTTGATTAGGCACTTAACTCCTGAACGCGCCCGCATTGGAGATGCCATGATCTTCTGCATTGAGCACGCAGATGCGGC
TGATGAAATCTGCGAGTGCATCGCCGAGTCTCTGTCAAATATCAATACATTGGCTTCAAAGAAGATTGCTCGACTTTATCTGATCTCAGATATAC
TGCACAACTGCACTGTTAAAGTTGCGAATGCTTCGTTCTTCCGTAAATCGTATGTATATATGTTTATCAAAGCATACACATTGAAATATCCCCTA
TTATTTAGTGTGGAAAAACAATTGTTGGACATCTTTGATAACCTGCATAACTACTACTTGAACATCGAGAGTAGATTGAAAGCTGAGGGCTTTAA
ATCCAGAGTCTGCAATGTTATCCGCACATGGGAGGAATGGACCATTTATCCCAAGGATTTTATGGCCCAGCTGACGGCCAAATTCTTGGGCAAAC CTGTTAGTTAATGAAATTCATTTCAAATTGTGCATGTAGTCTAATGGAATCTTGTGTTTAGTACGTCAAGCCAGTCAATAACTCACCTCAAGCCG
AGGAAACGCGATTTGATGAGGCTCTGGACGAAGATATCGACGGTGCGCCCCTTTCCGGAGAGGAAAAGGACGACGAGGATCTAGACGGAGTGCCA
CTAGATGGAGCTGCTTTGCTTAAGAGCGCCTTGAAGCGAGCCATACCTGATGCAGATGCTGGTACTCCAAAGCGTGACACACCTAAGAAAGATGA
ATACCTCGATGAAATCGATGGCATACCATGTAAGCATAAGAAAGTGATTTAAACCTTCTTACTACTAAGTAAATAATCCTTAATTCCAGTGGATG
ATGATCTCGACGGTGTACCGTTGGAAAAAGAAACCAAATCTACGGCTAAGTTGCCTGGCTTCATACCCTCAAAGTGGGAGACAGTTGATCCCCAG
CAAGTAGAAGCGCAGGCGATTACCACCAGCAAATGGGACACTCTCGATCCGCCAGATCCACCGAAGTTCTTTAGCTCGGACGACGACAGTGGAGA
AGACAATCCGCAAAAGTACACCGACGAGATGCGTCAGAAGTTAAGAGACATTGAGTCGAAAGCAATTCAGTACCAGGACGAACTGGAGTCCGGAA
AGCGCCGCCTGGAACCAGGTTGGAGTGTCCCCGAACAAGTGGAACAATTCCGGAAGCGATTACTTAAACAGGTAAGATTTGTAACATACAGTAAG
TCGGATGTAACAACTGAATTCTTTGCGAACGAACAGGACTCGCGATCTGAGGCAACTGTAGACTCCCCGCTCAGCTACATGCACATAAAATCCAA
GAGCTCCAAGGTGAGTGAGAGTCCAGCGCTGTTCAGAAGCAGTTCCCGCAAACGATCCCACTCGCCGTTCTCTGGTGGCGAATCCAAACGACGTG
ACTATTCACCCGAAACCTCGCGCTCATCCAAATCCTCGAAACGCAATCGGTCGCGTAGTCCGTCCAGTTCACCGAAGCGGTATACAGAGCGGTCG
TCTCGCAGCTCCCGCTACGAAACTCCTGCCTCCGGATCGTCGCGATCACGCAGTTCTCCAACCTCCTCGCGCTCCTCTCGCAGAGAAGAGCCATC
GCCGCCGAGACATCGCAGCGACAAGCACAAGCACAAACATAGGCACTAGAGTGTCTGCTCTTCGGACGATTTGTATTTAATTAAACATGGATTCT
ACATAAAAACACTTTCGTCGTTTGTTTTAAATACACAGTATATATAATTTTAAATCTAAATCGTTTGTTAGGAAGTGGGACACACGCAAAACAGA
CGGCCCAGGCAGTTCGATTCCGCTCTGCGAATTTGTCTAAAAACATGAATCTAAGCAAGCTATCTTAAAATGGTTACGTTTTGTTAAGGAAAGCC
GGCCAACCAACACCAGTCCTCGAACCGCCTGAGCCTGGTCATATAAGCAGTGGTGATTATCATAAGGTGAATACATAGATGTGGCTTAAAAGTAG
ATGCGAACAGCCTCCTCGGCATTCTGCTCCACGGGGCAGTAGGGGCACTTCAGTATGTGGCCAACACTCAGCTTGTGCAGGGCGTCGTTGGATAT
GACATGACCGCAGGTCAACTTCTTCGGCGGATTGTCCTCGGAAGTCTGCTGGCGCAATATGGGGCAGGCAAAGATCGAGTGGAATCGGAATTCCG
GCTGCAGATCGATCTCAATGGGCAACTCGTCGCAGCCGTTCCACATGCCAAGGACTTGGCGCGACTGCATCACCTGCTTGATATTGAGCAAGGCG
GGCAGGGCAGTGCATCCGGCATTGACCACAACAGACAGGGCGGAGTTCTTGCTAATGCCTAGCAGTTGGCATGCGTCTTTGAGGAATATGAACGA
CAGTTCGGTCCACTTCTCCTGGCCCAAGAAGTGCTTGTAAGGCGAGTTCTCCAGTCCACTGGGCAGATATATAAAGCTGGCCATCAAGTTGGCTA
TTTCGTGCTCATAGCGCACAGCAAACTTCTTGAAGTTCAGTCGAGCGTAGGAGATGGCCTCGCGCTGCGAGTCCAATCCGTAGGAGACCAGCTGC
ATGAAACGCATGCGGTGCAGCCGGAACTCTATGAGCGAGTGGCGGTCACTCAGCTGCTGGGAGTACATCTTTGCCCACTTGAGGGCGTCAGTCAG
ATCC
(SEQ ID NO: 1030)

Exon: 1001..1131
Exon: 1191..1307
Exon: 1364..1650
Exon: 1708..2126
Exon: 2187..2368
Exon: 2431..2474
Exon: 2542..2874
Exon: 2942..3184
Exon: 3239..3422
Exon: 3482..3734
Exon: 3795..4156
Exon: 4217..4609
Start ATG: 1075

Transcript No. : CT26551
CGTCGGTCACACTGGCAAATTGTTGGTTTTCCTATTTTCGTATTTGCTGATAATGTGCATATTGTGTGGAAAAGATGAGTAAACAAGGGAATAAA
AGCAAGGATTCGGCTGCCGCATCCGCCACTTTAAAACGGATAAGCGAAAAGAAGTTGGAGGCCTTCACGGTGGGCACCTTCTCCAAACGACAATT
GTCCAAAAAAGAGCTCGAGGACCAGAAAAAAAAGGAGGATGCAGCTGCTGCGGCACATGCCTTCAAAGAGTTCGTAGAGACTTTCCAAGATGCAC
CCACCCCCTCCTCGAAAGTTTGGGTCAAAGCCGGCACCTATGATGCAGGATCCCGGCGGGAGGACAAGTCGGAGAAGGGCAAGCTATACAAGCCG
GTCTCCAAGCTGATGGAAAAGAGCTCCTCGGACAAGGTCGAGGATTACGCCAAGACCCTGGCCTCGGATCTCAAAAAGGACTCGGGTCCATTGAA
GAAGAAAAACCAGGAGAAGAAAAAGAGCAACTTGGAGCTGTTCAAGGAGGAATTGAGACAGATTCAAGAGGAGCGTGAGGAGCGCCACAAGTACA
AGCACATGGCCTCAAGCCATTCCGCACCAGCACAGCAACCGGCTGCATCAGCTGCTCCTGTGCCCAGCAGCAGTGTCTCCACCACCTCCCAGAAC
TCAAGCAGCTCAAAGGAGTCTGGTTCGTTTGACACGGGCGATCCAAATACCACAAACCTGTACCTGGGCAACCTGAACCCCAAGATATCCGAGCA
GCAGCTTATGGAAATCTTTGGGCGATACGGTCCCTTGGCCAGTATCAAGATCATGTGGCCCCGCTCCGAAGAGGAGAAGCAAAGGGGACGCAATT
GCGGCTTTGTGGCCTACATGAGCCGCAAGGATGCGGAAAGGGCCCTAAAGACACTGAACGGGCGCTACATCATGGGCTACGAGATGCGTCTAGGA
TGGGGAAAGACTGTGCCCATAATGAATACGCCCATTTTTACACCGCAAGCATTGCTTGAGATGACCCTGCCTCCGCCTCCTTCAGGATTGCCCTT
CAATGCCCAACCTCCACCCAGTGAAGCTGATGTGCTGCCCAAGAAAAACTACAAGGAGTTCAACCAAGAGGACAAAGAGAATATGGAGCGGATAC
TTGCCAAATGCGTCGTTAAAGTCCATATACCCACAGAGAAGGCTGTTCTTAATGTTATCCATCGGATGATCGAGTTTGTAATACGCGAGGGACCG
ATGTTTGAGGCTTTGATCATGATTCGGGAAATGGAGAATCCGCTCTTTGCGTTCCTCTTCGACAACGAGAGTCCTGCCCACATCTACTACCGATG
GAAGCTGTTCTCTTTGCTACAGGGCGATACGCCCAATGAATGGCGGGAGGAGGAATTCCGTATGTTTAAAAACGGACCGGTTTGGAAGCCCCCGA
TTGCCAACTTCTACACTCAAGGCATGCCAGATGAGCTGGTTGTTGATCCCGATGCTCCTGTGGTGCACAAAGGAGCCTTGTCCAATGCGCAACGC
AACCGACTCGAGGATTTGATTAGGCACTTAACTCCTGAACGCGCCCGCATTGGAGATGCCATGATCTTCTGCATTGAGCACGCAGATGCGGCTGA
TGAAATCTGCGAGTGCATCGCCGAGTCTCTGTCAAATATCAATACATTGGCTTCAAAGAAGATTGCTCGACTTTATCTGATCTCAGATATACTGC
ACAACTGCACTGTTAAAGTTGCGAATGCTTCGTTCTTCCGTAAATCTGTGGAAAAACAATTGTTGGACATCTTTGATAACCTGCATAACTACTAC
TTGAACATCGAGAGTAGATTGAAAGCTGAGGGCTTTAAATCCAGAGTCTGCAATGTTATCCGCACATGGGAGGAATGGACCATTTATCCCAAGGA
TTTTATGGCCCAGCTGACGGCCAAATTCTTGGGCAAACCTTACGTCAAGCCAGTCAATAACTCACCTCAAGCCGAGGAAACGCGATTTGATGAGG
CTCTGGACGAAGATATCGACGGTGCGCCCCTTTCCGGAGAGGAAAAGGACGACGAGGATCTAGACGGAGTGCCACTAGATGGAGCTGCTTTGCTT
AAGAGCGCCTTGAAGCGAGCCATACCTGATGCAGATGCTGGTACTCCAAAGCGTGACACACCTAAGAAAGATGAATACCTCGATGAAATCGATGG
CATACCATTGGATGATGATCTCGACGGTGTACCGTTGGAAAAAGAAACCAAATCTACGGCTAAGTTGCCTGGCTTCATACCCTCAAAGTGGGAGA
CAGTTGATCCCCAGCAAGTAGAAGCGCAGGCGATTACCACCAGCAAATGGGACACTCTCGATCCGCCAGATCCACCGAAGTTCTTTAGCTCGGAC
GACGACAGTGGAGAAGACAATCCGCAAAAGTACACCGACGAGATGCGTCAGAAGTTAAGAGACATTGAGTCGAAAGCAATTCAGTACCAGGACGA
ACTGGAGTCCGGAAAGCGCCGCCTGGAACCAGGTTGGAGTGTCCCCGAACAAGTGGAACAATTCCGGAAGCGATTACTTAAACAGGACTCGCGAT
CTGAGGCAACTGTAGACTCCCCGCTCAGCTACATGCACATAAAATCCAAGAGCTCCAAGGTGAGTGAGAGTCCAGCGCTGTTCAGAAGCAGTTCC
CGCAAACGATCCCACTCGCCGTTCTCTGGTGGCGAATCCAAACGACGTGACTATTCACCCGAAACCTCGCGCTCATCCAAATCCTCGAAACGCAA
TCGGTCGCGTAGTCCGTCCAGTTCACCGAAGCGGTATACAGAGCGGTCGTCTCGCAGCTCCCGCTACGAAACTCCTGCCTCCGGATCGTCGCGAT CACGCAGTTCTCCAACCTCCTCGCGCTCCTCTCGCAGAGAAGAGCCATCGCCGCCGAGACATCGCAGCGACAAGCACAAGCACAAACATAGGCAC
TAG
(SEQ ID NO: 1031)

Start ATG: 75

MSKQGNKSKDSAAASATLKRISEKKLEAFTVGTFSKRQLSKKELEDQKKKEDAAAAAHAFKEFVETFQDAPTPSSKVWVKAGTYDAGSRREDKSE
KGKLYKPVSKLMEKSSSDKVEDYAKTLASDLKKDSGPLKKKNQEKKKSNLELFKEELRQIQEEREERHKYKHMASSHSAPAQQPAASAAPVPSSS
VSTTSQNSSSSKESGSFDTGDPNTTNLYLGNLNPKISEQQLMEIFGRYGPLASIKIMWPRSEEEKQRGRNCGFVAYMSRKDAERALKTLNGRYIM
GYEMRLGWGKTVPIMNTPIFTPQALLEMTLPPPPSGLPFNAQPPPSEADVLPKKNYKEFNQEDKENMERILAKCVVKVHIPTEKAVLNVIHRMIE
FVIREGPMFEALIMIREMENPLFAFLFDNESPAHIYYRWKLFSLLQGDTPNEWREEEFRMFKNGPVWKPPIANFYTQGMPDELVVDPDAPVVHKG
ALSNAQRNRLEDLIRHLTPERARIGDAMIFCIEHADAADEICECIAESLSNINTLASKKIARLYLISDILHNCTVKVANASFFRKSVEKQLLDIF
DNLHNYYLNIESRLKAEGFKSRVCNVIRTWEEWTIYPKDFMAQLTAKFLGKPYVKPVNNSPQAEETRFDEALDEDIDGAPLSGEEKDDEDLDGVP
LDGAALLKSALKRAIPDADAGTPKRDTPKKDEYLDEIDGIPLDDDLDGVPLEKETKSTAKLPGFIPSKWETVDPQQVEAQAITTSKWDTLDPPDP
PKFFSSDDDSGEDNPQKYTDEMRQKLRDIESKAIQYQDELESGKRRLEPGWSVPEQVEQFRKRLLKQDSRSEATVDSPLSYMHIKSKSSKVSESP
ALFRSSSRKRSHSPFSGGESKRRDYSPETSRSSKSSKRNRSRSPSSSPKRYTERSSRSSRYETPASGSSRSRSSPTSSRSSRREEPSPPRHRSDK
HKHKHRH*
(SEQ ID NO: 1032)

Name: RRM-type RNA binding protein
Classification: RNA_binding

Celera Sequence No. : 142000013384474
CCAGCAGAAAGAACGATATCTTCGGCATCAATGACGGACAGCTGGCGGCGGATGATCTTCCATATGCCACTCTGAGCTATGCCAATGGACCGGGC
TATGATAGTAACTACCTCAGGGAAGGCGGCGCTGTGCGGAGGAAAAATCTGAGAGCCATCAATATGAAGAACAAGGACTTCATGTTCCCCAGCAC
AGTTCCCTTGGAATCGGAAACGCACGGTGGCGATGATGTGGCCGTTTTTGCTAGTGGACCGTATGCCCAGCTTTTCACCGGAGTTTTCGAGCAGC
ATTTCATACCTCACGCCCTTGGTTACGCCTCTTGCCTCAGTGATCGTAACATGTGCGTGGATGGGGGCGTGGCACGGAGACCACGCTGAAACTTG
GCGGGGATCAAAGGTTAAGTGAAGCACAATGAGTCTAAGCGACAAACGTATTATTCTCGTTTAAGAGAGAAGCCACTAGAAGATAAGCAATCGTT
TAAGGGGGATACTAAAATAAATAATTGAAATCTAAAAAAAGCATCGATTACTATTTGTGCCAATATTATACGACATTTATTTGCAGATAAGAGTC
CGTTCCCGTGGTTATCTTATAATGTCGATTCTTTTTGCACTTTAGAATTTGATAGCAAAATGTCGATTTTACGCGGGGAGGTTATCGATTGACA
TGTGTCAACTGCTTAAATTTTGTTTCCTTTTCAGTGTTGGCTAATATCAACATGTGACTGCTTGCATCCGCACTAACTGTGGTTTTTGTCTTTAC
TAAATCTAACAGCGTACTGTTGCCAACACTAAAATGTTAAATTATTTTAAAACTAACAGACGACTTGGCGCCAAATTTGAAATAAAATTAAAATG
TTTTCGAATATAAAAGGGACAGACAACATTAATGACTAGGGTTTTATTGAAATATACATGGGGCTAATTGCTGGACATATCAGATTTAAATTATA
TTTTAATATGTATAAGTGTATATCATTTTCATTTTGTGCTGTTTTTATTTATCTTTTTACAATTAATGCCTTCTGGCTGCATATATAACATAAGG
ATTCACACAAGTGGCACTTAATTATACAAACTTAACTTTAAATTTCTACACAGTTTTTTTCCCTTTTGCGAAAACGAAGCACAAATAGTCAGGC
GAATTAGTAGCATAATACATTACGCATAATAACAATATTTAAAATTAGGCATACACATAGTTCACAGTATTTTGCACGATTGCTTGGACGTCGTC
TTTGGTTTCCTCTCCACGGCTCTAACCGCCTCCTCGAAGACCTGCTGCAGGTTCTGCTTCTTCTTGGCGGAGCACTCGACCAAGTTGAATGCGTG
TATCTCTTTGCGCATCTTTTTTCCCTCCTGAAAAAGTCGAGAAAACTTAGCATACAACTGTGTCAATCGTTTAGTTACTAACTAACCTGTGTGGT
CACGAACTTCTCCGAGTTGGGAATGCGCAAGTCCAGTTTGGTGCCCACGAGAACCACGGGAACGTGGGCGGAGAAGTGACGGATCTCCGGCCACC
ACTTGCTTTTCACGTTTTCGAATGAGGTCCTACTGCTGATCGAATAGCACAACAGGAAGCAGTTGGTCTGTGGAGCGAGTACGAAATGTATTAGC
AATAGGTAGGACTAATTTCCCTATCAGTAGTCAATGCTATCATACTTACACTGGGATAGCTCAGGGGGCGCAGCCTTTCGTAATCCTCCTGGCCG
GCAGTGTCCCAGAGGGTCAGATTGTAGTCCCGATCATCTACGGCTATGTTGCAGGCGTGATTGTCGAACACTGTGGGTATGTACTCCTCGGGGAA
CTCGTTCCGTGTGTAGGTTATCAGCATGCAGGTTTTGCCCACCATGCCATCGCCCACGATGGTTATTTTCAGCGGGCGCGGACTCTTCGTTATGT
TCGCCGTCATTCCCGGTTTTTTCCCCGTTCGTCTTTGTTAAGCAAGAACTGCAAAGAGGACAAAATAGAGGCGTCACAATCGGGATTGCAACAT
TTGGTGGCAGATGTTGGCGCACTGTGTGTTTATCTTGGCGCACCCACACTTTCATCCAACCGGAAATCTCCAGGCTTTGCCCCTAGCTGGCTTCA
CTTTGATACTTGCAGAATACAGCAGAAATGGGATTACTGCTCATACAGAATATAAGAATGTATAAGAATGAACTTCAATAGCATTAGCTGGAAAT
ATTGCTGAGTAAGTAAATACAATACACCAGTCTAATCTACATTCTATTTCAGTTGAGTTCGCTTGAAGGAATATCGGTTTCCATTGACGTTTTGA
AGTTTTCATTATTGCTGGAATGTGTTTTATAGAGTTAAATATATAAATGCCACATTTTAAACAAATTATACGTATCTATATCATAACAGCGAACA
GTCCACCTGAATTAACCTTGTTGATCATACAACCCATATCGCACATGAACTTCAAAACTTTTAATCTAATCGCCGGTCGAATTGAAAACGACAAA
AGTCTGGGCAATTGGAGCTTTTACGACGGGCCAACTGTGGACTGGACTTCATCAAGCGCAATTGATTCTGCGAAATCTCTAATGGAAATAAATGT
GCTTTTATGGCTGTCCCCCCCGTCTTACATAACAATTAAATAAAGGCCGGGCCAAAACTGAAAGACTTTCACCATCTGTCCAGGCACAAAAACAA
ACAAACTAACAAAACCGCATTTGTTTCATAAATTTTTCATTTTTAATTAAAACTGGTTTCGTCGGTTTCCAGTTGACCCAAAACATAGACTAGAT
TTCCCTACGCAGCCTCCATAACGACACAAAATCCAAATCAAAAGACATTTGCCCGATTTACAAATGAGCGATGCCGTTAGGTATTCGTATTCGTA
TTCATCTTGTGAGTGGGAATTCTTGGGGTACCCGTTTAAGCAGAAAACTCATGCGAATACCAGGAATTATTCACTGTTTGCGGCATGACTCATCG
CGTACACTTGTTGATGTCTCGGGCTCCATTCAGTTTCCTTACATAATTGCAAATCAGAGCGGTGGAAGCGTTTATTAGAAGAGCTAGACCACAAT
CTTGGCTTGGTGGCTGACTCATCGGTGAGGGAAAACGCTTCCTTCCCTCCAACCCACACCAAATTTCATCTTTGAGCTGCATTTTAAATTATTCA
GAAAATAAAGATTGAAAACCGGTTGCGTTGCGACATTCATCAGCATTCACCGTTCGACGGCACTGCACTTCCCAACTTTTGACCACGAAAGGCAC
AAAACCACAGCCAAAGATCCCCCTAATACATACATATAAAATAATAATTTAATTGTTCACCCCTATAAGTACAAAAGCTTATTCATATGGATGAT
TGAATTTAGCAAACAAAATGTTGTGTTAGAAGTCAAGTAATAAATACACTTTCCAACCAACCTATCAGTTCGCAAGAAGTAGATGATAACATTTA
GATAAGCAGTGAAAAGTGAAGAAAAGTACCAAATACACTGCAATTTCAAGCTAGTATAAAATTCACCAATATCTGGAATGCCTTGTAAGACGCGG
CAAATGCGTGAGTAATAAACATAAAACGCTTTCTTGGCACGCGATCCACAGATGCTGAACTTTGACTGGGGCACTTTGATGCCGGGGTCAACACA
ATTAAGCCCCCCATCATTGATGCGAGTGGCTTCAAGTTGGGGTTAAGTGCTATTCGCTTTTTTAGGTTCGCCATTTTTTGATTGATTTTGTAAAC
TTTTCCTAAAGCCTTGAATAGTTTAAATGTATTCCAACGATCAAGCTTCTGAACAAATTTTATTCCAATTCTGTATGAATGACGTTACCAAATTT
AAATCGGATGAGTTCGTTCCAGCAAAATGGCAGCAGAATCCCCAAATAGAAGCAGTGCTTTTTTTTCTCTACTTTTGTTGCCAAATTAGTAAACA
AATCCAAATGAACAATTGACCATTAGGTAGCCACTAGCGCAAAAATGGGCGAAAAAAAAATAAAGCGAACAAAAACACAAATTTGGCCAGAGAGC
AACAACGAAACTAAATAAACAGCACACTTTTGTTTTGGCCTCTTTGGACGCGTTTTAAATTATTATAAACAAACAGCTTTGGGTGCTGTTTTAGT
GACTACAGAAATGTGCAAATAATTAAGTCCCAATGCTACCGAATTCTTCTATTTATACAACCAGCTGATTAAGCAACACGTAGGAAGCAAACTCG
TGAATGAGTTTCCTCAGTTCCACGATGTAAACTTGTGGATTAAAAAACAGGTGTGCGAGCAATGGTCGAAACTTTCCAGGCATGCCACCAAGTGG
GTGGCAATACCCCCCTGCTACCCTGTACAATGCCGCATCATCATCATAACTTATGCCTTTCTATCAGTTCGGAAAACAGCGGAAACTCTTTATCA
AGCTCGCTGGCCGATGATGATGAAAATGAAACTGTATCGAGCGAGAGCGCGCGGCTCGTAATTAATACACATAATAAATTATTTAAACATAATTG CTGTGCATTTAATGCACTCCCTTGAAACATGAAGTGCACATGCCCGGCAGTCCGTGAACAACTTATTCCAGTTCATTGTTATCTACAGGCTTGGC
CTCTTGTAAACTTTTCATATCAAGTTACGAACTCGTCGTTCTCGGAATCTTGTCCCAAGAACAAGACTTGTCACATTTCACACTCTCTCTTTCTT
TGCATTGATTCGGTGGCGATGATTTCCCAAGATGAGGAAAGGTCTCAAAGCGACACATCTGCACTATGGCTACTCGTATTCATGTGCAATTCACT
TGGGTCACTCCAGTTCAAACCTCGTCTTGGAGGCGTCTCTTATCAGCCTCCTTAATAAATGGGTGCATGCATCAGTTGGATTCCCGTTCCCATAT
AGCAGACGGTCCACAAATAACTCAGTTACACAAAGGCGGAGTTAGTCAATAAGTGAATTATACGTATAGATGGATCATCCGACTACGCAATTAAT
TAAATAATTCCGCAATAACGAATGTGAAGCGACGTCAGTAGAATGTAGGTAATTCTTTTATATAACTAAGATTACTCGGCTTGAGTTTCTTAAGA
ATTTCGTTTTATTAGAACTTGCAGTGGAGCAGCAGTATAACTAATCGTACGCCCAAAACCAGATCGAATTGGTACTCCAAATCGTCTATATAGGT
AGGTACATTTCTATATAGACACCTATTTCTATTCTACACCAAAGCGAAAAAAAAACACTTTTATTCAACTCTGCTTCTTGTTGCGAAAAATATAC
GAACTGTATATGTGCATGTATTTTTATGGTTTCTCGCATGGGTTTTTGTATTTAATAAACTGATTAGATAAGATAGATGTCGGTGAATGCGGTGT
ACATAGGGAATTGGACTTGAAAGAGCAACGGCGATAAGTGGATGTGGAACCATGGCGAAAACCCATGGTTACCTGGTCAGAGGAGCCATCGAATC
CCCAGAATCAGATTGGATCCGGGCAGATTGCAAGGGCACGCGCTGCCAATTAGGTAAATTAATTGAGGTTAATGCGGAGTGTTTATTGTGCCATA
GGTCGCAATGAATTGATTAGCGACATTATGGATTGTATTGGATTGGGGCGACAGGCGATTCACGTACTCGGTTTCCTGCGACGTCCTCTAAATGG
CTGTGTAACCATATAATTGTTTGATAACTAAAAATGGTATCGAGCCCATTATGGTGGAGAATCAAGTCGCCTGCCAAGATCCCCGAAGAATAAGA
GAGCCCCACAACAGCGATTGGAATTGGAATTGGGACTGGAAGAGGAAGCGAGAGCAAGAGAGTTGGGATCGTAAACCGAAACAACTTGGCATTCC
AGAGCTGTGGACGGATGGGCGGTCGGATCGGGGGAGGTTTGGTGGGGGGGGGGGGGGGTGCGGTGACGTGAGCGCAATACAAAGTGACTCAGGT
GATGGTGAAAAAGGAGGAACGATCACGAAGATAACTCTCCCAGTGAGTGAGATCTATGCTAATAGTGTTTACAGCCAAAGATAAATGTTGTTATT
TTAACAGCTCGTGCAATCGCAGACCCACTGAGCGCCCACACCATCGCAAGGTCGTCGCAATTGGGTGTTATTGAATTCATTCTGCGCTGGATTCG
ACATTTGGCCAGCTAGCTGCTGGCGAGGATGAACTTAGTGGGATACGAGTGTTGCGTAGACGCTTTGAACTGGACGTACTTTTAGATACGGGACT
TGTGTGCCCGTACTTTTATCCGTATGCGTACTATTTGCAATAATCAATCGAACAACACGTCTGGCTGGCGATGACGTGCGACTTGATCGCAGTGT
GGATGTGGATTACTCGAACTGGCGGCGGCGAGAGTATAAAACCGGATAAACGAATAGCAACAACCGATCGCACGCGATGTCGTCGAACAACTGAA
CCTTTGGCGATTCCGATTCGTTTAGCTCGCAGAGTTCGAGTAGCTCGCAGATACGCGAAGAGCGAACGAAGAGAGCGCGGTGGAGCAGCTCTCTC
TCTTAGCACTTGGCACACAATGTTTCCTTATCAAAGGTTTCGGTTTGGATAAGAAGAATTTGGCGAACTACAGCTCCAGGTTTCTAATCCCTATA
AATATTTTTGCATTTCTTTTTGAGTAAATGATGTGATGTCTGCAATTCCAACTTAATGTTTCGTATTCAAGTTGATAACATTTTGGTTTGAATGC
TTATTTTTAGAATACAGAAGCTCAATGCTCATATAAGTACATAAATAAGCCCATGATTAAAAACCACCATAAATAAGTTCATAATGATAAATTAG
TTACTTCTATTTACGCATTTTCTACTACGAATAAAACGTTTGAATCAAACTTCGAAGTGCGTCAAATTATTAAGACTGAACTACTCACGCAATTA
CTTAACTGAGAACGCAAAATACTACTTTAAAGCTACTTGTGAGCTACAAATCCTGTTGCGTAATATCCCGCCCTGCAACCCGAGTATCTGGCATA
AGCCATTAATCAACGACATTCCGCAAGTGCGTGCCTCCAAACTGGGCTTTATATCTGTCCGATGTAGGGGTAATTAAGCCAAAGAACCGCCTTGC
GGGTTAGACCGAATAAAATGCGTTTACTGCGAGTATGTGGCACTGGCGTACATGAGTTCAATTAGCCGACACGTTGATGGGGCACTACATTAATT
AGAATTACCACTGCACTGGGCAAGTCACTGCCGTACAAAGAATAAAGGTCAAGTGACAAAGGCTTCGACCCAGACCCAAAAAGTCGGGCGGTCAC
AGCAAAGAGAAGAGCCGGAAAATTATTAATACACAAATATGAATGTGCAGCATTTCCAATTAGGGATAGCTACTTAAGCGAACACATGAGCAACA
TGTGTGCCACTACTGCAAACACCAAAGATACTTCTGGAAGACT
(SEQ ID NO: 1033)

Exon: 6358..6160
Exon: 1949..1665
Exon: 1587..1417
Exon: 1357..1001
Start ATG: 1910 (Reverse strand: CAT)

Transcript No. : CT26615
GTTCGACGACATCGCGTGCGATCGGTTGTTGCTATTCGTTTATCCGGTTTTATACTCTCGCCGCCGCCAGTTCGAGTAATCCACATCCACACTGC
GATCAAGTCGCACGTCATCGCCAGCCAGACGTGTTGTTCGATTGATTATTGCAAATAGTACGCATACGGATAAAAGTACGGGCACACAAGTCCCG
TATCTAAAATTCTTGCTTAACAAAGACGAACGGGGAAAAAAACCGGGAATGACGGCGAACATAACGAAGAGTCCGCGCCCGCTGAAAATAACCAT
CGTGGGCGATGGCATGGTGGGCAAAACCTGCATGCTGATAACCTACACACGGAACGAGTTCCCCGAGGAGTACATACCCACAGTGTTCGACAATC
ACGCCTGCAACATAGCCGTAGATGATCGGGACTACAATCTGACCCTCTGGGACACTGCCGGCCAGGAGGATTACGAAAGGCTGCGCCCCCTGAGC
TATCCCAGTACCAACTGCTTCCTGTTGTGCTATTCGATCAGCAGTAGGACCTCATTCGAAAACGTGAAAAGCAAGTGGTGGCCGGAGATCCGTCA
CTTCTCCGCCCACGTTCCCGTGGTTCTCGTGGGCACCAAACTGGACTTGCGCATTCCCAACTCGGAGAAGTTCGTGACCACACAGGAGGGAAAAA
AGATGCGCAAAGAGATACACGCATTCAACTTGGTCGAGTGCTCCGCCAAGAAGAAGCAGAACCTGCAGCAGGTCTTCGAGGAGGCGGTTAGAGCC
GTGGAGAGGAAACCAAAGACGACGTCCAAGCAATCGTGCAAAATACTGTGAACTATGTGTATGCCTAATTTTAAATATTGTTATTATGCGTAATG
TATTATGCTACTAATTCGCCTGACTATTTGTGCTTCGTTTTCGCAAAAGGGAAAAAAACTGTGTAGAAAATTTAAAGTTAAGTTTGTATAATTAA
GTGCCACTTGTGTGAATCCTTATGTTATATATGCAGCCAGAAGGCATTAATTGTAAAAAGAT
(SEQ ID NO: 1034)

Start ATG: 239 (Reverse strand: CAT)

MTANITKSPRPLKITIVGDGMVGKTCMLITYTRNEFPEEYIPTVFDNHACNIAVDDRDYNLTLWDTAGQEDYERLRPLSYPSTNCFLLCYSISSR
TSFENVKSKWWPEIRHFSAHVPVVLVGTKLDLRIPNSEKFVTTQEGKKMRKEIHAFNLVECSAKKKQNLQQVFEEAVRAVERKPKTTSKQSCKIL
*
(SEQ ID NO: 1035)

Classification: enzyme
Gene Symbol: RhoL
FlyBase ID: FBgn0014380

Celera Sequence No. : 142000013384474
CACCACCACCATCTCGCACAATGCGTCCGTATTGATCGCGCTGCTCGCCGTGATCCTCCTTGACCACCAGTTCGCGGCCATTCACCTCATAGCGG
TTCATTTTCTCCAAGGCCTTCTGTACGTTCTCCGGATCCTTGAACTCTACGATGCCACAGCCGCGAGCCTTGCCGCTCTCATCGAAGAACAGCTG
GACGTACTCAATGGAGCCGACGATGCGGCGGAACAGATCCTTCAGATCCTGCCAACGGTAGTCGTATGGAATGTTCGAAATGTAGACCCGGCAAT
TGCGACGTTCCCGGCTACGGTCGCGAGCAGCGACGCCACCTCCCTGACTACCAGCGCCGTTTCCATTGCCATCAGCGTCCGTGAAACGGGAGCCA
CGTGCTCCGCGTCCACGACGGTCGCGCTCCTTCTCGCGGCTCTCCACCGAGTTACTAGCGTCCATGCTCATTGTTGTCTGCAAGGGATTCGCAAT GCGTTTTGTAGTTCTTGCAATATTCGTAGTAGTACACACCCGGAGCGGCGTCCGCGAAAACAAAATGGCGACCGCGTCAATCGACTTTTTCGCCA
AATGTTCTTTTCTATGCTAGCGTTATGGCTTACCTTTTGATGTTGGCTGTGCTCTTAATACTGGTAATATTTCTATTTGCTGCTTTCGGCGTAG
TAAATTTTATACAATGAACAAACGCTTGTGACAAACTACAGTTTCCGAGATCAATAGAAAACCGTACAAAAGTCTATGTTAGAGTTGACAGTGAT
ACGATGACAGCACATTCATCGATGGTTTGATATTTGGACGTGTCTCAGATTTCTATCGACTAGACATCGCCGATATTCGAAAATGCTCTTCGAAT
TATCGAAATGTAGGCATACTGCAATTTACGCGCGCAACGCAAAAATTCAAATAATAGAATATTTGGCTCAACAAGACAGGAGACTTTAGATGGAA
AAATAGAATCCACAAAAGCAAAACTATGGAATAACTAAAACCACTTTTCATAAATAGTACACACAATCGATTTATTTCGTTTCTTTTTGTATGGC
AAAAATTAATACAAAAAATTAAATATTAAATGTATGTATGTATGTATAAAAAGCTTAAAGCAAACTATATAATGTAAATTTAATTGGCTGTTTGT
TTTCTCTCCGATTGATCTGTCAGTATGGTAAGTAGAAAGAAAGGCAAATCTCAAGAACTCATACGGATTATAATTTCATCATCGTAGCACCACAG
ATATGTGTTTAACCGAACATAAATCTAGTTTGGGGCTAGCGAATTTACTCGTTTGTGCGAAAGTTGCTGTGAGCTTATCGGCTTTTGCTTGTTTG
TTCTCTAATGATGAATACTAATGGAATTCTGCTCGTGCGTGTGTGCGAAAAAAGATTACATTTATGTATGACTGTCGGGTTGAAACCAATAGATA
ACAGGGCTGTAAAAATACACAATATTTGTTTACATCGCGTTTCGGTTTTAAGCACGGAGTATCTGTTGAAGTACAAACAACATAGAATCAAGTTA
AGTGCTGGTTGAAAACAAACGGATATAGCAGCTGAACCAAGGCAGTTACAACAGTATTCATAGTTTTTATGTAGAGGTACATATTCATTTTCATT
TTCGATTTGCTTCGTTCGTTTTTGTTTGCTTGTTATTGTTAATACTCTTAAAAGGGCGCCTCGCAGCCTTTCAAACGACACAAAACACACACATT
CACAAAATCATTTCGACGTACATAAAACTCTAGTTACTTAAATTAATTACAATTTCTCTTCTTTTATCTGACAATTGCACCGACCAACACGCTCC
CACATGTGTGTGTTTTTCGCATTGTGTGTCCAAAATGGACAAACCATCGAGCCCAGGACGATCGGCGATTCGCCGACGCACATACAGACAAACAG
GCGACATTTGAAGAAATAAAAAGTGAATAATAACCAATGCGTGGCCGTTTAGAGCATTTTACATTTAAATCTACGATTCGGCTTGTTCATTTTGC
GGCCCCTCCGCCCCTTGTTGTCCTTGTCCTTGCGGATTTCGCGCACCAGTGTGTAAAATGCATCGTCCACGCCCATGCGCGTCTTGGCGGATGTC
TCAATGTATGGAATGCCGTACTGTTTGGCCACCTGAGAACAACCATAATTAACGGAATGTTCGCTCGGAACTCTGAAGGCCGGTACTCACCTCTC
TTGCCTGCTCGTTGTTAACGTTCCACGAGGCCAGATCACATTTGTTGCCCACCAGCACCATGGGCACCTCTTCGGCATCCTTTACGCGCTTGATC
TGCTCACGGTAGGTGCCGATATCCTCGAAGGACTTCGCACTGTTGACGGCAAAGACCAGCAGGAATCCCTCGCCAGTCCGCATATACTGATCCCG
CATGGCCGAGTACTCCTCTTGGCCGGCGGTGTCCAGGATGTCCAGCAGGCAGGTCTCTCCATCTGCAGGGGAATATAAAATGCATTTGAATATCG
CAACTTCTTAAGGTCTCTTCTAGTATAAACGGGAAACCAAACCAGCGAAAGGGTGCAGAAATCTCTAGAGTATTTGGACCTGTGCAGCCCTAGCT
TTGCCAGATCTAAGTACATATAACTCACCGATAACCACTTGCTTTCGGTAAGAGTCCTCGATTGTGGGGTCGTACTCGTCCACGAAATGGTTCTG
GATTAGCTGGATGGTGAGCGCGGACTTGCCCACGCCTCCGGCTCCAACGACGACCAGTTTGTATTCCGTCATTTGGCTGTGGCGTCCGTTTTCGA
TTTGCCGTAGTCAAATGTCACAGTAACAGTCTCTTTCTCGCGATCGATGCTTACTCTCTTGTGAAGCGCCCGCAGATGCAGTCTCTCTCTCCGTA
CGCTTGTTGCGTGTGTTTGTGTGGGTGACTGTGCGTGTATGGGCTGCAAGTGGAGTAAATTATTAATTAAGATTGATTAAAATAAATTAAACGCA
TAATTAGGCAGGAATTAATGCACGTCACTGAGTCACTGTGACTAGGCGCTTACTCGCACAAACACACACGCACCACTGCATGCACACAGCCAGAC
GGGCAACACAAAAAAAAATGGGAAAAAGAGATCAATGACTCAAACTAAAATTAAAACCCATTCGCTCAATGCAAATTAGTTAGTCTCCCCCATAG
CCGAGTTGTTAACTAGGTGAATTTGCTAATTCGGCGGCGTTGTTTTTAGCCCTTTTCTTTATTATTTTTCTTTTGCCTGCCGGGGCTGCGGACCT
TCTTTGTTGCTGCCTCTTCAGCTAGCTCCTCCTTGTTTTTCCGCTCCGCTCCTCTCTATCAATACTCTGCCTCTCTCTTCTCGCGCGCGGCGCAG
TTGCTGGGCACGTTTCACGTCACTTTCGCGGCTAACGGTGCGACAGGCGGTACTCCTCGATGGCACCAATTTAATTGCCGTGCGGTAATTGCAAT
TAACAGCGCAGGAAAACAATAAATCCGTATGTGAAATGAAGATGAAATCTAGGCTGTACGTAGCTGTGAAGATACTAGAGCTGGCACCAAGCCGA
TGGCACTATCGATAGCGATGGCTGCATTCTGGCCGGCACCATCGATGGACTTGCAATAGCGATTGCTATATGAAAACTAATCTAAAGAGGTGGAT
GCACTTCAGTCGACTCTCTATAATTTGCTTAAACTAATAAATGATTTGATCAATACAGCTTTCTGTAAAAACTGGCAGACGCTTTCTGCTTTTAA
TAATTGTTAATTTAAGTTCAACGGGCTGGCATCACCGTTTCTTAGCACGGACTCAAGCCTGAGTCTATTATTTCAACCACCACTGTAACGAAAAC
AGCATGGACAGATTGAAATTCAATAATTTGGTAAATAAACGATTTTATTTAAAATTATAGAGTTTTAATTAAAAAGAACTTTTACAGGTGATATC
CAACAAGAAGGTCATTCAAAAGGCACGCGCCCAGACCATCGCCAAAATCGTACAAAAGCTGCGAAAGACAAAAGAGGCTCTGGCCAAAAATCCAG
ACAGTGAAAAGGAAAAGATTCGTTTACGCAAGAACACAGAATGCCTGGCCCAGTTGAAGGCTCTAAAATATATGGATATGGTACGCCAGTCGCTC
CTGCAGGAGGGCACAAATCCCAATGCGGTGATTGCTAACGAGCGCTCCACGCCGGATGAACTGGGCATTGCCATGCTGCGGCTAAACAAATTGAT
GCACGGACTGGTGGACAAGTTTGTGGAAACCTTGAAGCTGAGCACCACCGATAAGGAGGCCAAGTGGCGTGAGGAGATCCTAGAGACGAGCAAGC
GAAGGGCCAAAATAGAACGCACTGAGGAGCGGAAGAGGAAGCGCAAGGAGCTGAAGGAGCAGAAGGCCCAAACCAAAAACCGACTGGAGTGGTTA
GAGCAGAACAAAGTGGTGGATGCAGATGTTAATGGAGCAACTGCGGAAACGCCCACTCTTCAAGTCAGCAAAGTAAATGATCAGGAAATACCACA
GTCTTTTGCAAAAACTG
(SEQ ID NO: 1036)

Exon: 3482..3229
Exon: 2893..2594
Exon: 2437..2181
Exon: 2122..1001
Start ATG: 2732 (Reverse strand: CAT)

Transcript No. : CT26623
TACGTACAGCCTAGATTTCATCTTCATTTCACATACGGATTTATTGTTTTCCTGCGCTGTTAATTGCAATTACCGCACGGCAATTAAATTGGTGC
CATCGAGGAGTACCGCCTGTCGCACCGTTAGCCGCGAAAGTGACGTGAAACGTGCCCAGCAACTGCGCCGCGCGCGAGAAGAGAGAGGCAGAGTA
TTGATAGAGAGGAGCGGAGCGGAAAAACAAGGAGGAGCTAGCTGAAGAGGCAGCAACAAAGAAGCCCATACACGCACAGTCACCCACACAAACAC
ACGCAACAAGCGTACGGAGAGAGAGACTGCATCTGCGGGCGCTTCACAAGAGAGTAAGCATCGATCGCGAGAAAGAGACTGTTACTGTGACATTT
GACTACGGCAAATCGAAAACGGACGCCACAGCCAAATGACGGAATACAAACTGGTCGTCGTTGGAGCCGGAGGCGTGGGCAAGTCCGCGCTCACC
ATCCAGCTAATCCAGAACCATTTCGTGGACGAGTACGACCCCACAATCGAGGACTCTTACCGAAAGCAAGTGGTTATCGATGGAGAGACCTGCCT
GCTGGACATCCTGGACACCGCCGGCCAAGAGGAGTACTCGGCCATGCGGGATCAGTATATGCGGACTGGCGAGGGATTCCTGCTGGTCTTTGCCG
TCAACAGTGCGAAGTCCTTCGAGGATATCGGCACCTACCGTGAGCAGATCAAGCGCGTAAAGGATGCCGAAGAGGTGCCCATGGTGCTGGTGGGC
AACAAATGTGATCTGGCCTCGTGGAACGTTAACAACGAGCAGGCAAGAGAGGTGGCCAAACAGTACGGCATTCCATACATTGAGACATCCGCCAA
GACGCGCATGGGCGTGGACGATGCATTTTACACACTGGTGCGCGAAATCCGCAAGGACAAGGACAACAAGGGGCGGAGGGGCCGCAAAATGAACA
AGCCGAATCGTAGATTTAAATGTAAAATGCTCTAAACGGCCACGCATTGGTTATTATTCACTTTTTATTTCTTCAAATGTCGCCTGTTTGTCTGT
ATGTGCGTCGGCGAATCGCCGATCGTCCTGGGCTCGATGGTTTGTCCATTTTGGACACACAATGCGAAAAACACACACATGTGGGAGCGTGTTGG
TCGGTGCAATTGTCAGATAAAAGAAGAGAAATTGTAATTAATTTAAGTAACTAGAGTTTTATGTACGTCGAAATGATTTTGTGAATGTGTGTGTT
TTGTGTCGTTTGAAAGGCTGCGAGGCGCCCTTTTAAGAGTATTAACAATAACAAGCAAACAAAAACGAACGAAGCAAATCGAAAATGAAAATGAA
TATGTACCTCTACATAAAAACTATGAATACTGTTGTAACTGCCTTGGTTCAGCTGCTATATCCGTTTGTTTTCAACCAGCACTTAACTTGATTCT
ATGTTGTTTGTACTTCAACAGATACTCCGTGCTTAAAACCGAAACGCGATGTAAACAAATATTGTGTATTTTTACAGCCCTGTTATCTATTGGTT
TCAACCCGACAGTCATACATAAATGTAATCTTTTTTCGCACACACGCACGAGCAGAATTCCATTAGTATTCATCATTAGAGAACAAACAAGCAAA
AGCCGATAAGCTCACAGCAACTTTCGCACAAACGAGTAAATTCGCTAGCCCCAAACTAGATTTATGTTCGGTTAAACACATATCTGTGGTGCTAC
GATGATGAAATTATAATCCGTATGAGTTCTTGAGATTTGCCTTTCTTTCTACTTACCATACTGACAGATCAATCGGAGAGAAAACAAACAGCCAA TTAAATTTACATTATATAGTTTGCTTTAAGCTTTTTATACATACATACATACATTTAATATTTAATTTTTTGTATTAATTTTTGCCATACAAAAA
GAAACGAAATAAATCGATTGTGTGTACTATTTA
(SEQ ID NO: 1037)

Start ATG: 416 (Reverse strand: CAT)

MTEYKLVVVGAGGVGKSALTIQLIQNHFVDEYDPTIEDSYRKQVVIDGETCLLDILDTAGQEEYSAMRDQYMRTGEGFLLVFAVNSAKSFEDIGT
YREQIKRVKDAEEVPMVLVGNKCDLASWNVNNEQAREVAKQYGIPYIETSAKTRMGVDDAFYTLVREIRKDKDNKGRRGRKMNKPNRRFKCKML*
(SEQ ID NO: 1038)

Classification: signal_transduction
Gene Symbol: Ras85D
FlyBase ID: FBgn0003205

Celera Sequence No. : 142000013384590
GTTTGGCTTGCGTATTTCCGGCATTTCTGTATTTCTCGAAAATAACATCTTTTCTTTTTGTAAGATGATAAAAAGGTTAGGATGTTAAAGGTGGT
CGTGGTCCCACGATGAAAGAAGACATTTTTATTAGTAGTTTATAATTCGTATATTTATTTCGATAATACACCTATTATGAATACAGTTCGCATCT
TTGATTGTTTGTATTAATTTGCTTTGGTACAGTTAGGGACTTTTTCTTATCAGTATGCTATTTATTAAAAGTAATGAAAAACTTGTTACGATACT
TTAGATTTGGATAAAAACCAGAATTAATTATAACAGACATTCTAAAAAAATAATCACTGATACATACATACGTTTTAAAAGATTGCATTCGTATA
AATATTCGAGCATTAGAAGTAGAATACTGTCGGAATGGAATTAGTCGAATTAACATACAGATAAGGAAACGTCCCTAATGACTATACTAATACAA
AGTTCAGTGGAGATTTCGCTCTTTTCAAGGGCGCCTCAAACATTGTTCCTAACACTCTGGTCAGAATTCAACAATAAAATTAGAGAATACATTTG
AAAACAAACAAATAATTGATTCAAATAATGTTCAGCAATTACGATACGTTAAATTTGTCGTTTTCAAAGTGAATGCTTTGGTTTCTTATATTTTT
CGGTGTTTGGTTTCGCTTTTATAAAGGACAACTCGAACTACGGAACAATCTGAGGCTGGCTGCTTCCATCGTGGCTAACTATTAGCATGTGTACT
AACTGGTGAATAGCTGCGCTATGCTCCCACATACAACATCAACCATACCCATAACAACGCGCTTACATATCTTTGGCGAGTGACCACTACGTTCA
ATTGAATCGAAAAAAGGGAAGAGACTTGTGATGTGTGTAACGTATACAATGTCAAAGAGCTACAGTTAGAGAGTGTTTTTCGTGTGTGGTTTTCT
TAAAACGACGACAGATTTTGTGTTTGACCCTTCCGAACCAGTCCGAGGTCCTAAACAACCACTGCTCCTGCCTCCGAACGGCTAACTGGTAGATC
GGGACAATTCTTCCAGGTGTCCGAAAGCGGATCATAACATTCGACAGCATTGATAGTCACTTGGGCTCGGTAGAAGTTTACCTCGCAGGGCTGGC
AGAGAAGCATACAAAAACAATGATTAAATTATGAATCAAATAAATTGAAATATACTTGTTACCTGATCACCGCCAGCTACGTAGAGCAAGCCATC
GGCGGCGACCACGGCAGGAATGGCTCTGGGCACGTTTAATGCACACACTGTAGTCCACTTATCCTCGTCGAAGCTGTAGCGTTCCACGGAGCTGA
GAATGTCCTGACTGATGCTACTGCCTCCAACCACATACAAGTAGCGATCCAGAACGGCCACACCCATTTGACAGCGAGCTGTTTGCATGCGGGCC
AGCTCGTTCCACTCTTTTGTCACTGGATTGAAGCTGCAATGGATTTTTATAAAAATATATAACTACGAATATAAATATTTTTTGTTAAATACCTG
ATTAAATCCGGCAGATGACGGGTTGTTGTTGTGCAGCCACCGACAATGTAAATGAGACCCTCGAAACTGACCACACCCATGCTGAATCTAGGCTG
CGGCATGCTGCCCATTAATTTCCAGAGATCCTGCTCCGGATCATAGCACTCCATGGAGCCGCCGATGTCGTCGCCTATCCAACCGCCTACGGCAA
ACAGATTTCCGCCCATGGTGCAAAGACCGAACTCGCAGCGCGGCACAATCATCGGGGCAATCGGTTGCCAAACATCGTTCTGTGGATCATAGACC
TCGCCATTGGCCAGAATCTGTGAACCGCGCTCTCCTCCTACCACATAGATCTTGCCATTCAATGCTGATACACCTGGCAGGATGCGTCCCACCTC
CATAGGCGCCGTTTCCGTCCACTCGCGCCGGAATATATCGAATTTGGCCACCGTCTCGAAGATGCAGTCGGCCGAGTTCCAGGTTCGCGGCGTAT
CCCGATGAGATCCACCAATGATATATATGTTCTTCTTGGCCAGCTGACGCGGACATACCCGCAGCGGCACCAATTGTCCGCGCTTGGACGCAATG
TCCCGGCAAATGGAGCGCAGGGCTATCTTCACGGACATGTCGCGACAGTCGTCCTTCAGAGCCTTGTCGATCACCTTTACCGGAACAAGCGCCAT
GCGCACGTGGGACAGGACATCGAAGACGTAGCAGCGGCGCTGCGTCACGTCGTGCTTAATCCAACGAAGCGCCGCCTGGAACACCTGCGACTCGG
AGTCTACACGCAGCAGCTCCGAGTTCAGTAGCTGCGAGAGTAGAGTTTGTGGCGTTTCTAGGAACTCATCTTCAAGCGTTACCTGAACGAAGAAA
GGAAAGTACCAATCAGTTAAAATAGAAATATATATTTTTGCCAAATGCTCAAATTTAAACGATAAATTATTAGGTTCAAGGCAGAAATGAAAATA
ACTTTAAATATTATTATTTTGATATTTTTTATCGTTTATCTCGTTGAATATTTTCGTTTCCAATAAATATAGAACATTGCTTGACTATTTCCATG
ACCCACTTTTCGTTTGGGCGGTACACCTACAAATCAAGCCTTTCAAGTGCATCCAACTCACCGCTGGGAAATTCGCGTGGACAAAGTTCAGTGCA
CTCTTGGCCAACGACTCGCAGTTGTGGGCCTCGGCGAAGCGTAAAATGCCCAGGGCATTGGAGGCGTGCAGCTCGCGGCAGAGGAACTCGCAGCA
CCCGTCGACCACCTCGTTTAGCTGCAGCATGTCGGCGGCGGCCAGGAGCTCCTGGACATTGGACTGTAAGATCAAAGAAGGGATTAGAATTTGGA
GACCAAGCGACTAGGTGTATGGACTCACCTGGGTGATTTCGCAGCGACCCGTATAGATGAAGTCAAGCAGGATGTGCAGGATATCGCCGTCGATT
GTGTGCAGCACAACGGATTTTTGCTTGACCTCATTTAACCCGAGCTCGGGTCGAAACATGGCCTCGAAGTAGGCACTGGCTGCACTCAGGACAGC
CCGGTGGGCACTCAATGTTGCCATTCCGGCGATGATCTCCACGTCGCAGAAACGGGACTGCTCGCGCAGTTGGTTGAGATTGGAAAGCACCTTGA
ACGGATATTGGGCGTTGCAGTAGGAGGGCAGGTTTGTGCGATGGCTGGCCGCTGTGGCTCCAGATCCCAGATTTTGGCCAAAGAAGTCACCGTCG
CCGCCGCCGCCGGTGGGATTCTGATTGGCGTTCTGATTGGCATTCGCATTCGGACTGGTATTGCCATTGTATTCGTGTATCTGGTATGTTTTCAA
CGGTGGCATTTCGTCAACTGTTGGGTTTTTACTTTTCGGCGATCTTGAATCCGATATCGCCTTAATAAATGCACTTTTCGGGGGCGACAGCACAG
CTCAGACTCTTCGCATTCAATTGTTTGGCTTAATTAAACTTAATTGCTGCACTCTGCGCTCACTTCACCCTTTGTTGTTGCTGCTGCTGCTGTTG
TTGTTGTCGCAGTCCGTTTATTTTTCTCCAATCAAAAGGCGAGCACACACACCCACACACGCAATACAAACGACTGCAGGCAAAAGGTTAGCATA
TCACAAATTAAAACAACCGAAGTCCGCTACTAAGACAGCTATTTCCCCATTAAGATGAAATAGTGTTTTTAATATTTACAAACTGGCATATTTCT
TTGACTTTTCAATGCACTTTAGTATGTAGCTGGAACTGGAGTCGATGTTTTTGGGCGACTATCGATGTTGATAGAAGTTGCACTATGCCTGAATA
TCGATAAGTTCAGTTTTTATCCAGAACTTATTGATAGTAATCGCTGCTATCATCTTTGGTCCACCTCTTGTTGTTATTTAATTATTTGTATTTTA
TTTTCAATGAATTTTCAATGAAAAGCTGACAAAATGATATCGCGCAAACTACTAAACCTTCGACTGGGTTACCTGGCACGCCGTTGGGCCAGCAC
GGATCCGCTGAGCATTCAGAACGAGAAGCTGCAGGCTTATTTGGAGTCTCTACGCCAGGAATACTACGCCGTGCGAGTCAACGCCGCCGGAAACA
GCAAATCCTACGCCCGTCTCGCCCAGCTGGAGGGCGTGGTCAGTGCCCTGGAGCAGCGACGCGTACTAGAACGGCACATCACCAGCGCCAAGGAC
ATGGAAGCGGAGAAGGACGAGGATATGCGTGAGCTAATGCGCGAGGAGAACGAAGTCTATGTGGATCTACTGGGCAAGCAGGATCAGGCCTTACT
GCAGGAGCTGCTTACGCTCTCTGACGATGAGGAGTATCCGGCTCTGATCTTCGGCCTGAATGCCGGCGCCGGTGGCCAGGAGGCAATGCTATTCG
CCCAAGAATTGTACGAAATGTACACCGGCTATTTCGAGCACATGGGCTGGGAGTGGGAGGAGTTTGCCAGCGAGGGCACCGACATCGGGGGTCTG
CGGCACGCTAGTCTGATGGTGAGCGGCGAGGATGCCTTCCGCTGGCTGCGCTATGAGGCTGGAGTTCACCGCGTACAGCGGGTGCCGGCCACTGA
AAAGTCTGGACGCATGCACACCAGCACCGCCTCAATTACAGTGATTCCCCGACCCGCCGACATCCAAGTGCACATCGCTGAGAAGGATCTGAAGA
TCGAGACGAAGCGAGCGAGTGGAGCTGGTGGACAGCATGTTAACACCACCGACTCGGCTGTAAGAATTGTTCATCTGCCCACGGGTCTGGCGGTG
(SEQ ID NO: 1039)

Exon: 3750..2879
Exon: 2818..2627
Exon: 2362..1518

FIGURE SHEET 564

Exon: 1458..1203
Exon: 1135..1001
Start ATG: 3334 (Reverse strand: CAT)

Transcript No. : CT26720
TCGACTCCAGTTCCAGCTACATACTAAAGTGCATTGAAAAGTCAAAGAAATATGCCAGTTTGTAAATATTAAAAACACTATTTCATCTTAATGGG
GAAATAGCTGTCTTAGTAGCGGACTTCGGTTGTTTTAATTTGTGATATGCTAACCTTTTGCCTGCAGTCGTTTGTATTGCGTGTGTGGGTGTGTG
TGCTCGCCTTTTGATTGGAGAAAAATAAACGGACTGCGACAACAACAACAGCAGCAGCAGCAACAACAAAGGGTGAAGTGAGCGCAGAGTGCAGC
AATTAAGTTTAATTAAGCCAAACAATTGAATGCGAAGAGTCTGAGCTGTGCTGTCGCCCCCGAAAAGTGCATTTATTAAGGCGATATCGGATTCA
AGATCGCCGAAAAGTAAAAACCCAACAGTTGACGAAATGCCACCGTTGAAAACATACCAGATACACGAATACAATGGCAATACCAGTCCGAATGC
GAATGCCAATCAGAACGCCAATCAGAATCCCACCGGCGGCGGCGGCGACGGTGACTTCTTTGGCCAAAATCTGGGATCTGGAGCCACAGCGGCCA
GCCATCGCACAAACCTGCCCTCCTACTGCAACGCCCAATATCCGTTCAAGGTGCTTTCCAATCTCAACCAACTGCGCGAGCAGTCCCGTTTCTGC
GACGTGGAGATCATCGCCGGAATGGCAACATTGAGTGCCCACCGGGCTGTCCTGAGTGCAGCCAGTGCCTACTTCGAGGCCATGTTTCGACCCGA
GCTCGGGTTAAATGAGGTCAAGCAAAAATCCGTTGTGCTGCACACAATCGACGGCGATATCCTGCACATCCTGCTTGACTTCATCTATACGGGTC
GCTGCGAAATCACCCAGTCCAATGTCCAGGAGCTCCTGGCCGCCGCCGACATGCTGCAGCTAAACGAGGTGGTCGACGGGTGCTGCGAGTTCCTC
TGCCGCGAGCTGCACGCCTCCAATGCCCTGGGCATTTTACGCTTCGCCGAGGCCCACAACTGCGAGTCGTTGGCCAAGAGTGCACTGAACTTTGT
CCACGCGAATTTCCCAGCGGTAACGCTTGAAGATGAGTTCCTAGAAACGCCACAAACTCTACTCTCGCAGCTACTGAACTCGGAGCTGCTGCGTG
TAGACTCCGAGTCGCAGGTGTTCCAGGCGGCGCTTCGTTGGATTAAGCACGACGTGACGCAGCGCCGCTGCTACGTCTTCGATGTCCTGTCCCAC
GTGCGCATGGCGCTTGTTCCGGTAAAGGTGATCGACAAGGCTCTGAAGGACGACTGTCGCGACATGTCCGTGAAGATAGCCCTGCGCTCCATTTG
CCGGGACATTGCGTCCAAGCGCGGACAATTGGTGCCGCTGCGGGTATGTCCGCGTCAGCTGGCCAAGAAGAACATATATATCATTGGTGGATCTC
ATCGGGATACGCCGCGAACCTGGAACTCGGCCGACTGCATCTTCGAGACGGTGGCCAAATTCGATATATTCCGGCGCGAGTGGACGGAAACGGCG
CCTATGGAGGTGGGACGCATCCTGCCAGGTGTATCAGCATTGAATGGCAAGATCTATGTGGTAGGAGGAGAGCGCGGTTCACAGATTCTGGCCAA
TGGCGAGGTCTATGATCCACAGAACGATGTTTGGCAACCGATTGCCCCGATGATTGTGCCGCGCTGCGAGTTCGGTCTTTGCACCATGGGCGGAA
ATCTGTTTGCCGTAGGCGGTTGGATAGGCGACGACATCGGCGGCTCCATGGAGTGCTATGATCCGGAGCAGGATCTCTGGAAATTAATGGGCAGC
ATGCCGCAGCCTAGATTCAGCATGGGTGTGGTCAGTTTCGAGGGTCTCATTTACATTGTCGGTGGCTGCACAACAACAACCCGTCATCTGCCGGA
TTTAATCAGCTTCAATCCAGTGACAAAAGAGTGGAACGAGCTGGCCCGCATGCAAACAGCTCGCTGTCAAATGGGTGTGGCCGTTCTGGATCGCT
ACTTGTATGTGGTTGGAGGCAGTAGCATCAGTCAGGACATTCTCAGCTCCGTGGAACGCTACAGCTTCGACGAGGATAAGTGGACTACAGTGTGT
GCATTAAACGTGCCCAGAGCCATTCCTGCCGTGGTCGCCGCCGATGGCTTGCTCTACGTAGCTGGCGGTGATCAGCCCTGCGAGGTAAACTTCTA
CCGAGCCCAAGTGACTATCAATGCTGTCGAATGTTATGATCCGCTTTCGGACACCTGGAAGAATTGTCCCGATCTACCAGTTAGCCGTTCGGAGG
CAGGAGCAGTGGTTGTTTAG
(SEQ ID NO: 1040)

Start ATG: 417 (Reverse strand: CAT)

MPPLKTYQIHEYNGNTSPNANANQNANQNPTGGGGDGDFFGQNLGSGATAASHRTNLPSYCNAQYPFKVLSNLNQLREQSRFCDVEIIAGMATLS
AHRAVLSAASAYFEAMFRPELGLNEVKQKSVVLHTIDGDILHILLDFIYTGRCEITQSNVQELLAAADMLQLNEVVDGCCEFLCRELHASNALGI
LRFAEAHNCESLAKSALNFVHANFPAVTLEDEFLETPQTLLSQLLNSELLRVDSESQVFQAALRWIKHDVTQRRCYVFDVLSHVRMALVPVKVID
KALKDDCRDMSVKIALRSICRDIASKRGQLVPLRVCPRQLAKKNIYIIGGSHRDTPRTWNSADCIFETVAKFDIFRREWTETAPMEVGRILPGVS
ALNGKIYVVGGERGSQILANGEVYDPQNDVWQPIAPMIVPRCEFGLCTMGGNLFAVGGWIGDDIGGSMECYDPEQDLWKLMGSMPQPRFSMGVVS
FEGLIYIVGGCTTTTRHLPDLISFNPVTKEWNELARMQTARCQMGVAVLDRYLYVVGGSSISQDILSSVERYSFDEDKWTTVCALNVPRAIPAVV
AADGLLYVAGGDQPCEVNFYRAQVTINAVECYDPLSDTWKNCPDLPVSRSEAGAVVV*
(SEQ ID NO: 1041)

Name: KELCH RELATIVE
Classification: actin_binding

Celera Sequence No. : 142000013384252
TGGATAGTGTAGCGGATGCTACAGAAATGTTCTTGTGAATTCACACACTTGCCATGTGAGTGTGGCTATAGTTAGTTGTTTCAGAATTAAGCAAA
AATAACAGCAGCAGCAAGAACAGCGAAAAATCATTTTGTTGGCCCACCAACTGCTTGAGTTTTCTATTTTTAACACTAAAATTGTAGGTGGCTGT
GTCGGAAAGAGACGGATGGCCACGAATACTTTGTTGTTGGCCAACACATCACCGTGTGTGTATGTATGTACGTTGTACATATATATGTACATATG
TATGCCACATCTGCAAGTATTGAATTTATGCTTTTTTATAGGTAAATTCCTTCCTTTCTCCAAAATTCACACAAATTCGAATATCGTCTCCGGGG
AAAATCTCCCACGCTCGACAATTTCTATATTGTGATCCAACTTCAATAGATCAGTGCGAATCCCCAATTTTCATCCTGCTATCCACCGGCTTGTC
CAAATCACAGGGTTAGGGATTGGGTTGTGATTCGTGGTGTGGCGGATGAGAAGTTTTGTGGGGGGGGGTTATAGAGAAGAAGACGTCGTGCCGA
CAAAAACATAATCTGGCGCCGAGCCCAGACATTCATCTGCATTGCTTCTGTTGTTGTAATGTTTATTATTATACGTATACGTAATATGTGTGTCT
GCCTTGGTCGATAGCGAACGCGAAAATGAGAGATCTTGTTTTTTTAAAAAATTACTAAGAATTACTACTCGTACAGTGGTGATTGTATATATTTA
AGGTTGTGTCCTTTACCTAGGCCATCGACGTTAACTGGTCAGCAGGAGAGCTTAAGTAAAGATTGAATAAAATTGGTTTGGCCCACGCTAATTGG
TGCATTGTAAACTGGAATCTGAATCCCTAGCGTTCGATTTTAGCAAGCACCAACACACACTGGATTTTTCGGTTATTTGGGTTATGCAGTCAATA
AGGAAATACATATTTACATATCGAATTGCGGCATTGCGGAATAATCTTTTCATTTCAACTTTGGTATTACTGGAATCAGGAAAATTATGGTGGA
ATAAGGGTAAAACATTGTCAATGAATTAATTTGGGGGAAACAAAGTTTCAAAGTAGGTAATTATAAGGAGAGTGCAAGATAGAAGGTTCCCAGTA
CTGTTCACGGAAAACTTACCCATAACCCTGGGCGGGCATGTTTCATGATCTGGACCTGCAGTCGTTTGATAGAATAGATATTGGATTGATAAATT
GTCCTTTTGCATTTTGGCTCAAAGAGGGTTCGAAACACCGCCGGAAGAGAAATTATTATTATATATAGATAGCTATATTAAATGTTAAGTATGCC
GCCACTTAGCTTCGGTTAGTTACAAGTAGTATACGTATTTATAGATAGAGTACAGACATACGCAAAAGATATTGATTTATGGAATAGAATGTACA
GAATAGGTAGTTTTGAAAGTAGTTCTAGTACCTAGCTGTATGATTTTTAGTCACAAGAGAGCTAAACTGTTTGTGTTCGCTAAAAACTGCAACTG
CTTTGAAAAAGAATATCATCATTTCAAGTGTCCGACACTAGAGTGTTCGGAGTGCTAAACGTTTGAAGAACTATGTATGTGCTACGGTTAAGTCA
TTCACACTTACAGAACAGAACGGCTACGAAGTCGGTGTCCTCGATGATCTTCTGCAATATCTTGGCATTGACCTCCTCGATGCGATCGGGCAAGT
CCATGGCCTCCAAGGAGGTGAGGAAATCGAGCACTCCTTCCTCGTCCATGAGATCCCCATCATATATGATGGGCTCCTTTTCCCTGCGGTTTTCG
AGATATGGATTCGATTCGATTAGGTCTTGTGTCTTGTTTGTGGTGGGGGAATTACCTACCTGAAGTAGGTGAGGGCGGGGAAGTTCTTGATGCCA
TACTGTTTGGCTAGTCGTTTGTCGTTGATTTTCACGAAGTCCACACCGAAGGAGTCGGTGTCATCGTCGATTTTCTCGAGTTCCGCTAAAACCTT
ATCACAGGTCACGCAGCTTCGCGCATCTGAAATCGTAGAAGCCGAGCGTGTGAGTACTAAAGATCGATTATATGTAGATACCGGCAGCGATTGAC
AGTCGGCAACTGCTGCATGTGACGCCACAAGAGACCATAACTAAATTCCCATTCGAATTGAAAGCCCAAAGCCCAAAGCCCTGGCAGAAGTGGAG CCAAATGCCGCAAAGATTATTCATTCCTATATAGTAGATGCAGGATGCATCATCGGACCGCGCAATCGAAAATAAGCCTGAATGAATGAATGAAA
TGACAGCAGCGCCAGGCCAATTCTGTGCTATTAATGCGGCAGCAACTGCCAACAAATATGCTGAAATTCTAAATTAATTCATAAAATTCATGCGG
CCACTATTAGGGAAATGAATTGCAGCCCACAAAAGACCACCGTTGGCCCACGTCTCTACAAACGTTCTGGTTGGTTAAACGGCAGACCAGACTGC
AAAATCGGAATCATTAATACATCGCCGAGTAAACAGCCATTTCGATTGTTTGGCAATCCGTTCAAAACAATCTTTCACTGCTTGGAAAGTAATCG
CGAGTTGGCCGAATACCCCCCCCCCTGCCTACTCCATACTCCTAATGCTGTTATTTACGGGCTCCAACACTAAGGTGTTTCCTGTGTACACCAG
GTGCTTTGGAAAATCCACTGCAGGATGTTTGATTTAAAATCATCAGAGTGCTATCGCATGCAGTGCAATAACATAAATAGCGTTCACTTGAAATA
ATAAACACATTTAGCTTATCGATAGAATTCGTTTACATATTGAACTATCTGCGATTTAATTGCCAAAACTATTCAATGCTCTGCCATTTGCGTAG
ATATTCCATGATTATTTCGATTGTCGGCCAGCGTCATTGGGCCTGAGGCTTTGGACTTAAAATATTTTCATTGTCAACAATTATTTTTGGAATT
GCCGCCAATGCTAATGAAACACATCGTGAGGTATATGTACATATACATATAAAGGAGAATATTACAATCCGAAGATCACTTTCGTGTTTATTAAC
TTTGACATTGGGGAACAGCGCGCAAATGCCCAATCTATATTTAAACTGATTAAAGAGATTTAATAAATAAGCCATTCTTTCACGCGAACGGTAAC
CATTTTTTTTTTTTTTTTTTTTTTGGTTACCCAAAAACAGGTCACCAATGGGACCCACTGGACAAGGGGATTGAAAATAAATTTAAAAGGGCAGG
AAATCTGTTGGCAACTGCTGGAAGGAAATTAAATTCTGCTTCATAGGTATGTAGGTATATTTGTGCCAAAAGTTTGCGCCAAAATAGACTAAAA
AACCGAAAATATAAAAAGCTGCAAAGACGATTTCTCACAGCCAAGAGAGATTTCTCTACTCATAAACAGATCGCAAAGATAGCGCAGAAATGAAA
AAAATATAGAAAAGGGAAGGCAGCACAGACTACTGGCAACTCGGGGAGGAAATGAAGAAATAGAAAAAAAATAAAAAATTAACCCGAATGAAAAT
CGCGGACATTTCGAGCAACGAATTTTTCACATATTTTCATTTGTATGTGAATTTTTAGAATTTTCACTAGCGAAAATTTATATAATATGGCTTCT
GTTACTATTTCGAGTCCGGTACGGTCCGGTCTGACGATAAATGAGCGGTGCCCGGACGACCCCGAGAGCACTGGCATAACCACCCTCCCACTTAC
ACCAGAAAACGGCCACGTAATCCTTGTCGGCCAGGAGCTTCTCCAGCTGCTTGGCATTGACCTCCTCGATGACGGCCTCCGGCTCCGGAGGCGCC
ACTGGCTGCGAGCCCTTCTTGTTGTTGTTGTTGCCTGCACCACTCACATGTCCGGGAAAACTCAGGGCCAGCAGAGCACACACGAGCAGCGAGAG
AGTCTTGAGGCGGGTGAAAGTCATCCTGCGATCGGTTACGGTTCTGATGTGCTTTAGGCCCTTAACGCGAACATGCGTGCGCGTGTCTGCTCGTT
TTGGTGTGTTCTACAGTTTATAGTGTTATAATTGTATAATTGATTCGTTCTCGTCGTTTGGGGTCTTTCGTTATTAAAATTTGTATTCCTTTGAG
AATCGGTCACTATTTTTAGTTGATAATGGTGTTTCTTCTTTCGCAATTTATTTTATGTATAACAACTTTTTGTTCACTGATACATATATACGGGG
TTCGTATATGCACAGGCGAGATATATGTGGGGTATATACGAGAATAATTAGATTATATATGTGGTTTCTTGCTTCTATTAATTGAACGTTTTCCG
CGGACTGTACTCTTTGCTCTTCAGATTTTGTTCCACTCCGTGCAGAGGTCCGCTCGCAACTGAAATTATTTTGGTGGAATCTCGGTGCCATTCAA
GAGGCCTTGCCCGAGCTTTAGGGATCGGGATCGTGGACTTCGTGCTTTGGCGCAGCTTTTCCGCTCCCCCGAAAAGCTTTCGCGTCGAGCACAGG
AGCGCCAATCGAGTGAGCAGTGTGGTGAAATCAGGCAAAGAGCAAGAGTTTCCCTTTTGAATTGCAGTTCTCTGTTTATGCATTCGGTGCAAACA
AGAAAGTGACTACGAATAGTCCTATAAAAACAAACTCGGAGAATCGCTTTCATTATGCGCTACAACAATTCACAGTACTTTGTATTCCCCATTTT
CCCTTTGGTAAACACTTTTAACAATGTGTTTCGAGCTAACATTTTGTCAACGTTATGCTTAGTCTAAAATAGAAAGGATTAAACTTCCCTTTGCT
AAGAGACATAACGTGACATTGTTGAATCTTTAAGTTTTATAGTTCCAAAAATCTATGCGTTTATAGAGATAGGAGGACATGAACAGATCGAATCG
GTTAATGATCCTCAATAAGAATAAATGTAAATTCTAGGGACGGAAACGTTTCCTTCCAGCAGTCAACTATTATG
(SEQ ID NO: 1042)

Exon: 3919..3706
Exon: 2021..1865
Exon: 1793..1627
Exon: 1195..1160
Exon: 1020..1001
Start ATG: 3919 (Reverse strand: CAT)

Transcript No. : CT26754
ATGACTTTCACCCGCCTCAAGACTCTCTCGCTGCTCGTGTGTGCTCTGCTGGCCCTGAGTTTTCCCGGACATGTGAGTGGTGCAGGCAACAACAA
CAACAAGAAGGGCTCGCAGCCAGTGGCGCCTCCGGAGCCGGAGGCCGTCATCGAGGAGGTCAATGCCAAGCAGCTGGAGAAGCTCCTGGCCGACA
AGGATTACGTGGCCGTTTTCTGGTATGCGCGAAGCTGCGTGACCTGTGATAAGGTTTTAGCGGAACTCGAGAAAATCGACGATGACACCGACTCC
TTCGGTGTGGACTTCGTGAAAATCAACGACAAACGACTAGCCAAACAGTATGGCATCAAGAACTTCCCCGCCCTCACCTACTTCAGGGAAAAGGA
GCCCATCATATATGATGGGGATCTCATGGACGAGGAAGGAGTGCTCGATTTCCTCACCTCCTTGGAGGCCATGGACTTGCCCGATCGCATCGAGG
AGGTCAATGCCAAGATATTGCAGAAGATCATCGAGGACACCGACTTCGTAGCCGTTCTGTTCTGTCCAGATCATGAAACATGCCCGCCCAGGGTT
ATGGTAATACCAAAGTTGAAATGA
(SEQ ID NO: 1043)

Start ATG: 1 (Reverse strand: CAT)

MTFTRLKTLSLLVCALLALSFPGHVSGAGNNNNKKGSQPVAPPEPEAVIEEVNAKQLEKLLADKDYVAVFWYARSCVTCDKVLAELEKIDDDTDS
FGVDFVKINDKRLAKQYGIKNFPALTYFREKEPIIYDGDLMDEEGVLDFLTSLEAMDLPDRIEEVNAKILQKIIEDTDFVAVLFCPDHETCPPRV
MVIPKLK*
(SEQ ID NO: 1044)

Celera Sequence No. : 142000013384828
CTGGTGGCGCGACTGGCGCACTATCGAGTCGATTACATACAGCCCGGGTACTTTGTACTCCGGCTTGCACTTCAAGATGAACTTCTCCACACTCT
GGACGACGTGCTTATACAGCTTGATGGCCCGCATCGCCGACTTGGTGATGGCGGCCATCTTCGCTTTGGAAATGGGCGGTCGGCTGTCATAGAGT
CCGGAGAGCTAAGGAGAAATATAGATGTTACAGTACGGCTATAGTTTACGGATATCTGGGACATGGAGTTATCGTTATCGGGTGCTGGCCAAAAA
GCAACCCTGAGCGGTGCTGTTCGGTGCTCTGCCTGCGCCTCCAGCAGGATCTGTATACCTCCCGCACATTGGACAATCCGAATACCGACTTCAAG
CGGACATTGTGCAACCACGCCGGCTGCTCCATAACGAACCTCGTTTCTAATGCATCTATAGCTTACCTCATTGTTGAAGGCAACCACGGTTTCCA
TGTTCAATTGCTTGGTTCACTCACGGCACGCACACACAATATTTAGTTTTGCATACTTTGGTTGGTCAACACAATCGTTTAAAACTGGCGAAAAA
CAATTTTCTCGACCTTTCTGCGGTTTCCACGGCTTTTAAAAAAACTTTTTACAAAGCGTGAAAAAAATGGCTGCCCTAAAGCCTGAAGCGTTGCC
AGACCTGTAAAGTTGACATTTTCAAGGCATTTCTGGAAATTGTGCTGTTAATGGCAGTGTGACCGTATGTGGTGCATAACGTTTCGGTATTAAAA
AATTTTCCAAATATTTATAAAAAATAAAACGAAATAGAATTTTCATTATGGAATCCAAAAGTTTCATATAAAAAAATAATGACAACAAAATAAAA
ATGACCTTAAATAAATTTAAATGAAATCAAATCTTCTTAAATGTACTACCTTTTAAAAATAATCGCTATCGGCGGTGTCGATCTTTTTAGCATTG
TGTCGATGACAATACATCTGGCAACACTGGTCAATATTAAACATATATTAAACAAATTAAAATGAGCTCAAACCACCGTCCTCTGGACGATTCGG
ATATCCTCCTAATACAAACCATCCGCGAGACGCCGTCGCTGTACGATCCCCAGCTGCCCTCCTTTCGGCTGTCGCAGCGCAAAGAGGAGGACTGG
GCAAAAGTGGCGGATTTGCTAAACATCTCCATCTCAGACGCTCGGCGACGGTGGACGTGTCTGCGGGATCGCTATTCGCGGGAGCTTAAGCAGAA GCGCCTGCATCCGTCCGGCGAGTTTGGTCACAATGACTTCTTTCGGAAGATGGACTTCCTGCGGGACTTTGTGCGCAAGAGACGCGAGCGCAGAG
GACGCGAACGGGATCGGGAACAAAAGCCAACCGGGTGGATGAAGGTTGATTTACAGCGACGGCGTCGTACCCGCCTGCCTATTGACACAGAGACC
TTGATCGAGGAGCAAGGTTCGCACGCCTACGATGAGGGCGAGGAGCAACACGACTACGACGCTAAGCTGGAGTCTCATACCACACAATCGGAGAC
GTATTCGGTGGTCGTGGAGGCGGACGATGGGCAGGAGCCCGAACAGGAGAGCTTCGATGAGTTCCTGGGGGATGCGGAGTGCGAGCAAAAGGTCA
AGGTGGTCACAATTCATCCGGAAATCGCTGCTCCGAATGCGACGTCCGCACCTGAGCCTATTGAGTCTAACCACGCGGATCTGAACTACTTGGTC
TGTATGCCGCCCAATGCGAATCAGGAGCGAGAGCATTCCGCCCCAGAATTACCCAATCCCACGGCCGTCATCACCCAAAAGACTTGCGAAACAGA
GGACGACTTCTTTTGCAAGTCGATTGCCGCGTATTTGCGCCAACTGTCGCGCGTGCACAAGATCAAGGCCAAGGTGGAGATGTACCAGATTCTAG
AGAAGTACATACTGCTCGAGGAGTGCGGAAAGGGGTCGGGTGCGGGCGGATCAGGCTAAGCAGGTTGCATGCAATATGTACATAGGTTTTAACAT
AGTTTTTTAATGCAGTACAAATATACAAAGAGACGAAAATCTTTTGAGCTTAATCTAACTTTGTGCTTAGGAAAAAATGGAGTCTTAGCAGAAGT
CCTCGTTGATTATGTTGGCATCTACGGCCAGGCCTCGTTCCTTTAGTGCCTTGGATACTAGGCGGTGTTTCTCCTGCCGCTGCTCCTGTTCCCTA
CGCTGGGCGTCCAGGATTTCATCGACGGATATCTCTTTGAGTGGCAGTTTCTGCTCCTTTTCACGGTCCTTTTACGCATATTTAAAGGGTGTTAA
TCAGTCATATTGAAAAAGTATCGAGTAAAGCTTACTATTTCGCCCAGTAGCACCACATTCTCCCCGCGAATGATGAAGACTCCGCGAGGAATGTC
GCCGTATTCGTTGCCCACATGTATCCGCTCGATGGTGCGTTGCAGCACCAGGTTGGCGAACTGGTCCACGGACCGCAGGTATCCAATCAGAGTCC
GTCCGTCTCTCAAAAGTACCATCAGTTTCTCTGCAATGCGCCGGTTTTCAACGACTGGCCTTCCTTTCATTCGGATTTACTCACTGTCAACCTCT
TCCAGGAGGTGAGCCGTGCCCGCCAGCGGATTTAAGTCGTCCATGCTATGAAAATATGTGGGATTTAGATAAATAAATAAACTGAAGCAACTAAA
CTTTGGTCTAAATTTTAGTATTTAATATTAATGTAACCCTCGCTGAAGGGTTTAAAAAACCACAATGCTCTAGAAAAAAATACTAAAAATATTAC
TACACTGTTCAACGAAACTTATAAGATATTGCTTACTGAAATTGATGTTTTTAGTTTTAAAATGCATAGATATTAAATAGTTATTATTAATTTTC
AAACAGTTAAAAATAAGATTTCTGCTCTAACATCAAATATTTTTACGCTGTTCACAGAGTTACAAAATAAAAAGAAGTTGACCAAAAAAATATCA
AAACTTGTACTCAA
(SEQ ID NO: 1045)

Exon: 1001..1959
Start ATG: 1012

Transcript No. : CT26756
AACAAATTAAAATGAGCTCAAACCACCGTCCTCTGGACGATTCGGATATCCTCCTAATACAAACCATCCGCGAGACGCCGTCGCTGTACGATCCC
CAGCTGCCCTCCTTTCGGCTGTCGCAGCGCAAAGAGGAGGACTGGGCAAAAGTGGCGGATTTGCTAAACATCTCCATCTCAGACGCTCGGCGACG
GTGGACGTGTCTGCGGGATCGCTATTCGCGGGAGCTTAAGCAGAAGCGCCTGCATCCGTCCGGCGAGTTTGGTCACAATGACTTCTTTCGGAAGA
TGGACTTCCTGCGGGACTTTGTGCGCAAGAGACGCGAGCGCAGAGGACGCGAACGGGATCGGGAACAAAAGCCAACCGGGTGGATGAAGGTTGAT
TTACAGCGACGGCGTCGTACCCGCCTGCCTATTGACACAGAGACCTTGATCGAGGAGCAAGGTTCGCACGCCTACGATGAGGGCGAGGAGCAACA
CGACTACGACGCTAAGCTGGAGTCTCATACCACACAATCGGAGACGTATTCGGTGGTCGTGGAGGCGGACGATGGGCAGGAGCCCGAACAGGAGA
GCTTCGATGAGTTCCTGGGGGATGCGGAGTGCGAGCAAAAGGTCAAGGTGGTCACAATTCATCCGGAAATCGCTGCTCCGAATGCGACGTCCGCA
CCTGAGCCTATTGAGTCTAACCACGCGGATCTGAACTACTTGGTCTGTATGCCGCCCAATGCGAATCAGGAGCGAGAGCATTCCGCCCCAGAATT
ACCCAATCCCACGGCCGTCATCACCCAAAAGACTTGCGAAACAGAGGACGACTTCTTTTGCAAGTCGATTGCCGCGTATTTGCGCCAACTGTCGC
GCGTGCACAAGATCAAGGCCAAGGTGGAGATGTACCAGATTCTAGAGAAGTACATACTGCTCGAGGAGTGCGGAAAGGGGTCGGGTGCGGGCGGA
TCAGGCTAA
(SEQ ID NO: 1046)

Start ATG: 12

MSSNHRPLDDSDILLIQTIRETPSLYDPQLPSFRLSQRKEEDWAKVADLLNISISDARRRWTCLRDRYSRELKQKRLHPSGEFGHNDFFRKMDFL
RDFVRKRRERRGRERDREQKPTGWMKVDLQRRRRTRLPIDTETLIEEQGSHAYDEGEEQHDYDAKLESHTTQSETYSVVVEADDGQEPEQESFDE
FLGDAECEQKVKVVTIHPEIAAPNATSAPEPIESNHADLNYLVCMPPNANQEREHSAPELPNPTAVITQKTCETEDDFFCKSIAAYLRQLSRVHK
IKAKVEMYQILEKYILLEECGKGSGAGGSG*
(SEQ ID NO: 1047)

Celera Sequence No. : 142000013384828
AAGGAAAAATATTAGAGATATACATTATTTGAATATATCGTTATTTATTTATTTTAGTTTAACTTAAAAATTGTCCTAAATCAATTTAAAGTGCA
TCAGCCTGAAAGTAGGCAAGCTATTTTGCAACCGACTTGGTGGTGAAGCCTTTTCATCACGGCCAACAAGTATGCAATGGTTTTACAGGCTTAGA
GCATTCAGTTCCATGTTCAATCGACAATTCATTTTAATTGAATTACCAAATTGCTAATGAAAAAATCGTATTAATTCGATTTTAATTTATATATT
AATTTCGATTTTATTAGGCTTTTTCTTTACAATTTGTTCGGCCTGCGTTCTCTTAAAATGCTTTTGTATAGTCTCGTCGCTCTTCGTCTCTTTCA
CAACTACTACTCAATGCTCGCTTTTGATGACTTTCTTTCGCACCTTTTTTATCGCGCTCTCTCTGCGCCTCTCTCTTTTACGCTTATAGCCGGCA
AGTAAAGAAGAAGCATAAATAGAAATGAAATATAAGTAAGCGGAATGCAAAATACTTTTTCTTTGGCGCCTTCCTCCTCACACACACACATTCGC
ATTCGTATGTGAAACCAGAAAGAACAATATAGTATTCATACTGCACCTGTATATCGACTATAAAGTACGCTGTACGTTGTATGTTGTATTTTACC
ATATGTATAGCTTATGTGTTTCCTTTTTTAATGCGGTAGCCTAGGATGTTGAAAATTATTTTAATTACATTTTTAAATCCTTTTAAAAAGACCCT
TGGCTCGGGACTTTAAATTCACTATTTATTTATTTTTATTTTTTCTCACTTATACATTTACCCAACTTGCCTTCGTGACTATATACCCTGTGTAG
TTCACATATAGAGGGTATAATAAATCTCCCACCGGCTTTTCTTGTGGTGGCCAACGACGTCGACTGCGCTGCCGGTGGCTCTGCATTGGCATTTA
GGCATTTATGCCCACGGCAGTCGAACAGCCGCTTCAGATTCTCGTCATCGCTCGTGGAAGGCACATCGCAAACGCCGCTCTCGTTCTCGAATTTA
TTGTGAAAGCTCAGCCGCCCACCGCCCGCCGGAAAAGTCTCGCGAGTGTCCCGAAAAAATCGAGTTAACCCCCCAAAAAAATCTATCATATAAAA
TCCTAACAAAATGAGCAGTAAGTTGGGTCACAGCCAAATCCAGAGCAAGCAAAAAAGCAAGAAAATAAAAGAAAAAAAGAGTGTGTGTGTGTATG
CATGGCTAAAGCTGGAAACTGAGAACTGAAAAGTCGATAGAAAACAGCCTGCCCTAAGTTAAAGCTCCTTTGGCGTTTCCTGCTAATCAATCAAT
CAAGCAACAAATCGCCTATCCTTCCATTTCGTAACACTCGCTTCAGGTTGGAGTTATGCAAAATCCGAATTCGATTTGAATGCAAAATCAGAAGC
TGAATCGAAATCATAGCGATAATCCCACTACTATAATATATATAATTATAAATCGAGCATAGAGCGCGCGCGATGTTGGTGTGGCTACGACCTTT
ACTGACCTTCACTAGCGTACGACTCTGCCCACGGCCCCCCGCCTCATCACCATCACCGTCACCACCCCCTGTTTCGTCGCTCTCTCCCTTCGCTC
TTAGTTTCTCTCTATTTTGAAACACTAACGTGCAGGAAAACATTTCAAAAATGCGAACATTGCACTGGAAACCGAACCGCTGCCAGTCAGTCGTC
TGGCATATTTGTTTGTTTATGAAAAGTTTGTGCACAAAATCGCTGATAACGTGAAGCTCACATAACCTTCAAGAAGAGAGAGAGAGAGAGAGATA
GATGGGGAGAGAGAGCGAGCTTACAGTTATGTTAATTCCGTTTTGTTGTGATTCCATTACATCGATTTCTGCGCTTTGTACCTGTCGCAATGCTG
GGTGGTGACCCAGTAATCCCACGTAGCGCCATTAGCAGCCGCCTTATCATCCATCCGCCTTATCAGCAATGCGATTATTTCCGCATCTGCAGCCC
ATTGAGATTAGCGGCCCATTAAGGGATGCACTTCGCCTTGGCATTTTTCACACGCATTCGCTGACGTCCGGCGATCTTGTTTGAAGCAATACAAT ATTCACAATCTATATGTGGTACACCCCATGGATGTGTGATTCTATTTTTAAGTTCGATATGTATGGGTCGGAATTATGGCTGGCGACAGGCGCTA
ACAAGTTTTGTCTGTTTCGAAAATAATATTATATTTGCCTTTCAAAAAGTTTTCCACGCCCGAGAACATTCTTTTGTGTCGCATCGCCATCGCCC
ACTAGTAAAGTGTGTGATCTCTCACATTTTTCTCTTTCCTTGGAAATGCCATTAAATCTGCACGGATTTATGCCCGCATTAATCATCAACCTACG
GCCGGCCACAGCAGCTGCCTTCAATTTTCTAGCCCGCAGGGATCTCCAGCATCTCGCGTTTCGGTCATCTACAGACACATCCACATCCACAGCCA
CATCCATGAATCCATGGTGATTCAATTTTCTAAAATTGCTGCGTCGCCTGTACCGAAGCGATCCAATGCATCGCCTACCAACCAGCAGATACAAT
CTCATTTCATTTCACTTCGCATCGCCGGCGCTATTTTTAGTGGCCTGCTCTTTCGGATACAGCATCGGCATCCACAAGATACACACGCCGCCTGC
TGAGGTTTCCCGCAGAACTCGTTCCGCGCCTTGCACTCGCCAATTTGTGCGTTGGTGTCGCCGGCGATCCTCGACACGACTTCCTCCCAAGACCA
CTCCCTTCATTGCATACCATTATGCACTTCCAGCGTACAGGCCAACATGGATAACTCAAACTCTATGCTAGACATAACCATATATGTAGAAGGTG
ATGTTTGGTATATTATAAGCTACTTAAACACACAGGATAACCTACTAACTATACAGAATTTGCAATAGAGTTATTGTGCCGAGCTAGCCAGGCTT
GACTGTACTTCATTTCTTGTGCGCCGGCTGCAAATTATGCGATGCTTTAATGGGGACCCTGACAAACGGGTTTCAGCGAGGGAAGGGATGTCCCC
TTCAAGGTCTTGGCTGCCCATTCATCTAATTGGTGACCCCATTCATGGTGGTATCTGGCGTTAATCTGATCTGGGCCTCATCACGCCTGAACGGG
AATTTGTTCAGTCACTTGACCCAGACCCAAAAGCTCAACCCGCAGCCCACGACCCCCGACCTTTTTTCCCAATTGCTTTGGCAGGGCGCTTTATC
GGCTTTATTGTGCTACGGCCATACGCAATTGATAAAAGCGGGTAGTAGAAAACAGAGCGCAAACTCTGCTCAGCGAAGAGAGCGCTTAAGAGAGA
GTTAAAGGGAGAGCATATCTCCGAAGAGAGCTCTCTCTCCCTACACTGTCAAAAAGTTAAGGAATTTTCCCACAGTTAGCTGTCACATAAATT
GCTAATTTACCTATTTTTAAGTTTACGTGCTAAGCATATGTTTAAGTAAAATGTCGCGACGCATTCATTTTGACAATTTCAACAGTTGTTGAAAT
TTTTGTATATTTAGACCGAGTGTTGTTTATTTAATTTTGTTTAAATCGCCAAATTTATGACGATTGCCGAAAATTCCTTTTCACCGTTCTGCCAC
ATAAGTTTTATTGTTTTGTGAAATTTTTTGTCATTTTTCGCACACACATCCGGTAAGTCAGAAGTTATTAAGATTCATTCTAGTTTTGCCGAAAG
TAAATGATTTCATTTTTATTTTAGGCCCAACGAATCATTTCACAAGCACACACAAACGCAAATAGAAAAGAAAGCATCTGTGTATCTCTCACTCG
CACACACACCAATGCAAATACAAGACCCAGTCACACTCACCCACACACACACACACACACACATTAAAGAATCCGGCGGAGGATATAGATCGTCC
TGATCTCAGTCCAAATCAAGATCAAGATCAAGATTAGGATCAAGTTCAGCCTAGTGAATGCATTTGAATGCCGCTGATTAGCTCGCTGTGCAGCA
GTTACCATCAGAATGCGCATCCGCATCCGCAAATGTGTCCACATCCGTATCCGCATCCGTATCTGACTGCGAGAAGGTAGTTGTTGTTATCCACC
TACTTGTTGTATCCTACGCTTCACAGTTCCTTTTCAGTTCGCTTCTCTAAAACCAAACAACCAACAAAACCAAGCCCAAGCCCATGTAAACAGAACTCTAA
TCTGACACTTAACCCGACTAAAGTTAGCACAACGAAATGTATCAAGAATATAACATATATATACACACTTGTATATATATATATTCATCTATCTA
TCGATTTGTAGTATTAATACCCGAATAATAATGTTCTAAATTCCATTTACTTGTCAATAATCAAAATTGGAAATAAAAAATAATTCGTACATCTT
CTCTCTCTCTTTAACTCTAATGAATTTTTAATTATCTAAACAGCAAATCTGCATGGTTTAATAATTTATAGAAACGAGAATTTCTTCGAAATTCA
CTTGTAAATTGTGTACCATACGGATTCTAGAACTAATTCCCCATCGAGTGAGAAATCTGCACCGAAACAAAAAAAAATCAAACTCATAATCGCCT
CATAAACGTGTATATAGATACATTCATATGTATATCCTAGCCAGCGCCATGAATAATTATCTACAGCTTTTTTGCCCAACTAAATGCCAACTACG
CAAAATTCTAATTGCCCGTTCGGACGCGCCTGAAATATGCTCAGCTCGATTTTGCCAATTCATTAATGGATCTTTATTATTTTTTTTGTTTTTTT
TTGTTTTTTGCAATTTTATCCTCGCTAACAAAGCAAATGAATTTTGGTTGCATGTGGGCGATGCTGACGCAGTTGGAGATCTGCACACACCACTT
GAACATATATATCTATATATCTGTTCTATTTCGAATGGGGAACCCGAACAATCGCTTGTTTATTTATAATCCGTAACGTTTTTTGCTGAATCCGA
AACTAATAAATACAGCCAACTGCTGCAGTGAAACGTGCAGTGCGCAACAGTATCTTTTTGTGTTGTAACCCAATTTGTATCTCTGACTTTAGCTA
TATATCTCATCTCTCTTGGCTACTCCATCGATAGCGTTTAATTTGCAATTGTATCTCCATCTCTCGTTTCGAATAGAATTCGCTTGGGTGACGCT
GACGACAAATGACACGTACTCACTGGGTGCCTTGGTCTTGGCCCACTCACTGAAAAGGGCCAAGACCGCCCACCAGCTGGCCGTTCTGGTCACGC
CCAATGTCTCGCAGGCGATGCGCGACCGACTGAAGGAGGTCTACAATGTGGTGCAGGAGGTCAATGTGCTCGACTCACAGGATGCCGCCAATCTG
GCGCTCCTCTCGCGACCCGAACTAGGCGTGACCTTCACAAAACTCCACTGCTGGCGCCTCGTTCAGTTTGAGAAGTGCGTCTTCCTGGATGCGGA
CACACTGGTAAGATATGAAGTATTCCAAGGGCACAACATGTAACTTGTGAGCTAACAAAGACTTAAATAACTACTTTCAATTTGATTTCGTAGGT
CTTGCAAAACTGCGATGAGCTCTTCGAGCGCGAGGAACTGTCGGCTGCTCCGGATGTCAGCTGGCCGGATTGCTTCAATTCCGGCGTGTTTGTGT
TCAAACCTAGCGTGGACACCTTTGCCCAGATCACAGAGTTTGCCGTGAAGAATGGCAGCTTCGATGGCGGTGACCAGGGTCTGCTGAATCAGTTC
TTTGCCGACTGGTCGACGGCGGACATTAAGAAGCATTTGCCATTTGTGTACAATGTGACGGCTTATGCCTCGTACTGTTATCTGCCCGCCTTCAA
ACAGTAAGTTCGCTATCTCTGTGGAATGGAAAAGCAGTTTGTAATGGCATTTGTTTGCTTGCAGGTTCAGAGATAAGATTAAGATTTTGCATTTT
GCCGGCAAGCTGAAGCCCTGGCTGATTCAGTTCAACTCGGAAACAAAGGTGGCCAGCGTTTCGTCGGAGTATGCTCATGCCCAGGATTTGATTCA
GCTGTGGTGGAACATCTTTTGCGAAAATGTCATCCAGTCCCTGTCCACCGAAATGGTAAGTGCTATTTATACAATGGATAACGCACATTTTGGAA
ATTTCCAGCGTTACTTGGTGCCCCCAAATGATCTTATGTCTTCCCTTGTTTTGAACGCCAGACTGAAGCTAACCCTTTGATTTTTACTGTCTAA
CCCAATGTATTTGCTCCAAATCTCAAAAACAAAAAACCCTGCTTCGTTTTCTAACACGCTAATCGCAAGCAAACGCCAGGAAATGTTGCTAGTGA
TCGACCCGCGGGAGAAATGGCCCAAGGGTCCACTACTTTAGAGGTAAGCAGATCTTCAATTGCCGAATCGCACATATCGCACCAGATCTGTAGAT
ACCTTGAGCACAGCCCTGTGTAAATATCTTAATTATAACTTAAATATTTATTTATTTATTTAGCTAACGATTCAGTCATCTTTCTGTGCGCCAAG
TAAATAACCCAAGCAAACAAACTCAATTTCGATCTATTTGCCATTTGTTTTTTGCCGATAGCTGGCCTCGATATCGTTTCATTTCCCGCCTCTTT
TCTATCAACTCGGTTTGAATATACTTTGTTTTCGTTTTATTTATTTTTATTTTTTTGTATTGGTTTGCAATTTTCTGTTGATTTTTTCTCGATTA
GCAGCCACGCCCCAGAGTAACCCATTTTCCTTTTTTTTGTATATTTTCTTTCACTTTTTTGGCACCATAGGCAGACCAATTCTCAATTTATTTCT
TCTGTATTTTTTCTGTAATATTTGTGCAACTGTGTGTGTCTCTCGTGTGTGTGTGTGTGTGTGAGTGCTCGTCTTAGTGTTCACTTTCTTTCTGT
TTTCTTTTCCTTTCTAATTTGCATCGATTTGGCAAAGAGCCAGGAAAATGTTTCGGTTTACGCCATCGATAGATGGAAATGATTCAAATCAAGAT
GGTCGGTTGCGGGTGATGCCAAAAAAAAAACTCAACTGAATCATTAGATATATCCCATAACACAAACAAACACACACACACACACACTAGCACGC
ATTCGTGGGGATCTCCTCTCTCTTGATACACACAAAGAAATTTTGATATAGAATGGAAAAATAAATTTTATCTTATTCCAAATTCATTTAATTTA
AGAGAAATAAATAATTTTTTTTATATTATTAATTTATCAAATTTTGCTGTGTGTACTTTTCTTTTTCTCCCTTTGTTATGTTCGTGCCGTTGGGT
TCTTTATTTTTTGCAAATTGATTTACTTTTCATTTACTCTCTATTTTTTGAACTCTGCTCTCCTGTGTTGCGCATTCTGTAAATTTATACTTTGC
CATAAATAATACGTGGACTGCCGTATCGCATATAACTCTGTATATCTAACATTGTCTCAGTGCCTTTGCCTAAATATAATACGCACGCAAAGCGA
ATTCGCGGCGGATGAGCTGCATCAGCGGCAGCAGCATGAGTTCTACCAGCAGCAGAAGCTGCACCACCACCTGTTGCATGTGCGCCAGTTCCGCG
ATCCTTGGGCAGATTACTATGAGAATCTGGAGAAGGAGCCGCAGGAGCAGGAGCAGGAGCAACAGCGCCACCAGCACCAGCAGCAGCACCACAAT
CCCAGCCAGAATCACAGCCAGGACAATGGGAATGCGGATGCAGCTGCGCATGAGAATGATAGCACGATTGCAAATGCAAATGCCACTGACTGGCA
TCATGACGATGCATGCCACCCACCTGCGCCGACGAGGCCTCTGCCCCAAATTCAAAACCAAGCCCACAATGCCAATGCCACTGCCCAATGCCGAAG
ACTTTTCATTCGTAGATGTGAATAGCAATGAGCTAAACATTTCACAGCCACCTGAACACGCCTCCTACTCCTCCGACACAGCCACGCCCACTGCC
ACAGCCACGCCCACTGCCACGCCCACGCTAACGCCCACGCCTCATCATTCCGTGCATAGTCAGACAGTAGAAAAAGCGACAAGCCACCAACAAGA
ACATGAAGTTGCAGCCACAACGCCGCCTGAGGTAAAGGCAATCAATCCAAACCCGGCCTGAGAACTACACAGAAAAAAAAAATTCCCTAATGGTT
GTATGGGTTTTTCAAATCCAACATAGCCCTAAGCAAATGCTAGAACTTATTATTTATGATTTTCCTGGCACCTCATGCAAAATGGACTTCATGCT
TATATATGGAAATATCAGAATATTTAGTTACAAATTGGAATTTTTTCTGTGTAGGAATCCCGATTCCCAACCAAACAAACCAAATGCATTGGATA
ACGGTGTGCAAGTGTAAAAGTGCTAGTCCAAGTGATAGTGATAATGTAATGTCCTGGTTTTCGTCTAGTCACTGTTTTGCATACGAATTGTCATT
GTCGTCTTCATTGTCCTTCGGTCATCGTTCATTGTTCATGGTCCTTGGTCCATGGTTCTTGGTTCATGGTTCAGCGTTGTGTTTGTGGCCTGGAT
AAGGGGCATTTGTTGATTTATTATTAGTTGGCCTGGCACCTGGTCAAGCATTAATGTAGATGGAATATGGGGGGCCTCGCTACCCTACAACATAA
TCAACATCATCATCATTTGAAACCCAAACGCAGCAAAAGCCGGCACTCCATCCTCGTGTTGCATGCGCATTTATAGCCACCTGCATCTCCTGC
ATTCGGCCCACTTTCACATAGTAATCTGCCCGAGAGTTGCTGGGACACGCATTGCAAACGCAAGCAGCCGGAGCTCAACGCGTCGTATACTTGAT
TTATGCCTCGAGTAGCACTTCTGTTGTCACATTAATCATACGCCCTGTGCACCGTAACTAACATCTCAATGTTGTCAACCGCTCGTCTGCGTACT

FIGURE SHEET 568

AGTGCTAGTAAATGTTTAACCCGTAGTGCATGAAATGTCGTAATATACCACCCGACTGCATATGTATATTCTCCTCCCTTGCTCCATCATAATGC
AATCAAGCTCTTAATCAATTTAATTAACATACTTTCAGGCGGGTCTGGCTGGTGCTCTGTCACAGCTACGCATCGGTCAGCAGCGCACTCCCGAA
CAGGAGGCCTACGAGAACCAGATGCGCCGCCAGTGCTGGGAGTCTGGACAGATTGACTACACCGGCGCCGATTCGTTCGAGAATATCTGGAAGAA
AATATCGCAGACGCTGGAGAGGAAGACCGATAAGGAGTCGGAAGAAACTGGTAGCTCATAGATACAAAACCGAAACTAAACAGAACAAACAAATG
CAAATCGTTCGTTATTCGTCGTTTTGTTGCCATTTTTTTCTTGTACACGCGCACACACGTACACACTTAACACCCACCCCTTCTCCACCCTAAAA
TGAAAACCCCAAACACGCACACAATCGTATTTTATCCCCCCTCCCTCCCCACCTTTGGGAGGCAGGCGAACTGTTGCCAATGTCAAGGAGCCGCC
GGTCTAATTGAAATTTAAGGTTTGGCCAAAAAATGTTGTCGAAACGAATTCTTCAGAGTGTCATAAATGCAATTTTTATTTGCCTTCCCTGTTAC
AGCCACCCACCCCCCCGTCCACACACGCACACACACACACACACGCGCGCATCTTGTTAAAAAGAATGAGCGAGAAAGCAGAGAAATTTTAAT
TAAGTTTTCAAATTAAACTTTTTGCACTGCTGCTACTGCTACTGCTGCTGCTCTCGACATACGTGATGTGATGCGATGTGTATGTGGGCGACACA
CTTGGCACAGTTGCCCCAATGCCCTGCCCCTCCCCCTGCCCCTGCCAAGCCCTTGGACAAAATCGAGAAAAAATGAGGCCCGGCCACAAAGTTTT
ACACTTCATTGTGTTTTAATTGAAATTTTTGTACTTTCACCCAGTCGTGTGCTTACCGATTTATGGCGATGACTTTCCAGCTCATCTGCATCAAA
ACTCATTGTGGCATAAAGGCCATTTCCTGTCCTTGCCCCACCTATCCCACCCCTGACTACCCTTTTTCCCTCTGCCGCCCCCAAACACATATGTA
CATATGTTTTTCCTATGAATAAAACGCAAACAATGAGTGTATACAATAACTCTGGAAAAGATAAACGAAAACCATTTAAAATAAAGTAAAAATCA
AAAATGAAATTGTAGCCCACATGTTGTGGCTATTGTGTATATGTATCTATGTGTGTGTGTGTTTATGTGTGAGTTAGAGTGTGTGTGCGAAGTGC
CCCGCCCCCTTTTCGACCACTTTTCGGATCGAATTCGAGCTGAGCGTTAAATGTTTGTTTCAAGTGTTTTGGCAGCCTAAAATTTCTATCTATAT
ACGTATATATACCATTTATGTTATAATTTACATTTTGCAAATATTGTCGTAATATTTATTCGAGAACAACAACAACAAGAACAACAAAGAAATCC
CAAACAACACAAACAAAAAATTTTCAATTTATGAAACTATGTTTTCGAATTTGCATTTTTATTTTAGCAATTAAGTTAAGTTACGTTCTTCTTTC
CCATGTTGTCACCTTTTCAGTTGTGTACTTTTAAGCCATCTTAGCCATGGCAAGCATTGTGTCTAAGTCTTGGGTCTTAGAACCATCACATAGCC
ATAAGAGCCAGCACCATTCACCCATCGCATCTTAGCCATCAGCCATCTTCAGCCATCACCAGCAATACAGCAACGCAGACGATGTAGCTGAATCG
AATTAAAACTACTGTCTCGTTACCCCTAACCACATTTACAGATAATGATAACGATAGTGATCCCGCTAACCCACTAAGCTCAGCTCGATTGCTAA
ACGAAGCCGCCAGCATACTGCTGCATCCGCCCGAGAAATCACCAACTTCAAAGGCGATGAAAGCGAATGGGGCGACTGGGAATGGCTCCCATCTC
GACCAGTCGCATCCCACCAACTCCCCAGCAACTAACAAACAGCCTGCGAATGCTTCAGCTTCCCCCAATGCCTCCTTGAAACAAAATCCACAGAA
GCGACAGGAGAAACCGCAGCCCCAAGCGGAACCGGAACTGGAACCGAGACCACAACCACAACCGCAGCCAACAGAGCAGCACATCAGGATGCAGC
CAGGCGGCGGAAATGGCAGCGTCTCCAAGAGCGGCAAACAGAGGTCCGCACGCAAGTTCAAATAGCAATTACTGAAGCTGCTGATGCACTACAGC
TGCCTGCCACACCTGGCGTGCCGCTGCAAGTCGCAGTATCGGCGGCTGGAACCCAATCTGGATACCGAACCCCAACCCGTCCACGTCTAAACCCG
ACGATTGATAGACAGATCCGAGGAAGTACAAAGCGTATGCCACGATAAATGCTGTACAAATTGCTTGCTAAGTGGCTCTTAGACGAAAGTAAAGT
AATCAAATCGAAACGAACTAAATTTATATATTTATATTAAATTATTAATGCAACAATTATCAGAGCACACAGGATTTCAAAAGTATATAAATAGG
TTTTCATTAACTTTATATCGCTTGAGTCTTTGAAAGTAAATGTTTAAAAGAGAAAACTCTTTTAAAATGCATAGTAGGTTATATTTCTTGAGGCC
ATATAGCTCCACGACTTTTTTGATATCGTCTAAGGGTCCCTTGGTTTACCCAAATACCACGCTGCCTTACAAAGGAAACACATGCAATATCTTAA
ACTTAGCATATAGTGTAAGACAAGAGCTAATACTAGATGTAAGCCGCAAGTGCTTTGGATAACCCTAGATGCAAACACACACTCAGGAGCTTGGG
ATGATATCGCCTTATATGCCATATATACTATACACACATGCATCCACACACCACAGAGCTACTGACCTCCGCGGACATCGAAGACGGTAAGGTGG
AGTTCGACAAGGCCACGGGTGCCACCACCACGTACAAGGTGATCGAGGGTGGCTACGAGGTGATCACCACCTCTCCGCAGCCCAATGGAACCATC
AAGACCCAGGTGCGAACCTTCTGGGATCCCAAGCCCGTTAGCGAGGAGGATCTGAAGAAGGAGCAGGAGAACAAGAAGCTGGTCCAGAAGCGTCT
GGGCAAGGAGATTCGCATCGATGAGCGCACCACCATGCTGACCCGCGCCATCGAGGGTGGCTACGAGGAGGTGTACACCACCATCAACGAGGATG
GAACTCGCAGCTCTCGCACCAAAACCTTCTACGACTCCGTTCCAACCGAGGTGGATGAGAAGACGGCCGCCAAGTTGAACAAGAACAAGAAGAAC
GTGACCAGGAAGTCGTCGGTGGACTCTACCGATTCCACGGAATCCTCCCGTCGCATCGTCCAGAAGCAGCAGAAGAATCTGGTGCAGAACTATGA
TGAGCAGACCAACTCCACCACGACATCAGAGCGCAGGGTGTCGGTGACTCAGAACATCGAGATCACCGAGAACAATCGCACCGTGCGCAAGAACT
CGCTGCAGGAGCAGAACGTCAAGGCTATCACTACCACCTCGAACACCTCGTCCAGCGACAAGAAGCAGAAGAAGAAGCCCAAGTCATCGGCTCCA
CCACCACCCGCTGATTTCTTCCAGAACGATACCACCTCTGTGGCCTCGAAGCGTGTGCCCGGCGGTGTGGAGTACACCTATTCCACGCAGCTGGA
TTCTGGCAAGACCATCACCACCTCGAAGACTGTCTACGAGGAGGAGGAGGTGGAACTCACCGAGGAGGAGATCCGCCAGTACAAGAAGACCCTGA
AGGACGCCGAGAAGCACAAGAACGTCTCCACCACCAAGAAGCTCAAGTCCGAGTCGGGTACCAAGAAGATCGTTCCTTCCGAAAATCCCGGAGAT
GTGACCACCGTGGAGACCATTAAGATCGAAGGTGGCACCGAGTACCACTACACCACCGTGACATCCGAAGGCATCGTGAAGAAGGCCGTGAAGAC
CGTTTACGATCCAGTGCCCAGCCAGAAGTCCAATCCCGATGACACCGACGAGGAGGAGATTATCGAGGAGTACGAGGAGGAGATCATCGAGCCCG
GCGAGAAGAACGTCAAGACTATCGAGACCGTCAAGCAGCTGCCCAGCAAGTTCGAGGGTGAGGATAAGCCAGTCCACTTCATCCGCAGCTAGGTT
ATATTAACCCATTTTCTTTTTTTTCGCAGAGGAAGTGACCATCACTCATGAGAGGAAGGAGAAGAAGGTAAAGAAGTCCATGGTCATTAGCCAGT
AGAGATCGCCGCTTGCCCACACCGAAACACACTCAAACACACACGACACTCACACAACACACAAGGCACAAGAATACACACGAAAAAAAAAACAA
GCTTATGAAATGGCCGGAAAATAGAGAAGAAAGGCCCTGCGAAGATCCCGATCCCAAGCTAATTCTCCTGACCTATTTCAGCATCCAGTTCAGTT
AGTTGCTGGCGGTCTTTGCACGCTACTCGTTAGCTTTGTTATCAATTACCAGCTGTCTAGTGCCCTAGAAATGTATTACGAAATTATCCAAAATT
TATTACAAGAAACTATCTAACATAATTGTAGCCTCTTTTGTTAACAACAAAATAAAACTCAAGTTTTGGTTCTAATTCTTCTTGGTCTTCTTCTT
CGTCGGAGTGCTCTTCGGCTTGGAGCTCCTGCGGCAGATCAGGATTAGAACTACGATTGGCAACAGGATCACAGCGAGACCTAGACCCACAATGT
CCAGTAGGTAGAACTGGTACCAGGGTAGATGTACACCAGCGGCCACCAGATGAGGAGCACCTCGGTGCTCGATCACATAGTTGATCCAATATATG
GCCGTATCCATGGCACCGAGTGGTCGATCGCGGAATATCCGGGAGGCCTTCTTAATGTTATTCCTATACTTTGGATTCTCAATCAGTTCCATCAG
CAGACCTCGCAACTCCTCCACCGTGACTTTCCGGTAATCCAGTCCCAGTGCATATTCTGCACTCTTACCCTGGTTAATGTTCTGATGCTGATCAC
AGTAGACTGGCATTCCCAATATGGGAACACCATTGTACACCGCCTCCTGGGTGCCGAAGAGTCCTCCATGGGCAATGAAAACCTTGACATTCGGG
TGCGCCAGAATGTCGCCCTGAGGTAACCAACTTTGCACCTTAACGTTAGCCGGCAAATTGGGCAGAGATTCATCTTCGAATTTCCAGAGAACGCG
TTGCTTCAGACTGCCAAAGACTTCCAGGAATACTTTGAGCTTCTCAGGCGGC
(SEQ ID NO: 1048)

Exon: 1001..1157
Exon: 11742..12987
Exon: 13045..13112
Start ATG: 1151

Transcript No. : CT26824
CTCGTGGAAGGCACATCGCAAACGCCGCTCTCGTTCTCGAATTTATTGTGAAAGCTCAGCCGCCCACCGCCCGCCGGAAAAGTCTCGCGAGTGTC
CCGAAAAAAATCGAGTTAACCCCCCAAAAAAATCTATCATATAAAATCCTAACAAAATGAGCAAGCTACTGACCTCCGCGGACATCGAAGACGGTA
AGGTGGAGTTCGACAAGGCCACGGGTGCCACCACCACGTACAAGGTGATCGAGGGTGGCTACGAGGTGATCACCACCTCTCCGCAGCCCAATGGA
ACCATCAAGACCCAGGTGCGAACCTTCTGGGATCCCAAGCCCGTTAGCGAGGAGGATCTGAAGAAGGAGCAGGAGAACAAGAAGCTGGTCCAGAA
GCGTCTGGGCAAGGAGATTCGCATCGATGAGCGCACCACCATGCTGACCCGCGCCATCGAGGGTGGCTACGAGGAGGTGTACACCACCATCAACG
AGGATGGAACTCGCAGCTCTCGCACCAAAACCTTCTACGACTCCGTTCCAACCGAGGTGGATGAGAAGACGGCCGCCAAGTTGAACAAGAACAAG
AAGAACGTGACCAGGAAGTCGTCGGTGGACTCTACCGATTCCACGGAATCCTCCCGTCGCATCGTCCAGAAGCAGCAGAAGAATCTGGTGCAGAA CTATGATGAGCAGACCAACTCCACCACGACATCAGAGCGCAGGGTGTCGGTGACTCAGAACATCGAGATCACCGAGAACAATCGCACCGTGCGCA
AGAACTCGCTGCAGGAGCAGAACGTCAAGGCTATCACTACCACCTCGAACACCTCGTCCAGCGACAAGAAGCAGAAGAAGAAGCCCAAGTCATCG
GCTCCACCACCACCCGCTGATTTCTTCCAGAACGATACCACCTCTGTGGCCTCGAAGCGTGTGCCCGGCGGTGTGGAGTACACCTATTCCACGCA
GCTGGATTCTGGCAAGACCATCACCACCTCGAAGACTGTCTACGAGGAGGAGGAGGTGGAACTCACCGAGGAGGAGATCCGCCAGTACAAGAAGA
CCCTGAAGGACGCCGAGAAGCACAAGAACGTCTCCACCACCAAGAAGCTCAAGTCCGAGTCGGGTACCAAGAAGATCGTTCCTTCCGAAAATCCC
GGAGATGTGACCACCGTGGAGACCATTAAGATCGAAGGTGGCACCGAGTACCACTACACCACCGTGACATCCGAAGGCATCGTGAAGAAGGCCGT
GAAGACCGTTTACGATCCAGTGCCCAGCCAGAAGTCCAATCCCGATGACACCGACGAGGAGGAGATTATCGAGGAGTACGAGGAGGAGATCATCG
AGCCCGGCGAGAAGAACGTCAAGACTATCGAGACCGTCAAGCAGCTGCCCAGCAAGTTCGAGGGTGAGGATAAAGGAAGTGACCATCACTCATGA
GAGGAAGGAGAAGAAGGTAAAGAAGTCCATGGTCATTAGCCAGTAG
(SEQ ID NO: 1049)

Start ATG: 151

MSKLLTSADIEDGKVEFDKATGATTTYKVIEGGYEVITTSPQPNGTIKTQVRTFWDPKPVSEEDLKKEQENKKLVQKRLGKEIRIDERTTMLTRA
IEGGYEEVYTTINEDGTRSSRTKTFYDSVPTEVDEKTAAKLNKNKKNVTRKSSVDSTDSTESSRRIVQKQQKNLVQNYDEQTNSTTTSERRVSVT
QNIEITENNRTVRKNSLQEQNVKAITTTSNTSSSDKKQKKKPKSSAPPPPADFFQNDTTSVASKRVPGGVEYTYSTQLDSGKTITTSKTVYEEEE
VELTEEEIRQYKKTLKDAEKHKNVSTTKKLKSESGTKKIVPSENPGDVTTVETIKIEGGTEYHYTTVTSEGIVKKAVKTVYDPVPSQKSNPDDTD
EEEIIEEYEEEIIEPGEKNVKTIETVKQLPSKFEGEDKGSDHHS*
(SEQ ID NO: 1050)

Celera Sequence No. : 142000013384430
CTCTCGAATTGCTTCAAGTTCAGCCAGAAATTGAAACTGCAGTGGAGCTTGTTGGCTAGCCCAACAGCAGGGTATCAATAATAGTAAATAAAGTA
GAATCGTATGGACGTTATTTATTCTCTGTTGAAAATTCCATAAAACCAGAAATTGATTACCCACTACTAAGAATCTACAAATACATCACAAATGG
CCACTTCCCATTAAAATTTCAAGTATTTTCAGTGACTGCACGTGAATCCGGCTAATGATATCTACTAATATAGATAAATATAGCACACATGCTGC
AATTAAATATGAATTTTTTGCTTATCAAATAAACAGAGCTTAATTTCCTACTAATTAGCTATTTTGAAGTGCATGGTGGTAGTCGGCTCTCCGAT
GGATTAGATAAGACCTATCGCTCTGCAAAAAAAAATGTAGGTCAGCTGGAATTTCGAGCATCCAATTTCAGATTTTGGAGCTTTCGGGTGTTACC
CGTTGCTAATGGGTAGATCTTAATTGGACGACCTCCATGGCTTCAAGTTCAGTGCTGGTCAATCGTGGCATATGTGAGTGCTGTCAATAATACCA
CTGATACTTTTTTAATGCCGCTCGTTAAACGGTTCCCACCGACCCAGAGGGCGGTACTTGCTATTTGACACTCTTTCGGCTGGCGAGTGCTCCAT
ATTATATTAAATTGAATTTGGTGGCGATGTCTCGCTATAAAGCATGATACGCCCGTAGTCGATGTGTCCAATTCCCGTTAGGCAACCAAACGACT
GGAATCGAGCGATCCACCAATTCTCGATCGGGCTGCGAATCGATCCGATTACGATCCAAACCGAACCGATTCGGCGACATTCAGTTCGCCGTTCG
AAGAGCTCGAGTGCGCGTGTCAACTGGATCAGCTCCCCCCCCAATAGCTCCCCACAATCCCATCCCTCTGTACCTTTAAAGGCACTCATATATGT
ATATATATATAACTTTATTTTTTCAAGATCACGGCAGAGAGCAGGGCACCGCTCCTCCTTGCTCACACCTACAACTACACTCGCCTTTAACTCTC
TCAATCTCTCCAGTTCGGTGCTCGTGTCGGTCGTAAACATAACTCAAAAAGCGCTGCTGAAGTCAGTAGCCGGCTAAACGCGACTCGGATCGGAA
GTCTCCGCTCCTGGCAATCAGAAAATCCCCTCCACGCGATAAGGGTGTACATAAAAAAAAAAAAAATAAATAAAACAAGTTAAATAAATATATAAG
AAAATCACATAAGAAATGCAACTTTTCGACGACTTTTGCAAAAGCTTCAACAAGGAATTGCAAAGGGCGAATTTCGGCTTTGCGTACAATCGAGT
TCATTTATTCTACAGATCTCAGGTGAGGACAGTTTCACGTAATAGTCGTCCAAACACAGCCGTCTTCTTTATCGGTGCTGTTACAACTCAGGTGG
TGGTATCATACGTGCCAATGCAAATAGCAGTAGCGAAAAATAAGTACATATATACATAGTAGTCACTGTCATTAGTGTTCCGTGCAAAAACTTCG
TGTGAGATCACAGAGGCACGTGTTTCTTAAATATGAAAAGCCAAGGGGCTAGTTGTTCGTTCGCAAATGTCGAAGTCAATGCATTTGAAATGGTA
TTCCCACAATAATTGGCCTGTACAAACGACGTCGCACTACGACCCAGGCTATCAGCAAATTAACTAGATAAGTGCAATAAAAAACATGATAAGCA
AAACACCCGAAAAATAAAGGGTTTTTAAAGAGTAAACCATTAAAATTCCTATCATAACAATTTAACGAAGCTCCGCGCATTAAGCCAAAATATAA
CCTGAGTACCCCAGGGCATTCTATATCTGCCATCCATTAGAAATACACTTAAAAGGTAAAACTGGCTTGTATACCAAATGTTCATTAGAGTGTGC
TCAACAAAAAAAAAAAAGCGAAGTTCACAGAGAACATAAAATGTTATGGTGAGAACACATTGTACACGCAGGCATTGTTAATTAATTCGTATTTA
ATTAGCACAGCTAAACTAAAAGCTGGGCTCTATTCAAAGTTGTATTGCTCTAAACAAATATCACGAATAGAACAAACTAAAGTGTAACCCAAATG
GATATGAAACTATGTTTTAACCAACTGTTCATGAATGAAGGCAAACCATCAAAAACCATCAGTTAAGTGTAAAAGAATCTTTTATCACTATATA
TTTGTACACTCATGAGCAAATATAAAAGTTATATGGACAAAGATATCTACAAGACCATGATGATGATACCAAGTTAGATAAGAATTATGAAATTT
TGAGCTCCCTTTTTCGACAATTCATTCTGAGTATAATCCGGCAAGAAAATACCAATCGGCTACATTAATGTTTTTGTGTCAACATTATGAGTCAT
TTTAAAATCACCAAAATAAATTCCCTTAAAAAAGCCAAGTACTGAAAACCCCTGATAGTTATTGGAGCTCTTCCATAACACTGATTACACATTTC
TCACGAATGAAATACTAATCAAATCAAAACAGGAACCAGACAATAGTTTTGGCGCTCGCCATAAATATTCTTGCTAGACCTTATCAGACAGCCAA
CAACAAGCCATAAACATCCATGAAGGATCGCGTTATCTAACGAATCAATGTTTTTATTTCCGCAATATTTAAGTTCTAAACAAATAAATTTGAAT
AATACTACGCACGCAACAAAACTAAAAGCTGTGATGCGACGAAGGTGATATCAGTTAGACAGGCCCTAATTCGGACTACGTCATTGCTAGTGATA
AGCGCTTAGCATGTTTGTTAACGCGGGCAAAGGTGTGGAATATTTTAATTAAAATATTACATGATTATTAATCGATGATCATGTAAGGGTCAGAC
TGGTGCACGCGATAAGGAATTCGCTATCAATCGCTGTCACAGCAACAATGTAACAATGAATTATTGCCCATATATAATATATTTTTAATTTAATC
AATTGTATTACATTAATTATTAAATAGCTAAAACTATATAATTCTCGTATTGCAGTGGCAAAAAGATGAGATCAACACAATATACTTGCTCTACC
GATGGATTTGGGCACTGTTTTTCCTGGGCGTGTACATCATGTGCGTTATCGTTCAGTTTTGCGATGGAAAGTTCTTCATCTACATGACCAACTGG
GGATTCGGGCTCTGTACGATCACCATGCTGATTTCCGCCGTACAAGTCACCTGCTGGCACTTCGATGTGAGGAGCACCCGGAGCCTGGTACAGGA
GTCCGGTCACAAGGCGGAGACGTCGAGGGGCCTGAAAATCTACTGGTGGCTCTACAATATGACACTGTCGCTGGCTCTGATCATATCAACAGTAT
ACTGGGTGTTCCTCCATGGAAAAATGAGTGAGTATTGCCGTATCTGCGTTCATTATTTACATTGCTTTAAATGACAGTGGTGGGTGTGCAAGCTA
TTACATACCTTACGATATCTATGTGCAATAGAGAGAAAGAGGGCATATTTTATAACATATTTAATGAATTTCCTTTCGTTACAGACAAGCCCATG
CGATTCCCTGCCATCAGCATTATCACCCACGGCATGAATTCTGTGATGATGCTAATCGATTTCCTGGTCATTGCATTTCCGCTTAGGATACTTCA
CATGGTGTACGGAATGAGTCTGGCGATATTCTTCTTTTTATTCACGCTGATCTACCATTTATGCGGGGGAACAGATGAGTGAGTACTTGAAATCT
TACCCGTATACCTTGCAATTTAGAGCTAATCACCTTCACAATTCTCCTTCAGATTTGGCAATCACTACGTGTATCCCATTCTGGATTGGAACAAT
CCCAACCGCTGTATGGTGACCTTTGTGGGCATCTTCCTGCTCATTATGTGCTACTGGGTGCTGCTCTTTGGACTCTACAAGTTGAAGAGAATGTT
CAATAGGGCATTCAGTGTGGTTTGGTCTCCTCATGCTGTGGGTCTGATATGAGGGAGTTAATACAACAAAAAGTCATTGAATATCACCTCATGGG
CACCCGCACGTATACCATGTTCTTATATGCATTGCCAGCATTATGTAACTCCCATTAACAAATCCATCCAAAAACGACACTGAAAAGGGAGTCGC
ACACTTGCATGCATTTATTTATATCTAGTATTTCATATTGTAAGTTTTAATCATTTGGTTCCTTAACATTGAATTGGTTTAGTTAGGTTAATTCT
TATACATTATGTTGTTATTACATATTTGGTTTAAATAGTATAAATATGAAATTTGTTGAAAATACTCTACCCAAGGGTTAGATAAAAAGAATAAT
GGAATTGTATTAAAATATATCACGAATATCAAAAGTGGAAAGAAACGAAATAAAGAAAATGTGGCGTTATTGAATTTAATTGTGGAAATCGAATA
TTTTATTATTATAGACATGAACAGGATAATTTTTATAAAAGTAATATCTAAATTTATTTTCGCTGTTCGTTTTTAAACAATTATATAAGTAATT
GAAACTCATTATATTTCATTCAAAATTAAAACAATTGTAGATAACATTTTAATTGTTCTGCATTTCGAGCAAGCTTATCTCTAGTCTTTGGAAGC AATTTGTAAATAATTTTTCAAAATGTTTTTTTTTAATACCCTTTCATATTTTATCAGCACCGTAGAGATCATTAAAACATTTACTGTGAAGTGG
AACAGGTTGAATGACACTAAAGATTTCGGTAACCGGAATACTTACTTTTTCGCTTACTTTTCTAACCCAAATCTCGAAGACTTTTGTTATTCTTC
AATAAAATGCTTACTAAGCTTTTTTCGTTGTAATGCTGCAATTAGGTTACAAATCCAGTTTTAAGAAAGTGCTAAGATCTTTCTAAATATTACGA
AACAATTAAGACATTAACAAAAACGAGCTCTTTTCTTCTCTTTTATACCAAGCTGTACCCGCAGGTAAAATGTACTTTTATGTGGCTGCAAACAT
TTGCCAAATAAAAGCACACACAAATGCACATAATTTAGGTGAGCGAGTAATTAAGCCCAAAGTGGACAAAAGAGGAGGGCAAAAACGGAGCCAAA
AAGCATCCATCGTTTTTTATGGCTACTTGGTCGTTCGTTCTGTCAATACAATACCCAAACACTGTAAAAACCAATTGGAAGTTTTTATTGAAAA
CATTAATAAAGTCATTAATATTGTTGTTGTTATAGATTCCAGAGACATTAAATAGTAAATAGTATTTTAAAGTTAACAAACACATATTTATGTTA
CAAAATCCCTGAATTGTTTTCTCTGTACAGCTTCTCTCTTTCTCTCTTGGCTCTGCCGTAAAATACATGTGCGAGCACACCTGCCTGCGTCGACG
TCACCGTCGGCTGCGCAGTCGCCGCCGCGTCT
(SEQ ID NO: 1051)

Exon: 1001..1352
Exon: 3001..3352
Exon: 3505..3688
Exon: 3758..4352
Start ATG: 1251

Transcript No. : CT27002
GCTCCTCCTTGCTCACACCTACAACTACACTCGCCTTTAACTCTCTCAATCTCTCCAGTTCGGTGCTCGTGTCGGTCGTAAACATAACTCAAAAA
GCGCTGCTGAAGTCAGTAGCCGGCTAAACGCGACTCGGATCGGAAGTCTCCGCTCCTGGCAATCAGAAAATCCCCTCCACGCGATAAGGGTGTAC
ATAAAAAAAAAAAAATAAATAAAACAAGTTAAATAAATATATAAGAAAATCACATAAGAAATGCAACTTTTCGACGACTTTTGCAAAAGCTTCAA
CAAGGAATTGCAAAGGGCGAATTTCGGCTTTGCGTACAATCGAGTTCATTTATTCTACAGATCTCAGTGGCAAAAAGATGAGATCAACACAATAT
ACTTGCTCTACCGATGGATTTGGGCACTGTTTTTCCTGGGCGTGTACATCATGTGCGTTATCGTTCAGTTTTGCGATGGAAAGTTCTTCATCTAC
ATGACCAACTGGGGATTCGGGCTCTGTACGATCACCATGCTGATTTCCGCCGTACAAGTCACCTGCTGGCACTTCGATGTGAGGAGCACCCGGAG
CCTGGTACAGGAGTCCGGTCACAAGGCGGAGACGTCGAGGGGCCTGAAAATCTACTGGTGGCTCTACAATATGACACTGTCGCTGGCTCTGATCA
TATCAACAGTATACTGGGTGTTCCTCCATGGAAAAATGAACAAGCCCATGCGATTCCCTGCCATCAGCATTATCACCCACGGCATGAATTCTGTG
ATGATGCTAATCGATTTCCTGGTCATTGCATTTCCGCTTAGGATACTTCACATGGTGTACGGAATGAGTCTGGCGATATTCTTCTTTTTATTCAC
GCTGATCTACCATTTATGCGGGGGAACAGATGAATTTGGCAATCACTACGTGTATCCCATTCTGGATTGGAACAATCCCAACCGCTGTATGGTGA
CCTTTGTGGGCATCTTCCTGCTCATTATGTGCTACTGGGTGCTGCTCTTTGGACTCTACAAGTTGAAGAGAATGTTCAATAGGGCATTCAGTGTG
GTTTGGTCTCCTCATGCTGTGGGTCTGATATGAGGGAGTTAATACAACAAAAAGTCATTGAATATCACCTCATGGGCACCCGCACGTATACCATG
TTCTTATATGCATTGCCAGCATTATGTAACTCCCATTAACAAATCCATCCAAAAACGACACTGAAAAGGGAGTCGCACACTTGCATGCATTTATT
TATATCTAGTATTTCATATTGTAAGTTTTAATCATTTGGTTCCTTAACATTGAATTGGTTTAGTTAGGTTAATTCTTATACATTATGTTGTTATT
ACATATTTGGTTTAAATAGTATAAATATGAAATTTGTTGAAAATACTCTACCCAAGGGTTAGATAAAAAGAATAATGGAATTGTATTAAAATATA
TCACGAATATCAAAAGTGGAAAGAAACGAAATAAAGAAAATGTGGCGTTATTGAATTT
(SEQ ID NO: 1052)

Start ATG: 251

MQLFDDFCKSFNKELQRANFGFAYNRVHLFYRSQWQKDEINTIYLLYRWIWALFFLGVYIMCVIVQFCDGKFFIYMTNWGFGLCTITMLISAVQV
TCWHFDVRSTRSLVQESGHKAETSRGLKIYWWLYNMTLSLALIISTVYWVFLHGKMNKPMRFPAISIITHGMNSVMMLIDFLVIAFPLRILHMVY
GMSLAIFFFLFTLIYHLCGGTDEFGNHYVYPILDWNNPNRCMVTFVGIFLLIMCYWVLLFGLYKLKRMFNRAFSVVWSPHAVGLI*
(SEQ ID NO: 1053)

Classification: known_flybase_gene
Gene Symbol: rost
FlyBase ID: FBgn0011705

Celera Sequence No. : 142000013384623
TTTTTTCAATGTTGTTTTAGCTTGAGTTGCCTAATCTATGCAAACGAAATATATGAAGTGAAAATTGATATGCTGATCTCCACCATCCTATATAC
AATCCATAAATCGTATATACAGAAAGAGAAATGTATTAAACTCGGCCAATATCGAAACGCATTTTTTAGATGTTGTTTTTGTGTTTTGAACTGCA
TTCGACCGTTGACCGCAAATGTACCTAAGTGGCTATTGTTAAAACAAATCTGCTCTTTGGCAGTTGAATGTGCGAATACAAAGAATTACACAATT
TATACAAAACATATTTAACCCAAATGTATACCCTTATACAGACATCTCTATATAAATATATTTATGTGCAAGTATTTGATGAAATAAATATTCAA
ATTATTAAAAAGCATTTCTCCGATGAGTTGATATTTGTGTTTTGAATTTGGCATGGGAAATATATTTATTAATAGCTTGAAAAGAGAGGCAACGT
CTTTTTGAAATTAAAAACCTTTGTTATATGTATACCTTGTAATTTAAAATTATTGGTATTTTTACGTAAAGCGTATAACTTTAAAGGAATGAGAAA
CCATTGTAATGTAGAAAATATTTAATAATATTTCTTTAAATTCATTGTATGGTAACTTATGTAGTTACCGCTTTATTTAATTACTAAGTACAATA
TCTTGTTGTTTTATGCCGTAAGCTTGTTACGAGCGGAGCTGAAGTTCCAGTGTGTCCAGTCTGACGATAAGAAGACAGAAGATATCGTCCTCCAG
GAAAGGTCTTGGCGTTAGTACCTCTTTTCGCCGTGATGCCAGACCGGGTTTCAGTCTGGGCGCCACAATTGAAATAATAATTTTTTATTGCTATA
ATAGCCATGCTAAGATAATAGAAATTTTGAAAATTGAGTATTTTTTGAAAGTTGTTTCAATGACTTAATTTTATTTTAAATAAATGCGCCACTTT
GAAAGCTTGAAAAAAATACGGCTTCAGGGTCATGGTATTTAATGTCGTGGAAATACCACACTCTGGTAACTCTGAGCGGGCGTCACTCTTTTCGT
CTCTGGGCACACTGTCGGCCCTCGCACGCGTATTTTTCTGCCGATTTTGCGTGTAAATTTAATTGTGAAAACATAGTAAAACAGCTGCAATCATG
GCCAATTTCGATCTGACACGCATCAATTGCCAGTTTTTGGACAGGCATTTGACCTTCCCGCTGCTGGAGTTCTTGTGCGGCAAGGAGGTTAGAAA
AGCGACCAGGCGGTGCTCCGCTGGCGGTTGCCGAGTCACCAGTACATAACTATGGGAAATCTTCATATGTGTGACTTTCGTTGCAGATCTACAAC
CAGCAGGAGCTGCTGGAGTACATTTTGGAGACGGTGAACAAGACGAACATGATCGATTACACGATGGACACCCGCAAGCGTCTCAATCTCAGCCA
GGAGATGCCCGAGGAGCTCGTGCAGCGCAAGGCGGAGGTCCTGGCCACGCTTAAGCAGCTGCAGAACGAGGTGGCACCCATCATGAAGGCCACCG
ACATTCTTAAGAACGGTGAGAGCATGAAGGACTCGAAGACCTTCGTCAACGCCCTTCAGAAGGACTACAATTTTAAGGTGGAGCACCTGGAGAGC
GCCTACAAGCTGGCCAAGTACCTCTACGAGTGCGGCAACTATCAGGAGTCCACCTCTTACCTGTACTTCTGCCTCATCGTCATGTCGCCCAACGA
CAAGGTGCGTATGGAGCTAAATTAACATGAAAAGCGGCAAAAACCACTAAAACAAGAATATTAATTGATATTGTCTCCCAAATTTTGCAGAACTA
CCTTAATGTGCTGTGGGGCAAGCTGGCCGCCGAGATTCTGACCCTCAACTGGAACACTGCTCTGGAGGATCTGACGCGTTTGCGCGACTACATTG
ACAACGCCAACTTCAGCACCATCCAGGCCCTGCAGCAACGCACCTGGCTGATCCACTGGTCGGTCCTGGTCTTCTTCAATCACCCCAAGGGACGC
GATCTCATTATTGAGATGTTCCTGTACAAGCCCCTGTATTTGAACGCCATTCAGACAATGTGTCCGCACATCATGCGTTACTTGGCCACCGCCGT AGTCATCAACCGCACCCGCCGCAATGCTCTAAAGGATTTGATCAAGGTGATCCAACAGGAGTCGTACACGTACCGCGATCCCATCACCGAGTTTC
TGGAGTGTCTGTACGTGAACTTTGATTTCGAGGGAGCGCGTCTGAAGCTGCACGAGTGCCAGACGGTGATCCTCAACGACTTCTTCATCGTGGCC
TGCCTGAATGAGTTCGTGGAGGATGCCCGCTTGATGATCTTCGAGACATTCTGCCGCATCCACCAGTGCATCACCATCAGCATGCTGGCCGATAA
GCTGAACATGAAGCCCAACGAGGCTGAGTGCTGGATCGTCAACCTTATCCGCAATGCCCGTCTGAATGCCAAGATCGATTCGAAACTGGGTCATG
TGGTGATGGGCACCCAGCCCTTGAGTCCCTATCAGCAGCTGGTGGAGAAGATCGACTCGCTGTCCATGCGGTCGGAGCATTTGGCAGGTTTGATT
GAGCGCAAGAGCAAGCAGAAGCAGAATCAGGAGTCGGCCGACTCCTGGAAGTACTACTAGTTGCTGACTTTTTATCCACAATTAAGTTAAGACTC
TTTGTACCCTTTAAAAACCGATGATTGCGCGCAGTCGAGCGAATAAATTAACATCTTACTCATTCGCTCAATTCAACATTTGATTTTATTTCCTT
CGGAATCAAAATTAGTTATACAAAAAACAATACCAAGGCGGGAATTTGTAATTTCGCTAGCCTACAGAATGCAAACGTCTGCTAATCCTAGAATT
AGTTGTTTGTACCTACAAGTGGGTGCTGGATCTTTATGACGATCTGGCCCCGGATCACACTATTGATTGCTACCGCGATTTCTGCTTGACCACCA
ACCAGGATCTGACGGGCAGGTCCTGCAAGTAAACGATCCATTTGCGCACCAGCAGCAGCCACACTATGCCGTACAGAACGCAAATGCCCGACTCC
AAGTAGTACCCATCGAAGGTTATCTCGCACTTGCCAGCCGACGCTTCACAGCTCTGCGGGAGAAAATTAAGAAAAATATTTGTTTAGTTACTTTT
ATCTCATAACTGGCAAAGTTTATCTTTTCCTGGTTTGGGGTAAAACTTTCACCATACATATGTATCCATATACAATAATAATAATAATCTTGTAT
GCTGTAGAATCTCTCTCTGAGCACTCACCTGTTGCTCCTCCTTGCCCTGGCAGGTATTTTCCGCATTATTGGAGCACTGCTTCCAGGTGAGCACG
TCCACCAACCACAACACCACTGTGTTGGGCCAATTACCGCCCAGATTGCACAATGTGTTCAAAAATGTCATGTAAGTGCCACCGACGGCTGGATC
GGAGATCTTGGCGAAAAAGGCCATGGCGGCCACAAACATGGAGTACAGGAATACTTGGTAGATGGCATAACTGGTGATCAGCAGGACGTAGTAAT
AAGCAGGCACGGCTCCTCCACGGACAATATAGGGTGTGATGTAGGCCAAGCCAGTGGCCACTGTTGCCATGATGATGCGATAGGGAATGGCCTTC
AGATAGACGTCCATCGGACGTGGTCCGTTCGTATATCGACCGACCGCCAGCGGCAGAATGAGCTGCAGAGGAATTAGGGGAATGGCGAGTAAAGC
CAGCTTATCCTTCGGTACACCAGCGTCAATG
(SEQ ID NO: 1054)

Exon: 1001..1227
Exon: 1322..1714
Exon: 1801..2736
Start ATG: 1138

Transcript No. : CT27364
AAATACCACACTCTGGTAACTCTGAGCGGGCGTCACTCTTTTCGTCTCTGGGCACACTGTCGGCCCTCGCACGCGTATTTTTCTGCCGATTTTGC
GTGTAAATTTAATTGTGAAAACATAGTAAAACAGCTGCAATCATGGCCAATTTCGATCTGACACGCATCAATTGCCAGTTTTTGGACAGGCATTT
GACCTTCCCGCTGCTGGAGTTCTTGTGCGGCAAGGAGATCTACAACCAGCAGGAGCTGCTGGAGTACATTTTGGAGACGGTGAACAAGACGAACA
TGATCGATTACACGATGGACACCCGCAAGCGTCTCAATCTCAGCCAGGAGATGCCCGAGGAGCTCGTGCAGCGCAAGGCGGAGGTCCTGGCCACG
CTTAAGCAGCTGCAGAACGAGGTGGCACCCATCATGAAGGCCACCGACATTCTTAAGAACGGTGAGAGCATGAAGGACTCGAAGACCTTCGTCAA
CGCCCTTCAGAAGGACTACAATTTTAAGGTGGAGCACCTGGAGAGCGCCTACAAGCTGGCCAAGTACCTCTACGAGTGCGGCAACTATCAGGAGT
CCACCTCTTACCTGTACTTCTGCCTCATCGTCATGTCGCCCAACGACAAGAACTACCTTAATGTGCTGTGGGGCAAGCTGGCCGCCGAGATTCTG
ACCCTCAACTGGAACACTGCTCTGGAGGATCTGACGCGTTTGCGCGACTACATTGACAACGCCAACTTCAGCACCATCCAGGCCCTGCAGCAACG
CACCTGGCTGATCCACTGGTCGGTCCTGGTCTTCTTCAATCACCCCAAGGGACGCGATCTCATTATTGAGATGTTCCTGTACAAGCCCCTGTATT
TGAACGCCATTCAGACAATGTGTCCGCACATCATGCGTTACTTGGCCACCGCCGTAGTCATCAACCGCACCCGCCGCAATGCTCTAAAGGATTTG
ATCAAGGTGATCCAACAGGAGTCGTACACGTACCGCGATCCCATCACCGAGTTTCTGGAGTGTCTGTACGTGAACTTTGATTTCGAGGGAGCGCG
TCTGAAGCTGCACGAGTGCCAGACGGTGATCCTCAACGACTTCTTCATCGTGGCCTGCCTGAATGAGTTCGTGGAGGATGCCCGCTTGATGATCT
TCGAGACATTCTGCCGCATCCACCAGTGCATCACCATCAGCATGCTGGCCGATAAGCTGAACATGAAGCCCAACGAGGCTGAGTGCTGGATCGTC
AACCTTATCCGCAATGCCCGTCTGAATGCCAAGATCGATTCGAAACTGGGTCATGTGGTGATGGGCACCCAGCCCTTGAGTCCCTATCAGCAGCT
GGTGGAGAAGATCGACTCGCTGTCCATGCGGTCGGAGCATTTGGCAGGTTTGATTGAGCGCAAGAGCAAGCAGAAGCAGAATCAGGAGTCGGCCG
ACTCCTGGAAGTACTACTAGTTGCTGACTTTTTATCCACAATTAAGTTAAGACTCTTTGTACCCTTTAAAAACCGATGATTGCGCGCAGTCGAGC
GAATAAATTAACATCTTACTCATTCGCTCAATTCAA
(SEQ ID NO: 1055)

Start ATG: 138

MANFDLTRINCQFLDRHLTFPLLEFLCGKEIYNQQELLEYILETVNKTNMIDYTMDTRKRLNLSQEMPEELVQRKAEVLATLKQLQNEVAPIMKA
TDILKNGESMKDSKTFVNALQKDYNFKVEHLESAYKLAKYLYECGNYQESTSYLYFCLIVMSPNDKNYLNVLWGKLAAEILTLNWNTALEDLTRL
RDYIDNANFSTIQALQQRTWLIHWSVLVFFNHPKGRDLIIEMFLYKPLYLNAIQTMCPHIMRYLATAVVINRTRRNALKDLIKVIQQESYTYRDP
ITEFLECLYVNFDFEGARLKLHECQTVILNDFFIVACLNEFVEDARLMIFETFCRIHQCITISMLADKLNMKPNEAECWIVNLIRNARLNAKIDS
KLGHVVMGTQPLSPYQQLVEKIDSLSMRSEHLAGLIERKSKQKQNQESADSWKYY*
(SEQ ID NO: 1056)

Name: eIF3-p48
Classification: translation_factor
Gene Symbol: Int6
FlyBase ID: FBgn0025582

Celera Sequence No. : 142000012789666
TATTGCTTACAATGCCAGCTATCGATAGTAACGATAGTAGTGTCACAGTTAACTGTTTCATGGCTGGCTTCGTGCACAGCTCACCGAGACTATCG
ATAAATATCGCATCTGTGTGGCTGCACACCGAATTCGTAATACACCAAATACCGGTACCGTACTCGATGGCATTATTTAGGAACTTTCCCATCGC
CGCGGCAAGACTGAAATCGACTGGCCTTTAGATGCTCTTTGGCGGTGGGCGCCGCTTGACTTGCCAGACTCTCCAGGCCGAGTGTGTGTGTGTGT
AGTGGTTGTGCTAGCAGAGCTGTTGCAGAAACTAACTGGGAAAACACAAGATAGACGCGTGTGCGGCGAGCAGTAGCTAAATTGAACTGAAGTGA
ACAGAAAATATTTACACAAAATAATAGAGATACAACTTCGGAAAAGCAAGCATACAACACACCGGGACTCCGCAATACGGGTTTTTATTTCGTC
TACTCTTCCGTACCTGGGCAGAGATTTAGATTTATCGCCTCCTCCACCCACTACTTCATCATCGACATCACCAGTGCTGTTGTTGTTGCTGTCGT
TCCGCCTTCGCTCTCACGTAATCCGCCCCCGCACCACCTCGCCCGTCGGCCAACCGGCCCACAAACTAACTGACTGATAGACCAAAAATCGATTA
GCGGACTCTCTTCCTCTTCAACATCTTCGGCATTCGTGTGTGCGTTGCTTTGCGTTACGTTACGGTTACCGTTACGTCGCCCGCGCGTGTGTGTT
GGTGTGTGAGCAAGGTGTGGTGTGTATAGAAAATCGATTGGCAATTTGAACCGAAGAGCGCTATCGTCGCCGCAGTCGCCGCGTGTGTGCCGTTA
CGCGATTTTCAACAGCAGCCGCGCAGTAATATTGCTTTTATTTTTTTGCCTGTGAGTCCTCCTAAGTGAGTGCGAAAGAGAGAGAGCGAGAGTGA GCTCTCTAAAACCTCTGCAGAAAATAAAAAGGAAAAGAAAAACACCGGACATGGATAAATCAGCGGCCACGAACTCGGCCACTGCCGATGGCCAA
AACGAGGCAGCAGCAGCAGCCGCCGCCGCAGCAACAGCAGCTGGGTGTGGCAGCAACAACAGCAGCAGCACCAGCAGCAGCAACAACACTGCAAA
CAGCAATAATGCACTGCAGCGTTTGGCAACAACAACAAGTGCCGTTGTGGCATCCCCGATGACGATCAACCTGAACATCAGCACCACCACCGGCG
GCAATTTCGGCGTCAGCGTCGAGCCGCACATCAGTGTCGAGAGTCTGAAGAAGATCATCGCCAAGAAGCTGAAGGTGGCCAAGGATCGCATCTGT
CTGCTGCACCGGGAAAAGTGAGTACCCCTTTAGTATTTTTTTTAATTTACGTTACATTTAAAAGAAACTTGGCTTGAACTGTAATTTTTTGGCA
GTCAAGTTTTTTGTTGTTTGTTACTAATTTAAAAATTAATAACAGTTAATATGGCTTAGATCGCCAATTTTTATGTTATTTATCTGAACATTTTC
TTTTTGTTTAATTGACGAGACTAATGTTGAATGTTAAATATTACTTATTAATCTATGCATTATATTTGTTACATAAAAAGGATTGTTAAGGTTTA
ATAAGCCTGTGTTTGGACAAGTGTGTCATTTGCATATTGCCCAGAATATCTTATGATTGTGCCAATGAGGTAATATCAATAAACCAGAAATAACT
GATAATGCAAAATGTTTCGCAAAGAATATTATCTTGAAAGTCAGGTGAAAAGTTAAGTGTGATATCTTTTATAGAAAAATTCTTGAGGAGTGAAT
AAGTCCTGTTCTAATTAATCCTTGCGTTAAGAAAATCGTATGGCTTCGGTGAAACGCCTTGTATGTTGAGAGTTTTCTTTTTTATATTTTTATTG
GATATCCTCTTTTTTTCGAGCTTTGTTTGGTTAAAATGCTTTTGATTATCTTCTTTCACCGCTCCACCCCCCTCCACAGAGCTCCTTCTCTAACC
CCTTTGTTGAGCTTTGTTAGAGGGAGAGATATAGAGAGAGAGCGAGAGAGGTGTGCGTGTCTGTGTGTGAGCGTGTTTTTTAGTCGCTAAGCTGC
CATTGTTTAGTTGATTTGCTTGCTGTTCTCGTTATTATTATGATTATTATTGATATAACCTCCAAAATAATGGCATGTTTGAAGGGTTAAGCACA
AAGAGCTTGAGTGTGGTGGAGTCCTTGTGTGGAAGGGGGGGGGGGGGTGTACCAATTGATCTAATCACACACATACACACGTACACACATGTACA
CTTAGTCTGAAAGCGATTTCATAATCTATTTGTTATTATACAAAACAACGCAAAATAAAAGTAGCTAAATG
(SEQ ID NO: 1057)

Exon: 1001..1351
Start ATG: 1001

Transcript No. : CT27494
ATGGATAAATCAGCGGCCACGAACTCGGCCACTGCCGATGGCCAAAACGAGGCAGCAGCAGCAGCCGCCGCCGCAGCAACAGCAGCTGGGTGTGG
CAGCAACAACAGCAGCAGCACCAGCAGCAGCAACAACACTGCAAACAGCAATAATGCACTGCAGCGTTTGGCAACAACAACAAGTGCCGTTGTGG
CATCCCCGATGACGATCAACCTGAACATCAGCACCACCACCGGCGGCAATTTCGGCGTCAGCGTCGAGCCGCACATCAGTGTCGAGAGTCTGAAG
AAGATCATCGCCAAGAAGCTGAAGGTGGCCAAGGATCGCATCTGTCTGCTGCACCGGGAAAAGTGA
(SEQ ID NO: 1058)

Start ATG: 1

MDKSAATNSATADGQNEAAAAAAAAATAAGCGSNNSSSTSSSNNTANSNNALQRLATTTSAVVASPMTINLNISTTTGGNFGVSVEPHISVESLK
KIIAKKLKVAKDRICLLHREK*
(SEQ ID NO: 1059)

Celera Sequence No. : 142000013384504
AAACTATGCGTCACCCAGCGAGTATGTGGTCCTCTTCGGCTGCATGTGTATGACCTGCGTGGGCGGTTCGAGACCAAAGGGGTAACTCACTTGCA
AACAAATTTTTCGGTCGTTCGGCCATTGTGTGGTGGCTGAAAGTATCGATGCGCCTTTGTGTGGCTGTCCTAAGGATGTTTTGTCCGTTTTCT
GCAGGCGCCGCGCCCCGAATACAACACGTCGACTTGATGCTCCTTTGGCCCTCCGATCGCCTGGTTACTGGGCCGCCTTTGATGGGCTCTTCGCC
GTTTGCAACGCAACTACTTTTTCAGCAATCGAGCGCACTGATATGCACTTTTTCCGCAATTTCGCTAAACATTTACATAAATAGCAACCAAAACT
TAAAAGAGCTAGAGATGAAACATTGATTATTTGCGGCCAATCGATAGCCATCGATAGTATGCGCACTAGCTTGCGATAAGCAGTCCTGCAAGGTG
CAAAAGTAGTGAGGTGGGTAATAAAACGAATATAAAAATGTCACCTATAAATAATTATTTCTTTAAAACCAAGAGATTTGAGTTTCTATTTTTCA
CAAATTAATCCCAGCTTTGTTAAAGTTTTTACTAGTTGAAAAGTTACATTTCGTCAATAAGTGACGTCGACGCCTACATAAACCAATCTGCGCCA
CCTTAAAATCAATGCACAATCACCAGTGATTTAAAACCAGAAAATTAAAACATACATAATCATGTCCAGCGGATTTGTTCGCAGCAGCTACAAAT
TGTTCGTCGGCAACCTGCCATGGACGATAGGTAGCAAGGAACTGCGGACCTACTTCTCAAAGTACGGGCACGTGGCCAACGCGGAGGTGGTCTTT
GACCGGCAACTGGGCCTGTCCAAGCACTATGGCTTTGTGGTTTTCAGCCAACGGGATGCCTTCAACAGCGCCAGCAACCAGAACACCCATTTCCT
CGATGGACGAGTGCTCACAGTCCAGCGGGCGAATGAAAGTCCTCAGAGTTAATCAATGAAGAATTTAATGATTTATTGGTTAGACCAAAGGAAAA
GCATGAGAAATGTTTGTTAACAGCTTAGTTTTACACAAATGAATGCAGCACTTGCTTCAAATCGTGGCATCTTTGATTCATTTGGGCAAGTAGAA
CTTGCTGTTGGTGCCCACCACGTCCGCAACATTAGTGTGACCCAGCCGTGTGATCAGCGCCGACAGCTCCGCCTTAATGTCTTCCACAAGAGCGG
GTCCCTCGTACACTAAAGCCGTGTAGATTTGGACGTAGGAAGCTCCAGCTTCGATCTTTTCGTATGCATCATAGCCGGAAGCCACTCCGCCGACG
CCTATGATGGGAATCTTTCCATCGGTGAGCTGGTACATCTGGGCGATCATCTCTGTGGAGCGGGCCTTGAGTGGAGGACCACTTAATCCGCCAGT
TTCCTCGGCCAGCTTGTTCTTTTCGATGTTTTCCCGCGACACCGTGGTGTTTGAAACGATCAGGCCATCCACGCGGCTCTTCTTGCGCTTGATTA
CCCACACGATGTCCTTCATGTCGTCCAAAGATAGATCCGGCGAAAGTTTCAAGAGTATAGGCACATTCTTGTTCTTATCCAGGGAGGATTTCGTG
TCGTTGACCTGTTCCAGGAGCTCTCTTAGCTTCTCCTTGCTCTGCATATCGCGCAGGCCCTTGGTGTTCGGACTGCTCACATTAATGACCAGGTA
GTCTGCTACGGGCCCGAAAACCCGAACACCCTGTACATAATCCGCTATCGGGCTCATGGTGGTCTTGTTCCGGCCCAGATTCACGCCCACAACTC
CATTGAAGTTCTCCTTTTTGCGGAGCAAGCGCAGCCGTTGGAGCACGGCCTGATGCCCGTCGCTATTAAATCCGTACCGATTAATGATGGCCTTG
TCCTCGGTCAACCGGAATACTCTCGGCTTGGGATTGCCCTCCTGAGCCGCCGGGGTAACTGTGCCCACCTCTATAAATCCGAATCCTAGATCCTG
CAGGCCGTCCACCGCCTCCGCGTTCTTATCGAATCCCGCTGCAATGCCAATGGGATTGCTAAGCATCCGGCCAAAGAACGACGTGTGCAAGTTCT
GGTCATCATGGTACTGTGAAACCGGGCACAGGCGGTACTTGCACGCCAGCACGGCCAGTTGATGGCTGGCTTCCGCCGGAAGAAGTCGCACCGCT
GGCATCACGAAGGTCCGGAACAACTGGTCCTGGTTCTTGTATGCCGTAATGCCCGCCACCAAGGCAGCTCCTCCGACTGTAACGATTCCCAGCGA
CCGCAAACGACCCTGTGGGCGGAATCATTCTGTAATCCGGTCCCGTTTAAGCCGTACTTTACTCACAACTCTCCGCGTGGCGTTTTTAGCATTCT
TTAAGTGATCCTGATCCATGACGACTATCGCCGGATATCGATTGTACCCGATAGAGTATTAAAAGTATAATATGTAAAAAAGTAAATGCATGTAC
TAGAGTTTTAACGAAAATTCAATTTGGGAGTAAGTCTGGCCATTTTGAAGGAAAACTCATGCGATATATAGTTACTACGGCAAGCATCAATAATT
TTCTTTTTTTTCTGTGTAGCAAATGAACCCCTTCTATTCACAACCATGCCGAAGAGAATCGATAGTCCTCCAGTGTCACCTCTAATGGTTGAGTC
AGTTTGTTATGGCCAGCTAAAAATTAGAAATTTCGTTCTCTAAACGCTGATTTGGCCACCCGAGGCAACCATGAAGGGCGGCACCTTTCGCAACA
CGCAGTGGGATCCCACGCTGCTGTCCTCACAGATTGTGTCCATGCAGTTCTGCGTGTACTTCACCCTTGGCCTACTCGTCTTCGTGGCCAACAAG
TTGTCCGGGGACAACTATAGTCTGGATCACTTGTTCGAATACCATGTATGCCATATGCTATATACCATATATCATGGAAACCCCTCTCCTTACTT
TGATTTAATGTTGCTTAAAGGAGATCCACATCTACGACATGGGTGGCCGCCTGGTGATCTGCGCATTTGTTTTAAATGCGTTCTTAGCCTCCCTG
GCACTGTGGTGCATTGTGAGAAGAGCCAAGCTCTGTCTGGACTTTAGGTGGGCTTATAGCTAGTGCACACACTTAATCTTTTGCTTTTACAACTC
ATGCTTCCCTTTCATGGCAGTTGCACCTTCCACGTGCTGCATTTGCTGATCTGCTGGTGGTACAACCGCTCCTTTCCCGCGAACGCATCGTGGTG GCTACTGAATGTCATCACCGGCACAATAATGTGCATAGGCGGCGAGTTTCTCTGCCTGCAGACCGAGATGAAGGAGATCCCAGTGGGCTATGCGG
CCCTCAATCAAAAGTCGGACGTCTGACTCGAAGCCACCAACTTGTGATGCCTGCTACCCCCCCAACCAA
(SEQ ID NO: 1060)

Exon: 2394..2347
Exon: 2292..1001
Start ATG: 2394 (Reverse strand: CAT)

Transcript No. : CT27530
ATGGATCAGGATCACTTAAAGAATGCTAAAAACGCCACGCGGAGAGTTGGTCGTTTGCGGTCGCTGGGAATCGTTACAGTCGGAGGAGCTGCCTT
GGTGGCGGGCATTACGGCATACAAGAACCAGGACCAGTTGTTCCGGACCTTCGTGATGCCAGCGGTGCGACTTCTTCCGGCGGAAGCCAGCCATC
AACTGGCCGTGCTGGCGTGCAAGTACCGCCTGTGCCCGGTTTCACAGTACCATGATGACCAGAACTTGCACACGTCGTTCTTTGGCCGGATGCTT
AGCAATCCCATTGGCATTGCAGCGGGATTCGATAAGAACGCGGAGGCGGTGGACGGCCTGCAGGATCTAGGATTCGGATTTATAGAGGTGGGCAC
AGTTACCCCGGCGGCTCAGGAGGGCAATCCCAAGCCGAGAGTATTCCGGTTGACCGAGGACAAGGCCATCATTAATCGGTACGGATTTAATAGCG
ACGGGCATCAGGCCGTGCTCCAACGGCTGCGCTTGCTCCGCAAAAAGGAGAACTTCAATGGAGTTGTGGGCGTGAATCTGGGCCGGAACAAGACC
ACCATGAGCCCGATAGCGGATTATGTACAGGGTGTTCGGGTTTTCGGGCCCGTAGCAGACTACCTGGTCATTAATGTGAGCAGTCCGAACACCAA
GGGCCTGCGCGATATGCAGAGCAAGGAGAAGCTAAGAGAGCTCCTGGAACAGGTCAACGACACGAAATCCTCCCTGGATAAGAACAAGAATGTGC
CTATACTCTTGAAACTTTCGCCGGATCTATCTTTGGACGACATGAAGGACATCGTGTGGGTAATCAAGCGCAAGAAGAGCCGCGTGGATGGCCTG
ATCGTTTCAAACACCACGGTGTCGCGGGAAAACATCGAAAAGAACAAGCTGGCCGAGGAAACTGGCGGATTAAGTGGTCCTCCACTCAAGGCCCG
CTCCACAGAGATGATCGCCCAGATGTACCAGCTCACCGATGGAAAGATTCCCATCATAGGCGTCGGCGGAGTGGCTTCCGGCTATGATGCATACG
AAAAGATCGAAGCTGGAGCTTCCTACGTCCAAATCTACACGGCTTTAGTGTACGAGGGACCCGCTCTTGTGGAAGACATTAAGGCGGAGCTGTCG
GCGCTGATCACACGGCTGGGTCACACTAATGTTGCGGACGTGGTGGGCACCAACAGCAAGTTCTACTTGCCCAAATGAATCAAAGATGCCACGAT
TTGAAGCAAGTGCTGCATTCATTTGTGTAAAACTAAGCTGTTAACAAACATTTCTCATGCTTTTCCTTTGGTCTAACCAATAAATCATTAAATTC
TTCATTGATT
(SEQ ID NO: 1061)

Start ATG: 1 (Reverse strand: CAT)

MDQDHLKNAKNATRRVGRLRSLGIVTVGGAALVAGITAYKNQDQLFRTFVMPAVRLLPAEASHQLAVLACKYRLCPVSQYHDDQNLHTSFFGRML
SNPIGIAAGFDKNAEAVDGLQDLGFGFIEVGTVTPAAQEGNPKPRVFRLTEDKAIINRYGFNSDGHQAVLQRLRLLRKKENFNGVVGVNLGRNKT
TMSPIADYVQGVRVFGPVADYLVINVSSPNTKGLRDMQSKEKLRELLEQVNDTKSSLDKNKNVPILLKLSPDLSLDDMKDIVWVIKRKKSRVDGL
IVSNTTVSRENIEKNKLAEETGGLSGPPLKARSTEMIAQMYQLTDGKIPIIGVGGVASGYDAYEKIEAGASYVQIYTALVYEGPALVEDIKAELS
ALITRLGHTNVADVVGTNSKFYLPK*
(SEQ ID NO: 1062)

Name: DIHYDROOROTATE DEHYDROGENASE PRECURSOR
Classification: enzyme
Gene Symbol: Dhod
FlyBase ID: FBgn0000447

Celera Sequence No. : 142000013384507
GCAAACGTGCGAAATCAACAGAGAGAACGAGTGAGCATGCCCACAGAGTGCGAGAGAGAGCAAGAGCGGGGGTGCGAGCGCAAAAGACCGACAAT
TTATTTTACTTTTATTAACATGCGCGCAAAATATTTATATAAATTGATTACACATTTTCTTGTTCTTTTATCATCACCCCCTTTTTTATATTCAC
CCTGGCAAATGAATTACGCTGCCCCAGCCAAATTGTTTATATATTATTTATCAATCGATTTTAGGGGCATGCCAAATTTGATCAGACGCCAGTCG
CACACAAACACACACTTGAGCACACACATTCACAGACCAACACTCGCGCATACATACACACGCACCAGGGTGTTTGTTTTGTTTTTGTTTGCGGC
TTTTTTTTTTATCAATTTGTGATCTTTTTTCGCAGCCGCAAATTTGATTGTGATTTACCGCCGATTGGAAATGTAAACAATGCTGTCGAACTATC
AGCATAAGGCTGGCAGTTTTAAAATACTTTTCATATTTTATAGCTGTTGGGTACTCACACCTTAGCTTATTTGAAAAATTTACATATTACAAGCA
CGCCGTTCTAGGTCTGCTTCTTCTTACGCGCGAACATTTAGTGTGACCGCAGCTCGACCGTTCAAATATACCATTGCGAAGCGCACTGAGAAACA
CTCTCCAATAGTTCTAAGATACCAAAAATTTAGCATACTACTATATGTAAGTTATAATTTCATTTACTATCCCATTAGAGAAATTAATTGATTTT
TATGTTCTATAATGCATTTAACTAGTTGCCCTAGTTTTAATGTTGTTAAAATAGCATTACAACAATTACCGTTTATAACTTCACTTTCTTCAGAG
TGACCATATAATGTAAAGTACAGTGAACACTGTATATAAAGAATCAATACAACCATGGATTTACATATTTTTCCATCTGGTTTATATCAATAGAT
AATATATGTTAAATGATATATATATAAAAACTAAATTACACAAAATTTTTTTAGGTATAGTAGGTTTATTTAAACTTGTATACGATTGAAATTTCTG
CAATCAAATCAAATTTGTTGTTACAATAAAGTTCAGTTCTACTTCGGAACTTGAAATCTTCCCCAAATATGTTATTTATGTGTTATTTATTTGGT
AATTTCAATCCAAGTTGAAATCGTTTTCCGAGCTATGTGTCGTCATTACAGTGCAGTGCAGTTGTAAACGGTTTGTCCGATTTCTCAGCAATAAA
TCGGAATATATATGTAGACAAAGTGTGTTGTTTTAGGAGGGGAAGGTTCTCTAAAGTCCAAGTAGGTCCTATCCATTTTTGTGTTTTCTTCTCTT
ACTTGCAGATTTTTTTTCGTTTTTTTTTTTTTGCTTTTACAACATTCTTTTTTTTTTGTGTTGATTTTTGGGGAGGGGTGTGTGGAAATGTTTAT
AAATTGTATGTTTTAGGCAGCTACCGATTCGGAATCGTTGTAGTTATCCGAAACATAACCGTCGTTGGCATCATTTTCGCCATCGGAGTTCCATT
TGAGGCCATCTCCTTTGGTTGGTGTCCCATCCACGGCACGGTCCTCGTCGTTCGACTCCTTCTTGGAGTTGTGTTGGCCCTGATCGGCGGAATCA
GCATCATCTGCATCGTCATCAATATTTTTCGCTGGGCGACTACGGGGCTTTGTTGTTTCCTCTTTGGACACCTTGCCAGCGGCAAGAGAGGGACG
TCCACGTTTCTTCGGCGCCACTACCGTCTTCTCAGGCGAGCTGTGTTCCTCCTCCCCGGAGTTCTCATCGTCCTGATCGTCGTCATTGTCCTCGT
GCTTCTCGACGGGTGCAGCATTGGCCTTTGGACGACCGCGCGGACGACCGGTGGGTACGTAGCCAGTACTGCCACCGCTACCCGACTTGTTCTGT
GGTGGACGACCGCGTTTCTTGGGCACTTGTGGCTCCCCATCGCCATTGGACTCGACAGCCCGCTTCTTGGGTCTTCCCAGGCCGCGTCCCGTGCG
CGATATGTTCAGGTTGACGGATCCAGCCGACGGTCGGCCCACTGGGCGACGTTCTTCGATGCTGCTGTTGCCGTCGTCGTCCTCATCCTGATCGT
CTGTTTTGAAAGAAACAAAGCAATGTTAGTTAATAGGTATAATAATGAAATGAATCCAGGAATATATTTAAAGTAATATTTGTGAAGGTAAATCA
ATGGTCTATCGACCATTTACATATTTTTGATTTGATTGATTGCATGGTTGCGGAATGTTGAAATCATGACTCTACCTGTGATCTTCGAAAAAAA
ATCACCAGGTAGCGTAAAGATAAAAGTGCAAGTTTGGTGGAAGCAAACAGTGCTTAAATTTCCATTAATTGAATTGAGACCATGAAATGTTGGGG
ATTTACGTACTAACTGCACTACCATAGGCTCACCTTCATTCTCGCTATCGCTGGGCTGGTGCTTCTTGGGCCTGCCGGCCTTGCGCTTCTTGGCG
GAACCGGGCGTCTTCACCGAATCCCCGGATCCTGATCCGGCGCCACCACTGCTCTTGGGTCGTCCCCTGCCCTTCGTCGGCGAGGGTGATGAGTT
GTTTGCAAGCTCAGCGCCGGAGCCATCGCCATCGCCGTCCTCCTCCCCCTCGTCTTCGGGATCTTCGTCATTTTGGATTTTTGACGCCTTCGGTG
GGCGACCCCGCTGTCCACCACCGCCACTGGAGCCCTTGTTCTTGGCGGGACGACCGCGCTTTTTGATGCCTGGCGAGATTGCTGCAACCGCCGCT GTTGAAGATTTACCACCGACGGATGCCTTTGACGGTCGGCCGCGCTTCTTTACCGCAACTTCCTCCATTTCTCTGTACGGGATTCAATTAGCAAG
CGAATAAAAAAAATCCTTGTTTCTTCGCGTCCCCTCACACACACACGCGCACAAATGCTCTCTCTCACGAACACACGCTCACTCTTTTCGCTTGG
CTCCGCTCTTCTTCTTCACCTTTTTGTTTGCCGAAAATCAAGCTGGAAAAATATACAGAAAAACAATTTTGCATTAGGGCTTGAATGCGCATAAA
TGCTGCAAAAAATATTCTCAAAAAATTCTTAAAAATTCTAGTTTTTCCAGATCCGAAAGGGAATTACTTGCGTTACTTACTTTGCCTTCTCAATT
TGTAATTGTAAAATACGCGCACGCTAGTACAGTTCAAAGTAGTGATGTAAAAAAAAATATGTCGGTGCATCGAGCAGCGATAATTTTTGCGATAT
TTTTTTCGATTTGATATCGATTAAGCGCTGCATCGATGCGTTCAAAATTGAGGCCGTTTAATTTAAGTTTGCGTAAAACAATTCCCTTTCATTTG
GTCATATTGCATTTTAACTATGTATTAACATAAAATGAAACGTAGCTTTTGTGAAAAACTCTTTTTACTTTTGGAAATTGTAAGGTGTAAAAATT
GTCTACTTACAGTTTAGGAATATCAAAAGAAACAAATTTATAAAAAACTTGAACTAAAGCAATAACCAAAAATTATTTTTTGAACTTCCTTCTTG
CGTGAACAACCAAGTTAAGCTATCCATATGTCCAAAAGTTAAACAAGTTTGAAGTGACTACATGAGACGGCTGGCCTACTATTTTAAAATATGGT
ATGTTGTGTTCAAATTTTTTTTTTTGCTTGAAGCGCCAAGCTCCAAGTTTTTAAAACAAGAGAGTACAGTTTAGAAGCAACCGTTTATTAAATAG
TTACACATATTGCAGTTTATTAGGCTAATCACAGTTGAATAATTAAATACTATTTAGTGGGCGCTCACTTCCACAGCTTGATGACACCGTTTCGC
GATGCAGATGCTATGTAGATCTGGCCCTTGTCCTTGCACATCAGCAGATCCGTGATGGCATCGTGGTGACTGGCCGTTGGCATATCCGGCCCCGA
GCGGGGATTCTCCTCCGTGGACGATCGCAGCTGCTGCGAGTCGCCCGTGCTGGCCATGGAAATGATTTGCTCCTCGATCACTTGGCTGCCATCGA
TTAACCGGGCACTGAAGGGTGGAATGAATTGATAATTTTATTATATTATCATTATAATAACAGATCAATAATTACCCATAGTTGAAAGCCACATC
TGCCAGGTTGTCATTGGCAGCGGGTACTTTAAGCGATGAGTTCTTTGGGTTGGTGATGTCCCAGTACCGGATCCGCTGATCCGAACTGCCGGTGA
GAA
(SEQ ID NO: 1063)

Exon: 3183..3121
Exon: 2987..2409
Exon: 2090..1001
Start ATG: 2823 (Reverse strand: CAT)

Transcript No. : CT27541
ACATCACTACTTTGAACTGTACTAGCGTGCGCGTATTTTACAATTACAAATTGAGAAGGCAAACTTGATTTTCGGCAAACAAAAAGGTGAAGAAG
AAGAGCGGAGCCAAGCGAAAAGAGTGAGCGTGTGTTCGTGAGAGAGAGCATTTGTGCGCGTGTGTGTGTGAGGGGACGCGAAGAAACAAGGATTT
TTTTTATTCGCTTGCTAATTGAATCCCGTACAGAGAAATGGAGGAAGTTGCGGTAAAGAAGCGCGGCCGACCGTCAAAGGCATCCGTCGGTGGTA
AATCTTCAACAGCGGCGGTTGCAGCAATCTCGCCAGGCATCAAAAAGCGCGGTCGTCCCGCCAAGAACAAGGGCTCCAGTGGCGGTGGTGGACAG
CGGGGTCGCCCACCGAAGGCGTCAAAAATCCAAAATGACGAAGATCCCGAAGACGAGGGGGAGGAGGACGGCGATGGCGATGGCTCCGGCGCTGA
GCTTGCAAACAACTCATCACCCTCGCCGACGAAGGGCAGGGGACGACCCAAGAGCAGTGGTGGCGCCGGATCAGGATCCGGGGATTCGGTGAAGA
CGCCCGGTTCCGCCAAGAAGCGCAAGGCCGGCAGGCCCAAGAAGCACCAGCCCAGCGATAGCGAGAATGAAGACGATCAGGATGAGGACGACGAC
GGCAACAGCAGCATCGAAGAACGTCGCCCAGTGGGCCGACCGTCGGCTGGATCCGTCAACCTGAACATATCGCGCACGGGACGCGGCCTGGGAAG
ACCCAAGAAGCGGGCTGTCGAGTCCAATGGCGATGGGGAGCCACAAGTGCCCAAGAAACGCGGTCGTCCACCACAGAACAAGTCGGGTAGCGGTG
GCAGTACTGGCTACGTACCCACCGGTCGTCCGCGCGGTCGTCCAAAGGCCAATGCTGCACCCGTCGAGAAGCACGAGGACAATGACGACGATCAG
GACGATGAGAACTCCGGGGAGGAGGAACACAGCTCGCCTGAGAAGACGGTAGTGGCGCCGAAGAAACGTGGACGTCCCTCTCTTGCCGCTGGCAA
GGTGTCCAAAGAGGAAACAACAAAGCCCCGTAGTCGCCCAGCGAAAAATATTGATGACGATGCAGATGATGCTGATTCCGCCGATCAGGGCCAAC
ACAACTCCAAGAAGGAGTCGAACGACGAGGACCGTGCCGTGGATGGGACACCAACCAAAGGAGATGGCCTCAAATGGAACTCCGATGGCGAAAAT
GATGCCAACGACGGTTATGTTTCGGATAACTACAACGATTCCGAATCGGTAGCTGCCTAAAACATACAATTTATAAACATTTCCACACACCCCTC
CCCAAAAATCAACACAAAAAAAAAAGAATGTTGTAAAAGCAAAAAAAAAAAAACGAAAAAAAATCTGCAAGTAAGAGAAGAAAACACAAAAATGG
ATAGGACCTACTTGGACTTTAGAGAACCTTCCCCTCCTAAAACAACACACTTTGTCTACATATATATTCCGATTTATTGCTGAGAAATCGGACAA
ACCGTTTACAACTGCACTGCACTGTAATGACGACACATAGCTCGGAAAACGATTTCAACTTGGATTGAAATTACCAAATAAATAACACATAAATA
ACATATTTGGGGAAGATTTCAAGTTCCGAAGTAGAACTGAACTTTATTGTAACAACAAATTTGATTTGATTGCAGAAATTTCAATCGTATACAAG
TTTAAATAAACCTACTATACCT
(SEQ ID NO: 1064)

Start ATG: 228 (Reverse strand: CAT)

MEEVAVKKRGRPSKASVGGKSSTAAVAAISPGIKKRGRPAKNKGSSGGGGQRGRPPKASKIQNDEDPEDEGEEDGDGDGSGAELANNSSPSPTKG
RGRPKSSGGAGSGSGDSVKTPGSAKKRKAGRPKKHQPSDSENEDDQDEDDDGNSSIEERRPVGRPSAGSVNLNISRTGRGLGRPKKRAVESNGDG
EPQVPKKRGRPPQNKSGSGGSTGYVPTGRPRGRPKANAAPVEKHEDNDDDQDDENSGEEEHSSPEKTVVAPKKRGRPSLAAGKVSKEETTKPRSR
PAKNIDDDADDADSADQGQHNSKKESNDEDRAVDGTPTKGDGLKWNSDGENDANDGYVSDNYNDSESVAA*
(SEQ ID NO: 1065)

Name: CHROMOSOMAL PROTEIN D1
Classification: DNA_binding
Gene Symbol: D1
FlyBase ID: FBgn0000412

Celera Sequence No. : 142000013384504
GAACTAAAACCAAAGAACAGGCAACTTGCCAATTCTTATCAATGGAGCTAACTCAAAAAGTGATATCAGTAAGTAAATAAATCTTAATTGAACAT
ATTTATGAAAAGATAATAGGGCGCCAAGGAATTAGTAAACGTTGGTGCTTTACAGCGTTATCGGACACGATCTGCCAATCCCAAAAAAATCACCT
GTTACACCAAATGCAGAAAAAATTAAAAACAACCATGCGAGTTCTTTTTCTCATTTGCTAAATTATTAAGCTTTAGTTTAGCAAACTTGTTTTTT
TTTTGTTTTAATTACTTGTTTGTGTTGGTTTCTTGTTTCATATAGTACATTCTATCTCGATCTATATATTTAATAATATATATACCATTACTATT
TTTATGTTTTCTTCGTTTAAAATCATCAATTGAAGTTCAAGGATTTGCGCTTTCATCGTTTCGATCCGACATTGACAATATTTATGTCTAGATAT
ATATATATATATATATAAGAATACATATATATATATATATATATGTATATTAAGAGTTCCAAGAAAAATGATGTGTGAGAATTGTAACTTATG
GACAAAAATTCAAAATTTTATCATTTGCTTAAATATTCTTAATATTTGTGGTTGTTTAGCATATTTTAAATATGTATGTGTTTGCTTGCATATCC
TTCAACTACGCGCATCGAATTCATAAAATATAATGATGGGTGAGATGGAAATGGAGGGCGGCTTGGGCTGGCTATACATGAATGTAATATACTTT
CGCGATGGACTTGCACAGTTTATTATTAACGCTTGCTCCTGGTTTTTGAGGTTGTGAGAGAGGAGTGAATTGCTAAACGAGGGTGGGGTGGAGGG
TGCATCTGTGTATCTTTTCTGTATTTCGTGATTTGTGTTGCGCTGCGCACAGACAGTTTCTCTTTCACATTTGCTGTTCCTATATAGTATACGT
GTGTACACATATATAGTTGTTATCGACTTTGTTTTACTCCGTTTGGTTATTTGCGAAAGTGGCTACGATGCGACTGCTGATGCTGCTGCTGCTGC TGGCCCAGGTCCTTTGCCTGAAGCTGAGGCCTTGCTCATTGAGCCCACCAGTCGGGTGCGTTCGAAGAGTGCGAGGCACTGCCGCCGCCGTAGGA
GCCGCCATAGGAGCCACCACCGGCGCCGCCGCCATAGTATCCACCGCCGCCCGAATTGCCGCCTGTAAAGGAAATCCACTGTTAAGTTTCTGCCT
TTAAACTGATTACTGCTGATGGATGATTCCACACTCACCAAACTTACCGTACGAGTTTCCATTGCTGCGGTAACTGCCGCCGCCGCCTCCTGATC
CGGAACCACCGCTACGTGGTGGCGGTCCACTGCGTCCGCCACCGCCGCCGCCAGAGCTTTGACGGTAATCCCTGGAGCCGAAGCCGCCACCATAA
CGTCCACCACCGCCTCGTCCAGCCCGCTTGGCTCCGCCATGTCCGCGATCCGAACTCATATCCTCCATGAAACTGGGGATCTCCTGCTTCGTTTC
GATCAGCAGCTCCAAGAGATCGGAGCAAATGTTGCGGTTCTTTTCGTTGAAAAAGGAGGTGGCCACACCAAGATTACCCATACGTCCGGTACGCC
CGATACGGTGGACATACTCCTCCACATCCGAGGGCAGGTCAAAGTTAATAACGTGCTTAACGTGCGGAATGTCCAGGCCACGAGCGGCCACGGCT
GTGGCCACCAGGATGGGGCAGTCGCCCGATCGGAAGCAGCGCAGTGCCTCCTCGCGCTCCTTCTGCGTGCGATCACCGTGGATGCTAGTGACGGG
ATGATTGCACTGGTACAGGAACTCCTCCAGCGAGTCTGCACCCTTCTTAGTCTCCACAAAGATCAGTGTTAGGCTGTCTTTGGTGTATTCGGGGC
CATCGCGGATAGACGAGAGCAGATCCAGCAGATACGAGCGCTTGTCGGGTTCATAGACCCACAGGATTGTCTGCGTAATGTTCTCAGATGTGGAG
CCCACACGACCAACGGCCAAGAAAATGTAGTTGCTGAGGAAATCGCTGGCTAACTCCTGGATCTGCTTGGGGAATGTGGCCGAGAACATAAGCGT
CTGGCGCTGTCCGGTTGGCGGCATGTTTAGCTGTTCGACGATGCGACGGATCTGCGGCTCGAAACCCATGTCCAACATACGATCAGCCTCATCCA
GTACAAGGAATCGAATGTTCTCCAGTCCCACCTTTCCGCGTGTGATCATGTCCTCTAGGCGACCGGGTGTGGCCACAATCAGATGGCAACCGCGG
TCCAGCTCGCGCATCTGCTCGCTAGTATTGTTTCCGCCGTACAGCACTGCCGGGCGCATCCGGGAGCGATAGGCGAACTTCTTGGCCTCCTCAAA
GATCTGGGTGGCCAGTTCGCGGGTCGGCGCCAGCACCAGACCCAACGGATACTGCTTGCGCCGGCTGTACTGCCGGGTGCTTTGCGGCGGGGGCA
CATGTCCCAGCTCGTACATCTGGTTGAGAATCGGCACCAGGAAGGCGGCCGTCTTGCCGGATCCAGTCTGGGCGCAGGCCATTAGATCCCGGCCA
TTGATAATGATCGGAATGGCGTGCTTCTGCACCGGTGTCGGTTTGTCATAACGTGCTAAGGCCACGTTGTTGCGGATAATCTCCGTCAGCTGCAC
ATCATCGAACGATGTGATGTTCGGGGGCACATTCTGGCCCGTCGCCTCCACGGGTATATCCTCGTATTTGTCAAAATTGATTCCCGTATTGCCCA
CGCCGAACAGCTCCACCTCCAGGCGCTCATCTCGGGCGCCCAGCTTTGTGTAGTCGACGTTTGAGCCGCCGCCCTCCTTCCAGCGGCTGTTGTAA
CCGCCGCCTCCGCGCTCGCCGCGATTGTTGTAGCTTCTGTTGCCGCCGGCAGACTGTCCGCCCTCGCTGCCATCGAATCCGGCAGGACGTTCTGG
CTCCTGCCAACGATCGTTGCGCGGCTGCTGCTGCTGCTGTGCCTGGCCATCCTCGGCAGTCTGCTCGTTGAGGTTGCTACCGCTTCCGCCGCCAC
CGCCGCGGTACGATGGTCCGCGTCCAAATCCTCGACCTCCTCCGCCGCCTCCGCCGCTGCGATTCCAGTCACCGCCGCGACGCGAATCGAATTCA
CCACCTGCAAAAGTAATTACATTTTCTCTAATAATATGGGCATATTAGAGGACCAAGTATAAGTCGTACGCATTACGATTTTAAGGATCATTACA
TTATGGAGCTGTAAAAATTAATTAAATGTCCTTGTGCTTCTTGATAGTGAATAGACCACCTGTTAGCCAATAGTACCCACCGTTGTAGTTGTCCT
CGAAACGTCCACCGCCTCCACGTCGTCCTCCGCCGCCGCTTCCGTAACCGTAGTCGCCGCTCTGGCGATTGAAGCCGCGACCACCACCGCCGCCG
CCTCTGCGGTATTCGCCTCCGCCTCCGCGCGACTGTTGAGGGTCCCTAGTCTCCTGGCGCGGATTCCCGGATCTGGAGTCGAAGCCCTGACCCTG
GCCCTGTCCTTGGCCCTGGCTCTCTGCGTCCGCTGCGTTGTTATTGCCACCACCACCACGAAGGTGCGGGGGCACATACACACCACCGGTGACCG
AGTTAGTGGAAGTCTTGCTGGTTATGGGGCCGCTGTAGTCAGCAGAGCCGCCATTCAAGTCCAGACCAGCAACCTGCAAGTGATAAAGATTAAAT
GGTTAGTCTTCTTCAGAACTTGTGCAAAAAATGTGGCATCAAATGTGGTTTCCTAACACTTAAATTATAGGTTTTGTTCTATTTTTTTTGTACTT
AATCATTGGTTTAAGATTACTTTTCTTTGTTATATACCAAGTTTACGGGAACACAGTGCATTTAATGATAAGATCTATACCAGCAATGCAAAACT
AAGCTACACAAATAATCTTTGCTCCACTAATACAATTGATTTATAGTACACATGGCCAATTAACATATGTTGCCTGTAAGTTAGCCGGCACCAGT
TCAAGAATCAAGTTCAACAGTTTGGCAAAAGATTCGCCGGGGAAATTTTCTCCAGAACTGCCAAAATGAATTCGTTCCCGCTTAGCAACATGTGC
TATTTACCGCTCTTCCTCTTAGCAACGCAACGTGTATATATACATAGATACATATGTATGTACGTGCAAATCTCCGGAATACACAGATAGAGAGA
GGCGCAACTAGTTTAAAGCTTCGAATTTAGTGCTCTCCCTGTAAGCGTCTCTCTCGCACTCGCAGGCAAGCTATTACACAAAGAGAGTCCGCCTG
GTAACCCAACAAAAACAACACGTGAACGAGCCACCCACACATGGGAAAACAAATCGCACCGTAGGGGCAAAACACAAAGCCCGGTTGCGGGACCC
AAGTGGACAGAATGGTGATGAAAGCAAGGGAACTCTTTCAAGAACTAGTTTAAATGTATACAATGATTATTATTCCCGTATATCTTGTAATATTC
AATATTTTGCCTTCTTCATTTATATTAATTAACAAAGGCAGCTAAATATGTAATTCGCAGATTTTGTGGGGCGTCACTTAACGGCTAGATCGTTG
CTAGATTCATTGCGTGCATTTGAGGCATACAGAAATAGTAGTATTTAACTAAACTATTTCCATTTGAAAGCATTAACGTTTGTTTATTTCACATC
TCTAATAAAGTTTAATTCTTTTTAAGGACCTAACAAAGGCTTGTTAAAATAGTGTATGTAGATTACATGCTTTGCTTTTCTTCCATTTTTTTTTG
CCAAATCACCCTTGAAATTAATCACCAGATCGCTTACTCCTGGCAACCCTATTTACAACAGCTTCCACATGTGTGAGCAAGCGAGAGAGAGCGAG
ATATAACACACACACACGACCAGCCTTAGAACAGCGGCACTGCTCGCACACACGACACACTCAACGTGAGAGGCCGAATGGAAACTTTCATATGT
ATATATTATACATGTCAAATTGGAGGCAAGCGAGCAAAAATTATACAAAAGAAATTACAAATTGGAATGACGAAGAGGGACCCAGGCGCACACAC
ACACGCACATATATGCAAGCCATTGACACCGACACAATTCACCGTTGTAAAACGAGCGATAGAGACATTAGTGTGTTATGAAATCAATAAATTTC
TAGGCGAACTTTTTCAAATAGCCGCATGAGCATCACGAACACACACACACAGCCACCGCATACACATGCGTGTTCCATTCTTATATAGATGGTAA
ATGGTATTTTCAGCAGTTAAAAACGCTACTTACTTGCTGCTCTAGACCTGTGCCATTTTGGTTAATAGCATTACTCATATTATCCTCCAATCAGT
TGCTTTTTTTTTCTTGCTTTCCGTTTAGGAAAATTTTGCAATGGTTACGCTTTGAATTTTTTTTTTTGAATGCACACTTGCAATTTGCGACAAAA
AAATGTATACGATCGTTGTGTTGGTGTTGCACTTTGTGTCTATACGTTTTCCTTAGTTTTTCCGACAAAAAACTTCTTACGTTCCACAAGCTAC
TGCGTTCTCGTGTGAAATTTCAGGGTTCTTTTCGTTCCTCGCACACAATTCCCTTTGTTCGGCTTGAAACTGAGACGTTTCCGTATCGGATTTGG
CTGGCCTGCTTGTGCCAACAATTACAATTACAAGCGCTATGGGCTTGGAAAATGCTGCTTCTCCGACGAGTTCACGTTTTTTTCCGCTTTCAGAC
GCGTGTCTAAAAAATCAGGGCTGCTTTAGCACGTATATCGATGAGGAATCGATAGATGCGGTCGGTGGAGGTAGAGCAGAGACTCCAACCTGGGC
TCTCGGCGGCGGTTACTGGCAAAGACTCCGGCAAGGGCGTTGCCAGATCTATATCCTCGTCTCGCGGTCTATGAAATTCAAATTGAATTTTTTCA
CTTTTGCTTTTTCGGCGCGTCGATCCCTTCTAGGCTGTTGTTGTTTTTTGAATGGAAGAGAAATGAGGCTGGGCAGTTAAATTTTGTTTCTTAAA
GGCCAAAAATGTTTGTGTTTATGTTTAGGAATAGTTGTTTATAAGGCGTCAGCCGCTGTACCCCATTTCGTTATTTGAAGCAAAAGTCAAAGAAA
TTCAAATTAAATTTGAAATTTAGTATATATATGTGATTGCCGTAAAATAGGTATTAAAAATTTCCAAACAATTCCATACTCAAGTTCCCTCCAAG
TCTGTTAAAGAAAACTAAAATTCGAAGTTTCGAACTCTGGAATATATTCATTCACTTTCGTCTTCAGAATATACATATTGTGAATGTACATGTTT
ATATAGAATAAATGCTTTTGGTATTGGCCTTAGCTTGAGATTAGTTAGTGGAACAATAAATATGGCTATAAAGTATCGTATATATGTATATAATA
ATAATTTTCATATCGTTCAGCCCTTGAGCAGGCAGCGGGAGTAGAACTCCCGGTCGATAGCGTCGTTTGGAATGTATGAGCTCCACTTGAAGATC
AGCGCCAGCGTGTCCCCGGCGGACATGTGATCCAGAGCGATGTTGAGGAAACAGTTCCAGTTGTAGAAGAAGTGGCGTCCCAACTGTTCCTGTTC
CACGCCAGATATGCACTCGCAGTTGGCGCACACCAGTCGTCCGCCGCGTTGCAGTTCCACGAACTGTTCGAAGCAGCGGCCCCATGCGCTCACGC
TCAGTTGTTTGCCCACGTCAGCCAGAAGTTCGGGGAGTCCGTAGTTGAGGACGATGGCCACCACTTTGGTGAGATTCTGTTCGGCTAGGTAAAAT
TTAGCTAAGACGTCTAATAGTGCCGGCACTGATTGAACAACATCAAAGCACTTCAGTTGCTCGCCACGGGACCAGAAGTATCGCAGGAGCACTGC
TCCAAGCTCATGATACTGGCAGGAGGTATCGAAGCGAAGGGGGAACGAGCAATGCTCACACTTGACAATCTCCGCATTTTGCGAAGTATTTAGCA
GCACAAATCCGGCAGCTATGTGATCCCGCGTAGCGTCGTCCACTTCCCAGATCATCTCCGGATCCAGGTAATCGAAATACATCTCGTAGCAATTG
CGTTGCGCTTGGTC
(SEQ ID NO: 1066)

Exon: 6044..5259
Exon: 3683..3311
Exon: 3139..1283
Exon: 1202..1001
Start ATG: 5303 (Reverse strand: CAT)

FIGURE SHEET 576

Transcript No. : CT27543
ACAGCGGCTGACGCCTTATAAACAACTATTCCTAAACATAAACACAAACATTTTTGGCCTTTAAGAAACAAAATTTAACTGCCCAGCCTCATTTC
TCTTCCATTCAAAAAACAACAACAGCCTAGAAGGGATCGACGCGCCGAAAAAGCAAAAGTGAAAAAATTCAATTTGAATTTCATAGACCGCGAGA
CGAGGATATAGATCTGGCAACGCCCTTGCCGGAGTCTTTGCCAGTAACCGCCGCCGAGAGCCCAGGTTGGAGTCTCTGCTCTACCTCCACCGACC
GCATCTATCGATTCCTCATCGATATACGTGCTAAAGCAGCCCTGATTTTTTAGACACGCGTCTGAAAGCGGAAAAAAACGTGAACTCGTCGGAGA
AGCAGCATTTTCCAAGCCCATAGCGCTTGTAATTGTAATTGTTGGCACAAGCAGGCCAGCCAAATCCGATACGGAAACGTCTCAGTTTCAAGCCG
AACAAAGGGAATTGTGTGCGAGGAACGAAAAGAACCCTGAAATTTCACACGAGAACGCAGTAGCTTGTGGAACGTAAGAAGTTTTTTGTCGGAAA
AACTAAGGAAAAACGTATAGACACAAAGTGCAACACCAACACAACGATCGTATACATTTTTTTGTCGCAAATTGCAAGTGTGCATTCAAAAAAAA
AAATTCAAAGCGTAACCATTGCAAAATTTTCCTAAACGGAAAGCAAGAAAAAAAAAAGCAACTGATTGGAGGATAATATGAGTAATGCTATTAACC
AAAATGGCACAGGTCTAGAGCAGCAAGTTGCTGGTCTGGACTTGAATGGCGGCTCTGCTGACTACAGCGGCCCCATAACCAGCAAGACTTCCACT
AACTCGGTCACCGGTGGTGTGTATGTGCCCCCGCACCTTCGTGGTGGTGGTGGCAATAACAACGCAGCGGACGCAGAGAGCCAGGGCCAAGGACA
GGGCCAGGGTCAGGGCTTCGACTCCAGATCCGGGAATCCGCGCCAGGAGACTAGGGACCCTCAACAGTCGCGCGGAGGCGGAGGCGAATACCGCA
GAGGCGGCGGCGGTGGTGGTCGCGGCTTCAATCGCCAGAGCGGCGACTACGGTTACGGAAGCGGCGGCGGAGGACGACGTGGAGGCGGTGGACGT
TTCGAGGACAACTACAACGGTGGTGAATTCGATTCGCGTCGCGGCGGTGACTGGAATCGCAGCGGCGGAGGCGGCGGAGGAGGTCGAGGATTTGG
ACGCGGACCATCGTACCGCGGCGGTGGCGGCGGAAGCGGTAGCAACCTCAACGAGCAGACTGCCGAGGATGGCCAGGCACAGCAGCAGCAGCAGC
CGCGCAACGATCGTTGGCAGGAGCCAGAACGTCCTGCCGGATTCGATGGCAGCGAGGGCGGACAGTCTGCCGGCGGCAACAGAAGCTACAACAAT
CGCGGCGAGCGCGGAGGCGGCGGTTACAACAGCCGCTGGAAGGAGGGCGGCGGCTCAAACGTCGACTACACAAAGCTGGGCGCCCGAGATGAGCG
CCTGGAGGTGGAGCTGTTCGGCGTGGGCAATACGGGAATCAATTTTGACAAATACGAGGATATACCCGTGGAGGCGACGGGCCAGAATGTGCCCC
CGAACATCACATCGTTCGATGATGTGCAGCTGACGGAGATTATCCGCAACAACGTGGCCTTAGCACGTTATGACAAACCGACACCGGTGCAGAAG
CACGCCATTCCGATCATTATCAATGGCCGGGATCTAATGGCCTGCGCCCAGACTGGATCCGGCAAGACGGCCGCCTTCCTGGTGCCGATTCTCAA
CCAGATGTACGAGCTGGGACATGTGCCCCCGCCGCAAAGCACCCGGCAGTACAGCCGGCGCAAGCAGTATCCGTTGGGTCTGGTGCTGGCGCCGA
CCCGCGAACTGGCCACCCAGATCTTTGAGGAGGCCAAGAAGTTCGCCTATCGCTCCCGGATGCGCCCGGCAGTGCTGTACGGCGGAAACAATACT
AGCGAGCAGATGCGCGAGCTGGACCGCGGTTGCCATCTGATTGTGGCCACACCCGGTCGCCTAGAGGACATGATCACACGCGGAAAGGTGGGACT
GGAGAACATTCGATTCCTTGTACTGGATGAGGCTGATCGTATGTTGGACATGGGTTTCGAGCCGCAGATCCGTCGCATCGTCGAACAGCTAAACA
TGCCGCCAACCGGACAGCGCCAGACGCTTATGTTCTCGGCCACATTCCCCAAGCAGATCCAGGAGTTAGCCAGCGATTTCCTCAGCAACTACATT
TTCTTGGCCGTTGGTCGTGTGGGCTCCACATCTGAGAACATTACGCAGACAATCCTGTGGGTCTATGAACCCGACAAGCGCTCGTATCTGCTGGA
TCTGCTCTCGTCTATCCGCGATGGCCCCGAATACACCAAAGACAGCCTAACACTGATCTTTGTGGAGACTAAGAAGGGTGCAGACTCGCTGGAGG
AGTTCCTGTACCAGTGCAATCATCCCGTCACTAGCATCCACGGTGATCGCACGCAGAAGGAGCGCGAGGAGGCACTGCGCTGCTTCCGATCGGGC
GACTGCCCCATCCTGGTGGCCACAGCCGTGGCCGCTCGTGGCCTGGACATTCCGCACGTTAAGCACGTTATTAACTTTGACCTGCCCTCGGATGT
GGAGGAGTATGTCCACCGTATCGGGCGTACCGGACGTATGGGTAATCTTGGTGTGGCCACCTCCTTTTTCAACGAAAAGAACCGCAACATTTGCT
CCGATCTCTTGGAGCTGCTGATCGAAACGAAGCAGGAGATCCCCAGTTTCATGGAGGATATGAGTTCGGATCGCGGACATGGCGGAGCCAAGCGG
GCTGGACGAGGCGGTGGTGGACGTTATGGTGGCGGCTTCGGCTCCAGGGATTACCGTCAAAGCTCTGGCGGCGGCGGTGGCGGACGCAGTGGACC
GCCACCACGTAGCGGTGGTTCCGGATCAGGAGGCGGCGGCGGCAGTTACCGCAGCAATGGAAACTCGTACGGCGGCAATTCGGGCGGCGGTGGAT
ACTATGGCGGCGGCGCCGGTGGTGGCTCCTATGGCGGCTCCTACGGCGGCGGCAGTGCCTCGCACTCTTCGAACGCACCCGACTGGTGGGCTCAA
TGAGCAAGGCCTCAGCTTCAGGCAAAGGACCTGGGCCAGCAGCAGCAGCAGCATCAGCAGTCGCATCGTAGCCACTTTCGCAA
(SEQ ID NO: 1067)

Start ATG: 742 (Reverse strand: CAT)

MSNAINQNGTGLEQQVAGLDLNGGSADYSGPITSKTSTNSVTGGVYVPPHLRGGGGNNNAADAESQGQGQGQGQGFDSRSGNPRQETRDPQQSRG
GGGEYRRGGGGGGRGFNRQSGDYGYGSGGGGRRGGGGRFEDNYNGGEFDSRRGGDWNRSGGGGGGGRGFGRGPSYRGGGGGSGSNLNEQTAEDGQ
AQQQQQPRNDRWQEPERPAGFDGSEGGQSAGGNRSYNNRGERGGGGYNSRWKEGGGSNVDYTKLGARDERLEVELFGVGNTGINFDKYEDIPVEA
TGQNVPPNITSFDDVQLTEIIRNNVALARYDKPTPVQKHAIPIIINGRDLMACAQTGSGKTAAFLVPILNQMYELGHVPPPQSTRQYSRRKQYPL
GLVLAPTRELATQIFEEAKKFAYRSRMRPAVLYGGNNTSEQMRELDRGCHLIVATPGRLEDMITRGKVGLENIRFLVLDEADRMLDMGFEPQIRR
IVEQLNMPPTGQRQTLMFSATFPKQIQELASDFLSNYIFLAVGRVGSTSENITQTILWVYEPDKRSYLLDLLSSIRDGPEYTKDSLTLIFVETKK
GADSLEEFLYQCNHPVTSIHGDRTQKEREEALRCFRSGDCPILVATAVAARGLDIPHVKHVINFDLPSDVEEYVHRIGRTGRMGNLGVATSFFNE
KNRNICSDLLELLIETKQEIPSFMEDMSSDRGHGGAKRAGRGGGGRYGGGFGSRDYRQSSGGGGGGRSGPPPRSGGSGSGGGGGSYRSNGNSYGG
NSGGGGYYGGGAGGGSYGGSYGGGSASHSSNAPDWWAQ*
(SEQ ID NO: 1068)

Name: DEAD box helicase
Classification: RNA_binding

Celera Sequence No. : 142000013384638
AAGTTCTTTTTTTTTGAGCGTCCTAACTAGGGAGGGTGCACTGTACATACAGCTTGTATGACTTTATTTTAAATACGTGATTGGATTGTAAATGG
GAAATAAATTAATAATTTTCAAGCGTAAACTGAGATTAGTACACATCCTTTTTGACACCACTGTTTCAAAAGGTGACAAATCCTTTAGGCCGCCA
CTGTAAATGGGAGTAGGCTCCTTTGTCCCTCCACTGTTTGCACATACACACACGCAGAAGTTGAGTAAAAATTTCACAAGTTTCTTGTCGAAAAA
CGCAATTTCTGTGCAACAACAACCGATTAATTGCAAGTAAACTGCGCATTTGTGTCTAGCCTTTTTAAATGATATTTACTTTTTTGTTATACTAA
GTTACGAATTTCTATAAGTCACAAGAAATCATCACATTTTATACGAATGATGAATTTGTCTTAATCACGCTTTCGTTTCTCATTTCAGTTAAGTT
TTTACTCTGTTTGTGAGTCAGATTTAGCTAGGAAAGTACCTTTTATCAGTACGGGAAAAAATCTTCGTTAATTTTATACTGCCAGACGACGTTGT
TTTTGTCGATGGTTAGTGATGGCAAACTTTGGTTTGGCGAGCCCATTAGTGGTGCAAAAAAGCACAAATCTAACGAACACCAGAAAAACTTGTTC
GTGTCACGGAGCAGCATGCACGAAATATCGCTAAGAACTATTTATATAGTGACTGAATTCAAGTCTGTGTATATTGACAATGTCTAATAATAAGC
TTATAATTCTCTTCCCACGAATTACAAAATGGATTTTATATAAAAATTTAGATCGTAATAGCCGTTGTGAATTATTTTAATCTATTGTTCGCCAC
ATCTTCTTAACCTAAACAATTTATTTATTTTTTTAAACATTTTTAGTGCTTGAGCAGCAATAATCAACTCACTCTGCCATCTCTGCTGTTATCG
ATATATCAAAACAGAAAAACGGTCTGCAAAAAGTGTGACCGTTTGCCGTGCTGCTCGCAACTTTGACACGACCAGTTCCAAAATATCGTGAGATT
TACGCAAAACTACTAGAAAATGGTCGGTTGGAGCCGTTTGCTGTCGCCGGCGGCGAAGTTCGCCAGCTACCGGGCTGTCCTGCAAGAGCCCGCGT
GCCGGAATGGTGAGCATTTCTTGAAAATATCCGCCGTAAACACACTTCACATTACGCAACCATATATTCTGGATTTCTAGCCCTGCACCAACAGC
TGCGCAGAATGGGAGGCGATCATGGACACCACCAAATGATCATCAAGCCATCCCGCTTCCAGTGGGACAAGTTCAAGGATCTGTTGCACTTTTAC
GTAATGCTCGGCGTCATCCCAGTCACCGCATTGGTTCTCTACGCGAACATCTTTGTGGGACCCGCGCAGCTCGCCGAGATTCCCGAGGGCTATGA GCCCAAGCACTGGGAGTACGAGAAGGTATGATGGGCTCGGAAAGGCAACCAATCGATACTAAGATTGTAATTCCGAGATATCTCTTTATTATCTA
GCACCCCATCTCGCGCTTTATTTCCCGCTACATTTTGAACTCGGATCAGCAAAACTACGAGAAATCCCTGCACTATCTCTACGAGGAGAACGAAA
AAGCCCAGATTCGGTAATGCGACGGAAACAACCCAGTTATATCCCATTGTAAAACAATATATTTCCTTTCAGACTCCTTGAGGACGAAGTACGTC
GCAAGATGTCGGAGCGCAATGATTACCAGGCCTACTACTACCGACCATCGGTGGCCAAGTACCACAGGATTTCGAAAGAGGCTGCTGACGAGCTG
GAGGCTCTGCGCGGAGACTAGAACCCTTGTAATATTCTTTAAATACCATTGTTAGGATCCCGTTTTGTGGGAAATAAAGTGTGAAATCGACTTCG
CAACATCATCTTATTCACATTTAATAATATAAAAATTACACAGTAGTCGAATAAATACTTAAGACTTAGCAAAGTCATGTGCGTATCGATTTAGC
CCCACGCCTGATTCTTGCAGTAGTAGAGCACCAGTTTCCCATTGGTTCCATGGCACTCGTACAAGTTCTTGATTATCTGATCCGGGGCAGGTGCA
AATGTCTGATTAACGTACAGGAACTAAAAATTAAGATGACACATAAGATAGGGTTCTCTGGAACTTCATTTGTTACGTGCAATTTGCTCGCTGGC
ATCGAGTTTCAGAAACTTGTGGATGAACGTCTGTATCCAGCCGACTGTCTTGTTGGGATCTACGGTCCAGGTTCGCTTTTTGATGATGGGCACAT
TGCCAGTGGCGTTCAGAAGGATACAAACTGATAATGAAGCAAGTCTTTGTGATAAAACGAATGCAAAATATATAAAGTTAACTTTGATTCTCACT
TTTGGAACCATCCTTATCTGCAGGTGTGGAGGAGGAAGTGCTCAGCGCTGCCTGGGATTCTGGTGTCTCTGCCATTTATTTGGAATGTAACTAAA
TTAAATAGTTCCTAATTAATGAATTAAAACAGCCAATAATGTAAATAAAATATAATCTGTTAGAGATCAGAATTTTCTGAAGAAATTATCGATAG
GTGTCACGAGATTAGCGATTCAGCTAATTATTTGAGTAAAATATGCTGCATATCATCTGATTTTGTTTTAAGGAATTATTTACTCATTTTCTTGT
CATATTTTTATTTAAACATATTTTTATATTTGTCTATCACTTTGAGACTTTCAAAATTCGTTGTTAATTGTTCCACCTTTAGCGTTAACAGCGG
CTATGTTATTTTACATTCGACTGTTATTGTAACACGTGTGGAGTTTATAAAACAATCCAGGGAAATAAACAAAACTATGAATAATAATCTTTT
(SEQ ID NO: 1069)

Exon: 1001..1149
Exon: 1221..1450
Exon: 1522..1628
Exon: 1688..1848
Start ATG: 1065

Transcript No. : CT27589
CTGCTCGCAACTTTGACACGACCAGTTCCAAAATATCGTGAGATTTACGCAAAACTACTAGAAAATGGTCGGTTGGAGCCGTTTGCTGTCGCCGG
CGGCGAAGTTCGCCAGCTACCGGGCTGTCCTGCAAGAGCCCGCGTGCCGGAATGCCCTGCACCAACAGCTGCGCAGAATGGGAGGCGATCATGGA
CACCACCAAATGATCATCAAGCCATCCCGCTTCCAGTGGGACAAGTTCAAGGATCTGTTGCACTTTTACGTAATGCTCGGCGTCATCCCAGTCAC
CGCATTGGTTCTCTACGCGAACATCTTTGTGGGACCCGCGCAGCTCGCCGAGATTCCCGAGGGCTATGAGCCCAAGCACTGGGAGTACGAGAAGC
ACCCCATCTCGCGCTTTATTTCCCGCTACATTTTGAACTCGGATCAGCAAAACTACGAGAAATCCCTGCACTATCTCTACGAGGAGAACGAAAAA
GCCCAGATTCGACTCCTTGAGGACGAAGTACGTCGCAAGATGTCGGAGCGCAATGATTACCAGGCCTACTACTACCGACCATCGGTGGCCAAGTA
CCACAGGATTTCGAAAGAGGCTGCTGACGAGCTGGAGGCTCTGCGCGGAGACTAGAACCCTTGTAATATTCTTTAAA
(SEQ ID NO: 1070)

Start ATG: 65

MVGWSRLLSPAAKFASYRAVLQEPACRNALHQQLRRMGGDHGHHQMIIKPSRFQWDKFKDLLHFYVMLGVIPVTALVLYANIFVGPAQLAEIPEG
YEPKHWEYEKHPISRFISRYILNSDQQNYEKSLHYLYEENEKAQIRLLEDEVRRKMSERNDYQAYYYRPSVAKYHRISKEAADELEALRGD*
(SEQ ID NO: 1071)

Classification: enzyme

Celera Sequence No. : 142000013384438
AATATGCTAACAAAGTGGATGTCAATTCGACATGCTTAATAAAAACTTACAACTGAGTTCATAAATTTTTGGGAGGAACCAGTATCTGCTAATGT
AACACTGTAACTAATGTTATTGATTTAAAAAAAAAACTTCCGCATTCTGAGATTTAAATTTCGCCCAAAAGTATGCATTACGAATATATTTAAAT
TGGCCACACAAACTTTCATATGAAAAGTTTTTTTTTTAATTAATTTATATATTAAGGCATACGGGGAAATCTTGGAGCCCCTTTGTGTCCTTCTT
TCATATGAAAAGTGTGTTTTTTTATGCTCTTTAGAGTACCTTTTATTCTTCACCAGGATCAAGAATCAGCGCAGTCGATCTGGCCATGTTTGTCC
GCATGAACGTCAAGATCTCATGAACTATAAATGCTAGAAGATTAAGGATGCAGATTGCACAGAAAAGTGTAGGCGTAGCTCAAGTTTATCCTGGT
GCTACCAAACAATTGAAAGTTAAGTAACGCATATGATGCAACGAGGTGCTGGTTATAAAATGTAAGAAACTAGTTTTTAATAGAATGTGTTGTCA
TATTTCGTCACAAAATTTGATATTATAACTTTTGTGTGCCGAAGGTACGATCATCAAAGTTTGATATTAAAGAATATAAATATTACTATTCTTAC
AATAAACCCAGCACCGATGCGACTCCCTGAAACCCTATAGAATAGTGAAGCTCACCAAAGACTGAAACACAACATTTTGTTTTAGCAGTTGGGTG
CTAAATTTTCAGTTGCACATGCATTTATTTTGTTCCTGGTGATGAATACTGTTGTGTTTAAGAGTCTTCAGTAGATTCGAATGCTCCTACAAACG
CCACATGGTCGTTTAGTGTAGGTGTCACAGGATTCATGCTGATTCTTCAATTGAGTTATAAAAAAGATAATCCCATATATATTTTCTTTAGTATG
GAATGTCATTCTGACCAGAGTAATCGATACAAGTTTTGGTTTTTTTTTTTGGCGATCAGAGCACTTTATTACGTAGACCCCCCATTGATAAAAAAC
ACAATCAGTTTACAATGCCACCCTTAGTAGATATTACCACTTCAACAAACGCCGTCGTTCTAGGCGGTGGGCAGGAAGGTGAGCTTTTCGTTAAG
CTGCAGCTGGGTTTTGATGAGCTGGGAGAGCGTGATGACCAGCAGAAGGTTGCGTACGTTGGCGTTGAACATCTGAGTGAACTGCTCGTGGGTCA
TGTGCGGCACGGAGTGGATAAGGTCTAGCAGCTGGCGTCCGACGGCGTTGTCGGGGGTTACCTTGTGAGCGATCACGTCGTCAACGTACTTGAGA
ATAAGATCCAGCAGGGACTGCAGCTTCGTGGAGGCCTCCGAGATTTGGGCCAGGTCCAGCATTGGCGGAACGGTCTTGGGACGGTGAGCGGGCGA
AACGCCTACGGTCTTCTGAAGCAGCTTGAGCCCAAATGTCTCCGGCTCGTAGCTGGTCAGCTCGACGGAATGGGCGTGAACATGCAGCCCGCTCT
TGCCGCCGGGAACTCCTAGTTGAATGCAGACATAAGCACGCAGACCCATACGTCCGCCCTGCAGCGAAGTGTCCACGGTGAGGTGAACCGGGTTG
TTGCATTCGCGGGCGTAATACTCGTGGATCACCGAGCTGTGGTTGGTAACGTCGTTGCCGGTGGCCCACCAGCCTACCACGCTCTCGTTGGAGTT
CACCTTGCGGTTGAGGTCGTACATGTCCAGGGCGTAGCTCAGCTCTGCCTCCACCTGGTCATCGTGCTCCTTGTGCGGCACACAGAAACAGTTGG
TAACCTCCACCACACCTTTGTCCACAGAGCCGAGCAGGGTGCCGATGACGCGGTGCGAGTCCGCGTTCCGCCGCTCGAAGGCGTCCACCACCTGG
AAAAGCACCACCGGGTGCACGCGCACGGTCAGATTGAGAGCCGACATGGTAATTTTCGGTGGCCAAGATTTGCAAGGAAAATTTCCGCAATAATT
TCTATTCAGCCACGCTGCGCGTATGTTTTAGGGATGCAAGAAAAGGGCCTATCGATAGTGCGGGTGGGGGTTGATGGCTTTTGGAGCTATCGGTG
CGGTCGTGCGTGGCCTATCGTTTTATCGATGTAAAACCGGTGGCTAGCGTTAGTTAATCAAATACTATTCAAATTTGAATATGTCGGAGATGCCA
AGCGCGACTTTTCATTTACTTCAGCGTCCATATTGTCCAGCACATCAAGTCGCCTGCGTGTTGTTTCTTCTGTCGTTCTAAGCAGACTAATTTAC
TCAAGCGTCGCCCTTCGCGATGCTTTTCTTCTATTCCTCACCTTCACTCAATTATTTCATCCTTACTTCGTTTCCAGAAACTATACAACAACAACA
ACAGCCACACAAATGATGCCCACTCAATAACGGAACGCTTTCCGTGAATTTCATTGCTCGCTGCTCATTCTTAACATAACGGATCAATAACAAAA
TGTCGGTTACATTCTACTACTCAATCTTGCTTGTGAAATTTTGCTGATCAAACGTGCTTAAAGCGAATTATTAAATTTAATAAAATGCCTGGAAA GAGATAAACTTTGAAGTTACCCAATTAATAAACTATAACCACCAGTTGGGAAAATCTTTTCCAGAATAAGTATAAATGTTTTCTGTATCCCGTAA
GACCGTCTACTATTTTTTAAAAGGCTCGGAAAAAGAGGACAGGCTTGAACCTAAGA
(SEQ ID NO: 1072)

Exon: 2058..1001
Start ATG: 1947 (Reverse strand: CAT)

Transcript No. : CT27609
CCGCACTATCGATAGGCCCTTTTCTTGCATCCCTAAAACATACGCGCAGCGTGGCTGAATAGAAATTATTGCGGAAATTTTCCTTGCAAATCTTG
GCCACCGAAAATTACCATGTCGGCTCTCAATCTGACCGTGCGCGTGCACCCGGTGGTGCTTTTCCAGGTGGTGGACGCCTTCGAGCGGCGGAACG
CGGACTCGCACCGCGTCATCGGCACCCTGCTCGGCTCTGTGGACAAAGGTGTGGTGGAGGTTACCAACTGTTTCTGTGTGCCGCACAAGGAGCAC
GATGACCAGGTGGAGGCAGAGCTGAGCTACGCCCTGGACATGTACGACCTCAACCGCAAGGTGAACTCCAACGAGAGCGTGGTAGGCTGGTGGGC
CACCGGCAACGACGTTACCAACCACAGCTCGGTGATCCACGAGTATTACGCCCGCGAATGCAACAACCCGGTTCACCTCACCGTGGACACTTCGC
TGCAGGGCGGACGTATGGGTCTGCGTGCTTATGTCTGCATTCAACTAGGAGTTCCCGGCGGCAAGAGCGGCTGCATGTTCACGCCCATTCCTGTC
GAGCTGACCAGCTACGAGCCGGAGACATTTGGGCTCAAGCTGCTTCAGAAGACCGTAGGCGTTTCGCCCGCTCACCGTCCCAAGACCGTTCCGCC
AATGCTGGACCTGGCCCAAATCTCGGAGGCCTCCACGAAGCTGCAGTCCCTGCTGGATCTTATTCTCAAGTACGTTGACGACGTGATCGCTCACA
AGGTAACCCCCGACAACGCCGTCGGACGCCAGCTGCTAGACCTTATCCACTCCGTGCCGCACATGACCCACGAGCAGTTCACTCAGATGTTCAAC
GCCAACGTACGCAACCTTCTGCTGGTCATCACGCTCTCCCAGCTCATCAAAACCCAGCTGCAGCTTAACGAAAAGCTCACCTTCCTGCCCACCGC
CTAGAACGACGGCGTTTGTTGAAGTGGTAATATCTACTAAGGGTGGCATTGTAAACTGATTGTGTTTTTATCAATGGGGGTCTACGTAATAAAG
TGCTCTGATCGCC
(SEQ ID NO: 1073)

Start ATG: 112 (Reverse strand: CAT)

MSALNLTVRVHPVVLFQVVDAFERRNADSHRVIGTLLGSVDKGVVEVTNCFCVPHKEHDDQVEAELSYALDMYDLNRKVNSNESVVGWWATGNDV
TNHSSVIHEYYARECNNPVHLTVDTSLQGGRMGLRAYVCIQLGVPGGKSGCMFTPIPVELTSYEPETFGLKLLQKTVGVSPAHRPKTVPPMLDLA
QISEASTKLQSLLDLILKYVDDVIAHKVTPDNAVGRQLLDLIHSVPHMTHEQFTQMFNANVRNLLLVITLSQLIKTQLQLNEKLTFLPTA*
(SEQ ID NO: 1074)

Name: eiF3-epsilon-like
Classification: translation_factor

Celera Sequence No. : 142000013384852
ATTGGCATTAATGTAAACACTCGAGAGAGGAAGGAAAAGATAACAGTACTTGCCCTTGACTCCAATCTGTTCAAACTAAAAAAGGTACAATGAGT
CACCCAATTTTCCATTTAAAAATTCATTGTTTTTATACTATATTAAATATTTAAGAAAATAAACAAAAAATATGTCTTTTATCAAGGAAAGCATA
ATCAAGCCAATTCAAAACAAAATCATATAGGGAAACGACAAATATAAATATTTTCGATCTAGTTCGTAATCATAGGTTCAAGAACAAAGTTCGTA
TTGGACAGCCTGCCAAATTTAAAGATTCAGCAATATAAAAGTAACTAAAGCAAGAGAGAAGGCTATGGTCGAGTTCCTCGACTATCAGATACCCG
TCACCCGTGGCAACATGGGTCAACTAACTTGCGCTGGGTATTTGTCTCTAGAATCTGTATGCTTAATCTCAACCTTCTAGCTTTTATAGTTCCTG
AGATCTCGACTTTCATACGGACAGACGTACATGGCCAGATCGGCTATTGATCCTGGTCAAGAATATATGTACTTCATATGGTCGGGAACGCTTCC
TTCTGCCTGTTTCAACGAATCTAGTATACTCTATTACTCTACGAGTAACGGGTAGAAATATAAAATTGAAACTATTTTGAGTCATCCCTCCAATT
GGTAATTTTTTTATATATTAACGGAAATTTAAAGTGCGTTACAAAAGTAAAAATTCTTTTGGTGCTAGTATGCTTAACGGGGTGGACATTTCGGC
GTTTTCCACACTTCTTGGGAAATCACTTTAGACAAATTTGTACCAATGTCGGTACTTAATAGTATTTAACTATAACTTACCTTTTGCCTTTGGTG
TGAATAGGCTATTAAGCCAAAGAGTAAACATTCGTCGATTGTAACTCCCTTGTCATCGATGTTGGCCAATACGTGACAACATCGATAGTATCGAT
AACTATCAGGTTCAGGTTCGCCTGTATTGCACTATTTTGCTTCACACACGTAATTTCGGAATTTGCCAGAAAAACACCGATCTGCTATTGATCTT
AGTCCAAAATTGCGTTTTTAAGTCGAAAAGACACTTTTCGGCTTTTAGATGGATGAAGACTCGGCTACGATACAGCTGGGGATAGGCGTCTCGG
TAACGCGGTCGATCATGATCTGCTTCCAGGGCCACCCGGCGTCGATGAGAAAAGCGGAAACGAGAACTGCGAGCCCAGGAGCAGTGGGTCGGGAA
AGCGCGGCAAGTCGAATTCCAGGCGCCGTTCCACATCCCGTGGTCGGTCGGATTCCCGCAACACATCGCCGTCGAACACCCGGCGAAGGCATTCC
CTGTCCCGCTCGCTGACTCCACCGCGTCGTCGTTACGATTCGCCCGATTATGGGCGGTACTCCCGACGGCGCTTTGATCGTGATCGGCGACGCTC
CCCCGAACGCCGGCGCTCTCCGCCACGTCGCGGACGACGGTACGGACGATCCCGGTCCCGCAGCATGTCGCCCCCGACGGGGAGGTCGATGGTCAC
CAAAAAAAAAACCGTCGTCGCCGCCAGTGCCCCCTCCGCATGGAGGACCACATCCTCAAATGACCCCTGGCTATGGAGCTATGGCCGCACATATC
TACGGATCATACGTCGCTCCACCAGATGTTTACGGTCACCAATATGGAATTCCGCCTAACTCGTTTCCACCTCAGGGACCGGGGTACGGTATTCC
AGGTGCCCCGCCGGACCAAAGCTCTTTTGGCTCTGGCTACGGTCCGCTCCCACAAGCGCGTGGGACGTAAATGGTACGTTTCTAGACATTTAAC
GCCAAAAGCCCTTCATTTATTAAGCATATTATTTCCTGCAGTGTACGGTCAGCAGGTGTGGATTAACCAGCCTATTTCTGGGGTCCAGCCATCCG
CTTCAGACTCCCTGATCCAGCCACAGAAGGCCCGCGAAACTCTCTCTGGCAAGACGATAGGCGAGGAGCAGTCGGTGCCAGCGCTCGAAGGCGCA
GGTTTGACGCCTCAGGATGGTAAGTGTGGAAATGAATTACAATGTGATCACTACGAACATTCACATGCAAACCTCTCACATTGTTTTATTACTGT
TGTCATGATTACTTGTACTTGTAACTTAATTGCGCGCAAATGAATCGCATACCAGAAATTACCAAAAGTCTAGGGTAAAGATCAGATTAATCAGA
ATCTAGAAGTACACGCGCTGCAAGAACTAACCAAGACCAACCCGAGCGATAGTCTCGAAATGTTAATTCGTTTCAAAAAGAAAATGCAGAGTTTC
CGTTTTTGTGTGGCAGTCGAAACAAACAATTACGCCAACCTGGACGACCGCCGCCCCAACTGGCTCTTCATTCAACGAGGACTGGCAGAACAAGC
AATCACGGCGACTGCATCCGAGTGTAATTAGCCGATGAAATGCACTCGAGAATGCATTTGTAAATGAAATTTTAACTTTTATTTATCTAGGAAGA
ATGTTTATTAATTAAAACCTATATATTTATCCCCCATATATATACCGTCGATCGGCAGCTGTTGCCCAAGAAGCGGAGAAGCAAAAGGACGAGCT
TAAGAAACAGCGCGCTAACTATGTCAAAAAGGTATCGCTGCTCAAGAAGGAAATGAAAGTACTTAAGGACCAGCGCGAGGACCTGGCAGCAGGCG
ATGCCCCACCCTCGCCAACCACAAAGAATTTCATCGAAGAAAACGACCGCCTGCAGGTGAATTGGGATCCCAAAACCTTATCTGTTAGCCACTCT
ATGTAACCTGTTTTCATCCTGTATAGATGCAAATTAAGAAGAAACTTGACACAATTGAAAACGTTATAGATATGCTGAACGGCATAATTGGCTAC
GAAGAAGTTGAAGATGAACCATCTAACCAAAAGTCCCATGGCAAGACTCAACCGGAACAACAGGATAGTCGCTCGCACTCCTCCAGTGAGAGTTC
TGCAGATAGCTCTGAATCCAGCTCATCATCTAGTACTGCTTCCGATTCGTCATCCGATAACGAAGACGGGGAAGGGGCAGGCGGCGCCGTAGGAA
GTCCAACCAATCGGCTAAAGCACCGCGCCATAAAGTCGATGAAGTCAAAGCAGCTACATGGTGAAATGAAGGCAGTGCCAACCCAAGCACAAAAT
TACAATTTTGTGTTTTTCGATCCCGAGCAGCATTGGTGCGAGAGCTGTGGAGTTTTTCCAAAGTCTGCTCGAGACTATTTAAAGCACTTGCATGC
CGAGGAACACATGAATCGAGAAACCATAGAAACTCCGTGGCATGTGGGTATTGACCACGATCCCTTTCCCACATTTGAAAACGCACCTGCCAGGC
GCGTCCCCGTGAGGGGCATGCAATTTCTGGTGCCGGCTAACGCTTGGTTTTGCAAGCTCTGCAGTGTTTGGATTGGAGACTTGCACTGCGCTTCT
GCTCATCTTAAGTCTAGGCTTCACTCCAATAAGTATCAGGTGAGTAGTAATATACATCTTTTAAAGCTCTTATGAAATATTTACTGTCACAAATA TTCTTTACCATGTTAATTTAGGGTTTTGTATTTAATTAATAAAATATATATATTAAATATAAAAATACGGAGCTTGTAGGGCTGGTGGATAGAAG
TACTTCCCAAAAACAAAATTGAAACAATAGTTTTGTTAAGATTGAACGTTATTTACATATCGTGAAATCATTTCTACGTTTAGCTTACATCAAAA
GTTTTGTGTGTTAAATTTGCACTTAAGATATTTAGGTAAATTACGTTATTCACTTGTGCTTTCATGCATAAAAAAAGTTCGGATTTCAGGCATTT
GCCATTCGCACATAATATCAGCTGTCACTACCCTTGGCAATGATGTAGTGTATGAGCAGAACAAGTTTGAAGATTGCTCCAATTGTCAACTTTTT
TTTTTGCTGTAAAGTTGGCTTTTACCTTTGTGTCAATTTATTAATTATTAAATTGGCTTATTTTTAAAAGGTTAATTCTTCTTTTCCTTCCCAGC
AACAAAATTTAATGGTAAGATGGGAATGTGAATGTAAATGGAGTAGCCAACATGTGCTTTAAATATATTGTTAGTACTTATGTAATCTTACTACA
ATCATAAGTTAACAATAAATAAATGGAAGCCTATAGAGGCATGTCCGTTTGTATGAACATCGAATTTTTGGGAACTATAAAAGATACCTAAGCAT
GCAGATTCTATTGAGGTTTTCGTGGCGTAAGTTTCTTTTAGAACATTGTCACACCACAAAGGCCACAAACGGTGGCTATTCTATGGTATTTGACG
CCCAAAAACTGTCTCGCCCACACTTTTTAAAAATTTCATTATACCCGTTACTCGTAGTAAAAGGGTATACTAGATTCGTTGAAAAGTATGTTACA
GGTCGGACTCGTTTGTGGCCATATAAAATAAGGATATTCCTGATCAAGATCACTAGCCGAGTCTGGCCATGTCCGCCTGTCAGTCCGTTTGTATG
AACGTCGAGATCTCAGAAACTATAAGAAAAACTTCGAGAAGATTTAAGTTTATTCATTTCCCAATTTCTATCGACATGCCAAAAAAAATTTTATA
GCTCTCGTTCGCACTTCCACTGAGTCACCAAAGGGTATCTAATAGTCGGGGACCACTCTTGTCAAAACTAACATAGGCCTTCCACTTACCTTTCT
CGTATATATTTTATAATTGCTTTTATTAATTCTTCGCCTCATGCAATTATTCTCCTGTCAATTTGGAATATATTATTGACTTTTTGTACCCGTGC
ATTGCAGCAATTTTTAAATCAGAACCCCAACTATGAAATAGAGTGGCAAACAAACCGCGAGCGGGCCATGAATCAACAGAAAGATCACGATGATG
CCAAGAATAAAAAGTCCAAGAAAGACGAGGACAAGGCGTCCAAAAAGAGGAAAAAAAAGGGGTAAGGGTCATAAGAATAATTTGAATCCAGATTA
TATTTTATATTTGTTTCTTTTTTACAAACAGCGGGGACAAAAAAAAAAAGAAGCGCAAGCACGGAAAGAAGAGCAAACGTAGTACAATAGATGCA
AACAGCACATCGTCATCCTCCGATAGCTCTTCGTCGGAAGAGGAAAATGGACAGCAACCAAAGAAAGGTCGTACCGAACAGCAACCAATTTGTCA
ATCAGATAAGTCGACTAATGCAGCATCAATACGAGTGGCCATGAGAAAGCAGGAAAGCACACCAACAAATTTGAAGCCGGAAGTGCCTTGTCAGC
CTGTGGTGCCGCCACCGCCACCGATCATAAAGGATTCCACAATTCCTTCAGAACGGGGTAAATGGACTGCCGCCAGTGTCGAAGACCAAAGTAAG
GATCAAAAGAACCGGGATGATACCATGCTCAAGCAATGGAATAATGTGCAGCCTGTTATAAGTGAGAGTGAAAAAAAGTTGTTGGAGCAGCTTAA
AGGAAGGCTGAAGAACAAGGGAGCCCGCGACCAGAACAACCACAAAGCAGTACCAACAGAAGCGAATGATGAAAAGTTTAGGCGGGGTGGAGGAC
GTCATTCTCGTTCACGTTCTAAGCGGCGCAGCTACTCTCGAAGCATAAGTCGCGGGCGGGATCGAGATCGGCGGGATCGTGAGCGAGATAGAGAC
CGTGGTCGTAGGCGTCGGTCACGCAGTCGTGGCCGACACTTCTCTCGTTCGCCCATAAGATCTAGTCGAAGAAGTCGATCCCGTCAGGGCCGAAG
TCGACGCAGTCGTAGTCGCTCTATTGAACGGGTAGAGCGTCCCGTGGTCAAGCATTCCGAGTTTCGGCCCCGTACTGTGCCGGAACGCAAGCAAA
CTGATATAAAGCGCGACAAGAAGGATGCAGAAAGCAAGTCAAAGTCATCCAAGCCCAGTAACAATTCCTTGCCTGGAGGCAAAAAACTACCTTTC
ATCGGTAAGATGCCAGTATTTAAAAAGCAGTCTGTTCCATCTTTCAACTATGATGCTTCTGCTGTCTACACCAACGGCTGTTTGGAGGCACCACC
TCCACCGCCACCTCCATTGGGCGGAGCGACAAGTCAGATAGCTGTGCGTCAACAAGCACCGACAGCTGCGCAGATTCAGATGGCAATGATGGAAG
ATGCTTTTGGCAATGCTCCCCCATTTCATCCAGATGCGGGTATGATGGTAGATTACGATGAGCTAATGCCAGATCCTGTCCAGTTCGCCAATTTA
ATGACGAGCTGCCCACCACCTCCGCCGCCTGGAGAAGGCTCTGAAGGTGATGCCCATGGCCCTGAGGATGGCGATCAGCATGACAACGAAAACCG
AGAGGACGTCTTGCCCCCAGGCATTGATGAAGCTGAATCTGCCCTGGTACCGCATCCGTTAGACGCTGCGGCACAATCCCGAGACGGGGAACTCC
CAAAGGACCTGGTCGAAGCGCTTGACATAATATTCCCCAGCGACGTAGCGATTTTGGAGGCATCAAATGGAAACAGTGAAAAGCAGGAAGATGTG
ACTATCACCACCATTGTTGAAGATGACGCAGTGCTCAGTGTGATTCATCTTCAAGATTTAGCTAAAGAGGGTATTCACCTTGTAACTATCAATGA
AGCAGAGGTACCTAAAAAGTCACATATTCAAACATCGGAGAAGATTGAAAAGTTGCAGGATTTAAATGGCAAATCGGACGACGGAGTAAACATAA
AACTGATTGACGCAGAGGATATCCCAATGCCGAATTCGCCTCCGGCTGAGCCGTCATTTGACGAGGAGACGAAAAGCAAGGCCTTACAGAAGCAA
GCTGATATCTCAGAAATACCAGAGCCGGCTGTATCGCCTTCAGACAGTGAGAAGCTTCGTCGTCAGTCGGAGCTTGACGAGTTGGCTATGCTGGG
AATCGACAGGAGTGACATGGCGGCACAATGTATGTAGAACGTGTCTTTCTTTGCTATGTATATTATTCTTTTTTTTTAATTAAATTAGAAACTGT
GCTATTTGAGTCTTAAATGAGTTCTACATTATTTTTTCTATATATGTGCATAGATGCTCTGTAAGATTTGAGTTGACTTGGAGAGGGCGAAAGGC
AAGTCCCGACGCCGGATACACGGGCGGACGAATCGAATAACACGTCAAGGAGCCCCATAAAAAGGAACAGTTTTAGATTTTAGATTGGCACCTGT
GTATGAGTGTTTTTGACGGAATGTTTTAAATAAATGCGCATATATGTATGTAATATATGTAAGAATCCTAAAAACGTTTGATTTATAATTGCTTT
AACATACACTGCGCGTCATCAGATTAGAGCCCCCTGCATGTCCCCGTTTCTTCTTATGTTCTGTTTTTCTATTTTGTTTTATTTTGCCATTGCAT
AAAAATATATCAATTTAATTTTTTTTTTGTTCACTGATATTCACCTCTTTGAGGATAAAAAAAGGTCCTGAAAAAAACCGTTATCTTTTTAGTTC
TGCTTTGTTTTCTTTTCGGCGAAAAATTGGACACGTATATGGCATCATCAGATTAGCGCCCCATAATGAAGTTTGGAATATCTTCCATAATTTAA
AAGGTAGGACAACAAAATTTTGTATGCTGTTAAATTGAATAGTTTGCTTTAATTTTGCGAAAAAATGGGACGAGGCACGCGAAATCATAGCTTTC
TATGAATGCGGGCTTTCTTTTTATAAAATTGCAAACGGCAGACATCGCAAAACTATAGTCAATTTTATTAAAAACAAGTGAACTTATGGAAAAAA
CTATAAAGGTGGCAATAACATTCCTTATCGAATACCTTGCAATTCCCACGACTCCTCCGACAAAATTCGGGGTAAAAGTGGCGAAAACCCGAGCA
AATCTTTGATTCAAAGAGTGATTAAGAAAACTAAACATTTGAAACACAGAAAACTGAAAAAAAACATCTCTTTATAAGTTGCGAAAAAAAGCACG
ACTGAGTTTTGCTTGAGCTTATATGATCCGGTCTAAGGAGTGGCATTATGTTGTATTTTCGGACGAGAAGAAATTTATCTGGAGAAAGCAGACGG
CTATAGTAATTACAACCATGATTTGCGTATAGAGGAGCATATTTTGGTTCGCTTTCACAGACGGGTTGGAGGTGTCATGGTATGGAGCGCAGCAT
CTTATCATGGCCTCTGTGAATTCCAGTTTTTAACAGCAAAAATTATATTATTATATATAATTGTGTATTAAAAAACTGCATTTCCCTATTTTAAA
AACATTTTTGGAAAC
(SEQ ID NO: 1075)

Exon: 1001..1784
Exon: 1847..2014
Exon: 2529..2716
Exon: 2782..3459
Exon: 4758..4906
Exon: 4972..6869
Exon: 6989..7185
Start ATG: 1094

Transcript No. : CT27625
TAATTTCGGAATTTGCCAGAAAAACACCGATCTGCTATTGATCTTAGTCCAAAATTGCGTTTTTAAGTCGAAAAGACACTTTTCGGCTTTTAGAT
GGATGAAGACTCGGCTACGATACAGCTGGGGGATAGGCGTCTCGGTAACGCGGTCGATCATGATCTGCTTCCAGGGCCACCCGGCGTCGATGAGA
AAAGCGGAAACGAGAACTGCGAGCCCAGGAGCAGTGGGTCGGGAAAGCGCGGCAAGTCGAATTCCAGGCGCCGTTCCACATCCCGTGGTCGGTCG
GATTCCCGCAACACATCGCCGTCGAACACCCGGCGAAGGCATTCCCTGTCCCGCTCGCTGACTCCACCGCGTCGTCGTTACGATTCGCCCGATTA
TGGGCGGTACTCCCGACGGCGCTTTGATCGTGATCGGCGACGCTCCCCCGAACGCCGGCGCTCTCCGCCACGTCGCGGACGACGGTACGGACGAT
CCCGGTCCCGCAGCATGTCGCCCCGACGGGGAGGTCGATGGTCACCAAAAAAAAAACCGTCGTCGCCGCCAGTGCCCCCTCCGCATGGAGGACCA
CATCCTCAAATGACCCCTGGCTATGGAGCTATGGCCGCACATATCTACGGATCATACGTCGCTCCACCAGATGTTTACGGTCACCAATATGGAAT
TCCGCCTAACTCGTTTCCACCTCAGGGACCGGGGTACGGTATTCCAGGTGCCCCGCCGGACCAAAGCTCTTTTGGCTCTGGCTACGGTCCGCCTC
CCACAAGCGCGTGGACGTAAATGTGTACGGTCAGCAGGTGTGGATTAACCAGCCTATTTCTGGGGTCCAGCCATCCGCTTCAGACTCCCTGATC CAGCCACAGAAGGCCCGCGAAACTCTCTCTGGCAAGACGATAGGCGAGGAGCAGTCGGTGCCAGCGCTCGAAGGCGCAGGTTTGACGCCTCAGGA
TGCTGTTGCCCAAGAAGCGGAGAAGCAAAAGGACGAGCTTAAGAAACAGCGCGCTAACTATGTCAAAAAGGTATCGCTGCTCAAGAAGGAAATGA
AAGTACTTAAGGACCAGCGCGAGGACCTGGCAGCAGGCGATGCCCCACCCTCGCCAACCACAAAGAATTTCATCGAAGAAAACGACCGCCTGCAG
ATGCAAATTAAGAAGAAACTTGACACAATTGAAAACGTTATAGATATGCTGAACGGCATAATTGGCTACGAAGAAGTTGAAGATGAACCATCTAA
CCAAAAGTCCCATGGCAAGACTCAACCGGAACAACAGGATAGTCGCTCGCACTCCTCCAGTGAGAGTTCTGCAGATAGCTCTGAATCCAGCTCAT
CATCTAGTACTGCTTCCGATTCGTCATCCGATAACGAAGACGGGGAAGGGGCAGGCGGCGCCGTAGGAAGTCCAACCAATCGGCTAAAGCACCGC
GCCATAAAGTCGATGAAGTCAAAGCAGCTACATGGTGAAATGAAGGCAGTGCCAACCCAAGCACAAAATTACAATTTTGTGTTTTTCGATCCCGA
GCAGCATTGGTGCGAGAGCTGTGGAGTTTTTCCAAAGTCTGCTCGAGACTATTTAAAGCACTTGCATGCCGAGGAACACATGAATCGAGAAACCA
TAGAAACTCCGTGGCATGTGGGTATTGACCACGATCCCTTTCCCACATTTGAAAACGCACCTGCCAGGCGCGTCCCCGTGAGGGGCATGCAATTT
CTGGTGCCGGCTAACGCTTGGTTTTGCAAGCTCTGCAGTGTTTGGATTGGAGACTTGCACTGCGCTTCTGCTCATCTTAAGTCTAGGCTTCACTC
CAATAAGTATCAGCAATTTTTAAATCAGAACCCCAACTATGAAATAGAGTGGCAAACAAACCGCGAGCGGGCCATGAATCAACAGAAAGATCACG
ATGATGCCAAGAATAAAAAGTCCAAGAAAGACGAGGACAAGGCGTCCAAAAAGAGGAAAAAAAAGGGCGGGGACAAAAAAAAAAAGAAGCGCAAG
CACGGAAAGAAGAGCAAACGTAGTACAATAGATGCAAACAGCACATCGTCATCCTCCGATAGCTCTTCGTCGGAAGAGGAAAATGGACAGCAACC
AAAGAAAGGTCGTACCGAACAGCAACCAATTTGTCAATCAGATAAGTCGACTAATGCAGCATCAATACGAGTGGCCATGAGAAAGCAGGAAAGCA
CACCAACAAATTTGAAGCCGGAAGTGCCTTGTCAGCCTGTGGTGCCGCCACCGCCACCGATCATAAAGGATTCCACAATTCCTTCAGAACGGGGT
AAATGGACTGCCGCCAGTGTCGAAGACCAAAGTAAGGATCAAAAGAACCGGGATGATACCATGCTCAAGCAATGGAATAATGTGCAGCCTGTTAT
AAGTGAGAGTGAAAAAAAGTTGTTGGAGCAGCTTAAAGGAAGGCTGAAGAACAAGGGAGCCCGCGACCAGAACAACCACAAAGCAGTACCAACAG
AAGCGAATGATGAAAAGTTTAGGCGGGGTGGAGGACGTCATTCTCGTTCACGTTCTAAGCGGCGCAGCTACTCTCGAAGCATAAGTCGCGGGCGG
GATCGAGATCGGCGGGATCGTGAGCGAGATAGAGACCGTGGTCGTAGGCGTCGGTCACGCAGTCGTGGCCGACACTTCTCTCGTTCGCCCATAAG
ATCTAGTCGAAGAAGTCGATCCCGTCAGGGCCGAAGTCGACGCAGTCGTAGTCGCTCTATTGAACGGGTAGAGCGTCCCGTGGTCAAGCATTCCG
AGTTTCGGCCCCGTACTGTGCCGGAACGCAAGCAAACTGATATAAAGCGCGACAAGAAGGATGCAGAAAGCAAGTCAAAGTCATCCAAGCCCAGT
AACAATTCCTTGCCTGGAGGCAAAAAACTACCTTTCATCGGTAAGATGCCAGTATTTAAAAAGCAGTCTGTTCCATCTTTCAACTATGATGCTTC
TGCTGTCTACACCAACGGCTGTTTGGAGGCACCACCTCCACCGCCACCTCCATTGGGCGGAGCGACAAGTCAGATAGCTGTGCGTCAACAAGCAC
CGACAGCTGCGCAGATTCAGATGGCAATGATGGAAGATGCTTTTGGCAATGCTCCCCCATTTCATCCAGATGCGGGTATGATGGTAGATTACGAT
GAGCTAATGCCAGATCCTGTCCAGTTCGCCAATTTAATGACGAGCTGCCCACCACCTCCGCCGCCTGGAGAAGGCTCTGAAGGTGATGCCCATGG
CCCTGAGGATGGCGATCAGCATGACAACGAAAACCGAGAGGACGTCTTGCCCCCAGGCATTGATGAAGCTGAATCTGCCCTGGTACCGCATCCGT
TAGACGCTGCGGCACAATCCCGAGACGGGGAACTCCCAAAGGACCTGGTCGAAGCGCTTGACATAATATTCCCCAGCGACGTAGCGATTTTGGAG
GCATCAAATGGAAACAGTGAAAAGCAGGAAGATGTGACTATCACCACCATTGTTGAAGATGACGCAGTGCTCAGTGTGATTCATCTTCAAGATTT
AGCTAAAGAGGGTATTCACCTTGTAACTATCAATGAAGCAGAGGTACCTAAAAAGTCACATATTCAAACATCGGAGAAGATTGAAAAGTTGCAGG
ATTTAAATGGCAAATCGGACGACGGAGTAAACATAAAACTGATTGACGCAGAGGATATCCCAATGCCGAATTCGCCTCCGGCTGAGCCGTCATTT
GACGAGGAGACGAAAAGCAAGGCCTTACAGAAGCAAGCTGATATCTCAGAAATACCAGAGCCGGCTGTATCGCCTTCAGACAGTGAGAAGCTTCG
TCGTCAGTCGGAGCTTGACGAGTTGGCTATGCTGGGAATCGACAGGAGTGACATGGCGGCACAATATGCTCTGTAAGATTTGAGTTGACTTGGAG
AGGGCGAAAGGCAAGTCCCGACGCCGGATACACGGGCGGACGAATCGAATAACACGTCAAGGAGCCCCATAAAAAGGAACAGTTTTAGATTTTAG
ATTGGCACCTGTGTATGAGTGTTTTTGACGGAATGTTTTAAATAAATGCGCATATATGTATGTAATATATGT
(SEQ ID NO: 1076)

Start ATG: 94

MDEDSATIQLGDRRLGNAVDHDLLPGPPGVDEKSGNENCEPRSSGSGKRGKSNSRRRSTSRGRSDSRNTSPSNTRRRHSLSRSLTPPRRRYDSPD
YGRYSRRRFDRDRRRSPERRRSPPRRGRRYGRSRSRSMSPRRGGRWSPKKKPSSPPVPPPHGGPHPQMTPGYGAMAAHIYGSYVAPPDVYGHQYG
IPPNSFPPQGPGYGIPGAPPDQSSFGSGYGPPPTSAWDVNVYGQQVWINQPISGVQPSASDSLIQPQKARETLSGKTIGEEQSVPALEGAGLTPQ
DAVAQEAEKQKDELKKQRANYVKKVSLLKKEMKVLKDQREDLAAGDAPPSPTTKNFIEENDRLQMQIKKKLDTIENVIDMLNGIIGYEEVEDEPS
NQKSHGKTQPEQQDSRSHSSSESSADSSESSSSSSTASDSSSDNEDGEGAGGAVGSPTNRLKHRAIKSMKSKQLHGEMKAVPTQAQNYNFVFFDP
EQHWCESCGVFPKSARDYLKHLHAEEHMNRETIETPWHVGIDHDPFPTFENAPARRVPVRGMQFLVPANAWFCKLCSVWIGDLHCASAHLKSRLH
SNKYQQFLNQNPNYEIEWQTNRERAMNQQKDHDDAKNKKSKKDEDKASKKRKKKGGDKKKKKRKHGKKSKRSTIDANSTSSSSDSSSSEEENGQQ
PKKGRTEQQPICQSDKSTNAASIRVAMRKQESTPTNLKPEVPCQPVVPPPPPIIKDSTIPSERGKWTAASVEDQSKDQKNRDDTMLKQWNNVQPV
ISESEKKLLEQLKGRLKNKGARDQNNHKAVPTEANDEKFRRGGGRHSRSRSKRRSYSRSISRGRDRDRRDRERDRDRGRRRRSRSRGRHFSRSPI
RSSRRSRSRQGRSRRSRSRSIERVERPVVKHSEFRPRTVPERKQTDIKRDKKDAESKSKSSKPSNNSLPGGKKLPFIGKMPVFKKQSVPSFNYDA
SAVYTNGCLEAPPPPPPPLGGATSQIAVRQQAPTAAQIQMAMMEDAFGNAPPFHPDAGMMVDYDELMPDPVQFANLMTSCPPPPPPGEGSEGDAH
GPEDGDQHDNENREDVLPPGIDEAESALVPHPLDAAAQSRDGELPKDLVEALDIIFPSDVAILEASNGNSEKQEDVTITTIVEDDAVLSVIHLQD
LAKEGIHLVTINEAEVPKKSHIQTSEKIEKLQDLNGKSDDGVNIKLIDAEDIPMPNSPPAEPSFDEETKSKALQKQADISEIPEPAVSPSDSEKL
RRQSELDELAMLGIDRSDMAAQYAL*
(SEQ ID NO: 1077)

Gene Symbol: BcDNA:LD19168
FlyBase ID: FBgn0027866

Celera Sequence No. : 142000013384504
ACGTTTTTGCTTAACCTTGACGAGGAACCGACAAATTTTGTATTACATTTCTGTGCAATTAAAAGTTATAACGTTTGTGGATATGAATAAAAATT
TTACCATACCTACGTAGGTGATAAACGCGTACTTAGTAGATGGTTTCATTAAACTAAAACAACATTTTTATGGTGTTTGTAAAAGCGCAATTTTT
TAATGCGTTTACTCAATTATTTATTGCCCAGGCCCGTTTGCCACAGCCCATTTAGCAACTTTAGCTGTGCGTTACCAACTATTTATATGCGTTAC
CACATTTGAAATTGTATGAGACAGCTGGTATTACAAAGAGTATATCTTATTAATTCACATTGTAGCACTGGTGTAAAAGTGGCATATACATTGAA
TTACGAATGAGAGTGTAAAAATACGGTGTACATTTGTGTATTCTTATTATTTTTGGTAGTTTTAAACATTTGAGGCATTTCTGTCGTTTGCAATT
TACAAATAAATGGCTAAAAACTATGGCTGACGAATGAGAACACCAAATTGAAATCAACGAACTTAAGCGAAAGCTATATGAATATCGAAGTTACA
TGTGAGATATATCACCGTGTATGTATGCTTACGTAAATATATATATATATATGATTCCAAATGGGTATTTCTTGATCAAAGATACTAACGATTTT
CTGAAGGGTCCTTAAATATTTACGAGTAATTCACCTTTTTGTTGGGTGAAACTATTTAGTTATTAAACTTGTACAAAAATAAAAATAAAATTTTG
AAAATTTCACAAACTTTGTGGCAAATAATTCAACAATATATTGTAGGTCTATTACGATATAAAATGAATTGGCACTTCATGTATAAATATGTTAT
TAAAAAATCAAAACATAATATAATTCTAGTTTATTCAAGGCCCTAAAGAGAATGGTTTTTACTTTTGAGATAGAACTACCCATGCCGGAGATGCG
TGAGAAAAATGTATAAAAAGCTTAGTCGGCAGTCTAGCGTTTCCTCCAATTCAGAAATTCGTCTCCTTGAACTCCTTGGATTGCAGTACAGGCGA
AATAGCTCCCCCATCGCCGTTTTCATTTCCATTATTGTGCTCCTCTCCGCCGCCCACCGTGTAGGCCATCACAGTGGCATGATCCAATTTCCCGG GCAATGCTACAAAGGCGCTGCTGTCCACCACACGCTTCCTGGCCGCGCGATGCTGCATGCGGTTCAGTTGCACCTCACGCTTGGCGCCATCTGGT
CCCGTAGAGAGTTTATAGAAGAGTTCCCTTTGCTCCAGGGTCTTCCTCCTGGCTGACGTTATCATCCGTACAAAATCGATAAGCAAGTGGCAGAG
CCTGCGTGCCGATACGCAGGGCGAAAACGTGCCGTTGATGCCATAGCTGAGCAGATCCTCTAAGCGGTAGAGGGTAAGAGCATGCCGCTGGGGAC
CGGTAACAAGGGGCAGTCCTGAAATGGACTTCGGAATGCGTTGGGGCACCACCGATGGCGGTGGAGCTGATACCAATCCCTGGCGTGGTTCAATA
AGCGTTTGGGAGCGCATATACTTTGGTCGACTAGGCGCATTATTAGGCGGACTTTCCGCCTTGGACTGACGAGCTGGTCGCGTGGGCGGAGTCGA
AGGATGCAGACGGGCATAGATGGCGGATGCACTCTTGTTCTGCCGTTTGGGTGCCAAGTTGGCGGGCTTGACATGTCCCGACGTCTGAAGCTTAA
CATCCGGAGTCCAGGCTTCGGCAAACTTGCCCACAACTGGATCGAAGTTATCGCTGATTCCATCCGACGTTAAAAAGACTATGTCTCCACTTTCA
ATGCAGGTCATCGAGAAGGTTAGATTGCTCAGCTCTGGCTTGTTGCCATCCGCCGGTCCAAGGGCACCCAACGCATCGCGCATGTCCCTCATGGA
ACTGATGTCGTGGGATGCCTGTGTTAGTTCCCGTACTCCGTGCTTCTTGGAGTACACATAGCCCAGGGAATCGCCAACATTACACGAGCACACGA
CATATTTCCCTGGCGCTCCGTCCAGCGGCAGCACAACGGCTATGGTGAGAGTAGATAGGGCTCCTCCAACTTCCAGGATACAACCGTGTCCCTCC
CAAAGACTACGCAGCAAACTCACAAAAACCTCCTGGGTTGTGGTGGCTCGGCACTCCAGCGCCTGTCCGAAGACCGCCCGGTCCAGATAGTCCAA
ACAACCGTGAACAGCTGAACGGGCGGCCAGACGAGCGCCATCACCCCAGTTGACACCATCTGCCATGGCAGCTGAGTCTCCGCGCACTA
CCATTCCGTAGCAGTCGGCGATGGGATTGCCCATGGGTTCTTTAGTCAGCATGTTGGTCTCGTAGAGGGACACCGAGATACCATATGCGAAGTCG
CACTCCATGCGCCAGTTCTCCACGCCAGCGATCAAAGCTGCGGGATCAGAGCCACCCTGGTTGCTTACAGCTTCGCGGAGCAAACGTTCCCGCTC
TGAGTTGGGATCCCCATCCGTCGAGACCTCAGTCTTTGCATTTAACACATTCCTATTGTTCTGATCGCTGTTGGCTTTTCCAGCATCCGTGCCAG
CAGACGCAGCGGCCAGATTGGCTATGCTGCTTTTGGAATTCTTGCGGGAACGCATTCCCGACGCAGAAGCAGATCCGGAGGGCTGCTCCGCACTG
CTCTGTCTGCGAGGTCCTGCCGGCGGCCGTCCGAATTTGCTGGTAAGTCGGGTTGAGTTCTGTGTGGCCACCTGAACTGGTGGTGTACTCCTCCT
AACGCCATAGCAATCATCGTTCTCCTGCTGCGTATCTATGAAGTCAATGTCATCCGCGAAGCTGGTGCTCAAGTGCAGTTTGGAGCGCTTGATGC
CGGTGAGCCCCTCGTCAGGACCTGTGCAGGCGGCTGTTATAGAGCAGTTTCCAGCTTCGTATGTATCCAACTTGAGAACGGGCATGTCCGTGGGA
TTCTGGCCATTGTAAATCTCCGGACCCTCAACAAACTGACGCTGCATTCGGCTGTCGGTGAAGGTGGTCGGGTAAATATTTGAGCAACTTTCGCA
GGCTACTAGGTTTCTATTTACTTACCCCTCCAGATATTTAGTTATGAAGCTACCATCATCATCCTCGTGCTCGCTGGCCCGCCGGCGACCCTCGC
GAGGCTCCGCGATGAAGCTCAACTGGCGGAAGTAAGTGGTGACTTTCTGGCGCAGCGACGGCATCTTTAGTCGAGTTGCTCCCTCCTCCTCGCCA
GCAGTTCTCGCCCTCCAGTTAGGGTTCTCTTAATTGCCAGAGATGGAGGGGCTAAAAAATGGATGCTGGGATGCTGACCAGTTCGTTCACCTCAT
CAGTGGCAATTGTTGTGGGAGTCGAGTCACTCCAAACGAATCCAGCCGCCGACCCTGCAAAGAGGTTTAATTTAGAGCTTCATTTAATTATCAAT
AAATTATGCAATTAAATGGGACTGGGCAAACACGAAAGAATTACAAGCAAATTGCATAGGCAGCCGCATAACTGACATTACTCCCTCCTTTCAAC
CGCCTACTCCTAAATGACGAGATGTGCTTTTTAGTTGCCGCAGGCCCTGCATCCTTTCCCTGGCCACACAAAACCCTTCGCTCATCAGGAGCAGG
ATGTCAGAGGAGAAATCCCACCCTGTGAATGGGCTTTTACCCAGCTCATTGCGAATGCAGTAGACACTGAACTGATGCGGACACAGAAATCCCCT
CCTTCCTTCGGGGTTCAGATGACATAGCTTTTAGCAGGGCTCTCCGCATGTGTTCTGAACCAGAGATGCCAATTTGGTTCTTTGCTCAACTAATT
TTAAATTGTTTATGGATTAACTTATGTGCCAAACTACTTGCCTTTCAAAATAAACCATTTATAAAATCGAACGCAATAATTTGGGACTTGATTTA
TCACAACATTTATTTATTTATTTATATTAAACCCTTTTCAGGATCAACTTTCAAATAGTCCTTTAGCATGAATTAAGTAACTGGCATCACTGATGTGTT
GATGATTAATGAATGGACAAACCAACTGCCTGGGGCGACCTGCAACTCCAGCAGATGTTGGGTTTTCGGATTCTGACAGCATCAAGTTCGGTTTC
AATGGAAAGATGATATCATATAGGGGTAAGTTTGCCGGCGAGAAACACACCAAGGTCTGCTGTACAATTATGTATCTAACTCTCCGCCGCTATCG
CAGACGACATTTAATTGCCGTGTTAGGGCATTTAACTACCTGATCCATTCTCGTAGACAATGTAACGCCAAGACAGCCTTCATTTCGGCGAGATT
ACAATGGATCGCAAACACAATAAATGCTAATCTTCAGCAGCAATTGCCGTGGAGATGCTTTTCCTTAGACGATGTACACAAAACGATTTGTATAA
ATGATAAACAACAACAAAAAAGTCGGCACGGAAAGTAGTTTGATGGGGGCAATTATTCAAGATACCCCCCCTCCCTTGTTGTTGCTGAAAT
TTTCACAAATGCTTCAAAGATATATATAAAAAGAAAAAAACACAATCAACCACTTTAATTTGTGGCATAAGTACTTCAAGTGACAAATGAGTGGT
CAATTAAAAACTATGTCGATTAACGGTGAATACTGTGGGTCGGTACGCCTCTCTATGCGCTTCTCATAAACGGCACTTAACGGCACGCGAAAATC
GCATGAACCCTGAACCAATTGTTCGAGTTTCGATGAACTTGAACTGCACTCACGAATCAATCAGCGAGTAATGTAATTCAATTTCAATCTGATGG
CCCCAAGATGCGCGATTTCTTGGCAATTGCTGGGCACTGATCCGATTGCCACCACACCCGCATTCCTTGCGGCAAAGCATTAAAATCAAATTAAC
CCACATAACCATTAAGTGCAGGAGTGGGAGATTTCCCATTACCATATCCACATTTCCCAGATACAAATCAAATGAATTGAAAAGTCAGAGCCGCG
AGACAAAGTCGATCGCTGGACGAAAGGGATGGATAGCTGAGTGCCCATGTGGTTATAAAGATATATCTTTCTGTGGATGCATTGAGGCGCGGCCA
GCTGTGTGCACTCGTACCGGTCCAGGGCAATCAATACGGATGATTGAAAAGCCCACCTTCACATCACCACAAAACAATTCAATTTAGCCACAACA
ATGTGCAGCTTGCGATTAAATGTGCAGCCAAAGAGATTACAACTGCACCACAAGAGCCAACATTGAAGCTCAGCCACAAGCGTTTTGTAGTTCCC
ATCTGCAATTGCTCCAATTTCTTTACGCCTCCTCCAGATCTGCTCATCCACGTCAATCAGAGTCGTCATCACTTGACACACAATAGGCATCTGAC
TGTGACTTACTGGCTTCTCAATTCCCTCAGCTTTTTCGCTTATAAGTGTCCATTGTGGGATCTCACAAATTATTTAAGTTCTGACTTTTGTCCAC
CTGACGGCACGTGCCGAGAATAAAGTATAGGTTTTATAGAGATGGAAAAATCTCTGGATTGAGAAGTAAACTCATGTAAGATGCCCGTAGCAGCC
GTTTTGTTTACCCATGTACATATATTATTTTTTAATCTTTAATTGCATTTTATGTATGTATTCAATTGTATATGAAATGACACTCCCCCAAACAT
TAAACAAACAATTCTTCGAGGCGTGTGCCGCAATCAATCGACACTTTTCGATTGGATTTCGGGACCATCGAAATTTTCAACACTTGAAACTAATC
AAGCGTGGAAATGGGGAAATAGGAACGCGGTGCTGTGAGATCATTGTGCAAGATCTGGGTGGGGCGATCCGTGGTGTATAAAAACAACTGAGTAA
ATATTATCGGATGTGGCACAGATCTCGTGAGTCTTTCGAACTTTGTTTATGCTCGAAAACCAAAATAAACCATTTGCGCTTCCTCCAACCAAAAA
TAGTTGTGTTGGCCCGTATTTATAGCTGCCGCCCGTGGAAACAAAAAATGTCTGGGTGAATTTCTCGCTTGAAAAACTCATTTGGGCAAGGCTTT
GAAATGCATTTCCCGTCGCATTCGAAATCAGCTAAATTTTCTGAGCTAATCAAATGCGCAAAATTATTGTTTACACACTGGGTTAATTAGATGTG
GAGATTGGTTTCTCTGCTCCGCTTCGAGATTCTTTTGTGCTCTTTCGGCTTTGTGCATACTTAAAATGTGTGTGGATTTACGAGGGAGAAGTGCT
AAAACCCAATGCAAACAAGTCTGCTTTGGGGTCCAACCAAATGCTCCAACCAAATGCAAACACACCCGTGACATTCAGAGTCTGGATGCACTTGA
GGCAAGTGACAGTTGTCTGCAGATTATGTGCTATGTGCTGCATATTGTGGAATCTCAAGGTGCAGTCGGTGGGCCAAAGCCGCAGTCAAAGAAAA
AGCCTTAACAGCACAAGTCAAGTGAGGCTGCTCAAAGCCGTTTTGTGTGCTTCTGTTTGGGCCAGACAACAAACAACAAGAAGCTATAAAAGCAG
AGAGTGAAAATTTGTTGCATTCATTGCGTGTTTTCTTCGAAAGAAAGTTGAAGGCCATCGTTAAGCTGTAGATTAAATAGAGCTGTCTGCTTGAT
TACGAGCTCCCAAATATTTCAATCATTTCGAGCGACCCACTTTATGTATATTGCTTTTGTAGCGAGTTCCCTCCTTAACGTATAAGTTGTGTAGC
TTAGGTATTCTAAGACCTTAGATTAGATGATTCTCCCTTATGGGAATTATAATATATGAAACAAAACCGTATGCACAAACCACATACACGCGTCA
AGTGCTGATTCAACCGCAGTCAAGGCAATCTTGGATAGGAAATGCATGCTTAATTTTCATTTCCTCATATGCAATTTTTCTCATTTCAAGTCCAG
GCTGATCAAGCCGCATAAAAATAAAATATTAAGTAGCAAATGCATTAAGCAAAATGGACGGGGTTCCCCAACCCAGAGTTTTAAACTGACAAGCT
TTTGGCTTAAACCTTCCCCCAATATTTGACCATGTGTTGACTCATTGGACAAGCCGTCAGCTGCATTAATAATGCATTAGACCAGCCCCAGGACA
TAAAAGTCCCCCCATCGTGCTAAAGTGGGCGCAACACGGCCTGGGGCTTCATGAAAATCTGGCAATTAAAATGTTTTACATTATGTAAACCGCAC
GAAAACAATCACTAAAGAGTTCCTTCACCTCGAAATGGCGTCGTGAATATGAAGCGATATGTATGATGTGGGAAACAAAGGAGGAGTTGAGGAGT
CTCTTCCCGGTTTTCGAAGCATTTCTTATAAATTGCCACCTAATTGGCGTGTTCAACATTGTGACTGTGCGTGGTACGCCTCATTTCCTGTTGCA
ACAATTTGCATTAATAGAGGGTCTCATACCACAGATTCAGTTCGAGATCTCCCCATCCGTATGCGAATGCGAATCTATTCCAGTGAATGCATTTC
AGTACCATTCAATTGAAGGCGCGATGAAATGGAAAGTTAAGATCCCTTTGGAGGATTGGATGTGTGTCAGAAGTTGAGAAACATCCTTTGTTTTA
TGTGCCTTCCATGTGCATTCGCACTTAACGCCAATGCCAGGACCTAAGAGCACCCAAACCCACCCAGTTTTTCCCCACTGCATTTCCGCTTGCAT
GTTTTCCCTTGTTTTTCCGCTTTTCGGGTCGCGCCACTTGGCCCGCTTTTCAGCCACGAAAAACTATACTTGAAGAACTTGCCACACGCCGAATA
CAATAAACTAAAACTGGGGCAAGGCGAAATAATTCGGGCCTAGAAAGGCAATATCAAAGGAGTGCCGGAGCTTATGTATGGTATAAGGGTAAATT
ACCTTTCGGACTTACTGGGTATATAGCATCAAACCACCCTCACACAAAACATTTAGTATGATTGTTTTTAAAGCCATATAATTACGGCGAAGGAA

FIGURE SHEET 582

AGCCATTCCCATACCATTCTACTAATTGGTTGATTTTTTGTTGGATTTCGCAAACATCTGGCAGAAAAATTGATGCCGCCAAACAACTCCACACA
CATTTGGCAAGCCCACAAGATAATTTGCATAAATTGAATTGAAGTCTTTACTTGTTGGCCAGGTAGCGACAGCTGTCGTCGGTTTATGTAGGACT
TATATACGACTAATCCTGCATGAATAAATTAAATGGGAAGCCTCAACTAAGTCTGTCTGGCGGCGGATGGGTTTTGGGTTTGGCCTCTGCCGAAG
CCTTTGTTGCCAAGCATACAAATGAGTTGAATCCAAACTCCTGGGCGCTGTCACTCTATGCAAATCTAGAAAACCAGTAACCAGTTGTTGTAGGA
TGGAGAAGGCACGGTGGACGGACTTTCGGGGCGCTCAACTCACATATTAAATTAAATGTTAATGGCAACAAAGACAATTCAAACGGAGTCAAGGC
CCGGGCCAAAGAACTGTGGCTAACAAAGAGGCAAACAACACCAATTTCTCGACTGCCCCGCAGCAATTGAGCAACCAACGAGCCACTTTGTTCGC
CCCATATACCCCGCCCACATCCCAGCCCCTGTCCACCCGTGAAATCTGTTCTCCACCTCCAGCTACCTCTAGATAATATTGCACTGTTCGGTGTC
AAATGGCTGCCCACTGACGGACTTCTTGGTTTGTCAGGTGCCATGGTTATTCCACCTACAGTAGAAGCTCTTGAAAGTGGAATTTCTTTCTATCT
AATAATAAAAGATAATTGCCGAGACAGTTTTGGTTAAAAGTGGTCAAAGTGCTCAAAGACTCTCTATCGTCGGTTATGTACGTTAATCATATTAG
AAGTAAGTGAAAATGTCCCCAGAAAGGACGTTCATTACAAGGAGCCCCTACTGTACAAGACCTTGCGGCGGGTTAAGTGACCGATTGGCTGTCAG
TCCCCAGCCAACCAACCTCACCTCTCGGACTTCTAGTTTTAATTTGAATTTCATTCCGTCTCGTGTGGTGGCCAAACGCTTTGGTGGTTCGCTTA
GTCATATCACTCGGCTGACTAATCATTGAAAGCGGAGCGTGCTTGGAGGGAAACCTTAAGCCCCAGATATACCCCCCTTCTAACTCCAAACCATT
TACCGAAATCTCCACCCCGCCAAAACCCCACACAGCTGCAAATTCAATGAACCTTTGCTGCTGTTGACTTTGCTGATTAATTGGAAATTGGCAAA
ATGTTATTTATTTTCGCGCGGCTGGTCTAGCGCCAAATGGTTGTTTTTCATCAAAGGCATAAAGTTCTATAAATGTTCCCAGACAAATTGGTTTT
AATGAGCCGGAAACTTTTTCGGTTGAGCTCGGATTTTTACGGGTTTGGCGGATAGAAGGAGAAGCCACATATTGTACCCGATTGGCTTTAAACAA
ACACGGACATACTATACTGAGACAACTTCTTCAGTGGCTCGCTAATGCATTATACAAGAATGAACTCCTTTGCAGGCACGGCCGAGCAAACAAAC
TTCAACTTGTCCGGACCAACTGCGTCATAAAAGAGCCAACGGCAGCGCCAATCGCCATCTCCGTTTCCAGCGAGACAACAAAGGATGTTGGGCGC
CGGGAAGCAGGAGGAGCAGGACCTGGGAAACCAGCCAGTTGTGGATGGAGCGCAGACAGAACAACTTCATGCAACCCCATCCCCTGGGAACCAGA
CGGCAGCCAGGAGTCTGTGTGCCTGATCCTTGCCATCTCGAAACGAAAAAGAAGCCGGCGAAAAATATATAAAATGGAGAAACAAAATATTTTCC
CGATGTGCATGCATAGTTCAAAGTTAGTTTCAGGCATCTGTGCACCACCAAATACACCACATTCCCCACTACTTACAAGCAGAATTGTGAAAATT
TTTTGGTTGCCAAGCGAAAGTGATTGAATTCCTAGGGATTTTGTCGGGCGCCAGTTGAAAAGGAATTTTTGATGCGTTTAAGTGCCGAAGTTTCC
CTAAAAAAGTTTGGCCTTAGAGTCAGGGGATGTATTAAAAAGAAAAATGTCGAAAGTTTTTGAAAGAAGAGATTAACAATGATGTGTGATACAAT
GATTGTGTGTTTTGGTCTGGAGAATTTAAATCTCAATAAAAAACTACAAAATGTATATTAATGAGGCTAACGATGGTTATATTATGCAAACAAGT
GTTGGGGGGAATATAATTATTTAAAATAATTGCATTTTTTTGCGATTCCCACTTTGCAATTCTAATCCCTAATAAAACTAGAGATAACTTATCTT
ATGAAGCAATTTGTTTACTACTGCGACTGGTCTACAGAATATACTGATGCAATCGCTTTAGAAGTGTGGTAGGTAATCCCGTTCGTTCTCAGCCG
GAAATCACCCCCAATAAGAAGTTTAGATAATCTTAGATACGGTATCTGCTTGTTGTTTGCCACATGCATCTACACCCTGGATTCTAAACTTAGTT
CCCCCAAAATATCTGACCGAGTTGTCCCCTTTAATTTACAGCTTATATCCGGCATGTTTTTCTCCCGTTTGAATTTTGCCACAGTTTGCGCCAGA
AGTTGTGAAAAGGGCAGAAAGAGAACGAGTTGAAAGTTCCCATTAGAATGCCCAATCCAAGCCATCCTGTTCCTTTATTGCGTGGCCCCTTTTTT
TTACATTTTCCGTAATTCCCAGCCAGGCACCATCACGTGTCGGGTTTCTCCAAGGTATTGGGCTTCGTGGAGAATCGATTTTGTGGCCTGACGA
GCCTGTTATCCTTGGAGCGAGCGCTTTTGGCTTGTTTCAGGACATAGAAATTGCCTGCTGCATGTCCGAAAGGCTCAACGAGAAATTATGCTAGC
TACACTGAAATCTAAACTTCAGTTCAAGGAACTCAGGAAAGAAAATACTATTCAGAAAATGAAGTTTTTATGTTTTAAAACTTTTATAACAGTTT
ATAATATTATTGATACGATGTCAATATTTTATATTTGTTTTAGTTCGGTAAAATGAAGATTATCATGAATTTTTCTCAGTGTGCGAATGGAGGTG
AGTGCGAAAACGAGAAGGAGGAAGCATCCATCACATGCATCTGCAGTTGGCAGGCAGGTAAAAATGTTGTACAAAAAATGAATAACTGACATTTT
AAGTGGGAAAGTTTTTGCATCAAAATCAACTGCCTGCCAATGCTGCTACCGAAATTCAATATATTAACAAGTGCTCCGTAATTGTAAATTATCGC
CACTTTTTACAGTCATTACTATTAGTAAGTTTATAATTATGTGGGTAACAAAGCGGTAAAATATGCCAAACGAAAAACAACACCAGCTATTAGCA
CAGTTTCGAAATACGATAAAGCTTGAAAACCGGTTATTGCACCAACGAAAGCTGACTTTTGTTGTTCTTGTTTTGTTTGTTATTGTTATTTTTGC
TAGAGCAGCTGAGATTTCGCAGCTGCCCGTGAAGTTGAAAACAAAATAAGAGAAAAAAACAAACGGCAGGTGAATCAACAGCGGTTCAAGCGCCC
AACCCACCCACAAGTTTGTTGGAGGGGGGACGACGACGTAAAAAACAGAATAATAAAGACGTAAACCCAGTTAAATGGAAAAATCAAGGCGAACG
AACACACACGGAAGCAAAAGCACAAAACAAAAGGCGACAAAAACACGTCGAAGGCGGCAAAAAAATTGGAGAACCCAAAAATCAATAGAACTTC
GAAATATCCATAACCATGTAACACAGTGCACATTCACTTACAATAAGTGTGCCTTCCTCTTCTGGGTTGTTTTCTTATCGCTACTTTACATATGT
TGGCGCCACTTGCAATGGGGAAATATATGTAAGTGCGTGCGTTCCGTTGGTGGTGTGTATAAATATTTAACATTTGCCGGAGGGTGGTTCCATCG
CCCAGAACTTCGGCTTCTGCATGGAATACTAACATAAATCGCGCTGCACAGTCCACTTTTGTGTGTTGCACTTCGAGTCCCAATGGTTACCAATT
AATGTCGCTACGAAATGGAACTGCTAACGACTGTTTCCGCCGCGGACCGACGTTCCTGCTTCGATTTGAAATTCGAAGTGAATTGGCCAAGCCAA
GCGATATTTGTGGTAATCGAATCGTCGATATGAAACACACTATTCTATGTGCAACCAACCGAGTTGGCAGCTCCCAGCGCGATTTTTCAGTATAT
TTTGCAGTATTTTAATTGTTGCAGACGGCTTTTTAAAGCGCCACCAGTTCGTTCACATTGTCGCTATTTTTCAGCATTTCGCGGGATCTGTATTT
TTTATAGGCGAATATTGAAATTTGCATGGTCTAACATTGATTATAGTGTTGTATTCACCGAATATTTATTGGTTTTACTGTCCATTGCTTTGAAA
GCAATAGAAATAATTGAGGATCAAGTAAGTTTAAGATAAATTATTACAGTTAAATGCCGATGCAGGCACTCACGCACACTAACGCACCCAAAACA
GCGACACGCGAATTTGCGAATTTCGTTTTGGCCCGTTGTTTGTGTGTTGTTGCTGTTGTTACAACGTTGTTTGTGCTAAACATTAATTAATTGTC
GCAATGTCTGTTTCGCTATAAATATGCGAAACGTGCCGTTGTTATTTGCGCGAAACTAAATGGCCAATTGCGCTTTACCGGTGTTAGTGTAGGTG
TATGTGTTGTCTGTGTGTGTTTGTGGTTGCTGGCGCGGGCGAATGGCGGGTAATCCGCATACACTCGCACTTATTTTTTGCAAAGGGTTTATGCG
ACACTCGCTTTGATCACGATATTAAAAGCTCAAACACCACTCTACCATTATACAAATATTTATTTATGTAAAATAAATGCGGTTAAATAATTTAC
CTTAGAACTTGCCCTAAAGGATATTAAGTGCAATTAAAAGTAGAACAAACATTCATTGCTAAGTTACTAAATGAATAGCATTTTCTTTTGCAAAC
TTGTTCATTATAAACTACTCCTTCGAATATATATTTACTTAGTATATTTTCTGTTTCCACGACTTTGTCTCACACATAAACACGTAAAAGCGCGA
AACAGACAC
(SEQ ID NO: 1078)

Exon: 11929..11814
Exon: 3379..3066
Exon: 2996..1001
Start ATG: 3199 (Reverse strand: CAT)

Transcript No. : CT27700
AACGTCGGTCCGCGGCGGAAACAGTCGTTAGCAGTTCCATTTCGTAGCGACATTAATTGGTAACCATTGGGACTCGAAGTGCAACACACAAAAGT
GGACTGTGCAGCGCGATTTATGGTCGGCGGCTGGATTCGTTTGGAGTGACTCGACTCCCACAACAATTGCCACTGATGAGGTGAACGAACTGGTC
AGCATCCCAGCATCCATTTTTTAGCCCCTCCATCTCTGGCAATTAAGAGAACCCTAACTGGAGGGCGAGAACTGCTGGCGAGGAGGAGGGAGCAA
CTCGACTAAAGATGCCGTCGCTGCGCCAGAAAGTCACCACTTACTTCCGCCAGTTGAGCTTCATCGCGGAGCCTCGCGAGGGTCGCCGGCGGGCC
AGCGAGCACGAGGATGATGATGGTAGCTTCATAACTAAATATCTGGAGGGCCGAATGCAGCGTCAGTTTGTTGAGGGTCCGGAGATTTACAATGG
CCAGAATCCCACGGACATGCCCGTTCTCAAGTTGGATACATACGAAGCTGGAAACTGCTCTATAACAGCCGCCTGCACAGGTCCTGACGAGGGGC
TCACCGGCATCAAGCGCTCCAAACTGCACTTGAGCACCAGCTTCGCGGATGACATTGACTTCATAGATACGCAGCAGGAGAACGATGATTGCTAT
GGCGTTAGGAGGAGTACACCACCAGTTCAGGTGGCCACACAGAACTCAACCCGACTTACCAGCAAATTCGGACGGCCGCCGGCAGGACCTCGCAG
ACAGAGCAGTGCGGAGCAGCCCTCCGGATCTGCTTCTGCGTCGGGAATGCGTTCCCGCAAGAATTCCAAAAGCAGCATAGCCAATCTGGCCGCTG CGTCTGCTGGCACGGATGCTGGAAAAGCCAACAGCGATCAGAACAATAGGAATGTGTTAAATGCAAAGACTGAGGTCTCGACGGATGGGGATCCC
AACTCAGAGCGGGAACGTTTGCTCCGCGAAGCTGTAAGCAACCAGGGTGGCTCTGATCCCGCAGCTTTGATCGCTGGCGTGGAGAACTGGCGCAT
GGAGTGCGACTTCGCATATGGTATCTCGGTGTCCCTCTACGAGACCAACATGCTGACTAAAGAACCCATGGCAATCCCATCGCCGACTGCTACG
GAATGGTAGTGCGCGGAGACTCAGCTGCCATGGCCATGGCAGATGGTGTCAACTGGGGTGATGGCGCTCGTCTGGCCGCCCGTTCAGCTGTTCAC
GGTTGTTTGGACTATCTGGACCGGGCGGTCTTCGGACAGGCGCTGGAGTGCCGAGCCACCACAACCCAGGAGGTTTTTGTGAGTTTGCTGCGTAG
TCTTTGGGAGGGACACGGTTGTATCCTGGAAGTTGGAGGAGCCCTATCTACTCTCACCATAGCCGTTGTGCTGCCGCTGGACGGAGCGCCAGGGA
AATATGTCGTGTGCTCGTGTAATGTTGGCGATTCCCTGGGCTATGTGTACTCCAAGAAGCACGGAGTACGGGAACTAACACAGGCATCCCACGAC
ATCAGTTCCATGAGGGACATGCGCGATGCGTTGGGTGCCCTTGGACCGGCGGATGGCAACAAGCCAGAGCTGAGCAATCTAACCTTCTCGATGAC
CTGCATTGAAAGTGGAGACATAGTCTTTTTAACGTCGGATGGAATCAGCGATAACTTCGATCCAGTTGTGGGCAAGTTTGCCGAAGCCTGGACTC
CGGATGTTAAGCTTCAGACGTCGGGACATGTCAAGCCCGCCAACTTGGCACCCAAACGGCAGAACAAGAGTGCATCCGCCATCTATGCCCGTCTG
CATCCTTCGACTCCGCCCACGCGACCAGCTCGTCAGTCCAAGGCGGAAAGTCCGCCTAATAATGCGCCTAGTCGACCAAAGTATATGCGCTCCCA
AACGCTTATTGAACCACGCCAGGGATTGGTATCAGCTCCACCGCCATCGGTGGTGCCCCAACGCATTCCGAAGTCCATTTCAGGACTGCCCCTTG
TTACCGGTCCCCAGCGGCATGCTCTTACCCTCTACCGCTTAGAGGATCTGCTCAGCTATGGCATCAACGGCACGTTTTCGCCCTGCGTATCGGCA
CGCAGGCTCTGCCACTTGCTTATCGATTTTGTACGGATGATAACGTCAGCCAGGAGGAAGACCCTGGAGCAAAGGGAACTCTTCTATAAACTCTC
TACGGGACCAGATGGCGCCAAGCGTGAGGTGCAACTGAACCGCATGCAGCATCGCGCGGCCAGGAAGCGTGTGGTGGACAGCAGCGCCTTTGTAG
CATTGCCCGGGAAATTGGATCATGCCACTGTGATGGCCTACACGGTGGGCGGCGGAGAGGAGCACAATAATGGAAATGAAAACGGCGATGGGGGA
GCTATTTCGCCTGTACTGCAATCCAAGGAGTTCAAGGAGACGAATTTCTGA
(SEQ ID NO: 1079)

Start ATG: 297 (Reverse strand: CAT)

MPSLRQKVTTYFRQLSFIAEPREGRRRASEHEDDDGSFITKYLEGRMQRQFVEGPEIYNGQNPTDMPVLKLDTYEAGNCSITAACTGPDEGLTGI
KRSKLHLSTSFADDIDFIDTQQENDDCYGVRRSTPPVQVATQNSTRLTSKFGRPPAGPRRQSSAEQPSGSASASGMRSRKNSKSSIANLAAASAG
TDAGKANSDQNNRNVLNAKTEVSTDGDPNSERERLLREAVSNQGGSDPAALIAGVENWRMECDFAYGISVSLYETNMLTKEPMGNPIADCYGMVV
RGDSAAMAMADGVNWGDGARLAARSAVHGCLDYLDRAVFGQALECRATTTQEVFVSLLRSLWEGHGCILEVGGALSTLTIAVVLPLDGAPGKYVV
CSCNVGDSLGYVYSKKHGVRELTQASHDISSMRDMRDALGALGPADGNKPELSNLTFSMTCIESGDIVFLTSDGISDNFDPVVGKFAEAWTPDVK
LQTSGHVKPANLAPKRQNKSASAIYARLHPSTPPTRPARQSKAESPPNNAPSRPKYMRSQTLIEPRQGLVSAPPPSVVPQRIPKSISGLPLVTGP
QRHALTLYRLEDLLSYGINGTFSPCVSARRLCHLLIDFVRMITSARRKTLEQRELFYKLSTGPDGAKREVQLNRMQHRAARKRVVDSSAFVALPG
KLDHATVMAYTVGGGEEHNNGNENGDGGAISPVLQSKEFKETNF*
(SEQ ID NO: 1080)

Celera Sequence No. : 142000013384505
GGATCAATATATCTTAAGGTAGAGGAGAGTTACAGGTGTTGATTTGCTTTTCATAGGCAAGTTGAGTGCATTTTGCGCTGCGGCTCTGCTGCTGC
TCTGCTGCGGCGGCTGCGTTGAGTTGTTGTCGTTGAGTTTTTGTTTGAATTAGTCTTTGTGATTTGGTGGGTATACGATTTATAGTAGTTGCATT
ATTATTATTATTAGTTAATAGGTATTATCGTGTCTCTTGAATATACTCTGTTAGCTTTTGCTGCTCTCTGCATTTATTCTTTATCAACATTTAAG
GTACGTTGCACATTTTGTCCGCTTTTCGGGGATAAACATAAACTGTACGTTATGTTGCGCTTCTAGCGTCCATTTTTGAATTACTCATAAATAT
TATTATATTTATAATTTTACTTATTAATTAATTTTCAAGTCTATTTGCGTATCACGTTTAAAACAATGTTCAGTTGTGAAGTATCCGTTGTTAGA
CATATAAAGTTCTTCTTCCTCTAATCGGGCTTTTCCTTCGCTTAAGTCCTCTTTCCATTTGGTTTTCCTTGTATTTCAGCCAGGCATCCATTGAG
TGTTGTACTGGTTGCAGTTTGTCGATTGGCTGGCTGTCTCTATAAAGATTGCGCATTGAAGTTGACAGGGGAGTTTTGGAGTTTGGGGGAGATGT
TCTATGTAGCGGGGAATTTTGCATCTTTTTCGCTGTGTTGATTTGTTCTCATTGTCGTTCGTTGTTGATGTTCTTTTTTGTCGGTCGGTTGTGTG
AGGACAGTAGTTTGTGTGTTTTTACTTGTATTTTGTTTGCTTTCAGTTTTCTTTTCTTGAAACAGTTTTTCTCTTCTCACCTAATAGCTTCTCA
AATTGGTTTAATTGTTTTATGATACACACTTGAGATCACAAACATTACTCTTGTTTTTTTTTTTTGTTTTTGTTTAAAAAAGTTCAAATTTCCAG
TTGAAATGTTTTCGCTTTTTTTGTAAAAGTTTTTCATTTTCCATTTTTTGTTTTATGTTTTTGTTAATTTTTTTTTGTTGGTTTTATGTTCATA
TCGATTTTTTTTTGCAACTCATTGACGGGTTCGGGGTCCACCGGGTGTTCTTGCCATTCATGTCGGTCCTCCAGATCCATCTTCAGATCCAGCTC
TAGATCCAGATCCTGTTCCTGCTTTCCTACTCCAGACACTGATCCTCCAGCACCAGTGTGGTTACGACTGCACATTGAGCAGCAACTTTAGGTTG
TGCGTGTCGAAGTCATCGAGGAGATTCCGCTTCGAGCGGCCTGTCTGCATCGGCACCTGGAACTTGGGCATCGACGGCATCATCATGGGAAGCTT
ACCCTCCGACCTGGACAACGTCCAGTGCTGCGGTGGCTTGGGCAGCGCCGTTGGAGCTGGTGCATCAAAGCACTTGCTGCCCGCGAAATGCGTCA
GTGCGGTGGGTATGAGTGGGTGCTGCTGCATCTGGTGCTGGGGCGATATCTTTCCGCCCAACGAAGGGCTCTTCCTCTGCTTGCGAGCCGATCCT
CCGACGATTCCCGGCGAGAAACCTCCACCCAAAATGGTGGCTGGTGACTGCCGAACCTGCATAGCTCCCTGGGGCGAACGTCCTCCTCCGTTCCT
TCGGTTGTTGTTGGCAAAGAAGAAGCCTCCACCGCCTACAGAGGATCCCTGCTGCTGCTGCGGCGACTGGCGCTGCTGCTGCGACTGCTGATACT
TGTTCTTGGATCCGGTCGACTGGGACTGCAGTTGCCGTTGCCTCTGGTTCGGGGGCGTGGCAAGAGCGGATAGACCCAGGCCAAAACCGAGACTC
GTGGGCGAGGAGCTCAGGAATTGGGCGTTATTTGTACTGCTGGCAATACTGTTGGAATGTGCAGTTACCAAGGGCGTTGCTGGTGCGGATGCGGA
TACGGATGTGGGGGAGACGGGTGCGGATGTGGGCGAGGGGGTGGATGAGTTGGATGCGGAGGTCGCTGATGCTGCTCCCTTTTTTAATCGTATGG
ACTTGGTGGCCGATGCGGTTGTCATTCTGATGTTGTTTCTAACGCTATTGTGCGAGTATGTCATAGTAATTTCGTCGCTTTCCGATCTCTGGATC
GATATCTCTCTCTCTCCGATCTCCTCTTCTCTTTCTCTTATTAAAATTTCTGCTGTTTTCCCTTTTTGTTTTTGGTTAATTCGCTAAATTAATGC
TTAACGTTAAATATCACACGCACTTAAATCAATTCTTTATAAATCGAAACCAAACGCCTTCTGATTCTGATTCTGATTCTGCTTCTGCTGCTATT
GCTATTGAGATGTTGATCTAGCTGCGCCGCTCTATTTCTTTGGTAGCTGATAGTCGCCGAAGTTGAGATGACCTCCAAAATGGAAACGAAAAGG
GCGACGGGCGGCTGAGCACGTAGCTGCTTTTCCACTTCTCCTTTATGTTTTATGTACAGCTGTTGTTTACTTTACTTTTAGTTTTACTTGTAACG
TTATGTATTGTTTATCAGTCTGTTGATTTATTTTTTTTTACTCCGGTTAAGCTATCCTTAGCTATAATTTCGCAAACTCTCTGTTCTTCGCTGA
TTTAACTGCTGCTTTCGCATTCCAAGCCGTGCTGATCCTGTTTTTTGGAGAAGAGCGAAAGAAACCATTGAAAATTCGAAACGATACATATTGGC
TTATGTTAACAGGAAAATAGTTGAAGTCTTATTTCTTATGAAACTATTTATGAAATCAGCATCAACCGCATTAATTACAATGCAGTTTATTGAAA
TACATTCTTACGTTAAAAGGTCTATATTTAAATTTAGGTTGAGTAAGAAAGATAATATGTACATATACACATGGAAAAAACGTCAGTATACGACA
GAATACCTTTTTTACCTCAGTACGAAATGTAACGTTCCAAAGGTAAAACAAAACAGTTCTATTTCGATGGCCGCGTGTGTGTGTGTATAATAAGA
AACGGGAACCCGAAAAGGGGAAATAAGACATGTAACGATTACATTTCCAGGTAGCAACAACCTGTAACGTAGTGCTAACTACGTAACGGCTGCAT
TATCGTTTTAGCGTGTGACTGTGTGTAGACTGTGTGTGCTATTTACGTCAACAAAAGGTGTTTGTTTGGCTATTCAAGCAAACTTGGGACGTCAG
AGGGACGACCCCACATGTATATATAAAGATACATATGTACATTTATTTTGCGAGAATACCTGAATTAATGAATCAACACACACACGCGCATACAT
ACACACGCAGCGATTACTAACACAATTGCGACTTACTTTTTTGCCGTAGACCTCACACCAACGAGTGTGCTTGCGTGCGTGTGTGTGTCGCAGTT
TTCTCAGCCACTTCGTTATACAGATTTCGATATTTCGACAAGCGTTATATACAAAATGGGTTGAGTTTGGGTTAAAAGTTGCCTTGATTTGGATG
TTTCACTTTAAAATGTTGCGGAAATTGGTTTGTTTTGCGTTTTTTTTTTTGCTCTTTTCTTCGGATTTTATTTGGGGTTATATGTGGATGTGTTC GCAGCTGTGTATATATATGTGTGTGTGTGTGTTTTGTAAAATCACTTTCAAAATGGCGACGGGCTGGCTTCGTATTTATATATTTATATATATAT
ATATAGATGTAATTCCGCTTAAAGCTTTCTCTTCACTTACAGACAAAGGCTCAAAAAAATCACACTTTCAACTGATTCTGATTCGGATTTTGTTA
AACTCTTATGTACACCACCGTCTATTGCGCAGCGTTTATTTCGAATTTGATTTCCGTTATTTGCGCTCGCCAAGTACTCCACTTTAGTGTGTGCT
CTTCTGTAGCCTCACTCGTTGTACTTCGACGCGTATTAAAATATTAAACTTTACACAAATATTTGATTTATGTCACTTAACTTAGAACATTTACA
ATATGCGTTACATATATATTTATTTTTGTAGCAGAAATTTTAATCGATATCTTTATCTTCTTCGCTTATGCTTGTTCTTTGCGCATCGGTACGCT
TGCCTCGAATTTTCCACCATGACTCACACAAGCGCACGACTGCGCGGACTTTTATATGCCCGCAGCGGCATTGCCAAGCCTAAAAAATAAATTTC
CCTCTTTATGTATACATCGAAATATGTTTAGGCAACTCTGGGTTCGAGACACGGGTGAATCAGTGGATACTCAAGCCGGAAAAGCTGGAGGCCTG
TTCAGACATGCGGCGACCGCGGTTAGTAAATTAGTAATTATTTTTTATGACCAACCTATTGTTTTTACTCAAAATAGTCAATGTTGTGGATTCGG
GACTTGCACGTGAAACAAATGTTCAATATTGGTAAAACAAATTAAATCTACCTGTTTTTGATTACTACCTACCTACTAGAGTTGTTACATCTGCC
GTTATAAGAAAACAAAGTACGCGGCAATTTGAAATTGAATATAATACGACAGCTGGCATTTTGGAATGGATTTCGGCCTAAATCCGGATTATAGT
TATCTTATGTAAATAAATATTCAATTTGTTTTAGTTTGGCGCATAAGCGGTTGTTTTTGTATATCATTATATGAATAGTTAATAAAAATTGTGCA
TGTAAATTCAATAGATTAAGTGCACGTAAAATGAGAGCATTACGTTTGCAATTAAAAATTAAGCCATTAAACACGAAATTGAATCAATTAAAGAA
TGTCATCTTCTCCATATTCGGATTACTGTCTTAATTTTAATGGTTGAAGCTCAAATTGAATTCAACGCCCTTGCTATTTTTGTGTTTTTGGCAAA
TAAATTAGTGTTACACAATCTTTTTAAAAGAGAAGATAAATGTGATATTACATTTTATTGAACAGGATCAGTTGCACATATCTTTTGAAATCAGC
CGAAGTAGCTGAATAACACAAGTAATTACCTTATACAAATTCAATGCATCAAGAAATCTGACACAATGGGGTATAGTGGATGCCCCGTCAAGAG
GATAAATAAAATAAAATAGGATGATGAGAACCGCTTACAACCGGCGACGCGTGTCACTCAAAACC
(SEQ ID NO: 1081)

Exon: 4005..3651
Exon: 2602..1001
Start ATG: 2020 (Reverse strand: CAT)

Transcript No. : CT27750
GGAAAATTCGAGGCAAGCGTACCGATGCGCAAAGAACAAGCATAAGCGAAGAAGATAAAGATATCGATTAAAATTTCTGCTACAAAAATAAATAT
ATATGTAACGCATATTGTAAATGTTCTAAGTTAAGTGACATAAATCAAATATTTGTGTAAAGTTTAATATTTTAATACGCGTCGAAGTACAACGA
GTGAGGCTACAGAAGAGCACACACTAAAGTGGAGTACTTGGCGAGCGCAAATAACGGAAATCAAATTCGAAATAAACGCTGCGCAATAGACGGTG
GTGTACATAAGAGTTTAACAAAATCCGAATCAGAATCAGTTGAAAGTGTGATTTTTTTGAGCCTTTGTCTGATCAGCACGGCTTGGAATGCGAAA
GCAGCAGTTAAATCAGCGAAGAACAGAGAGTTTGCGAAATTATAGCTAAGGATAGCTTAACCGGAGTAAAAAAAAAATAAATCAACAGACTGATA
AACAATACATAACGTTACAAGTAAAACTAAAAGTAAAGTAAACAACAGCTGTACATAAAACATAAAGGAGAAGTGGAAAAGCAGCTACGTGCTCA
GCCGCCCGTCGCCCTTTTCGTTTCCATTTTGGAGGTCATCTCAACTTCGGCGACTATCAGCTACCAAAGAAAATAGAGCGGCGCAGCTAGATCAA
CATCTCAATAGCAATAGCAGCAGAAGCAGAATCAGAATCAGAATCAGAAGGCGTTTGGTTTCGATTTATAAAGAATTGATTTAAGTGCGTGTGAT
ATTTAACGTTAAGCATTAATTTAGCGAATTAACCAAAAACAAAAAGGGAAAACAGCAGAAATTTTAATAAGAGAAAGAGAAGAGGAGATCGGAGA
GAGAGAGATATCGATCCAGAGATCGGAAAGCGACGAAATTACTATGACATACTCGCACAATAGCGTTAGAAACAACATCAGAATGACAACCGCAT
CGGCCACCAAGTCCATACGATTAAAAAAGGGAGCAGCATCAGCGACCTCCGCATCCAACTCATCCACCCCCTCGCCCACATCCGCACCCGTCTCC
CCCACATCCGTATCCGCATCCGCACCAGCAACGCCCTTGGTAACTGCACATTCCAACAGTATTGCCAGCAGTACAAATAACGCCCAATTCCTGAG
CTCCTCGCCCACGAGTCTCGGTTTTGGCCTGGGTCTATCCGCTCTTGCCACGCCCCCGAACCAGAGGCAACGGCAACTGCAGTCCCAGTCGACCG
GATCCAAGAACAAGTATCAGCAGTCGCAGCAGCAGCGCCAGTCGCCGCAGCAGCAGCAGGGATCCTCTGTAGGCGGTGGAGGCTTCTTCTTTGCC
AACAACAACCGAAGGAACGGAGGAGGACGTTCGCCCCAGGGAGCTATGCAGGTTCGGCAGTCACCAGCCACCATTTTGGGTGGAGGTTTCTCGCC
GGGAATCGTCGGAGGATCGGCTCGCAAGCAGAGGAAGAGCCCTTCGTTGGGCGGAAAGATATCGCCCCAGCACCAGATGCAGCAGCACCCACTCA
TACCCACCGCACTGACGCATTTCGCGGGCAGCAAGTGCTTTGATGCACCAGCTCCAACGGCGCTGCCCAAGCCACCGCAGCACTGGACGTTGTCC
AGGTCGGAGGGTAAGCTTCCCATGATGATGCCGTCGATGCCCAAGTTCCAGGTGCCGATGCAGACAGGCCGCTCGAAGCGGAATCTCCTCGATGA
CTTCGACACGCACAACCTAAAGTTGCTGCTCAATGTGCAGTCGTAACCACACTGGTGCTGGAGGATCAGTGTCTGGAGTAGGAAAGCAGGAACAG
GATCTGGATCTAGAGCTGGATCTGAAGATGGATCTGGAGGACCGACATGAATGGCAAGAACACCCGGTGGACCCCGAACCCGTCAATGAGTTGCA
AAAAAAAATCGATATGAACATAAAACCAACAAAAAAAAAATTAACAAAAACATAAAAC
(SEQ ID NO: 1082)

Start ATG: 938 (Reverse strand: CAT)

MTTASATKSIRLKKGAASATSASNSSTPSPTSAPVSPTSVSASAPATPLVTAHSNSIASSTNNAQFLSSSPTSLGFGLGLSALATPPNQRQRQLQ
SQSTGSKNKYQQSQQQRQSPQQQQGSSVGGGGFFFANNNRRNGGGRSPQGAMQVRQSPATILGGGFSPGIVGGSARKQRKSPSLGGKISPQHQMQ
QHPLIPTALTHFAGSKCFDAPAPTALPKPPQHWTLSRSEGKLPMMMPSMPKFQVPMQTGRSKRNLLDDFDTHNLKLLLNVQS*
(SEQ ID NO: 1083)

Celera Sequence No. : 142000013384828
TGGATGGCATTTCAAACATGCGAGTGCTGAAATGGGCCAGCTTTAACTATTCCAATACCAACTATGCCATCCGCCTGAGTGATATCTACATTATT
AAGGTATAGTTAAGTTCTCACCACTTTGGTTGACAAAACTTTACTACTAACTTTGCTTTACAGTGCGAGGACTGGTATGCAACAAATGGTGGAAA
CTGTGAGGAGATAACACGGATTGCGGAGCAACTGGCTCGCAGTGCCTCGATGGCTCTGCTGCCACTTCTCGATCTTTTAGCAGCTGCTGGCATTA
ATAAGCTTGGCCTAAGAGCCACGCTCGATCAGGATAACGTATGTCTATTCAATGCGGAGGCAATTCAAATCACTAATAATATTATCCACTCCTAG
GTGGGCTATGAAGCCGGAGCTCGTGGCTCCAAGCTACCGCCGTTGTACATGAACGCGCTGGACAACCATCTGATAGCCACGCTGCATGGCGAATC
CTCCGGCATTCAAGAGCCCATCATTCTAGAGCTGATCTTTTACATACTGAACGCTTGACTTTAGTCCCTCGTAGTGCAATTCTCCCGCTGGATCC
GAAGACCAAACGGAAACATTCTTAACTCTAAGCTCGACGCGATCAAAGCCAATGGACAACTACACGAGTCCATGGGGCAAGAAATGAGGACATGT
TGGTATTGTTGGATGGCTCAGTTAACTGTGTATATATTTAAGTAGCTCATCGTTTGGTTTTTGTCTATACATTTCTACAACCCCCCCATTTCTAA
CCTTTCACTTCAACTGTTATATTATTTCTGATTTTTATTAGTTTTGAGTTTTCATTGAAAGTAAAACGTATCTAAGAAACCTAAATATATATATA
TTTGTATGTGATGTTCTTTAATATGCTTTACACATTTACCACTCGAGTATATATGAATAACAACTATATTAAAACTGTTGATCAAATGGCTGTTT
CACTTTGTGGATATAAGATAAATTAGAAAAAACAAAGGCCGCGTCTTGTTAAATTATTGATAGCAATTCTTTATTCAATTTAAAGTGTTTCAATT
GACTTCGTCTTGAGAGTGTGTCTGATTTACAATATACGATATTATACGATATTATCTTTACGATGGGTCTAAAAATCGTCACCACCCGCAGCCGA
CACAAAATATATAACAACCTATAAATGTATATAAAAATGATGTTCATTCTCTCTCAGATTGTACATAATTTAAACTACGTCTAGTACCGGGGTTA
CAGACACACAAACTACTAATGCACTCCTCTAATGTGTTGGTGTTTAGATGCAGATGCAGATGCTGATGCTGATGCTGATATGTATGCTATATACA
AAATGACATCGGGAAGCATTTGGTTGCACTCGATTTATTGCTCGGCTCGTGCCTCATCTGTTGTATATGTTCTATTTTTGTGTATATATTTGGGT TTTATATAACTTAAGCACTCGTGTCCCTTCGATGTTGACGGCAAACCAAGAACCCCCATTATTGAGCACTACAGCTCGTCGTGTTTGGGTCCCGA
GAACTCATCGTGCGAGATGAAACCGTTCTTATCCTTATCCTCGTGCTGAAAGATCTCCTCCACCAGCTTGTCGTTCTCAGCCAGCATGTTCTTCA
GCTCCTCGGAATCCTGTCCCTCCACGGCGGTCATCTGCTTCTTTAGATACTCGCTGACCTTTAGAGGAGAGATATAATATCCAGCATTAATTTAA
TTGTAGCTACTTTATATATTGCTCTAGTCTACTGAAAGCATAGGCTGGTTAGTAACTTATCCCACATCCAACGGATATTTCAGTGTAGAGAGACA
TGTATATGTAACAAAAGTGCGATCCATACATAGACGATTACCTCTTCGCGACTCAGCTGCTTGTCGGCATTATCGTCGATCTCCTTGAACACATT
GGTGGTGGGCGGGGCATTGCCGATGTTGATCAGCTCCACATCGAAGAGGAGGGTGGCCTTGGGCGGTATCACGTTGCCGGCACCCTGGTCACCAT
AGCCCAGCTGGGGAGGAATGGTCAGCTTGCGCTTCTCACCTGGATTTCAAAGTGAACTCCAAATTAATTTACACATTTTACCGAGCACTTCTCGC
AAGCACTTACCCACGCACATGTTGAGCAGACCCTGATCCCAACCCTTAATCACCTGGCCGGCGCCCAATTGGAATGTGAAGGGCTGGTCGCGGTC
GAAGCTGCAAAAAAAAAAAAAACGAGATGAAAAAAAACACGGGGACATACAAATTGTTAGACGCTTGTTGGCCACAAAGTTTCAAGTGCTTGCAG
GTGTCGTGGGCTGAAAGCCACCTTAAACCGAAACAATTCATCATTTCTTTATGACTGCTCTCTTTTTTTCATATCTTTCGTTATTTGCAGTCTAT
AAAAATTATTTATTTGATGGTTCCGCTAAGCGAATTTACTTTAATTTGCTAAACGTAAAAAAGGGGGGATATAAAGGCAATGGAGCTGCTCAGGT
ATGCATGAGAATGTCGCGCTTGTTGAGCTTGATGTATGATGTGGCACAGTTGCAGGCCATTTCGCGATGATTATGATATATAGAAATGGATTCAC
AGTAGCTCAGGGTTTGCTAAAAAGGTCGGGGGCATATCGCAAATGGAGCCATAAACACGCTGTAAAATGGCGTTTATAGGCCAACATGAGCTTAT
GGGCTTTAATTCAGTTTTGAATTGTGCATTTTTCAAGGGTGTTAATACAAATTAAGGCTAAGCCGCATATACAGATACATAAAACACGAACAATA
TAAATTCTAAGTACATTACACATCTCATTTCCACACAATTGAATTAATCAAAATTTGTTTATTTCAAAGCTTAAGTAACGATCTTCAGCTGAAAT
AATTAGTTAAGACTGTAATATAGCTGTTCTCCTATTGTTCGAAACATTTTAAAAGATTTTTTTTTATAATTTTTTGAACAAATGTTCTTAAAC
TTTCTGAAGCCTCTAGAGATCAGAAGTTGGCAATTGAAATGTGTCGCTTGGGCCTGCTGACTGCAGGAAAAGTTTCCTTGACGTTTTCCTTCGAA
AACTCTCCTGTTGTTCATCATTATATTATTATTGCTGTTTGTTAAGAAAGTTGTTTGGCTGTTGGGTTTTTAAGAACTTGTTGGTTATCCCCGTT
TAAATGGAGCCGAGACAGATTATTGCACTCGAGGCTGGGGAAAAGGAAACAAATGATTAACCAACCAGGAGGAGTCACCCACATGGCTGGAAAA
AGTTGTAGGGCATGTCTGTTAAATATTTTATGTGCATCTCTTGGGCATTTTGCAAAACATTTTTACATGCGCCGGCTGTTGTTTCAAATTCCAGT
TCAAGTCACAACCATGATGGGGCAAGTGGCAAGTGGCAAGTGGAGGTGCGGCAAGTGGCTCGGCGGATTGCCGCTGAATAATCCACCCAACCGGG
CCGCAAAAAAGAAAAAAAAACGAACATTCACATTCAGAGCGGTTAAGTGTTACGCTGGAGCGTAACCAAAGTGTCGTCGTTGCTGTTTTTGTCGC
CCGCCTTTCGCTCAAGTGCAAATCTCCAGATGGAATAAAAAAGCGTAAAAAATTTGTACCACCACCCCCCTTCCCAACCCACTTGAGATTCCGCA
TGTCCTGTGTGTGTTTCGGTTTGGTTTTCCAGGGATTACGCGGCATCTAAGACACCTTGGTGGCTTGTCTTTATTTCGGTGTCGCCGTCTGTGGC
TGTGAATTTTTATTGCATTATTTTCCATGAATATCTAGTACAATATGTGAAACATTTTATGGAGTCTCCCTTCCTTCCATTTCATATCCTTGGAG
TGTTTACTCCTGAATCCTCGCTAATTTATGCGATTTGCGAAGCTTACAACAAGCTCTACATGTTTATTTTTTTTTTGTACACTATTGAACGGGTA
TCTAAAATCGCTTATTCGCTTTTTAAGTTTTGAGTTAAAAACTGCTTATAAACTTTAATAAATAAGCATTAACTGCAATGACACTTTAATTAAAT
TTCAACAATATTACACCCCACAACTTTAAATGCGAAACCGTTTAAAAAACGGAGCTGTCGAGTCGTAAATAAATTAATAAAATCGTTTAAACGTG
TTGATTGTTTCAGTCAGCACGATTGAGCCCCCTCCCCCCCCTCTTCTCAACGGACTTCCGTGTCCTTCGTCCTGTTTGTCCCCCTGAAGCAATCA
AATATTTATGAATTACCGGACAAGACAAACAAAAGGTCAGCTGAGATCAGACCTGAATTCACTCGCAGGTGGGCAAACAAGTTGCAGTTGCTGTT
GCTGTTGCAGTTGTTGTGCAATTGGCAAATATCAAACGGAATTTCATCGATATTTTGCAAGCGATTCGCAGGTTTTTCCAGCTCGTCTCCAATGG
GGCTTAGATTGTGGTCTAAAGTGGGAAATAATGGGGGGTCTGCTGTCAGGGGGGGAGGCACAAGTGTGTGTTGCGGGGTGCTTCTTTTTACAT
TTTGGCTTTATGGCCAGCGCATTATCATAAAGTCAAGCAAAAAAATGTAAACTCATTCATCCACTCGCTAAATATTTAATAAGTTTCGATTTCATT
CTTCCACTGGCTGTGCCGTGTGTTGTTCCTTTTTTAACCCAATCCCAATTCGAATCCGTGTTGGTATCTGTATCTGTATCTGTATCTGTATCTGC
GAATTGCGAGCCAAGTCCCAACGCATCGCATAATTTAAAATGCAGCTGAATGGGCGCCCAAACATCCGTTTGCCGTTCTACGTGATTCCGCACCA
CGGGTGGTGGCATTTCGATGGGTGGGAATCTTTTGGCTGGGCATATGGCCACCCGAAATCATACCACGTCACTCCGCCGACTTCAGACACATTCA
ATCCAATCAAATTGAATCCTTTGGGTGGATCCCTTGATGACCTCGTTTTATGTGTCCGGCCAAGAAAAGTTATAAAATCAAATATGCAACCGCA
ATTCCTTTGCCTTCCGCTTTTTTGGATACCTCCCCATTGGGGCGACAACTTGCGATTAACGTGCACCAGAGAACAAGGACTCCAGCAGGACCTGC
GGCGCAGGATTTCTCTCGGCGGGAATGGTCAACGTGCGAACAATTCACACAAAAAGTCTAAAGTTTGAACAAGTTTGCAGCCCAGCAGCACTGAG
AGAAAACAGTTGGGTTTATGGTCTTTGAACTACTATAAGTTCTGAATGCATGGATGTTTTTTTTGTTTAATTAGGAAAATGAAATATTTGAAATA
TATTTAGTAAGTTTATAGACTTATTTCTTTCTATCTACGTATCCTTTTTTTTCAGTGTCGGCACAAGTACCTCAAAGGACACCCAAATTTATGCC
CCAGCTGGCGGCATCACGTTCCATCGCCCTTAACACACAACCCCGAAAAAAGCTGCTGTAAATTGTGGAAAATAAGAATTGCAACCGTTGAAGCT
CATTAATTATTTAAACTATCTACAAATGTCTGACGCGCGAGCCGAGTAAAATATACATTCGTGGCAAGAGTTGCCATAAAAGTCAGACGGCTGTT
GCAGTTGCAGTTGCAGAAACAGCCGCACTTGATTGCATCCACATGGTAATGAGCTTTAGATTTACTGGAGTCTGAGTCGCAGTCTGCAACGCCAC
AACTTTGTTCCAAGTGTTTTGCCATCAATGGTGTCAAGGTTTCTGTGGTCACTCGAGCAGAGCTTAAGGTCTCCTCCCACTCCCACTCCAGCTCC
CACTTCCACCTCCAACTCCCATTTCCACTCCATGGCCAGCAGCACCACATTCAAGGTTGTCCAGAGTGTAAGCTAAATAAAACTTTCACTTTGA
TGCATTTCTGGTTGCTGCTGCTATTTTTTTTTTTGTTTTTGTTTTTTTACGCACTCTGCTTTTGGACATTAAATTGCACTTGCTGCAAAAGAGTTG
ACACAAAGGGGGGAAAATTGGGAAGAAAAAGGCAGAAAAAAAATGGGGGACTTTGCACTTGGAACATACAAATCATGGCAGCCAGAAAGCGACAAC
ATCGCAAGTTATGGCCCGATGCTTCAGGTAACTGACTTGTGCTCCTCTTTATTTCCTCCCCTTGACTACTTCAACGTTACGTTGTCAAAAATTTT
TGTGAAACATGTTTTCGAGGATGCCAACAAAAGAGCCACTCCTCTTTTCATATTCAAACTACGGCTGGCACTGAAAGAAATGCTACTTGCGTACC
TTTGGACAGCAAAAGGTATTAATAAATCAATTAAAACATATTCATTATAGCATCGGACATTGCCTTTTGTGGTTTTATCATTTGGCTGTCTCAAC
TTTCACCCATACGAAATATGGCCCATTAACATGTTCATCAAAAGTGTCGCATAAAGGTGTGAATTGACCCCAAATACCATATATGGCTTTATAAA
ATACCAACTAAATATGTTTATGAAGAGCTCTAACTTAAAGCTCCTAAAATTTCCTTTACACTATCTCTCCATTTGTTTCAGCGAAACTTTAAGCG
AAAACATCACCAAGTTTGTTGCTGCAACTCAAGTAACAAATTAATTTCCCCGGAAAAGTGACACAGCGCACATGAAAATCTTGTGATGGGGGGCA
TACTAGTATACATATATCATAGCAGGTGAAAGGGAGCAGTGTAGTCATGTTACGCGTCAGGCTGATTAGAATATAGCGACGAAAGGCTGCATAAT
TTATGCGGCCAAAAGAAGGTCTGCGGGTCAAAAGTGGAGCTCAACTTGTTGCCACAAAAACGGGAGGCGCCGCGTCGCGAAATTCTAATGAAGAT
GTGGAGTGCGGACCAAAGTCATTGACAAACTGTGGCTGCACGTGACCCGGGTATGGCTATGACAGGTAGACATGATGGACTCCTCCGCCAGTTGG
ATCCCTAACCAAGGGACAATGGAGATAAAAGGCGGCAGGCACGTGACAGGACTCCAGCTCTGGTCCTGGTCCTCATTATTGAATTAGTTACGAGT
ATAAAATGCAAAGGGATGAGGGCAGTTGGGGGTATATTTGTAATTGTCCGAAATATAGTAGAGTTTCTTTTATGGCCAACCAAGTAGGTTGTAAT
CCATTTTAATATCAATTAAGCACGTATAGTCGTATATTCGTTTTCCGTTTCCCTATGCTTGTGTGCTTAGGACAGTTTTTCATTTTGATTGGCAT
TTCAATAAGAAATTCCATCGACAAACCCGTCAAAAGCAGAACAAAATCTTCGTACTTATCTCTCTCTCAAGGAGCATCGCATCTTCGTTTTAAAC
CCATTTTTTCAGGTGCTCTGCCGGCAAAAGCTTAATTATAGCCAAGTGAAGCTGGCTTTCAGCCAGCTAATTTCCGCTGCAAGGCGGAGACTGTT
TGGCCAAAAGCCGAAGCCGAAAATGGCAGAAGGAGCTGTGTTCGCAGCTTGAGGCTGAAAAGCAAGAAGTGGCTGAAAAGGATTTCTCGCACAAG
GCGAACAGAAGATGGCGAATGAGGAGGACGCCTGTCGACATCCTTGACTGCACTTGACTGGCACAAAGTGCCTTGTTTGTTAGCCAACTTCGAGG
GCATTTAAGCCGCAGCGCAACAGGTGGCAGGCCAGAGAGAAAAACGGCAAAGACGGGGACGCACTCTGATTGAGTTAGTTAGTTGGCCAACTCCG
CCATTCCTGCCTCACAGAGACTTTGCCACGCCAAATTTAACAGCAATTGCGAAACTTTTAAGCCCCGAAAGAGACGAATTGCAACTTCCACATAA
TTTGCAACCAAAATTTGTCTACCAAAACTCAAGGTAAGTGAAAGGACACAACATGTCCAATGAGATGGATGGAAAATGAAATGTTTTCCCTTTT
TAGCATATGACAAAACGGGTTAAGCCGGGGCAATTTGAAATACTTGGGGTCAGTCAGACGTTTATAAAATCGTTTCCCCTGCGAGAAACACAATT
TTCTGGTCGTAAAATTAAATCAAAATTTGATAACTGAGAGAGAGAGTGGTGGAGTAATGCCCTCACACTCAACGTATATTTTATTTATATGCAAT
CAACGGACAATATATCAGTTTAGTTAATCTAGTTGAGGTCGCTTATCGACAAGTTTTTGCCCCAGCTGATATTTATAAAACACTGATAATGAGTT
TTACCGCTTGCCAAACGGTTACACAAAGATTTTTTGTTTGCCTGGTGGCAAACAACCCACTTTGGGGTGTTAATTAGCCGCACATGTGAAATAAT TTGGTTATCCTTTAAATTTAATTGGTTTTTTGTATGGCTATCTGGGCTGGGAGCTCAAGTTTCGCTGTGGCTTTTATTTACAGGATTTATTACAA
GAAAGTCAAAGGTTGAATATGAGAAAGAATATTTGAGATAAGAAAATAAGTAGCGCCTTATCATTTTCTTTAATTGAAACTACTGCTTAAGAGCT
AACTATAGTTTGAAAACAAATTGTTTATGGGTAATATTTTTAAATGGTTTTTAAGAATCTTATTTGTACCGGAAAACGATTTCTTTGCTTAATGA
AGCCAAAAATTGAGGGCCGCGTCACTATAAACGCCCATAACCCACAGAAAAATGAAACAAAAAGCGGGAAAATGGGTTTGAGTTTGAGTTTGGGT
TGCAGGAAGAAGGGGGGCATTCAGGCATGGAAAATGCACCAGCAGCACAAGCAAAAAACAACAACAACAGCGTCAGCGACAATGCAACAATGAGA
TCGCTTATCAGTTGGCGTCTAATTTACGGCAATGAGCCGCCGCGACGACAGACTGACTATGCAGCACCAGCAGCTTTAATCCCATACGGAAAACA
CATGTATCTGCGAGTATGTTAATCTGCATCTCCAATGGATGCGTGTGTGTGGAGATTACGGACAGCATCGGCTTTAAAAATATTTCATCCTGAAC
TCTCTGACATTCTGCCGAAGTTTTTGGGGCAATGTGAAATAATCACTTTAGCATGGGATTTAGCTTAGTTCATTGATAACAAAGTGTGCCTATTT
TAGTTTTGTACACTTTAAGATCACTCACCTCGAGTCGAATTTCTTGCCATCGGCCTGCAGAGTTCCAGTGTAGTGCATGGTGAGGGAATCGCCGT
TCTTGGACTTTTGTTCGCACACCTCCGGCGTGCTGATCACCTCCACTTTCAGATCCTGAGCCCGGACCAGGCTGTTGCTGATGGCCACCAGCAGA
AGGCACGAGATAACGAGATTGGATTTCGACATGGCTGCAAGATAAATGGGCAAACTTGATTACCACAAAACGTAAGAGACTTTCAAAAAAAGGGG
AACGTGTTTATGCACTCGACTACAAGGAGTATAGTAAACCTTATAAAGAGTTTAAGATTTGCTAATCCTTAAAATTAACTGAGTTCGAACTACAG
ACGATAAGATCCACTAACTCGAAACTAAACCGAAGCACCAATGTCTTGCTCGGATTGATGTTCATCACTTTTATACACACAGATTCATCATCACT
ATCATCTACTCGCCATCATCTTCGTTTTAATCGCGTATTAGCGTTGCACAAGCGTTAAATGATGAATTTAAGCCAATTACCCGGAGAGGTGTAAC
AGTTGTTTGCTCAACAGTGTAAAGTTGAAATTGAAATCGTATGGATGGCGAGGGGTATTCGCAGCGATTGCGAATGGGATGCGCGAACAGCAAAA
ATTAGTCATTATGCAAATGTGCAATTCATTTTCGAGTGGGGAACCGAATTCGACCAACCAACCAGCTTTGACCATCTCGACCAGCTGGAGGGGAT
TATGCAAGCCAAGACCCAAAGCCAAGCGAAATTATTGCGCGTACGCGGTGGCGTATGCGTAATGACCATCGTAGTCATTTCCAATGGGATATGTT
GGTGGGTGTTTCTGGTTAAATGAAAGTTTTGAAAGCGCCTAGGTCACCCAAATATAAAAAAAAAGAAGCGAAAAAAATTCGAATAGCCGTAAAAT
AAAAAAACTAATAAGGCAAACAAAAAATAAAATATGGTGGGTCTTTATATAGTCGGAAAACTTTCACTAATGGAAAGGCAATGGTCAAGCCTCAA
TTACGTGAAATCGGCATTAACATCTCTTGATCTTCCTCTTCAACTGCTCTCTTTCGCTTCTGCTTCTTTTTCCTTATACAGTGAAATCTCAGAGA
CATGAACACACATATGCCTTACTTTTTTGCTTAAGCTTGAAAATGATTAATTACACTAATAAGTTCATATGCTATGATATGCAATTGTTACAGTT
AAGACCAAGCTGAAGCCAGAAAATCCACAGATTTAGGGACTAGAAATACTTCAAATACTATAAATAGATAAGACGAGATGGCCTCCTGTGGCTAA
TAATCCTAAAATCACATTTTCAAATATATTTCAAAATCTTTTTTTTCAGAAGCCGCTTCACTGTACTGAGCGTCCACTTTTTGGCCTTAAAACCT
GTTGGGCGATCCAGCTTCTTCGTTTACACACGTATCTTTTTGTTTCAGCTTTTTTTTTGTGTGTCTTTTATGAAAGGTTCAGTGAACTGGCGGTA
CGAAGTTTACCGTAAGCGATCCAATTTACAGACCGGCGCTAAATGTTTCGGAAAATCTTTTCCTAAGCGACACGTCAGGAGTTTTCCTCTTATTT
CGAATCAGAAATGCTAATTGCTGACCCGAGCCGATCTTTAGCAACAAAAGCAAGAGCAAATGACCGGCGATATTTTTTTATTTTTATTTTCATGG
ACTTGTAGCGATAAGCTCTCTTTCTCCTCCTCCATCATTCGGTTTTCTTGGGGCGTATGTGTGTGTATATATATTTATTTGTGTATGCATGTGTG
ATGGCGTGGACTGAATATGAATGGAAGAGACACGACAGCAATGGCAAAGTACACGCTTTCTTTCGATTTCTCGATTTTCATTTCTTAATGAGCAC
ATTTCCAAGATGTTTACGCTAAGCCAAGCACACGATTTACGATCTGATATCTGTAATATACCTTTGGTCTTCCACAGACGGATATCACTCGATTC
CGGCGAAGGGGCGGGGGCGGATGCGGCGGGCGAACAACAGAAAACACGCGAGCAAACGGCGGATGTGAAGTGCAAACACGTCCGATTCGATCGAA
GTGCGGGCGAGAAATGCTGGAACCGAAGCCGCCGACGTTGTTTTACTAACCGCTACTTCTACACTCAGAAACATTTTTGTGGCACTTTGCAAGTT
AGACCAGATTATTTTGTAGTTTAGTTTAAAATCTTATTTATATATATTGCATTCCTCCAAGTTTTTCATAAGATTATAGTTTTTTTTGTATTTCA
ATGTTTTTTTCATTATATTCCCTATCTTTTTTTTGGGTGCACCCCTATATAAAAAGAGTGGAAATCTTCAGAGAGACCCGGAAAGTGTGAGCGGG
AGGAGGCGGGGGATCGTGATCCACCACCATCCACACGTGTAAGAGTACGAGAGAGAGTGAAAGATCGTGTTTTTGTAGAGCCAAAAGAGATTCAC
ATACTGTGGGAACGCGATCCACAATACGGGGGGCAGAATAAGAGAGAGCACTTGTCCACGTAATCAAGCAGAAACTTGTTCAGGAGCGGATCAGG
CGGACTTAGGTTAAGACACAATCAAAGGTGTTCCTTATCCCAAATAAATTAGTTAATATGTAAGATTAATTTTTTAAAATTTAACTTTAAATTTA
TGATTAATCAGAACTTACAGGAACAATGTAATACCGAAATGTATTCCAAAAAGTTATTCATTTTTTATTAAGCTAATAATCGTTTTGAAAAATGT
AACAAAAACGAAAAATATATGGAACACGAAGGACACACAACCTATTCAAGCAATTGCTCAAGTTTAACTAAAAGGAGTTTCCAAAGAATATGCCG
TAGTCTACATGTTGCTGGCATCAAAGTTTAAGCAACATTATGCCTCGCCTACTTTTTCTAGTGCGCAGGCGCCTCTTTTATTTTATTTGTGGGTG
GAGCCTGATAAAGAGTTAATTTAATGATTGGCGAATTAAATTCGGCAAAATTATGTGACATTTTCTTTTGTTTTCATACTCTAATTTAATTTATT
ACAGTTTATTTTTAAACCGTGCTTGATAATTTTGTACACTGGTAGA
(SEQ ID NO: 1084)

Exon: 11016..10892
Exon: 9154..8959
Exon: 2189..2101
Exon: 2034..1847
Exon: 1673..1001
Start ATG: 9152 (Reverse strand: CAT)

Transcript No. : CT27794
ATCGAATCGGACGTGTTTGCACTTCACATCCGCCGTTTGCTCGCGTGTTTTCTGTTGTTCGCCCGCCGCATCCGCCCCCGCCCCTTCGCCGGAAT
CGAGTGATATCCGTCTGTGGAAGACCAAAGCCATGTCGAAATCCAATCTCGTTATCTCGTGCCTTCTGCTGGTGGCCATCAGCAACAGCCTGGTC
CGGGCTCAGGATCTGAAAGTGGAGGTGATCAGCACGCCGGAGGTGTGCGAACAAAAGTCCAAGAACGGCGATTCCCTCACCATGCACTACACTGG
AACTCTGCAGGCCGATGGCAAGAAATTCGACTCGAGCTTCGACCGCGACCAGCCCTTCACATTCCAATTGGGCGCCGGCCAGGTGATTAAGGGTT
GGGATCAGGGTCTGCTCAACATGTGCGTGGGTGAGAAGCGCAAGCTGACCATTCCTCCCCAGCTGGGCTATGGTGACCAGGGTGCCGGCAACGTG
ATACCGCCCAAGGCCACCCTCCTCTTCGATGTGGAGCTGATCAACATCGGCAATGCCCCGCCCACCACCAATGTGTTCAAGGAGATCGACGATAA
TGCCGACAAGCAGCTGAGTCGCGAAGAGGTCAGCGAGTATCTAAAGAAGCAGATGACCGCCGTGGAGGGACAGGATTCCGAGGAGCTGAAGAACA
TGCTGGCTGAGAACGACAAGCTGGTGGAGGAGATCTTTCAGCACGAGGATAAGGATAAGAACGGTTTCATCTCGCACGATGAGTTCTCGGGACCC
AAACACGACGAGCTGTAGTGCTCAATAATGGGGGTTCTTGGTTTGCCGTCAACATCGAAGGGACACGAGTGCTTAAGTTATATAAAACCCAAATA
TATACACAAAAATAGAACATATACAACAGATGAGGCACGAGCCGAGCAATAAATCGAGTGCAACCAAATGCTTCCCGATGTCATTTTGTATATAG
CATACATATCAGCATCAGCATCAGCATCTGCATCTGCATCTAAACACCAACACATTAGAGGAGTGCATTAGTAGTTTGTGTGTCTGTAACCCCGG
TACTAGACGTAGTTTAAATTATGTACAATCTGAGAGAGAATGAACATCATTTTTATATACATTTATAGGTTGTTATATATTTTGTGTCGGCTGCG
GGTGGTGACGATTTTTAGACCCATCGTAAAGATAATATCGTATAATATCGTATATTGTAAATCAGACACACTCTCAAGACGAAGTCAATTGAAAC
ACTTTAAATTGAATAAAGAATTGCTATCAATAATTT
(SEQ ID NO: 1085)

Start ATG: 128 (Reverse strand: CAT)

MSKSNLVISCLLLVAISNSLVRAQDLKVEVISTPEVCEQKSKNGDSLTMHYTGTLQADGKKFDSSFDRDQPFTFQLGAGQVIKGWDQGLLNMCVG
EKRKLTIPPQLGYGDQGAGNVIPPKATLLFDVELINIGNAPPTTNVFKEIDDNADKQLSREEVSEYLKKQMTAVEGQDSEELKNMLAENDKLVEE
IFQHEDKDKNGFISHDEFSGPKHDEL*
(SEQ ID NO: 1086)

Name: FK506 binding protein
Classification: chaperone
Gene Symbol: Fkbp13
FlyBase ID: FBgn0010470

Celera Sequence No. : 142000013384423
TTGTGTACGGCGTAAGCATACCCAACACTGAGGGCAGAGCAGGAATGGCAGCCATCTACGATCCCACTCGGGAGGTCAACGTCAGCCAGCTGGGC
GTGGAACTGGCCAAATCCCTGCCCAACTACGCCAGGCCGCAGTTTCTCAGATTCCTGCGCAAAATCGACCTGACGGGCACCTTCAAGTTGCGCAA
GGTGGAGCTTCAGCAGCAGGGCTTCAATCCGGAGATCATCGACGATGAACTCTTCTACGCCCAACCGGATGGCGTGTATGCTCCACTCACCCCAT
CCGTATACGAGAGGATAGTTAGAAACGAGCTGCGATTCTAGGAGCGCCGGACTTTGTTCTTGGGAAGAAGAAAAGTCAAGACTGTGCCTTGTATG
TTGGTGAAGAGGATATCCTTTGGATTCGGCTTGTGGTGCGCCAACTACTTTTAATTCTGGCTAAGTTTCTTATTGTCCGGACAATATAAACTTTA
GCATTGGAAATTTACTGTTGAAAGAGCGTTTCCGCGGGTAAATTATTATTTTGTAACTATTTCCTTCTACAATTCCTACATACATAAGTGTCACA
TCGTATTGTATACATTGTATAGATAATAAAAATAAAATTCAGCCAATGATAAATCCATATTGTGCTCTATTATGTGATTATAGCATTTTCCTTCT
GTAAGACAGGATTTTGATTGGTTTTCATTAGATTTGTAATTTAGTTTATTGTGCTTAGTTAAATAGTTTTTAAAAATGAAACTTACAATTGAAAG
AGCATCATTAGCCACTTTACGTTGGAGTAGTTAGAAAATCTAATATCCCGGCTTCCTTAAACAGTTCCAATCAAATCGGGATGGCTTTAGCTACG
ATTACACTTTTCAATAGAACCTAGGTTACATCCATTGCTTGAGCAACTGATGCCTTCAGCTTAAGTGGAACCAGATTTTCAGGTGAACGGATTTG
GAAACGGGGTCGTATAAAATACTTTCAGCAGTCTTTGGATCTATATCCGCTCAATCCTTGGGCGGCACATCCTTGCTCAACTCTGCACGCTTCCT
CTGCTCCATGCGCTCCTCTACCTGGTCCAAGCGCTCGCTCATGGCATCCAGGGAGCTCAGCAGTCCCGCCTGGATCTCGCCATATCGCTTCATGG
CCAGGACCAGACTCTCCTCGATAAGTTCGCTCTGCTGCGCGTACTCCCCGTTGTTCTGCGTTATGCCCTTTAGCTGCTCCAGACACTCGGCGGGA
ATGCTGCGGAAGTACTCCGCGCCCAGGGCCGGTTCCAGCTGCTTAATCCTCTCCAGCTGCTCGGCCTGCGTGTGCAGCTCGGGGGCCACGGCTTG
CAGGTACACCTCCTTGGAGCGCACCTGCTGGTGCTCCTCCAGGAAGTTGGGGTCCAGGTACTTCTCCAGCTCGTCAGATCTCTTCACGCACTGCT
GCAGTGCAGCACTTCCTGTGGTTGCTTCGCCCAGGATGGCGTGTGCCGAGCACAGGGCGTCGACCACGCCCTCGCCCACCTCAGAGTCCTGGACC
GGACCCAGGACTCGTGTCAGGGCATCGATGCGCTTCTCCAGAATGTCCAGTGCCTCCATTTTTCGCTGAATTTCTCTTTATTTTGTTCGTTTTGA
TGGGAATGATGTCAGTCTGCAAAACAATCGATGTCCAACGAAAAGGTGGCAACGTTAGCTTGGTGGCAAGGTTCTTGTACTCGCTAAGCAGAACG
AATTAACCCTTATGCGGACTAAAAAATATGGTATTTAAATAAAATATTTAGCTCCTCTGCATAAAGTTTTTGGTGCATACGTATCTATAAATATA
GTACACACTTAAATTCCATTGCTATTTACTTAGTTTCTTTTAAACGTAAACTGTACAATACAAAAATCTCAGTTACAACAGCTTAAAATTCTCGA
GGGACAACCGCTCCGCATCCTTGTTGATCTGCGCCAGACTATCCTCGGAGATGATGCGCACCGTATCGACGTCCGGGTCATCGCCTCCGGAATCA
TCCAGCACACACAGCAGACCATCGTTCTCGATGTACGGGAAGAAGAACTCGGGCTTGTCCCAGCTCTCCTTATCGCCGATTCCGTGGTGCGACTC
TTGTGCCATGTGCTCCACGAGCAGCTCCTCCTCGTCGAACTGCAGATCGCAGGTCACGCAGCGCAGCAGGCACATTTGGCGGCGCAGGTAGTTGA
CCACCTTGACGCGTTGGTAGAAGTTCAGAGAGCTGGTGGCCTTCTCGAAATCCAAGCGATGAACCTCGTGCATGTGCTTCTTGAGGGCGGTGAAG
TTGTCGCCGAGATGGTGGCAAAACAGGCACTTAATGGAGCTAGGCTCACCATCTGCCGCCCAATCCGACCAGTCCGAATCGTGTTCGCCATCCGA
ATCAGGGCGAGCGAAGTGCTTGTCGAAGTCCACGCTGCCGTTCAGGATCAGCAACTGTGGACACGGATGCCGTTTCCCGTCTTCGCTTTTGGA
GGTGCTGTTTCCGGGGCGTGGGGCCGTTGGTACACGATTGTAGTTGATAAGGAAGTACTTGTCGTACTCCCTTCGGTTCGGATTGATCCGCTTG
TGGCCCTTCTTGCGCATGTGTTCCTTGAGCGTGGGCCGATCCCTGAAGATCTTCTCGCAGTAGAGGCACATTAAC
(SEQ ID NO: 1087)

Exon: 1640..1001
Start ATG: 1579 (Reverse strand: CAT)

Transcript No. : CT27878
GTTTTGCAGACTGACATCATTCCCATCAAAACGAACAAAATAAAGAGAAATTCAGCGAAAAATGGAGGCACTGGACATTCTGGAGAAGCGCATCG
ATGCCCTGACACGAGTCCTGGGTCCGGTCCAGGACTCTGAGGTGGGCGAGGGCGTGGTCGACGCCCTGTGCTCGGCACACGCCATCCTGGGCGAA
GCAACCACAGGAAGTGCTGCACTGCAGCAGTGCGTGAAGAGATCTGACGAGCTGGAGAAGTACCTGGACCCCAACTTCCTGGAGGAGCACCAGCA
GGTGCGCTCCAAGGAGGTGTACCTGCAAGCCGTGGCCCCCGAGCTGCACACGCAGGCCGAGCAGCTGGAGAGGATTAAGCAGCTGGAACCGGCCC
TGGGCGCGGAGTACTTCCGCAGCATTCCCGCCGAGTGTCTGGAGCAGCTAAAGGGCATAACGCAGAACAACGGGGAGTACGCGCAGCAGAGCGAA
CTTATCGAGGAGAGTCTGGTCCTGGCCATGAAGCGATATGGCGAGATCCAGGCGGGACTGCTGAGCTCCCTGGATGCCATGAGCGAGCGCTTGGA
CCAGGTAGAGGAGCGCATGGAGCAGAGGAAGCGTGCAGAGTTGAGCAAGGATGTGCCGCCCAAGGATTGA
(SEQ ID NO: 1088)

Start ATG: 62 (Reverse strand: CAT)

MEALDILEKRIDALTRVLGPVQDSEVGEGVVDALCSAHAILGEATTGSAALQQCVKRSDELEKYLDPNFLEEHQQVRSKEVYLQAVAPELHTQAE
QLERIKQLEPALGAEYFRSIPAECLEQLKGITQNNGEYAQQSELIEESLVLAMKRYGEIQAGLLSSLDAMSERLDQVEERMEQRKRAELSKDVPP
KD*
(SEQ ID NO: 1089)

Celera Sequence No. : 142000013383801
AATGAATCTAAAATGAAAGGCCAAAACCATATAGAAGCTAATTTAGAGCGCAACTATTTCACAAATCCTCACCTGGTTATGTACTCGAGGGTCAC
GGGATCCTCGACATTGAGACGATGGCTCTGGCACTCCACCTGGGCACGATTGATCATGATGCGAGCGTCGGCCGTGAGACCGGCAAAAGCCATTA
CAACGTGGTTGTCGAGCATGCAAATCTTGCGCACCTTTCGATCCTCCTGCAGTTGGGCCACCGACTTCTTCTCCACGCCAAGCACAACGCAGTTG
GCGCCGCGAACTCCGACCTGCGAGGCGAAAAATTGGAAAAGTCCATGTTTGTTTCGGTTTGGCGGCACTGCGAACGGTACTAAATTGCACTTACC
GCAGTCGATCCCTTGCGAACGGCCTCCTGGGCATACTCCACCTGCAGGAGGTGACCGTCGGGAGAGAATATGGTTACAGCACGATCGTAGCGTGA
GGACATCTTGTTGCTTTATTCAATAGCTGAGGTACTTGCAGAATATTAACTTATAGCTTTTTCCTTCTCGAATTCGCCAGGCAATGATGATGCTT TTTTGAGGAAATGCCGCAGTGTGACCGCAGCATGGGTTCGATGAAAATTACTAAATTAATACCGTTTCGCAGTGAACGATATATCGTTGCTGAAA
TCATGTATCAGAATCAATTCAATTCTTGTTACTTCAGTCTATTTAATATTCTATTCCATTTAGTCTATTTAAATATTTAATTTAATACTTTTGTA
AACCGTTTTACAGCTTCAGGGCTGTAAATAATTTAGTAAAATATCAATTAATTTTTTTTCACATTATCTGTTATTATTGTTATTTAATAATACAA
ATTTATAATACAAATTATTTTCAATATATATATATATATGTATTAATAATTATAACCAACGACTGTTACTTAAATGTACAAAATGCAATCGCT
ATGCCGGCCCTGGTAATCGGTGTTCATCGACAGCTTGCTGCAGCCCTCGTCGTCGCTGTAATTACAATGTGATGTGCATTTGTTTTTGTTAATAA
GAATTGTCCGATTAAACATTTAGATTATCTGTTTTTAAACAATGCGATCACGGTGATATCGGTTCGTAAAGGTTTTACACACCGTGTGATTTTGT
TTCAGTGCGTTTTGTTGTTCGTTTCGTAAATAAGTGGGCTTCATTTTGCCCAAAAAAGACGGGAGCCCAGACAGCTGATCACAGACTTTGGCTCA
CACCTGCTACAAAAAGATAATATTTATTCGAAAACCTGGCATTCGGATCGAATTTAGCAGCTGCCAGCGTATTTATATAAGAACAATTTGATTGA
TTATGGCGCTGCCCAGAAAACTGATATCCAAGATCTGTAAGTAAACCGAATGTTCGAAAGTACCGTTGTATATTCCCACACACACACAAGCACGT
AGAAATACGACTGCATGTATATATGTGTGTGTGCGTGCGTGTTTGAAATCCTATCGTAAATTCTAGTGTTGCATGCAACTTCAGTAACTTTTAAA
ACAATACCACGCGTTCTTATAAACAATGCAGATATCCAATAGGAAAATCCCCAGGTGCACATATGTATGTATGTAGATACATATGAACATTGAGT
GCAGCTGCAGCTGAATTGTTCGTTTTAAAGTAATTAATATCTTGTTTTACAACGCAATATCAATATCAAATAAACATCATACGGCTTCTTCAGAC
TTTAAAATAATATTTGTATATAGCCTTTAGAAAACTTCAATTCAATCCCAAGAACTATAGAAGTTCAAAAAGGTTTTAATCTGGGAACAAGTTTT
CAATTTCTTTGAAATGCGTACATTTACGTACATATGTATGTACATATATACTGTACATATGTATGTATGTACATCGATTTCCTAGCTTTATTTTA
TCTGTTTTGCTTTTCAAAATACTAGTAATCCTTGTCATTCATAAATGTGGATAACGTAAAAGGTACTTATTTATTTATATCGACACAGTTTCCTT
TGAAAAGATTCAAAAATCATTATAAAATTGTATTTATTGAGTATATACTAATACGAAAATATCATATTTTTATTATTATATATTTGTTGTAAGTT
TTCCTTTTGATCTTGAAAAGCTGTTGTTTAAAGCATAGCTTAATCTGAACATACTAACTATATCATCATATCATGAAAACTTGCCGAAGAGGACT
AACCAATTCTCATCCTTTGCAGACGATATAAAGGCACATGATAGCAGGGTCACGAGCCTTGATCTTGGCGAAACTGGACGAGTGCTGGTCACCGG
AGGAGAGGATCGCAATGTGAACCTCTGGGCGATTGGTCAAAATGAGTGCTTTATGGTGAATATACTAACTACTTCCTAAATATATGTATGTACTA
ATCGGTGACCCTTTCCTTTCAGTCTCTGACGGGCCACAATCGTTCCATCGATTGCGTGCGTTTTGCTTATAAGGATAACTTTGTCTACTCCGCCG
ACGACATCGGTATAATCCGAAGATGGGATCTGAATTCACAGAAAATCTACTCCACGCTAAATGGCCACATGAAGAGTGTTCGCACTCTGGACTTT
AACCCGTCTGGAGAATATGTGGTGTCCGGGAGCAATGATACCACCGTCAGGTGAGCCAAGGACCGATATATAAATAGTCAGAGTAACCCATGAGT
CATTCGGAAGCTCTAGTTTCCTTATCAAGTGGCAGATTTAAAGTTTATTCGTTGATTGAAAAGGGATGGCGATATTCTCCCTCCCTCTTTTAGCT
GTGCTTAATCCTATAGAATCGCGTATTTTGGGTTTAATAATCTACACAAAAGAAAAATCTCATATTTAGAAATTAGAAATTTTATATCGGTTTAA
TGCACATACATATTAGATGCATTGTATCTATATGGTCTTTTCTTAGATATCACTTGACCTATATATGTGTAAAACAAAGATAATATGACTCACTA
CATTGCACAAAAGGGGACAGGCTGACAAAGATAATATCACTTTGTGTTGTTTAGCTAAAGTTGATATTTCTTTTGGGATCTCATATATCTTATCT
CTCAGATCTATTACATCCATGATCTTAAACAACATTGCATTTTCAGTTATGTGATGTTTTATTGGGAGTTTTATAAAAGTGTTACAAAAAAATAC
TTCTACCACCACGGGCGTTTAAACAATTGCATATGTATAGGCATATTTGTTATAGTGTATGTACAAAAAAAAACGGACGCGAAACGAATTATAAA
GTCAATGATAATCCATTGCGACTAAGGCAGACTATGTGTCTCTAGGTGATCCGCGCTTACAGCTTGGCCTGTGAGCTCTTCAGGTCGACATAGGC
GCCGGATATGACCTCCTTGCCGGTCTCCACGACCACGGTGCGGAAGTTGATGCGTGTGCCCTGCTTCCACAAGTCCACGCGCAAAGTCTGGCCCG
GAATTACGGGTCCGGAGAAGCGCACTTTGACAGCCTTGAACAGAGCCGGGTTGTTGTCCGCAAACTGAGCGAGCACGGCGCGCACCGAGAAGCCC
AGTGTGCAGAGTCCATGGAGGATGGGTGTCTTGAAGCCGGCCAGCAGGGCCATCTGGGGATCGATATGCAGGGGGTTCTTGTCGCCGGACAGACG
GTACAGCGCCGCCTGGTCCTCGCTGGTCGTATACTGGACGGTTGCGTCCGGTTGGCGATTGGGCGCCGGCTGCAGCGGAACTACACCAGCGATGG
GATCCTTCTTGCCTCCGAATTTGCCAGCGCCGACAATGAAAGTGGTGCTCTGGTTGCGCACCAACAGGCGGCCACTTTCGTCGAACGACTCGCTA
TTGGTGACGACCACGGCGCCGGATCCCTTGTCCATAACATCGAAGACCTTGCCGTTGGTCAGCAAAGTGCCACTGGTGGGCAGATCGTCAACGAT
CTCTAGGTACTGTTCGCCGTGCAGAATGTTGCTGAAGTCCACTTGGCTGTTGGGCAAAGCCTTGCTGAGCAGCTTGTCGGTGGACATTTGCAGCA
GAAGGCCGGGCAGAACGAAGAAAGTTGGAATGGCGGCGAAATCGGCATCGTTTTCGTACAGGAAGCGCATGTCCTTCGCGTTTTTGACGGATGCC
CCAATGCCCAGGGCGTAGGTAATAAGCTCTTTGCTATTGAACTCGAAGGCATCCTCGATGGCGTCGCCGCCGCCTTCCTTGAGCTTCTCAAGCAC
TTCCAGCAGGGTGCCGGAGGCCTCTGCGATGGCACCCAAGTGCTTGGCCTTGGACATGTCGGTCACATTCGACCACACATCCTTGACGTACTCAA
TGGTCACGGGGTCGTCCAGCGAAGGACGCAGCACAGCGCCCTTGCCGCGAACCATGTGCAGCTTGGTGGCCCAGCCGGCGGCACTCTCGATATAG
CTACCTGTGGATCGGAGAAGAGGGAGAGAGAAAACGTTTAATAAACCCTATATATACACACATGTACACATATTCCTGATAAACGGTCTAAGTTC
AAACGCTATCAGTATGAATTTCCCTAATCAGGCAGATTATGTTGACCATTTGGATTGGACTACTGGACATATTAAAGATGACTTAGCAGTGGTTG
GCCAAAAATTGCATAATTTTGTAGTTCTCAAAGGGTTAAATTGATACAAATTGATATGATAATCAATTCTGAGATAATGCAATTCTCGCATAACT
TCGGATCCCACTTACCATTATCCTCGCAGGACTCGTGGCACAAGTAGGCCACTACGGGAGCAATCAGCTTGGGCTTCAGCTCGTTGAAGAGAATG
TCGGGCAGAATGCCCTCGGTCATTCGACTGGCGGCAGTTGGCACGATGACGTTGCAAAGAACATTGTTGCGGGCTCCCTCGATGGCAACCGTGTT
GGCCAATCCGATGAGGCCCATCTTGGCGGCAGTGTAGTTGACCTGCCCGAAATTACCATAGATGCCCGAGTTGGACGATGTCATGATGATGCGGC
CATAGTTCTGCTTCTTCATGTACGGGAATGCCGCCTGGGTGCACTTAAAGCTGCCCTTCAGATGGACATCGTTGACCAGATTCCAGTCCTGTTCG
CTGGTCTTCACCAGACTCCTGTCGCGTAGAATGCCGGCATTGTTGACCAGGATATCGACGCGTCCGAAAGCTTTGATGGCCGTCTCGATGACCTT
TGCCCCATCGATTACCGAGTTGTAGTCGGCCACCGCCTCGCCGCCGGCCTTACGGATCTCATCCACCACAATGTCGGCGGCCCGCTGCGATGCTC
CATCGCCGGAGTGGGTGCCACCCAGATCGTTGACCACCACCTTGGCGCCACGCTCCGCGAAGAGCAGTGCGTACTCGCGGCCCAAACCGGCACCA
GCTCCCGTCACCACCGCCACACGGCCATCGTAACGAAGTTTTCCATCGGATGAGGACATGGTCTGTCTATTGGTCAATAGCAATCGCAATTTCTG
GTTTCGCTGCACAAATCCGGTCTCTGCGGCAACGCTTTTTCGGCTGTAAAACACGAATGAACCGATGAAAATAAACTGGTTGGCTAATAATCGAA
CAAGAAAGGAGAGTAGCACTACTTTTCAATCGTACTTAATCTCAAGCGATAATGCTATCTGCCCTGCCCTCGCATATGTGAGTGTAACTCTGGAC
TCTTCGGCTGAAGAACGTTACCCAGGCGATATGGTCCAAGTCCAGGGGTTCACGGTTCATAGTCAAGTGCTTTTCGGATGGCACCGAAATCGCCG
AAATCCGAGATACAAGATACATTTGCACAGTGACGACAGCACAGTTATTCGAACCGCGTGAAATGGCCCACACACACACACATTAAACAAGGGTT
AACTTACAGTTCTCGTAGATTCGCCGTATGATGGTATGGTATGCCCGAATATGCACAGATTAACCCAGTATCAGTGGTACAAAGTGCATCACTAT
TCGCTGCCGAGATAATTTTGCAATCGTTTAATCGGTTCAACCCATGAAAATGCACTAAAATATACTGCCCGCATTCATACGTTTGTGAGCACTAG
AAAGTAGTGCCGTCAAAATGCTGGAAAGCAGTGCATCGCGGACGTAAACCTCGGTTCGGAACTTCGCTAAGCCGTAGCAAAGACTCCAACCCGTT
TTCATTTTCCAGACGATTAAATTTAAAAATGAACAATTATGGAAATTACACTTATCTTCCACATTTCAAATTCAACTATGTCTCTTTATTTAACA
TAGAAATGTATAAAACAACAATAAATTGAGCAACAATAAATGAATTAACTAGGAGATTACATATATTATTGAAACTTTATGAATTACATATGCTT
TGTTGCTTATTTAGCAAACTATTAACTTTCATATGTCTGCAATCTCAGGCTTTGGGACGTGCAGAACGAAAACAACTGCATTAAGGTATGTCGCG
GCCACATGTCCCACGTGAATTCCGTAAAATTCTCGCCGGATGGTCTTTGGATTGCCTCTGCTGGCCTGGAGGGTTCCATACTCATCTGGGACATA
CGGAAGAGCAAACAGATAATGGAGTTCATAGCCGATCCGCCGGTTACGGCTATCACATGCGTGCAATTCCATCCGTTTGAGTTCCTGCTGGCCGC
CGGTCGCGTCGATGGCACCGTTTCCATTTACGATCTGGAACACCAGCAGCTCGTCTCGCAGACCACGCACTTCTATGGCCAGGCCATCAGGTGTA
TAACCTTTAGGTGAGTCCTGCAAAGAATAATCCGCAATCGTGAATTGATTTATGAAAAGAAATAGTAATATAGTAATTTTGCCAAAAAGTGCATA
AATTCTAATTATCTGCATGTTAAACTTTATTTATTTCAGTGACAATGGCGAGTGCCTTTTTGTTGGCAGTTCTTCGGGCATTTCGGTAATTGGAT
GGGAACCGGATCGTGAGCTGGACCATATAAAAAGCACCTGGTCCTCCTTGGCGGACATGAAAGTGGTCAACAATAAGTTGGTAAGTGAAAGCACT
TACTCATTAAGCGAAGCACCCTTCCAAATCTCGTCATCCCCGTTATCTTTTTGACAAAAATAATCAGTATTTTGGTCAGAATATTCTAAAAAAT
GGTCCAAATATGGAGTGTCATACCTCGTTGAGTTTGTTTTTTTAATCCAAATCGATTTGCATTCAAATTTGGGAATTCTAGGTTTTTTAAATTTT
TTGCAAATTTTGATGATAAAATTTTGATTATAAAAAAGGCGAAAAATTGGCCAAAAACTAATTTTACAAAATCCGTCCAAAAGTGAAAGGGGTGG
TTAGTATTGGTAATTAGGAGCACAAAACGGTATTTCTTTTGGCGGTGTGGCCATTTTTAGTCAAGTTATACCCAGAAAACCAATCTTAAATATTG

FIGURE SHEET 589

CATTTTATGCCAAAACTGGTTTCACTGATTTTATGCGAAAAAAATAATCGGTATTTTGAGCAAAACATTAAAAATAATGGCACAAATATGGAATG
TCATAACTTGTTGAGTTTCCGAATCAATTCGCATTCAAATTTAGGAAATCTAGGTTTTCACTTTTTGAAAAACCAATCTTAGATCTTAAATGTA
AAATGTCTACAAATGGAATATCCAATAAAAACCATTGCACTTCCTTTTGTAGATCTGTGGTTGTCATGAGATCGACACCGTTTCAATCAACACCA
TCAGTCTGGATCGAGTGATACCATTCTATCAGCCGCCAAACTCACTACCCAACTTTAAGCACAACTCGACGAACCGAAAGAGCTTTACACGTGGC
AACCAGAAGTTCAGGCTGTCAGTTGGCGGTGCCAAGCCGGCACAGGTGCAGGAGGAGCACGAGGGCGACAAGAGTGGATTGTCCTCGCCCAACTA
TAGTCTGGAGGTTGTGAACGAGGCGGTGCTGGAGTCGGCGGAGACTTCTCCAATGTCCTCGTTGCCACCTGTCCACTTGGCTTCGATGGCCGGAT
CGTCGGCGGACTTGGCGCCGCATCATGTCGTATATGGCGGAGCAATCGATTCTGCCCTAAGGCAGGGTAAGTACTCCAGAGTGCCTGATAATATG
GCCAGCTATGGCAGTAGTTACGGGGCCATCGATACCCGCCTGATGTCCTTGAACGAACCCAGTTCACTGCACAAGCCGGACATTTACAATCTATA
(SEQ ID NO: 1090)

Exon: 1001..1366
Exon: 2208..2335
Exon: 2398..2615
Exon: 6319..6660
Exon: 6785..6931
Exon: 7004..7075
Start ATG: 1333

Transcript No. : CT27906
CGTCGCTGTAATTACAATGTGATGTGCATTTGTTTTTGTTAATAAGAATTGTCCGATTAAACATTTAGATTATCTGTTTTTAAACAATGCGATCA
CGGTGATATCGGTTCGTAAAGGTTTTACACACCGTGTGATTTTGTTTCAGTGCGTTTTGTTGTTCGTTTCGTAAATAAGTGGGCTTCATTTTGCC
CAAAAAAGACGGGAGCCCAGACAGCTGATCACAGACTTTGGCTCACACCTGCTACAAAAAGATAATATTTATTCGAAAACCTGGCATTCGGATCG
AATTTAGCAGCTGCCAGCGTATTTATATAAGAACAATTTGATTGATTATGGCGCTGCCCAGAAAACTGATATCCAAGATCTACGATATAAAGGCA
CATGATAGCAGGGTCACGAGCCTTGATCTTGGCGAAACTGGACGAGTGCTGGTCACCGGAGGAGAGGATCGCAATGTGAACCTCTGGGCGATTGG
TCAAAATGAGTGCTTTATGTCTCTGACGGGCCACAATCGTTCCATCGATTGCGTGCGTTTTGCTTATAAGGATAACTTTGTCTACTCCGCCGACG
ACATCGGTATAATCCGAAGATGGGATCTGAATTCACAGAAAATCTACTCCACGCTAAATGGCCACATGAAGAGTGTTCGCACTCTGGACTTTAAC
CCGTCTGGAGAATATGTGGTGTCCGGGAGCAATGATACCACCGTCAGGCTTTGGGACGTGCAGAACGAAAACAACTGCATTAAGGTATGTCGCGG
CCACATGTCCCACGTGAATTCCGTAAAATTCTCGCCGGATGGTCTTTGGATTGCCTCTGCTGGCCTGGAGGGTTCCATACTCATCTGGGACATAC
GGAAGAGCAAACAGATAATGGAGTTCATAGCCGATCCGCCGGTTACGGCTATCACATGCGTGCAATTCCATCCGTTTGAGTTCCTGCTGGCCGCC
GGTCGCGTCGATGGCACCGTTTCCATTTACGATCTGGAACACCAGCAGCTCGTCTCGCAGACCACGCACTTCTATGGCCAGGCCATCAGGTGTAT
AACCTTTAGTGACAATGGCGAGTGCCTTTTTGTTGGCAGTTCTTCGGGCATTTCGGTAATTGGATGGGAACCGGATCGTGAGCTGGACCATATAA
AAAGCACCTGGTCCTCCTTGGCGGACATGAAAGTGGTCAACAATAAGTTGGTAAGTGAAAGTATTTTGGTCAGAATATTCTAAAAAATGGTCCAA
ATATGGAGTGTCATACCTCGTTGAGTTTGTTTTTTTAA
(SEQ ID NO: 1091)

Start ATG: 333

MALPRKLISKIYDIKAHDSRVTSLDLGETGRVLVTGGEDRNVNLWAIGQNECFMSLTGHNRSIDCVRFAYKDNFVYSADDIGIIRRWDLNSQKIY
STLNGHMKSVRTLDFNPSGEYVVSGSNDTTVRLWDVQNENNCIKVCRGHMSHVNSVKFSPDGLWIASAGLEGSILIWDIRKSKQIMEFIADPPVT
AITCVQFHPFEFLLAAGRVDGTVSIYDLEHQQLVSQTTHFYGQAIRCITFSDNGECLFVGSSSGISVIGWEPDRELDHIKSTWSSLADMKVVNNK
LVSESILVRIF*
(SEQ ID NO: 1092)

Classification: cytoskeletal_structural_protein

Celera Sequence No. : 142000013383801
ACTGGGAGTTAAAGGTCAATTAGGTGGTGAAAAGTACTCAGAGTAGTTGAGACCGTGCAGCTGCATTCATTACGTTTTCAGAAATGAATCACCAA
CTAGTTTTCACCTTGAACGCCATTTTCAAATTTCGCGGCAGAAAAACCACAACAAAGGCGCGAGAAAAAGCGGAAAACAAATTTGAAAACATTG
TTCCGATAATTGCTGATTATTTGTGAGCAATCATTTCAAGTAATCGAAAAATAATTTTGAAACAGGCTGTCTTGTTAGGTCAATTATTTTTTATC
GTGCCATTTAAACAAAAATTATTTATATTTATTTATTTATTTATTTCCATCGTTTCTCCAAATTACATTTAAAAGTTTGTAAGACTTAATACTGTAAA
ACACTATTATTAGTTATTAACTATAGTTTAAAATGGCAAAATAGAAAATGCGACACGCACAATTGAACTATCGAAACGTTAATATTTAAAACAAG
TAATTTAAAATAATGAATACATGTATAAAAATAATTAATACATTTGTTTTTAAAAAGCTATAGAAATAGCTGCATATATGCTTTAACAATTTATG
CTTAAAAAGTCTTTATAATAATCCTGTGATTTCGCCGTGATTTTTGGGTTTACAATGTGCTGTTTTAGAATAATGGTTATTTCAAAGTGACCACT
ATTTTTCAATTATCTTAATTTTTTAATAGTCTTGTGTTTATTTCAACTTTAAGTTTTATATTTTAATGGCTCTTTAAAAGCAAAAAAATATTTGA
TTTTTAGGAGTGATCGCTGATCACGATGCTGTAATTTTTTGTAAGATATTTACTTAACGAAGGCGAATGCGTTGTTTCGATTGGCGGTTTCAAAT
GAGCGCAAGTAAATGTATTTATTTATTATAAAAATTGTAAAAAGGGCGCATGAACGCGACCATTTATCCGTTTTGATGGGGGAATGGGCAGCACA
AAGTGCGTTTATGGGCGCCCTAAAGTGATGTAACAATTGCTGCGACCGCAGCAGCAGCGAAACGCGCGGAATGGAACGCACGGAACGATATCGTA
GTATCGTACATGCGGTCGCAAGCCATACACGATGGTCTCTTTTTGTGCAACTCTGATTCGACAGTTTCGGCACAGGTCGGCAGCGGCATTTCAGA
TTGCGGAGTCCGCCATTTTAGCTAACAAATCTATAACCCTAGCTTCGTCAGCGTGCAGTGTGAATAGGGGTCAGTTGCAGTTTGGAATTCAGATT
GTTCGCGAATATTCGAAAGCGTCAAAGATGAGTACTTTGCCTAGGGTGTTTTTTGATATGACCGCCGACAACGAGCCCCTCGGTCGGATCGTCAT
GGAGGTGAGTTATTTGCCCTTTTTTTTTAATTTTAAACTTAAGTTGAGGTTTTTTTTTTTGTGACATTTGACCAGAAAGTGAAAAACACGTGATT
TCCCATAAAGCCATTTCTTACGCCTAAAGCTAAGACTGTGTTTTACATTATTTGCCTCAGGTGATAAGTACATACCGTTTTTTTCTTTTTATTTT
TACGGATTTAAAACTTGTACCAAATATACACACAGCGCAAACTCGCCCTCTAATTTATAAGCGACAAGTGCAATTACTTTCCATGACTAATTGCA
TGACAATGCGCTATGGGTAAATTTTCAATTTTCCAACCCAATTGGACAGGCGCGTTTAATCGGAAAATCTCTATAATTATCTCTACATCGCTGAA
TTTTGAGCAAACAGGCAAGCAGGAGCACCAACCCCCGCAAATCGGCCATTTGGTGGTATTATCTTTATAGAATGGAATTTTCCTTATTTTAATTG
ACGTGTCGGCAAACTTTGGCCGAAATGGTGTGCAATTTTTACCGGTATTTTATATGCATCTGTGCATGTGTGCTATATATGTACATTCCGGCGTG
GTCTGCGTATGTGTGGCTCATACCCATACACACATGCAGATCAATACACGAACATAACCTCTAAGCGGTCACTCGCGTATGTCTGTATGTTCTTG
TCGTGCTTGCATATGTACATGTGTGCATGCGGGTAATGTACGCGCAGATGTACAGTGTACACACAGAGATATTCGGGTGTGAATGCGCGAGTTCT
GTAAACCCGTTTGCAAACATGAACTCACTATTAATTCCGCCGATGATGTAATGTACACCTAATTTTTGAATAGAGAAAAAGAATAGGAAACGCGA
ATGCTTGATGTATATTTTTAGTGGCCTGGGAATAAAGTCATTGCCCGCCAAGTAAACCAAGCCACATGTCTAGGATTTTCCTTCCAATAGGACAT ACATATGTACATACGCACACTTGAACATACATGCAGTGCGCGAAAAATTCTGCACTTCACGCCGAATTACTACACTAAACAATTGAAGATTTATA
GAGAAGCGGCATTAGGAAAAGCATTTACTTGACTAATTTATACAATTGTCTCGATTACTGGGTGAATTGGAAAATTGCTCAAATTCTAGTGCATT
TGCAAAGTTCTGTGCATTATATGTATTTTTTCCCTTGGTATAGATATGCACATACATATGAACATGCATATGTATATTATCAAAGGGCTAAAAAT
GGCGATGAAAAAAAAGCGGCGTCAAAAAACAGCTGATCATGTTTACTGCCGCTCAACATGAATTATACAGAAAATTGTCCAGTCCTCAAAAAAAA
AAAGAAATAAATAAGCAAAAAGTAGTGGCAAGGTCATCCGAGTTCGGATAAACAAACCTTGAAGAACTGAAAAAGAGTCATACTTTGTTAGCATT
AATTTCTTGTTTACTAACGAAATTTCTACCCTTTTGTTTGTATTTTGCAGCTGCGCTCCGATGTCGTGCCCAAGACCGCCGAGAACTTCCGCGCC
TTGTGCACCGGCGAGAAGGGATTCGGGTACAAGGGCTCCATTTTCCACCGCGTCATCCCCAACTTCATGTGCCAGGGCGGCGACTTCACCAACCA
CAACGGCACTGGCGGCAAGTCCATCTACGGCAACAAGTTCCCCGATGAGAACTTCGAGCTGAAGCACACCGGCTCCGGCATCCTGTCGATGGCCA
ACGCTGGCGCCAACACGAACGGCTCCCAGTTCTTTATTTGCACTGTGAAGACCGCCTGGTTGGACAACAAGCACGTCGTCTTCGGCGAGGTCGTC
GAGGGACTGGATGTGGTCAAGAAGATCGAATCTTATGGATCGCAGTCTGGCAAGACCTCCAAGAAGATCATTGTGGCTAACTCTGGTTCTCTTTA
AGAAGGTGCGATGCAAAAGCAACAGCAACATTGCAAGAAGAAAAATCTGTTAAGACGAAAACCATTTGCATTTTCTCCAAAACATTTTTTTTTAC
CAATTACTGTACTGTAATATTACGAGAAAAATACATAACAAACCAACATATTTTCAATAGACATGTTGGGTTTCCTTTGGCCAATCAATTGTATG
TGGGGGCCAAAAGTGAATAGAATTAGTGCCCACCAATGTCAGAAAGCGTTCAATTGGCTATATAATATGCATTAAATCTGTAACTTTAACATTTC
CATTCACAAAAAAAAAAACAAAGAAGAAAAACAATGAGACGACAAGAGTCGAGAGGGGCTTAGAAAAATGTTTGATCTTTTGATGTTGGCTTACT
TACTACTAATAATAGTATTAGTAATGCTGATTATCTAATTGCATATATATATATATATACCAACGTTCTACGCTATGTACCGGAATCGGAATTGT
ATTTCGTCTTAATAAATCTGAATAAACGGCAACCAACTACTCAATTGTTTGTTGTCACTGCTGGGATCTTTGGTTTGGTAAATGGACATATTT
TATTGGAAGAATATTTCGGAGCTACTCAAGGTGGCGTACAATAGATTGTATTCATGCTCGTAGGCGTTCACATGTCGTTCGGTTATCGCCACTGT
CTGGTGAAGCTTCTCGTCCAGCTGCTCCGGCGCCGTCCGCTGCTGGCCCGCCAAAATGTCGCGCACCTTGGAGCGCTCCGCGTTCAGGTGCTGCG
TGATCGTCTGGCTCCAGCCCAGCTCATGGAACTCCGTCTGCTGGTTCAGCATGTTGAGGATGTAGACCAGGCCGATGGCGAAGCCATCCTCGAAC
AGCGAGATCTTGGTCTGGTCCTTTTTGTAGATCTTTAGCTTCTGCTTGACCCGGTAGTCAATGTAGTTCATGATGAGCGCCGGTGTGATGAGGTA
GAAGGTTCGCAGGTGGTGGTTATGTGGATTGCACAAAAAGGGCTGAAAGCCTTGCAGAAGAAGCTGCAATATAAATCCATGGGTTAAGCTGGTTA
CCTAACTTGTTAAGATCGTAGACTGCACCTTGAAGTAATTTGTGCTATCGGAATAGCACTCCTTCATGTGACCCAGGCTCTTCTCGTACTCCCTG
ATGGAACCCTCCGTAGCCTCGTGCACTTTGGAGCCCCCGCAACTGAAGTTGCTGTCGAATCTGGTTTTATACGAGCGATTCCGGAAGTTGGCATT
CTTGCTTCCAGCCTGCAGGAGGCGCACATAGCCAACAGCGTTGCCTAAAAGCAATATTTACGTTTATATTTTAAGCATTTTCTTGAATTATGGTC
TTTAACCACCTACCGACTTGTGTGATAACCTTCCTGAAAAGATCCATATACGTCTCGCCATTGCTGGAGCAGCCTAGCCTTCTGATCTTCTTAAG
AAAACTATCGGCGCGCTCATAG
(SEQ ID NO: 1093)

Exon: 1001..1334
Exon: 2806..3677
Start ATG: 1263

Transcript No. : CT27926
GCAGCAGCGAAACGCGCGGAATGGAACGCACGGAACGATATCGTAGTATCGTACATGCGGTCGCAAGCCATACACGATGGTCTCTTTTTGTGCAA
CTCTGATTCGACAGTTTCGGCACAGGTCGGCAGCGGCATTTCAGATTGCGGAGTCCGCCATTTAGCTAACAAATCTATAACCCTAGCTTCGTCA
GCGTGCAGTGTGAATAGGGGTCAGTTGCAGTTTGGAATTCAGATTGTTCGCGAATATTCGAAAGCGTCAAAGATGAGTACTTTGCCTAGGGTGTT
TTTTGATATGACCGCCGACAACGAGCCCCTCGGTCGGATCGTCATGGAGCTGCGCTCCGATGTCGTGCCCAAGACCGCCGAGAACTTCCGCGCCT
TGTGCACCGGCGAGAAGGGATTCGGGTACAAGGGCTCCATTTTCCACCGCGTCATCCCCAACTTCATGTGCCAGGGCGGCGACTTCACCAACCAC
AACGGCACTGGCGGCAAGTCCATCTACGGCAACAAGTTCCCCGATGAGAACTTCGAGCTGAAGCACACCGGCTCCGGCATCCTGTCGATGGCCAA
CGCTGGCGCCAACACGAACGGCTCCCAGTTCTTTATTTGCACTGTGAAGACCGCCTGGTTGGACAACAAGCACGTCGTCTTCGGCGAGGTCGTCG
AGGGACTGGATGTGGTCAAGAAGATCGAATCTTATGGATCGCAGTCTGGCAAGACCTCCAAGAAGATCATTGTGGCTAACTCTGGTTCTCTTTAA
GAAGGTGCGATGCAAAAGCAACAGCAACATTGCAAGAAGAAAAATCTGTTAAGACGAAAACCATTTGCATTTTCTCCAAAACATTTTTTTTTACC
AATTACTGTACTGTAATATTACGAGAAAAATACATAACAAACCAACATATTTTCAATAGACATGTTGGGTTTCCTTTGGCCAATCAATTGTATGT
GGGGGCCAAAAGTGAATAGAATTAGTGCCCACCAATGTCAGAAAGCGTTCAATTGGCTATATAATATGCATTAAATCTGTAACTTTAACATTTCC
ATTCACAAAAAAAAAAACAAAGAAGAAAAACAATGAGACGACAAGAGTCGAGAGGGGCTTAGAAAAATGTTTGATCTTTTGATGTTGGCTTACTT
ACTACTAATAATAGTATTAGTAATGCTGATTATCTAATTGCATATATATATATATATACCAACGTT
(SEQ ID NO: 1094)

Start ATG: 263

MSTLPRVFFDMTADNEPLGRIVMELRSDVVPKTAENFRALCTGEKGFGYKGSIFHRVIPNFMCQGGDFTNHNGTGGKSIYGNKFPDENFELKHTG
SGILSMANAGANTNGSQFFICTVKTAWLDNKHVVFGEVVEGLDVVKKIESYGSQSGKTSKKIIVANSGSL*
(SEQ ID NO: 1095)

Name: PEPTIDYL-PROLYL CIS-TRANS ISOMERASE 7 (ROTAMASE) (CYCLOPHILIN)
Classification: chaperone
Gene Symbol: Cyp1
FlyBase ID: FBgn0004432

Celera Sequence No. : 142000013385215
GAACAAAAGGAAAGAGGAATTCGTTAAGCGATAAAAGATAAAGATGATGGTGAAATATGAAAACTTATTTGACTCAAGAATTGCAATATACATAT
ATGTATCTAGATTGAATAAAATTATCTGTTAGGCAAATTGAATCTTGAATTAAGTGAATAAAATTCACAATGACGATAAATCTTTTTAGTACTAT
AAATATTAATCTCCAATAGCCATAAACTACTGGTCATTAGACGACGATATTATATCAATTAAAAACTTATAAAGAAACCCATAACTTGGTTGTAT
ACAAACATATAGATCTGTACAAGTTGTTATTACTTTGGGCTCAAGTTCTCTAAACCAGTAACAAAATTCTTATAGGCTAAGGTTCGCAAGTACTT
GAAGACTGAATGCCCATTTGTAACCGAATCTCACCTTCCAGCAGTGGAGGCTCATCATCGAATTCGTTGCCGGCTCCTCCGCCAGCAGCTGACTT
TCCGCTCTTGTCCTGTCCGTAGCTCGTGTCGGTGTAGGCCGTGGATCGTAGAAGCCACCCAAGCCTTGGCTCGGCGGTTGGGCATAGGACGCAT
CGTAGTTCGGCGGCACTGAGGCCTGTGTGTTGTCGAAGGTTTGGAAATTCCTGCAAGCAAGTGGGGCAACAATTGTGAATGCTGTGAAATGGAAT
TCCGGGTAACTACTCACAGTTCCTGGCCAAATTCTGGCATATCGAAGTTGTAGCTGGCATCGGCCGAGGGCGCGGAGCCGTAAAAGTCATTGGGT
CCGCCGAACTGAGACATGATTACTTTAATTTAAGCGCAATTCATATATTTACAAAATGATATTTAATTTAACAACACGTCAACTAGAGGTGACCA
ATAGCTAAATGTAATCGATGAATTTCGATGTTACCTATCGTCTAACACCGGTGCTATCTGAAATCGATATTTTCTCGCCCATCGATTTGTTTTAA ATTCAAAAAATTGCGCCACTTTATAAGAAAGTAAATAAAAACCCGATCATTTTGTAACATTCATAATACATTTTATTTCCATAGCTCCATTTGCA
ACACACACAAGTTACTGAAATAGCTATCCTTTGGTAGTAGAGGTACATGCTTTTGGGGCTACGTTGTTATTGCGTTCTTTAAAGGTCTATAATAT
GTAGGAATATAATATTTTGTAATTTCGTAAAGATTCAAACGCCCTTTAGACTCGTCGTTTAGTTGGTTTAGTTTCACACAATAGGGTAACGAACA
CAATCGATAACTATATGAAAATTTACTAACAATACATAGCTGTGAATTATATTTATATATCAACATAGATAATTATACATATGTGTCATATATGT
ATGGTATTTATGTATATGGCTGGTTTAACTGCGTTCCATTTGCGCTACCGACTAATTATTGTTCGTCTTTCCTTTCGTTTTGCGTATCTTCTGGT
GATTCGATTCTGACCTGACTAGACCTGAAGCGGGCCAAACTGTTTGTTAAACTTATAAGTAAACTTGGATTCAAATATCTTATTATGCATTATGT
AAATATGACTAGATTGAATGGGGAATTCGAATAATAACCTAGCTTTGGTTTCTTATTTCGTTTGGTTTGCTTCTTTTTCCATTCCTCTCGCTAGG
AAAGCCCGCAGTTGGTTTCTGTCCGTTTCCGCTTAGTCCTCTAGATTTCGGAAGGCCTGCTGCAGATCCTCGTACAGCTGGTCGTAGTCCGCCTT
GATCTTTTGCTCGCCATCTTTCACCGGGTCCTTAAAATGTGAATTATTAATATAAATAATAGTTGGAATAGATAAACCCACTCACCTTGAACTTC
ATTGACGACAGCTGGTACATAATTCCGCCCATCGATTCCCTGATGGTGTTCCATGTGATCTTGTTGTCCGACTGGGCTGTGGACTCAACGGCATG
ACGGGCGGTCTCATAGAAGGCCATGATGTTTCTCAGCATGCCCACGGTCTTGTAGAAGGGACAAACGCGATCGTATGGTGAGTAGGAGTTCTGTT
GCAGAAAGTCGTCCTTCAGCAGCTTTGCCACTTCCAGGGTCACCTTGTCGGTCTCGGCCAGTGATGCTTTGCCCACCAGCTGAACGATCTCAGAC
AGATCCTCCTCCTCCTGCAGGATCTCCTTGACCTTGGTGCGTAGTGGCACGAACTCGGGGTAGTTCTTGTCATAGTATTCATCCAGAGCACGCAT
GTACTTCGAGTAGGAGATGAGCCAGTTGATCGAGGGGAAGTGCTTGCGCTGGGCCAATTTCTTGTCGAGACCCCAGAACACCTGCACGATACCCA
AAGTGGCGGAGGTCACGGGATCGGAGAAGTCACCACCAGGAGGAGACACAGCTCCGACAATGGACACGGATCCCTCGCGCTCCGGGTTACCCAAG
CACTTGACGCGCCCAGCACGCTCGTAGAATGTGGCCAGACGAGCTCCTAGATAAGCCGGGTAGCCAGAATCGGCAGGCATCTCAGCCAAACGACC
CGAAATCTCACGAAGTGCCTCAGCCCAACGGGAGGTGGAATCAGCCATCATGGCTACGTTGTAGCCCATATCACGGAAGTATTCAGACAGAGTGA
TTCCAGTGTAGATGGAGGCCTCACGAGCAGCCACCGGCATGTTGGAGGTGTTGGCCACCAGAGCAGTTCGCTTCATAATGGACTCGGTGACGCCA
TCTATCTCGCAGGTCAGTTCGGGAAAGTCACGCAGTACCTCAGACATCTCGTTACCGCGCTCGCCGCAACCGACGTAGATGATCACATCAGAGTT
GGAGTACTTGGACAGGGCCTACGGGTGGTTGAAGTGCAGATTGGAAGGGATGGTCATTTAATGAGATGTAAGATGTGGATTAAGTGAATAATTTG
CAACTTGCCTGCGAAATGACGGTCTTGCCGCAGCCAAAGGCACCGGGGATGGCAGTGGTGCCGCCCTGTACGCAGGGGAAGAGCGAGTCAAGGAC
GCGTTGGCCCGTGAAGAGCGGATGGTTGGCTGGCAGCTTCTCTGTGACGGGACGTGGCTGCCGCACTGGCCAGACCTGCAACATGGTGTGCTTGG
TTATCTCGCCGTCGAACTCCGTCTCCAGGACAATGTCCTCCAGGTTGTAGTTGCCCGCGGGGGCAATGTATCGAACGGTTCCCTTAGCCCTGGGT
GCCACAATCATGCGCTGCTTCACCAGCGTGTTCTCGTGTACCACTCCATACAGATCTCCTCCGGTGATGTGGGATCCCACCCGCACATTCAGCGG
ATTAAATTCCCACATCTCCGAGCGCGACAAAGCAGTTGTGTTGACACCTTTGGGTATATAGATGGAGTTGGTCATGACACCAATGTCCCGCAAAG
GACGTTGGATGCCGTCGAAGATGCTGCCCATAATGCCGGGTCCAAGTTCCACGGAAAGAGGTTTGCCGGTACGCAGCACCGGATCGCCGACAGTC
ACGCCAGAGGTCTCCTCGTACACCTGGATGGTGGCCATGTCGCCCTCCAGACGGATGATCTCGCCCACCAGCTCGTAGTAGCCGACGCGGACCAA
CTCGTACATAGCTGATCCAGACATGGCCTCAGCGGTGACCACTGAAGTGGATTTAAAGTTGTTGAAGGAGGAAAAGCAGGAGAAATATGATTAGC
AAGGAGTGGAGAGAGCAGCATAATGAGGAAGATTATGCGGAACAGGAGGAGGGGGAAGAAAGCATACAGAAATATGAAAAGGAGAAGGATAATAA
GGAAGGATAAAAAGGAAGATGTGGAGGAGTATAATTAAGAACAGAAGAAAGGCAGGATTAAGGATTACAGAACTTGGGGGTCAGCGCATGAAGGA
CGCTGGTGACGTCGCTTACCTGGTCCGGATACCGCGTAGACACGGCCATATTCCGACTCGCGCTCCTCGTCTTTGAATTTCCTCAAGTTGGACAT
GGTCGCGGTTGCTGCTCTTCTTCTTCTGCTTCGGTAACGGTCAAATCGTTCGTTGGCTGTGGAAAAAGTAACCGTTTTTCTTATAAACAAAAAC
ACGCATTTTCCATGCCCCCGAATGAGAGAGCGTTTTCCGCGAGGAAACGCATAGGTGGCGCTGATGTGCAGCAGCAGCCCCCAGTGAAAAGCTTC
ACACCCCCGCAGCACAGCATCGATTTTCCAATACAATTTTCACACATGCCACCAACGGCAAGGTGAATTTTCCACCTTTTACCCATCACAAAAGC
AATTTTCACACTTTCTTTTCATTCAACACCTTGTGGTCAGTGGTTTTGTGGCGTAAAAACTGCTTTTTCAGCTGCTCTAAAATTAAATAAGCTCA
CATTTGTTTCAACAGCTCTTATGAAAATTCTCTTGCTTTTTTGATTTCACTCTAGTATTGATCTATCGGTTATCGTCGAGGGCTCCAGGTTCTCT
ATAGAGATGGGCTCACATCAAACTCACGCACGTCACGATACATTAATAGTCGGATTCCACTAGCACATTCCGCAGTTAAATCTTGAAATACTTGT
TGGTAATTATTAAAAATTTAACATAAGCTTGCATTTTTGTGCTATTTTCCAAATTCTTCAATGCAACTTGTTCACTCCAGTAATATAAATGTTTT
GTACCACAACTTTAAGCCAATTTCTTTTTAATTGCTTATAATAAAGAACAAATTTATTAATTACTTTATTATTTTTATTTAATATGTTCTCTAAC
ATTTTAAATGCTTATAAGTCGCCGCCAAGTACAGAAGTATCAGCAAGAAAATATCGATTGTAAATTGATCGAATTCTGTTTTACATCACTAATCG
GCAGCGGCTGCAATAAATTTCCGTAAAAACCGAAGTAATCCGCAATTAAAGAAAGCAAAGGACCTGCATCCGTGTGAGATCGTTCGGCACCGGTG
CCGGCACATGAAATCCTATCGAGTGACCAGTGGAACAGTGCGTACAGCGCCCCGGGGCAACTGAAAAGATAACCTCCAAAGTCCGTAGACAGCAG
GCAGATGCACCTGCTCCACCCTTTCCCCTCCCAAATGCAAGTGAAAATCGCGTTTAAATAGTGAATAAACCCTGCCCAGCCATGTCGACGACGTC
GGTGGTGCAGCAGTTCGTCAACGGGCTTAAGTCCCGCAACCGGAATGTACAGAACAAGGCAACCCAGGATCTGCTCTTCTATGTGAAGACCGAGC
TACGCGAAATGTCCCAGGAGGAGCTGGCCCAATTTTTCGACGAGTTCGACCATCACATTTTCACGATGGTGAATGCGACAGATATCAACGAGAAA
AAAGGCGGTGCCCTGGCCATGAGTGAGTTCCTGGCTCCCCGGCAGTGCTTGAGAGGATTTAACGTCTTCCCTTTCAGAGTGCCTGATTAACTG
(SEQ ID NO: 1096)

Exon: 4318..4277
Exon: 3951..3820
Exon: 3556..2859
Exon: 2773..1796
Exon: 1740..1001
Start ATG: 3895 (Reverse strand: CAT)

Transcript No. : CT27956
CAAAAAAGCAAGAGAATTTTCATAAGAGCTGTTGAAACAAATCCAACGAACGATTTGACCGTTACCGAAGCAGAAGAAGAAGAGCAGCAACCGCG
ACCATGTCCAACTTGAGGAAATTCAAAGACGAGGAGCGCGAGTCGGAATATGGCCGTGTCTACGCGGTATCCGGACCAGTGGTCACCGCTGAGGC
CATGTCTGGATCAGCTATGTACGAGTTGGTCCGCGTCGGCTACTACGAGCTGGTGGGCGAGATCATCCGTCTGGAGGGCGACATGGCCACCATCC
AGGTGTACGAGGAGACCTCTGGCGTGACTGTCGGCGATCCGGTGCTGCGTACCGGCAAACCTCTTTCCGTGGAACTTGGACCCGGCATTATGGGC
AGCATCTTCGACGGCATCCAACGTCCTTTGCGGGACATTGGTGTCATGACCAACTCCATCTATATACCCAAAGGTGTCAACACAACTGCTTTGTC
GCGCTCGGAGATGTGGGAATTTAATCCGCTGAATGTGCGGGTGGGATCCCACATCACCGGAGGAGATCTGTATGGAGTGGTACACGAGAACACGC
TGGTGAAGCAGCGCATGATTGTGGCACCCAGGGCTAAGGGAACCGTTCGATACATTGCCCCCGCGGGCAACTACAACCTGGAGGACATTGTCCTG
GAGACGGAGTTCGACGGCGAGATAACCAAGCACACCATGTTGCAGGTCTGGCCAGTGCGGCAGCCACGTCCCGTCACAGAGAAGCTGCCAGCCAA
CCATCCGCTCTTCACGGGCCAACGCGTCCTTGACTCGCTCTTCCCCTGCGTACAGGGCGGCACCACTGCCATCCCCGGTGCCTTTGGCTGCGGCA
AGACCGTCATTTCGCAGGCCCTGTCCAAGTACTCCAACTCTGATGTGATCATCTACGTCGGTTGCGGCGAGCGCGGTAACGAGATGTCTGAGGTA
CTGCGTGACTTTCCCGAACTGACCTGCGAGATAGATGGCGTCACCGAGTCCATTATGAAGCGAACTGCTCTGGTGGCCAACACCTCCAACATGCC
GGTGGCTGCTCGTGAGGCCTCCATCTACACTGGAATCACTCTGTCTGAATACTTCCGTGATATGGGCTACAACGTAGCCATGATGGCTGATTCCA
CCTCCCGTTGGGCTGAGGCACTTCGTGAGATTTCGGGTCGTTTGGCTGAGATGCCTGCCGATTCTGGCTACCCGGCTTATCTAGGAGCTCGTCTG
GCCACATTCTACGAGCGTGCTGGGCGCGTCAAGTGCTTGGGTAACCCGGAGCGCGAGGGATCCGTGTCCATTGTCGGAGCTGTGTCTCCTCCTGG
TGGTGACTTCTCCGATCCCGTGACCTCCGCCACTTTGGGTATCGTGCAGGTGTTCTGGGGTCTCGACAAGAAATTGGCCCAGCGCAAGCACTTCC CCTCGATCAACTGGCTCATCTCCTACTCGAAGTACATGCGTGCTCTGGATGAATACTATGACAAGAACTACCCCGAGTTCGTGCCACTACGCACC
AAGGTCAAGGAGATCCTGCAGGAGGAGGAGGATCTGTCTGAGATCGTTCAGCTGGTGGGCAAAGCATCACTGGCCGAGACCGACAAGGTGACCCT
GGAAGTGGCAAAGCTGCTGAAGGACGACTTTCTGCAACAGAACTCCTACTCACCATACGATCGCGTTTGTCCCTTCTACAAGACCGTGGGCATGC
TGAGAAACATCATGGCCTTCTATGAGACCGCCCGTCATGCCGTTGAGTCCACAGCCCAGTCGGACAACAAGATCACATGGAACACCATCAGGGAA
TCGATGGGCGGAATTATGTACCAGCTGTCGTCAATGAAGTTCAAGGACCCGGTGAAAGATGGCGAGCAAAAGATCAAGGCGGACTACGACCAGCT
GTACGAGGATCTGCAGCAGGCCTTCCGAAATCTAGAGGACTAAGCGGAAACGGACAGAAACCAACTGCGGGCTTTCCTAGCGAGAGGAATGGAAA
AAGAAGCAAACCAAACGAAATAAGAAACCAAAGCTAGGTTATTATTCGAATTCCCCATTCAATCTAGTCATATTTACATAATGCATAATAAGATA
TTTGAATCCAAGTTTACTTATAAGTTTAACAAACAGTTTGGCCCGCTTCAGGTCTAGTCAGGTCAGAATCGAATCACCAGAAGATACGCAAAACG
AAAGGAAAGACGAACAATAATTAGTCGGTAGCGCAAATGGAACGCAGTTAAACCAGCCATATACATAAATACCATACATATATGACACATATGTA
TAATTATCTATGTTGATATATAAATATAATTCACAGCTATGTATTGTTAGTAAATTTTCATATAGTTATCGATTGTGTTCGTTACCCTATTGTGT
GAAACTAAACCAACTAAACGACGAGTCTAAAGGGCGTTTGAATCTTTACGAAATTACAAAATATTATATTCCTACATATTATAGACCTTTAAAGA
ACGCAATAACAACGTAGCCCCAAAAGCATGTACCTCTACTACCAAAGGATAGCTATTTCAGTAACTTGTGTGTGTTGCAAATGGAGCTATGGAAA
TAAAATGTATTATGAATGTTACAAA
(SEQ ID NO: 1097)

Start ATG: 99 (Reverse strand: CAT)

MSNLRKFKDEERESEYGRVYAVSGPVVTAEAMSGSAMYELVRVGYYELVGEIIRLEGDMATIQVYEETSGVTVGDPVLRTGKPLSVELGPGIMGS
IFDGIQRPLRDIGVMTNSIYIPKGVNTTALSRSEMWEFNPLNVRVGSHITGGDLYGVVHENTLVKQRMIVAPRAKGTVRYIAPAGNYNLEDIVLE
TEFDGEITKHTMLQVWPVRQPRPVTEKLPANHPLFTGQRVLDSLFPCVQGGTTAIPGAFGCGKTVISQALSKYSNSDVIIYVGCGERGNEMSEVL
RDFPELTCEIDGVTESIMKRTALVANTSNMPVAAREASIYTGITLSEYFRDMGYNVAMMADSTSRWAEALREISGRLAEMPADSGYPAYLGARLA
TFYERAGRVKCLGNPEREGSVSIVGAVSPPGGDFSDPVTSATLGIVQVFWGLDKKLAQRKHFPSINWLISYSKYMRALDEYYDKNYPEFVPLRTK
VKEILQEEEDLSEIVQLVGKASLAETDKVTLEVAKLLKDDFLQQNSYSPYDRVCPFYKTVGMLRNIMAFYETARHAVESTAQSDNKITWNTIRES
MGGIMYQLSSMKFKDPVKDGEQKIKADYDQLYEDLQQAFRNLED*
(SEQ ID NO: 1098)

Name: V-ATPASE A SUBUNIT
Classification: enzyme
Gene Symbol: Vha68
FlyBase ID: FBgn0013355

Celera Sequence No. : 142000013384830
TGTGTTTATGCAGTGTGTGTGTGTGCTGCCCACTCTCCTCGCCTTGCTCCCTGCGCTGTCCCCCGCCCTCTCTCCTGCTGCTTATCGCGCGTC
TCCATCGCCATGCACTTTGTTGCTGTCGGCCATAGCTGCAGTTGTTGTTGCCTGCTTTTTTCTTTTTCTCTCTGTTTCGTTTTTTTATCGCTGC
GTGCGTGTAAGCCGACGCTAGCGGCATCTCCCCTCTCGCTCTGGCCCCCTAGGAACACAACACTACACAACAACGCAGCAGAGCGAGCTCCATGG
GCAGAGCTGACCGGTCTTAGCGGGAAAATAGCTAGTTCTGGCTATGAAGAGTCATGTTAAGTAAATGTCGTTTGCAAGTAATTCTATAGTGTGCG
TTTTACTAGTATACAAAAGTCCCTTTTACAAAAGCTATGTTTTCTAAGCATAGAAACTGCAACGAAACTTCAGGTCATGTAAAAGGGACTTTACC
TAACTTTGAAGGACCGAATGTTCTCAAATAAACTCAAATAAATTTTTACATAGAAGGTTACGGAAGTCTGACTATAAAAAGAATATACGTTTAGG
ATATTTAGTGTATTGGATATTTTCTCATTTCAAAGCCTATTCTCAAAAAAGAAAATGTTTCTAACATCGAAAACATCACTAAACCGGCTGAGCTG
GCAGCTCTATCCCCCGACGTCGTCAGTCTCAGTCCCTTTTGCCCCAACTCCGCCCGCTCGCCATGCTTGCCTGCTTGCCAGTGTGTGTGCGTGTT
GTGTTGTGTGTGCCTCATTGTTTGCTTTTTGTTGTTGCTGCGTTGTTTTGTGCCTCTCTGCTCGTTTCTCGATTCGTACGAAAAAAATGTAGTAC
AGCGTGTGGTATGGCAAACGAAAGCTATGAGTTTTCAGTGTATCTTGTCTGCCCTCTCTTTCCCGCCCGGAATCTATGGTTGGGAATTATAAGAG
CCGCGAGCGGCCTCCTTCGCCGCACAGGCGTTGCAGTCGTGGTGGACGCATCACCTGACCAGCCAGAGGCCCAGGTTGAGCTTCTGCAGCTTGGG
CAGCTTCATGATGATGTCGATGCCCTTGGAACTGAGTTGCGTGCAGCCGTAGAGATCGATGGTCTTGAGATTAGTCAGATCCTCGGCCAGCGTTT
GCAGGCCCTTGTCCGTTATCCGGCTGCACTGTCCGATATTGAGGTTCTCCAACTCGTGCAATGCCTTGGCGATCTTTAGCATGCCGTGATCGGTG
ATCTGGCACTGATTGAGGGACAGGGATCTCAGTCTGTAGAGTCCCTGGGCTATGTGTGTCAGGGCCTGGTCGCTGATCTTGTCGCAGAAACTGAC
GTCCAGCGAGTTGATCCCGCTGCCGCCTTCCGTGAGGTAGGCCATTCCGATATCCGAGATGTTGTCGCAGGAGCGCAAGTTCAGCTGCTCGAGCT
TGGGCATCCGGGCCAGGTGCTTTAGTCCGCTGTCCGTCACCGAGACGCAGAAGCTCAGGTTGATCGACTTCAGCGAGGTCAGGCCCTGGGCAATG
TGGCCCAAAGCCTCGTCGCTTAGCCGCTGGCAATCCTGCAGACCCAAGTACTCCAGCTGCAGGTTGCCTTCGGCCGTTTCCCGCGAGAAACCAGC
CAGGTGTCCGATTCCCTGGTCGCTGATGTGCCAGCAGGAGCGCAGATTGAGGTGCTTCAGCTTCTTCAGGCCCCACGCAATGAGCAGCAGTCCTG
TGTTCGTGATGTTGCAACAGCCGCCCAGTTCCAGGGTCTCAAGATTCCTTAGATGCTGGGCGATGCGCCCCAGACTCGTGTCCGTGATCTGTTTA
CAGAGGGAGAGGTCCAGTGTCTTGAGGTTTGGCAGATCCACGCTAAAGGCATGGCCCAGGTTCATGTCCGCCACGTTGAAGCAGCCGCTCAGGTT
CAGAGAGGTCAGAGCCGGAACGCCCAGGACCAAATCCTTAAGCGAGCGGCGCAGCGATAGGATCTGCACCTTCTTGATGCCGCGCTTGACCAGGC
AGTTGAACAGGCTCGGACTGGAACGCTTAAGGTGCAGCTTGGCCTCGACTCCCTTCCAAACGCTCTTGGCATAGGCCGCATCCCGCCATGCGGTG
CAAACCTGAGCTGCCCGACCCAAATCCCTCACTGGTAGGTGCTCGAATATCTGCTCGAGGAGTTCTGGGAACAGGTTGCTTATGTGGGTGCCCTC
CACCGGCGGCGGGCTCTCCGGAGATGCTGGTCTGTGCGGGAGATGGTGGTGATGGTGATGATGGTGCTGGGCGTGGGCCGCTGCTGCTGCCGCTG
CCGCCGCAGCTGCTGCGGCATGCTGCAAGTAGAGGGCCGGCGGCAAGGTCTGCAGCTGGTGGTGCGGCGGTCGGTGGTGCAGGGCGTAGGGCGTG
AAGCGCAGCAGGTGGTGGTGGGTGGTGGTGGCTCCGGTTCGCGTCAGACCGGGCAGCTCAGTCTGTTGATAGAGTTCGTCCATGGCCCAGCTGGG
CGCTCCTCCGGCTCCTGCTCCGCCAATCGCCGCGCCGCCACTGGTGGCCGCTCCGTTGCTCCCGGATCCGCCACAGTGGCTATTCAGATTGTTCA
ACACCGCGATTGTTTGATGATGGAAGGGCAGCAGCTCCGTGTTGGTCGCCATCTCCTACTCTTGATTTTACACTTGGCTTGTCGCTTGACTGCTA
CTTTTGAAATTAACTGTTGGATTGGCTATCCTATATGCGCTGCATTTTACTGTTTGTATGCTTAGTTGAAGACTAGTAGGGTTCACTGTGGTTAT
TCACTGCACTTAACTCGAGCACTGTGTGTAGTTGGAAGTCCAAGTTCTATTTGTGTGTTCTTTGTTCTTGCGGCCGAGACGCGATGTGCACGAAC
CGGATGATAAAGAAAAACTGAACTCGCAGCGGCAAAGCGCCTTGCTTTTAGCCTGAAATACAGATGCAGATACAGATACGGGGGGTTTGTGTTGG
TATTGGTCATATTTTTATCTGAACGTATTCAGCGCTCTCACCGCTCTCTCGAGCGAGTAGAGAGTAGCGAGTAGGTATTCGTCCGTTCAGTCTGT
TGTATGTCCCGTGTGTGCGGTTCGGTCGTTCTTCCATTGCGATTGCACTTGGAATTGACTTTGTGCGGCATTTTTATTAGAATCATTGCAACGCG
TGGTTTTCTTGCTAATTTTGCCATAAGTTCTTATTAAAAGGTAGCTAGCATATGCTCTTTCTGTCCTTTATCACCAGTTCTGCGAGTCAATTTTT
AACCAGTTCGGCTTGTATATAAATAATTTAGGTTCAGACATAATCTCTATTGCTCGTAAGGAGTTTCACAAATTGTTTAAACTTAAAGTTTGAAG
ACCGTTTTGCGTATTCAACTCATCCGTGACCCATTTTTTTTATTATTTATCATATAAATATATTTATTATCTCGACATTGTGTGGCGTTCTACTT
AGGATCTCCTGCAGCTTATGATAAGAGAAGCTTCCCCATATTTCCTTTCTCGCCAGCTCTCTCATCACTAACGCTGGTTATAAGACCAGGCTTGG
ATTTATCTTTCGGGTTTTTCGGTTTTGGACGCCAGCTCCATGTTTCAGGTTATTCTTTACCCGTCGAGCCAAACTCAATGCCAAACTCCGACGCA TTTGTTGTTTCTGCTGCCGCTGCATTCCGAAGTCGAGCAGGTACCTGTCTTTCTCCCTCCCTCGCCATCTCTCTCGCTCTCTATCGCATCTGTGT
GAGTGCGATCGCTGCTCGCTACCTGCGAACGCAAGAGCAGCAACAACACAATCCCGGTTTCCAGGAAAATATTAACGATAACTCCAAAAAAAGCA
GAAACTCCGTTGCCGCACCACACACAGAAACTCAGA
(SEQ ID NO: 1099)

Exon: 2836..1001
Start ATG: 2617 (Reverse strand: CAT)

Transcript No. : CT28019
CGTCTCGGCCGCAAGAACAAAGAACACACAAATAGAACTTGGACTTCCAACTACACACAGTGCTCGAGTTAAGTGCAGTGAATAACCACAGTGAA
CCCTACTAGTCTTCAACTAAGCATACAAACAGTAAAATGCAGCGCATATAGGATAGCCAATCCAACAGTTAATTTCAAAAGTAGCAGTCAAGCGA
CAAGCCAAGTGTAAAATCAAGAGTAGGAGATGGCGACCAACACGGAGCTGCTGCCCTTCCATCATCAAACAATCGCGGTGTTGAACAATCTGAAT
AGCCACTGTGGCGGATCCGGGAGCAACGGAGCGGCCACCAGTGGCGGCGCGGCGATTGGCGGAGCAGGAGCCGGAGGAGCGCCCAGCTGGGCCAT
GGACGAACTCTATCAACAGACTGAGCTGCCCGGTCTGACGCGAACCGGAGCCACCACCACCCACCACCACCTGCTGCGCTTCACGCCCTACGCCC
TGCACCACCGACCGCCGCACCACCAGCTGCAGACCTTGCCGCCGGCCCTCTACTTGCAGCATGCCGCAGCAGCTGCGGCGGCAGCGGCAGCAGCA
GCGGCCCACGCCCAGCACCATCATCACCATCACCACCATCTCCCGCACAGACCAGCATCTCCGGAGAGCCCGCCGCCGGTGGAGGGCACCCACAT
AAGCAACCTGTTCCCAGAACTCCTCGAGCAGATATTCGAGCACCTACCAGTGAGGGATTTGGGTCGGGCAGCTCAGGTTTGCACCGCATGGCGGG
ATGCGGCCTATGCCAAGAGCGTTTGGAAGGGAGTCGAGGCCAAGCTGCACCTTAAGCGTTCCAGTCCGAGCCTGTTCAACTGCCTGGTCAAGCGC
GGCATCAAGAAGGTGCAGATCCTATCGCTGCGCCGCTCGCTTAAGGATTTGGTCCTGGGCGTTCCGGCTCTGACCTCTCTGAACCTGAGCGGCTG
CTTCAACGTGGCGGACATGAACCTGGGCCATGCCTTTAGCGTGGATCTGCCAAACCTCAAGACACTGGACCTCTCCCTCTGTAAACAGATCACGG
ACACGAGTCTGGGGCGCATCGCCCAGCATCTAAGGAATCTTGAGACCCTGGAACTGGGCGGCTGTTGCAACATCACGAACACAGGACTGCTGCTC
ATTGCGTGGGGCCTGAAGAAGCTGAAGCACCTCAATCTGCGCTCCTGCTGGCACATCAGCGACCAGGGAATCGGACACCTGGCTGGTTTCTCGCG
GGAAACGGCCGAAGGCAACCTGCAGCTGGAGTACTTGGGTCTGCAGGATTGCCAGCGGCTAAGCGACGAGGCTTTGGGCCACATTGCCCAGGGCC
TGACCTCGCTGAAGTCGATCAACCTGAGCTTCTGCGTCTCGGTGACGGACAGCGGACTAAAGCACCTGGCCCGGATGCCCAAGCTCGAGCAGCTG
AACTTGCGCTCCTGCGACAACATCTCGGATATCGGAATGGCCTACCTCACGGAAGGCGGCAGCGGGATCAACTCGCTGGACGTCAGTTTCTGCGA
CAAGATCAGCGACCAGGCCCTGACACACATAGCCCAGGGACTCTACAGACTGAGATCCCTGTCCCTCAATCAGTGCCAGATCACCGATCACGGCA
TGCTAAAGATCGCCAAGGCATTGCACGAGTTGGAGAACCTCAATATCGGACAGTGCAGCCGGATAACGGACAAGGGCCTGCAAACGCTGGCCGAG
GATCTGACTAATCTCAAGACCATCGATCTCTACGGCTGCACGCAACTCAGTTCCAAGGGCATCGACATCATCATGAAGCTGCCCAAGCTGCAGAA
GCTCAACCTGGGCCTCTGGCTGGTCAGGTGA
(SEQ ID NO: 1100)

Start ATG: 220 (Reverse strand: CAT)

MATNTELLPFHHQTIAVLNNLNSHCGGSGSNGAATSGGAAIGGAGAGGAPSWAMDELYQQTELPGLTRTGATTTHHHLLRFTPYALHHRPPHHQL
QTLPPALYLQHAAAAAAAAAAAAAHAQHHHHHHHLPHRPASPESPPPVEGTHISNLFPELLEQIFEHLPVRDLGRAAQVCTAWRDAAYAKSVWK
GVEAKLHLKRSSPSLFNCLVKRGIKKVQILSLRRSLKDLVLGVPALTSLNLSGCFNVADMNLGHAFSVDLPNLKTLDLSLCKQITDTSLGRIAQH
LRNLETLELGGCCNITNTGLLLIAWGLKKLKHLNLRSCWHISDQGIGHLAGFSRETAEGNLQLEYLGLQDCQRLSDEALGHIAQGLTSLKSINLS
FCVSVTDSGLKHLARMPKLEQLNLRSCDNISDIGMAYLTEGGSGINSLDVSFCDKISDQALTHIAQGLYRLRSLSLNQCQITDHGMLKIAKALHE
LENLNIGQCSRITDKGLQTLAEDLTNLKTIDLYGCTQLSSKGIDIIMKLPKLQKLNLGLWLVR*
(SEQ ID NO: 1101)

Classification: hypothetical

Celera Sequence No. : 142000013384811
GGGGAAATTGGAACAAGACCTTGGGTAACCGGCATACGAATGAAATTCTAATTTTATGAGGCCCAGCCAATTATAAAGTATGTGGGAAAAGTTTA
AGGGTAATCCTAAAACTGGACACCAGTTTACCAAGGAAAGAAATTCTAGTTAAATCGAGTACCATAGACTTTACGACCGTAGGTAGGATTATAAA
AAGTCATGTTAGTACCTTCAAATTTAGTATCGTAATATGACTTTTTACGAGAGTGCGTTTGTAATAAAGTAAAGTCGTTCTTAAAGAAGTCGTATT
TCTTTTAATAAGATACGTACTCCGCTCATTCAACTTTAAAATTGATATGTGTGGAAAATTAAGATGTACACATATCCTTGGCAACAGATCACTTG
AAAATCCTTAGTGGTCCTTGGGCCATTGAACTTGTTCTCAAGCCCGCACTTCACCTCGAATCCACCCAATCCAAACTTCAAACTGACGACATGCA
GCGCAATTTGAGATCCCAGATTCGGGAACCTTTCACGCACACATGTGCAACCTGATTTCCAAACGCTTAAAGGACACGCTGTGCCTGTGCCAGCG
GCATCTTAAGTGATTTCGAAAAGGAGCTGGGAAGCGGTAAAAGTATCTGGAGGATGCGCGGATGTCGGATCTCAGATACTCAGATACAAGAATTC
TTGAGTGCACGTCGTACGCAGGCACTTGGGCACACACACACTCCACTCATTGTAGGTTACTAGTTAAATCTGAAATCGAGGCAGCTGGAGAAAGA
GACGGCTGCCGCAGGGGCCGACAAAAAGAGACGGGACGAGGCACTTGGCCAAGGAACATCTGTTGCGCTGACATAAATCCTGAGTGACTGACCGC
TGGTGCGAAAGACCGCGAATCTCGAATGCGAATGTTCATGTGGATGCGACTTGGCCGCCGGCGCTCGTTTGAGGACCAAAACCAGTTTGCACCGA
TTCCCAGCTGCCCGTTTGGGTACAGTGGTTCAAAAGGTAATCTATCTGATTCAAATCTTGTCCACCTAACAACAATTTGAAGTCCGAAGATAAAG
CTCTTATTTCAATTAAAAAGAATGGCAGGATAGTAGGATAGCAGGAGAAACATTTCATTATTAAATTTGATTATCTACATTACATTTCGTACAGA
AAAGAAGTTAAAAGTGATTTAATGCCCGTAAAACCACTGTGCCCGCCAATTTCATTGAGTAACTTTTGCGCTGCCCGTGAATGAATCTGTGGGAT
ACTCCCCACCGCTTTCGTACTTCGATTCGGTGGGACAGGATCTGAGAATGGAAAACCAGTGAGCAGACTTACCTTCTTCTCGGTGAGCTTCTCGC
AGCGGCGCTGCTTGCAGATCTGGTGGCTCTTGTCGTTTCGGCAGGGGGCGCACTCCCCACAGTTGTCCTTGCGCTGGCATCCCACGCATTCGCCG
CACCGCTTGCGCTTCTTCTTGGACTGGAAAAGAGAGCAGGAAGAGGAGTTGTTGTCGTTGGAGTGGTTGTGGTTGTGGTTCTGGTGGTTATGGTT
GTGAGTGGTGGGTGTGATTGTGATTGTGGGTGGTGGCAGTGTCATTGGCGGGTGGTTCAGTGTGGGTGGCGGAAGATGGTGGCGACGACCGTAGT
CCTGTTAATCGCAGCGGTTGCCAGTTCGCCCCGTTTCGCAAGTTTATCGGTGGGGTTGTCGAAGATATCCGATATTTATCGATCAAAAACTATTC
ACTTCTTTTGCTTCTCGTTTGTAATGCAAATGGATCGTACAATCGATATATACCTTCGGCTTCAACATCCCCACCCTTCGATCACCTACCTGCTT
GTCGCATCCACTGGCATTGGCATCGTTGCTATCCCCCATGCCCAGGGCACTCAACGGACTCTTGAAGTTGGCCGTGCTGGAGACGGCGTCCACTT
GGCCAGGATTGCTGGGGTCTACGTCCATGCCGCTGGCCTCGCTCTCGGCACTGGACTCCAGCGAATTGGGCCGCTGTTTCCGGCGCTCTTTCTTC
CGCGCTTCTAGCCGAGCTATCGGCGACTGCAGCAACTTCTCGACCTTGACCGGAGTGGTGGTGGTGGGTGTGGGCTGGGTGGTGGTGGTGTGCGG
CGTGTGGCTGCCACTCCCACCGCCAGCCGCCTGCGGATAGCTGTTGTTGCTGTTGTTGCCATCATACGAGGTGGGCGTGTGCATGCCCATTGGTA
TGGGATGCGGCTGGCCGTGCTGCAGCGGATGGTGGATCAGTCCGGCGCCACCGCTGTTGCTGAGATCAAAGTCCTCCTTCTTGAGCAGCATCTCG
AAGTCGCTGCCGCCCGAGATCGGCTCCTTCTTGACACTCAACGGGGTGAATCCCGGATATAGTGGCAGCTCCGCGTAGGGCGTGGGATAACCGCT
GGCTCCTCGATGATGGTGGTGCGGATTGAGGGCGTGGTGGTGCGCGAAGGCGTTCGGCGGCGGTGGTGCCGGAAAACTGCCCGCTGATGGCGGTG TGATGCTGGTCTGCAGACTCGAGAGTTGGGTCAAAGGTGAGCCCACACTCATCATGCCCGGCGAGCTGACCGAAATGCTGGCCGGCGACATGGCC
ACCGTTTGCAGGGAACTCATGGCGGTGGGTCCCACGGGTCCTGCTACTGAATTGGGTCCTACGGAGCCAGGAGGTATGGAACCTGTTGCAGCTGC
TACTGCAGCTGCCGATCCTGGTGGCACTCCTGCTCCTATGGGCACAGGCATTGGTGTTCCATCCGGTAGTAATTGCTCATTGAAGCCATGGAACT
GGCTCTGAAACGACGGCAGCTTGGAGAACGGCTCGAAGCCGCTCTTCAGCTGCAGATGGGGTTGCGTTTGGGGGGTTGTGGCCCATTGTCCTTG
GACTCCATTTCCCAGGGACGCGTGTAGCTGCCGTTCGAGTTGGAATTGGAGTTCGAATTCGAGTTGGCGTTGCCGGCTGAGTTGTTCGGTTGCTG
GTTACCCGGATTTCCTACTGCGGCGGAGGCGGCGGAAATGGCATTGGCATTGGCATCGCCGTGCCGCTGGCCACTGTTGCCTCCACTTGCAGCAT
TAGCATGGTTGCTGCTGCTGTTGTTGCTGCTGCCCAAAGGCGCTGGAACCGTGGTATTGCTGCCGTCGGGGTTGCTGTTGTTGCCGTTGTTGCCG
TTGTTGCCGTTGTTGCTGCTGTTGCCGTTGGTGTTGCCGGTGGCGGCCGCTGGCTGTTGCTGTTGCTGCTGCTGCTGTTGATGTTGCTGCTGCTG
CCTGGCATAGTAGTCCCAGTGCTGCTGCTGCTGCTGCTGCTGTTGCTGCTGCTGCTGCTGATGTTGCTGCTGGGCGTGATGCTGCTGCTGTTGCT
GTTGCTGCAGATGTTGCTGCTGCGGATAGTGCTGCTGGTAGTGATGATGCGGATGCGAATGCGAATGCGGATGGTGGTACGGCGTGGTATAGTGC
TGGCTGAGGCTGCTCAGCTGGTTGAGATGGGTGTTGTGCAGGCTGGACACGGTGGCCTCCACAGATGTGGCTGCTGCTGCAGTTGCTCCCAAGTT
GCTGCTGTCGACGGTAGCACCTGTGCTGCTCTGGGCTAAAATTGAAGACGCCATTTAAGCACAAACACTGGCATGGCTATGCAGTTGTATTGAAA
AACTGCGGGGCTTTGTACTGATTTTTCGAAGATTCGTTTTTAGTTTTTGTACACTTATCGGTTCACTTTTCGTTTGTTCGTCTGCTTTTTGAGGT
AGAGTTCTTCGTAAAAATGTTTCTGATTCGACTGGTTTGTTTGTTGGCTAGTGTAAAACACTATGATTATATCCGTATAATAGATTTGTATACTA
TAATATAAGTTGAAGCTACTCCAAGATTTGTATTTCGTTTATTTTGAACTCACTGGTTTTGCGTGTTTGAATGCAAAGTTGAATATTTACTTGTT
ATGGTGTTCTTCTTTGTAAAGTGCTTTATTAAATTGTTGTTTAAAAATTGTTTAAGATTTGTGGTTGGTTGTTTTGTACTTTATTCTTTTGTTTG
TTTGTAAAACGGCAGCTAGGCAAAAATTTGTATTTTGATATTTGATTTAATTTGTAGCAGACTTGGTTTGGTTTTGGTTTTTCCTTTAAAAAATC
TTTGTAAATTTGTAATTTGTAAAATTTGTATTTCGTATGCGTTGTTGTTGTTGTTTTATTTACGTTATTAATTACTTGCTGTTTGTGGTTGATAA
TATTTGACGCTTGCTTGTTGTAAATTGATTAAGTTTTTGTACTCTGGTTTATGCTTCGTTTCTCAATTGAATTTGCTTGTAATATGTCGTCGGAT
ATAAAAATAATTTAAGTATTTACATCTAGTAAATTGTACTTATGCGTAGGCTTAAAAATCTTTGTCTTCCGTTTGTTTGTTTGTTTGGGTTCTGG
ACTTAACGATTAATTAAACATTAGCGCGTTACTTGTTATTGACTTTAATAGTAATAATATTTATATTTCATATAAGTTGTGTGTTTAGCCTAATT
CATTTTACGCCTTTTGTTCGTTTGCTTTTCAATTTTGATTTTGGGCCGAAAGGTTTCTTTTTGTTTTTGTAAGTTGCTTAAAGAGCTTCCAAAGT
ATTTTGTGT
(SEQ ID NO: 1102)

Exon: 3569..1800
Exon: 1616..1308
Exon: 1015..1001
Start ATG: 3569 (Reverse strand: CAT)

Transcript No. : CT28117
ATGGCGTCTTCAATTTTAGCCCAGAGCAGCACAGGTGCTACCGTCGACAGCAGCAACTTGGGAGCAACTGCAGCAGCAGCCACATCTGTGGAGGC
CACCGTGTCCAGCCTGCACAACACCCATCTCAACCAGCTGAGCAGCCTCAGCCAGCACTATACCACGCCGTACCACCATCCGCATTCGCATTCGC
ATCCGCATCATCACTACCAGCAGCACTATCCGCAGCAGCAACATCTGCAGCAACAGCAACAGCAGCAGCATCACGCCCAGCAGCAACATCAGCAG
CAGCAGCAGCAACAGCAGCAGCAGCAGCAGCAGCACTGGGACTACTATGCCAGGCAGCAGCAGCAACATCAACAGCAGCAGCAGCAACAGCAACA
GCCAGCGGCCGCCACCGGCAACACCAACGGCAACAGCAGCAACAACGGCAACAACGGCAACAACGGCAACAACAGCAACCCCGACGGCAGCAATA
CCACGGTTCCAGCGCCTTTGGGCAGCAGCAACAACAGCAGCAGCAACCATGCTAATGCTGCAAGTGGAGGCAACAGTGGCCAGCGGCACGGCGAT
GCCAATGCCAATGCCATTTCCGCCGCCTCCGCCGCAGTAGGAAATCCGGGTAACCAGCAACCGAACAACTCAGCCGGCAACGCCAACTCGAATTC
GAACTCCAATTCCAACTCGAACGGCAGCTACACGCGTCCCTGGGAAATGGAGTCCAAGGACAATGGGCCACAACCCCCCAAACGCAACCCCATC
TGCAGCTGAAGAGCGGCTTCGAGCCGTTCTCCAAGCTGCCGTCGTTTCAGAGCCAGTTCCATGGCTTCAATGAGCAATTACTACCGGATGGAACA
CCAATGCCTGTGCCCATAGGAGCAGGAGTGCCACCAGGATCGGCAGCTGCAGTAGCAGCTGCAACAGGTTCCATACCTCCTGGCTCCGTAGGACC
CAATTCAGTAGCAGGACCCGTGGGACCCACCGCCATGAGTTCCCTGCAAACGGTGGCCATGTCGCCGGCCAGCATTTCGGTCAGCTCGCCGGGCA
TGATGAGTGTGGGCTCACCTTTGACCCAACTCTCGAGTCTGCAGACCAGCATCACACCGCCATCAGCGGGCAGTTTTCCGGCACCACCGCCGCCG
AACGCCTTCGCGCACCACCACGCCCTCAATCCGCACCACCATCATCGAGGAGCCAGCGGTTATCCCACGCCCTACGCGGAGCTGCCACTATATCC
GGGATTCACCCCGTTGAGTGTCAAGAAGGAGCCGATCTCGGGCGGCAGCGACTTCGAGATGCTGCTCAAGAAGGAGGACTTTGATCTCAGCAACA
GCGGTGGCGCCGGACTGATCCACCATCCGCTGCAGCACGGCCAGCCGCATCCCATACCAATGGGCATGCACACGCCCACCTCGTATGATGGCAAC
AACAGCAACAACAGCTATCCGCAGGCGGCTGGCGGTGGGAGTGGCAGCCACACGCCGCACACCACCACCACCCAGCCCACACCCACCACCACCAC
TCCGGTCAAGGTCGAGAAGTTGCTGCAGTCGCCGATAGCTCGGCTAGAAGCGCGGAAGAAAGAGCGCCGGAAACAGCGGCCCAATTCGCTGGAGT
CCAGTGCCGAGAGCGAGGCCAGCGGCATGGACGTAGACCCCAGCAATCCTGGCCAAGTGGACGCCGTCTCCAGCACGGCCAACTTCAAGAGTCCG
TTGAGTGCCCTGGGCATGGGGGATAGCAACGATGCCAATGCCAGTGGATGCGACAAGCAGGACTACGGTCGTCGCCACCATCTTCCGCCACCCAC
ACTGAACCACCCGCCAATGACACTGCCACCACCCACAATCACAATCACACCCACCACTCACAACCATAACCACCAGAACCACAACCACAACCACT
CCAACGACAACAACTCCTCTTCCTGCTCTCTTTTCCAGTCCAAGAAGAAGCGCAAGCGGTGCGGCGAATGCGTGGGATGCCAGCGCAAGGACAAC
TGTGGGGAGTGCGCCCCCTGCCGAAACGACAAGAGCCACCAGATCTGCAAGCAGCGCCGCTGCGAGAAGCTCACCGAGAAGAAGGTGGACAAGAT
TTGA
(SEQ ID NO: 1103)

Start ATG: 1 (Reverse strand: CAT)

MASSILAQSSTGATVDSSNLGATAAAATSVEATVSSLHNTHLNQLSSLSQHYTTPYHHPHSHSHPHHHYQQHYPQQQHLQQQQQQHHAQQQHQQ
QQQQQQQQQQHWDYYARQQQQHQQQQQQQQQPAAATGNTNGNSSNNGNNGNNGNNSNPDGSNTTVPAPLGSSNNSSSNHANAASGGNSGQRHGD
ANANAISAASAAVGNPGNQQPNNSAGNANSNSNSNSNSNGSYTRPWEMESKDNGPQPPQTQPHLQLKSGFEPFSKLPSFQSQFHGFNEQLLPDGT
PMPVPIGAGVPPGSAAAVAAATGSIPPGSVGPNSVAGPVGPTAMSSLQTVAMSPASISVSSPGMMSVGSPLTQLSSLQTSITPPSAGSFPAPPPP
NAFAHHHALNPHHHHRGASGYPTPYAELPLYPGFTPLSVKKEPISGGSDFEMLLKKEDFDLSNSGGAGLIHHPLQHGQPHPIPMGMHTPTSYDGN
NSNNSYPQAAGGGSGSHTPHTTTTQPTPTTTTPVKVEKLLQSPIARLEARKKERRKQRPNSLESSAESEASGMDVDPSNPGQVDAVSSTANFKSP
LSALGMGDSNDANASGCDKQDYGRRHHLPPPTLNHPPMTLPPPTITITPTTHNHNHQNHNHNHSNDNNSSSCSLFQSKKKRKRCGECVGCQRKDN
CGECAPCRNDKSHQICKQRRCEKLTEKKVDKI*
(SEQ ID NO: 1104)

Celera Sequence No. : 142000013384445

FIGURE SHEET 595

ATAACAAGGAAATGTAACGGTGATTTACGCAATGAAAGACCAAGAGAGTGGGCAAGGGAAAGAGATAGACAGGGCAACTCACAGTCCAAGTGCTT
CTTCTTCGGGCCAATGCATTCCTCCGTGGTGGCCTTGCAAACGGACTTGGCGAGTCCTTGGCCCGCAAGGCTGTGACGGGCGGCCAGCAGCCTGT
CGTTGATCGTTTGCCCTGCCATGGTCATGATGAAGCTGTTGCTGTTGTTGTTTCTGCTGCCGCTCGCTGGTTTTTATTTACTTGATTAATTTAAT
TATGCACCAAAGGAGCTGACCACACCGACACACACACACACTCGAAAGCAGATACAGAGAGAGGGAGAGAGAGACACACACACACGCGTATGG
GGCGAGCGAGAGACAGAGAGGTATTGATTGATTGAGAATATTTCGAACGGGAAAACTCTGCTATGCGAGCCTCACGATTAAACTAACAGTAAAGA
TTTAGTGGTTCCTACGTCACAATCACTACACAATTTATCGCCGCGGTTTATGCGCTCTCTAACCGGTGCCTAACGCTGAAACGCGATTTTTTAAT
TCTCTATTTTTCCTCTGCCACAAATCGATAATGGCGACTGGCAAATGGAGCGAGCGTATGAGCAATGTCCTAAAGCGTCCACAAAGTGGAGCTAA
CGCGTGCAATCGACTTGAGTTTACGGCGTTAGGTGGGAAAATATCGATTGCCATAACGTAAGCGAATACGAAATAGCTGAACTTAGCTTTTACGA
TGTGTTCATATAAGTTCTGAAAATAAAAAAAAAATAATGATAAATAAATAAATAAAAATATAAAATATTAAGATACTATAAATAAATCTTTTTTA
TAACTTAGCACTTAAAATTCCCCAACAGCAGTTAAAAAGTAGCTAGATTTGTCGGAAGTGTAGCCAAACGTAACGTAAGCTAAGGGGCTGTCAAC
AGGAATTTTTAGTTTCGAGTAGGCGGTCATACTGGTCATTAAAATAAATAAAATTATACTAAAAAACAGTAGTTAGCACAATCAACAGTCTCGTA
ATAAAATTGTAAGATGTTGAATGGACAGATTGCACACAGTTATTTGGAGAACTCGTGCACGCTGATCATACCCCGCCCGCCTGTCCTGAATCAGT
CCTCAAAGTCGGCCCAGCCAGCAGCAGCTGCTGCTGCTTCTTCTTCCGCTGGTGAGGAGTTTGGTCAGGAAGCGGGGTCGGGGTTGGCGGAAGCG
GAGGCGTTGCATGTGGATCGCATAAGAAACTGCGATATATTCGTTGACGCGCACGATCTTTATTTCTACGCAGATGTTAAGCTGTACAAGTGAGT
CACATCCGGCAATCTGTCGTGCCCATGGTGGGCCATGGTGGCGAAATTCCAGCGATATCATTGCGTACTTGTACTCCCTTTTCGGACAGATTCCA
CAGCCGTCGCACCTTCGACTTGCGAGAGCTGAAGACGCTGTTGATAAAGTTCAACACGACAGAGAATCACTACCAAATTTGCCTGCGCTGTCTGC
CCCTAACAGCGGGTGCCCAGGAAGGACCCGGTGGAGAAAGAGGCGGAGGCGGTGGTACGGGGGATGCAGCCAAGCAGTGGAATAGTCGCAAAGAG
TACATAGCCGCATTCCTGCACCTACCCACACTGAGTGCCAATTTGCCGGACAAGCAGCCTCTGGTGCAGGAATGGAAACTCAAACGAATCACCGA
TCAGTGCCAATTGCAGCTCGACGACCACGAGCGCACCTACAAGCTGACCAACAATTTTGGGTACGGCTATGCTAGCGAATACAGCGGACCGCTAG
ACCTGAGTGAGGTGAGTTCAATTGGTTAACCTGCTCTTCCGCGCACTAAACACAGATGTTTTCACAGTTGGACAGAGCCACGTGCCGCGTGTCGG
AGCCACATCGCATGAGCCCCATCCAAAGGCGGCAAGAGCGCGTGGTCGATGAGATGAAGCGCTTTTCCCGCGAGCAGTACAAAATAAATTTTGTG
GAGCTACAGGTTCCGTCCGGTCACCAGAATCCTTTACGCTACAAACCGAAAATCTACGAGACTTCCATGACCCAGGAGCAAGCGCATCTGCTGCA
CAACATCAGCCGAATGCAGACACGGGAGCAGCAGCCGTGCGACGTTTTTCGGCAAAACGAGATCGATTGCGGGCTGATAAGCATTCTGTTGGCCA
TATGCTATGATGTGCGGACGACGAACAATGAGCCGACGTGTGAATCGGGCTGGACGCGAAGCATACTGTGCCCCGCTTTATTGCTACTTTGAGCAA
TTCGACAACTATCGGGACGTACTGGTTGCCTTCCTGCGGCGAATGATCACCTACCCGCTGTACCGCAATTTCGAGTTGGGCCGCCAATGTGTACG
GGATGCCATAGAAGTTTTAAAGGGCGGTCGCAACTGGTTAATTAATCAGCTGCTGCTAACGCACCAGCAGTTCGCCAGCAGTGATCCCAGTCGCG
ATAGCTTCAACAACTACTATTTGGAGGACTATATACGATATGTGACCAGCCCGAGCGCCTGCAGTGATGAGCACATGCGCCTTCTTGCCCGCAAC
CTTAAGAACGTGCTGATGGACGTAAACAAGCAACACTTGGGCCTGGGAGTGACCGAGATTGAGACTGAGCTGATCAAGGAGCTGATGCAGGAGAT
GCGCATCGATGCGGGAAGCCAGGGTTCCTCGCCGCAGCAGCAGCATGGCGATGATGACTTGGACCTTGATAACGATACTTCTGGACAGGAGGACG
AGACTACCACTGATGATGAAAGCGTCATAACTGACTCCTTCTACAGCGTGGACATGGACATGCGACTGATAGAGAACGAAATTGTATATGAGGAT
GACGAGGAGGACGAAGATGACGATGAAGATGGAGATGATGATGAAGATGGGGATGGGGATGAGGATGAGGATGAGGATGAAGACGAAGACGACAG
CAGTTCTTCCACAACCACCAGTAGCGAGGCGGAGGGAAACAGCGTCATCGAGCAGTGCAGCAACAGTGAGACAGCAGCCAGCACCACATAAATTG
CCACTTATGTCGAGTTCGGCAAGTCCTGCTCCTGCCTTGCCCAAAACAAACAAGCAACACAACCAACTTAATGTCAAAGAACGGAGGCTAAACAG
TGATTACTTTTAAAATTAAAACAAAGTAAAATACGAAACTAAAAACCAAGCCAAGTAAATGATGTAAGTTTACACAAGAATACCCAAAAAAGAAG
AACTTCTTATATCTTAATTGTACAATAATTTAACGAAAAGCAAACTCAAAGATTTGTTCACGCCAAATGCGAAAAGATATTTGAATATTTTTTCC
CCTTTGCTCTACAATTACTTCGATTATAATTACACATACAAGTAAATCAGAACTTTAGCATTTAGTATGGCATTAGAGTATGAAACATTTGAATT
TTGAATTCTGAAAAGCGAAATCTAGTTGTGCATTTGTATATACATCTATCGATATTGTTGGTGCTGCAAGCAAAGAAAACAAAATATGAATAAAA
TAAAATGGAAATGGAAAACAACCTCCAAACTTATCTACACAGTGGGCAAAAGTCATTAATGATTTACATGTTAATGTTGTATGAGTGTCTTATAA
AAAGAAAGACATGAAGTATGAACGAAAATTCTAATAAAATGGATAATACATATTTTTTTAAAAACATCGCGACATGAGTTCTTTATTATTTTATT
CTTCGTATCAACCAAGCTGTCGTTTAAAAAAGTGACAAATAGGTAGGTAAGCTTTTTGAAGGAGAAGTTATTTTTCATTTTACTTACAAACATTT
AAGTATCAGTATTTAAAATGCATATAAAACATACTGTTACTTTTAGTACGCTTAAATCAGAAGATCAGATACTTTGTATCTTCAACACAATTTTG
ATGGTTCAATCCGATAAGAAAAACATTTGCTTGGGTTTTATTATCTTTTCTTTATTTATCCATACTCACATACATACATATATGCATATCTATGT
ACGTTTTAAAAGCTAATTTAAATATTTATGGACTGTTAATTGAAGA
(SEQ ID NO: 1105)

Exon: 1001..1324
Exon: 1420..1816
Exon: 1873..3036
Start ATG: 1059

Transcript No. : CT28305
AAATTATACTAAAAAACAGTAGTTAGCACAATCAACAGTCTCGTAATAAAATTGTAAGATGTTGAATGGACAGATTGCACACAGTTATTTGGAGA
ACTCGTGCACGCTGATCATACCCCGCCCGCCTGTCCTGAATCAGTCCTCAAAGTCGGCCCAGCCAGCAGCAGCTGCTGCTGCTTCTTCTTCCGCT
GGTGAGGAGTTTGGTCAGGAAGCGGGGTCGGGGTTGGCGGAAGCGGAGGCGTTGCATGTGGATCGCATAAGAAACTGCGATATATTCGTTGACGC
GCACGATCTTTATTTCTACGCAGATGTTAAGCTGTACAAATTCCACAGCCGTCGCACCTTCGACTTGCGAGAGCTGAAGACGCTGTTGATAAAGT
TCAACACGACAGAGAATCACTACCAAATTTGCCTGCGCTGTCTGCCCCTAACAGCGGGTGCCCAGGAAGGACCCGGTGGAGAAAGAGGCGGAGGC
GGTGGTACGGGGGATGCAGCCAAGCAGTGGAATAGTCGCAAAGAGTACATAGCCGCATTCCTGCACCTACCCACACTGAGTGCCAATTTGCCGGA
CAAGCAGCCTCTGGTGCAGGAATGGAAACTCAAACGAATCACCGATCAGTGCCAATTGCAGCTCGACGACCACGAGCGCACCTACAAGCTGACCA
ACAATTTTGGGTACGGCTATGCTAGCGAATACAGCGGACCGCTAGACCTGAGTGAGTTGGACAGAGCCACGTGCCGCGTGTCGGAGCCACATCGC
ATGAGCCCCATCCAAAGGCGGCAAGAGCGCGTGGTCGATGAGATGAAGCGCTTTTCCCGCGAGCAGTACAAAATAAATTTTGTGGAGCTACAGGT
TCCGTCCGGTCACCAGAATCCTTTACGCTACAAACCGAAAATCTACGAGACTTCCATGACCCAGGAGCAAGCGCATCTGCTGCACAACATCAGCC
GAATGCAGACACGGGAGCAGCAGCCGTGCGACGTTTTTCGGCAAAACGAGATCGATTGCGGGCTGATAAGCATTCTGTTGGCCATATGCTATGAT
GTGCGGACGACGAACAATGAGCCGACGTGTGAATCGGGCTGGACGCGAAGCATACTGTGCCCCGCTTTATTGCTACTTTGAGCAATTCGACAACTA
TCGGGACGTACTGGTTGCCTTCCTGCGGCGAATGATCACCTACCCGCTGTACCGCAATTTCGAGTTGGGCCGCCAATGTGTACGGGATGCCATAG
AAGTTTTAAAGGGCGGTCGCAACTGGTTAATTAATCAGCTGCTGCTAACGCACCAGCAGTTCGCCAGCAGTGATCCCAGTCGCGATAGCTTCAAC
AACTACTATTTGGAGGACTATATACGATATGTGACCAGCCCGAGCGCCTGCAGTGATGAGCACATGCGCCTTCTTGCCCGCAACCTTAAGAACGT
GCTGATGGACGTAAACAAGCAACACTTGGGCCTGGGAGTGACCGAGATTGAGACTGAGCTGATCAAGGAGCTGATGCAGGAGATGCGCATCGATG
CGGGAAGCCAGGGTTCCTCGCCGCAGCAGCAGCATGGCGATGATGACTTGGACCTTGATAACGATACTTCTGGACAGGAGGACGAGACTACCACT
GATGATGAAAGCGTCATAACTGACTCCTTCTACAGCGTGGACATGGACATGCGACTGATAGAGAACGAAATTGTATATGAGGATGACGAGGAGGA
CGAAGATGACGATGAAGATGGAGATGATGATGAAGATGGGGATGGGGATGAGGATGAGGATGAGGATGAAGACGAAGACGACAGCAGTTCTTCCA
CAACCACCAGTAGCGAGGCGGAGGGAAACAGCGTCATCGAGCAGTGCAGCAACAGTGAGACAGCAGCCAGCACCACATAA (SEQ ID NO: 1106)

Start ATG: 59

MLNGQIAHSYLENSCTLIIPRPPVLNQSSKSAQPAAAAAASSSAGEEFGQEAGSGLAEAEALHVDRIRNCDIFVDAHDLYFYADVKLYKFHSRRT
FDLRELKTLLIKFNTTENHYQICLRCLPLTAGAQEGPGGERGGGGTGDAAKQWNSRKEYIAAFLHLPTLSANLPDKQPLVQEWKLKRITDQCQL
QLDDHERTYKLTNNFGYGYASEYSGPLDLSELDRATCRVSEPHRMSPIQRRQERVVDEMKRFSREQYKINFVELQVPSGHQNPLRYKPKIYETSM
TQEQAHLLHNISRMQTREQQPCDVFRQNEIDCGLISILLAICYDVRTTNNEPTCESGWTRSILCPLYCYFEQFDNYRDVLVAFLRRMITYPLYRN
FELGRQCVRDAIEVLKGGRNWLINQLLLTHQQFASSDPSRDSFNNYYLEDYIRYVTSPSACSDEHMRLLARNLKNVLMDVNKQHLGLGVTEIETE
LIKELMQEMRIDAGSQGSSPQQQHGDDDLDLDNDTSGQEDETTTDDESVITDSFYSVDMDMRLIENEIVYEDDEEDEDDDEDGDDDEDGDGDEDE
DEDEDEDDSSSSTTTSSEAEGNSVIEQCSNSETAASTT*
(SEQ ID NO: 1107)

Classification: hypothetical

Celera Sequence No. : 142000013384416
GTGGGCAGCGATCTGCAGGTGAAGCTGTGGGACTACAACAGTGGTGCTGTGGTGGGCATCGGATCGGAGCACGCCTCCTCCGTGATCAGTTGTGC
GTACAGTCCCTGCATGACCATGTTTGTCACCGGCAGCACGGACGGATCGCTGATCATATGGGATGTGCCGCGTGACTTCTGGGGCAGGCCCAATC
CGCCGGATGTCACCAAGTATTCGCTACCAAAGACATCGTCCAAAACCAGGATGAGTGACGTGCCGTCGCGGGTGAACTCGGGCACCAATCTAAAG
ACGACCAAGGGCGAGAACATCGATGGCCTGCTGAAGGCCACTCCCAAGGACGATCTCTGCTGCGTGGAGTGCCCGCCGTGCGCCAAAAAGGATAC
CAAGGGCGTGGATCCCTATGCCGAGTGCGGAATCGTTCCCGATGTCCGCAAGTGCTGAGATTTTCCTTTCCAATTTCTTTTTGTCGTGAAATAAA
GGCAGTTGTCCTTTCTAAGCTTGATTTAACTGAGATTATTTATGGGAGCTTGATTTTCTAGGATAGATTGGCCTTCTCTTTTATAAATCGTATTG
TAAGTCATAAGGAGATATGGCTTTGAATAATAGTCTTATTAGATTAAATTGATTGATTGCTGAAGGAAACCAATTTCAAATTCAATTTAATTTGA
TCAAATGAGTATTTGGTCACACTTAACAACTGTGTTGCATCAAACATGTTCGTCGAACCAATTTTCAAACATGAAAATGAGCAAGCAAAATATTT
TAAACTTAAAATTAAGTCTCAATGAAACAAAGAATATGGTAGTTCATATGTTTATGAACTATTAATTTGTTTAGAAACGAAAGTTTTATATTTTA
GATTCACAGTATGACCCTGCTGGCGTGTGGTGTAACGGGCGGCTCGCCCCGCGGTCACACTGAATTACTATTGGCCAGCCTTGTTGTTGTTGTTT
TTCGTGTTCGTAAACTAAGAGTTCGTGTGCATGGATTTTTAGCCGCATTGGTAGTAGTTACTGTCGCTCCGCCGCCGCGTGAAGTCAGATTTCTC
CGAGCGCTCAAACGAACAGCACGCGACATTCGCCGGAAAAAAAAACGAGAACCATAAGTTGTGGGAAATTCGCACAAGGGACAGAAGGAAGAAGA
AGCAGCAGCAGACGAAAGGGACGAACGGCGAAGCAAAACAAATCGAGCGACGAATAGCGGTGTGCAACGAAATGAAGGTCTGCTGCATTGGCGCT
GGTTATGTCGGCGGTCCGACCTGCGCGGTTATGGCGCTCAAATGCCCCGATATCGTGATAACTCTGGTGGACAAGAGCTCCGAGCGGATTGCCCA
GTGGAATTCGGATAAGTTGCCCATTTACGAGGTACGTTCGCTTTCCTCCTTCTCATCGTTTGTATGTACATAGGAAGTGCCACTGTTCTGTGTGT
GTGTGTGCTAGAGAGAGAGAGAGAGAGAGCGAGAGGGCACGATAGGTAGTGTGTGTGTGTGTGTGCTCACGCCTTAGCCTTGCAATTTGTGTTTT
TTTCTGCTTTTCGGGGCTTCCACTAATCATAAACAAACAAGTCATCATCCCTCAATCAATTCCCGATCCGAACCATCGAGCACAAACTAAAACGT
CGATGACCGCTCATATCCAAGTCGGTGAATACCCCACACCTCCCTCCACACTCCCCTTAAGTAAACCAGTTCCCTGCACACAGAAAATGCCAGAT
CTATTTGGAGATTTCTTGAATAATTCCATCCTATGAGATGGATTACATGGTTTATAGATATACTTAGCATTTATTTTGTAACACATTGAAATACT
ATTTGTAATTTAGCCATAAATAAGTTTGCTGCTATCCTGCTTGTTTTACTAGTAATCATTTGATATTTAGCCAGACCTACAAAACTCCATTGAGT
TTTCGCGCAGTGTAGTCCGTCTTCACTTGAACAACGCTGCGTGTCCGGCATTCTACTAAACTTCAGGTGCTTAACGCACTTGGCCCACAACAAGG
TCAATGGTCAGTCCATTAGTCACTCAAAATAAACCATGAAAAGCGCGCAGAGCCGTTTGATTGCTGAAATATGATTCGGAACGGAAAAGTAGCGT
GGGAATCGATTTTACTTTCCAGACTGCGTGACCATCGGCGTCGCTCCATTAGGCCTAAAATTCCAGATACTACAAAATGCGCCAAACGAAGCCAT
AAGGTGCAAGCGGATTGCCTCCCATCCACCACACCACTGGCGCATTTCCGTCCTGGCTTCCGTCCGCCCTCATTTCCCACTGTACATATGTCGAG
CTACCCACTCTTCTTATCGGCTCTGCGCCAAAACAAAGTCTCGGGTCGAGATAAGCTCGCTGGGCATGGCGTTTCTTTTCTTATATTTTTTTTT
TTGGTCTAGCGAGCGCACATTAGTTGGAAATTGTCCAATTACCCACGTTCCCGACAAACAGCCAGTATCTCTGGTGAAAAAAAGCACGAATAGAA
GTATGTACAATCAGCCAAACACTCAGTATATATGTTTTGTTTTCAATTAGACAATAATTTGGTATTTGTATCCTATAGCAGTAGTAACCATTATC
AGTTAAAAACCCATACATTTTGGAAGATGGTATAGGGCATATATTTAGTTCATTCTTATCGCCCTCCTATTGTATCCCTAAAAATAGTTAAAAAC
CCATTAAGAAAATACACTATTGACTGCAGTCTAGACCGTAAATGTTCTTACCTAGACCGAGTAATTCAAAAATATACTTTTCAAGATAAATTCCA
CTTAATGAAGTTCGATTGTAATCAATACCAATGTTATGTACGCAAAAAAAAAAAAAGATGCTGTTGGGTGCACTTGTAACCATTAGAGGAGGCTG
TCTAGCCAGTTTGCCATTATCGCTACTCACCAAGATTGCAGCACCACAAGCAAACAATTATGGCCAGCACTTGGAGTACTTCAATGCAATTTGCT
GGCGATGGCGATGTCAGGGCGAGCATGTCAACAACATCCTCTTGTTTATGGAATTTGCACAATTGGCGTACTTTCCATTGACACCGAAATATTGT
CAACATTTCCTAATCGTTGCACTCATTAATGTTCCATTAGCTTTTTCGCACATCGCAAAAACTTATCGGGCAAACAGTTGATATATTTTTCTGTT
TGATTTGCTTTTCTATCTAAGTTTTCAGCTAGAATTGTTTAGACTGATAGATTGTTTATCGCTTAGTCGTATCTCTCGATTGAAATGCGATGTAG
AAAGACAGTTATTAACACCTGCCCTCCATGGAGAAATTCGTATAAATACGTATGCAAATTTGGCTGGGCACGCAAAACGAGTTCAATGAACATTC
AAATCGTATCTGAAACGGAAACAAGTCTGGCTGAAACTGAATGCGTTGAATGAGAATGGTGAATGGGTGGGTGAATCAGGGGTTCGTGTGAATAC
ACGTATTGCATAAGCGGCTTGGTCATGGGATAGGGTCTTCCATAGCTTCTAAATTAATCACTAAATGCCAACAAGTGGACCACTCCAAGTGCGAT
GGCAGCACGTAAACAGAAGTAGAGCAAAGTTAATTGTGAGATAGCTTTCTTGGGAAAGCCAATCGGATAAGATCGACGTACAAAGTATATATATA
TATATATATCCATACAGAATGGTTATAATCTTATCGGACGACGAAGTGGGAACGTCACCAAGTGCTCAGCTTTGGGCGCGGGTTGTCGTGATTGG
CATTTTAAAGCACTGCAAAGCACTGACTGCAAACTAGGCCAACAACTTGTGGAATAACTTCTAAATTATATTAATGAGGCAATTTGGTTCTTCTT
TGTGGCAGCCCGGCTTGGATGAGGTGGTGAAGAAGTGCCGCAATGTGAACCTCTTCTTCTCAACGGACATCGAGACGGCCATCAAGGAGGCGGAC
CTCATCTTCATCTCGGTGAACACGCCCACAAAAACCTGCGGCAATGGCAAGGGTAAGTACTAAGTAAACAAATATAAAAAAAATAGAGAAATTAT
CATATAATATAGCATTATTCCAATTTGAAGGCTACAATCTGTTGATCATAAAGCTTCACAAGCTTGAATTATGGCTAATATCATGTCATAGCTTA
AAAATAACTGCCTATTAAAGCATAGATTTGTTAGTTAAATAGCCATAAAATAACCACAAATAGCTAAGCTAAGCTAACATAAATAATTACAGCAT
GAGTTAACACTTGAAAATATTAATTCTAAAAATAAAGAGCATAGTGCGAGTTTAATCAGAAATCGTTTGATAATCACACGCCACTAAAATCAAAT
TAATTGAAAAAGTAATTAAAGTCATCAAAATGTTGAACATTTCATGATTTCAAACACACGTTTATCATTGCTGGTGGAAAAATACTTTAAATTAG
ATCAAAAGTAAACATTGACATACTTAAGATCACTTAGTAATCCACTTTTTCAATCTGCAGGCCGAGCGGCGGACCTCAAGTACGTGGAGAGCGCA
GCGCGGATGATCGCCGAGATCGCGCAGTCCAACAAGATTGTGGTGGAGAAGAGCACGGTGCCCGTGCGGGCGGCGGAGAGCATCATGCACATACT
GCGAGCGAACCAGAAGCCGGGCATCCACTACGACATACTGTCCAATCCCGAGTTCCTCGCCGAGGGCACCGCCATCAATGACCTGCTAAATGCGG
ATCGTGTGCTGATCGGCGGCGAGGAGACGCCCGAGGGCCACCAGGCGGTGGAGAAGCTGTCGTGGATCTACGAGCACTGGATACCCAAGCAGAAC
ATACTCACGACGAACACGTGGAGCAGCGAGCTGTCTAAGCTGGCGGCCAACGCATTCCTCGCCCAGCGAATCTCCAGCATCAATTCGCTGTCGGC
AGTGTGCGAGGCCACGGGCGCAGATGTTTCCGAGGTGGCGAGGGCCGTGGGTCTAGACTCTCGCATCGGTTCCAAGTTCCTGCAGGCGTCGGTGG
GCTTCGGCGGCAGTTGCTTTCAGAAGGACATCCTCAATCTGATTTACATCTGCGAGAACCTCAATCTGCCCGAGGTGGCCGCCTACTGGCAGCAG
GTGATCGACATGAATGAGTACCAGAAGCGTCGATTCTCGCAGAAAATCATCGAGAGTCTGTTCAACACGGTGTCGGACAAGCGGATAGCGATCCT

FIGURE SHEET 597

GGGCTTTGCCTTCAAGAAGAATACGGGCGATACGCGCGAAACAGCCGCCATTACCGTGTGCCAAACTCTGCTGGAGGAGGGCGCCGCGCTGGATA
TCTACGATCCGAAGGTGGAACCCGAGCAGATCATCGATGACCTCACGCATCCCAGTGTCACGGAATCGCCGGAGAAGGTGAAGAAGGCGGTGCAG
ATCCACAGTGATCCGTACAGCGCAGTGCGTGCCACACATGCGTTGGTCATCTGCACGGAGTGGGATGAGTTTGTTGATCTGGACTTTAAGCGCAT
ATACCAATCGATGATGAAGCCAGCCTACATCTTCGACGGCCGCAAGATTCTCGACCACGAGCGCCTGCAGCAGATCGGCTTCCACGTCCAGACCA
TCGGCAAGAAGTACCAGCGCACCGGACTGCTCCGCTCGTGGGGCATTGTGCCGCAGCTTTAGGCGCGTCGGGCGGCGGAGGTGGTGGCATTTACA
CTTAAAGTTGGCGAAATTTCCAGTATTTGCGAGACTAAACTGTAAATATCCGTATTCTTTTCTGTAGCTGAGTGTATGTTAGATTGGGTCGATTA
AGCTTAAGTTGAATCATGTTTAGGAGAATAGAATCGTTTCAAATCATCAGAGGACTCTGTCAGTTTTAAGTGAAAAGTAAAGTTGAATTCTTGCA
TTTTGTATATTAGTTTCTAAAGGATATAAGCTTTTAAAACATTTCTGTATATAACTAGAAAGCGAATTACTTATTTGAACAACATAAGGCAATGA
TTGATTAACCACAAAGTTATAAAACGTAGTAACTATTTTTGATCAGACAATATAATATTATGTAGCTTTCCCCATATCGACCCAAACTAACGAGT
GTGTTTCTAAATAGTTAAAGTATTCAACTAGGCACACCCGCAAGGGAAACCCTCGAACCGTATTTGTATTCATATTCCTATTCCTATTCCCCTGT
CGATCCGCCACTCGAGGATCGGTAGTTGCAATATTAAGTCCCAGCAGGACAATAATCCCCTCCTGCGGCGGGCCAATAAAAACCAGCATTTACAC
GAGAGCATGTAAATTTTTATAATAAAAATAACAACAGTGCGTTTGATTTGGGTTCCCTTTTTCAGAAGGGTATCCTCTTGACTATTTGGCGGTAC
CACAAAAAGGAGGTGGCCGCCGATAGACTGAACCAGGTCACCAGGTACGACAGATGATCGTTGCGCAGGGTAACGCGTGTCTGTCCACCGATTGG
AGCATGTGCAGCCGTTTGCGGATCGTAGACGGCGTCCAGGAACACAGGAGCTGCTCCTGTGGCGGCGCACATGCGCGCCAAGTCGCGATAGAGAT
AGACATTGCCCTTGTGGTCGGGTGTGAACTGCGGACGCGCCTCTCCTTTGCGCACGACGGCGGTGAGCTCCACTTCCGCCTGTTGTTGGCCCAGC
GGCCTGGTTTCCGGCTCCACTTGCTTGCGGGACACCCAGCCCCGATTGACGAGCACTATGTCGCTGGGGGCGAAACGATATTAAGATGATTCTAT
GGGATTTCCTTGAGCACAACTTACTCTCTATCTGCCAGCTGAAAAGGGGTTACTATTAGATAGCCATTGCCCGAGTCGCGCTGCGAGAAGAGTCC
TCCTTGGGTTTCCACGCCATCGGGCCGTATCAGCGATCTCGGACCCAGGCGCATCTCCTTGTCGTGAAGGAAACGTCCACGGATCTTGACCAGGC
GGTACTCCATTTGGGCCAAGTCAGTGAGACTACAGGAGGGAATACACTATAGTGGGTGGGTATATAGTGGAGAATATGTGGGCAAACCTACTCGT
CTGGTAGAGCCACAGGCGCCGTGCTCAGCTGCTTGTTGAGATCCTTGATCAACTGCTCCTTCCAAATCTTGCGCTTCACTTGCCAGCAGCCCAAG
CCAAAAGTGGTGGCCGGTATGAGCTGGGGATTGGTTAATGGACAACAAGGATTAGTTGTGTGTATAGGTAGAGGAGTTGGTGTCTACCCACCAGG
AGGAACCATCCCAAAGGAGCTATCTTCTCCTTGTCCTTCGCCGCCTGATTGGGAATACTGGTTGTCCAATTCACCGGCGGTCGCTGTTGTGTCAT
CTTTCTGGTGATTAATCTCGGATTGTTCGCGGTGCCCGGGTTTCGGAATACAGTCTGTATATTAAAGGCCACTTGCCGGCACATTTGGTTCCCCA
AACGTATCATACTTTCTTTTATTTTGCTCTAAATTTTCTATTTATTTATTTATTTACATTTCCAACTGGAAGTTGATAGTAAGACCGTTTTGCAC
TGTTATGAACGGATAATAACTTCATGCGGTCACACCACTTCCGAATGTAAGCTCTTCTTGATTTTATGAATTAAGACTGCAAAGGTTTAAAGTAT
ATAAAAAATAAAGTAATAGTTATTACTTTTCACATGCAAAAAAAAAAACATTTTTCTTTCTTTACAAAGATTTGTATCTGTTACTGTTAATCATA
TGTTAGCAAGTCACTGTTAACATGTCGTTATACCCAAGTTGGCAGCCCCGTTACGATCAGCTGTTTTAGTCTGTTGTCGCGTGCAATTGGATTTT
TTAAACGATTTTGTTTTAGTAAATTTAGGATACATTTAAGAATGCAGTGCACTCGTGCAGTTGCAAGACTGGCCGGCGGCCTAGCGAGAACCGCA
TGGGTATGTTTAAAGCAGGGGTTGTACTTTATTTAGTCAAAACACGGTCATCCGAATGCACCGCCATCAACTCTTATATAAACGGATATAAAATT
TTTAAATTAAACATATTATAGGCAACACAACATACGTATAAGCACAGGCCAGCGATACTGGGACTGCTGGAGCAGCCATGCCGCTTGTGTTCATC
CACCGGCGTTGTGGATAATACCAATAAAACGAAACCCGGCACAGCGGAAGCCGCAGAAGGCGGTATTCTGAAGAGAGTGCTCAACAAAGTGGGCT
TCACACCGAACACAAAGGCGGTAGGACTCGGATTACTTTGCCCATTTGATTAATATTCATCGAAGTGATCCCATTTCAGCGCCTCAAGGTAACCA
GTCATCTGCTGTACGAAAGCGTCGCCGACAAGATCAACTATGTGACCTTTTTCCGCGACTTCAATCTGCCCAATACCTTTAACTCCTGGTTCTTG
GTCACCGAACTGCATGTTTGGCTACTCCTGATGCGCTCCATGGCCGAGGGCTCCGAAACGGGCGAGGATGGACGCTTCCTGCGCAACTGCATTGT
GGAGGCGATGTGGGGAGATGTTAACACACGCGCCAAGAAATTGGAGTAGGTTTTACTTTAGTTCACCTTTATATATATAATCTTTATGCTCTTC
ATATGTGTTTCCCAACAGGCTCACAATCCTTCACGCACCCGTCAGCAAATCGAGACCTTATCCGAGCAGTTCCAAGCGGCCCTAATCGCCTACGA
CG
(SEQ ID NO: 1108)

Exon: 1001..1361
Exon: 3809..3947
Exon: 4431..6194
Exon: 7542..7552
Start ATG: 1212

Transcript No. : CT28337
GTAGTAGTTACTGTCGCTCCGCCGCCGCGTGAAGTCAGATTTCTCCGAGCGCTCAAACGAACAGCACGCGACATTCGCCGGAAAAAAAAACGAGA
ACCATAAGTTGTGGGAAATTCGCACAAGGGACAGAAGGAAGAAGAAGCAGCAGCAGACGAAAGGGACGAACGGCGAAGCAAAACAAATCGAGCGA
CGAATAGCGGTGTGCAACGAAATGAAGGTCTGCTGCATTGGCGCTGGTTATGTCGGCGGTCCGACCTGCGCGGTTATGGCGCTCAAATGCCCCGA
TATCGTGATAACTCTGGTGGACAAGAGCTCCGAGCGGATTGCCCAGTGGAATTCGGATAAGTTGCCCATTTACGAGCCCGGCTTGGATGAGGTGG
TGAAGAAGTGCCGCAATGTGAACCTCTTCTTCTCAACGGACATCGAGACGGCCATCAAGGAGGCGGACCTCATCTTCATCTCGGTGAACACGCCC
ACAAAAACCTGCGGCAATGGCAAGGGCCGAGCGGCGGACCTCAAGTACGTGGAGAGCGCAGCGCGGATGATCGCCGAGATCGCGCAGTCCAACAA
GATTGTGGTGGAGAAGAGCACGGTGCCCGTGCGGGCGGCGGAGAGCATCATGCACATACTGCGAGCGAACCAGAAGCCGGGCATCCACTACGACA
TACTGTCCAATCCCGAGTTCCTCGCCGAGGGCACCGCCATCAATGACCTGCTAAATGCGGATCGTGTGCTGATCGGCGGCGAGGAGACGCCCGAG
GGCCACCAGGCGGTGGAGAAGCTGTCGTGGATCTACGAGCACTGGATACCCAAGCAGAACATACTCACGACGAACACGTGGAGCAGCGAGCTGTC
TAAGCTGGCGGCCAACGCATTCCTCGCCCAGCGAATCTCCAGCATCAATTCGCTGTCGGCAGTGTGCGAGGCCACGGGCGCAGATGTTTCCGAGG
TGGCGAGGGCCGTGGGTCTAGACTCTCGCATCGGTTCCAAGTTCCTGCAGGCGTCGGTGGGCTTCGGCGGCAGTTGCTTTCAGAAGGACATCCTC
AATCTGATTTACATCTGCGAGAACCTCAATCTGCCCGAGGTGGCCGCCTACTGGCAGCAGGTGATCGACATGAATGAGTACCAGAAGCGTCGATT
CTCGCAGAAAATCATCGAGAGTCTGTTCAACACGGTGTCGGACAAGCGGATAGCGATCCTGGGCTTTGCCTTCAAGAAGAATACGGGCGATACGC
GCGAAACAGCCGCCATTACCGTGTGCCAAACTCTGCTGGAGGAGGGCGCCGCGCTGGATATCTACGATCCGAAGGTGGAACCCGAGCAGATCATC
GATGACCTCACGCATCCCAGTGTCACGGAATCGCCGGAGAAGGTGAAGAAGGCGGTGCAGATCCACAGTGATCCGTACAGCGCAGTGCGTGCCAC
ACATGCGTTGGTCATCTGCACGGAGTGGGATGAGTTTGTTGATCTGGACTTTAAGCGCATATACCAATCGATGATGAAGCCAGCCTACATCTTCG
ACGGCCGCAAGATTCTCGACCACGAGCGCCTGCAGCAGATCGGCTTCCACGTCCAGACCATCGGCAAGAAGTACCAGCGCACCGGACTGCTCCGC
TCGTGGGGCATTGTGCCGCAGCTTTAGGCGCGTCGGGCGGCGGAGGTGGTGGCATTTACACTTAAAGTTGGCGAAATTTCCAGTATTTGCGAGAC
TAAACTGTAAATATCCGTATTCTTTTCTGTAGCTGAGTGTATGTTAGATTGGGTCGATTAAGCTTAAGTTGAATCATGTTTAGGAGAATAGAATC
GTTTCAAATCATCAGAGGACTCTGTCAGTTTTAAGTGAAAAGTAAAGTTGAATTCTTGCATTTTGTATATTAGTTTCTAAAGGATATAAGCTTTT
AAAACATTTCTGTATATAACTAGAAAGCGAATTACTTATTTGAACAACATAAGGCAATGATTGATTAACCACAAAGTTATAAAACGTAGTAACTA
TTTTTGATCAGACAATATAATATTATGTAGCTTTCCCCATATCGACCCAAACTAACGAGTGTGTTTCTAAATAGTTAAAGTATTCAACTAGGCAC
ACCCGCAAGGGAAACCCTCGAACCGTATTTGTATTCATATTCCTATTCCTATTCCCCTGTCGATCCGCCACTCGAGGATCGGTAGTTGCAATATT
AAGTCCCAGCAGGACAATAATCCCCTCCTGCGGCGGGCCAATAAAAACCAGCATTTACACGAGAGCATGTAAATTTTTACAAAAAAAAAA
(SEQ ID NO: 1109)

FIGURE SHEET 598

Start ATG: 212

MKVCCIGAGYVGGPTCAVMALKCPDIVITLVDKSSERIAQWNSDKLPIYEPGLDEVVKKCRNVNLFFSTDIETAIKEADLIFISVNTPTKTCGNG
KGRAADLKYVESAARMIAEIAQSNKIVVEKSTVPVRAAESIMHILRANQKPGIHYDILSNPEFLAEGTAINDLLNADRVLIGGEETPEGHQAVEK
LSWIYEHWIPKQNILTTNTWSSELSKLAANAFLAQRISSINSLSAVCEATGADVSEVARAVGLDSRIGSKFLQASVGFGGSCFQKDILNLIYICE
NLNLPEVAAYWQQVIDMNEYQKRRFSQKIIESLFNTVSDKRIAILGFAFKKNTGDTRETAAITVCQTLLEEGAALDIYDPKVEPEQIIDDLTHPS
VTESPEKVKKAVQIHSDPYSAVRATHALVICTEWDEFVDLDFKRIYQSMMKPAYIFDGRKILDHERLQQIGFHVQTIGKKYQRTGLLRSWGIVPQ
L*
(SEQ ID NO: 1110)

Name: UDP-GLUCOSE 6-DEHYDROGENASE
Classification: enzyme
Gene Symbol: sgl
FlyBase ID: FBgn0010851

Celera Sequence No. : 142000013384672
GAATTTTTAAAAATTATTTTATTTTATCATATTGCTACGAAATTGGCAAAAACTACCCTAATATGTACTATGTAAATTCATTTCTTCGATCAGAA
TTGATTTCGGCCCGAAAATCGTCTTCTAGCACAACACGCACACATATACAGAGTTCTCGACTCTTGTTTTTACTCACACAAGCAAGCAAATTAAA
TTTTTAGATTTCTTACGCTCTCAGCGGGAGTGAGCGGAAAGAGAGCAATTTTGGCCGTCGCTAAAAAATTGGCTGCATAGTGCCAAACCAATGTA
TGGCCGTTACGCATCTTGTTATTCTAGTGTCTTTGGTCTAATCCTCCAAATAGATTTCTTTCTCTCCAGGGTTTTTAGCTGTATATGGATTTAC
CTCTCTGTATAAGAGAAGATTGAAGCTGAAGGAATTCGAAACCATTACCAAAATGAAACAATTGAAGACATAAATTGGACGCTTTTGTGATGCGT
CTTGCCTGTGTCACAGCTGAAGCTGATGGCATTCTTTATGTATTTTATAATATATATAATGTATATGTATACTAGATTATTCATTGTATAAACTA
ACAACATCATCAGTATCAGTATCAGTTAGTTAACTCAATGTGCAACAGCCGATGATAGGCGTACACTCGTCGAACGAAGAAAATACACATTTCCA
ATCGAAGATCATCCGAAAAAATGAAAGAAAACTTATAGGCGATGTATAATTAAAGAAATTGCAAACTGTCTGCTTAATTGGTACTTGGTAGTTTG
TAGGTGGTGCGTATGTGGTGTTCATGTGTTTCATGTGTTATATGAAGGACATGTGGGTATTTGTGGGTGTCTGTGGAAGGCGCTTCGTGTATCCT
TGTTTCGTTGAGCAACTAATTTAGTTCAAATAGCGAAAACAATTTTGAAGGCGGCGGCTAGGCGACAGGCAAACAAATTATGCAGATTGCGAGCT
GATATATTTATGTGTACGTAGTGGTGACTCCAAAATCCCTGCCAGCTTAGCTAGCCCTCGATCTGAGATCGCAGGCGGGGCCGTGGCAAGTCCCC
AAAAACAGCCTCGCCATGGACACTTCTGGTCAGCGCTTGGATGCTTGCCGCTATGTCGATGTTGTCCATTCCCTGACAAAAAAGAAATCAGCCAT
TAGTTTCGTATGTTTTTTTTTTACTGTTAAATACTGATCTCACCTCCTCGCAGCCCTGCCCGAAGTTATTGTTGTTGGCCACAGCAGCTCTCTC
GGCCAGCGTGGTGTTTGCTATCTCGATGGCAGACTCCGGGCGAAGTTCATCAACTGCGCATGGCTAGGACGCCCTCCGCCTCGCACTGGTATGG
AAATGGAGCTATCCGGGTCCAGAGCATCTGTAAGTTGGAAACATATTGGGGGTAAATAAAAATGCTAGTGACGTACAATTTTCTAGAACTCACCT
TCAGCTTCATCCGCAGCTTCGTCATCTAGGACACTTCGTAGGCCATTTTGTTGGCTCAGCTGCTGGAAGGGATTGTGCTGAGGCTGCTGCTGGTA
GATCAGGCTACGCGTGTAGCTAGGCACAGGCACGGACTGAACCGGAACCGGAGCATCCACATCCTCCAGATCGAACAGGCAGTCATCTGCATCTT
CGTTAACACTGGACTGACCCACTCCATTTGGGGTCAACGTCTGGGTGGGTGGACCACCAGCACCGCCGGCTGCTGATTGCTGCCGGAAGGTGGGG
CTGTTGCCCACGCTCATGGGCGTGGCTTCTGGGGTGGCGGGCGGTGTGTCAAAGTGCGACATCTTCCTGGCCATCGAGACACTCTGCGGGGCCTG
CTGCTGCTGCTGCTGTTGCGCCTGCAACTGTTGCTGCTGTTGCTGCGCCAGCAACTGTTGCTGCGGCTGCTGGTTCAGCGATAGGAAGTTGGGCG
GATGTGTCAACGTAGTAGTGGGTGTGGTGGGTCCACCATTCAACTCCCGCCGGCTGCTGATGGTGTTCCTGCGCCGGGCAGTCGCACTCTGCGGC
TGATTGGCCGCCACATCAAGGGCAGGGAGCATGGCACGATCGAGTAGCTCCGAGGCCTGCTCGGGCAACGCACGAATAACTTTGAATAGCAACGC
GCAGTCCTGATCCGATTTCTCCCGGAAACTGTTTAGTAACTGGAACTGAGTGCGCGTATACCGCTCGATTCTCTCATTTGTCTCCACAATCTCCT
CCTGCAATCGCGCCTGCTGGTGCGCTTGTATCATTCTCAATCTCTGCACCCTGGCATCAGTGGGATTCGAAGACAGGGATCCGATGCTTAGACTC
GATGCGGAGTTGGATAGTCCACTGGTGGGTCGAGTGGATCCAGAGTCACTGCCTGTGTGATCCATGATCAGCAGCTCGAAGGTCTCCGAGAAGGC
TTTGTTGGACTTCCGTTGAGCCAGCTCCTCGCTGCTGGTCAACAGCGTGCAGTTGATGAGGTAGAGAGTGGGCGTGGCCCCGGCGCCCGCCGTCA
ATCGCTTGGCGCATAGCACCTCCTTGCAGTTGATGCACAGGCTCAGCTGCCAACTCTGGCCAGCGGCTTCCAGGGTGAGACCATACAACAGCTCC
CGCTGATTAATCACAGCCACGGTGAGGTCTGGAATGGGACCATAGGCCTGAAACGGCAAGAAAAAAGTTGAATATTATTGCTTGTTTAATTCTAT
TCTATTATTTAATTCCTTTATTCCTTTTTGTTAGATTTTTTATCAACCATACTACATGGTTATTGATTTGGGTATCAGGCTTTCCCTGGGTGCAA
TCCTCACATTCATATTAAATTGGATTACCTTTAGTCAACAAGTTGATAACACTTTCCACACAGTCAGTCTGGTCAATGTCTGATAAAGAGGGATT
ACCAATTCGCCCCATTATTATCTGCACTTTTGATCACAACAGAAAAGCCAGCCTTTCTTCGATGTTTACCCAGTCAACAACCCCGCCGCACAGTA
GTTCAAGTGCAAATTTGTCAATTATGTTCATTTCGAGTGGCGGCACCCGATTGTGTGAAGACTTTATCGGAAAACAAGAAACCGCTGATGAACAC
GAAAACAACAAACAATTAGTGCAATGGCAAAATGATGTTGATGATGGGTGCCATCATATAGAGCAGAAGACAACTTGAATTATTCTGGCTGTCAT
GGTGACAAACAGAAGATGTGATGGGTAAACAACAAGTTCATGATATCGCCGGAATAGATTAAAATAGTCTGGTTTCCAAATGCCAAAATAGAAAC
AAACAAGTTTGCAGTCTGCCAATGAAACCTAAATATATCTATCATCATAATGCCCCGCCAATTTAGACACATAGTTATGCAAAATAATTCCGGCA
TTTTTGGAATCGTAGCACGTGTTTGCCGACTGACACAGGAGAGAAAAACACTTTTTATAGACGTGCTTGGCTAAATTTGACACTCGCGTCCACCA
CAATCAAGTAATATTCATATAGCTTGGACAATGGAGAGCGCAGGGCGAGATGTGGAGCGGGTGGGACACTGGACACAAGTCCACACAAGTGCACA
AACAACCATTCGCACACGTAGATACACCGAATTAAATTGAATTAACGTACGAACTGCAAACGTCAACAGAAATCAAATGACAATGTTGCCCGACG
TCAGCTAAGCGCTTCTGAATCGCATAGCATCGTTTTCGTTTTCCACATAACCATCCTCATCACTTTTTGCCAGGTGGACAAGAGATCATCTCTCT
CATCTCTGATCCACATATCATTGAATAATATACTTTAATATATACTTCATATACATTCAATTAAATTCTTGAACTAAAACGAAATGTTTATCATT
CGTTCAAAAGGCTGATATTGTCATAATTTTGGCTGTCAACTCAATTTCCGGCATTTCAAAACTGCAGCTGCATTCGTTCGTCTTTATTTAGAAAT
TTGTTTTCGCATCCATTTTGGACAATAACAAGTTGCGGTCACACCCACTCAAAAAAAAAAAATTGTTTTCAATGCAAATTCCGAACTTGTTGTTT
ACAACGAGTGCGGTAATATCTAATCAGGCCCAGTCAGTCGGTGGCAATAATTATACATATGAATGAAACCGAAAAACAGGCACTAAAATGTGACA
CAGCAAATGCATTGTTGTCAAGTGTTTTGGCACTCGGCTGATATTATTGCCGGCAAACGCATAAACATATTTATGGGCTCAAGCCTATTTGCTCG
GTTTAAAATTGCAGTTTTATGGCTGTTTTCGTAACCGCAAGACCCGACTGACTGGCTGACCGACTGACTTGTTGTTCTTGCTGCTAATTTGCTGT
GCTGATACCCTGTAAGATGGGGATTTGGGCGCAATGAGTAATTATGCCTTTCTTCGATTGAGGAGCAGATAAGATAAGTGGTACGATTTTAGATT
TATGATTATATCTGCTGCGAAGGCGTAATTAAGAAATCGAGAAGTTACGAGTAAATGCCAACATATAAGTAACCCAAAAATATCTTGATCACATA
TAACCATTCCCCAAAAAATACAGCAATAAATATGGGTATTTAGAACGGAAAGTTTTCGCATCTAGGGTAACTGATAAATCGATCATTGCTGATTG
CCATCCATCATCATTCATTCAGCATTTTTTTGTTTAGCGTTATTTATGGTTTTATGGCACAAGCTGGCTAAGCTTGAAGTGGGTGTTTTTGTTGA
CTCGTTGGACGGGCCCCAAAACGCCCGACATTATCAGTTAAGATTTAAGACAAATCATCATCAGAGCCATCATACTGATTAGCTGCATTACCTCC
TATGCAGATGCAGTTTTACCCTTTGCTTGCCAAACATTTTGCATGCATTTTTCGCCCCTGCTGCGAATCGCGATCTGCCAAATGTCAATGACTCT
TCTCAGTGACTTTCAGACTGCAATGACAACAATTGAAGGCAATAGTTGCCTTCGTCGTTGTCGTCGTCGTTCTCGTCGTCGTCACTTCATTGGAT
TGCTTAATTAACCTAACTGCCTGTTCGAATGATCGACTCTTGCTTAATTGAAATTAAATGTCTGCGCGCTGTCCTGCTAATTATGTGACTGTGGC GCCACCTAGTGGCCGGAACCAGTGGCTGTTAGCTAATTAAATAACCGTTTACGTTCGACTTTGACGTATGACCATTTGCTTTATGGCCCAGGCCA
GCCAAGACGGGCATTTGATTAATTGTAATCGCGTCTTCTGGCCGAAATAATAAATAAAACATGGCGTGTTCTAACTGGTAGTGGTTGGCCGAAAG
AGATGCAAAATCGCCAAAGGAAACGCGCCGAGGAGCACGTAACTACTCAAGTCGCACGCTCTTCGCATATCGGAAATCAGTATGAAGCGATTTAA
TTGAATCGCGCGACATTTAAGTAATGTATGCAATCTAGACGGAATCAATTGCATTGGTGCCAACTGTCGAAAACGTTGTCCAACTGTCAGCTTGA
GTCCGTCGATCACTTAATATGCATAGTGGATAACTATAGAAAATCAAAATACTTTATTGCAACCAAAGACATGGTGTAATAATAAATGGATTCTA
GAACGAAGCTCAGAAACTATGGCAATTCATTAGATTAGATTTATTGATCTCTTTAATGTGTTAATGCTACGAAAGCAACTGAAACAGAATTTTAC
CTTCGTTTATATCATTATATGTTTGTATATAATTAAATAAACTGCATAATATGGCCGTAAAGTCGACTATAACTTGAGAGTTATGTATAAATCAT
GTAGCAATCTCGGACGGGAAGTACGAGTGCATTAAGATGGAGCTATCAAGTGATTCTGCTTTTCAGTTATGCTGCAAAGCAAATAATGACGTTTT
GCTATCATTGAAAAACCCTTGCGTACTTTTCAATTGCCTGTATCTATTTTATTTGGATTTTTTCTGTATTATACAAACGAGCGAGGCAATTGAAA
TTCATATCAGTGGGTAATGGTGTCTGGAAATAATGCATATTCCCTCGGCGCTGCTTATGCAACCAGAACGATTCCCATAAAACAAACAACTTTAG
AGCAAAATGTGTGTAATAATTTCTCGCATTTTGCACATTGCTGCATAATTAATTTGTTGTTGTTGTGCGAGGCGACTGTGCAGTTTAATTGATTG
AACGGCATTAATTAAGCCTGTAGTCTGTGACACTTGATGTGTCTAAATACTGGTCGCCTAACTAACTAACCACTTACTTATATTTCGATGCATAT
CAAATCGCTTTGCTATTGACTTGGCGAAAAACAAAAACATTAAGCTGTGTCCAAAGGGATAAATTAGTAGTTTGTCAGACATATTATAAAATATT
TTCACTTTCACAACGGCACAAATAAAGATGACATGCATAAAAAAGATACGAAGAGTAGCAACAAATTGTATTTTAAGCCTCTTAAATTATTCTGC
TTTTGTTATTCTCCTGTGAGATAATAATTTGCTTATCAGTTGATCTCGTATTAGTCTGATATCACACTTGAAAATCTAATAGATAACAAAAGGGA
GGGGATTGGCTGAAAATGCCGGGAGGGGGCATTAACCTGTTGCAAGTGCTGGCACCCTCGTTAATTACCAATAAATCAGATCGTCAATCATCCGT
AGCTGGCACACCTTTCGCCGAAAAAAAGATAGATTGAAAGAGAGAAAAGAAAATAACAATCAACCGCCCGATTGACGCATTTTCCTTTGTTTTGT
TTTCCATTTCTAATTCTATTTTCATTGGATTTTACTTTTTTTTATAGCTTTGAGATAACTCGCCCGTGTTGCGTTTCATCGGCAGAAACCGAAAC
TGAGCCAAAAAGAAAATAAGTTGTAAACAAATCAACTGGCAAAAGAAACTACGAAAATAATCTTTTATAGATTTGGATCCCCCTCGAAATGGGGA
TGGCAAGGAGGAGGGGTTCGCTCTGGGGTGCGACTTGGTTCGCCTCGCTGCTCGCGAATAATACAATAATATAATACCCTCTACATCTCCCTCTT
CCACTTCTTGCATTTTTTTCTTTTTTCATTTTCATTTTTTCTTTTTCGTTTTTTCTTTTTTTTTTCTTCATTTTTAGTTAGTTTTGCCTCTTTTT
TTTTTGTGTCGAAAAAAAGAGGCAAACACATTTCGCTCAGATACGTCGCCGTTCGTCGTTGGCCATTATCATAAACAACTTTAGACAGCTGGGGA
CACACGCGCTGGCTGGGCGTTTTCGCTCTGCGGATTGCGATGCCAATTTGTATTGCCGCGCTCGGTTTTTTTGTAAAAAAAAAAAAAAAAATTTCC
ACTACCAATCGGCGGGCTTGCGATTTGGCCAGTCCAGTCCATCTAGGGCTTTTGTTGTGCTCCTCCGTCCGTTTCTTGGGTTCTTTCTGGGCCGC
CAATGTGAGTCACTCGATGGCCTAAGCCCCTACATCAAAGTGCCTTTGGGTCACTTGTTGGTCGAAACTTGTTTTCCCAGCCATTTAATGGGCCT
AATATTTAGGGTTTTGGGTTCTGTTTTTTTTTTATTGGAATTAATTGTTTACCCAATTTAAAGGGCTTCGTTTTTGAATCGTAACAACGCATTTA
TAGCAGATTCTCATGAAGAGCAGCTTAGCTATACAAATTGTATTTTAAAGAATTTAAAATGCTGTTAGTCTTTCGACTAGTATTCAATCCACTTA
AGTTGTGGCTTTGTAAGCCTTAGTAAAAATTGATTATCACCCCAGCTTTTATTTAGATCGTACACGTATTACAAAATTAATTGCTGTCATGTTCA
ACTTTCTAAACCAATTTAAGCTTATTGTTTTCCAAGCCCTCCGTCCCCTGCACCCACCTCATTCGCACTTCCCTAATAAAATGTTGCCTTATCTA
CGAAAAAAAACAAAAAATAAAAGGAAAACTAGTAAAAAAAAAAGCGTATCATTCAATGTCGTTTGAAAACAAAATCTGATAACGCCCCAGACCCA
AAACATCGCATATAGTCTCGCCAGCCAAAGTGCCTACCGCACGCTCCCTCCTCCCCCTACCTCTCCACCGAGCCCTGCTCCCAAAAGATATATAT
TTCAATCGGGATTAGAATGAGGAACTGGAAAAAAGCTAGGGAAACGTGCACACGTGTGCTCCCCGCAGAAGGATTAAACTTTTTTTTTGTAAGTA
TGTAAATAAATGTGCTGAAATGAGTCGAATCTCGATTGTCTACACATGAAAATAAATTTACCTATAAAATTATTAATTATTAAATAAATAATTAT
TAAATAATATATGCTCCATAACAGTTTGTTTAAGCAACTAGACAAGAAAACATTATGTTTACTTAGCCAGTAAGTAGGTATGCTTTTATGAATAA
CATCAGATTAGATTATCAAATCAGATAACTTTTTGGTGTGACCTTACTTTACGAAAATATAAAAAAAGTTAAATGGTAAAAGCTTATTTTATTGA
AATCATAAATGCTCAGTTATTAATATATTATTAAAATCAATTATCAATAATTACGAATTTAATTTTAGGTATTTGACTTTTCAAGGCCCTTCTTT
ATATATATATTACACGGTCAAATCAACTCATCGATTTCGCTCAGTGTGTAACAGTAAATTAAGCGCAACAATGTTTGCCCATCGGCACTGCTAAA
CAGACTTCGAACAACGAAGTGTGCGAGGGGTAAAAAAGGGGTTGGGGGTTCTGGGGGGACTGCGAGGTACATAGGTGTGCCAGTGTTATCTAAAA
ACTTTGACAAACAAATTTACGTTGGCGTGGATTTTGTTTGCCCAGCGCGCACCGCACAGCCGGCTACAGCTCAAATTTAATAAGCAAACAGCAAA
GATGGCGGAATTCTCGGGCCTGCCCAACGTCTGCTGTTGTTAATTGTTAGTTTTATACACACTCACACAGCTCGTATAAATAATAATATGAATAT
ACGGCCACATATGTACATTTGTACTAGAATAATGAGATCATCTCATCTCTAGCGATCCCAAAACGCGACCTGCGCCTATTTTCGGAGCTACCGAA
TTATAGAGTTGTGATAAGACCTGCTTATTTGTGCAAACGGTCTAATTATAGCTTTTTTCCAGGCGTAATAATTACAAGACAGCCAAATATTGATA
AGACTATCAACACTAAGAAAAAATAATAATTAAACTGTTTGAAGAATACTGAAGAACACAAGATGTTGATGATCAAAAACGGACGTACTAGAATT
CATTTGTATAAGCGTTTTGAGAACAAGATTTTTGATTTCGATCTAAGAATTCTTCTACGTGCTCTACTCTTAATATCGTAAACTATTTGAATTTT
TTTTTTTTATTTTCCACTCCTATTTGCGTATCAAATTTAGACCCCTTGTTTCGTGTTTATCCGAAGTAAACAAATCTTTGTGGCCGCCGCACATT
TGACACAGTTTTCATTATTTATTTATTTCTCGCCTGGCCACTACTATTATTTCTATTTTTTCGGCTGCATTGTGTGTGTTGTTGTGCCTCAGAGC
AAATATTTATGCGAAACCATCATAATTTGGGGGAAGCGATCAAAATTAACCCCTCACCCGATAAAATCACGCATGCTAAACGTGATCGACGTGAT
CAAAAAGAAAAAAACAAAATAGAAAGAAAGAAAGAATGAAAAAATCAGAGAATCAACCCCCCGAACCCAAAATGCCACCACCCCTTTTGGCATTC
TTCAACCCTCTTGCACACGCAAAATAAATTATTCGCGTTTAGATATTTTGAAAAGAAGAGGTGTTTTCTTTGCTTTATTTTTATTTTTATTTTTA
GCCGGCTTGCGATTTCTCAATTCAAGAATTTATAGTTCTGTTTACACGAGAGCATTTTTGTACCATGTATGTATATGGCACTCAGTAGCTACATA
CATGTACATATGTATGTATTATGTACATTTTACAAGGCAAGTGAAAAAAGGTTAAGAGTTTACGAGCAAGGGCCAGGCTCATTAGATTGGCCCAA
AGATTGGTTCGCTGAAGTGTGTGGGCTTTATAACAGTACGGCAATCGACTGCCGCTGACTTCAAGGTTATATTTGTTAAAGATTAACATTGGTTT
TCAATTAACCGACACGCGCGCTGCAAGCAGCTGGTCATATGTATATGTATGTACATAAATGTATTTATTTTTCCATATGTATTTATGTGGGGTCA
AAGGGGTGGTTAACTGTGATTGACCAGCGTACTCTTCTGGGACTCTGAAGCTCTGACCTTGCCATATCATAATGGCAATCTCCTGCTTGGGATGA
TGTGTTGCTTTCCAAAGGGTCAGTAAATGAATATAAGCATAAGCAATCAGTCTAAAAGAGATAATTGAACTTGGCATATCAGGTGAAAAGTATAG
AATACAACCTCAACAATTTGCTTCCAATTTTAACTTTTTATTTTAGATGATAAGAGCCCGCCCGACTTTTTATAAAGGGCCATCTTAGAGAGTGA
TAATATAGCCCACAGTTTTGATAAGAAATTTCTTTTATAAGCAAATATAATACCTTCCAGTTTGCATTATTATTCATTTCCTAGACACATTTTAT
CATCATTGTTTTTTTTTTTTAGTTTTTTCTTTTTCGGCCCAGACAGCAATTAGGCCCTACTCGCCTGATTTTTGATAAAGTATTTGTGATTTCCC
ACTTATCATTCCACAATTCCACTTACTAGTATTGTTACACAAACCCATGCAGCAAAACCGCCTCGATTCACAGACTTTACATTTGATAATGACTA
TTTTTAGAGTACACAAACGTTGTCATTGCAGGCGCGCCTTATATTCTCAACCATATGAGGAAAATATAACTTAAACTGATTGATAACTCGTGCTT
GGGATTTGCTCTGTTGATATTTGCCTTGTGGGTAATCGGTGGATTGGAAAAGGGTTTTCGGTTTCATAACGCGATTAACTGGGATAAAAATAAAC
ATGGCCATTAGCATATGAATGCAGTTGTTTTGTTTTCTCTTGTTTTAGCTTTGTTCAACAAACTCGTTTCTCGACCCATTCAAAGATCGTGTATT
GTTTTGATTTTCAATTAACCAATTTTCACAGGTGAGAGTCCCAACAATTGAAGAAGGGCGGAGGAGATTAAAGGCTCTAATCATAAATAAACCAC
TTGGAAAGGCGAAACTGGGAGGCAGACATCGATTGACGACAGCGCGACTGGCAGCAATCGTTTTATACATATGTACTCGTATATATATACTCTAT
ACTACTATATAGAAAAGTGGCAGGGAGTATCAGTATTTGTGTCGCCGCGTTTTTACCGTTTGATAACCTAGAAAAGACGCCTAGGTAGGTGTGAG
TGTATGCAAGAGTGTATATATATATGTGTGTGTGTGGGCGCTGGACAATCAAAATTGATAAGGGGCGTGCGCACAATCACAATCACAGCTACTTT
TACTGCTGGATTAAGAGGCGATGACAAACAAACTGCAAGATACATGAATTCATTTTGTAAACAACATACATAGTCCTAATTCTAGTCCATTCGCA
CAGAAATATCCAAAAGAATGCGCAATAATTGTACATTCTTTTAGTTTACTGATTTATACAAAAAGTTCTAAAATGTTTAAACTTCATTTAATAGC
TACCATAAATAATATGAAACACATATTTAATTCGCTTTGTAGACAATTGTAGCCATATATTATTCATCACAAAATCATAAAAGCATAATTGAGTG
CTTTCAAAAACAATCATAATTACAAACAGATGTCACTTTAAGTGCGCGTTTCGAGTTAGCGAGCACTATTGTCAGTCAATTTCATTAGTGTTGCA
CAAGTCATTAGGAAGTTCGAGTTGACTAAATTCAAGCATATAGCCTTGTAATGGCCCATCACACATCTTGCCCATATGTCGTCCGGCATTTCAAC

FIGURE SHEET 600

AAATTTTATGCATAAATTCATAATTTAAACATTTCGGAGCCTACGCAGTGGAGAGCTTTTATGGCCAGGGTTGGGGTATTTTCAGTGGTGGGGAT
GATGGGGAGATGGTGGTGCTCCGACTTGTCAACTGGCCCATCAAGTGGGCCCGAAAAAGCCATTCGCCAGCAGTCCGCAAGCAGGCATTTATGCC
TTAGTGACCCCCTACCCGGCTTTCAATACATACATACATATGTATGTATGTACATAATATATGTATAGTTTTTATGGCTGCCTTTTGTACGCCTA
CACATGGCAAAACAAAGTAACATTGAAATGTTTATTAACCATGAAGAGAAACTACTAAGGCTAGAAAATGAAAATCAATTGACTAGAATAACTTA
ATCAAGAAAAGAGCGAATTTACAGGGTATAGGATAGTACAAGTTAAGTGTTGCTTATTGAACATTCCAAAAGCGGACAGAAATACACTCTACAGG
GTATGCGATAGTTCAAGTTGAGAATAGAAATAATCCGATTTTGCTTTCTTGATATGAAGTTGTTTTGATCCAAAGGTCTCCCAGCTGACCAATCC
CAAAGGATTAACAATTTATTTATCTAGCTAGCAGTATGGCACTACTGATATCGTTTGGAGTTTCTTCGAGTGAGCGCCTCTTGGAGCAACTCCCT
CTCTTTTGGGCGCCCAGTGGGCCTTTTGTAGCCCCCTTTCTTCCGCTGCCCGGCCAACTCCGTCGACTTTACGGCGGTCCAGTGCCCGGCCGGCC
GCATTTGGAAATCTCGAAAACTTGTTTATCCAACACACACACTCACACACACCCTCACACACACTCGAAAAAAAATATACTGCCAAGAGATGGGG
GAAAAAATTATAAACAAGTTTTTGTTTTGTATTTCGGCTCGACCGTTGTTGTTCTTCCTCTGCCTGTGCCTTCGCCTCTGCCCCTCGCCACGCC
CCGCTTGCCAACCCCTCGCGACCGCTCTTTGTGCTTTTTACTTCTTGCTTGTGTGTTTTGTCGCTGGTTTCGTAATTTATTCTAAAAGCGTTCCG
TTTTGGCTCTACATAGAAGTGTATACATATAAACACACGAGCCTGCATACTGATTTATACATACAGACTCATACTTGTGGCATATACATATGCTG
TGAGGGGTATTTTAATAACAGTTATACCCTCGATCGATGATATCGAAACTAATTTATCAGTTGTGTAAGATAGTTTCTTTTGATTTTAGATACCG
CTGCTCAAAAACCTATAGAGATTTTACAAGATTCAATATTTGTAATATCCTAAAAGATTTATGTTACTATTATGCTTAATTAGATATGCTTTATT
AAATTTTTAATGTCGACACTCATTTATAATACGAAAAATATATAAGAAGTGTTTGAAAGGTGAAGATAGCGTATCTGCAATTCGGTGTAGTTGCA
AATTTGGTTTACTTTGTTTTCATTTGGTTTTTTGTTTTGTTTTGTGAGCTTTGAATTATTCAAAATAACACTTTTGGTCTATTTGTCCGCGTTGC
TGTTGTTGTAGCACGCCTCAGCGCTTTTGAAGTGGGTGCAACACAACACACAAAGCAACAAAAGCAACAATAGCGGCTATAGCCGACGATCTGCC
AACCGCAAAAACAAAAACTAACAAGTCGTTGCCGTATTGGACAATTCAATTTTGCATTACAATAAATACAGCACTCGAGTTACAAACGTGCGGTG
AAGGTACTTTTGTGCAAGCACCGCGATAACCGATTTTCTAAAATATTAATGAGTCAATCTTCAATATATGTATGTATATTCAAAATGAAAAGATT
TCATTACATATATACATATATTTAAGCACTCAGGACTGCTTTAAGTTCGGAACATACATATGCAACTGGTAAAATCTAAGAAATAAAAATGATCC
TCCCGAGACCACGTCCACCCACTGGCTGTCAAACCTCGGGCCAGCAACTCCAGTGGCTGTCAAAATCTGACGAGTGGCGTGGTCGAAAGTGGGGA
TAAAACGGGGACAGAGCGAAAGAAAGGGGGGATACTGAGATTTAACCTTGAAAAGTGTGGACAAGACAAGCGGCGATGACGCAGATATTCAGTTG
TTTTTATTTTGTTAAATGGATAAGGTAGCACCAGGAACGAAAGATGGAAAAATTCGGCAAAACTTAATAATAACAACAATTACAGACATAAAAAG
TGAGGGGGAGAGGTTCCCGAAAAAAAAAACTTCGTATACAGCGCGGTCCACCAAAGTATTATTTGCCTGCAAATGTCAACTACTCAAGAACCAGT
TTACCTTCTTAATAAATACACTTATGATCCGTATTTATGCACATAATTTTAATATAAATATAATAAAAAGCAAATATTAACCATTCGATTATGAA
CTTTAATAAATTCATAATTCATAATCGAAATTTTAAATGCCAAGATAGCTACTACAAATAAACAACGTGATTATTTCCTTATATGCTATTTGTTA
GTGGCAAAAAAATGTATTTAAAATAAATAATTGCCGTGCTAACTTTTCATTCCAATCGCTTTACCAAAAACATTATTATTTGATTTATTCGCAAA
AAAAATTATTTTTTGCTGGTCTTGAGTTGATAAATTCAAGTTTGGGAATTTACCACTTGTTTATATCTTTCGACTAAGTTATGAAGAAACAAAAT
GAAAAACAACTACAATAACAATCAAGAAAATATGGGAAAGTTTTTCAAGAAATCCCCATTTTACAACAAAAGACCAGATATTAATTTGTGTATTT
AAGTAATGACTAATGACGACATCGGTGATCTATAAATTATACATACATATGTATACATACAGATACATACATACATATATAATCAGATAAAAATT
AAAAAATACATACATATGCATATATATAAATAAATATGAATGCTTGTAAGTACTACCTGTTATTTTTAATAATTAAATAATTGGTATAACAAAAT
ATTTCCAGGTGCATTTGTATAATTATTTTCTTGGTAGGGACACCCTTAAATTCTTTTACAAGAAGGACATAAATTTGCGACTTTATTAACCATTA
ACACACAACTTCCGAATTCCAGAACTGGAATATTCCACTTCGCTTAACCCCTGAATGCCAACCCCTTTGCAACTTTGTGACGTTTTTGGGAAAGC
GAAACCGAACTGAAAATTTACTAAACGAAATTATGCAAATTACTTGCAACTGAGGGTGTGACAAATGAAAAGCAAGAGCGAATAAATCATAAAAA
AACGCGAATAAAAACGGGAAAAAGAAGGCGAGTGAAACAGAAGCTGACGCAGGAAACTAAAAATACCGGCGATCAGGTTGGCAAAGAGAATACCG
AACCAGAACAGGGTGCTCCTGCTTGAAAAGGAGGAGCGAATGATAAACAGGTGCGGAACAGGAGGAGAGTGATAATGGTGGAAGAGGGGGGGAGG
GGAACGCGAAGGAGCGGGCAGACCAAAAATAAACCAGAAAATGTGAGGATTCCTCACGAGTTTCCTATGAGCAAATGGATGACCCTATTTCTTCT
TGCCCTTCCATATTCCCTACATCACTCAGTAGACCTTCTCCTTCCAATTCACGATTCCAGGCCTACATATGCACACACATATGTATGTATAGGCC
TATGTTTGTTTTGTGTGTGTGAGAATAGGCGGCACAGGCAGAAACGGCAAAAAAAATAAAGCCGGCACACAAAACATAAAGAACGATAATAAAAA
CACATAAACACACACTGACAGCGCAACAACGCAAATACAGTGAATTTCGCTTAACAATTACTTTGATTAATGCAACTAAATAGAGTGTACTGTTA
GGTTACACCAGCTCAATTAAGGGGAATAGCATATTAAGCGAAAAACTTTTAATACTTTTAAGCTATAATATATGCTTTTCATTGTGTTTGCATTT
TTTGTTAATAACAATGTATTAGCGGATTATTAATGCATTGCTTGAGCGAACATTGTGTTCTATTCCCCTGTGGTCCTTTTAATCGTATCTTCACT
GTGTGCCCGCAAAGAGAGCGAAAGAGCGCGAACTAGTGTCCCAGCATAGGCCTTTAGCCCATTGTTGTTGCCTTTTATGCTGCGCCGTTGTTGCC
TTTGCCTACTCCCCAATCAATACATATTCCGTCCTGCTCTGGCACGCTGGGCGATAATCGGTTGACGAACTATATAACGGCTATAGTTGAATACC
GAGAGAGACTTACGTGCTTAAAGAACTCCATGATATGGCTGTAGAAGACGAAGTCCAGAGGATACTTCTGCTGGAACACCTGCGACAGGAGGATC
GCGGTGGGTACCTCGCCGCTGGCGACCTCTGCACCGCCCACGCGGCCCCCTGCGCCGCTGCTGCTGTTGCTGCGCTGCAATTTCGAAGTCGAAGC
AACGAAATTCGAGCATTTGCACGAGATCAACATGATTTTGTTATTGCCGGTTAGCTGATAACGGTAATTGATGCGTTGCTCTCTTTCTCTCTCTC
TCTTTCTATATTTCTTCTCACTTCACTAGCAAAACACTTCGATGTTCTTCTTCCTCTTCCTAATTTATATCTTGCAGCGCTTGATAATAACTAAC
AACGAGTCCTTTAAATCACTTTCCCGCTCAATGTTGTTCGATACTTCGAGTGCAATTCAAGAACCCCTCGAGTCAGAAGTCGACGGGCATTTGCG
GGTATTCCGAGATTTACGAGTTTTCTTCTGGTGACCGAAAACAATCGAACATAGCATACACCCACAACCGTTCAATTTTTTTGTCGACTGTCTC
CGATATCAGGAGGTTGTTTGCCTGAAGCAATCGGTTATCGCAATTCAGTATGACCGAGGTGGAAATAGCCGGTCATTTTGGGAATTCCCTAAAAT
ATCTTCGCTGAAACAGTTCTTGGTAACACCAGATGAAAGTGATCTGGCAACTCTGAAAGTTACCAATGTTAACAGAGCGTGCGGCTAACAGTGAA
TAATATTATATCTAGGTGTTTAATTGCTGACATTAAATGTTATGTTCCAGGGATTATTATAAATAAGAATGTTTATTTAGCTTGCGCAAGAATTC
CATATCCTGTTTCATTAACAAACTTTCAGTATCGTCATGGGATAACCGTGAAAAAATCATATTTATACATGTGGGGAGTTGCCATCCAGGTTTGT
TAACTTGATTTTTTGAATCCAATAGTTAAAAGTCATATTGAAAAGTCTAGACTTCAACCATGTCAAATATATTATGCATCTGTCAAATGTCAAAT
ACGTAAGTAATATGTATATGCATAAAATATTTTTGTTAATTGCTTCTACATGTTATTCATATCAAGAGGGAATCCTTAACTTTATTCAAAGCTGA
AAATTTGCACAAAAAGATGGCTGCAAAATTGAAAAGTCTACACATTTTTCTTGTTTGCCAGAATTTTGATGAAAAGGAGCAAAAGGAATTCAAAT
AGCTGCTTATGAAATCTTTTCATGTTGTTATTATTAATTATTATTGTAAGATCGAAAAGATAATGTTTTTATTTTTGAATTCTTATTTGAAAGTA
ATATTATTTTTTTGTAAATTTTTATTATTTATTTTTATTTATAAATATAAGGATTAATTTAACAGATTAGTTTAAAAAGTGGAAATTTCAACCTG
GGAAAACCCCTCCTTCGCAAAATTCAGCACCACGAATCCGAGGAAGACTCTTAGAAGAGAAGCCGCAACGAGAAGAGACCACTCGAAGATGATAC
GGATAGAAGGACATAGCGAGATTCTTCTAGTATACCCTTTTAATTTACGGGCATAAAAATGAGTCTGGTGTGAATTTACGC
(SEQ ID NO: 1111)

Exon: 16561..15974
Exon: 2612..1424
Exon: 1357..1185
Exon: 1117..1001
Start ATG: 16183 (Reverse strand: CAT)

Transcript No. : CT28455

FIGURE SHEET 601

ATTGCTTCAGGCAAACAACCTCCTGATATCGGAGACAGTCGACAAAAAAATTGAACGGTTGTGGGTGTATGCTATGTTCGATTGTTTTCGGTCAC
CAGAAGAAAACTCGTAAAATCTCGGAATACCCGCAAATGCCCGTCGACTTCTGACTCGAGGGGTTCTTGAATTGCACTCGAAGTATCGAACAACA
TTGAGCGGGAAAGTGATTTAAAGGACTCGTTGTTAGTTATTATCAAGCGCTGCAAGATATAAATTAGGAAGAGGAAGAAGAACATCGAAGTGTTT
TGCTAGTGAAGTGAGAAGAAATATAGAAAGAGAGAGAGAGAAAGAGAGCAACGCATCAATTACCGTTATCAGCTAACCGGCAATAACAAAATCAT
GTTGATCTCGTGCAAATGCTCGAATTTCGTTGCTTCGACTTCGAAATTGCAGCGCAGCAACAGCAGCAGCGGCGCAGGGGGCCGCGTGGGCGGTG
CAGAGGTCGCCAGCGGCGAGGTACCCACCGCGATCCTCCTGTCGCAGGTGTTCCAGCAGAAGTATCCTCTGGACTTCGTCTTCTACAGCCATATC
ATGGAGTTCTTTAAGCACGCCTATGGTCCCATTCCAGACCTCACCGTGGCTGTGATTAATCAGCGGGAGCTGTTGTATGGTCTCACCCTGGAAGC
CGCTGGCCAGAGTTGGCAGCTGAGCCTGTGCATCAACTGCAAGGAGGTGCTATGCGCCAAGCGATTGACGGCGGGCGCCGGGGCCACGCCCACTC
TCTACCTCATCAACTGCACGCTGTTGACCAGCAGCGAGGAGCTGGCTCAACGGAAGTCCAACAAAGCCTTCTCGGAGACCTTCGAGCTGCTGATC
ATGGATCACACAGGCAGTGACTCTGGATCCACTCGACCCACCAGTGGACTATCCAACTCCGCATCGAGTCTAAGCATCGGATCCCTGTCTTCGAA
TCCCACTGATGCCAGGGTGCAGAGATTGAGAATGATACAAGCGCACCAGCAGGCGCGATTGCAGGAGGAGATTGTGGAGACAAATGAGAGAATCG
AGCGGTATACGCGCACTCAGTTCCAGTTACTAAACAGTTTCCGGGAGAAATCGGATCAGGACTGCGCGTTGCTATTCAAAGTTATTCGTGCGTTG
CCCGAGCAGGCCTCGGAGCTACTCGATCGTGCCATGCTCCCTGCCCTTGATGTGGCGGCCAATCAGCCGCAGAGTGCGACTGCCCGGCGCAGGAA
CACCATCAGCAGCCGGCGGGAGTTGAATGGTGGACCCACCACACCCACTACTACGTTGACACATCCGCCCAACTTCCTATCGCTGAACCAGCAGC
CGCAGCAACAGTTGCTGGCGCAGCAACAGCAGCAACAGTTGCAGGCGCAACAGCAGCAGCAGCAGCAGGCCCCGCAGAGTGTCTCGATGGCCAGG
AAGATGTCGCACTTTGACACACCGCCCGCCACCCCAGAAGCCACGCCCATGAGCGTGGGCAACAGCCCCACCTTCCGGCAGCAATCAGCAGCCGG
CGGTGCTGGTGGTCCACCCACCCAGACGTTGACCCCAAATGGAGTGGGTCAGTCCAGTGTTAACGAAGATGCAGATGACTGCCTGTTCGATCTGG
AGGATGTGGATGCTCCGGTTCCGGTTCAGTCCGTGCCTGTGCCTAGCTACACGCGTAGCCTGATCTACCAGCAGCAGCCTCAGCACAATCCCTTC
CAGCAGCTGAGCCAACAAAATGGCCTACGAAGTGTCCTAGATGACGAAGCTGCGGATGAAGCTGAAGATGCTCTGGACCCGGATAGCTCCATTTC
CATACCAGTGCGAGGCGGAGGGCGTCCTAGCCATGCGCAGTTGATGAACTTCGCCCGGAGTCTGCCCATCGAGATAGCAAACACCACGCTGGCCG
AGAGAGCTGCTGTGGCCAACAACAATAACTTCGGGCAGGGCTGCGAGGAGGGAATGGACAACATCGACATAGCGGCAAGCATCCAAGCGCTGACC
AGAAGTGTCCATGGCGAGGCTGTTTTTGGGGACTTGCCACGGCCCCGCCTGCGATCTCAGATCGAGGGCTAG
(SEQ ID NO: 1112)

Start ATG: 379 (Reverse strand: CAT)

MLISCKCSNFVASTSKLQRSNSSSGAGGRVGGAEVASGEVPTAILLSQVFQQKYPLDFVFYSHIMEFFKHAYGPIPDLTVAVINQRELLYGLTLE
AAGQSWQLSLCINCKEVLCAKRLTAGAGATPTLYLINCTLLTSSEELAQRKSNKAFSETFELLIMDHTGSDSGSTRPTSGLSNSASSLSIGSLSS
NPTDARVQRLRMIQAHQQARLQEEIVETNERIERYTRTQFQLLNSFREKSDQDCALLFKVIRALPEQASELLDRAMLPALDVAANQPQSATARRR
NTISSRRELNGGPTTPTTTLTHPPNFLSLNQQPQQQLLAQQQQQQLQAQQQQQQQAPQSVSMARKMSHFDTPPATPEATPMSVGNSPTFRQQSAA
GGAGGPPTQTLTPNGVGQSSVNEDADDCLFDLEDVDAPVPVQSVPVPSYTRSLIYQQQPQHNPFQQLSQQNGLRSVLDDEAADEAEDALDPDSSI
SIPVRGGGRPSHAQLMNFARSLPIEIANTTLAERAAVANNNNFGQGCEEGMDNIDIAASIQALTRSVHGEAVFGDLPRPRLRSQIEG*
(SEQ ID NO: 1113)

Celera Sequence No. : 142000013384483
TCCACCAACCACCAACCACCACCACCCACCAGGAATGTTATGTACTGGTGCTACTCCCAGTCGTATTTCATAATTTTGGACAAGTCACTGGGCCA
TAATTGACCCGCCGCTGATCGATAAGCTCGAGTGACACATTGCGCATTCGAACTGTGGGCCAAATGGCACGGAATTGATGATATGTGGGCGGGCG
TTCATTGTGGTCGCTTTTCATGTGTCGCAATCTCTATTAAGGGAACTACATTATGCGGCCAACGAAAATCGAACAAATCATAATGAAAATGTGTG
GCCAACGGGTGGAAGAATGTAATGATGCCGAAGGGAAATGTTCGTTAGGCAATGTTCAAACATATGCATAGATGGGTTATATTCCAACGTTTTCA
AATCTTACAAACTATTTTCTAAAGTTTACTCCATTTCTTTTTCTAGTAAAATTTCTAATTCTGTAGCACTTAGCGCGTTCATTAACCTTGGGCAA
CTCAATGAAGATCTTATTGAAGATTGGAATGCATCGCTGGGATTCCGCCTAAAGGTACAGTGCAGCTTCTTTAAAAAGAACACTGTAAGTTTAAT
GCTAGAACTTAACAAAAACATGTGTTTCTTACAAATTTCTTTCATTTTATATTAAAACACGATTTTCAAGATTTTTAAAGATTTTCCAGAGAAGT
AAAACAAAATGTAAAGAACTCGTTTTTGGGACCAGTTGGTGTGTTTGTTAGTTGTTCGATTTCTATTTAGAGTTCCAGCGGCACAAACAGCTGTA
CATAGGAAAGCACAACAACTCTTACATATGCGAATGGGAAAGCGAATATGGTGGAAGGCGAAACAACAATAATACTAAAGCCAAAGGTGAGAGC
GGAAAAAATAGAGAGAGCAGCGCCGCATTCGTGTTGTATTTGGTTTTTTATGACCGCCGCCGCCGACGACGACTAATTTTGTCGATGATAGCCGT
TCGTTTCGAGTCAAAGTTTCAGTCAATTTTTAGTCGTCAAAGCAGGCGGACGTCCAAGCAAAAAAAATTCAGAATCAAAAATATTGACAGTGACT
TGAGAGGATTACGTACTTAACTTAGCAACTCGCACCTCGCAAAAAGAAAAGAAAACACATTGCAAAAATGTCAGCACGCCGCGTCACATTGAACA
CACGCGTTTCGCGCGCCTCCACCTCCACGCCGGTGGGCGGGGCATCCACCTCGTCAAGGGTGGGCGCCACCTCACCCACCTCGCCCACGCGCACC
AGCCGGCAGCAGGAGAAGGAGGAACTGCAGCATTTGAACGATCGCCTGGCCTGCTACATCGATCGCATGCGCAACCTGGAGAACGAGAACAGCCG
GCTCACCCAGGAACTGAATCTCGCCCAGGATACCGTCAACAGGGAGACCTCTAATCTGAAGGCGGTCTATGAGAAGGAGCTGGCCGCCGCTCGCA
AGCTGCTCGATGAGACCGCCAAAGAGAAGGCCAAGCTTGAGATCGATATCAAGCGTCTGTGGGAGGAGAACGACGACTTGAAGCCCAGGTAAAGC
TCCAAGACGGCGGGTTCAGGTTTGGGCTCGGAATTGGTAACAGCGTATTATCAGCCAGTGATGTCATATGTACATATGTACCCATGCCGGGCCAC
TGGAGCGCGAGACACAGGCAGAAAATGGGGGCAACTTTGGGAGCCTTGTCAAGAAAATGTGGAATCAATAATGCACAGCACGAAAAGCAGCGAAA
TTTCTTCGATTTGTAAAGTAAAAGTACAGTCAGTCGAGATTTCTAGAAATGCACTACTTTTTATCAAATTGTTTTTTTTTTTTTACTTTTTTGTT
GTATTTTGTATTGAAATAAGCGAATTTTATATTTATTTCTTAGGTACAGTTGACCTAGAAGTTCAATTCCAGCTATGTAGTTATGTAGCGAAAAC
AATAACAAATTGTTTTATTTATAAAGGCAATATATTTAATTTTCATATTTCATGCTATTCGTAAGAAGAAAAGAGTTTTAGTAAGATACAAACTT
CAGTTTCCATGGTTGTTTTTTTTTTATATGTAGGGAGTGACAGAGACAGACAGAGAACGGGGCAGACTGAGAGCGAGCGAGGCCGATGATGTCAT
GCCAAAAGCACATTTTGAAAGCCAAGCACATGGGAAACTCTCTCGACTCTTTCGCTGTTGTTTATTTTTTGCATTTACACTTCCAGAATTCTCTA
GGCATTTTTATGCAAATGTTTAGTTCTCAGCTAATGTGTGAGTAGTAAACCAAAAGAAACCCAATGAAAATCAAAAAGGAAGAATCGAAATACCG
CCGTAAATCTCAATGAAGGTTACAAGACTATGATGTCATATGGCACTCAGTTACAGATCCATTTGTAATACCAGTTTCTGGTGGGAAGTCAACAA
AAGTTGGGTTGCTTAGCTTTTCCACTTGCGAGATTTCCGTTTCGCGTCGTTTGCGTTATCATATTTATTTTTGGTATTTACTGCGCGATGAGGCC
CAAAGCTTTTTCAATTCATAATAGCCACAATTTGTTGTTTGTGCGTTTTGCAATGCGTTAACGAAGTTAAGAGTTTGGCTAAAAGGCGGGTGCCT
AAATGTTGGGTAAACTTGATTTTTCGGCTACTTAAGGTGTGGCTTATACGTTGAGCAACGGACCGGAATAACCAAGGAAATTGTTTATGATGATT
ACGATTAGATACGATAAGATTGCAGCAGAATTATGGAACTTGTGATAAAAGATTTATCTTTTGTTGAGTGTCCATATTGCTTAAATTATTTTCAT
TTGTGAATGCTGGCTGTGCTTAATTATTTTAAATTTTTTTTTGAAGAATTTAGAAAGCCAAATATATTTTCATATTTATTCTTTGGTGACAATAG
CATACATATGTACAAGCGAATTAGGTCAGCGGAAGGAATTGGGGAGGAAAAATGGAACTTTAACACGCTCACACAAAACGCACAAAAAAAGGGGGA
AATTTATGAAAATCTAGAACGCAAACAAAACAACCTTGAATCTATTTTGTTTTTATATTTCCCCATTTTTACACAACTTTTCTTGATTAGCTACG
AAAACTGTTTACATTTTCTCGTTGCAACAGCAAAAACCGAAAGAAAATCGATAAAACAGAATAGAAGATTTTCAATCCATGAAAATAAACTTTCA
AAAATGGTCAACACAATCGCCGTAAAAGGCGCCAAACTATATATATAATTTTAATTACGTTTTCATTGAACGCATGACATGCAAAGTCAATTATT TCATAGTTGAAATTATTGGATTTGTTATAGAGAATAATTTAAAACGTGCCGACCACGCGAGTCGCCGATTGACAACCAAAATTGATATCCGAAAA
TATGCAGGGATTATTTGTGGAATTTTCGTAGCTATTTTTTATAGCGAGTTTGTTTTTGCCTAAATAGAATTTCAAATACAAAAAATAAAAGGCGC
TCATAAATCACAGGGGGTGGTGGGGTTTCGCAGGGGGGACGGGGTGAACTGGTCAGAAATAGCCGGGCTACTTTATGCTAATGGCATGTGACGAC
TTCTCCCAAGGCAAACAAAAACCTCGAAATGTTTGAGTATTTGATTCTTCTATGGAGGAGGATCGATGAACGAGTTTCCAAGCGACTATAGCATT
TAAATAAATGAAATGAATAATACATAAGCGATATAAAGAGAGCGGTTTAGCTTTCGCAAACAAATGTGAGTCGCAATGTGACTCAGTTATAATTA
TATAGATAAGTGACGTCATTCAATGAGCACATGTAGATAAAAGCAAAAAAAACAATTGCTCCTATGAACCGCCTAAATTTCGATAAGGGATTACT
CAGGCAAATAGGCTGATTAATTATTAAATTAAAAAGTTCTTTGTTATAAAAGATTATTAATTTTTAAACCAAATCCATTTTAAATTTAAGACTCG
ACAAAAAGACGAAGGAGGCTACCGTGGCAGAGAACAATGCCCGCCTGTATGAGAACCGCTACAACGAGGTGAATGGCAAGTACAACCAATCGTTG
GCCGATCGCAAGAAGTTCGAGGATCAGGCCAAGGAGCTCGCTCTGGAGAACGAACGCCTGCGCCGCCAACTGGATGATCTTCGCAAGCAGCTGGA
GGCGGAGACGCTGGCCCGCGTCGATCTGGAGAACCAGAACCAGAGCCTGCGCGAGGAGCTGGCCTTCAAGGATCAGGTGCACACCCAGGAGCTCA
CCGAGACCCGATCCCGTCGCCAGATCGAGATCAGCGAGATCGATGGCCGACTGTCGCGTCAATACGAGGCCAAGCTGCAGCAATCGCTCCAGGAA
CTGCGTGATCAGTACGAGGGTCAAATGCGCATCAATCGCGAGGAGATCGAGCTGCTGTACGACAATGAGATCCAGAACCTCAAGGCTGCTGCCAA
TAGGGCTGCCCAGGGATCCGCTCTTGCCACCGAGGAAGTCCGTCTCATGCGCACCAAGATCGATGGCTTGAACGCCAAGCTACAGAATCTGGAGG
ACACCAATGCTGGCTTGAATGTGAGTACTGCAATTGCCAAACTAAATTCCCCGTGTGATTTTAATGTTGACATTTTCTCATTTACCATAGGCTCG
CATTCGGGAGCTGGAGAACCTCTTGGACACGGAGCGCCAGCGCCACAACCAGTACATCGCCTCCTTGGAAGCCGAACTACAGCGTATGCGCGACG
AGATGGCTCACCAGCTGCAGGAGTACCAGGGTCTGATGGACATCAAGGTGTCGTTGGATCTCGAAATTGCCGCTTACGACAAACTGCTGTGCGGT
GAGGAGCGTCGCCTGAACATCGAGTCGCCCGGACGCCCGACTACCGACTCCGGTATCTCCAGCAATGGCAGCCACTTGACCGCCAGTGCCAGTTC
CCGATCCGGCAGGGTCACGCCCAGTGGCCGTCGCTCGGCTACACCTGGCATCTCTGGATCCAGCGCCGTGAAGCGTCGCCGCACCGTGATCGATG
AGAGCGAGGATCGCACTCTGTCCGAGTACTCGGTGAATGCCGCCGCCAAGGGAGATCTGGAGATCATCGAGGCGGACGTTGAGGGACGCTTCATC
AAGCTGCACAACAAGGGAACCGAGGAGATCAATCTGACTGGCTGGCAGCTAACCCGCATTGCCGGCGACGAGGAACTGGCCTTCAAGTTCTCGCG
CGGATCGAAGGTACTCGGCGGTGCTAGTGTAACCATTTGGTCCGTCGATGCTGGTACCGCACATGATCCACCCAACAATCTGGTGATGAAGAAGA
AGTGGCCGGTGGCCAACTCGATGCGATCGGTGCTGGCCAATGCCGACAAAGAGGTGAGAGTCTTGTCCATATACAACACATGCGGCACTTGCGAC
ATCTGCCGCCACTGCAGACACCTCGAATTCGTGCTCGACCAGTACGATATGCCATAGACCTTTGCATATTTCGACTATAATTTACGTTATATCTT
TTGCCTTTCAGGATGTTGCCAGCTACGACCGTGTCCGTGCTAACGTTTCCAGCCACACCTCGCGGCATCGCAGCAGTGGCACGCCCAGTACGGGC
TTTACCCTCGGTTCCGGAGCTGGCTCCACTGGCGTGAGGAGCCTCTTCTCCCTGCTCTTCTAGGCGGGAGCTTCAACTTCGAATCGGACTGGCTT
GGCTTGGATCCTGAGGCCCAGCCAAACAAAACCCAACTCACCGCAGAGACTCACAGACTCCGAGCTGCACATTCAAACCACACACAGATCTGTTC
TGCATATCAAGCTTATTGTGAAACTATGTACAACAATCAAAACTTGTTCAACTCTTAATGTTAAATGTTTAAGTGACCTTAGTACATGTCTTTGA
CTCTATGCGTCTCCTATGTTTAAGTAAGTTTTTTCACGCTCTACACCCTACTCTCACTCTCTCTCTCTGTAATTTATGACGAGAACATGCATTTT
GGTAAAAATACAAAAATAAACAAACAAATAAATGTTACAAGAAAGTTGGCTGGAAAATCAATTAATGAGATTTAGCCGTGCGGTCGCCTGCGTTG
ATATCTTTTTTGCGAGGAAGCCAAATCGGCTTAGGCCAGTGGAAAACTTCTTGAGATGCTGTCGCGGCATTTTGCACTATCTGGGATCCAGGACC
ATGGGCCAGGCCATAATGGACAGGTAAGTGGGGGAAATTAACTACAAGAAGTCAGGTGGACAGGTGCAGCTGGGAGCAAAACTGTGGGCTAAAAC
CGAACGAGGTCAACGAAAAAGTTTCGCAACTTTACAACTTGAAAATAAATTAGGTTGGATCACTGGGAAAGGTCGAGCAAACCGAAGCAAAAGTT
TTTAATGGAGCAAATATACAGCTTCAGGGCAGTTGTAGAAATATACTATTTAACAATTCTAGGGCTGCCATTCAAACTAATAAACGACTCGTTTC
GGATACAAAAATAATGCTTAGAAATACATATGTGCAATAAAAGCCAGTTGTACTAGTTCGTTTCTTTCTAATCTCCAACTAGAATACAGGAAAAA
CCTAGGCGTCCCACTGTTTAATCTGCATCCTTTGGCTTACTCCAAAGGAATTAGCATTGCCAGGACGAAGAAGAAGATCCCTTCACTTGGCGCCG
CCTTAGCCAAATTGCGTTATCTATTGCCCAGGCATTTCTCGCAGTGCATGAGCAGCCACTAAGGCAACTTAGCGGCGCTTGAGTGAGTGCACGAT
TCAATGGAATGAATGCGAGAGAAAGGCGGCGGAGAAAGGTGAAAGCGGCTGAGACGGCTGCGAAGACTGAGAGGGCTCAGAAGACTGAGGGGGCG
GGCAGACAGTTGACTTCAAAGTAGTTTTCCTTGGCAAAGTTTTTTTCCTCCTTGGCGCACGTTTGCATGCGCATAATAGGATTAGTCAAAGTAAT
AAGTTGTTTTTCTTCCTCCACTTTTAGCTGCTGATGCTACCTAGATTCCTGCTGCTCACAG
(SEQ ID NO: 1114)

Exon: 1001..1513
Exon: 3891..4485
Exon: 4556..5278
Exon: 5427..5901
Start ATG: 1113

Transcript No. : CT28479
CGTCCAAGCAAAAAAAATTCAGAATCAAAAATATTGACAGTGACTTGAGAGGATTACGTACTTAACTTAGCAACTCGCACCTCGCAAAAAGAAAA
GAAAACACATTGCAAAAATGTCAGCACGCCGCGTCACATTGAACACACGCGTTTCGCGCGCCTCCACCTCCACGCCGGTGGGCGGGGCATCCACC
TCGTCAAGGGTGGGCGCCACCTCACCCACCTCGCCCACGCGCACCAGCCGGCAGCAGGAGAAGGAGGAACTGCAGCATTTGAACGATCGCCTGGC
CTGCTACATCGATCGCATGCGCAACCTGGAGAACGAGAACAGCCGGCTCACCCAGGAACTGAATCTCGCCCAGGATACCGTCAACAGGGAGACCT
CTAATCTGAAGGCGGTCTATGAGAAGGAGCTGGCCGCCGCTCGCAAGCTGCTCGATGAGACCGCCAAAGAGAAGGCCAAGCTTGAGATCGATATC
AAGCGTCTGTGGGAGGAGAACGACGACTTGAAGCCCAGACTCGACAAAAAGACGAAGGAGGCTACCGTGGCAGAGAACAATGCCCGCCTGTATGA
GAACCGCTACAACGAGGTGAATGGCAAGTACAACCAATCGTTGGCCGATCGCAAGAAGTTCGAGGATCAGGCCAAGGAGCTCGCTCTGGAGAACG
AACGCCTGCGCCGCCAACTGGATGATCTTCGCAAGCAGCTGGAGGCGGAGACGCTGGCCCGCGTCGATCTGGAGAACCAGAACCAGAGCCTGCGC
GAGGAGCTGGCCTTCAAGGATCAGGTGCACACCCAGGAGCTCACCGAGACCCGATCCCGTCGCCAGATCGAGATCAGCGAGATCGATGGCCGACT
GTCGCGTCAATACGAGGCCAAGCTGCAGCAATCGCTCCAGGAACTGCGTGATCAGTACGAGGGTCAAATGCGCATCAATCGCGAGGAGATCGAGC
TGCTGTACGACAATGAGATCCAGAACCTCAAGGCTGCTGCCAATAGGGCTGCCCAGGGATCCGCTCTTGCCACCGAGGAAGTCCGTCTCATGCGC
ACCAAGATCGATGGCTTGAACGCCAAGCTACAGAATCTGGAGGACACCAATGCTGGCTTGAATGCTCGCATTCGGGAGCTGGAGAACCTCTTGGA
CACGGAGCGCCAGCGCCACAACCAGTACATCGCCTCCTTGGAAGCCGAACTACAGCGTATGCGCGACGAGATGGCTCACCAGCTGCAGGAGTACC
AGGGTCTGATGGACATCAAGGTGTCGTTGGATCTCGAAATTGCCGCTTACGACAAACTGCTGTGCGGTGAGGAGCGTCGCCTGAACATCGAGTCG
CCCGGACGCCCGACTACCGACTCCGGTATCTCCAGCAATGGCAGCCACTTGACCGCCAGTGCCAGTTCCCGATCCGGCAGGGTCACGCCCAGTGG
CCGTCGCTCGGCTACACCTGGCATCTCTGGATCCAGCGCCGTGAAGCGTCGCCGCACCGTGATCGATGAGAGCGAGGATCGCACTCTGTCCGAGT
ACTCGGTGAATGCCGCCGCCAAGGGAGATCTGGAGATCATCGAGGCGGACGTTGAGGGACGCTTCATCAAGCTGCACAACAAGGGAACCGAGGAG
ATCAATCTGACTGGCTGGCAGCTAACCCGCATTGCCGGCGACGAGGAACTGGCCTTCAAGTTCTCGCGCGGATCGAAGGTACTCGGCGGTGCTAG
TGTAACCATTTGGTCCGTCGATGCTGGTACCGCACATGATCCACCCAACAATCTGGTGATGAAGAAGAAGTGGCCGGTGGCCAACTCGATGCGAT
CGGTGCTGGCCAATGCCGACAAAGAGGATGTTGCCAGCTACGACCGTGTCCGTGCTAACGTTTCCAGCCACACCTCGCGGCATCGCAGCAGTGGC
ACGCCCAGTACGGGCTTTACCCTCGGTTCCGGAGCTGGCTCCACTGGCGTGAGGAGCCTCTTCTCCCTGCTCTTCTAGGCGGGAGCTTCAACTTC
GAATCGGACTGGCTTGGCTTGGATCCTGAGGCCCAGCCAAACAAAACCCAACTCACCGCAGAGACTCACAGACTCCGAGCTGCACATTCAAACCA
CACACAGATCTGTTCTGCATATCAAGCTTATTGTGAAACTATGTACAACAATCAAAACTTGTTCAACTCTTAATGTTAAATGTTTAAGTGACCTT AGTACATGTCTTTGACTCTATGCGTCTCCTATGTTTAAGTAAGTTTTTCACGCTCTACACCCTACTCTCACTCTCTCTCTCTGTAATTTATGAC
GAGAACATGCATTTTGGTAAAAATAC
(SEQ ID NO: 1115)

Start ATG: 113

MSARRVTLNTRVSRASTSTPVGGASTSSRVGATSPTSPTRTSRQQEKEELQHLNDRLACYIDRMRNLENENSRLTQELNLAQDTVNRETSNLKAV
YEKELAAARKLLDETAKEKAKLEIDIKRLWEENDDLKPRLDKKTKEATVAENNARLYENRYNEVNGKYNQSLADRKKFEDQAKELALENERLRRQ
LDDLRKQLEAETLARVDLENQNQSLREELAFKDQVHTQELTETRSRRQIEISEIDGRLSRQYEAKLQQSLQELRDQYEGQMRINREEIELLYDNE
IQNLKAAANRAAQGSALATEEVRLMRTKIDGLNAKLQNLEDTNAGLNARIRELENLLDTERQRHNQYIASLEAELQRMRDEMAHQLQEYQGLMDI
KVSLDLEIAAYDKLLCGEERRLNIESPGRPTTDSGISSNGSHLTASASSRSGRVTPSGRRSATPGISGSSAVKRRRTVIDESEDRTLSEYSVNAA
AKGDLEIIEADVEGRFIKLHNKGTEEINLTGWQLTRIAGDEELAFKFSRGSKVLGGASVTIWSVDAGTAHDPPNNLVMKKKWPVANSMRSVLANA
DKEDVASYDRVRANVSSHTSRHRSSGTPSTGFTLGSGAGSTGVRSLFSLLF*
(SEQ ID NO: 1116)

Name: LAMIN C
Classification: structural_protein
Gene Symbol: LamC
FlyBase ID: FBgn0010397

Celera Sequence No. : 142000013384657
CTAGTGTCCTCAATAGATCCTGCCATTTAACTGTCAAATTAAAGTCGGAGCAGTCCTTGCTCAATTTCGATATCGTCGTTTTGTCTATTATTAGC
ATTCTGGGCTGTCATGTTATCGCAACTGTTGTGCACCAATGTCAATTGCACAAGTCAAAAACTGCCTCATAGATGACTTTCGAGATACTTTGCCG
GCAATTACGTAGCTGTTTCATTGTTCCACCATTTCGAACAAGCTTCATAATATTTTCACTTTTATGGCAGGCAACATAAAAGACGACAGCTTTGG
CAATAGCAACAACATCATCATTATCAACACCATCAAAGCCCGGAAAATTTCACCTTCTGTGACTCCACCCCCCCTCCCAACGCCGTGCCTTTCGT
CTCCTTTTGTCCCCCTCAATTGTCGTAAAATCATAGGAAAAAAGAAAGGAGCCAACGGAGGCGAAAAGTGTGAGTGCGTAAATTTCTCTCTGGAC
TCGGAGTCGCTCAAGTGTCCTTCCATTCTGTGTCATAAAATTAACGCTTTATATGAACGAAAGCATAAGGCGCTCGATTTTTATCACCAAGGCCA
ACAAGATGGCCATAAACGAATCAGGAACATGGAAACGCAGAGGAAAAAAATAGGCAGCTAAGTATCTACAAATGAAAGTGTAATTACAAAAGATT
TATACTGATTTTTAAATAAACTTATAGCTAAATCTATATATAAATAAAAATGTATATTTTCCCAATTACAACCCACTTCGTACTGTTATTTTCTG
GCAGTGCATAAGCCCATAGCGAACCTTATGAGAACATAAAGAGTTAAGAGTTGAATTAGAAGCAGAAGAAACTGGGACCGAAGTACGTTGGGTAG
TAAGAGAGGTGGTCCAAAGAGTGCCTAATTATTTACGTGCAATGAAAGTTATGAATTGGGGAACAGGTCAAGTCGGCGAGGGTAAAAATACCCCC
GAACCTCCCTATGCCTTTACTGTCTGTGTGAATGGCTTCAGTCTGGTTTCGTAGCCAGCCCCTTATACACATTCTCGTGTTGTGGCTGTGAAATC
GTTTTTCCCAGGTGATCTGAAATTTTATTAGCATCCATTGTTATAAATTTGAATCAGTATAAAAGATCATTCGCCAAATACACTCAACCATGCTG
ACGACCCAGCAGACCGAATTCAAGATGATGGACAACGGCACCGAGACGCTGGCCGATTCTCCTTCGAGTTCCAGCGAGGATCTGAAAACGCTTTC
GGATATGGATATTCGCAAGCCCGTAACGGAGATTGTTGATTTGCGCCTTAAGCATCCGCTAGAGAACACTTGGACACTGTGGTACTTGGAGAATG
ATCGCAGCAAGAACTGGGAGGACATGCAGAACGAGATTACTAGCTTTGACATGGTCGAGGACTTCTGGAGTCTCTACAATCACATTAAGCAGCCA
TCTGAGATTAGAGTGGGCAGCGATTATTCTTTGTTCAAGAAGGGCATTCAGTAAGATTGGCTAGATTTATATACATGATTACCGATTTCCTATTC
ATTGCAGGCCAATGTGGGAGGATGATGCGAACAAGTTCGGCGGCCGTTGGGTCATCAATATGGGGCGTGGCTCCAAAGCGGAGCTCGACAAGCTT
TGGTTAGATGTGGTAAGTAGCTATTGGAGCTTTGTGTCCATCGCCTGTCATATCAGTTGCAACTGCACAACCTCTTTTCTGCCCACTGACAGCTA
CTCATACTGATTGGCGAGGCCTTTGAAAACACCGAGGAAGTCTGCGGCGCCGTTATCAACTTGCGCGGGAAGAGCAACAAAATTTGTGAGTATTA
CTGAAAAAAAAAAGATGTGCATGTGCATTAAAAAAGCTGGTTACAAATATTATATTTTACTAAAAACATTACACATGTTTTGTTTACTTCGCCAA
CCTATAAATATTAAGTGGTATACACCTAGGTTGGCTCTGTTTTTTTTTTTAAACATAGTTTACACATTGTAGTTTTGTAGTGTACTCAGCTTAA
GTAGCCAGTGGACACCACCATGACAACTACTAACCCAGCGCCTTTACTCCGCAAGCGATTTGGACCGCCAACGGGCACAACGAGCTGGCCGTCAT
GGAGATTGGACTCAAGTTACGCGACCTGCTCGTCCTGCCGCCCCACCAACTGCAGTACCAGCTGCACAAGGACACTATGTGCAAGCAGGGATCGG
TGATCAAAGCGGTTTATTGCGTGTAAGCCGTCTCCGTTTTGGATGCCACCCACCACTCCATCCACCAACCACCCACATTTCCATGGCCGCTTATG
CCTCTGAATGCTGTTTCCAGCGCGTGTATCCGAAAAATATAAAAAAAAAAATGTATCTTGAAACAGAACTGGTTTTATGAATTTGACCATGTTAA
AAATTGCAAAGAAAGATGTAAATACATAGTGTTGTGAATGCATATACGACGAGCCATCATTAAATTCCCCAGTTTTTAAGTCCCAAGGAGCTCTT
TTTATGCCGCTAGTTGGACCCTTTATGCTCCACAAAATGTTATGCAAACATATGCCGCACCAGAGCGCAAATAAAATGGTTTATATACACTTGCA
GTTTGTACTTTTGGCCGGGCCAGCTAGAAGTGCACAGTGACTGCAAAAGATAAACGTCCACTTGGTTCGCTTGGCTGGCCGAGCGAAAAACAAAA
GACCGAAAAGGGTCAACAATGGCCACGGCGGATTGTCCGTTTTAGCGAGTGCCACAGTACCCGGCGCTGAATCTCTGGGATCTCTGGTATCTGGA
ACTGGCGTCGAGGGCTTCCAAAATGGAGACAATTGAATTTTGATGAAAGGCCGAACGAAACGCCGTTGCCTCGCGCAGTATTAAAATTCATGCTA
TGAGCTTCGAGTTCGAGTTTGAAAAGAGACTCTTAATTTGCGTGTAAAAAATGTTATTTTAATAATTTAAAAAAAAACCTATTAAGTACGTTTTT
AAAGTATCTTTGGTATTCTAGTATCTATAACCATTATCGAATGACAAAGCTGTAGGTTCCCTCACATGCGGCTGGTAACGTTTATTCAACCCTTT
GTTCAGCCCCTGTGACGTAACGTTTTAGCCAACTCGGGTCACCAGGCCATTCAATCAACATTGAAATTCCGATGGCAGCGGCACGTGCAGTAGCA
ACTTCATTATGAGCCACTTTAAGCTGACAAAACTCATCTCCATCCGCATAGCCCGTTGACTGCATTTTATGGGCCCAGGTGGCGGCGGCTTACAT
GGGGAGCTGTTAAACCGAAACCGCATCAAAACCGCACACGTCCCACATGGCATCCAGGTGCCTTCACCTCTTGTTTGGCCCA
(SEQ ID NO: 1117)

Exon: 1001..1475
Exon: 1528..1627
Exon: 1708..1795
Exon: 2051..2312
Start ATG: 1135

Transcript No. : CT28485
GTAGCCAGCCCCTTATACACATTCTCGTGTTGTGGCTGTGAAATCGTTTTTCCCAGGTGATCTGAAATTTTATTAGCATCCATTGTTATAAATTT
GAATCAGTATAAAAGATCATTCGCCAAATACACTCAACCATGCTGACGACCCAGCAGACCGAATTCAAGATGATGGACAACGGCACCGAGACGCT
GGCCGATTCTCCTTCGAGTTCCAGCGAGGATCTGAAAACGCTTTCGGATATGGATATTCGCAAGCCCGTAACGGAGATTGTTGATTTGCGCCTTA
AGCATCCGCTAGAGAACACTTGGACACTGTGGTACTTGGAGAATGATCGCAGCAAGAACTGGGAGGACATGCAGAACGAGATTACTAGCTTTGAC
ATGGTCGAGGACTTCTGGAGTCTCTACAATCACATTAAGCAGCCATCTGAGATTAGAGTGGGCAGCGATTATTCTTTGTTCAAGAAGGGCATTCA GCCAATGTGGGAGGATGATGCGAACAAGTTCGGCGGCCGTTGGGTCATCAATATGGGGCGTGGCTCCAAAGCGGAGCTCGACAAGCTTTGGTTAG
ATGTGCTACTCATACTGATTGGCGAGGCCTTTGAAAACACCGAGGAAGTCTGCGGCGCCGTTATCAACTTGCGCGGGAAGAGCAACAAAATTTCG
ATTTGGACCGCCAACGGGCACAACGAGCTGGCCGTCATGGAGATTGGACTCAAGTTACGCGACCTGCTCGTCCTGCCGCCCCACCAACTGCAGTA
CCAGCTGCACAAGGACACTATGTGCAAGCAGGGATCGGTGATCAAAGCGGTTTATTGCGTGTAAGCCGTCTCCGTTTTGGATGCCACCCACCACT
CCATCCACCAACCACCCACATTTCCATGGCCGCTTATGCCTCTGAATGCTGTTTCCAGCGCGTGTATCCG
(SEQ ID NO: 1118)

Start ATG: 135

MLTTQQTEFKMMDNGTETLADSPSSSSEDLKTLSDMDIRKPVTEIVDLRLKHPLENTWTLWYLENDRSKNWEDMQNEITSFDMVEDFWSLYNHIK
QPSEIRVGSDYSLFKKGIQPMWEDDANKFGGRWVINMGRGSKAELDKLWLDVLLILIGEAFENTEEVCGAVINLRGKSNKISIWTANGHNELAVM
EIGLKLRDLLVLPPHQLQYQLHKDTMCKQGSVIKAVYCV*
(SEQ ID NO: 1119)

Name: eIF4E-related
Classification: translation_factor

Celera Sequence No. : 142000013384483
ATATGTGCAATAATCACTTCTTTTACGATCGAACGCCCTTTGAACAATTCCTGGCAGGTACCAGGTAATATATTTATTATATGATGGTTACCGCA
ATTATAAAATGTCTCATTTGCCAGTTCCGATCGACTGGTGATTGTAACAGATCCTCCATTTGGCTGTCGCACTGAACTGATTTCGCACACCCTGC
GCAGCCTTAGAAAACTGCATAATCAAATCAACCGATTGCCATCCACTCCACTGTCCATATTCTGGATATATCCCTATTATTCAGCTAACCACATC
AGGCAGGAAATGCCTGAGCTTGAAATGTGTGAATACAGGATCAATTACACTAATCACCTTAGATATACGAATGTGGGCAAGCAGAGTCGGTTTTG
TGGATCACCCGTGAGGCTGTTCACCAACGTGCCACTGCGACTTCTTCAATTGCCCCCTGAAGAGGGCTATAAGTACTGCCAAAAATGCGATTGTT
ACACTGCCAAGGAGAACCTGCACTGCAACCGCTGCGGGAAGTGCCCCTCGGTGAATGGCCAAACGTACAAGCACTGCGAGTCCTGCGATGCCTGT
GTGAAACCCAACTATGTGCATTGCTCCGACTGTAGAAGGTGCACGCAGAAGGAGGGACACAACTGCTCCTTCTATCAGACCAAACAACACTGCTG
GATGTGCGGCCAGAAAGGCCATATCGAAACCAAGTGCCCAAACTTCCGCAAGAGAAAGACGAACTATACCAAAGGCTGCCTTTTGTGCGGCAAAC
GAAATCACAGGGAAAAGCGATGCTCGTACCGCTCAAAATACTTCAGGGAACAGTGTTTTATGAACGAAACAACAATTCAGTGTCTTTAAGATACA
TACAAATATATATGTACAAAGATAAATACAAATTGCATTTCTTTATATACTGAGGGGCACTTTAGACTGTATGCATTTATGCAGTTTATAAGAAC
AACACTGACAAAACCTTCACTACCATCCATAAACAACAGGGCACACATTTGTTTAATACAAAATTTATTTGTTCTTAACACTTTTCGTTGAATGT
CTTACAAGTTCTTGAATTGCAACGGCTGCGCGCGGAATTTCTGATGCACATGACCACGATAAATTGTGGAATGAATTCTCAGCCCGCCGGATGAA
CGAACGGATTGGGGGAAAACGATTAAATTTTGAAAATATGCATTACGTTTAAACAGGTTTTTAACTTAAGCTTAGGTATAATTAATTTCATGTGG
AAACACACCAATGCCTCAACAAGCGGAATGGATCTCTTCTTATCTCGCCGCAAAAGAAATGATGACGTCGACATTGTTCACGCTCGTTGAGGTGA
AAGTATTTTATTGGCTACGAAATGCATGGCTTAAGAACGATTGTATTTGCCCCAAATGTGCAGCATGAAGACGGAAGCGATGAAGAGCAGCGACA
TGACCAGCACGGGTACGGGACCACTGCAGCAAAAGTCTCATTAGCACTGGGCCTTTAATATAAATATAGCCGAGTTATTCACTTACACTTTGATA
CCGGGCGAGTCGTCCGTGTAGAAACGCCACATGCCACCAGTTCCGGCTCCGCCGGGTGCACGGCTCCGGGCCGCTGTGGTGCTGGTGGTGGTCTT
GCGCTGCTTCAGGGTGCTGCCGCCTCCGGATCCGGCGCTACGTGGCGCCGACAATTTGCTGGGGGAGCGCGATCCGCTGCCCACGGACGTTGAAC
TGGCTGGAGCGGGCTGGCAAATGTGTTTTAATTAGTTGCCGCACTCAATTGCCATCTAGTTTAACTCACCATTTTGGGCTATCTGTTCCTCTGGA
CCGACTGACCTGGAAAATATGAACGGGCGAAGTGGAATCTGAACGTGAATCTGAATCTGACGTGCTCGGCTTCGTGTCGCTTCGTCTTTTTTCGT
TCCACGTCACTTTGGTGGTGGCACCGCTGCCGATAGGTCGTGACGCTGAGGTGACAGCTATCGTGCACTTAGACAGCTGGAGATGACAGGCTAAG
GCAACTCAACTATCGGCTGCTTTGGCTCTAAAATGAACTAGTAAAAAAAAAACGAAGAAATAATATATTCAAGTTATGAATTTAATAGATAACAA
TAATAGATAAAATATTAATTCTACAAAATGAATTGTTTAAATCAATTTGAATGAATCCTATTAATATAATTGGCTATTATTAAAACTCCGATAAT
AAATGCTATTATTCTTGATTTCCCTTGATTTAATTATATAATACATACTTAATAACTATATAATTATATAGAATAAAAACTTAATCACGCATTTA
ATAGATCATATAGATATAGAATATATAGAAAATCAATGAAATCGATTTTGATAGCGATAATGTGCAACCTTGCATGTAAGTTATTTTTAGATTTT
AGCTGGGCAAGCGCAATTTTCTTGGCGCGCACCAAACAATTTGTAAATAATATTTTTGCTTAACTGGTATTGGTTCGACTGCGAATCACTAAAAA
TTATTAAGTGACTTAAGCACCGTGTTTTAAACATTGTTAATCGGAACGGCCACACCGAAGCGCGGGCTCACTAAACGCTTTTGTCATTTTTGCAC
ATCTGTACAACGTTCACGTTAATTGCAGCGGCATCATCTTTGCTGGATTTCAAAGGAATATTTTGCGGTGAAAAGAACGAAAAAGTGCTTGCATT
TGTGCGCTAATGGGTATATGAGGTCCTTCTGCTAAAGGAATGCCAAGTCATACAAACTTTTCGCGATTCGCCTTAATGGAAATAGATAAGACGCG
GCGCAGTTGAAAGATTGCAAATTGATCCACCGATCGACCGACGCACATGAAAAGTGAAGTATGGAGGACATTGAATATTTAGACGAGTACAAAGA
CTTGGTGCTGCCAGGTGCGTGATTTCAGCTTCCAATGCTATAAATACTT
(SEQ ID NO: 1120)

Exon: 1899..1780
Exon: 1723..1512
Exon: 1448..1001
Start ATG: 1782 (Reverse strand: CAT)

Transcript No. : CT28511
CGAAAAAAGACGAAGCGACACGAAGCCGAGCACGTCAGATTCAGATTCACGTTCAGATTCCACTTCGCCCGTTCATATTTTCCAGGTCAGTCGGT
CCAGAGGAACAGATAGCCCAAAATGCCCGCTCCAGCCAGTTCAACGTCCGTGGGCAGCGGATCGCGCTCCCCCAGCAAATTGTCGGCGCCACGTA
GCGCCGGATCCGGAGGCGGCAGCACCCTGAAGCAGCGCAAGACCACCACCAGCACCACAGCGGCCCGGAGCCGTGCACCCGGCGGAGCCGGAACT
GGTGGCATGTGGCGTTTCTACACGGACGACTCGCCCGGTATCAAAGTTGGTCCCGTACCCGTGCTGGTCATGTCGCTGCTCTTCATCGCTTCCGT
CTTCATGCTGCACATTTGGGGCAAATACAATCGTTCTTAAGCCATGCATTTCGTAGCCAATAAAATACTTTCACCTCAACGAGCGTGAACAATGT
CGACGTCATCATTTCTTTTGCGGCGAGATAAGAAGAGATCCATTCCGCTTGTTGAGGCATTGGTGTGTTTCCACATGAAATTAATTATACCTAAG
CTTAAGTTAAAAACCTGTTTAAACGTAATGCATATTTTCAAAATTTAATCGTTTTCCCCCAATCCGTTCGTTCATCCGGCGGGCTGAGAATTCAT
TCCACAATTTATCGTGGTCATGTGCATCAGAAATTCCGCGCGCAGCCGTTGCAATTCAAGAACTTGTAAGACATTCAACGAAAAGTGTTAAGAAC
AAATAAATTTTGTATTAAAC
(SEQ ID NO: 1121)

Start ATG: 118 (Reverse strand: CAT)

FIGURE SHEET 605

MPAPASSTSVGSGSRSPSKLSAPRSAGSGGGSTLKQRKTTTSTTAARSRAPGGAGTGGMWRFYTDDSPGIKVGPVPVLVMSLLFIASVFMLHIWG
KYNRS*
(SEQ ID NO: 1122)

Name: sec61 beta-like
Classification: transporter

Celera Sequence No. : 142000013384134
TGCCACTTTTTGATAGATCCTTCAATTATTCGCACTTGCTTCAGATAAAAGTTAAATATTGTCCGCAGATTGTAACCGCTTGAGCGCCCAAGCGC
GACTGACTTCCCATCTTCCATGAGCATCCATTTAAATTTGCTGCGTACATATATCGCACCGTTCGGGTTCAAATTCTAATTGACCTTTCTCTTGG
GGTAGGTTCGAAGAGACTTGATTGATCAAGGAAAGAGTGTCAGTGGGAAATGTCGTCAAATACTCCGCACTGTCTCTTATATAAACAAAAAAGAT
AGATTGAAGTCTGCTTTGCTAAGTGATGGATTTTATTTCAAGGTATAACTATAAGAAGTGATTTCTTCATCTGTACAAAGGACACATTTGCATAC
ATTTTCTACATTCACATGCAGCGGATTATAATTACAGCATACAAACTTAGGCACTTATTTATCTGTACTTGTAAAGATACAAAATCTAGCTGGAT
AACAATCGCATATCACATACTGTGTTGGTTTACAAGTATTTACACTGCCTACACGAGATAGAGATTCATTAAAAAGTTATTCAAAGATTCAAACG
CTTAGCTTATATGGCAAGTGCCAAAACAATAAGTCAATTTCCTATTAACTAAGATAGTTATATACAATGCTATTCGCAGTTCCACGCGTTTCGTA
ATATTTGTTCAATATTTACTAGAATTTTCTTGAGCTGGTCTTATGAAGTAAAAAGGGTTTGAAGAAATTGGAATTATTAAATTTTAGTTAAACAT
TTAAATTGAATTTAAGTTAAACTCGATATGAGACTATCTGATCTGCTGCTTGAATTGCTAATAAAAAAGTGATTACTTGACTTCGAGGATAAAAT
CCTTGCAATAATCTTTCTTTTTCAGGCTACTAATAATATCATTTTTAGTGGTTCTGGGTGGCACAATGCCATTGCATCTTAAACCTAATTACGTG
GCTCGAATTCCGATCAAGTCTTAACTAATCTAATCCGACTGATAATAATGTCAGACGTACACCTCTCCGGTCTTTTGTTCCGGCTTGTGTTTGGC
CAGAGTTGAGGGGGCCGAGGATCCTCCGACTTCGCCCGTTTCCAGGCCTCCGCTCCTCTGAGGAATTGGCATCGTGCCTGAGTTGTCCACTGTGC
CCGTGGGACCCGCTGACCTCATCGAGGATCGTTGCTGCGGATCCTGCAGATTGAGGCTCAGGTTGAAACTGTTGTTTCGCGAAATGTTCTGGTTT
CCATTGAGGGGCTTAACGGACAGCAGTGCCGTAGTGGTGATACCGCCATTGCCATTGCTCGACCCACTGTTGCTATATCCATCCTGGACATCTGC
ACCGGTCAGCTCCACAATGGAAAGTGCTGACGGCGATCGCTGGATGGACAAGGACACCGGTATCGTGGTGATCACATCGTTAGGATCGTAGCCAC
TTGCCGTCGTCGTTATCGTGGGCAGCTGGGCATTCGCCGAAATGGGCAGGATGCTCAGTGTCCCAGTGGGCATCGTTTCCCCACCGGTGCTGGTC
ACGCTGAAGGGGAACGACAGAGTGGTGATGTTTGTGGCAGCTGGAATACCTGCAGGTTATCAGAGGAAACAATAAGTGAGAAAAGAATATAAATA
TTTAATCCATTAAGCTTTTAATATCCTCTTAAGAGTATGTATTGAACTCATCATTAACTATTCAGAGGCATTAAAAACTTCTAGATCTTGGATAT
TTCCACTTACTGCTCGGCGTGAATCCCTCCTTCATGCTGGCTGCCAAAGCTGCGGTAGCCGGATGACCTGGAATCAGAGTGTTATTGGACGATGA
GCTATCCATCTCTTTGATGGGCGAGAGCAGCAGCGTGCCCAGCACCTGACCGCTCTCCTGGTGCAGTAGTGTGTCGGGTGCGTAAGAGGAGGGGT
ACATGCCCGGTGGTGCGCTGGTGGTGCTCAGCTGCTGTGGTGCCATTAGGACCGAGCTGGTGGCTACATGGGAGTGGTGTGAATTGTACAAAAAG
TTGCAGGTTTGTGCGGGATTTGTGGGTTGTTACTCACCTGGATTCGTGTTGCCATCCTTGGCCACCTCGGGTGTGGGAATGCGCGGTCTGGTCT
TGGCCACATTGACATTCAAGCCATTTAATTTGGAGTCTTAAACATAGAAATAATTTTAAATTTAAAGCATACTCTTGGGGGTTTAAAGAAATTGT
GATTACTACCAAAAAAATTAGTTTGATTTTTATTAATATATTAATATTTTATTTAAAAATGTTTATTTCTATTGTTTTTACTTACTTTGCTTGATA
AGTTGGCGTTGTGCTCTCAACGATTTACGATGCACAAACTTTCCATAGAGACTTGATTTACTTGGCTGCGATCCGGCTTGCTGCTGCTGATGCGC
CTGCTGTAATTGCTGCTGCTGCAGGATGGTCAGTGGCAAGCCGGACTCGGGACTAGAGTAGACGGAGTTGAGGCGGTTCCGGTTGAATGGCATTC
CGCCGGAGGAGTAGGCCGTCGACTGGCTCCTCATGGAACCCATTCGGGAGAGCTGGCGAACCAGCCAGTTGTTTTTCCTCCTTTCCACCATTGGC
GTGTCCACGCTTTCCTGTTTGTGGTTAGTAATAATATTAAAATGTGACTCTTGACATGAAAAAGTCAGCTTCAAAAATATATGTAAATTCGTCTG
CATTAAATTATGATAGATTACCAATAAATGTGACAATAACTTAAGCATGAGAAATATTTTATAGCCTTTTAAGTTGAAGTTGTTAACCCTAAAAA
CGTTATGTTTGCTGGAAATATATCTCACAAAACGCAACTAATGTCTAAGTTACAGCAATAAAACGTTTGCTTTCAATGACTGTTAATATAAATGT
TAGGAGAATCTATGTGTTGAATGCAACTACGTTGGGAGAAATGTATGAAGATACTCACATAGTCCGCGTAGACATCGTCGCTGAGCATCCTCTTG
CCGCCGCCTGGCATTATCTTGGCGTACATGGCGTCCTCCTTCTTGACCTTGTACTTCTCGGCGGAGCCCTTGGGCTCGTCTTTCCGGTAGTGTTC
GGATGCCACCGTATAGGGCAGATCCTTGGGCACCACACACTCCCAGTACTGATCCCGCAGCAGCTCGGGGTGCTCCTCGTGCATCTCGTCCACGA
TCATGTAGGCAGCCTGAAAGCGGGTTTATCAAAAGTGGATCAGTCGAGGGCTGTTCAAAATCGAAACGTGTTCGCCATTTGCGATTTTTTGGGCC
ATTTCGAGGAGGCACTAAACCCAATTACGTCACAATAATTCAACCGTGGCTACTGTCCCACATCGAAACAAAAGAAAAAGTGAAATTGTTTACAA
GTTTTTAATTATTCCATAACAAAAATCAGCGCACAGCCCACTACAGAAAATTGCAAAAACAAAAAGAGGAAAAGAAATAACAATAAAAGTATAAG
CAATACTCATTTGCTTAATCATTTTGCCGCACTCTGTTTTCAATTTGCCATTTATGAGCGACTGAGCCAAGAGTCACGTCTGGTCGTGTGGAGTG
CAGTTGAAATGGGCCAGAAAACCTGGCATTAGCTCCCCGCTGATAACCGGGCTAAAAGCGACCGCTTGAGATGCATTTCCGAATTCGAGCAAACC
CAGCGCGCTGGGGTGACCATAAAAACACACACACACACACACATATACGAAACATTCAATGATAAAGCTCTACAAAAGAGGTTTCAATGTTTTCA
GCTCGTATGTTTTTTTTCACGATTTTCTCATTTTTTGAACAAAAACCTGTTTTCAATTTACTTTTGCTGCTGCTGCTGCTAACTTTTGTAAATAA
TTGCAAGCAACGGCAGGCCCCAGACACAGATACACACACACGCACTGCACACATGCAAAAATCGCTTCTAACACACACAAGCATCGACTTCCCAA
AGCCCAAGTCCAAAACTTCAATCAGCATCAGCAGCAGAAGGAAAGCCGAATAGAGATACCCTCATCTAAATCGAAATCGTAAGTTTGACTTTGGC
GGGTAAATTTGAATTTCACCAGAAGTAATTAAAATTCCCTTTCGAAGATTTATCTACTTTTATAAATGGAACGCTTTTCTAAGTCGCATTTATTT
AATATTTTAATAGAGTCTACTGAGACAGCTTCAAGTAAAATGTATCTAATTACACAGAATGCAAGTTCATAAATAAAGATTTATTAAGTTCGACT
TTCAGTCACATGTAAATTTGTAAGACCTACTTATAATGCACTCCGACTTTTCTTAGCTAGCATCTACTGATTTCATAATTCAACAATTACACATA
TTTCTTGTTTTGTTTTGGTACATTCTTTTTTTAGGGTACTCTGCAGTTCGTTTTGTTACACATTGCATTTGGCTCCTCAGTCTTTTGTTGGCTA
TGTAGAGAATGCCTGTTATTTTTAGCACGTGGCAGACAGACATGTTCTTTTCCTTTCAGTAGCAATCCAAGAAGTGGCTGACTCAAGCGATTATC
GCCTTAAGAGTGCAAAATCTTTACTTAGTTAGCACGCTAACCCAATTAGCGAATTCAGATTTTAGCAGTCATAATACTTGGAAACCTTTGGAATT
ATGATTATGCATATTATCCCCTTGAACAGATACGTATAGATAAGTATCTTGCGGATGTGGGCATCCCAAAGTTTGATTTAAAAGCTGGAAAATTA
AGTTTGGAAGTGGGTATTTCGATACAAAAGCCATCTGTTCCGAATTTGGTACTAATTTAATTTGGAAATTCGTGTATATATGTATCTACACCATG
CTAAATGAAATTAATTGGAAATCATTCAGGTTTTTTTGTGTGAACTTCAAAAGGGGGATCTTTTTCGCAACTCTAACGCAAAATGATTGTTTTAT
GGTTGTATGGACCGCAGGAATTATTGCCACCACTTATTAACAATGTTTAACGGATGGCTGGCGTATAGACAATGTGCCACATCGAATTACGTCAA
GATTGTGCGAATTATCTGCACTGATGACTCACCTTGATGTGTCGGTCAATTAGCCAGTTCAGCTCGATATCATCGTCATCTTCGCCAAAGGGATT
GATTAGCACCTCGGCCACCTTCAGCCAGCCCACGTAGAAAACAAACTGCAAAGATTAATTGAATGCGATTGGATTTTGGTTAATTATATCATGAA
AAACAGAGTCGGACAATTTCAGCAGAACTTGGGAATAATGTGAGAGGGTAAGCCAGGGAAAGCTTGGCAATTCCATTCACTTTTTGCGGCTTCAA
ATTATACGGCATGAACATTAACAGTTAATAATGATAGCTAAACACTTGTCACAGATTTATATCGCGGAGAAACACAAACCAGACCAGAGCTCGGC
AAAATGCCAATTTATTACGGGGAACGTGACCGCGAATCGTTTTACATAAGGCACTTGAAATGTGTCCCCAGCGGAGAACCGCAGAAACCAAAACG
GAAAACAGCAAACAGTTGTAACTGGCCATATCATGATATAGCCCAATATATATATAGTGCATCCGAGCGGCGTATCGCTAACAAGGTATAGCCAT
TACATTCGGCCACTCAGTTTGGCGGAAAAATTGGCAAAAACAATTGCGAACAACAAAAAACCGCAACAAGTTTTTAAACTTTTACAAAACGACGA
GACGTGCAAAATTGACTTTGATTTATAGTAAATAAGGCGGAACGTGCAAATTAAGATAACTTCTAAGCTGTCTTAAATCAAGCGAGAAAAATTAA
TGAATTCATTATATATGGAGCAATTGGAATCACCTGCAATACGGTAAACAGGGGGAAGAACAGATCGGGATCTTCGCGTCCACTTCTGTCCAGAA
CGTTGGGCAACATTTGACGGCCCAAAAGGGCAGCTATGAAATAGGTGTACAGCACCAGGGTGACTACCTGAAAATAAAGTTTTATAATTAATATT

FIGURE SHEET 606

CAATTAAAGAAGGGAAGGTTGGAATATGCTAGAAATATTGAATAAAACTCACCTGAGTGTAGACCAAAGGAACACAGACCGTGTCGTATCCAATA
AGACCACCTAAACGTCTACGAATATCCGAGAGCTCTACCAGTATGGTTTGCACAATATGATCCGAGGCGATTAGGCCATCCTTTCTGGCCCGGTT
TATGATGTTGGTAGCCCAAACGAGAGGCATCCAGTATTTGGACATGGGACTCTTCTGATTCAGTGCCTCAAAGATTTTCATCTCCGATTCGTGCA
TCAGACCCGCATCCACGAGATGTTGGGTTGTGGGAAAACGACGTTTTACACGAAGGGAAATTCGCTGAAGGGTAATCACATAGGCCAAGACCATA
TAGCGCATGATATTACGACGCATCAGGCGACCCGTTTCATTCTGTATTAAGAATTTTTATAGATTATTGTTGGGTTATTTGAAAAAAATTATTTT
CTTACATTTACACCGCCATTTGAGTTGGGAATAGCCGCGCTTATGAACAGGGCCAACGTATCTGGCCAGGGCAAAAGCCTATATTGCTCCCACCA
ACGTTTCACCACCAGATTCACATAGAAGCCCAGCACAAAGGACATGGGTATACTTTCACTCTGCTGCCCAAAATAAAGGCGAATTTTTTTAAAAA
TGCTGAAAATATATTAGTATTATATTATATATTATGTTACCATTTTATAACCCTATTCATACTTACGCTTGCTGACTTTCTGTCAGACCAAATCT
GTAGATAACATTTATGGTATAGTATAAACACAGATACGCAACTAATTCGCGCCAAATCAATTTGTAAACGCTGCCTCGCCATCTATTAAAAAAGG
GAAGGGATTTGAATTAAGTAACTTATAGGTAGTCGAGGAATTTATGGCTTTAATCTGTAACTAACTGGTTTTTGTTTTCTTATACAAACGATTTC
CTCATTCAGACTTTCAATCATTTCCCCCATCGCATTTCAGATTAGGTTTTCGTTTCTAATGAGTCGCCAGTTCTGCAAGATTTTTTATGGGGGTA
TTCCAATCTTGCATGTCAGTTCCAATGAATTCAAATGTCTTAAAGTGTGATTTGATACATTATAAAAAATATATATATGTATATTGATTGGCATA
ACCGCTTCGAAACTGGTACTATTCAGGTGGGGTCTTTGTTCTGTTTGTTTTGATCAAGGTTTCGCTTACCTTCTTCTCTTCAAAAATTTAGGTTG
GGCTCTGACATTATAAGCAAAAAGTAACTAACTCGAGGCTCCCATGAAAAACAATAAGTTGTTAGCCTTTTTTCACATTTTTCCAGTCCTAAAAG
TATCTTTCAATTAGTGAGTTCATTACTGAACGTGTGATAAGCTACAACTGAATTTTCAGAGCTTCGGCGTTTGGCTACCAATTATTCTTCTTTC
TGGTTTGAATGGCAAAAACTGGAACTGTGCAACAGTAACTGGAACTGGAATTGCTATTCTAACTGCCCAGTTACGAGTGACTGCACTTGGGAAAC
AATTAAAGCGAACTGGGGTTAAAAATAAACACACTCTAAAAACAAAATAGCCTGAAACCAGATGTTGTCGCCGCTGAGATGTCACTGTATGGTGG
(SEQ ID NO: 1123)

Exon: 6505..6371
Exon: 6311..5943
Exon: 5862..5734
Exon: 5080..4973
Exon: 3148..2909
Exon: 2579..2270
Exon: 2126..2034
Exon: 1963..1721
Exon: 1569..1001
Start ATG: 6505 (Reverse strand: CAT)

Transcript No. : CT28609
ATGTCCTTTGTGCTGGGCTTCTATGTGAATCTGGTGGTGAAACGTTGGTGGGAGCAATATAGGCTTTTGCCCTGGCCAGATACGTTGGCCCTGTT
CATAAGCGCGGCTATTCCCAACTCAAATGGCGGTGTAAATAATGAAACGGGTCGCCTGATGCGTCGTAATATCATGCGCTATATGGTCTTGGCCT
ATGTGATTACCCTTCAGCGAATTTCCCTTCGTGTAAAACGTCGTTTTCCCACAACCCAACATCTCGTGGATGCGGGTCTGATGCACGAATCGGAG
ATGAAAATCTTTGAGGCACTGAATCAGAAGAGTCCCATGTCCAAATACTGGATGCCTCTCGTTTGGGCTACCAACATCATAAACCGGGCCAGAAA
GGATGGCCTAATCGCCTCGGATCATATTGTGCAAACCATACTGGTAGAGCTCTCGGATATTCGTAGACGTTTAGGTGGTCTTATTGGATACGACA
CGGTCTGTGTTCCTTTGGTCTACACTCAGGTAGTCACCCTGGTGCTGTACACCTATTTCATAGCTGCCCTTTTGGGCCGTCAAATGTTGCCCAAC
GTTCTGGACAGAAGTGGACGCGAAGATCCCGATCTGTTCTTCCCCCTGTTTACCGTATTGCAGTTTGTTTTCTACGTGGGCTGGCTGAAGGTGGC
CGAGGTGCTAATCAATCCCTTTGGCGAAGATGACGATGATATCGAGCTGAACTGGCTAATTGACCGACACATCAAGGCTGCCTACATGATCGTGG
ACGAGATGCACGAGGAGCACCCCGAGCTGCTGCGGGATCAGTACTGGGAGTGTGTGGTGCCCAAGGATCTGCCCTATACGGTGGCATCCGAACAC
TACCGGAAAGACGAGCCCAAGGGCTCCGCCGAGAAGTACAAGGTCAAGAAGGAGGACGCCATGTACGCCAACATAATGCCAGGCGGCGGCAAGAG
GATGCTCAGCGACGATGTCTACGCGGACTATGAAAGCGTGGACACGCCAATGGTGGAAAGGAGGAAAAACAACTGGCTGGTTCGCCAGCTCTCCC
GAATGGGTTCCATGAGGAGCCAGTCGACGGCCTACTCCTCCGGCGGAATGCCATTCAACCGGAACCGCCTCAACTCCGTCTACTCTAGTCCCGAG
TCCGGCTTGCCACTGACCATCCTGCAGCAGCAGCAATTACAGCAGGCGCATCAGCAGCAGCAAGCCGGATCGCAGCCAAGTAAATCAAGTCTCTA
TGGAAAGTTTGTGCATCGTAAATCGTTGAGAGCACAACGCCAACTTATCAAGCAAAACTCCAAATTAAATGGCTTGAATGTCAATGTGGCCAAGA
CCAGACCGCGCATTCCCACACCCGAGGTGGCCAAGGATGGCAACACGAATCCAGCCACCAGCTCGGTCCTAATGGCACCACAGCAGCTGAGCACC
ACCAGCGCACCACCGGGCATGTACCCCTCCTCTTACGCACCCGACACACTACTGCACCAGGAGAGCGGTCAGGTGCTGGGCACGCTGCTGCTCTC
GCCCATCAAAGAGATGGATAGCTCATCGTCCAATAACACTCTGATTCCAGGTCATCCGGCTACCGCAGCTTTGGCAGCCAGCATGAAGGAGGGAT
TCACGCCGAGCAGTATTCCAGCTGCCACAAACATCACCACTCTGTCGTTCCCCTTCAGCGTGACCAGCACCGGTGGGGAAACGATGCCCACTGGG
ACACTGAGCATCCTGCCCATTTCGGCGAATGCCCAGCTGCCCACGATAACGACGACGGCAAGTGGCTACGATCCTAACGATGTGATCACCACGAT
ACCGGTGTCCTTGTCCATCCAGCGATCGCCGTCAGCACTTTCCATTGTGGAGCTGACCGGTGCAGATGTCCAGGATGGATATAGCAACAGTGGGT
CGAGCAATGGCAATGGCGGTATCACCACTACGGCACTGCTGTCCGTTAAGCCCCTCAATGGAAACCAGAACATTTCGCGAAACAACAGTTTCAAC
CTGAGCCTCAATCTGCAGGATCCGCAGCAACGATCCTCGATGAGGTCAGCGGGTCCCACGGGCACAGTGGACAACTCAGGCACGATGCCAATTCC
TCAGAGGAGCGGAGGCCTGGAAACGGGCGAAGTCGGAGGATCCTCGGCCCCCTCAACTCTGGCCAAACACAAGCCGGAACAAAAGACCGGAGAGG
TGTACGTCTGA
(SEQ ID NO: 1124)

Start ATG: 1 (Reverse strand: CAT)

MSFVLGFYVNLVVKRWWEQYRLLPWPDTLALFISAAIPNSNGGVNNETGRLMRRNIMRYMVLAYVITLQRISLRVKRRFPTTQHLVDAGLMHESE
MKIFEALNQKSPMSKYWMPLVWATNIINRARKDGLIASDHIVQTILVELSDIRRRLGGLIGYDTVCVPLVYTQVVTLVLYTYFIAALLGRQMLPN
VLDRSGREDPDLFFPLFTVLQFVFYVGWLKVAEVLINPFGEDDDDIELNWLIDRHIKAAYMIVDEMHEEHPELLRDQYWECVVPKDLPYTVASEH
YRKDEPKGSAEKYKVKKEDAMYANIMPGGGKRMLSDDVYADYESVDTPMVERRKNNWLVRQLSRMGSMRSQSTAYSSGGMPFNRNRLNSVYSSPE
SGLPLTILQQQQLQQAHQQQQAGSQPSKSSLYGKFVHRKSLRAQRQLIKQNSKLNGLNVNVAKTRPRIPTPEVAKDGNTNPATSSVLMAPQQLST
TSAPPGMYPSSYAPDTLLHQESGQVLGTLLLSPIKEMDSSSNNTLIPGHPATAALAASMKEGFTPSSIPAATNITTLSFPFSVTSTGGETMPTG
TLSILPISANAQLPTITTTASGYDPNDVITTIPVSLSIQRSPSALSIVELTGADVQDGYSNSGSSNGNGGITTTALLSVKPLNGNQNISRNNSFN
LSLNLQDPQQRSSMRSAGPTGTVDNSGTMPIPQRSGGLETGEVGGSSAPSTLAKHKPEQKTGEVYV*
(SEQ ID NO: 1125)

Name: BESTROPHIN-LIKE

Celera Sequence No. : 142000013384547
GCTGGCCCGTGCCTGCGCCGCTCAGACAAAGTCCACCTTCCTCAAGCTGGCAGGTCCCCAGTTGGTGCAAATGTTCATCGGTGATGGTGCCAAGC
TGGTGCGCGATGCCTTCGCCTTGGCCAAGGAGAAGGCGCCTGCCATTATCTTCATTGACGAGTTGGACGCCATTGGCACCAAGCGTTTCGATTCG
GAGAAGGCCGGTGACCGTGAGGTCCAGCGAACTATGTTGGAGCTTCTTAATCAGCTCGATGGCTTCAGTTCCACTGCAGATATTAAGGTGATTGC
GGCCACCAATCGCGTAGACATTCTGGATCCTGCTCTGCTGCGCTCTGGTCGTCTGGATCGTAAGATCGAGTTCCCACATCCCAACGAGGAAGCCC
GTGCCCGTATTATGCAGATTCACTCGCGTAAAATGAACGTTAGCAATGATGTGAATTTCGAGGAATTGTCCCGATCCACGGATGACTTCAACGGC
GCCCAGTGCAAAGCCGTCTGTGTGGAAGCTGGTATGATCGCACTGCGTCGCTCCGCCAATTCGGTTACGCACGAAGACTTCATGGACGCCATCAT
GGAAGTGCAGGCGAAGAAGAAGGCTAATCTTAACTACTACGCTTAGACTAAAAATTTGCAGTTTAACTTCACATTGTCAGCTCCCATTAAAATAA
ACCATGGAAATGTAAAATTTTTCAGTTTCGATCTGAGTTGCCCCTTGAAGATCGCCTTTAAAATAACATCGCAACGGCTCTTAAAAGTAACTAGA
ATGGGAGACGTACTGAAATCAATACCCAACCTTTTTAAAATAAACAAAAATATATATCAAATGTCGAGCGATTCATTGGTTTATCAGTACAACAT
TTACATTCTGAGTACGATATTTTTTAAATATCTAAAAAGGTCGGTTTTAGAATTAATAAAAAATATTACATCGGGCGAAATTAGATGATAAATAT
TTACACGCACACTAATTAACCTAGAGGGATGATTTACCAAGTTACTAAGACTAACCAGTGGGATCGAGTGTGTTAGCGCCATCCGGCGCCGCAGA
TGTCGTGCCACTTCCCCCTTGTGACGCTGCATCGACAAGGGACGTGGCAGTGGTTGATGAGGTTTCCGTAGAGGAGGACGCGGCCACAGCATCGT
GAGATGAAACTGCGGCGGCAGGTGGTGTGACGCCCACACCTTCGACCACTGCGGCTACAGGTGCTGCTTCCGCTCCAACCGGCGCCAAGTTAACT
GGCGCAGCAGCAATGTCATCTGCAGCTGGCTGCTGTGCCGGCTGATCCGGCTGCTGAAATGGACGCCTCATGTACATGATGATGCCCAGCAGTAG
AGTTAGAACGGTAATCATGTACAAGTCCCAATTGGCAGCAATATTTTCATCCATGTAGAAGATGAACCTGTAAGGTGACTAAAGGGGAACAACAT
TAAAAAGCTAGTAAACAGTTTATCCATAGGGTTGGGTAATCACCTCCTTGATTGATTCAATCGTGGCCAACATTTGTAGCTTAAAAAGCGCAATG
GCCACAGGCACTTTGGCGTCTGAATTGGTTTCCGCAGCCAAATCGTATAATCTCTTTGCCAGATGCCAGTCTTTCTTCATTCCGAGCCCTTGCTC
GTGCATGTATCCCAAGTTGAACATGGCTTGGGCATTATATTGCTGCTCAGAGGCTTTCCTGTAGGGATTGATGCGGTTATAAGTCGTTTTCACAC
TTCATAGTTCATATTCAACTAACCTGTAAAGAGCAGCGGCAGTCTCGAAGTCCGTCGAAGTACCCCAACCGTAGTAATAGTAATCGCCCAGCTTG
ACTTGGGCCGCAGAATAGCCCTGTCCGGCTGCTCGTTTCCAGTAGTAGAAGGCACGAATCAGATCTTCGTGCCGATCGTTGAACACATGCACCTC
CTTGCGGTCTAGTAAAAAGGCGGCATTACTTTGAGCCACCTCATAGCCCATTTCGGCCATCAACGAGTACTGCATGTAGGCCTCGTCGATGCGGT
TATTTTTATAGTCGCTGTAGGCCATCATCAATCGGCTGCTCCAACGGCCACGCTCCGAAACAGTCTTGAAGAACTGGAATTAGCAAATATGAAAC
GGGTTAGAAAATAATTAACATATTAATTGAACAATAAACTTACTTCTACTGCTGCTGGACATGAACGCAGCATTCCCATACCGTAGGCATTCATC
ACTCCCAGATTATAATAGGCTAAAACATGGCCTGATTGGGTGGCCAGGTTGAAGTACTTAAAGGCTAACTTGTAGTCGGTTTTTACACCATTGCC
AGCTGGAAAAGAAATTTAAATTGTATGGTTCCTAGAAACCCAATCAATAAAATGAAGGTTTATTTACTTACTGAAATACATGTTGCCCAGCTGCA
GTTGCCCATCAACCCAACCTTGATCAGCCGCCTGAGTGAAATAGGATAATGCCTTGATGGAGTCTTTGGGAACACCTAAACCCTTTAGATACATG
AGGCCCAGTCCGCTTTGACCAACTGGATCCCCCATTTCAGCGGCCTTGGAGAAGTACTAAGAAAAATATAATAATACATATTAGAAATATTAATC
AAAAACTGTTATCTACATTATGCGCACCCCAAATGCTGCATCATTATCGGCCCTGATTTGATCACTTCCTTCCAGATAAAGCTTGCCTAAAAACG
CGATGCCAACTGCACTACCTGCATCGGCGGCCATTTTGAAATATTCCAAAGCCTTTTGATGATCTTGCTCGGTGACCTTGCCGCCCTGATAGTAC
ACCTGACCCAATCCCACCTGCGACTGGATGTCGCCTTTATCGGCCAGAAGTTTGTAATAGTCGACAATCTCAGTTTCGGAACTGCCGGGATTCTC
TAGGTCATCCAGCAGTCTTACCCGATGCACAACCGGCCCATTGGCGAAGGTTATCTTGGAAGCCACTTTTTTGGCTACTCGCTTGTAGTGGATCA
GCGCCTTCTCACAGCTAATGGGCACATTGATGCCATAAAGATAGCGATACCCCATGGCCATTTGCGCCGGAGTATTATCACCGAGGGCAGCCAGG
CTATAGTGGATCAGTGCCAGGGGCTGGCTTACATTTTTACCGCCAACGCCCACCGAATAAAGGAATCCCAGGCCCATGTGAGCCTCTGGGACGCC
TTCGTTGGCCAGACTCTCAAACTCATCGACAGCATGGTTGAAATCAAAGTCCATCCATTGACCCAGTAGGGCGGCCCAGGCTAGTTCCGCCCTCG
CCTTGAGGTGATTAAATGCAGCAGCCTTCTTAAGCAAAATCATGGCTACTCGCTTATCCGTGCTTGGCTTGGCCAACATGTCCATTGCGTTGTCG
TACACGGTTTGAGCTGGAAAAATTGCAATCAGCAACTGCAAAACAAATAAAACGATGCCCACTTACCTTCTATTTGGTCTGGGGTAAGTTCTAAC
ACTTCAGTGGATTTGCGTTTGGCTTCGATGCGCTCGATCTCGGCTTTCAGCTTTTGCCGCCTGATCAGACTTTCGTTCCACAGGCGTTCGAACAG
GGAAGCCGGCATAACCTTCGTCCTGGAAGCAAACTTTGTGGACTCCTTGGGTTTGTCTGCCTTGCGTTCGTTGCTTTCCGACGGAACCCGCGACT
CTGATTCCGCCGTGGTCACCTCCTCCGCCTCCGCCTGGGTGGAGGGCTCATTGGGCAGCGTTGGCGTGGCTGTTCCCGTGCCCAATCCCGTTCCC
GTACCCGTACCTGTGGCCGAACCCAAACTGCTGCCCGTACCATCAATGTTGGGCCCTTGGAGCTCCTCCGCTCGCAGCTGCCAGGCGAGAAGCAG
CGCCAGCAGGCACATCCAGCTGTTGGCCTTCATCGTCGCCTATCTGCCTTTCTCGATGGCAATGTGGATGTACAACGGCAATTTTGGTCTTCGCC
TTTGCTGCGTCTATATGGTGCTCTTCCACTTCTGACGTGTTGTGTTATTTACTGTTTTCTTGGGGCGCAGGGTCGGCAAAAAGAGTGGATTGCTG
CTTCTGGGTGGATTCGTTTGACTTACTGGTAGCTCATTTTGGCCACCTCGACTTGGTGGTGGTTGGAATACCTTGGTTCGGTTTCCTTAATTTTT
CACACGTAAGATTCTTTTTAATCTTTTTTGTTGCAATGCTTAGTGCTGCGAACGGGCCGAGGTTTGTGTGCCAGTGCTGCAAAGCACCGCGTCTA
AAACAGTCTTTTCCAGGGGCGTCTCCAAAAATATTTTCGCGAATTAAAAAGGAGTAATAAAATCGAGACAGGCTTATAAATATTTAGTCAGGACG
ATATCAAAACTTAATTACAACTTTTTTTATTATTACAAGCTACATTTAATAATATTACAATTTGCCTAAGCCTGACGGTAAAACATAAAATTTT
AAAAATATTTGTACATTTCTTTAAAACGTATATGCACCAAAATGTGGAAATTATGCTCAACAATTATTTCCCGGGCAACTGCGATAGTTAACGTC
TAGAATGTCTTACCCCGAAAAATTCCCAGGGCTTGCTAGCTACGCCCCTGGATTTTCCGGCTGTTGTTTCGTTATGCAAAGGAACGCGCAGAGTT
TAACCAGAAGGAAATCTGAATTGGAACTGTTGACGCGCAATCGAAAGTGATAATTACGAGCGGGAATAATTAGAATACGAGGAAGATTTCCGCCC
GTGTGAATCACCAACTTTTGTCTCGTCCAATCCAAGTCAGCCACTGAGCAGCCGGCATGGAGATGAGTGTAAGTAGAAGCTGCGACCTGCGTGCC
AGACACCCAGACCCAAAAGTCACAGCCCAAAACCAAATTGAAAACCGAAACCAGTTCCAACCCGCGCTTCAACCGAGTGAGTCGCACAGCGAATC
ACTCTTCGAGCTCAGCCGTTAGTGCTGGTGAAAGTTACAGCTGTTGCGTTCGCTACGTTCGCTACCTAGTAACCGCCACCTGTGCCCCGATTCCT
AATCCTCCAGTCGACACCTGTTATTTCAGGCTGCCATGTTCGCACGCGTTTCCTTCTACCCCACCCTGCTGTACAATGTCCTGATGGAAAAGGCA
TCGGCCAGGAATTGGTACGATCGCATCGATGAGCATGTGATACTGGGAGCACTGCCCTTTCGCAGCCAGGCCAATGACGTAAGTATCCCCACGGA
ACCAAGCCTGAAATCCTTCTAAATCCTTGTTTAACCGCTCAGCTCATTGAAAAGGAGAACATGAAGGCGGTGGTGTCGATGAACGAGGACTATGA
GCTGACCGCCTTCTCCAACAACACGGAGAAGTGGCGAAAGCTTGGCATTGAGTTCCTGCAGCTGGCCACCACCGACATCTTTGAGTCGCCCAATC
AAGAAAAGCTCTT
(SEQ ID NO: 1126)

Exon: 4333..3392
Exon: 3338..2593
Exon: 2526..2352
Exon: 2282..2134
Exon: 2068..1734
Exon: 1673..1469
Exon: 1408..1001
Start ATG: 3833 (Reverse strand: CAT)

Transcript No. : CT28737

FIGURE SHEET 608

TAATATTATTAAATGTAGCTTGTAATAATAAAAAAAAGTTGTAATTAAGTTTTGATATCGTCCTGACTAAATATTTATAAGCCTGTCTCGATTTT
ATTACTCCTTTTTAATTCGCGAAAATATTTTTGGAGACGCCCCTGGAAAAGACTGTTTTAGACGCGGTGCTTTGCAGCACTGGCACACAAACCTC
GGCCCGTTCGCAGCACTAAGCATTGCAACAAAAAAGATTAAAAGAATCTTACGTGTGAAAAATTAAGGAAACCGAACCAAGGTATTCCAACCAC
CACCAAGTCGAGGTGGCCAAAATGAGCTACCAGTAAGTCAAACGAATCCACCCAGAAGCAGCAATCCACTCTTTTTGCCGACCCTGCGCCCCAAG
AAAACAGTAAATAACACAACACGTCAGAAGTGGAAGAGCACCATATAGACGCAGCAAAGGCGAAGACCAAAATTGCCGTTGTACATCCACATTGC
CATCGAGAAAGGCAGATAGGCGACGATGAAGGCCAACAGCTGGATGTGCCTGCTGGCGCTGCTTCTCGCCTGGCAGCTGCGAGCGGAGGAGCTCC
AAGGGCCCAACATTGATGGTACGGGCAGCAGTTTGGGTTCGGCCACAGGTACGGGTACGGGAACGGGATTGGGCACGGGAACAGCCACGCCAACG
CTGCCCAATGAGCCCTCCACCCAGGCGGAGGCGGAGGAGGTGACCACGGCGGAATCAGAGTCGCGGGTTCCGTCGGAAAGCAACGAACGCAAGGC
AGACAAACCCAAGGAGTCCACAAAGTTTGCTTCCAGGACGAAGGTTATGCCGGCTTCCCTGTTCGAACGCCTGTGGAACGAAAGTCTGATCAGGC
GGCAAAAGCTGAAAGCCGAGATCGAGCGCATCGAAGCCAAACGCAAATCCACTGAAGTGTTAGAACTTACCCCAGACCAAATAGAAGCTCAAACC
GTGTACGACAACGCAATGGACATGTTGGCCAAGCCAAGCACGGATAAGCGAGTAGCCATGATTTTGCTTAAGAAGGCTGCTGCATTTAATCACCT
CAAGGCGAGGGCGGAACTAGCCTGGGCCGCCCTACTGGGTCAATGGATGGACTTTGATTTCAACCATGCTGTCGATGAGTTTGAGAGTCTGGCCA
ACGAAGGCGTCCCAGAGGCTCACATGGGCCTGGGATTCCTTTATTCGGTGGGCGTTGGCGGTAAAAATGTAAGCCAGCCCCTGGCACTGATCCAC
TATAGCCTGGCTGCCCTCGGTGATAATACTCCGGCGCAAATGGCCATGGGGTATCGCTATCTTTATGGCATCAATGTGCCCATTAGCTGTGAGAA
GGCGCTGATCCACTACAAGCGAGTAGCCAAAAAAGTGGCTTCCAAGATAACCTTCGCCAATGGGCCGGTTGTGCATCGGGTAAGACTGCTGGATG
ACCTAGAGAATCCCGGCAGTTCCGAAACTGAGATTGTCGACTATTACAAACTTCTGGCCGATAAAGGCGACATCCAGTCGCAGGTGGGATTGGGT
CAGGTGTACTATCAGGGCGGCAAGGTCACCGAGCAAGATCATCAAAAGGCTTTGGAATATTTCAAAATGGCCGCCGATGCAGGTAGTGCAGTTGG
CATCGCGTTTTTAGGCAAGCTTTATCTGGAAGGAAGTGATCAAATCAGGGCCGATAATGATGCAGCATTTGGGTACTTCTCCAAGGCCGCTGAAA
TGGGGGATCCAGTTGGTCAAAGCGGACTGGGCCTCATGTATCTAAAGGGTTTAGGTGTTCCCAAAGACTCCATCAAGGCATTATCCTATTTCACT
CAGGCGGCTGATCAAGGTTGGGTTGATGGGCAACTGCAGCTGGGCAACATGTATTTCACTGGCAATGGTGTAAAAACCGACTACAAGTTAGCCTT
TAAGTACTTCAACCTGGCCACCCAATCAGGCCATGTTTTAGCCTATTATAATCTGGGAGTGATGAATGCCTACGGTATGGGAATGCTGCGTTCAT
GTCCAGCAGCAGTAGAATTCTTCAAGACTGTTTCGGAGCGTGGCCGTTGGAGCAGCCGATTGATGATGGCCTACAGCGACTATAAAAATAACCGC
ATCGACGAGGCCTACATGCAGTACTCGTTGATGGCCGAAATGGGCTATGAGGTGGCTCAAAGTAATGCCGCCTTTTTACTAGACCGCAAGGAGGT
GCATGTGTTCAACGATCGGCACGAAGATCTGATTCGTGCCTTCTACTACTGGAAACGAGCAGCCGGACAGGGCTATTCTGCGGCCCAAGTCAAGC
TGGGCGATTACTATTACTACGGTTGGGGTACTTCGACGGACTTCGAGACTGCCGCTGCTCTTTACAGGAAAGCCTCTGAGCAGCAATATAATGCC
CAAGCCATGTTCAACTTGGGATACATGCACGAGCAAGGGCTCGGAATGAAGAAAGACTGGCATCTGGCAAAGAGATTATACGATTTGGCTGCGGA
AACCAATTCAGACGCCAAAGTGCCTGTGGCCATTGCGCTTTTTAAGCTACAAATGTTGGCCACGATTGAATCAATCAAGGAGTCACCTTACAGGT
TCATCTTCTACATGGATGAAAATATTGCTGCCAATTGGGACTTGTACATGATTACCGTTCTAACTCTACTGCTGGGCATCATCATGTACATGAGG
CGTCCATTTCAGCAGCCGGATCAGCCGGCACAGCAGCCAGCTGCAGATGACATTGCTGCTGCGCCAGTTAACTTGGCGCCGGTTGGAGCGGAAGC
AGCACCTGTAGCCGCAGTGGTCGAAGGTGTGGGCGTCACACCACCTGCCGCCGCAGTTTCATCTCACGATGCTGTGGCCGCGTCCTCCTCTACGG
AAACCTCATCAACCACTGCCACGTCCCTTGTCGATGCAGCGTCACAAGGGGGAAGTGGCACGACATCTGCGGCGCCGGATGGCGCTAACACACTC
GATCCCACTGGTTAG
(SEQ ID NO: 1127)

Start ATG: 501 (Reverse strand: CAT)

MKANSWMCLLALLLAWQLRAEELQGPNIDGTGSSLGSATGTGTGTGLGTGTATPTLPNEPSTQAEAEEVTTAESESRVPSESNERKADKPKESTK
FASRTKVMPASLFERLWNESLIRRQKLKAEIERIEAKRKSTEVLELTPDQIEAQTVYDNAMDMLAKPSTDKRVAMILLKKAAAFNHLKARAELAW
AALLGQWMDFDFNHAVDEFESLANEGVPEAHMGLGFLYSVGVGGKNVSQPLALIHYSLAALGDNTPAQMAMGYRYLYGINVPISCEKALIHYKRV
AKKVASKITFANGPVVHRVRLLDDLENPGSSETEIVDYYKLLADKGDIQSQVGLGQVYYQGGKVTEQDHQKALEYFKMAADAGSAVGIAFLGKLY
LEGSDQIRADNDAAFGYFSKAAEMGDPVGQSGLGLMYLKGLGVPKDSIKALSYFTQAADQGWVDGQLQLGNMYFTGNGVKTDYKLAFKYFNLATQ
SGHVLAYYNLGVMNAYGMGMLRSCPAAVEFFKTVSERGRWSSRLMMAYSDYKNNRIDEAYMQYSLMAEMGYEVAQSNAAFLLDRKEVHVFNDRHE
DLIRAFYYWKRAAGQGYSAAQVKLGDYYYYGWGTSTDFETAAALYRKASEQQYNAQAMFNLGYMHEQGLGMKKDWHLAKRLYDLAAETNSDAKVP
VAIALFKLQMLATIESIKESPYRFIFYMDENIAANWDLYMITVLTLLLGIIMYMRRPFQQPDQPAQQPAADDIAAAPVNLAPVGAEAAPVAAVVE
GVGVTPPAAAVSSHDAVAASSSTETSSTTATSLVDAASQGGSGTTSAAPDGANTLDPTG*
(SEQ ID NO: 1128)

Classification: hypothetical
Gene Symbol: BcDNA:LD23587
FlyBase ID: FBgn0028475

Celera Sequence No. : 142000013384857
AGCAGTTTTCGTCCGATTTTGTCGCATATCCGAAAAGTATGCTTTAAATATGATATCTTTTTTATACCAATTCCTCGTGGAGTAAAATGTTATAC
TAAATTCGTAAAGGCCACAATTTTGAAGTCTTGAGATTTTGTTGATATCATTCTATCGATAGCCAAAAACTGTCACACCCTATTGTTCTATAAAT
ATTTTGAATTTATACTATTTTAACACAGTTTGGAAGAAGTATTTATTTTTTGAATCAATTTAAAAATGTTATGCAAATTTCCAGCGAGATTCCAT
AAGAATTTTGAATTGATCCCCCGCACCCACAATAGCTAAGTAAGAGGTATCTGATAGTCGATGATACCGTTCCGTTTTCCCTTTGTTTTCGTTTT
GAAATAAACTGACAGACTACGTGTCCTGGATCCTATTTAGTTTCTATTTACAAAAAAATAAAAGATAAAATATACCACAGCCAAGAACTTTTAAT
TTAATAAGAAACAGCGATTGATTAGCTTAGGTCCATTACGTTTATTTGTTGAAAGTAAATTAAATTTAGGTTACACTGCCACAGCATTTTTAAA
TATATATATTTGCATCTATGCCCTAATTGATTTCGTTTTATGGGAACAGCATTTTTGTTGCATAATTAATTATTTTTGGGAAAAAATAATCACA
AATGTGTGTGAGTGTGGCATCGGTTTTGACTTGAAATATAATTTGATCATATTTTAAAGACTCTGCTCTTCAAAGAAAAGATGAGTTGACAATCT
ATTGCATCAATGGATTTCAGTTTCATATGCTACACAGTAAACTTAAAATTAGTTAAAACGAGAATAATGTACAATATACAGGCCAGTGCCTCTCA
ATCATTTGATTTAATTGTTTTCATTGTAATAGTATTGAAAAGCAGTTCTCAAAAACATCGAAATAAAAAGACGATCTTAGCTAAAACGTAACTAT
GTTCGTGATTCAGTTTAATAGGTGTGCTGAGTGTTGCTTTAATATTTGTTTTTTTTTTTATTTTGTAGAACAACTGAATCAAAGATTCATGCGA
ATCAGGTAAACAATTTAATCTTAGATGTGGTAACTTGGTATTTTTTCTCTTCCATCTATCGTTTACATTTTTGGTTGGGAGTTTGCCGGCGAGGC
TGTATTTCGTTTGCCAATTATTGGGTTAATTGTAAAATGTATATAAAATAAATCACATTTCTATACGCACATAAATGACGCGTGTGTGTGTATC
GTGTCTGTGTGGATTTTTGTGGGTGGGTGCCCTGGAAGTGGGACAGCGCACAGTCCAACACAAGGTTCGGCTACATATTTATTAATATTAATAAT
AAACATATGTTAATTGTTTAAAACAAAGAAGCTGGCAGCCACAGCGCTGATCGCGAACCCAAACGAAAAACTCGTACCCAGGCTGGGCTCATGTC
TCATCTCTCAAGGATCGACGACCACCTACAACCTACAGGCTAAGGACTCGCGGCGAACTAGCTCGCCTCATATGAGAAACTGGCGATCGGATGCG
CTGTGCGGCAGGGCGGCCACGCCTATGCCGCCTTGCGTGGGCGTTTGCAGAAACGCCGAATCGTCGACTGTTGCTGAGTCAGCTGCAGGCGTGCT
GATTGCTATCGGTTCGTAGATCGAACGATGCGGTGGCATATCGTCTTCGTCCTTAAAGGAGCCGCTTAAATTCGGATTGAGGATGTTGTTCGATG CGGGCGAGGCTACAGCAATTGTCCCCGTCACCGGCAGACCCATGGCACTGGTACCGGACTCAACGCGCTCCAGATAGGGTGGCGCCGCCACACTA
ATAACAGCTGGCTGCCGGCGGAAGAACGAGCTAAAAGCAGTAAAAACAGGAAGTTATGCACCTTCTACCAGTGAGCTTCATCACAAATATATAAT
TACGCAAAATTTATTCTCGACCAGACCGAGCGACGACTCTCAGTTAACTGTTCGGCTAGGTGGGCCGGTAGATTCGGAGCACGATCAAAGGGATT
GATGCGTTCATGTGCTCCAGAAGACGTGGCCGGGCGCACAGTAGAGGCCAGCAGAGCTGTACAAGTAATAGGGTGTGTTATTTAAAAAAATCAAA
AAAAATATTTCGGCAGCAGACGTACCGTTCTCATCGTCAGAGCTTTGGGACTCCTCGAACGGATTTCGACCGGCGTGACCACGGCGGAAGGTTCC
ATGTCGCGTGGTTCCAGCGACAGCCGCCGCCGCAACGCTTGAGCTGCTCCCAGCTGCTCCACCAGCCGAAGAAGCCGAGCTCACTTGACCCACCT
GCCTACCATTGGACTGCTGTTGCTGCAGCAGCGGCGTTGTGTCGTCATCCGTATCCGTGACATTATCCAAAGAAGGCTGTCGACTCCGACTTGCA
CGCGCTTCGCCCTTCGTAAAAACCTTGCGCTTACAAATGGGACACACCCGACGGTTTTCGGTAAGCCATGGATCAATGCAGTGCGTGTGATAGGC
TGAAAGTAATAACGAATTAATATGTTGTCTTTGCATTAAAGAATTTTCTGGCGATGTCATATTAGTTTAAGCATTTGTATATGATATATTCTGAA
ACTACTAAAGCTGAGCAAATAACCAAGACTGTATCCCTTACGATGTGAGCAGGGCAGCACGCGAAGCTTATCGTCCTCTATGAAGTCCTCCAGAC
AGATCACACAGGTGTCGTACTTGTTGTTTGCGTTGTTCTTGGTATATCGGAGCACTGGCAATTTCTTCAGCATGCTCTTTGGCAGTCGATGGCGA
CGCAAGCGGCGCTGCTCGCGGATGCACTTGTAGATCATATAGATAACCTGTTCGGCAATCAAAGCAATTCAGTTGTGTAAAACAGCGTTAAAACT
CCAGATTTCTTACCATTATGATGAAGCACATACCGATCAGAATGGAAAACGGCAATATTAACTGTGTATTGATATTGAAGGGCAGCTCATCGTTG
ATGATTAGCACCACCTCGGTCGTAAAGTAAGTGGCCAGCGCTTTACCCGTCGTGTGGCCCACGAAAACCGAGGGTATTCTTATACCCGTTATGTT
TTCGGCGGACATTTGCTCTGTAATTGAATATGGGTTTAAACAAATCATATTTAGACCTGAGCACCTATGTGTAATCACTTACCCAAGTCATCGCC
TTCATTATTGTAAACAATCACAGCAGAATAACTCGCATTCTGGGCCACTCGTATCTTACGCTCAAAGACGCATTCGCCCACTACAAAAGATTTGAG
TTAGGTCGAACTGAAGTGTTTATATCTACCACATATAGCTTACCGCGCTACAAGTGCCACAAATTTGGCTGAGGGTGGGTATTTCAGGTGCGGTG
GTCTGTCCAGGCTATCACAACCGTAATAAGGGCGCCTAGCGGGAACCACATACACTTTGAGACCATTTGAAGGCAGATTGGGACCGAATTGAGCT
GGCAGATCATTGAACTCCTCGATCAACTGTGAGTAAACAATATACGATGGGCGTAATAAGTATTTGCAATTTGTAATAATATTTCTAAAATATTA
GCAAGTTAAACTTGTCATTAATTGAACTTGCCTGGCTGGTTGCTTTCCGGTAAACCAGCACGTGGCCCCCGACCAAGGTCGCCTCATGACAGACC
AGGCACAAGCCCAACAGGGTGAGTATCTGGCAACTTCTCTTGGACATTCTGTCGCGGAGGACACACGTTCTGGAGATGATCGGGACTTGGTCTGT
ACTGTTATTGCTCTAGTCCGCTATGTCCAGTGCTGTAGCGATTTGTCTTCAACATCCGCACCATTCGCATGTCTCATCTGTGTCCCACCGCCAGC
GATTCTGTGCGCTTGGACTTCGGACTTAAAACAAAAGAAAATGTTTTTTAACATATTATGAATGATTATTTATTTGGGTGCTATAACTATTTATA
TAAATAATAATAATAATTTTTGCAACTCGAGTATTATCCTGCGTGTAGTCAACCTAGGCGTAAACCTCTCCGCCTACGAGGCCATGGCAACAAAG
AGCTCAGCTGATAAGATAAACGGCCAACTGGGGGTATTGTTGATTTGCTTACTCTGAAAAAATTTGCGTTTCTTCAGTCACGCTGCACTTACAGC
TGGTTTGTTTGTTGACACAGTCAGGCAGACGACGGTTCGTTCGGGTTTTCGCGAATGCATTAATGGTTACTTCAAACAGAACAGAAAAATCAACG
CGTTTCGCTCCTTGGCTGCTATTGTACTCAATTTGCCATCAATTAATTTTATCGCGATCAAATAATAGTGGCCGAGATCTTGGGCGGCAGCTGCT
GTAGTCGGAACAAATAGGTTGATGAGTCACGAACACCGCTCCATGCTAAAACCAGAACCCAGACCGCATGCACATTTAACTATTTAGCGTCGACG
CACCGTCGGTCCACAGTTGGGGCAGAAAAAGTGGAAAGTTTCTATTCGTACATATATTACAAATTCTGCTAATACACAGCCGAGGGGAGGTGTGC
AAATATGTCACAAAATGTTTATTAAAGTTACGATTTGACAAAGAAAACGTCACTGGCATTAGCACATCGGTAGACAATCGGAGCAAAGGCTCCAA
TGAGAACGTGACTTTGTTTTTATTGGATGGTTAAACAATAAATGGGAGGCCGACATTCGTTGTTCCAATGAGAAATTCAATCTGGGGAGGCGCGT
GCGTTTAATAGAATTACGCCCTACGGATTGCCCAACAGTCTTTGCATTCAGGTATGAGTTGGTGATCCTACCATGTAACATTCTATTTCCATTTC
ATGGCATGTTATAAAGAAACGACTACGGTGTAGAAGGAGTTTGTTTTTAAGATGATTTCAACTAGAATGCTATTCCTTTGACAAACAAGTAGTTC
AACAAATTATTAAAATGTTGGTTACTATCGCATATGTTTCTACACAATTTTTTAGCAACTTGGCGATCTTTTGCCAATTAATAGTATGGTCATTT
CGCAATTTTCAAAACTTGTATATAATTTTCCTTGCAAAAGCGCTTGCAAAAAAGCTAGAGTAGCTATCTGGATATGTAGAGATACATATGTATTG
ACTGGATTGTTTTAAACAATCCTGACATACGGATTGAATGTTTAGCGACGAGGAATGCAATTCGCGTTAATTCGCTTTGTTTGGAAGGCCGATAT
CAATTTACACATTACACAGCGTACGCAGCCACCCACCAACACACAAACACGCGCACACACACACACCTTGAACTTTACAAGGCACGAGTGTG
GTTTCAAGGTTTTCCTTTTTGGGGGAGGGCATACGCTCACGCAAACACGCATACATACATACATAGGCACTAGGCAGGTGTTTCCTGAATGGTGT
ACAACGGTGGGTTACAGGTGAAAAGCGGCCTCGATTGGAGGCAGCAGCCCACAAGTTATTGCACTTAAATTTCGTATATTCGCTTTTGTTGTTTT
TTTTAGGCGCCTCTGTGTGCGTGCCTGCTACTGTGCTTGTGTGCGTTCAATTAGCACAACAACAAAGCAGCTGAGCGATTTCCTTTTGCTTTCCC
GACGCCCATTCGCGTAAATCCACTGGTCACTCACTTGATTAGGGCTTCTCGTGCTCTTAGTTGACCGTTTGGAGCGACTTCTGGCCAGTTCCTGT
ATCCAATCCTATTTTTTCAGCACTCGCTCGCCTCCTCACTCGTCGCCATCGCACTGGTATTGCGTTGTACTTTGTTTTGCTCCCTTTTGGGGCTC
GGACTCCTCGGGTTCCTTTAGTTGGTGGTCGTGGTTCAGCGGGGACAGCGCAGTGGCTGCGAAAAGAGCATGACAGTCGCGATAAGAACGCTTTG
GGTTTGGTTCACTTTTCTAATTATCGGATATTAGAATTTACATCCCACCCGAACACAGACACATATACAGGGCTAGAGCTGGAACTAAATCGATG
TATAGCTGCTGCTGGCTTCCTGACGGCGATGTTTCGTACATCGATTACTCCCATATTTCGATAGCTATCGACTAAAATTTTAAAAATATTAAAA
TCCAGTATTCTCAGCAACTGTTTCAGATCATTGTACAGAATTTAGAATTCTCAACTTCAGAACCTGAAACCATATAGAAATATAATACTAAGATA
TAGCATTAATAACTAGTTTTTAAGATTCTAGAAGTACAAATACAATGAATTGGTTAAAATCAGTTTCTGTGCAAAATACTACTTGCCTTTTCGAA
TTAACCAAGAAAATTAACCGATTTTCAGTGGTGCGTTTATATTTTGTGTTGAACAATAATGCATTTGAGTTATGAAACATTAAAATCACATGACT
GCGGGCTACTTGATCCAGAGATACATTTTCCCCTGGATGGTGTGCTTGACGGGATTGATCTTCTTCAGGATTTTCGTCATGGTCTCGACCAAACG
GTCGCTGGAGACAGGCGTCTTCTTGTTCTTGAACTTGGTGAGCAACTCGGTGGCGGTCAGGGGCTTTCGCTTAAGATACCGACGCACCGCCTCCT
CGGTGATGCCCGTAGTCCCTAAACAAAATACATGAAATTAGAATTAGGAATTCCAGTATATCACGGCTTTACTCACTCTACTTTGCCGCCAGAGAA
GGAAGTGGGCAGCGATGTGCTAATCTCGTTCTTAGGCCTCTTTGCTGGCGTGCTGGTGGGACTGTTGCTTGTGTCCGAAGCGGTGAGATCGCTGG
GTAAGCTGTTCATCTTGCGCTTGCTGGCATCCGTCGAGAGCGTTGGAGTGGCCGAGCGAGATTTATTGGCATTGCTGCTGCTGGCGATGACCTTG
CTGCTCGCAGCGCTCTCTTTCTCCTTTTCCTTTTCCTTGTCTTTGTCCTTGACGACGACCTTCTTCTTGGGCGGTCCGTTGCTAAGGTCGTCCTC
GGAGTCTG
(SEQ ID NO: 1129)

Exon: 5848..5545
Exon: 3824..3547
Exon: 3446..3274
Exon: 3214..3123
Exon: 3057..2864
Exon: 2802..2607
Exon: 2469..2116
Exon: 2051..1904
Exon: 1835..1001
Start ATG: 3657 (Reverse strand: CAT)

Transcript No. : CT28877
TTCGGGTGGGATGTAAATTCTAATATCCGATAATTAGAAAAGTGAACCAAACCCAAAGCGTTCTTATCGCGACTGTCATGCTCTTTTCGCAGCCA
CTGCGCTGTCCCCGCTGAACCACGACCACCAACTAAAGGAACCCGAGGAGTCCGAGCCCCAAAAGGGAGCAAAACAAAGTACAACGCAATACCAG TGCGATGGCGACGAGTGAGGAGGCGAGCGAGTGCTGAAAAAATAGGATTGGATACAGGAACTGGCCAGAAGTCGCTCCAAACGGTCAACTAAGAG
CACGAGAAGCCCTAATCAATCCGAAGTCCAAGCGCACAGAATCGCTGGCGGTGGGACACAGATGAGACATGCGAATGGTGCGGATGTTGAAGACA
AATCGCTACAGCACTGGACATAGCGGACTAGAGCAATAACAGTACAGACCAAGTCCCGATCATCTCCAGAACGTGTGTCCTCCGCGACAGAATGT
CCAAGAGAAGTTGCCAGATACTCACCCTGTTGGGCTTGTGCCTGGTCTGTCATGAGGCGACCTTGGTCGGGGGCCACGTGCTGGTTTACCGGAAA
GCAACCAGCCAGTTGATCGAGGAGTTCAATGATCTGCCAGCTCAATTCGGTCCCAATCTGCCTTCAAATGGTCTCAAAGTGTATGTGGTTCCCGC
TAGGCGCCCTTATTACGGTTGTGATAGCCTGGACAGACCACCGCACCTGAAATACCCACCCTCAGCCAAATTTGTGGCACTTGTAGCGCGTGGCG
AATGCGTCTTTGAGCGTAAGATACGAGTGGCCCAGAATGCGAGTTATTCTGCTGTGATTGTTTACAATAATGAAGGCGATGACTTGGAGCAAATG
TCCGCCGAAAACATAACGGGTATAAGAATACCCTCGGTTTTCGTGGGCCACACGACGGGTAAAGCGCTGGCCACTTACTTTACGACCGAGGTGGT
GCTAATCATCAACGATGAGCTGCCCTTCAATATCAATACACAGTTAATATTGCCGTTTTCCATTCTGATCGGTATGTGCTTCATCATAATGGTTA
TCTATATGATCTACAAGTGCATCCGCGAGCAGCGCCGCTTGCGTCGCCATCGACTGCCAAAGAGCATGCTGAAGAAATTGCCAGTGCTCCGATAT
ACCAAGAACAACGCAAACAACAAGTACGACACCTGTGTGATCTGTCTGGAGGACTTCATAGAGGACGATAAGCTTCGCGTGCTGCCCTGCTCACA
TCCCTATCACACGCACTGCATTGATCCATGGCTTACCGAAAACCGTCGGGTGTGTCCCATTTGTAAGCGCAAGGTTTTTACGAAGGGCGAAGCGC
GTGCAAGTCGGAGTCGACAGCCTTCTTTGGATAATGTCACGGATACGGATGACGACACAACGCCGCTGCTGCAGCAACAGCAGTCCAATGGTAGG
CAGGTGGGTCAAGTGAGCTCGGCTTCTTCGGCTGGTGGAGCAGCTGGGAGCAGCTCAAGCGTTGCGGCGGCGGCTGTCGCTGGAACCACGCGACA
TGGAACCTTCCGCCGTGGTCACGCCGGTCGAAATCCGTTCGAGGAGTCCCAAAGCTCTGACGATGAGAACGCTCTGCTGGCCTCTACTGTGCGCC
CGGCCACGTCTTCTGGAGCACATGAACGCATCAATCCCTTTGATCGTGCTCCGAATCTACCGGCCCACCTAGCCGAACAGTTAACTGAGAGTCGT
CGCTCGGTCTGGTCGAGAATAAATTTTGCCTCGTTCTTCCGCCGGCAGCCAGCTGTTATTAGTGTGGCGGCGCCACCCTATCTGGAGCGCGTTGA
GTCCGGTACCAGTGCCATGGGTCTGCCGGTGACGGGGACAATTGCTGTAGCCTCGCCCGCATCGAACAACATCCTCAATCCGAATTTAAGCGGCT
CCTTTAAGGACGAAGACGATATGCCACCGCATCGTTCGATCTACGAACCGATAGCAATCAGCACGCCTGCAGCTGACTCAGCAACAGTCGACGAT
TCGGCGTTTCTGCAAACGCCCACGCAAGGCGGCATAGGCGTGGCCGCCCTGCCGCACAGCGCATCCGATCGCCAGTTTCTCATATGAGGCGAGCT
AGTTCGCCGCGAGTCCTTAGCCTGTAGGTTGTAGGTGGTCGTCGATCCTTGAGAGATGAGACATGAGCCCAGCCTGGGTACGAGTTTTTCGTTTG
GGTTCGCGATCAGCGCTGTGGCTGCCAGCTTCTTTGTTTTAAACAATTAACATATGTTTATTATTAATATTAATAAATATGTAGCCGAACCTTGT
GTTGGACTGTGCGCTGTCCCACTTCCAGGGCACCCACCCACAAAAATCCACACAGACACGATACACACACACGCGTCATTTATGTGCGTATAGAA
ATTGTGATTTATTTTATATACATTTTACAATTAACCCAATAATTGGCAAACGAAATACAGCCTCGCCGGCAAACTCCCAACCAAAAATGTAAACG
ATAGATGGAAGAGAAAAAATACCAAGTTACCACATCTAAGATTAAATTGTTTACCTGATTCGCATGAATCTTTGATTCAGTTGTTCTACAAAATA
AAAAAAAAA
(SEQ ID NO: 1130)

Start ATG: 472 (Reverse strand: CAT)

MSKRSCQILTLLGLCLVCHEATLVGGHVLVYRKATSQLIEEFNDLPAQFGPNLPSNGLKVYVVPARRPYYGCDSLDRPPHLKYPPSAKFVALVAR
GECVFERKIRVAQNASYSAVIVYNNEGDDLEQMSAENITGIRIPSVFVGHTTGKALATYFTTEVVLIINDELPFNINTQLILPFSILIGMCFIIM
VIYMIYKCIREQRRLRRHRLPKSMLKKLPVLRYTKNNANNKYDTCVICLEDFIEDDKLRVLPCSHPYHTHCIDPWLTENRRVCPICKRKVFTKGE
ARASRSRQPSLDNVTDTDDDTTPLLQQQSNGRQVGQVSSASSAGGAAGSSSSVAAAAVAGTTRHGTFRRGHAGRNPFEESQSSDDENALLASTV
RPATSSGAHERINPFDRAPNLPAHLAEQLTESRRSVWSRINFASFFRRQPAVISVAAPPYLERVESGTSAMGLPVTGTIAVASPASNNILNPNLS
GSFKDEDDMPPHRSIYEPIAISTPAADSATVDDSAFLQTPTQGGIGVAALPHSASDRQFLI*
(SEQ ID NO: 1131)

Classification: hypothetical

Celera Sequence No. : 142000013384547
GCGCGGCTCTCCTCATACTCCCGGGCCACATCCGTCAGGCTCTTGGCCTCGGCGGACTCCTTGTTGTTGCTGCTGCTGCTGCAAATGGATGAGGA
GGCAGCGGCCTCGCTGGTCTCTGTGGTCTGGGCAGCGTTCTGAATGACGCTTGAGAAGAGCAATGGCGCCGAGGACGACGTAGCAGCGGTGGAGG
AGGAGGCAGCCTCCTGGGCTGATACCGAGCTGGCTGCCGTATCTGCATCCGGCTCAGCGGTGACCTGTTCAGCATTGGGGGCCACCACACGTTCA
TGCACATTCTGGCCGAAGACGAACCCGCTGGACTGAACATTTGGCATGTTGTTCTTGGCTGCTGCAAACATGCTGGAGCGCTCAATGCCATTGCT
ACGCAGCTTGGTCAGCGGATCCGGCCGCTCGTCGACATCGTCGTCCTCCTTGTCGCCAGTGGACTCGGCTGCCGCAGATCCGGTGGCCACCACCT
CCTCGTCATCGTCGTCGTCCTTGGACTCGCGCAGAAACGGATTATTCAGCAGGGCGCTGTCTTCACCTGCACTTGGGGATGTGGAACTATTGTTG
GAGCCGCTGCTGTTTGCCAAGACTGCTGGGCGCAGGACAGCACCGCCCAGGCGAGAAGCCTTCAAGGTGAAGCCACCTCGGAAACAGTTAGTTTC
GACTGACGCTTCTGGAAACAAGGGGGAAAAAACAAGACTCGTTTGTCAGTTTGTTGCGAACTCTTCAAGGGCACAAGATTCGCGATATTTGGCAA
CTTTAAGTTATAGCAAGCATTACAGCTTGTTTTGCTACGCTTACCATTATTTTCAGACATTGCAAACTAGTCTACTTGCAATTTTAAAATATAAA
TTGCCAAATCTTTTACAGAATAGAGCGTTCTGTGTAAAGCCTGCCGTATTGTTATCGCTGTGTTATCGCTGTCACTATCGATAAGCGCCGGCGAT
GGCGCTCTGTTGTCAACACTGACTTTTTCAGTGTTGCTTACTTGCCGCTGAAAAACAAGAAATTTACAAGTCATCGACAGAGTGTTTGCCCAAAA
AGATCGGCAATAATAGCATTTTAACAAAGAATTACATTCAGCAACGGCTAATCAACAATCGTATTAGACATGGCTCAGACTCTGGAGGATAAGTC
AATCTGGGAGGACGGGGAGGAGTCCCTGGGCGAGGAGGTGATGCGTATGTCCACCGATGAAATTGTGAGCAGGACTCGCCTGATGGACAACGAGA
TCAAGATCATGAAGAGCGAAGTGATACGCATAACGCACGAGATTCAGGCGCAAAATGAGAAGATCAAGGACAACACCGAAAAGATCAAGGTAGGG
ATGACAATGAAACGCCACCCTGCCAAATAGCCTCATTTGTTAAGTACTTCCCCATTAGGTCAACAAGACACTGCCCTACCTGGTGTCCAATGTAA
TAGAGCTGCTGGATGTGGATCCACAGGAGGAGGAGGACGACGGCTCCGTCACCGTTCTGGACAACCAGCGAAAGGGCAAGTGCGCCGTCATCAAA
ACATCCACTCGACAGGCGTATTTCCTGCCCGTCATCGGCCTGGTTGATGCCGAGAAACTGAAGCCAGGTGATCTGGTCGGAGTCAACAAAGACTC
CTATTTGATCCTGGAAACCCTGCCGGCAGAGTATGATGCCCGCGTAAAAGCCATGGAAGTGGACGAGCGACCTACAGAGCAGTACTCCGACATTG
GAGGTTTGGACAAGCAGATACAGGAGCTCATCGAGGCAGTGGTGCTGCCCATGACGCACAAGGAGAAGTTCAAAAACCTTGGCATTCACCCACCC
AAAGGTGGGTATCTCACTCGAACAAATGTCACACAACCATATTAATCCTTGCCATTTACAGGTGTCCTTTTGTACGGCCCCCCTGGAACTGGCAA
AACATTGCTGGCCCGTGCCTGCGCCGCTCAGACAAAGTCCACCTTCCTCAAGCTGGCAGGTCCCCAGTTGGTGCAAATGTTCATCGGTGATGGTG
CCAAGCTGGTGCGCGATGCCTTCGCCTTGGCCAAGGAGAAGGCGCCTGCCATTATCTTCATTGACGAGTTGGACGCCATTGGCACCAAGCGTTTC
GATTCGGAGAAGGCCGGTGACCGTGAGGTCCAGCGAACTATGTTGGAGCTTCTTAATCAGCTCGATGGCTTCAGTTCCACTGCAGATATTAAGGT
GATTGCGGCCACCAATCGCGTAGACATTCTGGATCCTGCTCTGCTGCGCTCTGGTCGTCTGGATCGTAAGATCGAGTTCCCACATCCCAACGAGG
AAGCCCGTGCCCGTATTATGCAGATTCACTCGCGTAAAATGAACGTTAGCAATGATGTGAATTTCGAGGAATTGTCCCGATCCACGGATGACTTC
AACGGCGCCCAGTGCAAAGCCGTCTGTGTGGAAGCTGGTATGATCGCACTGCGTCGCTCCGCCAATTCGGTTACGCACGAAGACTTCATGGACGC
CATCATGGAAGTGCAGGCGAAGAAGAAGGCTAATCTTAACTACTACGCTTAGACTAAAAATTTGCAGTTTAACTTCACATTGTCAGCTCCCATTA
AAATAAACCATGGAAATGTAAAATTTTTCAGTTTCGATCTGAGTTGCCCCTTGAAGATCGCCTTTAAAATAACATCGCAACGGCTCTTAAAAGTA
ACTAGAATGGGAGACGTACTGAAATCAATACCCAACCTTTTTAAAATAAACAAAAATATATATCAAATGTCGAGCGATTCATTGGTTTATCAGTA CAACATTTACATTCTGAGTACGATATTTTTAAATATCTAAAAAGGTCGGTTTTAGAATTAATAAAAAATATTACATCGGGCGAAATTAGATGAT
AAATATTTACACGCACACTAATTAACCTAGAGGGATGATTTACCAAGTTACTAAGACTAACCAGTGGGATCGAGTGTGTTAGCGCCATCCGGCGC
CGCAGATGTCGTGCCACTTCCCCCTTGTGACGCTGCATCGACAAGGGACGTGGCAGTGGTTGATGAGGTTTCCGTAGAGGAGGACGCGGCCACAG
CATCGTGAGATGAAACTGCGGCGGCAGGTGGTGTGACGCCCACACCTTCGACCACTGCGGCTACAGGTGCTGCTTCCGCTCCAACCGGCGCCAAG
TTAACTGGCGCAGCAGCAATGTCATCTGCAGCTGGCTGCTGTGCCGGCTGATCCGGCTGCTGAAATGGACGCCTCATGTACATGATGATGCCCAG
CAGTAGAGTTAGAACGGTAATCATGTACAAGTCCCAATTGGCAGCAATATTTCATCCATGTAGAAGATGAACCTGTAAGGTGACTAAAGGGGAA
CAACATTAAAAAGCTAGTAAACAGTTTATCCATAGGGTTGGGTAATCACCTCCTTGATTGATTCAATCGTGGCCAACATTTGTAGCTTAAAAAGC
GCAATGGCCACAGGCACTTTGGCGTCTGAATTGGTTTCCGCAGCCAAATCGTATAATCTCTTTGCCAGATGCCAGTCTTTCTTCATTCCGAGCCC
TTGCTCGTGCATGTATCCCAAGTTGAACATGGCTTGGGCATTATATTGCTGCTCAGAGGCTTTCCTGTAGGGATTGATGCGGTTATAAGTCGTTT
TCACACTTCATAGTTCATATTCAACTAACCTGTAAAGAGCAGCGGCAGTCTCGAAGTCCGTCGAAGTACCCCAACCGTAGTAATAGTAATCGCCC
AGCTTGACTTGGGCCGCAGAATAGCCCTGTCCGGCTGCTCGTTTCCAGTAGTAGAAGGCACGAATCAGATCTTCGTGCCGATCGTTGAACACATG
CACCTCCTTGCGGTCTAGTAAAAAGGCGGCATTACTTTGAGCCACCTCATAGCCCATTTCGGCCATCAACGAGTACTGCATGTAGGCCTCGTCG
(SEQ ID NO: 1132)

Exon: 1001..1324
Exon: 1389..1809
Exon: 1867..2894
Start ATG: 1115

Transcript No. : CT29122
AAAAACAAGAAATTTACAAGTCATCGACAGAGTGTTTGCCCAAAAAGATCGGCAATAATAGCATTTTAACAAAGAATTACATTCAGCAACGGCTA
ATCAACAATCGTATTAGACATGGCTCAGACTCTGGAGGATAAGTCAATCTGGGAGGACGGGGAGGAGTCCCTGGGCGAGGAGGTGATGCGTATGT
CCACCGATGAAATTGTGAGCAGGACTCGCCTGATGGACAACGAGATCAAGATCATGAAGAGCGAAGTGATACGCATAACGCACGAGATTCAGGCG
CAAAATGAGAAGATCAAGGACAACACCGAAAAGATCAAGGTCAACAAGACACTGCCCTACCTGGTGTCCAATGTAATAGAGCTGCTGGATGTGGA
TCCACAGGAGGAGGAGGACGACGGCTCCGTCACCGTTCTGGACAACCAGCGAAAGGGCAAGTGCGCCGTCATCAAAACATCCACTCGACAGGCGT
ATTTCCTGCCCGTCATCGGCCTGGTTGATGCCGAGAAACTGAAGCCAGGTGATCTGGTCGGAGTCAACAAAGACTCCTATTTGATCCTGGAAACC
CTGCCGGCAGAGTATGATGCCCGCGTAAAAGCCATGGAAGTGGACGAGCGACCTACAGAGCAGTACTCCGACATTGGAGGTTTGGACAAGCAGAT
ACAGGAGCTCATCGAGGCAGTGGTGCTGCCCATGACGCACAAGGAGAAGTTCAAAAACCTTGGCATTCACCCACCCAAAGGTGTCCTTTTGTACG
GCCCCCCTGGAACTGGCAAAACATTGCTGGCCCGTGCCTGCGCCGCTCAGACAAAGTCCACCTTCCTCAAGCTGGCAGGTCCCCAGTTGGTGCAA
ATGTTCATCGGTGATGGTGCCAAGCTGGTGCGCGATGCCTTCGCCTTGGCCAAGGAGAAGGCGCCTGCCATTATCTTCATTGACGAGTTGGACGC
CATTGGCACCAAGCGTTTCGATTCGGAGAAGGCCGGTGACCGTGAGGTCCAGCGAACTATGTTGGAGCTTCTTAATCAGCTCGATGGCTTCAGTT
CCACTGCAGATATTAAGGTGATTGCGGCCACCAATCGCGTAGACATTCTGGATCCTGCTCTGCTGCGCTCTGGTCGTCTGGATCGTAAGATCGAG
TTCCCACATCCCAACGAGGAAGCCCGTGCCCGTATTATGCAGATTCACTCGCGTAAAATGAACGTTAGCAATGATGTGAATTTCGAGGAATTGTC
CCGATCCACGGATGACTTCAACGGCGCCCAGTGCAAAGCCGTCTGTGTGGAAGCTGGTATGATCGCACTGCGTCGCTCCGCCAATTCGGTTACGC
ACGAAGACTTCATGGACGCCATCATGGAAGTGCAGGCGAAGAAGAAGGCTAATCTTAACTACTACGCTTAGACTAAAAATTTGCAGTTTAACTTC
ACATTGTCAGCTCCCATTAAAATAAACCATGGAAATGTAAAATTTTTCAGTTTCGATCTGAGTTGCCCCTTGAAGATCGCCTTTAAAATAACATC
GCAACGGCTCTTAAAAGTAACTAGAATGGGAGACGTACTGAAATCAATACCCAACCTTTTTAAAATAAACAAAAATATATATCAAATGTCGAGCG
ATTCATTGGTTTATCAGTACAACATTTACATTCTGAGTACGATATTTTTAAATATCTAAAAAGGTCGGTTTTAGAATTAATAAAAAATATTACA
TCGGGCGAAATTAGATGATAAATATTTACACGCACACTAATTAACCTAGAGGGATGATTTACC
(SEQ ID NO: 1133)

Start ATG: 115

MAQTLEDKSIWEDGEESLGEEVMRMSTDEIVSRTRLMDNEIKIMKSEVIRITHEIQAQNEKIKDNTEKIKVNKTLPYLVSNVIELLDVDPQEEED
DGSVTVLDNQRKGKCAVIKTSTRQAYFLPVIGLVDAEKLKPGDLVGVNKDSYLILETLPAEYDARVKAMEVDERPTEQYSDIGGLDKQIQELIEA
VVLPMTHKEKFKNLGIHPPKGVLLYGPPGTGKTLLARACAAQTKSTFLKLAGPQLVQMFIGDGAKLVRDAFALAKEKAPAIIFIDELDAIGTKRF
DSEKAGDREVQRTMLELLNQLDGFSSTADIKVIAATNRVDILDPALLRSGRLDRKIEFPHPNEEARARIMQIHSRKMNVSNDVNFEELSRSTDDF
NGAQCKAVCVEAGMIALRRSANSVTHEDFMDAIMEVQAKKKANLNYYA*
(SEQ ID NO: 1134)

Name: 26S proteasome regulatory subunit 6A
Classification: endopeptidase
Gene Symbol: Rpt5
FlyBase ID: FBgn0028684

Celera Sequence No. : 142000013384415
CAGCAATTAGCATATACTACATATATACATATGTATATGTATATTTGGTGTGTGATTGGCATGAAACCGGCATTCTGTTTATTTACCCATCCAAT
TGGCGCCAGGTGAGTCCAAATATTTCACTTTTGTCCACTTTGATGTGTTTGCGCAGCCAATTCCTAGACGCTGTCGTAGACATCGAGATTACAAC
GGATTTTCGGGGGCGAAATATGGTAATATATGCAAACACGCTTTTATTTATTACGTCGGGCTTGCCTGCAAATAATTTGGCATTTCAATTTTGA
GTTGGTTGATTCATCTGCGCGTAAACATGATTTCGTTTTTCTTTGTAAACTCAGTAAATACGTTTAGTTTATAACTAGTTTAGCTACGTTGTAAC
GAAGTGGAAAGCTTATGAATGGCGGTTACTTTTCAATTTTTAATGAATTCACGATGAGTTTGGGAATTTTTGGTGGCATTCTGGTTTGATGTGGT
TTAATCGTTCTGAATGGCATTAACTTTTTCTGGTTCTTAAATATTAATTTCAAGTCTGGAAATTTCTAGCAATGCTTGTTTTTCACAACAAACTA
AGGTTTAAAAATATTAATATTTGTGTTCGTTAGGGATAAAAATTAATTTGTTAGCGAAATAATGTTTGAAATCATTTAAAGTTTCCAACTATTCC
GGACTAAGAGCAAAAATTAACCATAAAAATTTTTACTTAATTTTTGTATTACTTATTTATATAAGATTTGGCTTGGAATGTCCAACAGCACAATC
TAATAAATATAAAGAAAGATTATAAAGCATACATATAGTTTACACTTTTTCAATACTTTAATATATTCTATTGTTTATAACGAATTTATTGATTA
CAAATATTTTCAAATTTGAAATTGAATTGTAACCGCCTTTGACTGGTTCCGAATCGACTGGCTCTCCACGGAACATATCGCCACATGCGGTATAA
TCAATGCAGCTCCCTACGGTCATACTATTAACCACATCCACATCAGAAGTCTGAAATCTGATTTAAAAACTCTCACGAAACTTACTTAAAACCAG
GTGAAATAAAGACTGAATACATTCTGGAGGCAAGACAAGCTGAAGCAGTATGAGTGGCAAGCAGGTAGTCATCCTTCTGGGCAGTGTCCTGATCC
TGGGATGCTTACAAGTGGCAGCGGCAACGGAAACGGATAACAAAACCAACGATTTCGTGGCCACCGACGAATGGCAGACGATTGCGGAAGGTTAA
TGGCTAGCCAGGCTAACTCTCGGATGACGTGTACTAAGTGAGCACTCTATATTTCCAGGTCAAGCTATTCCAAGGGGCCTGCACGTGCGCATCAA CCTACAAACGGGGCTCAAGGAAGCCAAACTCTTAGACGAAAGCGAACGTGGCACGTCGCTGCAGAGTCAACCGGATGATCAGAATGCTCGGGAAT
CTCACGATGACAACGAACCCCTGGCTCTGGACTATAAACCGGACATAATCGAGGAGTCTATACGGCGGGTCAAGGAGCAGAAGAAGAGCTATGCC
GAGCTACGCAAAGCGTACAAAGAGTTCCAGAAGAACTTTCGCACCGACGGAGAACTGATCGTCCAGTTAATCGATCAGTTTCGGAACTTCAGCAG
AACGCCGCTAGAGTCAGAGATGCGCTCCAAGCTGGACTGCCTGGAAAATCTGGAGTATTTGCTCCATCAGATAGACAATGCCTTGATGTTCATTG
ATAATGGGGGATTGGATGATGTACTACTGCCCATTGTTGTGAACGATACCAGTACATCCCTGAGAGTGTCGGCCATGCGTGTGTTGGGCTCGCTG
GCGAGCAACAATCCCAAGGCCCAGATCAAGGTGTTCGAAAAGAATTTCGGGTCTCATCTGGCTCAGATTCTGACCAGTTCCGGAAATGTCGGTGA
GATCTCCGCTGCATTGCACGCCTTTGGAGCCTTGTTGCGGAAATTTCCGCTAGCCCAGCAGCGAGTGCTTTCCACCTCGGGTACACAGGCTCTGA
TCAAGGTGCTCCAGAGTCCGGATGTGGAGCTGCGGAGCAAGGCGAAGGTAGTGACTCTCATAAGCGACCTAGTGCTGGAGAAGCGGTCAGTGCTG
GATGTCAGCAAAGATGATCCCGAAGCCTCATCCACAATGGCGCAATATGTGCTCTTGGACTTCGAGTCGTGGCTGAAAACGCCGGGCTACTGCGC
GGCGGTGGACACTGTGCTAACCAAGGAGTTCCTGCTCCTCCTAGAGCAACCGGAGGTGGTGGAACAGTTTGCCACCGCATTGGAGACCACCGAAG
ATATGTGCACCAGCACGTGGTCGCAAAGTTCCGGTCTCAGGCATGCACTATTAACCGTTCGCAATCGGTATGCCAACAGCACGGACGAGTACCGA
CTGGAGGTGTCCCAGATTTTGGCCAAACTGTGCGAGAGATTGTTCAACAAGCCCAAGCACACCGAACTGTAATCCTAGCCAATTTACTATGTTAT
TTATGTTAATTTCATTTAATTGTAAGCTGAGTTGGAATGAAATTCGCAGCCAAACCATAGAATACGATAGCTAAGATGCCAAGTACTTGTGATGC
AAAAATAATGCTCTTTGTCATTAACTTAGGATAGCAATCAATCATGCCAAACATCTACAGGATTTTCGTTATCAAATATAGTCTCTTACTTAAGA
TTATTTTAAGTGTGATTTTTTTTAATAGGCAGACGATTCACCAACGAGCACATCAAAATAATTATGTTGTTACACGTCATTAAACTAGCAAAAA
TTTGTATGCTACAGAATTGTTCTCCAAACAGATTATGAATCCTTAAAGCCTTAAGTTCTTGTTTATTGTAGCTACAATAATAAAGCAATGACCTA
ATGTTTAATTTAGAAATTCTTTCTTAAATCAGTTGACTTCTTTTCAGTGGCATATTCTTAAAATGTAGTGCTAAATTATGAAAGGAAATGTATTT
TCAATCAAGAAATCGCATTAGGAGATTGGATATTCCACCCCTATAGAACTACAGACCCATTTAAAGCCCGATAAGGCGAGCATAATCGACCGGGC
CATAAAGTAAGTCAAAAGTGTCGGAAGGAAAGCAAAAACGCCGAGGAAAGCATGTCCCAAAAAACCACTTGAAGTTTGAATGTGAGCCAAACGAA
GCCACAAGAACAGGGAAAACCTGGCACGGAACTGTACAGGAGGAGAAAGGACATCGGAGCAGGAGAGTGCAATTATGTGCCGGCAAAGTTGGAAG
TTGGAGTCGAAGTCCAGCGCGGGAATTACAGCAATTAGCGGCAGTCACATGCAAATGCAATGTCACTGGGGCTGAGTCACGACGGTGGATGGTCG
GATAGGTGGAGTGGTAAAGGTGAAGCAGCGCCTGGAAGGGAGCCGGCTAGGACGCCGCCTTGGTTCCCATGGCTACTCCATGCAATGTAAACAGA
GAAAAGGGGTTGCAAAGCCGGCTCAGT
(SEQ ID NO: 1135)

Exon: 1001..1230
Exon: 1294..2447
Start ATG: 1095

Transcript No. : CT29244
CTGAAATCTGATTTAAAAACTCTCACGAAACTTACTTAAAACCAGGTGAAATAAAGACTGAATACATTCTGGAGGCAAGACAAGCTGAAGCAGTA
TGAGTGGCAAGCAGGTAGTCATCCTTCTGGGCAGTGTCCTGATCCTGGGATGCTTACAAGTGGCAGCGGCAACGGAAACGGATAACAAAACCAAC
GATTTCGTGGCCACCGACGAATGGCAGACGATTGCGGAAGGTCAAGCTATTCCAAGGGGCCTGCACGTGCGCATCAACCTACAAACGGGGCTCAA
GGAAGCCAAACTCTTAGACGAAAGCGAACGTGGCACGTCGCTGCAGAGTCAACCGGATGATCAGAATGCTCGGGAATCTCACGATGACAACGAAC
CCCTGGCTCTGGACTATAAACCGGACATAATCGAGGAGTCTATACGGCGGGTCAAGGAGCAGAAGAAGAGCTATGCCGAGCTACGCAAAGCGTAC
AAAGAGTTCCAGAAGAACTTTCGCACCGACGGAGAACTGATCGTCCAGTTAATCGATCAGTTTCGGAACTTCAGCAGAACGCCGCTAGAGTCAGA
GATGCGCTCCAAGCTGGACTGCCTGGAAAATCTGGAGTATTTGCTCCATCAGATAGACAATGCCTTGATGTTCATTGATAATGGGGGATTGGATG
ATGTACTACTGCCCATTGTTGTGAACGATACCAGTACATCCCTGAGAGTGTCGGCCATGCGTGTGTTGGGCTCGCTGGCGAGCAACAATCCCAAG
GCCCAGATCAAGGTGTTCGAAAAGAATTTCGGGTCTCATCTGGCTCAGATTCTGACCAGTTCCGGAAATGTCGGTGAGATCTCCGCTGCATTGCA
CGCCTTTGGAGCCTTGTTGCGGAAATTTCCGCTAGCCCAGCAGCGAGTGCTTTCCACCTCGGGTACACAGGCTCTGATCAAGGTGCTCCAGAGTC
CGGATGTGGAGCTGCGGAGCAAGGCGAAGGTAGTGACTCTCATAAGCGACCTAGTGCTGGAGAAGCGGTCAGTGCTGGATGTCAGCAAAGATGAT
CCCGAAGCCTCATCCACAATGGCGCAATATGTGCTCTTGGACTTCGAGTCGTGGCTGAAAACGCCGGGCTACTGCGCGGCGGTGGACACTGTGCT
AACCAAGGAGTTCCTGCTCCTCCTAGAGCAACCGGAGGTGGTGGAACAGTTTGCCACCGCATTGGAGACCACCGAAGATATGTGCACCAGCACGT
GGTCGCAAAGTTCCGGTCTCAGGCATGCACTATTAACCGTTCGCAATCGGTATGCCAACAGCACGGACGAGTACCGACTGGAGGTGTCCCAGATT
TTGGCCAAACTGTGCGAGAGATTGTTCAACAAGCCCAAGCACACCGAACTGTAA
(SEQ ID NO: 1136)

Start ATG: 95

MSGKQVVILLGSVLILGCLQVAAATETDNKTNDFVATDEWQTIAEGQAIPRGLHVRINLQTGLKEAKLLDESERGTSLQSQPDDQNARESHDDNE
PLALDYKPDIIEESIRRVKEQKKSYAELRKAYKEFQKNFRTDGELIVQLIDQFRNFSRTPLESEMRSKLDCLENLEYLLHQIDNALMFIDNGGLD
DVLLPIVVNDTSTSLRVSAMRVLGSLASNNPKAQIKVFEKNFGSHLAQILTSSGNVGEISAALHAFGALLRKFPLAQQRVLSTSGTQALIKVLQS
PDVELRSKAKVVTLISDLVLEKRSVLDVSKDDPEASSTMAQYVLLDFESWLKTPGYCAAVDTVLTKEFLLLLEQPEVVEQFATALETTEDMCTST
WSQSSGLRHALLTVRNRYANSTDEYRLEVSQILAKLCERLFNKPKHTEL*
(SEQ ID NO: 1137)

Celera Sequence No. : 142000013384415
TAAAGAATGTTTCATAGGCTCTAAATCGAGATTTTGTGAGGCTTCTAATGATTGGGCATTCAGCATTTTTTCAAGAATTTTGTAACCGACTCAAA
AAATCTTTAGAATGGTTGGTTATTCGGATCGCATATACTTAGCTTGTTTGTCTTATTTTTATTTGGATGAGCGCCAAAATTTTGCTGCGTCAGTC
TGGAAAAAATTGAATCAAATGTGTATAGTTTTATAGAAGTTGGGAAGCGGAATTTATTTATTTATTTAAATATTTATAATTAAAAAAATGAAAAT
AGTCACGTTGTTTAACTAGTCAGTATTCGAACCAACAAATGTAAAATGTATACTGGTTTGTGTCTAAGCTAAGCTTGTCATATTAACGGAGCTGC
CAGATGTTAGGAAGTGGGGATGCCATACATTATTCTAAATTTGCGCGCAATTTTAGAAGCTTATCGTCGTCAGAATTACAAAAACAAATTGAATA
TGAAAATGGGTTATTGCTACTTCATTATTATTGTCACGATATATGATAATTTATACAAAATGTGATAAATCCCAAATTGTTAAATAATGCTTTGG
CTTGCTTTATACAAAACCACTAGATAATTAAAATATAGGTGGCCTAAATTGTTGCATGTTGTTTTATAATTAATCAGCAATTTGATTTGGTTGTG
ATCGACCAAATCAGTGTGTATAATTGTAGTTAAAATGTAAAGTTCGTAATGGATTATTGAATCGCATTTCAAATTTCTTTAAATGCGCCCGGGTC
AATGACCTTTTGAGGTGACCATAAATTGAAACTTATTTGTGCGACGGCAACCCTGTTCTGGGACTCGACATGATATCGATACGTTAACAACAAAG
AGTCTGGACGCCATCATTCTTCCTCTTTCTCCTGAATTCGCAGACAGCGTGGCGTCAGGCATTTCAAACGGTAAAAAGAACCTGGCGATAAGGAA
AGATTTAAAAGGCAAAAATCGAGTGATTTGTGTGATTTAACTTAAGAATAATGCTTAATGCACGTGACGTGTGTCCTGAGGGCAACGACGACCAG
CAGTTGGACCACAATTTTAAGCAGATGGAGGAGCATTTGGCCTTAATGGTGGAAGGCAATGAAAACGAAGATCCGAGGAAAGCCACTTGTGAGTA CGAGGATACGAACGAAGATGGTGCAACCTGCACATCGGGCGTTTATCCGAAATCCAGGAGAACTTCGGTAGACTCCGGTTGTGTGACGTTACTG
CACCACTCCTCGAATTCCACGGTTTGGATTGCTTGCAACAGATTCAAAAGCGCTCGCGCCATTTTGCATTCGACGGTTCTCCGGCCAAGAAGTCG
CGATCCGGAGGCGTGTTGGTCACCGGGCCAAAGCAGAAGCAACTGCAGAAGGAAAATGTGTGGAACCGGAAGAGTAAAGGCTCTGCGTCCGCGGA
TAATATTGAGAAACTGCCCATAACTATTGAGAAACTGCATATGATTGGTCTGCACGGCGATTGGTGAGTCTTCTGGAGTATATCCCAAATATATC
ACATAATAAAAAGCTCCTTATCTAAACAATAGCTTAGAGCACAACGCCGTGCTGCGTTTGATGAATCTGTTCAGATCCCTGCATGATCACCTGAC
CGCCGATTTGGGCTTCTCGCGCCAAAACTCAATGCCCTCGGACTATCTGTTCGATATGCCGGTGAAGAGCACGATGCCTAAGAGCTTGAATGTGC
GCTACCAACTGCAGGTGCTGTGCACCAAAGTAGAGCGCTTCCTTGTCCAGCAGCGCCGCACCTTGGAGGCGAATCGCCACTTCGATTTCGAGAAA
TACGACGAGTGTGACAAGTTGCTTAAGGGTTTCGCATCCTATTTGGACAACTTCAAACTGCTTTTAAAGCCCAAAATGCGCAATCGAAACGGAAA
CTCGGGGAGCAATGCGGACAAGTGTAAGCTGTAGATTTGCAAGCAACCATTCAGCTATTCCTGCAACGATTTTATTATTTACAGTCCATACTCAG
CGCATGGAGAGATTGCTAATTGGTCTGCGCGATTGGATCAAGGCTGCGCATCTCAGTGTGCACGTATTTAACTGGGAAATGGATCTGGAGCACCG
CTACTCCGGGGCCATGACCGAAAGCCACAAGTCGTTGAACGAGCGGGCCATCCTTTTGTCCGGTGCCGAGCTAAGGGCGGCCGAAGCGCGTGGAA
TCAGTGCGGAGGATCTGTTCATCGCCCAGAGATACAAACTGGGAGGTCCGATCTATTGCGTTCTGGAGCAGCATGAGTTCCTCTCCGCTCTGATC
GCCAATCCAGAGACCTATTTCCCGCCCAGTGTTGTCGCCATTTGCGGGCCACAGAAGCTTGGCGCAGTGAGCATGGAGCAGCCGTCAGCGTCGGA
GGAGGAGTTTGAGGAGACCGAGGAGGTGCCATCATCGCCACCTCGTCACACCGGACGTGTACCTCGCTTCAGAAGCTAAACTAATGCTGTGCACA
TCGATAAAAGAATGACAGCAAATATGCAATTTAAAAAAGCTACTCTTCTCATGGGAAGCAATAATTTCGTAAAGTAAACATATCTATAGTGTAAG
ATATATTTGTCCAATAGTGCGGACTCCATATTTGTATTCGTGAATAAGCTTATATAAGCTTTTAAAAATATTTATCAAATCGATACAAACAAAA
TCAAAATGAAAACGATTTATTACCCCTGTTTTGAGATTGATAACAAATTTATATAAGTTTAACTGTGTTTACATTTATTTGGCAAAACTACAAAT
GTGTTTGCTTTTCACTTTTATAAATCTGTATTTTACTTAAACTTTAGAAATAAGAAATCCTTTAGTGCCTGAATTTATTTTGCAACTACGTTTTA
TTTGTATGAGGAACTTACCAGTTTTTCTTATTTGCTTTGCATTTGTATTTTGAAAGTCAAATAAATATTTACGATTTGTGTTTGGACTAATTAGG
GTGTTTGTACTAAGGTCTTAGACTACAAAGAGCTGTTCGAGCGGCAGTTTGCCAAAGATCCTGTCCACCACCGACTTGGCTATCAGTCCGAAGGC
CTCGCCAATGCCCGGTTTCAGTTCATTGAAGATGTCCTTCCAGTTCTCATTGATAAGCGCGTGCATGTTCTCGCTGAGATCTTTCTGGCCGTTGA
ACAGATTTTCCAGCTGGTAGGTCACATGGGATGGATCCAGCTCAACCTTTATGTTCATCACCTCGGCGTAGGTTTGATGATCGCCCTTGGAGACG
CGCTTCAATTTGATCTGTGCACGTACCTTTGTTCTAGCTGCGAATTCCAGAAACACATTAAAAATTTTAGATTTCAAAGCTGTGGGAGGCAAATC
TTACTGAGGCGTATGTCAGCAATGCCATTTCCGGTGATGGGCAGAATGAGTATTCTTCCGTCCACCGAGTAGGGTCCTCTGACTCCTATTTCTGG
AACTTCCATGACCAGCTCGATGGAGCGGCTGAGA
(SEQ ID NO: 1138)

Exon: 1001..1488
Exon: 1553..1923
Exon: 1985..2454
Start ATG: 1001

Transcript No. : CT29276
ATGCTTAATGCACGTGACGTGTGTCCTGAGGGCAACGACGACCAGCAGTTGGACCACAATTTTAAGCAGATGGAGGAGCATTTGGCCTTAATGGT
GGAAGGCAATGAAAACGAAGATCCGAGGAAAGCCACTTGTGAGTACGAGGATACGAACGAAGATGGTGCAACCTGCACATCGGGCGTTTTATCCG
AAATCCAGGAGAACTTCGGTAGACTCCGGTTGTGTGACGTTACTGCACCACTCCTCGAATTCCACGGTTTGGATTGCTTGCAACAGATTCAAAAG
CGCTCGCGCCATTTTGCATTCGACGGTTCTCCGGCCAAGAAGTCGCGATCCGGAGGCGTGTTGGTCACCGGGCCAAAGCAGAAGCAACTGCAGAA
GGAAAATGTGTGGAACCGGAAGAGTAAAGGCTCTGCGTCCGCGGATAATATTGAGAAACTGCCCATAACTATTGAGAAACTGCATATGATTGGTC
TGCACGGCGATTGCTTAGAGCACAACGCCGTGCTGCGTTTGATGAATCTGTTCAGATCCCTGCATGATCACCTGACCGCCGATTTGGGCTTCTCG
CGCCAAAACTCAATGCCCTCGGACTATCTGTTCGATATGCCGGTGAAGAGCACGATGCCTAAGAGCTTGAATGTGCGCTACCAACTGCAGGTGCT
GTGCACCAAAGTAGAGCGCTTCCTTGTCCAGCAGCGCCGCACCTTGGAGGCGAATCGCCACTTCGATTTCGAGAAATACGACGAGTGTGACAAGT
TGCTTAAGGGTTTCGCATCCTATTTGGACAACTTCAAACTGCTTTTAAAGCCCAAAATGCGCAATCGAAACGGAAACTCGGGGAGCAATGCGGAC
AAGTTCCATACTCAGCGCATGGAGAGATTGCTAATTGGTCTGCGCGATTGGATCAAGGCTGCGCATCTCAGTGTGCACGTATTTAACTGGGAAAT
GGATCTGGAGCACCGCTACTCCGGGGCCATGACCGAAAGCCACAAGTCGTTGAACGAGCGGGCCATCCTTTTGTCCGGTGCCGAGCTAAGGGCGG
CCGAAGCGCGTGGAATCAGTGCGGAGGATCTGTTCATCGCCCAGAGATACAAACTGGGAGGTCCGATCTATTGCGTTCTGGAGCAGCATGAGTTC
CTCTCCGCTCTGATCGCCAATCCAGAGACCTATTTCCCGCCCAGTGTTGTCGCCATTTGCGGGCCACAGAAGCTTGGCGCAGTGAGCATGGAGCA
GCCGTCAGCGTCGGAGGAGGAGTTTGAGGAGACCGAGGAAGTGCCATCATCGCCACCTCGTCACACCGGACGTGTACCTCGCTTCAGAAGCTAA
(SEQ ID NO: 1139)

Start ATG: 1

MLNARDVCPEGNDDQQLDHNFKQMEEHLALMVEGNENEDPRKATCEYEDTNEDGATCTSGVLSEIQENFGRLRLCDVTAPLLEFHGLDCLQQIQK
RSRHFAFDGSPAKKSRSGGVLVTGPKQKQLQKENVWNRKSKGSASADNIEKLPITIEKLHMIGLHGDCLEHNAVLRLMNLFRSLHDHLTADLGFS
RQNSMPSDYLFDMPVKSTMPKSLNVRYQLQVLCTKVERFLVQQRRTLEANRHFDFEKYDECDKLLKGFASYLDNFKLLLKPKMRNRNGNSGSNAD
KFHTQRMERLLIGLRDWIKAAHLSVHVFNWEMDLEHRYSGAMTESHKSLNERAILLSGAELRAAEARGISAEDLFIAQRYKLGGPIYCVLEQHEF
LSALIANPETYFPPSVVAICGPQKLGAVSMEQPSASEEEFEETEEVPSSPPRHTGRVPRFRS*
(SEQ ID NO: 1140)

Classification: known_flybase_gene
Gene Symbol: bam
FlyBase ID: FBgn0000158

Celera Sequence No. : 142000013383897
CAAAATTACAATAAACCCAAAACGGAAAAAAACACCTGTAACTAAAGTACAATAGCTGGCAAATATCCTTCCTCAATAAACGTAATCTGCTCAAG
AACCTCTGCATCGCCTTTATTGAAGCACCCTGTATTTAGCATAAACAAAACCCGTGTCGGCGCTGCGCTGCGAATGTCATAAGATCCGGAGCGCA
CAAGGAACTCGGCAAAAGGCTGGTGGTTATGTATTCATCTCGATAGCTCCGCTCTCCAACCAGTTCATCCATGGCATTTCGGTTCTTTGGCAAGT
CCTTGCTGTACGCTCTGCCACTTGGCGTCACTTTCCTGGACTGCGTTGGTTATGTGGCCAGGGTGGATGGTGAGTCGTCCGGAGTTTATTCGCTC
CATGTTAGTGTGCGCTAATTAATCCACAACTTTTTGCAGGCATCTCCATGCAGCCCGCTCTCAATCCCGTGCCGGATGAAAAGGACTATGTGTTC
CTGCTGCGCTGGGGCACCCACAACAGTCAGGTGGAGCGCGGCGACATAATATCGCTCATTTCACCCAAGGATCCCGCCCAGAAGATTATCAAGCG
CGTGGTGGGGCTGCAGGGCGACGTCGTGTCCACGCTGGGCTACAAGCACGAGATCGTTCGCGTACCCGAAGGACATTGTTGGGTGGAGGGCGATC ACACAGGCCACTCCATGGACAGCAATACCTTTGGACCCGTCGCCCTGGGCCTGATGTCCGCGCGGGCAGTGGCCATCGTGTGGCCACCGGAACGC
TGGCGAATACTGGAGAACGAACTGCCGCGGCGACGGAGACCCATACAGGCCTCCAAGAACTCCAGCAACTACTACAACTAGACTGACCAACTGGC
GGAGAGCCTGCGCCCAAGATAGTTCCAATTGTGTACATACTGAACCGTATATTTTATAAACAATTTGTTGTGTTCCCGCATGCAAAGCAAAGTAG
GATGTTCCAAAGTAAAAATTAAAGTTAAAGCCAAAGGAATAGCTCTTATACTACATCATTTTTAGCTCCCGAATGCCGAACTCCTCCATGAGGCT
GAGTGTCGGCTTGAGAGCCACGCCGGCGCGCACTATTTCATAGTAGCCAGGAGTGGCCAGGTCAATGACCGTGGAGGCCAGTCGTCGCTCCTCGG
TCAGACCGATTCGACCGGCATCGAAGACGGCGCCCAATTGGGGCCATAGGGAACGGAACTCGGACACCTGCAGACTGCTGGGCGCACTGGAGCGA
TTGGCGCTGGTCAGGGCCAGGGGCTTCTCCTGCCACACGGCGCACAGGTCGCGCATGAAGTTGAAGTCCGGAATGCGTATGCCGATTTTGGAGGT
GCTGGGATTAAGGAAACGGTTGCTCAGCTGGGACGTCCGCTCGATCACGATGGTCAGGGGGCCCGGGAGCAAACGAGTTAGCAGCTCGTCGCTGA
GATGGGCAGCCTGACCAAAGCGTCGCAACGCATCGATGTTGTGAACGCAGATGGCCACGGGCTTGTGTTCATCGCGACCCTTAATCTCGTAGAGC
TGCTGTATGGCTGTCTCGTTGTTGGCATCGCAGGCCAGGCCATACACGGTATCGGTGGGCAGGGCAATCACTTGGCCACCAAGCAGGCACTGGCG
GGCCAACTGGAGAGCAGCCTCGTCGCCCACCGCGCACACTGGAGTCCTCAGCTCGCTCGCTTGGTGCTGCATTCTGCTGGATGTGTGGTGAGCAC
GGAGCAGTCGATAAAGGCTCGTTTGAAGGCGGCGCATTAGTCTCGCCAGGTGTGGTTGCACTCGTGGTTGCAGCACTTGTAAAACGTGGTCATGG
GCTCATCCGCCGACCGCGTCTGGATTTGCATAAAGTACGCCCGCTTATGGCCGCACGTTGGACACTCTGCGTCCGTGGAGTCTACGTTCTCCCAC
GCCGCCTTGCCGCCCAGCACGTGATCCACCTCCTGGAAACACAGATTATCAGAGATATTATCATAAATTCGTAGCAAATTGCATCATCCAGTGGA
AAATGATCATACCTTGAGGCGTGGAAAGGTTTTCGTGGAGATCTTGCGCCTGATCTTCGATATGTACGGGCAGGTGTTGCACGTGAAGCGATGGC
AGTTGGTGTCCTCCTCGATAATCAATATATTTCCGCACGACGGGCAGAAAAACAACATAGTTTCGGAGAATCCGAATCCGCGCTGTTTAGTTTTT
TGATTTGAGCACGTTGAATTCTCAGTGTGACCGCGTATACGCTTAGATATACTAACTCAATAACATCACAATGTATACTGCAATACCATATGTTC
CACCGTTCCTCCATAGATGCTAATTTGAAGCACATTATAATAATTAATTAATAAATTAATTATTTGTAATAAATAAAAAATATTTCAAATACTG
TTTGAAAATTTCATGTTCGGAATTTAGTGAATTTATTACTTAGCCCTAGCATATACTAACTGTATATTTTATGGTGAAATAAACGTATTTACCAT
CTTATAGTTTACGGTCATACTAATAGCATTATAAGAAATTTTGTTCGTTTTGCAAAAAACTATCAAAATAAACAATAAGCAACTCAATTTTTAGC
AGACATTAGAGTAGCAAAAGTTTTAAATCATGTCGGCCGATGTGCGTGATATTCTGGACATGGAGCGTGCCAACACGCCCGAGGTGACGCGGGAT
TCGTTTCTGGCCACCAAGAAGCGCAACTTTGAGCGGTAAACAAATGCATTTACATGTGTGCGATTCTCTAATTTACAATTTAATCATTTTAGGAC
CAAGACTGCGTCCCGGCGTCCGGAGGGCATGCATAGGGAGGTGTTTGCCCTGCTCTACACAGACAAGAAAGATGCTCCGCCTCTCCTGCCCACGG
ATACCGCTCTGGGAATCGGAGCGGGATACAAAGAGACGAAGGCCCGCCTGGGCATGAAGAAGGTGCGCAAGTGGGAGTGGGCGCCCTTTTCGAAT
CCGGCACGTAACGATTCGGCGGTTTTTCACCACTGGAAACGAGTCACCGACAATTCCACCGACTATCCGTTCGCCAAGTTCAACAAGCAACTGGA
GGTGCCCTCGTACACGATGACGGAGTACAATGCCCACTTAAGGAACAACATCAACAACTGGAGCAAGGTGCAGACCGATCACCTATTCGACCTGG
CCAGAAGGTAGACTCTTCATTAGACTTCTTATTAAGTAGCCAAAATTGTAAGCC
(SEQ ID NO: 1141)

Exon: 2189..2008
Exon: 1932..1001
Start ATG: 2148 (Reverse strand: CAT)

Transcript No. : CT29300
ATCAAAAAACTAAACAGCGCGGATTCGGATTCTCCGAAACTATGTTGTTTTTCTGCCCGTCGTGCGGAAATATATTGATTATCGAGGAGGACACC
AACTGCCATCGCTTCACGTGCAACACCTGCCCGTACATATCGAAGATCAGGCGCAAGATCTCCACGAAAACCTTTCCACGCCTCAAGGAGGTGGA
TCACGTGCTGGGCGGCAAGGCGGCGTGGGAGAACGTAGACTCCACGGACGCAGAGTGTCCAACGTGCGGCCATAAGCGGGCGTACTTTATGCAAA
TCCAGACGCGGTCGGCGGATGAGCCCATGACCACGTTTTACAAGTGCTGCAACCACGAGTGCAACCACACCTGGCGAGACTAATGCGCCGCCTTC
AAACGAGCCTTTATCGACTGCTCCGTGCTCACCACACATCCAGCAGAATGCAGCACCAAGCGAGCGAGCTGAGGACTCCAGTGTGCGCGGTGGGC
GACGAGGCTGCTCTCCAGTTGGCCCGCCAGTGCCTGCTTGGTGGCCAAGTGATTGCCCTGCCCACCGATACCGTGTATGGCCTGGCCTGCGATGC
CAACAACGAGACAGCCATACAGCAGCTCTACGAGATTAAGGGTCGCGATGAACACAAGCCCGTGGCCATCTGCGTTCACAACATCGATGCGTTGC
GACGCTTTGGTCAGGCTGCCCATCTCAGCGACGAGCTGCTAACTCGTTTGCTCCCGGGCCCCCTGACCATCGTGATCGAGCGGACGTCCCAGCTG
AGCAACCGTTTCCTTAATCCCAGCACCTCCAAAATCGGCATACGCATTCCGGACTTCAACTTCATGCGCGACCTGTGCGCCGTGTGGCAGGAGAA
GCCCCTGGCCCTGACCAGCGCCAATCGCTCCAGTGCGCCCAGCAGTCTGCAGGTGTCCGAGTTCCGTTCCCTATGGCCCCAATTGGGCGCCGTCT
TCGATGCCGGTCGAATCGGTCTGACCGAGGAGCGACGACTGGCCTCCACGGTCATTGACCTGGCCACTCCTGGCTACTATGAAATAGTGCGCGCC
GGCGTGGCTCTCAAGCCGACACTCAGCCTCATGGAGGAGTTCGGCATTCGGGAGCTAAAAATGATGTAG
(SEQ ID NO: 1142)

Start ATG: 42 (Reverse strand: CAT)

MLFFCPSCGNILIIEEDTNCHRFTCNTCPYISKIRRKISTKTFPRLKEVDHVLGGKAAWENVDSTDAECPTCGHKRAYFMQIQTRSADEPMTTFY
KCCNHECNHTWRD*
(SEQ ID NO: 1143)

Name: PUTATIVE DNA-DIRECTED RNA POLYMERASE III LIKE
Classification: enzyme

Celera Sequence No. : 142000013384661
TTAATAATGCGATACTCGTATTCGTACTCCATCACGCGCATTCGCCCGTCCAGTTCTATGGCTCGATATTGGTTCAATCCCTCCATGAACTGACC
GCGGCTGCACTGCACCGTGTCCAGGAGCTGCGAAAAGGTAAAGAGTAGCTTCTGCTCCACGCAGAACTCGTTCTCCGGCCCCGAATATCGAGTCA
GCTGCAGTAGTTCACCCAGCTTGCGAAAGCGCGGCTTTATCTCGCGGCACTCGAAGTACTCGTGGAACACCTTGAGCACCGGCCGCTGCTCCAGA
GTTCGCGGCACTTCCAGTTCATCCTCCGTGCTGTCATTGAGGCTGCGCTCCAGGGAGGCGTTGGCGTTGCCAGTGCGCGGACTCTTCAGCGGCGA
GGTGCTGGTGGCGGCGGCAAACTTGAGGTCCGGTACCAGCAAAAGGCTATTGGATATTTCCGCGCCCTTCACGTCGTACGTTCGCTCATCGGTGC
ACAGCACCAGCTTCTCGTTCTGGCCACCCTTGAAATATAGCGTCTGGCCGTCGCGGATTTGTCCAAGCATGTGCCCATCGAGCTCCAGAAGGCGC
AGATTGTCCGAATCCACGTCCGCCGAGGGAAAGTACAGAGCCTGGGTGAGTTGGGTCAACTGGCGCTCGTCCAGTTTCGCATGCTTCACAATGGC
CTTCACATCCTCCGGCGTGCGAACGTAGCTATGGCGGGTGGTTGGGTAACATTATAACTCCTACGCAGGCATACCAAAGGCACTCACAGCTGGGC
AGCAGACTCATCAACCTCCATGGATTCCATGTTCGCTGCATGTAAACAAAACAAAAAATTAACCAAAACAATGAGCGGGAAAAAGTAGTGGGACC
AAAGCACAGCAATGTTGCTTTCGTTGAGGGTATTCAATGGCCTTTCAATATGTAAGCTTAATGTGCTTGGAAAACATTACAGCATTAATCCGCAC
ACCCTGCAAGGGCACACTCACCGCTCAGCTGATCAGTTATTTAACGGTCGTAGCCTCGGCAAGAACGTTTCTTTTTTGAGCGGAGATTTCGCGAG
CACGCGTCTTGTTTTCCGCCGTTCGCCGTGCACTTGGACGCGCACTTTAGAAAGCGTTGACTGCGCCAAAGGTCATTGCTGGGCAAGAGAAGCGT CCAATCGCCGCTGGTGGTGACGCTTGTGGAAAAATCAATTCGGACCAGTGACGGACGTCGAACTTCCAGTTCTCTGACAAGCGGAATCCAGTCAA
CAACAACATGCCCGTGGGAACGTTTGACGCCTGGGATGCGGCCGTGCTGATCACCATCCTGGTCATATCGGCTCTGATTGGCATCTACTACCGGT
ATACAGGCGGCAAGCAAAAGACCACACAGGAGTATCTGATGGCGGACCAGAGCATGACCACTTTTCCGGTCTCCTTCAGCCTGATGGCAAGCTTC
ATGTCCGCCATCTCACTGATGGGCGTCTCCAACGAGTCCTACGAATTTGGTACCATCTTCTGTGTGATCAACATTGCCTACGTGCTGAGTACGCC
CATTGCCGCGTACTTCTTCCTTCCTGTTTCTACAGGATGCGGACGACCAGTGTGTACGAGTATCTGGAGCGGCGCTTTGGCCAGGCCACCCGGC
TGTCCGCCTCCCTGGCCTTCACCGTGCAAATGGTGCTTTACATGGGCATTGCACTCTATGCACCAGCGCTCGCTTTAGAAGCTGTAACCGGCATT
CATCGGTCAATGGCCATCGTGGTCATTGGACTGGTGTGCACCTTCTATTCGACACTTGGCGGCCTGAAGGCGGTGCTCATCACGGATGTGTTTCA
GTCCTTCCTCATGTTTGCCGCCATCTACGCCGTGATTGCCGTGTCGGCCATTAAAGCCGGCGGATTCGCGGCCATCTGGGATGTGGCTGTGGAGC
GAGGACGCGTGAACTTCATTGAGTTTTCATTGGATCCCACCGTGAGGCATACTTGGTGGTCTCTGATCATTGGCGGCATGGTCACTTACCTCTCC
TTGTATGGCGTTAATCAAACGCAAGTACAGCGACTCCTGAGTGTCCGCAATTTGAAGAGCGCTCAGTCGGCGCTTTGGTGGAACCTGCCCATCCT
AGGAATGCTTAGTTTTAGCACCATTTTCAGTGGACTGTCCATATTCTACTATTATCGAGATTGTGACCCTTTGCTAAAGGGACGCATCGACAAGC
GGGATCAGATCATGCCCCTTTTCGCACTGGAGACTATGGGTGAGTTGGAAAGACATCCAATAAGAATTAGCATTATTTGATTTCTTTTTCCGGCA
GGTCAATATCCTGGACTGTGTGGTCTGTTCGTGTCCGGAATATTCTCCGCCAGTCTTTCCACGATTTCGTCGGCAGTTACCTCGCTGTCGGCTGT
AACACTGGAGGATTACCTGAAGCCCTTGTACAAGGCGATATTTAAACGGACGCTAATTGACTCCAAGTCCACGATGCCCACCAAGATTGTGGCGT
GCATTTTTGGCCTGCTTTGCATCGGTCTAGCTTTTGTCGCTGGCTCCATGGGCGGAGTTCTTCAGGCATCGCTTACCATTTTCGGTGTGGTAGGC
GGTCCGCTGCTGGCCATTTTCACACTGGGAGTCTGCACTACACGCAGCAACCAAAGAGGCGTGCTGCTTGGCTTCCTCGTTTCCCTGATAGTTTC
CTTCTGGATGGGATTCGGCGGACCCAAACCAAAGCCAGTTACCTTGGAGTTTAGCACAGCGGGCTGTGAGAATGCCACCGCGGTAATGGCGCGTG
CCATCGAGCTCAGCTCAAAGAGCAGCGGAGTGGTCATCGAACCCGACTACTTCTGGTTATATCGAATTTCTTACTTGTGGCTGAGCGTCATCGGC
TTTCTTATTGCCGTGGTCGTCGGCTATTTCAGCAGCATTGTGCTGGCTCACTGTGGAAAGGCAGAAAACGCGGAAATCTATTTGGACAAGTCTCG
GAAGCAGCTGGACTACGATCTCTTCGCACCCATGCTGTCCCGCCGCTGGCGACGCCATAAAGAAGAACAAGACCAAACTGCCCAGGACGAAACGC
TCACCAAACTAACTGAGCAGTAGTTCCGCCCGGCTTAGATTTAGTGTAGAATATATACATACATATAAAAGAATTTCCAGAAGGCGTCGGCTATT
TGGTTAGTCGTGTTACGGATGTCGTACCTAAAAGTGCATAACTATGTGACCTTTTTGTATACCTGTGTGAACGAAACTGGCATACAGAGCGACCA
AAACAGAGTCTTCCATATACACGTAAACAACGATAATTAGTAGTTATTAGTCGTGTTGCAAATGTTCACAAGCGCATCATTAAGAGGCCTCTTAA
GAATAGTCAAATGTTTTTACAAGAACGTATCAAAAGTAGGAGTCTACCTCAATGAACTTTTACAGAGGGACAATAATCAATTTGGAGCCTAAAA
GCGAGTTGGCCGACTACTTTCCCATGTTGAGCATTGGCAGCCACAATGCCCCACATAAATTATTGATTTAGTAGTACATCTAATTTTAATGGGAT
ATTTATATTCATACCTCTTAGTTACTCGATATTTGCATACATAGATAACATAATAACATTACAATAATACACTACAGTGAGCACCGCCTATAAAT
AGTTACTACATGGCTCTTAAAGCATTACATTGCGCCACAGTGTGAATTCTGTTTACTTATATACCTCTACTATATGTACACAAATATACTATAGA
CTAATTATATACTCGTGTCGTGTCGCAATCAACCATTGAACAATAACTCGGAGCAGTGAAAGTTATGTGTATTTGTAAAAGCCAAACTGCTGATC
ATTAAAGAAATCTGTTCTACAAAATGTGATTGCCTTTTTTTTATTTGCTGCGGAAACATGATACTTGCAATCCCCAGCTGCAGCTTGGATTGAA
ATAATTACTTCGGTTGGCTCATGGGTGTTTTTCAGAAATCACGATTTGTCGAATACTTCCTGCGATAAGCAAATTCGTACGCTATCAGCTACCAA
GGTTATGCGAGGCTCTCCCAACATTGCTCACTCGATGAGGAATCTATTTCGGAACGAATGCCATAACTTTCAAGCGTTTACCTTTGCCAATTGAC
TATTGCGCCATGCGGGAACAAAGTCTAATTGCGGGTCGGAGACAGCAAATTGCTTAAAATTGGAGAAGCCATGGGTCAGCATGTGAATATGGGTT
CGCCTGTAAACAAATGCCAATTGATAGATTTGTCGAAACATCATTAATAAACCCAGACCACGCTCGTCTTGCTCATGGAAAGTTTTCAGAACGGA
TTGGGAGTTCAAAGTACGAATAGACTCGCATGACACACATTTTTGGCTAATGTTCTGGCGAAAGAGGAGACCAAAAGCGGTGGATAACATAGTTA
CGCCATAACCGATTTTTGTTTACTCTAACTTAGTGTGCGATTTACTATTTTTAACAATATTTATGTTAACCAACAAGAATCTTAAGGCATTTATT
TGTATTCATTAGCAACGTCATAAAATATAATAACCATACAGATTTACATATAAGAGTATCAATTTGGCGACTGATGATTGTTTAGCCTTCATTTT
TGCAACGCCAACAGATGATTTGGGCGATTTGTTAGCATTCGGAAGCAAAGCTTTCACAGATAGTTTCGCTGATACGATAAGGGTTTCGTTTGGAT
AGCATTCATTGAAGTGATTCATTGGGGAAGATTTATGGTTCTATTGATTCTGCTTCCTCACAAACTTCATGAACACATCCTGGAAAGTTGTATGG
CTGACCGAGTAGTACAATATCTGCATCTCATCCTTCAAGTTCTCCATGTACTCGAAGATCGCGGACCACT
(SEQ ID NO: 1144)

Exon: 1001..2224
Exon: 2282..3820
Start ATG: 1369

Transcript No. : CT29322
TAGCCTCGGCAAGAACGTTTCTTTTTTGAGCGGAGATTTCGCGAGCACGCGTCTTGTTTTCCGCCGTTCGCCGTGCACTTGGACGCGCACTTTAG
AAAGCGTTGACTGCGCCAAAGGTCATTGCTGGGCAAGAGAAGCGTCCAATCGCCGCTGGTGGTGACGCTTGTGGAAAAATCAATTCGGACCAGTG
ACGGACGTCGAACTTCCAGTTCTCTGACAAGCGGAATCCAGTCAACAACAACATGCCCGTGGGAACGTTTGACGCCTGGGATGCGGCCGTGCTGA
TCACCATCCTGGTCATATCGGCTCTGATTGGCATCTACTACCGGTATACAGGCGGCAAGCAAAAGACCACACAGGAGTATCTGATGGCGGACCAG
AGCATGACCACTTTTCCGGTCTCCTTCAGCCTGATGGCAAGCTTCATGTCCGCCATCTCACTGATGGGCGTCTCCAACGAGTCCTACGAATTTGG
TACCATCTTCTGTGTGATCAACATTGCCTACGTGCTGAGTACGCCCATTGCCGCGTACTTCTTCCTTCCTGTTTCTACAGGATGCGGACGACCA
GTGTGTACGAGTATCTGGAGCGGCGCTTTGGCCAGGCCACCCGGCTGTCCGCCTCCCTGGCCTTCACCGTGCAAATGGTGCTTTACATGGGCATT
GCACTCTATGCACCAGCGCTCGCTTTAGAAGCTGTAACCGGCATTCATCGGTCAATGGCCATCGTGGTCATTGGACTGGTGTGCACCTTCTATTC
GACACTTGGCGGCCTGAAGGCGGTGCTCATCACGGATGTGTTTCAGTCCTTCCTCATGTTTGCCGCCATCTACGCCGTGATTGCCGTGTCGGCCA
TTAAAGCCGGCGGATTCGCGGCCATCTGGGATGTGGCTGTGGAGCGAGGACGCGTGAACTTCATTGAGTTTTCATTGGATCCCACCGTGAGGCAT
ACTTGGTGGTCTCTGATCATTGGCGGCATGGTCACTTACCTCTCCTTGTATGGCGTTAATCAAACGCAAGTACAGCGACTCCTGAGTGTCCGCAA
TTTGAAGAGCGCTCAGTCGGCGCTTTGGTGGAACCTGCCCATCCTAGGAATGCTTAGTTTTAGCACCATTTTCAGTGGACTGTCCATATTCTACT
ATTATCGAGATTGTGACCCTTTGCTAAAGGGACGCATCGACAAGCGGGATCAGATCATGCCCCTTTTCGCACTGGAGACTATGGGTCAATATCCT
GGACTGTGTGGTCTGTTCGTGTCCGGAATATTCTCCGCCAGTCTTTCCACGATTTCGTCGGCAGTTACCTCGCTGTCGGCTGTAACACTGGAGGA
TTACCTGAAGCCCTTGTACAAGGCGATATTTAAACGGACGCTAATTGACTCCAAGTCCACGATGCCCACCAAGATTGTGGCGTGCATTTTTGGCC
TGCTTTGCATCGGTCTAGCTTTTGTCGCTGGCTCCATGGGCGGAGTTCTTCAGGCATCGCTTACCATTTTCGGTGTGGTAGGCGGTCCGCTGCTG
GCCATTTTCACACTGGGAGTCTGCACTACACGCAGCAACCAAAGAGGCGTGCTGCTTGGCTTCCTCGTTTCCCTGATAGTTTCCTTCTGGATGGG
ATTCGGCGGACCCAAACCAAAGCCAGTTACCTTGGAGTTTAGCACAGCGGGCTGTGAGAATGCCACCGCGGTAATGGCGCGTGCCATCGAGCTCA
GCTCAAAGAGCAGCGGAGTGGTCATCGAACCCGACTACTTCTGGTTATATCGAATTTCTTACTTGTGGCTGAGCGTCATCGGCTTTCTTATTGCC
GTGGTCGTCGGCTATTTCAGCAGCATTGTGCTGGCTCACTGTGGAAAGGCAGAAAACGCGGAAATCTATTTGGACAAGTCTCGGAAGCAGCTGGA
CTACGATCTCTTCGCACCCATGCTGTCCCGCCGCTGGCGACGCCATAAAGAAGAACAAGACCAAACTGCCCAGGACGAAACGCTCACCAAACTAA
CTGAGCAGTAGTTCCGCCCGGCTTAGATTTAGTGTAGAATATATACATACATATAAAAGAATTTCCAGAAGGCGTCGGCTATTTGGTTAGTCGTG
TTACGGATGTCGTACCTAAAAGTGCATAACTATGTGACCTTTTTGTATACCTGTGTGAACGAAACTGGCATACAGAGCGACCAAAACAGAGTCTT
CCATATACACGTAAACAACGATAATTAGTAGTTATTAGTCGTGTTGCAAATGTTCACAAGCGCATCATTAAGAGGCCTCTTAAGAATAGTCAAAT
GTTTTTACAAGAACGTATCAAAAGTAGGAGTCTACCTCAATGAACTTTTACAGAGGGACAATAATCAATTTGGAGCCTAAAAGCGAGTTGGCCG ACTACTTTCCCATGTTGAGCATTGGCAGCCACAATGCCCCACATAAATTATTGATTTAGTAGTACATCTAATTTTAATGGGATATTTATATTCAT
ACCTCTTAGTTACTCGATATTTGCATACATAGATAACATAATAACATTACAATAATACACTACAGTGAGCACCGCCTATAAATAGTTACTACATG
GCTCTTAAAGCATTACATTGCGCCACAGTGTGAATTCTGTTTACTTATATACCTCTACTATATGTACACAAATATACTATAGACTAATTATATAC
TCGTGTCGTGTCGCAATCAACCATTGAACAATAACTCGGAGCAGTGAAAGTTATGTGTATTTGTAAAAGCCAAACTGCTGATCATTAAAGAAATC
TGTTCTAC
(SEQ ID NO: 1145)

Start ATG: 369

MADQSMTTFPVSFSLMASFMSAISLMGVSNESYEFGTIFCVINIAYVLSTPIAAYFFLPVFYRMRTTSVYEYLERRFGQATRLSASLAFTVQMVL
YMGIALYAPALALEAVTGIHRSMAIVVIGLVCTFYSTLGGLKAVLITDVFQSFLMFAAIYAVIAVSAIKAGGFAAIWDVAVERGRVNFIEFSLDP
TVRHTWWSLIIGGMVTYLSLYGVNQTQVQRLLSVRNLKSAQSALWWNLPILGMLSFSTIFSGLSIFYYYRDCDPLLKGRIDKRDQIMPLFALETM
GQYPGLCGLFVSGIFSASLSTISSAVTSLSAVTLEDYLKPLYKAIFKRTLIDSKSTMPTKIVACIFGLLCIGLAFVAGSMGGVLQASLTIFGVVG
GPLLAIFTLGVCTTRSNQRGVLLGFLVSLIVSFWMGFGGPKPKPVTLEFSTAGCENATAVMARAIELSSKSSGVVIEPDYFWLYRISYLWLSVIG
FLIAVVVGYFSSIVLAHCGKAENAEIYLDKSRKQLDYDLFAPMLSRRWRRHKEEQDQTAQDETLTKLTEQ*
(SEQ ID NO: 1146)

Name: sodium-dependent multi-vitamin transporter homolog
Classification: transporter Celera Sequence No. : 142000013384329
GTAGAAATCATAATTCAATTGCAACGGATCGAGTACTTACATTATCACTCTTTTCTTGATCATTCCCCTTGACTACACAATCATCGATCTTAACA
ACTTCCGTTAAATCAGGACTGGTACTTTTGCACTTGTACTGCTTAAAAACTAGCTTGAACATGCTTCATAAACAATAAGTACAATATAAACAATA
AGTTAATATAAACGATAGCAATAGTGTGACTGCGTTTGGAGAAATCTTAAATGCTTTTGAGCACGTTTAGAAATCAGACATGTGGTGGAAATACT
ATGGGATAGATATAAAAATTAAAAATGAATGCAATTCATAAGAGACATTGCCGAAAAAGCTCGAATGTCCTTTTCATGGAAAAAATTTTAAGCCT
TTTTTCATGAGGTGATTCATTTGTGATTAATCTTATCGATATAAAGTTATCGATATATGAACGGGACTTTTAACTATTTTGAAATATTTTTGTTG
TTTTGAGACCGATTTTTTCATTGTTTACGTTTTTGCAGTGATCGTTTTCATTATTTCGGTCGAAGATACGTCTTAAGGGTTGCACAGGAAAAAAT
CAAGTGGGAACATTACACTTCAGAGCGATAATAGATCTTTATTTTTTATATTTTTATGAATTAATATTAAAAAAGGAGTTGAAATAAGAAAATGG
TATATTTATATGACATATTTATATATTTATATATGTTGTAGTTATTTTACTTTCATGTGAGGGGGCGTGCTTAATACTATATTCGGTTCAAAAGA
AAGGGGTACCACATTGTTTATATAAAATAAAATATGTTTTTAAAATATAACGTCTTTTGACAAATAAACTTTGAATAAATAAAGACAAGTTGGTA
TATTTGCCGGCTCTCTCCGTCCGCAGTGTGAACAGCCTGGCTGCCGAATATGTATCAATGCTATCGATATCCGCATACATCGATACTGCTTCCTT
GCACCCTTAATTTGTTTCTAGGTGTTGGCTGCCAATTGTAGAGTGCAAATGAAAAGTTACAGATTGGTGGCTTCGTTAACAAAATTTTCAGTTAT
TTGTGTAGTTGAAGACGGGAATTTGTTTTGCGTATAAAAAGTTAACACTGCGTGTAAGTAACGTATTGTCGTCATCAACAAACTGTCCAGTGAAT
GAAAATTGAAAGAAAAATTACTGATCTATGGTAATGTGTGTGTATGTGCTAAAAGGAAAAAAAAATTTTTCATACTCGCTGAACGACGAGTGATG
AAAATGCAGTCTCGATAGTTTTGCGCCTACATATATGTATGACTATTGCACAGATTTGGTTGTTTTTTTTTCTAAACGATTGCCAGTCGGCATG
GAAAATTAAATGAAATGAGCTCCATATATTTTGTGCCTGTGCCAGTGCCTTCCCAACGAAAAATGTTCAACGTTTAAAATTGATTATTTTTTTT
TATCTATTTCCCTCCTGCTCTTTGTCATGTGTACGCTTACGCGGTTGCTGCGCGTGCGAATGGGACACCGATTGCCGCGACTGTTTTTGTCTCAC
CGCCCGCTTTCGGGAACTTCTGACCTGCTTTCGCTGCCGCGCTTTCAATTGCGCACGGCTCGCATCCACTAGTCGTGCTCCTTGCTCCAATCGAA
AGGGCCACTTGCGCCGCGGTGGTGGTGCAAAACTTGCAATTTTGGTGTACAAAAAAAGCAAAAGGAATATATCCCATATATCCTACCCATCTATC
GGAAGAACGGAATTCGAAATCCAGCACATAAAAAGCATAAATCACATCAAAAAATTCGCATTTTCTCTGGTCCTTAGCACCAGATCGCTTTTTAT
GCATCCAATTCGGTTTCCTCTTTTTTTTTAGTATACCATCCCATCCGCGAGATAACATTCTGTATTAAACAAAACGCCCAACATCCTAATTACAA
ATCAGACGGGACGGAAAATCGAAAAAACTATAGGAACCTCTCTCTCCCCCCCCACTAACGTAGTTTATGTGTATTTAACAAGCGAAGAACTTTCT
GCAGAGGTCTGAAATACACCAATCGCACATACCAAACAAAAAGTAATAAAAAAGAAATAATTGAAAAACCAAATAGTTAAATTGGCAGAGCAAAC
ACAGGACGACGACTATGAACTAAAGTCAGAAATTAATGGACATCGTACCGAGAATATAATCCGTGAATAGTACTATACGATAAAACAGAAAAAGA
AAAAAAGTCAACTAAAAAGCAAAAAACCAACTCTTGCAGAACACAGTTCATGATTTATCCATACTAGAAGTGCACAAAATAAACGCCGTATGCAA
GCGTGATCATCCAAGGCTCATTATCCGACTAAGCTACTGGCCAGCTTAAAAAAAGTAAGCGTAAGTACACCCACAACTGACCATATAACTAGGTT
AATGAACGCCTCCATTTACTACTTCCCCATATGTATAGCACCATCTAACAAGAGCGAATCGAATCGAATCGACTTGGACGACCGACCGACCGACC
GCACAAAGAAGGATCTATCTGGAAAGCCGGCTAGCCGATTCCCGCATCCGATTCCGAATACGAATACGTATCCGTATCCGAATCCGAATTTGAAA
CCGAATCCTCAACCAAATCATCCCATAAGGACGCCGCTGTCTTCAACGATCACAAGATGAATGAACTAGACAGTCTCAGGCAGGAAGCCGAGTCC
CTAAAGAACGCCATTCGGGATGCCCGGAAGGCGGCCTGCGACACATCACTGTTGCAAGCGGCCACCTCGCTGGAACCCATCGGCCGCATACAGAT
GCGCACCCGTCGTACATTACGCGGCCATTTGGCGAAAATCTACGCCATGCATTGGGGCAACGATTCAAGGAATCTCGTATCAGCCTCACAGGACG
GCAAACTGATCGTTTGGGACTCGCATACCACGAACAAAGTCCATGCCATTCCACTGCGATCCTCGTGGGTGATGACCTGTGCGTACGCCCCATCC
GGTAGCTATGTGGCCTGCGGTGGCCTCGACAACATGTGTTCAATTTACAACCTAAAGACGCGCGAGGGCAACGTCCGGGTGTCCCGTGAGCTGCC
CGGCCATGGTGGCTATCTATCGTGCTGCCGCTTCCTGGACGACAATCAGATCGTGACCAGCTCCGGTGATATGTCGTGCGGATTGTGGGATATCG
AGACGGGACTGCAGGTAACCTCGTTTTTGGGCCACACCGGCGATGTGATGGCCCTCTCACTGGCGCCCCAATGCAAAACGTTCGTATCCGGCGCC
TGCGATGCGTCCGCCAAGCTATGGGACATCCGGGAGGGTGTCTGTAAACAAACCTTCCCCGGCCACGAATCCGATATCAATGCGGTCACATTTTT
CCCGAATGGTCAGGCATTCGCCACCGGTTCGGACGACGCAACCTGTCGATTGTTCGATATCCGTGCCGATCAGGAGTTGGCCATGTATTCGCACG
ACAACATCATATGCGGCATCACATCGGTGGCATTCTCGAAGAGCGGACGTCTGTTATTAGCGGGCTACGATGATTTCAACTGCAATGTATGGGAC
ACGATGAAGGCAGAACGGTCTGGCATACTCGCTGGCCACGACAACCGTGTATCCTGTTTGGGTGTCACCGAGAACGGCATGGCGGTGGCAACAGG
ATCGTGGGACTCCTTCTTGCGTGTATGGAACTAAAAATAAAACAGAAACAGAAACAGCAGCATAAGCAGAAACAGAAACAAAACAAAACAAAAAA
CAGAGAAAACCAAACAAACAAAGAACAACAAAAAAAGAGGAAAAAGAAAAAGAACTTGAAAATGCATTAAAGGGTGGGGTGGGGTGTCAGGTCAA
CGGTTGCGCAGTCTGCGGATAGTGTTTCACCCATCATCTACATTGTGATCTAATGTATATGATTCGGTGTTACCGTCTCTGTGGTAAATATTAAA
TGAGTGCCGGACGTTTTGAATATGTGGGCGCAGCTAGTTGACTAGAACGTAGACCACAACAACAAAGAACTTTATATACAACATTATTTATATTG
CTATATACTTATTAACTAAAATTATACAAAAAAACAAAATAAAACCAAAAAAAAAAACAACAAAAAACCGAAAAAAAAAACCGCAGACATACGCA
GCAACATACAAATAGACATACACACGCATACAAGAATATTATTAGTGTAAATGGAAAATTGAGAAAAGAAAAAATGAAAAACCAAGAACAAGCGA
TCAAGAAGAAACCAAAACGATAAAGAAATTGATGGAGTAACGATGGGCCCGCTGATAGTCAGAAGAGTAAGAGTCAGTTGTTTAGTCAGAATTCC
GGTTACAGCTACAGTTTAAAGCGTACGTAAATTAAACTTAGTTCAAATCGCATTTCAGCGGTGAGTGCGTGCAGCTGAGAGCACAAGGCTGCCAG
CCCCTGGACTCCTGGCATCCCGATCCTGGTCCTGATCCCGCATCGGAACCCGCATCCGTGTCCCAGGAGCCGCAGGAGTGGTGCTGGCCAGTCAG
TCAGTTAATCAGTGAGTCAGTCGTTTGCACTTTGTAAAAGAAAATGAAGATGGTATCATTGTAATCATGTATGTCAACAAGTAAATACATATTCT
TTTGCGTATAATACATAAAACTTCAGAATGTGTGGATGTGGATGATCCTGATGCAAGGTGGGGATGGTGGAGAAGTCAAATAAAGTTAAAGCATT TAAAAAAAATAAAATAAAAAAAGAATCACGGCAAACCTAAACGTAAAGCAAAACAAAAGAAAACAAAAATGAGAAAGAAAAGAAGATGAAGATGG
AGGAAACCAAACAAGAAACAAAAACAAAAATTGCGTAATAAACTTTATAAATCAAGTAATGAAAACAAAACAAAACAAAAAAAAAGTAAAGAAAA
CACTATAACAAATTTTTGTCTTATTATGTTTAAGTCCCTAATTTATATACAAACAAAAATAAGAATGATTTAAATAACATATATGTAAACTATGC
ATTAGTGAAAAAGTGGAAAACTATTTATATATA
(SEQ ID NO: 1147)

Exon: 1001..1098
Exon: 1988..2340
Exon: 2414..3973
Start ATG: 2622

Transcript No. : CT29492
GAAAAGTTACAGATTGGTGGCTTCGTTAACAAAATTTTCAGTTATTTGTGTAGTTGAAGACGGGAATTTGTTTTGCGTATAAAAAGTTAACACTG
CGTAACTTTCTGCAGAGGTCTGAAATACACCAATCGCACATACCAAACAAAAAGTAATAAAAAAGAAATAATTGAAAAACCAAATAGTTAAATTG
GCAGAGCAAACACAGGACGACGACTATGAACTAAAGTCAGAAATTAATGGACATCGTACCGAGAATATAATCCGTGAATAGTACTATACGATAAA
ACAGAAAAAGAAAAAAAGTCAACTAAAAAGCAAAAAACCAACTCTTGCAGAACACAGTTCATGATTTATCCATACTAGAAGTGCACAAAATAAAC
GCCGTATGCAAGCGTGATCATCCAAGGCTCATTATCCGACTAAGCTACTGGCCAGCTTAAAAAAAGTAAGCCACCATCTAACAAGAGCGAATCGA
ATCGAATCGACTTGGACGACCGACCGACCGACCGCACAAAGAAGGATCTATCTGGAAAGCCGGCTAGCCGATTCCCGCATCCGATTCCGAATACG
AATACGTATCCGTATCCGAATCCGAATTTGAAACCGAATCCTCAACCAAATCATCCCATAAGGACGCCGCTGTCTTCAACGATCACAAGATGAAT
GAACTAGACAGTCTCAGGCAGGAAGCCGAGTCCCTAAAGAACGCCATTCGGGATGCCCGGAAGGCGGCCTGCGACACATCACTGTTGCAAGCGGC
CACCTCGCTGGAACCCATCGGCCGCATACAGATGCGCACCCGTCGTACATTACGCGGCCATTTGGCGAAAATCTACGCCATGCATTGGGGCAACG
ATTCAAGGAATCTCGTATCAGCCTCACAGGACGGCAAACTGATCGTTTGGGACTCGCATACCACGAACAAAGTCCATGCCATTCCACTGCGATCC
TCGTGGGTGATGACCTGTGCGTACGCCCCATCCGGTAGCTATGTGGCCTGCGGTGGCCTCGACAACATGTGTTCAATTTACAACCTAAAGACGCG
CGAGGGCAACGTCCGGGTGTCCCGTGAGCTGCCCGGCCATGGTGGCTATCTATCGTGCTGCCGCTTCCTGGACGACAATCAGATCGTGACCAGCT
CCGGTGATATGTCGTGCGGATTGTGGGATATCGAGACGGGACTGCAGGTAACCTCGTTTTTGGGCCACACCGGCGATGTGATGGCCCTCTCACTG
GCGCCCCAATGCAAAACGTTCGTATCCGGCGCCTGCGATGCGTCCGCCAAGCTATGGGACATCCGGGAGGGTGTCTGTAAACAAACCTTCCCCGG
CCACGAATCCGATATCAATGCGGTCACATTTTTCCCGAATGGTCAGGCATTCGCCACCGGTTCGGACGACGCAACCTGTCGATTGTTCGATATCC
GTGCCGATCAGGAGTTGGCCATGTATTCGCACGACAACATCATATGCGGCATCACATCGGTGGCATTCTCGAAGAGCGGACGTCTGTTATTAGCG
GGCTACGATGATTTCAACTGCAATGTATGGGACACGATGAAGGCAGAACGGTCTGGCATACTCGCTGGCCACGACAACCGTGTATCCTGTTTGGG
TGTCACCGAGAACGGCATGGCGGTGGCAACAGGATCGTGGGACTCCTTCTTGCGTGTATGGAACTAAAAATAAAACAGAAACAGAAACAGCAGCA
TAAGCAGAAACAGAAACAAAACAAAACAAAAAACAGAGAAAACCAAACAAACAAAGAACAACAAAAAAAGAGGAAAAAGAAAAAGAACTTGAAAA
TGCATTAAAGGGTGGGGTGGGGTGTCAGGTCAACGGTTGCGCAGTCTGCGGATAGTGTTTCACCCATCATCTACATTGTGATCTAATGTATATGA
TTCGGTGTTACCGTCTCTGTGGTAAATATTAAATGAGTGCCGGACGTTTTGAATATGTGGGCGCAGCTAGTTGACTAGAACGTAGACCACAACAA
CAAAGAACTTTATATA
(SEQ ID NO: 1148)

Start ATG: 660

MNELDSLRQEAESLKNAIRDARKAACDTSLLQAATSLEPIGRIQMRTRRTLRGHLAKIYAMHWGNDSRNLVSASQDGKLIVWDSHTTNKVHAIPL
RSSWVMTCAYAPSGSYVACGGLDNMCSIYNLKTREGNVRVSRELPGHGGYLSCCRFLDDNQIVTSSGDMSCGLWDIETGLQVTSFLGHTGDVMAL
SLAPQCKTFVSGACDASAKLWDIREGVCKQTFPGHESDINAVTFFPNGQAFATGSDDATCRLFDIRADQELAMYSHDNIICGITSVAFSKSGRLL
LAGYDDFNCNVWDTMKAERSGILAGHDNRVSCLGVTENGMAVATGSWDSFLRVWN*
(SEQ ID NO: 1149)

Name: G protein beta-subunit 13F
Classification: signal_transduction
Gene Symbol: Gbeta13F
FlyBase ID: FBgn0001105

Celera Sequence No. : 142000013384690
TTAGTACAATCGCTTGTAGGTCAACAGTAAAACTAACTAAATACTAAACCTATTCCTTGGAGACGGGTTTGCAGGCTATCATGTACACTGGAAAG
AGTCCCTTGGGAAAGTTTTGTTGCTTGACCTTGCGTACAATGCGAAATCCGGCTTCCTTTAGGAAGTGTTCATAGCTGTCCAGAGGCCTCGTTAC
CGACGAGTCGTTCCTATCTTCCACTGTCTTCTTCGAGCTGCTCACGTTCTCCTTCAGACACAAGAAGGCGCCGGGCGCCAGTCCCTGCTTTATGC
GTCGAAAGAACGAGACCAGATCGCGGTCCGTGAGATGGCCCAGGACCCACTGGGTCCAAACGAGGTCGTACTGTTGCGTAGGCGTAAACTTCTGC
AATCCCACGTTATAGATCTGTCCCACCTTTCCACGGCTTCCGTCTTCCGAAGTGCAGTACTCCCGTGCTTTATCGGCAAACGCGGGATCCTGCTC
GACAAGATCCACGCAGCTGAAGCGGGGGATCAGGAGATTCCGAGTCACCCGACCAATGCCAGCTCCGCAGTCGAGGGCCAACCTGTTGCCCGGCA
CGCGGATCTCGCGCAGGAACACATTCGATCCCTGTATATCTATGGCACTAATGTAGCCCAGGCCGCCGAGCATCCCGTTAACAGTCGCCGGTACC
TCAGACCAATATTTTTGTGCCTTATTGTAAAATTCGGACTCCGGTGCGGCGACTTTGGTCGAACTATCGCTCGAAGAAGGGGACGCTGTCTTGGC
ATCTGAACTTGCGGCTATACTGCTATCATCCTTCTGCTTCGACGACCCCTGGACCTTATCCGTGGTCTCGTCCATCATCTGCAACTTGTCTGAAA
GCTGCTCTTCTAATGTAGTCGTCATTTTTGTCAGGATTTCGAAGGCCGCATGCTTTGTTTTGTTTTAGTGCGATAACCAGGGCTCCTAAACACAG
TGAGCCATTTAGGTTTTACGAAAGAGTGGCAACCCTTCACCAATCAGCTGTTCAACAAGCAACAAAATTGTCCGTTTGTTTATGTTACTAGTTTT
TTGTTTAATTTTTCTATTGTCCGGACAAAATGACTCTCGATTTGGATGCGCATAAGAAAGATGACAAGTTGCTGATCACAACCATACAGCAGGAG
TATAAAATTCTGGCCGAATAGTGAGTTTTCAGAGTTCACTGATAACTACGTGGAGTAAAACTAAACTTATTTAATTTCTTATGTTTTAGCAAAAT
GATTGAGTCGGAGAAGTTGAGTGGGATATATGTGATACCCAGCTATGCTAACTCCTTGCGTTAGTCTACCCACCTGCCAACCTGTATGCAGTCTT
TAGCTAATTTTATCTTTTGTTAATAGAGTGGTTTGGAGTCTTCTTTGGCCGACAGGGCTTGTATGCGGAAAGTGTTTTTCGATTCACAATTTTGC
TCCCAGATCGTTTTCCCGACGACAAAAGTCTTCCGGTGAGTAGGATCGGCAATAGAGCAAACGTATTTAACTCTACAAGTCCCCTTTAGAGCATA
ATTTCCAGCAGGATGTGATTCATCCCCATGTGTGCCCGTACACCCACAGTTTGGACGTGAGCCACGCCTTCCCGGAGTGGCGCTGTGGAGAGGA
TCACCTTTGGCAGCTTTTAAAGTACCTGCAAGTCATTTTCTCCGATCCCTTGGACAGTATTCGGGGCATTGAGGTAGATAAGCTCAAAAACAGCG
AGGCTGCGGAGCTGCTGATGAATAACAAGGAGGAGTATGTTGCTCGCGTACAGGAAAATATCAAGGAGAGCAAGGAGCATATATTTGACACCCCA
CCCACCGAAGATCCGCACTACATAGTATTCGAGAAGTTCCAGCAGGACGTGCACGGGCCCGTTCTGGAGCGCATCAAGGCCGGAAGAAGCAAGCT GACGGAGCCTTCAGCGCAACAAGCAAATGGTGGACATGCAACTGGTCTGTCATGGGTTAAGGAGGGCGAGTTTAAGCCACTTAGCATTGAGTAAA
ACCAATATACATATATTCTGTAAGTTATATTCTATCGTTGTCTCAATTTTAAAACGATTAAAGTTATTCAATTATTTACAATCCTCGTTCATGGG
AAATCGCTGAGTATTGTTAACCCACTCGTTCTGCAACTCTAAACGTTCTCCGTTCCATTGGAAATGTGTGGGGAAGCCTCGCCAGCGAGAAACT
CAAAGTGCTGGCTGAGCTCGATGGCCAGTTTGGAGCGGACTAGGCCTATTCCGCCCACCTGTGGCGCAGCTGGATGATAGACCCTTCCGTTTCGC
GGATCCATGTACAGTTTGTGGGGTTCGTAAGGCAGGGTAAGGACCTGTCCCGCGTGTGCATAGCTGAGCACCTCCGTATCGTCCTTCCTCAGCTG
TTCAGTAAACACAACAGGTGTGTCATCGCACCTAATAAAATTCCTTTCGCGGCCACAGAGGGAAATGTATGGAAATTCGCTTTCATATCTGCTCG
TTTTGTTTAGCCGCAGTCGGTTGAAAAAGAACTTGAGGAAATCCTTCTCCTTAAAGCAGCTGGTGAAGTTTTTCATCTTTGCATCGTCCAGGAAG
AGCTGCAAAACGGGTTATGCGAGTTGAAGCACAGATGCATAGTTGAGAGTCTCACCATTCCCTCATGATCGATATAGTAAAAGTATTCGCGAATT
TTTGGCTCCGGAGATTGACCTTGGTTATATTGTACGTAACGGCAAGATATGCTTGGAGATCTAACGAATTTTAGGTTTGTAAGGGATCTAGAACG
TAGTATAAACATTGTTCCTCTATCTGAGTACTGTGTCTTCTTATGAGCAACAAAAACAGCTGACTTTTGTTTACTACATCTGTAGGTGCATTTGA
TAACCTCCCATTATCAATTTAACGTTTTTACAGTTTTGTATTTTCTCAATAGGTAGCGATTATTTTTGCAAGTACATTTTTTGGCAGTCACATAT
TTTTGCATCGCGAATACAGCGATATACAGAAATGAAAACATTTTATTTAAAAAAAGGTGGCTATGTGACTGTCTATTGAATTCGACATTTGGTCG
AAAAGCTCAGGTTTTGCTTAAAATAGCA
(SEQ ID NO: 1150)

Exon: 1001..1160
Exon: 1230..1294
Exon: 1357..1460
Exon: 1515..2068
Start ATG: 1075

Transcript No. : CT29563
TTCAACAAGCAACAAAATTGTCCGTTTGTTTATGTTACTAGTTTTTTGTTTAATTTTTCTATTGTCCGGACAAAATGACTCTCGATTTGGATGCG
CATAAGAAAGATGACAAGTTGCTGATCACAACCATACAGCAGGAGTATAAAATTCTGGCCGAATACAAAATGATTGAGTCGGAGAAGTTGAGTGG
GATATATGTGATACCCAGCTATGCTAACTCCTTGCAGTGGTTTGGAGTCTTCTTTGGCCGACAGGGCTTGTATGCGGAAAGTGTTTTTCGATTCA
CAATTTTGCTCCCAGATCGTTTTCCCGACGACAAAAGTCTTCCGAGCATAATTTTCCAGCAGGATGTGATTCATCCCCATGTGTGCCCGTACACC
CACAGTTTGGACGTGAGCCACGCCTTCCCGGAGTGGCGCTGTGGAGAGGATCACCTTTGGCAGCTTTTAAAGTACCTGCAAGTCATTTTCTCCGA
TCCCTTGGACAGTATTCGGGGCATTGAGGTAGATAAGCTCAAAAACAGCGAGGCTGCGGAGCTGCTGATGAATAACAAGGAGGAGTATGTTGCTC
GCGTACAGGAAAATATCAAGGAGAGCAAGGAGCATATATTTGACACCCCACCCACCGAAGATCCGCACTACATAGTATTCGAGAAGTTCCAGCAG
GACGTGCACGGGCCCGTTCTGGAGCGCATCAAGGCCGGAAGAAGCAAGCTGACGGAGCCTTCAGCGCAACAAGCAAATGGTGGACATGCAACTGG
TCTGTCATGGGTTAAGGAGGGCGAGTTTAAGCCACTTAGCATTGAGTAAAACCAATATACATATATTCTGTAAGTTATATTCTATCGTTGTCTCA
ATTTTAAAACGATTAAAGTTATTCAATT
(SEQ ID NO: 1151)

Start ATG: 75

MTLDLDAHKKDDKLLITTIQQEYKILAEYKMIESEKLSGIYVIPSYANSLQWFGVFFGRQGLYAESVFRFTILLPDRFPDDKSLPSIIFQQDVIH
PHVCPYTHSLDVSHAFPEWRCGEDHLWQLLKYLQVIFSDPLDSIRGIEVDKLKNSEAAELLMNNKEEYVARVQENIKESKEHIFDTPPTEDPHYI
VFEKFQQDVHGPVLERIKAGRSKLTEPSAQQANGGHATGLSWVKEGEFKPLSIE*
(SEQ ID NO: 1152)

Classification: enzyme

Celera Sequence No. : 142000013384486
ATTAAAACTTAATTTTACAAAAAAAAAATTAAACGAAATGTTTGTTTGGTTGGCGGGGGGGGGGGGGTGTTTTCTCGATGCGAAGCTTTGGGAGC
TTTTAAGCGCCGTCAACCGAAATGGGGGCTCGTCAGCGGCTCTCAAACTGTGCCGAGGAAGTTTGAGAGCCTATGAAGGCGGTAACTAATTAATA
AATTTCCTTTTATTAGCACATGCCTTTTAAGTTTACACAATTTTAATAGTTTCTAAATGAAAGTGAAATGTAACTATTATTTATTTGATTAGTTT
TTTTTCTTTATTCAGTGGTTTCTATTTATGCTAGTGCCCTTTTTACGCTGCTCTTTCAAATGCCAATCATCGACGTTTCTTTATTTTTAGCCATT
TCCCACCTGGGCACGCAAATGGCAATTGATTAGCATAATTAATGGCAAAAACTTTGCAATAAAGTAAAAAGTTCGAAGAAGGGCCCCGAGCCAAG
TCAAATGACGGAGGCGCAAAAGCGAAAGTATGTTAGCATAAATCGATCAAGGAGGAGCAGCCGCCGGCCGAAAGGGGGAATCCCACCGAGGTGCC
GTAAGACGGGACCGCAAGGTGCAGGAGCAGCCGGCGGCTCCTTCGCCGGATTTGAGCGCTGTGTGCCCAATTGGATTGACTGTCAGGTGACACAC
GGCACAAGCGCATTGGACGAGCACATGCACACGGTCGTATGGCATTGGTACACTGAGAGAAAGGGAGCCGAGGAATTGGAAATATTTAGGATAAT
AGCATATCATTCTACAATTTGGAAAAGAGGAACATTATGTGCGTTCTCAATAATGAATTTATATTACTACTCCCATGTTTATCATGCTAAGATGC
ATCATAGTATTAGGTTAAACACCCTACTTTGGTGCAGTGTATGCTCTAAAGGGAAGGGGGGGGGGGAGGTATGACTGGGGCTAGTCAGCAACATAAC
AATAAATACCGCTAGGCAACCGTAAATTCCCTAGCATGAATCGATTTAACATGACCGCGGGAGCGGAGGGCAGGCCACTCAGTTCGCCAGCGAAG
CTCCTCCGTCCAACTCCGGCCGAGATTCCGAGCCAGGCAGCCAGCCAGCCAGGTACATACGATTTCCTGCCCGGTCTCCAGAGAAGTGTGCCAGG
TGGGTATAATCGAGTGTAGAGATTTGCAGTGACAGTTCCACTTTTTACCCAGCGCTCCTTGCATACATTTCTTATATACATACTTCTTATGCAAT
CTTAATCGCACCCAATCCCAGCGAGAAACATGTTGCCCAACCTGAAGTCGCGCCGCATCAGCGGCCTGCAGCTGGCCGGGAAGCACCTGGGTCCG
GTGGCCAAGTGCCCGCCCAGATATTCCGAGGAGGACTGGGACTATAACAACAAGATCAAGTTTCGAATCACCTGCGACCAGGAGAAGCTGGCGGA
GCGGATCGTGGAGTGAGTATATCGGGCGGGTGGCGGATTCATTGGGAGCGGATTCAAGTTGGTGACCCTATTCTATGCAGGGAGTCGCGTCGCGT
GGTGGACGAAACGAAGGACACCACAAAGAACTGGCAACGGAGGTGGAGCACCATATGCGCGAACGGACGAGCGAAATCCGATTCCTGGTGGACG
AGTTGAATCGCCAGAAGAAGACCGCCGCCCTGGAGGATGAGGCCTTGAACACCTATCGCAATCCGCGTGCTGAACTGCATCGAGTTCCTGAAGGAC
AAGTCGCTGGCCATTTGCAAGCAGTGCCTGATCCTACGCGAAGGTCGGATCGGTGTGGATTTGTGCGACGACGAGGTGGATCGCTCGCTGCGCCG
TGAGCTCAAGGTGATCAAGGGCTGTCAGGGATTGGCCGATGCCGCCCTCAAGGAAGCCGAGGAGCAGATCCGCAAGCTGCGCGCCGCCATCTATT
TGCTCGATCAGGATCTGGCCGCCAAGGATAAGTCACTGGCCATCGACGAGAAGAACCTGAAGCTCAAGGAGTTCCAGCACGACCTGGCTAAGGGA
CAGGATTTGTCCAAACAGCATTGGTAGGTTTTGAAAACTAGGTTGCATGTCAATCACACATGTTGGGGTTTCCTTTTTAAGGAATGATGAAGTG
GATTGATTATTAATCTTTTTTCTTTCACTTTTATGCGTAAGTCATTTCGGTGTTCATCAGTACAAGGAGTTTAAAAGGATAAACATTTTACTAGA
GTCTTATCCACAAATTCCATTACAAAGTCAAGTAGTTGTTCCCCTTTTCAGTTAGGAATGGAATTGAGGAAGGTCAAACCTAACAATGAAACCGC
AGTTTCCTTGGTGATATGGGATAGAGTTGTCCTGAGTCTATTTTAGTGCATTGGAATTAAGTGATTTATTTACAACCACTCAAATCGACCTGATA
GTTGCCATGACTCCACCATGCCTTTACCCCCTTCTCTTCCTTACCCAGCCAATTTTCGCTGACCGAGTGGCAGGCGCAGACGTACGAGAATCTGG AGGCCAACGCCAAGGCGCTGGTGTCCGCCGGGCAGCTGCGGGCCTACATCGATTTGCTGCTGAAGCAGGTGTGCGAGGATATGCAGAACCAGACG
GACAGGACCAACGAGGCCTTTGAGCGAAGGATCTCGGAGACGAAGCACGTGAAACAGTGTTTGGAGAACAAGCACAAGGACACCATGGATCACAT
CCATCAGGTGCAGCGCAACATGACCGAGCTGGAGAAGGAGATGATGGACAAGCAGCGGGCCATTACACTGTGCCAGACGCGGCTCAGCAATCGCG
CCCATCGTCCTGGCCTGGAGCTGACCTGCGACATGGTCCAGGATGCGCTTTACAACGAACTGCAGGCGCTGAAGGCATCCGTATGCAAGCTCAAT
CAGAAGCTGAACGAGAACAAGGCATCCATGCGCTACCTGATGCACGTCCAGGTGATGCAGGAGGAGGAGATCAACATCAAGGCGAACACCTGCAA
GATCGACGAGGTCGACTGCATGACCCTGCGACAGGCCCTGAAGTACCAAACATTTTAGTCGGGCAGCACTACATCCAGTACAGCACCAGTCCAGT
AGTCGCCACACAGCCCAGCCACCAATAATCAAATTAAAATCTAATTATTAGATGCATGTGCATTTCGTGTTCGATCCCAAATTACTTAATAAATT
GAAATTCACTTTCGATTTCCAGTTACCAAAACTATGGCTTTTTAATGCATTTTTAAATTGTTCATTTTATTCGAAATAGTTAATCATATATTTCT
TTTGCTTAATTTTCGTGAATTTAAATTTCCCGCTTTGAATCTAGTATTTTTAGTTTTACCTGCCTCTATTCGATATTTACCGCTAAGCACAGACA
TATAGTTATCGATAACGTGAACGCAAATGCGAGGGAGTATTGCAAATAGTGTTACCGTGCTGCTGTGAAAATTCCCAGGTGTGACCGCAGCCCGC
ATTCGATATTGATGAAGCCAGGCAAAACGTAGAAAAGCAAAAGAAAACCTTAATTAATGTTAAGTTAAAAGTGTATAAACCCGAGATTAAGGTAA
GTGGCCCACCACCATCTAGATTTTGAGTACACCGAAGGCATGGCGATGTTGGCAGTGGCGGGAGCGTTACGCCTCTACCGCCACCGCCTCCGCCG
CACACGATAAAAAATGGAGTACAGCCACGAATGGGCAAATCAATAATTTTCAACACTCCAATTGTTTTTACAACTGAAATCAGTCCTAATCTTGT
TTTCCGCAGTGCAAGGATGTCGAAACGGAGCGCCGACGACGCCACCGGCAGCAGCTGCTTGGTGGCCGCCGCAGCCGCCGGCCAGCCGCCCATCA
AGAAGGTGCACTTCGAGCCCCATCTGATTGGGCCGGTGTCCACGCTGGAGGAGATGGACATCAAGGTGCTGGAATTCCAGAACAAGAAGCTAGCA
CAGCGCATCGAACAGCGGATGCGAACGGAGGCGGAGCTGCGACATCGAATCGAGCAGCTGGAAAAGCGGCAAACGCAGGACGACGCCGTTCTAAA
CGTGGTCAATCGG
(SEQ ID NO: 1153)

Exon: 1001..1139
Exon: 1257..1437
Exon: 1506..2018
Exon: 2424..3003
Start ATG: 1001

Transcript No. : CT29571
ATGACCGCGGGAGCGGAGGGCAGGCCACTCAGTTCGCCAGCGAAGCTCCTCCGTCCAACTCCGGCCGAGATTCCGAGCCAGGCAGCCAGCCAGCC
AGGTACATACGATTTCCTGCCCGGTCTCCAGAGAAGTGTGCCAGCGAGAAACATGTTGCCCAACCTGAAGTCGCGCCGCATCAGCGGCCTGCAGC
TGGCCGGGAAGCACCTGGGTCCGGTGGCCAAGTGCCCGCCCAGATATTCCGAGGAGGACTGGGACTATAACAACAAGATCAAGTTTCGAATCACC
TGCGACCAGGAGAAGCTGGCGGAGCGGATCGTGGAGGAGTCGCGTCGCGTGGTGGACGAAACGAAGGACACCACAAAGAACTGGCAACGGGAGGT
GGAGCACCATATGCGCGAACGGACGAGCGAAATCCGATTCCTGGTGGACGAGTTGAATCGCCAGAAGAAGACCGCCGCCCTGGAGGATGAGGCCT
TGAACACCTATCGCAATCGCGTGCTGAACTGCATCGAGTTCCTGAAGGACAAGTCGCTGGCCATTTGCAAGCAGTGCCTGATCCTACGCGAAGGT
CGGATCGGTGTGGATTTGTGCGACGACGAGGTGGATCGCTCGCTGCGCCGTGAGCTCAAGGTGATCAAGGGCTGTCAGGGATTGGCCGATGCCGC
CCTCAAGGAAGCCGAGGAGCAGATCCGCAAGCTGCGCGCCGCCATCTATTTGCTCGATCAGGATCTGGCCGCCAAGGATAAGTCACTGGCCATCG
ACGAGAAGAACCTGAAGCTCAAGGAGTTCCAGCACGACCTGGCTAAGGGACAGGATTTGTCCAAACAGCATTGCCAATTTTCGCTGACCGAGTGG
CAGGCGCAGACGTACGAGAATCTGGAGGCCAACGCCAAGGCGCTGGTGTCCGCCGGGCAGCTGCGGGCCTACATCGATTTGCTGCTGAAGCAGGT
GTGCGAGGATATGCAGAACCAGACGGACAGGACCAACGAGGCCTTTGAGCGAAGGATCTCGGAGACGAAGCACGTGAAACAGTGTTTGGAGAACA
AGCACAAGGACACCATGGATCACATCCATCAGGTGCAGCGCAACATGACCGAGCTGGAGAAGGAGATGATGGACAAGCAGCGGGCCATTACACTG
TGCCAGACGCGGCTCAGCAATCGCGCCCATCGTCCTGGCCTGGAGCTGACCTGCGACATGGTCCAGGATGCGCTTTACAACGAACTGCAGGCGCT
GAAGGCATCCGTATGCAAGCTCAATCAGAAGCTGAACGAGAACAAGGCATCCATGCGCTACCTGATGCACGTCCAGGTGATGCAGGAGGAGGAGA
TCAACATCAAGGCGAACACCTGCAAGATCGACGAGGTCGACTGCATGACCCTGCGACAGGCCCTGAAGTACCAAACATTTTAG
(SEQ ID NO: 1154)

Start ATG: 1

MTAGAEGRPLSSPAKLLRPTPAEIPSQAASQPGTYDFLPGLQRSVPARNMLPNLKSRRISGLQLAGKHLGPVAKCPPRYSEEDWDYNNKIKFRIT
CDQEKLAERIVEESRRVVDETKDTTKNWQREVEHHMRERTSEIRFLVDELNRQKKTAALEDEALNTYRNRVLNCIEFLKDKSLAICKQCLILREG
RIGVDLCDDEVDRSLRRELKVIKGCQGLADAALKEAEEQIRKLRAAIYLLDQDLAAKDKSLAIDEKNLKLKEFQHDLAKGQDLSKQHCQFSLTEW
QAQTYENLEANAKALVSAGQLRAYIDLLLKQVCEDMQNQTDRTNEAFERRISETKHVKQCLENKHKDTMDHIHQVQRNMTELEKEMMDKQRAITL
CQTRLSNRAHRPGLELTCDMVQDALYNELQALKASVCKLNQKLNENKASMRYLMHVQVMQEEEINIKANTCKIDEVDCMTLRQALKYQTF*
(SEQ ID NO: 1155)

Name: TEKTIN
Classification: cytoskeletal_structural_protein

Celera Sequence No. : 142000013384486
ATTACACTGTGCCAGACGCGGCTCAGCAATCGCGCCCATCGTCCTGGCCTGGAGCTGACCTGCGACATGGTCCAGGATGCGCTTTACAACGAACT
GCAGGCGCTGAAGGCATCCGTATGCAAGCTCAATCAGAAGCTGAACGAGAACAAGGCATCCATGCGCTACCTGATGCACGTCCAGGTGATGCAGG
AGGAGGAGATCAACATCAAGGCGAACACCTGCAAGATCGACGAGGTCGACTGCATGACCCTGCGACAGGCCCTGAAGTACCAAACATTTTAGTCG
GGCAGCACTACATCCAGTACAGCACCAGTCCAGTAGTCGCCACACAGCCCAGCCACCAATAATCAAATTAAAATCTAATTATTAGATGCATGTGC
ATTTCGTGTTCGATCCCAAATTACTTAATAAATTGAAATTCACTTTCGATTTCCAGTTACCAAAACTATGGCTTTTTAATGCATTTTTAAATTGT
TCATTTTATTCGAAATAGTTAATCATATATTTCTTTTGCTTAATTTTCGTGAATTTAAATTTCCCGCTTTGAATCTAGTATTTTTAGTTTTACCT
GCCTCTATTCGATATTTACCGCTAAGCACAGACATATAGTTATCGATAACGTGAACGCAAATGCGAGGGAGTATTGCAAATAGTGTTACCGTGCT
GCTGTGAAAATTCCCAGGTGTGACCGCAGCCCGCATTCGATATTGATGAAGCCAGGCAAAACGTAGAAAAGCAAAAGAAAACCTTAATTAATGTT
AAGTTAAAAGTGTATAAACCCGAGATTAAGGTAAGTGGCCCACCACCATCTAGATTTTGAGTACACCGAAGGCATGGCGATGTTGGCAGTGGCGG
GAGCGTTACGCCTCTACCGCCACCGCCTCCGCCGCACACGATAAAAAATGGAGTACAGCCACGAATGGGCAAATCAATAATTTTCAACACTCCAA
TTGTTTTTACAACTGAAATCAGTCCTAATCTTGTTTTCCGCAGTGCAAGGATGTCGAAACGGAGCGCCGACGACGCCACCGGCAGCAGCTGCTTG
GTGGCCGCCGCAGCCGCCGGCCAGCCGCCCATCAAGAAGGTGCACTTCGAGCCCCATCTGATTGGGCCGGTGTCCACGCTGGAGGAGATGGACAT
CAAGGTGCTGGAATTCCAGAACAAGAAGCTAGCACAGCGCATCGAACAGCGGATGCGAACGGAGGCGGAGCTGCGACATCGAATCGAGCAGCTGG
AAAAGCGGCAAACGCAGGACGACGCCGTTCTAAACGTGGTCAATCGGTATTGGAATCAGCTGAACGAGGACATACGAGTCCTGCTGCAGCGCTTC GATGCCGAGACGGCCGACGAACTGGAGAACCGGAATGAGAACGAGGTGACCACCTCGTTTCTCGCCCAACTGTCCACCTGGGACAAGGAGGAGCT
GGACGAGAAGCTGGCCAACCGCGTCCAAGTGTCCAAAAGGGCGGTCGCCAAGATCGTACAGGTTATTGATAGGTTAATGCAACGCAATGAAAAGA
TAACTCATGTCTTGAAAGGTGATAGTCTGGCTTCAGCTGGCTCCGGTTCAGGAGCGGGAGCTGGCGGCGAGGAGGAGCAGCAGCAGGCCAGCGGC
GATGCGGAGACCACAACGTCATCGGCCGGTGTCCATGCGCTAGAGGAAACCCTGAAGCAAACGCACATCGAGATCATGAGCGAAAATCACAAGCT
GCAGAATCTGAATACCTCGCTGCACGAGAAGTTCCACACCATGTCGCTGAAGATGAAGGAGTACCAGGACGCTCATACCGCCAAGGAGACGGAGA
ACGCCGAACTGAAGAACCAGATAGACGAACTGCAATATGACCTAGAGAAGATCCATTGCCGGAATGATAAGCTGGAGAACCACTTGGCCGAGGCT
ATTGAAAAGCTGAAGGCCTACCACCAGATTTACGGTGATCCCAATAAGAGCACTAATAGTGCCAAGACACCAACTACCACAGGCAGCGGCGGCGC
CACCACCAGCGTTAATAGCCAGCTATTGGAGGAGCTGCAAAAGGAGCTGGAGGAGTACCGCGAACTGGCCAACAACCGACTGCAGGAGCTGGATA
AGCTTCACGCCACGCATCGCGAAACCCTGAAGGAGGTGGAGAAGCTTAAAATGGATGTAAGTTTTGAATGAATAATGTATTAGCTTATCTGGAGC
ATTGCTAATTATAGTTAGTCATTTCGTTTATATTTTCTTTGTATTATACTGATTCATCCTTAAAATCCATTCCAGATACGACAGTTGCCGGAATC
GGTAATTGTGGAAACCACGGAGTACAAGTGCCTGCAGAGCCAGTTTTCCGTGCTCTACAACGAGTCCATGCAGATAAAGACCATGCTGGACGAGA
CCCGAAACCAGCTTCAAACGAGCAAGAACCAGCATCTGCGACAAATCGAAGTGATGGAGAGCGAGGAACTTATTGCCCAGAAGAAGGTGCGCAGC
GAGATGATCCAGATGGAGGACGTTTTAGCCCTCATCCGAAAGGAGTACGAAACGCTACGCATTGAGTTCGAGCAGAACATGGCAGCCAACGAGCA
GACGGCACCCATCAATCGCGAGATGCGCCACCTGATCACCTCTCTACAAAACCACAATGGCCAACTGAAGGGTGAGGTGCAGCGCTACAAGCGAA
AGTACAAGGACACGTCCACGGACAACTTGAAGCTGCGTCAGGAGCTGGCCGATGCACTAGCTACACTCGAAGGCAACAAGTTGCAGGCGGCGACT
GGTGCGGCTGGCGAAGAAATCAAGCAGGAGAACTCAACAGGTGTGAAGGAGGAGAACTCCAACAACGTTTCCGCCAGTGGACAAACAAACCAAAC
AAATTCCGGCAACGATACCAACGTAGCCATCAAGGAGGAGAACCATATCTCGGCTGAAGATGAAGCTGATGACGAGGCCAGTGGTAAGGACGTAA
AAGACGGCATCAAGCAGGAGAAGCTCAGTTCTGGAGACGCGGCGGCAGCTGAGAAGAAGGATTCCCCTGGACCCGGAAACTCAACAAGTTCTGCG
ACCAATTCTGTTCCCGTCAAAAACGAAAAGGATTCCAAGGATGGTGTCAAGGGCAAGGATGTGAAGGCAGTGGAAAGTGAAACGGTGCGCGATCT
GAAGGCGCAACTAAAGTAAGTTTGTTCAGCAATTACGATTATCTATTTAACATTGTTTGATTTACAGAAAAGCACTGAACGACCAGAAAGAAATG
AAACTCCTGCTGGATATGTACAAAGGCGTATCGAAGGATCAGCGCGACAAGGTCCAGTTGATGGCCACCGAAAAGAAACTGCGCTCCGAGATCGA
GGAGCTCCGCCAGCAGCTGAAGAAGCTGCAGGAAAGCAAGCGCGAGGAACGCAAGAAGCTGGCCGACGAGGAGGCGTTACGTAAGATTAAGCAAT
TGGAGGAGCAGAAGTACGAGCTGCAAAAACAGATGGCCAACCACAAGCCAACGGATAATTCTTGGGGCAGTGGAGCCCCCGGCACAGCGAACTAC
ACGCGACCGTTTGTTGGTTCCCACGAAGAGGAGGCACTGCTGAACGAGATGGAGGTTACCGGCCAGGCGTTCGAGGACATGCAGGAGCAGAACTC
CCGGCTCATACAACAGCTGCGTGAGAAGGACGATGCGAACTTTAAGCTAATGTCGGAGCGCATCAAGGCCAACCAGCTGCACAAACTTCTGAGAG
AGGAAAAGACGGTGCTGGAGGATCAGATGGCAACGGCGACCACGCAAATCGAAGCCATGCACATTGTGCTGCGAAAGCTGGAGGAGAAGGAACGC
AGCCTGCAGGCCACCGTCGCGTCGATTGAGAAAGAGTTGATGCTGCGGCAGCAAGCAATGGAGATGCACAAACGCAAGGCGATTGAATCGGCGCA
ATCGGCAGCGGACCTCAAGCTGCATCTGGAAAAGTATCACGCGCAAATGAAGGAGGCGCAGCAAGTGGTGGCGGAGAAGACCAGTTCGCTGGAGG
CGGAGGCCTACAAGACCAAGCGGCTGCAGGAGGAGCTGGCGCAGTTTAAACGCAAGGCGGAGCGCATGAAGAAGATGGAAATGTCGGGCACCACC
ATCGACGAGGTGATGATTGAGGAGATCCGCGAATACAAAGAAACGCTCACGTGTCCCTCGTGCAAGGTGAAGCGGAAGGATGCTGTCCTGTCAAA
GTGTTTCCACGTCTTCTGCTACGACTGCCTGCGCACTAGATATGAAACGCGGCAGCGGAAGTGTCCCAAATGCAACTGCGCCTTCGGCGCCAACG
ATTATCATAGGCTATATCTGCAGTAGATAAGCGATAATTTAGATACGTTCCGGTCATGTCCTATTCATACACAAATCCACCCACGCCACACACCA
CTACCGCACACCCAGCATTCATGCCGGATTATTATTCATTATGCATATATTACCTACGTACTAATATTTGGTTAAGTAGTCTCCGAATAACTTTC
CCCCACCAGATTTCCCATGGCAATTATTTGAATTCGTTCATTCTGGCGCCAAGCAAAAGCATCTCATTATGAGTGCCGCGAGATCGTGACGCGGT
TTTTATGTAGCTTCTAGTTTTTGTAAATCAAACTATTTTTAAATGATTTCATTTGAAAACTAAATGTACGAACACTAATAAATGGCTAAAACCTA
TTGTTTAGCATGCCCCGAGTTATTTAGATACCCCATATATACATAAGTGTAGGTTCTTTGTCTTGCATTCAGTTAGCATTATATTAAGCGTATTC
TAATCTTAAGTTAAATACTCCTATTGTAATGATCAAACGTAGCATAGATATCAAATGTATAAACTTGGCGGAGAATCCGTTTAAAAGTCGCGCTT
TGCTTTGAAGGGCTGCTAACTTGGTTATAATTGATAAGTAATTGTAATAATGTATGATCGAAAATTGTTGTTCAGCTGAACAAAACGAGTTTTGA
TTGCTTTTTTGTTTGTGTGTAAATGTGTTCGTTCTTTATGTGTACTGTTTAACGAATAAAGAAACTAATGATCAGAAATCGTGACTTTCAATCAA
TGTTATCTCTCTACATGAAATCCACCTGTTAGAGCTGTTAGCACCCACGCACTCATGTTAATAACATCGATGCTTATCTGAAACCTGTAACCATT
GGCGCGCAACAGGTTATCGGGGTTTAAAACGCTATGCTGGTATTTTGTTCTCTACAGAAAGTAGGAAAGTGGCCATAACTATAATTTTATGTATA
AACAGTTTGATCATATTCTAAATTTCTATTTTATGGCACAAGAACATAAAACGAATGGTTAATTTAACTCAACTGG
(SEQ ID NO: 1156)

Exon: 1001..2146
Exon: 2261..2756
Exon: 2796..3150
Exon: 3203..4301
Start ATG: 1001

Transcript No. : CT29573
ATGTCGAAACGGAGCGCCGACGACGCCACCGGCAGCAGCTGCTTGGTGGCCGCCGCAGCCGCCGGCCAGCCGCCCATCAAGAAGGTGCACTTCGA
GCCCCATCTGATTGGGCCGGTGTCCACGCTGGAGGAGATGGACATCAAGGTGCTGGAATTCCAGAACAAGAAGCTAGCACAGCGCATCGAACAGC
GGATGCGAACGGAGGCGGAGCTGCGACATCGAATCGAGCAGCTGGAAAAGCGGCAAACGCAGGACGACGCCGTTCTAAACGTGGTCAATCGGTAT
TGGAATCAGCTGAACGAGGACATACGAGTCCTGCTGCAGCGCTTCGATGCCGAGACGGCCGACGAACTGGAGAACCGGAATGAGAACGAGGTGAC
CACCTCGTTTCTCGCCCAACTGTCCACCTGGGACAAGGAGGAGCTGGACGAGAAGCTGGCCAACCGCGTCCAAGTGTCCAAAAGGGCGGTCGCCA
AGATCGTACAGGTTATTGATAGGTTAATGCAACGCAATGAAAAGATAACTCATGTCTTGAAAGGTGATAGTCTGGCTTCAGCTGGCTCCGGTTCA
GGAGCGGGAGCTGGCGGCGAGGAGGAGCAGCAGCAGGCCAGCGGCGATGCGGAGACCACAACGTCATCGGCCGGTGTCCATGCGCTAGAGGAAAC
CCTGAAGCAAACGCACATCGAGATCATGAGCGAAAATCACAAGCTGCAGAATCTGAATACCTCGCTGCACGAGAAGTTCCACACCATGTCGCTGA
AGATGAAGGAGTACCAGGACGCTCATACCGCCAAGGAGACGGAGAACGCCGAACTGAAGAACCAGATAGACGAACTGCAATATGACCTAGAGAAG
ATCCATTGCCGGAATGATAAGCTGGAGAACCACTTGGCCGAGGCTATTGAAAAGCTGAAGGCCTACCACCAGATTTACGGTGATCCCAATAAGAG
CACTAATAGTGCCAAGACACCAACTACCACAGGCAGCGGCGGCGCCACCACCAGCGTTAATAGCCAGCTATTGGAGGAGCTGCAAAAGGAGCTGG
AGGAGTACCGCGAACTGGCCAACAACCGACTGCAGGAGCTGGATAAGCTTCACGCCACGCATCGCGAAACCCTGAAGGAGGTGGAGAAGCTTAAA
ATGGATATACGACAGTTGCCGGAATCGGTAATTGTGGAAACCACGGAGTACAAGTGCCTGCAGAGCCAGTTTTCCGTGCTCTACAACGAGTCCAT
GCAGATAAAGACCATGCTGGACGAGACCCGAAACCAGCTTCAAACGAGCAAGAACCAGCATCTGCGACAAATCGAAGTGATGGAGAGCGAGGAAC
TTATTGCCCAGAAGAAGGTGCGCAGCGAGATGATCCAGATGGAGGACGTTTTAGCCCTCATCCGAAAGGAGTACGAAACGCTACGCATTGAGTTC
GAGCAGAACATGGCAGCCAACGAGCAGACGGCACCCATCAATCGCGAGATGCGCCACCTGATCACCTCTCTACAAAACCACAATGGCCAACTGAA
GGGTGAGGTGCAGCGCTACAAGCGAAAGTACAAGGACACGTCCACGGACAACTTGAAGCTGCGTCAGGAGCTGGCCGATGCACTAGCTACACTCG
AAGGCAACAAGTTGCAGGCGGCGACTGGTGTGAAGGAGGAGAACTCCAACAACGTTTCCGCCAGTGGACAAACAAACCAAACAAATTCCGGCAAC
GATACCAACGTAGCCATCAAGGAGGAGAACCATATCTCGGCTGAAGATGAAGCTGATGACGAGGCCAGTGGTAAGGACGTAAAAGACGGCATCAA
GCAGGAGAAGCTCAGTTCTGGAGACGCGGCGGCAGCTGAGAAGAAGGATTCCCCTGGACCCGGAAACTCAACAAGTTCTGCGACCAATTCTGTTC CCGTCAAAAACGAAAAGGATTCCAAGGATGGTGTCAAGGGCAAGGATGTGAAGGCAGTGGAAAGTGAAACGGTGCGCGATCTGAAGGCGCAACTA
AAAAAAGCACTGAACGACCAGAAAGAAATGAAACTCCTGCTGGATATGTACAAAGGCGTATCGAAGGATCAGCGCGACAAGGTCCAGTTGATGGC
CACCGAAAAGAAACTGCGCTCCGAGATCGAGGAGCTCCGCCAGCAGCTGAAGAAGCTGCAGGAAAGCAAGCGCGAGGAACGCAAGAAGCTGGCCG
ACGAGGAGGCGTTACGTAAGATTAAGCAATTGGAGGAGCAGAAGTACGAGCTGCAAAAACAGATGGCCAACCACAAGCCAACGGATAATTCTTGG
GGCAGTGGAGCCCCCGGCACAGCGAACTACACGCGACCGTTTGTTGGTTCCCACGAAGAGGAGGCACTGCTGAACGAGATGGAGGTTACCGGCCA
GGCGTTCGAGGACATGCAGGAGCAGAACTCCCGGCTCATACAACAGCTGCGTGAGAAGGACGATGCGAACTTTAAGCTAATGTCGGAGCGCATCA
AGGCCAACCAGCTGCACAAACTTCTGAGAGAGGAAAAGACGGTGCTGGAGGATCAGATGGCAACGGCGACCACGCAAATCGAAGCCATGCACATT
GTGCTGCGAAAGCTGGAGGAGAAGGAACGCAGCCTGCAGGCCACCGTCGCGTCGATTGAGAAAGAGTTGATGCTGCGGCAGCAAGCAATGGAGAT
GCACAAACGCAAGGCGATTGAATCGGCGCAATCGGCAGCGGACCTCAAGCTGCATCTGGAAAAGTATCACGCGCAAATGAAGGAGGCGCAGCAAG
TGGTGGCGGAGAAGACCAGTTCGCTGGAGGCGGAGGCCTACAAGACCAAGCGGCTGCAGGAGGAGCTGGCGCAGTTTAAACGCAAGGCGGAGCGC
ATGAAGAAGATGGAAATGTCGGGCACCACCATCGACGAGGTGATGATTGAGGAGATCCGCGAATACAAAGAAACGCTCACGTGTCCCTCGTGCAA
GGTGAAGCGGAAGGATGCTGTCCTGTCAAAGTGTTTCCACGTCTTCTGCTACGACTGCCTGCGCACTAGATATGAAACGCGGCAGCGGAAGTGTC
CCAAATGCAACTGCGCCTTCGGCGCCAACGATTATCATAGGCTATATCTGCAGTAG
(SEQ ID NO: 1157)

Start ATG: 1

MSKRSADDATGSSCLVAAAAAGQPPIKKVHFEPHLIGPVSTLEEMDIKVLEFQNKKLAQRIEQRMRTEAELRHRIEQLEKRQTQDDAVLNVVNRY
WNQLNEDIRVLLQRFDAETADELENRNENEVTTSFLAQLSTWDKEELDEKLANRVQVSKRAVAKIVQVIDRLMQRNEKITHVLKGDSLASAGSGS
GAGAGGEEEQQQASGDAETTTSSAGVHALEETLKQTHIEIMSENHKLQNLNTSLHEKFHTMSLKMKEYQDAHTAKETENAELKNQIDELQYDLEK
IHCRNDKLENHLAEAIEKLKAYHQIYGDPNKSTNSAKTPTTTGSGGATTSVNSQLLEELQKELEEYRELANNRLQELDKLHATHRETLKEVEKLK
MDIRQLPESVIVETTEYKCLQSQFSVLYNESMQIKTMLDETRNQLQTSKNQHLRQIEVMESEELIAQKKVRSEMIQMEDVLALIRKEYETLRIEF
EQNMAANEQTAPINREMRHLITSLQNHNGQLKGEVQRYKRKYKDTSTDNLKLRQELADALATLEGNKLQAATGVKEENSNNVSASGQTNQTNSGN
DTNVAIKEENHISAEDEADDEASGKDVKDGIKQEKLSSGDAAAAEKKDSPGPGNSTSSATNSVPVKNEKDSKDGVKGKDVKAVESETVRDLKAQL
KKALNDQKEMKLLLDMYKGVSKDQRDKVQLMATEKKLRSEIEELRQQLKKLQESKREERKKLADEEALRKIKQLEEQKYELQKQMANHKPTDNSW
GSGAPGTANYTRPFVGSHEEEALLNEMEVTGQAFEDMQEQNSRLIQQLREKDDANFKLMSERIKANQLHKLLREEKTVLEDQMATATTQIEAMHI
VLRKLEEKERSLQATVASIEKELMLRQQAMEMHKRKAIESAQSAADLKLHLEKYHAQMKEAQQVVAEKTSSLEAEAYKTKRLQEELAQFKRKAER
MKKMEMSGTTIDEVMIEEIREYKETLTCPSCKVKRKDAVLSKCFHVFCYDCLRTRYETRQRKCPKCNCAFGANDYHRLYLQ*
(SEQ ID NO: 1158)

Classification: hypothetical

Celera Sequence No. : 142000013384486
AAGAAGGATTAGGGATTATTTTGGAACATTTCCAAATACTGCACTATATTACCAATCCCTGCCCGTAATCCTCGCCCCCCTCCTCGCCACCGGA
TGTACCGATGTGCTCCTGGATCTTGGCCTCGAGCCCATTGACGTCCGCACCCTGGACGCGATCGATCTTGGTCCTGTTCCTGTAGAAGATGAATG
TTGGCATGGCCGAAACGCCCTGTCCAGCAGCCGTGTCCTGGCACTTGTCCACATCCACTTTCAGGAAGATGGCCTTTGGGTACTTTGTTGGAAAC
GTCTCGAAGATGGGCGCAATCCGCTTGCAGGGACCACACCACGAAGCTGTGAAGTCCACCACAACCAATTGAATGCCCGCTTGGGCCAACTCCGC
CTGGAAGTGGGACTCGTCGTTGATCACGCGCACGGACATGGTGATAGGATTAGGTTTCTATTAATTGAGCTTTTGTTTCGGCAGCCGAATTGGAT
TTAAGCAAGTAAATGTTATTATTAACGTTCAATGCAAATTTTTTTGTTAAAGATGACTTGTAATATGCATTTAGTCCAAATTCGTGCTAAGAAA
AATACCGAATGCGGTATTCCACAAGCGGTCACACTGTGATGGTATCGATATTTCGAGCTCTTTGACTTCCTATTTTTAGAGGGACCATTTATGTG
TAATAGAAAAAAACCGAAACTTAATATTTAAACTTTTATTGAAATATTAGTGGATTACAATATGTAAAACTATGAAATATTCTCATTTGATATAG
CTCAAAGTGTTATTTAAAATTCATTCAGTGTTTACGACTAGCAATCTACGCTTTCACGCTCATCTTAAGCTTACCGCCCATTTGCCAGGGTTGTC
AAGGCGAATGAGCGGTCCCACCATACACGCCACTGGAACTTTCGATACCTGCGCTGCGCCTGGCCACACGTTCATTACCTCGTGGTGTTTCAGTC
GGTCGCATTTTCATTAAGTCGCCATTTTAAAATTATTAGAGTCAAGTACAATGGCAGATGTGGAAAAGGAGCCCGAGAAGACCATCGCCGAGGAT
TTGGTGGTGACCAAGTATAAGTTGGCCGGCGAAATCGTCAACAGTGAGTATTCCTTGGCCGGAAACAGCGAACGCTGGCCGATTCCTGGAGTCGC
TGCTACGTGGCGCTTACACAATGCACCGAATGCCGCTTTCCCTTGTGCGCCACGCGTTGGTTAATCTGCCTATTTCTGGACTCTGTCTGCTCGTT
TAATTTTAGAAACCCTCAAGGCGGTAATTGGACTCTGCGTGGTTGATGCCTCCGTCCGGGAGATCTGCACCCAGGGCGACAATCAGCTCACCGAG
GAGACCGGCAAAGTAAGTGGTGGCCACCTGGCGGTCATTCGCGCCAATTTCATGTCCAATGATTAAGACTTACACCTTTGAGGGTTTCCCGATGG
CGAGCCATGTGCTGTGCGGGCTGGGGATCACCTCGTGGTCGCCAGGCGCACGCGGGGACTCCAATGCTCCACGTGCCCGGCTTGTGTGCTCTCCA
AAAGGTCCCGAGGATTTACAGATTATGAGATCTGAGGACACACCGCGCACTATCATTGATATATAGTACAACGAACAAGCAATCTAATGCTTTTA
TCGATCTTTCACAAACAGGTATACAAAAAGGAGAAAGACCTGAAGAAGGGCATTGCCTTTCCCACCTGTCTGTCCGTCAACAACTGTGTCTGCCA
CTTCTCGCCAGCCAAAAACGATGCTGACTACACGTTAAAGGCCGGTGATGTGGTCAAAATGTAAGTTGAACCTCCTATTCCACATATACCGCCAC
TAAATACGTAACATTTCTTTTCTACAGCGATCTGGGTGCCCACATTGATGGTTTCATTGCCGTGGCCGCTCACACAATTGTGGTAGGCGCTGCTG
CGGATCAGAAGATCAGTGGTCGCCAGGCCGATGTCATCCTCGCCGCCTACTGGGCTGTCCAGGCTGCCTTACGTCTGCTCAAGTCCGGCGCCAAT
GTGAGTCCTCCCTTACTTCTAGGTAATCCTCCGTTAATCCCTGCAAGAAACGGATTGTCTGCCGCGATTCTCCAGCGACTGAACATCTCAACACT
TGCAAAGATCAGCTGTGGCAGCTGGTAATTGCCCTGGCCTATTATTCAGGACTGGAGGCTTCTTGTCAGTTGTCCACAAGGTTATTTCTTCTGCA
GGCAACGGATTGACTGCGCTCAAACTCTGACACAGATCAGCTCAACACCTGCGGATAGAAACTGTGTCAATTTCGTGAACTGAACAAGTTCATTC
CATAGAAGTGTTCGGTCTTTAAATTTGTCCACATCTCCAGTTTATAGATATGTCGGAATTGTAATCTGCAGGCAACGGATTGTCTGCTGCCTTAA
CTCGTGGCTCAGCACAGCTCAACGTCTGCAGAGATCAACAGTGTCGATTTCGTGAACTGAACAAGTTTAGATACTTGAAATGTTCGGTCTTTAAA
GTTGTCCACAATCGCAATGATAATGCCGATCAGTTATTGTTATTTTGCGTTATCTATAGTATACTATGATATTTGATTAAGATTAGTCAAAGGGA
ATTGGAATGTTTTCTTTATCTCTGCTTTGAACTATTTCCATTTTATTTCATACTTAATATTTATGTTTCAATTCTGTATCCTTACAGAACTACTC
CCTCACCGATGCAGTGCAACAAATCAGCGAGTCGTATAAGTGCAAGCCCATTGAGGGCATGCTCAGTCACGAGCTGAAGCAGTTCAAAATTGACG
GCGAGAAGACGATCATACAGAACCCCAGCGAGGCGCAGCGCAAGGAGCATGAGAAGTGCACCTTCGAAACGTACGAGGTGTATGCCATCGATGTT
ATCGTCAGTACCGGCGAAGGAGTGGTTAGTAATCCATCAATAGACACTACATCTCCACTAATTTGTTCGATGATTAAAAACACGCGCTTGAGGCT
GACTTTGCTGGAATGCGGTGTTTGTTGCGAGAGTGACTTGTTTGCTCGGCGTTTTTTATACTAAAATGCGGCACGTGCAGACACCAAGTTCCGG
CTGGCTGTTGTCCGAAGATTGCAAGATTATGAGATCTGAGAACGCCAAATTTAAGCTGGATCCTGGATCATCGCAGCCAGAGCATTATTGCTAAC
ATTATTCGTATTCGTTGCAGGGACGCGAAAAGGACACCAAGGTCTCAATTTACAAGAAGTCTGAGGAGAACTACATGCTCAAGATGAAGGCGTCC
CGTGCTCTGCTGGCAGAGGTGAAAACCAAGTACGGAAACATGCCATTCAACATCCGCAGCTTCGAGGAGGAGACCAAGGCCCGCATGGGAGTTGT
TGAGTGCGTCGGCCACAAGATGATTGAGCCCTTCCAAGTGCTGTACGAGAAGCCATGTAAGTGTGATGCATATTATTATTAATCCTATTCCCTAT
TATGCGAGTTGGCAGAACTTAATTCCGGACCTGGTACACCTTCGGGTGCTAAGTGCGGCCAGACATTTTGCCAGAACAAATTCCAGGCATTGTCG TCTTCAGCAGTTGCCTCAGTGTGGCCTCTGTCTGAACATGGCACTGTCACAATCGTATCCAATCTATTAACCTGTTTTCTTATACTTATTAAAGT
TAATTTAGAGACTAAACTAGTTTGAGCAACCTTTATAAAGTTCGAATTTTAGCCGGAAGTAATAGCAAAGTTAAACAATCCTTTTCCTTATCTTG
CATTACAGCCGAGATTGTGGCGCAGTTTAAGCACACGGTTCTGCTCATGCCTAACGGCGTCAACTTGGTCACCGGCATCCCATTCGAGGCGGAGA
ACTATGTGAGCGAGTACAGTGTTGCGCAGGAGGAGCTCAAGGTAAGCTGCAACAATTTCCTTGTATTCACGATGCGTACTCAATGAAATCTCAAC
TTTTTGCAGACTCTGCTCGCGCAGCCTTTGGGTCCTGTGAAGGGCAAGGGTAAGGGCAAGAAGGCAACAGCTGGGGCGGCGACAAAGGTGGAAAC
GGCGCCGGCCGTGGAGACCAAGGCATAGACCAGCCCGCTGATGATGATCCGCACCGCCAAGCCATCAACGGAAACACAATGTGAACAATTGCGCT
GCCCAACGCTGCGCTCCACAGATTTTTACTATCGAATTCGTTGCGTATTAGAGGACCCTTTTGACAACAGAACAGGACAGAAGAGAAGACGGCAA
CAATTTGAGGATACATTTCCCCAGAAATCCTCCATCCATCAACAAGGCGGGCGGTCGGTCGGTCCCGCGCCAACTTTACCTCTTTATTTCCTTTA
CTATAAGCTGCCTTCGTTTATCGGTCTGTTCAACATCATCGCAACGAAAAAGCAAAGCAAGAACTGTCATCAAATTGTAACAATTTTAACGCTAA
ATGATCTTAAAATATAATTCAAGTGAAACGTTATTAACGCTGCGTAGTAGGTATTAAATAAAATTAACATTTTCTATAAAACAGCCGATAAATGC
CAAACGATTTTTCATTTATTTACTTTCCGCTGGCGCCCAATTTTAATTCGATTTCGATACGCTTCTCATTCTAATAAATGCACTTGCGAGTTGTG
TTTATTTTATACGTTTAATTTAGTTTTGATGTTCACATTCACATTATACAATTTGTAATTTAGATTTCTTGCCTTTTGTTATTTTAAATTTTACA
GTCTCATCTTTGAACTCTTGTATTACGAAAGTTGCAAGAATAACTTCGTTATGTTAAACGTCACTTAGTGCTGTGCTCACTTGGCCACCCCAGTT
GTCCATCCCAGATCCAATCCCAACAAGACCAGACCAATTCGATGCCGTATACGGCGACTTTGCCCAACTCGCTGACCTCTTCCCTTGCGTCAAAC
AAAATAAAGAACAACAAAAAACGCAATTGCTGCGGATGAAGTATAGAAAACACGAGCAGCACTTGCAGACGACAAAGATATGTGGCCGGTGATCA
AAAGAGGATCTGGGATTTAATGGTCTGCCGTCGCTTACATACATGGTTTGGTGTACTTTTTTTTTTTTTGTTATGATC
(SEQ ID NO: 1159)

Exon: 1001..1088
Exon: 1245..1342
Exon: 1634..1770
Exon: 1833..1995
Exon: 2653..2874
Exon: 3156..3381
Exon: 3714..3841
Exon: 3905..4018
Start ATG: 1001

Transcript No. : CT29664
ATGGCAGATGTGGAAAAGGAGCCCGAGAAGACCATCGCCGAGGATTTGGTGGTGACCAAGTATAAGTTGGCCGGCGAAATCGTCAACAAAACCCT
CAAGGCGGTAATTGGACTCTGCGTGGTTGATGCCTCCGTCCGGGAGATCTGCACCCAGGGCGACAATCAGCTCACCGAGGAGACCGGCAAAGTAT
ACAAAAAGGAGAAAGACCTGAAGAAGGGCATTGCCTTTCCCACCTGTCTGTCCGTCAACAACTGTGTCTGCCACTTCTCGCCAGCCAAAAACGAT
GCTGACTACACGTTAAAGGCCGGTGATGTGGTCAAAATCGATCTGGGTGCCCACATTGATGGTTTCATTGCCGTGGCCGCTCACACAATTGTGGT
AGGCGCTGCTGCGGATCAGAAGATCAGTGGTCGCCAGGCCGATGTCATCCTCGCCGCCTACTGGGCTGTCCAGGCTGCCTTACGTCTGCTCAAGT
CCGGCGCCAATAACTACTCCCTCACCGATGCAGTGCAACAAATCAGCGAGTCGTATAAGTGCAAGCCCATTGAGGGCATGCTCAGTCACGAGCTG
AAGCAGTTCAAAATTGACGGCGAGAAGACGATCATACAGAACCCCAGCGAGGCGCAGCGCAAGGAGCATGAGAAGTGCACCTTCGAAACGTACGA
GGTGTATGCCATCGATGTTATCGTCAGTACCGGCGAAGGAGTGGGACGCGAAAAGGACACCAAGGTCTCAATTTACAAGAAGTCTGAGGAGAACT
ACATGCTCAAGATGAAGGCGTCCCGTGCTCTGCTGGCAGAGGTGAAAACCAAGTACGGAAACATGCCATTCAACATCCGCAGCTTCGAGGAGGAG
ACCAAGGCCCGCATGGGAGTTGTTGAGTGCGTCGGCCACAAGATGATTGAGCCCTTCCAAGTGCTGTACGAGAAGCCATCCGAGATTGTGGCGCA
GTTTAAGCACACGGTTCTGCTCATGCCTAACGGCGTCAACTTGGTCACCGGCATCCCATTCGAGGCGGAGAACTATGTGAGCGAGTACAGTGTTG
CGCAGGAGGAGCTCAAGACTCTGCTCGCGCAGCCTTTGGGTCCTGTGAAGGGCAAGGGTAAGGGCAAGAAGGCAACAGCTGGGGCGGCGACAAAG
GTGGAAACGGCGCCGGCCGTGGAGACCAAGGCATAG
(SEQ ID NO: 1160)

Start ATG: 1

MADVEKEPEKTIAEDLVVTKYKLAGEIVNKTLKAVIGLCVVDASVREICTQGDNQLTEETGKVYKKEKDLKKGIAFPTCLSVNNCVCHFSPAKND
ADYTLKAGDVVKIDLGAHIDGFIAVAAHTIVVGAAADQKISGRQADVILAAYWAVQAALRLLKSGANNYSLTDAVQQISESYKCKPIEGMLSHEL
KQFKIDGEKTIIQNPSEAQRKEHEKCTFETYEVYAIDVIVSTGEGVGREKDTKVSIYKKSEENYMLKMKASRALLAEVKTKYGNMPFNIRSFEEE
TKARMGVVECVGHKMIEPFQVLYEKPSEIVAQFKHTVLLMPNGVNLVTGIPFEAENYVSEYSVAQEELKTLLAQPLGPVKGKGKGKKATAGAATK
VETAPAVETKA*
(SEQ ID NO: 1161)

Name: methionine aminopeptidase
Classification: peptidase

Celera Sequence No. : 142000013383791
TCGACTATCCGCGCACCAGCTCAAATCGCGTCTGAGATTCCTTGAACTGAATTCTCTTCTTGTGCTGCACGTGGGCTTCACTGAGGAACAAAGTA
GACGCCACCAGGGTTAACACAGTACCCACACACGCCAGGATAAAGGACCAGCCAAACCAATTGTTCGCATGCTCCGGCATCCAGCCATTCCGGTT
GCCAAATCCAGCGAATACAATCACTGCAATGGCTGCACTTACTCCAGCACCGAGAAGCACATATCCCAACGATTTAATGAGCGTAATGAAGTGCT
TTTGATCCGGACCAGCACACAGGATGAAGACCAGTACTCCGATGGCAGATACCAACATCCCGATGAAGGCCAAAGTGTAGAAGAACTGAGTGGCT
ATCATGAAGGCGGGCAGCAGGAATCCACGGATCTCATCGTAACCCGTGGTAAATGGGTCATACACCCAACGGCAGCCCACGAAGAATCTCCGCTG
GCTATCGTCGTTCACGTCCGGCAGCGACCGGAAGCAGTGCACCCACAATCCCAGGCGATCCAGCTTGGCGCCCGTGATGCGGTAATCACTGACCA
ACCAACTGGGCGTTGCAAACGCAATCACGATGAAGGCAAAGGCGAACACGAAGACGCCAACGCCACAACTTCCGGATAGTGTGCGTCTCTTCATG
TTCACTGTGTGACTGTTTTGCGTGTGGCTGGTGGGCAGGTGCTCCTGGGAATCCTCGCGTGCGAAGTGGGATGGTTTTTGCATCCTTTGAGTGGG
AAATTCTATTGGAATTTCGCTGGTTTCCTGGGGAAATGTTTGTTTGGTTTGCTGTTTGGGTGTGGACTGCAGTGTGGCCGCACTGGTAATACCGC
AGAATACCATGGGGCCACAAAATAAATACCAAATGCTACGGTACCAATAAATTTCAAAACAGTAAATTAAACAATTTAGATTATACATTTTTTAA
ATTAAGAAATAAATGATTTTAAATTTAATTAATTTTTGATAGATGGCTAAGGTACTTCTTAAATCAAATAAAAAGCTTTTTATATAGAATATAAC
ATATTTTGGTTATATTGTCGATAAAAACTTATACTTAAAAGGCCCAACCGTTGTAAATGCTAATGAGCGTCGTTTCATTCTGGAAGACATGCTCT
CCTCAATCGTTCCCCTAATTAAGGGCTGCCACAGCCTTGTGGGCGGCATCATCCAAGTCACTGGCTGTCTGAATGGGCAGGCCCGAATTCTTCAG GATCTCGCGAGCCTGATTTACATTGGTGCCCTCCAGTCGCACAACCAGTGGAACATTCAGTTGCAGCTTTTTGGATGCAGCCACAATGCCATTGG
CAATGGTGGCACAATTGACAATGCCGCCAAAGACATTGACCAGGATTCCCTTGACTTTCGGGTCAGCAGTGAGGATCTCGAAGGCTTTGGCCACC
TGATCCTCCCTGACGCCACCGCCGACGTCCAAAAAGTTGGCGGGCTCGCCTCCATTCAGCTTGATGATGTCCATGGTGGCCATGGCCAGGCCGGC
ACCATTAACCAAGCAGCCAATGTTGCCATCCATGGCGACGTAGTTCAGATTGTACTTGGCCGCCTCCACTTCTCGGGGATCGGATTCCTCCTCGG
TGACGTCCATGGAGAAAATATCCTTCTGACGGAACTGGGCATTGTCGTCAAAGTTGAGCTTAGCATCAACGGAGATAACTTCTCCCTTATCCGTC
TCCGCCAGCGGGTTGATCTCGATCTGTACGGCATCCACAGCTTTGAAGAGAGTATAGAGTTTTTGAATTTCCTCAGCACAACGCTTTACAGAGTC
TCCCTTGAACTCCAAGAACTTGGCCACCTCCAAGAGCGTCGACTCCGGTATGGGCTTGCCAATGTCTAGCGGAACAGTCTTAATTTTCTCAGGGG
TTTCCTCGGCCACCGCCTCGATATCCATGCCACCGGCAGGTGAGGCAATCAGCACGGGTCCATTGTGCTCGCGGTCCAGCAAGATGCAGAGATAG
GTCTCGCGGGTGATGTTGATACTGCGTGCCACCATGACCTTGTTGACCAAAATTCCCGATTTGGGCGTTTGTTTCGTTATCAGTCGGTTTCCAAT
CATCTGCTGGGTAAGCGAAAGCACCTCGCTCTTGCTGGCAAAATGTTAAATAATTATTAGTATAAGCTGGTCTTATCACTTGTGTTTTTAAGGTA
CACTCTGGCTTTCACAAACTTTTATCATTTTCAATATGGGCAGAATGATAAGATTAATCTTATATACAAATGATATTGTAGAACATAAATAATAT
TAATTTTTTAGATAAAATGTGAATGTGAATAGCCGGAATAGACCTAATCTATAATACTTGGTGGTGATATGGACGCCGCCTTTGAATCCGTTGTC
GAAAGTTCCCTTGCCACGCCCACCGGCGAGAATCTGCGCCTTCACCACGTATTCCGGGCACTCTGAAACACAGAAGCACAGCATTTAACACCAAT
TAGCCCAGGGATTACATAAACACCGGCATGGTTCCGTCCTCCACTTACCAAAAGTCTTGACGACCTCGGCATCTGCCTTGGAGTTATTCAAGACC
TTGAATTGCTGTATGGCCACTCCATACTTCTGGAGGAGATCCTTGCTCTGGAACTCCAGCAGATTCAGGTTGCGCACGGGAACCTATCATCGAAA
GATAAACAAAGCCAAGACAAAGGTCACTTCAACTTCTCTTTTCGAAGAGTTGATATATTATAGAGGAATGTGAGTGCGAGGAAACCTTATGAACG
ATGTGACGGGCTGTGGTAACTGCTTTCAGTAGGAACGACATCTTGGCTGATCTGCGGTGGTAACTGAATACCTTGGCTAACTTGGTATTAATTTA
TTTTCGTAACTTTGTCGGTAAATTTAGTTTAAAAACACAACCGAAAATCGCCGCCGTTCCACGATGCTTATCACTGCACAATGTGACCAAGAAGC
ACGACTACTTTCCATGGTGATAAAAATATACCAAATGCCACTGCCATCTTGAACTAGTTCTCGCGAAGCAATGGTCTTACTGTTGCAGTCAGCTG
AAAATCAGCTGTCGTTGTGTACTTTTTTTCTTCGGCTAATAGTCAGCGAAGAATGACGAATAACACAAATTGAATGAAAAACCTGAGTGAGACGG
AAGCCGAAGTCACCATGCAAGAAAATGTAGTCCACGAATCATTGCCCCAGATCCCGGTGGCCACTTCGGTGAGCTGTTGCTTCGTTCTGGCTGTT
CTGTACGTGGGTAGCCTCTACATCTGGAGCACCAAACACAACCGGGATCATCCAACCACGGTCAAGAGAAGATTCGCCAGTGTGTCCATGGTGAT
GCTGGCAGCCCCGTTCTTCGTTTACTTCTTCTCATCGCCGGAGCTGCTCAGCCGGGTACCATTTCCCAAGCTGCTCGGTTTGCGCTTGGAGGGAT
TGTGGCAGGCTGTTGTTATACCATACAGCCTGACGGTGCTGCTCTTCCTGGGACCCATCTTTGTCAACATGCAGAACGAGTCCGTGCGCTCCTAC
TTCGGTAATAGTTAAAGCCCCTCTGCCTATCAGCCCCTTCTCACTGCTTGATTTGAATTGCAGATCTGGACTACTGGAGGGGATCATTTGGCAGC
ATCATCTGGGTGCGCAACCATGTGATAGCACCGCTGAGCGAGGAGTTCGTGTTCCGAGCCTGCATGATGCCCCTGATCCTGCAGAGCTTTTCGCC
CCTGGTCGCCGTTTTCATAACGCCGCTTTTCTTCGGAGTAGCCCACTTGCATCACATAGCCGAACGCCTGAGCTTAGGCGTGGAGTTGAGCACTG
CCCTATTGATTGGACTGTTCCAGTTCATCTACACCACGCTATTTGGCTTCTATTCGGCCTTTCTATTTGCCCGTACAGGTCATGTGATGGCTCCC
ATCTTGGTGCACGCGT
(SEQ ID NO: 1162)

Exon: 2911..2746
Exon: 2648..2519
Exon: 2437..2338
Exon: 2124..1001
Start ATG: 2796 (Reverse strand: CAT)

Transcript No. : CT29754
TGGAACGGCGGCGATTTTCGGTTGTGTTTTTAAACTAAATTTACCGACAAAGTTACGAAAATAAATTAATACCAAGTTAGCCAAGGTATTCAGTT
ACCACCGCAGATCAGCCAAGATGTCGTTCCTACTGAAAGCAGTTACCACAGCCCGTCACATCGTTCATAAGGTTCCCGTGCGCAACCTGAATCTG
CTGGAGTTCCAGAGCAAGGATCTCCTCCAGAAGTATGGAGTGGCCATACAGCAATTCAAGGTCTTGAATAACTCCAAGGCAGATGCCGAGGTCGT
CAAGACTTTTGAGTGCCCGGAATACGTGGTGAAGGCGCAGATTCTCGCCGGTGGGCGTGGCAAGGGAACTTTCGACAACGGATTCAAAGGCGGCG
TCCATATCACCACCAACAAGAGCGAGGTGCTTTCGCTTACCCAGCAGATGATTGGAAACCGACTGATAACGAAACAAACGCCCAAATCGGGAATT
TTGGTCAACAAGGTCATGGTGGCACGCAGTATCAACATCACCCGCGAGACCTATCTCTGCATCTTGCTGGACCGCGAGCACAATGGACCCGTGCT
GATTGCCTCACCTGCCGGTGGCATGGATATCGAGGCGGTGGCCGAGGAAACCCCTGAGAAAATTAAGACTGTTCCGCTAGACATTGGCAAGCCCA
TACCGGAGTCGACGCTCTTGGAGGTGGCCAAGTTCTTGGAGTTCAAGGGAGACTCTGTAAAGCGTTGTGCTGAGGAAATTCAAAAACTCTATACT
CTCTTCAAAGCTGTGGATGCCGTACAGATCGAGATCAACCCGCTGGCGGAGACGGATAAGGGAGAAGTTATCTCCGTTGATGCTAAGCTCAACTT
TGACGACAATGCCCAGTTCCGTCAGAAGGATATTTTCTCCATGGACGTCACCGAGGAGGAATCCGATCCCCGAGAAGTGGAGGCGGCCAAGTACA
ATCTGAACTACGTCGCCATGGATGGCAACATTGGCTGCTTGGTTAATGGTGCCGGCCTGGCCATGGCCACCATGGACATCATCAAGCTGAATGGA
GGCGAGCCCGCCAACTTTTTGGACGTCGGCGGTGGCGTCAGGGAGGATCAGGTGGCCAAAGCCTTCGAGATCCTCACTGCTGACCCGAAAGTCAA
GGGAATCCTGGTCAATGTCTTTGGCGGCATTGTCAATTGTGCCACCATTGCCAATGGCATTGTGGCTGCATCCAAAAAGCTGCAACTGAATGTTC
CACTGGTTGTGCGACTGGAGGGCACCAATGTAAATCAGGCTCGCGAGATCCTGAAGAATTCGGGCCTGCCCATTCAGACAGCCAGTGACTTGGAT
GATGCCGCCCACAAGGCTGTGGCAGCCCTTAATTAGGGGAACGATTGAGGAGAGCATGTCTTCCAGAATGAAACGACGCTCATTAGCATTTACAA
CGGTTGGGCCTTTTAAGTATAAGTTTTTATCGACAATATAACCAAAATATGTTATATTCTATATAAAAAGCTTTTTATTTGATTTAAGAAGTACC
(SEQ ID NO: 1163)

Start ATG: 116 (Reverse strand: CAT)

MSFLLKAVTTARHIVHKVPVRNLNLLEFQSKDLLQKYGVAIQQFKVLNNSKADAEVVKTFECPEYVVKAQILAGGRGKGTFDNGFKGGVHITTNK
SEVLSLTQQMIGNRLITKQTPKSGILVNKVMVARSINITRETYLCILLDREHNGPVLIASPAGGMDIEAVAEETPEKIKTVPLDIGKPIPESTLL
EVAKFLEFKGDSVKRCAEEIQKLYTLFKAVDAVQIEINPLAETDKGEVISVDAKLNFDDNAQFRQKDIFSMDVTEEESDPREVEAAKYNLNYVAM
DGNIGCLVNGAGLAMATMDIIKLNGGEPANFLDVGGGVREDQVAKAFEILTADPKVKGILVNVFGGIVNCATIANGIVAASKKLQLNVPLVVRLE
GTNVNQAREILKNSGLPIQTASDLDDAAHKAVAALN*
(SEQ ID NO: 1164)

Name: PROBABLE SUCCINYL-COA LIGASE LIKE
Classification: enzyme
Gene Symbol: Sucb
FlyBase ID: FBgn0029118

FIGURE SHEET 624

Celera Sequence No. : 142000013383791
TTTCGCTTACCTTTCTCTGGGTCACTTAATTAAGGCACTAGCTTAGCTGAAGTTTATGCAATTCAATGATCTCTATGGTTAGTCGCAGGTCAGTC
GTTCAGGTATGTTTATAACAATAATTTGTTTCAGGCACTACGAACTACACCATAATAGTTCTATCTAATTAAGGCACGAGTGTAATATTTCGAT
GCTAGTTCCGACTAGCCTGCGACTTTTGCTAAAGAAAAAAATAAACGTACAATTGCGGAGGGGTATGCTCTTTGTGTCTGGGCGTTAATTGAGCG
AAAATTGATATGCAAATACTGTAGAATACTCTACATGAACATGAGTCATCTAGTTGAGCGTCTTCGTTTGATGTTAGCTGTGCTTGGTTCTGGTT
TTCATTCGGAAAAACATTCAGTCTTCTCTTGGAACTGATCTGGTCGATTGGATGGATGATTATAAGTACCAAAAACTGAAAGCTTGTGAATCGGT
GCGGCCGTCAATTGCATAAACTTTTTAAATTAAAAACTACGAGTACAGTCGAACTTCTCTGAACTAAAATTAATTTCTTTAGGTATGTTAGAGAG
AAGCGATGAATATATGGCGAAAATTATTTTTATCCAAAATAACTTTGGTTCGTTAAAATTTTTCGAAATCTCCGCCAGTTGGGGAGTTATTTAAA
CGATTTAAGGTAATATAAAACGAATGTTACCGACATGAATACTTTAACCTATGCACAGGGAAACCATTGAATAAAATATAAAACGAACATAAACC
AACTTTAAAAACGTGCACTACCAGAAACTGTTAGTTAGAATATTTCGCCTTAGAGAAGTTCGACTGTAATGTTTAGGGTGAGAATTCTTTGAGGG
GACGGAATGTTTTTGTTTTGTTTTCCTCTTGGTTGGCTTGTGTTTTCCTTGGTGCAAGTGTGCCAGCTGCCACGGCTAAAATAGACAATGCAAGA
AGGTTAAGCGACCGACCCTGACTTGGATATAGTCAAGTACTTACCATCGACTATCCGCGCACCAGCTCAAATCGCGTCTGAGATTCCTTGAACTG
AATTCTCTTCTTGTGCTGCACGTGGGCTTCACTGAGGAACAAAGTAGACGCCACCAGGGTTAACACAGTACCCACACACGCCAGGATAAAGGACC
AGCCAAACCAATTGTTCGCATGCTCCGGCATCCAGCCATTCCGGTTGCCAAATCCAGCGAATACAATCACTGCAATGGCTGCACTTACTCCAGCA
CCGAGAAGCACATATCCCAACGATTTAATGAGCGTAATGAAGTGCTTTTGATCCGGACCAGCACACAGGATGAAGACCAGTACTCCGATGGCAGA
TACCAACATCCCGATGAAGGCCAAAGTGTAGAAGAACTGAGTGGCTATCATGAAGGCGGGCAGCAGGAATCCACGGATCTCATCGTAACCCGTGG
TAAATGGGTCATACACCCAACGGCAGCCCACGAAGAATCTCCGCTGGCTATCGTCGTTCACGTCCGGCAGCGACCGGAAGCAGTGCACCCACAAT
CCCAGGCGATCCAGCTTGGCGCCCGTGATGCGGTAATCACTGACCAACCAACTGGGCGTTGCAAACGCAATCACGATGAAGGCAAAGGCGAACAC
GAAGACGCCAACGCCACAACTTCCGGATAGTGTGCGTCTCTTCATGTTCACTGTGTGACTGTTTTGCGTGTGGCTGGTGGGCAGGTGCTCCTGGG
AATCCTCGCGTGCGAAGTGGGATGGTTTTTGCATCCTTTGAGTGGGAAATTCTATTGGAATTTCGCTGGTTTCCTGGGGAAATGTTTGTTTGGTT
TGCTGTTTGGGTGTGGACTGCAGTGTGGCCGCACTGGTAATACCGCAGAATACCATGGGGCCACAAAATAAATACCAAATGCTACGGTACCAATA
AATTTCAAAACAGTAAATTAAACAATTTAGATTATACATTTTTAAATTAAGAAATAAATGATTTTAAATTTAATTAATTTTTGATAGATGGCTA
AGGTACTTCTTAAATCAAATAAAAAGCTTTTTATATAGAATATAACATATTTTGGTTATATTGTCGATAAAAACTTATACTTAAAAGGCCCAACC
GTTGTAAATGCTAATGAGCGTCGTTTCATTCTGGAAGACATGCTCTCCTCAATCGTTCCCCTAATTAAGGGCTGCCACAGCCTTGTGGGCGGCAT
CATCCAAGTCACTGGCTGTCTGAATGGGCAGGCCCGAATTCTTCAGGATCTCGCGAGCCTGATTTACATTGGTGCCCTCCAGTCGCACAACCAGT
GGAACATTCAGTTGCAGCTTTTTGGATGCAGCCACAATGCCATTGGCAATGGTGGCACAATTGACAATGCCGCCAAAGACATTGACCAGGATTCC
CTTGACTTTCGGGTCAGCAGTGAGGATCTCGAAGGCTTTGGCCACCTGATCCTCCCTGACGCCACCGCCGACGTCCAAAAAGTTGGCGGGCTCGC
CTCCATTCAGCTTGATGATGTCCATGGTGGCCATGGCCAGGCCGGCACCATTAACCAAGCAGCCAATGTTGCCATCCATGGCGACGTAGTTCAGA
TTGTACTTGGCCGCCTCCACTTCTCGGGGATCGGATTCCTCCTCGGTGACGTCCATGGAGAAAATATCCTTCTGACGGAACTGGGCATTGTCGTC
AAAGTTGAGCTTAGCATCAACGGAGATAACTTCTCCCTTATCCGTCTCCGCCAGCGGGTTGATCTCGATCTGTACGGCATCCACAGCTTTGAAGA
GAGTATAGAGTTTTTGAATTTCCTCAGCACAACGCTTTACAGAGTCTCCCTTGAACTCCAAGAACTTGGCCACCTCCAAGAGCGTCGACTCCGGT
ATGGGCTTGCC
(SEQ ID NO: 1165)

Exon: 1861..1001
Start ATG: 1861 (Reverse strand: CAT)

Transcript No. : CT29760
ATGGTATTCTGCGGTATTACCAGTGCGGCCACACTGCAGTCCACACCCAAACAGCAAACCAAACAAACATTTCCCCAGGAAACCAGCGAAATTCC
AATAGAATTTCCCACTCAAAGGATGCAAAAACCATCCCACTTCGCACGCGAGGATTCCCAGGAGCACCTGCCCACCAGCCACACGCAAAACAGTC
ACACAGTGAACATGAAGAGACGCACACTATCCGGAAGTTGTGGCGTTGGCGTCTTCGTGTTCGCCTTTGCCTTCATCGTGATTGCGTTTGCAACG
CCCAGTTGGTTGGTCAGTGATTACCGCATCACGGGCGCCAAGCTGGATCGCCTGGGATTGTGGGTGCACTGCTTCCGGTCGCTGCCGGACGTGAA
CGACGATAGCCAGCGGAGATTCTTCGTGGGCTGCCGTTGGGTGTATGACCCATTTACCACGGGTTACGATGAGATCCGTGGATTCCTGCTGCCCG
CCTTCATGATAGCCACTCAGTTCTTCTACACTTTGGCCTTCATCGGGATGTTGGTATCTGCCATCGGAGTACTGGTCTTCATCCTGTGTGCTGGT
CCGGATCAAAAGCACTTCATTACGCTCATTAAATCGTTGGGATATGTGCTTCTCGGTGCTGGAGTAAGTGCAGCCATTGCAGTGATTGTATTCGC
TGGATTTGGCAACCGGAATGGCTGGATGCCGGAGCATGCGAACAATTGGTTTGGCTGGTCCTTTATCCTGGCGTGTGTGGGTACTGTGTTAACCC
TGGTGGCGTCTACTTTGTTCCTCAGTGAAGCCCACGTGCAGCACAAGAAGAGAATTCAGTTCAAGGAATCTCAGACGCGATTTGAGCTGGTGCGC
GGATAG
(SEQ ID NO: 1166)

Start ATG: 1 (Reverse strand: CAT)

MVFCGITSAATLQSTPKQQTKQTFPQETSEIPIEFPTQRMQKPSHFAREDSQEHLPTSHTQNSHTVNMKRRTLSGSCGVGVFVFAFAFIVIAFAT
PSWLVSDYRITGAKLDRLGLWVHCFRSLPDVNDDSQRRFFVGCRWVYDPFTTGYDEIRGFLLPAFMIATQFFYTLAFIGMLVSAIGVLVFILCAG
PDQKHFITLIKSLGYVLLGAGVSAAIAVIVFAGFGNRNGWMPEHANNWFGWSFILACVGTVLTLVASTLFLSEAHVQHKKRIQFKESQTRFELVR
G*
(SEQ ID NO: 1167)

Celera Sequence No. : 142000013383795
CCTGAACTGCAGCTGAGCTCCAAGGAACTGTGCTGCGGAACGCATGCAACCAACACCAGTGAGCTTTCGTGCTTCTGCATCGTGAATCTCAAGCA
AACCAATCGTGCGAGATTCGCATTTACCGCCGTTGCTGGCCAGGCGGCGGAAAATGTGAGTGGACTTATATATCGCCTTAGACTAGTCATTTAAT
CTTCTTACTCTGTTCCAAATAGGTGCTGAAAACGGCTGCCCTGCTGCGACACCGCGTTGATCTCCTCGAGAAGCAGTTCCAAACTGACAAACTCA
CAAACGCTACGGAGGCGGAACTGCAGACGATTCGGCACAACATGTTGCACACGGACATTAAACTGCCATACGCTTTTAAGATGGACACGCTGGAA
CGCATCACCGAGATGCTGAAGAGAATAAAAGATTCATCGCGCACAACCTTAAAGTAAGTTTAACTTATTAAAGTAATGTGCTCCATTTCTAAACT
CTACATTTTCAGAGAATTTGTGGACGTAGAGATGCGCACGCTGCTGCAGGAGAAGCCGTTGGACACACACCCCTTCATTCTGCACTACATCACCA
GTTCCGCGCTCGTGGAGGAGATTCCTTTGCAACGAGCCACCAAGCTGTGCCCGGATCGGCCCATCCTCGTAATCAGCGTGTGTGATAGCGTGGTC
AAGGCTCGCTGTTGTGTACCAGAAAAGTGTATCACGGAGAAATTCAACGCTTCCGCCTGGCTGCAATCCTTTGCCGACACCTTTAATGGACAAAT
AGCCGCGCCCAAGGGCCAAAATCCGCAGGCCGTGTGCAACATGAAGGGTCGACGGGTGAGCAATCTGTTCGAGGAACAGTTGGAGCAGGCAATGT
CCAAGGCACATGCATACGCTAAGCTTTATCTATAGGTATAAGTTGTGATTACCCTCCAAAATGTGCTAGCTGTAAGCTTGCCCTTTGAATAATTG CTCATGTGAGGAGCGAGTAAATGGCGAAGTTTTAAGGAATTTCAGAATCTTTAATCACTAATCACTACCAGGTCATCCTCCTCCTCATCTTCTGC
GTTATCCTCTTGATCCTGGGGCACCAAGCTGGAGTTCATCAACTCTTCAAAGACATCCGCATTATCGGAACTTTGATTGAAGAAGTAACTTATGT
TATCCAAGGGCTTCACTGGCGTTGGAATCTTTTCGCTGATGCGATGCTGCATCTTGAATCGCTCCACTGGCGTCCTGGCCAGCTTCTGCAGATCT
CCCTTGACCAGCAGATCAAAACTGTCCTCCAAGGAGAATCGCTTACTCTGCGGTAGTTGATCCACTTGAGAGAGATCTCTTTTCGTTTCCACTTT
GGGCGATTCATTCACATTTCCTAGACTCATCTGCGCCAGACGTAAGCTCAAATCTTCCGCCATGGGTTCGTAATGAAGCTGGTGACCATCGTGGT
TGGTCAGTGCTGGCTTGGCATTCGGATTCGAGATAATGCCTTTAACTATGTCCGACATATCGAACTCTTCGGCATCGCAATCGCTTTCCAGATCG
GAGGGCAGGAACTTGGTGATGGGGGTGGAGCATTGCTGACGTTGCGGAGCGGGAGCCTTGACCGGAGTACCTTCCTTCTTGCGCCCTAGGAATTG
GTGCAGTAATGGCTGGTTCTCTTCAGGCTGAGCCTTTATCTTTCTGACCACTCGCTTTGGTTTCGAATTCGGCTCGTTTTCCTTATTCTCCTCTT
CAGATGCGGTTTTCTTCTTTCGCGTGGTTTTCTTGGCGGGCTTCTCCTTCGACTTCAAAAAGGCCGCTACTAAATCGGGATACGCTGTCTCCAGC
ATGTCCAATGGCTCAATGGTGTAGTAAAGTTCCTCGATTCCCTTGGGATGCTCCGCTTCGTACTCCGCAATCTGCTTGTCCGGAATAAGACCCTT
GAAGATGCCACTGGGATCGTGCCAGCGCAATTCTAAGCTGGGCACACCCTTCACAGTTCGCTTTTTGATAATCTCGTGTGGCTGGATAAGTATCT
TCTCCTGCTTCGATTGCTGCACCTGCCAGCGTGTGAGTATGGGAAAGAACTTTTGGAAGCAGTATATTTCTGGCCACTGCAAGAGATGTCCGATT
TGTTTGATGAATTTGACAAGATTTGGTTGCCGCCAGTTGAGATTTAGATTGGGAATGGTGTCGGGTTCGCTGAGAAACTCGGCAATGATCTCTTC
GTTGGGAAAGTCAGGAGATAATAGGGCTTTCCGCCTCAAAGTCAACTCGGACTTAATGGATAGTCGTTGTTCTCTAAGGGAAGAGTTTAATAAAC
AAATGTTTATATTAGTTTTAGGAAATAGCTCACTTCCAGAGACTCTCATCGCAGCCTTTGTGTGTGCGACACACACTGCAGCCACTTTTTGTGTG
GCTCTGGGTCTTGCCAATGTGGCCACAATTGCTGCAGATGGATTTGTCGTCCACTCGGATCTCCAAGGCATTGTATTTATCGGTTTCACCACGCC
AGCTTCTCATTCTGCAGAAATAATAATCAAAGCTTATTAGCTTTAAAAATATAATATATGTAACAATGTAGTAGACTACCTATCCAAAATCTCAG
TCTCCTTGTACTTGTTGAACAGCTTTAGGACGCCATCCTTGCCAATGCCACCTATGCCATCAGGACAATAATCACAGCCGCAGAGCAAAGCCATC
ACAATGATCTTCTGTTGGCCAAAGTCCATTCGGGATGTGATCTCCCGCATGTCGTAGATGTCCACAGCTCCGCCGGCGGCTGCCTGGGCTCCTTG
GGTGGAAACGGAGAAGTTGCGATAGACACGAACGGCTCCATAGGCAAAGCAATCCGAGTCCTGGCTAATGACGCCGTCCACTAGCTGCGGACAGG
AATATAATCGGATTTGGTACAGAGTTCTTGTGAGGATGTAGTTGATATACGTACGCCATGCTTGTTGAGAAAGGCACAGTAGGCCTCCGCCTCGC
CGGGACCTTGGACGCACTGGATTCCCATGGAGAGCAGCAGCGTTTCGCACTGCTTGAGAACATGGTTGAACCGGCTGCGTCCCTTGTCGCCCTTG
GACGGCTGACTTTGGGTGCACTCAGGCGAATTCTTGGGCTTCACTCCCCGAAACTGGAGCTCATTCCTTTTGGCTATCACCTGGCTCTTGAGTTT
TGGAGCAACTCCCTCCAAAACGAAAACCGGAGTAACTTGCTCCCAAATCAAGTAGCAAGTGCGAAAGAAGAGGTTCCTGTTGGTAAAGCGTAAAT
ATTAATATTTTAAAAGAATATAAGGTATTAAGAATTTTTTAAACCTACTTTAAATGATGCCTTGGATGCACAAAGTAGTCCACAACATTAAGAGA
TTCGCACACCCAGCCGGCCAGGTCGATGGCCACTTTCTTTCCCCGCAGTTCATTAATGGGTTTACGTTCACAATGGGGCGTTAAAACACCCCATA
ATTCCTTGACGCCCATTTAAATAAGCTAAACAAAAACCCCGCGAGAAATTCGCAACAAATTTAAACAATCGCTTCTTCGTCAGAGTTGCCCAATC
AGTTACTTTCTAGCTACTTGAAGCTATATTCAAAAGCAGCCAAGTGCAAAGTTGTGACAATAATTGGCAATGATAACTTTTTTAACAATAATACA
TGATGCTATTTTCAATAACAAATATTATACATATAAATGTCATCTTATTCGATTTTAAGAACACATTTCGTTTTTAGCTTTTTTTGAGCTTGTCT
CTAGCTACATTTGACAGCACTGCGACTTCCGCCAGTCACTGCGAAGCATGCTCGATAACCGATAGCGGGCTTTGTTTTGACAGCTGCACAAGCGA
CCGCTGCGAATGGCCAGTGGTCAGCAGTCTCTTCTTCTTCCACGTCGACGTGTCGTGTCAGCCAAAAGAAAGTCGAAATAAAATATTGAATTGAA
GCTGCCCCTTTGCGAGTAGGCCCGACAAAATTCAGAAGCTGCCAGTCGTCCGTACGCCAAACCACACACAACCACCACCGGCAAGATGGTTCTCG
CGGATTTGGGTCGCAAGATAACAACGGCGCTGCACTCGCTCAGCAAGGCGACCGTAATCAATGAGGAGGCACTGAATTCCATGCTGAAGGAGATC
TGCGCAGCGCTCCTGGAGGCTGATGTGAATATCCGACTGGTTAAGCAGCTGCGCGAGAATGTGCGTGCCGTTATTGATTTCGATGAGATGGCCGG
TGGCCTGAACAAGAGGCGAATGATCCAATCGGCTGTGTTCAAGGAGCTCGTCAAACTGGTCGATCCCGGCGTGAAACCCTACCAACCCATCAAGG
GCAAGGCCAATGTGGTCATGTTTGTGGGTCTGCAGGGCTCCGGTAAGACCACCACCTGTACCAAGCTGGCCTATCACTACCAGAAGCGCAACTGG
AAGTCGTGTCTCGTGTGCGCGGATACCTTCCGTGCTGGTGCCTACGATCAGGTCAAGCAGAACGCC
(SEQ ID NO: 1168)

Exon: 3436..3279
Exon: 3211..2905
Exon: 2839..2550
Exon: 2481..2314
Exon: 2258..1001
Start ATG: 3436 (Reverse strand: CAT)

Transcript No. : CT29886
ATGGGCGTCAAGGAATTATGGGGTGTTTTAACGCCCCATTGTGAACGTAAACCCATTAATGAACTGCGGGGAAAGAAAGTGGCCATCGACCTGGC
CGGCTGGGTGTGCGAATCTCTTAATGTTGTGGACTACTTTGTGCATCCAAGGCATCATTTAAAGAACCTCTTCTTTCGCACTTGCTACTTGATTT
GGGAGCAAGTTACTCCGGTTTTCGTTTTGGAGGGAGTTGCTCCAAAACTCAAGAGCCAGGTGATAGCCAAAAGGAATGAGCTCCAGTTTCGGGGA
GTGAAGCCCAAGAATTCGCCTGAGTGCACCCAAAGTCAGCCGTCCAAGGGCGACAAGGGACGCAGCCGGTTCAACCATGTTCTCAAGCAGTGCGA
AACGCTGCTGCTCTCCATGGGAATCCAGTGCGTCCAAGGTCCCGGCGAGGCGGAGGCCTACTGTGCCTTTCTCAACAAGCATGGCCTAGTGGACG
GCGTCATTAGCCAGGACTCGGATTGCTTTGCCTATGGAGCCGTTCGTGTCTATCGCAACTTCTCCGTTTCCACCCAAGGAGCCCAGGCAGCCGCC
GGCGGAGCTGTGGACATCTACGACATGCGGGAGATCACATCCCGAATGGACTTTGGCCAACAGAAGATCATTGTGATGGCTTTGCTCTGCGGCTG
TGATTATTGTCCTGATGGCATAGGTGGCATTGGCAAGGATGGCGTCCTAAAGCTGTTCAACAAGTACAAGGAGACTGAGATTTTGGATAGAATGA
GAAGCTGGCGTGGTGAAACCGATAAATACAATGCCTTGGAGATCCGAGTGGACGACAAATCCATCTGCAGCAATTGTGGCCACATTGGCAAGACC
CAGAGCCACACAAAAAGTGGCTGCAGTGTGTGTCGCACACACAAAGGCTGCGATGAGAGTCTCTGGAAAGAACAACGACTATCCATTAAGTCCGA
GTTGACTTTGAGGCGGAAAGCCCTATTATCTCCTGACTTTCCCAACGAAGAGATCATTGCCGAGTTTCTCAGCGAACCCGACACCATTCCCAATC
TAAATCTCAACTGGCGGCAACCAAATCTTGTCAAATTCATCAAACAAATCGGACATCTCTTGCAGTGGCCAGAAATATACTGCTTCCAAAAGTTC
TTTCCCATACTCACACGCTGGCAGGTGCAGCAATCGAAGCAGGAGAAGATACTTATCCAGCCACACGAGATTATCAAAAAGCGAACTGTGAAGGG
TGTGCCCAGCTTAGAATTGCGCTGGCACGATCCCAGTGGCATCTTCAAGGGTCTTATTCCGGACAAGCAGATTGCGGAGTACGAAGCGGAGCATC
CCAAGGGAATCGAGGAACTTTACTACACCATTGAGCCATTGGACATGCTGGAGACAGCGTATCCCGATTTAGTAGCGGCCTTTTTGAAGTCGAAG
GAGAAGCCCGCCAAGAAAACCACGCGAAAGAAGAAAACCGCATCTGAAGAGGAGAATAAGGAAAACGAGCCGAATTCGAAACCAAAGCGAGTGGT
CAGAAAGATAAAGGCTCAGCCTGAAGAGAACCAGCCATTACTGCACCAATTCCTAGGGCGCAAGAAGGAAGGTACTCCGGTCAAGGCTCCCGCTC
CGCAACGTCAGCAATGCTCCACCCCCATCACCAAGTTCCTGCCCTCCGATCTGGAAAGCGATTGCGATGCCGAAGAGTTCGATATGTCGGACATA
GTTAAAGGCATTATCTCGAATCCGAATGCCAAGCCAGCACTGACCAACCACGATGGTCACCAGCTTCATTACGAACCCATGGCGGAAGATTTGAG
CTTACGTCTGGCGCAGATGAGTCTAGGAAATGTGAATGAATCGCCCAAAGTGGAAACGAAAAGAGATCTCTCTCAAGTGGATCAACTACCGCAGA
GTAAGCGATTCTCCTTGGAGGACAGTTTTGATCTGCTGGTCAAGGGAGATCTGCAGAAGCTGGCCAGGACGCCAGTGGAGCGATTCAAGATGCAG
CATCGCATCAGCGAAAAGATTCCAACGCCAGTGAAGCCCTTGGATAACATAAGTTACTTCTTCAATCAAAGTTCCGATAATGCGGATGTCTTTGA
AGAGTTGATGAACTCCAGCTTGGTGCCCCAGGATCAAGAGGATAACGCAGAAGATGAGGAGGAGGATGACCTGGTAGTGATTAGTGATTAA
(SEQ ID NO: 1169)

Start ATG: 1 (Reverse strand: CAT)

MGVKELWGVLTPHCERKPINELRGKKVAIDLAGWVCESLNVVDYFVHPRHHLKNLFFRTCYLIWEQVTPVFVLEGVAPKLKSQVIAKRNELQFRG
VKPKNSPECTQSQPSKGDKGRSRFNHVLKQCETLLLSMGIQCVQGPGEAEAYCAFLNKHGLVDGVISQDSDCFAYGAVRVYRNFSVSTQGAQAAA
GGAVDIYDMREITSRMDFGQQKIIVMALLCGCDYCPDGIGGIGKDGVLKLFNKYKETEILDRMRSWRGETDKYNALEIRVDDKSICSNCGHIGKT
QSHTKSGCSVCRTHKGCDESLWKEQRLSIKSELTLRRKALLSPDFPNEEIIAEFLSEPDTIPNLNLNWRQPNLVKFIKQIGHLLQWPEIYCFQKF
FPILTRWQVQQSKQEKILIQPHEIIKKRTVKGVPSLELRWHDPSGIFKGLIPDKQIAEYEAEHPKGIEELYYTIEPLDMLETAYPDLVAAFLKSK
EKPAKKTTRKKKTASEEENKENEPNSKPKRVVRKIKAQPEENQPLLHQFLGRKKEGTPVKAPAPQRQQCSTPITKFLPSDLESDCDAEEFDMSDI
VKGIISNPNAKPALTNHDGHQLHYEPMAEDLSLRLAQMSLGNVNESPKVETKRDLSQVDQLPQSKRFSLEDSFDLLVKGDLQKLARTPVERFKMQ
HRISEKIPTPVKPLDNISYFFNQSSDNADVFEELMNSSLVPQDQEDNAEDEEEDDLVVISD*
(SEQ ID NO: 1170)

Name: FEN1-like
Classification: DNA_repair_protein
Gene Symbol: BcDNA:GM10765
FlyBase ID: FBgn0027914

Celera Sequence No. : 142000013384133
TAAAAGCTGCCATTGGCAATCCGGTTGCAAACCCGCCCAATGGTTGCTCCAAAATACGGATTTCTCTCGCTCTGATAGCCCGCCAAATCGTCAAA
TCCGAGGGTCACGTCATCTATTTGACCGCTGGCATCAGGCGTCTTTATGCTGGTAATGGTGGCTCCACGGGTGATCAATTGCACGGACATTCCAG
CTCCATTTGTCAGGGTGAACCGCTTGATGGTGTCCTTTGACTTGGTGAACGGATTCACCGCTCCGTTGGCGAAGACGTCTTCCGTGACGTTGACC
ATTTTGGATCCGGCTGCAGCTGTGGAATGATTACGAGTGCCAATTGCACTGCGTTTTTATCTGACCCTCTCCAAGCCGTAAAGGTTAATCAGCAC
TCGATGTGCGTATGTGTTTGTTTTAATTATCGCAAAAAAGCCGCAAACAAAATGTACATATGTACGTACATATATAAACAGATCTAGTTATCACA
AATTGGTGGGAAAGTCTGCGATAAGGGGGATAGACACCTTGTGGAGTCTTTAAGAATTGTGCAATGTTCGTATTCCAAATTTAGCGGTAATTCAG
AAAATTCTTACTTAAATTATCTTTTAATCGCCGTAGTTGCAATTCAAATTTTAGAGTTGCCTTACCTATTTTAGACCAGCTGTTTTTACATGTGC
GTAGTAAGTAAAAATTCGCAGGGGCTTGTTTTAGTAGTTAAAAATTTGTTGGTAAAATTTTTTGATATTTGCTTATTAAGCCTTTTAAATAGAAC
AATTTTATTAACATACTTGAATACAATATACATTTTTTTATATATATGTTTAAATGCCCATCTTTGCTACACAGTGGTGGCAGTTGCAAAGATCT
GGCAGCCCTGCTCTAGAAATACCACACAGCAAATAGTCCACCTCTAAGCAACAGGTCGGTTGTTTATTGAATTCGTTTATTTAACTTTATGGGTA
GTTTGGCAAATAGAAAGCTAGCTAACCGGTGCAGTTAACCCTTTTTGTTGACAGAGAGCTCAGAGGAAACGGCAGATTAGATCCCCCTGAGTTCA
TCCCCACCCAGGCACCACTAATCCGACGAGTATAAATCCCAAAATGCAATTGACGTGGCAGAGAGATCAGATAAATCTAGTACTTCCGATTGCTC
TGATTTGTTGTTGTCTTTTGATCGACGTAACCAGCGCTCAGGAGGCCCAACAACCATGGTACGAGAATCTGCCAGCGGTGGCCATGGACTATAAG
GTGTGTGCTGATTTTAAGACTCCTCTAGAGCATCAAATTTCACCGGGAACGTGGTTTCTCTTTCAGGTTCACATAGATGCTGGTAAGGAGGACTG
CTACCATCAGTACGTTAAGGCAGGAGCCACCTTCTACGTGTCCTTTAGTGTAAGTTGATAGAATTTGGGATCAATAGCATGTTTCCGATCCAATG
GATGGGTTTCCCCTTGAGCAGTCTGTGATATTCTAAAATAAATCAAATCGAATCCATTAATACAGTAATATAATCTATCTAATACAATGAAATTA
TTCATATAAATTTTTTTTAGGTGGTGCGCGGAGGCGATGGAATGGCTGGTTTCGCCGTCCGCAATCCTGCTGGTGAAGTGGTGAAGCCCTACCAG
TGGCAGGCTACTGCGGACTACACGGATCAGGTATCGCCCGGTGGCTACTACTCCGTCTGCATTGACAACCAGTTCTCCCGATTCGCTGGCAAGCT
GGTCAACATCTATATCACGGTGGTGAAGTACGATGCATGGGACAAGTACGCCAAGGAGATCGAGCAGCTGCAGCTGAACATGCAAAACTTCACTG
TAAGCCAAACTGGTTTTCAGACACACCCAAACATCCATTTACAAATATTCACATTGATCTATTTCTTTAGGCCACCGTTGGCACTGTGGAGCGCA
ACATCAACGATATGATGGGCTATCAAGCCCACAGTCGTCATCGCGAATCGCGTGATTATGCGTTGCTCCTGGACAACAATGCCTATATTCAAACC
TTCTCGATTAGCCAAATTGTGGTCATATTGATCACGTGCTCTGTACAGGCGAGTATAGACATGTTTTTTGCTTTTCCTAAATTAATAACCTAATA
TTTGCAGGTATTCTTTGTGCGCAAACTATTTGAAGTAAAATCGAGCTCCAAAAGTCGCATCTAAGGCGCAAAGATACTTTTCAAAGACTTCGCAA
CATGTTTCTAAAATTCCATCCGCATTTCCAAGACATTCATTCTATTCTACCTGCTGAATGAGTTTTTGTAACTTATTTTATCACTGGCTAATTGA
TCAAGCGCAACTGAGCAGACTTTTTTATAATTGGGACTACTTATGTCATACGAGTTATAGACAGCAAAACTTATTGTGATAAGTGTACATTTGTG
TGTTTTGTTTAATTAAAAGATTGAAGATTTTTGTATTTGCTTTGTTTTATTTGGGAAAGAACCTTAAGGATTTATTCGAAGCCATTTGGGTTTGT
TAATTTACTAAAAGCTCTACAAGCTTTAAAGTTAAGCTGCTTTGGTAAGCTCACTTAACCGTTAAATTTCATTATCCTGGAAAGGATTTTAAACT
TAAAAATATATAATTCAGGTTGTTGTTTTAAGAAACCTGTTTTTCTTTTTATATGGGAGTAAGTTATTTTCAAATTACGACATTGTTGCAAAGAC
ATCTTCTCGTTGCCTAAAACCAATCTTAAATATTAAATACATGCTGTACATGAGCTCATTAGTTTAAATTGAGAGCTGAAGACATTTCGAAGACA
TTCCACAACTTGGGCTGGCAAATTAATCACCCCGAATGCCGCTTATCGCAAATTATCCTGCCCCATCCATCGCAGGACCTTAAATCATGTCACCA
GGCTCACCGCTTATCTAGACGTCATTTAGCACATGTGTGTGCTCTGCAGCAGCTGGCATGTTAATTATATCCTTTTTGGCAGGCAGCAGGAGC
ATCTGGGTATCTTGGCGGGTCTTTTGTGGCCACTGCTGCTCGAAATTAAAATGTTATTATGCGAGGCTTATCTGCGGGCCTTAAAGCCACCGCAA
AACTAAGGTCCTAATGGCCTCGCACACCAGCACACGCTCTTTAACTGTTTTAAACGCCATTGTTAAAATATTGCTCATACGCACTTCCGCCCAAA
ATGGGGTCTTCTCTCTTCGGCAGCACTAATGATGCCCCAAGAACGCGGAGCAAAGGACCCGGCGAAAGGCAGGAGCATCCACAGCCATAGCCACA
TCCACATCCACATCCCCGATGGCACAGAGTTGGCTCCGCCCACCAGCAGCCGATGACAGCGGCAGATAACAGAGCAGCGGCAAAGTGGGCGGTGG
ATGGGGTTGTGGTGCGGAGAGCGCGCCTGCGCATTAGCCGC
(SEQ ID NO: 1171)

Exon: 1001..1235
Exon: 1302..1379
Exon: 1541..1804
Exon: 1876..2016
Exon: 2098..2366
Start ATG: 1089

Transcript No. : CT30086
ACAGAGAGCTCAGAGGAAACGGCAGATTAGATCCCCCTGAGTTCATCCCCACCCAGGCACCACTAATCCGACGAGTATAAATCCCAAAATGCAAT
TGACGTGGCAGAGAGATCAGATAAATCTAGTACTTCCGATTGCTCTGATTTGTTGTTGTCTTTTGATCGACGTAACCAGCGCTCAGGAGGCCCAA
CAACCATGGTACGAGAATCTGCCAGCGGTGGCCATGGACTATAAGGTTCACATAGATGCTGGTAAGGAGGACTGCTACCATCAGTACGTTAAGGC
AGGAGCCACCTTCTACGTGTCCTTTAGTGTGGTGCGCGGAGGCGATGGAATGGCTGGTTTCGCCGTCCGCAATCCTGCTGGTGAAGTGGTGAAGC
CCTACCAGTGGCAGGCTACTGCGGACTACACGGATCAGGTATCGCCCGGTGGCTACTACTCCGTCTGCATTGACAACCAGTTCTCCCGATTCGCT GGCAAGCTGGTCAACATCTATATCACGGTGGTGAAGTACGATGCATGGGACAAGTACGCCAAGGAGATCGAGCAGCTGCAGCTGAACATGCAAAA
CTTCACTGCCACCGTTGGCACTGTGGAGCGCAACATCAACGATATGATGGGCTATCAAGCCCACAGTCGTCATCGCGAATCGCGTGATTATGCGT
TGCTCCTGGACAACAATGCCTATATTCAAACCTTCTCGATTAGCCAAATTGTGGTATTCTTTGTGCGCAAACTATTTGAAGTAAAATCGAGCTCC
AAAAGTCGCATCTAAGGCGCAAAGATACTTTTCAAAGACTTCGCAACATGTTTCTAAAATTCCATCCGCATTTCCAAGACATTCATTCTATTCTA
CCTGCTGAATGAGTTTTTGTAACTTATTTTATCACTGGCTAATTGATCAAGCGCAACTGAGCAGACTTTTTTATAATTGGGACTACTTATGTCAT
ACGAGTTATAGACAGCAAAACTTATTGTGATAAGTGT
(SEQ ID NO: 1172)

Start ATG: 89

MQLTWQRDQINLVLPIALICCCLLIDVTSAQEAQQPWYENLPAVAMDYKVHIDAGKEDCYHQYVKAGATFYVSFSVVRGGDGMAGFAVRNPAGEV
VKPYQWQATADYTDQVSPGGYYSVCIDNQFSRFAGKLVNIYITVVKYDAWDKYAKEIEQLQLNMQNFTATVGTVERNINDMMGYQAHSRHRESRD
YALLLDNNAYIQTFSISQIVVFFVRKLFEVKSSSKSRI*
(SEQ ID NO: 1173)

Celera Sequence No. : 142000013384504
ACGTTTTTGCTTAACCTTGACGAGGAACCGACAAATTTTGTATTACATTTCTGTGCAATTAAAAGTTATAACGTTTGTGGATATGAATAAAAATT
TTACCATACCTACGTAGGTGATAAACGCGTACTTAGTAGATGGTTTCATTAAACTAAAACAACATTTTTATGGTGTTTGTAAAAGCGCAATTTTT
TAATGCGTTTACTCAATTATTTATTGCCCAGGCCCGTTTGCCACAGCCCATTTAGCAACTTTAGCTGTGCGTTACCAACTATTTATATGCGTTAC
CACATTTGAAATTGTATGAGACAGCTGGTATTACAAAGAGTATATCTTATTAATTCACATTGTAGCACTGGTGTAAAAGTGGCATATACATTGAA
TTACGAATGAGAGTGTAAAAATACGGTGTACATTTGTGTATTCTTATTATTTTTGGTAGTTTTAAACATTTGAGGCATTTCTGTCGTTTGCAATT
TACAAATAAATGGCTAAAAACTATGGCTGACGAATGAGAACACCAAATTGAAATCAACGAACTTAAGCGAAAGCTATATGAATATCGAAGTTACA
TGTGAGATATATCACCGTGTATGTATGCTTACGTAAATATATATATATATATGATTCCAAATGGGTATTTCTTGATCAAAGATACTAACGATTTT
CTGAAGGGTCCTTAAATATTTACGAGTAATTCACCTTTTTGTTGGGTGAAACTATTTAGTTATTAAACTTGTACAAAAATAAAAATAAAATTTTG
AAAATTTCACAAACTTTGTGGCAAATAATTCAACAATATATTGTAGGTCTATTACGATATAAAATGAATTGGCACTTCATGTATAAATATGTTAT
TAAAAAATCAAAACATAATATAATTCTAGTTTATTCAAGGCCCTAAAGAGAATGGTTTTTACTTTTGAGATAGAACTACCCATGCCGGAGATGCG
TGAGAAAAATGTATAAAAAGCTTAGTCGGCAGTCTAGCGTTTCCTCCAATTCAGAAATTCGTCTCCTTGAACTCCTTGGATTGCAGTACAGGCGA
AATAGCTCCCCCATCGCCGTTTTCATTTCCATTATTGTGCTCCTCTCCGCCGCCCACCGTGTAGGCCATCACAGTGGCATGATCCAATTTCCCGG
GCAATGCTACAAAGGCGCTGCTGTCCACCACACGCTTCCTGGCCGCGCGATGCTGCATGCGGTTCAGTTGCACCTCACGCTTGGCGCCATCTGGT
CCCGTAGAGAGTTTATAGAAGAGTTCCCTTTGCTCCAGGGTCTTCCTCCTGGCTGACGTTATCATCCGTACAAAATCGATAAGCAAGTGGCAGAG
CCTGCGTGCCGATACGCAGGGCGAAAACGTGCCGTTGATGCCATAGCTGAGCAGATCCTCTAAGCGGTAGAGGGTAAGAGCATGCCGCTGGGGAC
CGGTAACAAGGGGCAGTCCTGAAATGGACTTCGGAATGCGTTGGGGCACCACCGATGGCGGTGGAGCTGATACCAATCCCTGGCGTGGTTCAATA
AGCGTTTGGGAGCGCATATACTTTGGTCGACTAGGCGCATTATTAGGCGGACTTTCCGCCTTGGACTGACGAGCTGGTCGCGTGGGCGGAGTCGA
AGGATGCAGACGGGCATAGATGGCGGATGCACTCTTGTTCTGCCGTTTGGGTGCCAAGTTGGCGGGCTTGACATGTCCCGACGTCTGAAGCTTAA
CATCCGGAGTCCAGGCTTCGGCAAACTTGCCCACAACTGGATCGAAGTTATCGCTGATTCCATCCGACGTTAAAAAGACTATGTCTCCACTTTCA
ATGCAGGTCATCGAGAAGGTTAGATTGCTCAGCTCTGGCTTGTTGCCATCCGCCGGTCCAAGGGCACCCAACGCATCGCGCATGTCCCTCATGGA
ACTGATGTCGTGGGATGCCTGTGTTAGTTCCCGTACTCCGTGCTTCTTGGAGTACACATAGCCCAGGGAATCGCCAACATTACACGAGCACACGA
CATATTTCCCTGGCGCTCCGTCCAGCGGCAGCACAACGGCTATGGTGAGAGTAGATAGGGCTCCTCCAACTTCCAGGATACAACCGTGTCCCTCC
CAAAGACTACGCAGCAAACTCACAAAAACCTCCTGGGTTGTGGTGGCTCGGCACTCCAGCGCCTGTCCGAAGACCGCCCGGTCCAGATAGTCCAA
ACAACCGTGAACAGCTGAACGGGCGGCCAGACGAGCGCCATCACCCCAGTTGACACCATCTGCCATGGCCATGGCAGCTGAGTCTCCGCGCACTA
CCATTCCGTAGCAGTCGGCGATGGGATTGCCCATGGGTTCTTTAGTCAGCATGTTGGTCTCGTAGAGGGACACCGAGATACCATATGCGAAGTCG
CACTCCATGCGCCAGTTCTCCACGCCAGCGATCAAAGCTGCGGGATCAGAGCCACCCTGGTTGCTTACAGCTTCGCGGAGCAAACGTTCCCGCTC
TGAGTTGGGATCCCCATCCGTCGAGACCTCAGTCTTTGCATTTAACACATTCCTATTGTTCTGATCGCTGTTGGCTTTTCCAGCATCCGTGCCAG
CAGACGCAGCGGCCAGATTGGCTATGCTGCTTTTGGAATTCTTGCGGGAACGCATTCCCGACGCAGAAGCAGATCCGGAGGGCTGCTCCGCACTG
CTCTGTCTGCGAGGTCCTGCCGGCGGCCGTCCGAATTTGCTGGTAAGTCGGGTTGAGTTCTGTGTGGCCACCTGAACTGGTGGTGTACTCCTCCT
AACGCCATAGCAATCATCGTTCTCCTGCTGCGTATCTATGAAGTCAATGTCATCCGCGAAGCTGGTGCTCAAGTGCAGTTTGGAGCGCTTGATGC
CGGTGAGCCCCTCGTCAGGACCTGTGCAGGCGGCTGTTATAGAGCAGTTTCCAGCTTCGTATGTATCCAACTTGAGAACGGGCATGTCCGTGGGA
TTCTGGCCATTGTAAATCTCCGGACCCTCAACAAACTGACGCTGCATTCGGCTGTCGGTGAAGGTGGTCGGGTAAATATTTGAGCAACTTTCGCA
GGCTACTAGGTTTCTATTTACTTACCCCTCCAGATATTTAGTTATGAAGCTACCATCATCATCCTCGTGCTCGCTGGCCCGCCGGCGACCCTCGC
GAGGCTCCGCGATGAAGCTCAACTGGCGGAAGTAAGTGGTGACTTTCTGGCGCAGCGACGGCATCTTTAGTCGAGTTGCTCCCTCCTCCTCGCCA
GCAGTTCTCGCCCTCCAGTTAGGGTTCTCTTAATTGCCAGAGATGGAGGGGCTAAAAAATGGATGCTGGGATGCTGACCAGTTCGTTCACCTCAT
CAGTGGCAATTGTTGTGGGAGTCGAGTCACTCCAAACGAATCCAGCCGCCGACCCTGCAAAGAGGTTTAATTTAGAGCTTCATTTAATTATCAAT
AAATTATGCAATTAAATGGGACTGGGCAAACACGAAAGAATTACAAGCAAATTGCATAGGCAGCCGCATAACTGACATTACTCCCTCCTTTCAAC
CGCCTACTCCTAAATGACGAGATGTGCTTTTTAGTTGCCGCAGGCCCTGCATCCTTTCCCTGGCCACACAAAACCCTTCGCTCATCAGGAGCAGG
ATGTCAGAGGAGAAATCCCACCCTGTGAATGGGCTTTTACCCAGCTCATTGCGAATGCAGTAGACACTGAACTGATGCGGACACAGAAATCCCCT
CCTTCCTTCGGGGTTCAGATGACATAGCTTTTAGCAGGGCTCTCCGCATGTGTTCTGAACCAGAGATGCCAATTTGGTTCTTTGCTCAACTAATT
TTAAATTGTTTATGGATTAACTTATGTGCCAAACTACTTGCCTTTCAAAATAAACCATTTATAAAATCGAACGCAATAATTTGGGACTTGATTTA
TCACAACATTTATTTATTTATATTAAACCCTTTTCAGGATCAACTTTCAAATAGTCCTTTAGCATGAATTAAGTAACTGGCATCACTGATGTGTT
GATGATTAATGAATGGACAAACCAACTGCCTGGGGCGACCTGCAACTCCAGCAGATGTTGGGTTTTCGGATTCTGACAGCATCAAGTTCGGTTTC
AATGGAAAGATGATATCATATAGGGGTAAGTTTGCCGGCGAGAAACACACCAAGGTCTGCTGTACAATTATGTATCTAACTCTCCGCCGCTATCG
CAGACGACATTTAATTGCCGTGTTAGGGCATTTAACTACCTGATCCATTCTCGTAGACAATGTAACGCCAAGACAGCCTTCATTTCGGCGAGATT
ACAATGGATCGCAAACACAATAAATGCTAATCTTCAGCAGCAATTGCCGTGGAGATGCTTTTCCTTAGACGATGTACACAAAACGATTTGTATAA
ATGATAAACAACAACAAAAAAGTCGGCACGGAAAGTAGTTTCGTTGATGGGGGCAATTATTCAAGATACCCCCCCTCCCTTGTTGTTGCTGAAAT
TTTCACAAATGCTTCAAAGATATATATAAAAAGAAAAAAACACAATCAACCACTTTAATTTGTGGCATAAGTACTTCAAGTGACAAATGAGTGGT
CAATTAAAAACTATGTCGATTAACGGTGAATACTGTGGGTCGGTACGCCTCTCTATGCGCTTCTCATAAACGGCACTTAACGGCACGCGAAAATC
GCATGAACCCTGAACCAATTGTTCGAGTTTCGATGAACTTGAACTGCACTCACGAATCAATCAGCGAGTAATGTAATTCAATTTCAATCTGATGG
CCCCAAGATGCGCGATTTCTTGGCAATTGCTGGGCACTGATCCGATTGCCACCACACCCGCATTCCTTGCGGCAAAGCATTAAAATCAAATTAAC
CCACATAACCATTAAGTGCAGGAGTGGGAGATTTCCCATTACCATATCCACATTTCCCAGATACAAATCAAATGAATTGAAAAGTCAGAGCCGCG
AGACAAAGTCGATCGCTGGACGAAAGGATGGATAGCTGAGTGCCCATGTGGTTATAAAGATATATCTTTCTGTGGATGCATTGAGGCGCGGCCA GCTGTGTGCACTCGTACCGGTCCAGGGCAATCAATACGGATGATTGAAAAGCCCACCTTCACATCACCACAAAACAATTCAATTTAGCCACAACA
ATGTGCAGCTTGCGATTAAATGTGCAGCCAAAGAGATTACAACTGCACCACAAGAGCCAACATTGAAGCTCAGCCACAAGCGTTTTGTAGTTCCC
ATCTGCAATTGCTCCAATTTCTTTACGCCTCCTCCAGATCTGCTCATCCACGTCAATCAGAGTCGTCATCACTTGACACACAATAGGCATCTGAC
TGTGACTTACTGGCTTCTCAATTCCCTCAGCTTTTTCGCTTATAAGTGTCCATTGTGGATCTCACAAATTATTTAAGTTCTGACTTTTGTCCAC
CTGACGGCACGTGCCGAGAATAAAGTATAGGTTTTATAGAGATGGAAAAATCTCTGGATTGAGAAGTAAACTCATGTAAGATGCCCGTAGCAGCC
GTTTTGTTTACCCATGTACATATATTATTTTTTAATCTTTAATTGCATTTTATGTATGTATTCAATTGTATATGAAATGACACTCCCCCAAACAT
TAAACAAACAATTCTTCGAGGCGTGTGCCGCAATCAATCGACACTTTTCGATTGGATTTCGGGACCATCGAAATTTTCAACACTTGAAACTAATC
AAGCGTGGAAATGGGGAAATAGGAACGCGGTGCTGTGAGATCATTGTGCAAGATCTGGGTGGGGCGATCCGTGGTGTATAAAAACAACTGAGTAA
ATATTATCGGATGTGGCACAGATCTCGTGAGTCTTTCGAACTTTGTTTATGCTCGAAAACCAAAATAAACCATTTGCGCTTCCTCCAACCAAAAA
TAGTTGTGTTGGCCCGTATTTATAGCTGCCGCCCGTGGAAACAAAAAATGTCTGGGTGAATTTCTCGCTTGAAAAACTCATTTGGGCAAGGCTTT
GAAATGCATTTCCCGTCGCATTCGAAATCAGCTAAATTTTCTGAGCTAATCAAATGCGCAAAATTATTGTTTACACACTGGGTTAATTAGATGTG
GAGATTGGTTTCTCTGCTCCGCTTCGAGATTCTTTTGTGCTCTTTCGGCTTTGTGCATACTTAAAATGTGTGTGGATTTACGAGGGAGAAGTGCT
AAAACCCAATGCAAACAAGTCTGCTTTGGGGTCCAACCAAATGCTCCAACCAAATGCAAACACACCCGTGACATTCAGAGTCTGGATGCACTTGA
GGCAAGTGACAGTTGTCTGCAGATTATGTGCTATGTGCTGCATATTGTGGAATCTCAAGGTGCAGTCGGTGGGCCAAAGCCGCAGTCAAAGAAAA
AGCCTTAACAGCACAAGTCAAGTGAGGCTGCTCAAAGCCGTTTTGTGTGCTTCTGTTTGGGCCAGACAACAAACAACAAGAAGCTATAAAAGCAG
AGAGTGAAAATTTGTTGCATTCATTGCGTGTTTTCTTCGAAAGAAAGTTGAAGGCCATCGTTAAGCTGTAGATTAAATAGAGCTGTCTGCTTGAT
TACGAGCTCCCAAATATTTCAATCATTTCGAGCGACCCACTTTATGTATATTGCTTTTGTAGCGAGTTCCCTCCTTAACGTATAAGTTGTGTAGC
TTAGGTATTCTAAGACCTTAGATTAGATGATTCTCCCTTATGGGAATTATAATATATGAAACAAAACCGTATGCACAAACCACATACACGCGTCA
AGTGCTGATTCAACCGCAGTCAAGGCAATCTTGGATAGGAAATGCATGCTTAATTTTCATTTCCTCATATGCAATTTTTCTCATTTCAAGTCCAG
GCTGATCAAGCCGCATAAAAATAAAATATTAAGTAGCAAATGCATTAAGCAAAATGGACGGGGTTCCCCAACCCAGAGTTTTAAACTGACAAGCT
TTTGGCTTAAACCTTCCCCCAATATTTGACCATGTGTTGACTCATTGGACAAGCCGTCAGCTGCATTAATAATGCATTAGACCAGCCCCAGGACA
TAAAAGTCCCCCCATCGTGCTAAAGTGGGCGCAACACGGCCTGGGGCTTCATGAAAATCTGGCAATTAAAATGTTTTACATTATGTAAACCGCAC
GAAAACAATCACTAAAGAGTTCCTTCACCTCGAAATGGCGTCGTGAATATGAAGCGATATGTATGATGTGGGAAACAAAGGAGGAGTTGAGGAGT
CTCTTCCCGGTTTTCGAAGCATTTCTTATAAATTGCCACCTAATTGGCGTGTTCAACATTGTGACTGTGCGTGGTACGCCTCATTTCCTGTTGCA
ACAATTTGCATTAATAGAGGGTCTCATACCACAGATTCAGTTCGAGATCTCCCCATCCGTATGCGAATGCGAATCTATTCCAGTGAATGCATTTC
AGTACCATTCAATTGAAGGCGCGATGAAATGGAAAGTTAAGATCCCTTTGGAGGATTGGATGTGTGTCAGAAGTTGAGAAACATCCTTTGTTTTA
TGTGCCTTCCATGTGCATTCGCACTTAACGCCAATGCCAGGACCTAAGAGCACCCAAACCCACCCAGTTTTTCCCCACTGCATTTCCGCTTGCAT
GTTTTCCCTTGTTTTTCCGCTTTTCGGGTCGCGCCACTTGGCCCGCTTTTCAGCCACGAAAAACTATACTTGAAGAACTTGCCACACGCCGAATA
CAATAAACTAAAACTGGGGCAAGGCGAAATAATTCGGGCCTAGAAAGGCAATATCAAAGGAGTGCCGGAGCTTATGTATGGTATAAGGGTAAATT
ACCTTTCGGACTTACTGGGTATATAGCATCAAACCACCCTCACACAAAACATTTAGTATGATTGTTTTTAAAGCCATATAATTACGGCGAAGGAA
AGCCATTCCCATACCATTCTACTAATTGGTTGATTTTTTGTTGGATTTCGCAAACATCTGGCAGAAAAATTGATGCCGCCAAACAACTCCACACA
CATTTGGCAAGCCCACAAGATAATTTGCATAAATTGAATTGAAGTCTTTACTTGTTGGCCAGGTAGCGACAGCTGTCGTCGGTTTATGTAGGACT
TATATACGACTAATCCTGCATGAATAAATTAAATGGGAAGCCTCAACTAAGTCTGTCTGGCGGCGGATGGGTTTTGGGTTTGGCCTCTGCCGAAG
CCTTTGTTGCCAAGCATACAAATGAGTTGAATCCAAACTCCTGGGCGCTGTCACTCTATGCAAATCTAGAAAACCAGTAACCAGTTGTTGTAGGA
TGGAGAAGGCACGGTGGACGGACTTTCGGGGCGCTCAACTCACATATTAAATTAAATGTTAATGGCAACAAAGACAATTCAAACGGAGTCAAGGC
CCGGGCCAAAGAACTGTGGCTAACAAAGAGGCAAACAACACCAATTTCTCGACTGCCCCGCAGCAATTGAGCAACCAACGAGCCACTTTGTTCGC
CCCATATACCCCGCCCACATCCCAGCCCCTGTCCACCCGTGAAATCTGTTCTCCACCTCCAGCTACCTCTAGATAATATTGCACTGTTCGGTGTC
AAATGGCTGCCCACTGACGGACTTCTTGGTTTGTCAGGTGCCATGGTTATTCCACCTACAGTAGAAGCTCTTGAAAGTGGAATTTCTTTCTATCT
AATAATAAAAGATAATTGCCGAGACAGTTTTGGTTAAAAGTGGTCAAAGTGCTCAAAGACTCTCTATCGTCGGTTATGTACGTTAATCATATTAG
AAGTAAGTGAAAATGTCCCCAGAAAGGACGTTCATTACAAGGAGCCCCTACTGTACAAGACCTTGCGGCGGGTTAAGTGACCGATTGGCTGTCAG
TCCCCAGCCAACCAACCTCACCTCTCGGACTTCTAGTTTTAATTTGAATTTCATTCCGTCTCGTGTGGTGGCCAAACGCTTTGGTGGTTCGCTTA
GTCATATCACTCGGCTGACTAATCATTGAAAGCGGAGCGTGCTTGGAGGGAAACCTTAAGCCCCAGATATACCCCCCTTCTAACTCCAAACCATT
TACCGAAATCTCCACCCCGCCAAAACCCCACACAGCTGCAAATTCAATGAACCTTTGCTGCTGTTGACTTTGCTGATTAATTGGAAATTGGCAAA
ATGTTATTTATTTTCGCGCGGCTGGTCTAGCGCCAAATGGTTGTTTTTCATCAAAGGCATAAAGTTCTATAAATGTTCCCAGACAAATTGGTTTT
AATGAGCCGGAAACTTTTTCGGTTGAGCTCGGATTTTTACGGGTTTGGCGGATAGAAGGAGAAGCCACATATTGTACCCGATTGGCTTTAAACAA
ACACGGACATACTATACTGAGACAACTTCTTCAGTGGCTCGCTAATGCATTATACAAGAATGAACTCCTTTGCAGGCACGGCCGAGCAAACAAAC
TTCAACTTGTCCGGACCAACTGCGTCATAAAAGAGCCAACGGCAGCGCCAATCGCCATCTCCGTTTCCAGCGAGACAACAAAGGATGTTGGGCGC
CGGGAAGCAGGAGGAGCAGGACCTGGGAAACCAGCCAGTTGTGGATGGAGCGCAGACAGAACAACTTCATGCAACCCCATCCCCTGGGAACCAGA
CGGCAGCCAGGAGTCTGTGTGCCTGATCCTTGCCATCTCGAAACGAAAAAGAAGCCGGCGAAAAATATATAAAATGGAGAAACAAAATATTTTCC
CGATGTGCATGCATAGTTCAAAGTTAGTTTCAGGCATCTGTGCACCACCAAATACACCACATTCCCCACTACTTACAAGCAGAATTGTGAAAATT
TTTTGGTTGCCAAGCGAAAGTGATTGAATTCCTAGGGATTTTGTCGGGCGCCAGTTGAAAAGGAATTTTTGATGCGTTTAAGTGCCGAAGTTTCC
CTAAAAAAGTTTGGCCTTAGAGTCAGGGGATGTATTAAAAAGAAAAATGTCGAAAGTTTTTGAAAGAAGAGATTAACAATGATGTGTGATACAAT
GATTGTGTGTTTTGGTCTGGAGAATTTAAATCTCAATAAAAAACTACAAAATGTATATTAATGAGGCTAACGATGGTTATATTATGCAAACAAGT
GTTGGGGGGAATATAATTATTTAAAATAATTGCATTTTTTTGCGATTCCCACTTTGCAATTCTAATCCCTAATAAAACTAGAGATAACTTATCTT
ATGAAGCAATTTGTTTACTACTGCGACTGGTCTACAGAATATACTGATGCAATCGCTTTAGAAGTGTGGTAGGTAATCCCGTTCGTTCTCAGCCG
GAAATCACCCCCAATAAGAAGTTTAGATAATCTTAGATACGGTATCTGCTTGTTGTTTGCCACATGCATCTACACCCTGGATTCTAAACTTAGTT
CCCCCAAAATATCTGACCGAGTTGTCCCCTTTAATTTACAGCTTATATCCGGCATGTTTTTCTCCCGTTTGAATTTTGCCACAGTTTGCGCCAGA
AGTTGTGAAAAGGGCAGAAAGAGAACGAGTTGAAAGTTCCCATTAGAATGCCCAATCCAAGCCATCCTGTTCCTTTATTGCGTGGCCCCTTTTTT
TTACATTTTCCGTAATTCCCAGCCAGGCACCATCACGTGTCGGGTTTTCTCCAAGGTATTGGGCTTCGTGGAGAATCGATTTTGTGGCCTGACGA
GCCTGTTATCCTTGGAGCGAGCGCTTTTGGCTTGTTTCAGGACATAGAAATTGCCTGCTGCATGTCCGAAAGGCTCAACGAGAAATTATGCTAGC
TACACTGAAATCTAAACTTCAGTTCAAGGAACTCAGGAAAGAAAATACTATTCAGAAAATGAAGTTTTTATGTTTTAAAACTTTTATAACAGTTT
ATAATATTATTGATACGATGTCAATATTTTATATTTGTTTTAGTTCGGTAAAATGAAGATTATCATGAATTTTTCTCAGTGTGCGAATGGAGGTG
AGTGCGAAAACGAGAAGGAGGAAGCATCCATCACATGCATCTGCAGTTGGCAGGCAGGTAAAAATGTTGTACAAAAAATGAATAACTGACATTTT
AAGTGGGAAAGTTTTTGCATCAAAATCAACTGCCTGCCAATGCTGCTACCGAAATTCAATATATTAACAAGTGCTCCGTAATTGTAAATTATCGC
CACTTTTTACAGTCATTACTATTAGTAAGTTTATAATTATGTGGGTAACAAAGCGGTAAAATATGCCAAACGAAAAACAACACCAGCTATTAGCA
CAGTTTCGAAATACGATAAAGCTTGAAAACCGGTTATTGCACCAACGAAAGCTGACTTTTGTTGTTCTTGTTTTGTTTGTTATTGTTATTTTTGC
TAGAGCAGCTGAGATTTCGCAGCTGCCCGTGAAGTTGAAAACAAAATAAGAGAAAAAAACAAACGGCAGGTGAATCAACAGCGGTTCAAGCGCCC
AACCCACCCACAAGTTTGTTGGAGGGGGGACGACGACGTAAAAAACAGAATAATAAAGACGTAAACCCAGTTAAATGGAAAAATCAAGGCGAACG
AACACACACGGAAGCAAAAGCACAAAACAAAAGGCGACAAAAACACGTCGAAGGCGGCAAAAAAATTTGGAGAACCCAAAAATCAATAGAACTTC
GAAATATCCATAACCATGTAACACAGTGCACATTCACTTACAATAAGTGTGCCTTCCTCTTCTGGGTTGTTTTCTTATCGCTACTTTACATATGT
TGGCGCCACTTGCAATGGGGAAATATATGTAAGTGCGTGCGTTCCGTTGGTGGTGTGTATAAATATTTAACATTTGCCGGAGGGTGGTTCCATCG

FIGURE SHEET 629

CCCAGAACTTCGGCTTCTGCATGGAATACTAACATAAATCGCGCTGCACAGTCCACTTTTGTGTGTTGCACTTCGAGTCCCAATGGTTACCAATT
AATGTCGCTACGAAATGGAACTGCTAACGACTGTTTCCGCCGCGGACCGACGTTCCTGCTTCGATTTGAAATTCGAAGTGAATTGGCCAAGCCAA
GCGATATTTGTGGTAATCGAATCGTCGATATGAAACACACTATTCTATGTGCAACCAACCGAGTTGGCAGCTCCCAGCGCGATTTTTCAGTATAT
TTTGCAGTATTTTAATTGTTGCAGACGGCTTTTTAAAGCGCCACCAGTTCGTTCACATTGTCGCTATTTTTCAGCATTTCGCGGGATCTGTATTT
TTTATAGGCGAATATTGAAATTTGCATGGTCTAACATTGATTATAGTGTTGTATTCACCGAATATTTATTGGTTTTACTGTCCATTGCTTTGAAA
GCAATAGAAATAATTGAGGATCAAGTAAGTTTAAGATAAATTATTACAGTTAAATGCCGATGCAGGCACTCACGCACACTAACGCACCCAAAACA
GCGACACGCGAATTTGCGAATTTCGTTTTGGCCCGTTGTTTGTGTGTTGTTGCTGTTGTTACAACGTTGTTTGTGCTAAACATTAATTAATTGTC
GCAATGTCTGTTTCGCTATAAATATGCGAAACGTGCCGTTGTTATTTGCGCGAAACTAAATGGCCAATTGCGCTTTACCGGTGTTAGTGTAGGTG
TATGTGTTGTCTGTGTGTGTTTGTGGTTGCTGGCGCGGGCGAATGGCGGGTAATCCGCATACACTCGCACTTATTTTTTGCAAAGGGTTTATGCG
ACACTCGCTTTGATCACGATATTAAAAGCTCAAACACCACTCTACCATTATACAAATATTTATTTATGTAAAATAAATGCGGTTAAATAATTTAC
CTTAGAACTTGCCCTAAAGGATATTAAGTGCAATTAAAAGTAGAACAAACATTCATTGCTAAGTTACTAAATGAATAGCATTTTCTTTTGCAAAC
TTGTTCATTATAAACTACTCCTTCGAATATATATTTACTTAGTATATTTTCTGTTTCCACGACTTTGTCTCACACATAAACACGTAAAAGCGCGA
AACAGACACAACGCACAC
(SEQ ID NO: 1174)

Exon: 11938..11632
Exon: 3379..3066
Exon: 2996..1001
Start ATG: 3199 (Reverse strand: CAT)

Transcript No. : CT36839
CGAAGCAGGAACGTCGGTCCGCGGCGGAAACAGTCGTTAGCAGTTCCATTTCGTAGCGACATTAATTGGTAACCATTGGGACTCGAAGTGCAACA
CACAAAAGTGGACTGTGCAGCGCGATTTATGTTAGTATTCCATGCAGAAGCCGAAGTTCTGGGCGATGGAACCACCCTCCGGCAAATGTTAAATA
TTTATACACACCACCAACGGAACGCACGCACTTACATATATTTCCCCATTGCAAGTGGCGCCAACATATGTAAAGTAGCGATAAGAAAACAACCC
AGAAGAGGAAGGCACACTTATTGGTCGGCGGCTGGATTCGTTTGGAGTGACTCGACTCCCACAACAATTGCCACTGATGAGGTGAACGAACTGGT
CAGCATCCCAGCATCCATTTTTTAGCCCCTCCATCTCTGGCAATTAAGAGAACCCTAACTGGAGGGCGAGAACTGCTGGCGAGGAGGAGGGAGCA
ACTCGACTAAAGATGCCGTCGCTGCGCCAGAAAGTCACCACTTACTTCCGCCAGTTGAGCTTCATCGCGGAGCCTCGCGAGGGTCGCCGGCGGGC
CAGCGAGCACGAGGATGATGATGGTAGCTTCATAACTAAATATCTGGAGGGCCGAATGCAGCGTCAGTTTGTTGAGGGTCCGGAGATTTACAATG
GCCAGAATCCCACGGACATGCCCGTTCTCAAGTTGGATACATACGAAGCTGGAAACTGCTCTATAACAGCCGCCTGCACAGGTCCTGACGAGGGG
CTCACCGGCATCAAGCGCTCCAAACTGCACTTGAGCACCAGCTTCGCGGATGACATTGACTTCATAGATACGCAGCAGGAGAACGATGATTGCTA
TGGCGTTAGGAGGAGTACACCACCAGTTCAGGTGGCCACACAGAACTCAACCCGACTTACCAGCAAATTCGGACGGCCGCCGGCAGGACCTCGCA
GACAGAGCAGTGCGGAGCAGCCCTCCGGATCTGCTTCTGCGTCGGGAATGCGTTCCCGCAAGAATTCCAAAAGCAGCATAGCCAATCTGGCCGCT
GCGTCTGCTGGCACGGATGCTGGAAAAGCCAACAGCGATCAGAACAATAGGAATGTGTTAAATGCAAAGACTGAGGTCTCGACGGATGGGGATCC
CAACTCAGAGCGGGAACGTTTGCTCCGCGAAGCTGTAAGCAACCAGGGTGGCTCTGATCCCGCAGCTTTGATCGCTGGCGTGGAGAACTGGCGCA
TGGAGTGCGACTTCGCATATGGTATCTCGGTGTCCCTCTACGAGACCAACATGCTGACTAAAGAACCCATGGGCAATCCCATCGCCGACTGCTAC
GGAATGGTAGTGCGCGGAGACTCAGCTGCCATGGCCATGGCAGATGGTGTCAACTGGGGTGATGGCGCTCGTCTGGCCGCCCGTTCAGCTGTTCA
CGGTTGTTTGGACTATCTGGACCGGGCGGTCTTCGGACAGGCGCTGGAGTGCCGAGCCACCACAACCCAGGAGGTTTTTGTGAGTTTGCTGCGTA
GTCTTTGGGAGGGACACGGTTGTATCCTGGAAGTTGGAGGAGCCCTATCTACTCTCACCATAGCCGTTGTGCTGCCGCTGGACGGAGCGCCAGGG
AAATATGTCGTGTGCTCGTGTAATGTTGGCGATTCCCTGGGCTATGTGTACTCCAAGAAGCACGGAGTACGGGAACTAACACAGGCATCCCACGA
CATCAGTTCCATGAGGGACATGCGCGATGCGTTGGGTGCCCTTGGACCGGCGGATGGCAACAAGCCAGAGCTGAGCAATCTAACCTTCTCGATGA
CCTGCATTGAAAGTGGAGACATAGTCTTTTTAACGTCGGATGGAATCAGCGATAACTTCGATCCAGTTGTGGGCAAGTTTGCCGAAGCCTGGACT
CCGGATGTTAAGCTTCAGACGTCGGGACATGTCAAGCCCGCCAACTTGGCACCCAAACGGCAGAACAAGAGTGCATCCGCCATCTATGCCCGTCT
GCATCCTTCGACTCCGCCCACGCGACCAGCTCGTCAGTCCAAGGCGGAAAGTCCGCCTAATAATGCGCCTAGTCGACCAAAGTATATGCGCTCCC
AAACGCTTATTGAACCACGCCAGGGATTGGTATCAGCTCCACCGCCATCGGTGGTGCCCCAACGCATTCCGAAGTCCATTTCAGGACTGCCCCTT
GTTACCGGTCCCCAGCGGCATGCTCTTACCCTCTACCGCTTAGAGGATCTGCTCAGCTATGGCATCAACGGCACGTTTTCGCCCTGCGTATCGGC
ACGCAGGCTCTGCCACTTGCTTATCGATTTTGTACGGATGATAACGTCAGCCAGGAGGAAGACCCTGGAGCAAAGGGAACTCTTCTATAAACTCT
CTACGGGACCAGATGGCGCCAAGCGTGAGGTGCAACTGAACCGCATGCAGCATCGCGCGGCCAGGAAGCGTGTGGTGGACAGCAGCGCCTTTGTA
GCATTGCCCGGGAAATTGGATCATGCCACTGTGATGGCCTACACGGTGGGCGGCGGAGAGGAGCACAATAATGGAAATGAAAACGGCGATGGGGG
AGCTATTTCGCCTGTACTGCAATCCAAGGAGTTCAAGGAGACGAATTTCTGA
(SEQ ID NO: 1175)

Start ATG: 488 (Reverse strand: CAT)

MPSLRQKVTTYFRQLSFIAEPREGRRRASEHEDDDGSFITKYLEGRMQRQFVEGPEIYNGQNPTDMPVLKLDTYEAGNCSITAACTGPDEGLTGI
KRSKLHLSTSFADDIDFIDTQQENDDCYGVRRSTPPVQVATQNSTRLTSKFGRPPAGPRRQSSAEQPSGSASASGMRSRKNSKSSIANLAAASAG
TDAGKANSDQNNRNVLNAKTEVSTDGDPNSERERLLREAVSNQGGSDPAALIAGVENWRMECDFAYGISVSLYETNMLTKEPMGNPIADCYGMVV
RGDSAAMAMADGVNWGDGARLAARSAVHGCLDYLDRAVFGQALECRATTTQEVFVSLLRSLWEGHGCILEVGGALSTLTIAVVLPLDGAPGKYVV
CSCNVGDSLGYVYSKKHGVRELTQASHDISSMRDMRDALGALGPADGNKPELSNLTFSMTCIESGDIVFLTSDGISDNFDPVVGKFAEAWTPDVK
LQTSGHVKPANLAPKRQNKSASAIYARLHPSTPPTRPARQSKAESPPNNAPSRPKYMRSQTLIEPRQGLVSAPPPSVVPQRIPKSISGLPLVTGP
QRHALTLYRLEDLLSYGINGTFSPCVSARRLCHLLIDFVRMITSARRKTLEQRELFYKLSTGPDGAKREVQLNRMQHRAARKRVVDSSAFVALPG
KLDHATVMAYTVGGGEEHNNGNENGDGGAISPVLQSKEFKETNF*
(SEQ ID NO: 1176)

Celera Sequence No. : 142000013383859
GACCTCTACAAGAACGGCGGCATATCGCATGGGGCACACCAAAAGTCGGTTGTCATTTCGGGGATCGAACTGTACTTTCAGCACAGGCGATGGAA
ACCTATACTTGTGTTCCAGTTCGCCGGTTAGCACATCCCAAATGCACACATTGTTGTCCGTGGAAGCTGAAAGTAACTGGAGTGGATTGGAAAAT
GTAGATGATCAGGTGTACGGCGAGCGAGGGCCTACCTTGTGACCATTCCTGGTCCAACTGAGACTGCAAACGGGATGCACATGGGCCGAAATAAT
CTTGGCAATGCCCCTCGTCAGAAAATCCCAGATTACAATGCGGCCATCATTGCATCCCACGGCCAAAAGGGTTCCGTATTTGTTAAAGGCACACG
TCACGGCCAACGAAATGCAATCCAGCGAGCCGTCGAACTCCTCTGGGTAGTTTTGTCCGAAAGATTCTTAATAAAGCTGGAGTTATTTACTACAT AAGCATAAAAAATGGGCGGCAATCTCACCTAGTAGCTCCAAATTCATTTTTGTTTACTATCTTCTTCTTTTAAAATGGCAACTGACACTCACACC
GAACGGCAATAACATATTATGTTATAAATGATAAGCATAACAGAAGACGAGTTTTTCGATAGTTAAGGTTATATTCTGTACAACTACTGAACATC
AATTATTATATTATAATACGAATTTAAAAATCTACGTATCTACGTTGGTGTTTTTTGTGGTTTTATTAATAGAATAAGTTTAGTTAATTTTAGAG
GTGAAATTAAATATTGAAATAGTTAAACATATAAAATAGATAAATTTGGTGAAGCGTAAGTAAATTTTAAACTGCATTAGTTATATCTTAATTCA
AGTTCCCCACTAATTTATGAGCGTTAGATGCGATAGTGTTATGTCTGGCGCAAGCGATTGTCTCGACGTTTCTTCGATATTTTAAGATATCGATA
ATGTCATCGGAGATTTGCCACCCCTATTTTTTGAGCTCTGTGCACGTTGTATGAGAAAAATTTATGCAGATGTATTCGCCAATTGTAACCAAGTC
CGGATTGTGAAATTGCACGCAGACAGCGAGCATCATAATAAGCGCTCTAATTGGAGAAGGCAGAAGTTTCGAATTAAGCCATTTCGGAGACGTTT
CGTCCGTGGCACGCGATTGTGTCAACGTCACCTTTGGAGCACTCGCCCTCTCTCGCTCGCTCCCGCTTTCGTTGCCAATTTTTTGCTTGCCCTCT
CTCGGTCACTCCCTTCGAAAGCTTAACGGTTAGAGTGTAATAATGAAATAACCCAGTTTCGAATTTCGTTCACAACAAAAGTGCGGGCCTTTCAT
GCCAAAATAACATTTGGTTTCGAATTGTTTTTCAAATTCGAATCGAGGTTTTCCAGCTTTCCAGTTTGACAGCGAGAGAACGAGAGAGAGCGAGG
GCGAATTACGGTGTTCGCGCTCTGCTTGTGCTTTCCACTCCACTCCCCTTCTTAACTTCCCCCCTCCCAGCCTATTTACTCTGTGTGCATGTGTA
AATGAATACTTTAAAACGTTTTTAATCGTTGCAGTGTATTCATCGCCAGCCACGTTAAAAGGAAGAACGTGTATGTGAATACGACCATCAGAGGA
TCTTAGCGAAGGATTCAGGAGCCCAAATTCTTAATCCCCATCCCACACACACACATATACTCGCACGTAGGCACGCTCTCTGTGAGAGGAAGGGT
AAATAAAAGAAGCAACGAGCAAAATGTCTGGCGAGGAAACGTCTGCCGATCGCAATGTCGAGATCTGGAAAATCAAGAAGCTCATCAAGAGCCTG
GAAATGGCCCGCGGGTGAGTCTTATCAATGATATACATGTCCTTTAACGTCCCCCCCAACGACTGTTTTGCGTACGTGTGTGGGGTATACACAAT
GCATGGCACGAAAACAACAACACTGGGGTGGAAGTGGGCGTACTGGACGTGGGTGTGGGTGGGGACTTGAGGGAGCGGCGAGTACAACCACCTTT
CCTTGTTGTCGCCGTGTGAATCTCCTTTGCATTGTTTCCAATCTTGGCAAGATCCCCCGCCTCACTCTATCTCTCTTTTTTGCATACGAGCAACA
CGTTTTTGTCGAGTTTTTATCAGTTCAAACTAGACTGATTGAGAGACGGAGAGAGAGAGAGAGAGAGAGGAGTGAGTGAGTGAGTGAGTAATCGC
CTCGTGGCTGTTGTGCGTATGCGTGCATGTGTGTGTGTGTTTTTCCCCCAAAATGGGCCAAGCTTTGTGGACCCCTCGCTCTCACTCATCCTGCC
TCGCTCACTCCCTTGACCCGGTCCTTACCGCTTCACACCGCTTTAGAGTGGGTAACAAGGTCAGCAAATCGAGTGACCCCCACAGGAGCATATCT
GCTATGTATATACATATATATGTATATTGTTGTCAATATGCTCCACAATTGGAGCTAACATTACACCTCTTCCAATTGGAGTTGGCCACTGTTGC
CAATTGGGATTCGCTTTGACAGATATCTTCCTATTGGTTTTCAGCCATATGCGAAATATATACACACATATGTATTTGTTTTTCTTTTTTTAAGT
TCTGTGCTATTTTTTGTTGTATTTTGCATTCCAACATTTTGTACAAATTACGATTGGCACTCCTCTGTATTATAACGAACGAGAAAATGATTTGC
ATCAGAGAAACAAACGTTTGGAAGTTACAGAAACGTATTTGTTTCAATAAATTAATCAAAGTTTAAATTTAGTCCAATAACCGAATGTCAAGTTT
AAAAGACATATGCCACGAAATTTCACGGCTAATTAAATAACTTTAAAGTAGGTTGCTATTATGTGCATCTGACGCGCAAATATACGATTGAATAG
CACTGTTGCTATGGGAGAAAGAGCCATTTCCGCGACTTATGTTCTCCCTTGTTTGGGTTTCTTGCAGCAATGGAACCAGCATGATTTCTTTGATT
ATTCCGCCAAAGGATCAAATCTCGCGCGTCAGCAAGATGTTGGCCGATGAGTTTGGAACGGCGTCGAACATCAAGTCGCGTGTAAATCGGTTGTC
CGTCCTCGGTGCCATTACGTCGGTACAGCACAGACTCAAATTATACACCAAAGGTAAGCTGAGCTAAGAAATTGTTCATAAACAATCGAACAAAC
GAACTCTAAACCGTATCACCAACCGCTTCAATTCAGTGCCTCCCAACGGTTTGGTCATCTACTGCGGCACAATAGTCACAGAGGAGGGCAAGGAG
AAGAAGGTGAACATAGACTTTGAGCCATTCAAGCCCATAAACACGTCGCTCTACCTCTGCGACAACAAGTTCCACACGGAGGCCCTCACTGCCCT
GCTCGCCGACGACAACAAATTTGGATTCATCGTGATGGATGGTAACGGAGCGCTATTCGGTACCCTTCAGGGCAACACGCGCGAGGTGCTCCACA
AGTTCACCGTCGATCTGCCGAAGAAGCACGGTCGTGGTGGTCAGTCCGCCCTTCGTTTCGCCCGTCTGCGTATGGAGAAGCGCCACAACTACGTG
CGGAAGGTCGCCGAGGTGGCCACCCAGCTCTTCATCACGAACGACAAGCCCAACATTGCCGGACTCATCCTGGCTGGTAGTGCGGATTTCAAGAC
TGAGCTTAGTCAGTCTGATATGTTCGATCCTGTAAGTGGGAGTTAACCTATTTCCATCGATGCCATATTAAGCCTTACACTTGAATCTTTTTTCA
GCGTTTGCAATCAAAAGTCATCAAGCTGGTGGACGTGTCGTATGGTGGGGAAAACGGTTTTAACCAGGCCATTGAACTGGCGGCCGAATCATTGC
AGAACGTTAAATTCATACAGGAGAAGAAACTCATTGGTCGCTACTTTGATGAAATTTCTCAGGTGAGTTGCCGGATACGAGTTCTGAGGCATTTC
GAAATTAAAAACCACATCCGTATGCTTTCTATATTTAAAAGGATACTGGCAAATACTGTTTTGGAGTGGAGGACACTTTGCGGGCACTGGAACTT
GGCTCTGTAGAGACTCTCATTTGTTGGGAGAACCTGGATATTCAACGTTATGTTCTCAAGAATCATGCCAACTCGACGTCAACGACAGTATTACA
TTTGACGCCCGAGCAGGAAAAGGACAAGTCGCACTTCACTGACAAGGAGGTGAGAGCTAAACTGAGTAATGATACTAATCCGCACGCTAACTGGG
AATTCAATCGTATAGAGCGGGGTAGAAATGGAGCTGATTGAGTCTCAGCCGCTGCTGGAATGGCTGGCAAACAACTACAAAATGTTCGGCGCCAC
ACTGGAGATTATCACGGATAAGTCCCAGGAAGGAAGTCAGTTCGTGCGAGGTTTCGGTGGAATCGGCGGTAAGTTTGAGCGGCCAAACAGCACGG
CTGGCTAGTTGTAGATTGGTTATGTACTAAACAAATGCTGCAACTATATCCATTCCTCTTCCCTCATGCTGCTTTCACACGGTCGTCAACGCTAT
AATGTAAATGTTAATTTGCAAACTGGTACCTCAATTCGATATGTAGGCATTTTGCGCTATAAAGTAGATTTCCAATCCCTACAGGCCGATGAGCC
GCTGGAGGATGTCGATCTCGATGACTATTAAGCCTGTTAAGGGTGGCTGCGAATGGGTCTCGATTATGCGTTACATACATAATAAACCAGTACT
TTTTGGGAAACCTCGTAAAGCAAAACGTTCAAATTGATTAGGAACCAATTTACTTGCCACATAGTTTTACCTATGTTCAGCGTAGCCGTTCAATA
TTTATCACCAATAGGGTCCCTCTCATCAGTCGGATGGTGCATTCCCTTGTCGATCAGATCAGCGTGCATCTAGATATGTACCTATACGTTTTACC
AAATTTTTTAATTAGTCGTGCACCAGGCGGAATCGCGTACTTTTAAGCAGCATATTAAATTCGTATTTCGTACTCGTAATTCGTAATTTGTATTT
CAATGGTCATGTAAAAGCGATGCGATAGATATTAGCGCATTCTCCGTTCATCTGGTTCGATTTCGACTGCGGTATTAGGAGCAAAAGATCTTCGG
TTAACTGCCACATGCCACTTTCGAACGTATCTGCATTTCCCCTATTCAAATTATAGCCGAGTGTTATAAGAAAGTATACAAATCTAATCCATAAA
ATTGTAATAAAAATTAAACCAGAATAAAAACACCACACAATGAGGATGGGGTATCCGTTTATATTCAGTCGCGAAGTACAACAAATATTTTATTT
AGTGTATGAAAAGTTAAATGTGGATACAAAGGAGGTGAGAATCTGAGTTTCGGTTGAACTATCCTGTGTGTTGATCCTTTTGTTTTTTCCTCTTC
ATTTATTTTTCAATTTTCAATCAGCTTCTGTTCTTCTATTTTTTTTTTTTTTTTTGTTTCTTATTTTAATTTAATTCAATTGCTGGGTGTGCCTCT
GCAGGTATCTTACGCTACAAGGTGGATTTCCAGAGTATGCAGCTCGATGAATTGGACAATGATGGCTTCGATCTAGATGATTACTAGGAAATGTA
TCTGTAGAAATGAATTTGCCACTACGTTCGACCGCAAACTGAACTGCAACTACAACTATATGAATCCAGGAAATCAAATAGAATATTTAAATAAT
ATGAGAAAACACAAACCTTCTTCCATTTTTACGTTGTTGGCGAAAAAAGTAAAATTTTAAATAATGCATATAGATACAAACGATAAAATGTTAAA
TCGAGGAAAACATATTAAAATGCAACCGTTTTACGTGAACAAATTTGCAATTTGAATATATTTTCGAGGGACTAGAGCTCTTGTTATATAATTAA
TTGTTCCTCTATAAATCTAAATCTAAATCTACATTGACAATACGCCACGTTTCCTAAAGTTTTTGGGTACAAGGAGAATTGTATCTGTGAGTTTT
AATCGTTCTATTATAGCTTGAAAACGAAATTTGCACCGAAAGCTGATAAAATTCCGACTCTGCTATCTGCTGGATAAGTAAAATGCTGGTAGCCA
CTTGGAGTACTACCAGTACAGCAATGAAAGTAAAGTGAAATGGGCATTTCATTTTCTACTTTCTATTTGCAGGCACACTGGAAACAGTTTACTGC
GAGATTCCCACTTCATTAGTTGGCAATGCACGTGGACGACAGCAAAAAGCACTCGTAGTACTTGTTTCGCCCTTGATTTGCATCTAAGAATCGCT
CAGATACATCTGGTGAGCTGAAACTCGTTTCTGAGCCGCAGTGTCGTGCAGGTATCCGTACTCGTTTGAATATTTGTAAGTAATCATTGCAGCGA
GACTTCCAAAAAGTAAGCTCAGCTAAGTTCTGCGGTGTTGGGCATCCAATTAGTTGACCAAGTTTTCTGGTGGCATGCACATGAAACTTGTTTAA
TCGATAGGGTAAATATGCAAATTTCGATTGAATTTGACGATAATGCGTCGAGATGAAAAGAAAACGAATTGTGCAGGATTTTGGTTACGAGATAA
GCCGAATCAGCTAATAAGGCACGTGCTTAATTGATATATATTGTATGTTTAAGTAACCTAAATATGCACGACTTTAATATCACTTTTATTTCGCT
TTCGTAATAAAACGAGGTTCACTCTAAAGAGCACAAGCGTGGAGGTGTATGTGTGTTCTTACAGCCCCGATCATTTGTATTTCCATTTGAGTGCG
AGCGAAGACGAGGGTTTACAACTTGATGAGAATTTGATCAAGATAACATTAAAACACAATCTGCTGCAGTCGGACGGGGCACTTCTGATT
(SEQ ID NO: 1177)

Exon: 1001..1034
Exon: 1555..1819
Exon: 2918..3093

Exon: 3172..3641
Exon: 3707..3862
Exon: 3937..4134
Exon: 4196..4343
Exon: 4512..4589
Exon: 5420..5740
Start ATG: 1734

Transcript No. : CT36935
ATGAGAAAAATTTATGCAGATGTATTCGCCAATTTGTATTCATCGCCAGCCACGTTAAAAGGAAGAACGTGTATGTGAATACGACCATCAGAGGA
TCTTAGCGAAGGATTCAGGAGCCCAAATTCTTAATCCCCATCCCACACACACACATATACTCGCACGTAGGCACGCTCTCTGTGAGAGGAAGGGT
AAATAAAAGAAGCAACGAGCAAAATGTCTGGCGAGGAAACGTCTGCCGATCGCAATGTCGAGATCTGGAAAATCAAGAAGCTCATCAAGAGCCTG
GAAATGGCCCGCGGCAATGGAACCAGCATGATTTCTTTGATTATTCCGCCAAAGGATCAAATCTCGCGCGTCAGCAAGATGTTGGCCGATGAGTT
TGGAACGGCGTCGAACATCAAGTCGCGTGTAAATCGGTTGTCCGTCCTCGGTGCCATTACGTCGGTACAGCACAGACTCAAATTATACACCAAAG
TGCCTCCCAACGGTTTGGTCATCTACTGCGGCACAATAGTCACAGAGGAGGGCAAGGAGAAGAAGGTGAACATAGACTTTGAGCCATTCAAGCCC
ATAAACACGTCGCTCTACCTCTGCGACAACAAGTTCCACACGGAGGCCCTCACTGCCCTGCTCGCCGACGACAACAAATTTGGATTCATCGTGAT
GGATGGTAACGGAGCGCTATTCGGTACCCTTCAGGGCAACACGCGCGAGGTGCTCCACAAGTTCACCGTCGATCTGCCGAAGAAGCACGGTCGTG
GTGGTCAGTCCGCCCTTCGTTTCGCCCGTCTGCGTATGGAGAAGCGCCACAACTACGTGCGGAAGGTCGCCGAGGTGGCCACCCAGCTCTTCATC
ACGAACGACAAGCCCAACATTGCCGGACTCATCCTGGCTGGTAGTGCGGATTTCAAGACTGAGCTTAGTCAGTCTGATATGTTCGATCCTCGTTT
GCAATCAAAAGTCATCAAGCTGGTGGACGTGTCGTATGGTGGGGAAAACGGTTTTAACCAGGCCATTGAACTGGCGGCCGAATCATTGCAGAACG
TTAAATTCATACAGGAGAAGAAACTCATTGGTCGCTACTTTGATGAAATTTCTCAGGATACTGGCAAATACTGTTTTGGAGTGGAGGACACTTTG
CGGGCACTGGAACTTGGCTCTGTAGAGACTCTCATTTGTTGGGAGAACCTGGATATTCAACGTTATGTTCTCAAGAATCATGCCAACTCGACGTC
AACGACAGTATTACATTTGACGCCCGAGCAGGAAAAGGACAAGTCGCACTTCACTGACAAGGAGAGCGGGGTAGAAATGGAGCTGATTGAGTCTC
AGCCGCTGCTGGAATGGCTGGCAAACAACTACAAAATGTTCGGCGCCACACTGGAGATTATCACGGATAAGTCCCAGGAAGGAAGTCAGTTCGTG
CGAGGTTTCGGTGGAATCGGCGGCATTTTGCGCTATAAAGTAGATTTCCAATCCCTACAGGCCGATGAGCCGCTGGAGGATGTCGATCTCGATGA
CTATTGTATCTTACGCTACAAGGTGGATTTCCAGAGTATGCAGCTCGATGAATTGGACAATGATGGCTTCGATCTAGATGATTACTAGGAAATGT
ATCTGTAGAAATGAATTTGCCACTACGTTCGACCGCAAACTGAACTGCAACTACAACTATATGAATCCAGGAAATCAAATAGAATATTTAAATAA
TATGAGAAAACACAAACCTTCTTCCATTTTTACGTTGTTGGCGAAAAAAGTAAAATTTTAAATAATGCATATAGATACAAACGATAAAATGTTAA
ATCGAGGAAAACATATTAAAATGCAACCGTTTTACGTGAAC
(SEQ ID NO: 1178)

Start ATG: 214

MSGEETSADRNVEIWKIKKLIKSLEMARGNGTSMISLIIPPKDQISRVSKMLADEFGTASNIKSRVNRLSVLGAITSVQHRLKLYTKVPPNGLVI
YCGTIVTEEGKEKKVNIDFEPFKPINTSLYLCDNKFHTEALTALLADDNKFGFIVMDGNGALFGTLQGNTREVLHKFTVDLPKKHGRGGQSALRF
ARLRMEKRHNYVRKVAEVATQLFITNDKPNIAGLILAGSADFKTELSQSDMFDPRLQSKVIKLVDVSYGGENGFNQAIELAAESLQNVKFIQEKK
LIGRYFDEISQDTGKYCFGVEDTLRALELGSVETLICWENLDIQRYVLKNHANSTSTTVLHLTPEQEKDKSHFTDKESGVEMELIESQPLLEWLA
NNYKMFGATLEIITDKSQEGSQFVRGFGGIGGILRYKVDFQSLQADEPLEDVDLDDYCILRYKVDFQSMQLDELDNDGFDLDDY*
(SEQ ID NO: 1179)

Celera Sequence No. : 142000013384822
TTCCCAATTCCTTCGAGGTGATGGCACCTTCGTTATCCTTATCCAATAAGCTATAGATATTCTTGAGCAGGTCCTGCTCTTCAACAGACAATTCA
TCCATTATGCTTTATATTATGGGAAGGAGAATATTATTATTATGCTAGTAGATATACTTTTTCGATAGGATTGATACTCAGTTGAGGTCTGATAA
GCTTTGAAGGAGTTCTACGATTGAAAATTGTTATTCAAAACATTCAATATAAATATTTTTGAAAAAAGCCAACTAAGAGTTAGCCTTCGGTCTTT
AACAGATATTAAACAATCTGCGTGCTCCATGAAGTTCATAAACTTTTACTGAAGATAAAGGCATTAAAAGAGCATTCTCACGCACAGTTTGGCAA
ACAAATCACGTGCTTTCCTGGACCCAAATGATATCATCTGGCGGAGAAACTCTTTGGCTTTACGCGTATTATTTTATAGTTGAACCAGAAATTGA
TGTCATCGGTGGCGGTAAAAAATGGGCGCCCAATCCGCCCAATGAGGAAATTCCAGGAAGCCGGGCAACTCCAACTGTCGGTGATGACAATTTGC
GTGGCATTTTAATTGAACTTTCTACGTGTTCGAGTGGTGTACTTTGATTTGATCCCCATCCACCGATTTTTCGTCGATTTGAGTCAATGTTAAAG
GCGTTGCCACAAACCGCAAACTGTCGTGTCTAGGAGGTTGGGGAGGGGCTTGGTGGCTGGGGCCTCGAAACGTGCCTGAAGTATTATTACCGCCG
TCTGTGATTGATGGCCTCATGCGAGTGAGTCAGTGGATTTTTATAACTCTACGCAGATCCCTTCCTTTCAATCAAGCGGCAAAAAATCTGGACAT
CGATCTCGCCGATATTAGCTAACTTCATTTCAACTTAACTGCCCGGAGTGCTTTGAATAAAGTGGATTTGAGGCGATGCCTTGGGATTCTTGGCC
AGATTAAGTCGATTTTTTTTTTTTACTTCAATGAAAAAAATGGCACGCAATTGTTTTTCATTATTAATGCATACTTTATTTGAAATCAACTAACT
CGCTATGGTTTGAATAAAATCATTTAAAATTGAAGGAAGACCATGGAATTCTATGGGTTGCTTATATTAACTACTGCAAAACTCTTAAAATTTAA
GCCTAATTACATAAGGTTCTACTGGAATGTTGCTTGTAGTTGGATTTTTGTTTATGCTCTGCTTTACACTAACTTTTACTTTCAACCATTTTTTT
CCCTACAGCAAAATCGATTAACGATTTTGTTTACTCATTAAGATTAGCTTACCGGATAAGGAAACATAAATAAAAAATTGGAATTCACTCAGCAA
ACAGCAACACTTAGTGTTGGGCCACACATTAAAAACTAATCGATAGACTCTCGTACTAAAGGCTTAAACATTTAAATCGGTAGATTTAAGCTAAA
ATCCTAACGCATAAGAGCTCTATAAAATGCAACAACGGAGTTTGTTTCGCTTACAATTATCGCTTAACTGATTTTATTACTTAGTTTAGGTCTAT
TGCCTTGCCTAGACATTGTACTAAAAAGTATTAAATTGTAGATCTAAATTTATTTTAATGTACTTGTGGGTCTAAAACGATAAATCCTCGTTTAA
CCATTGGGAACAATAACTGTTTGTCATTATGATATTCAACTGTTCATAAGACCTTCTAAATGAAATACCAGAAAAAACAACCGAGATATATATTT
ATTAGGAATACTACTACTTTTTGATATTTCAAATTCGTAAGAGCTTTGATAAATAGTTTTCCAAATTGTGTTGTTTTTCTATTCCGATTTTACCT
CCATTAATGGATTGTTTTCTAGTTCTTTCTCGGTTTACTTCTAACGCCTCATTATGTCCTCAATGCTGAACCCTGTTCTTCTCGGTGGTGCAGGC
GGTGGTGCTATGGGCGGTGCTGCCACTGGTGGTCCCTTTTCGGTGGTGGCTCCACTTGTTTCCGTACTCGGTGGTTTTCCCAGAAGCTGTCTGGG
GGGATGTCGCGACATATTCAAAGCATATATGCTGGGACTATCCACAAAGGTCCTTTGACCCAATCCAGGATGGTGGTGCGGATCCATCAAGTCCA
AGGTCGGTGCCGGAAGAATCCTCTTTCGCATGGGTATCGATCCCAGGAAGCTGGGCATAGCTTCATGCGGTGAATGCAAAGGTTGATTGGGTGGT
TTACCCGACTCCGGCTGGGTTATTATAGTGGGTGGTGTATGTGGTGGCGGTGGAACACCAGCCTTCGAAAGGTTCAAGCTCTTGTGGTGCAAGTC
GCGTCGAACGTGCAGAATGGGCAAATAGGGATCCCCGTTGGGTGGGAGTAAGTGTGGATGTCCTGGGTGCTGGTGGGTTGGCGGAGGAGCTCCAG
GTGGTGCAGGCGGCGGTCCAGCTGCCCCAGGTGGTACAGAATATCGCACAAAGGAAGGTGGAACGGTAGGCTGGCAATGCCAGAGTTCCCGGGT
TCCTCCTGATGTTTCTCGCCATGTGGCCGCATTGTGTAGGTTTCACCACCCTCATGATGACAGTGGGTGACTCCCTGGCGTTCCGGCTTGGTGCC
CACTGACGACGATGATTGCGATGTGGCGGCAGCCTTACTCGCCTGGAAACGCGCCACTAGTGCCACTTCTGCCTGCTCCTCGTCCTCGGGATCAA AGTCGTCGTCCTCTTCCCTGGGCAAATCGTGTACTCTTGGCAGATCCTGCAGTTCCTCTTCCTCGTCGAAGTCATCGAACTCCTCTTCGCTTTCC
TCATGATCGATGGCTGCCTTGCGCTTGAGTCTCATTCTTTCGGACTCAGATTTCTCACCCGATCCTCCAGACTCGCCCAAATTGTGAACTGGCGA
CTGGCGAGGCGAGTCCACTTCCAGCAACGAATCCTCCTCGTCGCCACTTAAATTTCTGGCCTCATCCTCTTCGCCCACATCCACATAGTCCCCGG
AGTTGACCTCACCCACTGCATGGGTCAAGGCATGGCGTCGTAGATCGCAGTTACGGCGGAAAACTTTGCCGCATGAAGAGCACTCGTAGGGCTTG
TGATCCGTGTGGGTGAGCAGATGGGTCTTCAGGTTGGAGCGCTGATTGAATGATCGACTGCAGACGGGGCACTTGTGGGGTGATTCCTCCATGTG
CAGGATCTTGTGGACAGCCAAGGTTCTCGATTGGCAGAATCCCTTGCCGCATTCCGTGCATTTGAAGGGTTTCTCCTTGGAGTGAATATACCTGG
GCGAATACAAGTGGAGAAACAATTAGACTTTATTGTTATAGCGTGGGCGTTTTCCTGGTAGCTGCAATTGGTAGCCCAGGTTGACAGTTATCTCT
GCTCAAATGCAGCCTTAACTTGAACCGATAAAGCTCACTGATATACAGCTTTACAATACTCTAACTAAGGATATAACTGGCTAGAGCAGACAATA
GAATAAATAATATAATACTATAGCATATAATACCTATCTTTCTCTTTCAAAATGAAACCTAACCTGGATTTGTTTTAACCTTAAACCCAATTCTT
TAAAGTTTTTCATTAAAGAAATCCTATGATTTTGTATCCTCTTAACTGATAGGGTATTTAACTTTCGTGTATGCGATCTGGCTGCATTAATTTTT
TATGTTTATGGCGGCCATCTTGGCAATGGCGTCCACTTGCTGTTGGATAGCAGCAGCCACAGTTAAAAGTTAAAGTCCCCATCTTCGACGGAGCC
ACAGATTCAGCATCGCATCGGAGGCAGCAGCTGCTGGTGGAAAAAAAAAAAATAAATGTATAAAAACCCAAAACAGGTTCTGCCTCCGAAGCACCG
AGATTCTTCTCCCATGCTCCGTGCGTTTCTGGTAAAAAAAAAATACAAAAAACTTAAGAAGAATTAGCCCCGCGGCAAAGCAAACAAACGACAAA
TGGACCGATACCGAACGATCAAAAGACAGAACGCTCGGACAGGCCGACACATTGAAGCCGGGATGCTGGACCTGCTGCCTGGCATCGGCATGGGC
ATCGGCACCGGGATACACAGACCCGATATATAGCCCCCAACCCCTTGGCCATCCCTCAATTTTAATGCTGGTGGAGGAGCCCCAAAGGAAAACCA
ACAGAGTTAATTAACTTTGTGTTGTACTCTGCGGCCGAGTTGAAGTTTTACTGGCCGTCAGAGGAGCTCTGATTTTGGGTCCGCTTTATGGGGAC
TTACTTATTTGAGTTGAGGTAGGAAAATTCGTCGTAAAGTTTAAACATTTCCTGGAAAATTCCTTATGGTAAAAGGGGTCTTTTGAAGCGATTGT
CTGATATATCTAAAATCAATAAAACTCCATCTACGAGTAGTGGTCGCCTTTCCCTTTTGGCCGAGATTACTGTCACACCTGTTCAGAATGTGTGT
ATAAACTGCCTAGTAAGCAATAAATTACATTGATCTAATTATCCTTTGCCTTTACAGGGTATTCCATTATTCGCCATTCGTTCACACTTTGAGCA
CAAAGAATAACTCCAGGCCTGATGGCAATTACCCGAGCAGACACTGCCCCCTTTTGTGATTACTTGTACCCCAACCTCGACTCACCTGTGATCCC
TCAGGTGATCCTGTCGCCGGAACGCCTTGCCGCAGATATCACAGGAATAGGGCCGCTCGTCCGTGTGTGTCCTCTCGTGGATGAGCAGATTGTAC
GACTTGGTGAATTGTCGATTGCAGAACTTGCAGATGAACTGTTTTTAGGCCGCGATGCCCGACCAGGAGCACGTAGCAGGCGCCTATCGAGTCC
GGCATGCATTCCAGGACCCAGGCCAGGTGGAAATAGAGCTGCGGCGGCGGCTCCTGGTGGAAATGGAAAACTTCCGGCTCCCGTGGGCGATGGAC
CCGGTCCGGTGAGATATGGCGGAGGTGGCACGCCAGCTGGTCCGTACAACACTCCAGGCGGTGGCACACCAGGACCGCCGGGTCCTCCAGGACCT
CGTCCTAACATTGCCGCCGCCGCAGCCCGCCTCCCTTAGGGCCAACTCCTTTCGCTTGTCCGCCCATCATGGCAATGATTTCGTAATTGGAATTACT
ACCCGGGCGCACCTTTCCGGTGGGCAGAACCGGCACAAAGGCAGAGATCTCGCGATGATGCGATGGTGGTGGCGGTGGCGGCGGACCATGCAGTC
CGGCCAAATGCTGCTGATAGGCCAGCTGTGTTTCATACGCTGAGATCCGGCTGGCCGATGAGTTGCGCGAATCGCCGTTGCCATTCTGGGAGCCA
CCATCCGATCCTCCGGATCCGCCGTTCCTATCCGCCGCACCAGGAAGACCGCCACCACCCACCGCCGCCGCTGCCGCCGCCATCGAGTTCATGAA
CTGATCCATCCGGGAAGGTCGCAGCATGGGTATCGCACCGCCTCCTCCGCCGGAGATCTCGCTGGATGAGCTTTCCGTGGGCATTATATTGGAGG
GGCTCTTCACATTCCGTTGGAACTGCCGGAGATAGGGATAGAACAGAAAAAGCCGAAAATAAAATAAGGGTAGTGGTAAATAACAATTAGTACAC
GATTGTGCTGGGTTAATTGGGCTCTCGTTTTTTTTTCGAGGCTTATCTTAATTGCGAACCGAGTGCAATAAACAGATATTTCCACGTTGTATTCT
TTATTGCTCCTAGGGTAGTACTGGGTATGATAAAAACTGACGCAAACTGGTTTAAAATAGATATATTACTATTAACTTAGTTTCTTCTTGGTGGG
AAGTTTCCTTGTAATTGAAATATTCATGATCTTGGTTTGGCAAGGCACAGGAATATATACAATATATACTATAGAATATTTACTCTTTTTATCTC
AACCGGTTGTAACTCACTTTTTAGATGTGAAATTCTTCAAATTTGCTTTTTGCACTTCTTATCACAAAATTAAACAGCTTTATGGGCAATTAACT
TGCAAATAGCCAAGGATTATCACATTAGCTGATCTTTCAGAATTTATCCACGTGAACGTGATTTAGTAGTCACAAAAAAAAAAATAATGAAGAAA
ATATTTTTCTCGAAAATAACCCATACGATTCTGAGAACGTTTTGGTATCACAGTACGTATATTTTCACAGGGTAACTAAGCAGTTTATCACATTA
TGGCCCTCGTCTATGGGTTTGTTGCTGTGTTTTTTCCATAGGAATTTTATTATTATTGTTGGTTTATTATTATCAGCGGCGGACTGCCGACGACG
GCGAGTGAAACTAAACTGAAAACGAGTCGCAGTTTGGCACCGCGATCGGTTGCTTCCAGTGCGCAGGTTAGATAAGATTGTGCGTCTAAAAAAAC
CTGCCTCCGAACCTCTGAGACTGAGTAAGCAGCACAGTAGTAACGATATAAACACACACACACACACAGTTATATTATATATGTGCCTGTGAT
ATATGGCATATCGGCAGATACCCCGGCACACTCAGATACAGATACAAAGATACAGATACAGAGGCAGGCAGCCAAGTTGCCGTCGGTTTTGGTAA
ATGACTCGAACCGAACTCGACCGACTGCTTACTGGATTTACGCAACAGGAGCCTCGACTTCTGAGTGCCTCGAAAGAAGAAGGGGCAGAGGCAGG
GGCAGGGGCAGGGGATCGGGTCCCGGAACGTGATCATCACGATAATAACAAAATAATGCACATAATAATGATCACAATGATGGCCGGACCATAAA
GTTTGTGGCCCCATATTGCAAACGCTTCTGGCTGCCATCTTCCCAACGCCTTGCACAGCAAAAAAAATGGCACCAATTTTGTACCCAATTCTATG
GAATTCTATTTTAAGATCTATCTTTTACGATAAGATTATATTTGTTATAATATTAAAGAATTTATAGTAATATGCTTTAAAATTTGTGGCTCGCA
AAGAGTGCGCCCCAGAGAGCAAAGTTTCCTCAGTAAGTCAACCTTTTTTTTCGGTGTACTATCCTCATTTAAATGTACAACCAGTTGAAAAAAAA
AATGCTTTAAAAATAACCCAGCTGTCGGTGCAATGACAGTTTTGCTTATCATTTTGCTAGAATCGTTCTCGCTGTCTCGGTTGATTTTAATGCAA
AATGCTGCAACGTCATTAAGACCAACATTAACATTCGGCTAACAACAAGTGAAGTGATCGTCATAGTTGGTTAAAAATGAGCTTAGCCAAGTTTT
TTGGAGAGGCGCCCATTGTTGAAGTTACCGTTCTTTCCGTACGGATGACTAGTCATTGTGGTGGTCTCTTATCTATGGAAATTATTTTGGCATTG
TCTGGCTGGAGAGTGCGCTGTCAGATTAGCTCTATAAAGTAGCTGAAATCATGACTTGATCATGAGTGTATCATTGTTATGGGGGAATGACTCTA
CGGACCACGTATAGTTCAAGTGGATGAGATATAAGCAGGTCCCAATTATTAATTCAAATAGCTGTTAGATGTGGGTAGGTCTTATCGTGCTATCA
TATCAGCGAGTCTTTAGTAGACAACGGAGCACGCAGTTAAGATATTAGGCAAATAGATGATCTAATTGTAATATTTACACTAGAAATGCTTACGA
AAGCCATATCGAAGCGTTTTTGTTTCCCTAATACGACTAGCACATGCCAAACTAATCTCCACGTTTATTAGATAGTAATTGGATAATTCTTTCAG
TTCAATACCTTTTAACTCTCACCCATGCGAGTTCTCGTGCCCTCACTGATAATCTGTCGCAGTCTATCTATATTCGATTCAATAAAGAACTTATC
TGATCTAATAAGTCCCCCAACTTAGGGAACCTTTGCTGTAGATGAGCGATGGCCCCGCCATGCCTCATTCGATTACGATCCCGATAATCCCATTC
CAATTTGGGCTCACGTATTTCTGGTAGCCTCGAAAAAAAAAAAAAAACTGAAGTGTAACCCGTTTTGGGTATTTATATATATTTTTTTCGATTTCA
GTACTTTTTCTAGGGATTGTTTCCACACTTTTGCATTTACGACCGCTTTGGACCCACGTTTCACCCCATACCCTGTGCACATACAATGTACAATT
CAGCGTTCATTATCTTTTTTGAAACATCGGCACTTTTGAAAACGTCAAGCCAAATAAGAAAAACAAATAAAATTCATGTAAATAATGGACATCAT
CAGCAAAAGCGACGGCACGTAGACTGCCGTAGAAATATTGAGAGAGAGTTGTGCGCACAGATACAGATACAGATGCGGAGATACAAAGATACTCG
TACTCAAAGATCCACAGATACGTTTGCGCAAACGGTTGCCCAGTAAATGAAGCCAAAGGCTTAAAGTTTCCAATATGTGTGCGTCTGAAGGTGCA
CTGGAAAAATTATTGTGCACTCTTGTGAATTATTTAATATTAAAAAAAAGAGTATATCAAATAATTCTGAATATATAGGGAAATGAACAAAAAAT
AATTAGTACGTACTTTTTTATGTAATATTGAAATGTGCATATTTAATTAGAGAGGTAATATTAATATCTTTTCTTTCTCTGTATCGTACATATAA
TAAAAAGAGCCAGAAGACCAACTACTGCTGGGAGGAAAATAAAAGATATCGAGGAGCAATTTGGCTGCCACTTTTTTCCCTCCTCTTCTTTTTGA
GCCGTCTTGCTTCTTTTCCTTGGATTTCTGGGTCCGGGATCGGTTCGTTTGCTGGGTTTTTGTGTGTAAACAACTGAGGCCAGCAGAAACCCAGG
GCCCAGCAGAGTGAAAAGGTTTTAGTTGATAAAAAAAAAAAACAGAAAAATATACAAACACACACAGACACACACTGAGCAAACGGATTTAGTAT
TTGTATAGAAAACGCAGAGAGCTGAGGAGGCGAGTTTGTCCCTCTGATGATGGCCTACGATGGCTGGAAATGTCCATGCGTCTTACTGCCCAGTG
ATTATGTATTGAAAGGGGTATATCAGGATTTCCCGACCAAGCCATTATATAACCTTTAATATCTTAGAAGGATCTGTGTATTTACAGAAAACAGA
ATGTTGCTCAATGACAAGAAAAAAATAATTTTGAATTAAATTATCATTTAACGTTATATGAATCAGTAAGATCAATCCCATGTTACCTACTAACC
GGAGCTCAACTATTTTAAAGGTTCTTAGCAATGGTTTTTGAAATAGGGACCGTTAGCTAGAAATACCTACCACAATTTTAAGGCCGAGGTACACC
CGCGGTCTATCAGTAAACCTTTTATTTCGGACCTTATCTTCTGGGCCGAGTGCTTACCGGGCCCCCATATGCACTTCAGTTTGCTTACAAAACAC
CGGCCAACAACAACAAACAAGCCAGAAGATGACGACGAAGAAAAGTGGAGTGGTGGGAGGAGTTCCCCGGAGGAGGAGAATGGGTATGGGTATGG
GTATGGGTATTACGGGTGAAGGAATGGAAAAAGGGTCGCCGAGATCCGCTGTGCAGTGCGGAATGCTCTTGGCCAGGCTGTGTGTTTTAATCCCT TCGGGATACTTTTTCTTCCACCGAGTGTGCATATGTTTGTGTGAAGGTAGCTAATAATCAAGACAGCGATGGAGAGGAGGAAAAACCGACGCAGA
CTTATAATTATAGTCGAAGAGGAGAACCAAAGAGACCTGCACTTCACATGCGTTAATCTGAAAACCCTTTCGGGCCCAAGCAGCATCTGAGATTA
TAGTCAAAGCTATTAAAAATCTAGCATAATCATTGCCCTCGGTGGAAAGCAAGTTGCGTTGTTGTTTTTCTCTTTTTTTTTTTTTTTTGCTCCCG
AGGTAGGCAGGCGATCTTCCTGCGCAGCCTTGTCTATAATTTTCTTGATTAATATCCATGAGATTTACACATTTGGAGTGCTGGCCAGAACCCTG
CACCTCAACCCTCCGCCACCCCCCGCGTTCCTGTGTGTGCTGGCCATTAATTTAAAAAGCTTTGCTAATTTCGCGGGGAAATCTGGAAACGAACA
ACTGCTAATGAAGTTTTATGGGTTCGGGAATGCAGCTGCAGCAGGATTGATAATGTCGTTAGCATAAATTGAAAATGCTTTCAAGTTACGACCAA
AGATTTGTTATGATTAAAGTATGGAGCACGCGGAGTGAGCAAGAATATCCACCAATGGATTTTTATTAAATGATAAATGGCGAGCTGCAGATAAC
CAGATTCCTCTGGTTGCTGAAATAAATATTTTTTTTTGAATTGAAACCTTCTTAGGATTAACTGAAGTTCAGACAGTTAGTTCCTAAAATTGAAT
TATTTCGGCTTAACTTTGACTCTTTCTAATCCCTCTTGAAGTAATCCACTTTGAATGCTAAGCCGATCTTCGTATAAATTCTATTGTCATATTGT
GCTGCTCCTTTCATTCGAACTAAATCCATTCAAAAATTTCACCCTTGAATAGAACTCTTAAGATCTTTTGTTGGTCGGATTGCTACTTTTTCAGG
CAATCTATTGTGTTATAATTTCAATGGGTCAATTCTTATTTATTGGAAGAGTTTATGCTAATAAGTGTAGAAGCACTAAGACTATGATTTATTAA
TTCAAATGCAATTGGATTATGCTAATTGCACACAAATCTTGGTACAAATTATTTATATATTTTTTTCTTCGACAACTTTTGGAACCCAGCCCAAA
ACTAAACATGTAAACTGATAATCACCTTTCCGCTGTCTGATTTCATTGATAGCATTAAAAATTCATATTCCCTAGACAACATCTAATTTCCCCAT
CAAAATTGATGAGTTCCCGTTCCAGAACAACAATAAATGAACTGGTCTATCAGGTGAATTATACACACGTGCCAAAACGAGGCGTGTCCATATAG
CCATTTCAATTTAAAACCCGAATATGGCGATCCCTAACGAGCCATTGTTCTGCGGTTTTATGGTAAATCTAAATTCATCAAGTATTTTGTCACGA
TTTTAATTAATTTCGATTTCAATTTTCCTGCCACAAGGCAATTACCAGCAACATTTTCCCCTGCTGCTGGTGCAACCGAAAAATGATAGTTGGTG
GCCCAAGATGGAGAGGAAAACCCACCCAAAGAGGTAAAGCGTAATAAACTTTTATGGTACTCCCTTTCTTATGCTAAAACTCTTTTTGGACACAA
AACCAAATGGCCCATAAAGCAAGACAATGAATATCCAAAATAGATCTCCACTGAGGCGAAACAAAAGCCAATAACTTTATAGAACCGCAACCAAA
AAATACAAAAAAAAAATAATAATAACTCAGACTGTGAGAGCGCGGGAGGCGTTCTACAAAAAAAAAGCTTAAAAATGAAGGAAAAAGTAAAGCAT
TTAAAAGAAATCAAGAGATGTAGATGACGATGATGATGATGGTCTGAGGTTGAGGCTGAATCCGAATCCGAATCGGTATCTGAACCCAACAGAAG
CTTGCGGCAATTGCGTTTCCTCTTTGGCCACACGTTCTGGACAATTAAAGCCCCAGCCGAGCTCCGAATCTGAATCGAGCCAAGTTAAGACAGCG
ACCACGACCGAAAACCGAAAACAGAAAACCAAAAAAACCGGATTCCAAGCCGAGAAGGAGCGAAAAAGACGGCGAGAGCGACCACTGGCCACTGG
CACTGGCTACAAGTGAACTGGTTTACAAAGAAAAGAAACAGAAATGAAAGAAACATGTGAAAAATCACGATCTATAAAGCCGATGCACTTAATAC
CCTAGGCAAAATAAGTAAATAATACTATAGATCAAACTAGAGTAGACTTGTTGAAAAAAAAACACTGGAATAAATAAGAAGCTTATAAACTATCA
GCTTATTAAACTAAGTTTGCCTAAATTTCGTAAAATATATTTTTAAAACCTAACGCGATGCTTTGAAATTCTGTAAAATTAAAGTTTTTCAGAAA
TGTAACGTTATTAACACCGATTAATATTTTTAAATAATATTTTACAAATTGTGTACACCATTTTCAAACGAAGTACCCTTACCAAGAGCACCCAT
AAGAGACCCCCAGAATTCCAAGCGAAGGTTTTTCGAGTCCGGCTCGAACCGACCAACTCGAACTGAGCGCCACAGCAACAACAATGGGGCAAGCG
GGTGGTTCAGGATGGTGGGGAAGTTTGCGGGGGGATGGGGGACGTACTCCACCGTGGACTGTGCGGCACCACACTGAGTTCAGTGGCAATGACAG
TGGCACATGCAGTTGTAGTGGAAGCCGCTTGTCGGTCGACAGTCCGCCAACCGCCAACGTTGTTGCGCTCTCTTTCCTGTTTTTTCGCCCCGTCT
CATTCTATTTGTGGAGCAGGTTTTGAGATATATCTTGGGTCTTTCTCTCTCTCTCCTTCTCTGTCTGCGTACTCGTTATATTTTTGTACTCGCTG
CCTTTTTGGCCAACGCAAAAAATACCAAAATAAAAAAATAATAAACGTAATTAGCTAGCCCTACGCCACAAACAGAAAACAAAAAAAAAAACAAC
AAAAAATAAAACAAGTAAAAATAAGTGGTGTGGAATTTTTGTGTTCATCTGGGAAGGCAGGGCCTGTTCTCGGCGGAATCTTACCTGTGGGTTAA
ACAGAAGAAAGCCCCAGGCTCTTTGGGCTTTATCTTTGCGTCCTAAAGTATCCAAGTAGTTGTTCAATATGATTTTGCTGGTTTTTTGTCAGTT
TGTAAGCTTTGAAATGCTTGGCATTGTTTTTGGTTTTTAAAGTAGTAATTTATATCATTTAAGTGGCACTTGAATTGTATGTTGTTTTTTCTTGT
TGTATTTGTTTGAAGACTTCTGTTAATACGATTCTGTGAATTTAAAAGTAAATAATTTTATTAAAATTTTCAAAATATTTGTCGGAAATTTTTTG
TTATATTTTCAGGTTTGATTTTAATTTTAACAAGTATTTCACCGAATCATTCTCAAGTAAATGTATTTAAAAAAACACGCACACTAAGGGACAAT
TTTGAGATTCAAATCACGGCACGATCGCCCCAGGGGGTGGGGCTGAGGGGGCGGCAGGGGGGCGGTTACGGGAGCAGCAGCAGCATCAACGGCAG
TCAGCTACCACAAACCACGTAGTTTTTTCCTTCCAAAATCCACGTACAACTCGCGCACAAACACACGATGTATTTGTATCTCACAGATATGAAA
ACCGAACGAAGAAAAACCCGAACCGAAACCTCAACCTCAACGAACTGAAAACCGAACGAGAACGAGAGATACACGGCAGCTGAAATGTGTTTTTC
TACATTTTGTTTGAAATAGGAGCTGAAGCCAGTGCAGCTACCAATTCGCTCCTCAAGTAGTCCCAAACTCTTCCCACACACAGAGTCAGTTGCAG
TTGAAAAGCGCTTTTCTCGAGGCAACTGGCGATGCAACAAGTTCACTCACACACACACACACACTAGCGCTCTGGGCCCGCTCAATAAGATACAT
CGGCGGCGAAAGATACAGATAGATATAGAGCGAGAGGCACTCACAATGCAGTTCACTTTTCCAACAGCTATTACCAGCGATCCGCGCGCAGGTGC
GTTGGCCACGATCAACTCTCGAAGACTGAGCCACGAACCCAAGAAACAGGGCCCGAATGGAAAAAGAGAGAATCGAGAGAATCGCGGGCTGAGAA
ATGCGTAGAAAGAGACAAGCGACGAGTAGCGAGCAGTGGCACTAAAACCAGCTTAGTGCACTGTGGAAAAAGTTTTAACAATTCTTAAATATCTG
AAGAGTAAGGCTCTAATTTTCTGTAAATAACAACAGTATAAATCTATCTGCTTAAATATACTAGATAAATAATGGATGCATTTACATATTTTTCT
GAATTAACTAGTAACTTATATTCAGTTTGAATATAGTACGACATTTCTTTCAGTGGAGGAGAGGAATTAAACCGAACTCAACCCAAACCCAACCG
GCCGCCAGTCGCACGCTGCTAAATGGACGGATGGGCCCGTGGACGGACTTATATGGAGACTGGCACTGGCGGAGCGTGGAACGTGCATTCGTACG
ACGAGTTATTGTCAGTTAGAGCGCTACCTGTTTACCGACCGACTACCGACTACCACCGACTGCTTTTTTTTTTTTGGCCCAGTCGAGAGGGTAGG
GTACAATTGGCCCGGGTGTTGCCAGATTGCCGTTGCTGCTGCTGCCCATGGATCGTTATGGTGGCTTCACCCGAAAAGGAGGAGGAGGGTGTAAC
TCTGGTAGTTCCCTGTTTATTGTTATGCCTTTTTAGTGGGGT
(SEQ ID NO: 1180)

Exon: 13103..12813
Exon: 12668..12435
Exon: 5437..4551
Exon: 3226..1001
Start ATG: 5404 (Reverse strand: CAT)

Transcript No. : CT37221
ACATTTCAGCTGCCGTGTATCTCTCGTTCTCGTTCGGTTTTCAGTTCGTTGAGGTTGAGGTTTCGGTTCGGGTTTTTCTTCGTTCGGTTTTCATA
TCTGTGAGATACAAATACATCGTGTGTTTGTGCGCGAGTTGTACGTGGATTTTGGAAGGAAAAAAACTACGTGGTTTGTGGTAGCTGACTGCCGT
TGATGCTGCTGCTGCTCCCGTAACCGCCCCCCTGCCGCCCCCTCAGCCCCACCCCCTGGGGCGATCGTGCCGTGATTTGAATCTCAAAATTGTCC
CTTAGTAATCGTATTAACAGAAGTCTTCAAACAAATACAACAAGAAAAAACAACATACAATTCAAGTGCCACTTAAATGATATAAATTACTACTT
TAAAAACCAAAAACAATGCCAAGCATTTCAAAGCTTACAAACTGACAAAAAACCAGCAAAATCATATTGAAACAACTACTTGGATACTTTAGGAC
GCAAAGATAAAGCCCAAAGAGCCTGGGGCTTTCTTCTGTTTAACCCACAGTTCCAACGGAATGTGAAGAGCCCCTCCAATATAATGCCCACGGAA
AGCTCATCCAGCGAGATCTCCGGCGGAGGAGGCGGTGCGATACCCATGCTGCGACCTTCCCGGATGGATCAGTTCATGAACTCGATGGCGGCGGC
AGCGGCGGCGGTGGGTGGTGGCGGTCTTCCTGGTGCGGCGGATAGGAACGGCCGGATCCGGAGGATCGGATGGTGGCTCCCAGAATGGCAACGGCG
ATTCGCGCAACTCATCGGCCAGCCAGCCGGATCTCAGCGTATGAAACACAGCTGGCCTATCAGCAGCATTTGGCCGGACTGCATGGTCCGCCGCCACCG
CCACCACCATCGCATCATCGCGAGATCTCTGCCTTTGTGCCGGTTCTGCCCACCGGAAAGGTGCGCCCGGGTAGTAATTCCAATTACGAAATCAT
TGCCATGATGGCGGACAAGCGAAAGGAGTTGGCCCTAAGGGAGGCGGCTGCGGCGGCGGCAATGTTAGGACGAGGTCCTGGAGGACCCGGCGGTC
CTGGTGTGCCACCGCCTGGAGTGTTGTACGGACCAGCTGGCGTGCCACCTCCGCCATATCTCACCGGACCGGGTCCATCGCCCACGGGAGCCGGA AGTTTTCCATTTCCACCAGGAGCCGCCGCCGCAGCTCTATTTCCACCTGGCCTGGGTCCTGGAATGCATGCCGGACTCGATAGGCGCCTGCTACG
TGCTCCTGGTCGGGCATCGCGGCCTAAAAAACAGTTCATCTGCAAGTTCTGCAATCGACAATTCACCAAGTCGTACAATCTGCTCATCCACGAGA
GGACACACACGGACGAGCGGCCCTATTCCTGTGATATCTGCGGCAAGGCGTTCCGGCGACAGGATCACCTGAGGGATCACAGGTATATTCACTCC
AAGGAGAAACCCTTCAAATGCACGGAATGCGGCAAGGGATTCTGCCAATCGAGAACCTTGGCTGTCCACAAGATCCTGCACATGGAGGAATCACC
CCACAAGTGCCCCGTCTGCAGTCGATCATTCAATCAGCGCTCCAACCTGAAGACCCATCTGCTCACCCACACGGATCACAAGCCCTACGAGTGCT
CTTCATGCGGCAAAGTTTTCCGCCGTAACTGCGATCTACGACGCCATGCCTTGACCCATGCAGTGGGTGAGGTCAACTCCGGGGACTATGTGGAT
GTGGGCGAAGAGGATGAGGCCAGAAATTTAAGTGGCGACGAGGAGGATTCGTTGCTGGAAGTGGACTCGCCTCGCCAGTCGCCAGTTCACAATTT
GGGCGAGTCTGGAGGATCGGGTGAGAAATCTGAGTCCGAAAGAATGAGACTCAAGCGCAAGGCAGCCATCGATCATGAGGAAAGCGAAGAGGAGT
TCGATGACTTCGACGAGGAAGAGGAACTGCAGGATCTGCCAAGAGTACACGATTTGCCCAGGGAAGAGGACGACGACTTTGATCCCGAGGACGAG
GAGCAGGCAGAAGTGGCACTAGTGGCGCGTTTCCAGGCGAGTAAGGCTGCCGCCACATCGCAATCATCGTCGTCAGTGGGCACCAAGCCGGAACG
CCAGGGAGTCACCCACTGTCATCATGAGGGTGGTGAAACCTACACAATGCGGCCACATGGCGAGAAACATCAGGAGGAACCCGGGAACTCTGGCA
TTGCCAGCCTACCCGTTCCACCTTCCTTTGTGCGATATTCTGTACCACCTGGGGCAGCTGGACCGCCGCCTGCACCACCTGGAGCTCCTCCGCCA
ACCCACCAGCACCCAGGACATCCACACTTACTCCCACCCAACGGGGATCCCTATTTGCCCATTCTGCACGTTCGACGCGACTTGCACCACAAGAG
CTTGAACCTTTCGAAGGCTGGTGTTCCACCGCCACCACATACACCACCCACTATAATAACCCAGCCGGAGTCGGGTAAACCACCCAATCAACCTT
TGCATTCACCGCATGAAGCTATGCCCAGCTTCCTGGGATCGATACCCATGCGAAAGAGGATTCTTCCGGCACCGACCTTGGACTTGATGGATCCG
CACCACCATCCTGGATTGGGTCAAAGGACCTTTGTGGATAGTCCCAGCATATATGCTTTGAATATGTCGCGACATCCCCCCAGACAGCTTCTGGG
AAAACCACCGAGTACGGAAACAAGTGGAGCCACCACCGAAAAGGGACCACCAGTGGCAGCACCGCCCATAGCACCACCGCCTGCACCACCGAGAA
GAACAGGGTTCAGCATTGAGGACATAATGAGGCGTTAGAAGTAAACCGAGAAAGAACTAGAAAACAATCCATTAATGGAGGTAAAATCGGAATAG
AAAAACAACACAATTTGGAAAACTATTTATCAAAGCTCTTACGAATTTGAAATATCAAAAAGTAGTAGTATTCCTAATAAATATATATCTCGGTT
GTTTTTTCTGGTATTTCATTTAGAAGGTCTTATGAACAGTTGAATATCATAATGACAAACAGTTATTGTTCCCAATGGTTAAACGAGGATTTATC
GTTTTAGACCCACAAGTACATTAAAATAAATTTAGATCTACAATTTAATACTTTTTAGTACAATGTCTAGGCAAGGCAATAGACCTAAACTAAGT
AATAAAATCAGTTAAGCGATAATTGTAAGCGAAACAAACTCCGTTGTTGCATTTTATAGAGCTCTTATGCGTTAGGATTTTAGCTTAAATCTACC
GATTTAAATGTTTAAGCCTTTAGTACGAGAGTCTATCGATTAGTTTTTAATGTGTGGCCCAACACTAAGTGTTGCTGTTTGCTGAGTGAATTCCA
ATTTTTTATTTATGTTTCCTTATCCGGTAAGCTAATCTTAATGAGTAAACAAAATCGTTAATCGATTTTGCTGTAGGGAAAAAAATGGTTGAAAG
TAAAAGTTAGTGTAAAGCAGAGCATAAACAAAAATCCAACTACAAGCAACATTCCAGTAGAACCTTATGTAATTAGGCTTAAATTTTAAGAGTTT
TGCAGTAGTTAATATAAGCAACCCATAGAATTCCATGGTCTTCCTTCAATTTTAAATGATTTTATTCAAACCATAGCGAGTTAGTTGATTTCAAA
TAAAGTATGCATTAATAATGAAAAACAA
(SEQ ID NO: 1181)

Start ATG: 559 (Reverse strand: CAT)

MPTESSSSEISGGGGGAIPMLRPSRMDQFMNSMAAAAAAVGGGGLPGAADRNGGSGGSDGGSQNGNGDSRNSSASRISAYETQLAYQQHLAGLHG
PPPPPPPSHHREISAFVPVLPTGKVRPGSNSNYEIIAMMADKRKELALREAAAAAAMLGRGPGGPGGPGVPPPGVLYGPAGVPPPPYLTGPGPSP
TGAGSFPFPPGAAAAALFPPGLGPGMHAGLDRRLLRAPGRASRPKKQFICKFCNRQFTKSYNLLIHERTHTDERPYSCDICGKAFRRQDHLRDHR
YIHSKEKPFKCTECGKGFCQSRTLAVHKILHMEESPHKCPVCSRSFNQRSNLKTHLLTHTDHKPYECSSCGKVFRRNCDLRRHALTHAVGEVNSG
DYVDVGEEDEARNLSGDEEDSLLEVDSPRQSPVHNLGESGGSGEKSESERMRLKRKAAIDHEESEEEFDDFDEEEELQDLPRVHDLPREEDDDFD
PEDEEQAEVALVARFQASKAAATSQSSSSVGTKPERQGVTHCHHEGGETYTMRPHGEKHQEEPGNSGIASLPVPPSFVRYSVPPGAAGPPPAPPG
APPPTHQHPGHPHLLPPNGDPYLPILHVRRDLHHKSLNLSKAGVPPPPHTPPTIITQPESGKPPNQPLHSPHEAMPSFLGSIPMRKRILPAPTLD
LMDPHHHPGLGQRTFVDSPSIYALNMSRHPPRQLLGKPPSTETSGATTEKGPPVAAPPIAPPPAPPRRTGFSIEDIMRR*
(SEQ ID NO: 1182)

Name: brother of odd with entrails limited
Classification: transcription_factor
Gene Symbol: bowl
FlyBase ID: FBgn0004893

Celera Sequence No. : 142000013384668
GGGCTATCCGGAGTTCGGACGCCTGCTCAATGAAACTGGTCGACCGATGGTATACTCCTGCAGTTGGCCCGCGTATCAGGAGGATGCAGGAGAAA
TGCCCGATTATGAGTCACTCAAGCAGCACTGTAATCTGTGGCGCAACTGGGACGACATCGAAGACTCGCTCGAGTCCCTTATGCAGATCATTGAC
TACTTTGCCAAGAATCAGGACAGGATTCAGCCGCATGGCGGACCAGGACATTGGAACGATCCAGATATGCTGCTGCTGGGAAACTACGGCTTGAG
CTACGATCAAAGCAAGCTGCAGATGGCGATTTGGGCCATTATGGCAGCTCCTCTAATTATGTCCAATGATCTGGCTGCAGTGCGTCCCGAGATCA
AGGCTATACTCCAGAATCGGTTGGTTAAGCTTCGATATCTTATCTTCTTGGACTTATTGGTAAACTTTTGTTATTTGCAGTGCGGTTATTGCTGT
GGACCAGGATGAGCTGGGCATCCAGGGGCGCCGTGTTTTGTCCCGCAACCAAATCGAAGTCTGGAAGCGTCCCATTACGCCAGTAACCAAGAGTG
GACATCACTCCTATGCTGTCGCCTTTGTCAGTCGCCGAGATGATGGCGCTCCCTACAGGATCCCCTTCACGGTCAAGGAGCTCGGATTGACGAAT
CCCAAGGGTTATAATGTGCAGGATCTGTACGATGCCAGCAGCAAGTTGGGCGTCTTCCAGTCTGAGAGTCAGTTCATCACACGCGTCAATCCCAA
TGGTAAAATCCGTTGCAAAACACTAACTAGCCCTGACTTACTTCATTTTCCCCTCCCCCAGGCGTAACTTTCTACAAGTTTACAGCGTTGTAAGC
CCAAGATATGCAAATCAGCCGCTGCCATCAAATCGAATATGCTCTTATATACACACTATTTCCACATTGTCCATTGACGTTGCATCGATGATCTG
TGTAATAAGTTAATTCCGACAATAAATACCAGGTAATCACTGAAGAGTTTGACTTTGTTGATTTTTATTGTTTATTAAACAATTGATTGTGTGCA
TTACACACAGGTATAAGTATTGTACAATTATAGGCATAGATTGCAGTACCGACGCTAGTTAAGACTTGTTCCATGATATAAATAAGGTCTGACTG
GATGAAAGAGTTAATTCGCAAGCTTGTATAAATAAGAAGTGTAGTACTATATACGCGACAAGGACCCGAATAAGAGCAAAAAGGATAGCGACCCC
TCGGGATCATACCAGTTATAAATAGATACCATCTACAGCTACTGCTTACATGGGTTTGGTCGAGAGAGTTAGAGTTATTGTCAAGTTGTAGGCGA
AACCGAAACCAAACCGAAGGAACCATAGCCCGGGGTTAGTGCACCCCATTGCTGATGGTCGGTGTGCGCTCGTAGGTGCGTCTATGCAGCGCATC
CACGTCCTTCAGGTAGTAGGTGCCGGGAAACAGTGCGGAGATGCTGCCCGTTGGCGTGTAGGGCGCCGCATGGTTGTTCTTCTCCCGCACCTCCA
TCAGCGCGGAGAACTGCTCGGGCGCAACCTTCTCCCGTGAATTCAGCAACGGCTGCACGTAGTCCAGCTGCGAGACGAACTTTTCGAAAGCAGCT
GCATCCTGGGTCACGCTGATCGAGTACATGGAAGCAGCCAGTCCGGATCCGTAGGAGAACAAACCAATGCGCTTTCCCACCAGCTCCTGGGCTGG
TCCGCTAATCAACAGAGACACCAAACCGGAGTACACCGAGGGTGTGTACATATTGCCCACTTGGTTGGCCAGCAGCAGCGATTTCTTGGTCTTGC
TGGCAAAGATGTTGGCGGACTGCGTCATGAAGGCCTTCTCCACATCGCGATCAAAGTAGGTGCTCTCCAGGGTAGCGGTATTAAAACGTTCCAGG
TCGGGAAACTGCTTCGTTCGCTCCTCCTCACTGCTCAGCAGGAAATCGTTGAAGCTCAGGCGACCCACAGATTTTTGCACCAACTTGCAGAACGG
TGTGTGGAATAGGATAGCATCGAAGGTGCTCAGGCTGGCCGGCTGCTTGGAAGTATCCTTCTGCTGCTGGTCGAACTTCTTGCGATACAGCCTGT
AGCAGGTGTCCAGAGCAGAAAGGTAGCACTGAATAGAGAGCTTTCCATCTACCGTTGGGTATTCGGAGCTGAGGTCCGGCTTGTAAAAGTCGTAG GCGTGCTCCATGTGCGTTGCGCGTAGTCCACGATCGAGGATAAGCGGCGCATTTGGACCCACCAGCATAGCCACAGCACCCGCACCACCAGTTGG
GCGCGCTGCACCCTTGGCGTACACGGCGATATCAGCACAAACGGCCAAAGCCAGGCGGCCGTCCCAGCTAGAAGATTCCACCCAATTGACGGCAT
TGAAGAGCGCCGCCGTGCCGCCGTAACAGGCGTTCGTGGTGTCGATGCCCTCGATGTCCGTGTTCCCGCTCTCGGCGAACAGCTGCATCAGCACG
GACTTCACCGACTTCGACTTGTCCACAATGGTCTCGGTGCCCACCTCCAGTCGTCCGATCTCCGAGTGCTTCACATGTTGCCGCTCCAGCAGGCG
GCTCACAACCGTCAGGCAGAGAGAGTTGACATCCTCGCGGTCCGAGCAGAAGCCCATCTTGGCCTGGCCCAGGCCAATTGTGTACTTGCCCGCGG
AGGCACCATCGAAGGTCTCCAGCTCCGTTTGGTCCACGTACTGGGAGGGGAAGAGAATCTCGATGGCGCGTATGCCAACGTTCTCGGGCCAGTGG
GATGCCATGATTGTATCCGGTTATCTATTTAATCCTGAGCTCTGTAAGAGAGACAATTTGTATACTTTTAGTGGGAGCTTTGGCATGAGAGTAAA
TATTTAATTCAATATCTTTGTTATTAACAACTATAACAATCACTATTTGCGTTTCGAAATTGCTTCATGATGTTGGGAGCTAAGGCCTTGTTTAA
TTTAATTTAAGCAGAGTTCTCGATGTGGCCCGAATTCCACTGCCAATTGGCATTGGGAAACTTTCTCCCCGCGCAATCACGGCGTATTTATAATG
CTTACAAATTGGACGAGGGCAGAGACAACCTGTTGCACGCTCGAGCTGCGTTGGACGTGTGTAAGCCAGTGACTTTGGCTGCGGCTGAAGAAGTC
ATCAAAGTCTGCCAGCCAGAGGCCCCCGTCTTGGGGGCCAACTGATTTCCCTGGCTGAGAAACTGAGCGTGTAGAGAGAGAGAGAGAGAGGGAGA
GAGAGCCGCCGGAGCGGAGAAAGTTTCCCCCGCTCAGGCGAGCTCCACAAAAGAGAACACTAAACCGCTGTGAAGTAAGCCAAAACACACGCATC
GCAATAAATGTAAGCCAACAAGACAAGCCCAAAGAGCCAAAGGGACAGGGGCGTGGATGCTGTGGCTACACGCAGAGAATTTATGATTACATTTA
TTTACAATAGATAATCATTTCTTTTAAACTTTTTTTGTCAGAGAACAAGCTACAAAAATGATTACTTTAACACAATAACTCTTTTTTCAAAACCG
CTTCCCCTGAAACTTCTCTACATTTTCACACATTTTAATTTCAGTTAGGCGCAAATTATAATTAAATCAAAATGATGATCGAAATATTATGATTT
CCTATCGAAATAGAATGGAATTTTGCTCGGTGGAGCATTGTGGGACAGGCTGGGAGCGTCTTCACCCATAAGTGGGTCATGCCCACCAAGCACTA
AGCACCAACCACCACTCTCCCTCAATCACACGCGTCCATATTGTATAACCGATAAGAGGTGCGAGTGTGGCCCAAACCCGAAAAGCGGTTGACAT
ATTTACCGTTACGTTTAGCACCTGCGACTACTGGCCTATTGACTATAGATTTTCACTTTTCGGCCCGGAACTTTGTGGATTTGTGAAAAAAGGCT
GGGTAGCGCGAAGCTCACTCGATCGGATCTCTCCGCGGACTGACGGCACTGGAGGCGCTGCACTGGCATATGAATATGACCATGACGACGGAATT
GGCAGTGGAGAAGCAGACACCTAGCCAACGAAGCCACCTAGCCACCGAGCAAACACAGAGGCGAGAATAGGCGCTGTAAGTCAATGCCAATTGCT
GAAAGCGCTCGGCGAACAAATAGCGATCGTGCATAATTACGGGAAATATTTATCGCTTAGATACGGCCAGCGAGCACGAAACACAATCGTCGGGG
ACTAAGAAGCCGCCAGACTATATAGATATGCACATCGATAGTCGTGGCCTTTTGCGATGGGGTAAAGATCAAAGGCTGTCCATCGCTGATAAGGC
CGAAACAAAGCGGCTTCCTTAAAAATGCCACCGAATAAGATGTGACACTCTGTCCATTTCAGTGACAAAAACTGGGAAGTGACTTCCAATAGCTT
TTCTCCGATTAATTACTTAAGACGTGCCCTTAGGAATTATTAATAGAAAATTATTTATAATTTGAGTTCTACTAATTTTCCTACTGGTATAACTT
AAATTGGATTATCATCTTTTCTGAACACTATCTTGAAACGTGATTTCAAATCACCTGAACACAATTGGTAATTGATAAAATATTCTACAGAAATC
ACTTAAAGTAAGATAATAACAAGACTACTTTAAGTAGTTGTGATATTACTTGAGTCGTACTTAAGTTAATTAATACAGTTTAGTTAAAGTAAGTA
AAATTAACAAATAAGAGAATACTTTGTCCTATTGTGCAAAAGAGTATGAATCATTATCCAAAGTCATGAAACTCTAATTTCAAGCAATTTAAGTG
ATTTAAGTCATTAATTCCTCGAGTGCCTGCGTGGAATACAGCTCACCCGGTGTTCCTAAGCAGCCCGTGGATTTAAGAATGGAAATTGATGCGCT
GTTTATGCGGAAAAGGAGTCATCGAAGGGAAGGGAACGGGGCACTGTTGTGGTTTTGTGGGCTTATTTTTAGCACTTCGGAATTGGGAAATATTT
GAATAAACATTTCCTGGAACTGCTGCGCACTTGGCTAATTGATTGCTCTTGAGTCATTCTTTTCTTTTTCGGCTGCAGGAGGGTGCGGAGGTGGA
GGAGGAGGAGGAGGAGGAGGTCAAAGGTCGGGATGTTCCCGATAGAAATACACGTGTATTTGAGAGCCGGGAGATAAGCATAGTTTAGGGGTCAG
GATTATGAAACTGATCTATGAGGTGACACATATCACTGGATGTTGATAATTTTTAAATCTACACTATTACACACGGCTGGAAAAACACTGTGAAA
CAGCTTTTCCCAATTTACAATAACCAATTCTAATTGCACACATATTATGTTCCTCCGACTTCTGGTTACATCAGCGCCCAAACTGACCACCTGCC
ACGCCCACAGCCCTCATCCAGCGCAGCACGAACAGTACTCGCACTCGCAATCAACTTACTTGCTAATATTAATGGTCCAGGGCGGGCGATATGTT
TTAAACTAAACTAATCTGGAATAAAATTAAGCAATGAAACTGCGGCACCTTAGCCGCAGGCAGTGTTGGAGAGCGCGCGGCGCTGGAACAGCTGC
TGGCGGAGTCAGCTGTTTGGCTCGCTGGCTAAGCAACACTGGCGCCATCACGTGAATCTCGTGGGCATTGTGAACTGTCACTTTTTTCGCCAGCG
CTTTTCTCACCACACAATTTCGTTCGCATTTGTGGGTGGCGGCGGTCGATTTGCGCTGATTTTTTGGCAAAGAAAAACGCACTTGCTGTTTTCAA
ATAGCACAAAAAGCACACCTGCTTCGTTTACAATCAACCATATTCGCTGAAAAGTAAGTGCCAACCGTAAGAAATAGTTAATTCGGCGGGTTTTC
CACGTCGCCGTGAAAAGTGCAAAAGTTACCCCCCGCCGAAAAAAAAGACCGATTACTACATCGCAGTAGGTCTGCTGACCAGGAAAAGTGCGCAA
ATCTCTTGTAGATTATTGAAGATAGTGAGAAAATTAGTTTTTGCAATGTGGCTATGATTTTTTTGTCGAAGCAGTGTGACCCTGAAAAAAAGAGTT
CGCCAGTTTGTTGCGTTTCGTTCGACGGCAGATTGCCGCGAGGTCTGCGGATGTATCTGGAAATATCCAGCTGATGATCGTGTGGGCTGGGGGCG
GGGAGTCGGGAAAATGTGCGAAAAGTGTTTTGGTTTTTGTGCTTAAATGAAAAACCCGTGAGCAGCGGAAAATTATCGATCGAAAAACTGTCATG
TGACTGTCAACGAACAGCTGACATTGCGAGAGCAACTCACCACAGCGAGTGGTGAAAAGAGCGCAATAGGCGCTTTGAAAATTGAAAGAGAACAC
AAAATTCTCTTTCGCTCTTTGGGTAAACAAAAAAAGTTGGAAAATGTTGTTTAAAAATTGAAATACTTTTCGGTTATTTTGCCATAAGGCACGTA
TTTCGCTGATTAATAGATCGTGTTGTGCGAAAACAAGCAAATACACTTTGATGCGCTGCACGAGGATTAATAAATAATCGTATTGCGTGCAACAA
GGACCTTGATGAAAACCAAGCACATATTATACATGATATATATACTCTACGAAACTGTAGGC
(SEQ ID NO: 1183)

Exon: 5522..5380
Exon: 2796..1001
Start ATG: 2763 (Reverse strand: CAT)

Transcript No. : CT37345
CTGACTCCGCCAGCAGCTGTTCCAGCGCCGCGCGCTCTCCAACACTGCCTGCGGCTAAGGTGCCGCAGTTTCATTGCTTAATTTTATTCCAGATT
AGTTTAGTTTAAAACATATCGCCCGCCCTGGACCATTAATATTAGCAAAGCTCAGGATTAAATAGATAACCGGATACAATCATGGCATCCCACTG
GCCCGAGAACGTTGGCATACGCGCCATCGAGATTCTCTTCCCCTCCCAGTACGTGGACCAAACGGAGCTGGAGACCTTCGATGGTGCCTCCGCGG
GCAAGTACACAATTGGCCTGGGCCAGGCCAAGATGGGCTTCTGCTCGGACCGCGAGGATGTCAACTCTCTCTGCCTGACGGTTGTGAGCCGCCTG
CTGGAGCGGCAACATGTGAAGCACTCGGAGATCGGACGACTGGAGGTGGGCACCGAGACCATTGTGGACAAGTCGAAGTCGGTGAAGTCCGTGCT
GATGCAGCTGTTCGCCGAGAGCGGGAACACGGACATCGAGGGCATCGACACCACGAACGCCTGTTACGGCGGCACGGCGGCGCTCTTCAATGCCG
TCAATTGGGTGGAATCTTCTAGCTGGGACGGCCGCCTGGCTTTGGCCGTTTGTGCTGATATCGCCGTGTACGCCAAGGGTGCAGCGCGCCCAACT
GGTGGTGCGGGTGCTGTGGCTATGCTGGTGGGTCCAAATGCGCCGCTTATCCTCGATCGTGGACTACGCGCAACGCACATGGAGCACGCCTACGA
CTTTTACAAGCCGGACCTCAGCTCCGAATACCCAACGGTAGATGGAAAGCTCTCTATTCAGTGCTACCTTTCTGCTCTGGACACCTGCTACAGGC
TGTATCGCAAGAAGTTCGACCAGCAGCAGAAGGATACTTCCAAGCAGCCGGCCAGCCTGAGCACCTTCGATGCTATCCTATTCCACACACCGTTC
TGCAAGTTGGTGCAAAAAATCTGTGGGTCGCCTGAGCTTCAACGATTTCCTGCTGAGCAGTGAGGAGGAGCGAACGAAGCAGTTTCCCGACCTGGA
ACGTTTTAATACCGCTACCCTGGAGAGCACCTACTTTGATCGCGATGTGGAGAAGGCCTTCATGACGCAGTCCGCCAACATCTTTGCCAGCAAGA
CCAAGAAATCGCTGCTGCTGGCCAACCAAGTGGGCAATATGTACACACCCTCGGTGTACTCCGGTTTGGTGTCTCTGTTGATTAGCGGACCAGCC
CAGGAGCTGGTGGAAAGCGCATTGGTTTGTTCTCCTACGGATCCGGACTGGCTGCTTCCATGTACTCGATCAGCGTGACCCAGGATGCAGCTGC
TTTCGAAAAGTTCGTCTCGCAGCTGGACTACGTGCAGCCGTTGCTGAATTCACGGGAGAAGGTTGCGCCCGAGCAGTTCTCCGCGCTGATGGAGG
TGCGGGAGAAGAACAACCATGCGGCGCCCTACACGCCAACGGGCAGCATCTCCGCACTGTTTCCCGGCACCTACTACCTGAAGGACGTGGATGCG
CTGCATAGACGCACCTACGAGCGCACACCGACCATCAGCAATGGGGTGCACTAACCCCGGGCTATGGTTCCTTCGGTTTGGTTTCGGTTTCGCCT
ACAACTTGACAATAACTCTAACTCTCTCGACCAAACCCATGTAAGCAGTAGCTGTAGATGGTATCTATTTATAACTGGTATGATCCCGAGGGGTC

FIGURE SHEET 636

GCTATCCTTTTTGCTCTTATTCGGGTCCTTGTCGCGTATATAGTACTACACTTCTTATTTATACAAGCTTGCGAATTAACTCTTTCATCCAGTCA
GACCTTATTTATATCATGGAACAAGTCTTAACTAGCGTCGGTACTGCAATCTATGCCTATAATTGTACAATACTTATACCTGTGTGTAATGCACA
CAATCAATTGTTAATAAACAATAAAAATCAACAAAGTC
(SEQ ID NO: 1184)

Start ATG: 177 (Reverse strand: CAT)

MASHWPENVGIRAIEILFPSQYVDQTELETFDGASAGKYTIGLGQAKMGFCSDREDVNSLCLTVVSRLLERQHVKHSEIGRLEVGTETIVDKSKS
VKSVLMQLFAESGNTDIEGIDTTNACYGGTAALFNAVNWVESSSWDGRLALAVCADIAVYAKGAARPTGGAGAVAMLVGPNAPLILDRGLRATHM
EHAYDFYKPDLSSEYPTVDGKLSIQCYLSALDTCYRLYRKKFDQQQKDTSKQPASLSTFDAILFHTPFCKLVQKSVGRLSFNDFLLSSEEERTKQ
FPDLERFNTATLESTYFDRDVEKAFMTQSANIFASKTKKSLLLANQVGNMYTPSVYSGLVSLLISGPAQELVGKRIGLFSYGSGLAASMYSISVT
QDAAAFEKFVSQLDYVQPLLNSREKVAPEQFSALMEVREKNNHAAPYTPTGSISALFPGTYYLKDVDALHRRTYERTPTISNGVH*
(SEQ ID NO: 1185)

Celera Sequence No. : 142000013385215
AGCACATTCGTTTTCCTCTTTAAATAAGGAGAATCCACTTAAAGAAATCTGATAATCGCTGCATATTGTGCTATTTATTTTATGTTAAAAAAGTA
TATTCGCAAGAGCATAAAAACAATCTGATCGGGTTAATCTTAACTTTTCGCTGCTCCATTCTCATTGATTACTACAGCACAAAAAAAAAGTGGG
GAAAGCGTGGAATCCTAACTAGAAGAACGGAAGATAGAATAATGGATAAAAAACAAAGGGGCAGGGCAGCAAAAACTTAAATCATTGGCAAATAC
CTTTTTACGATGCGGATTTTAATCAAAGTTTTTGCCACCGCTGTCAGTTTCTTTTTTTTACTTAAAATGGTAATAAAAAAAAAAGGGGAAACGAC
GATAAATAAACATTTTAAAATAATTGCTAACGGCGTGTTGTTGCGCTTTAGTGAACTTATTAGTCTACCCTCGCACCGGCCAATTTCCACAATTG
ATTAGTTTAAAATTGCATTTTTTGGACATTTAAATGGGAATCTAATTGATTGCCATTTTTATTGAGAGCACTTAACACTATACAATGGCAGGTTT
TGTATTTAAGCTATATATTCCTCGTTTATACAGTGTCAAATTAATTATTGATTTTATAAGCAGCTAAGAAAATGATTGTTTAATTTGGACCGATT
GATCATCGAGGACTTAAAATGGACTTAAAATAATTGGATATTAGCAACTTTGAAAAGATCCCGTTTACTCCCAAAACTTCAGAATCAACCCACGA
ACTTCTTTAAGCCAGTGTGACCCCACCCGCTCTTTAGCTCTCTTTCGCTCCATCTCGCTTCCGCACATCGATTGGCGAAAGCTTCGCTCGCACTC
GATATCAGCTCACAACTTCGCTTGCAAGCTCGCCGCGGAAAGCTCGCGATCACACGGGTCGAAATCGAAATCGAATCGCGGTAGAGAGCTTTTCG
AAGTGCGAGCGTCGACGTTTTATTTCTGCGGCTCAGTCGGTTTTAGTTCGTTCTGTTGGAGAAAAGCAGCAATCACACGTTCGCAAGGTGAACGC
GAAGACACAGCAAAGTAAGCCCTTCCCCCCCACCAACACACACACCCACCCAAAGCAAATAAGTAACAATAAATAATGGAATGGCTGGAAGACGG
TTCTGGGCGATTTAAACAATTAGCGAAAGAAAGCGGCATTGAAATCCGTCTTGAATTCGCCCCGAAAAAGTGACGAAGCAGCGATCAAAGCGCAG
AGCGAAAACACGCACACAGACTGCAAGTGTGTTAGATAATAAGTGCAGCACAAGTCCACACTTGAGTAAAATAATCCCTAAAAAAGCCGAATATC
AATTAGTTTTCCAAGGAGCTTGAAAAAGTGCGGTATGAAAACGTGAAAATTTGCGCGTGGAAAATTATTTTGCCTTGTCAGCTGACCCCCTTCCC
CGTGTTCGCTCCATCCCTGTCGCACCGCGGGTCTTGTGATCGCCGCCGCTCTTGCGCTCGCTTGCTCTCCCATTTCGAAACTCGAAACAGAAGTG
GGAGTTATTCGTATTCCGATAATGAAAAACCAATATGGAGAACGAGCGACGTAAAAAAGGCGGCCCAAAGATTTTTACCATTTCCCTTACCCACT
TTTTTTTCATTTGTCAGCTGACGGCAATGACAGTAGTCTTGTGATCAACGTCAAAAGCAATTGTCAAATATTCGAACTCGAATGGAGAGCGAGAG
AGCCAGAGCGGAGAGTTGCTCTCCCACTCCACCCTCTCTTGTTTTTCTTTGCTGATAATTATGAAAACCCGCATATTTTGAAAAACATGCATTTC
AGTTACATTCCTCCGTTGAATTTGTCAACCTGTGGTTGTTTTTTCACAGCTCTTATTTTATTTATTTAGCGATTAGTTTGACAAATTGCTCTCTT
CGAACTTTCAAAGCTCTGTCACGTGAAACGAAAGCTCTGCTTTTAAAGTTTTACGCAGCATAATCAAAGAGGGGGAGTTAAAAAAAAAATAATTA
AATCAATCGAAATTATTAGCTGCTAACCTACAACTTTATAACCTATAATCGAAAAATTTGGGAGCTGTGGGCTCTACAAAAACTTAACCTGTAAA
TGTAGCAGATACACCTGCCCCTTGTCAGCTGACAGAGGGCTGAGCAAGAAATTAGTGATAAGAAAATGTTCACCTTTATCTTCGCCCTTTTGCAG
CCAGCATTTAACAATTTTCCTCTTCTATTTTCCCTCCATTGCAGTCGAAAAAACAGAATAAAGCAAAATGTCCAACCTTAAGCGTTTCGATGATG
AGGAGCGTGAGTCCAAATATGGACGTGTCTTCGCTGTCTCCGGTCCTGGTAAGCACCTAACTATACTGACTAACCATAACTCATGCTATCTAAAA
GTTAATAAAAATAAGTTAATAATACCTGTGAACTGGAAACCTTACTTTGATGATTAGTCTAGAACTTACACTTCTGTGTGAAATAATGGCAACTT
TAGAAATGTGTCCACCTATTTGTGATTAATATTCAAACAACTCAAACATTTGGTTTCATTATTCAAAATTAAATGTGAATAATTTTAATAATTA
ATTAATTGTTTCTTTAAACTTTTTTCTATAATTCTAACAAAAACATCATCAAGTATCATTAATAATAAAAAATTTTAAAAGAAAATGTTCAATGG
AACCTATCTTCGTTTGCTGAGTTATAAAAACTTCTTGAATGAAATGTAGCCCCCCTAACCCGACCAACCGCTTCATTCCAGTCGTCACCGCCGAG
GCCATGTCTGGATCAGCTATGTACGAGTTGGTCCGCGTCGGCTACTACGAGCTGGTGGGCGAGATCATCCGTCTGGAGGGTGACATGGCCACCAT
CCAGGTGTACGAGGAGACCTCTGGCGTAACTGTCGGAGATCCGGTGCTGCGTACCGGCAAGCCTCTTTCCGTGGAGCTGGGACCCGGTATCATGG
GCAGCATCTTTGACGGTATCCAGCGTCCCCTGAAGGACATTAACGAGCTGACCGAATCCATCTACATCCCCAAGGGTGTGAACGTGCCCAGTTTG
TCCCGCGTGGCCAGCTGGGAGTTCAACCCCCTGAACGTCAAGGTCGGCTCCCACATCACCGGAGGTGACCTGTACGGTCTGGTGCATGAGAACAC
TCTGGTCAAGCACAAGATGATTGTGAACCCCCGCGCCAAGGGAACAGTGCGCTACATCGCCCCCCTCCGGCAACTACAAGGTCGACGATGTCGTCC
TGGAGACCGAGTTCGATGGAGAGATCACCAAGCACACCATGTTGCAGGTGTGGCCAGTGCGTCAGCCACGTCCCGTGACCGAGAAGCTGCCCGCC
AACCACCCCCTGCTCACCGGACAGCGTGTGCTCGACTCGCTCTTCCCCTGTGTCCAGGGCGGTACCACCGCCATTCCCGGAGCTTTCGGTTGCGG
CAAGACTGTGATCTCGCAGGTGAGAGTCCCACAAATTGAGAATTTAAGGAGCGATGCCTCGTGTAGCCTCCATACACTCAAGTTTCATAAAAATA
CAATCCCTAATAAATCATTTACTTGCTTGCAGGCTCTGTCCAAGTACTCCAACTCCGATGTCATCATCTACGTCGGTTGCGGTGAGCGTGGTAAC
GAGATGTCTGAGGTACTGCGTGACTTCCCCGAGCTGTCCGTGGAGATCGACGGTGTCACCGAGTCCATCATGAAGCGTACCGCCCTTGTGGCCAA
CACCTCCAACATGCCTGTGGCTGCTCGTGAGGCCTCCATCTACACTGGTATCACCTTGTCCGAATACTTCCGTGATATGGGTTACAACGTGTCCA
TGATGGCTGATTCCACCTCCCGTTGGGCTGAGGCTCTTCGTGAAATTTCTGGTCGTCTCGCTGAGATGCCTGCCGATTCCGGCTACCCAGCCTAC
TTGGGAGCCCGTCTGGCCTCCTTCTACGAGCGTGCCGGTCGCGTTAAGTGCTTGGGTAACCCCGAGCGCGAGGGATCCGTGTCCATTGTCGGAGC
TGTGTCTCCTCCTGGTGGTGACTTCTCCGATCCCGTGACCTCCGCCACTCTGGGTATCGTGCAGGTGTTCTGGGGTCTCGACAAGAAGTTGGCCC
AGCGCAAGCACTTCCCCTCGATCAACTGGCTCATCTCCTACTCGAAGTACATGCGTGCTCTGGATGACTTCTATGACAAGAACTTCCCCGAATTC
GTGCCGCTGCGTACCAAGGTCAAGGAGATCCTGCAGGAGGAGGAGGATCTGTCTGAGATCGTGCAACTGGTCGGCAAGGCCTCTCTGGCCGAAAC
CGACAAGATCACGCTGGAGGTGGCCAAGCTGCTGAAGGACGATTTCCTGCAGCAGAACTCCTACTCCTCGTACGATCGCTTCTGCCCCTTCTACA
AGACCGTGGGCATGTTGAGGAACATCATCGACTTCTACGACATGGCCCGTCACTCCGTGGAGTCTACGGCTCAGTCTGAGAACAAGATCACCTGG
AACGTGATTCGTGAGGCAATGGGCAACATTATGTACCAGCTGTCATCCATGAAGTTCAAGGTGGGTTAACACGCAAATTTATCCATTGCCTAGAC
ACTGGGTGACCACATTTTTCAATCCATTTCAGGACCCCGTTAAGGATGGTGAGGCCAAGATCAAGGCTGACTTCGAGCAGCTGCACGAGGACCTG
CAGCAGGCCTTCAGAAATCTGGAGGACTAGAGACCGCGCTGGCCCTACTTTTACACTCTAATCTTATATTTGTTATATAGTTAACGTTTAAAAAT
GAAAGCAGTCAAAAACCATCCGAAAAAGCCTAATCAAACACCAACAATTCCGTGCTGCATTCGATGAAAAACAAAAGTCCAACAAATACCACAAC
TTCTTGGTGCCTGCGAGAGATGTAAACATTCGGCCTGCGGTTAATACTTTCCCCTAACCACGCCCCCTCCGCCCCTTGAAGGGCAACTCTAGGC
AACAGCAACTACAACGTCCTGCTATGTACTTCCATTTACAACAACAACACCAACATACACTTGAATAAAAGTACACGGACACTGGCGCACACACA
ACACATACATAAAAGACACAAATACAAATGCATGCATAAATAGTATTATTGTTTAATGAATGGAAATTCTTGTTTATTTGTGAAAAAAGTCATGT TTTCTCCCTGTTTGTTTGTTAAATTTATGTAAATATTTAAAGTATGAAATATTAAATGTACGAATAAAGTGCAACAACAAATACATTTAATGTAA
TTGAAAGTGAATTTCACTGGCAGCAGAATGGATATTAAAAATGTGTCAACTCGATAAAAAGATAATAAGTTAAAATATTTTTTTGAATTTTAAAC
CTTCATTATATAAACATACTTGACTATATGAAAGCTAAGAAAATGGGAATATATTGAAAAGCATAATCTAAAATCCTATATCATTCTCAGTCATC
ACCTTAGTCTTTCCATAAACTTCTGCCCCATTTATTTTATTTATTTGACAATATTAGTAAAAATTGTACCAAGTGAAAAAATTGTATATATTTAA
ACCAAATGGAAAAGAAGTCCTGGGTTGCACCGCTTACCTCGTTCACCAACAGTAACGCAAGTAACGAAGACAGAGCCCGCAACTCGGGATCGTTA
AACCAAGATGGGGAGCCAAGGTCCGTGCCTCACCCAACGGTTCCGGCTAAGAAGTGCACATGTCCAACCTGCGCTTGCCAACGTAATGACCATAA
ATCCAATCCGGTACCCCCTCCCCCTCAATCACGCAAGCCTGTAGCCGAGCCGGAAAGTCCCCATGATACAGTCAATGACGAGGACAGTTTGAAGG
ACTTGAGACGTTCGACGGACCAATCCCACAAGAGCGCTCACATCGCCTTGGAGAAGAATGAGGACTCGGGTTTTGTGATCGAGCAGGTGGTTGAT
ACGCACAAATATTCGTCGGATGAAGAAGAGGAGGAGGCGACGATGGGTCGCATTTTCGGAGTCTCCGGTCCGGTGGTCAATGCCGAGGAGATGGC
CGGCGCAGCCATGTACGAGCTGGTTCGCGTTGGACACTCCCAGCTTGTTGGTGAGATCATTCGACTGGAGGGTGATATGGCCACCATTCAGGTTT
ACGAGGATACTTCGGGTGTGAGCGTGGGTGATCCCGTCTACCAGACGGGAAAGCCGCTCTCCGTGGAATTGGGACCCGGCATCATGGGCAGCATT
TTCGATGGTATCCAGCGACCATTGAGGTCCATCAGTGAACTAACCAACTC
(SEQ ID NO: 1186)

Exon: 1001..1037
Exon: 2230..2328
Exon: 2742..3439
Exon: 3548..4525
Exon: 4593..5225
Start ATG: 2253

Transcript No. : CT37353
TTCTGTTGGAGAAAAGCAGCAATCACACGTTCGCAAGTCGAAAAAACAGAATAAAGCAAAATGTCCAACCTTAAGCGTTTCGATGATGAGGAGCG
TGAGTCCAAATATGGACGTGTCTTCGCTGTCTCCGGTCCTGTCGTCACCGCCGAGGCCATGTCTGGATCAGCTATGTACGAGTTGGTCCGCGTCG
GCTACTACGAGCTGGTGGGCGAGATCATCCGTCTGGAGGGTGACATGGCCACCATCCAGGTGTACGAGGAGACCTCTGGCGTAACTGTCGGAGAT
CCGGTGCTGCGTACCGGCAAGCCTCTTTCCGTGGAGCTGGGACCCGGTATCATGGGCAGCATCTTTGACGGTATCCAGCGTCCCCTGAAGGACAT
TAACGAGCTGACCGAATCCATCTACATCCCCAAGGGTGTGAACGTGCCCAGTTTGTCCCGCGTGGCCAGCTGGGAGTTCAACCCCCTGAACGTCA
AGGTCGGCTCCCACATCACCGGAGGTGACCTGTACGGTCTGGTGCATGAGAACACTCTGGTCAAGCACAAGATGATTGTGAACCCCCGCGCCAAG
GGAACAGTGCGCTACATCGCCCCCTCCGGCAACTACAAGGTCGACGATGTCGTCCTGGAGACCGAGTTCGATGGAGAGATCACCAAGCACACCAT
GTTGCAGGTGTGGCCAGTGCGTCAGCCACGTCCCGTGACCGAGAAGCTGCCCGCCAACCACCCCCTGCTCACCGGACAGCGTGTGCTCGACTCGC
TCTTCCCCTGTGTCCAGGGCGGTACCACCGCCATTCCCGGAGCTTTCGGTTGCGGCAAGACTGTGATCTCGCAGGCTCTGTCCAAGTACTCCAAC
TCCGATGTCATCATCTACGTCGGTTGCGGTGAGCGTGGTAACGAGATGTCTGAGGTACTGCGTGACTTCCCCGAGCTGTCCGTGGAGATCGACGG
TGTCACCGAGTCCATCATGAAGCGTACCGCCCTTGTGGCCAACACCTCCAACATGCCTGTGGCTGCTCGTGAGGCCTCCATCTACACTGGTATCA
CCTTGTCCGAATACTTCCGTGATATGGGTTACAACGTGTCCATGATGGCTGATTCCACCTCCCGTTGGGCTGAGGCTCTTCGTGAAATTTCTGGT
CGTCTCGCTGAGATGCCTGCCGATTCCGGCTACCCAGCCTACTTGGGAGCCCGTCTGGCCTCCTTCTACGAGCGTGCCGGTCGCGTTAAGTGCTT
GGGTAACCCCGAGCGCGAGGGATCCGTGTCCATTGTCGGAGCTGTGTCTCCTCCTGGTGGTGACTTCTCCGATCCCGTGACCTCCGCCACTCTGG
GTATCGTGCAGGTGTTCTGGGGTCTCGACAAGAAGTTGGCCCAGCGCAAGCACTTCCCCTCGATCAACTGGCTCATCTCCTACTCGAAGTACATG
CGTGCTCTGGATGACTTCTATGACAAGAACTTCCCCGAATTCGTGCCGCTGCGTACCAAGGTCAAGGAGATCCTGCAGGAGGAGGAGGATCTGTC
TGAGATCGTGCAACTGGTCGGCAAGGCCTCTCTGGCCGAAACCGACAAGATCACGCTGGAGGTGGCCAAGCTGCTGAAGGACGATTTCCTGCAGC
AGAACTCCTACTCCTCGTACGATCGCTTCTGCCCCTTCTACAAGACCGTGGGCATGTTGAGGAACATCATCGACTTCTACGACATGGCCCGTCAC
TCCGTGGAGTCTACGGCTCAGTCTGAGAACAAGATCACCTGGAACGTGATTCGTGAGGCAATGGGCAACATTATGTACCAGCTGTCATCCATGAA
GTTCAAGGACCCCGTTAAGGATGGTGAGGCCAAGATCAAGGCTGACTTCGAGCAGCTGCACGAGGACCTGCAGCAGGCCTTCAGAAATCTGGAGG
ACTAGAGACCGCGCTGGCCCTACTTTTACACTCTAATCTTATATTTGTTATATAGTTAACGTTTAAAAATGAAAGCAGTCAAAAACCATCCGAAA
AAGCCTAATCAAACACCAACAATTCCGTGCTGCATTCGATGAAAAACAAAAGTCCAACAAATACCACAACTTCTTGGTGCCTGCGAGAGATGTAA
ACATTCCGGCCTGCGGTTAATACTTTCCCCTAACCACGCCCCCTCCGCCCCTTGAAGGGCAACTCTAGGCAACAGCAACTACAACGTCCTGCTAT
GTACTTCCATTTACAACAACAACACCAACATACACTTGAATAAAAGTACACGGACACTGGCGCACACACAACACATACATAAAAGACACAAATAC
AAATGCATGCATAAATAGTATTATTGTTTAATGAATGGAAATTCTTGTTTATTTGTGAAAAAAGTCATGTTTTCTCCCTGTTTGTTTGTTAAATT
TATGTAAATATTTAAAGTATGAAATATTAAATGTACGAATAAAGTGCAACAACAAATACATTTAATGTAA
(SEQ ID NO: 1187)

Start ATG: 61

MSNLKRFDDEERESKYGRVFAVSGPVVTAEAMSGSAMYELVRVGYYELVGEIIRLEGDMATIQVYEETSGVTVGDPVLRTGKPLSVELGPGIMGS
IFDGIQRPLKDINELTESIYIPKGVNVPSLSRVASWEFNPLNVKVGSHITGGDLYGLVHENTLVKHKMIVNPRAKGTVRYIAPSGNYKVDDVVLE
TEFDGEITKHTMLQVWPVRQPRPVTEKLPANHPLLTGQRVLDSLFPCVQGGTTAIPGAFGCGKTVISQALSKYSNSDVIIYVGCGERGNEMSEVL
RDFPELSVEIDGVTESIMKRTALVANTSNMPVAAREASIYTGITLSEYFRDMGYNVSMMADSTSRWAEALREISGRLAEMPADSGYPAYLGARLA
SFYERAGRVKCLGNPEREGSVSIVGAVSPPGGDFSDPVTSATLGIVQVFWGLDKKLAQRKHFPSINWLISYSKYMRALDDFYDKNFPEFVPLRTK
VKEILQEEEDLSEIVQLVGKASLAETDKITLEVAKLLKDDFLQQNSYSSYDRFCPFYKTVGMLRNIIDFYDMARHSVESTAQSENKITWNVIREA
MGNIMYQLSSMKFKDPVKDGEAKIKADFEQLHEDLQQAFRNLED*
(SEQ ID NO: 1188)

Name: vacuolar ATPase subunit A
Classification: enzyme

Celera Sequence No. : 142000013385215
AAAAAACAAAGGGGCAGGGCAGCAAAAACTTAAATCATTGGCAAATACCTTTTTACGATGCGGATTTTAATCAAAGTTTTTGCCACCGCTGTCAG
TTTCTTTTTTTTACTTAAAATGGTAATAAAAAAAAAAGGGGAAACGACGATAAATAAACATTTTAAAATAATTGCTAACGGCGTGTTGTTGCGCT
TTAGTGAACTTATTAGTCTACCCTCGCACCGGCCAATTTCCACAATTGATTAGTTTAAAATTGCATTTTTTGGACATTTAAATGGGAATCTAATT
GATTGCCATTTTTATTGAGAGCACTTAACACTATACAATGGCAGGTTTTGTATTTAAGCTATATATTCCTCGTTTATACAGTGTCAAATTAATTA
TTGATTTTATAAGCAGCTAAGAAAATGATTGTTTAATTTGGACCGATTGATCATCGAGGACTTAAAATGGACTTAAAATAATTGGATATTAGCAA CTTTGAAAAGATCCCGTTTACTCCCAAAACTTCAGAATCAACCCACGAACTTCTTTAAGCCAGTGTGACCCCACCCGCTCTTTAGCTCTCTTTCG
CTCCATCTCGCTTCCGCACATCGATTGGCGAAAGCTTCGCTCGCACTCGATATCAGCTCACAACTTCGCTTGCAAGCTCGCCGCGGAAAGCTCGC
GATCACACGGGTCGAAATCGAAATCGAATCGCGGTAGAGAGCTTTTCGAAGTGCGAGCGTCGACGTTTTATTTCTGCGGCTCAGTCGGTTTTAGT
TCGTTCTGTTGGAGAAAAGCAGCAATCACACGTTCGCAAGGTGAACGCGAAGACACAGCAAAGTAAGCCCTTCCCCCCCACCAACACACACACCC
ACCCAAAGCAAATAAGTAACAATAAATAATGGAATGGCTGGAAGACGGTTCTGGGCGATTTAAACAATTAGCGAAAGAAAGCGGCATTGAAATCC
GTCTTGAATTCGCCCCGAAAAAGTGACGAAGCAGCGATCAAAGCGCAGAGCGAAAACACGCACACAGACTGCAAGTGTGTTAGATAATAAGTGCA
GCACAAGTCCACACTTGAGTAAAATAATCCCTAAAAAAGCCGAATATCAATTAGTTTTCCAAGGAGCTTGAAAAAGTGCGGTATGAAAACGTGAA
AATTTGCGCGTGGAAAATTATTTTGCCTTGTCAGCTGACCCCCTTCCCCGTGTTCGCTCCATCCCTGTCGCACCGCGGGTCTTGTGATCGCCGCC
GCTCTTGCGCTCGCTTGCTCTCCCATTTCGAAACTCGAAACAGAAGTGGGAGTTATTCGTATTCCGATAATGAAAAACCAATATGGAGAACGAGC
GACGTAAAAAAGGCGGCCCAAAGATTTTTACCATTTCCCTTACCCACTTTTTTTCATTTGTCAGCTGACGGCAATGACAGTAGTCTTGTGATCA
ACGTCAAAAGCAATTGTCAAATATTCGAACTCGAATGGAGAGCGAGAGAGCCAGAGCGGAGAGTTGCTCTCCCACTCCACCCTCTCTTGTTTTTC
TTTGCTGATAATTATGAAAACCCGCATATTTTGAAAAACATGCATTTCAGTTACATTCCTCCGTTGAATTTGTCAACCTGTGGTTGTTTTTTCAC
AGCTCTTATTTTATTTATTTAGCGATTAGTTTGACAAATTGCTCTCTTCGAACTTTCAAAGCTCTGTCACGTGAAACGAAAGCTCTGCTTTTAAA
GTTTTACGCAGCATAATCAAAGAGGGGGAGTTAAAAAAAAAATAATTAAATCAATCGAAATTATTAGCTGCTAACCTACAACTTTATAACCTATA
ATCGAAAAATTTGGGAGCTGTGGGCTCTACAAAAACTTAACCTGTAAATGTAGCAGATACACCTGCCCCTTGTCAGCTGACAGAGGGCTGAGCAA
GAAATTAGTGATAAGAAAATGTTCACCTTTATCTTCGCCCTTTTGCAGCCAGCATTTAACAATTTTCCTCTTCTATTTTCCCTCCATTGCAGTCG
AAAAAACAGAATAAAGCAAAATGTCCAACCTTAAGCGTTTCGATGATGAGGAGCGTGAGTCCAAATATGGACGTGTCTTCGCTGTCTCCGGTCCT
GGTAAGCACCTAACTATACTGACTAACCATAACTCATGCTATCTAAAAGTTAATAAAAATAAGTTAATAATACCTGTGAACTGGAAACCTTACTT
TGATGATTAGTCTAGAACTTACACTTCTGTGTGAAATAATGGCAACTTTAGAAATGTGTCCACCTATTTGTGATTAATATTCAAACAACTCAAAC
ATTTTGGTTTCATTATTCAAAATTAAATGTGAATAATTTTAATAATTAATTAATTGTTTCTTTAAACTTTTTTCTATAATTCTAACAAAAACATC
ATCAAGTATCATTAATAATAAAAAATTTTAAAAGAAAATGTTCAATGGAACCTATCTTCGTTTGCTGAGTTATAAAAACTTCTTGAATGAAATGT
AGCCCCCCTAACCCGACCAACCGCTTCATTCCAGTCGTCACCGCCGAGGCCATGTCTGGATCAGCTATGTACGAGTTGGTCCGCGTCGGCTACTA
CGAGCTGGTGGGCGAGATCATCCGTCTGGAGGGTGACATGGCCACCATCCAGGTGTACGAGGAGACCTCTGGCGTAACTGTCGGAGATCCGGTGC
TGCGTACCGGCAAGCCTCTTTCCGTGGAGCTGGGACCCGGTATCATGGGCAGCATCTTTGACGGTATCCAGCGTCCCCTGAAGGACATTAACGAG
CTGACCGAATCCATCTACATCCCCAAGGGTGTGAACGTGCCCAGTTTGTCCCGCGTGGCCAGCTGGGAGTTCAACCCCCTGAACGTCAAGGTCGG
CTCCCACATCACCGGAGGTGACCTGTACGGTCTGGTGCATGAGAACACTCTGGTCAAGCACAAGATGATTGTGAACCCCCGCGCCAAGGGAACAG
TGCGCTACATCGCCCCCTCCGGCAACTACAAGGTCGACGATGTCGTCCTGGAGACCGAGTTCGATGGAGAGATCACCAAGCACACCATGTTGCAG
GTGTGGCCAGTGCGTCAGCCACGTCCCGTGACCGAGAAGCTGCCCGCCAACCACCCCCTGCTCACCGGACAGCGTGTGCTCGACTCGCTCTTCCC
CTGTGTCCAGGGCGGTACCACCGCCATTCCCGGAGCTTTCGGTTGCGGCAAGACTGTGATCTCGCAGGTGAGAGTCCCACAAATTGAGAATTTAA
GGAGCGATGCCTCGTGTAGCCTCCATACACTCAAGTTTCATAAAAATACAATCCCTAATAAATCATTTACTTGCTTGCAGGCTCTGTCCAAGTAC
TCCAACTCCGATGTCATCATCTACGTCGGTTGCGGTGAGCGTGGTAACGAGATGTCTGAGGTACTGCGTGACTTCCCCGAGCTGTCCGTGGAGAT
CGACGGTGTCACCGAGTCCATCATGAAGCGTACCGCCCTTGTGGCCAACACCTCCAACATGCCTGTGGCTGCTCGTGAGGCCTCCATCTACACTG
GTATCACCTTGTCCGAATACTTCCGTGATATGGGTTACAACGTGTCCATGATGGCTGATTCCACCTCCCGTTGGGCTGAGGCTCTTCGTGAAATT
TCTGGTCGTCTCGCTGAGATGCCTGCCGATTCCGGCTACCCAGCCTACTTGGGAGCCCGTCTGGCCTCCTTCTACGAGCGTGCCGGTCGCGTTAA
GTGCTTGGGTAACCCCGAGCGCGAGGGATCCGTGTCCATTGTCGGAGCTGTGTCTCCTCCTGGTGGTGACTTCTCCGATCCCGTGACCTCCGCCA
CTCTGGGTATCGTGCAGGTGTTCTGGGGTCTCGACAAGAAGTTGGCCCAGCGCAAGCACTTCCCCTCGATCAACTGGCTCATCTCCTACTCGAAG
TACATGCGTGCTCTGGATGACTTCTATGACAAGAACTTCCCCGAATTCGTGCCGCTGCGTACCAAGGTCAAGGAGATCCTGCAGGAGGAGGAGGA
TCTGTCTGAGATCGTGCAACTGGTCGGCAAGGCCTCTCTGGCCGAAACCGACAAGATCACGCTGGAGGTGGCCAAGCTGCTGAAGGACGATTTCC
TGCAGCAGAACTCCTACTCCTCGTACGATCGCTTCTGCCCCTTCTACAAGACCGTGGGCATGTTGAGGAACATCATCGACTTCTACGACATGGCC
CGTCACTCCGTGGAGTCTACGGCTCAGTCTGAGAACAAGATCACCTGGAACGTGATTCGTGAGGCAATGGGCAACATTATGTACCAGCTGTCATC
CATGAAGTTCAAGGTGGGTTAACACGCAAATTTATCCATTGCCTAGACACTGGGTGACCACATTTTTCAATCCATTTCAGGACCCCGTTAAGGAT
GGTGAGGCCAAGATCAAGGCTGACTTCGAGCAGCTGCACGAGGACCTGCAGCAGGCCTTCAGAAATCTGGAGGACTAGAGACCGCGCTGGCCCTA
CTTTTACACTCTAATCTTATATTTGTTATATAGTTAACGTTTAAAAATGAAAGCAGTCAAAAACCATCCGAAAAAGCCTAATCAAACACCAACAA
TTCCGTGCTGCATTCGATGAAAAACAAAAGTCCAACAAATACCACAACTTCTTGGTGCCTGCGAGAGATGTAAACATTCCGGCCTGCGGTTAATA
CTTTCCCCTAACCACGCCCCCTCCGCCCCTTGAAGGGCAACTCTAGGCAACAGCAACTACAACGTCCTGCTATGTACTTCCATTTACAACAACAA
CACCAACATACACTTGAATAAAAGTACACGGACACTGGCGCACACACAACACATACATAAAAGACACAAATACAAATGCATGCATAAATAGTATT
ATTGTTTAATGAATGGAAATTCTTGTTTATTTGTGAAAAAAGTCATGTTTTCTCCCTGTTTGTTTGTTAAATTTATGTAAATATTTAAAGTATGA
AATATTAAATGTACGAATAAAGTGCAACAACAAATACATTTAATGTAATTGAAAGTGAATTTCACTGGCAGCAGAATGGATATTAAAAATGTGTC
AACTCGATAAAAAGATAATAAGTTAAAATATTTTTTTGAATTTTAAACCTTCATTATATAAACATACTTGACTATATGAAAGCTAAGAAAATGGG
AATATATTGAAAAGCATAATCTAAAATCCTATATCATTCTCAGTCATCACCTTAGTCTTTCCATAAACTTCTGCCCCATTTATTTTATTTATTTG
ACAATATTAGTAAAAATTGTACCAAGTGAAAAAATTGTATATATTTAAACCAAATGGAAAAGAAGTCCTGGGTTGCACCGCTTACCTCGTTCACC
AACAGTAACGCAAGTAACGAAGACAGAGCCCGCAACTCGGGATCGTTAAACCAAGATGGGGAGCCAAGGTCCGTGCCTCACCCAACGGTTCCGGC
TAAGAAGTGCACATGTCCAACCTGCGCTTGCCAACGTAATGACCATAAATCCAATCCGGTACCCCCTCCCCCTCAATCACGCAAGCCTGTAGCCG
AGCCGGAAAGTCCCCATGATACAGTCAATGACGAGGACAGTTTGAAGGACTTGAGACGTTCGACGGACCAATCCCACAAGAGCGCTCACATCGCC
TTGGAGAAGAATGAGGACTCGGGTTTTGTGATCGAGCAGGTGGTTGATACGCACAAATATTCGTCGGATGAAGAAGAGGAGGAGGCGACGATGGG
TCGCATTTTCGGAGTCTCCGGTCCGGTGGTCAATGCCGAGGAGATGGCCGGCGCAGCCATGTACGAGCTGGTTCGCGTTGGACACTCCCAGCTTG
TTGGTGAGATCATTCGACTGGAGGGTGATATGGCCACCATTCAGGTTTACGAGGATACTTCGGGTGTGAGCGTGGGTGATCCCGTCTACCAGACG
GGAAAGCCGCTCTCCGTGGAATTGGGACCCGGCATCATGGGCAGCATTTTCGATGGTATCCAGCGACCATTGAGGTCCATCAGTGAACTAACCAA
CTC
(SEQ ID NO: 1189)

Exon: 1001..1125
Exon: 1993..2091
Exon: 2505..3202
Exon: 3311..4288
Exon: 4356..4988
Start ATG: 2016

Transcript No. : CT37359
CGAAAACACGCACACAGACTGCAAGTGTGTTAGATAATAAGTGCAGCACAAGTCCACACTTGAGTAAAATAATCCCTAAAAAAGCCGAATATCAA
TTAGTTTTCCAAGGAGCTTGAAAAAGTGCGTCGAAAAAACAGAATAAAGCAAAATGTCCAACCTTAAGCGTTTCGATGATGAGGAGCGTGAGTCC AAATATGGACGTGTCTTCGCTGTCTCCGGTCCTGTCGTCACCGCCGAGGCCATGTCTGGATCAGCTATGTACGAGTTGGTCCGCGTCGGCTACTA
CGAGCTGGTGGGCGAGATCATCCGTCTGGAGGGTGACATGGCCACCATCCAGGTGTACGAGGAGACCTCTGGCGTAACTGTCGGAGATCCGGTGC
TGCGTACCGGCAAGCCTCTTTCCGTGGAGCTGGGACCCGGTATCATGGGCAGCATCTTTGACGGTATCCAGCGTCCCCTGAAGGACATTAACGAG
CTGACCGAATCCATCTACATCCCCAAGGGTGTGAACGTGCCCAGTTTGTCCCGCGTGGCCAGCTGGGAGTTCAACCCCCTGAACGTCAAGGTCGG
CTCCCACATCACCGGAGGTGACCTGTACGGTCTGGTGCATGAGAACACTCTGGTCAAGCACAAGATGATTGTGAACCCCCGCGCCAAGGGAACAG
TGCGCTACATCGCCCCCTCCGGCAACTACAAGGTCGACGATGTCGTCCTGGAGACCGAGTTCGATGGAGAGATCACCAAGCACACCATGTTGCAG
GTGTGGCCAGTGCGTCAGCCACGTCCCGTGACCGAGAAGCTGCCCGCCAACCACCCCCTGCTCACCGGACAGCGTGTGCTCGACTCGCTCTTCCC
CTGTGTCCAGGGCGGTACCACCGCCATTCCCGGAGCTTTCGGTTGCGGCAAGACTGTGATCTCGCAGGCTCTGTCCAAGTACTCCAACTCCGATG
TCATCATCTACGTCGGTTGCGGTGAGCGTGGTAACGAGATGTCTGAGGTACTGCGTGACTTCCCCGAGCTGTCCGTGGAGATCGACGGTGTCACC
GAGTCCATCATGAAGCGTACCGCCCTTGTGGCCAACACCTCCAACATGCCTGTGGCTGCTCGTGAGGCCTCCATCTACACTGGTATCACCTTGTC
CGAATACTTCCGTGATATGGGTTACAACGTGTCCATGATGGCTGATTCCACCTCCCGTTGGGCTGAGGCTCTTCGTGAAATTTCTGGTCGTCTCG
CTGAGATGCCTGCCGATTCCGGCTACCCAGCCTACTTGGGAGCCCGTCTGGCCTCCTTCTACGAGCGTGCCGGTCGCGTTAAGTGCTTGGGTAAC
CCCGAGCGCGAGGGATCCGTGTCCATTGTCGGAGCTGTGTCTCCTCCTGGTGGTGACTTCTCCGATCCCGTGACCTCCGCCACTCTGGGTATCGT
GCAGGTGTTCTGGGGTCTCGACAAGAAGTTGGCCCAGCGCAAGCACTTCCCCTCGATCAACTGGCTCATCTCCTACTCGAAGTACATGCGTGCTC
TGGATGACTTCTATGACAAGAACTTCCCCGAATTCGTGCCGCTGCGTACCAAGGTCAAGGAGATCCTGCAGGAGGAGGAGGATCTGTCTGAGATC
GTGCAACTGGTCGGCAAGGCCTCTCTGGCCGAAACCGACAAGATCACGCTGGAGGTGGCCAAGCTGCTGAAGGACGATTTCCTGCAGCAGAACTC
CTACTCCTCGTACGATCGCTTCTGCCCCTTCTACAAGACCGTGGGCATGTTGAGGAACATCATCGACTTCTACGACATGGCCCGTCACTCCGTGG
AGTCTACGGCTCAGTCTGAGAACAAGATCACCTGGAACGTGATTCGTGAGGCAATGGGCAACATTATGTACCAGCTGTCATCCATGAAGTTCAAG
GACCCCGTTAAGGATGGTGAGGCCAAGATCAAGGCTGACTTCGAGCAGCTGCACGAGGACCTGCAGCAGGCCTTCAGAAATCTGGAGGACTAGAG
ACCGCGCTGGCCCTACTTTTACACTCTAATCTTATATTTGTTATATAGTTAACGTTTAAAAATGAAAGCAGTCAAAAACCATCCGAAAAAGCCTA
ATCAAACACCAACAATTCCGTGCTGCATTCGATGAAAAACAAAAGTCCAACAAATACCACAACTTCTTGGTGCCTGCGAGAGATGTAAACATTCC
GGCCTGCGGTTAATACTTTCCCCTAACCACGCCCCCTCCGCCCCTTGAAGGGCAACTCTAGGCAACAGCAACTACAACGTCCTGCTATGTACTTC
CATTTACAACAACAACACCAACATACACTTGAATAAAAGTACACGGACACTGGCGCACACACAACACATACATAAAAGACACAAATACAAATGCA
TGCATAAATAGTATTATTGTTTAATGAATGGAAATTCTTGTTTATTTGTGAAAAAAGTCATGTTTTCTCCCTGTTTGTTTGTTAAATTTATGTAA
ATATTTAAAGTATGAAATATTAAATGTACGAATAAAGTGCAACAACAAATACATTTAATGTAA
(SEQ ID NO: 1190)

Start ATG: 149

MSNLKRFDDEERESKYGRVFAVSGPVVTAEAMSGSAMYELVRVGYYELVGEIIRLEGDMATIQVYEETSGVTVGDPVLRTGKPLSVELGPGIMGS
IFDGIQRPLKDINELTESIYIPKGVNVPSLSRVASWEFNPLNVKVGSHITGGDLYGLVHENTLVKHKMIVNPRAKGTVRYIAPSGNYKVDDVVLE
TEFDGEITKHTMLQVWPVRQPRPVTEKLPANHPLLTGQRVLDSLFPCVQGGTTAIPGAFGCGKTVISQALSKYSNSDVIIYVGCGERGNEMSEVL
RDFPELSVEIDGVTESIMKRTALVANTSNMPVAAREASIYTGITLSEYFRDMGYNVSMMADSTSRWAEALREISGRLAEMPADSGYPAYLGARLA
SFYERAGRVKCLGNPEREGSVSIVGAVSPPGGDFSDPVTSATLGIVQVFWGLDKKLAQRKHFPSINWLISYSKYMRALDDFYDKNFPEFVPLRTK
VKEILQEEEDLSEIVQLVGKASLAETDKITLEVAKLLKDDFLQQNSYSSYDRFCPFYKTVGMLRNIIDFYDMARHSVESTAQSENKITWNVIREA
MGNIMYQLSSMKFKDPVKDGEAKIKADFEQLHEDLQQAFRNLED*
(SEQ ID NO: 1191)

Name: vacuolar ATPase subunit A
Classification: enzyme

Celera Sequence No. : 142000013384768
GAAATGAGTTTTGTTTTGTTTTGTTTCTTCCGAGTGTTTGTGTGTTTATGTGTGTGGGGAGGGGGTGTATTCTGTGTGCGGCGTGTTTTGAGTGA
GAGAGATAGAGAGAGAGCGCGAGTTGCTGCGGGTCGACGGTCGAAGGGGGTGGTGGTGGAGTTGGTGGTGGGGGGCTTGGTTTATACGACAAGTT
TTGATTTATTATTAAATTTAAATACCTATGTATATAAATTACGTTTCTGTTTATTATAATTATTGTTGTTTCCATCTTAATCATTTTGTTTTCTT
TCGCTTTTTATTTTTCATATTTTTTTTTTGTTTTTTGTATGTAGTGGGCAACTGCGGCATTTGTAAATTTCTTTATATTTAAATGTTCCTTTTGA
CTGTGTAAAAAATATCGATTTCCATCTGATCTTGTTTTGTAGTTACTATTCATGTATGCATTTGCTTTTCGTTTTAGTTAAATTACGTTAACGCTG
CATTCTGAACTCTCTGTTGCTGCTGATTCTGCTGCTTGTTCTTCGGATTCTTGATCGGATTCTTCTGATTCTTCATCTTGGCGCGCTTTCTATGC
TATTGAAATGTTGTTTGTGGTGCTGCTTACTGCCTTCTGGATCGGGATCCTATATTCCGCTCTGATCTGATCGGTTATGTTCATGTTATGTCGGG
TTGTGTGTGTCTGTGTTGTGTGTATGAGAGTGGAGTGTGTTGGGTGTTCGCATCTCGTTATATGTTGTATATATATATATATATATGTGTATATA
TATATATATATAATATATTATATGTATGTATAGTTAGTTGCTTAATAGTAGAATTTCTTGAATGTTGTTGTGGTAAAGTGTAGGTAATGTTGCTC
TATGTCTCTATGTCGACTCAACTGCACTACATACATATGTCTTTCCACCGGATACGCGGCGAACCGAAACGTGCCGAGCCGAACCGATCCCCGTT
TCTGACCCGCATCCGCATCCGTATCCGTATTTCGTTTCCTCACCTCCGCCTCATTCGCTGCGCAGTTTCTTTAGATCCGGTGACTTCTCCCCCAC
GCCCACACCCACTCCGCCGGCGTTCTTCAGCTCCATATCGCAGTGCAGGGCAGTACGCTTCTGTCCAATGGCTGGTGCCGAGTCTGCACCCGCTG
CTACCGGTGAAACCGCATCCACCGCCTTGTTCGCCGCCAGCTGCTGCAGTTTACTGTCCCTCACAATGCCGTTGCTGCTATTGCTCTCGTCAGCC
TCTAGCTCCGCCTCATTATCCTCCTCCTCGTCCAGCTCATCTTCCTCCTCGTCCTCCGCCTCATCCTCATCCTCGTCGCCCAGGACGCCGTTCCC
GTTACCATTTCCATTGGCTGGTGCTGCAGTCGCTTTGCTGGCTGGCTGTGGTGCTGCTGTAACCGCTTCCTCTTCTGCCAAAGGAGCAGGCTGAC
CGTTGTTGGTGATCGAATTGTTAGTTTTGTGGGGCTGGCTCGGCGACTGCTTTTGATTCTGATTCTGGCTCGAGTGCTGTGTGGGAGTCAGGATG
GGCAGGCTGTTGGTCTTGGGCGGCGCCTCCTGATTGCTTTCAGAGTCCGAGGCGAGCGGTGTTCCACTCGAACCGATGCCAATGCCAATGTCTAG
GGCGATGGGCTCACCGTCCTCTGTGGAAGTGGTGGCCGTTGTCTGTGTGGTGCCATCGTTGTCATCGATGATCGGCTCCTGGGAGGTGGAATCGT
TCGAAACAAAGTTGGAGTCACCGTCCTGCAGGGCGGCGCCAACGGCAGCTGCGTTGTTCTTGGCCTCGCCCGACTGTAGAGGCGTCAGAGCAGCC
GGGTTGGTGTTCTCATTCTCTGTCTCCGATTCTGTAGCAGTGTTGCGACCGCCTGGGGGATAGAAAGCATTGGATTAGCCATCAATGGTCAATTT
GTTAACTCGGCGAACTGCGGTCAGAGTAATCAAACAAAGAAACTCTGTGTTTGAAATTATTAGACATCCTAACACTTTTGAAAAGCTGCCAACAA
GTATAAGCTACTGATAATATGTTAAAAGTTAACTATTTTACAGTAGTAACTTTACAATTCCTCCTTTTTATTTAACATGACGCCACGAGTAACGA
ATAAATTGTAAATTGTAAATTGACCACTAGGCTACTACAAACATAATGTTTAATGGAAAATTCCGGATAGGAAAAATACTTGGTTTCTGGAAAAG
ACCACTCGGTTTGAGTGTTTTGTTGCAAGGGTGTATACTCAAGCCGCAGTTATCGGATCATCTTAGCTGCTTACCTGCTCCTTGGCTTTCGTCGT
CCAAATCAACACCCACACCATCGTTGGTATCGTCGCCATCGAGCACCTTGCTGCTGTTGCCGTTTGTGCTGAGTGAACCGGTGCCAGTGGAGGCG
CCGGATCCAGGCGGCGGCATATCGTCGAGCATCTCGGGACTGAGATCATTGGCCACATAGTGTGACCAGAGGGCCAGCTCCACGCGATGAGGCGA
CCAGTGCGGCGTATCCCCGCCCACCTCCGCATTGAGGCGCTCCACGGTGGCCTGAATGTGATTGACGAAGTTGAGGTACTCCTTGGTGGTGTAAT
CGATGCCCTCGATCTCTGGTATGGCCATCAGGCACTCGTCGGCCATGAATGGTGCCGAATCGGGAGCTGCGGCTGCCAGCAGTGCACTGGCCATT GTGGTGCCAACGCCCTTGAGGTTCGATAAAGCTGTGATCGCCTGCTCCAGATTGGGCAGCTTGCGGAAGGCCTTCTTTGTCTCCTGGATGACGGC
GCGCGGTGTGTTGACCTTGACCAGGTAGGATAGCTGCGGATAGAATTTGCCGCGCGACTGCTTCCACTTCATCGACTGGACGAGCTCATCGTATA
CCATATGCGCGTCCTTGCCGCGTGCCTTAATCAATTTGGGCAGTTCATTCTGATACCACTGATCCAGGCGGATCAGCTCTTGCGGCTTCTTGCAG
CGCTTCTCGGCCTTTAGCTTAAGAACCTGGGGATAGAGCTGGTAGCAGTACTCGAACTGTTTGGTGCTCCCGGTCTCGAAGAACGAGACCGTCGC
CTTGCCGTTGGACATCTTCTGCGGATGCGGATGTGTCGTTGTCGCCTGCTAATGATTGGTGGTATCGCTGTATCTCCTTATCGTGGTATCTATCG
CCTTGGGGCCCAGGACGTTGGCTGATCCGCAAGTGACCGGCTGGCTATATATGCGGCAATATATGTACTTTGGTGTAAGCTACTATACGCCAAAT
CAATTTATTGCTTACTGTTTAGTCTCCTGCTTTTCCTGTCCGTTCCGAGCTGCTCCTGTCAACGTACTGCTATTCGTGCGTTGAGAGTTCCCGGC
GAGAAAGAAGCGAGTACGTGAGAGACAGAGAGAATGCGAGTGCGAGAGAGGGAGCACGAAGAAGCAGCAACGCAAAGGAGAGTGGATGAAAAGAG
AAGAAAAGAGGCACACAATTAGGTTTACAGTTACGATTACATATGCAAGGGGGATCGGTGCGGTGGCATAGGGAGGTAGTTCGATTGATTACTGT
TAATGCTGCTGCTGCTGCGGCCGTGTCTCTGTTGTTTGTTGTATTTACTCAATCCGATAATCGCTCACTATTTGCCAAAAATCTGCTCGCTTCCG
CCGCCGTTTGCACAGCACACAAATCGAATTTTTACAGTGCTGTCGTCGGGTTCTTTTTAGTCCGCCATGCACTCACACAGTCAAACTGACAGGCA
CACGGATGGACACACACACACTTACTCAGCACACTCGCTCTCGCACACCCAAAGAGAGCCAGGCGCTCATACACAGGCAAAAACACGCACACAAC
ACACACACTGACTTAAACACGCACACACTTATATACTGAGGCAACAACAGCAGCAGCAGAAAATTTCTTTTTCATCTAGGTTTTCAAAAAAAATA
CGAACGCGAGCATTAAATAAACGAATGCTACTATTTTTCGCTGTTGTTGTTGTTTGTGCTTTTTTCGTACCTCTTGTCTTTTTGGCAAACGGTGA
GAACAGCTTTTCACTAGCGCACTGCACGCACACAGATGAGTGGGTGAACAACAAATACCTTTTAGTTAGTCGCCGCCAGTCTTCCTTTCCGTCCA
CATCCAAACAACTACTCCAATGCTTTGCTGTTTTTCTGTGTTGCCTCTGCTTTGCTTTGCTTCGCTTCGCCTCTGTGCTTGTGCTGTGCTGCGTG
CTTCGTGCTGTGCCCGTGCTGTGCTGCTTCTTCTTCTTCCTCTGCTGTTTCAGTTTCTGCTTTCTGCCTGCAGGGGCGCCGTTGACAACTGACAA
ATAAAAAGGGGTTACTCTGTTCTCGAAATGAGCACGCCACCGAAGGCACAACAAAAAATTAAAAAGGATCGGAGCGGAGCGATGCAGCTGTGCGA
TGTGCTGCTAACTCGTGTGACGGGAATTGGGAATTGGGATTGCGAATGGGAATGGGAGGGAATACGAGAAGCGAATATGGGAATGACGAACGACG
ACGAACCGGGAACAGGAGTTGTCGTTCTATCTCGCCCGCACTCGGTGCCCGAATGTATCTGTATCTCTCTGGCACCCTCGGCGTTCCATTTCATT
TTGCCGGCGACGTCCGTGCTCTCTGCCGCCGCTCTGCCATCGCCTCTGCCGCTGCGTTTATGCGCAGTGCGTCATTACACGAATACCTGTTTAAA
GCGGAGGCATAAACGCGGCTTTGTCGATC
(SEQ ID NO: 1192)

Exon: 3684..3513
Exon: 3299..3246
Exon: 3179..2260
Exon: 1857..1001
Start ATG: 3055 (Reverse strand: CAT)

Transcript No. : CT37627
GAGTGCATGGCGGACTAAAAAGAACCCGACGACAGCACTGTAAAAATTCGATTTGTGTGCTGTGCAAACGGCGGCGGAAGCGAGCAGATTTTTGG
CAAATAGTGAGCGATTATCGGATTGAGTAAATACAACAAACAACAGAGACACGGCCGCAGCAGCAGCAGCATTAACACAGTACGTTGACAGGAGC
AGCTCGGAACGGACAGGAAAAGCAGGAGACTAAACACCAGCCGGTCACTTGCGGATCAGCCAACGTCCTGGGCCCCAAGGCGATAGATACCACGA
TAAGGAGATACAGCGATACCACCAATCATTAGCAGGCGACAACGACACATCCGCATCCGCAGAAGATGTCCAACGGCAAGGCGACGGTCTCGTTC
TTCGAGACCGGGAGCACCAAACAGTTCGAGTACTGCTACCAGCTCTATCCCCAGGTTCTTAAGCTAAAGGCCGAGAAGCGCTGCAAGAAGCCGCA
AGAGCTGATCCGCCTGGATCAGTGGTATCAGAATGAACTGCCCAAATTGATTAAGGCACGCGGCAAGGACGCGCATATGGTATACGATGAGCTCG
TCCAGTCGATGAAGTGGAAGCAGTCGCGCGGCAAATTCTATCCGCAGCTATCCTACCTGGTCAAGGTCAACACACCGCGCGCCGTCATCCAGGAG
ACAAAGAAGGCCTTCCGCAAGCTGCCCAATCTGGAGCAGGCGATCACAGCTTTATCGAACCTCAAGGGCGTTGGCACCACAATGGCCAGTGCACT
GCTGGCAGCCGCAGCTCCCGATTCGGCACCATTCATGGCCGACGAGTGCCTGATGGCCATACCAGAGATCGAGGGCATCGATTACACCACCAAGG
AGTACCTCAACTTCGTCAATCACATTCAGGCCACCGTGGAGCGCCTCAATGCGGAGGTGGGCGGGGATACGCCGCACTGGTCGCCTCATCGCGTG
GAGCTGGCCCTCTGGTCACACTATGTGGCCAATGATCTCAGTCCCGAGATGCTCGACGATATGCCGCCGCCTGGATCCGGCGCCTCCACTGGCAC
CGGTTCACTCAGCACAAACGGCAACAGCAGCAAGGTGCTCGATGGCGACGATACCAACGATGGTGTGGGTGTTGATTTGGACGACGAAAGCCAAG
GAGCAGGCGGTCGCAACACTGCTACAGAATCGGAGACAGAGAATGAGAACACCAACCCGGCTGCTCTGACGCCTCTACAGTCGGGCGAGGCCAAG
AACAACGCAGCTGCCGTTGGCGCCGCCCTGCAGGACGGTGACTCCAACTTTGTTTCGAACGATTCCACCTCCCAGGAGCCGATCATCGATGACAA
CGATGGCACCACACAGACAACGGCCACCACTTCCACAGAGGACGGTGAGCCCATCGCCCTAGACATTGGCATTGGCATCGGTTCGAGTGGAACAC
CGCTCGCCTCGGACTCTGAAAGCAATCAGGAGGCGCCGCCCAAGACCAACAGCCTGCCCATCCTGACTCCCACACAGCACTCGAGCCAGAATCAG
AATCAAAAGCAGTCGCCGAGCCAGCCCCACAAAACTAACAATTCGATCACCAACAACGGTCAGCCTGCTCCTTTGGCAGAAGAGGAAGCGGTTAC
AGCAGCACCACAGCCAGCCAGCAAAGCGACTGCAGCACCAGCCAATGGAAATGGTAACGGGAACGGCGTCCTGGGCGACGAGGATGAGGATGAGG
CGGAGGACGAGGAGGAAGATGAGCTGGACGAGGAGGAGGATAATGAGGCGGAGCTAGAGGCTGACGAGAGCAATAGCAGCAACGGCATTGTGAGG
GACAGTAAACTGCAGCAGCTGGCGGCGAACAAGGCGGTGGATGCGGTTTCACCGGTAGCAGCGGGTGCAGACTCGGCACCAGCCATTGGACAGAA
GCGTACTGCCCTGCACTGCGATATGGAGCTGAAGAACGCCGGCGGAGTGGGTGTGGGCGTGGGGGAGAAGTCACCGGATCTAAAGAAACTGCGCA
GCGAATGA
(SEQ ID NO: 1193)

Start ATG: 351 (Reverse strand: CAT)

MSNGKATVSFFETGSTKQFEYCYQLYPQVLKLKAEKRCKKPQELIRLDQWYQNELPKLIKARGKDAHMVYDELVQSMKWKQSRGKFYPQLSYLVK
VNTPRAVIQETKKAFRKLPNLEQAITALSNLKGVGTTMASALLAAAAPDSAPFMADECLMAIPEIEGIDYTTKEYLNFVNHIQATVERLNAEVGG
DTPHWSPHRVELALWSHYVANDLSPEMLDDMPPPGSGASTGTGSLSTNGNSSKVLDGDDTNDGVGVDLDDESQGAGGRNTATESETENENTNPAA
LTPLQSGEAKNNAAAVGAALQDGDSNFVSNDSTSQEPIIDDNDGTTQTTATTSTEDGEPIALDIGIGIGSSGTPLASDSESNQEAPPKTNSLPIL
TPTQHSSQNQNQKQSPSQPHKTNNSITNNGQPAPLAEEEAVTAAPQPASKATAAPANGNGNGNGVLGDEDEDEAEDEEEDELDEEEDNEAELEAD
ESNSSNGIVRDSKLQQLAANKAVDAVSPVAAGADSAPAIGQKRTALHCDMELKNAGGVGVGVGEKSPDLKKLRSE*
(SEQ ID NO: 1194)

Celera Sequence No. : 142000013384589
GTGGCACCATCGAGCCCCTCAAAGAGGAGCACATTTTCGTGGTCCTCGACGCCGCTACTGCCGTGTCCACCGTCCGTGCCGCGACCCGTTAATGG
CGGCGAATGCGGTCGATGATCCAAATGGATGTCGTCGGCGTGGGCATGGCCATCCTCCTCCGCGACGACCATGTTGCAGGAGGAGGAGGCGGTTA
GGGGCAACGCCCACACACTGCGCGCCGCCCCCGGACTTGGATGCACCTTCGAGGCCATGTAGAACTCGAAGTCCACGCCCAGACGGTCCGCCGTT CCACCGTTGCCTTGATGCAGGGGGTTTTCCAGTAGGTGTGCAATCTTGTCGCCTTTTTCCGTTACGCTCCGACCGAAATTTGTACTCTGTTTGGC
CAATCTTAGGCGTGGAATGCTAGGTAAACACGACTGCACTCGATGGCGAGGAAATTATGTCAGCACTGTGAGAAAATCAATATTTGTCCCGAATC
GCAGGACTCGAATTGGGGCCACTTTCGAACTCGACTTGGCGCCAAACAAATCAACAGCTGACCGTTATTTTCGCAGTTGGGCGCGCAGTGTTGCC
AACACATACTGGTAATTAAGACTTTTCTCAGCGAGGGGTGATTTAAGATTTAAGTCAAGAAGTATTAAAGAAAAAAATATATATATTTAATTTGTT
GGAAGGTCAATTGTTGAAACCGAGGTATCATTTAGCTTAACTTAAATATACTAGAAATCTCGTGGCATAAGCAAACTAAAAAAAAAAGGTTTATC
AACTGACTTTTATATTAGTTTTAACATTATTGGGAAACATTTGTTTTCCGCCGCTAGAAACCTTTAAAATGTATACTACTATATTGCTTGGTACG
AATGTTGCATTTTGAACTGATGCTAGCATTGCATTTTGTAAGGTTCCCATGTCTCTGTTATTTTGCCACCTGGTAACACTGTGCCCCTTTTTGAT
AAATTTGTTTCGTAAAAAATGGGCGACAACGTGGTGACGGAACTAAATAACTTGGATTTGAACAATCAAAAGGCATGTTAAACTCTTTTCGAACT
GCATTCGAGTGTATGAGAAGTGCTAGTTAGCCGAATTATGTTGAAGTTGGCGCCGCAGGGCGGCAGATATTATAGCCAAATAAGCCGCATTTGCC
AGTGGATTTTGCCGAAAATTCAGACGCAGTCGAAGCCACCAAAACAACAACAACAACAGCAACCACAATTGAAAGAACAACAACAACACAGCTAC
GCAACTTTGGTTGGTGTTTTAAGCTAAAAAGAATTGACCTAAACTTCAATTTAAACGCCTGTTACTGCTGGCACGTGTAAATGTTATGCTTGTCT
GTGTGAGTGTATGCGATTCTCCAATGAATCAGTGCCGCCGGCTGTGACGTCACTAACAACCAACCAACTTCATGAGTGTCTGTTTTTTTTTGCTA
CTCTATTGCATCAGCCATAAAACGACGAAGATACGCTCAAAGACGGCTCGATAAAACAGAGATAGGAGCACCGAAAACATAGCACCGAAAAGTGC
TCATTGCCATGTCCCCAATTGTTTAAACAATAAGAAAACATCAGTCGAAAGTAGATACCGAAAAAGAGCATTTGTCTAATTGCATACGTAGCACA
CTTGTGGCCACTTGAATATCTCCGGTTTATATTGATTTTTAACCTATTTCCGATGGATTTGCAGGCTGCCAAGATGAAGAAGGAGAAAAAGGAGA
AGCCATCCGGCGGTGGAGATACTCGCAAGGGTAAGTAATTCTAACTAAGAATTAAAAACACAAAACGCACTTCCGTCTGTAAGATATGTAGCATA
TCTTTAAGATTAGCTGCCTTCTTCTCTCTAATACCTGAAATTCCACTGATCTCTGCTATATTGATTTCAGAACTCAGTCCCTTGCCCAAGTACAT
CGAGGAGCGCAATGTCTTCTGGGAGAAGTGCAAGGCGGAATACGAGGCCGAACTGGCGGCCAAGAAGCGTGAGCCCATCAAGGTGACACTGCCCG
ATGGCAAGCAGGTGGACGCCACCTCCTGGGAGACCACTCCGTACGAAGTGGCCCGCGGCATTAGTCAGGGTCTCGCTGACAACACCGTCATCTCC
AAGGTGAACGGCGAGGTGTGGGATTTGGACCGTGTGCTCGAGGGAAACTGCACCCTGCAGCTTCTCAAGTTCGACGACCCTGAGGCGCAGGCCGT
CTTCTGGCACAGCTCTGCCCACATCATGGGTGAGGCCATGGAGCGCATCTATGGTGGACACCTGTGCTACGGTCCGCCCATTGAAAACGGCTTCT
ACTACGACATGCATCTGGAGGGCGAGGGTGTAAGTAATTTGTGATGTTCAGTAAGAATTAAATTAAATTGAACGCCCAATTAGATCTCCACCAAC
GACTACGGCGCCATGGAGGGTCTGGTTAAGCAAATTGTCAAGGAGAAGCAGAACTTCGAACGTCTGGAGATGAAGAAGTCCGACCTGCTGGAGAT
GTTCAAATACAATGAGTTCAAGGTGCGCATTCTCAACGAGAAGGTGACCACCGACCGCACCACTGTCTACAAGTGCGGTTCTTTGATCGATCTCT
GCCGCGGACCTCATGTTCGTCACACCGGCAAGGTGAAGGCCCTGAAGATCACCAAGAACTCCTCTACCTACTGGGAGGGTAAGGCTGACGCTGAG
ACACTGCAACGCGTCTACGGCATCTCGTTCCCCGACCCGAAGCAGCTCAAGGAGTGGGAGAAACTTCAGGAGGAGGCGGCTAAGCGTGATCACCG
CAAAATCGGTCGCGAGCAGGAGCTGTTCTTCTTCCATGAACTTTCGCCTGGCTCATGCTTTTTCCAGCCGCGAGGAGCGCACATCTACAACACCC
TGATGGGCTTCATCAAGGCGGAATATAGAAAGCGTGGTTTCCAAGAAGTCATTTCCCCCAACATCTACAACGCTAAGTTGTGGATGACCTCCGGC
CACTGGCAGCACTATGCCGAGAACATGTTCTCCTTCGAGGCCGAGAAGGAGAAGTTCGCCCTCAAGCCCATGAATTGTCCAGGACATTGTCTCAT
CTTCGATAACCGCAATCGATCCTGGCGAGAGCTGCCACTGCGAATGGCCGACTTCGGTGTGCTTCATCGCAACGAGCTCTCCGGTGCTTTAACCG
GATTAACTCGCGTGCGTCGCTTCCAGCAGGACGATGCGCACATCTTCTGTGCCCCCGAGCAGATTAAAAGCGAAATGAAGGGCTGCCTGGAGTTC
CTGAAGTATGTGTATACCATTTTCGGATTCTCCTTCCAGCTGGTGCTGTCCACACGCCCGGATAATTACCTTGGCGAGTTGGAACAGTGGAATGA
TGCGGAAAAGGCGCTGGCTGAATCACTCAACGAGTTTGGAATGCCGTGGAAGGAGAACCCCGGCGATGGCGCCTTCTACGGACCGAAGATTGATA
TTACCATTATGGATGCACTGAAGCGTGCCCATCAGTGCGCCACCATCCAGTTGGACTTCCAGCTGCCAATTCGTTTTAATCTCAGCTACATCGCC
GACGATGGCGAGAAGAAGAGGCCGGTGATCATCCATCGCGCTATTCTTGGCTCAGTGGAGCGGATGATTGCCATTCTCACGGAGAACTTTGCTGG
CAAGTGGCCCTTCTGGCTATCACCGCGCCAGGTGATGGTCGTTCCAGTGGGTCCTGCCTATGATCAGTACGCCCAGTCAGTGCGGGATCAGTTGC
ACGATGCTGGATTCATGAGCGAGGCGGATTGCGATGCCGGCGACACGATGAACAAGAAGATACGCAATGCTCAGTTGGCCCAGTTCAACTTCATT
CTGGTGGTGGGCGACAAGGAGCGCTCCTCGAATACCGTTAACGTGCGCACTCGGGACAACAAGGTGCACGGCGAGGTCTCCGTGGCGGAACTCAT
CACAAAGCTGCAAAAGATTCGCGACGAATTCATCGCCAACGAGGACAGCTTCTAAGACTCTATTTCGAACTATTTATCAAAAGTATACTTAACAT
TTGCATAGCAAAGCAAGTACGCATTTTTGTTCTTTCTATGTATTTACGCTTACGAAACCGGAATTCACAAATAAAAAACCAAATCCAAACACATT
TTAAGGTGTTTCAAATAGAAGAGAAGAGCATGCAATCAAATAAAAGCAATTCGATTCAATATACGATTATTAAGCTTCCCCAACTAAAAATCGTA
TTTTTCTGATCCACCTTAAGCCGCCTATTTCACTCCAGTTTCTTGACGAATCAGTGGAATTTGTCAGCAATTGAGGACTAGTCATGCCGACACAG
AGGTGCGCTGTAGTCCATTCAGGAACGATTTGGAATGATAAGATAAGTCGGCCCACATTTGGCGGAAAACTTTTTGGGAAAGGTGTGCGTGCACC
CACAACGTATGAGTCATGTTTTGAATTTATTTTTTTGTATTAATTTATTGCTAGTATCTTGTATACTTTTCATTTTCATAATTTGATTTATTAAA
AATTGCATCAATAGTTTATGTTTTTATTCAATTATCAATTTTGTAAGCTTTTGCTTTTCGCGTAAAAAATGCACAAAGTTCTCTCGCTAATCGAA
GCAAAAATCGTTAATAATATTGTTAAGTGTTTGCTCTGCTCGTGCTCTGCTTATCTGTTTCAGTTTTAGTCATAAAAATACATATTTTATATTTG
TGTATATTTATTCATAAGATGCACGTGGCCAAGTCCTATGCCATCCACAGTTCCAGTTAGCAGTCGCGTTCGCTGTGCTAAAAAAAAAACCGAAA
TCCTAACCAAAACTGGCGAAACAAAAGCCGCAAACAGAACAGAACGGGGGCTAAAATTGGAAACAAAATGCCTGGCTGGTGGAATCATTGAACAC
AGACTGGCTGCGTGGTATCTACGACTGCTGGAGATGCCGAGAGCTGGAATGTCGGAGGATCCTGGGACCGCCTGGCCTGACATAAGTACATGGTC
TTGGGTTTTT
(SEQ ID NO: 1195)

Exon: 1001..1244
Exon: 1680..1740
Exon: 1876..2309
Exon: 2364..3950
Start ATG: 1689

Transcript No. : CT37701
CTTGGATTTGAACAATCAAAAGGCATGTTAAACTCTTTTCGAACTGCATTCGAGTGTATGAGAAGTGCTAGTTAGCCGAATTATGTTGAAGTTGG
CGCCGCAGGGCGGCAGATATTATAGCCAAATAAGCCGCATTTGCCAGTGGATTTTGCCGAAAATTCAGACGCAGTCGAAGCCACCAAAACAACAA
CAACAACAGCAACCACAATTGAAAGAACAACAACAACACAGCTACGCAACTTTGGCTGCCAAGATGAAGAAGGAGAAAAAGGAGAAGCCATCCGG
CGGTGGAGATACTCGCAAGGAACTCAGTCCCTTGCCCAAGTACATCGAGGAGCGCAATGTCTTCTGGGAGAAGTGCAAGGCGGAATACGAGGCCG
AACTGGCGGCCAAGAAGCGTGAGCCCATCAAGGTGACACTGCCCGATGGCAAGCAGGTGGACGCCACCTCCTGGGAGACCACTCCGTACGAAGTG
GCCCGCGGCATTAGTCAGGGTCTCGCTGACAACACCGTCATCTCCAAGGTGAACGGCGAGGTGTGGGATTTGGACCGTGTGCTCGAGGGAAACTG
CACCCTGCAGCTTCTCAAGTTCGACGACCCTGAGGCGCAGGCCGTCTTCTGGCACAGCTCTGCCCACATCATGGGTGAGGCCATGGAGCGCATCT
ATGGTGGACACCTGTGCTACGGTCCGCCCATTGAAAACGGCTTCTACTACGACATGCATCTGGAGGGCGAGGGTATCTCCACCAACGACTACGGC
GCCATGGAGGGTCTGGTTAAGCAAATTGTCAAGGAGAAGCAGAACTTCGAACGTCTGGAGATGAAGAAGTCCGACCTGCTGGAGATGTTCAAATA
CAATGAGTTCAAGGTGCGCATTCTCAACGAGAAGGTGACCACCGACCGCACCACTGTCTACAAGTGCGGTTCTTTGATCGATCTCTGCCGCGGAC
CTCATGTTCGTCACACCGGCAAGGTGAAGGCCCTGAAGATCACCAAGAACTCCTCTACCTACTGGGAGGGTAAGGCTGACGCTGAGACACTGCAA
CGCGTCTACGGCATCTCGTTCCCCGACCCGAAGCAGCTCAAGGAGTGGGAGAAACTTCAGGAGGAGGCGGCTAAGCGTGATCACCGCAAAATCGG TCGCGAGCAGGAGCTGTTCTTCTTCCATGAACTTTCGCCTGGCTCATGCTTTTTCCAGCCGCGAGGAGCGCACATCTACAACACCCTGATGGGCT
TCATCAAGGCGGAATATAGAAAGCGTGGTTTCCAAGAAGTCATTTCCCCCAACATCTACAACGCTAAGTTGTGGATGACCTCCGGCCACTGGCAG
CACTATGCCGAGAACATGTTCTCCTTCGAGGCCGAGAAGGAGAAGTTCGCCCTCAAGCCCATGAATTGTCCAGGACATTGTCTCATCTTCGATAA
CCGCAATCGATCCTGGCGAGAGCTGCCACTGCGAATGGCCGACTTCGGTGTGCTTCATCGCAACGAGCTCTCCGGTGCTTTAACCGGATTAACTC
GCGTGCGTCGCTTCCAGCAGGACGATGCGCACATCTTCTGTGCCCCCGAGCAGATTAAAAGCGAAATGAAGGGCTGCCTGGAGTTCCTGAAGTAT
GTGTATACCATTTTCGGATTCTCCTTCCAGCTGGTGCTGTCCACACGCCCGGATAATTACCTTGGCGAGTTGGAACAGTGGAATGATGCGGAAAA
GGCGCTGGCTGAATCACTCAACGAGTTTGGAATGCCGTGGAAGGAGAACCCCGGCGATGGCGCCTTCTACGGACCGAAGATTGATATTACCATTA
TGGATGCACTGAAGCGTGCCCATCAGTGCGCCACCATCCAGTTGGACTTCCAGCTGCCAATTCGTTTTAATCTCAGCTACATCGCCGACGATGGC
GAGAAGAAGAGGCCGGTGATCATCCATCGCGCTATTCTTGGCTCAGTGGAGCGGATGATTGCCATTCTCACGGAGAACTTTGCTGGCAAGTGGCC
CTTCTGGCTATCACCGCGCCAGGTGATGGTCGTTCCAGTGGGTCCTGCCTATGATCAGTACGCCCAGTCAGTGCGGGATCAGTTGCACGATGCTG
GATTCATGAGCGAGGCGGATTGCGATGCCGGCGACACGATGAACAAGAAGATACGCAATGCTCAGTTGGCCCAGTTCAACTTCATTCTGGTGGTG
GGCGACAAGGAGCGCTCCTCGAATACCGTTAACGTGCGCACTCGGGACAACAAGGTGCACGGCGAGGTCTCCGTGGCGGAACTCATCACAAAGCT
GCAAAAGATTCGCGACGAATTCATCGCCAACGAGGACAGCTTCTAA
(SEQ ID NO: 1196)

Start ATG: 254

MKKEKKEKPSGGGDTRKELSPLPKYIEERNVFWEKCKAEYEAELAAKKREPIKVTLPDGKQVDATSWETTPYEVARGISQGLADNTVISKVNGEV
WDLDRVLEGNCTLQLLKFDDPEAQAVFWHSSAHIMGEAMERIYGGHLCYGPPIENGFYYDMHLEGEGISTNDYGAMEGLVKQIVKEKQNFERLEM
KKSDLLEMFKYNEFKVRILNEKVTTDRTTVYKCGSLIDLCRGPHVRHTGKVKALKITKNSSTYWEGKADAETLQRVYGISFPDPKQLKEWEKLQE
EAAKRDHRKIGREQELFFFHELSPGSCFFQPRGAHIYNTLMGFIKAEYRKRGFQEVISPNIYNAKLWMTSGHWQHYAENMFSFEAEKEKFALKPM
NCPGHCLIFDNRNRSWRELPLRMADFGVLHRNELSGALTGLTRVRRFQQDDAHIFCAPEQIKSEMKGCLEFLKYVYTIFGFSFQLVLSTRPDNYL
GELEQWNDAEKALAESLNEFGMPWKENPGDGAFYGPKIDITIMDALKRAHQCATIQLDFQLPIRFNLSYIADDGEKKRPVIIHRAILGSVERMIA
ILTENFAGKWPFWLSPRQVMVVPVGPAYDQYAQSVRDQLHDAGFMSEADCDAGDTMNKKIRNAQLAQFNFILVVGDKERSSNTVNVRTRDNKVHG
EVSVAELITKLQKIRDEFIANEDSF*
(SEQ ID NO: 1197)

Name: threonyl-tRNA synthetase
Classification: enzyme

Celera Sequence No. : 142000013384832
GTAAAAAAGCGTAGCAAACTAGTTGGGCAACGGAAAAGGATGTGGCTGCTGCGATGGCGATGGCGATGGCCAATGGCAATTGGAATTGCAAGGAC
AACGCCAACGGCTGCTGCTAGGCACTGCTATGCCACGAAATCGAGCGGCCGGTTGAAGCCACCCTTGCGATTCATGTACTGGCGGTACTTTCGCT
TGAGGATTACATGCACTTCTCCGACATCGTTGCCCTCGACCTTCCTGTTCTTGGTGGTGTCGAACGTGCAGAATCCCATTGTCTTCAGCATCTCG
ACCTCTTCCGGCGATTTACCCTCCAGGTCCGCCTCGTTGATCTTGGGCCGGTCGGCAGCTGTGGCCGCCGCATTGTTCCTCGTCGTCCTTCGCGA
CGTCGATGGTCCGGAGCTGCTGTTGCCGCCGCTGCTTCCGCCGCCGCCTCCTCCTCCTCCTCCGGCGACCCTCGACCGCGATCTGCAAATTA
TGAATGTGTGTGCATAGTGAGTGGTGAGTGTTCTATAGATTTCGTTTGAGTGACAGGACCGACCAGTTGATTGCATTCGAATTGCAACGAGCCTG
GGAAATAACTGGGGCGACCTTGGGCGTTGTGCACCCGATTGTGCAATATGAAGTTTTAATTACGCGAAATGCGACACTTCTCAACCGGTCGGTTG
GCTTCATTAAAGACCATATTTACGTCTCGATTTTGGCAATCATCTGAAGACCCAAAATAACCGGCTTGTATATGCATATGCTAGAGAATTTCATT
CTAAGATTTAAAATCAAGCTCAAGATCCCTCTAAAATCCATTCTGAATCCATTTATATACCTAACAGACAATATTCCTCTATTCCTCTAGCTTAT
ATCTCAAAAACTTCCATTGGAAAATAGCTAATTGATGCTTGCAGCTCCCAGACTTTGTTTTAGTTTCGTGTTTTGTATTTCTTAAATGAAATGTA
GAAGATAACAGATAATCCTTATATCAAGTAGAAAGTGGGGAAAGTTTCGCTTAGGACATGTCCTCGATGAGGGCCGCACGCAGCTTGGTCGTCAC
TGTGGCGGGCTGTGCCTGGTTAAGCTTGAAGACGCTCTCGATCACGGAGATCTCTGTGGCCGTGGTGTTCATGCCCACGAAGGAGAGCCAGTCGT
TGACGACCATGCCGGCGGCGAGTACTTCGCTGCCCCGGTTCACTGTTCCGGCCACGAGGGGAACCTGCAGCAGGGACGACAGTTCGTCCTGGTCC
TGAATGCTCGTCTTGGGATGCACCATGCCGCCCTGGTTGCTCAGCACGGCGTAAGAGCCCACCAGTGAGTTGTCGGCAATGGTCTGGCGGAAGAC
CTCTACTTTGAGCACGTCCGCGATGATCTCCTCGGTCTCCTTGTCCAGATCCGGGTGCACCAGGGCCACATAATCATTGCAGGCGATAACGTTGC
CCAGCGCGGACAGGCGCTCCTCCACACGATAAATCTTCACGGCGTCTGGCAGGCTGTTACGCAGGTGTTGCAGCTCCTCGTCGGTGGTGGAGTTG
GGCACCAGCAGGCCGTTGCGGTTGCCCACGGTGAGGCGGCCGATGATCCGGCAGCCGCCCACATTCGCATGCACCACCGGGATGGTGTCGCCCAG
CTCCGCCTCGAAGGCGCTGTAGAAGGTCTCGGATCCACCGATGGCCACCAGGCAGTATGTGTTGGTTAGTTTAGTGAAGACGCCGATGTCGTCGT
TGTTCTCGAATTGGACGCGTAGAGCCATTTTCTCTGTATTTACGTGGATCCTCTTTTCCTGCTGGTTACTCTCTTTTCGGATTTACTGGCCTGAC
TGAGCCTGCTGCCGGATGAGTTCTGGATTCTGTTTATATGTCCGGAAATCAATTTAAATGTCGTGATGAAATTCGCACAATTTCGCTTCACGTGG
TAATTTTTTTTTGATGTTGGGACGCCAGAGCTGCATAGCCATCGATTGGCTGCCTATCGAAGTGTGGGTCTATCGATACTCGTGGGTAAATAAAC
AAGTTCTGAACGGCGATTTCGGGGGTTTGAGGGGTCAATTGTCCCCTGTGTTGGAATGTGTTCCTAAATCTACACAAACACTCCCTAAGCTTATC
CTAAACTTATAAATATTGGTTGCTATTTAAACCCCATTTCACGGTTATCCAGCACGCCCCTGAACTGTGACCCACATCCCCGATTTTAGTGACTA
GTTTTATACTTATCGTGGTTGGCATTTGGTACACTACACTTTCTTATTCACCTAGATCGCCGACTCCGCGCACGGTCGCGCTCCCGTTCCCGCTC
CCGATCTCGGCTGCGACTGCGGTCGCGATCCCGTTCCCGGTCGCGGCGACCGGCGCCTCCAGATCCGGATCCTCCGGCTGGCGCTACTCCGATGG
CCTCCCGCTCCCGGGAACGGCGCTCCCTGCGCTTCTTCCGCTCGGATCGCTCCTTCTCGCGTCTCCTGTGCGCCGGCGAGGCGGGACTTCGGCTG
CGGCCCATGGCTCCGTTTCGGTCTCTGCTTGTGTGGCGGTTTGAGTGATTGATGATGGTTTGCCTGCAGTGGATTTGAGCGGATGTTAGACTCCA
TGTACTCCAATTGCACCGCACGCATCCCGCTTACCGTTGCACTAGGCTGTGTCTAGCATTATTTGGGCGACACCGGCGGTGGGTAAAAACGCGCT
AACTTAAAACTAAAACCAAATAAACAACGCGCGTTATCTCGCCGCGACGCCGAAACGGAATGAGGAATGCAGAATGCGGATGATGATGCGAGGGA
TGCGATGCAAGGGCAAAACATGGCCACCTATCGGATATCGATTGATGGTCGATTTTATCTTCGATAAAAATGTATCCTATGTATATCGCATACCG
AATGTTTAAATCGATCTGTTTCCTTTTGAATATGAACTAT
(SEQ ID NO: 1198)

Exon: 1890..1001
Start ATG: 1738 (Reverse strand: CAT)

Transcript No. : CT38864
CGAAATTGTGCGAATTTCATCACGACATTTAAATTGATTTCCGGACATATAAACAGAATCCAGAACTCATCCGGCAGCAGGCTCAGTCAGGCCAG
TAAATCCGAAAAGAGAGTAACCAGCAGGAAAAGAGGATCCACGTAAATACAGAGAAAATGGCTCTACGCGTCCAATTCGAGAACAACGACGACAT CGGCGTCTTCACTAAACTAACCAACACATACTGCCTGGTGGCCATCGGTGGATCCGAGACCTTCTACAGCGCCTTCGAGGCGGAGCTGGGCGACA
CCATCCCGGTGGTGCATGCGAATGTGGGCGGCTGCCGGATCATCGGCCGCCTCACCGTGGGCAACCGCAACGGCCTGCTGGTGCCCAACTCCACC
ACCGACGAGGAGCTGCAACACCTGCGTAACAGCCTGCCAGACGCCGTGAAGATTTATCGTGTGGAGGAGCGCCTGTCCGCGCTGGGCAACGTTAT
CGCCTGCAATGATTATGTGGCCCTGGTGCACCCGGATCTGGACAAGGAGACCGAGGAGATCATCGCGGACGTGCTCAAAGTAGAGGTCTTCCGCC
AGACCATTGCCGACAACTCACTGGTGGGCTCTTACGCCGTGCTGAGCAACCAGGGCGGCATGGTGCATCCCAAGACGAGCATTCAGGACCAGGAC
GAACTGTCGTCCCTGCTGCAGGTTCCCCTCGTGGCCGGAACAGTGAACCGGGGCAGCGAAGTACTCGCCGCCGGCATGGTCGTCAACGACTGGCT
CTCCTTCGTGGGCATGAACACCACGGCCACAGAGATCTCCGTGATCGAGAGCGTCTTCAAGCTTAACCAGGCACAGCCCGCCACAGTGACGACCA
AGCTGCGTGCGGCCCTCATCGAGGACATGTCCTAA
(SEQ ID NO: 1199)

Start ATG: 153 (Reverse strand: CAT)

MALRVQFENNDDIGVFTKLTNTYCLVAIGGSETFYSAFEAELGDTIPVVHANVGGCRIIGRLTVGNRNGLLVPNSTTDEELQHLRNSLPDAVKIY
RVEERLSALGNVIACNDYVALVHPDLDKETEEIIADVLKVEVFRQTIADNSLVGSYAVLSNQGGMVHPKTSIQDQDELSSLLQVPLVAGTVNRGS
EVLAAGMVVNDWLSFVGMNTTATEISVIESVFKLNQAQPATVTTKLRAALIEDMS*
(SEQ ID NO: 1200)

Name: EIF-6 family protein
Classification: translation_factor

Celera Sequence No. : 142000013384665
ATCTCATCTCATATGAAAGCAATATCATATATGTATGTTAATATTAAATAGATATTAAACATAAAAATCCATCCCACCCACATTCCGCTGAAAAA
TGAAAACACTCGCTTTTGCCGAAGTGGAATTTTATTGTAATTAAATTTGTTGGGTGTACAAAGGTATGTTTTAAGGACTTTCTCTCTGCATTTAT
TACAATTTCTTCAAATGGTTTTAATTGCTGGGCTTTTGCTTCGAAGACGGGCAATCAAGTTTCAAGAATCCTATTTTCTTTAATCATACAAATTA
TGTTTTATTTCGCTTTAATATATAAGGATACATATATATATCTGCTATATATAGAAGTGTGTTGACTTGCGTATATTTCGTGAAAAGTAAAAGTT
TTCTTCTTCGCAATTTCCCTTGAACTAACATTCCAATTCGGGTTTTGGTTATGTTTTTTTTTTCTGTTTTACTCTCATTATTTTGTTTGTTTGTT
TTTTTTAAATAATTTTGCATTTTCTGCATACATGTGGTTTTGTGTTTTGCAATTTTTTCAATGATTTTTCCTTGGGTTTTTATTTGTTTTTAGTT
TTCGATTTGTTTAATAAAAAAATATGTATTTCACTGCCCAGAGCGAAAGCCATTTCTTACTTCCGCTTGCGTTAATATATCATTTTATGTATGTA
TGGTGTAAAAACATCATTTACTGGTAAAACTCTCGATATCCTTTGTAACAGAAATCGGAACGCAAATGAAATCGAGGCGACTTACCAGCTCCTTC
TCATTAAATACATATATGTTCTTGCAAATGTTTATAAATGTATGCATGTTTTTCCTTCTCTCGGATAATAGTGTAATCATAAAAATCCTGTCTGC
TTTTTTGTTGTTTATTAATATGCTTCATAAGTTGTTTACGCTTTAGCGCTTTTCATGTGTTTCTTGTATTTCTCATATATGTTGTGGTTGTTTAA
TATGTGTGTTGCTGTGTGTGTGTTTTTGTGTTTATATATATTATTTTTTTTTTGCTGTTTTTACATAGGTTTTGCCATTTTTTTGTAGTTTTTTC
GATTTATGTTTTGTTTTCATTTGTCAACATATTTTTTCAGCTGTTGGTATTCTGTATTTTCTCTCTTTTTTCAAAGTAGCAAAAACTTGACTCTC
ATATTCTTGCGGTTTTCTTTTTCTTTCTTTCTTTCTATTCTTCTGTTCTCTGCACAGTTTGCTTTCCATTTTTTCGTTTTTATTTTAACTCTTTT
GCAATTTTTTTGTTTTTTCTTTGCTTTTTTAAAAGTGTATGGTTGTCGCGTTTCTTTTTCTAAACAAAGCTTTCTTAAAGTTTGAATTTGAGAAA
AAAGAATTGAAAAAAATTACATATCGCTTTCGTGTTTGTTGTTGTTTGAAAGTGTGGATGGAAAAAGTGTACGAAAAACTCAATATGTATGTAAC
ACTAGAAACTTCTTTAAAATTTTTAAAACACAATTTCAATACTTGCAAGAAGCGGTTTACATGTATGCTTTGCTTTAATCTGTTTATTTTGCAAT
GGTTTTTTGGTGTTTTCATTATACGCATACAAAATAATATCGATCCAGTTAAAGCAATAACGAAATTTTTTTCATTTCACATTTTTCCGTTTTTT
TTTTTAATTAACATGTTTATGTAAAAAAAAAGAATTTATAAGTGGACTGCAGAATTTGATTGCGTGACTTTCTTCTTTTGCTTCGTGTACTTGCG
TAAATGCGTTCGAAATTAAATGATTGAAATTGCTTTTGTTGATGTTTCTGGGATTAGAAAAGAAAAAGCCGTAGATTTTTCGCTTTGTTTTTCTG
TGTTAATTGTGTGTCCTTGGCAATCCTCCCCTGCGCAAAGCATCAGTGAATGCGAATTTTTGTTGTTCATGTATTGAAAGATTAGTGGAAAACTG
CAAGGACAAAAGAGAGGCGAGTTTAGACAGCTTGAACTTTTCGGAAAATTTGTAGACTACTTACTTTTTGGGTGTAAAGTGTTCTTGTAAAATGT
TCATACGCTTGAGCTGTTCGAGCTTAGTTGGCGGGCTCGGTGACGCGGTGCACCTGAAGCACGGCCACAGCCTCCTCCACCTTGGCCTTAAGGGC
CTCCTGATCCTCGATCATGTGCAAGAGCTCAGAGTTTTCGATCTCCAACAACATGCCGGTGATCTTACCAGCCAAATTGGCGTGCATATGCTCAA
TCATCGGATACAGACGCTCGCCCAGGATCTGTTTCTGCTCCTGCGGCTTGGCGTTGGCCAGCAACGAGGCAATGAGCTTCTCAGAATCTGCAAGA
AAAATAGCAATGGTGCCATTAGTGACAAATTGTGCATATTTTCAGTCGACCTAAAACTTACTCTTTCCTTGCAATTGCTGTGGAATTGGCTGGGT
CTGATGCAACTGTGGCACTGGAGGATTGCGCATGTTTGAGGTGTACTTATAGTTGGAAGTACGCTGCTGGGCACCGCCAGCGATTTGGGCTCCGG
GGATCTGCATGTTGGGTGCTGCAGTTTGCTGGCCAGTAATAGCGCGTGCTCCAGTGTTGCGCATGTTGTTAGCCGCAGCAGCGGCGGCATGTGTG
CCCTGCACCTGAGGCTGTGCCCCGCGAGCGCCAGCAGCAGCCGAACGGAACTGAGTGGGCACCGCACCGGCTGTGCCCTGGAAGCCACCAGCAGC
GGCAGCTCCGGCCTGGACACCCTGTATGGCTGCTGGGGGACGCACCTGGGGCACCCAGCGGGGTGTGTTTCTCATCTGAGTGGCCACCTGGGAAC
CGAAGAAACGCTGATTTGACGGAAGGGTCGGCACAAAGAAGCCGCTAGCCGCGTTGGGCTGGTAGATCTGTCCCAGCTGCTGCATACGCATGCCG
GTCATGTGACGCATGTACTGCGAGGCGAGATGAGCCTTGCGCTCCTCCTTCCTTTGGGCCAAAGCAACGTACAACGGCTTACTGCCGACGACGCG
ACCGTTCAGCTCGGTGACGGCGCAGGTAGCCTCGCTTGCGGCATTGAAGCACACGAAGCCGAATCCCTTGGAGCGACCCTCCTCATCGGTCATGA
CCTTGGCCGATGTGATGTTGCCGTATGGAGAGAACGCGATGCGCAGACGATCGTCATCGATTGTGTCGTCCAGGTTCTTAACGTACAAGTTAACG
CCGAACACAGACTCGTGACGCTTCTGCTTCAGTTCCTCGAACTTGCGCTTCAGCTCCTGCTGGCGTTCGGCCTTCTTCTGGGCACGAGCCACGTA
CAGGGACTTGCCCTCTCCCATGTCCTTGCCATTGAGAGCCTGAACGGCCGCCTCAGCAGCCTCTGTTGTCTCGAATGCAACGAATCCGAAGCCCT
TGCTCTTGCCATCCTCCTTGGACATGACCTTGTAGCTGGTTATCTTGCCGTAGGGCTCAAAGAATTCCTTCAGTTTTTCATCGTCGAAATCCTCA
GTGAAGTTCTTCACATATACATTGGTGAAGAGCTTAGCCTTCTCGCCCAGCTCCTTCTCGCGCTCCTTGCGCGGGATGAACTTACCCACGTAGAC
CTTCTTGCCGTTGAGCAACATGCCATTGACTTTGTCGATGGACGTGTTTGCGGCCTCCTCGGTCTCGAAGTGGACGAATCCATAGCCCTTTGAGT
TGCCCTTTTCATCGGTGGCTACCTTGCAGCTTAAAATGTTGCCGAAGGCGGAGAAAGTGTCGTAGATTGCCTTGTTGTCGATGGCCCTATCTAAG
TTCTTGATGAACACGTTGCCCACACCTGAGCGACGAAGAGAAGGATCACGCTGAGACCACATAATGCGAATGGGCTTGTTGCGAACCAGGTCAAA
GTTCATGGTGTCCAAAGCACGCTCAGCTGTTGATGAAAATCGGGAAAACATTTGGTTACTACCGACACGATTTGGGTATATCAAGATCATTATAA
GTTGAAGGGGCTTAAATAACAATGTGACTCTTCAACTTCTGCACTGGCCATGAGCAAAAGCAGCGCAGTGCATGGTAAGTCAAGTCTGATCTTTT
ATCTGGCAACTATGAATCTTAGTCGTGTCAAAAAGGGTTGAATCTGACCAACCAATGGGTAGGAGTTGCTAGATGTCTAAATACAAGGACAATCT
TATCAGTCTAATCATGTGATACATTGAGTGTTTGTTATGCAGATGGTATGCAAAACCCATCAGCATGGTAAGTCGCATTGCTTTCTCTGGCAACT
ATGAATCTTAGTCGTGTCAAAATGGGTTAAATCTGACCAACCAATGGGTAGAAGTTGCTAGAAGCTTAGATAAGAAAGGGCATAATCCTTCGAGT
CTAATCATATGATGTATTATTTAGTGTTTGTTATGCTTCTACTTCTGTGGATGGCATAGATCAGCCATCTACATGGTAAGTTGCATTGCTTTCTC
TGGCAACATTGAATCTTAGTCGTGTCAAAAAGAGATAAATCTGACCAACCAATGGGTAGGAGTTGCGAGATATGAATCGAAAAAAGAAAAACATT
TAGGGTGTTACTAGTCTAGAACGAGATGGTATCATTTTTGAAAGGTCTGTTTTTCCAACCTAACCTTAACAGCTAGAGTTCAAGAAACTTGCTGG
AATGCGACAGACTTTCACACGCAGCGTAATCATCACCAACCGCCAGCTTTGTGCCATTGTGCGCTTAATTGAATAAACAAATGTAAGCGAACAAC GGGAATCGAAGAAGCACCAACTATGCGCAGTGAAAGTTTTGTTTTCGTTTTTTGTAAAAACAAGATTTTGATGGTTAAAAGAGAGGCCGAAAAGC
AGTTCACTGACATGTCAAGAATTTGGAAGTGTTGATGGATGGAATGCGGAGAGTATGGAAGATATGAGAAAGTGAAAGCAAAACAAAAGTTGGAG
GCAGTACGAAAACTAAAGAGCGAACGTGCGGAAACTCAGTTAATGGAATATAACCTAAAATAGATGAAGGCCAAAAAGAAATGGTCCAAACAACA
ATGAACACATGTTTTTGCGCGTCGGCGTGTGCGTGCGCGCAAGTTTGCCGCTTGGAAACAACACACATCACACGAATAAAACGAGAAGAACGGGC
AAGGAAACAATGAAACCACCAATGGGCGGGGCTGCGATAAGCAGTTTGGGCAGTATGGAACCATATTATTCCATCATAATTGCAATTTTGTGCGA
AATTGAGACGGAAATTTCTAGGCGAACAGTTGATGAGTGCCACGAGCCAGCTGTTTAGCCCCCATCATCCCCCCGCACAAATCGTATACATCCAG
AATAACTGGAACTGATATAATCATGTGTGTGTGTGTACACACTGGCGGGAATTGAGTGCGTGTGTGTGTGCGCGACGAGATTAACGTAAGCAGTG
CACTGTGGAACAAGTTATGAAACACTTGGAAGCCGTTTATCTGGTCTCCTATGAAAGACATCTTTCAATAAAGTCCAGTTTGGACTTGCGTTTAG
CCCCACTGTATGACATGCGCTAGTGTGCGTGCGTGTGTGAGTAAGCGAGTGCAAAACTGCACACGTGTTTTCTTTGTTTCGCGCGGAAGGGGGCT
ACTTTTGCGGGCAGTAAGACTAAAAAAATTACACTACTTTTGCGGGGATTACTCACCATCGGCTGGCTGCTGGAAGTTGACGTAGGCATAGCCCA
ACGAGCGACGGGTAATCACATCGCGGCAGACACGAATGGACAGCACTGGACCAGCAGACGAGAACTTGTCAAAAAGTCCCGATTCGTTGACGTCC
TGTGGGAGATCACCGACGTATAGAGAAGCCATATTTGGTGATCAGGTCTACCTGCAATTTTTAACAATTAATTTCCACTTTTTTGACACTGAATT
TTGGGTTTTTTCTTAATCTTTACGGACCGGATGGATTCGACCAGGCAGGCGGTGAAATAGAAAGAAAAAAAGCGGCGTGGCTTTCGGTCTTCTAT
TCGTCTCTCTGTCTGTGTGTCTGGGTGGCAACACTGGTACATGTGACAGTCGGTAGACATGGCAACGTTGGCATTTGCTTTGTTGTTGCTCTTTG
CTCTCCCCTTTTATTTCTCTTCGTGTTGGAAAATTTCCACACAGACACAAAGATAGACACGCGTTTGCCTGATCGAATTTTGGGGAATTCTTTGA
TTTTCTCGAAAATATGCGACAACTAGTTCCTAGACCACTATTTTGCGGGCAATCTGGCGTTTATAGACGCCATCTTTGAGCGAAGAACGACCGCA
AACAAAGCAAATTTCGATGGGAAAGGAAAATTTCCCTATTCGCTTTGTCGTGCGTTGCGCCCTCTCACTCTCTACACCATTGTAACCAATAGCTT
TACACTGTACTTACTTCTCAAACACGCTCGATTTTTTTTGCTACTTTTTACAATTTTTTTTGTTACGTTTTTGTGTTTTAATATTTTTTTTTATT
TTTTATATGTTTTTTCTTCACAAAAAATATGTGATAAGCCGTGTGCTGAAAGCGAATCCACGACCGCTCACGTAAACGGACTCTACACGACTCAT
AGAGAGGAGATTCGTTAGCGATGACCCCACAAAGTATCGATTAAATCCCACTGCACAATGCTGCCACATAGGGTTAGAGACAAATAAATGTCACT
AAAAAATCCGTGAGGACAATTTACTAATTACGAAGCATTATTTTGAATTTCAAAAAAGCCAGCCATCACACATAAAAAATTTTTATATTTAGCTA
ATTCCCGAAACATGAAATACTTGTGCATTTTCAGGGGTTCTTTGGTAACTCTGCTTCATTTATGTTCTGATATTTTCGCCAATGTCCTTGAATAC
TTTGTCTCATAAAACACAATCCAAAATTAGGAATGCAGTTTTTTTTCTTTTAAAAATGAGCGTAGACTTTTAGAAAATGATTTTTTGGCACTGC
ACAGATATTAGCGTATGCTCCGAAAACCGAATCCCATCTTTGTAATTCCCCACTGTGCGAACTTACCTAAATCAGAGAATAAAGCGATGAGGCTG
CAAGTCGACACTCCGAGAAGTGCTTGAGTACTTCTTTTCGTTCTCGATGGAAATCGGCACTACAGAGATTGAAGAATTTTTTAAGTTTTTTTTT
GTGTTTTTGTTTTTACGAAATAGACCACATTCAAGGATGGCTGAGGATAATTTTTTTTTTCTTTTTCCCGTTTTGAACGTCTGGTGCATGTGCCC
TATCTGGCGATCGAGTACCTAATGAAGCGGTGTGAGGCGTCGGTGCCTGACAAGCTTCAAAGCGAAGTGTCACTTTGGGCGCCTACTGGCGTGTC
CTGAGTAAAATCTTAAAAGATTTGACATTTCGGAAACATTTATTTGGGCATTATATACTTCATTAAACATATTTCGATCTGGTTTGGCCAAACAT
TTACTTGGCTTGAGAATTAGTTTGCTTTCAACTCAATTTTGATTTTTCGTAGCATTTAATAGTTAAACATAAAACGTACTGGCTTAATTCATTAT
TGTGTAGTTTTGCCTAGACTATGGGTGAAAATTATTG
(SEQ ID NO: 1201)

Exon: 6447..6285
Exon: 5751..5567
Exon: 3826..2342
Exon: 2272..1965
Exon: 1897..1001
Start ATG: 5732 (Reverse strand: CAT)

Transcript No. : CT39086
AGTCCGTTTACGTGAGCGGTCGTGGATTCGCTTTCAGCACACGGCTTATCACATATTTTTTGTGAAGAAAAAACATATAAAAAATAAAAAAAAAT
ATTAAAACACAAAAACGTAACAAAAAAAATTGTAAAAAGTAGCAAAAAAAAATCGAGCGTGTTTGAGAAGTAGACCTGATCACCAAATATGGCTTC
TCTATACGTCGGTGATCTCCCACAGGACGTCAACGAATCGGGACTTTTTGACAAGTTCTCGTCTGCTGGTCCAGTGCTGTCCATTCGTGTCTGCC
GCGATGTGATTACCCGTCGCTCGTTGGGCTATGCCTACGTCAACTTCCAGCAGCCAGCCGATGCTGAGCGTGCTTTGGACACCATGAACTTTGAC
CTGGTTCGCAACAAGCCCATTCGCATTATGTGGTCTCAGCGTGATCCTTCTCTTCGTCGCTCAGGTGTGGGCAACGTGTTCATCAAGAACTTAGA
TAGGGCCATCGACAACAAGGCAATCTACGACACTTTCTCCGCCTTCGGCAACATTTTAAGCTGCAAGGTAGCCACCGATGAAAAGGGCAACTCAA
AGGGCTATGGATTCGTCCACTTCGAGACCGAGGAGGCCGCAAACACGTCCATCGACAAAGTCAATGGCATGTTGCTCAACGGCAAGAAGGTCTAC
GTGGGTAAGTTCATCCCGCGCAAGGAGCGCGAGAAGGAGCTGGGCGAGAAGGCTAAGCTCTTCACCAATGTATATGTGAAGAACTTCACTGAGGA
TTTCGACGATGAAAAACTGAAGGAATTCTTTGAGCCCTACGGCAAGATAACCAGCTACAAGGTCATGTCCAAGGAGGATGGCAAGAGCAAGGGCT
TCGGATTCGTTGCATTCGAGACAACAGAGGCTGCTGAGGCGGCCGTTCAGGCTCTCAATGGCAAGGACATGGGAGAGGGCAAGTCCCTGTACGTG
GCTCGTGCCCAGAAGAAGGCCGAACGCCAGCAGGAGCTGAAGCGCAAGTTCGAGGAACTGAAGCAGAAGCGTCACGAGTCTGTGTTCGGCGTTAA
CTTGTACGTTAAGAACCTGGACGACACAATCGATGACGATCGTCTGCGCATCGCGTTCTCTCCATACGGCAACATCACATCGGCCAAGGTCATGA
CCGATGAGGAGGGTCGCTCCAAGGGATTCGGCTTCGTGTGCTTCAATGCCGCAAGCGAGGCTACCTGCGCCGTCACCGAGCTGAACGGTCGCGTC
GTCGGCAGTAAGCCGTTGTACGTTGCTTTGGCCCAAAGGAAGGAGGAGCGCAAGGCTCATCTCGCCTCGCAGTACATGCGTCACATGACCGGCAT
GCGTATGCAGCAGCTGGGACAGATCTACCAGCCCAACGCGGCTAGCGGCTTCTTTGTGCCGACCCTTCCGTCAAATCAGCGTTTCTTCGGTTCCC
AGGTGGCCACTCAGATGAGAAACACACCCCGCTGGGTGCCCCAGGTGCGTCCCCCAGCAGCCATACAGGGTGTCCAGGCCGGAGCTGCCGCTGCT
GGTGGCTTCCAGGGCACAGCCGGTGCGGTGCCCACTCAGTTCCGTTCGGCTGCTGCTGGCGCTCGCGGGGCACAGCCTCAGGTGCAGGGCACACA
TGCCGCCGCTGCTGCGGCTAACAACATGCGCAACACTGGAGCACGCGCTATTACTGGCCAGCAAACTGCAGCACCCAACATGCAGATCCCCGGAG
CCCAAATCGCTGGCGGTGCCCAGCAGCGTACTTCCAACTATAAGTACACCTCAAACATGCGCAATCCTCCAGTGCCACAGTTGCATCAGACCCAG
CCAATTCCACAGCAATTGCAAGGAAAGAATTCTGAGAAGCTCATTGCCTCGTTGCTGGCCAACGCCAAGCCGCAGGAGCAGAAACAGATCCTGGG
CGAGCGTCTGTATCCGATGATTGAGCATATGCACGCCAATTTGGCTGGTAAGATCACCGGCATGTTGTTGGAGATCGAAAACTCTGAGCTCTTGC
ACATGATCGAGGATCAGGAGGCCCTTAAGGCCAAGGTGGAGGAGGCTGTGGCCGTGCTTCAGGTGCACCGCGTCACCGAGCCCGCCAACTAAGCT
CGAACAGCTCAAGCGTATGAACATTTTACAAGAACACTTTACACCCAAAAATTTTCCACTAATCTTTCAATACATGAACAACAAAAATTCGCATT
CACTGATGCTTTGCGCAGGGGAGGATTGCCAAGGACACACAATTAACACAGAAAAACAAAGCGAAAAATCTACGGCTTTTTCTTTTCTAATCCCA
GAAACATCAACAAAAGCAATTTCAATCATTTAATTTCGAACGCATTTACGCAAGTACACGAAGCAAAAGAAGAAAGTCACGCAATCAAATTCTGC
AGTCCACTTATAAATTCTTTTTTTTACATAAACATGTTAATTAAAAAAAAAAACGGAAAAATGTGAAATGAAAAAAATTTCGTTATTGCTTTAA
CTGGATCGATATTATTTTGTATGCGTATAATGAAAACACCAAAAAACCATTGCAAAATAAACAGATTAAAGCAAAGCATACATGTAAACCGCTTC
TTGCAAGTATTGAAATTGTGTTTTAAAAATTTTAAAGAAGTTTCTAGTGTTACATACATATTGAGTTTTTCGTACACTTTTTCCATCCACACTTT
CAAACAACAACAAACACGAAAGCGATATGTAATTTTTTTCAATTCTTTTTTCTCAAATTCAAACTTTAAGAAAGCTTTGTTTAGAAAAAGAAACG
CGACAACCATACACTTTTAAAAAAGCAAAGAAAAAACAAAAAAATTGCAAAAGAGTTAAAATAAAAACGAAAAAATGGAAAGCAAACTGTGCAGA GAACAGAAGAATAGAAAGAAAGAAAGAAAAAGAAAACCGCAAGAATATGAGAGTCAAGTTTTTGCTACTTTGAAAAAAGAGAGAAAATACAGAAT
ACCAACAGCTGAAAAAATATGTTGACAAATGAAAACAAAACATAAATCGAAAAAACTACAAAAAAATGGCAAAACCTATGTAAAAACAGCAAA
(SEQ ID NO: 1202)

Start ATG: 183 (Reverse strand: CAT)

MASLYVGDLPQDVNESGLFDKFSSAGPVLSIRVCRDVITRRSLGYAYVNFQQPADAERALDTMNFDLVRNKPIRIMWSQRDPSLRRSGVGNVFIK
NLDRAIDNKAIYDTFSAFGNILSCKVATDEKGNSKGYGFVHFETEEAANTSIDKVNGMLLNGKKVYVGKFIPRKEREKELGEKAKLFTNVYVKNF
TEDFDDEKLKEFFEPYGKITSYKVMSKEDGKSKGFGFVAFETTEAAEAAVQALNGKDMGEGKSLYVARAQKKAERQQELKRKFEELKQKRHESVF
GVNLYVKNLDDTIDDDRLRIAFSPYGNITSAKVMTDEEGRSKGFGFVCFNAASEATCAVTELNGRVVGSKPLYVALAQRKEERKAHLASQYMRHM
TGMRMQQLGQIYQPNAASGFFVPTLPSNQRFFGSQVATQMRNTPRWVPQVRPPAAIQGVQAGAAAAGGFQGTAGAVPTQFRSAAAGARGAQPQVQ
GTHAAAAAAANNMRNTGARAITGQQTAAPNMQIPGAQIAGGAQQRTSNYKYTSNMRNPPVPQLHQTQPIPQQLQGKNSEKLIASLLANAKPQEQKQ
ILGERLYPMIEHMHANLAGKITGMLLEIENSELLHMIEDQEALKAKVEEAVAVLQVHRVTEPAN*
(SEQ ID NO: 1203)

Classification: RNA_binding
Gene Symbol: pAbp
FlyBase ID: FBgn0003031

Celera Sequence No. : 142000013384665
ATCTCATCTCATATGAAAGCAATATCATATATATGTATGTTAATATTAAATAGATATTAAACATAAAAATCCATCCCACCCACATTCCGCTGAAAAA
TGAAAACACTCGCTTTTGCCGAAGTGGAATTTTATTGTAATTAAATTTGTTGGGTGTACAAAGGTATGTTTTAAGGACTTTCTCTCTGCATTTAT
TACAATTTCTTCAAATGGTTTTAATTGCTGGGCTTTTGCTTCGAAGACGGGCAATCAAGTTTCAAGAATCCTATTTTCTTTAATCATACAAATTA
TGTTTTATTTCGCTTTAATATATAAGGATACATATATATATCTGCTATATATAGAAGTGTGTTGACTTGCGTATATTTCGTGAAAAGTAAAAGTT
TTCTTCTTCGCAATTTCCCTTGAACTAACATTCCAATTCGGGTTTTGGTTATGTTTTTTTTTTCTGTTTTACTCTCATTATTTTGTTTGTTTGTT
TTTTTTAAATAATTTTGCATTTTCTGCATACATGTGGTTTTGTGTTTTGCAATTTTTTCAATGATTTTTCCTTGGGTTTTTATTTGTTTTTAGTT
TTCGATTTGTTTAATAAAAAAATATGTATTTCACTGCCCAGAGCGAAAGCCATTTCTTACTTCCGCTTGCGTTAATATATCATTTTATGTATGTA
TGGTGTAAAAACATCATTTACTGGTAAAACTCTCGATATCCTTTGTAACAGAAATCGGAACGCAAATGAAATCGAGGCGACTTACCAGCTCCTTC
TCATTAAATACATATATGTTCTTGCAAATGTTTATAAATGTATGCATGTTTTTCCTTCTCTCGGATAATAGTGTAATCATAAAAATCCTGTCTGC
TTTTTTGTTGTTTATTAATATGCTTCATAAGTTGTTTACGCTTTAGCGCTTTTCATGTGTTTCTTGTATTTCTCATATATGTTGTGGTTGTTTAA
TATGTGTGTTGCTGTGTGTGTGTTTTTGTGTTTATATATATTATTTTTTTTTTGCTGTTTTTACATAGGTTTTGCCATTTTTTTGTAGTTTTTTC
GATTTATGTTTTGTTTTCATTTGTCAACATATTTTTTCAGCTGTTGGTATTCTGTATTTTCTCTCTTTTTTCAAAGTAGCAAAAACTTGACTCTC
ATATTCTTGCGGTTTTCTTTTTCTTTCTTTCTTCTATTCTTCTGTTCTTCTCTGCACAGTTTGCTTTCCATTTTTTCGTTTTTATTTTAACTCTTTT
GCAATTTTTTTGTTTTTTCTTTGCTTTTTTAAAAGTGTATGGTTGTCGCGTTTCTTTTTCTAAACAAAGCTTTCTTAAAGTTTGAATTTGAGAAA
AAAGAATTGAAAAAAATTACATATCGCTTTCGTGTTTGTTGTTGTTTGAAAGTGTGGATGGAAAAAGTGTACGAAAAACTCAATATGTATGTAAC
ACTAGAAACTTCTTTAAAATTTTTAAAACACAATTTCAATACTTGCAAGAAGCGGTTTACATGTATGCTTTGCTTTAATCTGTTTATTTTGCAAT
GGTTTTTTGGTGTTTTCATTATACGCATACAAAATAATATCGATCCAGTTAAAGCAATAACGAAATTTTTTTCATTTCACATTTTTCCGTTTTTT
TTTTTAATTAACATGTTTATGTAAAAAAAAAGAATTTATAAGTGGACTGCAGAATTTGATTGCGTGACTTTCTTCTCTTTTGCTTCGTGTACTTGCG
TAAATGCGTTCGAAATTAAATGATTGAAATTGCTTTTGTTGATGTTTCTGGGATTAGAAAAGAAAAAGCCGTAGATTTTTCGCTTTGTTTTTCTG
TGTTAATTGTGTGTCCTTGGCAATCCTCCCCTGCGCAAAGCATCAGTGAATGCGAATTTTTGTTGTTCATGTATTGAAAGATTAGTGGAAAACTG
CAAGGACAAAAGAGAGGCGAGTTTAGACAGCTTGAACTTTTCGGAAAATTTGTAGACTACTTACTTTTTGGGTGTAAAGTGTTCTTGTAAAATGT
TCATACGCTTGAGCTGTTCGAGCTTAGTTGGCGGGCTCGGTGACGCGGTGCACCTGAAGCACGGCCACAGCCTCCTCCACCTTGGCCTTAAGGGC
CTCCTGATCCTCGATCATGTGCAAGAGCTCAGAGTTTTCGATCTCCAACAACATGCCGGTGATCTTACCAGCCAAATTGGCGTGCATATGCTCAA
TCATCGGATACAGACGCTCGCCCAGGATCTGTTTCTGCTCCTGCGGCTTGGCGTTGGCCAGCAACGAGGCAATGAGCTTCTCAGAATCTGCAAGA
AAAATAGCAATGGTGCCATTAGTGACAAATTGTGCATATTTTCAGTCGACCTAAAACTTACTCTTTCCTTGCAATTGCTGTGGAATTGGCTGGGT
CTGATGCAACTGTGGCACTGGAGGATTGCGCATGTTTGAGGTGTACTTATAGTTGGAAGTACGCTGCTGGGCACCGCCAGCGATTTGGGCTCCGG
GGATCTGCATGTTGGGTGCTGCAGTTTGCTGGCCAGTAATAGCGCGTGCTCCAGTGTTGCGCATGTTGTTAGCCGCAGCAGCGGCGGCATGTGTG
CCCTGCACCTGAGGCTGTGCCCCGCGAGCGCCAGCAGCAGCCGAACGGAACTGAGTGGGCACCGCACCGGCTGTGCCCTGGAAGCCACCAGCAGC
GGCAGCTCCGGCCTGGACACCCTGTATGGCTGCTGGGGGACGCACCTGGGGCACCCAGCGGGGTGTGTTTCTCATCTGAGTGGCCACCTGGGAAC
CGAAGAAACGCTGATTTGACGGAAGGGTCGGCACAAAGAAGCCGCTAGCCGCGTTGGGCTGGTAGATCTGTCCCAGCTGCTGCATACGCATGCCG
GTCATGTGACGCATGTACTGCGAGGCGAGATGAGCCTTGCGCTCCTCCTTCCTTTGGGCCAAAGCAACGTACAACGGCTTACTGCCGACGACGCG
ACCGTTCAGCTCGGTGACGGCGCAGGTAGCCTCGCTTGCGGCATTGAAGCACACGAAGCCGAATCCCTTGGAGCGACCCTCCTCATCGGTCATGA
CCTTGGCCGATGTGATGTTGCCGTATGGAGAGAACGCGATGCGCAGACGATCGTCATCGATTGTGTCGTCCAGGTTCTTAACGTACAAGTTAACG
CCGAACACAGACTCGTGACGCTTCTGCTTCAGTTCCTCGAACTTGCGCTTCAGCTCCTGCTGGCGTTCGGCCTTCTTCTGGGCACGAGCCACGTA
CAGGGACTTGCCCTCTCCCATGTCCTTGCCATTGAGAGCCTGAACGGCCGCCTCAGCAGCCTCTGTTGTCTCGAATGCAACGAATCCGAAGCCCT
TGCTCTTGCCATCCTCCTTGGACATGACCTTGTAGCTGGTTATCTTGCCGTAGGGCTCAAAGAATTCCTTCAGTTTTTCATCGTCGAAATCCTCA
GTGAAGTTCTTCACATATACATTGGTGAAGAGCTTAGCCTTCTCGCCCAGCTCCTTCTCGCGCTCCTTGCGCGGGATGAACTTACCCACGTAGAC
CTTCTTGCCGTTGAGCAACATGCCATTGACTTTGTCGATGGACGTGTTTGCGGCCTCCTCGGTCTCGAAGTGGACGAATCCATAGCCCTTTGAGT
TGCCCTTTTCATCGGTGGCTACCTTGCAGCTTAAAATGTTGCCGAAGGCGGAGAAAGTGTCGTAGATTGCCTTGTTGTCGATGGCCCTATCTAAG
TTCTTGATGAACACGTTGCCCACACCTGAGCGACGAAGAGAAGGATCACGCTGAGACCACATAATGCGAATGGGCTTGTTGCGAACCAGGTCAAA
GTTCATGGTGTCCAAAGCACGCTCAGCTGTTGATGAAAATCGGGAAAACATTTGGTTACTACCGACACGATTTGGGTATATCAAGATCATTATAA
GTTGAAGGGGCTTAAATAACAATGTGACTCTTCAACTTCTGCACTGGCCATGAGCAAAAGCAGCGCAGTGCATGGTAAGTCAAGTCTGATCTTTT
ATCTGGCAACTATGAATCTTAGTCGTGTCAAAAAGGGTTGAATCTGACCAACCAATGGGTAGGAGTTGCTAGATGTCTAAATACAAGGACAATCT
TATCAGTCTAATCATGTGATACATTGAGTGTTTGTTATGCAGATGGTATGCAAAACCCATCAGCATGGTAAGTCGCATTGCTTTCTCTGGCAACT
ATGAATCTTAGTCGTGTCAAAATGGGTTAAATCTGACCAACCAATGGGTAGAAGTTGCTAGAAGCTTAGATAAGAAAGGGCATAATCCTTCGAGT
CTAATCATATGATGTATTATTTAGTGTTTGTTATGCTTCTACTTCTGTGGATGGCATAGATCAGCCATCTACATGGTAAGTTGCATTGCTTTCTC
TGGCAACATTGAATCTTAGTCGTGTCAAAAAGAGATAAATCTGACCAACCAATGGGTAGGAGTTGCGAGATATGAATCGAAAAAAGAAAAACATT
TAGGGTGTTACTAGTCTAGAACGAGATGGTATCATTTTTGAAAGGTCTGTTTTTCCAACCTAACCTTAACAGCTAGAGTTCAAGAAACTTGCTGG
AATGCGACAGACTTTCACACGCAGCGTAATCATCACCAACCGCCAGCTTTGTGCCATTGTGCGCTTAATTGAATAAACAAATGTAAGCGAACAAC
GGGAATCGAAGAAGCACCAACTATGCGCAGTGAAAGTTTTGTTTTCGTTTTTTGTAAAAACAAGATTTTGATGGTTAAAAGAGAGGCCGAAAAGC

FIGURE SHEET 646

AGTTCACTGACATGTCAAGAATTTGGAAGTGTTGATGGATGGAATGCGGAGAGTATGGAAGATATGAGAAAGTGAAAGCAAAACAAAAGTTGGAG
GCAGTACGAAAACTAAAGAGCGAACGTGCGGAAACTCAGTTAATGGAATATAACCTAAAATAGATGAAGGCCAAAAAGAAATGGTCCAAACAACA
ATGAACACATGTTTTTGCGCGTCGGCGTGTGCGTGCGCGCAAGTTTGCCGCTTGGAAACAACACACATCACACGAATAAAACGAGAAGAACGGGC
AAGGAAACAATGAAACCACCAATGGGCGGGGCTGCGATAAGCAGTTTGGGCAGTATGGAACCATATTATTCCATCATAATTGCAATTTTGTGCGA
AATTGAGACGGAAATTTCTAGGCGAACAGTTGATGAGTGCCACGAGCCAGCTGTTTAGCCCCCATCATCCCCCCGCACAAATCGTATACATCCAG
AATAACTGGAACTGATATAATCATGTGTGTGTGTACACACTGGCGGGAATTGAGTGCGTGTGTGTGCGCGACGAGATTAACGTAAGCAGTG
CACTGTGGAACAAGTTATGAAACACTTGGAAGCCGTTTATCTGGTCTCCTATGAAAGACATCTTTCAATAAAGTCCAGTTTGGACTTGCGTTTAG
CCCCACTGTATGACATGCGCTAGTGTGCGTGCGTGTGTGAGTAAGCGAGTGCAAAACTGCACACGTGTTTTCTTTGTTTCGCGCGGAAGGGGGCT
ACTTTTGCGGGCAGTAAGACTAAAAAAATTACACTACTTTTGCGGGATTACTCACCATCGGCTGGCTGCTGGAAGTTGACGTAGGCATAGCCCA
ACGAGCGACGGGTAATCACATCGCGGCAGACACGAATGGACAGCACTGGACCAGCAGACGAGAACTTGTCAAAAAGTCCCGATTCGTTGACGTCC
TGTGGGAGATCACCGACGTATAGAGAAGCCATATTTGGTGATCAGGTCTACCTGCAATTTTTAACAATTAATTTCCACTTTTTTGACACTGAATT
TTGGGTTTTTTCTTAATCTTTACGGACCGGATGGATTCGACCAGGCAGGCGGTGAAATAGAAAGAAAAAAAGCGGCGTGGCTTTCGGTCTTCTAT
TCGTCTCTCTGTCTGTGTGTCTGGGTGGCAACACTGGTACATGTGACAGTCGGTAGACATGGCAACGTTGGCATTTGCTTTGTTGTTGCTCTTTG
CTCTCCCCTTTTATTTCTCTTCGTGTTGGAAAATTTCCACACAGACACAAAGATAGACACGCGTTTGCCTGATCGAATTTTGGGGAATTCTTTGA
TTTTCTCGAAAATATGCGACAACTAGTTCCTAGACCACTATTTTGCGGGCAATCTGGCGTTTATAGACGCCATCTTTGAGCGAAGAACGACCGCA
AACAAAGCAAATTTCGATGGGAAAGGAAAATTTCCCTATTCGCTTTGTCGTGCGTTGCGCCCTCTCACTCTCTACACCATTGTAACCAATAGCTT
TACACTGTACTTACTTCTCAAACACGCTCGATTTTTTTTGCTACTTTTTACAATTTTTTTTGTTACGTTTTTGTGTTTTAATATTTTTTTTTATT
TTTTATATGTTTTTTCTTCACAAAAAATATGTGATAAGCCGTGTGCTGAAAGCGAATCCACGACCGCTCACGTAAACGGACTCTACACGACTCAT
AGAGAGGAGATTCGTTAGCGATGACCCCACAAAGTATCGATTAAATCCCACTGCACAATGCTGCCACATAGGGTTAGAGACAAATAAATGTCACT
AAAAAATCCGTGAGGACAATTTACTAATTACGAAGCATTATTTTGAATTTCAAAAAAGCCAGCCATCACACATAAAAAATTTTTATATTTAGCTA
ATTCCCGAAACATGAAATACTTGTGCATTTTCAGGGGTTCTTTGGTAACTCTGCTTCATTTATGTTCTGATATTTTCGCCAATGTCCTTGAATAC
TTTGTCTCATAAAACACAATCCAAAATTAGGAATGCAGTTTTTTTTTCTTTTAAAAATGAGCGTAGACTTTTAGAAAATGATTTTTTGGCACTGC
ACAGATATTAGCGTATGCTCCGAAAACCGAATCCCATCTTTGTAATTCCCCACTGTGCGAACTTACCTAAATCAGAGAATAAAGCGATGAGGCTG
CAAGTCGACACTCCGAGAAGTGCTTGAGTACTTCTTTTCGTTCTCGATGGAAATCGGCACTACAGAGATTGAAGAATTTTTTAAGTTTTTTTTTT
GTGTTTTTGTTTTTACGAAATAGACCACATTCAAGGATGGCTGAGGATAATTTTTTTTTTCTTTTTCCCGTTTTGAACGTCTGGTGCATGTGCCC
TATCTGGCGATCGAGTACCTAATGAAGCGGTGTGAGGCGTCGGTGCCTGACAAGCTTCAAAGCGAAGTGTCACTTTGGGCGCCTACTGGCGTGTC
CTGAGTAAAATCTTAAAAGATTTGACATTTCGGAAACATTTATTTGGGCATTATATACTTCATTAAACATATTTCGATCTGGTTTGGCCAAACAT
TTACTTGGCTTGAGAATTAGTTTGCTTTCAACTCAATTTTGATTTTTCGTAGCATTTAATAGTTAAACATAAAACGTACTGGCTTAATTCATTAT
TGTGTAGTTTTGCCTAGACTATGGGTGAAAATTATTGAACTAGTCCTACATTTTATTAAATTTGTGTGTATGTATGTATATCAATTGTTTTTTTT
TTGTATGCATGACATGATTTGTGAGTTTTCCCATTTGAAGGTATATTTTTCAAAAACATACATGGGCGTGGCGTATCGCTAAAGTACAGTACTGA
ACTTAACTGAATTGTTCTCATTATTTAATACGTTTTCATTCATCAGCGAATTTTACATAGGCTTCCAGATTAATCTTGTAATACTTTTACCAATT
TTGTGAAAACTTATTTATGTTCTGCTGCAACACTTAACTGCCATTGCACAATTATAACCTGTATTCAGTTGCTTTTTGCTTTTTTTTCGTTTTTT
TTTTTTACAATTTAACATTTTATCGCTTTAATGCTGAACCAATATTTTGAACAATCTTTTTCTATTTTGGCAGTGGGTTGGTAATAAACTTTTAA
ACATTAACAAATAAAGAGGCCCGTAGTTGGCAGCGTTCATTAATACATAATAACGAAAAGAAATGATAATGGAAATGAAGAATATAAAATTCATA
ATGAGTCGGTATGCCAAAGGGTTCAATTTCCAAGCAATCCAATCGCCGTTGTCGCTGTATCTCCGCCCCACTCCACCAGGTACTGGACCTGTCCA
TTTCCCATGCGCCGCTTGGCCCGAATGGCAAAGGGCTCACCAGCATCTATGCGATTC
(SEQ ID NO: 1204)

Exon: 7132..6907
Exon: 5751..5567
Exon: 3826..2342
Exon: 2272..1965
Exon: 1897..1001
Start ATG: 5732 (Reverse strand: CAT)

Transcript No. : CT39088
CCAGATAGGGCACATGCACCAGACGTTCAAAACGGGAAAAAGAAAAAAAAAATTATCCTCAGCCATCCTTGAATGTGGTCTATTTCGTAAAAACA
AAAACACAAAAAAAAAACTTAAAAAATTCTTCAATCTCTGTAGTGCCGATTTCCATCGAGAACGAAAAGAAGTACTCAAGCACTTCTCGGAGTGT
CGACTTGCAGCCTCATCGCTTTATTCTCTGATTTAGGTAGACCTGATCACCAAATATGGCTTCTCTATACGTCGGTGATCTCCCACAGGACGTCA
ACGAATCGGGACTTTTTGACAAGTTCTCGTCTGCTGGTCCAGTGCTGTCCATTCGTGTCTGCCGCGATGTGATTACCCGTCGCTCGTTGGGCTAT
GCCTACGTCAACTTCCAGCAGCCAGCCGATGCTGAGCGTGCTTTGGACACCATGAACTTTGACCTGGTTCGCAACAAGCCCATTCGCATTATGTG
GTCTCAGCGTGATCCTTCTCTTCGTCGCTCAGGTGTGGGCAACGTGTTCATCAAGAACTTAGATAGGGCCATCGACAACAAGGCAATCTACGACA
CTTTCTCCGCCTTCGGCAACATTTTAAGCTGCAAGGTAGCCACCGATGAAAAGGGCAACTCAAAGGGCTATGGATTCGTCCACTTCGAGACCGAG
GAGGCCGCAAACACGTCCATCGACAAAGTCAATGGCATGTTGCTCAACGGCAAGAAGGTCTACGTGGGTAAGTTCATCCCGCGCAAGGAGCGCGA
GAAGGAGCTGGGCGAGAAGGCTAAGCTCTTCACCAATGTATATGTGAAGAACTTCACTGAGGATTTCGACGATGAAAAACTGAAGGAATTCTTTG
AGCCCTACGGCAAGATAACCAGCTACAAGGTCATGTCCAAGGAGGATGGCAAGAGCAAGGGCTTCGGATTCGTTGCATTCGAGACAACAGAGGCT
GCTGAGGCGGCCGTTCAGGCTCTCAATGGCAAGGACATGGGAGAGGGCAAGTCCCTGTACGTGGCTCGTGCCCAGAAGAAGGCCGAACGCCAGCA
GGAGCTGAAGCGCAAGTTCGAGGAACTGAAGCAGAAGCGTCACGAGTCTGTGTTCGGCGTTAACTTGTACGTTAAGAACCTGGACGACACAATCG
ATGACGATCGTCTGCGCATCGCGTTCTCTCCATACGGCAACATCACATCGGCCAAGGTCATGACCGATGAGGAGGGTCGCTCCAAGGGATTCGGC
TTCGTGTGCTTCAATGCCGCAAGCGAGGCTACCTGCGCCGTCACCGAGCTGAACGGTCGCGTCGTCGGCAGTAAGCCGTTGTACGTTGCTTTGGC
CCAAAGGAAGGAGGAGCGCAAGGCTCATCTCGCCTCGCAGTACATGCGTCACATGACCGGCATGCGTATGCAGCAGCTGGGACAGATCTACCAGC
CCAACGCGGCTAGCGGCTTCTTTGTGCCGACCCTTCCGTCAAATCAGCGTTTCTTCGGTTCCCAGGTGGCCACTCAGATGAGAAACACACCCCGC
TGGGTGCCCCAGGTGCGTCCCCCAGCAGCCATACAGGGTGTCCAGGCCGGAGCTGCCGCTGCTGGTGGCTTCCAGGGCACAGCCGGTGCGGTGCC
CACTCAGTTCCGTTCGGCTGCTGCTGGCGCTCGCGGGGCACAGCCTCAGGTGCAGGGCACACATGCCGCCGCTGCTGCGGCTAACAACATGCGCA
ACACTGGAGCACGCGCTATTACTGGCCAGCAAACTGCAGCACCCAACATGCAGATCCCCGGAGCCCAAATCGCTGGCGGTGCCCAGCAGCGTACT
TCCAACTATAAGTACACCTCAAACATGCGCAATCCTCCAGTGCCACAGTTGCATCAGACCCAGCCAATTCCACAGCAATTGCAAGGAAAGAATTC
TGAGAAGCTCATTGCCTCGTTGCTGGCCAACGCCAAGCCGCAGGAGCAGAAACAGATCCTGGGCGAGCGTCTGTATCCGATGATTGAGCATATGC
ACGCCAATTTGGCTGGTAAGATCACCGGCATGTTGTTGGAGATCGAAAACTCTGAGCTCTTGCACATGATCGAGGATCAGGAGGCCCTTAAGGCC
AAGGTGGAGGAGGCTGTGGCCGTGCTTCAGGTGCACCGCGTCACCGAGCCCGCCAACTAAGCTCGAACAGCTCAAGCGTATGAACATTTTACAAG
AACACTTTACACCCAAAAATTTTCCACTAATCTTTCAATACATGAACAACAAAAATTCGCATTCACTGATGCTTTGCGCAGGGGAGGATTGCCAA
GGACACACAATTAACACAGAAAAACAAAGCGAAAAATCTACGGCTTTTTCTTTTCTAATCCCAGAAACATCAACAAAAGCAATTTCAATCATTTA

```
ATTTCGAACGCATTTACGCAAGTACACGAAGCAAAAGAAGAAAGTCACGCAATCAAATTCTGCAGTCCACTTATAAATTCTTTTTTTTTACATAA
ACATGTTAATTAAAAAAAAAAAACGGAAAAATGTGAAATGAAAAAAATTTCGTTATTGCTTTAACTGGATCGATATTATTTTGTATGCGTATAATG
AAAACACCAAAAAACCATTGCAAAATAAACAGATTAAAGCAAAGCATACATGTAAACCGCTTCTTGCAAGTATTGAAATTGTGTTTTAAAAATTT
TAAAGAAGTTTCTAGTGTTACATACATATTGAGTTTTTCGTACACTTTTTCCATCCACACTTTCAAACAACAACAAACACGAAAGCGATATGTAA
TTTTTTTCAATTCTTTTTTCTCAAATTCAAACTTTAAGAAAGCTTTGTTTAGAAAAAGAAACGCGACAACCATACACTTTTAAAAAAGCAAAGAA
AAAACAAAAAAATTGCAAAAGAGTTAAAATAAAAACGAAAAAATGGAAAGCAAACTGTGCAGAGAACAGAAGAATAGAAAGAAAGAAAGAAAAAG
AAAACCGCAAGAATATGAGAGTCAAGTTTTTGCTACTTTGAAAAAAGAGAGAAAATACAGAATACCAACAGCTGAAAAAATATGTTGACAAATGA
AAACAAAACATAAATCGAAAAAACTACAAAAAAATGGCAAAACCTATGTAAAAACAGCAAA
(SEQ ID NO: 1205)

Start ATG: 246 (Reverse strand: CAT)

MASLYVGDLPQDVNESGLFDKFSSAGPVLSIRVCRDVITRRSLGYAYVNFQQPADAERALDTMNFDLVRNKPIRIMWSQRDPSLRRSGVGNVFIK
NLDRAIDNKAIYDTFSAFGNILSCKVATDEKGNSKGYGFVHFETEEAANTSIDKVNGMLLNGKKVYVGKFIPRKEREKELGEKAKLFTNVYVKNF
TEDFDDEKLKEFFEPYGKITSYKVMSKEDGKSKGFGFVAFETTEAAEAAVQALNGKDMGEGKSLYVARAQKKAERQQELKRKFEELKQKRHESVF
GVNLYVKNLDDTIDDDRLRIAFSPYGNITSAKVMTDEEGRSKGFGFVCFNAASEATCAVTELNGRVVGSKPLYVALAQRKEERKAHLASQYMRHM
TGMRMQQLGQIYQPNAASGFFVPTLPSNQRFFGSQVATQMRNTPRWVPQVRPPAAIQGVQAGAAAAGGFQGTAGAVPTQFRSAAAGARGAQPQVQ
GTHAAAAAANNMRNTGARAITGQQTAAPNMQIPGAQIAGGAQQRTSNYKYTSNMRNPPVPQLHQTQPIPQQLQGKNSEKLIASLLANAKPQEQKQ
ILGERLYPMIEHMHANLAGKITGMLLEIENSELLHMIEDQEALKAKVEEAVAVLQVHRVTEPAN*
(SEQ ID NO: 1206)

Classification: RNA_binding
Gene Symbol: pAbp
FlyBase ID: FBgn0003031

Celera Sequence No. : 142000013384010
TTTTGGTTACTTGAAACGCTAAGACTGAAATGGCTTGTTATGGAGAAGAAAACACGTCCTGCAATACATTATATAATAAAAAGAACCCAGCAATT
TTCGCATCACCACATTACAGACAACAAAGTACTTTGTCCTCATCGTTCTGTGTGATCCAGATCCCCGACTATATATGATATATACACCTAGCTAG
ATTTAAGCGATTTGTACATACAGAAGCAAAAGCAAAACAATATACCAGAAAATTGCCTGTTAAATACATTTATATACACATATGAATTTAGTTAT
ATCACGATGACTAGTTTTTAGTTCTTAGAGGTTATTTAGTTAGTAAGGAGCCCAACTGACGTAACGTGAATAAATCAACTATATATGTGCCCATA
TATAAAGCGTACTATTTAATTATTTAGTTTTTACTGGACTTATGACACAACGAGCCACTGTAATGTCTTATTCAGCTCAATGCTCATAAACAAAA
TAAATATTTTTGGAAAAAATACTGTAGTTCTTCTTATTTAGCCAAGACGTCCAAACCTTTTTTTAATAAATTTAATTGAGATGAAGATTTGCATT
CGAATTCTATAGAAGCATCAAACAAATATTACAACAGTATCGAGTGGGTTAATTAAAAATTAAATATGTAAAAATCGCTCATTGTGTTAAAATATT
AATTATAATAGATTAGCTCAAACATCTTAAATCGACATTTTGTGCAACACATAAAAATTCTCGCAGACAATTGGCAGCTGATTACGATTAAACAA
AACCGAAATTAGCCGTTTTCCTTTAAAGCAATCAGCATTCGTGATCTCTTGTTTGGTTACCTCACAATGCTAGTTAGTTATAGCGCCATAAAACC
CCATTTTCAATGTCAGGGAAATCATAAGGTCATAAGGTTATCCCCACGATCGTTCTAATGTGATCACAGCCACAATCTATAATAACCAGTTCCCA
ATAGATAGACAAGATTAGAAAACGCAGCTTGGTAGAGTTTTTTATATTTTATAATTTAATTTATTCAGAGTGCTTTCTTGGGTATCGGGTCAGAC
AATTGAAACAGCATTAATATCATATTCGCATGTGTGGCCTGTGGGGGCAGCGGAGAGGAGATAACAAGGGGCTGGCCATCAAAGGTACAACATAC
GGACATACTTTCCAGCGAAAGCTAGACACACATAGGATTAAATATAGCACATAGTATAACAGAATATATATGGAATTGAATACTTTGAACTTGAG
TGTAGCTTAGTTTCGTACGATAGAATGTTTGGCTTTTAAAGTTAGAAAGATGTGTTTATAAAAAAGTGTGTATAAGTGCTGTGTTAGAGAAATGC
GTAAAGTGTTGTTTTGGAATGTACATGTGCAATGGCACACACGCAACATTAATGTATTCTTGCTGAGAAACAAGTATAAAGCATTTTCGCTATAC
TGAAACCGAAATTCGTTAGAAAGTAAAAGTATGTTGCTCCTGTGTCTGCCCACAATCGCTCCAACTAGTGAACTCTGTCCTTAAGGTAACCAATT
GGACTAGCCCACTTAATGCTGCTTGGCCTTCAGGCTAGCTGGCATCTCTGGTGGTGGTGGGCGGGAATGCCCAGGGCGACCTTCACACCATCGT
AGATGAACCACTGCAGAGCGGTCAGGGTACCGATCATGATAATACGAGGAGTCAATCCGTTCCACATGCCACTGAAGCCCAGCGACTTGGCCACG
CTGATGGCGCTAGCTCCCTTGGCCTGGTTCAGCTTGGACACCACCACATCAGCGGGATGCGACACCCACGGCACAGAACACACCGGCGATGTAGCC
AGCGGCGAAGGTCACGATCAGCTGCTCGCCCTTGGTGCAGTCGGCACGAGGCTTGGGCACCACATACCTGGGAAAAGTTGCATCATTAGTATTGA
TTTAACGGGGTTCGTTGGGGCTTGACAACCCGAACTGTGAACGGTATTGCTCTAGTTTTTACATTTGAACTTTCAGTGGCTACCTGCTAATTTGC
ACTTCAAAAGGAATGCTTTGCTTTTTTTTATTTTATCCATAGTAACAAACTAGTTCTGAAATAATATGATTTTCCTATATTTGAACAAGATAAGCA
TTCGTCGTTGGTTTTTATTCTGGCGTGCATTTATTAGATACGAATGGCATTCTTATCTGCTGACGCGCTAAAAGTTTATTTTATTATGAATACT
TTCAGTTTTGATCAATTAGCATATCACTTTTGAAATTTCACAGATTAACAGTCTACCTTTAAACTATTGTAATAGCAAAACGCTAATACGAATAC
AGATATTGTGCACAGCACTGGTAAGTTTTTCCGCTGTAGAAACTAGAGGATACCTAAAGAGGGAAATGTTACTTACTTGTAGAGCAGCTCCACGGT
GCGCTCGAAGCAAGCGAACTTCATCATGGTGTATGGGATCTGTCGCATCCACAGGGGAACCAGACCCTTGTAGAAGGCATTGACGCCCTCCTCCT
TTAGCATCTTGGGCACTGCCTCGCGGAAGTTGTTGGCGTATCCGGGAATAGTTCTGGATCTTCACCTTGGCGGCCTCGAACGGCGCCAGAGCGATA
TCGGCGAAGAACTCGGCCGAAGCGGAAGCAGCCAGATACAAGGAGGTGCGGTACAGGTAGGCGTTCTCCTCGCCAATGATTTCGGCGTACTTCAC
CTTGAACAACTCGTACAGACCGAACTTGCACAGACCCTGAAAGATACAGAAACGCGGATTAGCCTGCTGTTTCTCAGAAGTTATTTTTCAGTTTG
CAGTAGTATCCAAGATTTTATCTTCGGTATCTGTTTCTCCCGTAACCATAAAGTTGTCAAAGGTGTGTTGTTATTCTGAGGTATACTAAGATATC
AGCCTAGGAATCAAACTTCCTAATGTTCGATTCGAATCACTTTTATTGCTTCAAGCCCGGAACCGATGTAATTAAGGTCAGCCGACCTGGTCAC
GAGCATATAATTCGCCTCCAGACGATTATGCAACCCATAAAGTGAAGCCCAATCTCACCTGTGCCGAGTAGCCGAGCAGAGTGGGGAACCAGCCC
TTAGCCAGTCCGCGGGCGCCCTCCTCCGCCACGGTGACCTTGAATCCGTGCACCAGATTCTTGTACTTGGCCTGGTCGACCTGCAGACGGCACTT
CACCAGATCCAGTGGGACCACGAAGGTGTGGGTGGTGCCGCAGCTGAGAATGCCACCAATTCCGCACAGAGCGAAGTACTTGGTGCTGCCGAATT
CGCACGAATCCTGCTGGTTGGCCACCGGGGTAGCGGCGGCGGCGATCTGGCGACCCTCAACCGGCTGGGGTTCCACCACTGGGGCGGCGGCATCG
CATCTTGCCATCGACATGGGGGTGCGGAATGGCGAGTTCCGGGCAGTTTCAAAGAAGCTGGAGAACATCTTGATTCTGTTCTTGTTCTGGGGGTCG
GCTGAAAGTAGAGAGACCATCCATTAGTTACGTATATATGTACCTCGGAGGCGACATGTGCTTTATCTAATTATATATATAGCTGGGTAATCAGC
TGCTTTTCGCTTTTGTAGGTTACATAACGGCGTGCCTCGAATTCCGAGCACCCGGACTTACGACACCAAATTTACCCGAAAAGCGAAGGATTTTA
AGCAACCACGTAAATTTAGTGTATGTTAAGGGAGCGATAGAGCACCGCTCGGCTACTTTGATTTCGATTTTACAAAACTTATGCAATTTTCGCTC
GGAATTTTCGCACTTACTATTCGTCAGCAACGTTAGCGGCTCGTTGGCGAGGATTCAAAGAATGAGGGGGGGCTCACGGAGGTGCAGCGATTTCT
CACGAATACCAAAACGCCTTAATGGTTTTGCCGTGGAGAGGTGTAACTAGCGGATTGAGGATAGTTGGCCACACTCATGTCAAAATCTTCGGCTA
TGGACTGCAACCTTGGTGCAAAACTTTGGTGGCGCCTGAGCGTGGACTCGAACCATCTGCATACGAGGTATCAGGTGAGATTATTTTAATGCCAT
TGCCTTCGTTGTGAATAAAATATTAATTATTAATATTAATTTCATATTGATAACATTAGTTGTAAATATTTTGAAAAAATAATAAATTCATTTGT
AAAATCCTCATATTTTTGCATAGTATTTGTGATTTGTTTTCTATTTTTACACAATAAAACAAATTTTAATCTAAAGCTTTATTGTATTTAGAACT
```

CTCTGTAAAATATATAACAATTTTCAATTATATGTACATTTTAAATTTATAAGTTATAGCCCCATGGTAAAACTGGATAATTTTATGAGTAAATA
TGTGAAAATAAAGTTCTGCCATGATTTCACATGGGGTTGGCCCAATCCTTCACTTTTTACGCACGGACAGGAAATTAGGCCTTTGTATTCCATTT
TATATTTCACTCTGCAAGTGAAGCAAAATTCACCCTGGTGATCTTCAGTTAATAAGATTTGACAACCGATTTCTGGTGACCAAACGCAGCAGACT
TTGGCATTCATAGTATCTGTAAAATTAAAAAATTAGTCTTTTATTACTATTCAAATGCTTCTTATACCGATATGCAGTCCGGGTGGAACGCAAAC
ACCCTCTTTATTGGTTGTTTTGGGAATTCACCTTGTAGACGACCCAATCGCCTATAAAAGTTTCCTTCATAACAACTGAATCCTGTCTCTTTAA
TCCGACACATTTCCGTATTTTCCTTCCTACAATCTAAGCATCTC
(SEQ ID NO: 1207)

Exon: 3699..3591
Exon: 3421..3004
Exon: 2696..2356
Exon: 1872..1001
Start ATG: 3393 (Reverse strand: CAT)

Transcript No. : CT39178
AAATTGCATAAGTTTTGTAAAATCGAAATCAAAGTAGCCGAGCGGTGCTCTATCGCTCCCTTAACATACACTAAATTTACGTGGTTGCTTAAAAT
CCTTCGCTTTTCGGCCGACCCCAGAACAAGAACAGAATCAAGATGTTCTCCAGCTTCTTTGAAACTGCCCGGAACTCGCCATTCCGCACCCCCAT
GTCGATGGCAAGATGCGATGCCGCCGCCCCAGTGGTGGAACCCCAGCCGGTTGAGGGTCGCCAGATCGCCGCCGCCGCTACCCCGGTGGCCAACC
AGCAGGATTCGTGCGAATTCGGCAGCACCAAGTACTTCGCTCTGTGCGGAATTGGTGGCATTCTCAGCTGCGGCACCACCCACACCTTCGTGGTC
CCACTGGATCTGGTGAAGTGCCGTCTGCAGGTCGACCAGGCCAAGTACAAGAATCTGGTGCACGGATTCAAGGTCACCGTGGCGGAGGAGGGCGC
CCGCGGACTGGCTAAGGGCTGGTTCCCCACTCTGCTCGGCTACTCGGCACAGGGTCTGTGCAAGTTCGGTCTGTACGAGTTGTTCAAGGTGAAGT
ACGCCGAAATCATTGGCGAGGAGAACGCCTACCTGTACCGCACCTCCTTGTATCTGGCTGCTTCCGCTTCGGCCGAGTTCTTCGCCGATATCGCT
CTGGCGCCGTTCGAGGCCGCCAAGGTGAAGATCCAGACTATTCCCGGATACGCCAACAACTTCCGCGAGGCAGTGCCCAAGATGCTAAAGGAGGA
GGGCGTCAATGCCTTCTACAAGGGTCTGGTTCCCCTGTGGATGCGACAGATCCCATACACCATGATGAAGTTCGCTTGCTTCGAGCGCACCGTGG
AGCTGCTCTACAAGTATGTGGTGCCCAAGCCTCGTGCCGACTGCACCAAGGGCGAGCAGCTGATCGTGACCTTCGCCGCTGGCTACATCGCCGGT
GTGTTCTGTGCCGTGGTGTCGCATCCCGCTGATGTGGTGGTGTCCAAGCTGAACCAGGCCAAGGGAGCTAGCGCCATCAGCGTGGCCAAGTCGCT
GGGCTTCAGTGGCATGTGGAACGGATTGACTCCTCGTATTATCATGATCGGTACCCTGACCGCTCTGCAGTGGTTCATCTACGATGGTGTGAAGG
TCGCCCTGGGCATTCCCCGCCCACCACCACCAGAGATGCCAGCTAGCCTGAAGGCCAAGCAGCATTAAGTGGGCTAGTCCAATTGGTTACCTTAA
GGACAGAGTTCACTAGTTGGAGCGATTGTGGGCAGACACAGGAGCAACATACTTTTACTTTCTAACGAATTTCGGTTTCAGTATAGCGAAAATGC
TTTATACTTGTTTCTCAGCAAGAATACATTAATGTTGCGTGTGTGCCATTGCACATGTACATTCCAAAACAACACTTTACGCATTTCTCTAACAC
AGCACTTATACACACTTTTTATAAACACATCTTTCTAACTTTTAAAAGCCAAACATTCTATCGTACGAAACTAAGCTACACTCAAGTTCAAAGTA
TTCAATTCCATATATATTCTGTTATACTATGTGCTATATTTAATCCTATGTGTGTCTAGCTTTCGCTGGAAAGTATGTCCGTATGTTGTACCTTT
GATGGCCAGCCCCTTGTTATCTCCTCTCCGCTGCCCCCACAGGCCACACATGCGAATATGATATTAATGCTGTTTCAATTGTCTGACCCGATACC
CAAGAAAGCACTCTGAATAAATTAAATTAT
(SEQ ID NO: 1208)

Start ATG: 138 (Reverse strand: CAT)

MFSSFFETARNSPFRTPMSMARCDAAAPVVEPQPVEGRQIAAAATPVANQQDSCEFGSTKYFALCGIGGILSCGTTHTFVVPLDLVKCRLQVDQA
KYKNLVHGFKVTVAEEGARGLAKGWFPTLLGYSAQGLCKFGLYELFKVKYAEIIGEENAYLYRTSLYLAASASAEFFADIALAPFEAAKVKIQTI
PGYANNFREAVPKMLKEEGVNAFYKGLVPLWMRQIPYTMMKFACFERTVELLYKYVVPKPRADCTKGEQLIVTFAAGYIAGVFCAVVSHPADVVV
SKLNQAKGASAISVAKSLGFSGMWNGLTPRIIMIGTLTALQWFIYDGVKVALGIPRPPPPEMPASLKAKQH*
(SEQ ID NO: 1209)

Name: mitochondrial carrier protein; phosphate carrier
Classification: transporter
Gene Symbol: Mpcp
FlyBase ID: FBgn0026409

Celera Sequence No. : 142000013384645
ACTCATTGATTCATTCTTATGTTTGTTATTTTGTTATTAAATTCCAATTGATGATGCCAGTGTCTAAATAAAAACGAAGACCTAATTTTCAACCA
AAAATCAGGTTTTCTGGGCTTGTCCGTATTAAACATTTTTGATAATTATTTATAATATATTGTTATTTTTTGCTGGCTTCAAAACATCAACAAAT
TGTGTATGATAAATGACGATGACGTTGTTGTTGATGGCGATCGCGCTGTGGGAATCAGATGAAATGTCAATTAAGTTTGCATTTATATCTTTGAT
TGAAGCTCTAAGATTTGCTTTGCCATTTTATGCGGAAGTTAAGCTCGGTCAGTTCTTGAAAAAGTTCCCATGGGAGCAAGTTATTTGTTTTTTGA
CAATAAGAAGCGTTTATTTAAAATGGCTTATTATGGCCTCAATGATTCCTAATAGGCGTAACTTACTGGTTATAAACTTGTTTAATATCGTTTCA
TTTTAAACCTGGATGACAGAAAATGAATTTCGGTTCAAATACAAATATTACAATAGAAAGTATGATATTTAGCTCCGATAAACATTTAACAATTT
TAGTATTTTAATGGTGAAATGGTAAATTCCGCGCATGAAAAGAGATAGAAGAGATGACATATATGGAAACCTTAAAAACGTAACGGTTGCTTGGG
TTTTATAACAATCAGTCAGTGACAGGCATTTCCAGAGTTGCCCTGTTCAACAATCGATAGCTGCCTTCGGTCGCTCGTCACTAACTTTCCTTTAG
GCAACGGCCACACTGTCTGGCCACCAAAATCCCAAACTTAATTAAAGAATTAAATAATTCGAATAATAATTAAGCCCAGTAACCTACGCAGCTTG
AGTGCGTAACCGATATCTAGTATACATTTCGATACATCGAAATCATGGTAGTGTTGGAGACGGAGAAGGTAAGGCGAGAAACGGCGAGCCGCATG
GTTTCGATTTCGGCTGAGCCGTGGCAGGAACAACAAAAACAGGGTTGTTGCACAAGAGGGGAGGCGATAGTCGAGCGGAAAAGTGTGCAGTTGGC
GTGGCTACATCATCATTGTGTTCACCGATTATTTTTTGCACAATTGCTTAATATTAATTGTACTTGCACGCTATTGTCTACGTCATAGCTATCGC
TATCTCTGTCTGTCTCTATCAAGCTATCTCTCTTTCGCGGTCACTCGTTCTCTTTTTCTCTCCTTTCGCATTTGCATACGCATACCACACGTTTT
CAGTGTTCTCGCTCTCTCTCTCTTGTCAAGACATCGCGCGCGTGTGTGTGGGTGTGTTCTTCTTTAGCTACATATACATAAATAGGAGAGCGGAG
AGACAAATATGGAAAGAATGGAAAAAGAGTGAATTACTGCAATTAACCAGTCGCGAACAGTTAAATCATATTTTTGTCGGCCATTGCAGTAAATA
AACCGTTGGCTTTCCCTCTTCACTTTCCACCTCCTTTCTTTGACGTTAATTTTTTTCAGTTAATCGCGCCGCTGCTTTGAACTCGAACACGAATT
TTAGCCGCAACATAAAATAAAATCAAGTAACTCTTTTAACTCAAATATAAAACAACAATTCCAATTCTTTCAACAGGCAATCTGTGTTTTTATGT
CAGATACGTGCGCGTGTGTGTGTGTGCTGTAATTCCATCGCCCCTTTCGATTCCGAGTTCGTTAGGAACAGCATTAGTTCGCCTATTTTAGTAGT
AGCCTAGTCCGATTTTAAGTGAAACAGGATACTCCAACACCATATACTCAATAATTAGTTACAACACCCACTCAACCATACAGCAACAACAAGTT
TAACGAGTTTTTTGTATTATCATTACTTAGTTTTTTGGTTAATAATACACAAGTGAAGAGCGAACTGCAGGGGAGCGAGATATCACGAAACAATC CAAAATCCACACACACTCAAACAGAAATCAAAAGCTTCGCTCTCTCGCACACACACGCACCAACCAACTATCAACTATCACAAACACCGCGACAG
AGAGAGAGCGGCAAGTGAATCACGGCGAATCGAAACCGATCCGAACCCACTCCGGAGCCGAAAAAGAACTGATCCTACCATCAAACGCATCCAAT
AAACACGGCCGCCAACATGCAGAGCGACTTTCACAGAATGAAGAACTTTGCCAATCCCAAGTCCATGTTCAAAGTAATACTCTCAGTGCGCCTGT
CGCTAAGCCAAGCTAATCTAATCTTCTGATTCCCCTTCCCATCCATTGCCATCTTCTCCCGCAGACCAGCGCCCCCAGCACCGAGCAGGGTCGTC
CGGAACCACCAACTTCGGCTGCAGCGCCCGCCGAGGCTAAGGATGTCAAGCCCAAGGAGGACCCACAGGAGACTGGTGAACCAGCAGGCAACACT
GCAACCACTACTGCTCCTGCCGGCGACGATGCTGTGCGCACCGAGCATTTATACAAACACCCGCTCATGAATGTCTGGACGCTGTGGTACCTTGA
AAACGATCGGTCCAAGTCCTGGGAGGACATGCAAAACGAGATCACCAGCTTCGATACCGTCGAGGACTTCTGGAGCCTATACAACCACATCAAGC
CCCCATCAGAGATCAAGCTGGGTAGTGACTACTCGCTATTCAAGAAGAACATTCGGTGGGTTTGCTGTTTATTGCAATTCTGCCAAGATAACCTT
TACTAACTGATATCTCATTTGCAGTCCCATGTGGGAGGATGCAGCCAACAAACAGGGCGGTCGTTGGGTCATTACCCTTAACAAAAGCTCCAAGA
CCGATCTGGATAACCTATGGCTCGATGTGGTAAGTGCACAAAGAAACGAGTGGTGAGCGGATGGTCTATTTATAGTGAATGTACATTCTTGAAAT
GCAAAAATATAGAAATAGGTGTATGATTTTGCAATATAAATTATAACTTATAGAAAATATCAGCTAAAAATACGCTAGTGCTAGCTTTTGTCTTA
GGAACATTCAATAGTGAGCTTATATCATAAATATTTTTCGCATATGAGTAACTACAACTGTTTTGCCTTCCAGCTGCTCTGCCTGATTGGTGAGG
CCTTCGATCACTCTGATCAGATCTGCGGCGCTGTTATAAACATTCGCGGCAAGAGCAACAAGATATGTAAGTTTTCACGCACACCCAACTTCAGC
GGAATTCCTTTGTTTAACGATTAATGCTTTCCAGCCATCTGGACTGCCGACGGAAACAACGAGGAAGCTGCCCTTGAGATTGGTCACAAGCTGCG
CGATGCCCTGCGTCTGGGACGCAACAACTCGCTGCAGTATCAGTTGCACAAGGACACGATGGTCAAGCAGGGCTCCAACGTGAAATCGATCTACA
CTTTGTAGGCGGCTAATAACTGGCCGCTCCTTATTCGGTCCGATCCCACACTGATTATTTTGTCTTTCATTTATTTATCGTTATAAGCAACAGTA
GCGATTAATCGTGACTATTGTCTAAGACCCGCGTAACGAAACCGAAACGGAACCCCCTTTGTTATCAAAAATCGGCATAATATAAAATCTATCCG
CTTTTTGTAGTCACTGTCAATAATGGATTAGACGGAAAAGTATATTAATAAAAACCTACATTAAAACCGGATACTTTTGATCTTTGATTTTGGAG
ATATTTTAAAATAGAAAAAGTTAACCTATATTGTTTTTGGGATAATTACTTGTTGTATTACTAAAACGAGCTTGTATCCTAATATGGGCACCTA
AAGCAAAACTTCCAAATTTGGAATTCAATTTGTTGCTAAAAATACGTTAGCAATTTCTAGGGTGGCCAAAAAAAAATGTGTATCGATATATCGAT
AGGTTTCCTAAATAGACATTAAAATAATTTTAGCTTTTTACTTATATTGTTAGAGTAAATACGTTTGTATTTAAAAAATAAGTCAGTATTTTTTT
TTTATTAACCTATTATTGAATTTTATATGAGTGAGAGCTTTTCCATTCAGCCAAGAACGGTCACACTGCATGTGACATGTTTCAATTGTGTAGGC
GCAGTCACACTGGTCGCGTCGCTCGTAGATATCGTGTAAGGATATGTCTCCGTGTTTAGCTAAATAAAATACATAAAATATATGTGCAATTCTAA
CAAGCATAGCCATTTAGCGTAGAGTAGTGGAACGAACAGCTCGTACCGGGCCAGTAACAACAAATTAACAAGCAAACGCACTAAAGTTTGTCGCG
GAATAAAGATATAATAATAGACCAGCTAACCAACACAAACAAACACACACACGGCCAGAAGTTCGTTGGCGTTGAAAGGGAAAAATGAAACGAAA
TGAAAGGAGAATAACAGTGCAATAGATTCGGTTTACATTGTGCAAAAAATCGAAGTAGCCCCTGCCAACAGGGTCGCTAAAAATAAAGAAGGCGA
CAGCCTCTGTTTATCGTTGGGAATAAACAAATATATGGCCAGCGGAGGAGAATCATAACAAAGGCGCAAGACTAGCCAGCATAAAAGACAAAGGA
GCTCTCCTCCCCCGCGTCCGCCACCCCCCTCCCTTTTTGGGGTTGAAAACCCCCCACGCGTTGCGGTGCAGCATCGCCCCGACTATGCGATACCC
TGCAATCGAGTTTATAGTGCTATAG
(SEQ ID NO: 1210)

Exon: 1001..1104
Exon: 1836..2163
Exon: 2250..2620
Exon: 2685..2784
Exon: 3019..3106
Exon: 3170..3585
Start ATG: 2107

Transcript No. : CT39424
CACAAGAGGGGAGGCGATAGTCGAGCGGAAAAGTGTGCAGTTGGCGTGGCTACATCATCATTGTGTTCACCGATTATTTTTTGCACAATTGCTTA
ATATTAATTTTTTTTGGTTAATAATACACAAGTGAAGAGCGAACTGCAGGGGGAGCGAGATATCACGAAACAATCCAAAATCCACACACACTCAAA
CAGAAATCAAAAGCTTCGCTCTCTCGCACACACACGCACCAACCAACTATCAACTATCACAAACACCGCGACAGAGAGAGAGCGGCAAGTGAATC
ACGGCGAATCGAAACCGATCCGAACCCACTCCGGAGCCGAAAAAGAACTGATCCTACCATCAAACGCATCCAATAAACACGGCCGCCAACATGCA
GAGCGACTTTCACAGAATGAAGAACTTTGCCAATCCCAAGTCCATGTTCAAAACCAGCGCCCCCAGCACCGAGCAGGGTCGTCCGGAACCACCAA
CTTCGGCTGCAGCGCCCGCCGAGGCTAAGGATGTCAAGCCCAAGGAGGACCCACAGGAGACTGGTGAACCAGCAGGCAACACTGCAACCACTACT
GCTCCTGCCGGCGACGATGCTGTGCGCACCGAGCATTTATACAAACACCCGCTCATGAATGTCTGGACGCTGTGGTACCTTGAAAACGATCGGTC
CAAGTCCTGGGAGGACATGCAAAACGAGATCACCAGCTTCGATACCGTCGAGGACTTCTGGAGCCTATACAACCACATCAAGCCCCCATCAGAGA
TCAAGCTGGGTAGTGACTACTCGCTATTCAAGAAGAACATTCGTCCCATGTGGGAGGATGCAGCCAACAAACAGGGCGGTCGTTGGGTCATTACC
CTTAACAAAAGCTCCAAGACCGATCTGGATAACCTATGGCTCGATGTGCTGCTCTGCCTGATTGGTGAGGCCTTCGATCACTCTGATCAGATCTG
CGGCGCTGTTATAAACATTCGCGGCAAGAGCAACAAGATATCCATCTGGACTGCCGACGGAAACAACGAGGAAGCTGCCCTTGAGATTGGTCACA
AGCTGCGCGATGCCCTGCGTCTGGGACGCAACAACTCGCTGCAGTATCAGTTGCACAAGGACACGATGGTCAAGCAGGGCTCCAACGTGAAATCG
ATCTACACTTTGTAGGCGGCTAATAACTGGCCGCTCCTTATTCGGTCCGATCCCACACTGATTATTTTGTCTTTCATTTATTTATCGTTATAAGC
AACAGTAGCGATTAATCGTGACTATTGTCTAAGACCCGCGTAACGAAACCGAAACGGAACCCCCTTTGTTATCAAAAATCGGCATAATATAAAAT
CTATCCGCTTTTTGTAGTCACTGTCAATAATGGATTAGACGGAAAAGTATATTAATAAAAACCTACATTAAAACCGG
(SEQ ID NO: 1211)

Start ATG: 376

MQSDFHRMKNFANPKSMFKTSAPSTEQGRPEPPTSAAAPAEAKDVKPKEDPQETGEPAGNTATTAPAGDDAVRTEHLYKHPLMNVWTLWYLEND
RSKSWEDMQNEITSFDTVEDFWSLYNHIKPPSEIKLGSDYSLFKKNIRPMWEDAANKQGGRWVITLNKSSKTDLDNLWLDVLLCLIGEAFDHSDQ
ICGAVINIRGKSNKISIWTADGNNEEAALEIGHKLRDALRLGRNNSLQYQLHKDTMVKQGSNVKSIYTL*
(SEQ ID NO: 1212)

Name: eukaryotic initiation factor 4E
Gene Symbol: eIF-4E
FlyBase ID: FBgn0015218

Celera Sequence No. : 142000013384822

TTCCCAATTCCTTCGAGGTGATGGCACCTTCGTTATCCTTATCCAATAAGCTATAGATATTCTTGAGCAGGTCCTGCTCTTCAACAGACAATTCA
TCCATTATGCTTTATATTATGGGAAGGAGAATATTATTATTATGCTAGTAGATATACTTTTTCGATAGGATTGATACTCAGTTGAGGTCTGATAA
GCTTTGAAGGAGTTCTACGATTGAAAATTGTTATTCAAAACATTCAATATAAATATTTTTGAAAAAAGCCAACTAAGAGTTAGCCTTCGGTCTTT
AACAGATATTAAACAATCTGCGTGCTCCATGAAGTTCATAAACTTTTACTGAAGATAAAGGCATTAAAAGAGCATTCTCACGCACAGTTTGGCAA
ACAAATCACGTGCTTTCCTGGACCCAAATGATATCATCTGGCGGAGAAACTCTTTGGCTTTACGCGTATTATTTTATAGTTGAACCAGAAATTGA
TGTCATCGGTGGCGGTAAAAAATGGGCGCCCAATCCGCCCAATGAGGAAATTCCAGGAAGCCGGGCAACTCCAACTGTCGGTGATGACAATTTGC
GTGGCATTTTAATTGAACTTTCTACGTGTTCGAGTGGTGTACTTTGATTTGATCCCCATCCACCGATTTTTCGTCGATTTGAGTCAATGTTAAAG
GCGTTGCCACAAACCGCAAACTGTCGTGTCTAGGAGGTTGGGGAGGGGCTTGGTGGCTGGGGCCTCGAAACGTGCCTGAAGTATTATTACCGCCG
TCTGTGATTGATGGCCTCATGCGAGTGAGTCAGTGGATTTTTATAACTCTACGCAGATCCCTTCCTTTCAATCAAGCGGCAAAAAATCTGGACAT
CGATCTCGCCGATATTAGCTAACTTCATTTCAACTTAACTGCCCGGAGTGCTTTGAATAAAGTGGATTTGAGGCGATGCCTTGGGATTCTTGGCC
AGATTAAGTCGATTTTTTTTTTTTACTTCAATGAAAAAAATGGCACGCAATTGTTTTTCATTATTAATGCATACTTTATTTGAAATCAACTAACT
CGCTATGGTTTGAATAAAATCATTTAAAATTGAAGGAAGACCATGGAATTCTATGGGTTGCTTATATTAACTACTGCAAAACTCTTAAAATTTAA
GCCTAATTACATAAGGTTCTACTGGAATGTTGCTTGTAGTTGGATTTTTGTTTATGCTCTGCTTTACACTAACTTTTACTTTCAACCATTTTTTT
CCCTACAGCAAAATCGATTAACGATTTTGTTTACTCATTAAGATTAGCTTACCGGATAAGGAAACATAAATAAAAAATTGGAATTCACTCAGCAA
ACAGCAACACTTAGTGTTGGGCCACACATTAAAAACTAATCGATAGACTCTCGTACTAAAGGCTTAAACATTTAAATCGGTAGATTTAAGCTAAA
ATCCTAACGCATAAGAGCTCTATAAAATGCAACAACGGAGTTTGTTTCGCTTACAATTATCGCTTAACTGATTTTATTACTTAGTTTAGGTCTAT
TGCCTTGCCTAGACATTGTACTAAAAAGTATTAAATTGTAGATCTAAATTTATTTTAATGTACTTGTGGGTCTAAAACGATAAATCCTCGTTTAA
CCATTGGGAACAATAACTGTTTGTCATTATGATATTCAACTGTTCATAAGACCTTCTAAATGAAATACCAGAAAAAACAACCGAGATATATATTT
ATTAGGAATACTACTACTTTTTGATATTTCAAATTCGTAAGAGCTTTGATAAATAGTTTTCCAAATTGTGTTGTTTTTCTATTCCGATTTTACCT
CCATTAATGGATTGTTTTCTAGTTCTTTCTCGGTTTACTTCTAACGCCTCATTATGTCCTCAATGCTGAACCCTGTTCTTCTCGGTGGTGCAGGC
GGTGGTGCTATGGGCGGTGCTGCCACTGGTGGTCCCTTTTCGGTGGTGGCTCCACTTGTTTCCGTACTCGGTGGTTTTCCCAGAAGCTGTCTGGG
GGGATGTCGCGACATATTCAAAGCATATATGCTGGGACTATCCACAAAGGTCCTTTGACCCAATCCAGGATGGTGGTGCGGATCCATCAAGTCCA
AGGTCGGTGCCGGAAGAATCCTCTTTCGCATGGGTATCGATCCCAGGAAGCTGGGCATAGCTTCATGCGGTGAATGCAAAGGTTGATTGGGTGGT
TTACCCGACTCCGGCTGGGTTATTATAGTGGGTGGTGTATGTGGTGGCGGTGGAACACCAGCCTTCGAAAGGTTCAAGCTCTTGTGGTGCAAGTC
GCGTCGAACGTGCAGAATGGGCAAATAGGGATCCCCGTTGGGTGGGAGTAAGTGTGGATGTCCTGGGTGCTGGTGGGTTGGCGGAGGAGCTCCAG
GTGGTGCAGGCGGCGGTCCAGCTGCCCCAGGTGGTACAGAATATCGCACAAAGGAAGGTGGAACGGGTAGGCTGGCAATGCCAGAGTTCCCGGGT
TCCTCCTGATGTTTCTCGCCATGTGGCCGCATTGTGTAGGTTTCACCACCCTCATGATGACAGTGGGTGACTCCCTGGCGTTCCGGCTTGGTGCC
CACTGACGACGATGATTGCGATGTGGCGGCAGCCTTACTCGCCTGGAAACGCGCCACTAGTGCCACTTCTGCCTGCTCCTCGTCCTCGGGATCAA
AGTCGTCGTCCTCTTCCCTGGGCAAATCGTGTACTCTTGGCAGATCCTGCAGTTCCTCTTCCTCGTCGAAGTCATCGAACTCCTCTTCGCTTTCC
TCATGATCGATGGCTGCCTTGCGCTTGAGTCTCATTCTTTCGGACTCAGATTTCTCACCCGATCCTCCAGACTCGCCCAAATTGTGAACTGGCGA
CTGGCGAGGCGAGTCCACTTCCAGCAACGAATCCTCCTCGTCGCCACTTAAATTTCTGGCCTCATCCTCTTCGCCCACATCCACATAGTCCCCGG
AGTTGACCTCACCCACTGCATGGGTCAAGGCATGGCGTCGTAGATCGCAGTTACGGCGGAAAACTTTGCCGCATGAAGAGCACTCGTAGGGCTTG
TGATCCGTGTGGGTGAGCAGATGGGTCTTCAGGTTGGAGCGCTGATTGAATGATCGACTGCAGACGGGGCACTTGTGGGGTGATTCCTCCATGTG
CAGGATCTTGTGGACAGCCAAGGTTCTCGATTGGCAGAATCCCTTGCCGCATTCCGTGCATTTGAAGGGTTTCTCCTTGGAGTGAATATACCTGG.
GCGAATACAAGTGGAGAAACAATTAGACTTTATTGTTATAGCGTGGGCGTTTTCCTGGTAGCTGCAATTGGTAGCCCAGGTTGACAGTTATCTCT
GCTCAAATGCAGCCTTAACTTGAACCGATAAAGCTCACTGATATACAGCTTTACAATACTCTAACTAAGGATATAACTGGCTAGAGCAGACAATA
GAATAAATAATATAATACTATAGCATATAATACCTATCTTTCTCTTTCAAAATGAAACCTAACCTGGATTTGTTTTAACCTTAAACCCAATTCTT
TAAAGTTTTTCATTAAAGAAATCCTATGATTTTGTATCCTCTTAACTGATAGGGTATTTAACTTTCGTGTATGCGATCTGGCTGCATTAATTTTT
TATGTTTATGGCGGCCATCTTGGCAATGGCGTCCACTTGCTGTTGGATAGCAGCAGCCACAGTTAAAAGTTAAAGTCCCCATCTTCGACGGAGCC
ACAGATTCAGCATCGCATCGGAGGCAGCAGCTGCTGGTGGAAAAAAAAAAAATAAATGTATAAAAACCCAAAACAGGTTCTGCCTCCGAAGCACCG
AGATTCTTCTCCCATGCTCCGTGCGTTTCTGGTAAAAAAAAAATACAAAAAACTTAAGAAGAATTAGCCCCGCGGCAAAGCAAACAAACGACAAA
TGGACCGATACCGAACGATCAAAAGACAGAACGCTCGGACAGGCCGACACATTGAAGCCGGGATGCTGGACCTGCTGCCTGGCATCGGCATGGGC
ATCGGCACCGGGATACACAGACCCGATATATAGCCCCCAACCCCTTGGCCATCCCTCAATTTTAATGCTGGTGGAGGAGCCCCAAAGGAAAACCA
ACAGAGTTAATTAACTTTGTGTTGTACTCTGCGGCCGAGTTGAAGTTTTACTGGCCGTCAGAGGAGCTCTGATTTTGGGTCCGCTTTATGGGGAC
TTACTTATTTGAGTTGAGGTAGGAAAATTCGTCGTAAAGTTTAAACATTTCCTGGAAAATTCCTTATGGTAAAAGGGGTCTTTTGAAGCGATTGT
CTGATATATCTAAAATCAATAAAACTCCATCTACGAGTAGTGGTCGCCTTTCCCTTTTGGCCGAGATTACTGTCACACCTGTTCAGAATGTGTGT
ATAAACTGCCTAGTAAGCAATAAATTACATTGATCTAATTATCCTTTGCCTTTACAGGGTATTCCATTATTCGCCATTCGTTCACACTTTGAGCA
CAAAGAATAACTCCAGGCCTGATGGCAATTACCCGAGCAGACACTGCCCCCTTTTGTGATTACTTGTACCCCAACCTCGACTCACCTGTGATCCC
TCAGGTGATCCTGTCGCCGGAACGCCTTGCCGCAGATATCACAGGAATAGGGCCGCTCGTCCGTGTGTGTCCTCTCGTGGATGAGCAGATTGTAC
GACTTGGTGAATTGTCGATTGCAGAACTTGCAGATGAACTGTTTTTTAGGCCGCGATGCCCGACCAGGAGCACGTAGCAGGCGCCTATCGAGTCC
GGCATGCATTCCAGGACCCAGGCCAGGTGGAAATAGAGCTGCGGCGGCGGCTCCTGGTGGAAATGGAAAACTTCCGGCTCCCGTGGGCGATGGAC
CCGGTCCGGTGAGATATGGCGGAGGTGGCACGCCAGCTGGTCCGTACAACACTCCAGGCGGTGGCACACCAGGACCGCCGGGTCCTCCAGGACCT
CGTCCTAACATTGCCGCCGCCGCAGCCGCCTCCCTTAGGGCCAACTCCTTTCGCTTGTCCGCCATCATGGCAATGATTTCGTAATTGGAATTACT
ACCCGGGCGCACCTTTCCGGTGGGCAGAACCGGCACAAAGGCAGAGATCTCGCGATGATGCGATGGTGGTGGCGGTGGCGGCGGACCATGCAGTC
CGGCCAAATGCTGCTGATAGGCCAGCTGTGTTTCATACGCTGAGATCCGGCTGGCCGATGAGTTGCGCGAATCGCCGTTGCCATTCTGGGAGCCA
CCATCCGATCCTCCGGATCCGCCGTTCCTATCCGCCGCACCAGGAAGACCGCCACCACCCACCGCCGCCGCTGCCGCCGCCATCGAGTTCATGAA
CTGATCCATCCGGGAAGGTCGCAGCATGGGTATCGCACCGCCTCCTCCGCCGGAGATCTCGCTGGATGAGCTTTCCGTGGGCATTATATTGGAGG
GGCTCTTCACATTCCGTTGGAACTGCCGGAGATAGGGATAGAACAGAAAAAGCCGAAAATAAAATAAGGGTAGTGGTAAATAACAATTAGTACAC
GATTGTGCTGGGTTAATTGGGCTCTCGTTTTTTTTTCGAGGCTTATCTTAATTGCGAACCGAGTGCAATAAACAGATATTTCCACGTTGTATTCT
TTATTGCTCCTAGGGTAGTACTGGGTATGATAAAAACTGACGCAAACTGGTTTAAAATAGATATATTACTATTAACTTAGTTTCTTCTTGGTGGG
AAGTTTCCTTGTAATTGAAATATTCATGATCTTGGTTTGGCAAGGCACAGGAATATATACAATATATACTATAGAATATTTACTCTTTTTATCTC
AACCGGTTGTAACTCACTTTTTAGATGTGAAATTCTTCAAATTTGCTTTTTGCACTTCTTATCACAAAATTAAACAGCTTTATGGGCAATTAACT
TGCAAATAGCCAAGGATTATCACATTAGCTGATCTTTCAGAATTTATCCACGTGAACGTGATTTAGTAGTCACAAAAAAAAAAATAATGAAGAAA
ATATTTTTCTCGAAAATAACCCATACGATTCTGAGAACGTTTTGGTATCACAGTACGTATATTTTCACAGGGTAACTAAGCAGTTTATCACATTA
TGGCCCTCGTCTATGGGTTTGTTGCTGTGTTTTTTCCATAGGAATTTTATTATTATTGTTGGTTTATTATTATCAGCGGCGGACTGCCGACGACG
GCGAGTGAAACTAAACTGAAAACGAGTCGCAGTTTGGCACCGCGATCGGTTGCTTCCAGTGCGCAGGTTAGATAAGATTGTGCGTCTAAAAAAAC
CTGCCTCCGAACCTCTGAGACTGAGTAAGCAGCACAGTAGTAACGATATAAACACACACACACACACACAGTTATATTATATATGTGCCTGTGAT
ATATGGCATATCGGCAGATACCCCGGCACACTCAGATACAGATACAAAGATACAGATACAGAGGCAGGCAGCCAAGTTGCCGTCGGTTTTGGTAA
ATGACTCGAACCGAACTCGACCGACTGCTTACTGGATTTACGCAACAGGAGCCTCGACTTCTGAGTGCCTCGAAAGAAGAAGGGGCAGAGGCAGG
GGCAGGGGCAGGGGATCGGGTCCCGGAACGTGATCATCACGATAATAACAAAATAATGCACATAATAATGATCACAATGATGGCCGGACCATAAA
GTTTGTGGCCCCATATTGCAAACGCTTCTGGCTGCCATCTTCCCAACGCCTTGCACAGCAAAAAAAAATGGCACCAATTTTGTACCCAATTCTATG

FIGURE SHEET 651

GAATTCTATTTTAAGATCTATCTTTTACGATAAGATTATATTTGTTATAATATTAAAGAATTTATAGTAATATGCTTTAAAATTTGTGGCTCGCA
AAGAGTGCGCC
(SEQ ID NO: 1213)

Exon: 5851..5813
Exon: 5437..4551
Exon: 3226..1001
Start ATG: 5404 (Reverse strand: CAT)

Transcript No. : CT40018
AGTGCAAAAAGCAAATTTGAAGAATTTCACATCTAAAAATTCCAACGGAATGTGAAGAGCCCCTCCAATATAATGCCCACGGAAAGCTCATCCAG
CGAGATCTCCGGCGGAGGAGGCGGTGCGATACCCATGCTGCGACCTTCCCGGATGGATCAGTTCATGAACTCGATGGCGGCGGCAGCGGCGGCGG
TGGGTGGTGGCGGTCTTCCTGGTGCGGCGGATAGGAACGGCGGATCCGGAGGATCGGATGGTGGCTCCCAGAATGGCAACGGCGATTCGCGCAAC
TCATCGGCCAGCCGGATCTCAGCGTATGAAACACAGCTGGCCTATCAGCAGCATTTGGCCGGACTGCATGGTCCGCCGCCACCGCCACCACCATC
GCATCATCGCGAGATCTCTGCCTTTGTGCCGGTTCTGCCCACCGGAAAGGTGCGCCCGGGTAGTAATTCCAATTACGAAATCATTGCCATGATGG
CGGACAAGCGAAAGGAGTTGGCCCTAAGGGAGGCGGCTGCGGCGGCGGCAATGTTAGGACGAGGTCCTGGAGGACCCGGCGGTCCTGGTGTGCCA
CCGCCTGGAGTGTTGTACGGACCAGCTGGCGTGCCACCTCCGCCATATCTCACCGGACCGGGTCCATCGCCCACGGAGCCGGAAGTTTTCCATT
TCCACCAGGAGCCGCCGCCGCAGCTCTATTTCCACCTGGCCTGGGTCCTGGAATGCATGCCGGACTCGATAGGCGCCTGCTACGTGCTCCTGGTC
GGGCATCGCGGCCTAAAAAACAGTTCATCTGCAAGTTCTGCAATCGACAATTCACCAAGTCGTACAATCTGCTCATCCACGAGAGGACACACACG
GACGAGCGGCCCTATTCCTGTGATATCTGCGGCAAGGCGTTCCGGCGACAGGATCACCTGAGGGATCACAGGTATATTCACTCCAAGGAGAAACC
CTTCAAATGCACGGAATGCGGCAAGGGATTCTGCCAATCGAGAACCTTGGCTGTCCACAAGATCCTGCACATGGAGGAATCACCCCACAAGTGCC
CCGTCTGCAGTCGATCATTCAATCAGCGCTCCAACCTGAAGACCCATCTGCTCACCCACACGGATCACAAGCCCTACGAGTGCTCTTCATGCGGC
AAAGTTTTCCGCCGTAACTGCGATCTACGACGCCATGCCTTGACCCATGCAGTGGGTGAGGTCAACTCCGGGGACTATGTGGATGTGGGCGAAGA
GGATGAGGCCAGAAATTTAAGTGGCGACGAGGAGGATTCGTTGCTGGAAGTGGACTCGCCTCGCCAGTCGCCAGTTCACAATTTGGGCGAGTCTG
GAGGATCGGGTGAGAAATCTGAGTCCGAAAGAATGAGACTCAAGCGCAAGGCAGCCATCGATCATGAGGAAAGCGAAGAGGAGTTCGATGACTTC
GACGAGGAAGAGGAACTGCAGGATCTGCCAAGAGTACACGATTTGCCCAGGGAAGAGGACGACGACTTTGATCCCGAGGACGAGGAGCAGGCAGA
AGTGGCACTAGTGGCGCGTTTCCAGGCGAGTAAGGCTGCCGCCACATCGCAATCATCGTCGTCAGTGGGCACCAAGCCGGAACGCCAGGGAGTCA
CCCACTGTCATCATGAGGGTGGTGAAACCTACACAATGCGGCCACATGGCGAGAAACATCAGGAGGAACCCGGGAACTCTGGCATTGCCAGCCTA
CCCGTTCCACCTTCCTTTGTGCGATATTCTGTACCACCTGGGGCAGCTGGACCGCCGCCTGCACCACCTGGAGCTCCTCCGCCAACCCACCAGCA
CCCAGGACATCCACACTTACTCCCACCCAACGGGGATCCCTATTTGCCCATTCTGCACGTTCGACGCGACTTGCACCACAAGAGCTTGAACCTTT
CGAAGGCTGGTGTTCCACCGCCACCACATACACCACCCACTATAATAACCCAGCCGGAGTCGGGTAAACCACCCAATCAACCTTTGCATTCACCG
CATGAAGCTATGCCCAGCTTCCTGGGATCGATACCCATGCGAAAGAGGATTCTTCCGGCACCGACCTTGGACTTGATGGATCCGCACCACCATCC
TGGATTGGGTCAAAGGACCTTTGTGGATAGTCCCAGCATATATGCTTTGAATATGTCGCGACATCCCCCCAGACAGCTTCTGGAAAACCACCGA
GTACGGAAACAAGTGGAGCCACCACCGAAAAGGGACCACCAGTGGCAGCACCGCCCATAGCACCACCGCCTGCACCACCGAGAAGAACAGGGTTC
AGCATTGAGGACATAATGAGGCGTTAGAAGTAAACCGAGAAAGAACTAGAAAACAATCCATTAATGGAGGTAAAATCGGAATAGAAAAACAACAC
AATTTGGAAAACTATTTATCAAAGCTCTTACGAATTTGAAATATCAAAAAGTAGTAGTATTCCTAATAAATATATATCTCGGTTGTTTTTTCTGG
TATTTCATTTAGAAGGTCTTATGAACAGTTGAATATCATAATGACAAACAGTTATTGTTCCCAATGGTTAAACGAGGATTTATCGTTTTAGACCC
ACAAGTACATTAAAATAAATTTAGATCTACAATTTAATACTTTTTAGTACAATGTCTAGGCAAGGCAATAGACCTAAACTAAGTAATAAAATCAG
TTAAGCGATAATTGTAAGCGAAACAAACTCCGTTGTTGCATTTTATAGAGCTCTTATGCGTTAGGATTTTAGCTTAAATCTACCGATTTAAATGT
TTAAGCCTTTAGTACGAGAGTCTATCGATTAGTTTTTAATGTGTGGCCCAACACTAAGTGTTGCTGTTTGCTGAGTGAATTCCAATTTTTTATTT
ATGTTTCCTTATCCGGTAAGCTAATCTTAATGAGTAAACAAAATCGTTAATCGATTTTGCTGTAGGGAAAAAAATGGTTGAAAGTAAAAGTTAGT
GTAAAGCAGAGCATAAACAAAAATCCAACTACAAGCAACATTCCAGTAGAACCTTATGTAATTAGGCTTAAATTTTAAGAGTTTTGCAGTAGTTA
ATATAAGCAACCCATAGAATTCCATGGTCTTCCTTCAATTTTAAATGATTTTATTCAAACCATAGCGAGTTAGTTGATTTCAAATAAAGTATGCA
TTAATAATGAAAAACAA
(SEQ ID NO: 1214)

Start ATG: 73 (Reverse strand: CAT)

MPTESSSSEISGGGGGAIPMLRPSRMDQFMNSMAAAAAAVGGGGLPGAADRNGGSGGSDGGSQNGNGDSRNSSASRISAYETQLAYQQHLAGLHG
PPPPPPPSHHREISAFVPVLPTGKVRPGSNSNYEIIAMMADKRKELALREAAAAAAMLGRGPGGPGGPGVPPPGVLYGPAGVPPPPYLTGPGPSP
TGAGSFPFPPGAAAAALFPPGLGPGMHAGLDRRLLRAPGRASRPKKQFICKFCNRQFTKSYNLLIHERTHTDERPYSCDICGKAFRRQDHLRDHR
YIHSKEKPFKCTECGKGFCQSRTLAVHKILHMEESPHKCPVCSRSFNQRSNLKTHLLTHTDHKPYECSSCGKVFRRNCDLRRHALTHAVGEVNSG
DYVDVGEEDEARNLSGDEEDSLLEVDSPRQSPVHNLGESGGSGEKSESERMRLKRKAAIDHEESEEEFDDFDEEEELQDLPRVHDLPREEDDDFD
PEDEEQAEVALVARFQASKAAATSQSSSSVGTKPERQGVTHCHHEGGETYTMRPHGEKHQEEPGNSGIASLPVPPSFVRYSVPPGAAGPPPAPPG
APPPTHQHPGHPHLLPPNGDPYLPILHVRRDLHHKSLNLSKAGVPPPPHTPPTIITQPESGKPPNQPLHSPHEAMPSFLGSIPMRKRILPAPTLD
LMDPHHHPGLGQRTFVDSPSIYALNMSRHPPRQLLGKPPSTETSGATTEKGPPVAAPPIAPPPAPPRRTGFSIEDIMRR*
(SEQ ID NO: 1215)

Name: brother of odd with entrails limited
Classification: transcription_factor
Gene Symbol: bowl
FlyBase ID: FBgn0004893

Celera Sequence No. : 142000013384695
CACCTCGTTGATAATTCACCAGAAGCTGAAACCGCTCGAAAATATGATCATCCTAGACATCACTTGCGACAGGGAGTTCGTCATGGACTACATTG
TCACGGTGATCCTTACAGCATTGTCTCTTGTGCAGTACACCATATCAACTGGAGGAAATATAAGCGAGTGCGTGACCCATAAATAGCAACCCATC
TGGACCACACTATTAGGAGGATGAGATCATTATATAACTGTGGAGCTGGACACAGTTATCGTATAATTGCGTGGGTCAAAAGAACTTCCTTAGCG
CCTACAAAAGTGTATCTTTTGAAAGCAGAACTCAGAGCTCGTAATTATAAAGCACTAAATGCTTACTATTTAAATGCTACAAATGGTTTTATTGT
TTTTATACAAAATTAAGGTTTATTGACTGTAGTAGTAAACTTGTCAGATACGTGGTTTTACGCACTGCGATTCAACAACACAGGATTTCCCGTTT
GCATAGAGAATTATGAGAATTCGTTCGTTTCAAGAAAATCCCGTGACTCTAATGAGAACAAGAAAATGCTGTCACTGTCGATTTATCCCTTTAGT TTCGATTTCACGTGATGCTTAAGGTCCTGTTCTCGTTTCCTCGGCAGACAAGAGATGCTCAATTGTGCATAAGATTTGCCACACTGGAGCCCAGT
TTTATTTAGCTTACATATAGTTTAAATTTTATTTAGTAAATATGACACATGTTCCTATCTAACATATTACCTGAACTAACTATACGATTTACTTG
TAAAGTAACAATCAACCTAAATTATTGTAGTTAAGGTCCACGTAACAGGTAGGATATATGAATCAGGATATCATGTTCCTCGACTAGCAAATCCT
TTAATTGTTCTTATTACCTAGTACAGGCCATTGAATCTGGTATATCCTATTATACTAAGAGTGCGTACTTCAATAACCACGGCTGTTGTGAAATT
TAAGTGGCTTTAATTGCGACTAGCCCAATCACACTATTCCAGTAGCCCATTTACAGCGCAATTTTCGCCCACTTCTCGGACTGCGCCCACAACCA
CTGGGCCATCTGGTCGTCGAGGGCAGCGGGAGCTACCGGAGCCAGAGCGCAATCGCTGAAGTACTGACCCGACACTCTTTCGAGATCAGGATCCA
AGGCAGCATACAAGGTGGTCTGGGCCCCGTTCTTAGGCGTCTTCATCACGGCCCAAAGGAGCGGCCTCAAAATGGTTCTAAATGAAAACCAAAAA
TTAGTAAGTGTATAAAAAGAGAATTGAAAGAGGACACACTCTACCACATACTGAGCAAACTTTGTTTGGAAGAAGATCATGTTCCTGGCTATCTC
CGTGTCTGCTATTCCAGGATTAAGGGCGTTGACCGTCACGCCCGTTCCCTCCAACCGCTTGGCCAGTTCGCGGGTGAAGAGTATGTTGGCCAGCT
TACTTTGGCAGTAGGCTACTCCCTCGTCGTAAAAATCAGAGCTGTTGATGTCATCCACCTTAATCTGACCCCGTTCGTGGGCCCTGCTGGCGACC
ACCACCACCCGACTAGGAGCCGACCTCTCCAGCACGCCGAGCAGTAGGTTGGTTAGCAGGAAGTGTCCGATGTGGTTTACACCCAGGTGCATTTC
GAATCCCTCTTTCGTCAATCTATGCGGTTCCCAAAACACACCAGCATTGTTGATGAGGATGTGCAGCACCCTCTGCTCTTTCTTGAAGCTGTTTG
TGAATGAATTGTTAGTTCAAGAGAAAGACACTACGGAGTGGCATGACTCACTTCTCTGCAAACTTTCGAATGGAATCCAGGGACGACAAGTCGCA
CTCCCGTGAGAAGACATTGGAGTTTCCGGTCTCCTTTACGATTTCCCTGCGCGCTCTCTCCACCTTTTCTTTGTTGCGGCATGCCATGTAAACGG
TGGCTCCTCTCCTGGCCAACTCCATCACGGTCTCCTTGCCAAGACCCGTATTTCCGCCAGTAACGATGGCCACTTTTCCCGTCTCATCGGTCTGC
TTCCTAAACTTTCCGCCCTGCATATACAGCCTGATGTGTGTTAAAACAATGCATGTTAATCGGTGATAACTACTTTGTCGTCACTTTTATACGTC
GTCGATAACGCTTCTCAGCGTTACATTTTAAATTGGCGTCTCACTTACCTCACGCAGAAGGCGATAATGCCGACAATCCCATGGGCCAAGAAGAC
GGGTGCTATGCTTTGCAGAAACCTTATAACAATTTCCATACTGGCTAAGCGGTCCGCTCCTTCTTGTGGTCTATTCCAAAGTGCCACCGCGGGCG
AAATTGTGCGGGTTTTTAAGAGATCGCCGCAGCGATTACCGGACGACAACTGATAAAATTGATAGTACGGGCTTCTATAAGTGTTCTTTAATCAG
AGAACCGCTATTCGAACACATTCAAAATTGCTTATAGCGACAAGAAGCCGAAACCGTCAAACTTTACAAAGAGCGAAAATGTTGCATACTGCCGA
AATGAACCTAAACTTTTGGACCGAAGGCTCGGGTTAAAATGTAATGGATATACACGTCTATTTTAAACAAATGATGTAGAAATTGCCCCTAACCG
GTTTCGGGGTACGTAAGTTTGAACGCACACAAGCCCTGAGCTTTCAACTCTTATTAGTCGGCCACGTTAAAATAACTAAAACAAGACAAGTGGAA
TTGTGTAGACTGTAAGAAACTGAAAATTTATGCGAAGTAACAGAGGGATTGTCAGAAACATATTTCACAATACGAACTATTGTATTTTAATCATC
GTTGGCTTCGTCCACTTTTCACTGACTGCCCAAAGCCACTTTGCCGTTTGGGTGTCGGTGGCAGCCGGCGCCATTTCCTTCAGTTTGCAGTCGCT
GAAGTATTGTCCTGTCACCTTTTCTAGCTCGGGATCCAGAGCAACATACAACGAGGTCTGAGCACCATTTCTCGGAGTCTTAACAAAGGGCCAAA
ACAAAGGCTTAACAAAGAGTCTGAAAAGATAAGTATTTCGTAAAAAAGGTTTTAATGGCATTACTTCTCTACAAACCCAGCAAAAAAATTATTGA
AGAATCCCATGTGCCTGATTATTTCTGTGTCCACCACACCTGGATGCAGGGCATTCGCCGTTACGTTGGTGCCCTCTAATCGTTTGGCCAACTCC
CTTGTGAAGAGTACATTGGCCAACTTGCTCTGGCTGTAGGCCTTGCCTTCATCGTAGGATTTGTCACTGTTCAGATCGCCAGTGTTTATTTCTCC
TCGAGTGTGTGCCAAACTGGATACATTTACAATCCGACTGGGTGAGGATTTCTAGGAATAAAATGGTTATTAATCAGATTTAAGATCTAGTAAAG
CTGTGTGGTACCTTGAGTAGATCCAACAGTAAATTGGTAAGCAGGAAATGACCCATGTGATTAACCCCCAGCTGAAGTTCGATGCCATCTGAGGT
GAGAGATCTGGGACAGCGCATAACACCGGCGTTGTTGATCAGTACGTGCAGGTGCTCCTGTTCCCTCTTGAAGCTGCGGAGATGGATTGCGGAAT
AAACACAACTTAGGCCTTAGGTAGACTTACGCGGCAACAAAGTGACGGATGGACTCCTGGGAAGCCAGGTCACATTGCCGGCAGTACACATATTT
GTTCTTCGTTTCCAGCACGATTTCCTCGCGAGCCTGCACGCGAGAAGTATTTAGTCGTGTTTTAGGAAATTATCTCAATAAAGATCGTACCTCCT
CACATTTCTTTAGGTTTCTGCATGCCATGTAGACGGTGCCACCTCGCTTCGCAATCTCTCTCACCGTCTCCTTGCCGATCCCCGTGTTGGCACCG
GTGACAATAAACACCTTGCCGGTCTCATTGGTTTCTTTGGTGAACTGACCGCCTTGCATAAGATCCCTGTGAGGCGGTATAAAATGTGTAGTCAA
AACAAGGGAATTCTGTGTGAGAAGCAGATCACTCACTTCACGAAGAAGGCCAGTCCCGTCGTCGTGCCGGTGAAGCTCAGCCAGAACGCAGTGCG
GCTCTTGAGAAACGCAAATAGTGACATTTTAGGAACTCAAAAAATATACAAATTAGCTAATAAACGAAAACAGCTGTGTTTACCCTGTTAAGGCT
AACAGCGCTCGTTAACAGAGTCCTATCGATATTTTCGGTCATCTGTGACGGAGCTTTCCCTTTGTTGTTGTTCGTGGGCTGCTGCTTAGAACAAA
CTTTACACGTAAATAATCTAATTGCGTTAATTAACTGGCTTGAGCTAAACAACGACGTGCGATTTGATCGAGGGAAGGAACGTAGTTGAGATCTG
GGCCAGGAAATCCCGACTAGGCAAGCAGGAAAACAATGCGTCGCAATGCGTAAGTCAGCGCCAACTCGACTGTTGCTTTTTCCAAGAGATCCGAA
TGTGATCGGAGTTCTCCCCTCATCTTCAGGCGCCAACAACAACACAATCAGGAAGAAATCGGCCCCGACGACGTGGAAGACATCTTTGCCCGTCC
CGCCTACGATGACGACGAGTTCGAAGATCTGCTCCCTCTGGCCAGGAGGCCCAATGGCCACGCCCGACTCGGCCGCTACGAGAACACTCTGGAGG
TAAAGGTCCAAGAGGGAGACACACTCCAGGCGCTGGCCCTGCGCTTTCACTCCTCTGTGGCGGACATCAAGCGCCTGAACAAGATCGACCGCGAA
AATGAAATCCACGCACATCGGGTTATTCGCATTCCGGTTACAGTGCACAACGTCCTGCTGGGCAACGGGGGCCTCGAAGCCCTTCCTGCGGTCCA
CCGCAGCGGGAACAACAGTCCTAGACACAATATTGAGCGGGAACCAGCTCCCGAACGCAATCCCCTCGAGGATGCGCGGCAAATGCTGGATGAGC
GACTCCTGGTGGCGGCGGTAAATGCTTCAGGCGCCGTGGATCACGAGAAACCATCGACGAGCAGAGCTGCTGGACAATTCTACGAGGGAGCCCAG
GGTGCGCCGAATGACGAAGGTGAGTACAGAAGATGCAGTTGGGAATGAAAGCCCACAGTTCGCCGCGGTTTTAAAAATTTCTGAAATACTTTCA
(SEQ ID NO: 1216)

Exon: 4034..3932
Exon: 3866..3701
Exon: 3643..3546
Exon: 3493..3337
Exon: 3281..3105
Exon: 2928..2782
Exon: 2012..1762
Exon: 1703..1001
Start ATG: 4017 (Reverse strand: CAT)

Transcript No. : CT40158
TTTTTTGAGTTCCTAAAATGTCACTATTTGCGTTTCTCAAGAGCCGCACTGCGTTCTGGCTGAGCTTCACCGGCACGACGACGGGACTGGCCTTC
TTCGTGAAGGATCTTATGCAAGGCGGTCAGTTCACCAAAGAAACCAATGAGACCGGCAAGGTGTTTATTGTCACCGGTGCCAACACGGGGATCGG
CAAGGAGACGGTGAGAGAGATTGCGAAGCGAGGTGGCACCGTCTACATGGCATGCAGAAACCTAAAGAAATGTGAGGAGGCTCGCGAGGAAATCG
TGCTGGAAACGAAGAACAAATATGTGTACTGCCGGCAATGTGACCTGGCTTCCCAGGAGTCCATCCGTCACTTTGTTGCCGCCTTCAAGAGGGAA
CAGGAGCACCTGCACGTACTGATCAACAACGCCGGTGTTATGCGCTGTCCCAGATCTCTCACCTCAGATGGCATCGAACTTCAGCTGGGGGTTAA
TCACATGGGTCATTTCCTGCTTACCAATTTACTGTTGGATCTACTCAAGAAATCCTCACCCAGTCGGATTGTAAATGTATCCAGTTTGGCACACA
CTCGAGGAGAAATAAACACTGGCGATCTGAACAGTGACAAATCCTACGATGAAGGCAAGGCCTACAGCCAGAGCAAGTTGGCCAATGTACTCTTC
ACAAGGGAGTTGGCCAAACGATTAGAGGGCACCAACACTCCGAGAAATGGTGCTCAGACCTCGTTGTATGTTGCTCTGGATCCCGAGCTAGAAAA
GGTGACAGGACAATACTTCAGCGACTGCAAACTGAAGGAAATGGCGCCGGCTGCCACCGACACCCAAACGGCAAAGTGGCTTTGGGCAGGCGGAA
AGTTTAGGAAGCAGACCGATGAGACGGGAAAAGTGGCCATCGTTACTGGCGGAAATACGGGTCTTGGCAAGGAGACCGTGATGGAGTTGGCCAGG
AGAGGAGCCACCGTTTACATGGCATGCCGCAACAAAGAAAAGGTGGAGAGAGCGCGCAGGGAAATCGTAAAGGAGACCGGAAACTCCAATGTCTT CTCACGGGAGTGCGACTTGTCGTCCCTGGATTCCATTCGAAAGTTTGCAGAGAACTTCAAGAAAGAGCAGAGGGTGCTGCACATCCTCATCAACA
ATGCTGGTGTGTTTTGGGAACCGCATAGATTGACGAAAGAGGGATTCGAAATGCACCTGGGTGTAAACCACATCGGACACTTCCTGCTAACCAAC
CTACTGCTCGGCGTGCTGGAGAGGTCGGCTCCTAGTCGGGTGGTGGTGGTCGCCAGCAGGGCCCACGAACGGGGTCAGATTAAGGTGGATGACAT
CAACAGCTCTGATTTTTACGACGAGGGAGTAGCCTACTGCCAAAGTAAGCTGGCCAACATACTCTTCACCCGCGAACTGGCCAAGCGGTTGGAGG
GAACGGGCGTGACGGTCAACGCCCTTAATCCTGGAATAGCAGACACGGAGATAGCCAGGAACATGATCTTCTTCCAAACAAAGTTTGCTCAGTAT
GTGGTAGAGTGTGTCCTCTTTCAATTCTCTTTTTATACACTTACTAATTTTTGGTTTTCATTTAGAACCATTTTGAGGCCGCTCCTTTGGGCCGT
GATGAAGACGCCTAAGAACGGGGCCCAGACCACCTTGTATGCTGCCTTGGATCCTGATCTCGAAAGAGTGTCGGGTCAGTACTTCAGCGATTGCG
CTCTGGCTCCGGTAGCTCCCGCTGCCCTCGACGACCAGATGGCCCAGTGGTTGTGGGCGCAGTCCGAGAAGTGGGCGAAAATTGCGCTGTAA
(SEQ ID NO: 1217)

Start ATG: 18 (Reverse strand: CAT)

MSLFAFLKSRTAFWLSFTGTTTGLAFFVKDLMQGGQFTKETNETGKVFIVTGANTGIGKETVREIAKRGGTVYMACRNLKKCEEAREEIVLETKN
KYVYCRQCDLASQESIRHFVAAFKREQEHLHVLINNAGVMRCPRSLTSDGIELQLGVNHMGHFLLTNLLLDLLKKSSPSRIVNVSSLAHTRGEIN
TGDLNSDKSYDEGKAYSQSKLANVLFTRELAKRLEGTNTPRNGAQTSLYVALDPELEKVTGQYFSDCKLKEMAPAATDTQTAKWLWAGGKFRKQT
DETGKVAIVTGGNTGLGKETVMELARRGATVYMACRNKEKVERARREIVKETGNSNVFSRECDLSSLDSIRKFAENFKKEQRVLHILINNAGVFW
EPHRLTKEGFEMHLGVNHIGHFLLTNLLLGVLERSAPSRVVVVASRAHERGQIKVDDINSSDFYDEGVAYCQSKLANILFTRELAKRLEGTGVTV
NALNPGIADTEIARNMIFFQTKFAQYVVECVLFQFSFYTLTNFWFSFRTILRPLLWAVMKTPKNGAQTTLYAALDPDLERVSGQYFSDCALAPVA
PAALDDQMAQWLWAQSEKWAKIAL*
(SEQ ID NO: 1218)

Classification: enzyme

Celera Sequence No. : 142000013384703
TTTGTTGTCTGCATTTACCTTAAATGAATTTATTAACTAAGGCGATATTGTGCCTCTCGCTCAATCTCGCAAAACGATGCTTTGTCTGCTGCTTC
TCTGTGCGTGTGTCCGTCTCTTTCCACGGCTTTTCGTCGAGACTCACATATACAAACGGCGACACACTGGATTGGAGCTGGACTCCGTTTTGGAT
GGCTTGGCTTTGGCTGCGTACCCAAAATAAATCGCGCTTGCAGTCCCAAATCATTTTAGTTCTTGACGCCTTTGTTCCACAAAAACTTCCAACCG
CCGTCCATGGCTCGTGCTTTCTCTTTCGCTCGCGAGACGCTCCAAAAGTCGCGAGTATGGGAAGAGAATGTATCCCTCGCTCTTTCACGCCTAGA
AGCGGCTGTAGCACACACAAGCACACGTAAACCCAGCCGTATGCATATACATATATTCCCTCTACTAGCGAGACGTGTGTACGTGCGTATGTATG
TATGCTTTTTTCACTTCTTTCTCCTCTGCGTTCTTTGCACCAAGTGTCGCTGTTGCTATTTGCTACCGCCGCTCCTCTTGACGAATAAGTCGGGA
CTTGTATCAGCTCTAATTCGGACTTAGTTTACAAAATGCGGCTGCTTTTTTTCCGCGATACTCGGATTAGTGATGTAAAAAGACGTTGATGCTTC
GACCACTGAAGTCAGTGCGATATGTATCGATAATTGAATGCCATCGATTGCTACGATTAAAACTGCCACCGCAGTTAGCGGAGACGCTCACCATT
CTCTATTCGCCATTTGAAAGTATCGGTGTAATTTGTTTTCAGAGAAATTAATTTCCGTTTACTGTGCAATTCGGTGTGAAAGTGTTCAGATTTAT
CAATGCGTATTCTGCTTTCGACTTCGCCACCAATCTGTGCTGCAAGTTACCATTACCAGGTCCACCTGGTTCCCGCCAGTTTTCTTTCATTGTGG
CTAGTTGTTGTTCGTGCCTTCGATAAAGACGTTTAGAGGTGTTTTTAGAGTTTCGCCATCTGGTCACTATAGCCGTTTCGTTTTTTACGTGAGTA
TTGTGAATTTGGTGTGTTGATTTATATCTCAGTTGGAGCCTGCGTGGAAATAGTGTCAGTACGTTTAAAGGCATCATCGTAAGGTTAGTCGGAAA
ACAAATAAAAAGCCTACAAATAGCAAGCAAGAACGCTTTCGCAACCACAAGAAAAACGAACATACGCACGCATCCATCTGTGGTAGAGTCGGCTT
GTGTGGGGGTGAGTGGATGTGTGGGTGAGCATTTCTGGAAAGTGCCGTTCTCTATGTTTCGATTCTACTTATCCCTTCATCACCATTTCATCGTT
GAATCATCACGAAAGAAACATCGAAAGTGCACAATCGTTTGTTATCTTTGTACGAAAACAACGGTGATTTCCACACAGGCATAACCTGCAAGAGT
AATACGATACAAATTTTGATCTGATATGACCTCATTTTAGTCGGTTTGAATTTTAAAGAGAGCGACTCTGCAAACTGCAGGGATATGAACATACA
AAATTCACAAATGATTGTTTGCATCCTAGTTGCTTATATTCATTTACACGCATGCTTATATGCTTACATCTGTTATCAATAATTGACGACTTGGT
GCATGCGAAGCAAACGCATTGAAATGACTATTGGGATCCACACACTGTTAAAAAACACACTGATTGCACTGCCACACATTTCTCAACTAGAACCT
AATGTTTTATACTGAACTTAACTGCAGGAAAGCCCAAAATGCCCAGCATCAAGTTGCAATCTTCGGATGAGGAGATCTTTGACACGGATATCCAG
ATCGCCAAGTGCTCCGGCACTATCAAGACCATGCTGGAGGACTGCGGCATGGAGGACGATGAGAATGCCATTGTGCCGTTGCCCAATGTGAATTC
GACGATTCTTCGCAAGGTGCTTACCTGGGCTCACTACCACAAGGACGACCCCCAGCCAACGGAGGATGATGAGAGCAAGGAGAAGCGCACAGACG
ACATTATCTCATGGGATGCAGATTTCCTAAAAGTCGACCAGGGCACACTGTTTGAGCTGATATTGGCAGCGAACTATCTGGACATTAAGGGCCTT
CTGGAGCTCACCTGCAAGACTGTTGCAAACATGATTAAGGGAAAGACTCCCGAGGAAATACGCAAGACCTTCAACATTAAGAAGGACTTTTCGCC
CGCCGAGGAGGAGCAGGTGCGCAAGGAGAACGAGTGGTGCGAGGAGAAGTAAAGCGCGGCATTTCGCGGACCAACATTAAGTTGAAACAGCTAG
GGGATTCGGGAACGAATTGGATTTGCAGCATTGCAACTTTACTTAGTTGCTACTTTCATTTACATTTTTTTTATTTTTAACCCCAGCAGAGACT
CGATTTAAATTGTGTATAAATGATCTGTTGCTGATTTGATTCGCGGGGTTCATTTTTTGTCGTAAATATATCTCATATACATACATATGCGAGAT
TGTAACACTCTCTTTAACCTATTGGAGTAACACTTGATTTCACTTTAATAAATATAACTACCCAACACAAAGACACAGCCTATTTTGTGGGCTTC
CCGGAGGGGTTAGGGTCCAAGGACTTCTCAAATTAAGAAGTGCTCTTTATTCGTTATCTTGTGTTTAGAAACGTTTGCAAGCGTTTGAAATGGAT
ACGCATGCCATTTATGGTCCAGTCGGTAAAATTTTACGTGTTCCCAAGAAGGTACATATATATCTTAGATTATCTTATCTATAGAAACTACATTC
ATAAGATCACGCTTTCGGCGAATAGCGAGTAATACTGTAGCTGCCACTTTGCCACTTAGTGTGCAATTGAAATGCGCGCCAACGCATGTTCTCAT
ATGCGGAGCGTTTAGCAGCCCTTAAAAAGCTTTTCATGTTGCTTTTAAAAAGCTACGACGGGTGTGGAAATTAGATTTGTGACGCTTTATATATC
TTTTTTTTATATCGTCTGGGGTACAGCATGGTTTTAGGATTTTAGAAGAAAGCAGTAATTTTGTAAGAATCGAAGAACGGGGGGATATTTATAAT
TTTCATATTAACCTTGTCTTTGTTTGCTTTTGAAATTATGAATACTTCGAAAGATAATTATCTTGTGCGCATTCCATTCTGGCTTAGACTGGGTT
GAGCTAAAAATGATTTGAAATACAAATTTTTAGGTGTCCGCTGATATATAAACAGTATGATGTTTTTGCACTTTTTTCCCTGAAGTTTTCCTTGT
TGTCTCGCTTGCCAATGCTGAACAAAGTAGCCAAAGGACCTTTACTTGAAGCTTTGAGAGCGGAAAATATATTCGGGGACAATTGCTTTAAGTGT
GCACTAGGCTTGGCTAGATGCCCGTGCCAAACTTTCTTTGGAATTGATCGCTGGCCTTAGCCAAAAGTGGAAAAAAGAAAGGATAGGATAGTGCC
GCACGTATTAAGGGTCTTCTTACAAAAGGTAACTGATATTAATTCATTTGCATACTAAGCAAGCTAACTCATCTGTTTATTGCAAACAAGCGCCA
ATTGAAGTTTTATCGAAGCTCAG
(SEQ ID NO: 1219)

Exon: 1001..1128
Exon: 1738..2538
Start ATG: 1749

Transcript No. : CT40292

FIGURE SHEET 654

```
TTTCGCCATCTGGTCACTATAGCCGTTTCGTTTTTTACGTGAGTATTGTGAATTTGGTGTGTTGATTTATATCTCAGTTGGAGCCTGCGTGGAAA
TAGTGTCAGTACGTTTAAAGGCATCATCGTAAGGAAAGCCCAAAATGCCCAGCATCAAGTTGCAATCTTCGGATGAGGAGATCTTTGACACGGAT
ATCCAGATCGCCAAGTGCTCCGGCACTATCAAGACCATGCTGGAGGACTGCGGCATGGAGGACGATGAGAATGCCATTGTGCCGTTGCCCAATGT
GAATTCGACGATTCTTCGCAAGGTGCTTACCTGGGCTCACTACCACAAGGACGACCCCCAGCCAACGGAGGATGATGAGAGCAAGGAGAAGCGCA
CAGACGACATTATCTCATGGGATGCAGATTTCCTAAAAGTCGACCAGGGCACACTGTTTGAGCTGATATTGGCAGCGAACTATCTGGACATTAAG
GGCCTTCTGGAGCTCACCTGCAAGACTGTTGCAAACATGATTAAGGGAAAGACTCCCGAGGAAATACGCAAGACCTTCAACATTAAGAAGGACTT
TTCGCCCGCCGAGGAGGAGCAGGTGCGCAAGGAGAACGAGTGGTGCGAGGAGAAGTAAAGCGCGGCATTTCGCGGGACCAACATTAAGTTGAAAC
AGCTAGGGGATTCGGGAACGAATTGGATTTGCAGCATTGCAACTTTACTTAGTTGCTACTTTCATTTACATTTTTTTTTATTTTTAACCCCAGCA
GAGACTCGATTTAAATTGTGTATAAATGATCTGTTGCTGATTTGATTCGCGGGGTTCATTTTTTGTCGTAAATATATCTCATATACATACATATG
CGAGATTGTAACACTCTCTTTAACCTATTGGAGTAACACTTGATTTCACTTTAATAAATATAACTACCCAACAC
(SEQ ID NO: 1220)

Start ATG: 140

MPSIKLQSSDEEIFDTDIQIAKCSGTIKTMLEDCGMEDDENAIVPLPNVNSTILRKVLTWAHYHKDDPQPTEDDESKEKRTDDIISWDADFLKVD
QGTLFELILAANYLDIKGLLELTCKTVANMIKGKTPEEIRKTFNIKKDFSPAEEEQVRKENEWCEEK*
(SEQ ID NO: 1221)

Classification: cell_cycle_regulator
Gene Symbol: skpA
FlyBase ID: FBgn0025637

Celera Sequence No. : 142000013384703
GAAGAGAATGTATCCCTCGCTCTTTCACGCCTAGAAGCGGCTGTGTAGCACACACAAGCACACGTAAACCCAGCCGTATGCATATACATATATTCCC
TCTACTAGCGAGACGTGTGTACGTGCGTATGTATGTATGCTTTTTTCACTTCTTTCTCCTCTGCGTTCTTTGCACCAAGTGTCGCTGTTGCTATT
TGCTACCGCCGCTCCTCTTGACGAATAAGTCGGGACTTGTATCAGCTCTAATTCGGACTTAGTTTACAAAATGCGGCTGCTTTTTTTCCGCGATA
CTCGGATTAGTGATGTAAAAAGACGTTGATGCTTCGACCACTGAAGTCAGTGCGATATGTATCGATAATTGAATGCCATCGATTGCTACGATTAA
AACTGCCACCGCAGTTAGCGGAGACGCTCACCATTCTCTATTCGCCATTTGAAAGTATCGGTGTAATTTGTTTTCAGAGAAATTAATTTCCGTTT
ACTGTGCAATTCGGTGTGAAAGTGTTCAGATTTATCAATGCGTATTCTGCTTTCGACTTCGCCACCAATCTGTGCTGCAAGTTACCATTACCAGG
TCCACCTGGTTCCCGCCAGTTTTCTTTCATTGTGGCTAGTTGTTGTTCGTGCCTTCGATAAAGACGTTTAGAGGTGTTTTTAGAGTTTCGCCATC
TGGTCACTATAGCCGTTTCGTTTTTTACGTGAGTATTGTGAATTTGGTGTGTTGATTTATATCTCAGTTGGAGCCTGCGTGGAAATAGTGTCAGT
ACGTTTAAAGGCATCATCGTAAGGTTAGTCGGAAAACAAATAAAAAGCCTACAAATAGCAAGCAAGAACGCTTTCGCAACCACAAGAAAAACGAA
CATACGCACGCATCCATCTGTGGTAGAGTCGGCTTGTGTGGGGGTGAGTGGATGTGTGGGTGAGCATTTCTGGAAAGTGCCGTTCTCTATGTTTC
GATTCTACTTATCCCTTCATCACCATTTCATCGTTGAATCATCACGAAAGAAACATCGAAAGTGCACAATCGTTTGTTATCTTTGTACGAAAACA
ACGGTGATTTCCACACAGGCATAACCTGCAAGAGTAATACGATACAAATTTTGATCTGATATGACCTCATTTTAGTCGGTTTGAATTTTAAAGAG
AGCGACTCTGCAAACTGCAGGGATATGAACATACAAAATTCACAAATGATTGTTCATCCTAGTTGCTTATATTCATTTACACGCATGCTTATA
TGCTTACATCTGTTATCAATAATTGACGACTTGGTGCATGCGAAGCAAACGCATTGAAATGACTATTGGGATCCACACACTGTTAAAAAACACAC
TGATTGCACTGCCACACATTTCTCAACTAGAACCTAATGTTTTATACTGAACTTAACTGCAGGAAAGCCCAAAATGCCCAGCATCAAGTTGCAAT
CTTCGGATGAGGAGATCTTTGACACGGATATCCAGATCGCCAAGTGCTCCGGCACTATCAAGACCATGCTGGAGGACTGCGGCATGGAGGACGAT
GAGAATGCCATTGTGCCGTTGCCCAATGTGAATTCGACGATTCTTCGCAAGGTGCTTACCTGGGCTCACTACCACAAGGACGACCCCCAGCCAAC
GGAGGATGATGAGAGCAAGGAGAAGCGCACAGACGACATTATCTCATGGGATGCAGATTTCCTAAAAGTCGACCAGGGCACACTGTTTGAGCTGA
TATTGGCAGCGAACTATCTGGACATTAAGGGCCTTCTGGAGCTCACCTGCAAGACTGTTGCAAACATGATTAAGGGAAAGACTCCCGAGGAAATA
CGCAAGACCTTCAACATTAAGAAGGACTTTTCGCCCGCCGAGGAGGAGCAGGTGCGCAAGGAGAACGAGTGGTGCGAGGAGAAGTAAAGCGCGGC
ATTTCGCGGGACCAACATTAAGTTGAAACAGCTAGGGGATTCGGGAACGAATTGGATTTGCAGCATTGCAACTTTACTTAGTTGCTACTTTCATT
TACATTTTTTTTATTTTTAACCCCAGCAGAGACTCGATTTAAATTGTGTATAAATGATCTGTTGCTGATTTGATTCGCGGGGTTCATTTTTTGT
CGTAAATATATCTCATATACATACATATGCGAGATTGTAACACTCTCTTTAACCTATTGGAGTAACACTTGATTTCACTTTAATAAATATAACTA
CCCAACACAAAGACACAGCCTATTTTGTGGGCTTCCCGGAGGGGTTAGGGTCCAAGGACTTCTCAAATTAAGAAGTGCTCTTTATTCGTTATCTT
GTGTTTAGAAACGTTTGCAAGCGTTTGAAATGGATACGCATGCCATTTATGGTCCAGTCGGTAAAATTTTACGTGTTCCCAAGAAGGTACATATA
TATCTTAGATTATCTTATCTATAGAAACTACATTCATAAGATCACGCTTTCGGCGAATAGCGAGTAATACTGTAGCTGCCACTTTGCCACTTAGT
GTGCAATTGAAATGCGCGCCAACGCATGTTCTCATATGCGGAGCGTTTAGCAGCCCTTAAAAAGCTTTTCATGTTGCTTTTAAAAAGCTACGACG
GGTGTGGAAATTAGATTTGTGACGCTTTATATATCTTTTTTTTATATCGTCTGGGGTACAGCATGGTTTTAGGATTTTAGAAGAAAGCAGTAATT
TTGTAAGAATCGAAGAACGGGGGGATATTTATAATTTTCATATTAACCTTGTCTTTGTTTGCTTTTGAAATTATGAATACTTCGAAAGATAATTA
TCTTGTGCGCATTCCATTCTGGCTTAGACTGGGTTGAGCTAAAAATGATTTGAAATACAAATTTTTAGGTGTCCGCTGATATATAACAGTATGA
TGTTTTTGCACTTTTTTCCCTGAAGTTTTCCTTGTTGTCTCGCTTGCCAATGCTGAACAAAGTAGCCAAAGGACCTTTACTTGAAGCTTTGAGAG
CGGAAAATATATTCGGGGACAATTGCTTTAAGTGTGCACTAGGCTTGGCTAGATGCCCGTGCCAAACTTTCTTTGGAATTGATCGCTGGCCTTAG
CCAAAAGTGGAAAAAAGAAAGGATAGGATAGTGCCGCACGTATTAAGGGTCTTCTTACAAAAGGTAACTGATATTAATTCATTTGCATACTAAGC
AAGCTAACTCATCTGTTTATTGCAAACAAGCGCCAATTGAAGTTTTATCGAAGCTCAG
(SEQ ID NO: 1222)

Exon: 1001..1078
Exon: 1393..2193
Start ATG: 1404

Transcript No. : CT40294
AAACATCGAAAGTGCACAATCGTTTGTTATCTTTGTACGAAAACAACGGTGATTTCCACACAGGCATAACCTGCAAGAGAAAGCCCAAAATGCCC
AGCATCAAGTTGCAATCTTCGGATGAGGAGATCTTTGACACGGATATCCAGATCGCCAAGTGCTCCGGCACTATCAAGACCATGCTGGAGGACTG
CGGCATGGAGGACGATGAGAATGCCATTGTGCCGTTGCCCAATGTGAATTCGACGATTCTTCGCAAGGTGCTTACCTGGGCTCACTACCACAAGG
ACGACCCCCAGCCAACGGAGGATGATGAGAGCAAGGAGAAGCGCACAGACGACATTATCTCATGGGATGCAGATTTCCTAAAAGTCGACCAGGGC
ACACTGTTTGAGCTGATATTGGCAGCGAACTATCTGGACATTAAGGGCCTTCTGGAGCTCACCTGCAAGACTGTTGCAAACATGATTAAGGGAAA
GACTCCCGAGGAAATACGCAAGACCTTCAACATTAAGAAGGACTTTTCGCCCGCCGAGGAGGAGCAGGTGCGCAAGGAGAACGAGTGGTGCGAGG
```

AGAAGTAAAGCGCGGCATTTCGCGGGACCAACATTAAGTTGAAACAGCTAGGGGATTCGGGAACGAATTGGATTTGCAGCATTGCAACTTTACTT
AGTTGCTACTTTCATTTACATTTTTTTTATTTTAACCCCAGCAGAGACTCGATTTAAATTGTGTATAAATGATCTGTTGCTGATTTGATTCGC
GGGGTTCATTTTTGTCGTAAATATATCTCATATACATACATATGCGAGATTGTAACACTCTCTTTAACCTATTGGAGTAACACTTGATTTCACT
TTAATAAATATAACTACCCAACAC
(SEQ ID NO: 1223)

Start ATG: 90

MPSIKLQSSDEEIFDTDIQIAKCSGTIKTMLEDCGMEDDENAIVPLPNVNSTILRKVLTWAHYHKDDPQPTEDDESKEKRTDDIISWDADFLKVD
QGTLFELILAANYLDIKGLLELTCKTVANMIKGKTPEEIRKTFNIKKDFSPAEEEQVRKENEWCEEK*
(SEQ ID NO: 1224)

Classification: cell_cycle_regulator
Gene Symbol: skpA
FlyBase ID: FBgn0025637

Celera Sequence No. : 142000013384566
TTGTAAGGCGTATCACTTGATTCCGCACTCTACTCAACTCTCCAAGGACCTCTGTAATCTGATAGGCTTACTGAACCAACAGAGAGTAGAAACAA
AGTTTTGCTTTATTGTGATTTTACGAAATAACCTACAACTTCACCATTCCCAAAAACACAATTTCTTTTTCCTTAAACATTCCAGTTTTAAACAC
CTTTTTTACAGTTTTTCGTTGTAAGTTGGCCAAAATATGTCACAAGGCTGAAAAACGCACTTTTTTAGTCAGCTGGGGTCCTCAGCTAAAGACC
CATATCAATATTTGCTTTAATTTGGAAAAATAATTTTTCGGCCAAATTTCGCATTTTTTGTAAGGGGTAACATCATAAAAAATCGAAAAAATTTT
CAAACCAAAAATTTCTCTAAATGAGTTACCCGTCGTTTAGGAATATTTTTACAAGTTCAACGAGGTATTCCACTCCACAATTGGACGTGTCTTTC
CCAAGATATAGCACTTTTTCTGTGAAATCCCCATCGAAAATTATCAACAAGAATAAAATCACCCTCGTTTTCCATCTGAAAAAACTCCCTCAAAA
ACAAACGCATATACAGTTTATTTCGTTACATATATATTGTTATTTATTTAAGAACTTGCTCGTCTAATTGACAGAAAAATATAAAGATATAGGAT
GTATTGAATGGGTTGTGCTGAGTGTCTTACTATGCGAATGAGCGATTCCACTTAAGCCTAGGCGAAATCTCGGCGATTGCATAATGTGGAGCCCC
CTCCCGAGGTGTACGGAAATCACAAGTGGTTGATAAGAAAGAACAGACGTGGAATTTTGCTGTGCTGGTTTGAGGATCGCAGTCGAACGGATAAT
TTATTGGCCAGTCGCCGACTTGGCTGGTGATGATTTAATAGCGGACCCTCGGGAAGGCTCTCTGGGCTGACAGATAACAGATAACTCGACTGGCT
GATAATTTTGATGCGTGACTGGGCGCTGCGCCTTCTCTATCTCCACCTCCTTACAGGGTCTTGTCGAACAGGAACTCGCCCAGTTCGCCGTTGGT
GTCCATCATCTTCTTGAGAGTGGTCAGCTTGCCGGCGAGCTCGCGCTGTCCGTGGAGCTGCTCCTCCAGATAGACACCGGTCAGGTAGTCCACCA
GGTGGTAGTGGTTGTAGGGCTTGTTCTCGCAGGTCTGGATCAGCTTGCGGATGGACTTGGTCACCTTGATCTCCAGGTCGAGGGCGTCGGACAGG
GCGGCGGCACCATCGGTCCACTCCTGCTTGGCCACAGTCTGTGGGGGATTCGCCAGGATTAGCTGGGCTTTTGGGTTTTCTAGGCGAGTCGTCGA
CTTACCGGCACATTGATCAGATCGCTGACTCCCTCGGTCAGTTGACCGCGCATGGACAGGTACTCCACCAGCTTGGATCCGTGCTCACGTTCCTC
CTTGGCGGCCTTGAAGAAGTGCTCGGCGAATCCAGGGCGGTTGACGGTGTCGCGGGAGAAGTAGGCGCCCATGGCCAAGTACTGGTAGGAGGCGT
TGATCTCCTCCTGGATCTGATTGCGCATGCCCTTTATGCAGGCATCCTTCATGTCCACCCAGTCCTTGGTAATCTCAGGAACAGCCAGGGAGCCT
GCAATGGGATAAGGTTGGGTTAAGTCGGGGGACCACGATAACAATATATGGCTAGTATTCAGCTTTAAAAAATTTATTTTTGTAATCAGAACTTA
GGTAAATTTTAATATTTTAAAAACCTTTGCACTCTTGGTCTTGACCTTCATGGCTTAGGTTTTGTTTTTCTTTTAGTTGATGCTCTTCTCGCTCC
CTTTGAAGCTCTCTCACGAAACTCTTGCTTTCTTGCTTGGCTGAGGGGTAGGGCGTTGTTGGTTATTGCATTTAAGAGGGCGTAATTGCATAAAC
CTTTGAAATTGCGCTTGAAATGCCGCTATTCTAGGGCACAAAAACCGTGTGCAAAACTGTAATGGCCTACTCTCCCACTCTCTCTCTCTGTTTTT
GTAACTGCATTGGTAACGTGCGCAGCTCTCGCCGCCATAGTAACGGCATTTGTTTTCGTGTAGTGCCGTGTGCAAAAAGCATGGTTCACCATGCT
AGCTCACTCGGCCCGTAAAAGCCGTGTGCAAAGAGCGCCTTGAAATGTAACAACAAAAAGTCAAGCTTATTTATACCGCAATATTCATGGAAATG
AAAGCGAAATTCGCATTATTTAATTATGAAAATTTATGTATAAAAACTGGTTATCATTTCCCCAAAGCGCAACGGAAGTATCAATAACTTTTAAA
TCAACTGGTTTGGTAACTTCACTTCATTGACGAAAGAGAGTGAAAGAGCGTCAAAGAGAAACGGCGCATGCTCTTTTCAACGCATTACAAATGTT
TTGCTTCTCTTTGCGTATTGCGTCGAAATTTATTGTTTTTTTTCCGATGACCTGCCTTTGTTTTGTTTGAAATTCTGATGAATAAAACGTAACAT
TAGTACTTACACTTGAAATCTCCATAGGCCTGGGCCACCACGGCCAACAGGAGCAGGCTAGCAATTAGTTTCACCATCTTTGATCGTCGAACGTA
GTCTTTACACAAAATCACAGAACAAAAATTTGTTTTTCACTTTAGTTTGATTTGCTTGAAATGCACAAATGAGAATGAGGCGACTCGAGTTGAGC
TACAATGTTAAATAGGCGTTGAAATTGAAAATCTAGCTGCCTTTACACACACTGGCGCAGAAGGCGTCGCCTGCTTCAATTTGATGGGCTTGATT
GGGATTATTTTCGACTTCTCGAATGCTTTCCAGTACCTTCTGCTGACAGCTTTAATCTGATTTTTCAGTGGAGCTAAGGCCTTTCTACGTTGTGT
TTTAGCGAACTCGAAAGCGAACTGTCGCTCCGAACGGCGCACAAAACACTTTTAAGCGCGCGCGCTCTCGGTTTTTCTTCGTGTGTGTGTGAGTG
ATGGGAGAGTGTGCACTGTTATCTTTTCAACATGTCGCCCGTTCTTTGTTAACCGTTTAAATGGCTGATAATTGAATATTCCCGATAATTGCCGC
ACTCAATGTGATACACACGTCCTCAATATGGGTATACTTTGTATAAAGTCGGGTTTCCTAGTCAGATAATCCCCACTTACTAAGAAGTAAATTTA
TCAAATGCAATATGGCCGCTCTTTTGAGATGCGCATCAGCTGTTCTTTGTTTTTGTTTTGGCCGTGGGAGAGCACCACGTCATGTGTTGCCAGGC
GGTTTAATTATTGCTGACAATTTAATTCACATTTTGTCAAGTTGATTTGCACGTTCGAAGGGGGGATCAGTCACCCACTTTGATAACTGCTAATA
TGGCGACGGCTCTTTTTTACGTGTCGCTTGCAGAGCTCCAAGAATGACACTTGATAAGAAGGATACATGGTGGGAAAACTTACAAATTACATAAT
TTGTTTGTTGATTGGGGAAACCCTACATTATCTCCGAACCCAGCAATAATATGTATTGTAAATAGCAACAGTCTCAAGCTCGATGCTGCTGTGAA
TTACCAATATATCAAAACTTAAAACATTATCTTAGGAGGTAGATGGTTTATCTGCAGTTTATTTTCAATTCTCATCGTTAGCTGATAAAACTCTC
AGGAAACCACTTGAAATCCAAAGTGCAGCGTCCATATTTTGCACACGCTGACAACCCTGTCGTGAGTCACCTTCCAGCAGGCGCAGCAACAACAG
CACTGGCAGCGGCCATATTTGAATGACACCGAAATCCCGCACTGAGCGCAAAACAACACATGCCCATGCACGCTCTCCAAAACCACACACACACA
GCCATATCGATCGCATAGAAAGAGACGTACGCGACGCTATAAACAGCAGTTGATTTTCAGAGTTTCACCAAGAAGCACATAAAGCGATTGAATTA
TTAATAAAAGCACAGGCACTGGAAGTGAGTTTTAATATTACTAACTAACTACTTTGTGAGTGTTTAGTTACGAAAACTAGAAAATAATATTCTGG
AAACTGTGTTTTTAAACCGACCACCATATAAATTTAAAAACCAAAACATTCCATTGGTGGTGGTTTTGTTGTTAAAAAAGAGCACAGAAAATTCA
AGAAAACGCTACGACGCAAAACGAAAAAACTCGCCCAAAATGAAAACAAAAGTGTC
(SEQ ID NO: 1225)

Exon: 3141..2792
Exon: 2659..2481
Exon: 1613..1336
Exon: 1273..1001
Start ATG: 2547 (Reverse strand: CAT)

Transcript No. : CT40862

FIGURE SHEET 656

ATTTGATAAATTTACTTCTTAGTAAGTGGGGATTATCTGACTAGGAAACCCGACTTTATACAAAGTATACCCATATTGAGGACGTGTGTATCACA
TTGAGTGCGGCAATTATCGGGAATATTCAATTATCAGCCATTTAAACGGTTAACAAAGAACGGGCGACATGTTGAAAAGATAACAGTGCACACTC
TCCCATCACTCACACACACACGAAGAAAAACCGAGAGCGCGCGCGCTTAAAAGTGTTTTGTGCGCCGTTCGGAGCGACAGTTCGCTTTCGAGTTC
GCTAAAACACAACGTAGAAAGGCCTTAGCTCCACTGAAAAATCAGATTAAAGCTGTCAGCAGAAGCTCAACTCGAGTCGCCTCATTCTCATTTGT
GCATTTCAAGCAAATCAAACTAAAGTGAAAAACAAATTTTTGTTCTGTGATTTTGTGTAAAGACTACGTTCGACGATCAAAGATGGTGAAACTAA
TTGCTAGCCTGCTCCTGTTGGCCGTGGTGGCCCAGGCCTATGGAGATTTCAAGTGCTCCCTGGCTGTTCCTGAGATTACCAAGGACTGGGTGGAC
ATGAAGGATGCCTGCATAAAGGGCATGCGCAATCAGATCCAGGAGGAGATCAACGCCTCCTACCAGTACTTGGCCATGGGCGCCTACTTCTCCCG
CGACACCGTCAACCGCCCTGGATTCGCCGAGCACTTCTTCAAGGCCGCCAAGGAGGAACGTGAGCACGGATCCAAGCTGGTGGAGTACCTGTCCA
TGCGCGGTCAACTGACCGAGGGAGTCAGCGATCTGATCAATGTGCCGACTGTGGCCAAGCAGGAGTGGACCGATGGTGCCGCCGCCCTGTCCGAC
GCCCTCGACCTGGAGATCAAGGTGACCAAGTCCATCCGCAAGCTGATCCAGACCTGCGAGAACAAGCCCTACAACCACTACCACCTGGTGGACTA
CCTGACCGGTGTCTATCTGGAGGAGCAGCTCCACGGACAGCGCGAGCTCGCCGGCAAGCTGACCACTCTCAAGAAGATGATGGACACCAACGGCG
AACTGGGCGAGTTCCTGTTCGACAAGACCCTGTAA
(SEQ ID NO: 1226)

Start ATG: 463 (Reverse strand: CAT)

MVKLIASLLLLAVVAQAYGDFKCSLAVPEITKDWVDMKDACIKGMRNQIQEEINASYQYLAMGAYFSRDTVNRPGFAEHFFKAAKEEREHGSKLV
EYLSMRGQLTEGVSDLINVPTVAKQEWTDGAAALSDALDLEIKVTKSIRKLIQTCENKPYNHYHLVDYLTGVYLEEQLHGQRELAGKLTTLKKMM
DTNGELGEFLFDKTL*
(SEQ ID NO: 1227)

Name: FERRITIN RELATED PROTEIN
Classification: ligand_binding_or_carrier

Celera Sequence No. : 142000013384566
TTGTAAGGCGTATCACTTGATTCCGCACTCTACTCAACTCTCCAAGGACCTCTGTAATCTGATAGGCTTACTGAACCAACAGAGAGTAGAAACAA
AGTTTTGCTTTATTGTGATTTTACGAAATAACCTACAACTTCACCATTCCCAAAAACACAATTTCTTTTTCCTTAAACATTCCAGTTTTAAACAC
CTTTTTTACAGTTTTTTCGTTGTAAGTTGGCCAAAATATGTCACAAGGCTGAAAAACGCACTTTTTTAGTCAGCTGGGGTCCTCAGCTAAAGACC
CATATCAATATTTGCTTTAATTTGGAAAAATAATTTTTCGGCCAAATTTCGCATTTTTTGTAAGGGGTAACATCATAAAAAATCGAAAAAATTTT
CAAACCAAAAATTTCTCTAAATGAGTTACCCGTCGTTTAGGAATATTTTTACAAGTTCAACGAGGTATTCCACTCCACAATTGGACGTGTCTTTC
CCAAGATATAGCACTTTTTCTGTGAAATCCCCATCGAAAATTATCAACAAGAATAAAATCACCCTCGTTTTCCATCTGAAAAAACTCCCTCAAAA
ACAAACGCATATACAGTTTATTTCGTTACATATATATTGTTATTTATTTAAGAACTTGCTCGTCTAATTGACAGAAAAATATAAAGATATAGGAT
GTATTGAATGGGTTGTGCTGAGTGTCTTACTATGCGAATGAGCGATTCCACTTAAGCCTAGGCGAAATCTCGGCGATTGCATAATGTGGAGCCCC
CTCCCGAGGTGTACGGAAATCACAAGTGGTTGATAAGAAAGAACAGACGTGGAATTTTGCTGTGCTGGTTTGAGGATCGCAGTCGAACGGATAAT
TTATTGGCCAGTCGCCGACTTGGCTGGTGATGATTTAATAGCGGACCCTCGGGAAGGCTCTCTGGGCTGACAGATAACAGATAACTCGACTGGCT
GATAATTTTGATGCGTGACTGGGCGCTGCGCCTTCTCTATCTCCACCTCCTTACAGGGTCTTGTCGAACAGGAACTCGCCCAGTTCGCCGTTGGT
GTCCATCATCTTCTTGAGAGTGGTCAGCTTGCCGGCGAGCTCGCGCTGTCCGTGGAGCTGCTCCTCCAGATAGACACCGGTCAGGTAGTCCACCA
GGTGGTAGTGGTTGTAGGGCTTGTTCTCGCAGGTCTGGATCAGCTTGCGGATGGACTTGGTCACCTTGATCTCCAGGTCGAGGGCGTCGGACAGG
GCGGCGGCACCATCGGTCCACTCCTGCTTGGCCACAGTCTGTGGGGGATTCGCCAGGATTAGCTGGGCTTTTGGGTTTTCTAGGCGAGTCGTCGA
CTTACCGGCACATTGATCAGATCGCTGACTCCCTCGGTCAGTTGACCGCGCATGGACAGGTACTCCACCAGCTTGGATCCGTGCTCACGTTCCTC
CTTGGCGGCCTTGAAGAAGTGCTCGGCGAATCCAGGGCGGTTGACGGTGTCGCGGGAGAAGTAGGCGCCCATGGCCAAGTACTGGTAGGAGGCGT
TGATCTCCTCCTGGATCTGATTGCGCATGCCCTTTATGCAGGCATCCTTCATGTCCACCCAGTCCTTGGTAATCTCAGGAACAGCCAGGGAGCCT
GCAATGGGATAAGGTTGGGTTAAGTCGGGGGACCACGATAACAATATATGGCTAGTATTCAGCTTTAAAAAATTTATTTTTGTAATCAGAACTTA
GGTAAATTTTAATATTTTAAAAACCTTTGCACTCTTGGTCTTGACCTTCATGGCTTAGGTTTTGTTTTTCTTTTAGTTGATGCTCTTCTCGCTCC
CTTTGAAGCTCTCTCACGAAACTCTTGCTTTCTTGCTTGGCTGAGGGGTAGGGCGTTGTTGGTTATTGCATTTAAGAGGGCGTAATTGCATAAAC
CTTTGAAATTGCGCTTGAAATGCCGCTATTCTAGGGCACAAAAACCGTGTGCAAAACTGTAATGGCCTACTCTCCCACTCTCTCTCTCTGTTTTT
GTAACTGCATTGGTAACGTGCGCAGCTCTCGCCGCCATAGTAACGGCATTTGTTTTCGTGTAGTGCCGTGTGCAAAAAGCATGGTTCACCATGCT
AGCTCACTCGGCCCGTAAAAGCCGTGTGCAAAGAGCGCCTTGAAATGTAACAACAAAAAGTCAAGCTTATTTATACCGCAATATTCATGGAAATG
AAAGCGAAATTCGCATTATTTAATTATGAAAATTTATGTATAAAAACTGGTTATCATTTCCCCAAAGCGCAACGGAAGTATCAATAACTTTTAAA
TCAACTGGTTTGGTAACTTCACTTCATTGACGAAAGAGAGTGAAAGAGCGTCAAAGAGAAACGGCGCATGCTCTTTTCAACGCATTACAAATGTT
TTGCTTCTCTTTGCGTATTGCGTCGAAATTTATTGTTTTTTTTCCGATGACCTGCCTTTGTTTTGTTTGAAATTCTGATGAATAAAACGTAACAT
TAGTACTTACACTTGAAATCTCCATAGGCCTGGGCCACCACGGCCAACAGGAGCAGGCTAGCAATTAGTTTCACCATCTTTGATCGTCGAACGTA
GTCTTTACACAAAATCACAGAACAAAAATTTGTTTTTCACTTTAGTTTGATTTGCTTGAAATGCACAAATGAGAATGAGGCGACTCGAGTTGAGC
TACAATGTTAAATAGGCGTTGAAATTGAAAATCTAGCTGCCTTTACACACACTGGCGCAGAAGGCGTCGCCTGCTTCAATTTGATGGGCTTGATT
GGGATTATTTTCGACTTCTCGAATGCTTTCCAGTACCTTCTGCTGACAGCTTTAATCTGATTTTTCAGTGGAGCTAAGGCCTTTCTACGTTGTGT
TTTAGCGAACTCGAAAGCGAACTGTCGCTCCGAACGGCGCACAAAACACTTTTAAGCGCGCGCGCTCTCGGTTTTTCTTCGTGTGTGTGTGAGTG
ATGGGAGAGTGTGCACTGTTATCTTTTCAACATGTCGCCCGTTCTTTGTTAACCGTTTAAATGGCTGATAATTGAATATTCCCGATAATTGCCGC
ACTCAATGTGATACACACGTCCTCAATATGGGTATACTTTGTATAAAGTCGGGTTTCCTAGTCAGATAATCCCCACTTACTAAGAAGTAAATTTA
TCAAATGCAATATGGCCGCTCTTTTGAGATGCGCATCAGCTGTTCTTTGTTTTTGTTTTGGCCGTGGGAGAGCACCACGTCATGTGTTGCCAGGC
GGTTTAATTATTGCTGACAATTTAATTCACATTTTGTCAAGTTGATTTGCACGTTCGAAGGGGGGATCAGTCACCCACTTTGATAACTGCTAATA
TGGCGACGGCTCTTTTTTACGTGTCGCTTGCAGAGCTCCAAGAATGACACTTGATAAGAAGGATACATGGTGGGAAAACTTACAAATTACATAAT
TTGTTTGTTGATTGGGGAAACCCTACATTATCTCCGAACCCAGCAATAATATGTATTGTAAATAGCAACAGTCTCAAGCTCGATGCTGCTGTGAA
TTACCAATATATCAAAACTTAAAACATTATCTTAGGAGGTAGATGGTTTATCTGCAGTTTATTTTCAATTCTCATCGTTAGCTGATAAAACTCTC
AGGAAACCACTTGAAATCCAAAGTGCAGCGTCCATATTTTGCACACGCTGACAACCCTGTCGTGAGTCACCTTCCAGCAGGCGCAGCAACAACAG
CACTGGCAGCGGCCATATTTGAATGACACCGAAATCCCGCACTGAGCGCAAAACAACACATGCCCATGCACGCTCTCCAAAACCACACACACACA
GCCATATCGATCGCATAGAAAGAGACGTACGCGACGCTATAAACAGCAGTTGATTTTCAGAGTTTCACCAAGAAGCACATAAAGCGATTGAATTA
TTAATAAAAGCACAGGCACTGGAAGTGAGTTTTAATATTACTAACTAACTACTTTGTGAGTGTTTAGTTACGAAAACTAGAAAATAATATTCTGG
AAACTGTGTTTTTAAACCGACCACCATATAAATTTAAAAACCAAAACATTCCATTGGTGGTGGTTTTGTTGTTAAAAAAGAGCACAGAAAATTCA
AGAAAACGCTACGACGCAAAACGAAAAAACTCGCCCAAAATGAAAACAAAAGTGTC
(SEQ ID NO: 1228)

FIGURE SHEET 657

Exon: 3141..2792
Exon: 2619..2481
Exon: 1613..1336
Exon: 1273..1001
Start ATG: 2547 (Reverse strand: CAT)

Transcript No. : CT40864
ATTTGATAAATTTACTTCTTAGTAAGTGGGGATTATCTGACTAGGAAACCCGACTTTATACAAAGTATACCCATATTGAGGACGTGTGTATCACA
TTGAGTGCGGCAATTATCGGGAATATTCAATTATCAGCCATTTAAACGGTTAACAAAGAACGGGCGACATGTTGAAAAGATAACAGTGCACACTC
TCCCATCACTCACACACACACGAAGAAAAACCGAGAGCGCGCGCGCTTAAAAGTGTTTTGTGCGCCGTTCGGAGCGACAGTTCGCTTTCGAGTTC
GCTAAAACACAACGTAGAAAGGCCTTAGCTCCACTGAAAAATCAGATTAAAGCTGTCAGCAGAAGCAAATCAAACTAAAGTGAAAAACAAATTTT
TGTTCTGTGATTTTGTGTAAAGACTACGTTCGACGATCAAAGATGGTGAAACTAATTGCTAGCCTGCTCCTGTTGGCCGTGGTGGCCCAGGCCTA
TGGAGATTTCAAGTGCTCCCTGGCTGTTCCTGAGATTACCAAGGACTGGGTGGACATGAAGGATGCCTGCATAAAGGGCATGCGCAATCAGATCC
AGGAGGAGATCAACGCCTCCTACCAGTACTTGGCCATGGGCGCCTACTTCTCCCGCGACACCGTCAACCGCCCTGGATTCGCCGAGCACTTCTTC
AAGGCCGCCAAGGAGGAACGTGAGCACGGATCCAAGCTGGTGGAGTACCTGTCCATGCGCGGTCAACTGACCGAGGGAGTCAGCGATCTGATCAA
TGTGCCGACTGTGGCCAAGCAGGAGTGGACCGATGGTGCCGCCGCCCTGTCCGACGCCCTCGACCTGGAGATCAAGGTGACCAAGTCCATCCGCA
AGCTGATCCAGACCTGCGAGAACAAGCCCTACAACCACTACCACCTGGTGGACTACCTGACCGGTGTCTATCTGGAGGAGCAGCTCCACGGACAG
CGCGAGCTCGCCGGCAAGCTGACCACTCTCAAGAAGATGATGGACACCAACGGCGAACTGGGCGAGTTCCTGTTCGACAAGACCCTGTAA
(SEQ ID NO: 1229)

Start ATG: 423 (Reverse strand: CAT)

MVKLIASLLLLAVVAQAYGDFKCSLAVPEITKDWVDMKDACIKGMRNQIQEEINASYQYLAMGAYFSRDTVNRPGFAEHFFKAAKEEREHGSKLV
EYLSMRGQLTEGVSDLINVPTVAKQEWTDGAAALSDALDLEIKVTKSIRKLIQTCENKPYNHYHLVDYLTGVYLEEQLHGQRELAGKLTTLKKMM
DTNGELGEFLFDKTL*
(SEQ ID NO: 1230)

Name: ferritin subunit 1
Classification: ligand_binding_or_carrier
Gene Symbol: Fer1HCH
FlyBase ID: FBgn0015222

Celera Sequence No. : 142000013384566
TTGTAAGGCGTATCACTTGATTCCGCACTCTACTCAACTCTCCAAGGACCTCTGTAATCTGATAGGCTTACTGAACCAACAGAGAGTAGAAACAA
AGTTTTGCTTTATTGTGATTTTACGAAATAACCTACAACTTCACCATTCCCAAAAACACAATTTCTTTTTCCTTAAACATTCCAGTTTTAAACAC
CTTTTTTACAGTTTTTTCGTTGTAAGTTGGCCAAAATATGTCACAAGGCTGAAAAACGCACTTTTTTAGTCAGCTGGGGTCCTCAGCTAAAGACC
CATATCAATATTTGCTTTAATTTGGAAAAATAATTTTTCGGCCAAATTTCGCATTTTTTGTAAGGGGTAACATCATAAAAAAATCGAAAAAATTTT
CAAACCAAAAATTTCTCTAAATGAGTTACCCGTCGTTTAGGAATATTTTTACAAGTTCAACGAGGTATTCCACTCCACAATTGGACGTGTCTTTC
CCAAGATATAGCACTTTTTCTGTGAAATCCCCATCGAAAATTATCAACAAGAATAAAATCACCCTCGTTTTCCATCTGAAAAAACTCCCTCAAAA
ACAAACGCATATACAGTTTATTTCGTTACATATATATTGTTATTTATTTAAGAACTTGCTCGTCTAATTGACAGAAAAATATAAAGATATAGGAT
GTATTGAATGGGTTGTGCTGAGTGTCTTACTATGCGAATGAGCGATTCCACTTAAGCCTAGGCGAAATCTCGGCGATTGCATAATGTGGAGCCCC
CTCCCGAGGTGTACGGAAATCACAAGTGGTTGATAAGAAAGAACAGACGTGGAATTTTGCTGTGCTGGTTTGAGGATCGCAGTCGAACGGATAAT
TTATTGGCCAGTCGCCGACTTGGCTGGTGATGATTTAATAGCGGACCCTCGGGAAGGCTCTCTGGGCTGACAGATAACAGATAACTCGACTGGCT
GATAATTTTGATGCGTGACTGGGCGCTGCGCCTTCTCTATCTCCACCTCCTTACAGGGTCTTGTCGAACAGGAACTCGCCCAGTTCGCCGTTGGT
GTCCATCATCTTCTTGAGAGTGGTCAGCTTGCCGGCGAGCTCGCGCTGTCCGTGGAGCTGCTCCTCCAGATAGACACCGGTCAGGTAGTCCACCA
GGTGGTAGTGGTTGTAGGGCTTGTTCTCGCAGGTCTGGATCAGCTTGCGGATGGACTTGGTCACCTTGATCTCCAGGTCGAGGGCGTCGGACAGG
GCGGCGGCACCATCGGTCCACTCCTGCTTGGCCACAGTCTGTGGGGGATTCGCCAGGATTAGCTGGGCTTTTGGGTTTTCTAGGCGAGTCGTCGA
CTTACCGGCACATTGATCAGATCGCTGACTCCCTCGGTCAGTTGACCGCGCATGGACAGGTACTCCACCAGCTTGGATCCGTGCTCACGTTCCTC
CTTGGCGGCCTTGAAGAAGTGCTCGGCGAATCCAGGGCGGTTGACGGTGTCGCGGGAGAAGTAGGCGCCCATGGCCAAGTACTGGTAGGAGGCGT
TGATCTCCTCCTGGATCTGATTGCGCATGCCCTTTATGCAGGCATCCTTCATGTCCACCCAGTCCTTGGTAATCTCAGGAACAGCCAGGGAGCCT
GCAATGGGATAAGGTTGGGTTAAGTCGGGGGACCACGATAACAATATATGGCTAGTATTCAGCTTTAAAAAATTTATTTTTGTAATCAGAACTTA
GGTAAATTTTAATATTTTAAAAACCTTTGCACTCTTGGTCTTGACCTTCATGGCTTAGGTTTTGTTTTTCTTTTAGTTGATGCTCTTCTCGCTCC
CTTTGAAGCTCTCTCACGAAACTCTTGCTTTCTTGCTTGGCTGAGGGGTAGGGCGTTGTTGGTTATTGCATTTAAGAGGGCGTAATTGCATAAAC
CTTTGAAATTGCGCTTGAAATGCCGCTATTCTAGGGCACAAAAACCGTGTGCAAAACTGTAATGGCCTACTCTCCCACTCTCTCTCTCTGTTTTT
GTAACTGCATTGGTAACGTGCGCAGCTCTCGCCGCCATAGTAACGGCATTTGTTTTCGTGTAGTGCCGTGTGCAAAAAGCATGGTTCACCATGCT
AGCTCACTCGGCCCGTAAAAGCCGTGTGCAAAGAGCGCCTTGAAATGTAACAACAAAAAGTCAAGCTTATTTATACCGCAATATTCATGGAAATG
AAAGCGAAATTCGCATTATTTAATTATGAAAATTTATGTATAAAAACTGGTTATCATTTCCCCAAAGCGCAACGGAAGTATCAATAACTTTTAAA
TCAACTGGTTTGGTAACTTCACTTCATTGACGAAAGAGAGTGAAAGAGCGTCAAAGAGAAACGGCGCATGCTCTTTTCAACGCATTACAAATGTT
TTGCTTCTCTTTGCGTATTGCGTCGAAATTTATTGTTTTTTTTCCGATGACCTGCCTTTGTTTTGTTTGAAATTCTGATGAATAAAACGTAACAT
TAGTACTTACACTTGAAATCTCCATAGGCCTGGGCCACCACGGCCAACAGGAGCAGGCTAGCAATTAGTTTCACCATCTTTGATCGTCGAACGTA
GTCTTTACACAAAATCACAGAACAAAAATTTGTTTTTCACTTTAGTTTGATTTGCTTGAAATGCACAAATGAGAATGAGGCGACTCGAGTTGAGC
TACAATGTTAAATAGGCGTTGAAATTGAAAATCTAGCTGCCTTTACACACACTGGCGCAGAAGGCGTCGCCTGCTTCAATTTGATGGGCTTGATT
GGGATTATTTTCGACTTCTCGAATGCTTTCCAGTACCTTCTGCTGACAGCTTTAATCTGATTTTTCAGTGGAGCTAAGGCCTTTCTACGTTGTGT
TTTAGCGAACTCGAAAGCGAACTGTCGCTCCGAACGGCGCACAAAACACTTTTAAGCGCGCGCTCTCGGTTTTTCTTCGTGTGTGTGTGAGTG
ATGGGAGAGTGTGCACTGTTATCTTTTCAACATGTCGCCCGTTCTTTGTTAACCGTTTAAATGGCTGATAATTGAATATTCCCGATAATTGCCGC
ACTCAATGTGATACACACGTCCTCAATATGGGTATACTTTGTATAAAGTCGGGTTTCCTAGTCAGATAATCCCCACTTACTAAGAAGTAAATTTA
TCAAATGCAATATGGCCGCTCTTTTGAGATGCGCATCAGCTGTTCTTTGTTTTTGTTTTGGCCGTGGGAGAGCACCACGTCATGTGTTGCCAGGC
GGTTTAATTATTGCTGACAATTTAATTCACATTTTGTCAAGTTGATTTGCACGTTCGAAGGGGGGATCAGTCACCCACTTTGATAACTGCTAATA
TGGCGACGGCTCTTTTTTACGTGTCGCTTGCAGAGCTCCAAGAATGACACTTGATAAGAAGGATACATGGTGGGAAAACTTACAAATTACATAAT TTGTTTGTTGATTGGGGAAACCCTACATTATCTCCGAACCCAGCAATAATATGTATTGTAAATAGCAACAGTCTCAAGCTCGATGCTGCTGTGAA
TTACCAATATATCAAAACTTAAAACATTATCTTAGGAGGTAGATGGTTTATCTGCAGTTTATTTTCAATTCTCATCGTTAGCTGATAAAACTCTC
AGGAAACCACTTGAAATCCAAAGTGCAGCGTCCATATTTGCACACGCTGACAACCCTGTCGTGAGTCACCTTCCAGCAGGCGCAGCAACAACAG
CACTGGCAGCGGCCATATTTGAATGACACCGAAATCCCGCACTGAGCGCAAAACAACACATGCCCATGCACGCTCTCCAAAACCACACACACACA
GCCATATCGATCGCATAGAAAGAGACGTACGCGACGCTATAAACAGCAGTTGATTTTCAGAGTTTCACCAAGAAGCACATAAAGCGATTGAATTA
TTAATAAAAGCACAGGCACTGGAAGTGAGTTTTAATATTACTAACTAACTACTTTGTGAGTGTTTAGTTACGAAAACTAGAAAATAATATTCTGG
AAACTGTGTTTTTAAACCGACCACCATATAAATTTAAAAACCAAAACATTCCATTGGTGGTGGTTTTGTTGTTAAAAAAGAGCACAGAAAATTCA
AGAAAACGCTACGACGCAAAACGAAAAAACTCGCCCAAAATGAAAACAAAAGTGTC
(SEQ ID NO: 1231)

Exon: 3141..2792
Exon: 2567..2481
Exon: 1613..1336
Exon: 1273..1001
Start ATG: 2547 (Reverse strand: CAT)

Transcript No. : CT40866
ATTTGATAAATTTACTTCTTAGTAAGTGGGGATTATCTGACTAGGAAACCCGACTTTATACAAAGTATACCCATATTGAGGACGTGTGTATCACA
TTGAGTGCGGCAATTATCGGGAATATTCAATTATCAGCCATTTAAACGGTTAACAAAGAACGGGCGACATGTTGAAAAGATAACAGTGCACACTC
TCCCATCACTCACACACACACGAAGAAAAACCGAGAGCGCGCGCGCTTAAAAGTGTTTTGTGCGCCGTTCGGAGCGACAGTTCGCTTTCGAGTTC
GCTAAAACACAACGTAGAAAGGCCTTAGCTCCACTGAAAAATCAGATTAAAGCTGTCAGCAGAAGACTACGTTCGACGATCAAAGATGGTGAAAC
TAATTGCTAGCCTGCTCCTGTTGGCCGTGGTGGCCCAGGCCTATGGAGATTTCAAGTGCTCCCTGGCTGTTCCTGAGATTACCAAGGACTGGGTG
GACATGAAGGATGCCTGCATAAAGGGCATGCGCAATCAGATCCAGGAGGAGATCAACGCCTCCTACCAGTACTTGGCCATGGGCGCCTACTTCTC
CCGCGACACCGTCAACCGCCCTGGATTCGCCGAGCACTTCTTCAAGGCCGCCAAGGAGGAACGTGAGCACGGATCCAAGCTGGTGGAGTACCTGT
CCATGCGCGGTCAACTGACCGAGGGAGTCAGCGATCTGATCAATGTGCCGACTGTGGCCAAGCAGGAGTGGACCGATGGTGCCGCCGCCCTGTCC
GACGCCCTCGACCTGGAGATCAAGGTGACCAAGTCCATCCGCAAGCTGATCCAGACCTGCGAGAACAAGCCCTACAACCACTACCACCTGGTGGA
CTACCTGACCGGTGTCTATCTGGAGGAGCAGCTCCACGGACAGCGCGAGCTCGCCGGCAAGCTGACCACTCTCAAGAAGATGATGGACACCAACG
GCGAACTGGGCGAGTTCCTGTTCGACAAGACCCTGTAA
(SEQ ID NO: 1232)

Start ATG: 371 (Reverse strand: CAT)

MVKLIASLLLLAVVAQAYGDFKCSLAVPEITKDWVDMKDACIKGMRNQIQEEINASYQYLAMGAYFSRDTVNRPGFAEHFFKAAKEEREHGSKLV
EYLSMRGQLTEGVSDLINVPTVAKQEWTDGAAALSDALDLEIKVTKSIRKLIQTCENKPYNHYHLVDYLTGVYLEEQLHGQRELAGKLTTLKKMM
DTNGELGEFLFDKTL*
(SEQ ID NO: 1233)

Name: ferritin subunit 1
Classification: ligand_binding_or_carrier
Gene Symbol: Fer1HCH
FlyBase ID: FBgn0015222

Celera Sequence No. : 142000013383837
CGCGCATCCAGCGGGCCACCACACTCACCTCGTCCATGTCCCTGCCGGCGGAGTGCCTGGTTCTCTCCGTATCCATGCCCTCGCTCAACTCGGAG
CCCAAGCGTCCCAAGAGCGCGGGACCCAAGAAGAAGCCCGGCCAGGCCGTCCACTCGAAGCCATTCCGCCTATATTGAGCCTGTCGAGGAAGGAG
CTGCTCCACAAGTCGCACGTGACGTCACCCAATCGAAGCACTCAGAGATTTGTGCACAAGTTGATATCGAGGCACGCACTTCTAAAACATGCATA
TGCAGAATACATTTTATCAAACCGTTGATTGTTTAGAACCGAAATGGAAACGAAACTTGGCATTTACAACATAACAATAAACGACTAAATGAGAG
GCAAAGTTAAGCACAAAATACAGCTGTGGTTTGTTTGTTTGTTTCTTTATATAATTACAGTATATATTTTCGTAAGTATTAAATCTGTTTCACGG
CTACTACATCGCTGGAGCCAAACGGCCTTCGTTTACATTTCATTTACATAAGACTTGCGTTTGATTTTCTATATATAATTAGTACAAAAATTGTC
CTGGGATTTCGTTACGTCTCATTGCGTCTTTATCATCGTGCTCATTGTGTGTTTGGAAAACTGTGTGCTTTTCTTGGTTTCTTTAGGTTTTGTAT
TCGTTTTTGATTCTTGTTCCTTTCGATTATTCGAGTCGCGTCACATTTAAATGCATTTAGTTGCCTTTTTCCATTTACATCATCCTTTTGCTCTA
CTTAAGCCATAAAAGTTGTTTATACAATTCGTTTTTAAAGTTAGGGTAATAAATAGGTCATTATAAAATAATAAACAACAGTTGTTACATTTTCA
AAAGACATCGTCAAATGAGCTTCAAGTGATTATGATTATGATTCGAGGGTCGAGTTAGAATTAAAAAAATGCGCATGCTTGAATATCATAAAAAG
TGGCTTCTCTAAGAGCTCGTCGTCAAGTGAATTGGCCTGGTTTCAGATTTGGTTAGCTGCGGATTGGCTGCCTTAGCTCATGGCTATATATAACT
ATAATACATTTAATGGGAAACTAGGAAATGCATAGATGCTCGTGATATGCGAAACCAATGTTTGCTGCGGTTGTTATAATTTTCTCTTTCTGCCA
GATACTATTCGTACAATACATTCGATTCAATTGACTAGATTTCTACATATGTAGTGCATTAGATTTATGATTTATCTGTGGTACCGATTTTGTTA
ACAATGTTTTTTTAGTTGTTGCGGGAGGGAATCGTGGTTTGCCAAATGTGTGACAGCAACGATCCGCAGAAAAAAACAGCCAAACAAAGAGAAA
TTTCATACGAATTTTGATGGCAGTACATTTCGATTCACAGAATTTCGTACAATATTTATCGTTTGTTTAGAGTTTCTTTCCGGGTTCGGTGCCTT
TTACGAGAGTACGGAGAATTTTATAAATAAATACATGTAATTGATTTGTCGATGAGGGCGCTGCGTGAGTGTCAATTTGTTGTGGCCATTGTGCC
GGTGTACGTGTCGCTTCCGAGGAATCTCTATACTTCGCCAAAGCCAATAACATTCTACCTTATTTACATTATTAAACACTTTCGCTGGCGTCGCT
TTAGCGGCTCTGGTCTGAGCACCGCGCGCACCGCTTCCTCGAACACCTGAATTTGCAATCGGAGTGGGAAGGGAAATTTAATGATGAATAAGGGG
TAGGTGGAGGGTGTGCCGGGCACCGATGACTTACCGGCTTGAGACCGCGCTGCGTCAAGGCGGAGCACTCCATGTATTTCACAGCGCGTATCTTG
TTTGCCAGCTTCTGGCCCTGCTCGCGCTTCAGCGGCGTCAGTCCCTGCTCTGCCAGGCCGCTGAGTGTCTCTCGATCTTCGCGCAAATCGATTTT
GGTGCCTGGAATACGCCCAAAGATATATGTATGATTCTCGTTTTCTGATTGCAGTTTTCATGTCGCTTGGCAACTTACCAACTAGAATGATGGGC
GCATCGGGACAGTGGTGCTTTATCTCCGGATACCATTTCGAGGTGACGTTCTCAAAGGACGAGGGACTCGCCACGCTGTAGCATATCAGGAAAAC
GTCTGTCTGCGGGTAGGATAGCGGTCTCAGGCGGTCGTAGTCCTCCTGACCCGCCGTATCCCACAGTCCCAGCGAGACCTGTATTGTGTCCACTT
GCATGGGCGCCGAGTAGTTGTCGAAGCTGTGAAAGATATCATAGTAAAAGTTAGATATCGATCTGCGGTTTGCGGCTATCGAGGCACAAACTTAC
ACTGTGGGCACATATTCGCCGGGAAAGCAGTCTGTCGTGTAGGAGATTAGCATGCAGGTCTTTCCGACGGTGCCGTCACCAACGACTACACACTT
TATGGGCCTTCCGGTTGACATCGTGAGTGTGCTGAGTGTGCCTGTGCCGATAGCTGTGTACTGTCTGTGTGCTGTGGGCAAAATAAGATGGAAGA
TGAATGTCTTCGCCAGCTTAATTCAATTAATTAAGTTCTATTCGAGGCAATAAACCCGCCAGTGCCAACTGACCGCAAATTATTTCACAGTCGTA CTTCCTTAATAAAAATTCTTTAAAATAGAAACAAATGCTGTAGAAATACATATATGACACAATAAATTATCCTATTCGTTTTATTAGGTTTTTAT
AAATAAATTAACTACCACATCGTTTTTGGCGCGCAACTACATATATATAAGATAAACAATTGCTTAAATGGAATTTGGCAACTTTTAAAATTTGA
ATATCTAGACAAATTGAATCAGGATACTTGCTTCCTGAGTCGCAAACTATTTATATTGTATTAATGGAAGTTATACTTATTGGAGTATGCTACAT
CGTAAAGTGGGAATGTCCAAGCTGTGGAAGTACTACTGTACAGAGTATAATGGCGAAGGTCTACGGTATATCTCTGGGATGATCAAAGGCAGGGC
TCTCGAAAGGTGTGTCCCGGCCGCAAAAAGAAAGCAACCGCAGCGGCGGAGGCCCATAAAGCCTAATAAAACGAACGAGGGTCTCATTTCGGTTG
CGGTGGCACTTTGTTTTCGCAAATAAAATTTTCAAAAATAGATCATGATGGGCGACACAGACGGGGAAAAACAAAAAGCATAAATGGGAGCAGCG
GACCAAATGGCGACCGCCCCTCCAGTGGCGCCCCTTCGGCGGTGGCGGGGTCGCCCGAGTGTTGTGGTGACGCGGAAGCCACCGGCAGACGCAC
CGCATCGAGAAAAAGAAACACAAAATGGGAAAATGAACCGCCCGAAAATAGACACAATTAAGTTCTCATAACCGATTCAATTAAAGTTCAACACA
CAGAGGCGGCACATATTGCGCCACATGCAACGGGGCTGGGCGTGGCCGCGGGGGCGGGTGCGGTAGCAATGAAAATCTTTTGTTGTGGCACAACA
CCGAATGGGAATACAATATTATTTTACCGTTTTCACCACCACCTATCCTTTTCCTTTGTCTGTCGGCAGGCGGCGACTGTTTTGTACTTGGCTTA
TATCACTGTGCGTTTTCCGGCTACCGATATGCGTTCGAGGCGATGGTCCATGCGGCGCATTTAAATAATTGATTCGCACTATTTCGCAGCGGCTT
TTACTTATAAATATCTGTTTGAGGGACAAAACGCAGCGTCCCCGAATAATTTTCGTGTTTTTCCTTTTTGTTTCCACTCCACACAAACACACACC
CACCTTTTTGACAGCGCAGCGACGCTCTCTCTCTCGCCGTTGACAGTGGTGCCAACTTAGGGCCAGAAAATAGCTGACGGTAAATATAAAAAAAT
CACTTAAATGTATGGTACCAATAACTAAACTTAATAAGCATATCATCCAGTATAAAGTCGTTTTTCTTTTTCCAAAACTAAAATAAACTTTTTTT
TACAATTGGCACTTAAAAATCAGCTAGACTTGGCGTGAAAAAAGAGAGCGGGTAGTCCAGCTCCGCTCTCTCGAAACTGACAAGCAGTGCTGCAA
AAGGTGCAGGGCTCAGGCGGATTTGGCATTATACAATACTAATAGGCATGGTTGTGGGAGAGGGGTTGCAACCAATTTTCACATTGTAAACAAAA
TTATTTATTTAATTCTATTTCGAGCAGAATATTGTAATAATTACCTGTTAATTAAAAAATTATCATTTTAAAATTATCTTATGTAAGTTCAATAC
CCTTTAATTGCTATCGACTACGCCCATGCTGCCTATGTCCACTGTTGTTGTTTCGAGCGTCGTAATGAGCAGATTTGTTTATAAACTTTTACAGA
GTGCAAACCAAACTAGTTCGGGCTGCAGACGCATTTCTTTGGCTACTGTAAGAAATGCGGAAAGCGAATCTCAAGAGGGTGCCCCTGCCCGCACA
GTTCTGGTGGAGAAGGACTCGCACATAACACTTATTGGCCTAAATCGCGAGCAGCAGCGTAATTCCATTGATGCCAACACCGCGGAGCAGCTGAC
CGAAGCCATTAGCCAATTCGAAGCGGATGATACTTCTCCAGTGGGTGTGCTCTACGGCATAGGTGGCTCCTTTTGTGCAGGCTATGATCTGGAGG
AGCTAGAGGCGGAGGCGCAACGCGGCAGCCTCAACTTTCTGTTGCGTCACGAGGGCTCCGTCGGACCAACTAGGCGGCATCTCCGCAAGCCACTT
GTTTGCGGCATCAGCGGTTTCTGTGTG
(SEQ ID NO: 1234)

Exon: 3682..3448
Exon: 2446..2281
Exon: 2211..1979
Exon: 1905..1745
Exon: 1661..1001
Start ATG: 2396 (Reverse strand: CAT)

Transcript No. : CT40870
AACAAAAAGGAAAAACACGAAAATTATTCGGGGACGCTGCGTTTTGTCCCTCAAACAGATATTTATAAGTAAAAGCCGCTGCGAAATAGTGCGAA
TCAATTATTTAAATGCGCCGCATGGACCATCGCCTCGAACGCATATCGGTAGCCGGAAAACGCACAGTGATATAAGCCAAGTACAAAACAGTCGC
CGCCTGCCGACAGACAAAGGAAAAGGATAGGTGGTGGTGAAAACGCACACAGACAGTACACAGCTATCGGCACAGGCACACTCAGCACACTCACG
ATGTCAACCGGAAGGCCCATAAAGTGTGTAGTCGTTGGTGACGGCACCGTCGGAAAGACCTGCATGCTAATCTCCTACACGACAGACTGCTTTCC
CGGCGAATATGTGCCCACAGTCTTCGACAACTACTCGGCGCCCATGCAAGTGGACACAATACAGGTCTCGCTGGGACTGTGGGATACGGCGGGTC
AGGAGGACTACGACCGCCTGAGACCGCTATCCTACCCGCAGACAGACGTTTTCCTGATATGCTACAGCGTGGCGAGTCCCTCGTCCTTTGAGAAC
GTCACCTCGAAATGGTATCCGGAGATAAAGCACCACTGTCCCGATGCGCCCATCATTCTAGTTGGCACCAAAATCGATTTGCGCGAAGATCGAGA
GACACTCAGCGGCCTGGCAGAGCAGGGACTGACGCCGCTGAAGCGCGAGCAGGGCCAGAAGCTGGCAAACAAGATACGCGCTGTGAAATACATGG
AGTGCTCCGCCTTGACGCAGCGCGGTCTCAAGCCGGTGTTCGAGGAAGCGGTGCGCGCGGTGCTCAGACCAGAGCCGCTAAAGCGACGCCAGCGA
AAGTGTTTAATAATGTAAATAAGGTAGAATGTTATTGGCTTTGGCGAAGTATAGAGATTCCTCGGAAGCGACACGTACACCGGCACAATGGCCAC
AACAAATTGACACTCACGCAGCGCCCTCATCGACAAATCAATTACATGTATTTATTTATAAAATTCTCCGTACTCTCGTAAAAGGCACCGAACCC
GGAAAGAAACTCTAAACAAACGATAAATATTGTACGAAATTCTGTGAATCGAAATGTACTGCCATCAAAATTCGTATGAAATTTCTCTTTGTTTG
GCTGTTTTTTTCTGCGGATCGTTGCTGTCACACATTTGGCAAACCACGATTCCCTCCCGCAACAACTAAAAAAAACATTGTTAACAAAATCGGTA
CCACAGATAAATCATAAATCTAATGCACTACATATGTAGAAATCTAGTCAATTGAATCGAATGTATTGTACGAATAGTATCTGGCAGAAAGAGAA
AATTATAACAACCGCAGCAAACATTGGTTTCGCATATCACGAGCATCTATGCATTTCCTAGTTTCCCATTAAATGTATTATAGTTATATATAGCC
ATGAGCTAAGGCAGCCAATCCGCAGCTAACC
(SEQ ID NO: 1235)

Start ATG: 286 (Reverse strand: CAT)

MSTGRPIKCVVVGDGTVGKTCMLISYTTDCFPGEYVPTVFDNYSAPMQVDTIQVSLGLWDTAGQEDYDRLRPLSYPQTDVFLICYSVASPSSFEN
VTSKWYPEIKHHCPDAPIILVGTKIDLREDRETLSGLAEQGLTPLKREQGQKLANKIRAVKYMECSALTQRGLKPVFEEAVRAVLRPEPLKRRQR
KCLIM*
(SEQ ID NO: 1236)

Classification: enzyme

Celera Sequence No. : 142000013384543
CATTTCCAGTACTGCAGATGACCGCGCTTCTTGTTTCGGAAGAAGCGGAAGCCATTGATCACCAGCAACTTGCCGCCGTTCTTCTTGGAGTCCGC
GAAGTCAATGTGAAATGCTGTGAATGAAATAGAAAGTCTGGATTAGTTTGGGAATTCGTGAACAAGTGCTACGTCAAAAGCGTAGGTCTATTCTT
ATGGAAACAGATGTAGTTCGTCGTAAATTTCGTTTAAAATTAAAAGCAGTCATTTATTTAAAAGTGGATTGTTAGATGTCTTATGGTTTTGACAA
TGTGCACTTAAATGTAAGCCTATGACGCATCCAGAGATAGGGCCTTCTCCCTTTTTATGAGCACAGGCAGGTTTACGTTATTGCTAGGGAATTTC
CGGCTGTGATCATGCTCGTAGGTGCATTTGATGATTCGCTCCTGTGAGTTTTTGTCCACCGCGGTCACGACACGAGCCCTGCAGACCGTCACATC
CTGTTGGTGGGACAAAGGAATACGTCGTTACTTTAGTTTATAACAAGGAGTCTCTGTGCTTCTTGAAATTCTCTTTTTTAGAAATCTATTAATTA
TAAACTCTTGTTTCTTTAACTATGCATATTAAACGTATACATATATTTAATTAAAAAATCAAGGAATATACTATAATATTCTTAGCACAACACGA
AAAATGATGAGCAGACTTTATCTTAATGATTTCTCTTATACAAAACCTGAATTCTATGATTTTCAGCAAAATCTTGTAGTTTAACTTACCTTTTT
CGAGCATATCCAATAAGTACGAGAGGCGGAACATCGGTTCTTAACGAACTTCTCGTTTTGGAAGAGCAGCACGGTTCTTCCCCGCTGTCCAGTGC CGAAGACAGCCAGTTCTAAAAGGATTAAGCAGATAATTAGAATAACCATAAACTTGGGAGTGTCTTATCACTTGTGTATAACTACTAAACTAGGT
TTTAAACGAAGAATTGTAAGTTTATTGGTAATACAGCAATGTATACACGTCTACAAATGGTTGTGCACGCCTGAAATGGCTACATATGTGGGTTT
GTTTTTGTGGGTAATCATGTAGACGTTGCAGCTTAGTCGCTTTTTGGCACACCCCCAATATATGATATCGTTGTAGTTGGCTCGTCGATCATAAC
GATATCCGTCGTAGACCAGAACATCGCCGCTCCTGGTCCGATCATACCGGATGCGATCCCAGTCGTCCAGGGTGCGGACGCACTTCTGATCGGGC
GCCAGTCCACAGCGAACATTCTGTGGCCGTTTACCCTTGGTTTTGGGCAAGAAGCTCTCGTTACCAAAGTCAGCCAGGTTGCTAGGATTGAGTTC
ACCTAAATCTGAAAAATAAAACAAATTAGTGTGAATGCAAAATGTTATACATATTTAAAAAAATTAAAAGAAAAACAACACCGCATTGCGGAATA
AAGATTTATAAAAAAAATATATATTTAGGTACAGTAAAATAAAACAAGAGGTTGGTCTATTCATAAACATAAGTAAAGTTTTAAACAAGTCAATT
GCAACACACTCACCTTACCTTAATAAATACTATCTTCTGCAAAATAATCCTAAGCCTGTTTATATATCAAGCTTAAGATCTGACAAATTAAAAGG
TGTTATTGCGCAAAACTAGAAATGGATTTCGGTTCAATTTCGTTTACTACATCATTCTGTACAAAAAGCTGCCTAATCTATACAGCTATGTATGT
GTCCCGATTCAGACTTCTGAATGCTCTTTGATCTATGGATGATTATGCACGCCACTGACTGCGTAGCGGGATTGGCCATTCGGCAAGATGTGAGT
GATGACGCGGGAGCGGCATTGCTTGCGCCACTTGCTGCACTTCCAGTAGACCTTGTCCTTATAGGCGGCATTCCGCAGGTAACGATGCTCCCCAC
AGTGCAGAACGACATTCCCGGCCGGAGTGCGAACGTAGTGCACGCCCTCCATGGATTTGGACAAACGAACGCGCTTCATCAGCTGGTGTTGATCG
GGTTTTACGATGGGATCCGTTAACACATCAAATGTCACTAAAACATAGAAAAACAGGCAGAATTAGTTAAAGGCAACGCAATCATTCACACACAT
GCACATACAGTTAGTTTCTTTAAATCATATAGGACATTTCTGCTTAAATAAACAAGACAAAGAGTTTATTTTAGATTCACATATAAATAGTCTAC
TTCTAGTTCGCAAGCTATGGCTAGATTTTGAGTCTCGATTCATTGCAGGTTGTTAAGGTCCTCGATGCTTAAGTTGAGCGTCCTTAGCTCCAGTG
TTAAATCCTCGTCACCCTCCTCCTTTATGAAGCCCGTGGATACAGACTTTTCCGACTTGCTTCGCGCTTTCCCCACAACGTTTGTTACTGAAAGC
CGCTTTTTTCGCTCCGTGTTCAGGCAGGTGTGATGGCACGATTCCAGTACTATTTTGTGCACACCTTCAACTACATTGGTGACCACCCGAGCATT
GCATTTCGTGCTTCCCTGGAAGAAAGATAGGAACTAGCTAATTTCTGTCTGAAACTGTCACAAGAGTCATAATTTCATAGGTCGCTTAGTTTTCT
TTGGGGTTAATTAAATTTTATCTCACCTTTTTGGAGCATATCCAGTAGGTCTTCAGGTTACTGCGACGGTTTCGCACGTAGTTGTGGCCATTAAA
GGCCAGCAGTTTGCAGCCGCGCTGTCCCCGAATAAAAGTGAGTAGGCTGTGCTTGATGGCGCCCTTCATGTCATCCAGATCATCGCATACTGTAA
GAAACAAATTAGCTTTGAGTTAGCTTAAGTGTAAAGTCTACTACTGCAAAAACTGTTAAAGTGTAAATTTTACAAAATACGGTTTTTCGATTTTC
AAGATTTGTATTCTACAATAAATAAGCTATAAATTGATTCTATACAATGATCCAAAGTCGGCCGGTTTTAATATGATTCTTTAGTAGGGCGGATG
GTTATGTTGTCCGCATTTGATAGTCACATCGTGGTCTTGCGCGGTGACTACACGGGCCTTGCATTTGTGAACACCCGCTCGAGCGCAAGACCAAT
AAGTTTTCAATCCCGAGGTCTTGTTTCGAGTGAAGGAGAACTCTCCGATCTTAAGTTTTCGGCTCCCTCGAAAACCGGTGATGTACGAGTAGTAC
GCAACAGAACCTGTGAATAGAAAATATACACACTTGGTTAGTACAAACTGGTGGAGGAGTGCGACGCAGATCTAAAGCTAGAGGTCAAAGAGACG
CATGAAGAGCGAGAAACTTAGCTAACTTGATTTTTATTAAGTCAGACGAGTGTTGAGGTGATGCAATATTTTACACTTGGACTTAAGACTAGTGC
GCTATGTCGTTGTTGCCGGCGCTGAAGTGGCGGCCGTTTCCAATGGGTCCTGACGACGCTCCGCCCGGGCTGCCGCCTCGGCTTCCGCCCGCTGT
CGCTTCAGGGAGCCGTACTTTCGCGCCTTAGTGATAACTTCATGGTTGTGCTCGCTGTTCAGGATGGTGAGTGTATCCAATTTGGTCTTGAGCCG
CGCACGACATCGCAACACTGCGAACTAAAAGTAGAACCACAATAAATACATTTTTGGTGTAGATTTGGCTTAAACTGTGAAAGGAATGCAATTAA
CTTTACGAAATAACTAACAATTAATTACAGCTGTCTTCAACTCAGAAAAGTAGGCTCTACTTATCTTGCTCTCGACTAAGATTAAGTAGTAACTA
GATTAGTTATATTTTCTCAATATTTTAAGGAGAATTTAAAACAAAAACGTTTTTTCGAATGTATAGTTTTATCCAATTACCTGGCTGCAGCGCCA
ATAGGTGACGTCGTCCCGGCAGATGTGACGATTGAAGGTGTGTTGCTTGAGCATGATCTGCTTGGTGCCGTACTTGCTGACGATGAAGAAGGGAG
AGTTGCTGTTGACCACTCCGGCGGACGAGGCGTTGGCCAGCTGCATAGTGGCCTCGCCCACATCCACGCTGATCTGGTAGTCGAATTTGGCTACA
ATAAGAAGAGTTTTCCTCGTTAGTTGTGCGTGATGATTGGATTAGGGGGAATTATTAGTTCAGAAAAGGAAATAAAACACTTGGGATTGCTTTAA
TGGTAAAATGGTATTCGGTATATTGTACATTGCGGATTCGGCCTATGACTACATACACATCCTACATCCTAATAGCACTGCAGACAGTGCTGGGC
GTGCTCATGATGCCTGGTGAGTCGAGGTCGTCGGCTCAGCTCCACGAGGACGTAGTAGGTCGGGCAGTTCCTGGTCAAGCAATGGAAGTAGGTGC
GGTACTGCATGGCGCGGGTTTTTTGTAAGACTTCCCGTTGACCACCAGGAACTCGCCCTGAGCGGTGCGCTTCAAGAGGACGCCCTTGTTCTGG
TCTTTTGCTGAAGAGGATGAAGACGAAGATGAAGATGGTATGATGATGAAATGACTGCTGCCACATGAGTTTAATGAGCTTATGGTAGGTAATGC
ATGCAACTGGGTATAATCTTTTGGACAAATGACATTCTTTCGGGTTTATGTAATCTCATTTAATATTGCGGATAAAAAGCATCCTTGGGCATTAG
TTTAGCGGGCACCTTGCCACCCAAAAAGCGCGGCGGATGATTGTGGGCATTCTTCCCCAGCTTGATCCCTCCGTCGAACTTGGTGATGGCCCTCG
CGGAGCACTTGTTCTCGTTCAAACGCTTGCCATTTCCGTCGGAACAGATCCAATTGACCGTGGCCCGGAAACTGGCCTCCTTCTTGTACATGTAT
CCATTGAATACCAGGTTAAAACCCTGCTTCTGGTTTTTCAGGAAGAAGTACTCATGCTTATCAATCCACTGGCCACGCGGAATATCCCCGATGAA
CTGACCTGTAATGGAGGATCCAAGGAAACTGACTTTATTACCCGGGTGGTTTGAAAATAAAAAGGTATAGCCCAGAGAAAAACACATGGAAGTTT
GAGGTGCTGAGTAAACTATTTATTGCAGGCAATTCCCGATACACTCTTACTATTTATAGCCGCTTATTTTTATCATTTGTAGAAGGCTGTAGCTA
GTTTGCCTTTAACTGGCTACAAGTCGATTGATAGTCTAATATTCTAGTGTTTGGCTAGACATCCCTTTTGTGGTCAAGAAGGGTTGATTGGTAGC
AAGGTGGACTCACCTGGGGCATAAAGCACTTTCCACATTAATTCAACAACTACCAGAGCAGAAAAATCACTAAATATCACTAAAAACACTAGTTC
ACATTAAATTCAAATAGAACATCATCCTTTTTGGTACTTTTTTGGAGGGATTCCTTTTTGAGACACCAACAACAACAAAGATGACAATCGGTGCA
CACACACAGACGCACATACATACGCGCAGGGCCACACGCACTTACTCGCTGCATTTTCGCAGGATAATTCACATATTGTAAACTTCGGACATTAA
TATGCATGCTGCAGTTAGCCACATTTAAGCCACAACACCTTTTGTTAACTATAGACTTGCAATTTGTTTGACAAAAAACAAAAACTCAGCGAACA
CAACACGGCGAAAAAATAACAACTACAACAAAAATGGCGTGCCAACAGCAGCACAAGCAGTGCTGTTAGCGAAGCTATCGGTTATCGGCTGTTAA
CTGTGTTTGAATCGTAACGTATTTTATTTTTACATATCTATATTTACTGATATTCTTGCTATATTTTTTTATTTTCAGAATTCGCATTGTCTT
ATATCTGAAAAATTCCATAAATGTAAGCTCATAGCTCAACAATCGATGGTGTATCAAGGCAAGAAGAAGCACTATTACTATGAGAACATGTATTC
TAATATTACAGAAGCGATCCCTTACACATTTTTTCCTGCTAATCCCTTCGACTGATAAATAAATATAAATGATTTTGCAAAATAACATATTTAGC
CAAATAGAAAAGCACTAATCGATAATGTTAGGTGCCAAACATCGATAACATAGTGAGTGCCAGCTCTAAAGTACAGTGCTCTTCTTCTTTAAACC
GTGTTTTTCGTGCATTAAATATTTTATTTTATATATTTGTACATTACTCCCTGCTTGTAAACCAATAAAATACACAAGAACCAGCAAAAGACCTT
CCACAGTTGTTTTATTTTAATTTTTTCGCCCGAAAGGCCCAATCTTACCCAGATGTTCTAACCTGTTGCGTTTGATTCTCCAATTGACAGCCGCC
ACATCCGCATCTGCAACTAAGATTCCACCACGTAAACGCGGCAGACCGAAAACAAAGGTTGAGGATCAGACGCCCAAGCCGAAGCTCCTGGAAAA
ACTACAGGCGGCTACCCTGAACGAGGAGGCCAGCGAGCCTGCGGTGTACGCCTCCACCACGAAGGGTGAGTCCGAATCCTGGCTAGAAGCCAAAA
TCCTGATCCATGATAACCAAGCTAATTCACGCTCCATTCGCAGGCGGTGTCAAGCTAATCTTCAATGGTCACCTGTTCAAGTTCTCGTTCCGCAA
GGCGGACTATTCCGTGTTTCAGTGCTGCTACCGTGAGCACGGCGAGGAGTGCAAGGTGCGGGTGGTATGCGACCAGAAAAGAGTCTTTCCTTACG
AGGGCGAGCACGTGCACTTCATGCAGGCCAGCGACAAAAGCTGCCTACCCTCTCAATTCATGCCTGGCGAATCGGGAGTCATATCCTCGCTGTCG
CCCAGCAAGGAGCTGCTGATGAAGAATACCACCAAGCTCGAGGAAGCCGACGACAAGGAGGATGAAGATTTCGAGGAGTTTGAGATTCAGGAGAT
CGACGAGATTGAATTGGACGAACCGGAGAAGACGCCCGCCAAGGAGGAAGAAGTGGACCCCAATGATTTCCGTGAAAAAATCAAGCGACGACTGC
AAAAAGCACTGCAGAACAAGAAGAAGTGACACGGAATATGCCTTAGATCTTCAAACTACACCTTTTACTATATAAACTTAACTAAGATCGAGAAG
GCTCAAGAAGGCCCAACAGTACAAGATCTGAGCTGCCTAAGGGCTTCACATTATACTTTCTATATCCATTTGGGTCTTAAATAGCCCTAATAATT
CTAAATAATTAAGTTTTCGTAATAAAACGATGTCAATAAATCGGACCTTAAACCATTTCACTAGCTAGTAAGATCTAACTTAATACGTAGCTGT
ACTCAAAACCCCATTTAAATGATAAATAACATAAGCCCTTTCATGTCTTTCAGTGACCCAACACGTCCGCAACTGTGGTCCTCAGATGTTCCTGA
TCAGCCGCAAGGGCGGCACTCTGTTGACCATCAACAACTTTGTGTACCGCTCCAATCTTAAGTTCTTCGGCAAGAGCAATAATATCCTGTACTGG
GAGTGCGTCCAAAACCGATCGGTTAAGTGCCGCAGTCGCTTAAAGACCATCGGCGATGATCTCTATGTAACCAATGGTTCGTAAAGCGAAGTAAG
CAAATGCAAAGGCCATTTAATGGCTTCTTTCCATCTTCAGATGTGCACAATCACATGGGCGACAACAAGCGTATTGAGGCGGCCAAGGCGGCTGG
GATGCTGATCCACAAGAAGTTGAGTTCCCTCACAGCCGCCGACAAAATCCAGGGTTCCTGGAAAATGGACACCGAGGGCAACCCAGACCATCTGC

FIGURE SHEET 661

CCAAGATGTAGCCGCTTCCTATACATTCCCAACCCAAACGTTCGTGTTCTGTTAGGGCTAAGCTAATGTATTCTACTATTGTTCTTGAGCGTATA
TCATTGATTTAGACTGAGTGTCCCGAGCCTAGTTAGGATGGGTAAGTAGCCTGTTCATCTGGGATCTCAAAGTACCATTTTTGTAATTCTTAAAG
TCCCGGGTCATATTATTTATTCTGTTCTCATTGCTTAGACGCTTTTGGCCACGGCACTGACTTAAACAATGGCTTGTGTTACGTACAAAATATGA
ACTCTTAATAAAATCAGATGAACATCTAAACGAATTGGAATTATATGTATGATCTCATCATAATATAGAAGAGATTCTTTCATGCGTTCTAAATA
GTGTTTATTTTGTGCACTAAACGTATTTGCGTTAAGAGATCTTATCCCGTTTTTTGAAAGTTTTATGAATTAATCAATTCTCGTGGGTCCATATA
AATTTAAGTTTAGAGTTTAGCTATGCATGAGTATTTTGATATTTCACGTTGCGTTATTATGTTTCAGAAACTATCTGACTTTTTCAAGATATCCA
TATAAACTATATGCTAATTTTGGTGTACTTCTAAATAATCAATAATATTCTTGTTCTCTATATATCTCGTTCGCTGGTAAATATCTACGAACAAT
TAGAAGAAGCTGTGTCTATTACCTATGCAGTGCAGGGGTTGGAATGTACTTGACGATGAGAACAGGACCCTTTTTGGCCCTAGTCGGTAAAGACC
CAAGGCATCTTTAGGCTTTGTTGCTGACTCCTGACATTTTTGTGGTTGTGCGATGAGCACGTGCTGCGGTATTTCACCTCGGAGTCCACCATGAA
CGTAGTGGCTCGGGCCTTGCAGCCCTTGTGATGATACATGCAACGCCAGGATCCGATAAGGTTGTCCTTGCCCAAAATACGGTGGACGATAAAGT
GCTTGTTGGCAATGATTAGCCTCGGACGTCTATGAGCAGCAAGACTGAACTCCGCAGGCCCGTCGAAGTTCAGAAACTTTTTTGAGTAGCGTTTG
CGATCTGAAAGAAACAAAAAGCATCAAGTCAGTAAATTGTCTTGGTAATGTCCACAAAACTATTGTGTAACTAGCGTATTTGACTTAAACAGGAT
GGCAGAGTAGATGTTTCCATTATCTTTATTTCGGTTTGTAAATTGCTTAAGCTAATCAGGACCTATACAATTTTGCACTTAGCTTAGGTTTAGGT
GGCTCGATTTGCAGCATGCAATCTTTGGAATATTTCAAGTACTTTGCAGTAGCTTCCAATTCCACCGTGATGTTATTTATACAAACATGATATAT
GCCTGTCCTTAAAATTCTGCAAAGACTCCGCTGCCCGCTAAAAATCGCTCACCTTAGGTACACTCTACATCGACATTAGTTCAACAGATAATAAA
AACCACAGATTTTGGTGAGCCCACAACCGACGGGGCTAGTAATCTTTGCTAATGAAGACGGCACCGTGCGCCTGGTGCTGCTGCATCAGCGCCAT
CATTTGCGGTGTTTGAACGTGTGGCAGGGAGATGGGCATCGCCAAAGACATGGAGACGGGCACAGGTACCGTCACCGGCATGCCGAGGTGGGTGG
GCCCTGTGGCGTACGCCGCGGTCGGAGGCATCTGCGCAACTTGGGTCATCATTTCCATCGCAGGAGTGGGAGTCGCCGAGGTGAGCACATGGTTC
GGGTTGGGTGGTGAACTTTTAACCGCTGGCACAGTGCCGTTGGCCTTGGCCTGGCAGTAAAGTTGACACAGGGGCAGCAGCTCCTTGTGCCGCCT
CTTGATATGGCTGAGAAAGTTCCCCGTGGACTTGGTGGTGCCGGAGATCAGTCCGTGGCATGTTGTGCAGGTGGCCTGGATAGCACCTGGCGTCT
TCTGGTTCGGCTGGATGTTCTTGTAGAACTTACCGTCCAGTAGCTTGGGCAGGGTAAAGGGTTTCCGGAACGATTCCTCGTCGCTTAAGTAGGTG
ACGGCAAGGGCGGCCACAGCAGCATCCGATGAGTGCCCAGGCGTCGGCGAAGGCTCCATTTTGATCTTGACTGCAAAATGAAAAGATTAACAGAT
TAGTTGGGATTTAAGAATGCTTAACAACTATATAGTAGGTACAGAACGAGAACACTGATTACGTATTATGTGCACATTTAATTTAATTTATTTAT
GTTAAGGTAGAGCTGAAATCGATGAGTATATTATATATTAACTGCTGGTCCTCCGGAGCTTACTGCAGCTCCGGAAATTCGTCCAGCAGGTCAGTCG
TGAGATCCATCGAGCTGACCTCCGGAGCGTGGGTGTGCGGAGTGCCAGCGATGCGCAGGGTGACCTCCTGCACTTTGGAGGTCACCAAAGTGGCC
CGGCAGCTGTGTTTCACGTAGCGTGAGCACCGCCAGAAGACGTTCTTCAGGCTCTGACGATTCACGACATACCGATAACCCTCGTAGACCAGCAT
CACCCTGCCTCGTTGCGTCGTGGTGTACTGGATACTGGCACCGGTGGTTTTGCCCTCGAAGAGCGCCTTCAGCGACTGGATGACACCTGGAAAGG
GAGGTAGATGTGTTTGACAGACATTAGTTGAGGTTATTTTGGGAGATCCAGGTGAGACCACTAACTAGTGCACAATAGGTTTAAAGGGAAGTTC
TAGTACAGGCATTTATTTCGGTTTACGAATGCAACAATCAATTTAAACTATTTCCCCTCCTTTATAGGCATAAGTTTAAGAGTAGACAGCTTGTG
GTCAATGAACTCCTGTACTGCGGACGGGGTCAGCTGGTTGCCGCGCAGGGCAAACACTTTACACACATGGGCTGAAAAGATGGAAGACACACAGG
TTAGAACGACTAATCGTGCAACGGGCGCAGCCTCCCTTATGTACTTATGATGTCCTGGATCAGGTCCTTGTCCGTGGTCTCCTCGTGCTGGGCGA
TGCGCACCAGCTTGTCTTTACCAATCACCAGATCCATCACACGGCACGTATATATCATCGGCATGGGGATATACGCCTTGGCCAGAGCCACCTTG
GACACAAAGACCCGGCTGCCATCGAACAAGGGGATAGCGTCAGCATCTCTAGGGGACTTCTGCACGCTATCAGTTACTGGTTTCCTTGGATGCTC
CGCGGGCTTCGGGATGGCAGTGTCCTTGCTTGGGCCATCTGGAACGGCACACGATGGCAAAAACGATTAAAACACTTTAGCTTAGGAGGTCAACG
GAAAACATAAACAAAATAAAACACGGTTATTGCGGTTTTCTTTTTTACAAAGTCTTTATTTCATTTCGATTAGGAAGCTTTCGCCTACACTTTTA
GCGCAATTCTGGCGTCAAAACAGTTTTCCCATTATTTTTCACACTCGTTGCCCAATTTGACATATTAGAACACAAATTATTTATTGAAGTAAGTC
CACGCGAGTCACAGTAGACAAGGAAATGGCAGCAACAATGCCAGGGCTGCACTCGATGCACAGCGAGTCCTCGGTAAAAGGGCGAGCAAAATGCT
ACGTTGTTTGATCTAAAGTTTTTTTAATTATGAAAATGACATACCTTCTTTAATATTACTATACTCAAGTAAACATATTACTAAATTATAGCAAA
ATATGCATATTGGTATTGGTACTAATAAATACGTCATGCAAACAGCTCGTTCCGTGTTAGAAAACGATTTACCGGTTTTAAGATGGTCTATAATT
TTTCAGTAGTTTTGCGCATACCTATAGCTACTGTACTCCCGAACATTGCAGCCCTGGGTGCAAGCGCTTGATCTGGCAACTCTGTTAAAATGTCG
CCCACAGTTGTGAAAAAATGAAGTGATTTCCGAAAATTGTTGCTAAATTACTAAACAAAAGGTGAAATTAAGATTTGTAATGGCCCCGAAAAGTG
AATAGTGTTGGTGGAGTCCTAGTTGTGCATGAAAGAACCGCCTTCCAAAGAAGGGAGCCCAATGGCGAGTAATGAAGATGAATAAATGCCAACGA
CGCCTGGAATTTCAATCAAATGTGTACAAATGTTAAAACGAAATTGCAAAGCGACGCCATGCGCGCAATGTTAATAAAGTACAGAAACTAGAGTG
AAGCAGGGATATATTACTTGGCGGATCCTCTTGGGCAATCAATCAGTCAGAGCGTTCTAATCAATACCCCTTCCTCCCACTTCAATTTGTGTCTT
GCAGAACAGGAGGATGACTTCAAGTTGCACCTGCCTCTCCTCGTGACAAGAAGAAAGAAGACGCCCGGTGGCTCCCGCAAGCAGAGTTTTGACCA
CCTGGAGGTGAGCTTCACCAGAAGCAATAGGGGTAACAACTTGCTGACCATCGATGGGAAGCCCTTCACCCTCAATCGTCGGATCAAGGATGTGT
GCTACTGGGAGTGCGTCAAGCTGCGCTGCAAGTACATCAAGTGCTCCGCCCGTGTGGTGACCAAATCCAATCGGATCTCGGCACTGAGCGGGCTC
CACAACCATCCCTAAGTTACGAACTACCTGTGCCATCTCATTAGTCTAATAAAGGTGTTTACGTTGAATCAGTTTATATCTTCCGCCTCTCCTAT
CGTTGTTGATTCTATAGTGTCCTTGCGCAACTCAGGACGCCCTCTGACTAATCTCTTTCAATTCTTGCAGCATGCTACCAACTGGTGCCCAATCG
CCGCGGTGGGAAGAACCTCATCTTCCAGGGGCACATGTACTCCGTGGAGCGCAAGTACCGAAACAGCATCAACTGGGTATGTTCCAAGAACAGCA
ACAGCGTGCTTCGCTGCCCGGCGAGGTGCGTCACAAATCCGGAGAGTGGCAATGGCATCAAGCTGAGCCACCGACGCCACAATCATCCGGCGGAT
GCCTTTAAGCCCCACAAGCGCTGTCGAAAGCGTCCCGGCGATCGAAAGTAACAAGTAACCATGTTTCAGGATGCAAAGCATGCAGGCTTCGGCAA
TTGTTAGTCACACTAAATATAAATGTTTCTCATCGTTGTCGAATTGTAACATTTTGGTGTAATGGAATCACTGTTCATTTGGTTTTGGGCTTTCA
CATATCCGAATTACTTTACTAATACTCACTCATCAGCACGTTTCCCATAAACTAATTATAGTTTTAAGCTGTAGTTAATTCCAAACGACTTATGA
CTTACTATGAAAATCTCCTAACAGATTTTCGCCACAGTTGTGTTTGCCGACGGAACGGAGTTACGATAATCGATGGCTACCGCTTCGTGATCGGT
ACTACAAATCTGCGTCGCACCTATCTGAAGTGCGCCAACTTTCGCAGCAACTGCCGGGCCCGGGCCATTCTTAATACGGATACGAACAAAGTGCG
GATGAGGCACGACCGCCATAATCACTCCCGTACGGATGCTGTGAGCGGACGTATCTCTAAGAAGTAGCAGGTACCGAGCTGTCTAGAGGAATAAA
CATGCTGTTTCCGTTTAAAAATGTTTAACTGCTTTTCACTACCAACGAAAAACCATAATAACCTTACATCCTCACCCATAATTTGAAAGACCTGT
CCTAATCTAACTAAATTCGCCAATCTCTTGCAGATAACTCGAAAATAGCGCAGTATGTGCGCTCCAACCGAGGAACCGATCTCGTTTACCACGAG
GGAAACACCTACACACCCAATGAAAAGCTGAGGGAGGGACAAAAGAGTCGAGACTGGAAGTGCTCAATGTACCATAAGGCCAAGTGCCGGGCCCG
CCTGGTTACTCGCATTACCGGTGGAGGGGATATTATACACGTGACCAGCAACCTGCACACACATCCCACAATGTACACCACGCAGAAAACGGACA
TTAGCGTGGTTGACCAGAAACTGTGCCTCGAAAGGAATCCACTCTGCGTTAACACTCGATCGATTAAAATGTAGATCAAGTAAAGACCACCGACT
GATTACTCGTTACGATTAGCATGATCTTCAGTATAAATAACGTTTTAGATTTAAAAAGTATTAAAAAAATGCTCATATACATTCAATAATTTTTAA
GTAATTTCATTTATTTATAATAAGCATATTTTCTTAAGTTCTTTCACATTTGATTTGTTTACTACGACGAATTCCATTTTTAATTCAAAACCGTT
TTATTTACAGGACATCTTTCGACATTGCGCCATCTCCCAGTTGAGGCCATATTTGATGCGGACGGCAAACAGATGGACTTCATACCCAACATTCG
CGTCATCCGAAGTCAGCGGAAGACCATAAAGCTGATGTTTAAAAAATATGCCTACTCGAAGACCAACGAGCACGATACCACAACCTACTGGCACT
GCCGAAGTCGTCGCAATGGAAGGCCTGCGTGCAAGGCCCGGTTTTCCACCAAGAAGCTCAAGAACGGTAGCTACAAAGTATATCTGACCCAGCCG
GAGCACAATCATCCCCCAAAGAAGCGTCGCCTATAATCAGAATAACTATATTTTAAGAAGAATGATATATTAAAGAGCCATGTCTTGGCAAAATG
ACTTGCACCGACTCTGAATCTCTACTCTACTACTCTACTCTCAAATAGCCCAGCAAATGACCATTTACTAATTACAATGTGTTCCTTTCTCCTTC
CACAGAAAGCAGCGTGGCGATCTACTCGGCAACCTCCCGGGGACGAATGCAACTGATTTACGGCGGACAGCCATTCATCTTCGAGAAGACGCTGA
AACTGTCTTCGGGAGAGGAGAAGCGCTTCTGGCGCTGCAACCAATGGTGGAACCAAAAGTGTCGCTCGCGCGTCTTCACCATCAACGACGTTGTC

FIGURE SHEET 662

TGTCCGCTTAACCGATTCCACACGCACGAGGAGATCGTGCGGCGAAAGAAGCGAGTGCGCCGCGTGCCGCCGGTGGAGACGATTGCCAAGGTGGT
TGCCACAACACCCAGGCATCCGCAGCATCAACAGACAACCCAGCAGCAACAAGAGATTCAGCTGACCAGCGATGCAATTGCTGGAGCAATACTGG
ATGATGAATCCCCAGCTACAATCGATGTCAGCGAGCTGGGGATGCACCTGAAATACGAAGAAATCGTAGCGGATGTCACGGGCATTGTGGGCGGC
ACGCGAGTGGTCAGTCGCCGAAAGTGAAGATTGCTTTTTATTTCTGACGTAAGATCGCAGATTCAGATTCCTTCTTTGTAAAAACTCATGCTTT
GAGTTTTCATTTTTGAACTTGCCACGTCGAAAACCAAGAGCCGAACAGTTTTGATGAATTTAAAAAGGCTAAGCACAACCACTAGCCAATAAATA
CAATTTTTATTATTATTTTAAGGACATATTTTTAAAACTCTTTTTATTAAGCGTAATATTCCAAGGTTTCCTCCCCCATTTGTAAAATTTGATAA
ATACCCCATGATTTCCTTTGACATTTTGGAGTTGTTTAGAATAAAATCTGTTCCTTCTGTTATGCCTTTGTTCAAACAAAATTGACCTAGCCTAC
TCCCATAATTATTAATACAAAACTGCGTTTAAGAAGGCGGACAAGCTAGCTATTATGATACAGCTTATAAACAATTTATTATGTGTACATTTAAT
AAACGTAAGACCCAAACAGTGCAATTGAATCGTTGTAGAACCTCCGAACTTTCTCCACAACCCACTTGAGATCCTTCCTTCAAGCGAATATCACC
GACTTACTAACGCACCGGGTCACATATCTATTCTCTTTTAAGGTGACGCCACCCAGTTCTTCTTCACCAAGGGTCAGCGCGAATCGGTCAAACTC
AACTACTGCGGTCATAGCTACGTCAAGTTCATGGAGAATGGACGCGGCACCAAGTGGATTTGTGCCACGCGCTCCACCACCAAGTGCCGTGCTCG
CATCCGTACCACCAAAAACAACTACCTGGAGGTACTGTATGCGTCCCACAATCACGGTTTTCCGCCGCAGAAGAAGGATCGGGGTCGAGCCAGCC
AAAGGATGTGATCCAAAATGTAACTGAGAGTGTGACTGTGACTAAAGCCAACTTCCCCTACAATACAATTTCAATAGTTTACAAAACACTTGAAG
CCTCCTCTAAAACAGCTTGACTTTGAAACTATATATTGAAAAAAAGGCTGAGACAGCGCCAATCAATTTCCCAGCCAACCCAATCCTAGTGGTCA
ATCTGTCTAATGGATGTAGCCATATTTCCTTCCATTAACCAAGCTCAAAGTTTGCCAGATGCTTAGATTGGCTAACACTATTTTCGTTTTCAATA
CAAAAGAACGCCTATATGATCTTCCTAACTCGAAATCTGCGAGCGAGAAATATACTTACATGAACAGACTTTAAAAAAAAACGAGTTCACCATAA
TGAGGGCCCAAAAAGTGTGCTAAAGAAACATTTTATTCTTCATGGTTAAATTCTCTTACATACTTAAAGTGAATATTGTTAAATAGGAAATGAAA
TTAAATTTTTCGAGAGGTTACGACACACCACGAAGTGCAGAAATCAAAATAATATAGATCTTTTCTAACTTGTGTCTTTGAATTTGAACTTATAC
CTTGATTAAGTCGACCACTTTTTTTTTGGGTAATATCATCCTTTCCTCATCCACTCAAGAGTGGAGTTCCTCGAAGCAGGGCTCGCACATCCAGT
TGCTTCCAGGACATGTGTTGCACAGCGTATTGATCCTCCTCAGGCCCGTCCTGTTCTTTTTTAGGCAGTTCACGCACTTTCCCTTCATGCGAGGC
AATCCCACATACACAAAGTTGTGCTCGTTGGATGAGGTGCGGATGATGTTGTCCGGGTTCTTTAGGTTCAGCCTTCCAGCGGGCTCCAGTTTTAT
GATTGTGGCTAAAAATTTGTCATCCCGCACCTGCCGCACTTTTTGAATCGGTGCTATATGTCGTGCAGCCTTAAAAATCAAACCTGTAAGTTTAA
GAGGAGGAAAGATATATTATATGGTAATGATTTTCTTATGAATTTAAAGGGTATTAGAATAAAAATATACCATTAAATAGTTTAACTAAACTATC
GTTTGCTTGTTTCATTTAATAAATTATTACTCTTCGCTTATTTGTACACTGTTTTGTTCATTAATGCATTAAACTTTAATATTCAAGCCGTATGT
TTTCCCAATTGAGCGTCAGTCTTGCAAACGGTGTACAAATGTCACATTTAAATTTAAATATAAAAGATTTAGATTAGAGGAAAGTATCAAACTAA
TTTTATAGATTATAATGGTTCTTAAAATTTAATAATCCTCTTTATGAGGACGAGGTGGGCAATCGAGCACTCTGGGAACAAATGTCTTTAGTCGT
TCCGGCGGCTTGTGATTGTGAAATCCTCGGATTGATTTTATTGACTTTATGTGAGTGGTCAGCGCCGAAGTGCAGTGCATCTTTTTGTACATGGA
GCAGCGCCAGAAGGCCAGACATTTCCCGGGATTCCTGGAGTAACAGCTAAACGTGAATCCCTCGTGGACTAATTTTCCTCTATCGTCGTAGGTGA
GAACTGAAAGAGAAGTATTCAATTAGTCAATGGAGACAGGAACTAGGCCTACTCTTCGATACCTCGCCTCCTAATTGATCAGAACGAAGCTCGGT
TACTTTCATGAGTTCAGATCTTTATTTCACATGATCACATAGCCGTCAAGGGAATGGAACAATTGGATTTGCAAAGCATATGCGAACTTAAAAAA
ACCTTCATTGGTTAATCGAACTCAGGGGTCTTACAGCTATATTCACAATCTTATTCATTAAACTTCAAATTAAACTCGATTCGACACTTCAAAAT
GCATATTCGGGTAACTAGGATGAAAATATCGAAAATAAGTGTACATAGTCCATTTCCTAGATATGTACTTTTAATAGCTGTTACTTAGTAACTAC
ATTGCACTGCCAAGACCAGTTGGATAGCCAATCTATTCGTGCATGAGCATCATGGAGGCGTGCATCAGTTCTTGATCTGTCAACTGCAATGTGGC
CGCATCGCTAGTCAACTGGTGTTCATCGATGAACTCTTGCTTCTGCTCCTGAAGCTGCAGCTGTGTGAAGCTGTGCGTCCTGGAGAGCTTTCTTC
CTGTGCCGATCGCTGCCATTTTGTTACGCTGAATGATCTTGTCTATCTTCTCCGTGTGCGGCTGGTGGTTATGTAGTCCGCCTGTCACACTCTTA
AGGCGTCCGTTCTCCAGGACGCAGCGAGATCGACAGCGCATTTCATGCGCCTTTTGGAGTAGTTGTGGCAGCGCCAATACTGTTTATTGCTCTT
GCGACTGTGGCAGTTGTACATGTAGCCATTTAACACTAGGCACGGCGTCGACCAGGGGCTCTCTATAAAAACCAGCTCGTCCTCTGAAAAGAAGA
AGTTTTTATCGTTAGTTCAGTTGTCTACACTTAAGATATTTGGTTAATAACAATTGGGTTACCCAGTCCACAATGAGCTCCATCTTTTGTTTTGG
TCTTAATTTATTAGGAGCTAAGTATGAAATACGTTTACAGAACTCAGACAAGTCGCTTAAAATCTACTTTCGAGTGGTCGGGTCGATTTCTTTGG
GCAAAATGGTCTTGAGCCTTGTGGAATTGTGAATTTTTGCATGACTTACTAACATATAAAGATGTATTACTATTAAAATAAATATGTATTAATTA
TTACAGAGCTGGAAAGTTTAGGTTTTAAAAATAAGCCAAAATAATACCAGCTATGGCTTTCTTATCTTTATAAAGACTTTCCAACTGATTGACT
GTAGATTGGTTAAAAACTCCCAAGTGAAATCGACTCCTTCCGTGGTTCGAGATAAATAATTAGCTTAGGTGTTAGCTGATAACTCCTAGGGGTGC
TCGCTCTTCAGCAGGGATCGATGCTTGGCCTCTTCTGTCCGCCACCTGCCCACCCGTTGCCGATCCCGGATCCGCTCCTCTGCATGCCGCTCCTC
CTCATCTAACTCCTCCTCAGCGGCGTCCACAAGGGCCTGCATCTCGATCTCGGTAGCCTCGGCAGCGGGCAGGAACAACTTGCAGTCCTTGCCGT
CCTTGGCAGTCACAATGATGTTGCTACTGCCCAGATACTGTGATATCTTTGGGTTCGACGTGCAGATCTCGATGTACTCCTCCAGTTCCTGCTCC
ACCTTATACAGTTGTCGCTGGCCAATCCTCGAGGCGTGGGACTCGTGATTGTGCTGACGTCGTGCGTCGATGAAGTGTCCGTCGCGGGTGATGAC
CACCGCCTTGCAGCGCAGCTTGAGCACATCCGCACAGCGCCAGGTCGTCTGTCCATTGGCCTGGGTGAGCTTCTTGTTGTAGATGTAGTTGCGGA
ACACCAGCTGGGCGTTCTTCTTCTGGCTGCGAATGAAACTGATCTCCGTATCTGCGAGAGTCGAGGAAAACCGAAAGCATGGGGTTTAGTGGGCA
TAATATAATTGACAGATGATCTAGTTGCTATTCTAGTGAATGTACATATATGGCTTAAGCGTTAAGTTAGGATCGGCGAAATAAAACAACGTTTA
GTTTAGACTTTGGCTTTAAGCAGTTTATTCGCAATCAGTGAACCGGAGGACCCTTGGGTTTGGTGGTAGAAAACTTACCAAAATGCGGCGGGATG
GCATTTTACAACTTACGGTAGCATTTGCATCGCTTGGTTTTCAAATAAGCACTATCACAGATTATCAAAAGGGTGGAAATAGGGAGGCGTTGCCC
CCCTTACCAGCCCCATCACTTTAAATATTAAATAAACACCACACCAAACACACCGTCACAAGCTGGAAATAATTAATTGTGAACAAATAGGCCGT
GTAATTCGGATGCAATAAAATAACAAAACAAATTGGCTTGCATTTTTTTAATGAATTTGCACGGCGTTGCCACACAGCCGAAGCACCAGGGCTGC
ACATTCAATTAGGGTTTCCGGAAGTGGCAACACCGTCCTCAATTTCCACAAAATGGCAACTCCGCATTAATTCAAATTTTAATTCTTTATTTTTT
CATACTACAAATATATATATAATATATTCTGTGGATACTTTCTAAATATCCGGACCAGGCGCGCAAAATATAAATTACACGATTCAAACGTTAAT
ATAAATTTTCTCAAATACGCTTAACAATAAAAAAACGAAAATTACTACTACAAATAAAGGAAATATAAGTCGGAAATGCTTCAAGGCGGTCCAAC
CTTTTGTTCCAAGGTATATAAACTATCGCCTATATGAATTAAAACGGTTTATGATTATCTCTTACCAATTAGGTAAGAGGTCTAGTATATTCTGT
TTTTTTTGTTTAAGGTTACCGCGACATCCGTAAATATCGTGAAATTCTTCAGACACCCTTTAATTCGGAACCATATAAAAAAAACACGCAAAATG
TTCCATACAAAAAATTTGGAATGAAAAAACAAAATCAGCACGCAAAAAGTAAAACAGAATCGACGCTGCATGAAGAAATAAATTTCCTCTCCACT
GATAACGTTAAAAGAGTCTCCCTATACGTATTATTAAAATCTTTCCTTTTTTTTTTACGTGACCACTAAAACGATTAGAAATGAACCTTTACTAT
AACACAGCGTTATAAATACAATTTTTTTTTAAGACTCGGCAATCAATGCCGTTGCTGGATTTGCATCAGCAAGCTTTTACGTTGCTTAAACAAA
TCCAGACAACATCTTTAAGTACGAGTTTGAAAACATAAATAACAACAAACCTCAGTAGCCTTAGCATCACCAGAGGATCATTATTAAACAGAAAT
GCGCATGCCCAAATAATAACCCCCTGATCATGTAAGATTGAAAACTCCAATTACTCGCTTTGCTCAGTCAAATAAACAATTACAAATGCCTGCAA
ATTTTGGAAAAATATATGGATAGGTGTGGTTTTAAGAGTGCCGGTATTACCTTGAGTAGTTGCAGCTCTTCACGGGTTCGGCTTCACGTTGACAT
CAGATATCCATCGTAGCAGCTTCTTAAAATTTCATCACTCTACTTACCTTTTAACTGAATAAGTGTAAAACCGCGCGATCTCCGTCCAGCATTTA
ACAAATATGCATCGGACAGCAGATCTGCCTAGTGCTCTTTGTCGATTCGAAATAGAACACAGGCCCGTAAACTACTTATTAACTAATGGCCAGCG
AAGTATAGCTTAAGTTTGTTCAAAACAAAATTAAACGCACTTTGCCGAACTCTAAAAGGACATGATCCGCTTGCGACGCTAATAGATTTGGAAAG
TGTTCAAGTTTGGAATACATATGTGATCTTTTTTTTAACGTGTTTGCATTTCGCAAGCGGACTTAATGTCCTTTAAATATTGCTTATATCTATTG
GCCTCTGGCCATGTATGCTTTGCAATTCAACCAACCTTGAGCCTCTGTGTTGCCCTGATCCCCGCTGGTGTCGACAAACGATGATTCACTGTAGT
TCTGGGACTGTTGCTTGACCACAGCCTTGGAAGTGGTCGCCGTCACTCCGCCACCGCTCGTATTTGCCGCAGTCTGGTTGCCAGCATCCTCGTTT
TCAGTGAAGTAGCTGTCGTCGTAGCGCATGTCTCCGTAAGTATCGTCCTCCACATAGGTGCCCTCGGCATCGCCGGCGGCGTCGCCATGGTCCTC

FIGURE SHEET 663

AGAGTAGTCAGGTTCAGATTTCGTGGGCAATTCCATGGGGAGATCAATGTACTCGGCTTCCTCCTGTCGAACCTGCTGCGGCGATTGCTGGTGGA
GCTTTGCTTCTGCCGCAGAGACCACAGAGGTTTGCACGGTGATCTGTTGCGGCACAAGTTGGGCGGTTGTCGTGGCTCCAGTTTCAGTGGTCGAG
TCGAGAGGGTCCATAACATTTGCGGAGGTGCTTGTCTTGGAGCGCTTTACGCCGGCGCTCGAGGAGGCGGGGGTCAGGGAGGAGCGCTGGGCAGA
GCGTTTGTTTGTCGACACCAGCGTCGCCGTCGTCGTGGTTCCCGTCTGCAGCTGCTGCGATTGGATCTGCTGCGCCGCCTGCTGCGGTTGCTGCT
GTTGTACAATGGTGGCTTGGGGTGCGGCCGTGGTCTGGATGACGATCTGGGTGGTGCTCTGTTTCTCGTCGCCCAGGCCGTCGTCCACGGTCTCG
ATCTTGTAGCGGGCGGAGGCGCGAGGCTGCTGGCGCTGCACCCGCTGAGCCGGTATTTGCTGTTGTTGTACATGAGGTGCTGCTGGCGGCGGGCT
GGATTCCTGCGGCGGCTGAGGCGCAGGATCGTTCTGAAAAAAAAATATTGGTTTTTAATTATTAACATATATTTTAGGAATAAGTGAAAAGATA
TTTTGTATGTTCTAGCACCTCTTTAAAAATGAACCACGATCAAAACTTAATAAACTTTAAAAGTATCTGCATTTAATAAAATGGACGATTTCAAA
ACTATATGTTGAAAAGAATTATTCCGTTAGAATGGAATTTGCAAAGAAATAAGAAATCTGGCCATTAATTAGTAAAGTACGCCTTCCTTGAATTG
GGAAACAATAATACATTTTCTAGTTCCGATGCCTGTTTCTTTAGGTACAGCTGCACTAAATTTAATTTTGCAAATACGTTAATTTTAGTCGAAAA
CATTAAGAGATATTTCCCAATTTAAACATTAGTTTAAAAGCAAAAAATGTTTATGCTTTGGCATCGAATTCGCTGCGAGACAAAAACAACCACTC
CAATTTGCCGCTGCCGTGCGAGCCAGAGCGAGACAAACGCTTCGCGTATAGCCCCTGCAGTTGTCTCTCTCTGGCACGCGTGCCTTTTGGCATTT
GGTTTGCGAGAAATTTCTCGGTACAGTCAAACCATGCTCTTATACAGACGCCAGCCATCGCGTCTGTATGTATTGGGCGCGAAAGGTTGCGTTGT
AGTTGCTCGATTCGATATACCAGTATATCACGCACACAAATGTATACATATACTCACATCCGTTAGCCCCTTGATTTGCAGCGATTCCGCGGTGC
TAATAAACGCGGGCAGGGCGTCCTGCTTCACGTTGACCTCGCCGCAGTACATGAATTGGATGAGGTCCTTCAGCGCCGAGTGGCTGACGTTGTTC
AGGAATACTGCAAGATAGGCGAAGAGAGTATAAGGTAAAAAATCACGTAGAGCTACAGATCTGAGCTGAGGGGCACAAACTCACCGATAGCGTGG
GTGTTCGACGGCATCTGAGTGAACATCTTGCGGAAGAAGGGCGAGCAGACGGATAACACCAATCGGTGGGCCTTCACTATTTGGCCCTCGGCGGC
CAGCGAGACGTCCACCAGGTCGCCGCGGCATAGCGACTCGTGGAAGCCGGCCGACAAATTCGTGTTGAAGTTGTTCCAGCACAAGCTGAATTGCT
CGTCGTCCGCCATCTTGGACGAAAATCAATACTTTTCTGTATCTATGCGTTTGTTGGCTGCAGGCGAAAAAGTGCAATGCGCGTTTAAAACTCAA
TGCAGCGAGTGCTGAAAAATGGCAAAGGCACACACAAAATAGAATGCACTGCAGCCAAAAAAAACTGGGAAATTTTCACGCGTCTGTCTGTGTGT
GCGTGTGTGTAAATTACATTTATCTCGCTTAATGACCGCAACCTACTGTGTATATTCACTTGGGGCGCCATTACTCACCTCTTGACTAAATATTT
TTCCAATAAAATAACTAACTAAAGCCAGAGTTTTTTGCTAGCGCGGCCGACACGCAGAACGCGTCCGAGTTCTTTGACGTGAAAATTAGAAGTGT
TACCAGGCGACGAGATTGCTGGCGATGGCAAAACAAAAAGTGACAATATATCGATAGCTTAAAATATTTATATCGAAATACTTTTATGAATATTG
ATAGTTGATGTGCTTTGATATTTTTTTTTAAATGTTAGTACGAAAATCACATAATTAAGTTCATAACTTTTTGAAAACTTTTACATACTTTAGT
TTACATATGCTGTAGGATTTTAGTTTGCGGGTGTGTTAAAAAAGGTTGTAGGACTAAGAAAATATCGGCCTAAGTATACGATGTATTTATGTTAT
GACGAAATTTCTTATTTCACAACAGTTTTGTTGTCTAGCTTAATGTTTAATTTATTTTAAATGAAATAAAACAAAATACAAATTAACGAGTTTAA
AGACTAGCAGTCAAACTAGCACAACTAGAATAAAATTCATAAGATAAACAGAAAAATTTTAACTTTTTTAAATTCTCCTATTTTTTAAACTGGGC
CTTCGATTTTTTACGAATGGAGGATTATTTTCTAGCGGAATTCATTATAACTCTGACAAACTCTTATGGAGCGCATCGTCACTACGTAAACCCTA
CACTCTGAATGCACAAGGGCACTATATTTTTAAAAAAAAAGTGACTTAATAGGATTATAAGAAAGGCAAATATTCGCTAAAAGTTCTTAAACATA
CCAAACAAAATATGTATGTACATAATATGTATATCTGTGTACTGTATGTACATATGCACTACATATGCAATTATATACATATGTGAACACGTTTT
TGGTGCAATGCCAAGATTCGAAATGAAGGTATTCATCCCATAAAGGCGAAATATTATTAAAAATGTTGCTCTATTTAGACAACTTCACATATCCA
TGTTATTCATCTCTATTAAATCATAACAGTTTCAAGTGAAATAAACAATAATATATGAGAGCGTAACGTTTAAACCAAACATATTCCCCACGATT
TATTTATTTGTTAGCTTAGTACACTCTTAAA
(SEQ ID NO: 1237)

Exon: 23161..23069
Exon: 22857..22600
Exon: 22522..22383
Exon: 21693..20841
Exon: 1338..1001
Start ATG: 22813 (Reverse strand: CAT)

Transcript No. : CT40910
CAAAGAACTCGGACGCGTTCTGCGTGTCGGCCGCGCTAGCAAAAAACTCTGGCTTTAGTTAGTTATTTTATTGGAAAAATATTTAGTCAAGAGCC
AACAAACGCATAGATACAGAAAAGTATTGATTTTCGTCCAAGATGGCGGACGACGAGCAATTCAGCTTGTGCTGGAACAACTTCAACACGAATTT
GTCGGCCGGCTTCCACGAGTCGCTATGCCGCGGCGACCTGGTGGACGTCTCGCTGGCCGCCGAGGGCCAAATAGTGAAGGCCCACCGATTGGTGT
TATCCGTCTGCTCGCCCTTCTTCCGCAAGATGTTCACTCAGATGCCGTCGAACACCCACGCTATCGTATTCCTGAACAACGTCAGCCACTCGGCG
CTGAAGGACCTCATCCAATTCATGTACTGCGGCGAGGTCAACGTGAAGCAGGACGCCCTGCCCGCGTTTATTAGCACCGCGGAATCGCTGCAAAT
CAAGGGGCTAACGGATAACGATCCTGCGCCTCAGCCGCCGCAGGAATCCAGCCCGCCGCCAGCAGCACCTCATGTACAACAACAGCAAATACCGG
CTCAGCGGGTGCAGCGCCAGCAGCCTCGCGCCTCCGCCCGCTACAAGATCGAGACCGTGGACGACGGCCTGGGCGACGAGAAACAGAGCACCACC
CAGATCGTCATCCAGACCACGGCCGCACCCCAAGCCACCATTGTACAACAGCAGCAACCGCAGCAGGCGGCGCAGCAGATCCAATCGCAGCAGCT
GCAGACGGGAACCACGACGACGGCGACGCTGGTGTCGACAAACAAACGCTCTGCCCAGCGCTCCTCCCTGACCCCCGCCTCCTCGAGCGCCGGCG
TAAAGCGCTCCAAGACAAGCACCTCCGCAAATGTTATGGACCCTCTCGACTCGACCACTGAAACTGGAGCCACGACAACCGCCCAACTTGTGCCG
CAACAGATCACCGTGCAAACCTCTGTGGTCTCTGCGGCAGAAGCAAAGCTCCACCAGCAATCGCCGCAGCAGGTTCGACAGGAGGAAGCCGAGTA
CATTGATCTCCCCATGGAATTGCCCACGAAATCTGAACCTGACTACTCTGAGGACCATGGCGACGCCGCCGGCGATGCCGAGGGCACCTATGTGG
AGGACGATACTTACGGAGACATGCGCTACGACGACAGCTACTTCACTGAAAACGAGGATGCTGGCAACCAGACTGCGGCAAATACGAGCGGTGGC
GGAGTGACGGCGACCACTTCCAAGGCTGTGGTCAAGCAACAGTCCCAGAACTACAGTGAATCATCGTTTGTCGACACCAGCGGGGATCAGGGCAA
CACAGAGGCTCAAGATTTAGGTGAACTCAATCCTAGCAACCTGGCTGACTTTGGTAACGAGAGCTTCTTGCCCAAAACCAAGGGTAAACGGCCAC
AGAATGTTCGCTGTGGACTGGCGCCCGATCAGAAGTGCGTCCGCACCCTGGACGACTGGGATCGCATCCGGTATGATCGGACCAGGAGCGGCGAT
GTTCTGGTCTACGACGGATATCGTTATGATCGACGAGCCAACTACAACGATATCATATATTGGGGGTGTGCCAAAAAGCGACTAAGCTGCAACGT
CTACATGATTACCCACAAAAACAAACCCACATATGTAGCCATTTCAGGCGTGCACAACCATTTGTAG
(SEQ ID NO: 1238)

Start ATG: 138 (Reverse strand: CAT)

MADDEQFSLCWNNFNTNLSAGFHESLCRGDLVDVSLAAEGQIVKAHRLVLSVCSPFFRKMFTQMPSNTHAIVFLNNVSHSALKDLIQFMYCGEVN
VKQDALPAFISTAESLQIKGLTDNDPAPQPPQESSPPPAAPHVQQQIPAQRVQRQQPRASARYKIETVDDGLGDEKQSTTQIVIQTTAAPQATI
VQQQPQQAAQQIQSQQLQTGTTTTATLVSTNKRSAQRSSLTPASSSAGVKRSKTSTSANVMDPLDSTTETGATTTAQLVPQQITVQTSVVSAAE
AKLHQQSPQQVRQEEAEYIDLPMELPTKSEPDYSEDHGDAAGDAEGTYVEDDTYGDMRYDDSYFTENEDAGNQTAANTSGGGVTATTSKAVVKQQ
SQNYSESSFVDTSGDQGNTEAQDLGELNPSNLADFGNESFLPKTKGKRPQNVRCGLAPDQKCVRTLDDWDRIRYDRTRSGDVLVYDGYRYDRRAN
YNDIIYWGCAKKRLSCNVYMITHKNKPTYVAISGVHNHL*

FIGURE SHEET 664

(SEQ ID NO: 1239)

Classification: transcription_factor

Celera Sequence No. : 142000013384688
ATTTATTTTTATTTACTTGCTTTCCACTACAACGAAATACATTCCATAGATGATTTTATTAAGCTTTAATGAAACAAACTAATGACGACAAACTA
CAAACATTCACAAGAACAGATCTAACTAAATCCATGCAGAAATGTGCGGCCAGTAAAACTGTGCAACAAAAAAAAGAAAAACAATTATTTTTAGA
GCTTTGATTAAAACTTTATTACAAACATAGAACCTGAATGGGAAGACGAAAAATCTCGAATGCTTACGTATAAAATAATTTCTTTAAGAAACTAA
AATTCTTAAACAAAAAAAACATTGGTTATATAATTGCGGTGTTGGGCTAATTTAGCGACTCTTTATACAATGAAGAATAAACGAAACAATTTCTA
AAATTTTAAAATCGAAACATTATGGCAAGAGTGGAAAATTCCAAATTTTCTAAAAAACAATATTGTTGAACAATAGGAGAACATAAACCTTTATG
AATAGAGTATAATTTTTAATAAATAAAACACTTAATAAGACAACAAATACTCATTAAACAAACAGATTTAGCATACCATTATATATATAATATAT
ATATTTAATTTTTCTATGAATTGTTTGTAAAACTTTTTTGTAAATTGATGAAAAACCCCAAATTCAATGTGAAAAATATACAAATTCCATGTAAT
AAAACGCAAAAGAAACGAAAGTTGTTTGCAATAGTGAGTTGATAAATATTTTATTGATGTCTACGACTATAAGTTTTATTTTCTACACATACAGA
TATTATCATTTTATTTACTGCTTGTAAGTATTGATTTTAATTTTTTGTTATAATATTACACTATTTTTATTTCATTTTTGGAAACATTTTATTTC
GAAACACACAAATTATTGAAATATCAAAACTGGTTAGGCAATCATCGATTATAGGTACACATAAAAAAAATCTAATTTATAGTTTGAAACTTGCA
TTTAATATATGATAACTAATGAAAGCAACCCAATTACCTGACATTTTCAGATGAAGCTGGCCAGAACGAAGGTGGTGAGTCCAGGATTCGAGTCC
GTAATTGGCTAATGCTGGCTGACAAATCCATCATTGGAAAATCCTCAGACGAGCCCTCAGGTATTTTACACAACTACACTGACTACAGTTTTCTT
GTTTTATGCATAATTTGATTGATTTTGTCATTTACATATTATGGTTTTAACCTTTTTTTTGAACTTTCCAATAACTTTGTTTTCTTTTTACAGTC
TTACATATTGTTTTGTTGCTGAGCACACACAGACACATCATAAGTTTCTTACTCATTATCCAATCATTTATTGACAAGATTTACTAACTAAAACC
ATTCCCAATTTCTATTTCATGACTAACCAAACAAACAAAAAAAAAAAAAATACCGACAAACAACTAACCTTCAGACAAACTAACTCAGTCCAAAAA
ATCACTCATAAGCGATGCTAAAACCACTAACAAAACGTCGACGCCGATCCGACCAAAAGTTTCGACGACGACCACATCCACGTCCACGGCGGCGG
CTGCAGCAGCAGCAGCCACAATTGCAGCCAAGCAGGCGGCAGCTGCTATTGCCAGCAGCAACATCAACAACAATAACAGCAGTTTGACGCAAACG
GTCACTCAAACTGTGACTCGTATCGGGAGCATTGGACGCACAACCATTGCCTGCATCACGCCGGCGAACAATGGTAACAAGAGCTCGTCGAGCAA
CTGCAATGTGGATGCCGCATCGGCCGCTGCACTGGCGGCTGCCGGCGTGGAGCTGGACAGCATCGATGACACCATGACCGAGGTGATTGTAAAGA
TCGAGAATCCAGAGAGTATGCCGCTCAACGACGATGAAGACGATGCCGTTTGTAATGAGGCTATTGAGGATGAGAATACCTTCGACTATGACCTG
AAGCTGGGCAGTCCGTTGTCGTGGACCTACGATGCGGTGAAGATTGAGAATGAGGAGTTCGAGGATAGCTATCTGATGGATAACGACGATGATGA
TGATGATCTGCTGACCACAGCTGCGGCGACTCAAAAGCATGCCAAGCAATCGAATGAGAAGCAAATGGCCGGCTCTATGGTGGCTGGAGCTGGTA
GTGGAGGTGCCGTCAAGAAGATCGTGCTTAGTGCCCAGCAGCAACAGCAATTGCTCGAACAGCAGCAGCATCTGCAGCACTTGCAGCTACAGCCC
ACCAGTCAGTCGCTGCAGATTAAGTTGCCCGCCATACCAGCCACCATTACGACGATTTCGGCACCCAAGCAGATGATGTCAGGTGCGGGAACCAG
TGGCTCCCTAACCCCGAACAACAATTGCACGCTGATGAGCAACAAGCTGGGACTGCCCGTGAAGGGACAGAATCTCGATCTGCACTGGTCGCACT
CGGACGACAATCGTTATCGCGTCCTGGTCCAGAATAAGCGCACACGCAAGGAGTCGCTGGAGCACTCCGCCGATATGATCTACAATGCGGATATT
GAGAAGCCGTGGGTGTGCCGCAACTGCAATCGCACTTACAAGTGGAAGAACAGTCTTAAGTGTCATTTGAAGAACGAGTGCGGCTTGCCACCACG
CTACTTCTGCAGCAAGATGTGCGGCTATGCCACCAATGTCCACAGCAATCTGAAGCGTCACCTGAACACCAAGTGTCGTGATCGCGAGAAGGATG
CCGACGACGAGAAGAAACCCGGATCGGCCAGTGGCAACATGCCGGTGGTTGTGGGCGTTGGCAATGGGACCGCCGTTCCGGTCAGCAGCAGTAAT
AACAACAACAACGGCGGCGGCAGCAGCACCAGTAGCACCTACACCTTGGTGTTCCAGAACGATAGCGCTTAGGAGAGACTTGGACTTGTACAAAA
CGCAGGCAGCGGCTAAGATGGAAACGGCTTTGGAAACGAACATTCTGCTAGTGCAAATCTTGGTAAATCCATCGAGTTGAGTTTTATGGGCCATT
CGGAACTGTGGACCCTTCACAAATTCGTTATTTTCGTTGAACGAAGCCGGTGATGCCGTGGAAACTAGACGTAGTTTGCAATACATTGAACAAAA
AGACATGCAAAACAAATTATATTGTATTGCTTTAGCAAATTCTCACAACAAATTTAAACCTAATCTTTATAAATATGTGTAAATTTTTTTCCCAG
AAAAAAAGAAAGAAAAAAAAAAAAAACGAAACCAAACCAAACAGAAAATATATAAAACTAGTCATCAGCTAAATTTGTTTTAGGTGTGCTACAAAC
ACTACAAGAAACAAAAATAATAAAAAAAAGATGGGAAAATTTTGTAATAATATTATAATTTAAATAAAAAAAACCTTTAAACTATATGCATGGCA
TGAAGATAAAGCAAATGCCCCTCCACAGATACTTAAAGATAACAAAAATAATGATAAACTTTTTGATTTCGTATTATGTTTGCATTCGCAATAAT
TTTTATAATTTGTTAGAAACATTTTTCTGGTCACTAAGTTATGCTTATATAATAATAATTATTAACTAAAAATGATTATCTAGTCAAAACGAAAC
GATAATGAGATATAATATTTTCAATTTTAGACAAAAATTAAACCTTATTGATAAAGACAATGTTTATAAACATTAATTCGAAATATCATCAGCGC
ATGTATGCTTTGAAAATTGTTAGATTTAGTGAAAAAAAAAAAAACACGAACCACGACGAACGGCACTGAAACGCAGAAGTTGTACCATCAAATTA
CCTTACCTTACCAAATTGTAATGTAAACGAAAAAAAAATGACAAATACCTCTATGAAGTTGCAAGAGAGAATACCATTATATTGATTGAGTACGA
TTACCACTATGTATTTCCAATAAACTG
(SEQ ID NO: 1240)

Exon: 1001..1024
Exon: 1418..2827
Start ATG: 1001

Transcript No. : CT41779
ATGAAGCTGGCCAGAACGAAGGTGTCCAAAAAATCACTCATAAGCGATGCTAAAACCACTAACAAAACGTCGACGCCGATCCGACCAAAAGTTTC
GACGACGACCACATCCACGTCCACGGCGGCGGCTGCAGCAGCAGCAGCCACAATTGCAGCCAAGCAGGCGGCAGCTGCTATTGCCAGCAGCAACA
TCAACAACAATAACAGCAGTTTGACGCAAACGGTCACTCAAACTGTGACTCGTATCGGGAGCATTGGACGCACAACCATTGCCTGCATCACGCCG
GCGAACAATGGTAACAAGAGCTCGTCGAGCAACTGCAATGTGGATGCCGCATCGGCCGCTGCACTGGCGGCTGCCGGCGTGGAGCTGGACAGCAT
CGATGACACCATGACCGAGGTGATTGTAAAGATCGAGAATCCAGAGAGTATGCCGCTCAACGACGATGAAGACGATGCCGTTTGTAATGAGGCTA
TTGAGGATGAGAATACCTTCGACTATGACCTGAAGCTGGGCAGTCCGTTGTCGTGGACCTACGATGCGGTGAAGATTGAGAATGAGGAGTTCGAG
GATAGCTATCTGATGGATAACGACGATGATGATGATGATCTGCTGACCACAGCTGCGGCGACTCAAAAGCATGCCAAGCAATCGAATGAGAAGCA
AATGGCCGGCTCTATGGTGGCTGGAGCTGGTAGTGGAGGTGCCGTCAAGAAGATCGTGCTTAGTGCCCAGCAGCAACAGCAATTGCTCGAACAGC
AGCAGCATCTGCAGCACTTGCAGCTACAGCCCACCAGTCAGTCGCTGCAGATTAAGTTGCCCGCCATACCAGCCACCATTACGACGATTTCGGCA
CCCAAGCAGATGATGTCAGGTGCGGGAACCAGTGGCTCCCTAACCCCGAACAACAATTGCACGCTGATGAGCAACAAGCTGGGACTGCCCGTGAA
GGGACAGAATCTCGATCTGCACTGGTCGCACTCGGACGACAATCGTTATCGCGTCCTGGTCCAGAATAAGCGCACACGCAAGGAGTCGCTGGAGC
ACTCCGCCGATATGATCTACAATGCGGATATTGAGAAGCCGTGGGTGTGCCGCAACTGCAATCGCACTTACAAGTGGAAGAACAGTCTTAAGTGT
CATTTGAAGAACGAGTGCGGCTTGCCACCACGCTACTTCTGCAGCAAGATGTGCGGCTATGCCACCAATGTCCACAGCAATCTGAAGCGTCACCT
GAACACCAAGTGTCGTGATCGCGAGAAGGATGCCGACGACGAGAAGAAACCCGGATCGGCCAGTGGCAACATGCCGGTGGTTGTGGGCGTTGGCA
ATGGGACCGCCGTTCCGGTCAGCAGCAGTAATAACAACAACAACGGCGGCGGCAGCAGCACCAGTAGCACCTACACCTTGGTGTTCCAGAACGAT
AGCGCTTAG
(SEQ ID NO: 1241)

Start ATG: 1

MKLARTKVSKKSLISDAKTTNKTSTPIRPKVSTTTTSTSTAAAAAAAATIAAKQAAAAIASSNINNNNSSLTQTVTQTVTRIGSIGRTTIACITP
ANNGNKSSSSNCNVDAASAAALAAAGVELDSIDDTMTEVIVKIENPESMPLNDDEDDAVCNEAIEDENTFDYDLKLGSPLSWTYDAVKIENEEFE
DSYLMDNDDDDDDLLTTAAATQKHAKQSNEKQMAGSMVAGAGSGGAVKKIVLSAQQQQQLLEQQQHLQHLQLQPTSQSLQIKLPAIPATITTISA
PKQMMSGAGTSGSLTPNNNCTLMSNKLGLPVKGQNLDLHWSHSDDNRYRVLVQNKRTRKESLEHSADMIYNADIEKPWVCRNCNRTYKWKNSLKC
HLKNECGLPPRYFCSKMCGYATNVHSNLKRHLNTKCRDREKDADDEKKPGSASGNMPVVVGVGNGTAVPVSSSNNNNNGGGSSTSSTYTLVFQND
SA*
(SEQ ID NO: 1242)

Celera Sequence No. : 142000013384534
ATGTGGCCGCTCTGTTGACTATGCTGTCCGCCAGTCTCTCCAGGTCGTCCAGGCTCTGCTCGTTGATTTTCCGCTCGAAGTCGGCCATAAACTCA
TTGGTCATACGCTCAGCTAGGGGCTCCGAATAGTGCTTGCGGAATCCCCGCAGGATGCTGTCCCTTAAACAGGGCTTTATCACCACCAGATTGAG
TTTGGTGCCCTCCTTGATGTTGGGATATGACGCAATTGTCTGTTCATTGTTAAGCGGTCGCCCCAACAGCAGTAGCTTTTGATTTGTAGCCGATA
TCTGCAGTTCCGCCTCGATCTGGTGTTTCACCTCCAGAATCGTCGATGTCGGCGCCACCTGTGTGAAATATTACCATATTAGCGACCTCACTTGA
TTTTGGCAAGGTTCATTCTTACCTCGATGGTGCAGTCCTTGCCCTTCAGCACCTTGATTGTTATCTGCATAGCAATTGCCGTAAAATTTATTAAA
AAATTAAAAGTCAAACTCGAGAAGTCGAGCGATATAAACAATCTGTCTTTGGCGTTGCCACCTGTATTGCCACCAAGTGTCATTAGGCCAAGCGG
CCCTGGTTTGTAAAACAAGTGCCGCAATATTTGCTAATATATAATTTACAAAAATATTTCCTTATATTAATATATAGTACATATATATGATTCTT
GTAAATTGCCAAATGTTATTTAAAATTATTAATATTTTAATGCAGCTAGCACAAATTATGTACAAGCTATCGAAAACCACTCGAAGTTATTATTT
TACAAAATTAAAGAATAATGTGAGATCAACAATTAAATAACAGTTTGTAAACATTCGGTTTATTATAATTAATAATGATCTTTAAGTCTTTCGCA
TTTGGCAATAAGACAGTAGAGGAGAGTAAGGTATAAAGATAGTAAATATAAATAAGTAAATAGCATAAGCAAAAGCTCGTTTTAGCTTTTAAACG
GAGTCGGTAAAATCTTCCTAAAAGTAACTATCGAGGGTCGGCTGGGTCAGGCAACGCCGCCGCACGCCTGCAGCCCTGGTAACTCTATTTTCTAT
TGAGCACCGACAACGTTGCGTGTATAAGACAGTTTACATAAATTATTATTTACAATTGCACAGAGCGTTGATGTTGTGCGTTCTAAGCGAAAAGG
TGAACTTGACCCCGGTGCCGATAGACCGCCGAGCTATTGGGTGTGAAATTCGCGAGCGAGCCTTGTGGAATTCGCACGCGAAAATCGAAGCGAAT
CGCAGCGATCGAAGAAATTGCAGCGCAAATAATTCGTGTAGCCTCGACGACTGAATTTTAACGCGAGAGCGGGGTGTGCGTGTGTGTGTGTGCGC
TGTGCTGTGATTCTGTGTGCGTGTGCAAGCGTTTTTGTTAGAATTCGCATTTTACGCAAAGAACTAGCTTTTATCAGCAGTGAACTTGATGTTGG
CGAACCTATATCGCAGCAGGGCCAAATTGAACAAGTTCTTGCAGCTTCTGGCGGTAAATTGGCGAAATAAGACCCATTAAAAACCCCCCTCTGAA
AATATAACCCACAAATTAACCTCGCCCCTTGACATTCAAAGTTATATTTGTTTCCCCACTTATATATGTGCACATATATATATATAAATATATAT
ATATTTAATAATAATTGTGTGTTTGAGTCTTGGAAGTGCAACTACAACTATTAATCGTGCCTAGTACACATTTTACTTTTACGCTCTCGACTGTC
TCCGTCTCTCTCCCTCTCTGTTTCACCCCTTCCTTGCAACAACAAAACTTATGAGTACTTGCTGGGTGCCCCAACAATACTTGTGTTGATGATTG
CCCATCCTTGCACCTCCAAAAAGAAATGAAAAAAAAATTTGAAAAACACCAACACCACCCAAAAGCGCTCTTCCTTCCCCATTTCTATTGGCATG
TCTGGCAACCCTGGCAATTGGTCGACGGCCATTGCTTCTCAACTTGTTGCTCGTCTCGCTTGCTCTCCTCTCTCTCTCTACTCTCTTTTCAAGTA
CGCTCTCTCTGCGCCAGTGTTTTGGCATTTTTGTTACTTATTTTCGTTTCGAGTATAGTTTTATGCGAAATGAACAATGCCAAACAATGAAACGC
CTGAAGACCTGCATAAAGTGTTGATGCTAACATTTAAATGGGAATCCGAAATTCCACATCACCGACAACACCTGTCCACTTGGAAGTTACAGCAC
TAATCGGAGGAACGCTGCATGAACGTGTTTTCGGTACCGTTTAGAACCGGATTTTCTATGCTAGAGAATGAGAATATGATCGCGGTTCTGTGGGG
ACATCTTGTGACAACTTAGGAACTCCGATACGAAGCGGTTTTCCGCCATTAAGGCATTTCCAATTGGAAAGCGCGCAGCGAGAGATTCTTAAAGG
TTGCTCCGTTTCCCATTGGTAATGTGTTGTTTACAGTTATGGTTAAGTTAATAGCAGCGTGTTTATGTAATATATAGATAATTCGAGTTATGCAC
GTTCCACTGTACAGTGATCAAAGGGAAAAGAAACAGTATTGGAATTTCCATGAAGTTGCATAACAAATGAGGAATAGTAGTGATGAGAAGATTCG
TGGTAGATTTCAGTAAACCCTTAATTTACGTTGAGCGCCCCTCGAATGCGAATGTTAATGCGTGTGTGTGTGTGTGTGTCTGCTTGAGTGTGT
TGTTTTGTGGCTTAATTGCACGGTGTGTTGTGATGCTATTGTTATTTTTCCTTTAGTTATTGCTACGTTAATTTTTTTCTTTCGACCCTCCACAG
TGCAAATATAATTTTCAGATAGCAATCAACTGAGAGCGGTCCAGCCCGGCCTGTTGTATTTGTTTGTTTGTCCGGTTGTTTACGTTTTTTTCTCT
CGTTCTCGCTGCTTTTCATACGTATTTTATATTTTGTAAAAATAAAAAATCGTTATAAAAAACCAAAAACACACATAGAGGAGAGCACATCCAAA
GAGCCAAAAAGAGTCAGAACCGATTGCGTATTATGGATAACGAGGCGTTAGATCCAACAATAAAAAGCAGTACGTCGGCAGCGACGCCAACAGCA
GCAGCATCAGAAACGACAACAACAGCAGCATCTTCAGTTGTGGAAACCACAACAACAATCGCGGCGGCCACAGCCTCAGCGGCAGAATCAAAAAA
CGAAACAACGGCCACAAACAACAATAGCAACACAAGCGGCAGCATCAGCAGTAGTAGCAGCAACAATATAGTCATACCGGCATCGGCCACTAACG
GTATCAAAGAGAGTAACAGTAACTTAAGTACAACAACAACAGCAGCAGCAGTAGCGGCAGCAACAACTGTAGAAGGAGTAGCTCCAGCAATAACG
TCCACAATCGTGGTGACCGGCGGCACTCCTCCATTGAGCAGTTTGGTGAGTAGCTCTCCCCCAAAACACTAGCCCTCCCCACCACACTCCCTCAC
TCACTCTCTTTCTCTTGCTGTCTTTAAGCCACAGTCTCTCTCTGTTTCTGTTACGATCTCTCCCTGTCTTTCACTTGTCGCCCTATTTGCATGCC
TACCGTTATTTTGGCGTAACGTAAACCTCACTCGTAATGCTTACACGCACACTGTGCATTTGTGTGTGTGCCTAAGCCTTATCTTATCTAATCAG
TGCTAATGATGTGTGTTATTGTATCGCTGCTTCACCTTACCCCGCACGATTCAAGTTAGATTGACCAACACCAATTAGATTCACAATGTTGCCAA
TTGTTAAATGAGTGTATGTCGTTCGGATAACAAATCGAATCGTAATTGTATCGCAAGTGCTTGACAAACCGATATTCACTTTCCCCCTTTTCCTC
ATCTCCAATTTGACCAATTCGTTAGTCCTTAGAGAGATAAACTTATTAGATTTTAATTTTTTTAATTTTAAAAAATGATTTTTTAATTAATTTCA
TAAGTTTTTTTATACGAAATATGATGCATTTAATTATTTCTTTAAATAGAGGAAATACTCTTTATTTAACAAACGATATAAATAGCATTTAATGA
CCTTGTAAGTGGTAACAGTAATCTAGCAATCTTTATTGCTTTTCAATTTTGGTTTACAAATCGTTATCGTTTCAATTATATTACCTTGGGTTCTA
CTTTCTGATAAGACTTTTGCGATTGAATGAATAGATTGCCCTAAATCCTAGATTTTATACGATTTCCCGAAAGTTTTGTGTCAACAAAAGACGGA
GTTGATTATACAAATCTTTATACTCACATGCCTGTTATTAACTAGAAGAACTTTTAATGAAAATTTTTTACATTTTTGTCTCTCCAACGACAAAA
ATATTGAACATTTGCAATAAAACATAAAGTATAAGGCGAGCACTTTGCTTTTTGAAACTGCCAAAAAATTGCCCAATGAAATGCTTTAAAAAATA
CATAAATGTTAGTGCCTGGAAAATATATACATATATGCCACCACCTGATTCCCTGGTAGATGCCAGCAATATAATCCTATACGTGTATGGAGAGC
CTACGGAACTCCAGCTTCCTGATCCCAGAGCACATTTCAATGTTCGGCATTACTAAACTCAGACTAAAACACACCCACAGGCAGCTCAACTTAGG
CGTCAAGGATTCGCACAGTCCAAGGTAAAAGCGATGGCCGGCCAAAATGGCAGCGAGGGACCATCCCGAACTGAACTGCTTTGCTCTGATTTTGC
AAGTGCTACGTTTTGAGTATGCTTTTTATTTGACCGCATATTGCTTTGCATTCGTTGTTAAAATTATTTTCATTTACTAAGCATAAGCCAAACCG
TTGACATGGGAAAAGATAATCAGATAAGTGTCATTTATGCCCCTTTGCAGGCTAACAAACTCAAGGACAACACACCACCGTACGATGCACCGCCG
CCCACGCCGATCAGCAAGGTCCTGAACATCACCGGCACCCCGATCGTTCGCAAGGAGAAGCGCCAGACCAGCGCCCGGTACAATGCCTCCAAGAA
CTGCGAACTGACGGCCCTCATTCCGCTAAACGAGAGTGAGTAGCCTTGGAGTAGATCCTACTACTTAGTATATTACTTTATAATACATGTACTGC
CAGCTGTTCAGATCGATATCTCTTAAGCCTGCAGATCGGTTGCATGGGGTAGAACTTGGTCGTAGCCATGTCGTAGCATACATTTTAGGGCAGGG
TTCCGTTTAGGCGATATAAAATTACCTTTCTTACTGTCTACCAACATCGTCAATTAAGTTTTTATGCAACTATACACTCAAAACAGATTGTATAA
ATCGTAGTAATTCCCATTAACGATGCATAATTACATATATTATGTCAATTAACTCCGGTAAATTTCCATGATTATAAGTTCAGCTTTAACTTACA
AGAGGCATTCTCTGTAAAGTGTACCTACGACCTGCAAGCTTGTTGGGAATATTGATTGGCCGGCGCTTGATTAATTTCGCTCAGCTGTTGTAATT TGTTTATTATTTGTTAAAGTTAAAGGTCAAGGGAGTGTCGTCTGATTAGGTGGGTGGCAACACTGACGCACGGCCACTCACACATGTGAACCAAG
CAGCCGCATCAATTCACACCTCTCTCCACCTCTCTCACTCACCGGAATTTCAACACATGCGCTCTCTCCGCAGCCTCTCATTACACTGGGAGAAA
GCATCGTTAGAGGATTTCTCAGACCGTCTTAAATTTCATATATACACCGGCATTTCTTTATGACACAAATGTATTCGATTGATTTAAACTTGTGT
ATACAAATAATTAGAAAAACTGTATCCTGCAGGGAATTAATTTAAAAAAAAGCAAATTCAATATTTTTGAAAATCATATATGTACATATCTGCGC
GTAATGATTATGAAATTGCTACACTTTTTTTTTCTGTGCAGCATGAATGTCATCGCATTGCGTTATTCACATACCTTTCTGCTAATTGCTTGGGC
GGTTTCGACTCACAAATCGAATAAACAAATTTCGCTTGTTCAATACTATTTTATTTTATTAGGTTTTATTGTTATTGTGGCTCGCTCGCCCAC
(SEQ ID NO: 1243)

Exon: 1001..1139
Exon: 2756..3370
Exon: 4801..4983
Start ATG: 2978

Transcript No. : CT42545
GCAACGCCGCCGCACGCCTGCAGCCCTGGTAACTCTATTTTCTATTGAGCACCGACAACGTTGCGTGTATAAGACAGTTTACATAAATTATTATT
TACAATTGCACAGAGCGTTGATGTTGTGCGTTCTAAGCGAAAAGTGCAAATATAATTTTCAGATAGCAATCAACTGAGAGCGGTCCAGCCCGGCC
TGTTGTATTTGTTTGTTTGTCCGGTTGTTTACGTTTTTTTCTCTCGTTCTCGCTGCTTTTCATACGTATTTTATATTTTGTAAAAATAAAAAATC
GTTATAAAAAACCAAAAACACACATAGAGGAGAGCACATCCAAAGAGCCAAAAAGAGTCAGAACCGATTGCGTATTATGGATAACGAGGCGTTAG
ATCCAACAATAAAAAGCAGTACGTCGGCAGCGACGCCAACAGCAGCAGCATCAGAAACGACAACAACAGCAGCATCTTCAGTTGTGGAAACCACA
ACAACAATCGCGGCGGCCACAGCCTCAGCGGCAGAATCAAAAAACGAAACAACGGCCACAAACAACAATAGCAACACAAGCGGCAGCATCAGCAG
TAGTAGCAGCAACAATATAGTCATACCGGCATCGGCCACTAACGGTATCAAAGAGAGTAACAGTAACTTAAGTACAACAACAACAGCAGCAGCAG
TAGCGGCAGCAACAACTGTAGAAGGAGTAGCTCCAGCAATAACGTCCACAATCGTGGTGACCGGCGGCACTCCTCCATTGAGCAGTTTGGCTAAC
AAACTCAAGGACAACACACCACCGTACGATGCACCGCCGCCCACGCCGATCAGCAAGGTCCTGAACATCACCGGCACCCCGATCGTTCGCAAGGA
GAAGCGCCAGACCAGCGCCCGGTACAATGCCTCCAAGAACTGCGAACTGACGGCCCTCATTCCGCTAAACGAGAGTGAGTAG
(SEQ ID NO: 1244)

Start ATG: 362

MDNEALDPTIKSSTSAATPTAAASETTTTAASSVVETTTTIAAATASAAESKNETTATNNNSNTSGSISSSSSNNIVIPASATNGIKESNSNLST
TTTAAAVAAATTVEGVAPAITSTIVVTGGTPPLSSLANKLKDNTPPYDAPPPTPISKVLNITGTPIVRKEKRQTSARYNASKNCELTALIPLNES
E*
(SEQ ID NO: 1245)

Name: ---

Celera Sequence No. : 142000013384684
ACCCAGGCCGGAGGCTCCACGCATCCCGCTGCCAGTGCCAATTGCCACGGTTACGGGAAGCCGGACGCTTATCCCACTTTCCGGATACGATTGCC
TAGCAGATCTGCCGTCCGTACATATTGAACAGACCTTTGAGCTTAACGATGGTAAGTACAAGCCCAAAAATTAGCTAAAATCGCTTCTAATAGTT
CGTCTTCCCTTTGCAGCCCTAACAGGCGTCTCCTCGGAGAATCGATATGTGGTGCGATCTCCACTGGGTGATGCCATTTTCGCGGCCAACGAGAG
TTCCACAGAAAAAAATCGACTACTTTGGGGAGCTGGTCGACCCTTTCAGATGCACCTGCTGGATAAAACGCACCAGGAAGCTCTGGTTTTTCGCA
AAAAACTAGCGATGGGATCCATGTGCTGCCAGGCAAAAAGTCTAGAAATTTGGATACCACCTGGTAATTTGCTGGGTAAAGTGGTGCAGTCGCCC
ACCTTCATGCAGCCGGAGTTCTTTATCGAAGACGAAAGCACAGGACAACTAACATTCTGTGTAGAGGGTCCTGTCGGTTTAGGATTCTGCTGCTT
CAGTTTGCCCAAAGATTGTTATTTTAAGGTTGGTAGTAGCTTTAACATTCGGAACAGAATATTCAATTATAGTGTTTTTGTTCCCTTACAGATCC
ATTCGGGAGGCAATATGAGGGCTTCCATAGACCACAAATGGCTCGCCAGCAAGTCTCAGTACACCACAAATATATACTTTAGTGACGCCAAGCTA
ACCGCCAAGGAGCGGGCTTTGATACTGGGATCAGCCTTTCTACTGGTACTGTGCTCCTAGTTTATATACATATATCATTTGCCACAATAATGTTT
TGTATTCGTTTTTCAGGAATATCTATTCTTCCAAACCCGCTTTTGACGTGATTAATCAATAAAAAAAAACATTGTATATTCACATTGATTTCTTT
ATTTTTTGTCATTTTTTTGTATAAGATTTTATGTTTGTTTGTGTTTTGTTTTTTTTTTTTCTCAGTTTTTTGATATATTTTACAATAATGTAATA
GATCACTTCATTTTCTTGTTGTTTAACCACATACACACATTCAAATATATAGATATATATCTATGTGTATATATAGATTTTGCTGCAGCGCTTGC
CATAGCAGTTTGTACAATATTTCATTTATATCTATCAACTTTGTGTAGTTTGTTTATCTAACCTACCGCTTAATGCATATATGACAACATATTGA
TTATTTACAGTTAGCGTTTTTTTCATCATTTCGTTTCTCTTCTGTCAAATACAAAATTAAAAGAAACAATTAAATGAGTCTCGTGGTCTCGTTG
TTTAAAGAATTAAAACAAAACTAGGGGCGCAAGTCATTTCTCATTCACCGTTAATAGTTGCGCTTCAAAACTTGGTGTGATAACAATTTGAAATA
AGGAAGAACTACGTGATTTTCAAAGGGCAAAACTTGGATTTGGACATAGAAAACCAATATACTTAGTGTGCGGGTGTGTTCTGGTTCGGTTTGGA
GGTTCATTTTCGGGGCTAGGCCTTAAAAATAACACACTTCTCTCGCTCTCGGATCTTTACATTTGTAGATAGACTCACAGCACTTCAGGAGTTTT
TGCATTTATGCATTTCGAAAACAAATTATGGTTAAGTGTATACAATATAGATAGATTTATAAGTGTGCTCGTTGGTTGGCTTATAACTAGGGCTA
GCTGATGACGATTCCTTAACCTAAATACTTAAGAGGCAGATCGAAACGATCTGTGTGGGGTGACTGCCTTTTAAAACCGTAAAAGGCTTTGTATA
TGATTATTTTAGCGCAATTCGCCTAGAGTGTTTACACTGGAATAGCTGACTCGCTTATCTGGCTCCCCTATCGTTTGATTACTACTCGCGATTAG
CCCAATACTAGTTGGGCCCATCATCGAAGAGAGGTGGGTCTTATAGGCTAGCTCTAGAGTAAGTTGTGTGTGTGCCCATATGCGATATGCTTAGA
CATTTGATATGCGCTCGTTGGAGGTGGTTTGGTCATGGCGGCCCTCGATCCTGGAATTGTAGATGCCGTACTGACTGCTGTCCAGGTGGTAGACC
GCGGGATACTGATAACCTCAGCTGGGCTGCAGCATGTACATGTACTGTCAGTTGCTTGCCGCTGCTGAAGCAGCCACGGGAACGGCCACGGGAAC
AGGCAGCTCCTGGCCAGAACGAGCCCGCTTCTCGCCACTGCTTTCCGGTGGATTATCGCTCTCCTCGCCCGTACTGCTGAAACTGCCCGGCAAAC
GACGCTTCAGGCTATGGTTTAGGCCATTGGCCACCGTTTCATCCTCGGACATCGAGCTGGCTCGCTTGGGTGTGTTGCCAGCACTGTCGTTGTCC
AGCGAAGCTATAGCCGAGGCAATTGCGGCACTAAAGCCATCCTCGGACGCACTATCCTGCGAGACGGGACCTGCTGCATCCTGGGCCAGCTGCAT
CATGCCAGAAGGTGTGGTATAGCTACTGAGCTTACCAGGATCCTTCTCCTGCAGTTTCTGGGCCAGCAACTTGAGTGATATCAGCGAATTTTCAC
AGTCGCTTGTATCGATTTCAGTGAGACTAATTCCGGCACGTTCAATTTCAGCATAGGTCCCGAAGGGCAACTTCTGCAGACACTCTAGCTTCTGA
ACATGCGTCTTGGAGCGCAAATGCTTGGCCAAATGCCCATGGATGCGGAAGGCGATCTTGCAGTCGGTGCACTCGAAGGGTCGCGGATTTGAGGT
GGTTGGAACACCAAAAGTCGACGTCATCATAACCTTGTTTTTGTGCGCTTCCGATCGCTCGTGCTTCTGCAGATGTCCTTGCGTGCGGAAGGATA
TGCTGCATGGCTCGCACTTAAACTTTCGCTCCATGTAATGAATATTCATGTGCAGGGTCAGCTGATGTTGCCGCTGAAACGTCTTGGAGCACATG
GTGCAGGTGGGACGTGCATCACCTGCAATGGGAGCTGGCGGCACTCCTCTGCCATACGATACATGCTGGAGATCGCCGCTCTTGCTAGTGGGAGT
AGAGCTTTTGAAGCCATCTTCACCCACAATCACAGTACGCTGCGCGGGCTGAGTTGAGTTGGCAGTGGATGAGGGTGCCACAGGTGCAGCTGTTG
TTGTGCTTACTGAAGTAGCAGTAACAGACGATGTTGGTGGTGCAGTCGGATTTCCAAGTACTCCAGTAAATTCATTGACATCCGGTTGCTGCACT GCAGCAGGCAGATTGGCATTGTGTGGCTCTGCGATATTAGGCTCCTCGTTTTCTTCCTGGGCAATCTGAGCAAGAATAACCGGGGCCTGTTCAGG
TGCACTCCGAGGTGACTCAATGGCCTCTGGGGTCTTTACTTCGTGCACTTCGATGCTAGGTACCTCATTTACGCTCATAACGGGCCTGCTGTTGG
CGGTAAAGAGAGTGCTACTACTGCTCATTACAGGAGACGCCGCTGTGTATAATGTGTTGATCAGATAGCTGCGGCTAAACTGACTCTGCTTTATC
TTGGCTTGATGCAGCGCATGCTCCTTAATGTAGGTCTGTAGTTGAACATCCTCGCCCTCGGCCTCGTGCTTGGCCTGCTCTTCCATTTCGGCAGA
TATTCGCACTTTGTCCGAAACCGAGATTAGAGTCTTCATGAAACCGCTTTCGTTGCCGGAGGTTCCAAAGATAACATCGTGCATCTGTTGGGCCT
GCGATTTGGGAAGATCATGAGCGGGCACCGAAACAGGCGAGGGGGATATTAATAAGATGGAGCCGCGTGGCTTAGTGAGATCCATGGGAGCACTC
TCCTCGTTGGCCACACTCCGTTTCGGTTTGGACTCCTCCGGATTGGAGTAATACTGTTCCTGCTTTTGGTAGTCGAAAGGCGGCTTCGGCGATGT
AAAGGAGCACACTAATCTTTTAGGTTGCGAACCCGAAGAGCCAATGCTGTTTGCAGGACTGGCCGCTGGTAGGGGTGTATCCTGCAACTGCGGAT
AGGGCGATACGCTCTGCGGTATGGGCGGCGTCATTGATAACGAGAGTAGGCCTCTGGCTGCTTCGTGCTCTTTCTGTCGCGACTTGGACTCATCC
GTATCTGTGAAGAGATTATAATGAATCAGCTATTTGAACATATAAGTGTATATGATTGCTTTCTTACCACTACTTTCAGATTCATTATCACTGTA
GTCATCGGAATCCGATTCCCCAGCCATCGATGATGTGCGTCCTCCTGCCGAAGTGGATGACTGCTGGTCAAAGTCCATATCTACATCCAAGAACT
CGCTGTCTGGCGGCATTGGTCCCGGATTTATTCCCAGTTCAATGCACTTCTTAAAGTGAGTTTTCGATTGCATATGCTTGGTCAGATTTCCCTTG
GTCTTAAAACTGTGGAATGGAACAAAGTTTATAATAAGTTATCTCTTAAGTACGGAAAAAATGCAATGACTCACCTGAAGTTGCAATGGCTGCAT
GTGAATGGCCTCACGTCCGTGTGAGTGCGAATGTGCTTCTTGAGCATCGACGGCTTCTTGCAACGAATTCCGCACTCGGAGCAAACATATCTTCC
CCTTCCGCGGCCACGGATGTACGTGTAATCCTCATGAGACTCGTAGCCACCCACCAGGGGCTGCCCGGATGGACTTGTCTCCAACTTTTTGGCCT
GTGCCTCCTCATTCGCCTTGGCCGCCACATTTGCCTCACTGAGAGCGGCAATCGTGACAGTGGGTGGGGTCTTTAGGGGTCCTTGATAGAAAGCA
CTGCTAGTGGAGGACGTCGAGGGGGAGGATACGATTTGCTGGGAAGCGACTAAGTTGTAGCTAAGTTTTCCCGATCCAGCCATGGCGGTTGAGCT
GCCATTTCCTAACATCCTTTGACGTGAGTCGTAGAGTGCCATAACTTGCTTTAGTTTGAATCCAAGTGGATGTGGCTGGTTCTCCTCGCAAACCT
GCCACACACTATACATCGATAGTTTGTGCATTCCTGCCACATACGAAGGCTGTGGACAGTTCACCGTACAGTAAAACATCTTTGTGCTGCATTTG
AGGCCCAGATATGTGTAGGCGTGTCCATTGAGATACAGTTGCACACAGGATTTGGACGGCCTGGGGGTCTCCGGCGAGATCAGCGGCAATGTATT
GGCTGTCGGTGTAATGCCATGATGGCGTTTAGGAGTAAAAGTACCGGGTTTAAGTGGCAAACTAGTAGGCCGCAGAAACTTGGACTTCGCCGATG
CTGAGGCACTGGCTACGGGACTGGTCTCTTCTGGAGCGTTTCCGTTGGGAGTATCAACATGTAGCGGTGTTAGGGGCAACTCTTGCTGTTTCCCA
GAAATCACATTTTCCAAATTAAAGTGTCGAACTTCAGGTTCAGTGGTCTTCACATTATCAGCCATGCGTAGAAAGTTAAATGGTGCTTTCTTCGG
TGCCTCCTTGCTGTTCCACTGCAGCGCTTGCCGCTGGGCAGGAGTTGGTGGCTGTCGACTGAACTCGCTTGGCACATTCTGAACTCCACCGAATG
GCGATAGGGCCTTCAGTTCACCGGATCCTCCTCCCAACAGCAGCGGACTGGGTTGCTTTCGATTTGGACTGCGACCTCGACTAGAGGGAATGGGT
AGCTGCAGCTGTTGTGGCGGAGGCGGCAGTAGCGGCATTTGTGGTGTCAGACTACCGGGTCCTGGCATTCCAGGCACATGAGGTATTGGTGTTAC
TGGAGTGGTTTTATCTCCACCGCTCATCGGTGGCAGCGTTAGCGGATTGAAGGCAGTTATTGAGTTAATGGGCGGAAATTGAAAGTGCTGCGGAC
CTGAGCTAACGCCGAGAAGTCCACTGCCACTGACCAGTGCCATCAGCTTGCGCTCCTTACTGGATGATCCTGTTTCGTTGTTGACTTTGACCGAA
ACATCCTGGAAGCTTCCGCCGGACAGCAACGGTGTTCTAATCATCTTGGGGCTGTTGTCCAAGTCTGGGCACTCCGAAATGGGAATCATGCTGCC
TCCCGAAGAGGTGAATCTGCGCAGTCGCTCCTCCTTGGAGGACTGCAATTCCGGCACACTATTACTGCTATTCTGATTATTAAAGGAAAAGTTGA
AACTTGTCGGTTGCTGAGAGGAGGATGCTACAACCAAATCGCTAGTCTTGATGCGTTTGGCAGGCTGAGCTTCAATCACAAATTGCCGATCCTCG
TGCATTTTGGTTATGACCACAGAATCCTGGGCCTTGCGTGGTGTACTTTGCTGAGCATAGTCCACTAAGGGAGTTTTTCCCAACAATGGACCAGG
CGATGGTAGAGGCGCATCCACAAAGCGCAGTGCTTCAATCTGGGGGGCAGGTGCTGATGATGGAGCAGTGACCGTAGCAACAGCAGGAGCTGGGG
CAGAAGCGGTTACAGTGGGAGCTGTTACAGTTGATGTCCTTGCTGGCGTCTGTGCTGCACTTAGGCGACTTAATACCAAACTGCTCCTTTTGGTC
TTCAACTGCGACCAGGCCAACTTGGCCAGAGATAAGGGATTCTTCGAGTTGGCCATGTGGCTCTTCAGCTCCGGTAGACTCAGCGAGATCGAGTT
GGAGCGGAATGGCGAAGATGCTGGACTCATTGGGGCACTTGAGCTCGCATCCTGACAGTAAGTGCTGTTGTGCAGCTTCAAATCGTCCGCACTGC
GGAATTCGCTTGCACAGATAGGACACGAATAAACAGCATCATCGCCTTCGCCAATCGGCACGGCCAATCCTCGAGCATTAAGCAGTAGGTTCTTA
ATTATCGAGTTATTAACCTGAGCAGGTGGTGGAGCAGTTTTGGAGCTACTAGTCGGATTGGTAGAAGTCGTTGGAGTCGGTGCCAGAGAACTGGT
GGACAAGGAACTGACGGGCACAGTGACCAGAGTTGGTTTAGGCTTCGCTGATAGATTCAGAGGCATAACAGGCACTGCCGTCGTCGGTTGCTCAA
TTTTCGTCACTGGTGTTGCAGGATCCTGGCGATATTGCATTGTTTGCATGGGCAACGGGGACGGCGGTGGAGGAAGTTGCTGCTGTTGCTTCACC
GGCGTAGTCATCACTACTCCAGGCTTATAGGCATTCCTTTTAACCACCCCATTTGGTGGTTCGAGCTGTTGCTGTTGGCATTCCTGTTGCTGTTG
GATGTACGTATAGTAGTTCTGTTGCTCGAGCTGCTGCTGCTGCTGGGTTATCTGCTGCTGTTGCTGTTGCTGAAGCTGATGTTGCTGTTTCT
GGAAGATGGCCTGTGCCAAATTCACTTTAGTCTCGCGCTCCGGCATCTGTGCGTTGGTGTTGTTTTGACTATTGTTTGCATGCAATGCCGACGCG
TTGCTCCCGTGCTGCGAAGCATTATTGCTGTTGGCATTGTTGAAACTGCGGGAACGACTAAGCTGTTTGGGGTACTTCTTCTGCAACAATATCTC
CTTGTTTTCAACTATGGCTTCATTTTGAGAGATCAACTTGGAAATGTGTTCCTGCACTTTCGCCACATTCTGAAAAGGATAACACAAATTTTAGT
TTAGTTTTTCTGTAAAAATAAACTTTTAGTGCAACACTCACTACTTGCTTGCCACCACTTGAGCTGGCAAAAGTGCTGAGATTGGCGGCGGGCGT
GGGAGTGGCTGGTGCTGTTGCTACACTGGAAATCTGGCTATTGGCACGCACCAACTGTAAACAATAAAGGTATATAGATTATAATTAATCTCCTC
GTTCAAAAACAATCGTTCTTAACCAACCTGTTGCGGCGGGAGACTCGGAGGTTGTTGCATTGGTGGTGTCGCCTTGACCAACGGTGGGTGTTGCT
GCTGCTGTTGTTGCTGCTGCTGTGCCAGGTGGATTTGGAATTGCTGAATGGCTAACGCATGCTGGTGAATGGCAGCCGCTGTATCTTGGTTGTAG
TATGAAGGTTGCCCCAGGTAATACACCCCGCCAGGTGGCATGGCAGCTAGCAATGATTGCTGGGCCAAAAGGGATTGCTGCTGCTGCAATTGCAA
CTGGATCTGATGCGAGTTAATGTGGTGCTTCATCTTCATTTGCGTGCTTGGCGAAAGCGTGGGATGCGCCAGTGACGGCTGCTGAACCAGAGGAA
GCTGAATGGACAGCTTTTGCTGCGCCAATTGGTGTTGCTGTTGCTGTTGCTGTATCTGCAGTTGCTGCTGCTGCTGTTGCAGCTCCTTACTGCTA
CATGAGTACAACGAGGCATTGTGGAACTTGGGCTTATATGGCTTATAGTCGATCGACTGGCGATGCTGGGCAGTGGCCGAGTGGTGATTGTCCGC
TGTGGTGGGTGGCAATGTTCCTGCTGCCGGCGAGCCCAGAGGCAATTGCTGCATGTAAGTGGGCAGCGGAGGCTGTTGAATGTATGCGCTCTTGG
CCGCAGACAGTGTGGAAGGTGAGGGTGTGGGCGAATTGATTGGCTCCTCGTAAGGCGAACCAGCGCGACTCGGCTGCAAAAACGTAAGGAGTTAC
ACATGTTTGCGATAACAATCACAGTTATATTTGACTTACCAACTCTGAACTACTGTTGCTCAGCTCTGCATCCTGATCGGATAAACCATCGTCCG
CATCGGCTGGCACTTCCAGGCCCCGCGCTCTTGCCGCATGCGATCTCGAGCGGCAATGTTTGTACAAATTACTCTTCGTCTTAAACGCAATGCCG
CACGTGTCGCACGGATACGGCCGTTCGTTCGTGTGGGCCCGTATGTGCTTCTCCAGCACCGAGGGCTTGGCACAGATCAAGTTACAGTACTGACA
AACGTATCGTCCGGACTTCTCGCATGCAGGATTTGGCGCTGCTGCTCCGCCTGGAATACCAGGACTCACTGTTGTTGGCTGCGTCAATTGCTGAT
GCTGGGCAAATGAAGCCGGTGACAGTGTGGCATTTGCTGCATGGTTACTGTTGCTGTTGCTGGTGCTGTTCGTGTTACTGTTGCTGTTGGCTAGA
GGCGTTCGCGTTCTTCCCGCCGCTTTGTAGCCACTATTGCTGATGATGCTCTCCTCATGACCAATGGCATTGACATGATTGCTATTTACAAAATT
GGCACTGAATTCATGTATTGCTACTGAAGGCGGCGGCGTCTGTTGCTGCTGCTGCTGCTGCACTTGCTGGTGGCTTTGTTGTTGGGTCATCA
GATGGTGACCGTTGGCCAGCGGCGTTGTTGGTGGCGGTGAAAGCGAACTGTTTGAGGAGAGCGATGTGGTGCGAACGGCATCGCCACTTGCTTGC
AGTGCTCCGCCGCCATTCGTCGCACTCCAGCTGTCCACCTCGGTGGTGCTGGCCAAACGTTTGAACTTCTTGTGCAGATAGCGTGAAATATTTGA
CCGATCCCCCAACGGAGCCTCATCGGTGGCGGGTGTGGCATTTACGGTGGTCTGCTGGCTGTTGATGATGCTCGAGTTGCTCATCGTGTTGGCCA
CATTGGGAGCCACTGGCTCCTGGTTGCTGCTGACTGCTGCCATCTGTTGTAGCGTCATTTTGCTATCACTTAGACTTGCTTTATCTCTACTCTTA
AATTCATAATTATTCTCACTAATACTATTATCACTGTGGTGGTTGTTGTTGTTATTATTACTTGTGTTGTTATTGTTATTATTATTATTGTTGTT
GCTGATGATGTGGTTGCTGTCAACAGTCGGCAGCGGCACCTCGCCTAGCTTATCTCGTGTGCTTGTGCTGGGTTTGCTGCTGCTGTTGCTGTTGC
CACTAGCAGCATCTGTTGTTGCTGCTGCTGTTGCTGCCGCTTTAGAAGCTGTTAATGTTGCATCTGTTGCTGTTGCTGTTGCAGATGCTGATGCT
GATGCTGTTGCCTCTGTTGCTGCTGCCAATGCAATTGCTGCAGCGATGTTGGCCTTGTTGGTTGATCTCTGAGTGACTATGGTTGCTGTTGCAGT
TTCCCGATATGTCCGCTTCTTGGTTGGCGTTGCTGCTGTTGTTACTGTTGTGGTTGCTGCTGCTGCTGCTGCTGCTGCCGCTGCTGCTGTGGCAC

FIGURE SHEET 668

GTCGCGTATTGTTCACTTTATTGGTCTTGTACTGTTTGCCTGCGGTTTTGTAATGCTTGGCCGTTGTGGTGGTTGCATTTTCCATATTATTATCG
AATTTATTATCCTGTGACGTATTTGCAGTGGGCTCATCTATACCGAAACGAGAAGATAGAGGGAGAGGGAGAGAGAAAACCGAAATTAATTCAAT
GTGTTTCGCATAATTTAATTTAAATAGCAATGCTAATTGATACATTCATGATAAGCCCATTTATATACACTGATATCCCTGCTAGGTAATCCAGT
AGAAATCAACCACATCTGACTTTGTGGATTTGCAAATCTTCGGACGATTAAATATTTAATATTAGTTTCTAATACACCCTTGTCCCCTATAAGTC
CTCACATGATTAGTGAGAGGTTTGGTTTTATCTTTTATATGTTAATTGCGCTGTTATGTTACTGTTACTGCATTGTATTGATTCATCGCTTCTAA
ATAAATAAATATATAAAAAAAAAAAACCCTTGTCCCCTGGCCAATAAACATCTGCGGTTTGCATTTGGGTTTCCCAAGACGAGTTCCCTGCCCAT
ATAGTACACTTTTATTTCGAGCCCCATTATCAGCACTAATTCGGGCTCAATCTTATCAACGCGTAGCCGAGAATGCCAGATACGGAGCACGCTAA
TTCTCTCCATGGCGATCAATCCGTCAGGTGAATCACAAGCTGGCGAATTCCCGTGCTCTATTGAAAATCAATTTCCCACTCTGTGAACGTGTCAA
CATCGATAAAGCACAGTGGCGAAAATATACGAACACACACAAATGTATATTCGCCTTGTTTCTTTTTATCAACTTTCTATTTTGAATTCCCAACT
TAGCTGGGGTTCAGGCCCCACCTGCCGAAAACCAGACATGCGACCAAAAGATACAAAAATCCAAGAAAAGTGACAAGTGAAGTGTAATGACTGGT
GTCGCTGGCATTTCGTTTGTTGTTGGGGGCTTCCTTATCACCGCTCGTGCACACATGTGTGACAACAGTGCGTATCAGTACTGTAAAGCTGCTGG
CAGGTGTGTGATTAGCAATGGGATTATAAAGCGTTGCCAAATATGAAGAGTGAGTATTTGAGAACTCCATTTGCTCGCATTAATTAAGGCTTCAG
TTTGAAAAACAATTTAGGCAGTCTTTGGTAAATTCTTTGTTTTGTGCATGCCAAACGAAACGAAAAGCTGCAAAAATCTTTTAAAAATTTTTCAC
TTTTGCTGCTATTTATGTGAGCCCCACTGTCTGCATAGATGGTATTATATGACTCTTGGCCGGCTGGGCTGTCGGGCGATTAGTAAGCCGGGGCA
GTTCTCAAATCACAATCGCACACAGACTGAACACAAAAAACGCTCACTGGCAACCGAGCTGGGTCGCGTTAATTGACTCGACTGCGGCGACTGTT
TAGCATTCAGCGTTATTATTATACACATTATACGGCATTATGCGATCGCAGCGACTCTCGTCGCGTACCAATGTTTACTCAATTTGTTATCAGCA
CGGCTGGCTAATAAGGCTTTCAAACCGTGCGACCGCAAAAAAAAAAATAAATAAATAAAAAAAAAAATGAAAAAAATTGCCCAAAAGTTCCATTGA
TAATGCCAAGCTCTACATGCACAGGCGGTAAGGTAAGTATTTTCGGTACGTGTGTTTGCCAGATTCATTATCAGTTATCAGTGGGGACTATCGTG
CGCGCCTGAGTCAGAAACAGAGCACCCGATAAGCGAGCCCCGTTGTAAGCCACCAAGTGATTGCCAATTTGCCGGAGTTCAGACGCGTTGACGTC
AGTTATCCGATACGTAGTACTATTCGTTCGCAATCGTAAGGGGCTATATCAGATTGTCAACTCATTGGGCAATTAAGTGGCATTCGCTGGCGATT
AGCTGTTCGAGGATACAAATCCTAATTACATAATCATGTGTAGTAAATATGTGTATGCACTCGACTTATTAATAAAACGAGTGAGTGGGTCAATT
ACAAGGCGCCAACTGCGCCACAATTGAAATGCATACATATGTGTGGCGATTACACGGAATGTGTTGTTTCTTGCTAGTGAAAACAAAAGCGGAGC
AGACAGTGTGTGTGAGCATTTTGACTAAATAAGTAGAATAAAGTTTAATAACACAACGCCCAGAATCTGTCTTTCGAAATAATATTTACATTTGT
GTTCATTCGCTGTGCGAGAAACTATTGAAGTTCAACTGTACATAATGACAAAGTGGGCTATACATTCATTATACAGCAGAAACTGGCGAAACTAA
TGCCATCATCTACAGTCACGACAGTATAATAAAGTCAAGCGGGAATAAAGAAGATAAGCTAATCAGAAGTAGGCGCTTATAAAAACGCCAGCAAT
TAAAACCAGAATACTCATATGCAAGATACCCCGCCACCCAATGTGCAAACAATTAGCGCAAAGTGCACAGTGACGTTTAAAGATCCCAAGTTCGT
TTATCCACCATTTAGTTTATTGTTAGCCACGTAAATCCAATTGTCAGAGTCATCAATATCAATACGACGTTTTCATTATCACGAACTTTTGTTTA
ACGATCGGGGGTCTTCTAATTACGCCTGTTTGCCAGCATTTTGAGGCGTGAAAACGGCAAGTGAACGCGAAACACATGGGAACGTATTTCAATAT
ATGTGAACAAACTGGAACTGCATTTGCATTGGCATTTTCATTTGCATGCACATTTTTATTGAGCCAAGCGAAATACAATTGCCCCTGTTCAAAGT
GCACATAAATAAAGCGCCACGGCAAATAATCGAATAGGGTTCGGTACACTCTTACAAATATCTAAAAATTGGTTGCAATTAGTAGTTCTTCTAAC
CAGTAAATAAACACACAATCTTAGATTTTAAACACCAACTTCCGCGCCAAACTTCATGAATATCTAAGATACATAAATAAATCACTTCTTATTAA
ATCATATTTACATTTGTTCAGAGAGTTTGTTTTTCGAAGCATATGGAAATGCTGGCATTGTTTCTGTGTAGAAAAGCTTGATAAGTTTGCAGCTC
ATATTGAGCACACGCTATCTCGCCTACGTCACAAGTGCATTTCGCGTTTGACTGAGTGACTGCCTGAATTCGAAATTATAATAAAACCAAAAAAA
AAACGAGAATACATATAAAAACACCCACACCAGCGCAGCGAAATAATGAAAAATAAATAACAAAATCAACGAGGTGCGGCGGCAACGGCGCCACA
AAGTCCACACATCTGTCTGACGGTCAGTCTGTCAGTCCGTCACTCTGTCAATCGGTCATTCGCTCAATCCGCGCGATGACGACTACGTCATCGCA
GAGCAAAAAGCACTAAGCACTCGCCCACTTGGCAATTGTTTATAATTTATTAGTAAGAAGCGTTTTACAGCGGTTGAGCAGAACGAACGAAAAAT
GCATATGTAATAGTATAATACGTCAAAAAAAATTCGCGGAAAAGATTCCGAAATTCCAGCGAACGGCCAAAATGCGAAATGCCCGACAAAAATGA
CGAAAACGGCACAAACGGTAAAGAGAAACATACCCAAGTTTAATTGTGACCACACGCATTTTTCCGCCTGTACCGCTCATTTGCATAGTTGGTGT
TGTTGTTCGTTTGGTTTGAAGCGCAACAATTGGAAGTGCACGGCGAGAAAAATCTGGCGGCGCGAATAGCAAGAAATCGAAAAGGCGACAATCGA
CAATCGACGACAACCGACGCGCCTGAAACATTTAAGGCAACTAGACGAGGCGACCAGCGAAATTCATTCAGAGTGTGCTCAGCGTGTGTGCTTGT
GTGTGCATGTGTGTGGTGTGTGCGAAAAGAAAACGAAGAAGCGACCGAACGAAGCAAAAACAACAAGTAAGAAGCCCAAAGTCGCACTAGTCGAC
TACAATGTACCCTTGAGTGGCAGTAAAAGTTATTCTTACTACAAATTACGTATAATTAGTAGGAATAGGCTAAACGTTTTGGCATTCTGCGATTT
TGAGTTGAGCATAACGAAAATATCAGTTCAGAAAATAAGTATATATTAGGAAAGTTGAAGTCTTCATGCCCGAAAAGGTTTTATAGGGCAGTCTA
TATCCCAGAATATTCGGTAGTAGCTCCAATAGATCATAAGCTTATTAATTTTTCTCATATTGAAAATACATCTGTATTCAAATAAAGATAGGTGG
AAAGATTTCTTGCTATAGCGTTTTTTGGTAAATCTATTAATTGGTATAATATTAAGAAGTTGTTTTGTAATATCTTTACTTATTTTAAAAATGCC
ATATACCCATGTTTTCATTCAGTTACTGAGTGTTAAAGAGGCGCGACGTCAGCGCAGGCAGCAAAAAAAGTACAATAATCAAATAATTGCGGCAG
CTTCGTCGTCGCCCCCCGCACACTCACACACAAACACACACATGTGCTCTCAATCTCCTCTCCACTCATTCGCAATTGTCAATCAAATGTAAGCA
CAGGGTCGCCACTTCTTTTTGTTCAGCTTTTGATTTTGCGGCAGCCACTGAGAAATGATCAAATCAAGCAAAAATTAAGACTCAAAAAAAAGTAT
AAAAATTAAACAACAACAGGTGACGCGAAGTACGAAGCGAAATGAAACGAAACGATTCGAAATGAAAGACTGTCGCCAGCCAGTCAGACGTTGCT
GTTGTTGCTGCAGTTGTTGTTATTTCCCCCTATTGTTGATTACGTACCCCATACACACACACTCACACACAAGTGCGCTCCGTAAAACACGCGCA
CGCACACCAACAAACGACCCCATCGGCGACCACATTCCCCCGCACAAATATGCGAAATTTTGCTGACTAAGGAAGGTCTGGGGAGCACCAGGCAG
AAAAAAACAGCAAAAAGCAAAAAGAGGCTAAAAAGCACAACGCGATAACAACAAAAGCATTTAAAACGTAGAAGCACAAAACGAAGCAACGGAAA
AAGTGATAATAAAATAATAATTGCTACAGCGCACACCGATCGCGCGCTCGAGAGAGAGAGAGCAGGCCAGAGTTGCCATATTAGCTGCGAGAGAG
AAACCCCATCAGCAACCCCCACTCCATCCCCAATCTACTAATTCAGCACGATCTGCCCAACTGTGTATCACCTTAACTTGTTTATAGCTGACCTT
TTTTTTTTGTAAGTCAGTTAGGACTATCGTAAGAGATATAATTTAGAGCATATAATGTCATGCTTTAAGAAGGAAGTCTGGTTTTGTACAATTCG
AACGCTGAATATACACACATTAACAGTAAGCTTTTATTTACTAGACGGCATCGCTTTAATTATCTACAGGTATTCTTAGCTTTTTTTAGATCTGG
CTACTTTTCCATGGCTGCATCACTGTCTGCCATGTGGCGACGAAGCCCCACAGCCAGAGCCAGTGCTCCCCCGCTCCCCGCTCCATACCTCTAGC
GGTTCGCTCGCGAACATGACTAAGCCAAACAACTTGACAACACTGTCGGGAATTGTTGCTGCTTTTGAGTCAATTCATAAGAAACGAGGAAACCC
GCCGCCATATCGTTGTTGCTGCCGTATTTATTTACGTACATATGCCTGTGTATATATGCATGTGAGATTGTTGGTGTGCTGGCATGAGCATGAAT
CAAGTTAAAAATTTAATAATTTTGCCCGATGTTGTGGTTGAAAACGAGTTTAGCTTGTTGAGCTTGAGTGTGTGTGTATGTATTTCAGTGCGGC
TACTTGTTTTCTTCAGTCCTCTTCTTCTTCTTCCTAGTCGTCGTCTTCTCTTCTTCTTGCTCCAGCTTGGACACTGCGATAATATTTTACACTCA
TGCACACATACATTTACACTACGACGAACAGAAGAGCTTGATAAGCGCTTTGTGCGCCATCTCCCTCTTTGGTAATTGAAAGGCAAGGGGAAAGG
GTAGGCGGCTGTGACGTACCCGTGTCTCACTGTTATTGTTGTTGCCCACTCAGCCGTGCTGAAGTGTTATAGGAAATCAAATTAAGGCGATTAAA
GAGCGAGTGCATGCGCTCTCGAACGAAAAAAAAGAGAGAGAGAGTGACGATCGCTCTTGACGGAAGATAGAAGATGACTACTTAAGTGGGGCATT
CGTGAAGATTGATACCCTACGATGATAATTACTGTTTGCCTACAAAAAGCTTTTTTACTTTGATGTCTTGTCAACTTTAACATACAGATGGAATA
GTTATGCTTTATCTTTTTGACCAAAACATACTTTGAAACAAAAAGGAAAGTTTATAAGATGTGTTTCTTTTTAAATTTTTTCCTTTTAAATTGCA
CACAAACGACGTACATATGAGAAGCAAATGTTTAATATTAAACTGTTTAATGAATTTAACTATTTATGACCCATAAATAGTCAACCCATAGTGTC
CAAGAACTGATAAGAACAAAGACATCTTGCCTTTGAGCAGAACTTTGCCATTTGCTGATAAGTTTGAAAGCGATGCGAGCCAAGTCGGTATACAG
TTTCATTTATTTATTATTTATTTAAAATGGGTTTCCAATGCAGAATATTGAAATAAACAAGCACAACGCCAAACGGTTGATATATTATGGGGAAT
TGCGAAAACAGTTCTCGAAAAGTGCTCTGACGTCGATCACTTGACTAATCTGGCGTTCTTTTCGAGAAATAAATTTCGATTACGGAGGCTTATCA
ATCGACGGGCCGTGGACTCTTTTGTGGAAAGTGAAAGGTCAAGGTACGCTTACGGAAATTGGTAAATAGATAAGACATTTCGATGGAATATTTGT

FIGURE SHEET 669

TGGGTCTATAAGCCTCTTTGCAGGAGATCTATTTCGTTTATCTATCGTCGAATGAGTAAGCAATATATTAAGCGATTTGGCGTACACAACCAAAT
TCTCGGCACATTATACACTTTTCACATTAGCACGGAAATTCCCAAATTTTCTTTGACGTCAGCAGAGAAAATTTGTAAAATTTCTCGAGAGTAAA
AATCATGTTCTTTTCGTACTGAAATGTTTTCCGATTGCCAAGGTCTCTGGGTTTACATGTATGTAGGTGAAAATCTGTATAAACAAAATTGATTT
TTGGCACAGCAAAACAAAACAGTTTAAACAATATAATTTAGCACTTTTTAGACATTCCTCTATAGATTTATGGACTATTAAAATATATCTAATTT
AATAAAGGTGCCTAAAGGAAAAGCTTAAAAACTTAGCAAAAACGAATAAATTTTCCAGATTCATAATCATATATTTTCGAATATTATTATGATTA
TTGCTTGGGGGCACGATAATCGTAAATATGATATGAGTTCAAAGTAAATATCGAATTATTTCCTTCTCCGTATTGCGAAATTGGTAAGAGAACCC
CTTTAAATATAGGAATTCGTGGCCAAAAGTGTTAAATAATTGCCAGGCCAACAATTTTTTGTTTACACACAAAGCGAAGCGAAACACAGCAGAAG
ATCAAGAAAAGCAGACAGAAATCGTTCGATAATTTGTGTTTATTTTTATTTTCCCACTGTCTTTGACTTTTGACTTTGCTCTGCTGGCTGATAGA
ATGTGATTTTCTCCATTTTCTTGATTTTCTTGATTTTCAATTTTGTTTTGGTGCCGCCGCCTCGCTAGAAAAGTATTTTTAAATGCTCCAACTAC
GTAAGACGACATTCAAGTGTTTTATTTTAGACAGTAGACGGTATAGAGCCAACTAGTCGGCTATATATACACACATTGGCGTCTATATATCTGCA
TAAATATTTTTAGTTGCCTCTATTGGCCTTTTGCGTTAGCACATTTTTGTTAAATATTATCTATTTGTATTTGCCTTTATGACAGCAAAATGGAA
AACTCGAAACACTTCGATTACGCAATTTGGCGCAGCCCATAACGATCATAATTCAATTTCGCCCCCCCATAAAACGAATCTTGAAACATTCTCGA
TATTTCAAACTTTATGGCGCCGCAAAAGCAAAGGCTGGTGCTTTTTTTTTATCTAATGTCACGTTATTTCGTATATTTCTTATTTCGTGGTCTAA
TTAAATTAAACTGTTTATAAATACTTCTGCTCTATCAAAGGCCACCAAAGCAAACGATTAAAGAAAAGAATCTCCAAATCGTGCATTTGAGAGCA
AACCAAAAAATGTTTCCCAGCGCCAAGCCATCAAAATAAAAATTTTCACAAATTGTGTGCGTTGTTCTTTCTTGAAATTTTTTTTCTTTTCTTTTC
GTTTTTTTCTTTCTTCTTCTTTCTGCTTGTCTTGGCGTTTTGGCATTTGAAGGACGGAAATACGTTGGCGGCGTTGTGAATTTTTGCATATTAGC
AAAAAGTGAGAAAAAAGAAATAGCCATAAATACACAAAAATTTTGATAAATTCAAAGCGCTTACGTAGGCAAACTCATGGGGCTATGCGAATGAT
TCGCTTCGATTCAATTCGATTCGATTCGATTCGAATCGAGCCGATGAAATGTATGCACAGGCATGCGCATTGGCCGTGAAAAAAAATGGTAACAG
ATTTCCAGACGCGCACCGAAAGTATCTGTATCTGTATCGGTATCTGTGTCTGTGGCTGTGGCTGTGAGTGCGGAGTATCTGTTGCTCTGTAGCTC
TGTTGTCAAGGTCATGACTGCTCTTTAGGGGTTGCCCCGTCGATAAACATGTGTCGTCATTCCCCAGGCGGCAGGGCATTCCTCAAAACTCACAA
GCGGCACACAGGCAGCAAAGGCGGAACGTATTATAACTGTTGCATGTTTAATTGTTCGCAAAACACTTGAGAGCAGCAGTCTTAAGACCCTGAGA
TATGTACGTGTACAGTGAAACTCCGCCATGGGAAACATCAAGCTGAAGTACTGACAATCTGATTTTTTAAGTGATTGTATTTTTAATATATAGTT
TAAAAAGATCGATAAATGCTTAATTCGACTCCTAATTTTTTCACGCTACTTTATATCCTAGTTTTAGATACATCCCGCAGAATCTTTAGTTTCTA
AAGATTTCAAAGAGCAAATGTTTAAGTTCGGGTCGTAACTTGCAACAAATTGGTGTCATGCTAGAAGTTTCCACTGTGGCAGCAGGAACAGCAAC
AGCAACAGCGATTTCGGCTGAACGCCCCGTGGTGCAGTCTTAAGTGGATTTCCACCTTAAGTTGCATTAGTATCGATGTTGTTGCTGCTCACGTT
GCACATCGATGTGGTTGTTGTTGCTGCTGCTGCCGCCGCTGCTGGCGTGTCAATGACGTTGCAAGCCTTTTGTTTGTCTTTCTACCTAGCCAGGT
ATCCTGGCGCCGGCTTAATTTACGAAAAGGTAAAGGTAAACGGCAGGTAAAACGCCTCAAAGTAGTTCAAGTCCAATCAGCATGCTCTCCCGCTC
CCGCACGCACACCAACCAATGCACCTTTTTACCCACACCAATGCAGAGATTATCCATCCACTCACCCGCACACGTTGCTCTTCTTGTTGCTGTAG
AAACTAACACTAATACTAATCTGAGAGATATTGCGGCCCGGCCGCGCGGGGTTGCCCAGATTTAAGTGTTGTTTTTGTGTTGCTTCTCCTTCGGT
ATTGTATTCTCTTGTGAGTGGGACGGGGGGTTGGGGGGATCGCTCTTTCGACTTTTGTTTATTTCGAATTTTCACAGTTTTTCTTGGAATTCCTT
CCACACTCGCTTGCTCACTCGCACGCACTTACTCACTCGCTCTCTTTTCTATTTCCTTTACTTTTTAAGAGAGATACTTTGAAATTTGCACTTTG
ATTCCGTGCGTGTTTTCGTATACTATTTTTGCACCGTAGCTAATTAGCATATTATGACATTCATTTCGCTGTAACCTTTTCCTCTTCGTGGCTCT
TGCCGTGCACTCTTTTGCGCGCTATGATCTAATTTGATTAATACAAAACTTGTTGTGGCGGCTGCACTCGCACTTCTCGCCCACACACACTATTA
TACACAAACATGCATGCACACACAAGTATGCTGAGCAGAAACATACGCGCGATTGTTCCGTTCTTTTGTGGTTTCTTTTCTGCCTTTTGTTTATG
TTGTGCTGCGTTGTTGTTTATTCCGACTTCGTTCGAATTAATTCATCGCACCGCCGAAAAATTAATTAATAGCCACCGCCGCACCGAACAAGCGAAC
AACCGCACCGAACGACGAAAGATCGAAGAATGGCGCGCCTCGACTGTTTTTTTCGCCGTCGACGCTGGCAGCGACGCGGGCAGCGCAGCAGGCAG
CGACGCTTAACCCTTGTGTAGACTTTCGAAGAGCTGCAAAGTGCAGGTGCCAACTCTCAGTTGATCTTGATCATAAAGTTATAGATCTAACGCGG
TTATCATGATTTAGTTTATTTAATTTTCGTATCTATATACGCATTGCTTAAAAGTTTAGTTTTATTATTAAAATATGATATTTTTACATTCAGAT
GAGATGTTTTTCCAGTTTTATTATTGAAGCTAAGACGATATGTTATCAACACCATTTAAGACATTCCCTATTACCATTTATTTAATCTTTATGAC
ATTGCCAGGAGTGGAAATACTAATTATTATTTTATCCGTACCCTAACCCTGAACCAGTCGA
(SEQ ID NO: 1246)

Exon: 19486..19351
Exon: 10107..8495
Exon: 8433..7723
Exon: 7654..7547
Exon: 7479..4445
Exon: 4379..4153
Exon: 4089..1001
Start ATG: 10060 (Reverse strand: CAT)

Transcript No. : CT42591
GAGAATACAATACCGAAGGAGAAGCAACACAAAAACAACACTTAAATCTGGGCAACCCCGCGCGGCCGGGCCGCAATATCTCTCAGATTAGTATT
AGTGTTAGTTTCTACAGCAACAAGAAGAGCAACGTGTGCGGATGAGCCCACTGCAAATACGTCACAGGATAATAAATTCGATAATAATATGGAAA
ATGCAACCACCACAACGGCCAAGCATTACAAAACCGCAGGCAAACAGTACAAGACCAATAAAGTGAACAATACGCGACGTGCCACAGCAGCAGCG
GCAGCAGCAGCAGCAGCAGCAGCAACCACAACAGTAACAACAGCAGCAACGCCAACCAAGAAGCGGACATATCGGGAAACTGCAACAGCAACCAT
AGTCACTCAGAGATCAACCAACAAGGCCAACATCGCTGCAGCAATTGCATTGGCAGCAGCAACAGAGGCAACAGCATCAGCATCAGCATCTGCAA
CAGCAACAGCAACAGATGCAACATTAACAGCTTCTAAAGCGGCAGCAACAGCAGCAGCAACAACAGATGCTGCTAGTGGCAACAGCAACAGCAGC
AGCAAACCCAGCACAAGCACACGAGATAAGCTAGGCGAGGTGCCGCTGCCGACTGTTGACAGCAACCACATCATCAGCAACAACAATAATAATAA
TAACAATAACAACAACAAGTAATAATAACAACCACCACAGTGATAATAGTATTAGTGAGAATAATTATGAATTTAAGAGTAGAGATAAAG
CAAGTCTAAGTGATAGCAAAATGACGCTACAACAGATGGCAGCAGTCAGCAGCAACCAGGAGCCAGTGGCTCCCAATGTGGCCAACACGATGAGC
AACTCGAGCATCATCAACAGCCAGCAGACCACCGTAAATGCCACACCCGCCACCGATGAGGCTCCGTTGGGGGATCGGTCAAATATTTCACGCTA
TCTGCACAAGAAGTTCAAACGTTTGGCCAGCACCACCGAGGTGGACAGCTGGAGTGCGACGAATGGCGGCGGAGCACTGCAAGCAAGTGGCGATG
CCGTTCGCACCACATCGCTCTCCTCAAACAGTTCGCTTTCACCGCCACCAACAACGCCGCTGGCCAACGGTCACCATCTGATGACCCAACAACAA
AGCCACCAGCAAGTGCAGCAGCAGCAGCAGCAGCAACAGACGCCGCCGCCCTTCAGTAGCAATACATGAATTCAGTGCCAATTTTGTAAATAGCAA
TCATGTCAATGCCATTGGTCATGAGGAGAGCATCATCAGCAATAGTGGCTACAAAGCGGCGGGAAGAACGCGAACGCCTCTAGCCAACAGCAACA
GTAACACGAACAGCACCAGCAACAGCAACAGTAACCATGCAGCAAATGCCACACTGTCACCGGCTTCATTTGCCCAGCATCAGCAATTGACGCAG
CCAACAACAGTGAGTCCTGGTATTCCAGGCGGAGCAGCAGCGCCAAATCCTGCATGCGAGAAGTCCGGACGATACGTTTGTCAGTACTGTAACTT
GATCTGTGCCAAGCCCTCGGTGCTGGAGAAGCACATACGGGCCCACACGAACGAACGGCCGTATCCGTGCGACACGTGCGGCATTGCGTTTAAGA
CGAAGAGTAATTTGTACAAACATTGCCGCTCGAGATCGCATGCGGCAAGAGCGCGGGGCCTGGAAGTGCCAGCCGATGCGGACGATGGTTTATCC
GATCAGGATGCAGAGCTGAGCAACAGTAGTTCAGAGTTGCCGAGTCGCGCTGGTTCGCCTTACGAGGAGCCAATCAATTCGCCCACACCCTCACC TTCCACACTGTCTGCGGCCAAGAGCGCATACATTCAACAGCCTCCGCTGCCCACTTACATGCAGCAATTGCCTCTGGGCTCGCCGGCAGCAGGAA
CATTGCCACCCACCACAGCGGACAATCACCACTCGGCCACTGCCCAGCATCGCCAGTCGATCGACTATAAGCCATATAAGCCCAAGTTCCACAAT
GCCTCGTTGTACTCATGTAGCAGTAAGGAGCTGCAACAGCAGCAGCAGCAACTGCAGATACAGCAACAGCAACAGCAACACCAATTGGCGCAGCA
AAAGCTGTCCATTCAGCTTCCTCTGGTTCAGCAGCCGTCACTGGCGCATCCCACGCTTTCGCCAAGCACGCAAATGAAGATGAAGCACCACATTA
ACTCGCATCAGATCCAGTTGCAATTGCAGCAGCAGCAATCCCTTTTGGCCCAGCAATCATTGCTAGCTGCCATGCCACCTGGCGGGGTGTATTAC
CTGGGGCAACCTTCATACTACAACCAAGATACAGCGGCTGCCATTCACCAGCATGCGTTAGCCATTCAGCAATTCCAAATCCACCTGGCACAGCA
GCAGCAACAACAGCAGCAGCAACACCCACCGTTGGTCAAGGCGACACCACCAATGCAACAACCTCCGAGTCTCCCGCCGCAACAGTTGGTGCGTG
CCAATAGCCAGATTTCCAGTGTAGCAACAGCACCAGCCACTCCCACGCCCGCCGCCAATCTCAGCACTTTTGCCAGCTCAAGTGGTGGCAAGCAA
GTAAATGTGGCGAAAGTGCAGGAACACATTTCCAAGTTGATCTCTCAAAATGAAGCCATAGTTGAAAACAAGGAGATATTGTTGCAGAAGAAGTA
CCCCAAACAGCTTAGTCGTTCCCGCAGTTTCAACAATGCCAACAGCAATAATGCTTCGCAGCACGGGAGCAACGCGTCGGCATTGCATGCAAACA
ATAGTCAAAACAACACCAACGCACAGATGCCGGAGCGCGAGACTAAAGTGAATTTGGCACAGGCCATCTTCCAGAAACAGCAACATCAGCTTCAG
CAACAGCAACAGCAGCAGATAACCCAGCAGCAGCAGCAGCAGCTCGAGCAACAGAACTACTATACGTACATCCAACAGCAACAGGAATGCCAACA
GCAACAGCTCGAACCACCAAATGGGGTGGTTAAAAGGAATGCCTATAAGCCTGGAGTAGTGATGACTACGCCGGTGAAGCAACAGCAGCAACTTC
CTCCACCGCCGTCCCCGTTGCCCATGCAAACAATGCAATATCGCCAGGATCCTGCAACACCAGTGACGAAAATTGAGCAACCGACGACGGCAGTG
CCTGTTATGCCTCTGAATCTATCAGCGAAGCCTAAACCAACTCTGGTCACTGTGCCCGTCAGTTCCTTGTCCACCAGTTCTCTGGCACCGACTCC
AACGACTTCTACCAATCCGACTAGTAGCTCCAAAACTGCTCCACCACCTGCTCAGGTTAATAACTCGATAATTAAGAACCTACTGCTTAATGCTC
GAGGATTGGCCGTGCCGATTGGCGAAGGCGATGATGCTGTTTATTCGTGTCCTATCTGTGCAAGCGAATTCCGCAGTGCGGACGATTTGAAGCTG
CACAACAGCACTTACTGTCAGGATGCGAGCTCAAGTGCCCCAATGAGTCCAGCATCTTCGCCATTCCGCTCCAACTCGATCTCGCTGAGTCTACC
GGAGCTGAAGAGCCACATGGCCAACTCGAAGAATCCCTTATCTCTGGCCAAGTTGGCCTGGTCGCAGTTGAAGACCAAAAGGAGCAGTTTGGTAT
TAAGTCGCCTAAGTGCAGCACAGACGCCAGCAAGGACATCAACTGTAACAGCTCCCACTGTAACCGCTTCTGCCCCAGCTCCTGCTGTTGCTACG
GTCACTGCTCCATCATCAGCACCTGCCCCCCAGATTGAAGCACTGCGCTTTGTGGATGCGCCTCTACCATCGCCTGGTCCATTGTTGGGAAAAAC
TCCCTTAGTGGACTATGCTCAGCAAAGTACACCACGCAAGGCCCAGGATTCTGTGGTCATAACCAAAATGCACGAGGATCGGCAATTTGTGATTG
AAGCTCAGCCTGCCAAACGCATCAAGACTAGCGATTTGGTTGTAGCATCCTCCTCTCAGCAACCGACAAGTTTCAACTTTTCCTTTAATAATCAG
AATAGCAGTAATAGTGTGCCGGAATTGCAGTCCTCCAAGGAGGAGCGACTGCGCAGATTCACCTCTTCGGGAGGCAGCATGATTCCCATTTCGGA
GTGCCCAGACTTGGACAACAGCCCCAAGATGATTAGAACACCGTTGCTGTCCGGCGGAAGCTTCCAGGATGTTTCGGTCAAAGTCAACAACGAAA
CAGGATCATCCAGTAAGGAGCGCAAGCTGATGGCACTGGTCAGTGGCAGTGGACTTCTCGGCGTTAGCTCAGGTCCGCAGCACTTTCAATTTCCG
CCCATTAACTCAATAACTGCCTTCAATCCGCTAACGCTGCCACCGATGAGCGGTGGAGATAAAACCACTCCAGTAACACCAATACCTCATGTGCC
TGGAATGCCAGGACCCGGTAGTCTGACACCACAAATGCCGCTACTGCCGCCTCCGCCACAACAGCTGCAGCTACCCATTCCCTCTAGTCGAGGTC
GCAGTCCAAATCGAAAGCAACCCAGTCCGCTGCTGTTGGGAGGAGGATCCGGTGAACTGAAGGCCCTATCGCCATTCGGTGGAGTTCAGAATGTG
CCAAGCGAGTTCAGTCGACAGCCACCAACTCCTGCCCAGCGGCAAGCGCTGCAGTGGAACAGCAAGGAGGCACCGAAGAAAGCACCATTTAACTT
TCTACGCATGGCTGATAATGTGAAGACCACTGAACCTGAAGTTCGACACTTTAATTTGGAAAATGTGATTTCTGGGAAACAGCAAGAGTTGCCCC
TAACACCGCTACATGTTGATACTCCCAACGGAAACGCTCCAGAAGAGACCAGTCCCGTAGCCAGTGCCTCAGCATCGGCGAAGTCCAAGTTTCTG
CGGCCTACTAGTTTGCCACTTAAACCCGGTACTTTTACTCCTAAACGCCATCATGGCATTACACCGACAGCCAATACATTGCCGCTGATCTCGCC
GGAGACCCCCAGGCCGTCCAAATCCTGTGTGCAACTGTATCTCAATGGACACGCCTACACATATCTGGGCCTCAAATGCAGCACAAAGATGTTTT
ACTGTACGGTGAACTGTCCACAGCCTTCGTATGTGGCAGGAATGCACAAACTATCGATGTATAGTGTGTGGCAGGTTTGCGAGGAGAACCAGCCA
CATCCACTTGGATTCAAACTAAAGCAAGTTATGGCACTCTACGACTCACGTCAAAGGATGTTAGGAAATGGCAGCTCAACCGCCATGGCTGGATC
GGGAAAACTTAGCTACAACTTAGTCGCTTCCCAGCAAATCGTATCCTCCCCCTCGACGTCCTCCACTAGCAGTGCTTTCTATCAAGGACCCCTAA
AGACCCCACCCACTGTCACGATTGCCGCTCTCAGTGAGGCAAATGTGGCGGCCAAGGCGAATGAGGAGGCACAGGCCAAAAAGTTGGAGACAAGT
CCATCCGGGCAGCCCCTGGTGGGTGGCTACGAGTCTCATGAGGATTACACGTACATCCGTGGCCGCGGAAGGGGAAGATATGTTTGCTCCGAGTG
CGGAATTCGTTGCAAGAAGCCGTCGATGCTCAAGAAGCACATTCGCACTCACACGGACGTGAGGCCATTCACATGCAGCCATTGCAACTTCAGTT
TTAAGACCAAGGGAAATCTGACCAAGCATATGCAATCGAAAACTCACTTTAAGAAGTGCATTGAACTGGGAATAAATCCGGGACCAATGCCGCCA
GACAGCGAGTTCTTGGATGTAGATATGGACTTTGACCAGCAGTCATCCACTTCGGCAGGAGGACGCACATCATCGATGGCTGGGGAATCGGATTC
CGATGACTACAGTGATAATGAATCTGAAAGTAGTGATACGGATGAGTCCAAGTCGCGACAGAAAGAGCACGAAGCAGCCAGAGGCCTACTCTCGT
TATCAATGACGCCGCCCATACCGCAGAGCGTATCGCCCTATCCGCAGTTGCAGGATACACCCCTACCAGCGGCCAGTCCTGCAAACAGCATTGGC
TCTTCGGGTTCGCAACCTAAAAGATTAGTGTGCTCCTTTACATCGCCGAAGCCGCCTTTCGACTACCAAAAGCAGGAACAGTATTACTCCAATCC
GGAGGAGTCCAAACCGAAACGGAGTGTGGCCAACGAGGAGAGTGCTCCCATGGATCTCACTAAGCCACGCGGCTCCATCTTATTAATATCCCCCT
CGCCTGTTTCGGTGCCCGCTCATGATCTTCCCAAATCGCAGGCCCAACAGATGCACGATGTTATCTTTGGAACCTCCGGCAACGAAAGCGGTTTC
ATGAAGACTCTAATCTCGGTTTCGGACAAAGTGCGAATATCTGCCGAAATGGAAGAGCAGGCCAAGCACGAGGCCGAGGGCGAGGATGTTCAACT
ACAGACCTACATTAAGGAGCATGCGCTGCATCAAGCCAAGATAAAGCAGAGTCAGTTTAGCCGCAGCTATCTGATCAACACATTATACACAGCGG
CGTCTCCTGTAATGAGCAGTAGTAGCACTCTCTTTACCGCCAACAGCAGGCCCGTTATGAGCGTAAATGAGGTACCTAGCATCGAAGTGCACGAA
GTAAAGACCCCAGAGGCCATTGAGTCACCTCGGAGTGCACCTGAACAGGCCCCGGTTATTCTTGCTCAGATTGCCCAGGAAGAAAACGAGGAGCC
TAATATCGCAGAGCCACACAATGCCAATCTGCCTGCTGCAGTGCAGCAACCGGATGTCAATGAATTTACTGGAGTACTTGGAAATCCGACTGCAC
CACCAACATCGTCTGTTACTGCTACTTCAGTAAGCACAACAACAGCTGCACCTGTGGCACCCTCATCCACTGCCAACTCAACTCAGCCCGCGCAG
CGTACTGTGATTGTGGGTGAAGATGGCTTCAAAAGCTCTACTCCCACTAGCAAGAGCGGCGATCTCCAGCATGTATCGTATGGCAGAGGAGTGCC
GCCAGCTCCCATTGCAGGTGATGCACGTCCCACCTGCACCATGTGCTCCAAGACGTTTCAGCGGCAACATCAGCTGACCCTGCACATGAATATTC
ATTACATGGAGCGAAAGTTTAAGTGCGAGCCATGCAGCATATCCTTCCGCACGCAAGGACATCTGCAGAAGCACGAGCGATCGGAAGCGCACAAA
AACAAGGTTATGATGACGTCGACTTTTGGTGTTCCAACCACCTCAAATCCGCGACCCTTCGAGTGCACCGACTGCAAGATCGCCTTCCGCATCCA
TGGGCATTTGGCCAAGCATTTGCGCTCCAAGACGCATGTTCAGAAGCTAGAGTGTCTGCAGAAGTTGCCCTTCGGGACCTATGCTGAAATTGAAC
GTGCCGGAATTAGTCTCACTGAAATCGATACAAGCGACTGTGAAAATTCGCTGATATCACTCAAGTTGCTGGCCCAGAAACTGCAGGAGAAGGAT
CCTGGTAAGCTCAGTAGCTATACCACACCTTCTGGCATGATGCAGCTGGCCCAGGATGCAGCAGGTCCCGTCTCGCAGGATAGTGCGTCCGAGGA
TGGCTTTAGTGCCGCAATTGCCTCGGCTATAGCTTCGCTGGACAACGACAGTGCTGGCAACACACCCAAGCGAGCCAGCTCGATGTCCGAGGATG
AAACGGTGGCCAATGGCCTAAACCATAGCCTGAAGCGTCGTTTGCCGGGCAGTTTCAGCAGTACGGGCGAGGAGAGCGATAATCCACCGGAAAGC
AGTGGCGAGAAGCGGGCTCGTTCTGGCCAGGAGCTGCCTGTTCCCGTGGCCGTTCCCGTGGCTGCTTCAGCAGCGGCAAGCAACTGACAGTACAT
GTACATGCTGCAGCCCAGCTGAGGTTATCAGTATCCCGCGGTCTACCACCTGGACAGCAGTCAGTACGGCATCTACAATTCCAGGATCGAGGGCC
GCCATGACCAAACCACCTCCAACGAGCGCATATCAAATGTCTAAGCATATCGCATATGGGCACACACACAACTTACTCTAGAGCTAGCCTATAAG
ACCCACCTCTCTTCGATGATGGGCCCAACTAGTATTGGGCTAATCGCGAGTAGTAATCAAACGATAGGGGAGCCAGATAAGCGAGTCAGCTATTC
CAGTGTAAACACTCTAGGCGAATTGCGCTAAAATAATCATATACAAAGCCTTTTACGGTTTTAAAAGGCAGTCACCCCACACAGATCGTTTCGAT
CTGCCTCTTAAGTATTTAGGTTAAGGAATCGTCATCAGCTAGCCCTAGTTATAAGCCAACCAACGAGCACACTTATAAATCTATCTATATTGTAT
ACACTTAACCATAATTTGTTTTCGAAATGCATAAATGCAAAAACTCCTGAAGTGCTGTGAGTCTATCTACAAATGTAAAGATCCGAGAGCGAGAG
AAGTGTGTTATTTTTAAGGCCTAGCCCCGAAAATGAACCTCCAAACCGAACCAGAACACACCCGCACACTAAGTATATTGGTTTTCTATGTCCAA
ATCCAAGTTTTGCCCTTTGAAAATCACGTAGTTCTTCCTTATTTCAAATTGTTATCACACCAAGTTTTGAAGCGCAACTATTAACGGTGAATGAG

FIGURE SHEET 671

AAATGACTTGCGCCCCTAGTTTTGTTTTAATTCTTTAAACAACGAGACCACGAGACTCATTTAATTGTTTCTTTTAATTTTGTATTTGACAGAAG
AGAAACGAAATGATGAAAAAAAACGCTAACTGTAAATAATCAATATGTTGTCATATATGCATTAAGCGGTAGGTTAGATAAACAAACTACACAAA
GTTGATAGATATAAATGAAATATTGTACAAACTGCTATGGCAAGCGCTGCAGCAAAATCTATATATACACATAGATATATATCTATATATTTGAA
TGTGTGTATGTGGTTAAACAACAAGAAAATGAAGTGATCTATTACATTATTGTAAAATATATCAAAAAACTGAGAAAAAAAAAA
(SEQ ID NO: 1247)

Start ATG: 184 (Reverse strand: CAT)

MENATTTTAKHYKTAGKQYKTNKVNNTRRATAAAAAAAAAAAATTTVTTAATPTKKRTYRETATATIVTQRSTNKANIAAAIALAAATEATASASA
SATATATDATLTASKAAATAAATTDAASGNSNSSSKPSTSTRDKLGEVPLPTVDSNHIISNNNNNNNNNNTSNNNNNNHHSDNSISENNYEFKSR
DKASLSDSKMTLQQMAAVSSNQEPVAPNVANTMSNSSIINSQQTTVNATPATDEAPLGDRSNISRYLHKKFKRLASTTEVDSWSATNGGGALQAS
GDAVRTTSLSSNSSLSPPPTTPLANGHHLMTQQQSHQQVQQQQQQQQTPPPSVAIHEFSANFVNSNHVNAIGHEESIISNSGYKAAGRTRTPLAN
SNSNTNSTSNSNSNHAANATLSPASFAQHQQLTQPTTVSPGIPGGAAAPNPACEKSGRYVCQYCNLICAKPSVLEKHIRAHTNERPYPCDTCGIA
FKTKSNLYKHCRSRSHAARARGLEVPADADDGLSDQDAELSNSSSELPSRAGSPYEEPINSPTPSPSTLSAAKSAYIQQPPLPTYMQQLPLGSPA
AGTLPPTTADNHHSATAQHRQSIDYKPYKPKFHNASLYSCSSKELQQQQQLQIQQQQQQHQLAQQKLSIQLPLVQQPSLAHPTLSPSTQMKMKH
HINSHQIQLQLQQQQSLLAQQSLLAAMPPGGVYYLGQPSYYNQDTAAAIHQHALAIQQFQIHLAQQQQQQQQQHPPLVKATPPMQQPPSLPPQQL
VRANSQISSVATAPATPTPAANLSTFASSSGGKQVNVAKVQEHISKLISQNEAIVENKEILLQKKYPKQLSRSRSFNNANSNNASQHGSNASALH
ANNSQNNTNAQMPERETKVNLAQAIFQKQQHQLQQQQQQQITQQQQQQLEQQNYYTYIQQQQECQQQQLEPPNGVVKRNAYKPGVVMTTPVKQQQ
QLPPPPSPLPMQTMQYRQDPATPVTKIEQPTTAVPVMPLNLSAKPKPTLVTVPVSSLSTSSLAPTPTTSTNPTSSSKTAPPPAQVNNSIIKNLLL
NARGLAVPIGEGDDAVYSCPICASEFRSADDLKLHNSTYCQDASSSAPMSPASSPFRSNSISLSLPELKSHMANSKNPLSLAKLAWSQLKTKRSS
LVLSRLSAAQTPARTSTVTAPTVTASAPAPAVATVTAPSSAPAPQIEALRFVDAPLPSPGPLLGKTPLVDYAQQSTPRKAQDSVVITKMHEDRQF
VIEAQPAKRIKTSDLVVASSSQQPTSFNFSFNNQNSSNSVPELQSSKEERLRRFTSSGGSMIPISECPDLDNSPKMIRTPLLSGGSFQDVSVKVN
NETGSSSKERKLMALVSGSGLLGVSSGPQHFQFPPINSITAFNPLTLPPMSGGDKTTPVTPIPHVPGMPGPGSLTPQMPLLPPPPQQLQLPIPSS
RGRSPNRKQPSPLLLGGGSGELKALSPFGGVQNVPSEFSRQPPTPAQRQALQWNSKEAPKKAPFNFLRMADNVKTTEPEVRHFNLENVISGKQQE
LPLTPLHVDTPNGNAPEETSPVASASASAKSKFLRPTSLPLKPGTFTPKRHHGITPTANTLPLISPETPRPSKSCVQLYLNGHAYTYLGLKCSTK
MFYCTVNCPQPSYVAGMHKLSMYSVWQVCEENQPHPLGFKLKQVMALYDSRQRMLGNGSSTAMAGSGKLSYNLVASQQIVSSPSTSSTSSAFYQG
PLKTPPTVTIAALSEANVAAKANEEAQAKKLETSPSGQPLVGGYESHEDYTYIRGRGRGRYVCSECGIRCKKPSMLKKHIRTHTDVRPFTCSHCN
FSFKTKGNLTKHMQSKTHFKKCIELGINPGPMPPDSEFLDVDMDFDQQSSTSAGGRTSSMAGESDSDDYSDNESESSDTDESKSRQKEHEAARGL
LSLSMTPPIPQSVSPYPQLQDTPLPAASPANSIGSSGSQPKRLVCSFTSPKPPFDYQKQEQYYSNPEESKPKRSVANEESAPMDLTKPRGSILLI
SPSPVSVPAHDLPKSQAQQMHDVIFGTSGNESGFMKTLISVSDKVRISAEMEEQAKHEAEGEDVQLQTYIKEHALHQAKIKQSQFSRSYLINTLY
TAASPVMSSSSTLFTANSRPVMSVNEVPSIEVHEVKTPEAIESPRSAPEQAPVILAQIAQEENEEPNIAEPHNANLPAAVQQPDVNEFTGVLGNP
TAPPTSSVTATSVSTTTAAPVAPSSTANSTQPAQRTVIVGEDGFKSSTPTSKSGDLQHVSYGRGVPPAPIAGDARPTCTMCSKTFQRQHQLTLHM
NIHYMERKFKCEPCSISFRTQGHLQKHERSEAHKNKVMMTSTFGVPTTSNPRPFECTDCKIAFRIHGHLAKHLRSKTHVQKLECLQKLPFGTYAE
IERAGISLTEIDTSDCENSLISLKLLAQKLQEKDPGKLSSYTTPSGMMQLAQDAAGPVSQDSASEDGFSAAIASAIASLDNDSAGNTPKRASSMS
EDETVANGLNHSLKRRLPGSFSSTGEESDNPPESSGEKRARSGQELPVPVAVPVAASAAASN*
(SEQ ID NO: 1248)

Name: schnurri
Classification: transcription_factor
Gene Symbol: shn
FlyBase ID: FBgn0003396

Celera Sequence No. : 142000013384567
TTTACGTGTTCTCATAAGATATAGTTTATATTAATGTATATTCATATTTTTACCCATTCATTATCTCTTGGCGCATTTAGAATTTAAGTTTTTTT
TTTGCATTTTCCTTTTTTATTTTACGGTTTGGTATTACTTATAAACAAATTTCATATTATAGCTATAGTTTATTAGCTAGCGTTGTGTAACTTTC
CTCCGCAGGGCCATTACTTACATTGTTAAATCGAAACGTTAATGCAATTGTTTTGTTGTGTATGTCTAACGCAATTTATATGCTCTCTATCTTAG
TTACATGATTTTGTTGCGTAAACAAAGGGCTGCCCCAACTCCCAGCTCCCACATCTCGCATCCCATTTGCCCACCGCTCGGGAAATGCGCGCTTA
AGTGTTTAAAAATCGGAAAGATATATATGAACACAGGCAGCAAAGTGCAGACCACGAAAGTATATATATATATATATATATATATATATATATAT
ATATATATATATATATATATATATATATATATATATAAATATATATATATAGATAGGGGAGTAGGCGGTACAGAAGGTTACATAATATAACATAG
GAGGGCCTTATAAGTCAGAGCGTTGCTTAAAGCTAGAGAACTGCACGTGGTAATCGCAATCATTTTACCATCAACTTAGGTTACAATGTGGGTGC
CTTGCTGTGTGGCATATGCTTTTGTATGGATTGGATTCGCTAGAGCTAGAGCCTATAGTCTAGGGTTAGGGACACTCGCTGAACGCGGTGTCCTT
TGTTTCTTTTACACAAATATTACACTTACAATCGAGTTATTATGTGTTCATGATCGGTTCTGCATGTTCTGCCTGATTTGGTCTGGGACTTCAAG
TTAACAAAGAAAAAGTTGAGCCGGCCAAGAGCAAATAGTCAAATGCAAAACAGAATTAAATGCCTGCGTGTCCTGCTAACCCTCCTCCCAAACCC
TTCCGCGGACCCCTAATCAACCGCCGATCTATTGGCCAATCTTCAGGCAGGGATCTCAAATCAATTGAACAGTGCGGTTTGTTGCAGTTTCTTGC
AGCCAGGTTGCAATCGTTTATGTTCTAATAGTATAAATTAAATTAATCATAGGCTAGTTAATTAATAATAAGCGCGCTCAACGTTCTAACATCTG
GGAGCAGAAACCAAAATGTCAAAAAACAAACGAAAATGTACACACAAAAAAAGAAAAGCGCTGCGCTTTGCTATGCTCTGCTCTTCTTCTCTCAC
TGCTCTTGTCCTCCGTTTCTGGCAGGGACCTGGTCATCCTGCCGCTTGGATACATTCAACGTGTTTTACCGCATATATAAAGCAAGTATTATATA
TATTAGGTATATATAACTATATATACTACATGTATAGTTTGTTGAGTTCTGTTGTTGTTTGTCTACTGTGTCGTGTCCAGCGTCGCAACCTAAAC
GATAAAATATTATTTGGCGTTCCCCACGCCACCGCCCCCTCCGCCGCTCGGCATACCGCCTACGCCCACTCCACCGCCGCCACCACCGCCTCCCT
GCCGCATCCGTATCGAAGGCCGACGCTCCGGCGTGTCGTACGGCGGTCTCGACGAGTTGGTGGCCGCCATCGAGTCGTCCATGTTGAGTCCGTTG
CCGCCGATCAGTTGGCTGCCGTTACCGCCTCCATTGCCGCCCAGCATCGCCAGCGTTTGGCCGCCCTGGAGTTGCTGTTGCGCTGCACTGCCTCC
TCCGCCACCCAGCGCCGCATTGACCTTGTGCTGCTGTTGTTGATGCGAGGAGGCGGCTGCCGCTGCTGCCACCGCCGCTGCTGCGGCCACCGCAT
CATGACCCGCCTGGCCGTCCGCTCCGTCCTGCGCCTGCTGAATCGCCTGGGGATTGCGAGGTCCGCCAAACTTAAGCAGGTTCCAGTCAAACACA
TAGTCGTAAGTGAAGCCCAAACGGTGGAACAAGTTGCGGAAGAGTTTGCGCAGGTGGCAGTAATCGGGACGCTGGTCGAAATGCATCTGGCGACA
GAAGTTCAGATAGTTGACGAACTCGCTGGGGAAGCCCTTGCACAGCACCACAATCGAGGTGGACAGCTTCTTCTCCGAGATCCTCTCGTACTTTT
GCCTCTTGTTGGCTGCCTTTAAGCCCTGCCAGGGCAAGGCGCCCAGATTGAAGTACATTAGGACGTAGCCCAGGGACTCCAGGTCGTCACGACGC
GATTGCTCAATGCCCAAATGTGTGTTGATGGAGGCATAGCGGGCAGTGCCCGTGAGGTTCTTGTTTTCCCGATAGGGAATGTGCTTCAGCGACCG
GGCATCGCGGAATTTCTTGGCCAGGCCAAAGTCAATGATGTACACCAGGTTGCCCTTTTTGCCAAGACCCATGAGGAAGTTATCCGGCTTGATGT
CGCGATGGATGAAGTCCCGCGAGTGTATGTAATCGATGCGGGAGATCATCTGGTCCGCCAGCAGCAGAACCGTCTTCAACGAAAAGCGGCGTGAA
CAAAAGTTGAAGAGGTCCTCCAGCGAGGGTCCGAGTAGCTCCATCACCATCACATTGTAGTCGCCCTCGCTGCCGCACCAGATTATGCGGGGTAT GCCTATGCCACCCTGCATCGTCTTGTAGAACTTTGACTCGATGTGCAGCTGGGGGTGTTTGGTGCGGATGCACTCCAGCTTGATGGCCACCTCCT
CGCCAGTGTTGATCGTGGTGCCCAGGTAGATGTCGCCGAACGATCCCGATCCTATCTTGCGGCCCAGGCGATATTTGTTACCCACGCGCAGCTCC
ATTTTGTTACGTCTGTTTCTGTGGGTTTCTGTGTGGTAGAGTTCGGACTCCTCGGGTTCCTCGGATTTGCGTTGCCTTTCTGCGGGACCGGAGAA
TTGAAATTTAGTTTTAATTTTACAACACATTGCCTCGAAAAGAAGGCTGTACGCTTTTCTTACTCATAATACTACACGCTACACGAATTGATCGA
TCCCAGTTCAGATTAGCTGCGCTTAAAATATTATACAGATTTAAATATCTACGCCAAGGACTAAAACTTTTACTTTGTAATCGCGAAAGGATATT
GAAAGGTTGCTACGATGCAGGCAAATTGTTGAATTCGATCAGAATGTAAATATTCGTAGTATTCTTAGTTGCTTTGACTAATCATAGAAATAGCA
GCGGCGTCACAGGTTTTTACGAGTAAATATGAATCAAGTGACTTCGAAAATTCGGCTATTGACCACTAGCAACAATGTGTGATATTATTAGAAGA
GATTATTTGCAAGCAACAACACAATATCGAACGCCTTGTTAGCGATAGTGATAAAATATTCGTCGGATTTTGTTTGCTACAACTTTTGATTCTTC
TGACACTATATTGTGACACGTGATGACAACCCTGCTGTTTTGTACAGTTTGCTAAAAGTCTAATTTTGAGAGCTAACGGAGCTTCGTGAGTATTT
TCCAACACTTCTCCACTTTTCTCACCTGGCACTGTCCTTTCGTCTGAGCTCCTTTCTTCTTCTTGTTCCGATTTGTTCAAGGCAGTCGCTTATGG
CTTTGTATTCGAAGGGTTCTGTAATAGGAGGTACTAAGTTAATTTTTTTTTAGATCCTCAACATGGTTAATCGAAATTCGACCCGTCTCGCGATC
ACTTATATATAGAGAGTAATCCCCTGTTTTTATCGCATCTGCAGCGTAAGCCCGAAAAACGTGCAGAATTCGCTTTTGTTTGTGGTGATAAGGAT
TGTGGCACACAGACATGAAAACAACGCACGGCAACAATCGATATCGAAAATAGAAAACCGTTAGCTAAGAATAAAACAAGAGAGAGAGAGCGGGA
GAGAAGTAAGCTTGGCTTACGTTGACAACACAAAAATAGCAGAGAAAAGCGTACCAAAAGCAATTCGAAATGCAAATGCACAGTGGGCAAAAATG
ATAAGAACCCGAACCTCGCACAAAGTAAAAGTTTATCTCGTATATTTATATTTAAGAGTGAGTGCGTCATTGCATTCGGCTGTGTGTATTGATTA
CGAATGGGGAAAACAACAGATTTAATAAGTGATGAGTAACGATAATTTATATGCACAGAGCAAAATAGCACTACTTTTTGACATTCGTCACATTA
TTGTTTTAGTCATTTTAATATTATATTGTACTATTATAAAATAAAGCAAATGTGCCGTAGTGCTTTTACATCCTTGAATAGATATAATTCTTTTT
TTCAAGTGTATTTTTTACGTGACGACACCAGAAACATGGAGGTGAATCAGCAATCAGGAAAAGACAACGAAGAGATTAACAACAAATAGATAAAA
GAGACGTGTGTTTGTGTATGCGTGGAGTAAACAATCGGCGACAAAAGGGAGAGAAGTAAAATAAAACGCAGCGACTGTGAAAATGCCACTTAAAT
GACACTTTCAGTGGTGGAAAGCACAAACAAATAGCGAAGATAAAGCGCATGGAAGTCAGAAAACGAAGCAACAAGCCGAAAGTTTTCACTTGCCG
GTCAAATATCACAAAAATTTAGTTTAATTGTTTTCGGCGGCTCTCACTCACTAACCCCTTCCCACTCCTCTTTCCCACATTCTGTGCGCTTTCTT
TTACCGCTCACGCATTTCGATCGCTCTCTCTCTTTCTCTCTCTCTCTCTCTCCTCCTTTTCCCGACTCTTTATCACTCACTCTGCGGTTCTAACC
TCAAAACCTGCCTGTGTTTGTTGTTGTTTTCGCCTTGGCTTTGATTTATTTAACCGAAATGTACCGTTTTTTATTTGTATCTCCCATGTTCTACA
CAGAAAGAAATCACTGTATAAGCACTGTAAGTCAAATTGAAATGTGGTATTAATTTTAGGAGCTTTAATTTGTTTACTGGAAGGCTAGCAGGGAA
AACGCGGTCTTTCCTATTGGTAACTAAATATTTCCCAGGGTATCCAGCAGTTGTTTCGGACCAGCGGGTAAACACGAATTGATTACAATTGCAAA
ACAGCTGCACGTTGCGTTGGCGGCTGCCGAAAAGCTTCCGCAAAAAAACGCACTGGAGAACAAAGAAGATACAAAAAACAGTTGTTCCAGCAGGC
GCCACAAAAGTAAAAAGCTTAAGTAAACAGGGAAGAGCAAATGGAAAAACCAAAAACCAGAGCAAAACCAACGGGGAAACCTCAGAAGGGGAAGG
AAACTTGCAATTAATTGTCAAACGCTAATGGCCTCCGAAAACTAACGGCACTCCACGAATGCACTGCGAATAACGGGGCTGATAAGGAGCAGCCG
ATAGCGGGTGGAGAAGGGAAACTTGAACGCACAGTGGAACAAATTCCGCACTTACCGTGGCTTGTTTTTCTTATATTCCTTGTTTCCTATTCCGC
TTTGCCCACTTCCTCTGCTGGCGACGCTGCTTTTCCTTCTTCTAATTCGACTGAAATCGAAATCGAATTTTTTAATTGGATTGATTCTGCCACAA
TAATTTTCATTTTCTTTGTTTTAGAGCCCAGACGTTGTTTTTGTTGTAGTTGCCACAGTCGCACACAAACACACGCACACAGTCGCACTTTTTGG
GGCCACACGCAAGCGCATTTTATGCAATAATTTTAATAATACTGCATTGCTGCCATATTTCAGTTATTTTTATCGTTTATCTTCGAGTCGGTTAT
GCTGTTCTTCTCTGATTTTATGGCCACATTGATTAGCATCTTGTTGCCAATCAACTCGAGAAAATTAAACGAAACCAAACGGAACTCGGACTCTT
ATTAAAAAAACCAAACTTATGCGAGTCGTTTGCCCTGGCAATAGATTCGTGCACACTAGTCGTCCCGCCCGCACTCGCACGGTTTCTACCGCGAG
CACGTTGCTATCCCTCCTGCTTCAGCATTTTCACACCAACACAAAGACGAGGGCACTCACTCACACACTCGCACTCTCAATGAGCACTGAAATGC
TGTTGGGAAATTCGAGTTTTCCTGCGCGTGGTAACCGCCGCTTTTTCGCTCGCAAACGGGTCTGTCGATCCGAAACGCTACTGACCACTTACGTT
TTGCATCAACGCTGCGCTTTCGTTTCAATTTTTCTGGCTATTTCACATAGATTTCGACGATTTTTACAAATTTACGCCATCTTGATATTCGCAG
TGTGACCGCGCCGATAATGAAGAAAATTACCATCTGGTATTTACTCCTCAGCGAATGTCTAGAAGATATGTAATTGTGAAAAACTGTGATTCATA
TACTAAGTTAAGATAGTCCAAAGTTGGTTTCGAAGTACCACATTAAGAAAATAGCGCAAGAGTATTGGAAAATCAAAAGAAAAACGAAATTATAT
CCTTGCAGCTAGCCATAAGTTCAAAGTTCGAGTAACTGGAAAGCTGTGAAATAGCCAAGTTGACAACGCTGTTTTTGTTATATGGGCACACTAGT
TCTTACATAGACCCAGTGCTGCCAGATGGACGAAAAATATTTTTGAGCTGCGCCACCTAGCGGATGAGTTGGCGAAAGTGGTATCCAGGTGGCGC
CCGAAACAAAAGGTGGCGCCTTATTTCAGAAATGCAATTGAAAATATCTAAAGTTATGAAAGTTTTTGAATTATGCATTCAAAGGCCCATCTGC
TTAATTTTATTTTCAAAGAGAATACAATAAACAATACAAAAAAAAAAAAATCATTCTGAAATGATATTTATACTAATATACAAATTTGATAACTC
AATAATATGTAAATAAAATTTATGTCTTAATTTGCAATGTTTCTTAAGAAAAGTTGTTAACTCTTTTTACAGGCTTGTGCTCCAAATTCTCGTGTA
AATAGAAATTGAAAATGGATTTCATTGGCATGTCTTGCAGTTATAGGTAGCATGCCAATTTTGATGTTACACAGATGTATCGAAATACCTGAAAC
GTATACTTTTATTGCAGCAATACGAATAAAGCAAAACACGTGTGAATTCCATTAGTCCGCCCAACCGCTTTCCCCATTTACCCTCACATCGTGCA
TTTTCCGGCTGTGTAACCCAAGAAACGATGACATAAAAAAAGGAAGCAGATCCAGTTATGTATGCATATATGAGAAAATGTGTTTTTTTTTTTTT
GGGAGTATGTGCCAAGGTGTGTTTCTTTTT
(SEQ ID NO: 1249)

Exon: 6060..5983
Exon: 3533..3446
Exon: 2834..1001
Start ATG: 2757 (Reverse strand: CAT)

Transcript No. : CT42623
TAAATTTGTAAAAAATCGTCGAAATCTATGTGAAATAGCCAGAAAAATTGAAACGAAAGCGCAGCGTTGATGCAAAACAACCCTTCGAATACAAA
GCCATAAGCGACTGCCTTGAACAAATCGGAACAAGAAGAAGAAAGGAGCTCAGACGAAAGGACAGTGCCAGAAAGGCAACGCAAATCCGAGGAAC
CCGAGGAGTCCGAACTCTACCACACAGAAACCCACAGAAACAGACGTAACAAAATGGAGCTGCGCGTGGGTAACAAATATCGCCTGGGCCGCAAG
ATAGGATCGGGATCGTTCGGCGACATCTACCTGGGCACCACGATCAACACTGGCGAGGAGGTGGCCATCAAGCTGGAGTGCATCCGCACCAAACA
CCCCCAGCTGCACATCGAGTCAAAGTTCTACAAGACGATGCAGGGTGGCATAGGCATACCCCGCATAATCTGGTGCGGCAGCGAGGGCGACTACA
ATGTGATGGTGATGGAGCTACTCGGACCCTCGCTGGAGGACCTCTTCAACTTTTGTTCACGCCGCTTTTCGTTGAAGACGGTTCTGCTGCTGGCG
GACCAGATGATCTCCCGCATCGATTACATACACTCGCGGGACTTCATCCATCGCGACATCAAGCCGGATAACTTCCTCATGGGTCTTGGCAAAAA
GGGCAACCTGGTGTACATCATTGACTTTGGCCTGGCCAAGAAATTCCGCGATGCCCGGTCGCTGAAGCACATTCCCTATCGGGAAAACAAGAACC
TCACGGGCACTGCCCGCTATGCCTCCATCAACACACATTTGGGCATTGAGCAATCGCGTCGTGACGACCTGGAGTCCCTGGGCTACGTCCTAATG
TACTTCAATCTGGGCGCCTTGCCCTGGCAGGGCTTAAAGGCAGCCAACAAGAGGCAAAAGTACGAGAGGATCTCGGAGAAGAAGCTGTCCACCTC
GATTGTGGTGCTGTGCAAGGGCTTCCCCAGCGAGTTCGTCAACTATCTGAACTTCTGTCGCCAGATGCATTTCGACCAGCGTCCCGATTACTGCC
ACCTGCGCAAACTCTTCCGCAACTTGTTCCACCGTTTGGGCTTCACTTACGACTATGTGTTTGACTGGAACCTGCTTAAGTTTGGCGGACCTCGC
AATCCCCAGGCGATTCAGCAGGCGCAGGACGGAGCGGACGGCCAGGCGGGTCATGATGCGGTGGCCGCAGCAGCGGCGGTGGCAGCAGCGGCAGC
CGCCTCCTCGCATCAACAACAGCAGCACAAGGTCAATGCGGCGCTGGGTGGCGGAGGAGGCAGTGCAGCGCAACAGCAACTCCAGGGCGGCCAAA
CGCTGGCGATGCTGGGCGGCAATGGAGGCGGTAACGGCAGCCAACTGATCGGCGGCAACGGACTCAACATGGACGACTCGATGGCGGCCACCAAC TCGTCGAGACCGCCGTACGACACGCCGGAGCGTCGGCCTTCGATACGGATGCGGCAGGGAGGCGGTGGTGGCGGCGGTGGAGTGGGCGTAGGCGG
TATGCCGAGCGGCGGAGGGGGCGGTGGCGTGGGGAACGCCAAATAATATTTTATCGTTTAGGTTGCGACGCTGGACACGACACAGTAGACAAACA
ACAACAGAACTCAACAAACTATACATGTAGTATATATAGTTATATATACCTAATATATATAATACTTGCTTTATATATGCGGTAAAACACGTTGA
ATGTATCCAAGCGGCAGGATGACCAGGTCCCTGCCAGAAACGGAGGACAAGAGCAGTGAGAGAAGAAGAGCAGAGCATAGCAAAGCGCAGCGCTT
TTCTTTTTTTGTGTGTACATTTTCGTTTGTTTTTTGACATTTTGGTTTCTGCTCCCAGATGTTAGAACGTTGAGCGCGCTTATTATTAATTAACT
AGCCTATGATTAATTTAATTTATACTATTAGAACATAAACGATTGCAACCTGGCTGCAAGAAACTGCAACAAACCGCACTGTTCAATTGATTTGA
GATCC
(SEQ ID NO: 1250)

Start ATG: 244 (Reverse strand: CAT)

MELRVGNKYRLGRKIGSGSFGDIYLGTTINTGEEVAIKLECIRTKHPQLHIESKFYKTMQGGIGIPRIIWCGSEGDYNVMVMELLGPSLEDLFNF
CSRRFSLKTVLLLADQMISRIDYIHSRDFIHRDIKPDNFLMGLGKKGNLVYIIDFGLAKKFRDARSLKHIPYRENKNLTGTARYASINTHLGIEQ
SRRDDLESLGYVLMYFNLGALPWQGLKAANKRQKYERISEKKLSTSIVVLCKGFPSEFVNYLNFCRQMHFDQRPDYCHLRKLFRNLFHRLGFTYD
YVFDWNLLKFGGPRNPQAIQQAQDGADGQAGHDAVAAAAAVAAAAAASSHQQQQHKVNAALGGGGGSAAQQQLQGGQTLAMLGGNGGGNGSQLIG
GNGLNMDDSMAATNSSRPPYDTPERRPSIRMRQGGGGGGGGVGVGGMPSGGGGGGVGNAK*
(SEQ ID NO: 1251)

Name: DOUBLE-TIME PROTEIN KINASE (EC 2.7.1.-)
Classification: protein_kinase

Celera Sequence No. : 142000013384567
TTTACGTGTTCTCATAAGATATAGTTTATATTAATGTATATTCATATTTTTACCCATTCATTATCTCTTGGCGCATTTAGAATTTAAGTTTTTTT
TTTGCATTTTCCTTTTTTATTTTACGGTTTGGTATTACTTATAAACAAATTTCATATTATAGCTATAGTTTATTAGCTAGCGTTGTGTAACTTTC
CTCCGCAGGGCCATTACTTACATTGTTAAATCGAAACGTTAATGCAATTGTTTTGTTGTGTATGTCTAACGCAATTTATATGCTCTCTATCTTAG
TTACATGATTTTGTTGCGTAAACAAAGGGCTGCCCCAACTCCCAGCTCCCACATCTCGCATCCCATTTGCCCACCGCTCGGGAAATGCGCGCTTA
AGTGTTTAAAAATCGGAAAGATATATATGAACACAGGCAGCAAAGTGCAGACCACGAAAGTATATATATATATATATATATATATATATATATAT
ATATATATATATATATATATATATATATATATATATATAAATATATATATATAGATAGGGGAGTAGGCGGTACAGAAGGTTACATAATATAACATAG
GAGGGCCTTATAAGTCAGAGCGTTGCTTAAAGCTAGAGAACTGCACGTGGTAATCGCAATCATTTTACCATCAACTTAGGTTACAATGTGGGTGC
CTTGCTGTGTGGCATATGCTTTTGTATGGATTGGATTCGCTAGAGCTAGAGCCTATAGTCTAGGGTTAGGGACACTCGCTGAACGCGGTGTCCTT
TGTTTCTTTTACACAAATATTACACTTACAATCGAGTTATTATGTGTTCATGATCGGTTCTGCATGTTCTGCCTGATTTGGTCTGGGACTTCAAG
TTAACAAAGAAAAAGTTGAGCCGGCCAAGAGCAAATAGTCAAATGCAAAACAGAATTAAATGCCTGCGTGTCCTGCTAACCCTCCTCCCAAACCC
TTCCGCGGACCCCTAATCAACCGCCGATCTATTGGCCAATCTTCAGGCAGGGATCTCAAATCAATTGAACAGTGCGGTTTGTTGCAGTTTCTTGC
AGCCAGGTTGCAATCGTTTATGTTCTAATAGTATAAATTAAATTAATCATAGGCTAGTTAATTAATAATAAGCGCGCTCAACGTTCTAACATCTG
GGAGCAGAAACCAAAATGTCAAAAAACAAACGAAAATGTACACACAAAAAAAGAAAAGCGCTGCGCTTTGCTATGCTCTGCTCTTCTTCTCTCAC
TGCTCTTGTCCTCCGTTTCTGGCAGGGACCTGGTCATCCTGCCGCTTGGATACATTCAACGTGTTTTACCGCATATATAAAGCAAGTATTATATA
TATTAGGTATATATAACTATATATACTACATGTATAGTTTGTTGAGTTCTGTTGTTGTTTGTCTACTGTGTCGTGTCCAGCGTCGCAACCTAAAC
GATAAAATATTATTTGGCGTTCCCCACGCCACCGCCCCCTCCGCCGCTCGGCATACCGCCTACGCCCACTCCACCGCCGCCACCACCGCCTCCCT
GCCGCATCCGTATCGAAGGCCGACGCTCCGGCGTGTCGTACGGCGGTCTCGACGAGTTGGTGGCCGCCATCGAGTCGTCCATGTTGAGTCCGTTG
CCGCCGATCAGTTGGCTGCCGTTACCGCCTCCATTGCCGCCCAGCATCGCCAGCGTTTGGCCGCCCTGGAGTTGCTGTTGCGCTGCACTGCCTCC
TCCGCCACCCAGCGCCGCATTGACCTTGTGCTGCTGTTGTTGATGCGAGGAGGCGGCTGCCGCTGCTGCCCACCGCCGCTGCTGCGGCCACCGCAT
CATGACCCGCCTGGCCGTCCGCTCCGTCCTGCGCCTGCTGAATCGCCTGGGGATTGCGAGGTCCGCCAAACTTAAGCAGGTTCCAGTCAAACACA
TAGTCGTAAGTGAAGCCCAAACGGTGGAACAAGTTGCGGAAGAGTTTGCGCAGGTGGCAGTAATCGGGACGCTGGTCGAAATGCATCTGGCGACA
GAAGTTCAGATAGTTGACGAACTCGCTGGGGAAGCCCTTGCACAGCACCACAATCGAGGTGGACAGCTTCTTCTCCGAGATCCTCTCGTACTTTT
GCCTCTTGTTGGCTGCCTTTAAGCCCTGCCAGGGCAAGGCGCCCAGATTGAAGTACATTAGGACGTAGCCCAGGGACTCCAGGTCGTCACGACGC
GATTGCTCAATGCCCAAATGTGTGTTGATGGAGGCATAGCGGGCAGTGCCCGTGAGGTTCTTGTTTTCCCGATAGGGAATGTGCTTCAGCGACCG
GGCATCGCGGAATTTCTTGGCCAGGCCAAAGTCAATGATGTACACCAGGTTGCCCTTTTTGCCAAGACCCATGAGGAAGTTATCCGGCTTGATGT
CGCGATGGATGAAGTCCCGCGAGTGTATGTAATCGATGCGGGAGATCATCTGGTCCGCCAGCAGCAGAACCGTCTTCAACGAAAAGCGGCGTGAA
CAAAAGTTGAAGAGGTCCTCCAGCGAGGGTCCGAGTAGCTCCATCACCATCACATTGTAGTCGCCCTCGCTGCCGCACCAGATTATGCGGGGTAT
GCCTATGCCACCCTGCATCGTCTTGTAGAACTTTGACTCGATGTGCAGCTGGGGGTGTTTGGTGCGGATGCACTCCAGCTTGATGGCCACCTCCT
CGCCAGTGTTGATCGTGGTGCCCAGGTAGATGTCGCCGAACGATCCCGATCCTATCTTGCGGCCCAGGCGATATTTGTTACCCACGCGCAGCTCC
ATTTTGTTACGTCTGTTTCTGTGGGTTTCTGTGTGGTAGAGTTCGGACTCCTCGGGTTCCTCGGATTTGCGTTGCCTTTCTGCGGGACCGGAGAA
TTGAAATTTAGTTTTAATTTTACAACACATTGCCTCGAAAAGAAGGCTGTACGCTTTTCTTACTCATAATACTACACGCTACACGAATTGATCGA
TCCCAGTTCAGATTAGCTGCGCTTAAAATATTATACAGATTTAAATATCTACGCCAAGGACTAAAACTTTTACTTTGTAATCGCGAAAGGATATT
GAAAGGTTGCTACGATGCAGGCAAATTGTTGAATTCGATCAGAATGTAAATATTCGTAGTATTCTTAGTTGCTTTGACTAATCATAGAAATAGCA
GCGGCGTCACAGGTTTTTACGAGTAAATATGAATCAAGTGACTTCGAAAATTCGGCTATTGACCACTAGCAACAATGTGTGATATTATTAGAAGA
GATTATTTGCAAGCAACAACACAATATCGAACGCCTTGTTAGCGATAGTGATAAAATATTCGTCGGATTTTGTTTGCTACAACTTTTGATTCTTC
TGACACTATATTGTGACACGTGATGACAACCCTGCTGTTTTGTACAGTTTGCTAAAAGTCTAATTTTGAGAGCTAACGGAGCTTCGTGAGTATTT
TCCAACACTTCTCCACTTTTCTCACCTGGCACTGTCCTTTCGTCTGAGCTCCTTTCTTCTTCTTGTTCCGATTTGTTCAAGGCAGTCGCTTATGG
CTTTGTATTCGAAGGGTTCTGTAATAGGAGGTACTAAGTTAATTTTTTTTTAGATCCTCAACATGGTTAATCGAAATTCGACCCGTCTCGCGATC
ACTTATATATAGAGAGTAATCCCCTGTTTTTATCGCATCTGCAGCGTAAGCCCGAAAAACGTGCAGAATTCGCTTTTGTTTGTGGTGATAAGGAT
TGTGGCACACAGACATGAAAACAACGCACGGCAACAATCGATATCGAAAATAGAAAACCGTTAGCTAAGAATAAAACAAGAGAGAGAGAGCGGGA
GAGAAGTAAGCTTGGCTTACGTTGACAACACAAAAATAGCAGAGAAAAGCGTACCAAAAGCAATTCGAAATGCAAATGCACAGTGGGCAAAAATG
ATAAGAACCCGAACCTCGCACAAAGTAAAAGTTTATCTCGTATATTTATATTTAAGAGTGAGTGCGTCATTGCATTCGGCTGTGTGTATTGATTA
CGAATGGGGAAAACAACAGATTTAATAAGTGATGAGTAACGATAATTTATATGCACAGAGCAAAATAGCACTACTTTTTGACATTCGTCACATTA
TTGTTTTAGTCATTTTAATATTATATTGTACTATTATAAAATAAAGCAAATGTGCCGTAGTGCTTTTACATCCTTGAATAGATATAATTCTTTTT
TTCAAGTGTATTTTTTACGTGACGACACCAGAAACATGGAGGTGAATCAGCAATCAGGAAAAGACAACGAAGAGATTAACAACAAATAGATAAAA
GAGACGTGTGTTTGTGTATGCGTGGAGTAAACAATCGGCGACAAAAGGGAGAGAAGTAAAATAAAACGCAGCGACTGTGAAAATGCCACTTAAAT
GACACTTTCAGTGGTGGAAAGCACAAACAAATAGCGAAGATAAAGCGCATGGAAGTCAGAAAACGAAGCAACAAGCCGAAAGTTTTCACTTGCCG
GTCAAATATCACAAAAATTTAGTTTAATTGTTTTCGGCGGCTCTCACTCACTAACCCCTTCCCACTCCTCTTTCCCACATTCTGTGCGCTTTCTT TTACCGCTCACGCATTTCGATCGCTCTCTCTCTTTCTCTCTCTCTCTCTCTCCTCCTTTTCCCGACTCTTTATCACTCACTCTGCGGTTCTAACC
TCAAAACCTGCCTGTGTTTGTTGTTGTTTTCGCCTTGGCTTTGATTTATTTAACCGAAATGTACCGTTTTTTATTTGTATCTCCCATGTTCTACA
CAGAAAGAAATCACTGTATAAGCACTGTAAGTCAAATTGAAATGTGGTATTAATTTTAGGAGCTTTAATTTGTTTACTGGAAGGCTAGCAGGGAA
AACGCGGTCTTTCCTATTGGTAACTAAATATTTCCCAGGGTATCCAGCAGTTGTTTCGGACCAGCGGGTAAACACGAATTGATTACAATTGCAAA
ACAGCTGCACGTTGCGTTGGCGGCTGCCGAAAAGCTTCCGCAAAAAAACGCACTGGAGAACAAAGAAGATACAAAAAACAGTTGTTCCAGCAGGC
GCCACAAAAGTAAAAAGCTTAAGTAAACAGGGAAGAGCAAATGGAAAAACCAAAAACCAGAGCAAAACCAACGGGGAAACCTCAGAAGGGGAAGG
AAACTTGCAATTAATTGTCAAACGCTAATGGCCTCCGAAAACTAACGGCACTCCACGAATGCACTGCGAATAACGGGGCTGATAAGGAGCAGCCG
ATAGCGGGTGGAGAAGGGAAACTTGAACGCACAGTGGAACAAATTCCGCACTTACCGTGGCTTGTTTTTCTTATATTCCTTGTTTCCTATTCCGC
TTTGCCCACTTCCTCTGCTGGCGACGCTGCTTTTCCTTCTTCTAATTCGACTGAAATCGAAATCGAATTTTTTAATTGGATTGATTCTGCCACAA
TAATTTTCATTTTCTTTGTTTTAGAGCCCAGACGTTGTTTTTGTTGTAGTTGCCACAGTCGCACACAAACACACGCACACAGTCGCACTTTTTGG
GGCCACACGCAAGCGCATTTTATGCAATAATTTTAATAATACTGCATTGCTGCCATATTTCAGTTATTTTTATCGTTTATCTTCGAGTCGGTAT
GCTGTTCTTCTCTGATTTTATGGCCACATTGATTAGCATCTTGTTGCCAATCAACTCGAGAAAATTAAACGAAACCAAACGGAACTCGGACTCTT
ATTAAAAAAACCAAACTTATGCGAGTCGTTTGCCCTGGCAATAGATTCGTGCACACTAGTCGTCCCGCCCGCACTCGCACGGTTTCTACCGCGAG
CACGTTGCTATCCCTCCTGCTTCAGCATTTTCACACCAACACAAAGACGAGGGCACTCACTCACACACTCGCACTCTCAATGAGCACTGAAATGC
TGTTGGGAAATTCGAGTTTTCCTGCGCGTGGTAACCGCCGCTTTTTCGCTCGCAAACGGGTCTGTCGATCCGAAACGCTACTGACCACTTACGTT
TTGCATCAACGCTGCGCTTTCGTTTCAATTTTTCTGGCTATTTCACATAGATTTCGACGATTTTTTACAAATTTACGCCATCTTGATATTCGCAG
TGTGACCGCGCCGATAATGAAGAAAATTACCATCTGGTATTTACTCCTCAGCGAATGTCTAGAAGATATGTAATTGTGAAAAACTGTGATTCATA
TACTAAGTTAAGATAGTCCAAAGTTGGTTTCGAAGTACCACATTAAGAAAATAGCGCAAGAGTATTGGAAAATCAAAAGAAAAACGAAATTATAT
CCTTGCAGCTAGCCATAAGTTCAAAGTTCGAGTAACTGGAAAGCTGTGAAATAGCCAAGTTGACAACGCTGTTTTTGTTATATGGGCACACTAGT
TCTTACATAGACCCAGTGCTGCCAGATGGACGAAAAATATTTTTGAGCTGCGCCACCTAGCGGATGAGTTGGCGAAAGTGGTATCCAGGTGGCGC
CCGAAACAAAAGGTGGCGCCTTATTTCAGAAATGCAATTGAAAATATCTAAAGTTATTGAAAGTTTTTGAATTATGCATTCAAAGGCCCATCTGC
TTAATTTTATTTTCAAAGAGAATACAATAAACAATACAAAAAAAAAAAAAATCATTCTGAAATGATATTTATACTAATATACAAATTTGATAACTC
AATAATATGTAAATAAAATTTATGTCTTA
(SEQ ID NO: 1252)

Exon: 5679..5281
Exon: 3533..3446
Exon: 2834..1001
Start ATG: 2757 (Reverse strand: CAT)

Transcript No. : CT42625
TTTCGTTTAATTTTCTCGAGTTGATTGGCAACAAGATGCTAATCAATGTGGCCATAAAATCAGAGAAGAACAGCATAACCGACTCGAAGATAAAC
GATAAAAATAACTGAAATATGGCAGCAATGCAGTATTATTAAAATTATTGCATAAAATGCGCTTGCGTGTGGCCCCAAAAGTGCGACTGTGTGC
GTGTGTTTGTGTGCGACTGTGGCAACTACAACAAAAACAACGTCTGGGCTCTAAAACAAAGAAAATGAAAATTATTGTGGCAGAATCAATCCAAT
TAAAAAATTCGATTTCGATTTCAGTCGAATTAGAAGAAGGAAAAGCAGCGTCGCCAGCAGAGGAAGTGGGCAAAGCGGAATAGGAAACAAGGAAT
ATAAGAAAAACAAGCCACGAACCCTTCGAATACAAAGCCATAAGCGACTGCCTTGAACAAATCGGAACAAGAAGAAGAAAGGAGCTCAGACGAAA
GGACAGTGCCAGAAAGGCAACGCAAATCCGAGGAACCCGAGGAGTCCGAACTCTACCACACAGAAACCCACAGAAACAGACGTAACAAAATGGAG
CTGCGCGTGGGTAACAAATATCGCCTGGGCCGCAAGATAGGATCGGGATCGTTCGGCGACATCTACCTGGGCACCACGATCAACACTGGCGAGGA
GGTGGCCATCAAGCTGGAGTGCATCCGCACCAAACACCCCCAGCTGCACATCGAGTCAAAGTTCTACAAGACGATGCAGGGTGGCATAGGCATAC
CCCGCATAATCTGGTGCGGCAGCGAGGGCGACTACAATGTGATGGTGATGGAGCTACTCGGACCCTCGCTGGAGGACCTCTTCAACTTTTGTTCA
CGCCGCTTTTCGTTGAAGACGGTTCTGCTGCTGGCGGACCAGATGATCTCCCGCATCGATTACATACACTCGCGGGACTTCATCCATCGCGACAT
CAAGCCGGATAACTTCCTCATGGGTCTTGGCAAAAAGGGCAACCTGGTGTACATCATTGACTTTGGCCTGGCCAAGAAATTCCGCGATGCCCGGT
CGCTGAAGCACATTCCCTATCGGGAAAACAAGAACCTCACGGGCACTGCCCGCTATGCCTCCATCAACACACATTTGGGCATTGAGCAATCGCGT
CGTGACGACCTGGAGTCCCTGGGCTACGTCCTAATGTACTTCAATCTGGGCGCCTTGCCCTGGCAGGGCTTAAAGGCAGCCAACAAGAGGCAAAA
GTACGAGAGGATCTCGGAGAAGAAGCTGTCCACCTCGATTGTGGTGCTGTGCAAGGGCTTCCCCAGCGAGTTCGTCAACTATCTGAACTTCTGTC
GCCAGATGCATTTCGACCAGCGTCCCGATTACTGCCACCTGCGCAAACTCTTCCGCAACTTGTTCCACCGTTTGGGCTTCACTTACGACTATGTG
TTTGACTGGAACCTGCTTAAGTTTGGCGGACCTCGCAATCCCCAGGCGATTCAGCAGGCGCAGGACGGAGCGGACGGCCAGGCGGGTCATGATGC
GGTGGCCGCAGCAGCGGCGGTGGCAGCAGCGGCAGCCGCCTCCTCGCATCAACAACAGCAGCACAAGGTCAATGCGGCGCTGGGTGGCGGAGGAG
GCAGTGCAGCGCAACAGCAACTCCAGGGCGGCCAAACGCTGGCGATGCTGGGCGGCAATGGAGGCGGTAACGGCAGCCAACTGATCGGCGGCAAC
GGACTCAACATGGACGACTCGATGGCGGCCACCAACTCGTCGAGACCGCCGTACGACACGCCGGAGCGTCGGCCTTCGATACGGATGCGGCAGGG
AGGCGGTGGTGGCGGCGGTGGAGTGGGCGTAGGCGGTATGCCGAGCGGCGGAGGGGGCGGTGGCGTGGGGAACGCCAAATAATATTTTATCGTTT
AGGTTGCGACGCTGGACACGACACAGTAGACAAACAACAACAGAACTCAACAAACTATACATGTAGTATATATAGTTATATATACCTAATATATA
TAATACTTGCTTTATATATGCGGTAAAACACGTTGAATGTATCCAAGCGGCAGGATGACCAGGTCCCTGCCAGAAACGGAGGACAAGAGCAGTGA
GAGAAGAAGAGCAGAGCATAGCAAAGCGCAGCGCTTTTCTTTTTTTGTGTGTACATTTTCGTTTGTTTTTTGACATTTTGGTTTCTGCTCCCAGA
TGTTAGAACGTTGAGCGCGCTTATTATTAATTAACTAGCCTATGATTAATTTAATTTATACTATTAGAACATAAACGATTGCAACCTGGCTGCAA
GAAACTGCAACAAACCGCACTGTTCAATTGATTTGAGATCC
(SEQ ID NO: 1253)

Start ATG: 565 (Reverse strand: CAT)

MELRVGNKYRLGRKIGSGSFGDIYLGTTINTGEEVAIKLECIRTKHPQLHIESKFYKTMQGGIGIPRIIWCGSEGDYNVMVMELLGPSLEDLFNF
CSRRFSLKTVLLLADQMISRIDYIHSRDFIHRDIKPDNFLMGLGKKGNLVYIIDFGLAKKFRDARSLKHIPYRENKNLTGTARYASINTHLGIEQ
SRRDDLESLGYVLMYFNLGALPWQGLKAANKRQKYERISEKKLSTSIVVLCKGFPSEFVNYLNFCRQMHFDQRPDYCHLRKLFRNLFHRLGFTYD
YVFDWNLLKFGGPRNPQAIQQAQDGADGQAGHDAVAAAAAVAAAAAASSHQQQQHKVNAALGGGGGSAAQQQLQGGQTLAMLGGNGGGNGSQLIG
GNGLNMDDSMAATNSSRPPYDTPERRPSIRMRQGGGGGGGGVGVGGMPSGGGGGGVGNAK*
(SEQ ID NO: 1254)

Name: DOUBLE-TIME PROTEIN KINASE (EC 2.7.1.-)
Classification: protein_kinase

Celera Sequence No. : 142000013384244
TGGACTAAACTCGCAGATTCCTGTAACTTGGAAGCACCACGAGTTTGCTTTAGAAGATGCCTTTCCGTTGAACTAAAACTAGACGAGTAAAGCGT
ATCTCAAACATTGTATCTTCCGAACCAAAATAGTGCTGCATACTTTTCGGGATATGTCTTATTCAATGTAAGTAATACAAAAAGAAAAAAGGTAA
CTTCTTAAAACTTGTAATATTTGTCACAAATGAATGACGACTAGATTTGGCCATGTCTGTAACAATAAACGTACAAAATATTCGAAGTTGCAGAA
ATGGGGATCCAGCATTCGGATTTGGTTTTTTGTCAAACTTTTAAATATAGAATCGGACCACATCTTTTTAAGACCTTAAAAAACTGATTTGAAGT
TAGACCCCTCATAATGCCAACTAAATTTGTTAAACAAAAATATGCCCCTATATGCCAATCAAATTTAAATACAATGCTTTCTCAGCGTTTCAGTT
AAATACTTTGGGTTGTTTAATGGTTTTATACGTATACATGTGCTAAGTCCATGTATCTTATATTTCGTAAATCCATAGATTTTGTTCGACGAAAC
TTTGCTAAATGATATTGATCTTTCAAATATAACTTGTTAATTTCCTTTCATCGCCGTGGCAAATCCTTCGAGAGTGAGTACTACTTGTTAAACGC
ATATATGAGGAAAATTTATTGATGAATAATGCGAACATGCAAACGGAACACATCCCCGAATTCACACAAAGCATCTCTGTGGTATCTCTTTTGGT
TTTTTATTTGTTGCATCAACTCCGCGGAACTCCAGCTACCTCACTGCAGGTCGTAGTAGTCGACGTTATTGGCGGTCAGATGTTCTCTATTAATT
TGGAGCGTGCTGCTGTTTCCACTTCAAACTTTTATTAACATATATAGTATGGGTTTGCCGGTATATTGCAAACGGGAACTAAGTGTAGATTCGTG
AATGATATCAGACTGGACTGCAAACGTTTAGTTTCTAGCATGTTTTTTTACTCTCTCCTTTATTTGTTGGAATTTTTGAGTTTTATATAGGTGG
AGTTTTCAAAATGACATTAATTCATAGGGGTGAGTTTTATATATAGTTCGACTGGCTGTTGCAGGTGCTGGTTTCGAATTTTTGGATGGGGATGC
TAAAGGGCGGCTCCGTTTGTGTTCATCCTCATTTAGCCATCAACCAAGTTCTTACTCGCCATTCTTTTGTTCGTCCTCAGATTCGGATTCTGAAA
GAGAATAGAATACAAAATGTTAGTATGGGGGCTTCAATTGGTACAAACTGAAAAGATGTGCAGCTCCGGTTATGCTGTCCAAATGATTATTGGCC
AAATTTAACTATGGAAAGTTATCTGGACACCCAACCATTCAAATGCTTTGGCACAACTCCCCGCTTGGCTCAATCGAATGAAGCAACCATTCGGA
GCTTTTATGAGGGGATTGTGCATGCGGACTAGGACAAATGCAGCTGTCCAAACGATTATTGGCCAAATTAACCACGGCATTGGGTTATATGGGCA
CCCAATCATTCTTTCGCTTTTGCATACTGTACATGAACCCTTTAAAACTGGTTCCTAATAATGGGAACACTTTAAAAGCTTGGTAAGAAGCATGC
TCGGTGAAGTCAGCTATTTGTGTCCAAGTTTTCATTGGCCTTTGATGCTCGGATTTTGTGAGGCAACAAGGCAAGCAAAAACTCAAATGCTCTTG
CAATTTTGTACAATGAAAATGTCATCCAGGACAAGACCATTCTCAAAAAGTGCACTGTGTAAAGTTTCGAAGGAAGCAAAATTTGAATATTTATA
TTGTCCAGGTTTTCATTGGCCTACGTTGTTCAGTGAATGGAAATCAACGAGGCAAGCAAAAAACCCAAATTTCTCTTGCAATTACGTACCAGAAT
CAAGCTATTTAAGACAAGACCATTCTCAAAAATTGCACGCTGATAACATTTATCAAAACATACTAACCTTCTTCGGCTGACTGAAGCCATTCGAC
AAACTTTCGCATTTGTTCAAGGAAATGCATTTTGCCCTTGTTTGAGTGGCCCTCCTTGTACCAGCGCAAGATGATCTCCTCGGACAGGACCTCGG
TCTTGTAGAACAACAAAATGATTTTCTGGAAGGCCTTCATGAAGTTCATGTTCTCGTAGCAGAATTCCTGCACCTTCAAGATTAGGGCCAATTCC
GAACGGTCGGTCGAGGCGAAAGCCTGCAACAGTGGGCAGTAGTTCTTCAGATGACGAACAGCCTGATCGGTAACCAGCTCCTCCTTCTTGTTCCA
TTCGCCCAATGACATGATGGTGGACCAAATCTGGTAAAGATCATACATGAGATTTAGTAAGGAAATCATCCAGTTGGATTATTTACGCATCGACT
TACAATAACAATTATTTCATGATCGGGAATGTTGGTGCGCTGCGAGAAGTCCTTAATGTCTGAGGTTATCTCATTATATGGCTTCTCATCGTTGA
TATCATCGATGAGCGCCTGCTGCAACTCACGCTTCGCCTCCTGGCTAGCCTGAGCCTTATGTAGCTTGACGATCTCGTTAAGTTCTTTGTCAAGA
AAAACTTGTTTAAAATATTCCTCAGTACGTTTGTTCGGTGGGAAAAAGTCCATAAGTCTGGAAAAACGTGAAAAAGTGGAACCATTATTAATAAT
TTAAGTTAACGCATTCAATAATCAACCTTAAATGACGTATTGAGGTGTACGAAATTAAATCAGCACCCAAATGAAGCGAAAGGTCATTTGCGAAT
TGGGTAAAACTCCGTCGAACTTTCTTACTCTAGGAATATCAATTAAAGATGCACAACTGGATCATTGAGTCATCTTCCTGAGAACATTCCGGGGC
TAAAAACAAATCACAACTAAAAACTTACTTGCTTTCCAGTCCACCCTTCTTAAGCGCCTGAATCAGATATGCAATGCCCTTCTCTTGCTTGAACG
TCTGGAACAGCTCTAGTAGAAACTCCAATGCAATGCCATCCTTGATTAGGTGCTCGTTGTTTAGTACCAGTAAAACATTTGGCGGTACAGAACCG
TTGACTGTTGATCAAAAATAGGGTTAAATATAGGGTTAGTCAAATGTTTTCGCAAAACAAGTTTAGACGGCCGGCTAGCAATCCTGTCCTTGGGC
TCGTGGCCCTTAGATGTGGTTAGTTCATCCAAGAGTCAGTATACCAAGTGAAGGATTACTTTAGCCCCTCAGCTGCAAGTTGAACAAGTGTTTAT
CGAAACAACTAATTGAAAGACCGAATGGGCAGACGCAAGCAATGCACAGGAGGAACAGGAACATAAATGTTAAGACTTACCTAACCAGAGCGCTG
TCATACGCGCAAGCTTGATGCGTTCACTAGGAGTAAAGCCCTTTACGAATAATAGAACCTTTCCCATCTCCTCTTCGAACATTTTCTCAAGGTAC
TTGTACCGTCTGATGAGCTTGACAAATACCTGGAAAAGGTAAAGTGTGATTGCCCCTGTTAGCGGATGGTGAAATTTTACTGTGTTCTCACGCAG
GAGGCTTTTGTATTTGTTGTTGCAACATTAGAAATCTTTAGATTGCTGGCGGTAGTAATTTTACAAAATAAAGACAAGTAAAATGTGGCTTTTTA
TTTTGCATATTTTGACACCGATTGAGTTGTTGAGATGCATAACCGGTTCTAATAATATGCACTTTGATTCAATAGCGTGACCTTCGCAGTGGTTG
CATGCATATAGTATATATATATAGTGTTGAATAAAGAGTAGTTGTTGACACATAAGAAATCTTCAGAACGTTAGTGTTTAGGACAAACCAAAGAC
AAGTAAATGTGTTGATTGTTATTGCATATTCTTGACACCGATTACATTTTTGAAACTTTATAGTCAGCTCTAATGATATGCAGCCACTTCACGAA
TTTCATACTTTTAAGTGGATCCGAAGAAAATCATTTAGTAGTAAATAAACGTTTTAGCTTGGAAAACAACAAGAGCTCAACTTGTGTTGCAATCA
AACCAATTTTCGTTTACTCATAATCATAATTTAAGTATGACCTGCTAAAAGATTACAAACCTGCTCATGGTTGCGCATGCTCTCCATGCTCTCGG
GCGCATCGAAGATGCAGTAGCTTGTGCGCGGCTTTTCGCCATCCTGAGATATAGAACCACCAGGCACTGCAATTGAAACGAGGATGGAAAAGGGT
CAGTGAAGAGACTAAACACATTACTTGCAGCGGAAAACTTACCTAGTAGACCTCCTGCAATCAATATGTCAAAGAGAACTTCACCGTAGCGACGA
TAGTCGAGCTTGTTGCCCGCGCTGTCTAGATATTTAGAGATTTGTTCCAGGTCGCCTTCAGTTTTTTCGAGACCAGCAATGACCGCATCACGGAA
TCCCGTTGGGTCATATTTTTCTCTTTCATCTCTTTTTCTGGTCTTGATGCGTTGACCCGATAGCACTGGTCTTTCAGTTTTTTGACTCATACAAT
AAATTGCTGCAAAGGTAAATGTGGATCAGAGATGGAAGCGGTTTTGGTTTGCCCCTGTAAGTTTTTATTTCTGACCAGACTAAATTATCATGGCC
ACTAGATTCATTTTTAGATTTATCTTAATTTTAGTGTAAGATGACTAAGGTGGTCTCCAAGCGGTGGAAAACCGTTCCCTGTATATGTATTCTCG
TTGCGCTCATAATCAAACTACAACATTTTCACCTATGACCGGCGTTTAAGTGGAAACTCTAGTGAAAACTGAGCCTAAGAAAGCCTTAACCTAAA
AATGCCAGCGTACATGTGCTTTAAACACACACATTCAAGAGCGGAGAACGGGCACACTTCACATCTCTTTTTAATTATCTCTCTTTTTCACACAC
ACATACCCACTGTGCATTTTACAGTTTGATAATGTCGACAAAAGAAATAAAAAGAATTGAGAGGTGAGGCGACCAAGAAATCGACATAGAAACGC
AGAATAAAGTGAAATTTTGACGTGGTTACTTGTGTTAGGTAGCGCGCTGGGGAAATGAGGTCATTGTGCATGTAGTGCACATAAAAACGCGCCGA
TGACTGTGTGCTAGTTGGCCGGGAAAATTGTCATAGCAGCGAAAACGCAAAAATTAAATTATCTAGGCTATCAAGTACACATTGGTACATATAAG
GAACGGCAACTTACGCTTTCACCCAAGGATATTAAGTCTGGCCCTGTGTTTGCCGCTTCCGCGTGTCCTTGCAATCAATTGAAATCAGTCGTGTG
CGAGTGTAGTGTGTATGTGTGTGTGTGTGCCTGTTGCTTTTTCACAACTAACGAACGTGCGAGAATATGTAATTTAATTTAACCTCACGAAGC
GCTGGCTGGTTAATGCTTCTCACTCGAGTCGACGAAAAACAAAGAGACAGATGGCAGATCCCTTCTTTTCTTACCTCTCTTTTCTTATGAGCGAG
CTTTTGCACGGTAAAATTGACACGCACGCACACACACAACAACAAAGAAAAGGGGAGAGCAAATAGAAAATATAATTTTTTGTAACGGAATTTAC
TTTTATGCCTTCAAAATAAACGTTAACAATTTTGCTCAGACTACGTCCGGAATTCTATTTTTAACAGCTATCACAATCGGTTACTAGGTATATGT
GTTGTTTGCCTCGAATCCAGCGCCCCTCTGCTCGCACCACTTTGTTAAACGAAATTCGGAGAGCGAATGAGACGACACACGAGCGCACGAACGAA
GCGGACGAGCCGAGAACGAAGACATGTGGTTCGGCGCCATTTTGAAGCGATACACTGACATGGCGAAAGCGGAATGATGGGCACAGGGAAAACGA
AAATTAGGGGGAAACGGTGAGAAAAAATGTGGGATGGGGGTTCAAAGTGTGTATATTGCTGTCGCGCTTATTAAATAATGAGCAAGGTACAGTCG
AACAAAGGCCGACGGCCACCAAATGATTTTTTGCATGAATATATGACTGCCCGATGACTAATCTGGCCTTAGGTACGCACGCAGTTCGTACATAA
CCCCTTTTCCAACGAAAGCGCAGACAAAGGATTGGTCAAGGCCAGAGAAATGACCAGGACCGCGATTTTACTCGCCCTATTTGTCTTTCTGTGTA
CTTAGGTCTACTCTAGCGCTATTTTTCACTCCTATACTTACGATTAAAACAAAAAAATCTGTTTTGCTGCGAATAAAAGTAACTTTTTGCGTAGC
TGTTGGGCTGCTTCTTCTGGATGACTTGCGGTATGACCGTGGCCTGCTTCGTACGCAATGGTACAGAGCTCACTAAGGTGTCCAAAAGGTGGCAA
CATTTTGGTGAAGCTGTTGGCTGGCCCCACTAACCGGACCTGAAAATGGTGCAGCGCTGCCGGACATTTAACGGAATCAAAGATTCCACAAAAGT
CATGTTTGCATTAACAAAATTCATATTTAACCTTAACAAATTCAACAAATTAAGTTAAGTCCATTTTAGTAGCGTTGCGAGGAGTTTATTTTCGA
AAATACGCCTTTGTATATATTATATATTTTTCCTCCACTTTAAACAAAATCGAAAGGTGTCCATTTGTCAGCTATTTAAACAATATGGCATCGCC

FIGURE SHEET 676

GCCTTACTTGCTCAGTAAGAAAATTTAACTGTTTTTTTTTTGCGCACCTGAAAGCGGCGATAGACATTGTTTACTTTTAGTTTATATTTACATTA
TCCA
(SEQ ID NO: 1255)

Exon: 5654..5595
Exon: 5415..5145
Exon: 4471..4223
Exon: 4151..4051
Exon: 3449..3311
Exon: 3044..2879
Exon: 2622..2379
Exon: 2310..1968
Exon: 1229..1001
Start ATG: 4460 (Reverse strand: CAT)

Transcript No. : CT42831
TTTAACAAAGTGGTGCGAGCAGAGGGGCGCTGGATTCGAGGCAAACAACACATATACCTACTCGCTCATAAGAAAAGAGAGGTAAGAAAAGAAGG
GATCTGCCATCTGTCTCTTTGTTTTTCGTCGACTCGAGTGAGAAGCATTAACCAGCCAGCGCTTCGTGAGGTTAAATTAAATTACATATTCTCGC
ACGTTCGTTAGTTGTGAAAAAGCAACAGGCACACACACACACACATACACACTACACTCGCACACGACTGATTTCAATTGATTGCAAGGACACGC
GGAAGCGGCAAACACAGGGCCAGACTTAATATCCTTGGGTGAAAGCCAATTTATTGTATGAGTCAAAAAACTGAAAGACCAGTGCTATCGGGTCA
ACGCATCAAGACCAGAAAAAGAGATGAAAGAGAAAAATATGACCCAACGGGATTCCGTGATGCGGTCATTGCTGGTCTCGAAAAAACTGAAGGCG
ACCTGGAACAAATCTCTAAATATCTAGACAGCGCGGGCAACAAGCTCGACTATCGTCGCTACGGTGAAGTTCTCTTTGACATATTGATTGCAGGA
GGTCTACTAGTGCCTGGTGGTTCTATATCTCAGGATGGCGAAAAGCCGCGCACAAGCTACTGCATCTTCGATGCGCCCGAGAGCATGGAGAGCAT
GCGCAACCATGAGCAGGTATTTGTCAAGCTCATCAGACGGTACAAGTACCTTGAGAAAATGTTCGAAGAGGAGATGGGAAAGGTTCTATTATTCG
TAAAGGGCTTTACTCCTAGTGAACGCATCAAGCTTGCGCGTATGACAGCGCTCTGGTTAGTCAACGGTTCTGTACCGCCAAATGTTTTACTGGTA
CTAAACAACGAGCACCTAATCAAGGATGGCATTGCATTGGAGTTTCTACTAGAGCTGTTCCAGACGTTCAAGCAAGAGAAGGGCATTGCATATCT
GATTCAGGCGCTTAAGAAGGGTGGACTGGAAAGCAAACTTATGGACTTTTTCCCACCGAACAAACGTACTGAGGAATATTTTAAACAAGTTTTTC
TTGACAAAGAACTTAACGAGATCGTCAAGCTACATAAGGCTCAGGCTAGCCAGGAGGCGAAGCGTGAGTTGCAGCAGGCGCTCATCGATGATATC
AACGATGAGAAGCCATATAATGAGATAACCTCAGACATTAAGGACTTCTCGCAGCGCACCAACATTCCCGATCATGAAATAATTGTTATTATTTG
GTCCACCATCATGTCATTGGGCGAATGGAACAAGAAGGAGGAGCTGGTTACCGATCAGGCTGTTCGTCATCTGAAGAACTACTGCCCACTGTTGC
AGGCTTTCGCCTCGACCGACCGTTCGGAATTGGCCCTAATCTTGAAGGTGCAGGAATTCTGCTACGAGAACATGAACTTCATGAAGGCCTTCCAG
AAAATCATTTTGTTGTTCTACAAGACCGAGGTCCTGTCCGAGGAGATCATCTTGCGCTGGTACAAGGAGGGCCACTCAAACAAGGGCAAAATGCA
TTTCCTTGAACAAATGCGAAAGTTTGTCGAATGGCTTCAGTCAGCCGAAGAAGAATCCGAATCTGAGGACGAACAAAAGAATGGCGAGTAAGAAC
TTGGTTGATGGCTAAATGAGGATGAACACAAACGGAGCCGCCCTTTAGCATCCCCATCCAAAAATTCGAAACCAGCACCTGCAACAGCCAGTCGA
ACTATATATAAAACTCACCCCTATGAATTAATGTCATTTTGAAAACTCCACCTATATAAAACTCAAAAATTCCAACAAATAAAGGAGAGAGT
(SEQ ID NO: 1256)

Start ATG: 343 (Reverse strand: CAT)

MSQKTERPVLSGQRIKTRKRDEREKYDPTGFRDAVIAGLEKTEGDLEQISKYLDSAGNKLDYRRYGEVLFDILIAGGLLVPGGSISQDGEKPRTS
YCIFDAPESMESMRNHEQVFVKLIRRYKYLEKMFEEEMGKVLLFVKGFTPSERIKLARMTALWLVNGSVPPNVLLVLNNEHLIKDGIALEFLLEL
FQTFKQEKGIAYLIQALKKGGLESKLMDFFPPNKRTEEYFKQVFLDKELNEIVKLHKAQASQEAKRELQQALIDDINDEKPYNEITSDIKDFSQR
TNIPDHEIIVIIWSTIMSLGEWNKKEELVTDQAVRHLKNYCPLLQAFASTDRSELALILKVQEFCYENMNFMKAFQKIILLFYKTEVLSEEIILR
WYKEGHSNKGKMHFLEQMRKFVEWLQSAEEESESEDEQKNGE*
(SEQ ID NO: 1257)

Celera Sequence No. : 142000013385192
TGCTTCGACGACCTCCTGGTTGACTACCAGACCAGGTACAAAATCGAAAAGATCAAGGTAATGGGTTGGACCTATATGGTGGCCTGTGGCCTCGA
AACGGACCACTACACGGACTTCTCCATCGACATTCCGGTCAAGCAACCGGAAGCTGATTCCGAAATTAGACGAGGATCCAGCGGTGACTATTTCC
CACGACTAGATTAGAGTACAATTGTAAAAGGTACATCTATTCAGTTCTGACTGTCCATTTTGGAAGTACCGAGGACGATGAGATGAGCGGCGATA
ATGTCAGCCAGCCCTACGCCCAAGTGCAAGATGTCGCCGTCCTGGTGATGACCGAGTTTGCCCTGGACTTACTTCGCATCATGCACGACATTCGG
TACAACTACGTGTTCTCGGAGTACGATACATTCTTAACGGGGAGCTTGAAGATAGGTGGGCTGCATTACCTTCACCGTTATCCTAATCCATCCAA
TGATATCTAAGGCATCTCCCATGGATCCGTGATGGCCGGCGTTGTTGGACTCTCGAAACCACACTATGATATCTGGGGTCATACCGTCAATATGG
CCTCCCGGATGTCCTCCACTGGATTGCTGGACAACATCCAAGTAACTCGGCACACGGCAAAGGTGCTGCGACAATTTAACATCCGCTGCAACTAC
CGAGGGCACACGGAGGTAAAGGGAGTGGGCAAGGTGCCCACCTACCTGGTGGTCGTAGACCCGGATCTCACATTCCAAGATCACGACCAAGTGAG
CATGAGTATGAAGGACTCAAAAAGCTGGGTCATCGACACTCTTTCACTGTCATTCACCCCGAGCTTCGTGCCCCCAAAGTCTTCCACTTCGGATG
AAGAGGAGGCTGAAGGAGAGCTCGAGGAAAATGTATCTGAAGGCGATGAACTGGAGGTCTCGATACATGAGCGCCAAAAGGGAGGCATCTTTCTG
GCCGGGAACCTTCATTAATTTAAATTTATTTTAATAGATATATATATATATATATTTATTTAAGCATATATAACACACATATATAGATGTATT
CGTACAGTTCAAAGCAAATGTTTTTCTTGAGGTTAAATACGTTATGATTTGAGCACTCGCTGAAATCATTGCACAACTGGTGACCAAAGTATACG
TATGTTCATAATTCAGAGTCATACATAGTCGTTAGGTTATGTACATGCTACAGATAATACACTCATCTTGACGAATCTCCATCTCCATCACTAAG
AAAGCACCATCCGTGTGATCAGGTTCGGTTTCGTTTGGTTTTGTGCACAGTTTTTAGCTTAAGTAAGCATTGCAGTTGATTTGGGGCATGGGCAT
AGCCCTTACTCGTTGACAGAACTGGAGTTCAGCAGAGCCGTGTCCTCGGGAATGGGCTTCCGCTTGTAGGAGGGCTCAGTGGCTAGGTAGACAAC
CAGCGCCCCGAAGACCACGTACATTACTCCAATCACATTGGCCAACACACCAGCCGGTGGAAGAGTGGAGTAAGCCGGAGTTTTGCTAGAAATGT
CGTCATGGATTAGTCAAGTGATCGATCTAGAATGCATATACACCTACATGGCGAAGATGGCCTTCTCGGTTATGCCCATCAGGGCACTAGCAATA
GCCAGAACGAATCCAAAGAGTCCGAAGTAGATGTGCAGCGGCATCATGGCGATCCTGTAGTTCTCCCTCAACCCCGGCGCCAAAAAGGCCACAAA
TCCGGCCACATACTGCAGCGAGAAGACGATCACCGCGGAGAGCCCCAGCCAAGAGTGCAGGGAGTACATGTTGGGAATGGGCGGATTGGCCAAGT
TGTGGGAATCGAAGACCGTCTTCAGGGCAATCACCGTCAGAATGAATGCACCCATGTGGATGCCGGCGTGGGTAAGCTTCAGAGTCTTCTTGCGC
GTGGTGCGGAAACCACGATAGATCAGAATGGCTGTGGGATTGAATTGAGTTGGATTACCATTTCGAAGCTAGTCAATGGGAGTGGCGTGGCACCT
CTTCCGCTGCATTTACTCACAGTTGCCATACAGGTAAATGAAGCCAATGGTCATGAACAGCGGATGCCAGTTGAACTCCACGCCGGGATTTGAGG TGCCGGCCAGACCGCCGAAGTGCTGGCCAATCCAGGTGGCCACCAGGACGATCATGGTCAGGCCGCACAGCTGGGTGAGCACATAGAGCACCTTA
AAGTTGATCAGCGCTGGATCCATGTTGGCCTTGCCGCTGCCTGAAAAATCCAATAAAAGCTGGGGATGAGCTAAAAATAGAGGCCATTTTACGCA
CAGCACGCATTGGCGATCTAATCGCATAACTCATTCAAGGGTAGAGATATCGGGGCATCGAAAGGGGAAGGGGATCTCAAGCACTCGTTTATATT
TTCCATACTTTTGGTTTATAGCCTCTGCTACGTAAACATGATTCAATTACATGTTCCACCTGCCCGCAGATTAAAATAACCCCCAAGCACTTGCT
GATAACATGCGACCAGAAGTTTAGGGAGCCAATAGGCTTCCCAAAAACCCACTTTAACAGTTGTACATCTGATCCGCTTCGATGGCAGCTGCACT
CGTTGGGTAAACAAACAGTTCCTTTGCCGCCAGCCATCCGATACTGCGATAAACAAGATCTCATCATATCGACTGGCCCTGAGTTAATGGGAAC
GGCCTGTTCCCAGGCACTGGGACACACCCACGACCCCTTTCGCCGGCCACTCACCAGGCGTAATTTGGCTAATTCATGCGTAAACATTTGCGCTT
GTTTACCCAACATTAATTTTCAACGCCAGAGCGTTCTGCCCACTTTATCTGTCGCCTTATCAGTATGTTCTCCAGATAGTCCGAACATCTGATAT
TAAATCGCTTTAAATAGCATCGTACAAGTTCCTCGTGCTTGATGTTGCAGCATGATACATTAAATAAATTAAAGTTCGATTCATTTTACGGAACG
TACGGGTAGTGAAAGTAGCCGTGTTCATAGTTTGGTATAGTATAGATTGGACTTGACTAAGATAGTTTAAAAGGCTAGTAAACTTGTAGGTGCAG
ATGCACTCGATAAGGGCCGCTATCAGCCGCCCTAATTGGCGTTTGGTATGCAAATGGTGTTTTAATTTCGACTCGGGCGAATAATAAGCAAATGA
GCCAAACTGCCAAGTGTTGGCTTGTAAATTGGCTGATAAGTGCGCCGGAGACACTTGTAGCTGGCAATCGCAATTATAAATGCTGGTAACTGGCA
GCAGCCACGCGTCCCCGGTTACTCAATGGGCTCCAGTTGGAGTGCTCCATTTCGACGCAGCTCTGGGTTCCGAGTGAAATTAATTGGCACATTAG
CTGTGACTATGACTGTTAATTATTAGGGTTAAGTGGGCGTGCCAAAGACGCTGACCAGCAAAGCGTTGCAGCAGATCGTGCGCAAAATTTGAAAT
AAACAATCCACATAGGCGCACCAAAAGACCGAAAGTAAAACCCGGGCAGATGACTTTGGATGAATTTGGAAAAGCGTACAAGTCCGAAGACAGCG
GAGCAAAATAAATAAAGTCTGGAAAACCAAAGTGAAATTCAGCTGGTTACTGGTTACTGGTTACTAGTGGCTGCTTGCTGATCGCGGATCGTGAT
GCCGATGGTGATGGTGAAAACCGCGGCGGGGAAAGGGGACGGCTGCAGTCTGTCTTTCGGTGCGTTTTGCTTTAACTTTTACTATAACTAAACAC
TCGGCTTGTTGGTTTATTTTACTTGGCACTAATCAAACTTGCAGCCAAAATCCAATGCCATGCACAGTCTACCTGTTGGTGGTGAAGTTGCCGCC
GCCGTTGGAGTGGCCAACTCAATGCCAGCGATGGTTGTTGCAGGTTGCACTTGTTCTGCTGTCGCAGGTGTTGCAGTTGTTGCTGGTGTCGCTGC
CGCTGGCTTTTCCCCATTAGTCACCGCGATCACTGTGGTCGCCGTGGAGATGGTGGTCGGAACGGCGGCCTGTGGCTGCTCCGGAATCGCTGGCT
CCACCTGGACAACTCCGCTCTCCGGCTTGGTCGCCTGCTCCACGTCCGCGTCCTTCGACATGGTCTGTGCACTTTAAATCAATAATTCACCAATG
GTTCAACCACAAAAAGACATGCAACGTATAATGGACGGTGTTAATTGCCCTAAGACACAGCACAAAAACACTGGTAAATGCTAGTAACTAACTAC
TAGTAACTAATCCGCACGACACCCCGTTAATACAACCGAACACTTCGGCGTGCAATGCGCAACTGAATTTAAAGTTTTCCAGCCGCCGCCCGGCG
ATGGTTAGGAAAAGCTTTTTCCGCTCGCAAATCTCTCGCATGCGACATCGCACACACATATTGCTCATTTCGGTGTGGATAATTGTTTGGTTCTC
GATGCGGATAGGATTCCAGTGGGGTTGGGTTTGCTTTTGACTTTGCCTTTGGCTTTGGGTGCCAACGAATGCTGGTTAGTATGCCGGACCAGGTC
GATCGCTTCTGGTTGGGAAGGGGGTGCATTGATGATTATTTGCATTTCGCATTCCTCGGATCTATTCAAACCATTGTCACTGCGCGGCATTTCAA
TTGCGACTTTGACTTTGATGTTCTGTGCATAGTAATGGGATGGTGCAGTGGAACTGCTTCAATTGGAACTACTTTTTGCCAGAAGGAGTGGAATC
CAAAACGTAAAAGGGTTTACAAAAAGTTTTTGGGTAAAATTTGTTAGTAACAACTATTTCAATATTGTTCTTAGTTTCGAAAGTACATCTACAGT
AAAGTGAAACCTTTAAGGACAACAAGTAGCTTTCCCTCTTAAAGAGCTTAAGTTCATGCTGTGCAATAATGACTGTATGTGCACTTCAACTCACC
CAGTGAGAACAACATGGCGTATACTTGATTGATGCTTCACTCTGCTCAGATAATGCCTGTTTCAATACCGCCTGCTCTTATCTTTAGCAGCAATT
AGTGACTTTAAAGCGATGACGATGGGTTTTTCGCGATTACTTCTGATTTTCGTGGCTACTGCCACGCACTTTACTCTACTTGTTGAACAAACTGC
TTAAAATGCAGGAAGCTGGGCCTTCCATATGGAGGAAAAGCCGTGGAAATTCTGCACAGGCTGCGTGGGCGTGAAAGCCCTAAAGCCCCGCCCAC
TCTGCCGCACTTGGCCATTTCATTTGGCATTTCCACGAGCTTTTCGTTGGAAGCTCAGAACTGTAAACGCCGAAGCACACATGCAAACAAACTTT
CGGGCTCACACCACTGTAGAAAAACCACTTGTTGGATATTATATTAATGGAAAGCCACAACCAAATTATAACTGTTTGTAAACTACATTTAAAGA
CGTAGTTGAAATAGAAACAGGTAAACTTACAGATTTGAAATGAATCAGTAATCCAATAATGTGTTTTGTTTGGAATATTTCCAAAATGTCTTCAA
CGGAAGAGGCAAGAACACAAACAGAAACGGCACAAACACAAAGAGATAATTTGGCAGCATAAGAGAGCGGAATGCTGTGCGAATTTACTACGTCA
GCATTATTATTAACAAGTTAAACTTAAAGCGGCACATTCATTGATACTTAATTTAGTACAGCAAGTCAAGGACACGGTCAAACTTTCACTATCAA
AGGGTTTTAAACTGTAACTCGATCTGTTAACCGCTTCGATTTCTGTTTACTCATTTGGAAAAAAGCGGGACAACCAGGGATGCGAGAATCATAC
TGTAGCTGCGTGTGCTGAAAAAATAGTGTGCATTTAATATACGTTCACATGATGATAGAAAGTACTGACTGTGTGAGTTTTAATTTTAAAAATTT
ACAAACTTTATATTCATATTTAACTAGAGCTTGGAAAACATTTACTTCGAGACCCTGGATTCCCTTATGCCGCCAGTGTGGCCCATTGAGCACGA
CTGAAACACGCTAACGCCTTTAGCTCGGCAGCACTGGCAGCTCCAACAAAAAGCTTCAATTTAAAATAATATTTAGGTAGTCCCACAATAAATGC
TAACAAAATGCT
(SEQ ID NO: 1258)

Exon: 4997..4845
Exon: 2225..2016
Exon: 1931..1568
Exon: 1510..1001
Start ATG: 4860 (Reverse strand: CAT)

Transcript No. : CT42934
AGCCACGAAAATCAGAAGTAATCGCGAAAAACCCATCGTCATCGCTTTAAAGTCACTAATTGCTGCTAAAGATAAGAGCAGGCGGTATTGAAACA
GGCATTATCTGAGCAGAGTGAAGCATCAATCAAGTATACGCCATGTTGTTCTCACTGGGCAGCGGCAAGGCCAACATGGATCCAGCGCTGATCAA
CTTTAAGGTGCTCTATGTGCTCACCCAGCTGTGCGGCCTGACCATGATCGTCCTGGTGGCCACCTGGATTGGCCAGCACTTCGGCGGTCTGGCCG
GCACCTCAAATCCCGGCGTGGAGTTCAACTGGCATCCGCTGTTCATGACCATTGGCTTCATTTACCTGTATGGCAACTCCATTCTGATCTATCGT
GGTTTCCGCACCACGCGCAAGAAGACTCTGAAGCTTACCCACGCCGGCATCCACATGGGTGCATTCATTCTGACGGTGATTGCCCTGAAGACGGT
CTTCGATTCCCACAACTTGGCCAATCCGCCCATTCCCAACATGTACTCCCTGCACTCTTGGCTGGGGCTCTCCGCGGTGATCGTCTTCTCGCTGC
AGTATGTGGCCGGATTTGTGGCCTTTTTGGCGCCGGGGTTGAGGGAGAACTACAGGATCGCCATGATGCCGCTGCACATCTACTTCGGACTCTTT
GGATTCGTTCTGGCTATTGCTAGTGCCCTGATGGGCATAACCGAGAAGGCCATCTTCGCCATCAAAACTCCGGCTTACTCCACTCTTCCACCGGC
TGGTGTGTTGGCCAATGTGATTGGAGTAATGTACGTGGTCTTCGGGGCGCTGGTTGTCTACCTAGCCACTGAGCCCTCCTACAAGCGGAAGCCCA
TTCCCGAGGACACGGCTCTGCTGAACTCCAGTTCTGTCAACGAGTAAGGGCTATGCCCATGCCCCAAATCAACTGCAATGCTTACTTAAGCTAAA
AACTGTGCACAAAACCAAACGAAACCGAACCTGATCACACGGATGGTGCTTTCTTAGTGATGGAGATGGAGATTCGTCAAGATGAGTGTATTATC
TGTAGCATGTACATAACCTAACGACTATGTATGACTCTGAATTATGAACATACGTATACTTTGGTCACCAGTTGTGCAATGATTTCAGCGAGTGC
TCAAATCATAACGTATTTAACCTCAAGAAAAACATTTGCTTTGAACTGTACGAATACATCTATATATGTGTGTTATATATGCTTAAATAAATATA
TA
(SEQ ID NO: 1259)

Start ATG: 138 (Reverse strand: CAT)

MLFSLGSGKANMDPALINFKVLYVLTQLCGLTMIVLVATWIGQHFGGLAGTSNPGVEFNWHPLFMTIGFIYLYGNSILIYRGFRTTRKKTLKLTH
AGIHMGAFILTVIALKTVFDSHNLANPPIPNMYSLHSWLGLSAVIVFSLQYVAGFVAFLAPGLRENYRIAMMPLHIYFGLFGFVLAIASALMGIT
EKAIFAIKTPAYSTLPPAGVLANVIGVMYVVFGALVVYLATEPSYKRKPIPEDTALLNSSSVNE*
(SEQ ID NO: 1260)

Celera Sequence No. : 142000013384600
TCTTTTTAGTAGTACATTTAATGATCACCTAACAGGCAACAAAAATCCTAAAAGGCACTCACTAATAGATTCCCTTCTCGCCAACAGGGATGACC
GCCTTCGTACTGTGCATTCTGGCCATGTCCTCGGGACTGGCTGCACTTTTCTCCAGCCGCATCAAGAAGCTAATCACACCATTGCTGAACAAGAC
GTTCCACAACTTCCTGGGATTCGCGTGCTTTGTGATCGCACTGGTGACCCAGTACTATGGCTACCAGACGGGCTACTTTAAGAGCCGAAGTGAGA
CGGATTTCCAAATCCTGATGAAGTGCCTCACCCTCATATCGTTGGTCCTGTCGAGCTACGGACCGATGAAGGCACTCTATCAGAAATGCAAAAAT
ATATCGCAACAGTTTTAGATAGGATGAAAAGAATCACTCGAATGTATGTAGATAAATAAATGTAATTTTTTCTAAAACCCCATTTTATCGACCTA
TCCAACTATACCAACAACGATTCAAAATTTTATACCTGTTTATTGGTACAACGTGTGATCCATAAACATGACTAAGTATTTTTACAATGCCTCAT
TAGGGAAAACCCGGTTAACCAGCGGTCAGACTTTCATCGTCCGGTACTCCCCCCTGTAAAAGTTATATAACCACCCTTTTGATTGATTTGATTTG
ATAAGGTCTGAAAAAGTAATGAATTGACTATTAGATACACTGCAATTTGCATTTAAGTTTAACCGCTCACTCAAAAAGCCAGCATTTGAATTAAT
CAATCAAAATTATGATCATTTATAATTTAAGTTATACTATTATTCATTTTCCTATAACAGCATTGGGTAGCATGCATCATTTTAAAATCCAAAAC
ATGACCGGGTTTTTTATCTGATCGGTTTGTGACACTTGGAGGCCGCATAATTGATAGTAACTGTCCCAAATAAGTCCAAACTTTTGAAGCCCCGT
AAAAAGAAGATCTTGACTTCCGGCACCTTAAATTAAAAAACCGTGTATTTTGCATGGTGCAGTTTCGTATGTTTATTTAGAAAATCCATATCATT
TCTTCTTAAATCTCTCGCAATAAATAATACTTGGCGCGTGTGTCGCGTTGTGTGTGTGATACGTATATCAGTTAGCAGTAATAATAAATAGCTAG
CGTTAGGTATTAAAATTCATAGTCAATTGGGTAATACAAGGCTGTCTGGCTTTAAAACCCCCTTTCTGGGTAACTTTTGGTAAGAGAAAGTCAAG
ATCTCTATATAGAATCGGGTGAACAGATCTTTAGCATGCGGTAGGTAAATAGGAGTTATCAGCTATCGACTAAAGCCCAGTTAAGAATTGTGTGT
TGGGCAAGGCATATTCGAAATTCGACTTTCTATATCTTTTCATAGTTTCCATAGTTCGCTCCGCTCACAGCTTGTTGCTGCGTCGAATGGCGAAG
GACATTAGCGCGTGCTCCAGCCGCATGTGGTAGGGTAGCTTGCGCTCCAGAATGACTGGCTCCTGGCCATCTGGACAGCACCGGTTGCGGCAGCA
CTCGCACTGGCCGTCGTCATCGTCGTATTCCTGCTGCAGTTCCTGCTCCAGTTCGTAGGCCTTCTTGGCAGCCCGCTGCTCGAAGCGCAAATAGA
AGGCCAGGCAGACAAACAGCATAAATACCAGGGCACACATGGCTCCACTGGCAATGCTCGCCTTCTCCAACATCGGACGCGGCCTCTTGGGCAGG
TAAGTATTGTCGATCTCCTTGTATTCGCATCGCTGTCCCATAAAGCCAATCGCGCACTCGCAGCTGTAAACCGGTAGATCGGCTATCTTCACCGC
AAAGCAATGGGCATCGTTCAAACAGTACCAGGCATCGAAGGTTTCCGGACATTTGTATGTGGGGAATGTAATATTGGGCCTGGGCGTGGTCGTCG
TGGTGGTGCGCATTGTGGTGCTACTAGTGACTGGAGCCTGGGTCGGCGGCAATGCCGTGCCGGACATGGACGAGGAGATCGAAGAGCGCGGCTTG
GGCACCGTACGGCTGGAGCAGGCCTCGACGTGCCACGGATGTGCCAGACAGCCGATCAGTACCAGGGCAACCAGCCCATGTTGTACACTCATTGT
GGAATGCATTACAATTTGTAGCTTTTTAGCGTAGCGTATCGGCTTGTTCGTTTTTTGGCGTGCAACGTTTGGTTGTTTAAAAGCTTAAGAATATT
AAAACTAGTGACTATCACATAAATAAATTAGAATATTCGTTGTCCGCTGCTAGGGCGTCGTCAAATCTCTTTGGAATCGGGTTTCTCTACATAGG
TATGCTGCTGGTGGAACGTAAACGTTGAGTTAGGGGTGATGTGTGTATCTGTGGGGAAGATGGAAAGACATTAGTGGCCAGTAGTCTCCAAGCAC
CATCGATGGTTTTTAACTCTAAAACTGTGTACTCAACAGAAGGGGGAAAATCAAACTGCGTAAAATCATAATTATATATGTATGTATTTATAAAA
GTATAAACTATAATAGATCGCTTTGAATAGTAGTTATGTTACAATCAGCAAATTTTACTCCTTTCTTCACATCCAATTCACTTTCGGTTTAAAAT
TTCATTTACGTTGTCTCCCGTTGATTATCCTAGCTCATCAAAGCTGGCTGTGATATGCGTTGGGTATCCATATCACAACCACTTGATGAGGCTTA
GATAATCAACATCGTACAGGTAAGGAACAGTTTCCTTAACTTTATGAATTAGTAACATGGTTAGTAACAATATTGCACCGCATGTGTGTAAGTCA
GTTCGATAGGGCCCCCTAAGTCTGAGGTGCCAGTCCACCAGTTGAGCCATTTTTCGGTGCTGTGGCATGCATCTGTCCCCCGTTGTTCCGAATTC
AGATCTCTGTTAGCCGCGTTTATTTTCCGATTGCATTTCACTACAAATATTATACAGATTTGAGGCGGACATAGTGTGTTTTATTTATGATGGGC
GTGTGAATTATGTGGCGGGAGGTATTATTATGATTTGATGTACGATACATTACGCTAAGCTCATCAAAGCTGGCTGTGATATGCCGCGCAAAGCG
GAAATGCATTTCACAACCACTTTGAGAGCCCAGCATGAATGCGCCAATATAGTTTTATTGATTGAGGTTTCGGGATACTTGACTGCGGGAGTTCA
GAATTTTCAATTTTGGTTTTCATGCTCATGTAATGATATAAACAAAATCAGACACTTGTTACCGTTTTTATACTTTTTGTGTTCAATTATGCTTT
TTTTTTGGAATTTTCAAATTGTTTTTTGATTGATTTTTTTTTTGCCTTGAGCATCGCGTCGCTCCTCAAAGCTGGCTGTGATATGAATAGGCATA
AAAAGGCAAACATTTCACAACCACTTTGAAGAATGACACAATTCTCCTGTTTCGATTCGATGAGAGCCGAGGTGCAGATTCAGATTCAGATTCTT
CTAGGGGTCTTTTTGCAACGTTCTCACGGCCGTCGGCTTTGAGCCTTGTACTTTTTTGCAGCCACGGCACAATAAACAAATATGAAAAAAGTACG
TAAATAAATAAATGCGACGACGAGACTACAACACGATGATAATGACGATCATGACGACGACGACGATAATGATGATTATGATGATGAGACTACTG
GTACTGGTGATAGATAATACGCAAATGTTGATTGCAATGAATGGCGACAGAGCGAGCGCAAGTGAATGGGACAATTTCGTACATATCTACGCTAT
AGACTGGCCATTGTTTCAACAACAACAACAAAATTCAACAGACACAAACGCACACAACACCGAAGAACAACACTGAAAGAGGGCAAAAAGCAATG
CACCCCAAATAATTATAATAAAAATGTAAACATAATTTTGGCGCCAGCCTTTGGCAATTTGACGCCAAATTTGTTTTTAGATGATTTCTGAGTTC
AAGTTCGGGAATTCAAACTGATAAGAAATGCAAACGATGAATAACAAAACGGAAGAACCGAATTCAGTTGATCCTCCAGAAGATCATTTAAATAA
TCGATTTTATCGAAAAATTTTAAATGCATTACTGACGAAGTTCAATCACTTTAAAATGTGAGCAAAACAAAAACTTTTTATATGAAAAGACGAAT
GCTGTTCACCATTTCGAGCGCCCACTGTGGTGCAATGCAAAAACAGTTATACGTTGGGTGTGGAGACTTATTTATGTATTAGAATGCTTTTACGG
TTAACAATTGCTGCACTCTCTACCCTCTCTTTCTCGCTCACGCGCGGCAAGCGGGCAGCTTATTAAAATTTCCGTTATAAAAATTAAATCCACCG
CCGCTGCTTTTATGTTCATAAATACATGTGATACGTCGCATGCATGTACACATGCACAAATGTATGTATATACACATGTATGTGCGTTTGTGTGC
GAGAGGAAGTCGAAGTAAGGTAATGAGCGTAAAGTCAAGTTGAATAGCCATATAAAATGCGCTGAACTTGCGAGCGTGTAGGTCAAGATCAGCGG
CGGCCGTTTATAATATTTTGTTGGTTTTCGCAAATAGCAATTGACGAAAGTTCGATGATCTTGTAGTACATTTCAATAATGGGGGAATGAGCCAA
CTAGCACGATAGCAACAACAGCAATATATACAAGCATCACAATAATTACAACAGCAACAACAACAACGATCAACTATATTAGAGTGTGGACGGCA
AAAAGTGTGCATACATACATGACAACAAAAACACCCGCTAATAAAAAATACTGTTGTGGCTGCTTCTTCTTCTGCTCTTGCGTCTTTTACAACTT
CTTCGGCAAGCCAGTTGTTGTTGCTGTAATTTTCATGTTGCCTTGCTCTCTTTCATTCTTGGGCGTCGCTGCGAGTTCGTTGGCTCTTCTCGTTT
CTGTATGTGTGTGTGTTTAGAAAACTGTAAGGAAAGCAAAGTGTGTGAAAAATATGGTTAAGGTAAAAAATGCCAATACAGGAACAACAACACAG
CTCGCTCTCTTTTCTCTGCCTGCAGTTTCGAAAAAAAATTTACCGGTTTTTATGTTTTCGCAAAAAAGCTCAAGAAACAAGTCCTACAAGTTTTA
AATCGAGAGAGGAGAGAGCAGAAAAGGCGTGAGAGCCCAAAGAATGCGCATTTAGCAGAGACAACAACCTTTTGAGGTGTGTTGCGTATACGTGC
ATATTCGCACACACACACCACCAACGCTTCAGCTCTCGCTCTCTTTTTCTCGCTTCGCCATCTCACTCTTACTCCATGCCTTTCAGGGGATAAAT
TATGTATGTATATATGTACCATGCGTGTGTGTGTGCGCGGGAATGTTGTGAGGAATTCTAAGAATTTTGCACAAGCGACAAATGAAACGGGGCGC
GGACCACACATACATATATGTATATTCCAAAACCAAACAAAAGTTTTAATAGTTCAAAAAGAAAATTGATTATGCGTCGGTATGCGAGAAGCGCC
AACAGCCGAATGCGAAATATATCACACCAACACAAATACAGTGAAAGCAGAAAAGACGCAGAAGATGGGAAAATTCGAAGACACCGCGTGTAGGC
GTTAAAACCTATTTTTTTTGCCCAACACCAAGCTAAATGAAACACTGCTCACTAAAACACCAATTCACTATGCTTTATCTTCACAAATTACCAAC
TGTTTGCATTTAAACTTGGACAACATTAGGGGGCAGAACGCCGACAACGCACACCGCGCACACGAAAAAACACAACCGCACCGCCAAAGATTCGA
AAACCGAATGCCGAACAACAACAAAATTGGTTCTGAAGATGGAGGTGTTTTTCAGCAGAGCGAGATTCCCTGGCTCACGCTGAGCGGGAGAGAAC
GAGAGCGACAAAGTCTCTCCTCTAAAAATGCGGCATAATAACAACAAAGTGGCGAGCGGCTTTCGAGCTCATGCTGTATGTTGTTGTATACCCGT
TACTTGGAGAGTTAATTGGGTATACGGTGATGGGCTCTTAGGCAAAGAATTTTTCCAAAATACACTTTGCATAATTACTCAAATAAATTGCCTCA GAAGCTACTTTACTCGTTTAAATCTTAAATTAATATTATTCCATTAATGTCAAGCCACACAATACAAAATTCAATAGGAATCACTCACCTATAGC
TGTCATTGCAAACAAATGATATTACCTATTGGACTAAAGGGTATATCTGAGTAGTTACGCTTCGTAAAAAGGGCTCTCTCTTGTTTTGGTTTTTG
TTTTGGTGTTGCCAGAAGATTTCGCACGATGTAGGATCAACATGTTATTGACACGACGTCGCCGACGCCGCCACTTTTAAGCTTGGCGGAGCAAA
AGGCACACAAACAAGAAGCGACGCAGAGCGGCGGTGCAAAAGCACAAAAAAAAAGAGGAAAAATGCGCTCGAGAGCGGAGGGCGTGGCGGTGCGC
AGGGGCGGGGCAGGTAGCCGGACAAACAGGACGAACAGGATGAAACCCAGACGAGTTCGGCCCCACTGCAGATTTCATGGAACTGGCCGAAGGTT
GAGGATGCGGATGCGATGCGCAGGCGCGCAAGTAAACAACATTCCATTCCTCGGGAAATTTCTTCTGGCCGCTCGAGAAGCGCGCCAAAAATAAA
GCTCCGACCGATGTCGTTGCCATAAATATTGCTATTTTGACTTTCCAGATTCTCGCGATTCAACGCCCCTTGAAATGGGAGCAACTTGCTGGAGA
TTCGCGTATCAGGGCTGGAAGAGGGTTTCTCCAATAACTGCAC
(SEQ ID NO: 1261)

Exon: 5693..5602
Exon: 2328..1001
Start ATG: 2087 (Reverse strand: CAT)

Transcript No. : CT43122
TTTGGCGGTGCGGTTGTGTTTTTCGTGTGCGCGGTGTGCGTTGTCGGCGTTCTGCCCCCTAATGTTGTCCAAGTTTAAATGCAAACAGTTGATA
CACACATCACCCCTAACTCAACGTTTACGTTCCACCAGCAGCATACCTATGTAGAGAAACCCGATTCCAAAGAGATTTGACGACGCCCTAGCAGC
GGACAACGAATATTCTAATTTATTTATGTGATAGTCACTAGTTTTAATATTCTTAAGCTTTTAAACAACCAAACGTTGCACGCCAAAAAACGAAC
AAGCCGATACGCTACGCTAAAAAGCTACAAATTGTAATGCATTCCACAATGAGTGTACAACATGGGCTGGTTGCCCTGGTACTGATCGGCTGTCT
GGCACATCCGTGGCACGTCGAGGCCTGCTCCAGCCGTACGGTGCCCAAGCCGCGCTCTTCGATCTCCTCGTCCATGTCCGGCACGGCATTGCCGC
CGACCCAGGCTCCAGTCACTAGTAGCACCACAATGCGCACCACCACGACGACCACGCCCAGGCCCAATATTACATTCCCCACATACAAATGTCCG
GAAACCTTCGATGCCTGGTACTGTTTGAACGATGCCCATTGCTTTGCGGTGAAGATAGCCGATCTACCGGTTTACAGCTGCGAGTGCGCGATTGG
CTTTATGGGACAGCGATGCGAATACAAGGAGATCGACAATACTTACCTGCCCAAGAGGCCGCGTCCGATGTTGGAGAAGGCGAGCATTGCCAGTG
GAGCCATGTGTGCCCTGGTATTTATGCTGTTTGTCTGCCTGGCCTTCTATTTGCGCTTCGAGCAGCGGGCTGCCAAGAAGGCCTACGAACTGGAG
CAGGAACTGCAGCAGGAATACGACGATGACGACGGCCAGTGCGAGTGCTGCCGCAACCGGTGCTGTCCAGATGGCCAGGAGCCAGTCATTCTGGA
GCGCAAGCTACCCTACCACATGCGGCTGGAGCACGCGCTAATGTCCTTCGCCATTCGACGCAGCAACAAGCTGTGAGCGGAGCGAACTATGGAAA
CTATGAAAAGATATAGAAAGTCGAATTTCGAATATGCCTTGCCCAACACACAATTCTTAACTGGGCTTTAGTCGATAGCTGATAACTCCTATTTA
CCTACCGCATGCTAAAGATCTGTTCACCCGATTCTATATAGAGATCTTGACTTTCTCTTACCAAAAGTTACCCAGAAAGGGGGTTTTAAAGCCAG
ACAGCCTTGTATTACCCAATTGACTATGAATTTTAATACCTAACGCTAGCTATTTATTATTACTGCTAACTGATATACGTATCACACACACAACG
CGACACACGCGCCAAGTATTATTTATTGCGAGAGATTTAAGAAGAAATGATATGGATTTTCTAAATAAACATACGAAACTGCACCATGCA
(SEQ ID NO: 1262)

Start ATG: 334 (Reverse strand: CAT)

MSVQHGLVALVLIGCLAHPWHVEACSSRTVPKPRSSISSSMSGTALPPTQAPVTSSTTMRTTTTTTPRPNITFPTYKCPETFDAWYCLNDAHCFA
VKIADLPVYSCECAIGFMGQRCEYKEIDNTYLPKRPRPMLEKASIASGAMCALVFMLFVCLAFYLRFEQRAAKKAYELEQELQQEYDDDDGQCEC
CRNRCCPDGQEPVILERKLPYHMRLEHALMSFAIRRSNKL*
(SEQ ID NO: 1263)

Celera Sequence No. : 142000013384827
GTTACGGTGCTTTTTTGCTCGTTTCTTTTGTGCACTCCTTCTATGCGGTGCCAAATATGAGGAGGTACCTGAAGCTTGGTTGATTTTGTGAGTGT
CTTTTTCCACAGCATATTTTTGTGTATTGGCTACTTTAAAAATTCTATTATATCGTTGTGCTCGTAATGTTGTCCATTCCTTTTAAATATTTTCG
AATTAAATATACCATAGATGTTTCCCTATTACCATAATAGTTTAATAAATATACGTATATGAAATTTTTTTTATCCTATGTTAGTATAAACATGT
TATTCAACAAATAAAAGTAGGTCAGAGGTAATCGCCATCCAGCTCCAGAAAGAGGGGGGAGCTGATAAGATTGCGTTTATGTACCTAATGGGTTG
GGTAAGTGGCTTGGTTTCACAAACACCCTTATTTCAGGTACAAAATAAGTATGTCATAGACGGCGTAAAATTGATAAGATTTTAAAGTCAAAAGA
AAATGAGTTTATTCGCCTGTAACTGCGTTAGAAATCCAAATACACCCGCAATATTATATGTATAGAAAGAAAAAGTTTGATGCAACAACAAATTT
AAAGTTGTTTGGTATTTTGTAATGGAAAGTTTGTGTCACTAAATATGGTTTTACTTGAACGCAGATTGGACATGGTCACACTGCCCACAAAATCA
CGACATTGCGTTATAAATGAAGCACATCTAGTTTTGTGTTGAAAATGTGGTTCACAATTTATATAGCAGGTTATGGTAAAACATCGATCGTTCCG
AAAAATTCCGCTCGTTGGCACATTTCCTAAATTTTTCGTGCGACAGCGGTGATTAATTACAAAAATTATTATTATAATTATATAAAAGTTGGCGA
CCATATCAAAAAGGTTGCTATAAAAACAAATGACAATTTATAGCGGAGTTTCACTCCCAAAGCGATGTTCTCCACCCATTCCAGTCAGTCATGGA
AAATATACCTTCTAAAAAATATATGATTTTTTCGATAGAGATACACGGGCACACTAGACCCACCGATCGCGACTTTGTGTGTGTTAAAATGACGC
GCATATCGTTTTGGGCTAATAATATTGTTCACGTTTTATAAAACAGATACACGGTTAAGCTCTGACCGGTCGTATTATTATCTGTGTGTTCTTGG
TTGACACGTTTATTTCATTTATTCTCATTTAAAGCAACGATGTGAAGAACAGTGCGGGCGTTTCTCAACATAAGAATACATACAAACTTATGCGT
GATGGTGAGCAAATAAAATAGTTCAAAAAATTACTCGGCCACCGCCTTAACCGTACAAACGGAAATACATAAAGGTAAAGGGCTCAACAACAGTA
TTACTGATTAGGCAATTGATTTATATTTCAAACTTCTTAAATAAAGTGTCCACAAATATGTATGTTCTTAGCATAGAGGCGTAGTCGGTGAGTCA
GCCACGCCAACAGTTAACAGTCGTCATTTTGCTGTCTGTCTAACACGCAATTTGTGTGTGTATATGTGAATAAACAGATACCGGTATGCAATCGC
AAAGCTGGTCAACTGTAAAGATCGGTATGTACTCAAAATTAGGTCATCACCTTGTTATGCAGATACATTTGGGAAACAGTTGACTTACTTGGTAT
TGGTTATCAGCCGAAAAGCAAATGGTGATACGGTTTTGCACCTCAGCTTACTCACGGATACATACCTACGTACATAAATGTATGTATACGGTATA
CAGTCTTAGAAAAAATATTAGTACCGACCAGCTAGCGTTTGCCTAAAACGCTTTTACAAAAATAAACGTATATGTTTTAAGTTGTTTTTTGTCAT
AATTAATACATTTATTATTATTTATTTATGAATTTCAGAGCTTTAATAGTAACTAAATTGTTTAAACAAACTTAAAAAAAGATTTCCAAATAAAA
AAATATTTCGTGTGCGTGACGGAATTGCTAGTTCATTAAAGGGAGGTACATATGTACATACATACACATTGCAAAGAGTACAGATCGCTCATCTT
GCATCTCATTTTTCCTAATGTACATATACATATGTACAAACATGTTTATTAAACTGCCTACATGCAAATCTTTGAAGTTTTAAGAAAATAAGCAC
AACTAGTTTGGAAAATCTTGGGAGCCAAGATCTATCTGTCCACTGAATTTCCTATGACCAAGAATGTAAAACCCTTTTTGTTAAACAAATTTTGA
TTAAAGTATACCAGAATAATATTAAACGTATCGTCCGTATCTATAAAAGGTATTAATAGTATTACCTAAATTTAATTTCTCGGTTTTATTCATAA
GAGTGAAAAAATATACAAGTTCCTTTTTAATTTTTTACTTATTGAAAATGTGATTAATTTTTATTTATTATTTTCAGTTTAGAATAAATACGGCC
ACAATTAGTATACATATTTATTCATCGAAACCAACCCACCACAAGAGCATAACCAATTATGTTAAAGTTTATCAGAGGAAAAGGGCAGCAGCCCA
GTGCTGACAGACACCGCCTACAGAAGGACCTTTTTGCTTATCGTAAGGTACAACAAACAATTTCTCTTTCCATTCTATTTTATTTTTTTTTTTT
CGTATATGTAGCCGATTGGTATATTTTGTGGGGTGTCATTTATTTTGATCCTGGGTGGTAAATACATTTTTATGGAAGTTAGAAGAAAGCTTATA
ATTTATTAAGAATAAATAAATACCTCCTTTTCAATCTTTTGTTATGTCTTCTCCTATGTGCATACTTTTGGGCATTAACATTTAGGTAAATTTTT TCCACCGCAACTACAAGTAAACCGCATACACACACAGTATTTTGTAGACTCGCGCCACAAAGCACCGCATAAAAAAGGTTACGGTGCTTTTTGC
TCGTTTCTTTTGTGCACTCCTTCTATGCGGTGCCAAATATGAGGAGGTACCTGAAGCTTTGTTGATTTTGTGAGTGTCTTTTTCCACCGCCTGTT
TTTGGCTACTTTAAAAATTCTATTATATCGTTGTGCTCGTAATGTTGTCCATTCCTTTTAAATATTTTCGAATTAAATATACCATAGATGTTTCC
CTATTACCATAATAGTTTAATAAATATACGTATATGAAATTTTATAAGAATTTTTTTATCCCATGTTAGTATAAACATGTTATTAAACAAATAA
AAGTAGGTCAGAGGTAATCGCCATCCAGCTCCAGAAAGAGGGGGGAGCTGATAAGATTGCTTTTATGTGCTTAATGGGTTGGGTAAATGGCTTGG
TTTCACAAACACCCTTATTTCAGGCACAAAATAAGTATGTCATAGACGGCGTAAAATTGATAAGATTTTAAAGTCAAAAGAAAAAGAATTTATTC
GCCTGTAACTGCGTTAGAAATCCAAATACACCTGCAATATGAATCAAACAAAATCAACTCATAACGAGATCTGATAGCAACTTCTTAAAACTTTT
TTTGTATAAAAATACAATTTATACAATTAGATAAGATTTACCAAACCTTTTTCGATCAATGTAAATATAGTATGATAGTAGGACTGCTGTCTA
CAGTGATGTTTATAAGAGACATACTTAAGAGCAGCATTTAAAGCTTTGGGCGCTTTTTGAACTTAATTTAAATTCAAACCTCAATATTTATTGAG
GTTTTTATTCCCGTTAATTGTAAAGAAAAATGCTGTATTAGATTCGGTAAAAGTATGTAAATGGTTTAAGAAAGCGTTCCCGACTCTATAAAGTG
GCAAGTAATCTGACGATTTACCAGATCTTGGGAACTGAAAAAACTAGAATGTTTTGGAAAACCCTTTTACAATTAAGAAATGAACCAAACAATTT
TGAATTATTAAGAATCTGTAATTGCTTTTTGAAACTTTTTAATATTTTTTTCTTTTAGACGGCACAGCATGGCTTTCCTCATAAGCCTTCGGCTC
TTGCGTATGATCCAGTTTTGAAACTTATGGCAATAGGGACGCAAACAGGGGCTTTAAAAGTTTTCGGTCAACCCGGAGTTGAATTGTACGGTCAG
CATACTTTGTTAAACAATTCAGCATCGGAGCTTAATGTACAATTACTTGAATGGGTGTATGGAACTGGTCGCATACTTTCGTTGACGGCAGCGAA
TCAATTAATTCTATGGGAGCCAGTTGGAGCAACGTTGCTGCCAATCAAAACACTACCGTTTGACGGCAACTTAAAAAAGTTTCATCGCTGTGCT
GTTCTCTCAGTAAGGATCTGCTATGGATTGGAACAGAAGGTGGAAACATCTATCAACTGGATTTACATACATTTACCATTAAGGAGCCTGTAATT
TACCATGACGTTGTGCTAGAGCAGGTGCCACCAGCCTACAAGCTAAATCCTGGTGCAATTGAGTCAATCCGCCAACTTCCAAACTCCCCTAGCAA
ACTTCTAGTTGCATACAATCGCGGCCTTTGTGTTTTGTGGGATTTTGAAAGCGCATCTGTCCAGCGAGCATACATAGCCCCTGGACATGGACAGA
GCGTTGGTCTTACAGTGAACTTCGAAGGATCTGAATTTACCTGGTACCACGCTGATGGTTCATACGCCACTTGGAGCATAGATAACCCAGAACCG
CCGTCGAATGTTAATTATGTGCCTTATGGACCTGATCCATGCAAAAGCATAAATCGACTGTACAAAGGCAAGCGAAGGTTAATATAACTTAAACA
CAAAGTTTTTTAGATGTGTACTAATTTCTCGTTCTTTTAGATCCAACGATGTAATTGTTTTTTCCGGCGGCATGCCACGGTCAGCATATGGTGAT
CACAATTGTGTGTCCGTTCACGCCAGCGATGGACACAAAGTGTGTCTTGACTTTACGTCTAAAGTGATTGACTTTTTTGTGACCTTTGAAAATAA
TAGAGATGTCGCTGAAGTTCTTGTTGTACTACTTGAAGAGGAACTCTGCGCTTACGATCTTACTGACCCTAATATTTGTGCTATCAAAGCGCCAT
ATCTTCACTCTGTCCATGCATCAGCTGTCACTTGCAATTACCTTGCTTCTGAAGTCGTACAGTCGGTATATGAAAGTATTTTAAGAGCTGGAGAT
GAACAAGACATTGACTATAGCAATATTAGCTGGCCTATCACTGGCGGTACTCTCCCGGATAACTTAGAAGAATCTGTAGAAGAGGACGCGACTAA
GCTTTATGAGATTTTGTTAACTGGTCACGAAGATGGTTCTGTTAAATTTTGGGACTGCACTGGAGTGTTGCTTAAACCAATTTATAATTTTAAAA
CTAGCAGCATTTTTGGAAGTGAGTCAGACTTCCGAGATGACGCAGCTGCAGATATGAGTGCCGGAACAAGTCGATGAAGGAGAACCGCCATTTCGG
AAATCAGGACTTTTTGATCCTTATTCAGATGACCCTCGTTTAGCAGTGAAGAAAATAGCATTCTGCCCAAAAAACCGGACAACTTATTGTTGGTGG
CACAGCGGGCCAAATAGTTATAGCCGACTTCATAGACTTACCCGAAAAAGTGTCTTTAAAATACATTTCAATGAATTTGGTCAGCGATCGTGATG
GATTTGTGTGGAAGGGTCACGATCAGTTAAACGTGCGATCGAACTTATTAGACGGAGAAGCAATTCCTACGACGGAACGTGGTGTAAATATATCG
GGAGTACTGCAAGTTTTGCCGCCAGCCAGCATAACATGCATGGCACTCGAAGCAAGCTGGGGCCTAGTATCTGGTGGGACTGCGCACGGCTTAGT
TCTCTTTGACTTCAAAAACTTTGTTCCAGTATTTCATCGCTGCACTTTAAACCCAAATGATCTTACTGGAGCAGGAGAGCAGCTGTCTCGTCGAA
AGTCTTTTAAGAAATCATTGAGGGAGTCATTTAGAAAGCTTCGCAAGGGTCGATCGACCAGGACCAACCAGAGCAATCAAGTACCAACAACGGTT
AGTAAGATAATATATACTCAACTAGTCTTTTATATTAAATTCACAATCCTACAGCTGGAAGCAAGACCCGTCGAGAGGCAAATAGAGGCTCGTTG
TGCAGATGACGGGCTAGGATCCATGGTGCGATGTTTACTATTTGCCAAAACTTATGTTACTAATGGTAATCAACATTTTGTACTGTTATTAGTTT
TGATGTAACGATAAAAAAAAAAAAAGGTAACGGAAATAGTCTCTGAACCACGGCCTCGCGAGAATTGAACCCAAAAGCTAAAAACATACAGTGCT
TTTCATTTTGGGACGCCCAGAGCTTTAATTATATTTTTGTGCAACAAATTTTTATGCATTGGATATATTGATCAAAGTTTTAAAGGTATATGTAT
TTATGATCAGTTTAAACAGCCGACTACATTTGACTATGTCCGTCCTTAGAAAGAAATTCAGTCATTACAATATTCCTTGCTAGTCTATCGATATG
CTATAAGTGTTAAAAGTGCTTTTGCATTTACTCTGGTTTGACAATATATTTTATTGATATTGATTTCGTTTCATTTACTAGTTGGAAAACAGTTC
TTAAACTAATTAAATCATAGTCTTTTTGTTTTCGCGATTTCGATCTATATGGCAAATTTTGTTTTTAAAATTTCACCTATCCTCCTACTATTTCT
GTAATGGGTAACTCGACTGTAGCGTCTATTCTTTTGGTGTTCTGTATATGTACATCTAATTTGTTGTATAATTTTTACATTTTCAGTCAACATAA
CGTCGCCAACTTTGTGGTCAGCAACAAATGCCAGTACAGTCTCGGTTTTCCTTCTGCATTTGCCACCAGCGCAGACCGCGGCAACTGCCGTCCCG
TCGGCAAGTGGCAATGCACCACCACACATGCCCCGCCGAATTTCTGCGCAGCTTGCTAAAGAAATACAATTAAAACATCGTGCTCCTGTGGTGGG
TATTTCTATTTTGATCAGGCGGGTAGCCCTGTCGATCAGCTGAACGCCGGTGAAAACGGGAGTCCACCGCATCGTGTACTTATTGCTTCCGAGG
AACAGTTCAAGGTGTTTTCACTTCCGCAACTAAAGCCGATTAACAAATATAAGCTTACCGCTAACGAAGGTGCTCGGATTCGCCGCATCCATTTT
GGTTCGTTTAGTTGTCGCATATCCCCGGAAACACTGCAGAGTATGCACGGTTGTAGCCCAACTAAGTCCACGCGTTCACATGGCGATGGAGAGGC
GGATCCTAATATCAGTGGAAGCTTGGCTGTAAGTCGTGGAGATGTATATAACGAAACAGCATTGATATGTTTAACGAATATGGGCGATATCATGG
TTTTATCAGTACCTGAATTAAAAAGACAGCTGAATGCCGCAGCAGTGCGACGGGAAGACATTAAGTAAGTCACGCATAGTGCTATTATTTTAATT
TTTTGGACCTAATACTGTATTTTAACTTTTCAGTGGAGTTTCGTCACTTTGCTTTACAAACTCTGGAGAAGCACTGTATATGATGTCTTCTTCTG
AACTGCAGCGTATTGCTTTAGCCACGTCCAGAGTCGTGCAACCCACTGGCGTTGTTCCAGTAGAACCATTAGAAAATGAAGAGTCTGTGTTGGAA
GAAAATGATGCAGAGAATAATAAGGAAACCTACGCATGTGATGAAGTTGTGAATACATATGAAATTAAAAATCCATCAGGCATTTCAATATGCAC
AAGGCCTGCAGAGGAAAACGTTGGAAGAAATAGTGTTCAGCAAGTTAATGGAGTCAACATTTCAAATTCACCTAATCAAGCTAACGAGACTATCA
GCAGCTCTATTGGCGATATTACCGTTGACTCGGTGCGCGACCATTTAAATATGACGACCACCACTTTGTGTTCTATTAATACAGAGGAAACCATT
GGTGAGTAATCATTTATTTACTAACATTATTCCACCTATTTTAATTTGCTGTTTTGTACGTATCTACATTTAAATGTTTTCGTTTCGACATTAGT
TACTTTCGGCAACATAATTCTTATAAAAATTTACTTTTTAAAAACTTGATTTTAAGTATACGCACCAAACAACTTTAAATATATACTTTTATCTT
ATTTTAAAAGCACGGGCCCACATTATATCTGTACATAACTTTTTTTTTCTGTCATCTCTATGAAAATGTAGGTCGCCTATCTGTACTTAGCACGC
AAACCAACAAAGCCAGTACTACCGTAAACATGAGTGAAATTCCAAATATTAATATTTCTAATTTAGAGGACTTGGAATCGAAAAGGTGTGCTTCT
ACAAGAAACATTGACATAAGCTTTAACCTACTAATTTTTTTTTTTTTACCTAACAGAAATACGACGGAAACGAGTACTAGTTCTGTTGTAATTAAA
TCTATAATTACAAACATTTCTCATGAAAAAACGAACGGAGACAACAAAATAGGAACGCCAAAAACAGCGCCTGAAGAAAGCCAATTTTAACATTG
ACAGAAGCCGTAACCTACTAATTATTTTATACCTTTACAGAAATACGACGCAAACGAGTACTAGTCCTGATGTAATTTAATCTATAATTACAAAC
ATGTCTCACTAAAAATCGAACGGGGACAGCAAAATAGGAACGCAAAAAAATTAAATTAAATTAAACGCGATTTACATACAAACAGAAATGACAGA
ATGATAATATAAAATATTCATTTTTTATTTGGCTTAAGCGATGTTGTTGTTCCAAAACCATATAATTATTTATGATTTTATGTAATGTTTTCATG
TATTTTCGCGTAGTGACTTTATACCCTTTACCCGTATGATGAAACGAAACATGATATTTGTAGAAAGGTACAAAGGATAAAAGTTGACATTTAAG
GCCGATTGTAAAATATTAAAACGCAACCTGGATAACATGCCGATTAATTACTTCTGTTCGTCCGTATAAACACAAATACCGATAAATTGGTCCGT
CCCCATTTAATAAATTGTATATTAAAATGGTCTTTATTTTGGATAAATAATTCAAATTATATAGGAACATTTGGGTTTTAAGGGATAGAAACAGC
GCTGGTGTCTTTCATTTCCGTTCGTATGACCGTTCAAAGATTATAAAAAAATTGTCGTGCCCACATTTTTTAAATTTCTTTTATTTTCGGTTAAA
ATATTGTGATACAAAAAAATGCCCTTACAAAATTAGGACAACAACAATTTGCTTTATTATGATGAACAAATTAGGAGTACAAAAAATAGCCTGAT
GCAAGGATGGGGAGAAAAAAGACCTTGAAGTTCAAAAGAATTTGTTGTATCAAATCCTCAATAAGAAAACTACTTAAAATTAAAAGCGTGTTTCA
AATTAATTGTAGAATATTTCGTAAAATGAAATTGCAAACTTTTTTAGCACGAAATTACATGTATTTAATTCTTTGGCTAATACGTCAGTTAAAAA
AGGCTACATTTTGATGATACTCACAAATGTAATTTTTGCATTCTACACAGGTGCAATTAAAAAATTATGGTTTTTATGAGTTTTAGAGGGAAGAA
AATATGTCAATATGAGAAGTAAGTTAATGAGCCTTCAAGTACTTTAGTACATAATGTAATTTAATTTTAGAAATCCTACGGCTTTATATTCAATT

FIGURE SHEET 681

GTAAAGTATTTTAAAATTCCTGACGATTTGTAGTAATTGTTTTGTTCTTAGCTTTTTTGCATTCTCCTCCGTTACTCCGTTACTCGTATAGTAAA
AGGTATAGTATATACAATAGTATTGTAGATTCGTTGAGAAGTATGTTACAGGCAGAAGGAAGCTTTTCCGACCATATAAAGTATATAATTGAGTA
TTTAGCTTAGGATTATTAATAAAACATGTATTTTATTTAACAAACTGGCTTTACAATATTTTGTGGAAGAACACCGATCTATTTAGTTGTAGGTC
TCAAACTGAAAACTCCTAATTTTGACTTATTTAAAGATCATACCTCGGTTTTGAGCCTTAGAGGTTTGTATGAGTGATTTTCTAGAATGATCTTT
GTACTTCGTTACAATAAATTGTTTTCTTCTACTCTAATATAGTTGGAATCGAGTAATCCCTAGATAAGAGTTAGGCTTAAAATAGTAAATTACAA
ATATTGAATTGGACATTACAATTGCATATTCTCAGCTTGCTGTATTGTAAAAATTAATTATTAACTCGAAGAGATTCGGCAATTAATACGTCCCT
ATTCGCATTGTTTTTACTTGGGGAAATTTTATTGAAAAACTAGATTCTCTGTTACAATCAGATATGAGAACAAGTTATTGCACCAGCACATCTCT
CGGCCAGCTCAATTCAATTAAATAGCTAAGCACTTGTTGCGAATTCATGCTTGGAGTGTTTACGTAAGATTTGTAAAAATAACTAAACTGGATTC
TCCACATTCTTGCGTAGCTGTGTGATTCTACTGTCACAACTCTCCGTCGACGATTTCTAGAGCCATCTTCTTGCGGAAGTACAACATTTCCGACT
GGGTAAAGGTAATTGGCACATCACACGTTATATACTCGGCGAACATGCAGCTGAAGATACCGCAATCGCTGCCATCTAACTGTCGTGGTATATTC
TGCACGCTCTCAATAACAAAATCGCTGGTATCAAACTGCTTTTTGGGCTTGAATATTGACTCTTCGCGTAGATATTTCTCTAGAGCGTCCAGCAC
TGGTCGGTTTGGCTTTCCCTTTGAGTCATAATACCGGATTGTCTTGTTCCGCAAGTGTATGATGGCCATGCACCAGTGGACGCCGTTGCAGTGCA
CTGGTACCGGGATTATGTCCTTGCTGAACAAGTCCACTTTGCGAGTCCAGCGCTTAATGCCTGCATGCCCAGCTTGCAGGAGGCGGGGCACGAA
(SEQ ID NO: 1264)

Exon: 1001..1309
Exon: 2358..2517
Exon: 3859..4637
Exon: 4696..5887
Exon: 5945..6050
Exon: 6642..7284
Exon: 7349..7791
Exon: 8052..8160
Exon: 8226..9734
Start ATG: 2434

Transcript No. : CT43225
ACACTAGACCCACCGATCGCGACTTTGTGTGTGTTAAAATGACGCGCATATCGTTTTGGGCTAATAATATTGTTCACGTTTTATAAAACAGATAC
ACGGTTAAGCTCTGACCGGTCGTATTATTATCTGTGTGTTCTTGGTTGACACGTTTATTTCATTTATTCTCATTTAAAGCAACGATGTGAAGAAC
AGTGCGGGCGTTTCTCAACATAAGAATACATACAAACTTATGCGTGATGGTGAGCAAATAAAATAGTTCAAAAAATTACTCGGCCACCGCCTTAA
CCGTACAAACGGAAATACATAAAGTTTAGAATAAATACGGCCACAATTAGTATACATATTTATTCATCGAAACCAACCCACCACAAGAGCATAAC
CAATTATGTTAAAGTTTATCAGAGGAAAAGGGCAGCAGCCCAGTGCTGACAGACACCGCCTACAGAAGGACCTTTTTGCTTATCGTAAGACGGCA
CAGCATGGCTTTCCTCATAAGCCTTCGGCTCTTGCGTATGATCCAGTTTTGAAACTTATGGCAATAGGGACGCAAACAGGGGCTTTAAAAGTTTT
CGGTCAACCCGGAGTTGAATTGTACGGTCAGCATACTTTGTTAAACAATTCAGCATCGGAGCTTAATGTACAATTACTTGAATGGGTGTATGGAA
CTGGTCGCATACTTTCGTTGACGGCAGCGAATCAATTAATTCTATGGGAGCCAGTTGGAGCAACGTTGCTGCCAATCAAAACACTACCGTTTGAC
GGCAAACTTAAAAAAGTTTCATCGCTGTGCTGTTCTCTCAGTAAGGATCTGCTATGGATTGGAACAGAAGGTGGAAACATCTATCAACTGGATTT
ACATACATTTACCATTAAGGAGCCTGTAATTTACCATGACGTTGTGCTAGAGCAGGTGCCACCAGCCTACAAGCTAAATCCTGGTGCAATTGAGT
CAATCCGCCAACTTCCAAACTCCCCTAGCAAACTTCTAGTTGCATACAATCGCGGCCTTTGTGTTTTGTGGGATTTTGAAAGCGCATCTGTCCAG
CGAGCATACATAGCCCCTGGACATGGACAGAGCGTTGGTCTTACAGTGAACTTCGAAGGATCTGAATTTACCTGGTACCACGCTGATGGTTCATA
CGCCACTTGGAGCATAGATAACCCAGAACCGCCGTCGAATGTTAATTATGTGCCTTATGGACCTGATCCATGCAAAAGCATAAATCGACTGTACA
AAGGCAAGCGAAGATCCAACGATGTAATTGTTTTTTCCGGCGGCATGCCACGGTCAGCATATGGTGATCACAATTGTGTGTCCGTTCACGCCAGC
GATGGACACAAAGTGTGTCTTGACTTTACGTCTAAAGTGATTGACTTTTTTGTGACCTTTGAAAATAATAGAGATGTCGCTGAAGTTCTTGTTGT
ACTACTTGAAGAGGAACTCTGCGCTTACGATCTTACTGACCCTAATATTTGTGCTATCAAAGCGCCATATCTTCACTCTGTCCATGCATCAGCTG
TCACTTGCAATTACCTTGCTTCTGAAGTCGTACAGTCGGTATATGAAAGTATTTTAAGAGCTGGAGATGAACAAGACATTGACTATAGCAATATT
AGCTGGCCTATCACTGGCGGTACTCTCCCGGATAACTTAGAAGAATCTGTAGAAGAGGACGCGACTAAGCTTTATGAGATTTTGTTAACTGGTCA
CGAAGATGGTTCTGTTAAATTTTGGGACTGCACTGGAGTGTTGCTTAAACCAATTTATAATTTTAAAACTAGCAGCATTTTTGGAAGTGAGTCAG
ACTTCCGAGATGACGCAGCTGCAGATATGAGTGCGGAACAAGTCGATGAAGGAGAACCGCCATTTCGGAAATCAGGACTTTTTGATCCTTATTCA
GATGACCCTCGTTTAGCAGTGAAGAAAATAGCATTCTGCCCAAAAACCGGACAACTTATTGTTGGTGGCACAGCGGGCCAAATAGTTATAGCCGA
CTTCATAGACTTACCCGAAAAAGTGTCTTTAAAATACATTTCAATGAATTTGGTCAGCGATCGTGATGGATTTGTGTGGAAGGGTCACGATCAGT
TAAACGTGCGATCGAACTTATTAGACGGAGAAGCAATTCCTACGACGGAACGTGGTGTAAATATATCGGGAGTACTGCAAGTTTTGCCGCCAGCC
AGCATAACATGCATGGCACTCGAAGCAAGCTGGGGCCTAGTATCTGGTGGACTGCGCACGGCTTAGTTCTCTTTGACTTCAAAAACTTTGTTCC
AGTATTTCATCGCTGCACTTTAAACCCAAATGATCTTACTGGAGCAGGAGAGCAGCTGTCTCGTCGAAAGTCTTTTAAGAAATCATTGAGGGAGT
CATTTAGAAAGCTTCGCAAGGGTCGATCGACCAGGACCAACCAGAGCAATCAAGTACCAACAACGCTGGAAGCAAGACCCGTCGAGAGGCAAATA
GAGGCTCGTTGTGCAGATGACGGGCTAGGATCCATGGTGCGATGTTTACTATTTGCCAAAACTTATGTTACTAATGTCAACATAACGTCGCCAAC
TTTGTGGTCAGCAACAAATGCCAGTACAGTCTCGGTTTTCCTTCTGCATTTGCCACCAGCGCAGACCGCGGCAACTGCCGTCCCGTCGGCAAGTG
GCAATGCACCACCACACATGCCCCGCCGAATTTCTGCGCAGCTTGCTAAAGAAATACAATTAAAACATCGTGCTCCTGTGGTGGGTATTTCTATT
TTTGATCAGGCGGGTAGCCCTGTCGATCAGCTGAACGCCGGTGAAAACGGAGTCCACCGCATCGTGTACTTATTGCTTCCGAGGAACAGTTCAA
GGTGTTTTCACTTCCGCAACTAAAGCCGATTAACAAATATAAGCTTACCGCTAACGAAGGTGCTCGGATTCGCCGCATCCATTTTGGTTCGTTTA
GTTGTCGCATATCCCCGGAAACACTGCAGAGTATGCACGGTTGTAGCCCAACTAAGTCCACGCGTTCACATGGCGATGGAGAGGCGGATCCTAAT
ATCAGTGGAAGCTTGGCTGTAAGTCGTGGAGATGTATATAACGAAACAGCATTGATATGTTTAACGAATATGGGCGATATCATGGTTTTATCAGT
ACCTGAATTAAAAAGACAGCTGAATGCCGCAGCAGTGCGACGGGAAGACATTAATGGAGTTTCGTCACTTTGCTTTACAAACTCTGGAGAAGCAC
TGTATATGATGTCTTCTTCTGAACTGCAGCGTATTGCTTTAGCCACGTCCAGAGTCGTGCAACCCACTGGCGTTGTTCCAGTAGAACCATTAGAA
AATGAAGAGTCTGTGTTGGAAGAAAATGATGCAGAGAATAATAAGGAAACCTACGCATGTGATGAAGTTGTGAATACATATGAAATTAAAAATCC
ATCAGGCATTTCAATATGCACAAGGCCTGCAGAGGAAAACGTTGGAAGAAATAGTGTTCAGCAAGTTAATGGAGTCAACATTTCAAATTCACCTA
ATCAAGCTAACGAGACTATCAGCAGCTCTATTGGCGATATTACCGTTGACTCGGTGCGCGACCATTTAAATATGACGACCACCACTTTGTGTTCT
ATTAATACAGAGGAAACCATTGGTCGCCTATCTGTACTTAGCACGCAAACCAACAAAGCCAGTACTACCGTAAACATGAGTGAAATTCCAAATAT
TAATATTTCTAATTTAGAGGACTTGGAATCGAAAAGAAATACGACGGAAACGAGTACTAGTTCTGTTGTAATTAAATCTATAATTACAAACATTT
CTCATGAAAAAACGAACGGAGACAACAAAATAGGAACGCCAAAAACAGCGCCTGAAGAAAGCCAATTTTAACATTGACAGAAGCCGTAACCTACT
AATTATTTTATACCTTTACAGAAATACGACGCAAACGAGTACTAGTCCTGATGTAATTTAATCTATAATTACAAACATGTCTCACTAAAAATCGA
ACGGGGACAGCAAAATAGGAACGCAAAAAAATTAAATTAAATTAAACGCGATTTACATACAAACAGAAATGACAGAATGATAATATAAAATATTC
ATTTTTTATTTGGCTTAAGCGATGTTGTTGTTCCAAAACCATATAATTATTTATGATTTTATGTAATGTTTTCATGTATTTTCGCGTAGTGACTT TATACCCTTTACCCGTATGATGAAACGAAACATGATATTTGTAGAAAGGTACAAAGGATAAAAGTTGACATTTAAGGCCGATTGTAAAATATTAA
AACGCAACCTGGATAACATGCCGATTAATTACTTCTGTTCGTCCGTATAAACACAAATACCGATAAATTGGTCCGTCCCCATTTAATAAATTGTA
TATTAAAATGGTCTTTATTTTGGATAAATAATTCAAATTATATAGGAACATTTGGGTTTTAAGGGATAGAAACAGCGCTGGTGTCTTTCATTTCC
GTTCGTATGACCGTTCAAAGATTATAAAAAAATTGTCGTGCCCACATTTTTTAAATTTCTTTTATTTTCGGTTAAAATATTGTGATACAAAAAAA
TGCCCTTACAAAATTAGGACAACAACAATTTGCTTTATTATGATGAACAAATTAGGAGTACAAAAAATAGCCTGATGCAAGGATGGGGAGAAAAA
AGACCTTGAAGTTCAAAAGAATTTGTTGTATCAAATCCTCAATAAGAAAACTACTTAAAATTAAAAGCGTGTTTCAAATTAATTGTAGAATATTT
CGTAAAATGAAATTGCAAACTTTTTTAGCACGAAATTACATGTATTTAATTCTTTGGCTAATACGTCAGTTAAAAAAGGCTACATTTTGATGATA
CTCACAAATGTAATTTTTGCATTCTACACAGGTGCAATTAAAAAATTATGGTTTTTATGAGTTTTAGAGGGAAGAAAATATGTCAATATGAGAAG
TAAGTTAATGAGCCTTCAAGTACTTTAGTACATAATGTAATTTAATTTTAGAAATCCTACGGCTTTATATTCAATTGTAAAGTATTTTAAAATTC
CTGACGATTTGTAGTAATTGTTTTGTTCTTAGCTTTTTTGCATTCTCCTCCGTTACTCCGTTACTCGTATAGTAAAAGGTATAGTATATACAATA
GTATTGTAGATTCGTTGAGAAGTATGTTACAGGCAGAAGGAAGCTTTTCCGACCATATAAAGTATATAATTGAGTATTTAGCTTAGGATTATTAA
TAAAACATGTATTTTATTTAACAAA
(SEQ ID NO: 1265)

Start ATG: 386

MLKFIRGKGQQPSADRHRLQKDLFAYRKTAQHGFPHKPSALAYDPVLKLMAIGTQTGALKVFGQPGVELYGQHTLLNNSASELNVQLLEWVYGTG
RILSLTAANQLILWEPVGATLLPIKTLPFDGKLKKVSSLCCSLSKDLLWIGTEGGNIYQLDLHTFTIKEPVIYHDVVLEQVPPAYKLNPGAIESI
RQLPNSPSKLLVAYNRGLCVLWDFESASVQRAYIAPGHGQSVGLTVNFEGSEFTWYHADGSYATWSIDNPEPPSNVNYVPYGPDPCKSINRLYKG
KRRSNDVIVFSGGMPRSAYGDHNCVSVHASDGHKVCLDFTSKVIDFFVTFENNRDVAEVLVVLLEEELCAYDLTDPNICAIKAPYLHSVHASAVT
CNYLASEVVQSVYESILRAGDEQDIDYSNISWPITGGTLPDNLEESVEEDATKLYEILLTGHEDGSVKFWDCTGVLLKPIYNFKTSSIFGSESDF
RDDAAADMSAEQVDEGEPPFRKSGLFDPYSDDPRLAVKKIAFCPKTGQLIVGGTAGQIVIADFIDLPEKVSLKYISMNLVSDRDGFVWKGHDQLN
VRSNLLDGEAIPTTERGVNISGVLQVLPPASITCMALEASWGLVSGGTAHGLVLFDFKNFVPVFHRCTLNPNDLTGAGEQLSRRKSFKKSLRESF
RKLRKGRSTRTNQSNQVPTTLEARPVERQIEARCADDGLGSMVRCLLFAKTYVTNVNITSPTLWSATNASTVSVFLLHLPPAQTAATAVPSASGN
APPHMPRRISAQLAKEIQLKHRAPVVGISIFDQAGSPVDQLNAGENGSPPHRVLIASEEQFKVFSLPQLKPINKYKLTANEGARIRRIHFGSFSC
RISPETLQSMHGCSPTKSTRSHGDGEADPNISGSLAVSRGDVYNETALICLTNMGDIMVLSVPELKRQLNAAAVRREDINGVSSLCFTNSGEALY
MMSSSELQRIALATSRVVQPTGVVPVEPLENEESVLEENDAENNKETYACDEVVNTYEIKNPSGISICTRPAEENVGRNSVQQVNGVNISNSPNQ
ANETISSSIGDITVDSVRDHLNMTTTTLCSINTEETIGRLSVLSTQTNKASTTVNMSEIPNINISNLEDLESKRNTTETSTSSVVIKSIITNISH
EKTNGDNKIGTPKTAPEESQF*
(SEQ ID NO: 1266)

Celera Sequence No. : 142000013384827
CGTTTCTTTTGTGCACTCCTTCTATGCGGTGCCAAATATGAGGAGGTACCTGAAGCTTGGTTGATTTTGTGAGTGTCTTTTTCCACAGCATATTT
TTGTGTATTGGCTACTTTAAAAATTCTATTATATCGTTGTGCTCGTAATGTTGTCCATTCCTTTTAAATATTTTCGAATTAAATATACCATAGAT
GTTTCCCTATTACCATAATAGTTTAATAAATATACGTATATGAAATTTTTTTTATCCTATGTTAGTATAAACATGTTATTCAACAAATAAAAGTA
GGTCAGAGGTAATCGCCATCCAGCTCCAGAAAGAGGGGGGAGCTGATAAGATTGCGTTTATGTACCTAATGGGTTGGGTAAGTGGCTTGGTTTCA
CAAACACCCTTATTTCAGGTACAAAATAAGTATGTCATAGACGGCGTAAAATTGATAAGATTTTAAAGTCAAAAGAAAATGAGTTTATTCGCCTG
TAACTGCGTTAGAAATCCAAATACACCCGCAATATTATATGTATAGAAAGAAAAAGTTTGATGCAACAACAAATTTAAAGTTGTTTGGTATTTTG
TAATGGAAAGTTTGTGTCACTAAATATGGTTTTACTTGAACGCAGATTGGACATGGTCACACTGCCCACAAAATCACGACATTGCGTTATAAATG
AAGCACATCTAGTTTTGTGTTGAAAATGTGGTTCACAATTTATATAGCAGGTTATGGTAAAACATCGATCGTTCCGAAAAATTCCGCTCGTTGGC
ACATTTCCTAAATTTTTCGTGCGACAGCGGTGATTAATTACAAAAATTATTATTATAATTATATAAAAGTTGGCGACCATATCAAAAAGGTTGCT
ATAAAAACAAATGACAATTTATAGCGGAGTTTCACTCCCAAAGCGATGTTCTCCACCCATTCCAGTCAGTCATGGAAAATATACCTTCTAAAAAA
TATATGATTTTTTCGATAGAGATACACGGGCACACTAGACCCACCGATCGCGACTTTGTGTGTGTTAAAATGACGCGCATATCGTTTTGGCTAA
TAATATTGTTCACGTTTTATAAAACAGATACACGGTTAAGCTCTGACCGGTCGTATTATTATCTGTGTGTTCTTGGTTGACACGTTTATTTCATT
TATTCTCATTTAAAGCAACGATGTGAAGAACAGTGCGGGCGTTTCTCAACATAAGAATACATACAAACTTATGCGTGATGGTGAGCAAATAAAAT
AGTTCAAAAAATTACTCGGCCACCGCCTTAACCGTACAAACGGAAATACATAAAGGTAAAGGGCTCAACAACAGTATTACTGATTAGGCAATTGA
TTTATATTTCAAACTTCTTAAATAAAGTGTCCACAAATATGTATGTTCTTAGCATAGAGGCGTAGTCGGTGAGTCAGCCACGCCAACAGTTAACA
GTCGTCATTTTGCTGTCTGTCTAACACGCAATTTGTGTGTGTATATGTGAATAAACAGATACCGGTATGCAATCGCAAAGCTGGTCAACTGTAAA
GATCGGTATGTACTCAAAATTAGGTCATCACCTTGTTATGCAGATACATTTGGGAAACAGTTGACTTACTTGGTATTGGTTATCAGCCGAAAAGC
AAATGGTGATACGGTTTTGCACCTCAGCTTACTCACGGATACATACCTACGTACATAAATGTATGTATACGGTATACAGTCTTAGAAAAAATATT
AGTACCGACCAGCTAGCGTTTGCCTAAAACGCTTTTACAAAAATAAACGTATATGTTTTAAGTTGTTTTTTGTCATAATTAATACATTTATTATT
ATTTATTTATGAATTTCAGAGCTTTAATAGTAACTAAATTGTTTAAACAAACTTAAAAAAAGATTTCCAAATAAAAAAATATTTCGTGTGCGTGA
CGGAATTGCTAGTTCATTAAAGGGAGGTACATATGTACATACATACACATTGCAAAGAGTACAGATCGCTCATCTTGCATCTCATTTTTCCTAAT
GTACATATACATATGTACAAACATGTTTATTAAACTGCCTACATGCAAATCTTTGAAGTTTTAAGAAAATAAGCACAACTAGTTTGGAAAATCTT
GGGAGCCAAGATCTATCTGTCCACTGAATTTCCTATGACCAAGAATGTAAAACCCTTTTTGTTAAACAAATTTTGATTAAAGTATACCAGAATAA
TATTAAACGTATCGTCCGTATCTATAAAAGGTATTAATAGTATTACCTAAATTTAATTTCTCGGTTTTATTCATAAGAGTGAAAAAATATACAAG
TTCCTTTTTAATTTTTTACTTATTGAAAATGTGATTAATTTTTATTTATTATTTTCAGTTTAGAATAAATACGGCCACAATTAGTATACATATTT
ATTCATCGAAACCAACCCACCACAAGAGCATAACCAATTATGTTAAAGTTTATCAGAGGAAAAGGGCAGCAGCCCAGTGCTGACAGACACCGCCT
ACAGAAGGACCTTTTTGCTTATCGTAAGGTACAACAAACAATTTTCTCTTTCCATTCTATTTTATTTTTTTTTTTTCGTATATGTAGCCGATTGG
TATATTTTGTGGGGTGTCATTTATTTTGATCCTGGGTGGTAAATACATTTTTATGGAAGTTAGAAGAAAGCTTATAATTTATTAAGAATAAATAA
ATACCTCCTTTTCAATCTTTTGTTATGTCTTCTCCTATGTGCATACTTTTGGGCATTAACATTTAGGTAAATTTTTTCCACCGCAACTACAAGTA
AACCGCATACACACACAGTATTTTGTAGACTCGCGCCACAAAGCACCGCATAAAAAAGGTTACGGTGCTTTTTTGCTCGTTTCTTTTGTGCACTC
CTTCTATGCGGTGCCAAATATGAGGAGGTACCTGAAGCTTTGTTGATTTTGTGAGTGTCTTTTTCCACCGCCTGTTTTTGGCTACTTTAAAAATT
CTATTATATCGTTGTGCTCGTAATGTTGTCCATTCCTTTTAAATATTTTCGAATTAAATATACCATAGATGTTTCCCTATTACCATAATAGTTTA
ATAAATATACGTATATGAAATTTTATAAGAATTTTTTTATCCCATGTTAGTATAAACATGTTATTAAACAAATAAAAGTAGGTCAGAGGTAATC
GCCATCCAGCTCCAGAAAGAGGGGGGAGCTGATAAGATTGCTTTTATGTGCTTAATGGGTTGGGTAAATGGCTTGGTTTCACAAACACCCTTATT
TCAGGCACAAAATAAGTATGTCATAGACGGCGTAAAATTGATAAGATTTTAAAGTCAAAAGAAAAAGAATTTATTCGCCTGTAACTGCGTTAGAA
ATCCAAATACACCTGCAATATGAATCAAACAAAATCAACTCATAACGAGATCTGATAGCAACTTCTTAAAACTTTTTTTGTATAAAAAATACAATT
TATACAATTAGATAAGATTTACCAAACCTTTTTTCGATCAATGTAAATATAGTATGATAGTAGGGACTGCTGTCTACAGTGATGTTTATAAGAGA CATACTTAAGAGCAGCATTTAAAGCTTTGGGCGCTTTTTGAACTTAATTTAAATTCAAACCTCAATATTTATTGAGGTTTTTATTCCCGTTAATT
GTAAAGAAAAATGCTGTATTAGATTCGGTAAAAGTATGTAAATGGTTTAAGAAAGCGTTCCCGACTCTATAAAGTGGCAAGTAATCTGACGATTT
ACCAGATCTTGGGAACTGAAAAAACTAGAATGTTTTGGAAAACCCTTTTACAATTAAGAAATGAACCAAACAATTTTGAATTATTAAGAATCTGT
AATTGCTTTTTGAAACTTTTTAATATTTTTTTCTTTTAGACGGCACAGCATGGCTTTCCTCATAAGCCTTCGGCTCTTGCGTATGATCCAGTTTT
GAAACTTATGGCAATAGGGACGCAAACAGGGGCTTTAAAAGTTTTCGGTCAACCCGGAGTTGAATTGTACGGTCAGCATACTTTGTTAAACAATT
CAGCATCGGAGCTTAATGTACAATTACTTGAATGGGTGTATGGAACTGGTCGCATACTTTCGTTGACGGCAGCGAATCAATTAATTCTATGGGAG
CCAGTTGGAGCAACGTTGCTGCCAATCAAAACACTACCGTTTGACGGCAAACTTAAAAAAGTTTCATCGCTGTGCTGTTCTCTCAGTAAGGATCT
GCTATGGATTGGAACAGAAGGTGGAAACATCTATCAACTGGATTTACATACATTTACCATTAAGGAGCCTGTAATTTACCATGACGTTGTGCTAG
AGCAGGTGCCACCAGCCTACAAGCTAAATCCTGGTGCAATTGAGTCAATCCGCCAACTTCCAAACTCCCCTAGCAAACTTCTAGTTGCATACAAT
CGCGGCCTTTGTGTTTTGTGGGATTTTGAAAGCGCATCTGTCCAGCGAGCATACATAGCCCCTGGACATGGACAGAGCGTTGGTCTTACAGTGAA
CTTCGAAGGATCTGAATTTACCTGGTACCACGCTGATGGTTCATACGCCACTTGGAGCATAGATAACCCAGAACCGCCGTCGAATGTTAATTATG
TGCCTTATGGACCTGATCCATGCAAAAGCATAAATCGACTGTACAAAGGCAAGCGAAGGTTAATATAACTTAAACACAAAGTTTTTTAGATGTGT
ACTAATTTCTCGTTCTTTTAGATCCAACGATGTAATTGTTTTTTCCGGCGGCATGCCACGGTCAGCATATGGTGATCACAATTGTGTGTCCGTTC
ACGCCAGCGATGGACACAAAGTGTGTCTTGACTTTACGTCTAAAGTGATTGACTTTTTTGTGACCTTTGAAAATAATAGAGATGTCGCTGAAGTT
CTTGTTGTACTACTTGAAGAGGAACTCTGCGCTTACGATCTTACTGACCCTAATATTTGTGCTATCAAAGCGCCATATCTTCACTCTGTCCATGC
ATCAGCTGTCACTTGCAATTACCTTGCTTCTGAAGTCGTACAGTCGGTATATGAAAGTATTTTAAGAGCTGGAGATGAACAAGACATTGACTATA
GCAATATTAGCTGGCCTATCACTGGCGGTACTCTCCCGGATAACTTAGAAGAATCTGTAGAAGAGGACGCGACTAAGCTTTATGAGATTTTGTTA
ACTGGTCACGAAGATGGTTCTGTTAAATTTTGGGACTGCACTGGAGTGTTGCTTAAACCAATTTATAATTTTAAAACTAGCAGCATTTTTGGAAG
TGAGTCAGACTTCCGAGATGACGCAGCTGCAGATATGAGTGCGGAACAAGTCGATGAAGGAGAACCGCCATTTCGGAAATCAGGACTTTTTGATC
CTTATTCAGATGACCCTCGTTTAGCAGTGAAGAAAATAGCATTCTGCCCAAAAACCGGACAACTTATTGTTGGTGGCACAGCGGGCCAAATAGTT
ATAGCCGACTTCATAGACTTACCCGAAAAAGTGTCTTTAAAATACATTTCAATGAATTTGGTCAGCGATCGTGATGGATTTGTGTGGAAGGGTCA
CGATCAGTTAAACGTGCGATCGAACTTATTAGACGGAGAAGCAATTCCTACGACGGAACGTGGTGTAAATATATCGGGAGTACTGCAAGTTTTGC
CGCCAGCCAGCATAACATGCATGGCACTCGAAGCAAGCTGGGGCCTAGTATCTGGTGGGACTGCGCACGGCTTAGTTCTCTTTGACTTCAAAAAC
TTTGTTCCAGTATTTCATCGCTGCACTTTAAACCCAAATGATCTTACTGGAGCAGGAGAGCAGCTGTCTCGTCGAAAGTCTTTTAAGAAATCATT
GAGGGAGTCATTTAGAAAGCTTCGCAAGGGTCGATCGACCAGGACCAACCAGAGCAATCAAGTACCAACAACGGTTAGTAAGATAATATATACTC
AACTAGTCTTTTATATTAAATTCACAATCCTACAGCTGGAAGCAAGACCCGTCGAGAGGCAAATAGAGGCTCGTTGTGCAGATGACGGGCTAGGA
TCCATGGTGCGATGTTTACTATTTGCCAAAACTTATGTTACTAATGGTAATCAACATTTTGTACTGTTATTAGTTTTGATGTAACGATAAAAAAA
AAAAAAGGTAACGGAAATAGTCTCTGAACCACGGCCTCGCGAGAATTGAACCCAAAAGCTAAAAACATACAGTGCTTTTCATTTTGGGACGCCCA
GAGCTTTAATTATATTTTTGTGCAACAAATTTTTATGCATTGGATATATTGATCAAAGTTTTAAAGGTATATGTATTTATGATCAGTTTAAACAG
CCGACTACATTTGACTATGTCCGTCCTTAGAAAGAAATTCAGTCATTACAATATTCCTTGCTAGTCTATCGATATGCTATAAGTGTTAAAAGTGC
TTTTGCATTTACTCTGGTTTGACAATATATTTTATTGATATTGATTTCGTTTCATTTACTAGTTGGAAAAACAGTTCTTAAACTAATTAAATCATA
GTCTTTTTGTTTTCGCGATTTCGATCTATATGGCAAATTTTGTTTTTAAAATTTCACCTATCCTCCTACTATTTCTGTAATGGGTAACTCGACTG
TAGCGTCTATTCTTTTGGTGTTCTGTATATGTACATCTAATTTGTTGTATAATTTTTACATTTTCAGTCAACATAACGTCGCCAACTTTGTGGTC
AGCAACAAATGCCAGTACAGTCTCGGTTTTCCTTCTGCATTTGCCACCAGCGCAGACCGCGGCAACTGCCGTCCCGTCGGCAAGTGGCAATGCAC
CACCACACATGCCCCGCCGAATTTCTGCGCAGCTTGCTAAAGAAATACAATTAAAACATCGTGCTCCTGTGGTGGGTATTTCTATTTTTGATCAG
GCGGGTAGCCCTGTCGATCAGCTGAACGCCGGTGAAAACGGGAGTCCACCGCATCGTGTACTTATTGCTTCCGAGGAACAGTTCAAGGTGTTTTC
ACTTCCGCAACTAAAGCCGATTAACAAATATAAGCTTACCGCTAACGAAGGTGCTCGGATTCGCCGCATCCATTTTGGTTCGTTTAGTTGTCGCA
TATCCCCGGAAACACTGCAGAGTATGCACGGTTGTAGCCCAACTAAGTCCACGCGTTCACATGGCGATGGAGAGGCGGATCCTAATATCAGTGGA
AGCTTGGCTGTAAGTCGTGGAGATGTATATAACGAAACAGCATTGATATGTTTAACGAATATGGGCGATATCATGGTTTTATCAGTACCTGAATT
AAAAAGACAGCTGAATGCCGCAGCAGTGCGACGGGAAGACATTAAGTAAGTCACGCATAGTGCTATTATTTTAATTTTTTGGACCTAATACTGTA
TTTTAACTTTTCAGTGGAGTTTCGTCACTTTGCTTTACAAACTCTGGAGAAGCACTGTATATGATGTCTTCTTCTGAACTGCAGCGTATTGCTTT
AGCCACGTCCAGAGTCGTGCAACCCACTGGCGTTGTTCCAGTAGAACCATTAGAAAATGAAGAGTCTGTGTTGGAAGAAAATGATGCAGAGAATA
ATAAGGAAACCTACGCATGTGATGAAGTTGTGAATACATATGAAATTAAAAATCCATCAGGCATTTCAATATGCACAAGGCCTGCAGAGGAAAAC
GTTGGAAGAAATAGTGTTCAGCAAGTTAATGGAGTCAACATTTCAAATTCACCTAATCAAGCTAACGAGACTATCAGCAGCTCTATTGGCGATAT
TACCGTTGACTCGGTGCGCGACCATTTAAATATGACGACCACCACTTTGTGTTCTATTAATACAGAGGAAACCATTGGTGAGTAATCATTTATTT
ACTAACATTATTCCACCTATTTTAATTTGCTGTTTTGTACGTATCTACATTTAAATGTTTTCGTTTCGACATTAGTTACTTTCGGCAACATAATT
CTTATAAAAATTTACTTTTTAAAAACTTGATTTTAAGTATACGCACCAAACAACTTTAAATATATACTTTTATCTTATTTTAAAAGCACGGGCCC
ACATTATATCTGTACATAACTTTTTTTTTCTGTCATCTCTATGAAAATGTAGGTCGCCTATCTGTACTTAGCACGCAAACCAACAAAGCCAGTAC
TACCGTAAACATGAGTGAAATTCCAAATATTAATATTTCTAATTTAGAGGACTTGGAATCGAAAAGGTGTGCTTCTACAAGAAACATTGACATAA
GCTTTAACCTACTAATTTTTTTTTTTTACCTAACAGAAATACGACGGAAACGAGTACTAGTTCTGTTGTAATTAAATCTATAATTACAAACATTT
CTCATGAAAAAACGAACGGAGACAACAAAATAGGAACGCCAAAAACAGCGCCTGAAGAAAGCCAATTTTAACATTGACAGAAGCCGTAACCTACT
AATTATTTTATACCTTTACAGAAATACGACGCAAACGAGTACTAGTCCTGATGTAATTTAATCTATAATTACAAACATGTCTCACTAAAAATCGA
ACGGGGACAGCAAAATAGGAACGCAAAAAAATTAAATTAAATTAAACGCGATTTACATACAAACAGAAATGACAGAATGATAATATAAAATATTC
ATTTTTTATTTGGCTTAAGCGATGTTGTTGTTCCAAAACCATATAATTATTTATGATTTTATGTAATGTTTTCATGTATTTTCGCGTAGTGACTT
TATACCCTTTACCCGTATGATGAAACGAAACATGATATTTGTAGAAAGGTACAAAGGATAAAAGTTGACATTTAAGGCCGATTGTAAAATATTAA
AACGCAACCTGGATAACATGCCGATTAATTACTTCTGTTCGTCCGTATAAACACAAATACCGATAAATTGGTCCGTCCCCATTTAATAAATTGTA
TATTAAAATGGTCTTTATTTTGGATAAATAATTCAAATTATATAGGAACATTTGGGTTTTAAGGGATAGAAACAGCGCTGGTGTCTTTCATTTCC
GTTCGTATGACCGTTCAAAGATTATAAAAAAATTGTCGTGCCCACATTTTTTAAATTTCTTTTATTTTCGGTTAAAATATTGTGATACAAAAAAA
TGCCCTTACAAAATTAGGACAACAACAATTTGCTTTATTATGATGAACAAATTAGGAGTACAAAAAATAGCCTGATGCAAGGATGGGGAGAAAAA
AGACCTTGAAGTTCAAAAGAATTTGTTGTATCAAATCCTCAATAAGAAAACTACTTAAAATTAAAAGCGTGTTTCAAATTAATTGTAGAATATTT
CGTAAAATGAAATTGCAAACTTTTTTAGCACGAAATTACATGTATTTAATTCTTTGGCTAATACGTCAGTTAAAAAAGGCTACATTTTGATGATA
CTCACAAATGTAATTTTTGCATTCTACACAGGTGCAATTAAAAAATTATGGTTTTTATGAGTTTTAGAGGGAAGAAAATATGTCAATATGAGAAG
TAAGTTAATGAGCCTTCAAGTACTTTAGTACATAATGTAATTTAATTTTAGAAATCCTACGGCTTTATATTCAATTGTAAAGTATTTTAAAATTC
CTGACGATTTGTAGTAATTGTTTTGTTCTTAGCTTTTTTGCATTCTCCTCCGTTACTCCGTTACTCGTATAGTAAAAGGTATAGTATATACAATA
GTATTGTAGATTCGTTGAGAAGTATGTTACAGGCAGAAGGAAGCTTTTCCGACCATATAAAGTATATAATTGAGTATTTAGCTTAGGATTATTAA
TAAAACATGTATTTTATTTAACAAACTGGCTTTACAATATTTTGTGGAAGAACACCGATCTATTTAGTTGTAGGTCTCAAACTGAAAACTCCTAA
TTTTGACTTATTTAAAGATCATACCTCGGTTTTGAGCCTTAGAGGTTTGTATGAGTGATTTTCTAGAATGATCTTTGTACTTCGTTACAATAAAT
TGTTTTCTTCTACTCTAATATAGTTGGAATCGAGTAATCCCTAGATAAGAGTTAGGCTTAAAATAGTAAATTACAAATATTGAATTGGACATTAC
AATTGCATATTCTCAGCTTGCTGTATTGTAAAAATTAATTATTAACTCGAAGAGATTCGGCAATTAATACGTCCCTATTCGCATTGTTTTTACTT
GGGGAAATTTTATTGAAAAACTAGATTCTCTGTTACAATCAGATATGAGAACAAGTTATTGCACCAGCACATCTCTCGGCCAGCTCAATTCAATT
AAATAGCTAAGCACTTGTTGCGAATTCATGCTTGGAGTGTTTACGTAAGATTTGTAAAAATAACTAAACTGGATTCTCCACATTCTTGCGTAGCT

FIGURE SHEET 684

GTGTGATTCTACTGTCACAACTCTCCGTCGACGATTTCTAGAGCCATCTTCTTGCGGAAGTACAACATTTCCGACTGGGTAAAGGTAATTGGCAC
ATCACACGTTATATACTCGGCGAACATGCAGCTGAAGATACCGCAATCGCTGCCATCTAACTGTCGTGGTATATTCTGCACGCTCTCAATAACAA
AATCGCTGGTATCAAACTGCTTTTTGGGCTTGAATATTGACTCTTCGCGTAGATATTTCTCTAGAGCGTCCAGCACTGGTCGGTTTGGCTTTCCC
TTTGAGTCATAATACCGGATTGTCTTGTTCCGCAAGTGTATGATGGCCATGCACCAGTGGACGCCGTTGCAGTGCACTGGTACCGGGATTATGTC
CTTGCTGAACAAGTCCACTTTGCGAGTCCAGCGCTTAATGCCTGCATGCCCAGCTTGCAGGAGGCGGGGCACGAA
(SEQ ID NO: 1267)

Exon: 1001..1290
Exon: 1383..1525
Exon: 2339..2498
Exon: 3840..4618
Exon: 4677..5868
Exon: 5926..6031
Exon: 6623..7265
Exon: 7330..7772
Exon: 8033..8141
Exon: 8207..9715
Start ATG: 2415

Transcript No. : CT43227
CGACTTTGTGTGTGTTAAAATGACGCGCATATCGTTTTGGGCTAATAATATTGTTCACGTTTTATAAAACAGATACACGGTTAAGCTCTGACCGG
TCGTATTATTATCTGTGTGTTCTTGGTTGACACGTTTATTTCATTTATTCTCATTTAAAGCAACGATGTGAAGAACAGTGCGGGCGTTTCTCAAC
ATAAGAATACATACAAACTTATGCGTGATGGTGAGCAAATAAAATAGTTCAAAAAATTACTCGGCCACCGCCTTAACCGTACAAACGGAAATACA
TAAAGCATAGAGGCGTAGTCGGTGAGTCAGCCACGCCAACAGTTAACAGTCGTCATTTTGCTGTCTGTCTAACACGCAATTTGTGTGTGTATATG
TGAATAAACAGATACCGGTATGCAATCGCAAAGCTGGTCAACTGTAAAGATCGTTTAGAATAAATACGGCCACAATTAGTATACATATTTATTCA
TCGAAACCAACCCACCACAAGAGCATAACCAATTATGTTAAAGTTTATCAGAGGAAAAGGGCAGCAGCCCAGTGCTGACAGACACCGCCTACAGA
AGGACCTTTTTGCTTATCGTAAGACGGCACAGCATGGCTTTCCTCATAAGCCTTCGGCTCTTGCGTATGATCCAGTTTTGAAACTTATGGCAATA
GGGACGCAAACAGGGGCTTTAAAAGTTTTCGGTCAACCCGGAGTTGAATTGTACGGTCAGCATACTTTGTTAAACAATTCAGCATCGGAGCTTAA
TGTACAATTACTTGAATGGGTGTATGGAACTGGTCGCATACTTTCGTTGACGGCAGCGAATCAATTAATTCTATGGGAGCCAGTTGGAGCAACGT
TGCTGCCAATCAAAACACTACCGTTTGACGGCAAACTTAAAAAAGTTTCATCGCTGTGCTGTTCTCTCAGTAAGGATCTGCTATGGATTGGAACA
GAAGGTGGAAACATCTATCAACTGGATTTACATACATTTACCATTAAGGAGCCTGTAATTTACCATGACGTTGTGCTAGAGCAGGTGCCACCAGC
CTACAAGCTAAATCCTGGTGCAATTGAGTCAATCCGCCAACTTCCAAACTCCCCTAGCAAACTTCTAGTTGCATACAATCGCGGCCTTTGTGTTT
TGTGGGATTTTGAAAGCGCATCTGTCCAGCGAGCATACATAGCCCCTGGACATGGACAGAGCGTTGGTCTTACAGTGAACTTCGAAGGATCTGAA
TTTACCTGGTACCACGCTGATGGTTCATACGCCACTTGGAGCATAGATAACCCAGAACCGCCGTCGAATGTTAATTATGTGCCTTATGGACCTGA
TCCATGCAAAAGCATAAATCGACTGTACAAAGGCAAGCGAAGATCCAACGATGTAATTGTTTTTCCGGCGGCATGCCACGGTCAGCATATGGTG
ATCACAATTGTGTGTCCGTTCACGCCAGCGATGGACACAAAGTGTGTCTTGACTTTACGTCTAAAGTGATTGACTTTTTTGTGACCTTTGAAAAT
AATAGAGATGTCGCTGAAGTTCTTGTTGTACTACTTGAAGAGGAACTCTGCGCTTACGATCTTACTGACCCTAATATTTGTGCTATCAAAGCGCC
ATATCTTCACTCTGTCCATGCATCAGCTGTCACTTGCAATTACCTTGCTTCTGAAGTCGTACAGTCGGTATATGAAAGTATTTTAAGAGCTGGAG
ATGAACAAGACATTGACTATAGCAATATTAGCTGGCCTATCACTGGCGGTACTCTCCCGGATAACTTAGAAGAATCTGTAGAAGAGGACGCGACT
AAGCTTTATGAGATTTTGTTAACTGGTCACGAAGATGGTTCTGTTAAATTTTGGGACTGCACTGGAGTGTTGCTTAAACCAATTTATAATTTTAA
AACTAGCAGCATTTTTGGAAGTGAGTCAGACTTCCGAGATGACGCAGCTGCAGATATGAGTGCGGAACAAGTCGATGAAGGAGAACCGCCATTTC
GGAAATCAGGACTTTTTGATCCTTATTCAGATGACCCTCGTTTAGCAGTGAAGAAAATAGCATTCTGCCCAAAAACCGGACAACTTATTGTTGGT
GGCACAGCGGGCCAAATAGTTATAGCCGACTTCATAGACTTACCCGAAAAAGTGTCTTTAAAATACATTTCAATGAATTTGGTCAGCGATCGTGA
TGGATTTGTGTGGAAGGGTCACGATCAGTTAAACGTGCGATCGAACTTATTAGACGGAGAAGCAATTCCTACGACGGAACGTGGTGTAAATATAT
CGGGAGTACTGCAAGTTTTGCCGCCAGCCAGCATAACATGCATGGCACTCGAAGCAAGCTGGGGCCTAGTATCTGGTGGACTGCGCACGGCTTA
GTTCTCTTTGACTTCAAAAACTTTGTTCCAGTATTTCATCGCTGCACTTTAAACCCAAATGATCTTACTGGAGCAGGAGAGCAGCTGTCTCGTCG
AAAGTCTTTTAAGAAATCATTGAGGGAGTCATTTAGAAAGCTTCGCAAGGGTCGATCGACCAGGACCAACCAGAGCAATCAAGTACCAACAACGC
TGGAAGCAAGACCCGTCGAGAGGCAAATAGAGGCTCGTTGTGCAGATGACGGGCTAGGATCCATGGTGCGATGTTTACTATTTGCCAAAACTTAT
GTTACTAATGTCAACATAACGTCGCCAACTTTGTGGTCAGCAACAAATGCCAGTACAGTCTCGGTTTTCCTTCTGCATTTGCCACCAGCGCAGAC
CGCGGCAACTGCCGTCCCGTCGGCAAGTGGCAATGCACCACCACACATGCCCCGCCGAATTTCTGCGCAGCTTGCTAAAGAAATACAATTAAAAC
ATCGTGCTCCTGTGGTGGGTATTTCTATTTTTGATCAGGCGGGTAGCCCTGTCGATCAGCTGAACGCCGGTGAAAACGGGAGTCCACCGCATCGT
GTACTTATTGCTTCCGAGGAACAGTTCAAGGTGTTTTCACTTCCGCAACTAAAGCCGATTAACAAATATAAGCTTACCGCTAACGAAGGTGCTCG
GATTCGCCGCATCCATTTTGGTTCGTTTAGTTGTCGCATATCCCCGGAAACACTGCAGAGTATGCACGGTTGTAGCCCAACTAAGTCCACGCGTT
CACATGGCGATGGAGAGGCGGATCCTAATATCAGTGGAAGCTTGGCTGTAAGTCGTGGAGATGTATATAACGAAACAGCATTGATATGTTTAACG
AATATGGGCGATATCATGGTTTTATCAGTACCTGAATTAAAAAGACAGCTGAATGCCGCAGCAGTGCGACGGGAAGACATTAATGGAGTTTCGTC
ACTTTGCTTTACAAACTCTGGAGAAGCACTGTATATGATGTCTTCTTCTGAACTGCAGCGTATTGCTTTAGCCACGTCCAGAGTCGTGCAACCCA
CTGGCGTTGTTCCAGTAGAACCATTAGAAAATGAAGAGTCTGTGTTGGAAGAAAATGATGCAGAGAATAATAAGGAAACCTACGCATGTGATGAA
GTTGTGAATACATATGAAATTAAAAATCCATCAGGCATTTCAATATGCACAAGGCCTGCAGAGGAAAACGTTGGAAGAAATAGTGTTCAGCAAGT
TAATGGAGTCAACATTTCAAATTCACCTAATCAAGCTAACGAGACTATCAGCAGCTCTATTGGCGATATTACCGTTGACTCGGTGCGCGACCATT
TAAATATGACGACCACCACTTTGTGTTCTATTAATACAGAGGAAACCATTGGTCGCCTATCTGTACTTAGCACGCAAACCAACAAAGCCAGTACT
ACCGTAAACATGAGTGAAATTCCAAATATTAATATTTCTAATTTAGAGGACTTGGAATCGAAAAGAAATACGACGGAAACGAGTACTAGTTCTGT
TGTAATTAAATCTATAATTACAAACATTTCTCATGAAAAAACGAACGGAGACAACAAAATAGGAACGCCAAAAACAGCGCCTGAAGAAAGCCAAT
TTTAACATTGACAGAAGCCGTAACCTACTAATTATTTTATACCTTTACAGAAATACGACGCAAACGAGTACTAGTCCTGATGTAATTTAATCTAT
AATTACAAACATGTCTCACTAAAAATCGAACGGGGACAGCAAAATAGGAACGCAAAAAAATTAAATTAAATTAAACGCGATTTACATACAAACAG
AAATGACAGAATGATAATATAAAATATTCATTTTTTATTTGGCTTAAGCGATGTTGTTGTTCCAAAACCATATAATTATTTATGATTTTATGTAA
TGTTTTCATGTATTTTCGCGTAGTGACTTTATACCCTTTACCCGTATGATGAAACGAAACATGATATTTGTAGAAAGGTACAAAGGATAAAAGTT
GACATTTAAGGCCGATTGTAAAATATTAAAACGCAACCTGGATAACATGCCGATTAATTACTTCTGTTCGTCCGTATAAACACAAATACCGATAA
ATTGGTCCGTCCCCATTTAATAAATTGTATATTAAAATGGTCTTTATTTTGGATAAATAATTCAAATTATATAGGAACATTTGGGTTTTAAGGGA
TAGAAACAGCGCTGGTGTCTTTCATTTCCGTTCGTATGACCGTTCAAAGATTATAAAAAAATTGTCGTGCCCACATTTTTTAAATTTCTTTTATT
TTCGGTTAAAATATTGTGATACAAAAAAATGCCCTTACAAAATTAGGACAACAACAATTTGCTTTATTATGATGAACAAATTAGGAGTACAAAAA
ATAGCCTGATGCAAGGATGGGGAGAAAAAAGACCTTGAAGTTCAAAAGAATTTGTTGTATCAAATCCTCAATAAGAAAACTACTTAAAATTAAAA GCGTGTTTCAAATTAATTGTAGAATATTTCGTAAAATGAAATTGCAAACTTTTTTAGCACGAAATTACATGTATTTAATTCTTTGGCTAATACGT
CAGTTAAAAAAGGCTACATTTTGATGATACTCACAAATGTAATTTTTGCATTCTACACAGGTGCAATTAAAAAATTATGGTTTTTATGAGTTTTA
GAGGGAAGAAAATATGTCAATATGAGAAGTAAGTTAATGAGCCTTCAAGTACTTTAGTACATAATGTAATTTAATTTTAGAAATCCTACGGCTTT
ATATTCAATTGTAAAGTATTTTAAAATTCCTGACGATTTGTAGTAATTGTTTTGTTCTTAGCTTTTTTGCATTCTCCTCCGTTACTCCGTTACTC
GTATAGTAAAAGGTATAGTATATACAATAGTATTGTAGATTCGTTGAGAAGTATGTTACAGGCAGAAGGAAGCTTTTCCGACCATATAAAGTATA
TAATTGAGTATTTAGCTTAGGATTATTAATAAAACATGTATTTTATTTAACAAA
(SEQ ID NO: 1268)

Start ATG: 510

MLKFIRGKGQQPSADRHRLQKDLFAYRKTAQHGFPHKPSALAYDPVLKLMAIGTQTGALKVFGQPGVELYGQHTLLNNSASELNVQLLEWVYGTG
RILSLTAANQLILWEPVGATLLPIKTLPFDGKLKKVSSLCCSLSKDLLWIGTEGGNIYQLDLHTFTIKEPVIYHDVVLEQVPPAYKLNPGAIESI
RQLPNSPSKLLVAYNRGLCVLWDFESASVQRAYIAPGHGQSVGLTVNFEGSEFTWYHADGSYATWSIDNPEPPSNVNYVPYGPDPCKSINRLYKG
KRRSNDVIVFSGGMPRSAYGDHNCVSVHASDGHKVCLDFTSKVIDFFVTFENNRDVAEVLVVLLEEELCAYDLTDPNICAIKAPYLHSVHASAVT
CNYLASEVVQSVYESILRAGDEQDIDYSNISWPITGGTLPDNLEESVEEDATKLYEILLTGHEDGSVKFWDCTGVLLKPIYNFKTSSIFGSESDF
RDDAAADMSAEQVDEGEPPFRKSGLFDPYSDDPRLAVKKIAFCPKTGQLIVGGTAGQIVIADFIDLPEKVSLKYISMNLVSDRDGFVWKGHDQLN
VRSNLLDGEAIPTTERGVNISGVLQVLPPASITCMALEASWGLVSGGTAHGLVLFDFKNFVPVFHRCTLNPNDLTGAGEQLSRRKSFKKSLRESF
RKLRKGRSTRTNQSNQVPTTLEARPVERQIEARCADDGLGSMVRCLLFAKTYVTNVNITSPTLWSATNASTVSVFLLHLPPAQTAATAVPSASGN
APPHMPRRISAQLAKEIQLKHRAPVVGISIFDQAGSPVDQLNAGENGSPPHRVLIASEEQFKVFSLPQLKPINKYKLTANEGARIRRIHFGSFSC
RISPETLQSMHGCSPTKSTRSHGDGEADPNISGSLAVSRGDVYNETALICLTNMGDIMVLSVPELKRQLNAAAVRREDINGVSSLCFTNSGEALY
MMSSSELQRIALATSRVVQPTGVVPVEPLENEESVLEENDAENNKETYACDEVVNTYEIKNPSGISICTRPAEENVGRNSVQQVNGVNISNSPNQ
ANETISSSIGDITVDSVRDHLNMTTTTLCSINTEETIGRLSVLSTQTNKASTTVNMSEIPNINISNLEDLESKRNTTETSTSSVVIKSIITNISH
EKTNGDNKIGTPKTAPEESQF*
(SEQ ID NO: 1269)

Celera Sequence No. : 142000013384703
TTAACTAAGGCGATATTGTGCCTCTCGCTCAATCTCGCAAAACGATGCTTTGTCTGCTGCTTCTCTGTGCGTGTGTCCGTCTCTTTCCACGGCTT
TTCGTCGAGACTCACATATACAAACGGCGACACACTGGATTGGAGCTGGACTCCGTTTTGGATGGCTTGGCTTTGGCTGCGTACCCAAAATAAAT
CGCGCTTGCAGTCCCAAATCATTTTAGTTCTTGACGCCTTTGTTCCACAAAAACTTCCAACCGCCGTCCATGGCTCGTGCTTTCTCTTTCGCTCG
CGAGACGCTCCAAAAGTCGCGAGTATGGGAAGAGAATGTATCCCTCGCTCTTTCACGCCTAGAAGCGGCTGTAGCACACACAAGCACACGTAAAC
CCAGCCGTATGCATATACATATATTCCCTCTACTAGCGAGACGTGTGTACGTGCGTATGTATGTATGCTTTTTTCACTTCTTTCTCCTCTGCGTT
CTTTGCACCAAGTGTCGCTGTTGCTATTTGCTACCGCCGCTCCTCTTGACGAATAAGTCGGGACTTGTATCAGCTCTAATTCGGACTTAGTTTAC
AAAATGCGGCTGCTTTTTTTCCGCGATACTCGGATTAGTGATGTAAAAAGACGTTGATGCTTCGACCACTGAAGTCAGTGCGATATGTATCGATA
ATTGAATGCCATCGATTGCTACGATTAAAACTGCCACCGCAGTTAGCGGAGACGCTCACCATTCTCTATTCGCCATTTGAAAGTATCGGTGTAAT
TTGTTTTCAGAGAAATTAATTTCCGTTTACTGTGCAATTCGGTGTGAAAGTGTTCAGATTTATCAATGCGTATTCTGCTTTCGACTTCGCCACCA
ATCTGTGCTGCAAGTTACCATTACCAGGTCCACCTGGTTCCCGCCAGTTTTCTTTCATTGTGGCTAGTTGTTGTTCGTGCCTTCGATAAAGACGT
TTAGAGGTGTTTTTAGAGTTTCGCCATCTGGTCACTATAGCCGTTTCGTTTTTTACGTGAGTATTGTGAATTTGGTGTGTTGATTTATATCTCAG
TTGGAGCCTGCGTGGAAATAGTGTCAGTACGTTTAAAGGCATCATCGTAAGGTTAGTCGGAAAACAAATAAAAAGCCTACAAATAGCAAGCAAGA
ACGCTTTCGCAACCACAAGAAAAACGAACATACGCACGCATCCATCTGTGGTAGAGTCGGCTTGTGTGGGGGTGAGTGGATGTGTGGGTGAGCAT
TTCTGGAAAGTGCCGTTCTCTATGTTTCGATTCTACTTATCCCTTCATCACCATTTCATCGTTGAATCATCACGAAAGAAACATCGAAAGTGCAC
AATCGTTTGTTATCTTTGTACGAAAACAACGGTGATTTCCACACAGGCATAACCTGCAAGAGTAATACGATACAAATTTTGATCTGATATGACCT
CATTTTAGTCGGTTTGAATTTTAAAGAGAGCGACTCTGCAAACTGCAGGGATATGAACATACAAAATTCACAAATGATTGTTTGCATCCTAGTTG
CTTATATTCATTTACACGCATGCTTATATGCTTACATCTGTTATCAATAATTGACGACTTGGTGCATGCGAAGCAAACGCATTGAAATGACTATT
GGGATCCACACACTGTTAAAAAACACACTGATTGCACTGCCACACATTTCTCAACTAGAACCTAATGTTTTATACTGAACTTAACTGCAGGAAAG
CCCAAAATGCCCAGCATCAAGTTGCAATCTTCGGATGAGGAGATCTTTGACACGGATATCCAGATCGCCAAGTGCTCCGGCACTATCAAGACCAT
GCTGGAGGACTGCGGCATGGAGGACGATGAGAATGCCATTGTGCCGTTGCCCAATGTGAATTCGACGATTCTTCGCAAGGTGCTTACCTGGGCTC
ACTACCACAAGGACGACCCCCAGCCAACGGAGGATGATGAGAGCAAGGAGAAGCGCACAGACGACATTATCTCATGGGATGCAGATTTCCTAAAA
GTCGACCAGGGCACACTGTTTGAGCTGATATTGGCAGCGAACTATCTGGACATTAAGGGCCTTCTGGAGCTCACCTGCAAGACTGTTGCAAACAT
GATTAAGGGAAAGACTCCCGAGGAAATACGCAAGACCTTCAACATTAAGAAGGACTTTTCGCCCGCCGAGGAGGAGCAGGTGCGCAAGGAGAACG
AGTGGTGCGAGGAGAAGTAAAGCGCGGCATTTCGCGGGACCAACATTAAGTTGAAACAGCTAGGGGATTCGGGAACGAATTGGATTTGCAGCATT
GCAACTTTACTTAGTTGCTACTTTCATTTACATTTTTTTTTATTTTTAACCCCAGCAGAGACTCGATTTAAATTGTGTATAAATGATCTGTTGCT
GATTTGATTCGCGGGGTTCATTTTTTGTCGTAAATATATCTCATATACATACATATGCGAGATTGTAACACTCTCTTTAACCTATTGGAGTAACA
CTTGATTTCACTTTAATAAATATAACTACCCAACACAAAGACACAGCCTATTTTGTGGGCTTCCCGGAGGGGTTAGGGTCCAAGGACTTCTCAAA
TTAAGAAGTGCTCTTTATTCGTTATCTTGTGTTTAGAAACGTTTGCAAGCGTTTGAAATGGATACGCATGCCATTTATGGTCCAGTCGGTAAAAT
TTTACGTGTTCCCAAGAAGGTACATATATATCTTAGATTATCTTATCTATAGAAACTACATTCATAAGATCACGCTTTCGGCGAATAGCGAGTAA
TACTGTAGCTGCCACTTTGCCACTTAGTGTGCAATTGAAATGCGCGCCAACGCATGTTCTCATATGCGGAGCGTTTAGCAGCCCTTAAAAAGCTT
TTCATGTTGCTTTTAAAAAGCTACGACGGGTGTGGAAATTAGATTTGTGACGCTTTATATATCTTTTTTTTATATCGTCTGGGGTACAGCATGGT
TTTAGGATTTTAGAAGAAAGCAGTAATTTTGTAAGAATCGAAGAACGGGGGGATATTTATAATTTTCATATTAACCTTGTCTTTGTTTGCTTTTG
AAATTATGAATACTTCGAAAGATAATTATCTTGTGCGCATTCCATTCTGGCTTAGACTGGGTTGAGCTAAAAATGATTTGAAATACAAATTTTTA
GGTGTCCGCTGATATATAAACAGTATGATGTTTTTGCACTTTTTTCCCTGAAGTTTTCCTTGTTGTCTCGCTTGCCAATGCTGAACAAAGTAGCC
AAAGGACCTTTACTTGAAGCTTTGAGAGCGGAAAATATATTCGGGGACAATTGCTTTAAGTGTGCACTAGGCTTGGCTAGATGCCCGTGCCAAAC
TTTCTTTGGAATTGATCGCTGGCCTTAGCCAAAAGTGGAAAAAAGAAAGGATAGGATAGTGCCGCACGTATTAAGGGTCTTCTTACAAAAGGTAA
CTGATATTAATTCATTTGCATACTAAGCAAGCTAACTCATCTGTTT
(SEQ ID NO: 1270)

Exon: 1001..2466
Start ATG: 1717

Transcript No. : CT43239

FIGURE SHEET 686

TTTTACGTGAGTATTGTGAATTTGGTGTGTTGATTTATATCTCAGTTGGAGCCTGCGTGGAAATAGTGTCAGTACGTTTAAAGGCATCATCGTAA
GGTTAGTCGGAAAACAAATAAAAAGCCTACAAATAGCAAGCAAGAACGCTTTCGCAACCACAAGAAAAACGAACATACGCACGCATCCATCTGTG
GTAGAGTCGGCTTGTGTGGGGGTGAGTGGATGTGTGGGTGAGCATTTCTGGAAAGTGCCGTTCTCTATGTTTCGATTCTACTTATCCCTTCATCA
CCATTTCATCGTTGAATCATCACGAAAGAAACATCGAAAGTGCACAATCGTTTGTTATCTTTGTACGAAAACAACGGTGATTTCCACACAGGCAT
AACCTGCAAGAGTAATACGATACAAATTTTGATCTGATATGACCTCATTTTAGTCGGTTTGAATTTTAAAGAGAGCGACTCTGCAAACTGCAGGG
ATATGAACATACAAAATTCACAAATGATTGTTTGCATCCTAGTTGCTTATATTCATTTACACGCATGCTTATATGCTTACATCTGTTATCAATAA
TTGACGACTTGGTGCATGCGAAGCAAACGCATTGAAATGACTATTGGGATCCACACACTGTTAAAAAACACACTGATTGCACTGCCACACATTTC
TCAACTAGAACCTAATGTTTTATACTGAACTTAACTGCAGGAAAGCCCAAAATGCCCAGCATCAAGTTGCAATCTTCGGATGAGGAGATCTTTGA
CACGGATATCCAGATCGCCAAGTGCTCCGGCACTATCAAGACCATGCTGGAGGACTGCGGCATGGAGGACGATGAGAATGCCATTGTGCCGTTGC
CCAATGTGAATTCGACGATTCTTCGCAAGGTGCTTACCTGGGCTCACTACCACAAGGACGACCCCCAGCCAACGGAGGATGATGAGAGCAAGGAG
AAGCGCACAGACGACATTATCTCATGGGATGCAGATTTCCTAAAAGTCGACCAGGGCACACTGTTTGAGCTGATATTGGCAGCGAACTATCTGGA
CATTAAGGGCCTTCTGGAGCTCACCTGCAAGACTGTTGCAAACATGATTAAGGGAAAGACTCCCGAGGAAATACGCAAGACCTTCAACATTAAGA
AGGACTTTTCGCCCGCCGAGGAGGAGCAGGTGCGCAAGGAGAACGAGTGGTGCGAGGAGAAGTAAAGCGCGGCATTTCGCGGGACCAACATTAAG
TTGAAACAGCTAGGGGATTCGGGAACGAATTGGATTTGCAGCATTGCAACTTTACTTAGTTGCTACTTCATTTACATTTTTTTTATTTTTAAC
CCCAGCAGAGACTCGATTTAAATTGTGTATAAATGATCTGTTGCTGATTTGATTCGCGGGGTTCATTTTTTGTCGTAAATATATCTCATATACAT
ACATATGCGAGATTGTAACACTCTCTTTAACCTATTGGAGT
(SEQ ID NO: 1271)

Start ATG: 717

MPSIKLQSSDEEIFDTDIQIAKCSGTIKTMLEDCGMEDDENAIVPLPNVNSTILRKVLTWAHYHKDDPQPTEDDESKEKRTDDIISWDADFLKVD
QGTLFELILAANYLDIKGLLELTCKTVANMIKGKTPEEIRKTFNIKKDFSPAEEEQVRKENEWCEEK*
(SEQ ID NO: 1272)

Celera Sequence No. : 142000013384225
CATAGATCACCCTGCCCGAGTCGCAGGATACCACGAACAGGAAACCATCGGCCGCCTCCAGGATAAGATGCTTAAGCTCCTGGTCGGTCAGGAAG
GAGGGCTTGTAAGTGCCATCGCTGCTGGTATTTCCTGTGCCACGCAGTGCCTTCATGTGAGCCACTGCCATGCGGAGAATGGTGAGCTTGTCCGG
TTTGCGGGCCAGGGCACTGCAGGTGGGCACCATGTCCGAGAGTTCCGTGATGTAGGCCGTCATCTTGTTGCGGCGACGTCGTTCAATCTCGCAAT
GGTTCTCGCGGCTGGCGAACCGCTCCTTGTCCTGTATGTTCGCCTCGTCCATGCTTGGAATGCGTAATTAGAAAACGTTCGTCGTAATTTGGGTC
GCCTGTGCTCTGTGGAAAAAGGTTCGTGGAATTGAGAGAGGGGCGGGGTAGGGGTAGGGGTTAGTATTTTGTCTACGTCGTGCTTGTGTGTGTAC
ACTTGCTGGCTGGCCAGTAACCTTATTTCCCTCGCTTTTTTTACCCTTCTACTCACCAATGGGGGGTGTACAGAGGTACTTGGTTTATCCAGGCA
ATTTTATTCGGCTGGTCTTATGCGCTTTTACCATTAATTCTGTACTTTTCTTCTACACTACACGATAAAATCTCTGTTTACTGCGCGAAGTGTGA
CCGTAGTGTGGACTAACAAATATGCCGATGCAGTGTATAGCAAATCGATAACAATGCGCTAGGTGGCAACACAGGTGCGTTGAATCAAGACCAAG
TGGCATTACTATAAAACTAGAACGTTACATTTTAAAATTTTCATCCTAAAAAATAAACACAAATATACAATAAAATTTTAATTTAATATTGACTT
TTTTAAGGCCCAGCTATCTGTTGGCTAATTAAGTAAATCAATTTACCGCTTGTCGTGTGGTGAAAATGTTTTTATCTTTCAAAAACATACAAGAT
CGGCGTCCATTTAAAAAATCGCTTTTCCCAGAAAATAAATAAAACCATCATTGTTTCTGATATTGTTGTCAGTATTTAATGGTATTACAGCATTG
CGTTTTCTTACATATATCAAATATAATTTCATAAATACATTTAAATGTTTAGTCATAACTAGGCGCAGTATCGTAATTTTACGAACTATGATTCT
TTAAAAAATTAAAAGTTTATTATTAGTGGCAATAACATGTCTTCATTTACTCCTATCCGGATGCATTCTTATAACAAAATAGTAAGCTTGCGCTT
TATTCCATTTCGCATATTTCTTTGTGTTCTTTGCTTATTACATTTTTTCAGTTTTAATACAATCTTAGGTAAAGTTTTATCCGCTTTGCTTGTCC
TTCATGTTAAATCTGCTTGGTATTGTTAATTAATTATTGGCAATTTTCTAACTGCATGGTTTATTTAGATGGGCATTCCATTTTCCATATTTCAT
TCAAGCTGTTGGTACAACATACAAGTCTTTTGTTCTATGTTTATAGTTAAATATATTTAAGTCTCCATTAAAATACGTGCACTACTTAAGTGTAA
TTTAAAATGCGGCTTCATTAAAATAGCTTAGCGTGCTTAATACGTCTTTTTTGTGGTGTCTTTGTTGGATGAAGTCCGGTTTAGATTTAACTTCA
GCATAATTCGTTGACTAGAAATTAACTTAAGTACTTAGGGCTAGACTAATATTAACTTTAAACAAACACGCTCTTGCAGTTTTCTATTTTGGTTT
ACGTGCATAAGTGTTTTCTGATCAATCTTTGTTCATTAATTTGTGCTGCAAACTTATTTGAGTTGCGTCGATATCCATTTCCTTGCTGGAAAGTA
GTCAATATTTGCTTCTTGTGATTTCATATCAAATTAAGGTCATTCGTAGTTGCTGCAAGCTTAAACATAACTTTTCAAATCCGTTAACAATTTTA
TTTTGCCTTTCAAAACATTTAGCACCAAAATGATTAATCGCCAAATAAAGAATCCTTGTAGTTTGTGTTTGTTAATTTTGCACATCGTTTGGAAT
TTAGACATAGAGAAAAACTAAGTAAATTTGCAACAACTTTCAATTAATTCCAATTTAAATTCAAAATACTATAAACTCCTATACAATACTTTGGT
TTTTCAGTATACAACGCACAAATGGGCGATTCAAGGTTTGAAAAAAAATTGAAAAAACGAAGATATCTTTGTTGGATTGAACAATACATAGTTTTG
GCTCTGGGGCGCACTTACTTATAACATCACAAAAAAATTAAACATACGTGTGATAAATTAGTTGATAGTTTCATACACTAATCTAGCTGCGTAAA
CTATCTAATCTTTAGTCTGCAAAAATAATGCCTATCTCTCCAATATAATATTCTTTGCGCTCAATTGCGTTTAAAATGCAACAACTTGTGTGTAT
GGTATAATGTGTAGCTTTAGTAGGTTTGATTGCGAGTAAATGTTGCTTGGCTAGGAAACGCCCCGCGACCTTTCTACGTGGTGTAGGTGCGGATGA
CGTCCCGGATCACCGCCCGGCACAGTGGGCACTGGCCACCACCCACTCCGCGCCACTGCTCGATGGCGCAGTCGTAGCACATGCACATGTGTCCG
CACATGTACAGCACCGAGTCGATGGGATTCTCGTAGCAGATGGTGCATTCGGCACTCGAATCGGTGCTCTGCTGGTCGCTCAGGCTGTCCTTCCA
CTTGTTGGCCGCATTATTTGTGCTATTGGCAATGGGCTGCTGATAAAGTAGGCATTAGTATATGTCTAGGGAGTATTTCACAAAGCTTTGACACT
CACCTCGATGTACTGGCTGCTGGTGGTGCTGATAAGGGTGCCGCTGGAGCAGGCTCCGGCCAGAACACCGCTGGAGGTTACCGTGGCCGTTGGCC
TGGCCGCGAGTTGGCCGTTTATATCGTGCGAGCTGCTAGCAGGTGGCAGGTTGACCACCAGAACGGTGCCACCACCATTCGGCTGGATCTGGAGA
ATATCTCCGTTGGAGGGCATGCTGATCATGCGGCTGCCATTGACTCCGCCAGCTGAGGCCAAAGTGCTCGTACTCTGGGCTACGCTCAGCTGCGA
GGGATGATGCAACAGCTTGGCAGTGGCTCCGGCATTCAGACTGCTCATCGACTCGGTCATGGGCAGCATGCGGGACGTGGAGGCAGCGTTGCAGG
CGGACGAGCTGCTGGCATTCACATTGACCTGCGGCTGCGATGGATACGCAACCATGTTGGGTAACTGCTGGCGGAACATCCTCAGAGACTGCGTC
GAGCCGTAGACATCCAGGAAGGCCCACAGCTGGAGGGACTGGTCCACATGCATCACCACCACAGCTGGTCCGTTGTTCTTGCTGATGCTCACTTC
ACCGTTGGGCGCCACGAAGAAGGCAATCTCATCGCCGCGCTGAGGAGCAGCTGCAATATCCTTGCTCACCACCCAGTACTCGGGGCGATCGAGCA
GGAAATCCGAATCATTGGGCAAATCATTGGGCTGCAACATGGCCGGATTGCAGGAGGTCAGACCCAAAGCCAAGGCACCCACGTACATCTGTTCC
GTTTTCAGGACCTGCACAATCAGCTTCTCACCAATGCGAATGGGACGGGCAGTGAACACATATCCCTGGCAGAAGTCAGATTCCGTACGAGAAGC
CACAAAGCGATCCTGCGAGAGCCGCACATTCCGGCCCTTGGTGTTGTGGAAGGGCACTGGAATCAGTCGTCCGTTGGCATTGTAGCGCAGAGGAG
GCAGTCCATTGGCCAAATCATGAGCAATGGCCGCCTGTTCTACGCTAGCCACGCTTCCACCGTTTCCTGCCAAGTGCAGGGATTGCAGGGACGGC
ATCACATGGCGCTCCAGATCGTGCTCGATGGCCGCAGTGTGTCCTGGCAGGGATCTCCTCGACTGCTGATGCGGGTGATGGGAATTCAGGGCGGA
GGAGGCATTGGCAGCTGGCTGGGGCATTTGCTGTTGCTGGGCGGGCACAGTGGCCATTGGTATAGCCGCTGGCTGCTGCTGGTACATGTAAATGC
GAGAATCGAGAAACTCAATGCCCGTGCAGTTGCCATAGATATCGATCACCGTCCACAGCAGGCTTCTCGTATCGATGCCGGTCAGTATCACACCC
TTCTCCTCGTTGTTTATACCATAGATCACATCGCCAGCTCCATTGACATAGTAGTAAAGTATGTTGTCCTTCTCGCAGTACTGCTCGTGCAGAGC CTTGGCCCAGAAGCCAGGCCTGTTGGTCAGATCCGGACAGGCGTACTTGGGCAGCGTTCCCTCCAGCGTTACAGGATCGTTGCTGGTGAATCCAA
AGCGAATTCCACCGTTCCAGTTGTTCGAGATCTCAGCAAACTTCACGCAGATCCTCTCGTTGATGCGAACCGGACGCGCTGAAAAGGTGATGGCC
CTGCAGAAGCTCTCAAAGCGACGGGCCAGGGTTCCGTCCCTTGAAATTCGGATGTTGTCGCCATGTACGGAGTGGAATTGCAGCGGAGGCAGGTT
GTTGGGGCCAGGACATGAAGAGGGTGAGCGGCGAACTGAAATGGTATATGTGAAAGTTGAGTTAGTTAGGATTTTTTATATAGTATTATATTTC
ATTTAAATTTCTTGCAATACGAACATGATTTAAGCTGTTAGTTTTATCCCACAAATCATTTGGAAACCTTGAATATACTTTCGCATTCACGAAAT
GCTGCCTTCCCACAATCCATTTATCTATTAGTTACATCTTCTGCCACATTGTTTTAAAATCTTTTTCCCAACGCCAGTTCCCCGTATCAAATTAC
GCATCTTCAGAAAGATGTCTCCAGGTAGCCGAACATTCAACCATGTGCTAGCGATCGAATTACGCAGAAGCCCAAACTGATCTTCCTGGGTGAGT
CAATAACCCCCAACCCAAGACCCAAATTTAGTTGGTATTCAAGCACAGGGCACGTGACTGTATTGAAGACTATTGAACCATTGGGTTTTGGGGAT
TTGTTGCCTTGGGAAAAAACGCGGACTCAAAAGGATTTACCATGGTCATCGCCAGCTGCTGGCCCATTTTCTTGGAAAATCAAAGTCACATACGT
GTGAAGTACAAGAATTACTTGAGGAATAGATAAATATTGGTGTAGGTTAGGCTAGAGAATTCTTACAATTTTCAAGCGATTTCAAATTCCTAGAT
ATATATTTGAATTGTTATTTTTGTTACTAACTCGTTATACTGGATAGGCGTTTTTTATTACCAATGAATAGCTTGTTGCTATCGGGCTTATGGT
AAATTCTTTGCAATTATATAGGGAAGCACTTCAATGGCAGAGGAATACTTTAGGAATCCCTTAAACATATTCCCGAAATTGACTTAATTATTGCA
CCTTGCAAATCTACGTATATCAGCAGCTGCTGACAATTACCACAAAAGACTAAGTCAGGGCAGAAAAACCTATAACCGATCCATATGGCCATACA
TATAAATAATTACTTGAGGACGAGGAGTCTTTGGATGGCGACAGGTTTCTGCTCAGGTCGCTGGAATATGCCCAACATCAGACGATTCCGGCGGC
ATGTCAACAGTTGCAGTAAAAAAATATATAAACTCAGTTTATAAGAAAGCCATGGCGAAGGACCTGAAGCAGATGAGGCTGATGTTGCTGGTGAT
TACCATGTTGATATGCGGCGCGTGGCACTGAAGATCAATGTGTTTGCTTTGGAGCGGCATGTGGCAGCTGTCCTTTTTCCCTTCTTCTCGATTCC
TTTTGCAGCCTTTGTTGTGCGGAGGAAGAAATAGGAAGGTCAGAAGAAAGCAGCTGTACGGTTGGAACAGGTAAAACAACCCCTATGGAGAGCGA
GAGTCTGTCCCCGTTTTTCGAGGGTAGTTTTCAACGTTTTCGATCGCTTAGGGGTTGCTGCAGTTTCACAGTCTGCAGCTGTTCAAATTTCGAAA
AAAAAATACTGCAAGACAGATACAAGATACAAATGCTTGGGTATCTGAAAGATTCCCCTGGCTTGGCAGTGTCTTTGGGGTTGAAATTTAATCCT
AAGCCAGGGCCAATGACTTGCACACGAAATCTGTACTGTCTGCTTCCCGAAAAAATCCAATCCTCAAGTGCTTCCGCTGCACGAAGTGGAAAGGG
AGCACCAGCTTCCGGTGGCTCCCATTCTAAAGGAAACATCGCGCCTTTGGAGATTCGCCATGGAGGAGGAGGAGAACCAAGGTGGAGTAGAAAGC
CGGCCCAAAGACTTCTACTACGAGTGCAATACCCCAACCATCCATATTTATGAAGTGACCGCGACGAGGAAGTAGGAAATCACGTACTACGCACA
TACGTGTACTGGATTGGGGCCTATTAGCTGCAGGATGTTGTCGTCTCACTAGCCTGGCCAACTGGCGACGCCTACTTTTTATCGGCCCAGACAGT
CGTCAGTCAATGGATGGAATTGCAGCGGCGATCACTAGCATTCGCTGGCATCAATGAATGAATGAATGAGTTAAATACGCGCCTCGCATTTTTCC
TTAAACTCGCAGTCCCAGAAACGGTGCTTCATAGACGCGTTGATACTTTCAATTAGCCAGGCCACAATTAATTAAGTGCAGCGAGGCTTTAATGA
TACCCTCCACCCCATGATAACTAATTGCATTAAATGTATAAACGATAGACTTGTCGGTTGGGCAGCAAACAGTGGCGGCTCGAAAGCGTTCAATA
CGCTTTCAGAGTAGGAAATTATTAAATGAATACCTTACGGTAGGGCTGGCTTTCCGGCACTCTTAACTATGATTAAGGATACATAAAGATAATAC
TTGTGAAACAAGCCAGTAGCGATGAAGACCAAGAAATTATCCATTTCCCAGGCCATCCAATCATCATCCAGTTTCGACACAATATTTGCCAAATA
ACAACAGAAGATGAAAAGTTCAAACTTTCGGTGGTGGTCATGGTGCGTTTGGAGTTTGCCGCTCTGCCGCAGCAAAGGTTCCCAAACGCCGATTC
CCGAACTGGCAAAACGAAGACCCTGGCACATCCGATCGACTGCAAACGATCTGGCGGTGGCTGCTGCAGTTGCAGGCAAATTTTCGTTGCTTTGC
CAAAATGGAAAACCTGATTTACCGTTCGGCGCGGATCGGGAACGTCTTTGGATTCGCCACCAGCAAGCGAAGCAAAACATTTCCCACGCTGAGCA
CTGGGCAAAAATCAAACACAAACTCCGTAGAGACAATTCCCACGACTCCAAATTTGTATATATAGGAGATATATAGTAAATTTGCGGCTGCCGAA
CATCGAAAACCTGTAACAAGCCGCGGTAATTGCGAGAAGAGAGTGCGCAGTTCGCAGTTCGGATCTTCCCGAATCTTTTGGCGAACTAGAGAAGA
AGCTGCAGCTGGGTGATCGAGCGGGTGGAAAATGTGAAAATCATGCAGGTGTCATAAAACAAAACCCCGCTTCAATGGAAAAAAAAGGAAACCAA
AACCAGTGAGGCAATTGTGCGGCCATCGTTAGGCGAAATCATTTTAACGATCTGATGAAGATCTCCAAACATTCAAAATCCCATTGAGCGCAGAC
ATCATTAGATTTCGATTGGCACTCGTGAGTCGAGTTTGGCGATCATTAAAGGCAGATTACGATGATGTCTGAATGAAGGCTAACAAGGGGATACG
ATGTGAAGCTAAGCATCAACTTATTGAAACGATCGGTTCTAGCAAATCGCATCAAAGTTAATTAGTTCGGTAGCATTCAGGCTGTGGGAAATCAT
TGGATCGCTTTAATATCAAAATCTTTACTATAAAATAAACTAATTTTCAAAGTATGGGTATACAAAGCATTATCTTGACATAAACAACCAACCAT
TGCTGACTGCAACATTGTTCCCGCTGCCACCCACTTGAACTCCCTACCCGTTTGCACCGATTGAGGTCACAGGTCACGTGCTGCCCCGCCCCCTG
CGCCGTGCCTGTTGTTGTCAGCCCACGTGCGTGTGTCAGAAGACGTGTGCGGACAATTAACACGCCCCAGGCCGTTTAATTGCACCGGAAGTGTC
CCATAAAAGCCGGGGCTTTCGTTCAAATGCCGGCTTGGCATGCCGAGGTGGAGCAATGGATCATTTATACAAATTGTATCAATTGGTCAAGCATT
TGGCATAAATTATCGGCATTTTGCAGCGCCGCAATCAGTCAGATCGAGTGGGTGAATGAGCCGGATTGAGTTGGACCTAAGCATTTTGACTTCCA
CGGGCTTGTCAATGGATCGACCCACGCCGATAAATAACTTATAAGCGTATCTATGGCCAGCCACTCCGCATAGTGTGCTTATTTTTCTACATTTT
CCTTTTCGACATATCAGTGAAATTAGTTGAGGAAACAGTGTGTGGGTCGTTTGTTAGTTAGTCAGAGACTTGATCTGTGGGCAGAAAAGCCAAGC
GTTGGTCGCAGCTTAAGAGCTGAACAATTGTCCATCGAATGGCTTGTAAAACAATTCTCACAGCAATAAAAGCAATGCTAAATTCTTGTCTTAAA
TATACGTAAATGAGCCTAATGAATGTTAATTAATCGCTCGCAAACAAACAATTTGCATGGGGCGGGAAAATATGAAAGTTTTCCTCACAACAGAT
GAAATTTTGTTTTGTTTTGTTTGTCGGCGTTTTTAAGTTTTCCTTTCTAACCACAAAATACCAAGCATTTCATCCCAATCAATTTTCCAGTTTGT
TTTTTTTTTTTTTTTTGATTTGGTGCTAAATGCACTTAGCAAAGAAGTTCGACTGAATCGAAAAACCCAACCATTGAGTTGATGCGAAAACCAC
TTCCGTTCTGCTTGAGCCGCTGACCAGTACAGCGGAAATTGCACTGAGATCCACTCATTGCGAGCTGCTGGAGCGGGAAACTCTCTCTTGCGGTG
TGGATTCCCCCACCGGTTTGGCCCCTCCTGGCAGCGCATGTAACTCTAGAAGCTTAGCAAGAATGGACGCAACATAGACTCTCTGCAAATATAAT
AAAAATAATTACACAACGGAAAAGGGGCCGACTGGTGGCGGCGGCTGGCGGCGTTGACAGCAATGAAACCAGAGGTCAAACTATGCCAAGTTGCT
GCAACCAGTTGTTATTGTGTCTGAGCAGCTTTACTTCTTCCCAAGTACATTGCACTTTTCATGCGATTAAGCGAAATCTGATACTGCACGCCATG
TGAACTAAAAATCAAAGAAATCACAGCAGCAGCAACTCTAAGTATATCAACCATTTAGATAAAGACTCTTCAATGAAACTATCGATAATACAGAA
AAAAGTGACTAATCAATGAAAGTGCATCAGGAAATTTCCCACAGGAAGTTCGAAGTAATCAGGGAAGACCATAAAGATAATCGGTTATCTTACAT
GAAGAAATTAGTGTTCAAAATGCTTGGTTTTGCACTTGCTTAAGAAATCCACCTTACATATTGATCACACCTCTCTCAATGGGTTCAATGACTCC
CAATGACTTTTCTCCCCGTTCGGCATAAATTTTCCGACTTTCCACGCACATACACACAAATTAGTTATAAACACCCGGATGAGGAGGCGCAGCTC
CCCTTCTAATATAATTAGCCACCGAAAGGGAGAGATATAGAAAAGCATATATATAGAGAGAGAGAGACGGAGAAGCGCTGAAGGGTGGGTGGCCA
AATCAAATTTACATGTTTATTTTTACAAGCCTACAGAAAGCAACTCAGTGGAATGGGAGCACCTCTCTATCGATGCACATGATATATCCGCGTAT
ATGTATATAGTATAAATATCTATGGTTGTTTTTTTTTTATTTGGGCACTGAAGCATGCAGGAGGCCCCAGCCAAGAAGAACTCAACTTTTTCAGC
TCCGAATAGACATAAAACCGATCTAAATATACACGCGTAGATATAAGGAAGCAAAAGGGAACCATAAAACGCACAATAAACAACATTGTCTCTTA
AAGTGTTGACGGTTTCTGCAGAATAAATCGTATGGATGAAATATGAAATGAAATAGTTGGACTTCTCTTTAGTTGAAGCAACTTAATTATTAAGG
AAGCAATTAATACCGCGTTTCGTTGCAGTACTGTACTTTCGAGAGCTCAGATACGATAAGCCCGGCTTTCTTCCGCTACGTTTTGTTGCGCTTTG
TAGGCTTGCTGTTTATCGAAGCGTTGCAATTACTGCAAAGGGCCAGTGGTGGGGTCTACATAAATGTACAGAAAAACATATATACGAGTACAATA
TAGAAAAGTTGATAGTTACTACCATACAACTTGCATTTCCTCGCACTTGACTGCACAAGACACCCACCCCCGCGATTCTCTACAGTCTGCCAACT
CTTTGTGTAATTAAATCACTCGAGCGTTGAGGGGGAGCCCACAATAACAGCTTGAAGTTGCGCTGAGTGGAATGGAATGGACTCGAAGAGTCGTC
TTGTGATAGGAACACATCATTATTACATTATAACGCTGTTATTACAATGGCTGACACAGACAATTCAAGTGTTTTGGACTGCGGAATTCGATAGT
TTTTGATGCCACCGGTTGCATTGTTATCGGCCATCTCATTAAAACTTAGTGTTATAGCCAAACCATGCAAATTTCGAAGATTTTAACATATTAAA
TACCCCGAACAGATGCAAAGCTAAAACCAATCTAGTTTTGGTTCCTCCCAAAATAGGTGTACATATTAATTACATTAAAGTTCTGCCCGAATTTC
GGGCCACAAACGCTAAAGGCCAAAAACCAAAATCCAAAAAACTCGATCTGGCCAAGTTGCTAGCGATGGATAGCCGAACAGCTGCTGCTGCTGGA
CATAGAGGCAGGCATAGATTAAATACCCGTAGGTGTTCGAACCGAGTAGATATACCGACGGTGATTTATGCCTAGCAACCAGCACATCGCCCGCC
CTAACCCGTCTGGAAAACACGCCCTCCCGAAAGGCCTACAAAATTGACCCAAAGATGCCTTTGGATATCTTTTCGTCTCACTTTGCGTGAGTTAA

FIGURE SHEET 688

TTGCAGCTGATTTCTTGGCCAGGTATATACTATGTGCTATGTGGTATTGCTATATTATATGTTTCTACCTGTAGCTACCTGAACTCCACCTTTTG
TCTTGCGTCAGTTGCAACACCCTGCGGTGTAGCGTATCTACTTAGATTTTTTCTTTATCTATGGGGTGGTGTGCGTTTTTATCTTTCGGCACAGA
CAAAATGTTAACAATTTTGTACTACACATTTGGGTCGTGAGGAGAACTAAGGCGATACAGACAATGGTTATAATATACTTTTCATTTTCAATTTT
CATTTAGTTATACACTAGGTTAGAATTGTGAGATAAATCGAAAAGATTTGTTAACCGATGTTCACTGTACTCGTCTTCAAGCTACCAACTTAGTT
CAATAACTGATAAGCGAAAGATGTGGGAGGCACTAAATAGGTCACAAGATAGCTAGCTCTTTAGAAAAAAGCTAGCAAAGTTAGCACAAGCATCT
TTGTGTATATCCCCAATAGTTAACAACTGGTATTTATAGTTAATCAGTTGCAAAACGTTTACACTTGTAGAGATAACATTTCGCAGTGTCCGTTA
TCAAAGCGCGAAATTAAGCAGTGCTTCATATCAGCTATATGAACTATACTATACTACAATAACTATACGCAAACTTCAGAATGACACATCGAGAT
GATGACCTCATGAGGGGGAGAAAAATAAGTGAAAAAATAACGAAGGGGATGCATGAAAGTGGAAAAATATAGCAACAGATGTATGTAGCGAAAAT
GCTCAGCATACAACTGTGCTCAACAGAAAATGGCTTACTGGGAAATCAACAATAATATGTTAATATTGAAGCAATATTAGCAAAATGTCTCTTAA
ACATTATGTTTACAGAAATTTGTTTTTAAGCGGCGACTTACATATTTTGAACTTAATAGAATAACATTTTAGGTCTCAGAAGTTAATGTATGTAT
ATTTATGGTGACCAACATTGTACTTAGATATGTACTTATATGTACAAACTTCCTTGGGGGGTGCGTACCGTCATTAACAATTGACTATTTACTTT
TGGCCAACAATCGAAGGTCGGCGACAATTTGTATTTGTGTGTCCCATAATCGGGGTCTCAAAGACGAGTTGGCAGTGCTCAGTTGCAAGCACAC
GCACGGCCAAGCAAACCATTTCGAAAAGTAAACCGTGAGAAGCTAAGTAAAAGCCAAGAGCAGATAAACTTTTTAGCCAAAGCAAACGTGGCATG
CCAACACACAATAATAATAACAACAACAAACAAGGTACGAAATGTAATAGAAAATGCAGGTACAAAAAAGCAAAAGCAGCTGACGCCGAGCAAAA
CAACAACAAAGCAATTTCATTGATTACCGATAGGCAACGCACGTTCAAAACAAACGGACTGGAGCCGCCGCATAAAACATAAACCATTGCGGGCT
TAAGCGCTCAGCAGAAAAATAAAAACTCCAAACACACTCAAGCTTCAAAGCCACGCCTCTTCCTCTTCTCATCCCGCTAGTCCATGGCTCTTCTC
TTCTTCTCCTGCCGTGGATCGTTTGCTTTTCTGTTGTTGCTACCTTTGTTTTTGCTTTTGCCGATGGCGGCAACGGCGCTTCGCGTACAATTCCC
CGAAAGGCAACAGCAACAACAACAAGCAATACTGAATGAGGCAGATGCAAAAACAGTGGTGGCGGGAAAAATGGAATCTCTTAAATACAGTACAA
TATTTTGCATAGCCACTTTTGACAAATAAAACTATTCCAGTGCTGAAGGACTAAATTAATAACTTTTTTTATTATTCATATTGCGTCGTTCGTT
GATATTCGACTGCTAGTTGTGCGACCACAATTGTTCGTAGGAGGCCAGTAAAAATAAAAAAAAAAGGGGTAGAAGCTTAGCCTATGCGTCACTGG
CTTTGCTTTGCTTTTGCTTCGCCTGCTTTGGCCAAAAAAGAGAGCATTGAAGCCGAGAATGCAATTGAGCCAAAGTCAAAAAAAAAAGGTGATTT
GTTGTTTTTACTTCTTTTTTTTTGTCTTTCCTTAGCTCAGCTGCTTGCAACCAAAACAAAAACAGCGCAACAAATTCCCCAGCCCAGATAATCGT
TATGATAAACATAATCGCTCCTTGGGAAAATTGCTTTTGGTGGTATTTTCTTCAACTCAAGATCCCTCCGATCTGGTCTTCTCGATCAATTTGCG
GTTACTTGGGTGCGATTGAAAAATTCAGTTTTCGAGAACTGACATTTCCGGCGAAAAAGTCGGAGTGTCGATGTTAAATTCTGCCGAAAAAGCCT
TGAGAGAATTTCACATTTAAGATTTTTTCGCGCTTCTTTTGTGTCTATCTAGTCGGAAAAAAACAATTACTATTATAATCGCAAACTGGGCGTGT
TCTGGGTGAGCATTTATTCATTAGCTTTTTGTTTTAAACTAACTCAAACTTTTTCGGTTTTTGCTCTTATCTTTCGTTATTTGTTATTGTTCTTG
AGACGTAAAATGCTAATGTATGCATAAATGATTGCGGCTGGCTGTGTTTCTCGCTTATTTATCTTGCCGCTTTAATTAACCGAATGAATGAAAGA
GCGATAGGTCAGACCACATGCTAATATTATGTGGGAATATCGCTGGAGATAAAAATACGATTCCCAGATCGATGAATAATGTATTTAAGGCATTT
TCGCACGCGGTAATTACATTTGCTTCAAGACTTTAATGGTCAGATATCACGAAGGAAGTTTTATATTGTTAAAATGTACTACATCTACTTTAGAA
CCCAATCACACTGATTTTAAAAATTATTCCTGGATATTCCGAGAATTGTACGTCCTTTGAAAAACGACTTGGAAATTAACTGAATATTCTTGTTA
ATATATCCATCGATATCCTTAGCCCGATTCTTAGCCTGGTACTAATGCGACTACTAACCCAATCCAAAGCGCTTCTTGATCTTCTTGAGCAAGTG
CATTTTCTTCTTGCTAGAGAGCTTGTCCTTGGTGCTCATGAGCAGCTCGTTGGACTCCATGGCCAGGACCTGGGCGGCCTGCTGGGCGGGAGTGG
GCATGGCGTTGTGCAGCTGCTGCATCTGTTGCAGATGCTGCAAGTGCTGCTGATTCTGGTGGTGCTGCTGCTGCTGCGGATGGAGAGTTAGGTGCGGA
TGGCTGCCCTGCATATAGTTGGCTGGTATATCCGATAGACCCATGGTAGTGGATTATTTCTTATTTCGTTATTTAAATTAAAACAGACGAACTAA
ACGAACACGCGTAATGCTAATGAAAATGCACAAGCTGCTTGCGTATTTTATTTGGCATTAAATTAAGCGATAGAGTTCTTCTTCGAATTTGAATG
TTTTCCGTTAAAACATTTTGAATTTGGTTGGTTGTTTGTCTGCGCGCAACGGGAACAAACGAAACGAAACGATACGAAACACAAAGACCGACGAC
GACAACTTCGAGACAACCTTTCGCTGAGTTTTTTTCAACAAATAAACGGTGGTGCAGCCTTTTATAGCTTCGCACCAGCGCGACGTCGCTGACG
CAGCTCAGCTGGAGAGTAACGGATAGTACTGGCGCGCAGAAATTCTCCCGTCAGATTTGGCTTTTTTAGTATATGTTTTCAAGATATTTAGAAG
TTTAGGTATGCCAGTAAGACATATTTGGAAATTTAAGTTTTTATAATTACTATTAACGTTTAGTGACAATTTGGGCTGTAGATTTGAATAACAT
TTCCTGTTTTACAATTTAATTAAAATCAAGAAACGGTAACTAAATTACATTAAAAATGCTTCAATTTATTTAAACTTATAATTTGTAAGCAATCT
ATTCAAATAATTTAAAATTTATCCATTTTCTGGCTAAGGGCTGTCAGCCCTGAGCGTGGATGGAGCGAAAAAGAGAGCTCAAGAGAGAAAATTAT
GAGACGCCATCGCTCTCTTTCTCTCTCTGGCAGCTGTTTCTTATTTACTATGGTTTCGCTTTGTGCCTGCTATTCGCGTGTATAGAGCCTCCCTT
ATAATTTACCTTTATGCCTCTAACTCTGCACCTTGATCAGGGATTCCTCCACATCTTCTCCTGCTGTTGCTCTTCCTGCTTCTTGTTGTTGTTGC
TCTAGGCCTGCATTTGGGATTTTGGCCATAGTGCTCTGATCTTCACTAACAGTTATTCTCCTCACCTTAGTGTGTGTGTAGTTCAGCCAGGTTCA
AAGCAATTCTTTTTCTTTTTCGCAGGGTTTACAAGGTCTGGCTCATATAACTAGAAAACTATTTCAATTGCCCTAATGCTTTTGATCGTGAACTT
TGTGGGCCAAATATCACACGTACATACATATGTGTGTATGTATGTACTCAGTTGGAGTATGTATGGAGTAATTCCATGGGAATTAAAAAAAATTC
CCAAACGTTTCTTGATAATAATAATAAATTTCTTCTTTTCCCAATTGTTTCGGCACATTTAATTGTCCAT
(SEQ ID NO: 1273)

Exon: 14366..13834
Exon: 4500..2759
Exon: 2699..1001
Start ATG: 14104 (Reverse strand: CAT)

Transcript No. : CT32118
AAAGGTTGTCTCGAAGTTGTCGTCGTCGGTCTTTGTGTTTCGTATCGTTTCGTTTCGTTTGTTCCCGTTGCGCGCAGACAAACAACCAACCAAAT
TCAAAATGTTTTAACGGAAAACATTCAAATTCGAAGAAGAACTCTATCGCTTAATTTAATGCCAAATAAAATACGCAAGCAGCTTGTGCATTTTC
ATTAGCATTACGCGTGTTCGTTTAGTTCGTCTGTTTTAATTTAAATAACGAAATAAGAAATAATCCACTACCATGGGTCTATCGGATATACCAGC
CAACTATATGCAGGGCAGCCATCCGCACCTAACTCTCCATCCGCAGCAGCAGCACCACCAGAATCAGCAGCACTTGCAGCATCTGCAACAGATGC
AGCAGCTGCACAACGCCATGCCCACTCCCGCCCAGCAGGCCGCCCAGGTCCTGGCCATGGAGTCCAACGAGCTGCTCATGAGCACCAAGGACAAG
CTCTCTAGCAAGAAGAAAATGCACTTGCTCAAGAAGATCAAGAAGCGCTTTGGATTGGTTCGCCGCTCACCCTCTTCATGTCCTGGCCCCAACAA
CCTGCCTCCGCTGCAATTCCACTCCGTACATGGCGACAACATCCGAATTTCAAGGGACGGAACCCTGGCCCGTCGCTTTGAGAGCTTCTGCAGGG
CCATCACCTTTTCAGCGCGTCCGGTTCGCATCAACGAGAGGATCTGCGTGAAGTTTGCTGAGATCTCGAACAACTGGAACGGTGGAATTCGCTTT
GGATTCACCAGCAACGATCCTGTAACGCTGGAGGGAACGCTGCCCAAGTACGCCTGTCCGGATCTGACCAACAGGCCTGGCTTCTGGGCCAAGGC
TCTGCACGAGCAGTACTGCGAGAAGGACAACATACTTTACTACTATGTCAATGGAGCTGGCGATGTGATCTATGGTATAAACAACGAGGAGAAGG
GTGTGATACTGACCGGCATCGATACGAGAAGCCTGCTGTGGACGGTGATCGATATCTATGGCAACTGCACGGGCATTGAGTTTCTCGATTCTCGC
ATTTACATGTACCAGCAGCAGCCAGCGGCTATACCAATGGCCACTGTGCCCGCCCAGCAACAGCAAATGCCCCAGCCAGCTGCCAATGCCTCCTC
CGCCCTGAATTCCCATCACCCGCATCAGCAGTCGAGGAGATCCCTGCCAGGACACACTGCGGCCATCGAGCACGATCTGGAGCGCCATGTGATGC
CGTCCCTGCAATCCCTGCACTTGGCAGGAAACGGTGGAAGCGTGGCTAGCGTAGAACAGGCGGCCATTGCTCATGATTTGGCCAATGGACTGCCT
CCTCTGCGCTACAATGCCAACGGACGACTGATTCCAGTGCCCTTCCACAACACCAAGGGCCGGAATGTGCGGCTCTCGCAGGATCGCTTTGTGGC
TTCTCGTACGGAATCTGACTTCTGCCAGGGATATGTGTTCACTGCCCGTCCCATTCGCATTGGTGAGAAGCTGATTGTGCAGGTCCTGAAAACGG AACAGATGTACGTGGGTGCCTTGGCTTTGGGTCTGACCTCCTGCAATCCGGCCATGTTGCAGCCCAATGATTTGCCCAATGATTCGGATTTCCTG
CTCGATCGCCCCGAGTACTGGGTGGTGAGCAAGGATATTGCAGCTGCTCCTCAGCGCGGCGATGAGATTGCCTTCTTCGTGGCGCCCAACGGTGA
AGTGAGCATCAGCAAGAACAACGGACCAGCTGTGGTGGTGATGCATGTGGACCAGTCCCTCCAGCTGTGGGCCTTCCTGGATGTCTACGGCTCGA
CGCAGTCTCTGAGGATGTTCCGCCAGCAGTTACCCAACATGGTTGCGTATCCATCGCAGCCGCAGGTCAATGTGAATGCCAGCAGCTCGTCCGCC
TGCAACGCTGCCTCCACGTCCCGCATGCTGCCCATGACCGAGTCGATGAGCAGTCTGAATGCCGGAGCCACTGCCAAGCTGTTGCATCATCCCTC
GCAGCTGAGCGTAGCCCAGAGTACGAGCACTTTGGCCTCAGCTGGCGGAGTCAATGGCAGCCGCATGATCAGCATGCCCTCCAACGGAGATATTC
TCCAGATCCAGCCGAATGGTGGTGGCACCGTTCTGGTGGTCAACCTGCCACCTGCTAGCAGCTCGCACGATATAAACGGCCAACTCGCGGCCAGG
CCAACGGCCACGGTAACCTCCAGCGGTGTTCTGGCCGGAGCCTGCTCCAGCGGCACCCTTATCAGCACCACCAGCAGCCAGTACATCGAGCAGCC
CATTGCCAATAGCACAAATAATGCGGCCAACAAGTGGAAGGACAGCCTGAGCGACCAGCAGAGCACCGATTCGAGTGCCGAATGCACCATCTGCT
ACGAGAATCCCATCGACTCGGTGCTGTACATGTGCGGACACATGTGCATGTGCTACGACTGCGCCATCGAGCAGTGGCGCGGAGTGGGTGGTGGC
CAGTGCCCACTGTGCCGGGCGGTGATCCGGGACGTCATCCGCACCTACACCACGTAGAAAGGTCGCGGGCGTTTCCTAGCCAAGCAACATTTACT
CGCAATCAAACCTACTAAAGCTACACATTATACCATACACACAAGTTGTTGCATTTTAAACGCAATTGAGCGCAAAGAATATTATATTGGAGAGA
TAGGCATTATTTTTGCAGACTAAAGATTAGATAGTTTACGCAGCTAGATTAGTGTATGAAACTATCAACTAATTTATCACACGTATGTTTAATTT
TTTTGTGATGTTATAAGTAAGTGCGCCCCAGAGCCAAAACTATGTATTGTTCAATCCAACAAAGATATCTTCGTTTTTTCAATTTTTTTCAAACC
TTGAATCGCCCATTTGTGCGTTGTATACTGAAAAACCAAAGTATTGTATAGGAGTTTATAGTATTTTGAATTTAAATTGGAATTAATTGAAAGTT
GTTGCAAATTTACTTAGTTTTTCTCTATGTCTAAATTCCAAACGATGTGCAAAATTAACAAACACAAACTACAAGGATTCTTTATTTGGCGATTA
ATCATTTTGGTGCTAAATGTTTTGAAAGGCAAAATAAAATTGTTAACGGATTTGAAAAGTTATGTTTAAGCTTGCAGCAACTACGAATGACCTTA
ATTTGATATGAAATCACAAGAAGCAAATATTGACTACTTTCCAGCAAGGAAATGGATATCGACGCAACTCAAATAAGTTTGCAGCACAAATTAAT
GAACAAAGATTGATCAGAAAACACTTATGCACGTAAACCAAAATAGAAAACTGCAAGAGCGTGTTTGTTTAAAGTTAATATTAGTCTAGCCCTAA
GTACTTAAGTTAATTTCTAGTCAACGAATTATGCTGAAGTTAAATCTAAACCGGACTTCATCCAACAAAGACACCACAAAAAAGACGTATTAAGC
ACGCTAAGCTATTTTAATGAAGCCGCATTTTAAATTACACTTAAGTAGTGCACGTATTTTAATGGAGACTTAAATATATTTAACTATAAACATAG
AACAAAAGACTTGTATGTTGTACCAACAGCTTGAATGAAATATGGAAAATGGAATGCCCATCTAAATAAACCATGCAGTTAGAAAATTGCCAATA
ATTAATTAACAATACCAAGCAGATTTAACATGAAGGACAAGCAAAGCGGATAAAACTTTACCTAAGATTGTATTAAAACTGAAAAAATGTAATAA
GCAAAGAACACAAAGAAATATGCGAAATGGAATAAAGCGCAAGCTTACTATTTTGTTATAAGAATGCATCCGGATAGGAGTAAATGAAGACATGT
TATTGCCACTAATAATAAACTTTTAATTTTTAAAGAATCATAGTTCGTAAAATTACGATACTGCGCCTAGTTATGACTAAACATTTAAATGTAT
TTATGAAATTATATTTGATATATGTAAGAAAACGCAATGCTGTAATACCATTAAATACTGACAACAATATCAGAAACAA
(SEQ ID NO: 1274)

Start ATG: 263 (Reverse strand: CAT)

MGLSDIPANYMQGSHPHLTLHPQQQHHQNQQHLQHLQQMQQLHNAMPTPAQQAAQVLAMESNELLMSTKDKLSSKKKMHLLKKIKKRFGLVRRSP
SSCPGPNNLPPLQFHSVHGDNIRISRDGTLARRFESFCRAITFSARPVRINERICVKFAEISNNWNGGIRFGFTSNDPVTLEGTLPKYACPDLTN
RPGFWAKALHEQYCEKDNILYYYVNGAGDVIYGINNEEKGVILTGIDTRSLLWTVIDIYGNCTGIEFLDSRIYMYQQQPAAIPMATVPAQQQQMP
QPAANASSALNSHHPHQQSRRSLPGHTAAIEHDLERHVMPSLQSLHLAGNGGSVASVEQAAIAHDLANGLPPLRYNANGRLIPVPFHNTKGRNVR
LSQDRFVASRTESDFCQGYVFTARPIRIGEKLIVQVLKTEQMYVGALALGLTSCNPAMLQPNDLPNDSDFLLDRPEYWVVSKDIAAAPQRGDEIA
FFVAPNGEVSISKNNGPAVVVMHVDQSLQLWAFLDVYGSTQSLRMFRQQLPNMVAYPSQPQVNVNASSSSACNAASTSRMLPMTESMSSLNAGAT
AKLLHHPSQLSVAQSTSTLASAGGVNGSRMISMPSNGDILQIQPNGGGTVLVVNLPPASSSHDINGQLAARPTATVTSSGVLAGACSSGTLISTT
SSQYIEQPIANSTNNAANKWKDSLSDQQSTDSSAECTICYENPIDSVLYMCGHMCMCYDCAIEQWRGVGGGQCPLCRAVIRDVIRTYTT*
(SEQ ID NO: 1275)

Name: neuralized
Classification: DNA_binding
Gene Symbol: neur
FlyBase ID: FBgn0002932

Celera Sequence No. : 142000013384626
CAAGAATCAGGCCGTACACAGAAAAAAAATAAGCGTTCACCTAAATAATATTTCTGTTTTTAGGAAATTTTAAAACCGCGTTATCACTTGCAACT
TCTTTATATTAATCTATAATTACCCAATAGCCATTATTATTCTCAAAATATTAAAAACTACGAAGGTACTACACTTCTTTGCGCTTGCTAAGTTA
TGTTCTTTTCAGTGTATCTGGCATATTCTTTGCTTGGCCGACGTGTGTCTGGAATGACTAATTGAATAGTGCATGGGCTCGTATATCTCGCAGAT
ACGTATCCGCCAGATACGTTAGGGAAGGCGTGTGCCCGGCCTAATGGCTTAGCTTAGCAACATGTTGCAATTAGCGATCTTCGTTTGGCAACATT
CGCTGCCAAAAGCTGGCAACATGCACAGAGAAACATAAACACACCAAGATTTTTTCACAAAGAGAGTGCTTCATAATTTTCTCTTTATCGAACTG
CGCTCGCCGGTTGCGAAGACGATCACAATTGGAATCGCGCGGCTCGCAACATGTTGCCTTCAAACCGGTCTGGCCATGAACTTGGTGAAAGAAGC
TACCATGGCGAAGCTCCAGTTGGGAGAAAAGTCTGCGCCGCGTTTTCCGCTTGGAAATTTTTAAAAGACGCTGCCATCCAGCGGCCTGGAACATT
TGTAATCCGACGTTAGAAGTCTGCGGATCGTGGCCAAAAATCGGAGTGTCCCAGCCAGCTGTCATTCTGACTCCTCCTGACTCTGCTCTGAACTT
CGCGTGTGTGTCTGTCTGAGTGTCCGAAGATTTGGAGTTACTGTTAGTTGACACTAATACGAGAGCGAGTGAAATACGAGAAATACAAGAAAAAA
CCGAACGTGAATCGCGCGAGTGCAAAAAGTAAAGAAAATAGAAAGAAGAAGAAAACCCCAAACAAACAAACAAACAAAAAAAAATAGTGCGAAAA
ATCGATATAAGAAAACCTGAAGAAAACGAAACTCGGCAATCGTGGTCAAAATGGTGCGGTTAAGTGCAGCCTGGAGCTGCTGTTTTTTGGCCCTG
ATTGCGTTGGTATCCACTGTCGCCTCCTCCGCTGCGGATTATCCGGGTGTCATCGAACTGGTGGGTTATAGCAATCGCCGCGCACGGACTTACTT
CCAAGAGCAACCCCGCTCCAATCCCAATCCCAAGCCGGGTTTGACTTCGGCCAAAACCCGGGCGGATATTGAGACCGTGAAGCGGAATATCCGTA
AATACGATCGTTTGCTAGAGTTGGATACGAAAAATCTGCCAGAGCAGCAAAAGGATATGCTCGCCAGGATTGTGGAGCGAGTGGCCAGGCTCAAG
GAATCCCTGGACATTGAGGAGCAGCAATTTAACCAGCAGGAAGCTACCTCCTCCAGGAGCAGTAGTAGTACCACCACTAGTGCATCCAGTACTCA
AGAATCGCAAACAGAAGCGGAAACGGAGCTGGATCAGGAGCCGATCGAGCAGAGCACACAGCTGCCCACTGGAGCCACCGAAGCTGAAACGGATC
CCACCCTAATCCTAGACGAAACTACGCTGCTGGAGCTGCAGAACACGATGAACGAGCAGGCTGCCATGAGCACCATAATGAAGGAAATGCCCACG
ACCACGGATATGAGTCAGCAGGAAGCGGAATCGGAGGTCCCCGACGAGGAGGGAGAGACCACCTCACCAAATCTGACCACCCAATCGGAGGCAGC
GACGACCAGTGATGAATCCCTCACCGATTCCACTGATCCCGATGATCAATTCGTAGCTGCCAGATCGAATAACAATATAGCGGCCATAACGGCAG
CGGATGATGCCGATGGCACCACCACAACCACCGCCAATACGGGCAGTCAGCAGCGCACGTTGACCACCATGGGAAAACTTAAGAATCGGGCCACC
AAGCGACCCTTCGCCCACAAGGTCACCGCCGCCCTGAAACGAGGAGGTCAGCGTCCGAGTAGCGTGAGTGCGGCAGCTGCGAGTGCGGCAGCGGC
CTCAAAACCCAGTAGCAGCACCACCACCGCCGCCGCCGCCAGCAGCACCACCCAGAAACAGAAATTGGCCACCAACAGTTTCCAGCAGAAGCAGC
AGCAAGCGAAGCCCCTGCAAAAGGTCACACCTTCGATTGGCGGTGGTGGATCATCCAACCCGTCCTCGGCATCCATTCCCTCGGCTACCACGAAT
TCCGCAGCTCCCTCCTTGCCTATCGAGCAATTGTATACCCGTACTCCCCAGGCCAATATCCCATTGGCAGCAGCAGCAGCAGCAGCAACCTCATC CGCCTCAGCAGCGGCAGCAGCAGGATCAGCAGGATCGGGAGCCACACCAGCCACCTACAGCAGCCAGCATGACAGCATGGTATACGATGGACATG
TCAATGCGTCGGCCTTGATCGACAGCCTGAACACAAACGCTCGGGAGGAATACTACCAGCAGAAACTAGGAGCAGGCAACAAGGATAACAAGGTA
AGGCATTTACCACTTACCTATACTTTTGGAAACTTATCTTTTTACTATTCGCTAAAAGCTAAAAGACCATTTAAACGCTAGTGAGATATATTATT
TAAAATTTCTAATAAAGAGAGATCTTTCAAATAAGACCATAATTAAGGTAAAATTTTTGTGCACTATAAATATTTATAATATTAAACCCTTATTG
AAAGGGTTAATTTGTCATCGTTTGCAAAACTAGGCAGCCATATTGATAGTAACAATACATTCTTTTTACTATAAACTGAAAATCATCCAATAAAT
AGCTCAATAACAGGGCCCAAGGTAGCTGACATATTGACTCCTTTCCAAAATACTGTCCCATCTTTGGCTTAATTAGCAATGACCACCAAAAAGTA
ACAAAGCTCGAAGGTTAAATGTAGAAAGGGGAAAGGCGGCGAACGCCTGTCAAGCTAGATACATATTTCCCAAGACAATGGGCTAAGTCGCCGGG
ACAGAGACATCTCTGGACAAAAAAAAAAAGACGGAAACCGTTTCGGGCTATGTAAACAAAAACTGGAAGAACCGAAGTAAACCCCGTTGAATGTC
AAATGCAGAATTATTGGAACAACTTGACTCTCAAACTATAACAACAAAGCAACAAGCGATGACAACGACCATGACAACACCAACAACACGAAGCT
ATCGAAGGCTTAGTAGGAGCCACAAAAAGTTCAAAGCCAAACAGAGAGAAAAATTGTGCTTACTAGAAAATATATGAAAGTGTTATAAATTAGTT
ACAAGCTAATTTTTATCTTCTTCGTCATTTTATGCTTTTGTATTCAAATTATTCCAATTGGAAATATCGATCGGCAATTGAATTTTATTTGAAGC
ACCTCTCTCTGCGCTTCTCAAAGTATGTAGTGTGTTGCTCGGCTTATCTTCTTTAGCTTTTGATCTTATATAACACAACTAAAACATATGTTTCT
AATCTATGGATCTGAAAGCCACTAGATTTAGATATTTAGTGTCGTTCTTTGGCTGGTTACAAGATAACATTTTTTGTAACTGTAAGGGGGTACTG
TCTTGGATAGTTGGCCAAAGCTGGCCACTTGTTATA
(SEQ ID NO: 1276)

Exon: 1001..2551
Start ATG: 1001

Transcript No. : CT32253
ATGGTGCGGTTAAGTGCAGCCTGGAGCTGCTGTTTTTTGGCCCTGATTGCGTTGGTATCCACTGTCGCCTCCTCCGCTGCGGATTATCCGGGTGT
CATCGAACTGGTGGGTTATAGCAATCGCCGCGCACGGACTTACTTCCAAGAGCAACCCCGCTCCAATCCCAATCCCAAGCCGGGTTTGACTTCGG
CCAAAACCCGGGCGGATATTGAGACCGTGAAGCGGAATATCCGTAAATACGATCGTTTGCTAGAGTTGGATACGAAAAATCTGCCAGAGCAGCAA
AAGGATATGCTCGCCAGGATTGTGGAGCGAGTGGCCAGGCTCAAGGAATCCCTGGACATTGAGGAGCAGCAATTTAACCAGCAGGAAGCTACCTC
CTCCAGGAGCAGTAGTAGTACCACCACTAGTGCATCCAGTACTCAAGAATCGCAAACAGAAGCGGAAACGGAGCTGGATCAGGAGCCGATCGAGC
AGAGCACACAGCTGCCCACTGGAGCCACCGAAGCTGAAACGGATCCCACCCTAATCCTAGACGAAACTACGCTGCTGGAGCTGCAGAACACGATG
AACGAGCAGGCTGCCATGAGCACCATAATGAAGGAAATGCCCACGACCACGGATATGAGTCAGCAGGAAGCGGAATCGGAGGTCCCCGACGAGGA
GGGAGAGACCACCTCACCAAATCTGACCACCCAATCGGAGGCAGCGACGACCAGTGATGAATCCCTCACCGATTCCACTGATCCCGATGATCAAT
TCGTAGCTGCCAGATCGAATAACAATATAGCGGCCATAACGGCAGCGGATGATGCCGATGGCACCACCACAACCACCGCCAATACGGGCAGTCAG
CAGCGCACGTTGACCACCATGGGAAAACTTAAGAATCGGGCCACCAAGCGACCCTTCGCCCACAAGGTCACCGCCGCCCTGAAACGAGGAGGTCA
GCGTCCGAGTAGCGTGAGTGCGGCAGCTGCGAGTGCGGCAGCGGCCTCAAAACCCAGTAGCAGCACCACCACCGCCGCCGCCGCCAGCAGCACCA
CCCAGAAACAGAAATTGGCCACCAACAGTTTCCAGCAGAAGCAGCAGCAAGCGAAGCCCCTGCAAAAGGTCACACCTTCGATTGGCGGTGGTGGA
TCATCCAACCCGTCCTCGGCATCCATTCCCTCGGCTACCACGAATTCCGCAGCTCCCTCCTTGCCTATCGAGCAATTGTATACCCGTACTCCCCA
GGCCAATATCCCATTGGCAGCAGCAGCAGCAGCAGCAACCTCATCCGCCTCAGCAGCGGCAGCAGCAGGATCAGCAGGATCGGGAGCCACACCAG
CCACCTACAGCAGCCAGCATGACAGCATGGTATACGATGGACATGTCAATGCGTCGGCCTTGATCGACAGCCTGAACACAAACGCTCGGGAGGAA
TACTACCAGCAGAAACTAGGAGCAGGCAACAAGGATAACAAGGTAAGGCATTTACCACTTACCTATACTTTTGGAAACTTATCTTTTTACTATTC
GCTAAAAGCTAAAAGACCATTTAAACGCTAG
(SEQ ID NO: 1277)

Start ATG: 1

MVRLSAAWSCCFLALIALVSTVASSAADYPGVIELVGYSNRRARTYFQEQPRSNPNPKPGLTSAKTRADIETVKRNIRKYDRLLELDTKNLPEQQ
KDMLARIVERVARLKESLDIEEQQFNQQEATSSRSSSSTTTSASSTQESQTEAETELDQEPIEQSTQLPTGATEAETDPTLILDETTLLELQNTM
NEQAAMSTIMKEMPTTTDMSQQEAESEVPDEEGETTSPNLTTQSEAATTSDESLTDSTDPDDQFVAARSNNNIAAITAADDADGTTTTTANTGSQ
QRTLTTMGKLKNRATKRPFAHKVTAALKRGGQRPSSVSAAAASAAAASKPSSSTTTAAAASSTTQKQKLATNSFQQKQQQAKPLQKVTPSIGGGG
SSNPSSASIPSATTNSAAPSLPIEQLYTRTPQANIPLAAAAAAATSSASAAAAAGSAGSGATPATYSSQHDSMVYDGHVNASALIDSLNTNAREE
YYQQKLGAGNKDNKVRHLPLTYTFGNLSFYYSLKAKRPFKR*
(SEQ ID NO: 1278)

Celera Sequence No. : 142000013383859
TGCCTATGGACTTTAATTTGATTTTCCCAATAGAATTATTAGATTTTCTTGACTTTTGCTGCGGGGACGGCACTCGTTGCTCTGCGGATTCTGTA
AACGAGCAGATTGGAGATTTGTCTATCAATTTGGGTCACTAACTTGGCCTTTCGCGTTTGCTGTTTGGATCTTCCACAAAGTGCTCTTTAAAAGT
TGGCTGACTTCATTAACTTAAACTTCGAATAAAATAGAAAAAATAAAGTATATAAAAAAAATTTAAGTATAACAGAATTTATATAAAGATCGGTG
GTAGCTGTTAAGTTTATTGCAAATATATGTGAGTGTAAAAATTGATACAAAAGATATAAGCACTCACCGCGGTCTTAAGCTACTAAGTCATCAAT
ATACCTAAAGCATATGTTGATAACGATTTGAACTAATGGTAAAGTATACCTTAGAAATAAATTTACGACTATGGTTGCGTATCAGCCAACTTCAC
ATATTAAATTCACTTTGTGAAGGCTCCCAGCAATCGCTCCAGGCTGATTGAACATTTCACTTAACATATATTGCTTGCTTTTTTGTGATTGCAAT
GTTTCGCAGGTCTAACTATTACTTTTTGAAATTAATTACGTATTTCAATTCTTTAGGTAGTTAAGTACAGTTTATGTTCGATGTTCGACTTAGCT
GTTGTTTGTACAATAGTTCGTGAGTTTAACAATTTATACAGAATACTTATTGGCTGAGTCGTTAGCTGATTGTTTTTTTTTTTTACAAAATTTGA
ATTTTTGGTATATGGTAGGTATGTGCATTGCGGATATTTTCAATTCAATTGCTCCTTTGCGTTAATTTGCTTTCTGAGTGATATGCGAACATTTT
TCGATACATTGTCGGCTGTTTAGCAAATATAAAGAGGAGAGACGCGTCGCTCGGTGAACTGTTGCATGTGTTTCTTGTGCGCTTTTCTCAGCTACAGTAC
ATGTTTTGGGTTATATATGTACATTTTGAGTTTTGTGTGAACGAGGGCCCCTAAATCATGTGCGACATCATGCAACGACTCACATCACGGTTGGC
GCGATGCAAATGACCTTGATAATGCTGATGAATGCGCTGATATTGATGTGGCTGCTGTGGATGTTGCTGTTGCTCTTGATGTTGCTGCTGCTGCG
CTGGAAAACTCGTCTCCGATTCCATCATCATCATGCCGCCGGTGGCCTGCATCTCGTAATCCATCAAAGAGGCCTGCGTTCCAATTATTTGTGTG
GCAGGCAAGGAAAAGAAATCTGCAAGGCAATAAACCGATCATTAAGTTACATTAACTTATATAAAATAATTTACAATTTATTATATAATTGTATGTA
CAAACTGAAGTCTATTCCGATTTTTCTCAGTGCAACGGCAATGCAACGCAACACGTTGACACTATCGATGCTTGGCCCAATTACCGATCGTTTAT
TTATAACCAATTCGGAGCAGAGCAGTGTGTTGTCATTTCTTATCTACGAGTTAGTTTCTTTTTTTCTGCTTTTTGTTTGTGCTGATAACCTTATC
AACGCAATCGGAAACTATAAGGTAACGAAGGCAAAACGGAGTGCACAGATTAACAACAACTAATTAAGTGTAGTCATAGTTGCAAAAATACATAT
GTATATTTATTCCAATAGAAAACATTTAAAATTGTATTTCTATTATTTTGTACCCCTTTTAAAAATATTAATATAGATCAAAAAAAATTGAGATAT
ATATTTAAGTAAATCGTGGACAAAACTAAATGAAATATTCGTACATATCATTGAAATCACTTAAAAACATTTAAGAAGCGTTTATACCCTCAGAA AGAGTATAGATTATTGATTCACTCCCGCAGATATACACATTTCTTTTACCGGCTGTATATATTTACGCCCACACTGCCTTCCCCCTTTGTTTTCT
TCTATTGTTGGAACACTTTTGCGAATGCAGATTGATTAAACTGGCGGTGTAAGAAGAATCGTAACACTCTGTTGACCCAGTGTACATAGTCATCT
CCGCAGTACCTCCAGTTAATCCCCACTACTTGTGTGTTTTGTTTAGTAGGCCAAACACACCGATATACATATATGCATATGTATGTCTATAAAGA
CTGAGTCAAGCCGGTTTTTCTTTGCTAAATTTAAGCGGCTGTCAAGTGCTATCGTTTCGAGTCCGGTACCCTCTGTATGCCACAGATAGTCCGGA
TCCCACCGAATAACTGAAC
(SEQ ID NO: 1279)

Exon: 1204..1001
Start ATG: 1204 (Reverse strand: CAT)

Transcript No. : CT32502
ATGGATTACGAGATGCAGGCCACCGGCGGCATGATGATGATGGAATCGGAGACGAGTTTTCCAGCGCAGCAGCAGCAACATCAAGAGCAACAGCA
ACATCCACAGCAGCCACATCAATATCAGCGCATTCATCAGCATTATCAAGGTCATTTGCATCGCGCCAACCGTGATGTGAGTCGTTGCATGATGT
CGCACATGATTTAG
(SEQ ID NO: 1280)

Start ATG: 1 (Reverse strand: CAT)

MDYEMQATGGMMMMESETSFPAQQQQHQEQQQHPQQPHQYQRIHQHYQGHLHRANRDVSRCMMSHMI*
(SEQ ID NO: 1281)

Celera Sequence No. : 142000013384334
AAGTAAAGCCATCTACTTTTAGAACTTTTTAAAGGTAAGCCATTAAAAATTATTTAACATATTTTCGTGTCTTAAAATATGGGTTGAGTATGCAT
GCCTAAACTTTCTATATGACTGTGAATAAATAGTGACATTTTTGCAAATCACAATCACAACTTAGAAGTGCGGATATGAGAATATTGTAAGTATA
CATATGTATACCAAACCGAAAAAGCACGCTTTAGTCGAGTTCTTCGACTATCACATACCCATTACATGGCTAGCAATGGAAAAACAAAAACAAAT
TTGTGAAGAAATTAATTCAAAATTGTGGACATGAAAGCTTTTTGCAGTTTGTTGCCGATACCAGTGGACGTGACCAAAATGTTCTCGTTTTGAGA
AGTTCGATTTTAAAATCTAGCCAAGATCTAATCATTCTCAGCATACTCAAATCGAGATCAAACCATTCTCAGATTGCAAATGATTTTGCTTTCAT
TTGTCTTCCTCTCTTTTTCAGACTCTTCGACAATCTTACACCCAATACTTCTTCCGAAAAATAAAAAATATAAACGTTGAGATCATTTTCGTCT
CGAAACCAAGAAGGTTTATTTATTCACTGAGTACGCTGAGCGCAACCGACCTCTATTTTTTTGTTCTCAATTTTTCCGAGTGCAGGAAATGCTTA
CCTCCCCGCCCGTTTCGTACTTTTATCTAGCCGATAATACTCTTTAGTCTACAAGAAAAGGGTATAAATATATAAATACAAATCTCGCACTAT
TTGTCTGTATTAAATTATAAATTATAAAAATGTTTGGATATATTTCATACATATCGTTCGAGGGATAGCTTTTTATTATTGACTCATTTTATCTA
ATGAGTCATATCCCTTTAGGTTTGCAATATATTTTTTTTAGCATGCATAGTGATAGGCTTTTAAAACTTTGTTGCTTAAATTGCGTTATTTATTA
AAGTAATAATTTGTAAATTATTGTGGAAATAAAGCCCGCTTGTTGTTTTTTTAACTTAATATCTTTAGATTAGACTCACCGGCCATAAGTTCGCT
GTTTTGCTGATCCTGCAGCATTGGGATCACCGGCTCGCCGCCAGGTGGCGCATCTGGCATATCATCGGCCGTATGATCGTGACCGTGGGCGGTGG
GGGCGTGGCCCTGGGTGGGCGGTGGCTCGGCAAAGAGCATCTCGAAGCGCAGCCGGGTCTTGATTGGACAGACCCTCAGCTGCTGTTGCTGTTGC
ACTTGTTCGAGCGGGCCACCGATCTCCAGGTGACGATATAGAGCATAAATTTCGGTTTTATGCTCGAAATGGCTCCAAGTGCCGTTATGGGCGGC
GTATTTACCGTTGGCGTGATGGCAGCCTGCTTCTCTGACGTCACAGCAGCCGGCTGATTCAACAGCGACAATTTCGCTTTCGACGGCACCAAACT
GGCGTAAATAATCTAAAAATAAGACGAGGTTTTTTTTCCTCTGTACACGGGGAGGCTGATGCCGCTTCTTCTTCTTGTTATTTGCCCTTTGCTTC
TGCTGAAGCTGCTGCTTCTTCTTGCTATGTTCCCTTTCCTCTTGCTTTTTCTTCTTATCCTCCTCGCCTGCTAGATTCTCCTTCTTCTTACTACT
CTTATCCTTTACCCCTTGCTTGTGACAGAGCTCCTCCTCTTTCCGTTCCGCGTGCAGTTGTTGTTGTTGTTGCTGCTGCTGCTTGTTTGACCTTT
TCTTTTGGCCAAACTTTCTGCCCCCGTCGACGTCACAGCTGATCGATTTGCTGCACTCGCTCGGCGATTTATCCGCCTCCTGGCTTTGCCTGCTT
TTTCGATTTTCCCAATTCACATTCGTCGTCGGCCGTGGGAATTCTGCTATCATAATTTGTATGCCACTTATGCCATAATTATCACACTCACTCTC
ACTCACACGCACAAAAACGCGAAAAGAGAGGCGGGCGCGCGCTTGTGTTGTTGTTGATATATTCTTTTTCACCGCTTAACCAAGCTGAAAAGTT
GAAAATCTTTACACACACCAAAAACACACACACACACAGACTCAGAAAACTTGGGAAATCGAATTTTCCGTACTATGATTTTCCGGCCATAAATC
TGCACGGGCGTAAGTTTCGGAGGAAACTGCTGCAGAAAAGCTCCTGGTCGCAAAGGAAGAAAAATCGGACGGGCGAAGCGTTGCCAGACGATGAC
AGCGATTTCATTTGTTTTGATTTAGTTGCCGGAGCGATGTCACCTCAATAAGATACCGAAAAATACCAAAGGTATTTCGAGCTGCCAATCTTTTT
TCCGACATCAAACTTTTCTAGCCATTTGACTTTTTTTTCAAAAGTATTTATAAATTTTTTTATATTTAAATGCACGAAATAAATACATATATCAA
TGTCTATATAATATTTGGAAATATAAGTTTCCTTCGTTGTCATTGGGTCTTTCGACTTCTCTTTATTGACGCATCGCCTTAAACAATTCCAACTA
AAAATTTCCAATCAACACAGACAGCTACTTCGCTCCGCTTAGGCAAACAGACGCAGTTCATCGCGCGCCTCGATGCACTTGGGCGGCGAGGGAGT
CTCGAACTCGCCCAGCTCGGCGTCGTAGTAGAGGGCGGCGCGGTAGGGACGCAGCTCCCATGGCACCTGCTGCTCCATTGTGGTCAGCGTGACGC
CCAAATCCTCAAGCGTGGGGACACCAGTCAGAACCTTGTCGGTGACAGCCTCGCGTTCGATGCGAGCGGGATGCAGACCGCCAATCGGGGTGCCG
GGGCAGATGAAGCTGTTCAGCTTGGCTTTCAGCAGGAAGGTGGGGTCCCAGCGCATGTCGTAGCGCATGTAGCCCCAGCGCTTCTGGTCCTTGCG
CATCAGGCGGTGGAACCAGTCGACCAGCTCGCTCAACTGATAGCGTTTAGGTCTGCAGAGAATAAAGGAAATTAAGAAAATGTACATGGTACAAA
TACTTGGACTCGGAGATTGACTTACCCCACAGCCTGGTAGATGCGGCCAGCGCTGTCCGGATCCTTGGCGGCGTTGATGATGGCCTGGGCCACGT
CCGAAACGTAGACGGGCTGCTTGACGGTCTTCTCTCCCTTGTGCCACAGCGGCATCGAGCGGAACTGACGGCGCCAGATGTGGGCGTAGTAGCGC
AAGAAGCGATCCTCGGATCCGTAG
(SEQ ID NO: 1282)

Exon: 2159..1001
Start ATG: 1858 (Reverse strand: CAT)

Transcript No. : CT32503
TCCGATTTTTCTTCCTTTGCGACCAGGAGCTTTTCTGCAGCAGTTTCCTCCGAAACTTACGCCCGTGCAGATTTATGGCCGGAAAATCATAGTAC
GGAAAATTCGATTTCCCAAGTTTTCTGAGTCTGTGTGTGTGTGTGTTTTTGGTGTGTGTAAAGATTTTCAACTTTTCAGCTTGGTTAAGCGGTGA
AAAAAGAATATATCAACAACAACACAAGCGCGCGCCCGCCTCTCTTTTCGCGTTTTTGTGCGTGTGAGTGAGAGTGAGTGTGATAATTATGGCAT
AAGTGGCATACAAATTATGATAGCAGAATTCCCACGGCCGACGACGAATGTGAATTGGGAAAATCGAAAAAGCAGGCAAAGCCAGGAGGCGGATA
AATCGCCGAGCGAGTGCAGCAAATCGATCAGCTGTGACGTCGACGGGGGCAGAAAGTTTGGCCAAAAGAAAAGGTCAAACAAGCAGCAGCAGCAA
CAACAACAACAACTGCACGCGGAACGGAAAGAGGAGGAGCTCTGTCACAAGCAAGGGGTAAAGGATAAGAGTAGTAAGAAGAAGGAGAATCTAGC
AGGCGAGGAGGATAAGAAGAAAAAGCAAGAGGAAAGGGAACATAGCAAGAAGAAGCAGCAGCTTCAGCAGAAGCAAAGGGCAAATAACAAGAAGA AGAAGCGGCATCAGCCTCCCCGTGTACAGAGGAAAAAAAACCTCGTCTTATTTTTAGATTATTTACGCCAGTTTGGTGCCGTCGAAAGCGAAATT
GTCGCTGTTGAATCAGCCGGCTGCTGTGACGTCAGAGAAGCAGGCTGCCATCACGCCAACGGTAAATACGCCGCCCATAACGGCACTTGGAGCCA
TTTCGAGCATAAAACCGAAATTTATGCTCTATATCGTCACCTGGAGATCGGTGGCCCGCTCGAACAAGTGCAACAGCAACAGCAGCTGAGGGTCT
GTCCAATCAAGACCCGGCTGCGCTTCGAGATGCTCTTTGCCGAGCCACCGCCCACCCAGGGCCACGCCCCCACCGCCCACGGTCACGATCATACG
GCCGATGATATGCCAGATGCGCCACCTGGCGGCGAGCCGGTGATCCCAATGCTGCAGGATCAGCAAAACAGCGAACTTATGGCCGGTGAGTCTAA
TCTAAAGATATTAAGTTAA
(SEQ ID NO: 1283)

Start ATG: 302 (Reverse strand: CAT)

MIAEFPRPTTNVNWENRKSRQSQEADKSPSECSKSISCDVDGGRKFGQKKRSNKQQQQQQQLHAERKEEELCHKQGVKDKSSKKKENLAGEEDK
KKKQEEREHSKKKQQLQQKQRANNKKKKRHQPPRVQRKKNLVLFLDYLRQFGAVESEIVAVESAGCCDVREAGCHHANGKYAAHNGTWSHFEHKT
EIYALYRHLEIGGPLEQVQQQQQLRVCPIKTRLRFEMLFAEPPPTQGHAPTAHGHDHTADDMPDAPPGGEPVIPMLQDQQNSELMAGESNLKILS
*
(SEQ ID NO: 1284)

Celera Sequence No. : 142000013384885
GCACTTTACAAAACAACAACCAAGTTAACGTGATATTAAAGAAATCACTGGAGGGACCCCAGGACATCGAGTTGGAGTTAAGTATGACAGTGTAC
ACAAACGGAATGCCTCGTGGAAAAAGTGTAGCAAAATTATTTCTGTTTGTTTCTCAACATACATTTTAAAAATTATAATATTTCATTTGCTGCGA
ACATGTATACCTTTAGATTCCCTACAAACCTATACAGTAGACACAAATAAAAATTATGCAGAAAAAGTACACACATACCTGCTCTGCTGATAAAT
TTTACATTTTTAAATCATTTTAAATAAATAAAATCATCATAAATAATAGCTTATGTTCAAAGTTGTTGAATTGTTGAGTAACAAGTTTGTGATTA
ATTTATTTTTCAAGATACACTTAAGTAAAAGTATTTTAATGTCCAAAAAACTCACGGGATTTGTACTGCTTGTGAGGACTTGGCCGCAGAACACA
CTTCACCTCGTATATTCCATGTGCATGGATTATATAAATGCATGTGATATTCACACATTCATGCGGTTAAAAAAACTTACTCTGCCTCCTCACCG
ACACTATTGGTAATAAAAAATAACGTAAGTTATTTTAACATTTAATAAAGATTTTAACACTAAAAACAAGAGAGAATTCTTTTTTGCTAGTTCTT
CGGCTATATATACCCGATATTGAAGACTACTAAAGATTACAAGGCCAATTGAAAGTAGAACAAAAAATCTAAAAAAATTTTAAACATGTGGGCGT
TACAGCTTTTGGCGGATTGAGTTTGCGTGGTAACGTGTCGAGCATTTTTATACCCGTTAAAGGGTATACTAGATTTGTTGAAAAGTATGTAACAG
GCAAAAACGCTTCCGACCTCAAAAAGTATATATATTCTTGATCAGGATCAATAGCCGAGTCGATCTGACTATGTCTGTCTGTCCGTATGAACACC
TCGAATTCTGGACTATTAAAGCTAAAATGTTGAGATGAAGCATACAGATTCTAGGAACATAGACAGCACAAGTTTGTTGACCCATGTTGCCATTC
CTGATCAGGATCAATAGCCGAGACGATCTGGTCATGTCCGTCTGTCCGTATGAACGTCACGATTACAGGAACTATAAAAGCTAGAAGGATGAGAT
TCAGCATACAGAATCTAGAAAAGACGCAGCGCAGCGTTGACCCATGTTGCCACGCCCACTCTAACGCCTACAAACCGCGCAAAACTGCCACGCCC
GCACTTTTGAAAAAGTGTGTTGATATTCTTTAAATATTTTGATTAGTCTTGTAATTTTCTATCGATTTCCCAAAAAACTTTTTGCCACGGCCACT
CTAACGCCCTTCAGCCGCCCAAAAATGCTTTGTCGCCCGTTATCAACGTGGTAGCTAGTGGTTTGCTTAGGACCTCTCGTGTTTAGAAGCATTCT
CGGCAGAGAACCAGTAGTAGCGCTGGCCTTTTTGTGGGCGTACTCTAGGTGCTCTCGGAACGTGGTATCAGGAGAAGCACTAACTAACTATTGAT
CTAAAGATACACATTATTTTAACGTTCCAGGAAGATAGGTCTTGCGTGATAATCCACACGAACGACATGAATGAAATCATATGATGCTGCAAAGT
ATATGTCATAGTTTTAATACTGCGTTGGTGATGCGTCGGTGATTAAGGATTCGACGTCAAATTAGTTTGGGCAGCTTGTAGAGTTGGTGCCTTAG
AGGTAGGTTCTGTTAGCCTCGAATTATGGACGTTTGGAAATATCAAATTTTGGAAGGTGGTCGAAGGGCCAAATAAGGACCTCTTTGCGGGTGAT
AAAAAAACTTCTGGCGTTCTGGCGTTACTCGGAGATGTATCCGGCTTTTGGGGTCTTTGTATATTGAACAGCCTTTATATGGTCAGAAGCGCTTT
CTTCCACCTGTTACATACTTTTCAACGAACCTATTGTAGTATTCCCTTTTACTCTACGAGTAACGGGTATAAAAAATATAAGGCCCAAAGGGTTT
TCTGTAGCACCTACCGTTTAGTTACACAATTCATAAAAAAAACCAAATCGATTTTCAAATTCATAATTTTTTTGTATAAGAATCATACGAAAAAA
CGGTAAAAATTTATTATGTCCTTCGTACCCGTTTATTTTTATTTTACTTAATAAGA
(SEQ ID NO: 1285)

Exon: 1147..1001
Start ATG: 1147 (Reverse strand: CAT)

Transcript No. : CT32593
ATGCTGAATCTCATCCTTCTAGCTTTTATAGTTCCTGTAATCGTGACGTTCATACGGACAGACGGACATGACCAGATCGTCTCGGCTATTGATCC
TGATCAGGAATGGCAACATGGGTCAACAAACTTGTGCTGTCTATGTTCCTAG
(SEQ ID NO: 1286)

Start ATG: 1 (Reverse strand: CAT)

MLNLILLAFIVPVIVTFIRTDGHDQIVSAIDPDQEWQHGSTNLCCLCS*
(SEQ ID NO: 1287)

Celera Sequence No. : 142000013384703
CGGGTGTTTACAATAAATTTCGCTGGGTGGATGTAGCTTTGTAATTTGAGTTCGCCAATTTTTTTTGTTGTTAACAGCATTTCGAAGCGGTTGCC
AACCCTAGACGCTGGCTGGTTGCATGGTAACGAAAAATGGCGGCGCCTGTTACACACACTCACACACACATGCACGCACAGTCTGCTGTGTTTAT
GCACTTCATGCTGTTCCGATTTTTTTTTTGCACTTTTTCGATTTGTTGTCTGCATTTACCTTAAATGAATTTATTAACTAAGGCGATATTGTGCC
TCTCGCTCAATCTCGCAAAACGATGCTTTGTCTGCTGCTTCTCTGTGCGTGTGTCCGTCTCTTTCCACGGCTTTTCGTCGAGACTCACATATACA
AACGGCGACACACTGGATTGGAGCTGGACTCCGTTTTGGATGGCTTGGCTTTGGCTGCGTACCCAAAATAAATCGCGCTTGCAGTCCCAAATCAT
TTTAGTTCTTGACGCCTTTGTTCCACAAAAACTTCCAACCGCCGTCCATGGCTCGTGCTTTCTCTTTCGCTCGCGAGACGCTCCAAAAGTCGCGA
GTATGGGAAGAGAATGTATCCCTCGCTCTTTCACGCCTAGAAGCGGCTGTAGCACACACAAGCACACGTAAACCCAGCCGTATGCATATACATAT
ATTCCCTCTACTAGCGAGACGTGTGTACGTGCGTATGTATGTATGCTTTTTTCACTTCTTTCTCCTCTGCGTTCTTTGCACCAAGTGTCGCTGTT
GCTATTTGCTACCGCCGCTCCTCTTGACGAATAAGTCGGGACTTGTATCAGCTCTAATTCGGACTTAGTTTACAAAATGCGGCTGCTTTTTTTCC
GCGATACTCGGATTAGTGATGTAAAAAGACGTTGATGCTTCGACCACTGAAGTCAGTGCGATATGTATCGATAATTGAATGCCATCGATTGCTAC
GATTAAAACTGCCACCGCAGTTAGCGGAGACGCTCACCATTCTCTATTCGCCATTTGAAAGTATCGGTGTAATTTGTTTTCAGAGAAATTAATTT CCGTTTACTGTGCAATTCGGTGTGAAAGTGTTCAGATTTATCAATGCGTATTCTGCTTTCGACTTCGCCACCAATCTGTGCTGCAAGTTACCATT
ACCAGGTCCACCTGGTTCCCGCCAGTTTTCTTTCATTGTGGCTAGTTGTTGTTCGTGCCTTCGATAAAGACGTTTAGAGGTGTTTTTAGAGTTTC
GCCATCTGGTCACTATAGCCGTTTCGTTTTTACGTGAGTATTGTGAATTTGGTGTGTTGATTTATATCTCAGTTGGAGCCTGCGTGGAAATAGT
GTCAGTACGTTTAAAGGCATCATCGTAAGGTTAGTCGGAAAACAAATAAAAAGCCTACAAATAGCAAGCAAGAACGCTTTCGCAACCACAAGAAA
AACGAACATACGCACGCATCCATCTGTGGTAGAGTCGGCTTGTGTGGGGGTGAGTGGATGTGTGGGTGAGCATTTCTGGAAAGTGCCGTTCTCTA
TGTTTCGATTCTACTTATCCCTTCATCACCATTTCATCGTTGAATCATCACGAAAGAAACATCGAAAGTGCACAATCGTTTGTTATCTTTGTACG
AAAACAACGGTGATTTCCACACAGGCATAACCTGCAAGAGTAATACGATACAAATTTTGATCTGATATGACCTCATTTTAGTCGGTTTGAATTTT
AAAGAGAGCGACTCTGCAAACTGCAGGGATATGAACATACAAAATTCACAAATGATTGTTTGCATCCTAGTTGCTTATATTCATTTACACGCATG
CTTATATGCTTACATCTGTTATCAATAATTGACGACTTGGTGCATGCGAAGCAAACGCATTGAAATGACTATTGGGATCCACACACTGTTAAAAA
ACACACTGATTGCACTGCCACACATTTCTCAACTAGAACCTAATGTTTTATACTGAACTTAACTGCAGGAAAGCCCAAAATGCCCAGCATCAAGT
TGCAATCTTCGGATGAGGAGATCTTTGACACGGATATCCAGATCGCCAAGTGCTCCGGCACTATCAAGACCATGCTGGAGGACTGCGGCATGGAG
GACGATGAGAATGCCATTGTGCCGTTGCCCAATGTGAATTCGACGATTCTTCGCAAGGTGCTTACCTGGGCTCACTACCACAAGGACGACCCCCA
GCCAACGGAGGATGATGAGAGCAAGGAGAAGCGCACAGACGACATTATCTCATGGGATGCAGATTTCCTAAAAGTCGACCAGGGCACACTGTTTG
AGCTGATATTGGCAGCGAACTATCTGGACATTAAGGGCCTTCTGGAGCTCACCTGCAAGACTGTTGCAAACATGATTAAGGGAAAGACTCCCGAG
GAAATACGCAAGACCTTCAACATTAAGAAGGACTTTTCGCCCGCCGAGGAGGAGCAGGTGCGCAAGGAGAACGAGTGGTGCGAGGAGAAGTAAAG
CGCGGCATTTCGCGGACCAACATTAAGTTGAAACAGCTAGGGGATTCGGGAACGAATTGGATTTGCAGCATTGCAACTTTACTTAGTTGCTACT
TTCATTTACATTTTTTTTTATTTTTAACCCCAGCAGAGACTCGATTTAAATTGTGTATAAATGATCTGTTGCTGATTTGATTCGCGGGGTTCATT
TTTTGTCGTAAATATATCTCATATACATACATATGCGAGATTGTAACACTCTCTTTAACCTATTGGAGTAACACTTGATTTCACTTTAATAAATA
TAACTACCCAACACAAAGACACAGCCTATTTTGTGGGCTTCCCGGAGGGGTTAGGGTCCAAGGACTTCTCAAATTAAGAAGTGCTCTTTATTCGT
TATCTTGTGTTTAGAAACGTTTGCAAGCGTTTGAAATGGATACGCATGCCATTTATGGTCCAGTCGGTAAAATTTTACGTGTTCCCAAGAAGGTA
CATATATATCTTAGATTATCTTATCTATAGAAACTACATTCATAAGATCACGCTTTCGGCGAATAGCGAGTAATACTGTAGCTGCCACTTTGCCA
CTTAGTGTGCAATTGAAATGCGCGCCAACGCATGTTCTCATATGCGGAGCGTTTAGCAGCCCTTAAAAAGCTTTTCATGTTGCTTTTAAAAAGCT
ACGACGGGTGTGGAAATTAGATTTGTGACGCTTTATATATCTTTTTTTTATATCGTCTGGGGTACAGCATGGTTTTAGGATTTTAGAAGAAAGCA
GTAATTTTGTAAGAATCGAAGAACGGGGGGATATTTATAATTTCATATTAACCTTGTCTTTGTTTGCTTTTGAAATTATGAATACTTCGAAAGA
TAATTATCTTGTGCGCATTCCATTCTGGCTTAGACTGGGTTGAGCTAAAAATGATTTGAAATACAAATTTTTAGGTGTCCGCTGATATATAAACA
GTATGATGTTTTTGCACTTTTTTCCCTGAAGTTTTCCTTGTTGTCTCGCTTGCCAATGCTGAACAAAGTAGCCAAAGGACCTTTACTTGAAGCTT
TGAGAGCGGAAAATATATTCGGGGACAATTGCTTTAAGTGTGCACTAGGCTTGGCTAGATGCCCGTGCCAAACTTTCTTTGGAATTGATCGCTGG
CCTTAGCCAAAAGTGGAAAAAAGAAAGGATAGGATAGTGCCGCACGTATTAAGGGTCTTCTTACAAAAGGTAACTGATATTAATTCATTTGCATA
CTAAGCAAGCTAACTCATCTGTTTATTGCAAACAAGCGCCAATTGAAGTTTTATCGAAGCTCAG
(SEQ ID NO: 1288)

Exon: 1001..1269
Exon: 1980..2769
Start ATG: 1980

Transcript No. : CT32694
CCATTTGAAAGTATCGGTGTAATTTGTTTTCAGAGAAATTAATTTCCGTTTACTGTGCAATTCGGTGTGAAAGTGTTCAGATTTATCAATGCGTA
TTCTGCTTTCGACTTCGCCACCAATCTGTGCTGCAAGTTACCATTACCAGGTCCACCTGGTTCCCGCCAGTTTTCTTTCATTGTGGCTAGTTGTT
GTTCGTGCCTTCGATAAAGACGTTTAGAGGTGTTTTTAGAGTTTCGCCATCTGGTCACTATAGCCGTTTCGTTTTTACATGCCCAGCATCAAGT
TGCAATCTTCGGATGAGGAGATCTTTGACACGGATATCCAGATCGCCAAGTGCTCCGGCACTATCAAGACCATGCTGGAGGACTGCGGCATGGAG
GACGATGAGAATGCCATTGTGCCGTTGCCCAATGTGAATTCGACGATTCTTCGCAAGGTGCTTACCTGGGCTCACTACCACAAGGACGACCCCCA
GCCAACGGAGGATGATGAGAGCAAGGAGAAGCGCACAGACGACATTATCTCATGGGATGCAGATTTCCTAAAAGTCGACCAGGGCACACTGTTTG
AGCTGATATTGGCAGCGAACTATCTGGACATTAAGGGCCTTCTGGAGCTCACCTGCAAGACTGTTGCAAACATGATTAAGGGAAAGACTCCCGAG
GAAATACGCAAGACCTTCAACATTAAGAAGGACTTTTCGCCCGCCGAGGAGGAGCAGGTGCGCAAGGAGAACGAGTGGTGCGAGGAGAAGTAAAG
CGCGGCATTTCGCGGACCAACATTAAGTTGAAACAGCTAGGGGATTCGGGAACGAATTGGATTTGCAGCATTGCAACTTTACTTAGTTGCTACT
TTCATTTACATTTTTTTTTATTTTTAACCCCAGCAGAGACTCGATTTAAATTGTGTATAAATGATCTGTTGCTGATTTGATTCGCGGGGTTCATT
TTTTGTCGTAAATATATCTCATATACATACATATGCGAGATTGTAACACTCTCTTTAACCTATTGGAGTAACACTTGATTTCACTTTAATAAATA
TAACTACCCAACAC
(SEQ ID NO: 1289)

Start ATG: 270

MPSIKLQSSDEEIFDTDIQIAKCSGTIKTMLEDCGMEDDENAIVPLPNVNSTILRKVLTWAHYHKDDPQPTEDDESKEKRTDDIISWDADFLKVD
QGTLFELILAANYLDIKGLLELTCKTVANMIKGKTPEEIRKTFNIKKDFSPAEEEQVRKENEWCEEK*
(SEQ ID NO: 1290)

Classification: cell_cycle_regulator
Gene Symbol: skpA
FlyBase ID: FBgn0025637

Celera Sequence No. : 142000013384583
CTTTTACAGCAAGTCGAACTGGGAGCTGAAGTCTACCAGCAATTACTTGCTATTTACCTCTATCAAAACAAACTGTAAGTGATTGATATAAAAGA
AATACATATTTTAATCTTGTGCTACAGGGCTGATGCCAAGTTGTTGTGGATGAGAGTTCCAGCTAACCTAAGGGATGACAAGGAACTGATCCAGC
TGAACCTGCTCAATATTGCCCTGCAGAACAATAACTATGCCGATTTCTTCAAACACATCAAGTATGAGTGGTCGGAAAGAGTAAAGTCACCTGTG
GAGGATCTTCTAAGTATGGCTATGCCTAAAAGCTTACTAATTGGATATAAAAACTTATAATGTATCTACTTAGATAAGCAACGCGAAGAGCTGTT
CAAACTAATGGGCAGCGCATATATGTCCATTTACCAGCACAATCTACTGGAATTGTCACTAATGTCGGAGGACGAACTGAAACACGCCTGTGCGG
CCTTAAATTGGACTGAGGAACTGGACGGTGACCGGGTAATCCTGAAGCCCAAGGTTCAGGAAGCACCGCCAGCTCGTGGAAACGATGACCAGTTG
CTTAAGTTGACCGAGTTTGTAACCTTCCTAGAGAATTAAGCCTCAATAAATTTCAATACATTTAATTGGATTTTTGTATACATTTGAAGAAAAGT
TATGGTCACACAGCCTGTGTCAATCTAAAAAACACTCGATTAATATCGTTATTAGACATATTTATAAATATTAGCTAAATCACCGAATTGGCGCC
ATTGGGTTTTGTACGAATTAGCTTTTGGAAGTATACCTAAAAATTAGGAACTAGAAACTAAGGCTACAGAATTATAATTTTCCATGTAATCTATG TAGATATATAATCATATTCTTGGCCTAATTTAATAAGTGTGATTTTAATATTCTTCAGAATTCAGTTAAATAAAATATATTTCAGAAAATCTATC
GACGCGCGGAAACGCCGATAGTATCGAATGATAACCGATATGCGTTCCACCTCTACCGTTGTGTCACTTGAAGAAAAAAAATATTAATTTGCACC
AACGACGTACGTTTTTCGTTCGAAAAGAACAGCAATCAGCGGATAATTGTATGGATTCTTAGAAAATTTGCAGCGACGAAATATAGTACCTTGCG
AAATTATTTTGTAACCTTGAAGAAGTAAACTGCGAATCGCCAGAGGGCCAAATAGAAATCTCGTCGTTTGCCTGCAGAATAGAAGACCCGATTTT
CAGTGCGCTTGTGTTTGTGTGTGAGCAGCAGAAACAGCAGAAAAAATGGCAGCAAGCGACAAATCGGTCGACGATTCACTATATCCCATTGCGGT
TCTAATCGATGAACTGAAAAACGAGGACGTTCAGGTTTGTCATGTCCTAAAACCTGAAATCCAATTGTATCTCGCGAAGAATGTGCAGAAATATT
CTAGTGATTAAATTTTGGGGTAGCGTGCCCACACTCCCTGCTTTATCTGCGATTGTATTTGTGCAAAAATGCGTCACGGTGTGTGTGTGCGTGTG
TGCATGGGCATTTGTGTTGGTGCGAGTGTGTGCATCGAAATTATACCGAATTTCGATATACACAAGATTAGCGTTTTGCGAAAAAAATTACTATT
ATCAATTAATTGCAATTATGGGTATACGTCTTTATCCGCTTTTTATTTGTAGATTTTGTTATCCTTCATTTATGTATGTATAAGTATAAGTTTTT
ACGCATTTGCTATTTGCAAAAACAATTTACAACTGCGCGTGTTAAAAATAGATCAACTTCAATCAATAGTAATACCATAACTGATTTTAAAATGA
GATAGTAAGATGAAATATTTCGTTACATCGAATAATCTAATCACTTATCTTATCTAAAAAAGATATCTTAAGTAAATATATATGCTACGTTTTT
TTTTGAAAATAAAATGTAGGGTACAGGTTGACCACCGCTTTTGTAAAAAAAAACCAATAGCCCTATCAATAATAACCTCAAAATCGTAGAATTAG
TTACCACTTATCCTAAATTTGAATACCCTATTAAAATAATCATCTTTAATATTTTCCCTTACCAAAACAGCTTCGGTTGAACTCCATCAAGAAAC
TGTCCACCATTGCACTCGCTTTGGGCGAGGAGCGCACACGGTCCGAGTTGATTCCCTTCCTCACCGAGACCATATACGATGAGGACGAGGTACTG
CTGGCCCTGGCCGACCAACTGGGCAACTTTACTAGTGAGCAAAGATATAATTTCTAATGAAAACATTTCCAACCATGTTCCGCCGTTACTTTCCA
GGTCTCGTTGGTGGGCCAGAGTTTGCCATGTACTTGATTCCGCCCCTCGAGAGTTTGGCCACCGTAGAGGAAACCGTGGTGCGAGACAAGGCTGT
GGAATCTCTACGCACCGTGGCCGCTGAGCACAGCGCCCAGGATTTGGAGATCCATGTGGTGCCGACACTGCAGCGATTGGTTTCCGGTGACTGGT
TCACCTCACGCACCTCTGCCTGCGGCCTCTTCTCGGTCTGCTATCCACGCGTCACACAGCCAGTGAAGGCCGAGCTGCGCGCCAACTTCCGAAAG
CTCTGCCAGGATGAGACACCCATGGTGCGCCGTGCAGCGGCCAACAAGCTGGGCGAGTTTGCCAAGGTCGTTGAGACGGAGTATCTGAAGTCCGA
TTTGATTCCCAACTTTGTCCAGCTGGCACAGGATGATCAGGTAAGCACCTGATTAAGACCAATTTAACAACACTCCAAAATATCAATCCTTATCC
TTAATTTCCAGGACTCTGTCCGTCTGCTGGCTGTAGAGGCATGCGTAAGCATTGCCCAGCTGCTGCCTCAGGATGATGTAGAGCACGTAAGTTGA
TCAGCGCTGAAATTGTTAATACCTGTTGGCTTACAAAAAATATTCCATAGCTGGTTCTGCCCACGCTGCGCCAGTGCGCCAGCGACTCTTCCTGG
AGGGTGCGTTACATGGTGGCCGAGAAGTTTGTTGATCTGCAAAAGGCTGTGGGCCCAGAGATTACTAGGGTGGACTTGGTGCCTGCCTTCCAGTA
CTTGCTCAAGGATGCCGAGGCCGAGGTTCGCGCTGCAGTGGCCACCAAGGTGAAGGACTTCTGCGCCAATCTGGACAAGGTCAACCAGGTGCAAA
TCATCCTTAGTTCCATTTTGCCCTATGTCCGCGATCTTGTCTCGGACCCCAATCCTCATGTGAAGTCAGCTCTGGCCTCAGTGATCATGGGCTTG
AGTCCCATGCTGGGCGCCTATCAGACTGTGGAGCAATTGCTCCCCCTGTTCCTTATTCAACTCAAGGATGAGTGCCCAGAAGTGCGCCTAAACAT
CATCTCAAACCTGGATTGCGTTAACGACGTCATCGGTATCCAGCAACTGTCACAGTCGCTTCTGCCCGCCATCGTCGAGCTGGCCGAGGACTCCA
AGTGGCGTGTGCGTCTAGCCATCATCGAGTACATGCCTGCTCTGGCCGGTCAGTTGGGTCAGGAATTCTTTGACCAAAAACTGCGCGGTCTCTGC
ATGGGATGGCTCAACGATCACGTGTACGCCATTCGTGAGGCAGCCACCCTCAACATGAAGAAGCTCGTCGAGCAGTTCGGAGCTCCCTGGGCCGA
ACAGGCCATAATTCCAATGATTCTGGTTATGTCGCGCAACAAGAACTATTTGCACAGTAAGTTATCGAATTGAAATTGTAATGATCAATATATGC
TTATGGTTCTTATGATTTTTAGGAATGACTTGCTTGTTCTGCCTGAATGTTTTGGCAGAGGTCTGCGGCACAGATATCACCACCAAGTTGCTGCT
GCCCACAGTTCTCCTGCTTGCCGCTGATCCCGTTGCCAATGTTCGTTTCAACGTGGCAAAGACCCTGCAGAAGATCTCGCCCTTCCTGGAGGCCA
GCGTCATTGATGCCCAAGTAAAGCCCACACTCGACAAACTGAACACAGACACAGATGTGGATGTCAAGCATTTTGCTGCACAGGCCATTGCCGGC
ATAGCTGCAGGTAAGCAATAAACAGTCTAATATAAACAAGGTTAGCGTTTGACAGGGATAGAAAGGGTCTAACTTATAGAACAATATATAACATT
ATTCATTATCACAAGTTTTAAGGCATGCAGGGAATCTGAGAGTTACACAAATCATAAATGTCAGTTAGTAGTAAGACTTTAATTTTAATTAAA
ATCCTGCCATAGAAATGGAACTGAATGTGTTTAGAACGGCAATACCGCCGTGCATGGGCGCCAAAATTGAGGCGGCAATGGACTCAAAGCTGATA
GTGGAACCGCCCCGACAGCCGGAGGCAGCTGACAATGACATTTTGCAGGAGATGAATGGCAAGGCAGCGGAGCCGCCCACGCTTGACTCGGAATG
TTAGAGGATGAGTAGCCAACCACATGACGTGTGATGTGCCTCCCGCTGTCTCCAGCCAGTTCCACAAGCCAATGTGTTTAATCCTCCCCGTCATA
ATCGTATTCACATTTGATTGTTTGTTTGTTCAAGATAACCAGGCTAGATGTCCGATCTGATTAAAGTGCGAGTGCAGTGGATCAAATATTTAACC
GATACTAATGTTGTGCCATATTTTTTTGTCTCTTTCCCGGTATCATCGCCATCACCACGTGGTTATCTCACCATTCCCCACTCTGTGTTCGTCTG
CAATAATGTGTTTTGTATATTTGTTTATAGCGTAATCAACCTTCTTGCATCTTTTTTTATTCTATTTTTAAAACTGTATGTATTTAACGCCGGCA
ACAAAACATATTATGTAGCAACAACACTTAAGAACGGAAAATTGTAGTGGATCCCGGAAGGTGTTAAACGCTGCAGCCGATGCTGGATGAGGGAT
GAATGGAGCCAGGAGTCAGAGGAAGGAGAGAATCGGAGAATCAGCATGGGAGGAGACCCACTAAACGCGACACACAACTAAACATTACTACTTAC
ATACTTATATTATATATAAATTACCATAGGCATAACGATCATTATTAAAAACATTTGTAGAGTTTGGAACATTTGATCGCATCTGAATGCAAAAA
TAAAATTGTAGTGAAACAATATCACACGATCTATTGAAAAGTTTAATGTGGAGCAAAATTGAATATTTAACTCCCAAAATTGTATACCAATTTCT
AGGTTTCAGTTGTCAGTTCAAAGTTTGGAAATGTAATATTTTCCTTTTTATAGTTTCGTTCAAATTAAGCTTTATATACATTCTGATTATTTGGC
AGGTGCATTGATTATTTATAATTTGTGAGAGGTATGGCTATGAAAAGCATAGATTATACAAACAAAATACTTGTATTTTTACATTTTAAAAATAC
TGTTAATTTATTTTGAAATCCTAAAATCATTCCAGCAGTAAACGATTTTGATAGCAAGCTAGACTGATATCGATAGGCGCCAAACAGACACCTGG
CGATAGTTGGGGCTTCTTTTTGGTTTTTAATTGGATGATGGTGGTGGTGGTGGTGGTGGTGGCGAGCAGTTTCTAGCGAGAGATCAGTTGGACT
TTTGCGACGAAGCGATACGCTTGTTTGTTTTGCCGTTCCGCTGCGCGTTGGCCAATGTTTGCCTAACTCTCGAATCGAATTCCGAAACCGAGTGT
GGACGCGTAAGTGCCATTGAATTATTCCGTCTGACGCTCGAGCGCCATCGAATCGGATGCGGCGTGGAATGTGGTGGAGTCAATGGGGGGATCAG
ATGCAAATTTGATTGGGCAAATGGGTGGAACCAATCAATTGTGTGTATACAATAAAACGAGGTGTTTGTGTGTGCCCAACCAAACACAGCCAAAT
GCGGAACATTATCAGTTTACCCACGGCTGTCGCAATCTCCGCGTCCGTTTACCGTCCACTGACCTACGATCCACCTGCCCCCGTGGACGCAACAA
GTGTCCGAATATTTATAGTCTATGGGCTCTATGCATTAATTACTCGCATATGTCAAAAACGCTGAGCTGTTATTACAATTAGTGCTTCATTATTT
AGCCCGATTTCCCCAAGTGGCGCGTTTCGCTAAGCGTTATTATTTTTACCTTCCGCTAAACACTTGGCGC
(SEQ ID NO: 1291)

Exon: 1001..1364
Exon: 2066..2219
Exon: 2282..2700
Exon: 2767..2841
Exon: 2901..3666
Exon: 3728..4000
Exon: 4686..5055
Start ATG: 1281

Transcript No. : CT32725
CTCTACCGTTGTGTCACTTGAAGAAAAAAAATATTAATTTGCACCAACGACGTACGTTTTTCGTTCGAAAAGAACAGCAATCAGCGGATAATTGT
ATGGATTCTTAGAAAATTTGCAGCGACGAAATATAGTACCTTGCGAAATTATTTTGTAACCTTGAAGAAGTAAACTGCGAATCGCCAGAGGGCCA
AATAGAAATCTCGTCGTTTGCCTGCAGAATAGAAGACCCGATTTTCAGTGCGCTTGTGTTTGTGTGTGAGCAGCAGAAACAGCAGAAAAAATGGC
AGCAAGCGACAAATCGGTCGACGATTCACTATATCCCATTGCGGTTCTAATCGATGAACTGAAAAACGAGGACGTTCAGCTTCGGTTGAACTCCA TCAAGAAACTGTCCACCATTGCACTCGCTTTGGGCGAGGAGCGCACACGGTCCGAGTTGATTCCCTTCCTCACCGAGACCATATACGATGAGGAC
GAGGTACTGCTGGCCCTGGCCGACCAACTGGGCAACTTTACTAGTCTCGTTGGTGGGCCAGAGTTTGCCATGTACTTGATTCCGCCCCTCGAGAG
TTTGGCCACCGTAGAGGAAACCGTGGTGCGAGACAAGGCTGTGGAATCTCTACGCACCGTGGCCGCTGAGCACAGCGCCCAGGATTTGGAGATCC
ATGTGGTGCCGACACTGCAGCGATTGGTTTCCGGTGACTGGTTCACCTCACGCACCTCTGCCTGCGGCCTCTTCTCGGTCTGCTATCCACGCGTC
ACACAGCCAGTGAAGGCCGAGCTGCGCGCCAACTTCCGAAAGCTCTGCCAGGATGAGACACCCATGGTGCGCCGTGCAGCGGCCAACAAGCTGGG
CGAGTTTGCCAAGGTCGTTGAGACGGAGTATCTGAAGTCCGATTTGATTCCCAACTTTGTCCAGCTGGCACAGGATGATCAGGACTCTGTCCGTC
TGCTGGCTGTAGAGGCATGCGTAAGCATTGCCCAGCTGCTGCCTCAGGATGATGTAGAGCACCTGGTTCTGCCCACGCTGCGCCAGTGCGCCAGC
GACTCTTCCTGGAGGGTGCGTTACATGGTGGCCGAGAAGTTTGTTGATCTGCAAAAGGCTGTGGGCCCAGAGATTACTAGGGTGGACTTGGTGCC
TGCCTTCCAGTACTTGCTCAAGGATGCCGAGGCCGAGGTTCGCGCTGCAGTGGCCACCAAGGTGAAGGACTTCTGCGCCAATCTGGACAAGGTCA
ACCAGGTGCAAATCATCCTTAGTTCCATTTTGCCCTATGTCCGCGATCTTGTCTCGGACCCCAATCCTCATGTGAAGTCAGCTCTGGCCTCAGTG
ATCATGGGCTTGAGTCCCATGCTGGGCGCCTATCAGACTGTGGAGCAATTGCTCCCCCTGTTCCTTATTCAACTCAAGGATGAGTGCCCAGAAGT
GCGCCTAAACATCATCTCAAACCTGGATTGCGTTAACGACGTCATCGGTATCCAGCAACTGTCACAGTCGCTTCTGCCCGCCATCGTCGAGCTGG
CCGAGGACTCCAAGTGGCGTGTGCGTCTAGCCATCATCGAGTACATGCCTGCTCTGGCCGGTCAGTTGGGTCAGGAATTCTTTGACCAAAAACTG
CGCGGTCTCTGCATGGGATGGCTCAACGATCACGTGTACGCCATTCGTGAGGCAGCCACCCTCAACATGAAGAAGCTCGTCGAGCAGTTCGGAGC
TCCCTGGGCCGAACAGGCCATAATTCCAATGATTCTGGTTATGTCGCGCAACAAGAACTATTTGCACAGAATGACTTGCTTGTTCTGCCTGAATG
TTTTGGCAGAGGTCTGCGGCACAGATATCACCACCAAGTTGCTGCTGCCCACAGTTCTCCTGCTTGCCGCTGATCCCGTTGCCAATGTTCGTTTC
AACGTGGCAAAGACCCTGCAGAAGATCTCGCCCTTCCTGGAGGCCAGCGTCATTGATGCCCAAGTAAAGCCCACACTCGACAAACTGAACACAGA
CACAGATGTGGATGTCAAGCATTTTGCTGCACAGGCCATTGCCGGCATAGCTGCAGCGTAATCAACCTTCTTGCATCTTTTTTTATTCTATTTTT
AAAACTGTATGTATTTAACGCCGGCAACAAAACATATTATGTAGCAACAACACTTAAGAACGGAAAATTGTAGTGGATCCCGGAAGGTGTTAAAC
GCTGCAGCCGATGCTGGATGAGGGATGAATGGAGCCAGGAGTCAGAGGAAGGAGAGAATCGGAGAATCAGCATGGGAGGAGACCCACTAAACGCG
ACACACAACTAAACATTACTACTTACATACTTATATTATATATAAATTACCATAGGCATAACGATCATTATTAAAAACATTTGTAGAGTTTGGAA
CATTTGATCGCATCTGAATGCAAAAATAAAATTGTAGTGAAACAAT
(SEQ ID NO: 1292)

Start ATG: 281

MAASDKSVDDSLYPIAVLIDELKNEDVQLRLNSIKKLSTIALALGEERTRSELIPFLTETIYDEDEVLLALADQLGNFTSLVGGPEFAMYLIPPL
ESLATVEETVVRDKAVESLRTVAAEHSAQDLEIHVVPTLQRLVSGDWFTSRTSACGLFSVCYPRVTQPVKAELRANFRKLCQDETPMVRRAAANK
LGEFAKVVETEYLKSDLIPNFVQLAQDDQDSVRLLAVEACVSIAQLLPQDDVEHLVLPTLRQCASDSSWRVRYMVAEKFVDLQKAVGPEITRVDL
VPAFQYLLKDAEAEVRAAVATKVKDFCANLDKVNQVQIILSSILPYVRDLVSDPNPHVKSALASVIMGLSPMLGAYQTVEQLLPLFLIQLKDECP
EVRLNIISNLDCVNDVIGIQQLSQSLLPAIVELAEDSKWRVRLAIIEYMPALAGQLGQEFFDQKLRGLCMGWLNDHVYAIREAATLNMKKLVEQF
GAPWAEQAIIPMILVMSRNKNYLHRMTCLFCLNVLAEVCGTDITTKLLLPTVLLLAADPVANVRFNVAKTLQKISPFLEASVIDAQVKPTLDKLN
TDTDVDVKHFAAQAIAGIAAA*
(SEQ ID NO: 1293)

Name: Protein Phosphatase 2A
Classification: protein_phosphatase
FlyBase ID: FBgn0005776

Celera Sequence No. : 142000013384583
TTTTTTATATTTAAAATTAAGTCCACTTGCTTAATTTACATTAATTGCACTCTAGAACCCTCCAGATATATGTAAAAAATCACAAATTTTAAAAA
ATGCATTTAGAATAAGCTCTTAAATGCGCCTCTATTTGAGCTAGTTAACAATGTGTAACAATTAAAAGTCCATTCGCTGTGGCAAGTGTTCCTCC
TCCACCTGGTGCTCGATCTCCCTCATGCGTAACATAAGTTTAAAGTTCTGCTTGTCCTCCTGGCCAGTAAGGAACATGGTTAGCAGGGCCTGCAG
GCCGATTAAGGTTCCTAAGGCTGGGACAATGGGGCGTGTAAATTTCCGCCACAACAGAAACACTTCTCTGGGATTTTCCGTAATCGAGGGAATAC
GGTACGTGTAGCAGCGGGTTGCGAACAGAAATGCGGCGAATGGGGCCAGAATTGTGGGATATACGATGCCCAGACTTGTCTGAAAGGCAGCACTG
CGCATCTGGATGCACACCGGGCACTCGCCCAGCGGATTTAGTAGGATGGGCCGCTGAATAAAGAACTTGTGCGCCAGCATGGTAAATATGGCGGG
AACGGCGACAATCGGAGGTAAGTGGACAATCGACCATGTCCTCCAAGTCGCAGCTTGGTGCGATAATGATTATTTATGTAGGCGCCCGTTCCCG
CAGCCAAAGCACTCAGAATTCCGGGCGTGTAGCGCAACGACCATCTACAAGGCAATATTTTGATCGCTTGTTAGGTAAGCGGCAACTTTAGAAGG
CTTCATGCACTCACACTTCGCCTATTTTGTCCCAGGAAGTTATAATCTTCCATTGGTATTTGAGGGCCTGATCCTCTGTTATGACCACCGCGTCC
CTGGGCAGTTCGTCGGGCTTGGCGCGTGATAATGCCATTTTTCATTAATTTATCAAAATATTTGGTTCTCAGAAAACAGCTGCTTATGGGTCAGT
GTTGTATAAGTCCCGAACCGGTGTGAGAATGTTGAATACAGTGGGTATCGGAAAAAGGTCTCGGAAAGTAACGCGAAATTTACAGATGATGACAT
ATCAGTGCTGTTAAATGGTCAAATCAGTGTTGCGTGCTGTTTTATATCAGAGGCGAATTGAAGTGTACTACCATAATTCTTGCGAGTCTGCTTAA
AATGCCTCACAAACGTAGGAACCGAGTACATGCGAACCAAAGGAATTTCACAGCGCGACGCGTTTCTGTGGCCAAACTGTCGTCTGCACCGCCGA
ATGTGCTCGTCGAATCCTGCAACGGTTCTCATGCGGATAACAGTTCGCCGGACAGTCCGAAAGCCAAAGAAGGTGCAATGACCAACGGGAAAAAC
CCGGAGATCAAGTTAGCCGTGCCCAAATGCAACACCACCGTGCGCAAGCAGAACGAGGCCCATATCATATCCAACATTAAGCTGGATATGAACCT
TAATAAGGATTCTAACTTTATCGCCCCACAGGTTAATTAAGGTTTTCAATTATGTATACTGTTTTATAATAACATATTCTGTAACTACCCCAAAG
ATCACCAAAAAGATGAACTTCGCTCCGAATCGTGTTGTATTCGGGGTCCTGGTGCCTCTCAATGTCAACGATTCTGTGCTGGTGCCGCACAATAG
AAAACCGGATGCCTTAAAGCACACATCGAAAGAATCGGAATCATGCAAGGCCATAAGCGAGCCCCAGCTAGCCGACTATGCGGAGAAAGTAGATC
CCATGATCATGGCTGTTAAGGAACCAGTACTCCACTTGGATTGGGAACCAGGACCCTTCGATTTTTTCGGCGCATATAGGAGAACATACAATTAG
AGTTACATTTTATTTATAAATATATCCGAGAATATCAGAATGTTTGTAGCTTTGTTAACCGATGAAGTTCATGACCACCAGATGAAGGATCACAT
GAGCGAAGATGAAGTCGGCGAAACCGCGTTCCGGCGAAATGCCGGCAAACACGCTCTTGTTCTGGGGATTGGCCTGCAGGCGTAGGCACACTGCC
AGGACGAAACAGCTGACGGTGCTGATGAAACCAGATAGGAAGGAGTTGAACGGGAAGGTTCCAACCAGGCAGCAGTAAACAAACTGGATGATGCC
GGTGAGCAGAATGTAGCCGAGGTAGATGTCCACCAGCTTCAGTTTCTTGGGCGTATTCTGCACGTAGTCGTTGTAGAACTTGGAAATGACGCTCG
ACAGCTCCACCATTTTGCTATTTTATGTGATATTTGTCCGGATATTTAAGGATAAAGGCGCTTTTTAACAAATTAATCGCAGACACGTCACAAAT
TGGGAGAGAACTCAAAAGTAGGACCGTTCGTCTAGTTGAAAATAATACTGATAGCTTTATCGATGAAGGCGCAAGTACAGTGGGCACTCAATAC
CTTGAAGTTTAATAAAGAATAGGTTTATATATTAAAAAATTTTTGTGTTTTAGTTAAAACTAAAACATAACAAATCTTATAGATTAATGACCGCT
ATCGATTCTTTTTTAATGTTGCATATGTTTGAGAGGTAATGTTATAATTTAATTTATATAAAAAGAAACACAAATTCTTTTTCTAACCCGTTAAT
AAAGTTTTCTATCCGATTTTCACTGTACCGCCAAATCAGCGAATTAATCGATAGATACGGAAAGTCATCCTCGATTGTTGTGTCTTGCTTTGCTT
CTTCAGTGCTTGTTTTGGGGTGAGAGGCAATTGTTATTGCGAGTTGAGTTCGAAGAAATTAGTAACGTATGTATTTAAAACACCACAAAAGGGTA
TGATGTGCGTTGCAACGTTACAATAAACATTTGCTATCCAATGTGCAACA (SEQ ID NO: 1294)

Exon: 1001..1456
Exon: 1521..1805
Start ATG: 1142

Transcript No. : CT32729
GAAAAAGGTCTCGGAAAGTAACGCGAAATTTACAGATGATGACATATCAGTGCTGTTAAATGGTCAAATCAGTGTTGCGTGCTGTTTTATATCAG
AGGCGAATTGAAGTGTACTACCATAATTCTTGCGAGTCTGCTTAAAATGCCTCACAAACGTAGGAACCGAGTACATGCGAACCAAAGGAATTTCA
CAGCGCGACGCGTTTCTGTGGCCAAACTGTCGTCTGCACCGCCGAATGTGCTCGTCGAATCCTGCAACGGTTCTCATGCGGATAACAGTTCGCCG
GACAGTCCGAAAGCCAAAGAAGGTGCAATGACCAACGGGAAAAACCCGGAGATCAAGTTAGCCGTGCCCAAATGCAACACCACCGTGCGCAAGCA
GAACGAGGCCCATATCATATCCAACATTAAGCTGGATATGAACCTTAATAAGGATTCTAACTTTATCGCCCCACAGATCACCAAAAAGATGAACT
TCGCTCCGAATCGTGTTGTATTCGGGGTCCTGGTGCCTCTCAATGTCAACGATTCTGTGCTGGTGCCGCACAATAGAAAACCGGATGCCTTAAAG
CACACATCGAAAGAATCGGAATCATGCAAGGCCATAAGCGAGCCCCAGCTAGCCGACTATGCGGAGAAAGTAGATCCCATGATCATGGCTGTTAA
GGAACCAGTACTCCACTTGGATTGGGAACCAGGACCCTTCGATTTTTTCGGCGCATATAGGAGAACATACAATTAG
(SEQ ID NO: 1295)

Start ATG: 142

MPHKRRNRVHANQRNFTARRVSVAKLSSAPPNVLVESCNGSHADNSSPDSPKAKEGAMTNGKNPEIKLAVPKCNTTVRKQNEAHIISNIKLDMNL
NKDSNFIAPQITKKMNFAPNRVVFGVLVPLNVNDSVLVPHNRKPDALKHTSKESESCKAISEPQLADYAEKVDPMIMAVKEPVLHLDWEPGPFDF
FGAYRRTYN*
(SEQ ID NO: 1296)

Celera Sequence No. : 142000013384301
ATGGTAGTTGAAATGCATATAGCTCAAGAAATGAATACCAATAAAATCTCCAGCAACAGATTTATGGAAATCCTAGCGCTTTGAATCAAATAAAA
AATGTGCAACTGCGTACAAACTTCTTAGATTGTAAATACCCTTCGCAAGAAAGTAACATGTTAATAATAATAAATTCTTGTAATCCGCCACACGA
TCTGAATACTAATGTTTACCAAGTAATTGGTAATAACATTCTGAATAAGGAAATCACTGGCATTTACTTGTCTACCATTAATTTATGGTATTGTC
GAACGCTTATGTTTGGTGAAAATATATTAAAATGCCCGCTTAGAATTTATGGCCAGTGTAATGGTTTCCACAGAAGCACTAATAAAATGTCGAAA
TTTATTCATTTTCACGATGTTGCCAAATTTATAGTGACTCCTATGAAATTTTCTTGCCGTGGATTCCTAGAAGTGAGTGGATACATTCTTAAATT
TAATTTTAATTTAATTTAGACATTGCCAAGAATAAAAACTTTTCTGATTTGCTCAAATATTAAAAATTGATTCAAGTATTTTTTTAATTCATTTA
AATGATCTGAATAAAAAGTAAAGTGATTTACAGTGCTAAGCTAGCACCATGTTTTATCAATAAATTCCAGAATGACTAATTCATTCGCTATTCGA
ATTATTATTTAGGGAATTTAAAAAAGTCTCTCAAACAAAAGGTTTGTTTGTGAATTTTCTTATCAATGGAATTCCGTTCTTGCTGAATCAGTGAA
GAGCCCATTTCAGATTTACGCTATTCATAATTAGAAATTTCATATATTTTATATGTATCCTTTTCTTTTCTTCAAAATCAATTTTGATTCGTAAA
GATAAAGTTTTCTGTATGCTAACATAAAAAACATTAATGCATAAAATAGGCCCTAACGAAATATACATTTTTCTGTAGCTGTTGCTAACTTCGCG
ACCCCCATAGTGTTGGGTGGCCCCAGCGGCAGGCCCCACCTTCTTGCCACTCACCTGTGCAGTCGCTCCGTTTGCTCGGCTTCGTTTTGCAGATC
ATTGATGGCGAACAGCTCCATCTCGCCGCTGCGCCCGAATATCCCATTGGGGATCTTGCGCAGGAACTTCTTGAGCACGCTGGCGATGGTGAACA
CCGAATAGTTGTCCACGTTGACGAGCCGACCGGCCTGCAGGAAGTGGATGAGCTTCTTCATTGCGCCCTGGTGGCCGGGTGCGCGGAATACATCG
CGGCGGTTCGGTGACTCCTTGTTCAGTTTGAGGATCAGGACGAGCAGGGGCCCGGGAATGTTGTTGTTGTGCTTGCACACCTCCTCCAGCGGCAC
ACCGAATTTGACCTTTTCGAGGCGGTACGGGTAGGCGGGAGCGGTGGCTGGGTGGCCGCAGGAGGTCACCACGTTGCCCAAATCCGCGGCGCGCC
TATGGACGCGTTCTGCCCAGCTGGACATGGTTTTTCACGCGATTTTCCTGCCTCCCTGCCTTCCTGCCTGTGTTTGTGTGCTTTTGCGTGCGCGT
GTGTGCGTGTATGTATGTGCTGGCGAGTTTTTCAGCGAGCAGAGGAAAATGTGCTCGGCAGATTTTATGGTTTTATGCTGGCCACAAACATGTTC
ACTTGACTGGAATGTTAATTTGTTCGCCTGCCCAATATGCGGAAAATATCTTTCAGATTTTCACTATTTATTATTTTTTATTATTTTTTACTTTA
TTTTCGACACCTACTCTCGCGTCGCAGCCCCAGATTTTAGCCCAAAATGAGCAGCTTTGAAAAGCCAGCTTTGATTAAAAAATCGCCACCACTCC
TGCTGTATGCATTTTTCTCTTCTCTTCTTCGCGTCTCTCTTTTACACTGCGTTTCTCCGTTTCTTTTGCGCTTTTCTTCTTTTTGGCCAACGCCT
CGGAGCTGCTATGCCTTTTGCGCCCCTTCGCTTACTGAATTAAACGCTCGCCTATCGCATTTCGCTTGGATTTGTTGAGAACGCGGCGTTCGGCG
TCACTTTCGGTTAGTTTAGCACTAGTTTAGTTGTGTTATTTCGGGGAGTGTTTAATTATTTTGCTGCGCTCGCCCGCACGCTCGACTTTTTTCGC
TGTATATTGAAAACGGAGTGTGGACATCAAGCGGTAGCTGCAGAATGCCTGAGGCTCAGCGCTTCGCTGCGAAATACCAACGGAATATACCAAGA
AATTATACTGCACAAGTACTGTGATAGTAGGGGTGTTCCAGCATTCGTTAAGTTTCAAAATGCCAAAGCCAAAGATAAAAAGATATAAAAAAAAT
TAACGCACTTATGCAATACCAAAAACGAATAAATACATAATGTTACTACTTTTATCAGGGAACTTGGCTTAACAAAGTTTATACAAATGCACAAT
GAAATTAAATCTACTTAACTGCTAACTGTTATTATTAGTTATTTCATACGATATGCAGGAGGCAGAAAGTTGCTTATTAAACATATATTTTCATA
AATATTTCACGAAAGTATGAGAAAATTTCAAAATCGTTTGATAATATACTAATACGCTATTTAGCCACATATATAAGTCTCTAATGTATTTCTTA
AATAAATCATTTGTAAAGCTATAAACTAAATTCTTTTATAAAATCTACTCCCAAAAAAAACAGCAGCATCAAACCTTAGCGTCTTAATATTAATT
CAAATGAACACTCATCGCTTGCCGATTCAAAATCGTAAGGTTTTCTTTTAAATTCAAAACTCGCTGGAATGCCGAGACTTGTGACGTCACACGCC
ATCTTCATGCTGCGCGGCGAGAAACATGCGCAAACGTCACCTTCTCAGCGGCAGACTCAGGTTGTCCATCCCTGGTTCAAGTAATGTCACCCTGG
TTTTTGTTTTGTAAAGTGAAATTGTTGCAAGTCAAACAACAATAATAAAAATCATTAAAAGCGCGTACAAGAAGTCAAAAAGAATTGCCCACACA
AGTACGTATTGACGGGCTGTCAGCTTTGCTATATGGAAATCAATTTTCCACTCAACTTTTACTTGGAAATCGGTATTTAATTTTGTGTTGTCTGC
TGTGAAAGTAACAACAACAAAATCAAGAGTAACGTCAAGAGCAAAAATAGTTTTCCCCATTTTCAAAATTGACAAATATAG
(SEQ ID NO: 1297)

Exon: 2121..1001
Start ATG: 1453 (Reverse strand: CAT)

Transcript No. : CT32814
CTTGATGTCCACACTCCGTTTTCAATATACAGCGAAAAAAGTCGAGCGTGCGGGCGAGCGCAGCAAAATAATTAAACACTCCCCGAAATAACACA
ACTAAACTAGTGCTAAACTAACCGAAAGTGACGCCGAACGCCGCGTTCTCAACAAATCCAAGCGAAATGCGATAGGCGAGCGTTTAATTCAGTAA
GCGAAGGGGCGCAAAAGGCATAGCAGCTCCGAGGCGTTGGCCAAAAAGAAGAAAAGCGCAAAAGAAACGGAGAAACGCAGTGTAAAAGAGAGACG
CGAAGAAGAGAAGAGAAAAATGCATACAGCAGGAGTGGTGGCGATTTTTTAATCAAAGCTGGCTTTTCAAAGCTGCTCATTTTGGGCTAAAATCT
GGGGCTGCGACGCGAGAGTAGGTGTCGAAAATAAAGTAAAAAATAATAAAAAATAATAAATAGTGAAAATCTGAAAGATATTTTCCGCATATTGG GCAGGCGAACAAATTAACATTCCAGTCAAGTGAACATGTTTGTGGCCAGCATAAAACCATAAAATCTGCCGAGCACATTTTCCTCTGCTCGCTGA
AAAACTCGCCAGCACATACATACACGCACACACGCGCACGCAAAAGCACACAAACACAGGCAGGAAGGCAGGGAGGCAGGAAAATCGCGTGAAAA
ACCATGTCCAGCTGGGCAGAACGCGTCCATAGGCGCGCCGCGGATTTGGGCAACGTGGTGACCTCCTGCGGCCACCCAGCCACCGCTCCCGCCTA
CCCGTACCGCCTCGAAAAGGTCAAATTCGGTGTGCCGCTGGAGGAGGTGTGCAAGCACAACAACAACATTCCCGGGCCCCTGCTCGTCCTGATCC
TCAAACTGAACAAGGAGTCACCGAACCGCCGCGATGTATTCCGCGCACCCGGCCACCAGGGCGCAATGAAGAAGCTCATCCACTTCCTGCAGGCC
GGTCGGCTCGTCAACGTGGACAACTATTCGGTGTTCACCATCGCCAGCGTGCTCAAGAAGTTCCTGCGCAAGATCCCCAATGGGATATTCGGGCG
CAGCGGCGAGATGGAGCTGTTCGCCATCAATGATCTGCAAAACGAAGCCGAGCAAACGGAGCGACTGCACAGGTGA
(SEQ ID NO: 1298)

Start ATG: 669 (Reverse strand: CAT)

MSSWAERVHRRAADLGNVVTSCGHPATAPAYPYRLEKVKFGVPLEEVCKHNNNIPGPLLVLILKLNKESPNRRDVFRAPGHQGAMKKLIHFLQAG
RLVNVDNYSVFTIASVLKKFLRKIPNGIFGRSGEMELFAINDLQNEAEQTERLHR*
(SEQ ID NO: 1299)

Celera Sequence No. : 142000013384429
AACCCTTATTTAGCTTTAAAGTCAAAAATTCAACTTATTTCACAGTGTGTAAACAGTTTCTTGACAAACTGTATGTACATAACCTTAAATGTAA
AGATATATTGATGTCAAATGTTCAATTTCGCTTCATCTTTCAGATTTTAATAAGTTTATAATTGAGTTAAAATGTCGGATCTGGTATAAATTAA
GATTAAGATTTACAGATTTGAGCAGATTTTAATTCTTAATTGTTTGATGCTTCTGCCTAAAGCACAACTGTTACATTTCATAGCAAAATTCATTT
TTTTAAATATAAAGGAATTTTAATTTAGTTATGTTAAGGGGAAATTCAATAACTGTTATATACAGTAGAATTCACCTTTAAGTATAATACACACA
TACATAGGTTCTATACAACCATGGCAGTTGAATTTCATCATGGCTGCCACGAATTCGGGAATTCCCAGGCATTTCGAAAGTTTATGGAGCATTTG
ATTGCAAATGGTAAATCCATATGTACAAAACATATGTATGTACATGCATGCATACATCTATTTTTTGCCTACGCCGATATATCGCACTTTGCACT
TACTTTGTTGTTGTTGCTGATGCGGTTGTTGTTGTTGCTGCTGCTGTGGTTGTTGCAGCTGCTGTGGTTGTTGCAGCTGCTGTGGTTGTTGCAGC
TGCTGTGGTTGTTGCTGCCGTTGTTGTTGTTGCTTTTGCTGCTGCTGGGGCTGTGGTGCTGCAGCGCTATCCTGTCCTCCTTTCTTGTTCTCTGG
GGTGGTAATTGGAAAGTGCATATATTTGAATAGCTGTATGGTCCTGCAGGTGGGACAACTCACTATCTTTTTTTCCCATGATTTACTTTTGAGGG
TTTCGAGTTAACTGACGACTTTTAATAGACGATTTTTTAATGCGTCACAGTCTTTTTTAGTGATGGGAGGCCTTAGGGGTGGGCGATAAGTTATT
GAGCGGCACAGCTAAAGTGTTTTCTGTTATCGATTATTGATAGGAACATACGGACTAGGCGGGCCATTCAAGTGGGGACTCTATTTATATTTGTA
TATTTTTATACATGTTTTGTATACATGTTGCTTGTTGAGTCAAATGTATGCTATATTCGTTGAAAAGCATGTATCCGGCAAAAGAAACCGATTTC
GACCTAATAAATTATATATATTATAATATATTATATATATTATATATATAAGGACCAATAGCCGAGTCGATCTAGCCATGTCCGTCTTTCCGTCC
ATCTGTCAGTCCGTACGAACGTCGAGATCTCAGGATGAATAAGAAGCTAGAAAATTGAGATTACGGAAAGCCCCCAAAACTTCCCACGCACATTT
TCAAAATGTTTTGACATTTTCATATTTTTATTAGTCTTGTAAATTTCCATCGATCTGCCAAAAAACTTTAAATTGCCACGCCCACAGTTATGCA
AAATGTGATATTTTTCATATTTTGATTAGTCTTGTAAATTTCTATTGATCTGCCAAACTACTATTACTCCCACAAACCGCCGAAAAGCCACGCTT
ACAATTTTTAACAATTTAATTTTTTTCTTATTTTATTCACCAATATCTAATTTGCGTTCGCATTTCCAATAGTTGAGTAACTGGCATCTGATT
ATCGGGGAAGTTTAAAATAGGAAAAAAATTTTAATTTACTAGTTTTTTTTTTTAAATTTTATTTTGGAAGAAGACATCAGTAAGAATCAATAAAT
TTAATCACCACTGCTAGAAAGCATTATTTTTATTTTTCCGCCTTTAAGTGAAAAATAGTTTTACATTCCAG
(SEQ ID NO: 1300)

Exon: 781..533
Start ATG: 781 (Reverse strand: CAT)

Transcript No. : CT32815
ATGCACTTTCCAATTACCACCCCAGAGAACAAGAAAGGAGGACAGGATAGCGCTGCAGCACCACAGCCCCAGCAGCAGCAAAAGCAACAACAACA
ACGGCAGCAACAACCACAGCAGCTGCAACAACCACAGCAGCTGCAACAACCACAGCAGCTGCAACAACCACAGCAGCAGCAACAACAACAACCGC
ATCAGCAACAACAACAAAGTAAGTGCAAAGTGCGATATATCGGCGTAGGCAAAAAATAG
(SEQ ID NO: 1301)

Start ATG: 1 (Reverse strand: CAT)

MHFPITTPENKKGGQDSAAAPQPQQQQKQQQQRQQQPQQLQQPQQLQQPQQLQQPQQQQQQQPHQQQQQSKCKVRYIGVGKK*
(SEQ ID NO: 1302)

Celera Sequence No. : 142000013384829
TTATATTCTTACATCAACGAGACTGCTTTGGTAGTTTGTAGTCTGCACTGATTCATCAGCTTTTGAAGATTTCTTTCTGTGTACATTATGCGTCG
GTCGATGCACAAGCAAATGTCACATCAATTAGCCGCACCGAGGGCCACAAGATGTGGCGATTGCAGCTGGCTTGGCTAAGTTGGCTAACTTTAGC
TAGCTGGTTAGCAGACTCATAAAACATCAAATTAGCTTTGACTAGGTTGGCTAATTTGAAAAGTAAGAGGCAGTTGGGTGAATTGGCCATCTCCA
GTTGTGGTTGCGCCGTGGTTGAGTGGTTCAATGGCCGCCCGGCCACCCACACGCCAGCTGTTCGCTGACCTTCGCCGCCTGACGTTGACTTTCCT
TGATTTCTACACGTATCAGTCGGAAAATGTCGAGCAAATATTGCGATACCAGCTGTGGGTAAAAACAAAAGTCACAGCAGCAGAGCAAATATTAT
ATAAGCACACACATCATACTGTGTGCTGAGCGTGTTTTCAGTTGTTTTTTATTACTGTCTGATAATCACCTCTGATCCGTTTGTTGAACCGATAA
GAAAAGATCCATTCGCCTATGGGTAAGTGTCGACCAATTGATAAGCACTTATTTATAGACATTAACTACTCTATAAATAATGTCATCAGTCATTC
ATCATAACTCCTCCGCAATTAAACAGAGTGAAATGGGAAGCAATCACTGTCTCGGAACTGTAATCTGGAGTAGTACAATAAGATCAAAGCCAAGA
AAGTAGGAAATCGATAGTTAACCATTGGCCATGCTGTTCGTTCAAGTTACTGTGGCAGCGGCAACAGCAACACTTCAAAATTTGCTGCAATTTGC
TTTAATTATACGCTCCGTTGGACGAAAAAAACAGCAACGAACAAATAGGGAATGTCGATCGAGATTGCAGACAAATTTAGGCCATACAAAGC
TCTACTTTGTTTTCGCTTTTCCCGAAAAATTAACCCACAATTTTCCCCCAATTGCAGAAACACCAACATAGTATGCGTCTCTTCAAAACGCGCAA
ATCCACGGATACCTACAGCACACTAGCCGCGCAGCAACAGCAACAGCAGCAGCAGCAACAACAACATCAAGCGGAAGGCAGCAACATTTCCCACA
GCAGCAACAGCAGCAGCAACAAGAGTCACACACCGGCAACATGCAGCAACAGACTGAACAAGAGCATTGTGAGCAGCACCAGCATATCGTCATCG
CTGCCTGATCTGCATGACAAGTCGCCCGTCATGATCCTCAGCTGCACCACCCTGGCCAGCAATGGAGCCACCGCCACGGCAGCGGTCACAGCAAC
AGCCACCGGCACAGCAGCAACATCTGGCGGCTCGCTGCAGCAGCAACAACAGCAGCATCTGCAACACCAGCAGCAGCAGCAGCCGTTACGCACGG CCACGCCCACGTGTCTGCTGAGTGGCCGTCAGACGCCATCGGCCATATCGGTGATGTCGCTCCAAGAGGCCACCAGTCTGCACCGCCAGCAACAG
CAGCCACACCAGCCACCCACCATCTACGTGCCGGTGCCTACGAAACTTGGCAACAATGTCAACACTGGCAACAGCTCGGCCACTCTGCTGCTCAG
CTATGGCAGCACCAGCAGCATCGCCAACCTGCAACAGCAGCAGCAGCAGCATGCCGCCCAGTACCAGCAGTATGTTGCACAGCGGCTGCACGCCG
CTTCCAGCAGTTGTTTGTACGAGAAGGGGTCGAATGCCAGCGGTGGGGCGAGCAGCAACAAAAGCAGTCTATCCCTGACCCCAAATGGTAAGTAC
TTTACTATAAAGTGAAGTAGAATACTCATATTACTAATGGGGTAGCCCAGGAGTTGTGCTTACATTAATTTTTATTATTGGCTGATAATATCATG
GGTAAAAACTTGCAATCATTTAGCTGCCAGTGGCAGTTACTTTCCGTATCCGTATTCACCGATTTCTCAAAGTAAGTCATACTCTTCAGTACACA
AAAAGCTTTTGCTACATTGTTGGGCGCAGTGAACAGGACATGTGATGCACCTTGTGATAACATGGTGATGAAGAAATGGCTCTTATCTTCGCAGA
CATTCACGAGCCTCAGCCAGTGATACTTGTTTTCCTCCTCAACCTCCCAAATGCTGCAGTTACTATTGGCGCCCAATTCCAGTTGATTTCCAGCA
GTTATATAGAACAATTCCTTCTTGTGTTCGAGACACAAGCGACGAGTTTTCACCAGAAGCCTCAGAGGTCTTGGTAAACTCTGCAACATGTTTTG
GAGATCATTGTTCCACTGTTCTGGATGATTACTCTTGAGGTTCCTCAATTCCCGTGCAAAGTTAGAGAGAAGAATCTCGTTTAAAAGACGAAAAC
GTCGTAGATGCCAATGAAAGCTCATCCAAAGCTTCAGCTTGAAGGGATTTCCGGTATTGAGATGGCTTTGCAGATCTTGCGGTGCTTTTTGTGTC
TCTAAAATATCCGACCAGGGAATATTCCATGCCACGCGCTGTTGCTGCTCTTCATTCAGTGATAAACTGATGTCCTTACTCCACTTATCGAAATC
CAAAGGGCTTGCATTTAATTGTGTAGGCACAAGTCCAATCAGTACATGAATATCGTCTTTAATTACGGTCTGAACTGGATTTAGTAGTGAACTTA
GGCACAAAAGTATTATGAGAGCAATGTAAACGACCATTGCGATGGAAAATCTTATTTAAACTGATCTATGGATTCCCTATTTGTTCAGTTTGCTC
TGTGGGATTTCCGGGTATTTGGCGCTTATCGCTGGTTTTTGATAATTCCTTGATATTCAGTGGGGCCAACGCCCTGGTTTTCATTTCCTCAAAC
CCAACTGATACCAATTCCTGTTCCCACAGGTCACTTGCCCGACTACAAGTTGGTGACAGCGATGCCAGTTGTTGTCCTGGACGATGAACACAAAT
CCAATTCATTGCCGGCCACTGAAGCGAGTCGCAACAGCAACAGCAGCAGCAACATGAACGGCAGCAGCAACAGCAACAGCCTTGACGTCAGCAAC
AGCAACTCGCATTCGGGGAGCTCCACTTCTTTGGCCAGCACCACGAGAAATGGTAAGTACTTTGGCCAAAAATAGAAGTGAAATCCGGGCAAATG
CCTGGAAATTGATTTTCCCTTCAAGTGGCGGCGCCTCGAGGGTTTTTATTCCCCGTGGAGTATATTTTATTTTGGGGCACATTCAACCGAGAGTG
TTGGGTCAATGGAGAGGGGGAAAATGAGCCCATAAATTATAGAGCGGCAGAGGGTGTGTTGTCAGCCAGGTATTAAGAGCTCAATTTGGAGCACA
TTTTAATTGAAACAATTAATTTTCCATGGCTAAACATAGGAAACAGCACTCCCAGTGCTTCCGTGTTTAGCAAAGGCAAAATCAGCGCCAATCAG
AGTTGCCAATTGTCATCGATACGATGCGTATTGTGTCGCATGGCACATACTCTACTCCAAAATACCGTATTGACCCGATTTCGCATCAATGCGCG
CCGCCAACATCGGCGCTGTAATGCGATCCCATGTCTGCAACTGGAATTTGTATTGTTTCAGCCGGGCACGAGTTGGTGCTGCTGTGGTCTCGAT
TTTGAAGAGGAGCCCACCCTAAAAGCCTAAACTACACAGGGAGAAACCCTACTTGGGAACTTGGGAATAAGTCATAAATCTGCTAAAGAAAACTT
TATTATAAACACCTTTCTTTAAAATGATTATACATGACACAGATTTTTCTAATATTATCAGAAATAAATGTTGCTTCCATACTATTCTTTCAGTG
TAGAATATCTCCCAGCCAACAGCCGACCAAGTGTGACAAAGCTGGGCATTATATGTCATTCAATGCAGTTCAGTTGAGTTCACTTTACTTTGGTT
GAGTTCAGTTTAGTTGTAATGATTTGCACAAAGAGCACTTTATTTACTTTTATTTTTGCCCGGTTATGTGATATATGATTGAGGTTTTCGGTTGT
ATAGATGGGTGGAGTTGTGAGTAATAGATATGGGTATTAGAGCGGCTAGTTAGATAAACGAGGAATTGAGGGCAGGAAATGGCTGATGATGTGAT
TGGCAAATCAAAACATGAGAAAATATGAGT
(SEQ ID NO: 1303)

Exon: 1001..1797
Exon: 2880..3115
Start ATG: 1023

Transcript No. : CT32873
ATTGCAGAAACACCAACATAGTATGCGTCTCTTCAAAACGCGCAAATCCACGGATACCTACAGCACACTAGCCGCGCAGCAACAGCAACAGCAGC
AGCAGCAACAACAACATCAAGCGGAAGGCAGCAACATTTCCCACAGCAGCAACAGCAGCAGCAACAAGAGTCACACACCGGCAACATGCAGCAAC
AGACTGAACAAGAGCATTGTGAGCAGCACCAGCATATCGTCATCGCTGCCTGATCTGCATGACAAGTCGCCCGTCATGATCCTCAGCTGCACCAC
CCTGGCCAGCAATGGAGCCACCGCCACGGCAGCGGTCACAGCAACAGCCACCGGCACAGCAGCAACATCTGGCGGCTCGCTGCAGCAGCAACAAC
AGCAGCATCTGCAACACCAGCAGCAGCAGCAGCCGTTACGCACGGCCACGCCCACGTGTCTGCTGAGTGGCCGTCAGACGCCATCGGCCATATCG
GTGATGTCGCTCCAAGAGGCCACCAGTCTGCACCGCCAGCAACAGCAGCCACACCAGCCACCCACCATCTACGTGCCGGTGCCTACGAAACTTGG
CAACAATGTCAACACTGGCAACAGCTCGGCCACTCTGCTGCTCAGCTATGGCAGCACCAGCAGCATCGCCAACCTGCAACAGCAGCAGCAGCAGC
ATGCCGCCCAGTACCAGCAGTATGTTGCACAGCGGCTGCACGCCGCTTCCAGCAGTTGTTTGTACGAGAAGGGGTCGAATGCCAGCGGTGGGGCG
AGCAGCAACAAAAGCAGTCTATCCCTGACCCCAAATGGTCACTTGCCCGACTACAAGTTGGTGACAGCGATGCCAGTTGTTGTCCTGGACGATGA
ACACAAATCCAATTCATTGCCGGCCACTGAAGCGAGTCGCAACAGCAACAGCAGCAGCAACATGAACGGCAGCAGCAACAGCAACAGCCTTGACG
TCAGCAACAGCAACTCGCATTCGGGGAGCTCCACTTCTTTGGCCAGCACCACGAGAAATGGTAAGTACTTTGGCCAAAAATAG
(SEQ ID NO: 1304)

Start ATG: 23

MRLFKTRKSTDTYSTLAAQQQQQQQQQQQHQAEGSNISHSSNSSSNKSHTPATCSNRLNKSIVSSTSISSSLPDLHDKSPVMILSCTTLASNGAT
ATAAVTATATGTAATSGGSLQQQQQQHLQHQQQQQPLRTATPTCLLSGRQTPSAISVMSLQEATSLHRQQQQPHQPPTIYVPVPTKLGNNVNTGN
SSATLLLSYGSTSSIANLQQQQQQHAAQYQQYVAQRLHAASSSCLYEKGSNASGGASSNKSSLSLTPNGHLPDYKLVTAMPVVVLDDEHKSNSLP
ATEASRNSNSSSNMNGSSNSNSLDVSNSNSHSGSSTSLASTTRNGKYFGQK*
(SEQ ID NO: 1305)

Celera Sequence No. : 142000013384693
AGTGTTACGGATACTGGGAAATGCAATTACGGGATAGTGGATTTGGGGTGGTGTGCTTGGTTGCTAGTGCTTGTGTGGCTTCGCCGAAGGGCTTG
GTCTTTGATCTTTGGCTTTGGCTTATCTTATCGTATGATTCTGGGAATACTGGTTTGGATGGATCTTAATGGCTGGCTGGAAATAACAAGTTGGT
TATATGTAGTTTAGATATCTCATTCTTTGTACAGGCTTCCCCATACGGGCACAACATCGAACAGGCGACACAAAGCTATAACATATGTGTACATT
TTCGCGATTCTAGACAGAGATAGTTGGTAGATTGGTGTAGTTTAGTCAGTGTTTAGTACTAGGCGGGAAGTTAGGATAGCTAGATAGTGAGTCAC
ACTACGCATTAACATATGTGTTATTTTGTGGCACATGTAAAGAACCGAACGCAGGCATTGGTTTCATCGATCGCATTGCTGATTAACTTTCCAGC
CGAACTGGAAGCCTTGACGCGAACAAGTGCAAGGTTATTAACTGACCCCAAGTGGGCGTGGTGGTGGGCGGTGGGCGCTACTTGTGCCAGCACAT
GGAGAACCCGAGTTGTGTGCAAAAAACACTGCTCAACTCGTTGGGAACACCGAAAATTAGTTTTTTATGCAGAAATAGTGAAGGAGAACACACAC
ACAAACACACGAAGGCGTACTGCGCCGTGTGGTTAGCAGAGGGATTATAGTGGAAAAGTGAAGTTTTCGACGGATGCACACACAACACACATAACTA
TATTTGCACACTATTTGTTAATTACCAGCTCCGGCTTATATGTTTTTTTTTTTTTTAAATCTCGAACTCTACGGGCTAAAATCGAGCAAAGTTGA
CGAATAAAAGTGGATACACACCCAAACTAGTGATGTGCCGCGCGGCGATAGTTCGGGTGCGTGAGCGCACCCGCATACCATCGCTAATATTCGCG
CAGAAAAACATACAATACGTATCAGTTTTAGTTCCATGCGCTCTGCAAAATGATGGCCAAGGACAAGGGTCTGGCTGTGGCCGGAACGGCGGCC CCCTTACCGGCCGCCCTCGACCACGAGTGGTCCGCCGAGGAAGAGCTGCAGCTGTTCCATGCAATGGAAGGCCTGCGCCCGGTGGGCATCAACAA
GCACTTCTACATGTCCTGCATTGTCCAGCGTCTGTCCAAGTCGCTGAACCGTGAAATGCCCAGCGAGCTGATCTGGCGCCACCTGGGCACCATGT
ACAAGCTGAAGGAACTGGACGATCTGGAGTCGCTGCCCTTTCCCAACGAGGAGCGCGAGTTCAGCCTGCCGGAGCAGGATTACGGAACGCTACAG
ACCAAAAAGACGGTGGAAGTGCATGCCAACGAGGAGGCTGCAGAGGCACAGTCGGCCCCTCCAACAGCAGAGACCAATGGCAAAGGTAGTTCGTT
AGTTATCATCAGGATTCATTCACTTGTAATGTTGTTTTACAGCTCCACCTGCAACCAAAACGCCGGTACCGACGAATTCCACCAAGGACGGCGAC
AAAAAGCCCGTCGCCAAGCCCCAGGAGCAGCTGCCCAAGCGTCCGGCCAAGCGCACACGCGGCTCCATGTCCAACGAGTCCATCAGCCCCTCCAC
TACGCCGCCGCCGGTGCAGAGCAACAAGCGCCGTCGCATATAGGTGACCCCCGCCCGAAACTGACGATTGTTGATCCGTTTTAGCTCATTAGTTT
TACTGTACTCTAATAAAAGGATTTATTCTTCGAAATCGTTGTCCTCCTCGTTGGAGCCGTTCCCGTTCTCCTGCGCCAGAACCTCGGTGGCCTGC
ATGTTTTCCAGGAGCGATTTGAGAAGGCGTCGGTTGAGATGGTCGGTCTGCGTCAGTTCCCGGACTGCCTGGGGCGGAGCATTCTCGTCTGCCGG
TGCAGGGCTGTTCTCAGCTGGAGTCGGAGTCTCTGCCATGGCTTTGATGTGCTCCAAAACAGGCATTTTTCCCCCGAGAAATTTCAGCTTTTGCT
ATGACACACAGTCCGCTGGGTGACTCGTGCACTTGGAAACTTGGCTAAGTGTAGGGTACACTCGATAAAGTATCGATAAGTTGGCGTTTTACGTC
AGCCCTAGTTCCACCCCTAAGTCGATCGACTTCCAATTGGACAGATTCTCCCGCTCGAATTTAATTTAATCGGCAAATATAAACAAATACGCTCC
AAATGTTTGTTCCCGAAACGGAGGATATGCTGCCCAGACTAGCGCCCAGGCCGAGTGCAGCAGTGCCCATGGGCCACACCAATGAGATTATAGGG
CCCACCGTGCCGGAGGTATCCATATTGTTTGGCCAGCCGCCGCAGGATCCGCAGATGCAGCCGCAGCAGCCAAATCATGCACATCAGGAGTCATC
CCCTCGTGCTGCACCCACCTTCGCGTCCTGGAAGAAGCAAATGCTGCCCAGGGTCAACTTTTCGCCCATTTTGGCCACAGAACTGGGTCCTCGCA
CCGCTCCCAGCAGCAATAGTCCGTGCTCCTCGAAGGAATACCAAGTAATGCCCCGGGATCGCAACTATGCAAGCGATGCGCAGCAGACTACCAAT
CATATGAACTGCAATGCTGGTGGCTATAATGCCGAGCCCAAGCAACAGGCATATCAATCTAGGCGCTTGTCCAGCTCCTCCAACGCAGATGTC
(SEQ ID NO: 1306)

Exon: 1001..1415
Exon: 1468..1658
Start ATG: 1001

Transcript No. : CT33222
ATGATGGCCAAGGACAAGGGTCTGGCTGTGGCCGGAACGGCGGCCCCCTTACCGGCCGCCCTCGACCACGAGTGGTCCGCCGAGGAAGAGCTGCA
GCTGTTCCATGCAATGGAAGGCCTGCGCCCGGTGGGCATCAACAAGCACTTCTACATGTCCTGCATTGTCCAGCGTCTGTCCAAGTCGCTGAACC
GTGAAATGCCCAGCGAGCTGATCTGGCGCCACCTGGGCACCATGTACAAGCTGAAGGAACTGGACGATCTGGAGTCGCTGCCCTTTCCCAACGAG
GAGCGCGAGTTCAGCCTGCCGGAGCAGGATTACGGAACGCTACAGACCAAAAAGACGGTGGAAGTGCATGCCAACGAGGAGGCTGCAGAGGCACA
GTCGGCCCCTCCAACAGCAGAGACCAATGGCAAAGCTCCACCTGCAACCAAAACGCCGGTACCGACGAATTCCACCAAGGACGGCGACAAAAAGC
CCGTCGCCAAGCCCCAGGAGCAGCTGCCCAAGCGTCCGGCCAAGCGCACACGCGGCTCCATGTCCAACGAGTCCATCAGCCCCTCCACTACGCCG
CCGCCGGTGCAGAGCAACAAGCGCCGTCGCATATAG
(SEQ ID NO: 1307)

Start ATG: 1

MMAKDKGLAVAGTAAPLPAALDHEWSAEEELQLFHAMEGLRPVGINKHFYMSCIVQRLSKSLNREMPSELIWRHLGTMYKLKELDDLESLPFPNE
EREFSLPEQDYGTLQTKKTVEVHANEEAAEAQSAPPTAETNGKAPPATKTPVPTNSTKDGDKKPVAKPQEQLPKRPAKRTRGSMSNESISPSTTP
PPVQSNKRRRI*
(SEQ ID NO: 1308)

Classification: hypothetical

Celera Sequence No. : 142000013384547
GCACTGTATGGAGTTGCAGTTGCACTCTCACTCTATAAGATGGCCATTATGACGACGATGATGATGACTATGATGATGGCTCAAAAAAAACAGGA
CATTGTGAGGTGCGGGGCGCTGCAAAAAGGATAATACAACTTTCTCGCTCTATTTGCCACGCACACACATGTTGTTACAGTGCCGTGATTTTTGT
TGCATCAAATTGGAATTTTTTCCTTAAATATGGTAAACATCGATGGGGCAGAGATTTATGTATAGTGCAGCGGCGCGTTGATGAAAATGACTCGC
CGCTGCATTGACCGTGTTTACTGTTTGTCAGACAGGGCAGCAATTTACGCCCACATGCAAAAAACATTAATTTGCATGCAAGTCAATTATCAGGA
GGCAGCAAACAGACAGGCGCTAGTTACCAGTTTTCAGTATTCAGTTTTCTGTTTTGAGTTTTCAGTTTTCAGTTTTTCAATTTCTTTTGCACAAA
CATTGGTGTTATTATTCCGCCATAAGGATGCAAGGACTAATGGAGATACTCTTGAAATGGGTCATGATATTCCAAAAGAATCGCATATGGCGCAG
AAAGATTTATTTTGTTTTTCATTAAAGTACCATACAAACCATTAATTTAGCTCGCTACTCTTATAGAGCATCTGCAGGTTGTTGAGCTCAACGTG
GACACTCAATGGCGAGGACTTTCAAACTGCCAGGCCAGCACATTTCTAAATGTTTTTATTAATTAAAAATATTGCAAATTAAACACATTTCCAAA
TTGCGTTTTGCATTTTTCGTATAAATACGCGGTCGATGGAAAAAATGCAAATATAATTTACAAAGCATACATTTCACATTTTATTCTTATTTTAT
GTTCATTGCATTTTGGTTTGCTCTATCGCCGCTTTCGCAGCCATCAGTTCTTAAACTTGCCTCAAAGCTCTTAAACACGATTACTACCTGCTAAT
TAGCTTAGAATACCTATGTTTTGGGACCAGTCTTGGGTGCATGATGGGGTCTACCTGCTTTTGATGGTCACCTCGCACTTGGCAGCCAGATTGCG
GAGGGTGAGGAACTGGCCGGATGCCCTAATCTCCGGCCAGCTGCACCGGAGCGAGTGAGCAGGTCCCAGGAATCGGTGGCCCGGAGTCTCGATGA
CAGTCTCGAAAGTGGGTCCATGTGGCAGGTGGTCTAGGTGCCACAGGAAGACGGCGTGCTCATCGCCGCCGCCGATCGCAATGACAGCCAAGAAA
AATGTGTGCACTCTGACGTGGCCAAAAGTGGAGGACTCCTCGCTCAGCCGCAGGCAGGCCACGCCCTCCAGGGGCAGCTGGGGGCGGACGTGCAA
GCGTTCGCCGAACGTGCCGTAGATTTGCAACACTGCCAGCCGGTGGTCGCCGCTCAAATGTCGCAACAACTGCCATTCCCGCCGACCTATTGACC
CCGCCTCCAGTGGCAGCTCCTGATTTACTCCGGCTGCCGGCGCCTGTTTATGGCTCCCCGCTGATAAGGATGCACCTCCCGAGTTCTCAACCACC
GCCAGCGCCTGCATCGCGACTGTTGACAATTTGTTGGCCACTGGCTGGCCAAGTTGGTAACTGTGGCTGCTGCATGATTTCCCAGTTGGGCAATG
ATAATTTTGATACTCGCTCTCGCTGCTTGCTGACTTCTCATGCCCCAGCTGCTGCCGCTCCTGCTGCTGCTGTTGCTCCTGCACCTGGACACCAT
TATTTATGGTGGCAACTTCATCGCAGCGCAATCCGTCTTGATCTGGCCCAGTAATCCGCCAACTTTTCTTACTCAACTTTAACTTTGGTTTAACG
AGCATATTGTTGTGACCTTCCTCCGAAAAGTGCTCGACAGCGGCCTCCTGATGCTGCACTTTTATCAGCGTGCAACGTGGCAGGACAGCCTCCTG
CACCGCCTGCTCCTGCTCCTGCCCCTGCTGACTCTTTCTTCTGATTTCCCGAGGACTTTGGTCCACCAAAACTGTTTCGAGTTGCCTGGAGATTT
GCTTGCCGCACTTGGACTTGCCGGAACTCGTCTTCGCCAGCGCCATTTTCGGTTGATTATGATATTCATTTGTGCACTTGTTGACGCTGCTCAGC
TTTCCATGGCCCTGGGAGGCAGCCACCTTGTTGGTTTTCCCTGAAAAGAGGCACCGAAACGGAGGACCATTACAAAAAGTACGAAATGTAAATAT
AATAAATACAACTGGGACAACTGGATGGATATGCACGCAAGTTGTCCATTTGCGCTCGTTTGTGTTTTGCCCCCAAATCCCTTGACACAAACTCC
CTTGAACTTCTTCAAGTGGCAAATGAAAATAGAGCAGAAACTAAGTAAATATCCGCGTACCTGCATCTGTATAAAAATGGTTGAACTATGGCTGA
ACTATGGGTGAATCCGGGCGAATCATAAAGAATGCACACTTAATGTAGACGCAATAAAAACGCACTAAGCACGGCATAATCTGGGAAAAAACAAA
GCGAAGGACCCTGAAGTGGGTAAAAGTGGCAAAAAATGAAGACCAGCAGGGAAAAACAAATGCAGACAACGGCGGAAAATTCTGTTGCTGCTTGT TACCTCCGCTGTAAACTTCACTCCAAGTTAACTTGGTCGACACAGATTGAAAATGGCAACAAGGGCGGCTAAACTTTAAACGAAGCCGCCCAGTG
GCAAAGCAAGAAAAGCAACGCCAACAACAATCTTCCGGCAAGATGGCAACGCAGCTAAGCGCGAAAAACTTTAGCAATTTATGTTACATAATTAT
GCCATAAAAAGAACAACAAGCGAAGATGAGCCATTGCGCTCAATTTCAAGCACTCTTGACTCGGCTCCGCTTTCTCGTCACATTTTTCTTTCATT
TGCGCCGCATCTCGGTCGAGATTTAAGTGAAACATTGACACTTGCCGCTGTCGAAAAGTTATGGCCCACACAAATGAGGATTCCCCGCTCCCAGC
CAGGATGTTGCCATTACCGCAGGATGTATTACAGCGGGGCGGGCACAAAGGTTATTTCCACAGGGTTTTGCATTACATGAAATAGAATACCTTTC
G
(SEQ ID NO: 1309)

Exon: 2041..1001
Start ATG: 2041 (Reverse strand: CAT)

Transcript No. : CT33342
ATGGCGCTGGCGAAGACGAGTTCCGGCAAGTCCAAGTGCGGCAAGCAAATCTCCAGGCAACTCGAAACAGTTTTGGTGGACCAAAGTCCTCGGGA
AATCAGAAGAAAGAGTCAGCAGGGGCAGGAGCAGGAGCAGGCGGTGCAGGAGGCTGTCCTGCCACGTTGCACGCTGATAAAAGTGCAGCATCAGG
AGGCCGCTGTCGAGCACTTTTCGGAGGAAGGTCACAACAATATGCTCGTTAAACCAAAGTTAAAGTTGAGTAAGAAAAGTTGGCGGATTACTGGG
CCAGATCAAGACGGATTGCGCTGCGATGAAGTTGCCACCATAAATAATGGTGTCCAGGTGCAGGAGCAACAGCAGCAGCAGGAGCGGCAGCAGCT
GGGGCATGAGAAGTCAGCAAGCAGCGAGAGCGAGTATCAAAATTATCATTGCCCAACTGGGAAATCATGCAGCAGCCACAGTTACCAACTTGGCC
AGCCAGTGGCCAACAAATTGTCAACAGTCGCGATGCAGGCGCTGGCGGTGGTTGAGAACTCGGGAGGTGCATCCTTATCAGCGGGGAGCCATAAA
CAGGCGCCGGCAGCCGGAGTAAATCAGGAGCTGCCACTGGAGGCGGGGTCAATAGGTCGGCGGGAATGGCAGTTGTTGCGACATTTGAGCGGCGA
CCACCGGCTGGCAGTGTTGCAAATCTACGGCACGTTCGGCGAACGCTTGCACGTCCGCCCCCAGCTGCCCCTGGAGGGCGTGGCCTGCCTGCGGC
TGAGCGAGGAGTCCTCCACTTTTGGCCACGTCAGAGTGCACACATTTTTCTTGGCTGTCATTGCGATCGGCGGCGGCGATGAGCACGCCGTCTTC
CTGTGGCACCTAGACCACCTGCCACATGGACCCACTTTCGAGACTGTCATCGAGACTCCGGGCCACCGATTCCTGGGACCTGCTCACTCGCTCCG
GTGCAGCTGGCCGGAGATTAGGGCATCCGGCCAGTTCCTCACCCTCCGCAATCTGGCTGCCAAGTGCGAGGTGACCATCAAAAGCAGGTAG
(SEQ ID NO: 1310)

Start ATG: 1 (Reverse strand: CAT)

MALAKTSSGKSKCGKQISRQLETVLVDQSPREIRRKSQQGQEQEQAVQEAVLPRCTLIKVQHQEAAVEHFSEEGHNNMLVKPKLKLSKKSWRITG
PDQDGLRCDEVATINNGVQVQEQQQQERQQLGHEKSASSESEYQNYHCPTGKSCSSHSYQLGQPVANKLSTVAMQALAVVENSGGASLSAGSHK
QAPAAGVNQELPLEAGSIGRREWQLLRHLSGDHRLAVLQIYGTFGERLHVRPQLPLEGVACLRLSEESSTFGHVRVHTFFLAVIAIGGGDEHAVF
LWHLDHLPHGPTFETVIETPGHRFLGPAHSLRCSWPEIRASGQFLTLRNLAAKCEVTIKSR*
(SEQ ID NO: 1311)

Celera Sequence No. : 142000013384809
CTTTCATTTCTTTGGATCGGACAGCGTGTGCAACGTGTCACACACGCACAGAGTCTATACGCGTCTCACTCGCACTTGTCAGAGTTGCACTAGAG
CTGCTTTGGTAGGCGCTGCCGCGTTTGCCACGCCGATAGGAGGATAGTACCTCTTAGTTTGGACGAACTTTCTTTTCAAGGAGTCTGCGCACTGA
AATCCTAGCCACGAGTTTCATCCCAGAGCCGCAGACCAATCCGACTTACCTGCTTTACAATGCCGGACAACGACTTTGTAGGCGCTGGCGGGGCG
TCTTTAGCTGCTCCGGCAGCTGTCGCGGTGTTCGCTGCTGTTGCCATTTTTTTATTGAATGCGGGGGAGATACTAGCAGAGGGCCGTGGCACTAG
GCTTCAATAGCGGAATATTGCGTTGATTGCGTTTCGGAGCTAAACACCGCTTTCAACCTAATGAAGTTTGACCAAGAGAAGAACCGCTCTCAAAA
TCTAAAAAATTTTCACTGAAGTGACACTGCTAGCTAGAGCTGAGAAGTCAGCGCGATAGCATCGATATTTTCGTGACACGCTTGTCATCCGATAG
GTAGTGCTAAACATTTTTCTTAATTGCCAACTTAATTTACAAAAAATATGAATGACGGTAAAATTGAGAGGGATTTGGGATCCTTTATATTGGGA
ATTTTTATATATTCATATTTATTTTAATTGTATTTATGCGTAATTTATCAGACGAACTTTGGAATTTCCAATAATTCTAGATTTTTTTGTTTCAT
TTCAAAACTAATTTTAATTCGCTTAACGAGTGCATATCTATATTATGTTTACTTTAAATTTATCTGTGGGGGCAGCCTTAGATGTTCACATTGCA
GGCCATAGTGTCGATAGATCCAGGCGCCAAAAGAGTATCGCTATCGATAAATGGTCGCCAGCTGTTCGGCGAATGTTACGTGATTTCCTATTTGT
AACATTGCTAAAAATCGAGTAAAATGAATCAAGCCGATGTAACAAAGCTCATGTCACAGCTGCGTATAGCGGTCAGGCCCAACAAGCGCCATCTG
AAGAATGTCGATGGCCCGGAAGGTCGGCTGCTGAAGCTGCGTAAGACCGTCACTGCGTTGGTGAAGCACGAGCGTATTGAACTGTTCTACAACCG
TGCCGATGAAGCTCGTGGCTACGCCGAACTGGTAAGAGACCACCGGCGATACGCCAAAGGCTGGAATCCAAATAAAGTTTCCTCCCCTCGCAGCT
CATTTCCAATGCCATACGCCATGGGGACCGACACCAAGCCACCATGGAACTGGCGGACTATTGGCTGCTGGAAAAGCAACTGGTTCATAAGCTCT
TCAAGGTGCTGGTACCGCGCTATGAGACTTACAATGTGTCCTACACTCGCATGTACAAAGCCCCTCGGGAGTATCCTGGCATTTACTACAGGCGG
TCTGTGCTGGAGCTTCGGGGCAATCCCTACCCTTCGCTGGCGGCGGATCATTCTCAGAACCGGAATCTGCTGCACAATGTGCTTCTGGACGAGGC
GAGAAAGGAGTTTAGGCGTCAAAAACTGTCGGAGTTAGTTCACTAATAGCTCTTTTCACTAACCGCCTGTTTATTTAGTAGATTAGCAAGCAGTT
TGTCGCTTAGAATTCACGTAAGACTTAAAAGCATCTTTATTATAAATGTATGTATACACAAAACGAATTGTTTGAATTAAGAGTTGAACTTATAC
AAACGACTAAAGTCTACTGACATTGCAGTGATTGAAGTAATCCGGTTTCCAATCTACCGAGTTAGAGAATTAGCTTTAGAATGATTCAATTTCTG
AACGGATAACTTACCCTTTCCCGTAAGGCAGGCATCCAGCAACATTTCACAAATGCTGTAGAAGAATTGGTGCTCATTTGTCGACGATGCGCAGA
CAGGCAAAAACGGATCACAATTGGTAATAGCACTACAACCCGAGTTGCTGCTCAATACTGGCAGACATACGGACAGCGCGAGGAACATTATGATG
TTGAAGATCAGGAACCAAGCCAAATAGATATTCATTTTGGATGAATTCGCAGAATTATCATTCACTAGCGTATTAAATGACATCGTCACCTAAAA
ATTATTTCATAGCAGCAAACAGATTGGGAGCGAATCTTTTTTCGCAGATCAATCTTTATATGTATATATTTTATTTATTTTGAAATATGATCCGT
TAAAGTTCCTCTTTACGTTCCATTCGGTCACAGAATGTAAATCCGAATTTGGCTGCCGACATGAACAGCCATCTAACAACTGATAAGCACTGGGG
GACCTACGCGCTGATGCATACTAATTCGCTCATGTTCCTGAACCCCAAAGTTACCATGGAAACGAGCTCGGAACACTGACCAATGAATCAATGAT
AACTTCACCTCTATTTTTCACCGGAAGCTTTTGTTCGTTTCCTCCCAGACTTCGGTATGAATGGGGTTGCTCAACTGACTGGAACCCAGCGTTCT
TTGTAGTTTCGCGTACATTTAATCCGGCCGGCCCCGATATGTTTGTAAACTAGTGCAACTTTGCGGATGAAATGGTGTTGGAGAGCATGTTTGAT
A
(SEQ ID NO: 1312)

Exon: 1001..1171
Exon: 1234..1566
Start ATG: 1001

Transcript No. : CT33407

ATGTCACAGCTGCGTATAGCGGTCAGGCCCAACAAGCGCCATCTGAAGAATGTCGATGGCCCGGAAGGTCGGCTGCTGAAGCTGCGTAAGACCGT
CACTGCGTTGGTGAAGCACGAGCGTATTGAACTGTTCTACAACCGTGCCGATGAAGCTCGTGGCTACGCCGAACTGCTCATTTCCAATGCCATAC
GCCATGGGGACCGACACCAAGCCACCATGGAACTGGCGGACTATTGGCTGCTGGAAAAGCAACTGGTTCATAAGCTCTTCAAGGTGCTGGTACCG
CGCTATGAGACTTACAATGTGTCCTACACTCGCATGTACAAAGCCCCTCGGGAGTATCCTGGCATTTACTACAGGCGGTCTGTGCTGGAGCTTCG
GGGCAATCCCTACCCTTCGCTGGCGGCGGATCATTCTCAGAACCGGAATCTGCTGCACAATGTGCTTCTGGACGAGGCGAGAAAGGAGTTTAGGC
GTCAAAAACTGTCGGAGTTAGTTCACTAA
(SEQ ID NO: 1313)

Start ATG: 1

MSQLRIAVRPNKRHLKNVDGPEGRLLKLRKTVTALVKHERIELFYNRADEARGYAELLISNAIRHGDRHQATMELADYWLLEKQLVHKLFKVLVP
RYETYNVSYTRMYKAPREYPGIYYRRSVLELRGNPYPSLAADHSQNRNLLHNVLLDEARKEFRRQKLSELVH*
(SEQ ID NO: 1314)

Celera Sequence No. : 142000013384809
GCACATACACACAAGTGCACGCACTGCAGTCGATTTTGTTTTTTTGCATAAAACTTTATTTCATGTATGCCACTTGTACATTGTTTGTCACCAA
TTTGCGTATTTTGTACATCAAATTTTATTTTACTTTTCGTTGCCTTCCTTATTATTTTCCTAATCTTCACATGCACTTTTTTAGCGACGCCAACA
CACACATTTGCACACGCACACACATGGCGAGGATGAGAGAGGAGAAAGAGAGCAAAACACCGTTTTCGTTGCTTCCTTTTCGCTTATTCCTCTTT
AGCCGCTTCTTTTCGATTCTGGCTCTTTTTGGCACTTTTAGCCCCAAGTTGCTAGCAATTCACTTAGCGTACGAGCACTAACAATTAAAACGAAT
AAGACTCGAAAAATACGATGGAAACGCGAACATATAAACAAAAATCTACATTGGTTTTATTGCAGCGCTACGCAGGTGTGTTTTTACGCGCTCAT
CGCGCAATTAAATTAGAACGCTGCAGATTTACTTAGTTCACTCCAGTCTGCCCAATGCGCGCCGCACACCTCGGAGCCGCAAATTATAAACACGA
CTGTCTTCGATTTAACGGGCTGGCCTATCGGTCCTATCGATGACTCGATAGTGCGAGCTGGAGTGTGACCATTTCTTGGTAAAAGCAAAATCGTG
AAGAGTAAGTGTGCGATACTATCGAACTGTCATATACTCAACCAAATAACATCTGAAATCTGTTTCTCACTAAAACCGAAATTTCCATCAGGGTT
AGGAAAATATAGTTTACGCACATCAAGTTGCATAGGTCAATCCTACGTAAAAAAGGCTCGATATAGGTAAGGTGGACCTCAGCCTGAACAGGGCC
TAATGCAAATACATTCGATAAATAGATGTTATCGATAACCATTTGGTATATACCAGTAAATGCTTTGTTTTGGTTTTCATTCAGAAAATTGACAT
ACATTTCTTAGTCTGCCTAAAGTTCCTTGGATTGAAAAGAGCAGTGCAGAATGTCGCACCGCCACCAGGACATTCCCATCCGCCCACGTTACGGT
TATGTGGCCGAGGAGAGTGGCCCATCGGAAGGGGCAGCCAGGAGTTCTGGATCCGGAGCCACGCCCGCCTCCTCCTACACGGAAATTCCGTTCCT
GGCTCAGTATCCGGGAGCGGTGCCAGAGCACGTGCTCCAGGATCTGACGCCCACAGCCACTGGCCATGCTGCGATTCCCGGAAGCACAAAGACAA
GACCCAACGGCGAGAAATACCTTAACCTGGATTCGGGCGAGGATCCCGACGAGGAAGACGATCCCTTGGAGGAGGAGGACAACAGCAACTCGAAT
AGCAACTCTAAGGGCAGTTCCGGCGACATCGAAAGGCACAGACTGAAGGCAGAGAGCAGTGGGTTCTAGGTTATCTACCCATAGTTCCTGACTAA
AGCATCTTCCTTCTTTCAGCTGTGCCCTACGAGCTGGACGGCGAAACCAGTGACTCCGACGGGATGCGCCACTTTGTGGCCCACGATCTAGAGGC
CAAGTTGCGCGAGCGCGTGGCGGCTTCGGCCTACTCCTCGGAGCACACCACGCCCCTGAGCTCCATGGGTCCCATTGGAGCCACTTCCGGCAACG
GTCTGCTCACGCGGCGGTTCCTGCAGTCGCGCAACATTCCCGAAGTGGACGGCAGCGTCTTGAGCGACATCGAACTGGAGGCTCAGTACTTGGCC
AGCTCGGTGGACAATCTGATGGAAAACCTGGGCAACCTGCTGCACTCAATCTCCTCCATAACGGCCGACAACGTGGAGGTCCATCGCAACGCGGT
CAACAAGCTGACGGACACTTTGGACGCGAATATCAAGTGCCAGTACCAATTGCTGGCCAAGGCGGAGGAAATCACCAAGTCGATGAAACCCCACAG
AGCAGCTGGGTCAGCGCATGTAAGTGGGTCAATTCAAGACAGATCCCTTTAGTGTAATGGACTTTCTCTTCCGCAGAAGGCAGATCAAGCGGCTG
GTGGACATGTTGGACAGCACCATGTAAAATAGGGCTACGCTATCCTGTGATCAACCAATCAAAGAGATCTTGTCTTTCTAGTCATTCCGTAAATA
CATATAATCAGTGTTATAAAATCCATATGGAAAGATACCTTTCGCTTGTTTAAATCGTACTTATTCTAGCAGTTCCTCCAAAAAATCCACCTCCT
TGGCTCACAGCTTCTCCACCTTGGCCTTGATGATCCTTAGGGGATCCACGGGGCGATCGTTCTTGTCGGTTTCCACCATGCCGATCCGCTTGACC
ACCTCCATGCCCGTGTAGACCCTGCCGAAGATCGTGTGCTTGCCATCCAGCCACTGCGTGGGCGCCAGCGTGATGAAGAACTGGGACCCGTTGGT
GTCCGGTCCAGAGTTGGCCATCGAGAGGATGCCCGCGCCCGTGTGCCTCAAGTCGCCGTGCAGCTCGTCCGCGAACTCCGATCCGTAGATGGAGG
CGCCTCCGCGGCCAGTGCCCGTGGGATCGCCGCCCTGGATCATGAAGTCCCTGATGATCCGGTGGAACACCACGTTGTTGTAGTAGCCCCTTCTC
GAGAGTTCGGCAAAGTTGCGGCAGGTGTTGGGCGCGTGTTTCCAGTACAGCTCCACGGTGATTTCTCCCATGCTGCGCGGGGCACAAATGCCACA
AATAATGTGATAAACAAATGCTCAGTCTTCAGTTTCGGCGATTATCGAGCATTCAAGCTCCGGACTCACCTCGTTTCCAGGGTCACGAAGTGCGG
CTGCCACGCCTTGTCGGGAATGCCACCAGCATTGTTGGGATCGCTTAGGGACAGCATAACTATATTTGTTGTTAAATTAGCGAGACTTCAGTAAA
ATTGTTAAAACCGGCAGAGTCAGAGTGACCAGCTTAAGCGTAGTCACTTAGGCCGCCTGGCAACCCTGAACTGCTGCGGTATACTTCTGGTATAT
ATATAGTATAGTATATAGACGCACCTTGGTATTTTTTAGGGTTTTTGTGAGCACACGCAAGGGTATTTTTCAATTAGTTCCATTTCAAAATTCGA
CGAAAAAATCGTGGAAAATATTTAGCGGACGGAATTTTTCGTCGGGCTCGCGAGAAAA
(SEQ ID NO: 1315)

Exon: 1001..1388
Exon: 1445..1919
Exon: 1977..2098
Start ATG: 1001

Transcript No. : CT33418
ATGTCGCACCGCCACCAGGACATTCCCATCCGCCCACGTTACGGTTATGTGGCCGAGGAGAGTGGCCCATCGGAAGGGGCAGCCAGGAGTTCTGG
ATCCGGAGCCACGCCCGCCTCCTCCTACACGGAAATTCCGTTCCTGGCTCAGTATCCGGGAGCGGTGCCAGAGCACGTGCTCCAGGATCTGACGC
CCACAGCCACTGGCCATGCTGCGATTCCCGGAAGCACAAAGACAAGACCCAACGGCGAGAAATACCTTAACCTGGATTCGGGCGAGGATCCCGAC
GAGGAAGACGATCCCTTGGAGGAGGAGGACAACAGCAACTCGAATAGCAACTCTAAGGGCAGTTCCGGCGACATCGAAAGGCACAGACTGAAGGC
AGAGAGCACTGTGCCCTACGAGCTGGACGGCGAAACCAGTGACTCCGACGGGATGCGCCACTTTGTGGCCCACGATCTAGAGGCCAAGTTGCGCG
AGCGCGTGGCGGCTTCGGCCTACTCCTCGGAGCACACCACGCCCCTGAGCTCCATGGGTCCCATTGGAGCCACTTCCGGCAACGGTCTGCTCACG
CGGCGGTTCCTGCAGTCGCGCAACATTCCCGAAGTGGACGGCAGCGTCTTGAGCGACATCGAACTGGAGGCTCAGTACTTGGCCAGCTCGGTGGA
CAATCTGATGGAAAACCTGGGCAACCTGCTGCACTCAATCTCCTCCATAACGGCCGACAACGTGGAGGTCCATCGCAACGCGGTCAACAAGCTGA
CGGACACTTTGGACGCGAATATCAAGTGCCAGTACCAATTGCTGGCCAAGGCGGAGGAAATCACCAAGTCGATGAAACCCCACAGAGCAGCTGGGT
CAGCGCATAAGGCAGATCAAGCGGCTGGTGGACATGTTGGACAGCACCATGTAAAATAGGGCTACGCTATCCTGTGATCAACCAATCAAAGAGAT
CTTGTCTTTCTAGTCATTCCGTAAATACATATAAT
(SEQ ID NO: 1316)

FIGURE SHEET 702

Start ATG: 1

MSHRHQDIPIRPRYGYVAEESGPSEGAARSSGSGATPASSYTEIPFLAQYPGAVPEHVLQDLTPTATGHAAIPGSTKTRPNGEKYLNLDSGEDPD
EEDDPLEEEDNSNSNSNSKGSSGDIERHRLKAESTVPYELDGETSDSDGMRHFVAHDLEAKLRERVAASAYSSEHTTPLSSMGPIGATSGNGLLT
RRFLQSRNIPEVDGSVLSDIELEAQYLASSVDNLMENLGNLLHSISSITADNVEVHRNAVNKLTDTLDANIKCQYQLLAKAEEITKSMKPTEQLG
QRIRQIKRLVDMLDSTM*
(SEQ ID NO: 1317)

Celera Sequence No. : 142000013384809
TATGGCGAAACTTTGCCGCAACCGGAACGGATGGCGATGTAGCAATGGCGATGTGGCGTATCCAACGCTCCATAGACCCGGTTGTGTAATCGTAG
CGCCCTCAATCGACACTGCGACAAAAGTTTAATACACTTTCTACATATTTCCGATATGTCTTGACTTAGCAACTTCATAACTTATAATGTAGCTA
ACAGGTATATATATTTATCTTAAATACTATATAACAAAACCAACAAGCGATTACGTTTCTTTCAGTGCACTTACATATATGCTCTGCAATCTGTA
GGTGCGAGTGTGATTGTGAGTGTCCACCTTCTGGCACCGCAAGGTCCCTCACCGGGATGCTGCGCTGCTGGCATCCTCTTCCCCCATATATCCTC
AGCCCTTCGGACTTCGCCCTCCGCAGCCCACCTCCGGGCTGTACTCCCATCTAGAATTGATGTAGCACCTACGGTGCGCCCTCTCCATCTGCCCA
CTTCCGGAGCTTCTGTTCCACGCACGTTCAACTTCAACTTCGTTGCAGGTCATTCGGACTCGTTCAGTCTCATCCCACATCCCACCATCGCGTAA
AGTTTTAGAGGACGAACGTAAAGTTTTAGCGCTGATTGTTAGTCTCGCTGGGGCGAGTGGAAAGTTGCCTTATAGCTTGGAAACCTGGTCAAAGA
CCCAGATAGCCGTGCCATGAGAACAGATATATGGGTGCATCACCTTGACAATGTCAATCTTTGTTACTATTCAAGTGAACGGTGGGTAAACGTAT
TCGTTTTGAAACATGTTATTCAAGAACAATTACATAATATTTATATTCATTTTATATGCGTGTTTGAAGCTTGTATTTGATTTACAAATAGTTAG
TTTACGCTTGCTTGTTTGTTTTAAATTAAATACACATTTTCAGTGAAATAACGCAGTTTTCATAAAGCCTATCTTATACCCTGCAGAGGGTACTC
AAAGATCTAAACATACTTATAACCTAAGGCACATGTTTTTGGTTTGGTACTTATTCTAAGGATTTGTCCATTTCCTCACTCTTTTTCGCAGCGGA
CTCAAAGATCTTCTCCAGCTGCGTGAGCAGGCCAATGGCTCGATAGTTCTCCTCCATTAGGACGAATTCCTCCAGGGGCTTCAGTAGACGCAGTG
CGTCCTTGTAGCTTTCTACGCAGCGCGGCAGATGTGCCTCATCGCTGGTCTCTGAATAATGACCGGGACTATTGGCTGGAAGTAGTTCCGTATCC
TCAGGCAATGACTCATTGAGCGATTGAATCTTCTGAATCTTCAAGCCACATGGTATTGGGCCGCCGTTCTCGTCTGATTTTCGTTTAGTAGCCCT
TTCTGGCAAATCCTCATTATCATTATGCTCATCGTCATTATCCTCATCATCCTTTATTTCTATGAGCTCAGGTGGCACTTCAATGGCCACGCAAT
CATCGTCTTCTTCGTGCTCAAATTCTTCGGGTTTTGGTTCCACCTGTGGGCATTGGTCCACCTCTGGCTTGTCGCTCTGGCTCAGTTCTTCCTGC
GACTTCTTGTGGTCCAGCGTGATCTTATGTTCATTCCGGCCGCAATAACTAACTATATCTCTTAGGTCCAGGGAAAGCGGCAAGCGGCGGTTCGT
CACCTGAACTCCCACCGTGAAATTAAAGTTATAGCGACTCTTAAAGTGCTTCAACCACACTTTGTCGGGAAAGAAGGAGTCGATTTTGAGGATGT
CCCTTAAACTAATGGCCACAAAGCGCAAATTGTCTAGGTCAAGACGACCCTGGCGAACCAACTGTGATCGCTGGATGTACTCATAAACGCATTTC
TCCAGGAACGCTAACTTTCGCTTTCTACGCAGGTGCACTTCATCCGAGGTGGCTTGATTTTGGCTAGAGGTGGTGACCAATGTCTTTGTACGATA
AAGAGGTCGATCACTGCTAGTGAGCGCAGGTTCCGGCGATCTAGGCGCTAAGCTACAAGACATCGAGGTGTGTCGTCCACAGTACGACATAATGT
CCCTCAAGTCCATAGATCGTGGTGGTCGGCGGACTATCGTGATCTGACGATTCGACAGTGTTATATTATAGGCGGCCTTGAAGTGATTGATCCAC
GGTTTGTTCGGCACAAAACCATCGAGTTGCATGAGATCCCGGAACTCGATCGCACGGTTGCGGATCATCTCCTCGTTCACATCGCTGTGGAGGTA
AAACTGGGCCCTCTGGATGTACTCGTACAGGCAGTGGCCCAGAAAGTTCAGCTTGCGCCGGCGCAGCTCGGCATCCTTATTGGCCGGCTGGCTGA
GCCGATTGGTGGCCTTGTGGAACTCCAGGATGGCTTCCCGATTGGAGACTATGCTCTTGATTTGCTCCCAGCTGCAATTAAAGTTCCTCGCAATC
TTACTGTACATGGGCACAATGTCGTACTGTCGGATGGCAGCCACACGCTCCTCCAAAGTCAGCACGTTCCGTATGCGATGCGATCCATTCGAGTT
TTTGTGGGTGTCATCATTCTGAAATTGAATCATGGTTTATTTCTTTATAAAATCCGATTTCTAGGCTTAGTTACATGTATGTTATTGATACAGAA
CTCAAATTATCTGTATGCGTGTATATCATGAATGCCTTATACATATTTATGTATGTATATTTACAAAACATGCCCTCTTCTTATTCGCAAATGGG
TCTCGCATATTTTAGCTCAGAGATAACAAATTTCAAAAGATTTTACTAAAACGAAGCATTGCACTCTCACTTACTCACTACGAAAGTATACTTAC
GTCAGAGTACATTTCCACTCCCGCTCTCACACTTTCAGGTTCTCCACTCTCTCTTAGCGTGCTCGCACTCCCAGTCTGGCCCCCCCTCCTCACGT
GACCAATATAATTCTGTTCCTTTAACAATGAAATTAAAACGAAATAGTTATTATACAGAGAAGAGCTAGAAATCTTGTTTACATACCTCAGTCGG
AAAGCTTAGAGCATAAAGTACACTTTGTTGAAAATATACAGCAGTTTTTAGGCACATTAAACAGAAAATATGTGCGGTCGCACGTGTTTAAAGT
TGCCAGAGCGAGTGCAACTCAATGACTGAGCATGCGGTCCGAACATTGCAGAGATCTGGACTCTCCTCCGTTTGGCGGAGCGGCAAAAACCGTAT
CTTTGCGAGAGACATTCCGCTCTTTCTCTCGCGATCTAAACCGACTTCCCACGTTCCGATTCCGATCGTGGTGGTATTCGTTCGCGGTATGGGAT
TTATTTTCGGATCGAGAGTAAATATTCTCTCGCTAAAGCAGCTATAACTGGTTTAACATGCCGAAAAACACAAATCGCATTACCACCTAATCTGA
GCTGAAACTGGTTTGATATGTACACATACATATATATAAAGCTATTTTTGCTCAAATTATATCTAGTGCTTAATTTAACGTTTACCACATTTAAG
TGGGACCCTGTTGGTTATTCCACTCTATAAACTCTTTTCGCATATTACAATTATTTACACATTTTGGGTCTTGACTCTCAAAGGCAGGACACACG
AACATTTTAATTGTAGATTACATATAAAAACTAAACTTTATTTTTGTGGCGTCAATAAGATCATAGATCGAAATCCTCGTTCTGAGGCGGATTTA
AAACTGATTTTTCAACTTCAGTAAGTAGTCCAATGGCCCGATAGTTATCATTTAACATGGCGTACTCCTGTAAGACCTTCACGTAGGCCAAGGCC
ATATTTTTACAGTCGATGGATTTCAGTGAATTTTGTAAGGAAGCGACTACTTTGGGGTCCAC
(SEQ ID NO: 1318)

Exon: 2767..2756
Exon: 2488..1001
Start ATG: 2767 (Reverse strand: CAT)

Transcript No. : CT33430
ATGTACTCTGACAATGATGACACCCACAAAAACTCGAATGGATCGCATCGCATACGGAACGTGCTGACTTTGGAGGAGCGTGTGGCTGCCATCCG
ACAGTACGACATTGTGCCCATGTACAGTAAGATTGCGAGGAACTTTAATTGCAGCTGGGAGCAAATCAAGAGCATAGTCTCCAATCGGGAAGCCA
TCCTGGAGTTCCACAAGGCCACCAATCGGCTCAGCCAGCCGGCCAATAAGGATGCCGAGCTGCGCCGGCGCAAGCTGAACTTTCTGGGCCACTGC
CTGTACGAGTACATCCAGAGGGCCCAGTTTTACCTCCACAGCGATGTGAACGAGGAGATGATCCGCAACCGTGCGATCGAGTTCCGGGATCTCAT
GCAACTCGATGGTTTTGTGCCGAACAAACCGTGGATCAATCACTTCAAGGCCGCCTATAATATAACACTGTCGAATCGTCAGATCACGATAGTCC
GCCGACCACCACGATCTATGGACTTGAGGGACATTATGTCGTACTGTGGACGACACACCTCGATGTCTTGTAGCTTAGCGCCTAGATCGCCGGAA
CCTGCGCTCACTAGCAGTGATCGACCTCTTTATCGTACAAAGACATTGGTCACCACCTCTAGCCAAAATCAAGCCACCTCGGATGAAGTGCACCT
GCGTAGAAAGCGAAAGTTAGCGTTCCTGGAGAAATGCGTTTATGAGTACATCCAGCGATCACAGTTGGTTCGCCAGGGTCGTCTTGACCTAGACA
ATTTGCGCTTTGTGGCCATTAGTTTAAGGGACATCCTCAAAATCGACTCCTTCTTTCCCGACAAAGTGTGGTTGAAGCACTTTAAGAGTCGCTAT
AACTTTAATTTCACGGTGGGAGTTCAGGTGACGAACCGCCGCTTGCCGCTTTCCCTGGACCTAAGAGATATAGTTAGTTATTGCGGCCGGAATGA
ACATAAGATCACGCTGGACCACAAGAAGTCGCAGGAAGAACTGAGCCAGAGCGACAAGCCAGAGGTGGACCAATGCCCACAGGTGGAACCAAAAC
CCGAAGAATTTGAGCACGAAGAAGACGATGATTGCGTGGCCATTGAAGTGCCACCTGAGCTCATAGAAATAAAGGATGATGAGGATAATGACGAT
GAGCATAATGATAATGAGGATTTGCCAGAAAGGGCTACTAAACGAAAATCAGACGAGAACGGCGGCCCAATACCATGTGGCTTGAAGATTCAGAA GATTCAATCGCTCAATGAGTCATTGCCTGAGGATACGGAACTACTTCCAGCCAATAGTCCCGGTCATTATTCAGAGACCAGCGATGAGGCACATC
TGCCGCGCTGCGTAGAAAGCTACAAGGACGCACTGCGTCTACTGAAGCCCCTGGAGGAATTCGTCCTAATGGAGGAGAACTATCGAGCCATTGGC
CTGCTCACGCAGCTGGAGAAGATCTTTGAGTCCGCTGCGAAAAAGAGTGAGGAAATGGACAAATCCTTAGAATAA
(SEQ ID NO: 1319)

Start ATG: 1 (Reverse strand: CAT)

MYSDNDDTHKNSNGSHRIRNVLTLEERVAAIRQYDIVPMYSKIARNFNCSWEQIKSIVSNREAILEFHKATNRLSQPANKDAELRRRKLNFLGHC
LYEYIQRAQFYLHSDVNEEMIRNRAIEFRDLMQLDGFVPNKPWINHFKAAYNITLSNRQITIVRRPPRSMDLRDIMSYCGRHTSMSCSLAPRSPE
PALTSSDRPLYRTKTLVTTSSQNQATSDEVHLRRKRKLAFLEKCVYEYIQRSQLVRQGRLDLDNLRFVAISLRDILKIDSFFPDKVWLKHFKSRY
NFNFTVGVQVTNRRLPLSLDLRDIVSYCGRNEHKITLDHKKSQEELSQSDKPEVDQCPQVEPKPEEFEHEEDDDCVAIEVPPELIEIKDDEDNDD
EHNDNEDLPERATKRKSDENGGPIPCGLKIQKIQSLNESLPEDTELLPANSPGHYSETSDEAHLPRCVESYKDALRLLKPLEEFVLMEENYRAIG
LLTQLEKIFESAAKKSEEMDKSLE*
(SEQ ID NO: 1320)

Celera Sequence No. : 142000013384692
CACTTAGACACTTCGCCCATCGTTCTGGCCTGTCAGCAGAATCGCCAGCCAAGACGACACTCGTGTATCGAGTGCAATAATCATCACTGCTCCCC
CACGAGTGCCGAATTTCGAATGCCGCCTTTTCTGTGGACCTCAGCACTTTGACATTGCCCGTTTCCCTTCCAGGGCGTTGCTCGCCAAACGTGGC
TAATCTGCGCCCTTCGATCTCCAAGGCATTTGCTGAAAATTTATTAAGCTCTGCCAAAATGCATGGGCAGGGTGCTCAAAGTAGTTGAACCAGTT
GAAATGGCTGAAATGCTACTCGAAATAGAGGATAATAGAATAAATCTTTAAGTTCATAAGCTTTGATTAGGCATACTTATATAAAGTGCTAAGTA
TTAATCACATTCCAATCATAAATCATTTAAATAACTCGAATTAGGCTTTTACTTAGCAATTGTATATATCGAATTTCCCAAGTTGCATCTTTCAA
TTGGTTCAAATTGGCATCGTTGAAAGTCTTGAAAACTTTACGCCCAAAAGAATTGATTTGTTTTCATTTCATTTTTGCTGTGTTCCTCAAGAAAT
CATTGAGCCGGGCTCCACTTGCCGAAACTTTCTGATAACTCGTAACTTGTTACTCAGCGCACACAGCACTAATGAAGACGGCACACACACAACAA
ACACAATAAGGGGTGTCTTGTTGGCTGTTTGTTTTCCACTGGCCAAGAGCAGAGCACCGGTCACCAGGGAGCAGCAGGCTGATTCAAGTGTTAAA
ATCAATGGGATTCACAGCTGAGTGCAGCTGAAGCCCCTAAGGGGGCGGTCAAGACGTTCCTCGATTTAATTGAATAATTGTGAGGCAGGCCACGT
TCGCCGAATTCCTGGTAAATCAGCGAAAATTCCGTAACTAAACAGAAATAGAAGCCAGTCGTCCAGAGAGAGAGAGAGAGAGCGCCCCAAAATAGGC
AACAAAGATGGGGCACAAAAGCCCGGGAAATCTTCAGCCAGGAGACTGCGTCAGGCTTTGTTTTTCGGTCCCGATGCAAATGCAGCTGCAGCTGC
AACACCTGCCGAAAACCCCGCCAGCAATTTATGCGCCGCATTTGAAATTCGGTGATACCAAATCCTCGAGACTTACCGTTCCCAAGTGGCACATT
CGTTTGCGTTGTTGTCGATTGTTGCTGTTGCTGCTGCTGCTGCTCGCTTGTCACCGCGTTGGACAATTTATTTGATGTTGTCGCTGTGGCCGGAA
CTGGCACCGCTGTGGTTGTGCTCGTCGTTGCCTCCAGCTTGCTTGCTCCATTAATGGCCACCGTGGTGGCGCTTTTTCCCAGCCTTAGTATGGTG
GTGGCCGTAGATGATGTTGCTCCGGCTGATGAGGCTCCCCCGCTAGTGGCTGTTGTGGCTGCTGCCGCCTTGAGCTTGTGCAGCGCTCCTGCCAC
GCCTTTGGCCGCCTTCGTGGTGCGCGTCACGCTTAGAATACTTGAGGTGGCAAGACTGTTGCCATTTGGTGGCGAAGTGGCCATGGAAGTGTTGG
TTGCAGCGGTCGACGCCGTGGAGTTGCGTATGACCAGTATGGATTGAGACTTCTCCAGACGCTTCAGCGTTTGCAGCACAAAGGGTGACTTGCTG
TCGCAGTTGCTCTCGGAACTCAAGCTGCGTGTGGCCTGTAAAAGTGATGGAACAAGTTGGTAAAATACAACACAAATGTCACTGCACATCTCTTA
CATGTTTTAGCATAAAGGGTCTCTCCACCATCTTGGTTTGCGTGGCGTTGGCCTGCTTGGAACGCTCTTGGGCCTTTAGAACGCTCTCCAACTGA
CTGGCATTGATGGGGGTTTGCAGAAGGATCGTGTTGCTACTGGCCTCCTTGTTGTTGCTGTTGGCCACAATGGAAATGGTGGAGCTGCTGCTGCT
GCTGCTGCTGCCGGCTCCACTCGAGCCCTGCACAATGGTCTTTCTAGCCACCGTTGTGGCCGTGGGCAGCTGGTTGAGCGTAATGGCCGTGGAGG
AGTGACTTTTCTCCTGCTGCTGCTGCTGTTGTTGTTCGCTGAGCAGGCTAAGAATGTCCTGCTTGTTCTGGATGATGATCTGGCCATTTTCGTTG
CGTGTGCCGCGCAGCAGGATGATGTTGCCGCCACTCGTGGCCTGATGCTGCTGCTGGTGTTGCTGCTTCTGCTGTTGCATGGCCCCGATCTTGAG
CTTGGCCGCTCGCAGAGTCGTCGTTGTACTGGTTGTTGCTGCTGGCTTTGCTGATTTCGCTTCATTGCTGCTTAGCTTGCCACTGCTCTGCGATC
GGATCAAGACATTTTTGGAGGTGATTTGGCCTAGAAAGGAATAACAAAAGTAAATCAGTCTTAAATAATCAATTCAATGTACATACAATATATAA
AAGGTATTTATCCAGGTAAAACAACAAAATTAAAAATGTACATCCTAGAACGTCTGGATGTATAAAAAGAGTAGATCTTATTTATTTATTTGTAA
GTTATCTAAACAGCGTGTTGGTTTCATTTTTGGTGTAAGTGCTCCTGTAACATTTTGTTCTCGATTTCTCGAATTGAGCAATTTCGAGTGGCCCC
AAAAAACGGACAGCCCCATTGTATGCAAATTCAATGGAAACTTCATAAGCGGCGCAAGATTTATGACTCCATCTTGATCGAATTTGGAAAGCCTT
GCATTAGAAGCGCATGTGACAGGGGAGGCAGGAGGCGTGGCTGCCATTGTTGCACTTTCCCAGGGTCCGTAAAAATGAACTGAAAGGGACGTCGA
GCATTACGTATACGCGACGTATGCCTAGAGCGGTCAGTGGCTCGGACACTCTATTTTGTTGGCCAACAAATGGGGAGGATGGGCGGTAGCCAAAC
GCTAAATCAAGCGAAAGACGACATGTTTATGGCAGGGACGAAGGACTACTTAGCCGACGAGCCCCAGCACAAAACGCAATAAAAGTGCAACAAAC
AAACAGCGAGTTTTCAGCCAAGAAAGGAGGAGAAAGTAATGGGGTAGGTTCACGGGTGTAGGCAAATGGGGGTCTCTGCCCTGGCATGCGTTGCC
AAATATAGACTCTCAAGGCTGAAGGCGACACGGAACGTAAAGTGCGCGCCGGAAACATTTCGAAATGTAGCCTAAACACTTGTCCGGCTCCCCTG
CTTTTCCCGCCTCCCCCCGCCGCCGGCATCCAGCACCCTTTCCTGGGTATTTCCACACCCCCAAAAACCATGTGTGTTTGTTTTCGCAAAAACGT
GCGGGTCATAATTAGCCGTTGACGCCGCCTTCAGTCGGCTGTGCTTTGGGGAAAAGCGGAAAAGCAGAAAAGCGGGCAGGGGAAAGCGCCACATG
CGACCATCTGACCCCAAGTGGACAAGTGTCTGCGCCCCCTTCGCCTTCCTTGGAGTGTCTGTGCAAAAAGGTCGCCTGCCGCCAGGCAAAATAAA
CCGCCTGAATTGGACCAGGATCGGAATAGAATAGGTGGGGCCACTGGCTGTTGGCTGGCCATCCATTCGAGCGCACA
(SEQ ID NO: 1321)

Exon: 2497..2482
Exon: 2310..1712
Exon: 1650..1122
Exon: 1050..1001
Start ATG: 2497 (Reverse strand: CAT)

Transcript No. : CT33502
ATGAAACCAACACGCTGCCAAATCACCTCCAAAAATGTCTTGATCCGATCGCAGAGCAGTGGCAAGCTAAGCAGCAATGAAGCGAAATCAGCAAA
GCCAGCAGCAACAACCAGTACAACGACGACTCTGCGAGCGGCCAAGCTCAAGATCGGGGCCATGCAACAGCAGAAGCAGCAACACCAGCAGCAGC
ATCAGGCCACGAGTGGCGGCAACATCATCCTGCTGCGCGGCACACGCAACGAAAATGGCCAGATCATCATCCAGAACAAGCAGGACATTCTTAGC
CTGCTCAGCGAACAACAACAGCAGCAGCAGCAGGAGAAAAGTCACTCCTCCACGGCCATTACGCTCAACCAGCTGCCCACGGCCACAACGGTGGC
TAGAAAGACCATTGTGCAGGGCTCGAGTGGAGCCGGCAGCAGCAGCAGCAGCAGCAGCTCCACCATTTCCATTGTGGCCAACAGCAACAACAAGG
AGGCCAGTAGCAACACGATCCTTCTGCAAACCCCCATCAATGCCAGTCAGTTGGAGAGCGTTCTAAAGGCCCAAGAGCGTTCCAAGCAGGCCAAC
GCCACGCAAACCAAGATGGTGGAGAGACCCTTTATGCTAAAACATGCCACACGCAGCTTGAGTTCCGAGAGCAACTGCGACAGCAAGTCACCCTT TGTGCTGCAAACGCTGAAGCGTCTGGAGAAGTCTCAATCCATACTGGTCATACGCAACTCCACGGCGTCGACCGCTGCAACCAACACTTCCATGG
CCACTTCGCCACCAAATGGCAACAGTCTTGCCACCTCAAGTATTCTAAGCGTGACGCGCACCACGAAGGCGGCCAAAGGCGTGGCAGGAGCGCTG
CACAAGCTCAAGGCGGCAGCAGCCACAACAGCCACTAGCGGGGGAGCCTCATCAGCCGGAGCAACATCATCTACGGCCACCACCATACTAAGGCT
GGGAAAAAGCGCCACCACGGTGGCCATTAATGGAGCAAGCAAGCTGGAGGCAACGACGAGCACAACCACAGCGGTGCCAGTTCCGGCCACAGCGA
CAACATCAAATAAATTGTCCAACGCGGTGACAAGCGAGCAGCAGCAGCAGCAACAGCAACAATCGACAACAACGCAAACGAATGTGCCACTTGGG
AACGGTGTTGCAGCTGCAGCTGCATTTGCATCGGGACCGAAAAACAAAGCCTGA
(SEQ ID NO: 1322)

Start ATG: 1 (Reverse strand: CAT)

MKPTRCQITSKNVLIRSQSSGKLSSNEAKSAKPAATTSTTTTLRAAKLKIGAMQQQKQQHQQQHQATSGGNIILLRGTRNENGQIIIQNKQDILS
LLSEQQQQQQQEKSHSSTAITLNQLPTATTVARKTIVQGSSGAGSSSSSSSSTISIVANSNNKEASSNTILLQTPINASQLESVLKAQERSKQAN
ATQTKMVERPFMLKHATRSLSSESNCDSKSPFVLQTLKRLEKSQSILVIRNSTASTAATNTSMATSPPNGNSLATSSILSVTRTTKAAKGVAGAL
HKLKAAAATTATSGGASSAGATSSTATTILRLGKSATTVAINGASKLEATTSTTTAVPVPATATTSNKLSNAVTSEQQQQQQQSTTTQTNVPLG
NGVAAAAAFASGPKNKA*
(SEQ ID NO: 1323)

Celera Sequence No. : 142000013384576
CGATGGACGAGAACGTGCTGTTGCTTTACTTCGGCCAACTAAAACTGCTGGCAGGTGAGTAAAGTTGTTTTATACATACTTCAAGTAGATATGCT
AAGATATATATACTTCTTGTAGAAAAGACCAGAGACCAAGCATTCATCAACAATCCCGACGCCCTGATTGTGGTTCAGGATATGCTCTTCATCAT
GCGCCGCATTTGCTATTGCACCAAGGGAATGGGTAAAGAGAAGAACTCTCGTGGCGAGGGCGACAATATCGATGAAGGTGAAGATGCGTCATCGG
AGCCAGCAACTCCACCAACTAGACCAGAAGCAGGCGAGGCAACAAGCAGAGGAAGAGGGCGAAAGGCGGACATGTCCGAGGAGCCAGTATGTAAA
TCTAACTGATTAACTTTTCCCCCTTGAGCTAAATGTTCAAATTCCTTTGCAGCTCAAGCAACTGGAACGCTGTCTTCGCTTTGTGGAAGAAACCC
ATCGCAACATAGTGCCCGTCATGAGTCCCGAGCTTAGTCACAACTTTGAATCCTTTTGCCGAGCGATGGCCATGAGATTCCCCAACTACATTGAG
TTCGCCCAGCCCGCGCAATTTTGGCGGCAGTTTCGATCATCGGCGAAAGCTCCCAGAGCGAGCAGAAGCAAGCGACGACGTATGGAGGAGGGCGA
AGTCGAGTCCCATGAGGAGCACGAGTCGGAGAGCGACAGTGACAGTGAGCTGCCGCTGGACAGGCACAAGACCACGCCGACTGCCTCCCGTTTGT
CCCAAAGGAAAACCAGCTGCGATATGCTTGTCACCGAGCTGATTTTCCAGCCACCCGATTGGTAGTTTCAATTTTTGCGACCTTGCAAACTGAAT
TTCTCAATTATTTAGTTTTACACAAATCGAATATTGTATTATTTTGCATTATAAAATGTACATATGTATGTATCTATAAGCCAAAAATGGAATCA
AGTTATTCTTGACCTTGAAACTATTTAATAAGCCATTTTGACGTTTTGAGTTAATAATAATCCTTGCTGTACTCGCATATTTTCTCCAAAATGTT
CTTGTAGCCGCGCATAAACTCTTCGAGCACCAGCTGGCACACTTGGAGCTCGTTCAGGCCCAACTGTTCGGCTTCCGTGGCCTGGATGAGCATGC
ACTCCAGCAGAGCCGCGTTCACCGGCTGCACGAAGAGATTCCGATCCCTGCGATCGTCGTGCCGCACCGGAATGATCAGATTGACGGGCATCGGA
GGTTCCGCCGGTTGCTTCACTGCCCTGGCTGGAGTGGCGGCAGTCGCTATGGGTCGTGAGATGGGTATGGGGTTAATGTGACTACTAGCCATCGG
TGGTTTGCCAGCCACTAGGGTATACTTTGGCGGCGTCATTAGCGCCTTGCCGGGCAACGCCAAAGTGGATGCCGCCACCTGGAGCGCCTTGCCCT
GGACATCGATGCCCGCCTTGGCAGCTGCGGCTGCTGCCTTGGCGCTCATCGCAGCCGCCTTCTGCCTTTTCACAGCGCTGGAATTCTTGGCCACG
GAGTTGGGGTCCACCAACTCGCGCACCTCTGTGTTCCTGCAGCCTGCATTACAGGGTATATGAGTGCCGTAGGGTATATTTATGCTTATAGAAAT
GAAATCATACCAACGCATCGACAGAACTTGGTGCAGATGGCCATGGACTGATAGCAGTCGCAGTAGTTCTTGATGCACTGCGACCGCTTGCAGCA
GCATCCCTTCACGCCGCCTGCTCCTTGACCCTTGCCCTTCTTGCCATCCGCTTTATCCACACTTCTTTTCTTGGGCGATGGCATGTTGCTGCCTT
AATCTCTTCCAGAAACGAACTGATGACAGCTCCAACAAAAAAAATCAGTGTTGAAAGGATGGCAACCCTTATACATATAAAAATATATATGTATA
AATAAAACAGCAATATTGTGGGCACTAAACTATTAAAGCTTAGATAAAGTATTTATATGTCGTACTGGTAATAAAGTTAAAATTTGTTAAGTACC
AATCGTTTAACAAGTGTCTAGTTTATATCGTTATAACATAGATAATTTCCTTTGGTGTCTACATAATATGGCATGGCATTAAGTTATGATATTGT
TCTCCTCTACTCGTTTAGTCTACGATAATTGAAAGCTATTTTATATTATAGATGTAATAAAAAGAGTTACATTATTAATTGATATCAATTGTAAT
TGCTTTCCTTTCATATATATTCTGTGTCGAGTGATTTGGCAGCGAAACCAACTCAAACCTCTTCTCAAAATTCTCTTTTTTTGATTGGCGTTTAG
TACTTAAATTACTTATGTAATTGGAATGAAGTGCGTTGCATTTCCCGCCAAAAAACTCGACATTTGGGCGCGCGTTTTCAAAAATATCACTATCA
AAACGATATATTTATGCAGTGTGTAAATGTGTGCAGCAGAAGACTTCTTAACAGTTGGAAAGTAATTGAGTGGCCTGCAATCGTTGCTATTGCTT
CTAAAGTAACTAGGATTATCTCCGCTGCGCTCCTAACTAGTCCCACTTGGTGCGCTCCTAGCATATGGTTCCATTGAGCAGCTCGTAACAGTTGG
GCGGCGATGCTGGCGAGGCTGCTGCCGCCGCCTCCTGTCGCGTCTTCAGAAAGTTGCCCACCCAATGGGCCGTGAGATCCAGATATTTCGTTCTC
GAGCCCGGATTGTAGTCGAGGAAGCCGGCGCGTGGCATCACCTCCTCGATCTGGCTGCCATCCGGCCAGTTGTTGTAGCTGGCTATGTTGATGAA
GCCCACGTGGTTGAGAATGGCTGTCCGCCAGGCCACGCC
(SEQ ID NO: 1324)

Exon: 1794..1626
Exon: 1563..1001
Start ATG: 1794 (Reverse strand: CAT)

Transcript No. : CT33573
ATGCCATCGCCCAAGAAAAGAAGTGTGGATAAAGCGGATGGCAAGAAGGGCAAGGGTCAAGGAGCAGGCGGCGTGAAGGGATGCTGCTGCAAGCG
GTCGCAGTGCATCAAGAACTACTGCGACTGCTATCAGTCCATGGCCATCTGCACCAAGTTCTGTCGATGCGTTGGCTGCAGGAACACAGAGGTGC
GCGAGTTGGTGGACCCCAACTCCGTGGCCAAGAATTCCAGCGCTGTGAAAAGGCAGAAGGCGGCTGCGATGAGCGCCAAGGCAGCAGCCGCAGCT
GCCAAGGCGGGCATCGATGTCCAGGGCAAGGCGCTCCAGGTGGCGGCATCCACTTTGGCGTTGCCCGGCAAGGCGCTAATGACGCCGCCAAAGTA
TACCCTAGTGGCTGGCAAACCACCGATGGCTAGTAGTCACATTAACCCCATACCCATCTCACGACCCATAGCGACTGCCGCCACTCCAGCCAGGG
CAGTGAAGCAACCGGCGGAACCTCCGATGCCCGTCAATCTGATCATTCCGGTGCGGCACGACGATCGCAGGGATCGGAATCTCTTCGTGCAGCCG
GTGAACGCGGCTCTGCTGGAGTGCATGCTCATCCAGGCCACGGAAGCCGAACAGTTGGGCCTGAACGAGCTCCAAGTGTGCCAGCTGGTGCTCGA
AGAGTTTATGCGCGGCTACAAGAACATTTTGGAGAAAATATGCGAGTACAGCAAGGATTATTATTAA
(SEQ ID NO: 1325)

Start ATG: 1 (Reverse strand: CAT)

MPSPKKRSVDKADGKKGKGQGAGGVKGCCCKRSQCIKNYCDCYQSMAICTKFCRCVGCRNTEVRELVDPNSVAKNSSAVKRQKAAAMSAKAAAAA
AKAGIDVQGKALQVAASTLALPGKALMTPPKYTLVAGKPPMASSHINPIPISRPIATAATPARAVKQPAEPPMPVNLIIPVRHDDRRDRNLFVQP
VNAALLECMLIQATEAEQLGLNELQVCQLVLEEFMRGYKNILEKICEYSKDYY*
(SEQ ID NO: 1326)

Celera Sequence No. : 142000013384574
CTCTGAGAATGGAGCCAGGGGAGCGGAGAAGCCCCGCTCGGCATTCATAAAGTCGGTGGTCAGTCCACTGATGCCCTGCTTCACCTCCTTGCCAG
CGTCGCGCAGAAAGTCCTCGAAATCATCAGTCTTCTGTGCAAACTTGGTGTCCAAATCGAGTTTGGCATCCTTAGCGTCGGCGGCCAGGCGTTGG
ACAAACTCCTGCGCATCGCCAAAGTCCAACTTCTTTTGCTCGTTGGCGAAGTAGTGCTCCGTGTGGGCATTATCGTCCTGGGCACCACCACTCAC
ATTGCCAGTATCGCCACCAAGTGCAGAGTCTTCGTAGGCACGTTGCGCCTGCTTGAAGATGTCCTCGTTGGTGGCAGCGGCCTCCTTTTTCAGTT
CGTCGAAGTTCCGATCCATATTCTACAGTGTTTTGATTTCAAAATATAACACTTGTGATCAATAAGAAATTTTCACAGATGTGTTTGAATATCCT
GGCCTTCTGATTGGAACTTCGCACACACACACACGTACGCACGCACACGACACACCCACACACACACGCACAGGCACCGAGCTACAGCTGATTTT
GCCGGTTGAAATTAATATGATTTTTTTTAGCCGACTTAAGTGCCTTCTGGTGACTAAAAGGCCGCAATTCGCAGTGTTTTGTGCTCGGGAACGTT
GAATTTAATTTGAACCACAGCGACTCTTTTACAGGCGCCGTCGATGCAGACGTTTGAAAAGTTTCAATGGACCTGCGCTAGAGGTGGCACAGCGG
TCGATACTATCGATGACGCTCACAGCATAATTGCCTAAAAATGGACAAATACCTTGAACAGCCATGTTTCGAACCAAAGTTTTGATGTTGCCGGC
ATCTTTAGCCATGACATTAACCCAATGGCTCTGGCAAATTGGCTAAAATTCACGACAGCTAAAATTTGTTGTATGTATTTCCAGAAACTTCGCGC
AATTCAGTTATGCCTAATGTTTGATTTATTTGTAAACATAACAACCATGCTCAGGCCGTCCACTTGAGGCAGCGCGTGTCCTGGTGCGTTTGCAG
GCATCTAACGCAACAGTATCGCGTTCCGCAGGCGGTGCACGAGTACAACGAGAAGTTGCCGCAAACGGCGCAGAAATGCCGCAGTGGCTTTTGTG
GAGCCGGCGCTGCGGCGCTCTCGTAGTTGGGCTGCTTGTCCTTGTCCTCCTCGAGCAGTTGCTGGAAGTTCTTGCGATACTTGACGAGAAAGTAT
TCGGCGCCCTTGCGCTTGCCTTTCTTCTCCTTGCCGGTCTTCAGGCTGTCCTGGAATTTGGGCAACTTCTTGGACATGACAAGGTCGGCGTGTGG
GTCATCGTGGTAGTTGTCCTGCTCCAGAGCCTCCAAGGCTTTGCGGGCACGCCGCTGGCGGGCTGTGGAGTCCAGGACACGCTTCTTTTCAGCGT
CCTTGATGCGGTTGGATTCGCGACCCGTCATGGTTGTTTTTAGGTTTTTACTTTTGGCTATTGGATTTTATGGGTTGTGTAGGTTCTAAGCGTCC
TTGTCGTGCAGCGGAAAGCTTATCCGATCCATCAAGTCGTCCACTCGCGCCTGCAAAACTTCCACAATGTCCGTGGAGATAAACAAATGGTTCTC
GTCCAGATCCTGGATAATGAATTTGCGTCCCAGAGCCAGTTTTTCGTCCAAGTGCAGCAGGAATTGTTTCATAGCAGGATCACTGCGGGGATTGG
GTTGAATATAGCGAAACCAACGCATACCAAACGTATACCACTTACCACTCCACCAGCACTCCTTTCATAACATTTACCATGTTGCCAGCATTTGT
TTGCCGAAATTAATAAACAATCTCACCAATTCTCAGAGCTGAATGACATATTCACAGTGAAACGTAGGCTAGAGGTGGCAGTCTTTACTATCGAT
ATTTTTTTGACTTTACTTGATAATTTAATCAATAATTTCAGCATGGCAATATAATATTTACAATCAACGAAATATAACACATTGCTTTAAACCAG
CACCCGATATTAACTATATTATGTTAGTTTCACCGTCGGAAGTTTCGTACTTTAAGAAATATAGCTATTTTGCCAGCCCTATCAGTGCTACTCAC
TACGAAAAGTAGACAGAAGTAGCGGGGTATTTGCCAGTCACACGGACAAACACCAAGGCAAAAGTGTGAGGAAATATTGAATTCCAAATTAAATT
CCTAATTAAATCAGACCATAAGCACGCAATGGAAAGGCTGACCGGAAGGAATGTGGCACTACTGGTGCTGTGCCTGTGCGCCGGATACGCCCTGG
TGTTCGCCGAGGGCGAGAAGGAGATACCGGTTACCAAATTCGGACAGAACATAGCGCCGACGATGACTTTCCTTTACTGGTGCGTTATATGCGGG
GCAATTAACATAATTGATAACAATGACCTCTGTGTTTCTCACCATTGATTCGCCAAATAGCTACTCCTGCGGCTATCGCAA
(SEQ ID NO: 1327)

Exon: 1456..1001
Start ATG: 1456 (Reverse strand: CAT)

Transcript No. : CT33597
ATGACGGGTCGCGAATCCAACCGCATCAAGGACGCTGAAAAGAAGCGTGTCCTGGACTCCACAGCCCGCCAGCGGCGTGCCCGCAAAGCCTTGGA
GGCTCTGGAGCAGGACAACTACCACGATGACCCACACGCCGACCTTGTCATGTCCAAGAAGTTGCCCAAATTCCAGGACAGCCTGAAGACCGGCA
AGGAGAAGAAAGGCAAGCGCAAGGGCGCCGAATACTTTCTCGTCAAGTATCGCAAGAACTTCCAGCAACTGCTCGAGGAGGACAAGGACAAGCAG
CCCAACTACGAGAGCGCCGCAGCGCCGGCTCCACAAAAGCCACTGCGGCATTTCTGCGCCGTTTGCGGCAACTTCTCGTTGTACTCGTGCACCGC
CTGCGGAACGCGATACTGTTGCGTTAGATGCCTGCAAACGCACCAGGACACGCGCTGCCTCAAGTGGACGGCCTGA
(SEQ ID NO: 1328)

Start ATG: 1 (Reverse strand: CAT)

MTGRESNRIKDAEKKRVLDSTARQRRARKALEALEQDNYHDDPHADLVMSKKLPKFQDSLKTGKEKKGKRKGAEYFLVKYRKNFQQLLEEDKDKQ
PNYESAAAPAPQKPLRHFCAVCGNFSLYSCTACGTRYCCVRCLQTHQDTRCLKWTA*
(SEQ ID NO: 1329)

Celera Sequence No. : 142000013384645
TTATCTGATTTGTCACACCTGCCTGTTGGAACCGCATACTCATATAAGGGTTAATCTTATCAGAGGCCCACCGTTGTTGCCACCGCCTTTCAAAT
CAAATCAGACCGCTTTGCCATAGTAATGGTCTGGCAACAACAAATGAGTATCGCTACATGGAAATGTGCGCGTGTGTGTGAGAGACCAACAACAA
AACAAGAAAACAAGCAAACGCACGAAGAAAGTTGTGAAAATTCAATTTTCCAATGGCCCAGTCTGATTGGGACTGCCTTGAAGCGTCCTCTAATC
AGATAACTATCAATGTAAATGCGTAAATATCAACGCATATGCGTTGTATTTGTGGAAAATATTACGCTTTAACCACATATACACACACCCCCGCT
TCCGGTGGGTGTTTTTTTACGCTGGAGGGGGGAGGGTGGTTTACTCACCTATGCGCTGGCCAACTGGAGTGGAGAAAACATTTCCCAAGGCGCC
AACGTTGAAAAATGAAGCCATCGTGGAGAAGTTTCTTATTAATGCTCGCCGTTGGGTTGCAGTGCGGTTAAAATTGTTCTTTATTTACTTTTTGT
TCACCTGGATGAAATGTTTATGCACTTGTCTACAGCAGAGTGACCATGGCTGGCCTCAGCGAAAAATACCCACAAAGAAATGCATTACAATAAGT
GGGTAAATAGGAATAGGTTTTTTCCAGGGCTGCAGCATTTTATTTCATTTTATTTAAAAGAATTATCCACAGTTTTTGAGATAATGACATAGTT
ATACCCGTTACTCGTAGAGTAAAAGGGTTTATTAGATTCGTTGAAAAGTATGTAACAGGCAGACCATATAAAGTATATATATTCTTGATCAGGAT
CAGTAGCCGAGTCGATCTGGCGATGTCCGCCTGTCTGTACGTTTGAACGTCGAGATCTCAGGAACTATTTAAGCTAGAATGTTTAGATTAAGCGT
GCAGATTCCAGAGACATAGACGCAGCCCAAGATTGTTGACCCATGTTTCCATGACCACTCCAACGCCCACATTAGATTGTTCTTAGTTTTATTGT
TCACCTTGCACCTTGCACCTTTTGGATTGTAATCACACCCACATCTTTAAACAATTTTAATTTTTTCTCATTTTATTCGCAATCCGACTAGCTGA
GTAACGGGTACCTCATAGTCATGGTTGTTCACAGAGCGTGTTATGTATCTCAAAAACTTTGTAATTTCAAAGAGTTATTTCACAATTCATTCCAC
AGATTTCGTGGATAATGAATTTTCGATTGTTCAACCTTGCACCTGTCTCAAAAATGAGCTTTCCGTCAGCGGTCCTTCTGACGGTACCGCTGGCG
GTCCCACTGATGGTTCCGCTGATGGTCCCGTTGATAGCCCCACGGACGGTCCCCTTGACGGTTCCGCTGACGGTCCCTTCGATGGTTCCGCTGCC GGTCGTGCTGACGGCCCCGTCGACGGTCCGGCTGATGGTCCCTTCGACGGTCCCGCTGAGGGTTCCGCTGAGGATCCCGCTGAGAGTCCCACTGA
ATGGCATTGGAACGAACTCGTTGATGACCAATCCAATGACGGTCGCGCTGACGGTCCCGCTGACGGTAGCGCTGACGGTCTGGCTGAGGGTCCCG
CTGAAGGCTCCTCTAGCGTTCCCGCTGACTTTCCCGCTGACGTTCCCGCTGACGTTCCCGCTGACGTTCGCGCTGACGCTAACGCTCCTGCTGAC
GGGCACGTCGTCGGTCTCGCTGTCAGTGATCTCCATGTCGACGGCCCAGATTTCCGAGGACAGTTCATAGGATTCGTCCTCTGAAAGAAGAGAAC
GTAGGGTATATTAGTGAGTGAGGCTTTGAGACTTATATTTGATAGTCCCGACTTGGTTAGTCGGCTAAACTTCTCTGTTCCAAGACCCATAATC
TTAAGCCCATTTAGATCTAACTATAAGTTGCATGATTCTTACAGAATATTGTGTTCTGACTATAATAGTCATTATCCTATTATCTGTAATCTTTG
CTCTCTGCCGCTCTTAAAGCAATCAATCAAATCAATCGGTGCATTATTCACAAATACGACGCAAAATTTGTTTTTGGTTAGATTAAGGAATATAT
GAGTTAGCGGTTCCAACAGGCTGATAGGACAAATCATATGCCTCGCACGTAGGGTATAAACTGAGAAGAAACGTGTTTTTCCCCGGAATTCTTTG
CGACACATACAGTTTGTCAAGAAACTGTTTACACACTGTGAAATAAGTTGAATTTTTGACTTTAAAGCTAAAAATAAAGGGTTTTTTGCTTAATT
AAACGCAATTTTTTTATAAAATATAATTAAACAATATTTATTTTACTTATAAATCAAAAAACAAATTAAAAATATTAAATATACAAGAAAATAAA
CAACAAATTCCAAGTTTACACACTTTTGAGACTGTCAAGAAACTCTTTACACATTTTGTTTTCCTACTTTGTTTTGTTCTTTTTCTTAGAACGAA
CTCGATTTTTCCGTTATTTTTGGCTTTGCATTGCTTTTTACAACGCTTCCTATTGAAATTTTGTTGACTTTGCTTGTGAAATTTTGCTGATCAAA
CGTGCTTAAAGCGAATTATTAAATTTAATAAAATGCCTGGAAAGAGATTAACTTTTGAAGTTACCCAATTAATAAACTATAACCACCAGTTGGGA
AAATCTTTTCCAGAATTAGTATAAATGTTTCCTGTATCCCGTAAGACCGTCTACAATGTTTTAAAAGGCTCGGAAAAAGAGGGCAGGCTTGAACC
TAAGAGCGGTGGTGGGCGGAAAATTAAAATTAAAAAGCG
(SEQ ID NO: 1330)

Exon: 1001..1028
Exon: 1238..1794
Start ATG: 1001

Transcript No. : CT33785
ATGACCACTCCAACGCCCACATTAGATTATTTCGTGGATAATGAATTTTCGATTGTTCAACCTTGCACCTGTCTCAAAAATGAGCTTTCCGTCAG
CGGTCCTTCTGACGGTACCGCTGGCGGTCCCACTGATGGTTCCGCTGATGGTCCCGTTGATAGCCCCACGGACGGTCCCCTTGACGGTTCCGCTG
ACGGTCCCTTCGATGGTTCCGCTGCCGGTCGTGCTGACGGCCCCGTCGACGGTCCGGCTGATGGTCCCTTCGACGGTCCCGCTGAGGGTTCCGCT
GAGGATCCCGCTGAGAGTCCCACTGAATGGCATTGGAACGAACTCGTTGATGACCAATCCAATGACGGTCGCGCTGACGGTCCCGCTGACGGTAG
CGCTGACGGTCTGGCTGAGGGTCCCGCTGAAGGCTCCTCTAGCGTTCCCGCTGACTTTCCCGCTGACGTTCCCGCTGACGTTCCCGCTGACGTTC
GCGCTGACGCTAACGCTCCTGCTGACGGGCACGTCGTCGGTCTCGCTGTCAGTGATCTCCATGTCGACGGCCCAGATTTCCGAGGACAGTTCATA
GGATTCGTCCTCTGA
(SEQ ID NO: 1331)

Start ATG: 1

MTTPTPTLDYFVDNEFSIVQPCTCLKNELSVSGPSDGTAGGPTDGSADGPVDSPTDGPLDGSADGPFDGSAAGRADGPVDGPADGPFDGPAEGSA
EDPAESPTEWHWNELVDDQSNDGRADGPADGSADGLAEGPAEGSSSVPADFPADVPADVPADVRADANAPADGHVVGLAVSDLHVDGPDFRGQFI
GFVL*
(SEQ ID NO: 1332)

Celera Sequence No. : 142000013384184
AAGTTAGAACCTTCGCGTCTACTAACAGATTACTTTTCGCCCCGATATCCACTAACCTGTGGCTGCCCCAGTCGAAACTTGGGGTCTGGGCGGTG
GCGCCCATTATCCTGCTGCATAATAATGCTAATTCCTAAAGTTTGTCTATCCCGGGAGCTGTATTGTTTTACAGCTTTAGTGTTAAACCTACAGA
TTCTCAGAGAACAGATGGCTACTCATTCGTTGACTAGAAGGGAGGGCGGAGGGCCTTTGCTGAGAGACTCTCAAAATTGAAAGTTTTACCTGGTT
CGTCGTAAAACTTTTTTTGTTTTGAGTTCAAATTAATGTTTTATAAATGAAATAATAAATAACTAAATAATAATAATAAATAAATAATAAATAAA
TAAGCTTATATAATAAGATCCATTTTAATTGTTTTTCATAAAACAAAATGAGTGATTTTTTTATAATTACAAATGAAACACTTGAATTACCGA
AACAAAAACGCTTAACTGTGCCATCACTAATACTTATTGGCAATAAATAAGTGCGATTTTATGACAACAAAGACGTATCGATAAGATGCATGTGC
AAAATGCGGTGTGTGTATTAACTTAATACTTGGCCTAAGGCTTATCGATAAGGATATCGATACTAAAAAGTCCGGCACCATTGTCGCTATCGAAT
GCCCAAGTATACAAGACAAGCTATGAGAACGAATATAAGGTGGTCAGTTTTAAGTAATTCAAAAAATTCTAAGTCAAAATGTGTCGCAAGTGTAG
TTACTTGATTTAATCGCGAAATTTACTCGTGGATTATGTCTTAAGATAATATCGATATATTGCCGGCGTCATCGATTGCTGACACATATCGAAAG
GTCCGGCCACACTGCTCACCGTCTTCTTCTTGTCATCCCTTCCGTTTCCCTTTCTTTTCGTCTTCACGTTTCCGGTGAGTGCGTGTGCTCCGCGA
ATTTTTAAGCAAAACTCCCTATTAAATACCTCCAATTCTCTTTTTTACTTGCAGCGGGAGTATTACGATACGTTCGCGTTCGTGTAACTTTGTGT
TTGCAAATCAATCCAGGTAATTGTCGCCGAAAACCCCCATTTTCAAGCGGCCGCACCGGGAAAATATGCGCCCAATGTTGTTCCCGAATGCATGT
GTACATTTTTTTTTTGTGTGGACAAAGAAGCGAGTCTTTCAGACTCAATAAACAATGTGTGAATTGGATACCACATGGATGATCTGTAGATATAT
CCTGGCAATGAACCGAATCTAATTGCTATTTTTTTTTTTTGTTGTTTGTGCAGAATGTTTATGCCAAAGGCCCATCGTGTCGCGATCTACGAGTA
CCTCTTCAAGGAGGGCGTGATCGTGGCCAAGAAGGATTTCCATGCCCAGAAGCACCCGGAACTGGAGTCGATCCCCAACTTGCACGTGATCAAGG
CGATGCAGTCGCTCCACTCGCGCGGACTGGTTAAGGAGCAGTTCGCCTGGCGCCACTACTACTGGTACCTCACCAACGAGGGGAATCGAGGAGCTG
CGCAGCTACCTCCACCTGCCGCCCGAGATCGTGCCCTCGACGCTGAAGCGCCCTGCCCGCTCGGAGACCGTCCGTCCCCGTCCCGCCGTTGGCGG
CCCACGCGGACCCGGTGACGCCTCCAAGACCGGAGAGGATCGCTCCGCCTACCGACGTGCTCCCGGCGGCAGCGGAGTGGACAAGAAGGGCGATG
TTGGACCCGGTGCCGGAGAGGTCGAGTTCCGTGGCGGATTCGGACGCGGATCGCGCAACTAAACAACCCAGGCGCTTCAGTTTTTTTTTCTAATG
TATAAAAAATTACTCAGTAAAATGTTCAACTGAAGATCCATACCCTTAACAATAGAAGAAACCAACATCTGAAAAATGTGTGTGTGTTTTATGAT
ATGACGATCAATTATAAAGCAAACGCAAGTGAAATTCCGTGCTCCCCTCTATTTTTTTTTTTTGTTTTGTTTTGTTGTTTGGTCCAGTGATTGT
GGTGTGCAAATCGGACGTGGATTCAGATCCCAAGCGTGGCTAAATAGTATAGTAAACCCGATGCCCGGCCAAACTGAAACTGCTAACCCAACACA
TTTTTGCAAGAAGCTCTTCAGATAACTTTAGAAGTAGGATTTTGCAGATAATTCAGTTTATTTTGCGAGGTTCTGTCGAGAGGAAAGAAGGAATT
CTAGCGTAAATACGTTTTTTTGAATACAATACATGCATTCAATTTTGGTAATTTCAAAAGATTGTTGTATATAGATTTGGATATTTGTCGATTTG
TAGCTCTTTATTATAAAAATATGTGCAGAAATTCATCGCATTCGTTTATAGCTGTGTGCCAAAACATAGTAGACTTGGGTTGGAATAAACCAGTT
GGCTCGAAATACTACATTCAAATATTTAAATAACATTAGAATCCAATTGCTCATAACAAAAACGGCATGAATTGCAAGGACATAGATTAAATTTG
ATTTACCATCAAAGGAAATGGTATATTTTCTAAACGATAAGCCAAAATCTTCGTATGTGGAGGAACGTAACTTAAATGCTCAATTTCGTTTTATT
TGTTCACGCTACTTAAACGTTCACAATTAGTTAAATAACTAGTTTACTTAAATAGTCTTCTTTTGCTCACGAGCATCCTTTTGTTGTTCTGTAGC
TGCCTTTTACTTATATATTAATTCTAATTTTATAAATACACTAGTTTCACATTTCCCAAAGTTAGGTTTTAGTTAAATCTTATGTGTCTACTAAT ATTATTTAAAAGCTTATGTGCTTCTCCATTTAACGTTGATTACTTTCAACTAATATTTTATGTAAACAAGTAAGTATGCTGCTATGCTCGGACCA
TAAAGAATTCGAATCGCTTAGATTATTTATTTAGGCCGACCAAAAGAACTACAACAATATACGACGAATGGCATTATTCTAGGT
(SEQ ID NO: 1333)

Exon: 1001..1934
Start ATG: 1296

Transcript No. : CT33819
GCAGCGGGAGTATTACGATACGTTCGCGTTCGTGTAACTTTGTGTTTGCAAATCAATCCAGGTAATTGTCGCCGAAAACCCCCATTTTCAAGCGG
CCGCACCGGGAAAATATGCGCCCAATGTTGTTCCCGAATGCATGTGTACATTTTTTTTTTGTGTGGACAAAGAAGCGAGTCTTTCAGACTCAATA
AACAATGTGTGAATTGGATACCACATGGATGATCTGTAGATATATCCTGGCAATGAACCGAATCTAATTGCTATTTTTTTTTTTTTGTTGTTTGTG
CAGAATGTTTATGCCAAAGGCCCATCGTGTCGCGATCTACGAGTACCTCTTCAAGGAGGGCGTGATCGTGGCCAAGAAGGATTTCCATGCCCAGA
AGCACCCGGAACTGGAGTCGATCCCCAACTTGCACGTGATCAAGGCGATGCAGTCGCTCCACTCGCGCGGACTGGTTAAGGAGCAGTTCGCCTGG
CGCCACTACTACTGGTACCTCACCAACGAGGGAATCGAGGAGCTGCGCAGCTACCTCCACCTGCCGCCCGAGATCGTGCCCTCGACGCTGAAGCG
CCCTGCCCGCTCGGAGACCGTCCGTCCCCGTCCCGCCGTTGGCGGCCCACGCGGACCCGGTGACGCCTCCAAGACCGGAGAGGATCGCTCCGCCT
ACCGACGTGCTCCCGGCGGCAGCGGAGTGGACAAGAAGGGCGATGTTGGACCCGGTGCCGGAGAGGTCGAGTTCCGTGGCGGATTCGGACGCGGA
TCGCGCAACTAAACAACCCAGGCGCTTCAGTTTTTTTTTCTAATGTATAAAAAATTACTCAGTAAAATGTTCAACTGAAGATCCATACCCTTAAC
AATAGAAGAAACCAACATCTGAAAAATGTGTGTGTGTTTTATGATATGACGATCAATTATAAAGCAAACGCAAGTGAAA
(SEQ ID NO: 1334)

Start ATG: 296

MPKAHRVAIYEYLFKEGVIVAKKDFHAQKHPELESIPNLHVIKAMQSLHSRGLVKEQFAWRHYYWYLTNEGIEELRSYLHLPPEIVPSTLKRPAR
SETVRPRPAVGGPRGPGDASKTGEDRSAYRRAPGGSGVDKKGDVGPGAGEVEFRGGFGRGSRN*
(SEQ ID NO: 1335)

Name: ribosomal protein S10-like
Classification: ribosomal_protein

Celera Sequence No. : 142000013384111
CTGGGCCGATATCGTTTCCTGCAGCTTCCGGCGAAAGGCAAACTTGCGGTTACGCTGATCCTCCAGCAATTTGGTCAAGTTACTGTCATCGAAAG
GCATCTTGGCATTCATCATGATGAACAGAATGACTCCCAAGGACCAGGCGTCCGCTAGCTTTGGATCATATGGTCGTCCACAAACTACTTCAGGT
GCAGCATAAGCAGCTGATCCGCAGTATGTCTCAGATTTCATCTCCCGGCCATTATCGTCGCGACAATAGCGAGCAAATCCGAAATCGGCCAGCTT
GATGTTGAGCCGCTTGGAGAGAAGAATGTTCTCGCACTTGAGATCCCGATGGGCAATGTCCAGGTTGTGCAGATACTTCAGTGCCTTGGACATCT
GAAAGAACCAGATCTTCGATTGCTTCTCATCGATGGGACCCGACCTCTTGATGTGCGACAACAAATCCCCATTCTCTGCGTAACGCATAAAGATG
AAGATCTTGGGACCGCGCTGAAGGATGCTATGGATCTGAATAATGTTGGAATGATCAATCTTTGTCAGGATCTCCAGTTCGCGCGGAAAGAACTT
GTTCACGAAATCAGTGGGCGCCTTGGCTTTGTCAATGATTTTACAGGCCAAATGTACTCCATGTCCATGATCATCGGCATAACCGGCGGTTATAA
CAGTGGCATAAGACCCCTCGCCGATCTTGTGACCCACATTGTAGCCCCGCTGTGCCAGTGCATCCACATCCGAACTTCGAGTACCCAACTGACGG
ATCCCAGCGCTAGAATTGTATTTGGACATGGCTCTTGTTTCCTCGGCGTGCGTGTAGTGTAGTTTTCCGAGAGTTTGCAACTAGGTGATTTGGTA
ATGGCATCAAGCGAATGATTCTTTTCTAAACAGCGGACATAATTACCCTTAAGTTGGTTGATTTCACAAACAATAATTTTATGCCACTTGTGTAT
TTTACTTACTAAATTCGAATCCAGAAATTTTGACAAAACCTACAAACGTTATGAGGTGTGAAAGAAATATAAAAAAGGGTAATGCACAGCCTTCT
ACCATAACTGACAAATCTGAACCAAAGTATAAGGTTACTACGTCCCAAATATTATTATGCTAGCATGCGAAATGCTAATAAGAGGGCATAAAAAT
AATATATAATATATGGATAAGGAAAAACTGTTTAAAGTTGAGTATTTGTTTTGAGACATTTTAAAAGCCTTAAATTGATAAATTAAGTAAAAAAA
AAAAACTGTGTTCTGAAAGCAACTAAAGTTTTAATATTTCTATATTACAGTTGCCATTCTTGTTTCCTCGAGCCAAGCCACTGGCTCTGCGTCCC
AACCAGCTCCAATCAATAGAAATCCCCGAGGCAGCCACAACAGCAGTGGCATTGGCGACTCTGAGCTAAGTGCCTCAGAGCGAAGTCGACGATTG
ATACCCTACATGGCCTTCTATCTGCCGGCGCCCGAGTTGCCCATTAATCAGCAGTATGCCACCAAGCACTCGTCGTCGGCTGGCGGAGCACAGCT
GCAGGCACCGCTGCCAGGTCCTGGAAGGATACCAGTGCCGGTGGCCTACATGCCGCAGCAGAAGCACCATCCCCACCACCATGGACCACCGCATC
CGCCACCAGGGCCGCATTATCAGTCGGGAGCAGGCGAGGTCTATCACTCCCTTGCGATTGGAGGCCACCAGCATCAGCATGCGCCCCCACATCCG
CCACCTGGTCATGTCAAGGAGCAGCAGGCGATCACCAATTCGGGTGCCACGTATATTGCATACAAGCCATTAAACCCGACGCATAAGGCAAGTAT
TTGAATAATAAGTGTTTTTAAAAAGGCTATGTCGCCTTGGGAAAGAATATATATCAAATGGAGCTAAATTAGTGCTGAATCGGTTTAGATTGCTT
CCTTCTAAAGTCCATCAATCGTGAAATACCAGCAATATTGCGAATATTGGAATATGAAACGTCGAGGGTATTGAAAAAGCACTTGGATACCTATC
CACTCTCCTTCATTACAATTGATTTCATGGGTCATAAATAAGCAGAAATAATCACGTAATTCATAATTTACACGCACGCAGCACAAGACAGTGCA
GCATTTTCCGCCACTACCGCCGTCGCCCAAGGAGCAAGTGCAGCAGCAGCATCCACAGCAGCACCACCACCTTCTGCACCACCAGCAGCAGCAGC
AGCAGCAGCAGCAGCAACCACAGCAATACGAGATCCTATCATCGAGCTTAGTGGCATCCCAGGCGCAGCGACAGCGGGGCAAACAATCAAAAATC
AATTTAACACCATTTACAGCGCAGAACACATTGCCGGGACAGTTTATACCCATTATTTATACGCCAGTGAGCAGCAGCAAACCGGGCTCCCCCGG
CGATGCCATCAATTACAATAACATCCAAAGCAACCTGAAGCAGCCAGAAATTGTCTATAAAAATTCCCATCAAACACAAATCGTTACGGATTATG
CAGCCGGAGCGGCTGCCTCCGCCGAACAGCCACCACTATCGTCATCTGGCGAGGAGGTGGATGAGACGAATGGCGAGAAGATGGTGGAGCAGCAG
CAGGAGGACCATAGAGCCCAGGAGGAGGCGGTGGAGCAGCAGCAGCAGCAGCCGCAACTACACCAGCAAGTGCAAAACAATCCAAGGTAAGATTT
CTTGTCACTCTTGTGACTCTCATGCCCAAACGGAAAACAGAGCGCTGGCGCGAAAGCCCAAAAGTAAGCCAGGTCTGATCTTTGATCTCATGGAA
TATCCAAAGCCTCGTCTGCTTAATAGGCAGTTCTCACAGCCACGCCCACTTATATATCGTGAGGTAGTTGCAATATCGCATGTAGAATACAAATT
AAAATGTTGCCACTATGGCTGTCTTTAAAACAGTTTCATGTCATCCATACATTTTTAACAACTTTACACAACGAACCTTTAATTGGTCTTAAAAA
AAAAATGCTATACAGATTACTTTTAAGACACAACCCACTTAATTAACTTACGTTACGAAAGGTTGCTAAACTTATTGTTTCGCCATCCAAAGATG
TCAATAATTAATTGGGAACAGCCAGTTATCAACAAACTGCAGTCCAATTCAATATTCGATAATGCAACAGCGACTTTAATATGCTTCTGTTTAAA
ACGCATGCAATTGGGATTTCTGAGTCTGAGACGGATACTGCTGTTGCAACGCTATGCCCTTGGGCAGAAAAATCAATTGCATTTCATGCACCAGC
CCAGTCCACTCCAATGTCCGGCTGCGACACAGACCGCGTCCGCTCTTCTCCATCTCTGAATCCGGTCGTCCACATCGTCACCATCTTTGCAACTG
CACTGGTGACGTAAGATCCATGACGACAACGATTGCGACTCCAATTGCCGTTCGATGTACAGCAGGAGGCACAGCCAGTGGGCAACAAAAAGGTG
GGCTGAGGAGACTTGACCTGGCCGGCCAGTGTCTCATGTATGTATGTACATAACTCCTCTCCACATTCTCATGTAGTAATTGTCAAATGGCAAAT
TCATGTCATAAGTAGCCAGCGGGCTCAGGTCAAAAATTTGTCATACAATGCTTATCAGATGAGGAGTGGGAAATGGAAAAACATGCCAATCAGCG
AAGATTTTTACAACCACCACACTTCAGTTGAACACATTTCGATGCTGCACCTTTGTTTTTCGGTTAAAATCATTCAATAAGTTACACTTTAAGGT
GCAAACGAAATAAATTATGCTTAATAGGCATATTACGATTTCAAGAGTAGGGAAAGTCAGGATATAAAGGAATACAATTTGTCAAATTATTTGGC TGTTATCTACTAGTCATGGATAGATAATCAGATACAAATTAAAACTTCTTAAGGAATAATGAATAAATTTGAAAATATCACAATGAAATAGGGCA
ACCTAACGTACACTCTCATGACATTTATGCTTGAAACCGAAATCATAACCGCTTTGCATGATTAACCTCCAACAGCATCGGCTACGCTTCTGTGT
CGGTTCCCGATTCGAGCGCAATTACCGCGACCACATCCTCCAAAAACGCATTGATAATACATCAGAAATCACCGGCTTTCGGGCACGTTAGCAAA
TACGAAAGCTACTTCAATATGGCCCCGCCCTCGACTAGTCTTGGTCATTCTCCTCATCAGCAGCATTCACACATGACGCCGCAGGAGAAATATGT
GCTTTACTTACAACAGCGCATGAAACACCAAAAACATCAGCAACATCTGCAGCAGCAGGAGCAGCAACAGCAACAGCATTACGACTTTTCACATC
CGGTGGTGCCGGCACAAAGCAATACATTGGCTGGTAGCCACCATTCGCAACACACCCATCTGCATCCCCATCATCCCCAAACCAAGACCCATCAT
CCAAACAAGTACGATGCCCTCTACGTAAGACCGGATGCGACTGCTGGCCAACAGGTGCTGCATATCCCGCTGCGCGCACTCATGGCCCACGTCCA
AGAGCAGTCGCACTCCCAGTCGCAATTACAAGCGGAGTCGCAGGCACAGTCGCCACGTCACGATTTCGCCAAGGATGAGCCACTTGGGTAAGTTC
TTTGCTTGGGAGGAGGAGCAAGGATCGTTGAGAGGAAACAAGTTGCTTAGGTCTTACCAACGCAATAATGATTCTCCCTTCTCAAGAAAAAAGTA
TTCTACGAGTTTATTTAATAAGAAAAACTATCTAAATTGATAGTGATGGTCTAAAGATAATCCACATTACTAAGATATATAAAACTGCTTAGTAA
GTACACAAAGTACTCAATACGTCCTTCAAAAACTAATCATTTCTAAGTAACAAGTGCATCATGAAATCATAATTTAGCCTCCCAAAAGACCTTAC
TTTAGATCTGAACATTTCTTTTAGTTCCCCAGCACCACCGCAGTTTATAGACTATCTAATTGATGGGCCAAGACAATCGCTGGAGGAAGAGCAGC
AGCACTCCCAGCATGAGCGACCATCGGCTCATCAGCCGCCCCAGCATGCCTACATCCTGGTGACCACGACAGCTCCACATATCGAGCATCAGCCT
GCACCGCAAATGCATCCAGAGATTTCCACACCGCGTCCACCGATTCTCGATTCTATAACCAACAGCCCACACTTCGATTACGTCCCGTGCATACTTACAA
GGCCACCAGGCGTCCCATTTACGTGACCACACCCGCACCCGCAGTGTCGCCGACTTCAAGTCACACGGTAGAGATTACGCCCAAATTTGTTTACG
TTTCGGGGAAGCCTCCTACTGGCCAAAACCCAGAGTTACCGCTTAGAGAACCATCTACGGTAACGCCTATTAAACTTAAGCCCGTTTACAAATAC
GCCCATGAGCGCCCTCCATTAACGCCTGCATACGTACCAGAGGATCAGGATCAGCTACCAGATATTCGCACCTCATCACTGGCCGAAATCCTTCA
CAAGCTTCAAGCGAGCAATCATCTTCCGCAAACCCTAACACCCGACAACATCGACAACTCCATCAAAACATTGATCCGCATACTGCAAAATCTAA
AGCAAACCCAAACCATTGTGGCTAATCCTCCGCAGCATCACGACGAGCACAAGTCCAGTGCCCAGGATTATGATTACAATACGGGCAGCGAAGAG
GAACACCATTCTCAATCAGAGGAAGCGATTGCCAGACCCAAGGGACCAAGTGAGTAGCCTTTACTTTATTATGTTTCCCTATTTTATTTCCATTT
GAATAGATAAACATCCAGGACCAAGCACTGGAAGACCTGGCATCGATTATCCGAACTATGCGGAGATCCCTCAAACCAGTTTTGAGTGCACCAAG
CAACGCTACAAGGGATTCTTTGGCGATCCGGAGACCAATTGCCAGGTCTGGCATTACTGTGATCTCAATGGAGGAAAGGCTTCGTTCCTTTGCCC
CAATGGAACCATATTTAGTCAGGTAAATGGGCGAACTTATGTTATACACATGTTAAGAATTAAACAATTAAAAACATATATAAAAACAGATTGCC
TTAACTTGCGATTGGTGGTTCAATGTCAAATGTTCAACAACCGCACAACTTTATGTGCTGAACGAACGACTTTACAAGTACATTCTGCCTTTTAA
TCCAAAGTTCCCCGAGGACTACAACGGACCTATTGTGGATAAGTAAGACACTCTTATATGATTCGAAAGTATTAATTAACAAACGTGTCATTTAC
TTAAGGTATCTGGCAATGAAATTCCAGGAAATGGAGGAGAAGATGCGCCTGGAGAAACAACGCAAGGCGGCCCAAGAGGCACAGAAGCCCGAAGA
AGCACCATCTACTCTACCTGCGTTGCCCAAAAATCACAAGCCAGAACCGAAACATGGTAGCGGAATAAATGCCCAGGTCTATGAGCAAAGCTCTG
AGAAAAACTTGCTGATCGATGATGAGATAGATGATATTTCGGAGCGTGGGACCTACGATACGTACGACCAGACCGCACCCACAACTATAATGGCA
CCCACGAGCACCCAGGACACGCAGTCCTTTGTCCTTAAACCAATCGTAGTTTCCTCCACTCCACAACCGCTGCCAGAGATTGATTTCGAAGTTGA
GCCAACAGCTCCAGGCAGCAGCGAAGAGGAGGATCACCTGCAAAGTCTAAGGGAAACTAAGGAAGCTGAGAAGAAAACGCGTGAATCCACAAAGG
TGAGCGTGGAAAAGCTGGAAGTAATCGAGATCAAAACCGATGGAAACACCGGACAACTAATGCCCATCAAGAGCAGTAGCAAATGAGCATTTTGT
GGAGAGGATGAATAGCTCTTGCCATATTTGTAATGAGAAATTTGTTTGCGACTTGGTTGTATAATCCCTAAATTATTCTTAGCGAGCAAGTACTG
TAAATAGCTAGCTGTAAATGCAACTGTATACATACCTATAGCTATAGTGAAATAAAATCTGACAAGTAAGTAAAAACGATCATAGCACTTACCTG
TTTGCCATTGAGGACATGAATATGAGCCATGTTGAGTGAGTTTAAAGTCGTGGGAATCTCGGAAGCATAGCTTTGATTCTGTGGAAGAAATCAAT
TAATATTAGGTGGATTATTATTATTAGATTAATCACGATATTTCAAGTTGCTAGTGCGCAACGTAATGGATTTATAAGTACAATGCCACAATTTA
TGTGTACCTCATAGATATGTAAATTCTAAAGCATGTACGTTTTGTAAGCTAGCATTTGAAACCATATTGTAGATCTCAAAACTAACGTGCTTAAA
ATCTTATTCAGAACATTTAAATAAGCAATTACATATACAAATATGGCAGGGAAATGTTTCAATATTTCAAAAATTATACTAACAATCTCGATTAG
CTTCCGTATGCGATGCCCGCTATGATGCACGGTGGAGCAAATTTGGCAGTGGGATCGGTAACACTTCATACAGTACTTGTCTTTGGGCATTCGGT
GATGGATGCAAAGGTTCTGACTCGGCAATGTGAAGTACTGATCCCCCACTCTGAGTTTCTTGCTGAAACTACTGTCCTGTTCCGTAGAATTGCGA
AAAATATGCGACTTTAGTACGCGACTACGTTTGTGGACAGCATCAAAGCAACGGCGGCAGTAGAAGGCATTGCATTGCCTGCACTCTCCGCTGGC
AGTGGCATTCCCGCACTCGCTGCACTTGACGGTCTGGACAATCTCGCTGATCGAACTGGGGCTCAGCGATTGGTTTGCCGAGTCCTTGGCAAATG
GCAGAAGGTAGCTGAGGCTACTGGTCCTACCCAGCACGTGG
(SEQ ID NO: 1336)

Exon: 1001..1028
Exon: 1286..1801
Exon: 1894..1967
Exon: 2077..2651
Exon: 3230..3457
Exon: 3971..4552
Exon: 4870..5654
Exon: 5707..5912
Exon: 6088..6122
Exon: 6181..6736
Start ATG: 1001

Transcript No. : CT33934
ATGAGGTGTGAAAGAAATATAAAAAAGGTTGCCATTCTTGTTTCCTCGAGCCAAGCCACTGGCTCTGCGTCCCAACCAGCTCCAATCAATAGAAA
TCCCCGAGGCAGCCACAACAGCAGTGGCATTGGCGACTCTGAGCTAAGTGCCTCAGAGCGAAGTCGACGATTGATACCCTACATGGCCTTCTATC
TGCCGGCGCCCGAGTTGCCCATTAATCAGCAGTATGCCACCAAGCACTCGTCGTCGGCTGGCGGAGCACAGCTGCAGGCACCGCTGCCAGGTCCT
GGAAGGATACCAGTGCCGGTGGCCTACATGCCGCAGCAGAAGCACCATCCCCACCACCATGGACCACCGCATCCGCCACCAGGGCCGCATTATCA
GTCGGGAGCAGGCGAGGTCTATCACTCCCTTGCGATTGGAGGCCACCAGCATCAGCATGCGCCCCCACATCCGCCACCTGGTCATGTCAAGGAGC
AGCAGGCGATCACCAATTCGGGTGCCACGTATATTGCATACAAGCCATTAAACCCGACGCATAAGGCAAATTGCTTCCTTCTAAAGTCCATCAAT
CGTGAAATACCAGCAATATTGCGAATATTGGAATATGAAACGTCGAGGCACAAGACAGTGCAGCATTTTCCGCCACTACCGCCGTCGCCCAAGGA
GCAAGTGCAGCAGCAGCATCCACAGCAGCACCACCACCTTCTGCACCACCAGCAGCAGCAGCAGCAGCAGCAGCAGCAACCACAGCAATACGAGA
TCCTATCATCGAGCTTAGTGGCATCCCAGGCGCAGCGACAGCGGGGCAAACAATCAAAAATCAATTTAACACCATTTACAGCGCAGAACACATTG
CCGGGACAGTTTATACCCATTATTTATACGCCAGTGAGCAGCAGCAAACCGGGCTCCCCCGGCGATGCCATCAATTACAATAACATCCAAAGCAA
CCTGAAGCAGCCAGAAATTGTCTATAAAAATTCCCATCAAACACAAATCGTTACGGATTATGCAGCCGGAGCGGCTGCCTCCGCCGAACAGCCAC
CACTATCGTCATCTGGCGAGGAGGTGGATGAGACGAATGGCGAGAAGATGGTGGAGCAGCAGGAGGACCATAGAGCCCAGGAGGAGGCGGTG
GAGCAGCAGCAGCAGCAGCCGCAACTACACCAGCAAGTGCAAAACAATCCAAGCCCAGTCCACTCCAATGTCCGGCTGCGACACAGACCGCGTCC
GCTCTTCTCCATCTCTGAATCCGGTCGTCCACATCGTCACCATCTTTGCAACTGCACTGGTGACGTAAGATCCATGACGACAACGATTGCGACTC CAATTGCCGTTCGATGTACAGCAGGAGGCACAGCCAGTGGGCAACAAAAAGGTGGGCTGAGGAGACTTGACCTGGCCGGCCAGTGTCTCATCATC
GGCTACGCTTCTGTGTCGGTTCCCGATTCGAGCGCAATTACCGCGACCACATCCTCCAAAAACGCATTGATAATACATCAGAAATCACCGGCTTT
CGGGCACGTTAGCAAATACGAAAGCTACTTCAATATGGCCCCGCCCTCGACTAGTCTTGGTCATTCTCCTCATCAGCAGCATTCACACATGACGC
CGCAGGAGAAATATGTGCTTTACTTACAACAGCGCATGAAACACCAAAAACATCAGCAACATCTGCAGCAGCAGGAGCAGCAACAGCAACAGCAT
TACGACTTTTCACATCCGGTGGTGCCGGCACAAAGCAATACATTGGCTGGTAGCCACCATTCGCAACACACCCATCTGCATCCCCATCATCCCCA
AACCAAGACCCATCATCCAAACAAGTACGATGCCCTCTACGTAAGACCGGATGCGACTGCTGGCCAACAGGTGCTGCATATCCCGCTGCGCGCAC
TCATGGCCCACGTCCAAGAGCAGTCGCACTCCCAGTCGCAATTACAAGCGGAGTCGCAGGCACAGTCGCCACGTCACGATTTCGCCAAGGATGAG
CCACTTGGTTCCCCAGCACCACCGCAGTTTATAGACTATCTAATTGATGGGCCAAGACAATCGCTGGAGGAAGAGCAGCAGCACTCCCAGCATGA
GCGACCATCGGCTCATCAGCCGCCCCAGCATGCCTACATCCTGGTGACCACGACAGCTCCACATATCGAGCATCAGCCTGCACCGCAAATGCATC
CAGAGATTTCCACACCGCGTCCACCGATTCTCTATAACCAACAGCCCACACTTCGATTACGTCCCGTGCATACTTACAAGGCCACCAGGCGTCCC
ATTTACGTGACCACACCCGCACCCGCAGTGTCGCCGACTTCAAGTCACACGGTAGAGATTACGCCCAAATTTGTTTACGTTTCGGGGAAGCCTCC
TACTGGCCAAAACCCAGAGTTACCGCTTAGAGAACCATCTACGGTAACGCCTATTAAACTTAAGCCCGTTTACAAATACGCCCATGAGCGCCCTC
CATTAACGCCTGCATACGTACCAGAGGATCAGGATCAGCTACCAGATATTCGCACCTCATCACTGGCCGAAATCCTTCACAAGCTTCAAGCGAGC
AATCATCTTCCGCAAACCCTAACACCCGACAACATCGACAACTCCATCAAAACATTGATCCGCATACTGCAAAATCTAAAGCAAACCCAAACCAT
TGTGGCTAATCCTCCGCAGCATCACGACGAGCACAAGTCCAGTGCCCAGGATTATGATTACAATACGGGCAGCGAAGAGGAACACCATTCTCAAT
CAGAGGAAGCGATTGCCAGACCCAAGGGACCAAATAAACATCCAGGACCAAGCACTGGAAGACCTGGCATCGATTATCCGAACTATGCGGAGATC
CCTCAAACCAGTTTTGAGTGCACCAAGCAACGCTACAAGGGATTCTTTGGCGATCCGGAGACCAATTGCCAGGTCTGGCATTACTGTGATCTCAA
TGGAGGAAAGGCTTCGTTCCTTTGCCCCAATGGAACCATATTTAGTCAGTTCCCCGAGGACTACAACGGACCTATTGTGGATAAGTATCTGGCAA
TGAAATTCCAGGAAATGGAGGAGAAGATGCGCCTGGAGAAACAACGCAAGGCGGCCCAAGAGGCACAGAAGCCCGAAGAAGCACCATCTACTCTA
CCTGCGTTGCCCAAAAATCACAAGCCAGAACCGAAACATGGTAGCGGAATAAATGCCCAGGTCTATGAGCAAAGCTCTGAGAAAAACTTGCTGAT
CGATGATGAGATAGATGATATTTCGGAGCGTGGGACCTACGATACGTACGACCAGACCGCACCCACAACTATAATGGCACCCACGAGCACCCAGG
ACACGCAGTCCTTTGTCCTTAAACCAATCGTAGTTTCCTCCACTCCACAACCGCTGCCAGAGATTGATTTCGAAGTTGAGCCAACAGCTCCAGGC
AGCAGCGAAGAGGAGGATCACCTGCAAAGTCTAAGGGAAACTAAGGAAGCTGAGAAGAAAACGCGTGAATCCACAAAGGTGAGCGTGGAAAAGCT
GGAAGTAATCGAGATCAAAACCGATGGAAACACCGGACAACTAATGCCCATCAAGAGCAGTAGCAAATGA
(SEQ ID NO: 1337)

Start ATG: 1

MRCERNIKKVAILVSSSQATGSASQPAPINRNPRGSHNSSGIGDSELSASERSRRLIPYMAFYLPAPELPINQQYATKHSSSAGGAQLQAPLPGP
GRIPVPVAYMPQQKHHPHHHGPPHPPPGPHYQSGAGEVYHSLAIGGHQHQHAPPHPPPGHVKEQQAITNSGATYIAYKPLNPTHKANCFLLKSIN
REIPAILRILEYETSRHKTVQHFPPLPPSPKEQVQQHPQQHHHLLHHQQQQQQQQQPQQYEILSSSLVASQAQRQRGKQSKINLTPFTAQNTL
PGQFIPIIYTPVSSSKPGSPGDAINYNNIQSNLKQPEIVYKNSHQTQIVTDYAAGAAASAEQPPLSSSGEEVDETNGEKMVEQQQEDHRAQEEAV
EQQQQQPQLHQQVQNNPSPVHSNVRLRHRPRPLFSISESGRPHRHHLCNCTGDVRSMTTTIATPIAVRCTAGGTASGQQKGGLRRLDLAGQCLII
GYASVSVPDSSAITATTSSKNALIIHQKSPAFGHVSKYESYFNMAPPSTSLGHSPHQQHSHMTPQEKYVLYLQQRMKHQKHQQHLQQQEQQQQQH
YDFSHPVVPAQSNTLAGSHHSQHTHLHPHHPQTKTHHPNKYDALYVRPDATAGQQVLHIPLRALMAHVQEQSHSQSQLQAESQAQSPRHDFAKDE
PLGSPAPPQFIDYLIDGPRQSLEEEQQHSQHERPSAHQPPQHAYILVTTTAPHIEHQPAPQMHPEISTPRPPILYNQQPTLRLRPVHTYKATRRP
IYVTTPAPAVSPTSSHTVEITPKFVYVSGKPPTGQNPELPLREPSTVTPIKLKPVYKYAHERPPLTPAYVPEDQDQLPDIRTSSLAEILHKLQAS
NHLPQTLTPDNIDNSIKTLIRILQNLKQTQTIVANPPQHHDEHKSSAQDYDYNTGSEEEHHSQSEEAIARPKGPNKHPGPSTGRPGIDYPNYAEI
PQTSFECTKQRYKGFFGDPETNCQVWHYCDLNGGKASFLCPNGTIFSQFPEDYNGPIVDKYLAMKFQEMEEKMRLEKQRKAAQEAQKPEEAPSTL
PALPKNHKPEPKHGSGINAQVYEQSSEKNLLIDDEIDDISERGTYDTYDQTAPTTIMAPTSTQDTQSFVLKPIVVSSTPQPLPEIDFEVEPTAPG
SSEEEDHLQSLRETKEAEKKTRESTKVSVEKLEVIEIKTDGNTGQLMPIKSSSK*
(SEQ ID NO: 1338)

Celera Sequence No. : 142000013383898
GAATCTGCAACAGGATACAGCAATGCATTCACGTAGTTTAAAAACAGAACAAATTTTCGGACTGATTTAGATGAATTTTCATTTGGCTAAATATG
TAAACTAAAAGATAATTTAAAATAACCCAAATCATAAGCATCTGGAGCAATGACCTAGTGAAATGTGAAGATGCAGCAGATTAAATTTGATACAG
TAAAAAAGTACTTATAGGAATGTCAATTTTATCGCGCAACAGAATGTCGTACAATAACATTTAGAAGCCATATGAAGAACAAAGAAATCAAGATA
TACGTATTAATTATAGTATACTGAAAGTGTCATAGCAATTAGACGTTGGTGATTCCAAAAACACATAAGTGCATGTCTGTCGCTCAAATAGGTTT
CTTTTTAGATATGTACGATATTATTTGCATACCTAGTATATAATTGTATTGTATAAAGTATTAATTATGATATTCCTTCCCAGTTGTGGTGGCTA
GCATTTGCTCAATTAGTTCTTTAGCTCTCTACTGCGCACTCTTACGCACCGGTGTACCTACTATTTTAAGAACGAGAAACTATTTTTATGATCAA
TCCAGTTTTTTACACACACTTGTTATGTTTACACAAAAGCTCACTGACACAAAAAATGGCTGGGTAAATTGGAATGATATCCAATTTTGAAATATT
TCGAAATATTTCCCAGCTGCACATCACAAACGAACAAAATCCTACAGAATCTTTCCTAATCTCTGTAACCAAATGGTTGTAAGAAATTCTCACTA
TATCAATTTAGTTTACAATTCCCTCCCTATAATGTGGTACTATTTTTGTATATTTGAGTTTACAAAATTAGAGAAATTTTTAGAACTGATGTATA
TTAGAAATTAATCAATTCGTCCCGTTTTGCAATATATTTATACCCTATTTTATAATTTGTATTTGTTTTTTTTTGCAATAAAGAAGATATGATAT
ATAAACGAATGACTTTGTCTTTTATTCCCAGCTCAATAAATACAAGCACTTCACTACATTGTGCAAACGATTAATTTTTATTGATTAAATGTTTA
GGATGTGTTAAATATAAATTTATGCTGTATGTTTATATATACGCAGCAATCGCTTAAAGTTCTGCAATTTATTTGGTTAGAAACAGCGATTGCAT
TTTAATTAGAGCTCGATGTTGAAGGCAGGGCAGCGAGGATTTCTTCGATGAAGTTGTCCGGGTGCTCGATGAGATGCAGGAGACCTAAGATGTTG
AACAATTTAAATTAAATGACGAAATTCAAATGGAGCTGCCACGGACACTCACCTGCAACATCACAGAATTCGACAAAGGAAGTGCAGGGCAGGAA
CTCCTCCGTTAGGGTCTGCAGGATGCTATCCGTGGACTTGAGCAAAGCCTCATCGTTCTTACGAAGATAGTCGAACAGGGAAATCGGCCAATCCT
CCTCCTTGGGCGTGCTTACCGTCTTGAACAGATTGTCGTAGATCAAGTCCACCAATGCCCACATCATAAGGAAGGGCTTGTAAACAGTGTAATCC
TTGACCTGGCGGTCTGCAGGAGCCAACAAGGCTTTGCACAGCACGGCGGGTGAGACGTGGCGACCCTGGGCCACTGCAATCATCCTCTTCAGATG
TGCTAGCTTATGCTTATTCCATAGCTCTCGGCTGTGCAGTGACAGCGAAATGGTTGCCATGAAAAGCGGACCATCCACCTCATATCCGCATTCCA
ACCACTTCTCGCTGGGCGGCGCCTGCAAATACGTCAGCAGAGTCTTGCTGTCTCTAGCCGCTGATCGCGACGAAAGCAACAGATAGACGGAGTAG
AAGAGCAGGTAGGGTACGAAGTGCATGTTCGATTGCGGACCACCTCCGCCGGCATCGTCATGGAAGCTGCGTTCCCAAGCAAATCGTACCAACAG
CAGCTTCAAGTCATGCACACTGCTGGTGTAGGAGATGTCACAGCGCTGGGTACTCTCCTGCATATAACTGCTGTGGCGGGTCATGCAAGCGGAGA
AGGCCGCCTCTCCAACGGCGGGTCCCCAAAGGGGCAGCAGTCCATTACATCTGGTGTTGGCATTTGCAAACTAGCACGCTCCCATTCATCCCTG
CCACGTGTCAATCTTATGGCTGATGTGTGGCAGTCCACATGGACCACATTGAAGTGTGTGACGGTGGTATAGCCAATGGTTTTTCTCGACTTCAG
CTCAAACTCCTCGACATTGCAGCGCTTGGTGAAGGTGTAGATACCAAGCACCTTGTCTGGCTGGCAGGCGTAGCCTTCGCGACAAATAAAGCAAG
TTAGTCCTGTTTCGTCGCGCAGTTTTTCGATCTTCTGCAGGATGGAGCCCTTGGCCGTCACCTGGCCCTTTTCATTCGTGCGCATTCCCAATGCA TCCAACTGTTTCTCGCGCGTGGCCATTGCCAGCCGCTTCTTCTCTGCCCTTGTGAAGTCACGCACTTGCTGCACCCTCGCTGCTGTCGCCGAATC
GGTGGAGAGAGCTTCCAAAAGGTTCTCGGCCAGACTGCCCACATGCTCATCGCTGGATACTTGTTCCAGGCGATGAATAATGGGTATAATGTCCT
TGCTAATAGCCACCTGAGTTGCCTCATGATGATTTGAGAGGCCGGTGAGGAAACGAAGAATATACTTCAAGCTTGGCCGCGAGATGAATTCTTTC
AGCTCATCGGAGTCGGTTCGCAGGAGAGTGGGCTTGACACAAGGCGCATGCTCGGTGATGTAGGCTAGCGATCGCTCAACGATGCCGAGACTTAC
TATGTAGTCCTTGAGAGTGCCGCCAATGCAGTTGTGCTCAATTTGGTTAGTCAGCACGCAGAAGAGTTCCAGCTTGAACTCTTCTTCAGGTGTGC
GCTCGTTGTCAAAGCGATTAAAGTTCAAAGTGTCCTGAAAATATAACAATATTAATCCTCGATCGTATAAGCAAGAAGTAACACCTTACCTTGAA
ATGCTCGCAAAGTAGAGCCATCTTCACCTCGTTGCCATAGACCAAAGCGGCTAGGACACGAATAAGATGGCGGAGCACCGAAGGATTGTTTCTAA
CATTGGGACAGTCTGTGCACGATATTAGTGCGCTTACATACTCCGGTCCACCGAATGTCAAGGAGAACTGCAGGAACGAGTCCAACGTATCGCTG
GCCGCCTTCGATAGTATTGTTTCCATGATCTCCAATAACTGCTCGGTAACCGCCGATTGAATCGAATCGTTCTCCGACTGGAGACACATTTGTAG
CACCTTAAGCAGCGTGTTGATGGCTCCGATCTCGGGTTGGCAAAGCACCTCTTGGCAACGGCGCACTTTCACACAAATAAGGAATAGCTTAAGCA
GTACCTGGATAAGTTCTCGGTTGCGCGATATGCGCTGCAGGCTGCCAATTCTTTCCAACATTACGCGTAGGCCGTTGCAATCAGCCAGCACATTG
GCCATGCGATACAGCTGCTCGGTGTCCACCTGCTCCTGGCTTTTGTTGTTCAGCGTTTCCACAAATTCCTCTGTGGCGTCTCCCAGGAGACCGCG
CATGCGATATACAATTCTCATGGCATCTCGGTCGCCTCCTTCAGCTAACCAAACTTTCTTGTAAACATCCTTAACGGGCAGATCCAAGCTTATTA
TTTTGTTGTTGACCAGCAATTCCATGCCGTTATCATCTTCCAACAGGGCGATTAGTTCACAATCCGTACAAATCTTATTCTTCACATCCCGCATC
AATGGACCCAATCCCATTTCACTCGAGGGGTAAGGATTACCCAGCATGCGACCTTGCAGAAAGTCCTCCTGCTGGGGATCTTTCTCTAATGTCAT
ATAGAACTCGCTTTCGTCATGCTCCTCGGGATGAATAATGGAATATAAGCGCTCGAAGACAAACACCGGTGTTTTAATGTCATTCATGCGGGTCT
TCTCTACGGTGTCAATAAGGATTTCCATAAAGGCACGTGTCTCCTCCTCGGTTCCGCTGGTCATATCCTCTAGCATCTCTAACAGCTTCTCCTGT
GCGTCGTCAATGAGTCGCGTACGCTGCACGACTAAGCTTCTTAGGGCAAGATAGCTTTCCAGAACTGGTCCTAGCATGCGAGTCTTGTAGGTTCT
GCGGATATTTGGACACTCTAGGAGTAGCCACAACAATTCCACATACTGGCGCAGTGCATATCCTAAGGATAAATCTGAAGAAAGCGAGTACTCCT
CCATGCGGTGCACCTTGCTGATTTCAATAGCCAGAAGCTGTGAGATTTGACTTAATACTCCTTTCAGGACCAAATACTGCAGCCAGGGTTGCTCT
GTGGCCATGTTCTTGTACAGCATTAAGTACTCTGCACTGGCTTCCCCTGCTTCGCCTACATGTTTCAAGAACGATGTCAGCATATTCAGAGCCTG
TTGCCGCCGTTCGTTAGTTCGGCTCAAGCTGCTCAGCAAGGAGCAGGCCAGCTGGCGACCGAATCTGGAGTTTGCATTAAATAGCAACGGTTGTA
TCCACTTGGCGTTGAATACAAGAGGTTTAATCACTCGTTGCTTGTCCAGCACACGTTCCCGCCAGCGTTTTCCGTACTTTTCGCTAAGGAATGCG
ACTCGCACCTCCCTCCTGCTCTTCGGCGGTGCATCTGATCCGCCGGATGCCGCCACATTCTGATCCTTGGCATTCTTTAGCTTAGCCTGGTTGTT
TGACGGCATCCGCTTGCTCCACGCTGCGTATTCATGATTACGGTCTGAGTTCAGCCAGGCCCTATAGTCCACCGTGTTGCCCTCAAACATCTTCA
TGCTACACAAATCTGTAGTGGCCACCTTCTGATTGGGCTTGCTGCCGGGCAGAACCGGGCAGATGAGATTCTGCATGATGCGCAGACAGGGGTGT
AGTACTGCTGTTACCGGACCACGAGGCAAACTGTAGAAAGAATTTAAATTATATCACATTTATATTATTTTCTAATATAAAACTTACCGGCAGTT
GCTAATGAACAGCTCAAAGATGACCTTTAGCTTGTATTCCCAGCAGATGTCGTCCTGGCCCAAGAGCACCTCCAAAAGTGTCATTTCTTGGTGCA
CAGCTGCCTCTAAACTTATCAGAGGAATCGATCCCATCAGAGCATTCTTCACCCTTGTGGTCACCAACTGCAACAGATGCATGCATGCCTCGGCA
TTATCCTTAGTCAGTACGACCAACAGGTTGCGCACTTCCTCCTGAATTAGGGGAGTGCCTCGTCGCAGGTTGTGCTCAGCCAGTTCACTGACGAG
TCCCTGACTATACAAGCACACGCGACAATCGTAATTGTAAGCCATGGCTCGCAGAAGCGTCAGACACTGCTCGGTAGATGCCAGTGCACAGCCGT
AGCAGCGATTTGTGGTGGGATTTTCGGCACCGGTTGTTGAGCCGGGATTAACCGGCGGCTGGTCCTGCTGTTGACGATCGTAGGCCACTAGTTCG
CTAAAATTAAAATTATTATTAGCCAAAAATTATAATTTCTAAATCAGTGATAGTACCTTCGACATGCCTTGACCTTCTGAACGATCTTGCTTAGC
TCCTCGAAACTGGTGCGCGATTCCACACAGTATTTCTGGGCGAGCAGCTGTATAATCTTGTTTACTTGAGAAGTGCTGTGCACGCTGGCCATGTT
GTCCTCGACCATTCGATCACTGCTACGATGCTCGGCCACCTTTTGAATAAGAAGCTCCAGCATTTGCTTGTTGGTCAGCAGCTGGCGGTAATTTC
TATCGGCTCGTTCTAGGGAGCTGTGAATCAGTGAAACAGTCTTGACCCTATCCTCTGCCGATTCTATAGGATCAACAGCGCAGCAAACACGGGCA
TACATGCTGAAATCAAATTTGGCATATTTGCAGAAGCCACAGGAGTGGCACAGGAACGGGTCCTTCTCATCGTAGTTAATGGCCCGACATTTGTG
GCACTGGAACACGTTCTCACCGCAATTTCCGCAGACTCCCGGATAAGCCGGCACTGCTGCACTACAACGTGGACATTGTAAATTCTCACTGGATC
CACTCACAGTTTCAAAGAAATCAGCAAACTCGATCATCAAATTGCATGCGGTGATTGGTAGTGGAAAATCGATCTTCAGTTCGGTCTGTGCCGAT
TGCAGGGATACTGAGCGAGCTTTGTGCCACAGAGCTGGGCGATTTTTTAGCTCCACTACCGCCTGGACACTGCGGTTGTTGTAGTAAACATTAAT
GGTTCTCACCATCTTTGTCCGCTTTAAGTCGGCAATCCGCACGATCAACTTGGAAATAGTATGGCATTGGACTAGCTTATAAATCATTGTGGTTG
TGGTGTACTTAGAGTCTGATTTAACTGATGGCAACTTTATATTAGCCATCGGCACCTCTGGATTGTTGCACACTAAACAAGGTTCCGATTCTAGG
TAGTAACCATTTACTTGAAGTATAGACTCCAAGGTGGTGTATATTGGGGCATTTGGATGCTTGCAAAGCAGTTCGTTCTGCTGCCTGAGAACATC
CACAGCGCGGGAAACGAACTCTGGCAGTCGTTCTGTTATACTTCTGGTACTTAGGGTTAGATACCCCAATAGGTCGACAAACTGCGCTGTCCTAC
GACCGTAGGTGGGCACCAATGGCCACAGGTTCCAAAATATGTTGAGAAGTTTCTCACGCTGCCGTTCATTGGCATGCTCAAAAAGTCCGGTCATA
AATGAGTGGGCCTGCCATCTCAGCTGAGTAATGTTGTTCTCCAACAGGAATATTCGCACAAATCTGATTATCAGCGCATCGCATGCGTATCTAAA
GATCTGGTGCACAAATGTACCACACTGGGCTGGATCAAACTTGGAGTAGTAGGCGTCTGTATCCTCGCTCTTCTCACGATCTGTTCGAAGTTTTC
CGGAGGCAGACGAGGTCGATGGCTGCGGCTGGGCCTGCTTAGATCCACTAGGAGGGGGTAAGTTGCAAACGGCCGCCTGTAGCAATTGTATAATA
ATAGGCGACACGCCATCATCCAACTGATAACAGGCGATTTCCATCAGCATGGCCAACGCATCTTCATGGACGACGCAGAACTTCTGCCAGTTGCC
CGTGCGCATTTGGCTTATCTCCTGGCAAGTACGTAGGTGTTCCGTCAACTCTACCAGTGCATCGTATGAAAGCATAGGAGGATTAGCGTTGTAAG
GAGCACCAGTCTGAATGCAAAAATTAAAGAATATTAATATTTAAGATAATAGTTACAATATACCAAATCACCTTGCTGCTGACAATGTTGCACAC
CCGCTTGACCACCCGGAAATGAGCGTCGAGGGAGTGACCGTCGCGATACATGCGGAACTTTTCCTTGCTGCCGCAAATGTACATCAGGAGCTTTC
GCACTTGCCGACGAAGCAGTGTGTTCAAATTTAGCATCATGTACTCACAAAGTGTAAAGGTCATCGCTTCGCAGAATCCACTATCGTAGTTATCC
GGATGGGCGCTACTTAAGCGCAGAATTTGATATGGCAATCGCACGATAATTTCAGTTAGGAGTCCATCGTAGGACTCGAAAATATCCGGGTAGTT
TTTCAGATAGTTGTGCGGTATAAGTATGGATATGTCAGGTTTAGGACCATGTTTAATGGGCTTCAGTAGCTGAACTCCGGGACCTGAAGCTCCGC
CACTGGCTTGTGCCGACTGTGAGGCTAATCCGCCACCGGCTGCATAAGGATCTCCTAGCACATTCTTCCAGTGCACCAGTAGCGTGTTTAGTGCT
TCTAGGGCGTAAACGAATGCTCCACTCTTACTGAGAACATTTGCTGTGGTACTGGCCACAAAGGAGCTATTGTCCTTAAATTGATGCGGCGGCGA
TGTTGTTCCAGTTTGCTTTGACTTTGTTTTGCCCATCAGAACTCCGAACAGGGAAAGCAATGCGAGGCGCACCTCATTGCCAGGACACTTTGTCT
CCATCTGCAATTTAAATGTTTAGATATATTTTATAGAATAATTTTTATTTACCCTTGCGGCAGCTCCTCGCTTTCCAATTTCCACATAGTCCAC
TAGAGCAGTAAGCAGATCGTGAAGCACTTGTTGATCCCTTTCGTTGTTTCCATTGAGATCGGTAGTCAACATGAGTATAACCTGGATCAGTGGGA
TTGCCTGCAGGCCATTGCACAAGTCGAATGTTCCTAGATGTTGGATAATGCTCTCCAGCACAGCAATTCTATAATGGAACATAATTGATATACCC
TAACAGCATATGATATATTTTTACACTTACCTAAGGTCATGTAGCTTGCTGAGCTTATCGTCCTCGTTTGCTTCATTATCCTCACTGCTGCTCAT
GGCACTCAAAACAGCAACACCACCGGAGCCAGCAACGCCACTGGGACCTGGCTGCTCTTGATCGTCCTTGGTGGATCCCTGACGCGGCGGCGAGG
CATTCGCGTGGTCGCCAAAGTTGCTGCTCCTGGCGGATGTTCCACCAATACTCTCTACTCCACTGCCTCCACTCTCTGATCCACCGCTGCCAGCA
GGCTCTGCTGGAGAAGTACGCAATGTTGATCCATCGGTTGCCACATTGGAACCTTCATCATCATCGGATCCACCTAGGGAGACATTGGCAGCTGC
GTTCACAGCTGCTGCCATGGCAGTAGCTTGACGGATGCCCTGAAGATTGGCCAATCCTTGCTGAAGAGACTGCAAGGCGTTTGCATCCCCACCGT
GCTGTTGGAGACTCAATGCGATGGCAATATCCATGATGGCCTCATCGTCGGCATCTTCGGGTAGGCCGAGTAAGCGAGGGAAACCGCCACCCATG
AATGCCTCCAGATTGAGCATTTGCTGCTGACCGACTCCTCCTACTCCAACTGCAGCACCTTCCGCGTCCGCATTCGGTTCGGGTAATCCACCTCC
TCCAACTGACCCATCAACAACAACGCCAGCTGCTTCCTCGATGATATCACTTGCAGCTGAAGAAGCCGCTGCTTGCAGTGCCTGCATGGTAGACG
TTGAGGGAGTCGGTGTTGAACATGCTGGGGGTGTAACTATGGCCACCTTTCTGCGCTTCATTCTTGGACTAAGCAAAAGGATCAGGGCCTCTTTG
GCGCTGTGGCTAATCACGCTAGCATCATGCTTCAGCAAATCAATGAAGTACTTGGTCATGCGACCAACCTGTCCGGGATCGGCCAAGGCAAATCC

FIGURE SHEET 711

GTACATTATCTCTACCAGACAATGGACAATGGTCTCCGGCTGGCACAAGCCTCGCTTCACAATATTCACGGGTTCGTCTAGCGTCGGTGTAACCT
TATGCAACTCCAAGACAATTCCCATGAGGGTTGGAACAATATCATAGTTGTTCTCCACGCAGATCTTCGCTAGCGATTGGGGTCGTGCGTTGGCA
ATGCCACGGACCATCAGAACTAGGCGGTAGAAAGCCTCAGGGTCGATCTCCCGCAGAGTTTCAAGTTTTCAAGCTTCGGCTGCATTGACTGTAG
TTCTCTATTTACAAACTGAAGAAGCACTCCATCCTTGTAGTTATGGTACAATGCTCTAGTTCCGTATAGAGTGGCCAGCACGTAGCGCGCCTGGG
TCTGAACAGGATTGGGCGTTGGCAGTAGCAATAGGGCACTCGCTGTTTTAACTGCCTTTTGACGCATAGAAGCAGGTACTCCAGATCCCAACAAA
TGCAGTGCACAATCCATTACTTCCAAAAGGTGATTAGCCATTCGATCCAGCTGAGTAATGCAATTGAATCCTTCTCCAAAGTTAGCGCTACTTGC
CTGGGAGGAAGATACTGCTGGCGCACTGGATCCTGGGACAGTAACATCCTCGCTTTCGTCGGGCCAGCCCACCAGCTCTTTCGATTTTCCATATA
CCTCAATGCAATCCAGTAATGTCACATGCTCCGGATCTGGAGCTTTAGCAAACACGACTTTCAATAACTTGTCGGACTGGAGCATTTCTTCCCGG
GTCAGGGGGATATCGAACCAACGTGCCCTCCTGACCGGTGTGGGTATAGTACGTCCCAGAATAGTCACAGATTGGGGAGCACGCTGTACGTCCTG
AGTTCCAATTAACACTCTTATTCCCACGATTACAACATTGGGATCATTATTGATCACCTCCAGAGTAAAGCCATTCGATCGGGTGCTGGCCACAA
ACATTCCCGTTGAGAACAGACGCGTCTTTAGTTTTGTTTGTTGTAAATCTGGAGCAGATCGTTGCCTCCAAATTCCACATCGGCTAGCATGTTG
CAGTGCTCGAAAAAGTCAATTGGGAAAACGGGCTGACCTCCAGCTGTGGGTTGCTTCTGTTGTTGGCTTGCCTTTCTGCTGGTCATCTTTCCAGA
TGCTGTATTTGATTTGGACTTTGAAGTCGAACCAGATCCACCTCCCTTAGCCATCAAGGTGGACGAGTACAACTGATTACCAAATGGCTGAACCT
GTGGCGATAGCCAGAAGCTAGTGTATTCTGGTTGAGCGGAAAAGATCCTCAAGCTTCCATCCTCGCAGAGGAGCAAAAGCGTAGTTTTTTCCACT
CCGGCAACCGCATGACGAATGCCAACAACGTCCATGATTCGTGACTTGGCCGATTGTGCCTTGATCTCTTGCAGGTAAATCCGTTCAGGGGTTAT
CATCAATATAATCGGATTATTCGATGTCTGCATGCTGGCGTAAACCAATCCTGGATGCCCTGTAACCTCTGTCCACTGCACGAGAGGCTGTAGTG
GTCCCTTCGAAGCTGACTTACTAGCCGAATTTGTGTCCAGGTGATATATTCCCTTCACGCCTTCACTTACATTGGTGAGTGGTGAAAAGAAGCTC
CTTCCGCAAGAATAACTGTAGAAGAGCAGCTGTAGGGTATGCGAATAGTAGATGGATACTCCACCGCCTCCGATATGACCGGCAATATCCTTGAT
ATGTTGGTGGCTCAGCTCCAAAGTGTTGGTTACATAGAAATCTCCATGAACCGCTAGACTCTGTTGATCCAACTGCTGAGTATAGATGTATCCGC
TGCTTGCAAAGGTCAGCATATTGTAGTTGCCATCCTGGTACACAAACGTGCAATCTCTAATTTTGCCAACGGCCACTAGGTAATAGTACTTTGGG
CTATATGTATCCACTGCCAAATCGTAAATCTTTACATAATCCGAAGTTACAACGGCAAGAAGAGTCTGTGAGCCAGGCAGCCACACAGCTTTCTT
GATGTAGTTTCCATTTTCCAGTTGGGGGTTCACTACTATGTGTTCGTTAGTACTGCCACTGCTTGAGAAGGTGAGAATGTGACACTCTTTTAGGC
CACAAACTGCAAGGCAATCCTCATTGCACGGATTAGCAGCTAGGGAGATAACCGTGCAGGCAATGGGTGCAGAACTCAATTGCGTTAGAGTTAAC
TTTCTCTTGGAGGCATCTGCTTGCTTCAACAGTGCCGACAGCTGGAGGATGGTCACCTTTCCCTTCTCATGGGATACAGCCAACTGTTGACGACG
TCCATGTGGCGAGGACAAACAGCAGAAGGCAACACGGCGGACAACTCCGGATGATAGTAGGTGCTTTATAGTCTGACCTTGGTCGCCAGAATAGT
TCATTCGAACATTCTCAAAAGCTCCCTCTTGTGAGCCCAAAGTTGCAAACATCAGTTGATCGGTTACCTGGAAGCTCTGTTCAAGCAGGTGGAGT
CTCTCCAAGGCCGCAGTTGCTCTCTTGTGGCAGCCGACAATGGAGTATAGCATACAATTTTCGTTTATTGATGGTAGCAGCAGGTCAAAATACTC
TAGGATGCATCTTACGACCAGCAGCCACTGATCCTGGTGCTGAAGTGTCTCTCTGTAAGGTTCCAACAGTTTGGTAAGTACTGCGATCCGTTCAT
TAGTCAATGAATCCTTTCGCGTAAGTACTGGCTGGCCAACTGGTAAGCTGCTCCTCTTCTTTCCAGCGAGTAAGCTCATGTGGGACGGTAGATAG
CTGCCAATTCCAGCTGAATCTCTAACCTCATTGCTGCCGATACGCCTACTCAATGCCTGACAGGATCCGTCCTCCTTGGCTCCGCAGTCACAGAA
GAAATTTCCATATTTGGCGTAACTGACATCATGTCCCTTATGGCAAACCCTTGCGCACACAGAACAGACGCCAACTGTGTTTATCATGTTGCAAG
TATGACAATGATACCAATGTTGGTTCATGAACTCCTTTTGGGTCTGCGAGAAGGTACACAGCTTGTTGTTCAACGTGTCCTCGTCGGAATCGTCA
AGCAACGAGTCTTGCTCACCTTCCTCGGCTAGCTCGTCATATAGCTCATCAATATCGGTCTGTAGTTCATCATCCCACGGCGGGTTATGTTGCCT
ACTGCCTCGGAAGCCAATGCTCTGAAGAAGTTCGCTTAAATAGCGCAACTGGGCACTTACGTTCTCTGCATGTTTCAAGTGTTTGTCCGGTAATT
GCAATTTGGCCAGTTCCAGCCAAAGGAGGGTGGTATTGAACAAGGCGACATGGCCGCGTGCTGGACTGGCGTCAGCTAGAGTAATCATTATCTGT
AGTACATCTGCAAAATCGCAGCCTTCCTGGGGTGGTGAAATTAATGTTTGTCCGAGCTGAAGCAAAGCTTGGAACAGTGGTGGAGCTATCTGCGA
TGCTTTGCTTTGATCTTTCACCAATGACTTCACGAAGCTTAAGAGCAACGCGCCATTTCGTTCGCTATCACTATGATCGCAAGCCTGTGAAGATT
CTTCCGACGGATTTGGCTGCGCAGCCTGCCACAAACTCAGAATCTGCGAGGTATTGGCTGCAGCTCCTCCGGTTCCTGGGTTACTTTCTCCGCCT
CCCGCTGCAGTTCCGCAATCGTATTCAATTTCCATGGGATCCAACTGGTCTGAGATACTTGGCATAGCCGAAACGGTGGCCATATTTGTTGGCGT
CTGAGCATTGCTGCTGGAGCTACTCGACGGCTGCAAAATGCTGGTGAGCATCCGGCAGGTGGTGTCTAATGCCTCGGAGGTGCTTACATCGGTAC
TCACATTAGGGCCGTAGATAATGTGGCCCAACCATTGCTTTAAACGAGCTACGTCAACTGTGGCCAGTTCCGAGAAACACTCAACCAGATCTTCA
TGCTGGAACTGTGAATCCGCTTGTAAGGATAGCTGGAAAAGTCGGTTAACAAATTGCAGCATCTTGCGCGCATAGCTAACAGGCAGACTGGTGCC
AGTGAACGATAGCAAAAGTGTGGTAAGACTCCCAGAGCGCTGATCTTTGAAAAACTGGCGCATGGCCTGAACTGCCACCGGCTTTTCCAGCATTT
TGAACATAGTTTTAAGCACGGCAAACAGCATGGACTCGTTAAACATAGCACGATCCTGATCAAGAGGAGCTCCGCCACTAGGCCCCGCAGACTGG
GGCTGACGAAGATCGGCAGCAAACTCTTTGAGCATGCGATAGCAATATCCAACCATGTGCTCGTAAAGCAGCAGCTTTTGTGCCTCTTGTGTCAG
ACCACTGAGGATCTCGCGCAGACAATGCTCGCTGTGTCCTTGCAAGTAATCCGTTCGCATGTCCAGCATTGAGGAGATAAGCAATTGCTTTAGCT
GAGTCTCTACTTCTGCGTTCGCGGTGCGATGTGGTAGCAGCAACTCAAACAATTGCAGGATAGACTTTAAGCAGTGTTTCAGAGTGTGCAGGGTA
GAGTAATTGGATCCTCGTGTCAGCTCAATAATGTGAGCATCAATAACGTTCAAAATATATGGTTCCACCGGATGTTGCTTTCCATTGAATGCAAA
ATCATTGACCATTAGGCACTTTGGCCATTCGTTTGCTATTAGTTGTTTGTCCTCGTTGGGCAGGAGTTTTAGAAAAGCTGCATGGAGTTCTAACA
TAATTGCTGGCTTATCGCTTACAATGGGCACAATCAAATTCAGTGCCTTCTCCGGTGTTGAACTTGACAACTGCTTTAGCATTTGGCCACGCACG
ATCACCGAAAGCAATTGGTAAGAATTCATGAGCTTTACCATTAGCTCGTTTACAAGTTGATTATACTTTTGCAAATCACTTGACAGCTTACCGTC
GTCGTCTTGTTTCAATTTTTGATCATCAATTGATTCGTTGGAAGAATAAAGTTCCGGATCGTTTGACGATGAAGTTAAGGATGTACCAGCGGACT
GCTCGCCAGCGGCATCTTCGCTCTCTTTTCGCGGCCACTTGAGGCCCTCCTTGTTTGCCCAGGCTACCGCCTGCATGTGCGCCACCAAAGAATCA
AAAAGGATGAGATCGGAGAGGCGGGGAGTTCCTGCAAAATGAATATTTTCAATACATTGTGGTTTGTTTTTAACCATATTATAAGTTTTTTAGTA
CTTACCATTTCCATTCATTTGACTATTGAACGCCTCCACACCAAGAATTGTTTGCTTGAGACTATATTTTATATCGGCACCTATGTCGCCCACAT
GAGTCCACAACGTCTCAGCGTACTGGGTATACATTCCCTGCTTGATTAGGCTGCTAACGACTAGGTAGTGAGAACTGGCCAGGGGTAGACGTATA
CTCCACATCAGTGAGTGCAGATTGGGTGATCGCTCTGCCTTCAGCGACTCTACGTGAGAAGTAGAGGGCGGCAAACCCAAATTCAGCTTCCAGGC
AATCGTAAAGCAATACTGTATAGCGCAAAGATTATGCATGCTCGCTTCCTTGTCCTTTTCCTTGGAATACATTGACATGTCGGTGATGGATAGTA
TGTCAGTCAATGCATCCACCAGTAGCGGATATTTAAGCTTATCCGGTGTGCAGAGAATAAAGTTCCAAGCCAAACCATCCAGCTTAAATTCCTGA
GCCCAGTAGGATATCTCGGGATCACCCATTACCAGAGAGTAAAAAGTTGGGCGAATTGCTAAAAAAAAAATCAAGATGGTTGAGTATCGCTGGAA
TTGGAGATTAAATTCTCCACTTACATGAGCCATATTCGCCGGCCGACTTGCGGAAATTCTCTTCAATATCATGGCGGCAATAGGAATTCAGTTTG
GTTCGGCAGTTTAGCAGATCCGTGATCTTTTGGGTGTCCGGCATGCTGCTCACACTAAAAAGATTCCAGCGCACCTGGTCTAGCAATTCCGGAGG
CGCATTGTACAAGTGCTTCATAAGATACTCCAAAAAGAGCAGCAAGCGAGACAGCAGCATAATTTGGCTGTTTTTTACGGGTCTATCCTCGCTGA
TTCCACGACAAACTTCTGCGCAACGGATAACACCGCCAGCCGTTAAAAGCAGAATGGATTTCTTTTGCATCAGATTGAGCGAATGAAATAGGAAA
AGCAGCAGTTGGGCGTGCTCAATGTTAAGGTCTTCATAGTCAGAATCACTGGCGGTATTCGAAGAACAAACTCCTTCCACCAACGTGTTAATAAG
GCGGTGCCACACGGACAGGCAGGCGGCTTCCTTCTCTTGTGTTGGCTTCAGCAAAAGAATTTGCACCAGTACAGACAGAGTACTCGGATAAACTT
GTAAAGGCCAGGTGTTTGTATCAGTAGACCATGGCGATATAGACAAGTGCTGCAGCAGATTTGACTGCAATTGCTCGGACAGCAATGAAGTGGAA
ATCAAATTGTGAATATATCGGCCTGCAGCTCCCGAAAATCGAATCATCGACGTCTGCCACTTGGTAGAAGCTCCTGCAGAGGTTCCTGCTCCTGC
ACTGGCAGCTGGGGCATTTCCCGACCCCTGATCGCTCTCATTTCGCATCACGTCGCGGTCAAAATCTTTGATTATATTTGCCATTAACAGCATTT
GCTGATCACTAACGCCTGCCTTTACATAGCGCTGCATGTAGGCATGTCGATTGGCCAAAAATTGATCCAGGAAACAGAATATGTCTGCGGCCAAG
TCTAAATACTCATGTGGCTCATCTAGCTTGGGGACAAGGGCGCTCTTCTGTTCAGCACGCTCTTGTGTGGATGTGTTTGCATTATCATCATGGGT

FIGURE SHEET 712

TTCTGGAGAAAGAGTTTCCTTAAACCAGTGGCCCAGGTAACTCTCACTATCGTCCTCCTCGGAGTTGTCCGAACAGGAGAGAGAATCGTTGAAAT
AAGTCGTAGAATCTGAGTAGCTTATGGGTTCGCATTCCGTACGATCCTTGGCGGAAGCGCGCTTTAAGGTGCATGCCTTGCGATAAGCCACAGTG
GCTAGAAAAGTGAAAAGTTGATGCAGAGTGGCTGTATTCAGCACGCGGACAATCCGCTCCAGCGAACTGTAGTTCTGCAAAATATCGAACTGTGC
AGGCTCCGGGAGCTCTGTGGATTCGAGACTCTGTCCGCATGCGGCTTCAACCTTTAGATCTTCTATTAGCTCTGAGAGCAATTTAATGCTGTGGT
TAGCAATAGCTGCATTGAGTTCTCCAAATCCTTGCTGTACCTTGAAAAGGTTGACTCTGGCAATAGGTGTAGTAGGTGCGGTTCCAGCCTCACTA
CCAGACTTGGTCGCTTTTGACGCCGACTTCGATGCCGAATCCGAGCTAGATCCACCGCTTCCAGAGGCGCCCATTGCTCCTTGTATACCGCTAAT
TAGCAGCCAGCTGCCATAGCAGAGATGGTTCTGATATACATGAATCCTGGCCGAAGTTTTGAACATGTGACCAATATTGGAGTAGATCTCTAAAG
CTTTGTTCACTATGCTACAGGCCTGATCCTCAAAGTCGTCATGGTCTTTGTTGGATTGCCCACCACTAGAACCTCCTACTCCGCTTCCTTGACTA
GTGGATGCAGTCTGTTTCTGAGAGCTGCTGGCCTGGCTCATACCGAGAACACTGGTGGCTATTGAGGTCAACACAGCATTGTATAGCGCAGCAAT
ACCACACATTGATAGTCGTTCAATTCTACTGGGAGTCAGTGGCTGCATCTCGATCAGGGCTTGGGCCTGACTCAAAATAGTCAGATCAGTAAGCA
TGTGATTCATGCTCGATTTCACTGCAGTGGCCTCCACTTGGGTCAGTGGCAAATAAAGCGATTTACCGCCGTTGATGGTCTCCATATATTTGGAT
CGGTATCGATTGAGTATGGGCAGGCTCACACACACATCCAGCAGGGTATCCACTCCGTTTTGCTCCTGGAAGTACTCCACATTGGCCGCCAGGAT
TTGTTCCTGAAAGAAGTAAGCTTTTAATATTGCGTATCTCGTTTTTAAGAAAATATAAATTTGCTCATAGCTAATAGTTATACACAACTTCTAAA
TTGATCGAGTAGGATAAATATTTTCATTAGATAGAATATTGCATTTTAGTTTAGTTGTGTAATATATCCGTACCTACTCAATTCAAGAGTAATTT
ATAATAATAACAGACAAATATGACCGATCTTAGGGAAGCTATTAAAACAGGAGTTTAAGTTATTTGCTCACAGTGCAGTCGGTGACCTCCTCGCT
GAGTGGAACCCAAGTCATCTTGCCGGGCTCTAAAGGAGCAATCAGTTGCTGCAGAATAACCGAGGACAGGTCCGACCGGGATCGCTTAATCTCCG
ACTTGGGCGACTCCTTGTCGTTGCTGGCCCCACTTCCGGAGGAACTGCTGCTGGGCATAATGCTCTTGGTGGTCGACTCGGGATGTTTGCAGCTT
TTAAGAACATTAGCCACCGCATTGTAGTCGAACATGGATGACGACGCTGATGCTGGGCACTCCCGGCCCTCGCAGAGCATCTTGAGGGCGCCCAG
GAGCCACTTGGTCTCGTAGACGGACACCCTGGGCAGTCTATAGATAATAAACCGGATAAGCACGGCGGTGGCATCGTGCAACTGACAAATCTGCG
TCTGGCAAACTGAAAAGCACCAAGATGATAAATGTAGCGAACGCGAATTGGCGCAAGTGAATCACTCGATTCTTGGCCAAACATTTCTTTGTTTT
GTTTTCATTTGGCGAAAAATCATTAGGGTGCACTTACTTGTCTTGATTTGCATAAGTTTGTCCGCCGCCAGGGCCGCAAAGGCCGTGTAAAACTG
CGTGAAATTGCTTTCCTCCTCGAAAAAGTCATGTTCGCTATGCAAATATCGGAATAGAGCGTTGTTAGTTCTCGATATTAAAGAATTTTCAAAGC
TTTTTGCTATTTCGTCACCGGAGCGGCCATATTTAATTTTGCAAGTCACTTTTTGCACTAGCAGAAAATTTTTCACTACGCCATTCGGTAGGCGA
AAAGTTCTAGATGATCGTTTGTACTTACCATCGCGTGATAGCTTTGAGCAAATTAACAACTTCGTTCTTGTTTAAGGCTCCTGTACGGTTAAGTA
TCAGGGCTTTAACAACGGAATTCCAATCCGTTCCGCCGCTGTGGGCCGACATTATTGTTTAAATAATCTCGTCAATTTGCCCGATAGTACTGAGT
ACTCGGCCTACTGTGTGGCCAGATTTCATTAACGGTAAAATGCCGTGCGAGCAGGGATACCACACAGCTTTAATCATTATTCCAATCAGCTGTTT
TAAAAATACATAAAAAAGTAGTGAATAACCAATATATGAAAAAAACTGTACACTGCACAAAATATATATATATATATATATATAACTATAATATT
TTAAACGTATTTGGACAAGCTAATAAATGTTTTGTTTATTCGTCTAAAATATGTAAAGCAAACTAGTGATGCTAGCTTTAAAATAATGATTATTT
AATTATTAAATATTAGCGACATATGTATATTTTTTTGTTTAAATTATCTTCTAAACATCTTAATCGGCTGCAGGCTC
(SEQ ID NO: 1339)

Exon: 18222..18079
Exon: 17897..17803
Exon: 17679..17267
Exon: 17011..14845
Exon: 14783..14256
Exon: 14186..8201
Exon: 8143..7939
Exon: 7889..7197
Exon: 7135..5472
Exon: 5415..4933
Exon: 4875..2940
Exon: 2884..1288
Exon: 1224..1001
Start ATG: 18197 (Reverse strand: CAT)

Transcript No. : CT34171
AATTGACGAGATTATTTAAACAATAATGTCGGCCCACAGCGGCGGAACGGATTGGAATTCCGTTGTTAAAGCCCTGATACTTAACCGTACAGGAG
CCTTAAACAAGAACGAAGTTGTTAATTTGCTCAAAGCTATCACGCGATGCGAACATGACTTTTTCGAGGAGGAAAGCAATTTCACGCAGTTTTAC
ACGGCCTTTGCGGCCCTGGCGGCGGACAAACTTATGCAAATCAAGACAATTTGCCAGACGCAGATTTGTCAGTTGCACGATGCCACCGCCGTGCT
TATCCGGTTTATTATCTATAGACTGCCCAGGGTGTCCGTCTACGAGACCAAGTGGCTCCTGGGCGCCCTCAAGATGCTCTGCGAGGGCCGGGAGT
GCCCAGCATCAGCGTCGTCATCCATGTTCGACTACAATGCGGTGGCTAATGTTCTTAAAAGCTGCAAACATCCCGAGTCGACCACCAAGAGCATT
ATGCCCAGCAGCAGTTCCTCCGGAAGTGGGGCCAGCAACGACAAGGAGTCGCCCAAGTCGGAGATTAAGCGATCCCGGTCGGACCTGTCCTCGGT
TATTCTGCAGCAACTGATTGCTCCTTTAGAGCCCGGCAAGATGACTTGGGTTCCACTCAGCGAGGAGGTCACCGACTGCACTGAACAAATCCTGG
CGGCCAATGTGGAGTACTTCCAGGAGCAAAACGGAGTGGATACCCTGCTGGATGTGTGTGTGAGCCTGCCCATACTCAATCGATACCGATCCAAA
TATATGGAGACCATCAACGGCGGTAAATCGCTTTATTTGCCACTGACCCAAGTGGAGGCCACTGCAGTGAAATCGAGCATGAATCACATGCTTAC
TGATCTGACTATTTTGAGTCAGGCCCAAGCCCTGATCGAGATGCAGCCACTGACTCCCAGTAGAATTGAACGACTATCAATGTGTGGTATTGCTG
CGCTATACAATGCTGTGTTGACCTCAATAGCCACCAGTGTTCTCGGTATGAGCCAGGCCAGCAGCTCTCAGAAACAGACTGCATCCACTAGTCAA
GGAAGCGGAGTAGGAGGTTCTAGTGGTGGGCAATCCAACAAAGACCATGACGACTTTGAGGATCAGGCCTGTAGCATAGTGAACAAAGCTTTAGA
GATCTACTCCAATATTGGTCACATGTTCAAAACTTCGGCCAGGATTCATGTATATCAGAACCATCTCTGCTATGGCAGCTGGCTGCTAATTAGCG
GTATACAAGGAGCAATGGGCGCCTCTGGAAGCGGTGGATCTAGCTCGGATTCGGCATCGAAGTCGGCGTCAAAAGCGACCAAGTCTGGTAGTGAG
GCTGGAACCGCACCTACTACACCTATTGCCAGAGTCAACCTTTTCAAGGTACAGCAAGGATTTGGAGAACTCAATGCAGCTATTGCTAACCACAG
CATTAAATTGCTCTCAGAGCTAATAGAAGATCTAAAGGTTGAAGCCGCATGCGGACAGAGTCTCGAATCCACACAGAGCTCCCGGAGCCTGCACAGT
TCGATATTTTGCAGAACTACAGTTCGCTGGAGCGGATTGTCCGCGTGCTGAATACAGCCACTCTGCATCAACTTTTCACTTTTCTAGCCACTGTG
GCTTATCGCAAGGCATGCACCTTAAAGCGCGCTTCCGCCAAGGATCGTACGGAATGCGAACCCATAAGCTACTCAGATTCTACGACTTATTTCAA
CGATTCTCTCTCCTGTTCGGACAACTCCGAGGAGGACGATAGTGAGAGTTACCTGGGCCACTGGTTTAAGGAAACTCTTTCTCCAGAAACCCATG
ATGATAATGCAAACACATCCACACAAGAGCGTGCTGAACAGAAGAGCGCCCTTGTCCCCAAGCTAGATGAGCCACATGAGTATTTAGACTTGGCC
GCAGACATATTCTGTTTCCTGGATCAATTTTTGGCCAATCGACATGCCTACATGCAGCGCTATGTAAAGGCAGGCGTTAGTGATCAGCAAATGCT
GTTAATGGCAAATATAATCAAAGATTTTGACCGCGACGTGATGCGAAATGAGAGCGATCAGGGGTCGGGAAATGCCCCAGCTGCCAGTGCAGGAG
CAGGAACCTCTGCAGGAGCTTCTACCAAGTGGCAGACGTCGATGATTCGATTTTCGGGAGCTGCAGGCCGATATATTCACAATTTGATTTCCACT
TCATTGCTGTCCGAGCAATTGCAGTCAAATCTGCTGCAGCACTTGTCTATATCGCCATGGTCTACTGATACAAACACCTGGCCTTTACAAGTTTA TCCGAGTACTCTGTCTGTACTGGTGCAAATTCTTTTGCTGAAGCCAACACAAGAGAAGGAAGCCGCCTGCCTGTCCGTGTGGCACCGCCTTATTA
ACACGTTGGTGGAAGGAGTTTGTTCTTCGAATACCGCCAGTGATTCTGACTATGAAGACCTTAACATTGAGCACGCCCAACTGCTGCTTTTCCTA
TTTCATTCGCTCAATCTGATGCAAAAGAAATCCATTCTGCTTTTAACGGCTGGCGGTGTTATCCGTTGCGCAGAAGTTTGTCGTGGAATCAGCGA
GGATAGACCCGTAAAAAACAGCCAAATTATGCTGCTGTCTCGCTTGCTGCTCTTTTTGGAGTATCTTATGAAGCACTTGTACAATGCGCCTCCGG
AATTGCTAGACCAGGTGCGCTGGAATCTTTTTAGTGTGAGCAGCATGCCGGACACCCAAAAGATCACGGATCTGCTAAACTGCCGAACCAAACTG
AATTCCTATTGCCGCCATGATATTGAAGAGAATTTCCGCAAGTCGGCCGGCGAATATGGCTCATCAATTCGCCCAACTTTTTACTCTCTGGTAAT
GGGTGATCCCGAGATATCCTACTGGGCTCAGGAATTTAAGCTGGATGGTTTGGCTTGGAACTTTATTCTCTGCACACCGGATAAGCTTAAATATC
CGCTACTGGTGGATGCATTGACTGACATACTATCCATCACCGACATGTCAATGTATTCCAAGGAAAAGGACAAGGAAGCGAGCATGCATAATCTT
TGCGCTATACAGTATTGCTTTACGATTGCCTGGAAGCTGAATTTGGGTTTGCCGCCCTCTACTTCTCACGTAGAGTCGCTGAAGGCAGAGCGATC
ACCCAATCTGCACTCACTGATGTGGAGTATACGTCTACCCCTGGCCAGTTCTCACTACCTAGTCGTTAGCAGCCTAATCAAGCAGGGAATGTATA
CCCAGTACGCTGAGACGTTGTGGACTCATGTGGGCGACATAGGTGCCGATATAAAATATAGTCTCAAGCAAACAATTCTTGGTGTGGAGGCGTTC
AATAGTCAAATGAATGGAAATGGAACTCCCCGCCTCTCCGATCTCATCCTTTTTGATTCTTTGGTGGCGCACATGCAGGCGGTAGCCTGGGCAAA
CAAGGAGGGCCTCAAGTGGCCGCGAAAAGAGAGCGAAGATGCCGCTGGCGAGCAGTCCGCTGGTACATCCTTAACTTCATCGTCAAACGATCCGG
AACTTTATTCTTCCAACGAATCAATTGATGATCAAAAATTGAAACAAGACGACGACGGTAAGCTGTCAAGTGATTTGCAAAAGTATAATCAACTT
GTAAACGAGCTAATGGTAAAGCTCATGAATTCTTACCAATTGCTTTCGGTGATCGTGCGTGGCCAAATGCTAAAGCAGTTGTCAAGTTCAACACC
GGAGAAGGCACTGAATTTGATTGTGCCCATTGTAAGCGATAAGCCAGCAATTATGTTAGAACTCCATGCAGCTTTTCTAAAACTCCTGCCCAACG
AGGACAAACAACTAATAGCAAACGAATGGCCAAAGTGCCTAATGGTCAATGATTTTGCATTCAATGGAAAGCAACATCCGGTGGAACCATATATT
TTGAACGTTATTGATGCTCACATTATTGAGCTGACACGAGGATCCAATTACTCTACCCTGCACACTCTGAAACACTGCTTAAAGTCTATCCTGCA
ATTGTTTGAGTTGCTGCTACCACATCGCACCGCGAACGCAGAAGTAGAGACTCAGCTAAAGCAATTGCTTATCTCCTCAATGCTGGACATGCGAA
CGGATTACTTGCAAGGACACAGCGAGCATTGTCTGCGCGAGATCCTCAGTGGTCTGACACAAGAGGCACAAAAGCTGCTGCTTTACGAGCACATG
GTTGGATATTGCTATCGCATGCTCAAAGAGTTTGCTGCCGATCTTCGTCAGCCCCAGTCTGCGGGGCCTAGTGGCGGAGCTCCTCTTGATCAGGA
TCGTGCTATGTTTAACGAGTCCATGCTGTTTGCCGTGCTTAAAACTATGTTCAAAATGCTGGAAAAGCCGGTGGCAGTTCAGGCCATGCGCCAGT
TTTTCAAAGATCAGCGCTCTGGGAGTCTTACCACACTTTTGCTATCGTTCACTGGCACCAGTCTGCCTGTTAGCTATGCGCGCAAGATGCTGCAA
TTTGTTAACCGACTTTTCCAGCTATCCTTACAAGCGGATTCACAGTTCCAGCATGAAGATCTGGTTGAGTGTTTCTCGGAACTGGCCACAGTTGA
CGTAGCTCGTTTAAAGCAATGGTTGGGCCACATTATCTACGGCCCTAATGTGAGTACCGATGTAAGCACCTCCGAGGCATTAGACACCACCTGCC
GGATGCTCACCAGCATTTTGCAGCCGTCGAGTAGCTCCAGCAGCAATGCTCAGACGCCAACAAATATGGCCACCGTTTCGGCTATGCCAAGTATC
TCAGACCAGTTGGATCCCATGGAAATTGAATACGATTGCGGAACTGCAGCGGGAGGCGGAGAAAGTAACCCAGGAACCGGAGGAGCTGCAGCCAA
TACCTCGCAGATTCTGAGTTTGTGGCAGGCTGCGCAGCCAAATCCGTCGGAAGAATCTTCACAGGCTTGCGATCATAGTGATAGCGAACGAAATG
GCGCGTTGCTCTTAAGCTTCGTGAAGTCATTGGTGAAAGATCAAAGCAAAGCATCGCAGATAGCTCCACCACTGTTCCAAGCTTTGCTTCAGCTC
GGACAAACATTAATTTCACCACCCCAGGAAGGCTGCGATTTTGCAGATGTACTACAGATAATGATTACTCTAGCTGACGCCAGTCCAGCACGCGG
CCATGTCGCCTTGTTCAATACCACCCTCCTTTGGCTGGAACTGGCCAAATTGCAATTACCGGACAAACACTTGAAACATGCAGAGAACGTAAGTG
CCCAGTTGCGCTATTTAAGCGAACTTCTTCAGAGCATTGGCTTCCGAGGCAGTAGGCAACATAACCCGCCGTGGGATGATGAACTACAGACCGAT
ATTGATGAGCTATATGACGAGCTAGCCGAGGAAGGTGAGCAAGACTCGTTGCTTGACGATTCCGACGAGGACACGTTGAACAACAAGCTGTGTAC
CTTCTCGCAGACCCAAAAGGAGTTCATGAACCAACATTGGTATCATTGTCATACTTGCAACATGATAAACACAGTTGGCGTCTGTTCTGTGTGCG
CAAGGGTTTGCCATAAGGGACATGATGTCAGTTACGCCAAATATGGAAATTTCTTCTGTGACTGCGGAGCCAAGGAGGACGGATCCTGTCAGGCA
TTGAGTAGGCGTATCGGCAGCAATGAGGTTAGAGATTCAGCTGGAATTGGCAGCTATCTACCGTCCCACATGAGCTTACTCGCTGGAAAGAAGAG
GAGCAGCTTACCAGTTGGCCAGCCAGTACTTACGCGAAAGGATTCATTGACTAATGAACGGATCGCAGTACTTACCAAACTGTTGGAACCTTACA
GAGAGACACTTCAGCACCAGGATCAGTGGCTGCTGGTCGTAAGATGCATCCTAGAGTATTTTGACCTGCTGCTACCATCAATAAACGAAAATTGT
ATGCTATACTCCATTGTCGGCTGCCACAAGAGAGCAACTGCGGCCTTGGAGAGACTCCACCTGCTTGAACAGAGCTTCCAGGTAACCGATCAACT
GATGTTTGCAACTTTGGGCTCACAAGAGGGAGCTTTTGAGAATGTTCGAATGAACTATTCTGGCGACCAAGGTCAGACTATAAAGCACCTACTAT
CATCCGGAGTTGTCCGCCGTGTTGCCTTCTGCTGTTTGTCCTCGCCACATGGACGTCGTCAACAGTTGGCTGTATCCCATGAGAAGGGAAAGGTG
ACCATCCTCCAGCTGTCGGCACTGTTGAAGCAAGCAGATGCCTCCAAGAGAAAGTTAACTCTAACGCAATTGAGTTCTGCACCCATTGCCTGCAC
GGTTATCTCCCTAGCTGCTAATCCGTGCAATGAGGATTGCCTTGCAGTTTGTGGCCTAAAAGAGTGTCACATTCTCACCTTCTCAAGCAGTGGCA
GTACTAACGAACACATAGTAGTGAACCCCCAACTGGAAAATGGAAACTACATCAAGAAAGCTGTGTGGCTGCCTGGCTCACAGACTCTTCTTGCC
GTTGTAACTTCGGATTATGTAAAGATTTACGATTTGGCAGTGGATACATATAGCCCAAAGTACTATTACCTAGTGGCCGTTGGCAAAATTAGAGA
TTGCACGTTTGTGTACCAGGATGGCAACTACAATATGCTGACCTTTGCAAGCAGCGGATACATCTATACTCAGCAGTTGGATCAACAGAGTCTAG
CGGTTCATGGAGATTTCTATGTAACCAACACTTTGGAGCTGAGCCACCAACATATCAAGGATATTGCCGGTCATATCGGAGGCGGTGGAGTATCC
ATCTACTATTCGCATACCCTACAGCTGCTCTTCTACAGTTATTCTTGCGGAAGGAGCTTCTTTTCACCACTCACCAATGTAAGTGAAGGCGTGAA
GGGAATATATCACCTGGACACAAATTCGGCTAGTAAGTCAGCTTCGAAGGGACCACTACAGCCTCTCGTGCAGTGGACAGAGGTTACAGGGCATC
CAGGATTGGTTTACGCCAGCATGCAGACATCGAATAATCCGATTATATTGATGATAACCCCTGAACGGATTTACCTGCAAGAGATCAAGGCACAA
TCGGCCAAGTCACGAATCATGGACGTTGTTGGCATTCGTCATGCGGTTGCCGGAGTGGAAAAAACTACGCTTTTGCTCCTCTGCGAGGATGGAAG
CTTGAGGATCTTTTCCGCTCAACCAGAATACACTAGCTTCTGGCTATCGCCACAGGTTCAGCCATTTGGTAATCAGTTGTACTCGTCCACCTTGA
TGGCTAAGGGAGGTGGATCTGGTTCGACTTCAAAGTCCAAATCAAATACAGCATCTGGAAAGATGACCAGCAGAAAGGCAAGCCAACAACAGAAG
CAACCCACAGCTGGAGGTCAGCCCGTTTTCCCAATTGACTTTTTCGAGCACTGCAACATGCTAGCCGATGTGGAATTTGGAGGCAACGATCTGCT
CCAGATTTACAACAAACAAAAACTAAAGACGCGTCTGTTCTCAACGGGAATGTTTGTGGCCAGCACCCGATCGAATGGCTTTACTCTGGAGGTGA
TCAATAATGATCCCAATGTTGTAATCGTGGGAATAAGAGTGTTAATTGGAACTCAGGACGTACAGCGTGCTCCCCAATCTGTGACTATTCTGGGA
CGTACTATACCCACACCGGTCAGGAGGGCACGTTGGTTCGATATCCCCCTGACCCGGGAAGAAATGCTCCAGTCCGACAAGTTATTGAAAGTCGT
GTTTGCTAAAGCTCCAGATCCGGAGCATGTGACATTACTGGATTGCATTGAGGTATATGGAAAATCGAAAGAGCTGGTGGGCTGGCCCGACGAAA
GCGAGGATGTTACTGTCCCAGGATCCAGTGCGCCAGCAGTATCTTCCTCCCAGGCAAGTAGCGCTAACTTTGGAGAAGGATTCAATTGCATTACT
CAGCTGGATCGAATGGCTAATCACCTTTTGGAAGTAATGGATTGTGCACTGCATTTGTTGGGATCTGGAGTACCTGCTTCTATGCGTCAAAAGGC
AGTTAAAACAGCGAGTGCCCTATTGCTACTGCCAACGCCCAATCCTGTTCAGACCCAGGCGCGCTACGTGCTGGCCACTCTATACGGAACTAGAG
CATTGTACCATAACTACAAGGATGGAGTGCTTCTTCAGTTTGTAAATAGAGAACTACAGTCAATGCAGCCGAAGCTTGAAAAACTTGAAACTCTG
CGGGAGATCGACCCTGAGGCTTTCTACCGCCTAGTTCTGATGGTCCGTGGCATTGCCAACGCACGACCCCAATCGCTAGCGAAGATCTGCGTGGA
GAACAACTATGATATTGTTCCAACCCTCATGGGAATTGTCTTGGAGTTGCATAAGGTTACACCGACGCTAGACGAACCCGTGAATATTGTGAAGC
GAGGCTTGTGCCAGCCGGAGACCATTGTCCATTGTCTGGTAGAGATAATGTACGGATTTGCCTTGGCCGATCCCGGACAGGTTGGTCGCATGACC
AAGTACTTCATTGATTTGCTGAAGCATGATGCTAGCGTGATTAGCCACAGCGCCAAAGAGGCCCTGATCCTTTTGCTTAGTCCAAGAATGAAGCG
CAGAAAGGTGGCCATAGTTACACCCCCAGCATGTTCAACACCGACTCCCTCAACGTCTACCATGCAGGCACTGCAAGCAGCGGCTTCTTCAGCTG
CAAGTGATATCATCGAGGAAGCAGCTGGCGTTGTTGTTGATGGGTCAGTTGGAGGAGGTGGATTACCCGAACCGAATGCGGACGCGGAAGGTGCT
GCAGTTGGAGTAGGAGGAGTCGGTCAGCAGCAAATGCTCAATCTGGAGGCATTCATGGGTGGCGGTTTCCCTCGCTTACTCGGCCTACCCGAAGA
TGCCGACGATGAGGCCATCATGGATATTGCCATCGCATTGAGTCTCCAACAGCACGGTGGGGATGCAAACGCCTTGCAGTCTCTTCAGCAAGGAT
TGGCCAATCTTCAGGGCATCCGTCAAGCTACTGCCATGGCAGCAGCTGTGAACGCAGCTGCCAATGTCTCCCTAGGTGGATCCGATGATGATGAA

FIGURE SHEET 714

GGTTCCAATGTGGCAACCGATGGATCAACATTGCGTACTTCTCCAGCAGAGCCTGCTGGCAGCGGTGGATCAGAGAGTGGAGGCAGTGGAGTAGA
GAGTATTGGTGGAACATCCGCCAGGAGCAGCAACTTTGGCGACCACGCGAATGCCTCGCCGCCGCGTCAGGGATCCACCAAGGACGATCAAGAGC
AGCCAGGTCCCAGTGGCGTTGCTGGCTCCGGTGGTGTTGCTGTTTTGAGTGCCATGAGCAGCAGTGAGGATAATGAAGCAAACGAGGACGATAAG
CTCAGCAAGCTACATGACCTTAGAATTGCTGTGCTGGAGAGCATTATCCAACATCTAGGAACATTCGACTTGTGCAATGGCCTGCAGGCAATCCC
ACTGATCCAGGTTATACTCATGTTGACTACCGATCTCAATGGAAACAACGAAAGGGATCAACAAGTGCTTCACGATCTGCTTACTGCTCTAGTGG
ACTATGTGGAAATTGGAAAGCGAGGAGCTGCCGCAAGGATGGAGACAAAGTGTCCTGGCAATGAGGTGCGCCTCGCATTGCTTTCCCTGTTCGGA
GTTCTGATGGGCAAAACAAAGTCAAAGCAAACTGGAACAACATCGCCGCCGCATCAATTTAAGGACAATAGCTCCTTTGTGGCCAGTACCACAGC
AAATGTTCTCAGTAAGAGTGGAGCATTCGTTTACGCCCTAGAAGCACTAAACACGCTACTGGTGCACTGGAAGAATGTGCTAGGAGATCCTTATG
CAGCCGGTGGCGGATTAGCCTCACAGTCGGCACAAGCCAGTGGCGGAGCTTCAGGTCCCGGAGTTCAGCTACTGAAGCCCATTAAACATGGTCCT
AAACCTGACATATCCATACTTATACCGCACAACTATCTGAAAAACTACCCGGATATTTTCGAGTCCTACGATGGACTCCTAACTGAAATTATCGT
GCGATTGCCATATCAAATTCTGCGCTTAAGTAGCGCCCATCCGGATAACTACGATAGTGGATTCTGCGAAGCGATGACCTTTACACTTTGTGAGT
ACATGATGCTAAATTTGAACACACTGCTTCGTCGGCAAGTGCGAAAGCTCCTGATGTACATTTGCGGCAGCAAGGAAAAGTTCCGCATGTATCGC
GACGGTCACTCCCTCGACGCTCATTTCCGGGTGGTCAAGCGGGTGTGCAACATTGTCAGCAGCAAGACTGGTGCTCCTTACAACGCTAATCCTCC
TATGCTTTCATACGATGCACTGGTAGAGTTGACGGAACACCTACGTACTTGCCAGGAGATAAGCCAAATGCGCACGGGCAACTGGCAGAAGTTCT
GCGTCGTCCATGAAGATGCGTTGGCCATGCTGATGGAAATCGCCTGTTATCAGTTGGATGATGGCGTGTCGCCTATTATTATACAATTGCTACAG
GCGGCCGTTTGCAACTTACCCCCTCCTAGTGGATCTAAGCAGGCCCAGCCGCAGCCATCGACCTCGTCTGCCTCCGGAAAACTTCGAACAGATCG
TGAGAAGAGCGAGGATACAGACGCCTACTACTCCAAGTTTGATCCAGCCCAGTGTGGTACATTTGTGCACCAGATCTTTAGATACGCATGCGATG
CGCTGATAATCAGATTTGTGCGAATATTCCTGTTGGAGAACAACATTACTCAGCTGAGATGGCAGGCCCACTCATTTATGACCGGACTTTTTGAG
CATGCCAATGAACGGCAGCGTGAGAAACTTCTCAACATATTTTGGAACCTGTGGCCATTGGTGCCCACCTACGGTCGTAGGACAGCGCAGTTTGT
CGACCTATTGGGGTATCTAACCCTAAGTACCAGAAGTATAACAGAACGACTGCCAGAGTTCGTTTCCCGCGCTGTGGATGTTCTCAGGCAGCAGA
ACGAACTGCTTTGCAAGCATCCAAATGCCCCAATATACACCACCTTGGAGTCTATACTTCAAGTAAATGGTTACTACCTAGAATCGGAACCTTGT
TTAGTGTGCAACAATCCAGAGGTGCCGATGGCTAATATAAAGTTGCCATCAGTTAAATCAGACTCTAAGTACACCACAACCACAATGATTTATAA
GCTAGTCCAATGCCATACTATTTCCAAGTTGATCGTGCGGATTGCCGACTTAAAGCGGACAAAGATGGTGAGAACCATTAATGTTTACTACAACA
ACCGCAGTGTCCAGGCGGTAGTGGAGCTAAAAAATCGCCCAGCTCTGTGGCACAAAGCTCGCTCAGTATCCCTGCAATCGGCACAGACCGAACTG
AAGATCGATTTTCCACTACCAATCACCGCATGCAATTTGATGATCGAGTTTGCTGATTTCTTTGAAACTGTGAGTGGATCCAGTGAGAATTTACA
ATGTCCACGTTGTAGTGCAGCAGTGCCGGCTTATCCGGGAGTCTGCGGAAATTGCGGTGAGAACGTGTTCCAGTGCCACAAATGTCGGGCCATTA
ACTACGATGAGAAGGACCCGTTCCTGTGCCACTCCTGTGGCTTCTGCAAATATGCCAAATTTGATTTCAGCATGTATGCCCGTGTTTGCTGCGCT
GTTGATCCTATAGAATCGGCAGAGGATAGGGTCAAGACTGTTTCACTGATTCACAGCTCCCTAGAACGAGCCGATAGAAATTACCGCCAGCTGCT
GACCAACAAGCAAATGCTGGAGCTTCTTATTCAAAAGGTGGCCGAGCATCGTAGCAGTGATCGAATGGTCGAGGACAACATGGCCAGCGTGCACA
GCACTTCTCAAGTAAACAAGATTATACAGCTGCTCGCCCAGAAATACTGTGTGGAATCGCGCACCAGTTTCGAGGAGCTAAGCAAGATCGTTCAG
AAGGTCAAGGCATGTCGAAGCGAACTAGTGGCCTACGATCGTCAACAGCAGGACCAGCCGCCGGTTAATCCCGGCTCAACAACCGGTGCCGAAAA
TCCCACCACAAATCGCTGCTACGGCTGTGCACTGGCATCTACCGAGCAGTGTCTGACGCTTCTGCGAGCCATGGCTTACAATTACGATTGTCGCG
TGTGCTTGTATAGTCAGGGACTCGTCAGTGAACTGGCTGAGCACAACCTGCGACGAGGCACTCCCCTAATTCAGGAGGAAGTGCGCAACCTGTTG
GTCGTACTGACTAAGGATAATGCCGAGGCATGCATGCATCTGTTGCAGTTGGTGACCACAAGGGTGAAGAATGCTCTGATGGGATCGATTCCTCT
GATAAGTTTAGAGGCAGCTGTGCACCAAGAAATGACACTTTTGGAGGTGCTCTTGGGCCAGGACGACATCTGCTGGGAATACAAGCTAAAGGTCA
TCTTTGAGCTGTTCATTAGCAACTGCCGTTTGCCTCGTGGTCCGGTAACAGCAGTACTACACCCCTGTCTGCGCATCATGCAGAATCTCATCTGC
CCGGTTCTGCCCGGCAGCAAGCCCAATCAGAAGGTGGCCACTACAGATTTGTGTAGCATGAAGATGTTTGAGGGCAACACGGTGGACTATAGGGC
CTGGCTGAACTCAGACCGTAATCATGAATACGCAGCGTGGAGCAAGCGGATGCCGTCAAACAACCAGGCTAAGCTAAAGAATGCCAAGGATCAGA
ATGTGGCGGCATCCGGCGGATCAGATGCACCGCCGAAGAGCAGGAGGGAGGTGCGAGTCGCATTCCTTAGCGAAAAGTACGGAAAACGCTGGCGG
GAACGTGTGCTGGACAAGCAACGAGTGATTAAACCTCTTGTATTCAACGCCAAGTGGATACAACCGTTGCTATTTAATGCAAACTCCAGATTCGG
TCGCCAGCTGGCCTGCTCCTTGCTGAGCAGCTTGAGCCGAACTAACGAACGGCGGCAACAGGCTCTGAATATGCTGACATCGTTCTTGAAACATG
TAGGCGAAGCAGGGGAAGCCAGTGCAGAGTACTTAATGCTGTACAAGAACATGGCCACAGAGCAACCCTGGCTGCAGTATTTGGTCCTGAAAGGA
GTATTAAGTCAAATCTCACAGCTTCTGGCTATTGAAATCAGCAAGGTGCACCGCATGGAGGAGTACTCGCTTTCTTCAGATTTATCCTTAGGATA
TGCACTGCGCCAGTATGTGGAATTGTTGTGGCTACTCCTAGAGTGTCCAAATATCCGCAGAACCTACAAGACTCGCATGCTAGGACCAGTTCTGG
AAAGCTATCTTGCCCTAAGAAGCTTAGTCGTGCAGCGTACGCGACTCATTGACGACGCACAGGAGAAGCTGTTAGAGATGCTAGAGGATATGACC
AGCGGAACCGAGGAGGAGACACGTGCCTTTATGGAAATCCTTATTGACACCGTAGAGAAGACCCGCATGAATGACATTAAAACACCGGTGTTTGT
CTTCGAGCGCTTATATTCCATTATTCATCCCGAGGAGCATGACGAAAGCGAGTTCTATATGACATTAGAGAAAGATCCCCAGCAGGAGGACTTTC
TGCAAGGTCGCATGCTGGGTAATCCTTACCCCTCGAGTGAAATGGGATTGGGTCCATTGATGCGGGATGTGAAGAATAAGATTTGTACGGATTGT
GAACTAATCGCCCTGTTGGAAGATGATAACGGCATGGAATTGCTGGTCAACAACAAAATAATAAGCTTGGATCTGCCCGTTAAGGATGTTTACAA
GAAAGTTTGGTTAGCTGAAGGAGGCGACCGAGATGCCATGAGAATTGTATATCGCATGCGCGGTCTCCTGGGAGACGCCACAGAGGAATTTGTGG
AAACGCTGAACAACAAAAGCCAGGAGCAGGTGGACACCGAGCAGCTGTATCGCATGGCCAATGTGCTGGCTGATTGCAACGGCCTACGCGTAATG
TTGGAAAGAATTGGCAGCCTGCAGCGCATATCGCGCAACCGAGAACTTATCCAGGTACTGCTTAAGCTATTCCTTATTTGTGTGAAAGTGCGCCG
TTGCCAAGAGGTGCTTTGCCAACCCGAGATCGGAGCCATCAACACGCTGCTTAAGGTGCTACAAATGTGTCTCCAGTCGGAGAACGATTCGATTC
AATCGGCGGTTACCGAGCAGTTATTGGAGATCATGGAAACAATACTATCGAAGGCGGCCAGCGATACGTTGGACTCGTTCCTGCAGTTCTCCTTG
ACATTCGGTGGACCGGAGTATGTAAGCGCACTAATATCGTGCACAGACTGTCCCAATGTTAGAAACAATCCTTCGGTGCTCCGCCATCTTATTCG
TGTCCTAGCCGCTTTGGTCTATGGCAACGAGGTGAAGATGGCTCTACTTTGCGAGCATTTCAAGGACACTTTGAACTTTAATCGCTTTGACAACG
AGCGCACACCTGAAGAAGAGTTCAAGCTGGAACTCTTCTGCGTGCTGACTAACCAAATTGAGCACAACTGCATTGGCGGCACTCTCAAGGACTAC
ATAGTAAGTCTCGGCATCGTTGAGCGATCGCTAGCCTACATCACCGAGCATGCGCCTTGTGTCAAGCCCACTCTCCTGCGAACCGACTCCGATGA
GCTGAAAGAATTCATCTCGCGGCCAAGCTTGAAGTATATTCTTCGTTTCCTCACCGGCCTCTCAAATCATCATGAGGCAACTCAGGTGGCTATTA
GCAAGGACATTATACCCATTATTCATCGCCTGGAACAAGTATCCAGCGATGAGCATGTGGGCAGTCTGGCCGAGAACCTTTTGGAAGCTCTCTCC
ACCGATTCGGCGACAGCAGCGAGGGTGCAGCAAGTGCGTGACTTCACAAGGGCAGAGAAGAAGCGGCTGGCAATGGCCACGCGCGAGAAACAGTT
GGATGCATTGGGAATGCGCACGAATGAAAAGGGCCAGGTGACGGCCAAGGGCTCCATCCTGCAGAAGATCGAAAAACTGCGCGACGAAACAGGAC
TAACTTGCTTTATTTGTCGCGAAGGCTACGCCTGCCAGCCAGACAAGGTGCTTGGTATCTACACCTTCACCAAGCGCTGCAATGTCGAGGAGTTT
GAGCTGAAGTCGAGAAAAACCATTGGCTATACCACCGTCACACACTTCAATGTGGTCCATGTGGACTGCCACACATCAGCCATAAGATTGACACG
TGGCAGGGATGAATGGGAGCGTGCTAGTTTGCAAAATGCCAACACCAGATGTAATGGACTGCTGCCCCTTTGGGGACCCGCCGTTGGAGAGGCGG
CCTTCTCCGCTTGCATGACCCGCCACAGCAGTTATATGCAGGAGAGTACCCAGCGCTGTGACATCTCCTACACCAGCAGTGTGCATGACTTGAAG
CTGCTGTTGGTACGATTTGCTTGGGAACGCAGCTTCCATGACGATGCCGGCGGAGGTGGTCCGCAATCGAACATGCACTTCGTACCCTACCTGCT
CTTCTACTCCGTCTATCTGTTGCTTTCGTCGCGATCAGCGGCTAGAGACAGCAAGACTCTGCTGACGTATTTGCAGGCGCCGCCCAGCGAGAAGT
GGTTGGAATGCGGATATGAGGTGGATGGTCCGCTTTTCATGGCAACCATTTCGCTGTCACTGCACAGCCGAGAGCTATGGAATAAGCATAAGCTA
GCACATCTGAAGAGGATGATTGCAGTGGCCCAGGGTCGCCACGTCTCACCCGCCGTGCTGTGCAAAGCCTTGTTGGCTCCTGCAGACCGCCAGGT
CAAGGATTACACTGTTTACAAGCCCTTCCTTATGATGTGGGCATTGGTGGACTTGATCTACGACAATCTGTTCAAGACGGTAAGCACGCCCAAGG

FIGURE SHEET 715

AGGAGGATTGGCCGATTTCCCTGTTCGACTATCTTCGTAAGAACGATGAGGCTTTGCTCAAGTCCACGGATAGCATCCTGCAGACCCTAACGGAG
GAGTTCCTGCCCTGCACTTCCTTTGTCGAATTCTGTGATGTTGCAGGTCTCCTGCATCTCATCGAGCACCCGGACAACTTCATCGAAGAAATCCT
CGCTGCCCTGCCTTCAACATCGAGCTCTAATTAAAATGCAATCGCTGTTTCTAACCAAATAAATTGCAGAACTTTAAGCGATTGCTGCGTATATA
TAAACATACAGCATAAATTTATATTTAACACATCCTAAACATTTAATCAATAAAAATTAATCGTTTGCACAATGTAGTGA
(SEQ ID NO: 1340)

Start ATG: 26 (Reverse strand: CAT)

MSAHSGGTDWNSVVKALILNRTGALNKNEVVNLLKAITRCEHDFFEEESNFTQFYTAFAALAADKLMQIKTICQTQICQLHDATAVLIRFIIYRL
PRVSVYETKWLLGALKMLCEGRECPASASSSMFDYNAVANVLKSCKHPESTTKSIMPSSSSSGSGASNDKESPKSEIKRSRSDLSSVILQQLIAP
LEPGKMTWVPLSEEVTDCTEQILAANVEYFQEQNGVDTLLDVCVSLPILNRYRSKYMETINGGKSLYLPLTQVEATAVKSSMNHMLTDLTILSQA
QALIEMQPLTPSRIERLSMCGIAALYNAVLTSIATSVLGMSQASSSQKQTASTSQGSGVGGSSGGQSNKDHDDFEDQACSIVNKALEIYSNIGHM
FKTSARIHVYQNHLCYGSWLLISGIQGAMGASGSGGSSSDSASKSASKATKSGSEAGTAPTTPIARVNLFKVQQGFGELNAAIANHSIKLLSELI
EDLKVEAACGQSLESTELPEPAQFDILQNYSSLERIVRVLNTATLHQLFTFLATVAYRKACTLKRASAKDRTECEPISYSDSTTYFNDSLSCSDN
SEEDDSESYLGHWFKETLSPETHDDNANTSTQERAEQKSALVPKLDEPHEYLDLAADIFCFLDQFLANRHAYMQRYVKAGVSDQQMLLMANIIKD
FDRDVMRNESDQGSGNAPAASAGAGTSAGASTKWQTSMIRFSGAAGRYIHNLISTSLLSEQLQSNLLQHLSISPWSTDTNTWPLQVYPSTLSVLV
QILLLKPTQEKEAACLSVWHRLINTLVEGVCSSNTASDSDYEDLNIEHAQLLLFLFHSLNLMQKKSILLLTAGGVIRCAEVCRGISEDRPVKNSQ
IMLLSRLLLFLEYLMKHLYNAPPELLDQVRWNLFSVSSMPDTQKITDLLNCRTKLNSYCRHDIEENFRKSAGEYGSSIRPTFYSLVMGDPEISYW
AQEFKLDGLAWNFILCTPDKLKYPLLVDALTDILSITDMSMYSKEKDKEASMHNLCAIQYCFTIAWKLNLGLPPSTSHVESLKAERSPNLHSLMW
SIRLPLASSHYLVVSSLIKQGMYTQYAETLWTHVGDIGADIKYSLKQTILGVEAFNSQMNGNGTPRLSDLILFDSLVAHMQAVAWANKEGLKWPR
KESEDAAGEQSAGTSLTSSSNDPELYSSNESIDDQKLKQDDDGKLSSDLQKYNQLVNELMVKLMNSYQLLSVIVRGQMLKQLSSSTPEKALNLIV
PIVSDKPAIMLELHAAFLKLLPNEDKQLIANEWPKCLMVNDFAFNGKQHPVEPYILNVIDAHIIELTRGSNYSTLHTLKHCLKSILQLFELLLPH
RTANAEVETQLKQLLISSMLDMRTDYLQGHSEHCLREILSGLTQEAQKLLLYEHMVGYCYRMLKEFAADLRQPQSAGPSGGAPLDQDRAMFNESM
LFAVLKTMFKMLEKPVAVQAMRQFFKDQRSGSLTTLLLSFTGTSLPVSYARKMLQFVNRLFQLSLQADSQFQHEDLVECFSELATVDVARLKQWL
GHIIYGPNVSTDVSTSEALDTTCRMLTSILQPSSSSSSNAQTPTNMATVSAMPSISDQLDPMEIEYDCGTAAGGGESNPGTGGAAANTSQILSLW
QAAQPNPSEESSQACDHSDSERNGALLLSFVKSLVKDQSKASQIAPPLFQALLQLGQTLISPPQEGCDFADVLQIMITLADASPARGHVALFNTT
LLWLELAKLQLPDKHLKHAENVSAQLRYLSELLQSIGFRGSRQHNPPWDDELQTDIDELYDELAEEGEQDSLLDDSDEDTLNNKLCTFSQTQKEF
MNQHWYHCHTCNMINTVGVCSVCARVCHKGHDVSYAKYGNFFCDCGAKEDGSCQALSRRIGSNEVRDSAGIGSYLPSHMSLLAGKKRSSLPVGQP
VLTRKDSLTNERIAVLTKLLEPYRETLQHQDQWLLVVRCILEYFDLLLPSINENCMLYSIVGCHKRATAALERLHLLEQSFQVTDQLMFATLGSQ
EGAFENVRMNYSGDQGQTIKHLLSSGVVRRVAFCCLSSPHGRRQQLAVSHEKGKVTILQLSALLKQADASKRKLTLTQLSSAPIACTVISLAANP
CNEDCLAVCGLKECHILTFSSSGSTNEHIVVNPQLENGNYIKKAVWLPGSQTLLAVVTSDYVKIYDLAVDTYSPKYYYLVAVGKIRDCTFVYQDG
NYNMLTFASSGYIYTQQLDQQSLAVHGDFYVTNTLELSHQHIKDIAGHIGGGGVSIYYSHTLQLLFYSYSCGRSFFSPLTNVSEGVKGIYHLDTN
SASKSASKGPLQPLVQWTEVTGHPGLVYASMQTSNNPIILMITPERIYLQEIKAQSAKSRIMDVVGIRHAVAGVEKTTLLLLCEDGSLRIFSAQP
EYTSFWLSPQVQPFGNQLYSSTLMAKGGGSGSTSKSKSNTASGKMTSRKASQQQKQPTAGGQPVFPIDFFEHCNMLADVEFGGNDLLQIYNKQKL
KTRLFSTGMFVASTRSNGFTLEVINNDPNVVIVGIRVLIGTQDVQRAPQSVTILGRTIPTPVRRARWFDIPLTREEMLQSDKLLKVVFAKAPDPE
HVTLLDCIEVYGKSKELVGWPDESEDVTVPGSSAPAVSSSQASSANFGEGFNCITQLDRMANHLLEVMDCALHLLGSGVPASMRQKAVKTASALL
LLPTPNPVQTQARYVLATLYGTRALYHNYKDGVLLQFVNRELQSMQPKLEKLETLREIDPEAFYRLVLMVRGIANARPQSLAKICVENNYDIVPT
LMGIVLELHKVTPTLDEPVNIVKRGLCQPETIVHCLVEIMYGFALADPGQVGRMTKYFIDLLKHDASVISHSAKEALILLLSPRMKRRKVAIVTP
PACSTPTPSTSTMQALQAAASSAASDIIEEAAGVVVDGSVGGGGLPEPNADAEGAAVGVGGVGQQQMLNLEAFMGGGFPRLLGLPEDADDEAIMD
IAIALSLQQHGGDANALQSLQQGLANLQGIRQATAMAAAVNAAANVSLGGSDDDEGSNVATDGSTLRTSPAEPAGSGGSESGGSGVESIGGTSAR
SSNFGDHANASPPRQGSTKDDQEQPGPSGVAGSGGVAVLSAMSSSEDNEANEDDKLSKLHDLRIAVLESIIQHLGTFDLCNGLQAIPLIQVILML
TTDLNGNNERDQQVLHDLLTALVDYVEIGKRGAAARMETKCPGNEVRLALLSLFGVLMGKTKSKQTGTTSPPHQFKDNSSFVASTTANVLSKSGA
FVYALEALNTLLVHWKNVLGDPYAAGGGLASQSAQASGGASGPGVQLLKPIKHGPKPDISILIPHNYLKNYPDIFESYDGLLTEIIVRLPYQILR
LSSAHPDNYDSGFCEAMTFTLCEYMMLNLNTLLRRQVRKLLMYICGSKEKFRMYRDGHSLDAHFRVVKRVCNIVSSKTGAPYNANPPMLSYDALV
ELTEHLRTCQEISQMRTGNWQKFCVVHEDALAMLMEIACYQLDDGVSPIIIQLLQAAVCNLPPPSGSKQAQPQPSTSSASGKLRTDREKSEDTDA
YYSKFDPAQCGTFVHQIFRYACDALIIRFVRIFLLENNITQLRWQAHSFMTGLFEHANERQREKLLNIFWNLWPLVPTYGRRTAQFVDLLGYLTL
STRSITERLPEFVSRAVDVLRQQNELLCKHPNAPIYTTLESILQVNGYYLESEPCLVCNNPEVPMANIKLPSVKSDSKYTTTTMIYKLVQCHTIS
KLIVRIADLKRTKMVRTINVYYNNRSVQAVVELKNRPALWHKARSVSLQSAQTELKIDFPLPITACNLMIEFADFFETVSGSSENLQCPRCSAAV
PAYPGVCGNCGENVFQCHKCRAINYDEKDPFLCHSCGFCKYAKFDFSMYARVCCAVDPIESAEDRVKTVSLIHSSLERADRNYRQLLTNKQMLEL
LIQKVAEHRSSDRMVEDNMASVHSTSQVNKIIQLLAQKYCVESRTSFEELSKIVQKVKACRSELVAYDRQQQDQPPVNPGSTTGAENPTTNRCYG
CALASTEQCLTLLRAMAYNYDCRVCLYSQGLVSELAEHNLRRGTPLIQEEVRNLLVVLTKDNAEACMHLLQLVTTRVKNALMGSIPLISLEAAVH
QEMTLLEVLLGQDDICWEYKLKVIFELFISNCRLPRGPVTAVLHPCLRIMQNLICPVLPGSKPNQKVATTDLCSMKMFEGNTVDYRAWLNSDRNH
EYAAWSKRMPSNNQAKLKNAKDQNVAASGGSDAPPKSRREVRVAFLSEKYGKRWRERVLDKQRVIKPLVFNAKWIQPLLFNANSRFGRQLACSLL
SSLSRTNERRQQALNMLTSFLKHVGEAGEASAEYLMLYKNMATEQPWLQYLVLKGVLSQISQLLAIEISKVHRMEEYSLSSDLSLGYALRQYVEL
LWLLLECPNIRRTYKTRMLGPVLESYLALRSLVVQRTRLIDDAQEKLLEMLEDMTSGTEEETRAFMEILIDTVEKTRMNDIKTPVFVFERLYSII
HPEEHDESEFYMTLEKDPQQEDFLQGRMLGNPYPSSEMGLGPLMRDVKNKICTDCELIALLEDDNGMELLVNNKIISLDLPVKDVYKKVWLAEGG
DRDAMRIVYRMRGLLGDATEEFVETLNNKSQEQVDTEQLYRMANVLADCNGLRVMLERIGSLQRISRNRELIQVLLKLFLICVKVRRCQEVLCQP
EIGAINTLLKVLQMCLQSENDSIQSAVTEQLLEIMETILSKAASDTLDSFLQFSLTFGGPEYVSALISCTDCPNVRNNPSVLRHLIRVLAALVYG
NEVKMALLCEHFKDTLNFNRFDNERTPEEEFKLELFCVLTNQIEHNCIGGTLKDYIVSLGIVERSLAYITEHAPCVKPTLLRTDSDELKEFISRP
SLKYILRFLTGLSNHHEATQVAISKDIIPIIHRLEQVSSDEHVGSLAENLLEALSTDSATAARVQQVRDFTRAEKKRLAMATREKQLDALGMRTN
EKGQVTAKGSILQKIEKLRDETGLTCFICREGYACQPDKVLGIYTFTKRCNVEEFELKSRKTIGYTTVTHFNVVHVDCHTSAIRLTRGRDEWERA
SLQNANTRCNGLLPLWGPAVGEAAFSACMTRHSSYMQESTQRCDISYTSSVHDLKLLLVRFAWERSFHDDAGGGGPQSNMHFVPYLLFYSVYLLL
SSRSAARDSKTLLTYLQAPPSEKWLECGYEVDGPLFMATISLSLHSRELWNKHKLAHLKRMIAVAQGRHVSPAVLCKALLAPADRQVKDYTVYKP
FLMMWALVDLIYDNLFKTVSTPKEEDWPISLFDYLRKNDEALLKSTDSILQTLTEEFLPCTSFVEFCDVAGLLHLIEHPDNFIEEILAALPSTSS
SN*
(SEQ ID NO: 1341)

Celera Sequence No. : 142000013384665

FIGURE SHEET 716

TAGTTGAGGTGAGCGCTGGTTTAAATTAGCACAAAAAAGGCGGCTGGCATTATACGGTTTTGAGTTCTTGCAACAGCGAATAATTGTGGTTTTGA
TGTGAATGCTTTCTAAGAGTTTTATCTAAATCGATTTTTGCTGACAGCTTAGCTTTTGCCAAAGGAATCTGTGGGATTTGTATTTAACCAAAATA
TTTCTGACCTTAAGGATGTACTCAAAAGTGGCAGGGTATCCTTTCTACTGAGCACAACTGCAATGACTTATTTTTTCCTCTTCAAGGAATCCACA
GTCATATTTCGGTGGGTATTCCTTTTATATTGCTGCTTTTTTGGTGCATGCAAGACGCAGATTACGTAATCCCTGGCTCAGAGTGCACATGATCC
TTGCAGCTCCTGATCTCGTTCAATCTGACAAAGGGGATAAAGCGCAGTCAACTGGAGGAATCAGCTTAAGCGCTTACGTTTGTGCTCACGCTTAC
GTCATGCGATGTTGTCATTGACTTTTAGTTGATATGCAACCAGCAAGCCAGAGAGCCCAGATTAGTCGGACTGCAGACTGCCGGGGTGGACTCTG
CAGATGGAATAGGATCGGATAAGCAGGAGGAGGCGCAGGAGAAGCAAATGCAAGTGGTACGGGCGGAGAAGAGCAAGCTTTACGGCTTGGTTCCC
CTTCTGTCGGCTCCAATCATATGCGGCCACATTTCCACGGAATCTGAACTCATTGAATGCGCGCTACACGCCAATGCCTCTAATTTTCCATACTT
TCGCTATATAGTGATGACTTGGATACATGAATCTTTTTTAACGTACTTATCACATAATATTTTTGAAACAATTTAAAGGCTCTACAAATAGATAC
ATTTGGCAAGCTTACTTTCACAGTATATGCAAATTGAATTAACTAAATTTTCAAATTTTGGTCTTTGAATTGGTTTTAATACTTTGGAATTACTT
GTTGCAAAATATACAGATTGAAGTAAATGTTACCTTTCTCATCACTGGTCTTACCTTTGGTTGATGTTGCTGCTGCGGCTGCGACGCTCCAGCAA
CAATTGCTCCTGCTCCTCCATCGGCTGCAGCCAGTCGATGTTGCTGTTGTCCTTGATGATGCTGTTGCTGTTGCCATTGCTGTTGCTATTACTAT
TGCTGTTGTCCTGGTCTTTGTTCTGGTCCTGGGTAACAGCAAACCTGCCCATACCTTGAACGGCCGCATTTAAGTCGGACAATTGCAGACGGAAG
TCGTTGCGAGCATTCTCTGGATCATCATCAAACTGTCCCAGTCCCATTTCCATTCCCAATCCCTGTTGCTGCTGTTCGAGTTGCTGCTGTTGATG
TTGCTGTTGTTGCTGCTGCTCATGTTGCTGCTGCTGCTGCCGTTGTAGATGTTGCTGCCTGTCGTATATGCTGTGGATGGGATTTCCGTAGAGTT
TTTGCTGCTGTTGCTGCTGCCATTTGGCCGGTGCTTTGTTGTAGTTATAGTTGTCATTGTTGTCGTCCTCGTTGCTATCTGCAATGCCATCAACG
TCCACATCCCCGTGCTCCCACTTGTAGTTGTAATCGTTGTAGTTGTTGTCCGTGGCGCTTCTATAGCCATATCTATTGTTTTTGAGCCCCGGCGT
CGATTCCATCGTCTCCTCGCAGGCCATGGCGAGCGTTCGTCTGGAAGAGCCACTACCAAAACAGCGAGCAGCTAGAATGACGGCCAGGAGCAGCT
GCAAATGTGGCAGAAACAAAGAGATTTGCTCGATAAGAAGGGTGCGGCACAAGGCAACGGAAATGTTAAACAATTGTTGTGTGGCTAATAAACTG
CAAAGTGTCAACAGTTGTCGAAGGGGAAAGTGGGAGGGGGCTTGATATGCAAATACCCCTCAATTCGAATGGCAAACAATGCATGTGGATTAATA
TTTATCACATGCGATTAGGCATCGCAATGAATAGGTTTATAAAAATATTTGTTGGGTATTTGGGCATCAAAGGCTTATTCAAACCCCTGGATTAG
TGGGTAAGTCAATGAGATTCTTATAAAGGGTTTATAGCAAGCTATATGCATTATGGTTATTCATTGTAGTCTTAGTTGTTATTAATACCTTATCA
GTTGAATGAATTCCTTAGGTACTATACTTTGACAATGATACCAATTATCTTGATAAATAACTCTTTAATTTCTTGAAAAATAAAGTTCTTCCCCA
ATTTCGCATTTTATTGTTTTGCACGTGACGTAGATATTTTATTCTTATCAACATGAAGATACTTAAGGAAAGCCTTGCGATAGGAATCAAATGAT
AATCAATACGCTCTGCTGATAGGCATGGTTATCAGTTGTACAAATATTACAACATGTCTAAAATTACCACAGTAATTACGAAACACGATTGTTGC
TACGTTATAAAATTCCTAGAAAATCCATCGATAACTTTTTAATTTCATTACAACTACGAATTTAGTTTTTATTCCTAATTTTTTTTGGAAGCTCT
GCAGTCTACTACTGCCAACCGAAAATCGACCGCTAATTCAACTAAGAACTCAACAAAATTCCGATTGACGAAACCGAAAACTTAAGCCTAAACAG
CCTCCAAGTTCCCACTGAGCCGGCTGAAGGGGAAAGTTGAATTCCCTGCTGGATGTTGACAATCAATGTGCTTGGGG
(SEQ ID NO: 1342)

Exon: 1642..1001
Start ATG: 1642 (Reverse strand: CAT)

Transcript No. : CT34209
ATGGCCTGCGAGGAGACGATGGAATCGACGCCGGGGCTCAAAAACAATAGATATGGCTATAGAAGCGCCACGGACAACAACTACAACGATTACAA
CTACAAGTGGGAGCACGGGGATGTGGACGTTGATGGCATTGCAGATAGCAACGAGGACGACAACAATGACAACTATAACTACAACAAAGCACCGG
CCAAATGGCAGCAGCAACAGCAGCAAAAACTCTACGGAAATCCCATCCACAGCATATACGACAGGCAGCAACATCTACAACGGCAGCAGCAGCAG
CAACATGAGCAGCAGCAACAACAGCAACATCAACAGCAGCAACTCGAACAGCAGCAACAGGGATTGGGAATGGAAATGGGACTGGGACAGTTTGA
TGATGATCCAGAGAATGCTCGCAACGACTTCCGTCTGCAATTGTCCGACTTAAATGCGGCCGTTCAAGGTATGGGCAGGTTTGCTGTTACCCAGG
ACCAGAACAAAGACCAGGACAACAGCAATAGTAATAGCAACAGCAATGGCAACAGCAACAGCATCATCAAGGACAACAGCAACATCGACTGGCTG
CAGCCGATGGAGGAGCAGGAGCAATTGTTGCTGGAGCGTCGCAGCCGCAGCAGCAACATCAACCAAAGGTAA
(SEQ ID NO: 1343)

Start ATG: 1 (Reverse strand: CAT)

MACEETMESTPGLKNNRYGYRSATDNNYNDYNYKWEHGDVDVDGIADSNEDDNNDNYNYNKAPAKWQQQQQQKLYGNPIHSIYDRQQHLQRQQQQ
QHEQQQQQQHQQQQLEQQQQGLGMEMGLGQFDDDPENARNDFRLQLSDLNAAVQGMGRFAVTQDQNKDQDNSNSNSNSNGNSNSIIKDNSNIDWL
QPMEEQEQLLLERRSRSSNINQR*
(SEQ ID NO: 1344)

Celera Sequence No. : 142000013384562
CTGCACCAGACTGGGCTCATGCGACCAGAGCTTGTCCCCAAAGAGGTGGAGCATCTTGATGGCCACACCGTGACCTCCGCACATGTACAGTTCAT
CGCTGGAGCGAGCCAACTGGCCCACGCCCACCGCAGATTTGTTGTTTGTGAGGTTTACGGCCACTGAAAAAGACAATGAGATCAATACTCGTTAC
CTGGGGAATCCCAAGCAGATACCCACTCAACTGTCCCTTTTTGAAGTGCCCGTACATGCTCAGTCCCACGCCCAGGGGCACCACTCCGGGCAGCA
TGAGATCCGCTCCGTTCGTCAGCTTGGGTAACACACCCTCGTGGGTGGTGAAATAGGGCAGGATGTCCGGAACGATCCACAGGGTGTACAGGGTG
GGCACAAGTTGACCGCCGTCCAGCTCGAAGAACAAAGGCAACTTGTCCACGCAGTAGACCATGCTCTGAACACCGCCGTGCGTTAGGATCTTCAC
CTGGGTCACCGCCGCCTTCGCCGGCACCAGCTGATCCACGGACACATGGGGGAACGCCGCCTCCACGCGCTGCCGGAACTTCTTGCTATCGGATC
CCTTGAGGGCAGCACTGCTCTTGGGTCTGTACGGCTTGAGAAACATCTGTGTTTGGTGGTGTGCACTTGAGGAGTTCGTGAAATGGTTTGGAGTG
GCACATGCACAGTGAAAACAAACAACTGGCAAACGGGGGTGCTGCTTTAGCTATTTTCTCGCCAGTTTGTATATTTAAAAAAATATCAATGGGAT
TCGATATTCTAAAACCAAGTATAAGAAACATAAGAATAAGATGCAGAAAAAGAAATTAACATAAAATAAAGAAGTGAGTCCTGTCTTTTCTTTTC
ACAATAACTCTACCCTAAATCAAAATTAGTTAAGAGCAGACGTTATTACAAGGACAGCACGCGCAGTAAAAATGCCGGCGGTCCGGAAAATTTCG
AATCACCAAGGACTTCCTCAGGTAGCAAACGACAGAAAACCCAGGATCTTGTAAGACGCCATTTTATTCAACAAAACATCTGCGTAACAATTCCC
CGTACACGGCCTTGTGACTCGAAGATGCGTGTTTGATTCATAGTTTTAACTTTGTACTTGAAATAAAAATTAGTAGTTAAACCCCCGATATTTGA
AAAACATAGCCCGGCCCGGTAACAAGATTCGATCCTAGTCAGAATCCGAGTCGGAATTACTGTCCTTGGCCGTGTCGCGCGCTTGTGTAGGTGGA
TCATAGATGTGGAGGCTTTTGCGCCAGATCTTCACGAGCCCATCGAAGGCGCGGCGGCTGTACTTTCCATACTTGTTCGGGGTGCGCGGATGATC
GCGAGTCCGCTCGTCCTTTGGCACCATTTCCACATAGCGCTCGTAGGCGGCAGTATTCTTTCCGTAATCTATTTGCTTCTGCCTGCGACTTAGGA
TGGCGGGATCGGCTTCGGTGTAGGAGGATGACGATGAGGTGGAGGACGTGTAGCTGTTGTGGCGCACCCGTTTCTCCTCCTTGTGGGCGCGGAAG
TTGCCAGACTTTTTTGAGTTCCTCGAATGGGGATTGTTGCCGCCTTTGGGCGCAGCTGCATCTCCGTTGGCCGAGGAGTTGCTGCTGTTTGGACT
GTTGGAGCGACTGTTCTCGTTGCTGGGCGGCGTGAACGAGTGTCGGCGCTTGTAGGGCGTTTTTAGCTTCTCTCCTCCTTGACCAGGCGCTCGAACT TTACCTCGTTGACGCCATCCAGGAACTCAAATGCCATCTCCCGGCCCTCGCCATCTTTGGACTCCAGATTACCGTCGGCTGTCTCCTTTTTGGCC
AAGGAACCGCAGCTGGCAGCGCTGCTATTCAAGGAACTGGAGGCCTGCACGTGCAAACAAGAGAATTAATTGTGTTCCCGATCGTAGCAGCCAAC
CTTCACTTACCTCGTCACTGTGGCCAAACTCCGCGCGGACCTCCTGGGCCCAGCTCTGCATGGTGGGCTTCACATCGATCGAAATGGAGGATGCT
GAGGAATTCAGGCTGCCGGAGCCTTTCTGCGGTGTGTTCTCCACGGACATGTGCTGATCCTCGCAGAGCATGTTGTGCAATTATCTTTCGTTTGT
TTACTGTGCTGTGTATGATGCGGTCCGCTGCTCCAGGATGTTGTCGCGGCGGTGTTTTGCGTTTTCTGCGCAAACCTTCGCGCGTTTTTTGTTGT
AGATGCGATGCTCAGTGTGCCCAGAAGTGGAGGTGGTAAGAAGGCGGCAAAAAGGTACCACAACACAGAACAACCTGGTCACTCACAACTAATTT
CAAACTATGCTCCAAATGTATTACATTTCATTTCAATTTTGTTAAAATTTGATGTCCAATACATATTTAAACATACAGAAAATTAACAGCGATTT
TTAAATTGTCTGAGGGAGGCTCAAACAATATCGATGCATCGGTACACATCGATAGCAAGACATCGAGCAACCAACCATTACCAACACTGTCTGCT
TACCGAGTGATTTAGCATTTTTTCGGCACAAAAGAAAACTGAAAATTAAAACGGTGCAATTGTTGGTTAGTACGCAAAAGAACGATTTGTTTTCA
TAGCAAACGTAAAGTTTTCGAGCCCAAGTTGAACATACGTCACTTTAAAATCCGTAGAACATATTTTTGACTGGAAACAACGCAGCTGGAAAATG
AGTCTTACGTCCGCCGCGGGGATAATTTCCCTACTCGATGAGCCAATGCCGGATCTTAAGGTGTTCGCCCTCAAAAAGCTGGACAACATCGTGGA
TGAGTTCTGGCCGGAGATCTCGGAGTCCATCGAGAAGATCGAGATGCTGCACGAGGATCGCAGCTTCCCCGAAAACAAGCTAGCTGGCATGGTGG
CCTCCAAGGTGTTCTATCACCTGGGCTCCTTCGAGGACGCTCTGACGTACGCCCTGGGCGCTGGTGATCTGTTCGACGTGAATGCCCGCAATGAG
TACACGGAGACCATCATTGCCAAGTGCATCGACTTCTACATTGCCCAGCGGGTGGAGTTCATCGAGAACCCTAAGGAGGCGAGTGTCGTGGACGA
GCGGCTGGAGGGCATTGTGAACAGGATGATTCAGCGCTGTCTGGACGACAACCAGTTCCGCCAGGCTCTGGGCATCGCTCTGGAGACCCGTCGCA
TGGACACCTTCAAGGACGCTATCATGAAG
(SEQ ID NO: 1345)

Exon: 2164..1911
Exon: 1849..1001
Start ATG: 2066 (Reverse strand: CAT)

Transcript No. : CT34229
TTTGCGCAGAAAACGCAAAACACCGCCGCGACAACATCCTGGAGCAGCGGACCGCATCATACACAGCACAGTAAACAAACGAAAGATAATTGCAC
AACATGCTCTGCGAGGATCAGCACATGTCCGTGGAGAACACACCGCAGAAAGGCTCCGGCAGCCTGAATTCCTCAGCATCCTCCATTTCGATCGA
TGTGAAGCCCACCATGCAGAGCTGGGCCCAGGAGGTCCGCGCGGAGTTTGGCCACAGTGACGAGGCCTCCAGTTCCTTGAATAGCAGCGCTGCCA
GCTGCGGTTCCTTGGCCAAAAAGGAGACAGCCGACGGTAATCTGGAGTCCAAAGATGGCGAGGGCCGGGAGATGGCATTTGAGTTCCTGGATGGC
GTCAACGAGGTAAAGTTCGAGCGCCTGGTCAAGGAGGAGAAGCTAAAAACGCCCTACAAGCGCCGACACTCGTTCACGCCGCCCAGCAACGAGAA
CAGTCGCTCCAACAGTCCAAACAGCAGCAACTCCTCGGCCAACGGAGATGCAGCTGCGCCCAAAGGCGGCAACAATCCCCATTCGAGGAACTCAA
AAAAGTCTGGCAACTTCCGCGCCCACAAGGAGGAGAAACGGGTGCGCCACAACAGCTACACGTCCTCCACCTCATCGTCATCCTCCTACACCGAA
GCCGATCCCGCCATCCTAAGTCGCAGGCAGAAGCAAATAGATTACGGAAAGAATACTGCCGCCTACGAGCGCTATGTGGAAATGGTGCCAAAGGA
CGAGCGGACTCGCGATCATCCGCGCACCCCGAACAAGTATGGAAAGTACAGCCGCCGCGCCTTCGATGGGCTCGTGAAGATCTGGCGCAAAAGCC
TCCACATCTATGATCCACCTACACAAGCGCGCGACACGGCCAAGGACAGTAATTCCGACTCGGATTCTGACTAGGATCGAATCTTGTTACCGGGC
CGGGCTATGTTTTTCAAATATCGGGGGTTTAACTACTAATTTTTATTTCAAGTACAAAGTTAAAACTATGAATCAAACACGCATCTTCGAGTCAC
AAGGCCGTGTACGGGGAATTGTTACGCAGATGTTTTGTTGAATAAAATGGCGTCTTAC
(SEQ ID NO: 1346)

Start ATG: 99 (Reverse strand: CAT)

MLCEDQHMSVENTPQKGSGSLNSSASSISIDVKPTMQSWAQEVRAEFGHSDEASSSLNSSAASCGSLAKKETADGNLESKDGEGREMAFEFLDGV
NEVKFERLVKEEKLKTPYKRRHSFTPPSNENSRSNSPNSSNSSANGDAAAPKGGNNPHSRNSKKSGNFRAHKEEKRVRHNSYTSSTSSSSSYTEA
DPAILSRRQKQIDYGKNTAAYERYVEMVPKDERTRDHPRTPNKYGKYSRRAFDGLVKIWRKSLHIYDPPTQARDTAKDSNSDSDSD*
(SEQ ID NO: 1347)

Celera Sequence No. : 142000013384851
CGAAACTATTAAGAAATCACAGCCTATCTAATTACCCATAAAAAGTTTCATTAATTTATTACGAATAAATTATGCCGCTAAGCTACATAAATCCG
AAAACGCGAAATGAACTTGCATCTTTTGATCTTAGAAAACGGTGTATGCCCAACAACCACACAGCAACATCAAATACAGATTAAAAACACAAAAG
GGACTAACCATAAGATCGATCCACTTCAAAGCGAGCATTAAATTAGTAAATTGTTGCAATCAAAAAACAAAATAGACTGTAAGTCCCACACTCTA
GGTATGCAATTGCAATACGTTTTGTATGCGTAATAGCCATTTTTGTGCAAACATTACCTATGTAATTAATATTATACAAATACAAAAACAAAAAT
ATGTAGAAAATTAGGTGGAAATGGAGTGGAGCATTTTTTCAATAAAATCACTAAAATTAACTACTACAGCCTTAATTTATCTAGCCAGCCAACCA
TTTCAATTTCGGAGAAATCGCATTTTCCATTCACAAGATTAAGGGTCATATGTTGCGTTAATTATAATTTTATTAACATTATTGTTGGTTTAATT
TGAATGTGTTAAATTATAAACGTGTGCCGTCGCATTTGCTTAAAAATTTATGAAAATAGTAAAGTTAGAACTTAGAACTAAAGCTTATGCTAAGA
ACTACGTGTGACAAGCTGGCCGTCGAAGAGGGAGCAAAAACAAAATATTAAAACATAGATGTAGTGGAAGGCAATTTTACAATTCAATGTGTCAA
AAAACGTCACGTAATGAAATCAAACCAGCTCCAAGAGTTGATATGGCCTTTGAACTAAAAAACATACAACTTCGGGCGCTGTAGGTCCTTACGGT
TAGAGTAGGAAATGTGGATGGACAGGTGCTGCAGTCGCGGTTTGCTTGGAAGTGAGTTAAGGCCAATCAGCCGACGGCGACACATTGGGTAGATT
ATAAGTGTATGTTAGAGATTTTAAAACACTTAAGACTATGACCGTGAGGCTTAGTTACGTCGCGTTCGACGACGAGCATTTCCTGCAAAGGCGTT
GTGCGCCCCCGGATGCTGTCCGCTGTACAAGTTGTCCAAGAACTCATGCAATGTAGCCTCGCTGCAAAGTGAGATTGTTTTATTTTATGTTTTGC
AGATTGCTCGAAGAAGTTCGCCCTTACCTAACGCCGCTCACTCCCCCACCAGGATGATGTACACCCCGATCGTGATGTGGCTGCTGCGGGTGCTG
GTGGTGTTGTTGTTGTTGCTGCTGCTGCTGCTGCTGTTGTTGTTGCTGCTGCTGCTGAGCACCGCGCACGATGCGGTACTGCACCATGTGCGAGT
TTGGTTCCAAATGTGACAGAGCTCCTTTTTGGCAGTTAGCCCACTCGGTTATGTCATAGACCTTGCCGTCCATTAGCGCCAAGTATTTCCACCGC
AAGCCCATCATGCTTGTCTCGGCCCAAATGTCACCCTATTGCGAAAACAAAAACACATTTTTCAAAGTATGAGTATATCCAACTGTGGATTTCTG
CACCCTTACATCTTTGGCGGAGTGCCGTATTTTGCAGGAAGCACACTCACGCGCCGCATAGTGAGGGCGTTCGGTTAGCTTGCGAGGATGACGCT
GGGCACAAGTGCTGCACCTGTATTAAGCGGTAACCAGAACGATTAGTAATTTGCTATCTATAGAGACGCGTTTGGTACATACGCACCTTATGGTA
TTGGCCGCCTCAGCCATTTTGGTTTGAAGTTGGGAAAGCAGGTCGTGCAACTCCGTCCACGCCTTCTCGGTGTGCAGAGTTTCGGCAATGCTTTG
GTCGTAAATTAGTCGATTCTCCTGCAAAGGAAACTTTTAAGATAGCCATCGATCATTTAAAGTGACAATGCATTACCGGTTCTCCGATTAACTC
AAAGGCGCGCTGCAGCACCTTAAAAGCCTCCTCAGCACCGGCTTGTTTGTTTTTGTCGGGATGTACAAGCACGGCAATCTTTTTGTAGTGCTTGC
GGATCTGCTCCTGGGAGCTGTCTGGGGGAACACCAAGTATGCTAGAACAAGAAGTAAGAACTGTTGCACACGTTCATTAATAGTTGAGCAGAGCT
CACCTGTATGCATCCTTTCCCTTGCAATTAAGCAGAGAGTACATTGCTTCTTCACCCGTTTGTGGCAGACGACCAGTTTTGAATTGCTCGGAAGT
GGTTTCTGGCGGTTTGCGTTTGTAGAAAAGTCGCCATACGGCCAGGCGCGAGTTCTTAGCAAAGCGAGCGTCGAATCGCCGCCAATAACTTCGCC ACCATATGCTTGGCTTGCCAGAGTTCTGCTTCAGTTCCTTTTGCAGCTGCCGCGCATAAGCCAATGCAGCCACATAGGCCAACGTTATCCGCTCG
TATCCCATGCTAAAGCCCAGAACCACGATATCGTACACCAAATAAAACAGCCACGTTAAAAGTTTCAGGGTGTAAATCCACCAGGTGTGGATAAT
ACGTTTGGCCAACTCGTAGTTGCGGTTACTGGAAAAGCTGTTGGCATGGGTGGGCGAGTTTGTCGACGAATAGGCATTGCTTCGATTGCGCTTCG
ATGAGTAGGAGTAGCCAGAACTGTTGTTCGGGTTAAGATTCGAGGAGGAATACCGTTTGGCCGAAGAGGAACTAACATTGTTATTGCTGGAGTAA
TTTACGCTGCTACTGCTACTGCTGCTTCCCGCATGTGTGTTTGCGCCAGTGTGATTCGAGTGACTCGCGTTGGAGTTGATTTTGTTACTGCCTGA
TTTACGTGATGAAGTGCTAGAATTCGTTGCCGGAGTAAAATTGAGAACATTGCTGTGGTTCTGCAAGCTGCTGTTGGCGGACACCGGAGTGGTCT
TATGCTCCGAAAACTTAGGGGCGTTGCTATTTACGTTCTTCGGTTGCAGTGGCCGCTTCTTTTCCGGATTATTTAGTTTGTTTGATTTAATCTGC
GGCTGTAGATTTGGCTGTGCTAGAGACTGAGACTGTTGAACCTTGAGCGGCGGTCTGGCTGACTTTACTTCGCTTCTTGCCTCGGCTGGCATG
CGCATGACCAACACCGGGCACAAACGAACCCGTCTCCTTGGCATCGTGCAGCGGTGAACGTTTTGACGTCCGCATCTCGCGATTTCCATATGCAT
CCTCCTTTTCCGGACGCCTCTGCGATTGTACACTGTAGTCCCCACCGTTGTCTGCGCGCATATCTCGCCCTGCAGCACTCGGTTTTGTGCCTTTG
CTGAGCACATCGGAGTACGACATGGGCATGGGCTTCACCTCGGCCACGATTCGCTTTTTGCCTTCGGGTTGGCCAGGCACGGCGACGCTCGACTT
GTTGATGGCAGTTGGTGAAACGGTGGCAGTGGCCAAAGGCATTTTCAGAGACTTGGCTGGCTTGGAAGCCGCTGGCAGTGTATTGACGGATTGCG
ACAGTGGCTCAGGCTGCTGCAGGTTCTGATTAGGAACCTGTGGCTGTTGGGCTATCGAAGTCTCGAGAACGACGTCCATCTCGTTGGCCTCGCCA
TCAAATTGAATGTAGCTTCCACCAGTCAAATTGGGCGACCAGTTGTTTACAAGGTTGTTAATGAGAAGGTTAGCACTGCTCGACGAGTGATTGAC
TTGGGACACTGTTGGGGCCTGAGTCTGCGTCTGTTGGGGCTGTCGATGCTGGGCGTCTTGCTGCTGTGCATGTGGTAAAGTCAAAGGATTTGTGG
CAAACAGTTCATACAGTGGAGTCGGCTGCGAAGGTGTCGGCGGAGCGGCCTGGTGTTGGTGCTGCAGCTGATGGTGATTAATCGAGGCCATGTTG
ATATGCGTGAAGAGTGGGGTGCCGGCTTCGCTGACCTGGTTGTCCGGGCAGTGGTACACTTTGAGAAAGTTGCCGGGTCCCACAGGCAGCACGGA
GTAGGTCTCTGGCTGGCCTGGCTGACCGGAGTAGGACAGATTGAAGAGATACTCATTGTACATGTGGGGCTGCTGCTGCTGAAGATGGGGCGCAA
ATGGGGGGCCGGCTAGGTGCGGTGGTGGAGGTGGCCACATCAGCGGGACAGGTGCTTGTCCATGCTGCTGCTGGTGGATCAGATAGTTTTGGGTT
TGATGTTGATGCTGCTGCTGTTGCTGTTGCTGCTGTTGGTGGGCCAGGTAGTTGCCCACTTCGTCAGTGTGGGGCAGGACGCGAAAGGGTGCAGA
CTCAGTGCTGCCCCCTCCAATCTCGTCGTCCTGACGAGTCGCCATGTCCTGCGATGGGGCCTATGCTTTTTGCGCACCAGCTCCGCTCGCCTATT
GGAATTTCAAGCGTGCTCCATGTATTCACCGCAGCGAGTCTGTCACGGATGTGCTGCAATCGCAGGTGACAGGTAGTTGGTTTTCTGTGGCCCTA
GCCCACTTTTTCACTCCAAACTCTAAATAATTCGCAGAGCGTCCGTGTAAGAGTTTTATATCTTTTTATTGCAAACGTCAAATGTAGTGTTGC
CAGATGGGTGGAATTCCATTTTCCTAACTGCCCTCGACCAACCCTGGTAGTAACCTATCGAAAGATTTCCCTCCAACGTATTTTCCGAATTGTTG
TTAAACTGTTGGATTATTAATCGAAGTTTCCTCAAATAAAAAAACAAATTTCGCCAACTTTTCCATTGCCACCAATCAGCCGTTTTTGAAGATAC
ATATATTGATGAACCCGCTGATCGTGCAGCCCTGGTTAATATTTGTTGTTTTAAACGTTGCAGTCAAATGATTTTTAAACAATTAAAAAAATGCC
TTTTGTCCGACCGCTGGTGACCGTGGTGCGGGCCGGGCGGCATAGCTATTCAGCAGGATTACAGCTACAGCAACGTCTTGCAAGGTCCAACCAGA
TCCTGAATCCGCCAGCGGAGTTCCGAAACTACCTGGTGCTTCAGGAGCACGACCCGGTCTACACAGTCGGACTAAGGACAAAGGACTATACGGCG
CAGGATGAAGACCGACTCCGCCGGCTAGGAGCAGACTTCCATCGCACAGATCGCGGTGGCTTGATCACATTTCACGGCCCCGGCCAGTTGGTGGC
CTATCCCATTCTGCACCTGGGTCAGTTCGTGCCGAGCATCCGCTGGTACGTGGCGACGTTGGAGCGGATGGTTGTCGAGGCCTGCCACCAGATGG
GCATTTCCAGTGCCAAGGCGACCAAGGACACCGGTATCTGGGTGGGTGACAACAAGATCTGTGCCATCGGTATCCACGGCTCGCGTTACGTCACC
ACGCATGGAATCGGCCTCAATTGCTGCACGGATCTGCAGTGGTTTGAGCACATTGTGCCCTGCGGAATCGAAGGCAAGGGGGTCACCTCGCTCAG
CAAAGAGCTGGACAGACATTTTCCTGTCGAGGAGGCCAGTGGCGCACTCCTCAATAGTTTCGCTAAAGTTTTCGAATGCCGCCTTCAGGAACACG
CCAAAAAACCAGCAAGTTCTGCTGAAATCGGA
(SEQ ID NO: 1348)

Exon: 4447..2094
Exon: 2036..1883
Exon: 1826..1702
Exon: 1632..1530
Exon: 1460..1168
Exon: 1106..1001
Start ATG: 4225 (Reverse strand: CAT)

Transcript No. : CT34422
TTTGCAATAAAAAGATATAAAACTCTTACACACGGACGCTCTGCGAATTATTTAGAGTTTGGAGTGAAAAAGTGGGCTAGGGCCACAGAAAACCA
ACTACCTGTCACCTGCGATTGCAGCACATCCGTGACAGACTCGCTGCGGTGAATACATGGAGCACGCTTGAAATTCCAATAGGCGAGCGGAGCTG
GTGCGCAAAAAGCATAGGCCCCATCGCAGGACATGGCGACTCGTCAGGACGACGAGATTGGAGGGGGCAGCACTGAGTCTGCACCCTTTCGCGTC
CTGCCCCACACTGACGAAGTGGGCAACTACCTGGCCCACCAACAGCAGCAACAGCAACAGCAGCAGCATCAACATCAAACCCAAAACTATCTGAT
CCACCAGCAGCAGCATGGACAAGCACCTGTCCCGCTGATGTGGCCACCTCCACCACCGCACCTAGCCGGCCCCCCATTTGCGCCCCATCTTCAGC
AGCAGCAGCCCCACATGTACAATGAGTATCTCTTCAATCTGTCCTACTCCGGTCAGCCAGGCCAGCCAGAGACCTACTCCGTGCTGCCTGTGGGA
CCCGGCAACTTTCTCAAAGTGTACCACTGCCCGGACAACCAGGTCAGCGAAGCCGGCACCCCACTCTTCACGCATATCAACATGGCCTCGATTAA
TCACCATCAGCTGCAGCACCAACACCAGGCCGCTCCGCCGACACCTTCGCAGCCGACTCCACTGTATGAACTGTTTGCCACAAATCCTTTGACTT
TACCACATGCACAGCAGCAAGACGCCCAGCATCGACAGCCCCAACAGACGCAGACTCAGGCCCCAACAGTGTCCCAAGTCAATCACTCGTCGAGC
AGTGCTAACCTTCTCATTAACAACCTTGTAAACAACTGGTCGCCCAATTTGACTGGTGGAAGCTACATTCAATTTGATGGCGAGGCCAACGAGAT
GGACGTCGTTCTCGAGACTTCGATAGCCCAACAGCCACAGGTTCCTAATCAGAACCTGCAGCAGCCTGAGCCACTGTCGCAATCCGTCAATACAC
TGCCAGCGGCTTCCAAGCCAGCCAAGTCTCTGAAAATGCCTTTGGCCACTGCCACCGTTTCACCAACTGCCATCAACAAGTCGAGCGTCGCCGTG
CCTGGCCAACCCGAAGGCAAAAAGCGAATCGTGGCCGAGGTGAAGCCCATGCCCATGTCGTACTCCGATGTGCTCAGCAAAGGCACAAAACCGAG
TGCTGCAGGGCGAGATATGCGCGCAGACAACGGTGGGGACTACAGTGTACAATCGCAGAGGCGTCCGGAAAAGGAGGATGCATATGGAAATCGCG
AGATGCGGACGTCAAAACGTTCACCGCTGCACGATGCCAAGGAGACGGGTTCGTTTGTGCCCGGTGTTGGTCATGCGCATGCCAGCCGAGGCAAG
AAGCGAAGTAAAGTCAGCCAGACCGCGCCGCTCAAGGTTCAACAGTCTCAGTCTCTAGCACAGCCAAATCTACAGCCGCAGATTAAATCAAACAA
ACTAAATAATCCGGAAAAGAAGCGGCCACTGCAACCGAAGAACGTAAATAGCAACGCCCCTAAGTTTTCGGAGCATAAGACCACTCCGGTGTCCG
CCAACAGCAGCTTGCAGAACCACAGCAATGTTCTCAATTTTACTCCGGCAACGAATTCTAGCACTTCATCACGTAAATCAGGCAGTAACAAAATC
AACTCCAACGCGAGTCACTCGAATCACACTGGCGCAAACACACATGCGGGAAGCAGCAGTAGCAGTAGCAGCAGCGTAAATTACTCCAGCAATAACAA
TGTTAGTTCCTCTTCGGCCAAACGGTATTCCTCCTCGAATCTTAACCCGAACAACAGTTCTGGCTACTCCTACTCATCGAAGCGCAATCGAAGCA
ATGCCTATTCGTCGACAAACTCGCCCACCCATGCCAACAGCTTTTCCAGTAACCGCAACTACGAGTTGGCCAAACGTATTATCCACACCTGGTGG
ATTTACACCCTGAAACTTTTAACGTGGCTGTTTTATTTGGTGTACGATATCGTGGTTCTGGGCTTTAGCATGGGATACGAGCGGATAACGTTGGC
CTATGTGGCTGCATTGGCTTATGCGCGGCAGCTGCAAAAGGAACTGAAGCAGAACTCTGGCAAGCCAAGCATATGGTGGCGAAGTTATTGGCGGC
GATTCGACGCTCGCTTTGCTAAGAACTCGCGCCTGGCCGTATGGCGACTTTTCTACAAACGCAAACCGCCAGAAACCACTTCCGAGCAATTCAAA
ACTGGTCGTCTGCCACAAACGGGTGAAGAAGCAATGTACTCTCTGCTTAATTGCAAGGGAAAGGATGCATACAGCATACTTGGTGTTCCCCCAGA
CAGCTCCCAGGAGCAGATCCGCAAGCACTACAAAAAGATTGCCGTGCTTGTACATCCCGACAAAAACAAACAAGCCGGTGCTGAGGAGGCTTTTA AGGTGCTGCAGCGCGCCTTTGAGTTAATCGGAGAACCGGAGAATCGACTAATTTACGACCAAAGCATTGCCGAAACTCTGCACACCGAGAAGGCG
TGGACGGAGTTGCACGACCTGCTTTCCCAACTTCAAACCAAAATGGCTGAGGCGGCCAATACCATAAGGTGCAGCACTTGTGCCCAGCGTCATCC
TCGCAAGCTAACCGAACGCCCTCACTATGCGGCGCGTGAGTGTGCTTCCTGCAAAATACGGCACTCCGCCAAAGATGGTGACATTTGGGCCGAGA
CAAGCATGATGGGCTTGCGGTGGAAATACTTGGCGCTAATGGACGGCAAGGTCTATGACATAACCGAGTGGGCTAACTGCCAAAAAGGAGCTCTG
TCACATTTGGAACCAAACTCGCACATGGTGCAGTACCGCATCGTGCGCGGTGCTCAGCAGCAGCAGCAACAACAACAGCAGCAGCAGCAGCAGCA
ACAACAACAACACCACCAGCACCCGCAGCAGCCACATCACGATCGGGGTGTACATCATCCTGGTGGGGGAGTGAGCGGCGTTAGCGAGGCTACAT
TGCATGAGTTCTTGGACAACTTGTACAGCGGACAGCATCCGGGGGCGCACAACGCCTTTGCAGGAAATGCTCGTCGTCGAACGCGACGTAACTAA
(SEQ ID NO: 1349)

Start ATG: 223 (Reverse strand: CAT)

MATRQDDEIGGGSTESAPFRVLPHTDEVGNYLAHQQQQQQQQQHQHQTQNYLIHQQQHGQAPVPLMWPPPPPHLAGPPFAPHLQQQQPHMYNEYL
FNLSYSGQPGQPETYSVLPVGPGNFLKVYHCPDNQVSEAGTPLFTHINMASINHHQLQHQHQAAPPTPSQPTPLYELFATNPLTLPHAQQQDAQH
RQPQQTQTQAPTVSQVNHSSSSANLLINNLVNNWSPNLTGGSYIQFDGEANEMDVVLETSIAQQPQVPNQNLQQPEPLSQSVNTLPAASKPAKSL
KMPLATATVSPTAINKSSVAVPGQPEGKKRIVAEVKPMPMSYSDVLSKGTKPSAAGRDMRADNGGDYSVQSQRRPEKEDAYGNREMRTSKRSPLH
DAKETGSFVPGVGHAHASRGKKRSKVSQTAPLKVQQSQSLAQPNLQPQIKSNKLNNPEKKRPLQPKNVNSNAPKFSEHKTTPVSANSSLQNHSNV
LNFTPATNSSTSSRKSGSNKINSNASHSNHTGANTHAGSSSSSSSVNYSSNNNVSSSSAKRYSSSNLNPNNSSGYSYSSKRNRSNAYSSTNSPTH
ANSFSSNRNYELAKRIIHTWWIYTLKLLTWLFYLVYDIVVLGFSMGYERITLAYVAALAYARQLQKELKQNSGKPSIWWRSYWRRFDARFAKNSR
LAVWRLFYKRKPPETTSEQFKTGRLPQTGEEAMYSLLNCKGKDAYSILGVPPDSSQEQIRKHYKKIAVLVHPDKNKQAGAEEAFKVLQRAFELIG
EPENRLIYDQSIAETLHTEKAWTELHDLLSQLQTKMAEAANTIRCSTCAQRHPRKLTERPHYAARECASCKIRHSAKDGDIWAETSMMGLRWKYL
ALMDGKVYDITEWANCQKGALSHLEPNSHMVQYRIVRGAQQQQQQQQQQQQQQQQQHHQHPQQPHHDRGVHHPGGGVSGVSEATLHEFLDNLYSG
QHPGAHNAFAGNARRRTRRN*
(SEQ ID NO: 1350)

Classification: hypothetical

Celera Sequence No. : 142000013384693
TCAAAACAACGATCTCTTGCTGTTGAACCGCCACCATGACACATACAAGAATCTTACCGCGAAGCTCATGCAGTCCCTGTATATCCTGAGACGCC
ACTACGAGTTCTCGTATATGCTGAAAGTGGACGACGATACCTATGTTAAGCTGGACAGTCTAGTTAATACGCTGGTTTCCTACGATCGCAAGTTG
CTGCGCAAGAGGTCGGAGTATAGGGACCATGTGTTGCCTCAGCTTTACTGGGGCTACTTTAACGGCCGATCCACAATTAAAACGAAGGGCCAGTG
GAAGGAGTCTAGTTACTACCTTAGCAAAAACTACCTGCCGTATGCACTGGGCGGGGGATACGTTCTGTCCCGAAGTCTGTGTGACTACATTGTCA
ATAACTCCCAACTGCTATCGCACTATGGGTCCGAGGATGTCTCCGTTGGCACCTGGCTCGCCCCACTGCGCCACGTCTATCGGTGGCACGATCCC
AGATTCGACACCTCCTACGCACCGCGCAAGTGTCGGTCCTATCACATGGTGCTGCACAAACGCAATGGGCAGATGATGAGGGACATTCATGACGG
TGAACTCTGCAGTGGCATTGGTTCGAGTATATTGTCCGATTACTATTACGATTGGACGAGAACAGCGGACAAATGTTGCGACAGCTTAGTAGCGT
AGTCGTGTGGACAGGCTAACCAGCGCTCAACTGGCCATTCTATAGGATTTTCCTTTCCTTCACGACTAGCTACCACGACTCAGCCGGCTGTGCAG
AGCTCCTCGCTATGCTTTGTATTTGCAGCCGAGCAGCATCCTCCACTGCGATGGCCAAAAACCAACACTCGCTTTGCGGCTAGTGGGGCACGTTT
GCATGCGTAGAAGTAGTTTGAAATGTCGAGACTGCAATGGCAGGTAATAAAAAAGTATTAAAGATGTACATTTTACAATACTTTACTCCATTATG
ACATAATTCGGGATGCGCCACAAGACAAGGTAAACAATTAGAATGGACACTTAGAAGAACTTAACGCCGTGGCTGCCGTCCATCTCGATCAGCTC
ACACCTGCCCTTTTCCTCCAGCAACCGGAGGGCACTGAGCAGCACCGCCTCGTCCACGCCGTAAAAGTCCAGGTGAGAGGTGTTCTCGCCGGAGG
CTATTTCGTACAGCGTGCAGATGGTGTTCGTCTGGCCCGTTTCCTGCACCCAGTCGTACACCATGTTGCCGTACTCCTCGAGGGTGAACCAGTAC
ACCTGCCACTCCTGGCGTCGCTTGTCCAGCGGATTCGCATGCCCGCTCCGCTCCAGCTCGCCCAGAATGGCCAGGACGAGTTCCGGCGAGAGGCG
GCGCTTCAGCGCTTCGTTGTGGAACAGCGGCGAGTTCTGGTCCCCAATGCTGAGAGTAAACCTATTCGTGTGCCTGAGGTATTTGAGAAAGAGAT
CTGTCCAGACCTTCAGCTGCTGCTGTCTGGTTTCTTCGTGGGGCTGTAGTCTGAAACCCGGGTGTTAGTCGAGTGATGGAGCATCTCCTGGTCGG
AACTCACGTAAAGAAGGGTGGGAAGGTGTACTCCCAGGGCCACTGGAACTCCGCCATGCTGATTAACTACGATCTAAACATTTGTTTTTCCAATG
TAAGTTATTACTAATGGCCTAGAGTGACCATATGCGCTAAATAGCAAAATACCTTGCTATTCAAAAACCATTCAAAAGTAAAAAAATTCGTTACT
TTTTAGTTTTATTATTGTATCCTTATATTTAATATTCGCATTAATAAAAAAAGTTACGAGTTTCCTTAACTTTCTTTTGCATAGCACTTAGCTTA
CGAGGAATTTAAAGCCATTTTTGAAAGCAAACTATTTAAATTAAACACCCGTTTTAAATTTTGAACCCAATATCCCAAGAAAACACTTATTTGTC
ATTTACAGTAAAATGCAATCCATTTCTTGTATTTTGTCTTAAATAGAAAAAATTGTGTACATTAACATTTTCATCGGGCTTTTTATGAACTTTGA
TTTGGGCGTCTGGTTTTCAGTTTCGGTTTCTGCTTTATTCAAAATCTCTGATTTATCAATTCAATGCCTAGGTCTAGAATCAATTTCGCGAGAAT
GTGGCGACAAAAGAGGGGGATTGCAATGGCTTGCATCGTCAATATACACGCACATATATACTCGTATCTGATAAATCTGCTTTATTATTTATAAG
TAAAGTTCTAGGAGGCGCAACACTATACATTCAATATCTGCTATTCTGTATTCCTCTTTCAAACACGCGATTTCCGAACCAATTTAGACACTTTA
TGTGTGGCATGCTGCGGGTGCTTAGTTACTAACTTTATCGATTGTGTGCTAATGTTTCGTTCAAGTTTAACTTGCTGATCGGATCGGATCGAATC
GGATCAGATCAAATGGGATCGAGCTGGGCCTGCTGCCCCCACGGAGCTTCCTTGGCTTGGTATGTACGACATATATGGTAATCATCTTGTTTGCA
CTATATTTTATTTGGTTTTTGTACACATGCGTGAAATTCTAGGGAGAATGCCATTCGGGGAGTAGGAATAGAGTACAGTTTAGTGTTAGGATTGG
ATTTCAGCTGGC
(SEQ ID NO: 1351)

Exon: 1577..1528
Exon: 1475..1001
Start ATG: 1577 (Reverse strand: CAT)

Transcript No. : CT34551
ATGGCGGAGTTCCAGTGGCCCTGGGAGTACACCTTCCCACCCTTCTTTACACTACAGCCCCACGAAGAAACCAGACAGCAGCAGCTGAAGGTCTG
GACAGATCTCTTTCTCAAATACCTCAGGCACACGAATAGGTTTACTCTCAGCATTGGGGACCAGAACTCGCCGCTGTTCCACAACGAAGCGCTGA
AGCGCCGCCTCTCGCCGGAACTCGTCCTGGCCATTCTGGGCGAGCTGGAGCGGAGCGGGCATGCGAATCCGCTGGACAAGCGACGCCAGGAGTGG
CAGGTGTACTGGTTCACCCTCGAGGAGTACGGCAACATGGTGTACGACTGGGTGCAGGAAACGGGCCAGACGAACACCATCTGCACGCTGTACGA
AATAGCCTCCGGCGAGAACACCTCTCACCTGGACTTTTACGGCGTGGACGAGGCGGTGCTGCTCAGTGCCCTCCGGTTGCTGGAGGAAAAGGGCA
GGTGTGAGCTGATCGAGATGGACGGCAGCCACGGCGTTAAGTTCTTCTAA
(SEQ ID NO: 1352)

FIGURE SHEET 720

Start ATG: 1 (Reverse strand: CAT)

MAEFQWPWEYTFPPFFTLQPHEETRQQQLKVWTDLFLKYLRHTNRFTLSIGDQNSPLFHNEALKRRLSPELVLAILGELERSGHANPLDKRRQEW
QVYWFTLEEYGNMVYDWVQETGQTNTICTLYEIASGENTSHLDFYGVDEAVLLSALRLLEEKGRCELIEMDGSHGVKFF*
(SEQ ID NO: 1353)

Classification: hypothetical

Celera Sequence No. : 142000013384523
AATATAAAAGGCATTATGCCGAAATGAGTTTCCATACGATTTCTCTTTTAATGATTAATATGTTTTCCTCGATATTAAAATGCATAACTACGATT
AAGTATGTGCTTGCGTTCTTAAAAAACAGTATGGTTTTCAGGGTAATTTTCTGTGTTATATGCATGTAGGTAACCATTTTTTTGATATATCTAAC
AATTTGTACTTGGTTTTTAGCTCCACTAAGGAGTGTCTTGTTTTTTATTCAAACCATCCCTTATCCCCCATCTCTAAGTGACACAGCAAAGTTCA
AAGCCCGCCTGCACCCATGTTTTTGAGCAGCGAGTTCGAGTTCCATTGACCAAGCGGTATATAATTGTTGGCCACAAAAGCGAAAACAGCTTTTC
GGCCAAATAATAGTTGGAGAATAGAAAAAAAACTACAATCGACGCCCCCGCCAAGCGGAACAGAGCCACACATCCACAACCACAACCACATCCGT
ATCCATGAAGTGCTCCACACATCGAAAACTACTTCTACATACATCTGGAGCCACATTAACACACTCTGACTACGCAACTGTGCGAAAATCGCTTT
AGACGCTAACTGGAAACCGAGAAGCAGTTGGCTATGAGTGGGGCGCTTAATATGGATACAGTTAATTGACCTTGATTGAGTTTATTTCGGTTAAG
GCAGCTGTCTGCGAGCCAAATGTCTCCATTCTGTTTGGTGTGAGTGTGTATCTGTGAGTGGGCTTCATCAACATCATTATCATTATGGAAGGTCT
GCGGGAGGAAGTGGCACATTCCCGAGATTCCTGCCACAGCCTAATCAGCATAAAATAGTTCAGGGTGCAACTGCCTGCTTTCCAAAGTTTGAGAA
AATATGACGAACTTCTTGCTACTATACTAATATTATTATACCGTTTCTCAAAATATATGTTGTAATTTAAATTAAATTGGTATACTTGTATACTT
TTCATTTTTCAGTGTAGACCTCGCCTTAAGGTTATCTGTCTCCTTCTCGTCTAAGGATCAGATTCCCCCAGAACTTTTATGCCTGCAAATGCCCA
ACTCCTTACACTTGGAGTGAGGAATTTTTCATTAGGAAGGAAGCAATTTCATGGCCAGTTATTTGAGCCCTCCGGCTGACGCCTGTGCGTGTCGC
ACTAGAAACGCACCACCACCCATGCCCAACCCGCCCCCACACTGAAGGTGTGGCCACCATCCCCGCCCCGAGGTATGCAAAAGGTAAACATTGGG
CATTGAGCAACTCACCAGCTGACATGTTGAGACGTTTGCGCGCATCGCGTTTGGAGTAGAGGAACTGGAAGCCCGCGCCTAGTTTTTTGCCCGTC
GAACCACTGCTGGCACCCACACCAACACCACCACTTGAGCCACCTCCTGCCCCACTGACGGCCGCTGCTCGAGCTGCCAATCCTGGCGAGCGGTA
TCTCGCACTCTTGGCACTGCCAGTGGCCGAAACGGTGGACAAATTAGAGGGCGTGTGGTTGAGGGCGCTCTGAGACTTTGTCTTGGGGGTGCTGG
TTATGGGAGCACCAACACCGGTGGTGGGTAACCGGGGTAGTGAATTCGTGCTAGCCACCACTTGGTTGGGATTCAGACTGCGCGGCAACGTGGAT
CTGGCGCCGCCAAACTGATGCGAAGCTGCCTCATCGCTGGAGTCCGTCTCGTAAATGGCATCCGGTACACTGGAACGCCGCACATCCTTCGTAGA
ATCACCGCCAATCGAGGATCCCGCGGAGGAGAGCCACGGCTTGGCCGGCGAGGACTCCAACTGGTGGTGATGGGCATCGCCGCCTCCAATGCTGC
CGCAGGATCGGACGCGATCCAATTGCTCGCGGCTCAGGCTCTGCTGGTGCTGGCTGAAGAGAAGGTCGCCTGCCGATCGGCGCTTTGCCACAGCC
AAAGCGGACGCAGACGACGAGTTATCCCTGTCCAGTTGGCTCAGCTGGCTGAGCCTCGTTCTGCTGTCGCCATTAGCCAGTAATGCCGACTCAAA
ACTGCCGCGCCACGAGAATCGCTCGTAGTCGCTGGTCACGCCGCACTCCTCCCCGGCGTTGTCCGAGTGTCCGGGTCCGCCGGATCCTCCCGCTC
CCGATCCCACGCCGCCGGCTGGATAATGCACCGTGGCATGGTGGTGCAGGTGATGCGAATGCGGCGTAGTGCCGTCCAGCAGTAGATCATGGGAT
TTGCTTCGCAGCTTTAGCTGCTTGATGGGCATGGCTTTCAGTTGCTCCGCCACCTCATCTTCCTCATCCTCCGTCGTGGTGGCCGAGATCTTGGC
CTGCAGTCTTCGATGATGCCGCTGTCCTTGCGGGGATGGAGTGGGTGTTTCATTGCCACTGCTAACTTCGTGCATCAGAGCTACCAATCTGGTAC
CAATATGCTGCATCACCTTGGCAAACAGTTGCGGGGATCTCTCCGTGGACGGTTCTGCTTCCTCCACCGCTTTGGTGGCTTCTGTTTCCGGTTCT
CCACCCGCCGCCACTTTGCTAAAGGAAGCTACCAATTTCTGATACACCAATGCTTCCATAGGCACACTTTGGCTCTCGTCCAGCAGTCCACCATC
ACCACGATCACCCTCCTCGTCAATTTCAAACTTGTTGATGATCTGCTGACAGCTGGCGGAGATCTGAGCCTTCAGTTGGCCCTTCCTTTCACCGC
CCTCCAGATCGGAGCTCGTGTAGTCCGAAGAATCGTAGGAATCAGACCATGTATCCTCACTGCTCAGGTACTCCACTATTTCGCGCACCTGCTCA
TCATTGATGCCCGGCACGGTTTTCATCAGTCGGGTCAGCTCATTCTCAAAGTAGGCCAACTGAGCTGGCCGGGATTTGGCCAATCTGCGCTGGGA
ACTGGGCGTGGTGTTGACATTGGTGGTGCTGGGCCCTTGATTGGGCGTGGAGGGCTTGCTCTGCTGTGCATTGGCGGTGGCGACAATGAGGTTCT
TAAAGAACTGCCGCATCTTGCTCATCATCAGGTTGGTCTCCTCGTCGGAGCTCCAATTGTTGAAGCTATCCTTTCGCACCAGATTGGGCAGGGCA
AGATTTTTCAGTTGGCTGGAAAGTGTGCTGGCTACAGCTGCAGCTGCTGAAGTGCTTGGTTGATCCATCCTGGCCAGACTAATCTGACTATGGAC
CGGTTCCCGATCCTCACTGATCTGCTCCAGAGCTGGCGTTGGGCTCTTGGGTGGCTCACAATCTGGTGCCGCCTTCAGGAGATCATCGTTGCTGC
CCACAAAGCCACTGTCCCGGCTGTGGTGATGCTGCTGTTGTTGCTTTTTCGCCTGCGACTGCATCTGCACTTGACCACTGCTGCCCGGGGTGGGA
GTCCGGCACTCGGAAGGCTCTAGATCGTGGAGCTTCTTCTCGTCCAGAGAGTCGTGACGCTTGCGCAGTTGCTTCTTGCGTTTAATGGTGTCCGA
GGAGGAACCATCCGAAGCTCCGGCATTGGCCAAATGAATCACAGTGTCGTCACAGCCCGCCTCCGATTCCGAGGTGTCCTCTACAGTGGCTGCAG
CTGCTCCGCCTGCAGAAGTAACTGTGGCATCCAGGGTGTCTGATTCTGGCAGTAGCAAATTATCCAACGAGGAGTTGTGACTTCTAGGTGTTCCC
CTGGCTCTTACCAGTCGCTTTCTCCGCTGACTGGGACTCGGTTGTCCTTCACTATCACTGCCTACACTGCCACCACTTTCATCGCTCTCCGCCTG
CTTTTCTGCACCACTGAATCCCATGAAGCCGGAGAGGAAGTACTTTTCCAGACGGGAAGAGGCCAGATCGGAAGCTCCACTTGTATCCAACAGCT
GATCCTCATGCGGTAGGGAGTCAAGACTCTCAGAGCACTCGGAACTCACTTCGGATGCAGTGTCATCTCCGCGTGTATCAATAGAACTCATTACT
CGACCATCTCCCAGCCCAAAGAAGAAGTACTTCTCTAGTTCAGAGGCACTTAGTCGATGGTGGTGCTGCAAGGTGCGCTGCCTTCTCCGTTCGGA
TAGATCCTCATCCTCCAGCTCGACGTCTTCATTGTCCGCCCGCATGGAGGCCACCTCGCTCTCCTCACAACTCTCCTCGACGATGGTGTGCAGGG
TGAAGTCGATGGCAGATCTATTGTATCCCCTTAGGTCCTCCTCTCGATCCATATATCCATGTCGCCGGGCTCCTTCACCTTCTCCCTCCGCATCT
TCGGAGTCTGTGGCCGTGGGTGTGGTGGTAGCATTGCTGAGATCTTCGTCCTCATCCTCGCCGCGCTGACTCAGTTCCTCCACCCAGGAGTCGTC
ATCAGCCAAGCCGTCCTCTACGCTGAGTTCCGGCACAGCAGGCGGTTCGTTTAGCGAGTCCACACTGTACGCTTCGCGATCGCTGCTCACGAGTT
CCGTTGGTTCCATGGCGCGAAATGAGTCACTCGCAAAGTTCTGGCCAACAGTGTGGCTGTTGTTGCTACTGGTCGGGTCTTTGTGTCTGATGTTG
CTGAAGTTGCTGCTGCTGTTTGCCATTTCGTAATCGCCAGCTGCACTTTCATTGTCTTTGTTGATCATGACCAAACTGCGATACTTGGCTGAAAG
TGAATTTTTGGGCGAAGCCAGTTCGCTGGGCGATGTTGCAGGTGTTGCAGATGTTGCTGCTGCTGCTGCTGTTGCTGCAACTGCTGCTGATGCACTTG
GAGTGTTTTGCTGATGACTACCAAATATTTTGTCGAAGTCACACTCGTTTTCACCACTCACATTTGAATTCACACTCACTACGTCACTAATATCG
CAGCCGACAACCACACTCGAGCCGCTATTTCTCGTCTTTTGTGCTGCGAAAGCGTCATTATTATTATGGCCAAGTTCGCCGTCGTTGTTGTTAGT
GTTTTCGTTATTGCTATTATCGTTTCTGTGTGTGTTGTTGTTATTGCTGCCGAGAAGCGCGGCACGAGAAGCGACCGCAACGTTTAACATTTCAT
TTTCGACTGGCGACTCCGCCGACTCCGATTTCGCTCCACGGCGATATCGTTGCTCGCGAGCGTCGGCAGGTAGGCCGAGCACTCTCTTCTACCTGC
TGGAGCGGCTGCTGCTGCTGCTGCTCAGGTGCCAACAAACTCGCCGAAGTTGCCGAGAGTGAATCCAGCGAGTAGTCACTGTTGTCGTTTATTTT
GCATGCTTGGCTGCATGTGACGACCCTCTCCTCGGTTTGCTCAGCTGTTCGGCCATTCCGCTCATCCCGCAGTTTGCCATCAGCTCTGTTTGCTT
CTACCTCAACCACTGCCTCTACCTGCCGTAAGCAGGTGAGACTCAGCGGACCAACGTCATTAGAACTTAGCACGGTCGAGGGGCTTTTCCGAGAA
GAAGGGCTATTGCATTCGTCGGGTTTCCCGGCACTACCTGGCTGCGTTGTGCAGTGGGTGGCAGCCACATCAGTGCCCGTGGTGGAGAGCTGCAG
ATCCTCATTGATTTCGGCCACTCCCTGGCGCAAGCGTTGGAGCTTCAACTCCAGCTGAGAGTTCTGCTTGTGCAGCGCCAGCAATCGATTGACAT
CGTTCGAGATGCTGTGCAGCTCATCGCAGGCGGCCAGGGCATCGCTGGCGTCTATCTCATGCGCTTGGCGGCGCTCTGATTGCTCGCCATCGAAC
TCGACGTCTGGCAGCGATCGCATGTGGTGCAGCACCACGCCGGCGGCGGCGTCGTCCGTCTGTCCGCCCACCACTACAATGCAGTTGGCCAGCTC
ATCGGTTGAGTTGGCAACACGGCGTTCACTTTCATCATCGTTAATGTTGTCTTCGTCACTTGATTGGCAATCACGTGCAGCTGTCGGCGGCTCCT CCTCCGCCTTCTTGGGCTCCTCCTCTAGGGGTTTCACGTAGTTGAGCACAATTCCACAATCGGTGCGCTCGGTGTCTGTATCATTGTCAGAGGAA
TCCTCCAAATTGGCCTCCGAGGAAGACAGAGAATCGCCCTCGGTGGAGGAACTGCGTCTTACCCGGCCGCCGGGCTGTCGATTTACGACGAACAC
CTTGTTGAACCTCCTTCTCTTGGGCCTGCGATCGCGCACAGTTCCCGTATCATCGGAGTCACACGATTCCGAGCTGGAGCTGGAGTTTGAGCTGC
TGCTGGAGCTGGAATCGCTGGTGGTGCTGTGGTGTCGTTGCTCCACTGCATCCACTTCTCCTAGTTGCTGCTCCTCCATCATTCCCGCAACGTTG
TAGCTTCTTTGCGTGGTCCTACGCGGCTTTTGCTCCGCCTGCTCCTCCAACTCACGCTCCCTATCCTGATCTCCATCCTGGCTGCTGTTGCTGCT
GGCCTCATCTGGACTACTGGCCGCATAGCTTTCGCTCTGCAGATGGGCCGCCGTCGATGGTGATGCCTCATCGGACATCTTGATGTTCTCTATAA
GTCGATTGGAGGACAAATTCTTGGCAGTCTCCGCCGTCGCTCGATGCCGATCTATCTGCTCTGGGTGCTGGGCTCTGGGTTTGGGCTTGGGAATG
GGACTGGCGGCACTGGCACTAGCACTTTCAGCCACATTTCCAACAGCATTTTCGACTGCAAGTCCGCCGAAACGAGTTATTACCGCAGGAGCCGC
AGCTCTAGTTGCTGTTTGTATTTGTGCTGTTGCTGCGGCTGCCGCTGCTGGTACTTGATTTTTATGTATATTCGTTTCGTCTGCTGCTTCCACTT
CTTCGTGGCTGTTTTTACTGGCCAGGTAGGTTTGTGTTGTTGCCGCTGACTGGGTTTCGCATAGATTTCGGCTCTGGTATTTGCTGGCCACTCTC
AGAGCGGTTCCCTTTGTGGATGTCGCTGGTGTTGCTGCTGGCTCTGCTTTTGTTGATATTGCTGCTGTCGCGGCACTCTTATCTACACTGGCAAC
ATGTGCCTGAACGCACTGAGGCACTGGCAATGTGCCGGTTTTATCATAAACATTACACAATCTACCCGTTGTGGGCGTTGCGTTGTTGCTGTTGC
TGTTGGCGTTGTCGTCGCTCTCACTGTTGCTGCTGCCGCGACGCGCGTTGCTCGTTTCTAGTTGCTCACCCGTCGGCGAACGCGAAGCTACTAAA
CTTGTTGGCTTTGGCTTGAAAGCACTGCTGGCCATTTGTTGATGTTGCTCTTGGTATTGTTGCTGCTGCTGCTGCATCGAGTTGGCAGCTCGCAT
TGGACTGGCCAGCGTTTCCAGGCTCCTACCCGCCGTCCCATAGCCCGAGGTGCTCGACGACGACGAGGAGGATATGGTGGAGCAGAGCGACTGCG
TCATCAGTGATCCCAGCGAGGCACTCAGCTCCGGTGCCGAGGACTTGAAGCCACCCAGTCCGCGCAAGCGCTCCGGAATTGGCGGCGGAGTGGTA
GGCAGTTGTTGGTAGCTCTTGCTGGTCACCGGCGGCGTTGCATCGAACATGTTGCCACTGGCCGCTGCAAATTGCTGCGAATAGGCGGCAACTAT
GGCGGCAAATTGCTGCTGGTGACCGGCCGCCTTCCATAGCTGCTGCAGACTGGCAGCCAGCTGCTCGTCCTGTTCCAGTAGTGGATTGCCTGACA
CTTCTGGCCAGTTGGGATAGGCGGCCATGGGCACTGGTATGGGCACCGGGACGGGAATGGGCACGTACTGCGGCTGCTGCTGCTGCTGGCCGGGA
TTGCAGTTGCATCGGTTGTGGCTGTGGTGGTGATGATTCTTTAAGAATCGCGTCTTAATCCGGGTCTTCATGCTCAGCGGATGTGGCGGTGGTGG
CACGGGTGGTGGTGTTTGATCGGAGCTGGTCTGCGAACTGCTTTCGGTGTTCAGCACAAACTCCTCGTCGGTGCCGGTGTCACTCTCCCTGATCC
TGGGACAATAGATATTCCTGGGCTGTTGGGGTCGCCTTTGCACCTGGGGAGAATCGCTATCGCTCGACTGACGCCTTACACGCGGCGGTGGAGTG
GGCGTGGCTCGGGCTGTAGTATAGGCAATCATGGTAGTTGTCGTGGTCGTCGTGGTGGAGATCATGGAGGGCTCAAAGTAATCCCAATCGCAGTC
TTCCACATTGCTCACAATGCTGTGACAGTGGTGCGTGGAGCAGGATGAATCCGTGTCATCCTCCTCCCCGTCCTCCTCCTCCTCTTCTTCCTCTT
CGCCGTGACAGGACGACGATGAATCCGAGTTGAGAAAGACGAGCTTGAACTCGTCCGCTTCAACGCTATATTGCGACTGCTGCTGCTGTCGTCCG
TGCTGAGTGGAACACCTGAAGTCTAGCTCCGATGACGACGAGGTTTCCACGGCATCGCCCCCACCTCCACATCCACCGATATCAACGGAAACCAC
GGACAGCTGCTGCCCTATGCCTGTGGAGTAGCAGGGATGAAGTTTCGGGAACATACGTAAGTTCGGAGACAACCACTTTGTCGTTGACCAACACC
ACGAAGCTGTTCGCAAATACTGGTTATTAGCACCAAACAAATACACACAGGTGAAATACTGGTTAGCCGGAGGGTGAGTTTTTCCACACCAAAGT
TAAAGGTTGCAGATGGGCTAAGCACATGGACGGGTGGTGGTTGAACAAAAACTTACGGCTAGCATGGGTTAAGCTTGGATGGTTACACCGAAATA
CCACAGATATTAATAGATAGAAAAGGCTGGGAAGGAGTGTTAGTCATTTTATCAAGCCCATTTTATAGATTTCAATGTTAATGGGTATGAACAAG
TTTGTTAGCTGTCTAGTTACACGCCTTGTTAAAAAATGATTTCTACTTCAAATCGATATTAAGTTCTTGCACTGATATAAACAACATATTTAATA
ACCCAGCACCAGGTTGAATAACTTCCCTATAAATATGTTCTGTTTATAATTGAGCGATAGAATGTTCAATAACTAAACTCAACATATACAGAACA
CAATGATGAGTGATCGTAATGTCTATCCAGTTCCAATTTCATACAAACTTGAAACTTAAAATTTAAATGGATTCCATATTACTTTTATTTTGACA
ACACTAAAAGTTTCTCCGAAAAAATGCACTTCTTCCCAATAAGTTCAGAGCTGGGAAAAATCTTTAGTGCTGCAACGACCTTGAGTAAGTGAACT
TCATCCTGACTAAAATTAAATATTCCGAAAATCATTTCCCCTGCTGTTCAAGTACCCATCCTGTCAGGAAGCAGTTCAAAGACCCTTGATTGATT
ATGGTTGTTTGCCACAAGTTTTTCTGCCCAAGACAAGTACTAGCGAAAATTTGCCAAAAAGCTTTTAAAGTTGCCAACATCGCCGTCCTTCAAAC
CCTTCTGCTTGGTTGGTTGCCCTAACAAAAACTGCAACAGCGGCGGATGCACATAGCGTCAATCCCTCGTAGCCACAAAGTAAACATTTGATCGC
TGCCCACCCTGCTGTATGAGACACTGCGAGAAATATTTCAGAGAATTTTTAAAACTTCTTCTACCCACTCTTGCAACTAATAGTACAGGTGTTCA
GTTTTTGGACACTTTAATATTAAGTAAACTCATTTTTAAGTCAAATATATTGTTCTGAGTGCTCAGAAGTTCTTGTCTAAACGCAAACTGTGCAC
CGTTTTAGTCATTCACAGAGCAAAACCCACATAGGAGCACAAAAGGTTCAGGAGATAAGACTAATGCCACAGTTCTGCCGCTCCACGTGGTCCAA
AAATCCGACGGGTGACAGCGTGGCTTTGGTGTGTACGTGGGCACCGACAGAACAAGGTACCAAATTCTGGAATCCTTCGAGGCGACAGTCCACCG
CATCTCGAATTCGCACATAGACACAGGCTGCGTTGGTGGTCACAAAACCGAACGTACACCCACAAATCGCCAAATTGAAACATAACAAAAGGCGG
CAAAGGCGTTTGGATACCCTGCCTTCCGCCCGGAAAATCCCCGCCTGAAAACTCTTGAAGTGCGGGGGAAGTGGTGTGGGTGGGGCGGTGGGAAA
TCGATTTATGAGTTGCCAAAAAATTATCCCGCCAGCCCACGGCTAGGTTTTTGTATTTGTTTCGGTCCCGTGCCACAAAATCTTTTGAAACCCG
CCAACTTTGCTCTTAAATTTGGTTCTTCGGTCGTTTGTGGTCATGCCGCCAATAGCTTCGGGAAAAAATTTAATTCCAATGGTGAATGGAAAGTCT
GCCGTGAAGAAGGCGAAAATTGATGGAATACTTTTAGGAACTCGCAAGAGAAGTGAGCGAGAAAAAGTGTTGCACTCTTTTTGGAAACGCTTCTT
AAAAAATTGATGAGGGAGATGGTTTCCGAAAAGAACCTGAATGTAAAATAGGACAGTTGCCAAGTACATCGATTATTTGAAACTCTGATTCTCTG
CTACAGATTTGATGATTTTACTTAGCTTAACGTGTATGTATGTATTTTAATTTGAATGCATAATCCCTTAAGCTAAAACTATTTTAAAGCACTTT
AGTCCATTAGCACAACTAGTTTTCTATGATTAAATTGATAGGATTAGTTTTTTAGGTTAGTTTCGCCCAATTAAAGTGAATAAAGTCCAGGGCAA
CTTCTGGTTAAGCACTAATTTTTAGACACTGACAACCAAAGAAGCGCCCACCTTCATTCCCAGAAGTGGAGCTTAATTATTTGAGCCAAATTAGA
CTGAAGGCGAAGCCCTTCACAAAGAGTTTGTTAGTCACCCAACTACCCTCTATCCGCATCAGCATCAAAAGTAGCATTACCATCACCAAGTTAAT
TACGCTCCAAACATACATTTAGCTACACAAAGACAACTACAGGGTATGCACTGAGACAAAGTCTTGGAAAATAAAATTCGCAGAAATTATACTTT
AAAACATCATTTTAGTAATGTGACTGAACTTTTTGATAAATAGTTCTCGTAAAAAGGATAGTTTATTTTTGACTTTCCATTGACTTTTCTCTCAG
TGTACCGAGGCTAAGGACACTTCTTATCACTAACCTTCTTCGGCGGCCTTCTCCTTCTCCTTGCGACGCTGCAGCACGACCTTCTTGAAGACAAC
CGCCGCGGCCTCCACTGCATTCTGCAGCTCCTGTTCGCCCAAAGTGCTTGTGTGGGTGGCCTCCTAATGAAAAATGAAATGGGGGAGCAGGATGA
AAAGGTTTCACGCTTAAGCCTACTGGTCTCCGGACGCTTGATGTTCTACTCACCGCCGAGCTGTTGGGATCGCCGCCCTCCTTGTTCGCCGAGGA
CTCGAGGGACTTGCCATTGACCGGCTGCTCCGCTCCAGATCCTTGGCCGGATTCCCCGTGGGGCTTCTCCTCCTCTTGCCCTGTGGATGCTACTG
AGGCGACAGGAATTTCTGTTTTTTCAGGCGCATGGCTAAATCAGAGTTTCTATGCATAAGCTGTTGATGGAAGGAGTAAATGTGCTGGGGCGTG
CTACCTGTGGGGGCGGTTAACAGGAGGGGGTGCAAAGCGTTCATCAATCGGGTGCCGAAACAAGCGCAGCTACTCAAGGTTCTACCAGGGACCGC
AAAAATTAATTAATTAATTAATTCATTCATTAGCCGTAAATACATAGTTACTTATGCGCAGGCAATCACTACTTTGGGAAGCTGGGGTGGGGATA
CTTCACTTGTATTAGGTGTAAAAATTTAAGTTTCTAATCACTGAATGGTTTATTGCTTGAACTTATATTTGTTAAGGAAAGCGATTTAAATTTTA
CTAAGGGGTGTAATATTGGCTTTATATTCTTTTAATAGAATAATAGTATAACTTTTGATAAAACAGACATTGAACATGCAATTTATCAAATAAA
GAGCACAACAATAATCACTTGAAGCTAGATTTGTTTTTTTTTTGTAGTTTTGCTTAAGCGAGGGACAAAGTTTGAATAGTTTATTTTGTAGTGTG
TAATGTATATTTTCTACAAAATATATTTGTACAGATAGCTATCTACATAATATTGCTTTACCATCTTTGGTTTATTGTGTATATTTGATATGTTT
CTAATGACAGTGAGCGATTATTTTATGGCTTAAAACTTGTGAATGCAAATGATAGGTGCTTGTGAAATAATTGGTAATAATTGCGGTCCCTGGGT
TCTACGGATGCGTGATCGCAGATTGCAACCATAGCTACTATCAAAAATGACGTATCCTCGGTACTTACCCTCCTCAGCTTCGCCGATTCCTGTGC
GACTGTTGCGGCGCCTCGCCTGCGGAATCTTCGAGTTGCCACGCGTTTATCCAGGATATCAGCCAGAGGACGAGGGCTGGGTATTTTCGATATT
TCCGTTTTCTTTGTGGGCTGATCAGCGAAGTATTAATTAATGTATTTTCACCTAGATCAAGGTTGAGGTCAACTCACCTGAGTGTCCTTTTCGG
GATGCGAGAAGGATCGTCGTGTGACGGGCTTGGGCGTGGTCTTCGCTCCAGAATCCTCGGAAACAGAGCGCATCTGCTCCGGTTTTCTTCTCTCG
GCAGCATGGCTATCGGTGGCACTTCCACTGGCTGCACCTTCATTGCCCGAACCTTTGCCATTGGCATCCGAGACCTGTGAGAGTTGGGCCAGTTC
CTCCTGCTGCATCTGCAGTTCCCTGGATTGTCGGCGCCTAATGCGATTGTGCATTAGAGGAGTACGGGGTAGTGCTGCTCCGCCATAGAAGCCTT

FIGURE SHEET 722

GTGGGGTGCCCATGTCCGGATAATAGCCGGGCACACCACCTGAACCGCCACTGGCGCCTAGTCCCACGCCAGCTCCTCCCCCGTAACCCGAATCA
GCAAGGACATTCTCGGCACTGTAAATCGGTCTTTGGGAGGAGTTCTGGTAGCTTCCATCATCCGAACCATTGTTGTAGATGATACGTGGCTCACT
GCTAAATCCGGCATTATAGTTTCGTTCGTACTGCACCTCGTCGGACTCCAAGAAACTGGTCGCACTGTCGCCAAAGTAATCCACATATTCCGGGC
GATTATCCAGCTCCTCAGTGACATCGGGAAACTGATGGAACTGCTGCTTGGCCTCCCCGAAAGTTCTTTCCTCCTTCAGGCAATCCTGGCGCACC
AGGCGACTGGGCGATCGACCACCAGGCCGCTGCACAGCCGTTGGGATCTCCGGCAGCAATCTTCTGTTCTCCGGGTGTCCCTTGGTGTTCGAGTA
CTCCTCGTTGCTGTGGCTGCGCACCTTGATCATCTTGGAATGCGGATCACGGGAGTGATGGATGTTTACACTCTGACTACTGGAGTACTGCTCAC
CACCGCCGACGACCCCGGTGCTGGCCACACTGCCTCCGCTTCCCAGTTCGGTGCCTCCCACGGCGGGCACATGTGGCTGCGAGAGAAATTGCCGG
GGATTCGGAACACTTGGGAAAAGGAAATTCTGTTTGGCCCTCGGCGAAATAGGCATGAATTTTGCCGGAGGAGTAGAGTGCACGGTGAGTGTGTT
TCCACTGCTAAACGCTTCCGGATTTGGCAGAGTTTGCTGACGCATGAATTCCGGAGAACGTCGGAATTGCGGGGAAGTCTGTCGCTTTGGCGGAG
ATGTGGGCAGTAGCTTGACATGCTGCTCGGGATTTGGTAGAGTTGCCTGCCGCGTCATTCTCGGCTTGGGCATGGGTCCCACATCCTGCTCGTCG
CTGGCCAAACTGGACGTTTGTGATTCGTAATTCAGTGGTGGCGGAGCCACTGTCGGCGGAGGTGCTCCCGTGCTGGGCAGCAATTTGGTGCGATG
ATAGGTGCTGGGCGGCTCTGGGAACGAGGTCTGCCTCATGAAGGGCGGATAGCGCTGCTGCTCACCCGGCGATCTTTCCGGGGAGCGACTGTACA
GCCGGTTCGGGGATGTGGACATATATATAGCCGGAGTTGGTTGAGCTGGCAGCGTGGATTGGCGGCGCACCTGAAGCCGATGATGCGTGGGTGTC
ACCTCCAGTTGGGGCTGCTGTTGCTGCGGCTGCTGCTGCTGTACGTAGTTCTCGCAGTCACCCACCGTCACACCAACTCCCACTCCCATTCCGGG
CATGGTGTTCATGTGGATGACGTCGTCGCTGTTGTAGGCGCTCGGATAGAGCGGACTCTTCTGCAGTTGATGCGGCGATGTGGGCGCCGTTAGAT
TCACGGAATTGTAATTGGCCAGATTGCCACCACTGCCGCTGAGAGCCGGGTCGTTGTTCAGGCTACTCGGAAGCGTCGACTGACGCAGGACCCTC
CGTCCCAGCTGCCACTTGCTACTGGTTGTGGGCGTGGCAGTGCCACTTCCGTAATTGATGCCGTGCGTGGGTCGCGGCTGTGGGGGCAGGTGATG
CTGCTGGTGGTGCTGGTGCAGGGTGGGGTAGCTGCCCGCTGATTGGGCCTCAATCAAATGCTGCTGCTGCGGATATAGGTTGTCCGCCACCGGCT
GTTGTGAGTTGGGATTGTTCGGATCGTCCTCGGGATCTGTCGGGATAAAGGATTTTCAATAATCCGTTCTAACAAATTGCAATATTTTTTTTTT
AAAAAATCTTGGAAAAACTATTAAGCACTTAAAACTTATTTAAATGCATGACTTTTGCTGTTCGCAGTCTGTTTAAAAAATGTACTTACGTAGT
TGAATAATCCTTGAAGGATTCTTTCAAACATGCATATACTCAATCAAAGTCTCTTAGCCATATAATGAAAGTAAAATCCAGAGTACTTACTCGAT
ATGGTCCAAGAACGCCGGATGCTCTTCCTCAAGACGTCGCTGGTGGTCAGATGGTCGACGGCACTGCAGGATCCCAGGGCATAGGCGTCCTTCAG
CCACTCGCCGCTGGCCGACTGTATCTCCCTGCAAGAGCAACAACATTGCCACTTTAGAAACCAGAAAACCTCGCCAAACATTTTCCCAACTTTCG
TTGGAGACGTCAAACAGTCAACAAGTAAATCGGCGACTCAGCGGTATCACGTCTGTCTGTCCTCGCGACATTTGGCAGACTGGCTGGCTGACTTA
CTCAAACGAACACTGAATGCCGGATTGTCGGTGTCACAGCAGCAGCAACAGCAACATGGAACATGAAACACCAACACACACCATGACTTTAAGCC
AAGGTGTGAGCCAACGGAAGAGTTAAAGCCAGCACAGACTGCCTTGGGTTCGCACAAACAGACAGAAATGTATTTTTGGGGAAAAATTTGACGGC
GAAACCACAACGGAAAAGTTTGGGGCTCAGATACCAAAGAAATAATTACATATTTAATGAATAAGACAAACTTCAACCGGAAGTTGGTCCTGCTT
ATGTTTAACTTTAATCTCACGTTTGGGTTTTAAATAATATTAAAAGTTAGCTTCATATGGCCATACATTGCATTACACTTCCATTTAATTTGAAT
AGCCATACTAAGAACTGGAAACGTATTTATAATTACCAAGAACTATATGATTGGAAAAGCATTTGTACAATTTAATTAAGTTCCTGGGAAAGATA
AACTCTTTATTAAATTTCTGAAAACTTGATTATTTTAGCGGGTGATATAACACCCACTTATGTATTAAGCAAATAATAATTTATATATTACTAGA
AAAGCTTTTTGGTAACGCACAATGGGGTTTCGAGAAAAAAGCGTTATTAATAACCCATTTGTACGTATATACAATTTAATATAATCAATGCGTGG
TTGCCCAGATACAATAAAAAATAAGAATTCAATGTCTGGCCAGAAATTCATGAAATAATTGTATTTCTTCGGCCAGACACTGTGCTTTTGTGCCT
GACTTGGGGGTGCAGTCGAAGCAATTGGATAAATTCCTGCTGAGAGGCAGACGCAAATGCAGACGCCCTCCATCAAAATAAAAAAGGGGCTGGGT
CCATCGTGGTAGTCATCATGTGGCATTCATAATTAT
(SEQ ID NO: 1354)

Exon: 14711..14531
Exon: 14286..12762
Exon: 12665..12239
Exon: 12177..12039
Exon: 11309..11074
Exon: 10988..10865
Exon: 8285..1251
Exon: 1032..1001
Start ATG: 14711 (Reverse strand: CAT)

Transcript No. : CT34675
ATGTTTGGCGAGGTTTTCTGGTTTCTAAAGTGGCAATGTTGTTGCTCTTGCAGGGAGATACAGTCGGCCAGCGGCGAGTGGCTGAAGGACGCCTA
TGCCCTGGGATCCTGCAGTGCCGTCGACCATCTGACCACCAGCGACGTCTTGAGGAAGAGCATCCGGCGTTCTTGGACCATATCGAATCCCGAGG
ACGATCCGAACAATCCCAACTCACAACAGCCGGTGGCGGACAACCTATATCCGCAGCAGCAGCATTTGATTGAGGCCCAATCAGCGGGCAGCTAC
CCCACCCTGCACCAGCACCACCAGCAGCATCACCTGCCCCCACAGCCGCGACCCACGCACGGCATCAATTACGGAAGTGGCACTGCCACGCCCAC
AACCAGTAGCAAGTGGCAGCTGGGACGGAGGGTCCTGCGTCAGTCGACGCTTCCGAGTAGCCTGAACAACGACCCGGCTCTCAGCGGCAGTGGTG
GCAATCTGGCCAATTACAATTCCGTGAATCTAACGGCGCCCACATCGCCGCATCAACTGCAGAAGAGTCCGCTCTATCCGAGCGCCTACAACAGC
GACGACGTCATCCACATGAACACCATGCCCGGAATGGGAGTGGGAGTTGGTGTGACGGTGGGTGACTGCGAGAACTACGTACAGCAGCAGCAGCC
GCAGCAACAGCAGCCCCAACTGGAGGTGACACCCACGCATCATCGGCTTCAGGTGCGCCGCCAATCCACGCTGCCAGCTCAACCAACTCCGGCTA
TATATATGTCCACATCCCCGAACCGGCTGTACAGTCGCTCCCCGGAAAGATCGCCGGGTGAGCAGCAGCGCTATCCGCCCTTCATGAGGCAGACC
TCGTTCCCAGAGCCGCCCAGCACCTATCATCGCACCAAATTGCTGCCCAGCACGGGAGCACCTCCGCCGACAGTGGCTCCGCCACCACTGAATTA
CGAATCACAAACGTCCAGTTTGGCCAGCGACGAGCAGGATGTGGGACCCATGCCCAAGCCGAGAATGACGCGGCAGGCAACTCTACCAAATCCCG
AGCAGCATGTCAAGCTACTGCCCACATCTCCGCCAAAGCGACAGACTTCCCCGCAATTCCGACGTTCTCCGGAATTCATGCGTCAGCAAACTCTG
CCAAATCCGGAAGCGTTTAGCAGTGGAAACACACTCACCGTGCACTCTACTCCTCCGGCAAAATTCATGCCTATTTCGCCGAGGGCCAAACAGAA
TTTCCTTTTCCCAAGTGTTCCGAATCCCCGGCAATTTCTCTCGCAGCCACATGTGCCCGCCGTGGGAGGCACCGAACTGGGAAGCGGAGGCAGTG
TGGCCAGCACCGGGGTCGTCGGCGGTGGTGAGCAGTACTCCAGTAGTCAGAGTGTAAACATCCATCACTCCCGTGATCCGCATTCCAAGATGATC
AAGGTGCGCAGCCACAGCAACGAGGAGTACTCGAACACCAAGGGACACCCGGAGAACAGAAGATTGCTGCCGGAGATCCCAACGGCTGTGCAGCG
GCCTGGTGGTCGATCGCCCAGTCGCCTGGTGCGCCAGGATTGCCTGAAGGAGGAAAGAACTTTCGGGGAGGCCAAGCAGCAGTTCCATCAGTTTC
CCGATGTCACTGAGGAGCTGGATAATCGCCCGGAATATGTGGATTACTTTGGCGACAGTGCGACCAGTTTCTTGGAGTCCGACGAGGTGCAACCG
ATTTACAGTGCCGAGAATGTCCTTGCTGATTCGGGTTACGGGGGAGGAGCTGGCGTGGGACTAGGCGCCAGTGGCGGTTCAGGTGGTGTGCCCGG
CTATTATCCGGACATGGGCACCCCACAAGGCTTCTATGGCGGAGCAGCACTACCCCGTACTCCTCTAATGCACAATCGCATTAGGCGCCGACAAT
CCAGGGAACTGCAGATGCAGCAGGAGGAACTGGCCCAACTCTCACAGGTCTCGGATGCCAATGGCAAAGGTTCGGGCAATGAAGGTGCAGCCAGT
GGAAGTGCCACCGATAGCCATGCTGCCGAGAGAAGAAAACCGGAGCAGATGCGCTCTGTTTCCGAGGATTCTGGAGCGAAGACCACGCCCAAGCC
CGTCACACGACGATCCTTCTCGCATCCCGAAAAGGACACTCAGCCCACAAAGAAAACGGAAATATCGAAAATACCCAGCCCTCGTCCTCTGGCTG
ATATCCTGGATAAAACGCGTGGCAACTCGAAGATTCCGCAGGCGAGGCGCCGCAACAGTCGCACAGGAATCGGCGAAGCTGAGGAGGGTAGCACG CCCCAGCACATTTACTCCTTCCATCAACAGCTTATGCATAGAAACTCTGATTTAGCCATGCGCCTGAAAAAAACAGAAATTCCTGTCGCCTCAGT
AGCATCCACAGGGCAAGAGGAGGAGAAGCCCCACGGGGAATCCGGCCAAGGATCTGGAGCGGAGCAGCCGGTCAATGGCAAGTCCCTCGAGTCCT
CGGCGAACAAGGAGGGCGGCGATCCCAACAGCTCGGCGGAGGCCACCCACACAAGCACTTTGGGCGAACAGGAGCTGCAGAATGCAGTGGAGGCC
GCGGCGGTTGTCTTCAAGAAGGTCGTGCTGCAGCGTCGCAAGGAGAAGGAGAAGGCCGCCGAAGAAGGCATAGGGCAGCAGCTGTCCGTGGTTTC
CGTTGATATCGGTGGATGTGGAGGTGGGGGCGATGCCGTGGAAACCTCGTCGTCATCGGAGCTAGACTTCAGGTGTTCCACTCAGCACGGACGAC
AGCAGCAGCAGTCGCAATATAGCGTTGAAGCGGACGAGTTCAAGCTCGTCTTTCTCAACTCGGATTCATCGTCGTCCTGTCACGGCGAAGAGGAA
GAAGAGGAGGAGGAGGACGGGGAGGAGGATGACACGGATTCATCCTGCTCCACGCACCACTGTCACAGCATTGTGAGCAATGTGGAAGACTGCGA
TTGGGATTACTTTGAGCCCTCCATGATCTCCACCACGACGACCACGACAACTACCATGATTGCCTATACTACAGCCCGAGCCACGCCCACTCCAC
CGCCGCGTGTAAGGCGTCAGTCGAGCGATAGCGATTCTCCCCAGGTGCAAAGGCGACCCCAACAGCCCAGGAATATCTATTGTCCCAGGATCAGG
GAGAGTGACACCGGCACCGACGAGGAGTTTGTGCTGAACACCGAAAGCAGTTCGCAGACCAGCTCCGATCAAACACCACCACCCGTGCCACCACC
GCCACATCCGCTGAGCATGAAGACCCGGATTAAGACGCGATTCTTAAAGAATCATCACCACCACAGCCACAACCGATGCAACTGCAATCCCGGCC
AGCAGCAGCAGCAGCCGCAGTACGTGCCCATTCCCGTCCCGGTGCCCATACCAGTGCCCATGGCCGCCTATCCCAACTGGCCAGAAGTGTCAGGC
AATCCACTACTGGAACAGGACGAGCAGCTGGCTGCCAGTCTGCAGCAGCTATGGAAGGCGGCCGGTCACCAGCAGCAATTTGCCGCCATAGTTGC
CGCCTATTCGCAGCAATTTGCAGCGGCCAGTGGCAACATGTTCGATGCAACGCCGCCGGTGACCAGCAAGAGCTACCAACAACTGCCTACCACTC
CGCCGCCAATTCCGGAGCGCTTGCGCGGACTGGGTGGCTTCAAGTCCTCGGCACCGGAGCTGAGTGCCTCGCTGGGATCACTGATGACGCAGTCG
CTCTGCTCCACCATATCCTCCTCGTCGTCGTCGAGCACCTCGGGCTATGGGACGGCGGGTAGGAGCCTGGAAACGCTGGCCAGTCCAATGCGAGC
TGCCAACTCGATGCAGCAGCAGCAGCAACAATACCAAGAGCAACATCAACAAATGGCCAGCAGTGCTTTCAAGCCAAAGCCAACAAGTTTAGTAG
CTTCGCGTTCGCCGACGGGTGAGCAACTAGAAACGAGCAACGCGCGTCGCGGCAGCAGCAACAGTGAGAGCGACGACAACGCCAACAGCAACAGC
AACAACGCAACGCCCACAACGGGTAGATTGTGTAATGTTTATGATAAAACCGGCACATTGCCAGTGCCTCAGTGCGTTCAGGCACATGTTGCCAG
TGTAGATAAGAGTGCCGCGACAGCAGCAATATCAACAAAAGCAGAGCCAGCAGCAACACCAGCGACATCCACAAAGGGAACCGCTCTGAGAGTGG
CCAGCAAATACCAGAGCCGAAATCTATGCGAAACCCAGTCAGCGGCAACAACACAAACCTACCTGGCCAGTAAAAACAGCCACGAAGAAGTGGAA
GCAGCAGACGAAACGAATATACATAAAAATCAAGTACCAGCAGCGGCAGCCGCAGCAACAGCACAAATACAAACAGCAACTAGAGCTGCGGCTCC
TGCGGTAATAACTCGTTTCGGCGGACTTGCAGTCGAAAATGCTGTTGGAAATGTGGCTGAAAGTGCTAGTGCCAGTGCCGCCAGTCCCATTCCCA
AGCCCAAACCCAGAGCCCAGCACCCAGAGCAGATAGATCGGCATCGAGCGACGGCGGAGACTGCCAAGAATTTGTCCTCCAATCGACTTATAGAG
AACATCAAGATGTCCGATGAGGCATCACCATCGACGGCGGCCCATCTGCAGAGCGAAAGCTATGCGGCCAGTAGTCCAGATGAGGCCAGCAGCAA
CAGCAGCCAGGATGGAGATCAGGATAGGGAGCGTGAGTTGGAGGAGCAGGCGGAGCAAAAGCCGCGTAGGACCACGCAAAGAAGCTACAACGTTG
CGGGAATGATGGAGGAGCAGCAACTAGGAGAAGTGGATGCAGTGGAGCAACGACACCACAGCACCACCAGCGATTCCAGCTCCAGCAGCAGCTCA
AACTCCAGCTCCAGCTCGGAATCGTGTGACTCCGATGATACGGGAACTGTGCGCGATCGCAGGCCCAAGAGAAGGAGGTTCAACAAGGTGTTCGT
CGTAAATCGACAGCCCGGCGGCCGGGTAAGACGCAGTTCCTCCACCGAGGGCGATTCTCTGTCTTCCTCGGAGGCCAATTTGGAGGATTCCTCTG
ACAATGATACAGACACCGAGCGCACCGATTGTGGAATTGTGCTCAACTACGTGAAACCCCTAGAGGAGGAGCCCAAGAAGGCGGAGGAGGAGCCG
CCGACAGCTGCACGTGATTGCCAATCAAGTGACGAAGACAACATTAACGATGATGAAAGTGAACGCCGTGTTGCCAACTCAACCGATGAGCTGGC
CAACTGCATTGTAGTGGTGGGCGGACAGACGGACGACGCCGCCGCCGGCGTGGTGCTGCACCACATGCGATCGCTGCCAGACGTCGAGTTCGATG
GCGAGCAATCAGAGCGCCGCCAAGCGCATGAGATAGACGCCAGCGATGCCCTGGCCGCCTGCGATGAGCTGCACAGCATCTCGAACGATGTCAAT
CGATTGCTGGCGCTGCACAAGCAGAACTCTCAGCTGGAGTTGAAGCTCCAACGCTTGCGCCAGGGAGTGGCCGAAATCAATGAGGATCTGCAGCT
CTCCACCACGGGCACTGATGTGGCTGCCACCCACTGCACAACGCAGCCAGGTAGTGCCGGGAAACCCGACGAATGCAATAGCCCTTCTTCTCGGA
AAAGCCCCTCGACCGTGCTAAGTTCTAATGACGTTGGTCCGCTGAGTCTCACCTGCTTACGGCAGGTAGAGGCAGTGGTTGAGGTAGAAGCAAAC
AGAGCTGATGGCAAACTGCGGGATGAGCGGAATGGCCGAACAGCTGAGCAAACCGAGGAGAGGGTCGTCACATGCAGCCAAGCATGCAAAATAAA
CGACAACAGTGACTACTCGCTGGATTCACTCTCGGCAACTTCGGCGAGTTTGTTGGCACCTGAGCAGCAGCAGCAGCAGCCGCTCCAGCAGGTAG
AAGAGAGTGCTCGCCTACCTGCCGACGCTCGCGAGCAACGATATCGCCGTGGAGCGAAATCGGAGTCGGCGGAGTCGCCAGTCGAAAATGAAATG
TTAAACGTTGCGGTCGCTTCTCGTGCCGCGCTTCTCGGCAGCAATAACAACAACACACACAGAAACGATAATAGCAATAACGAAAACACTAACAA
CAACGACGGCGAACTTGGCCATAATAATAATGACGCTTTCGCAGCACAAAAGACGAGAAATAGCGGCTCGAGTGTGGTTGTCGGCTGCGATATTA
GTGACGTAGTGAGTGTGAATTCAAATGTGAGTGGTGAAAACGAGTGTGACTTCGACAAAATATTTGGTAGTCATCAGCAAAACACTCCAAGTGCA
TCAGCAGCAGTTGCAGCAACAGCAGCAGCAGCAACATCTGACACACCTGCAACATCGCCCAGCGAACTGGCTTCGCCCAAAAATTCACTTTCAGC
CAAGTATCGCAGTTTGGTCATGATCAACAAAGACAATGAAAGTGCAGCTGGCGATTACGAAATGGCAAACAGCAGCAGCAACTTCAGCAACATCA
GACACAAAGACCCGACCAGTAGCAACAACAGCCACACTGTTGGCCAGAACTTTGCGAGTGACTCATTTCGCGCCATGGAACCAACGGAACTCGTG
AGCAGCGATCGCGAAGCGTACAGTGTGGACTCGCTAAACGAACCGCCTGCTGTGCCGGAACTCAGCGTAGAGGACGGCTTGGCTGATGACGACTC
CTGGGTGGAGGAACTGAGTCAGCGCGGCGAGGATGAGGACGAAGATCTCAGCAATGCTACCACCACACCCACGGCCACAGACTCCGAAGATGCGG
AGGGAGAAGGTGAAGGAGCCCGGCGACATGGATATATGGATCGAGAGGAGGACCTAAGGGGATACAATAGATCTGCCATCGACTTCACCCTGCAC
ACCATCGTCGAGGAGAGTTGTGAGGAGAGCGAGGTGGCCTCCATGCGGGCGGACAATGAAGACGTCGAGCTGGAGGATGAGGATCTATCCGAACG
GAGAAGGCAGCGCACCTTGCAGCACCACCATCGACTAAGTGCCTCTGAACTAGAGAAGTACTTCTTCTTTGGGCTGGGAGATGGTCGAGTAATGA
GTTCTATTGATACACGCGGAGATGACACTGCATCCGAAGTGAGTTCCGAGTGCTCTGAGAGTCTTGACTCCCTACCGCATGAGGATCAGCTGTTG
GATACAAGTGGAGCTTCCGATCTGGCCTCTTCCCGTCTGGAAAAGTACTTCCTCTCCGGCTTCATGGGATTCAGTGGTGCAGAAAAGCAGGCGGA
GAGCGATGAAAGTGGTGGCAGTGTAGGCAGTGATAGTGAAGGACAACCGAGTCCCAGTCAGCGGAGAAAGCGACTGGTAAGAGCCAGGGGAACAC
CTAGAAGTCACAACTCCTCGTTGGATAATTTGCTACTGCCAGAATCAGACACCCTGGATGCCACAGTTACTTCTGCAGGCGGAGCAGCTGCAGCC
ACTGTAGAGGACACCTCGGAATCGGAGGCGGGCTGTGACGACACTGTGATTCATTTGGCCAATGCCGGAGCTTCGGATGGTTCCTCCTCGGACAC
CATTAAACGCAAGAAGCAACTGCGCAAGCGTCACGACTCTCTGGACGAGAAGAAGCTCCACGATCTAGAGCCTTCCGAGTGCCGGACTCCCACCC
CGGGCAGCAGTGGTCAAGTGCAGATGCAGTCGCAGGCGAAAAAGCAACAACAGCAGCATCACCACAGCCGGGACAGTGGCTTTGTGGGCAGCAAC
GATGATCTCCTGAAGGCGGCACCAGATTGTGAGCCACCCAAGAGCCCAACGCCAGCTCTGGAGCAGATCAGTGAGGATCGGGAACCGGTCCATAG
TCAGATTAGTCTGGCCAGGATGGATCAACCAAGCACTTCAGCAGCTGCAGCTGTAGCCAGCACACTTTCCAGCCAACTGAAAAATCTTGCCCTGC
CCAATCTGGTGCGAAAGGATAGCTTCAACAATTGGAGCTCCGACGAGGAGACCAACCTGATGATGAGCAAGATGCGGCAGTTCTTTAAGAACCTC
ATTGTCGCCACCGCCAATGCACAGCAGAGCAAGCCCTCCACGCCCAATCAAGGGCCCAGCACCACCAATGTCAACACCACGCCCAGTTCCCAGCG
CAGATTGGCCAAATCCCGGCCAGCTCAGTTGGCCTACTTTGAGAATGAGCTGACCCGACTGATGAAAACCGTGCCGGGCATCAATGATGAGCAGG
TGCGCGAAATAGTGGAGTACCTGAGCAGTGAGGATACATGGTCTGATTCCTACGATTCTTCGGACTACACGAGCTCCGATCTGGAGGGCGGTGAA
AGGAAGGGCCAACTGAAGGCTCAGATCTCCGCCAGCTGTCAGCAGATCATCAACAAGTTTGAAATTGACGAGGAGGGTGATCGTGGTGATGGTGG
ACTGCTGGACGAGAGCCAAAGTGTGCCTATGGAAGCATTGGTGTATCAGAAATTGGTAGCTTCCTTTAGCAAAGTGGCGGCGGGTGGAGAACCGG
AAACAGAAGCCACCAAAGCGGTGGAGGAAGCAGAACCGTCCACGGAGAGATCCCCGCAACTGTTTGCCAAGGTGATGCAGCATATTGGTACCAGA
TTGGTAGCTCTGATGCACGAAGTTAGCAGTGGCAATGAAACACCCACTCCATCCCCGCAAGGACAGCGGCATCATCGAAGACTGCAGGCCAAGAT
CTCGGCCACCACGACGGAGGATGAGGAAGATGAGGTGGCGGAGCAACTGAAAGCCATGCCCATCAAGCAGCTAAAGCTGCGAAGCAAATCCCATG
ATCTACTGCTGGACGGCACTACGCCGCATTCGCATCACCTGCACCACCATGCCACGGTGCATTATCCAGCCGGCGGCGTGGGATCGGGAGCGGGA
GGATCCGGCGGACCCGGACACTCGGACAACGCCGGGGAGGAGTGCGGCGTGACCAGCGACTACGAGCGATTCTCGTGGCGCGGCAGTTTTGAGTC
GGCATTACTGGCTAATGGCGACAGCAGAACGAGGCTCAGCCAGCTGAGCCAACTGGACAGGGATAACTCGTCGTCTGCGTCCGCTTTGGCTGTGG

FIGURE SHEET 724

CAAAGCGCCGATCGGCAGGCGACCTTCTCTTCAGCCAGCACCAGCAGAGCCTGAGCCGCGAGCAATTGGATCGCGTCCGATCCTGCGGCAGCATT
GGAGGCGGCGATGCCCATCACCACCAGTTGGAGTCCTCGCCGGCCAAGCCGTGGCTCTCCTCCGCGGGATCCTCGATTGGCGGTGATTCTACGAA
GGATGTGCGGCGTTCCAGTGTACCGGATGCCATTTACGAGACGGACTCCAGCGATGAGGCAGCTTCGCATCAGTTTGGCGGCGCCAGATCCACGT
TGCCGCGCAGTCTGAATCCCAACCAAGTGGTGGCTAGCACGAATTCACTACCCCGGTTACCCACCACCGGTGTTGGTGCTCCCATAACCAGCACC
CCCAAGACAAAGTCTCAGAGCGCCCTCAACCACACGCCCTCTAATTTGTCCACCGTTTCGGCCACTGGCAGTGCCAAGAGTGCGAGATACCGCTC
GCCAGGATTGGCAGCTCGAGCAGCGGCCGTCAGTGGGGCAGGAGGTGGCTCAAGTGGTGGTGTTGGTGTGGGTGCCAGCAGTGGTTCGACGGGCA
AAAAACTAGGCGCGGGCTTCCAGTTCCTCTACTCCAAACGCGATGCGCGCAAACGTCTCAACATGTCAGCTGGCATAAAAGTTCTGGGGGAATCT
GATCCTTAG
(SEQ ID NO: 1355)

Start ATG: 1 (Reverse strand: CAT)

MFGEVFWFLKWQCCCSCREIQSASGEWLKDAYALGSCSAVDHLTTSDVLRKSIRRSWTISNPEDDPNNPNSQQPVADNLYPQQQHLIEAQSAGSY
PTLHQHHQQHHLPPQPRPTHGINYGSGTATPTTSSKWQLGRRVLRQSTLPSSLNNDPALSGSGGNLANYNSVNLTAPTSPHQLQKSPLYPSAYNS
DDVIHMNTMPGMGVGVGVTVGDCENYVQQQQPQQQQPQLEVTPTHHRLQVRRQSTLPAQPTPAIYMSTSPNRLYSRSPERSPGEQQRYPPFMRQT
SFPEPPSTYHRTKLLPSTGAPPPTVAPPPLNYESQTSSLASDEQDVGPMPKPRMTRQATLPNPEQHVKLLPTSPPKRQTSPQFRRSPEFMRQQTL
PNPEAFSSGNTLTVHSTPPAKFMPISPRAKQNFLFPSVPNPRQFLSQPHVPAVGGTELGSGGSVASTGVVGGGEQYSSSQSVNIHHSRDPHSKMI
KVRSHSNEEYSNTKGHPENRRLLPEIPTAVQRPGGRSPSRLVRQDCLKEERTFGEAKQQFHQFPDVTEELDNRPEYVDYFGDSATSFLESDEVQP
IYSAENVLADSGYGGGAGVGLGASGGSGGVPGYYPDMGTPQGFYGGAALPRTPLMHNRIRRRQSRELQMQQEELAQLSQVSDANGKGSGNEGAAS
GSATDSHAAERRKPEQMRSVSEDSGAKTTPKPVTRRSFSHPEKDTQPTKKTEISKIPSPRPLADILDKTRGNSKIPQARRRNSRTGIGEAEEGST
PQHIYSFHQQLMHRNSDLAMRLKKTEIPVASVASTGQEEEKPHGESGQGSGAEQPVNGKSLESSANKEGGDPNSSAEATHTSTLGEQELQNAVEA
AAVVFKKVVLQRRKEKEKAAEEGIGQQLSVVSVDIGGCGGGDAVETSSSSELDFRCSTQHGRQQQQSQYSVEADEFKLVFLNSDSSSSCHGEEE
EEEEEDGEEDDTDSSCSTHHCHSIVSNVEDCDWDYFEPSMISTTTTTTTTMIAYTTARATPTPPPRVRRQSSDSDSPQVQRRPQQPRNIYCPRIR
ESDTGTDEEFVLNTESSSQTSSDQTPPPVPPPPHPLSMKTRIKTRFLKNHHHHSHNRCNCNPGQQQQQPQYVPIPVPVPIPVPMAAYPNWPEVSG
NPLLEQDEQLAASLQQLWKAAGHQQQFAAIVAAYSQQFAAASGNMFDATPPVTSKSYQQLPTTPPPIPERLRGLGGFKSSAPELSASLGSLMTQS
LCSTISSSSSSSTSGYGTAGRSLETLASPMRAANSMQQQQQQYQEQHQQMASSAFKPKPTSLVASRSPTGEQLETSNARRGSSNSESDDNANSNS
NNATPTTGRLCNVYDKTGTLPVPQCVQAHVASVDKSAATAAISTKAEPAATPATSTKGTALRVASKYQSRNLCETQSAATTQTYLASKNSHEEVE
AADETNIHKNQVPAAAAAATAQIQTATRAAAPAVITRFGGLAVENAVGNVAESASASAASPIPKPKPRAQHPEQIDRHRATAETAKNLSSNRLIE
NIKMSDEASPSTAAHLQSESYAASSPDEASSNSSQDGDQDRERELEEQAEQKPRRTTQRSYNVAGMMEEQQLGEVDAVEQRHHSTTSDSSSSSS
NSSSSSESCDSDDTGTVRDRRPKRRRFNKVFVVNRQPGGRVRRSSSTEGDSLSSSEANLEDSSDNDTDTERTDCGIVLNYVKPLEEEPKKAEEEP
PTAARDCQSSDEDNINDDESERRVANSTDELANCIVVVGGQTDDAAAGVVLHHMRSLPDVEFDGEQSERRQAHEIDASDALAACDELHSISNDVN
RLLALHKQNSQLELKLQRLRQGVAEINEDLQLSTTGTDVAATHCTTQPGSAGKPDECNSPSSRKSPSTVLSSNDVGPLSLTCLRQVEAVVEVEAN
RADGKLRDERNGRTAEQTEERVVTCSQACKINDNSDYSLDSLSATSASLLAPEQQQQPLQQVEESARLPADAREQRYRRGAKSESAESPVENEM
LNVAVASRAALLGSNNNNTHRNDNSNNENTNNNDGELGHNNNDAFAAQKTRNSGSSVVVGCDISDVVSVNSNVSGENECDFDKIFGSHQQNTPSA
SAAVAATAAAATSDTPATSPSELASPKNSLSAKYRSLVMINKDNESAAGDYEMANSSSNFSNIRHKDPTSSNNSHTVGQNFASDSFRAMEPTELV
SSDREAYSVDSLNEPPAVPELSVEDGLADDDSWVEELSQRGEDEDEDLSNATTTPTATDSEDAEGEGEGARRHGYMDREEDLRGYNRSAIDFTLH
TIVEESCEESEVASMRADNEDVELEDEDLSERRRQRTLQHHHRLSASELEKYFFFGLGDGRVMSSIDTRGDDTASEVSSECSESLDSLPHEDQLL
DTSGASDLASSRLEKYFLSGFMGFSGAEKQAESDESGGSVGSDSEGQPSPSQRRKRLVRARGTPRSHNSSLDNLLLPESDTLDATVTSAGGAAAA
TVEDTSESEAGCDDTVIHLANAGASDGSSSDTIKRKKQLRKRHDSLDEKKLHDLEPSECRTPTPGSSGQVQMQSQAKKQQQQHHHSRDSGFVGSN
DDLLKAAPDCEPPKSPTPALEQISEDREPVHSQISLARMDQPSTSAAAAVASTLSSQLKNLALPNLVRKDSFNNWSSDEETNLMMSKMRQFFKNL
IVATANAQQSKPSTPNQGPSTTNVNTTPSSQRRLAKSRPAQLAYFENELTRLMKTVPGINDEQVREIVEYLSSEDTWSDSYDSSDYTSSDLEGGE
RKGQLKAQISASCQQIINKFEIDEEGDRGDGGLLDESQSVPMEALVYQKLVASFSKVAAGGEPETEATKAVEEAEPSTERSPQLFAKVMQHIGTR
LVALMHEVSSGNETPTPSPQGQRHHRRLQAKISATTTEDEEDEVAEQLKAMPIKQLKLRSKSHDLLLDGTTPHSHHLHHHATVHYPAGGVGSGAG
GSGGPGHSDNAGEECGVTSDYERFSWRGSFESALLANGDSRTRLSQLSQLDRDNSSSASALAVAKRRSAGDLLFSQHQQSLSREQLDRVRSCGSI
GGGDAHHHQLESSPAKPWLSSAGSSIGGDSTKDVRRSSVPDAIYETDSSDEAASHQFGGARSTLPRSLNPNQVVASTNSLPRLPTTGVGAPITST
PKTKSQSALNHTPSNLSTVSATGSAKSARYRSPGLAARAAAVSGAGGGSSGGVGVGASSGSTGKKLGAGFQFLYSKRDARKRLNMSAGIKVLGES
DP*
(SEQ ID NO: 1356)

Celera Sequence No. : 142000013383764
GTTAACGCAAGTTCCACTTGCATCAGGGTTCTCGGCACTCGCTGCCGCATACCTCACCTTGATATGACAACCAACATGCTGTGGTTCTCCAAATA
ATAGTCAAGATAGTTAAGAGGGTTCGAGTTTACGATTAGCTTTATTTTAAGATTCAGTTCGCGATCTGCTAGCGGTTCCGTTATGTGTCCGTTCG
AGACTGGGACCTCTTCTCCCGCCCCGCTGCTTTTATATCCGCTTCCCCCGTTGACCCCTCACCCTGAGTGCGACCAACGGCACTTGTTCCGAATG
CACACATACACAAACATGTTCCTAGACAGGCCCCGAGTCGCCTGCTGACGGGGCCCGAAAACACGAGAGCCGAGCGCTGGTGAGTCCTGACGAAG
ATCGCAAGAAGAGGGTTCGTAACTTACACGAACATGTTACTAGACAGGCCCCGAGTCGCCTGCTGACGGGGCCCGAAAACACGAGAGCCGAGCGC
TGGTGAGTCCTGACGAAGAGCGCAAGAAGAGGGTTCTTAACTTATATGTATATATTTGCATTACCTACATATATATGTATATATTAAGAAGCAAT
TTTAATTACTTAAAAAAAAAAACGCTTGCAAAATCGGTTCTTGCATGTATAAGCTATGAAAGTTAGAAAAAAGTATACCACGCCGTATATGGTCA
TGAAGCTGGCTCCAAGAAAGAGGCCAATGGCTCCACCAAACGACATTATCAACTGATCCGTGCTGAATACAACCCGCCGATTTATGCCCATCCTC
GAAATTTGCAGGTTGATGATCAGCGTCCGCTCGAACCTCTCGCCAGAGTAGTTGTCATCGCCCTGAAGAAAGTAAATTCTAAATTGCAATAATTG
GGGGCTTAAGGATACAACATTCTTTCACCCACCCCAGTCTGGTCAGACACTTTGAAGATGGTAAAGGTTTCCTCGCGACAAGACGGATAGCAATC
GCATGGTCTTTCAAGCCACTTGGACCGGGCTAGGCAGAGCATTCCGGATACTGTGCAGATTGGAACTTCGGGAGCTGCTACGTAGAAATAGGGCT
TGCAGTTGCACAGGCTCAGGGCCCATTTGATTCGGCACTCAAGTCGGCAAAGACTTGGGTGGTAGGGCTAAAAGGACATGTTGCTGTTTTGATTG
GACGCAATTGGTACGGGTAAAGGTCTAAAACTCACACTGTAATACTGCAGATTGTTTTCGTCACTGAAGCGACACTTGCGATATGCTACCGGTAG
ATTTCGCACCTCGCTTTCCGCCGATGTGGTATGTAGCATAATATCGAGATCCTTGGATTCGATGTCTTTAGCATCAAAAGAGGGAGTTCGCATGT
CGTCGGGTAGCATCATTTCTTCGACATCGTGAAGGTACTGTAAAGTTGGATTCGCTTAACAGTGTATTTCAAAAAAGAATGATAAATGCTGCCTA
CCATAAATATGGGGGCAACAATGCTATTTATAGGCTTCAGAGATGTGATGCAATTACTCAAATAGCCGCACTGTTTCATGGGTTCCATATCCTGT
GTTTCTCTTAGATAAAAGCGTTAAGTAAAAATGTAAATGTAAATTCTCTTGATGGGCACAAAAAATATGTAAAGCAAAAAGCGAAATTAAAGAAA
GAATAGCTTATTTATTTTATTATTTAATAATTTATTTTTTTTGTTTTATATTTAATGTTATTTAGGCGCAGACTTACAGTTTGCCGTAGGGATTT
CCGTATCGGTTTAACTGGCTGGATGTTTGGCACAGACCCACCTCAGTAATGATTGGCGCCAGTTCTGGCGGGATTTTAACCGCTATTACCTTTTT TTGCAGCGTGAGCAAAATGTTCAAGTAATTCACGTTGTCCAAAGTGGTATCATTCTCGAAGGGTTCCAGCGTCTCCAGAGTGGAGTAACGAAGGC
CGTTGATTGCAAGCAGAAACTTTCTGTAGTACACAGCTTTTTCTTTGTCTTCGCTGGGATCCACTCCCCAAGTTCTTGATATTTTATAATATATT
AGTGCTTTCAATTTACCAATGTAAATCGAAACACTCACTGATTTATAAGCCTTGGGATCTCCGTTTCGTCGTGGTACCTAGGGCACAGTGTTATC
CCCACGAAGGGGAAGATGCGCAGCCCAAAGAGATATTCGTACTCGTAGACAATAGGATTGTCCCGGAACCGGTACCATTGGTTAAGGCAGCTGCT
GATGGCGTAGTAGGCCGAGCCCAGGATTATGAATGTCCAAAAGAGGCGCTCGGCCCAGTGTAGATCCCTGCGGGCGATGTAGGGCATGCCGTGGA
TGGAGGACTCCTGGCACAGCTCGGCGAGCCAGTCCGGTTGCTTCGGCCGACTCATTTTGGATTCCATGATGAACTGAACAGAAGTTCAGAAGTTC
GCATTCAACTTTAGCGACCCGTGTAATGACACACAACAACACCACACCCTCCCCCCCCTCACCACCATTATTCACCTTGTTTGATGTGCTCCAAT
TATAGACTTTAATGGTGTTTCGCTGTATGTTCAGCATGCATATACAATTGTCGTGATTAGACCTGTCCTGCAGTTCCACGGAACTCTATGCAAAT
GGGAACTGGGCGCCTTACATTGCGCTTATCGAAGGCCTCTATTTGGACCACCAGCTTGTAGCGCCCATCCAGATTCGGAACATTCAAGCTGGTCT
TCAAGTCCAGTTCGTAGTCTTTGTACTTTAAAACGGCCTACAATATTGTGTTTATGAGAAATGACCAGTGACCAAACTAGGAGGTACATTTTCTT
ACCCCTGGTGTGGTCAAGCACTTTTCCTTAATCTCGTCGGAGTTGCTAATATACTTTGTCCAGAAATTATACCAGTATTGGTTCTTATCAAACAT
GTTTTTGCAAAAGTTATTGGAGCTGGCCGTAAACATAGTCTTCTGCCAAGTGCCCTTATCCAGGCGATAGACTTGACCAAATACCTGCGCGATAT
TCAAATAGTTTATTAGGAAAAGTTTCCTTAGGGACTTGCCTTTAATGTGTCTCCAGGCTGGACATCTTTCCAGACCACTTTCTGCTCTCCTTCAA
TTCGAACTTTCGAACCAAGGTTATGTACTTTAAGGGAGGAAGTATCCACCATCGCTTCAAAACCAGAAGGATTTCCGGGCTGATTCTCGCATGGT
GCTAACAAGCCATCTTTGTCCAATGTTAACTGGTACTCAGTCGCTCCAGCCAAACAGATGACCACTTGGAGCACCAGGATTGTAAAAGTAGCCTT
CATATTAACAAGCTTTCCAGTATGAGGATGGGTACATAGTGCTAAAAACTGCACGTTATATACAGCTTAGGGGTCGTCTATGATTCTAATTGCAC
ACAGTATAATATGATTATGATATGATAAAATCATTGTCTTTAATAATTTAAAAAGGGCGTATCTCTTTTGGCACGAAAATAAGTATGTTCGATTA
AAAATTCGCGTGACTGTTTTTCTAAACTAAATATTAGACGAATGTCAAGTTCATAACCCCATTTACCCCATATATTTTCCGGAGTTTTGGCAGAC
AGCAAATTCATTTACCTGCCCGGCTAGCTCAGTCGGTAGAGCATGAGACTCTTAATCTCAGGGTCGTGGGTTCGAGCCCCACGTTGGGCGACCAA
TATTTTGTAGTAAATATTCAAATTTTAATAGTTAATTGATTACCAGAGAAAATCAATTGTCGAGACTCTCGACTATCGGATATCTTTTAATTAAC
TAATTAGGCTTAAAGCATATGCGAACATGGATGGATGTAATTATATATAAAAATGATTTTTATACCCGTTACTCGTAAATTAAATTGGTTGAGGA
GTATGTAACAGGCATGAGGAAGCGTTTGCGACTATATAAAGTAGACATATTCTTAATCAGGATCAATAGCCTAGTCGATCTAGCCATGCCCGTCT
GTCCGTATGAGCGTCGAGATCTATAAAAGCTAGAAGGTTGAGATTCAGCATACAGATTCTAGAGACTTGAGACAAAGACGCAGGGCAATTTTGTT
GACCCATGCTGCCACGCTCACTGTAACGCCCTAAAACCGCCAAAATCGGCTGCGCCCACATATATTTGAAAAATTGTTGGACATTTTTTCATAAT
GTTATTAGTTGCTTAAATTTCTATAGATTTGCTAAAAAAAAACTTTTTGCCACGTCCACTCTAACGTTCTAAACCTTTCCAATTTTTCTATATCT
ATCAATATCCCAGAAAAATTATGAAATTTCGCGTTCGCATTCACACTAGCTGA
(SEQ ID NO: 1357)

Exon: 3233..3090
Exon: 2934..2758
Exon: 2697..2584
Exon: 2353..2034
Exon: 1974..1693
Exon: 1526..1427
Exon: 1367..1176
Exon: 1112..888
Exon: 822..649
Exon: 484..404
Start ATG: 3233 (Reverse strand: CAT)

Transcript No. : CT35185
ATGAAGGCTACTTTTACAATCCTGGTGCTCCAAGTGGTCATCTGTTTGGCTGGAGCGACTGAGTACCAGTTAACATTGGACAAAGATGGCTTGTT
AGCACCATGCGAGAATCAGCCCGGAAATCCTTCTGGTTTTGAAGCGATGGTATTTGGTCAAGTCTATCGCCTGGATAAGGGCACTTGGCAGAAGA
CTATGTTTACGGCCAGCTCCAATAACTTTTGCAAAAACATGTTTGATAAGAACCAATACTGGTATAATTTCTGGACAAAGTATATTAGCAACTCC
GACGAGATTAAGGAAAAGTGCTTGACCACACCAGGGGCCGTTTTAAAGTACAAAGACTACGAACTGGACTTGAAGACCAGCTTGAATGTTCCGAA
TCTGGATGGGCGCTACAAGCTGGTGGTCCAAATAGAGGCCTTCGATAAGCGCAATTTCATCATGGAATCCAAAATGAGTCGGCCGAAGCAACCGG
ACTGGCTCGCCGAGCTGTGCCAGGAGTCCTCCATCCACGGCATGCCCTACATCGCCCGCAGGGATCTACACTGGGCCGAGCGCCTCTTTTGGACA
TTCATAATCCTGGGCTCGGCCTACTACGCCATCAGCAGCTGCCTTAACCAATGGTACCGGTTCCGGGACAATCCTATTGTCTACGAGTACGAATA
TCTCTTTGGGCTGCGCATCTTCCCCTTCGTGGGGATAACACTGTGCCCTAGGTACCACGACGAAACGGAGATCCCAAGGCTTATAAATCAAACTT
GGGGAGTGGATCCCAGCGAAGACAAAGAAAAAGCTGTGTACTACAGAAAGTTTCTGCTTGCAATCAACGGCCTTCGTTACTCCACTCTGGAGACG
CTGGAACCCTTCGAGAATGATACCACTTTGGACAACGTGAATTACTTGAACATTTTGCTCACGCTGCAAAAAAAGGTAATAGCGGTTAAAATCCC
GCCAGAACTGGCGCCAATCATTACTGAGGTGGGTCTGTGCCAAACATCCAGCCAGTTAAACCGATACGGAAATCCCTACGGCAAACTAGAAACAC
AGGATATGGAACCCATGAAACAGTGCGGCTATTTGAGTAATTGCATCACATCTCTGAAGCCTATAAATAGCATTGTTGCCCCCATATTTATGTAC
CTTCACGATGTCGAAGAAATGATGCTACCCGACGACATGCGAACTCCCTCTTTTGATGCTAAAGACATCGAATCCAAGGATCTCGATATTATGCT
ACATACCACATCGGCGGAAAGCGAGGTGCGAAATCTACCGGTAGCATATCGCAAGTGTCGCTTCAGTGACGAAAACAATCTGCAGTATTACAGTC
CCTACCACCCAAGTCTTTGCCGACTTGAGTGCCGAATCAAATGGGCCCTGAGCCTGTGCAACTGCAAGCCCTATTTCTACGTAGCAGCTCCCGAA
GTTCCAATCTGCACAGTATCCGGAATGCTCTGCCTAGCCCGGTCCAAGTGGCTTGAAAGACCATGCGATTGCTATCCGTCTTGTCGCGAGGAAAC
CTTTACCATCTTCAAAGTGTCTGACCAGACTGGGGGCGATGACAACTACTCTGGCGAGAGGTTCGAGCGGACGCTGATCATCAACCTGCAAATTT
CGAGGATGGGCATAAATCGGCGGGTTGTATTCAGCACGGATCAGTTGATAATGTCGTTTGGTGGAGCCATTGGCCTCTTTCTTGGAGCCAGCTTC
ATGACCATATACGGCGTGGACTCACCAGCGCTCGGCTCTCGTGTTTTCGGGCCCCGTCAGCAGGCGACTCGGGGCCTGTCTAGTAACATGTTCGT
GTAA
(SEQ ID NO: 1358)

Start ATG: 1 (Reverse strand: CAT)

MKATFTILVLQVVICLAGATEYQLTLDKDGLLAPCENQPGNPSGFEAMVFGQVYRLDKGTWQKTMFTASSNNFCKNMFDKNQYWYNFWTKYISNS
DEIKEKCLTTPGAVLKYKDYELDLKTSLNVPNLDGRYKLVVQIEAFDKRNFIMESKMSRPKQPDWLAELCQESSIHGMPYIARRDLHWAERLFWT
FIILGSAYYAISSCLNQWYRFRDNPIVYEYEYLFGLRIFPFVGITLCPRYHDETEIPRLINQTWGVDPSEDKEKAVYYRKFLLAINGLRYSTLET
LEPFENDTTLDNVNYLNILLTLQKKVIAVKIPPELAPIITEVGLCQTSSQLNRYGNPYGKLETQDMEPMKQCGYLSNCITSLKPINSIVAPIFMY
LHDVEEMMLPDDMRTPSFDAKDIESKDLDIMLHTTSAESEVRNLPVAYRKCRFSDENNLQYYSPYHPSLCRLECRIKWALSLCNCKPYFYVAAPE

VPICTVSGMLCLARSKWLERPCDCYPSCREETFTIFKVSDQTGGDDNYSGERFERTLIINLQISRMGINRRVVFSTDQLIMSFGGAIGLFLGASF
MTIYGVDSPALGSRVFGPRQQATRGLSSNMFV*
(SEQ ID NO: 1359)

Name: sodium channel, putative
Classification: ion_channel

Celera Sequence No. : 142000013384333
AATAACAACAAATATAAGCATTTTGAGCACTAGCTGAAACGACAACAACAACAGCAACAACAAAACGCATGCTCACCCAATTGCTTTGACACACA
AACCCACACATAGAAATTAAAACAAAACGCCCGCGGCAGCAGCGCCAGCAATAACAACACTGCAACAGCAACGTGGAGAGAGAGCACCATACCGC
AAGAGCGAAAGAGAGAGAGAGAGTGAGCTAGCTACGGAGAGTGGCTGCTGCTGCCGGGAGTGACACTTCCGCGCCACACGTGCAAGCGAGACGAA
GCGAGTTGCCCCGAAGGCACACCGTTGCGGCCAAAAACAACCACCATGATGGTGCCGAGAGCGAGAGAGAGCGAGAGCTGGCTCAGCGCTCAGTG
GCGATAGACGAGTGCGAGAATGTGACAGCACGAGCAGCAGCAGCGCTGCCGCTGCCCTCTGCCCGCGCCTCTGCCCGCAGCCAAGTGGATTCGTT
TTGTACGTTGTTAGACTCTCTCGCCGCGTTTTGGAATTCAGTCGACAATCGACGATAATTACCGGTGGTTGTATCACATCACATCACGCGCAGCA
GCAGCAGCACTACGAACGAAAGAAGAAGAAGCAGAAGAGCCAGCCGCAGTGGCAGCAGAGAAACTCGCTCGTTTTCGGATCTATATATATATATA
TGCATATAGATTTGTATATATAGAGGGATATATATATATATATATTTGCACGCAGCATTGGCGAATTTTCGGCCGCCTTTAATTTGTTTGTGTTT
TTTCCGTGTTCTCCTCCGCGTGCTCGCAATTACGTGCGCGGCAGCAAAAGACTATAATTATAAAACTAAAGTGAAAAGCGTGCCATAATTACACG
AGCGAATATCAATAAGTGCAAGAGCAATGTGCGAAAATTGTTAACGAACGCAGTAGCAACCAGAAGCAGTAAAACGCAGCAGCAATCGCAGCAGT
AGGATCCAAACAAATCTCAGCGCAACATTAAAATCGCAAGCGTTTTCAACATGATCGATGCGGCCTGCAATTACTTAAATCCCTATGCGCAACAG
CATCAGGCGCAGCAGCAGCAACATGCGCAACATCAGCAACACGCGCAACAACAGCAACATCATCTGCACATGCAGCAGGCGCAACATCATCTGCA
CTTGTCGCATCAGCAGGCGCAACAGCAGCATATGCAACACTTGACACAGCAACAGCAGCAGCAGCAACAACAACAGCAGCAACAGCAGCAGCAAC
AGCAGCAACAACAACAGCCGCAACAGCAGCAACATGACTTCCTCAGCGCCGCCGCCCTGCTGTCCGCCCCACCATCCCTATCCGGCTCGAGTTCC
GGCTCCAGCTCCGGCAGTTCTCCGCTATATGGAAAGCCGCCAATGAAGCTGGAACTGCCGTATCCACAGGCCTCATCCACGGGCACCGCATCGCC
CAACTCCAGCATACAATCGGCGCCATCATCGGCCTCCGTGTCGCCCAGCATCTTCCCATCACCTGCCCAGTCATTCGCCTCCATTTCGGCTAGTC
CATCCACGCCCACCACGACCTTGGCGCCACCAACAACGGCGGCAGCGGGCGCCCTAGCGGGATCACCCACATCCTCCTCACCATCCTCGTCAGCA
GCATCGGCTGCAGCGGCGGCAGCAGCAGCTGCGGCGGCAGCAGCGGACCTTGGAGCAGCGGCGGTCGCCAGTGCCGCCTACGGCTGGAATACCGC
CTACTCCGGATTGGGGCCAGCGAGGTAAATATCCCTATATATAGGATTTACAGAAGTTGAGTTGGGAATCATTCGTAAGAAAGAAACTTTAAAAT
GCTAGTGATCAATAAATCAAAGCTTATAGATCATCAAATTTGTGGTTATTAGGGATACACTAATTTCGATCTGAATTAGATCTCCTTTTAATAGA
ATAACTACAGGCTGATTGTATTTCGATCATGAGCGAGATAAAGACATATATCTTTTGCAAATTATACAGTTTAATACATAGGAATATATTAATCA
AATTATCCCGAAGATTGAAATGGATTAGCATACAAATAATCTCATAAACTTATAAAATGATAGGTACCACTTGAATACATTACAATTTAGTATTC
CGATAGCAGGTGTACCCATTAAGTAAATGATTAAAAAAAACCAAATTAACCATTCTCTGTCTTCATTTCTTTTCTCCATCTAGAAGTCAGTTTCC
ATATGCCCAGTACGCCTCCGATTATTACGGCAATGCGGTGGGCATGTCCTCCTCGGCCGCTTGGTTCTCGCATCAGGAGCGCCTCTATCAGCCAT
GGAGTTCACAGAGCTATCCGGGCTTCAATTTCGACGACATCGCCTTCCAGACGCAATTGCAACGCCGCTCCGTTCGCTGCACGTGTCCCAATTGC
ACCAACGAGATGAGCGGCCTGCCACCGATTGTGGGTCCGGATGAGCGCGGACGCAAGCAGCATATCTGCCACATTCCGGGCTGCGAACGGCTATA
CGGTAAGGCGTCGCATCTGAAGACCCACCTGCGCTGGCACACCGGCGAGCGGCCCTTCCTGTGCCTCACGTGCGGCAAGCGTTTCTCCCGATCGG
ATGAGCTGCAGCGGCACGGACGTACGCACACCAATTACCGCCCGTATGCCTGCCCCATTTGCTCCAAGAAGTTTTCGCGCAGCGATCACCTCAGC
AAGCACAAGAAGACCCATTTCAAGGACAAGAAGAGCAAGAAGGTATTGGCCGCCGAGGCCAAGGAGCAGGCGGCTGCGGCGATAAAGCTGGAAAA
GAAGGAGAAGAAGTCGGGTAAGCCACTGACGCCACCCGTGGAATTCAAGCAGGAGCAGCCGGATACGACACCGCTGGTCAACTATGCGCCCTATG
CCAATCTCTATCAGCATTCCACATCCGCCGGATCGAGTGTGAATCCTCCGCCGCCACCGCCGCCGCTCTTCCAGCAGCAGATGACGACGACAACA
TCATCGGCGGCGGCCAGCTTTGTGGAGCAGCCGTGGAGCAGTAGCAGCAGCCGTGCCATACAACCAGCCACTACCTCAGCCAGTTCATCCTCATC
CTCCAGCGCCAGTTCCCCAGCGGCAGCGGTCGTTTCTGCCATTGGATCTGCATCTTCCCCAGCCGCATCAGCCACGGCGCTGGCCCAGCATCATT
ATGCCGCACTTGCCATGCAAAGTGAGTCCCAGCTGGCGGCGGAATATGGGCTAACCATGAGCGGATTGGCCAGCGGAGCTAGCCAGGATTCCAGC
TCCAGTTGCCACATGAAGTCCGAGTATGCGGCCAGTTATCCGGCTGATTTTGGTGCGGGAACAGCCAGTTACGGTTATCCGCATCCACATCCGCA
CCATCACAATGCGTGGGCAGCGGCCTATCATCCACATGCCACCGCCTAGGATGTCCCCGATCCTTCCCAAAATTGTTACAGTTGAAAGTTGATGA
AACAAATGCCATAATGTCCCAAAACCCAGAACGGCAACAAAGCAAGCGTAGAACGAAAATCTAGTGTGTGTTTTTTTTTCAGTGTTTATTGTTGA
TATAAAAATATAATGTGAAAATCAAAAAAAAATTTGAATTCACAAAATACCGTATAAGGCATTATATAATATTATATAAATATATATATATATAT
ATACATACACATATATTAACTATACATGTAGAGACTAGAACTTGAATTTTTTTCATTTTTTTTCCCCCAATCTAGTAGCTAAGGCATTTTTTTTT
GCATGTCTGTACATACAAACATATATAGCGTTCTTTTTAAGCCATACCATATAGAATGAGAGAAACCATCTAGTTGTGTACCATAATAATTGTTA
ATTGTCTTTAAGATAAATTATATACAACAACAAAAAGTGAAAAATCCAAGGCGACAAAATCCCCACACTGAAATGAAATCCTAACAATAAAAAAA
AAAAACGAACAAAATAATATCGGAAAACAAAGCGAATCCAGTTTTTTATTATTCTCTCCGATCCCGACGCACCCTTGTTAATGGGTTCCTGGCTT
GGTTAGATTTCAGGGTTGTTTGATCTCCGCCAGGGGTTGCTTTCTTGCATATAAATCGAGGGATCCAGGAAGCTTCCCGACTTCCGGCGAACTTG
ATCTGCTTTTGGGTGCTGACCTTTGGCGGTATTTGGATAATAATAGAAACTTTTTCAATAGCAATCATTATAGCTGTCTGCATTTCTAGTTATAA
TTTCATCAACGTCGGCCATCGCTTTAAAATTGCAAAAACATTGTTAGCTTGGGAGATGTACATCATTTATAGATTGCTTTACTTTAAAATGTGCA
TAAATAAAGGTACGAATGTGATATGTATATATCCTTAAATACAATGATTTATTTAGTCAAGATACACATAGTTGTAGAATTTCATAACAATCGGA
TGTG
(SEQ ID NO: 1360)

Exon: 1001..1734
Exon: 2174..3374
Start ATG: 1001

Transcript No. : CT35305
ATGATCGATGCGGCCTGCAATTACTTAAATCCCTATGCGCAACAGCATCAGGCGCAGCAGCAGCAACATGCGCAACATCAGCAACACGCGCAACA
ACAGCAACATCATCTGCACATGCAGCAGGCGCAACATCATCTGCACTTGTCGCATCAGCAGGCGCAACAGCAGCATATGCAACACTTGACACAGC
AACAGCAGCAGCAGCAACAACAACAGCAGCAACAGCAGCAGCAACAGCAGCAACAACAACAGCCGCAACAGCAGCAACATGACTTCCTCAGCGCC
GCCGCCCTGCTGTCCGCCCCACCATCCCTATCCGGCTCGAGTTCCGGCTCCAGCTCCGGCAGTTCTCCGCTATATGGAAAGCCGCCAATGAAGCT
GGAACTGCCGTATCCACAGGCCTCATCCACGGGCACCGCATCGCCCAACTCCAGCATACAATCGGCGCCATCATCGGCCTCCGTGTCGCCCAGCA
TCTTCCCATCACCTGCCCAGTCATTCGCCTCCATTTCGGCTAGTCCATCCACGCCCACCACGACCTTGGCGCCACCAACAACGGCGGCAGCGGGC
GCCCTAGCGGGATCACCCACATCCTCCTCACCATCCTCGTCAGCAGCATCGGCTGCAGCGGCGGCAGCAGCAGCTGCGGCGGCAGCAGCGGACCT
TGGAGCAGCGGCGGTCGCCAGTGCCGCCTACGGCTGGAATACCGCCTACTCCGGATTGGGGCCAGCGAGAAGTCAGTTTCCATATGCCCAGTACG CCTCCGATTATTACGGCAATGCGGTGGGCATGTCCTCCTCGGCCGCTTGGTTCTCGCATCAGGAGCGCCTCTATCAGCCATGGAGTTCACAGAGC
TATCCGGGCTTCAATTTCGACGACATCGCCTTCCAGACGCAATTGCAACGCCGCTCCGTTCGCTGCACGTGTCCCAATTGCACCAACGAGATGAG
CGGCCTGCCACCGATTGTGGGTCCGGATGAGCGCGGACGCAAGCAGCATATCTGCCACATTCCGGGCTGCGAACGGCTATACGGTAAGGCGTCGC
ATCTGAAGACCCACCTGCGCTGGCACACCGGCGAGCGGCCCTTCCTGTGCCTCACGTGCGGCAAGCGTTTCTCCCGATCGGATGAGCTGCAGCGG
CACGGACGTACGCACACCAATTACCGCCCGTATGCCTGCCCCATTTGCTCCAAGAAGTTTTCGCGCAGCGATCACCTCAGCAAGCACAAGAAGAC
CCATTTCAAGGACAAGAAGAGCAAGAAGGTATTGGCCGCCGAGGCCAAGGAGCAGGCGGCTGCGGCGATAAAGCTGGAAAAGAAGGAGAAGAAGT
CGGGTAAGCCACTGACGCCACCCGTGGAATTCAAGCAGGAGCAGCCGGATACGACACCGCTGGTCAACTATGCGCCCTATGCCAATCTCTATCAG
CATTCCACATCCGCCGGATCGAGTGTGAATCCTCCGCCGCCACCGCCGCCGCTCTTCCAGCAGCAGATGACGACGACAACATCATCGGCGGCGGC
CAGCTTTGTGGAGCAGCCGTGGAGCAGTAGCAGCAGCCGTGCCATACAACCAGCCACTACCTCAGCCAGTTCATCCTCATCCTCCAGCGCCAGTT
CCCCAGCGGCAGCGGTCGTTTCTGCCATTGGATCTGCATCTTCCCCAGCCGCATCAGCCACGGCGCTGGCCCAGCATCATTATGCCGCACTTGCC
ATGCAAAGTGAGTCCCAGCTGGCGGCGGAATATGGGCTAACCATGAGCGGATTGGCCAGCGGAGCTAGCCAGGATTCCAGCTCCAGTTGCCACAT
GAAGTCCGAGTATGCGGCCAGTTATCCGGCTGATTTTGGTGCGGGAACAGCCAGTTACGGTTATCCGCATCCACATCCGCACCATCACAATGCGT
GGGCAGCGGCCTATCATCCACATGCCACCGCCTAG
(SEQ ID NO: 1361)

Start ATG: 1

MIDAACNYLNPYAQQHQAQQQQHAQHQQHAQQQQHHLHMQQAQHHLHLSHQQAQQQHMQHLTQQQQQQQQQQQQQQQQQQQQQPQQQQHDFLSA
AALLSAPPSLSGSSSGSSSGSSPLYGKPPMKLELPYPQASSTGTASPNSSIQSAPSSASVSPSIFPSPAQSFASISASPSTPTTTLAPPTTAAAG
ALAGSPTSSSPSSSAASAAAAAAAAAAAAADLGAAAVASAAYGWNTAYSGLGPARSQFPYAQYASDYYGNAVGMSSSAAWFSHQERLYQPWSSQS
YPGFNFDDIAFQTQLQRRSVRCTCPNCTNEMSGLPPIVGPDERGRKQHICHIPGCERLYGKASHLKTHLRWHTGERPFLCLTCGKRFSRSDELQR
HGRTHTNYRPYACPICSKKFSRSDHLSKHKKTHFKDKKSKKVLAAEAKEQAAAAIKLEKKEKKSGKPLTPPVEFKQEQPDTTPLVNYAPYANLYQ
HSTSAGSSVNPPPPPPPLFQQQMTTTTSSAAASFVEQPWSSSSSRAIQPATTSASSSSSSSASSPAAAVVSAIGSASSPAASATALAQHHYAALA
MQSESQLAAEYGLTMSGLASGASQDSSSSCHMKSEYAASYPADFGAGTASYGYPHPHPHHHNAWAAAYHPHATA*
(SEQ ID NO: 1362)

Name: buttonhead
Classification: transcription_factor
Gene Symbol: btd
FlyBase ID: FBgn0000233

Celera Sequence No. : 142000013383980
AAAGCAATTCCACACCCCATTCCAGTGCCCAGAAAGCCAAGGCATTACATAAAGGCGGTAAATATATATGACTAAATAAACCAAAGTCCCAGAAT
CAAAAGGGGCAAGGGGGGGGGACAAAACAGCTGTCAAAGATTCCTCAGTTGAGAGTTAGGATTTGTGCTGACCTACGGCAATTAACCGTCGTCA
TTTGCCATCGCAAAGGAGGAAGCAGCCATTTCTTCCGGTTCGGTGGCGTATACGTAACGTTTGCTGGCCGTAAGGATAGCTCAATCGCCAGGACA
CTGACTTATGCTGGCTCCAGTTAGACGCACAGATGACTACGCATTTATTTCTCGCCATCCTTCGTCGTCCCTGCGAACTTTTCAGAACTTGTTTT
TTGCACCCAGTGTGCTTATTTTTATTTATTTTTTTTTTTTTTGTAGCCAGAGTTTGGAGCTGGCGCCGTCTACTGTCTGTTGATTCAGATTCG
GTTATAGATTCTGGATTCATTTACGGTTTCTGTGTCTGACTTTCGGGCATTGACTTGGCGGCAACTTGGCTCTGTTTCTGACCCCAAGCCAAAAA
CGTCGCATCTCCCTGCCATCTTTTGGCATTTTCCGCTGTTGCGAACATTACGCATTCGCCCTGTGGGACGGCTAAATCTCGGTGAGCAAGCTAAT
TATGCCCATGTGGCACTCGCTTATAATTCCTATCAATTTAATTTTGTCGAATGTATGAGAGGTGTTACACCAGTCTATTCAGATTTCAATCGACT
TGACTTGATTAAAGCATTTGTAAACCATTTCAAAATTTGGAAAGCAAATTAAAACAATTACGAATTCATTTTAAATGGCAAAGGTTTTAAATAAG
TTCAAGCTTTGTCAAATTTCGCTACGTTGCAACTAGTGTCACATGGGCATAAAATTAAATTTGCAACTTTGGTGCTTGAGGCGAGTAGAATCAAC
AAGGCGAAAAAGCATTGAGAAGCGATAAAGCAAAGCGGTATTCAAACTAATTAAAATACTATGTATTTGCAGGTATTCTTAATCGTTTTATTCAA
ATCGTTACAAGCAAGAAAATCAAACGAATTGCAGCAAATGGCGTAAATCAAATGGTAATAGAAGCACTTGTTTTGCCGCATAATTTTCATAGATA
TTTTGATATTTGTTTTTTTTTTATCATTTTTTGTTTCGTATAGGTGAGGCTTAAGAGCGGTGGGTGCTTTTGGATTTTTGGTGATGGGTACTTC
TCATAGGGGTTGTCCTTCTTCTTGCTGGCCGCAGGTGTGCTCTTCCTGGGTCGATTCATCATTGGATCGTCCATGGTTCGCGATGATTGCTGTCT
CGTGTGCGCCGGCGGTCCAGGTGGCTTCTTTTTCTTCTTTTTCCCAGCTTCAGGTTGCAATGGATTGAAGGCGAACTGCAGATGTTGCTGCTGCT
GCGTCTGTTGCAGATGTTGCTGCTGTTGCTGCTGCTGCTGCTGCTGCTGCTGCTGCTCGCGGCGCTCGAGGAAGGCGGCATTGGCCGAGGCTACC
GTTGCTATTCTCTGCTGCTGCTCCAGATCCTCTAGTTCCTTCTCCCGCTTCTTGGTCATTTGCACCAACTGCGAACTGCGCCGCCTGAGGGCGGC
TGCATAGGGTGTGGGCGTTGCCACCGGCGGCACCATGTCTCCCACACCGAATAGCCGCCTGATGCGCCGCCGACTGTTGATGAAGCCCAGCCCTA
GCTGCACGCCCAATCCCAAACCCGCACCCGCCGGCGCTGTCGTCTGGCTGAGGGAACTGCTCGCGCCACCCTCACTGCCGGCGCCCAGCATCTGG
CTGAAGTTACTGTCCAGATCGCAACTGCTGGCCGAGTCGGCGCCACAGGGAAAGAGATATGTATTCAGGGTGCTTAGGGTTGTGGATGTGGACGT
GCCAGTTCCGGTCATGGTTCCAATGCGACTAATGGCGCCCGTATTGCTGCCACCCAGCGGATTTTGCTGTTGCGAGTCGAGAGATGCTGATCCTG
CTGCTGCTCCTGCTGCCGATGGCTGATGTTGCAGGTTAAGCGGGAGACTCAGTGGCAGTGGCAGCATAACTGCCGTGGAACCACTCACGCTGCCG
GTGGTGCTGCTGTCGTAGCTGTGCGGATTCACATAAATGTGGTTGTTGTTGGTGGCGGTTGATGATGCAGTTGCTCCAGCTGTAGTGCTTCCTCC
TGCTGCCGTGCTACCAGCTGATGCAGTGCTGCTCGTGTTGACCACCAATGTGCTGTTGCTGCTCTCATGGTGATTGTTGTTGCTGGCTTGGTTAG
CGTTGTTGCTGCTGCTGCTGCAGCTGGTGGTGTTGTTGTTGATGCTGCTGCTGTTCGTGTTGCTCAGGTTGACCCTGTAAAAGCTGGTGCTGCTG
GTGGCAATATTGTTGTTGTTGCTGCTGCTGCTGGAGCGTGCAGGCGCCGTTGCAGGTCGCGATGCCTGTGATCCCGATCCCGATCCTGATCCGGA
TCCAGGTGCACTAGCCTCCGGAGGGGCAGTGGTTGTTGCTGCTGCAGCTGGTGTTGCAACTGATGTGGCAGGCGTCGCCTGCTGCTGCTGCTGTT
GCGAATGATCGTTGCCATTGTTGCTGCTCATTGCTGTGGTTGTTTGACGCCTTTTTGCGTTAAGTTCTCGATTTTAAATATACTTCATTAATGTT
TATAGCTCATTTTTAATAACCCAATCATTATATTACATTTACTTCAATTATATGTGCTCGATAGCTCATTTACTTTTTAATAATGATAGTGAACA
CTTATTAACATTTTTAAGGGAGGTACTTCGTTTCACTAGTAAGCTATTTTGAGAAAAGTTTTATGTTCTCGTGGTGTAATATCACAAACTAGTGA
AATCTTTAAGATTTAATGAAATATAACATCTTTGGTTTTCTAAATTAAACTTAATAATTTATTTTTATTTCGTTAGATTTTAAGTTCACTTCATA
ACTTTTTCTTCGGTAAATTCTAGTTACGGTGCAGTGGCTATTAGTTTATTTGTTTTTAACCGTTTAACAGTGTTTAACTTTACATTTATTGATGT
TATTAAATTGCTTCTAGGTGTTTATTGTGCATAGATTTGTTTGATTTAGTTATATATACATTTATGCTAGTTCGTTTGCTATGACTCCTTTAAAG
ACCCTCCTTTTACATATTACAATTCATGTATCTTCTTTTGGATGGCATCCAAATGGAGTTGAATGCACTGCTCCGATTGCTGGTAAATGGCAAAT
GGCGACTACTAAACGGTTATGGCCAGACGTTAGCTAATCGCTCAGTTTTCCCGGACCTTTCACGCACTTTTCTCTCGCGGCACTCGAACAAAAAT
CACAGACAGTGGGGTCAGGAGGTCAATGAAGCTTATCACTGGCACGCACATTTACGCAGCACCGCAGGACACTTGCAAAAAAAAAATTACTTAAA
AAAATGGCTGTTTTTACGCGGCATTTTTTAAATGATTTTTATTAATTTTTATTTGATTTAGACAGACAGAGTTCTGTTATCAGTCAGAGCCACGT
GCTTAACGCGCCGCGTGTCACAATTGTATGAACTTTGTGCCGCGTTGTTGACAATGCCAAAAGCCAACAGCAGCAGCAGTT (SEQ ID NO: 1363)

Exon: 2596..1001
Start ATG: 2596 (Reverse strand: CAT)

Transcript No. : CT35411
ATGAGCAGCAACAATGGCAACGATCATTCGCAACAGCAGCAGCAGCAGGCGACGCCTGCCACATCAGTTGCAACACCAGCTGCAGCAGCAACAAC
CACTGCCCCTCCGGAGGCTAGTGCACCTGGATCCGGATCAGGATCGGGATCGGGATCACAGGCATCGCGACCTGCAACGGCGCCTGCACGCTCCA
GCAGCAGCAGCAACAACAACAATATTGCCACCAGCAGCACCAGCTTTTACAGGGTCAACCTGAGCAACACGAACAGCAGCAGCATCAACAACAAC
ACCACCAGCTGCAGCAGCAGCAGCAACAACGCTAACCAAGCCAGCAACAACAATCACCATGAGAGCAGCAACAGCACATTGGTGGTCAACACGAG
CAGCACTGCATCAGCTGGTAGCACGGCAGCAGGAGGAAGCACTACAGCTGGAGCAACTGCATCATCAACCGCCACCAACAACAACCACATTTATG
TGAATCCGCACAGCTACGACAGCAGCACCACCGGCAGCGTGAGTGGTTCCACGGCAGTTATGCTGCCACTGCCACTGAGTCTCCCGCTTAACCTG
CAACATCAGCCATCGGCAGCAGGAGCAGCAGCAGGATCAGCATCTCTCGACTCGCAACAGCAAAATCCGCTGGGTGGCAGCAATACGGGCGCCAT
TAGTCGCATTGGAACCATGACCGGAACTGGCACGTCCACATCCACAACCCTAAGCACCCTGAATACATATCTCTTTCCCTGTGGCGCCGACTCGG
CCAGCAGTTGCGATCTGGACAGTAACTTCAGCCAGATGCTGGGCGCCGGCAGTGAGGGTGGCGCGAGCAGTTCCCTCAGCCAGACGACAGCGCCG
GCGGGTGCGGGTTTGGGATTGGGCGTGCAGCTAGGGCTGGGCTTCATCAACAGTCGGCGGCGCATCAGGCGGCTATTCGGTGTGGGAGACATGGT
GCCGCCGGTGGCAACGCCCACACCCTATGCAGCCGCCCTCAGGCGGCGCAGTTCGCAGTTGGTGCAAATGACCAAGAAGCGGGAGAAGGAACTAG
AGGATCTGGAGCAGCAGCAGAGAATAGCAACGGTAGCCTCGGCCAATGCCGCCTTCCTCGAGCGCCGCGAGCAGCAGCAGCAGCAGCAGCAGCAG
CAGCAACAGCAGCAACATCTGCAACAGACGCAGCAGCAGCAACATCTGCAGTTCGCCTTCAATCCATTGCAACCTGAAGCTGGGAAAAAGAAGAA
AAAGAAGCCACCTGGACCGCCGGCGCACACGAGACAGCAATCATCGCGAACCATGGACGATCCAATGATGAATCGACCCAGGAAGAGCACACCTG
CGGCCAGCAAGAAGAAGGACAACCCCTATGAGAAGTACCCATCACCAAAAATCCAAAAGCACCCACCGCTCTTAAGCCTCACCTATACGAAACAA
AAAATGATAAAAAAAAAAACAAATATCAAAATATCTATGAAAATTATGCGGCAAAACAAGTGCTTCTATTACCATTTGATTTACGCCATTTGCTG
CAATTCGTTTGATTTTCTTGCTTGTAACGATTTGAATAAAACGATTAAGAATACCTGCAAATACATAGTATTTTAA
(SEQ ID NO: 1364)

Start ATG: 1 (Reverse strand: CAT)

MSSNNGNDHSQQQQQQATPATSVATPAAAATTTAPPEASAPGSGSGSGSGSQASRPATAPARSSSSSNNNNIATSSTSFYRVNLSNTNSSSINNN
TTSCSSSSNNANQASNNNHHESSNSTLVVNTSSTASAGSTAAGGSTTAGATASSTATNNNHIYVNPHSYDSSTTGSVSGSTAVMLPLPLSLPLNL
QHQPSAAGAAAGSASLDSQQQNPLGGSNTGAISRIGTMTGTGTSTSTTLSTLNTYLFPCGADSASSCDLDSNFSQMLGAGSEGGASSSLSQTTAP
AGAGLGLGVQLGLGFINSRRRIRRLFGVGDMVPPVATPTPYAAALRRRSSQLVQMTKKREKELEDLEQQQRIATVASANAAFLERREQQQQQQQ
QQQQQHLQQTQQQQHLQFAFNPLQPEAGKKKKKKPPGPPAHTRQQSSRTMDDPMMNRPRKSTPAASKKKDNPYEKYPSPKIQKHPPLLSLTYTKQ
KMIKKKTNIKISMKIMRQNKCFYYHLIYAICCNSFDFLACNDLNKTIKNTCKYIVF*
(SEQ ID NO: 1365)

Classification: receptor

Celera Sequence No. : 142000013385196
GCATATTTAATGACCCCAAAGTTAAGTCTCACATGTTCGCACCTGGAATCTGCGAGGCGCGACCGAGACCAAACCGGCGGTGGATTGGATAAGGC
ATGACATAGCCGATGAGCAGCAAGAGCGGAAAAACCAGAACGGCCGAAAGTGGGTTGGCTTGCATTTCGAGCCGTTTACTTCCGCATCTTCCTGT
CCCGCGAGCGGTGATCTTTCTTAATGAACGTGATACGGGCAAATTGGCCAAGCAGAATCAGGCCAAACAGCTCGGCGGTAGTTTAAGTTTGTCCC
GAAAACCACGTAGAAAAGCGAGGAAAGCTTAACAGTGGACCTGTAGCCATTGGTCATAAAGCATCGCAATTAAAGTACTTAGGAAATCAAAGGCC
CATTGATGAGTATGGAAATATGTTATTTGTTGCATTGTATTTCGAGTTAGCAGATTTTTCATAAAGTGGTTTTCCTCTTGGCATTCAAAAATAAC
AGTCAAAGTTTACAATAAGTAAATAAAGTAATTGTGAGCATACTCCATCAACTGATCAGCAGAGTTAGAAACTAATTAAAAAGAGTGACCACAAG
AAAGTTGCTCCAAATCGTAAATAGACAACAATTGCGTTGATTACTTGATTCTGCGAAGTCATCGCCCTGAACAGTTTATATCGATTCGCATCCAA
ATCGTCCAGCTTTAAGTCCAGTTAAGGCTGGAATTTGAATCTAAGCTGAATCTAACAATATATGCACAAAATTAAGTCTGCTATCTGAAAGTGAG
TAACAGTTGTGCTCTGTTAAGCCCAATTTATTGCCCTGCATCATGATGAATCAGTTGCTGGAGCATCCCAAATATTTGTTGAGTATTCTTTCGCC
TTTAGCGGTAGCTTAAGCTTAGGTTGTGGTTTGAACTTTGTACAATGTTTAGGGTTAAATATTACGGCATAAGTTAGCTTTTAACATTAGAGTTT
AGGCGTTAGCCCGCCATAGGTTGCCTCCGTCCCTGGCTATCTCCGCAGGCTTAGAGCGGCTCCAGGGCCGCCGGTCCATGTGGACTGCCCTCCAG
TTTGCGCCAGACCACGTTGCACATCTCGCGGACCAGCGCCTTCTCGCCGTCATCCATCTGGTCGAGTGCGCTTCCAGCTAGGTTGCCAAGCCGAT
CGCGCTCCAGCTGCTCCCGCACCTCGAGCACCTGGAGGGCTCGAACCACCGCCTCTGGTCGTCCGGCAATCGGCTCCGGCAGTTGGATAGCAGCT
GCTGCCGCCGCTGCAGCGGCCACGATGTCTTGCTGCTGCTGTTGATGTTGCTGCTGCTGCTGCTGCTGGTGGGGCGATGCTGCTGATTTGGC
TGGAGTGGCTGCAGATGTGACCGTTGGCGTGGGCGTGGCCTGCGGCGTGGGCGTCGTCGGCTGTTGTAGATGGGCCGTGGGCGTGGTGCGCTCCT
CCTCCAGTTGCTGGATGCGGCGCTCCAGTGAGCGCACATACTGAAGCGTCTGGTCGTTCAGCGTGTGGGCATGACGTAGATCCTGTTGGGAATCA
AATTGAAATCGCCATTAGGTCAAGTTCTTATTGCTGTTCGTTTTTTTTTTTTGCTCACCTGGGGTAGTTGCCGCTGCTCTGCATAGTTCCTCAAG
GCGGTGATGGTCTCATCTGCATTCGTGCTGGAGCTGGAACCATCGCCGTCATCTCGAAGCGCATTCCTAGTGGCTGCTCCGCAACCGGCGCACAG
CGCATTTGCCGCCACATGGGCACGCTCCTCGTCCAAGTAGAGGCAGAGCTCCTTGAGCTCTAGATTATCGGTGATTAGCTCTTGCTGCTTATCAT
CCAGCTGACGTAGTTTGTTCTGCAAAGAGTATGTCAAGTCAATTAGTATTCAAAGATCTGGAGTTTCGTTCGGGGCTGGACCCACCTGGTACGCG
GCCACCTCCTGCCGCATCACGCTGGCCGTGTATCGCCCAAATCTTTGCCATTCCCGCGCCAGCTTGCGTCCCTTCTGCCGGTCGTCGTCCAGGAA
GCAGCACAGATCCCGCAACTCCTGGTTGTCGTCCAGCAGGCGCTGATTCTGCTCCTTCAGCGCACGCAGTTCGTTGACCAACGACTGCAACTGCC
GGTTCTGCTCGGCGGTCAGGCGACCTCCGCCATTGGCCGTGGGTATTCCCGTGCCGCTGGACGTGACCGAGGCATTGGGCGATGGGTGTTCCTGG
TCTGGCTTGCGCACAAACTTCAGCATATCCTTCGCTCCCGGCTGGTGTGCTGGTAGATATCGCGACTGTTGCTGCTGTTGTTGTTGTTGCTGCTG
CTTGATGGAGTCGGGAATGTAGATGCTAGATAGCTGGGGGATATCCGGCGGATACTTGAGTGGCAAGTGCGGCTTTAGGATCCCGGTGGCCGGCT
GCGGCGGTGGCTGGTATCTCGGCGGATGGAGTGGGCGGGTGCCGGTGCCTTCAGCTGCGGGCTGCGCAGAGATTGCTGCTGATTTTGCAACTGG
TAGTGGAAGCTGCGGCGCTGCTGGCCGGCTAGATTGGGCAATTCTTTAGTCGATTGCTGCTGGATGGGCAGGCGGGAAGTCAATGCCTGCTGCTG
CGTGGAGTGCGGCTGGTGTATCGTGGCCACCGTCTGCAATTGATGTGATTGTTGCTGCTGCTGCTGCTGTTTTTGGGCTGCCGACTGAGCTGTTG
GCGTTGGCGTTCCGCTTTGTTGCTGCGATGAGTGTGGCTGGTGGGGATTCGTTGCTCCTCCTGTTGCTGGCAGCAATGAGCGACGCTGGTGGATT
TGTTGTTGTTGGTGCTGCTGCTGCTGCTGCTGCTGTAGTTTGTTAATTGCCTGCGTTGCTGCCTGACTTTTGCCTACTATTTTGTCAACGCTATT
TATTTTTATCAAATTATGGCCCAAAGTGGTTGCTTCGTTTGTTGCTGCTGCTGCCGCGTTGTTAGTTAATGACTTCTGTTGCTGTTGCTGCTGCT
GTTGATTGCCGGACATTTTCGTGTTGGTTCCTTGTTCGCCTTGTGTCGTTTCGGTGTTCCGTCCGTCCTCTGCCCGTCCCTCGCCCTGATTTCCC GGTGTCTATGACCTCGCAGTCATATTGTCAAGTCACTGCAAGATAGCACAAAAAAAAATGGGCAGGGCATTAGCGAAAATCTTAAGTGGAAAAAG
CTATAGGCCAGCCATAAATCAAGCCATTGCTCGATGTAATTTATGCGACAGCCGAGGGCACGCCGCCGGAGCAGCATAATTAAACCTCCATTAGA
CTGCCGCGAGACGCTGATAGAAAGTGAAATGAGCATTTATCGCACCACTGGAGCCATGACATGGCACACGAGGCGGGCACACACGTCCACATCCA
CATCCACATCCACATCCAAGTCCACGTCCTCGCCACGGAGTGCTCAACAAAGTGCAGCGAAGCGTCGCCAAAATGTCGCCAGTACACGGAGAAAA
AAGGTCCCCCCAACTAATATTATATATAATGATTTTTCATATGACTCATGGAATTTTTATGTTTTTGTTTTTAGGACACGCCATCATAGAAATTC
TTAATCAACACTCTGACATACAATAACTTGTTTAGCCTTGGAGGCTCTTATTTCTTTCGGTGTGGCAAAGGGAACATGTCGTCGGTCTCCGCTTT
CTGGCTGGGATCGGATGGGCTGGCGCTGAAGCGTCTAATCACCAGATGTGCGTCAACTAAACGGAGGCTTCCGCTTCTGGTTTGGAAACCGAAAG
CCAGCCCGATGCACTGAATCAACACATATCACCGCATTTGTATCTGGAAAGTGAAATTGTTCATGCTTTGATGGATGGCGGCTCTCTGGGGCAGG
AAAATTGAAATGTTGCAGAGTTCGGAGATTGACGTGATTATGGTAGTTAGGTAGAGCAATTTGTGGTAATAACAAGATTGGTATTGCAACAGAAC
GTTTCACCAAAATATGTTTGGCATAATATATTTATATAATAGGGTGCTAGTCATATCAATGATCCA
(SEQ ID NO: 1366)

Exon: 2961..1891
Exon: 1824..1579
Exon: 1507..1001
Start ATG: 2961 (Reverse strand: CAT)

Transcript No. : CT35453
ATGTCCGGCAATCAACAGCAGCAGCAACAGCAACAGAAGTCATTAACTAACAACGCGGCAGCAGCAGCAACAAACGAAGCAACCACTTTGGGCCA
TAATTTGATAAAAATAAATAGCGTTGACAAAATAGTAGGCAAAAGTCAGGCAGCAACGCAGGCAATTAACAAACTACAGCAGCAGCAGCAGCAGC
AGCACCAACAACAACAACAAATCCACCAGCGTCGCTCATTGCTGCCAGCAACAGGAGGAGCAACGAATCCCCACCAGCCACACTCATCGCAGCAACAA
AGCGGAACGCCAACGCCAACAGCTCAGTCGGCAGCCCAAAAACAGCAGCAGCAGCAGCAACAATCACATCAATTGCAGACGGTGGCCACGATACA
CCAGCCGCACTCCACGCAGCAGCAGGCATTGACTTCCCGCCTGCCCATCCAGCAGCAATCGACTAAAGAATTGCCCAATCTAGCCGGCCAGCAGC
GCCGCAGCTTCCACTACCAGTTGCAAAATCAGCAGCAATCTCTGCGCAGCCCGCAGCTGAAGGCACCGGCACCCGCCCACTCCATCCCGCCGAGA
TACCAGCCACCGCCGCAGCCGGCCACCGGGATCCTAAAGCCGCACTTGCCACTCAAGTATCCGCCGGATATCCCCCAGCTATCTAGCATCTACAT
TCCCGACTCCATCAAGCAGCAGCAACAACAACAACAGCAGCAACAGTCGCGATATCTACCAGCACACCAGCCGGGAGCGAAGGATATGCTGAAGT
TTGTGCGCAAGCCAGACCAGGAACACCCATCGCCCAATGCCTCGGTCACGTCCAGCGGCACGGGAATACCCACGGCCAATGGCGGAGGTCGCCTG
ACCGCCGAGCAGAACCGGCAGTTGCAGTCGTTGGTCAACGAACTGCGTGCGCTGAAGGAGCAGAATCAGCGCCTGCTGGACGACAACCAGGAGTT
GCGGGATCTGTGCTGCTTCCTGGACGACGACCGGCAGAAGGGACGCAAGCTGGCGCGGGAATGGCAAAGATTTGGGCGATACACGGCCAGCGTGA
TGCGGCAGGAGGTGGCCGCGTACCAGAACAAACTACGTCAGCTGGATGATAAGCAGCAGAGCTAATCACCGATAATCTAGAGCTCAAGGAGCTC
TGCCTCTACTTGGACGAGGAGCGTGCCCATGTGGCGGCAAATGCGCTGTGCGCCGGTTGCGGAGCAGCCACTAGGAATGCGCTTCGAGATGACGG
CGATGGTTCCAGCTCCAGCACGAATGCAGATGAGACCATCACCGCCTTGAGGAACTATGCAGAGCAGCGGCAACTACCCCAGGATCTACGTCATG
CCCACACGCTGAACGACCAGACGCTTCAGTATGTGCGCTCACTGGAGCGCCGCATCCAGCAACTGGAGGAGGAGCGCACCACGCCCACGGCCCAT
CTACAACAGCCGACGACGCCCACGCCGCAGGCCACGCCCACGCCAACGGTCACATCTGCAGCCACTCCAGCCAAATCAGCAGCATCGCCCCACCA
GCAGCAGCAGCAGCAGCAGCAACATCAACAGCAGCAGCAAGACATCGTGGCCGCTGCAGCGGCGGCAGCAGCTGCTATCCAACTGCCGGAGCCGA
TTGCCGGACGACCAGAGGCGGTGGTTCGAGCCCTCCAGGTGCTCGAGGTGCGGGAGCAGCTGGAGCGCGATCGGCTTGGCAACCTAGCTGGAAGC
GCACTCGACCAGATGGATGACGGCGAGAAGGCGCTGGTCCGCGAGATGTGCAACGTGGTCTGGCGCAAACTGGAGGGCAGTCCACATGGACCGGC
GGCCCTGGAGCCGCTCTAA
(SEQ ID NO: 1367)

Start ATG: 1 (Reverse strand: CAT)

MSGNQQQQQQQKSLTNNAAAAATNEATTLGHNLIKINSVDKIVGKSQAATQAINKLQQQQQQQHQQQQIHQRRSLLPATGGATNPHQPHSSQQQ
SGTPTPTAQSAAQKQQQQQQQSHQLQTVATIHQPHSTQQQALTSRLPIQQQSTKELPNLAGQQRRSFHYQLQNQQQSLRSPQLKAPAPAHSIPPR
YQPPPQPATGILKPHLPLKYPPDIPQLSSIYIPDSIKQQQQQQQQQQSRYLPAHQPGAKDMLKFVRKPDQEHPSPNASVTSSGTGIPTANGGGRL
TAEQNRQLQSLVNELRALKEQNQRLLDDNQELRDLCCFLDDDRQKGRKLAREWQRFGRYTASVMRQEVAAYQNKLRQLDDKQQELITDNLELKEL
CLYLDEERAHVAANALCAGCGAATRNALRDDGDGSSSSTNADETITALRNYAEQRQLPQDLRHAHTLNDQTLQYVRSLERRIQQLEEERTTPTAH
LQQPTTPTPQATPTPTVTSAATPAKSAASPHQQQQQQQQHQQQQQDIVAAAAAAAAIQLPEPIAGRPEAVVRALQVLEVREQLERDRLGNLAGS
ALDQMDDGEKALVREMCNVVWRKLEGSPHGPAALEPL*
(SEQ ID NO: 1368)

Name: putative delta antigen interacting protein A ortholog
Classification: nucleic_acid_binding Celera Sequence No. : 142000013384668
GGGTGAGCTGAAACAGCAAATTAGCTGACTCGCAGAAGAGCCAGAAGTTCAGGGCGACAGCCACCACCAGCAGGATAGATTCCTGTGATAAGGAG
ATCCCGATGGCCTCCACGGCCTGTCCCACGTGACGCACGACAACCGGATATAGTGGATAGAAGGCCAACGTGTTTTCGTAGCTGTACAGATTCTC
GGCTATATGCAGAAAGTATTCTCCATCCCAGTGCCGTAATCCTCCCAAGCAGCGCTTAATCACCTTGTCTATCCAGGAGGCATTCTGATCTGACG
AAACCGGCATCCGGAATACATCTGGTTTGTGCTCTGGCAGGGCTCCGTTGGCGACCAATTGTACCAGGAGGACGATAAGGCGACTGGCCAGCGCC
AGTTTAGTCACTTTCTCTGTCATTTCAGATTTCTAGGTCTTGGGTGGAGTCGATTATCATTCGGCGGGCATGTGATTCATATCAGGTCGAGGGCA
TACCTCACAGCTAAAACGATGTGGACGGATCTTCTGGCCTGGACACTGCTGCGGAGGGAAAAAGGCAAATCAGCTCCTCGGTTGCTTCTTGAACT
GCCTTCTCTTTTGGTGACATTTACTTTGTGAAGCGGTTTTATTATTATATATTATTTTTGGGCAGAAGCCCGGAAAAGCAGAGCATGGTGTGACC
AGAGGGTTTGAGGAAGCATTAGACACTTTCGATATATTATCGATACGAGAATAATATATTTAATAAACAGAATTAAATTAATATGTAAACTTAAT
TCTCGTTGCTCTCGAACTATTAATTTAGTGTACAATACAGCCTTATAATTTAATTTAAAAATAAACAGTTAATACGTCACGTGAATTGCAATCGA
TACTATCAAACTAATATCGTTGATTGCCCCACCTCAAATCGATATGGCACATTATAGTGGCGGCATTTCCTAAATAAACTGCCGCTTTTATTTGG
CAGTTGGGTTGAATTTAAGCTAAAATTTCACTCATAAATGAAGTGTCGCAATGCCGAGCAGTGCAAAGAAGTCGGACTCTGCAAAGAGCAATAGC
TCGACGCCACGAAGACCGCGAAAGCGCAAACGAGTGGATCGCCAGAGCCTGGACTCGCAGGTCGATGAGGATGCCAAGGAGATCGATCGCCCGGCT
ACGGAAAGTGGCCAAGAAGAACTCCATCAGTGCCGAGGACATGCAAAAGGTGGTCCGGAAGGTGGTGCGCAACGATCATGTTCTGGCATTAGTCA
CTTTGAAGGCGGAGGACGAGCTGGCGCGGGAGAAGTTGGAGTCGGCGGAGCAGCAAAAGCGGGGTGCCATCATCATAACGGACACTCCATCTGTG
CCCAAGCTAACGCGAGCGAAAGCACGGGAACTGAACTGCACGCCTGGGATCTCGCTGCCCCAGCTCAATGAAACTTCCACCGACAATAATGGTAT AGAGGCTCTAATACGTGAGGATTTGCACTCTGATGAGGAGGACGAGGAGTATACCTTCAAGGAGGAGGACTTTCATGTGAGTATAAACATTGAGG
CCAATTGATCGTTGTTCAATAATTGTTATTATTCCTTTATTATCAGTCCGATGATGATCCTAACACTACAGCATCGGATTTCGACTCCAATCCCT
GCACGCCTCAAACTCCTCTTACTGCCAATGAGGAATCTCCTATCAAATTCTCTGATGACGGTTGTTTCAAGGTGCCGTTGGACAGAAATTTTCAG
GATAAAGAGGATCTTAGGATTGCCACTAGAACGCGCTCCAAATTTTGTTTGCAGCAAACTACCATTGAGGATTTGCAGTCGGAATTTGTCCCGCC
GGACGTGGAGCCTAGCGATGTGGTGGAGAACGAAATGACCGCCAACGATGCGGATTGGATGCAGTTCCTCAATGACTTTACAAAGCCTTTAAGTA
TGTAGTATCAATGGATGCTTTTATGCTCTCCCTAACTTTAATATCTTACAGACAATACGGTCCAGGGCGACGATGATGATCCTATTAACGATCCA
GAATATGTGGCCGCTGATCACTTGGAATCGGAATATGAGAACGCCGAGGAGCTGCGCGATGTAAATATATCTAAAAAAGAGTTAACTGACCTGGT
CTCTGAGCTGTTTGCTGGTTTGCTGGAAGAAGGAGTCTCTCTGGAATCGATTGAATTGGAAACACCTCAAAAATTCGTTGAAAGTGCCAACGTTT
CGATGATTCCCATTGATCAAGTGTCCCGTAACATCGATTTTGATGGCCAGCAGATAAATGCTAATCAGCAGGAGCTGTCCGTTTTTCAACCTAAT
CTAATGCCGCCTCCTTGCGAAGGGAACGAAATGGGCATGGGTGTGCCTGTCCCTGTGGCTGTGCTGCAGGAGGAAACTGGTGGATCCGCTTGCAA
TGTGGTAAACATACCTTCCGAGGCGCTGACTGTTCCCCCCGAACTAATAGCTGTTCCAATACCTGGGCAACCTAATTGCTTCCAAATCGCCAAAG
TTGTAGGCAATGATTCAACTGTTGGTCTTCCATTAACTGAAGAGACACTGCAGAACTTTTCTAGCTTGCATCCAATGGAACCCCCCGTGGTAGCT
GCAAGCAATGGAGATCGATATAAAAAACCATTTGATACGAACTTCACCTGGGAATACATCTCGGTTAGGAAACATATATATTCGGAGTATGAGGA
AAAGTTTGAGAGCCTGCGAAACGTAGAGCCAGTAAACCTCAATCATCTCGCCAGGAGCAGGGGATTTACCCAGTCTCAGCATGATATGCTTCAGC
AGCAGCTTCGCATTCACACGCAGTTGCTCAGTCAAAGCTATCTGCAAACCTACTCCCATCCTACGTTGTACCCCATGGCCAAGAAGCCCAGAGAA
ATGTTGGAAGAATTGCACAAAATGGCAACTAAAGATCCCAGTTTTAATTGCTGGAATCTGCAGGAGGCTGTTCAGCTGGTTAGAAAATGGGAACA
TGATCTGTCCAGTGATGAGTTTAAGGAGGAGAACGAGAAGATGATGGACTTCATCAATAAGGAAACGGATCTGACGTAAGTTGGTGAAACTTTAA
ACAAAACATGCTGCTGTACAACTTGTATTTACTATTTTAGTGATGGCCACACGCGCCAGGTTCCCAGGCTGGCGCCTCGTATTATGGATCTCATG
CTGGATAGCCGGGTGTTTATGTATCCGCAGTACCTACCCCGTATGGCGTTTCAACCGAAACTGACTCAAACCCACCGCTTACGCACCATCCGAATA
TCAGCTTATTGCCATTGGCCTAGAGAAGCACTTGGCATTAATGGTAAAAGCCAAGAGACAACTACGCAAAGGTGCAGATCCCATTCGCGTTGCCT
GTAAGCGAATGATTAAGGATACGATTTGTGGAAAGACTGCCCGCCGAATTTTCTTGAAAATCGCGGAGCTACGCAACTCAAAACAGTACAATCCA
GTGAAGTATTTCTTTGAACATCGTCGAGCACCGCCCGCTAACGCCATCCTTTGGGGATTCGCTGGTGGGCTGGTGAGAACTCCGCGGGAACGACA
CATGGAGCTTCCCAGTGGCTGGCAATACTACATTGAGGTAAGGAATACAATGGGTTATTATCGGATACATTGTTTAACATTTAATAAGCATCAAA
AAGGGGGAAAATCTCAAAGGGTAAATAAGATGGGATTAGGAAAACTAGCTTAGTTGGTGGCCCACTCGATCTCTGGGTATGAGGCGCAGCTCGGA
TCCGTGCTTTAGGAACACATTACCAGCAGTCTGCTGTGGGCTGATGCCAATTCCATCGTCCGTGATGATGGCACTCGTCTCCGCCGGAACCTTGA
ACTCTTCAGAGGCGAATTTCAGCACAGCCGTAAAGGGAGTTCCCTCCGGAACACTAAGCACCTTAAAGGGCAGCTTGGGGTCCGAAGTTAGCGTG
ATTTTGAAGGTTACTTTGCTCATAGTGGAATGTGCAGACGTGGTCAGTTTTGATACTCTATGGGAATAAACGGGTTTCCGATGTTTTCCACAGGC
AGAGTGTTTGAGCCCTGGTGGTTAAAGTTTAAACAAGTATAAATTAGTTGGTTTGAAAATAGTTTTAAGGGGTATTTTATTTAAAAACAATAAAA
TATGTTGACGCTCTTACTTTAGTGCGGTCAATATTACGATAGGCAAGGCAGCGAGTTATCGTCTGTGATGAGTAATATTTGCATAAATGTACCTA
TGTCCGTACCTAATTAGGAATACATGTTTAGAACTTTATTAATTTTTCTCTTAAATTTTAAGTAATATACTTGCTAGTGATTGTTGGCAGAATTA
TTTTACGAAATAAATCACTGGTCATCGGTGGCTAGGTACCATCGACCAAAGTTATCGATATCAATATACATAGCTTGTGCCATCGCTGTGTTTAT
AAATCGCGGACAATTTTCAATCTATTATTTTTCAGAAAACTTGGGATCAAAAGCGCACACGTCGCAATTTTAAAGCATCGAAAGCATCGTCGGTG
GCTAGTGCTTCTTATTTGGAGTTTGTACGCGAGGCGGTCGGCGAGGACCTGCTGCTGCCAGAGACTTTTGGTCAGGCTGCGGTCCCCAATGGCAG
TGCTGCTGGTTCGGAACCGCCCAAGGAGAGCAAACCGAAGAAAAGGCCAGCGCAAAGGAGACCCCGCCCTGCGGAAAACCCACCACAGCTTACCA
TCAATGTGAATTATGTTTTTGGCGGGAATACGAGCGCGGGAAACATACCCGGGGTCTCTGGGGTTTCGGTGCCCTTGGTGGCCGGCGGAAATCTG
GCCGAGAACGTACTGAACATCAATCGCAGCTTATACACCGCCGCCGAGTGCAGTAGTCTGCTGGCCTTGCCGCCTGCTCCTCCACCATTGGATGA
AAATGCTCCGCCAGCCATCAACTTCACAGTAGACAAGTTCACTAACACACTACAAATCTGAATTGGAGGAATCCAGCAAGGCCGTACAGCCGG
ATCTGTTGCCTGCGCAGGATACCCCTTCCGTCCCAGGCAGAAACGCCAAAAGGGCGCGATACCAAATCTTTAAGCCAAAGGTTCAATCCGCCAAT
AAATCGCGAAAAGGGTCAACACCAACCCGCAGTCGATACCATATATTGCGCGAACGTTTGCGCCATAAACTAAGCCAGCGCTGTCATTCCCTAAT
CACCACCTATGAATCCTACCTGCGTCATCACATCGAAAAATATAAAGACTGCGAGTTGGTACAGGTCGTGCACAATCGTTTTTTCGCCCTCGAAC
TGTACACTCAACTTCTGGTCGATCTGAGGATGTTCTGCAGCAATACAAACTCTAAAACGGCAGCGCAGCCAAAGAGATCTAGGAGTGATGATGAG
GCGGCGAAGCTGAGAAGAGCCAACCGGCAGGAGGAGATGCTTCGCCAAATGCTCCAGCCGGATACTACAGAAGAGCGCAATCGCAAAGATGCCAG
TAAGTTTTAGTTCAATCCCATTTAATGAAATTCAACTTGAATAATTTTATTATTTTGCACGTTCAGTTTTTGCCATGAATTTTTATGAAAAGGTA
GAGGAGGCCTTGCTGAGTGCCAATCGCCTAGATGATTGCAAAAAAATTCAACAGTATTTTGCAAAACTTCGACCCCAGGCAGGAGAAAGTTTCATC
TTTGTATTTGGTATGTATCACTTAAGTGTCTTACTCTTATTGCATTCTAATTTTTTTTGGGGTTCTTAGAAAGTGGAAGAAATTTTGCTACCCA
CTCATCCCGAACTGGCTGAAGTATTCCTCAACTTTTTGCTACCTGCCGAGGCCGCTGAGATGGGAAAATTCTTTGAGCACTTTATGATATGCAAT
GCTACCAACTTTATCAACAAACTTAACATTTACTTCAGTAAGCAGCCAGCTCAAATCAGGAAGATTTATGCCTGTCTAAACGAGTTGGCCGAAAT
GCCTAATGTCAGCATGAAAAAAGTTGAAAATAAGATAATGCCCTTGCTCAAGGGCAATCAATTTCTGATCGATTGGTTTGTGCAACAATTCCCAC
AGGGAAAACCACCAAAAAGGTAAGAATGGTAAACAAAATACTCGAGATTGATTTAATGTAACATTGTCTTTTATTTCCAGAATCCTTTCTCCTGT
AGAGACCATAAATTTGCATGACGTTCAAAACAATACAACGGGAGAATATACGGAAACTATTCAAGAGTTTACAGATGTACCTACGCCAAGTAAAC
CAGGTTGTCACTTAAAGTATATCAATGGTCGCATATTTTATGGAGCCAAGATCCTATTGCCTGCCAAACTGTCTTTTATGGCTGCCAGTATTTAC
AATGAACAATCTCATGACGTGCCACCCGTCTCCAGTGACTCGATAAACTGCGCCCATGGTATTCGTGCCCAGGGAGAAAAACTTCTTAGTATGGC
TTCCAATACAGATAGCGACGATGGCGCGGATCGGAGTGAGGAAGATGATGCCAGCCGCGCCTTGATTATTGATACCACGAGTGATGAGCAGAACA
GCTGCTCATCTATTGAGATGTGCGATGAGACAGGCTTAAGAGCACATGCAATCAGATTGAATCCCGGCTTGTATACCAACTCAAGCTTTAACAAT
GCAGCGACCAGTACGCCCAATCTGGGCAACTCTCACCAATCCCATCATCCGCACGCCAAAAAAACTGCCATAAACTTTGGTGAAATATCCCCACG
CAAGCAATCGGCATTTAACAACTCGGGATTGAGTCCCTTATCGGCGGCCCCCAACAGTTCCCCTCAAGTCGACAAACGAAAGTCACCTACTAAGA
AGATCCGATCTCCTCTTAATCAAACTCAGAGCAGACAACGTGCCAATAATCAGCCAATGGTTGTTATCCATGAGTCTCAGCCTTCATCTTCGCCA
GCCATTGAGTGTGCAAAGCGCTTGCGCACGCTGATCGATCAGGAGAGCGTGCGGGATGCAGCAGATACAAAGGCGGGCATTCGAATTATTGCGCA
AGCCAAGCAGCAACCTCCAAACCAATGCAGCTCTGAAGCTATTACGAAAGTCGAGGTAGTCAGCCTGGATGAAAGTGCCGAGAATATGCCTTTCT
GTACAAATCTCAAAATGGACACAGATCAATCGGAGGAGGAGCTGGAGCCACTGCAATTAAGTGCTGGCAACACACCACAGCACGTGATCACAACA
CAATTCGATAGCGATGAGGACTGCAAGCTGGATGTTGTGGCCACGCTGGCGAACTGCACCACCACCGAAGATAGATCGGAATCGGCAGCGGCATT
ACCTGCCACCACATCGCACTCTGAGTCTGGTAGTTCCCACTCGGCACCTTGGACTCGTGAAGAGGACAAAGTAATCCTGATCGAAATGAAAATAG
GGGCACGGGATCGAGAGCAGCTCATTCGGCGTATGCGCGCCAAGCTAAAGAATCGCAGTATAGAAGAACTACGTAGTAGGCATCAGTTTCTTATG
GACTTTCTGTCCAAATTGCAGGGAAAGTGAGGTTTCTCTAAGATGGTCTTTTGTGTATTATAATCCAAGCTGAAATAGGATACTAATAATAACTG
TATATAAACGAAATGGTTTACCCCATACCTACAAACCAAACTTTTTGAAGGGAATTCTTTGTTGTACTGATTACCTATTTAAGCATACAAAAATT
CCCTTCAGAATACTTAGTTTTATTATTAAAAATTTGAATATTTTGAAATCTACTGTACGTTGAAATTGACTATTAATAGATATATTGAAACCATG
AATTTAATATTTTTGTGTCCGTCTAAGTTTACTTTTCTATATGATAAGAAGGTCGCATTGTTTGAATTTGATTATTCTATTCTATAGTTTTGGTT
AACGAGCACATTGTTTTCCATTGTCTTAAAGATTGTAAATATATAAAAATATAACATTTTTTAAAATCTCTAAAATGTATCTGATATTGTCAAAC
CAGCTTGTTCGGGAACTTCAAACGTATTCGCATTTGAGAACTTAAACAAACCTGGAATTGTTCCTTTAAGAAGTACGACGTAAGACTAAAATATG
GAGCTCTCGTTGGATGAACCGCAATGCGCATCCTTCTTTTGCATCCTGGGTGCCGTGTGCGCCATTGTCTTTTCGACATTGGGAGCCGCCTACGG
AACAGCGAAGGCTTCTGTGGGAATCTCTTCGATGTCAATCAAGCATCCGCAGCTGATCATGAAGGCGATTGTTCCAGTGGTTATGGCTGGCATTA

FIGURE SHEET 731

TAGCCATTTATGGACTGGTGATCGCGGTCCTGCTTGCTGGATCACTTAGCAGCCCCTATAGCGCCTACAAGGGTTTCCTAAACCTCAGTGCTGGA
CTGGCGGTGGGAGTCTCTGGGATGGGGGCTGGAATTGCTATTGGCGTGGTGGGCGAAGCTGGAGTCCGTGCATCTGCCCAGCAGCCAAAACTCTT
TGTGGCCATCATTTTAATATTGATATTTGCCGAGGTCTTGGGTCTGTATGGTCTCATAGTGGCCATTTATTTGTTTTCCA
(SEQ ID NO: 1369)

Exon: 1001..1501
Exon: 1567..1897
Exon: 1952..3020
Exon: 3081..3552
Exon: 4406..5414
Exon: 5482..5615
Exon: 5676..6004
Exon: 6066..7440
Start ATG: 1001

Transcript No. : CT35746
ATGCCGAGCAGTGCAAAGAAGTCGGACTCTGCAAAGAGCAATAGCTCGACGCCACGAAGACCGCGAAAGCGCAAACGAGTGGATCGCCAGAGCCT
GGACTCGCAGGTCGATGAGGATGCCAAGGAGATCGATCGCCGGCTACGGAAAGTGGCCAAGAAGAACTCCATCAGTGCCGAGGACATGCAAAAGG
TGGTCCGGAAGGTGGTGCGCAACGATCATGTTCTGGCATTAGTCACTTTGAAGGCGGAGGACGAGCTGGCGCGGGAGAAGTTGGAGTCGGCGGAG
CAGCAAAAGCGGGGTGCCATCATCATAACGGACACTCCATCTGTGCCCAAGCTAACGCGAGCGAAAGCACGGGAACTGAACTGCACGCCTGGGAT
CTCGCTGCCCCAGCTCAATGAAACTTCCACCGACAATAATGGTATAGAGGCTCTAATACGTGAGGATTTGCACTCTGATGAGGAGGACGAGGAGT
ATACCTTCAAGGAGGAGGACTTTCATTCCGATGATGATCCTAACACTACAGCATCGGATTTCGACTCCAATCCCTGCACGCCTCAAACTCCTCTT
ACTGCCAATGAGGAATCTCCTATCAAATTCTCTGATGACGGTTGTTTCAAGGTGCCGTTGGACAGAAATTTTCAGGATAAAGAGGATCTTAGGAT
TGCCACTAGAACGCGCTCCAAATTTTGTTTGCAGCAAACTACCATTGAGGATTTGCAGTCGGAATTTGTCCCGCCGGACGTGGAGCCTAGCGATG
TGGTGGAGAACGAAATGACCGCCAACGATGCGGATTGGATGCAGTTCCTCAATGACTTTACAAAGCCTTTAAACAATACGGTCCAGGGCGACGAT
GATGATCCTATTAACGATCCAGAATATGTGGCCGCTGATCACTTGGAATCGGAATATGAGAACGCCGAGGAGCTGCGCGATGTAAATATATCTAA
AAAAGAGTTAACTGACCTGGTCTCTGAGCTGTTTGCTGGTTTGCTGGAAGAAGGAGTCTCTCTGGAATCGATTGAATTGGAAACACCTCAAAAAT
TCGTTGAAAGTGCCAACGTTTCGATGATTCCCATTGATCAAGTGTCCCGTAACATCGATTTTGATGGCCAGCAGATAAATGCTAATCAGCAGGAG
CTGTCCGTTTTTCAACCTAATCTAATGCCGCCTCCTTGCGAAGGGAACGAAATGGGCATGGGTGTGCCTGTCCCTGTGGCTGTGCTGCAGGAGGA
AACTGGTGGATCCGCTTGCAATGTGGTAAACATACCTTCCGAGGCGCTGACTGTTCCCCCCGAACTAATAGCTGTTCCAATACCTGGGCAACCTA
ATTGCTTCCAAATCGCCAAAGTTGTAGGCAATGATTCAACTGTTGGTCTTCCATTAACTGAAGAGACACTGCAGAACTTTTCTAGCTTGCATCCA
ATGGAACCCCCCGTGGTAGCTGCAAGCAATGGAGATCGATATAAAAAACCATTTGATACGAACTTCACCTGGGAATACATCTCGGTTAGGAAACA
TATATATTCGGAGTATGAGGAAAAGTTTGAGAGCCTGCGAAACGTAGAGCCAGTAAACCTCAATCATCTCGCCAGGAGCAGGGGATTTACCCAGT
CTCAGCATGATATGCTTCAGCAGCAGCTTCGCATTCACACGCAGTTGCTCAGTCAAAGCTATCTGCAAACCTACTCCCATCCTACGTTGTACCCC
ATGGCCAAGAAGCCCAGAGAAATGTTGGAAGAATTGCACAAAATGGCAACTAAAGATCCCAGTTTTAATTGCTGGAATCTGCAGGAGGCTGTTCA
GCTGGTTAGAAAATGGGAACATGATCTGTCCAGTGATGAGTTTAAGGAGGAGAACGAGAAGATGATGGACTTCATCAATAAGGAAACGGATCTGA
CTGATGGCCACACGCGCCAGGTTCCCAGGCTGGCGCCTCGTATTATGGATCTCATGCTGGATAGCCGGGTGTTTATGTATCCGCAGTACCTACCC
CGTATGGCGTTTCAACCGAAACTGACTCAAACCCACCGCTTACGCACCATCCGAATATCAGCTTATTGCCATTGGCCTAGAGAAGCACTTGGCATT
AATGGTAAAAGCCAAGAGACAACTACGCAAAGGTGCAGATCCCATTCGCGTTGCCTGTAAGCGAATGATTAAGGATACGATTTGTGGAAAGACTG
CCCGCCGAATTTTCTTGAAAATCGCGGAGCTACGCAACTCAAAACAGTACAATCCAGTGAAGTATTTCTTTGAACATCGTCGAGCACCGCCCGCT
AACGCCATCCTTTGGGGATTCGCTGGTGGGCTGGTGAGAACTCCGCGGGAACGACACATGGAGCTTCCCAGTGGCTGGCAATACTACATTGAGAA
AACTTGGGATCAAAAGCGCACACGTCGCAATTTTAAAGCATCGAAAGCATCGTCGGTGGCTAGTGCTTCTTATTTGGAGTTTGTACGCGAGGCGG
TCGGCGAGGACCTGCTGCTGCCAGAGACTTTTGGTCAGGCTGCGGTCCCCAATGGCAGTGCTGCTGGTTCGGAACCGCCCAAGGAGAGCAAACCG
AAGAAAAGGCCAGCGCAAAGGAGACCCCGCCCTGCGGAAAACCCACCACAGCTTACCATCAATGTGAATTATGTTTTTGGCGGGAATACGAGCGC
GGGAAACATACCCGGGGTCTCTGGGGTTTCGGTGCCCTTGGTGGCCGGCGGAAATCTGGCCGAGAACGTACTGAACATCAATCGCAGCTTATACA
CCGCCGCCGAGTGCAGTAGTCTGCTGGCCTTGCCGCCTGCTCCTCCACCATTGGATGAAAATGCTCCGCCAGCCATCAACTTCACAGTAGACAAG
TTCACTAACACACTACAAATCTGCGAATTGGAGGAATCCAGCAAGGCCGTACAGCCGGATCTGTTGCCTGCGCAGGATACCCCTTCCGTCCCAGG
CAGAAACGCCAAAAGGGCGCGATACCAAATCTTTAAGCCAAAGGTTCAATCCGCCAATAAATCGCGAAAAGGGTCAACACCAACCCGCAGTCGAT
ACCATATATTGCGCGAACGTTTGCGCCATAAACTAAGCCAGCGCTGTCATTCCCTAATCACCACCTATGAATCCTACCTGCGTCATCACATCGAA
AAATATAAAGACTGCGAGTTGGTACAGGTCGTCGCACAATCGTTTTTTCGCCCTCGAACTGTACACTCAACTTCTGGTCGATCTGAGGATGTTCTG
CAGCAATACAAACTCTAAAACGGCAGCGCAGCCAAAGAGATCTAGGAGTGATGATGAGGCGGCGAAGCTGAGAAGAGCCAACCGGCAGGAGGAGA
TGCTTCGCCAAATGCTCCAGCCGGATACTACAGAAGAGCGCAATCGCAAAGATGCCATTTTTGCCATGAATTTTTATGAAAAGGTAGAGGAGGCC
TTGCTGAGTGCCAATCGCCTAGATGATTGCAAAAAATTCAACAGTATTTTGCAAAACTTCGACCCCAGGCAGGAGAAAGTTTCATCTTTGTATTT
GAAAGTGGAAGAAATTTTGCTACCCACTCATCCCGAACTGGCTGAAGTATTCCTCAACTTTTTGCTACCTGCCGAGGCCGCTGAGATGGGAAAAT
TCTTTGAGCACTTTATGATATGCAATGCTACCAACTTTATCAACAAACTTAACATTTACTTCAGTAAGCAGCCAGCTCAAATCAGGAAGATTTAT
GCCTGTCTAAACGAGTTGGCCGAAATGCCTAATGTCAGCATGAAAAAAGTTGAAAATAAGATAATGCCCTTGCTCAAGGGCAATCAATTTCTGAT
CGATTGGTTTGTGCAACAATTCCCACAGGGAAAACCACCAAAAAGAATCCTTTCTCCTGTAGAGACCATAAATTTGCATGACGTTCAAAACAATA
CAACGGGAGAATATACGGAAACTATTCAAGAGTTTACAGATGTACCTACGCCAAGTAAACCAGGTTGTCACTTAAAGTATATCAATGGTCGCATA
TTTTATGGAGCCAAGATCCTATTGCCTGCCAAACTGTCTTTTATGGCTGCCAGTATTTACAATGAACAATCTCATGACGTGCCACCCGTCTCCAG
TGACTCGATAAACTGCGCCCATGGTATTCGTGCCCAGGGAGAAAAACTTCTTAGTATGGCTTCCAATACAGATAGCGACGATGGCGCGGATCGGA
GTGAGGAAGATGATGCCAGCCGCGCCTTGATTATTGATACCACGAGTGATGAGCAGAACAGCTGCTCATCTATTGAGATGTGCGATGAGACAGGC
TTAAGAGCACATGCAATCAGATTGAATCCCGGCTTGTATACCAACTCAAGCTTTAACAATGCAGCGACCAGTACGCCCAATCTGGGCAACTCTCA
CCAATCCCATCATCCGCACGCCAAAAAAACTGCCATAAACTTTGGTGAAATATCCCCACGCAAGCAATCGGCATTTAACAACTCGGGATTGAGTC
CCTTATCGGCGGCCCCCAACAGTTCCCCTCAAGTCGACAAACGAAAGTCACCTACTAAGAAGATCCGATCTCCTCTTAATCAAACTCAGAGCAGA
CAACGTGCCAATAATCAGCCAATGGTTGTTATCCATGAGTCTCAGCCTTCATCTTCGCCAGCCATTGAGTGTGCAAAGCGCTTGCGCACGCTGAT
CGATCAGGAGAGCGTGCGGGATGCAGCAGATACAAAGGCGGGCATTCGAATTATTGCGCAAGCCAAGCAGCAACCTCCAAACCAATGCAGCTCTG
AAGCTATTACGAAAGTCGAGGTAGTCAGCCTGGATGAAAGTGCCGAGAATATGCCTTTCTGTACAAATCTCAAAATGGACACAGATCAATCGGAG
GAGGAGCTGGAGCCACTGCAATTAAGTGCTGGCAACACACCACAGCACGTGATCACAACACAATTCGATAGCGATGAGGACTGCAAGCTGGATGT
TGTGGCCACGCTGGCGAACTGCACCACCACCGAAGATAGATCGGAATCGGCAGCGGCATTACCTGCCACCACATCGCACTCTGAGTCTGGTAGTT
CCCACTCGGCACCTTGGACTCGTGAAGGACAAAGTAATCCTGATCGAAATGAAAATAGGGGCACGGGATCGAGAGCAGCTCATTCGGCGTATG
CGCGCCAAGCTAAAGAATCGCAGTATAGAAGAACTACGTAGTAGGCATCAGTTTCTTATGGACTTTCTGTCCAAATTGCAGGGAAAGTGA

FIGURE SHEET 732

(SEQ ID NO: 1370)

Start ATG: 1

MPSSAKKSDSAKSNSSTPRRPRKRKRVDRQSLDSQVDEDAKEIDRRLRKVAKKNSISAEDMQKVVRKVVRNDHVLALVTLKAEDELAREKLESAE
QQKRGAIIITDTPSVPKLTRAKARELNCTPGISLPQLNETSTDNNGIEALIREDLHSDEEDEEYTFKEEDFHSDDDPNTTASDFDSNPCTPQTPL
TANEESPIKFSDDGCFKVPLDRNFQDKEDLRIATRTRSKFCLQQTTIEDLQSEFVPPDVEPSDVVENEMTANDADWMQFLNDFTKPLNNTVQGDD
DDPINDPEYVAADHLESEYENAEELRDVNISKKELTDLVSELFAGLLEEGVSLESIELETPQKFVESANVSMIPIDQVSRNIDFDGQQINANQQE
LSVFQPNLMPPPCEGNEMGMGVPVPVAVLQEETGGSACNVVNIPSEALTVPPELIAVPIPGQPNCFQIAKVVGNDSTVGLPLTEETLQNFSSLHP
MEPPVVAASNGDRYKKPFDTNFTWEYISVRKHIYSEYEEKFESLRNVEPVNLNHLARSRGFTQSQHDMLQQQLRIHTQLLSQSYLQTYSHPTLYP
MAKKPREMLEELHKMATKDPSFNCWNLQEAVQLVRKWEHDLSSDEFKEENEKMMDFINKETDLTDGHTRQVPRLAPRIMDLMLDSRVFMYPQYLP
RMAFQPKLTQTTAYAPSEYQLIAIGLEKHLALMVKAKRQLRKGADPIRVACKRMIKDTICGKTARRIFLKIAELRNSKQYNPVKYFFEHRRAPPA
NAILWGFAGGLVRTPRERHMELPSGWQYYIEKTWDQKRTRRNFKASKASSVASASYLEFVREAVGEDLLLPETFGQAAVPNGSAAGSEPPKESKP
KKRPAQRRPRPAENPPQLTINVNYVFGGNTSAGNIPGVSGVSVPLVAGGNLAENVLNINRSLYTAAECSSLLALPPAPPPLDENAPPAINFTVDK
FTNTLQICELEESSKAVQPDLLPAQDTPSVPGRNAKRARYQIFKPKVQSANKSRKGSTPTRSRYHILRERLRHKLSQRCHSLITTYESYLRHHIE
KYKDCELVQVVHNRFFALELYTQLLVDLRMFCSNTNSKTAAQPKRSRSDDEAAKLRRANRQEEMLRQMLQPDTTEERNRKDAIFAMNFYEKVEEA
LLSANRLDDCKKFNSILQNFDPRQEKVSSLYLKVEEILLPTHPELAEVFLNFLLPAEAAEMGKFFEHFMICNATNFINKLNIYFSKQPAQIRKIY
ACLNELAEMPNVSMKKVENKIMPLLKGNQFLIDWFVQQFPQGKPPKRILSPVETINLHDVQNNTTGEYTETIQEFTDVPTPSKPGCHLKYINGRI
FYGAKILLPAKLSFMAASIYNEQSHDVPPVSSDSINCAHGIRAQGEKLLSMASNTDSDDGADRSEEDDASRALIIDTTSDEQNSCSSIEMCDETG
LRAHAIRLNPGLYTNSSFNNAATSTPNLGNSHQSHHPHAKKTAINFGEISPRKQSAFNNSGLSPLSAAPNSSPQVDKRKSPTKKIRSPLNQTQSR
QRANNQPMVVIHESQPSSSPAIECAKRLRTLIDQESVRDAADTKAGIRIIAQAKQQPPNQCSSEAITKVEVVSLDESAENMPFCTNLKMDTDQSE
EELEPLQLSAGNTPQHVITTQFDSDEDCKLDVVATLANCTTTEDRSESAAALPATTSHSESGSSHSAPWTREEDKVILIEMKIGARDREQLIRRM
RAKLKNRSIEELRSRHQFLMDFLSKLQGK*
(SEQ ID NO: 1371)

Name: putative DNA binding protein
Classification: DNA_binding

Celera Sequence No. : 142000013384591
TGTTATCAATTCACTAATTACTAAGCAAACCAATGCCAAGCGTATCCTAAAATTAATGTTCTTTGCTCTACATTCACATACTCCTTGTTCGGCGC
CGTTTATCTGCTATTAAAAAAACTGCCAATTCTATTTGCCATCTTTGTGCTCAATAATCCCAAGACCTTGAAAAGAGCCCTTCCATGCCAATTAA
ATCAACTATTAATTGTTTATCCCTTCTGCCTCGGATGATAGATGATGCACGAACTGGCTTAACACCTGCACCGATATATAAAATTTGTGTGGATA
AATGGTTAACTTAGCTAATTAAAAAAGTTCCTAACTTAAATCATTGTAGGCAGTATGTCATTATGTTTTCTCGGTTTTCTCTTGCTGTGTGGATT
TGAAAATAATTGCTGACAGTGTGTTAATTTGTTATTTGAACACAATTGCTTGATTATGTCATAAAATACATAGATAACTGAGTTGCAAATTAAAT
ACTGTGAGTGGGTTTCGTTAAATGTAAATATCATGTTCAACTTAGTCCATTAAAACTTTTTAAACTGTTGGAACGACTTGCAGCAAAGATTACCA
TCCAAAAAAAATTCCGAATACACTCAACGGTAATCCTTCGCATTAATGGAACAATTCTAATATTCTAAAACTTTTGCGTGCTATATTTGCATGCA
TGCTATGCGGCACACTGAGAAGCGTCTACACATTTAAAAAGGATTGGCAAAGCTTTTACAAAATTACGAAACTACGGTTACAAACTACTTTGCCA
AAAAAAAAATTAGCAATACCATGTGCAATACTGATTTGAGCCCGATCAATCGATTTGGCCTGGCAGGTATATTCGAAAACTAGACGTCTCGAAAG
CAAATCTAAAAACTAACCACTGTGCTCATGCCAAATGGCGCTCCTCCTCGCAGATGGCACTGCGCGTCGCCTCGCACTGGGCACAGTGCTTCTCC
AGAAACTTCATGGACAAGTGGAACGTATACCGGTGCCGGGTGCAACGCCTTTACATCTTGTACTCGACGATTTTGTTGGGATTGAGGAACTGCTC
CCGTTGCGACGCATCCAAATGGGCTACGGTGCGCGTCAGTGCCGAGCCCGAACCCGATCCCGATCCCGATCCCTGTCCCTGACCCTGACCCTGAC
CCGATCCTGTTCCAGTTGCTGATCCCGAGGAGGACTTGTGCTTGCCATCGCCGCCGCCGCCACTGGTGCGTCCAGTATCCGTGCCAATGGGCTGG
TAAACGCCCTCTGCACTGATCACACCCACATTGACGCCGGCGACCACTGGCTGTTGGAGATATCCGGAATACTGTGGCGGCAGCTGGTAATTGCC
CGGCGGCTGCTGCTGCTGCTGTTGGTGGCTGCCCGCCCGCGGCTGCTCCGTGTGGGCAATGGGATACTGCTGCTGATGGGCGTAGTCCTGGCTGC
TGCCCACAGCGCCAGCGCCAGCCACCGAGCCGCCAGCTGCTCCTCCGCCACCGGCTGATCCTCCAGCACCGCCACCGCCCATCCGGGAACCGGAA
TCATCGTTCAGGCCCTCACCCATTTCACCATCCCGATTGCGCCGTCCGCGGATGCACAGTTTGGTGAAGAGCCAGACTCGTCCGCGGTAAAGGAG
GTAACAACAGAAGTGAACGAAGAACGTAAAGATGATCGCACAGGCCGTCACTATGATCGCCTTGCCCGGCTTGGTCCAGTCCATCATGGGATAGA
TAGCAGTTTGATTTTTCCTGCAAACACAATCGTCATTATCATCCAAATTTGATCAATCATTTTCAGTGCGTATGAAAATCACCTGTCTGTTCCGC
CGGCCAAGAAATAGATTCCCGTGAATATGGCGTAGGCCAGGCCAATGCCAGTGGTAAAGTAGGCGTGGCTCATCTTTATCGGATGCCCCACAATG
GCCAAATCGATGAGCATTATAATCGTGTTGAGCACATGGACCATTATGTTTAGCGCATCGATCTTATGGATTTCTGAAAGATAAAAGATGTATAA
AAGATATGTTCTCTAATTAAATGGTTTCCCTTTTCTAAAGAACTCGATTAAAATGCACTTCGTTCTATTCATATATTTGGCCCTGCAGGGGAGGC
TTTTTCACAGGTGTCCAATTTAGGAAATCCCTAATCCATGAACATCTCCCACTGGCTCTTAACGGATCTGGACAAAAACTTTTGATTTGCCGTCT
GGCCAGCGTAGTAGAACTCAAAACCAACGTCATTGGCGGAGTCAAGAAAGATGTAGCAGGCGAGAAAGTCGAACAGGAGCATCGTGGAGCACAGC
GGCCTATCCAGAATTGGCGGTAAATTCTCCCAATAGCCGGATATGACCTGCGCCTGGAACACAATCAATGGGCATATAACTTGCCAGAGCACAAA
GTGGGTGGCTACTTCATAGGAGAATATCTGATCTGAAACGTGTACACAAACGGCGGCCATTAGGACGGAGGAGAGCACAACGAATATGAACCAAG
TGAGGAACAAGTAGGCCATTGCAGGGCATTCGGGCAATAGATATGAGCCGACCAGCAGGAGCAGCGCCATCATGACAAGAATCTCCATGCTCAGC
AGCAGGACGTGTCCCGTCCGCTGGTTTGAAAGGATACACACCGTTCCCAGTGCCAGACAGGCTGCTATGCAGCAGCTGACTATCCAGTTGAAGGG
GAACTTCCGGCGCAGCCAAGTGACGTTGACATAGACGCACAGGGTGACCAATCCGATGACAAAGAAGCAATAGGTAGCCACTACATCCGGAACCA
GGAGGTATCGTCTGAACAGGCCCGGCAAGATGAGCAGCCCAATGGCCAGGACAATGAACAGCGCCGCAATGCCGTAGATCCACTGGGCCACCTTG
AGACGAAGGCGCACGACGCCATCGACTGGCTGATCATTCATCGATGTGGGGATTTCCTCGTTTTCTGCTTGTTTCCCGGCGCCCGTGTCAAGTG
TCAAAGGCGACAGTTCGGCCTGACAGCCAGTATGTTAAGTGTAACCAGATCGGCATCAGCCCCAAATTTCAGCGTGCGATCCGTTGTAACCTATA
GCTCCACGAGCCACTTCGAGGCAAATCATAGTGTGAGTGATAGTCCGTTCTCGGAAGTGGATCGTTTTGTGGAGGCTGCCACCAGCATCAACCGT
TTTCCAAAGAGGCGGAAACTCTCCTCCTGCATTTTCCGAACCTACGTCTGCCTGCTGTTGGTCATCCAGGTCATCCTGGCATCGCTGCAGTGGCT
CGGATCCACGTACCGCTGGAAACCGCAGCTGAGTGCGGCCAACCGCGGCCTGTCCGTCCTGCTACTCCTGATTTCGTGGATCAACCTGACGCTGG
CCTTCATGGGCTTCCGGCGGCTGCAGTTCACCTTCCCGCTCAATTGGATTGTCTTTGGGTGCATCTTCGAGAGCCTCACGCTGCTGGTGGTATGT
CTGCACATTCTGGAACAGGACCTAACGTGGCCGTTTGTGCTAATTGGCATTGGCGTGCTGGTTGTCTATACGCTGCTGGGGCTGTGGGTACCTGG
ATTCCTCACAGCCAACTTGTGGATCCTAATCCTGGCAAGCATTGTGGTCTTCCTGGTCTCGACAGTGGCCTTGAGCGTTCGCCTGCAGATGCGAT
ACTACGTGCCCGCTAGCGTCTGTTTGGTTTTCTTCGGACCCTGGACCATGTACAACTCCCAGAAGTTGTTCCTGCACCACAAGCGGTCTGGTTAC
GTAGCTCACCAGTATTTGGAGGCGTCCGCCAAGATGTTCATCAATTATGCCTTCACTGTGAGTGGCATTATATTTGCCCACCGCTTCTCGGTGGA
CACATTGGATGCCCACAGTTAGGATATGGTGATTTCTTGGCTGCCATTTTTGTGGTTTAGATTTTTTATAAGTCTTTCTAAGTGCTGTGCA (SEQ ID NO: 1372)

Exon: 2891..2210
Exon: 1973..1793
Exon: 1727..1001
Start ATG: 2891 (Reverse strand: CAT)

Transcript No. : CT35813
ATGAATGATCAGCCAGTCGATGGCGTCGTGCGCCTTCGTCTCAAGGTGGCCCAGTGGATCTACGGCATTGCGGCGCTGTTCATTGTCCTGGCCAT
TGGGCTGCTCATCTTGCCGGGCCTGTTCAGACGATACCTCCTGGTTCCGGATGTAGTGGCTACCTATTGCTTCTTTGTCATCGGATTGGTCACCC
TGTGCGTCTATGTCAACGTCACTTGGCTGCGCCGGAAGTTCCCCTTCAACTGGATAGTCAGCTGCTGCATAGCAGCCTGTCTGGCACTGGGAACG
GTGTGTATCCTTTCAAACCAGCGGACGGACACGTCCTGCTGCTGAGCATGGAGATTCTTGTCATGATGGCGCTGCTCCTGCTGGTCGGCTCATA
TCTATTGCCCGAATGCCCTGCAATGGCCTACTTGTTCCTCACTTGGTTCATATTCGTTGTGCTCTCCTCCGTCCTAATGGCCGCCGTTTGTGTAC
ACGTTTCAGATCAGATATTCTCCTATGAAGTAGCCACCCACTTTGTGCTCTGGCAAGTTATATGCCCATTGATTGTGTTCCAGGCGCAGGTCATA
TCCGGCTATTGGGAGAATTTACCGCCAATTCTGGATAGGCCGCTGTGCTCCACGATGCTCCTGTTCGACTTTCTCGCCTGCTACATCTTTCTTGA
CTCCGCCAATGACGTTGAAATCCATAAGATCGATGCGCTAAACATAATGGTCCATGTGCTCAACACGATTATAATGCTCATCGATTTGGCCATTG
TGGGGCATCCGATAAAGATGAGCCACGCCTACTTTACCACTGGCATTGGCCTGGCCTACGCCATATTCACGGGAATCTATTTCTTGGCCGGCGGA
ACAGACAGGAAAAATCAAACTGCTATCTATCCCATGATGGACTGGACCAAGCCGGGCAAGGCGATCATAGTGACGGCCTGTGCGATCATCTTTAC
GTTCTTCGTTCACTTCTGTTGTTACCTCCTTTACCGCGGACGAGTCTGGCTCTTCACCAAACTGTGCATCCGCGGACGGCGCAATCGGGATGGTG
AAATGGGTGAGGGCCTGAACGATGATTCCGGTTCCCGGATGGGCGGTGGCGGTGCTGGAGGATCAGCCGGTGGCGGAGGAGCAGCTGGCGGCTCG
GTGGCTGGCGCTGGCGCTGTGGGCAGCAGCCAGGACTACGCCCATCAGCAGCAGTATCCCATTGCCCACACGGAGCAGCCGCGGGCGGGCAGCCA
CCAACAGCAGCAGCAGCAGCCGCCGGGCAATTACCAGCTGCCGCCACAGTATTCCGGATATCTCCAACAGCCAGTGGTCGCCGGCGTCAATGTGG
GTGTGATCAGTGCAGAGGGCGTTTACCAGCCCATTGGCACGGATACTGGACGCACCAGTGGCGGCGGCGGCGATGGCAAGCACAAGTCCTCCTCG
GGATCAGCAACTGGAACAGGATCGGGTCAGGGTCAGGGTCAGGGACAGGGATCGGGATCGGGATCGGGTTCGGGCTCGGCACTGACGCGCACCGT
AGCCCATTTGGATGCGTCGCAACGGGAGCAGTTCCTCAATCCCAACAAAATCGTCGAGTACAAGATGTAA
(SEQ ID NO: 1373)

Start ATG: 1 (Reverse strand: CAT)

MNDQPVDGVVRLRLKVAQWIYGIAALFIVLAIGLLILPGLFRRYLLVPDVVATYCFFVIGLVTLCVYVNVTWLRRKFPFNWIVSCCIAACLALGT
VCILSNQRTGHVLLLSMEILVMMALLLLVGSYLLPECPAMAYLFLTWFIFVVLSSVLMAAVCVHVSDQIFSYEVATHFVLWQVICPLIVFQAQVI
SGYWENLPPILDRPLCSTMLLFDFLACYIFLDSANDVEIHKIDALNIMVHVLNTIIMLIDLAIVGHPIKMSHAYFTTGIGLAYAIFTGIYFLAGG
TDRKNQTAIYPMMDWTKPGKAIIVTACAIIFTFFVHFCCYLLYRGRVWLFTKLCIRGRRNRDGEMGEGLNDDSGSRMGGGGAGGSAGGGGAAGGS
VAGAGAVGSSQDYAHQQQYPIAHTEQPRAGSHQQQQQQPPGNYQLPPQYSGYLQQPVVAGVNVGVISAEGVYQPIGTDTGRTSGGGGDGKHKSSS
GSATGTGSGQGQGQGQGSGSGSGSGSALTRTVAHLDASQREQFLNPNKIVEYKM*
(SEQ ID NO: 1374)

Classification: receptor

Celera Sequence No. : 142000013384768
GAAATGAGTTTTGTTTTGTTTTGTTTCTTCCGAGTGTTTGTGTGTTTATGTGTGTGGGGAGGGGGTGTATTCTGTGTGCGGCGTGTTTTGAGTGA
GAGAGATAGAGAGAGAGCGCGAGTTGCTGCGGGTCGACGGTCGAAGGGGGTGGTGGTGGAGTTGGTGGTGGGGGGCTTGGTTTATACGACAAGTT
TTGATTTATTATTAAATTTAAATACCTATGTATATAAATTACGTTTCTGTTTATTATAATTATTGTTGTTTCCATCTTAATCATTTTGTTTTCTT
TCGCTTTTTATTTTTCATATTTTTTTTTTGTTTTTTGTATGTAGTGGGCAACTGCGGCATTTGTAAATTTCTTTATATTTAAATGTTCCTTTTGA
CTGTGTAAAAAATATCGATTTCCATCTGATCTTGTTTTGTAGTTACTATTCATGTATGCATTTGCTTTTCGTTTTAGTTAAATTACGTTAACGCTG
CATTCTGAACTCTCTGTTGCTGCTGATTCTGCTGCTTGTTCTTCGGATTCTTGATCGGATTCTTCTGATTCTTCATCTTGGCGCGCTTTCTATGC
TATTGAAATGTTGTTTGTGGTGCTGCTTACTGCCTTCTGGATCGGGATCCTATATTCCGCTCTGATCTGATCGGTTATGTTCATGTTATGTCGGG
TTGTGTGTGTCTGTGTTGTGTGTATGAGAGTGGAGTGTGTTGGGTGTTCGCATCTCGTTATATGTTGTATATATATATATATATATGTGTATATA
TATATATATATAATATATTATATGTATGTATAGTTAGTTGCTTAATAGTAGAATTTCTTGAATGTTGTTGTGGTAAAGTGTAGGTAATGTTGCTC
TATGTCTCTATGTCGACTCAACTGCACTACATACATATGTCTTTCCACCGGATACGCGGCGAACCGAAACGTGCCGAGCCGAACCGATCCCCGTT
TCTGACCCGCATCCGCATCCGTATCCGTATTTCGTTTCCTCACCTCCGCCTCATTCGCTGCGCAGTTTCTTTAGATCCGGTGACTTCTCCCCCAC
GCCCACACCCACTCCGCCGGCGTTCTTCAGCTCCATATCGCAGTGCAGGGCAGTACGCTTCTGTCCAATGGCTGGTGCCGAGTCTGCACCCGCTG
CTACCGGTGAAACCGCATCCACCGCCTTGTTCGCCGCCAGCTGCTGCAGTTTACTGTCCCTCACAATGCCGTTGCTGCTATTGCTCTCGTCAGCC
TCTAGCTCCGCCTCATTATCCTCCTCCTCGTCCAGCTCATCTTCCTCCTCGTCCTCCGCCTCATCCTCATCCTCGTCGCCCAGGACGCCGTTCCC
GTTACCATTTCCATTGGCTGGTGCTGCAGTCGCTTTGCTGGCTGGCTGTGGTGCTGCTGTAACCGCTTCCTCTTCTGCCAAAGGAGCAGGCTGAC
CGTTGTTGGTGATCGAATTGTTAGTTTTGTGGGGCTGGCTCGGCGACTGCTTTTGATTCTGATTCTGGCTCGAGTGCTGTGTGGGAGTCAGGATG
GGCAGGCTGTTGGTCTTGGGCGGCGCCTCCTGATTGCTTTCAGAGTCCGAGGCGAGCGGTGTTCCACTCGAACCGATGCCAATGCCAATGTCTAG
GGCGATGGGCTCACCGTCCTCTGTGGAAGTGGTGGCCGTTGTCTGTGTGGTGCCATCGTTGTCATCGATGATCGGCTCCTGGGAGGTGGAATCGT
TCGAAACAAAGTTGGAGTCACCGTCCTGCAGGGCGGCGCCAACGGCAGCTGCGTTGTTCTTGGCCTCGCCCGACTGTAGAGGCGTCAGAGCAGCC
GGGTTGGTGTTCTCATTCTCTGTCTCCGATTCTGTAGCAGTGTTGCGACCGCCTGGGGGATAGAAAGCATTGGATTAGCCATCAATGGTCAATTT
GTTAACTCGGCGAACTGCGGTCAGAGTAATCAAACAAAGAAACTCTGTGTTTGAAATTATTAGACATCCTAACACTTTTGAAAAGCTGCCAACAA
GTATAAGCTACTGATAATATGTTAAAAGTTAACTATTTTACAGTAGTAACTTTACAATTCCTCCTTTTTATTTAACATGACGCCACGAGTAACGA
ATAAATTGTAAATTGTAAATTGACCACTAGGCTACTACAAACATAATGTTTAATGGAAAATTCCGGATAGGAAAAATACTTGGTTTCTGGAAAAG
ACCACTCGGTTTGAGTGTTTTGTTGCAAGGGTGTATACTCAAGCCGCAGTTATCGGATCATCTTAGCTGCTTACCTGCTCCTTGGCTTTCGTCGT
CCAAATCAACACCCACACCATCGTTGGTATCGTCGCCATCGAGCACCTTGCTGCTGTTGCCGTTTGTGCTGAGTGAACCGGTGCCAGTGGAGGCG
CCGGATCCAGGCGGCGGCATATCGTCGAGCATCTCGGGACTGAGATCATTGGCCACATAGTGTGACCAGAGGGCCAGCTCCACGCGATGAGGCGA
CCAGTGCGGCGTATCCCCGCCCACCTCCGCATTGAGGCGCTCCACGGTGGCCTGAATGTGATTGACGAAGTTGAGGTACTCCTTGGTGGTGTAAT
CGATGCCCTCGATCTCTGGTATGGCCATCAGGCACTCGTCGGCCATGAATGGTGCCGAATCGGGAGCTGCGGCTGCCAGCAGTGCACTGGCCATT
GTGGTGCCAACGCCCTTGAGGTTCGATAAAGCTGTGATCGCCTGCTCCAGATTGGGCAGCTTGCGGAAGGCCTTCTTTGTCTCCTGGATGACGGC
GCGCGGTGTGTTGACCTTGACCAGGTAGGATAGCTGCGGATAGAATTTGCCGCGCGACTGCTTCCACTTCATCGACTGGACGAGCTCATCGTATA CCATATGCGCGTCCTTGCCGCGTGCCTTAATCAATTTGGGCAGTTCATTCTGATACCACTGATCCAGGCGGATCAGCTCTTGCGGCTTCTTGCAG
CGCTTCTCGGCCTTTAGCTTAAGAACCTGGGGATAGAGCTGGTAGCAGTACTCGAACTGTTTGGTGCTCCCGGTCTCGAAGAACGAGACCGTCGC
CTTGCCGTTGGACATCTTCTGCGGATGCGGATGTGTCGTTGTCGCCTGCTAATGATTGGTGGTATCGCTGTATCTCCTTATCGTGGTATCTATCG
CCTTGGGGCCCAGGACGTTGGCTGATCCGCAAGTGACCGGCTGGCTATATATGCGGCAATATATGTACTTTGGTGTAAGCTACTATACGCCAAAT
CAATTTATTGCTTACTGTTTAGTCTCCTGCTTTTCCTGTCCGTTCCGAGCTGCTCCTGTCAACGTACTGCTATTCGTGCGTTGAGAGTTCCCGGC
GAGAAAGAAGCGAGTACGTGAGAGACAGAGAGAATGCGAGTGCGAGAGAGGGAGCACGAAGAAGCAGCAACGCAAAGGAGAGTGGATGAAAAGAG
AAGAAAAGAGGCACACAATTAGGTTTACAGTTACGATTACATATGCAAGGGGGATCGGTGCGGTGGCATAGGGAGGTAGTTCGATTGATTACTGT
TAATGCTGCTGCTGCTGCGGCCGTGTCTCTGTTGTTTGTTGTATTTACTCAATCCGATAATCGCTCACTATTTGCCAAAAATCTGCTCGCTTCCG
CCGCCGTTTGCACAGCACACAAATCGAATTTTTACAGTGCTGTCGTCGGGTTCTTTTTAGTCCGCCATGCACTCACACAGTCAAACTGACAGGCA
CACGGATGGACACACACACACTTACTCAGCACACTCGCTCTCGCACACCCAAAGAGAGCCAGGCGCTCATACACAGGCAAAAACACGCACACAAC
ACACACACTGACTTAAACACGCACACACTTATATACTGAGGCAACAACAGCAGCAGCAGAAAATTTCTTTTTCATCTAGGTTTTCAAAAAAAATA
CGAACGCGAGCATTAAATAAACGAATGCTACTATTTTTCGCTGTTGTTGTTGTTTGTGCTTTTTTCGTACCTCTTGTCTTTTTGGCAAACGGTGA
GAACAGCTTTTCACTAGCGCACTGCACGCACACAGATGAGTGGGTGAACAACAAATACCTTTTAGTTAGTCGCCGCCAGTCTTCCTTTCCGTCCA
CATCCAAACAACTACTCCAATGCTTTGCTGTTTTTCTGTGTTGCCTCTGCTTTGCTTTGCTTCGCTTCGCCTCTGTGCTTGTGCTGTGCTGCGTG
CTTCGTGCTGTGCCCGTGCTGTGCTGCTTCTTCTTCTTCCTCTGCTGTTTCAGTTTCTGCTTTCTGCCTGCAGGGGCGCCGTTGACAACTGACAA
ATAAAAAGGGGTTACTCTGTTCTCGAAATGAGCACGCCACCGAAGGCACAACAAAAAATTAAAAAGGATCGGAGCGGAGCGATGCAGCTGTGCGA
TGTGCTGCTAACTCGTGTGACGGGAATTGGGAATTGGGATTGCGAATGGGAATGGGAGGGAATACGAGAAGCGAATATGGGAATGACGAACGACG
ACGAACCGGGAACAGGAGTTGTCGTTCTATCTCGCCCGCACTCGGTGCCCGAATGTATCTGTATCTCTCTGGCACCCTCGGCGTTCCATTTCATT
TTGCCGGCGACGTCCGTGCTCTCTGCCGCCGCTCTGCCATCGCCTCTGCCGCTGCGTTTATGCGCAGTGCGTCATTACACGAATACCTGTTTAAA
GCGGAGGCATAAACGCGGCTTTGTCGATCAACATCCATGTTACCGAAACCCATGTTCGAGTTATAGAAACTTCGAGTAACAAATATCTATATTCT
AGCAATGTTTACCCTTATTAGCTTAGTTAGTGCAATTATGTTTCATGTTTTTACAAACAGCAGAATGTTTTTAACAATAGTTATCTCTATATTCA
GGTCCTTCAATTAAATCAAAAAGGAATGGGTTTTGTGAGTGGGTTGGGCTCCAGTGAGACTTGTTAATAATTTAAGAATTCGCGATATTCTAGTG
TAAACAGCGCGTCACTGCATGTTCGCTGCTTTTGTTGTGCCAGTTGCCAGCGACAGCGGCGTCGT
(SEQ ID NO: 1375)

Exon: 4005..3966
Exon: 3299..2260
Exon: 1857..1001
Start ATG: 3055 (Reverse strand: CAT)

Transcript No. : CT43088
AGTGAAAAGCTGTTCTCACCGTTTGCCAAAAAGACAAGAGCAGTACGTTGACAGGAGCAGCTCGGAACGGACAGGAAAAGCAGGAGACTAAACAG
TAAGCAATAAATTGATTTGGCGTATAGTAGCTTACACCAAAGTACATATATTGCCGCATATATAGCCAGCCGGTCACTTGCGGATCAGCCAACGT
CCTGGGCCCCAAGGCGATAGATACCACGATAAGGAGATACAGCGATACCACCAATCATTAGCAGGCGACAACGACACATCCGCATCCGCAGAAGA
TGTCCAACGGCAAGGCGACGGTCTCGTTCTTCGAGACCGGGAGCACCAAACAGTTCGAGTACTGCTACCAGCTCTATCCCCAGGTTCTTAAGCTA
AAGGCCGAGAAGCGCTGCAAGAAGCCGCAAGAGCTGATCCGCCTGGATCAGTGGTATCAGAATGAACTGCCCAAATTGATTAAGGCACGCGGCAA
GGACGCGCATATGGTATACGATGAGCTCGTCCAGTCGATGAAGTGGAAGCAGTCGCGCGGCAAATTCTATCCGCAGCTATCCTACCTGGTCAAGG
TCAACACACCGCGCGCCGTCATCCAGGAGACAAAGAAGGCCTTCCGCAAGCTGCCCAATCTGGAGCAGGCGATCACAGCTTTATCGAACCTCAAG
GGCGTTGGCACCACAATGGCCAGTGCACTGCTGGCAGCCGCAGCTCCCGATTCGGCACCATTCATGGCCGACGAGTGCCTGATGGCCATACCAGA
GATCGAGGGCATCGATTACACCACCAAGGAGTACCTCAACTTCGTCAATCACATTCAGGCCACCGTGGAGCGCCTCAATGCGGAGGTGGGCGGGG
ATACGCCGCACTGGTCGCCTCATCGCGTGGAGCTGGCCCTCTGGTCACACTATGTGGCCAATGATCTCAGTCCCGAGATGCTCGACGATATGCCG
CCGCCTGGATCCGGCGCCTCCACTGGCACCGGTTCACTCAGCACAAACGGCAACAGCAGCAAGGTGCTCGATGGCGACGATACCAACGATGGTGT
GGGTGTTGATTTGGACGACGAAAGCCAAGGAGCAGGCGGTCGCAACACTGCTACAGAATCGGAGACAGAGAATGAGAACACCAACCCGGCTGCTC
TGACGCCTCTACAGTCGGGCGAGGCCAAGAACAACGCAGCTGCCGTTGGCGCCGCCCTGCAGGACGGTGACTCCAACTTTGTTTCGAACGATTCC
ACCTCCCAGGAGCCGATCATCGATGACAACGATGGCACCACACAGACAACGGCCACCACTTCCACAGAGGACGGTGAGCCCATCGCCCTAGACAT
TGGCATTGGCATCGGTTCGAGTGGAACACCGCTCGCCTCGGACTCTGAAAGCAATCAGGAGGCGCCGCCCAAGACCAACAGCCTGCCCATCCTGA
CTCCCACACAGCACTCGAGCCAGAATCAGAATCAAAAGCAGTCGCCGAGCCAGCCCCACAAAACTAACAATTCGATCACCAACAACGGTCAGCCT
GCTCCTTTGGCAGAAGAGGAAGCGGTTACAGCAGCACCACAGCCAGCCAGCAAAGCGACTGCAGCACCAGCCAATGGAAATGGTAACGGGAACGG
CGTCCTGGGCGACGAGGATGAGGATGAGGCGGAGGACGAGGAGGAAGATGAGCTGGACGAGGAGGAGGATAATGAGGCGGAGCTAGAGGCTGACG
AGAGCAATAGCAGCAACGGCATTGTGAGGGACAGTAAACTGCAGCAGCTGGCGGCGAACAAGGCGGTGGATGCGGTTTCACCGGTAGCAGCGGGT
GCAGACTCGGCACCAGCCATTGGACAGAAGCGTACTGCCCTGCACTGCGATATGGAGCTGAAGAACGCCGGCGGAGTGGGTGTGGGCGTGGGGGA
GAAGTCACCGGATCTAAAGAAACTGCGCAGCGAATGA
(SEQ ID NO: 1376)

Start ATG: 285 (Reverse strand: CAT)

MSNGKATVSFFETGSTKQFEYCYQLYPQVLKLKAEKRCKKPQELIRLDQWYQNELPKLIKARGKDAHMVYDELVQSMKWKQSRGKFYPQLSYLVK
VNTPRAVIQETKKAFRKLPNLEQAITALSNLKGVGTTMASALLAAAAPDSAPFMADECLMAIPEIEGIDYTTKEYLNFVNHIQATVERLNAEVGG
DTPHWSPHRVELALWSHYVANDLSPEMLDDMPPPGSGASTGTGSLSTNGNSSKVLDGDDTNDGVGVDLDDESQGAGGRNTATESETENENTNPAA
LTPLQSGEAKNNAAAVGAALQDGDSNFVSNDSTSQEPIIDDNDGTTQTTATTSTEDGEPIALDIGIGIGSSGTPLASDSESNQEAPPKTNSLPIL
TPTQHSSQNQNQKQSPSQPHKTNNSITNNGQPAPLAEEEAVTAAPQPASKATAAPANGNGNGNGVLGDEDEDEAEDEEEDELDEEEDNEAELEAD
ESNSSNGIVRDSKLQQLAANKAVDAVSPVAAGADSAPAIGQKRTALHCDMELKNAGGVGVGVGEKSPDLKKLRSE*
(SEQ ID NO: 1377)

Celera Sequence No. : 142000013384528
TGCAAGCGATGCAGCGCTCCTCTCCACTGGGATAACGACGAAGGGCATGTTCTCCGCGGAATCGCGGGCTCAGTGGTCCCTTTTCAAAGGGATAG
TTGATAGTGGCCGGTTCCTTGAAGATGTGCGCCAGGGTGACGGCAAATCCACGTAAGAGTTCACCGAAGAACATGGTGGATGCAGCACGGTCCGT
GATGTCGGCAAACTCCATGCTCAGTTCCTTGTTGTTTACATACACATAGCCCTTGGGAACCTCGACGATATCTTTGGGTTCTGCTCGCTGGGCGG
CCAGCAGCCGGGCTCCATGGCTGCCAAACAGGCGCTGTCCTGTGGGGAGAACATTTTACCATTAAATAACATGCTTAAGTCGAAAAGTTATACTG AATTAAGCGAGTTTAGACTTTTGTTTTGGTATGACATAAGCTTACATAACCTCACTCGCCGCGATTTCCACGAAAATGGGAAATTTCCCGGAAAA
CAACGGATGTGAGGGGATGGGTCGCCACCTACCGTTGCGCGATGCGGTGAAAATTCGCATAGTTAGCGACATTTTTGCGACCAAATTAAACTAAA
ATTGCCAAAGAAGTTGTTTTGCTATTGAATTTGCCCGAACAAATTAGAGCTGGGTTTCTTTCGATTACCCACATAAATTCAATGCTCAAATATCG
TATTCAAATATATCGTAGTTTCTTAATGACATAAACCAAAAATAAAATATGAGATATAAAATATAAATAATGTAACAAAGAATTAAATATTCGTG
TAAAAATAATAAATAATATTAACAAATAATCCAGAAAGACTGTGAGAAAAAAAAGAAAACATTTTTTTATACGAATACCCCTAATAAAAACCTT
AAAGCTTCGATAATGGCACTATCGATATAAATTCGCACTTTTACACTTTTCAACATTGACTTTGAAAATCCCCACCACTACAATTTACAGTTTAA
CTTTTCCCGCTACGCGGAATTGTGAAATTTTTCATTGTTTATGTCGGAAAATGGATCAGGAGGTTATGGATTTCTTTGACTTCTCGAAGGAGTTG
AAGCGCGTGGCCGCCGCCCCGCAAGGCTACATCAGCAGCGATCCGAGGCTAATGGCCACGAAGTTCAAATCATCCGAAGTGCCCAACCGCGAGTT
GATCGGCACCGACTATGTCAGCAAAATCGTCGCCAAGGAAAAGTGTCTCCTGAACGGGGTGAGAACTGGAAGCTTGCGTCAGCACTTCTGTTTGT
TTATGTGTAATTCGATCCAGACGCTGCTCAACGAACAGCCTCAAGGCAAACGCATTCGAACGCTGGACGATTTGGACACCGACGATGAGGGGGAA
GAGACCGAAATTCGCCGGGATGACGAGTACTACAAGAAGTTCAGATTCAATCTGAATCGCGACAAGAACTTGTCCATCTACGCCAAGCGCGAGGA
AATATTGGCGGCCATCAATGCTCATCCGGTAGTCATTATTAAGGGCGAAACAGGATGTGGCAAGACCACGCAGGTGAGCAAAACTTAAATAAAAT
CCTAACTTTTTTATTAAGTCTATATTTTAATAAAGCCAACGCAAGCGAATTATAATTAAACCTTTTATCCTCGACTTTTGAAATTCAAATCCAAA
CTAGTCGAGAGTATTTAATATTATATAATAAATAATAATCTTCAATATACTTTTCAACTCTTTATATAAGAATAGCAAAGCCTAGGAAACTTATA
TCCTATATAGTTATATATCCTATCCTACATACTTAAATACAATGAATATTTTATGTGCAACAGATAAACAAGATCACATCGCGCAAAAATGCTAG
TTATTTAATTATGTAAAAGTTTTATAAACTAACTCAAGTATCCAAAATAGCTTTGAGTTCTTCTTCCGTGACCTCCTCGCTTTCACCCACTTCCA
TTTCCTCGTCGTCACTAAACTCAATCATCTCATACTCTTGCTGCACGTCTGCTGGAAGTTCCCTCTGAAAAACGGTGGCCGAGGACATGCGGCGT
TGATAAGTCTCGTTGACCTCCAGCTGCACTTCTAGTTCATCCGCCTGGTTTTGCGGCTCCCGTTCCTCGACGCCGTACATGGCCTTGTTCCGCAC
CCTCTGGCGCACTTCCAACTGGTTGCCTGTAGATGTTGTGGTACAATTCTCATCTGGAGTACTCTTTCTAGCTCCTAGAACACTTTGGATATCGG
CAAAGACTTCTCGCAAATGGCCGAATATTTGAGAGGGCGGCAAAGCGTGCTCATGACCAGCCGCCAATTGCTTCTTTTGGGCATTGTATGCCGCT
TCCAGTTCACACAATGGCTGGCTTGCCTGGTCCAGTGCTCGCAGACCCTCCAGTTCGTATGTGAGACTGACGCCGTTCGCACGCTGTTGCTTCTG
CATCAAGGCACTCTGCCTCTGTTCCTTGGCACCCGCTACGGTCTCCACACGGTCGTAGTCCACCAGATTGTCCAACCCCTGGCAATAGTCGAGCG
CGGTGAAGCGGAAGGCCTGCTCCTGGGTCAGGCGCCACAGCATGTAGGCGATCTGATGAGTGTCCTTCCGCTCCGGACTATCCTTGCGCAGATCT
AGAGCGTAGTCTGTTAGTTCTTGCCAAGTGCGCGGTGAGACCTCGATCTTAATAAAGTTGTGCGTGGGCTGCTTGTAGTAGATTACGTAGAGCAG
AAAGAAACCTCCGATCCTTTGAGCGCGAGATGCCGGGAAAACGTCCCCGGTGGTGCGTCGGGAGCACGACAGTCGCTTGGCCACATGCAGGGCCG
CCAGTGTGGTGGCTATCACCTCTGTGTGGTTCGTCTGGGCAGTGAAGAGGTGCTGCAGCTGCAGTTCTCGCCAGCACCGGCAGAACACCTCGAAC
TCGCAGTTTTCGCCATCATTAACCAATCGCTGAAATCGTTGCACCAGCTCCCAGCAGTCGTCAAAGATATTCAGCTCCATTCTGAATCTTAATTA
CGCGAAATATATGCGCATCTCTCATTCAAAAGAGCCTCAAAATATAAACAATAACATTCGCCGGGAATAAGCTTTTACAACACTAGCCGGGGAGT
TCATCGATAAATATGTAGTGTTCATAACTGCTTAGCTATTTTCAAAAAAAAAGCGCAAAACTATAAAAACTGTTTGAAAAATGTGTAAAAAATAC
AATTACATTTTTGTTCTGCTTTGTAAATATTTAGATATTTTCTTATAATTATTATTAGTATTCAATCAATTATTCTTACAGGTGCCCCAATACAT
TTTGGATGAGGCCTATAAAAGCGGTAAATACTGCAACATTGTGGTGACACAACCCCGGCGCATAGCTGCCATCTCCATAGCGAATAGAGTTTGCC
AGGAGCGCGAGTGGCAGCAGAACACGGTGTGCAGCTTCCAGGTGGGCCTGCACCGCCCGAACTCTTTGGAGGACACTCGTCTGTTGTACTGCACC
ACCGGGGTGCTGCTGAACAATTTGATTAACAACAAGACGTTGACCCACTACACCCACATTGTGCTGGACGAGGTGCATGAAAGAGACCAGAACAT
GGATTTTCTTCTGATCGTGGTGCGTCGCTTGCTGGCCACGAACTCGCGGCATGTAAAGATTATCCTGATGTCGGCCACCATCGATGCCAAGGAAC
TGTCCGACTACTTTACCACCACTAACTCAATTCCGCCAGTGATCACCACCAATCATCGACGTAAGCACTCGATCGAGAAGTTCTACCGTGACCAG
CTCGGCAGCATTATTTGGAATGAGGAAGATGTGGGACACCAGCAGGTGCCAGAAATCAACAAACACGGTTACAGGGCAGCGGTAAAGATCATAGT
GATTATTGACAACATGGAACGGAAGGCTGCAATCCAGTCGCGGCAGAGCTATGACGAGGCCCTGCGCTATGGAGCTGTGCTCATCTTTCTGCCAG
GCATCTACGAAATCGACACGATGGCAGAAAATCTTACTTGTATGCTGGAAAACGAGTAAGCATTGTTATCCGTGAGAATTGCTCACTGTACAAAT
TTTGAAGTAGCTAAAATTGTATCATTATAATTTCCAATCTTTATTGTTTAATTGCAGCCCCAACATTAAGGTCTCTATTGTTCGCTGTTTTTCGT
TAATGACACCGGAAAACCAACGGGATGTCTTCAATCCCCCGCCTCCCGGTTTCCGCAAGATCATTCTGACCACAAACATTGCTGAGAGCTCCATC
ACGGTGCCAGATGTCTCATACGTTATTGACTTTTGTCTTGCCAAAGTAAAGGTAACCGATACGGCTAGCAGCTTCTCTTCGCTCCGCTTAACCTG
GGCGTCCAAAGCCAATTGTCGTCAGCGTGCCGGCCGCGTTGGTCGTCTTCGTAGTGGACGCGTTTACCGTATGGTTAATAAACACTTCTATCAGA
GGGAAATGCCCGAGTTTGGAATACCAGAAATGTTGCGCTTGCCCTTGCAAAACTCGGTGCTCAAGGCCAAAGTGCTGAATATGGGATCACCGGTG
GAAATCTTGGCATTGGCTCTATCTCCGCCGAATCTGTCGGACATACACAATACAATATTGCTTCTGAAAGAGGTGGGTGCTCTGTACTTAACAGT
AGACGGCATCTACGACCCGTTGGATGGCGATCTTACCTACTGGGGCACAATCATGTCTCGGCTGCCGTTGGACACACGTCAGTCCCGGCTTATCA
TATTGGGTTATATTTTTAACATGCTCGAAGAAGCTATTATTATAGGTAAGCGGGCAACAGTAGTTAAGCTTTAGGATAACGGGGGGAATATTCTT
TGTCTTGCATTAATGATTTTTTTTTAAATATGTTGTAGCTGCTGGCTTATCGACGCCTGGCTTGTTTGCGCACGAAGGTGGTAGGTCTCAATTA
GGCGATTCATTTTGGATGCACTATATCTTCTCCGATGGATCTGGCTCCGACTTGGTGGCCATTTGGCGCGTGTATCTGGTAAGTTATGCGATGCA
TTACTAATAGCGTAATAACTTGTTTCTTCGGCAGACATATTTGAACATTGTGGAAAATGGTCACGACCAGGAGTCTGCTATCCGTTGGGCCAAAC
GTTTCCACGTCTCCTTGCGGTCACTTAAGGAGATACACTTGTTGGTGCAGGAACTGCGTGTGCGATGCACGCATCTCGGTCTGATTCCGTTTCCT
GTTAATCCTAACCAAATGATGGACGATCGTGAAAAAGCGATCATGCTCAAAGTGATCATTGCAGGTGCCTTCTACCCAAACTACTTTACGCGTTC
CAAAGAGTCGTGTGCAGACACAGATCGCAATATATACCAGACAATATCGGGCCACGATCCCTGCCGCACCGTATATTTTACCAATTTTAAGCCTG
CCTACATGGGCGAGTTGTACACTAGGCGCATTAAGGAGCTATTTCAGGAGGTCAGGATTCCGCCGGAAAACATGGACGTTACTTTTCAAGAGGGT
TCGCAAAAGGTCTTTGTCACTTTCAAACAGGATGACTGGATTGAAGGTTCATCTAAGTATGTTCCTGTGTCGGGCAGAGTTCAAAGTGAGGTGTA
CAAGGCAGTTATGATGCGACAAAATCGTGTCGAACGGCCAATCCACATAATGAAGTGAGTTATCAAGGCTTTTACTATCGATTATGAAGCTTATG
TTTAATCATTTACAGTCCGAGTGCATTTATGAGCTACGTACAGCAGCGAGGGATTGGAGATGTGATTGAGGGCCGTTGGATTCCACCCACAAAGC
CTTTAAACGTCGAGCTTCTTGCGCTGCCATCTGTCTTTGACAAAACTATTTCAGGGTCGATTACTTGCGTAAGCTGCTGCACCACACAAATCTAG
AGAATTTCAAAGTATTTTTTTATTTTTCCTATCTTACAGATCGTCAACTGTGGCAAGTTCTTTTTTCAACCCCAATCTTTTGAAGAGTGCATTC
GAAATATGTCTGAAATTTTCAATGCTCCACAGCAACTAAGAAATTACGTAACTAACGCGAGTGCCATCGCAAAGGGCATGATGGTGTTGGCCAAA
CGCGATAGTTATTTCCAGCGCGCCACAGTGATCCGGCCAGAGAATCAGAGCAATCGCCAACCAATGTTCTACGTTCGCTTCATCGACTATGGTAA
TTGCACTTTGCTGCCCATGCAGCTAATGCGTTTGATGCCGAGAGAGCTAACTGAACAGTACGGCGACCTTCCGCCACGTGTTTTTGAGTGCAGGC
TGGCAATGGTTCAGCCCTCTTCAGTGGTCAGTGGAAACAATAGGTGGTCCACCGCGGCTAATGATATGCTCAAGACAGTGGCCCAATGCGGTCTA
ATCGATATTGAGGTGTATTCGCTTTTCAATAATGTAGCAGCTGTTCTCATTCATATGAGAGATGGCATAATCAACGATAAGCTAGTAGAGCTTAT
GTTGTGCCGTCGATCCGACGAAGATTATATGTCTAGAAAAGATCATGATTTCCGTTTGCGACGTCAAGAATCTGCCCGGAACTTGAGCACGGCGC
AGCGTCAACAGATCAATGAGGAATATCTGCGATCCTGTCAGCTGCCGCAAGACCACGATCTACCACCGCCTCCGCTGGAAAAGTGCAAGACCGTT
GTAATGTTGAAAGGACCCAACAGTCCTTTGGAATGTACTATGCGATCCATTACTCGTGTGGGCTTAAGTAAACGGGTGAATATAGACCATTTGTC
CGTTAATGCACTTCTCCTGGATGCTGATCCTCAAGATCACCACGATCATTTGATAGTGGCCCACGAAATCGCGGAGAGTAGAAACGGGCAGACAC
TGACAGCCCGTGGAACCACCCTGATGCCCAATGTGCAGGGATTCGGTGCTCTAATGGTTATGCTATTTAGTCCCACTATGCAACTTAAATGCAAT
AAAGAAGGCACATCATATGTCTCTGTTCTGGGAGGATTGGGTTGTGACCCGGACACAAACGAGCCCTACTTCGCAGAGCATGACGTGTTGATTAA
TCTGGATGTCAACATTCTCGAAGATGATGTGATTTTGGTGAGCACGCATAGTACGAATATATACAGAATTGCATTAATTTCTGATATTTATTTT
AGATTAATCAAATTCGCTACTATATAGATAGTGTCTTCTTCAACTTTAAGGAAGAAAACAATCCAGCTGTTAGCGTAAATGAACGTGTTTCTATA

FIGURE SHEET 736

TACACTCAGCTGCGTAGCCTTATAAATAGGTAAGATTGCTGCGCTTAAAGTCATGCTAATTAAATGATTTCACTAAATTTGATTTCGCAGGCTCC
TTTGCAAGGATCGTAGATATATCGAAAGAAATATGAGCAATGCGGATTTTGAATGGGAAACCAATCCCGAACTACCACTGCCGAATGAACCTTTT
GGCAAGAGGGCCATATTTCCGATGCACTCACTTACTGAGCTCCAAGAGGAAGACACGGGTCGCTTGGTGCAACTGAGAGAGAACTGCAGCATGTT
GCACAAATGGCGCAACTTGTAAGACTGGTGCTTGTTTACAAGAATATATTGCATTACTTATATTTAACTTATATTTTAGCGAAGGCACTTTAC
CCCATATGACTTGCAAACTGTGCAATCAGTTGTTGGAATCGGTTCCCCAGCTCCGTTTGCATCTCCTGACCATATTGCATCGTGATCGTGAAAAG
CAAATCGACTATTGCAACCAATAAGAATGGTTACATCGTTTAATATGAAAACAGCTGATTTTGAACTTTTTGATTTCTCATTTCTTTTCTTAAAG
GACACACTTCACTTGTTTGGTTTAAAAAAATGACGTATTCATGGAATGAAAACAAGTTTTGAATTGAATCTAAACCTACAGAAATCTTCATTACG
TTAAATATTTTCTATGTTATGTTGAATGATCTCTCTTCGTTCAATTACGAAGTGTAAAATGTGAAATATAATTTTTTGTTAATTACATCTTTAAA
GATATCATTAAATACGAAGACAGCTATACTAACCAGTTCATTACAAGCAAAAATCCATAAACTGCTTGCTGTTTATAAAAATCAAAGCCCTGGGG
CGTGCATGTTCTCCCTTTTTGGGCTCTTTTTTTTATTTAGATTAAACTCACACATTATATTTATGCAACTACAACTACATCGGAGGAATTCTGC
AGCGGCACAGGAGTTGGAGTGTTTGCCTCCAGCTCGCAGATCGTATAATTCTGCATGCGGTTTAGGGGCTTGCTGCACAGCCCACACATCTGGTG
CTTATACACGCCGTATATCTCGAAATTCAGGATGTTGTACAGATCGAACTGGATGGTGGAGGACAGCTGCGTACACTCCACAATTAAAATATTTT
GCTCGTTAAGTTCCACGCTGAAAGGGCATATGGCGTTTATAAAATTGTATATAAAAGCTAAAAAGCATTCTTACCGGAAGTCGTAGTCACTAGTC
TCAATTGGCCATTGATATGGCTTTTTGCGCACGTTGTGCGGTGTTTGATCCTGGTTAAGATATATGAGCACTGGTTCATCCGTGGGCAGGCTGCT
GTTGTCTGTGCGGGCGCGGAAGTTGAAGTAGTTTTGCCCGATATGGACTCGTAATCCATAGTTGGTGGACAGTCCTTGAACAGGCGAAGGCGTAA
CAAACACTGCAATCTGTGGCAATGGCGAACAGTCAGCCACCAGCAGCGTGAGACAGTCGGGACGCACCGCAATCTCTCTGAGATTGATTAGGTAA
TCATCGAAGGTATTGACTATGCCATTGATTACTGAGCAGGAGCGCTTAAGTCCTGAGTCGAAGGTAAGCTCGTGGGAAGCGTCGAACTTCGAGTC
CAGCTTGTAGAAGAAGGGGATCTGATGGAAACGCCACTTCACTCCGTTGACCTCCACAGCCAGCCTGAACTGGTCCTGAGGAGTTTGCATTGATA
TATTTATCTCCTGGCTCATATGCAGACTGTCCACCTTGTCGGCGGATAAGGCGGACACTAAGTGGTCCAGTCGATTCGACCACAGCTCGAACCAG
GCGG
(SEQ ID NO: 1378)

Exon: 1001..1198
Exon: 1256..1498
Exon: 3217..3950
Exon: 4048..4700
Exon: 4790..4923
Exon: 4975..5564
Exon: 5621..5768
Exon: 5836..6972
Exon: 7033..7154
Exon: 7216..7428
Exon: 7492..7934
Start ATG: 1001

Transcript No. : CT10340
ATGGATCAGGAGGTTATGGATTTCTTTGACTTCTCGAAGGAGTTGAAGCGCGTGGCCGCCGCCCCGCAAGGCTACATCAGCAGCGATCCGAGGCT
AATGGCCACGAAGTTCAAATCATCCGAAGTGCCCAACCGCGAGTTGATCGGCACCGACTATGTCAGCAAAATCGTCGCCAAGGAAAAGTGTCTCC
TGAACGGGACGCTGCTCAACGAACAGCCTCAAGGCAAACGCATTCGAACGCTGGACGATTTGGACACCGACGATGAGGGGGAAGAGACCGAAATT
CGCCGGGATGACGAGTACTACAAGAAGTTCAGATTCAATCTGAATCGCGACAAGAACTTGTCCATCTACGCCAAGCGCGAGGAAATATTGGCGGC
CATCAATGCTCATCCGGTAGTCATTATTAAGGGCGAAACAGGATGTGGCAAGACCACGCAGGTGCCCCAATACATTTTGGATGAGGCCTATAAAA
GCGGTAAATACTGCAACATTGTGGTGACACAACCCCGGCGCATAGCTGCCATCTCCATAGCGAATAGAGTTTGCCAGGAGCGCGAGTGGCAGCAG
AACACGGTGTGCAGCTTCCAGGTGGGCCTGCACCGCCCGAACTCTTTGGAGGACACTCGTCTGTTGTACTGCACCACCGGGGTGCTGCTGAACAA
TTTGATTAACAACAAGACGTTGACCCACTACACCCACATTGTGCTGGACGAGGTGCATGAAAGAGACCAGAACATGGATTTTCTTCTGATCGTGG
TGCGTCGCTTGCTGGCCACGAACTCGCGGCATGTAAAGATTATCCTGATGTCGGCCACCATCGATGCCAAGGAACTGTCCGACTACTTTACCACC
ACTAACTCAATTCCGCCAGTGATCACCACCAATCATCGACGTAAGCACTCGATCGAGAAGTTCTACCGTGACCAGCTCGGCAGCATTATTTGGAA
TGAGGAAGATGTGGGACACCAGCAGGTGCCAGAAATCAACAAACACGGTTACAGGGCAGCGGTAAAGATCATAGTGATTATTGACAACATGGAAC
GGAAGGCTGCAATCCAGTCGCGGCAGAGCTATGACGAGGCCCTGCGCTATGGAGCTGTGCTCATCTTTCTGCCAGGCATCTACGAAATCGACACG
ATGGCAGAAAATCTTACTTGTATGCTGGAAAACGACCCCAACATTAAGGTCTCTATTGTTCGCTGTTTTTCGTTAATGACACCGGAAAACCAACG
GGATGTCTTCAATCCCCCGCCTCCCGGTTTCCGCAAGATCATTCTGACCACAAACATTGCTGAGAGCTCCATCACGGTGCCAGATGTCTCATACG
TTATTGACTTTTGTCTTGCCAAAGTAAAGGTAACCGATACGGCTAGCAGCTTCTCTTCGCTCCGCTTAACCTGGGCGTCCAAAGCCAATTGTCGT
CAGCGTGCCGGCCGCGTTGGTCGTCTTCGTAGTGGACGCGTTTACCGTATGGTTAATAAACACTTCTATCAGAGGGAAATGCCCGAGTTTGGAAT
ACCAGAAATGTTGCGCTTGCCCTTGCAAAACTCGGTGCTCAAGGCCAAAGTGCTGAATATGGGATCACCGGTGGAAATCTTGGCATTGGCTCTAT
CTCCGCCGAATCTGTCGGACATACACAATACAATATTGCTTCTGAAAGAGGTGGGTGCTCTGTACTTAACAGTAGACGGCATCTACGACCCGTTG
GATGGCGATCTTACCTACTGGGGCACAATCATGTCTCGGCTGCCGTTGGACACACGTCAGTCCCGGCTTATCATATTGGGTTATATTTTTAACAT
GCTCGAAGAAGCTATTATTATAGCTGCTGGCTTATCGACGCCTGGCTTGTTTGCGCACGAAGGTGGTAGGTCTCAATTAGGCGATTCATTTTGGA
TGCACTATATCTTCTCCGATGGATCTGGCTCCGACTTGGTGGCCATTTGGCGCGTGTATCTGACATATTTGAACATTGTGGAAAATGGTCACGAC
CAGGAGTCTGCTATCCGTTGGGCCAAACGTTTCCACGTCTCCTTGCGGTCACTTAAGGAGATACACTTGTTGGTGCAGGAACTGCGTGTGCGATG
CACGCATCTCGGTCTGATTCCGTTTCCTGTTAATCCTAACCAAATGATGGACGATCGTGAAAAAGCGATCATGCTCAAAGTGATCATTGCAGGTG
CCTTCTACCCAAACTACTTTACGCGTTCCAAAGAGTCGTGTGCAGACACAGATCGCAATATATACCAGACAATATCGGGCCACGATCCCTGCCGC
ACCGTATATTTTACCAATTTTAAGCCTGCCTACATGGGCGAGTTGTACACTAGGCGCATTAAGGAGCTATTTCAGGAGGTCAGGATTCCGCCGGA
AAACATGGACGTTACTTTTCAAGAGGGTTCGCAAAAGGTCTTTGTCACTTTCAAACAGGATGACTGGATTGAAGGTTCATCTAAGTATGTTCCTG
TGTCGGGCAGAGTTCAAAGTGAGGTGTACAAGGCAGTTATGATGCGACAAAATCGTGTCGAACGGCCAATCCACATAATGAATCCGAGTGCATTT
ATGAGCTACGTACAGCAGCGAGGGATTGGAGATGTGATTGAGGGCCGTTGGATTCCACCCACAAAGCCTTTAAACGTCGAGCTTCTTGCGCTGCC
ATCTGTCTTTGACAAAACTATTTCAGGGTCGATTACTTGCATCGTCAACTGTGGCAAGTTCTTTTTTCAACCCCAATCTTTTGAAGAGTGCATTC
GAAATATGTCTGAAATTTTCAATGCTCCACAGCAACTAAGAAATTACGTAACTAACGCGAGTGCCATCGCAAAGGGCATGATGGTGTTGGCCAAA
CGCGATAGTTATTTCCAGCGCGCCACAGTGATCCGGCCAGAGAATCAGAGCAATCGCCAACCAATGTTCTACGTTCGCTTCATCGACTATGGTAA
TTGCACTTTGCTGCCCATGCAGCTAATGCGTTTGATGCCGAGAGAGCTAACTGAACAGTACGGCGACCTTCCGCCACGTGTTTTTGAGTGCAGGC
TGGCAATGGTTCAGCCCTCTTCAGTGGTCAGTGGAAACAATAGGTGGTCCACCGCGGCTAATGATATGCTCAAGACAGTGGCCCAATGCGGTCTA
ATCGATATTGAGGTGTATTCGCTTTTCAATAATGTAGCAGCTGTTCTCATTCATATGAGAGATGGCATAATCAACGATAAGCTAGTAGAGCTTAT
GTTGTGCCGTCGATCCGACGAAGATTATATGTCTAGAAAAGATCATGATTTCCGTTTGCGACGTCAAGAATCTGCCCGGAACTTGAGCACGGCGC AGCGTCAACAGATCAATGAGGAATATCTGCGATCCTGTCAGCTGCCGCAAGACCACGATCTACCACCGCCTCCGCTGGAAAAGTGCAAGACCGTT
GTAATGTTGAAAGGACCCAACAGTCCTTTGGAATGTACTATGCGATCCATTACTCGTGTGGGCTTAAGTAAACGGGTGAATATAGACCATTTGTC
CGTTAATGCACTTCTCCTGGATGCTGATCCTCAAGATCACCACGATCATTTGATAGTGGCCCACGAAATCGCGGAGAGTAGAAACGGGCAGACAC
TGACAGCCCGTGGAACCACCCTGATGCCCAATGTGCAGGGATTCGGTGCTCTAATGGTTATGCTATTTAGTCCCACTATGCAACTTAAATGCAAT
AAAGAAGGCACATCATATGTCTCTGTTCTGGGAGGATTGGGTTGTGACCCGGACACAAACGAGCCCTACTTCGCAGAGCATGACGTGTTGATTAA
TCTGGATGTCAACATTCTCGAAGATGATGTGATTTTGATTAATCAAATTCGCTACTATATAGATAGTGTCTTCTTCAACTTTAAGGAAGAAAACA
ATCCAGCTGTTAGCGTAAATGAACGTGTTTCTATATACACTCAGCTGCGTAGCCTTATAAATAGGCTCCTTTGCAAGGATCGTAGATATATCGAA
AGAAATATGAGCAATGCGGATTTTGAATGGGAAACCAATCCCGAACTACCACTGCCGAATGAACCTTTTGGCAAGAGGGCCATATTTCCGATGCA
CTCACTTACTGAGCTCCAAGAGGAAGACACGGGTCGCTTGGTGCAACTGAGAGAGAACTGCAGCATGTTGCACAAATGGCGCAACTTCGAAGGCA
CTTTACCCCATATGACTTGCAAACTGTGCAATCAGTTGTTGGAATCGGTTCCCCAGCTCCGTTTGCATCTCCTGACCATATTGCATCGTGATCGT
GAAAAGCAAATCGACTATTGCAACCAATAAGAATGGTTACATCGTTTAATATGAAAACAGCTGATTTTGAACTTTTTGATTTCTCATTTCTTTTC
TTAAAGGACACACTTCACTTGTTTGGTTTAAAAAAATGACGTATTCATGGAATGAAAACAAGTTTTGAATTGAATCTAAACCTACAGAAATCTTC
ATTACGTTAAATATTTTCTATGTTATGTTGAATGATCTCTCTTCGTTCAATTACGAAGTGTAAAATGTGAAATATAATTTTTTGTTAATTACATC
TTTAAAGATATCATTAAATACGAAGACAGCTATACTAACCAGTTCATTACAAGCA
(SEQ ID NO: 1379)

Start ATG: 1

MDQEVMDFFDFSKELKRVAAAPQGYISSDPRLMATKFKSSEVPNRELIGTDYVSKIVAKEKCLLNGTLLNEQPQGKRIRTLDDLDTDDEGEETEI
RRDDEYYKKFRFNLNRDKNLSIYAKREEILAAINAHPVVIIKGETGCGKTTQVPQYILDEAYKSGKYCNIVVTQPRRIAAISIANRVCQEREWQQ
NTVCSFQVGLHRPNSLEDTRLLYCTTGVLLNNLINNKTLTHYTHIVLDEVHERDQNMDFLLIVVRRLLATNSRHVKIILMSATIDAKELSDYFTT
TNSIPPVITTNHRRKHSIEKFYRDQLGSIIWNEEDVGHQQVPEINKHGYRAAVKIIVIIDNMERKAAIQSRQSYDEALRYGAVLIFLPGIYEIDT
MAENLTCMLENDPNIKVSIVRCFSLMTPENQRDVFNPPPPGFRKIILTTNIAESSITVPDVSYVIDFCLAKVKVTDTASSFSSLRLTWASKANCR
QRAGRVGRLRSGRVYRMVNKHFYQREMPEFGIPEMLRLPLQNSVLKAKVLNMGSPVEILALALSPPNLSDIHNTILLLKEVGALYLTVDGIYDPL
DGDLTYWGTIMSRLPLDTRQSRLIILGYIFNMLEEAIIIAAGLSTPGLFAHEGGRSQLGDSFWMHYIFSDGSGSDLVAIWRVYLTYLNIVENGHD
QESAIRWAKRFHVSLRSLKEIHLLVQELRVRCTHLGLIPFPVNPNQMMDDREKAIMLKVIIAGAFYPNYFTRSKESCADTDRNIYQTISGHDPCR
TVYFTNFKPAYMGELYTRRIKELFQEVRIPPENMDVTFQEGSQKVFVTFKQDDWIEGSSKYVPVSGRVQSEVYKAVMMRQNRVERPIHIMNPSAF
MSYVQQRGIGDVIEGRWIPPTKPLNVELLALPSVFDKTISGSITCIVNCGKFFFQPQSFEECIRNNMSEIFNAPQQLRNYVTNASAIAKGMMVLAK
RDSYFQRATVIRPENQSNRQPMFYVRFIDYGNCTLLPMQLMRLMPRELTEQYGDLPPRVFECRLAMVQPSSVVSGNNRWSTAANDMLKTVAQCGL
IDIEVYSLFNNVAAVLIHMRDGIINDKLVELMLCRRSDEDYMSRKDHDFRLRRQESARNLSTAQRQQINEEYLRSCQLPQDHDLPPPPLEKCKTV
VMLKGPNSPLECTMRSITRVGLSKRVNIDHLSVNALLLDADPQDHHDHLIVAHEIAESRNGQTLTARGTTLMPNVQGFGALMVMLFSPTMQLKCN
KEGTSYVSVLGGLGCDPDTNEPYFAEHDVLINLDVNILEDDVILINQIRYYIDSVFFNFKEENNPAVSVNERVSIYTQLRSLINRLLCKDRRYIE
RNMSNADFEWETNPELPLPNEPFGKRAIFPMHSLTELQEEDTGRLVQLRENCSMLHKWRNFEGTLPHMTCKLCNQLLESVPQLRLHLLTILHRDR
EKQIDYCNQ*
(SEQ ID NO: 1380)

Name: DEAH-box helicase
Classification: RNA_binding
Gene Symbol: spn-E
FlyBase ID: FBgn0003483

Celera Sequence No. : 142000013384633
TGTCCCGCTCCCGTATCCAAGCATTGTCGCTTGATAGTTCCCCCAGGAGCATGTTGCCCCCTGTGTGCTGGAGGAGCCTTCAGGATAATCTACTC
CAGAAAGCAATTCGATCGCGCCATGTACGGACTAAGGGCACAGAGCAGCACTCTTTTGACATTGCAAGGAGTGCTGCAGCAGCTGGATGGACTGG
TGCAGGTTAGCGAATGTCAACTGACTGGATTTCTCACCATGGAAGTGGGCATTTTTGTGGCCATAGTACCGTCCAGCAGTATCAAGAGACCGACT
CACCTTCAATTGGAGGCCTGCGCCCGGGAGGCGGAGAAGATATCCTCCCTAATCAATGCCCAATCACCCAGAATTACAACCAATCTAGCTCTATC
CTGTTTGACAGTATCGCATCTACTAGAACCCACGCCAAATGGAGCTACATCTTATGGTCCCCACGCCATTTGGATACTCCCCTTACTTTTGTTAG
TTTCTAGAGTAATCATAGCTTAAGATAGTCCTAGAAGGAGTGTGTATGATCTGACTCAATCAAGTGAATTCTTGGTGCCAATTAACCCGTTATTC
TAAGGAGATGGAAAGTGCCTTCAACTGTAAGGAATTGACCCTCTGTACCATGTGATATTAGCTAAATTAATTCTTAAGCTTTAATGTTCTTTTAT
AGTTATTATTTAATTTATGCCAGGGTCCGTAAATCACCAAAACCCCCTTTTTGTTTTACCTAATTTAAATGTATTTAATAATTCAAATCATTGCT
CCATGGTAATATTTAAATTTAAAATAATTATTTAAAATCTGGATCGTAAAAGTACAAAGAGATTGATGGACCAAAACTCGACACTGTGCCCTAAC
CATGTGGAAACATTCTTAAATTTGGAAAACATTGTAATATAATTATTTTTTGGTCCCTGGCTAGGAGTTCGTTAATGACCAAAGCATTGTCCGCC
TAGGAGTATCGCTAGTCTAATAAAAACCCCAGAAAAAAACACAGCAACTTAAGATGAAGCATGGCTTCCTTTATTGAACCACTCCATATAGATCC
TGCCGAAGCTTTATTATAATAAATGTACGAAAAGGGTAGAAAGGGGAATCGCTTTAAGAAATCTCCATGGGCACCGCCTGGACGCGTTCGGTGAC
GAGTAGGTCCTTAATGTTGGTGTGCAGCACGGTTGAGGTTCCGGTCTTGAAGCGGTAGTCCAACTGGCGCTTGCCCTTCTTGTTAGCCAGCTCAT
AGTTGCGCAGATACTCAACACTGCCCTTGCGGATAACACACAGATCGATGTTGGATCCCGAACCCAGATCGTTAAACACTCCGGAGGCGATGGCA
TCGCGCACCAGTTTCTTGCCCTCCTCTTCGGACAAGTCAGGTTTCCAGCGACTTTCGAAAACGGTCATGGCGGCCAGGGAACCCGATCCCATGGT
GGCGTACGGCAGCTTATCCGAACTTCCATGTGGGTGAATGGAATAGATGTGGGGTCCAGTCTTATCCACTCCACCAAGCACCAGAGCGGCACTGA
TATGACCCTGGTAGCGGAAAAGCATCTGCTTCAACATCGTATTGGCGGCCACAACGCGCACCTCACGATCTGTCTGCAAGCGATGCAGCTCCAGC
TGGGAGGAGATGAGATCCGTAGTCATCTCAGTGTCCGCAGCGGTTCCAGCTCCACAGCAGCTGAAGGTAAATATTTTCGTTAGGTATTGGGAGAT
ACTTGCATGTTAGAAAGTACACATATTTTTAAGTTAGAGCAACATAAGCTACACCCTAAGATCCTCAACTTAAAACACGGGCCCCTTAAAATTGG
AGACAAATTGATCTAAGCCGGCGAGGACAAGGAAATAGGCCCACATTTGAAATGCAGGAAAAAATACCGTAATCCCTCTTATAGTATTATTAGGT
TCCCTGTGCACTTAAAGGCGCATACCGTCGGTGGACTTACTATATGTTTTTGGCCAGGTAATGGATCTTGGCGCAGTTCTTGTCCGAGACAATGG
GTCCCTCGGTGGCTCGCGTATCGGCGCCCAGAATAACACCATCCTTGTAGATGATGCCAACGATTGTGGTTCCCGTCTTGGTGGTGGTCGGTGGC
TTGAAGCCTCGATTCAAAAGAGTTGCATTGCTGAAAGCAAATAAAACACCAATTAATAAAAGCCGATGGGGTATTGCTGAACAACTTGGACGATT
CTTACCGCTTGCAGTTGTCGAAATTGAAACCAGCGCGGGGCAGATCGCGTGCGTTATCCAAATCCATTATATATATTCTTCAATTCAACTATATT
AGCAAGGAAAACTAAGGTTTTAATTCTGCCGAGCGCGATGACAAACAAAATTGTTAAATGCTTGCTAGAGCTGGAAGTACAATCGATATTGTATC
GATATATATTCATGGACTCAACTAGAGCGATAGTATTGAAGAAATAAATTATTAATAATTTGACGTTATTAATAATTTGACTTATGTAACTTAAA
TTATTCAATGTTGTATTATTTTAATATTTTAATGTTGCATTGTATAATTTTAAAACTTTTTAATGTTTGGAAATATTCCCCGCAGTATACATGCA
ATAAGTGCTTAGGAAGGCCCCTTATCTTTTGTAAGCGAATAGTCATGTTTGAAAAAATATCGATATACTGTTTCCACCTGACCATCTTGGCATAGT ACCATCACTTTTGTGAACTGCATCCCTGAAGAGTATTTTGGTAATTTACCATGTCTGCGGCCACCAAATTACATAAAACAAGCTGGTGCGCCCTG
CGGCAGCTTCAACAATACAGAACTAAGGGTAAGTAACACTAATTAGGAGTCCTTTTATTGACCAAAGATGGAGGAAGTGGTTTACATAATGCCGG
CAGTCATTCACGTTCCGCGGAGCTCTTCGGCTAGTGATGGCAGTTCGTTGATGTCTTGGCGGAAAAATCGCTAGAATTTCTATAGATCCCAGTTA
TTATTTTAGATAGTCAACCATAATTTAAATTCAATTTGTTGAAACTGTACTATAAAATATGTCTTTTAACTTATTAATTATCCCTACAGCCAACT
TTAGTGGCAGTTCTGCATCGTTAGCCAAGCGGAATGACCTGTTCAACCAGGAGCAGCGCCGTCAACGGGATGCAGTGGGTCGAATCGATAAGATC
GAGGTGCGGTATCTGGGACTTCCCGAGGATGTCACTCTGGTGATGAACGGCAACATCTCAACGCCCCTCAATTGCGCCCAGCATCTGAGTGAGGG
GCACTGTAAGCGATCGGCACTGGCCTTGATCGACGGCAGTGTTCCCTGGGATATGCACAGACCCTTGCAGGAATCCTGTACTCTGCAGCTGCTTA
ACTTCCATGTTTCCGAGCC
(SEQ ID NO: 1381)

Exon: 2344..2191
Exon: 2120..1941
Exon: 1675..1001
Start ATG: 2252 (Reverse strand: CAT)

Transcript No. : CT10524
CAAGCATTTAACAATTTTGTTTGTCATCGCGCTCGGCAGAATTAAAACCTTAGTTTTCCTTGCTAATATAGTTGAATTGAAGAATATATATAATG
GATTTGGATAACGCACGCGATCTGCCCCGCGCTGGTTTCAATTTCGACAACTGCAAGCGCAATGCAACTCTTTTGAATCGAGGCTTCAAGCCACC
GACCACCACCAAGACGGGAACCACAATCGTTGGCATCATCTACAAGGATGGTGTTATTCTGGGCGCCGATACGCGAGCCACCGAGGGACCCATTG
TCTCGGACAAGAACTGCGCCAAGATCCATTACCTGGCCAAAAACATATACTGCTGTGGAGCTGGAACCGCTGCGGACACTGAGATGACTACGGAT
CTCATCTCCTCCCAGCTGGAGCTGCATCGCTTGCAGACAGATCGTGAGGTGCGCGTTGTGGCCGCCAATACGATGTTGAAGCAGATGCTTTTCCG
CTACCAGGGTCATATCAGTGCCGCTCTGGTGCTTGGTGGAGTGGATAAGACTGGACCCCACATCTATTCCATTCACCCACATGGAAGTTCGGATA
AGCTGCCGTACGCCACCATGGGATCGGGTTCCCTGGCCGCCATGACCGTTTTCGAAAGTCGCTGGAAACCTGACTTGTCCGAAGAGGAGGGCAAG
AAACTGGTGCGCGATGCCATCGCCTCCGGAGTGTTTAACGATCTGGGTTCGGGATCCAACATCGATCTGTGTGTTATCCGCAAGGGCAGTGTTGA
GTATCTGCGCAACTATGAGCTGGCTAACAAGAAGGGCAAGCGCCAGTTGGACTACCGCTTCAAGACCGGAACCTCAACCGTGCTGCACACCAACA
TTAAGGACCTACTCGTCACCGAACGCGTCCAGGCGGTGCCCATGGAGATTTCTTAAAGCGATTCCCCTTTCTACCCTTTTCGTACATTTATTATA
ATAAAGCTTCGGCAGGATCTATATGGAGTGGTTCAATAAAGGAAGCCATGCTTCATCTT
(SEQ ID NO: 1382)

Start ATG: 93 (Reverse strand: CAT)

MDLDNARDLPRAGFNFDNCKRNATLLNRGFKPPTTTKTGTTIVGIIYKDGVILGADTRATEGPIVSDKNCAKIHYLAKNIYCCGAGTAADTEMTT
DLISSQLELHRLQTDREVRVVAANTMLKQMLFRYQGHISAALVLGGVDKTGPHIYSIHPHGSSDKLPYATMGSGSLAAMTVFESRWKPDLSEEEG
KKLVRDAIASGVFNDLGSGSNIDLCVIRKGSVEYLRNYELANKKGKRQLDYRFKTGTSTVLHTNIKDLLVTERVQAVPMEIS*
(SEQ ID NO: 1383)

Name: 20S proteasome beta2 subunit
Classification: endopeptidase
Gene Symbol: Prosbeta2
FlyBase ID: FBgn0023174

Celera Sequence No. : 142000013384528
AGATATATACTAAATGTGCATGTGTATATATAATATATATAAACATATTTGAATGATCGCAAAACGCTTTAATCAATGTTGCTTCTAGGTTTCTT
TTTGATGCGCGCCTCGTCAATGAATAATTACGTCATATTCTTTTATTAGTTTCTGATACAGTTGGGATTATCAACTAGGTTACTCTCACGTACAC
ACAAACACGGAACACTTGAGTAGCCTCATGGCCTGCTACTTGCTACTAGCTACTTCCTTCCGAGGTCGTGGCACTCGCTTTTCCACAGATCTTCC
GACGCTTTTCACTTCGCGCACAGATTTCTCAATGTAGTATCAGTGAATATATGTATATATATTATATATAATATATATATCAACGCGACTGTATA
TTATCAGATTTTTCAAAGAAGCCGACGCTTTTCCTCCTTTATCGCCAACGCGTCTAATTCCCGGATCACAGCTCGACACGTCCGCTCTGTTCGCG
ATCCAAGCTCAAACTGAGCGGACATAACAGCCGGATGGTTGGCCTTGCTGGAGGTTTCGTTGATAAGAATCATGCTGCGAAGAGCAGCTTGGCAG
CTGGGCTCTCTTACGATCTCTTGGGAAATGTCCTATAAATAGATTTTTGCCGCGTCCACTGGAACAACGTCTTACGGACCAGAAAACGGATTCTC
AAATCTGATACATTCTGTTTAGAGGATTTTAAGATATCTTGCATAACATTATCTTACAATATTCCCAAGGACAATTTCGTATCCCTTCAAGACTT
AATAATTTAATAAGGACTAGAAATACACAATATTGCGCTATTTATTTGGTACCAGACACATTTAAATTATATTAAATCTCGCGGATTGTCTATAA
AAATCTACGTTATTTATTAGTATAAGAGTAGCATATAAGGTTACTTATAGACGAACTAAGACTTTGACGAGCTGCTCTCATACGTATAACAATAC
ACCACAAATCACATGGAATCAGGAATATCAGAAACTACTCTGTATGTCACTTAAGGCTAGCGTGCTCCCCCATGAGCATGTCCTGCCCTGAAGTG
GGCACCACCCGTTCCAGTACCACTTGGTCCTCCTGCTCCTCCTGCCCTGCGTTTCTCCGATCCCGATTCTGCACTAGCGTCTCCGTTATCAGAAC
CACCACTCTGTTCTGCATCTAGATTCTTGAGTTGCTGTTGCCACATGTCCGCGTAGATGCCATCTTCGCGCAGCACAAGCTCTTCGTGTCGCCCA
CGCTCCGCTATGCTTCCCTGCTGCAGGACCAGAATCTCGTCCGCATGGATGATGGTGGAAAGACGATGGGCAACAATGATGGTGGTACGATTTGC
GCACACCCTGGCCAAAGCAGCCTGAATATTGCGTTCTGTGTGGGTGTCCAAAGCTGAGGTGGCTTCATCCAGGAGCACAATAATGGGCGCCTTAA
GAAGCGTTCTGGCGATGGCTACGCGTTGCTTTTCACCTCCACTGAGCCGCAGACCTCGTTCGCCCACCTTTGTCTCATATTTCTCCGGAAAGCCG
AGAATCCTTTCGTGAATGTCGGCGGCGCGAGCAGCCTCATAGACAGCTTCGTCCGAAGCGCCCAACTTGGCATATTCAATGTTGTAGAAGATGGT
GTTGTTAAAGAGAACCGTATCCTGGGGCACCACTCCAATGGCCTTTCGCAGACTCTGCTGCTGCACAAGCTTGATGTTTTGTCCGTCAATCAGGA
TAGCACCAGTCTGCACATCGTAAAAGCGGAAAAGCAGCCGCATGATGGTGCTCTTACCGGCTCCAGAGGGTCCAACAATCGCTACCGTCTTACCG
GCCGGAACTGTGAAGCTCACATTGCGCAGCACTATCTTCTCCGGTGAATAGCCAAAGGTCACGTTTGAGAACTCAATGCCACCGCCGGCAGTTAG
AAGGGGCGAACAGCCTGGGGCATCCACAATCTCTTCCTCCTCTTTCAGCAGATCGAACATGTTCTCCATGTCCACGAAGTTCTTCTGTATGGCTC
GGTAATAGGTGCCGAACCAATTCAGTGGCATGTACAATTCCATCAGATAGGTGGAGAAGAGCACAAAATCGCCCACGGTGAGGGTTTGATGGTGA
ACTACCAAGTATACACAGAGCAGCGATCCGGCCAGTAGGCCCAAGCACAAAATAATATTCTGGGCTGTGTTCAGCATGTTGAGTGTCAGCATTGA
GAGGAACTCTTCCCTTTTGGTACTTGAGAATGGCCTCCCTGTAGCAATCCACCTCGTAGTGCTCCGCTCCGTAGTACTTGACTGTTTCGAAATTGA
GAAGGGAGTCCACGCTGCGAGCTCGCTGCTCATTGTCCGCCAGGTTCATTCTCCTCTGGTACTTGGTTCTCCATTCAGTGATTGCAATGGTAGAG
GCTGTAAAACGGAAGGATATTTTGAAATACGAATGGAATTAATCGAATAATTTTTATCACTTACCTATATACAGGAACATGGTGAGGAAGACGAT
TAGGCCAAACCACCAATTGAAGGCGTAAACAAAGTATGCCACGGCAACGAGTAGATCGAGAATGGTTGGTGCGATCGAGAAGACAATATAGTTGA
GGAGGTTGTTGATCGAGTCCGTGCCGCGATCCATGACACGCAACACCTCTCCCGTTTTGCGTTGCAAGTGCCATCTAAGCGAAAGCTGGTGCAGA TGCCGGAACAGCTCAATCTCGATCTCCCGGGTCGTGTACTGTTGAACCCGTATCCAGAGGAAGGTGCGAAGGTTATTAAATAATCCCATGCTACC
AGTGCCGCCACCCTGGAGGAAGGACAATGCCACATAGATCAGCACAAAGTCCCAGCGAAAGACGATCGGTGCAATGGTAAGACTGTCAACTGTCG
AAACAGGAGATTAGCAATGAATTACTTAACGAATTACGTTCATAATTCTTGACCTACCCAACTTCTTGCGATAAATCGGCAAAAACAGCTTTATG
ACTCGACCGGCAAGCAGCAGTATAATGCAAACGATGACGGCTATCTGCAGAGCAATATTCTTTTTAGGCCAGAGGTACGGAAAGACGGTGCGCAG
CTTGCGCCATCCGTTCCTGAAAGCAGATCCTGTCTGCACGTTTCCCTGCGATTCGTTGGCGGTATCATTGTCCAGCCGCTGATGTGGATTGTACG
GGGCCATGATGCCAGGAGCTTTCAGACCCAAAACGAAGATGAGCAGGGAGCACAGGAACCGGGTGACAAACAAGCCCATCTCAATTTGATCCTTG
TTCCTGCGAGTAGTAAAGGCGGTACTATAGATTATCCGTTTTACAGCCGTTTGCATTACTTACGTTTTTAGGTGGAACCACCAGTCCTCGTGGCG
CAAATTTATGAAGGCCAGCGACTCGTTAATGAAAGCCAACGTCCAGAATAGCAATAGAACAAGTCCATGTCCTCGGGTGGGCATTGAGGGCAGCT
GGTAGTAGCGCTCCTTGAGTATCAAACAGATGCTGAACGGGTAGGAGAAGCACACAACGCAAGTGGAGAAGATCTGCAGAAAAGATTTCGATCAG
TAATTGTTTCTTCTTGATCATTTTCATACTTACCATATAGCCGTACACCGCACTATCTGGATAAATACGTGCATTCATCAGAAACCGCAATAGAG
CCAAAACCGGGAGCAGGAGCAACAGAAAGAGTTGCATCGCGAACAGTCGTGACTTGGAGATTTGCGTGGGATCCGTAATCCTGGTGGCATACTTC
CGGTACATCAGCAACTGAATGCTGCCGAAGAGCAGAAGGAATCCACCGTATACCGCCGGTCCCACGGTGTCCATGAAGCAATGCGAGATGCCATG
CTGCGTCCACACCTCGCTGAGGGTCACGTTGGGCGGGCAGTACAGCATGGTGAAGTCGGTGTACCTGCGCGGCGACGAGGAAAGGCAATTGCGGA
ACGATAAGCTCTGATAGAAACGTGCCAGATAAAGTGGAGCTGTCACTGGGAAACAGCTCGGTGAACACAATTGCTTTGTTTTATGGGCTGGCGGC
AATTTCGCAATTATTCACCCAAATTATCAGACGCCCCCAAAGGGGAAATCACTATTTTTTTCCTCCGGGTAAGCGGAGTGCAGATTGTGAATTGA
TAATTGGTGCCCTTGCAGCACGGCACCAAGAGATCCGAAATACCCTGGAGTCCGGCAACCGTGGAAACTGCAACTCATCCAGCCCATTGGATATG
CTAAATTATGCAATGTTGCGTATGCTCGATTCGCCGGCGGGTCTAGTGCTCCCCTCTTACCCGCTATAAGAAGTCGCGATCTGGTGGAAACACCG
CAATCAGTCGTGTGACAGGTGATAACTCAACTAATGGACAACTGGCGGGCAACTCCGACCCAATCACCACCAACTACGATCAACATAAATAATTT
TGACCCAAGGGTTCGGTATGGCCGTTTCTGCTTACACACAACATACCACATACACATTGTACAGTGGAAACAGGTGAGATTCATTTAAATGAACA
TAGCTTAATATATAACATTTTCGATTGCTATAATAAATTCAGGGAGAGTTTGTTTAAGTGATTTAATTTTAAGCTATCAAAGGTTTAAAGTAATT
CTCTTATCAAATTGAAGGTAACAAATTTTCTGGAAACGGTCACGCTAGCTTTCAGCCCTGGTTTTCAGCTTGGCGCCCAGTTTTCAAACCATTTT
CTTATCAGAATTTGCGATTACTTTACCATTCCTGGTTTTCAACACACCATCTTATCAGAAATTGTGATTATTTCAATATTCCTTGTTTTTAAAAC
CCTATTTCGACATACTGCGGGTAAAATATACAGATTATATAGATTTCTTTATTCGTCAATTCTCAAAATAAATATTCAATGTTCATCTAATACTT
TACATTCAAGAAATTTTCACAAATTGTCTACGCTTAACCTTAGGTAATAACTAAGCTAAGTTTTTGAGTTTGTAGAGAATGAATATTCAAAGCAC
AAGGAACAAATTGATTGGGAGTAAGTTTCTATTTACATCTAGAGTTGCCTTTTTTGTTTTTATTTTTGTTTAATTTGAGGTTTGGTTAAATATAA
AATTCGCTACTTATGAGTAAGGGGATGGGGCGATTAAAACCTAGGAAACATTTTAGAAGATTTCCCGTACGAATTTCGAATTTGATTCGGTCGAC
TATTGACTAACCACTAACTTGTTCAACTTGGGTTTAACTTATTATCACAAACAAGTACATTTAATATGCATATGATTACAGTGAAGAGGGAGTCG
ACTCCCCCCCATACAGCTATGAGTTGATCTTGGCCAGCAGTGGCTGGGTGACGGCACTGCCCGCCACCGGTGGGCACTGCTGCTTGTAGCTCTTC
ACCAGGAAGCCGTAGTGGCTGCTGTCCGCCGGAATGTTCTGGCCACTGCCGCTCCGTTGCGGA
(SEQ ID NO: 1384)

Exon: 4383..4238
Exon: 3865..3549
Exon: 3493..3294
Exon: 3233..2908
Exon: 2844..2440
Exon: 2376..1001
Start ATG: 3848 (Reverse strand: CAT)

Transcript No. : CT10897
AACCCTTGGGTCAAAATTATTTATGTTGATCGTAGTTGGTGGTGATTGGGTCGGAGTTGCCCGCCAGTTGTCCATTAGTTGAGTTATCACCTGTC
ACACGACTGATTGCGGTGTTTCCACCAGATCGCGACTTCTTATAGCGGGTAGGTACACCGACTTCACCATGCTGTACTGCCCGCCCAACGTGACC
CTCAGCGAGGTGTGGACGCAGCATGGCATCTCGCATTGCTTCATGGACACCGTGGGACCGGCGGTATACGGTGGATTCCTTCTGCTCTTCGGCAG
CATTCAGTTGCTGATGTACCGGAAGTATGCCACCAGGATTACGGATCCCACGCAAATCTCCAAGTCACGACTGTTCGCGATGCAACTCTTTCTGT
TGCTCCTGCTCCCGGTTTTGGCTCTATTGCGGTTTCTGATGAATGCACGTATTTATCCAGATAGTGCGGTGTACGGCTATATGATCTTCTCCACT
TGCGTTGTGTGCTTCTCCTACCCGTTCAGCATCTGTTTGATACTCAAGGAGCGCTACTACCAGCTGCCCTCAATGCCCACCCGAGGACATGGACT
TGTTCTATTGCTATTCTGGACGTTGGCTTTCATTAACGAGTCGCTGGCCTTCATAAATTTGCGCCACGAGGACTGGTGGTTCCACCTAAAAACGA
ACAAGGATCAAATTGAGATGGGCTTGTTTGTCACCCGGTTCCTGTGCTCCCTGCTCATCTTCGTTTTGGGTCTGAAAGCTCCTGGCATCATGGCC
CCGTACAATCCACATCAGCGGCTGGACAATGATACCGCCAACGAATCGCAGGGAAACGTGCAGACAGGATCTGCTTTCAGGAACGGATGGCGCAA
GCTGCGCACCGTCTTTCCGTACCTCTGGCCTAAAAAGAATATTGCTCTGCAGATAGCCGTCATCGTTTGCATTATACTGCTGCTTGCCGGTCGAG
TCATAAAGCTGTTTTTGCCGATTTATCGCAAGAAGTTGGTTGACAGTCTTACCATTGCACCGATCGTCTTTCGCTGGGACTTTGTGCTGATCTAT
GTGGCATTGTCCTTCCTCCAGGGTGGCGGCACTGGTAGCATGGGATTATTTAATAACCTTCGCACCTTCCTCTGGATACGGGTTCAACAGTACAC
GACCCGGGAGATCGAGATTGAGCTGTTCCGGCATCTGCACCAGCTTTCGCTTAGATGGCACTTGCAACGCAAAACGGGAGAGGTGTTGCGTGTCA
TGGATCGCGGCACGGACTCGATCAACAACCTCCTCAACTATATTGTCTTCTCGATCGCACCAACCATTCTCGATCTACTCGTTGCCGTGGCATAC
TTTGTTTACGCCTTCAATTGGTGGTTTGGCCTAATCGTCTTCCTCACCATGTTCCTGTATATAGCCTCTACCATTGCAATCACTGAATGGAGAAC
CAAGTACCAGAGGAGAATGAACCTGGCGGACAATGAGCAGCGAGCTCGCAGCGTGGACTCCCTTCTCAATTTCGAAACAGTCAAGTACTACGGAG
CGGAGCACTACGAGGTGGATTGCTACAGGGAGGCCATTCTCAAGTACCAAAAGGAAGAGTTCCTCTCAATGCTGACACTCAACATGCTGAACACA
GCCCAGAATATTATTTTGTGCTTGGGCCTACTGGCCGGATCGCTGCTCTGTGTATACTTGGTAGTTCACCATCAAACCCTCACCGTGGGCGATTT
TGTGCTCTTCTCCACCTATCTGATGGAATTGTACATGCCACTGAATTGGTTCGGCACCTATTACCGAGCCATACAGAAGAACTTCGTGGACATGG
AGAACATGTTCGATCTGCTGAAAGAGGAGGAAGAGATTGTGGATGCCCCAGGCTGTTCGCCCCTTCTAACTGCCGGCGGTGGCATTGAGTTCTCA
AACGTGACCTTTGGCTATTCACCGGAGAAGATAGTGCTGCGCAATGTGAGCTTCACAGTTCCGGCCGGTAAGACGGTAGCGATTGTTGGACCCTC
TGGAGCCGGTAAGAGCACCATCATGCGGCTGCTTTTCCGCTTTTACGATGTGCAGACTGGTGCTATCCTGATTGACGGACAAAACATCAAGCTTG
TGCAGCAGCAGAGTCTGCGAAAGGCCATTGGAGTGGTGCCCCAGGATACGGTTCTCTTTAACAACACCATCTTCTACAACATTGAATATGCCAAG
TTGGGCGCTTCGGACGAAGCTGTCTATGAGGCTGCTCGCGCCGCCGACATTCACGAAAGGATTCTCGGCTTTCCGGAGAAATATGAGACAAAGGT
GGGCGAACGAGGTCTGCGGCTCAGTGGAGGTGAAAAGCAACGCGTAGCCATCGCCAGAACGCTTCTTAAGGCGCCCATTATTGTGCTCCTGGATG
AAGCCACCTCAGCTTTGGACACCCACACAGAACGCAATATTCAGGCTGCTTTGGCCAGGGTGTGCGCAAATCGTACCACCATCATTGTTGCCCAT
CGTCTTTCCACCATCATCCATGCGGACGAGATTCTGGTCCTGCAGCAGGGAAGCATAGCGGAGCGTGGGCGACACGAAGAGCTTGTGCTGCGCGA
AGATGGCATCTACGCGGACATGTGGCAACAGCAACTCAAGAATCTAGATGCAGAACAGAGTGGTGGTTCTGATAACGGAGACGCTAGTGCAGAAT
CGGGATCGGAGAAACGCAGGGCAGGAGGAGCAGGAGGACCAAGTGGTACTGGAACGGGTGGTGCCCACTTCAGGGCAGGACATGCTCATGGGGGA
GCACGCTAGCCTTAA
(SEQ ID NO: 1385)

FIGURE SHEET 740

Start ATG: 164 (Reverse strand: CAT)

MLYCPPNVTLSEVWTQHGISHCFMDTVGPAVYGGFLLLFGSIQLLMYRKYATRITDPTQISKSRLFAMQLFLLLLLPVLALLRFLMNARIYPDSA
VYGYMIFSTCVVCFSYPFSICLILKERYYQLPSMPTRGHGLVLLLFWTLAFINESLAFINLRHEDWWFHLKTNKDQIEMGLFVTRFLCSLLIFVL
GLKAPGIMAPYNPHQRLDNDTANESQGNVQTGSAFRNGWRKLRTVFPYLWPKKNIALQIAVIVCIILLLAGRVIKLFLPIYRKKLVDSLTIAPIV
FRWDFVLIYVALSFLQGGGTGSMGLFNNLRTFLWIRVQQYTTREIEIELFRHLHQLSLRWHLQRKTGEVLRVMDRGTDSINNLLNYIVFSIAPTI
LDLLVAVAYFVYAFNWWFGLIVFLTMFLYIASTIAITEWRTKYQRRMNLADNEQRARSVDSLLNFETVKYYGAEHYEVDCYREAILKYQKEEFLS
MLTLNMLNTAQNIILCLGLLAGSLLCVYLVVHHQTLTVGDFVLFSTYLMELYMPLNWFGTYYRAIQKNFVDMENMFDLLKEEEEIVDAPGCSPLL
TAGGGIEFSNVTFGYSPEKIVLRNVSFTVPAGKTVAIVGPSGAGKSTIMRLLFRFYDVQTGAILIDGQNIKLVQQQSLRKAIGVVPQDTVLFNNT
IFYNIEYAKLGASDEAVYEAARAADIHERILGFPEKYETKVGERGLRLSGGEKQRVAIARTLLKAPIIVLLDEATSALDTHTERNIQAALARVCA
NRTTIIVAHRLSTIIHADEILVLQQGSIAERGRHEELVLREDGIYADMWQQQLKNLDAEQSGGSDNGDASAESGSEKRRAGGAGGPSGTGTGGAH
FRAGHAHGGAR*
(SEQ ID NO: 1386)

Name: ATP-binding cassette transporter
Classification: transporter

Celera Sequence No. : 142000013384529
GCTTTGAACTTCATCACGCGCAGGCTGCCCGGGAACTCGAGGGACAGCTGCTTGGTACACTTGGTGGCGATGTCAAAGCGAGCCGTATCCAATGC
CGCGATGATCACCTGCTCCAGGATGAGATGCCGCTCGTTGCCGGTCTTGTGCACCTTGTCCTCTAGCACAGCAACCCACAGCTGGACCACCTCCT
CGCTGTGGCGACCCGTCTCCTCGCGCCACGTTCTGAACTGATCCCGTACATCTGAAAGGATGATCATACGCTTATGATACGGCACTTTTCATTCA
TGGCAATTGGGAGCAACCCACTGACGTGGTCTGCACCTGTCTGGAGCCGGGAAAAGCCGAAAACTTACCCGACCAGCTCATCTTCTCATAATCTA
GCGACATATTCACTTAGGCGGACTTAAATATCTCATCAATTTAATTTAATTTCCCAATTGTAATCATTAACTAGCGATTTCCTTCTTGGCAAAAT
AAAAGTGTGGCAGCGTAATGAGCCGTTAGATTATACCAAATAACACTAGCGTGGCGCTGCCAACCTGCTTTTTGAATATCGTAAAGTCTAGAAAT
GAAGTCAGAGGTAATTTTTTAAAACTTTTTATTATAAAGAGACTTCTAAAGTTAAGTTTTTCTACATATACCTTGTTTCCGATATTTGCAAAGTT
AATTAAACTGTTAATACTTCTGAAATACTTGTAGGTCCTTGAAAAGGATTCTTTAATGAATTATTTTACCATGCATTAATCTTATTTTGTCCAAA
CTTTGTGCATTGCTTATCCATTTTAACAGATTTCTAAGTCAAGTGCACATTTGAAAAGCGCGCCAACGAAAACATGAAACATGATAGTTTTTCTT
CCAGCGACGGTCACACTAACAAATCAAATAATTGTGGTACCGTCAACAAAAGCCAAGTCTCTCGTGCTCTCCGGGTATTAAAGCCGTGGAATCGG
GCAGTGCCGCATGCGGTGCTGTGTTTAATTTCCCCAACTCCCAACAGATCCGGAAGCAGTTTGAACATGGGTCCGCCAAAGCAGCTGAAACGAAC
CTTTCTTGGCTTCGACTTGAGCACGCAAAAGGTGAGAACTGGAACTGCCTACGTAGTATCTTTGCATCTGAGATGTGGAGGCGTCTCCAAATCGA
CTACATCTGGGCCAATTGCGTGCGAATGGTGTTACTGGAAAAGGTCAAACGGTACTCGGGAACTTGAAACACGAACTACTCTTATCAGTTGCGGT
GACCGGGGCTCGATTTTCGCTTATCTGCTAAAGACGCGAGCGCCAACCGATTTAACTATTATGGTTTGATTATTGAAATTCATGTTCGGAGGTAT
TGGCCCCCGACATTATCTTAATAGAGCCGCAATAACTTTCACAATCCCTGAATGACGCTGGCGGTGACTCCTAGTTGCCCTCTATGTTTGATCGT
TATTTTCGAGGTGTGTCTCCATATCGCTAATTGCTGCCCCATTTACTCCTCTCAGCTCAAAGCCGTCCTGCTGGGCTCCAGTTTGGAGGTGGTTG
CCGCGGCTGAAGTGAAATTCGACACCGACTTGCCGGAGTTCCGGACCACCGGTGGAGCCAACGCTGGATCCATCAAAAATGAGTGAGTCTGTTTC
ACCACTATCCATTACTCCAATTGAAGATTTTAATGGGATGATTGTTTGCGTAAAGCAAATAGGGGGATATATTTTACGTTTTTATATCTTGCGCT
GTGGGGTATTTGTCCGATAATACTTAGGGCCCTATTTCATAGCAGTTGTTTTATTACACCACAATGGGTCTCTATCACTTCAAGTTTTTTTTAAC
CTTCCTATAACAGGGACCATATATACAATGGGTACTATAAAATATATATGTGCTAACCTGACTCCACCTTTACTTGTTCTTCTTTAGATACTTTG
TACAACCAGTGATGTGGGTGAAGGCCATGGACATTGTCCTGGACCGACTGGTTATGCAGCAAGCGGATCTTAGCACCGTAGCTGCCATCAGTGGC
TCCGGACAGCAGCACGGATCGCTCTACTGGTCCAAACATGGAATCAACACGCTGCAAAACCTCGATTCCGAGAAGTTCCTTCACGCACAAATCGA
CGACTCCGCCTTTGTGGTAAATCGTACTCCGATTTGGATGGACGCCACCACCACCAAACAGTGCCTAGAGATGGAGATGGCTGTTGGTGGCAAAC
TTAACATGGTGGAACTGACGGGCTCGAAGTGCTACGAACGTTTTACGGGTCCCCAAATTAGAAAGATATATCAGCAACGCTGCCACGCCTACGAA
GAGGCCAACCGAATCTCATTGGTCAGCAGTTTTATATCATCGCTATTTCTGGGCTCCGTCGCTCCAATTGACTTCAGTGATGGTTCCGGCATGAA
TCTGCTGGACATCCGCAAGAAGAACTGGTCCAAAGAATGCCTAAATGTTTGTGCACCCGATTTGGACAAGCGCCTGGACATTCCGGTCAGTCCAA
ATTCGATTTTAGGCAACGTCTCTCCGTACTTTGTGGAGCGCTTTAGTTTTTCGCCCGATTGCAAAGTGGCTGCTAGCACGGGGGACAATCCTTCG
GCGCTGTCTGGAATGTTGGTGGGCAGCAGCTGGCTTACCATTTCCATGGCACAAGTGACACCCTAATGATGAGCTTGAAGGAGCCGCTAAACTG
GGAGGAGGGTCATATACTCTGCCATCCAACTGAAACGGAAGAATTCATGGGCCTTCTATGGTAAATTATTCCTGGGACATTATATCTTAAAATTA
GTTTATTTAAATGTCTTTTTCAGTTTTAGAAATGCTTCATTGGTCCGTGAGGAAATGAACAAGAAGACAACCGGCGGCGATTGGGATAAATTCAA
TGAGTATCTCGACTCCACGCCCCGTGGAAACTTTGGGAACATGGCCGTGCACTTTAACGACATGGAAATCATTCCCAAGGCGCAGGGTATTCTGC
GATGGAACAGGGAAATGGATCCCAGTTCCCCGGACGCGGCTAGGGGTGTAATCAAGTAAGTCTGATTGAAAATTTAGCTGTTTTAGGTCCGACAT
GAAAGCAATGACTCATAATCAGTTAACAGACATCTGTAAATAGTTATTTTTAGAAATGACTTTTTACCAACATGATCATGTTTTTTGTCGTTTAT
ACTTTTTCTTAATGCCTATTTCCCTTCTACTGAATTCTTTAAAATGTATAAAATATTCCTGACCTCTTTCGCTTTATAGATTCAGCTCGCCCCAA
ATCGAAATTCGAGCCCTAGTTGAAGGTCAGATGCTGCATCACCGGGCTGTGGCTGAAGACCTTGGCTACAAATTCGGACCCGAGACACAAATCCT
TGTCACAGGAGGCGCATCTGTTAACAAATCAATCCTGCAAACAATTGCCGATGTGTTCAATGCTCCCGTCCATATCCAGGTTAGTTCATACCAAC
TGTTTCTCAAGTGCAAGCAATTTAAGCAACATGTTTCTTGCAGGATGAAGGATTTGAGGCTGCCCTACTGGGAGCCGCTTATCGATCCGCCTACG
CTCTGTACCTTCAAGAGGCAGGTGATGGGGTGACGCCTCTCTGTTACCGAGATTATATCCTAAGTCTGACAAGTAACAAACTGAGCCTTGTATGC
GAACCACACAAGGACAGCGAGGAAATCTACGCTCCAATGCTACAACGATATCGCGAAATGGCGCGCGTCCTGTCCAATCCTAACACATAAACTCT
CCGAAAGCCCAACGTAACATTCCAGTTTATACTCCGTACATTCACAAACTGATTCCTTCTTAAACGTCTCCTGTAATTGACAGAACTTAAGTGCA
ATTAACAAATTCTGTGATTGACGATTTATTACAAATTTATGCGAAACCATATACAAATAAATTTTTATATATGGCCCACTCCTTATTGTGTCTGG
TATGCCTTTAATCTTTGATCCGCCTACTTTTTGCGTCCACCACGCTCCTTGACCTGTAAATGCACCGTGGTTCCGTTTACCAGATTGTAAAAAGC
CATGGTATTGCTGTCTTTGAAGAACATTCCCTGAAGGATAGATGTTATTGAAATAATAGTTTTCGAAACATTAGTTGTATTTCTTACCTCATAAA
ATATCTTCTGCTTGGCCGGTGGCATGCCAGTTTCGTCCTGCAGCTTCGTCTTCAGATTGGCAATGGGTTCAGAAAGTGCCATGGTCACGGCTATC
ATCTGTCCATTAAGCTTCCACTCTGATTTGTCGGAATTGGGTACCAAAACCTGAATGGTCACAGGGCTCTGAAATAATTTAAGATGGGTTATATA
CCAATAGATAGCCAGATATCAAAATCAAACTTACCTTGTGGGTGGCAATAAAGTCTGCTTCTGGAATCAGGTTGTCCTCGCTTCGAATCTTTTTA
GAAGGCGGCTCCTCCTCCATTATATCAACAGGTGGAGCAGGTGCAATTTGCTGAGGGATTCCACCAGGCTGCATGTTCATGTAGCCTCCACCACC
AGCTCCAAAAGGCGGCTCTGCAAAATAAAAACGCTAAGCCCTCGACGAGATTTGCATACTATTTGTTACTTACGCATCATGGTTGGACGCAGTTG
CATCAGCTGCATCACCGGTTGAGGCTGCTGCGGCGGGTGATGGTGGTGCGACTGGTGAGGTGGCGCCTGCTGATGCGGTGGATGGTGATGATGAG
GATTATGATGCCCGTGGTGACCACCTCCGCCACCTTGGTGGTGTTGACTCTGGCTGGAGTGACTGTGCTGCGACTTGGTTGACGGCTGCGGCGGA GCTGAAAGCGTCGCCTTGTTGCCCACCGGTTTGGGGCCGATTTTCTCCTTCTCCTCGTCGGGCAGCAGTCCCTTAACCTTGTGGATTTGATGAAT
TTGTTCCTCCAGAGTGATATTTGCACGTGCTG
(SEQ ID NO: 1387)

Exon: 1001..1076
Exon: 1481..1602
Exon: 1893..2720
Exon: 2779..3000
Exon: 3215..3404
Exon: 3464..3877
Start ATG: 1017

Transcript No. : CT11741
CGGAAGCAGTTTGAACATGGGTCCGCCAAAGCAGCTGAAACGAACCTTTCTTGGCTTCGACTTGAGCACGCAAAAGCTCAAAGCCGTCCTGCTGG
GCTCCAGTTTGGAGGTGGTTGCCGCGGCTGAAGTGAAATTCGACACCGACTTGCCGGAGTTCCGGACCACCGGTGGAGCCAACGCTGGATCCATC
AAAAATGAATACTTTGTACAACCAGTGATGTGGGTGAAGGCCATGGACATTGTCCTGGACCGACTGGTTATGCAGCAAGCGGATCTTAGCACCGT
AGCTGCCATCAGTGGCTCCGGACAGCAGCACGGATCGCTCTACTGGTCCAAACATGGAATCAACACGCTGCAAAACCTCGATTCCGAGAAGTTCC
TTCACGCACAAATCGACGACTCCGCCTTTGTGGTAAATCGTACTCCGATTTGGATGGACGCCACCACCACCAAACAGTGCCTAGAGATGGAGATG
GCTGTTGGTGGCAAACTTAACATGGTGGAACTGACGGGCTCGAAGTGCTACGAACGTTTTACGGGTCCCCAAATTAGAAAGATATATCAGCAACG
CTGCCACGCCTACGAAGAGGCCAACCGAATCTCATTGGTCAGCAGTTTTATATCATCGCTATTTCTGGGCTCCGTCGCTCCAATTGACTTCAGTG
ATGGTTCCGGCATGAATCTGCTGGACATCCGCAAGAAGAACTGGTCCAAAGAATGCCTAAATGTTTGTGCACCCGATTTGGACAAGCGCCTGGAC
ATTCCGGTCAGTCCAAATTCGATTTTAGGCAACGTCTCTCCGTACTTTGTGGAGCGCTTTAGTTTTTCGCCCGATTGCAAAGTGGCTGCTAGCAC
GGGGGACAATCCTTCGGCGCTGTCTGGAATGTTGGTGGGCAGCAGCTGGCTTACCATTTCCATGGGCACAAGTGACACCCTAATGATGAGCTTGA
AGGAGCCGCTAAACTGGGAGGAGGGTCATATACTCTGCCATCCAACTGAAACGGAAGAATTCATGGGCCTTCTATGTTTTAGAAATGCTTCATTG
GTCCGTGAGGAAATGAACAAGAAGACAACCGGCGGCGATTGGGATAAATTCAATGAGTATCTCGACTCCACGCCCCGTGGAAACTTTGGGAACAT
GGCCGTGCACTTTAACGACATGGAAATCATTCCCAAGGCGCAGGGTATTCTGCGATGGAACAGGGAAATGGATCCCAGTTCCCCGGACGCGGCTA
GGGGTGTAATCAAATTCAGCTCGCCCCAAATCGAAATTCGAGCCCTAGTTGAAGGTCAGATGCTGCATCACCGGGCTGTGGCTGAAGACCTTGGC
TACAAATTCGGACCCGAGACACAAATCCTTGTCACAGGAGGCGCATCTGTTAACAAATCAATCCTGCAAACAATTGCCGATGTGTTCAATGCTCC
CGTCCATATCCAGGATGAAGGATTTGAGGCTGCCCTACTGGGAGCCGCTTATCGATCCGCCTACGCTCTGTACCTTCAAGAGGCAGGTGATGGGG
TGACGCCTCTCTGTTACCGAGATTATATCCTAAGTCTGACAAGTAACAAACTGAGCCTTGTATGCGAACCACACAAGGACAGCGAGGAAATCTAC
GCTCCAATGCTACAACGATATCGCGAAATGGCGCGCGTCCTGTCCAATCCTAACACATAAACTCTCCGAAAGCCCAACGTAACATTCCAGTTTAT
ACTCCGTACATTCACAAACTGATTCCTTCTTAAACGTCTCCTGTAATTGACAGAACTTAAGTGCAATTAACAAATTCTGTGATTGACGATTTATT
ACAAATTTATGCGAAACCATATACAAATAAATTTTTATATATGGCCC
(SEQ ID NO: 1388)

Start ATG: 17

MGPPKQLKRTFLGFDLSTQKLKAVLLGSSLEVVAAAEVKFDTDLPEFRTTGGANAGSIKNEYFVQPVMWVKAMDIVLDRLVMQQADLSTVAAISG
SGQQHGSLYWSKHGINTLQNLDSEKFLHAQIDDSAFVVNRTPIWMDATTTKQCLEMEMAVGGKLNMVELTGSKCYERFTGPQIRKIYQQRCHAYE
EANRISLVSSFISSLFLGSVAPIDFSDGSGMNLLDIRKKNWSKECLNVCAPDLDKRLDIPVSPNSILGNVSPYFVERFSFSPDCKVAASTGDNPS
ALSGMLVGSSWLTISMGTSDTLMMSLKEPLNWEEGHILCHPTETEEFMGLLCFRNASLVREEMNKKTTGGDWDKFNEYLDSTPRGNFGNMAVHFN
DMEIIPKAQGILRWNREMDPSSPDAARGVIKFSSPQIEIRALVEGQMLHHRAVAEDLGYKFGPETQILVTGGASVNKSILQTIADVFNAPVHIQD
EGFEAALLGAAYRSAYALYLQEAGDGVTPLCYRDYILSLTSNKLSLVCEPHKDSEEIYAPMLQRYREMARVLSNPNT*
(SEQ ID NO: 1389)

Classification: enzyme

Celera Sequence No. : 142000013384516
CATCAGGTTCTGCACATTCTGGTTGTCGATGCGCACTTGGCCGCTGTAAACATAGTTGATCAGACTCTCCAGGGCACTTGGCTCTATGGCGCTCT
CCTTCATGGTGATCTCCTTGATCCGACTCTCTGCCATGTTGTTGGTGAACATCGCATAGAAATACGGGATGGTGGCCGCCAGCACAACGCGGTGC
GCTGAGAAGGTCTGATCTTCAACCTGCAATAATTGGGATGGCATTTTATATTTAGACGCTAGATAATGAACGTATCTCTGAGCTGCGGGTGATTG
AATGCCCCAGTCTGCACGCAAACAACCTTTAGGGTGACATCGCACAGCTTGCCCATCCTGCGGATTTCCTTGAACAGGGGGAAACTCTCGCCGAA
TAGCTTATCATGCTTGTAAACAAAGTATTGATCCTCCACTTGGCTATTATCACTCAAATCCATCACTTTAACGGATCAAGAAAATGATAAACAGT
AGAGATGCCAAATGTTGCTTGTACTGCAGAGCTAGTGGTGGTCAGTGGTGAGCGGTCACATTAATCGATAGTTGAGGTTCCTTCGATAGTTGAAC
AACACCAATAGTAGTGAAACAAATTTATTGAATCATATTGTTTAATTTTAAAGGTAACGTTCTTGGACCAAAATGTAATTTCATAATACTTATTA
AAAAGTTGAGCCCTTTTTATGCAACAGTGATAATTAAATCCTTAAAAAGCACATATTTTTAAGACAATATTATTCTTTCATTTAATTTTAATTAG
TAATTTTTCCGTTTTTGCGTCACCTTCTTAAAAAAAGACGCTCATCACTAATTGGGCGGTGATGACAGCCCTATCAGCTGTTAGTGTGGCTGGAG
TGTTTTCTTCGCTCGGATTGATTAAGGGTCCAAAAACATTTTCGAGTAATCTGGGTCGCTTGCTAATTGGAAAACCACTGATCTGAGTTAAGACA
TAAATGTTTGGACCGCTATTAAATGCAAGGATACGAAAATAGCAAGTAACATGGAAGCCGCATCACCGAGGGAAACCCAGGTGAGTAAAAAGGTG
TCGCTAGAATTGATGATGACGTCTCATCTTGTTATTTGCATTTGCAGAAGAACCCGAATCCGATCGAGGCGCTGAGCAAAGATGAAATCATCAGC
AAATACAAAGGCCTGCTCAACATCGCTAAAAAGGCGAAACAGGCAAAAGATGGTAAGTTTGATGGAGAGTTTCAGGGAATCTTCCAGAATAATGC
AAGCCACTCTCTTTCAGAACTCACCGAGGAAAATCACCGACTCAAGGATGCCCTTAAACGGGCGGCGGAGAAGCAGAGCAGCCTGCCAGCCATGC
AGGAAATGGTCCAGGACTTCACCGATAAGAACCTCATCCTCACCGAGGAAGTGAATAATCTGAAACGAAAGACCAAAGAGGATGCCGATCGACTG
ACGCAATTCGAGATCGAGAACGAGAGCCTAAAGCGCCAACTTGGGCGACTGAGTGATGAAAACGATGCCCTCCTTGCCAATGTGGATCGCATGGA
AAAGGCTATGCAACAGGTCAATGCTCTGGGTAACGAGCAGCGCAAGAATCTGGAACTTTTGGAAGTGGACATTGCCAAAATTAAGGAAGCGGAGG
CGGAAAACGCTAGTCTTCGCCAGCAAGTCGCCACGATGGAAGAAGAGTCGAGTGTGCTGCAGCAAAAGTACCAAAACATCAAGGAACTTAACTCT
GAGCAACGCAAGAAGTTTAATTCTCTAAAGGACCGCTTCATTGATGTACACCGCAAGTTGAAGAACCTCAAGGAGTGCAAGTGCGTGCTGCTGGA
AACGCAGCACGAGTACGCCGCATCCGTTTCCAAATGGCAGGTGGAGATTATCAAAGCTTCGCAACTGTTGTGCGCAAAGATGGCATCCCTGCAGG
CCGAGAATGAAAAACTGAAGCTGAACAATGGAAAGTCAGACAATAATCCTCAAACAATTGACACTGGAATTGACCGCAAGCGCTTGCTGCAAAGA
GTTCAGGAAATGGATCGGCTAGCCAAAATAGTGAAGCAGAAGCAAAAGAACCAAAGGAGCAATTTGAATGTGGAGTACCTACTTAAGAAGATAAC CGCTCTCGAAGAGCTTGCAGTCATTATAAAGCAGCAGCATAGAATTGACAAGGAACAATTGATAAGTGTAACGAAGGAGCAGGAAAACACCAAAA
ATCACGCCAGGAACCTTAATGTAAGCTTATTCCAGACCAAGCTTGATCAAATGCAAAATCTGGTCAAAGTCATTGCAAAGGAGCGTGATAATCAG
CAGAGGAAGTTGCAGGAGTTGGAAGCCATCTGCATAGAACTGCGCCAACACAACGAGGATTTGCTTACGCGATACCACCTCAAGGAGCAAGAGCA
TGGAGAGTTGCTAACGGAGATGCGGGAACTGAACGAGGCGCTCAAAGGACGCGGTGATGCCATTTCACGCCTTCAAGAACAGCACGAAGCGGAGG
TCAAGCGACAACGAGACTTGGAGGCTCAACTATCTAATAGTCAGCAGGCGGCGCAGGAGAAGTTACAGAAGATCAAACAACTCCAGAGCCGTGTT
GAGGAATTGGAGCAGGCGAATGCTGATGCCCAGAGTGATGTTCTGTCGACATCCACAATATCACGAGCCGAAGAACTAAGCCGCCTGCGTGAACT
GGACGAAGGCTACGAGGAGAAGTACCATAAGCTCAGAGCCATAGCTGCCAAGCTGAAAAAGAAACTGCAGGAGCAGACGCAGCAGCTGAATGAAA
TGGAACAGAGCGGTGCCCTAAAGGAGGAGTTGGAGGCAATCAAGTTGGCACAGGCCCAACTGCAACAGGATTTAAATGCAGCTCGAGCTGAAAAC
CAGAAGCTAAAGTCCAAGGAGAAAGTAAAGCACTCCAGTGTCCTTAATTTGGAAATTGAAGCAGCTGAAAAATCCCTGAGCGAAGTTAGTGCGAA
GCTGACAGCTAAGTCTAGCGAACTAGAAGCCGTTAAGGAATCACTGGCCAGCAAGGAAAACACCATCGTCCAGCTGCGCAAGGAGATCGCTATCC
TAGAGGAGGCCAAAAACGGCGAAGCGGCCCACTCCCTAGAACTTAAGGAGCAGATTGATCGCATGCAGGTCCAGGTCAAAGACGCAGTTCACAGC
AAGCAACAGGCGCTCACTCAGAACAAGGATTTGGAACATGGCGTTGAACAGGCCAAGCTCGAGGCGGAGCAATTGCGTCTCCAGCTGTCGGAGAG
CGCCCAACAATACGAATCGAAGCTAAACACGGCCACCCAACAACTACTAAGCCAAACCCAGGAGCTGGAAATGCACCTGGCAGAGCAAAAGCGAT
TGGAGACGGCGCTTCGAAATGCGGAACGAGCTCTGGAGGACCTGCGAGTAGAGTACACCGAATACAAGTTGAAGGCACAGTCTGTGCTGCGCAAA
AACCAAAATAAGGGCTCCAACCGCGAACAGGAGTTGGAAGAAGAGTTGGTTGCGCTTCGAGAGAGTGAACGCAATCTGCGCGCCAGCAACGATGG
AAGAGCTGCCCGCCTGGCCCAGTTGGATAGTCAAATAGAGGAATTGCGACAGGATAACACTGATCTGCAAAAGCGTAGCAAAGAGCTCGTCTCTC
TAGTTGACGAACTGCGTCAGCAAAACGACCTGCTGTCGCTAGAAAACCAACGCCAGTTGCAATTCCAACACGACCTGATGCAGCAGCATCGCCAG
CAAGTTGATGAGCTGGACGCCGGGCACCAGTTGCAATTAACGCAGGTGCAGGAGCAACTGGAGGAAGCGCAAAAGATGCAAGCAAACGTCTCTCA
GCATACCACTGCATCCGCCGCGAGCGTGGACACCAGTCCAGAGCAGGCAAAGATCGATTACTTGCTTATGGACCACGAAACAGGCTTGGATGGCC
ACGCTGGAGACGTCTCTCTGGCCCAACTGGCTGCTCAGCGAAAGATATCTACTGCCTCGAGACGTTCCCACGACTTCATGCCGCTTGACGAGCTG
CTCAACACATCAATGAACCAAATAACCAGCGATACCGTGACTACCATCTCTAATTTCGGACGCAGCGTTTCGCAGCAGGAGGACGAGGAAGCGGA
AATGGCCGCACGGGGAGACTTTTCCGTCCAAAGTGCCCAGCTTCAGGCCACAAAAGAACGCCTAAGCATCCAGGAAAGTCGTGTCAAGCACTTGA
CTGCCCTGTTGGCCGAAAACGAACAGGATTTGGCTAAACTGACCCAAATGAACGACATGCTCAAGGAAGAATTGCGCCGCCAAGAGCGCTCCGAG
GAACGTGAACAACACATGCACAACTCCGAGTACTTGAAGAACGTCTTCTTAAAGGTGAGATCAGGAACGCAATAACTATATCCACGGGCTTAATC
TATTTACTTTATAAACTTGCAGTTCCTTACGTTAAACAATGTCGATGAGCGGCAGCGCTTGGTTCCCGTGCTAAATACCATTCTCCGCCTGAGTC
GCAACGAAATGGAAATGCTGAACTGTGTGGCCAAGGGACAGAAAGGTAACTACTAGCAGAAAAATTTAAATTTTAGTATGGTTTCTTGTATTAAG
ATATTGCTTTTAGTTTCTGCAGATGGTAGCAGTCGCAGCTGGACGGGATTCCTCACTGCGTGGAGTGGAGGAGGCAGTCCCAATAATAACAACTA
GCGAACATCATAGGATATATAATATATAAATATTCGTCTTGTTGGATGCGGATAGTCGTCAGTCGTTGGGCAGTTGCATAGCATTCATTCTGTAA
ATCTTGTACAATTTCCCTTTTATATATAATGTATTTTAAAATTGCTCGTTGCTGTTTGGCACATCGTACTTTGTACACTCTTGTAATTTGTCCAC
ACCCGTTGTGTTGAGTGCCCTATACAGCACCACCGGCAATATGCGCGTTGTAGATTGAAGAAAGCCTTTGCATATATTTAAAAACAATGTTTTTC
AATGGTTTGTTTAATTTGAAATTCTATTACCATATAGATCAGACTATAAATCAGATGCATTGTCTATAAATTAGTATTCCATTATTTGTATTGTA
TGTACTATATATAAATAGGATCGGTATTTATGCTTACATTTACACTTTTAAACGGTGTATATTGTTTACACACAATATAAAATATCATTAACATA
AATCTTACATAAATTTCATTAAAACCAAAAGTGAGTAATCAAGTTAAATAAAAATTCTGTCTTGGCGGAATACATATGCAGGTGAACGATTTGAA
TCGAAATGCGCCAAAAGATTAAAGATCACAAGTCGAATAACTACTTAAATACTAATCAGTATTGTGAGCCCGGATCGGATCCTATGCCAATCTAT
TGCCAAACGCCCGCATAGTTGCCCACCAAAGTCGCCGGCAGTGGTCCTCCTGCAGCGAAGAGGCGCATCCTAGTGCTGTCATAGCAGTGGGTGTA
GATGGCGGGCACATACTTCACCTGCTGGAAGCCATCCATCTCATCCTCCGGATACTGAAATGTACAAAACAGTTAGGTGAATTGGTGTATTTTGT
GGAACTGTAAC
(SEQ ID NO: 1390)

Exon: 1001..1030
Exon: 1093..4329
Exon: 4393..4521
Start ATG: 1001

Transcript No. : CT11878
ATGGAAGCCGCATCACCGAGGGAAACCCAGAAGAACCCGAATCCGATCGAGGCGCTGAGCAAAGATGAAATCATCAGCAAATACAAAGGCCTGCT
CAACATCGCTAAAAAGGCGAAACAGGCAAAAGATGGTAAGTTTGATGGAGAGTTTCAGGGAATCTTCCAGAATAATGCAAGCCACTCTCTTTCAG
AACTCACCGAGGAAAATCACCGACTCAAGGATGCCCTTAAACGGCGGCGGAGAAGCAGAGCAGCCTGCCAGCCATGCAGGAAATGGTCCAGGAC
TTCACCGATAAGAACCTCATCCTCACCGAGGAAGTGAATAATCTGAAACGAAAGACCAAAGAGGATGCCGATCGACTGACGCAATTCGAGATCGA
GAACGAGAGCCTAAAGCGCCAACTTGGGCGACTGAGTGATGAAAACGATGCCCTCCTTGCCAATGTGGATCGCATGGAAAAGGCTATGCAACAGG
TCAATGCTCTGGGTAACGAGCAGCGCAAGAATCTGGAACTTTTGGAAGTGGACATTGCCAAAATTAAGGAAGCGGAGGCGGAAAACGCTAGTCTT
CGCCAGCAAGTCGCCACGATGGAAGAAGAGTCGAGTGTGCTGCAGCAAAAGTACCAAAACATCAAGGAACTTAACTCTGAGCAACGCAAGAAGTT
TAATTCTCTAAAGGACCGCTTCATTGATGTACACCGCAAGTTGAAGAACCTCAAGGAGTGCAAGTGCGTGCTGCTGGAAACGCAGCACGAGTACG
CCGCATCCGTTTCCAAATGGCAGGTGGAGATTATCAAAGCTTCGCAACTGTTGTGCGCAAAGATGGCATCCCTGCAGGCCGAGAATGAAAAACTG
AAGCTGAACAATGGAAAGTCAGACAATAATCCTCAAACAATTGACACTGGAATTGACCGCAAGCGCTTGCTGCAAAGAGTTCAGGAAATGGATCG
GCTAGCCAAAATAGTGAAGCAGAAGCAAAAGAACCAAAGGAGCAATTTGAATGTGGAGTACCTACTTAAGAAGATAACCGCTCTCGAAGAGCTTG
CAGTCATTATAAAGCAGCAGCATAGAATTGACAAGGAACAATTGATAAGTGTAACGAAGGAGCAGGAAAACACCAAAAATCACGCCAGGAACCTT
AATGTAAGCTTATTCCAGACCAAGCTTGATCAAATGCAAAATCTGGTCAAAGTCATTGCAAAGGAGCGTGATAATCAGCAGAGGAAGTTGCAGGA
GTTGGAAGCCATCTGCATAGAACTGCGCCAACACAACGAGGATTTGCTTACGCGATACCACCTCAAGGAGCAAGAGCATGGAGAGTTGCTAACGG
AGATGCGGGAACTGAACGAGGCGCTCAAAGGACGCGGTGATGCCATTTCACGCCTTCAAGAACAGCACGAAGCGGAGGTCAAGCGACAACGAGAC
TTGGAGGCTCAACTATCTAATAGTCAGCAGGCGGCGCAGGAGAAGTTACAGAAGATCAAACAACTCCAGAGCCGTGTTGAGGAATTGGAGCAGGC
GAATGCTGATGCCCAGAGTGATGTTCTGTCGACATCCACAATATCACGAGCCGAAGAACTAAGCCGCCTGCGTGAACTGGACGAAGGCTACGAGG
AGAAGTACCATAAGCTCAGAGCCATAGCTGCCAAGCTGAAAAAGAAACTGCAGGAGCAGACGCAGCAGCTGAATGAAATGGAACAGAGCGGTGCC
CTAAAGGAGGAGTTGGAGGCAATCAAGTTGGCACAGGCCCAACTGCAACAGGATTTAAATGCAGCTCGAGCTGAAAACCAGAAGCTAAAGTCCAA
GGAGAAAGTAAAGCACTCCAGTGTCCTTAATTTGGAAATTGAAGCAGCTGAAAAATCCCTGAGCGAAGTTAGTGCGAAGCTGACAGCTAAGTCTA
GCGAACTAGAAGCCGTTAAGGAATCACTGGCCAGCAAGGAAAACACCATCGTCCAGCTGCGCAAGGAGATCGCTATCCTAGAGGAGGCCAAAAAC
GGCGAAGCGGCCCACTCCCTAGAACTTAAGGAGCAGATTGATCGCATGCAGGTCCAGGTCAAAGACGCAGTTCACAGCAAGCAACAGGCGCTCAC
TCAGAACAAGGATTTGGAACATGGCGTTGAACAGGCCAAGCTCGAGGCGGAGCAATTGCGTCTCCAGCTGTCGGAGAGCGCCCAACAATACGAAT
CGAAGCTAAACACGGCCACCCAACAACTACTAAGCCAAACCCAGGAGCTGGAAATGCACCTGGCAGAGCAAAAGCGATTGGAGACGGCGCTTCGA
AATGCGGAACGAGCTCTGGAGGACCTGCGAGTAGAGTACACCGAATACAAGTTGAAGGCACAGTCTGTGCTGCGCAAAAACCAAAATAAGGGCTC
CAACCGCGAACAGGAGTTGGAAGAAGAGTTGGTTGCGCTTCGAGAGAGTGAACGCAATCTGCGCGCCAGCAACGATGGAAGAGCTGCCCGCCTGG CCCAGTTGGATAGTCAAATAGAGGAATTGCGACAGGATAACACTGATCTGCAAAAGCGTAGCAAAGAGCTCGTCTCTCTAGTTGACGAACTGCGT
CAGCAAAACGACCTGCTGTCGCTAGAAAACCAACGCCAGTTGCAATTCCAACACGACCTGATGCAGCAGCATCGCCAGCAAGTTGATGAGCTGGA
CGCCGGGCACCAGTTGCAATTAACGCAGGTGCAGGAGCAACTGGAGGAAGCGCAAAAGATGCAAGCAAACGTCTCTCAGCATACCACTGCATCCG
CCGCGAGCGTGGACACCAGTCCAGAGCAGGCAAAGATCGATTACTTGCTTATGGACCACGAAACAGGCTTGGATGGCCACGCTGGAGACGTCTCT
CTGGCCCAACTGGCTGCTCAGCGAAAGATATCTACTGCCTCGAGACGTTCCCACGACTTCATGCCGCTTGACGAGCTGCTCAACACATCAATGAA
CCAAATAACCAGCGATACCGTGACTACCATCTCTAATTTCGGACGCAGCGTTTCGCAGCAGGAGGACGAGGAAGCGGAAATGGCCGCACGGGGAG
ACTTTTCCGTCCAAAGTGCCCAGCTTCAGGCCACAAAAGAACGCCTAAGCATCCAGGAAAGTCGTGTCAAGCACTTGACTGCCCTGTTGGCCGAA
AACGAACAGGATTTGGCTAAACTGACCCAAATGAACGACATGCTCAAGGAAGAATTGCGCCGCCAAGAGCGCTCCGAGGAACGTGAACAACACAT
GCACAACTCCGAGTACTTGAAGAACGTCTTCTTAAAGTTCCTTACGTTAAACAATGTCGATGAGCGGCAGCGCTTGGTTCCCGTGCTAAATACCA
TTCTCCGCCTGAGTCGCAACGAAATGGAAATGCTGAACTGTGTGGCCAAGGGACAGAAAGGTAACTACTAG
(SEQ ID NO: 1391)

Start ATG: 1

MEAASPRETQKNPNPIEALSKDEIISKYKGLLNIAKKAKQAKDGKFDGEFQGIFQNNASHSLSELTEENHRLKDALKRAAEKQSSLPAMQEMVQD
FTDKNLILTEEVNNLKRKTKEDADRLTQFEIENESLKRQLGRLSDENDALLANVDRMEKAMQQVNALGNEQRKNLELLEVDIAKIKEAEAENASL
RQQVATMEEESSVLQQKYQNIKELNSEQRKKFNSLKDRFIDVHRKLKNLKECKCVLLETQHEYAASVSKWQVEIIKASQLLCAKMASLQAENEKL
KLNNGKSDNNPQTIDTGIDRKRLLQRVQEMDRLAKIVKQKQKNQRSNLNVEYLLKKITALEELAVIIKQQHRIDKEQLISVTKEQENTKNHARNL
NVSLFQTKLDQMQNLVKVIAKERDNQQRKLQELEAICIELRQHNEDLLTRYHLKEQEHGELLTEMRELNEALKGRGDAISRLQEQHEAEVKRQRD
LEAQLSNSQQAAQEKLQKIKQLQSRVEELEQANADAQSDVLSTSTISRAEELSRLRELDEGYEEKYHKLRAIAAKLKKKLQEQTQQLNEMEQSGA
LKEELEAIKLAQAQLQQDLNAARAENQKLKSKEKVKHSSVLNLEIEAAEKSLSEVSAKLTAKSSELEAVKESLASKENTIVQLRKEIAILEEAKN
GEAAHSLELKEQIDRMQVQVKDAVHSKQQALTQNKDLEHGVEQAKLEAEQLRLQLSESAQQYESKLNTATQQLLSQTQELEMHLAEQKRLETALR
NAERALEDLRVEYTEYKLKAQSVLRKNQNKGSNREQELEEELVALRESERNLRASNDGRAARLAQLDSQIEELRQDNTDLQKRSKELVSLVDELR
QQNDLLSLENQRQLQFQHDLMQQHRQQVDELDAGHQLQLTQVQEQLEEAQKMQANVSQHTTASAASVDTSPEQAKIDYLLMDHETGLDGHAGDVS
LAQLAAQRKISTASRRSHDFMPLDELLNTSMNQITSDTVTTISNFGRSVSQQEDEEAEMAARGDFSVQSAQLQATKERLSIQESRVKHLTALLAE
NEQDLAKLTQMNDMLKEELRRQERSEEREQHMHNSEYLKNVFLKFLTLNNVDERQRLVPVLNTILRLSRNEMEMLNCVAKGQKGNY*
(SEQ ID NO: 1392)

Celera Sequence No. : 142000013384367
CAGATCTTTCGTTTAAACTTACGTGAATTAGGTTTAAAAATGCTCCAATTAATCGATGTCAGTGCTTTTATCACGAGTTTTGGCTTATTAAGTTC
GGGCTCAAGCCGCTCGTTGCTTCCGTGCACGCGGCAGTTGTTGGCGTGGACGCCGGAGTTGCTGCTATTACAAGTGTTTAGCAACTTTGAACACT
GCGATTTCGTGCTGCTGCCAACAAGTGATGCAGTTGTAAATGAATGTTGCAATTTCAAATAGCAATTGTTCTTGATTTTAAAGCACATGAGCACT
AGACTGATTCGAATTGGACATTTGAATCTTTAACGGGCGGAGAATATAAAACACCGGCAAAATAAATAAAGAAAGGAGCCACAACAAACGGAAAG
CCAGAGGCGTAGTCATTCTCTTCGCAAATCAGCGGGGGTTACCATTCGAGCAGCATACAACCCTCTCTGAGAGAGAATTGACATGCCACTGGATC
TCACACATACAATGAAAGGCACACTCACTCAAAGTAGACAGCACTGCCAGACTTAATGCAATAGTATAGCAGTTGGTGTTGGCAGTGCCATTTGA
TCGCTGGAGGTGCTGCCAACGCATTTACCAATTAATTAATGACCACCCCTAAATGTTGTAAATTATAAAAATTATTCAAGAATATTACGATTTTG
GTTAAATTAATGTACAAAATAAAATATTTCATATTTGTATTGGCTGTCAAATGAAGTTATTTTATTTTAAGATAAATGCTAACAAATCTTAGAGA
AACTGGAAAACAAGGTTGAGCGGTTTTGAGAATTATGAACAACGCGTAAAAAACATTATTTATAAACGTAAAAAAATATTATAGTCTAGCCCGAC
AGGTAAAAAATAAATTTATCCGGGGCCACCTTGGTCAACCCTCGTCAACGACCGTTCGGCCTGCCAACTCGCTTTTCCCTGCAACGCAAGGCGCC
GCTCTCTGCTCACACTCTCACTTGGCTGTGTGTGTGTGCTCAATACTCGCTTTTAGTTTTCGCTGCAGTCGGTCGCCGTTTTTAGTCTCAGCTGC
TGCGCGCGTGTGTTGTGATTGTGTGAATTGCGTTTGCGTTTGTAGCATAACACAAAACCGATAAATTCCTGGCGAAGCGAGCTCTCTCGATTGGA
TTCTTGCAAAGTGAACTAGCGATGAGCGCCGCCTCTGAGGTGAACCTGATGTTGCTGCGGTCAGTGGAGAAGCAGACTGCGCTTTATGATCGTAC
CGACGAAAACTATAGGAAGCGCCTGCCGAGTGAGAACGCCTGGGACATGGTTGCCTCCGAAGTTGGAGAGTCGGGTGAGTCGTGAGTGCGAGCGG
GATAGCAATCGACGTTGCGTAGTTTTCTGCCAGTGCTGCACAGCGTCAACGCGCGCACAACAGTCAGTCGTCCCCGAATTATCGGCCGTCGATAG
TTGTGTGCGAGTTGGCAGCGCCATGTATGCCATCACAAAGCAGCTGGCATCGATTAATTCGAATATAACGAGTCTCCTGTTGAATGCGTAGTCGT
TTGGGATGAAATTGCTTCTTGCTGTGACATAATTTTTGTAAATAGCTGGAAAGTAATTTATATTAGTTATTTGGCAACTGCAATAATTGCATGGT
AAAAACTAAACAAAGTTATTTCGTTTGTTGTTATTATTATTTTTTAATTTAACATTTTATAATTTATAATTCTCCAACAAGCTTGTTATTTCAT
ATTAAAAAAATGTCTTATTTGAATATTACATTATTTTAGAAGGATTTAAAAATAAATAAATTAAATACAGAAAAACCAAAATATGACAAATAATA
ATATCTAGTCTATTCAGTAGCCAAATCCATTTCATTTAATTCTTATTAGCTTTATAAATTTTTTTTAAATGATTTGAATCCTTCTGCACGTTTTG
GTAACACTGGTAACACTAATCGCCCATTAGCTGAGTAAAATTTAACCTTAGAAAATTGGTATATTGTATTATATTGGTATATTATGAGTGGGTAG
TTCCATTTATCCATGCATCTCTGATTTTGTTGTCGGTGTATATCGATTGACCCATATATATTTCCCTGGAAAGATCTTTTGGCCAAACTTTTCGA
GCAGTACAATATAAGTTGGCTCTTTTTCATTTGAGAACTGAAAAAATATTGCCAATGATGGGGGACTTCTTATTCGAGAATTCTTGCTGTAAGTT
TTATTTATATATCGCAAAAGAAAGAAAAATCCTTTTTAGTGTACATATGTACATACACACGTGCATGTACATATTTAAGTATGATTCTCAATTTG
ATTGCGATTATTTCCACGTGGTTTCTGACACCTTTTACTAAACTTTACACGATTCCTTAACACAACTATTTTTTAAGTAATGTGTTTGGATATCA
GATAAAGGGTGTTTCAGCAATGTCTACAGGTTTTGTTAACTAACAAATTAAAACGTATCTTAGAAGTTTGGGCGTCGGAAACCTGCACGCCTTAT
AAATATGTATGATATGTACATCCATGTACGTTCCCATGTATGTATGTCGGAAATCTGCATATATATATATTTATATAAATATATATGGTCATGTA
TGGTCATGCAGATAAATGGACGCTTCTAATTTGTATACCCCTTACTCGTAGATTTAAAGGGTATACGTTGGAAGGGATTCGTTGCAAAGTATGTA
TGCAACTGGTATGAAGGTCGATCTCAGGAACTATAGAAACAAAAAGGTTCAAATTAAACATATAGATTAAAGGGACTTAGACGCAGCGAAAGTTT
GTTTTTTCATAATTTTTAATTAGTTTTGTAAATTTATATTGACTTTTTGAACAGTTTTTTTAAAATTTTCTCATTTGACTCCCCAATATCTATCT
ATATGCCATATCTATATGCATTATAAAGCTTCCCACTTCCATTATTCATTCTCTTATTATTTGTTTTTGTGGTGATTTATTGCACTGTAAATTAA
TTTTTTGCAAAAATGCTTTGTCTTAAAAATATAAAGTAATTTCCTACAATTTTTCTTGTATATGTTATAGCTGATATTATTTTATCACTTTAAAA
AATTGTTATGTTTGGCTAGAAAAAAGCTTATTTTTTATGACCCGATTTTTATTTGAACTATCCTTATGCAAGGACAAGAATTGAAATGGCACCGA
ACACAAAATTTCATGTGTCAGTTTTGTCAGATTTTGGCCGCGGTAATTGAAAATAACCTTCCGCAGCGTAGTTAGTTACATACTGTTACAAACCA
TATTAATCGGCGAGTATAAAGGCAGATAACTAAGAAGCAGTTTTGGCACGTAGAAGCTAAGAATTTCTTGTCTATTACTCCAAATCAATTTTGCC
ACTTCCTCCAATGGAAAGAGCCATACGAATTTGATCAATTAAAAAATAATATGGAAATATCTAATACCGAAGACCATATTTAGACCATTAAGACC
ATTAATTAGCTAATCATTTTCCGACTGTTGGTATTGAAAATATAGTTTTTCGATTTTAATAAATGTAATCCAAAATTTATATATATATTTCCAAGAT
CTAGTGTATTCTTATTAAAAACAAGTAATGTGCCATCCGGGTTGTAGGACCCGTGATTCAGGGTTCGCGGTGCGTACTGGATGCCCCGATTTTGT
GACTAGCAGTTACACACTGCAGTGCTTTTATTTTTATTTTTAAAAATTTACATACATGTATAGCTTAATTATTAAATACTGCTACCTTCAGGCAG
CTAAAAAATTATATATAAACTGCAGTGCATGTACTCGCCACCGAATACTCATTTATACTCATTTAGATATTCATACATAGCATACTTTCAAGCGA AACTTGCATTTACGGAACCATGTACAATGTTGGTTTTTTGAAATTAAAAATAATTTAACTAGTGTCTCTTCCCATTATTAATAAGCATTCCTGAG
CTCTTATTACCTGTTCATGTAAAATGCACACAAAGTTTTATGAGCTAAGATTAAAGTGGAATTTTCCGGGCAATCAGGGGGTGTTATGCTATTGA
GAAGTAAAGGTTGGGCCGCTACCTGTTGCCTGATATATATTACGTATCATATCTTCTTACCTAGCCTTATCATTTCCCTCTTGTTCCCTCTTGCA
GTGGAAAAATGCAAGCGACGCTGGCGTCAGCTGCGAAATGACTATACCCGCTGGTGCAACGCCGACGCCAACCGGCGACGAAATGGCCAGCGTCG
TTTGGCTTATCCGCTGGCCGATGAGCTGCGCTTTTTGGACCGCCATCTAAACATAGCTGACGACATGGCTGCCGACGATGACCGCAGCGTATCAT
CGGACAAGGACAGGGATAACAATAGAGACAGCGAGGGCGTGGATCATCATGCTCAGGCGTCATTAAAAGAACGCGCATCATCGACAAGCAAGTTA
GTTAAGGAGGTCAAGCTGGCAAGTCAAGTTCGTAAGGAAAAATCGTCCCAAGACAAGAGAGAAAATTGGGAAAATCCTGGAGATAAACAGCGATC
TAGGAAGAAAAGTGCTGAAGAGAAGCTGAATGATTTGGAGGAATCGGACGAACCAGAGAAGGTTCCTGAACTCGATAGTTTTCTGCAGTCTGATA
ATGAAGACGACGAGTGCATGGACGAGGAGCACCTAGAAGATCTGGAAGGTTTCGATTTTGACTTGGAACAATCGAATCAGGAAAAGGAGTTAACG
CCGGAGAAGTCTCTAGAGAAGAATAACACCGACTCAACTGTTAGCCAGCCGGAGTTCTTTGTCAAGCAAACCAGAGATCCTCGTTTGCTAATTAT
TGGCAGAAAGAATTCGACGTCTTCGTTTGCTGAATCCAAGGCTTCAAAATCTATTTCCGGGGATCCTCTGGAAACGGCTATGGAAGATAGTGGCG
ATGAATATGGTAGGGATGGTGAAAAACGCGTCACAGGCAGCGACACTACTTCTCCAACCCGACGTCCACGTCGCGCAGCCCGTGCATCAATAAGT
TTCGCTGGCATAAGGGATTTACCGATCCAGAAACCAGGCCAAGCACAACGAATGACGCGATTGCAGCGCAGGAAATCTATGAGTTTAGCGGCTGT
ACACAGTGTAAGGAGCTCCACATCGCCTGTGAAAATGACTCCAGTCCCCAGGTCTCAGCCGATCAACAAGCCGCCATCCGGGCCAGTCCAGATCA
CGAAAATCAGTCATCGGGATGACATCTTCCCGAGACCTGCGGTGCCATCTGGAGTTGTGAATATAAATCAAAACCAACTCAAGACTCAACAACAG
CAGAAGACGCTGATCTTTCCGACGACCGATGAAGCGATCGCTAACCCGCAGGGATCTGGTCCACCACAAAGGAGGTCCGTGGGTAGGCCGCCCAA
GAAGCTACCTATGGTGCAGCGAATAGTTGCGCCGGAAACGCAGACCAAGCCACAGTCGCCCATAAACACCAAAGTCCTGACCATTGGCAAGCCCA
CCAGCTCCGTCGCGAGTGGTAACATAAATAATATTGCTATCAAAAGCAACGTCGTTACTAGCATAAGCAGCAGCACCGCTACTACTAATACCATT
ACCAAAGGTACCAGTAACAACAGCATCAAAACTACTGAAAACGTTAATGTAATAAGCTACAGTCCGAATTCATCTAGCACCAGCAGCAGCAGCAA
GGCCACCACTGGTGCCTCTGGTGCGGTGATAACTAATATACCCACAACCACCACAGCTGGAACATCCGTTCCGGTCGGAAAGAGTATAACCCAAT
TGAAAATGACTGAGCGAGGCACTCAAACCGGAGTCCAGAATCCTTTCTCCGATAATTACTTTCTCGAAATGATCAAGCCCCAGATGCAGGAAATG
AACCCCCGTCAGAAGATGCACTTTAAGAAGAAAGTATTCCAAGCGCTGATGGAAACCTTTGATGATGCTACCGATTTCCCAACGTCTAAAGAACT
GCAGCATTTTAATATAAACACTCCTTCAGGATTTGAGCACATTACAGATCCGGAACTTCGATTGGTCAGGGAGCTAGTCAGCATGGTGAGCGCGG
CTAAGGTTACCCTAATTAGACCGCCAGGAGAAGCTACAGCTATAGCTACAGCTTCCCGCAGTGGAATTGCTCCTGAGGTACAGCGAGGACCCCGA
ACAAATATGACACGCCAAGTCATTCAGAGGGTATACAAGCCAGGCACTGGACAAGAGATCGCCCCCACCAGCCCGGCGGGTGGACTAGATAAGAG
GTTGTTCAGGTTAGCGGCTATGGGTGGTAAACCGAATGGCAACTTGAGTGCCACTCAGGAAATTTTGCGCAAGGATAGTGTTGACAGTAACCATA
GTGTGGTCAAGGTGGCCAACCACGCCCCAACAGGCAGTCCCAAAGGAGCTGCTGTAGTGGCTGCTATAAGGCCGCAGGGTTCATTGATCAACAGT
TTCTTTGGACAAGGCAATGGACCGACGACGGCCAAGGGAGCTGCCTCCGAGAATATCCGCGCCATGTCCAGGAGGTATTCCGTGTGCGGTAGCAG
CAATCCACCCAATGCCCAAAACGCTAGCCAAGGTTCCGCCAATGGCAGCACCATAAACTCCAATGCTAGCGCTATGGAAGCGTCTATGCTTAAGC
GGCGATTGATAGCAGCTGGGCATGGAATGGTGCCACCTACCCAACGCCCTCGGTATTCTGCCGTAGGTGCTAGTCAAATGACCACTGCATCGCAA
GGCAGCAGTTTACTAGTGAGGAAGTCTGTGGGCTGCGTTCCTGCTTACCAAAAGCAAATCTCACCCACTGGCGGTGCCTCCCTGCTTCAGAAAAC
TCCGCAGATTGCCAGTGTGCAAGGATCTGCCTTCAATGACTTTGCCCAGCCCAAGCCCGCTGCAACGGCCTCTGTAAACGGCGAAGAAAGTTCGC
CTACCTCGGCGCTGAAGCGCAGCTTGGTGGTGGCTAATACCAAAACCTCCTTTCAGGACCTTCTTCAGCAGGCCAGTCAGACGGTGCAGAGAAAT
AAAATTGAATCCTCGGAGACAGCAGCCACTATTGCTGCGGATGATTTTTCGCTGGACAACCTTAAGCGAGAGCCAGTGGATCCCGCGGAGGATCA
CAATGACATACTCGGTGTTTAAGACCAGGCCAAAGAAATTTCCGAGTATTGATTAAAGAGTAAAGAATTAAGACAGATTCATTAAATCGTAAATA
ACACGTTGAAAAATTGTTAAGCTATCTAATGCACTTATAATGTTGCGTTAAACATTTTTTATAGTTCCCTATAATTTTAAGAATTTCGAATTTTT
TTTTTTTGGAAAAAGTTTTTAACTTTTTCTATTTTGTTCATAATTTTTAGACGATAGAAAACCGACAGTTTTGTTCAAAATTTGCACAAGAAAA
ATGATTAATGAGAAATCGAATCTTAACTTTATTTCACATTTTCTAGTTATATATATCGAATAAAAATTGCCCTTATAAGTTAAACAAAAAGGACA
ACTGAAAAAATATTTAAATATGTTTTTATGGAAATATATTTCTATACATAGTTAGGTCAAAGTCACTAGAATATTATTCTAATGTCTTTGGTTAG
GTAGTGAAATATATTGCAGTACATTTATGCGAAACAACCATCACGAAAATTTGAAAATTAGTTTGGTTGGTGAACCAAACTGGAGGGTGGGTGCT
CCAGACGTTGTTCTAGCAGAGACATAAGTAAAATTATGAAAATTAATTAATTCTAATAATTATGACAATATCTTTGGTTCGGGTACCGATTCTGG
AGTATTTCCAAAGCTTCAGAGTATTTAGATACTGATCAATAATATTAAATTGTTTTTATCAATACATCAGTGAGTCGGTGGAATTAACAGTTCCA
AAGCACACAAACTGATGCAATTACCACTATCAGGATATATACGTGGACCTAACTACGAAGTAACACATCATCGATAACAGAAGATTAGATATGAA
AACGCTGACGCAGCTAAGAAAAGCCTAAACATAACAATTCAGTAATAACATAAAACCTTCTTGTATTTATAAATAGAATAAAAAAATAAATTTGC
AAATTTGATCAAACGTAATTCCAACGTTATTGAAATACTTCCCGTTTTGGGTGAACCACCGGTAAAGATTTACAAGGTACCAGTACCATTCAATA
TGCTGTTCTTTTTGCACATTTGGCTGGGAATCTAATCTGGAGAGGTCTACCGCGAATGGGCCGTAAATAAGGGAGTCAGTGCCCAGATAAGGCAG
CTATATAACCTCTCTTCAAGTGGCCGCGAGGTTCAGTCGAATTCGAGACATCACCATGAAACTCTTTGCCATTTGTGCCCTCCTCATCCTTCCGC
TGGTAAGCGGTGGAATCGTGCCACGCACACCTACTAGGCACTTTGTGGCCTACGAGATCCATTCTACCCATAATCTCCCCCAGATGGAAGGTAAG
AGACAGTATTAGTTATACCAGATGGTACAATTCGCTGGATGGATTACGCTTAGC
(SEQ ID NO: 1393)

Exon: 1001..1309
Exon: 4087..7414
Start ATG: 1162

Transcript No. : CT12739
TTTTAGTTTTCGCTGCAGTCGGTCGCCGTTTTTAGTCTCAGCTGCTGCGCGCGTGTGTTGTGATTGTGTGAATTGCGTTTGCGTTTGTAGCATAA
CACAAAACCGATAAATTCCTGGCGAAGCGAGCTCTCTCGATTGGATTCTTGCAAAGTGAACTAGCGATGAGCGCCGCCTCTGAGGTGAACCTGAT
GTTGCTGCGGTCAGTGGAGAAGCAGACTGCGCTTTATGATCGTACCGACGAAAACTATAGGAAGCGCCTGCCGAGTGAGAACGCCTGGGACATGG
TTGCCTCCGAAGTTGGAGAGTCGGTGGAAAAATGCAAGCGACGCTGGCGTCAGCTGCGAAATGACTATACCCGCTGGTGCAACGCCGACGCCAAC
CGGCGACGAAATGGCCAGCGTCGTTTGGCTTATCCGCTGGCCGATGAGCTGCGCTTTTTGGACCGCCATCTAAACATAGCTGACGACATGGCTGC
CGACGATGACCGCAGCGTATCATCGGACAAGGACAGGGATAACAATAGAGACAGCGAGGGCGTGGATCATCATGCTCAGGCGTCATTAAAAGAAC
GCGCATCATCGACAAGCAAGTTAGTTAAGGAGGTCAAGCTGGCAAGTCAAGTTCGTAAGGAAAAATCGTCCCAAGACAAGAGAGAAAATTGGGAA
AATCCTGGAGATAAACAGCGATCTAGGAAGAAAAGTGCTGAAGAGAAGCTGAATGATTTGGAGGAATCGGACGAACCAGAGAAGGTTCCTGAACT
CGATAGTTTTCTGCAGTCTGATAATGAAGACGACGAGTGCATGGACGAGGAGCACCTAGAAGATCTGGAAGGTTTCGATTTTGACTTGGAACAAT
CGAATCAGGAAAAGGAGTTAACGCCGGAGAAGTCTCTAGAGAAGAATAACACCGACTCAACTGTTAGCCAGCCGGAGTTCTTTGTCAAGCAAACC
AGAGATCCTCGTTTGCTAATTATTGGCAGAAAGAATTCGACGTCTTCGTTTGCTGAATCCAAGGCTTCAAAATCTATTTCCGGGGATCCTCTGGA
AACGGCTATGGAAGATAGTGGCGATGAATATGGTAGGGATGGTGAAAAACGCGTCACAGGCAGCGACACTACTTCTCCAACCCGACGTCCACGTC
GCGCAGCCCGTGCATCAATAAGTTTCGCTGGCATAAGGGATTTACCGATCCAGAAACCAGGCCAAGCACAACGAATGACGCGATTGCAGCGCAGG
AAATCTATGAGTTTAGCGGCTGTACACAGTGTAAGGAGCTCCACATCGCCTGTGAAAATGACTCCAGTCCCCAGGTCTCAGCCGATCAACAAGCC
GCCATCCGGGCCAGTCCAGATCACGAAAATCAGTCATCGGGATGACATCTTCCCGAGACCTGCGGTGCCATCTGGAGTTGTGAATATAAATCAAA ACCAACTCAAGACTCAACAACAGCAGAAGACGCTGATCTTTCCGACGACCGATGAAGCGATCGCTAACCCGCAGGGATCTGGTCCACCACAAAGG
AGGTCCGTGGGTAGGCCGCCCAAGAAGCTACCTATGGTGCAGCGAATAGTTGCGCCGGAAACGCAGACCAAGCCACAGTCGCCCATAAACACCAA
AGTCCTGACCATTGGCAAGCCCACCAGCTCCGTCGCGAGTGGTAACATAAATAATATTGCTATCAAAAGCAACGTCGTTACTAGCATAAGCAGCA
GCACCGCTACTACTAATACCATTACCAAAGGTACCAGTAACAACAGCATCAAAACTACTGAAAACGTTAATGTAATAAGCTACAGTCCGAATTCA
TCTAGCACCAGCAGCAGCAGCAAGGCCACCACTGGTGCCTCTGGTGCGGTGATAACTAATATACCCACAACCACCACAGCTGGAACATCCGTTCC
GGTCGGAAAGAGTATAACCCAATTGAAAATGACTGAGCGAGGCACTCAAACCGGAGTCCAGAATCCTTTCTCCGATAATTACTTTCTCGAAATGA
TCAAGCCCCAGATGCAGGAAATGAACCCCCGTCAGAAGATGCACTTTAAGAAGAAAGTATTCCAAGCGCTGATGGAAACCTTTGATGATGCTACC
GATTTCCCAACGTCTAAAGAACTGCAGCATTTTAATATAAACACTCCTTCAGGATTTGAGCACATTACAGATCCGGAACTTCGATTGGTCAGGGA
GCTAGTCAGCATGGTGAGCGCGGCTAAGGTTACCCTAATTAGACCGCCAGGAGAAGCTACAGCTATAGCTACAGCTTCCCGCAGTGGAATTGCTC
CTGAGGTACAGCGAGGACCCCGAACAAATATGACACGCCAAGTCATTCAGAGGGTATACAAGCCAGGCACTGGACAAGAGATCGCCCCCACCAGC
CCGGCGGGTGGACTAGATAAGAGGTTGTTCAGGTTAGCGGCTATGGGTGGTAAACCGAATGGCAACTTGAGTGCCACTCAGGAAATTTTGCGCAA
GGATAGTGTTGACAGTAACCATAGTGTGGTCAAGGTGGCCAACCACGCCCCAACAGGCAGTCCCAAAGGAGCTGCTGTAGTGGCTGCTATAAGGC
CGCAGGGTTCATTGATCAACAGTTTCTTTGGACAAGGCAATGGACCGACGACGGCCAAGGGAGCTGCCTCCGAGAATATCCGCGCCATGTCCAGG
AGGTATTCCGTGTGCGGTAGCAGCAATCCACCCAATGCCCAAAACGCTAGCCAAGGTTCCGCCAATGGCAGCACCATAAACTCCAATGCTAGCGC
TATGGAAGCGTCTATGCTTAAGCGGCGATTGATAGCAGCTGGGCATGGAATGGTGCCACCTACCCAACGCCCTCGGTATTCTGCCGTAGGTGCTA
GTCAAATGACCACTGCATCGCAAGGCAGCAGTTTACTAGTGAGGAAGTCTGTGGGCTGCGTTCCTGCTTACCAAAAGCAAATCTCACCCACTGGC
GGTGCCTCCCTGCTTCAGAAAACTCCGCAGATTGCCAGTGTGCAAGGATCTGCCTTCAATGACTTTGCCCAGCCCAAGCCCGCTGCAACGGCCTC
TGTAAACGGCGAAGAAAGTTCGCCTACCTCGGCGCTGAAGCGCAGCTTGGTGGTGGCTAATACCAAAACCTCCTTTCAGGACCTTCTTCAGCAGG
CCAGTCAGACGGTGCAGAGAAATAAAATTGAATCCTCGGAGACAGCAGCCACTATTGCTGCGGATGATTTTTCGCTGGACAACCTTAAGCGAGAG
CCAGTGGATCCCGCGGAGGATCACAATGACATACTCGGTGTTTAAGACCAGGCCAAAGAAATTTCCGAGTATTGATTAAAGAGTAAAGAATTAAG
ACAGATTCATTAAATCGTAAATAACACGTTGAAAAATTGTTAAGCTATCTAATGCACTTATAATGTTGCGTTAAACATTTTTTATAGTTCCCTAT
AATTTTAAGAATTTCGAATTTTTTTTTTTTGGAAAAAGTTTTTAACTTTTTCTATTTTGTTCATAATTTTTTAGACGATAGAAAACCGACAGTTT
TGTTCAAAATTTGCACAAGAAAAAATGATTAATGAGAAATCGAATCTTAACTTTATTTCACATTTTCTAGTTATATATATCGAATAAAAAATTGCCC
TTATAAGTTAAACAAAAAGGACAACTG
(SEQ ID NO: 1394)

Start ATG: 162

MSAASEVNLMLLRSVEKQTALYDRTDENYRKRLPSENAWDMVASEVGESVEKCKRRWRQLRNDYTRWCNADANRRRNGQRRLAYPLADELRFLDR
HLNIADDMAADDDRSVSSDKDRDNNRDSEGVDHHAQASLKERASSTSKLVKEVKLASQVRKEKSSQDKRENWENPGDKQRSRKKSAEEKLNDLEE
SDEPEKVPELDSFLQSDNEDDECMDEEHLEDLEGFDFDLEQSNQEKELTPEKSLEKNNTDSTVSQPEFFVKQTRDPRLLIIGRKNSTSSFAESKA
SKSISGDPLETAMEDSGDEYGRDGEKRVTGSDTTSPTRRPRRAARASISFAGIRDLPIQKPGQAQRMTRLQRRKSMSLAAVHSVRSSTSPVKMTP
VPRSQPINKPPSGPVQITKISHRDDIFPRPAVPSGVVNINQNQLKTQQQQKTLIFPTTDEAIANPQGSGPPQRRSVGRPPKKLPMVQRIVAPETQ
TKPQSPINTKVLTIGKPTSSVASGNINNIAIKSNVVTSISSSTATTNTITKGTSNNSIKTTENVNVISYSPNSSSTSSSSKATTGASGAVITNIP
TTTTAGTSVPVGKSITQLKMTERGTQTGVQNPFSDNYFLEMIKPQMQEMNPRQKMHFKKKVFQALMETFDDATDFPTSKELQHFNINTPSGFEHI
TDPELRLVRELVSMVSAAKVTLIRPPGEATAIATASRSGIAPEVQRGPRTNMTRQVIQRVYKPGTGQEIAPTSPAGGLDKRLFRLAAMGGKPNGN
LSATQEILRKDSVDSNHSVVKVANHAPTGSPKGAAVVAAIRPQGSLINSFFGQGNGPTTAKGAASENIRAMSRRYSVCGSSNPPNAQNASQGSAN
GSTINSNASAMEASMLKRRLIAAGHGMVPPTQRPRYSAVGASQMTTASQGSSLLVRKSVGCVPAYQKQISPTGGASLLQKTPQIASVQGSAFNDF
AQPKPAATASVNGEESSPTSALKRSLVVANTKTSFQDLLQQASQTVQRNKIESSETAATIAADDFSLDNLKREPVDPAEDHNDILGV*
(SEQ ID NO: 1395)

Name: stonewall
Classification: transcription_factor
Gene Symbol: stwl
FlyBase ID: FBgn0003459

Celera Sequence No. : 142000013384367
TAAGGTTAATTTGTCATCCTTCCTTTAAAGCGATTATTAATGAAGGTTGTGTTTCTTAACCAGGTGGTGCCGCCCAGAAGACCAACCAGGTGCGC
AATGGCGACGAAATCCTTAGCATCAATGGTGCCTCCACGTCGCGGATGACACGTGTGGATGCCTGGAACTATATGAAGCAACTGCCGCTGGGACC
GGTCAAGATTTGTTTCGCCTAGATGAAATGGTCTAAATGAAATACCAACGATGGGGAAGAATGCGCCACAATTTTCATAGATTTAAGCCAATTAG
CTTGGTTACCCCTTAACCGGTCTAACCTTGGGGGTCTTGCCAATTCGATGGATCAATGCTGCGAGCGATTTGTTTTGCATTTAAACGAACCTTTA
ATTGTATGCCTAATTTGATAGATATTTAATTTAAAGTGCAATTGTTTAAACCCTTACAACGTTTTCATGCCCTGCTTACCTACCTATAACTGATC
GATGATTGTACATATTACTAATCGAGACTAATTTACGTATTTAAACCTTTAATCAAATTGAAGCCAGCTATCGGGCAGCCCTATTTCCTTATACA
CAACTTATATTCAAAAAAACATAACGAAAAAAAAAACAATTATATTTATGCCATAAATTATACGGGAACGTTATACATGTATATTATTTTAAT
AATTATTATTTTATTTAAAGAACAACAAAAACAATGTTTACGTATACAAAAGTATTTGCTAAAAATAAACATACAACATATATGAAATTAACCTG
AATGTAATTTTTTTAAATTGTCTGGATTGTTTTAATTTCCTTCACAAAAAAATTTTAGTTTTCACAAAAAAGTCTAGTTTTAAATTTAGAAAAAT
TTATTTATTTAGTTTCAACTTCACATTTTTCTGTTTATACATTATGGGAACATTTCTAAAAACAACTTAAAATGTTATTTGTCCTATGTACTGTA
CATAAATTTGATATCAGTGTATTAAAGCTGTTCAATGAGCAGTTCGCAAGCTACAAATCTTTGGATGCCTTGGACACCAGCTTTGGCAGCTGCAG
CATAAGTCCCATGTGCTGTAGTGGATTCGCCGAGGAGAGACTCGAGGTAGTGGATAGCGTTCCATTGACATTCTCCCTGGGATGCGGCTGCGCTG
GGTGGGTTGATGAGGCTGACTGCTCGGAATGGAATATCTCGCCAAGCAGGTCGTACACACGTCGCTTGAAGTACAGCTTCTGGTGGAAGTTCATG
TGCTTGATTTCGGGACGCAGTCCCTGCAGGAATGCGTCATCGAAATCCATGATTGGCAATGCTTCAATACAGCGGGTTGATGTCTGAAATAAGAA
AATAACAAATCATAAATAAACGCTGTACAAATTAAATTTTGCACTTAATAGATTGTTACTTTGGGGAATTCAAGCAATGGCACTCTATATAAAGT
AATTTCTCCCACCTTGGCCTCCTTCTCACTGCTGTCGCTCTCTGTGCGCATTTCTGCCGGGACCGTGTCCTCGAAATCCATGATTGATGATGGTT
CATTATTAAATTGTGTTGCCTGAAGAATTAAAGGAAACTGCATCATTAAAATTATAAATGCAAATTTCAGCTTTGAAATAAAAACGGGCACACAG
TATAAAACTAAGCTAATTTGCACAGCTTTAACTTTTGACCAAAAATATAGCATACATCATTTTTTACTTTAAAGTATAGTTCATAACGCTAAAC
AAGGTTGTAATAATTTAAGGCCTCAGCAAAATGCATCTGAGTATTGCTCCCACCTCAACGTCCGTCGCCGATGCAGGGTCGGTGCTGTGACGGCT
CTGCGCATGCTCCGAATTCAGAAAGCTCGGGGAGTGCACCATCTCGAGGATTGCCTCTACGGGAGTTTCGGGATCCCCTTCGTCGTGCTCCTCCT
GTCCCTTGGGTCTTGACCTACGACCTCTGAGCGGAACGGGCACTCCGGGAGTGATGTGCTTTTGCAGGAACTTCAGCTCGCTGTTAAGATAGTAC
GTATTCGCACCGTGATGCAACTTTATTGAGCGGGCATAGCTGGAGCGAATGTTGCGCCAACGTTCCTTGCAGCTTTTAACTGAAATGATCAATAG
CAGTCAATAAGATTGTAAGATAATATTATATATAATATTTATATAATATAAATTGTAAGATTTTATAAGAGATTATATTTTATTTTATATTATGTAT CGACATAGTAAAATCGTGCTTATAAAAATATAAACATCTCCTAATGAAATGTAAATTTAATAATTAAAGTAAATTTAGTTAATATGCAATATGTC
GAAATATAGATAAAAACCCACCCGAATTTCGCATCTCATTGGATATTTCCTTCCACGCATTTTTCACAGTCGATTTCCGCAAGTAGTTGTCATCG
TGACGATCGTAAAGACAAGGATGTAGTTTCACCAAATGACATATTTTGGCATTGATGGCGTAAACGTTCGGTGGTGGAGCTATGGACCGACGGCG
TGTATTCATTTCATATATAAAAACTAAATATGCAAATTTAATTAATTAATATAATTAATAGAGTTAAAGTAGAAGACCCGAAATCGAATCTGAAA
CATGTGTCGCCTGACCGTGCAACAGCTGTTTGCCGCTACTTTGCTTCTCTGCTCCCGCTTTCAACAACAGTTATTTTCTCTGAAACCAGATCTTTC
GTTTAAACTTACGTGAATTAGGTTTAAAAATGCTCCAATTAATCGATGTCAGTGCTTTTATCACGAGTTTTGGCTTATTAAGTTCGGGCTCAAGC
CGCTCGTTGCTTCCGTGCACGCGGCAGTTGTTGGCGTGGACGCCGGAGTTGCTGCTATTACAAGTGTTTAGCAACTTTGAACACTGCGATTTCGT
GCTGCTGCCAACAAGTGATGCAGTTGTAAATGAATGTTGCAATTTCAAATAGCAATTGTTCTTGATTTTAAAGCACATGAGCACTAGACTGATTC
GAATTGGACATTTGAATCTTTAACGGGCGGAGAATATAAAACACCGGCAAAATAAATAAAGAAAGGAGCCACAACAAACGGAAAGCCAGAGGCGT
AGTCATTCTCTTCGCAAATCAGCGGGGTTACCATTCGAGCAGCATACAACCCTCTCTGAGAGAGAATTGACATGCCACTGGATCTCACACATAC
AATGAAAGGCACACTCACTCAAAGTAGACAGCACTGCCAGACTTAATGCAATAGTATAGCAGTTGGTGTTGGCAGTGCCATTTGATCGCTGGAGG
TGCTGCCAACGCATTTACCAATTAATTAATGACCACCCCTAAATGTTGTAAATTATAAAAATTATTCAAGAATATTACGATTTTGGTTAAATTAA
TGTACAAAATAAAATATTTCATATTTGTATTGGCTGTCAAATGAAGTTATTTTATTTTAAGATAAATGCTAACAAATCTTAGAGAAACTGGAAAA
CAAGGTTGAGCGGTTTTGAGAATTATGAACAACGCGTAAAAAACATTATTTATAAACGTAAAAAAATATTATAGTCTAGCCCGACAGGTAAAAAA
TAAATTTATCCGGGGCCACCTTGGTCAACCCTCGTCAACGACCGTTCGGCCTGCCAACTCGCTTTTCCCTGCAACGCAAGGCGCCGCTCTCTGCT
CACACTCTCACTTGGCTGTGTGTGTGTGCTCAATACTCGCTTTTAGTTTTCGCTGCAGTCGGTCGCCGTTTTTAGTCTCAGCTGCTGCGCGCGTG
TGTTGTGATTGTGTGAATTGCGTTTGCGTTTGTAGCATAACACAAAACCGATAAATTCCTGGCGAAGCGAGCTCTCTCGATTGGATTCTTGCAAA
GTGAACTAGCGATGAGCGCCGCCTCTGAGGTGAACCTGATGTTGCTGCGGTCAGTGGAGAAGCAGACTGCGCTTTATGATCGTACCGACGAAAAC
TATAGGAAGCGCCTGCCGAGTGAGAACGCCTGGGACATGGTTGCCTCCGAAGT
(SEQ ID NO: 1396)

Exon: 2948..2673
Exon: 2493..2302
Exon: 2074..1764
Exon: 1539..1438
Exon: 1318..1001
Start ATG: 2479 (Reverse strand: CAT)

Transcript No. : CT13005
TTCGAATCAGTCTAGTGCTCATGTGCTTTAAAATCAAGAACAATTGCTATTTGAAATTGCAACATTCATTTACAACTGCATCACTTGTTGGCAGC
AGCACGAAATCGCAGTGTTCAAAGTTGCTAAACACTTGTAATAGCAGCAACTCCGGCGTCCACGCCAACAACTGCCGCGTGCACGGAAGCAACGA
GCGGCTTGAGCCCGAACTTAATAAGCCAAAACTCGTGATAAAAGCACTGACATCGATTAATTGGAGCATTTTTAAACCTAATTCACTTTTTATAT
ATGAAATGAATACACGCCGTCGGTCCATAGCTCCACCACCGAACGTTTACGCCATCAATGCCAAAATATGTCATTTGGTGAAACTACATCCTTGT
CTTTACGATCGTCACGATGACAACTACTTGCGGAAATCGACTGTGAAAAATGCGTGGAAGGAAATATCCAATGAGATGCGAAATTCGGTTAAAAG
CTGCAAGGAACGTTGGCGCAACATTCGCTCCAGCTATGCCCGCTCAATAAAGTTGCATCACGGTGCGAATACGTACTATCTTAACAGCGAGCTGA
AGTTCCTGCAAAAGCACATCACTCCCGGAGTGCCCGTTCCGCTCAGAGGTCGTAGGTCAAGACCCAAGGGACAGGAGGAGCACGACGAAGGGGAT
CCCGAAACTCCCGTAGAGGCAATCCTCGAGATGGTGCACTCCCCGAGCTTTCTGAATTCGGAGCATGCGCAGAGCCGTCACAGCACCGACCCTGC
ATCGGCGACGGACGTTGAGGCAACACAATTTAATAATGAACCATCATCAATCATGGATTTCGAGGACACGGTCCCGGCAGAAATGCGCACAGAGA
GCGACAGCAGTGAGAAGGAGGCCAAGACATCAACCCGCTGTATTGAAGCATTGCCAATCATGGATTTCGATGACGCATTCCTGCAGGGACTGCGT
CCCGAAATCAAGCACATGAACTTCCACCAGAAGCTGTACTTCAAGCGACGTGTGTACGACCTGCTTGGCGAGATATTCCATTCCGAGCAGTCAGC
CTCATCAACCCACCCAGCGCAGCCGCATCCCAGGGAGAATGTCAATGGAACGCTATCCACTACCTCGAGTCTCTCCTCGGCGAATCCACTACAGC
ACATGGGACTTATGCTGCAGCTGCCAAAGCTGGTGTCCAAGGCATCCAAAGATTTGTAG
(SEQ ID NO: 1397)

Start ATG: 291 (Reverse strand: CAT)

MNTRRRSIAPPPNVYAINAKICHLVKLHPCLYDRHDDNYLRKSTVKNAWKEISNEMRNSVKSCKERWRNIRSSYARSIKLHHGANTYYLNSELKF
LQKHITPGVPVPLRGRRSRPKGQEEHDEGDPETPVEAILEMVHSPSFLNSEHAQSRHSTDPASATDVEATQFNNEPSSIMDFEDTVPAEMRTESD
SSEKEAKTSTRCIEALPIMDFDDAFLQGLRPEIKHMNFHQKLYFKRRVYDLLGEIFHSEQSASSTHPAQPHPRENVNGTLSTTSSLSSANPLQHM
GLMLQLPKLVSKASKDL*
(SEQ ID NO: 1398)

Name: stwl-like
Classification: transcription_factor

Celera Sequence No. : 142000013384637
CTTGCCTACGAAGTGGGTCTGCTGGTCCAGAAACTGGCCGGCGGAGTTGGCCCCCCATTGACGAAGCCCAACAGCAGTGCCCACCTGTAGAGCGG
AATGACGAACTAACCTCTCACGGGAATCGACAATTGACACAGATCCTGGATGGAGCAATAAATCTCTTTACTCTAAGGTGCTCAATAACTTAAAA
AAAAAACAACTTAACTCTCAAACGCATTTATTCTGCAAATGTTCACTGTCTTTTGTGTTCTAAAGATGACATATTTTTTGCCATTATTTATAAAG
TTCTTTTCAAGTTTATTTATACATATGTACATTGTGAAAGTTGCAATTTTATGTCCTTCGCTATTTTGTAATTGAAGAATTTAATGAAAATGCAA
CCGCTACGTTGATTTTTTTGTTGAGCTGCTAGCGGTAACTATTGAAATTATAAAAGAATTGATAGTAGAGATTAATGAACCTAATCAAGTTTGTA
TTGCTATTTTCTATAAAAGTATTTTTTAAACAATCTAAAGATCCTTTTACTTTAGGTCGAATATAAATCAGTTTTCACTTCATTTGGAATTTACT
ATGCTGTACGCACAATTTATGGCAAATTTAAATCACTGTCCCGGCAAATAAATTAAAATTTTGCCAACTTTTATTTTTAAACTTAACATTTTAAT
AAATGTTAATGGAGCTGGCAGAATTGAAACGCGCCATCTGGCGGTCAGTAGCGGAGACATGTAGGACAGTAATTGATAAGGACTACTGTTAACTG
TTACAATGTAAGCAAATACTTCAAAACTGTTATACTTGTGTTAATTAAAGCATACGTTCAAAAGTCGAGTTGAGTTATTGAATGTTAACTGTTCG
TAGTTCGAAAGTTATCTAATTTAGCTAACTAATTTAGCAATTGTTTATAAAAAAGTTTTACTTGAATATTATTAATACTCGGTATATCTATGCAA
ATGGTATTAAAAGTATATTTTCGCATGCCGGATGGTTTACTCGTCTAAAACTCAGCCGGTCACACCGTCTGATTGCCGTGCTGTCACTTTGGCTG
ATGCAATTGCAGTTTTTTAGTTAAAACAAAATTAGTTTCCAGTCAACTAGTATTCAAACAGCCCAGACACAATGGACGCGGAAGACGTAAGTTC
CCGGAACACCGGCTAGTGCGTTTCATACGCGGAAAACTTGCGTGGAAAATTCGCATATTATCGTACATGTGCGCCCTTGTTTGCGTATGTGTATG
TGTGTATTTACACATTTGTGTATGAGAACTGGGCGAACATTGAGGTTATGTTTGCTTGATCCGGATTTAAACCATATTGAAATTCCAATGATTTT CGCAGGGTTTTGATCCCACTTTGCTGAAAAAGAAGAAGAAGAAGAAGACCACGTTCGATCTGGACGCGGCATTGGGTCTGGAGGATGACACCAAG
AAGGAGGATCCCCAGGATGAGGCATCGGCGGAAGGAGGTGCCGCCGCCGAGGAGGATAATCTAGATCTGGAGAGTTTCGGCAAGAAGAAGAAAAA
GAAGAAGAAGCCCTTCAACATGGACGAAATCGAAGCGGCCATACCCAGCTTTGGCGGCGATGATGTGGCCGCCAGCGAGGAGCCCGAGGAGGAGG
AGATCAATCTGGACATGGACTTCTCGATGGCCAAAAAGAAGAAGAAGAGCAAGAAGAAGGAACTGGACGAGCTGTTTGCGGACCAAGCGGACGAC
GACAAGAGCGAAGACAAAGAGAACGGTACGGTGACGAATTGCAGAGCAGCCAGGGAAGCTTAGGGTTATAGAATCATCCCAACCAAGATTGGCAG
CCATATAAGCTTGTTGTCACTTGACAAAGGCAAAGCTATACGATTCTTAAAGTGTATAACTTGGCTTTCGCCTTTTCCGAAGCATTAAAACTCAG
TGTATGAAGTGAACTAGAAATGCTTAGCCAGTGAGTTAGCATGTAGCTGTTCCAACTTTAAATAGACTCCAGATTTCAAAGCTCTCACTTAGCAA
ATAAGCTTATACCATACCCTTTTAAATAACGTTTTCATCCGTTTACAGACGAGGACAACAGCTCAACCTGGTTTGGCTCCGACCGCGATTACACA
TACGACGAGTTGCTGAAGCGGGTCTTCGAAATCATTCTCGACAAGAATCCGGACATGGCCGCCGGCCGAAAGCCAAAGTTCGTGATGCGACCGCC
GCAGGTGCTGCGCGTGGGAACCAAGAAGACCTCCTTTGCCAACTTCATGGACATTGCGAAAACGCTGCATCGCCTGCCCAAGCATCTGCTCGATT
TCCTGCTGGCCGAGTTGGGTACCAGTGGCTCCATGGACGGCAACCAGCAGCTGATCATCAAGGGCCGTTTCCAGCCCAAACAGATCGAGAATGTG
CTGCGTCGCTACATCAAGGAGTACGTCACCTGTCACACCTGCCGCTCCCCGGAAACGATATTGCAGAAGGACACGCGTCTCTTCTTCCTGCAGTG
CGAATCCTGTGGCTCCCGCTGCTCGGTGGCCAGCATTAAGTCAGGTTTCCAGGCTGTCACCGGCAAACGTGCCGCCATACGAGCAAAAACAACCT
AAATTCTCCTTATTTAAAACTTTTTGAATTTTTATTACCAGTAAAATTTCAATACAAAAAACCAACGATACTATTTATTTGTTGTATTCTGCATT
GTTTTATGCCTTCGTTGCCAGTCGGTTAGGTAGTCTACGAAGCCAATTTCCATATTCCGCGATCGGCCGCTGTCTATGAAGAACTGAAAAGCGTC
CAGACCCATCTTGCCGCGGAACCTATTCGGACGACCGCGCAGGAATAGGCTGTGGCCCCTCGAGATGCGCGTGGGATCAATGTACTCCATGGAGA
CCTGCAGCAGCCGCATCATGCTCACGGCAATGCTCTTGTAGGCCTCGGACGAGGCCAGCGAACTGGCTTCACTGTACAGGCTGCTGATCACGCGT
CCATTGAAGGGTTTTTTGGTGATGCTGGCCTCCAGGGAGCCGGTGCCATCATCGATCATGAACTTCATGAACGACTCGTTGTGCGTTCCATTGCC
AGTTACAAAGGCGTAGATGATGCAGGTGCAGAAGTGAATCGGATGCACGTCGTCTGTGATGAACACATTCTCGTTCTCCGGATCCTGAGTTGCGC
GCTCAATCTGGGATATGGTCAGCGGCACGTTGTCGTGGACCTCCGGACCACATTTGCCCGTGGACTTTTCACTCTGTTGATTCTTGCGTATCACG
AAGTTATCCAGCTGGCTTTCTATGTCCTCGAAACTCTGATTAAAATCCATTCTATTTGCTTAGTCTGCGATTTCAAAGGGGATTTCTTTATTGCA
GTGCATTTTGCATTAGCGCCAAAAAAAAAAACAGTTGTGAGCATGGGCGTAGACTTCGTATTTTCTTACAAATAATATTAATTAAAATTAATTTT
GTGAGCAATTTTCACACAATTGTATTATAAGTTAAAACCAGGGTCACATTAATTTGCAGAACCGCGCAATATTTTCTTTTTAACCCCCTTACAAA
TTTTCAGTTGTTTTGACTACGCCCCTGCTAATTTTTACTTATTAAATTCAAAGTCTAAAAACATTGTCACCAGATAATACGAGTATACACTATAT
GGACAAACGTAAAATCGT
(SEQ ID NO: 1399)

Exon: 1001..1132
Exon: 1336..1735
Exon: 2044..2628
Start ATG: 1118

Transcript No. : CT13682
CTCAGCCGGTCACACCGTCTGATTGCCGTGCTGTCACTTTGGCTGATGCAATTGCAGTTTTTTTAGTTAAAACAAAATTAGTTTCCAGTCAACTA
GTATTCAAACAGCCCAGACACAATGGACGCGGAAGACGGTTTTGATCCCACTTTGCTGAAAAAGAAGAAGAAGAAGAAGACCACGTTCGATCTGG
ACGCGGCATTGGGTCTGGAGGATGACACCAAGAAGGAGGATCCCCAGGATGAGGCATCGGCGGAAGGAGGTGCCGCCGCCGAGGAGGATAATCTA
GATCTGGAGAGTTTCGGCAAGAAGAAGAAAAAGAAGAAGAAGCCCTTCAACATGGACGAAATCGAAGCGGCCATACCCAGCTTTGGCGGCGATGA
TGTGGCCGCCAGCGAGGAGCCCGAGGAGGAGGAGATCAATCTGGACATGGACTTCTCGATGGCCAAAAAGAAGAAGAAGAGCAAGAAGAAGGAAC
TGGACGAGCTGTTTGCGGACCAAGCGGACGACGACAAGAGCGAAGACAAAGAGAACGACGAGGACAACAGCTCAACCTGGTTTGGCTCCGACCGC
GATTACACATACGACGAGTTGCTGAAGCGGGTCTTCGAAATCATTCTCGACAAGAATCCGGACATGGCCGCCGGCCGAAAGCCAAAGTTCGTGAT
GCGACCGCCGCAGGTGCTGCGCGTGGGAACCAAGAAGACCTCCTTTGCCAACTTCATGGACATTGCGAAAACGCTGCATCGCCTGCCCAAGCATC
TGCTCGATTTCCTGCTGGCCGAGTTGGGTACCAGTGGCTCCATGGACGGCAACCAGCAGCTGATCATCAAGGGCCGTTTCCAGCCCAAACAGATC
GAGAATGTGCTGCGTCGCTACATCAAGGAGTACGTCACCTGTCACACCTGCCGCTCCCCGGAAACGATATTGCAGAAGGACACGCGTCTCTTCTT
CCTGCAGTGCGAATCCTGTGGCTCCCGCTGCTCGGTGGCCAGCATTAAGTCAGGTTTCCAGGCTGTCACCGGCAAACGTGCCGCCATACGAGCAA
AAACAACCTAAATTCTCCTTATTTAAAACTTTTTGAATTTTTATTACCAGTAAAATTTCAATACAAAAAACC
(SEQ ID NO: 1400)

Start ATG: 118

MDAEDGFDPTLLKKKKKKKTTFDLDAALGLEDDTKKEDPQDEASAEGGAAAEEDNLDLESFGKKKKKKKKPFNMDEIEAAIPSFGGDDVAASEEP
EEEEINLDMDFSMAKKKKKKSKKKELDELFADQADDDKSEDKENDEDNSSTWFGSDRDYTYDELLKRVFEIILDKNPDMAAGRKPKFVMRPPQVLR
VGTKKTSFANFMDIAKTLHRLPKHLLDFLLAELGTSGSMDGNQQLIIKGRFQPKQIENVLRRYIKEYVTCHTCRSPETILQKDTRLFFLQCESCG
SRCSVASIKSGFQAVTGKRAAIRAKTT*
(SEQ ID NO: 1401)

Name: eIF2-beta
Classification: translation_factor
Gene Symbol: eIF-2beta
FlyBase ID: FBgn0004926

Celera Sequence No. : 142000013384528
GAATCTAAGTGGCATCAGAAATCTGATCACGACTACATAATGGCGGGATCTGGAGTTGCCAAGCAGATATTTGCCCTCGATTTCGAGATCTTTGG
ACGAGTGCAAGGTATGCAATGCATTTTTCTGATTCGGCTTGTTAAACAGCGTATTAAATTTTGCAGGTGTGTTCTTCCGCAAAGTAAGTACTGGG
AGGCCTATATATATATCTGGAAATCAACATTTAACTTATGTACATTTTTGGCTTAGCACACGTCGCATGAGGCTAAAAGATTGGGAGTTAGGGGC
TGGTGCATGAATACCCGGGATGGGACCGTCAAGGGACAACTGGAGGCTCCTATGATGAATTTAATGGAAATGTAGGTACCGCTGCACTCCACTAA
TTCAATCATTTAACCATCGCCCACTAATTTGAAGGAAACATTGGCTGGAGAACAACCGAATTCCCAACGCTAAGGTCTCAAAGGCTGAATTTTCG
CAAATCCAGGAAATCGAGGACTATACGTTCACTTCCTTTGACATAAAACATTAAAAACGAATTATTAGCTCTTTCGTTGTCCATCCAATTCCGAA
ACAAAGTCTAAATAAATTACCAGGGCTGCAACTTGCGTAAGCAGGCATATCTGCATTGCTATCGACTGAGTCGATAACATTCGATAGTATGAACA
TAAGAAATATTACGTTTCGCAAAACTGAACCCAGTACTGAAGTACAACAATAAATAAATAATAAATTATTTAAAACAAGGCGGAAAATTATTCCG
AGAATCGATAGTCGCTAGTCGAAAGTGCGCACCACTCCAGTATCTACTCGATATATTGCTATCACAGCCGATAGTTTGCAGCTCCCTGCCATAGA CACTGGTCATCTCGCTCGCACACACAACAGTGGGCCGCGCCACCGCCATAGGCGGCGCACGTGCAAGAGCGAGACAACCAGCTGGGCGACAGCGC
ACTTTGGTCTGGCACAGAAACGAGTACAGCTTCGATACACGTCGTTTTGCCAAAAGCGTAGCAGAGCAGTCTAAGCGATGAAAAAAATAAATGAG
GAAAAAAGTCCGTGAAGCGAAAACCGTAATTCCTACAGTGCGAGTCACGCCATTGTGTTTGCAAAAAATATTTGCCAATTGTGCTACGGGCAATT
TTTCGGAACGGCCGAATTGTGCGTATAATGAAAAAAAATACTACTTAATTTTTAAGCAATTTACAAATTCTTGCGTGCTGCCTGCCTGCTGTCGG
TGTGTTCTTGCTTGCATGTGTTAGTGAGTACGATTACTTTCGCGCTGAAAACCTTTTTCCACTGCCCTTTCGCTGGAATCTGGGCGAATATAGAT
AGGACACAAAGCACATATAACTGATTTTTACTGCAGAATTGATCGAGACATGTGGAATACAATAAATGAGATTGTGTAAATAACTGAATATAGTG
GCGCATACAGTTGCACGTGTGTGTGTGCTAGCATGTGCGTGTGTGTGTGTAAAGGCGCGAGTTTCCGTTTGCCTAGGCTAATTGTAGTGGAAAAA
CTCAATAAACGGAATTACATAAAAACATGGTGGCATGATCGGCAGTTTCCCGCCGGCAGAAGATGCCCAATCTTGGAAAATTGTAATTTTCGAAA
GTAACCGCAATGATTTCGTCAGTATGTAAAGTAGTCTGTCAGTCCCTGCATATGTTTGTGTGTGTGTGTTCTATACAGTTTTTTTATTGCGCAT
CATGGTGTGCAATAGCGCGCTTTCTGACCTCTCTCTCGCTCTCATGGGTTCTCTTGTTGGCCAAAGCGACGCTGTGTGTGTGTTGTGTACGCATA
TGTAGCATATGTACATAACACGCCGGAAAAGACAAAAAAAAAAAACCATTCCAAATTTTGAAATCTTACGGAGGCGGGCGGTTTAAACGAGATAA
AAAATAAATACACCAATATTGTTCTTTTATATGATAACGCAGTAGTCTCGGACCGAATAGTATGCCTTTATTTTGTCGTCCTAACGCTGAATTGC
CGAAAAATAATAGCCCGTTTTTGGAAAATTCTCGACAGGATTAGCATAAAGAGACGCCTTAGGAGTCGAACGAACCAAATGCCGCAGCAGCCGGC
CAACGTATTAGCATCAGAACGATGGCCCCAGCGCTCACAGCCGAGCCACTAAGTCCAAAGGAGAAGCTAACCAGCACCGCCTCGCCCTCGGCCCG
CAGCTCCTCGGAAAGCGGAGGAGTTGGATGTGCAGTTGGCTTGGTCAAGAAGCCGGCAACACCCACGCCGGCCACGGCCACCACGCGGATTACCC
GCTCATCAGCGGCAGCGGCCTCAGTTACCGCTTCCCCGCATCTACAACAGCAGCGATCCTCGCTAGCAATCAATAACAAGCGAAAGTCGGGCAAC
GCTAAAGCCAGCAATGAACCAATGGGGCTGAGCACAGCCCCGACTCCACACAGCACCACTTCACCAAATCCCTCGACGGATACTGCGGCAGCCTC
CACCTCTGCCGTGGAGCACAACAATAACGACAGCAACAGTACCTCCGCCGGCAACAGCACCTCCGCCGACAACAGCTCCACGCCCAAGGACAACT
CCACCGCTCAGCTACTGGCGGATCTAACCATCAACTTTGAGGAGACCATATCCGCGGAGATTTGCCTGAGGAAAACCCTACCCGATGTGAGTCTG
GGGAAAGAGCCGGTTCCGCCTGCCTCGGTGCTGGCAGTGGCCACAAGTTCAACGAGTGCTGGCAGCGCTCTATCCTTATCTGCAGTGGATGAGGT
GACCAAGATAGAAATAGATAATATAGAAGGTGGGTCTAAGGAATCACTCCAAATAAATAGTCTTGACTCAAAATTTCTCTCGCCCACTGTTTCAG
AGCGTCTCAGCCAGCTAGATGGGAATGCCACTGGAAGGCCCGAGGAGCATGTGGCACCACCTTCTGTTCCGGTACCCGTGCAGGAGGCGCCAAAC
ACGCCCACCAGGCCACAGGCGCCACCAAGTGCCCATCTTGAGTCTCCGCAGCCGGCGCGAACACAGCAGCAGTCCATTCAACAGATGACGCCGCA
AAGCACCACCAGTTCCAACAATTTTCTCAAAGACGGAGCAGCTGGTGCTGTTCTAGAGGATCAGGATATCGAGGAGGTGCTTAAAGCGCTCAAAA
CATTTGACGGTGGCCATGTTAATCCAGATACCATTTGCGAGTTTTTCGACGAAGTTTGGGAAGAGGCAGCACCGGCAGCGCCATTGCCGCCCGCG
CCACCCGAAAATGTGGTGGATGTGCCGGGCGCGAAGCCCAGCTGCAGTGGCATCCTCGTTAGCGGCAGCAACATTTCCCAGCCGAATGTGATTAT
TAAGCAGGAGCAGCGGCCCTGGCAGGAGAGTCATGCTGAGTTGGAGCAGCAGCAGCACGTTATCTCGCGCAGGATCGAGTTTTTGCTACGCAGGA
TGCGCAAGCTCCAGGCGCGAGCGATGTGCCGTCACGCGAGCGAGGAGGTGGTTGGTATCATGGAGTGGTCTGCCCGCAGTTCCCATAAGGCTCCA
GTTCCAGCGAGAAGTTCCACGCTGACTGAGCAGGAGGCCACTGTCCTATCGATTGTCTCAGGGCGTCCGAGCTCAACCTTCTGGGAGGAGCAGAA
CAAGCATCCGCTGCCTGCTAGCCAGATGAGTAATGTGATCCGGCATATTGCGACGGCGGCAAAGCATCAGCAAATCTGCCACTCAGCCAGCGGAA
GCTCTGCTACTCTGGCGCCATCCTCCAGCTGGTACAACAGCTGCAACAGCTCTGCGCTGCCGATGAAGCGTCCACGAAAGAATCAACTTGATGCT
TCGGTTGCAACGGGTGCCACACCCACTGCACCTGCGCCAGGAGCGGTAACATCTAGACAGGCAGCTGGCACGACGGGATCCGCAACGGGTTCGAA
TACACCGCGGGCGGATGATATCGTGCCCGGCTACGACACCTATGTGACTAATGAACTCACCCATGTGTCTGGCCTGCTGCACACGGAGCTTCGAG
AAGTACAGAATGCCATCGACTCGGACGCCACGGAGTCAAGTTCTGGTGGAGAATCCGCTGACGAGATGGTAACCTACAACAACAACCAGCAGCTC
TCGCTACCAATGTGAGTACTTCGTATTATTTATGTACATACTTAGGTTATCGGGAATATTTTACAAGTAAACTTTCTTCCATCTTTTTTTGAGGG
GGGTTTTCAGCTTCTGTCATCTTTTTAAGATCATTCTTTTGCTATAGAATTTGTCCGATTAATGTTGGCTCGGTAGTTTTCTTTCAAAATTGTTT
TGCTTTGACAGGCATTTTAAACATGATTTAACGTCGTCCTTAGCAATTGAAAAGTTGTAATAGGCTTTGATTAGAGTTGTTGTACCTAATTATCG
CATTTACAATGCGATATTTCAACTATTTCAACAGTTTTTATTAAAATTGTTAATTAGCGATTATATATTTCTTTTAGCTTTTTTTTTGTGGTATT
CTCTTTCCTAATGCTCTTGAAATTTGATTCTTTGCAGCACTCGACGCGCTGTCTGGCGATATTCGAGAGATCGTGCAGCCATTGCCCTGCGCTGG
TCCTGGCTCTGCTCCCAGCTGACCGATTTGGAGATGAAGATCCGTCAGCACAGCGACCTTTACATGGATCTAACTCAGTCCAAGGGCGAGATCCA
GCTGGAGTCCACAGCTAAGACCTCACCGTCGCTAGCACAGCCGGCAAATGGCATTAAGGAGGAGCCCGGATCCGACTACCTCTGCAGTCGGGCAC
GTCCATTGGTGCTGTCCGAGTTCCGCAAACGCAAGCTCTTCCAGACCACGAACATGCACACGATTTCCAAGAAAGCCGCACGCCCCAGCAACATT
AAGTGTGGCTGCCAGTGGCCGCAGGTGCCATGCACACTGTGCACGGGTCGGACAGACCCTACGGCGCCCAGGGATCTGGTCGAGACGATGATGCC
GCAAAACCGGGTGGCATTGCTCGATGCTGGCTACCATCCAGTGCTCAGCTTCGCCAGCGGTGAGTGGGAGGTTACACTGAGTGGACCCATTTGGT
TTTCGTCCATGATTATTTCTTATCATCTGTGATGGTTTAACATTATTTATTCTACACTTGAGATTTGAACTGAATTGATTAAAAAGTAAAACTTT
AAAATGCAATACTTGCAAATAATTTTTATTCGAAACTAAAACATTAAAATCCTCGTATTCTTTACATTGGATTCCAAAATGAAAAGAAATAGTCG
GATGATGACAGCTAAAGTGGAATTATGTTTGAATATATTCTTATCCCTATCATTCTTGTTTCCCAGATGTCAGTCAGTCGGTTCACTTGGAGGCC
GTTGCCCGCCAGCCGGACTGGCAGTACCGCGTCATGCGCAGCCAGCCCAAGGCCATTGTCAAGGCCATGTGGAAGGCGGAGCGCGAGACGATAGC
CTCAGGCGGTGTCGGCGGACAAGGTGGCAGCCGGCGGTCGGGCGATGCGGCGAAGCGGCGTTATATACGACGCAAGGAGCGCAACAACAACTCAA
ATAAGGAGGCTGGGAGCGGAGCTAAAGCTGCTGCTGTCGCCGCAGGAGGAGCAGGCGGAAACGGAAGCAGTAGCGTCGGGGGAGGGGATAGCGGA
AACGGTACTGGTACTGCTACTACTTCTTCTTCTACTACGCCTACTACAACGCCACTTGTGGCCAACAGTAAATTATTGTAAACATGACGAAATTC
GATAATTGTTATTAACATAAAACAACAACAATCTTTTGCATCTCTTCTTCTTCTTTTTCTTTGCATCGATCAACCAAAACACGAAATTCCACCAA
CACCATCAACAAACACCACCACCAACAACAACAACGAAAAACCCCACCAATTGTTTTATTTTGCCATTCCGTTCTTGTCTCCGTTTCGTCCCCGT
TCCGCATCCAAATCACGGACTTGACGCAACATCAGCAGCGGCCAGGGGCAAGCGGCAACCACAACACCCAACTGGAGCGAACAGTTCCAGCTCGC
TGTGGCCAGACTCTCGCCAACGCCAACGACAACGCCACCACAGTCCCTCCTCAACCTCGATCTCGGCACTGAGCGGCGCTAAGAAGGCACGCAAA
TCCGCAACCAACAGCAGCAGCAGCAATTCCACACAGCAGCAGCAGAATCACCACGGCACCAAAATCAACAATCATCATCTCAATGGCTACGGCGA
TCAGTGGGGGGAGCAAAGCAGGAGTCGTCGCAACTCTTCGCCCTCCAACAGTCATAAAAATGAGAGGTATGTTTCGGATTCAATAACTGATCCCA
GGGATTCGCGATAAGTAGTCCTGCTTTTTTTTTATAAGATAGATTGTTATATATAATTTATATGTATGTTTCCCTTGCAGAACCTCTGAGCGTCG
CGTTCGTCCCATCTACGACATCAATAACATCGTTATACCCTACAGTATGCTAGCCCAGTCGAAAATGGAGATAATTCCCTACAAGGAAATACCCA
TACCCAAGTAAGTATTCAATTTTGCGCTAAGTCCTTATTTTATATATATATGTCGCATAATGTAAAATACCAAGATTTGTGTATATCTATTAAAA
TCACCCATTCCATCTTTGCTTTCAGGTGGCGCATTGTAGACAGTGATAACGATAAGGGAAAACATTCGTCAGATGAGTCAATGGAGCGCAAACTG
AGCAATGGCTGTGTCGCATCAAAGTCAGAGGAGCTAGCCAAACAACAGCTACCACCACCACCAGATCAAGATCAAGAGCAGCCGGCCCTGCAGCC
TCCGAAGGTTAATGGTTTAAAGGAAAATCAAGCAGTCAAGCACAATAACAATAATAATACAAACAATAATAATAATAAAAATGGACTGGTAAATG
GTAACGCCAAAAAGGATGAACTTAAGGCTGCAGAGGATCACGATACGCAATCAAAAGAAGACGACGATCCAAAGGAAAAGGTGGTCAAACCCAAG
CTCAACGGAAACTTGATAAAGAATCCGATTGACAAAACTGCCGAAACGCAAGACAAAATTGCTCAGCCAGCACCAGAACCACCACTGCCAAAGCG
ACCCAAGCTGGAAACTCCAACCTCCAACGAGGTCACCAAGGCTAATGGGCAGTTGGTGCAGCAACAGCTGGAATCCCGTGAGAGCGAGGAGGAGC
CACAGCATGTCGACGAAGATCTTTCGGATGAAGCGTTTATTATGCGACATCAGCGAGCTCTTCTCGAGGAGCGACGCCGCTTCGAGACTTTCCTT
AAGTTCCCCTGGAGCACCCGATCGCGTGCAAATAGGCGCGTCGATAGTCGTGCCGAATCTAGTGGCGCCAACACACCGGATCCCGCCTCACCAGC
TCCTCATCTAGGCGGCCCTGGTCACGACAACGAAAGCATTCCCTCGCCGCTGGCGTACCCACTGGACGCTTTTAACGAAAGCGGTGAGCTGCTGA
CTGGCGGACAGGCACGCCAAGCTCGTCGTCGGACTACGTCTAGCAAGCTTAAGGATCAGCTGGAACGGCGCAGCACCACGCCCGATCTGCGGGAG
GTAAGTCGATGTCCAAGTTTCACATTTGTTGAACTCATATATAAAATAAATTCTGGTTGTGCCTATTACTTTTGCCGAATTTTGTTTTCAAACTG

FIGURE SHEET 749

CTTTGAATGTTCAAATACTGATTGTATAGAATAGTTTTCTAATTGAAACCCTTTTCCTTTTTGTATAGTCTTACACTGTGATGCCATCTCCCTTT
GAGCCCTTGAACTTTCCGCTCTCCGACGAGGTCTACCAGCGATTGCTAGCCGAGACATATGCGCCGCCCAGGTCAATGACCGTCTCAAAGCGGGC
CAAAAGCAAGTCGATATCCTCGAACTGTGATGGTGGGAACACCTTCACAGGAGGCAGCGGCAGTCGGCGCAGCAGCAAGTGCAAGATTAAGCCAA
ATGGTCAGCTAAATGGCCAGCTCAATGGCCACCCTGCGGCGGCGAAGTTGAACGGAATAGATGCGGCAAATGAAGGTGGAATTTCTGAGCCGGAA
GAGGAAGAGATGCTGCTAGAAGACGAGGATGACGACTATCCCAAGCATCATCTGGCGCCGCTGGATGACGAGGAGCCGTCGACACCAGATGTCGA
GCATGAGCTTTACGACTCGGCGATCGATGCCTATCTCGCTGATCCGGAGGCGCTAGAGGAGGATATGGGCGAGGATCCCTTCGAGGACGACGATC
CCAACGATCCGGAGTGGAAGACACGGACCGAGGGTGTTCGCAGCAGACGCATCTAAGACCAAAATCCAAAGTTTTCGTTATTTAAGACTTTTAAA
CGATTTGTCAATTTTTAAAGCCACAACACACACACACCCACAAATCAGCCGGAGCAGACCAACAAATTTTAATTTGTTTCAAACGGTTTGGTTTG
CACTCACAACAGCATTGCGTACTCTAAGCAATCGTCTAAGTTATTTAGTTCTACGAGCCCACAACAAAAAAAAAAAACACAGATACGCTACACAC
AAGTACACAACAAAACAAACACGAAGCAGAAGCGAAAATCTTGAAACAATGTAAATACAAGCTAAACGCATAGAGCTAAGCAGTTACTGATAATT
GTACACTAACCAACGATCAAGAAATCATCGAACGCACCCACCACGTCGCGTGGACGTGGTGGATGCGGTCGGTTGGAGCACTGGTCAGCGGTTAA
GTAGGCACCACAACAAACCCACTTGGGCTTCAAGCCGAAGTGCGCTAATGATAAAAATATTAAGCTAATCTAAATATATATATATATACGAAAAC
ATTTAAATATATACCATATGCATACATTAACGTGTAAATGCCGAAGAGAGCAGTTAGCTGAAGATTTGAAATGTATTCGCACCTGCACACAAACG
ATATAACAACTAAGCTATAGAAGGCAATTATCTGTAAATTGATCAAGCTTAACCATTAGCTAACCAACCATTAGCCTTTAGCCCAGCAAGTAATC
AGTCGGCGTTGGGGCCGTGTTTTTCTTATATTTTAAAAAGTTTATCAGCTGTAAATGTATAGAGCGGAATTCGAAAGGCGGTGTGTGAAAATGGA
TCGAACGATAAATGTATGTATATGTATTTTAGTTGCTTAGGCGTTTTCATTTCTACCTTATAAACACGTTAGCGGCTAATTGTAGCAATTAATAC
TATAAAACACAAAAAAAAAAAACAAAAACAAAAAACAACAACCATAAGGAAACCTAGCGCGGCTATGTCCGTGAAAATGTTTATTCTAATTTCGTT
TTTACTATCTACTGCGTATGTTTCACCGCAAAGCTAGAATCCAGTTTAATTCGTTAAAACTTGAAAAGAAATACAACAGAAATGTGAAGATTAAC
TAAGGACCGCAAAAATACAGAATTATATATTCTTAAAAATGACACATGGAGCGCCAGAAGTGATATGCTGGGACCACCATCGCCAGATGGTGGAA
TCTGGCCAACATGTGTGTCG
(SEQ ID NO: 1402)

Exon: 1001..1052
Exon: 2034..2784
Exon: 2851..4096
Exon: 4503..4999
Exon: 5292..5672
Exon: 5926..6241
Exon: 6351..6467
Exon: 6581..7505
Exon: 7669..8425
Start ATG: 2112

Transcript No. : CT14929
CAAAAGCGTAGCAGAGCAGTCTAAGCGATGAAAAAAATAAATGAGGAAAAAAGATTAGCATAAAGAGACGCCTTAGGAGTCGAACGAACCAAATG
CCGCAGCAGCCGGCCAACGTATTAGCATCAGAACGATGGCCCCAGCGCTCACAGCCGAGCCACTAAGTCCAAAGGAGAAGCTAACCAGCACCGCC
TCGCCCTCGGCCCGCAGCTCCTCGGAAAGCGGAGGAGTTGGATGTGCAGTTGGCTTGGTCAAGAAGCCGGCAACACCCACGCCGGCCACGGCCAC
CACGCGGATTACCCGCTCATCAGCGGCAGCGGCCTCAGTTACCGCTTCCCCGCATCTACAACAGCAGCGATCCTCGCTAGCAATCAATAACAAGC
GAAAGTCGGGCAACGCTAAAGCCAGCAATGAACCAATGGGGCTGAGCACAGCCCCGACTCCACACAGCACCACTTCACCAAATCCCTCGACGGAT
ACTGCGGCAGCCTCCACCTCTGCCGTGGAGCACAACAATAACGACAGCAACAGTACCTCCGCCGGCAACAGCACCTCCGCCGACAACAGCTCCAC
GCCCAAGGACAACTCCACCGCTCAGCTACTGGCGGATCTAACCATCAACTTTGAGGAGACCATATCCGCGGAGATTTGCCTGAGGAAAACCCTAC
CCGATGTGAGTCTGGGGAAAGAGCCGGTTCCGCCTGCCTCGGTGCTGGCAGTGGCCACAAGTTCAACGAGTGCTGGCAGCGCTCTATCCTTATCT
GCAGTGGATGAGGTGACCAAGATAGAAATAGATAATATAGAAGAGCGTCTCAGCCAGCTAGATGGGAATGCCACTGGAAGGCCCGAGGAGCATGT
GGCACCACCTTCTGTTCCGGTACCCGTGCAGGAGGCGCCAAACACGCCCACCAGGCCACAGGCGCCACCAAGTGCCCATCTTGAGTCTCCGCAGC
CGGCGCGAACACAGCAGCAGTCCATTCAACAGATGACGCCCGCAAAGCACCACCAGTTCCAACAATTTTCTCAAAGACGGAGCAGCTGGTGCTGTT
CTAGAGGATCAGGATATCGAGGAGGTGCTTAAAGCGCTCAAAACATTTGACGGTGGCCATGTTAATCCAGATACCATTTGCGAGTTTTTCGACGA
AGTTTGGGAAGAGGCAGCACCGGCAGCGCCATTGCCGCCCGCGCCACCCGAAAATGTGGTGGATGTGCCGGGCGCGAAGCCCAGCTGCAGTGGCA
TCCTCGTTAGCGGCAGCAACATTTCCCAGCCGAATGTGATTATTAAGCAGGAGCAGCGGCCCTGGCAGGAGAGTCATGCTGAGTTGGAGCAGCAG
CAGCACGTTATCTCGCGCAGGATCGAGTTTTTGCTACGCAGGATGCGCAAGCTCCAGGCGCGAGCGATGTGCCGTCACGCGAGCGAGGAGGTGGT
TGGTATCATGGAGTGGTCTGCCCCGCAGTTCCCATAAGGCTCCAGTTCCAGCGAGAAGTTCCACGCTGACTGAGCAGGAGGCCACTGTCCTATCGA
TTGTCTCAGGGCGTCCGAGCTCAACCTTCTGGGAGGAGCAGAACAAGCATCCGCTGCCTGCTAGCCAGATGAGTAATGTGATCCGGCATATTGCG
ACGGCGGCAAAGCATCAGCAAATCTGCCACTCAGCCAGCGGAAGCTCTGCTACTCTGGCGCCATCCTCCAGCTGGTACAACAGCTGCAACAGCTC
TGCGCTGCCGATGAAGCGTCCACGAAAGAATCAACTTGATGCTTCGGTTGCAACGGGTGCCACACCCACTGCACCTGCGCCAGGAGCGGTAACAT
CTAGACAGGCAGCTGGCACGACGGGATCCGCAACGGGTTCGAATACACCGCGGGCGGATGATATCGTGCCCGGCTACGACACCTATGTGACTAAT
GAACTCACCCATGTGTCTGGCCTGCTGCACACGGAGCTTCGAGAAGTACAGAATGCCATCGACTCGGACGCCACGGAGTCAAGTTCTGGTGGAGA
ATCCGCTGACGAGATGGTAACCTACAACAACAACCAGCAGCTCTCGCTACCAATCACTCGACGCGCTGTCTGGCGATATTCGAGAGATCGTGCAG
CCATTGCCCTGCGCTGGTCCTGGCTCTGCTCCCAGCTGACCGATTTGGAGATGAAGATCCGTCAGCACAGCGACCTTTACATGGATCTAACTCAG
TCCAAGGGCGAGATCCAGCTGGAGTCCACAGCTAAGACCTCACCGTCGCTAGCACAGCCGGCAAATGGCATTAAGGAGGAGCCCGGATCCGACTA
CCTCTGCAGTCGGGCACGTCCATTGGTGCTGTCCGAGTTCCGCAAACGCAAGCTCTTCCAGACCACGAACATGCACACGATTTCCAAGAAAGCCG
CACGCCCCAGCAACATTAAGTGTGGCTGCCAGTGGCCGCAGGTGCCATGCACACTGTGCACGGGTCGGACAGACCCTACGGCGCCCAGGGATCTG
GTCGAGACGATGATGCCGCAAAACCGGGTGGCATTGCTCGATGCTGGCTACCATCCAGTGCTCAGCTTCGCCAGCGATGTCAGTCAGTCGGTTCA
CTTGGAGGCCGTTGCCCGCCAGCCGGACTGGCAGTACCGCGTCATGCGCAGCCAGCCCAAGGCCATTGTCAAGGCCATGTGGAAGGCGGAGCGCG
AGACGATAGCCTCAGGCGGTGTCGGCGGACAAGGTGGCAGCCGGCGGTCGGGCGATGCGGCGAAGCGGCGTTATATACGACGCAAGGAGCGCAAC
AACAACTCAAATAAGGAGGCTGGGAGCGGAGCTAAAGCTGCTGCTGTCGCCGCAGGAGGAGCAGGCGGAAACGGAAGCAGTAGCGTCGGGGGAGG
GGATAGCGGAAACGGTACTGGTACTGCTACTACTTCTTCTTCTACTACGCCTACTACAACGCCACTTGTGGCCAACACAGCGGCCAGGGGCAAGC
GGCAACCACAACACCCAACTGGAGCGAACAGTTCCAGCTCGCTGTGGCCAGACTCTCGCCAACGCCAACGACAACGCCACCACAGTCCCTCCTCA
ACCTCGATCTCGGCACTGAGCGGCGCTAAGAAGGCACGCAAATCCGCAACCAACAGCAGCAGCAGCAATTCCACACAGCAGCAGCAGAATCACCA
CGGCACCAAAATCAACAATCATCATCTCAATGGCTACGGCGATCAGTGGGGGGAGCAAAGCAGGAGTCGTCGCAACTCTTCGCCCTCCAACAGTC
ATAAAAATGAGAGAACCTCTGAGCGTCGCGTTCGTCCCATCTACGACATCAATAACATCGTTATACCCTACAGTATGCTAGCCCAGTCGAAAATG
GAGATAATTCCCTACAAGGAAATACCCATACCCAAGTGGCGCATTGTAGACAGTGATAACGATAAGGGAAAACATTCGTCAGATGAGTCAATGGA
GCGCAAACTGAGCAATGGCTGTGTCGCATCAAAGTCAGAGGAGCTAGCCAAACAACAGCTACCACCACCACCAGATCAAGATCAAGAGCAGCCGG CCCTGCAGCCTCCGAAGGTTAATGGTTTAAAGGAAAATCAAGCAGTCAAGCACAATAACAATAATAATACAAACAATAATAATAATAAAAATGGA
CTGGTAAATGGTAACGCCAAAAAGGATGAACTTAAGGCTGCAGAGGATCACGATACGCAATCAAAAGAAGACGACGATCCAAAGGAAAAGGTGGT
CAAACCCAAGCTCAACGGAAACTTGATAAAGAATCCGATTGACAAAACTGCCGAAACGCAAGACAAAATTGCTCAGCCAGCACCAGAACCACCAC
TGCCAAAGCGACCCAAGCTGGAAACTCCAACCTCCAACGAGGTCACCAAGGCTAATGGGCAGTTGGTGCAGCAACAGCTGGAATCCCGTGAGAGC
GAGGAGGAGCCACAGCATGTCGACGAAGATCTTTCGGATGAAGCGTTTATTATGCGACATCAGCGAGCTCTTCTCGAGGAGCGACGCCGCTTCGA
GACTTTCCTTAAGTTCCCCTGGAGCACCCGATCGCGTGCAAATAGGCGCGTCGATAGTCGTGCCGAATCTAGTGGCGCCAACACACCGGATCCCG
CCTCACCAGCTCCTCATCTAGGCGGCCCTGGTCACGACAACGAAAGCATTCCCTCGCCGCTGGCGTACCCACTGGACGCTTTTAACGAAAGCGGT
GAGCTGCTGACTGGCGGACAGGCACGCCAAGCTCGTCGTCGGACTACGTCTAGCAAGCTTAAGGATCAGCTGGAACGGCGCAGCACCACGCCCGA
TCTGCGGGAGTCTTACACTGTGATGCCATCTCCCTTTGAGCCCTTGAACTTTCCGCTCTCCGACGAGGTCTACCAGCGATTGCTAGCCGAGACAT
ATGCGCCGCCCAGGTCAATGACCGTCTCAAAGCGGGCCAAAAGCAAGTCGATATCCTCGAACTGTGATGGTGGAACACCTTCACAGGAGGCAGC
GGCAGTCGGCGCAGCAGCAAGTGCAAGATTAAGCCAAATGGTCAGCTAAATGGCCAGCTCAATGGCCACCCTGCGGCGGCGAAGTTGAACGGAAT
AGATGCGGCAAATGAAGGTGGAATTTCTGAGCCGGAAGAGGAAGAGATGCTGCTAGAAGACGAGGATGACGACTATCCCAAGCATCATCTGGCGC
CGCTGGATGACGAGGAGCCGTCGACACCAGATGTCGAGCATGAGCTTTACGACTCGGCGATCGATGCCTATCTCGCTGATCCGGAGGCGCTAGAG
GAGGATATGGGCGAGGATCCCTTCGAGGACGACGATCCCAACGATCCGGAGTGGAAGACACGGACCGAGGGTGTTCGCAGCAGACGCATCTAAGA
CCAAAATCCAAAGTTTTCGTTATTTAAGACTTTTAAACGATTTGTCAATTTTTAAAGCCACAACACACACACACCCACAAATCAGCCGGAGCAGA
CCAACAAATTTTAATTTGTTTCAAACGGTTTGGTTTGCACTCACAACAGCATTGCGTACTCTAAGCAATCGTCTAAGTTATTTAGTTCTACGAGC
CCACAAC
(SEQ ID NO: 1403)

Start ATG: 131

MAPALTAEPLSPKEKLTSTASPSARSSSESGGVGCAVGLVKKPATPTPATATTRITRSSAAAASVTASPHLQQQRSSLAINNKRKSGNAKASNEP
MGLSTAPTPHSTTSPNPSTDTAAASTSAVEHNNNDSNSTSAGNSTSADNSSTPKDNSTAQLLADLTINFEETISAEICLRKTLPDVSLGKEPVPP
ASVLAVATSSTSAGSALSLSAVDEVTKIEIDNIEERLSQLDGNATGRPEEHVAPPSVPVPVQEAPNTPTRPQAPPSAHLESPQPARTQQQSIQQM
TPQSTTSSNNFLKDGAAGAVLEDQDIEEVLKALKTFDGGHVNPDTICEFFDEVWEEAAPAAPLPPAPPENVVDVPGAKPSCSGILVSGSNISQPN
VIIKQEQRPWQESHAELEQQQHVISRRIEFLLRRMRKLQARAMCRHASEEVVGIMEWSARSSHKAPVPARSSTLTEQEATVLSIVSGRPSSTFWE
EQNKHPLPASQMSNVIRHIATAAKHQQICHSASGSSATLAPSSSWYNSCNSSALPMKRPRKNQLDASVATGATPTAPAPGAVTSRQAAGTTGSAT
GSNTPRADDIVPGYDTYVTNELTHVSGLLHTELREVQNAIDSDATESSSGGESADEMVTYNNNQQLSLPITRRAVWRYSRDRAAIALRWSWLCSQ
LTDLEMKIRQHSDLYMDLTQSKGEIQLESTAKTSPSLAQPANGIKEEPGSDYLCSRARPLVLSEFRKRKLFQTTNMHTISKKAARPSNIKCGCQW
PQVPCTLCTGRTDPTAPRDLVETMMPQNRVALLDAGYHPVLSFASDVSQSVHLEAVARQPDWQYRVMRSQPKAIVKAMWKAERETIASGGVGGQG
GSRRSGDAAKRRYIRRKERNNNSNKEAGSGAKAAAVAAGGAGGNGSSSVGGGDSGNGTGTATTSSSTTPTTTPLVANTAARGKRQPQHPTGANSS
SSLWPDSRQRQRQRHHSPSSTSISALSGAKKARKSATNSSSSNSTQQQQNHHGTKINNHHLNGYGDQWGEQSRSRRNSSPSNSHKNERTSERRVR
PIYDINNIVIPYSMLAQSKMEIIPYKEIPIPKWRIVDSDNDKGKHSSDESMERKLSNGCVASKSEELAKQQLPPPPDQDQEQPALQPPKVNGLKE
NQAVKHNNNNNTNNNNNKNGLVNGNAKKDELKAAEDHDTQSKEDDDPKEKVVKPKLNGNLIKNPIDKTAETQDKIAQPAPEPPLPKRPKLETPTS
NEVTKANGQLVQQQLESRESEEEPQHVDEDLSDEAFIMRHQRALLEERRRFETFLKFPWSTRSRANRRVDSRAESSGANTPDPASPAPHLGGPGH
DNESIPSPLAYPLDAFNESGELLTGGQARQARRRTTSSKLKDQLERRSTTPDLRESYTVMPSPFEPLNFPLSDEVYQRLLAETYAPPRSMTVSKR
AKSKSISSNCDGGNTFTGGSGSRRSSKCKIKPNGQLNGQLNGHPAAAKLNGIDAANEGGISEPEEEEMLLEDEDDDYPKHHLAPLDDEEPSTPDV
EHELYDSAIDAYLADPEALEEDMGEDPFEDDDPNDPEWKTRTEGVRSRRI*
(SEQ ID NO: 1404)

Celera Sequence No. : 142000013384528
AATGGCGGGATCTGGAGTTGCCAAGCAGATATTTGCCCTCGATTTCGAGATCTTTGGACGAGTGCAAGGTATGCAATGCATTTTTCTGATTCGGC
TTGTTAAACAGCGTATTAAATTTTGCAGGTGTGTTCTTCCGCAAAGTAAGTACTGGGAGGCCTATATATATATCTGGAAATCAACATTTAACTTA
TGTACATTTTTGGCTTAGCACACGTCGCATGAGGCTAAAAGATTGGGAGTTAGGGGCTGGTGCATGAATACCCGGGATGGGACCGTCAAGGGACA
ACTGGAGGCTCCTATGATGAATTTAATGGAAATGTAGGTACCGCTGCACTCCACTAATTCAATCATTTAACCATCGCCCACTAATTTGAAGGAAA
CATTGGCTGGAGAACAACCGAATTCCCAACGCTAAGGTCTCAAAGGCTGAATTTTCGCAAATCCAGGAAATCGAGGACTATACGTTCACTTCCTT
TGACATAAAACATTAAAAACGAATTATTAGCTCTTTCGTTGTCCATCCAATTCCGAAACAAAGTCTAAATAAATTACCAGGGCTGCAACTTGCGT
AAGCAGGCATATCTGCATTGCTATCGACTGAGTCGATAACATTCGATAGTATGAACATAAGAAATATTACGTTTCGCAAAACTGAACCCAGTACT
GAAGTACAACAATAAATAAATAATAAATTATTTAAAACAAGGCGGAAAATTATTCCGAGAATCGATAGTCGCTAGTCGAAAGTGCGCACCACTCC
AGTATCTACTCGATATATTGCTATCACAGCCGATAGTTTGCAGCTCCCTGCCATAGACACTGGTCATCTCGCTCGCACACACAACAGTGGGCCGC
GCCACCGCCATAGGCGGCGCACGTGCAAGAGCGAGACAACCAGCTGGGCGACAGCGCACTTTGGTCTGGCACAGAAACGAGTACAGCTTCGATAC
ACGTCGTTTTGCCAAAAGCGTAGCAGAGCAGTCTAAGCGATGAAAAAAATAAATGAGGAAAAAAGTCCGTGAAGCGAAAACCGTAATTCCTACAG
TGCGAGTCACGCCATTGTGTTTGCAAAAAATATTTGCCAATTGTGCTACGGGCAATTTTTCGGAACGGCCGAATTGTGCGTATAATGAAAAAAAA
TACTACTTAATTTTTAAGCAATTTACAAATTCTTGCGTGCTGCCTGCCTGCTGTCGGTGTGTTCTTGCTTGCATGTGTTAGTGAGTACGATTACT
TTCGCGCTGAAAACCTTTTTCCACTGCCCTTTCGCTGGAATCTGGGCGAATATAGATAGGACACAAAGCACATATAACTGATTTTTACTGCAGAA
TTGATCGAGACATGTGGAATACAATAAATGAGATTGTGTAAATAACTGAATATAGTGGCGCATACAGTTGCACGTGTGTGTGTGCTAGCATGTGC
GTGTGTGTGTGTAAAGGCGCGAGTTTCCGTTTGCCTAGGCTAATTGTAGTGGAAAAACTCAATAAACGGAATTACATAAAAACATGGTGGCATGA
TCGGCAGTTTCCCGCCGGCAGAAGATGCCCAATCTTGGAAAATTGTAATTTTCGAAAGTAACCGCAATGATTTCGTCAGTATGTAAAGTAGTCTG
TCAGTCCCTGCATATGTTTGTGTGTGTGTGTTCTATACAGTTTTTTTATTGCGCATCATGGTGTGCAATAGCGCGCTTTCTGACCTCTCTCTCG
CTCTCATGGGTTCTCTTGTTGGCCAAAGCGACGCTGTGTGTGTGTTGTGTACGCATATGTAGCATATGTACATAACACGCCGGAAAAGACAAAAA
AAAAAAACCATTCCAAATTTTGAAATCTTACGGAGGCGGGCGGTTTAAACGAGATAAAAAATAAATACACCAATATTGTTCTTTTATATGATAAC
GCAGTAGTCTCGGACCGAATAGTATGCCTTTATTTTGTCGTCCTAACGCTGAATTGCCGAAAAATAATAGCCCGTTTTTGGAAAATTCTCGACAG
GATTAGCATAAAGAGACGCCTTAGGAGTCGAACGAACCAAATGCCGCAGCAGCCGGCCAACGTATTAGCATCAGAACGATGGCCCCAGCGCTCAC
AGCCGAGCCACTAAGTCCAAAGGAGAAGCTAACCAGCACCGCCTCGCCCTCGGCCCGCAGCTCCTCGGAAAGCGGAGGAGTTGGATGTGCAGTTG
GCTTGGTCAAGAAGCCGGCAACACCCACGCCGGCCACGGCCACCACGCGGATTACCCGCTCATCAGCGGCAGCGGCCTCAGTTACCGCTTCCCCG
CATCTACAACAGCAGCGATCCTCGCTAGCAATCAATAACAAGCGAAAGTCGGGCAACGCTAAAGCCAGCAATGAACCAATGGGGCTGAGCACAGC
CCCGACTCCACACAGCACCACTTCACCAAATCCCTCGACGGATACTGCGGCAGCCTCCACCTCTGCCGTGGAGCACAACAATAACGACAGCAACA
GTACCTCCGCCGGCAACAGCACCTCCGCCGACAACAGCTCCACGCCCAAGGACAACTCCACCGCTCAGCTACTGGCGGATCTAACCATCAACTTT
GAGGAGACCATATCCGCGGAGATTTGCCTGAGGAAAACCCTACCCGATGTGAGTCTGGGGAAAGAGCCGGTTCCGCCTGCCTCGGTGCTGGCAGT GGCCACAAGTTCAACGAGTGCTGGCAGCGCTCTATCCTTATCTGCAGTGGATGAGGTGACCAAGATAGAAATAGATAATATAGAAGGTGGGTCTA
AGGAATCACTCCAAATAAATAGTCTTGACTCAAAATTTCTCTCGCCCACTGTTTCAGAGCGTCTCAGCCAGCTAGATGGGAATGCCACTGGAAGG
CCCGAGGAGCATGTGGCACCACCTTCTGTTCCGGTACCCGTGCAGGAGGCGCCAAACACGCCCACCAGGCCACAGGCGCCACCAAGTGCCCATCT
TGAGTCTCCGCAGCCGGCGCGAACACAGCAGCAGTCCATTCAACAGATGACGCCGCAAAGCACCACCAGTTCCAACAATTTTCTCAAAGACGGAG
CAGCTGGTGCTGTTCTAGAGGATCAGGATATCGAGGAGGTGCTTAAAGCGCTCAAAACATTTGACGGTGGCCATGTTAATCCAGATACCATTTGC
GAGTTTTTCGACGAAGTTTGGGAAGAGGCAGCACCGGCAGCGCCATTGCCGCCCGCGCCACCCGAAAATGTGGTGGATGTGCCGGGCGCGAAGCC
CAGCTGCAGTGGCATCCTCGTTAGCGGCAGCAACATTTCCCAGCCGAATGTGATTATTAAGCAGGAGCAGCGGCCCTGGCAGGAGAGTCATGCTG
AGTTGGAGCAGCAGCAGCACGTTATCTCGCGCAGGATCGAGTTTTTGCTACGCAGGATGCGCAAGCTCCAGGCGCGAGCGATGTGCCGTCACGCG
AGCGAGGAGGTGGTTGGTATCATGGAGTGGTCTGCCCGCAGTTCCCATAAGGCTCCAGTTCCAGCGAGAAGTTCCACGCTGACTGAGCAGGAGGC
CACTGTCCTATCGATTGTCTCAGGGCGTCCGAGCTCAACCTTCTGGGAGGAGCAGAACAAGCATCCGCTGCCTGCTAGCCAGATGAGTAATGTGA
TCCGGCATATTGCGACGGCGGCAAAGCATCAGCAAATCTGCCACTCAGCCAGCGGAAGCTCTGCTACTCTGGCGCCATCCTCCAGCTGGTACAAC
AGCTGCAACAGCTCTGCGCTGCCGATGAAGCGTCCACGAAAGAATCAACTTGATGCTTCGGTTGCAACGGGTGCCACACCCACTGCACCTGCGCC
AGGAGCGGTAACATCTAGACAGGCAGCTGGCACGACGGGATCCGCAACGGGTTCGAATACACCGCGGGCGGATGATATCGTGCCCGGCTACGACA
CCTATGTGACTAATGAACTCACCCATGTGTCTGGCCTGCTGCACACGGAGCTTCGAGAAGTACAGAATGCCATCGACTCGGACGCCACGGAGTCA
AGTTCTGGTGGAGAATCCGCTGACGAGATGGTAACCTACAACAACAACCAGCAGCTCTCGCTACCAATGTGAGTACTTCGTATTATTTATGTACA
TACTTAGGTTATCGGGAATATTTTACAAGTAAACTTTCTTCCATCTTTTTTTGAGGGGGGTTTTCAGCTTCTGTCATCTTTTTAAGATCATTCTT
TTGCTATAGAATTTGTCCGATTAATGTTGGCTCGGTAGTTTTCTTTCAAAATTGTTTTGCTTTGACAGGCATTTTAAACATGATTTAACGTCGTC
CTTAGCAATTGAAAAGTTGTAATAGGCTTTGATTAGAGTTGTTGTACCTAATTATCGCATTTACAATGCGATATTTCAACTATTTCAACAGTTTT
TATTAAAATTGTTAATTAGCGATTATATATTTCTTTTAGCTTTTTTTTTGTGGTATTCTCTTTCCTAATGCTCTTGAAATTTGATTCTTTGCAGC
ACTCGACGCGCTGTCTGGCGATATTCGAGAGATCGTGCAGCCATTGCCCTGCGCTGGTCCTGGCTCTGCTCCCAGCTGACCGATTTGGAGATGAA
GATCCGTCAGCACAGCGACCTTTACATGGATCTAACTCAGTCCAAGGGCGAGATCCAGCTGGAGTCCACAGCTAAGACCTCACCGTCGCTAGCAC
AGCCGGCAAATGGCATTAAGGAGGAGCCCGGATCCGACTACCTCTGCAGTCGGGCACGTCCATTGGTGCTGTCCGAGTTCCGCAAACGCAAGCTC
TTCCAGACCACGAACATGCACACGATTTCCAAGAAAGCCGCACGCCCCAGCAACATTAAGTGTGGCTGCCAGTGGCCGCAGGTGCCATGCACACT
GTGCACGGGTCGGACAGACCCTACGGCGCCCAGGGATCTGGTCGAGACGATGATGCCGCAAAACCGGGTGGCATTGCTCGATGCTGGCTACCATC
CAGTGCTCAGCTTCGCCAGCGGTGAGTGGGAGGTTACACTGAGTGGACCCATTTGGTTTTCGTCCATGATTATTTCTTATCATCTGTGATGGTTT
AACATTATTTATTCTACACTTGAGATTTGAACTGAATTGATTAAAAAGTAAAACTTTAAAATGCAATACTTGCAAATAATTTTTATTCGAAACTA
AAACATTAAAATCCTCGTATTCTTTACATTGGATTCCAAAATGAAAAGAAATAGTCGGATGATGACAGCTAAAGTGGAATTATGTTTGAATATAT
TCTTATCCCTATCATTCTTGTTTCCCAGATGTCAGTCAGTCGGTTCACTTGGAGGCCGTTGCCCGCCAGCCGGACTGGCAGTACCGCGTCATGCG
CAGCCAGCCCAAGGCCATTGTCAAGGCCATGTGGAAGGCGGAGCGCGAGACGATAGCCTCAGGCGGTGTCGGCGGACAAGGTGGCAGCCGGCGGT
CGGGCGATGCGGCGAAGCGGCGTTATATACGACGCAAGGAGCGCAACAACAACTCAAATAAGGAGGCTGGGAGCGGAGCTAAAGCTGCTGCTGTC
GCCGCAGGAGGAGCAGGCGGAAACGGAAGCAGTAGCGTCGGGGGAGGGGATAGCGGAAACGGTACTGGTACTGCTACTACTTCTTCTTCTACTAC
GCCTACTACAACGCCACTTGTGGCCAACAGTAAATTATTGTAAACATGACGAAATTCGATAATTGTTATTAACATAAAACAACAACAATCTTTTG
CATCTCTTCTTCTTCTTTTTCTTTGCATCGATCAACCAAAACACGAAATTCCACCAACACCATCAACAAACACCACCACCAACAACAACAACGAA
AAACCCCACCAATTGTTTTATTTTGCCATTCCGTTCTTGTCTCCGTTTCGTCCCCGTTCCGCATCCAAATCACGGACTTGACGCAACATCAGCAG
CGGCCAGGGGCAAGCGGCAACCACAACACCCAACTGGAGCGAACAGTTCCAGCTCGCTGTGGCCAGACTCTCGCCAACGCCAACGACAACGCCAC
CACAGTCCCTCCTCAACCTCGATCTCGGCACTGAGCGGCGCTAAGAAGGCACGCAAATCCGCAACCAACAGCAGCAGCAGCAATTCCACACAGCA
GCAGCAGAATCACCACGGCACCAAAATCAACAATCATCATCTCAATGGCTACGGCGATCAGTGGGGGGAGCAAAGCAGGAGTCGTCGCAACTCTT
CGCCCTCCAACAGTCATAAAAATGAGAGGTATGTTTCGGATTCAATAACTGATCCCAGGGATTCGCGATAAGTAGTCCTGCTTTTTTTTTATAAG
ATAGATTGTTATATATAATTTATATGTATGTTTCCCTTGCAGAACCTCTGAGCGTCGCGTTCGTCCCATCTACGACATCAATAACATCGTTATAC
CCTACAGTATGCTAGCCCAGTCGAAAATGGAGATAATTCCCTACAAGGAAATACCCATACCCAAGTAAGTATTCAATTTTGCGCTAAGTCCTTAT
TTTATATATATATGTCGCATAATGTAAAATACCAAGATTTGTGTATATCTATTAAAATCACCCATTCCATCTTTGCTTTCAGGTGGCGCATTGTA
GACAGTGATAACGATAAGGGAAAACATTCGTCAGATGAGTCAATGGAGCGCAAACTGAGCAATGGCTGTGTCGCATCAAAGTCAGAGGAGCTAGC
CAAACAACAGCTACCACCACCACCAGATCAAGATCAAGAGCAGCCGGCCCTGCAGCCTCCGAAGGTTAATGGTTTAAAGGAAAATCAAGCAGTCA
AGCACAATAACAATAATAATACAAACAATAATAATAATAAAAATGGACTGGTAAATGGTAACGCCAAAAAGGATGAACTTAAGGCTGCAGAGGAT
CACGATACGCAATCAAAAGAAGACGACGATCCAAAGGAAAAGGTGGTCAAACCCAAGCTCAACGGAAACTTGATAAAGAATCCGATTGACAAAAC
TGCCGAAACGCAAGACAAAATTGCTCAGCCAGCACCAGAACCACCACTGCCAAAGCGACCCAAGCTGGAAACTCCAACCTCCAACGAGGTCACCA
AGGCTAATGGGCAGTTGGTGCAGCAACAGCTGGAATCCCGTGAGAGCGAGGAGGAGCCACAGCATGTCGACGAAGATCTTTCGGATGAAGCGTTT
ATTATGCGACATCAGCGAGCTCTTCTCGAGGAGCGACGCCGCTTCGAGACTTTCCTTAAGTTCCCCTGGAGCACCCGATCGCGTGCAAATAGGCG
CGTCGATAGTCGTGCCGAATCTAGTGGCGCCAACACACCGGATCCCGCCTCACCAGCTCCTCATCTAGGCGGCCCTGGTCACGACAACGAAAGCA
TTCCCTCGCCGCTGGCGTACCCACTGGACGCTTTTAACGAAAGCGGTGAGCTGCTGACTGGCGGACAGGCACGCCAAGCTCGTCGTCGGACTACG
TCTAGCAAGCTTAAGGATCAGCTGGAACGGCGCAGCACCACGCCCGATCTGCGGGAGGTAAGTCGATGTCCAAGTTTCACATTTGTTGAACTCAT
ATATAAAATAAATTCTGGTTGTGCCTATTACTTTTGCCGAATTTTGTTTTCAAACTGCTTTGAATGTTCAAATACTGATTGTATAGAATAGTTTT
CTAATTGAAACCCTTTTCCTTTTTGTATAGTCTTACACTGTGATGCCATCTCCCTTTGAGCCCTTGAACTTTCCGCTCTCCGACGAGGTCTACCA
GCGATTGCTAGCCGAGACATATGCGCCGCCCAGGTCAATGACCGTCTCAAAGCGGGCCAAAAGCAAGTCGATATCCTCGAACTGTGATGGTGGGA
ACACCTTCACAGGAGGCAGCGGCAGTCGGCGCAGCAGCAAGTGCAAGATTAAGCCAAATGGTCAGCTAAATGGCCAGCTCAATGGCCACCCTGCG
GCGGCGAAGTTGAACGGAATAGATGCGGCAAATGAAGGTGGAATTTCTGAGCCGGAAGAGGAAGAGATGCTGCTAGAAGACGAGGATGACGACTA
TCCCAAGCATCATCTGGCGCCGCTGGATGACGAGGAGCCGTCGACACCAGATGTCGAGCATGAGCTTTACGACTCGGCGATCGATGCCTATCTCG
CTGATCCGGAGGCGCTAGAGGAGGATATGGGCGAGGATCCCTTCGAGGACGACGATCCCAACGATCCGGAGTGGAAGACACGGACCGAGGGTGTT
CGCAGCAGACGCATCTAAGACCAAAATCCAAAGTTTTCGTTATTTAAGACTTTTAAACGATTTGTCAATTTTTAAAGCCACAACACACACACACC
CACAAATCAGCCGGAGCAGACCAACAAATTTTAATTTGTTTCAAACGGTTTGGTTTGCACTCACAACAGCATTGCGTACTCTAAGCAATCGTCTA
AGTTATTTAGTTCTACGAGCCCACAACAAAAAAAAAAAAACACAGATACGCTACACACAAGTACACAACAAAACAAACACGAAGCAGAAGCGAAAA
TCTTGAAACAATGTAAATACAAGCTAAACGCATAGAGCTAAGCAGTTACTGATAATTGTACACTAACCAACGATCAAGAAATCATCGAACGCACC
CACCACGTCGCGTGGACGTGGTGGATGCGGTCGGTTGGAGCACTGGTCAGCGGTTAAGTAGGCACCACAACAAACCCACTTGGGCTTCAAGCCGA
AGTGCGCTAATGATAAAAATATTAAGCTAATCTAAATATATATATATATACGAAAACATTTAAATATATACCATATGCATACATTAACGTGTAAA
TGCCGAAGAGAGCAGTTAGCTGAAGATTTGAAATGTATTCGCACCTGCACACAAACGATATAACAACTAAGCTATAGAAGGCAATTATCTGTAAA
TTGATCAAGCTTAACCATTAGCTAACCAACCATTAGCCTTTAGCCCAGCAAGTAATCAGTCGGCGTTGGGGCCGTGTTTTTCTTATATTTTAAAA
AGTTTATCAGCTGTAAATGTATAGAGCGGAATTCGAAAGGCGGTGTGTGAAAATGGATCGAACGATAAATGTATGTATATGTATTTTAGTTGCTT
AGGCGTTTTCATTTCTACCTTATAAACACGTTAGCGGCTAATTGTAGCAATTAATACTATAAAACACAAAAAAAAAAACAAAAACAAAAAACAAC
AACCATAAGGAAACCTAGCGCGGCTATGTCCGTGAAAATGTTTATTCTAATTTCGTTTTTACTATCTACTGCGTATGTTTCACCGCAAAGCTAGA
ATCCAGTTTAATTCGTTAAAACTTGAAAAGAAATACAACAGAAATGTGAAGATTAACTAAGGACCGCAAAAATACAGAATTATATATTCTTAAAA
ATGACACATGGAGCGCCAGAAGTGATATGCTGGGACCACCATCGCCAGATGGTGGAATCTGGCCAACATGTGTGTCG

FIGURE SHEET 752

(SEQ ID NO: 1405)

Exon: 1001..1120
Exon: 1996..2746
Exon: 2813..4058
Exon: 4465..4961
Exon: 5254..5634
Exon: 5888..6203
Exon: 6313..6429
Exon: 6543..7467
Exon: 7631..8387
Start ATG: 2074

Transcript No. : CT14980
AAATGAGGAAAAAAGTCCGTGAAGCGAAAACCGTAATTCCTACAGTGCGAGTCACGCCATTGTGTTTGCAAAAAATATTTGCCAATTGTGCTACG
GGCAATTTTTCGGAACGGCCGAATTGATTAGCATAAAGAGACGCCTTAGGAGTCGAACGAACCAAATGCCGCAGCAGCCGGCCAACGTATTAGCA
TCAGAACGATGGCCCCAGCGCTCACAGCCGAGCCACTAAGTCCAAAGGAGAAGCTAACCAGCACCGCCTCGCCCTCGGCCCGCAGCTCCTCGGAA
AGCGGAGGAGTTGGATGTGCAGTTGGCTTGGTCAAGAAGCCGGCAACACCCACGCCGGCCACGGCCACCACGCGGATTACCCGCTCATCAGCGGC
AGCGGCCTCAGTTACCGCTTCCCCGCATCTACAACAGCAGCGATCCTCGCTAGCAATCAATAACAAGCGAAAGTCGGGCAACGCTAAAGCCAGCA
ATGAACCAATGGGGCTGAGCACAGCCCCGACTCCACACAGCACCACTTCACCAAATCCCTCGACGGATACTGCGGCAGCCTCCACCTCTGCCGTG
GAGCACAACAATAACGACAGCAACAGTACCTCCGCCGGCAACAGCACCTCCGCCGACAACAGCTCCACGCCCAAGGACAACTCCACCGCTCAGCT
ACTGGCGGATCTAACCATCAACTTTGAGGAGACCATATCCGCGGAGATTTGCCTGAGGAAAACCCTACCCGATGTGAGTCTGGGGAAAGAGCCGG
TTCCGCCTGCCTCGGTGCTGGCAGTGGCCACAAGTTCAACGAGTGCTGGCAGCGCTCTATCCTTATCTGCAGTGGATGAGGTGACCAAGATAGAA
ATAGATAATATAGAAGAGCGTCTCAGCCAGCTAGATGGGAATGCCACTGGAAGGCCCGAGGAGCATGTGGCACCACCTTCTGTTCCGGTACCCGT
GCAGGAGGCGCCAAACACGCCCACCAGGCCACAGGCGCCACCAAGTGCCCATCTTGAGTCTCCGCAGCCGGCGCGAACACAGCAGCAGTCCATTC
AACAGATGACGCCGCAAAGCACCACCAGTTCCAACAATTTTCTCAAAGACGGAGCAGCTGGTGCTGTTCTAGAGGATCAGGATATCGAGGAGGTG
CTTAAAGCGCTCAAAACATTTGACGGTGGCCATGTTAATCCAGATACCATTTGCGAGTTTTTCGACGAAGTTTGGGAAGAGGCAGCACCGGCAGC
GCCATTGCCGCCCGCGCCACCCGAAAATGTGGTGGATGTGCCGGGCGCGAAGCCCAGCTGCAGTGGCATCCTCGTTAGCGGCAGCAACATTTCCC
AGCCGAATGTGATTATTAAGCAGGAGCAGCGGCCCTGGCAGGAGAGTCATGCTGAGTTGGAGCAGCAGCAGCACGTTATCTCGCGCAGGATCGAG
TTTTTGCTACGCAGGATGCGCAAGCTCCAGGCGCGAGCGATGTGCCGTCACGCGAGCGAGGAGGTGGTTGGTATCATGGAGTGGTCTGCCCGCAG
TTCCCATAAGGCTCCAGTTCCAGCGAGAAGTTCCACGCTGACTGAGCAGGAGGCCACTGTCCTATCGATTGTCTCAGGGCGTCCGAGCTCAACCT
TCTGGGAGGAGCAGAACAAGCATCCGCTGCCTGCTAGCCAGATGAGTAATGTGATCCGGCATATTGCGACGGCGGCAAAGCATCAGCAAATCTGC
CACTCAGCCAGCGGAAGCTCTGCTACTCTGGCGCCATCCTCCAGCTGGTACAACAGCTGCAACAGCTCTGCGCTGCCGATGAAGCGTCCACGAAA
GAATCAACTTGATGCTTCGGTTGCAACGGGTGCCACACCCACTGCACCTGCGCCAGGAGCGGTAACATCTAGACAGGCAGCTGGCACGACGGGAT
CCGCAACGGGTTCGAATACACCGCGGGCGGATGATATCGTGCCCGGCTACGACACCTATGTGACTAATGAACTCACCCATGTGTCTGGCCTGCTG
CACACGGAGCTTCGAGAAGTACAGAATGCCATCGACTCGGACGCCACGGAGTCAAGTTCTGGTGGAGAATCCGCTGACGAGATGGTAACCTACAA
CAACAACCAGCAGCTCTCGCTACCAATCACTCGACGCGCTGTCTGGCGATATTCGAGAGATCGTGCAGCCATTGCCCTGCGCTGGTCCTGGCTCT
GCTCCCAGCTGACCGATTTGGAGATGAAGATCCGTCAGCACAGCGACCTTTACATGGATCTAACTCAGTCCAAGGGCGAGATCCAGCTGGAGTCC
ACAGCTAAGACCTCACCGTCGCTAGCACAGCCGGCAAATGGCATTAAGGAGGAGCCCGGATCCGACTACCTCTGCAGTCGGGCACGTCCATTGGT
GCTGTCCGAGTTCCGCAAACGCAAGCTCTTCCAGACCACGAACATGCACACGATTTCCAAGAAAGCCGCACGCCCCAGCAACATTAAGTGTGGCT
GCCAGTGGCCGCAGGTGCCATGCACACTGTGCACGGGTCGGACAGACCCTACGGCGCCCAGGGATCTGGTCGAGACGATGATGCCGCAAAACCGG
GTGGCATTGCTCGATGCTGGCTACCATCCAGTGCTCAGCTTCGCCAGCGATGTCAGTCAGTCGGTTCACTTGGAGGCCGTTGCCCGCCAGCCGGA
CTGGCAGTACCGCGTCATGCGCAGCCAGCCCAAGGCCATTGTCAAGGCCATGTGGAAGGCGGAGCGCGAGACGATAGCCTCAGGCGGTGTCGGCG
GACAAGGTGGCAGCCGGCGGTCGGGCGATGCGGCGAAGCGGCGTTATATACGACGCAAGGAGCGCAACAACAACTCAAATAAGGAGGCTGGGAGC
GGAGCTAAAGCTGCTGCTGTCGCCGCAGGAGGAGCAGGCGGAAACGGAAGCAGTAGCGTCGGGGGAGGGGATAGCGGAAACGGTACTGGTACTGC
TACTACTTCTTCTTCTACTACGCCTACTACAACGCCACTTGTGGCCAACACAGCGGCCAGGGGCAAGCGGCAACCACAACACCCAACTGGAGCGA
ACAGTTCCAGCTCGCTGTGGCCAGACTCTCGCCAACGCCAACGACAACGCCACCACAGTCCCTCCTCAACCTCGATCTCGGCACTGAGCGGCGCT
AAGAAGGCACGCAAATCCGCAACCAACAGCAGCAGCAGCAATTCCACACAGCAGCAGCAGAATCACCACGGCACCAAAATCAACAATCATCATCT
CAATGGCTACGGCGATCAGTGGGGGAGCAAAGCAGGAGTCGTCGCAACTCTTCGCCCTCCAACAGTCATAAAAATGAGAGAACCTCTGAGCGTC
GCGTTCGTCCCATCTACGACATCAATAACATCGTTATACCCTACAGTATGCTAGCCCAGTCGAAAATGGAGATAATTCCCTACAAGGAAATACCC
ATACCCAAGTGGCGCATTGTAGACAGTGATAACGATAAGGGAAAACATTCGTCAGATGAGTCAATGGAGCGCAAACTGAGCAATGGCTGTGTCGC
ATCAAAGTCAGAGGAGCTAGCCAAACAACAGCTACCACCACCACCAGATCAAGATCAAGAGCAGCCGGCCCTGCAGCCTCCGAAGGTTAATGGTT
TAAAGGAAAATCAAGCAGTCAAGCACAATAACAATAATAATACAAACAATAATAATAATAAAAATGGACTGGTAAATGGTAACGCCAAAAAGGAT
GAACTTAAGGCTGCAGAGGATCACGATACGCAATCAAAAGAAGACGACGATCCAAAGGAAAAGGTGGTCAAACCCAAGCTCAACGGAAACTTGAT
AAAGAATCCGATTGACAAAACTGCCGAAACGCAAGACAAAATTGCTCAGCCAGCACCAGAACCACCACTGCCAAAGCGACCCAAGCTGGAAACTC
CAACCTCCAACGAGGTCACCAAGGCTAATGGGCAGTTGGTGCAGCAACAGCTGGAATCCCGTGAGAGCGAGGAGGAGCCACAGCATGTCGACGAA
GATCTTTCGGATGAAGCGTTTATTATGCGACATCAGCGAGCTCTTCTCGAGGAGCGACGCCGCTTCGAGACTTTCCTTAAGTTCCCCTGGAGCAC
CCGATCGCGTGCAAATAGGCGCGTCGATAGTCGTGCCGAATCTAGTGGCGCCAACACACCGGATCCCGCCTCACCAGCTCCTCATCTAGGCGGCC
CTGGTCACGACAACGAAAGCATTCCCTCGCCGCTGGCGTACCCACTGGACGCTTTTAACGAAAGCGGTGAGCTGCTGACTGGCGGACAGGCACGC
CAAGCTCGTCGTCGGACTACGTCTAGCAAGCTTAAGGATCAGCTGGAACGGCGCAGCACCACGCCCGATCTGCGGGAGTCTTACACTGTGATGCC
ATCTCCCTTTGAGCCCTTGAACTTTCCGCTCTCCGACGAGGTCTACCAGCGATTGCTAGCCGAGACATATGCGCCGCCCAGGTCAATGACCGTCT
CAAAGCGGGCCAAAAGCAAGTCGATATCCTCGAACTGTGATGGTGGGAACACCTTCACAGGAGGCAGCGGCAGTCGGCGCAGCAGCAAGTGCAAG
ATTAAGCCAAATGGTCAGCTAAATGGCCAGCTCAATGGCCACCCTGCGGCGGCGAAGTTGAACGGAATAGATGCGGCAAATGAAGGTGGAATTTC
TGAGCCGGAAGAGGAAGAGATGCTGCTAGAAGACGAGGATGACGACTATCCCAAGCATCATCTGGCGCCGCTGGATGACGAGGAGCCGTCGACAC
CAGATGTCGAGCATGAGCTTTACGACTCGGCGATCGATGCCTATCTCGCTGATCCGGAGGCGCTAGAGGAGGATATGGGCGAGGATCCCTTCGAG
GACGACGATCCCAACGATCCGGAGTGGAAGACACGGACCGAGGGTGTTCGCAGCAGACGCATCTAAGACCAAAATCCAAAGTTTTCGTTATTTAA
GACTTTTAAACGATTTGTCAATTTTTAAAGCCACAACACACACACACCCACAAATCAGCCGGAGCAGACCAACAAATTTTAATTTGTTTCAAACG
GTTTGGTTTGCACTCACAACAGCATTGCGTACTCTAAGCAATCGTCTAAGTTATTTAGTTCTACGAGCCCACAAC
(SEQ ID NO: 1406)

Start ATG: 199

FIGURE SHEET 753

MAPALTAEPLSPKEKLTSTASPSARSSSESGGVGCAVGLVKKPATPTPATATTRITRSSAAAASVTASPHLQQQRSSLAINNKRKSGNAKASNEP
MGLSTAPTPHSTTSPNPSTDTAAASTSAVEHNNNDSNSTSAGNSTSADNSSTPKDNSTAQLLADLTINFEETISAEICLRKTLPDVSLGKEPVPP
ASVLAVATSSTSAGSALSLSAVDEVTKIEIDNIEERLSQLDGNATGRPEEHVAPPSVPVPVQEAPNTPTRPQAPPSAHLESPQPARTQQQSIQQM
TPQSTTSSNNFLKDGAAGAVLEDQDIEEVLKALKTFDGGHVNPDTICEFFDEVWEEAAPAAPLPPAPPENVVDVPGAKPSCSGILVSGSNISQPN
VIIKQEQRPWQESHAELEQQQHVISRRIEFLLRRMRKLQARAMCRHASEEVVGIMEWSARSSHKAPVPARSSTLTEQEATVLSIVSGRPSSTFWE
EQNKHPLPASQMSNVIRHIATAAKHQQICHSASGSSATLAPSSSWYNSCNSSALPMKRPRKNQLDASVATGATPTAPAPGAVTSRQAAGTTGSAT
GSNTPRADDIVPGYDTYVTNELTHVSGLLHTELREVQNAIDSDATESSSGGESADEMVTYNNNQQLSLPITRRAVWRYSRDRAAIALRWSWLCSQ
LTDLEMKIRQHSDLYMDLTQSKGEIQLESTAKTSPSLAQPANGIKEEPGSDYLCSRARPLVLSEFRKRKLFQTTNMHTISKKAARPSNIKCGCQW
PQVPCTLCTGRTDPTAPRDLVETMMPQNRVALLDAGYHPVLSFASDVSQSVHLEAVARQPDWQYRVMRSQPKAIVKAMWKAERETIASGGVGGQG
GSRRSGDAAKRRYIRRKERNNNSNKEAGSGAKAAAVAAGGAGGNGSSSVGGGDSGNGTGTATTSSSTTPTTTPLVANTAARGKRQPQHPTGANSS
SSLWPDSRQRQRQRHHSPSSTSISALSGAKKARKSATNSSSSNSTQQQQNHHGTKINNHHLNGYGDQWGEQSRSRRNSSPSNSHKNERTSERRVR
PIYDINNIVIPYSMLAQSKMEIIPYKEIPIPKWRIVDSDNDKGKHSSDESMERKLSNGCVASKSEELAKQQLPPPPDQDQEQPALQPPKVNGLKE
NQAVKHNNNNNTNNNNNKNGLVNGNAKKDELKAAEDHDTQSKEDDDPKEKVVKPKLNGNLIKNPIDKTAETQDKIAQPAPEPPLPKRPKLETPTS
NEVTKANGQLVQQQLESRESEEEPQHVDEDLSDEAFIMRHQRALLEERRRFETFLKFPWSTRSRANRRVDSRAESSGANTPDPASPAPHLGGPGH
DNESIPSPLAYPLDAFNESGELLTGGQARQARRRTTSSKLKDQLERRSTTPDLRESYTVMPSPFEPLNFPLSDEVYQRLLAETYAPPRSMTVSKR
AKSKSISSNCDGGNTFTGGSGSRRSSKCKIKPNGQLNGQLNGHPAAAKLNGIDAANEGGISEPEEEEMLLEDEDDDYPKHHLAPLDDEEPSTPDV
EHELYDSAIDAYLADPEALEEDMGEDPFEDDDPNDPEWKTRTEGVRSRRI*
(SEQ ID NO: 1407)

Celera Sequence No. : 142000012807541
ACACTGCCATCGCTGCCATCCCGTCGCTTGGTGGGCGTGGCAGGGGCACTGGCCGCGCCTGATTTGTAGGCGGGATGATCCCGCTCAGCATCGCC
GGCGGAGGAGAAGGAGGTGTCCAGTAGCGCGTCGCCCGACGAGGTCGGGGTGCCACGTGAATTAGTGCGCTTCTTCATCGCCTAACTACAAATTC
GATTATCAAATGTAGGCGGGTGGCGTGATGTGGTTGTTGTTAGGTGGTTGGTGGCTCGGAATCGGTTTGGTGGCTAAGTACATGCGGGGACTGAA
GGTTGCGCAACATTCGATTCGATTCCACCAAGACTTGCCACTCGGCTCTCCTCGCAGCGGTTTCTATGGCTCCCGGCTCGAGTGACCTCGATTGC
TATGGCGTGGGCACGGCTCCTGGATCCTCGACTCGCGTTCGATCGGCGCACGTTTATTTATCATTTGCCAGCTACCGTCCGTTGTTGTCAATTA
ACATGCTGCGCGCGGCTTGGACCAATAAAAATCGACACTTGCCGGCGGTGGTGTTGCCGGAGGGTTGAAATGTGTGACTTGATAACAGGGGCGTT
GCCAGATGAATAGCGGAACGTTGGGGGTGATCCAGGTATCTTATGATGACAAATATTTTGTATATTTTCAGATCGTATTCGAAAAGCAGTCATCA
CCCTACTTTATAACAAGATTATATTGTCACTATTTTAGAGTTATATAGCGTTAGTTATATAACTTAGTTCTTTACCTTATTTTTTCTATATAATA
ACTTTCTAGGCAGCATTTATGGCATTCCCGAGGATAAAATGATTTTTTGTTTACAAACAGTCAAATAATAATGAGGTCACGCATAACATTATTCA
GATTGGATATTTCAACATAGTGGAATCCTGGAACACCCCTAATGCTATGACTGTAGCCCTGAACAGCTGATTGCACTTGTTGACTAAAACGCAAT
CCACGACTTTGCATTGGTTTCGGAATAAATTGCTTTTAAATCGCTTTATAATGCTGGACAAGGTTAAAAATGTTATCGTAGTGCTATCAGGCAAG
GGCGGAGTAGGAAAATCCACAGTGAGCACCCAATTATCGCTGGCACTGCGAAAAAACGGATTTAAGGTAAGCCAAACCATTTCACCACAAAAACA
TTACCGATGAATTTTGAATGGTACTCATATGAACAATCTATTAGGTTGGTCTGCTCGATATAGATCTGTGTGGACCGAGTGTGCCATATCTATTG
GGTCTGGAAGGACGGGATATCTTCCAGTGCGACGATGGATGGGTTCCTGTCTATACAGATGAATCCCAAACCTTGGCGGTGATGTCCATTGGATT
TTTATTGAAGAACCGTGAGGATCCGGTCATTTGGCGTGGTCCCAAAAAGACCATGATGATCCGGCAGTTCCTCACCGACGTCAGGTGGGATGAGC
TGGATTACCTAATTATCGATACGCCACCCGGCACTTCGGATGAGCACATCACCGTAATGGAGTGCCTGAAGGAGGTTGGTTGCCACGGAGCCATA
ATTGTGACCACACCGCAGGAGGTGGCCCTGGACGATGTACGCAAGGAGATCACCTTCTGCAAGAAGACCGGCATCAATATCCTGGGCATCGTCGA
GAATATGAGTGGGTAAGTTATTTGAGTTTGTTAAGCCGCAAGACAGACAACAAAATAGGATTCATTTTAATTTGTCCTCAAAAAATTGGAACTCC
AATGCAATGCAACGAGAACGATATCCATCCCTGACTGAAAAGAGTTTTACAAGCTTCTGATAAGCATTTCTACTGTATTTGATGCTGACTAATTG
AAAATGCAAATATACATAGATATTAATTGGACGCCTTTGCGTGTCAAGTTTACGGCAGGGCGACACCTGTGGACTTTAACCAGGTGATAATTATC
TCATGTTTGACTAAATTATCTTATATTTGATTGTCACAGGTTCGTGTGCCCCCATTGCACCTCGTGCACCAATATATTCTCGTCAAACGGTGGCG
TCTCACTGGCCACTTACGCCCAAGTACCACATCTAGGAACTCTGCCCATAGATCCCCGTGTTGGCATTTTGGCGGGCACCACTACGTCCGTCTTG
GATGAGCTTCCGGATTCCACGACAGCGGAGGTGCTGACGCATATAGTTGAGAAGTTGAAAACGATGTTGGTCTCCTAAATAAATACCAACATAAC
AATTTTGTAAATATGATAGCTTGTTTCATTATTCAGTTTATGAATATAACCATTTTCTTCAGGAAACGATTTAATTTGCCATGGTATTTAATTGG
TAAACTTAAATAGGGACTCCCATTGTTAAACACATTTTAGCTTTTGTTTAGCTTTGGTTTCTTTTTCTTTATTTTTGTATGCTTTGGAATGAATG
TAGTTGATGAGTTTTGGGTATAATAATTTAAAATTATATGAGTGCGAGCGTTTGATATGTAATCACTCTAATGCAACAATTCTGCGTGTGCAGTA
ATTATAATTTACAATCAAACTAATACTTTCCAATTATAATTAATAACGTATTCCTTAACTGCTTAACTCCTACTGCTAAACCTAATCGCTTTATT
TATTGATTTGAGCATAGTTTAAAGATCAAATTGTATGCTTATCTCTGGACTGACGACAAAGTATAGTTTCTTTTCCTAAGTAGTACTATCATGCA
GACTTCATCCACTGTTTTGGTATAATTTTTAAGATCAAAAATCAGTCTGCAGGAGGATGGAATTCACACAGAGAAAAAACGAACTGATAAACTGA
GATGGCAACCTGGAACTATAATTTTCTCTCTGTGCAGGAATCACAACTTTTGCTCCGTCTTCGCTTTCTCCGTTTCATTCAGCTTTCGAACTGGA
TTTAATGGTATGGCATGGTATTTTTTGTTTTTCGAATATCTCTTCACGATGGCATAAAGGGATATAAACACTATAAGTATAACAAAGCCCATTAT
AACCACGCATTCCAAAGGCCAATCGGTTTGGATGCGCTCCTGGGGCACCTCTGCGTAGGGATACCTTATTTGCTGGATCTCCATACTGTTGAGAT
CCTTAATCTGACTGGTCGATTCGGGCGCCACGACCGCCGGTTGATTCGTGATGGGATTATCGGTCACCACGGATAAGAAGTTAGTTGCATTGACT
AAGATCACGGTGGGCTCATCAGTTGCTTTCGGT
(SEQ ID NO: 1408)

Exon: 1001..1111
Exon: 1185..1627
Exon: 1940..2168
Start ATG: 1001

Transcript No. : CT15597
ATGCTGGACAAGGTTAAAAATGTTATCGTAGTGCTATCAGGCAAGGGCGGAGTAGGAAAATCCACAGTGAGCACCCAATTATCGCTGGCACTGCG
AAAAAACGGATTTAAGGTTGGTCTGCTCGATATAGATCTGTGTGGACCGAGTGTGCCATATCTATTGGGTCTGGAAGGACGGGATATCTTCCAGT
GCGACGATGGATGGGTTCCTGTCTATACAGATGAATCCCAAACCTTGGCGGTGATGTCCATTGGATTTTTATTGAAGAACCGTGAGGATCCGGTC
ATTTGGCGTGGTCCCAAAAAGACCATGATGATCCGGCAGTTCCTCACCGACGTCAGGTGGGATGAGCTGGATTACCTAATTATCGATACGCCACC
CGGCACTTCGGATGAGCACATCACCGTAATGGAGTGCCTGAAGGAGGTTGGTTGCCACGGAGCCATAATTGTGACCACACCGCAGGAGGTGGCCC
TGGACGATGTACGCAAGGAGATCACCTTCTGCAAGAAGACCGGCATCAATATCCTGGGCATCGTCGAGAATATGAGTGGGTTCGTGTGCCCCCAT TGCACCTCGTGCACCAATATATTCTCGTCAAACGGTGGCGTCTCACTGGCCACTTACGCCCAAGTACCACATCTAGGAACTCTGCCCATAGATCC
CCGTGTTGGCATTTTGGCGGGCACCACTACGTCCGTCTTGGATGAGCTTCCGGATTCCACGACAGCGGAGGTGCTGACGCATATAGTTGAGAAGT
TGAAAACGATGTTGGTCTCCTAA
(SEQ ID NO: 1409)

Start ATG: 1

MLDKVKNVIVVLSGKGGVGKSTVSTQLSLALRKNGFKVGLLDIDLCGPSVPYLLGLEGRDIFQCDDGWVPVYTDESQTLAVMSIGFLLKNREDPV
IWRGPKKTMMIRQFLTDVRWDELDYLIIDTPPGTSDEHITVMECLKEVGCHGAIIVTTPQEVALDDVRKEITFCKKTGINILGIVENMSGFVCPH
CTSCTNIFSSNGGVSLATYAQVPHLGTLPIDPRVGILAGTTTSVLDELPDSTTAEVLTHIVEKLKTMLVS*
(SEQ ID NO: 1410)

Classification: hypothetical

Celera Sequence No. : 142000013384010
TTTTGGTTACTTGAAACGCTAAGACTGAAATGGCTTGTTATGGAGAAGAAAACACGTCCTGCAATACATTATATAATAAAAAGAACCCAGCAATT
TTCGCATCACCACATTACAGACAACAAAGTACTTTGTCCTCATCGTTCTGTGTGATCCAGATCCCCGACTATATATGATATATACACCTAGCTAG
ATTTAAGCGATTTGTACATACAGAAGCAAAAGCAAAACAATATACCAGAAAATTGCCTGTTAAATACATTTATATACACATATGAATTTAGTTAT
ATCACGATGACTAGTTTTTAGTTCTTAGAGGTTATTTAGTTAGTAAGGAGCCCAACTGACGTAACGTGAATAAATCAACTATATATGTGCCCATA
TATAAAGCGTACTATTTAATTATTTAGTTTTTACTGGACTTATGACACAACGAGCCACTGTAATGTCTTATTCAGCTCAATGCTCATAAACAAAA
TAAATATTTTTGGAAAAAATACTGTAGTTCTTCTTATTTAGCCAAGACGTCCAAACCTTTTTTTAATAAATTTAATTGAGATGAAGATTTGCATT
CGAATTCTATAGAAGCATCAAACAAATATTACAACAGTATCGAGTGGGTTATTAAAAATTAAATATGTAAAAATCGCTCATTGTGTTAAAATATT
AATTATAATAGATTAGCTCAAACATCTTAAATCGACATTTTGTGCAACACATAAAAATTCTCGCAGACAATTGGCAGCTGATTACGATTAAACAA
AACCGAAATTAGCCGTTTTCCTTTAAAGCAATCAGCATTCGTGATCTCTTGTTTGGTTACCTCACAATGCTAGTTAGTTATAGCGCCATAAAACC
CCATTTTCAATGTCAGGGAAATCATAAGGTCATAAGGTTATCCCCACGATCGTTCTAATGTGATCACAGCCACAATCTATAATAACCAGTTCCCA
ATAGATAGACAAGATTAGAAAACGCAGCTTGGTAGAGTTTTTATATTTTATAATTTAATTTATTCAGAGTGCTTTCTTGGGTATCGGGTCAGAC
AATTGAAACAGCATTAATATCATATTCGCATGTGTGGCCTGTGGGGGCAGCGGAGAGGAGATAACAAGGGGCTGGCCATCAAAGGTACAACATAC
GGACATACTTTCCAGCGAAAGCTAGACACACATAGGATTAAATATAGCACATAGTATAACAGAATATATATGGAATTGAATACTTTGAACTTGAG
TGTAGCTTAGTTTCGTACGATAGAATGTTTGGCTTTTAAAGTTAGAAAGATGTGTTTATAAAAAAGTGTGTATAAGTGCTGTGTTAGAGAAATGC
GTAAAGTGTTGTTTTGGAATGTACATGTGCAATGGCACACACGCAACATTAATGTATTCTTGCTGAGAAACAAGTATAAAGCATTTTCGCTATAC
TGAAACCGAAATTCGTTAGAAAGTAAAAGTATGTTGCTCCTGTGTCTGCCCACAATCGCTCCAACTAGTGAACTCTGTCCTTAAGGTAACCAATT
GGACTAGCCCACTTAATGCTGCTTGGCCTTCAGGCTAGCTGGCATCTCTGGTGGTGGTGGGCGGGGAATGCCCAGGGCGACCTTCACACCATCGT
AGATGAACCACTGCAGAGCGGTCAGGGTACCGATCATGATAATACGAGGAGTCAATCCGTTCCACATGCCACTGAAGCCCAGCGACTTGGCCACG
CTGATGGCGCTAGCTCCCTTGGCCTGGTTCAGCTTGGACACCACCACATCAGCGGGATGCGACACCACGGCACAGAACACACCGGCGATGTAGCC
AGCGGCGAAGGTCACGATCAGCTGCTCGCCCTTGGTGCAGTCGGCACGAGGCTTGGGCACCACATACCTGGGAAAAGTTGCATCATTAGTATTGA
TTTAACGGGGTTCGTTGGGGCTTGACAACCCGAACTGTGAACGGTATTGCTCTAGTTTTTACATTTGAACTTTCAGTGGCTACCTGCTAATTTGC
ACTTCAAAAGGAATGCTTTGCTTTTTTTATTTTATCCATAGTAACAAACTAGTTCTGAAATAATATGATTTTCCTATATTTGAACAAGATAAGCA
TTCGTCGTTGGTTTTTATTCTGGCGTGCCATTTATTAGATACGAATGGCATTCTTATCTGCTGACGCGCTAAAAGTTTATTTTATTATGAATACT
TTCAGTTTTGATCAATTAGCATATCACTTTTGAAATTTCACAGATTAACAGTCTACCTTTAAACTATTGTAATAGCAAAACGCTAATACGAATAC
AGATATTGTGCACAGCACTGGTAAGTTTTTCCGCTGTAGAAACTAGAGGATACCTAAAGAGGAAATGTTACTTACTTGTAGAGCAGCTCCACGGT
GCGCTCGAAGCAAGCGAACTTCATCATGGTGTATGGGATCTGTCGCATCCACAGGGGAACCAGACCCTTGTAGAAGGCATTGACGCCCTCCTCCT
TTAGCATCTTGGGCACTGCCTCGCGGAAGTTGTTGGCGTATCCGGGAATAGTCTGGATCTTCACCTTGGCGGCCTCGAACGGCGCCAGAGCGATA.
TCGGCGAAGAACTCGGCCGAAGCGGAAGCAGCCAGATACAAGGAGGTGCGGTACAGGTAGGCGTTCTCCTCGCCAATGATTTCGGCGTACTTCAC
CTTGAACAACTCGTACAGACCGAACTTGCACAGACCCTGAAAGATACAGAAACGCGGATTAGCCTGCTGTTTCTCAGAAGTTATTTTTCAGTTTG
CAGTAGTATCCAAGATTTATCTTCGGTATCTGTTTCTCCCGTAACCATAAAGTTGTCAAAGGTGTGTTGTTATTCTGAGGTATACTAAGATATC
AGCCTAGGAATCAAACTTCCTAATGTTCGATTCGAATCACTTTTATCTGCTTCAAGCCCGGAACCGATGTAATTAAGGTCAGCCGACCTGGTCAC
GAGCATATAATTCGCCTCCAGACGATTATGCAACCCATAAAGTGAAGCCCAATCTCACCTGTGCCGAGTAGCCGAGCAGAGTGGGGAACCAGCCC
TTAGCCAGTCCGCGGGCGCCCTCCTCCGCCACGGTGACCTTGAATCCGTGCACCAGATTCTTGTACTTGGCCTGGTCGACCTGCAGACGGCACTT
CACCAGATCCAGTGGGACCACGAAGGTGTGGGTGGTGCCGCAGCTGAGAATGCCACCAATTCCGCACAGAGCGAAGTACTTGGTGCTGCCGAATT
CGCACGAATCCTGCTGGTTGGCCACCGGGGTAGCGGCGGCGGCGATCTGGCGACCCTCAACCGGCTGGGGTTCCACCACTGGGGCGGCGGCATCG
CATCTTGCCATCGACATGGGGGTGCGGAATGGCGAGTTCCGGGCAGTTTCAAAGAAGCTGGAGAACATCTTGATTCTGTTCTTGTTCTGGGGTCG
GCTGAAAGTAGAGAGACCATCCATTAGTTACGTATATATGTACCTCGGAGGCGACATGTGCTTTATCTAATTATATATATAGCTGGGTAATCAGC
TGCTTTTCGCTTTTGTAGGTTACATAACGGCGTGCCTCGAATTCCGAGCACCCGGACTTACGACACCAAATTTACCCGAAAAGCGAAGGATTTTA
AGCAACCACGTAAATTTAGTGTATGTTAAGGGAGCGATAGAGCACCGCTCGGCTACTTTGATTTCGATTTTACAAAACTTATGCAATTTTCGCTC
GGAATTTTCGCACTTACTATTCGTCAGCAACGTTAGCGGCTCGTTGGCGAGGATTCAAAGAATGAGGGGGGGCTCACGGAGGTGCAGCGATTTCT
CACGAATACCAAAACGCCTTAATGGTTTTGCCGTGGAGAGGTGTAACTAGCGGATTGAGGATAGTTGGCCACACTCATGTCAAAATCTTCGGCTA
TGGACTGCAACCTTGGTGCAAAACTTTGGTGGCGCCTGAGCGTGGACTCGAACCATCTGCATACGAGGTATCAGGTGAGATTATTTTAATGCCAT
TGCCTTCGTTGTGAATAAAATATTAATTATTAATATTAATTTCATATTGATAACATTAGTTGTAAATATTTTGAAAAAATAATAAATTCATTTGT
AAAATCCTCATATTTTTGCATAGTATTTGTGATTTGTTTTCTATTTTTACACAATAAAACAAATTTTAATCTAAAGCTTTATTGTATTTAGAACT
CTCTGTAAAATATATAACAATTTTCAATTATATGTACATTTTAAATTTATAAGTTATAGCCCCATGGTAAAACTGGATAATTTTATGAGTAAATA
TGTGAAAATAAAGTTCTGCCATGATTTCACATGGGGTTGGCCCAATCCTTCACTTTTTACGCACGGACAGGAAATTAGGCCTTTGTATTCCATTT
TATATTTCACTCTGCAAGTGAAGCAAAATTCACCCTGGTGATCTTCAGTTAATAAGATTTGACAACCGATTTCTGGTGACCAAACGCAGCAGACT
TTGGCATTCATAGTATCTGTAAAATTAAAAAATTAGTCTTTTATTACTATTCAAATGCTTCTTATACCGATATGCAGTCCGGGTGGAACGCAAAC
ACCCTCTTTATTGGTTGTTTTGGGAATTCACCTTGTAGACGACCCAATCGCCTATAAAAGTTTCCTTCATAACAACTGAATCCTGTCTCTTTAA
TCCGACACATTTCCGTATTTTCCTTCCTACAATCTAAGCATCTCCCATTTTCTATTATAGATACGTTTTTTTCGGCACAGGTGATCAACAGTCTC
CCACTGAGTATAATAAGAAAATATATA
(SEQ ID NO: 1411)

Exon: 3777..3723
Exon: 3421..3004

FIGURE SHEET 755

Exon: 2696..2356
Exon: 1872..1001
Start ATG: 3393 (Reverse strand: CAT)

Transcript No. : CT15958
CCCCCCCTCATTCTTTGAATCCTCGCCAACGAGCCGCTAACGTTGCTGACGAATACCGACCCCAGAACAAGAACAGAATCAAGATGTTCTCCAGC
TTCTTTGAAACTGCCCGGAACTCGCCATTCCGCACCCCCATGTCGATGGCAAGATGCGATGCCGCCGCCCCAGTGGTGGAACCCCAGCCGGTTGA
GGGTCGCCAGATCGCCGCCGCCGCTACCCCGGTGGCCAACCAGCAGGATTCGTGCGAATTCGGCAGCACCAAGTACTTCGCTCTGTGCGGAATTG
GTGGCATTCTCAGCTGCGGCACCACCCACACCTTCGTGGTCCCACTGGATCTGGTGAAGTGCCGTCTGCAGGTCGACCAGGCCAAGTACAAGAAT
CTGGTGCACGGATTCAAGGTCACCGTGGCGGAGGAGGGCGCCCGCGGACTGGCTAAGGGCTGGTTCCCCACTCTGCTCGGCTACTCGGCACAGGG
TCTGTGCAAGTTCGGTCTGTACGAGTTGTTCAAGGTGAAGTACGCCGAAATCATTGGCGAGGAGAACGCCTACCTGTACCGCACCTCCTTGTATC
TGGCTGCTTCCGCTTCGGCCGAGTTCTTCGCCGATATCGCTCTGGCGCCGTTCGAGGCCGCCAAGGTGAAGATCCAGACTATTCCCGGATACGCC
AACAACTTCCGCGAGGCAGTGCCCAAGATGCTAAAGGAGGAGGGCGTCAATGCCTTCTACAAGGGTCTGGTTCCCCTGTGGATGCGACAGATCCC
ATACACCATGATGAAGTTCGCTTGCTTCGAGCGCACCGTGGAGCTGCTCTACAAGTATGTGGTGCCCAAGCCTCGTGCCGACTGCACCAAGGGCG
AGCAGCTGATCGTGACCTTCGCCGCTGGCTACATCGCCGGTGTGTTCTGTGCCGTGGTGTCGCATCCCGCTGATGTGGTGGTGTCCAAGCTGAAC
CAGGCCAAGGGAGCTAGCGCCATCAGCGTGGCCAAGTCGCTGGGCTTCAGTGGCATGTGGAACGGATTGACTCCTCGTATTATCATGATCGGTAC
CCTGACCGCTCTGCAGTGGTTCATCTACGATGGTGTGAAGGTCGCCCTGGGCATTCCCCGCCCACCACCACCAGAGATGCCAGCTAGCCTGAAGG
CCAAGCAGCATTAAGTGGGCTAGTCCAATTGGTTACCTTAAGGACAGAGTTCACTAGTTGGAGCGATTGTGGGCAGACACAGGAGCAACATACTT
TTACTTTCTAACGAATTTCGGTTTCAGTATAGCGAAAATGCTTTATACTTGTTTCTCAGCAAGAATACATTAATGTTGCGTGTGTGCCATTGCAC
ATGTACATTCCAAAACAACACTTTACGCATTTCTCTAACACAGCACTTATACACACTTTTTATAAACACATCTTTCTAACTTTAAAAGCCAAAC
ATTCTATCGTACGAAACTAAGCTACACTCAAGTTCAAAGTATTCAATTCCATATATATTCTGTTATACTATGTGCTATATTTAATCCTATGTGTG
TCTAGCTTTCGCTGGAAAGTATGTCCGTATGTTGTACCTTTGATGGCCAGCCCCTTGTTATCTCCTCTCCGCTGCCCCCACAGGCCACACATGCG
AATATGATATTAATGCTGTTTCAATTGTCTGACCCGATACCCAAGAAAGCACTCTGAATAAATTAAATTAT
(SEQ ID NO: 1412)

Start ATG: 84 (Reverse strand: CAT)

MFSSFFETARNSPFRTPMSMARCDAAAPVVEPQPVEGRQIAAAATPVANQQDSCEFGSTKYFALCGIGGILSCGTTHTFVVPLDLVKCRLQVDQA
KYKNLVHGFKVTVAEEGARGLAKGWFPTLLGYSAQGLCKFGLYELFKVKYAEIIGEENAYLYRTSLYLAASASAEFFADIALAPFEAAKVKIQTI
PGYANNFREAVPKMLKEEGVNAFYKGLVPLWMRQIPYTMMKFACFERTVELLYKYVVPKPRADCTKGEQLIVTFAAGYIAGVFCAVVSHPADVVV
SKLNQAKGASAISVAKSLGFSGMWNGLTPRIIMIGTLTALQWFIYDGVKVALGIPRPPPPEMPASLKAKQH*
(SEQ ID NO: 1413)

Name: mitochondrial carrier protein; phosphate transporter
Classification: transporter
Gene Symbol: Mpcp
FlyBase ID: FBgn0026409

Celera Sequence No. : 142000013385184
CGACGGCCTCCTTGGTGGGCAGGGTTTTGAGGATAACCACCACATCGGCTACATTGTTGCCCGTCAGTATGGTGCCCTTCTTGAAGGAGCCAACC
TGACGCACTTCCTCCAGTTGCTGTGGAATAATCAGAACAGTTTAAACATGCAAATCACAAGGAGTTGTGTAATGTACTCACACAAGTTGTCAGAT
CCCCGGGTGCAACCACCAGATTGTCGAGAACAGCCTGCACCTTGGTCACTAGATTGCCAATAGCCGTCTGCTCGCTGGGAGTGGGACTCAGGTCC
TGGTTACGCTTCAGCAGCGCCTGAAATGCAATTGTTTTCCCATTGCAGACACCTTGGATACGCAAGTAATTTATTGATTTACCGCAGTCAAAGCA
GAATCGTCAACGGCGCCGGCGGATGGAACTTTGGGAAAGAAGACCTCCGCGAGGGTCAGATCGAAGGGGTGGCGCGGCACGAATGTCTTTTTGAA
CGGCGGACGTATGCCGCCGCGCATGGGGCGGCCACCTCGGAGAGCTCCGCGAACCATATTCCTGTGGGGATGAATTTTTAATAATTTTCGCAACG
CCGGAGCGTTCTGTTTTTTTAACAGATAGGTAAACAGTGTGACCGAAGCTGGACCGGTAAGGAAACGACATCAAAGATGGGCTAAGCGCGTTTT
CAAAGTATACCGCATAAAATATTTTTAGAGGGCAAACATTTTGAACATTTAAACATTTTACTACATTAGAATGCATAAATTGATTGAATTAAAAT
ACGGAGACTGGTGTTTTTAATCTGCATAATTTTGTAGTTGTAGCTAGTGCAACAAGGTTTCTATCAGTTCCAGGAAAACGCTTTGTTTACAAGCA
AAGTGCTGATTTTTATGTTGATGGTCTTACCCTTTTGTTGTACAAAATTCCGGTGCTAAAATCGGATTAAAAGCGCATGAAGTTATTCGTAAGTA
GTTGAAAATCGCACTAGAGATGAATCCTAATGTTTATAGTTTTCAGAACTATGGATCTGGCGAACGTAGATCAACGCCCCGTGAAGGACGAACCA
CCTCAAGAAGACACTTTCGAAGAAGAATTAATCTTCATTTCTAACAGCGACTTCGAAGAGCTTGAAAGCGAAATAAAGATTGAGAACTTCTGTAG
TTATGGCAAAGATTTGGAGCCAGTTAAAGGCGTCCCGTCGAAGCTGAAGACGTGTAAATCCAAAATAGCAAAGAAGCGCCCCTTGCGAAAGCAAA
CAGATACGTTTAAGTGTACCCAATGCCAAAAGACGTTTACAAGAAAGGAAAACCTCGAATCACACTTGCGACTTCACGCAGAAGAACGTCCGTTC
GAGTGTTCCCACTGCTCCAAGAGCTTTGGACGCAGGACGCATTACAAGCGACACTTGCTCAAACACGAAAAGCGACCTCATAAGTGTTCCCACTG
CTCAAAAACCTTTACCCAGAATTCATCGCTTAAACAACATCTGCATGAGCACACAGGAGAGCGCCCCTTTAAGTGTACCCAGTGCTCGACGTCGT
TCGCGCGAAAATCTCATCTTCAGGTACACTTACGTACGCATAGTGAAGAACGACCCTTTGAGTGTACCCATTGCGAAAAGGCATTTAAAAACAAT
TCACATCTCCAGGAACACTTGCGAACGCATCAGGAGGCACGGCCCTTTAAGTGTTCCCACTGCTCAAAGAGTTTTAAGCTAAGATCAATTCTACA
AAAGCACTTGCTGACGCACGCCGAACGATCCTTTAAGTGTACCCAGTGCCCGAAGACTTTTCTGCAGAATGATAGTTTGCAAATTCATTTGCGAG
TGCACGCGGGCGAAGACCCGTTCAAGTGTCCCCATTGCTCAGAGACCTTTGCAAGGAATTCGAGACTTCAACTACACTTACTTGAGCACGCTGGA
AAAGAGCCCCTGAAGTGTTCCCAGTGCTCAGCCACCTTTGCCATGAGGTCACTTTATCGAGTCCACGTGCGTTTGCATACAAGAGAGCGACAGTA
CAAGTGCGCCGAATGCTCGAAATCTTTCTTCAAGAAGTCACATCTTGTGGAGCATCAGCAAGTGCATACGGGAGAGCGGCCCTTTAAGTGTACCC
ACTGTTTCAAGGACTTCAAATGTCGTACGCATCTTCGGGTGCATATGCTTGATCATATTGGAGAAAAGGTACCCAAGTGTTCCTACTGCTCGAAG
GAGTTTAAACTAAGCTCGCAACTGCTGGTGCACCTGCAAGAGCATACTGGAAAAAACCAATTCGAGTGTCCCCACTGCTCGAAGTCCTATACAAC
TAGCTCGACTCTTCACATGCATTTGCGAACGCACACGGGAGAATTGCCCTTCAAGTGTTCGCACTGCTCAAAATTGTTTGCGAGAAGCGCAGAAC
ACCAGGAACACTTGCGAACGCATACGGGGGAAAAACCCTACAAGTGTTCACACTGCTCAACCCGATACACACAAAAGTCCAGTCTTGGGCGACAC
CTGCGGCGAACCCTATGCGGCACTAAATCGGATTAAAACCAATTAGTTTAGAATTAACTTAGAAATAATGTAATAAGAAGTAAAGTAGGCGAAAA
TAAATAAATGAGTTTAAATATTTTTTTAAGTTTAGAAATCGGTAGTGTGCCCATTTGTTTAGTCCCCCTGATCGACCTGTACCATATTTGGCATT
CAGCATTCGGTCACACTGCCGCCCAATTGCTGTGTCATTTTTGTTTCTGTGCGAAATAAGTCGGCTTTTTCATTTTACACATCAAATCACTGCAT
TTGCGGCCCAGGAAATATGGCTACCGAACGATACAGCTTTTCGTTGACCACGTTCAGGTGAGAGCATCGCTATAGCCGGAGCGGAGCATTCGCTT
CGCCCCGCGCAACACAAACTGCCGCCATGACTGGGCAATAAGTACAATTTTCTACCGTTTGCAGTCCTTCCGGAAAACTCGTCCAACTGGAGTAT GCATTGGCGGCCGTATCTGGCGGAGCTCCCTCCGTGGGCATTATAGGTTAGCATGCCGCACAGCCAGTCAGCCTGTCAGCCAGTACTGTGCATTC
AACTAACACACTATTATTTATTTTTCTTGGCTGTAGCTTCCAACGGCGTCGTCATTGCCACAGAGAACAAACACAAGTCACCGCTGTATGAGCAG
CACAGTGTACATCGCGTGGAGATGATCTACAACCACATCGGCATGGTGTACTCGGGAATGGGTCCGGACTACCGCCTGCTGGTCAAGCAGGCCCG
CAAGATCGCCCAGACGTACTACCTGACCTACAAGGAGCCGATTCCAGTGTCACAGCTGGTGCAGCGCGTGGCCACGCTCATGCAGGAGTACACTC
AGTCCGGGTAAGTGTGCGCGCTTTTCTCGACTTTGGGTTCCCATAGATAATCGTATGCAATCCCACCAACAGTGGCGTTCGTCCCTTTGGCGTTT
CCCTACTGATCTGCGGCTGGGACAATGATCGTCCGTATCTCTACCAATCCGATCCTTCGGGCGCCTACTTCGCCTGGAAGGCCACT
(SEQ ID NO: 1414)

Exon: 1001..2506
Start ATG: 1001

Transcript No. : CT16741
ATGGATCTGGCGAACGTAGATCAACGCCCCGTGAAGGACGAACCACCTCAAGAAGACACTTTCGAAGAAGAATTAATCTTCATTTCTAACAGCGA
CTTCGAAGAGCTTGAAAGCGAAATAAAGATTGAGAACTTCTGTAGTTATGGCAAAGATTTGGAGCCAGTTAAAGGCGTCCCGTCGAAGCTGAAGA
CGTGTAAATCCAAAATAGCAAAGAAGCGCCCCTTGCGAAAGCAAACAGATACGTTTAAGTGTACCCAATGCCAAAAGACGTTTACAAGAAAGGAA
AACCTCGAATCACACTTGCGACTTCACGCAGAAGAACGTCCGTTCGAGTGTTCCCACTGCTCCAAGAGCTTTGGACGCAGGACGCATTACAAGCG
ACACTTGCTCAAACACGAAAAGCGACCTCATAAGTGTTCCCACTGCTCAAAAACCTTTACCCAGAATTCATCGCTTAAACAACATCTGCATGAGC
ACACAGGAGAGCGCCCCTTTAAGTGTACCCAGTGCTCGACGTCGTTCGCGCGAAAATCTCATCTTCAGGTACACTTACGTACGCATAGTGAAGAA
CGACCCTTTGAGTGTACCCATTGCGAAAAGGCATTTAAAAACAATTCACATCTCCAGGAACACTTGCGAACGCATCAGGAGGCACGGCCCTTTAA
GTGTTCCCACTGCTCAAAGAGTTTTAAGCTAAGATCAATTCTACAAAAGCACTTGCTGACGCACGCCGAACGATCCTTTAAGTGTACCCAGTGCC
CGAAGACTTTTCTGCAGAATGATAGTTTGCAAATTCATTTGCGAGTGCACGCGGGCGAAGACCCGTTCAAGTGTCCCCATTGCTCAGAGACCTTT
GCAAGGAATTCGAGACTTCAACTACACTTACTTGAGCACGCTGGAAAAGAGCCCCTGAAGTGTTCCCAGTGCTCAGCCACCTTTGCCATGAGGTC
ACTTTATCGAGTCCACGTGCGTTTGCATACAAGAGAGCGACAGTACAAGTGCGCCGAATGCTCGAAATCTTTCTTCAAGAAGTCACATCTTGTGG
AGCATCAGCAAGTGCATACGGGAGAGCGGCCCTTTAAGTGTACCCACTGTTTCAAGGACTTCAAATGTCGTACGCATCTTCGGGTGCATATGCTT
GATCATATTGGAGAAAAGGTACCCAAGTGTTCCTACTGCTCGAAGGAGTTTAAACTAAGCTCGCAACTGCTGGTGCACCTGCAAGAGCATACTGG
AAAAAACCAATTCGAGTGTCCCCACTGCTCGAAGTCCTATACAACTAGCTCGACTCTTCACATGCATTTGCGAACGCACACGGGAGAATTGCCCT
TCAAGTGTTCGCACTGCTCAAAATTGTTTGCGAGAAGCGCAGAACACCAGGAACACTTGCGAACGCATACGGGGGAAAAACCCTACAAGTGTTCA
CACTGCTCAACCCGATACACACAAAAGTCCAGTCTTGGGCGACACCTGCGGCGAACCCTATGCGGCACTAAATCGGATTAA
(SEQ ID NO: 1415)

Start ATG: 1

MDLANVDQRPVKDEPPQEDTFEEELIFISNSDFEELESEIKIENFCSYGKDLEPVKGVPSKLKTCKSKIAKKRPLRKQTDTFKCTQCQKTFTRKE
NLESHLRLHAEERPFECSHCSKSFGRRTHYKRHLLKHEKRPHKCSHCSKTFTQNSSLKQHLHEHTGERPFKCTQCSTSFARKSHLQVHLRTHSEE
RPFECTHCEKAFKNNSHLQEHLRTHQEARPFKCSHCSKSFKLRSILQKHLLTHAERSFKCTQCPKTFLQNDSLQIHLRVHAGEDPFKCPHCSETF
ARNSRLQLHLLEHAGKEPLKCSQCSATFAMRSLYRVHVRLHTRERQYKCAECSKSFFKKSHLVEHQQVHTGERPFKCTHCFKDFKCRTHLRVHML
DHIGEKVPKCSYCSKEFKLSSQLLVHLQEHTGKNQFECPHCSKSYTTSSTLHMHLRTHTGELPFKCSHCSKLFARSAEHQEHLRTHTGEKPYKCS
HCSTRYTQKSSLGRHLRRTLCGTKSD*
(SEQ ID NO: 1416)

Name: zinc finger protein
Classification: transcription_factor

Celera Sequence No. : 142000013384536
GTTTAATTCAAGGATTCCTCTTGTTTGGGCATTTCAGATATTGGCAGTTATCTAGTGTTGTTTGGTGTCTTTGAAAACTGTTCGAAAATGGAATA
ACAAATAATCTTGGGCAATTCCCATTACAATATGAAGTTGTTATTCTTCGCAGCCAGATGGACTGTAATGCAATCGTAGATCACAGCTAACTCCA
CTCGCAAGCGGTTCATAAATCATTCAAGCTAACCCATGAAAGGCAACTGTTTGCCAAGTCAATCCAGGCCAAGACCCCCCAGACTCTCCTCGTAT
TCGTGGTTATCTTGGGATTGGATTGTTATACATTGACTTTTTGAAATGCAAATCACATGCAGACCACAGATGCATAGCCAATGAATGCAAATAGA
CAAAGACCTGCATAGGCTCCTATTTACATACATGTTCTCAGAAAATCACATATTCAAACTGCTCCTATCTCCCACCTCTTGCCCTCCCCTGCAGG
TCGGATGTTTGCGTTTAACTTTTTACATTAACTGTCATTTGGTTTATTTCACAATTTACAAAATGCAACTTAAACAATGGTCTTAGACGTGGTGC
TGGCCATGCGTGGAGGAGAGTGTCGTCAACAGATGTCCTTTGTGTTGTTCGGCATCCTGGTTACATTTTACATACAGTGCAGTGGAAGGAACTTA
ACTAACTTACTGCGGTTGCAACCGTTTCTCGGGTTCTTTAATTTGTTGTCGTGTGCTACACTAGTACTAAGCTTTGCTGCTGCGGTTGCCGTACA
CTTGGTGTTCGCTTAGTTTGCCTTTGTTTCAGTTGACGCTGCTGTGGCTTCACATTGCTTTAATTTTGTTTCATTTTGTTTTCATGGTGTTAGTT
TATATCGTAAATTTATTTATGCAATTTTATCTCAATTTCATTAATCTGTTTTGCTTTGTTTTGCTTTTCTTTGCCTTTTAGTTTTGTTTTCTTGT
TTTGCCTGATTTTTACATACACATATTTTGTTTACAATTTTCTACTAGACTTAATCGGCATCCGCGCGCATACCCCGCACCTCGCCCACCTGCCG
CGCCTTGTCCAGCTCCTCCTTCGTCTGGTCCTCGATGGCGCGAATGTCCTCCATTGTTAGACCGTACCAGCGATCGGTTGAACAGAAAACTTGGC
TAAAAATAGAAATGAAAAGACGATCAATAAGGAGTTTCCATCCAGGGCATACTAAAAAGGTATTCATGCATATCGAACTTTATAGATTTTAAGCA
GTTCAAGGATATACAATTTCAAGACTATTACCGATGGAAGTTTGTAAAGAGGCGACGCTCCGATTTCTGTATGAAATTCTCTACTCTTGTTTGCA
GGCCGAACCATTTGAACTCGCACGTGACCAGCTTGTAGCAGGTCATGACAGGATTAACATGCTTTTTCCAGTCGGATCCCACCAGGGGACCGCGG
CCCGTCTTCTTTGACTGGTAGCTGAAAGGATGATCGAAACGTAAATTTCTAATTCACATCACATTATTCAATATTAACGCTTACGTGGTTGGATC
CTCATCGGGCTTGTAGTCCGCGGGCAGCACCGGATCGTTGGCAATGTCGATGTGCACTATCTCTCGCACTTTCAGCTTATCCGGCGTCAGCTCGT
GCACCTGCAATATCGAAGAGCCATGGCGATATATCTTAGATCCATACATTTTATTAACTTATCGAACACAAAAAGCGTTTACTACATAGACATGA
ACATGGATCGATGGCGGATAAGAACTACAAAGCCGAATCGAGCAGAGACAGCAAATGAAATACAAAACAAACGAAACTTACGTTGTCAACAGTGC
CAAGGTCATTTTCTATGTGTTGCGAATAAATGTCTATTTTAAAGTTTTTATCCATATAACCAGGATTCTTAATCGATAACCAAAGGATTACAAAA
CCAAACCAAAAAAGCCAAACAAAATGATGGTAGGATTTTGACAAAATCATATTGCAGGATGATCGAGTTAGTAGTTAGTTTTCACAAATAAATGT
AGGGTTGAGATGTGATGATGTTATGGAGAGAAAAGAAGAAAACACACGTTAGTCATATCATGCTGTGGATTCTTGACTTACATTTTCTGAATCGC
CCGCATCTCCGACGTGCAGAGTGTCGATGATTATTTTGAAAGCATCTTTCATAAACTTGGGGTTCTAGAAATTCAATATAATCACAGTAATCATC
AGGTTGCCTCACATTGCAGTACATTGCTAATGCTAAACCAATTCATTTGTTGATTTGTTTCTAACCCCCATTTTGTTACAACTATTAAATTTAAG
TGCTCTCCCCATTTACCGTGATAATCGTTCGACAATAGGGATAGGCATTCCATGCCTCCTCGTGGATCTCCAATGAGCCCTTGGGTGCCAATAGT
CTTATGTAGGCTGGAACTTTTGATTGCAGATGGTAGATCTTATATGTATATTGACCGGAATTGTATTTGCCACCTGTAGGAATCGAAAAACTCTC TGTTAGCCCGCAACTATTCATTACCAATCGGTATTTGCTTACCCAGCAGGGGAAAATCTTCGAAGGGTTCGTTTTTAACACCTCGATGCCCTCG
CCGCCACCCGTATTCTCCTTTGACGCCTCGGCCACCGAGAATAATTGTGCAACTTGATACTGTGGAGCAGAAAAAAAAAGGAGTTGGGAAAATTG
TTATCCTCGTGACAAGGGGCTTTTTGCCCAGTTAACTCTCTTACCTCTTCCACAGTCAATGGCAAAGTCACACGGCTGCAACGAGAAAAAAAAAT
GAATATGTCAGCGAATGTGTGTGTAAAGGCTACGTGATTTTAATTAAGTTTAATATAACCATTTTAATTAAATACCATGCCTGTGCATAAAAAGC
TGTTGATACCTTTCGCGCTACTTCGGGTGTATGGAGTATATCGAGTTTAGTACGAGGCGGAATATACAAATTATTAGCAATAACCAGTGAAATGC
AACCAGTTATTATTGCTCTATTTAAAGGAGCGGTATTCAGACTACGTTTTAGTAGTAAATATGCCAGTGTCTTTTGTGCAAATAAATTAAATATG
CATTCAGAAACAATAAATGTCACCCACTCACTACATGCAAATAGTTTAGACTGCATTTCTTTTAGTTTACAACAGGTGTACTTAAATCTCGATGG
TTTTTCTGTTTGTCAATAAATAATCCGCTTTGTAATAGGAACGCTTTCCTCTTAAGGCCAACTTTGAATTGTCTGTTCCACTTTAAGTTCTAAGT
AGCAAGGCACACAAATTGCCTCAAATTACAAGCCCTCTACTCTGGTTTTACATTTTCTAAGGCAATCAACTCAAGCCCCAAAGTATGCAGCACCT
ATTCAAACAAGGAATCTTGAGACTACTTGCAAGAATGACCATCGGTAATTTTGGCTAGAGCCAATCAATCGTGGCCAATTGATACTTGTTGAGAT
AAGATCTCAGGTAATTTATATGAGCACTTAATACAAACTGTTGAAAAAGGTTAATATCACTGCACGATTTAAACGATATATTTTTAATTAAAAGC
TTACACGAGTGGGCGGAGCATTGGCATTGAAAAGAAACAAAAACAAAGGGTTTCCACAGCATAAAAGCTTCACAAGCCTTTTTGCATTTTATTTG
CATGCATATGAGTTTGAACACGCCAAACCGAAAACCCACCCACTTCCGGGCCACATACTCATCCTCTAATTACCAAAAAGGTTGCCAGGCAGCAA
AAGAGTAGGAAAAAGCGGCGAAAAGTGTTCTGGGACCTCCATATACATAATTATGCCAGCCTTGAAACTTGTACGCATCGCTTGACTTTTGTTGC
GGTTTTGGCGGGGACAATTTAATTGCAAAAAATTAATTTTTTACAACGAATATGAAATGCTCTTAAAGGATGGAAAAAAGTCTATTAACTTTTAT
AGCTTTGAGTTTAGAAACTTTACTTTAATAGAACAAAAGAGGATTAAAACCTGTAACCTATATTATCATCGCTTTATAATCTCCTGCCAATGTTT
CCATTTTGAGAGTTAATGACGCAAAAATGTTCTATGCATTCCCAAACTTTTTTGATGGTTTTTTAATTTTTTTTTATAGAGAAATAGTTAGGCCA
AAGTTCTTTAATTTTGATACAGCAAGCATAAAACTGTGATGAGTGAAAAAGAGGAGCATAAAAACCTCTGGTATTTCGCCTTGATCTCTGGGAAT
TTACAACCCGTAGTCGCAATGTTGAAATTTAGCTACAAACTGTAAGCCAAGGAAAGTCAACAGTCAACGGCTTGGCAAATGAAATATTCCCCGGC
AAATAAAGGCCAAATTGCTCCCCGGTGCGAGGGAAGCCTTGGAATGCATTCGCAAGGTGCGAACTGGAGCTCCTTGGCCATAAAGAACCTGAACC
TCGTGCTGGCCCGGCTTTATGGGCTGTCAGCCGTTCTCGCCTCCCCACACATAATACACATAATACACGGCAAATGCCAAACAATGAGACACAAG
AAAACACGACACGACTCGAGAACAATCAAAGTGATGTGGCGAAAGTGGGGGAAATTCGGGCCTTTGCTTGCCGGTTGTCTTGCAGACGCAATTAA
CCTTTTGGCCCACTGTTGACACTCGTAATGATGTGTTTCCTAATTGCCAGTCGACTCGAGCAACTGGTGGGCGTGGCAGAGGGACAGAACCAGGC
GCTTTAATGCTGCCTACTCAAAAGTTGGCCAACTACGCGCCGGCCCTGAAAAGGTTAAAGTTCTAAGAGCACTCTTTTTATGGCGGTAGGGGATC
AAGTTCAACTTTCGGCCGAGTTCATCTGGGGGGTTATTCTCCAAACAAGGTGGATGATTTAGGAGTGTGTGCGTGTCGGGGGAATGGGGCTCCAA
AAAGTTGGAACTATAAAGGGACTTAGGGAGAGGTAGAACATTGTATTGCGGTGTTTAATTGTTAATGAAGTTATTCGGAACTTTACTTAATCATT
GCATAATCAAGAGGAACGATTTGAGCTCTTGTGGTGTGTGTGTGTTCAACGGGTTGGAATTAAAGTTTTCGCTTAAGTCATTTAAAACGGAAATT
CTAAGGTAAATTGCTTATGCTTTGCATTTTTGGTCAATTAACAACAGCCCATCTATACTTATGTAAATAAATGCCTAAGTAATTCCAAATAAATA
TTCGAAATGGTTACCATCCAATTTAATTACCCATTTATGTGCCAACGTATCATCAATTCATTTAATTATGCAAACAGTATAACTTTTCTTTTCAA
CAAATTTCCACGCAGCATTTGTCGTTCAATCAAATCTGATTGTAAAACTTTAGCGCAAAAAATTGCCCATAAAAATTGGTCTTCTGCACAAACTT
TTCCTGTTCCGCAAAAAAAGAAAGCATTTCATTTCTTGAAAGGCAAAAAAACTTGCTAAAGCTTAAAACCCAGAAGAGGGAAAACCATTAGAGGA
CAAACCAGAACGTGTTTTTGTGACAAAATCGCTGTTCCAATAAGTTTAGTGGTAAATAAATTTCCCTGAAATTGTCGAAACAACATTCAACTGGG
TTGAACAACATCAGCAAATGCGAGAGATCAAACGATATAGTCGCGTTTCTCCATGGGGTTTTTGGGTTTCCTATGAATCACAGCACAATCAGAGC
ATTGAAGAAATTATGCAAATCAAAAATAGAAACATACAACAAATCCCCACACATGAATGGTGGTAGAGGGGGGCCAAAAAGTACAAAAGTACAAA
AGTAAAGCAAAAACAAGCGTCTGAGAATATTGAAGAACTCTTAATGAGACCAAAGTTGCCGAAAGAAACACTCGGGAGACCCCTTGGCACTCAAC
CCTCTTTTGTGGCCATGAACAAGGGAAATTGTTTGCTCTTGTTGGCATAATTGAAAATGGAAAGTGATTGTTTGGGGCTCTGTGGTCTTCGCATC
CCAAAGAGGTGGTGTGTGTGTGTGTGTGGTGTGTGGTGTGTGAGTTGTGTGGGTGGGTCGAGGGGAAAGCTAGTGGCCAAGGCTCTTGTGGTG
GCCATTATTGAGCGACGCCCACTGGCCATTGTCGCAATTGAAGGCCGAAGCCAAGTAATAATTGATTTACCCGCAATAAAGATGTCACACAGAGA
TTGCTCAGTCGATTGTTCAGTGAATAAGGCAGCAACGAGTCATTCGAGCTTGAAATTAAAGCATTTGTGCTAAACCTTCGTCTAACTAACAATAC
ATATAACAAAACGATATTATCCCTGTTAAGCAGTAGGTGTTTGCATTAACATAAGTAGATATTCTGATGTGTTTATAATTTAAGCCATTTACAAG
CCATAAGTAATTAGCTATCTAAATAGCCAAACCATTTATATACTATTCTTAAGCGTAACTGATAACTGACAAAGCTCATATGGAAATCAAGTGAA
ATTATAATATGGCCATGCACCATTGAAGAGAAGTTGTTTTTAAATCAAGGCCGCATTTCGCGGTTTGCCCCCATTCGGATAATAGCATACTATG
TATCTCCATATTTGGAGCCCAATTATGCTGGCGCTTAGTAGCCGGCACGCTCAATTGCCAAACATTTTCGAAACAACCGAAGCCCGAAACACTCG
AAACGTGTAATGAGTACAGTGCCGATGTGAAGTAAAACGACGCATTGAAGTCGAAAGCCAAACACTGCGTGTTATCTTATCGCAGTACATAAAAA
AGCGCACAAATGGCGGAACTAAATTGGAGCTCGTGCCATTTTCAAATTGATTGCTGGCTGGGCGAGCGGGGAGGGCGAAGGGAGAACTGTATCTG
ACGGATACATGTGTGGTGTACAAAGAGGCCAATCAGTTTGGGGCAGTAAAAGTCACGCTACAGCTGGTTTATGACGAGCACCATAAAGGACCGAC
ATTGAAAACAACAAGCTTTTGCTTTCAGAGATCAAAGTTGAGACGGTTGAAAGTTGAAAAAAGAAACCTGCACTCACACCAACTTTATTGTCGCA
AAAACGTGGCCTATGGACGAGGGTAAATGAATTTGCTTGATGGTTGGCCGTACAGCAATAAGATCGATTTCATTAAATTCTAAGAATATATAATC
TATTTGAACCATTGTTTATTTATTTAAACTTTCCAGCCAATTGCTGATATAATCACGTAAATATAGTTAACATTATTGGCTTGATTCCACAATAA
ATTCTGTATTCTAAATTCACTAGCTATATTTACTATGTCAACAAATAAAGTGCAGCACTTTAAACATTTTGTGAACAATAAAACACAATTTCAGA
TAAATCATGCCAAGTGCAGACTATCACAATTCGTTGTTGTTACCTTTTCAGCTGCTTTTTATTCATTTGGCCACTTTGCCCGCCGGCCATTCAAA
ATTGTTTATCAGCCTGCAGCAACCTGTGATGCGGCACGCGTTGCCTTTATTTGCACCTTTGTTTTTCATTTAATGACGATGCTGAAATGTTCATT
GCCAAATGGTTTACACGCCAACAGGCGGCAGACGAAAAAAAATGCGAAAATCTGGCAGGAAAAACATTTTGAAATGCAAATGCTACGGGCTTCGG
ATTCGTGTTGGGATTACGGCGTCGAGAACAATTAAACATTAATGCCTCTCGTGAAGACTGCCCGTCAACTTATGCGTATTTAAATAAATAAAATA
AAAAAAATTTTATTGTGCAGTAAAATGCAGTTGCCTTAAATCTTCCATATTCTCTGTTAAAAATTTCGAGCAATACAAAACGTTCCCAGAAATGT
ATATTATTTAAAGACCGGCAGAAGTATATTTTCACCTATACTTCATGAGCTTTAGTTTACTTTTTGGTCGTTGCACACTTGAATACATATCGTAC
ACCATATGATAAATATTAATGATATAAATACATTTTATGGGTAATCTAAATAGGAATTGTGTACATTTCTGTGAACGAACGCTGTAATGAACTAC
CAAATGCCACGGATTTTTCGCTAGCTTTTAAAAATTTTCCATTTTAAAATTTTTCCATATCATTTCTTCTTTATGATTAATGATATACCTATGTT
TTTGTTGCAATAATATTCTTAAATGATATGTAATTAAAAATAAGCTATACAATACAAGCTTAGCAACACAAAAGTAGAAATCGATTTCTGTGTAC
TTTAAGCCAGAAACCGATCGTATGAGAATTAATAGCTTACAAAACCGATACACTTAACACCTATCAGTAAAAGGTGCTGTTTATATACAATTGAG
TTTCCATTATAAGATTGATGCGAATGATTGCGCATACGAAAAATGATAAGACCGAGATTGTGTGTTTGAGCTTTCAGTTTCAATCTCCTGTATGC
AAGCCGCTCGGATTTTCCTTGATTTTCCGACAGCTGTCAAAGTCAAAGCAATTATAAGCCGAGCCATTTGATGTCAGACTTTTGACAATTTCCGT
TAATAAATTAAAAGTATCATTGCCAAAATGGGAATGTGAGGGTGGCAAACGTGAGCCATTTGCAAATGAGAAGAATGTATGAGAAGAATGTCACC
TGGTGCTTTGCGACCGAAAAGGATTAAAGATGCACGATGAGTCAGTTTAGTGGGGTTAACGCAACGACCTTATCGCACTTAACAACTTGTTTGAT
TAAAATCGCAGGGCCCAAAGCCGAAAAGAGAGTAATGGGAAAAGAGAGGCGCAAAAGAGAGTGACTCACTGAAAAAGTCGACAACGTGGCGTCGC
CGAGCGCCTAAAAAGCATTATCTTTACGTATATAGTATAGATTATCGATGATTCAAAGGAGTTTCCAAAACTAATTAGCAGTGGCATTGGTTATA
AGAAGTAAGTTTTGGCTTACGTAGCTCCAAAATGTGACTTAAACTCATTACGTCATCGCCACAGCTGCAAAATACCTGAGATAGAGCGAGATGGA
AAGAGAGGGGGTGTGCGGAAAAGGGGGCGTCAGGGGGCTGATAAGAAAACGGTTCTGTTGTTGTTGCGGAAAATGCCCGCAAACTTAAATACAAC
AAAAGCAACTACTGAGAGAACTGAGAGAGCAGCAACACACGCGACCAGAGAGAAATGGAGAGAGCGAATGTCACGAAGAGAGTGTAAAATCGATT
TGTCACAAATAATTTGCGGCTTGCCCAGATTTTTTTTTGCGATTTAAACATCAAATAATCACAGGTAAATGGTAAAAACATACAGTTTTGTACTC
ACAATTCTTTGATCTGCATCTTTGCCAATTATTATCCGGTATTTTCCTGCTTGATTCGCTGCGAGAGAGTACAAAATACAGAATTAGATTTAATG

FIGURE SHEET 758

CGAATTCGCTGGCGGATTTCAACTAAATTGTAGCATTTATTATTTCCAAATATAAATGCACTTGCACTCTACGCTTAACCTTCGCACGCACTTTC
TATATTTAATTTACATATATATCTGCCAATAACACTTTGGTGTTTTTGTTTCGCTGCCAAATCGCTGCGCCCGCACTTTTTGTTTATGTTTGGCC
AAGCCAACTTTAGTTTAGTTAGCCAATTGGGATTCTAATGCTTTTTCTCCAATTGTCGGCTAAACGCACGAGTCATATGCACACACACACTCTCT
TGCAAATACACACGCACACACAGCGGGCGGAATATCAATAGCAATTTATGCGATTTGCCGCTGATTTATTACTTAAGTGATGACGTACAACTGGG
GAGTGCGATTGGCCTGGTATCGGGATCGGTACGCGTTTGCAAATCGGCGGCAGTAATATACTAGTAATGAGTTTGTTATTTAGCTACTGCGTGTC
CGGAGCGGAGCTAAAGTTCGATGTTCGTGCAAAACACTTCGATTCCGATAGGCGGATGCTATCGATTTCGGCGATGCCCCTTGGTCACACTTGGT
GGTGGGCGCTGCCCGTCGCCGACTATCGATAGCACAAGCGGGTTATCTAGGTGTGCGCAGCTTGTTAGGGTGACTCATGCTGTTAAAATTATTAT
AAAAAGTTAATGAATATAATATAGTTATAATAAAATTATATATAAATCTATAAGATCAAAGATCATCAGTTATCATTTATCATTTGATTATATGA
AAAACAAGAACAGAAACAAGATTTAATAGGTTTTTGAAATGTGAAAATGTGGGTTACCCCCAATTCTTATTCGAAATTAAATAACCTAAAGAACA
CCTACACAGATAGGTAATTTGCACATAAGCAAATTTTGTCTAGAATTCCAAATGGTAATAATAGTAGTAATAGATTCCAATTCTTATAAGCTTGG
TGGCTCCGTCATTTCCTCCTTCTTGGCATCATTTCCCATTGCGTCTAGTGCGTCCTTCTCATCCTCTGGCGGTGGCGGCAATTCTAATCCTCCGA
GCATACTTTCTGGTCGATTTGGAGATGGCGGTTCGGGAACGAGCTCTTCGGATTCGAGATCTATTTCGCGGGGTGCCTTACGAGTGGAGGGCCTT
TCGAAATCCGGATTGCCGTCATCATCGGTGCGCATGCTCAGCGCGAACTTGATAATTCCCATGCCCTGGTAGTCATCGTCGATGGGTATGTTTCG
GGCCCACACCTTGCAGCTGAAGAAGGTCTTCGCATTCTCGGGCATCTTGTTCATCTGGATGGCCACCACGCGCGTCACTCCTCTCATGTTCTCGG
AGGCCTCGAAATATGGACCCGGATAGAAGACCATTTCGGGCTTGGGCCCATTGGTCACCTCGCAGGTGATCCAAATCTTGGGCGTGTTGCCCAGC
TTGCCCACGGTGTCCTGAAGGCTCGCTGGCGCCTCCTTGGGCAAGTCATCTGGCGTGTCGTAGGTCTCCGGCACATAGCCAATA
(SEQ ID NO: 1417)

Exon: 9724..9589
Exon: 9178..9123
Exon: 2735..2705
Exon: 2624..2513
Exon: 2448..2297
Exon: 2154..2077
Exon: 1619..1510
Exon: 1446..1267
Exon: 1139..1001
Start ATG: 9139 (Reverse strand: CAT)

Transcript No. : CT16783
TTTTGCACGAACATCGAACTTTAGCTCCGCTCCGGACACGCAGTAGCTAAATAACAAACTCATTACTAGTATATTACTGCCGCCGATTTGCAAAC
GCGTACCGATCCCGATACCAGGCCAATCGCACTCCCCAGTTCGAATCAAGCAGGAAAATACCGGATAATAATTGGCAAAGATGCAGATCAAAGAA
TTCCGTGTGACTTTGCCATTGACTGTGGAAGAGTATCAAGTTGCACAATTATTCTCGGTGGCCGAGGCGTCAAAGGAGAATACGGGTGGCGGCGA
GGGCATCGAGGTGTTAAAAAACGAACCCTTCGAAGATTTTCCCCTGCTGGGTGGCAAATACAATTCCGGTCAATATACATATAAGATCTACCATC
TGCAATCAAAAGTTCCAGCCTACATAAGACTATTGGCACCCAAGGGCTCATTGGAGATCCACGAGGAGGCATGGAATGCCTATCCCTATTGTCGA
ACGATTATCACGAACCCCAAGTTTATGAAAGATGCTTTCAAAATAATCATCGACACTCTGCACGTCGGAGATGCGGGCGATTCAGAAAATGTGCA
CGAGCTGACGCCGGATAAGCTGAAAGTGCGAGAGATAGTGCACATCGACATTGCCAACGATCCGGTGCTGCCCGCGGACTACAAGCCCGATGAGG
ATCCAACCACCTACCAGTCAAAGAAGACGGGCCGCGGTCCCCTGGTGGGATCCGACTGGAAAAAGCATGTTAATCCTGTCATGACCTGCTACAAG
CTGGTCACGTGCGAGTTCAAATGGTTCGGCCTGCAAACAAGAGTAGAGAATTTCATACAGAAATCGGAGCGTCGCCTCTTTACAAACTTCCATCG
CCAAGTTTTCTGTTCAACCGATCGCTGGTACGGTCTAACAATGGAGGACATTCGCGCCATCGAGGACCAGACGAAGGAGGAGCTGGACAAGGCGC
GGCAGGTGGGCGAGGTGCGGGGTATGCGCGCGGATGCCGATTAA
(SEQ ID NO: 1418)

Start ATG: 176 (Reverse strand: CAT)

MQIKEFRVTLPLTVEEYQVAQLFSVAEASKENTGGGEGIEVLKNEPFEDFPLLGGKYNSGQYTYKIYHLQSKVPAYIRLLAPKGSLEIHEEAWNA
YPYCRTIITNPKFMKDAFKIIIDTLHVGDAGDSENVHELTPDKLKVREIVHIDIANDPVLPADYKPDEDPTTYQSKKTGRGPLVGSDWKKHVNPV
MTCYKLVTCEFKWFGLQTRVENFIQKSERRLFTNFHRQVFCSTDRWYGLTMEDIRAIEDQTKEELDKARQVGEVRGMRADAD*
(SEQ ID NO: 1419)

Name: PHOSPHATIDYLINOSITOL TRANSFER  B like protein
Classification: ligand_binding_or_carrier Celera Sequence No. : 142000013384535
AAGCCGATCATCACCATGGAGGATGCGATCAAGGCGGAATCGTTCCGCCTAGCCAAGAGCAGTTACTACAAGCAACAGATGAAGGTTTAGAGAGG
GCGAATCCAGCTCTGGAGCAGAGGCTCTGGCAGCTTTTGCAGCGTTTATATAACATGAAATATATATACGCATTCCGATCAAAGCTGGGTTAACC
AGATAGATAGATAGTAACGTTTAAATAGCGCCTGGCGCGTTCGATTTTAAAGAGATTTAGAGCGTTATCCCGTGCCTATAGATCTTATAGTATAG
ACAACGAACGATCACTCAAATCCAAGTCAATAATTCAAGAATTTATGTCTGTTTCTGTGAAAGGGAAACTAATTTTGTTAAAGAAGACTTACAAT
ATCGTAATACTTGTTCAATCGTCGTGGCCGATAGAAATATCTTACAATCCGAAAGTTGATGAATGGAATTGGTCTGCAACTGGTCGCCTTCATTT
CGTAAAATGTTCGCTTGCGGCCGAAAAATTTCGATATATCTACAATTGATCTACAATCTTTACTAAATTTTGAAAAAGGAACACTTTGAATTTCG
AACTGTCAATCGTATCATTAGAATTTAATCTAAATTTAAATCTTGCTAAAGGAAATAGCAAGGAACACTTTCGTCGTCGGCTACGCATTCATTGT
AAAATTTTAAATTTTGACATTCCGCACTTTTTGATAGATAAGCGAAGAGTATTTTTATTACATGTATCGCAAGTATTCATTTCAACACACATATC
TATATATATATATATATATATATATATATATATATATATATATATGTTATATATTTATTCAATTTTGTTTACCATTGATCAATTTTTCACACATGAA
ACAACCGCCAGCATTATATAATTTTTTTATTTTTTTAAAAAATGTGTACACATATTCTGAAAATGAAAAATTCAATGGCTCGAGTGCCAAATAAA
GAAATGGTTACAATTTAAGGAAACAAATGTCCTTCTTGCGTTTGAAACAACTAATCCTTTTCGCCCTCGCGGCGTTTCTCGAAAAGGGCCAGGAA
GATGCCATCGGTAAGATCACTGTCCGGCTGGCAATACAGGACGTTCTTGCCAATATTGGGATAGTCCTTGTCGCCCACATTGTGCCACTTGTTGC
GCAAGGCCTTCTTGCAGCTGAGCAGCTTGAAGGATGGATTTAGCTGAAGACAACGCTGCACCACCTGCTCGTTTTCCTCCTTCCACAGCGAACAC
GTGCAGTAGGCAATGCGTTTGACGTTCGGAAAGGCGCCCATCGCGTGCGACAGGATCTTAATTTGCAAACCCTGCAGCTTTTGCAGCCGCTTGTC
CTCCTTCGGCTCGTCGCACACGGTCATGCGGTTTTGCATTCCGCTGCCAGAGCAACTAGGGTCCACCAGGATGTACTCTACGTCCGGAAAGCGTT
CGGGTGCTGAAATTCAAACGTGTTACTTTTTTAAATATTCATTGTGAAATATATAAATATAAAACTCACTTAGGTTCAAGGCGTCTCCCAAAATG GGTTTTACAATATCGCAACCAGCATCCTTTGTTATTTCGCACAGCGTATTGTAGCGTACGTGGTCCTGCTCCACGGAGTAGATGCATCCCTTGTT
CTGCATCACATTGCATATGTGCACTGTCTTCATACCGGGAGCTGCGCACATATCCAGCACAGTGGCCCCAGACGGCGGAGCAAGTAGTTCGGCGG
CCAAACAGGTGGCCTTGTTCTGCAGTATAAACCTCTTGCTGTGCACCAACGGATGGCGGACCCAGTAGTTGGACCACTTGGCAGGAAAAATGAGC
ACACCCTCAACGTGCAGATCGGTCATGAACTCGTTCTCCGCCAGCGATTTGATGGCAGTCAGAAAATCCGCATAGCTGGCGTCCGCAGGCAGCTC
CTTGCGCCGCCAGTCGCTTTTATGCAGGTAGTCCAAGGCCTCCGCCAAGCTGTATAGATTTGTGTTGATGCGCACATATCGAGGATTGGGTTCTG
TGTGGGCAAACAAAAAGACGAGTTCAAAATTGTAGCCAAAGTAAGATTTATTAAGAGTTGTTAAGAGTCGTTACTGGTCCTTTAAACGATCGAAA
TAATCTGGACTTGGCTGGCAGCACTTAAGTTACTGTTCTTTCTTTGGCTCCGCAGCTTCCGGCTCGTCGTCCTCATCCTGCTGCACGGGTTCCAA
GGGTGGTGGGGGCTTCTCGCGGAAAGCCTTTAATACATACATGGCCACCACGAGGTTAACAACCACAACAGCCGTGAGAACTGACCAACAGTTGA
CCGTGAAAAGGTCCAAATGGGGGAAGGACTCCTGCAGCCAGCTGCGGACGCCATAGAAGCCCAAGAAGGGCAGCGTGAACATGAGCACACTGTAG
GCCAACAGCCAGAGGAAGACCTCCGCACTGGTGTCCTCCTGCTGCGTATGATGCTCCACGGGAGAATCAATGACAGCCGGGGAATCATCAGTGGT
AGCTGGCACCACATCGACATGCTGTTGTTTCCTGTTCTTCTTGCCCATCTCAGCCGGCTAATACTGGTAATCGGTGTGATAACCTGCCTTTTCGC
TGGACACCGAAATCTCTGATGGAATTTAGCAGTCGATCCTTGTAACTTCGCACCGTTTGCACGGGTTTGCTTTCGCCGTTCAGCTCCTTCCTGCC
AAACAGCAGTTCGGTGACTAGAATCTTGGCCAAACTGGGATCAAAACTGGGATTGTCCCTGAGCAGTCCTGTCTCTTCGATGGCCTTTTCCAGTG
CCACACGATTTTCGCTAAATTTTTTCAGAACCGTATGCAAAGAGCGTGTACGCTACAAGTGAAGTGCGAGAGGGAAAAGTTATACGCATATTGGT
TTGATCTGCGGACGAGAGGTCCAATCCACTTACGGCATGCTTCTCTGCAAATATTAGGGTCTTGATGCACTTCTGCTGCTCCAGTGCCGCCTTCA
AAATCTTGGCAGTCGCCCTGTATTGGGTGGGAACTTTTATGGAATGCGGTTTTTTACTCATTGTCGTCACGTGCACGTGTATGTGTTGTTTGCGC
TAGAATAGGTGCAACCCCAATCACGACTTTATCGATATATGCTTATCGAATGTCAGGGCTGGAGATAAGCATGTGGCGTTTGAAACAAATCATAT
TGTTATTCATGTTTTGAAAATATCTACAATTAATGTAAAGGTTGTTCTAATTTTGCCAACGATAACTACAAAACATATATGTTCTATCCAATATA
TTTACATACAGGGTATCAAATTTACAAATAAATTGGCAGTGTGGCCATACGTTGCGAGCAAAAATTACTGTACTTCAAGCATTGCCAACACAAGA
ATATTTTCATGGTTAAAAATTTTGGCGCGATAAAGCCGCAGTTTAAAATGTCAAAGTGTGCGCGTTCTTGGAGGTTTACCAAAATTTAGAATCAT
GCTTTTATTTATCGTGCATAAGTTGGTAAATTGGAATTAAATCAAGTTTTTCCAATTTGTTTCTGGTGTGTCGTTTGTTTTGGGGTCTGTACGG
CTGCTTTAATTAAAAAATATTAAAATGAAGCACGCTATTCTTTAAGGACTTTAAGGAAACGTACCTTTCTATGTTTGCCCAGGAGTTGATAGACG
ATATCAAGGCTGAGGATCGCATCCTACAATGTCCTTGGTGCGAAGAACAGACGTTGAGTCCATCAGCCAGCACCCGGAAACTTTTGTATTGGCTT
TTAACGCTTTCAATTCGACTTTCAGAAAAGAGTCTCCTCGAAAATCACGACTGATATCCATGTAAATGAATCGGTAGATACTTGCACTTTCTTTT
TAGTTATTAAAACTGACACACTGTCACTTTGCAGGTTTTAACCGCTGGCGGAAATGAAGAAGGAATCCGGGAATATTCATTTCAGTCCATTGTGG
TGCACAGCGGAACTCCCCTCAGGAACAATCTTAGCCCACTAAACATCAATAAACTACTAAAATAACTTTGACTGCTGCTTAATTTCAAATATACA
TAAATTAATATTTTTTATTTTTAAGTTAAATTTTTTAATTCTTTTGGAG
(SEQ ID NO: 1420)

Exon: 3039..2884
Exon: 2807..2558
Exon: 1992..1495
Exon: 1431..1001
Start ATG: 3006 (Reverse strand: CAT)

Transcript No. : CT17524
CGCAAACAACACATACACGTGCACGTGACGACAATGAGTAAAAAACCGCATTCCATAAAAGTTCCCACCCAATACAGGGCGACTGCCAAGATTTT
GAAGGCGGCACTGGAGCAGCAGAAGTGCATCAAGACCCTAATATTTGCAGAGAAGCATGCCCGTACACGCTCTTTGCATACGGTTCTGAAAAAAT
TTAGCGAAAATCGTGTGGCACTGGAAAAGGCCATCGAAGAGACAGGACTGCTCAGGGACAATCCCAGTTTTGATCCCAGTTTGGCCAAGATTCTA
GTCACCGAACTGCTGTTTGGCAGGAAGGAGCTGAACGGCGAAAGCAAACCCGTGCAAACGGTGCGAAGTTACAAGGATCGACTGCTAAATTCCAT
CAGAGATTTCGGTGTCCAGCGAAAAGAACCCAATCCTCGATATGTGCGCATCAACACAAATCTATACAGCTTGGCGGAGGCCTTGGACTACCTGC
ATAAAAGCGACTGGCGGCGCAAGGAGCTGCCTGCGGACGCCAGCTATGCGGATTTTCTGACTGCCATCAAATCGCTGGCGGAGAACGAGTTCATG
ACCGATCTGCACGTTGAGGGTGTGCTCATTTTTCCTGCCAAGTGGTCCAACTACTGGGTCCGCCATCCGTTGGTGCACAGCAAGAGGTTTATACT
GCAGAACAAGGCCACCTGTTTGGCCGCCGAACTACTTGCTCCGCCGTCTGGGGCCACTGTGCTGGATATGTGCGCAGCTCCCGGTATGAAGACAG
TGCACATATGCAATGTGATGCAGAACAAGGGATGCATCTACTCCGTGGAGCAGGACCACGTACGCTACAATACGCTGTGCGAAATAACAAAGGAT
GCTGGTTGCGATATTGTAAAACCCATTTTGGGAGACGCCTTGAACCTAACACCCGAACGCTTTCCGGACGTAGAGTACATCCTGGTGGACCCTAG
TTGCTCTGGCAGCGGAATGCAAAACCGCATGACCGTGTGCGACGAGCCGAAGGAGGACAAGCGGCTGCAAAAGCTGCAGGGTTTGCAAATTAAGA
TCCTGTCGCACGCGATGGGCGCCTTTCCGAACGTCAAACGCATTGCCTACTGCACGTGTTCGCTGTGGAAGGAGGAAAACGAGCAGGTGGTGCAG
CGTTGTCTTCAGCTAAATCCATCCTTCAAGCTGCTCAGCTGCAAGAAGGCCTTGCGCAACAAGTGGCACAATGTGGGCGACAAGGACTATCCCAA
TATTGGCAAGAACGTCCTGTATTGCCAGCCGGACAGTGATCTTACCGATGGCATCTTCCTGGCCCTTTTCGAGAAACGCCGCGAGGGCGAAAAGG
ATTAG
(SEQ ID NO: 1421)

Start ATG: 34 (Reverse strand: CAT)

MSKKPHSIKVPTQYRATAKILKAALEQQKCIKTLIFAEKHARTRSLHTVLKKFSENRVALEKAIEETGLLRDNPSFDPSLAKILVTELLFGRKEL
NGESKPVQTVRSYKDRLLNSIRDFGVQRKEPNPRYVRINTNLYSLAEALDYLHKSDWRRKELPADASYADFLTAIKSLAENEFMTDLHVEGVLIF
PAKWSNYWVRHPLVHSKRFILQNKATCLAAELLAPPSGATVLDMCAAPGMKTVHICNVMQNKGCIYSVEQDHVRYNTLCEITKDAGCDIVKPILG
DALNLTPERFPDVEYILVDPSCSGSGMQNRMTVCDEPKEDKRLQKLQGLQIKILSHAMGAFPNVKRIAYCTCSLWKEENEQVVQRCLQLNPSFKL
LSCKKALRNKWHNVGDKDYPNIGKNVLYCQPDSDLTDGIFLALFEKRREGEKD*
(SEQ ID NO: 1422)

Classification: hypothetical

Celera Sequence No. : 142000013383859
TGTGTTCCAGTTCGCCGGTTAGCACATCCCAAATGCACACATTGTTGTCCGTGGAAGCTGAAAGTAACTGGAGTGGATTGGAAAATGTAGATGAT
CAGGTGTACGGCGAGCGAGGGCCTACCTTGTGACCATTCCTGGTCCAACTGAGACTGCAAACGGGATGCACATGGGCCGAAATAATCTTGGCAAT
GCCCCTCGTCAGAAAATCCCAGATTACAATGCGGCCATCATTGCATCCCACGGCCAAAAGGGTTCCGTATTTGTTAAAGGCACACGTCACGGCCA
ACGAAATGCAATCCAGCGAGCCGTCGAACTCCTCTGGGTAGTTTTGTCCGAAAGATTCTTAATAAAGCTGGAGTTATTTACTACATAAGCATAAA
AAATGGGCGGCAATCTCACCTAGTAGCTCCAAATTCATTTTTGTTTACTATCTTCTTCTTTTAAAATGGCAACTGACACTCACACCGAACGGCAA TAACATATTATGTTATAAATGATAAGCATAACAGAAGACGAGTTTTTCGATAGTTAAGGTTATATTCTGTACAACTACTGAACATCAATTATTAT
ATTATAATACGAATTTAAAAATCTACGTATCTACGTTGGTGTTTTTTGTGGTTTTATTAATAGAATAAGTTTAGTTAATTTTAGAGGTGAAATTA
AATATTGAAATAGTTAAACATATAAAATAGATAAATTTGGTGAAGCGTAAGTAAATTTTAAACTGCATTAGTTATATCTTAATTCAAGTTCCCCA
CTAATTTATGAGCGTTAGATGCGATAGTGTTATGTCTGGCGCAAGCGATTGTCTCGACGTTTCTTCGATATTTTAAGATATCGATAATGTCATCG
GAGATTTGCCACCCCTATTTTTTGAGCTCTGTGCACGTTGTATGAGAAAAATTTATGCAGATGTATTCGCCAATTGTAACCAAGTCCGGATTGTG
AAATTGCACGCAGACAGCGAGCATCATAATAAGCGCTCTAATTGGAGAAGGCAGAAGTTTCGAATTAAGCCATTTCGGAGACGTTTCGTCCGTGG
CACGCGATTGTGTCAACGTCACCTTTGGAGCACTCGCCCTCTCTCGCTCGCTCCCGCTTTCGTTGCCAATTTTTTGCTTGCCCTCTCTCGGTCAC
TCCCTTCGAAAGCTTAACGGTTAGAGTGTAATAATGAAATAACCCAGTTTCGAATTTCGTTCACAACAAAAGTGCGGGCCTTTCATGCCAAAATA
ACATTTGGTTTCGAATTGTTTTTCAAATTCGAATCGAGGTTTTCCAGCTTTCCAGTTTGACAGCGAGAGAACGAGAGAGAGCGAGGGCGAATTAC
GGTGTTCGCGCTCTGCTTGTGCTTTCCACTCCACTCCCCTTCTTAACTTCCCCCCTCCCAGCCTATTTACTCTGTGTGCATGTGTAAATGAATAC
TTTAAAACGTTTTTAATCGTTGCAGTGTATTCATCGCCAGCCACGTTAAAAGGAAGAACGTGTATGTGAATACGACCATCAGAGGATCTTAGCGA
AGGATTCAGGAGCCCAAATTCTTAATCCCCATCCCACACACACACATATACTCGCACGTAGGCACGCTCTCTGTGAGAGGAAGGGTAAATAAAAG
AAGCAACGAGCAAAATGTCTGGCGAGGAAACGTCTGCCGATCGCAATGTCGAGATCTGGAAAATCAAGAAGCTCATCAAGAGCCTGGAAATGGCC
CGCGGGTGAGTCTTATCAATGATATACATGTCCTTTAACGTCCCCCCCAACGACTGTTTTGCGTACGTGTGTGGGGTATACACAATGCATGGCAC
GAAAACAACAACACTGGGGTGGAAGTGGGCGTACTGGACGTGGGTGTGGGTGGGGACTTGAGGGAGCGGCGAGTACAACCACCTTTCCTTGTTGT
CGCCGTGTGAATCTCCTTTGCATTGTTTCCAATCTTGGCAAGATCCCCCGCCTCACTCTATCTCTCTTTTTTGCATACGAGCAACACGTTTTTGT
CGAGTTTTTATCAGTTCAAACTAGACTGATTGAGAGACGGAGAGAGAGAGAGAGAGAGAGGAGTGAGTGAGTGAGTGAGTAATCGCCTCGTGGCT
GTTGTGCGTATGCGTGCATGTGTGTGTGTGTTTTTCCCCCAAAATGGGCCAAGCTTTGTGGACCCCTCGCTCTCACTCATCCTGCCTCGCTCACT
CCCTTGACCCGGTCCTTACCGCTTCACACCGCTTTAGAGTGGGTAACAAGGTCAGCAAATCGAGTGACCCCCACAGGAGCATATCTGCTATGTAT
ATACATATATATGTATATTGTTGTCAATATGCTCCACAATTGGAGCTAACATTACACCTCTTCCAATTGGAGTTGGCCACTGTTGCCAATTGGGA
TTCGCTTTGACAGATATCTTCCTATTGGTTTTCAGCCATATGCGAAATATATACACACATATGTATTTGTTTTTCTTTTTTTAAGTTCTGTGCTA
TTTTTTGTTGTATTTTGCATTCCAACATTTTGTACAAATTACGATTGGCACTCCTCTGTATTATAACGAACGAGAAAATGATTTGCATCAGAGAA
ACAAACGTTTGGAAGTTACAGAAACGTATTTGTTTCAATAAATTAATCAAAGTTTAAATTTAGTCCAATAACCGAATGTCAAGTTTAAAAGACAT
ATGCCACGAAATTTCACGGCTAATTAAATAACTTTAAAGTAGGTTGCTATTATGTGCATCTGACGCGCAAATATACGATTGAATAGCACTGTTGC
TATGGGAGAAAGAGCCATTTCCGCGACTTATGTTCTCCCTTGTTTGGGTTTCTTGCAGCAATGGAACCAGCATGATTTCTTTGATTATTCCGCCA
AAGGATCAAATCTCGCGCGTCAGCAAGATGTTGGCCGATGAGTTTGGAACGGCGTCGAACATCAAGTCGCGTGTAAATCGGTTGTCCGTCCTCGG
TGCCATTACGTCGGTACAGCACAGACTCAAATTATACACCAAAGGTAAGCTGAGCTAAGAAATTGTTCATAAACAATCGAACAAACGAACTCTAA
ACCGTATCACCAACCGCTTCAATTCAGTGCCTCCCAACGGTTTGGTCATCTACTGCGGCACAATAGTCACAGAGGAGGGCAAGGAGAAGAAGGTG
AACATAGACTTTGAGCCATTCAAGCCCATAAACACGTCGCTCTACCTCTGCGACAACAAGTTCCACACGGAGGCCCTCACTGCCCTGCTCGCCGA
CGACAACAAATTTGGATTCATCGTGATGGATGGTAACGGAGCGCTATTCGGTACCCTTCAGGGCAACACGCGCGAGGTGCTCCACAAGTTCACCG
TCGATCTGCCGAAGAAGCACGGTCGTGGTGGTCAGTCCGCCCTTCGTTTCGCCCGTCTGCGTATGGAGAAGCGCCACAACTACGTGCGGAAGGTC
GCCGAGGTGGCCACCCAGCTCTTCATCACGAACGACAAGCCCAACATTGCCGGACTCATCCTGGCTGGTAGTGCGGATTTCAAGACTGAGCTTAG
TCAGTCTGATATGTTCGATCCTGTAAGTGGGAGTTAACCTATTTCCATCGATGCCATATTAAGCCTTACACTTGAATCTTTTTTCAGCGTTTGCA
ATCAAAAGTCATCAAGCTGGTGGACGTGTCGTATGGTGGGGAAAACGGTTTTAACCAGGCCATTGAACTGGCGGCCGAATCATTGCAGAACGTTA
AATTCATACAGGAGAAGAAACTCATTGGTCGCTACTTTGATGAAATTTCTCAGGTGAGTTGCCGGATACGAGTTCTGAGGCATTTCGAAATTAAA
AACCACATCCGTATGCTTTCTATATTTAAAAGGATACTGGCAAATACTGTTTTGGAGTGGAGGACACTTTGCGGGCACTGGAACTTGGCTCTGTA
GAGACTCTCATTTGTTGGGAGAACCTGGATATTCAACGTTATGTTCTCAAGAATCATGCCAACTCGACGTCAACGACAGTATTACATTTGACGCC
CGAGCAGGAAAAGGACAAGTCGCACTTCACTGACAAGGAGGTGAGAGCTAAACTGAGTAATGATACTAATCCGCACGCTAACTGGGAATTCAATC
GTATAGAGCGGGGTAGAAATGGAGCTGATTGAGTCTCAGCCGCTGCTGGAATGGCTGGCAAACAACTACAAAATGTTCGGCGCCACACTGGAGAT
TATCACGGATAAGTCCCAGGAAGGAAGTCAGTTCGTGCGAGGTTTCGGTGGAATCGGCGGTAAGTTTGAGCGGCCAAACAGCACGGCTGGCTAGT
TGTAGATTGGTTATGTACTAAACAAATGCTGCAACTATATCCATTCCTCTTCCCTCATGCTGCTTTCACACGGTCGTCAACGCTATAATGTAAAT
GTTAATTTGCAAACTGGTACCTCAATTCGATATGTAGGCATTTTGCGCTATAAAGTAGATTTCCAATCCCTACAGGCCGATGAGCCGCTGGAGGA
TGTCGATCTCGATGACTATTAAGCCTGTTAAGGGTGGGCTGCGAATGGGTCTCGATTATGCGTTACATACATAATAAACCAGTACTTTTTGGGAA
ACCTCGTAAAGCAAAACGTTCAAATTGATTAGGAACCAATTTACTTGCCACATAGTTTTACCTATGTTCAGCGTAGCCGTTCAATATTTATCACC
AATAGGGTCCCTCTCATCAGTCGGATGGTGCATTCCCTTGTCGATCAGATCAGCGTGCATCTAGATATGTACCTATACGTTTTACCAAATTTTTT
AATTAGTCGTGCACCAGGCGGAATCGCGTACTTTTAAGCAGCATATTAAATTCGTATTTCGTACTCGTAATTCGTAATTTGTATTTCAATGGTCA
TGTAAAAGCGATGCGATAGATATTAGCGCATTCTCCGTTCATCTGGTTCGATTTCGACTGCGGTATTAGGAGCAAAAGATCTTCGGTTAACTGCC
ACATGCCACTTTCGAACGTATCTGCATTTCCCCTATTCAAATTATAGCCGAGTGTTATAAGAAAGTATACAAATCTAATCCATAAAATTGTAATA
AAAATTAAACCAGAATAAAAACACCACACAATGAGGATGGGGTATCCGTTTATATTCAGTCGCGAAGTACAACAAATATTTTATTTAGTGTATGA
AAAGTTAAATGTGGATACAAAGGAGGTGAGAATCTGAGTTTCGGTTGAACTATCCTGTGTGTTGATCCTTTTGTTTTTTCCTCTTCATTTATTTT
TCAATTTTCAATCAGCTTCTGTTCTTCTATTTTTTTTTTTTTTTTGTTTCTTATTTTAATTTAATTCAATTGCTGGGTGTGCCTCTGCAGGTATC
TTACGCTACAAGGTGGATTTCCAGAGTATGCAGCTCGATGAATTGGACAATGATGGCTTCGATCTAGATGATTACTAGGAAATGTATCTGTAGAA
ATGAATTTGCCACTACGTTCGACCGCAAACTGAACTGCAACTACAACTATATGAATCCAGGAAATCAAATAGAATATTTAAATAATATGAGAAAA
CACAAACCTTCTTCCATTTTTACGTTGTTGGCGAAAAAAGTAAAATTTTAAATAATGCATATAGATACAAACGATAAAATGTTAAATCGAGGAAA
ACATATTAAAATGCAACCGTTTTACGTGAACAAATTTGCAATTTGAATATATTTTCGAGGGACTAGAGCTCTTGTTATATAATTAATTGTTCCTC
TATAAATCTAAATCTAAATCTACATTGACAATACGCCACGTTTCCTAAAGTTTTTGGGTACAAGGAGAATTGTATCTGTGAGTTTTAATCGTTCT
ATTATAGCTTGAAAACGAAATTTGCACCGAAAGCTGATAAAATTCCGACTCTGCTATCTGCTGGATAAGTAAAATGCTGGTAGCCACTTGGAGTA
CTACCAGTACAGCAATGAAAGTAAAGTGAAATGGGCATTTCATTTTCTACTTTCTATTTGCAGGCACACTGGAAACAGTTTACTGCGAGATTCCC
ACTTCATTAGTTGGCAATGCACGTGGACGACAGCAAAAAGCACTCGTAGTACTTGTTTCGCCCTTGATTTGCATCTAAGAATCGCTCAGATACAT
CTGGTGAGCTGAAACTCGTTTCTGAGCCGCAGTGTCGTGCAGGTATCCGTACTCGTTTGAATATTTGTAAGTAATCATTGCAGCGAGACTTCCAA
AAAGTAAGCTCAGCTAAGTTCTGCGGTGTTGGGCATCCAATTAGTTGACCAAGTTTTCTGGTGGCATGCACATGAAACTTGTTTAATCGATAGGG
TAAATATGCAAATTTCGATTGAATTTGACGATAATGCGTCGAGATGAAAAGAAAACGAATTGTGCAGGATTTTGGTTACGAGATAAGCCGAATCA
GCTAATAAGGCACGTGCTTAATTGATATATATTGTATGTTTAAGTAACCTAAATATGCACGACTTTAATATCACTTTTATTTCGCTTTCGTAATA
AAACGAGGTTCACTCTAAAGAGCACAAGCGTGGAGGTGTATGTGTGTTCTTACAGCCCCGATCATTTGTATTTCCATTTGAGTGCGAGCGAAGAC
GAGGGTTTACAACTTGATGAGAATTTGATCAAGATA
(SEQ ID NO: 1423)

Exon: 1001..1715
Exon: 2814..2989
Exon: 3068..3537
Exon: 3603..3758

FIGURE SHEET 761

Exon: 3833..4030
Exon: 4092..4239
Exon: 4408..4485
Exon: 5316..5591
Start ATG: 1630

Transcript No. : CT17696
GCAGAAGTTTCGAATTAAGCCATTTCGGAGACGTTTCGTCCGTGGCACGCGATTGTGTCAACGTCACCTTTGGAGCACTCGCCCTCTCTCGCTCG
CTCCCGCTTTCGTTGCCAATTTTTTGCTTGCCCTCTCTCGGTCACTCCCTTCGAAAGCTTAACGGTTAGAGTGTAATAATGAAATAACCCAGTTT
CGAATTTCGTTCACAACAAAAGTGCGGGCCTTTCATGCCAAAATAACATTTGGTTTCGAATTGTTTTTCAAATTCGAATCGAGGTTTTCCAGCTT
TCCAGTTTGACAGCGAGAGAACGAGAGAGAGCGAGGGCGAATTACGGTGTTCGCGCTCTGCTTGTGCTTTCCACTCCACTCCCCTTCTTAACTTC
CCCCCTCCCAGCCTATTTACTCTGTGTGCATGTGTAAATGAATACTTTAAAACGTTTTTAATCGTTGCAGTGTATTCATCGCCAGCCACGTTAAA
AGGAAGAACGTGTATGTGAATACGACCATCAGAGGATCTTAGCGAAGGATTCAGGAGCCCAAATTCTTAATCCCCATCCCACACACACACATATA
CTCGCACGTAGGCACGCTCTCTGTGAGAGGAAGGGTAAATAAAAGAAGCAACGAGCAAAATGTCTGGCGAGGAAACGTCTGCCGATCGCAATGTC
GAGATCTGGAAAATCAAGAAGCTCATCAAGAGCCTGGAAATGGCCCGCGGCAATGGAACCAGCATGATTTCTTTGATTATTCCGCCAAAGGATCA
AATCTCGCGCGTCAGCAAGATGTTGGCCGATGAGTTTGGAACGGCGTCGAACATCAAGTCGCGTGTAAATCGGTTGTCCGTCCTCGGTGCCATTA
CGTCGGTACAGCACAGACTCAAATTATACACCAAAGTGCCTCCCAACGGTTTGGTCATCTACTGCGGCACAATAGTCACAGAGGAGGGCAAGGAG
AAGAAGGTGAACATAGACTTTGAGCCATTCAAGCCCATAAACACGTCGCTCTACCTCTGCGACAACAAGTTCCACACGGAGGCCCTCACTGCCCT
GCTCGCCGACGACAACAAATTTGGATTCATCGTGATGGATGGTAACGGAGCGCTATTCGGTACCCTTCAGGGCAACACGCGCGAGGTGCTCCACA
AGTTCACCGTCGATCTGCCGAAGAAGCACGGTCGTGGTGGTCAGTCCGCCCTTCGTTTCGCCCGTCTGCGTATGGAGAAGCGCCACAACTACGTG
CGGAAGGTCGCCGAGGTGGCCACCCAGCTCTTCATCACGAACGACAAGCCCAACATTGCCGGACTCATCCTGGCTGGTAGTGCGGATTTCAAGAC
TGAGCTTAGTCAGTCTGATATGTTCGATCCTCGTTTGCAATCAAAAGTCATCAAGCTGGTGGACGTGTCGTATGGTGGGGAAAACGGTTTTAACC
AGGCCATTGAACTGGCGGCCGAATCATTGCAGAACGTTAAATTCATACAGGAGAAGAAACTCATTGGTCGCTACTTTGATGAAATTTCTCAGGAT
ACTGGCAAATACTGTTTTGGAGTGGAGGACACTTTGCGGGCACTGGAACTTGGCTCTGTAGAGACTCTCATTTGTTGGGAGAACCTGGATATTCA
ACGTTATGTTCTCAAGAATCATGCCAACTCGACGTCAACGACAGTATTACATTTGACGCCCGAGCAGGAAAAGGACAAGTCGCACTTCACTGACA
AGGAGAGCGGGGTAGAAATGGAGCTGATTGAGTCTCAGCCGCTGCTGGAATGGCTGGCAAACAACTACAAAATGTTCGGCGCCACACTGGAGATT
ATCACGGATAAGTCCCAGGAAGGAAGTCAGTTCGTGCGAGGTTTCGGTGGAATCGGCGGCATTTTGCGCTATAAAGTAGATTTCCAATCCCTACA
GGCCGATGAGCCGCTGGAGGATGTCGATCTCGATGACTATTGTATCTTACGCTACAAGGTGGATTTCCAGAGTATGCAGCTCGATGAATTGGACA
ATGATGGCTTCGATCTAGATGATTACTAGGAAATGTATCTGTAGAAATGAATTTGCCACTACGTTCGACCGCAAACTGAACTGCAACTACAACTA
TATGAATCCAGGAAATCAAATAGAATATTTAAATAATATGAGAAAACACAAACCTTCTTCCATTTTTACGTTGTTGGCGAAAAAAGTAAAATTTT
AAATAATGCATATAGATACAAACGATAAAATG
(SEQ ID NO: 1424)

Start ATG: 630

MSGEETSADRNVEIWKIKKLIKSLEMARGNGTSMISLIIPPKDQISRVSKMLADEFGTASNIKSRVNRLSVLGAITSVQHRLKLYTKVPPNGLVI
YCGTIVTEEGKEKKVNIDFEPFKPINTSLYLCDNKFHTEALTALLADDNKFGFIVMDGNGALFGTLQGNTREVLHKFTVDLPKKHGRGGQSALRF
ARLRMEKRHNYVRKVAEVATQLFITNDKPNIAGLILAGSADFKTELSQSDMFDPRLQSKVIKLVDVSYGGENGFNQAIELAAESLQNVKFIQEKK
LIGRYFDEISQDTGKYCFGVEDTLRALELGSVETLICWENLDIQRYVLKNHANSTSTTVLHLTPEQEKDKSHFTDKESGVEMELIESQPLLEWLA
NNYKMFGATLEIITDKSQEGSQFVRGFGGIGGILRYKVDFQSLQADEPLEDVDLDDYCILRYKVDFQSMQLDELDNDGFDLDDY*
(SEQ ID NO: 1425)

Name: translational release factor 1
Classification: translation_factor

Celera Sequence No. : 142000013384535
TTTTCTCCCTCAAAACAGCAAGTTTATACTACTTATTAACCAAGGTAAAATTAAAATGTTTTACAACTGTCATCGGAAAATAAAGCATTCCATGT
TTTAAAAACACCCAATCGAATGGATTATGTAAAAGTATTGGATTTTTTTATTTTGCCCACTTAGTAGCAAGTGGCGCTTACGGATGCCCGATCC
ATGGGGCAACCATAAACTTGGATGTCTGTGATTAGGGTAAGGAAACATAACACTTATTTCACAAGAATTCGCCAGCTGCTTAAATGGTACATGTA
AAAATATTGAAGTATTTTTATTTTTCTAGACATTCTGAGTGGCGCTCGATGTGTACGTACATACAACTCTTTGGATTCTGTGTGTACAGTCAATT
TACGATGCCCAAGCCGCCCTGAGCGAATTCCATATTTACAAGAGAAGGGGGTGGGGATTGGGAGGGGGGGGGGTGTCGGAAAGGGTTGGGGCCTT
AAAATACCTAAACTCAACTACACTCAACAATTTGCTTATGGTCACTACTTATACGCCTTATACACCGGCGGTTGCACTTTAAGCTTCAACGTTAT
AGATTTGGCCAGGACACCAGCGGAGGAACCACGATCCCGACGGCCAATCCCCGCACCGAACACTCCTTCCGTGCTAGCCGGAAGTGGATCGGCGG
TGGGCGTGGCCGCAAGGAACGGCCAACCGGGGCGTCATTTGGGATATGAGCCGCGCCGGAGCCGGCAGTCTGCTGTGCCCGGAATTCGTGGGGGA
ATCGTTCACGGGACCGACCAGCAGCCCCTGCCGGGCGGACGCAGTTGACTAGTGGCGGACAAAACTTTCAAAGCAATCGAAAGCGAAACCTTTGT
ACACACTTAATAGATTCCTGCGGGTCGAGTTCGTGGTCAGTTCGTCGTCAATGCTCAGTGTCCAGTAATCTTTTCGTTTGTTTTTTGGATGAGAA
AATGAGGGAAACTTAAACGGCTCGGTAAAAAAGAAAGGCGTGGCAGCGCGCTAAACAAATTGCTCTGAGCTGTTGGCGGACAGCTCCATCAGCCG
CCAGGCAGCCTTGGGGTTGAGTTCGTTGCGGTCGCGGCACAGCACCCAGACGTAGTGAACCCGCATCACCTTCTCCGGATCTCCCTCGACGACCT
GACTCTTCTGGTCCCGCACGCACATAATCTGCTGGGCTTGGAACGTGATAATCAGTACCGGGCCCTGCTCCATAACCTTGCCCATTGCCAGTTCA
ATGTTCTCGATGTCGAGGATCTTGGAGTCCAGGTACACGCCGGCCTTCTTAGCCTCCTTAATGGGATTTGCGATAATATTGAAAGTGCTCTCAAA
GCACCAATCCTTCAGAATCTCCAGATCCCCACGGACAATCGATTCCAGAATATTTGGAATGATGTCCGTTTCGCAATCGCGGAGGAAATCCTTCT
GATCAAAGCTCGGATCGATTTTCACCAGCTCCGTCATCGTTTCCGAAAGCTCTGTCTTTGAAAAGAGTCCACCCATGACGTCGGACACTTTATCG
GTCAGCAGGCGGGAGGCACGAATAACAGGGTTCTCGGACTCGTCGTATTTAACCTTCCAGTCAAGCACCTTGTTCACGTAGGTATTGTTGTTCTT
GAAGTTCTCCCACGACTCGTAGAACTTGGAGTCCTTGTGCAGCTCCATACCTGAAAAGTAACATTACATTATGGCCATGACCTTTGATCTTATTG
AAGGAAAAAGATGGAGACTCACCAGTGGCTTCCGTGTTGGGCTCCACAACGCGATCACTATCGCTCATGACGAGCTGGACGCGCTTTCGCAACTT
GGCAGGAGCACGATAGACACGATTCTCTATGCTCGCGCTGTCCATCTCCTTCTTGATGGTCGTCGTCGTGTTAGAGATAGCCTGGAATGCGCTGG
TCTGGCCCAGCTTGCCACTGGTGTCGGAGATCGTGTCGCTGACCCCCCTAGCCTTCTTCGAGAGCTCCTCGGTAACCTTTTTGGCCAGGTGGGAT
TTGCTGGCGTCCTCCAGAACATCGCCTACGCGCTCCTTGATGGCGCCCAGCTGCTCCTTTAGCATGCTAGACGACTTTTGCGCCTCCGATTCGAC
AATGTTAAACTTTTGCCGCGCCGATTTCAGGGCATCCGATTCTTCCAGCTTCTGGGCCTCCTCACGGAACTTTCGGATATTGTCCTTGATCTCCT
TGTTCTTATCCATCTCCGCCTTCATGTTGTCGAAGAACTGCGAGAAGAAGCCGGCCCTGCGACCTGGCGCACTATAAAAGCGGGGCTGCGGAGTA AAGTCATGACTTAGGCCGGTTGCGCCATGGGGTTTTATGAGCCAAACTCTAACCTGCTGCTGCTGCAGGTTCTGCGAGGCCTGCTGGCACGTGAA
GAGACAGGCGCGATCCCGCACAAGGGCAGCTATTCTGTACTGCAAGGAGAAAAAATCATTGAAAGCTTCGACCGTTTTAACCTCGAAATATGCAC
ATGTAAGGACGGATGTGAGCGAACGCCAGTGATGACCGGGATCAGAGGTAACCTACCATGGTGGGGATTAGGTGACCGTTCGCAGGTAGTTTGAT
CGGAGCGAATGTTCGGGGGGTCTGGCGTCAGAGGCTCTAAACTTTATGTAATTCCTGCCGCGAAACACGCACGTATCAAGCAGTCAGCTGTTCTC
TTCGTTCAGCGCGCGCCGGTGTTGCAAAACGAGCGCTCTTCGCCGGCGGTGGCTCGTGCGATAGTTCGTTTTGTCGGTAATCCGATGTTGCCGCG
CCGATATCATGTGATGTTGTCACAGTGCGCGAAATTCGAATGGTGGTGTGCAGTGATTGTGTTGTGACGGCGAGTGGCGCGTGTGGGTGCTTAGT
TTTGGGAGATGTTTTCGTATTTTTTTGTTGATAACTCAGGCTTTGTTGCTGTGTTGTAGTACTATTTTCCATTGCGCGGTGTCCAGCTTTTAATT
AGTGGCACATATTCTTAGCAAGTAAAAATTATTTTGCATACTATTAAATTTCTTATAAATTATTTTCTAAAATTAAGTTTACCTTTTCAATTTTA
CTAAAAATATCGATATATTTATTATCGCTGGAAAACTACATTATTCCACCTCTAAGCAAGAACCGTTAGTTGGCGCGTAGCTTTACCACAAAATT
CCTGGAATTGCCGTACGCTTCGCAGTTGTTTCAAGTTGTCTAAGGGACATACGATTTTTTTTGCCTCTGCGTCACGATTTTAACCCAAAAGCGAG
TTTAGTTACATGTACATTATTATTAGATAAAGAAGTATCGCGAATACTTCAGTTGAATAAACTGTGCTTGGTTTTTGGGTGAGGATTTGTGGAAA
GTAGAGTGCGCGATAACCGTAACTTTCGACCCGGATTTTCGCCATGTTCCGCAGCAACTTGGAGGGCAGTGGCGCAGCAGCAGTAGGTGTTGCAA
ATCCCCCCTCGTTGGCTCAGTCTGGAAAGATTTTCCAATTGCAGGATAACTTTTCTGCTTTTCACGCCAGAGGAGGGCTCAACATTCTGGGCCTG
CAGGACATGTATTTGGATACCAGTGGGGCCAACTCGTCGGCCACTTTGAGTCCGCCCATTACGCCGGTGACCCCTGACCCGTCGACGTCTGCGCA
GTCGACGCACTTCCCTTTTCTGGCCGACAGCGCAGCCACCGCCAATTCGCTCCTTATGCAGCGACAGTACCACTACCACTTGCTGCTCCAGCAGC
AGCAGCAACTGGCCATGGCGCAGCACCAATTGGCGCTGGCTGCATCAGCGGCAGCGGCTAGTGCGAGTCACCAGCAAACGGACGAGATTGCGCGA
TCCTTGAAAATCTTTGCGCAGGTGACGACGGGCGCAGCAGGTAAGAAGAAATGGCGAATATGGCGTCGTTTAAAACAGAATAGCCAAAAACAGTG
CGCGGGAGCGAGATGACTATCTGTACAAGTACAGTTATGCCAAAGTCAATGGCCATGGGCTTAGTTAAAGGGGCAACGAAAGCACAGAGCAAAAC
AGAAGTAAAATTGTGTAAATGTATAATTGCTGCAGAGGTCAGAGGATTTTCGCCATTTAGTGTAGTATATTTTTTATTTTACTATTTTGTATGTG
CTTTAAAATATATCTTTGCCCAACACTTGTATCCCCTTCAAGAGGTTTTTCGAGCGCCCCTGAATTTTCGGCCATTGACCTTAGCATTTTCGCTA
TTCCTTTTTGTTTTAACTTCGGAAAGCCATTTTGCGTCTTACATTTTCTAGAAGTTCTTTGCTTTTTCTCGTCTGTTCTTGTTTTTTTTTTGTAT
GCAAAAACTAATCCGTATTTGCTTATTACATTTCTGAAATGCAATTGAAACGCGAATAATAAAAAAAAATACGTTCAGGACAAGGTAATGAAAAGC
TTGCTATTCCCAGAAAATGCGGCTGGCTCGATGCAGGATGTGATGCAGGAGTTCGCGACCAATGGCTATGCCAGCGATGATCTCGGTCGCATGTC
CTACGGGAGTGCTCCGCCACAGGTGCAAATGCCACCGCAGCAGCAGCATCAGCAACAGCAGGGGCTGCACCTGCCACTGGGCCGCAATCCTGCCC
AGCTGCAGACCAATGGCGGCAACTTAATGCCCATTCCACTCGCCACCCACTGGCTGAACAACTACCGGGAGCATCTGAACAACGTGTGGCGAAAC
ATGTCGTATATACCAGCCGCTCCCAATACAATGGGTTTGCAGGCCCAAACAGCGGCCACTGTGTCCACCAATCTCGGCGTGGGAATGGGTCTGGG
ATTGCCCGTGCAGGGCGAACAGCTGCGCGGAGCTTCCAATTCCAGTAACAATAATAACAACAACAACAAGGTGTACAAGCGTTACAACAGCAAGG
CCAAAGAGGTGAGTGGATCTGATCCAGGATTCGCAGAATTAAAACTTGCAAAATATATTTGTTATCTTGTTTCTCCAACAGATCAGCCGCCACTG
CGTCTTTTGTGAGAATAACAACGAACCAGAGGCGGTTATCAATAGCCACTCAGTGCGAGATAACTTTAACCGAGTGCTGTGCCCCAAACTACGCA
CCTACGTGTGCCCCATCTGCGGGGCATCTGGGGACTCGGCGCACACGATTAAGTACTGCCCCAAGAAGCCGATCATCACCATGGAGGATGCGATC
AAGGCGGAATCGTTCCGCCTAGCCAAGAGCAGTTACTACAAGCAACAGATGAAGGTTTAGAGAGGGCGAATCCAGCTCTGGAGCAGAGGCTCTGG
CAGCTTTTGCAGCGTTTATATAACATGAAATATATATACGCATTCCGATCAAAGCTGGGTTAACCAGATAGATAGATAGTAACGTTTAAATAGCG
CCTGGCGCGTTCGATTTTAAAGAGATTTAGAGCGTTATCCCGTGCCTATAGATCTTATAGTATAGACAACGAACGATCACTCAAATCCAAGTCAA
TAATTCAAGAATTTATGTCTGTTTCTGTGAAAGGGAAACTAATTTTGTTAAAGAAGACTTACAATATCGTAATACTTGTTCAATCGTCGTGGCCG
ATAGAAATATCTTACAATCCGAAAGTTGATGAATGGAATTGGTCTGCAACTGGTCGCCTTCATTTCGTAAAATGTTCGCTTGCGGCCGAAAAATT
TCGATATATCTACAATTGATCTACAATCTTTACTAAATTTTGAAAAAGGAACACTTTGAATTTCGAACTGTCAATCGTATCATTAGAATTTAATC
TAAATTTAAATCTTGCTAAAGGAAATAGCAAGGAACACTTTCGTCGTCGGCTACGCATTCATTGTAAAATTTTAAATTTTGACATTCCGCACTTT
TTGATAGATAAGCGAAGAGTATTTTTATTACATGTATCGCAAGTATTCATTTCAACACACATATCTATATATATATATATATATATATATATATA
TATATATATATATGTTATATATTTATTCAATTTTGTTTACCATTGATCAATTTTTCACACATGAAACAACCGCCAGCATTATATAATTTTTTTAT
TTTTTTAAAAAATGTGTACACATATTCTGAAAATGAAAAATTCAATGGCTCGAGTGCCAAATAAAGAAATGGTTACAATTTAAGGAAACAAATGT
CCTTCTTGCGTTTGAAACAACTAATCCTTTTCGCCCTCGCGGCGTTTCTCGAAAAGGGCCAGGAAGATGCCATCGGTAAGATCACTGTCCGGCTG
GCAATACAGGACGTTCTTGCCAATATTGGGATAGTCCTTGTCGCCCACATTGTGCCACTTGTTGCGCAAGGCCTTCTTGCAGCTGAGCAGCTTGA
AGGATGGATTTAGCTGAAGACAACGCTGCACCACCTGCTCGTTTTCCTCCTTCCACAGCGAACACGTGCAGTAGGCAATGCGTTTGACGTTCGGA
AAGGCGCCCATCGCGTGCGACAGGATCTTAATTTGCAAACCCTGCAGCTTTTGCAGCCGCTTGTCCTCCTTCGGCTCGTCGCACACGGTCATGCG
GTTTTGCATTCCGCTGCCAGAGCAACTAGGGTCCACCAGGATGTACTCTACGTCCGGAAAGCGTTCGGGTGCTGAAATTCAAACGTGTTACTTTT
TTAAATATTCATTGTGAAATATATAAATATAAAACTCACTTAGGTTCAAGGCGTCTCCCAAAATGGGTTTTACAATATCGCAACCAGCATCCTTT
GTTATTTCGCACAGCGTATTGTAGCG
(SEQ ID NO: 1426)

Exon: 5676..5478
Exon: 2414..2334
Exon: 2270..1733
Exon: 1665..1001
Start ATG: 5573 (Reverse strand: CAT)

Transcript No. : CT17728
ACAGTTCGAAATTCAAAGTGTTCCTTTTTCAAAATTTAGTAAAGATTGTAGATCAATTGTAGATATATCGAAATTTTTCGGCCGCAAGCGAACAT
TTTACGAAATGAAGGCGACCAGTTGCAGACCAATTCCATTCATCAACTTTCGGATTGTAAGATATTTCTATCGGCCACGACGATTGAACAAGTAT
TACGATATTTACAGAATAGCTGCCCTTGTGCGGGATCGCGCCTGTCTCTTCACGTGCCAGCAGGCCTCGCAGAACCTGCAGCAGCAGCAGCCCCG
CTTTTATAGTGCGCCAGGTCGCAGGGCCGGCTTCTTCTCGCAGTTCTTCGACAACATGAAGGCGGAGATGGATAAGAACAAGGAGATCAAGGACA
ATATCCGAAAGTTCCGTGAGGAGGCCCAGAAGCTGGAAGAATCGGATGCCCTGAAATCGGCGCGGCAAAAGTTTAACATTGTCGAATCGGAGGCG
CAAAAGTCGTCTAGCATGCTAAAGGAGCAGCTGGGCGCCATCAAGGAGCGCGTAGGCGATGTTCTGGAGGACGCCAGCAAATCCCACCTGGCCAA
AAAGGTTACCGAGGAGCTCTCGAAGAAGGCTAGGGGGGTCAGCGACACGATCTCCGACACCAGTGGCAAGCTGGGCCAGACCAGCGCATTCCAGG
CTATCTCTAACACGACGACGACCATCAAGAAGGAGATGGACAGCGCGAGCATAGAGAATCGTGTCTATCGTGCTCCTGCCAAGTTGCGAAAGCGC
GTCCAGCTCGTCATGAGCGATAGTGATCGCGTTGTGGAGCCCAACACGGAAGCCACTGGTATGGAGCTGCACAAGGACTCCAAGTTCTACGAGTC
GTGGGAGAACTTCAAGAACAACAATACCTACGTGAACAAGGTGCTTGACTGGAAGGTTAAATACGACGAGTCCGAGAACCCTGTTATTCGTGCCT
CCCGCCTGCTGACCGATAAAGTGTCCGACGTCATGGGTGGACTCTTTTCAAAGACAGAGCTTTCGGAAACGATGACGGAGCTGGTGAAAATCGAT
CCGAGCTTTGATCAGAAGGATTTCCTCCGCGATTGCGAAACGGACATCATTCCAAATATTCTGGAATCGATTGTCCGTGGGGATCTGGAGATTCT
GAAGGATTGGTGCTTTGAGAGCACTTTCAATATTATCGCAAATCCCATTAAGGAGGCTAAGAAGGCCGGCGTGTACCTGGACTCCAAGATCCTCG
ACATCGAGAACATTGAACTGGCAATGGGCAAGGTTATGGAGCAGGGCCCGGTACTGATTATCACGTTCCAAGCCCAGCAGATTATGTGCGTGCGG GACCAGAAGAGTCAGGTCGTCGAGGGAGATCCGGAGAAGGTGATGCGGGTTCACTACGTCTGGGTGCTGTGCCGCGACCGCAACGAACTCAACCC
CAAGGCTGCCTGGCGGCTGATGGAGCTGTCCGCCAACAGCTCAGAGCAATTTGTTTAG
(SEQ ID NO: 1427)

Start ATG: 104 (Reverse strand: CAT)

MKATSCRPIPFINFRIVRYFYRPRRLNKYYDIYRIAALVRDRACLFTCQQASQNLQQQPRFYSAPGRRAGFFSQFFDNMKAEMDKNKEIKDNIR
KFREEAQKLEESDALKSARQKFNIVESEAQKSSSMLKEQLGAIKERVGDVLEDASKSHLAKKVTEELSKKARGVSDTISDTSGKLGQTSAFQAIS
NTTTTIKKEMDSASIENRVYRAPAKLRKRVQLVMSDSDRVVEPNTEATGMELHKDSKFYESWENFKNNNTYVNKVLDWKVKYDESENPVIRASRL
LTDKVSDVMGGLFSKTELSETMTELVKIDPSFDQKDFLRDCETDIIPNILESIVRGDLEILKDWCFESTFNIIANPIKEAKKAGVYLDSKILDIE
NIELAMGKVMEQGPVLIITFQAQQIMCVRDQKSQVVEGDPEKVMRVHYVWVLCRDRNELNPKAAWRLMELSANSSEQFV*
(SEQ ID NO: 1428)

Name: probable mitochondrial inner membrane protein import receptor (translocase)
Classification: receptor Celera Sequence No. : 142000013385184
CCAGCGTCTGCGCGCCATCATCAACGGCATCAATCCCGACGTGCTCCAGGGTCATCAGCCAGTGGCTTCAAGTGAAGTAGTGGTCGCAACGGAGG
CGCCACAGACCGTGGCCGAGTCCACTGAGGCGGCGGAGCAGCAGCAGCAGCAGCAGCAGCAGGAGAACGGCGAGACTGAGCTGGAGAAACCTAAC
GAAAGTTCGGCGGACGTTGCGGAGATAACTGCCGCTGTGGAGGCCTGCCAGATTGAGGGGAACTCGGTGGTGACCACCGATGAAGCCGCACAGCC
AAGCCCAACCGTCCAAGCTGAAGCCAGTGGCTCCAGTGAGTAGATCTCAGATGACAGCAGCACGTGCCAGCACACACCAAACGTAAAAACAAAAA
CATCCCATTTAGAACGCATTCATTTAGAAGAAATGTTAAGTATTTTCCGGAATTTACATGTAAATAAAGCGAAATAAAGCATGAGCGCATGCAGC
GTATTATGGATTTTTCAAATGTGTTTATTGAAATCAGTTTCATAATTCATACACGTTTTATATCATTTGTTTATTAATACAAAGGATTATTGATA
ATACATATTAATAATAGTTAATTTTTAAAAAACACATCCTTAAAATGACGGGAAGCGGACGTTTGAATAGCTGATGAATGGTAAGGAGTTTTAGG
GACAAACTAATATATTTCGCTGATTTTCTTGCAGATATTTCTCTGGCTGGCTGGCTGGCTGGTCCATTCGGTCGGACTGCATTGTGGACGAACAA
AAAAAAAACTGATTCAAGGTCGAAACTTAGTGCTTATAATTCCTCTTTATACTTCTTGGCAAGCATTCGCCTCCACCTCCTCGGTTCAACGATTT
CCCCTCTTCGATTTTTTGTTTCTTGTTTTGTTTTCACTTGCTCTATACTCTTAAGGCCAACGAGCACTACAGGGCCCCCACATCTGTATGCTTTG
TGACCGACTGGCGTCCAGTCGCTCCTCTGCTGCTCCGTTTCCATCTAATCTGCATGGTTATGCGCTTGGTGCTCTGCTCGAACGGTCAGTTGATT
AACCTAGTGTTTAAATTTTGGACAAAACCTATAAAAGCGCTGGTGTTCAAATGTGTGTACATGTGTGTGCGTGGGTGAATGGTTGGTCGGTCGGT
AGATATACATATATATATATATATACGGGGGCTATTACAAATAAATATGTGGCTTTTAATCATGGTATTTGTCAATGTGTTTGTAATTGCGATTT
AAATCTCAATGGGTGTGGGGTGGAAGGGGAAAACTGCAGTCATCTGCTGGAAGGGATGTCTCTGGGGATGTCCTTTGATCGTGGCGCTGCTATTC
CATACCAAATTAATGGTGCAATTTCTTGTGGATTTCGACTCGCCCCGGCTGCCGATGATAAAAGTGACCAAAAACAGAGATAAGGTTGGGGTGAG
AGTGTGATTCACTAGTTTGTTACTCTGCGTCAGCAGCCCATACTTACGTTTCATGCATCATTTGATGTGTTGTTTCAAAGGATTTTATTTCTGGT
TGATTGTGTGGTTGGGTTTGTGGTTGTTTTTGTCGTGTTTATCTTTTGTATCTTGTTTGGATTTCTTATTGATCTGTTTTAGATAGAAAAAGACT
GCTCGTGGTGCTGCAGTTGTGTGATATTACTTTTTACGCTTGTCGGCTGGCTTGAGGATTTGGAACGAGCACATCAGCGTATCGTCCACGGACAT
CATGGCGCCGGCATTGTCGAACTCGCCGCAGTAGTTGGGCGCCGAGAACAGGGTGACCAGCATGCGTTTGGCAAAGAACTCGTACCCATCCTCGA
CGACTTGATGGGCTCGGCAGATGAGATCGAACTCGTGCTTCTGCAAAAACTTGGCCACCACCTCGGCACCGAAGGTGAAGCTAACGCCGCGGTCG
TTTTCGCCCCAGCCCATGGTATCCTTATCGGGATCGGACCACAGGAGATCGCACAGCAGTCCCTGGTCGGGCACATCGGTTGGCCGCATAATGCG
ACGGATCTGCTCCATGGAGGTCAAATCGGGACTGAGACCACCGTGGCAGCAGAAGATCTTCTCGTCGACAATGGCCGCCACTGGCAGGCAGTTGA
AGCAGTCCGTGAATGTCTTCCACAACTTGATGCTGTAGCGACGCTTGCATTCGTCGTAGAATCCGTATATGCGATTAATGCTGGCGCATTCGTGG
TTGCCGCGCAGCAGGAAGAAATTCTCCGAGTATTTGATCTTGTAGGCGAGCAGCAGGCAGATCGTCTCCAGCGATTGCTTGCCGCGATCGACGTA
GTCGCCGAGGAACAGGTAATTCGATTCCGGCGGAAAGCCGCCGTACTCGAACAGACGCAACAGATCGTAGTACTGTCCATGGATGTCGCCGCAGA
TCTTCAACGGTGCCTCTAGCTCGAGCAGAATGGGCTGCGACAGGAAGATCTCGCGCGACTTCAAGCAAAGTCCCCGGATCTCGCCCTCCGAGAGC
TGTACGTTTTTACCTGGCCGTGCCCCACGCACCTCGAGAAGTCGCGATATTATGCTGTCGATATTCATCACGTCGCCCATGTTTGCGTGCGAAAG
TGTGGATCTGGTGCACTAGTGCTGCTGTTGGGTGTCGAGGTTACCGCGAACGATCGTTGGTAGCGCCGAAATAGCCTCGAAATCTTTAATTTCCG
AAATCTATTTCTGCTAAATACTTTTCACAGCTAACAAGTATGAAAATTTCTTCGTATGCTGTTGCGTGAGTGCGGGCGGGATGGCGAGTGTGCTT
CTAGCTGATGTTGCCACACTGCCGGAAGTCGCGGATATGGCCAGATAATAGACGCCATCTTATCTAATCGATAACATGCAAATATAGTGCATAAT
CGATAACGAAGTTGCTGTAATATTACTCTTATTACATTAAGGACATTTCCAATCCATTGCAAGAGTTCCGCAATAGCTCTACTTTTATATTTTCA
TTCGAAACGGGTCTTCTCGACCCTATAGTGGCTCGAAACTGCTGTTAGTAATCGATTAAACGCATGGCGTCCAGTTACTCTATTTCAGCGGTGTG
GCAGCCTGATCAGGGGGACACTAGCCATCCCGCTTGCACTCAGGCACGCCTGGCATGACTTACTGTGGAAAAGAGATGGGAGACTGATGCATTTG
GCGAGGCTATTCGATATACCGGTAACAAGGGGATATTTAAATACATTGGAAATTCAAATAAGCCAATAAGAATATTCGTTTACAGAACATAGGTT
AATTCATTTTCCTTATTGGAATAACTTCCACATGAGTTATGATTTAAAATGCCAAATTTCCCTTAAATTCTCACAAAACTAAATAATATATTGAT
AGATATATTAACAATCACACTATGTAAAAATTTTGTATGAAATGTGCTCATGTCTTGTTATCGATAATTCGATACTCTATGCATTTCCTGCCTAC
GCCCGCTAATCATTTAATTAACTGTTAAATAGGCGGGTTTCAATTTAATCAAAATGCTGTTAAACGATATCATAAGCGGAAAATTAGTTGATTCC
GTCTATATTATAGCGGAAATTGGCCAAAATCACCAAGGTTGTGTGGAAACAGCGAAGAAAATGATATGGGAGGCCAAAAAAGCCGGTTGCCACTG
CGTCAAGTTTCAAAAATCGGATTTGCCAGCAAAGTTTACGAGATCCGCTCTAGATCGCGAATATATCAGTGATCACGCCTGGGAAAAACGTACG
GGGAGCACAAGGAGTACCTGGAGTTCTCCAAAGATCAGTATCTCCAGCTGCAGGCCCACTGCAAGGAGTTAA
(SEQ ID NO: 1429)

Exon: 2777..1473
Exon: 1378..1001
Start ATG: 2550 (Reverse strand: CAT)

Transcript No. : CT17842
GCAGTGTGGCAACATCAGCTAGAAGCACACTCGCCATCCCGCCCGCACTCACGCAACAGCATACGAAGAAATTTTCATACTTGTTAGCTGTGAAA
AGTATTTAGCAGAAATAGATTTCGGAAATTAAAGATTTCGAGGCTATTTCGGCGCTACCAACGATCGTTCGCGGTAACCTCGACACCCAACAGCA
GCACTAGTGCACCAGATCCACACTTTCGCACGCAAACATGGGCGACGTGATGAATATCGACAGCATAATATCGCGACTTCTCGAGGTGCGTGGGG
CACGGCCAGGTAAAAACGTACAGCTCTCGGAGGGCGAGATCCGGGGACTTTGCTTGAAGTCGCGCGAGATCTTCCTGTCGCAGCCCATTCTGCTC
GAGCTAGAGGCACCGTTGAAGATCTGCGGCGACATCCATGGACAGTACTACGATCTGTTGCGTCTGTTCGAGTACGGCGGCTTTCCGCCGGAATC
GAATTACCTGTTCCTCGGCGACTACGTCGATCGCGGCAAGCAATCGCTGGAGACGATCTGCCTGCTGCTCGCCTACAAGATCAAATACTCGGAGA ATTTCTTCCTGCTGCGCGGCAACCACGAATGCGCCAGCATTAATCGCATATACGGATTCTACGACGAATGCAAGCGTCGCTACAGCATCAAGTTG
TGGAAGACATTCACGGACTGCTTCAACTGCCTGCCAGTGGCGGCCATTGTCGACGAGAAGATCTTCTGCTGCCACGGTGGTCTCAGTCCCGATTT
GACCTCCATGGAGCAGATCCGTCGCATTATGCGGCCAACCGATGTGCCCGACCAGGGACTGCTGTGCGATCTCCTGTGGTCCGATCCCGATAAGG
ATACCATGGGCTGGGGCGAAAACGACCGCGGCGTTAGCTTCACCTTCGGTGCCGAGGTGGTGGCCAAGTTTTTGCAGAAGCACGAGTTCGATCTC
ATCTGCCGAGCCCATCAAGTCGTCGAGGATGGGTACGAGTTCTTTGCCAAACGCATGCTGGTCACCCTGTTCTCGGCGCCCAACTACTGCGGCGA
GTTCGACAATGCCGGCGCCATGATGTCCGTGGACGATACGCTGATGTGCTCGTTCCAAATCCTCAAGCCAGCCGACAAGCGTAAAAAGTAATATC
ACACAACTGCAGCACCACGAGCAGTCTTTTTCTATCTAAAACAGATCAATAAGAAATCCAAACAAGATACAAAAGATAAACACGACAAAAACAAC
CACAAACCCAACCACACAATCAACCAGAAATAAAATCCTTTGAAACAACACATCAAATGATGCATGAAACCCGGGGCGAGTCGAAATCCACAAGA
AATTGCACCATTAATTTGGTATGGAATAGCAGCGCCACGATCAAAGGACATCCCCAGAGACATCCCTTCCAGCAGATGACTGCAGTTTTCCCCTT
CCACCCCACACCCATTGAGATTTAAATCGCAATTACAAACACATTGACAAATACCATGATTAAAAGCCACATATTTATTTGTAATAGCCCCCGTA
TATATATATATATATGTATATCTACCGACCGACCAACCATTCACCCACGCACACACATGTACACACATTTGAACACCAGCGCTTTTATAGGTTTT
GTCCAAAATTTAAACACTAGGTTAATCAACTGACCGTTCGAGCAGAGCACCAAGCGCATAACCATGCA
(SEQ ID NO: 1430)

Start ATG: 228 (Reverse strand: CAT)

MGDVMNIDSIISRLLEVRGARPGKNVQLSEGEIRGLCLKSREIFLSQPILLELEAPLKICGDIHGQYYDLLRLFEYGGFPPESNYLFLGDYVDRG
KQSLETICLLLAYKIKYSENFFLLRGNHECASINRIYGFYDECKRRYSIKLWKTFTDCFNCLPVAAIVDEKIFCCHGGLSPDLTSMEQIRRIMRP
TDVPDQGLLCDLLWSDPDKDTMGWGENDRGVSFTFGAEVVAKFLQKHEFDLICRAHQVVEDGYEFFAKRMLVTLFSAPNYCGEFDNAGAMMSVDD
TLMCSFQILKPADKRKK*
(SEQ ID NO: 1431)

Name: Serine-Threonine Phosphatase Alpha-2
Classification: protein_phosphatase
Gene Symbol: Pp1-87B
FlyBase ID: FBgn0004103

Celera Sequence No. : 142000013383859
CATCTGTGTTGGGATCGCTGATGAGCAGGACCTTTAGTCCATTTTCTAGTTGCAATCCGCGGTAGTCGCGTGTGTCCTGCAGCGACTTTTCAATG
TTGTTCAGCCTATAAACGACGAACCATTGCCTTTCGACGACCTCTAAGATGCGTAACGTGCACTTACCTCAATATGGGCTCCATGCTGTCTGGCT
TCCTAGTTGCGGACTTTTGCGAGCTTTCGGCTATTGTCATCTTGGGTTTTATAAGCGTGCCAATCGTTCGATGTGTTACTGAAATGCTGGCCCTC
AACGCACTTGACCTGTGCGAAATAAATGCGATTTAGTGGTGCCCGTTAGCGGAAATTTGTTTAATTGCTGCCAACCGTCGACCAAAAACCGCTGT
TAAGGCAAAAATCGATTTTCTGCACGTAAGATACATTGAGTTTGTGAAATACTCTTGACGACGCTACTCCGGCTTTACGTAGCGCGCACAAGAAA
TCTTAGAGTGGGAGGAGTAGATTTCCAAGCCGGTCGGTTACACGTTCAATCAATTTTAATCGCTTTTTGGACCGAAAAATAAATTCTAACTAGTT
TCGCAACAACTAAAATAGCAAACAATCATCTGTTCGCAGAGCTGCCAACTCACCGCGCACGCAGAACTAGTTTAATATGTTGCCAGATCGTTTAT
TTTGTGAGTGGTTCCAGATTTGAAATTCCCAATTGGAGAAATTTTACAAAGTGGTAGGCCATATTTTCAAATACGAAAGACTTAATAAGTTTAAA
GTGATGATTTTTAATAGTTCTAATGTAACTTTGGACTAAAGTAAGCTGCATATTCACCTTACCTAGGATAGATGGCGATTTCAAAATGTATTTCA
AATGCTTGAAATTTTTCCAACGACCATACAATAAATATTGGGCAACCCTGATAACAGTCATTATAAAAATAAATATTCCGTGAATTCCCGTTCTC
CGTCAATCTGGCAGTGCTCCGCGCCCAACCGCCGCCGTTTTCCAACACTGGCCGGTTGCCGTCAAAGCGCGTAGAAGAATTGCGGGCTGTAACTG
CAATTTATTATTTTTTAATTTCATTTATAGTGCACCTGGTCAGCGAGCACTGGCTCATCCGCAGCCATCCGTCGGCAACCAGCTCGCAGCGATGT
TAAACTTGTGCCAGCCGTAAAGATTTCGCGTGTTTGCGAACCACAAACTGCGTCGCCATCGGTGTGTGGGTGCAGAAATAAATGCAAATTGTTGT
AAAATGCCGTGCTTTGGTGTGCGTGTTGATAAGTGCAATACGCAAAAGTAAGAACATTGAGGCAAATCCGTGCAATTCGTGCAATCCGTGGGATC
AGGCGTTTTCAGAGGTGAGTGCTGCAGTGCTACGTCCGCGGAGATTTATGAGTTCGGGAATTCTGTGCTCTCCCCTTCGGCCAGCAGTCGAAGAA
TTAGGTTCTAATCAGGTTTTAATTGTTTACCCACCAACATGCGTTTCCTCGAGAAAAAGTGCAAGTGTTCAACGATTTTTCTCCCCTAAATGGG
TCAAGTTTGCCGGAATGTCGAGTCCGAACTTCAAGATCCCCTCCTAAAAGTCCCTTCTGTGCCTCCTTGTGTGCGAGTCTGAATGTGTGTGTGGT
TTGGTAACGGTATTTGTGGCCGTTTTGCAATGGCACGAGAAAATCAATAAGCTGGCAAAATTGAAGAAAGGAGACTTCCCAGACATGGCAAAACA
GCGCAGAGTTTGTTAATAATGCTAATATGCTGGCGTGTTCTGCGAATTCTCGCGAATCAAAATGTCTAATTAAACCACAGGTTCACACCTCGCAT
GAGAAATAAATTGGAACCAGTCCCTAAATAAACTTTGTTTTTATTTCCCAAGATTATGGTTGGTGCAAATATTTTACAATGAAAACTAAGAACAT
ACCTTTTAAAAACTAAAAAATACGATCTTTCCATTTTCAAAATACCTGATATCTTCAAAAACTAACAGTTGTTTACCTTCACAACGTCTTCTTTC
TTTGTTTCTTTGTTTTTGCTTCACTTTGCTTAAGACTGGGCACTTAAATAATATATTTTAAAAATATTTCTACAAGGAAATAATAAAAATAAAAA
CGGTATTTTATAGTAGTTATATCAGACATTAATTTTTCAATATTTGAAGAATATTCTTCCCTCTTTAACCTTCATAAAGTCAATTCAAATGGCTC
TAAATAGATTGAACACATAAATTATAGAAAATCAAAGCAAAAGTGGAACCGATTGCCATGTATTCCAGAGGTCAACGATCCACAATATTGACAGT
AACTTAAAGTCTTCGCACGAACAAAAGACTTTCCTGTGGAGAACAACGATCGCTTCTGGCGACCACTTGAAGTACTTTCAATTGCATGGTTATTG
TTTTGGGTTTAAAGCGCGTCCCAAAATAGACAGACTGCAGCTCGTCGAGAAGATCGGACAATGGATTGCCATGAAGCGTGGGCCACGCAGGAAGA
AGTGTGCTCATTGCGACCGGAGGATTGAAGGCAGATATATTTTTAGTGCAGCCCAATTAAGTTCAATTAGAGGTTCAAAGAGAGAGAGCGAGCTT
ATCGCTCCGTATCCGAGGTACTTACTCCAACTTCCTCCGCGACAAGTGGATCAAGTGGGGGTCAATGAATTGGCTGGTTTTATAGCCTCCGTTTG
CGGGATCCAATAGATTTCTAAGTAAATGATACGAAGCTGGTATCTGATTTCACTATAGTTATTTTCACAGTGCGCAGCGAGTAAACAAACAAAAT
TGCCTATTGGCGTAGATCAGTTATTCTGGCTTTACGTATAACTGAACGTAGAAGTGAATTTTCCCAGTGCGTAGATTATTTCAAACTATGTATTT
CTATTTTGGGAAGCACTTAGGTATCTAGATTAAAATCAAATTAATCACGTGATGAAACCATTTTGCCTTCACACAAAACGTTAATGCAGACGACA
CTTTGTGTAACTTAGTAATTAGCAGGTCGATTGTTAGTCGAGAATTTAGCATCTGCTTATCAGAACTGAAAAACATTAAGGCAGCTATTCTACGT
AGTTCACTTATTTATATTAGAAGGGGTGTCAGCAGTTTATTTTATTTTCAATATTTTCATTTATGTATGTTTTCCTCAGGAGAGACCACATTTTA
TTAAATCACACAAAAATCCAATACTATTTTCATTTCAGATTCCATAAGCTGGTTCTGCTATTTGTGCATGCCCAAAATGGACAACGAGCAGCCGC
ATCAAGAGCTAGTGAAGTGCGTCCTGGTGGGGGACACGGCCGTGGGCAAGACGCGACTGATCTGCGCGAGGGCCTGCAACAAACACGTCTCGCTA
TCTCAGCTCCTCTCTACGCACGTGCCGACCGTGTGGGCCATTGACCAGTATCGCATATATAAGGATGTGGGTTACCATTCTCTCAAGAGTCATAG
TTATTGCATTTAACCGAATCCATATACATTAAAGGTACTCGAGCGATCATGGGAGGTGGTCGATGGAGTGAATGTCTCACTTCGCCTATGGGACA
CATTTGGTGACCACGACAAGGATCGGCGCTTCGCATACGGCAGGTGTGTAGAGCTCATGTAGCAGCATTTTCGCCATACGAATCAATAAGATGCC
TTCTTGACCTACAGATCCGATGTGGTGCTGCTGTGCTTTTCCATTGCCAGTCCGATTTCCCTGCGCAACTGCAAGATGATGTGGTATCCGGAAAT
TCGCCGCTTTTGTCCGGATGTTCCCGTCATTCTAGTTGGCTGCAAGAACGACCTGCGCTACATGTATCGCGACGAGAACTATCTCTCGTATTTCG
GCGAGAAGGGAACCTTTGTTCGGTATGCATAGCTAGCAGGTTTCAGCCGGTTTTGAGTGGCTTTCACTTTTTAATGTTGTTCTTTAATCAAATCA
ATTCAATTATTCACCATAATTTAATTATATTTAGAACACACGAAAGATATAATTCAATGTTTAGCCCACTATAGCAAATTAATCTGTTTATATGT

FIGURE SHEET 765

TCAGAGATATTCTATTTAATTGGATTAAATTAAAGGCAATCATTACTATAATCTTTTTTTAAAGAGCCGCGTTGAAGAGTGACCTGGTTATGCCG
GATGAGGCGCGTGCCGTCGCCAAAGAGCTAGGAGTGGCGTACTACGAGACCAGTGTTTTCACATACTTTGGGGTGAACGAGGTGTTTGAAAACGC
CATCCGATCCGCGTTGATTGCACGCCGACAGCAGCGCTTCTGGATGACAAACCTGAAGAAGGTGCAGAAGCCCCTGCTGCAGGCGCCGTTCCGGC
CACCGAAGCCACCACCACCGGAGGTCACCGTCATGGTCGGCAACTATCGGCAGGACATCTACAACATGTTCCTGTCGCAGGCCTACACCGACCTC
GTCCTGGTCGGGGCGGGTGGCACCAAGTTCGCCGTGCACAGGTTCATGCTAGCCGCCGCGTCCAGCATCTTCCAGCGCCTGCTTAGCACTGAGCT
GACTGATATGGGCGGGCGGAGCAGCAGCGAATCTAGCATGGTCAGCTCAACATTCGGGGAGGCCACCATTGCGGACTTTAACGATGACACGGAGG
CCCTGATCCGCTACGAATCACGCACACAACGGTGGGTGCTGCCTCCCGATTGCATTGAGCCCATTTGACTTTGAATACATTTTGCACCCACAGAA
TGTGGGAACACTTGAAGCGCCGCTCCAGCTACCAGGCGTTGCCTCTCATGGAGTCTAAGCGGTCCAACGATTTGTACAGGGAGCTGCATCATCCG
GTCCTGCAGAGCATTCGCCTGGTGCACGTGGAAAACCATCGGGGTGTAAATGGTCTGCAGACGATTGTCACCCTTAGCAAACTTATCTCTCCGCA
AGCTCTGCACCAGTGCCTGAGATTTATTTATACCGGTACCATTGACAAGGATTGCGATAATATCGAGGTAGGAAATGTTTCAATGTATTCTGTGT
TAAGTTTGACCTACTAATATATTGTTAATTCTCACAGGAAATTCGAGAAGCTGCCGATCTATTAGAACTGCCGCAACTGACTCAGCTACTTTCCA
GGCCTCAAACCGTTATGGAGAACTCCAGCGATGAGCCAAATCCGCACATTTGCCTGGTGAGCGCATTGATGTCATGATATCTATTTTATGATCCT
AACCATTTTCTGTTACATACATTAGCGCATCAAAGAAAGCATGGAACGGCATTGCATTGGTGACGGGTGCTTCAGTGATGTCACCTTTGAATTGG
ACGATGGCTTAATGAAGGTACATACATATGTCTGTTGAATTACTATATGAAGCACAATCGTTTACACTTACCTTTGCTGCATTGCAGGCACACCG
CGCTGTGTTGGTTGGTCGTTGTGATGTCATGCGCGCAATGTTGTTAGGCGACTTTCGCGAGGCTCATTCCAATGTGGTAGGAACGGGCACAATAC
CCCTTAACTAAGGACAGTTGTCATAAATTTCCTTTACCTTAGATCGTATTCCCTGGCGTTACCATTTACACATTCCACAAGCTGCTGTGCTATTT
GTACACAGACCAGATTCCGCCAATCTCGGCCGTCAAGTGCCTCAATCTGCTGGAGCTGGCCAATAGACTCTGCCTGCCGCGGCTGCTCAACCTGG
TTGAATGCCGCGTTATTGAAGATCTCACTCTGATTTCTCAGAACGAAACCAATGAAACGGTGGATCACTGTCTAAAGCTGCTCGAGCCAGTGAAG
GTACACATAGAGAGATCAGTTAAAAATGATATACCGAAATTCAATACTTTTCTTTTTTTTTCAGCTGCACAACGCACATCAATTGGCCGAGTGGT
GCATGTCATACCTGTGCGTCAATTACAACCTTATTTGTAAGTTTTCACTCAAGGGCCTAAAGGCGCTACACCAGGATAATCAGGAGTACTTGCGC
GAGCACCGATGGCCTCCAGTCTGGTATCTGAAAGACTATGATTACTATCAGCGATGCCTGAACGAGCTGAACAAGGAGCTTAAGCTAAAGACTTC
GAGGCGGGAATCGCCTAGCGATGACGAGGGCTGTCTGTGCTTTACGGGCGGTAAGTGTTGCTACATTTACGGAACTATCTGCTCCACATCCCACC
ACACTTAACATCCCAGTCCAATACTCCAGTCGGAGGATCAGCTCAGGTTTTAGTTTCAGCTAGCTTTAGAGGACAATGTATGTATCATGACGGCG
GTTTGTATTCGTAGCTAGGTGTCTCGTTATTGTTTTCCTTTCCTGTTGATTTCCTTGCTCATTTACAACGACAACGCCATCATCATAATATTAAT
GTCCGAAATTTGGTCAAAGTATTCTCTTGCTGGCTGTTAGGTAAATCGAAGCGAAGCGCTGATGTGAGTGGAACCACGGATAACAGCAACGCAGA
TAATCAGATCTTCAACAGCGCCGGCAACTCGCTCAACCACATTGATCTGGAGGCGGACATGGACCTGAATCTCTGACACCCAGCCCTAGGGCAAG
GAAGGTGTGTTGATATTAATGTCAAAGTAAGGATTCTTCGATATTTATGATTTACTTCGATACTTTGATTCCAGATCACTGCGCTTCATTGTGAT
CCTGCCGGTCCTGATCTGTTTTATCTGTACGATTTTAAGTATTTTGATACTTTTCCAAATCCATACATAACAAACCTCAAGGGCACGATTTAGAG
TGGTCGGGGAGATAAGGGTTGGAAATGGAGGGGGCGTGGCGCGTCTGCTTTTGACATTACGCAATATATAGAGCGCAAATTTGCCTTAGTGATTA
ACGATTAATAAGTCCAACGTAGCTCGACCCAGAACAAGGGAGCATACTGCAGAGTGCTTCGGATTTCTTATATTTATACGCCTATATAAAACGCA
AAGCATAGACGAGTATGTATGCACATGCACCTCGGCGCTGCGAAGCATTTCGCTGTATTGCCTTACGATATATCGGTGTACACTCAACTTGTTCT
GCACGATCCCTCCCATGGAATGTGGACAGCCGAAGGACGCAGACATGTGTATATCCATATATTTGTACCTTTACCTAAGACATGTATGTATGTAT
ATTTTTGAATTCCTACTTACGGAAACATTTGTCTAGCCATAGCTCTAAGCAATTCTCTACGATAAGGACGCATTTTGTACAGAATGATAGAATAA
AAAAGCAATTACGAACAAATCTCACGTTTCTTCCTTGTAATAAAAACGCATTTTACAATGTAATAAATTTAGAATTATAACAGTTCACATGCCAT
TTAAAAAAACACAACATTTATATCGCAGTTTTCACGGATTTTACACTGGATTGCGATACAGTACCATCCTCCACCTCAAGATCCTGCAGCATGGC
AATCATCTCCTCGTCCGTAATCACAACCTCCGCCCTTAGGTTGTTATTAATATGTGGACTAAACGTAGCCGGCGCAGATTCTCCAGCCAGTTCAC
GCAATTCCTGCTCAAGTTGATCATCTTCCTGGCTCGCGTTCTCCACAACGCTATTGGACATTATGTCCTGAACTTCCCGATGCTGGTCGAGCGTG
TCCCGCACATCGGCCAATACTTCGTCGACATTGTCGTACTTCAATCCAGAATTCGAGAGAACCTTCTTCAAGGTATTTGATCCGATCTTGTAGGC
ATCCAGAACAACGCCACTGTTCTGGGCCTCATCCACACTGGACAGAAGAGATTCGATGTTGTGCAGGGCAAGACTGCGACGTTCTAATTAGAGAA
TTTTCAAAGAACATTATTCACAAAAGCCAGATAAGGGGTGTCTACAATAAAGATTACCATGATTCTTTTCCAGGAGATGCCTTTTTCGTAGATAG
GTTTTTGCCATTTGCCGTTTGTTCTCCTTCATGTACTGGCGCACTTTGTCATCGTTCACCTTGATCTCCTCCTCTAGGTCCTCCAACTGCTTGAG
TAACTGAGCTTGGGTATTCTGAAGATTGTGGACGGCCTGGTCTTCTTGGCTTATATTAAGATCGTCGCCAGGTTTTTCTATAACAAAAATTATAG
TTTAATAATACATACTAACTACTTGAGAACCTTTTAAACTTGCTTGGTATTTTGATCAAGTGAATTTGGCGTATGCCTTTTTCTACTTTAAATTC
TAGGCCCAAGATTTGACGAACATTTAAGGCCAACAGGCAAGCGCATAGATCTTTGTCTGAGTAAGTGGGAACTCCGTGAGTCTTACAAAGCGTTT
TCAAAGCATTAAAGTGCAGTAGTTTTCCAGTGTTTTCCGACAGGACTTTTTCGCCGATGAGATCGCAAGTGTTCTGGAAAGTTAATTATGTAGGA
TTCCTATAATCATTGGATGATATCACATACGTTTAAGGCATCTAGGTGAATCCATTCAATTAAAGCGGAGGCTTCCAGGTCCTCCGTCACCACGC
TGTGCTTGATTTCGACCAGCTCCATGAAAGGGGGCGCTTTACCAGGCTGTTGACGAGCCAACCACCCCAGGAATTGGCCGGATCGTACTCAAAT
TCACTGCGAGAGCGGATCTGCTTCCTCTGCTGCATCTCGGATATCACGGTGTCCAGGCAGGCGGGCAGTTGGTCA
(SEQ ID NO: 1432)

Exon: 1001..1344
Exon: 3174..3391
Exon: 3455..3558
Exon: 3625..3822
Exon: 4055..4591
Exon: 4654..4912
Exon: 4978..5091
Exon: 5156..5242
Exon: 5313..5396
Exon: 5458..5700
Exon: 5765..6035
Exon: 6311..6441
Exon: 7148..7530
Start ATG: 3212

Transcript No. : CT17926
GCCGGTTGCCGTCAAAGCGCGTAGAAGAATTGCGGGCTGTAACTGCAATTTATTATTTTTTAATTTCATTTATAGTGCACCTGGTCAGCGAGCAC
TGGCTCATCCGCAGCCATCCGTCGGCAACCAGCTCGCAGCGATGTTAAACTTGTGCCAGCCGTAAAGATTTCGCGTGTTTGCGAACCACAAACTG
CGTCGCCATCGGTGTGTGGGTGCAGAAATAAATGCAAATTGTTGTAAAATGCCGTGCTTTGGTGTGCGTGTTGATAAGTGCAATACGCAAAAGTA
AGAACATTGAGGCAAATCCGTGCAATTCGTGCAATCCGTGGGATCAGGCGTTTTCAGAGATTCCATAAGCTGGTTCTGCTATTTGTGCATGCCCA
AAATGGACAACGAGCAGCCGCATCAAGAGCTAGTGAAGTGCGTCCTGGTGGGGGACACGGCCGTGGGCAAGACGCGACTGATCTGCGCGAGGGCC TGCAACAAACACGTCTCGCTATCTCAGCTCCTCTCTACGCACGTGCCGACCGTGTGGGCCATTGACCAGTATCGCATATATAAGGATGTACTCGA
GCGATCATGGGAGGTGGTCGATGGAGTGAATGTCTCACTTCGCCTATGGGACACATTTGGTGACCACGACAAGGATCGGCGCTTCGCATACGGCA
GATCCGATGTGGTGCTGCTGTGCTTTTCCATTGCCAGTCCGATTTCCCTGCGCAACTGCAAGATGATGTGGTATCCGGAAATTCGCCGCTTTTGT
CCGGATGTTCCCGTCATTCTAGTTGGCTGCAAGAACGACCTGCGCTACATGTATCGCGACGAGAACTATCTCTCGTATTTCGGCGAGAAGGGAAC
CTTTGTTCGAGCCGCGTTGAAGAGTGACCTGGTTATGCCGGATGAGGCGCGTGCCGTCGCCAAAGAGCTAGGAGTGGCGTACTACGAGACCAGTG
TTTTCACATACTTTGGGGTGAACGAGGTGTTTGAAAACGCCATCCGATCCGCGTTGATTGCACGCCGACAGCAGCGCTTCTGGATGACAAACCTG
AAGAAGGTGCAGAAGCCCCTGCTGCAGGCGCCGTTCCGGCCACCGAAGCCACCACCACCGGAGGTCACCGTCATGGTCGGCAACTATCGGCAGGA
CATCTACAACATGTTCCTGTCGCAGGCCTACACCGACCTCGTCCTGGTCGGGGCGGGTGGCACCAAGTTCGCCGTGCACAGGTTCATGCTAGCCG
CCGCGTCCAGCATCTTCCAGCGCCTGCTTAGCACTGAGCTGACTGATATGGGCGGGCGGAGCAGCAGCGAATCTAGCATGGTCAGCTCAACATTC
GGGGAGGCCACCATTGCGGACTTTAACGATGACACGGAGGCCCTGATCCGCTACGAATCACGCACACAACGAATGTGGGAACACTTGAAGCGCCG
CTCCAGCTACCAGGCGTTGCCTCTCATGGAGTCTAAGCGGTCCAACGATTTGTACAGGGAGCTGCATCATCCGGTCCTGCAGAGCATTCGCCTGG
TGCACGTGGAAAACCATCGGGGTGTAAATGGTCTGCAGACGATTGTCACCCTTAGCAAACTTATCTCTCCGCAAGCTCTGCACCAGTGCCTGAGA
TTTATTTATACCGGTACCATTGACAAGGATTGCGATAATATCGAGGAAATTCGAGAAGCTGCCGATCTATTAGAACTGCCGCAACTGACTCAGCT
ACTTTCCAGGCCTCAAACCGTTATGGAGAACTCCAGCGATGAGCCAAATCCGCACATTTGCCTGCGCATCAAAGAAAGCATGGAACGGCATTGCA
TTGGTGACGGGTGCTTCAGTGATGTCACCTTTGAATTGGACGATGGCTTAATGAAGGCACACCGCGCTGTGTTGGTTGGTCGTTGTGATGTCATG
CGCGCAATGTTGTTAGGCGACTTTCGCGAGGCTCATTCCAATGTGATCGTATTCCCTGGCGTTACCATTTACACATTCCACAAGCTGCTGTGCTA
TTTGTACACAGACCAGATTCCGCCAATCTCGGCCGTCAAGTGCCTCAATCTGCTGGAGCTGGCCAATAGACTCTGCCTGCCGCGGCTGCTCAACC
TGGTTGAATGCCGCGTTATTGAAGATCTCACTCTGATTTCTCAGAACGAAACCAATGAAACGGTGGATCACTGTCTAAAGCTGCTCGAGCCAGTG
AAGCTGCACAACGCACATCAATTGGCCGAGTGGTGCATGTCATACCTGTGCGTCAATTACAACCTTATTTGTAAGTTTTCACTCAAGGGCCTAAA
GGCGCTACACCAGGATAATCAGGAGTACTTGCGCGAGCACCGATGGCCTCCAGTCTGGTATCTGAAAGACTATGATTACTATCAGCGATGCCTGA
ACGAGCTGAACAAGGAGCTTAAGCTAAAGACTTCGAGGCGGGAATCGCCTAGCGATGACGAGGGCTGTCTGTGCTTTACGGGCGGTAAATCGAAG
CGAAGCGCTGATGTGAGTGGAACCACGGATAACAGCAACGCAGATAATCAGATCTTCAACAGCGCCGGCAACTCGCTCAACCACATTGATCTGGA
GGCGGACATGGACCTGAATCTCTGACACGTTTCTTCCTTGTAATAAAAACGCATTTTACAATGTAATAAATTTAGAATTATAACAGTTCACATGC
CATTTAAAAAAACACAACATTTATATCGCAGTTTTCACGGATTTTACACTGGATTGCGATACAGTACCATCCTCCACCTCAAGATCCTGCAGCAT
GGCAATCATCTCCTCGTCCGTAATCACAACCTCCGCCCTTAGGTTGTTATTAATATGTGGACTAAACGTAGCCGGCGCAGATTCTCCAGCCAGTT
CACGCAATTCCTGCTCAAGTTGATCATCTTCCTGGCTCGCGTTCTCCACAACGCTATTGGACATTATGTCCTGAACTTCCCGATGCTGGTCGAGC
GTGTCCCGCACATCGGCCAATACTTCGT
(SEQ ID NO: 1433)

Start ATG: 383

MDNEQPHQELVKCVLVGDTAVGKTRLICARACNKHVSLSQLLSTHVPTVWAIDQYRIYKDVLERSWEVVDGVNVSLRLWDTFGDHDKDRRFAYGR
SDVVLLCFSIASPISLRNCKMMWYPEIRRFCPDVPVILVGCKNDLRYMYRDENYLSYFGEKGTFVRAALKSDLVMPDEARAVAKELGVAYYETSV
FTYFGVNEVFENAIRSALIARRQQRFWMTNLKKVQKPLLQAPFRPPKPPPEVTVMVGNYRQDIYNMFLSQAYTDLVLVGAGGTKFAVHRFMLAA
ASSIFQRLLSTELTDMGGRSSSESSMVSSTFGEATIADFNDDTEALIRYESRTQRMWEHLKRRSSYQALPLMESKRSNDLYRELHHPVLQSIRLV
HVENHRGVNGLQTIVTLSKLISPQALHQCLRFIYTGTIDKDCDNIEEIREAADLLELPQLTQLLSRPQTVMENSSDEPNPHICLRIKESMERHCI
GDGCFSDVTFELDDGLMKAHRAVLVGRCDVMRAMLLGDFREAHSNVIVFPGVTIYTFHKLLCYLYTDQIPPISAVKCLNLLELANRLCLPRLLNL
VECRVIEDLTLISQNETNETVDHCLKLLEPVKLHNAHQLAEWCMSYLCVNYNLICKFSLKGLKALHQDNQEYLREHRWPPVWYLKDYDYYQRCLN
ELNKELKLKTSRRESPSDDEGCLCFTGGKSKRSADVSGTTDNSNADNQIFNSAGNSLNHIDLEADMDLNL*
(SEQ ID NO: 1434)

Classification: enzyme

Celera Sequence No. : 142000013384535
TAAACAAACAGACGTGATATAAATTTTTTCTAATAGACAATAACTTTTTACCCATCTTAAACAAATTTTACAGTAAAATAATTTTTTAGTGTATA
CTTTTAGGATGAGACAGTTAATAATCTTGCACGCATTACTTATACGACGACCCTGGTTAACGTTATCCAATACCCAATGATAAAATATAGAATCT
GTGGATTTACTATATCAGTATCTTTATTATACGAGTACATTAATTCAGTTTACAGTTTTACAAAATTATTTGTTTGCCTGACATGTTTTCGTTCT
TCGATTTTAAATTTACGTTGTTTTAACATCTATTAAAAGTCGAAATTAATTTCGTTTGTGTCTGGGATGGACTGCGATTTCAATGTTGATAATAA
TATATGTATATATATAATACTTATTCGTCATCGACCCAAGTCGGTCGGTAAAGTGCATTAAAATGATTGATTGGCAACCGGAAATGAATTTTAAA
TTCATGATTTTCTAATGTTTGGCTTTACTTAGAACCCATTAACAAGACGATGCAATGAGGTTGACGTGTTATGATCAAATGGACGACTTAAATTT
CATAACAATCTTCTTTATATGTACACATATCGTACTTTATCTACAACTGCCACGGAATTCGCACTTATCTTAATTAATTATTTAATTTTCTGTTC
AACAGTGTCTAAGTTGGTAAAGTAAGATGCTTCAGTTGGAGCCATTATTTCCTAAAGAATTCTTGATAATATATTCAATTTACGGATATATTTTC
CTATCATCAGTATAATGGAAACTACTAGCCAATTGAAAAATGATGGCTCAGTCTTCGCCTTGCTCTTGCAATATATGTTATAATTGAAGTATAAT
TGCAGCCAAATTTAATTTACCAAATATATGTAAGTTCGATTGTAAAGGGCATACAGAAATAAATAAAACAAAAGATCATGTCCCATAATACTCTT
TATAAAATCTGAATTTATCAGCTAATATATGAAATTGATCTGCTGGGTGTAATGTATACTTATGTATTTATTTGTAATGCAGATACCCACATATT
TGTAACGTATGAATCTAAAACTAAAGTCATAAGTCGTGTTTAAGCCGAACGGGATTGGCCAATGATAAGTGTTCTTGCTTCTCAAATCGATCCGG
GATCATCTGTACAATTTTCGAGGGAAAGGGGGCTTTAAGTCTTAAAACCTCAAGTCGGTAAGTCTATGTAATTATTTAAATTGGACCTTACGCGG
TAATTAATCGTTACAGGTAAAATGTATACATTGCAATATGCCATTTTATGTATAAATGTGTGTATATTTGTTGTATTGTATTTTAAACATAATAT
TTTTATACAGAGTTTAGACAAAATCAAATAAATAGCGCGATAAACTTAAAATTATATGTAAATGTATTCATAAAGAACAGCTATGCCATTTCATA
GGAGTTTACCAGCGACAGATATAATTATTAAGAATAAATACTTTCCATGATTGGTTTTTGAATACTCGCTATTTAGCATAATGTATGTAGCGAAG
TAAATTTGAAGGACTAGGAACCAGTACGACGTATGATTATGTTTATCTATATGCTTATAAATGGTAATTATATATAATTTTTCAACTTATACAAA
CGAAATTGGGTTTCTTATTGTAAGAGCGTGCATAATTTTTAGTAGAACATTTTGGCTTACTTACAATTGCGCTCTATACACTTGACAATAAGGAA
ATAACTATTTACTTACAAATTAAACCTTTAGGCATCGTAAACTAACCAACTTTTGTGGGCAAAATTATTTTGCGATTATTTTTTGTATTTTTATCA
AGTGGTACTGCCAGGTATAAAGGAATCGTGTATGGGGATAAAAATCTCAAAGAATCGAAGAAATAAGTTATTAAATATGAATCAGGTCGGGGTTT
TCATCACAAGGTCCCCACCACAGCTAGCCGCCTTGCTGTTGCTTCTTTTTATCGAATATGGGAAGCTTCGACTTGACCGCACCCTCGCACACCAT
CATCCTTTGCTGCGCCGGCTTCTTGTCCAGATCGAAGCACAGGCCATCCGCGTTCAGGTGCCGCTTGAAGTCCGAATAGCGACGCGACTCGTACG
AAAGGTAGTTGGAACCCAGGGCAGAGGCAGCCACAGCAGCTGCTACCGTCCCGTTCCCATTGCGATGGTGCACCGAAGGCGGCGAGGAGTCCTGT
CGCTTTCGCTCAAAATACTCCACTATCTTGGCAATCTGTGCGGATCTTGTACTGGGCAGTGCCGTGAAGGAGCGGTCGTCCCAGAGCAGGGAGTC
AGAGCCGGCCAAGCTACTTATATCATCGGAGCTATCCGTGTATATGGACGAGGTGCGGTTCTTACAGTACAATAGTTGATTCGTTGCAAAAGGAC
TACGCTGAAGCAGAGTATGTATCTCCGAGTCTAAAGCCAGACGATTGATCAGGCTCGCCGTAGCCGCCATTTGGGATTCGCTGCCATTCCCGCTG AGCAACGCATGGTGGCAAGTGTATCGTCGCTGGTGTGTGCGCCGCGATGCCACAATGTCCGCGTCCAAGTCATCCATCGAGTCCAACGCTGTGGA
TGATGAGGTATTTCCACCGATCACAGCGGGATCATTGTCGATCAGCAGCACCGACGATGAGGTCGAGGACGTATCGTTGAGCAAGTGGCTCTGCT
GTTGTTGCTGGGCCGCAGCAGCGGCTGCAGTTACGGCGGCATTCGATGTCGAGGTGGCGTAGTAGCAGCAGCGACACAAACTCGCCAGTTTATCG
CTAGAAGATAAAATCATAATCAGTAAAATCAGATGCCAAGAACACAAATACAGCAGGCCCTACTTCATGTACCAAAAACATCAGACAAACATTCG
AATAGCTTTTGAAAATGCTTAATGGCTTTGTGATGAACATCGACTAATAAGATGATATTACACAATTAGCACGATCAAGAAAAAAGTGACTTATG
ATTGTGATTTTTATGCTTTAGCTAAACAAGTCACTTACGTTGCTTGTGCGTTAGGTGCTCGATATTTATACCGTGGCTGTGTTTAACCTGGGGTA
TGCCGAAATAATTATCATATATGCAACATTTTTCAAATTTAAGTTTGTATACGTATATTCACAGATCATTTAGCTAACATCTAATACATCCATTA
TAAAAATCTATTTTGATTCTAAGCCATTTAAGATACAATATGGTCATTACAATTCAGTTAAATTGAAATCTATACAATTAAGAGATTTACTCGAA
AGTCTTCTTCTAATACGGTACGATTTTACGAGGCAAGTTAAAAAAATATCTAATATCTACTCACTTGATTTCACTATCTGCGCTGACGCATGCAT
CGAGCATAAGCTGCGTCTTCAATTTCTCATAGCAGCAGTTGCTACTGTTGCCCCCGCCGCCGCAACCAAACCCCAACGATCCAATCCCGTTCAGC
TGCCGTCCGAAACTGTTGTTGGTTATCGCCGCATCGGACTCTTCGTTAAAGCACGAGAAGAAGCCACTTTCTATAGAGTCCCGCCTCGTTAGGTT
TGTCTTCAAGGGAAGCTGCTCACACGAGTTCTTCAATTCGTTCAGATCGCAGGTGTTTTTCAGTTCGTCGAGCTCAAGATCAGTGCAGGATGAAA
CGGACACCGGGGTTTCCACCAACCTGGTGGAGCAGCCAGACATGGGAGTGGGCAAAGCCTGCACCGCCGCTGTTGCACCGCTACTCGCTTGCTCT
TTTGATTTTCTGGCGCTTTCAGTCAGATCCTCACACGAATTGGTCGCACCCACTGACGCAGTCAACGTGATTGTAGATGCGCTGGCCTTCAGTAG
AGTTGGACTCTCGAATTCACCAGTACTGGTACTTTTCATGCTGGTGCCATTGGAGCCGCGAAAAAGCGGATGCGCATACAAGGAATTCGCGCGGT
ATTTTCGAGCGGTTGGCACAGTGGACGGACGCACGGCGCTGTCATCGCTGCTTGATTCCGCATCTGCACAGTTGCCACCGCCATCGGGATCCTCA
CCTTCCGAATTGCAATCATCGCAGTCATCCTCATCGGTTGGCAATGCTATTGATGGTGGTGGAGCACTGGTAACTGCTGGAGGAGCAGCATTGCT
GATTCGCTGAGGAAGTCGAAGCTCGATGGCGCTGTATTTGCGCGTCATATGCGGCGACACTGGCAGGCTCTTTGGTTCACTGGGCGTTGCTGCCG
AAGCCTTGTTACCCGTTGATGTTTCCTCCGTACTCGTTCCTCCGCCCTGAGCCCCCGCTTTGCTCTGCATTGCGGCCAGTTCTTTGAAGAACGGC
GCTAGCATCTCGAAGCATGAGCTGAATAGATCTCCCACCCCTGCTGCATAGGTTTTCGGATTGGCGTCCAGGATTTTCTTGACACCACGCAGTTG
CGCCAGCGCTTCAAACGGATTGGGTTTAGAGCCGTTGTGATCCTTTTCAGATGTCGGCTTGTACTGTGGATCGCCCACTTTGCGCAGTGTGAGTA
CCGCTGGAACGGGCTTGGGAAGCGGTGGGGATCTGGAATAGACGTGGCGGGCAACTGAACCGAGGAAAGCTGCCTTGGGGGCGTTGGTGAGTGT
GTTGAGGAGCGCTGTCGCTGCATCTGATGACACCGCGCCTTGTCACTTGGCGACGTGTGCATGGGGAAGTGGATGATGTTCTCGCTTAGCGAACG
CCGGTGCAACAAGATCTCGGCCTCCAACTTCTGAGTAGCCCGTCGCACTCTAGACTTCAGTATATGATCATCAAAGCCACTGCTTCCAGCAGATC
CATTTGGCGTGCCCGGAAGCGCAGCCGAAGCAGACTTTTTACTTGGAAATCGGAAGCCGTCCTCGTCCACTTCCTGTAGATGGCGCGGTGTTAAA
GTGCCAGCAGGAGCAGTACAAATAGTGGCCACCGTGGGTACTGATGCTCGGGGTGTCAACGTTACGTTCTCCGAATCGCTGCCTCCTGGTGAGCA
GTTGATCAACTCCAGGGAACTGAGTGGACTTGCTCCGGCCGACGACTCGTGCTCGTATTTCTCCAGCAGCAAAGTCAACTTTTTGGTGGCATCGT
GGAACGTGGGTCGGCTCTTGGCATCGTACTGTAAGTTATCGGATGGGTTACAACACATTCTTATATTGATTATAATTCCAAAACTCACCAGACAG
CAGTAGAAGGCCAGACGTAAAAACACAGGAGGAGTGTCCATCGGACACAATTCTACAAATGCCAGGTAGTCCAGTCCAAACGACGCCGTGCGCGG
CATCATATCCGGGTCCGCTTCGATGCGGGCTATGATCTCGCATTGAATGATGCCAAAGGAGAAGACATCGCTTGTCTGATCGTACCACTGGCCCT
TCAGGCACTCCGGACTGACCCAATACGGTGAGCCGACTGTCTCAAGGCGTGATTTTCTGCTGTAAGCAAGCCCATTTTGGATTCGTTTAATTATA
TTACACTTATGTTATGCTTAGACCAAGATATACTTACGATTTGACTGGTATCTTTGCGGCTAGACCAAAGTCACCCACTACAGCTTCGTACTGAT
CGTTGGCCAGATTGCGAATAAGTACATTCTGAATGAAGAATCGGATTAGCATACTAATTATTGGAGTTCCTTGCAGTTAGCGCTCACCTTGCTCG
TCAGATCCCTGTGAAAGATGCCCGCGTCGTGAACGTAGGACATGCCGCGCGCTATACCCAGCGCCAGTCTTATCTTCTGCGTGGCGCTGAGCACC
ACCTCCTTGTTGGCCAGCAGCTGCTCCAGGGAGCCGCCGTTGATGTACTCGGTCAGGGCGTGCAGTTGGCCCTCCTGCACGCAAACGCCCATGAA
GCTGAAGCGAAAGAGGAAGGAACACGCTTAGTTAAAGTTTGCCACTGCAGTGCAACTATTCGGTATGGCCCGAATAAGTTTCACTTTCAATCACA
CAACTTGACGGGCACTGCAACTTCGCGGAGCCCAGATTTCTTATCGCCGGTCGACATGCAATCGGCCACCCCCCACTGATTGTTGGCATTGTTTC
AGCCTTGATTCGATGCAAAATGAAATTGTAATTCGAATCCCCCGATGCGGCAGGAGCACGCAATAAAAAGAGAAAGTTTTCCCTTCAATGGACAC
ACAGTTCCTTGGAATAGGGAGTTGGATTGGAATCTCCTAGGATTTAAAGAACAAAGAAACCACTTCCTAAGCACTCATCTCCGCTTCCTGCTCAG
ACAATGTCAATGACTCCTAAGCCTAAGGAGCTGCTCGCTCACCAGCCGCCAACCACCGACTCACTCCTGGCGGCAGCACAATCTGAGGTCACCAG
GCTCTGCAACCGGAACTGTAAGCTTATTAAGAAAATGGCAACGCATGCGTCTACCTTCTTGCTAACTCCACTCCTTCCTCAAAACTGTGTGCAGC
CAGGTAAAAAAAAAGGTGAACTGCTGCCAGACAGGGCTGACGATGATGCTTCAAGGTGACAATGAACTTTAGCGGAACTATGAAAGCATGTCAGC
GTGCACATCATACTATGTATACCCTTAAAATCAGGGTAGTTATATAAAACACATTTGGTTAATAATCATGCTGAGATGTTCTTGTAGAAATATAT
AGAAATAATATATAATATAGCCGATTAGCGCATGTGACTGAAGTCCCGTGCAGGTGTTCATATCGATAAGGGTTCACTTCCATTCCGTCTTCTGT
CAAATGGTCTAATCGGACTTGCAGGCTTTATCTGCGCACATGTTTCTTTTTGGCCAGACCCAGGTTATAGCCATGGCCCAAAAGAGTTGGCCAAA
TGGTTCCAAACTCTGCGTCGTGTGCCAGATAAGCTTTATCGCCTATATAATATATATTCGCCACACTGCCCCGCACAAACTCAAGTGGCGTTTGA
AAAGTTTGACTTACGTTTATGTGCGCGATTGGGCCATTAATTCTTCGCTCATAGTAAATATTTATTTAATTAGTTCAACCGCAGAGCAAAGTAAA
TCGCTAATAAATTTAGCAAACGGTGTGTGGGTCGGAAATAATTGCTTTGAGCACGCAACCCGTCACCTCATCCACCGCAGAACAGACACCTTTCC
GTCAGGCTGTCAATAAGGATACGACAACAGGGTCTCCAGGGTGCGACTGGGCGCGTGACGTCAGGGCACTGGCAATCAAATGTTATGGCCACCCC
GACGCGTTTTAACAACCGAGTGGTCTCAACGCATTAACATACGAGTTGCAAAGGGGTTGGCCCAGAACACCAGTTGCATCGTTTGCCGACTGACA
TTGGGAATCACAGCAGATAGAATCATCAGCGGTCTGCGGGGAAGCTTAATTGAAATCAGTCAGGTCACTGGCTTTCCGGCAGTGAATTCAGGTGA
GGACACTACAGTGGAAACTGTACAAAATAACTTGTTTTTATATACGGCGTAGGATCTGACTATTTAAAACCATTCATGGTTTAAATAAATATTTA
TTATTTCAAAAATTTGGATGGAATCGATTGTGGTATTTGTTCATGAGGGATATCTATACGCTTTTGTAACTCAATTAGTTTGTTCTCAGAAAATT
CGATCTACAAAGGATCGACTGTATTACCATACACAATGCGCTATTACGCTGCATAAAAAATGGAAATGTCTTGGCCAAGAGGGCATGACCCTTTT
ATATTTTCTTGATAGATATGCCACGCCAGTGTGTGGCAGACACATGTCAGCCCTTCAGACAGCCCAAGGGCTCGGCTCGACGCGGATCTGAAATG
AAGTTATCACAAAGGCGAGACAAGCTCGATGATCCCAGGTGTTGACGGCGAAGGTAGGGGCTCCAAGGCCCGAGGGTTTTTGTCTGCCGCACATC
CTCTCCAGCAGGAGAGACACACCTATGCCTCACACCCCCCCCCCCACCAATCACTCTTCTCGCGACTCGTGACCGTGGGTGCAGCATGCCGCAC
TTCCATTTGCATGACCATCGCAGGGATTTACGGTTCTAATTCAATTTATTTCACTGCGTGATACACGATTAGCGCCCCGAGTGAGTGTACCCCCC
ATCCACTCCATGCCCTTTTCCTGCCCATTAGCGGCTTACATTAAGAGGATTTGCCTGCAGTTAACACCTTTAATGTACGCTCTAAGCCATTCTCA
ACTCAACGTGGCTTTGAAGAAGAGATCTGTTGACGGAAAGGATTTAATTGAAAAGCACAGAAACTGGTTTCTGTTTTAAAATGAGAGTGAGGCTG
CCAACATCGTTTGATTGCACGCAAAGTACTTTGTTAATTGGGCAGTTAATTTATAACGCATTCATCAGGCTGGGTGCAATGTTATTTTCGGAACG
CAAAAAGATTAATTAATTATCAAAAGGGGCAAAGGCAGAGCCATTTGCAGTGGGCGTCGCCAGACATTTTGAGGCGGGTTCGTCGACATCAAGCA
GCATTGCCTGCAAATGCAAAGCAGTCAGTAGCTGGCCAAAAGAGGAGGAGGTGGAGGTACCAAAGGCGAAGGTGTCTCCATTCCATTCCATTCTC
TAGCAGGAAATGAATACACGTCGAGGGGCCCACTTGAGAAACTGCAGCTAAAGGATGCCGGGAGCAGGAAGCGAAACCTACTCAAGCGGTTATAA
GCCTCTGAAACTGCCGAAGAATCATTGTTCTGGCAGCGTTTAGTTTTTCAATTTCTTTTTTTTTGTTTCGCCAGCATTTTCGCCAGTTTTCTACC
GTTTTTACCCTGCAGCCAAAAGAGATGTGATGTGGTGTTAAATTGAAATGTACTGCTTCGCTAGGTGTTACAATATTTGTTACGAGCATATTACA
CTGTTTTCCCGGGAAAACGCTGTACGTTCAACAGTCGGCAAATCGTCAGCCGGCATTTCTCTTGCAAGTTGCAATGAAAACCATAAATTGACACG
TTTGCACGTTTCTCTCCCAAGACTGCGCCAATTGGTTTCCCAGACTTTTCACAGACGAAGTCGTAGTAGTCCAACTAAGTCCGCTAACTGCCGCT
GGCCAGGCCAGCTTGGTTATTAGATAGACTAATGAAATGAAAAATCCCGCTGGAATTCTTTCACCCGTGTGTTGCAATAGCCGCCGCCGCCGCCG
CCGAAGCATTTTATGTTGGCAAATCGAATTGGAGCATTGAAGCATTTTGCGCTTAATTGAAAATTATTACCACAACATCAGTGGCAGCAACAGAT
ATTGCAACTACAGCAGCAGCACCAACAGCAGCAGCAACAACAGCAGCAGCGGCACGATCGCGGGGTTAAAAGGTTGACACAAAGTAAACAAAATT

FIGURE SHEET 768

CGCTTTTAGGCAAACAGTAAATAACCCAAGACCAGGCCCAATGCCCAACTTCCAAATGAGACGGTGGCACTGGAGCAGCAGCCGCAGCCGGGGGC
GTGGCAATGGGCGTTATAAATGGTCCTAAACGCTGCCAACTGCAATTACCATTCGGCATTTGCTGCTGTCGGGTAGTAACAACAGAGCAACAGTC
ACAGCAACAGCAACAGCATTGCGAAATGAAATGATTGAATTTGGTTTTCAATTAGAAAAATATGCAAAACGTGATGCGAAAATTATGCAGATTGC
AGCTGCAGCAGCAGCAGCGGCGGCAACAGCAACAGCTACAGCAACAGCAGCAACATCCAACAGTGGTGGCCATAACTTCCTCTTCTTGTTTTCAC
TGCTGACCGATTTTCAATCTAGTGGAAGCTAGTGCAGCCCAAAAAGAAAGCTCATATATCGCGGGGTGTTGCATAAATCTGAATATCTAATGCCC
GCTTTTTGTTGTGAAAAATTGATTGAAGTGTATTGAAATTGATTGAAAGTTGATGACATAATTTCGTGCATACGAAAAACGCAGGCCAGAGACAA
AAGACAATGGCCAAACGCAAACGCAAACGCAAATTGGAAGTGAATGTTGGCAGTCAGCCGGGCCAAAAGACGGGCGAGAGAGATGAATGTTTTAT
GGGACATCGGGCCTGCCTGACACACGTTTATTTACCATTTTACGGCTCTATTTTGTTTAGCTTATTTTTTCATGCGGAAGTTGACAATTACACAA
GTGCGATTTATGCAGACAAATATGAGACGATTTATCGCTGGGAGATAAACTAACTAAAAATCCAGCGGACGCACAGTAGTGAGTAATTGCTGTCA
AGAAACTTGTTACAACACGGCATCAGCAGCACGCAACTTGAGCAAAATAATAATAAAAAACCAAAACAAAATGGAATGCAAGGCAGGCTCTCATT
AAATTCCAATCTGTATCTGTATCTGTATCTGTATCTGTATCTGCATCTGTTGCCGAAAAAACGCTGGGTATTGTGCGATACACATTACTCATGCT
CTTGCTCGTTTTTTTTTTCGGGTACATCAATCCTGCTGCTCTTCTTTTTATACTTTTACATGTGTTAGCACTTACAGCGACAACAACACAATGTA
ATAATAATAATGCCGTGGGTTCAATGACTTGCAATTGCGTCGCATTGTCTTGTGTACTATACATATACATATTATTGTGGCTGAGACATAAAGCA
TTACCAAAATAAATAAAAATAACAGCAATATGCATACCCCAGTTTTGGGTCAGTGAGTTTAGTTGTGCTTGGCATTGCCAAAAAGGCCAAAAAAC
AAAAAAAAAACATCTCCCTTCCCACCAAAGTGGATGATGATCCATCGATAATTGCTGGCTCTATGGAATGCATAATTTCGTGTTTGCTGTAAACA
CACACTATTGGTTTAAATTTAGCACACACCTACATACTCTACGCTCCATAAATAGGCGGCATTCGGAAGTGCTAATGAAAATCCGTGATGCAAAT
ACTGCAGATGCTGATTCAGATACAGATACACTGACGTCAATGCAATTGACGATCGAATCCAAATCGAACACACTGATCACACGGGCGTCTGAAAA
ACAAGCTGCCTAATGAAATTGCGCGCGACAGTTTACCAGGCCATGTTGATCATCAATCAGAAATTAACCCAATTTAGCTTTCTTGCACTGCCTGC
AATGGCAACGATTCGTGCCACACGGCAAAACACGGAGGCAGCCGAGCAGCTTCAATTACAGGCCATCGATCGACAATTGACAAACCCCAATCGAC
GAGCAAACATGAAAAGCTGCGCTGATAAAAGTGCGCTGCAAGTAGTCAACCAGTCTGGCAGTCCCGTCGTCCAGGGTATCCATTAAGCAATAAAA
AGAAATGTTTATATGGCCGCAATCATGACACGCTCTCTTTCGGCCTCATGTTGCTGCTGCTGCAGCTAATGTTGCAGCAGGTGTTGCTGCTGCAA
CTTGTCAAAGTCTAAAAGTCTGGTAACTGTACAAACTACCCGGCGGCCAGAAATTAAGTACTCAATTTGGCCAGACACTAAATCCCCCATTAAAC
TACTTACATCTACTATACACACATATAGAACTTAATTATATATGCACGGATTTCGGAATTCACTCAAACTGCTGTCGCGCTGCATGAATGGCCAA
TTGAACCCATCTTGCACAATAAAATTCTCATTAAATTGTCAACAATTTTTTTTTTTTTTCGCCCGTTCTCGGCAATCTTTTCATTAGCCCGACA
ATGTGCCACCACCGATGAGGGCGCCCATTCAATTCAAGGCCAGCCATCTCGGTTTATTGGCAAGCATTTCATTTTGCTTCGTTTCATAAAAGGGG
ACAGAAATGAGCCGCCAACGCTCGGCGACACACAAATCCAGCCAAGACAAATAATGGCCGAGAGACAACAATGTGCAGTGGCCCCTCGAAAAATG
GAGGCTTGTGGCAAACACATCATCGCATCTATACTACGGTACCATACCATACCATACTATACTATACCATTGTATACTACCTATATGCAGGCATT
CCGCCACCACAGACGACCTTCAAGTGACGCCGCGACTTTACTCATCGCAAGATGAGTGGTGGTGGTAGCTCGATCGTCTGACTGGCTATTCAATT
AAGTGCAATCTGACCTTAGTGAAACCTCTTGCAACGCCAACGCCGGGTTTATATCAATAGCTGAGCTGACTGATTGCTGATTGCCCAAGTCGCTT
TATTGTAGATCGGGGTCAAAAAGCTCAACTGCAACTTGTGCGGTAGAAAGGGTGAGAGCTCAGTGGTCCAATCCGGTGGGTTAGCACCTTAAGTC
ATTAACCCGCGCGCATTTGCATTCGCATGCCAACAATTTGTCAACATTTGCCCGACAACTTATCACCTGCTTAGCATCGCAGCCAGGCGCAAAGA
TCAAGTGCCGCCAAAGCAAAAGCTGAAACAGCAGCTCCAGCGGAATTTCCACCATTGTTTGTGGCCCGTAATGATCCGGGCTAAGAACTGTCACA
TGTCTTTGCGCGGTCTGAGTCGCGTTAAATGAGCGTTTAAATGGCTGTGAGCCAAAGCGGCAGCTTGTTTACCATTCCCCCCCTGCTCGGTTGTT
ACAAGTGGAGTAGTTGTTGTTTCACCAGTTGATATATAAATGTATGTATGTATATACCATAAAAAAAAGGGGGCAAAACAAAGTGTAGAGCACCC
GGCGCCATCAGCGTCATCGCTGTGTTTACATTCAGAGAGAGCCACTCAATAATGTAAGTCAACTTGCAATGGGATTTGTGAGTCAAACGATGGGT
ATGCTGCGCTATCAAGAATTACGTATTAAATATAAGGAGATATAAGGAGATATAAGGTATCCAATAATATGAATAGTATATTATTGCTTAATAAG
AAAAAGATATCAAGGTTATGTGTGCATTTAATTTATGAAATAATAATGCGTAGATGCATGCGTGTCGATGCATACTACCGATGATAAGTAAACTA
TCACGTTAATTACATTTTCTATTTGAATGACCATTTGAATTCATGTATAATTTTGGAGACCAGCCCCTAGAAACAAATACTACTACTACAATTAG
CCACATTTTCGCAGTGCATTAGTGTTGCTGCTGGGGAGCAGAGTATGGAGCAAACTATCTGTCAAGTTGGTGGCAGCTTGGGAGCGGCGACAGCT
ACAAGCCATGCCATGTGGGTGGCTGGGTGCCGTTGCTCCAGTGGGCCAATAGAGAGGGGAGGCGTGCCAAAGGCTGGGCGGGGAATGCCATTCGC
AATTGCCCGACTCGCTGGCTGTTCGTTCTCATTGTGCGACATTCCGCATTACGGCGGCCGCGTGATAAGCCCATAAAAAATACACGCCGCCAACG
GCAACCACTCAACTAACTATCCTCAGTCGAGTGTGTTGTGAGAGTTTCAGTTTCAGTTTCAGTTTTGTGGCCAATAAGTCAGCGATTCGGGCGTG
GGTGTGCATACTATTCGATGCATTGCTGTAGTACATGGCGTGCTGCCGGCTAGAAAGGCGGTTTCAATTACCCAAAAGATTAGTTCTATTGACGC
TCGACTGCATCGGCATTACACTGATAGTCGGAGGATGCAACGGTACAGCTAGTTCTGGCAGCCAATCAATAGGCTTCATTAGCCGGATCGGATCG
GATCGGATCGTAGAAGGCCGCCATGGGAGGCGGCCCGCATGGACGCCCAGCGGTGTAGCTGTTAAAATTTGACAGTTAGCCGACAGCCGCGATCG
TTAGGCATCATTAAACGCGCCCGCCAACAAGAGCAGCGCCTAACTAACTAACTAACTAACTAACTAACTGTCAGTCAACCCGGTCAGTCATTCGT
ACAGTTGATCATTTGGACGACCTGGGAGCGGAGTGTTTAGCGATCCACGTCACTGATAAAATCACAAACGCGGATCGAGGATCGCGGATATGAGC
GGGATTCAATCGGGCGGAACAGGCATAGGTACTAGTACCTAAATGCATACACTGAGACAAATAATAACGCTGTTAAATATATATAAAAGTACATA
TTAAAATTGATTGAAATGCAGCGCTTACAGAATAAGCTATAAATAATTATAAAGCATCTCATTTGAAGTGCTTAAATAGCTTTAAGGTGTAAAAT
AAAGTTTGAAAAATGAAAAATATTTAAATCCTGTTAATTCCAACATATTGTTTTTGATTGCAACTACTTGTTCTCGCAGTGTCGCATTAATTGGC
CTCAGTGTAAATATATAAATAGCTTTGCTGCAGGGGATCCATAAAACAAAGAATTAAATGCGTGCGCCTGAATTTTAATTTCACTATCCAGTCGA
CCGATGGCGCCACAGCTGCATTCCAGAGTTTTTAGAATTTTCATTTAGTGCCGACGAATAAAGAAAAGTTGGCAGCTGCATGGATTCGCTTTAGA
CTGGCTGTGTTCCGCTGACCCAAATCCATCTCTCAACGAGCCCGGCGCACACAGCGAAATAAGTTGGCCAGCCAGGGCATTTAATCAACAGAATC
CGTTGCATTTAATACCCCGACCGCGATTCGTTGCACGTTTCTCACTTAGCTCTGTGTCAGAAACAGTCGCTAATGACAGATGTCATAAAATCAGG
TGGGCTCTACCAATACTAACTCTTGGAAAATCCCGAGTGAGGTCAGATCAAATCGCGTTGCCTTCTTAACGTTTAATCTTTCGGATTATACGAGT
TTAAAGTTTGAATGCCTAAAAAACAAAAGAATGGCAGCTAATATAGAAGACATGTCTCTTGCCATTTTCGGGGTGTTAACGTGGTAAATGAAAGG
GCGGGTCCACAACACACACACACACAGAGAGAAAGAGAAAAAGGTCTTAGCCAGAAATTGCATATTCATGGAGGCGAGCAGGAAAAGATGGGCGG
TGCAAAATGGATTGGTCTGTCTGGTCTGGCATTTTGCGGAAAAAATCGCTAAAATAGAAAACGGCAACAGCAGCAGCAAAAAGTCCCTGAGAATT
GCATACAATTGAAGTCGCTGCCATCAGACACTCATTGTTGCGTGCAGTCACGTGAGGATGAAAAACAAACTGAAAAAATAGTAGAAATATATTCG
AAAAAACAGAAACAAAAAACAAACGCCAGCGAAGTGAGTAAGCTCTACGCAGCTTGGCAATTAAATCTAGTCAGGTCCGACAGACAACAATGTCA
TGAGCCTTTGCCATATTGTTTCAGACTCTGCCACTCAGCCAGCCAATTACATCAGCAGTTTGTTTTTTTTTTTTCTGTGACCCGTGAGAGGGTCC
CCCCCCCAAACTCTGCTAACCCCCCAAACCCACCCAACACACCTGGTCACTGCCAAGGTAATTACACAGCAGAGACTCTGCTGCAGCCTGAACTT
GACCTTTGCGCGAGCATCGGAAATGTGTTGTGCGATTTTGGTCTTGAACCCGCTGCTCTGAACTCCAACTGGGGGTACTCTTTCAAAATGCCAAA
TAGCAAATGGCCAGTCGAAAAATATAAACAAATCGGCGAAACCATAACAGACCAATCTCATTGCGGTAAACAGTAAATATTTGCACATTATTAAT
TTGAAAGCACTCATGCTGCCATAAATACATTTGTGTGTAAAAATAATATCCATAATGATGTCAGTGGAGTGAGCGGCCCCAGAAGCACAGATGTC
AAGAGTTACGACGACAGGCTGAAAGTGAATCATACCCCTCATATACTACATACATACATACATACATATATGATCATTTCCATTTTAGCATAGGT
CAGTATTATTTTGATGATGCCAGCAGAAGCAGCCCCTAACCTAAGTGCTGAGAAATCATGTGTAAAATATGCCAAAAACTGAATTGAAACCGACC
GAGAAGAACATGGGCATTATTTGCGTAGAATTTAAAATAAAGACCCCGCGCGATGAACCCATTAAATTGTTTACGTAATCCATTTAAATGAATGG
TCAATTCGCGTCGAGGTGCGAACTGAATGCGTAAACACAATCGGGCCACATGATCATCAAAAGCTAAGGGGGGAGTAGTATATATGTATATATGT
CAATATATGTGTGTGTAAATACATATTATCATCCAGAGTGGACAACAACAAGTAGCATTCATACATAAATAAGTAACGCAGTCAAGTTTGCAATT
AAAATCAGTGAATGAGTCAGACCATCGAGTTTGGCATTGACCCATAAGATGCTTTGGCTTGCTCGCGATTAGAATGGGTATTTTTAGACGATAAG

FIGURE SHEET 769

CTGGCTGGACCACAAACTTCATATTATAGACCATATAAATATAATATTATAGACTTACCTCAATATATTCGCATGCGAAAGTTTATTCAACAGCT
GCACCTCCCGCAGCATATTCGGTCGATTGGCCCGCAACTGATTCATCTTGAGCACCATCACCTGGCCGGTTGTACGATGTGTGACCTGCAAAATC
GGAATCAGCAAACAGAAATCAGTATAAACATTGCCAAAATCAGAAACATGAAAATATATACATATATGTAGAAGCAGATCCATAAATCGTTCTGC
CAGTCAGACAATTCAAGTGCAAAATGTGAGGACACGACTAAACTAAAAACTGAACCAGGTACAAAAACACATGTTCGAATTCCAGGGTCAAGTTC
GCGTGGAAAGTTGTTGGCGAGTGCAAGGCAAATAGTTCGAGAGCTGGTGGATAATTGCATCGAAACAAGTGAGACAACAAGCAAAGTGGTTTTCA
TGGATTTGTGCAGACCAAATGAAAAATCAATAAACCCGTCTAACTGTCTGCGCTGGCAATTTTTGGTCCAATGCAATTTGATGGTCGGTGGTTTG
CGCGCCAGAGAAGTCGTCTGCAATCACAATTAAAATTGTTAATTGAATTCGCCTTTTCCAGATGGGTTGGGTTGGTAATAGGTACATACGCCCAC
CAAAAAGGGTTAAATGTCATTTGGTATGTAGGTGCTATTCCTGTACATCTACACTAGAAGCAGAAATTAAATTACTTAATTGAGTTAGCAAATTA
ACCCCAGGCTAGACATCGTTTAAATCATCTTACAATATTCTAGACGACGTGTGAAAAGGTTAAAATATTTTAAAATAACCTAGAACTGTTGCCAT
CTAAACTTGAAACCAAATAACAAAGAACATTAGTATCTTTATTTGAAGATTATACTTTAGATTTAAGAGCGACTTTTTCTCAGTTTCGAGCTGGT
CGTTGGGCGTCTGAGCCGGGATTGCCACTTGGCGCCAGACAACATTATTCACAATTCACTTAAACAAATAGCCCCAAGTTGCTGCCAAAGCACAC
ACACGTACACACGAACAACACTCGTTTTTATGTGGACAATGGCAACTAGTGTTCAACTCTTCTTGAATTTTAGTATTCTATTCTATTTTTATGCC
AACAAACACACTGCAAATACGTAGTGAAAACAAACAGCAGGCTGTGGCACTTCCACACACTTCTATTCCTTGAGCGCGAATTTCTCGGCTCTTTG
CTAATGGCAGCAAATTAAGTTTCCTTGTCCCTTGCAATTCGCTCGAGCGGAATCTACATACATACATATATATATATATAGATATGTAGGTGAGTAA
GCTGATACAGGCCGGATGGATGGATGGCTGGATGGCTGGATAGATAGATAGGATACGGGGACACTTGGAGACCGGGAACACGTGTGCGTGGGTG
ACACACACGACGCCGACAACTACCATGCTACCATTACCTGCAGTACCTTTTTATGTGTACAAACAACCAAGTCGTAACCAAGTCATTCCCAAGTC
GTTCTTTATTGTCCTGTTGCGCTTTTAGCTCATTTCGACTGTGAGCTGGCCTCCATTCTCTATCTGCTAGCTGCCTTTGCGTCGGTGTTAACAAA
TTTATGAAGTTTCTGTTGCCATTTGCTACAAGATATTCGCTTACGCCCAGCGGCCGAAGTCCAATTCACGGCGGTCTGCAGTCATGAGTTGTTTG
GCTTGTTGTCTCCGCCGGCAGCAGAATGTGGCAATCAAAATCAAAAGCAGAGGGTAAGGAAAAGAGGTGGTTGCCCAGATTCTTAACTCGGCTCA
GAATTCGATTTCCGCTTGGTGTCACTTTATTTTCGGCTAGCTTCTCATGTCATTCGCTCATTTGCTTATCTGCCACTCAAAAAGCTTTCAATATA
CTTATAAGTTATATTTATACCTATATGCTTTCCGCAATAAAATCACCTCATAATGCTGACACACCCAGCCGGATGGACTCGAAAAAATATATTTG
CAGTAAGGCAGTTCTCTTTTAAATCGCTGCTGTTCATCATACATATATCGATTATAATGGCAAGACTAATTTTGTGAGAAAACCAAATAATATAT
GTAATATATATTAAATTTGCAATATCATATCTTATCTATCATATCAATAGCAATTTCTTTAAATAATTCATACTTTTATCTATGATATAGGGGAC
TTCCATGTATTTTTCTATTTCTTTGAAATCTTGATTCCTGAAAGTTTCCCACCTAGTGAGGTCTCACTGTATTTCTTGCTTTAATTGCCTAATTA
TTTGTGCGTGACCAATAAAGTTGATGGCTTTACGTCCGTTTGCCAAATTGATTTGCATAAAACGAGACCGTGTACCTTACAGACAACATTCTGTC
ACACAGCCCTGTCATCCCGAGCGACAGGCCATCAAAAGGGCCACTCCCCAAGTGTGTGTGTCCATTGAGTGTTTGCCGGGACAATTAAACCATTA
AATGCCATTTTAGAATGCTTTCGAAGCGCTTAATGAGCGCTGCAGATGAAAAGCGGCAGTGCAGTTTCCACAAACTACGTGGTGTATTTAACCAA
AAATGTTCGAACCGTTCGTGCCGCAGACAAAGCGAATGAGCCGCCTCTCCTCCGGCTGGTGCAGTGGACCAAAAAGTGGCACGTCCGTGTTCCTA
AGTCCGAAGAGCCAGTCTCTGCAACTGTGCTAAAAGAGAACTCACTCCACATCCATCATACATACATATGTGAGCTGAGCTGTGTGTGGATTGAT
CTTTTGCTCGGCGGCCAGCTTCAAAGACTGTCCATTTGGTCGGTTGGTCGGTCGGTTTCTTATTGAAAAGCGTTTAGGCCAGCAATGACGTGAGA
AAAGAATTACCCACAGAACGCAAACATACTCATACATCATAGCCCAGCATCGATGGGCTTCCAAAATAATCAATTACGGGCGAAATCCGAAAACG
AAGGTGTTCCAGTGAAAGAAACCACCATTGATCTGGGTCGTCGTCGCCGTCGTCGTCGTGTGTGGGAAAGTTACTCCCAAGATTGGATTCTA
AAAGCTTTTTAGCAGCTTAGAAAAATCCAGGAATTTTCCCCCGAAATTCATCGTTTCATTTTTTAGCCCCAAAATGTGTGATAAACAATAGTCGA
ACGTAAACAGCAGAACAAGAAATCAATTATGAAGGCGCATGAAGAGCATTTTCAACTTATTGGCTCTGTTTGCTTATTTCGAAGCATGGAAACGC
TTTTAATTTTTCGTTTGCACTGCAAATAATGTCCAACTTAAAGTTCCGCCAATGAAGACGACCGGCCAATAACCGCAGGAGGTGAGAGTGAAGTC
ACAGTTGTGCGTTCTGCGCATTCAAATGAAACGCATCAAATGATTATTACTTAACCAGTTTTAATGGCCAGCTGAGAGGCTACTCATCTCATTGG
ATTGCATCGATGGTTATGTCAACAGGCGGCAGCAAGTCAGCAGGCATTTCGGCATGCAAACAAATTTCTTGCCTTTTGCCGTAAAATACTCGTAT
TTTCACTTTCAGTTGGGGCAAAAATGAAAACAACAAAAACAACGCCACAATAAAAATGGTGGCGGTTGCGGAAACAAAACAACAACGAAAGTTGC
CGCACCAGCTCGCCAAAAAAAAACATCCTTTTTGACCAAAAGTCCAGGCATTTGGCCGAAAACCAGTCGCCACTCACACTGACATTTCGGCCGG
CGGAAAGGAAAAGAAAGATGCAAGCAAAAAACCAACAAAATATTGGTAATCGGTAGGCAGAGAGAGAAAAACCCGCTCATTTTTTGGCCTGTAAG
CGCGCTCGTTACATACTCGTGATTAATTTTGTTGGCCAAAAAACGCGTTTTGAGCCAAACGGACGCGGCATGGGGCACACGTGTGACATTCGATC
TTCGACTCGATTGCACCGGCTACCACCAGTTAGTTAGTTGCTTTTGGTGTTGAAAATATTCCAGCTATTTACACGGCGTTGTTGCGTTTTCGTTC
ATTTTGCTGCTTGACAAATACTTAATGCGATTTACAGTTGGGTTTTTTCATTCACCAGAGTCAGAGCCATGCCTGGTCAATCATCTTTCACATGG
TAGGCAGCGCGTTGTGGCAACACCAGTTAGCGGTACAATGTCACCGGCGGAACGGCTCCGTAGTGGCAGTGAGTCTGGCCAAAACGTGTTCTGGC
ACACTCCGTCGCGTTTTCACACCGTTGCGCGAACCCAAAGCCCAATGCCCAGAAATACGCACTCCGAGACGACAGAGAAATGTCGGCTAAAACC
ATGTAGTAAGACAAATATTAGGCGAGGTGTTGCTGCCACCAACTTCTGGTCATTCCCATTCCCATTCCCATTCCCATTGCCAACAACTTGTTGGC
AGGAAAAGAACCAGCTGGCGAGCTGAGCGATGGAAGCCGGCTTTTGAATGGAATTTAACCCAGTTTGCTTTCTTCTTTCTCGCTGGCTGGCAGAT
AGCAGATAACTGCTGCTAGCCGGCTTGTTGTCTTCATTTCTACCACGACAACTGGCTTTTCAGTTTTGCTTTTGGGCGTCAGGGGCCGCTCTAAC
TAAATGGCCTTTATATTGCTATGGTCAGTTATAACGAGCCAATGCAGAGAGACAGGTGACTTTGTTTGGAAATTTGCATGGAGCTGAAATCGGGT
TAAATGGTATTAATATTGCACGCTCTATTGTCACGAGAACGAGCCAAGTATAATAAGGATTTTAACCTAAATCTATCTTATAAGAAGTGTGTGCT
TCAAGCTTTTTAATTTACATTTGCCTATAAGGTATGGTTTATATCTTCTTCACTTATGGCAGAACTAAAATTAACCTTGACAGCTGCACTGACGT
AGGCACAAATATTTTTAGACATTATTTGACCGTATCAAAATTGTTTTAGCCTTATCTGGCTGAACATGAACATATATAAAACCTACATATTCTCT
GGTTATATCAGCACAGTCAAGTACTAGGATTATAATTCAATGGGTAATCTAATCAGCCTAGCTTATCATCGGCAAGTATGGAAAGTTCAACTGCC
CAAGGGCAAACTTATGATTGGGCCATAAAAATGCATCCGTTGGCCGAAGGGATGGGATCCCCAATTAATTAGCCAAAAAGCGAGAGAGCGAGAGC
GTGTGCATCAATCACCATAAACGTTTATTAAGCCGACAATAGCGGAACACAAGTGCAGATAAAACTTCAGCCAGCCAGCGCCAAATAAAAGATAT
ATATCTCTCTATATTATATGCCCGGGCCACAAACAGAGTCGTAAACAACGGCAAAAAACCATAAGCTCAAGTGCCGTTTTAAGCGATTTCGAATT
TGGTTTTCATGTGAAACGAGCGGAATTCGCTGTTGCACCTTATACATTCACACCATCACTATTGCTTTTTCTTTTTTTTTTCCAAATGCTTTAAT
TGGGCGGTGGGCGGTGCAACATGTGGTATATGCACCATGTGTGTGGGCGACCAGGAAGTTGTCCGTGTTGTCCATTTTGAGGAGTGCAAATCAAA
GAATATTCGAGGCTGTGTGCTGCAAGCTGCAATTATCGGGGGCAAGATACAGTTTCAGATTTATGCAACCTTTTATTGAACTTGTTGGATAATAA
TGTGTGTCTGTGTGTGTGTGCCTCGGACGTCGGATGATTATTATTATGGTTTGTGGCACCGTGTGTGTTTGTGCTTTTAATTGTTAACGGAAGCC
TTGGCGCGCAGTTATGCAAATCTTTTTTGCTTTAGTTTGGAATGTTTGTTTTTTTCTGTTTTGTGTTGTTGTTTTTTTTTTTTTTCAGGCGTTTA
CCGTCTTTTCTTTGCCATGCAGCTCCTGCCTGTTGTTTCACCTTTTCCTTTGCGGCACAGCACATGTTTAACAAAATTTTATTTCGTGTTAAGCA
AATAATTTAGCAAAGTAAAATGTTGTTGCCATTAGATGTTGCCGGGGCAGGAAGCAACAACGGCAACAGCTGCAGCTACAATAGCAACAGCAACA
TCAGCAGCAAGCTCACGCATATTGCACAACTTTTAGTGGGAGGATGAGGTGGGAGCTGGCAATTTCTTTTGCCAGTCTGTTTTTTTTTTGTAACA
ACAGCAATTATTAGCTGTTAGTTGTAGGCAACATGGAAATTCGATATCAAATTGAAAAAACCCGAGGGGTAAGGAAAAGCGAATGTTGTTTTGGC
GGAGGCGGGGACAATTAACGCATACTAAACTAAAAACCGCTATGCATCACGAACACGCGGAAATTGCCAGTGCACATCTCATGTATTTATCAGCT
AAGCTCAAAGTAATAATAATAATAATAACAAACATTGCATAATCAATTAAATCTGACAAGGAGGCCTCACTTGCTATCAGCCTTCGAGATCACCT
TCAGCAGTTCATTGCACGTTCGTTCGCTGGCTGGGTAGATGGGTTGGACGACTAACTGCCAGTCGGTCTATAACTAAGTATAGTTTAATGGCCCA
TGTTATGTCACCGTCATCATCCTCGTGCCCCTGCCCCTGCCCCTTCCCCCAGCCACTGCCCATCCATCGATTCATTTTAAAGACCCCGTAATGCT
GTTCTCACGAACTGAGAGACTCTAGGACTCTTGGCTTTAATGACATCGGACGACAGCAAAAGTTTACGATTACACGACCGGCGTCGTTTCTCGGC
CATAAAAAGCATTCAAAATCGAACACGTTCTACATATTGAATTATAACAATGTCACACAATAGTAACAATCCAGCCATTCCAGCTATACAACCGT

FIGURE SHEET 770

CATGTGTAGGATGACTCGGCAACTGGGGTATATTCTTTTCAGTTTTCAGTTCCAGCAGTTTGAGGTGGGTCGTATCATACGACTTGCATACGCTT
AAGGGTTCGTGAGCGATATCTTTGGGAAGTGCTGCTCCTACTGCTCACCTCTGAAATTAATAATAAACTGGACTACGACGTGCCTGCCATGGATA
CGGAATGGCTGTTTGTTTAGGTGAGGCGCACGACGACGACGACGACGACAACAAGACATTCTTGGCTTGGATCGAACCTGATTTGTTTATGGGCTTGC
CCAGCTGCATATTTCCCCCTAGATCATTCGAAATCACTCTAAACGAAGAGAACGTCGACGACCCCCGCCAAGACGAAAAATTATAGTACAACTAT
TACCTATTACCTATCCGCCGATCCGAAGGTCATAATTATTCATATTCGTATTCTTGGAGATATCAATCATTTGCGGTTGTGGAATGTGCTGAAAT
GGGCAATCCGCTATATATATATATATAATGACTTAATAATTTGCCGAACAATATATTAGACTGATTTATAGTTGATAGAATGCTATCTCACTCCGGC
TTCACCTCTATTTGTGTACTTTACGATACTCCGCTATAGCAGACCGTACAATAATAAAATTAAAAGCCGCTTAACTTGTTTACTTTTGCATCAAT
GGCATGGCAAAAGACATAATAAATGGGTTAAGCAAACACACTCTCACAAACGCACCTCAAAAAAAAAAAAAATAAAATAAAACAAAAAAAAACCAG
CAACGTCATTAACCGACCCCACGTTTCGGGCCCGTTGAGTGCCTTCAGATAGTCGAGGGATCTTAGATTGCAGATTGTACATACATATCTATGTA
TATATATATGTACATATAACTAGCACTATTCACGTAGCGATTGCATGGGCATTACGCTTTTCAGTTATTTCGTTTTCTCTAATATTCGGCGCGGA
AAAAACTCCCCAAGGTAGTTCCGCAAAAACTCTGTCGTTTAAAAATTTTAACGGGGTGCCTTAGAAAGTGTTAGAAACACCACTCACACGACTGA
GCTTATAATAGACTCACAGGGGAGATACATATGCATATATATTCAGAAATTATCATAAAACCTAGTGCACTTTTATAGCCAGTCGGTATGATGCA
AGCAAATGCATTCCAAACATGTTCCTCTTTCCGTTTGTTATCAGTACACGTTAAAACTTCTGATACAAGAACTAAAGCTACAATCCATATTTAT
AAGCACAGTGCCATTGCCACACCGAGTATGAGAAATAAATTAATCTTCGATACATGGTTAAGGCAATTAAATGGATAAATGTAACACAAAATCAA
TTAAAGACGTCTTGTTGTACATGAGCAGCAGCTATAGACACCTCTATATATATCTATATATTTATATATATATATGGGTATATGTATCTATATCG
ACAAGTTGCCGCCTCTAACAAACTGTGCTAAATACCAGAAATGAAATAAAAACAAAAACCGCACAAGACAGTAGCAAACTGTTAATTGGATGTGG
CGACTGTCAATCGATAGGTGGAAGTGAAAAGCCAGAACTGAAGCGTAGATACATATATGTATCTGTACGACTTGCAGTGCGTTTTTCAAGTACAT
ACATACGTCAAAAAGGGGAGGGATTAGGAGGGGTGTGCTGCAAAATAATTTGACCTTAGAGCCACTAAATTGATCGAATTGCCAATTGAAAGGGG
CTTCGATGGGGTGGAAAATACACAAACAAATTTATCGAACAGAGAAGCTAGTTTTTCAGTTTTAATTTCAAACCAATCCATTCGATTCTACGGC
GCCAGACAATCCCTTCTTGCCACTAAGCTCTTTGATCACTTATGCACGGCGAGTAAGTCATACAATTTAATTGCTTTTATCGCACGCCTTAAATC
GCAAACATCAATGGATGTGGGCTCTGTCAATTAAATTAGAAAAGCACGCGTGTCTGTGAGTAGTACCTTTTTGCCACACAGCAGTTGCACTCACA
CACATTCACCACCACCACCACCAACAACAACAACAACAACAGATGCATTTGGCCAGTTGTGACACGTCCCTGTGATTAAAATCAACATAAAATCC
AGACACACGCCTTCCGCTGGCTTACCCATCCCCATCCCCGTTCCTAGGTTTTCATTAAATGACAACAACAAGCACTTCCGTTTCCATCGCTTTTC
TCCGGCTATTCGACTAAGTGTGGCGCATTTGCCATAAGCAGTCCCAGCGCCCATGTCGCCACCATTCCACCATTGGCCCAAAGACCAAACAGTCC
AAGCCGATCCAATCAAGACGACTTGGGTCGCTTCGGATCGGATTGGATCGGTGTCCGTTGCATGGTGACCATTAAAGGGTCACTGGCATGCTGCT
GGCGATTAGCACAAGCAAGATGCCATGCGAAAGGGTTTTCGCCTCCCTATTTGGCTAGAGAAAACTCCGACAAGATGGGAAAGTTGCAAGGCAAC
ACAGAAATGGGGAATACCCTATCTTTGCTCAACTAAGAGAGATTTATAGAAGTTTTTACTATCCTTATAACCTTATGATAATGTATGTTACTATC
CACTTTAGAATCGAATCTTTTAATATCCTTTTAAGGCTGGCAAGGATCATGAGTGTCCATCTTGGAGAAAGGGTATTTCAGCTAGAGAAACGACG
AGTCTCTTGAGAGATCTTTGGCACAAAGAGCTGCATTCGAAATCCACGCAATTTCCATACCCAGAACGGCTCGAACTTTGTCGGCTTGTTAAGTG
CGCGATCGGGTACGAAATGTAATTGGTTTGGCGCGTTAATAATCAATTGGCGTTTACATTTTAAATGTGGCATGCCGCGGACAGGGAAAGGCGGC
TGCGTTTGTTCTCCCAGCGAGACACCGAGGAATGCCAGCCAGCCAGCCAACCAGCCAGCCAGGCCAAACGGAGCCAGCACTCTAAACTCTCCATT
GAGATCGTGGCGACGTCTGCCCTTGATGAAGTGCCACATGCTGCCGGTTGCCACAGTAGCCAGTCCGTATGATGGAAGACCCTTGCCCCCGCCCT
TTTCTCCCCCCGCCACCATCACCGCCAGTTAGCGTTTGTGCAACTCATGTCAAGTGGGCCGGACTGGTCGGCGACTACACGTGTCGCCCAACGTC
ATCGCCATCGCCAGCACCCAACTAGTTCTAATCGAAGCCGGATCGTATTGCACGTTAAAAAAAGAATATCAACTACATGGATAATAGTTTAAAAA
ATTGGGTTATCTTTCAATACCTATTTAAGATTTTAGTTTGAGCTTCCATTTCTGTAAGCTGAATCAATCTTAAGGTTTAAAGTCTTTAACTATT
GTATTTTCCAAGATAAGTAATTCAATTCCTGAGTGTTAATTGAAGATTACTTCAATCTGAAACTGATTTTACTTAAAAGTGTCAACTTTTGTGAG
GAAAAACTTATAAAATATGTGCAAAACTTAGTTCAAGTCTGCAGATCAGATCATCTAAAAGCCCTCTTTTAATCTGTTGTAATGTTCTGTTAGTT
CAATCTAATAAGATTTTGTTCTGAGTGCAGAAACCAGTTGGACTGGTGGCGATTGGTGGCGTTTCAAGCTCAAGTCCATCAATCAGCGGCTTGTT
TGGGAGCTGAGTGAGCCATGGGCTGCAGACCCGGGCTAAAATAGCTTTTTAATTGTCGCAAATATTTATAGGAAATTTCTCACGCACAGCCGAAT
GGAGTCGTGCAAATTACCTGGTCTCAGTTACCTCAGTAGTCACTCGAATGTCGTGCAATTAAATCCAAGGATTTGACAATAAGGAACGAAAAAAA
GCTCACCTGAAAGCAGAGAGAAGGAAAAACATTTATTAATTCGGTGCTACGCGTGCGATGGCAATGAACTTATATTCGTTTAACAATCTACTTTT
GATAATTAAAATGTGCGCATAAATTATTGTACACTTCATGAGCAATCAGAAACAGAAACAAAGTGCAAACGCTCCACATAAAGAAAGTAGAGAAG
AAAGAAACATAAAAACAACACACAATAAACAATTTAATTACGCATCGTTTGTGCATTGAGTGTATAACCCGCACAAAAGTGAAATGCAGTTATAA
ACACTCAAAAAATGAATAATCTTATATTGCCAAAGCAAATAAACAAAGACACGGCCCACAACAGTTGGCTGCACATTTCAAATTGGCCAAGAGAG
CGGACAAGTAAGCCCCGCTACGAATTCATTACGTTTTCGAATGTGAGAAAATTTTCGAGATGAATTCCTGACTCTAGTCGCCTGGAAGTTTTTTA
ATTCATAAACACGAGGGCAATAAATTACTTTGTATTGGAAAAACCTACGCAGATGTGCCTGCTGCTTACATGTCGCGTGTTAGTTGGTTCAAAAA
GAAAGTCTGCACTATATATATGATTGCTTTGTTTCGTTTTCCACACCATTGTTAGTTAGCGGTTTTCCAAATATTTCAGCTCCTTTGGCAAATTA
TGTTATGTCGAAATCAAGTTTAAAATAAATCAGAAAACTTAGTCAAAAAACCCAATCTCAACTGCAACATCTGCATAGCATCTTGTCATGTCGCT
TGTCGCTCAACTTTTCCAACGCGCTCCTCCTCTGTTTTTATTACTCCATTGCCGCGGAGGGATGGATATGAATGGTTGAATGGTCGGATAGTTGG
ATGGTCCAATGGCTGGATCACTGGATGGGTGTCTGACTGGAGGAGAGCCTGCGACATGTCAACTATTTCAAGGCTAAATCAGCGAGGCAGTCAGT
CGTCGTGTGTCAACAGTGTGTTTCACCCTCGCCAACCGAGCGAGGTCATCGAACTCCGGACACTGCAGCTCGGATTTATGGAACAAGTCGGAATG
CATTTGCCTGTCATTTCGTTAATTGAAAGTTGGTGACAACAAACAGCAGAGGCAGTCGAGAGCCGGGTCCCGTCTCGGTGAGTAATTTCATTTGG
ATATCCTTCATTCAGGCACTCCGAATTACGGCCCAGATGGAATGCAAACAAATAAGTACAAGCAGACTAACTAAATGCAAACTCGCAATCAATTA
GAACAAACAGAGCTCTGTTTTTCCCAGGCCCATTTGGCGACTCGTTAAAATAGCTTACTCACAAACAAGCACCGCGCCGCACCCTCACTGCCACA
AAAAAAAATGTTGCTCATTATTTTTCGGTCTTTTAGCGTTTTTTTGTTTTGGTTTTTCTGCTGTGTTTTTCCAATGCGTTCGAAAATAAATAAAT
AATAATAATAAAGTTGCACGACACCCATATTCGTATGAATAAAGGCCGAGTATCTCGAAATTTATTTAATTTTGTACCTCTTTTTTTTGGGCACA
TTTGCTGGGAGCAGCCGTCAATTCGTCAGATGCGTTTTAGTTGCCTCATAAAAAAAAAAACCCAGTCTGGGCTTAGAAAATGCAACACAGGAAAAT
AATAACATTTCGTGGTTTCTGGCGCCGTGACAAATTTAAATGAGCTCTACTTTTGGGTGCAGCCCCTGCGACACCAAAACAACAACAACAACAGC
AAGTAAAAAAAAAAACGAAAAAGGGGCAACAGCATATATATATATAGTCATAATAATGGGGTCATATATTACTAATGTGTTTGGATCGCCGGCGTC
TGCCCGAAGCTCCAAAATGAATCAATGCAAAACTATGAAATGCATATCGCAACGACAGCAACAACAACAGTGACAACACAGTTGACAAGCGCTGC
CCGCGGTGCACAGTGGTCAAAACACTTGAATTATCGTGTAAAATAATAGTAATTATAAAGTTAAATCTCTTGCCATTGCTAAGCTAATAACAAGA
CAATTTTATTGTAAAAATCGTAATAAGAGATTATAAAAACCTGTTAAGGGTCTAAAGCTAGTTTTTCCACAGTAGCTATTGAGTAATGAATTGTT
GAAATATAAGCTATAATTTATAATTGCGTATAACAATTATCATATACCCATTACCGGACCCACTGTGCTGCAACACGCTGGCGATGAATCAGTTC
TACAGCGGATGGAGGCTGGGCAATCATCGTCGTCGTCGTCGTCGTCAAGGGGCAATATGCTCAAGGCCTTGTGTCAGAATGCATTTTTATGAATG
AACGCGCGAAGGCATACAATTTACACGTATTGAGTGCGCTTAAATGCTCCGCCAATCGCCGGCGAGCGAAACTGCTGCAGATAGCTGGGATCTCA
AAAGCTAAACTATTTTTGCCAGCATCCTCGATGATTTCGAAGTTCGCCAGAGTTCGCTGAAAAGCCAATGCAATGCAATATGGCTATGAGATAGC
GAAGTGCATTGAACTCCGGCCATCGGATGGATCAACCAGTTGAGCAGTCAAACAAACGTTTAAACGCTCAACAGTCAATTCCATGCGACTCCATT
CAATTCAATTCAATTCAACTTGATTCGATTCGAGTATCTGCTAAAAGCAGATATTACCAACTGGCTTTGGCCAGCCCGTTTTTTGGCCGTTGCCT
ATTTGGTAGGATATCGTGTTGGCCGCGGCAGTTCGCTTTTTGGGCGGCCCCATCCTCCAAAAAGCGAGTGAGCGCGCCCAGCCGGTCACGTTTCA
ACTATCAACTGGAAATGGCTTTTTGATTGGCCATCCTCCCCAGAGCAATGCCTATATAGTTCTCGAAATGCGGAAGTTATGAGCCTAGCCAAGAT
TAACCTGCGCCCTCCTCCTCCTCCTCCCTTCGCTAATGGCGTATATTTTCTAATCAATTTTCGAACACACTGAAAAGTGCCTTGCAGCGTTAAAT

FIGURE SHEET 771

CGATAAATTGCGATGGGGCAGCTATATGTGGCGATGTTGTTGCTGCTGGTGTTGTTGTTGTCTTCCCCATTAGACAACAGGCTGTGCAATCTTTA
GTGTCGTTTGTCACCATATTTGCCACTGCAGTTGACACTGATGGGGACCAACAACCGAGAACCACACAGAAACCCACCCAGACAGCCAGCCTCT
CTGCTGTCAGCTTCGTCTGGGTCTATGTTTGCACTGAAAGAAATGCACTTGGAAGTCGTATTTATGGTTTCAATATACGGAAACCTATATAAAAG
CTATCTTTTTATGCATTATCAATATGATATTGATTTGCATATGCAACTCCCCCGTAAATTCAAAATTTTCCCTCAGTGCATTGAAGCCACCACCA
AACTTGTTGCTTGCCTGCGCCCTTCATTAATCGTGAAGCTGGTTGGGAAAACACAACTGTGTGTGCGGTGATGGCATTTGATGTGATCCTGAACC
TGCGGGCTCTGACTGACTCCCCTGGGTGGTGGTGAGCACAGCGCAGGTTTTTGGTTGGAATTTGATTATGCACCAGACCAGAGCCAGTGTTTGCA
GCAACAAGAGCTCCCCGTACCATTCCCATTACCATTTCCTATTCCCATTCCCATTCCCATTCCCTGGTTGCATCTGCGCAAAAGCGTCGAGTGCA
ACTTGTCATTGTTTATCTGCTGTGGCAGTGCCAAACGATAGCTTCGGCTTCTGCTTCTGCTTCTGCTCCAGCTTCTGATTCTGATTCCGCTTCCG
CTGGATGGTGGTGGAGCTGAGATGTTCCTGCTGCAGCTGCCTACAATGCGGCTTGCTTGTGCCATTTCCATTTCCATTTTCTTTGCCTGCCCAAA
TGTGCGCAACTGCAGCTTATCTAAAAAAAAAAAAAAACGAAGGGGCACAAGAAGGGTTTGGCGAAGCCGGGGTTCCATGTCTTGCCATTCACCACT
GCTTCTATTTAGGGTTCTTCTCTGCCACTGAAGAGGCGGCCATAGAAGTGCCCGCGTCCAAAGTTCTCAGCTGCTGCTAATTAAAAGAGCCTGCC
AGAGACAAGATACAGATACATGCGGGATCCACTGCGAAGATCGTGCACAGCAAGAAAAACTGGAACCTTTATGCTTTACATATGATTTAAAGCAA
AGAAGAAGAAGTTCTTTCATTTGTATTCATTTACATTACTATTTTACCATATTGTTATTAGACTCGGTCATTATATATTTTTTCAGATACTGGA
ATCATTTGATTGCAATCTTTTTTCGAACAATTGCCGCAGTGTGGCTTAGTAAGTGATATCACAGAGAGGCATCACCCAAGACACAGACAAAACAC
GAGCTGCAACTGCAACTGCAACTGCAACTGTAACTGCATCTGCAGCAACATCAGCCCCAGCAACATCGCAAGCATCCATCGCAAGGGGGCAGCGC
TTGGGTGGCAGCCTGTTAAATGCATTTGCTGCCCTGACCCCTATATATTGTGACTATCAGGCCATTTGGCGGAAATTTAAATTTAATTAGAGCGC
TCTGCCTCTGTCCAAGATGTCCGAGAACGGAAAGCACAAACTCCGGGACTCCGGGATCGTAGTATCGCAATCGTATCGGTTCGTTAGGACGGTCG
TTGGGTCTTTGATGGCGCTCAATTGAGGAATTGAACAAAGGAATGAAGAATATACATATTAGAAGACTTCGATAATATTTTTGATACTATACTGG
AATGGAAAACGACAACGGATGCGTGGGAATACGCAGTCGATGCTATAAACACATATATTCATTTGTTTTCTTTATGTCTCTTTATTTCTGTTTAA
AGGGAAGATATTCGAGATGTTCATTGTCCCACGGATTTATGATGGCAGATAGTATCTATGTATATTCTGTATGGGGGTGTGGTGCGCATTATAGC
TGTCATTTTACTATTGTCGTATAGTTTATTTGCATACTTATACCGATTGTTTCATACGTTTCTTTTCGCTGATGAATCGCTGCTGGTGGTGGCAT
GACGCAGTTCCCATCCATACTGGCAATAAATATATATTCATCTATGGCCAGACAATCGGAAAAAGAGAGCGCCGAAAAGTACGCACTTGAGTCAC
TAAAAAAAATATTATGTGTGATTGAAAGAAATGGGGGAAAGGGTTGCAGAACATAGACATATGATATATGCACGCATAGGTTTCTCAAGGGGTGC
GCACAACACTTTAGAGAAGGAAATTTTTAAATTTCGAAATTGTCTGACACTCAGACAATTGAGTTATGACAGCCGGCTGAGTGTTTAGTTCTATT
AAAGTGCCTCCGCAGATGCTCCAACTTGATATGGGATACCTAGATCCATAGATAGATACAAATTCGGATATTTCCGAGCCAGAGTTTGCCTGAGT
TTCGCCCGTTTGCAGAGTTCGGCCAATCAATTTGCCTCAACAAATTTGCAGCACAAATAGAAACGCTTAGATATTTAACCAAATGGTCAATTGTC
ACGCCAATTTAAGACGCCAAAGTCTCCTTTGGCGACTGCCGCTTGACGCTGTGATATTTTCCCCATTCAAGCCGATTTGTTTGTTTTATGCCGCG
AGCCAAAACCAAACTGACCATGAAACAAACAGCCAGTTAGCTCCGAGCGGATAGTTCAATACGAAATATTTCAAAAAAAATATATATGTCTCCGA
CTTCTCTGCGCCACGCTTGACCGCTTCGAAGGGTATATATTTAGTTCAAGTGATTTGTAAAATGGAAAAAATACAATACAAAAAATACAACATTG
TGAAGCCGGCGATTTTCTATTTACATTTAGGTGATGGATAGCTTGGGCTAGAGAAACCCCTGGATAAACCACAATTAATTACGATCCAGCGACAG
TCGATCGATTGCCGACTTTGACTTTGGCTCCGATATTATCTCGACTTCGTCTCGAGTTTTTTTTTGAAAAAAATTCTGGGCATTTGAGTTTTTCA
ACTTCAACTGTCGGGTATAGTTTTTCAAACAAATACGCACATGGGTGTTGGTTTCCCCTCCTCGATCGGTTCTCGGTTGTAGTTGCGTTTTTCGC
TGGAAATCATTGGGGGAGAGTGCTTTCTTTTTTTGAGCGATGCGTGCCTACAAAGGCGCCCCACGAGTTCAATGACCATGGTCAGCCAAGATCGC
TTGTATGTAAGTAAGTATGTCCCATGGGAAGGGGGTGAACCATTGTGTGTATATTGTACATACGAATATGATGTATAGTGTGCGCATATGTTGGG
CATAAAGCTGCTTTATCCTGGGGATGCGGTCTAGGGCATTTCACTGGGCTTTTGTACTCTGTATTTCTGTATTGTGCGCTCGCAGCAATTCATGC
ACATTCATTGTTTGCATAGCCAGATGTTTAAGACCGAAAAAATGTCTCGTTAATTGACTCTTACTTAACTCTCCCACTCCCACTGAAAATTGCAA
TTAGATGACTTAATGGGCGCACGCGGCCAACGGGCTGTTTGCAAAATAGCTGAGTTAATTGGAATTATTCCGATATCAACCCACCTTGCGCAAAG
TTTTCCTTTTGGCTTAATTGTTTATTTACACCTAGAAAGATAAGAGAATTTGTGGCTGTTTCGCTGTTTACGATCTGGAGAATGTGGAGTGAGAA
CAATAAAGTATTCCACAGTCTATATATAAAGCTCAATTTATGGATATGTACTCCCCAAATACACCCATTCTTTTCACTGAATATTTGCATAGCCG
ATAAAGAAGGCCCCAAGTCTGACACATCGGACAACTGACAAAGCCAGGGAGGAGCACAGTCCATGGCGAATGGAGCATCTTCAGGGCGGAGTAGT
GGAGATTAAGTTAATTACAATTTCGCGCTGCTCTGGCAAAGTCAGCCAAGCTGGCCAAGCTGTACACGCTGGCAACCTGTAACGTGCAACGTGCA
ATAAGCAACTTGCAACATTGTAGCGATTGCCACTGAATACTTTGTGCTGAACTTGATCGCTGGGCCAGGGCAGTGTGGAAATGCCTATGCCATCG
ATGGCTATATATGTATGTATGTACGTTGACCAACTTTTGAAGACACCAAACAATACCAAGTGCAAGACGGTATACCCATTCTCCCATTCATTCAT
AGGTCGTCGACGTCTGGCACCCACGTAGCAAAACAAAGCAAAAAGCGAAACTAAATCGTGATTTATGATGATTATATTTGAATTGCTCATTGTCT
CTCACACCCCAAACATCCCAGATTCGCCTTTAGATCGTCCAAACATTTGGCTCTAACGAACGATTTTATTTTTTTTTTTATCTCATTGCAAATAA
ATAAAAATCAAAATTGGGACTCACTGGAAGTGATGGTGGCCTGACCATGACCATGTTGCAGCTGCTGCAAATGCAGTTTTCCATCGAGCAGCGAT
AGTTGGAAAAGCCCCCTACCACCAAAAAAAAAAAAAGGGAGCTCTAGTGCAGTTTCACTTTGACTCTCCCTTCGGGGTTTAAGTTCCTCGTGGCG
TTGCATTGGGGGGTCTGGGTCTGTAGGGCGCCGGGAAAGTTAATTAATTTTTCAGCGAAAGTTGCCTTAATTAATGCACATCAGAGACTGCATTT
TGGGGTCATCTACTAAACTCGCCAAGCATAAACCTTAATCCACTACGGCCAGCAAGCAACCCCTTAAAGTTCGTATTACCAAAGTCCTGGCATTT
GCTATTAGCAGCAGCGTTTTAAATTACAGTTTCACTTTTTAATTAGACCCCGCCCGGGCCAGACGTCTATGCAAAGTCGAATAGAGAGCACCGGA
GGCAGCAGCTCATGGAAAGGAAATTTTAATTAAACAGTCTGCGAGAGGGTTGCCGCAAACAGTAACAAAAAAAACCTAAATAAAAACCAGCACAT
CGCACAACGAACTCCAATGGTCGGAGTCACACACAACTGCGAGTGCTGGTCAGTTGCGAAAAATGTTTCGAGGGCTTGGCCAGGAAAAGGAGGCG
GGCCCATCCTTTTCAGAGGGTAAAATACAAAAAACACACTATTACTCGTACTAGACTGTACTGGAAAACTTGAAATACAAAGTGCTGCCAAAGTC
CAAACTCATCAATGATTTGTATAGTAAAGACTGCATTCCTTAAAATACACAATTGTGAGTAAACCTCTAGAGCAAGCTCACAAGTAAAATGCTTA
GAAAATCGCTGTTGTATTATGCTCATAATATATATATATATGCTCAGTAAAAGCATAGAACACAAATAACTAAACTCAACTGCAAATGTTAAGGA
ACTCGATCGATACATTTTTCACCATCTTTGTTTGGGTATTTCAATTTCAGTTTTTCGCAGTGTAAGAGCCAGCGATGAACTAAGTCATTTGCAGA
CCTGACTGAGGGATTCGAATAGGGCACGGCATTCAGCTTTCGGCTCAGATCGGTTTGGCTCGCTTTGGCCGGGGTTCCTGGTTTAATAGCTTCGC
TCTTGGCATTGAAATATTTATCATGTCGTGCTAATATTGCCCAGAACCTCGAGGACTGGACACGCTCGATTGGACACTTGGATAGGGCGCAGCTA
GCTCTGGAGGAGCTGGCCAAAGTAAAAGCCAGGTCGCTTGCCTGGCTGCCTGGTTGGTTAGTTGTAGTCAGTCCGTCTATCTATGTATTCCAGAG
ACTCCGAATCCCTTCCCCCTTTCGACTGCTTCTTGCGTTGCCCCTGTCATCATTGACACGCGAATTGCAAAAGTTAATTTAAGTAGTTTTGGCCA
AAAGACGACAACAAGTCAGGGAAACCAAACTGCACTGCACTCCTGAAGGCTCTGAGCTTCGGCTTTGGCTAGTCATGGGCAGATTTATATGGCCA
TTTGGCTAATGAATTGCGGCCAGAGGCGAAGGAAGAAATAAGAGCTGATCCATGGGCGCATATAAATCATGAGAACTCAACTTCGTTGCTGCCTT
TAAAAACTTCGATTTCATTCCTGAGAAGCCAGATCATCGATGAGCTCGTTTTTTTTTTTTTGTTTTTTCCAGCCATCAGCATATTTTGTTTGGG
CCCGCATTGGTTGTTGTTGTTTTTTTTTTTCGAATGCCATTTGCTTATTTTTGTTGGCCATCTCGTCGCACGCCATGTGAATTATGTGGGAGTTT
TGTTGGCCCTGCGCAAACATTTCAATTCGAATCGTTTGTAATTATTGCGCAAATGTGACAAGACAAACAGTTTGTTGAACACATGTCTGTGAGAA
AGGCGAAACCATCGAGTAAAACAGAAGAAACAACCTAAATGGATGGCAAGGTCACAAACAGCAGCGAGCTGAAATCCCTTCGAAAAGGTTTCTTT
TTTCGTGGCTTTATGGCCGAAACAAAAATAATGAATGCGGGCCCCAAAGGAAATGCCCAGAATATACATGTACTGAGTCATCGCACCGTCAAAAG
ATCTTGCAAAATAGGAAATAAGCATTAGATCGCACTGCTAAACAAAGCGAGTCCCCACAAATTAAGGCAACGTCAAGCGGCGTGAAATGAAAAG
GCAAAATTCGAAATAAATTCACGAGACGAATCGCCGCTAAAGTTGAGCAAACGAAACCAGCCCCAAACACCTCTCATAAACAAAACATATTTATA
TTTATATTTATATCGAGAATATTCTCCGAGCTGCATCCCATCTGATCTGATCCAATCCATCCACCGGGCAAGTAGCACATCGTGCATTTATTACA
TTTTTGACTCACAGAAATAATCAACGTGAAATATTTGGCACACATTCAACCAAGAGGAGAAAAAAAGCGATTGGGGCACGCGACGTTTGGCGGGG

FIGURE SHEET 772

GCCTGGCGTCCCGATCAATAAAAATAGCCACTCGCAATCCGCGGCAAGACGTGGGCGAGCAACATCATCATCATCATCATCTCTAGTATCCGAAA
CCGAATCGAAAACAACATCATCATCGCCGGATGATGGCCCGATGGAATGCCATCTATGCCACAGTTAAGAGGCAAACAAAGTGCAAGGACGTCCC
AAGGGGCCCGTACTCATCCCTCCCCGTTTGGCTGGATATAAAAATATCTTCTTCTCGGTATCTTTGGCCACTCCACTCTCCAGAGGTGAATGAAT
CCGAAAATATTTCTGCACGCAAGTTGTGCGCGTAATTGCACGTTGCTGCACCTCGCTCTCGGTTATGGGAGTCACTCAGTCGCAGCCGTGGAGTA
GGAGCCATCCAGATTGGGATCCAGACTCTGTGGGCTGTGCGACGGACGGCATCTTCTTCTGGCTTAACCCACATACAGGCAGGCAAACTTCCCTT
TGCAACACATTCCTAGCGCTTTTACTGCGACATGCTGATTGGCGGCAGCATCCCTGCCGCAGTATCTAACTGCATCTAAATGGAGTTGTGGGCTT
CAGTTCTTTGAACCAGCCAGCCTAGGAGCACTAGGATCCACGAAAGTAGTGAATATGACAGTATTACCGCACTTCTGGAAAGTAACTAACTGTTA
CTTTCGGTAACGAGTAACGAGTGACCAAAACTAAATATGTCAAAGAACGTATATCAATCTTAAAAGTGCATAGTATTCATAGTATTCATAGTACT
CAGTTTGTGGAGAAGAACTATCAACTATTTTGCATACTACTACACTGAAATAAATACACAGTCAGGTTTCCCCTTTTCGCACAAAAATGTCGCAA
TTTATGGGCTCTAATATGAAATTCATTGCTTTTCTCGCCCGCTCCGCATTTTTCGCCGACTTGGCTCCTCGAAAATGCAGCAACTCGTTAGACGC
ATTAGGGCCTGGGACATGGGACATCAGTTCACTTCCCTGCGGATGACATATGGCCAAGTGGGGATCTGCTTGCCTCCCAGCTCACATACCTGTGG
TGGTGGCGGCGCGTCTTATTAGAATTTATGATTCCCATCTTTTTCTTTTTTGCTTTCTTCGGCGCCGTCGTTTCGTGGACTTTGGTTTACTTGCT
TTGCTTTGCTGGCTGGCTGGCTGCCTTTGCCCAGCTGGCATTTACTCTTAGTTTATTATTTATCAGGCACTTTATGGAGCCCCGAACAGCACACG
TATATATTTGCATTTATAATTTCAAATTGTTTATGGCCAAGCGTGAAAATGCCTCACAAGACAACAAGAAAATGGCAAAACTGCAAGCTTAAAAC
AAAAAAAAAAAATCAGAAAAGAAAAGTGGGCAGCAACAAATCTTTTCCTAATGCATGAAATTTAATGTGCATGACGCATCCGACACATGAACTAA
AGAACTGAATATATTTACAACTTATACGAGAGTCAACTAATTGAATTCGATTATTCAGCAGGAAGCACTTGTAGTGGATAAGCCGCGGATTTGCA
ATAAATTTCCCACCCGCTCAGCAGTTTATGAAGATAAATACACAAAACAGCTGCGATCAAAATCAAAGCAGCGTTTGTATAAAATAAAAAAAAAT
TGAAAAAAAATTAAATGTTTGTACAACTAATGAACCTTCAATTGGCTTAATTATGAAAACATTTGGTTAATGCCTGAAGATTAATTAATGACAAA
TTTGGGCGGTCGTATCGCAATTAATGGGACAGCTGATCTAATAAATTACCTGTTCCTTGATTTTGCAATCATGGGCATGTGCAAATAAATACCCA
ATACGTTGCGCTTATCAATGAAAATCGTATTTCGCAATACACCACTGCAATGACTAGAAGAATTCTATTTCACAGCAATAAATCTATTATTAATG
AATGAAACGCTACGCTGGATGCCCACGTAGGCGAAACAAAGCACAAATATTTGCATATTTCAAAATCATATTTACGAGCTCGACGACTTCAATCA
ATTAACGCATTAACATGGTTTTATTATGTATCGCATTCAAATTGGGCAAATCGGCGGTAGCCAAAGTGCGAAAAAACTTGTTCTCGGCGCCATTA
CCAAAAAAATATAAAAAAAAATAAAACAGCGAACTACACAAATGTTGCCAACGTGGGCGATCGATCGATCCCAAAGTGAGTAAGTATTATAACTT
AATTAGCTGGCTAGCGATTTGCACAGTTGCTTGAATGGAAATCAAATATTTTCGTTGCTCATTGTGAAGTGTTTACGGTAAATATTTAGCTGTGT
ATATATTTTTGGCCCATTGCATAACTTGTTTTGTTTGCAATTTCTTTCAAAGAGTGCAAAATTCATTTGGGCTTTTGTTATTGAAATCGCCGCCG
GTTGGTTTGATTAGTGCGTTAAGCACTTTTACTTTTTTCGAACCAAAGACAAAGCCTTTGGATATGCAAATGGGATTTCAATTTCTCACATTTAT
AGGCCCGAGGCCCTAACTAAGCAAACTTTGTTTTTAGCTTGGACATTAAGTATTTTTAATCAAGCCCAAAGGTAAGATGCATTATAACATTCGAG
GGAAATTAATTTGGGGCGCATCAGGGTTCGTCTATAACAAATAAGCGCTTTTTCTGCTGAATATGTTCGGTTTCGCTGTAAACATTTGCATGCAC
ATCAAAAGTAACTGTAACCGAATGTTTGCCTGGCCAGCAAAAAAGTAAGAAACAACCAGCAGACGAGGCAGGCAACAACAACAACAACAGCAGCA
ACAAAAGATCAAAATCAATTGAAAAATTGTTTGGCGAAATGGTAAGACCAAATCGAAGATGGAAAATGTGTGTGCAGCAGGCGGCAGCAACGGGA
CAAAAGGAGGGAAAAACGAGTGGCCAGCGGAAGAAACAAACCAACCACTCCCGGACCAATGCAGATGTTGCAGTTGCAGCAACTGCTGCTGCTGC
TGCTGCTGCTGCTGCTGCTGATGTTGCTGTTGCAGTTTCTAAATGCCGCCGCGCACCAATTCACCGACAGTGAGGCAGGCACAGGCAGCGAGAAT
GCAAACTTTGCATAATTTATGGCAATCAATTTCGCGTGAACATCAACACGGTTGCAACGCAAAGAGATACAAAGCCGTGCCAAAAGCAAAACGCA
AAGATGGCGAAAAAGAAAAGAAGAAATTGTGGCAGCAACAACAGCAAATGCAACAGCAACGGCAACTGCATGCCATCCGTCTATCGAATGCCACT
ATCAACTTATTTAGTTCTACTTAAATGTTTACTTTCATCAATTCGCAACGAATGCGACTGCCAGCGGTGCAATGTCAATTGGCTGCGGATCGAAT
CGGATCGGCTTGGATTGTCTGATGTGGCTTTTTGGTCACAAAACTGTAGCTGGTCAAGAGCGACTAAGACTCTCTAGTCGCCTCAACAGGATGCC
CGCCATCGCAGCTACAGATACATTCACTTTGCCAACTCCGTCGCTTAGTGGAACACTTTTCGCAAAAACAAAAAAAAAACAAAAAAGGATGAAAA
AAAATCATGCAAAGGCAGCCGGGGAGTACGATTTCGCCTGGCCCTAATCTAATTGCCATCGCCTAACCCAATTTCCCAGTTCTTCAATTGCAACT
TAGAACTTTCACTCGCTGCCTTGGCCAGCGCGAATCAACCAACCACAATTGTTTTGCACTTGCAAGAGGATGGCTTTGAGGTCTCCTCGCTCAAA
ATACATATCATTTTACATAATAAATTTAATGCCGCACAATCCGATCTTCTTTGTCTGCAATTTGCTCACATAGGAACCCCTCATTGTGTCTACTG
TAGTTATCAAATAAATACTAAGCACTTTAGTCAAACTCTACTCTACTTCCATTCTGCTTGAGTGCCGTCTACACTGGCGTTATGCATTCACCGTT
GCTTTTGGCCCACTTACTAACAACACTTACTTACGAAAACTGAAAACTGAAAAAGAAAAAACCAAACTTGAACGAAAAAACCAAGTTTTTCCTGA
TTTATGTCCGAACAAATTGTGTGTTGGCTTGGCGTTTTCCGTATGCGACATGATTTAGCTAAATTATGTTGTGATCTTTTGATATGTACAATGAA
AACGAATGAAAACGGTTCCTCTCATCTCCGATTAAAATCGGGAATATGCAGAGGTCGTTATTAATTTTCCCACTTATGGACGCTTTCCCGCCTGA
TTAACCCCATCTGTGTGAGGTTAAAATCCGCCAGCTTCTATGCATCTTGCAGCTAAACCGCATCGTTTACAGTTGGTATCCGTTGCACGCAACAG
ATGGAAATAGATGGGAAATTGTGAAAGAGTTTTAATCAAAGTGGGAACCGCTTGCTGCTCCTCCGTTTGATATCTTTCTCGCGACTGCCTTGACA
CGCAATTGAGCAGCAGTTCCCACCCAGGGCCAAAAATAAATCTCGAAGAGATTCTTCATTTCGAAATATATGTATCTTTGGGAGGGAGCAGAAAT
TGGGGCCAAAAGCGTGGCAGTCGAGATGAAAATCCATGCGTGCACTTGACGCCGCTGAACCCACAAATTGGTCGTGTCATTAGGCAGATATTGAT
TTGAATTTATTGGCAATTCAATTAACTCTAACCGAATGATCGGGGGCTGGCTTCAATTATTTTCCTTCTATTTTTTATCGATATGAAGGGAAGGG
GTGAAGTTTTTTCTACTGCTGCTGCAGACATTAATTGTCTGGCAGCTGGCGCATTACAATGCGGAAATGCAGTTGAATCGAATGGATCCGAATGG
AATGGAATCGAACGCACTTCACACGCAAATAAACAGTCCGTTTGTTGGTTTGGTCTGGAAGTTATCTTCGGGATGCACGGCAGCCATATATTCTC
CATCGAGGGGTGAAGTGAACTGGGCATATTGAATGGGGGGGGCAACTGCGAACTGGGAATGGCGAGCAGTTATGCAAATCAGCAGGTAGTCTCCC
CCGGAAAGGTAGAGGAACAGAACCATACATAGGTCGGTCATTCACCGCTAGATTCACAAGTATCCATGAGATACGCGCAACTCGCATGCAATTTG
CGGCATTAGAATATGCGCACATGAATAGATAGAAAGGATCCTTGTGTTGTGTTGACCACGAATGAATGGAGCAGATTTCCATTTAACCGCAGCTC
ATTGTGCACATTCATTAGACAACTGAAATATAATTGCAAGTAAGGTTGCCATTGGTGCTGTTGGGAAAGCTGGGTGAAAATAATGGCAACAAATA
ACCGAATAACGCCCGTGAAACACAATAAACATTCACGAAAGAAATGTGTAAATATCACTTAAAAACGAAAATGAAAGTGAAACCGTTTTCATTCA
TCCATTCAGACATATGAATCTGAAAAAATAGATGAGAAAGTTCAATATAACTCGGGTGAAAGAGTTGTCGTATCATTTAGAAAAGCTTGGTGTTC
ACATTGATTTCAATTTCCACTACCATGTCCCCCCCATCGATCTATGCAGCTAACTAACCCATCATCTAGATGGCCGTGTACATTGTACCAGTAC
CAATGTCACTGTTGATTGCATAATCACCTGACCGTCACTAATTCCTACGTAATTGGAAAGCCATAATGTCAGAGTCTTTGTGCCGGTCGTTTGGG
CCCTCCTCCCATCGCATCATGCATCGCATCGCATTGCATCGCCTCATATGCCATGCACCACATCTGTTGCAACTTATTAATTTTTGGGGCCAACA
ACCGTTCCGAGCTGTAAGCGAAATGCCCAAATAGCAACCCGCAACAAAGCAGCTTACACTCTTAAGTGTTGGGCCGAGGCTAAAACTAAACGCTA
TTAAATTTTACACACGGTTTCACTGCAGTTCGAATGCGTTTTCATGAGCTCTCCGCTCGGAATTTTTTTTATAGCTCCCAGCCAGCTAGCTAA
GCTGCAGTGGCAATGGGTTTGGATTTTTGAGTCAGCTCTGGCTCTGGTCTGGGCCATTGTTTTGCAATTTTGTTTCATTTTGGCCCAGAGAGAAG
GGGGGGGGGGGTGGATGATGCGGCGGCGGGGCGGCATGATGATGATAATGAATGATGAGCCGGCCGAACAACCGCCACAATACCTATTGAGTA
ATTACAAAAATTTTAAAGTTTAATTAAAATTGTGTAAATAATCGCATTTGTTTGGCTTTGTTACCGTTGGCGGGTGTTACCGTTGCGAAAACGAA
AGTGCCATCAAATTATGATGCTCAATTGTGGGAACAACAGCTGCCTTTTGACAAGCTCACCGCCTGCCTGCCACTCGATGAATTTCAAATGCTTG
TCATTGAGGCGGCAAAGTATCTGCATGGATCCTATGACTAATGGCAGGGAGTGAAAATCATCAAACAGATTGATCACTTCATTTAACAGTGTACC
AAAATATTTCTTATCTGAGACATGCGCCCACGAGCAAGATACTTTTCAGCGAGATACGTGTCAATGATTTAAAAATAAAAAAATGAAACCAATTG
TAAAAACTAAAGAATTGATTCTTATGCTTATTCAAGTGCGGAATTGTCACTTACCTTGTAAACCTCCGAGAAGAATCCCGATCCAATTTTCTCCT
TGACGAAGTCATCCACGGAGTATAATGCTGAGACGGCAGTGCGCAGCGCCCGACACGAGCTGCCGGTGACCAGGCGATCCGATGATATGGTCCGC
GTCACGGGCGCCGGCGGAAGACCATTTCCGATCCAGCCGCCGTTGTGGAGCGGCTGATGTTTCACTGGTGCTTCCGCGGTGGCGTCTCCATTGGT

FIGURE SHEET 773

CGATGTTGTGACGGTGGTGGCGGTGGTGCACATACCCGCTGTGCTCGGCCAGATGAAAGGGGAGGCGGCCGATGAGTCCACCTGGTCCACCGATA
ATCCGCAGATCTCCGACGGCGGGCCGGGTCCACTGTGCTGATTCAGGCTCATGTTTATCAGCTACGACGTATGTTGCTGTCGTAACCGGATGTGT
ATGTGAAGTTGGTTTAAGTTTGTTTTTTTTGGCGTTGGACGACCTCGCCTTGCCTGCTTGTTGTGGGGTGATGGATCTCTGGGGATCGAGTTG
GGAACTGTGTGGTTTGGCTAATGCTGATGTTCTCTTGGCTACACCATGGTGTCGTTCATCGCAAGACAATAGTTAGCGGATTGACGCGACAGTTA
GACGGGCACGATTTGTTCAACGGATGATATATTTTAGTGTTTGCTTATGGAACGCAGCACGAAACATTTATGGGACCCATAGGTCTGAATTTGAC
AATTTTAAAAATTTTGAAACAGGAAAAAAAATTGTGGAGAACTAACTATCAATCACTTTTTGCTTGCTTCGTAATAGAGAAACTTGTGTATTTAG
TTGTTGGATATTTGGAATGCATTTGATTGTTCTTCGATTCTTGGCACGTTGCAATTGTGTTGGAAGCTGCACTGGAAGCGCTCGCAGTTGGAAGT
CTGAAAGAAATGCAGGCAATAGTTAAAAAGTTAATAAAATTCAATCAAACTCGTCGCTGCTCTAATGAAATGTAAACAAATGCGTCTATAGATAG
GTATATATTTGCTCGAAAAAACAGCGAAGCGGGCCGCGTGATCAACATTTCTGTGTTTATTCCTTTTTTATGAGGTGCAAATTAAAATACTTCAA
AGAATTCGCCTTATTTTCTGTTGTCACGCGCCACTCAAAGTAATATCCCAGTGTCAGCAATAAATTCTAGAATATAGGAACATAAGATATTTAAA
AAGTATAAAAGGGGCAGAAATCAAGACAATGCAAATTTATTCAGGCCTAATAAGAGCTAAAAGTTTAATATTTTAAATGGTGTAGATAGGAATCT
GATTCTTACTCGGAAGAAGCTGATAAGTTTTTTCGAAGAAACTTAAGCCTCTTCATCACGAAATCGTTTCTTCATTTAATACTCAAACAGCGGCC
TTATTTATTTATCATTCCAGTTTTTCGTAGACATTTTGCATTAGCACATGGCGAAAAAAAACATCGCAAGCTAACAAAACTAACAAGAATGAATT
AATCGACCCCGCTGGAAATTGCTAATAAATATTCAGGGTCAAAGTCGACAAAATTGGCAAAGTTTTGCTTATCAGCGGGCTCTTGCGGTGTGATA
GCCGCTTAATATATGTACAGGTATTTGTTGCCGTTTGATAAGGCGGCCTTTTTAAGTGCGATAAAGCACACAACCCATCAAATGTCCCCAAAGCC
AGCAGACTTCATTCAGCATTTGCTTTTTTTTCGAACTAACAATGTAATTTAGCAGCAATTTTGTTATCATTACGCTTACTTTTGTCGTCGTCGTT
TGTTTTTCGTCGTTGTCTTGAGAGGGGGGCAAATGAGTTCAGTTCATCAGCAAATAATTGAGATAAACACGATCACTAAAACCTTGGCCTTGCGC
CTTGAAAACTACGTCTGTTTTGAGTGGCTTCAAGGAGTTAGTTACATTCGGCAAGGGAGGTCGCTGAAGAGTTCCACAATCGGAAAAACACCACC
ACCCACCGCGAAGTACTCAGTTTCAGTTTTTTGAGATAAGTTCGGAAATGATATAACCAAATATTTTGCTGCTTGCTATTAGACCGGCGAACAAT
GGCAACAGGTTGGAATTTTTTGATTTGCCATTCCTTATCGCAATAACCACATATATATTCGGCGATAAGATACTGAGAAATAGCTTTTGGGCGAC
ACAACAAAATTGAATTTGGCTCGTAAAGGATCATGCGAGTGGCCAAAAGGCGATCATGCCCACAGAGATAACAGCTCAAAGCCACAAAGCTCACA
ATTAAAACTATAACAAAATAATTACACCAAATTTCGACATAATGATAATGATAGCAGCGAACGGACACAGAGCTCTCACTTTTCCGCTGCTGGCC
AAAGTCAAAATAAAACTCAAATTACCAAGCACATTTTTGCACTCGGCAAATAAACGGGGAAGTTATGCGAATTGGGATTTGCTATTTGCTATTTG
CCGTTTTGGCATTTTGTGTGTGTCTTTCCTTCTCTTGCGAAATCTGTCCAAATAGCCAGTTGAAGTCAAAGCCGGCAGCAGGCCATAATTAGGGT
CAATTGCGGCTAACCGCCGCCAATTGACGACAACGAAAGCTTTTGGCCAAATGAAGCGGCCGGGGAAAAAGTGCTACACTTCATTAGGTGCCATG
ACAAACGAAGAGCTGCAGCAAAAAGTGGGCTTGTGGCTTCGACTTAATAGCACCCAAGGATCGTTTTCGCGCCCACCACGCCCCCAGAATACAGT
TGTCCAATTACAGGCAGGTCTTTGTCAAATTATCTCGTTTTGAGCTGTGAAATGAATACGTGCTATCTTCACCAGTCAGCTGTGAAAGTTTCCAT
ACACCCTAATGAGTGGCAAACTTAAATATATTTTTAAAAAAAAATTGTAAACATTAAACTCGGCTATCATGGTGAAGAGTTAGCTGGGAGAGAG
TGCCTATCATCGATGAAGAGGAAAATCCATTTCGTGGCCCACAAAAATGAGTTTAGCACGCTCCGCGAAACTAAGTCAAGGCCCCAAGCAACGAT
TTTCGTTACCGATTTGGGTGAGCAAATCTATCGAGTCGAGAAAAACACTTAAGCGGTCGCTTTTATTTCGACTCTTGCATACATTTATTTTCCCA
TCACGTTTCAAACTATATACACATGTATTCCGCGTGGAAAGCCGCAGCAGTAAAGCATCAAAATATTTATGTTTCAATAGGAATGGCAGCCAAAC
AAATGTCAGTCCGCATCCGTGGTTGTTGCCAAACATATGGAAAATAGATGATGAGCCCCACAACACCGGAATGCTGCAATCTTAAAAGTCAGCAG
TTCCACGAAGATTAAATGCCCTAAAGGCATTGAAGCAGCTGAATATAATTTAAAAATCTAAAAAAAAAAAAAGGCGGAACACGACGTGCAATAAAT
TTAGGCAATTTTAGAAAATACATCTTGTGGTGTCGCAAGAACTCAAAACTAAAGAAATCACGTTCAAAACAGCAGATAATAGGTATTTCTACATC
AACAAGTTGACTTAGGCAAGAAAGTTTCTATATCTGAAAGTTGGTGGGATTCTGCACCGACTTAAGAACAACTTTTCTCCAAATATTAACTCTAC
TAATCGTTCAAAATCGAGGCTATTTAATTAATACATTTCCTAATATGTTTGCTAGAGAGAAACCAATGAAATTAATTTCAGCACACCACTTATCG
CCGTTTGCTTTCGATGGCGTTTATGGCATTTTCCAAAACGAATGTTAAACCGTTAACCGCCACAAGGTTCGAGTCAATAAACCGCTGTCGACTGC
GGTGACTTTGTTGCCGTGCTGTGAGATCAAGTTGCATTTTTATGGGGCCAAGGGTCGTCGCGGCCACCACCGTCTGCATCATCATCATCATCAGC
AGCAGCATCATCGTGGTATCTTCGCCTACGTAGACGCGTGCCAGGAGAATTGTGTGCAATGCACACTGCATCGTTTCAGCTGGGCCATTAAAGAG
GCATAAATCTTGGTTATGAAATTGGAAATGATTTGCTGTTCAGGCACATTCAAGTAGGGAGCAAGTAACGCACCGAGAAGTGATGCGTTCAGGAA
GCGTCTTGCGTTTAGAGTCCGAAAAAAGCGTTAATGAAAAGGAAAGTTGGTCAGCGGCAGAAAAAATGCCACTTCATTGCCGTGTAGAAAGAAAA
ACAAAGACGAGGAGACGGCGAAAAGAAGCCAAGGCAGCTCAAGAAGAAATTTCTATAAACAAAGAGATGAGACGCCGAGGCAGAGCAAAATT
ATCAAAGAACAACAAAAACCGAGAAACACAAAAAAAAAAGAAGTGGAAAATGGGACATGGCACACTCTTGGGCCCACAGAAACAACAAAGACTGA
ATGAAATTCATGTCGTTGTCGCGCTCATAAATTCTTCTACGCCTATATATCGCTGGCTATCTGAGAGATACAGATACACCCACACTTGGAAAAAC
TACCAACTCATTCAGCCGGGGAGGTGCTGGCTGCATCCGCTCTCTACCTATATGTATGCCTACTTATGAAAAAGAATCTATGTATGTAAATTTGG
TGTATTTTGAATAAATTCCAAGCCCATCGAAGGTGTGAGGTGCCAGTTATCGTTAGTTTTTATTCTCTTGAGTTTAAAGTTTAGACTCCAGAGG
CCGTACAACAAGTGATTCACGTAACGAAATGGAAAGCGAGGAGAAATATGTGTGTATACAAATCTACCAAATAAATTCAAAGGCAATGGAATTTT
CGACTGAAAGCATAAGATAAGCTTAATTAGCCGGGCAGACAAAAATTTCACTTTCCTTTGGTACAGAACCGTCGTTTTCTAAACTATTTCTGAAT
GTCCAACGATCACTGCGCCATTTAGACATTTCGACTAATTGGCAGCCAGTCGGCTTTCGGGGGGAGGGCACTCACGTGCCGCCCATCGATCTGCA
GCAAAACTATACGTAAATAAACTTTAGGATCGAAGAAATCCAACAAGAACGTCAACAAAAACGAAAACCAAATGGGTTTATTTTCAGCCTCAAGT
GCAAGTCCTATAAGAAGATCGAACAAAACAAAACACTTGATGAATGCAACCGAAGGAGGTGCAAAAATCGAACAATAACAAATACAATAGGAAGG
GCGCGTAGAGTGAGCACAAATCGTTTCGTTTATTTTATTTATTTTATTCCCCTCTATGCGGACACACACAAATGAAAACAAATTAGCTTAGGCAG
CATTAACAGCCAGCTGCCAAGGGCGGAAGTACGGGGGAGTTTACTGTTAATTTTATAAACACCACGAAAGACCACAACGAAAAAAAAAAAAAACAC
CACAAAAATGCAGCAGTAGCAACAGCCAACAACCACCAAACCGGCAAAATCCCAATAGGGCAGCTGCATTTCGGGAGGAAACCCAAGTGGAATGT
GCATTCGAATTGGGAGCTATAGCTTCTCGATCCCCGGATAATGAGCCGTGAACATCTGTCGCAGTTTACGTGGAAAACTGTCTTTCCGCTGAAT
CGACCGAATCGGAAAAAAAGGGAGAAACTGAGACTAAGGAGAGAGCGAATGCTGGGAAAACCAGCACCAACATCGGAAGCATCTTCATCATAACT
TGCAAATGTGTTTGTGTTATTTTTACATTTCCGCTGCTTACGAAAATATTTACGCTCCCCTTCGCACAAAACCTTCCCCATTTCGAATTTCAAAT
TTCGAATTCCAGACGCTCGCACACACGCACGTGTTAGAGATGAGCCAGATTTCCGAGTGCATCGCATGGTGACAACAGGTTCGATTCAAATGAAT
ATGGAAATGATTCTGCTGAGCTCACAAAAAATTTAAGCATTTGCTTTTCAAATTAGATCATATGGCTATGCTATTCGAAACAGATGTGAAAAAGT
AACAAGTTTTAGCTCTACAATGTTTACTTTAAATTTAGCATTTACGAAGTATAAATAGACACATTATTTACGCATTATGTTTTATTATATATTTAAG
ACAAAATACAATCAACGTAAGTTAAAATATAAGATTGCAAACCTATTTACCCTCAATTCTAAATGTTTAAATATACAATAGTACATGACAATTTT
GCATTTCCCGTTACGAAATTATATTTGTGTTTTTATCTCGGTAGAACCTTGAAAACCATGTTGTGTCAAGATGCAGCGAAAGCAGCGGGTGGCAA
CTTTTGGCAGGCAGTGTGCGAAAGCTAAGGTCAGGCCCATCTCTAGGTTGCTTCCGCACACAGACACGCACGCACACAGCGATGGGGAAATGCCA
ACGATAGCACAGGTCTAATCCATTTAATTCTGGCTTTTAACCGATTTCTGCTAATACTATTTATTTACCCGTTTGGTTTTGGCGACTGCTCTCTC
TCTCTCCCTCCGTTCTTATTGCCGTGTGGCCATAATCCAATTATGCTTGTGTTTGTGTGTATGTGTCTGCTCTCTATTGCAATTGCAGTTATTCG
CATCCGCCGTGATATGCAACCAACACATTCGCACTCGCGCACTCACACGCACCCGCAGACATCACAAATGCGAGGACCGAAAATCCTGAGCGTCA
ACAAAATAAATATAGCTCTGGTGTTTTAAAATAGGTTTTCACTCGATTCTGCGTTTGCTGTCTCGTCTTGTTTATGTGCATTCGTCGTTGGTTGT
GTGTACTTGTTTTTTTTTTTTTTTGTTAGACGCGACTGTCCATTCAACATTACCACTCAGCCGACGCAGAGCGAGATTATAATTCGGTAACCGAT
TCACTGGCACTGCTCTAACGGGCTATAGCCTATGATCCAGTCTGGAATGGAGCTAAAGATATGTTGCTTTCATTTATGTCTGCACTCGCGAAAAA
GCGTCCACAAATTAACAGTTCTTCGGGAGCGACGCGCAGCTAGACGTCCGACTTTGTTTTCCGACTCGATTAGAGTGACCGTTGTGGGATGGTGG
AAAAAAGTGGAGGGCCCATGCTGAAACCGATAACAAAAATACCAGATGTGCGATATACACTATCGATAACGAGCACAATTTCTTAATTCTAATTT

FIGURE SHEET 774

AAAACAATTATATAACGGGCTTTCGTGTTTTATTTAACAAATAGTGAATAAAATGCGGCTACTTCTTTTTGATGTACTTCATGTACTTCTTGGCG
TTGAAGTTGTCCTCCACCTCCTCCATGATCTTGACCTTCTTGCGCGGCTTGCGGGCCTCCAATCTCGCTCTGCGCTCCGCATCGGTTAAGGTGCT
CAGATCCAAGGGAAGCTAGTAGATGGTACTCGTTAATTATGGTTTCGTTAAGTTATAGTAACTAACGTTACCTTGATAATCTTCCTGGGCTCGTG
ATAGCGGATGTTTATCGTGGATCCATCGGGTTGCACCACAACTGTGGGATATAGCCGGCAGTAAACCGAGCGATGCAGCCTGGTAACCGCCGTCG
TGGCCGATGAGATGCAGCGTATCTGCTGAACAGCCTGGGGCAACTGTTTCAGCAACATTTTAATTGATAATCACAATATTTACACTAAATAAGAG
CTACACTTAAATCGTGTTTTTGCTGCCAGGCAGCTGATAGTGTGACCGACCCGAGGGTAAGATTTAAAGACTCCTAAATTAGTTATTAAGAATCT
GTGGTAGCCCTGGTTCAGTTTCCACATTATGTGGTATTTTCCCCAGCTCTGGTCACATTCGTACTCAAAGTGTAAGTGTTGGTTGCAGAGGCAGA
AATTCTTATTTTTCTCCTTGAAAATATAAGTACGTTACGTTAAACACTGCAAAAATAATAAAAAAAAAGCGCACGGTTGGGCTACAACAGCGATT
AGTCTGCAAGCCTCGAGGAAAGGACTGCAAACGCGTTTTTAGTTTGAAGGAACATTGAGGATTGAAAAAAATTACATAATTTTTGCGAGCATAAC
TCGCCGTGCATTATGTCGATAAGTCTGCAACTAAA
(SEQ ID NO: 1435)

Exon: 49575..48994
Exon: 43605..42710
Exon: 16140..16019
Exon: 5796..5598
Exon: 5538..5453
Exon: 5379..5124
Exon: 5063..3295
Exon: 2755..1001
Start ATG: 43087 (Reverse strand: CAT)

Transcript No. : CT18533
GGTCACTCTAATCGAGTCGGAAAACAAAGTCGGACGTCTAGCTGCGCGTCGCTCCCGAAGAACTGTTAATTTGTGGACGCTTTTTCGCGAGTGCA
GACATAAATGAAAGCAACATATCTTTAGCTCCATTCCAGACTGGATCATAGGCTATAGCCCGTTAGAGCAGTGCCAGTGAATCGGTTACCGAATT
ATAATCTCGCTCTGCGTCGGCTGAGTGGTAATGTTGAATGGACAGTCGCGTCTAACAAAAAAAAAAAAAAAACAAGTACACACAACCAACGACGAA
TGCACATAAACAAGACGAGACAGCAAACGCAGAATCGAGTGAAAACCTATTTTAAAACACCAGAGCTATATTTATTTTGTTGACGCTCAGGATTT
TCGGTCCTCGCATTTGTGATGTCTGCGGGTGCGTGTGAGTGCGCGAGTGCGAATGTGTTGGTTGCATATCACGGCGGATGCGAATAACTGCAATT
GCAATAGAGAGCAGACACATACACACAAACACAAGCATAATTGGATTATGGCCACACGGCAATAAGAACGGAGGGAGAGAGAGAGAGCAGTCGCC
AAAACCAAACGGACTTCCAACTGCGAGCGCTTCCAGTGCAGCTTCCAACACAATTGCAACGTGCCAAGAATCGAAGAACAATCAAATGCATTCCA
AATATCCAACAACTAAATACACAAGTTTCTCTATTACGAAGCAAGCAAAAAGTGATTGATAGTTAGTTCTCCACAATTTTTTTTCCTGTTTCAAA
ATTTTTAAAATTGTCAAATTCAGACCTATGGGTCCCATAAATGTTTCGTGCTGCGTTCCATAAGCAAACACTAAAATATATCATCCGTTGAACAA
ATCGTGCCCGTCTAACTGTCGCGTCAATCCGCTAACTATTGTCTTGCGATGAACGACACCATGGTGTAGCCAAGAGAACATCAGCATTAGCCAAA
CCACACAGTTCCCAACTCGATCCCCAGAGATCCATCACCCCCACAACAAGCAGGCAAGGCGAGGTCGTCCAACGCCAAAAAAAAACAAACTTAAA
CCAACTTCACATACACATCCGGTTACGACAGCAACATACGTCGTAGCTGATAAACATGAGCCTGAATCAGCACAGTGGACCCGGCCCGCCGTCGG
AGATCTGCGGATTATCGGTGGACCAGGTGGACTCATCGGCCGCCTCCCCTTTCATCTGGCCGAGCACAGCGGGTATGTGCACCACCGCCACCACC
GTCACAACATCGACCAATGGAGACGCCACCGCGGAAGCACCAGTGAAACATCAGCCGCTCCACAACGGCGGCTGGATCGGAAATGGTCTTCCGCC
GGCGCCCGTGACGCGGACCATATCATCGGATCGCCTGGTCACCGGCAGCTCGTGTCGGGCGCTGCGCACTGCCGTCTCAGCATTATACTCCGTGG
ATGACTTCGTCAAGGAGAAAATTGGATCGGGATTCTTCTCGGAGGTTTACAAGGTCACACATCGTACAACCGGCCAGGTGATGGTGCTCAAGATG
AATCAGTTGCGGGCCAATCGACCGAATATGCTGCGGGAGGTGCAGCTGTTGAATAAACTTTCGCATGCGAATATATTGAGCTTCATGGGCGTTTG
CGTGCAGGAGGGCCAACTGCACGCCCTGACCGAGTACATCAACGGCGGCTCCCTGGAGCAGCTGCTGGCCAACAAGGAGGTGGTGCTCAGCGCCA
CGCAGAAGATAAGACTGGCGCTGGGTATAGCGCGCGGCATGTCCTACGTTCACGACGCGGGCATCTTTCACAGGGATCTGACGAGCAAGAATGTA
CTTATTCGCAATCTGGCCAACGATCAGTACGAAGCTGTAGTGGGTGACTTTGGTCTAGCCGCAAAGATACCAGTCAAATCCAGAAAATCACGCCT
TGAGACAGTCGGCTCACCGTATTGGGTCAGTCCGGAGTGCCTGAAGGGCCAGTGGTACGATCAGACAAGCGATGTCTTCTCCTTTGGCATCATTC
AATGCGAGATCATAGCCCGCATCGAAGCGGACCCGGATATGATGCCGCGCACGGCGTCGTTTGGACTGGACTACCTGGCATTTGTAGAATTGTGT
CCGATGGACACTCCTCCTGTGTTTTTACGTCTGGCCTTCTACTGCTGTCTGTACGATGCCAAGAGCCGACCCACGTTCCACGATGCCACCAAAAA
GTTGACTTTGCTGCTGGAGAAATACGAGCACGAGTCGTCGGCCGGAGCAAGTCCACTCAGTTCCCTGGAGTTGATCAACTGCTCACCAGGAGGCA
GCGATTCGGAGAACGTAACGTTGACACCCCGAGCATCAGTACCCACGGTGGCCACTATTTGTACTGCTCCTGCTGGCACTTTAACACCGCGCCAT
CTACAGGAAGTGGACGAGGACGGCTTCCGATTTCCAAGTAAAAAGTCTGCTTCGGCTGCGCTTCCGGGCACGCCAAATGGATCTGCTGGAAGCAG
TGGCTTTGATGATCATATACTGAAGTCTAGAGTGCGACGGGCTACTCAGAAGTTGGAGGCCGAGATCTTGTTGCACCGGCGTTCGCTAAGCGAGA
ACATCATCCACTTCCCCATGCACACGTCGCCAAGTGACAAGGCGCGGTGTCATCAGATGCAGCGACAGCGCTCCTCAACACACTCACCAACGCCC
CCAAGGCAGCTTTCCTCGGTTCAGTTGCCCGCCACGTCTATTCCAGATCCCCCACCGCTTCCCAAGCCCGTTCCAGCGGTACTCACACTGCGCAA
AGTGGGCGATCCACAGTACAAGCCGACATCTGAAAAGGATCACAACGGCTCTAAACCCAATCCGTTTGAAGCGCTGGCGCAACTGCGTGGTGTCA
AGAAAATCCTGGACGCCAATCCGAAAACCTATGCAGCAGGGGTGGAGATCTATTCAGCTCATGCTTCGAGATGCTAGCGCCGTTCTTCAAAGAA
CTGGCCGCAATGCAGAGCAAAGCGGGGGCTCAGGGCGGAGGAACGAGTACGGAGGAAACATCAACGGGTAACAAGGCTTCGGCAGCAACGCCCAG
TGAACCAAAGAGCCTGCCAGTGTCGCCGCATATGACGCGCAAATACAGCGCCATCGAGCTTCGACTTCCTCAGCGAATCAGCAATGCTGCTCCTC
CAGCAGTTACCAGTGCTCCACCACCATCAATAGCATTGCCAACCGATGAGGATGACTGCGATGATTGCAATTCGGAAGGTGAGGATCCCGATGGC
GGTGGCAACTGTGCAGATGCGGAATCAAGCAGCGATGACAGCGCCGTGCGTCCGTCCACTGTGCCAACCGCTCGAAAATACCGCGCGAATTCCTT
GTATGCGCATCCGCTTTTTCGCGGCTCCAATGGCACCAGCATGAAAAGTACCAGTACTGGTGAATTCGAGAGTCCAACTCTACTGAAGGCCAGCG
CATCTACAATCACGTTGACTGCGTCAGTGGGTGCGACCAATTCGTGTGAGGATCTGACTGAAAGCGCCAGAAAATCAAAAGAGCAAGCGAGTAGC
GGTGCAACAGCGGCGGTGCAGGCTTTGCCCACTCCCATGTCTGGCTGCTCCACCAGGTTGGTGGAAACCCCGGTGTCCGTTTCATCCTGCACTGA
TCTTGAGCTCGACGAACTGAAAAACACCTGCGATCTGAACGAATTGAAGAACTCGTGTGAGCAGCTTCCCTTGAAGACAAACCTAACGAGGCGGG
ACTCTATAGAAAGTGGCTTCTTCTCGTGCTTTAACGAAGAGTCCGATGCGGCGATAACCAACAACAGTTTCGGACGGCAGCTGAACGGGATTGGA
TCGTTGGGGTTTGGTTGCGGCGGCGGGGGCAACAGTAGCAACTGCTGCTATGAGAAATTGAAGACGCAGCTTATGCTCGATGCATGCGTCAGCGC
AGATAGTGAAATCAACGATAAACTGGCGAGTTTGTGTCGCTGCTGCTACTACGCCACCTCGACATCGAATGCCGCCGTAACTGCAGCCGCTGCTG
CGGCCCAGCAACAACAGCAGAGCCACTTGCTCAACGATACGTCCTCGACCTCATCGTCGGTGCTGCTGATCGACAATGATCCCGCTGTGATCGGT
GGAAATACCTCATCATCCACAGCGTTGGACTCGATGGATGACTTGGACGCGGACATTGTGGCATCGCGGCGCACACACCAGCGACGATACACTTG
CCACCATGCGTTGCTCAGCGGGAATGGCAGCGAATCCCAAATGGCGGCTACGGCGAGCCTGATCAATCGTCTGGCTTTAGACTCGGAGATACATA
CTCTGCTTCAGCGTAGTCCTTTTGCAACGAATCAACTATTGTACTGTAAGAACCGCACCTCGTCCATATACACGGATAGCTCCGATGATATAAGT
AGCTTGGCCGGCTCTGACTCCCTGCTCTGGGACGACCGCTCCTTCACGGCACTGCCCAGTACAAGATCCGCACAGATTGCCAAGATAGTGGAGTA
TTTTGAGCGAAAGCGACAGGACTCCTCGCCGCCTTCGGTGCACCATCGCAATGGGAACGGGACGGTAGCAGCTGCTGTGGCTGCCTCTGCCCTGG GTTCCAACTACCTTTCGTACGAGTCGCGTCGCTATTCGGACTTCAAGCGGCACCTGAACGCGGATGGCCTGTGCTTCGATCTGGACAAGAAGCCG
GCGCAGCAAAGGATGATGGTGTGCGAGGGTGCGGTCAAGTCGAAGCTTCCCATATTCGATAAAAAGAAGCAACAGCAAGGCGGCTAGCTGTGGTG
GGGACCTTGTGATGAAAACCCCGACCTGATTCATATTTAATAACTTATTTCTTCGATTCTTTGAGATTTTTATCCCCATACACGATTCCTTTATA
CCTGGCAGTACCACTTGATAAAAATACAAAAAATAATCGCAAATAATTTTGCCCACAAAAGTTGGTTAGTTTACGATGCCTAAAGGTTTAATTTG
TAAGTAAATAGTTATTTCCTTATTGTCAAGTGTATAGAGCGCAATTGTAAGTAAGCCAAAATGTTCTACTAAAAATTATGCACGCTCTTACAATA
AGAAACCCAATTTCGTTTGTATAAGTTGAAAAATTATATATAATTACCATTTATAAGCATATAGATAAACATAATCATACGTCGTACTGGTTCCT
AGTCCTTCAAATTTACTTCGCTACATACATTATGCTAAATAGCGAGTATTCAAAAACCAATCATGGAAAGTATTTATTCTTAATAATTATATCTG
TCGCTGGTAAACTCCTATGAAATGGCATAGCTGTTCTTTATGAATACATTTACATATAATTTTAAGTTTATCGCGCTATTTATTTGATTTTGTCT
AAACTCTGTATAAAAATATTATGTTTAAAATACAATACAACAAATATACACACATTTATACATAAAATGGCATATTGCAATGTATACATTTTACC
TGTAACGATTAATTACCGCGTAAGGTCCAATTTAAATAATTACATAGACTTACCGACTTGAGGTTTTAAGACTTAAAGCCCCCTTTCCCTCGAAA
ATTGTACAGATGATCCCGGATCGATTTGAGAAGCAAGAACACTTATCATTGGCCAATCCCGTTCGGCTTAAACACGACTTATGACTTTAGTTTTA
GATTCATACGTTACAAATATGTGGGTATCTGCATTACAAATAAATACATAAGTATACATT
(SEQ ID NO: 1436)

Start ATG: 1101 (Reverse strand: CAT)

MSLNQHSGPGPPSEICGLSVDQVDSSAASPFIWPSTAGMCTTATTVTTSTNGDATAEAPVKHQPLHNGGWIGNGLPPAPVTRTISSDRLVTGSSC
RALRTAVSALYSVDDFVKEKIGSGFFSEVYKVTHRTTGQVMVLKMNQLRANRPNMLREVQLLNKLSHANILSFMGVCVQEGQLHALTEYINGGSL
EQLLANKEVVLSATQKIRLALGIARGMSYVHDAGIFHRDLTSKNVLIRNLANDQYEAVVGDFGLAAKIPVKSRKSRLETVGSPYWVSPECLKGQW
YDQTSDVFSFGIIQCEIIARIEADPDMMPRTASFGLDYLAFVELCPMDTPPVFLRLAFYCCLYDAKSRPTFHDATKKLTLLLEKYEHESSAGASP
LSSLELINCSPGGSDSENVTLTPRASVPTVATICTAPAGTLTPRHLQEVDEDGFRFPSKKSASAALPGTPNGSAGSSGFDDHILKSRVRRATQKL
EAEILLHRRSLSENIIHFPMHTSPSDKARCHQMQRQRSSTHSPTPPRQLSSVQLPATSIPDPPPLPKPVPAVLTLRKVGDPQYKPTSEKDHNGSK
PNPFEALAQLRGVKKILDANPKTYAAGVGDLFSSCFEMLAPFFKELAAMQSKAGAQGGGTSTEETSTGNKASAATPSEPKSLPVSPHMTRKYSAI
ELRLPQRISNAAPPAVTSAPPPSIALPTDEDDCDDCNSEGEDPDGGGNCADAESSSDDSAVRPSTVPTARKYRANSLYAHPLFRGSNGTSMKSTS
TGEFESPTLLKASASTITLTASVGATNSCEDLTESARKSKEQASSGATAAVQALPTPMSGCSTRLVETPVSVSSCTDLELDELKNTCDLNELKNS
CEQLPLKTNLTRRDSIESGFFSCFNEESDAAITNNSFGRQLNGIGSLGFGCGGGGNSSNCCYEKLKTQLMLDACVSADSEINDKLASLCRCCYYA
TSTSNAAVTAAAAAAQQQQQSHLLNDTSSTSSSVLLIDNDPAVIGGNTSSSTALDSMDDLDADIVASRRTHQRRYTCHHALLSGNGSESQMAATA
SLINRLALDSEIHTLLQRSPFATNQLLYCKNRTSSIYTDSSDDISSLAGSDSLLWDDRSFTALPSTRSAQIAKIVEYFERKRQDSSPPSVHHRNG
NGTVAAAVAASALGSNYLSYESRRYSDFKRHLNADGLCFDLDKKPAQQRMMVCEGAVKSKLPIFDKKKQQQGG*
(SEQ ID NO: 1437)

Name: SERINE/THREONINE PROTEIN KINASE
Classification: protein_kinase
Gene Symbol: cdi
FlyBase ID: FBgn0004876

Celera Sequence No. : 142000013384325
ACAATTACTCAGCCGAACTGTTTCCCACCGTGGTGCGGAACTCGGCCATGGGATTGGGATCGATGTGTGCCCGTTTGTCGGGAGCCCTTACTCCG
CTCATTACATTGCTGGACTCATTTGATCCGAAGATACCGGCCGTGCTGTTCGGCGTGGTGGCCCTGATCTCGGGCTTCTGGGTTATGTTCCTGCC
GGAGACAATGAACCAGCCCATGCCCGAGTCCATTGAGGATGGAGAGAACTTCGGAAAGGGAGATACTTGGTTCAGTCAGTGTGCTGGTCGCAAAA
AGCGCCAGAATAGCGTATATCCCGACGATCCGGAGCAAATGGTGCCGCTCAAGAACATCGAGAGCAAGTAGAACCTAGCCAAAGACGATTGTTTC
CCAAGTCCAAAATCCAGCTTAAATTCCTTGTTACCCTGTGTTTTCTTGTTAAGAATTCTACTCTTCTGCCTAGTAGTAAGATTTAATAGTTTCTA
TTCATTCCAAGCGAATAAAACGATGTGCAGAATATGGGGAATCCTAATTTGTGGATTCACTCATTTCTGAGTGTCCCTTTGTTGTTTGTACGGAT
TTTTTCTTTTAATTTTTTCGGTGGTAAAATTTAGTTTAAAGGAAATTTAAATGCTTGACGAGCATTTTTACTGATTAGTGTTGTCTACTTTTAGG
CTCTATCAATTTAGGCGCAGATTCATAGCTTGAATTTCAATTTTCTCTACGGTAAAACCAGTACACACCAAAAAATTATTTCCCAACTATTTCCA
ATTAAAGTTTATTCTCCGACCGACACAGCCAATTCGGGTTCGTCTGGCCTTGCAAAGTTTCAGTAATTTCCACTCAATTGCACTATCGAATTGCC
AATTGCCGACAGGGATTTCCAATGTCAAATCCATAACCCATCGCTTCCCTTTGCTCCACATGATGTTTAACCCGCCAATTAAAGTTTGTTTAAAG
AGAGAGTTTTGGTTTTTCGGTTTTTGTTTCTTGTTTGGTAATTCTTCATTTTGTTTTGTTTGGTACATTTGAGAACATTCATTTCGAATTTGAAT
ATATTTTCAATTTAAATTTTAACTACACGTAGGCATATAGATTTATAAACGTATGTATGTGTATGCCGATATCTGATGCGATATCGTTACACGAT
TTCGCTGGCTTAGAATTACATTAACATTTACATAGATATAGTAGCTTTATATCTGGGATTTCGGATCGCGGTTCTCGGTAGCGCCTCTGTCAGCG
ATTTCCCGTCGAAGGTACACAGAGATATATGTAGATATTGTTAGCAGGTATTTGCGATGGCTTAACATCAATATTCTTACACATAGACACACTCA
AATCGCGAGATAAACACATCTAGATGCGGTTGTTAGCCAATGAACTTGTATCAGAAGCCAACTGGGGTAAATGCTACGCTTGAAGGAAGGGTGGG
AAAGTATGTCGGGTATGGAGTTCGAGTGCCTATTAATACAAACATACGAACGTAGCTAAATATATGTATGTGTAAATTAATCACAATTGAATCG
GAAAATATTTACAAAAAATACTCAATCGAAGCCCCAACCATCCGCAGAGCATGAGTCCCAACCCGTTGTCCCGATCGTTTGGTTTTACAACTCAG
GTTTTCAGCTTTAGTTTCGTCACCACCTTATGATTATGCCCGTTCCGGGCACTTGGTCTGGACAATTGGCGCCTTCACCTGCAGTCCCGGCCCGG
TCTCCGCCAGCATGGCCGTGTGCACAATAATGGCCGGCTGGTCCTCGCTCTGAGGATGCAGCTCGTGCGACTCGCCGGGTGTGAGGCTAGCCAAC
GCGGCCAAAAGATCATGGTTGACCAGTGGCTCGCCTTCCTCGCGCGGCTCCCAGCCGGCTGGCGGCGAAGCGGGCGGGGAGATGAGGAACTGTTT
GACCGGCGCCGGTGGCTGCAGGTTCTTGTTGCTGACCGGTGTCACCGGCTGGGCAAAGTAGCAGGTGATAACCGTCTTCTTGTTAAACTCGTACT
GGTGCAGCTTGATTCGCGCATTTGCCGCCGCAATGGCATTGTCATAGTTAACACGCAGGCGACGGAAGCTGCGCAGCCACTGGAACGTAGCCGAT
TCGCTGAATGTGCGGAATAACTCCTCCATGGCGTGCTTCAGCTCTGGATTGGCAAACACCTCGGAGTGGATGTTGGTCACGATGATTGAGGTGGG
TAGGTCGTCGAACGAGTCTGCATCCACCTCCGGCTCTGTGTCGCTATCCACGTCTCCCTCCTTTGGGAGCGACGGATGCTGATTGGGCAGGCCGT
CGGCGGCGTTGATGAAAATGTCCTGGTCCGGCGACAGCTTGTCTATGCTGCCGCCTCCACTGCTGTTCTGTGTCGACTTCAGTTTGTTCTTGCTT
CTGCCGTTGGCGCTGTTGTTGTTGTTGTGATTGCCACGCGGAGTTGTCGGAGTGGCTGCATTGGCCGCGTCAGCTTCGCCAGTGGCGTCAGGAGT
GGTCGGATCAGGTGCATCGGCGGACGCATTGTTGTTGGACTTGGCCGCGTCGGACATGGCTGGCTGAAAAGGAAATGAAAGCTACTTTAAATAAT
GTTTACAATAAAACGTTTTTATCGAATATGGCGAATAGCAGCCAAGAAATATACTTCTGTTAACCATCCATTTATTATTTACGAAGCATAAACCC
TTTTTATGTTGTTAAACAACTAATTATTGGGGTCAAATAAATGAATTCCTCGTAAAGTTCATTTAAAAGCTTGTTTTTAATGGCAAATGTATGTG
GGAAGTGGCCGCTGTTCAAGGATTTATTTTTGTGATAGCCATTAATGCTATATTTATGTTATACGGCCTTTAATTATAGCCCAACGAGCACGGAC
TTTACAGTAATTGGATTCAACAAGTCAGTGACATTCTCCATAAATAGAACTGTCAGCTAGTTAACCTTCACCTCCAAAACATTTTTAAAAAATTG
GTAAACAGCACTCGCAAATTAATTCCGCACAAGCGACGAGGGGGTTGGATAAACACCTCAGCACAACGACAGGATAGGGTTTTTGTTTGCGTAAT
ATATTTGTAACAAATTTCGAGCGCCACGCTACGTCAAAAGAATTGCTACCGCTTTTCACGGAACTGGCAGCCCTTCAAAGCAAACCAATTACGGT ACCAAAAACTACAGACGTGTCTAAGTTTGGGAAGGAGCGGGGACCACAAGGAAGTGGGTCTCCGGCAGGCGAGGACCTTAAGTAGCGACACGTG
AAGCTAATCAATAGGTCTATCAAAGGGGTTGGAGTTAAAATAGGGATCTCCGATGGTGACGCACTGTTGATTCACAACTGCTCTTGATTTTATTG
TTATGCCTGCTAGCCACAAACTTTTGGCGAAGGGAAAGCGCCAGACGGTTGATTAATAGTAGCGAAATTTTTATGAATGAATGAATTAGTGAGGA
ATTGGCGTCAGAATAAAAATGGTGACGTGTGTCTGCTTCTGCTTCGCACCTGTGACCGCCATGAAACCCATTCCCAACGAATCCAAGGGAACCCT
TGGTGGGTTTCATTATAATAACTGCCAGTCGTAGTTCTGGATGGGTGCCCATTTGTATGCTATAAAAATAGCATTCTTCTTAGTGTTTTATTGTG
GCCCATGAATCAGCAATATGCAGTGAGTTAATTATACGCTGTTTACCCGGACAGGGAGTTATTTCAGACAAATGCAAATGGGTTTTTGTGCTAGC
TTGGGCTAACAAAATTGGCTTAGTTTTTGGGTGCGAAATGTGCGAAGTTTTTATGAGTTTCCATGCAAGGATTCGGCCCAGCAGCTGAAAATGTT
TGCTTTGTATTTCTTAATTAATAATTTTTGGCATAAATTAAATTTCCAAGAACTTTTAATGAATTTTAATTGGGATTTGGATTTTATGGTTTCCA
TAACTCAATTGATTTTATGCCGGCAACTATATTATAATTTTGTTTTTGTTATTTCTTAAAAAATGACTGTTAATAGACTAAGTTTTACGTGCTAA
TGCGATTATATATATTTTTAAAGGAAGGCAAATGGAGCGTTGAAGGATAACTAAAATAGCTTAAGGGTTATTCTTGGCTATCAAATAAAGTAAGA
AATTCCAATTACTACCTTATCTATGAAATATGTTTTCTTGGAACTAAGCCATTCTTCGTGTGAAGTAAATTGCTTTTTAAAGCGATTAAATTGTA
ATACCATCTTTGTGTTAAGCTTATACTTATGATTTTCGGAAAATAAATAATCACTTGAAGGAATGACAAGGCCAAGGACTGGGGTTTTAAAGCTC
ACCAGACGCGACGCAAGAACCTCTTTGGCTACTGAATTCCCAAAGCTTATGCTTTGTTAGTACTTTCACTTTTCTTTTATGGCTATTTTATTTTT
TGTTGACTTTCACCTCAACGCAGGTCAGCAGAGCAACAACAGTAAGCGCCGTAGCTAACAATAAAAACAAAGGCCAAAAAAGAACCCAACGACGA
GTTGATCTATTTCCGTATGATTGATTTCCTTGAAAGGACACACCCACGCAATTGCGACTTTTGCTTCCAGCGGCAGTTGGAGATGCTACTGTTGT
TCATGACGTGTGTACTTTGTTTGCCGTAGAGCTTGATCCCTATCTCAGGAGCAGCATGGGAATGAGGACGCGTGTAAGTGCAAGTCAGCATGAAC
GAGCTGCTGGCATGCAAATCGCATGGGCCGCGTGTGACGTCACCGTTCCTGCACGCAATCCATAAAAAAAAAACGAAGAAAGCGGGCCGATAGCG
CACTTTAAACTAGACAAAAGTAGCTCTCAGCCCCGCCCACTTTTGAAAGCGGTGCCGTGGTTTCGACATGATGATGAATTGCCTGCCGGTCGTTA
GCCAACGACCTTCACTCATTCATAATTGCTGTCATCATTATATCAAGTGGTTGCTGCCCCCCACCATAGGACTCCTGCTCTCTATCCAACCATCC
ATATCCATGTAATCATTTGCCAATCCATCCATCCTTTTGCTCATCCCGCCATGTCAGGCTTTGCAGATTTTTAGCCATAAGTAGCCCGCATGTAA
GCCACCTCAAAGACACGCAAAAGCTCTCTAAATCATTTGAGACGGCTTCAGTGGGCCACTCAAAAAAAAATCAGCAACAAAGGGATATAAACAAA
TTCATGTAACATTTTAAGCTGAACACTAATACAATGCGTTGCCTTTTATTACTTTAATAATATTGATCAGAAGCTCTAGGACATCCTTAAATGTT
TAAGTTGCCATTTAATTGAAGCTCACGTCCCTCACTTAAAATTGATCGGATGTGTTCGTGGAATACGAGTGTGAGTGAATTGTGGCCTTATTTA
CATTATCGTCCCGATTTCGTGACAAAAGGAAAATCCCACGAGTGCGCTTTCCACTCTCCATTACAGCTGCTGCTATTGCATTTGCCGCTGCTGCT
ACTGCTGCAGTTGCAATTTCAGTTTACCCTATTTGAATGCAAATGCAAATAACGCTGGGGGAAGATTAATTTGATTTTCTGCTGAAATTTTAAAC
TTTCTCCTGGCAGATACCACGCGTCTGAGCCAGATATTTGCGATTGATGTAAACCGCCTGGAATTTAATTAAATTGTTCCTGGCCTTTATAGAGA
GCTCAAAGCGGCGCTCTGTTATTACAGCTCCTTGCGGTTGCCGATGGAGGTTTTGCTGCTCATATTTGTGCCTGCAAGTGTCGGCTTCGTTTGCC
ACATGTCACATGTTGCTGCAACCGGAATCCTTTCAAGGCAACTGCAAAAGCAAAAGGTCAGGCGGTCAGGTACTGCTACAGTTCGGTCACTGCTC
GTTGGGCTTGCTCGAAGCAAGCATTACATCAGGAGTTCTGTGGCAGGACGACACGCGAATCGTGTGCGAAACTTAAGATATTTTGCTGAAAGCTT
CGTCAACTAAATTAATTGAATCCTAATTAGTTTGGAACTTCCCTTTGTTCACTGTTCAATCTGGGCTGGATTGCTTCTGCTGTAGGCTTAGAAAT
TTCCCACACACGATGCTCATTGTTGGAAATTTAAATACTCGTATCTGTGGGCTGCACCTGAAAGTATGCTATTCTTCCCACACACATGGAGATTC
TCTGTAATTTAGCTCCACTAAACCAAACCAGCTTTGCTTTCACGGCTGCTGTGGCTGGATAATTACTACCAAAGGTGAAACGTTCACCGAAAACT
CGCCCAGCATCATGAGCGGTTTTGCGTGGGAGCGGCATAGCCTTGGTGAGTGCGTGGTTGTGGCTGGAACGGAACAAATCCTGCTGATTGGCAGG
ACATTGATTGGCCGCATGAGCCATGTGTGGAAAATGCAAAATGCTTAAAAGCTTAGCTTTGGACTGCAGATCAGCGAGATTTGTATTTGATTTCT
ATATACACTGCGAAGATATTATTTATTCTATCACTAGAAAAATCACAATGAAACAAGAACGCTAGAGTATTTTAAGTAAACAGTTAAGTAAAAAG
TTAAATATTTAAGATTTATACCCAGCAGAATAAAGCAGACTACAATAAATTTATAGGAAATCGAATTACCAGGAAAGTTTAATTCCAGTAAACTG
ACCAATGCAAATTGTAATTATCCCAAATTATGCAATATTTTAAAAATCAATTTTTTTTTATTTTAGCACGTAACTAATATGCTTACTAATTCTAC
GGGGAACTGTGTGGGTTTGCTTTGTGGAAACATTAAACGTAATCCCTTTATCCAGTGGATAGTTGTTCACCACCCGTCAACCGGTCACAAGATAA
CAACTATATAGCTTTGTTAATGCCGATACCTTTGTAGGCTGCGCACAGCATCCGAGGGAAAATCACGGAATTTGCTGAATTTACCTTTGGCTTGC
ATGACAATATCAGGTTTTCGTAATTACCCGACACTTCCAGGCATGAACTGTTAATTAAATCATTTACACACCGATGAATCGCACCGCAATTGGAT
TGTTAACACATTTGTACCAAGTGAATGTATGAAAAATGGTTTCTCTTTTTGGGGTCAGAAAATTCCTGGCATTTCGATTGACCTTCGACGAAATT
GTAAATTCTAATGCGGCCCCCATACACATACCATAACAGCTCATCCATCCCCGCCCACTACTTTTACAAATTGGATTGTTATCACTCAAAGTCCT
TGGGCGATTCCGAGGAGTTTTCACTTGCCTCAGACTCAAACTGATTCGACCAGCCCCTTTGTTGTCGACTGTCACTCGCAACTGTGCGGCTCCAA
GTGCAAATGTATCTGTGTATCTGTAGGTTTCTGTGTGCGCCCGTCTTGTCAGCGCTTTGACATGAAAATAGTTTGGGCCAACTTGGCTATGCAAA
AGCGATTTCTATTAGGAGCCGCCATCGCCGACATGTGCTGCCGAAATTCGGTGATTTGGGTAGGATGAAGAGATTACCAAAAGTTTACAGTGGTT
CTTGCTTCCAAGCAAGGAAGGAATTAAAATCCTGTTCAGCAAATATTCCAATAAATCGCTTTTAAGCAAGTGTTATCAGCAGTTCAATGTTGAGT
TCAACCGGTTGAAACCCGCTGGTTATCGTAAATCATGGCCACGGTAGTTCCCTCGATTCGCTTCTTATCGCGACGACAGTCCCCACTGACGCACC
AAATGGACGTATTTAGACTCCATAGATAACATTTGGCTATTGTTACTATGGTTAATTGAGACATTTACAACTCAAGTATACCTCAAGTCAAGCAG
AACATACGTATGCGCGCATATACAGTCGAATGGAATCGACGTCGCTGCCAATCAGGCCGATGTGTTAAGTGAGTTAGGGGCACTTTTGCTTTTGG
GACGTGACGTCAGTGCAAACTGCAGCTAGATCCAGTCAAGCCAATTGACGAAAGAGCCGACGGCAGCGGTCTGTACGTATTCAATTCATCAATTG
GCAAAACCCTGGCAAAAAGGCAAGAAGATGGAAAACAAAACAAAAGCGAACGCAAACAGAAATAGCATAAAATGGACAACAGACGCGACAACACA
GGCACCAATCGTAGGGGCAAAAATTATGAGTTGCTTTTATTTTAAAATCGTTTCATTTATTTTGCGTCAGCAGCGCCTCTCAATGAGGAAACGCT
GCGTATACATAATTTTCTGGCCACATATACGCACTCCCATATCTTTCTCCCATCGATTCAGTGGTCGTTCGCAATCAAAGGCACAGACGAGTGAT
CTTTCCTTGGCCTTTTGCAGTCTCTTAAAGACGGGTTGTTTTCGAGTGTTTTTTGCAGCAGAATGGTAATCAGAATGCTCTCGGCAATTCTTTAT
TGAACGACCGTTCAATAAATTTCACAAAAGGAAATGTTATCAGCGGGTATTCTTAAAATAACTCAATCTTTAACAACTTATATTTGGAATCAATC
ACATCAACCCGTAATCAGATAACTGATAACATTTTAGAGGAAATAGTTTGTACCGGCACATTAACAAGTTAATGGTTTTGTTATTCGCCTTATCG
TGAAATACTGTAAATAAATTTTTTAATTGCTTTTCGAAAGTAGTTGTTTACAACTTAATTTATCAGAGTGTTTTTGTTCTCCGCTCAGAATTAAT
CACGAAGTGGGGTGGTAATCCAGATTAACATAAGAAAAAAACAATTTTAAAATATAATATTAAGTCGCCATTATGCATGAGTAACAACTAACAAA
TTGCTATAAATAATAGGAGATAATCTTGAATACTGCTAGAAAGTGTAATACAATGTAAGGCAATTAAATGTGCAATAAAATCAATGTTATTATCA
GCATGATTGTATATGTCGGAGCGCGACTCTTCGCATTCCAGAAATTCCTTCTGTGATTTCATATTCTGATGAAATTGTAATATTGCGGTAAAATT
CTGTCGAGCGCTGCGGCAGAGGCACGAACAGCCTCTGCAGCTGAGTGAGGTCCGATCGAGTGGTCATAAATAGTGTGTTAGAGAGAGATGACAAT
GTGGCACACGCCAGTGTGTATAGCCATTAGAGAATATGATGAAGAAGGGACATGTAAGAAGATCCCTTCAGTGAAGTTTGACTGCTGACGTCGAT
CGGAACTTGCTGCGCTGACGTACAAAATCGCGAAGTGAATAAATAATATGGATGAGACTCCTGTTTCGCCGACATATACAATAGTGCTCAAGACC
CTAATGGAATTATACGTTAATAACCAGCCACATTTCTTAGATATTTCTAATATGAGCCATCTGCTGCAGGTTCTTTCCAATATCTAATTCTAGAT
CTTCTTCGAATACGACCTTTTTGGCCATGAAACGATGATTTGCCACTTCATTCACAAGCATTAATTTGTCATGATTCTCTTAAGCGTGCACTTTA
TCTGAAAGTCTGAACAGCTGGCTGCGAAATGGATTCCCCGGATTGGAAATGGCAAGTAAATCTGTCCTCGCTACAAACAAGTGGGCACCACTGGG
CATTCGGGGAATAGGGATATGGGTAGGAATGGGGATATATTGTGGCATTGGCGAAAGGTCGCTATGCAAAGCCAAGGTCGAGACTTACACCCAGG
ACATTGTGTTGTGCGGCTGGCAGTAGAAACGCCCACGCACACGCCCCTGTCAACTGGCCGGGTAAAAAATAGAATCAAATACATATGTATACAGA
ACAGGAGTTGAAGCAAAGCTCGCATTTTATTTGCATTTGTGAATTTATTGCTTTCGGTTACGTCTGCTTCGCCTTGCCACTTTTCCAAACTCGTT
GTGCTGCTGCTTGGGGAATTTTCGGAAATTCGAAGTGATTGGGTTTGGAGCAGTAGCCAAGGGCTTCTACTGTTGCTCAAAGCAATTAATATTTG
AGAAAAAATAACGAAAACGAAGTAAGGCGGCAGCAACAAAGCGACCGCAACAGTGGCAACAAATCGCCCCACACCGCACGTCTTCAGTTTACAAC

FIGURE SHEET 777

CAAGGACTTGGCACGTTTAAAATTCAGCCAGCAGCCGCAGCAACGAACACGGACAGTGGGCGGAATTTAATTTCGAAAAACATATTACTTTATTG
TTCACATCTTTACCCACCTTCCGATTCGAGTACATACGATTCCACTGAAGCCACTGAAGACTTACTTCACTTAAAGTACATTTTCTTCAACTTCG
TGGGGTCTTTCTAGAACTTAAGACTTATTCTAACTTAAAAAGACTATAAAGTTTTTAAACATTCCGTTGTTTTGTCAAATTTGAATAATTTACGA
ATGTGAATTTGTCGCAGAAGTATTGCTGAGTATTATCTTTATAAATTTTTCATTTTTTAAAGTGACTAAAGAAACAGCTTTAATGCGTCTTACTT
CATATTGGTCATCCCGACCACAGTGCACTGGTTACCAAAGTATGCGATAACAATAACATCGTCCACTATGTGGTCGTTGCTGGGGTTACGGGCAG
TCAGTCACGGTCACGGCTGCAACCCCTCCGCTCCGGCCAAAACGAGTCCACAGAACAATGGCCAAGGACGAAGGGGGGGGAGGGGGGATTCAATA
ACAACAGCAGGAACAACAAACATTCTGCTCCCACGCAAGAGCAGCAGGAACTGTGGCAAAAACAGCTGCTGCAGGATCAACGAGGTGGGAGTGGA
TTCGAGGACTTTAAAACACGAGCCAACTAAAAATATTCAGACACGCCGAAGCGAAAATACCCTTTAGCAGGGGGTTAATTCAAGTGGGGTATTTT
CCCCTTCTAGTGTTTTTCTTTTACCAGGGTAATCACAGATTCTGTTTCTGTGCACTTAAACGGGGTTTATTCCGTTTCTAAAAATATCAAATGTC
TGGATTGACTTATTTCTTGGTATTTGACTAAAAATAAAAACAAATATGCAGCTTTTGGGAAACTGATTCCTTGTTGACACAATAGAAACCACCAT
ATGACCACACCTTCCACGCTACTGCAATAACTAGAACATTTAGAACAACAAACAGAATGGCACTATTATCGGCAAATGATGGCGCATGCATAAAA
ATGAGGAGATCGAAAGTGGGTGGCTGGGGATGGGATAACCTTGTACTTCTTGAGATAAAAACAGTTCAGTATTTAGCAGCGGCTTATTCCTGAAT
GTTTATAAACAAATCGAGCGAGAGAGCGATGCATAAATGAAATATGAGGGGGGGTGAAGGGTGGTTGCAAAGAGGGTGACTTTTCGCAGACGCTG
CGGCACCAACACAAGCAAAGCAACGGCAACAATTTGCACGTAAAACTCAGCTGCTGCTGCTGCTGCTGTTGCCGTTACATAAGAAACTCTTGCAA
AAAGTGCAAATCTCAATTCGGTATGCAAATGGACCGCTGCCACAATGTACTCACCGTTTTTAGAAACTATTCAGTGGCCAAATTGCGATTCTGCT
TTTATGCGCCAATAACAAACGGCTCTTCTCCACCGTTGTTGTTGCTCTCCTCCTTGTTGTTGTGGTCGCAGCTACTGCTTAGCGAAGCAGTTGTT
ATTGTTGTTGCGGCAACAGTAATTTGCAAGTGCACCGCTATTGTTGAATGTTTTTAGACGATTGTCATGCCAGTGGAAGCTTCCAGTCTGCGTCA
TTCGCGGAGACGCGTAGTTTCACGTTCGACGACACAACCGCTCACAGCGAATTTTGTTTTCGGACTAGAGCTGAGAAACGGCGAATTTTGGTGCT
TCTGGAAACATCGATTAAACTAAAACCCGATAAGTATGCGACAAGCGGTCACACTCGGCGATGTGCGATAGGATTGCTGCATTCGATTATATAGT
TATCGAAAAGAGCAAAGAGAAGCCGGAATATACGGCATTAAAAGTGCATTTTGTATTAAAATTAAGAAAATTAGTAACGATATACCGCAGAATAG
GGAGACATGGCCAACGTGGAATCTATGATTGTGGAGGAAAAGACGCAGGTCAAGCAGATTGACCGCGAGAAGGTTTGTTTGTGACCCCGGTCATG
TTTACTTCGCGTTTGCTCTAGATGTGTTAATAAGTTTATGTATTTTCCAGACCTGTCCTATGCTGCTCCGTGTCTTCTGCTCTACGGGACGACAC
CACTCCGTGTCGGAGTATATGTTCGGCAACGTGCCCACCAACGAGCTTCAGATTTACACCTGGCAAGACGCCACCCTGCACGAACTGACCTCTCT
GGTGCGAGACGTCAATCCGGACACCCGGAAGAAGGGCACCTACTTTGACTTTGCTGTCGTGTACCCCAACTTCCGGAGTAATCACTTCCAGATGC
GCGAAATCGGAGTGACCTGCACGGGTCAAAAAGGAATCGATGATAATAAGACACTTGCTCAGGCCAAATTCAGCATTGGAGACTTTCTGGACATC
TCGATTACTCCGCCCAACCGACTGCCGCCAACCGCCAGGCGCCAGCGTCCGTACTGATTCTTCACTTTCATCTATTCTAATCATTTTAATCTTTC
ACTTGACACTCAATGGAGTATGAACATAATTATAAGTGGAATACAAGTAAGACGAACTACGAGCTGCTTGACTTAAGGGACTATATGTTGTGGGG
AGTATCAGTTCCTGTAAAAGCCGTTCGGGCGCTTCGACTTCTTCTTGCCCAACTGCGTCATGTCGATCTCCAGACCATTGGGCAGCACGGCGCGA
TTCTCTTCGT
(SEQ ID NO: 1438)

Exon: 11550..11265
Exon: 2534..1001
Start ATG: 2527 (Reverse strand: CAT)

Transcript No. : CT19005
AAAATTCGCTGTGAGCGGTTGTGTCGTCGAACGTGAAACTACGCGTCTCCGCGAATGACGCAGACTGGAAGCTTCCACTGGCATGACAATCGTCT
AAAAACATTCAACAATAGCGGTGCACTTGCAAATTACTGTTGCCGCAACAACAATAACAACTGCTTCGCTAAGCAGTAGCTGCGACCACAACAAC
AAGGAGGAGAGCAACAACAACGGTGGAGAAGAGCCGTTTGTTATTGGCGCATAAAAGCAGAATCGCAATTTGGCCACTGAATAGTTTCTAAAAAC
GGCCAGCCATGTCCGACGCGGCCAAGTCCAACAACAATGCGTCCGCCGATGCACCTGATCCGACCACTCCTGACGCCACTGGCGAAGCTGACGCG
GCCAATGCAGCCACTCCGACAACTCCGCGTGGCAATCACAACAACAACAACAGCGCCAACGGCAGAAGCAAGAACAAACTGAAGTCGACACAGAA
CAGCAGTGGAGGCGGCAGCATAGACAAGCTGTCGCCGGACCAGGACATTTTCATCAACGCCGCCGACGGCCTGCCCAATCAGCATCCGTCGCTCC
CAAAGGAGGGAGACGTGGATAGCGACACAGAGCCGGAGGTGGATGCAGACTCGTTCGACGACCTACCCACCTCAATCATCGTGACCAACATCCAC
TCCGAGGTGTTTGCCAATCCAGAGCTGAAGCACGCCATGGAGGAGTTATTCCGCACATTCAGCGAATCGGCTACGTTCCAGTGGCTGCGCAGCTT
CCGTCGCCTGCGTGTTAACTATGACAATGCCATTGCGGCGGCAAATGCGCGAATCAAGCTGCACCAGTACGAGTTTAACAAGAAGACGGTTATCA
CCTGCTACTTTGCCCAGCCGGTGACACCGGTCAGCAACAAGAACCTGCAGCCACCGGCGCCGGTCAAACAGTTCCTCATCTCCCCGCCCGCTTCG
CCGCCAGCCGGCTGGGAGCCGCGCGAGGAAGGCGAGCCACTGGTCAACCATGATCTTTTGGCCGCGTTGGCTAGCCTCACACCCGGCGAGTCGCA
CGAGCTGCATCCTCAGAGCGAGGACCAGCCGGCCATTATTGTGCACACGGCCATGCTGGCGGAGACCGGGCCGGGACTGCAGGTGAAGGCGCCAA
TTGTCCAGACCAAGTGCCCGGAACGGGCATAATCATAAGGTGGTGACGAAACTAAAGCTGAAAACCTGAGTTGTAAAACCAAACGATCGGGACAA
CGGGTTGGGACTCATGCTCTGCGGATGGTTGGGGCTTCGATTGAGTATTTTTTGTAAATATTTTCCGATTCAATTGTGATTAATTTACACATACA
TATATTTAGCTACGTTCGTATGTTTGTATTAATAGGCACTCGAACTCCCATACCCGACATACTTTCCCACCCTTCCTTCAAGCGTAGCATTTACC
CCAGTTGGCTTCTGATACAAGTTCATTGGCTAACAACCGCATCTAGATGTGTTTATCTCGCGATTTGAGTGTGTCTATGTGTAAGAATATTGATG
TTAAGCCATCGCAAATACCTGCTAACAATATCTACATATATCTCTGTGTACCTTCGACGGGAAATCGCTGACAGAGGCGCTACCGAGAACCGCGA
TCCGAAATCCCAGATATAAAGCTACTATATCTATGTAAATGTTAATGTAATTCTAAGCCAGCGAAATCGTGTAACGATATCGCATCAGATATCGG
CATACACATACATACGTTTATAAATCTATATGCCTACGTGTAGTTAAAATTTAAATTGAAAATATATTCAAATTCGAAATGAATGTTCTCAAATG
TACCAAACAAAACAA
(SEQ ID NO: 1439)

Start ATG: 294 (Reverse strand: CAT)

MSDAAKSNNNASADAPDPTTPDATGEADAANAATPTTPRGNHNNNNSANGRSKNKLKSTQNSSGGGSIDKLSPDQDIFINAADGLPNQHPSLPKE
GDVDSDTEPEVDADSFDDLPTSIIVTNIHSEVFANPELKHAMEELFRTFSESATFQWLRSFRRLRVNYDNAIAAANARIKLHQYEFNKKTVITCY
FAQPVTPVSNKNLQPPAPVKQFLISPPASPPAGWEPREEGEPLVNHDLLAALASLTPGESHELHPQSEDQPAIIVHTAMLAETGPGLQVKAPIVQ
TKCPERA*
(SEQ ID NO: 1440)

Classification: known_flybase_gene
Gene Symbol: nla
FlyBase ID: FBgn0026629

Celera Sequence No. : 142000013384485
GATAGCCATTCCACCAAGGCGACGACATCTGAAGGACCATCGAGTGGGGACCGCGAGTCCCAGCTTAAGCATTGCTTGGACAATTTTAATTTGAA
GCTTTTAACAGGAATTTATTCTACATTTGCCAGTTTAATATTCGTATACTTAAGTGTATAAAAATATATGTGTAATGTGTGTTTAAACAGTGCGT
TTCGCCGATGTAAGACAGTTGTGGAAAAGGCAGTTCGTTTTCTAAATCCAAAGGCATTCAAAACGAAGCAGATTGCAATAGTTCTATGGCCTGGA
AACAACAAAATATTAATAATAATAAGACCAAACAATTTGTGTAAGCCATAAAAATAAGAGATTTACAAATTCTTGAGAATACAAATGTATTTGTA
ACAGAACGAAATTTAAGCTCATAACATTTAAGGTCCAATTATCACATACTTTTTGTTTCAAATAAAAATGTTTCAAATATTTCGACAAATACAGG
GAACTTAAGGTCACAACTATCTTTCAGTGCTGAATCGCTTGTTTAATTCGTTGAGGCATTTTTCATTATGATTTGAAACCAAGTGCGCAAAAACAA
ATTGTAAGTAGGAATGGCTCAAATATGTCAAAAAAGTAAAATTAGTGACTAACATAACTTAGGACTAGGTGACATTCGTTTCCGAGTTTCGATGC
TGTTGCATTAGGAATAATTTTGAACACGTGGAATTTACGTTTATGATGAGAAGGCATACATATACAGAATTCAGCATCTTCGCCTAAAACTCATC
TGGATATGTGGTCTCATGGGATTCGTTGCTTTCTTCGTGCTATCGGTTGAGCATATTCGTCAGATTTGTGTGAAGGTAACGCGTTTCTAAGGTCA
CTAAGGTGCTAAACATGCCGAGTTCATGTCCATCCAGCGGGGGAATGCATCGGGGTTTCGTCCTGGCCTTCTATTCGAGTCTTTCATTGCAGGTT
TCTAGTGAAATACTATGCAGTCTTTGCCTGTCCCATTGTGATAGCCGATCCTACAACTGTGCCGCGAGTCCGGAGGCAGAGATGTTGTCGCCAGC
CCCAGCCGTTTTTCTGGCTTCGCGACACACCAGCACCGGGGCCACACAGATTTCCACCTCTAGCCGTTGCCGGTGACGACCGTACTGGATATACT
CCCGCCAACAGGGCACGGGACTGGCTGCACCAATGCGCATTCGCGGCGCATCCGCCTGAGCCGAGGTGGCGAAACTGTCATCTAGAACCTGCAGC
ACTGCCTCCGGGTTAATCTGCGGATGAAAGAATTATCAGTTCAAAACTAAAACATACTACACATAAATGCGTACTCACAAATTGGGATTTGCAGA
CGTATCGGTGAGCAGTGAGCGCTGCCTTTGCAGCGGCAGCACGTGTGTTTTTCCACTTGGAGCCCGCTGTGGTAAGGATCGCCTGATAGGCCAAC
GTGTGCACATGTATGCGCGAGATAGAGCGACGCTTGGCATCGCTTGAGCTTCGGTCTTCGTAATCTTCAAGGAGACTAATGAAAACCTGCCGCAT
CTGGTCAAGGGTGTGAGCTATGCGCGGATTCCAGTCGGTGGCTAAGGTCGTCCGTCCGTGAGCAAGAACCTGCTGCAGGTTAGAGAGCTCTTGTT
CGTTCATTCCCAGGGAGTCTACGTAGGGCAGTACAAAGTGTCGAAGCTGTTGAAGCAGCTGCAACTCCACGTAAGAAGCCATCTCGAAGTGGTTC
AGAGTGCCCTGCGGCTGGCTGGTTAGTTGCCTTTGTACTTGCTGCAGGCGCGCCTCTCGCTCACCAGACTTAAAGGTGAACATGTCCATCATTTG
CAGCCCGCTGACAACCAACAGCTGTGGCTGATACATCTTCAAAGCATCCGTCAACTGCTCCACGGCCCGCAGATGCGGATTATTTCGATCGTTGT
GCAGAATGTAGCGATTGGCGCGAGGTGCCACATATGGGCCCCATTTGTCACCAGCCTTGTACTCCAGAATAAGATGGATGTCATCGTTTGGAATC
TCGTCACCAGCCAGACGAATCTCCTTTGGCAGCAGTGGCCGCAGCCTGAAGAAGTTTTTACATTAAGTTCCATGAAATAATTTGTTATTCAGATA
GGTAATTACTTTCTAGACATGTGGGCGCCCAGTAGCACTTGAGCTCCCTCCATAAAAAAGCGCACGGCCATCAGTGGGGCGTTACCACCCATGTA
CCAATTGATCCTCTCCTTGTCCATCACCTTGGCGTAGCCCACCAGCTGTGTGAAGAGGGTACTGTTTGCCATCACTCGCCTGAAAAGTGGACCAG
TATGAAATACTTTGTTAGTAACTTGCATAGCCAATAAAATATTGGATATCCAAGATCCTTCCATGCAACTTACTCCGCTGCAGCGCCGTTCTGAA
AGTAATAGGCAAAGGACTGCAAGAGCTCGTCCTCGTTGTTCACGACCGCCCGAGATCCTGTAGTGGCTGCTGCGACTGGAATCCGGCGCCCATAG
TAGCGATCCAGAAATTCAGTGGCGTTTATCTGCAAGTCCGTGCAGGCTCCGTAGCCGATGGCCACCTTGGGTGCCGGTTCCAACGCGGTCCGCTT
CAGGGATCTGAAATACAAATGCATATATAGCTAGTGCTGCAGTGTAGCCGAATGAACTCACCCCTCGATTGCCAGGAGACCGGTGAGCAGGACAG
TCGTCCTGTTAAGCGTCTGCAGGGCGATGAATGCCTGCCAAATTATGGAAACAAAGGCCGTTAGGACGGAACAGCCGGTGATCCATCCCATGTAT
CGCAGGGCGGTCATTGTGGGCGTGGATTGTTGTGTGATTGGTTCGCCTCAGTTTGGGCTTTCCAAACTATTTTGTATGTGACAATCCGCCTTCCG
GCTACGCCAACTTTCTTATCAGAATTATCGCTCTTTTTCCTTTGAGATGCTTCAAAGCTAGCGATGACACTATCTGCAGTTCTTGGACTACAGCG
ATAGTCCAACCAACAGTTACATTTGAATGCTATACTGCTATACTATATTTGAATATATTAAAATAAATTTAAATTGAAATGTGCACTTATAAGAG
CGCCCTCTCAATGTGTTAATTTGTTCAATGCATAGAACAGCTTACATTGTGTTTAAACATCTTTTTTGAGCATATTTTTTCGCTAACATATTGG
GAATATGTATGTTTATTTGATCCTCGTAGTTTATATTTAATTTTTAAGCAAACAAATAAAATTGCAATTGCTTATCGATGACAACAATGGTTT
GAGCCACAGCTACTCGAAGCTGGACAGTTCAGTATTGAGCAACTGTAGTTTCGATAAACGATATGTTCCGAAATAACGCCTTCTGCTATCGAAGA
CAGTCTTGCGTCTGTAAAGTGATAAAATAATTTACAATTGAGTCGCTTGGGAATTTCAGTCACTCTCCACACACCAAATACATAGCTCGTGTA
ACAGCCTGATTTAGTCGAACAGCACATCATTTGCCGGAATCGTTAGCGAATAGCAGCACTCTCCGCTAAGTCGGCACGCTAATTGGCAAAACCGA
TTCGATTCCAGGGAAGGAGACACACTGATAGACGGGTGAAGAACAAAAGGAGAAGGAAAACAACAGTTAATCGTCAAATTTTACAGGCAAAAGGT
GAGCAACTACGCCTTGCACACAAACAACCGCATCGACGAGCAAACGCACGCACACACAAGCCTTATCGCCTGCGTAGTGGTTGGTGTATATAAAA
AATTAAAACAATATTTGCACATCCGATTATTACTATAATATTTCGCGTCCACATATATTAGCAAGTGTGCGTGCGCCTGCCCTGGATTTACGTGC
CAGTGTTTGTGCGAGCCTAGCGCGTTTGTGTCTGTGTGTGTGTGTAATGAAATGCAATTTTCTCTTGGCATTTTGCGCGCCTCCGATTTTCGCTG
CCCCTCTGCAAT
(SEQ ID NO: 1441)

Exon: 2907..2627
Exon: 2572..2354
Exon: 2264..2100
Exon: 2040..1314
Exon: 1252..1001
Start ATG: 2769 (Reverse strand: CAT)

Transcript No. : CT20604
CTTTGAAGCATCTCAAAGGAAAAAGAGCGATAATTCTGATAAGAAAGTTGGCGTAGCCGGAAGGCGGATTGTCACATACAAAATAGTTTGGAAAG
CCCAAACTGAGGCGAACCAATCACACAACAATCCACGCCCACAATGACCGCCCTGCGATACATGGGATGGATCACCGGCTGTTCCGTCCTAACGG
CCTTTGTTTCCATAATTTGGCAGGCATTCATCGCCCTGCAGACGCTTAACAGGACGACTGTCCTGCTCACCGGTCTCCTGGCAATCGAGGGATCC
CTGAAGCGGACCGCGTTGGAACCGGCACCCAAGGTGGCCATCGGCTACGGAGCCTGCACGGACTTGCAGATAAACGCCACTGAATTTCTGGATCG
CTACTATGGGCGCCGGATTCCAGTCGCAGCAGCCACTACAGGATCTCGGGCGGTCGTGAACAACGAGGACGAGCTCTTGCAGTCCTTTGCCTATT
ACTTTCAGAACGGCGCTGCAGCGGAGCGAGTGATGGCAAACAGTACCCTCTTCACACAGCTGGTGGGCTACGCCAAGGTGATGGACAAGGAGAGG
ATCAATTGGTACATGGGTGGTAACGCCCCACTGATGGCCGTGCGCTTTTTTATGGAGGGAGCTCAAGTGCTACTGGGCGCCCACATGTCTAGAAA
GCTGCGGCCACTGCTGCCAAAGGAGATTCGTCTGGCTGGTGACGAGATTCCAAACGATGACATCCATCTTATTCTGGAGTACAAGGCTGGTGACA
AATGGGGCCCATATGTGGCACCTCGCGCCAATCGCTACATTCTGCACAACGATCGAAATAATCCGCATCTGCGGGCCGTGGAGCAGTTGACGGAT
GCTTTGAAGATGTATCAGCCACAGCTGTTGGTTGTCAGCGGGCTGCAAATGATGGACATGTTCACCTTTAAGTCTGGTGAGCGAGAGGCGCGCCT
GCAGCAAGTACAAAGGCAACTAACCAGCCAGCCGCAGGGCACTCTGAACCACTTCGAGATGGCTTCTTACGTGGAGTTGCAGCTGCTTCAACAGC
TTCGACACTTTGTACTGCCCTACGTAGACTCCCTGGGAATGAACGAACAAGAGCTCTCTAACCTGCAGCAGGTTCTTGCTCACGGACGGACGACC
TTAGCCACCGACTGGAATCCGCGCATAGCTCACACCCTTGACCAGATGCGGCAGGTTTTCATTAGTCTCCTTGAAGATTACGAAGACCGAAGCTC
AAGCGATGCCAAGCGTCGCTCTATCTCGCGCATACATGTGCACACGTTGGCCTATCAGGCGATCCTTACCACAGCGGGCTCCAAGTGGAAAAACA
CACGTGCTGCCGCTGCAAAGGCAGCGCTCACTGCTCACCGATACGTCTGCAAATCCCAATTTATTAACCCGGAGGCAGTGCTGCAGGTTCTAGAT
GACAGTTTCGCCACCTCGGCTCAGGCGGATGCGCCCGCGAATGCGCATTGGTGCAGCCAGTCCCGTGCCCTGTTGGCGGGAGTATATCCAGTACGG
TCGTCACCGGCAACGGCTAGAGGTGGAAATCTGTGTGGCCCCGGTGCTGGTGTGTCGCGAAGCCAGAAAAACGGCTGGGGCTGGCGACAACATCT
CTGCCTCCGGACTCGCGGCACAGTTGTAG

FIGURE SHEET 779

(SEQ ID NO: 1442)

Start ATG: 139 (Reverse strand: CAT)

MTALRYMGWITGCSVLTAFVSIIWQAFIALQTLNRTTVLLTGLLAIEGSLKRTALEPAPKVAIGYGACTDLQINATEFLDRYYGRRIPVAAATTG
SRAVVNNEDELLQSFAYYFQNGAAAERVMANSTLFTQLVGYAKVMDKERINWYMGGNAPLMAVRFFMEGAQVLLGAHMSRKLRPLLPKEIRLAGD
EIPNDDIHLILEYKAGDKWGPYVAPRANRYILHNDRNNPHLRAVEQLTDALKMYQPQLLVVSGLQMMDMFTFKSGEREARLQQVQRQLTSQPQGT
LNHFEMASYVELQLLQQLRHFVLPYVDSLGMNEQELSNLQQVLAHGRTTLATDWNPRIAHTLDQMRQVFISLLEDYEDRSSSDAKRRSISRIHVH
TLAYQAILTTAGSKWKNTRAAAAKAALTAHRYVCKSQFINPEAVLQVLDDSFATSAQADAPRMRIGAASPVPCWREYIQYGRHRQRLEVEICVAP
VLVCREARKTAGAGDNISASGLAAQL*
(SEQ ID NO: 1443)

Name: transacylase-like
Classification: enzyme

Celera Sequence No. : 142000013384485
GTCTGCGCACGGAAACCAAAGACTGGCGGGAAAACACCCTAAATGTGCCGAAAACTGCGCTTAGCAAAGTTTTAAGCCAGTTGATTTAATTAATA
TGCATTTTTGTGGTAATTGCCAACGGTCGCACTTAAAATAAAAAAACATTTGTTTTACATTTCGGATCCAAGGAAATAAGCCATTATTGGCTTAA
ATAAGCTTTAACGACTGCAATCATGAGCACCCCTCGCAAGAACTATAACAACCTGCCGCCCTACTGCCCACAAGGCGGCCAGTACCCATCGCAGT
CCGCGGATTACAGAGCGCAGCAATTCGGTGGCCAGCAGAAGCCACAAAATCCAAACGTTGGCTTCTACGAGGACAAACAGGGCCAGCAAAATGTT
CCTCATTTCTACCAGAACAAATCCCCACAGGAGCCGCAGCGCCATCGGCCCTACGGTCAGGGCAGGAATTTCGGACGCGGCGGCAGCTTCAATCG
CAGGAACCAACAGAACTGGGATCATCCGAGGAGCCACCAGAACAGGGAACAAAACCAGAGCGGCAGCTCCTTCGGCCAGTACTTTCATCCCTCCA
TGCTGGAGGATCCTTGGCGGGAGCTAATGGAACGGCACGAGGCCATCCACGGACCCAGTACTAGCCGAACTTCACCGAAAGAGGTGGCGGCTTCC
TAAAATGTAGAATACAACACTAAGAGCTAGTTAAGCCCTGTAGGATAATTTCCCCAAAGCAAAGAAAGAATTTTAATTTTAGCTTTCCGATATTA
AACAAAAGAATGTGTAAACATAAAAATGGTTTCATCATGAGATCCGAGCCTGCTTTTGAGTGGCACATTACGTGCTGAAAACCGCTCCGATGCCT
TCAAGAAAGAACTATGGCTAAGGTTGTAACATTTTATACATTTAAGCAACAGTTTCACGTGAATGAAACCCGTGTGTATACTTAAAAATTTAAGA
CTACCGTAATGGAACACCCCTCAGTGCAATGGGGCTCCCCGAGTGAGCTGCTAATAGTGCTGCTGTTGATGCCGCTTCTTCTCCAGATACTTCTC
CCAGTCGACGGCAACGCGATTGTAGATACCCATGGCGGCACGTGCATCCTCCACGGAATTATGCTCGCCCGTTTGGATCTCCTGACCCAGAACGG
CCTTTGTCAGGCGTTTTAAGCTGGGCGTGTGGGTATTAGAGATGAGTTTGCACAGCGGCTTATAATGCGACGTATCACGAATGTCATGGAACGGA
TGGCGGATGCCCAGTACGGCAAGATCGTTGCGCAGGCCGTGTCCCACCAGAATGCGGCCATGTATCAGCTTCATCACTTCGTTTTGCACGGCGGC
AAAGTCCTCACCGTTAGCGATGTCCTGCGGCCGAATGCCGGACACGCTGGTGCGGTAGTCGGTGACCTCCTTTCGCGGCTTCACATACTTGTCCA
GCAGCACGTGTCCCATGCGATTCACGATGGACACGCGTGCCAGCATGTCGTCCCGTGTGTTGTGTCCCACGCCCACCATCTCGCAGTCCATGGCC
AAAATGCGATTGCGGTGTGCCTTCTTTTTCATGCGCATGCGTGCCGATTTGCTTAGTGGTGCTGACTCCGTCGCCTTGGCATCCTGGTTTTCACT
TCCAGCTGCTGCTGCTGCTCCACCGCCAGCAGCGGCCATCCAGTTGGAGCCGGCTGCCCGGCGACTTGTGTTCACCTGTTGCACCTGTAGGCGCT
CCATGGAGGCTTGCAGCTTGCGTTGATTGTGTTGCGGGGAAACCACATTTTTCGTGCTGTCCGTGGTGTTTTTGTTGTTGGCAGACCCGCTTCTG
CTGCTGTCCAAGTTATTGGCCCGGCTACGATTCATGTCGAACTGCTTCTGGCGTGGCGTAGCGGACATGGCGTCGGGGCATCTATATATTCCAAA
TAAATATCCAGCTTAAGACAATCTCGAATAACAAATGTGTTTCTTTATTTAGTAACACCGACCAGTGTGACCGTCTTGGGGTTGCTGGAGTATT
ACTGTCGACGGGCTTTTGGTATTTAAACAGTGTCAATGGGTGCGTTCAGCAGGTAAATAGCAATCACGCCTTATGTAGCCTGTGAACGCATTCAC
TGCGTCAATAATATGTGCATTGATCGCTCGAACAAATAAGACCGTAAAAATCGCTATTCATTTACAGTTTCAGACGTTGAAGTAGTGTAAGTTCA
TTAAAATATTGAAGAAATGTGGGAGTATTGACTAATATTCTAAAATCACTTATGGCGGTTTTATATTTTAACAAATCGTAAAAAATATCAAACTAA
CGGATTTTATACATATGCATGTGCACACTCGAGATTGGGCTTGAAGTTTTGGATATCCACTGCGAAGTGCGCACTTGATAAAGATGTTCGTATGC
AAGGAGTTTTAAACTGGCTCCCGCGTATTTCGTTCGGAGTGCATCCTGGAGCACATAGATGTCAAGTAAGCGCAGCTTACTTAATTCGCATTAAG
GCATATGGTCGTCGAGGAAGTAAAACTTTACTTGAAAAGCGGGGCGTGGCCCCTATCTGCATTCGGCCCCTTCGGCGGCCTGGGCAACTTTCCCA
ATCACATCGAGGATTATTCATTTGAGGAATGCCGTTTGCAGCATTACATGGCTCAACAGGAGGATCGCCTCACTATTTATGAGTTGCAGTATGCT
CGCGAAATTGACTTGGCCACCATGAAAATTATTTGATTAAGATGTCGCCCCAAAAACTACTGGAAACATTGATTGAAATTTACGATCAGCCTCTA
ATCGACAGTTCCTCTGTCGCATCCGTCAGGGACCAGACTTCGGACGAGAGAAAATGCCAAGTTCAGCCTCAAAGCTTCCCAGGTTTTCAAACCAA
CTTTTCAAACCAACTGCCAGTTAAACATCTCCGGTGACACGGCGAGGCCGTCCAACAGAGCATGCTTAAGATGCTGGAAGGCAGCGTGGTTAGCC
TAACCGACCGGGAACAACTGTTTTAAAACTAATAT
(SEQ ID NO: 1444)

Exon: 1980..1001
Start ATG: 1873 (Reverse strand: CAT)

Transcript No. : CT21153
CCAAGACGGTCACACTGGTCGGTGTTACTAAAATAAAGAAACACATTTGTTATTCGAGATTGTCTTAAGCTGGATATTTATTTGGAATATATAGA
TGCCCCGACGCCATGTCCGCTACGCCACGCCAGAAGCAGTTCGACATGAATCGTAGCCGGGCCAATAACTTGGACAGCAGCAGAAGCGGGTCTGC
CAACAACAAAAACACCACGGACAGCACGAAAAATGTGGTTTCCCCGCAACACAATCAACGCAAGCTGCAAGCCTCCATGGAGCGCCTACAGGTGC
AACAGGTGAACACAAGTCGCCGGGCAGCCGGCTCCAACTGGATGGCCGCTGCTGGCGGTGGAGCAGCAGCAGCAGCTGGAAGTGAAAACCAGGAT
GCCAAGGCGACGGAGTCAGCACCACTAAGCAAATCGGCACGCATGCGCATGAAAAAGAAGGCACACCGCAATCGCATTTTGGCCATGGACTGCGA
GATGGTGGGCGTGGGACACAACACACGGGACGACATGCTGGCACGCGTGTCCATCGTGAATCGCATGGGACACGTGCTGCTGGACAAGTATGTGA
AGCCGCGAAAGGAGGTCACCGACTACCGCACCAGCGTGTCCGGCATTCGGCCGCAGGACATCGCTAACGGTGAGGACTTTGCCGCCGTGCAAAAC
GAAGTGATGAAGCTGATACATGGCCGCATTCTGGTGGGACACGGCCTGCGCAACGATCTTGCCGTACTGGGCATCCGCCATCCGTTCCATGACAT
TCGTGATACGTCGCATTATAAGCCGCTGTGCAAACTCATCTCTAATACCCACACGCCCAGCTTAAAACGCCTGACAAAGGCCGTTCTGGGTCAGG
AGATCCAAACGGGCGAGCATAATTCCGTGGAGGATGCACGTGCCGCCATGGGTATCTACAATCGCGTTGCCGTCGACTGGGAGAAGTATCTGGAG
AAGAAGCGGCATCAACAGCAGCACTATTAG
(SEQ ID NO: 1445)

Start ATG: 108 (Reverse strand: CAT)

MSATPRQKQFDMNRSRANNLDSSRSGSANNKNTTDSTKNVVSPQHNQRKLQASMERLQVQQVNTSRRAAGSNWMAAAGGGAAAAAGSENQDAKAT
ESAPLSKSARMRMKKKAHRNRILAMDCEMVGVGHNTRDDMLARVSIVNRMGHVLLDKYVKPRKEVTDYRTSVSGIRPQDIANGEDFAAVQNEVMK
LIHGRILVGHGLRNDLAVLGIRHPFHDIRDTSHYKPLCKLISNTHTPSLKRLTKAVLGQEIQTGEHNSVEDARAAMGIYNRVAVDWEKYLEKKRH
QQQHY*
(SEQ ID NO: 1446)

Name: EXONUCLEASE-LIKE
Classification: enzyme

Celera Sequence No. : 142000013384534
AAATTCGCAGCCTAATTGCTCCTATTATTAATTAGGAATATGGCAAGTTCTCAGCTCGTTAAGGCTCATTTTAGAATGTTTGTCGGGCAATTGTT
TTCAACATCTTTATGGCATTATTAAATTACTATTGGCGTGCGCCGAAACAGCAGGTGGGGAAATCCTTATAGAGCGGGTCTCTCCAATTTAAAG
CGGCTACTTGTTAAATTTATAATGCAATTTGGCGGTGTTAACTATTAACGAGGTTAAGTGGCGCAATTTGAAACCACATTTGAAGGATTTCCCAT
GGTTTAATGGTGTGCATTTTTAAGCACCCTAGTGCACGGCATTTCTAGTACTTGGCTTAATAATAAATGTAAGAACAAACTTATAGACCAATTAG
GTTCTAGCAATTTATCAAAACGTTACGACGTGTTGTATTCTTTCTAAGGCGTAGAAAATAGCGAATGGGAAAGCTTCTTATTTATAATTCATTGT
TTGAGGTAATTTACTATTGAAGGTTTATCACTTAAAAGCGGAAACAGATATGGCTCAGACTTTAACCTAGGCATTATATGTAGATATGAAACCTA
TTTACAAGTTTTATATTTCTCTCTGAACTCAAAATAGAATTAATATATAGTATTAAAGATATACTGCTGTGCAATATATAGGAACAAAACTAAGC
TTCCAATTATAATAAATGCAATAAATTAGTATAAATTCACATGAAACCCTTACCTCCGCCGACGAGAATTACCTCCAAAACTCGATTGGCTTTAA
AAAAAAAACCGGTAATAGAATTGTAACTCGCCTGCTCAAATGTTGTTTAATGATTCAACGAGCGCACTTTCGTTTATAATGAATTCAACCAAAAG
TCCAGTTTCCAATTGCGATAGCCCAATATCGCAATATCACAGTTCACACGCACAGCTCGAACACTAAAAAAACACTGAGCCAGCTGAGAGGCAAC
TGCTAACTGCTAACTGTAAACCAGTTCGACTTCAAAACAACAACTAAGTGCCGTTCGCTCTCTTCGCCTTCTCTTTTCTCTCCCGCTTTCTTCTC
TCCACCTCTTCACTGCTTTGCTGGTCAATCTAGCCTTGTGTGCGTGAGTGTGGGTGCGCCTATCACGATGTACAGGTAAACTTTTATTATTACTA
AATGTCCAGAAGTCTTTAATTAAAATAATTACTTATTGCGACAATAAGTAAGAAGGTGAAATGTAAGACTTCCCAAATTGCAATAAGAACAATAG
CTGTGAGAGCAATAATAATCTTCAGCTTTTATCACTGAGCGGAGCGACATAAGCAAGCTGCACTGTACTTCAGATGCAATGTTGTTGTTTCAGTT
GTTGTAGCTGCTCCTTGGCTTTCACACGCGAGTTGTGGGTGAGCCTTAATCACATTTATTCGATGGTGAGTGGAGAAGGAGGTGCTGAGTGGGCG
AGGGAGCGGCGCCGAGAGAGCGAACGAGCGGTTGACATTGACAACCCCCCTTTTTTGCTGTTGGGAGCGGGCGCACGCCCATGTGTGAGTAGGCT
AATATCGCTACACTTCGAAGTTTCGTTGAATTTGCGCTCTGTTTTGTTTGCTTCTCTCTTTATCGCTCTGCGCTTTGGCTCTCCCGTTCGCTATT
TGTTGTTAATTCGAATACGAATATAACTTCTAGTTTTTATGGTGCCTTTGCGCTCGGTTTTATGACAAAACCATTTTTTTTCCACTGCGGGTAAT
TAAGAACTCGCTGGCACGAATAACCGAACCAATTCAATGTGAATCCACAGTGGAGGCGATCGAGGAACAAAAACAGTCCGCACCATCATTTATTA
ACGCCAATTGTCAGTTCAATTCATTTTCTTCAACTGCTTCTGTGCGAAGAAACCGTTTCATTGCGTCACAAAGATGATTATGCTCATATATTATC
GAACTAATGGGGGGAATTCAAAATTATATAGAGCTGTAAAACAGGAGCCAGCTAATAAATCGGCTAGTATCAACTCCTTATAAATAGCCTCTTTA
CGCAATACTATTGAATACAGAAAAATAAGCCATCAAAGTCAGCATTATTTGCAGTGTTTGCCGACCACTTCCCCGATAAGCCATACATATAGAGT
TACGTAACTGGAGATCGGCGACTCGAGTGGCCGGGCTTTGGCTTTATATAGCTAATTAACTGGACGATCGACCAGGAGCACTTGTGTGCAACTCG
GCAAAATACTATACTTCAGATGTGAAATTGCTAGATTTCTAGAATCGATCAGATTTTCCCCATTCATAAACTGGGTCTGCGACTGTGGCTAATCA
GCGCAATACTGATTGATCGATTGGAAGTGCCATTGGACAATTTATAGAGCGATCCATAAATCATAATCGACTGGTATTTATTGTGCGCTATTCGC
AACTACTCGAGCCCAGCTTTTAGGGTTTCCGTTCCAGCTGGAGATCTTTGTGGGGACGCAAGGCTTCTGGAAACCGAGACCCCGAGAAAAAGATC
ACATGATAGAACCCCCCCATATGATTATGATGATTGCATAAAACTCGAAAACTCGCGACTTTGCAAAGAGAGCGCGACTCACAGATACTCTGGAG
AGTATTATATTCACATGACAAGGGTTCGACTAACACACACACACACTGCGAACGTAGTAGGTGCGTACCTGAGTATCTCAGAGATACTCGGGGCT
TACGAAAGAGATAGCGCTACGCGTATCTGCCGCTCTGACTTTAGCTGCGACTTCTGGCAGGTGTTTGCACAATGGGTCCCATGACAGGTGTGCCC
CGCAGCCCCCAGTAAGCTCACTTTTCCGACCAGTAGCTGTCAGCAGCCAGCATCACGTGCCAAAGTGCATTCAAATTGGGCTTAATTGCACATAC
TCCCTGCTGCCAAAGCACGTGCTTTGGATGGCTAGTTTACAGGGGATATGGATATATACGGGTGGATAACCCGTGGCACAGCTTTTACACCTCG
AACCCGCCGGGTTTTTCCAGTTGCTTCGAGTTTTTTCGAGTTTTTCGCTTACCTTCACAGCTCCGAAAACGCTTTTTATGTCAAAGACACACCAG
ATTCGATTCCCCGCGAGTGCGAGCGATAAATTTAGAACTTGTTTGTTGCCGAGCGAGAGTATCTTTATTCGAATCTGAATCTGAATGGAGCGCAG
CACACGTCTGCTCACCGCCAGCGATCGACTGCGTTTAAATTTGGCACTCGCTGCCGCGACTTCGGTTCGAAAATCTCGCGATCGCCTCGAAATGC
CTCGCACTCTCTGTTACTCAGCACACACACCCTGTGAATTCAGGCGGCTCTCTCGGCGCGGGCATGCCAACTATGTATGATCGGTGACCGTTATC
GCAAATCAGAAATCGACAAATACCCGTACTAAAGTCAAAATCCTCGAGTGCTACATGTGTCTACCAAAAAAATGGTCAGTTTCCAAAAACCTAAT
CACTCTTAGGATCACCCAATTAATCACCATTAATATGTGATATTTTTGCAGTAACTAGATGTGCTTGTTGATAGTGAGGAAGCCAATCTCAAAAA
AAAACCAATTGAACTAACACTTCTTACAATTTAAACTTTTAATTAGAATTTAGAATATAAAATAATATTAAGCTAATTTGGTAACAGTTTCATTT
TAAATTTCAACTGTTTTAAGTGCTGTAAAGTGCATAAAGTGTTAACAGGTGGCTCCACGCACAACGCGTTAGTACCTTACCAAATAGCGTTTTCA
CTGCACCGCTCACCACGGCCACACTCTGCCTTTGTTTTGTTTTGATATTCCCACTGCATCGCATTTAATTTATTAAAAGCTGTTACCAAATTATG
TCCTACGCCGGCTATAGCCAGCTGCCCAGCGGCAGCGACCAGGAGCGCAGGCAGGCGCAGCTCGCGGCCAGCACCTACGACGTGCTACAGCGGAC
GACGGACAGTATCCAGCGATCCAACCAGATTGCCATCGAAACGGAGAACATGGGGGCGGAGGTAATTACCCAGATAGTAGCCATTAACAGGGCTA
ACTAATGCTCGCTTACGCATCAACAGGTACTCGGCGAACTGGGCGAGCAGAGGGAGTCGCTGCTACGCACCACGCGCCGCCTGGAGGACGCCGAT
CAGGATCTGTCCAAATCGAGGGTCATCATTCGGAAGTTGAGCAGGGAGGTGCTCTACAACAAGATCATCCTAATCCTGATTATCATTCTGGAGGT
GGGCATACTCGTCGGCTTGCTGGTGCTGAAGTTCGCTCACCTGTGAGCCAATGCCATTCTATTCCAAAGTCGTAACCACCAAACAGGCGATGGAC
TATATATACCTATTAATCGTTACGAATTCTTTGTCCTAGTTAATAAGCTTATAAATGTATATACTCCACTAAAATGCACTTCCAATTCAAAAAGG
TCAGTTTTAGGATATACCCAGCGATGAATCGGGTGGTTGATTATGTTTATTCATGTTGGCTAAAGCGTTAATGCCTTAGACGTCTATAATATGTA
TTATGGTAGTAAAACACAGATAAAATCGGGTCTGGACATCGGAAGCTCTGCACTCCGAAGAGTTTAGCCCAGTCCCAACGCATATACATACGTAT
GCTATAACAATGATAATATGTAGTTCGTGCAGCACGCTATGCCACGACTATTTGGCAAAAAGCAACGTTAATTACATTCAGTGGGCGACAACGAG
ATAGTAGAACATCCTGAACAATGTCTGCATAATACTTGATCTATGATAAACGGTTACATATATGTAAGTATGTGGGCATCGCTTTGGGGATGCTT
CTTTGTTCGAGAGATGTTTGGGATTTCGCAGAGCTGCGCCTCCTCATTCCTTTGGTGCAGCAGCTCTCCGCTTCAGTTGCCTTCAATTGTCCTTC
GGAAGAACGATGGACCAGCCGAAAACGCGGCGATCGAAGCCGCAGGAGAAGAGATCGCAGTCCAGCAGCGGCTCCTCCGCCCACGCTACAGACGA
CACCATCCGTCGGTGGCCCTGCCGACTGGTCCGTGGCAATCGGGCGACTCTCTGCCCGTTCAAATCGAACAGTCGGATCTGTCGATTGTCATGCG
GTATGGCGATAATTCCACCAGTGGAGACCGCCAAACGATTGACCGAGGAATCCGTTCGAATGGTGGCCAAGGCGGATCGCATGTTGCGCAGCTCC
CAGACCTTGATTGTACGATCATCTGATC
(SEQ ID NO: 1447)

Exon: 1001..1509
Exon: 3818..3956
Exon: 4017..4158

FIGURE SHEET 781

Start ATG: 1506

Transcript No. : CT23167
CCGTTCGCTCTCTTCGCCTTCTCTTTTCTCTCCCGCTTTCTTCTCTCCACCTCTTCACTGCTTTGCTGGTCAATCTAGCCTTGTGTGCGTGAGTG
TGGGTGCGCCTATCACGATGTACAGGTAAACTTTTATTATTACTAAATGTCCAGAAGTCTTTAATTAAAATAATTACTTATTGCGACAATAAGTA
AGAAGGTGAAATGTAAGACTTCCCAAATTGCAATAAGAACAATAGCTGTGAGAGCAATAATAATCTTCAGCTTTTATCACTGAGCGGAGCGACAT
AAGCAAGCTGCACTGTACTTCAGATGCAATGTTGTTGTTTCAGTTGTTGTAGCTGCTCCTTGGCTTTCACACGCGAGTTGTGGGTGAGCCTTAAT
CACATTTATTCGATGGTGAGTGGAGAAGGAGGTGCTGAGTGGGCGAGGGAGCGGCGCCGAGAGAGCGAACGAGCGGTTGACATTGACAACCCCCC
TTTTTTGCTGTTGGGAGCGGGCGCACGCCCATGTCCAGCTGCCCAGCGGCAGCGACCAGGAGCGCAGGCAGGCGCAGCTCGCGGCCAGCACCTAC
GACGTGCTACAGCGGACGACGGACAGTATCCAGCGATCCAACCAGATTGCCATCGAAACGGAGAACATGGGGGCGGAGGTACTCGGCGAACTGGG
CGAGCAGAGGGAGTCGCTGCTACGCACCACGCGCCGCCTGGAGGACGCCGATCAGGATCTGTCCAAATCGAGGGTCATCATTCGGAAGTTGAGCA
GGGAGGTGCTCTACAACAAGATCATCCTAA
(SEQ ID NO: 1448)

Start ATG: 506

MSSCPAAATRSAGRRSSRPAPTTCYSGRRTVSSDPTRLPSKRRTWGRRYSANWASRGSRCYAPRAAWRTPIRICPNRGSSFGS*
(SEQ ID NO: 1449)

Celera Sequence No. : 142000013384250
TGTCGCCCACATAGATGCTGTTTCTCTTGTCCGGCGAGGATTCAAACGACGTGGAGGCGGATACGTCCATGGTCGTGTTCAGTTGGGTCAGTTGG
AGGCCTGGAAGAATCGGTTGCTAGTGGAAATTCGGTTTCGGTTGCTGGCGAGGCGACGTTTAAACATCTGGCGAAGAACTGTGGAGTACCCAGAG
TTGAAGAGCGATTATCAGAGACATGTATATAGATAATACGTTTGCCTTACTCTCTGCAAACTGCAAATTTGTTTTACTTTTCTGCCTACGTGTCG
TACATTGCCAGTTGATTATGTTCAGTCGGGTTTTCTCGACTGACTTTAAAGTCTGCGCCACACACGCACACACATTTGTGCTCCACATATTTGCC
TTAGAATTTGTGTAATTCACCTGGGCATTCTGTGTTTTCTTAATTTACTCACCTGAAAATTTGTGTTTAGTGTGGGTGTTGTTGCACTGCTGGAT
GTTTGGGGCACATTGGCAGAGGCCTTAATTGACGACTGTCTGCTGATTGAAAACTCAATTTGATTGGCGCTGATTACGTTTTTGATTCAATGCGT
GCTCTTAATTTAAATAAAAACCCAAAAAACTAAAGAAATTAAATTGTGATTAAATTCTTCTTGCTAGCGTCGACCAGTGTTGCCTAATGCTTAAA
ATGCAATTATAAGAGCGACTCTAGTGCAAGAAACGAGTAATCGATTCTGGTTCGATAGGCAACGACTTCGATAAGGCGCAAATTAAACTAGTTGT
AAAGGTTTTACGCTATATGTTGTATGCAAGAAAATCAACATAATTTAGCTATAAATATAGGCTACACTTATTTTTAATTATAAGTCCAAATTTCT
TAGTGCATAGGAGTGGAATAACTAATTTTATATCAGTTTTTGGAATGCCCCTAACATGTCCGTGGTATTATTATTTAGTAACGTCAGGGTCACAC
TTTTGTTTTGTTTTGCTTTGCAACTTGACTTTTAAAATTGCAATTGCAGCATGGCCGAAGAACCCGAGGAACCCGCCAAGGTATGGATTACATAA
ATCTATTGGACATCAGGTGCCTGATTAAGCTTTAACTATGTTTAATCTCCCATAGAGCTTCGTTATCTTCGGACGCGATGTGGCGCAGATCCCGT
GCTTTCGTAACAGTTTTCTCTACGGAATCAGCGGAGGAATCGGCATCGGCTTGCTGACTTTTCTGGGCACCTCGCGAACCCACCTGTCCACCCAC
GTGGGCTTCGGCTCCTTCTTCTGCGGCACCATCGCCTACTGGATGACCTGCAGGTAAGTGACTGTGATTAAAACCGTGCGGCGCCCTTATCACTT
AATTATCAATGTGGCATCCGCAGGTATCAATGGTCCGTCAGGAGATTCGAGCAGCAGCAATTGCGTGAGGCGATGAGACGACAAGCCCTTTATGA
GGGCACCCAAAGGGAGAGAGACTTAGATCTGAAGTCGGCGTAGCATAAGTCAGATCCTTCATTACTACTTCGATGTTTGTTTTCACTCTAGGATA
CCAAGTAATCCTGGCATTGTTAAATCCCTTGTGTTGTAAACTACCTTTTGTTACCAAACTTTATAGTAGCCAATATATTATATATATGTTGTAAG
TGAAATCTTAGCTTGCCACTCGTAGGGAATTAATTATGCCACCATCTTTGATTTGGGATTGACAGAAATCAATCCATCATTTTAATGATTGTGGT
TCCTAAAACCTGTTGGGCTTTATTGTGCTTTCGATTTGATTTAAGCTGATAGAGCTAGTTGTTTACTTTTGAAGAACCTTGAACCCATTTTGACG
ACCTTTTAACTTTTTAATAGTTTTTTTTTACCATTTACATAAAAGCAAAATTTACAGTCTAAAAGTTGTATATTCAATACGTTCTGGTACGTAAA
AGGGTTATTTAATGCACCATTTTTACAACTTTAGATAGTATACTTTTTACTTGAGTGGGAGCCATATCACAAAAATGAAATGAAAGGTTAAAAAA
GTATCTAAAAGTAAGTTTCAATTAATATTCTGAAAAATAATTGCATTTCATGTACGTTTCTCTGAAATACCCCTAATTCGATACTATTTATAAAT
CTGGAAGATATATAGCTAGGAAATAGATTTATATATTTGCCTAGTTTGAACACCTTGTGAACATTTTGTTTAAAAAAAAAGCGTATCGTGGTACT
AGAAAACTTTAAGATACAGATAAATAACTTCACTATACCGAGGTTTTGGTGTTTCTTGAGACTGAAGGACAATCTTCAAAATGGTCTTAATTCTT
GAGATAGAAAAGCTGCAGTTCTCATGCTGAATAGTGATCAGTACGATTTTATCTGACAGATTGCTTCCTAGCTGACCACACCGATCTCGGATGG
GTATCTGCTCTAATCCGAGATAGCAGGTAGTAGAACTGCTGCCTCGTAACCCCTAGACATGGCCATTTCCACGCACATGTAGGCGATCCTGCA
(SEQ ID NO: 1450)

Exon: 1001..1030
Exon: 1101..1288
Exon: 1354..1468
Start ATG: 1001

Transcript No. : CT23225
ATGGCCGAAGAACCCGAGGAACCCGCCAAGAGCTTCGTTATCTTCGGACGCGATGTGGCGCAGATCCCGTGCTTTCGTAACAGTTTTCTCTACGG
AATCAGCGGAGGAATCGGCATCGGCTTGCTGACTTTTCTGGGCACCTCGCGAACCCACCTGTCCACCCACGTGGGCTTCGGCTCCTTCTTCTGCG
GCACCATCGCCTACTGGATGACCTGCAGGTATCAATGGTCCGTCAGGAGATTCGAGCAGCAGCAATTGCGTGAGGCGATGAGACGACAAGCCCTT
TATGAGGGCACCCAAAGGGAGAGAGACTTAGATCTGAAGTCGGCGTAG
(SEQ ID NO: 1451)

Start ATG: 1

MAEEPEEPAKSFVIFGRDVAQIPCFRNSFLYGISGGIGIGLLTFLGTSRTHLSTHVGFGSFFCGTIAYWMTCRYQWSVRRFEQQQLREAMRRQAL
YEGTQRERDLDLKSA*
(SEQ ID NO: 1452)

Classification: hypothetical
Gene Symbol: l(3)87Df
FlyBase ID: FBgn0002354

FIGURE SHEET 782

Celera Sequence No. : 142000013383919
GGTTGGATCCATACTGACAATATGTAAACTTTGGGACTGCCTTCTGTGTCATCTGTATTCATTGGAACACAGTTGCCATCAGCGCGTTTAATTAA
CTTATCTGAATTGATTTACATGCATACCAAATTCCAAAGATCGCTCACAGAGTATAAAGGAACTTGAAACCGATGTTCGTTTCTTTACAATTATA
TATTTCAAGTTGCTTGACATATATACGTGCATGCATATATTTGGGCGTGTTTGCGGCCTGTGTTTGTTTGTTTTGGGTGTGAATCTGGAGTTTAT
GGAAGTGGAAAGCGGGATTGTTCACCTATCCTTACATTTTACGGGGATCACTAGGTGTTAGGAAGCATCACTATTTCTGAATTGATTTGTGCCGA
TTTCGGAACTTAATTTTCATCAAATGTTTGTGTTTAAATCGATTTATTTAGTGTAATTGTTGAGTTATCTTGTAAATACATACATTTATTATATT
CCAAGTTTCTCACATAAACTCTATGTTTATACATTTTTTGTCGCTTTCATCTTGCAGTTTTGTCTATACTATTACTAAACCTAGATACGATATTT
AAGAGGCAACCAAAGAGATCTGGCTTGAGATCCCTGGCAGCCTAGTGCGAAACGGACCGAATGAACAATTTGATTTATTGAATTAGTTTTTTTCC
TTTGCTTGGGTAATAAGAAATCTTTCTTTTAGTTTACTGGAGTGTTTAATACATATACTAAATGTAAATATATATTGAAAAGGTTCGTGTGTGTA
TTTTTCTGTCTTCGTGTTCAGTTGTCTGTAAAGTTGGTTCGGTTGTGGGTGTCAGGGAGTGGGTTTCAAATTGGGGTGTGCAAAAGTCCTCCAGA
GATCTTGAGCGTGCCCACAGCTAAAACCTAAAACAAACGAAAAAGTATGAATATCCCAGTTCACGCTGGTGATTCCTTTAACTTACCAGTCCTCT
TCGCATGCCAGTATGGTATAGTGGTCATGACCACGCCCCTAGGGCCAATCCTAGTCGGTCTTTGTCTCCGTAAACTCCTCCAGGGCAAAAAAGCT
GCCGCCGGAGGGGCCACCAGTGCTGCTGGCCGTGCTCGTGGCAACAACGGTGGTGGATGCCGTGCCACTAGATGCCTCCGACACTTGCACTTCCT
CGCCGGCCGAGTCGGCAGCCGCCTCCTTGTCATCTGCACCTCCGGAAGCGCTGGCTGCCTGCTGTGCGGCCTCCAGGACCTGTTGCTGAACCTGG
ACGATGGGCTGGCCATCTTCCGTGTACGACACGGACACTGGGATGCGGGTACCATCCTCGCTAATGACATGAGCGCCTTCCTCACCATCCTGTCC
CTGCTGGATAATTAACTGCCCCTCGGAGTTCAACAGGGAGGCATCGATAAGCTGCTGTTCATTGTTGTCACCATGGACAAGTACCATCTGGCCAC
TGCCATCGGTCATCATCTGGAGGGTTTCGCCCTCAAGTCCCTCGCCGGACTGCAGAACTCCTACACTTTGGAGCAGCTGCTGTATTTGCTCGGGA
TCTTGCACAATTATTTGGTTGCCTTCGGCGTCCGTCAGGATGTGGTTGTCCAGCTGGAGGAGATGGCCGTTCTCGTTAACAATGAACTTGATCTG
GCCACCTTCCACCTGTGCCTGCATGGCTTCGTCAAGTTCCATGGCAACATGCTCGCCACCTGCAGCTTCACCCGCCTCGCCCTCGGCTCCAGTAC
TGGCAGTAACCTCGCCTTCGCCAGATTCACCGGCTTCAGCGGTCGTGGCATTGGCCTCCGACTCAGTTGTGGGCGTATCTGTAGCCTCACGCTTA
GCAACTACGTCTCCTTCGTCAGATGGTTGTGGTTCCTCAGCAGCGGCGGCTTCCTTTGACTTGGCGCTTTCTCCAGCCTTGGCCTTGGCTTTCTC
TTGACCTGCTTTGCTAGCCGTCTTGGTTTCCTCTGAGGCCTCAGCTTCAGCAGCTGCAGCCTCGTTGTCATCATCTAAACTGGGCATGGAAACCG
GTGCGGCATTGGATTTGCTATCGGCAGAGGAGGCCTCGCCGCTTTCGCCCTTGGCATCGATGCTGCCCTGGGACTGTGATTCGTCTTCGGCTTGA
TCCAAATTTGGCATGTCAATGCTAACAGAGACAGGTGCTGTGGTATTGGGCGAATCCTTTTGCGATTGGTCTCCGTCCGGTTGCGGGATAGTAAT
GTTGAAGGTTATGCCTCCACTGCCCTCCTGCGAGGTAATAACCATCTCGCCGCCTTTGCTTCCCGGTTTGGGCGCCTCACCGCTCTCGTTCTTGT
CGGAGTGGAGCTTTTCAAACAGGCTCTCAATGTCGGCCTCTGCGTTTTGCTCGCCGCTCTCGTCACCGGCCTTACCAGTTGCCTCTCCGGGCTCA
TCGCTTAGTAAAGCCGTAGCTGCCGAATTTAGGGCAGTGGCTCCGGCCGAAGTTGCCTTCTTGTCACGTCTGTGGGTCTCCATGTGGTGGTTGTA
GTATGTCTCCTGGATGAAAGTCAGTGAGCAAATGCTGCACGAGAAGAAGCGTATGTTGTTCTCCGACTCGGTGGTTGCCACCACAGCAGCTGTCG
AAGCAGGCAGGCTATCGCTCAGTGCCTCATCAATGGTCTCTTGAAGGAGCTTCTGGGTGTTCAGGTTCTGGCTAACTGACTGCTTGGGCGATACC
GTCGATGCGGAAGGACTCTGATGCACTTCGAAGTGCTTAACAAGCATCTCCCGTTTCGGGAAGGTCATCGAACAAGTGCCGCACTTGAAGAAGTT
GGTCTGATGCTGTTTGGCATGCACAGTAGCAGCTTCGCGCGTCTCAAAGCGCTGAGAGCACAGGCGGCACTTAAAAGGCTTAGGTTTACCAGCGG
CATGCTTGCGCATATGCTCATCAAAAACGACCTTGTCCGTTGACTTGAACTGGCAATGATTGCATGTGTATAGCGATGTTCCAACCAGATTCTCG
TTGGCAGCAGCTGCAGCGGCAGCTGCAGCAGCAGCCACGGGAGCAGCTGATGCCGGTATGGTGGTGGTGCTGGTCACCAGTACATTGGTAGCGTG
ATTCGTCTCCATGTGCTTGCGCAGGCTGTTCTCGTTCACGAAGTTAATGTGACACATGGCACACGTGTTATCCATGGCGGTATTGTGGTCGCGCA
CCATGTGCTGCTTCATGGCCCCAAAGTGCGGGAAGATTTTGCGGCAGGTCTTGCACTGGAAGGTCTGCTGCTTGCAGGTTTCATAATGCGTGTTG
AACAGCCGCATATCCGAGGTTTTATAGTCACACGAGGTGCATTTATAAATCTTGGTGGCCTTGCGTTGGACTGTCTGGGTGCCTTGGACGCTGCT
CTGGGTGGTTCCTGGGGCGATCTTGGACTGGCCAACTGTACGATTGCAGAATATGCATTAGGAAAGCTTTATAATTTCTGTATTTATGTACTTAC
CTGGGTTTCCCTGCAGGAGTTTACGTGGACGCAGCAAATCCGCACTAGGACTCTCCTCCAACGAGCGATTGGCGGATCCGCCGACCATTTTCTGC
ATCTTGAGCGGCGGACTGCCTTCCTGGCCCATATCCTCGTTAATGGCATACTTCTTGTTAAGCAAACTGATGAGGTTCGTCTTGACGCGCTCCAC
ATCGTTTTCCAGGCGGTCGTAGTAGTTCACCAGGTTGGTACAGCGTGAGCACACGTAATCCTCGCCGCAAACAATCACGAGGAAACCCTCGCCCA
CGAGCTGGGCCAGTTTGTTGGGGAATTTGGTGGAAGTGTGCGTGGTGCACATATCGGTTAGCGAAGTCTGTGGCTCGCAGCGGTCATCGCAGATA
TAGCATCGCGTGGCTAATCCGCCGATACCCACGCCACCCGACTCTGCATCGTTGACCGCCTGCTGCTGTGCTACGCCGCCAACGGCTGAGGCTCC
TCCGGCAGAGGCACCTCCTCCTCCGCCACCACCGGGTACCACCATACGCGTCGACTTGAGGATTCGCGGCTGGCTGGGACCGGTCACAGTGACCG
CTCCGCTACTGAGCAGATTGTTAAACTTGCGGTAGGTGGCCGGATTCAGTTGGTTGTTCATTTCGTGGCGTTTTGGATTCAGGTGAGCACGCCGT
AGTGATGGTGTTATTCGGTTTGTGCGGGCGCTACACGCGCAACTGCAAGCCGCTACCTTTCAATATTAATCGGCGATTACGACAAACTACACTTC
TGCACTCCGGTTTGGCAGCTTGCTGGGATTTATGTATCGATCGGGTACGGATGAGCCACTCGAACGAAACAATCTATCTTTTTTGGACACCAGGA
ACAACAATCTCTTCCGTTTTTAATTTTCGGTTTCGTTCTGAGTTGTCGCGGCGTCACTTTGACTGTACTAAAGACTCGGTGCTGTATTTTTTAGG
GTTAAAAATGCGTATGTGCTGTAGCAGTTCTCGACGGACGCGTATGGTCGTCTCGCTCTTTAGCATGCTCGCTGCCCTGGCACGGCGGGAAAACA
TGGGCTAGTCGTTTCACTCGCACGCCACGGAAATGGCGGCTGCCTGGGAGGTCAACCATGGTCAGACAGAGAAAATCTCACAGCGTTGCCGTTCA
TTACGATAACGTAATTATTTACTTGAAATAATAAAGCATTTATTTTTCTTATTGCGATTGCTGAGTGGTTAAATACAAATAAATACTTACTTGTT
GTGCTTGTATTTGTAAAAGGTAAATAATTAGCACATTTTGTCTTGAAAAAAGGCTCAGCGTCATTCCTATCATGCAATGTCAAAATTAACAGTGC
GTTTTGTAGACAGTAGAGGGCGCCTTTGCCCGCCCACTTTAAATTCACAAATATTCTCCTCGTAAATATTTGGCATACCCAACCTGTGAGGTAAG
CATTAAATACTTGCATTTACGCAGTGATAAAGGCCAACATCACTAATGTGCTAATACATAGGACCGATAAGATTCCGAAATTCCAGTTTTACCTA
TTCGATTTAGGTATATCTTTTAGCCAAAGGAAAGTTGAAGGGAAGGGGGCTCTCTTATCAGTAGCGATAATATAACATACGACCTGATAAACGTT
CCAGCCAAACCACAGAATTCAGTTAACGAACGAAACGAAAAGCGAGCGGATACCGCCTCGATCGAAGCGAAACATAAAAAATAAAAGCCCCTGGC
CAGTTGGCTTTTTGTTATAAGAGCCATTATCGCAAGGTTTATCGGGAAATATAGTAAACGGGTGGCGAACTCAATTGTCCGGCTCGATCGTTCAG
TTGGCCAACAGACGTCGCGTACTGCAAAAGCGCACTCAACCCGATCGATTTGAGTCCCGCATACGGGGCGTGAGAATATCTCCCAGTATCTGGAA
ACCACCCCTATATATCGAACAGTCACTGCAAAATGTATTCAGCACCAGCGGCAAAAATCAAGCACTTTGGCTCCCTTAAAACGGTAGCAGCTTGG
GCCGGAATTC
(SEQ ID NO: 1453)

Exon: 4425..3421
Exon: 3360..1001
Start ATG: 4051 (Reverse strand: CAT)

Transcript No. : CT23578
CGAGACGACCATACGCGTCCGTCGAGAACTGCTACAGCACATACGCATTTTTAACCCTAAAAAATACAGCACCGAGTCTTTAGTACAGTCAAAGT
GACGCCGCGACAACTCAGAACGAAACCGAAAATTAAAAACGGAAGAGATTGTTGTTCCTGGTGTCCAAAAAAGATAGATTGTTTCGTTCGAGTGG
CTCATCCGTACCCGATCGATACATAAATCCCAGCAAGCTGCCAAACCGGAGTGCAGAAGTGTAGTTTGTCGTAATCGCCGATTAATATTGAAAGG TAGCGGCTTGCAGTTGCGCGTGTAGCGCCCGCACAAACCGAATAACACCATCACTACGGCGTGCTCACCTGAATCCAAAACGCCACGAAATGAAC
AACCAACTGAATCCGGCCACCTACCGCAAGTTTAACAATCTGCTCAGTAGCGGAGCGGTCACTGTGACCGGTCCCAGCCAGCCGCGAATCCTCAA
GTCGACGCGTATGGTGGTACCCGGTGGTGGCGGAGGAGGAGGTGCCTCTGCCGGAGGAGCCTCAGCCGTTGGCGGCGTAGCACAGCAGCAGGCGG
TCAACGATGCAGAGTCGGGTGGCGTGGGTATCGGCGGATTAGCCACGCGATGCTATATCTGCGATGACCGCTGCGAGCCACAGACTTCGCTAACC
GATATGTGCACCACGCACACTTCCACCAAATTCCCCAACAAACTGGCCCAGCTCGTGGGCGAGGGTTTCCTCGTGATTGTTTGCGGCGAGGATTA
CGTGTGCTCACGCTGTACCAACCTGGTGAACTACTACGACCGCCTGGAAAACGATGTGGAGCGCGTCAAGACGAACCTCATCAGTTTGCTTAACA
AGAAGTATGCCATTAACGAGGATATGGGCCAGGAAGGCAGTCCGCCGCTCAAGATGCAGAAAATGGTCGGCGGATCCGCCAATCGCTCGTTGGAG
GAGAGTCCTAGTGCGGATTTGCTGCGTCCACGTAAACTCCTGCAGGGAAACCCAGTTGGCCAGTCCAAGATCGCCCCAGGAACCACCCAGAGCAG
CGTCCAAGGCACCCAGACAGTCCAACGCAAGGCCACCAAGATTTATAAATGCACCTCGTGTGACTATAAAACCTCGGATATGCGGCTGTTCAACA
CGCATTATGAAACCTGCAAGCAGCAGACCTTCCAGTGCAAGACCTGCCGCAAAATCTTCCCGCACTTTGGGGCCATGAAGCAGCACATGGTGCGC
GACCACAATACCGCCATGGATAACACGTGTGCCATGTGTCACATTAACTTCGTGAACGAGAACAGCCTGCGCAAGCACATGGAGACGAATCACGC
TACCAATGTACTGGTGACCAGCACCACCACCATACCGGCATCAGCTGCTCCCGTGGCTGCTGCTGCAGCTGCCGCTGCAGCTGCTGCCAACGAGA
ATCTGGTTGGAACATCGCTATACACATGCAATCATTGCCAGTTCAAGTCAACGGACAAGGTCGTTTTTGATGAGCATATGCGCAAGCATGCCGCT
GGTAAACCTAAGCCTTTTAAGTGCCGCCTGTGCTCTCAGCGCTTTGAGACGCGCGAAGCTGCTACTGTGCATGCCAAACAGCATCAGACCAACTT
CTTCAAGTGCGGCACTTGTTCGATGACCTTCCCGAAACGGGAGATGCTTGTTAAGCACTTCGAAGTGCATCAGAGTCCTTCCGCATCGACGGTAT
CGCCCAAGCAGTCAGTTAGCCAGAACCTGAACACCCAGAAGCTCCTTCAAGAGACCATTGATGAGGCACTGAGCGATAGCCTGCCTGCTTCGACA
GCTGCTGTGGTGGCAACCACCGAGTCGGAGAACAACATACGCTTCTTCTCGTGCAGCATTTGCTCACTGACTTTCATCCAGGAGACATACTACAA
CCACCACATGGAGACCCACAGACGTGACAAGAAGGCAACTTCGGCCGGAGCCACTGCCCTAAATTCGGCAGCTACGGCTTTACTAAGCGATGAGC
CCGGAGAGGCAACTGGTAAGGCCGGTGACGAGAGCGGCGAGCAAAACGCAGAGGCCGACATTGAGAGCCTGTTTGAAAAGCTCCACTCCGACAAG
AACGAGAGCGGTGAGGCGCCCAAACCGGGAAGCAAAGGCGGCGAGATGGTTATTACCTCGCAGGAGGGCAGTGGAGGCATAACCTTCAACATTAC
TATCCCGCAACCGGACGGAGACCAATCGCAAAAGGATTCGCCCAATACCACAGCACCTGTCTCTGTTAGCATTGACATGCCAAATTTGGATCAAG
CCGAAGACGAATCACAGTCCCAGGGCAGCATCGATGCCAAGGGCGAAAGCGGCGAGGCCTCCTCTGCCGATAGCAAATCCAATGCCGCACCGGTT
TCCATGCCCAGTTTAGATGATGACAACGAGGCTGCAGCTGCTGAAGCTGAGGCCTCAGAGGAAACCAAGACGGCTAGCAAAGCAGGTCAAGAGAA
AGCCAAGGCCAAGGCTGGAGAAAGCGCCAAGTCAAAGGAAGCCGCCGCTGCTGAGGAACCACAACCATCTGACGAAGGAGACGTAGTTGCTAAGC
GTGAGGCTACAGATACGCCCACAACTGAGTCGGAGGCCAATGCCACGACCGCTGAAGCCGGTGAATCTGGCGAAGGCGAGGTTACTGCCAGTACT
GGAGCCGAGGGCGAGGCGGGTGAAGCTGCAGGTGGCGAGCATGTTGCCATGGAACTTGACGAAGCCATGCAGGCACAGGTGGAAGGTGGCCAGAT
CAAGTTCATTGTTAACGAGAACGGCCATCTCCTCCAGCTGGACAACCACATCCTGACGGACGCCGAAGGCAACCAAATAATTGTGCAAGATCCCG
AGCAAATACAGCAGCTGCTCCAAAGTGTAGGAGTTCTGCAGTCCGGCGAGGGACTTGAGGGCGAAACCCTCCAGATGATGACCGATGGCAGTGGC
CAGATGGTACTTGTCCATGGTGACAACAATGAACAGCAGCTTATCGATGCCTCCCTGTTGAACTCCGAGGGGCAGTTAATTATCCAGCAGGGACA
GGATGGTGAGGAAGGCGCTCATGTCATTAGCGAGGATGGTACCCGCATCCCAGTGTCCGTGTCGTACACGGAAGATGGCCAGCCCATCGTCCAGG
TTCAGCAACAGGTCCTGGAGGCCGCACAGCAGGCAGCCAGCGCTTCCGGAGGTGCAGATGACAAGGAGGCGGCTGCCGACTCGGCCGGCGAGGAA
GTGCAAGTGTCGGAGGCATCTAGTGGCACGGCATCCACCACCGTTGTTGCCACGAGCACGGCCAGCAGCACTGGTGGCCCCTCCGGCGGCAGCTT
TTTTGCCCTGGAGGAGTTTACGGAGACAAAGACCGACTAG
(SEQ ID NO: 1454)

Start ATG: 375 (Reverse strand: CAT)

MNNQLNPATYRKFNNLLSSGAVTVTGPSQPRILKSTRMVVPGGGGGGGASAGGASAVGGVAQQQAVNDAESGGVGIGGLATRCYICDDRCEPQTS
LTDMCTTHTSTKFPNKLAQLVGEGFLVIVCGEDYVCSRCTNLVNYYDRLENDVERVKTNLISLLNKKYAINEDMGQEGSPPLKMQKMVGGSANRS
LEESPSADLLRPRKLLQGNPVGQSKIAPGTTQSSVQGTQTVQRKATKIYKCTSCDYKTSDMRLFNTHYETCKQQTFQCKTCRKIFPHFGAMKQHM
VRDHNTAMDNTCAMCHINFVNENSLRKHMETNHATNVLVTSTTTIPASAAPVAAAAAAAAAANENLVGTSLYTCNHCQFKSTDKVVFDEHMRKH
AAGKPKPFKCRLCSQRFETREAATVHAKQHQTNFFKCGTCSMTFPKREMLVKHFEVHQSPSASTVSPKQSVSQNLNTQKLLQETIDEALSDSLPA
STAAVVATTESENNIRFFSCSICSLTFIQETYYNHHMETHRRDKKATSAGATALNSAATALLSDEPGEATGKAGDESGEQNAEADIESLFEKLHS
DKNESGEAPKPGSKGGEMVITSQEGSGGITFNITIPQPDGDQSQKDSPNTTAPVSVSIDMPNLDQAEDESQSQGSIDAKGESGEASSADSKSNAA
PVSMPSLDDDNEAAAAEAEASEETKTASKAGQEKAKAKAGESAKSKEAAAAEEPQPSDEGDVVAKREATDTPTTESEANATTAEAGESGEGEVTA
STGAEGEAGEAAGGEHVAMELDEAMQAQVEGGQIKFIVNENGHLLQLDNHILTDAEGNQIIVQDPEQIQQLLQSVGVLQSGEGLEGETLQMMTDG
SGQMVLVHGDNNEQQLIDASLLNSEGQLIIQQGQDGEEGAHVISEDGTRIPVSVSYTEDGQPIVQVQQQVLEAAQQAASASGGADDKEAAADSAG
EEVQVSEASSGTASTTVVATSTASSTGGPSGGSFFALEEFTETKTD*
(SEQ ID NO: 1455)

Name: zinc finger protein
Classification: transcription_factor

Celera Sequence No. : 142000013383919
TTGGCGCCGTCCAGGCTCGCGCCATTCACCTGACAAGCCTTCTAGCCAAAGGTAAGGCAATTGTTTATGCAATAGCCACTGAATCTCAAACTGTA
ATCCCCGCCAGAACGCCGATACACAAACAAACACGAGTGGGTGGAGGTGGTATCCGGCAGCAATGCCATAGTAGGCATCTCCAGCTACGCCCAGG
AGGCTCTCGGGGATGTGGTGTTCGCCCAACTCCCAGAACCCGGCACGGAACTCAAGCAGGATGACGAATGTGGGGCCCTGGAGAGCGTTAAAGCG
GCTAGCGAGGTGTATTCACCCGTTAGTGGCAAGGTAATTGAAAAGAATGCCGAGGTGGAGGACACACCGGCCCTAGTCAACAGCAGTTGCTATGA
GAAGGGTAAGATTTGCGTGAAGACCCCTTTTTAACTTCACTTGAAACACGTACTTTTCTTTTACAGGCTGGCTTTTCAAGGTGGACCTGAAGAAT
CCCAAGGAACTCGAAGCCCTTATGACCGAGGATCAGTACAAAGCCTTCCTGAGCAGCAGTGGGGATCACTAGAACCAGCAGCTAATCCTAACCCT
AAAGCATCTTGACTGTAGCCTTTAAAACGAGTAATTGTTAGCATTTGTTATCAGCTGAATAACGCTACACTCATACCCAAATATCACCAACCAAA
CTCATCGCCATACACACGTTGTTGTAGCTCTTGAAATTTGTTACGAATAAGAATCAACAATAAATCCAAATGTTATATTTAAATTGGGCATCTTG
ACCTGCGGGTGGCAGACGTCGTCTGCTCCCCCATGGAAACCTTCTAGGTGATAAGACCAAAAGACCGAAGAGAAAACGTGTTGAGAGTTGCTCAA
AGATAAGAAGTCACTCAACAGAAGATTAAGAGAGCGGACAAGGCACTCAGTTTCATAATAATACAGATCAGCTTAATACGGCGTGCTTGGCTGGA
ATTAAGAAAAAACATTTAACACTGTTGCTTGGACACGCGATGGCGCACGCCACGGCACTCAGCCATCACCTGATGGATTCGATGATGGACCGATG
ACACACCTACCTCTCTGGAAAGTTACGCCGTGCTCTGGCGATAAGGATGTCCAAGTCGCGCCTTGAAAATACATATGCCCGATCAAGTTGATAAG
CCTTACAAAAAGCGCCGCCCATGTCTCATTGAACTTGAAGAGCGTGTTCGCGGAAGCTTTTCCATTCGGAAAGCTATGGCAACGGAGGCGAAAAG
CTTGGCAGTAGCTCATTCGAATGGTCAGTGCTCAAAAAGAACTCATTCCGTGCGGTGCGAGAAGCGCATGCTGCTCGAGAACCAACCCCTGAAAA
TAATAAAAACAATCACACAAAGCTAAGGATAATTGCAAAACAGGATAATTGAAAACCTAAAGCAAGGAAAAACAGTTGAAGGACATACACAAATA
ACTAAAACCACAACTCAATAACAAAATGCCAGCGGAAAAATCAATATACGATCCCAACCCGGCCATCAGCCAAAATGCCTACATATCCAGCTTCG AGGAGTACCAGAAGTTCTACCAGGAGTCACTGGACAATCCGGCCGAGTTCTGGTCCCGCGTGGCCAAGCAGTTCCACTGGGAAACGCCAGCCGAT
CAGGATAAGTTCCTCAAGTACAACTTCAACATCTCGAAGGGACCCATTTCGATCAAATGGATGGAGGGTGCCTCCACCAATCTGTGCTACAATCT
CCTAGATCGCAACGTTAGGAACGGCCTGGGCGACCAGATAGCCTACTACTGGTGAGTTCCCTTGCAAATCCTCGCTCACTTTCGCTCTGGGTGGC
GTAGGTCGCACGAAAACAAAAGTATTTGGTTGGCAGCGCAGGATTATTGATTTTTCGCCTGGTTACGAAACTCTCGCCTTGTGACGTAGAACGGT
GGTCTCCTCTTGCACAGGATTTACTGCGCAGGCACCATACCGAAACAGATGATAGCACTCCTTTGTATAATTTAAATACATATGTGCACAAGGAT
GCAGCTCAATGGCACATCCCACCTGCCATCGATTTTGGTTGAAGAATCTTCCCTTATTACCTTTGTGCCTGGTAATCTGAGCGATTATTTTCGTT
TTGATTGTCGCAAATAATTGGTTTAATCGTCTGCATGCCAAATGTGACAGTGGGACTAATGACCGATCAGTTCAACTTTGGGCGGTTTTTGGTTT
TCCAAATGCGCTTTGCTAGACACTCCGACTCTGGGTCAATGTCAGGGCTACTCTTCGTTCCTCGATACGACACGACCCTCATAAGGGGGTGACCC
GGCCATGCTTATTTATTCAGTTTAAATCGATTTACAATTAAACCGGTTGGGGAAGCCCTGAAACATAGAAGCTTTGGTCTTATTTGATTTCACAC
ACTGTTTACTGTGAGTAAGAATGTTTTTCTTTATTCATAAAATTAAATTTAAATGTCGGTTTTTTACCAATACTTCCAATTATTTTAAGTACATT
TCCTGTGTTTTTGAATGTAAAGCAAAGCTTAAGGGTCATTGTCAGTTGTGTTGTTAAGCTCACTAAAACATTAATAACTAAGGCAGCGTGTGGTT
TTTTTTATTAGCAGACCGTAATACTTGCCCCAAAAGTACAATATCCGTACTTTCTGATGTCTTATCTAATTGTCAGTCTATAACTCATCTTTGCG
TTTTTGTTTGTTTCTCCACACGAGGAGGCATTCATTCGTAACAAATTAAGCTAAATTAAACAATCGAATGCGATACTAACTAGGGACTGCTCCCA
CTGTATATGTTCTTTCCTCTTCAAATCAACATACTTCGGTGACTGCGATTAAGCAACAGACACTCCCTTTCGCTGATTAGCTACCGAGGAGGAGT
CCAGTGCCGTATATTACCTTATGAGGTTCTCAAGTGCCCACTCAAATCGCAATTAAATTGAAAAGCTCGGACTGGATGGACGGAATAAGTATTTT
GTTTTGGTTGCGCGAGAAGATTTTTTGTTGTTTTCAGACCCAAAGTTCACCGAGCAATGCGTCAGGGCGCAAAAAAACACAAAGTTAAACAAATG
TTAATGCTAATGAGCTTATCTCCGGGTTATCATTTGAGAGGCGGGTTAGGGGGCGGGGCACGTGTGCCGGAGGAAATGCAAATGAAAGTCAGGTA
ACTGAAAGGCAATTACAAGGTCATTGCAAGTATTGGTTCGCATTCAGCCTCGAACTTACGACGGCCCATCACTACTACTATTCTCGGCCATTTCG
CACTTTTGTTGGGAATTATTTAATCCCAGCCCACAATCTGTCCTCACTTTCCTCAGATAAGATAAAATGGGGAACACAGGCCCAAAAAGGCTGAA
AAAAAAACGGTGTGCACGTAATGAGTAATAATTAACGCTTTCCGAACCGCCGTCTCAGATAATTTTACTGCAAACCAAAGCAAGCTAAAATCTTA
AAAGTTATATGTCCCAGTTTTATTGCATAGATAGACGCAGCGAATCGGAAAAGCTGGAGAATCGGTTATTGGGAATTGGCTTTGGCCTGATTAAT
ATTGCTAAAATTGCGTTTTGGTGCAATTTATGTAATTTTTCAACTTGAAAAACAATATTTTGGGATGTCTTAAATATTTGTGTGCACCTTCCGTC
GAACTAAACAAGGTTGTTGTACCTTTGTCCCAAAATAACCGTTTCGAACCCAACCGATTTACGCAAACTGTTTTCAATTTCGAGAGTCGTTAGCA
ACAAAATTAAGTCGAATTAAACACACGAAAGCCTGAAGCGAAAGCCGAGCAATATTATGTAAACGATTTGACAAAGCGCGCAAATTGTTTATTCA
AATTAATGGAAGCGCGTCTTTGCGTTAAACAGTTTGCTATTTTTCCTTGCCTTTAATTTGTGTGTCAGTCGGCGTCTGGGCAAAAGGTGGATTAT
AATCGATATATTCACTGGGAAATTGAATAAAAAGATCCAAAACAGTTGAAAGCGTGTAAAAATGAAAAGTTTACCCAAAATTATCGAAATAAGGT
ATTTCTAATATTCCAGTGAGCGCCAACAGTTTTACAGCCACTGCGCGTCTAGAAAATCACGCGATCACATCGTCTGATTCACTCACAACCAATTA
GAGAGCCACTGTGCTCCCTCCCTCCACGCACGTTGAAAGACTAAGAGAGAGGTAGTGGTTGTTGTGGAAGGGGGGGGGGGGCAGTGCTGCTGCGCT
AAAGTAGAATTGACTGTCTGTCTTACCTGCTAAGAAATAAGAGAGCCTCAAAAAACAACATGTAGCCAGCTACCTAGGCTACTTTTCTTGACTTA
CCTCGCTTTGTTATCAGTGTTTCCACCTGGAAAAGGTTGACAGGCCCATTTCCGTAAATTATGTAAGCGACTCTATTCACACAAATCAAAGATGC
GCCAATCCGTAAAAACAAATAACCGATCTTTAGATAAACATAGTAGATGAGCATCGTACGATAATGTCTCTCAAACTGTAGGGCCCGGGCAGACA
CGGAGACGCGATAGAGAGAGATAGAAGAAGTCACCGCAAGAAATCAGATGGTTTTGTGGCTAAACAATTTTTGATCTTAGAAAGTCTCAATATTA
CTGCTTGAGTTTGTTTGGAGAGTATCTACAAGCATTTTGTAACAACTAAAAAAATTCCGTCAGAACGTATGGTAAACAATTCCGTGGGATTTTAA
AAAATCACTCAGTTTAAGGCCATGTAGGTTACACAAAGTAATTTTTTCCGCTCATAAATACGAGTGCTTGAGAAATTAATAGTAATAGGAAATCT
AACAACAACCGATGCAATAAAAATCACACATCTTAAGTAAATATAAATTGGTTTCTATCAGCATTTCCTAAGCAAATTATTTTCAGGCGTTTACT
AATATTCAAAATATAGTAAGCACAAGGATATTTGTACAGTGTAGGAAAGAAACCCAAAACATTCCATGCGATCAATACGACACGCGAATCAACAG
CTGATGTTATTGTTATTAAGATAAGTCGCCGGCACTTATTGTTTTTTCCATGGATTTTAGGCCATTCCTCATCATTTTTTCATTTTTGGCTCGCA
CGTGTGGTGAGAGTGGCTGTTTCTAGTATATTTTCGGATTTTTGATTTCTGATAAGCGGGAGACGGCCACGCGTCTTCCCTTGGTCAAGAGGTGA
ACGGTAGATGGCGGACCGGGACGGTGCATGAGGTGTTTCTAAGGCGGCATGGAAAATTTCTTGTCTGGCGATCCGGCGGCGAGATTAGGAGGCGA
GTGGCCCGATTACGCCTCTAAATTGGAAATTAATACACTCGTCGCGACACATTTCTCCCACTGGTTTGATTACTATGCGGAGAAGGAGGAGGCG
CCTCTGGTGCTCCAAACTCTGATAAGTGGAGAAGACGTCCGCAAACACACAACATAGTTTTCCGTGACTGATGGGAATTTCGGCCCAGTTTGGCA
ATCACCATATACATATATATTATAAGTTTGATTATATTTATTTGATCTTATCCATAACAGTGATGTTGACGTTAGATGGCTGTCAAGGTGGAGAC
CAAGGTTAAGGACAAACAGTCTGTTAAGGGTAGACGTTATCAAAATTTGTAAGCCTGGAAAATTCGGCACATTTCAATATAGGCGATATTAATCT
GTACGAAGGGAAAAATGATCTGTACCTGTCTTCGATTAGTTATGTCTATTGCTTATAACATTCTTTTTATGAAATTGCTGGTTTGTGGGGATTAC
AAATGACATTAGTTTCTGATCGTGATCCCTTTTTCGGCCTGCGGGCTTCACTTTGGGGATCCAAATCTCCATTGGGGATCCCTCCTTGTTGGCAG
CTGCGAGGAGTACCGACTCCAGTGCATCGGCATAGCAATCGATGTCCTCCCTGAAGTTGAGCTCCTGGGTTAGTTCAACGCGGGAACTTTCATAC
TCATTGGTTTTAAGTCAGGTGGTTTCCGGGCTTCGGAGAAGAGTTATCAGCATTGGTAAGTGTTCTCCGATGATAAGTCCAATTGCGTGTTTGCA
GTTATTAGATTGTGAGACATGTTTCTTGCCACAAAAACCCAATCAATCAAAATTTCTAACATCTGTAGGCCAGTATTTAGGACTGCCTGGTAAAC
GCAGTCCAGTTTTTATGATTTCAATATGGTTTCCTTTCTTTAGGGGTCGTCGGGCAAAATCCCCCAATGAATACGGGTGTCAGCCCTAATCTCCG
TCGCATACTGTCATATTTGGCCAAGAGCAAGACTCTAAAGTATAGATAGGGTCCAGGAAGAAAATGACTAAGCTCGAAAATAACAGCTCGAGTCA
CAATCGAGGGGTGTTTTCATTGCGTATTTTATTTATTTTTACCAACTTACTAATTGACAAGTACAAGTACAAACAGGTATTTCGTTCAAGTGGAA
TATCATTTCACCGGGGCGGTTTTGGCCCAGTTGAATCAGTCCAAACCCCAAACCCCTTCGCTGGGCGAACTTTGAACACAGCGGTACTTTGACAG
TCAGCGGTACTAAAATAACCCCCAAAAAACGTCACAAGGGGAGCTTTTGCCGTTGTTCCGACTGCTTCCTGCTTTTCTCTTTGGCCATACACATT
TTGGGCCAAAATAATAGACGCTTTATTGCCGGCTAATTCTAATGCTTATCGCAGGCGACGGACAACAGGTGATGATTTACACTCCGCTGATTGCA
TTGTCTGCCTTTCTAGTCCACCTGTCGTGTAGTTTATTACTGTTTTCTGCGTTGCTAATCTGCCTTGACCTCCACAACTGCCATGGAAATGGCTT
TCCCCATTACTTTCATAGTTTCATGACTGACCGTCGGCGATCGCGAGTGTTTATATCCGTTTTGAACGCCGAAACCGTTCACGATTTACCCCAGT
CACGAAATTTGTTTACCCATTCAAAGCTTTCAAAGCTCTGACACATTCCATTTAGTGTTTAATTTTATATTCATTCATTTAATAGCAACAATTAG
GGAAGCATTTACATTGCCTCATATATGTATGTGAATTTTGGATTATTAGGATTGGAAATGCGATTCGGTTTTATTCTTTTATTTATTTTTAGATA
CATACCTTAGTTGTACATAGTTTTGGTAACTTGTGTACTCGTTCAAAGACTTTTTGCAGCTGCTGTAAATAAAGTAAAGTAGGTTATTGGCACTG
GCTTCTGTTGCCAAGTTCAGAACAAAAAGGGAAAGGCATACAAAGTATATACAATTACACAATGCTAAGTCATATTACATATGTACACGGTAGGA
ACACAAGCGGCACACAAAAGGGGATTGGATTTAAATGCATTTTTAAATATTTTGTTGGAAATCTTACCGTAGCTCTAAAATATCTCTTTGAAATT
AGGTGACAATTTGAGTTCAGAAAATCGAATTAAGTCGGGTGGGCAATTAGGAAGCCTCGCATAAAAGTAAGTGATCCAATTATGGTCGGGGTAAT
TAGCCCAATTGTGGGGCACCCGGTATGCGGCCACCCATTTGAGAACGCCATCGGCGCGTGCTCAATGTAATACTATAGAAGGAATACTAAGTATG
TGTTTCCTCACGGTCGTGTTTCTTTTTTGACATTGTTTCAGGGAGGGCAACCACCCCGACGATTATTCCCGGGGTCTCACCTATCGCAAGTTGCT
GGAGGAGGTGTGCCGCTTCGCCAACGTGCTGAAGGATCATGGCATTCGAAAGGGCGATCGTGTATCCATTTACATGCCCATGATTCTGGAGCTGC
CTATCGCGATGCTGGCCTGCGCTCGCATTGGAGCCGTGCACTCGATCGTATTCGCCGGATTCTCACCGGACTCACTGGCGGAGCGGATGTTCGAT
TGCAAGGCCAAGCTGCTGATTACGGCGGATGGAGCCTGGCGTGGAGAGAAACCCCTGTACCTGAAGGCTCTGTGCGACACGGCCTTGGAGAAAGT
CGAGGAGATGGGGCACTCCGTGGAGAAGTGCATCGTGGTGTCGCATTTGAAGCGAGTGACTCCGTGCCAGCCGGATCATGTCGAGGAGGAAATCC
CATGGACCGATGACCGCGATTACTGGTGGCACGAGGAGATGGAGGACAAGGAGCCGGCCTGCTATCCGGAGTGGATGGACGCCGAGGATCCATTG
TTCATGCTCTACACCAGTGGCTCCACTGGCAAGCCCAAGGGAGTGCTCCACACGACTGCCGGATATCTGCTGTATGCGGCCACGACCTTTAAGAT
CGTATTTGACTATAAGCCAGGGGATATCTACTGGTGCACCGCCGATGTTGGCTGGATCACGGGACACACCTACGTGGTGTACGGACCATTGGCCA

FIGURE SHEET 785

ATGGAGCCACTTCAGTGATTGTAAGTGCCTGATTAGATCTAACAAATAATGGATTTTTCTGACTAACTGTCCCTATTACTTCGTAATTGCAGTT
CGAAGGCACACCATTCTTCCCTGGAAACGATCGGTACTGGAGTGTCATTGACAAATATAAGGTAACTCAGTTCTACACAGCTCCAACGGCGATTC
GTGCCCTCATGAAGTTCGGCGAGGGTCCCGTTCTAAAGCACAACCTGAGCGGACTCAAGTACGTTTATTTATACTTCTATAACAATTTTCGTAAT
GACTTTATTCATTTGCAGAGTTTTGGGCAGCGTGGGTGAGCCCATCAACCCGGAGGCCTGGCTCTGGTATTACAAATACATTGGAAAGGAGCAGT
GCTCCATTGTGGACACCTTTTGGCAAACGGAAACCGGTGGTCATGTCATTACACCTCTGCCTGGAGCGACTCCCATGAAGCCGGGATCTGCTGTA
AGATAAATCCTTTGGCTAGTTGATGTCAGTACTAAAATTTATTGTCTTCTACTCTTAGTCATTCCCCTTCTTTGGAGTGAAGCCCACTTTGCTGG
ATGAGTGCGGCATTGAAATTAAGGGGGAGGGAGAGGGCTACTTGGTCTTCTCGCAACCTTGGCCGGGAATGATGCGCACTTTGTACAACAACCAT
GAACGCTTCGAGGACACTTATTTCTCCAAGTTCCCAGGCTACTACTGCACTGGCGATGGTGAGTCTTGAAGTTTTAGACTGTTTTTCATTGTGAT
TTTAAAGTGGATTAGGATTGTTAATTATTTATGTTTGCTTTGATTTTTTTCGCACAGGAGCCCGACGCGATGCTGACGGCTATTTGTGGATCACT
GGTCGTGTGGACGACATGTTAAACGTGTCCGGGCACCTGATGTCCACTGCCGAGGTAGAGTCGGTTCTCACAGAGCATCCTCGCGTGGCTGAGTC
CGCCGTGGTTTCCCGTCCGCATCCCGTCAAGGGCGAGTGTCTCTACTGCTTCATAACGCCGAACGAGAACGAGGTATTCGACCAGAAGCTAATTT
CGGACCTGAAGAAGATGGTGCGAGAACGTATCGGACCTTTTGCCATGCCGGATGTCATTCAAAACGCTCCCGGACTGCCCAAAACTCGTTCCGGC
AAGATTATGCGTCGTGTGCTGCGCAAGATCGCGGTTAACGATCGCAACGTGGGCGACACATCTACCTTGGCCGATGAGCAAATTGTGGAGCAACT
GTTCGCCAACCGGCCAGTGGAGGCCAAGTAGATGGTAGCTGTTGGACCAACTGGCAGCAGCCAGGATCCCTTAACCCAAGGCTTTCTCCGGTTGC
ACTGACCACTCCACTTTGCCATCGCATTTCCACCACTTACGTATCGCGATTACGTATCCTGTAAATCTCCCTCTACTTATATGAATTACCCACTG
CTTAATGTTTGTTCCGTTCCGGGCTACGGCGTGGTTAGCACCTTTCAAATTCTACTTAGCTCGTAAGCCTAAGCGTGTGCGTAAGTAAGTGACTG
GATGGTTTCCGATCCCAGTTATATATCGTCTATATGATTTTGTGTACTTGCCTGTTCATCGTAGTTGACATGCTCACCACGCACACATTTTCCAG
TTCTTTTGTTTCTTCGTTGTAGTCGTAGTTTAAGTTCTCGCTAATTCGTTGTGATACAAATTTAATTATATCTTACTTATGTATGTATTTTTAGT
AGAATTGATATGAGACAAAATATATACACGATTCCAATTGTCGCCACAATTTACACAGATCACCTTTTTTAGTTGTATCTTTTTTTTGTAGTGT
TTCTTTCACACCTTTTCAGATCTGAGGAGATGCGCACGTAAGTTCGGAAACCATAGGGGATATCGGTTTCTTCCCCGTCCCATTAGCCCATAAGT
TTGAGAACGATACATATCTGTGTGGCATTATGCTTGCCACATTCCTACATACGATCTACATGTTAAAGAGAACCACGCGGATATACTATATACAC
TATATATATATATATGTTATAAGGTCAGAAGACTTACTGCAACGAAACATATCATTGAAGTTACTGCTGCAAGCCTATGGATATTATAGAAGCTT
TTATTGTTAGAGATCGTTATCTTGAGGGGAGATCGGCTAGAAAGTAATGGATATCTTGGATTGGCTGATTAGGGGCAGCGGTGCCCAGTCTGAAT
GTAAAAAGATTGTTAGTTATACAGCGATGGCGAACGAAAGATTGCAATTTACATATCTATAAATATATATATATATATTTCTGTATATGAACATA
TGTGTATAATAAAGTTTATTGTTTTAATGTGTTTGAACCTGCAAGTGCAACGACTATATTTTATAGTTAGAAATTCGTATGAAGTGTCAGTCCTG
AGAATTAAGATCGCACTAGCCGAGCATGATACTTCCTTGTGAATCAGTCAACTCTCGGCCTTTGTCACACTTGTTTTGCTGAATTTAGGCTCGGT
CTTTCAACACCTTGGTGGCAGTAACAGATCTTTGTCCGGGTTGTTGTTTGGGGCTGTGGACGAGCACCACCAGAATGGTCGACGAAAAGCTACCA
CCAAGCAAGGAACCGGCTGAACGGCCTCCAGACCAGACCACCCCCGGAAACGCGGCTACCCGATTCGGCTTGGAGGATCACGAGGCCACTCAGCA
GGATGCCCGGGTGAACA
(SEQ ID NO: 1456)

Exon: 1001..1761
Exon: 7547..8285
Exon: 8359..8513
Exon: 8569..8737
Exon: 8799..8988
Exon: 9083..9942
Start ATG: 1451

Transcript No. : CT23612
CACGGCACTCAGCCATCACCTGATGGATTCGATGATGGACCGATGACACACCTACCTCTCTGGAAAGTTACGCCGTGCTCTGGCGATAAGGATGT
CCAAGTCGCGCCTTGAAAATACATATGCCCGATCAAGTTGATAAGCCTTACAAAAAGCGCCGCCCATGTCTCATTGAACTTGAAGAGCGTGTTCG
CGGAAGCTTTTCCATTCGGAAAGCTATGGCAACGGAGGCGAAAAGCTTGGCAGTAGCTCATTCGAATGGTCAGTGCTCAAAAAGAACTCATTCCG
TGCGGTGCGAGAAGCGCATGCTGCTCGAGAACCAACCCCTGAAAATAATAAAAACAATCACACAAAGCTAAGGATAATTGCAAAACAGGATAATT
GAAAACCTAAAGCAAGGAAAAACAGTTGAAGGACATACACAAATAACTAAAACCACAACTCAATAACAAAATGCCAGCGGAAAAATCAATATACG
ATCCCAACCCGGCCATCAGCCAAAATGCCTACATATCCAGCTTCGAGGAGTACCAGAAGTTCTACCAGGAGTCACTGGACAATCCGGCCGAGTTC
TGGTCCCGCGTGGCCAAGCAGTTCCACTGGGAAACGCCAGCCGATCAGGATAAGTTCCTCAAGTACAACTTCAACATCTCGAAGGGACCCATTTC
GATCAAATGGATGGAGGGTGCCTCCACCAATCTGTGCTACAATCTCCTAGATCGCAACGTTAGGAACGGCCTGGGCGACCAGATAGCCTACTACT
GGGAGGGCAACCACCCCGACGATTATTCCCGGGGTCTCACCTATCGCAAGTTGCTGGAGGAGGTGTGCCGCTTCGCCAACGTGCTGAAGGATCAT
GGCATTCGAAAGGGCGATCGTGTATCCATTTACATGCCCATGATTCTGGAGCTGCCTATCGCGATGCTGGCCTGCGCTCGCATTGGAGCCGTGCA
CTCGATCGTATTCGCCGGATTCTCACCGGACTCACTGGCGGAGCGGATGTTCGATTGCAAGGCCAAGCTGCTGATTACGGCGGATGGAGCCTGGC
GTGGAGAGAAACCCCTGTACCTGAAGGCTCTGTGCGACACGGCCTTGGAGAAAGTCGAGGAGATGGGGCACTCCGTGGAGAAGTGCATCGTGGTG
TCGCATTTGAAGCGAGTGACTCCGTGCCAGCCGGATCATGTCGAGGAGGAAATCCCATGGACCGATGACCGCGATTACTGGTGGCACGAGGAGAT
GGAGGACAAGGAGCCGGCCTGCTATCCGGAGTGGATGGACGCCGAGGATCCATTGTTCATGCTCTACACCAGTGGCTCCACTGGCAAGCCCAAGG
GAGTGCTCCACACGACTGCCGGATATCTGCTGTATGCGGCCACGACCTTTAAGATCGTATTTGACTATAAGCCAGGGGATATCTACTGGTGCACC
GCCGATGTTGGCTGGATCACGGGACACACCTACGTGGTGTACGGACCATTGGCCAATGGAGCCACTTCAGTGATTTTCGAAGGCACACCATTCTT
CCCTGGAAACGATCGGTACTGGAGTGTCATTGACAAATATAAGGTAACTCAGTTCTACACAGCTCCAACGGCGATTCGTGCCCTCATGAAGTTCG
GCGAGGGTCCCGTTCTAAAGCACAACCTGAGCGGACTCAAAGTTTTGGGCAGCGTGGGTGAGCCCATCAACCCGGAGGCCTGGCTCTGGTATTAC
AAATACATTGGAAAGGAGCAGTGCTCCATTGTGGACACCTTTTGGCAAACGGAAACCGGTGGTCATGTCATTACACCTCTGCCTGGAGCGACTCC
CATGAAGCCGGGATCTGCTTCATTCCCCTTCTTTGGAGTGAAGCCCACTTTGCTGGATGAGTGCGGCATTGAAATTAAGGGGGAGGGAGAGGGCT
ACTTGGTCTTCTCGCAACCTTGGCCGGGAATGATGCGCACTTTGTACAACAACCATGAACGCTTCGAGGACACTTATTTCTCCAAGTTCCCAGGC
TACTACTGCACTGGCGATGGAGCCCGACGCGATGCTGACGGCTATTTGTGGATCACTGGTCGTGTGGACGACATGTTAAACGTGTCCGGGCACCT
GATGTCCACTGCCGAGGTAGAGTCGGTTCTCACAGAGCATCCTCGCGTGGCTGAGTCCGCCGTGGTTTCCCGTCCGCATCCCGTCAAGGGCGAGT
GTCTCTACTGCTTCATAACGCCGAACGAGAACGAGGTATTCGACCAGAAGCTAATTTCGGACCTGAAGAAGATGGTGCGAGAACGTATCGGACCT
TTTGCCATGCCGGATGTCATTCAAAACGCTCCCGGACTGCCCAAAACTCGTTCCGGCAAGATTATGCGTCGTGTGCTGCGCAAGATCGCGGTTAA
CGATCGCAACGTGGGCGACACATCTACCTTGGCCGATGAGCAAATTGTGGAGCAACTGTTCGCCAACCGGCCAGTGGAGGCCAAGTAGATGGTAG
CTGTTGGACCAACTGGCAGCAGCCAGGATCCCTTAACCCAAGGCTTTCTCCGGTTGCACTGACCACTCCACTTTGCCATCGCATTTCCACCACTT
ACGTATCGCGATTACGTATCCTGTAAATCTCCCTCTACTTATATGAATTACCCACTGCTTAATGTTTGTTCCGTTCCGGGCTACGGCGTGGTTAG
CACCTTTCAAATTCTACTTAGCTCGTAAGCCTAAGCGTGTGCGTAAGTAAGTGACTGGATGGTTTCCGATCCCAGTTATATATCGTCTATATGAT
TTTGTGTACTTGCCTGTTCATCGTAGTTGACATGCTCACCACGCACACATTTTCCAGTTCTTTTGTTTCTTCGTTGTAGTCGTAGTTTAAGTTCT
CGCTAATTCGTTGTGATACAAATT (SEQ ID NO: 1457)

Start ATG: 451

MPAEKSIYDPNPAISQNAYISSFEEYQKFYQESLDNPAEFWSRVAKQFHWETPADQDKFLKYNFNISKGPISIKWMEGASTNLCYNLLDRNVRNG
LGDQIAYYWEGNHPDDYSRGLTYRKLLEEVCRFANVLKDHGIRKGDRVSIYMPMILELPIAMLACARIGAVHSIVFAGFSPDSLAERMFDCKAKL
LITADGAWRGEKPLYLKALCDTALEKVEEMGHSVEKCIVVSHLKRVTPCQPDHVEEEIPWTDDRDYWWHEEMEDKEPACYPEWMDAEDPLFMLYT
SGSTGKPKGVLHTTAGYLLYAATTFKIVFDYKPGDIYWCTADVGWITGHTYVVYGPLANGATSVIFEGTPFFPGNDRYWSVIDKYKVTQFYTAPT
AIRALMKFGEGPVLKHNLSGLKVLGSVGEPINPEAWLWYYKYIGKEQCSIVDTFWQTETGGHVITPLPGATPMKPGSASFPFFGVKPTLLDECGI
EIKGEGEGYLVFSQPWPGMMRTLYNNHERFEDTYFSKFPGYYCTGDGARRDADGYLWITGRVDDMLNVSGHLMSTAEVESVLTEHPRVAESAVVS
RPHPVKGECLYCFITPNENEVFDQKLISDLKKMVRERIGPFAMPDVIQNAPGLPKTRSGKIMRRVLRKIAVNDRNVGDTSTLADEQIVEQLFANR
PVEAK*
(SEQ ID NO: 1458)

Name: acetyl CoA synthase
Classification: enzyme
Gene Symbol: AcCoAS
FlyBase ID: FBgn0012034

Celera Sequence No. : 142000013384612
CCGGGAGATGGAAACAATGCGTTTGGGAGAACATGGGAAAGAGATCTGGGGATCTGAAGATACATATGTATATTCAAACAACTCAGGCTGATCAA
ATAGATTGATAAATTCAAACATATTCCACAGCTGTAGGTGAATTTTTTCGGCCCACTTGTTCTAATAGAGTTAGAGAAATTGGGTTTGCTCAGCT
TTTTTGGGCACAGGGCCACATATGTACATATCTAATACTCACCGTCTTTTGACGCTTTTTGCTGCTCTCCGGAACTTCACTCATTTCTCGAGGGG
AACTGTGCTCGCCTATTATGACCCACCAAAGTAGCACGTCCTCCTGCCAAGCAATTCCAAACAAAACTGCGAAAAGTAGTACTTCGAGTCGGAAT
TCGGTGCAATCGATGAATGAAGTGCGCCACGGAAGTAACCGTTGGCTGGCTTACTGTTTTCCAAATAGGTGTAGCACTCGCAGCAGCTGGACTAT
TGCACTAAATAGCTTAAAGTCTAGTTATATCGCAAGCAAACGTTTAAATTTGGGATACGAGAACTGTATTATTACTAATTCACATGCACACAAAC
ACCCACGCACACCAACGCAGCCATCGGCGCTCAGCTGATTAGAGGTGGCCCAAGTGTACGATGGTTAAACGATAGCCCACTACATTGCTAATGTA
AAAACAAATTTATTAATTTAATTAATATTTTAACTAAACTATCGCATAGTTGTAAGAAAAATTCCAATTGCAAATTAAATTAAAGTCAATACTAC
TTTTTTATAACCGCTTTTTAGTAACCCATTGAAACATAACTTATGTTCCAATGGATGAAAAAATAGACAAAAAAAGTTGAAACTTTATTAAAATG
TAGCTGCTAAATATTTAATATTTTTGTAATATCCCAAATCAAATTTGTATGAAAAACAAAGTTCGTTCTGAATGTACGTTTATTGCAAATTCATC
TGATAAATAAAGGATTAGGACTAGGCTTACGATTAAGAAGTGTCTTCGATCTAGTACGGTGGTGGTTGATACTGCTGCTGGCCCATCATGTTCTG
CCGCTGGAGCTGAGCCACCAGATTCGGCGTTTGTTGCTGGTTCATGCTCTGCTGCTGCGGCACCATTCCGCCTCCGGCGCCACCGCCAACGGCGC
CACCCCCCTGCTGAGGCCCGGCTCCCATGCCGCCGCCTGCCCCACCACCCATACCCTGCAACTGCATCATTTGGTGCCTCAGCTGCTGTTGTTGC
TGTTGCTGCTGCTGGAACTGCTGCTGGGTGTTGAGGACGCCGGGTTTGCCTCCTCCCGCCGACTGCTGACGGGCGTACGGAGGCACCTGGCCGAC
GACGCCACCCGGCCCCGGACCCATCATGGTGGACATGGTTACGTTGGGCGCCTGGTTCATGTACTGGTTCCGGTTGCCGGCCATCATTCCTCCGG
GAACAACGCGCTGTTGCTGTTGTTGTTGTTGCTGCTGCTGGGCAACCGCTGCGGCGGCCATAAAGTCGGGATTGTTGCGATTCCCCTGCTGCATC
TGCGGATTGAAGTTGCCCATCATGTTGGCCTGCTGCTGTTGCTGCTGATTGGGCGCCATGCCGACGCCCACTCCAACGCCTGCTCCACCGCCCTG
TTGCTGCATGCCCTGCTGTTGCTGCTGCTGGTACTGATTCTGGAAGTTCTGGAACTGCACCTGCTGCTGCGGCTGTTGCTGCGGCTGCTGTTGTA
TCATGCCTTGCTGAGGCATGCCTCCCATGCCCATGTTGGGATTGTTGCCGGCACCGCCAACGCCGACGCCAACACCAACGCCCACACCGTTGCCT
CCCTGAGCTCCACCGCTCTGCATCATTTGGTTGGCATTCGGGTTGACCATGCCCACCATATTCTGTGGGATTTGTTGCTGCATCATCGGATTCTG
CGACATGCCTTGACCTCCCATGTTCATCTGATTCATCTGGTTGGGCGCCATGCCGGGTCGCATGTTGCCGCCGCGCATGAACTGCTGCTGTTGCT
GCTGGTTGGGATTCATCTGTTGCTGCTGGGCGTTCTGCTGCGGCTGCTGCTGCATGGCGTTGAATGCAGCGACAGACTGAGGATTTTGCTGGGGA
TTCATTTGCTGCTGGCGCATTTGGTTGGGGTTCATCTGCTGCTGAGGACCGGGCTGTTGTTGCGAAGCCTGTGGTTGTTGCTGCATCGGATTGAA
ACCACCCCCCGGACCCTGTTGCGCTTGCTGCTGGAATGGTTGTCGTTGTCGTAGCATCTGTGATAGCGCCTGCTTGGAGTTGGCATTCAACGGCG
GGCGCTCGATGCGATTTGCTGCAATGGTAAGTGACACGGATTACAATCTTTAACCGTATATAATATCAAACACTCGACTTACACTGCATGTTCTG
CTGATGCGGAGCGTATTGGTTGTGGTACGGTTGTGGCGGCTGCTGCTGCTGCGGCGCATTGTGCCACTGTTGCTGCTGGCCAGGCATACCCTGCG
GTCCGGCTCCACCGCCCCCTGGTCCCTGCTGCATGAAGTTCATCTGGGGATTTGGCTGCCCGTTCCCACCGCCCACATTCAGCTGCTGCTGCATC
GGGTTGTTGCCCATTTGCTGCATCTGCTGCTGCTGCTGCTGTTGTAACATGGCATTCTGCTGCATCATGTTGTTCGGATTGGGTGCAAACTGCTG
CATGTTCATCTGTGGAAAAAATTTATATGAGTTATAATTTAAACTCGAAGGTAACAGAAGAATGGTTTAGCACCGAAAAAGGTTAAGAAAATCTG
GATTACAAGTTTACAACTTTCGAATTTTTCTGCCATCATGTTGCTTTAAGAGGCTTGCTTCGATTCCTTCATAAACCAAATCTAAGAATTTAACT
ATTAACGAAAACAATTTTATTACCGGCATGTTCATTGGCATCTGGCCCATTTGGTTGGGCTGCATCTGCTGCTGTTGCATGTGCTGCTGCTGCAT
GTGCTGCTGTTGTTGCTGCTGCTGTTGCAACTGCTGTTGCTGCACATTCTGCGGCTGTTGAGGCTGCTGTGCCAGCTGAGGCTGCTGTTGCTGAG
TATTGACCACCGGTGGCGTTTTCGGGTTCTTCGGCTTGCGTTTCCGCGTGGTCGTTCCCTTGCCGCGACCTCTTCCCGTGCCGCCAACCACAGCG
CTTGGCGACTGATCCACCGACGAGGGCGTGTCCGCCTTCATTTCATCCTTCTACGAAATAGAAACAATGCATTTAGAAAGGGGCAAAGGGAAATG
CAAAAGGAAATACAAAATGGACTTACTATGCAAATCTTCTCGGGAACAGGCTCAATGTCTTCAGGTGGCAGTGGCAACGGTTCATAGTAATAACT
ACTGGGCTTGACCAGACTGTGCGTGTGATACTTCAGGTTGCGGTGAGCCTCCTCGTAAGTAAGGGGCTTGCGCTCCAGCTTGACTGCACCAAACC
ACACCCAGGACAAAGGAGCCGGGTTCTTGTGACCCTCAAGGATGTCCCACACGCTGATACGCTGTTTGTCCGAAATGCGTAGTTGTTTTTTGTCT
ATATCGCAGATCTTGTTGCCCTTGGTGTCCATTCCAGAGTGTTCGCACGCAATCACCTAAAGGGAGAAATACCACTCAGTTTCCAAGCTCGTTCA
GTTTTGGGTCATCTACTCACCTCAGTAGGCTGCTTGTAAAGTGGAAGAAGCTGCCGAATAACCCGAATGGAGGCGTTGTTCTTCTCTCCGATTTC
CTTCTTTAGCTTCTTCATCAGGTTCATGTAGTGCCTCTCGTCATCAGAGACCAGCGTTGAGTGCACCAATGTGGCCAACATGTCCACAACGGTGG
TGAACAGCTCACGATTGCAGCTGAGATCTACCACGCCCTGGCAAACCAATTGGGCCAGAAGAATAGCCCAGTCTGTGGTGGGGGTACTGTTCTTT
TGGATAGCCTCGAACATGCCGCCCACCAGCGAAAAGCGCAACTGCAGCGCATCGAGGATCTCCTCGCGCGCCTGCGGCTCATCAATGCCACCGAT
TGTGTCCAGCTAAAAGGAGTCATGTTACTAGTAAGTTTAACTTTAAGGATAGAAAGTAAACACTCACCTCAGCAAAGGATTGCAGACATTGTGAT
AACTGGGCATAGAGCGAAACCAGTAAGTTTTCCTTGTACTCGTCCTGGCCTTTCAGGCAAGTTAGGATGAGACCCAGGAAAGGCTGATAATCAAG
CGGCATCTTCTTGTTGCGTGCGGGCACGCCGCCCAGTCCATAGCTATTGCTACTGTGACAACTGTTGCTCTTCTCGCGCTCGTCACCACTGCCCG
AGCTATTGCAATCGGACTTGGACACCTTGGAGAAATAGTTCATGCTCTCAAGAACCTGACCAGCCACTCGAAGTATCCTGCCCTGCACCGCTGGT
GTTAGTTTAGCGATGAGTGGAGCCACTAGCCAGGTGGACGGTTTGGGTTTGTGGGTCGCCTTCACGGCACCCGGCAGGACAACTTCCTCCATGTG
GAAGACGTCGATTGCCGCGCGTGCCACTGTGTCGAGCCAAACATTAAGCTCCGCGTTGTTGCTCAGCGATTGGCGGTACATAAGCTGAAGATCCA
GCCACGAGATACGCAGTGTCCACTGTCCGAGATTCTCTAGTATGCGTACGATCATTGAGCGCTGATCCAGTTCGGAGATGATGTTAAACTCAGGC
TCCGGATAGCAGATCATGTGCAGAACCCGCTGTGCCTGTTTCGCGGTCAGCATTTCGTCGATTATCATGTCGCAGAGTTGCTCTGCGTTCTTTAG GCATCTTTCCAGAACGTGTTCCTGGGCGCAGATCTGCTTGAGCACCGCCTGGGCGAACTCCAACAGCGAGATCTGCTCCATTCCTCCGACCGATG
GCTGTTGCAGGGCTTCGGGTTCGCTTGTCAAACTGCTGCCCAATTGTAAATCGCTGGTGCCCAGGATCTGGCTGAGATCGGCCGGTCGTTGTTCG
TTGCTCTTGGGTGTGCTTCCCGGATGGACCGGTGTATTGAAGCCACTACGCTTGCCGCTTCCAAAAGCTCCGCCCAATCCGCCAGAGGAGGTGCC
GCTGCCGGAAGCCAATGGTGTTTTAAGCGCCGCATTGTCCACAACAATGAGAATGGCCTTGAGCACGGCAAGCACTGCGGCAATGGGAATGGTCT
TATGGGCACCCACCAGAAGATGACGATCGCAGCTCAGCCGAATGCTAAAGTCGTTTCCCACAGCGTGCAGTGGATTCGGGGAAGTGCTTACCGAG
TACATGCCAGGTTGAGGAATCTCCAAGGTCTTAAACAGCTTCAGCACCAAGTGACATGTAAGACGAGCACCTGCCTCTGCATCTACACTCAGTTC
GGCTCCACCAGCGCTTACCGATCGGGCCAATGTAGGCAGGGCGAACTTACTTACAAAGTCGGCTAGTGAGAAGCAATGTCTGGCCACCAGAATGC
ATACGAACACGGCCAGGGCGTTGTGAGTCTTAAGTTGTCCAATGTCGACCTGTCCGCCCAGGTGCGGATAACGCGGACTCTTACTGCCGCTGCAC
AGACTCTGCAGTGCGTATATCCACTCCTCAGACAAGACGTTGCAGCTGGCGGTCAGTTCGGCACATGCGAGGGCCACATCGTTCAGCCGCTCGTT
GTCCGTCTCTCGGCAGACGGCTATTAATGCGTTAGACACGAAACTGTATACATTGGCCGGCGACTCGTGCAGGGTTCCCAGCCAGTGAGGATCCA
GTTTACCACCGCGTCGAGGGGCCATGAAAAGCTCCTGCAACAACAGTGGGTTGTAACCCTGAGGTGGTAGGCTAAATAAAAAATGGTAATATTTG
TTAATATTATATATTATATTATTGGGGAAGAACTTGCGATCTAAACTCACTCAAGCTGCTCTGGAGTGTTGAATATGTCCTTGAACCGCTTGATG
CACTGCAGCTGCTGGTAGTACTCCGTGGATTGTTCCTTTCCCTGGAGCAAAACACACGACTCGTGTAGGTCGCTCAGGTAGGCAATAATGCAGCG
CTCCGCCGAAGTGCACTCACTCGGATTCGATACGTGCCGAATGGTACGACAGACTCCCTCAAAAACAGACAGCGTCTGCTCCGGTGAAAGAAGAA
GGCAGCTGTGGTAGCGCCGCAGGATGCTGACGATGTAGAGGGCAAGTGAAGTGGTGTAACTGCGCACTAGGTTTGACTTCTTTAGCTGCAACTGG
TGCTCCACCTCAGGCAACTCCTTCAACAGACTATCGCACAGTTCCAAAAGACTGTAGATATTAAGAGCCAGCTCCATCAGATCAAAGAGGAACGC
CACGTGCTCCTGTACCGGCAGGTAGTTGTTGTTCCCTAACGCGAATCCGTTCAGCTGCTCCAGGACATTGGCCGCACATTGGGCTGTGACCACAT
GCTGGTCGAAATAAGCCATCTGCTGGCACTTGGACGTGGTAGCTTCGAAGTTAAACTCGTTGCGCGAGTGCTTCTTCACATGACCGGCCGCCGCC
ACATCTATGCTAAACTTTTTTGTGAAAAGCTTTCCAATTTCCTTAGACATCTTCTTGACAGCATGCTTCTTCTCGTCCCTCTCTTTGCCGACTCC
GAAGAGCAGGATGTATCGCTGGTTGCTTTCACTGCTGTAGCTGCTCATGCTGGGATCATCCTGGGGGATGGGGAAGTGCTTGGTGTACACGTAAT
GCCGCGATATGCTACCGCCAGGATTGGTTTCTCCATCGCCTGGAGGACCAATCTTGGGACTGTCTGGAGCTTCGTGCTGTTGTCCTTTCTCCTTA
ATATTTTGCACCAGTTTGTCCAAATCGTCGTCCACATTGGAATCATCAAATTCGTTGTGTTTGAAGTCCAGGCCCCCGCCGAATCCGTCATCATC
GAAACCGTGCGTCGTCGTTGGTGGTGGAGCTGGAGGTGGCGGCGATGTTTTCGTGGCCGTTGTTCCTGATTTGATCACCAGCACCGACTCCAGGA
GCAGATCTCCTCGTGAAATTAGAGTGTGCATGTACGCGTTGTGCGAAAAGACATCGTGGCGAATCAATGCACTGAACAGCTGAACAAGGTTGGTA
AATTCCGTGCGCTGCTGTGGACTGCTCACGTGCTCATCGAGGACGGGAGCATCGTGGTCAAGGAAGTGCATTAACACGTGCTGAAACACAGGCAG
GCCATCAATTAAGCCGGCGCCCGAAGCTAGCGAGTCCTTGTCATCCTTATCACTGGATTGTTGATCCGCCGGCGTGCTTGTCACGTCGATCTGGC
GCTTGTCAAGTAGAATGGCCACCACCATGGCTCTGTGTTCTCCCCAACGCTGCCCCGACACAGCCCACTCGCACAGAATGCGTACCGTGTCCTTG
TCTTGTTTGGGTTCATAAGGCGGACGAGGTTCCACCTGATCCTCCTCCCGCCTGCGACTGACAGTTGGGCTGGGAAATATTTGTGCGTATAGGGT
ATCGATACTATTATTGTGTTCCATGCGATCGAAGCAGTGCGTGTCCAAGTGGTCCAGTGTAGCCAGCACACTGGTGTATTGATTCTTGCCGGCAC
TCAGCCACTTGGCTGCAAACCAGCGCTGCTCTGCATGCTGAGTGCGCAATACGATGTCCGACTCGGCGGCCCGCAATTGACGTCGAATCTCGTGA
TTGGTTCGCGGACAGCGTGTGGGCATCGGCAAGACTGAGGGCGCCAAAGGCAAATGGTCCAGCGGACTACCCAACAACGAGGAGGGTGCTCGGTG
AGCTGCTATCCCACTCCAGACCAGAGCTGTGGGGCACTCGATTGTGATGATCTGTAGGATCGTGCTTAAATACAGCACTATATCCCGATGATGGG
GACAACTCATTTGTTCCTGAAGCGCCAGCTCATAGGGATCTTGTTGCAACTTCGGCTCGTCCAACTCTTTGATGGTCTGCTGTTCTACGACAGTG
TTCAGCAACTGGGCCAGTTTTTTGGACACTATGTAGGCCATCTTTCTGCAAAGACGCTCCGACTGGACGAAGTCGTGCATGTACTGAAGGGCAAA
GCTGAGCACCAATTTCTTCAACGGTTCGTCGAAGCTTGCCTGCGTACGCATCTTGTCCAAAAGGTCGAGGATCCAGTTTAGAAATTCCTGTCGGT
CCAAAAGTGATTCCTCGTACATGTACTTGCTCAATTGGTGGCAGTATTTCCAATACTTAAGCGCATTGCGACTATCTTCGAACTGGCTTCCAATT
CCAGAAATTGTAGAGCCTGGTGGAACTGCAGCTCCTGCACCCGCTGCGCCTCCTACCACAGAAGACCCCGGCCCACCGACTACTCCGCCAAGGCT
TCCCGTCGTCGGCATGACACTGCCGGCATTCACTCCTCCGCCAGGAGCTGCCTGTTGGCCATTAGCTGGGCTATGAATCGGTGGCAGTGGACTGG
CCATGCTGGGTACCGGGATTACGTTCGTGGAAGCACTGCTACCGGTGACGGAGTTAATAGAGCTGGTGCCAGTGGAGCCATTGCTGGCAGGACCA
TTACCGGCGGCGGTCAGGCTTCCGGAAGTGGTGCCATTCGAAGAGGACTTGTCGTGGTCTAAAATCAAGAAGTTGAATAAGGGAGTTGATAGATT
ATAGAACTTAAGGACTGTACTCACTCTGCTGATAATACTCTTGGAGCTTGGGAAGCAGCTCTTTCATGAACTTGATCATGTTGCCGGTCCACTCG
GCAGCCGGGTCGTAAATGGATCGCTTTTTGTTCTTAGACTCGGTGAAGCTAAGCGTATAGGCGGCGCTCAGCTTGATGAACCAGGTGGCGCGTTG
CATGTTCACCTGGTTCTCGCACAGAGTAATGAAGATCTCCTCCTTCTTGTTGAACGATGGAGCCCGTTTGGCTAGGCTAAGTAGGGGTTTGTTAC
CGGCGAGGTCCTTAAACCAGGCGTCCACCGTACACTTGCGACGCGGCGAAACGGGCCAGAAGTTGTCCTTGCAGTTGATCTGCTGCTTCTTGCGC
CCCGTGTCCGGCAGGGTCATCAGCTCCTCCTTCTTGGCCAGGACGCCGCTAAAGAATGCGCTCACTTTGCTGGCGTTCACATTCGAGTTGTGGGC
CGTACCGAATTCATCGGACAGCGGTGGCGTCGTCGTGAATCCGTGCTTCACATTCGTGGGCGTCAGCTCGTCCTCTCGCTGCTTCGCGTCCTGCG
GATAGATGTCCGGCGGACCCAGACGGGTGCGCTTCAGCGGACGCTTCTCCTGCAGCATGGACAGCATCTTCGCGGCCCTCTAGTTGCGTTTTATA
AACAGATTTTCTTAGCGAATTCCCGATTTCCTCTGTTCGCCAACCCAACAACAAATCAAAATATCAGTGGTGGGGCGAAAAAATGCGATGAGCCA
TCGATAGTTCGATAACATCCCGCGAACAATCTAGCGGATGCAATCGAATTTAAGCTAAGTGTTAAATGGTTGTAAATATTACAAATGTAATCTTA
TCATGTTCAGCCACACATCCCCAATCAACCTGATACAGTACTTTAAATATGACGTAATTTTTTAATTATGCAGTGAAAAAGTTACATCGTTGTGC
ACTAACAAAAGAAATACCACTCAAAGTGGTAAGATCACGAATAAAGCTGCGTATAAATATTAAATAATTTACGTTGTATTTTTGGTAATGATTGA
AGAAACATTCGTTGTTAAACGAATAAGGCCTCACAAGGCTTGGCGATCGAATTCCGGCTCATCGGCATAAAAGTGTCCGCCGCTTGTCATTCCAT
CGCTGCACTCGAAGTTCAAACAGAGCATTTTCAGGGGAAATTCGTGCGGTAGCTGCAAACGAAGCACAAAGTGTCACATTAACATAAGGACTTTC
GAATATATGTATGTGCTTTAAATATTACTCACCCGTTCCATGATGTCATGCCTAATGTCAGTGGCCGCGGCAAATAGCTCTAGGGTTTGATGAGC
TGAGCGTTTCGATAAGCTGGCCAGCGTGTCCAAGACGAAGGCGTCTGTGATGCCCAGGCAATAGCAAATGTTCAGATACCGAAGGCGCTCATTGT
TGGCCACCAAAAGGGAGAGCTGCGTTTCTCCAATCTCACGAGCGGACTGTATGGAAAGGCACTCTAATCGACTCAACTTCGCCAAGTGGTGAACA
CACAGATCGTCACGAGGCTTGCAGACCAGCCACCGGAGACACTTCAAAGCACTGATGTACTGCGCCTGCTCCTCGTCAATCCAGCGTTTGCGGTG
CAGGATGAGGTATTCCAACTGA
(SEQ ID NO: 1459)

Exon: 9187..8575
Exon: 8513..5846
Exon: 5771..4058
Exon: 3999..3631
Exon: 3571..3257
Exon: 3185..2874
Exon: 2669..2363
Exon: 2298..1676
Exon: 1614..1001
Start ATG: 9178 (Reverse strand: CAT)

FIGURE SHEET 788

Transcript No. : CT24825

ATGCTGTCCATGCTGCAGGAGAAGCGTCCGCTGAAGCGCACCCGTCTGGGTCCGCCGGACATCTATCCGCAGGACGCGAAGCAGCGAGAGGACGA
GCTGACGCCCACGAATGTGAAGCACGGATTCACGACGACGCCACCGCTGTCCGATGAATTCGGTACGGCCCACAACTCGAATGTGAACGCCAGCA
AAGTGAGCGCATTCTTTAGCGGCGTCCTGGCCAAGAAGGAGGAGCTGATGACCCTGCCGGACACGGGGCGCAAGAAGCAGCAGATCAACTGCAAG
GACAACTTCTGGCCCGTTTCGCCGCGTCGCAAGTGTACGGTGGACGCCTGGTTTAAGGACCTCGCCGGTAACAAACCCCTACTTAGCCTAGCCAA
ACGGGCTCCATCGTTCAACAAGAAGGAGGAGATCTTCATTACTCTGTGCGAGAACCAGGTGAACATGCAACGCGCCACCTGGTTCATCAAGCTGA
GCGCCGCCTATACGCTTAGCTTCACCGAGTCTAAGAACAAAAAGCGATCCATTTACGACCCGGCTGCCGAGTGGACCGGCAACATGATCAAGTTC
ATGAAAGAGCTGCTTCCCAAGCTCCAAGAGTATTATCAGCAGAACCACGACAAGTCCTCTTCGAATGGCACCACTTCCGGAAGCCTGACCGCCGC
CGGTAATGGTCCTGCCAGCAATGGCTCCACTGGCACCAGCTCTATTAACTCCGTCACCGGTAGCAGTGCTTCCACGAACGTAATCCCGGTACCCA
GCATGGCCAGTCCACTGCCACCGATTCATAGCCCAGCTAATGGCCAACAGGCAGCTCCTGGCGGAGGAGTGAATGCCGGCAGTGTCATGCCGACG
ACGGGAAGCCTTGGCGGAGTAGTCGGTGGGCCGGGGTCTTCTGTGGTAGGAGGCGCAGCGGGTGCAGGAGCTGCAGTTCCACCAGGCTCTACAAT
TTCTGGAATTGGAAGCCAGTTCGAAGATAGTCGCAATGCGCTTAAGTATTGGAAATACTGCCACCAATTGAGCAAGTACATGTACGAGGAATCAC
TTTTGGACCGACAGGAATTTCTAAACTGGATCCTCGACCTTTTGGACAAGATGCGTACGCAGGCAAGCTTCGACGAACCGTTGAAGAAATTGGTG
CTCAGCTTTGCCCTTCAGTACATGCACGACTTCGTCCAGTCGGAGCGTCTTTGCAGAAAGATGGCCTACATAGTGTCCAAAAAACTGGCCCAGTT
GCTGAACACTGTCGTAGAACAGCAGACCATCAAAGAGTTGGACGAGCCGAAGTTGCAACAAGATCCCTATGAGCTGGCGCTTCAGGAACAAATGA
GTTGTCCCCATCATCGGGATATAGTGCTGTATTTAAGCACGATCCTACAGATCATCACAATCGAGTGCCCCACAGCTCTGGTCTGGAGTGGGATA
GCAGCTCACCGAGCACCCTCCTCGTTGTTGGGTAGTCCGCTGGACCATTTGCCTTTGGCGCCCTCAGTCTTGCCGATGCCCACACGCTGTCCGCG
AACCAATCACGAGATTCGACGTCAATTGCGGGCCGCCGAGTCGGACATCGTATTGCGCACTCAGCATGCAGAGCAGCGCTGGTTTGCAGCCAAGT
GGCTGAGTGCCGGCAAGAATCAATACACCAGTGTGCTGGCTACACTGGACCACTTGGACACGCACTGCTTCGATCGCATGGAACACAATAATAGT
ATCGATACCCTATACGCACAAATATTTCCCAGCCCAACTGTCAGTCGCAGGCGGGAGGAGGATCAGGTGGAACCTCGTCCGCCTTATGAACCCAA
ACAAGACAAGGACACGGTACGCATTCTGTGCGAGTGGGCTGTGTCGGGGCAGCGTTGGGGAGAACACAGAGCCATGGTGGTGGCCATTCTACTTG
ACAAGCGCCAGATCGACGTGACAAGCACGCCGGCGGATCAACAATCCAGTGATAAGGATGACAAGGACTCGCTAGCTTCGGGCGCCGGCTTAATT
GATGGCCTGCCTGTGTTTCAGCACGTGTTAATGCACTTCCTTGACCACGATGCTCCCGTCCTCGATGAGCACGTGAGCAGTCCACAGCAGCGCAC
GGAATTTACCAACCTTGTTCAGCTGTTCAGTGCATTGATTCGCCACGATGTCTTTTCGCACAACGCGTACATGCACACTCTAATTTCACGAGGAG
ATCTGCTCCTGGAGTCGGTGCTGGTGATCAAATCAGGAACAACGGCCACGAAAACATCGCCGCCACCTCCAGCTCCACCACCAACGACGACGCAC
GGTTTCGATGATGACGGATTCGGCGGGGGCCTGGACTTCAAACACAACGAATTTGATGATTCCAATGTGGACGACGATTTGGACAAACTGGTGCA
AAATATTAAGGAGAAAGGACAACAGCACGAAGCTCCAGACAGTCCCAAGATTGGTCCTCCAGGCGATGGAGAAACCAATCCTGGCGGTAGCATAT
CGCGGCATTACGTGTACACCAAGCACTTCCCCATCCCCCAGGATGATCCCAGCATGAGCAGCTACAGCAGTGAAAGCAACCAGCGATACATCCTG
CTCTTCGGAGTCGGCAAAGAGAGGGACGAGAAGAAGCATGCTGTCAAGAAGATGTCTAAGGAAATTGGAAAGCTTTTCACAAAAAAGTTTAGCAT
AGATGTGGCGGCGGCCGGTCATGTGAAGAAGCACTCGCGCAACGAGTTTAACTTCGAAGCTACCACGTCCAAGTGCCAGCAGATGGCTTATTTCG
ACCAGCATGTGGTCACAGCCCAATGTGCGGCCAATGTCCTGGAGCAGCTGAACGGATTCGCGTTAGGGAACAACAACTACCTGCCGGTACAGGAG
CACGTGGCGTTCCTCTTTGATCTGATGGAGCTGGCTCTTAATATCTACAGTCTTTTGGAACTGTGCGATAGTCTGTTGAAGGAGTTGCCTGAGGT
GGAGCACCAGTTGCAGCTAAAGAAGTCAAACCTAGTGCGCAGTTACACCACTTCACTTGCCCTCTACATCGTCAGCATCCTGCGGCGCTACCACA
GCTGCCTTCTTCTTTCACCGGAGCAGACGCTGTCTGTTTTTGAGGGAGTCTGTCGTACCATTCGGCACGTATCGAATCCGAGTGAGTGCACTTCG
GCGGAGCGCTGCATTATTGCCTACCTGAGCGACCTACACGAGTCGTGTGTTTTGCTCCAGGGAAAGGAACAATCCACGGAGTACTACCAGCAGCT
GCAGTGCATCAAGCGGTTCAAGGACATATTCAACACTCCAGAGCAGCTTGACCTACCACCTCAGGGTTACAACCCACTGTTGTTGCAGGAGCTTT
TCATGGCCCCTCGACGCGGTGGTAAACTGGATCCTCACTGGCTGGGAACCCTGCACGAGTCGCCGGCCAATGTATACAGTTTCGTGTCTAACGCA
TTAATAGCCGTCTGCCGAGAGACGGACAACGAGCGGCTGAACGATGTGGCCCTCGCATGTGCCGAACTGACCGCCAGCTGCAACGTCTTGTCTGA
GGAGTGGATATACGCACTGCAGAGTCTGTGCAGCGGCAGTAAGAGTCCGCGTTATCCGCACCTGGGCGGACAGGTCGACATTGGACAACTTAAGA
CTCACAACGCCCTGGCCGTGTTCGTATGCATTCTGGTGGCCAGACATTGCTTCTCACTAGCCGACTTTGTAAGTAAGTTCGCCCTGCCTACATTG
GCCCGATCGGTAAGCGCTGGTGGAGCCGAACTGAGTGTAGATGCAGAGGCAGGTGCTCGTCTTACATGTCACTTGGTGCTGAAGCTGTTTAAGAC
CTTGGAGATTCCTCAACCTGGCATGTACTCGGTAAGCACTTCCCCGAATCCACTGCACGCTGTGGGAAACGACTTTAGCATTCGGCTGAGCTGCG
ATCGTCATCTTCTGGTGGGTGCCCATAAGACCATTCCCATTGCCGCAGTGCTTGCCGTGCTCAAGGCCATTCTCATTGTTGTGGACAATGCGGCG
CTTAAAACACCATTGGCTTCCGGCAGCGGCACCTCCTCTGGCGGATTGGGCGGAGCTTTTGGAAGCGGCAAGCGTAGTGGCTTCAATACACCGGT
CCATCCGGGAAGCACACCCAAGAGCAACGAACAACGACCGGCCGATCTCAGCCAGATCCTGGGCACCAGCGATTTACAATTGGGCAGCAGTTTGA
CAAGCGAACCCGAAGCCCTGCAACAGCCATCGGTCGGAGGAATGGAGCAGATCTCGCTGTTGGAGTTCGCCCAGGCGGTGCTCAAGCAGATCTGC
GCCCAGGAACACGTTCTGGAAAGATGCCTAAAGAACGCAGAGCAACTCTGCGACATGATAATCGACGAAATGCTGACCGCGAAACAGGCACAGCG
GGTTCTGCACATGATCTGCTATCCGGAGCCTGAGTTTAACATCATCTCCGAACTGGATCAGCGCTCAATGATCGTACGCATACTAGAGAATCTCG
GACAGTGGACACTGCGTATCTCGTGGCTGGATCTTCAGCTTATGTACCGCCAATCGCTGAGCAACAACGCGGAGCTTAATGTTTGGCTCGACACA
GTGGCACGCGCGGCAATCGACGTCTTCCACATGGAGGAAGTTGTCCTGCCGGGTGCCGTGAAGGCGACCCACAAACCCAAACCGTCCACCTGGCT
AGTGGCTCCACTCATCGCTAAACTAACACCAGCGGTGCAGGGCAGGATACTTCGAGTGGCTGGTCAGGTTCTTGAGAGCATGAACTATTTCTCCA
AGGTGTCCAAGTCCGATTGCAATAGCTCGGGCAGTGGTGACGAGCGCGAGAAGAGCAACAGTTGTCACAGTAGCAATAGCTATGGACTGGGCGGC
GTGCCCGCACGCAACAAGAAGATGCCGCTTGATTATCAGCCTTTCCTGGGTCTCATCCTAACTTGCCTGAAAGGCCAGGACGAGTACAAGGAAAA
CTTACTGGTTTCGCTCTATGCCCAGTTATCACAATGTCTGCAATCCTTTGCTGAGCTGGACACAATCGGTGGCATTGATGAGCCGCAGGCGCGCG
AGGAGATCCTCGATGCGCTGCAGTTGCGCTTTTCGCTGGTGGGCGGCATGTTCGAGGCTATCCAAAAGAACAGTACCCCCACCACAGACTGGGCT
ATTCTTCTGGCCCAATTGGTTTGCCAGGGCGTGGTAGATCTCAGCTGCAATCGTGAGCTGTTCACCACCGTTGTGGACATGTTGGCCACATTGGT
GCACTCAACGCTGGTCTCTGATGACGAGAGGCACTACATGAACCTGATGAAGAAGCTAAAGAAGGAAATCGGAGAGAAGAACAACGCCTCCATTC
GGGTTATTCGGCAGCTTCTTCCACTTTACAAGCAGCCTACTGAGGTGATTGCGTGCGAACACTCTGGAATGGACACCAAGGGCAACAAGATCTGC
GATATAGACAAAAAACAACTACGCATTTCGGACAAACAGCGTATCAGCGTGTGGGACATCCTTGAGGGTCACAAGAACCCGGCTCCTTTGTCCTG
GGTGTGGTTTGGTGCAGTCAAGCTGGAGCGCAAGCCCCTTACTTACGAGGAGGCTCACCGCAACCTGAAGTATCACACGCACAGTCTGGTCAAGC
CCAGTAGTTATTACTATGAACCGTTGCCACTGCCACCTGAAGACATTGAGCCTGTTCCCGAGAAGATTTGCATAAAGGATGAAATGAAGGCGGAC
ACGCCCTCGTCGGTGGATCAGTCGCCAAGCGCTGTGGTTGGCGGCACGGGAAGAGGTCGCGGCAAGGGAACGACCACGCGGAAACGCAAGCCGAA
GAACCCGAAAACGCCACCGGTGGTCAATACTCAGCAACAGCAGCCTCAGCTGGCACAGCAGCCTCAACAGCCGCAGAATGTGCAGCAACAGCAGT
TGCAACAGCAGCAGCAACAACAGCAGCACATGCAGCAGCAGCACATGCAACAGCAGCAGATGCAGCCCAACCAAATGGGCCAGATGCCAATGAAC
ATGCCGATGAACATGCAGCAGTTTGCACCCAATCCGAACAACATGATGCAGCAGAATGCCATGTTACAACAGCAGCAGCAGCAGCAGATGCAGCA
AATGGGCAACAACCCGATGCAGCAGCAGCTGAATGTGGGCGGTGGAACGGGCAGCCAAATCCCCAGATGAACTTCATGCAGCAGGGACCAGGGG
GCGGTGGAGCCGGACCGCAGGGTATGCCTGGCCAGCAGCAACAGTGGCACAATGCGCCGCAGCAGCAGCAGCCGCCACAACCGTACCACAACCAA
TACGCTCCGCATCAGCAGAACATGCAGTCAAATCGCATCGAGCGCCCGCCGTTGAATGCCAACTCCAAGCAGGCGCTATCACAGATGCTACGACA
ACGACAACCATTCCAGCAGCAAGCGCAACAGGGTCCGGGGGGTGGTTTCAATCCGATGCAGCAACAACCACAGGCTTCGCAACAACAGCCCGGTC
CTCAGCAGCAGATGAACCCCAACCAAATGCGCCAGCAGCAAATGAATCCCCAGCAAAATCCTCAGTCTGTCGCTGCATTCAACGCCATGCAGCAG
CAGCCGCAGCAGAACGCCCAGCAGCAACAGATGAATCCCAACCAGCAGCAACAGCAGCAGTTCATGCGCGGCGGCAACATGCGACCCGGCATGGC

FIGURE SHEET 789

GCCCAACCAGATGAATCAGATGAACATGGGAGGTCAAGGCATGTCGCAGAATCCGATGATGCAGCAACAAATCCCACAGAATATGGTGGGCATGG
TCAACCCGAATGCCAACCAAATGATGCAGAGCGGTGGAGCTCAGGGAGGCAACGGTGTGGGCGTTGGTGTTGGCGTCGGCGTTGGCGGTGCCGGC
AACAATCCCAACATGGGCATGGGAGGCATGCCTCAGCAAGGCATGATACAACAGCAGCCGCAGCAACAGCCGCAGCAGCAGAGGGCGGTGGAGCA
GGCGTTGGAGTGGGCGTCGGCATGGCGCCCAATCAGCAGCAACAGCAGCAGGCCAACATGATGGGCAACTTCAATCCGCAGATGCAGCAGGGGAA
TCGCAACAATCCCGACTTTATGGCCGCCGCAGCGGTTGCCCAGCAGCAGCAACAACAACAACAGCAACAGCGCGTTGTTCCCGGAGGAATGATGG
CCGGCAACCGGAACCAGTACATGAACCAGGCGCCCAACGTAACCATGTCCACCATGATGGGTCCGGGGCCGGGTGGCGTCGTCGGCCAGGTGCCT
CCGTACGCCCGTCAGCAGTCGGCGGGAGGAGGCAAACCCGGCGTCCTCAACACCCAGCAGCAGTTCCAGCAGCAGCAACAGCAACAACAACAGCAGCT
GAGGCACCAAATGATGCAGTTGCAGGGTATGGGTGGTGGGGCAGGCGGCGGCATGGGAGCCGGGCCTCAGCAGGGGGGTGGCGCCGTTGGCGGTG
GCGCCGGAGGCGGAATGGTGCCGCAGCAGCAGAGCATGAACCAGCAACAAACGCCGAATCTGGTGGCTCAGCTCCAGCGGCAGAACATGATGGGC
CAGCAGCAGTATCAACCACCACCGTACTAG
(SEQ ID NO: 1460)

Start ATG: 10 (Reverse strand: CAT)

MLQEKRPLKRTRLGPPDIYPQDAKQREDELTPTNVKHGFTTTPPLSDEFGTAHNSNVNASKVSAFFSGVLAKKEELMTLPDTGRKKQQINCKDNF
WPVSPRRKCTVDAWFKDLAGNKPLLSLAKRAPSFNKKEEIFITLCENQVNMQRATWFIKLSAAYTLSFTESKNKKRSIYDPAAEWTGNMIKFMKE
LLPKLQEYYQQNHDKSSSNGTTSGSLTAAGNGPASNGSTGTSSINSVTGSSASTNVIPVPSMASPLPPIHSPANGQQAAPGGGVNAGSVMPTTGS
LGGVVGGPGSSVVGGAAGAGAAVPPGSTISGIGSQFEDSRNALKYWKYCHQLSKYMYEESLLDRQEFLNWILDLLDKMRTQASFDEPLKKLVLSF
ALQYMHDFVQSERLCRKMAYIVSKKLAQLLNTVVEQQTIKELDEPKLQQDPYELALQEQMSCPHHRDIVLYLSTILQIITIECPTALVWSGIAAH
RAPSSLLGSPLDHLPLAPSVLPMPTRCPRTNHEIRRQLRAAESDIVLRTQHAEQRWFAAKWLSAGKNQYTSVLATLDHLDTHCFDRMEHNNSIDT
LYAQIFPSPTVSRRREEDQVEPRPPYEPKQDKDTVRILCEWAVSGQRWGEHRAMVVAILLDKRQIDVTSTPADQQSSDKDDKDSLASGAGLIDGL
PVFQHVLMHFLDHDAPVLDEHVSSPQQRTEFTNLVQLFSALIRHDVFSHNAYMHTLISRGDLLLESVLVIKSGTTATKTSPPPPAPPPTTHGFD
DDGFGGGLDFKHNEFDDSNVDDDLDKLVQNIKEKGQQHEAPDSPKIGPPGDGETNPGGSISRHYVYTKHFPIPQDDPSMSSYSSESNQRYILLFG
VGKERDEKKHAVKKMSKEIGKLFTKKFSIDVAAAGHVKKHSRNEFNFEATTSKCQQMAYFDQHVVTAQCAANVLEQLNGFALGNNNYLPVQEHVA
FLFDLMELALNIYSLLELCDSLLKELPEVEHQLQLKKSNLVRSYTTSLALYIVSILRRYHSCLLLSPEQTLSVFEGVCRTIRHVSNPSECTSAER
CIIAYLSDLHESCVLLQGKEQSTEYYQQLQCIKRFKDIFNTPEQLDLPPQGYNPLLLQELFMAPRRGGKLDPHWLGTLHESPANVYSFVSNALIA
VCRETDNERLNDVALACAELTASCNVLSEEWIYALQSLCSGSKSPRYPHLGGQVDIGQLKTHNALAVFVCILVARHCFSLADFVSKFALPTLARS
VSAGGAELSVDAEAGARLTCHLVLKLFKTLEIPQPGMYSVSTSPNPLHAVGNDFSIRLSCDRHLLVGAHKTIPIAAVLAVLKAILIVVDNAALKT
PLASGSGTSSGGLGGAFGSGKRSGFNTPVHPGSTPKSNEQRPADLSQILGTSDLQLGSSLTSEPEALQQPSVGGMEQISLLEFAQAVLKQICAQE
HVLERCLKNAEQLCDMIIDEMLTAKQAQRVLHMICYPEPEFNIISELDQRSMIVRILENLGQWTLRISWLDLQLMYRQSLSNNAELNVWLDTVAR
AAIDVFHMEEVVLPGAVKATHKPKPSTWLVAPLIAKLTPAVQGRILRVAGQVLESMNYFSKVSKSDCNSSGSGDEREKSNSCHSSNSYGLGGVPA
RNKKMPLDYQPFLGLILTCLKGQDEYKENLLVSLYAQLSQCLQSFAELDTIGGIDEPQAREEILDALQLRFSLVGGMFEAIQKNSTPTTDWAILL
AQLVCQGVVDLSCNRELFTTVVDMLATLVHSTLVSDDERHYMNLMKKLKKEIGEKNNASIRVIRQLLPLYKQPTEVIACEHSGMDTKGNKICDID
KKQLRISDKQRISVWDILEGHKNPAPLSWVWFGAVKLERKPLTYEEAHRNLKYHTHSLVKPSSYYYEPLPLPPEDIEPVPEKICIKDEMKADTPS
SVDQSPSAVVGGTGRGRGKGTTTRKRKPKNPKTPPVVNTQQQQPQLAQQPQQPQNVQQQQLQQQQQQQQHMQQQHMQQQQMQPNQMGQMPMNMPM
NMQQFAPNPNNMMQQNAMLQQQQQQQMQQMGNNPMQQQLNVGGGNGQPNPQMNFMQQGPGGGAGPQGQQQWHNAPQQQQPPQPYHNQYAP
HQQNMQSNRIERPPLNANSKQALSQMLRQRQPFQQQAQQGPGGGFNPMQQQPQASQQQPGPQQQMNPNQMRQQQMNPQQNPQSVAAFNAMQQQPQ
QNAQQQQMNPNQQQQQQFMRGGNMRPGMAPNQMNQMNMGGQGMSQNPMMQQQIPQNMVGMVNPNANQMMQSGGAQGGNGVGVGVGVGVGGAGNNP
NMGMGGMPQQGMIQQQPQQQPQQQRAVEQALEWASAWRPISSNSSRPT*
(SEQ ID NO: 1461)

Classification: receptor

Celera Sequence No. : 142000013384518
ATCCATACGAGACATGCAACCACTCTGAGGTCAACCGGTTGTCTAATTTATCTATTCTAGAGAGTTGAAGATCAGCCATTCAGCCATTTGGCCAA
CTTATTTTTGTTGCCAACTCTATGTGGCGATGTCTCGGCACCCGCAATTATTTAAATGTCCCAGAGACAGAGATTTGTAAATTGCACGGCTACAA
AGTGCATATTGTATGGTGCCATTAAATGGACCCACAGGGCGTATGCGCAATGTGTCGCACTGAACTTTTTCACCTAGCCCCAGCTCATGAATTAA
TTCAGCTCTGCATAAATAACAAAGTTATTCAAATTCGCGAACTGTCTACCTAAATCACCAATGACTTTGGACTCCTCAATGCATTTCATAGAATT
TTCCACATTTTTCCAGCAGTATGCAGTATCGTATAAAATGATCTTGAAAGAACCTTAACGTTTGGGGCACAACTATTGGGGTTCTTGACCAACCT
TTTCTGGTTTTCAATGATAGAGTCAAACATACGTTTGTAAAGAATGGATATGCAAATATTCCATTCGTCGTGTACAACATTAAAAAAAATATATT
GATTGTTTTTCTGCGGGGATTTTGTTGTTTCGATTTATTCGGCTTCGGTTTTGGATTTCGTTTTATTCGGAATTCTCTTTTTGCGCTTCCGGCTT
GCTATCTTTGTATCAGTTTTGAGTATCATTGAAGCTGGCCAACTGCCGAAGGTCGCCGATCGGCACTCACCTCAATTGTGGTCCATAATTAGTCG
TGCAGCTGGGGTGATACCTTCCATATGAAGATTCATAGTGCCATAGTGAAATAGCAATGCGTCCTGCATTTAAATGAGGGAAAGCACTGCCACAG
AGGAGCACCCACAGATAGATTTGCATCTCCGTGCGGGCTCCACATAGTCGAGACGACAGGCCATAAATCAGAATGAAGAATACTATTGAATGCTA
ATGTTGTATACTAATTGCCGAATATGTATCTTTTCCGGTTACGCTTGCAGATGTCGCCCAACATAATAGGCAGTACCTTTATATTGGCCGAGACG
GCCATTGCCGATGGCAACAACAACAAAATGGCTGCCACACCAGCTGCTTCCGCCGCCCCTTCAGCAGCCACGCCCAGCCAGAAGGTGGCCAAGAA
AGCGGAGGCCAAGACGCCCGAGAACAAGCCCTACGAACTGGAGATCGTCTGGCGCAACGTGGGACTCTTCGTCATCCTCCACTCGATGGCCCTGT
ACGGTCTGTACTTGGTGTTCGCCGAGAGTGCCTATTGGGAACTCTTGCCAGGTGAGTTTGAGTATCAACACGTTTCGTCTTTGCCTTACTAAGCG
TCTTGGTTCATCTGCAGTCTATGCCACCATGTTCCTCGGCGGTCTGGGCATCACGGCCGGAGTGCATCGTCTGTGGTCGCACAAGGCCTACAAGG
CCAAGCTGCCACTGCGCATCTTCCTCATGCTGTGCCAGTCACTGGCCTTCCAGAACAGCATCTGGGAGTGGACCCGTGACCACCGCGTGCATCAC
AAGTTCACCGACACACACGCCGATCCCCACAACTCCCGACGAGGCTTCTTCTTCGCTCATATGGGCTGGCTGATGTGCAAGAAGCACCCCGATGT
GACCAGCAAGGGCAAGCAGATCTCCATGGAGGATATTGAGCAGGATCCCGTCGTTATGTTCCAGAAGAAGTGAGTAGTGTGCTATCTATGATTTG
AAGGCTATAGTATAATAGATCTGAAAGGTTTATACATCCAGGGTGTTCTTGAAGTTTCCCAAGTAATTAATTTGCTCGCCCAAAAGTAGGCAATG
AACAATAAACAATGTTCTATTGATTCTTAGAAGTTTAACTTTAATCCCTCTATTATATGTACTTATAACACCTCTTATTTCCTTAGAATGTACTT
TGTGGTTATGCCCATCTGCTGCTTCGCCCTGCCCATGATCTTCCCCTACTACGTGATGGGCAGCTCGCTGCGCGTCTGCTTCTTCACCTGCTCCA
TGCTGCGCTTCTGCCTGTCGCTGCACTTCACGTGGCTGGTAAACAGCGCCGCCCACTTCTACGGCATGAAGCCCTACGATGTCAATGTGAGCGCC
ATGAACAACAAGCTGGTATCCACCCTGACCATCGGCGAGGGATGGCACAACTACCACCACGTCTTCCCCTGGGATTACAAGGCAGCCGAGCTGGG
CACCTACAGTTTCAACTGGACGACGGCCTTTATCGATGTGATGGCTAAGATCGGTAGGTTCTGCTGCGCTCCATGCCCTTGCATATTAACTTTAT
CTTTATCTCTCATAGGACAAGCCTATGACCTGAAGTTCGTCTCGCAGGAGATGGTCTACAAGCGAGTCCTTCGCACTGGCGATGGCTCCCACATT
GCCGCCCTGCTGGATGCCAACAACAATAGTGCCATTCCGACCAGCGAGCTGGTGGCCCACCTGGATCACGAGAAGGAGGAGCATGCCATTTGGGG ATGGGACGACAAGGATATCAGCGAGGAGGATCGCAAGGGAGCCAATGTGGTGAACAAGGAATCCGAATGCAAGCTGGATTAGAGATCGGGGATCA
GTGGGAGCTCACCCAAAACGAACACACTTCTTGCTGCCACATCGGGTCTTCAGTATTTAATTATATTAATTGCCTATTCTCCGTACTGCCTGTGC
ATCTGAGTGGTGGCTGTAAACTGCAAACTGAAAATAACTACCTAAGGGGGATTCCGATCGTGGGACCTGGTATGATGGTAGCAAGGACATCTTAT
ATATCAATGGCTTCAATTCCAAATACTACAAAACAAATGAAAACTATTCGAGATTAGTCAATGCAACTCGTTCGCAGCAACAGAGTGTTAAAAAA
AACCTGCACCCTCTACACAATCCCAATCTCGCACTTGTCGTTCGGGGATAATGAACACATCTGCCACCCTCTCCCTCTCACTATCTCTATCTCTA
TTTTTATATATATTAATTAACTGTATATTTACGCAAGAGGTTCTAGAATTAAGCGTACCTGCTAAGATCTATTTTAAGCATCGACTTTTATGTGT
GTGTACATTGTGTTAGTTATGTAGGTCTAAATTGTATATTTCGATCCAACTATTGTTGAAAATTATAACAAAAATTATAAAAAACCAAACAAAAA
ATATTGTAAGCAACTTATTATCGAAAAGGGATGAAATACGCAATACTTCTCAAGATCCAAATGAGTGTTTAATTGCTTAATTGATTAAATATTTT
CATAGTGAGAACTAATTGTAATGGTGAGTAAGTACAACATATCAATAAACATTAATACATTTGTTTAACTCGTGCCTACTCTCGGTTTCTAAATG
TTTACGACTTCTACTGTGTATAATTGCTGTAATTATATTTTGAAGTACAATAAATTTCCCCATTTCAAATTTATTAGGTGTCATTAACCTTTTAA
CACCTTGAAAGGGCTTTAATTCTGTAGTTAGCTTAAAGTTGGTCGTTAAACTAAAAAGTCAAATGCATTTTGCGATTGCATTGCAATGCATTTGC
GGATAATAAATAAATATGGCAAAAAGTTTATATTTTT
(SEQ ID NO: 1462)

Exon: 1001..1286
Exon: 1348..1684
Exon: 1892..2238
Exon: 2296..2552
Start ATG: 1073

Transcript No. : CT25031
ATGTCGCCCAACATAATAGGCAGTACCTTTATATTGGCCGAGACGGCCATTGCCGATGGCAACAACAACAAAATGGCTGCCACACCAGCTGCTTC
CGCCGCCCCTTCAGCAGCCACGCCCAGCCAGAAGGTGGCCAAGAAAGCGGAGGCCAAGACGCCCGAGAACAAGCCCTACGAACTGGAGATCGTCT
GGCGCAACGTGGGACTCTTCGTCATCCTCCACTCGATGGCCCTGTACGGTCTGTACTTGGTGTTCGCCGAGAGTGCCTATTGGGAACTCTTGCCA
GTCTATGCCACCATGTTCCTCGGCGGTCTGGGCATCACGGCCGGAGTGCATCGTCTGTGGTCGCACAAGGCCTACAAGGCCAAGCTGCCACTGCG
CATCTTCCTCATGCTGTGCCAGTCACTGGCCTTCCAGAACAGCATCTGGGAGTGGACCCGTGACCACCGCGTGCATCACAAGTTCACCGACACAC
ACGCCGATCCCCACAACTCCCGACGAGGCTTCTTCTTCGCTCATATGGGCTGGCTGATGTGCAAGAAGCACCCCGATGTGACCAGCAAGGGCAAG
CAGATCTCCATGGAGGATATTGAGCAGGATCCCGTCGTTATGTTCCAGAAGAAAATGTACTTTGTGGTTATGCCCATCTGCTGCTTCGCCCTGCC
CATGATCTTCCCCTACTACGTGATGGGCAGCTCGCTGCGCGTCTGCTTCTTCACCTGCTCCATGCTGCGCTTCTGCCTGTCGCTGCACTTCACGT
GGCTGGTAAACAGCGCCGCCCACTTCTACGGCATGAAGCCCTACGATGTCAATGTGAGCGCCATGAACAACAAGCTGGTATCCACCCTGACCATC
GGCGAGGGATGGCACAACTACCACCACGTCTTCCCCTGGGATTACAAGGCAGCCGAGCTGGGCACCTACAGTTTCAACTGGACGACGGCCTTTAT
CGATGTGATGGCTAAGATCGGACAAGCCTATGACCTGAAGTTCGTCTCGCAGGAGATGGTCTACAAGCGAGTCCTTCGCACTGGCGATGGCTCCC
ACATTGCCGCCCTGCTGGATGCCAACAACAATAGTGCCATTCCGACCAGCGAGCTGGTGGCCCACCTGGATCACGAGAAGGAGGAGCATGCCATT
TGGGGATGGGACGACAAGGATATCAGCGAGGAGGATCGCAAGGGAGCCAATGTGGTGAACAAGGAATCCGAATGCAAGCTGGATTAG
(SEQ ID NO: 1463)

Start ATG: 73

MAATPAASAAPSAATPSQKVAKKAEAKTPENKPYELEIVWRNVGLFVILHSMALYGLYLVFAESAYWELLPVYATMFLGGLGITAGVHRLWSHKA
YKAKLPLRIFLMLCQSLAFQNSIWEWTRDHRVHHKFTDTHADPHNSRRGFFFAHMGWLMCKKHPDVTSKGKQISMEDIEQDPVVMFQKKMYFVVM
PICCFALPMIFPYYVMGSSLRVCFFTCSMLRFCLSLHFTWLVNSAAHFYGMKPYDVNVSAMNNKLVSTLTIGEGWHNYHHVFPWDYKAAELGTYS
FNWTTAFIDVMAKIGQAYDLKFVSQEMVYKRVLRTGDGSHIAALLDANNNSAIPTSELVAHLDHEKEEHAIWGWDDKDISEEDRKGANVVNKESE
CKLD*
(SEQ ID NO: 1464)

Classification: enzyme

Celera Sequence No. : 142000013383864
AATCCAAAATCTTGCCCTGAACTTGACTGTCTGCATGTGATACGGTTGAACGCCTTTTGCGGAAATTATTGCAATTTTCTTGTCTTGTCTTCTAG
CCGAACACACATAGCACCGTACATTGGGGTTTTGACGGTGGGTTTACTTTCACTTTTGCCGCACTTACTCAACAAGTTGTGGGGGCCCGCTGAAG
TTTGCTCACAGGGGAAACATTCATCAAAAGATTGAAGAGCTCGTCTTTTCGCTCTAACTCAAATAAGAAGTTAAGTGCATAAGTGAAGTTAGCTG
CACATAAAAATAGTTTTTTATTGCAGCGCAATTTTTTCTAGTTTCTAGCGAGTTTTAAAAGCGTTGTGTTTACAATCTTTTAAAAAGAAATTTCA
AAGATTTTTACTACGAAGTATTCTTTGCATTACTCCTTATATAAGTTCTACTTTATATTGAGATCAAATATTAAAGTCTTGTCTTAAAGCTTGAT
AGAACTTAGTAATGACTTATAAGCTTCAAATTAGAGTATTTAATTACACAGAATAATTAGTTAGTTAAATTGAATTCATTGGTGTGACTTAGAAA
GCGCCACAATTCCTTTTGTTTATTTTCCCTCACTTTTCCAAACGAGTGCAACGTCAAACCCTTAAACAAAGTCCACTCCACACTGATTGCAACTT
TGCCAAAGACCAACAAATCATTTAAACAAATCAAACATCAACAGGCGACCGGCGAACAACATGGAGACCTATTTGACGGAGATCAAACAGTTGCG
CATACCACGCCCGAAATTTGAGCCCAACAGTTGCCATCAGCAGCACCATCATGCGGTGACAGCCGTCGGAGCCACGCCCATCCAGCCGCCCCCGC
CCCTGCACCACCGTCAGTGGCGACACTTTGTGCGACCCTTTACGCCGCCACGCGATTACCATCTGCCCATGGTGGCCGAGGGCTCCTCCATGCAC
GACAAGATGTGAGGAGGATTCACATTCAGTGGATGGGCAAACATGATGCATTACTCCCACACATAGCCCCACATAATATACGATACCTACTTAGG
ATAGTGCTTAAGTCTAGATGTTAGCTTAGTTAACGTACGATAGATACAGATACAGTTGCAGATACAAAGAATTAAAGTATACAAAAAATGGAGAT
TTCTTTATAATTCGGGTTTTAAGTAAGTGTGCTGATCATGAAATGAAACTTCATGGCATGAGCAAATGGATTTTTGAGAGTGTTACTTGGAACT
ATGTTGATAATCTGTTGCTCTACCATTTATAAAATATTATATTTAATACCCAGAGATATCAGAACCTACGACAAAATCACGATCGTTTCGCTTAC
TCACCGCATCTGGTTCGTATTCCGGTAAAAGGGTTTCGCTGCCCCGGCGAGTTCTGTGCTCATCACAGCCGTATTCCTAAGCCGGGATAAAAGAA
TTTACAAGATACATTTTTCAGCGGCTTATGTGCTTCTTTGCTCGACGACCAATTCGGTTTGGCACTGGTCTAAATGCGACTTAACAGTATTACAA
CACTCAATAGCCAATTGGACAACATTTAATAAGGAAGTACAACATAACCGGAAACAGAGACAAAAACGCAAACATCAACCACATTGAGCAGTTGG
ACAAACATGGAAAAAGATTCAAAAGTATAAAAAACGACAATAGACGTTACACACAACAAGAGACAAAGATACAAAAAGTAGATAGACAGAGAGAG
ATAAAACCACTAAAGATACAAAATAAAGTAAGACATATACAACAGACAGACAAGAGCTGCAGATTGCAAAACTCGGCGATGTAACAGCCGAATGT
CAATTTTTTTCAATAAAAGCTTAGAAAAACTTAAAATACAGCATATTCATCAGGCAGAGATTTCGGTGCCAAAAAAAAAATATTGTTAGAAAATA
AAGAGGAAACTTTATCAGGAGACTCATCGAGTAATTTTCTTCAAAGAGCCTAGATACGAATGTTTCAAGATAGGTATCTTTGACAGATTAAAAGT
TTTTAGAACAGCTTGCGGAACAGTGAAATTAGACCTTCAGTGGTAACAATATACATATATAGAACTTTTTCAGCTTGCTACCCTATTCGCGCGAC TCGCTTCAGTCCTGACCTGTTGCTGATTGTCTTTGGTCTGCCTGAATTTCAATTGACTTGGTCCCAACGGATGGTGATGATGACGACCGGATCCC
ACGTTGCCGCCGATACCGCCCAGATGACGCAATGAGGCATGGTGGGGTTGATAGTGTTGCTGCTGCTGTTGTTGTTGTTGTGGAGGCGACAATGA
TGATGAGGACTGGTTGCTGCCTGTCTGATAATGTGATGCTGGCTGTGAGCGATGCAGTATGGGTCCCGCCGACATGGGACGATGGGGCAACTGTA
GTGCGGGTCTAGCGTATACATATACACAGGTCAGTTAACGGTTATGATGGGAAATGGGTGCTTAGGGGTCAGTGTTGGGAAATTCCTGAATAATA
TTTTCGAGCTATATATCTATATAGCTATATATCTATATATATATATCTATATATAGTATATATATATATACTTTTATAATAAGTAAAATTTTAAT
TTACACAATGCTAAAATTTTGTAGTTCCGAATAAAAGCACTTTTAGTTCTATAAGCATTAATCATCATCATCTTTTCTTTTCACACTATGATAAT
GTTAAAAACGCATTTGTGAATCTTTTGTAAACTACTACTACCCTATCCAACACTGTTCAGGATGGGATATTTTGGAATATGGGATTATATGGATT
TTAGGTAAGTGGCTAGGTACCGTTTGTATATATCCGTTACGGTCATGCCCAGGCCCGAGTCCGACGAAGGACTCCGTCCGGTGGCGGCTATTATT
TCCAAATCATCAGCAGTTACCTGTTGGCGAACGGAACGGAATGGTACGGAATGGAACGAATCGAACGATTTGGTTTGCATACGATTTGCGAGTGA
GACAGTGACAGCTGAAAGGTTTGACAGTGAGTGAGAGTGAGAGGGGCTCTAGCCTAGGCTTCTGTAGAATTCTACCAAGCATAGACAGAGAGATG
AAGAGAGAGCGAGTCAGAGAGAGAGCCTAGGTAGAGCGACAAAGATAGAGTGATAGGGAGTGCATTCGTACTTCGATCGGTTGTTAAATCAATTG
GTATTTTATATATTGGTGCTGATTCATGGTGACTGTTGTGGTTTCTTGGTTATCCTTTTAAGTGCATTTTTAACGTGGGATTACATGAGATCAAT
TTGATATTGTACAATAATTTTATTACTTAGTGTACTAAATCTAAAGATTACTATTAGGTTGAGCTTTGTCATACCCCAATTATCAAAGCAGATAT
GTTTTTTATATTCCGTATGTATGTACATCTACAGTTTGGCTCATTTGGAGTCAACTGCACTTTTGAAAATAATTAAATTGGATTAAGTTTCCACA
AAGCAATTTTTCCGATCGATTTGGTTTTCTTTTTGGCTTAAAATACATAATTTTACAAACAGTCTTCTTCTTATTGCTATAAAATATGTAAAAAC
TTCGCCACTACAATGTAGAGTAAAGTTGTATGTATTTATATGTGGGTATTGGTTGGAAAAATTGACATTCGATTTGATTGTTTTTGTTTTGAAAT
GCAATTTTACTTGCAAAGGGCCGAATCAGATGTAAGCGAGTTTCTGAAAGCTTTCTCAAAAGTAAATAAAAGAAAATTACATGCATTTGTTTTGT
AAATGAAAGAAGCAATAACTGGTTTAGAGTCGGGTGCCTAAAGAAAGTATCAAGTGTACGTATCTCGTTCAACAATTAAACTACAAGTTTTGTTT
TGATTTTCTTTTGTCGAGTGTTATTTGTATTTTTTCTACAGTTGGAACAAATAAGTTAAAGTAAAAGTTACAAACATACAGTGACAACAATTATT
AACGACAACAGCAAGAAGAGAAAGATATACTAAACAATAAACACATTGTGGGAATTATATAGTATAGTATAGGTAGTAGAGTAGGTATATAGACG
AATAGTAGACAGTAGACCGGTTGAACAGTAGTCAAAGTTATTTAGAGTTTATTTGGCTGAACATGCTCAGTGTGTATTTTTGGGGGATATAGTCG
TGTCTCCCTCTTAACTAAGTGTATATAGTGTCTGTGTCGTAGAATAAATCTTCTAAAAAGCTTACCGGCAAATCACGGGCGGGGTCTCCCTTACG
CTGTAAAAGATTATAAAGTTTACATATGGGATTAACAGGGTATAGAGATCAACGGGCTTACCCTATGCCTATCCACGCTATAAGGATCGCGTTCT
CTGCGATAGACGAGCTCATCGTATCGCGTGCGATCCTCGGGGAAAACTAATTCCCGTATTTCCGTCACTAGCGTGTGCTAAGATGGGAAATTGAT
TGATGTATATTAAGTTTCTCTTATTCTCTTATCAGGTATCCCTTGACTAGGTTAAACACTCACCTTTTCGTACGTATCTAACATCTCTAACAAGA
CGGCAACAAAGGCATCTATGGTCATTGCTTTCGCACTATATTCGGCAATATAGTAGGAAAGGCTTGCAAAGTGATGACGGGGCAGCAGGGAGCGC
GCCTTCTCCTCCACCATGGTCGCAATTTGACCTTTTCGGCGTGCTCTGTAAGGCAAAAGCTAGATGTTGTAGAATCTCTTGAAAAGAGATTTTAG
ATCAGTCGAGACCCACCGTGTGCCCGTTGGACTGTAGGCGTCCCAGGGCTCCATCTCGATGGAGGTGCAGGAGTGGGGCACCTTGCCCACGTCAC
GTATCACCAGCGACATGCGTTTGTGGTACTTCAACTGACCCACCGCCTCGTCGTGCGTCACATCGAGAAAGGATTGCCCATTGACCTCGAGGATC
TCGTCGCCAATCATCAGTCCGGATCGATCTGCCACGCTGTCCTTATCTACGCCGGTGACAAAGATCCCCAGGCCGTACTCCACGCCGCCACGGAT
CATCAGGCCCAGAGACTGACCAGGTTCGATCAGCAGCTCCACGCGACGTATGCTATCGGGTATAGAGTGTTAAGTTGTTAACTAAGAGCTAGAAG
CTAGATGAGGTAGGAAAAACAGGTATGTATTTAAGGGTAAACCCTATATTTATCGGGACGACATTATCAAATTTTTTAGTTCAATCTCAGAGTAG
CGAATCCTAAGTATTATGAATATTGGTACATTTTAGTGCCTTTTGTTAAAATTTTTTTTTTTTTTTTCAAAAAGGTCTGCTTTATTTTGAAATAT
TCTATATATACTCACCGATCCCTTCGCTCGCTGCGCCTGCCCCCGTACTCCATGGGCGGGGAGGCGGGTCGTCCGTGGCGGTCCATCCAGGAGCA
GGTCTGGCGGAAGGGCAGACCCGCCCCGGAGGCCGCCGCCGCCGCTGCTGCCGCTGCCGCCTGGTTCTGTGGGTGCAGGGGGGGAGCCATCGATG
CGTACATGGGGTCGCGGGAGGGCGGACCGAAGCCGTGGAGCGGGGCGGTCGAGTTCAGAGTGGGCGGCGCTCGCACCGTCATACTGATTTGACGT
GACGATTTCAATATCTGCACACATCTCTGCGTTAAGAAAAAAATGTGGCAATAGAAGAGACACAAAAAAGAGAGGACAGATGCAAGCAGAACGGAA
CGAACCAACAAGAGAAGAGAGAAAGAGAGAGAGAGAGTGGGAAAATGGAGCAAAGTACTAAAGGAAAATTAACAAAATGAAATGGAAATTCGCCA
ATTGCTTGGACAAAAACGTGTACGTAACGTGGTGCCAGAATTTTCCGATATTATTAATTAACTTTTACTGTGAGCGTGTTCGTTACTCGAAATAC
CACCCAAAATTTCGCCTGACTTTCATTTGTCGGCGGCCTTTTGCGGTCTGATTTTGTTGTCCGTTCTCAGTGAAGCTTGCCACAATTTGCTGTCA
TTATTTTAATTGTTTCTGACCAAAAAACTAATGTGAGAATGTGCAAAGTTGTGTTGGTCCATGGAGAAAGGGGCTATGTGCGGGTGCTTTGTGCA
AATTGGTCTGTGAATTCTCGCAGGTGTTGCCTGCTTTTAGGGGCTTCCAGGTTCGGTTAAAGTCCTAATTTTTCGGTTTGTGGTGAACTTTTCGG
CCAACTGCACTTATTTTTAATAAATGTATAAGGATTATATCAAACTGAAGTGCAGCATCATAGCATTTGTGGTTAGATTCCTTGACATCCAGCAA
GGATGTAAATGTGTTGTGAAATGCTTTTCAGCTCAGTTTTCTAGTTAAAAGGATGTGTGGCAGCGTTATGGAATCTTAAATTTATAAAATTCGAG
CTCTCTACTGTGTTGGCAGAAACGTCAGTCCTTTGCAGTCGGTCAACAGAAGCTAACAACTAAAAGTGTGTAAATAAAAAGCATTTAACAATAAT
AGAACATACCAAAATAATTCTGATACAAAATGCGACTAATCTATTGCCAATTTTTTCTCAGTGTATATTTGTATTAGTGTATTATTGATTTTATA
TTCATGGTTTTTCTCAAATATATGTTCGTATTTGGTT
(SEQ ID NO: 1465)

Exon: 5497..5241
Exon: 4992..4672
Exon: 4605..4434
Exon: 4352..4242
Exon: 4180..4151
Exon: 2870..2796
Exon: 2370..2107
Exon: 1406..1335
Exon: 1036..1001
Start ATG: 5497 (Reverse strand: CAT)

Transcript No. : CT25276
ATGACGGTGCGAGCGCCGCCCACTCTGAACTCGACCGCCCCGCTCCACGGCTTCGGTCCGCCCTCCCGCGACCCCATGTACGCATCGATGGCTCC
CCCCCTGCACCCACAGAACCAGGCGGCAGCGGCAGCAGCGGCGGCGGCGGCCTCCGGGGCGGGTCTGCCCTTCCGCCAGACCTGCTCCTGGATGG
ACCGCCACGGACGACCCGCCTCCCCGCCCATGGAGTACGGGGGCAGGCGCAGCGAGCGAAGGGATCGCATACGTCGCGTGGAGCTGCTGATCGAA
CCTGGTCAGTCTCTGGGCCTGATGATCCGTGGCGGCGTGGAGTACGGCCTGGGGATCTTTGTCACCGGCGTAGATAAGGACAGCGTGGCAGATCG
ATCCGGACTGATGATTGGCGACGAGATCCTCGAGGTCAATGGGCAATCCTTTCTCGATGTGACGCACGACGAGGCGGTGGGTCAGTTGAAGTACC
ACAAACGCATGTCGCTGGTGATACGTGACGTGGGCAAGGTGCCCCACTCCTGCACCTCCATCGAGATGGAGCCCTGGGACGCCTACAGTCCAACG
GGCACACGAGCACGCCGAAAAGGTCAAATTGCGACCATGGTGGAGGAGAAGGCGCGCTCCCTGCTGCCCCGTCATCACTTTGCAAGCCTTTCCTA
CTATATTGCCGAATATAGTGCGAAAGCAATGACCATAGATGCCTTTGTTGCCGTCTTGTTAGAGATGTTAGATACGTACGAAAAGCACACGCTAG
TGACGGAAATACGGGAATTAGTTTCCCCGAGGATCGCACGCGATACGATGAGCTCGTCTATCGCAGAGAACGCGATCCTTATAGCGTGGATAGG
CATAGGCGTAAGGGAGACCCCGCCCGTGATTTGCCGGTAACTGCTGATGATTTGGAAATAATAGCCGCCACCGGACGGAGTCCTTCGTCGGACTC GGGCCTGGGCATGACCTTGCCCCATCGTCCCATGTCGGCGGGACCCATACTGCATCGCTCACAGCCAGCATCACATTATCAGACAGGCAGCAACC
AGTCCTCATCATCATTGTCGCCTCCACAACAACAACAACAGCAGCAGCAACACTATCAACCCCACCATGCCTCATTGCGTCATCTGGGCGGTATC
GGCGGCAACGTGGGATCCGGTCGTCATCATCACCATCCGTTGGGACCAAGTCAATTGAAATTCAGGCAGACCAAAGACAATCAGCAACAGGAATA
CGGCTGTGATGAGCACAGAACTCGCCGGGGCAGCGAAACCCTTTTACCGGAATACGAACCAGATGCGGTATCGTATATTATGTGGGGCTATGTGT
GGGAGTAA
(SEQ ID NO: 1466)

Start ATG: 1 (Reverse strand: CAT)

MTVRAPPTLNSTAPLHGFGPPSRDPMYASMAPPLHPQNQAAAAAAAAAASGAGLPFRQTCSWMDRHGRPASPPMEYGGRRSERRDRIRRVELLIE
PGQSLGLMIRGGVEYGLGIFVTGVDKDSVADRSGLMIGDEILEVNGQSFLDVTHDEAVGQLKYHKRMSLVIRDVGKVPHSCTSIEMEPWDAYSPT
GTRARRKGQIATMVEEKARSLLPRHHFASLSYYIAEYSAKAMTIDAFVAVLLEMLDTYEKHTLVTEIRELVFPEDRTRYDELVYRRERDPYSVDR
HRRKGDPARDLPVTADDLEIIAATGRSPSSDSGLGMTLPHRPMSAGPILHRSQPASHYQTGSNQSSSSLSPPQQQQQQQHYQPHHASLRHLGGI
GGNVGSGRHHHHPLGPSQLKFRQTKDNQQQEYGCDEHRTRRGSETLLPEYEPDAVSYIMWGYVWE*
(SEQ ID NO: 1467)

Classification: enzyme

Celera Sequence No. : 142000012806290
TCTGACATCACTCCTGCCTTATCTCATTACATATGTACGTATGTGAATTCGGTTTTTACATTCCTTTTTGTACTTGTTAATCATTTTCATTTGAT
ACTTGATGAACGTGAGCTGGGGCTTCGCTTCGATTTATGCTTTTGTCGGCAAATTGTAATCAGCTTGAAAATTTCCACTGTCAAATTGATAGAGC
TTAAAAGCTTCGACAGTCCCGAATTTTTCAATTGTTGTGTTTGTTTATCACAAAAATATACCTATCATTATAATTGGAATCATTGTTGCTTCCGA
TCACATTACGCTGAGATAATCTCGAAATTCCACACTTGCTGGTGTGTAAGGGGTATCTGATAGTCGAGACAGTCTTTACCTGCGTTTACTCTAGT
TTAAATTTTCTCTTAATTCAAATATCTTAACGGAATAAGAATATATTATTATTAAAATAGTTTACCTAACTACTTACTTTTGCTTAATCCATTGA
CAGTCGACCTAGTCGTTCCATAATAATTTCACGTATTTATTTGATTTCTCATTAATAATTTATGGGCTTAAGAATTTACAACTAGTTTGCTTAGA
GATGATAATTATTCTCATTTATCGTATATTGTTTGTTTCGTTATCAATCAAACATTTAACAATTATAGCACGTTCAGGGAAACTACGAGTAGTAC
ATACATACTGATATTACATAATACGACCGTTGAGAAGGCAACTCAAAAATTGCACTAAAACATTCTTTTACACAGAACCAATTCCATTCGAAATG
AAAACAAAATCAATTTTACATGTAGAATTTATACAGGGCAAAAACATTGGGATTCCACCACACTCTTTTTTTTTTTTTTTTTTTTTTTTTGGTGG
GCGTGGCTGGTGTTGCCTACTTTGGGGATGCCCCATTAACCACTTCGGCTCGTCGCGTTTCATTAGCTACCTCGAATACAATATGTTCTTAATTA
ATTTTAATAAATTCACGCTTTGATTGCTATTATCCCATCCACTCCTCCGCTCACTCCATGGCCTGCGAAACGCTCTGCTGCGGAGATTGGGCAGG
TGAAAGGCTGCGGGGCGTTGCCGTGGCGCCGCCCGAATCCCCAATTCCGATCCCACTGCCATTTCCGTTTCCGTTGGCGGCCGCCCTCTGTTGAT
TCTGGGCCTGGCTGAGAAGCTCCTTGTTCAGCCGGTAGCTGCTCATGACGTTGGCACAACTCTGGTGGAAGTAAAAGTTACGGCCGCGCAGAAAC
GCATCCGTGTTGAGATCCTTTAAGCCTGTCTTGAAATACACAAGAAAAGCGGTCGCAAATTATAGAAGTTAGAGATGAAGATTTACGTCTTAAGT
GTGCATTGACTAGTTAAAATTGCTAGAGTGGAAAGCGAAAGTTAGGGGTTCTCGGGATTGTGCATAGATCGAGCTGATCGAGGTAAAGTGAAAAC
TGAAGCAAACTGAGAAATTACCTTACAAATGAAACATTTGTTTTCATCGTCCGGTTTAAATCCGAACTAATCCCCACCTTTGTGTCCAATTGCG
TTAATCCCGGCACGCCCATCGACGACAACTGCGACAGGCTGTTCTCCATGCTCTCTGCGTATTTCGTCGACGGATTGTTGTTGTTATTACTGTTG
CTATTGTTGTTGTTGTTGTTGTTGTTATTGTTGTTGTTGTGAGATATGTCCATGGGTCCGGGTTCGGTGCTGCTCACCTGCGGCTCCGACCGCGG
TCGCTCCTCCACCGGTGAGATGTTCTCGAGGGATCTGTAAGTGATAAATATTTTGGGATAAATACTTGGCGCAGAACATGCCCACCAGCAGCTAT
CGTGCACAAAAAAAGATACTGATTCCAAAAGCAATAAGAATATGCAGAAAAAGCAGACTTTAATCTTTATCTTTTTTTTTTTAACAAATGTTAAC
CTTTTGAATAAATAAATACACCAGAAGTGTCCTTTGTTACGCAGTATGCACAAGTTTGAATAAACTGTATAAACCTAAACATATTTATATAGGTA
TCTCCGTACTTAAGAAATCTTTAAACGCTTTAAATCTTTCAGTAAGCATTACTTATATACAAATAATAAGATTTGATTTCATCATTATCGAAAAA
ATCTTGCAATACACCACCAAGCAAGTTACTAAAGTTTTGGTTTCTAGGAAGTAATTGTTATTATTCGAACGACTGGAACGACCGCCTCACCTGCT
GCTGCCGACGTTCTGCTCGTCCTGGCGGCGCTGAATCTTGCCATAGTTGATTTTGCTCGTCAGCTTCACGGTGTCGTCGTCGTCCACAATCACGT
CCTCGTCGCTGTCGTTTTGGCAGGAGGCCGTGTCCATCATCAGATCCTTGTTGCTGCCACCGCCGTTGTTGTGGGTGCTGCTGCTGCTGTTGGTG
TCGTTTACGCCCACGCCGCATGAGTCCGCGTTGTAGTAGTGGTGTGTGGTGGATGACAGCTCGCTGACGGTTTTAACTGCGGGTTAAGTGGAATG
GGACAATTTGCATAAGTTGCGGGACATAGATATAAGTCTCATAAAACAAACCAAATCTAAATAACTGATATGGTTTTGGAAATCTTTGGATTTGG
TTCATTTCAACTTCTAATCAGTAATATTCTTTGATAAAACTAAGCTTATATTTTGAATGTAGATTTTGGATTCAAGCAATATAGGACATTTGAAT
CTGACAACTGGAAACCCACCACTGATATGTGCCTGGGTTGGTGCCTCTCCCGGCCAACTACTGCTGCTCGCCGTTGTCACATTGGTGCTCACGTC
ATGCTCGTCGGGATGCGGATCCTTCTGGCTGAGCACACAGCCCGTCCGGTAGAGAATCCCGTCCAGCTTGCCCGGCTGCGAGTTGCTGTTGTGCA
TACTGGAGGGCGGCATAACCGTGCCGGATGACCCAGAACTCGGAGTAGCCAGCTCCGAACCTGAGTCGGGCACTTCGTCGTTGCAGCTCTCCACA
TCCACCGTTTCGATCTCCTCCTGCGATTTGGCATCGTCCTGGAAATATAAAGGAGTTCATTTTAATATTAATATTGAGATATTTTAATATCTAGA
ACTTTGTATTCCTTTAAATTTAATTTAAGACTGATATTTATTGTAGGACATTCCACTTACCTCCGGAGGAATCTTCCCCGTCTCCAAGGCGTACT
TCCTCTTGCAGATCGGACAACTGCTACAGTAAAGACTCTCCATCATGTACATTTCGCCGTACTTGCGCTTTCGCACTTTGAGTCTCAGTCGGTTC
TGGCGATTGTTACGTATTCTCTGAAAGGTCTGGGGAAATCGAGAAGATAAATGGTTAGATTCGCACCAGATTAGCTCCTGAGGAACACCCACCTC
CCAGCGGTTGTGACTGGTGCGAATGGCGTTCTCCTGCGCGGGACATGGAGGAGCAAACATGTAGGTGGCCTGCAGACTGGCCCTCTCGAATCCCG
CACTCAGCTTGTAGAGCCTGTCCAGTTCGGTGAGGAAGTGGGTGTGCCACTCCTCGGCGCTCAGCTTCAGTCCGCAAACGGGGCACATCTCGGGA
ATAGCACCGCCGGCAGCTGCCGCCTGCAGCCCACTGACCAGGCTCAATCCGCCGGGAACTGCTCGCAGACCCGCCATGCTCAAGCTGGCCAAGGC
CGCGTGGTGGGCGGCGTGGTGGTGCGACAGCGGATGGGGATGGGCCATGTGGTGGTGCGTCGTCACCGCCGTGGACACCGGAGGTGCCCCCACAT
GGTGGCCCACGTGGTGATGGCTATGGGCGTGCGGATGGGCCAACGGATGCGGGTGCGAGTGGGCGTGCGTGTGGGGGTGATGGTGCGGCGAGGAG
GCGGCCAGGTGGCTGGCCATCGAAACGGCAACGCTGCTGGTCGCCGTGCTGATGGCGGGATTGCTGGTGGAGCAGGAGGAGGACGAGGAGCTGGA
CGCCGACGAGGAAGTGGCCAGTGCCTGGTGGCTCTTCCCCGCATTATGCAGATCTGTGTGGGCGGGAAGAGGAGAAGACATCGTTGAATTCCAGT
CAAGTGCGCAATCATTAATCATGAGTTGATACAATTGAAATGGAAAACACAATCTAGCATGGATTGGCTGGCACTTAAAGAAATATTAAATAGTA
TCTACAAATTTCTAGAATCTAGAATTGTTAGCTAACCCTATATACTTTAATTAAAGCTCAAATAGAAGTAAATTTATAATGGATCAATCTTATAT
GAATTTATCTTAAATCGATTTTTCCAGTGCAATTTCCACCTTTTTTTTCCAGCCAATAAATCTGCCAGGCATTTTCTAATTGCCTCATGCCTCTT
TTCAGCACATCGGTGGAAATTAATTGGAGCTCGTAATTCTTAAAGCGAATCTGGTTGCCACCAACTGGGGATCAGGGAATCCAGGAGTCCGCTGC
AGGCTTCCTGATGTCAGACACACGTCGACCCCATGTATTCCGGGGTCGAAATACCACTGGCGAAAAAATGAATAAACCACCGGCAACCACAATAA
ATACAAACTGTTTGCTGCGAACCCAGCAAACAAAATGTGTCCGCCGTTCTGCACGTGACTGCGGCCGGCAATTAAAATAATATTACAATAAACAT
ATCGCAGTACGTTCCGAACAGGCCCAGTCTAGCAGCGGTCCAACAGTAAAACAGTTTTATTTATATTCTTCTAAATTATTGCCCAACAAAATATG
TCGGTTAACCGCGCCCATCACCGCCACTCGAATGGATATGCTTAACATAAATGGAGATACATTCGAGTCGTGACTCCGGTTCAAATTAGCTGGCA
GTTTGGTGCTCCACATCTCTCACTTTAGCTGGGGTTGCTCCTGGTTACCATTTAGCTAGTTCATAAACTTCACTTTTGAGATCAGAATTTGGAAA ACTAAGCGAAATTTAATTTTTGTGGCTATTTTGTTGTATGTATTTCATAAGAAAATTTAGCTCTATATTAAAACAGCAACTGTTGAAAGAAGAAA
TACCATTTGAGTAAGATACAATCGAGAGCAATACAGATTACAACTAGTTTCAGTAGTTTTATTTTTGTGATTAGCTAAATCTGCATAATAACTTC
TTGGAACCCATGGGGCATTGTATAAACTCTTTGTAGTATGCAATATATATAGTACTCATGACTGGCATAACTGAAAATATGTCCAGGTTCGATGA
CCACCCACTCCACGCCGATTTGTGACACGTGCTCAACGATGCTATTTCATAATCCTCCCCGTCCAAGGAATGGGCGTTTCATATATCGCCGGATG
AAATATGACTTTGCCATTAATATTACGGAAATTAATATGAAAATTCCAAGTGTGCATTCAATATAATACATCATCGGCGAACAAAAACCGCGGAG
CAGAAGTAATAGCAATAATAACGCTCGTCATAACAATGGCAAACAATGCAATCAAAGCGATTCGCAACACTTGCGCATCCTTTGAGCCAACAAAT
CGCAGAGTAAACCGAAAAAGTGTGTCCCCCAGCCGGCGATAAATGAGCAAACATTATGGAATCTCGAGGGTGGCTACACAATGCCTCCGGAAGAG
TTGCGGCAATGTCCTGGATGAGTAATTAGCCGCCACTGGAGAGGACGTCTTCGTGTGCCGAGCACGAGCCGCCCGAAAGGATGTGCGGTCGGTTT
GACTTTGTAGTCAAGTGGTCGGGTTGCCTGGAATGGGGTTGTTGTAACATTTCATTGGGACCACTCCAGTCAAGTATCCTTGTATCCTTACACGT
ATATATCCTTGTGCCATTTAAAACACTTACGACATGCACCCCTTCTCTTAACCCTTTGCCGCCCTCTCATTCCTCGGATGCCCTTTTGACTTCTG
CCCCGCAGTGGGGTTAAATTGGCCTGTTCGTCGCTAACCTTCAGTTAGTTTAACCCATTGATGAATGCTGGCCTGCGCTGCAGCTTCAGCTAATT
AAAAGTGTATTATTTATCGAAATTAATTTATGGCGCTCCTGTCTATCCACGACTACACGCTAATCTAAAAGTTAAACACAAATATCCACATGTTG
AGTATGGGTGGTGGGTTCATGTGGCGAGGGAAAACTGGTTTTCCGGCTTAAGTTGAAAGGCAAATAATGGCCGAAAGATAAACAGAGTTGTCACT
GTTTTAAGCAGAGGTGTTGGAAAGGGGGGGTCGACAAGTGAATATCATTAAATAAATTTTACATTTTATGTGTAATATTTATTGCAAAAATCTAA
CATTTCATGTTCCAACTCCCGGTTTTCAACTGAATATTCTAATTGGTATATCTTCTAATTAGAGTGCCTTATAATGCCTACATAATGTAACATTT
AGGAAACCCTTTTGAACTCTCTTGGCACTACGCCCCTGTCATTTATCCCATTTGCTTTATTCATTTGCATTCATATTTATCATTTTCATATGCTG
CAGCCCGATTTTTGTCATAAGGCGCTTAACTCGATCAGCTTTACTAGACCAATTAGCAACGCATTTGCAGACGAGACGGTTTAGCCTACTTTTTG
GTAAGGTTGGGATGGAAATTTGGGGAAAACGGAAAAGCTGGAACAGAAACCACCCCCAGGTAAATAAAAGAGAATTTAAGCAACATTTATCTGGA
CTCGAGAAAACTAATAAAAAACGAATTGAAGTGCAGGAGATGAGAGGTCCTGTCGCTGTCCTTACGCCTGCCAGTCAAAGTTAACCTACTGAAGC
GTTAAAATTGCTCGGCAAAAGTAAAATTGAAACAAATACGCCCGGCGATTTTTATCAGCAAAAAAAAAAAACGGGAGTTCGAAAGGGCAGAACTTT
CCAATTTTTCCTTTTATCGCAAACATGCAAATTTTTTTGTGCGATGTCGATGTAAATTTGCTAAATAAATAAATGCGGTGCAAGCAACCCTACTT
ACGTCTCAAATCCCTGGGATCCTGAGAATTATTGCTGCGCGGACTTTCACCCTTTTCAACGGCATCGTAATCCTGTGATCCCTCCATGGATTCGT
GCGATGTGCATGTGGGGCTGGCCGAATCCGTGCGAAATGATTCGCTGCCATTGAACAGATTCTGCCGGATGGAAATCGAAGTGCAAATCCCATTA
TGACACGTGTCAATCTTGCGCCGATTAACAGCTCATAGCATCAGCGGATTCCGCAGCGGATTCCGATTGGATACCATCCCAACCCGATCCCAACT
CACCTGATCCAGGGATATGCCGATGTACTTGGGCGGCGAGAAGGCCGACGGCAGCGAGAAGTTGGACAGCACCGACGGCTTGCCCAGCGGCGAGC
GGTCACTGGCAAAGTAGCTGGCCGGTCCCGCTCCCGCCGCCGCCGCTGCCGCCGCCGCTCCGTTGGCCACCAGCATCCCGTGGTTGAGCAGCAGG
TGCGGATTGAAGTAGTTGCCGACTAGTGACATATTGTGCAGATCTTTGGCGTCGGGTAGCTGCAAGAGGGGGAAATCGAAAGGGATTACCTAGGA
AGCACAGTTGGGGCGAGAGAAATGGGGAAAGTATTGTAGAATCGTGGCATTAGCAAGTTTTCATTCATTTTATATTACTGGATTTTCGTTGGGTA
CCATTATACATATATCAAGGTCGATGCATCTATTCAGTTTATGAGTGGGAGCAAATCCAACAAAATATTTACCAAAAATTTATAGATACTTCTTT
GTGTGAGAGAAGAAAGCAAAACTTTAATACTGCTAACTAAAACTGCTAACTTAAACAAATTTATATGTATTCAAATAAATTTGCATACATATTTA
TTATATACTTTTAATACTATTGTTAAATAACAAATCGATTTATTAAACCGAAGTGGAATTTTATAGTTAAGCTAATGCCAAAAATGTATTGTATT
CGTTGCATAATTAAGAAATAGTAATAGTAGTTGTTATAATCTAGATTAAGTTCCTTTAAAGAATCCTTCAGGTATTTTATCCTACCTTCCCTTAT
CTAAGCTTGTAATTCTTTAAAACGTGAGAATCTAAATATATAAATATGAGATCTAAATATCTATAAATTACAAGAGGATATTTAACCGCAAATAA
GAATGGAAATAAAAATGCTAGGAAGCATGCTTAGTAAGCATCTAAGCCTAGAGTTTTTAAAAGTTAAGTGAGCGTATAATTTAAGCGTTAAATAT
GCGCATTACTCGAGTCTGAGCATCGGAACGCGCAACAAATTATGGGAGCTACATGACTTGGCGTTAAAATTAGCCAATTATGGAAGGTGGAGGCC
CAAACGCGGATGTGTGTAACATATGCCAAGGCTTGGAAAGGTTTGGAAAAGCAGGAAAACTGCGATACCTAATCCCATTCCCCTGGAGAAAAGAT
GGAAGAATCTGCGAAGGGCGGCGTCGATTTGCATCGATACAAATTGTGAACAAAAATGTTTAATTTACGACGAATAAATGTTAAATTGAGAGATT
TTAGAATTACGATATCGAACATTGCCATAAACTGTGTCAATATCGAAGGGAAGTGGCGGATAGCTCACTTCCAATGGGGTGTAAAATAACGAGAA
AAACGCTTTGGCCCCCGCCCCAAACTTTCTCCGATCCAAAATTCACACAAGGACTCTGGTAAATGATATGGGTGAAGTGGCAGGGTGAGTCCGC
TGTAGTCCGTGGTCTGGGGCAGATAACCCACAGGACTCACAGACAGCGTTCCCAACAAATTGAGGCTGACGAGTGAGCTAAGCGGCGGTTGCCGC
ACAGACAAGATACGAAGATACGAGTAGAACATAAGCGGCGACATGTGTGACAAGTATTAACCCTCACCCACACCACCGTCACTCCAACGACCCCT
CAGCCACGGCAAACTTGGGAACAGCAAAATTTACATACAAATTTGTCTGCCAGGAAGTATTTTTACGGCGAAAAATGCGAGCAAATTATGGGATC
AATGTTTTTGCAGGAAACTGTAGGTTATTCCATTTAAAATCCAATCTAAATATTATCCATAACGAATATATTTAACTGGTTATAGTAAATAGTAG
TGGTTAGTAGTAGTTCTAAACTTATGTGCTACTTGATAAACTAAAAAATCGATTATAGTTGTATTGAAGTTATGTTTTCAGTACGGAATTGACAC
TTTAGTCAATCAATCTCATTAATTACAGTTGATTAATCTGGTCCCAAGTCCATCGTAATCCTGGTCACACGCTGCACCCAAGGCGAGTCCAATAA
ATTGGGGATTATCAAGTGAAATTAGCACCTTCACTTGGGCGCATATGTTGCCACATCGGATCTGAATAATCACCACATCACATCATCCCCATCTT
CATTAGGCTCGAATGTTACAAGTCAGTGGGAGCAGGAGGAGATTGGGGTATTGCAACCGCATGAGTTGCACTTTGTCTAAGTCTGTACATTGGTC
CACGCGTGTTTAGGGGCTCCATTCCGGGGTTGGAATCGAAAACCCCAACAGAAGTGGTCAGCCACTTGGCACTCCCATTCCAAACGACTTTTTAA
TGCAATGCGTGATGGAGGATTTTCAGCGTGACTTTCGCCGATTGATTTATGCCCGTTAATCAGTGCAATAAATGCCATGCACAGGGAAATGCTTC
TGATTAACCAATTTGGATAGTGCACTGAAAGTTTAAATGTTCTAATGGCTTAATGGTATCTATTGTATATTTCAAAGTTTGATTCATTTAGAGTG
TGATTGTGTAACTTTAGACAAAGGCATTAAAATAGTTAAGAGATAAAAAACAAAATCTAAAATGTTTAAATTCTCATTTAACTAAGCACTTTGGA
TGTCTACAATTCAGATTTGAAACCCATTCTCCATAGAGGTGAATACAAAAGTATTATAAGATGGCACTATGGATTAATTCATTTTTCCCAGTGCA
GGAGCAGGTGCTCGTTTTATCCCTTGGCTGGAGTGAGGAGTTTGGTTCTACTCCCGCTTTGTTTGCTTTTCTATTAGCGCCGGGCGGGTGATTTG
TTATCCCAAATTGTAGCATTCCTTATCCGGCGAGGGGGATGATGACTGCGACCAGATTTGCATAAATTCGTTCTGTTTGCCCTTAGCACTTGAGT
TATTGGCGTTTGCCACTCGCCCCGCGGAGGGGACGCACTTATTCGGTGCAACTCTCAGCTGCATCACATACATACCAGCAACAACAATAACAGCT
TAATTACAACAACACGATAACGAGTGGCAAATAGCAATTGTCCACATACAATTGCCAATTTCGCTTAACTTGGCCATAAAACACGGAAAGCGACG
GCAGACGGCCCAGAAGAGCAAAGCAAACAACTTGGCCTCCGCGCCACTCCGCAAATAAATCTCAATTTGTGGCACTAACACGGAGTAAACGAGGC
TCAAATCGAACCGAAGAGCGGCTGGCGATGCTAAAAACGCTTAGCAATTGGCAATTTTCGCAAACTAAATGTTTATGGCTGGCCTCAACCTGTTC
GACTTTGGCCTTTTCCGTGCCCCAAAGCTACGGAACTCAAGGAGCAGAAAATTGCGATGCCAGTGGATGGCGTAGCATACCTCTGGGCGTCTTTT
AAGTTTGGCGAGAGCGACGGGAGTTGTGTGTTACTTTAATCTAATACTTTTAAATTAAAAATATTGTATTTGATTAATGTTTCAGTTCACAAACA
ATCTTTGCCAGCATAGATGACAAAAAAGCCAAGAATGTGCAACGCTTTTGTTTAGTTTCATTATAGCATCATCATAAATGCGTATACGTAATAAT
AATAATTTTAAGTTGGCAACTAACTTGCGGATGTGCATAGGCAACAAGGCCTATTTATATATGAGGATTATTCCGATTTGATGGTTAAGTTCATA
TGATTTAACCCAAAAATAAAACGGTCCCGATATTAATTCGCCTGGTGATAAAATAAAGTTGCTGTGACCAACTCAAAACAACACCATTTCTAACT
TCATAACTGAGTTGGGGTTTTCAATTAGGTGATACGACTTTAACACTTGCAAATTTCTTTTTTGATATTGATATTTTCCTTAATTCATGTATTTG
TACATACATATGTTCATTTCAAATAAGAAACCGCTTGTAAGGAACATGATATCACCTCTCCCTATCTCTACATTCTGTTGGAATTCTCTTGGCTA
ACTATCACTGACCATTTGGACATAATACTCCATTTGGTAGTAAGTACTGCTGGTTAAACGCCTCGCTGCCTCCGCATTTCGCTGCTTGGTTCCTA
GCTGCCTTCCTGATAAATTGCCATAAATTAAATTAGGCTCAGACACACACACACACACACACACAGATAAATATAGAGACACACACTCGCATATG
CAACACAACTCAACTACTCATACTTAGTGGCAATAAGTGGCAAAAAAATGAATTATTTTTCATATGTTGGCCCGCCTCAGTGCCATAACTCTGCC
CAACCCAACTTGACTGCCATTTTCTGAAGGGGTCAGTCTGTTTACCTTTTGTTGTTCCTGCTGCCGTCGTGGTTACAGAATTGTTATGGTGCCTG
GTGGGTTTCTTTTCCGCTGCCCTTCACCCACCCAAACAATCAGGTCGGTGGTTGAAGGTTCGTTGGCAAGCGGAGTGGAGGAGTGGAGGAGGCAG
TTCCACTGGAAGCAGGCCCATATTAAACCATTTGACATTGCTTTTAATATGCTCGCTCGGCTTGTTTTTATTAATTTTTATGGTTTGCCCCATGC

FIGURE SHEET 794

CCAATTGTAATCGGTTTCATAAATTATGCTAGATAAGCGACTTGTGCAGTGGCCTTAGAAGGAATCGTCATTGGAAGAAGAAATGGCAAAGAAAG
CTGAAGAAACTAATACTCAGCTATGGAATGCAGAGAAAGCTAGCTGAAGATGTATGTATGCTAAAAGATATTTAAAGATATTGAAAAGTAAAAAT
TTACTTCTTGTTCTTCTTATATAACAGATTTAAACCTATATCTAGTATTGCATTTTATGATGATTATTTATTAAGAACTTTATTGAAAATATTTA
AGTGACATTGAGGCGGCTAAAACTTGATAGGTATCAATATAGGCCCTGTTTCGCGACAAGAATTCCTCAAAAGCAAGGTAAATACTTGATCTTTC
TAAGCGATATTCCTGCTTTTCCACTGTCTTCCGTGGCGAAAATCGGTTCCTCACAACCCAACTCGCATCTGAACGCCGAGGACATATTGTTGTCA
TGTTTAACATATCTTAACGCTACTCAATGCTATGCAGGGCAGAGATACATATGTACGTTCCTATTCGGACTGCAGCTCCGATCGGAATAACCAGT
TTCGCCAAGCGGACTGTTCGAACATCATCAGCGCCCGAGTTCTTCATCATTTGTAGCATCAGCGTCAAGATCATTGCTCATGTTTACAATGATGA
CAGGCAGCAGAATGAGCAGAAGCTGGCCGGGAATCGACTTCCAGCCAAATCAAATGGGTCTGCTCTGTGGGATCGGTATTGGGACTGGAATCGGA
ATCGGGCCAGTAGTTAACTGCGGCCCGCTTCCACTTCCACTCCATCAGGCCCGACTCGCAGTTCGGAATTGAAGCTATCATAAATCTGTTCGTCG
CAAAAATCTACACACAATGGGGCGTTTGCAAACGCATTCGCCGATCGGAATGCGAAGACGAACTCTCTGAATCTGCCTCTTGACTGACTGCCGCA
TTGGAAATGCGATCGTGATCGGGCAGTTCTTTTGGGATATAGGAAAGAACAGAAATTGTATGAGAGGATGGAAAAATTCGACTATTGAACTATTT
AGAAGTGTTCCTATAGAGCTTTTATCTTTGCTTTAAATAGGAACGCGAAATAAAAACACCCATATTCTCTCAATGGAGAAGTTCATTCAAACTAT
GTTCAATTTAGGGTCCAGATACCGAAAATTTGATTATCGTTGTAGTTGTTTCTTTTTTTTTTTTGTAAATTAACATTATGAGATCTATCATTTTG
AACAAGGATACTGGCTTCCTTTATGTACATATTATATATAATAACTCCATTTTAACCTATGCTCCATCTAAATAAAGTAGCTCACATTATACACT
GCACTTAAACGAGCTCTCACAGCTTTCTCCTCACTTTCTCTCTACGTAATGGATCCTTAATTGAGTGCATGATCGGCAATCACGCTGTCATCCCT
AGGCGCATCGCCAACTGGAAGTTCACTTGGAACTTCTGGTCGGATTTGTTGTTTTACAATGCAGCATTGTTTTGCTTGCTGTTGGGGTTTTGGCC
GCCGTTTCGCGATTCCTTTGCCTCGCTAGCGGTGTGCTGATTTATGGCATCTTTCGGCATTTCGGCTACCGGCCCCCAGTCTTTATGATTTGTCA
TAAATATGTCCCCTCTCCGTCCGATCAGAATCGATCGGCTGGGCGATTCCAATCAGCGGCTGTCCGGATGGTTTGGGCTGAGGTTGAGTTTCTGG
GCTCTACTTACTCTCGATGGAAACGGACGTTGTCCACGTAGAGCCTCGTGCAGACCGGAAGCGGCTTCCGAGAGGACAACGAGCGCTTGGGACGG
CAAATGGCTGCTGCCAAATGCGTTGCTTTCCATCTGCAGCTCGTTTGTGTTTTGTTTTGGTTTTGGTTTAGACTAATTTGGCACTAGGGGGCACT
CATAACCTCACTTTCGCTTGTGTTTCAATGTTGGCACATGCAAAGATCACTCGGTATCGGTGATAATCGGTTGGGAATTGTATTTGCGCGTCGGT
AAAACGGTAAAGCTCGGATCAGCTGACAGCTCGCTCGCTCTCCTTCTCTCTAAAACTCTCTCGCTCGCTCGACACAGGACACCCGCACGTACGCG
CTGCAGAAATCCAACTGAAGCCAAATGGAAACCAGTTGCCGTTAGTTGGCCCGTGTTCTTCCTCTTCTCCAGCCTTGCCGCTGCGCAGTCGGCGT
CGGCGTCGCCGCGTAACGCCTCACGACCTCTGATTGGCCAGCGGCCACAACCGGTTTGTCTACACTGTCGCCATCCCGCTCTCGCGCACGCCCAC
TCCCACTGCGGCAGTGTCTTTACATTATGTTCTCACCTCCTTGGGCGCGCAGTTTGTTGTTGCCGCTGCATTATTATCCCAAAATGGTTGCGTTT
GTCCATCCGTTGGCCATTGAACGCCTGTTTGTCTGGCAGCACCTGGTACTCGCACTCGAACTGGTACTGGCACTGGTACTGGCACTCTCCGGGTT
TCCCCGCCCCCACAACCATTTTCCACCTCGATCAGCTCCCCTCCCTTGGACGTAAACTTCTGACATTTTGTGTAAATAAACCGTATGGGAAACAT
TTTTACTTTTGGCTTTGGCATTTTGTTGTTGTTTGTCGGACACTGTCCCGGACAAAAGTATCTTGGAAGTAGTCTCTTTCCTTTTTTCTGCCCCT
GCAGCTGGGTTTTTGCACACCGTCCACTTAATATAGCGCATTACTGTGGTATTTATTGGGCGCGAAGTGGCGAAAATATTTCGGAAGCAGGGTGT
CAAGAAAATTGGAATTTAATAGGCCGCGACTGCTATTCTGGTTAAAAGAACCAAGTCAATTGCACAACGACAAAATATTGTTA
(SEQ ID NO: 1468)

Exon: 13428..13312
Exon: 7374..7129
Exon: 6996..6843
Exon: 3948..3323
Exon: 3259..3101
Exon: 2983..2680
Exon: 2451..2181
Exon: 1744..1504
Exon: 1264..1001
Start ATG: 13428 (Reverse strand: CAT)

Transcript No. : CT25312
ATGGAAAGCAACGCATTTGGCAGCAGCCATTTGCCGTCCCAAGCGCTCGTTGTCCTCTCGGAAGCCGCTTCCGGTCTGCACGAGGCTCTACGTGG
ACAACGTCCGTTTCCATCGAGACTACCCGACGCCAAAGATCTGCACAATATGTCACTAGTCGGCAACTACTTCAATCCGCACCTGCTGCTCAACC
ACGGGATGCTGGTGGCCAACGGAGCGGCGGCGGCAGCGGCGGCGGCGGGAGCGGGACCGGCCAGCTACTTTGCCAGTGACCGCTCGCCGCTGGGC
AAGCCGTCGGTGCTGTCCAACTTCTCGCTGCCGTCGGCCTTCTCGCCGCCCAAGTACATCGGCATATCCCTGGATCAGAATCTGTTCAATGGCAG
CGAATCATTTCGCACGGATTCGGCCAGCCCCACATGCACATCGCACGAATCCATGGAGGGATCACAGGATTACGATGCCGTTGAAAAGGGTGAAA
GTCCGCGCAGCAATAATTCTCAGGATCCCAGGGATTTGAGACATCTGCATAATGCGGGGAAGAGCCACCAGGCACTGGCCACTTCCTCGTCGGCG
TCCAGCTCCTCGTCCTCCTCCTGCTCCACCAGCAATCCCGCCATCAGCACGGCGACCAGCAGCGTTGCCGTTTCGATGGCCAGCCACCTGGCCGC
CTCCTCGCCGCACCATCACCCCCACACGCACGCCCACTCGCACCCGCATCCGTTGGCCCATCCGCACGCCCATAGCCATCACCACGTGGGCCACC
ATGTGGGGGCACCTCCGGTGTCCACGGCGGTGACGACGCACCACCACATGGCCCATCCCCATCCGCTGTCGCACCACCACGCCGCCCACCACGCG
GCCTTGGCCAGCTTGAGCATGGCGGGTCTGCGAGCAGTTCCCGGCGGATTGAGCCTGGTCAGTGGGCTGCAGGCGGCAGCTGCCGGCGGTGCTAT
TCCCGAGATGTGCCCCGTTTGCGGACTGAAGCTGAGCGCCGAGGAGTGGCACACCCACTTCCTCACCGAACTGGACAGGCTCTACAAGCTGAGTG
CGGGATTCGAGAGGGCCAGTCTGCAGGCCACCTACATGTTTGCTCCTCCATGTCCCGCGCAGGAGAACGCCATTCGCACCAGTCACAACCGCTGG
GAGACCTTTCAGAGAATACGTAACAATCGCCAGAACCGACTGAGACTCAAAGTGCGAAAGCGCAAGTACGGCGAAATGTACATGATGGAGAGTCT
TTACTGTAGCAGTTGTCCGATCTGCAAGAGGAAGTACGCCTTGGAGACGGGGAAGATTCCTCCGGAGGACGATGCCAAATCGCAGGAGGAGATCG
AAACGGTGGATGTGGAGAGCTGCAACGACGAAGTGCCCGACTCAGGTTCGGAGCTGGCTACTCCGAGTTCTGGGTCATCCGGCACGGTTATGCCG
CCCTCCAGTATGCACAACAGCAACTCGCAGCCGGGCAAGCTGGACGGGATTCTCTACCGGACGGGCTGTGTGCTCAGCCAGAAGGATCCGCATCC
CGACGAGCATGACGTGAGCACCAATGTGACAACGGCGAGCAGCAGTAGTTGGCCGGGAGAGGCACCAACCCAGGCACATATCAGTGTTAAAACCG
TCAGCGAGCTGTCATCCACCACACACCACTACTACAACGCGGACTCATGCGGCGTGGGCGTAAACGACACCAACAGCAGCAGCAGCACCCACAAC
AACGGCGGTGGCAGCAACAAGGATCTGATGATGGACACGGCCTCCTGCCAAAACGACAGCGACGAGGACGTGATTGTGGACGACGACGACACCGT
GAAGCTGACGAGCAAAATCAACTATGGCAAGATTCAGCGCCGCCAGGACGAGCAGAACGTCGGCAGCAGCAGATCCCTCGAGAACATCTCACCGG
TGGAGGAGCGACCGCGGTCGGAGCCGCAGGTGAGCAGCACCGAACCCGGACCCATGGACATATCTCACAACAACAACAATAACAACAACAACAAC
AACAACAATAGCAACAGTAATAACAACAACAATCCGTCGACGAAATACGCAGAGAGCATGGAGAACAGCCTGTCGCAGTTGTCGTCGATGGGCGT
GCCGGGATTAACGCAATTGGACACAAAGACAGGCTTAAAGGATCTCAACACGGATGCGTTTCTGCGCGGCCGTAACTTTTACTTCCACCAGAGTT
GTGCCAACGTCATGAGCAGCTACCGGCTGAACAAGGAGCTTCTCAGCCAGGCCCAGAATCAACAGAGGGCGGCCGCCAACGGAAACGGAAATGGC
AGTGGGATCGGAATTGGGGATTCGGGCGGCGCCACGGCAACGCCCCGCAGCCTTTCACCTGCCCAATCTCCGCAGCAGAGCGTTTCGCAGGCCAT
GGAGTGA
(SEQ ID NO: 1469)

FIGURE SHEET 795

Start ATG: 1 (Reverse strand: CAT)

MESNAFGSSHLPSQALVVLSEAASGLHEALRGQRPFPSRLPDAKDLHNMSLVGNYFNPHLLLNHGMLVANGAAAAAAAAGAGPASYFASDRSPLG
KPSVLSNFSLPSAFSPPKYIGISLDQNLFNGSESFRTDSASPTCTSHESMEGSQDYDAVEKGESPRSNNSQDPRDLRHLHNAGKSHQALATSSSA
SSSSSSSCSTSNPAISTATSSVAVSMASHLAASSPHHHPHTHAHSHPHPLAHPHAHSHHHVGHHVGAPPVSTAVTTHHHMAHPHPLSHHHAAHHA
ALASLSMAGLRAVPGGLSLVSGLQAAAAGGAIPEMCPVCGLKLSAEEWHTHFLTELDRLYKLSAGFERASLQATYMFAPPCPAQENAIRTSHNRW
ETFQRIRNNRQNRLRLKVRKRKYGEMYMMESLYCSSCPICKRKYALETGKIPPEDDAKSQEEIETVDVESCNDEVPDSGSELATPSSGSSGTVMP
PSSMHNSNSQPGKLDGILYRTGCVLSQKDPHPDEHDVSTNVTTASSSSWPGEAPTQAHISVKTVSELSSTTHHYYNADSCGVGVNDTNSSSSTHN
NGGGSNKDLMMDTASCQNDSDEDVIVDDDDTVKLTSKINYGKIQRRQDEQNVGSSRSLENISPVEERPRSEPQVSSTEPGPMDISHNNNNNNNNN
NNNSNSNNNNNPSTKYAESMENSLSQLSSMGVPGLTQLDTKTGLKDLNTDAFLRGRNFYFHQSCANVMSSYRLNKELLSQAQNQQRAAANGNGNG
SGIGIGDSGGATATPRSLSPAQSPQQSVSQAME*
(SEQ ID NO: 1470)

Name: Om protein

Celera Sequence No. : 142000013384150
GTTATCGGTGGCTTTAAATTCGTAATAAATCTATTGTTGAATAAAATATTCCATTCCCCCCGAAATTTGAAAAATGAGAATCGCATACAGGCACA
TTTCGAGTTAACATTATTTTTATTTTTCATACAATTCGTACAATGCCTACCTATAATTAATATTAAATCGCAAAATATTGGCTTTACCTAGTGAA
AAGTACTTAGCATCCTAATAGCCGATAATATAAATTTCTGTGAAACATTTCGTATACTTTAGGAATAATATGTGTATATTTGCGTGACTTCCTAA
AGGTGAAGGTTCCGGAACCTACAAAAATATATAAAATGATTGTTTGAACTGGTTATCGTAACACTAATTAAGGTAGTTCTTTGTTACACGCTAGA
TTATATATTTCTATACATATCGGTCGAGCTGTATATTAATTATGAACAATTAACGATTCTGAAAACTAAGAACTCGTTGGGGACTGTTCAAGCTT
TGCGAAATAATAGAGATATTTGTACATTTATATAAACCTAATGATTTAAGCGATCCGCATTAATACCAATCAGCATTAACACATCAAAAATATGG
ATCGCTCTATATATAATTATAGATTCTACTTGTGGATTACAAGAAGATTAAGAACGAAAAGATTTCGATTCCCAAGTATATTTACAATTTAAATT
GAGCTGGCGCTTTGAAAAAATTGAAAAAATTAACTATTTTAAAGTAGGGGGATGCAATAAATTTGTCTAGCTGTGACCGATATGCCGATGTGCCC
GAGACCCTATAAACTCATTCGTTCCGGCATGCCCGATTGAATTGACGAACTCTATGGACTAGTTTCGCGTTGGTATATCATAAGAAATTGGCGCG
GCCTACAACATCAATGGCCAATGACATTGCGCAGTGGCAATGTCATACCCATACGTATTTGATAACAGCTCGCATAAATTCTTTTGTGACTATAC
AGCGAGTCTGAGACCTTATCTCAGCTCTACAGCAACCAAAACACTCGGCGCTAGGACTTATTACTATTGCAGCTATTGACATTGTTATTGTTGTA
CAAGTATGGTATAAGATTGGGCTCAATCTCCAGCTGCTGCCTGAGTATCGAGCTCATGACGAACTCCGTTGAAACGATATGACACTTGGGATTTC
CGTGCCGCGTGAGATCCGCACAGAGATGCATGTCCGTGGGACAGGTTACTATGATGTAGGAATCGGGCGCTTGCATGTGTGTTTCCGCCACAGAT
GCACCGCTTCTCCGCTTCGGCTCCACTTTACCACCAGACGATTCAATCATTCGTATAATTTCTTCGCGAGCTGGGAACACGTCCGGCGTCACATG
GAAGTATTTGCCGGCAAACAGCGTTGAACGAGTGGGGGCGCACAGCACGGTATTCAGATTGAACTGCAGGTTCTCGTCCACCGGTATGTGCTGAA
TGCGGTATGGATCTGTAGGCACAAATTTACCAGCTTTGGCACTATCAGCAATCCAGCTCGACTTCAGCACATAATCGACGTGGCAGCAGGCCTGG
ATTAGCTTGCATGTACGACTCTCGCGTGTCATTACCAGGTGAGTGGCATCTGCAGGGCTGTCCACCACAATTCCACCCAAAATTCTAAAAAAAAA
AAAAGGGAAAAGTTAAAAAACGAAACTAAGAATACGTTGTATTATACTTACAACACAGCTTTTTTAAGAGCCTCGGCATCTGCGACCTGGGAAAA
TATGACCTTTGGTGGTTTGGTGGTAGTTGGATATTCTACGCAGACAATTTGCTCTGGCAGCTGCTCCTGCTGGAATGCGTTCATCTTCTGGCGCT
TAAGTTTTTGCTCGTTGCCGTAAGGATCGGATAAGTGTCGCTTGACCCGTTCGTGTGCCTCCTGAGTTAGATTGATGGGCGCCTTCCAAGCAGCT
GTTAAGAAACAAATCGTCAAATGATTTTACAATATAATACGAGTTTAGTTTGTACTTACTTAGCAGATGAGCCACCAGATTGCATTCGATGCGGA
AGGGAGCGACCAAGTTGTACTGCTGATACTTGGGATTCTCATACTGGGAGAGGCCACTAAGGTTACCGATGCACACGTCGCTTAACCAAAGCGCA
TTGACCATCGGTATGTTCCACTCCTTGGCGGCATTAAACTTGTTGCCCTCGAGCTGCTTGCACACGACCACTGTGTTCACCTTGGACAGATAGGA
TGTGTAGATGGCACCGCACTCCTCTGCCATCTGCTGTAGTCTCACAACCTCCTCGCCTTCAAATCCCTCGGAGGTTATGATGTAGCGTTCTAGGG
GCTTACGATAGCCAAACTGGCTGGGGAACGGTAGGTGCAACGGCTGCCACGGTGGCATCAGTTGGCGCTTTAAGCAAATATCACTCAGCCAGTAG
GCAGTGACGCAGCGCTTGGCATCCCGCAACGCCTGCATCACCACGCCATGACGCTGAGTGCGACAAATAACATGGGTTACTCGGGGGCAGTAAAC
ACGTTCGATGTCACCGCCAAACTGTCTAATCGTATCTAGCCAAATGGGCAGTTCATCACCGTCTGTTTCATCGTATTCCACAATGTAGAACGTAC
AGCCCACCAAAAAGAGATCGGCTGGTAACTTTAGGTTCGGATTGTGCCCGTAGAACTGCGGCATAGGGATCGGTTGCTGACCAGGACGAGTTTGA
ATGTAGCCGTGAGGAGTCCGCTGCACTGGCACACCCACGCCCACTCCCACAGCCATCTGTTGCTGCTGCTGGGGGGACTGTGTCGGAGCGACTAC
GATCTGTTGTTGGACTAGATGTTGCTGCGGTGCCTGCTGCTGTTGTGGCAGGGCGACAACTCTGCGCATTTGCTGCTGTTGCAGCAGTTGTTGTT
GCTGCTGTTGCTGCAACATGAGCAACTCCTGCTGAGTTCGCGGTGGTCCAGGAACTCCGGCTGTTGCGTTATGTTGCTGGCCCATCATTCTAAGA
GCACCAGCTGCCGACGGTGGCTCGACGTGTTGCTGTGGTGGTAATTGCTGTTGGACAACCATTTGTTGTTGTTGCTGCTGCTGCTGTTGCTGTTG
TAATAGTAATTGTTGCTGCTGCTGCTGAATGGCTCCGGTCACCACCACCTGTTGTACAATCTGCTGTTGCTGTGGCTGCTGTCCATCGGGAAGTT
GAATTATTTGCTGTTGTGGTGTTTGAGCTCCATTATTTCCTAAGCGATTGCTCAACATGTTGGCCAGGGCTGTCTTCGTTTTGAGGTTCATTTGC
TGCGGTGATTGTTGCGGCTGTCCATCGGGAGCTGTGCAAAAGGAATTGGTTACTATGTGCATTGTCCTTTTTTTAATGATTAAAGATGATTCGTA
TAATTGTAAAAGTCACTGTAGCAGACAAATGCATTTACTTACTCGTTGATGTCATGACCAAAGTTTGCGTCATTATGTTGGCATTTCCGGGAAGA
ACACCTCCTGCTCCTGGAGTTGTAGGTGTGCCTGGTGCGGACTGCTGCTGCGGCTGTTGGACGATGGTCTGTTGTTCAATCAGCTGACCATTGG
TCCGGTGATAAGCTGCACTGTTTGCTTGCCCAGCTGCTGAGGTCCCTGTTGCTGAATGGGAATCTGCTGGACTCGCAACTGCTGCCCGCTGCATCA
GCATTTGCTGGTTGGGATCATTGGGGTTGAAGGGCTGCTGTTGAGGAGACTGCTGCTGTTGCTGTGGTCCCGCTCCTGGCTGCTGTTGAATCGGA
CTCAAGCCAGGTGTTCCGGCGCGTACAACAACCTGTCGTTTTCCCTGCTGCTGTTGCAGCCAGAGGACTTGTTGCTGCTGTGTTAATCCGGGTGG
CATTTGGTGTTGGACAATAATGTGCCCGGGCGGAACCGGACCTGCCGGTCGCGTCGCTACTATGCTGCCCCGGTGCTCCAGGTCGCGGCTGGTAGG
CAACCTGTTGGCGAAGCATTACTCGAGGTTTGTTCTGCTGATTCAACTTAGTAATATATTCGGCTCTTTTGTGAGCATCCAATGACATGAGGTGT
GCATGCGTTTTTTCGTCCACCACGATTTTTTGTTGCTGTGGCTGTTGCATTACCAACTGTTGTTGCTGACCAAGATGCTGTTGCTGCTGCTGCGG
CTGTTGTTGTTGCGGTGGCGGCAGCACGATCTGTTGCTGTTGTTGAGTGGGTTGAGGCTGTTGCTGTTGAGGCTGGCCGGGCCAAGAGGTTTGCG
GCCGCAATCCACGCGGAACAAATTGCTGCTGAGGCTGCGGCTGCGGCGTTGTTGGTCCACCGGGCAGGGGTGATTGCATCCCAACACTGGTGGGT
GTGCCTGGAGTGCTGGACGCCATTTGACCGCCAGCAGGACTTTGCGGTGACCAATGCTGCTGCTGCATTTGTGGATGGTGTTGTGGAGACTGCTG
TTGTTGCTGAAGCAACAACTGTTGTTGTTGCTGCTGCTGCGGAGGCGGCGTGCGTTGAGGCAGTTGTTGCTGCGTGATAAGCTGCATTATTTGTT
GCTGCTGATTATCGTTGGACAGTTTTTGCTGCAGTATCTGCTGTTGTTGGGGCGTTTGCTGCTGTTGTATAAGGATTTGCTGTTGTTGTTGTCCC
ACTAGCTGTTGTTGTTGTTGCTGCTGCTGCTGCTGTTGTTGTTGTTGCTGTTGTTGCTGCTGCTGTTGCTGTTTTTGCATTAACTGCTGTTGTTG
TAGGTACTGCAAGCGCTGTGGATCACTGAGTATTTGCTGGTTAACAACAATCTGCTGCGGCTGCTGCTGCATTTGCATCCTCTGCTGTTGCTGCT
GTTGTGGTATAATCTGCTGCTGCTGCAACATTTGTTGTTGCTGCACAAGTTGCTGTTGTGTCTGATTGACCACGTAAACGTTTTGGCTCTGCGGA
TTTTGGGCTAGGATTTGCTGTTGCTGTTGTACGCTAAGCTGATTAAAGTGCTGCTGGCTAATTATAAAGGTCTTTTGTTGCTGCTGCTGTTGTTG
TGGCTGCTGAACTCCAGAAATTTGCTGGTGTGAATCAAACGAAAATTTATTGGGGTAAATATTTAAAAAAAAAAGACAAAAAACTAAGAGTAGGCA TACCTGCTGTGGTTGTTGTTGCAGCTGCTGTTGCTGGGGAAATTGACCAATAATCTGCTGTTGTTGTTGTTGTGGAACCTGCTGCTGTTGCTGAA
CATTGGTTGGTGGACGTTGTATGGTTTGTTGAATTATCCGCACTTGACCACCAGCTCCAAGTGCTATTTGCTGCTGTTGTGTAAACTGAACTTGT
TGCGGTTGTTGTTGTTGAACTTGGTGCTGTTGCGGAAGCTGTTGCTGCTGCTGTGCCGGTGGCAGTTGCTGCACTTGAGTAATCTGTTGTTGCTG
CTGCGGCTGCTGTTGTGCTTGTTGTTGAACGTGCAACAATTGCTGCTGCTTCTGCAAGGCCAAAGACATATGACTTTGAATGATTTGTTGTCCTT
GAGCCGTGGATGTGTTTATAACATGGCGCTGAGTGATGACTTGTTGCTGTTGTCCAGGCTGTGGCTGTTGCTGCGTCAGGACCTGCTGTTGTTGC
TGCTGCTGTTGTTGTTGCTGCTGCTGCTGCTGTTGTTGTTGTTGTTGCTGCTGTATTTGCTAAAAAGAAGTAATCATTAATTTCCGGTAAAAAAT
AATATATGTTCTTTATTTACTTGAGCGTTTTGTTGGTTTGGCTGCTGTTGCAAGGTGGGGGTAGTAGGTTGCTGTTGCAGTGGCGATTGTCGCG
GAGAAGGGGTGTGCTGCTGTTGTGGTTGCTGCTGCTGCTGCTGTTGCGGTTGCTGTGCCATTTGCTGCTGCTGGGGCTGCGGTGCCATTTGTTGT
TGCTGTTGCATCTGTTGTTGCTGCTTCAATTGTTGCTGCCTCATTATCAACGAGTCCTGATTGCTGCTCAATGCAGATCGACTGAGCACTTGAGC
TACCTGAACGGGGTCCGTTGGGTCGATAGGCTTCTGCTGGGAGAATGATTGCTGCGGCTGAGTGGCTTGTCCAGGAACCACCTGATGCTGATGCA
GCTTTGCCTGCATGGGTGGAGTTTGAGAAATCTGGGGCGATTGCGGAGAAATATGCTGGGGACTCTGCTGTTGCTGTTGTTGCTGCTGTTGGGCC
AATTGTTGTTGCTGCTGCAATTGCATGCGCTGCTGTTGATGGACGGGCTGTTGAAAGGGCTGCATCTGTTGCTGCTGTTGCGGCGACATCATAGA
TTGTGGTTGAGGTTGTTGTGGCGAGCCCATCATGTGCTGTTGTCGATTCTGTTGCATTTGCTGTTGCTGGCGCAAATGTTGTTGCTGGGCGTTTT
GCGGCGAGGGCGGAGGTGGCGGAGTCATTTGGGGAGCTGGGGATTGCAGTTGTCGCGGCGATTGTGGCGGCAACATATTGCTAGTTGCATGATGC
TGCTGTTGCTGCAACGATGGGGATGGCGTACTTGGTGGCATTACCGGCGAACGGTTTTGCACCATCCGAGGCGACTGTTGTTGTTGTAGATTCTG
TTGCTGTTGTTGCTGCTGCATTTGCATCTGTAATTGCTGCTGCTGCTGCATAACTTGTTGCAGCTGTTGTTGAATTTGTCTCTGTTGCTGCTGCT
GTTGCGGCGTCAATGCTTGTCCGCTTTGCACGATTTGCTGCAATTGCATTTGATTCTGGTTCAAAATTTGTTGCTGCCGCATTAGATGTTGGTGT
ATGATTTGCGGCGAAACCGGCACAGATTGTTGTTGTGGCTGCTGTTGCTGAACAACTTGCTGCTGAACAATTTGCTGTTGCTGAACTATCTGCTG
CTGCTGTACCATCGTTTGCTGCTGGCCCACTTGTTGCTGCACCACCTGTTGCTGTTGAACTATCTGCTGGTGGTGCTGAGGGGATTGCACGGGCT
GCGGCGTTGTAGATGGTGTACGTGGTGTCTGCCGGCCTGTTGGAGTCGTTGGCAGTCGGGGCGACTGCTGTTGCTGAGGAATTTGTTGTGGATGT
TGTTGAGAAAGTTGCTGTGGAAGTTGCTGTGCGATTTGTTGCGGGTGTTGTTGCGCAAGCTGCTGTTGAAGTGGTTGAGGATGCGGGCTGTTGC
(SEQ ID NO: 1471)

Exon: 6757..5627
Exon: 5569..5039
Exon: 4964..3368
Exon: 3261..1960
Exon: 1898..1667
Exon: 1604..1001
Start ATG: 6757 (Reverse strand: CAT)

Transcript No. : CT25344
ATGGTACAGCAGCAGCAGATAGTTCAGCAACAGCAAATTGTTCAGCAGCAAGTTGTTCAGCAACAGCAGCCACAACAACAATCTGTGCCGGTTTC
GCCGCAAATCATACACCAACATCTAATGCGGCAGCAACAAATTTTGAACCAGAATCAAATGCAATTGCAGCAAATCGTGCAAAGCGGACAAGCAT
TGACGCCGCAACAGCAGCAGCAACAGAGACAAATTCAACAACAGCTGCAACAAGTTATGCAGCAGCAGCAGCAATTACAGATGCAAATGCAGCAG
CAACAACAGCAACAGAATCTACAACAACAACAGTCGCCTCGGATGGTGCAAAACCGTTCGCCGGTAATGCCACCAAGTACGCCATCCCCATCGTT
GCAGCAACAGCAGCATCATGCAACTAGCAATATGTTGCCGCCACAATCGCCGCGACAACTGCAATCCCCAGCTCCCCAAATGACTCCGCCACCTC
CGCCCTCGCCGCAAAACGCCCAGCAACAACATTTGCGCCAGCAACAGCAAATGCAACAGAATCGACAACAGCACATGATGGGCTCGCCACAACAA
CCTCAACCACAATCTATGATGTCGCCGCAACAGCAGCAACAGATGCAGCCCTTTCAACAGCCCGTCCATCAACAGCAGCGCATGCAATTGCAGCA
GCAACAACAATTGGCCCAACAGCAGCAACAACAGCAACAGCAGAGTCCCCAGCATATTTCTCCGCAATCGCCCCAGATTTCTCAAACTCCACCCA
TGCAGGCAAAGCTGCATCAGCATCAGGTGGTTCCTGGACAAGCCACTCAGCCGCAGCAATCATTCTCCCAGCAGAAGCCTATCGACCCAACGGAC
CCCGTTCAGGTAGCTCAAGTGCTCAGTCGATCTGCATTGAGCAGCAATCAGGACTCGTTGATAATGAGGCAGCAACAATTGAAGCAGCAACAACA
GATGCAACAGCAACAACAAATGGCACCGCAGCCCCAGCAGCAGCAAATGGCACAGCAACCGCAACAGCAGCAGCAGCAGCAACCACAACAGCAGC
ACACCCCTTCTCCGCGACAATCGCCACTGCAACAGCAACCTACTACCCCCACCTTGCAACAGCAGCCAAACCAACAAAACGCTCAACAAATACAG
CAGCAACAACAACAACAACAGCAGCAGCAGCAGCAACAACAACAGCAGCAGCAACAACAGCAGGTCCTGACGCAGCAACAGCCACAGCCTGGACA
ACAGCAACAAGTCATCACTCAGCGCCATGTTATAAACACATCCACGGCTCAAGGACAACAAATCATTCAAAGTCATATGTCTTTGGCCTTGCAGA
AGCAGCAGCAATTGTTGCACGTTCAACAACAAGCACAACAGCAGCCGCAGCAGCAACAACAGATTACTCAAGTGCAGCAACTGCCACCGGCACAG
CAGCAGCAACAGCTTCCGCAACAGCACCAAGTTCAACAACAACAACCGCAACAAGTTCAGTTTACACAACAGCAGCAAATAGCACTTGGAGCTGG
TGGTCAAGTGCGGATAATTCAACAAACCATACAACGTCCACCAACCAATGTTCAGCAACAGCAGCAGGTTCCACAACAACAACAACAGCAGATTA
TTGGTCAATTTCCCCAGCAACAGCAGCTGCAACAACAACCACAGCAGCAAATTTCTGGAGTTCAGCAGCCACAACAACAGCAGCAGCAACAAAAG
ACCTTTATAATTAGCCAGCAGCACTTTAATCAGCTTAGCGTACAACAGCAACAGCAAATCCTAGCCCAAAATCCGCAGAGCCAAAACGTTTACGT
GGTCAATCAGACACAACAGCAACTTGTGCAGCAACAACAAATGTTGCAGCAGCAGCAGATTATACCACAACAGCAGCAACAGCAGAGGATGCAAA
TGCAGCAGCAGCCGCAGCAGATTGTTGTTAACCAGCAAATACTCAGTGATCCACAGCGCTTGCAGTACCTACAACAACAGCAGTTAATGCAAAAA
CAGCAACAGCAGCAGCAACAACAGCAACAACAACAACAGCAGCAGCAGCAGCAACAACAACAACAGCTAGTGGGACAACAACAACAGCAAATCCT
TATACAACAGCAGCAAACGCCCCAACAACAGCAGATACTGCAGCAAAAACTGTCCAACGATAATCAGCAGCAACAAATAATGCAGCTTATCACGC
AGCAACAACTGCCTCAACGCACGCCGCCTCCGCAGCAGCAGCAACAACAACAGTTGTTGCTTCAGCAACAACAGCAGTCTCCACAACACCATCCA
CAAATGCAGCAGCAGCATTGGTCACCGCAAAGTCCTGCTGGCGGTCAAATGGCGTCCAGCACTCCAGGCACACCCACCAGTGTTGGGATGCAATC
ACCCCTGCCCGGTGGACCAACAACGCCGCAGCCGCAGCCTCAGCAGCAATTTGTTCCGCGTGGATTGCGGCCGCAAACCTCTTGGCCCGGCCAGC
CTCAACAGCAACAGCCTCAACCCACTCAACAACAGCAACAGATCGTGCTGCCGCCACCGCAACAACAACAGCCGCAGCAGCAGCAACAGCATCTT
GGTCAGCAACAACAGTTGGTAATGCAACAGCCACAGCAACAAAAAATCGTGGTGGACGAAAAAACGCATGCACACCTCATGTCATTGGATGCTCA
CAAAAGAGCCGAATATATTACTAAGTTGAATCAGCAGAACAAACCTCGAGTAATGCTTCGCCAACAGGTTGCCTACCAGCCGCGACCTGGAGCAC
CGGGCAGCATAGTAGCGACGCGACCGGCAGGTCCGGTTCCGCCCGGGCACATTATTGTCCAACACCAAATGCCACCCGGATTAACACAGCAGCAA
CAAGTCCTCTGGCTGCAACAGCAGCAGGGAAAACGACAGGTTGTTGTACGCGCCGGAACACCTGGCTTGAGTCCGATTCAACAGCAGCCAGGAGC
GGGACCACAGCAACAGCAGCAGTCTCCTCAACAGCAGCCCTTCAACCCCAATGATCCCAACCAGCAAATGCTGATGCAGCGGCAGCAGTTGCGAG
TCCAGCAGATTCCCATTCAGCAACAGGGACCTCAGCAGCTGGGCAAGCAAACAGTGCAGCTTATCACCGGACCCAATGGTCAGCTGATTGAACAA
CAGACCATCGTCCAACAGCCGCAGCAGCAGTCCGCACCAGGCACACCTACAACTCCAGGAGCAGGAGGTGTTCTTCCCGGAAATGCCAACATAAT
GACGCAAACTTTGGTCATGACATCAACGACTCCCGATGGACAGCCGCAACAATCACCGCAGCAAATGAACCTCAAAACGAAGACAGCCCTGGCCA
ACATGTTGAGCAATCGCTTAGGAAATAATGGAGCTCAAACACCACAACAGCAAATAATTCAACTTCCCGATGGACAGCAGCCACAGCAACAGCAG
ATTGTACAACAGGTGGTGGTGACCGGAGCCATTCAGCAGCAGCAGCAACAATTACTATTACAACAGCAACAGCAGCAGCAGCAACAACAACAAAT
GGTTGTCCAACAGCAATTACCACCACAGCAACACGTCGAGCCACCGTCGGCAGCTGGTGCTCTTAGAATGATGGGCCAGCAACATAACGCAACAG
CCGGAGTTCCTGGACCACCGCGAACTCAGCAGGAGTTGCTCATGTTGCAGCAACAGCAGCAACAACAACTGCTGCAACAGCAGCAAATGCGCAGA GTTGTCGCCCTGCCACAACAGCAGCAGGCACCGCAGCAACATCTAGTCCAACAACAGATCGTAGTCGCTCCGACACAGTCCCCCAGCAGCAGCA
ACAGATGGCTGTGGGAGTGGGCGTGGGTGTGCCAGTGCAGCGGACTCCTCACGGCTACATTCAAACTCGTCCTGGTCAGCAACCGATCCCTATGC
CGCAGTTCTACGGGCACAATCCGAACCTAAAGTTACCAGCCGATCTCTTTTGGTGGGCTGTACGTTCTACATTGTGGAATACGATGAAACAGAC
GGTGATGAACTGCCCATTTGGCTAGATACGATTAGACAGTTTGGCGGTGACATCGAACGTGTTTACTGCCCCCGAGTAACCCATGTTATTTGTCG
CACTCAGCGTCATGGCGTGGTGATGCAGGCGTTGCGGGATGCCAAGCGCTGCGTCACTGCCTACTGGCTGAGTGATATTTGCTTAAAGCGCCAAC
TGATGCCACCGTGGCAGCCGTTGCACCTACCGTTCCCCAGCCAGTTTGGCTATCGTAAGCCCCTAGAACGCTACATCATAACCTCCGAGGGATTT
GAAGGCGAGGAGGTTGTGAGACTACAGCAGATGGCAGAGGAGTGCGGTGCCATCTACACATCCTATCTGTCCAAGGTGAACACAGTGGTCGTGTG
CAAGCAGCTCGAGGGCAACAAGTTTAATGCCGCCAAGGAGTGGAACATACCGATGGTCAATGCGCTTTGGTTAAGCGACGTGTGCATCGGTAACC
TTAGTGGCCTCTCCCAGTATGAGAATCCCAAGTATCAGCAGTACAACTTGGTCGCTCCCTTCCGCATCGAATGCAATCTGGTGGCTCATCTGCTA
ACTGCTTGGAAGGCGCCCATCAATCTAACTCAGGAGGCACACGAACGGGTCAAGCGACACTTATCCGATCCTTACGGCAACGAGCAAAAACTTAA
GCGCCAGAAGATGAACGCATTCCAGCAGGAGCAGCTGCCAGAGCAAATTGTCTGCGTAGAATATCCAACTACCACCAAACCACCAAAGGTCATAT
TTTCCCAGGTCGCAGATGCCGAGGCTCTTAAAAAAGCTGTGTTAATTTTGGGTGGAATTGTGGTGGACAGCCCTGCAGATGCCACTCACCTGGTA
ATGACACGCGAGAGTCGTACATGCAAGCTAATCCAGGCCTGCTGCCACGTCGATTATGTGCTGAAGTCGAGCTGGATTGCTGATAGTGCCAAAGC
TGGTAAATTTGTGCCTACAGATCCATACCGCATTCAGCACATACCGGTGGACGAGAACCTGCAGTTCAATCTGAATACCGTGCTGTGCGCCCCCA
CTCGTTCAACGCTGTTTGCCGGCAAATACTTCCATGTGACGCCGGACGTGTTCCCAGCTCGCGAAGAAATTATACGAATGATTGAATCGTCTGGT
GGTAAAGTGGAGCCGAAGCGGAGAAGCGGTGCATCTGTGGCGGAAACACACATGCAAGCGCCCGATTCCTACATCATAGTAACCTGTCCCACGGA
CATGCATCTCTGTGCGGATCTCACGCGGCACGGAAATCCCAAGTGTCATATCGTTTCAACGGAGTTCGTCATGAGCTCGATACTCAGGCAGCAGC
TGGAGATTGAGCCCAATCTTATACCATACTTGTACAACAATAACAATGTCAATAGCTGCAATAGTAATAAGTCCTAG
(SEQ ID NO: 1472)

Start ATG: 1 (Reverse strand: CAT)

MVQQQQIVQQQQIVQQQVVQQQQPQQQSVPVSPQIIHQHLMRQQQILNQNQMQLQQIVQSGQALTPQQQQQQRQIQQQLQQVMQQQQQLQMQMQQ
QQQQQNLQQQQSPRMVQNRSPVMPPSTPSPSLQQQQHHATSNMLPPQSPRQLQSPAPQMTPPPPPSPQNAQQQHLRQQQQMQQNRQQHMMGSPQQ
PQPQSMMSPQQQQQMQPFQQPVHQQQRMQLQQQQQLAQQQQQQQQQSPQHISPQSPQISQTPPMQAKLHQHQVVPGQATQPQQSFSQQKPIDPTD
PVQVAQVLSRSALSSNQDSLIMRQQQLKQQQQMQQQQQMAPQPQQQQMAQQPQQQQQQQPQQQHTPSPRQSPLQQQPTTPTLQQQPNQQNAQQIQ
QQQQQQQQQQQQQQQQQQQQQVLTQQQPQPGQQQQVITQRHVINTSTAQGQQIIQSHMSLALQKQQQLLHVQQQAQQQPQQQQQITQVQQLPPAQ
QQQQLPQQHQVQQQQPQQVQFTQQQQIALGAGGQVRIIQQTIQRPPTNVQQQQQVPQQQQQQIIGQFPQQQQLQQQPQQQISGVQQPQQQQQQQK
TFIISQQHFNQLSVQQQQQILAQNPQSQNVYVVNQTQQQLVQQQQMLQQQQIIPQQQQQQRMQMQQQPQQIVVNQQILSDPQRLQYLQQQQLMQK
QQQQQQQQQQQQQQQQQQQQQQLVGQQQQQILIQQQQTPQQQQILQQKLSNDNQQQQIMQLITQQQLPQRTPPPQQQQQQQLLLQQQQQSPQHHP
QMQQQHWSPQSPAGGQMASSTPGTPTSVGMQSPLPGGPTTPQPQPQQQFVPRGLRPQTSWPGQPQQQQPQPTQQQQQIVLPPPQQQQPQQQQQHL
GQQQQLVMQQPQQQKIVVDEKTHAHLMSLDAHKRAEYITKLNQQNKPRVMLRQQVAYQPRPGAPGSIVATRPAGPVPPGHIIVQHQMPPGLTQQQ
QVLWLQQQQGKRQVVVRAGTPGLSPIQQQPGAGPQQQQQSPQQQPFNPNDPNQQMLMQRQQLRVQQIPIQQQGPQQLGKQTVQLITGPNGQLIEQ
QTIVQQPQQQSAPGTPTTPGAGGVLPGNANIMTQTLVMTSTTPDGQPQQSPQQMNLKTKTALANMLSNRLGNNGAQTPQQQIIQLPDGQQPQQQQ
IVQQVVVTGAIQQQQQQLLLQQQQQQQQQQQMVVQQQLPPQQHVEPPSAAGALRMMGQQHNATAGVPGPPRTQQELLMLQQQQQQQLLQQQQMRR
VVALPQQQQAPQQHLVQQQIVVAPTQSPQQQQQMAVGVGVGVPVQRTPHGYIQTRPGQQPIPMPQFYGHNPNLKLPADLFLVGCTFYIVEYDETD
GDELPIWLDTIRQFGGDIERVYCPRVTHVICRTQRHGVVMQALRDAKRCVTAYWLSDICLKRQLMPPWQPLHLPFPSQFGYRKPLERYIITSEGF
EGEEVVRLQQMAEECGAIYTSYLSKVNTVVVCKQLEGNKFNAAKEWNIPMVNALWLSDVCIGNLSGLSQYENPKYQQYNLVAPFRIECNLVAHLL
TAWKAPINLTQEAHERVKRHLSDPYGNEQKLKRQKMNAFQQEQLPEQIVCVEYPTTTKPPKVIFSQVADAEALKKAVLILGGIVVDSPADATHLV
MTRESRTCKLIQACCHVDYVLKSSWIADSAKAGKFVPTDPYRIQHIPVDENLQFNLNTVLCAPTRSTLFAGKYFHVTPDVFPAREEIIRMIESSG
GKVEPKRRSGASVAETHMQAPDSYIIVTCPTDMHLCADLTRHGNPKCHIVSTEFVMSSILRQQLEIEPNLIPYLYNNNNVNSCNSNKS*
(SEQ ID NO: 1473)

Classification: hypothetical

Celera Sequence No. : 142000013384150
CATTAATTGTAATTATTTGATTGGGTATTTTCGATAAGCTACAAATTCAGGGATTTCGTTGTATACCTTTTAGATTTTCATGCTGCTTGATTACA
TATACTTTTTTTGTTGCTGCCACTTTTGTGCACTTTTTTTTTCACACACAAACTCGAAACAGAAAATGCCATTAATGATACTGTTGTTGTTGTTG
TTGTCTTGAGCACTGGAAATTTTCGTTACGCTTTGGCAGACATTACGAGCCACGCTCCGCATCCGCGACCCCCAATCCACAACATCCGCAATCCG
CTAGCGATATGATGATGGCTATATCTATATTGTTGTTGCCGCGGTTTTTTTTTTTGGACTACTGGGATCCGAACTCGGACTCGTCTATCTTTGG
TTACACGTAGTTTGCGACTGAGCTGAGAGCACCTGGCGAAGCACACGCCGAACTCAAAACTGAAGCTGGTCCCGTCTTTTGGCCAAGAGCCTCAC
TCTCGCTCTCACTCTCTCTCTCTCTCTGCGGATGTTAACAAAGGCAGGCGGCTGCAGCGGAGAGCCAGGTAGCTTTGATTTTTTGACCAAACG
ATCTACCTGGGTAAATAGCACCACCGAGGCCCATGTTAAAAAGATCCAGCGAATATCGTAGCATTGCTATACCTGTACGGATAAGTAAGAATCTC
TTTGACACCATAGAGTTCTGATCGAGACTCGTACTCCCTCCCAATTCCAATTGATATTAGAAACACTACTGTTGATGATCAATCGCCTGACAGTC
ACAGTTACAGTTCCGATTTACAACTATTTAAACCAAGATCAAAAGATCTTAAGATCTTAATAAAAACTAATGTCTCGATCATTCACACTTTAAA
CATCTAACTGTAAACTGTTTGGTGATAGCGACAGTTGTAAAAAAAAGCAATCCAATTTGACCAAGCCCAATGTTTAATTAACCAGTAAGTGATTG
ACTTTAAAATGGAGAGAAAGCCAATTTATTTTATTTACTACTATTTACAGTCAATGTTTGCTCTTCTTCTTCTTCTTCTTGGCCTTGTGCTTGGA
TTCTTCGCTCTTTTTCGATTTTTTCTTGGACTTCAGCTTCGATTTCTTAGACTTTTTCGAGCTGGAGCCCTTGTGCGATTTCTTGGGCTTACTGA
GTTTGGATCTCTTGTCATTGTCATCAGAAGAATCGGATGATGAGGATTCGTTGCTAGAACTAGCATCGCTATCTTCGCTGCCGGATATGCATTTC
TTTTCCACCCACTTTTCAGCTTTGCGCTTTTTAGGCGCGTGCTGCTGCCAAAGCTGTTGAAGTCTGTCGTCAATATTCGCCTCTGCCTGAATCTC
TGGAGCAGCCGGCTTTTGAGGAGGTGCTGTCGGTAACTTTGGTCCATAAATATCCTCTGGCGCCACCTCAGCCATTGCCAACTCCCTATCGTTTC
TCAGTCGCTCCTTTCGTGGTTTGTATGCGATTTTCAGTTTGCTTCCCTCGATGGGACCAAACTTGGTCGGTGCTGGTTCTTTGGCAGCATCCTTT
ATCTTAGGACTAAATAGGGAAGCAAAGATTCCTCTGGGTGGCGAAGTGTTTCTCAGGACATTTTGGGCGGCAGCTGAGGTGGTCGATGTTACGGG
TAAGCCAAAAGACTCTTGCAGGATAGCTAATTTATCCTGCTCGGATAGTTCCGTCTCTTCCTCATCGCTGTCCTCGAAAATGCTTTTGAACAGGT
CCACTTTCTCTGAGATGGGTTTGTTGCGGGATTCATCTACAGCCTGCTCCAGGGGAGTTTCGGCACGAAAGTATGCTTAGACGGCTCTTCTTTT
GTATTAGGTTTATCCTGTATCTCAGCTTCTGGTTGAGGAGCTGGTGGCGGGGATGGTGGTGTTTCTACCTTTTCCGGAATTGATTTTTCGATGTG
CTTGGGAAAAATAGAGGGGGTTTCGAAGTTTGCTTTAGTGTTTACGGATGTCTCTAGATAATCAAATACTGAAATTTTTGCCTTGGCTTTCAGTT
CCTTTTCTGGTTCCAGCATGGCACCACCAAAGGGCTCGGCTATATTGTACCGCTTGCACAGCAGTGCGGTGGGTTTCCACATGGTCTTGGTCCTC
TCCATCACGATCTTTCGCTCCTCCGGCGGCTTCTCTTGCTGCTCTACTTTCTCTGCTTGAACATTGGCTTCCGAAACGAACCTGTCATTCATAAG
GCCAACTAATGGTCGATATATCTTTGCCGCCTGAATAAACTCCTTCTTCTCCATCTCCCTATCCCACAGAGATAGTGTAACTGGTTGCATTCTCG

FIGURE SHEET 798

CCAGGAACTCCGTAATTTCCTTGTCATCCGTAAGCTTTGATGATACGAATTTCTCATATCGCAGCTGCTTAGCTTCATCAGCTATAAAAGGTTTA
AAAGCGCTTGAAGAATTCATAGCAGAAGCTGAAATAATTGAAATGTTATAATATAATAATTTCTAGGCACTGTAAATTTTGCTTACGCAAGTCCT
TCGTCTTGAGGGCTGCTCTCTCTTGTATGGCGGCATTTGCCTCCTTTACTTCCTTGGCTAGTTCAGTTTGCTGCTCCTCGCCATTTTCGGTTATC
ACTCCGCCCTTGGTAAAGCCCTCAGTTCTGGCATTAATGCGTTCCATTAAAGATTTACTATGATCCTTAAAGGGATTTCGTTTTGGCTGCTCTTC
CGCAGTCTTTTCCTCTTGTTGTTGCTCGCCTAAGATCTGCGCACGTTGATCCGGATTGAGATCGTGTCTTCCCAGACCAGACCGTTTGTACTCTG
AGGCTGTCTCCAGTTTCTGGGCTCTTTCTTTGTCCATCGGTGCAAAGCGGCTTCGTCGCTGCAGCCAGTTTCTGGGCTGAAAATCCCTAGGTAAA
TCAATGGCATAAGGCCTCTGCAGCACTGCCGGCGAGTTGTCCTCACTGAAGCCATCGATGACATGACGCTGTTGGACATGCTGCTGCTTTTTTTG
CTTGGGTTTCTTGTCCGCCAGGGAGAAATCGTAGCGGGTCATATCATCGCGGGCATATATATCCTCGTCCTCTTCCTCAAAGGCTCCCACTCCGA
AGGCTTGACCTCGTATGGATAGTTGCTTTTTGTTAGCCTGCGCCTCCATCTCACCAAATAGATTGATGTGTTGCATAGGCTTGGCAGAAGAAGAA
GACGATTTGGACAGAATGGGATCACGGTTGAGACCGGAGTAGCTCATGCCAAAGCGGTTCTCCTTGGGTGTGTAAAAGATCGGCTCGTAGTCGTC
CGGAGCAAATGTAATATCTTCATCGTCTTCGTCCTCATTATTGCTATCTTCTTCTCCTTTGTTCTCTTTATTAGATGGTAGTCCCTCCGCGCCGT
AGTGTTCCATAAGATACTGCTCTTTGGAATTTCTGGCCGTAGCTTGGCGCTTCTCCTTTCGAGTTTGCCGCGGGCCTACACCTTGGCCAGGTTTC
CAGCCCATGCTTTTAAGTATTCGCACGGCCACTTTATCTCGAACCGGTCGTAGAAGTTGCTCCAGCACTGGAAGACCTGGTATGGCCCCGACACC
CAACTCAGGCTGCATTAACTTGCGGCGCCTCTGATCAGAACGTTGCTTCTGCTCGTCCTCATTGGCGAACTCATCACGCGTGCGAATGCCTTGCG
GTGCGATGCCAAACTCGCCCAGATCCTCCTGGTCCATAAAGTCTTCCGGTTTCAGCTGAGCCTTTGACGACGCCCGCTCGCCCCGCGAACTTTTA
AAGGTCTGCGGCGTCCAGCCCTCCAGTGAGCCAACCGTGTTCCAGAAGCCCGCACTGAAGCCGCCGGTGAAGGCTCCATGGAATCTCCGCTTTCC
ATTTTCGTCCTTCACAATTTGATCCTCGATGGCCACTGGCTTTTTAGCCGGCACAACATCTGTAAAAGAGGTTTTAATGGTATTGGGAAAGCTGA
TAAATATTTATTACAGTACTCACCCTTTTGCAAGGCTGGCAGCGGAGTTCCAAATCGGTGTAAATGCTCCTCCTCGTCCATTCTATGCTACAAAT
TCCATATATTAGCGAAACAATTTGTTTGGTCTGGGCGCCAGTGAGTGCACACCACATTACAGATGACAGCTGACTGGAGTGTTCGCCTATCGGTC
ACGTTTTGCTGAAAACTGTGACCGGAACTTTAATACGAAATTATTAAAAAAAATTAAAACAAGAAATAAGCTAATTTATTGAAATACTAAAATAC
TAAAGTTTTAAAATTAAAAATAAAAAACTACAGTAATACTTTAAAAAATGTTACAAATTATGTTAATGTTAATTTTTAAAGCCGGCGGCTTACTT
GTCTGAACTAAATTATTAAAATACCGTTTACTTAATTATTTATCAATCTGGTATTAAAAAAAAACTTGTGAAGAAATAATAAGCAATATTTCAAT
TACTATTGATGTTTAACTGACCATTGCAATCACGGCTTTGAGTAGCGATATTATTTGCAATCCGACAGGTGAGTTCTGCCATCTCTAGTTCAACC
GCACGGTCACATTTAAGACATTGCAAATATTTTAGAGGAACTATTTCGTTGCAATTTTCAGCTGCCTGCAACGGAAATACAGTGCAAATGGTAAG
CGCAACGGCGGTGACAAAGAAAGGCACACCTATCCGATTGGAAAACCAGGTAAATACCGAGAATAAGACCAGAACGGGAGTCGCGACAGACTGGA
GCTACCTGTGCTGCCTGTATGGGTGACTAATGATGTCAACATTTTCTGTTTTCTCTCCTCAAGCCGACGGCCATTTTTGGCTAGCTAAGACGTGA
TTATTGGCCCGAAAGCACAAGAAGTGCAGCGCAGTAAGTAGGCTGGCATTCCGTGTCCAGGGAACCCGATAACCACAGCTCCATTCCCAACGAAC
AGCAATCATAAGTACATCAGTTATACCCACATCCTGGTCTCATACACGCACACAAACACAGCGAGAGCGAGATGTCCGAGAAAAACCTGAAAGTG
GGCGCCCGGGTCGAGCTGACCGGCAAGGATCTGCTTGGCACGGTTGCCTACGTGGGGATGACCAGCTTCGCCGTCGGCAAGTGGG
(SEQ ID NO: 1474)

Exon: 4025..3919
Exon: 3859..2462
Exon: 2403..1001
Start ATG: 3976 (Reverse strand: CAT)

Transcript No. : CT25382
CCCAGACCAAACAAATTGTTTCGCTAATATATGGAATTTGTAGCATAGAATGGACGAGGAGGAGCATTTACACCGATTTGGAACTCCGCTGCCAG
CCTTGCAAAAGGATGTTGTGCCGGCTAAAAAGCCAGTGGCCATCGAGGATCAAATTGTGAAGGACGAAAATGGAAAGCGGAGATTCCATGGAGCC
TTCACCGGCGGCTTCAGTGCGGGCTTCTGGAACACGGTTGGCTCACTGGAGGGCTGGACGCCGCAGACCTTTAAAAGTTCGCGGGGCGAGCGGGC
GTCGTCAAAGGCTCAGCTGAAACCGGAAGACTTTATGGACCAGGAGGATCTGGGCGAGTTTGGCATCGCACCGCAAGGCATTCGCACGCGTGATG
AGTTCGCCAATGAGGACGAGCAGAAGCAACGTTCTGATCAGAGGCGCCGCAAGTTAATGCAGCCTGAGTTGGGTGTCGGGGCCATACCAGGTCTT
CCAGTGCTGGAGCAACTTCTACGACCGGTTCGAGATAAAGTGGCCGTGCGAATACTTAAAAGCATGGGCTGGAAACCTGGCCAAGGTGTAGGCCC
GCGGCAAACTCGAAAGGAGAAGCGCCAAGCTACGGCCAGAAATTCCAAAGAGCAGTATCTTATGGAACACTACGGCGCGGAGGGACTACCATCTA
ATAAAGAGAACAAAGGAGAAGAAGATAGCAATAATGAGGACGAAGACGATGAAGATATTACATTTGCTCCGGACGACTACGAGCCGATCTTTTAC
ACACCCAAGGAGAACCGCTTTGGCATGAGCTACTCCGGTCTCAACCGTGATCCCATTCTGTCCAAATCGTCTTCTTCTTCTGCCAAGCCTATGCA
ACACATCAATCTATTTGGTGAGATGGAGGCGCAGGCTAACAAAAAGCAACTATCCATACGAGGTCAAGCCTTCGGAGTGGGAGCCTTTGAGGAAG
AGGACGAGGATATATATGCCCGCGATGATATGACCCGCTACGATTTCTCCCTGGCGGACAAGAAACCCAAGCAAAAAAAGCAGCAGCATGTCCAA
CAGCGTCATGTCATCGATGGCTTCAGTGAGGACAACTCGCCGGCAGTGCTGCAGAGGCCTTATGCCATTGATTTACCTAGGGATTTTCAGCCCAG
AAACTGGCTGCAGCGACGAAGCCGCTTTGCACCGATGGACAAAGAAAGAGCCCAGAAACTGGAGACAGCCTCAGAGTACAAACGGTCTGGTCTGG
GAAGACACGATCTCAATCCGGATCAACGTGCGCAGATCTTAGGCGAGCAACAACAAGAGGAAAAGACTGCGGAAGAGCAGCCAAAACGAAATCCC
TTTAAGGATCATAGTAAATCTTTAATGGAACGCATTAATGCCAGAACTGAGGGCTTTACCAAGGGCGGAGTGATAACCGAAAATGGCGAGGAGCA
GCAAACTGAACTAGCCAAGGAAGTAAAGGAGGCAAATGCCGCCATACAAGAGAGAGCAGCCCTCAAGACGAAGGACTTGCCTTCTGCTATGAATT
CTTCAAGCGCTTTTAAACCTTTTATAGCTGATGAAGCTAAGCAGCTGCGATATGAGAAATTCGTATCATCAAAGCTTACGGATGACAAGGAAATT
ACGGAGTTCCTGGCGAGAATGCAACCAGTTACACTATCTCTGTGGGATAGGGAGATGGAGAAGAAGGAGTTTATTCAGGCGGCAAAGATATATCG
ACCATTAGTTGGCCTTATGAATGACAGGTTCGTTTCGGAAGCCAATGTTCAAGCAGAGAAAGTAGAGCAGCAAGAGAAGCCGCCGGAGGAGCGAA
AGATCGTGATGGAGAGGACCAAGACCATGTGGAAACCCACCGCACTGCTGTGCAAGCGGTACAATATAGCCGAGCCCTTTGGTGGTGCCATGCTG
GAACCAGAAAAGGAACTGAAAGCCAAGGCAAAAATTTCAGTATTTGATTATCTAGAGACATCCGTAAACACTAAAGCAAACTTCGAAACCCCCTC
TATTTTTCCCAAGCACATCGAAAAATCAATTCCGGAAAAGGTAGAAACACCACCATCCCCGCCACCAGCTCCTCAACCAGAAGCTGAGATACAGG
ATAAACCTAATACAAAAGAAGAGCCGTCTAAGCATACTTTCGTGCCGAAAACTCCCCTGGAGCAGGCTGTAGATGAATCCCGCAACAAACCCATC
TCAGAGAAAGTGGACCTGTTCAAAAGCATTTTCGAGGACAGCGATGAGGAAGAGACGGAACTATCCGAGCAGGATAAATTAGCTATCCTGCAAGA
GTCTTTTGGCTTACCCGTAACATCGACCACCTCAGCTGCCGCCCAAAATGTCCTGAGAAACACTTCGCCACCCAGAGGAATCTTTGCTTCCCTAT
TTAGTCCTAAGATAAAGGATGCTGCCAAAGAACCAGCACCGACCAAGTTTGGTCCCATCGAGGGAAGCAAACTGAAAATCGCATACAAACCACGA
AAGGAGCGACTGAGAAACGATAGGGAGTTGGCAATGGCTGAGGTGGCGCCAGAGGATATTTATGGACCAAAGTTACCGACAGCACCTCCTCAAAA
GCCGGCTGCTCCAGAGATTCAGGCAGAGGCGAATATTGACGACAGACTTCAACAGCTTTGGCAGCAGCACGCGCCTAAAAAGCGCAAAGCTGAAA
AGTGGGTGGAAAAGAAATGCATATCCGGCAGCGAAGATAGCGATGCTAGTTCTAGCAACGAATCCTCATCATCCGATTCTTCTGATGACAATGAC
AAGAGATCCAAACTCAGTAAGCCCAAGAAATCGCACAAGGGCTCCAGCTCGAAAAAGTCTAAGAAATCGAAGCTGAAGTCCAAGAAAAAAATCGAA
AAAGAGCGAAGAATCCAAGCACAAGGCCAAGAAGAAGAAGAAGAAGAGCAAACATTGA
(SEQ ID NO: 1475)

Start ATG: 50 (Reverse strand: CAT)

FIGURE SHEET 799

MDEEEHLHRFGTPLPALQKDVVPAKKPVAIEDQIVKDENGKRRFHGAFTGGFSAGFWNTVGSLEGWTPQTFKSSRGERASSKAQLKPEDFMDQED
LGEFGIAPQGIRTRDEFANEDEQKQRSDQRRRKLMQPELGVGAIPGLPVLEQLLRPVRDKVAVRILKSMGWKPGQGVGPRQTRKEKRQATARNSK
EQYLMEHYGAEGLPSNKENKGEEDSNNEDEDDEDITFAPDDYEPIFYTPKENRFGMSYSGLNRDPILSKSSSSSAKPMQHINLFGEMEAQANKKQ
LSIRGQAFGVGAFEEEDEDIYARDDMTRYDFSLADKKPKQKKQQHVQQRHVIDGFSEDNSPAVLQRPYAIDLPRDFQPRNWLQRRSRFAPMDKER
AQKLETASEYKRSGLGRHDLNPDQRAQILGEQQQEEKTAEEQPKRNPFKDHSKSLMERINARTEGFTKGGVITENGEEQQTELAKEVKEANAAIQ
ERAALKTKDLPSAMNSSSAFKPFIADEAKQLRYEKFVSSKLTDDKEITEFLARMQPVTLSLWDREMEKKEFIQAAKIYRPLVGLMNDRFVSEANV
QAEKVEQQEKPPEERKIVMERTKTMWKPTALLCKRYNIAEPFGGAMLEPEKELKAKAKISVFDYLETSVNTKANFETPSIFPKHIEKSIPEKVET
PPSPPPAPQPEAEIQDKPNTKEEPSKHTFVPKTPLEQAVDESRNKPISEKVDLFKSIFEDSDEEETELSEQDKLAILQESFGLPVTSTTSAAAQN
VLRNTSPPRGIFASLFSPKIKDAAKEPAPTKFGPIEGSKLKIAYKPRKERLRNDRELAMAEVAPEDIYGPKLPTAPPQKPAAPEIQAEANIDDRL
QQLWQQHAPKKRKAEKWVEKKCISGSEDSDASSSNESSSSDSSDDNDKRSKLSKPKKSHKGSSSKKSKKSKLKSKKKSKKSEESKHKAKKKKKKS
KH*
(SEQ ID NO: 1476)

Celera Sequence No. : 142000013384150
ACATTTGTGTCCAATGGATCCTCGCAACCAACTATCTCGAAGGGTATTAATGGGTTCATAGTACCTCTTCTGCAATGGGATCTACTCAGATTTGA
GTTTGATTTATCGAGCTGGAGGAGCTGGGAAAAGAACTGAAAACTCTGCTCACACTTGTGACGGAAGTGAAAGGCATTTTGAGCGGCCACCAGGC
AGGTAGGACAGATCTTTTGTGGCATTTCATCCCGTTTCACGCGACAGATCTCCGGCAGAATTGAGTTCAACATTTCCCAAATGGGGGGATCAGAG
ATCTCCTTGGAGAAAAGGTCCACCAGTATGGATGAGTGTTCGGCGCAGGCTCGGCAGTTCTTTCCCATGCTGGCGTCCACTGATCTTTCCATTTT
TCCCGATGATCTCCCAACCATAGAGGCCGGAATTTCAAAAGAATCAACAAATGTTGGGCACTTGCTCTCCTGCCAAGTAGTCAATGTGAACGTAT
TCGCACAGAGTTGTCAGCTGCATCCGATGATTACTCGATAGTCGATAAGGTTTCATATGCCATCTCCATTAACGTCGTGAGGTTAACTGTGACTG
GGAACAAATCTGCGGCATTCAAAACAATGGTGTCGATAGGTAGGATTCCAATCATATTTAAATCAAAATGTATGTAAATCTATATTAAAGGCATT
AACAATGAAAATAAGAATATTAGAGATAATTTTAATTTTAATAAATAATTTACAAATCAAGTAAAGTTACAAATCAGTCTGTATTATAAAAACGT
TTAATTAACATATAATCTTTAACAAGCGTGCATGCAATGATTTAGGTATTAAAGGTTATCATTTTAATATTTATCTTCATATTTAAGTTGAAATT
TGCTAACTTTGCCAACAGCTGCAATAATTACTTTCACTTTCGCTTTCACAGTCACAAGATTGACTCATCGGCTTAAAAATACCAGTGACTCGCCA
CGGAATCGCGGATATCGCTCATCTCTATCAGCTTTGAGCAAAATTAGTATCTTGTATTGGCCAAACAGACAAGCGAGCGAAGGCCTTTTTGTTGT
CGTTTCTGGCAATGATTTAGGTCTTCATCAAGTGTTATTAAGCTAGGCATAAAGTTTTACCCATCGCTGGACATGGATATCCTGGACATCGATGA
GGCACTAAAGGATGATTCATATATGTGAGTGAAACCACTCCTGTTGTTTTTGTTCCTGTTGTTGTTGCTGCTGCAGCTGCTGCTACTGCTGCTGG
CACTTCACAGGCAGAGGCATCGATGCTATAAATACTCATATGCCTGGTACTCCTTGGCAGATTTCTGGCGGATAAGACCCACGACGATGTCTCCA
ACATATTGCAGCAGTGGAAGACGAACAATCAGCCGCCGTTGCAGCAATTGCACTTGCAGTACAACAACGAGGGTAAGCCTTTTCCACACATACCG
ATGCACCCGATCACAAACATACACACATGTGCAGCACATCATGCAGTTGCGCTTTCTAAATCAAATTTGGGTTAAACTGGCGGCTACGTTGACAA
AGTTCAAGTCGCATGTGGGCAGCATTACTTGGCCAGTAGTTACCGTTGTCTTTCAAAGTGGCCGATTGCCATAATTGGCAACAGCGCCAATGTTA
TTGTTACGGTAATTAATCAAGTCTCAATACGCACACACACACACGCGTTCCCATTGCAAACAGCTGTGCGTGGTACGGCAATAATATTGAAGGAA
AAAAACTGGCTATGCTAATATGGCAAGAATCTCGCATTATACGCAAACATTATTATATAAATCCAATTTACTTCCTGCCCAGCCAGCGAAAGTCA
ATCAAGCAATACGCAAATAAACTATTTGCGTACAATTAAATAAACAATTACCACCGAACTAAAGACGAGGATCAAAAATCGATTAGGCGATTTAA
TTTGAGTGAAATATTGTCATGCTGAGCTATTTTTAATGATTTCCAAAGTGGAATGCCAGAATTCCAAATATTGCTAAAAATATAAGTTAAATAA
AACTATTTACAACAAAGTTCATACTTAATAGTCATTCCTGTAAATGTATGCAATGGTTAAACTCAGCATAGATAAATATTTTAAATAGCTTAAAT
AATATATACAAAATATTCTTTTAAGCGATAACAATAGTAGAAGTGGAAGTAAGAAAATTACGTTAACAAACAACAATTACTTATAATTATATATG
AAAGCTTCAGGGCGTTTATCCAGTAAGTTAAAAAATAGCTAAATGCTAACTTAACGGTAAAATATCAAATAGTGTGCTGAACACATCGCTTTTGC
GAAGCGTCCTTTGGATCTTTACTAACACTAAAAAAATTGTAAACTCCCGGAGATTGCTAGTAGTGTGCACGGAATTTAATTACTGGGTTTATTTC
CTCAAAAGATTTTGTAATTTTACTAGTTTCCTGAAAACTTTGCGATGCAAATATTTGCCACTTTCAAATCCCACGAGCCGGACAGCCGCTTGATC
CAAAACTTCAAAAAGCACGTGAATTCGCAGTCGCCACTTGACGATTTGCGAAAAAATCTAAATGAAAAAAGTAAAATTCGAGAATATGTACAAGA
GCTGATTGGAAATGAGCAACAAATGGGATCCGTGCTGGACACGATCTCTTCCACCGAAGAGGACCACCGCGTGGCCACTGTGACCGGATGGTCCA
CGGTGAACATCGCCAACTGCGCCGGCGTTTCCAATTCTTCAATTTTTGTGGCACTGAAGTGGGTGATGATGCCCATTAAGGTGGAGATATTCAAC
TTCAAGCGAAGTGGACCGGAAGATAATATGGCACGTGGACAATTTCTGTTGGACAACCTGTTAAGCGCAAATCGCCTAAAACGCTTGCAAGAGGA
AGTAGCAGTTATTAACACGTGCCAGAAAATCGAGGTGCGTGTCACACCCGGTCTGCCCAAATCGATGATGTGTGCCCAGATAACAGACGAATTTA
CAACTGCCATTCAGGAGGCCCTTAGATCACGCTATGAGGTGGATTCACGCACCTTAGATCTCTCCAGGTTCCACGCCAGTCCGGAGTTGTCTCTG
CACTTTTGTCCGCTGCATATGGTCAAGCTGCTAGAAACAGTGCTAGTTCTTTCAAACCATTTATTTCCCCATGTGACCAGCCTAGTACTGAGCAA
CAATTATTTGTGTTCCCTGAAAGCGTTTGCGGGAAATTCCCAAAGTTTTGCCAGCCTAGAGCGGTTGGACATAAGCGCAAACAGGATTCAAGATT
TGGGAGAACTCAATTACATCAACAAACTGAGTTGCAAGACGATCTTCTTGGCAGGAAACGGTTTGGCCAAGCTAAGCGTGGACGTCATTCGAAAA
ATGCTACCACAGTTGAAAAATGTTCATGGCTGTGTGCAGTTGGGGGAAAGTACAGAAGCTGTTGATAATATTCCGAAGTCTCAACAACTTCAAGG
CGGTGGGACTAATGGTTTAAAGTTTTGCCAGGACTTCATAAGTTCATACTACACTTTCTTTGACGATACCGAAGAGCGTTTCAAACTTAAGAAGT
ATTACGACGACCAAGCCATGTTCTCGCTTAGCGTGCCGGTACAACTAAATTATGTCTACGGCTACAAGCTGTACAACAGAAACCAGAAGCGCCAG
CATTCCTCGTTTGCACAAAACGCCAAGCTGCAAGTGGGTAGAGCTGCGCTACTTCTCGCTTTAAGCCGCTTGCCTTTGATGCATACAGACTTAGA
GAATGTCGGGCTAGACATCCAGGTGTTCACTTCGAGTCTACGCATCTTTACGTTGACGGATACTTTAAGGAGATATCATCGGATACTCTGGAAC
CACGACGCTTTCAGCGCACATTCGTATTGCAGACTTCCAATAGCCCCGGCTGGTTGATAACCAACGACATGCTGTGCATAACTTCGACTATGCCG
GACCCGAAAAAAACCATTAAATTTAAACCAGAAACTAATATGATAAATACCGACCCGTCGGTAGAAAAAATAAATAAACCTGCAGTGACAGTTTT
AGACAGAAAGTCTAAAGAGGATGTCCAAATTTCTAGACCCCTATCAGGAAAAGAGCTGAATCCTCTTAATAAGGCAGTGCAGAAAATGAGCCTTT
CCCAGGTGGACCATCTTCCCAGTGAGAACTTCAACGATATGCCACCATTAGTAGCCATTGGTCCATTGACTACCGGGCAAAATTGTTTGGACTAT
GAAATGGAGGATATTTTAGTGGCCGATGAGAATAACTTTGACTTGGACATTGATGATGACATCCTGTTTGGATGCGATGACCTTTAAATATGAAC
AAAAAAAATTAAACAATTCAAACAAATAGCTTTTAGAAACCTTGCACCTATCGGTTAAGACACCATACATTACTATTCATTACTTTAACGAGTGC
AGAACTCAAGGATCTAATTTATTTTTAAACTTTTATATTTTACGAAAGCCTTCAAAAACAATTCGAAAACCTTTACTCGCCCAAAGCGTCGGAAT
CTGGATTTCGTAAGTACAAATAAGCAATTGCAACTAATTTGTATATTAAAGTATCTTATTTTTTCAGAGCCAAAATGGAGCGGGAAATGACAGCG
GTGTTGGAACCGGGTCGGTCGCGGGTGCCCCAGCAATGCTTCAGCTGGAAATTGGCGGTCTTGTCACGACGAATATGCACAAATCCTTCCTGCAA
GACACCTCACCGCCGTCTTCCATCTGCTCCTCCATGAACACTGAACGGATGAACAACTCGCTAATCACCTCAGCAGACTTTACGAACTTGAACTT
CCTTCAATCCACAATTGGTCTTGAGCAGGATCCAAACCTTACCACTACGCTTACCAACCAGACAACTGATAACATGGGAATCGGCGGCAGCATAG
GCGGATATACGCTCAGTGACATGATCCGGGATCGCAAGGCGCTGGAGTCGCTGACCATGTGTGAGGACGATGGGACTCTTATCAAAGACTCGCAC
ATCGGGCAAATTGACGAAATATCGTTGACACTGAGCAAAACTGCTTCCGGCTGCAGCACAATGGACAACAGCACAGACAGTATGTCCATTCCCCT
GGCCGCAGATCGAACGATGCCCGTTGTGGTATCGGCAGTTTGTCCTGCCCTACAGCGTACCATGATTTAGGGGAGGAGATGATCGGCGACACAA CTTTTAACCTCGTGGATAGCCTTACAACTTCTGCGCTGCAATCAGAGTCTGAGTCTCTGCCAGTCGATGGAAATGCGACATTCAAAAGACCCACT
GCGAGTGCTACTACAGCGGACGAAACCCAGGTGCTAACAGGTAGGCAGATGAATACTACCTTCACCGACGGTTGCAACACTCCTGAGGGCCGCTG
TGAAACGCCTGAAAATATTGACAGGAAGCTGGCCTTGCTCACCATGGAATCCTCCACACCACTTACAACAAACATGCGCTCACACTGCTACCACA
ATAACAACAATAATAACAAGGCAGGATATACCCCTACCCTAAAGGGAAGGGGAGATATGAACCTGTCCCCAATTGTTGGCGCAACACCGCAAAAA
CCAACTGGAACCGCACCAGGGCGATTAAACAACACCTTTGAGCCCGTGGCAAAAACAGCTCCGTTCAACGGCGAGAAGTTCGTGCTGGACACTAT
GGAGCTCTTGGAGCAGATCGAACAGCCGCTGGATGGCACTTACAACCTGCAAATGTCTGAACAGCACAGGCAGATGCAATGCGTCATGGACTTGG
CTGAGGCGGAAGTGGAGATGCTGGCCCAGCAGGGCGACGAAGAGCAATTCGAGAATATGCTTGCCGAGCTGGGCAAGGTGAATACCCTAAACGAG
GAGCAACTGAAGATGCAAAAGTCGCTAGATACCATCAAACGGCGCTTCCATAGAGATGAGGCGGAGGCAGAGGAGCGTGAAGAGGAATTGCAGCA
GTCGGCAGCCGAAAAGGTGGACACCCCAGTTCTAAATCAGAGCCACTCCAGCAGCAACAGCAGCGGCGGTGGTGGCGAACGGCTGCTCAGTCGCC
GAAGTCGTCTCTACGACGATGTCAACCTTAGTGCAATGCACGGCAGTAATGGAAGTTCGACCAGCACCAACTCTGCCTCATTCATCGTCCAGCGT
AGAGATATGCCACAAGTGGAGCAGCCTGCACCAGATCCTGATCCCGAACCAGCGGAAGAGCCTCCAAAGTCCCAGGTGACAGCAGAGATTGATCC
GGCAAGCTATAAGCTGCCGGAGCGAAGAGAGCGGGATCGCGATCGCTTCAAGACCATTAAGATTTCGAAAGAAATGCGACTGCAGCCGGAAATTA
TTGTGCCTTGTATAGACGATGAACCACAGCAACTCGAGGACGAGCAAAAGCAATTAGTAGAAGATGTTCGGTACGAGGAGGATCAGCGACAGGGT
TCACCACCGGGTCGACTTTCTCGTCGAGATCAGACCACAGCAATTAGCAACAACGCAGATGCTAGTGCGAGTAACTATCTGACCTACAAAAAACC
CAAGGAAAAGAGCCTTATCCAACGACGTCCGCAGCAGCAGGAAGCGCCTTTATTAGCCGAGCCAGCGCCTGCGTCGACTCTTCCCCAGCCGCGTT
CCTTGTCCAGGCCTCGCTACATCAGTGGTCTTCAGAAGTTTACTACGGTGAGCAAGGCAACTTCAGCCGGAGCGGGACTAAACGCCACTCCAGCC
GCTGCTATGCCGACTACTGTTACAGTGCCGGCCAACGGTAACGGGGAGCTGAAGAGCCCTATGGGTATTAAATCCAAATCTTTCCACAACTTGTC
CTCCACAATGAGCGGCGTTGGCTCTGGAGCCCTGCCAAGACCTAGTTTGGGCGGTGGACTGCGGCGTCCCAGTGCGCAGCCGAGCAAGCTTATGA
GCGGATTGCGTGGACCAACTCAAGCCCAAGAGGTTCGTTTCGAAACTATTTTTCTTATCGACCTGTTTAATTCTCATATTTTTGACTTTTCAGGA
TGACTCCGCTGTATTTAAAGTACCGAAATTGGTGAGTGGGCTGCGTGCTCCTGGCCTTGCCCCGAAACGAGCAGGAGCTAATGGTTTAGCTCGAC
CTTCGTCCGGATATTACAGTCTGAGTGTTAAGACGGCACCAGAGGCAGACACTCCTGAGGTTAGTTAATGCAAGATTTGTTAAGGGAACGCTCAA
GATCTAGCTTTTGTGCTTAGTTAAAACTAAAATTGGAAACTGCCAATCTTGGCGCAAAATATTTCAGAGCCTCTCCTCAGCCTCTTCGCGTGGCA
GCCTCTATGGCCACAAGGACTCCGGTAGAACCGTTAACGGCGGAAATGTTCCTCAACAGAATCCACAGCAAACCTTCGACATGCAGGCGCTTACC
TCTAAGCTGACCCAGGTGACTACGGGAGCGACCGGCATACCAAAGCCCTCGGGGTTGAGACCACCATCGCAAATAAAGCGTAGCGGTCTGCCGCG
ACCTTCCAGCATTGTTAGGCGCTGAGAGCTGATCACTTCCTCCGCCGCCGATTGTATGCATATGTCACACACCCGCCTGAACCGACTTTCCATGT
TATCAGTAAAATAGTCTAAATCTATTCTTTTTGTACTTTGTGTTCAGTTCTATTTTTGTGTTTGTCATCCCAGCATAGATGCTCATCTTGCCTAG
TGGTTTCAAGGCACTAGCAACTATGATTTTGAATTAATATTACGACAAATTGTGCATTTAGTTGAACGATACATAAATAGAGAACTTGGCGACTT
GTAAAACAATTACGCACTCCCAGAACCGCTTACATTTATATATAGAACAAATACATCAACACGAACTTTGCCTTACGAACCATAATAATAAAACA
AACGATTTAGGGGATGAGAAAGAGAAGATTGAAGCGAGAAATAATAACGATAATGAATTGATAATAACTGTATATTTTTGTAAAGCGATGCAAAA
ATTCTACGAACGTTATTTTTTGTTGGAGCGGCAAAGCAAGCAAGCAAGCAAATCGAATAAATATTACTAAATAACGAATATACAATAAGATCCTGCTCA
GTGGCCACTAAACCACAAAAAAAAAGGAACGTATAAAACCAAACTGAAATTGATAGTAACTGATAAGAGTATTGAGAAACGTGTTAAAAATCGAA
CTTACAATATTATCTATTATTATCGCATATATATACAAATACAAAAAAGAAAAAAAACGACAGCAATATACATTGACTCATCAGATACTTAGACC
AGAAGGTTAATGACCTGTTTATATTTTGCTATTGCTAGTTCTGAAACGAAAATGATCATACTTGTAATTTCATGAGGTGCACAGTATATTACAAT
TCCCTTTGTACCCCAATGAAAATTATAAACTTCGGCTCTGCTGATGTGCTATATACATACATATTATATAGATTTTTGTAAACCATCTGAAAAAT
TAAGTTTTCAGTTATTTTCGGTTGCCAAATTGAAAAGTGAAACTAAACTTTTGTTAGTTACCATCGAAAAATGTCTTAATAAATCTATGCCGTAT
TGGTCAAAAATAAAATTCCTAAAGATCTTCAATCTATTGAAGCCTTTGTCCATCACACATGCATATCCTAAGTTAAGTTTAGTGCGCATTGTTTA
ACCCTAATGTAGAATTAGTTTAATCTGTAAGGGACAAGTATTGTTTCACCCTCATCAACTAACCAATAACCACATAACTAACCCAAACCAAGCCT
CTATTTTGTATTCTAGCGCTAACCCATTAAGCTTTAATCCTATTCGGTGATGATTTGCATGGATCGAATTTAGTTAGCTACTAAGACTAGTATGG
ATTATTATTTTTGCTAACGCTTTCATATGAGCCTTATA
(SEQ ID NO: 1477)

Exon: 1001..1164
Exon: 1296..1402
Exon: 4419..4474
Exon: 4533..6872
Exon: 6934..7089
Exon: 7193..7778
Start ATG: 1118

Transcript No. : CT25798
CTTGTATTGGCCAAACAGACAAGCGAGCGAAGGCCTTTTTGTTGTCGTTTCTGGCAATGATTTAGGTCTTCATCAAGTGTTATTAAGCTAGGCAT
AAAGTTTTACCCATCGCTGGACATGGATATCCTGGACATCGATGAGGCACTAAAGGATGATTCATATATATTTCTGGCGGATAAGACCCACGACG
ATGTCTCCAACATATTGCAGCAGTGGAAGACGAACAATCAGCCGCCGTTGCAGCAATTGCACTTGCAGTACAACAACGAGGCCTTCAAAAACAAT
TCGAAAACCTTTACTCGCCCAAAGCGTCGGAATCTGGATTTCAGCCAAAATGGAGCGGGAAATGACAGCGGTGTTGGAACCGGGTCGGTCGCGGG
TGCCCCAGCAATGCTTCAGCTGGAAATTGGCGGTCTTGTCACGACGAATATGCACAAATCCTTCCTGCAAGACACCTCACCGCCGTCTTCCATCT
GCTCCTCCATGAACACTGAACGGATGAACAACTCGCTAATCACCTCAGCAGACTTTACGAACTTGAACTTCCTTCAATCCACAATTGGTCTTGAG
CAGGATCCAAACCTTACCACTACGCTTACCAACCAGACAACTGATAACATGGGAATCGGCGGCAGCATAGGCGGATATACGCTCAGTGACATGAT
CCGGGATCGCAAGGCGCTGGAGTCGCTGACCATGTGTGAGGACGATGGGACTCTTATCAAAGACTCGCACATCGGGCAAATTGACGAAATATCGT
TGACACTGAGCAAAACTGCTTCCGGCTGCAGCACAATGGACAACAGCACAGACAGTATGTCCATTCCCCTGGCCGCAGATCGAACGATGCCCGTT
GTGGTATCGGCAGTTTGTCCTGCCCTACAGCGTACCATGATTTTAGGGGAGGAGATGATCGGCGACACAACTTTTAACCTCGTGGATAGCCTTAC
AACTTCTGCGCTGCAATCAGAGTCTGAGTCTCTGCCAGTCGATGGAAATGCGACATTCAAAAGACCCACTGCGAGTGCTACTACAGCGGACGAAA
CCCAGGTGCTAACAGGTAGGCAGATGAATACTACCTTCACCGACGGTTGCAACACTCCTGAGGGCCGCTGTGAAACGCCTGAAAATATTGACAGG
AAGCTGGCCTTGCTCACCATGGAATCCTCCACACCACTTACAACAAACATGCGCTCACACTGCTACCACAATAACAACAATAATAACAAGGCAGG
ATATACCCCTACCCTAAAGGGAAGGGGAGATATGAACCTGTCCCCAATTGTTGGCGCAACACCGCAAAAACCAACTGGAACCGCACCAGGGCGAT
TAAACAACACCTTTGAGCCCGTGGCAAAAACAGCTCCGTTCAACGGCGAGAAGTTCGTGCTGGACACTATGGAGCTCTTGGAGCAGATCGAACAG
CCGCTGGATGGCACTTACAACCTGCAAATGTCTGAACAGCACAGGCAGATGCAATGCGTCATGGACTTGGCTGAGGCGGAAGTGGAGATGCTGGC
CCAGCAGGGCGACGAAGAGCAATTCGAGAATATGCTTGCCGAGCTGGGCAAGGTGAATACCCTAAACGAGGAGCAACTGAAGATGCAAAAGTCGC
TAGATACCATCAAACGGCGCTTCCATAGAGATGAGGCGGAGGCAGAGGAGCGTGAAGAGGAATTGCAGCAGTCGGCAGCCGAAAAGGTGGACACC
CCAGTTCTAAATCAGAGCCACTCCAGCAGCAACAGCAGCGGCGGTGGTGGCGAACGGCTGCTCAGTCGCCGAAGTCGTCTCTACGACGATGTCAA
CCTTAGTGCAATGCACGGCAGTAATGGAAGTTCGACCAGCACCAACTCTGCCTCATTCATCGTCCAGCGTAGAGATATGCCACAAGTGGAGCAGC
CTGCACCAGATCCTGATCCCGAACCAGCGGAAGAGCCTCCAAAGTCCCAGGTGACAGCAGAGATTGATCCGGCAAGCTATAAGCTGCCGGAGCGA AGAGAGCGGGATCGCGATCGCTTCAAGACCATTAAGATTTCGAAAGAAATGCGACTGCAGCCGGAAATTATTGTGCCTTGTATAGACGATGAACC
ACAGCAACTCGAGGACGAGCAAAAGCAATTAGTAGAAGATGTTCGGTACGAGGAGGATCAGCGACAGGGTTCACCACCGGGTCGACTTTCTCGTC
GAGATCAGACCACAGCAATTAGCAACAACGCAGATGCTAGTGCGAGTAACTATCTGACCTACAAAAAACCCAAGGAAAAGAGCCTTATCCAACGA
CGTCCGCAGCAGCAGGAAGCGCCTTTATTAGCCGAGCCAGCGCCTGCGTCGACTCTTCCCCAGCCGCGTTCCTTGTCCAGGCCTCGCTACATCAG
TGGTCTTCAGAAGTTTACTACGGTGAGCAAGGCAACTTCAGCCGGAGCGGGACTAAACGCCACTCCAGCCGCTGCTATGCCGACTACTGTTACAG
TGCCGGCCAACGGTAACGGGGAGCTGAAGAGCCCTATGGGTATTAAATCCAAATCTTTCCACAACTTGTCCTCCACAATGAGCGGCGTTGGCTCT
GGAGCCCTGCCAAGACCTAGTTTGGGCGGTGGACTGCGGCGTCCCAGTGCGCAGCCGAGCAAGCTTATGAGCGGATTGCGTGGACCAACTCAAGC
CCAAGAGGATGACTCCGCTGTATTTAAAGTACCGAAATTGGTGAGTGGGCTGCGTGCTCCTGGCCTTGCCCCGAAACGAGCAGGAGCTAATGGTT
TAGCTCGACCTTCGTCCGGATATTACAGTCTGAGTGTTAAGACGGCACCAGAGGCAGACACTCCTGAGAGCCTCTCCTCAGCCTCTTCGCGTGGC
AGCCTCTATGGCCACAAGGACTCCGGTAGAACCGTTAACGGCGGAAATGTTCCTCAACAGAATCCACAGCAAACCTTCGACATGCAGGCGCTTAC
CTCTAAGCTGACCCAGGTGACTACGGGAGCGACCGGCATACCAAAGCCCTCGGGGTTGAGACCACCATCGCAAATAAAGCGTAGCGGTCTGCCGC
GACCTTCCAGCATTGTTAGGCGCTGAGAGCTGATCACTTCCTCCGCCGCCGATTGTATGCATATGTCACACACCCGCCTGAACCGACTTTCCATG
TTATCAGTAAAATAGTCTAAATCTATTCTTTTTGTACTTTGTGTTCAGTTCTATTTTTGTGTTTGTCATCCCAGCATAGATGCTCATCTTGCCTA
GTGGTTTCAAGGCACTAGCAACTATGATTTTGAATTAATATTACGACAAATTGTGCATTTAGTTGAACGATACATAAATAGAGAACTTGGCGACT
TGTAAAACAATTACGCACTCCCAGAACCGCTTACATTTATATATAGAACAAATACATCAACACGAACTTTGCCTTACGAACCAT
(SEQ ID NO: 1478)

Start ATG: 118

MDILDIDEALKDDSYIFLADKTHDDVSNILQQWKTNNQPPLQQLHLQYNNEAFKNNSKTFTRPKRRNLDFSQNGAGNDSGVGTGSVAGAPAMLQL
EIGGLVTTNMHKSFLQDTSPPSSICSSMNTERMNNSLITSADFTNLNFLQSTIGLEQDPNLTTTLTNQTTDNMGIGGSIGGYTLSDMIRDRKALE
SLTMCEDDGTLIKDSHIGQIDEISLTLSKTASGCSTMDNSTDSMSIPLAADRTMPVVVSAVCPALQRTMILGEEMIGDTTFNLVDSLTTSALQSE
SESLPVDGNATFKRPTASATTADETQVLTGRQMNTTFTDGCNTPEGRCETPENIDRKLALLTMESSTPLTTNMRSHCYHNNNNNNKAGYTPTLKG
RGDMNLSPIVGATPQKPTGTAPGRLNNTFEPVAKTAPFNGEKFVLDTMELLEQIEQPLDGTYNLQMSEQHRQMQCVMDLAEAEVEMLAQQGDEEQ
FENMLAELGKVNTLNEEQLKMQKSLDTIKRRFHRDEAEAEEREEELQQSAAEKVDTPVLNQSHSSSNSSGGGGERLLSRRSRLYDDVNLSAMHGS
NGSSTSTNSASFIVQRRDMPQVEQPAPDPDPEPAEEPPKSQVTAEIDPASYKLPERRERDRDRFKTIKISKEMRLQPEIIVPCIDDEPQQLEDEQ
KQLVEDVRYEEDQRQGSPPGRLSRRDQTTAISNNADASASNYLTYKKPKEKSLIQRRPQQQEAPLLAEPAPASTLPQPRSLSRPRYISGLQKFTT
VSKATSAGAGLNATPAAAMPTTVTVPANGNGELKSPMGIKSKSFHNLSSTMSGVGSGALPRPSLGGGLRRPSAQPSKLMSGLRGPTQAQEDDSAV
FKVPKLVSGLRAPGLAPKRAGANGLARPSSGYYSLSVKTAPEADTPESLSSASSRGSLYGHKDSGRTVNGGNVPQQNPQQTFDMQALTSKLTQVT
TGATGIPKPSGLRPPSQIKRSGLPRPSSIVRR*
(SEQ ID NO: 1479)

Celera Sequence No. : 142000013384010
TTTTATAAGTTCAGCAATGAAAATAGACTAAAAGTGTCTCATTCACGAGACCCTAATGGAAGGCCTAATTGATTTACATATGTCAGGGGAGCACC
CTCACATAAAAGAAATGCGTGGGCAGACACATAAAACCAAAACCCACTCACAAATGAGTCGAGTGGTGAATAATGTCCCATATTCAATTGAGTGC
GGAAGAGGCCCTTATAAATCTGTGTGTGAAATATCTTTTATAATAAAAAACAATTTAACTAATAATACCAATTCTAGTTCGTAAGGCTATAAATA
TTGAACTGAACAGACCAGAGGCTATAACCTATCGACTTCGATAAGATAAATATTTAAAAAGCTGAGACGGAAAAAGTGTTTGCCAAACTCCTTGA
AATTCACTTGAGCGCCACGAGGCTCAGTGGGAAATTTGATTTTGGGAGATGGGATGCTTCCCGTGCATGTGATCATGTCTCGAGGGGCTGACACC
CGTTTTGACTTTTGTCACCGCCAGTGGCGCCAAAACTAATCAAAGCAACTAGGACCGACGCTAAATCGAAACCACAACTACAATCACTGCGGAAT
ACCAAAATGCAATCAAAATATGCAAGCCACGTCGATCAGGAGAGAGAGAGAGAGAGTGAGAGAGAGACCGGGGCTATTCTAGAAACCTAACGCGAGT
TCAGAACGCTGAATTATGTATACCCTTTAAAGTACTAACAGAGCAGAAAACTTAACTGTTTTATGTGGTCGTTCATTAGTAGTAAAAATGGGATG
ATTTTATTTTATTCTGCTTTACTGTTATTTCTGTTTTCTGTTTTTATATACTGGCCTCTTGAATATATAACATTCTGATAACATTACAAACGCTC
CACTAACATGTCTATATGTCTTGGAAGGGAATTCAAACAACCAATCTCTCTCTTTTTCTTTTTCTCTCTCTCTCTTTTTCTGTCGCCCCGATCAA
GTCTTAACGGCAAGTTGCAGCAACAAACATTTTCATTCGTTTTCGCATCGTCGAAGCGTACGGTTCATAGGAGGAACGGAACGAAGCGGGGAACG
CGACGGAAACTAGTTGCTGTTTTTTTGTCCGTGTTAAATAATTGACACAAGAAAATTTAGCTACACTTAAGCAAAGTCCGCGAAAAATCTATTAA
AAATCGTTCGTCGTTTTGTGTGTGTGACCACGAAAAAAGTGCCCCGATCGGAGGATTTTAATAAATTCAATTAAGGTTCCGTCCCAACGATCGTT
TTTCATTGTCTGACGCTCACGCGTGATGTACAAATGAAAAAGTAAAAATTTAAATAAGATCAAAGAAAGAAAGATCCCAGTAAAATTTAAAGTGG
ATTGACTGCACAAGAAAAAGAAAAGTTCCTTACCTCCTAGCCAGAAGTCAAAAGTGAAGCGGAAAACAGAGTGGAGATAACAATTAACGGTTAGT
TGTAAAGCTAAAACTACACAATAAACATATCATGAAAAACTTTATAAAACATAAGAAGGGGGGCATTTTATTATTTTGGGTATCAGCATTTACAT
CACCTTGTTTCGAATCAAACTGATTTTAACATGCATTTGGACCAAACTAACAACGTTTCGAATGTTATCTCTTATGGAAATGGTATTGCTATATT
ATACCATCATTAATTCCGATTCCACCTGAGATTAGCAATTAATATGAAATTTCATAAACATATATTATATATTCGGATCATGCATTCTATTTACA
CATTACTTTCCAATTAAACGTTCATTTATTGCCGCGCTTCGATTAGCAACAAAAACAAATCGTTAATTTTCTATATTTTTCCACAGGGGCTTCCA
TACCAAAGTTCCTTGTTTGTAGAGATCATTGTAATCAGCGCAGATCGAAGCCATATATAAAATGATTTCGCACAGTCCGCCCATATTCAGTCACA
GTCCACCCGTTAGTTTTCTGGCGGACTTCATGAGCGGACATCCCCGTCAATCGTTGAAGTAAGTTTACAAAAGTATATAACTCATAAATAAATAT
AGCCAGCAATTGGACTAATTTAACACAGAATTGCTCTAAGTGAATCCACGAGTTTCGGCAGCCAATCAAAACAAATTAAATAGCCAAACATCATT
GAAAGAGTACCAATTCTCAGGTTTTTTCATGTCGAAAGAAAATATTTTTTTAACTTTCTTATCGATTGATAAGGAACTAGAAGCATTTTCTGATG
CATCATCTTTTATGAATTTAACAAGTGGTGTACGTGTTAATAAGAGAAACGATATAAATGTCTGATAACCTGAAAAACCATGTGATAGTAAATGA
ATTAAACTGAGAGATAAAAAATACATAACAGATAAAAATGATTAATACCCTTTTGCATTAGGCGTTCTCTCTGGCGAATATTTAAACAATAATTT
TAAACATTCAAATTTAAAACAAATTTCAAAATACCCAAACATAACCCACATTAACAAAATAAACAGACCGGAATGCCGTAATTCCATTTAATGAA
TATAAGAACTCAGTTGTTTACACAATCCAGAAAAGGAATATTATCGATCTCTCGAGGGCTGCCCATATTGATTCACATGAAACACCTGTTTCAAG
TGTCGTCTATGGAAATTTTAACACCTGATCAAAGGCAGGAAACATGTCTTACCCAATACATAGTATTAAAACCTGAGAACTATTCGAAAACACAA
TGAATGCAGGTACTAAAAATATTCGTGCTAAGGCTCGTTTTTGGTTGACAACAACAGATTGGCAAAATATGAAAAGCAAGCATTCAAGATCAAGG
CAAGACAGAATACTGAACCAAAACAAACATTTCGCCGATTCTGAGGTGATCTTTCGCTGGTGGAGCCAACTGAGATTTGAAGATTCGTTCACGAG
TCGTGGGGGTGACGCCAAAAATTTGCTTGGCGACAATTTGCGCGTGGCGCTTGACGCAACTTTTTTCTCAGGGGCACACGAGCAAGCCGAAAAT
TTGACAAATTGGTAAAGGGAAGAAGGGTAATATCTATATATTATATTTATACAGAGGCGAGAGCAATTGATTGAATTAAAGCAATTTGCCGTGCT
TCATTTGCTGCACGCGCTGCATTTTCATCATATTTGTTGAGAGTATTTTATTTTTGGGAATGATAAATATACAATACCGAAAATTCGTATAACTT
ATATTCGTATATATGAGGACTTCAGCTAAAAATAAATCTATATCTAGAGTATGGCCAAGCAAAACAAACGCTACAAGAACCGGTAAAAAACTAAA
TAATCAGTTAAGATTAAAGAGGTTCAGTAGATAAAACTGTGGGAGGTAATACATGCGAAAGCCCTACTGCGATCCCTACAACTATGAACATTTCT
TATCGGGGCACGTGAGCGGCATGCCTTCAAACAAACCGAGTACTCCAACCAACTCAAGTAACTCAGCTGCTAATGCGTCAACTCACTTGAAATTT CACAGCGTGATTTTACAACAGTTTACCCCACCCAATACCTAGAACTACCCACGTAACTGGGCGGGTCGTCATCGAAAATGATTGAATTCTTTTGG
TTGCCAACTCAAGCACTAAATATGCTGATATTGTCTCCAGACAGCGCCAATTAGCCAAAAAAAGTTGATGATAACAGCAGAGCAGACGGAAATGT
TCCCATAGCCAGGCCCACGCCGAAAAAGACGTATCAGCATGCCGTCAACATATGTTTAGCATGCAAAAGTCCACGCGAACCCCATTGAACGATCC
TTATCAACCATTGACTTTTAGTTTTATGAATGTCTAGCCGAAAAATTATGATAACTACAAATGGGATGTGAACTGTGCCAAATGAGTAAGACCAG
CGAGTCTCTCCGACTATACAATTTTAGAAATGACTCACTGAAGAACCCAAACAAATATGCTTCATATTCATACTATACATTTCCCACCCACGGCA
AACCCGAATTAAGTGAGGAGGTCGCGCGCAACTCCTCTTATCAGCGATGTTTCTTTATAGACAATATACACGTATCAGTAGGACTACACAAGTAC
AAGTACAAATACAAGTAGTACATGGGCCTCCGAACAATGAAGGCAGGCATTGAGGCAGTAAAAATTAAAGCCACCACTCTTATCAGGACTGATAA
AAGGCAGCTTAATGCGTAGATGCTTGAAATAAAAGACTGATCTTGGGAATTTCTTTTCTGCTTTCCAAACGAAAAAAGAATCACAAAAAATGGTC
AAAACAATTGAAAGATGGCTACCATCTGCTGATGTTTAAATATAGAAATTATATTTTCAATTAGTGGTGTTAGAGATATATATTTTAACTGATTG
TGATATATTCAACCTTCGATATTCAACCTTTTGATTTTTTGAACGAATTCAACACTCATTTAAAAGGACAGAATAGTAACGAAATTAAGTTATGA
AATAAATATTAAATAAATTTATTTTAAGAAACATTTTTATAGTTATTAATTTAAGTTTTGAAATACAAAAATAAACCAATTAAACTTGCATACCT
TGTTTCAGCTACAATGACGAGCCCAACAGAGCGTCGCGCTACTGCCGGCCCCAAGTGATAACGCTGGCCTCCAAAGCCATGGTCAACAACGCCTC
GGCGGCGGTCCAGGGTCAGGGTCCCAGTCAGCAGAAGGCGGGTGCCACGCCCCTGGGCGTGGGCAGTCGTTCCGGACGGAGTTACCTGGAGCGAA
TGGCCTCGGCGCCGCTACTCACCAATCAGCCCAAATCCTGTCTCAGCCGCAAATCCTGCCTGCACAAATCCCAGAACACTACAGCCAGTTCCGCA
GATCTCTCGCCGACGGACACCGATGTCGCGGACAGTGCCAGTCATAGCTGTATCTGCAGCAAGGATAGTGACAGCAACGGCGAAGTGAGGTGAGT
GTGCGGGCGATAAGATTACGTAATGTAGGTAACTCGATACAGCGGCGCCGAAACGATCAAGAAGGCTGTAAATGCCGGCGGACTCAGTCACTTTG
ACGTCAGGCCTTCAAAGATTATGGCGCCGCACTTATTAAACCACCAACTGAACTAGATGGGAACTTAGTGGTGTGAGAGCCTGGGTAATTGTGGT
CAGAATTGGGTGTATCAACCTATAACAGATTCATTAAATAGTAAGATGTCAATTGAGGGGAAATCTTAAGGAAAGTCCGAGAAAGTAACACAAGA
AGCTGTAGATGGTTTTCATAGCGCATCTTAACTATGTAGACTGTGGTCAAAAAGAAATCGAAAGCTTATGATTCAAACTTAAATCTTTGAATTTT
AATATGGGGAGGATAGGATTTTGGTTCTAAAAATTGGAACGTGAAAAGATCATTTCTTATAAAACTGCGAAAATACCACTTCCGCCATAATATTT
TATAAACAAAGATTAATCGTTTATAAGACATTTGCAATAGTTCTAGTAAAAGGAATAAGAAAATCTGTTGGCAGTCGAACAACTTTCCCACAGAC
GTCATAGCCGAGCACATGTCATTTATTAAATAAGCTGAGAAAGCCAATTGCAGACGGCCGCCAGGCTAAACAAATGCAAAAAGATCATGAAATAT
ACTTGAAAATATATTTTATATATTTTTAAGAGCATGCAATTTCACAAAAACAAAATATAAATTATCTAAATGACTGTAGAAATAAGCCAAAATAA
AAACACGCCACTGCATCGCGAGTCGAGAATCTGTATCTCGTATATCTGAGATAAAAAATCTCACATTTTAAGACTCAAATGGGAATAGACTGGTA
TTTAGTATAGACCCCAACAGCGAGGCGCCATTATTTTCGTTTTCCATTTCCATTTATTCGCTATATATAGGGAAGATACATTATCGATTCATGTG
CAGGCCATGAAAATATTTGGGTTATCGATGTCTCGCAGATATTTTGTAAAATTGTATACATATGTATATTTCGCTTTCAACGAGCCCTAGAAATA
ATTTCCTTTTTGCACTTGAATCTGACATTTTGAGAAATGCCTAAAAATACATATGCCACGAGATAGAGAAAATAATTTATACGTTCATTTGCGTC
AAATGCGAACACTATTTCTATTTGGGCTGCGTCTCTAGACAAGAGATCAGGCTTAAAGCTACGCAGCTACTCAAACGAATGCAATTAACCATAAT
ATTATCAATGTAAACCAGACGTGTGCTTGTTGCTGTTGGAGATTTTGTGTACACTTTGCGGTTGCGTATTTTGTATGCCTCGTTTTATCAGTTAC
GAAATCCACTGGGAAAAAATTAATTTACCAATTCAAATCTTCAGAGTAAATTATAATTCATTTAAGTTAACACAAGAACGTAAAGCAATGCAATA
GAAAAATTATTAAGAATTATATTTATTGGAGGCTTGATTTAAGAATTGAAGACCTTATTCATCACCTTCCAAAGCATATCGCATCTGCTCGTCAC
CCATTTGGCCCCACATTTTACAATGAGTTTTGACAGCCAATGAAAGATCTTTCTTTTGTCTTAATTAGCCTCCCCAAAAAATCATCAAGATCAACC
ACAAAACGAGGCAGACGGTTCACGTCAAGGCCGAAGAATTATTAGCATAGAAGCGTGATCAAGCGAAAGGCGTCATCTCATAAAAGACACAATTT
TTTCGGGTGTAATGTAACTAAAAATATTTCAACATTACAAGCCTCGGAATACGAATGCACACAAACGTAAGGTTATATATAGAGATGGGGAGATA
TGTCTGATGTTCATGCAAAGATCACGTGAATCGATCGGAAAAGTGAGCTGGGGCACATGGGTCTGCTGTAAAAATGTTGGCGCACCTTTAGCTG
AAAAATGTGAAAGAATTTCGTACATTTACAACAATTTTATTTCATTCGTAATTAAATTTATATTTATTGGTAGCGATCGAGATAATTAAGAAAAA
CCAAATCCACGACAGAATTTTCCGAGTTAAAACTATTTTCAGTCTCTTACTATTGGACTTTGCTTAAAATTTCAGAAAAATATAAACGATAGGTA
TATTTGGCGAAACTGAAATTCTTATGGGGGAAATAAAATAGAAAATACAGAAAATTTGGCGACATACAATACGGAACTACCTTGATTCGTTTACA
AAAAAGTAGTTCGATTGTAAGGTCAACCAGAATGACCATCAAATCAGTCAGTTGTAAAAATTTCAACAGGTCTTGCCAGAATATTTTTATCGGAC
AGGTTATTGACTTTAGAAAATGAGGGAACTCGAACAAGGTCTGCAAATTGAAAACTGAGGAAATTAAAAAGTATTTTTAAACACAATTTTCATTT
ACATTACAAGCGTTTCGATTTTAAAAAGCCCTTTTGGTGCAGCCAAAACTTGTTTCTCCTGCACCCATCAACGATCTTAATGCGGCTTGCATATT
GAGGAGTTTACAAATTTATGGACTTTAAACCGGACCCACGAAAATAAATGCGTTCCGTAACGCATACGGAATTGTGACTGCCTTTGGGTTTTAAG
AAAAAACAGTTGATAGTCGTATCTCGTTTCCCTTGGAGAAAATGTAAGCCAAGTCGGGGAAAATCAATGAAAATGTAAATGATTTTTTTTTTTA
ATTTGATTTTTCGGGTGATCTCTTTCAAGTTGACAAGTTTTAGGAAAGCGGTCGGTAAAAAAATGAGACCCGTCCGCGGTCTCCGGTTTCTGGTTG
GCGGCCTGCTGGGCGTTGAGACCCACCCCACACACACCAGATAAGCGATCGCTAAGAAACCTGTTGAAGAAAATGCAGCAACAGCAGGCGCACAC
CGATCATGCCCTCGATGCGTGATGTCGTCGATGTCGGTAGTCGGTAGTCGTTACGATCCGATTCTGGCCGAGTCGGGTGGTACGATCTGCCATCT
CAGATACACCATCACCATCACCGATCTCTGGCAATACGGCTGGGGTACAATCAACAGAGAGCCAGTCTGTCGATAGCCATTTCAATTGTTGGCTA
TTTGTACTTCCCATATATATTTAGCACTCGATGCGTTCCCGCCGACTCTCCTCCAATTTGCAGACCAAATAGAGTCTGCTCTGTGTGGGGCCATT
AGTCGTAGGTCTGCTCCAACTGACGGAAACTTTTCGCTTTGGGTTTGGCAACAGCAAAGAACCATACAAAAATCGAGCCCCTACCGAAGCTGATT
AGCCAAAATTAGTCGCTATATCTTATCGAATTTATGGCCAACTTTCTAAATAGAACTTGTATGCGTATTTTTTTCAGTAATATGAAAGTCAAAAG
GGCGGAACATTTGTTCGAAGAGTTTGGAAAGTAATTAACTGCAGCAAACATTTGTATTGAACACAATATATTATTATATTGTATTATTCGTATCT
GCATTTAAATTAGGTAAAATTTTAAAAGTCCAATGAATTTCAGATTCCAACTAAATTTCGTTGAATAACTTATATATTTTGAATCACGAGTTATC
CTCTATATTTTATATATCTTAGTGGGTGTGTTTTTATTTACATTTAAGCAAAAGAACCGTGGAAGAGTCGCCCAATAACATGGGTGCAAAAAGA
AAGGAAAAGCAAAAGTAGGCGTGATTTACATATAGATTAAGGCAAATCTTTGGCAAAGCCGTACGTGACTTCTAAAAATAAAACCAACAAAAAAA
TATACAATACACATTACTCTTTTTATGACGCAGGGAATTTTTCGGGAAACGCAAAGGAATAAAAATGATCAGCAGAATAGAAAAAAAAAAACACT
AAAGGAAAAGTTTCACTCGACCGGGATTTTATATTACCAATTGTCAGACAATCGACAACTTTGGCACATATAGTAGGAGCTTTCAAAAATGGTTT
TAAAAACTGCATTTGGCAAAGACGCAGTTTGCTTAACTAAAGTAAAAACAAACCAATAAAATGAAACTGTTAAGGATAGAAATCCGGCAAAGAA
AGATGCTGAGTCAATGACCACAAAGAAATAAAATAAATTATTCTGAATGGGGGGTCAAGTCAAACTGATAAAGCCAGGGTCAAATCTATATTTGA
TAATGTATATTTTAATAATTAATAATTTGCTTATAATAGATTGCGATGTACTCAATGGATGGTATTTCTTTTTTTACTTTTTGCAGCCGTGGCCC
CAAAAAGCATGTGATCTTCGCTGATGATGAGGGTCTATCGCTAACCGAGGTTCGTGTGATGTCCGAACCCTCGAATGTGCCGCCATATTGGAGCA
TGAAGTTTCTGGAGCAAATTACACAGGGCCTGGTCAGCCCACATCCTCCGGATCAGTGGACAGTGGACTTCAAGCAGCCAGCCTCAGACTATCTA
TCATTTAGGTTGGTACCCTATTTACACAACTGTAAAATATATACGAGTATTCTAAATATTTGTATTTACACAGACAAAAGATAGAACGCGACTTT
GTTTCCTTGGAGAATGTGATCGTCAAGGATGAGGAATCGATTGTCGTGGGCACCATCAAGGTGAAGAATATCGACTTCCAGAAGGAGATCATTGT
CCGTGTGACCTGGGATGATTGGAAGAGCCAGCAGGATATCTTCTGTACATACGCCAGGGCCTATGGACCGGCTACTTGTGCTCATGTAGTCTTCG
ATACATTCTCCTTCAAAATCACCTTGCCGCCATCCTCCAAGCGCCTGGAATTCTGCATCTGCTATCGCACCAACGAAACAGAATATTGGGATAAT
AATGATGTGAGTTTGGCATCAAAATAACTTAAAAAATATTTTACATAATTTGTATTTGCTTACAGGGTAAAAACTACACCATTAGCAAGCGATCG
CCCTTTTATTACAACGCCTTGTCGCCCTATGATAAGGGTCAGAATCGCAACTCGAGCCAGCAAATAAGGTCCACCCTGACCGATGCCTTGGCCAA
GGTGCAAGACCAAAATGGCTGGCACCAGGAGCCACATACGCCATATTGGTGAAATCGCCTGGGAACGGGATTGGATTTTCCTGACCCAAGCGATT
GAATAAAGTTTCTCATTTAGGCCACATGAACAGAAAGAAACAGAATTGGAAAAGATTTAAAGTGTTATAATCAGTTTCATTGACAGAGGGAGAGT
CCAAAAGATTTTACCACTAACGAAACTTTTTGACCTAAGCTAATACCCGGTACAAATATCCCAATTTTAATGTGCCATTGACTTGAGGTTTACTC
AATATAAAATGAGATAGGAGGGCTTATAACTACTTCTACTGAGCGAAGCCCGAATTTGTATGTCTTGTCTTTAGTCAACTTGATGGAATTTCAAA

FIGURE SHEET 803

ATCTATGTATAACTTTTTAAAATGTTTTATGTTTGACTGTAAAGAATTTTTGGAAAAGATAGATTTATATGTTTACCTGTATGCCTGTGTGATCG
TCTACATCTATATAACTGATACTAGATTTATGTTAACTAAAAACGAAAAAAAAAAACCTTATAAAAATGAAAGGAGATGAATTTTGAGGCGTGAAG
CATTCAAGCAAACCATTGTTTCGAAATTTACTGCAACTGCAAAATAAAGAAAACAAAAACCAACAAAACACACATTATGAAAGAACACAAGAAAA
GCAACAAAATTGTAGCCCTAAGTTTATTCGTTTTATTACTTTTTATTTCTATTCTTTTTATTTCATTATACACTTTTATCTTTTTGGTTACTTGA
AACGCTAAGACTGAAATGGCTTGTTATGGAGAAGAAAACACGTCCTGCAATACATTATATAATAAAAAGAACCCAGCAATTTTCGCATCACCACA
TTACAGACAACAAAGTACTTTGTCCTCATCGTTCTGTGTGATCCAGATCCCCGACTATATATGATATATACACCTAGCTAGATTTAAGCGATTTG
TACATACAGAAGCAAAAGCAAAACAATATACCAGAAAATTGCCTGTTAAATACATTTATATACACATATGAATTTAGTTATATCACGATGACTAG
TTTTTAG
(SEQ ID NO: 1480)

Exon: 1001..1419
Exon: 1797..1958
Exon: 4474..4839
Exon: 9017..9223
Exon: 9289..9601
Exon: 9661..9837
Start ATG: 1867

Transcript No. : CT26380
TCGAAGCGTACGGTTCATAGGAGGAACGGAACGAAGCGGGGAACGCGACGGAAACTAGTTGCTGTTTTTTTGTCCGTGTTAAATAATTGACACAA
GAAAATTTAGCTACACTTAAGCAAAGTCCGCGAAAAATCTATTAAAAATCGTTCGTCGTTTTGTGTGTGTGACCACGAAAAAAGTGCCCCGATCG
GAGGATTTTAATAAATTCAATTAAGGTTCCGTCCCAACGATCGTTTTTCATTGTCTGACGCTCACGCGTGATGTACAAATGAAAAAGTAAAAATT
TAAATAAGATCAAAGAAAGAAAGATCCCAGTAAAATTTAAAGTGGATTGACTGCACAAGAAAAAGAAAAGTTCCTTACCTCCTAGCCAGAAGTCA
AAAGTGAAGCGGAAAACAGAGTGGAGATAACAATTAACGGGGCTTCCATACCAAAGTTCCTTGTTTGTAGAGATCATTGTAATCAGCGCAGATCG
AAGCCATATATAAAATGATTTCGCACAGTCCGCCCATATTCAGTCACAGTCCACCCGTTAGTTTTCTGGCGGACTTCATGAGCGGACATCCCCGT
CAATCGTTGAACTACAATGACGAGCCCAACAGAGCGTCGCGCTACTGCCGGCCCCAAGTGATAACGCTGGCCTCCAAAGCCATGGTCAACAACGC
CTCGGCGGCGGTCCAGGGTCAGGGTCCCAGTCAGCAGAAGGCGGGTGCCACGCCCCTGGGCGTGGGCAGTCGTTCCGGACGGAGTTACCTGGAGC
GAATGGCCTCGGCGCCGCTACTCACCAATCAGCCCAAATCCTGTCTCAGCCGCAAATCCTGCCTGCACAAATCCCAGAACACTACAGCCAGTTCC
GCAGATCTCTCGCCGACGGACACCGATGTCGCGGACAGTGCCAGTCATAGCTGTATCTGCAGCAAGGATAGTGACAGCAACGGCGAAGTGAGCCG
TGGCCCCAAAAAGCATGTGATCTTCGCTGATGATGAGGGTCTATCGCTAACCGAGGTTCGTGTGATGTCCGAACCCTCGAATGTGCCGCCATATT
GGAGCATGAAGTTTCTGGAGCAAATTACACAGGGCCTGGTCAGCCCACATCCTCCGGATCAGTGGACAGTGGACTTCAAGCAGCCAGCCTCAGAC
TATCTATCATTTAGACAAAAGATAGAACGCGACTTTGTTTCCTTGGAGAATGTGATCGTCAAGGATGAGGAATCGATTGTCGTGGGCACCATCAA
GGTGAAGAATATCGACTTCCAGAAGGAGATCATTGTCCGTGTGACCTGGGATGATTGGAAGAGCCAGCAGGATATCTTCTGTACATACGCCAGGG
CCTATGGACCGGCTACTTGTGCTCATGTAGTCTTCGATACATTCTCCTTCAAAATCACCTTGCCGCCATCCTCCAAGCGCCTGGAATTCTGCATC
TGCTATCGCACCAACGAAACAGAATATTGGGATAATAATGATGGTAAAAACTACACCATTAGCAAGCGATCGCCCTTTTATTACAACGCCTTGTC
GCCCTATGATAAGGGTCAGAATCGCAACTCGAGCCAGCAAATAAGGTCCACCCTGACCGATGCCTTGGCCAAGGTGCAAGACCAAAATGGCTGGC
ACCAGGAGCCACATACGCCATATTGGTGA
(SEQ ID NO: 1481)

Start ATG: 490

MISHSPPIFSHSPPVSFLADFMSGHPRQSLNYNDEPNRASRYCRPQVITLASKAMVNNASAAVQGQGPSQQKAGATPLGVGSRSGRSYLERMASA
PLLTNQPKSCLSRKSCLHKSQNTTASSADLSPTDTDVADSASHSCICSKDSDSNGEVSRGPKKHVIFADDEGLSLTEVRVMSEPSNVPPYWSMKF
LEQITQGLVSPHPPDQWTVDFKQPASDYLSFRQKIERDFVSLENVIVKDEESIVVGTIKVKNIDFQKEIIVRVTWDDWKSQQDIFCTYARAYGPA
TCAHVVFDTFSFKITLPPSSKRLEFCICYRTNETEYWDNNDGKNYTISKRSPFYYNALSPYDKGQNRNSSQQIRSTLTDALAKVQDQNGWHQEPH
TPYW*
(SEQ ID NO: 1482)

Name: putative protein phosphatase
Classification: protein_phosphatase

Celera Sequence No. : 142000013384010
TTTTATAAGTTCAGCAATGAAAATAGACTAAAAGTGTCTCATTCACGAGACCCTAATGGAAGGCCTAATTGATTTACATATGTCAGGGGGAGCACC
CTCACATAAAAGAAATGCGTGGGCAGACACATAAAACCAAAACCCACTCACAAATGAGTCGAGTGGTGAATAATGTCCCATATTCAATTGAGTGC
GGAAGAGGCCCCTTATAAATCTGTGTGTGAAATATCTTTTATAATAAAAACAATTTAACTAATAATACCAATTCTAGTTCGTAAGGCTATAAATA
TTGAACTGAACAGACCAGAGGCTATAACCTATCGACTTCGATAAGATAAATATTTAAAAAGCTGAGACGGAAAAAGTGTTTGCCAAACTCCTTGA
AATTCACTTGAGCGCCACGAGGCTCAGTGGGAAATTTGATTTTGGGAGATGGGATGCTTCCCGTGCATGTGATCATGTCTCGAGGGGCTGACACC
CGTTTTGACTTTTGTCACCGCCAGTGGCGCCAAAACTAATCAAAGCAACTAGGACCGACGCTAAATCGAAACCACAACTACAATCACTGCGGAAT
ACCAAAATGCAATCAAAATATGCAAGCCACGTCGATCAGGAGAGAGAGAGAGAGAGTGAGAGAGAGACCGGGGCTATTCTAGAAACCTAACGCGAGT
TCAGAACGCTGAATTATGTATACCCTTTAAAGTACTAACAGAGCAGAAAACTTAACTGTTTTATGTGGTCGTTCATTAGTAGTAAAAATGGGATG
ATTTTATTTTATTCTGCTTTACTGTTATTTCTGTTTTCTGTTTTTATATACTGGCCTCTTGAATATATAACATTCTGATAACATTACAAACGCTC
CACTAACATGTCTATATGTCTTGGAAGGGAATTCAAACAACCAATCTCTCTCTTTTTCTTTTTCTCTCTCTCTCTTTTTCTGTCGCCCCGATCAA
GTCTTAACGGCAAGTTGCAGCAACAAACATTTTCATTCGTTTTCGCATCGTCGAAGCGTACGGTTCATAGGAGGAACGGAACGAAGCGGGGAACG
CGACGGAAACTAGTTGCTGTTTTTTTGTCCGTGTTAAATAATTGACACAAGAAAATTTAGCTACACTTAAGCAAAGTCCGCGAAAAATCTATTAA
AAATCGTTCGTCGTTTTGTGTGTGTGACCACGAAAAAAGTGCCCCGATCGGAGGATTTTAATAAATTCAATTAAGGTTCCGTCCCAACGATCGTT
TTTCATTGTCTGACGCTCACGCGTGATGTACAAATGAAAAAGTAAAAATTTAAATAAGATCAAAGAAAGAAAGATCCCAGTAAAATTTAAAGTGG
ATTGACTGCACAAGAAAAAGAAAAGTTCCTTACCTCCTAGCCAGAAGTCAAAAGTGAAGCGGAAAACAGAGTGGAGATAACAATTAACGGTTAGT
TGTAAAGCTAAAACTACACAATAAACATATCATGAAAAACTTTATAAAACATAAGAAGGGGGGCATTTTATTATTTTGGGTATCAGCATTTACAT
CACCTTGTTTCGAATCAAACTGATTTTAACATGCATTTGGACCAAACTAACAACGTTTCGAATGTTATCTCTTATGGAAATGGTATTGCTATATT
ATACCATCATTAATTCCGATTCCACCTGAGATTAGCAATTAATATGAAATTTCATAAACATATATTATATATTCGGATCATGCATTCTATTTACA CATTACTTTCCAATTAAACGTTCATTTATTGCCGCGCTTCGATTAGCAACAAAAACAAATCGTTAATTTTCTATATTTTTCCACAGGGGCTTCCA
TACCAAAGTTCCTTGTTTGTAGAGATCATTGTAATCAGCGCAGATCGAAGCCATATATAAAATGATTTCGCACAGTCCGCCCATATTCAGTCACA
GTCCACCCGTTAGTTTTCTGGCGGACTTCATGAGCGGACATCCCCGTCAATCGTTGAAGTAAGTTTACAAAAGTATATAACTCATAAATAAATAT
AGCCAGCAATTGGACTAATTTAACACAGAATTGCTCTAAGTGAATCCACGAGTTTCGGCAGCCAATCAAAACAAATTAAATAGCCAAACATCATT
GAAAGAGTACCAATTCTCAGGTTTTTTCATGTCGAAAGAAAATATTTTTTTAACTTTCTTATCGATTGATAAGGAACTAGAAGCATTTTTCTGATG
CATCATCTTTTATGAATTTAACAAGTGGTGTACGTGTTAATAAGAGAAACGATATAAATGTCTGATAACCTGAAAAACCATGTGATAGTAAATGA
ATTAAACTGAGAGATAAAAAATACATAACAGATAAAAATGATTAATACCCTTTTGCATTAGGCGTTCTCTCTGGCGAATATTTAAACAATAATTT
TAAACATTCAAATTTAAAACAAATTTCAAAATACCCAAACATAACCCACATTAACAAAATAAACAGACCGGAATGCCGTAATTCCATTTAATGAA
TATAAGAACTCAGTTGTTTACACAATCCAGAAAAGGAATATTATCGATCTCTCGAGGGCTGCCCATATTGATTCACATGAAACACCTGTTTCAAG
TGTCGTCTATGGAAATTTTAACACCTGATCAAAGGCAGGAAACATGTCTTACCCAATACATAGTATTAAAACCTGAGAACTATTCGAAAACACAA
TGAATGCAGGTACTAAAAATATTCGTGCTAAGGCTCGTTTTTGGTTGACAACAACAGATTGGCAAAATATGAAAAGCAAGCATTCAAGATCAAGG
CAAGACAGAATACTGAACCAAAACAAACATTTCGCCGATTCTGAGGTGATCTTTCGCTGGTGGAGCCAACTGAGATTTGAAGATTCGTTCACGAG
TCGTGGGGGTGACGCCAAAAATTTGCTTGGCGACAATTTGCGCGTGGCGCTTGACGCAACTTTTTTCTCAGGGGCACACGAGCAAGCCGAAAAT
TTGACAAATTGGTAAAGGGAAGAAGGGTAATATCTATATATTATATTTATACAGAGGCGAGAGCAATTGATTGAATTAAAGCAATTTGCCGTGCT
TCATTTGCTGCACGCGCTGCATTTTCATCATATTTGTTGAGAGTATTTTATTTTTGGGAATGATAAATATACAATACCGAAAATTCGTATAACTT
ATATTCGTATATATGAGGACTTCAGCTAAAAATAAATCTATATCTAGAGTATGGCCAAGCAAAACAAACGCTACAAGAACCGGTAAAAAACTAAA
TAATCAGTTAAGATTAAAGAGGTTCAGTAGATAAAACTGTGGGAGGTAATACATGCGAAAGCCCTACTGCGATCCCTACAACTATGAACATTTCT
TATCGGGGCACGTGAGCGGCATGCCTTCAAACAAACCGAGTACTCCAACCAACTCAAGTAACTCAGCTGCTAATGCGTCAACTCACTTGAAATTT
CACAGCGTGATTTTACAACAGTTACCCCACCCAATACCTAGAACTACCCACGTAACTGGGCGGGTCGTCATCGAAAATGATTGAATTCTTTTGG
TTGCCAACTCAAGCACTAAATATGCTGATATTGTCTCCAGACAGCGCCAATTAGCCAAAAAAAGTTGATGATAACAGCAGAGCAGACGGAAATGT
TCCCATAGCCAGGCCCACGCCGAAAAAGACGTATCAGCATGCCGTCAACATATGTTTAGCATGCAAAAGTCCACGCGAACCCCATTGAACGATCC
TTATCAACCATTGACTTTTAGTTTTATGAATGTCTAGCCGAAAAATTATGATAACTACAAATGGGATGTGAACTGTGCCAAATGAGTAAGACCAG
CGAGTCTCTCCGACTATACAATTTTAGAAATGACTCACTGAAGAACCCAAACAAATATGCTTCATATTCATACTATACATTTCCCACCCACGGCA
AACCCGAATTAAGTGAGGAGGTCGCGCGCAACTCCTCTTATCAGCGATGTTTCTTTATAGACAATATACACGTATCAGTAGGACTACACAAGTAC
AAGTACAAATACAAGTAGTACATGGGCCTCCGAACAATGAAGGCAGGCATTGAGGCAGTAAAAATTAAAGCCACCACTCTTATCAGGACTGATAA
AAGGCAGCTTAATGCGTAGATGCTTGAAATAAAAGACTGATCTTGGGAATTTCTTTTCTGCTTTCCAAACGAAAAAAGAATCACAAAAAATGGTC
AAAACAATTGAAAGATGGCTACCATCTGCTGATGTTTAAATATAGAAATTATATTTCAATTAGTGGTGTTAGAGATATATATTTTAACTGATTG
TGATATATTCAACCTTCGATATTCAACCTTTTGATTTTTTGAACGAATTCAACACTCATTTAAAAGGACAGAATAGTAACGAAATTAAGTTATGA
AATAAATATTAAATAAATTTATTTTAAGAAACATTTTATAGTTATTAATTTAAGTTTTGAAATACAAAAATAAACCAATTAAACTTGCATACCT
TGTTTCAGCTACAATGACGAGCCCAACAGAGCGTCGCGCTACTGCCGGCCCCAAGTGATAACGCTGGCCTCCAAAGCCATGGTCAACAACGCCTC
GGCGGCGGTCCAGGGTCAGGGTCCCAGTCAGCAGAAGGCGGGTGCCACGCCCCTGGGCGTGGGCAGTCGTTCCGGACGGAGTTACCTGGAGCGAA
TGGCCTCGGCGCCGCTACTCACCAATCAGCCCAAATCCTGTCTCAGCCGCAAATCCTGCCTGCACAAATCCCAGAACACTACAGCCAGTTCCGCA
GATCTCTCGCCGACGGACACCGATGTCGCGGACAGTGCCAGTCATAGCTGTATCTGCAGCAAGGATAGTGACAGCAACGGCGAAGTGAGGTGAGT
GTGCGGGGCGATAAGATTACGTAATGTAGGTAACTCGATACAGCGGCGCCGAAACGATCAAGAAGGCTGTAAATGCCGGCGGACTCAGTCACTTTG
ACGTCAGGCCTTCAAAGATTATGGCGCCGCACTTATTAAACCACCAACTGAACTAGATGGGAACTTAGTGGTGTGAGAGCCTGGGTAATTGTGGT
CAGAATTGGGTGTATCAACCTATAACAGATTCATTAAATAGTAAGATGTCAATTGAGGGGAAATCTTAAGGAAAGTCCGAGAAAGTAACACAAGA
AGCTGTAGATGGTTTCATAGCGCATCTTAACTATGTAGACTGTGGTCAAAAAGAAATCGAAAGCTTATGATTCAAACTTAAATCTTTGAATTTT
AATATGGGGAGGATAGGATTTTGGTTCTAAAAATTGGAACGTGAAAAGATCATTTCTTATAAAACTGCGAAAATACCACTTCCGCCATAATATTT
TATAAACAAAGATTAATCGTTTATAAGACATTTGCAATAGTTCTAGTAAAAGGAATAAGAAAATCTGTTGGCAGTCGAACAACTTTCCCACAGAC
GTCATAGCCGAGCACATGTCATTTATTAAATAAGCTGAGAAAGCCAATTGCAGACGGCCGCCAGGCTAAACAAATGCAAAAAGATCATGAAATAT
ACTTGAAAATATATTTATATATTTTTAAGAGCATGCAATTTCACAAAAACAAAATATAAATTATCTAAATGACTGTAGAAATAAGCCAAAATAA
AAACACGCCACTGCATCGCGAGTCGAGAATCTGTATCTCGTATATCTGAGATAAAAAATCTCACATTTTAAGACTCAAATGGGAATAGACTGGTA
TTTAGTATAGACCCCAACAGCGAGGCGCCATTATTTTCGTTTTCCATTTCCATTTATTCGCTATATATAGGGAAGATACATTATCGATTCATGTG
CAGGCCATGAAAATATTTGGGTTATCGATGTCTCGCAGATATTTTGTAAAATTGTATACATATGTATATTTCGCTTTCAACGAGCCCTAGAAATA
ATTTCCTTTTTGCACTTGAATCTGACATTTTGAGAAATGCCTAAAAATACATATGCCACGAGATAGAGAAAATAATTTATACGTTCATTTGCGTC
AAATGCGAACACTATTTCTATTTGGGCTGCGTCTCTAGACAAGAGATCAGGCTTAAAGCTACGCAGCTACTCAAACGAATGCAATTAACCATAAT
ATTATCAATGTAAACCAGACGTGTGCTTGTTGCTGTTGGAGATTTTGTGTACACTTTGCGGTTGCGTATTTTGTATGCCTCGTTTTATCAGTTAC
GAAATCCACTGGGAAAAAATTAATTTACCAATTCAAATCTTCAGAGTAAATTATAATTCATTTAAGTTAACACAAGAACGTAAAGCAATGCAATA
GAAAAATTATTAAGAATTATATTTATTGGAGGCTTGATTTAAGAATTGAAGACCTTATTCATCACCTTCCAAAGCATATCGCATCTGCTCGTCAC
CCATTTGGCCCCACATTTTACAATGAGTTTTGACAGCCAATGAAAGATCTTTCTTTTGTCTTAATTAGCCTCCCCAAAAATCATCAAGATCAACC
ACAAAACGAGGCAGACGGTTCACGTCAAGGCCGAAGAATTATTAGCATAGAAGCGTGATCAAGCGAAAGGCGTCATCTCATAAAAGACACAATTT
TTTCGGGTGTAATGTAACTAAAAATATTTCAACATTACAAGCCTCGGAATACGAATGCACACAAACGTAAGGTTATATATAGAGATGGGGAGATA
TGTCTGATGTTCATGCAAAGATCACGTGAATCGATCGGAAAAGTGAGTCTGGGGCACATGGGTCTGCTGTAAAAATGTTGGCGCACCTTTAGCTG
AAAAATGTGAAAGAATTTCGTACATTTACAACAATTTTATTTCATTCGTAATTAAATTTATATTTATTGGTAGCGATCGAGATAATTAAGAAAAA
CCAAATCCACGACAGAATTTTCCGAGTTAAAACTATTTTCAGTCTCTTACTATTGGACTTTGCTTAAAATTTCAGAAAAATATAAACGATAGGTA
TATTTGGCGAAACTGAAATTCTTATGGGGAAATAAAATAGAAAATACAGAAAATTTGGCGACATACAATACGGAACTACCTTGATTCGTTTACA
AAAAAGTAGTTCGATTGTAAGGTCAACCAGAATGACCATCAAATCAGTCAGTTGTAAAAATTTCAACAGGTCTTGCCAGAATATTTTTATCGGAC
AGGTTATTGACTTTAGAAAATGAGGGAACTCGAACAAGGTCTGCAAATTGAAAACTGAGGAAATTAAAAAGTATTTTTAAACACAATTTTCATTT
ACATTACAAGCGTTTCGATTTTAAAAAGCCCTTTTGGTGCAGCCAAAACTTGTTTCTCCTGCACCCATCAACGATCTTAATGCGGCTTGCATATT
GAGGAGTTTACAAATTTATGGACTTTAAACCGGACCCACGAAAATAAATGCGTTCCGTAACGCATACGGAATTGTGACTGCCTTTGGGTTTTAAG
AAAAAACAGTTGATAGTCGTATCTCGTTTCCCTTGGAGAAAATGTAAGCCAAGTCGGGGAAAATCAATGAAAATGTAAATGATTTTTTTTTTTA
ATTTGATTTTTCGGGTGATCTCTTTCAAGTTGACAAGTTTTAGGAAAGCGGTCGGTAAAAAATGAGACCCGTCCGCGGTCTCCGGTTTCTGGTTG
GCGGCCTGCTGGGCGTTGAGACCCACCCCACACACACCAGATAAGCGATCGCTAAGAAACCTGTTGAAGAAAATGCAGCAACAGCAGGCGCACAC
CGATCATGCCCTCGATGCGTGATGTCGTCGATGTCGGTAGTCGGTAGTCGTTACGATCCGATTCTGGCCGAGTCGGGTGGTACGATCTGCCATCT
CAGATACACCATCACCATCACCGATCTCTGGCAATACGGCTGGGGTACAATCAACAGAGAGCCAGTCTGTCGATAGCCATTTCAATTGTTGGCTA
TTTGTACTTCCCATATATATTTAGCACTCGATGCGTTCCCGCCGACTCTCCTCCAATTTGCAGACCAAATAGAGTCTGCTCTGTGTGGGGCCATT
AGTCGTAGGTCTGCTCCAACTGACGGAAACTTTTCGCTTTGGGTTTGGCAACAGCAAAGAACCATACAAAAATCGAGCCCCTACCGAAGCTGATT
AGCCAAAATTAGTCGCTATATCTTATCGAATTTATGGCCAACTTTCTAAATAGAACTTGTATGCGTATTTTTTTCAGTAATATGAAAGTCAAAAG
GGCGGAACATTTGTTCGAAGAGTTTGGAAAGTAATTAACTGCAGCAAACATTTGTATTGAACACAATATATTATTATATTGTATTATTCGTATCT
GCATTTAAATTAGGTAAAATTTTAAAAGTCCAATGAATTTCAGATTCCAACTAAATTTCGTTGAATAACTTATATATTTTGAATCACGAGTTATC
CTCTATATTTTATATATCTTAGTGGGTGTGTTTTTATTTACATTTAAGCAAAAGAACCGTGGGAAGAGTCGCCCAATAACATGGGTGCAAAAAGA AAGGAAAAGCAAAAGTAGGCGTGATTTACATATAGATTAAGGCAAATCTTTGGCAAAGCCGTACGTGACTTCTAAAAATAAAACCAACAAAAAAA
TATACAATACACATTACTCTTTTTATGACGCAGGGAATTTTTCGGGAAACGCAAAGGAATAAAAATGATCAGCAGAATAGAAAAAAAAAAAACACT
AAAGGAAAAGTTTCACTCGACCGGGATTTTATATTACCAATTGTCAGACAATCGACAACTTTGGCACATATAGTAGGAGCTTTCAAAAATGGTTT
TAAAAACTGCATTTGGCAAAGACGCAGTTTGCTTAACTAAAGTAAAAACAAACCAATAAAATGAAACTGTTAAGGATAGAAATCCGGGCAAAGAA
AGATGCTGAGTCAATGACCACAAAGAAATAAAATAAATAATTCTGAATGGGGGGTCAAGTCAAACTGATAAAGCCAGGGTCAAATCTATATTTGA
TAATGTATATTTTAATAATTAATAATTTGCTTATAATAGATTGCGATGTACTCAATGGATGGTATTTCTTTTTTTACTTTTTGCAGCCGTGGCCC
CAAAAAGCATGTGATCTTCGCTGATGATGAGGGTCTATCGCTAACCGAGGTTCGTGTGATGTCCGAACCCTCGAATGTGCCGCCATATTGGAGCA
TGAAGTTTCTGGAGCAAATTACACAGGGCCTGGTCAGCCCACATCCTCCGGATCAGTGGACAGTGGACTTCAAGCAGCCAGCCTCAGACTATCTA
TCATTTAGGTTGGTACCCTATTTACACAACTGTAAAATATATACGAGTATTCTAAATATTTGTATTTACACAGACAAAAGATAGAACGCGACTTT
GTTTCCTTGGAGAATGTGATCGTCAAGGATGAGGAATCGATTGTCGTGGGCACCATCAAGGTGAAGAATATCGACTTCCAGAAGGAGATCATTGT
CCGTGTGACCTGGGATGATTGGAAGAGCCAGCAGGATATCTTCTGTACATACGCCAGGGCCTATGGACCGGCTACTTGTGCTCATGTAGTCTTCG
ATACATTCTCCTTCAAAATCACCTTGCCGCCATCCTCCAAGCGCCTGGAATTCTGCATCTGCTATCGCACCAACGAAACAGAATATTGGGATAAT
AATGATGTGAGTTTGGCATCAAAATAACTTAAAAAATATTTTACATAATTTGTATTTGCTTACAGGGTAAAAACTACACCATTAGCAAGCGATCG
CCCTTTTATTACAACGCCTTGTCGCCCTATGATAAGGGTCAGAATCGCAACTCGAGCCAGCAAATAAGGTCCACCCTGACCGATGCCTTGGCCAA
GGTGCAAGACCAAAATGGCTGGCACCAGGAGCCACATACGCCATATTGGTGAAATCGCCTGGGAACGGGATTGGATTTTCCTGACCCAAGCGATT
GAATAAAGTTTCTCATTTAGGCCACATGAACAGAAAGAAACAGAATTGGAAAAGATTTAAAGTGTTATAATCAGTTTCATTGACAGAGGGAGAGT
CCAAAAGATTTTACCACTAACGAAACTTTTTGACCTAAGCTAATACCCGGTACAAATATCCCAATTTTAATGTGCCATTGACTTGAGGTTTACTC
AATATAAAATGAGATAGGAGGGCTTATAACTACTTCTACTGAGCGAAGCCCGAATTTGTATGTCTTGTCTTTAGTCAACTTGATGGAATTTCAAA
ATCTATGTATAACTTTTTAAAATGTTTTATGTTTGACTGTAAAGAATTTTTGGAAAAGATAGATTTATATGTTTACCTGTATGCCTGTGTGATCG
TCTACATCTATATAACTGATACTAGATTTATGTTAACTAAAACGAAAAAAAAAACCTTATAAAAATGAAAGGAGATGAATTTTGAGGCGTGAAG
CATTCAAGCAAACCATTGTTTCGAAATTTACTGCAACTGCAAAATAAAGAAAACAAAAACCAACAAAACACACATTATGAAAGAACACAAGAAAA
GCAACAAAATTGTAGCCCTAAGTTTATTCGTTTTATTACTTTTTATTTCTATTCTTTTTATTTCATTATACACTTTTATCTTTTTGGTTACTTGA
AACGCTAAGACTGAAATGGCTTGTTATGGAGAAGAAAACACGTCCTGCAATACATTATATAATAAAAAGAACCCAGCAATTTTCGCATCACCACA
TTACAGACAACAAAGTACTTTGTCCTCATCGTTCTGTGTGATGCAGATCCCCGACTATATATGATATATACACCTAGCTAGATTTAAGCGATTTG
TACATACAGAAGCAAAAGCAAAACAATATACCAGAAAATTGCCTGTTAAATACATTTATATACACATATGAATTTAGTTATATCACGATGACTAG
TTTTTAG
(SEQ ID NO: 1483)

Exon: 1001..1419
Exon: 4474..4839
Exon: 9017..9223
Exon: 9289..9601
Exon: 9661..9837
Start ATG: 4544

Transcript No. : CT26388
TCGAAGCGTACGGTTCATAGGAGGAACGGAACGAAGCGGGGAACGCGACGGAAACTAGTTGCTGTTTTTTTGTCCGTGTTAAATAATTGACACAA
GAAAATTTAGCTACACTTAAGCAAAGTCCGCGAAAAATCTATTAAAAATCGTTCGTCGTTTTGTGTGTGTGACCACGAAAAAAGTGCCCCGATCG
GAGGATTTTAATAAATTCAATTAAGGTTCCGTCCCAACGATCGTTTTTCATTGTCTGACGCTCACGCGTGATGTACAAATGAAAAAGTAAAAATT
TAAATAAGATCAAAGAAAGAAAGATCCCAGTAAAATTTAAAGTGGATTGACTGCACAAGAAAAAGAAAAGTTCCTTACCTCCTAGCCAGAAGTCA
AAAGTGAAGCGGAAAACAGAGTGGAGATAACAATTAACGCTACAATGACGAGCCCAACAGAGCGTCGCGCTACTGCCGGCCCCAAGTGATAACGC
TGGCCTCCAAAGCCATGGTCAACAACGCCTCGGCGGCGGTCCAGGGTCAGGGTCCCAGTCAGCAGAAGGCGGGTGCCACGCCCCTGGGCGTGGGC
AGTCGTTCCGGACGGAGTTACCTGGAGCGAATGGCCTCGGCGCCGCTACTCACCAATCAGCCCAAATCCTGTCTCAGCCGCAAATCCTGCCTGCA
CAAATCCCAGAACACTACAGCCAGTTCCGCAGATCTCTCGCCGACGGACACCGATGTCGCGGACAGTGCCAGTCATAGCTGTATCTGCAGCAAGG
ATAGTGACAGCAACGGCGAAGTGAGCCGTGGCCCCAAAAAGCATGTGATCTTCGCTGATGATGAGGGTCTATCGCTAACCGAGGTTCGTGTGATG
TCCGAACCCTCGAATGTGCCGCCATATTGGAGCATGAAGTTTCTGGAGCAAATTACACAGGGCCTGGTCAGCCCACATCCTCCGGATCAGTGGAC
AGTGGACTTCAAGCAGCCAGCCTCAGACTATCTATCATTTAGACAAAAGATAGAACGCGACTTTGTTTCCTTGGAGAATGTGATCGTCAAGGATG
AGGAATCGATTGTCGTGGGCACCATCAAGGTGAAGAATATCGACTTCCAGAAGGAGATCATTGTCCGTGTGACCTGGGATGATTGGAAGAGCCAG
CAGGATATCTTCTGTACATACGCCAGGGCCTATGGACCGGCTACTTGTGCTCATGTAGTCTTCGATACATTCTCCTTCAAAATCACCTTGCCGCC
ATCCTCCAAGCGCCTGGAATTCTGCATCTGCTATCGCACCAACGAAACAGAATATTGGGATAATAATGATGGTAAAAACTACACCATTAGCAAGC
GATCGCCCTTTTATTACAACGCCTTGTCGCCCTATGATAAGGGTCAGAATCGCAACTCGAGCCAGCAAATAAGGTCCACCCTGACCGATGCCTTG
GCCAAGGTGCAAGACCAAAATGGCTGGCACCAGGAGCCACATACGCCATATTGGTGA
(SEQ ID NO: 1484)

Start ATG: 490

MVNNASAAVQGQGPSQQKAGATPLGVGSRSGRSYLERMASAPLLTNQPKSCLSRKSCLHKSQNTTASSADLSPTDTDVADSASHSCICSKDSDSN
GEVSRGPKKHVIFADDEGLSLTEVRVMSEPSNVPPYWSMKFLEQITQGLVSPHPPDQWTVDFKQPASDYLSFRQKIERDFVSLENVIVKDEESIV
VGTIKVKNIDFQKEIIVRVTWDDWKSQQDIFCTYARAYGPATCAHVVFDTFSFKITLPPSSKRLEFCICYRTNETEYWDNNDGKNYTISKRSPFY
YNALSPYDKGQNRNSSQQIRSTLTDALAKVQDQNGWHQEPHTPYW*
(SEQ ID NO: 1485)

Name: putative protein phosphatase
Classification: protein_phosphatase

Celera Sequence No. : 142000013385203
CGTAAGAGCGAACCGGCTTTTCTACCATTTGTTATTATTACTTTCACAGGATCTGTTAATATTTCGGAACCGAAGAGAAACCCAGTCCCGATACA
TGTCTATTTTAATCTAAACCTATCAGATTCTTTTGATTCCTGTGTAACCCTCAGTAGCATTACACTTGTTCCCAGAAAAATGGAATCTGGTATCT
TAAAAAGAAAACTGAAAGTAATTTATTCTGAACCCAATACCCTTCTAGATTTTGGTGATCAAACATAATAAATTGTTAGATTAGGGACTCGTTCT
ACGAAAATCTGCTTATCGATTTAATCATAGCTAATGTTGGAATTTATTTTTAATACAATTGCTCGATACCTTAGCTAGAATAATTCAAAAACGTT CTGAATTGTTTATCCTTCATTTTTAAACTGTAAAATTTGAGCTTATTCAGAGTGGAGTAGTATAAGAAAATGTTGAATATTTTGATACCGGATCC
GATAGTTATAGAACCGGAACCTACGGATCCCGTTGACCTTTTTCTTATCGCACTCTGATATTCCAACCGGTCGGACACATGTGTTTTTCATCCGT
GAAGTCGGCCCAGAATATTTCCATCATTCAATATTTACCACCTTTTATAGTTTTGTTTACTATCTTGCCGACTTTTTTGTCTTGCCGTCTTGCTC
TCCTCTCCATCCTAAAAATACTCTTCCTGCGCTCCATCTGGCAATGCCGCTCGACAACTGTACTTCAAAGAGCGTTGCCAGGCAGGTCACTTCTC
TCATAGATACACAGATACAGGCGCGCACGCACACCAGCACGCAAAATAACCACCACCAGCAGTACAGAAATTACACATTTTCTCCCCGAGTAGAG
AACTGAAAAACTGGCCGCGCTGGCAGCGCCGGAGCAGCGAAATTCGATCGAAACCATTTACTCAGTCTCAGTTCGAGTTATCCAACGTTGGCGAG
CGGACAAACAAGCAGGAGAAAAAAGCGTACGGGCAAGAGAAAGAGAGGCACAAAATCACCCACAGCCACTGAAATTTTCTTTTGCGCTCCGGTG
AGAAGATAATTTCACAAACCAAAACCGAACCAACAAACAAAAAAAGTGCGCTCCGTGAGCGGGAAAACAATAACAAAATCAAGAGACATGCGATT
ATAAAACGAACAAAATAACTGAGTGACAAAAAAAAATTAAATGCGTGTCTCATGGCTTGACTGTACTGTGTATTAAAAAATGTGATTGTGTCGGC
TGTCCGTCTGTCTGAGTTTGTGCGCGTGTGTGCTGTTGGCGTTTTTAAATGTGGCGCGCTATTTTTGTGTGATTTTTGTGGGCAGCAACGAAT
TTTGAAACATCAATTGTATACTAGTTGTCAGTCCCCTTGTGAAAAAGTCTTCTCCAACAACAAAATTCCTGTGAGCAGCCTACACACATGCGTTG
TCTCGCTCTCGCGCGCTCTGGCCCCCAAAGAGTGCGAGAGCGGGAGAGTGAGACCGAGAAAGAGAGAGAGAGAGAGAGAGCTAATAACTAACGTC
TGTACTCTTTTTCTTTTCCATTTTTCATTTCAGTTTCGAGAAAGCAGCGCGCCAAGCAGCAAGAAGAGGAAGAGCAAAGGGAGTTGGAAAAGCAG
TGGCGTCGTGGAGGAGGAGTAGAAAGGGGATTTTTGCGAAAAATCCCAACTTGAAGAGAATTTTCCCCGTAACCGTTAAACATTAAATCGTCGTG
TTGGAGACAAATAGCAGCGAATACGCTAGCAACGCTGGGGAGGAACAACAATTGTTGGATTTGGACGCGACCGCTTTGATGTCGCTGCCAATGAA
TTCGCTGTATTCGCTCACCTGGGGCGATTACGGCACCAGCCTCGTATCGGCAATCCAATTGTTGCGCTGCCATGGCGACCTCGTCGATTGCACGT
TGGCCGCCGGCGGGCGGAGTTTTCCCGCCCACAAGATAGTCCTGTGCGCCGCCTCCCCCTTTCTGCTGGACTTGCTAAAGGTAAGTGCTCGGTTC
GGAAACACTGCCTAAAACACCTTTCAATAAGAGAGCTTGTACATAACCTCAAACGTTTCGTACAGTTTGTAAACAGAGAAATCCAATCGCAGAAA
TAGGTTAATGTTTGGAGCGCAGAGAAACTGACACTCGCACGCAAATGCATACATATGTATAAATAACGCAGATTTACGCTCCGCTCCAAAAGTTG
TCTAGAGATTTTTGTACAAGTTTTCCACTGTCAATTGAGTTGAATGAGTGGCTCCGCCCCCCGCATTCCCGCCGTCTATCTTGCTTATCAGCTTT
TTCTTGTTGCAAAGTTCACCGGAGAACGAGAGAGTGAGACGTAGAGACAGAGCGCAGACAGAGAGGGAGAGAGCGAGAGAACCAGTTGGTTCGGT
CGACAGAAAAGTGGTTTTGGGCCCGGTGGTGTAACAGAGAGGGGAGAGCCGAAAGCTGGTGCGCCAACTTTTAAATCGCATGTGTTAGAGCGAGC
GCAAACGAGAGCGCCAAAAGCAGCGCGGCAACTGTTGTAGTTGTTGGATGGTTGGAGCTTTCGTCTTGCCTTTTGGTTCTTGCTGTTGTTGGGTG
CACACGAGCGCGACCTCTTTCTTCACAGACAGAACTGTACAGTTGGCTCTGGCTAGGGGGAACTTGAAATATTGGGGGGAATATGGATACATATA
CAAAGATAATTAAAATTAAATTTGTATTGATTGGTTTGATTTCCTTAACCCATTTCCTAAGCTAAGTCTTTTGTATTTTGTATGTCACCATTTTA
GATTGCTAGATTGATTGTCTAACAGCAAACTTCGCTCAATTAAAAGTTCCTGGACTTTAATAGACTTATCTACTTCAAATCTTTATTTAAACTTA
TAACATAGTGACCAAGTCCAGATTGTACCAAAGATAAGCAAGCCTGTCTGGTGCGCTTCCCTCGTATCGAATCCAACCCGTATTTCTATAAACTA
AAGCATTTCATATTAGGAAGGCGCACTTTTAAATGGAGCTTGCAAGTTTTTTCATGAGCTGTATTGCGATACTGTACTTTTTAACAACTCATTTG
CACTTTAACTTTGACGCTTTTCCGCCACTCTGTCGATTGTTCAAAGTGTGCGCTTAAGTATGAAAGTTGGACCGTCTTCAATGCGTGGCCCTATC
GTAATGGAAATACTGACCAAAACAGAGCGCGGCCAGCGAAATGAAAACACCTGATGCGACGCCGACAGCGGCTACTCTGCGCTTCGCTCCCCCTT
ATTCTCAGCGCTCCTCATCTCTCCTCTCCTTTTCTGGGCCGTGAAAAAGTAAACAGAGCGAAATTTTTGAAAACGCCGCTCAGAGCCGTCGTGGG
GAAATGTCAAAGAAAAAAAAAAAAAAAACAAAAAGAACGGGACCAATGCGGCTGTGAACTCTGCAAGAGTCCGAAAAGTACAAGATGTACTGATCT
CGTTACACTCACACACGCACGCAAAAACACATGGCGGTCGCTCTTTGTTGCTCTTGCTCCCTCTCCCTTGCTCCTACGGCAAATGGAATGCAACT
CTGAAAAATCGATGAGCGAGACTTTGGTTGGAGGCAGAGTTCAAAGAGCGCAAATGGGAGTGCGGTGAGATGTGTCATTTCAAGAGATTGGCATT
GGATGAAGGGAGGGTGTTGGTTGGTGAGTCCGTAAATGGAGAGGGGTTGTTTTCTGAGCAATGCTATATAATTAAATGTTTGGAGCGGGAGCGGG
AGCGGGAGAGGACACAGAAGAAGAACAGCTAAGCGCTCTTTCTTTAAGCGCTGCTCTGTTTTCTTTTTCAGCATCTGAAATCTCAAAATCCTGCT
GCAGAATGTGCAGAGCGCGCAAAAGTAAAAGCCGGTTGTCTTTTGTCTGTGTCACTGTGTGCGTGAGCGGAGGAGAGTGTGAGCGACGCGTCGCA
CCGCGAGTTTCCATTATTTCCATCTCCGTCCGACTGTTTTTGTTATTGTTTTTATTTGGATTGGCGGACGGACGAACGGGCCTCTCAATTCACGC
CAAAAATGTGAGACGATTTCAAAACAAACACAACTCTCTACGATGAAGTTCGAGCCAAGAGAAATGTTGGATGAAGAGCCTACGAACTTTGCAAA
GTGTCAAGAAGTTTTTCTTATAGAACATTTTTAGATTTCAATTAGAAAATTTCTATAACTTACTAGAAACCGGTTTTGGTTATCGTACATACCTT
AAACAATAGAGAAATATTTATATATCATTTAAAATCAATTTATCTTGCCCTATTCTTAATAACTCCTTTTAATCTCATTAGTTTTACTTATATAA
ATACAAACTTATCAGCTCTAAATAAATTAGATTATATATGTCTTCTCGATATTTACAGAATACACCATGCAAGCATCCAGTGGTTATGTTGGCTG
GCGTCAATGCGAACGATCTGGAGGCGCTGCTGGAGTTTGTGTACCGCGGAGAGGTGAGCGTGGATCACGCCCAGCTGCCGTCGCTACTGCAGGCT
GCCCAGTGCCTGAACATCCAGGGACTGGCACCGCAGACGGTTACCAAGGACGACTACACCACGCACTCGATACAACTGCAGCACATGATTCCACA
ACATCACGACCAAGACCAACTGATTGCCACGATCGCCACGGCTCCACAGCAAACGGTTCATGCCCAGGTGGTGGAGGACATCCATCATCAGGGCC
AGATTCTCCAGGCAACGACCCAGACCAACGCAGCAGGACAACAGCAGACCATTGTGACAACCGACGCGGCTAAACATGACCAGGCAGTGATTCAG
GCTTTTCTTCCGGCACGCAAACGCAAACCACGCGTAAAGAAAATGTCACGTAAGTTAAAAACTTATTTTTGTAAACAGTTGATTCAGAAAATTTG
TCCAATAAACTCTGAACGTATTGGGTAAGAATTAGAAACAAAAAATAATAACATGCATTTCTACTTGTGCAGCTACGGCACCGAAAATAAGCAAA
GTTGAAGGAATGGATACGATTATGGGCACACCGACCTCTTCACACGGCTCTGGATCCGTGCAGCAGGTGCTTGGCGAAAATGGAGCCGAGGGCCA
ACTGCTATCATCCACACCGATCATCAAGAGCGAAGGACAAAAGGTAGAGACTATTGTGACCATGGACCCCAACAACATGATACCGGTAACGTCGG
CTAATGCGGCAACTGGCGAGATAACACCAGCACAAGGAGCCACTGGCTCATCTGGCGGCAATACAAGCGGCGTCCTATCCACGCCAAAGGCAAAA
CGCGCTAAACATCCGCCCGGAACAGAGAGTGAGTTTTAATTTCGGTGTATTCACTTGCCGGCTTAAAGTTATTACTAATTATAAGTATATATTTG
AGAATAATGCATTTTGTTAGAGCCAGTGAATACCCAATATACCATCCCACAACGTGTTCCAAGAACTAAAGAACGCTATTTTCCGTTTTTAGAAC
CACGTTCACGATCACAATCTGAACAACCTGCTACTTGCCCCATTTGCTATGCTGTCATTCGTCAATCCCGGAACCTGCGGCGCCATCTCGAGCTG
CGGCATTTTGCCAAACCCGGCGTGAAGAAGGAGAAGAAAAGTAAGTCCGGTAACGATACAACCCTAGACTCCAGCATGGAGATGAACACCACGGC
AGAGGGCGACAACACAGTGGGCAGTGATGGAGCAGGCGGAGCAGGATCAGCAGGAGGACAATCATCTGGTACGACGCCAACGAGAGTGATATCGA
ATGCACCGCAGGCCGCGGGGGCGCCGGCCATCCTGGCCCAAGGTGTGCTGCCCCAGCAGCAGCAACAGCAGCAACTGCAGCAGCAACACCAGCAG
CACTTGACAGCAACATTAGCGGGTGGTGGACAGGCATACATCAAACATGAGGGCGGCGGCGGGGGCGGCACTGGGCAGCAGCAGCAACAGCAAGC
GGCACAACAGCAGGGCATGCAGAACGTCATACACATTGTGGGCGATCAGGTCTTCATACCGCAGCAGCAACAGCCGCAGCCGCAGTAGCCACCTC
CAGCCGAGCCTTCAATCATTCCAACGCACCAACGACACCATCATCCACATTTCCAAAAAAACATTAAAAAAAAAAACATAACACTCACAAAAACG
ATTTGTAAATAACAATCAGCAAACAAACAAATTCCCCGTGATCTGATCGAATGATTTGTGTTCATTTCCTGTATCATTTTTAATTTTTCCATAAT
TAATTGCTGCGTAAGTTTATATTTTGCATAACTTTTCAAAATTGCGCTTTTTAACATATAACATTTTCTTATGCAGTATTTTCTTGCATATTGTA
GCACAGAGAAAAGGACAAAAAGAGAGAATTCCGTATGTCTCCACCTAAATGAATACTCGATTAACTTACTTAAATAATCTAATTAGTAGTGTCGC
AAATAATTGTTGTAAAAATTAATTGTACAATTACAATCGAGGATCGCAATCGGTTTAAGTTTCTCTATTTTAGATATTATATTACAAATTGTTTA
ATTAATAAAATATTATATATTTTTTATATAACAAAAACAAAACCAAAATTAATCTCTGCCTGTGGCACGGACTTTAATTTACTGCAATTGGCTG
TTTATAATTATTGTTTCTCTTAGTTGCAAGAAAATACTGTTGGTCGATTTCCAAACCTACTAACTTCGTACTGATCTTTGTAATGTTTCGCAATT
CCTCTGGAGCAAATCTTGCGCATTTAGAATTGACAATCTGGCTGATAATCGTATTTAAAAGTCTTGAATTAACGTTGAATATTGTTACGTTGTTT
TTGTATCTTTTTTAATTATAACTACACGTTTGTTTTATTTTTTAACAGTTTTTCACTAGATTTTTTTTATTTCTATTATTAGTTTTGTTATTTGT
TGTTCATATTGATTTAAACCTATATTAATATTTGTTTTGTCTTGCGTTTTTAAGTTTTTTGTTTGTAACACCTTTCATCTACACAATCAACACAT
CTTCATGTCCTGTTTCCGGCTGTAGTCCTTAAAGGCCGCGTTGTTTCTCTTTTGGGCCAGAGATGTTGCTGTAGTGTCGTCCTCTCGCTCTGTAT
TACTCCTACTATCCAACAGTCTACCTTGGCTAACTCCAGCGGCAGTCTTCTCACCAGCAACTCATTCCTTCCTTGCAGCAACCAGTGGCAAGAAG

FIGURE SHEET 807

TCTAGTAGCGGATCCAGCGGTTCAGGCAGTGGGGCACTGAGCTCCAGTGGCAGTGTGCCGCAGGTCCAGACGGTTCAATCCCTGCACACTTTACA
GGGTGTGCAAGTCAAGAAGGATCCGGATGCCCAGCAACAGCAGCAGCAGCAGCAGCAACAACAACAACAACAGCAGCAAGCAATGACAGTGA
GCGGTGCGACGGGCGGACAAGTGCAACAACAGGTGCAGCAAGTGCAGCAGCAGGTCCAGCAGCAACAGCAGCAGCAGCAACAACAACAACAACAG
CTGCAACATCACCAAATCATAGACTCGTCGGGCAACATTACAACAGCAACAACGAGTGCTCAAGCGGCAGCTGCCGCACAGCAACAGGCGGCTGG
CCAGCAGCAGCAACTGGTGGCACAATCCGATGGCAGCGAGAGTGGAGCTCCGCTTTCAATTGCCCAGGTGCAGACGCTGCAGGGCCATCAGATCA
TAGGCAATTTAAATCAGGTGAATATAACTGACTTTCAACAACAACAACCGCAGCAGCAACAACAGCAGCAGCAACAACAGCAGCAACAACAACAA
CAGCAACAGCAAACACAACAGACGCTCTGATCGGACCGAAGTCTTAGATCCATCTTGTACTATTCTATACAATTATTAATTTGGGTTTTTGCTAA
ACGCTTTAAATATTCTCTTTGCGGAATGCGTAGACAAATTCTAAATTAGTTTTAGAAAGCCAGAAAGGCATATTTAGTTGTTTACCGTTTTGTTG
TACAATCTTATGACTTTAAATGTTGATTTACCCCTCCTACAACTTATTTTGTTGCTAGACAAACGCTTAAGTGCTCTATGGTTATTGGAAATTAC
GTGCATATTTTACATACTTTATAAATATTATCATTTTGTATGGTTTTACAAATGTCCCAATGCTAGAGGACCTCTAGTCATTTTGAAGTCCTGCA
GATCAGTAAACACCTTAATCCAACAAGGATCCCTTGCTCACGTCCAGATTTTGGCCATGAACGAATGCACCTTGATTTAAAAAATATTAACAAAT
ACATTAAGTTTAAAAATCCTTGAGTTACAAAGATTTACTTAAGCAGCTCAAAAGTAATTGATCTGATCAAAAGAGAGTTCGCTCAACAAGGTTTC
TAAAAACCCACCCACCAACAATCACTTAAGTAATCAATCAACCAATCAATAAATCAACTCGATATCTCTGCTTTCGTTTTTGTTTAAGAACTAGG
CGTTCTATGTTTAAATTGAACCAATTTTATATGTATATTACTTAATTTTAATAGTTGCAAATTTTTCCTAAAATTTAGACCCCGTTGTACTAGTT
TTGGATGATGAAATATACATATTCCTGGAAACTATGATTTAATTATATAAATTTGAACGAAAGGGTATATTTCATCTACCTAAACTGGACGAATT
ATTGTTAGTCTTCTTACACACTTAAATAAAATCTAATTTTATTTAAAACCAATTACAAAAAATAAGTTTAATAAAACAAAACTTTTTCAAACAAA
ATTATTATTAGTATTTTCTTTTGTTTTTCGCTTTTCGGTGATGGAACTTTTTGATTTAATTTTTCAATTAATTTACTCATAGTCCCTTTAGCAAC
CAACCTTACCTATTAATTAAGTATTTCTGTAATTTACAGCATGAATTAACGTTTTAAATATTTTTTGTATATTAGTTTTTTGCTTTTCCTGATTT
GCAGTACGGCTGACCTAAAAAATGAAGACAAACTTAATTGAAAAATCAAATAGTGACTAATGACACTTCACACACCAGCAACGAAAACTCACCAA
CACCACATGCATTCTGCACTGCAGTTTACACCATTTTGCAACACATGAGCAATCATTAACAAATCGTTTTTATCTTGTCTTCTTCTCTTTCTCGC
TGCCACGTTAATAACAACTAAACGTCATCTAACCAATCAAATTCAATACATCTGTGTGTAAAAACTAAACATTCATGCATCCGACAACAAATCAA
AATCATTCAAAAAAAAAAAAAAACAGGGCAACAACAAGAACATTTTGGTAAAGAAGGTTTTCATTTTGAAAGGCGGTAATAATACGTAATGATGA
TCCAACGATATGTCCAGCGGCCCTGGAGGAGGAGGAGGAGGAGGAGAAGGTGGAGGCGGCGGCAGCGGGCAACAGCAGCATAACACCAGCAGCTC
GAGCCACAACAACAGCAGCAACAACTGCGGCACGGCAGCAGCAACTCAATTGAGCAGCAGCAGCAACAGCAGAAGCATCACACCAGCAACATCGA
CATCATCGACTGGAACTGGAACAGGAACCACATCCACGCTGCAGCGTCGTATACTGCGCGGTCATGCGGCGCAAACGACCAGCGGCGAGCGTGTC
CTGCTCATCAACTATGTGCCACAAACAGGAGCATCAGCCACCGCATCCACTCAAAGTACTTCTCAATTGCCCACCCGTAAGATACTCCAGGCCAG
AGCCTCAGCGGCAGCAGCAGCGGCGGCAGCATCATCGTCATCATCTG
(SEQ ID NO: 1486)

Exon: 1001..1400
Exon: 1554..1980
Exon: 4334..4799
Exon: 4918..5253
Exon: 5413..5550
Exon: 7109..8642
Start ATG: 1789

Transcript No. : CT26545
ACAAAATCACCCACAGCCACTGAAATTTTCTTTTGCGCTCCGGTGAGAAGATAATTTCACAAACCAAAACCGAACCAACAAACAAAAAAAGTGCG
CTCCGTGAGCGGGAAAACAATAACAAAATCAAGAGACATGCGATTATAAAACGAACAAAATAACTGAGTGACAAAAAAAAATTAAATGCGTGTCT
CATGGCTTGACTGTACTGTGTATTAAAAAATGTGATTGTGTCGGCTGTCCGTCTGTCTGAGTTTGTGCGCGTGTGTGCTGTTGGCGTTTTTAA
ATGTGGCGCGCTATTTTTGTGTGATTTTTGTGGGCAGCAACGAATTTTGAAACATCAATTGTATACTAGTTGTCAGTCCCCTTGTGAAAAAGTCT
TCTCCAACAACAAAATTCCTTTTCGAGAAAGCAGCGCGCCAAGCAGCAAGAAGAGGAAGAGCAAAGGGAGTTGGAAAAGCAGTGGCGTCGTGGAG
GAGGAGTAGAAAGGGGATTTTTGCGAAAAATCCCAACTTGAAGAGAATTTTCCCCGTAACCGTTAAACATTAAATCGTCGTGTTGGAGACAAATA
GCAGCGAATACGCTAGCAACGCTGGGGAGGAACAACAATTGTTGGATTTGGACGCGACCGCTTTGATGTCGCTGCCAATGAATTCGCTGTATTCG
CTCACCTGGGGCGATTACGGCACCAGCCTCGTATCGGCAATCCAATTGTTGCGCTGCCATGGCGACCTCGTCGATTGCACGTTGGCCGCCGGCGG
GCGGAGTTTTCCCGCCCACAAGATAGTCCTGTGCGCCGCCTCCCCCTTTCTGCTGGACTTGCTAAAGAATACACCATGCAAGCATCCAGTGGTTA
TGTTGGCTGGCGTCAATGCGAACGATCTGGAGGCGCTGCTGGAGTTTGTGTACCGCGGAGAGGTGAGCGTGGATCACGCCCAGCTGCCGTCGCTA
CTGCAGGCTGCCCAGTGCCTGAACATCCAGGGACTGGCACCGCAGACGGTTACCAAGGACGACTACACCACGCACTCGATACAACTGCAGCACAT
GATTCCACAACATCACGACCAAGACCAACTGATTGCCACGATCGCCACGGCTCCACAGCAAACGGTTCATGCCCAGGTGGTGGAGGACATCCATC
ATCAGGGCCAGATTCTCCAGGCAACGACCCAGACCAACGCAGCAGGACAACAGCAGACCATTGTGACAACCGACGCGGCTAAACATGACCAGGCA
GTGATTCAGGCTTTTCTTCCGGCACGCAAACGCAAACCACGCGTAAAGAAAATGTCACCTACGGCACCGAAAATAAGCAAAGTTGAAGGAATGGA
TACGATTATGGGCACACCGACCTCTTCACACGGCTCTGGATCCGTGCAGCAGGTGCTTGGCGAAAATGGAGCCGAGGGCCAACTGCTATCATCCA
CACCGATCATCAAGAGCGAAGGACAAAAGGTAGAGACTATTGTGACCATGGACCCCAACAACATGATACCGGTAACGTCGGCTAATGCGGCAACT
GGCGAGATAACACCAGCACAAGGAGCCACTGGCTCATCTGGCGGCAATACAAGCGGCGTCCTATCCACGCCAAAGGCAAAACGCGCTAAACATCC
GCCCGGAACAGAGAAACCACGTTCACGATCACAATCTGAACAACCTGCTACTTGCCCCATTTGCTATGCTGTCATTCGTCAATCCCGGAACCTGC
GGCGCCATCTCGAGCTGCGGCATTTTGCCAAACCCGGCGTGAAGAAGGAGAAGAAAACAACCAGTGGCAAGAAGTCTAGTAGCGGATCCAGCGGT
TCAGGCAGTGGGGCACTGAGCTCCAGTGGCAGTGTGCCGCAGGTCCAGACGGTTCAATCCCTGCACACTTTACAGGGTGTGCAAGTCAAGAAGGA
TCCGGATGCCCAGCAACAGCAGCAGCAGCAGCAGCAGCAACAACAACAACAACAGCAGCAAGCAATGACAGTGAGCGGTGCGACGGGCGGACAAG
TGCAACAACAGGTGCAGCAAGTGCAGCAGCAGGTCCAGCAGCAACAGCAGCAGCAGCAACAACAACAACAACAGCTGCAACATCACCAAATCATA
GACTCGTCGGGCAACATTACAACAGCAACAACGAGTGCTCAAGCGGCAGCTGCCGCACAGCAACAGGCGGCTGGCCAGCAGCAGCAACTGGTGGC
ACAATCCGATGGCAGCGAGAGTGGAGCTCCGCTTTCAATTGCCCAGGTGCAGACGCTGCAGGGCCATCAGATCATAGGCAATTTAAATCAGGTGA
ATATAACTGACTTTCAACAACAACAACCGCAGCAGCAACAACAGCAGCAGCAACAACAGCAGCAACAACAACAACAGCAACAGCAAACACAACAG
ACGCTCTGATCGGACCGAAGTCTTAGATCCATCTTGTACTATTCTATACAATTATTAATTTGGGTTTTTGCTAAACGCTTTAAATATTCTCTTTG
CGGAATGCGTAGACAAATTCTAAATTAGTTTTAGAAAGCCAGAAAGGCATATTTAGTTGTTTACCGTTTTGTTGTACAATCTTATGACTTTAAAT
GTTGATTTACCCCTCCTACAACTTATTTTGTTGCTAGACAAACGCTTAAGTGCTCTATGGTTATTGGAAATTACGTGCATATTTTACATACTTTA
TAAATATTATCATTTTGTATGGTTTTACAAATGTCCCAATGCTAGAGGACCTCTAGTCATTTTGAAGTCCTGCAGATCAGTAAACACCTTAATCC
AACAAGGATCCCTTGCTCACGTCCAGATTTTGGCCATGAACGAATGCACCTTGATTTAAAAAATATTAACAAATACATTAAGTTTAAAAATCCTT
GAGTTACAAAGATTTACTTAAGCAGCTCAAAAGTAATTGATCTGATCAAAAGAGAGTTCGCTCAACAAGGTTTCTAAAAACCCACCCACCAACAA
TCACTTAAGTAATCAATCAACCAATCAATAAATCAACTCGATATCTCTGCTTTCGTTTTTGTTTAAGAACTAGGCGTTCTATGTTTAAATTGAAC
CAATTTTATATGTATATTACTTAATTTTAATAGTTGCAAATTTTTCCTAAAATTTAGACCCCGTTGTACTAGTTTTGGATGATGAAATATACATA TTCCTGGAAACTATGATTTAATTATATAAATTTGAACGAAAGGGTATATTTCATCTACCTAAACTGGACGAATTATTGTTAGTCTTCTTACACAC
TTAAATAAAATCTAATTTTATTTAAAACCAATTACAAAAAATAAGTTTAATAAAACAAAACTTTTTCAAAC
(SEQ ID NO: 1487)

Start ATG: 636

MSLPMNSLYSLTWGDYGTSLVSAIQLLRCHGDLVDCTLAAGGRSFPAHKIVLCAASPFLLDLLKNTPCKHPVVMLAGVNANDLEALLEFVYRGEV
SVDHAQLPSLLQAAQCLNIQGLAPQTVTKDDYTTHSIQLQHMIPQHHDQDQLIATIATAPQQTVHAQVVEDIHHQGQILQATTQTNAAGQQQTIV
TTDAAKHDQAVIQAFLPARKRKPRVKKMSPTAPKISKVEGMDTIMGTPTSSHGSGSVQQVLGENGAEGQLLSSTPIIKSEGQKVETIVTMDPNNM
IPVTSANAATGEITPAQGATGSSGGNTSGVLSTPKAKRAKHPPGTEKPRSRSQSEQPATCPICYAVIRQSRNLRRHLELRHFAKPGVKKEKKTTS
GKKSSSGSSGSGSGALSSSGSVPQVQTVQSLHTLQGVQVKKDPDAQQQQQQQQQQQQQQQQAMTVSGATGGQVQQQVQQVQQQVQQQQQQQQQ
QQQLQHHQIIDSSGNITTATTSAQAAAAAQQQAAGQQQQLVAQSDGSESGAPLSIAQVQTLQGHQIIGNLNQVNITDFQQQQPQQQQQQQQQQQ
QQQQQQQTQQTL*
(SEQ ID NO: 1488)

Name: Trithorax-like
Classification: transcription_factor
Gene Symbol: Trl
FlyBase ID: FBgn0013263

Celera Sequence No. : 142000013384405
CCAGTCTGCAAATATCCATGGAATTATTTACTACGGGCATCATTATTAACCACCGCGGTTGCTACTCACGCGAGCTTGATGAGATTGGGGCTGGT
CAGCAGCTGCGGACAACTGTGCCCATTGCTCACCGTCTCTATGAAGTGCTTAAGCTGATCCAACAGGTTCTGGCGCAGCATTTTGTCGTCCTAGG
CATCGGGAACGCAGCACCGAAGTTGGCCAAGTGAGCAAATGCATCGCAGCAGCGGGTCGCTGCGTCTTTCACTCGGAATACCAAAACGACGGGGC
ACAACTGCAGGCATTTGGAATCCGCCGCCACCTGGCCACACTAAGGCGGCAGAAAATTCGAAATTCTTTAATATCTGAAAATCATAAAATTAACA
GAATAATAAATATCTTAGCACTCTAACGTGTCATTACATTCATTATAAACTAGCACCTGAGATTAGTTTAAGATGACACTTTACATTCAAGTTAA
ATTAAGCTGGAAAAGATTTCTAATCGGAATTATGTGTTTACTACAATGCTAACTTTCGAATCGAGGATGTAATTACTGAGTAATCAAACTGTTTG
CTCTTTTTAATACTAAGTAAACGTACTTATAGCTCTATTTTCTAATTTTATAATATTTAACGTGTTTTTGTTTTAAAATATTATCGTAACAGTAG
GGAGTGCGAAAAACGGTAACACCAAAACCCAGTTCGTGCATTATTGCACACTCTTTTGGGGCGAATCAAGAGCGAAAGACAACATGGCGTCGAAG
CGGCGAATCTGTCTCGCAGTTTGTCGTGCTGTTTGCTTTTTTCTGCTCTGATTTGTACAAATATTCATTCAAGGTGCTCCAGTTTTGCCAAGTAT
ATGTTAATAGAGTACCATAACAATGGTGGCGTCACAGGGGTGCTAGAGTTCGATATCGATAACAGCTCACATTCTCGTCATATGCAACTATCGCT
GTACTCTCTGGCCGAGTATCGATACGCAGATATTATCGTCGTGGTCAGACCAACGCTCTAGCGTCGGTCCGCGGAAAATAGCGAAAATTACAATT
ATCCGGGAAGATATATTGGTCGAAAACTAACTCGTGATCCCCCAATAAATATGCGCAAGAGAAAATTGTATATAAACTGATCGAATGCAGCCAGC
GTGCTAAGCACTAAAAGCGAAAAACGCCAGAAACAGAAACAAGGAATTGCAGCGTGAGTGTATAACTTTTTGGTTTTTGCCCCCGCGCTCTTTCT
CTCTCTTTGCTGCTCTCTCTCTCCCGCTCTCTTTTGCCCTCTTGCGGCTTCTGTGTTGTCTGCGTGCTAGTGTGTGTGTGTTTGAATTTTACTGT
GAATGTGACCGACGGTGTGTTCTCACGTACTCCGTGGATGATTTGCGGCCTTGCCAGGGAATCGGACTATATATCCCGGCAATAGCCCATATTGG
ATCCCGATTTTGAATACAACTCGGCTGATTTGCTTCTTTCAGTGTCTCCCCTTTTATCGCACTTTATGCAACAACGCATACCGTCGTGTTGAATT
TCCTCGCTCTCCGCTGTGTGTGGTTTGTAGGTGTGCGTGTGTTCGAGGTGAGTTAGCCGTCGTCTGTTTTTCTTTTCCCTGCGTTTTGTGTGCGT
TTCAATGAAATGCAAAATCGCCAGCGAATATCGCGGAAATGCGCTGCTCCTAAATATTATGTATACATAAATAAAGTATCGAATCAAAACAAAAT
CGGCTTGCAACAACAACAAAAACATTGCAGAGTGTGGGTGGCGCGTGTAGCGATCAAAATTGCGTGCATGTGTAATGTGTGTGGTGGAGAGACGG
CATTTTTCTTTACCACACGCCTCTTCTTCTTTCCCACAATACACTGCAATTTTTGCGATTCTGTTTTGCGCCTGCCATTCGCAATAATTTTATTG
AATGAACCGCAAAAGAGACGGCCCAAAAAGCGATGTACTTGCCAGACGTTGTGTCTGTGTGCGTCCAAGTGTCTGTAGCGCGTTGTGTGTGTATC
GCGTATGAAAATACATCAACTGTTGGGCATCAACAAAAAAACGGAATCAAAAATTTATAATAAAAAATGAAAGGAAATTAGCTGACTTTGTAATC
GCAATCGGAGAGTGTTTACTTGCTAAATTTTCGAGTTCTCCGCCCGTCTCTTTCCCTTCATCCCTCCTGCCTTCACCGCCAATACCACCCCAAAA
AATTGCATACATGCACACACGCCTTCGGTTGTGCGAGTGGTTTAGTGTGTGAGCGCGCGCGTATTCTGCACACATTGTCATGCATGCAAAAAACA
AGATACGACGCGTTCGCAATCGTTAGATTCCGTCTCCCCCAATTCATGGCGTTTCATTGCTGGGGGCGAAAGTAAGAAGATAACGAAAGGGATAT
GCGAACCACTTCCTAATGAAGTCCTGCATCCTTAGCTTTTGGATTCCCACCTCTTCGCCTTCTCCTTCTTCACACGGACACTTGCAGCGTTCGCG
CCCATGCGTGTGTATGTGTGCGAAGAACAGGAAGAGAGCAGCGAGACTCCAATTATCCATTTACAGTTGCGGTTGAAATGATGGAGCATAGTTGT
ATTATTTGTATTCACACAATTACCGGTGGTATTTAAAGTCTTAACAATATTTATTAATTTCCTGCTACCTTCCTAAATTTTATTCATAGTTTTAA
TACTGTACCCAAGTACCTTAAGTTCCCTAATCAGATGTAAACTTGTTGATAGGCATAATTCCTATCTTAGTTTGTATTTTTGTCTACTATAACCT
AAACTTAATTCTACTACGAATTTAATTACAACATACTAAGACTGTAATCTACAAACCAAACGAAAATGCCTTGAATAAAAGAGGTCTAGTGATTC
ATAATACGATTTGCACACGTGTTATTAACTAGGTAGTAGCGAAATAGAGTCAAAAAGGCCACCGACTTGTTCACAACTGTATCTCTTACTAACTT
CCCTATAAAAACTAATTGTTGCTGGGGCGAAAAAATACTGCCAAGTTGTCATATTTGCCGGACTTTATTGATGACTCGACTCCAGAGCTCTATAT
TTCGCACACAGATTTTCTCTCGGCACTTTTCGCAACCTTCTGCGGCCGCTGGTTATTAATAAAAATTAATAATAAACGAAATCTGTGGCGCTGTG
CGGCACTTGGACACACTTATGTACACATGAGCATTCTCGTGTTTTTCGCAGCTGATTGCGTAAACGAAACCGCTCGCTACGTTTGTTTTGAATTG
CTACTTTTGTTTTGGTACCGATTCAGACTTGGAATCCGATTCAGTTACAGATTGAGATTGAGATTGAGATACTCAGGCTCTCCGCCTGGGCTTCA
ATTCTCCTGCGGGCGTTATCAGTGGCCTATGGCGCTTTATTGGAATTACCATGGAAGTGGGAACTTAATCGCTGTGCAAATCGCTTCGAAACAGC
GCAGCACGCATTTTCCCCGACGTCTTGCAACCTTGGGCGAGTGGCACTGCGGGCGGTGGGTGGTGAGCGGTTGGGTGATCTAGAGTGACGTAAAT
ATTTGTGGTGGACAGTCAACATTGAGGTGGCGCTCTTCAACGATGACGTAGCTTTTGCCACTTCTGTTTACTCGCACATTATTTCACACACTTCT
CCATTGATTTTCGCCGTGCAGATAACGAAATAGTGGACTGATTGTTAACTGTGTATAAATGAAAATATGGGTATGATATGTGTTTATTTACACTT
TTTTTCTGTGTACGAGAATGGTTAGATTACTCCCCTTCCTCGTTTTGAGTCACCCGCTCTCTGGCCCTCGCCGCTGTTTGTTTTCTTCGCGCGCG
TGTTTGCTCTCGCCGTGGGGCGAAAGCGCAGCGATAATAGTGGCTCAGATATAGTGTATACTATATGTATAGTAAACCTACTCATACCGAAAACC
CCATCGCACAGATACGGATACATTTACAGATACACGCGCGCACTGCGGAAGGCCTAGATCTAATGGAAAACGCTAAATGTTTGTAAACAGACCGG
GCACATTTCTTTTCTTTTCTTAATTATTTTTTGCATTTCGCATTTTAGTTGGCATGGTCTTCTCACGGCTTCTCTCTCTTCACACATCTTTCTTC
CGAAAATACACTCACACACACGCACACCGAACGTAGCTTTCACATTTTCATTCATCGCAATCTTCGCCATGAAGTGTTGCAAAGGCCCCAAGATA
AGATATAGGATGCACTTGGATACCTTAACCTCACCTTTTTGCGACAATAGCACACGAATAATCCAATTTTTTGTATGACGTTGTTGGGCGAACAA
TTTTATAAGTCTTGGAAAGGAATTTCTGTGCTGTGTTGATACACAAAACAACAAAATAATAAAAAATTATAAATGGTATTGAACTACTGTACTAG
TGAATAGTTTGAACCAGACTTTAAATTAAAGGCAATTATGATGTTGAAAATATTTAAGTACCTTTATGCATGCATATAGTTAAAATACAATTTTT
TAGATAACAAACAACATATGCGTTTACTGTCATTAAAAAAGGGATTATAAAACCATAAAAAAAGGATTTCGAAAAAGTAGTGTTTTTTAATATTG
TATGATCTTTGAACGTTTTTTTTTTTAATTGTTTTATTTTCCTAACTTGCAGTGCAGTCTCGTCGTGCGCCCATCCCAATCCCATCAGACCCCAC CCGGCGTTGGAGTGCAAGAATAACATGGATATAGAAGTCAAGCATAAAGATTAGCCGAATCCTTTGAATTTTAAATTCAAGATCCTAATTTAAAT
TAGCTAAGTAGCATAGCCTAGCCAATAGTCCCTAGCCAGAGGAACGGTTCCAAGCCGCAAGCACTCGCGTTCATAGTCCCGATCGAAATTCAAAC
GAATCCCAAGGGCACCAACAGCGTGTAGAACCGCAGAAGCACAGCAAGGAGGAACATCATCATGACGACTGACACCCGCCGACGCGTCAAGCTGT
ACGCGCTGAATGCGGAACGGCAATGGGATGATCGTGGCACTGGCCACGTGTCATCCACCTATGTGGAAAGACTAAAAGGTGGGTTTACGAAATTA
ATGAAGCCTTGCGAAGTGATTTAAGTTTCCTATTGCTCACTAACAACTTACAGGCATCTCGCTTTTGGTGCGAGCCGAATCCGATGGATCTCTAC
TTTTGGAGAGCAAGATACAACCGGACACCGCATACCAGAAGCAACAGGATACGCTGATCGTGTGGTCCGAGGGGGATAACTTTGATCTGGCCCTG
AGTTTCCAGGAAAAGGCGGGCTGCGACGAAATATGGGAAAAGATATGTCAGGTAAGCGTCGTTGAATAAGCATATGCAGTTATAAATGTGCTTAT
CTATATATCAATGAACTTAAACAATTTCTATATGGTTTTCACATCAATTGCCAACTAAAACTTTTGCAGGTGCAAGGCAAGGATCCATCTGTAGA
AATAACTCAAGACATCGTCGAAGAGTCTGAGGATGAGCGGTTTGAGGACATGTCGGATACTGCGCCACCCATTGAGCTACCACCCTGCGAGCTTT
CCCGGCTGGAGGACATCTCGGAAACGATACAAAGCTGTCTCTCCACGCCGCTGCGAAAGGAAAAGTTGTCGATGGCTCTGGAGTCGGAGAGCTAT
ATCAAGAAGCTGCTGAACTTGTTCCACGTGTGTGAGGACCTGGACAATACCGAGGGCCTGCATCACCTTTTTGAGATCTTCAAGAACATCTTCTT
GCTAAATAAGAACGCGCTCTTTGAGATTATGTTTGCGGATGATACCATCTTTGATGTGGTCGGGTGCCTGGAGTACGATCCGAGTGTGTCTCAGC
CCAAAAAGCATCGACAGTATCTGAAGCAGTTAGCCAAGTTCCGCGAGGCAGTGCCGATTAAAAACCTGGACCTGCTGGCTAAGATTCACCAGACG
TTCCGGGTGCAGTACATCCAGGACATTATCCTGCCCACACCATCGGTCTTTGTCGAAGACAACATGCTGAACACCCTGTCCAGCTTCATCTTCTT
CAACAAGGTGGAGATTGTCACGATGATCCAGGACGACGAGCGGTATCTCCTGGATGTGTTTGCTGTTCTCACCGATCCCACCACCGGAGACGCGA
AACGCCGCGACACAGTTCTCTTCCTCAAGGAGTTCTGCAACTATGCCCAGAACCTGCAGCCGCAGGGCAAGGACTCGTTCTACAAAACTCTCACC
TGCCTAGGCATTCTGCAGGCGCTGGAACTCACTCTCGTGATGAACGACAAGAAGACCAAATCGGCCTCCATCGACATCCTCACGGCCATCGTAGA
GTTCTCGCCTCTGGTAGTGCGCAATTACACGCTCAACCAGGCCAATCGGCCAGAAGTGGTAAGTTAACCTGGAATATGAAGATAGTCTAGATATG
ACTATGATTTACATGATTTCTTTTTTTTTCACACCAGGAGCGTATGCTACTGAACATTGCCATCGAACAAATGCTGAATGACTCGGAGCCGGAG
CTTGGAATTGCGGTGCAGCTAATGGGTATCGTCAAGATTCTGTTGGAGCCGGAAAACATGCTCACCGAGAAGGGCGATTTTCTCAACTTCTTTTA
CAAATACAGTGTGCAAACGTTAGTGGGTAAGTGCGAGTACTCTATACCAGCATATTCTAGAGACTAACTGCTTAATGGGTTATAGCCCCGGTGAT
ACTTAACACGATAGGCGACCGTCCGCAAAACGAGGACTATCAGACGGCCCAGCTGCTGGGAATCGTCCTGGACATTCTTTCGTTCTGCGTGGAAC
ACCACAGTTATCACATTAAAAACTTTTTGTTGCAAAAGGATCTCCTCAAGCGAATACTGGTGCTAATGAAGAGCACACATACGTTCCTTGTCCTC
GGCGCTCTGCGATTACTGCGCAAGATAATTGCACTTAAAGATGAGTTTTACAATAGGTAAGCGTCCCCAAAAACTCTTATGGTTAAACAATATAA
CCAACTTACCTTACTTACAGACACATTGTCAAGTGCAATCTGTTTGCGCCGGTGGTAGATGCCTTCATTCGCAACAACGGCCGATACAACCTTCT
GGAGTCAGCAATTCTGGAGCTGTTTGAGTTTATAAAACTCGAGGATATCCGCACTCTGTGCGTTTACTTCGTGGAGAACTTCAGCAAGATATTTG
ATGAAATCGAATACGTGCAGACATTTAAGTACTTGAAGAATCGCTACGATCAGTACCAGGATCGGCTTAAGGACCGCGACAAGATGGAAAACCGA
ACTGACGGGTAAGTTTTGCTGCAGCGCCTTGTGCTACAACACAATGTGAAAATATTTGGCTGTATTATCTTAAAGTGGCCTGCCCATCATCCGTA
GCGGTGGCCGGTTTCGTCGGGATCAGCGGCAAATGGAGGAGGAAGAGGAAATGTGGTTTAACGAGGAGGACGATTTCACCGAGGAAATCGACACA
TACAACAATGTCATGAAATGTTAGTACTAAATTAATATCGTTTTAGCATTACCAAACCAAATATATTGTGGCGAATATCTAAGCAAAAAAGCTAA
TATTCAAAAACATTACATTATTATTTATGTACCATTGATGAATTGTAAATATATTCCGATCTCGACTTGCAGCCGTCAGCGAAAAGAATGGCCCG
CAAACGCAAAACCAGCAGAAATCCTCTCCGCCACACAGCACGTCGCCGCACAGTGGATTGTTGGGAAGCCTGAGCACCACCGCGTCATCCACTGC
CACATCCGCCACGTCAGGTGCACCGGTGGCCAGCGGCAGCAGTAGCCCCGAGGCCATCTCCGCCGACGAGCAGACGCAGGCGGCGGTGCATTTGG
CTGCCGCTGCCCTTCAGCACCACCAGCAACAGCAACAGCAGCAGCAGCAGAACCCATTCCAGCAACAGACACAGCCCGAGATCGCGGAGCTACAA
CAGCAGCTGAGCAGCGTGGAAGCGCCTCAAAGCCAGGAGTTGGAGCTGTCACAATCGGCCGCCGCCAGTGCATCGCCCACTTCGTCATCCTCGTC
TCTGGAAGCCTCGACGTCCTCTTCATCGGCGTCATCGTCTTCATCCTCGTCGTCCTCGTCCTCGCCGCCCGGCTCATCGGCCGCAGCATCGCTAT
GCGATTCGGCGACAGTAGCCGCCGTGGCAGCATCACAGTTTCTCTCAACGATCGCCACAGCCATGGCGGCCTCTGTGACGGCGGCGGCGGCAACA
AACAGCTCCCCGAGCATTTCGCCAGCTCCAGCTGTGTCCAGTCCGGATATCGAGAACGCCGACGCCCAGTTGCCGCCCAGCGATGACGCCAGCAG
CCCGGCCAGTGGGGAGCAAGACGCTAACAGCACGGAAGGTACCAGCAGTGAGGCCGACAAGACGACGGCCAAAAAGGTAAGTTGTGGAACCCATA
AAATGGGAATGTCATAGTGTTTTCTGTAGTATTACTTGTGAATTGTGGATTTTATCTTCAAAATGCGTGCTTAAATATTTCTATAATGAATCAAT
GTTTAAGTTGTAAATATAGGAGCATTGGCAAATATTTAAATAAAAAGCTAAAATTCCCTCACAAACTTGAAGCAACAATATGCCTGCATGTATGG
GTATACAATTACCTTCTATTCTGTGACGATTAAAGTGCACGACTATTATAAGAAGTTTAAGTAGCGTTACGTATGAATAACAAATGTGTGGATGC
ATTAATTATATTATTTTCGTTACCATAAACAGGGTCTGGTGGACTATGAGAGTGATTCTGGCGAAGATGACTACGAGGAGGATGAGTACTCCGAG
GGGCCACAAGCACAAAAGCGCGCGCGTCAGGCATAGTTGGCCGATGACGAGCACAGCGGCATCAATTATAAATTAGTACACACATAACAGAATAC
AAGAAACCACGGCAAACAACAAGCAACAAACAACACACAGACCCCACACACCAACACCAACGAATGTTAGGATTGCATTGGCGGCAACGACATAC
AGCACAGTAGGCAAGCAAGCAAATAGCCGTACGATGTAAGATCGAACAAGAAAGCATAAATTTAAATTTTAGCATAAAATTTATTTTAAAGGAGA
AGCAAAAACACCTAAAGTAAACGAGAAATTATAAATCTTACTTTACTAAATTAAATAACTACATATAGATATATATATATATATTCAAATATATA
TGCATATGAAAACACAGATAACTATAACTGATCAGCATCCACAAGCAGAGATGTAGTTGAGTGCGTGTTGTTGGAAAGTTGGCAAAGCAAAGCAT
TAACGAAACAAACCAAAATAAATTGTATTTAGTAGTTAAATCCCCCTCTCTCCAAACTGATATGAACAGCAGCAGCAGCGCCAGCGCAATGGAGG
TGTGGTCAGGTGGTGAGGGAGATTTGTATACAGCCAGCGCCAGCACATCCATTTGCAATGTCTATCGTATGAGATCGTATGAGTTAACAGATCCT
GTGAAGTTGGCTGCTGGCCCAGAATGTTTGTGCAATACTTTCGTGTCGATATTTAAATAACAATTGCAAAAGGGTGTATTTAGTTCTAAAGCCTA
GACTTAACCATTTTTACGATCCTTCTCACCATTGAGATGGATTTTCTGCCAATTGTACTATCACTATCACGATACAGCGCTGTTTTCACTTGACA
ATTTCATTAAATAATTCTTATCGCGAAAGCATTTTATGAAAGTTTCTATTGCAAGCAGTGCTGTAAATAGATGTTTTTAATTTTAAAATTTAAAC
TATTCCCACAGCAGTAAAATGTTTTTTTTTCCATTAGGATTGCTTCTGTTTTTTGTGTAATTGCGATTGTTTTCTGAATATCAACCAGATTGCCA
GGGCCAACTTGACGAAGTTTGTTAGCCGGCCCCTTGAGTTAAATGCAGATAACACTTGAACCCAATGAACCTTGTATATAATTTAGTCACTCTCA
ATGCGCGATTAGTTGATAACTGCCCTTGCACCACTGACGCCGACATTAAACGCATATATTTGCACTTGGAGATATCGAAATCTTTGCACATTATC
GTGCTGTTCGAAATCCAGAGTCTTGAGATGTGTTGTCTGTGTAATTGACTGTGTAATTACAAACAATTGTTGCGCTATCCTTGCATTATTGAAAC
ACACAAACAAAAACACAACACACATCAATAAATTATTAATGATAATGATAACAAATAGGACGTAAAGTTAAACTAATGTGGGGCAAACAGACATC
AGCAAGCAGAGATAACAATAAAATAAAGTCTTAAGTAAAATAGTCTTCTTGAGTTTTCGAGTAAGTTTTTTTCGTATTTAACTATAATATTAATT
TGTATTTAACGAATGTAGTAGGGCTCACTTGGAACCAATCCAATCCAATTCAATCCACACTCATA
(SEQ ID NO: 1489)

Exon: 1001..1193
Exon: 4613..5018
Exon: 5089..5276
Exon: 5390..5466
Exon: 5545..6328
Exon: 6404..6581
Exon: 6641..6896
Exon: 6956..7228
Exon: 7296..7429

Exon: 7578..8341
Exon: 8678..9232
Exon: 9291..9325
Start ATG: 4907

Transcript No. : CT26561
CAACGCTCTAGCGTCGGTCCGCGGAAAATAGCGAAAATTACAATTATCCGGGAAGATATATTGGTCGAAAACTAACTCGTGATCCCCCAATAAAT
ATGCGCAAGAGAAAATTGTATATAAACTGATCGAATGCAGCCAGCGTGCTAAGCACTAAAAGCGAAAAACGCCAGAAACAGAAACAAGGAATTGC
AGCTGCAGTCTCGTCGTGCGCCCATCCCAATCCCATCAGACCCCACCCGGCGTTGGAGTGCAAGAATAACATGGATATAGAAGTCAAGCATAAAG
ATTAGCCGAATCCTTTGAATTTTAAATTCAAGATCCTAATTTAAATTAGCTAAGTAGCATAGCCTAGCCAATAGTCCCTAGCCAGAGGAACGGTT
CCAAGCCGCAAGCACTCGCGTTCATAGTCCCGATCGAAATTCAAACGAATCCCAAGGGCACCAACAGCGTGTAGAACCGCAGAAGCACAGCAAGG
AGGAACATCATCATGACGACTGACACCCGCCGACGCGTCAAGCTGTACGCGCTGAATGCGGAACGGCAATGGGATGATCGTGGCACTGGCCACGT
GTCATCCACCTATGTGGAAAGACTAAAAGGCATCTCGCTTTTGGTGCGAGCCGAATCCGATGGATCTCTACTTTTGGAGAGCAAGATACAACCGG
ACACCGCATACCAGAAGCAACAGGATACGCTGATCGTGTGGTCCGAGGGGGATAACTTTGATCTGGCCCTGAGTTTCCAGGAAAAGGCGGGCTGC
GACGAAATATGGGAAAAGATATGTCAGGTGCAAGGCAAGGATCCATCTGTAGAAATAACTCAAGACATCGTCGAAGAGTCTGAGGATGAGCGGTT
TGAGGACATCTGTCTCTCCACGCCGCTGCGAAAGGAAAAGTTGTCGATGGCTCTGGAGTCGGAGAGCTATATCAAGAAGCTGCTGAACTTGTTCC
ACGTGTGTGAGGACCTGGACAATACCGAGGGCCTGCATCACCTTTTTGAGATCTTCAAGAACATCTTCTTGCTAAATAAGAACGCGCTCTTTGAG
ATTATGTTTGCGGATGATACCATCTTTGATGTGGTCGGGTGCCTGGAGTACGATCCGAGTGTGTCTCAGCCCAAAAAGCATCGACAGTATCTGAA
GCAGTTAGCCAAGTTCCGCGAGGCAGTGCCGATTAAAAACCTGGACCTGCTGGCTAAGATTCACCAGACGTTCCGGGTGCAGTACATCCAGGACA
TTATCCTGCCCACACCATCGGTCTTTGTCGAAGACAACATGCTGAACACCCTGTCCAGCTTCATCTTCTTCAACAAGGTGGAGATTGTCACGATG
ATCCAGGACGACGAGCGGTATCTCCTGGATGTGTTTGCTGTTCTCACCGATCCCACCACCGGAGACGCGAAACGCCGCGACACAGTTCTCTTCCT
CAAGGAGTTCTGCAACTATGCCCAGAACCTGCAGCCGCAGGGCAAGGACTCGTTCTACAAAACTCTCACCTGCCTAGGCATTCTGCAGGCGCTGG
AACTCACTCTCGTGATGAACGACAAGAAGACCAAATCGGCCTCCATCGACATCCTCACGGCCATCGTAGAGTTCTCGCCTCTGGTAGTGCGCAAT
TACACGCTCAACCAGGCCAATCGGCCAGAAGTGGAGCGTATGCTACTGAACATTGCCATCGAACAAATGCTGAATGACTCGGAGCCGGAGCTTGG
AATTGCGGTGCAGCTAATGGGTATCGTCAAGATTCTGTTGGAGCCGGAAAACATGCTCACCGAGAAGGGCGATTTTCTCAACTTCTTTTACAAAT
ACAGTGTGCAAACGTTAGTGGCCCCGGTGATACTTAACACGATAGGCGACCGTCCGCAAAACGAGGACTATCAGACGGCCCAGCTGCTGGGAATC
GTCCTGGACATTCTTTCGTTCTGCGTGGAACACCACAGTTATCACATTAAAAACTTTTTGTTGCAAAAGGATCTCCTCAAGCGAATACTGGTGCT
AATGAAGAGCACACATACGTTCCTTGTCCTCGGCGCTCTGCGATTACTGCGCAAGATAATTGCACTTAAAGATGAGTTTTACAATAGACACATTG
TCAAGTGCAATCTGTTTGCGCCGGTGGTAGATGCCTTCATTCGCAACAACGGCCGATACAACCTTCTGGAGTCAGCAATTCTGGAGCTGTTTGAG
TTTATAAAACTCGAGGATATCCGCACTCTGTGCGTTTACTTCGTGGAGAACTTCAGCAAGATATTTGATGAAATCGAATACGTGCAGACATTTAA
GTACTTGAAGAATCGCTACGATCAGTACCAGGATCGGCTTAAGGACCGCGACAAGATGGAAAACCGAACTGACGGTGGCCTGCCCATCATCCGTA
GCGGTGGCCGGTTTCGTCGGGATCAGCGGCAAATGGAGGAGGAAGAGGAAATGTGGTTTAACGAGGAGGACGATTTCACCGAGGAAATCGACACA
TACAACAATGTCATGAAATCCGTCAGCGAAAAGAATGGCCCGCAAACGCAAAACCAGCAGAAATCCTCTCCGCCACACAGCACGTCGCCGCACAG
TGGATTGTTGGGAAGCCTGAGCACCACCGCGTCATCCACTGCCACATCCGCCACGTCAGGTGCACCGGTGGCCAGCGGCAGCAGTAGCCCCGAGG
CCATCTCCGCCGACGAGCAGACGCAGGCGGCGGTGCATTTGGCTGCCGCTGCCCTTCAGCACCACCAGCAACAGCAACAGCAGCAGCAGCAGAAC
CCATTCCAGCAACAGACACAGCCCGAGATCGCGGAGCTACAACAGCAGCTGAGCAGCGTGGAAGCGCCTCAAAGCCAGGAGTTGGAGCTGTCACA
ATCGGCCGCCGCCAGTGCATCGCCCACTTCGTCATCCTCGTCTCTGGAAGCCTCGACGTCCTCTTCATCGGCGTCATCGTCTTCATCCTCGTCGT
CCTCGTCCTCGCCGCCCGGCTCATCGGCCGCAGCATCGCTATGCGATTCGGCGACAGTAGCCGCCGTGGCAGCATCACAGTTTCTCTCAACGATC
GCCACAGCCATGGCGGCCTCTGTGACGGCGGCGGCGGCAACAAACAGCTCCCCGAGCATTTCGCCAGCTCCAGCTGTGTCCAGTCCGGATATCGA
GAACGCCGACGCCCAGTTGCCGCCCAGCGATGACGCCAGCAGCCCGGCCAGTGGGGAGCAAGACGCTAACAGCACGGAAGGTACCAGCAGTGAGG
CCGACAAGACGACGGCCAAAAAGGGTCTGGTGGACTATGAGAGTGATTCTGGCGAAGATGACTACGAGGAGGATGAGTACTCCGAGGGGCCACAA
GCACAAAAGCGCGCGCGTCAGGCATAGTTGGCCGATGACGAGCACAGCGGCATCAATTATAAATTAGTACACACATAACAGAATACAAGAAACCA
CGGCAAACAACAAGCAACAAACAACACACAGACCCCACACACCAACACCAACGAATGTTAGGATTGCATTGGCGGCAACGACATACAGCACAGTA
GGCAAGCAAGCAAATAGCCGTACGATGTAAGATCGAACAAGAAAGCATAAATTTAAATTTTAGCATAAAATTTATTTTAAAGGAGAAGCAAAAAC
ACCTAAAGTAAACGAGAAATTATAAATCTTACTTTACTAAATTAAATAACTACATATAGATATATATATATATATTCAAATATATATGCATATGA
AAACACAGATAACTATAACTGATCAGCATCCACAAGCAGAGATGTAGTTGAGTGCGTGTTGTTGGAAAGTTGGCAAAGCAAAGCATTAACGAAAC
AAACCAAACAGCGCCAGCGCAATGGAGGTGTGGTCAGGTGGTG
(SEQ ID NO: 1490)

Start ATG: 488

MTTDTRRRVKLYALNAERQWDDRGTGHVSSTYVERLKGISLLVRAESDGSLLLESKIQPDTAYQKQQDTLIVWSEGDNFDLALSFQEKAGCDEIW
EKICQVQGKDPSVEITQDIVEESEDERFEDICLSTPLRKEKLSMALESESYIKKLLNLFHVCEDLDNTEGLHHLFEIFKNIFLLNKNALFEIMFA
DDTIFDVVGCLEYDPSVSQPKKHRQYLKQLAKFREAVPIKNLDLLAKIHQTFRVQYIQDIILPTPSVFVEDNMLNTLSSFIFFNKVEIVTMIQDD
ERYLLDVFAVLTDPTTGDAKRRDTVLFLKEFCNYAQNLQPQGKDSFYKTLTCLGILQALELTLVMNDKKTKSASIDILTAIVEFSPLVVRNYTLN
QANRPEVERMLLNIAIEQMLNDSEPELGIAVQLMGIVKILLEPENMLTEKGDFLNFFYKYSVQTLVAPVILNTIGDRPQNEDYQTAQLLGIVLDI
LSFCVEHHSYHIKNFLLQKDLLKRILVLMKSTHTFLVLGALRLLRKIIALKDEFYNRHIVKCNLFAPVVDAFIRNNGRYNLLESAILELFEFIKL
EDIRTLCVYFVENFSKIFDEIEYVQTFKYLKNRYDQYQDRLKDRDKMENRTDGGLPIIRSGGRFRRDQRQMEEEEEMWFNEEDDFTEEIDTYNNV
MKSVSEKNGPQTQNQQKSSPPHSTSPHSGLLGSLSTTASSTATSATSGAPVASGSSSPEAISADEQTQAAVHLAAAALQHHQQQQQQQQNPFQQ
QTQPEIAELQQQLSSVEAPQSQELELSQSAAASASPTSSSSSLEASTSSSSASSSSSSSSSSPPGSSAAASLCDSATVAAVAASQFLSTIATAM
AASVTAAAATNSSPSISPAPAVSSPDIENADAQLPPSDDASSPASGEQDANSTEGTSSEADKTTAKKGLVDYESDSGEDDYEEDEYSEGPQAQKR
ARQA*
(SEQ ID NO: 1491)

Classification: hypothetical

Celera Sequence No. : 142000013384405
AACGCCTCTCTCTGCAGGAAATACGCCACGACACGTAAGTAGGAATATTCCTTGATTGCACTTCATGATAACTGATTGTTATAATCTGCTTTTAG
TTGGTTCCGATCCGCACCGGTTAAGACCGGCCCACCGATACCCATTCCCCCCCTGAAGGGTGACAAATACCGCAACTCCACGGTGATACCTTACT
TGGAAGCTTACCACTACGGCACCCAGGAGGAGGATGTCTACTTTACAGAACACGACGTAAATCGTACGTACCAACATCAATCTAATGCCGAGTGA ACTACTTTCATGGTTACCTTTACAGAGGAGCTCGCCCGCCAAGCGGCAGCTGCTGCCTCCGAAATTCGGGCCAAACAGTCGGCGGCAGCCCTAGC
CGCCTGCCACACCTACGAACCGCCCTCCACAAGTGCCGCAGCCGCCAGCAATTCGCTGGGCAACGGTAGCAGAGAGGAGGCGCCCGTCAAGAAGA
AGGGATCGGCACTGAAGAGGCGCGCCAAGAAGCTGACGTCCTGCATCTCCGTGCGCAAGCTGAGCCACTGCCGAACTTCGTAGGCGCCTTAGATG
CCTCCACTAAACATAGATGCTAAGATTTATCGAAAGGAATAACTTTGTTAACAAATTGTGAGCAACTTTTTGGTTTTGTTTTCCCGTTTTTATTC
TGTTGTCCTACATTCGCCAAGTATTTGTAACCATAGAATCATGTAGGAAATTCAGGCGCAACCTCGTACCGCCCGAGCAGCAGGAGCAGCAGCGG
TCGCATCAACAGCAGCAACAGCCCGCATCAGCGGAGTTGGCTGTGGAATTGGGGAGCTATGGGAGCGACACGAAAGCTATATATCCATGTGACAA
TACTGTGTATTATATGAAACAAATGAATGCGTAAATTAGTCGTTAATATATTATGATGTACTGAAGGCAGCCGAGGATTGCCGGAGGAGACGGTG
CCCATTGGTGCGTCGCACACATAAAGAAATATGTTCAAGTGAAATTGTTTGTTGGCTTCGTTATATTCTAAACTACACACGACGAATGATGCGAT
TTTCAGGCGCCGTCGGTACAATAACTGCTGGACAGTATTTGCAAGGCCTAGGTTGAGATTTTAATTTTTACAAACCAATGAAACGAAAATAAAAG
AACCCATTGAATATCAAAATACAAACACTGCATTTAGTTCGCACATTTCGCACATTCCAAATTCCACACTCAACACTCGCAGACGCTCCATTATT
CCATGCACACACGCTCATGCTCACACTACAACATTAGGCTAGCTAACTACGTTTGCTTAATCTATTTCAACGATCTGCAGCCGGGCCGTCGGATC
TGGCTCTGAGTCGCCCTCCATCAGCTCGCCCATGATGAACATCTGATGGTAGTGGGGGCCCAGGGTGGACAGCTTACGCTGCATTAGGTGGCGCA
ACGGGTCCACATATTGCGGCGGCACCTTGGCCAGCTGTGTATTCGTGTTGCGCCAGTGCAGCCCGTTGTTGTCCACGTGAAACAGCGCCGGCGAG
GGCACGTGATCTTTAAGATAGTTCCAGATGCACTCGCGCAGCAGCAGGGCAATCTGGAAATGTCATACATTAGTTGGTGCTACTACACAGTTTGG
GCAAATAATGGATCTACCTCTGCCGATTCAAAGTGCTCGATGATGAGATGCAGATTGGTGAGTGGAGGTGGAATTAGTTGGCTCATAGCCAGCAG
TTGCAGCATCTTCTTGGTGCACAGCATCAGCTCATCGTTCGCAGCAGTGGGCTGGAATCGATTGACTGCAAACGTATAATATGATTAGGCACCTT
TATAGAAAATAAGCAAGTAAAGTGACAAGCTCACCATTCTTGCCCCGCCAGTGATGCAAGCAGGTGGCGCACAGTGCGCGCAGTAGCACGGAGGA
ATAGCAAAGCGCCGGCCTATGACCGGCGATCAGTCCCAAAACAGCCCACAGCACTGGGGAGTTGATGAACGCTCTCCTGATTAGCATGTCCCGCT
CCATTGTGACCCTGGTGAACTCCTCATCCGGAAAGGGCAGGCCGTTGTACATGACATCCGTGGAGACCAGCTCGACCAGCAGCAGCGAGACCAGC
GAGTAGCCCTCCACGTTGTTGGGCTTCTCCAGATCGGCGCAGCATGCATTCAATGCCTTAAGATACAGCGCCTGCTTCTCCGCATCGCAGTTCCG
CTCGCTGGGGGGCAGCACTGGTCGCAGACCTCTGCCTATAATACCGGAATGCAGCACGGAGCGATTCGAGTTGGCGCCAGAGCTGGTGTGCAGAT
TCTGCAGGATGAGGTGTTCGTGCTCGGGTATCTCAAGCTCATCGAGCTGATACACCTCCAGCTGACCAAGCAAGTGACCGTGATAAAAGAGCGCG
CGCTCCACCAGCTCGCGCAGGCAGACGGTTCTCGCGATTTTCCGGGCGGAACACTGCCTCTGCAACAGCGTGTAGGAGCGATGCGAAGCCGCTGC
TCGACGGATCACAGCTAGAATGAGATATGGTTAATATATTGAGGCAAGGCTAAGGAACAACTATTGCGCTTACTCTTCTCGGTTAAGCCCACAAA
GAAGTACTTTACGCTTAGCGTGGCCAGCTTGAGGACTAATGGAGTGCGCAGGACAGTTGTCCGGCTGCCGGCTTCAATGTTGTTCAACAGATCCA
CAATGAGATGGGCCAAGCGCATGCGGGTAGCGTCCTCATCATCCACCTTATCTTCTCCCGGCTCCAATTTTGTGCGCTTTCCGTAATCCTTGCCA
TTGCACAATTCATTGTTGTTATTGCTATTTTTACTTTGCTGCGCCCGGAATTTATCCGCTATCCGCTCGGCGGCATCCCTGTCTATCCTCAGGAC
CAGTTTGTTAACGGTGCAGTCGAAGATTTGAAGGATTTTGGGAAGACATTCGTTGAGGGCTTGGTTCAAATGCTGCGCTTTGATGTACGGAGCCA
CATTCTTGCTCTTGTGCATCCTGATGGAGATTATGAATTTGAAACACTAATTATATGTATCTAACAATAGTAATAATTACCTGGCAAGTATGTTT
AGGTTGGAGAAAGTGTTAAAGGCTTCTGTGGGTGTGCCCGGCGGAACTGGCAATCGATTGTTAACTTGAACATCCAACGTGATGTCCTCCAAGAC
CATCTTGAAACCTGGCGTGAATCCCGGAAAGTTAACCATGCCGCTTTGTCCGCCAAGTAAGCGAATTAATGCGCCAATGCCATTGGGATTTTGAG
CATACGACTTCTTTAGAAGTTGGGATATAGTTTGGTAGTAAATATTCGGGTGCTGGGATGCTAGAAAAATAGTTCGTAAAGTCTGCCATTTCAAT
ATCTGAAGAACTTTCTACTCACAGACCACCAGCAGTAATCTCACCGCTGTTTGCTGCTCGAAGAGATTGGTGCTGAGGCAGCTCTTCCACAGCAT
GTACTTGGTTTCCTCATAGGCCAGATCGGCCAGCAACGGGAAGTTCCGCTGGTTGAGCACCCACTGTTCCAGCTCCTGCATCGAATTGTCCAGGA
AATCCTGACACCAAACATACTTCTCGGCCATTTTGGCTGCCGTAAGGAGCAACGTCGCTCCACGCTCGTTCAGGCGCAGCACGGCATTATTCAGC
GTGGGCTGCATACCGGCAAACATTTTGTTGCTCAGCCACAACGGCGCCTTCTGCACTATCACCTCGCACATGTCCTCGGTATCTACATGACATTG
TGTTAGAGAAATAATATATCTCTTTATTCAACCAGTACTTACAGATTTCGACTAGCACATTGACCAAGCTCTGCAGGATCGTGTCCGAGTAGTTG
GTGGTGATCAGCAGGAAAGGAACAACGGCCACGTCCAGCGGCTTCTTCGGTGCGAATCCCTCCCTAAGCATCTCACGAAAGGCTGCCCTAAGGTG
CTGTTCGTGGCACGAGGTCATATAATCGAGGATGCCCGCCTCCGAATCCAGGTGGCAGCGGTAGTCATCGACGAATCGCTTGATGCCGCACTGTA
GAATCTGCATGATGATCTTGTAAGGGAAACAGCCGCCCAATCTCGCCACAATCCAGTCGAAGGTCATGGAAACCGGTGAAAGGCATTGAGCATG
ATCTCCACGCAGGCCTCCTCCTCCGGTTGGGTTAACTTTCGGAAACAACTATTTATAAGGGTCATCAGCCCGTGCATGGCGCTGCACTCCAGCCA
ATAGTTGCAGCTGGCCGTGATGGTCATCCGCCGCTGGGTGTACTTATCGGACAGCTTGGCCACTAGTTCCAGACTCCAGTTGGCGATGAGCGGCG
ACCAGGCGGGCGGTCCCTTCCACACCAGACTCTGCAGCGCGGTCTTTACCAGATTGAAAGCCTCGTATTCCGGAGCACGTTGCTGCTGCTGGCGA
TTCCCGGCCAGCTTCACCTGGGATACCGGCATACCGGTCTTTGGGTCGGCCATCTCCGGCGACACATACAGCTGCACACTGATTTCGGCCAGCAG
GGCGAAGTATTCGAACACAATGTCTCGCGTGGCGGGCAGCTCCTCCAGGAATCCCAGTCTGCAAATATCCATGGAATTATTTACTACGGGCATCA
TTATTAACCACCGCGGTTGCTACTCACGCGAGCTTGATGAGATTGGGGCTGGTCAGCAGCTGCGGACAACTGTGCCCATTGCTCACCGTCTCTAT
GAAGTGCTTAAGCTGATCCAACAGGTTCTGGCGCAGCATTTTGTCGTCCTAGGCATCGGGAACGCAGCACCGAAGTTGGCCAAGTGAGCAAATGC
ATCGCAGCAGCGGGTCGCTGCGTCTTTCACTCGGAATACCAAAACGACGGGGCACAACTGCAGGCATTTGGAATCCGCCGCCACCTGGCCACACT
AAGGCGGCAGAAAATTCGAAATTCTTTAATATCTGAAAATCATAAAATTAACAGAATAATAAATATCTTAGCACTCTAACGTGTCATTACATTCA
TTATAAACTAGCACCTGAGATTAGTTTAAGATGACACTTTACATTCAAGTTAAATTAAGCTGGAAAAGATTTCTAATCGGAATTATGTGTTTACT
ACAATGCTAACTTTCGAATCGAGGATGTAATTACTGAGTAATCAAACTGTTTGCTCTTTTTAATACTAAGTAAACGTACTTATAGCTCTATTTTC
TAATTTTATAATATTTAACGTGTTTTTGTTTTAAAATATTATCGTAACAGTAGGGAGTGCGAAAAACGGTAACACCAAAACCCAGTTCGTGCATT
ATTGCACACTCTTTTGGGGCGAATCAAGAGCGAAAGACAACATGGCGTCGAAGCGGCGAATCTGTCTCGCAGTTTGTCGTGCTGTTTGCTTTTTT
CTGCTCTGATTTGTACAAATATTCATTCAAGGTGCTCCAGTTTTGCCAAGTATATGTTAATAGAGTACCATAACAATGGTGGCGTCACAGGGGTG
CTAGAGTTCGATATCGATAACAGCTCACATTCTCGTCATATGCAACTATCGCTGTACTCTCTGGCCGAGTATCGATACGCAGATATTATCGTCGT
GGTCAGACCAACGCTCTAGCGTCGGTCCGCGGAAAATAGCGAAAATTACAATTATCCGGGAAGATATATTGGTCGAAAACTAACTCGTGATCCCC
CAATAAATATGCGCAAGAGAAAATTGTATATAAACTGATCGAATGCAGCCAGCGTGCTAAGCACTAAAAGCGAAAAACGCCAGAAACAGAAACAA
GGAATTGCAGCGTGAGTGTATA
(SEQ ID NO: 1492)

Exon: 4722..4588
Exon: 4523..3748
Exon: 3692..3598
Exon: 3519..3348
Exon: 3290..3026
Exon: 2965..2544
Exon: 2484..1840
Exon: 1775..1633
Exon: 1573..1001
Start ATG: 4423 (Reverse strand: CAT)

FIGURE SHEET 812

Transcript No. : CT27084
CTGCGTTCCCGATGCCTAGGACGACAAAATGCTGCGCCAGAACCTGTTGGATCAGCTTAAGCACTTCATAGAGACGGTGAGCAATGGGCACAGTT
GTCCGCAGCTGCTGACCAGCCCCAATCTCATCAAGCTCGCACTGGGATTCCTGGAGGAGCTGCCCGCCACGCGAGACATTGTGTTCGAATACTTC
GCCCTGCTGGCCGAAATCAGTGTGCAGCTGTATGTGTCGCCGGAGATGGCCGACCCAAAGACCGGTATGCCGGTATCCCAGGTGAAGCTGGCCGG
GAATCGCCAGCAGCAGCAACGTGCTCCGGAATACGAGGCTTTCAATCTGGTAAAGACCGCGCTGCAGAGTCTGGTGTGGAAGGGACCGCCCGCCT
GGTCGCCGCTCATCGCCAACTGGAGTCTGGAACTAGTGGCCAAGCTGTCCGATAAGTACACCCAGCGGCGGATGACCATCACGGCCAGCTGCAAC
TATTGGCTGGAGTGCAGCGCCATGCACGGGCTGATGACCCTTATAAATAGTTGTTTCCGAAAGTTAACCCAACCGGAGGAGGAGGCCTGCGTGGA
GATCATGCTCAATGCCTTTCACCGGTTTCCCATGACCTTCGACTGGATTGTGGCGAGATTGGGCGGCTGTTTCCCTTACAAGATCATCATGCAGA
TTCTACAGTGCGGCATCAAGCGATTCGTCGATGACTACCGCTGCCACCTGGATTCGGAGGCGGGCATCCTCGATTATATGACCTCGTGCCACGAA
CAGCACCTTAGGGCAGCCTTTCGTGAGATGCTTAGGGAGGGATTCGCACCGAAGAAGCCGCTGGACGTGGCCGTTGTTCCTTTCCTGCTGATCAC
CACCAACTACTCGGACACGATCCTGCAGAGCTTGGTCAATGTGCTAGTCGAAATCTATACCGAGGACATGTGCGAGGTGATAGTGCAGAAGGCGC
CGTTGTGGCTGAGCAACAAAATGTTTGCCGGTATGCAGCCCACGCTGAATAATGCCGATTTCCTGGACAATTCGATGCAGGAGCTGGAACAGTGG
GTGCTCAACCAGCGGAACTTCCCGTTGCTGGCCGATCTGGCCTATGAGGAAACCAAGTACATGCTGTGGAAGAGCTGCCTCAGCACCAATCTCTT
CGAGCAGCAAACAGCGGTGAGATTACTGCTGGTGGTCTCATCCCAGCACCCGAATATTTACTACCAAACTATATCCCAACTTCTAAAGAAGTCGT
ATGCTCAAAATCCCAATGGCATTGGCGCATTAATTCGCTTACTTGGCGGACAAAGCGGCATGGTTAACTTTCCGGGATTCACGCCAGGTTTCAAG
ATGGTCTTGGAGGACATCACGTTGGATGTTCAAGTTAACAATCGATTGCCAGTTCCGCCGGGCACACCCACAGAAGCCTTTAACACTTTCTCCAA
CCTAAACATACTTGCCAGGATGCACAAGAGCAAGAATGTGGCTCCGTACATCAAAGCGCAGCATTTGAACCAAGCCCTCAACGAATGTCTTCCCA
AAATCCTTCAAATCTTCGACTGCACCGTTAACAAACTGGTCCTGAGGATAGACAGGGATGCCGCCGAGCGGATAGCGGATAAATTCCGGGCGCAG
CAAAGTAAAAATAGCAATAACAACAATGAATTGTGCAATGGCAAGGATTACGGAAAGCGCACAAAATTGGAGCCGGGAGAAGATAAGGTGGATGA
TGAGGACGCTACCCGCATGCGCTTGGCCCATCTCATTGTGGATCTGTTGAACAACATTGAAGCCGGCAGCCGGACAACTGTCCTGCGCACTCCAT
TAGTCCTCAAGCTGGCCACGCTAAGCGTAAAGTACTTCTTTGTGGGCTTAACCGAGAAGACTGTGATCCGTCGAGCAGCGGCTTCGCATCGCTCC
TACACGCTGTTGCAGAGGCAGTGTTCCGCCCGGAAAATCGCGAGAACCGTCTGCCTGCGCGAGCTGGTGGAGCGCGCGCTCTTTTATCACGGTCA
CTTGCTTGGTCAGCTGGAGGTGTATCAGCTCGATGAGCTTGAGATACCCGAGCACGAACACCTCATCCTGCAGAATCTGCACACCAGCTCTGGCG
CCAACTCGAATCGCTCCGTGCTGCATTCCGGTATTATAGGCAGAGGTCTGCGACCAGTGCTGCCCCCCAGCGAGCGGAACTGCGATGCGGAGAAG
CAGGCGCTGTATCTTAAGGCATTGAATGCATGCTGCGCCGATCTGGAGAAGCCCAACAACGTGGAGGGCTACTCGCTGGTCTCGCTGCTGCTGGT
CGAGCTGGTCTCCACGGATGTCATGTACAACGGCCTGCCCTTTCCGGATGAGGAGTTCACCAGGGTCACAATGGAGCGGGACATGCTAATCAGGA
GAGCGTTCATCAACTCCCCAGTGCTGTGGGCTGTTTTGGGACTGATCGCCGGTCATAGGCCGGCGCTTTGCTATTCCTCCGTGCTACTGCGCGCA
CTGTGCGCCACCTGCTTGCATCACTGGCGGGGCAAGAATGTCAATCGATTCCAGCCCACTGCTGCGAACGATGAGCTGATGCTGTGCACCAAGAA
GATGCTGCAACTGCTGGCTATGAGCCAACTAATTCCACCTCCACTCACCAATCTGCATCTCATCATCGAGCACTTTGAATCGGCAGAGATTGCCC
TGCTGCTGCGCGAGTGCATCTGGAACTATCTTAAAGATCACGTGCCCTCGCCGGCGCTGTTTCACGTGGACAACAACGGGCTGCACTGGCGCAAC
ACGAATACACAGCTGGCCAAGGTGCCGCCGCAATATGTGGACCCGTTGCGCCACCTAATGCAGCGTAAGCTGTCCACCCTGGGCCCCCACTACCA
TCAGATGTTCATCATGGGCGAGCTGATGGAGGGCGACTCAGAGCCAGATCCGACGGCCCGGCTGCAGATCGTTGAAATAGATTAAGCAAACGTAG
TTAGCTAGCCTAATGTTGTAGTGTGAGCATGAGCGTGTGTGCATGGAATAATGGAGCGTCTGCGAGTGTTGAGTGTGGAATTTGGAATGTGCGAA
ATGTGCGAACTAAATGCAGTGTTTGTATTTTGATATTCAATGGGTTCTTTTATTTTCGTTTCATTGGTTTGTAAAAATTAAAATCTCAACCTAGG
CCTTGCAAATACTGTCCAGCAGTTATTGTACCGACGGCGCCTGAAAATCGCATCATTCGTCGTGTGTAGTTTAGAATATAACGAAGCCAAC
(SEQ ID NO: 1493)

Start ATG: 236 (Reverse strand: CAT)

MADPKTGMPVSQVKLAGNRQQQQRAPEYEAFNLVKTALQSLVWKGPPAWSPLIANWSLELVAKLSDKYTQRRMTITASCNYWLECSAMHGLMTLI
NSCFRKLTQPEEEACVEIMLNAFHRFPMTFDWIVARLGGCFPYKIIMQILQCGIKRFVDDYRCHLDSEAGILDYMTSCHEQHLRAAFREMLREGF
APKKPLDVAVVPFLLITTNYSDTILQSLVNVLVEIYTEDMCEVIVQKAPLWLSNKMFAGMQPTLNNADFLDNSMQELEQWVLNQRNFPLLADLAY
EETKYMLWKSCLSTNLFEQQTAVRLLLVVSSQHPNIYYQTISQLLKKSYAQNPNGIGALIRLLGGQSGMVNFPGFTPGFKMVLEDITLDVQVNNR
LPVPPGTPTEAFNTFSNLNILARMHKSKNVAPYIKAQHLNQALNECLPKILQIFDCTVNKLVLRIDRDAAERIADKFRAQQSKNSNNNNELCNGK
DYGKRTKLEPGEDKVDDEDATRMRLAHLIVDLLNNIEAGSRTTVLRTPLVLKLATLSVKYFFVGLTEKTVIRRAAASHRSYTLLQRQCSARKIAR
TVCLRELVERALFYHGHLLGQLEVYQLDELEIPEHEHLILQNLHTSSGANSNRSVLHSGIIGRGLRPVLPPSERNCDAEKQALYLKALNACCADL
EKPNNVEGYSLVSLLLVELVSTDVMYNGLPFPDEEFTRVTMERDMLIRRAFINSPVLWAVLGLIAGHRPALCYSSVLLRALCATCLHHWRGKNVN
RFQPTAANDELMLCTKKMLQLLAMSQLIPPPLTNLHLIIEHFESAEIALLLRECIWNYLKDHVPSPALFHVDNNGLHWRNTNTQLAKVPPQYVDP
LRHLMQRKLSTLGPHYHQMFIMGELMEGDSEPDPTARLQIVEID*
(SEQ ID NO: 1494)

Celera Sequence No. : 142000013384600
CTGGCTAAGATATTTTTATGGTCCCTAGCGCTACACACTCAGAAATGCACTCTTAAAAAGAAAAGCACTCTATATGTATATATATATACAAATGT
ATATATGAGATCCAATTACTCACCTTGTTTGAATTGAAAATCGGCTAATCCACAAATAGTTGGCTGGTACAGTGGAAATCCTTCGGAACTCCCGT
TCGACTCCGATATATGTACCTAGTGAGCTTGGGTCGCGTTTGAAGACTGAAAATACAAAGCTGCTTGTCAAATCGTTTTATAGCCGCCCCTTTTA
TGCACTGCGTGCATTGCACATATGTATTGTACGACAAAGTTATAGTTATCAAGATATATACATAGGTCGGTCGGAATAGTCGGGCACTCGTAAGG
CCAGCGCGACTTAATAGGTCATTATAAGCGACCGATTCGAGTTAAGAGCTCTAAAGATCACGTCGCGAATCGCCGCATGGGATCTTCTTTTTTTT
TTTTGGCTTGTTTTGCATAAGTTCACCTGAAAATGGTTCACTGAGCTCAGCATTAATTTTATGTTATTTCCATTGTTTTTAGTACGTTAAAGTGC
CAAGACAAGTGCGGTATTTCTCACGGTGCAGCGCACTCAATCGATTTTCCACAGCAATTAACATTATTAAATATAATGTTGCAGAAGGTACACTG
AAAGTAAGTGAGTACTACAAAATTCAAGAACTTTCTTCACTTTGTGTGCACTTTTAGAAATGTTCTTGACTTAAAACAATATAGTTATTATTATT
ATTATTGAAAAAATCCGTACTTTCTATCAGGAAATCCACTTTGCTATATTTTGTAACTATATACACTTTGTAACTTGTACTGTTTAGCACTTTCG
AGAAATTCTCATCTGCCACTTGCGAAAAGTCCACTTCCTATATTTGTTCTAGAATGTAAACGAAGGAATATTTTCATTTCTCGTCGCAAAATACG
AAATTTTTAAGTTAGCTATATAGCATCGGGGCACTTTCGCAATCGCGGCACAGCTTTATATATGTATATATATTTATATTAAGTGCGTGTTCTGA
GCGTTTCGCACAGTGTATCGTGGTTAATCTTCTGATGGTTACGCGACTTGGATGCAATTAGACTTGAACTTTTGAACGCTCCGTACACGAGTAGT
TTAAAGACTAATCGCCTTCGCCACTGTGACTGAGTGAAAAACGAGTTTGTAATCCCTCTTACGGATCGTAAGTGTGTAAGTTATTGCTTTGGCTA
TCACTCCTCCCGTTCGACACAACAGTAACTTTCTGCTTTTCTGCCGGACACTAGCTAATGTACCTTCTTTCGACTGGCGTGTCCGCGTTCCACGA
TCAAGTGATCAACTGACTGACGGGGGCTGTGGGTAATTCGAGCTCATTTGCTTTTAGTTTCAAGCACGAGCAATTAATTAAGTATTTCACTGCTC
GCCGTTTCCAAATGTATTTCCATGCCATTTCTTGCGCTTGCCTGAGCCCATTCTGCGTGTCGGACCGCCATTCCGCCATTTAGCCATTCGGTCAT
TCCGTCCTCCAGTCAGACGATCACCTTCGAGCACGGAGCTACGTCAGCCTTTAAAGTCCGGCGGAATTTCGTTGGGCAGCCAAGTGCAATTAGCT AAGTCGAAGTACAGAACGCTGAAAGTTAAAAGTAACCCACTGATGGCATTAATCAATTTACGAACACGCAATCCCAGCGACAGCTGTTGATACGC
ACAGCGCGCTTCACATGGACATACAGACAGACAGACGGACAGACACTCCATTATCTATTAGGTATTTACATGCATTTAATTTGAATGTCAAATTC
AGATTTATGGCCTAGCCTATGAGAGTTACAAACAATGAGAGTCGATTACATATGAATTTACACCTATTTCTAGTTCTACGTATGCATATCGATTC
AATTCATCCATTCATTCCGTTGTATTGTCGAGTATAAAACGTACATTTGACTAATCATATAGAGATATTGTGCAGACAATTGTTGCTAGATATTG
CTTACGATGAACTACAAAAGCGTTCTCGCCTGTTTTATACGTTTAAAGCTTAGACTACGTACAAAAGGTTTGGGTTAGTAATATGTCAACGATAT
TCAATGCTAAAGTCTTAGGTAGCGCTTAAGTGTACGGATGAGTTACTCTTAAGTACAGATCAAATCTATGCGAAGGAGAATTACGTATTTACAAT
ACAATTGTCGGAGACTCCTGGTTAGATCACTGGAGTCGGCCGAATCCTCGCTCTGCGACTCCGTCGCCTCCTCTGCAATCATTTGGGCCGAATCT
TCTCGTACATGAATTTCTGCACGTGCTTGTTGTCCGGCTGCATGAGCTTCTTCTTGTTGAACTCGAATTGGGCCAGCGCGAAATCGTACAGATCG
TTTTCCATTTGCCAGATTTTTGTCTTTTGAATGGATTTAATTGTCGATTCGCTGGGCGGAAGCTTGGAAGATGTCACCCGCAGATGAGATTTGTT
TGAATTATGATAGTGCTCACGAAAGCCGTGAAAAATTCTGCAAAAGAAAAAAAAAGAACAGGTCAATGAAGCAACTGGAGTATTCTAAAACAGAC
AATAACATATGGTTGGGAGGCACACCTTGGAAGGGATCTCTCGAGCAGATCCACAAACTCGTACATCTGCTCTGTGACTCCGACTAGGAAGTATT
CGTTGACTAGATTGCGCTTGGCCTGGTCCAAGGCCCAACTGCTGCCGGGTTCCCAGCACTCGGCTGCATGGCCACAGAAGAAGGGTATCTGCAGC
CACATGTTTTTGGGATCACAGTCGGGTTGTTTCTGCACCACGCACTCATCGAAGGTCTGCAAAGATGTGTGAGGGCTTTGGTTACAGGGAGGTTA
ATACCTTGATGCTCTACCTACAATTTTATTGCCCGCCTTCTTGCGGACTAAATTCGGTCGGTAGTTGTCGCCAAAGCGTAGAAAGTAATAGTAGG
AGACAAGTCTGTCGAGCGGTTTGCGCACCAAATTGATGTAGATGGGCTTGTGGGCGATTTGGAATCTGCAAAGGAGTAATGCAATTGAGACGGGC
TCTGCTGGATTGGCTAGATGTTACCTACTTTGAGAAGTCTAGGAAGGCCATGTGGCCGTGATAAAGAGCTGGCTTCATCTCGTGCCACCTGGAAA
CATTGCGCACGAATTGGATTTGATTGGGAAGCGAGAGGACGTGCATGTTGGCAGTGACATTGATGTGCAGCACATGGAATTTATTGGGCTTGCAC
AGATCGTATGCTATGTTAACAAAGCTGGTGGATCCCGTTTTCGGTACGCGATTGTAAAGCACCACTAGGTGCTCCTCGAAGTCAAAGTCATCGGT
GGTGGACGAGGCATGCTGATCTGGGCTCAGAGAATCGCCCAGCTTGGAAAGCGGCTTGAAGGCTGCACAAAGTAGGTAATGGGTGTAAAAGTGAT
ATGGTTTTGCCTAACTACCGGACTCCACTTACCATGTTCCAGGCGAATCTCTGACCAAAGCAACCAGTAACCTGCACAGGTGACCGCGCACAGGG
CTATCAGGATCAGCCAGTGGGTGGGTCGGAGCAGAATCCACATCTTAAGCAGTTTCCTAAACATGCCTCGTGTCGGTTTGCCCTACAGGTCAGCA
CGGTAGCTCATATCAGCGTATTTATTTCAGCATAATCTCAGGTCGTTGTTTTCCTTGTTTTTTTTCTGCAACCAACATCGAGCAGTGTTGGTCAG
CAGCTGCTGGACAGTGCTGCAAGGCACTGAAATCTGGTGAATCTGTGGGAATGTGCAGCTGTAGCTGAGATGACTAAATTAGTGATGGAAAATAG
CTCAAAATGCTAGCTCGGATAATTGCATTTAATTTCCAGCTAGGAATCCGTAAATTAATTGCCTTATATTTATAACTTCAATAAATATGTTTTTC
CTAAAACACAACACAGAATATTTTAGGCCAGTCACAACCAGATCTGCATCACCCTTCAGCAACCCTTTTGCCTTGAGCATCACTGTTTTTATTAG
TGTGACCACCCTTGCCGGCAAATAATACCAAGCAATGCCAAAATTCTAGCGCCCATTTTTGCGAGGTTAAAATAAATTTCGCAAGCCGGCTGCAA
TCGCAAAGTACAGTGCGACTTATATACACTCGTATAAAATAATTCCATTTAAAAGCAAGCATGTCCACCTTTAACTTCGCCAGCATGGCCGCCCA
ACTGGGCCAGGAGCAGGGAATATCATTCGAGAACAAGGTGCTTTCCTGGAACACAGCTGCCGATGGTAAGTTTGGGTGACGCTTTGGGTACTCCA
TGCAGTGGCTATATTGAGGCTTTTTACAGTCCAGGATGTGGTGGATGCCCTTAACAAACAGACCACCGTGCACTATCTGAATCTGGACGGGAACA
CACTGGGCGTTGAGGCCGCCAAGGCGATTGGTGAGGGTCTGAAGCGTCATCCAGAGTTTCGGAAGGCGCTGTGGAAGAACATGTTTACTGGTCGT
CTCATATCGGAGATTCCGGAGGCACTCAAGCACCTGGGAGCCGCGCTAATTGTCGCGGGCGCCAAACTGACAGTCCTGGATCTCAGCGACAATGC
CTTAGGACCGAATGGCATGCGAGGCTTAGAGGAGTTACTGCGATCCCCGGTCTGCTACTCGCTGCAGGAGCTGCTGCTGTGCAATTGTGGCCTTG
GTCCCGAGGGCGGTAGTATGCTGTCCCGGGCTCTGATCGATCTGCATGCCAATGCCAACAAGGCGGGCTTCCCGCTCCAGCTGCGTGTGTTCATA
GGTTCGCGCAATCGTCTCGAGGATGCCGGTGCTACGGAAATGGCAACCGCATTCCAAACCCTCAAGACCTTCGAGGAGATTGTTCTGGAGCAAAA
CTCCATTTACATCGAAGGCGTCGAGGCCCTTGCCGAATCCTTCAAGCATAATCCTCATCTACGAGTGCTAAACATGAACGACAATACTCTAAAGT
CCGAGGGAGCTGAAAAAATAGCTGAGGCTCTTCCCTTCTTGCCACTGTGAGTCGGTTATAAAGTTTTTGATGAGGGAGAGTGAGTGAGTGTTATG
TGATATCTTTTTGCTTTGCAGGCTGCGTGAAATGAGCTTTGGAGACTGCCTGATCAAAACTAATGGCGCCTACCACTTCGGTGAGGCTCTGGAGA
GAGGAAACGAACGACTGGAAGTTATCGACTTAGGTTTTAACGAAATCAACAGCGACGGCGGCTTGGTGTTGGTGAATGCTATGGGAAACAAGCCC
AAGCTACGCATCTTGAATCTAGATGGCAATAGCTTTGGAGAAGAAGGCAGCGAGAAGATAATCAGCGAGATGAGTAAGTTGCCAACTGCTGCCGC
ACTGCAACCGTTTCAGCACCAGGAAGAGGAGGATTTGGAAGATGAATACCAGGCTGACAAGCAGGACGCAGATTACGAAGAGGAAGAGGAAGTAC
ACGAGCACGCCAACGATACTACCGAAGAAGCAGATGAGGATAGCGAGGGCGACGAGGACGACGAGGAAGACGAGGGAGACGAGGAGTACAGCAAC
GTCGCGGAGGAGACTGCCTATGTCACTACGAATGCCTACACGACCAAGGTTAGTTTATACTTCGGAGTACTGTGCAAATGGTAACAGCAATTAAT
CGAATTATCTTTAATTTTAAATTTTCACAGCTTTTTAACGACACAACCAACTCGATGGCCAGCGAAACTTTTGCGGTCGCGAACAAGACGATCAG
CCAAAAATGCACTCCAGAGAAGTTCTGTTTGAGCCAGAAACCCTGCTCCCAGGAAGATTTCGATTCGCTAGATATGGATAACAAACTTGAGGCTT
TGCAGTCGATTGTCAACGTAAGATATTCTCAATAATTAGAATGCAATTAGAGTAACGTAACATTTTTGTACAGCAATTCACCGGCGACAACCATT
TGCTACTGCTCGTCTTCACCACCTTGAAGTGCGCGCATTTGTCGCAATCCTCGAAAGCTGCGTTGGATCTGGCCGTCTCCTTGTACCAGGCCACC
TTTGACTATGCCATCAAGACAAAGCAGGAGACACGTGTACTCAACTATGTACTGATGCAGCTCCGTTTGTTGCCCTGCAAGGAGGTATTCCATTC
GGACTACGATGTCAAGAACTGTCGATTTGCTCTTCGCGAGGCTCTCAAGCAACCAACGTTTGCCAACGACAACATTAAGAATTCCTTTAAGACTT
TCCTGGAGGGTGCGGAGTCGTAAAGAGAATTAGAGAAGAGATTACCTTTATTTCCCACTTTCCGATTTGTGTAGCTTTCGCGAATAAAAACGTAT
TATTCCTAACCCGTAGTGGTGTTTTTTTTTTACCCAAAAAACCAATCGAAATTTAATGTATTAGCCATTCGGCAAAAGTGATTTATTTACATGAA
GAAAACTCGTATGAGACTACAAACTATCTTTATGGAACATGTTAATACATCGATATTACGTTTGTAAATTCCTCTTGGTGGCTTTCTTGCTGCTC
TGGAACAGAATCAGCTACAGTGAACGAATGTAGCGAAGTGTTTATCTATAGTTAATAAAAACACGAATTATAAAACATTGACGTTAACATCGAGG
AGAACATTGAAAGATTATAAAATAACGAACGATCGTGGCGAGCAAGTCCGCAAAAAAAAGTGCCTCCTCGAGATTCTCGATGCGGATAATGCTGA
TTCTAAGAGTCCATCTTCTATCAATATCCTGTGTGGAAATGTGTTCCTTAACAATTAAAATCAGAATCATCATCATCATCTTCATCAATCTCGAT
ATCATCATCATCGCTTTCAATTACAGCTCGCCTCTTCTTGGGCGGAGCTTTCTTTTTGGCTCCTCCACTGCTCTCATCCTCTCGTCCACGCTTAG
CTGGACGCTTGGGCGAATCATCATCGCTGGCATTGCCATCATCATCAGAGCCAACGTTGCCACCGTCTTCCTCCTCATCCGAGAAGAGCGAGCTG
TAGTCTATCTTCTTACTGGCCTGTCGACGTCCAGGACGCTCTGCACGAGGAGTTACTTCCTCCACGTCATCGTCGCTCTTTTTCGCCTAAAGATG
AAAAATATTAATTGACAATTAAATACAGATTTGGGTTTAAAAACAAATATGGGCAATTACTGAAACACTTACCTTGGCCTTGCTGAAGTCAATCT
TGCTCTGCTTGAGCCCGCCGCCGTTCTCCTTCTTTTGGCGCGGCTTTTTTTCTCCCGGCTCCTTCTTGACAACCGCCTTCTTGGCCTTGGGTGAG
GTCTTAGAGCCGCCCTCGACCATTGCATCAAATTCGTCCACCTCATCGCCGCTGGCA
(SEQ ID NO: 1495)

Exon: 1001..1215
Exon: 3912..4245
Exon: 4305..4986
Exon: 5057..5558
Exon: 5636..5812
Exon: 5869..6277
Start ATG: 4146

Transcript No. : CT28175

FIGURE SHEET 814

CAGCTTTATATATGTATATATATTTATATTAAGTGCGTGTTCTGAGCGTTTCGCACAGTGTATCGTGGTTAATCTTCTGATGGTTACGCGACTTG
GATGCAATTAGACTTGAACTTTTGAACGCTCCGTACACGAGTAGTTTAAAGACTAATCGCCTTCGCCACTGTGACTGAGTGAAAAACGAGTTTGT
AATCCCTCTTACGGATCGTAAGTGTAATATTTTAGGCCAGTCACAACCAGATCTGCATCACCCTTCAGCAACCCTTTTGCCTTGAGCATCACTGT
TTTTATTAGTGTGACCACCCTTGCCGGCAAATAATACCAAGCAATGCCAAAATTCTAGCGCCCATTTTTGCGAGGTTAAAATAAATTTCGCAAGC
CGGCTGCAATCGCAAAGTACAGTGCGACTTATATACACTCGTATAAAATAATTCCATTTAAAAGCAAGCATGTCCACCTTTAACTTCGCCAGCAT
GGCCGCCCAACTGGGCCAGGAGCAGGGAATATCATTCGAGAACAAGGTGCTTTCCTGGAACACAGCTGCCGATGTCCAGGATGTGGTGGATGCCC
TTAACAAACAGACCACCGTGCACTATCTGAATCTGGACGGGAACACACTGGGCGTTGAGGCCGCCAAGGCGATTGGTGAGGGTCTGAAGCGTCAT
CCAGAGTTTCGGAAGGCGCTGTGGAAGAACATGTTTACTGGTCGTCTCATATCGGAGATTCCGGAGGCACTCAAGCACCTGGGAGCCGCGCTAAT
TGTCGCGGGCGCCAAACTGACAGTCCTGGATCTCAGCGACAATGCCTTAGGACCGAATGGCATGCGAGGCTTAGAGGAGTTACTGCGATCCCCGG
TCTGCTACTCGCTGCAGGAGCTGCTGCTGTGCAATTGTGGCCTTGGTCCCGAGGGCGGTAGTATGCTGTCCCGGGCTCTGATCGATCTGCATGCC
AATGCCAACAAGGCGGGCTTCCCGCTCCAGCTGCGTGTGTTCATAGGTTCGCGCAATCGTCTCGAGGATGCCGGTGCTACGGAAATGGCAACCGC
ATTCCAAACCCTCAAGACCTTCGAGGAGATTGTTCTGGAGCAAAACTCCATTTACATCGAAGGCGTCGAGGCCCTTGCCGAATCCTTCAAGCATA
ATCCTCATCTACGAGTGCTAAACATGAACGACAATACTCTAAAGTCCGAGGGAGCTGAAAAAATAGCTGAGGCTCTTCCCTTCTTGCCACTGCTG
CGTGAAATGAGCTTTGGAGACTGCCTGATCAAAACTAATGGCGCCTACCACTTCGGTGAGGCTCTGGAGAGAGGAAACGAACGACTGGAAGTTAT
CGACTTAGGTTTTAACGAAATCAACAGCGACGGCGGCTTGGTGTTGGTGAATGCTATGGGAAACAAGCCCAAGCTACGCATCTTGAATCTAGATG
GCAATAGCTTTGGAGAAGAAGGCAGCGAGAAGATAATCAGCGAGATGAGTAAGTTGCCAACTGCTGCCGCACTGCAACCGTTTCAGCACCAGGAA
GAGGAGGATTTGGAAGATGAATACCAGGCTGACAAGCAGGACGCAGATTACGAAGAGGAAGAGGAAGTACACGAGCACGCCAACGATACTACCGA
AGAAGCAGATGAGGATAGCGAGGGCGACGAGGACGACGAGGAAGACGAGGGAGACGAGGAGTACAGCAACGTCGCGGAGGAGACTGCCTATGTCA
CTACGAATGCCTACACGACCAAGCTTTTTAACGACACAACCAACTCGATGGCCAGCGAAACTTTTGCGGTCGCGAACAAGACGATCAGCCAAAAA
TGCACTCCAGAGAAGTTCTGTTTGAGCCAGAAACCCTGCTCCCAGGAAGATTTCGATTCGCTAGATATGGATAACAAACTTGAGGCTTTGCAGTC
GATTGTCAACCAATTCACCGGCGACAACCATTTGCTACTGCTCGTCTTCACCACCTTGAAGTGCGCGCATTTGTCGCAATCCTCGAAAGCTGCGT
TGGATCTGGCCGTCTCCTTGTACCAGGCCACCTTTGACTATGCCATCAAGACAAAGCAGGAGACACGTGTACTCAACTATGTACTGATGCAGCTC
CGTTTGTTGCCCTGCAAGGAGGTATTCCATTCGGACTACGATGTCAAGAACTGTCGATTTGCTCTTCGCGAGGCTCTCAAGCAACCAACGTTTGC
CAACGACAACATTAAGAATTCCTTTAAGACTTTCCTGGAGGGTGCGGAGTCGTAAAGAGAATTAGAGAAGAGATTACCTTTATTTCCCACTTTCC
GATTTGTGTAGCTTTCGCGAATAAAAACGTATTATTCCT
(SEQ ID NO: 1496)

Start ATG: 450

MSTFNFASMAAQLGQEQGISFENKVLSWNTAADVQDVVDALNKQTTVHYLNLDGNTLGVEAAKAIGEGLKRHPEFRKALWKNMFTGRLISEIPEA
LKHLGAALIVAGAKLTVLDLSDNALGPNGMRGLEELLRSPVCYSLQELLLCNCGLGPEGGSMLSRALIDLHANANKAGFPLQLRVFIGSRNRLED
AGATEMATAFQTLKTFEEIVLEQNSIYIEGVEALAESFKHNPHLRVLNMNDNTLKSEGAEKIAEALPFLPLLREMSFGDCLIKTNGAYHFGEALE
RGNERLEVIDLGFNEINSDGGLVLVNAMGNKPKLRILNLDGNSFGEEGSEKIISEMSKLPTAAALQPFQHQEEEDLEDEYQADKQDADYEEEEEV
HEHANDTTEEADEDSEGDEDDEEDEGDEEYSNVAEETAYVTTNAYTTKLFNDTTNSMASETFAVANKTISQKCTPEKFCLSQKPCSQEDFDSLDM
DNKLEALQSIVNQFTGDNHLLLLVFTTLKCAHLSQSSKAALDLAVSLYQATFDYAIKTKQETRVLNYVLMQLRLLPCKEVFHSDYDVKNCRFALR
EALKQPTFANDNIKNSFKTFLEGAES*
(SEQ ID NO: 1497)

Name: RAN-GTPASE ACTIVATING PROTEIN
Classification: signal_transduction
Gene Symbol: Sd
FlyBase ID: FBgn0003346

Celera Sequence No. : 142000013384249
TTGGATATTTCCGTTTCCTGGCTGTGCATTCTCCTTGTCGTCCGCTTGCATTCCTTTCTCCAGCGCCATTAAGGTGCTGTTTCCGAAGTTGAACG
ACTGCGAGAATGCCATTGCGCCGGTGCGTTTTTATACTGAACTAAGAATTGTTGCAAACTGCTTGTTACAAGTGAAATGAATAAAATGAAAACGA
AACGTCGCGCGGTCAATGTGGCCGTCTTATGATTAGTTTCAAATATACTATTCATGTTTGTGACACTTTGAATGAACTGTTTACACCGCCAGCGG
TCCCACTGAAACCTTGTTCACACTGCACGCGACTTTCTTACAAAATATCTTAATTAAACAGATTTTATTTATACCGTTACTTTCCGAATTCCATA
TGCGTGCTATGGGGCATTTAGCACAAAGCTAAGGTCCCACTAAAACCTTGTTCACACTGCACGCGCCTTTCTTACAAAATATCTTAATTAGACAG
ATTTTATTTATACCGTTACTTTCCGAATTCCATATGCGTGCTATAGGGCATTTAGCACAAAGCTAAGGTCCCACTAAAACCTTGTTCACACTGCA
CGCGCCTTTCTTACAAAATATCTTAATTAGACAGATTTTATTTATACCGTTACTTTCCGAATTCCATATGCGTGCTATAGGGCATTTAGCACAAA
GCTAAGGTCCCACTAAAACCTTGTTCACACTGCACGCGCCTTTCTTACAAAATATCTTGATTAGACTGATTTCATTTATACCTTTACTTTCTTGC
TAAGTGTAAGCTAAGTGTAGTTAAGTGTAAGCCTGAAATCCAAGCCCAAGACCAAAACTGAAAGCAAAAGACCCACAGCAAAAACTCAAAAAACT
CCACGACGCAACAAACTCGCGTTCGAATCGCAAGCAAGCTGCGCTGAAATCGCTAACAAGCCAACCAAAAGCCGCACGAAAGTTGCGCCCAAGCC
GCAATGAATTTAACGCTGACTTTATGAACTTTAAAAGAAACCTTTGGCTTATTTTTGTTTATTTCTTTATTTGTATATATCCTTAGAATAGTTTG
TGTTGTTCAAGATTACATAAAATTTGTTTACATATCTATTAGATCAATATCCCATTTACATAGTTAGCATTATACAAAATCGCGCGCCGCAAGCT
GATGACATTCCATTTTAGTTGGTTTTTTTTATAATATGGTTGTTGGTGGATAGTGTGTGGTTGTGGTTAATTAGCCGCGATACAAATTTGGATA
TTATGCTAGACGACAAATGTGCGACATTATAAAATAAATAACATGGTTACTGCTCGCCGCCCTTGCCGGATATCTTTTGATGGCCACTCCTTTTG
GTTTCTGGGGTTAGGCGGAATGGATCCTCATCATCTGGCCATCATCTACATCTTATAGGTGGCGGGCACGGATCGGGGATAGTCCAGATCGTACA
TCTGGGCCTTGATGAACGCCAGCTTATTGACCGGCTCTGGACGAACAGTGGCCAATCCGTTTTTGTAGGCGTACTCCACAATCCTTTCGGCAATG
GCCATCGAACAGCTGACAATGGAGCTGAGTGGTGGATACAAGCTGCCCTTGGCCAGGTCGTCCTTGGAGACCAGCTCCGCCAAGCGCTCGGCGGC
GACCAAGAATACCTGCTCGGGAATGTTCAGCATGCCGGCACACAGAACACCCAGTGCCACGCCAGGGAAAATGTACGAGTTGTTGCCCTGACCCG
GATAGAACTTCTTGTTGTTGTACGTCACAGGAGCAAAAGGCGAACCGCTGGCGAAGATGCAGCGCCCCTTGGTGTACGTATACGCCTCCTCGGCG
GTGCACTCCGCCTTGCTGGTCGGATTGGACAGTGCAAAGATGATCGGCGTCTCATTAATATCGGCCATCAGCTCAAGGATCTCCTGGTTGAAGGC
GCCGCCCTGCGCAGCCGCTCCAATCAGGACATTGGGACGCACCTTTCGCACCGCCTCTGCCAAAGTATCGATGGGTTCGTGCAGCTGGGCAAAGT
GCAGCTTGTGTTCGGTGAGTCCGCCCTTTGGACGATCGCGGGTGATGACACCACGGCTACATAGAAAGCATCTATAAGTATCAGGATGTATTTTG
ATTATATATCGACCTACCTATCCACCATCCAGATGCGGGCCTTGGCCTCCTCCTCGGTGAGACCCTCCACCTTCATGGCCATCAGGCACAGGTTG
GCAATACCAAGAGCCGCTTCTCCGGCGCCCAGGAACAACAGCGTGTTATCCTTCAGCTGGGTCTTCTTGATCTTTAGCGAGGCCAGCAGACCAGC
CACGGCCACCGACGCGGTTCCTTGAATATCGTCGTTGAAGGTGCAGAAGGAGTCGCGGTATTTGGACAACAGCCTGAAGGCATTGGCGTTGGCAA
AGTCCTCGAACTGGATTAGGCAGTTTTGACCAAAGCGACGAACGCAGGCATGCATGAACTCATCGATGAACTCATCGTACAGATCTCCAGTGGCC CTGCGTTCGCGCAGACCGATGTACAGGGGATCCTCCAGGATGGATTCGGTATTGGTGCCCACATCCAAGGTGATGGGCAGGCACTGCGATGGCTT
AATGCCCGCCAAGGCCGTATACAGGGACAGTTTGCCCACGGGTATACCCATTCCGTTGGCGCCCAGATCTCCCAGTCCCAGGATGCGCTCGCCGT
CCGTGACAACGATGGCACGCACATCCGTTTCCGGCCAGTTCTTTAGCACGTCGTAGATGTGTCCCTTGTCCTTGATGGATATGAACATGCCCTTG
GCGTTCTGGTGGATCAAACTGTAGCGCTGGCAGGCCAATCCCACGGTGGGCGTGTACACCAGTGGCATCATGTAGGCGATGTCTGAGCTGAGCAC
GTTGTAGAACAGACGCTCGTTCCGCTCCGATAGGCTGATCAGGTACATGTACTTGTCCAGATCCTGATCCAGTCGCGCCAGCAGAGCGCGGCAGT
GCTCCACCTGCTCACTGGGCTCACGGACCACATAGGGCAGCATGCCATGGATGCCCAACTGCTGGCGCTCCTCGTGTGTGAAGGCCAGGCCCTGA
AATTGAAAGGGATATGCATTTTAGTTACCAATACCTACTATTAATATCTGTAGGATTCGTAATAGGATGGCATGATCGCCTCATTGAATGATTAT
AGAATCTCCTCTCAAATCAAAACAAACAAAATGTAGGATGGTGGAAAAGTTTGACCCGCTTATCATGGACTTGAATTCCCAGGCACGCGCCCCTA
TTCATATAGAGTATTCCACGGCTACTAGCCACCGAGACAGAGGCAGTTATTACCGATGCTTCGCAGATCCGAGGAGATAGATCCCTCGACTTCAC
GAGTCGGGCATCAAGTTCAAAGTCGTTTCTAGCGCCCAGTCGCTTGAAAACATATTTGCAATCGCAGCTTTAATTAAAACACATTTTTTTTCGA
GGGGGAAGTGAATCAGCGCTGGCCTCGATTCACACGCACAGCTAATATGTTTAGTACGAGATTTTGAAAGTTTTTGCTCCGTAATTGCTGCGGTT
ATTATCGAAATGGACAAAGCAGGCGGGGATTATGTTGGGGGCGTTGCTGCCGACATTAAATAAAAAAATACGTGCAAGTTGGCATTCAAATAGAA
ATCACGCTGGATTATGTGGTTTTTGTTTTTAAACTACGGATGTACCTGCTAATATGCACATTAGGGAATAATTACTCGTGCTTTGGGTTACTTTT
CCGAGTGGCTGCTGTTTTCAAATCGTGCTCATTACAAAGGTTTTCTTAATGAGTCTATTTTAAGCTTCTTGGGACATTTGATTTAGCTTAATAAT
AAATGCACATTTTTATTTCCAAGCGATATATCAAAATGCAACCAATTCCAAATCTGTTGTGTAAGTTTTCCGAATTATTTTTGTAAATTGAATAT
TTTGTTAGTATGTCAAATTAAGTTATTATTGGAAATTATACTTGATAGGTTTTCTATCATTTATCATCATTTAAAATTAATCTCGTTTGTTTCGG
TCACGCAATAATAAATTTATAGTTTTTCATATGAATTTTTAGTTTTCCGATAAAAACAAACTATTCGTATTCTAGTTAATTGATTCGTAATTCGT
ATTCTAGTTAACGTTTTTGATGCCTATCACTATGAATAAGCAATATTTAAAATAATTTTGGTCAGCTTGCAAAATATCATATATCATATTAAGAG
CTGACACAGATAAATAATATTGTTGTGTTTTTAAGGAATTTTAGCTGGAAATCGAGCTGATTCCCCTTTTTTTTTTTAAGTTTGCGAAGTAAAAT
ACATATGTATTTACATACGCATCAAATTCAATTAGCTCTGAACTGGCTGTTTGGACAATAAACACTGAAGTGATCCCCATAAACAATTGTTTACT
GCCAGAATTGCCTCGAACTTAACCATTATCGTGTGGCTACGTCATCGGTGGGCTGGTGAAATACATCCATATGTACATACATACGTTAAAAAAAG
ATTGAGAGAACGACACCGTTGACATTGAAAGCGACACACGACCGTCGATAAGCGTGCGAAAGTGTTTTCGAACCGCCTGGCAACAAGTTCTCCCC
ATTCTCCAGCACATATATGTACATACATATATATATGATGGATTAATATTCATGTATTCATGCCCCCAGCAATTGCCTCCAAACTTGCCACATCA
TGCCTAAGTCATATGAACTAAACTATAGTTTCATCATCCTCATCACCTTTTCAAGTTCTGACTTTAGTTTGTATTATATTAGTAGTTATAGCAAA
TCATGTAAGATTGCTTATAAAGAGGGGGCACCAAAAATCGAATCCAGACATGCGTATACGTAATGTGCAACTCCGATATTACGCATACACATTTC
GCATGGTATTGCAAAAAGGCAAAACGAAACGAAAACTGACAAAAGTCGCAGCCACAAGCAAAACCAAACCAAAAAATCACAAAAATGAGCTGGTT
CATATTTTTTTTACACTGTCTGGCGCGACCAGTTCGATCATCATCATCGCAGCGGTGATCATCATTATAGCAATGGCTAATCATTAAGTCGACT
ATCAACGACCGTCTGTGTCTGAACTTTGAATACGGACTCGGATCGGATGACGAAAGCGTCGCTTTAATCAGCAACAGTTGAGCAGACACACAGAC
AACGGGCAATCTCAGCTGATTGTTTCCCTTCTGGCAAAGGTGAGCTGATGAAGGGTTTTTTTTTTCTGTACCAGCCTCCCTCCCAGCAGGTGAA
ACGCTGCTGCTCTTTTGTGGGTCATACGATGTGGAATGATGACACAGGATGAATGCGCCACTGAATCGGAGCATAATAGTTTATGATGCACACTG
CAAAAATGCGCGTAATCTTTGAGTAATTTAGGTTATCCAAAAGGAAAACATAAATTCCAACCTATATATGTAAGCTATTTCAAAGCATTTCAGCC
ATTAATTGCAATTGACAAGCACACTATTATATATTATTCTTTCTTTAGTTGCCCAATATAAGCAATCGATAAATCATTGGGTAAACAATGAAATA
ATCCAACTATTTCAACAAGTTTCGAGCTCGCCCCGCTCTTTCGGCACATTGACCGCCTGAATTTGTTTAAATTTTTAATTTCCTCAGAGCGCCAA
TAAATAACAACAAAGAGCAGGGGAATATAATTCTATTCGCCAACTGCATGTGGTGTGAGCAAACCACACAGATAAATATTTAATGTGTGTATATA
CATATATAGGGCTGATACCAAGTGTTTTTGTGGTGATTATCGTCATTCGGTTGTTTATTTCTGCGGTTCGAAACAGAGTTAAATTTATTGCTGAA
TGTAGGTCAGTTTTCGCGGACTGGCTTTAATTTTGTTTCTTATTTTTTTCATTGGAGATAGGCACTCGAAAACTTTCCATGGGTAAATCAAAACA
AAGCTCAGCTGTTCGGGGAAGGAGGTTGAGATAAACAAGAGTCACTTGTTGGCAGCGTGTAAGAAGTACATAATAACAATCTGTAGTAAACAAGT
GCCAGCCCCTACTCGATAAGGAAACCCAAGATAATTTCTCGCTAAATTGTTAAATTATTATTTTTAAGTCTTTTCGTCCGATTGTGCCGTGACGT
AAGCGGGAAAAAAATCCACTTGGTTGTCATGGGGAAACACCATTCTGGATGGCCCTCCATTATTCTCAGTGGAGCTTCTGTTTACAATGCCAAAT
GGTTGGCCCCTTTTGGTCAGTTTTTTTTTTTAGTAGCTACACGGGGGAAAATAATGTCTTTACTAGAAATTACGTAATTTCTTTAGATTCCTAGC
ATTTTAAATTGTAATATCCGTTCTAACCATTACCACCTTTACATTAAAACTCTGTTTTTTCAGTGCAACTGTTTTAAATAAACAAACGCAAAGCC
CATGCGCGCTCTCTCTTCTCTCTTTCAAAAATGCTCTCTAATTTTATATTTGTGAAACAATTCGTGCATTAGCTCATTCATGTCTGCGTGGGAA
AAAAGCGTAGAAGCCAATGCAAGCTGAAAAACTGCACAAGCATTGAACTTGAAAATGCAATCTGAGATAAATTTGTAAACGAAATCTGCGTGACC
GATTCGTGTCAACTATTTCATACCGTACAATTTCGGCATGTGCCACAGACAGCTAATTGCCTCAATTATAAAAGTTGGTCTATCGATTTTCTTCG
GCTAAGGCACCAGAAAAAAAATGAAAAAAAGCAACAAAAAAAACTGACAAAAACAATGAGCTTTGGTCTTCCAGAGTGGCGCGTGTGCCATTTGC
CATCCCTTTCACTCGCTATGTCATCTAAAGGTCACCCACACCACTTGCCGAAAAATGAAGCCACTGCCAAAAAGTATCTTTTTTTCGCTCTGAAC
TCAGCAGCTGACGTTTCCGCCTAATAGTTATTTATGTATTTATGATTTGGAATTTTTTTATTCTCGTGCTTGTGGTAAAAATAGCAGGTGGCCTA
GAATAAATTCACACTTTTTCAAGAAGAAATTCCAACATTGGAACTCACTTCTAGCGAAATTTCACATAATTAACGATTATTAGTAAATATCTTTC
AGATACATATGGATGGCTAAGGTAAGTTCTAAGGTAAGGCTTAAGTTCTTCAAATTCTAGACCAATTAAACTTCTTCTAATAGTCTATAATTATG
ACTCTACCTCTAAATATTTACCCAAACACGGTTCACTAACACAATTCGCCGATATGGGGAGCGGAAAAAAAAAACCGAATGCGAACCCACCCTTAA
AAACCTTTGCCTGGTATTTTTCCACTAAGTTCACGGAACTGGGCAACTTAAAAGCGTATTCGCATATTCCTACTTGTGGAACTCACCTTTGAGTA
GCGCTTGTCCAAGAGTCGGGTGAATCCGGAGAGGCTGCCGACCACCTCATTGTCACCAGTGCCCCAAAGGCCCAGGCGATCGCGCTGCGCGTATT
TATCTAGTTTCGAATCGGGTTTGCTCATCTTGTCTTCCAAATTTGTTTCGCTAGTGGAGCTGTATGAACGTAGTTGCTGTTGTTGTTGCTGTTGC
TGGTGGTGAAGGGCGTGCAAACTGCTCTGCAGCTGATTCCAGTGGTGTCGCGAGGATAACGATAACGGCAGACCCTTGGGCAGTTCCAAATCGGT
GGCTAAGGCTATATTACCCGGATTCGAATCTCTGTCCCTATGCGTTTCCGTATCCGTATGCGGCGATGTGTCCACTTCGGCGGCACTTTGCGTTG
TGATTCGTGTCGTTAGTTTTGCGAAATTGGAAAGTTCGTATTCGAGTGTGGTTGTCGTTGTGGTCGTATGATTTTTACACACACGACTACTACAA
CAGCTCTGACTCTCTCTCTCATGGCTATTGTTGTTGTTGCTGTTGCTGTTTCTCTTCGTGTAACAGCCGAGCTCGCGCTCTTTGCCGCGACTATA
TGAGGAAGGACTCTGCGAATTGTTGGCGGTGGGATAAACCGGCGTGCTGAGGGAGAGAGAGAGAGCAGACAATATGTGAATGAATGTCAATGCGG
GAGTGACAATAACAACCAATTCGTCACCAACATTCGGATACTCTTTCTGAAAGAACCGATGTTAACATTTTTAATTGAATTTTAATCGTACACAC
TCCACGTTCCCACACTAACAATTGTTAATAATATATATATTACATTTTAATAGTATATATATCTTATTTGAATAGTATATTATATAACAGTATAT
AATAATATATGAATTTCACCATAAAAAGCTTTTTGTAATAGCCAAAAAGTCGTAGAGCAATAAAATGGTATTTAGGGTTAAAAGAGGCCCTTAAA
GGGTGGGTACTCTTCGTTTCAGATTCCTTATCAAGGTTTTCAGAACCTTTGAAATGCGCTGATATGTTTGAACGTATGTGCATGGTCATATGATG
AGGCGATGCATCGCAGACACGCCTTCCAGATGGAAACCGATAAGTGGTGCCAAAGTGACACTGATTATTGCCAATTCAGAAACACACCCTCTTGA
TCTGTGGTCCAATCGTATGACACCACATTATACTTGTTATTCTGAAATTCTTGCATTCGACTCACGGTCCAAAAGTTTTTCTGATACCAGAACAG
CGTCGTAGGATCGAGTACATGGCGGTGCTCTTAAAAGTCTTCTATATTATATACTTATTAGTATATTGATTTGCCGACAATTATCTCACTGAGTA
TTTGACTTTTGTCTGCGTTGCTGCAGCTTTCGTGCTGAACTGAACCGCAGTATTCGATTTGTTTTGCTACCACCATATGTATACACTTTGCGATT
TTGTTTTGTTTCCGCGCTCTTTGGCTCTTTCTCTCCGATTAGTTTCAGTTGTGTGGGGTATATCAGCTGACTGATAAGGGCGGTGCAAACACTAT
CTGCACATATAAACGCCATTAAACAACGATTATTACCATCAAATCATTTGTCTGGGACCTGGAAAACATTGCGATGCGGCGTGAATAGCATGCGA
AAAGTTTCCGTGAGAACAGCAGCGGTCGAAATAATAGTATTCAAATTAGACTATAGAGTATTGCAGTTAGCAATTTCTTATCTACTATTATTTAT
AATCAGTAGCTTTGATTTTAATGTAAACTTAAGTACAACGTGCGTGCATTACTTGAATTAAATAAACCGAACCTTTTCTATTAGAGATTATTAGA
CTCGATGGCGTTAAATATAAACCAATAATACCTCCTGAACTTGTGGCATCTGACTAAGTATAAATTATTTAAAGAGACGCCTCAAGGTAGAAGCC

FIGURE SHEET 816

CCAAACCCCAACCTTAACCTTCAGTGTCCCGAATCGCTTCAGTTCCCGCCCCACTTTGCACTTGACTCACTCATACGACCGGTGGGCCCGTTCCG
CTTTTGCTCGGATGTCTGTTTGATATATTCAATTATTACACAAAAATTGAAAGTAAAACACGGCAGGCGAATAAATTGGAATATATCACACATGT
TTGTGTGTGTGCCCGAGCAACCTTCATAAATATTAACAATTTACTTCAGCTTTGCCAACGAATTACATTTTCCAAGTACCTTCGTGAGCAAAACA
CACCTGTCGCTCTAACTTTTTTTTTTCTTTTTACTTCGAAAATCGTTAATTAAGAAGGTGGTGCTCTAATTTTTTATCGATGGCGTGTGTCAGAA
GTTATTCTTTTTATCGCAACGCCGACGAGTCGCCTGTAAATCGTTGATAAAACACTAGTAAAACGAATCATTGACCACT
(SEQ ID NO: 1498)

Exon: 8675..8521
Exon: 7931..7307
Exon: 3036..2108
Exon: 2051..1001
Start ATG: 8570 (Reverse strand: CAT)

Transcript No. : CT28469
AAAGCTGCAGCAACGCAGACAAAAGTCAAATACTCAGTGAGATAATTGTCGGCAAATCAATATACTAATAAGTATATAATATAGAAGACTTTTAA
GAGCACCGCCATGTACTCGATCCTACGACGCTGTTCTGGTATCAGAAAAACTTTTGGACCCACGCCGGTTTATCCCACCGCCAACAATTCGCAGA
GTCCTTCCTCATATAGTCGCGGCAAAGAGCGCGAGCTCGGCTGTTACACGAAGAGAAACAGCAACAGCAACAACAACAATAGCCATGAGAGAGAG
AGTCAGAGCTGTTGTAGTAGTCGTGTGTGTAAAAATCATACGACCACAACGACAACCACACTCGAATACGAACTTTCCAATTTCGCAAAACTAAC
GACACGAATCACAACGCAAAGTGCCGCCGAAGTGGACACATCGCCGCATACGGATACGGAAACGCATAGGGACAGAGATTCGAATCCGGGTAATA
TAGCCTTAGCCACCGATTTGGAACTGCCCAAGGGTCTGCCGTTATCGTTATCCTCGCGACACCACTGGAATCAGCTGCAGAGCAGTTTGCACGCC
CTTCACCACCAGCAACAGCAACAACAACAGCAACTACGTTCATACAGCTCCACTAGCGAAACAAATTTGGAAGACAAGATGAGCAAACCCGATTC
GAAACTAGATAAATACGCGCAGCGCGATCGCCTGGGCCTTTGGGGCACTGGTGACAATGAGGTGGTCGGCAGCCTCTCCGGATTCACCCGACTCT
TGGACAAGCGCTACTCAAAGGGCCTGGCCTTCACACACGAGGAGCGCCAGCAGTTGGGCATCCATGGCATGCTGCCCTATGTGGTCCGTGAGCCC
AGTGAGCAGGTGGAGCACTGCCGCGCTCTGCTGGCGCGACTGGATCAGGATCTGGACAAGTACATGTACCTGATCAGCCTATCGGAGCGGAACGA
GCGTCTGTTCTACAACGTGCTCAGCTCAGACATCGCCTACATGATGCCACTGGTGTACACGCCCACCGTGGGATTGGCCTGCCAGCGCTACAGTT
TGATCCACCAGAACGCCAAGGGCATGTTCATATCCATCAAGGACAAGGGACACATCTACGACGTGCTAAAGAACTGGCCGGAAACGGATGTGCGT
GCCATCGTTGTCACGGACGGCGAGCGCATCCTGGGACTGGGAGATCTGGGCGCCAACGGAATGGGTATACCCGTGGGCAAACTGTCCCTGTATAC
GGCCTTGGCGGGCATTAAGCCATCGCAGTGCCTGCCCATCACCTTGGATGTGGGCACCAATACCGAATCCATCCTGGAGGATCCCCTGTACATCG
GTCTGCGCGAACGCAGGGCCACTGGAGATCTGTACGATGAGTTCATCGATGAGTTCATGCATGCCTGCGTTCGTCGCTTTGGTCAAAACTGCCTA
ATCCAGTTCGAGGACTTTGCCAACGCCAATGCCTTCAGGCTGTTGTCCAAATACCGCGACTCCTTCTGCACCTTCAACGACGATATTCAAGGAAC
CGCGTCGGTGGCCGTGGCTGGTCTGCTGGCCTCGCTAAAGATCAAGAAGACCCAGCTGAAGGATAACACGCTGTTGTTCCTGGGCGCCGGAGAAG
CGGCTCTTGGTATTGCCAACCTGTGCCTGATGGCCATGAAGGTGGAGGGTCTCACCGAGGAGGAGGCCAAGGCCCGCATCTGGATGGTGGATAGC
CGTGGTGTCATCACCCGCGATCGTCCAAAGGGCGGACTCACCGAACACAAGCTGCACTTTGCCCAGCTGCACGAACCCATCGATACTTTGGCAGA
GGCGGTGCGAAAGGTGCGTCCCAATGTCCTGATTGGAGCGGCTGCGCAGGGCGGCGCCTTCAACCAGGAGATCCTTGAGCTGATGGCCGATATTA
ATGAGACGCCGATCATCTTTGCACTGTCCAATCCGACCAGCAAGGCGGAGTGCACCGCCGAGGAGGCGTATACGTACACCAAGGGGCGCTGCATC
TTCGCCAGCGGTTCGCCTTTTGCTCCTGTGACGTACAACAACAAGAAGTTCTATCCGGGTCAGGGCAACAACTCGTACATTTTCCCTGGCGTGGC
ACTGGGTGTTCTGTGTGCCGGCATGCTGAACATTCCCGAGCAGGTATTCTTGGTCGCCGCCGAGCGCTTGGCGGAGCTGGTCTCCAAGGACGACC
TGGCCAAGGGCAGCTTGTATCCACCACTCAGCTCCATTGTCAGCTGTTCGATGGCCATTGCCGAAAGGATTGTGGAGTACGCCTACAAAAACGGA
TTGGCCACTGTTCGTCCAGAGCCGGTCAATAAGCTGGCGTTCATCAAGGCCCAGATGTACGATCTGGACTATCCCCGATCCGTGCCCGCCACCTA
TAAGATGTAGATGATGGCCAGATGATGAGGATCCATTCCGCCTAACCCCAGAAACCAAAAGGAGTGGCCATCAAAAGATATCCGGCAAGGGCGGC
GAGCAGTAACCATGTTATTTATTTTATAATGTCGCACATTTGTCGTCTAGCATAATATCCAAATTTGTATCGCGGCTAATTAACCACAACCACAC
ACTATCCACCAACAACCATATTATAAAAAAAAACCAACTAAAATGGAATGTCATCAGCTTGCGGCGCGCGATTTTGTATAATGCTAACTATGTAA
ATGGGATATTGATCTAATAGATATGTAAACAAATTTTATGTAATCTTGAACAACACAAACTATTCTAAGGATATATACAAATAAAGAAATAAACA
AAAAT
(SEQ ID NO: 1499)

Start ATG: 106 (Reverse strand: CAT)

MYSILRRCSGIRKTFGPTPVYPTANNSQSPSSYSRGKERELGCYTKRNSNSNNNNSHERESQSCCSSRVCKNHTTTTTTTLEYELSNFAKLTTRI
TTQSAAEVDTSPHTDTETHRDRDSNPGNIALATDLELPKGLPLSLSSRHHWNQLQSSLHALHHQQQQQQQLRSYSSTSETNLEDKMSKPDSKLD
KYAQRDRLGLWGTGDNEVVGSLSGFTRLLDKRYSKGLAFTHEERQQLGIHGMLPYVVREPSEQVEHCRALLARLDQDLDKYMYLISLSERNERLF
YNVLSSDIAYMMPLVYTPTVGLACQRYSLIHQNAKGMFISIKDKGHIYDVLKNWPETDVRAIVVTDGERILGLGDLGANGMGIPVGKLSLYTALA
GIKPSQCLPITLDVGTNTESILEDPLYIGLRERRATGDLYDEFIDEFMHACVRRFGQNCLIQFEDFANANAFRLLSKYRDSFCTFNDDIQGTASV
AVAGLLASLKIKKTQLKDNTLLFLGAGEAALGIANLCLMAMKVEGLTEEEAKARIWMVDSRGVITRDRPKGGLTEHKLHFAQLHEPIDTLAEAVR
KVRPNVLIGAAAQGGAFNQEILELMADINETPIIFALSNPTSKAECTAEEAYTYTKGRCIFASGSPFAPVTYNNKKFYPGQGNNSYIFPGVALGV
LCAGMLNIPEQVFLVAAERLAELVSKDDLAKGSLYPPLSSIVSCSMAIAERIVEYAYKNGLATVRPEPVNKLAFIKAQMYDLDYPRSVPATYKM*
(SEQ ID NO: 1500)

Name: MALATE OXIDOREDUCTASE HOMOLOG
Classification: enzyme

Celera Sequence No. : 142000013384351
TCACGTTCTCCTGGCAAAATGAAACAAACGCAGTGCCGCTGCAAAACTAGATATTCTCCGTCATTTGCGATTCCTGCATTAATGAAGCACTCGCT
GTGCGGCGCGCGAATGTGCGATAATTTATTAGTGCCACATTTGCGACACAGATTTCGATTTCGGACCGCCGCCGGTGGCCACCAAGTCAATTCAA
TTTCCTCACGCGCACACCGCCTGACCCCTTTTGGCCACAAATAATAATGCCGGGCCTATGTCAGTCTATAAGTCTATCAGCACCAAATTTCGCCA
AATCCCGTGGCCCATCGACACGATCCATTTAGCCACCCATCCATCCATCCGTCATCCGCCACCTGTTGCTCGAATCGCACCAGCTGAACTTCGAA
TCCGCGCGAATGTCGGGCATGCAAAAGAGGTGACGACCCTGATCCTCCTCTGAGTCGCTGGTGAAATCAATTGTATTTCACAAAACAAATAGAGC
ACCGACCGTATTCGAAAACAATTTGTTTCTATCACAAACACTCGACACGCGTCGTCTTGTTTGCATTCCAGTCCGCTCCACTTCCAATCCGACTG
TCCGCAGCTTCGCGCGCGTCTTGAAAGTCCCGCACTCGCAAACACACTCGCGTCCAGTGGGACCGCGCCGAAAGCGCTGGAAAATACCAAGCGAC
TTGCAAATAAATACCACAGTTCTCAACACCATTGCAGTTTCAGAAAATACCACTTATATTTCTATACCACCAAATTCAAATTAATTATTAAAAGC AAAATCAAAATCAAAATGCACGCTAGACAACCTCTATAAGATAGATAGTAAGATCTTTCTTTTCTTAGCATTTTTGCATTTCACCGACGCGAATT
TGACCCTTATCGATTTTTTCGGAATACCTTGCTTACTTACTTTAAAAACGTAACAAAAATTACAATAATAAATGTTTCAATTTAATTTGTGTATA
ATATATTATTTATTTAATACGTCATTTGGTGAAACTAATTAAATTCACTGCAGCACTTCAGTTTAACTTTCACTGAAAACCAGAACCCCACATTA
CACTGCGCTGATAAGGTCCACTCTAGCGGAAAATGCGTTAGTGCGTGTTGTTTACCGGCATGTCCGAGGTCGAAAGAGCTCTGGATGTTCTGCTC
CAGGAAGCGGAGGAGCTGTGCATCGGGAGCAGCGTAGTGGAGCTGGACAGGATTCCAACCGCCTTGGAGTTTTGTCGGGAATTCTACTCCAAAAA
CCAGCCGGTGGTCATTCGCAAGGCACTCAATTGGCCCGCGATTGGCAAATGGACGCCAAAGTACCTGATCGAGGCTCTCGGGGACAGGAGCGTGG
ATGTGGCAATCACCCCGAATGGCTATGCCGACGGCTTGGCCACTCAAAATGGACAGGAGTACTTCGTTTTGCCGCTGGAGACGAAAATGAAGCTG
TCCGAGGTGGTCCGCCGCCTGGATGATCCCACTGGTGCTGTCCACTACATACAAAAGCAGAACTCTAACCTCAGTGTGGACCTACCGGAACTGGC
TGCTGATCTGCGGGTCAGTGATCTCGACTTTGCGCAGCAGTCCTTTAACAAACCGCCTGATGCTGTTAACTTTTGGCTGGGCGACGAGCGCGCCG
TTACCTCCATGCACAAGGATCCATACGAGAACGTGTACTGCGTGATATCCGGTCACAAGGACTTCGTTCTCATCCCGCCGCACCAGCTTAGCTGC
GTACCGCGAGGAATTTACCCTACAGGCGTTTACAAGACCTCAGATAGTGGTCAGTTCTACATTGAACCGTTGAGGGATGAGGAAGGCAGCGATCA
GTTCACAGAATGGGTCAGCGTTGATCCCTTGTCACCCGACCTGGCCAAATATCCGGAGTACGCCCGGGCCAAGCCTCTGAAAGTACGTGTTCACG
CGGGAGACATCCTATACCTGCCCAACTACTGGTTCCACCATGTGTCCCAAAGCCACAAGTGCATCGCCGTGAACTTCTGGTACGATCTGGACTAC
GATAGCCGGTACTGCTACTACCGCATGCTGGAGCAGATGACGTCCGCAAGGAGTGGCTAATAGAATCCGGAGAAGTATTTATTCTCAGGGATTGT
TAGGTGAATTCAAAACCCTTCTTGTTTTCAGTGTATTTATATATATTATTGTTACATAATTTAGTGTTAAATAAAAAACTGATACCCAAAATGAG
TTGCGAACTACGACTAAGGACACGACCATAAAAGATTTATCTTTTCCGAAATTCGTAAATGAAATATGAAATATCCGTACAGATGATGACTTCTT
AAATAAGGAATGTTTGCTTTGTTGGGTTATTCTCTAGTCTATTCGAGACTGACGTCCTGTTTTTCTGCGCCGGAAGGCTCCGCTGCAGCCTGTCC
ATCTGCCTCCTCGTCGGGATTTTCGTTGTTCTCGCACTCCAGTTCGCCATTTCCCGCGGAGGAGACGTTCTTTTGGTCCGCCTCGGCCAAGTCTG
CATCGTTATTCGAGTCCTGCGACTGGGATTGGGACTGTTTGCGCACACGCTGGTTCTTCAGCTTGGCCGGACTGGCTCCAGAAGGTGTCACCTTC
GACTTGGTCTTGCAGCTATCCTGCGGCTGTTCCACCACAAACAGCTGCTCCAAATAAGAACGGTACCAAAGCAGGAACTCGTCCCGCTGTCGTGG
TATGTCCATCTTCTTGATCTTGGCATATATGCGTTTGGGCGAAATTAGTGGCGAGCTGGCGGTCGAATTCTGGGCAGCAGTGGCCGTCAGCTTTG
ATACCTCTGCCAGTAGGGAGTCATTGATGACGGTGTTGTTGTGCGTCTGATTGCGAATGCGTTTGATAATGTACTCGATTAGTTCGTGATCCGGT
GCCAGTTCTATGCTGGTCCCTGGTCCTGATCCCGAGCCAGAGGCTTGTTCTAGTTTTCCCTCGAGGATTTGCTGGTAAGGAAGACGCAATTATGA
GTTAATCGATCCAGTTTACGAAAGCCTTTCTTACCTCTTCGTTCTCGGTCCTAAGAGAAGAGATAACAGCAGAAGCACTGTCCTCCATTTCATCC
AGGTGCTGCCCGTTC
(SEQ ID NO: 1501)

Exon: 1001..2055
Start ATG: 1105

Transcript No. : CT28505
CAGCACTTCAGTTTAACTTTCACTGAAAACCAGAACCCCACATTACACTGCGCTGATAAGGTCCACTCTAGCGGAAAATGCGTTAGTGCGTGTTG
TTTACCGGCATGTCCGAGGTCGAAAGAGCTCTGGATGTTCTGCTCCAGGAAGCGGAGGAGCTGTGCATCGGGAGCAGCGTAGTGGAGCTGGACAG
GATTCCAACCGCCTTGGAGTTTTGTCGGGAATTCTACTCCAAAAACCAGCCGGTGGTCATTCGCAAGGCACTCAATTGGCCCGCGATTGGCAAAT
GGACGCCAAAGTACCTGATCGAGGCTCTCGGGGACAGGAGCGTGGATGTGGCAATCACCCCGAATGGCTATGCCGACGGCTTGGCCACTCAAAAT
GGACAGGAGTACTTCGTTTTGCCGCTGGAGACGAAAATGAAGCTGTCCGAGGTGGTCCGCCGCCTGGATGATCCCACTGGTGCTGTCCACTACAT
ACAAAAGCAGAACTCTAACCTCAGTGTGGACCTACCGGAACTGGCTGCTGATCTGCGGGTCAGTGATCTCGACTTTGCGCAGCAGTCCTTTAACA
AACCGCCTGATGCTGTTAACTTTTGGCTGGGCGACGAGCGCGCCGTTACCTCCATGCACAAGGATCCATACGAGAACGTGTACTGCGTGATATCC
GGTCACAAGGACTTCGTTCTCATCCCGCCGCACCAGCTTAGCTGCGTACCGCGAGGAATTTACCCTACAGGCGTTTACAAGACCTCAGATAGTGG
TCAGTTCTACATTGAACCGTTGAGGGATGAGGAAGGCAGCGATCAGTTCACAGAATGGGTCAGCGTTGATCCCTTGTCACCCGACCTGGCCAAAT
ATCCGGAGTACGCCCGGGCCAAGCCTCTGAAAGTACGTGTTCACGCGGGAGACATCCTATACCTGCCCAACTACTGGTTCCACCATGTGTCCCAA
AGCCACAAGTGCATCGCCGTGAACTTCTGGTACGATCTGGACTACGATAGCCGGTACTGCTACTACCGCATGCTGGAGCAGATGACGTCCGCAAG
GAGTGGCTAA
(SEQ ID NO: 1502)

Start ATG: 105

MSEVERALDVLLQEAEELCIGSSVVELDRIPTALEFCREFYSKNQPVVIRKALNWPAIGKWTPKYLIEALGDRSVDVAITPNGYADGLATQNGQE
YFVLPLETKMKLSEVVRRLDDPTGAVHYIQKQNSNLSVDLPELAADLRVSDLDFAQQSFNKPPDAVNFWLGDERAVTSMHKDPYENVYCVISGHK
DFVLIPPHQLSCVPRGIYPTGVYKTSDSGQFYIEPLRDEEGSDQFTEWVSVDPLSPDLAKYPEYARAKPLKVRVHAGDILYLPNYWFHHVSQSHK
CIAVNFWYDLDYDSRYCYYRMLEQMTSARSG*
(SEQ ID NO: 1503)

Celera Sequence No. : 142000013384598
TTTTAAGTAGTTTACCCAACTCCTCCGCCTCCTGACTCCTGGATTTTAAGCAGATGGAGCCCGGAAATGAGATATCACACACGACTTAATCGCAG
GAACACGAACAGGAAACAGATGGAATCGTCGATGATGGAAGTCTACTACGTATGAGTAGGTATAAGTTATTACCACTGAAGTATTAAAAAACCAC
ATTATTAAGTAATGACAGAACACCTTCTGTGAATTACACGGTCATGTTTCATACAAATACATAGCTTGCATATCAACGATTTCCTTATAAAAGAT
ATTCTTAGTTAGAAAGAAAACTTTCACCCAATAGCAGTTTTCTCCATTAACTTTGGTATATGAACAACTAAAACAGTATTAACTGTTTATTTTAT
TACTGTACTTACTATTTACTTACTTATCAAGTCCTCGAGCATTTTTAACATTTGAAAAATAAGAACCAGTGCTAAGGAATAATTATTCTTCGCTA
TGCACATGCAATATTAATCTGCTCTTACCCAATTGGATAATATATTTACGTACAATAAGATCTTTATGAATGCATCATTGCAAATGCAGATGGTT
AACTAAGTTTGTAATTCACAAATATTCTTCCAAAGGGGCTTTACTCAACATTTAATGTCACTGACCATTCAGCCAAGTAAATCACCTTCCCAAAC
TAATTTACCAGTGATTAATTGGGCTAGCAAGTGTAGGTGATTGGAGTATACTAGCCTTATCTACCTTCGGATCATTCCTTATCAAAAGCACGGTT
GTTTGGGAGAGCCCGCCAAAAAGCCGGACTCTATATGTAGACGGAAAGCTGCTTGATGGAGGGTCTACTGACCCGGTGTCTTCTTACAATCACTG
TTTCTCAAATAAATTGGTAGGGACAACACACTAAATACACTGTAGATTTGAAACCAAGATGGTTCCACATTAGAAGGGCCCGGTGACATTAGTGG
ATGTAGTTACTTGTTTGTAGGTAGTAGCTGTTTCCCAATGAAGCACGCTGTTTATTTGAAATTAAAAAAGAACTGGATGCATATATTTCGTCTGC
TTATCTTGGCGATTCCTCGACGCCAGAGCGGAACGCACTGGGGCGCGAGTCCGGCTAGATTGGTAGACTCCATATGGAGATGTCAGGTGGTGCAC
CCAGTGCTCCTCTCCTCCGGCTGGACGAGACCTCTACTTCCTGTTCTGGTTGTTGCGGGCCATGTCCTTGGGGAAGGAACGCAGTGGCGGCGTGC
GGATGCGGCGGGCCTCGCGCGAACGGTTGCGCACCACCTTGGAGTGGATTGCGCAGGACACGCAGTAGTGGAGCTTCGCATAGAGCTTGGGCAGC
ACGTACGAGTCCCAGATGCTGGCCTCCGTGATGTCGCGCACGGCGGCAGCCTCCACGATGTTGCGGATGACGAACTTCTTGATTGCCTTGTCCTT GGGCACGCAGCGGGCGCAGTTGGTGCAGCGCACGGGCTTCACATGGCCGCGATTGTGCTTGTTGCGTCCTCCGTTACGGCGCTTCTTGGTCATCT
TGGCGGCTGCTTGTCAGTGGGGGAAACAGTTTGCACGGCCATTAGCATTTAGCACTGCCTTTGCTCAGCGGATGGCTGCCATAATTACCTTATTT
ATCAATTTCAAAATCCGCCCAGCGAAATCCGCGTGTGTTCACGTTTCGGGAAACGAAAAGAAAGAAAATAGTGTGGACGCACCCGGCGAAACTCG
GATAAACGGCCTAAAAAATACCTAGCCAGAGCGACTAGCGTGTTTGGCAACCAGGGCTGACATTTTTACCCGCTAAAACTGGTTTGGTATTCCAA
GTTCTTTGCTTTCCTTTTTAATCTATCAGACTCTTTTAATATATTGGAAATTCGAACTGCTTACACTAAAAAATGTCACCTGAAGAATATTAGTA
AAAACGATAAAGGTTACACATTTAGCTATATATCCATATCTTATTAGCTAGATACAGCTTTAATCTGATTAGAAGTTGGCAACGCAACATGGTGT
GGCCAGGTTCCACATCGAAGTAAAATTGTTTTTAGCGGGACATTTCTTTAAAAAAGAGATGAATAACATAACTATAAATTGCTTAATTTAATGTA
CTAAATATAATATATCCTTCGATATTCCTGAAATTACCCGTATTTTTATAGCAATCTTACGATTTTAAATTTGTTTTAGAAATTTACTTGTAAAT
TACATTACTAAATTTGGTATAACAATAAATAATCTTCCGTTCAAAAAATTCCAGACAACTTCAAAAACGTATAATTTAGACTACAGCTTTTTAAG
AAAATTTGTATAAAATTTCAACAAGAAAAAAAAATTAATAATAGGCGCAAGCAAAGCCTAAATTGAATTTTTTAAAGTTATTTTTTTTAATTAAGC
ATCAAATTTTAGATTTTTTTAAAAAAATTTAAAACGAATAAGTCAGTAAATAAATATTTTTTGTATCGGTGAAAATAAAAATGGAATTATAATATA
TTCATTATTATAAATGATAAATATTTATAAGTGTTAAAGACCTTATATAGTATATAATCTGGTAATGTTCGTCCGTCTGTTCGTATGAACGAAGT
GAAATCAAGAATTATTACAAGCTAGAAGTTTAAAATTAAGCATACTTATTATAAAAACGGAAATTTTTTTGGAAGATGTCCCACAAACATCCCAA
ATCAGTTATTC
(SEQ ID NO: 1504)

Exon: 1671..1609
Exon: 1528..1001
Start ATG: 1518 (Reverse strand: CAT)

Transcript No. : CT28945
TCGTTTCCCGAAACGTGAACACACGCGGATTTCGCTGGGCGGATTTTGAAATTGATAAATAAGAGCCGCCAAGATGACCAAGAAGCGCCGTAACG
GAGGACGCAACAAGCACAATCGCGGCCATGTGAAGCCCGTGCGCTGCACCAACTGCGCCCCGCTGCGTGCCCAAGGACAAGGCAATCAAGAAGTTC
GTCATCCGCAACATCGTGGAGGCTGCCGCCGTGCGCGACATCACGGAGGCCAGCATCTGGGACTCGTACGTGCTGCCCAAGCTCTATGCGAAGCT
CCACTACTGCGTGTCCTGCGCAATCCACTCCAAGGTGGTGCGCAACCGTTCGCGCGAGGCCCGCCGCATCCGCACGCCGCCACTGCGTTCCTTCC
CCAAGGACATGGCCCGCAACAACCAGAACAGGAAGTAGAGGTCTCGTCCAGCCGGAGGAGAGGAGCACTGGGTGCACCACCTGACATCTCCATAT
GGAGTCTACCAATCTAGCCGGACTCGCGCCCCAGTGCGTTCCGCTCTGGCGTCGAGGAATCGCCAAGATAAGCAGACGAAATATATGCATCCAGT
TCTTTTTTAATTTCAAATAAA
(SEQ ID NO: 1505)

Start ATG: 74 (Reverse strand: CAT)

MTKKRRNGGRNKHNRGHVKPVRCTNCARCVPKDKAIKKFVIRNIVEAAAVRDITEASIWDSYVLPKLYAKLHYCVSCAIHSKVVRNRSREARRIR
TPPLRSFPKDMARNNQNRK*
(SEQ ID NO: 1506)

Classification: ribosomal_protein
Gene Symbol: RpS26
FlyBase ID: FBgn0004413

Celera Sequence No. : 142000013384600
TCTTTTTAGTAGTACATTTAATGATCACCTAACAGGCAACAAAAATCCTAAAAGGCACTCACTAATAGATTCCCTTCTCGCCAACAGGGATGACC
GCCTTCGTACTGTGCATTCTGGCCATGTCCTCGGGACTGGCTGCACTTTTCTCCAGCCGCATCAAGAAGCTAATCACACCATTGCTGAACAAGAC
GTTCCACAACTTCCTGGGATTCGCGTGCTTTGTGATCGCACTGGTGACCCAGTACTATGGCTACCAGACGGGCTACTTTAAGAGCCGAAGTGAGA
CGGATTTCCAAATCCTGATGAAGTGCCTCACCCTCATATCGTTGGTCCTGTCGAGCTACGGACCGATGAAGGCACTCTATCAGAAATGCAAAAAT
ATATCGCAACAGTTTTAGATAGGATGAAAAGAATCACTCGAATGTATGTAGATAAATAAATGTAATTTTTTCTAAAACCCCATTTTATCGACCTA
TCCAACTATACCAACAACGATTCAAAATTTTATACCTGTTTATTGGTACAACGTGTGATCCATAAACATGACTAAGTATTTTTACAATGCCTCAT
TAGGGAAAACCCGGTTAACCAGCGGTCAGACTTTCATCGTCCGGTACTCCCCCCTGTAAAAGTTATATAACCACCCTTTTGATTGATTTGATTTG
ATAAGGTCTGAAAAAGTAATGAATTGACTATTAGATACACTGCAATTTGCATTTAAGTTTAACCGCTCACTCAAAAAGCCAGCATTTGAATTAAT
CAATCAAAATTATGATCATTTATAATTTAAGTTATACTATTATTCATTTTCCTATAACAGCATTGGGTAGCATGCATCATTTTAAAATCCAAAAC
ATGACCGGGTTTTTTATCTGATCGGTTTGTGACACTTGGAGGCCGCATAATTGATAGTAACTGTCCCAAATAAGTCCAAACTTTTGAAGCCCCGT
AAAAAGAAGATCTTGACTTCCGGCACCTTAAATTAAAAAACCGTGTATTTTGCATGGTGCAGTTTCGTATGTTTATTTAGAAAATCCATATCATT
TCTTCTTAAATCTCTCGCAATAAATAATACTTGGCGCGTGTGTCGCGTTGTGTGTGTGATACGTATATCAGTTAGCAGTAATAATAAATAGCTAG
CGTTAGGTATTAAAATTCATAGTCAATTGGGTAATACAAGGCTGTCTGGCTTTAAAACCCCCTTTCTGGGTAACTTTTGGTAAGAGAAAGTCAAG
ATCTCTATATAGAATCGGGTGAACAGATCTTTAGCATGCGGTAGGTAAATAGGAGTTATCAGCTATCGACTAAAGCCCAGTTAAGAATTGTGTGT
TGGGCAAGGCATATTCGAAATTCGACTTTCTATATCTTTTCATAGTTTCCATAGTTCGCTCCGCTCACAGCTTGTTGCTGCGTCGAATGGCGAAG
GACATTAGCGCGTGCTCCAGCCGCATGTGGTAGGGTAGCTTGCGCTCCAGAATGACTGGCTCCTGGCCATCTGGACAGCACCGGTTGCGGCAGCA
CTCGCACTGGCCGTCGTCATCGTCGTATTCCTGCTGCAGTTCCTGCTCCAGTTCGTAGGCCTTCTTGGCAGCCCGCTGCTCGAAGCGCAAATAGA
AGGCCAGGCAGACAAACAGCATAAATACCAGGGCACACATGGCTCCACTGGCAATGCTCGCCTTCTCCAACATCGGACGCGGCCTCTTGGCAGG
TAAGTATTGTCGATCTCCTTGTATTCGCATCGCTGTCCCATAAAGCCAATCGCGCACTCGCAGCTGTAAACCGGTAGATCGGCTATCTTCACCGC
AAAGCAATGGGCATCGTTCAAACAGTACCAGGCATCGAAGGTTTCCGGACATTTGTATGTGGGGAATGTAATATTGGGCCTGGGCGTGGTCGTCG
TGGTGGTGCGCATTGTGGTGCTACTAGTGACTGGAGCCTGGGTCGGCGGCAATGCCGTGCCGGACATGGACGAGGAGATCGAAGAGCGCGGCTTG
GGCACCGTACGGCTGGAGCAGGCCTCGACGTGCCACGGATGTGCCAGACAGCCGATCAGTACCAGGGCAACCAGCCCATGTTGTACACTCATTGT
GGAATGCATTACAATTTGTAGCTTTTTAGCGTAGCGTATCGGCTTGTTCGTTTTTTGGCGTGCAACGTTTGGTTGTTTAAAAGCTTAAGAATATT
AAAACTAGTGACTATCACATAAATAAATTAGAATATTCGTTGTCCGCTGCTAGGGCGTCGTCAAATCTCTTTGGAATCGGGTTTCTCTACATAGG
TATGCTGCTGGTGGAACGTAAACGTTGAGTTAGGGGTGATGTGTGTATCTGTGGGGAAGATGGAAAGACATTAGTGGCCAGTAGTCTCCAAGCAC
CATCGATGGTTTTTAACTCTAAAACTGTGTACTCAACAGAAGGGGGAAAATCAAACTGCGTAAAATCATAATTATATATGTATGTATTTATAAAA
GTATAAACTATAATAGATCGCTTTGAATAGTAGTTATGTTACAATCAGCAAATTTTACTCCTTTCTTCACATCCAATTCACTTTCGGTTTAAAAT
TTCATTTACGTTGTCTCCCGTTGATTATCCTAGCTCATCAAAGCTGGCTGTGATATGCGTTGGGTATCCATATCACAACCACTTGATGAGGCTTA
GATAATCAACATCGTACAGGTAAGGAACAGTTTCCTTAACTTTATGAATTAGTAACATGGTTAGTAACAATATTGCACCGCATGTGTGTAAGTCA GTTCGATAGGGCCCCCTAAGTCTGAGGTGCCAGTCCACCAGTTGAGCCATTTTTCGGTGCTGTGGCATGCATCTGTCCCCCGTTGTTCCGAATTC
AGATCTCTGTTAGCCGCGTTTATTTTCCGATTGCATTTCACTACAAATATTATACAGATTTGAGGCGGACATAGTGTGTTTTATTTATGATGGGC
GTGTGAATTATGTGGCGGGAGGTATTATTATGATTTGATGTACGATACATTACGCTAAGCTCATCAAAGCTGGCTGTGATATGCCGCGCAAAGCG
GAAATGCATTTCACAACCACTTTGAGAGCCCAGCATGAATGCGCCAATATAGTTTTATTGATTGAGGTTTCGGGATACTTGACTGCGGGAGTTCA
GAATTTTCAATTTTGGTTTTCATGCTCATGTAATGATATAAACAAAATCAGACACTTGTTACCGTTTTTATACTTTTTGTGTTCAATTATGCTTT
TTTTTTGGAATTTTCAAATTGTTTTTTGATTGATTTTTTTTTTGCCTTGAGCATCGCGTCGCTCCTCAAAGCTGGCTGTGATATGAATAGGCATA
AAAAGGCAAACATTTCACAACCACTTTGAAGAATGACACAATTCTCCTGTTTCGATTCGATGAGAGCCGAGGTGCAGATTCAGATTCAGATTCTT
CTAGGGGTCTTTTTGCAACGTTCTCACGGCCGTCGGCTTTGAGCCTTGTACTTTTTTGCAGCCACGGCACAATAAACAAATATGAAAAAAGTACG
TAAATAAATAAATGCGACGACGAGACTACAACACGATGATAATGACGATCATGACGACGACGACGATAATGATGATTATGATGATGAGACTACTG
GTACTGGTGATAGATAATACGCAAATGTTGATTGCAATGAATGGCGACAGAGCGAGCGCAAGTGAATGGGACAATTTCGTACATATCTACGCTAT
AGACTGGCCATTGTTTCAACAACAACAACAAAATTCAACAGACACAAACGCACACAACACCGAAGAACAACACTGAAAGAGGGCAAAAAGCAATG
CACCCCAAATAATTATAATAAAAATGTAAACATAATTTTGGCGCCAGCCTTTGGCAATTTGACGCCAAATTTGTTTTAGATGATTTCTGAGTTC
AAGTTCGGGAATTCAAACTGATAAGAAATGCAAACGATGAATAACAAAACGGAAGAACCGAATTCAGTTGATCCTCCAGAAGATCATTTAAATAA
TCGATTTTATCGAAAAATTTTAAATGCATTACTGACGAAGTTCAATCACTTTAAAATGTGAGCAAAACAAAAACTTTTTATATGAAAAGACGAAT
GCTGTTCACCATTTCGAGCGCCCACTGTGGTGCAATGCAAAAACAGTTATACGTTGGGTGTGGAGACTTATTTATGTATTAGAATGCTTTTACGG
TTAACAATTGCTGCACTCTCTACCCTCTCTTTCTCGCTCACGCGCGGCAAGCGGGCAGCTTATTAAAATTTCCGTTATAAAAATTAAATCCACCG
CCGCTGCTTTTATGTTCATAAATACATGTGATACGTCGCATGCATGTACACATGCACAAATGTATGTATATACACATGTATGTGCGTTTGTGTGC
GAGAGGAAGTCGAAGTAAGGTAATGAGCGTAAAGTCAAGTTGAATAGCCATATAAAATGCGCTGAACTTGCGAGCGTGTAGGTCAAGATCAGCGG
CGGCCGTTTATAATATTTTGTTGGTTTTCGCAAATAGCAATTGACGAAAGTTCGATGATCTTGTAGTACATTTCAATAATGGGGGAATGAGCCAA
CTAGCACGATAGCAACAACAGCAATATATACAAGCATCACAATAATTACAACAGCAACAACAACAACGATCAACTATATTAGAGTGTGGACGGCA
AAAAGTGTGCATACATACATGACAACAAAAACACCCGCTAATAAAAAATACTGTTGTGGCTGCTTCTTCTTCTGCTCTTGCGTCTTTTACAACTT
CTTCGGCAAGCCAGTTGTTGTTGCTGTAATTTTCATGTTGCCTTGCTCTCTTTCATTCTTGGGCGTCGCTGCGAGTTCGTTGGCTCTTCTCGTTT
CTGTATGTGTGTGTGTTTAGAAAACTGTAAGGAAAGCAAAGTGTGTGAAAAATATGGTTAAGGTAAAAAATGCCAATACAGGAACAACAACACAG
CTCGCTCTCTTTTCTCTGCCTGCAGTTTCGAAAAAAAATTTACCGGTTTTTATGTTTTCGCAAAAAAGCTCAAGAAACAAGTCCTACAAGTTTTA
AATCGAGAGAGGAGAGAGCAGAAAAGGCGTGAGAGCCCAAAGAATGCGCATTTAGCAGAGACAACAACCTTTTGAGGTGTGTTGCGTATACGTGC
ATATTCGCACACACACACCACCAACGCTTCAGCTCTCGCTCTCTTTTTCTCGCTTCGCCATCTCACTCTTACTCCATGCCTTTCAGGGGATAAAT
TATGTATGTATATATGTACCATGCGTGTGTGTGTGCGCGGGAATGTTGTGAGGAATTCTAAGAATTTTGCACAAGCGACAAATGAAACGGGGCGC
GGACCACACATACATATATGTATATTCCAAAACCAAACAAAAGTTTTAATAGTTCAAAAAGAAAATTGATTATGCGTCGGTATGCGAGAAGCGCC
AACAGCCGAATGCGAAATATATCACACCAACACAAATACAGTGAAAGCAGAAAAGACGCAGAAGATGGGAAAATTCGAAGACACCGCGTGTAGGC
GTTAAAACCTATTTTTTTTGCCCAACACCAAGCTAAATGAAACACTGCTCACTAAAACACCAATTCACTATGCTTTATCTTCACAAATTACCAAC
TGTTTGCATTTAAACTTGGACAACATTAGGGGGCAGAACGCCGACAACGCACACCGCGCACACGAAAAAACACAACCGCACCGCCAAAGATTCGA
AAACCGAATGCCGAACAACAACAAAATTGGTTCTGAAGATGGAGGTGTTTTTCAGCAGAGCGAGATTCCCTGGCTCACGCTGAGCGGGAGAGAAC
GAGAGCGACAAAGTCTCTCCTCTAAAAATGCGGCATAATAACAACAAAGTGGCGAGCGGCTTTCGAGCTCATGCTGTATGTTGTTGTATACCCGT
TACTTGGAGAGTTAATTGGGTATACGGTGATGGGCTCTTAGGCAAAGAATTTTTCCAAAATACACTTTGCATAATTACTCAAATAAATTGCCTCA
GAAGCTACTTTACTCGTTTAAATCTTAAATTAATATTATTCCATTAATGTCAAGCCACACAATACAAAATTCAATAGGAATCACTCACCTATAGC
TGTCATTGCAAACAAATGATATTACCTATTGGACTAAAGGGTATATCTGAGTAGTTACGCTTCGTAAAAAGGGCTCTCTCTTGTTTTGGTTTTTG
TTTTGGTGTTGCCAGAAGATTTCGCACGATGTAGGATCAACATGTTATTGACACGACGTCGCCGACGCCGCCACTTTTAAGCTTGGCGGAGCAAA
AGGCACACAAACAAGAAGCGACGCAGAGCGGCGGTGCAAAAGCACAAAAAAAAAGAGGAAAAATGCGCTCGAGAGCGGAGGGCGTGGCGGTGCGC
AGGGGCGGGGCAGGTAGCCGGACAAACAGGACGAACAGGATGAAACCCAGACGAGTTCGGCCCCACTGCAGATTTCATGGAACTGGCCGAAGGTT
GAGGATGCGGATGCGATGCGCAGGCGCGCAAGTAAACAACATTCCATTCCTCGGGAAATTTCTTCTGGCCGCTCGAGAAGCGCGCCAAAAATAAA
GCTCCGACCGATGTCGTTGCCATAAATATTGCTATTTTGACTTTCCAGATTCTCGCGATTCAACGCCCCTTGAAATGGGAGCAACTTGCTGGAGA
TTCGCGTATCAGGGCTGGAAGAGGGTTTCTCCAATAACTGCACATTCACTCAAAAATATGGTAAAAAGGTGTGCTGCAGCTTCGAGAGCTCCCAA
GAGGTAACTTTATGTTATAAAATTACATATATTTATTTTATGTATATATTCTGGGAAAATCCATACGCGATCTAAAACATTTGGGGCGCGGTTTT
CACAGGTAAATGAGATTTTGGAATTCCTTTACTGAAATGCCAACGTCGATGTCGTCGATTTTTTCAAAAAATCACAAACATCGATGTTTTTCGAG
GAATCATCGATGTTTCTCCACCTCTAATAAGGCGGATTCGACCTATGTACATGTACTGCATGTATGAAAGCGGCACAACTACCCGTTTCCGGTGG
GCAGTCGGTCCGCAATGTGGGCCGCAGACACCATTCCACAGCCAATTGACGTCACAAGCGACACAACAGCAACAACCTGGCACACGCTTTCTGGG
TTATGTCGGAATGCATCCAAAAGCGGGAGAAAAGTAGAAAAAGGCAGGAAAAGAAAGAAACCAAGAGTCACCCGGATGGCAATTCGATTCTGGTG
AGATTTGGACAATCAATCGGCTTAGTTCACAGCCCAGCGGGACGGGACTCAGTGCTACAGGTTCAACTGTACAATAATACCAAGAAGATGACGAC
GATGACGATGACGATGATGATGGGGGATGGGCGATGGGCAAAATGTTAATGGATTGCCCTAGGACCTGCCCTCATTCCGTTTGCCATCTTCGTCG
CTTCGCTTCTGCATTTGTGCATTCCCATTCCCAATCCGATTCCCCCATCAAGTTGTGCTTCTTTGCCACACCGCTTTTCTGCCCCTTTTGCGGTG
TTCTGTTGCTTTGTTGATGTTACAATTGTTGCACTTGTTGTGTGCGGCTTAGGACGTTGAACCACAGCCGGCAGAAATGCAGAAATGCACGCAAC
TGAGTGGCAAGTGTACAGCTGCAGTCACAGCACTAGCAATGCTTTGCGAAGGATTCCTCCAGACCGCTTTGTAATTGGTTTTCTTTCGCGTAATT
TGGCCGATATTAGTTAGTTCATATCTGCAATCTAAATGTTACGAACCAGCAGAGTTCCTAGAGCCCTAGAGACATTAATGTACTTTTAATTGCCC
CACTGTATGAATTTTTTTCAGTGCATTCTTGCAATTTGCTAACGTTTTTACCGCCATTACCGTCATTGTCGGTATATATTTGTATGCTCATTCGG
AAAGCCAATTCGAAGGCAATGCTAATAAAATCAATAAACAACATTACTGTCACGCACACATACATACATACATATGCATATAGCTTGGATGTCCG
GTTGAAACGATGACGATGAAAGGTCACGACGAAGAATTTTTCGCCAATTGCCTGGTGGGTCGCACAGTCTGGGTCGCGAGACGTCTGACTAGACA
ACATGCAAATAGTAACGGTAATCATTAGACGCACACACTCGCACCTATTTGCATGCACACTCTCTCTGGCTGTGGTTCTGGTCGTGGGCCCCCAT
ATTTCATCTATCTCGCGGCCGCTCTTTCTTTCGCTCACCATTTTCTATGCTGAGTTCGACGGCCTTCTTACGTAAAATCAACAACAACGCTCTGC
GGTATTTCTCTTCTAATAAGCGGGTGCTTGGGGCTTGGGGTTGGGGGGATGTGCACTCGCCGACAGAGTTGCCATATCTAGCCAGACATCAAACT
CGTTTTCACTGTTTTGGCTCCACACACACACACACACACGCATGTGAGTGGCTTTGCAACTGTACAAGAACAATAAGTAGGGGCAGCATAAAAGC
AACAACACACGGCGCAGACGCCAAGCAACCGCTCCCCTCCCAACGCTCCACTCAATGTTTGTCTGTCTGTCCGGAACGTCTGTTTATGTATGCTT
TAGGCGTATACATGCATGAGTGTGTGTGAGCAATTTTTATTTTTCTGAATGTAAAGGAAGTGGCACGTACTGTACTACTCAACTCACCGCTGCCG
CAACAACAAGAGCAGTGACAGCCGGATCAGGCTGGGAATTCGAATAAGAGCGGAGCGCGTCGCATTCGGATGTTCCGATTCCCCATCGTTCCCAG
CCGCAAAGCGGTCAGCGTTCCAATGCCAACGGCACAGTGGTTGCGATGCGTAAGGTAACGTGCTACGGAACCGAAACTCGCGGATGATCGTAAGT
GGGAGATATGTACGTGGGATAAGAGCGAAAGTAGACGGATATCCGATTTGCAAAAAGATGTAGTATTAATTTAAAATGTTTAGAATAACAAAAAT
AAGCTAACAAAACTATAACCATGACAAACTATGACGATAACAATATATTTGCTATGCGTTACGATTTACAAACTTTGAATACTTTTTAAAAGATG
CTTATTTAGGATCGATCCATTGTGCAGCGAGATGAGCGGAACGAAAGGCGAAAGGGACGCTGGTTTGCGTCTCCGCTGTACGCCAGACAGACAGA
CAGACAAGACGCCGCAATATTATAAACAGGAAATGGAATTTACCCACACGGATGCAGCGCGGTGAAGTGTGTGTCTGTGTAAATTGCTGATGAGC
CGACAAACGGACGTGGTGCTCAATTGACAGATGAGCACGAGAGAGACAGGCAGAGCATAGCACACCGCCGAATGAGCGAAGGAGAAGGCCAGAGC
GCGCTTCAAAGTTGATTGAAATCAATATACGTACATACGTATGTATACACACATAGCGTGCCGGTGTGAGTGTGCTAAGACCGCTCGTGGAATGT
TTGAAAAACGCGGTCAAGCGACGGGAAGAGCAAGAATGTTGAACTCTGGAAGTGGGAAGAAGTTTCTGTAAATAGAAGCCAGGTGGAAGGGGCTT

FIGURE SHEET 820

TTGCACCTGCCACGCCCAGCAGCCCCTGGAATCAATTAACATGTTGCACAACTGCAGCGGCTCCTATATACATAGTTCATATAATGTACTTGTGA
TACAGTGACTTACGCACACAGAGGTGCAATTGCAGATGGCGACGAGTGTAGCGTGTAGTTTTTCTCGGAAATGAGCAATGAATGAAATTCGGTTG
TTTTCAGTACTCACACGCACACGAACGCAGATGCATACACTCGCAATTTGGAGCAAGAGAGAAAGTCTGCACGACATGCGCTCTGGCGTTTGTGT
GTATACAATTTGCTTACTTTTTGCGCTACAATTGGCAAATAAAACAATAGCGCAATTTTACGCAGCACTTTAGCTTACTAACCCACATTGATGGC
TCCACAAAGCGAGCAAAATAATTTGTCTGCCTAATTGAAATAAAATAAATAAAACTAAGCAGAAAAAATGTCGGCAAAAAACAAGGCGCAGCTGT
ATTGTGCGCTAGTGTGTGTAAAAAGGAGACGGCCATAGAAAAAAAAAAACACATATACACACAGGAGAATTTACTGCTGCTTGCGGCGCCCACACA
CACATACACAAAAACACTCGCCTATTTAGTACAGCAACTGCGTAAATTCAATAAAAATAGTCATCTGGAGTAAAAAAACCCAGTTTCCTGTCTTC
ATTTCCCTTTTTCCGTGAAGGTACACAGTCACTACTGTTATAATTTAGCACACACACTCGCGCATTTATGTATGCATTTGGGTTGCTTTCATTTG
GATGTTTATCACTTACTTTACCACTTACTTTGGGATTTAGCTCTTCGTTTGTCGCACTTTTTTGGCCTGTTTTCATGCCATTTTCTTTTTGAAAA
ACTGAAAGAGTACAATTCGTTGTGTCGCGTCTTAAATGAACAAGTGTTGCCAGACTTTAGCTGGAGGGAGATGACACTATCGCGAGGCAGCATAA
AAATCAGTGCTGTAAAGCGAAATTAAAAAAAATATCTGATAACTTTAATATTAGTTTATTTGTTTACTGAATTTTACATTTTCTTATGTACTATA
AATAAAAATCAATTCATAAATTTATTTGAGAGGAGTAAAACAAGAAGAATCCACCTAAACATTACAGACTTAAGTTCTAAATATCCCAAACGTTG
TTTAATTTCTATTTATATTTGTAACGATTAGTTAGTTATTAGTAATAATGAAAGAACTAGTGATAAAATCCATTTGTAATCACTGCTAGAATTGG
CTTGAAAATAGCTAGACTGACGTTAACAATACTGTTACCAGTTGGCATTTCCTGATCCGGCAACTCCACACGACGCCATTTCAAAACAAATGCGC
GGCAACGATTTTATTTTACCCCGCAACATTTAGTGAGAAGTCGCAAAATAAGTCAGATTATTTGATTAAAATGGGAGCAAAGGCAACAAAAATGG
AAGGTGAATATCTGCCGGATACGCCGACACTAAACAAAATGCGCCTGGCCAGCGAAAAGCGAGAACAAATGGAAATGACGACGCCGAATCGAGAG
CAAAACAACGCTTTGCTCGATCCTCGATCACCAAATGGCTGCCGCACGCCTTTAACCGTGAGTTTATAGGCATTAGGTATTTTTTGATATTACTA
ACCCTAGTAATGATGGCTGCGTTGTAGTTCTTGCAGGCGTCAAAACCTCGCGTTGAGGAGGAGGAGCAGCATGTGACCACCAGTGAAAATGCCTT
CTCCATGCTGCGAAAACGTTTGCTCAAGGGCTTCTCCCTGAACGATCCTCGCTCTCCTCAGCTGAATCGCACTCCACTGGTCCTCGATGAGGTTC
GTTCGCTTAATATGGATGACACATTCGCCGATCTCTTCGTGGACACCAGGGTGGGTACAGCACAGAGAGCAGTGC
(SEQ ID NO: 1507)

Exon: 10380..10289
Exon: 4869..4674
Exon: 2328..1001
Start ATG: 2087 (Reverse strand: CAT)

Transcript No. : CT29014
ACACAACGAATTGTACTCTTTCAGTTTTTCAAAAAGAAAATGGCATGAAAACAGGCCAAAAAAGTGCGACAAACGAAGAGCTAAATCCCAAATTT
TCTAAACACACACACATACAGAAACGAGAAGAGCCAACGAACTCGCAGCGACGCCCAAGAATGAAAGAGAGCAAGGCAACATGAAAATTACAGCA
ACAACAACTGGCTTGCCGAAGAAGTTGTAAAAGACGCAAGAGCAGAAGAAGAAGCAGCCACAACAGTATTTTTTATTAGCGGGTGTTTTTGTTGT
CATATACACACATCACCCCTAACTCAACGTTTACGTTCCACCAGCAGCATACCTATGTAGAGAAACCCGATTCCAAAGAGATTTGACGACGCCCT
AGCAGCGGACAACGAATATTCTAATTTATTTATGTGATAGTCACTAGTTTTAATATTCTTAAGCTTTTAAACAACCAAACGTTGCACGCCAAAAA
ACGAACAAGCCGATACGCTACGCTAAAAAGCTACAAATTGTAATGCATTCCACAATGAGTGTACAACATGGGCTGGTTGCCCTGGTACTGATCGG
CTGTCTGGCACATCCGTGGCACGTCGAGGCCTGCTCCAGCCGTACGGTGCCCAAGCCGCGCTCTTCGATCTCCTCGTCCATGTCCGGCACGGCAT
TGCCGCCGACCCAGGCTCCAGTCACTAGTAGCACCACAATGCGCACCACCACGACGACCACGCCCAGGCCCAATATTACATTCCCCACATACAAA
TGTCCGGAAACCTTCGATGCCTGGTACTGTTTGAACGATGCCCATTGCTTTGCGGTGAAGATAGCCGATCTACCGGTTTACAGCTGCGAGTGCGC
GATTGGCTTTATGGGACAGCGATGCGAATACAAGGAGATCGACAATACTTACCTGCCCAAGAGGCCGCGTCCGATGTTGGAGAAGGCGAGCATTG
CCAGTGGAGCCATGTGTGCCCTGGTATTTATGCTGTTTGTCTGCCTGGCCTTCTATTTGCGCTTCGAGCAGCGGGCTGCCAAGAAGGCCTACGAA
CTGGAGCAGGAACTGCAGCAGGAATACGACGATGACGACGGCCAGTGCGAGTGCTGCCGCAACCGGTGCTGTCCAGATGGCCAGGAGCCAGTCAT
TCTGGAGCGCAAGCTACCCTACCACATGCGGCTGGAGCACGCGCTAATGTCCTTCGCCATTCGACGCAGCAACAAGCTGTGAGCGGAGCGAACTA
TGGAAACTATGAAAAGATATAGAAAGTCGAATTTCGAATATGCCTTGCCCAACACACAATTCTTAACTGGGCTTTAGTCGATAGCTGATAACTCC
TATTTACCTACCGCATGCTAAAGATCTGTTCACCCGATTCTATATAGAGATCTTGACTTTCTCTTACCAAAAGTTACCCAGAAAGGGGGTTTTAA
AGCCAGACAGCCTTGTATTACCCAATTGACTATGAATTTTAATACCTAACGCTAGCTATTTATTATTACTGCTAACTGATATACGTATCACACAC
ACAACGCGACACACGCGCCAAGTATTATTTATTGCGAGAGATTTAAGAAGAAATGATATGGATTTTCTAAATAAACATACGAAACTGCACCATGC
A
(SEQ ID NO: 1508)

Start ATG: 530 (Reverse strand: CAT)

MSVQHGLVALVLIGCLAHPWHVEACSSRTVPKPRSSISSSMSGTALPPTQAPVTSSTTMRTTTTTTPRPNITFPTYKCPETFDAWYCLNDAHCFA
VKIADLPVYSCECAIGFMGQRCEYKEIDNTYLPKRPRPMLEKASIASGAMCALVFMLFVCLAFYLRFEQRAAKKAYELEQELQQEYDDDDGQCEC
CRNRCCPDGQEPVILERKLPYHMRLEHALMSFAIRRSNKL*
(SEQ ID NO: 1509)

Name: PROTEIN SPITZ PRECURSOR
Classification: signal_transduction
Gene Symbol: spi
FlyBase ID: FBgn0005672

Celera Sequence No. : 142000013384600
CACTGAACAATATTTAAAAAGTTCAAAATCACTGTACAGTACTTGGTATTTTAAACATCCATCACTTTTCCATTCAAAATATATAAATATTGAAA
AGCATGACATACGATGTTTTTTTTTTTTTATTTTAACTTAGTGTGTCAACTATCTTTATAAAAAAAATTAAAATTTTCTGGGAATCCAATAGAAA
GCTCAGTCTGGAGATGAATCCTCGAAAGCGGAGCTAATTTGCAAGCAAGACTCGGCATCCAATAGTGGATATCTGCAGATCGTCCGATTTGAGAA
CTCCGAAATCATATGCTTTTCATTCCTATTTTCTTTAGATCCCGGACAATTGATTTCTGTTTTTTTTCTGTTTTGATTTTCATCATCGATTGATT
AATTTCCATGAGGACATTGTTTTCAAAGCTTTTAAGACCGCGAATAAATCCAGTCTCATTCAGTAAAGATTCGTGAAGGCAATTTCGTGTGATAT
CAAGATATATATGTATATTCGGAAATAATGTTCACGTGAACCTCGCGATTTGGAAGTTCAATCCTTTGAAGGATTGAATGATTAGGACGCCATCC
TTTATATGTTTTAGATATAAATATCACCCTTCACCTTCTCCAGTTTGATACCTATCAATATTACTAGGGAATGCATTACGACGGAATTCAAAACA
TCTTGAAAAACCTCCAATTACCCCAGTTCAGATTGACCGTTTTATTGCCTCCCATTTTTATAGTTCCGAAGAAAATTACGAACGCAGAGGCATCA
TTTTAGATTACCTAGATTGCCAAGTTTCATAAAACAAAACCATCTTTAGATTAGGTTTTCAATATTTCGGGTTTGCTGATTTCGATATCGATAAG AAACTGACGTATGTATGTGTGAAGTTTTAATGGGTAAAAATATCGATATTCTGGCGAAATTTTATGTAAAGCAAAATGTGAATGTAAAAATACTA
AAAGTGGTGAGTTCGATAGAGCCGCGTAAAAATATTTTCATTATCGATAACCGAAGTATTATTAATCTTTGCCAAAGACCAGCTTTGGCATTACA
ATACAATTTTGGGGATAGATTAACTAGTGCAGCCCAGCAGGCAGCACCGTGATTTGCAACAATTTGAGCCTCACTCATTCAAGAACCTTCCAGCA
ACTAGTTCGCCTAGTATATATACCTGCTCTCACCCAGCTGCACTTGTATACACAATCGAACGGCCGAACAAAAACTACGCAGTAGTCGAGAGCTC
CAAATTAATAGAATCCGTCACATAAATTCGCCGCAACAAGTTAAACGAGAATAAAAGCGTCAGCATCGATATATATACATACATATATTCAAAAG
TCTGTCGAAACTACAGAATACGTTGCGAAAATGCCGGAGAAGCTGTTGAAAATCACCTACCAGGGCGCTGGACCCCAGAAAAAGATAAATGCATA
CCTGCGGATGCCCTCCCAGAATTACACCATATTGCGTCGCGAAATCGAGCTGTATCTTTTCCAGGAGCGCCAGTTACCCAAATGCGACGTAAGGA
CCTTCTGGATCGGTGAGTTTTACAATGAAAATGCCGCAGAGTGAATGTTTGCTATACATACAAACAGTTATTCGCAATTGCAATCGAGTCGCAAA
GATTGCAACATATGTGCATGGTATAAGTACATTCGTTTCCATACATAACTGCATCCGTCCGAGCAGTGCTGACCATTTAGCTTTTAAGTCTCGTT
ACTTAAAAACCAGCCCAAATTATTGCGTACTTTGCCCAACAAAGCAGGGATTCACCTAGATAGTATTCCTGCTCAATGCTTATCATTGGCAAAAT
TGTGTTGACACATTAGCTGATAAATATGTACATATATATTTTTATGGTACAAACGTGGTCAACATATTAGATGCACTGTTTCATAAATGGCACAC
ATACAAAACATTTTTGATTTTACATATTTCTGAATTCTCGAATTATACATATATATTTTAAATACATCTAACGCGCTTTTTAATTTGTAAAGTAT
GTGTACATGTACTCATATACATTTACATAGATCAAACGGGTTGTGCTGGTACAACCACAACTGTAGCTAATTTGTCTAACTAGAGCCCTCAGTGA
TTCACCTTTGATAACAAAACTTCACTGATTCATAATTGATTTTATTTTCCTTTGCCTATTCTAACTTTTGCAGACGCTGATAAAGATGAAATCGA
AATAGTCAACCAAAATGACTATGAGATTTTCCTGGCCAAGTGCGAGAGCAATATGCACGTTCAGGTGGCTCCACTGGCGCCCGTAGAGGAGCCAA
AGGCCACCAAGCAAGAGGGTTCTTCGGCCAACGCTGAAGCTCCTTCTGTCGACGATCCGAGCAATTTCACCATCCACGACGCCGTTGAATGCGAT
GGCTGCGGCTTGGCTCCCTTGATTGGGTTCCGCTACAAGTGCGTTCAGTGCAGCAACTATGATCTTTGCCAGAAATGCGAGTTGGCTCACAAGCA
TCCTGAGCACTTGATGCTACGCATGCCGACCAACAATGGACCCGGTATGGTCGATGCCTGGTTCACAGGTCCAGGATTGGGACGCCGCAGTGGCC
GGCGCTCCAGGGGACATTGCCCGTTTCAGGAGACGAACCAGGCAGATCCTGCTGGCGAACCCGCAAGGGATAGTCGCCGTGAACGGCGTCAGGCC
CGCCGCCATGCCGGAGTCTTGACTCAGTTTGTCGAGATGATGACCAACTTGCCGCTGAACACAACAACGGCCACGGCACCAGCCGAACCGCAGAA
ACCGAAGGCTGCAGAACAAACTGAAAGTCCTCCACAAGCTGAGCCCACTGTTACCGCTGAAAAGGCAGCTGAATCCGAGGCCAAACCAACTGAGC
CGAAGAAGGTTAACACTGATCAAAGTGTCCCTAGAACCGAAGATCCAGTGACGACTCCACGTTCCACTCAGCCAACTACTCCAGTGATTAATCTG
GATAACATTTCGCAGATTGTGCCACCCGAGTACATGAGTGCTGGCATCGAAATCCTTAATAACTTCAGCGAAATGTTTTCCAAGATTATCGATAC
CACTGAGGGCGGTGATTCGGGAATTTTTGCGCCCTCAACGACTCCCAGTGCTGAGAATAAGAAACCAGAAGAGCAGGGTCAATCCAGTGGCCAGT
CGGGGGCATCCTCGGCCAACCAGTCAGCTGTTCCCTCTGCCGCTCCATCGGCTAATCAGTCTAATGTCCCATCTGCTAACCAGTCGGCCACTCCA
TCAATTTCTGGTTCGATCCCTGATGCTCAGCTTGAGACAGAGCCCCTGAATCCTAAGCCATCGGAAACCACCACCGAAACAGAGCAGGAAAGACG
CCGTTCAGACAGCTTGGATCCAGAGTGGCAGCTTATTGACAATGCATACTCTGCAAACAATAGTAACTTGATCAATCTGGACACAACCAATCCCA
CTGCTGCTCCTCAGGAGCCGGTGCGTGATTTTGGTCAGCTGGGCGAACTATTGCGTCAGCACATGAATGAGGAGGCTCGCGTGGAGCAGGCTTCG
GCCAACACCCAGACTGCTCAAGTTGATACGGTGAGTACATCGACCTCGACCACATCGGTGACCACCAATAGCGTCGGCACCTCCCCAGCAGCTCC
CGACGACAAGCGCACGGTCCCCGTCTACCACACTGGTAAGTGCCGAATTAAATAACTAATCGCTTTGTATTAATTATGTCTCCTAATTAGATGAA
AGCATCAATAAATCGATCCATGCCATGATGGCCATGGGTTTCAGCAACGAGGGCGCCTGGCTAACCCAGCTCCTAGAGTCGGTTCAGGGCAATAT
CTCAGCTGCCTTGGACGTAATGAACGTATCGCAGAACCGCAACTAAATATTCATATTCAATATCGATATATCTACAATGTATCTTCAATATCTAT
AGAACCCAATGAAAAAGGGATTTTACTTTATCGTATCAGTTTACTACGTAGCTTAGTTTTTCTGTGGTGCTAGATTTATCTCGTAGCCAAAATAA
ATGTGAAAATAGATATATGTTATGTTTTAAATAATCAACAAAATGTTATCGTATATATATGTATGTGTGAAATTGCAATAAAGGCACAAAGTAAA
ATGATTTAAAATGCCTGCTTTATACCTGATATGGTTTTGTTTAGTAGAGTACGATTGACAGACAACAAAAGCCTCCTCCACTTAGATAATGTGTT
TATACGTATGGTATAAATCGATTCTGGTTTTTCAGAGTTCAAATCCGCAAAGCACTCGAATTATTTCTTGAGTGATACACAAATCCACAATACTG
TGTTTCGGAATTCGATTCGTTTCCTGTAGTATTGATATTCCAGTGTGAACACTACTCGCTTGTCGAAAGAGCCTCAAAGATCTTCTCTAGCTTCT
GCTGCATCTGATCCAATAAAATAGTCTGTCGCCAAGCCGGCAACATCTCGCACAAATCTCCGGAGTTCGTAATTTGCAGTCGTAATGGTGGCAAT
AAATGTGAAAAATTTGAAGAGCTTCTGGTGGTGTGCCTTCCACTGTCGCCGACCGAATCCCGTGTTATATCCGAACATTTGAGATACCATCAGAA
CGAGGAATCCGGACAATCCGAAAAATCGATGAAGCATTTTCAAGGCGAAGCCACTGTTGATGAAATACAGCGGAAGACCGCTCAGAACGCTACCC
AGAAGAAGAGCACAACCGATTATACCTGATGGGCGAAAGATGGAGGCATAAATTATCATTATATTTGGGAAAAGAACCGACGAGAACACACCGTA
AAAAGCATGGTTGCTCTTAAAGTGACGAACGGTGGCATTGGGGTCTTCCCGTTTGCGCTCCAGCTTCTGCCATGTCTTGATTCCGATTCCGCCGG
CTCCGACCAGGAATGCCAACAGCCCCAGGACGGCGTGCAGGCGGTTGAGGTTCAATGGACCCAACGAGGACTCCAAATATGCGCTATTCCGGACC
AGCAATGCTTCGCCCATGAAAAACACAAACTATAATGAAATAGAAGATAGATGGAACAATGATTTAGGACGGGTAAAAATTTCAGGAGATAGTAA
ACCAGTTTATATTTAGGTCTTCCGGGTACAGAAAACTCTCACTCGAGAAATATATATCCTTGAAACCATTAGATTATTTGTTAACCGTGGCCTCA
AACTTTCACTTTTTCACATATGTTTCTAAATCTTTTAATATCCGAAATCAAAATACTTACGCCGATTGTGCAGTAGAAGGCATGTCCGGCGGTGT
GCACCAATTTGAGCACCAGACACTTGTAAACAATGGCTACGGTGATCCCCGCCAGAAGCACATGCGAGATCAGTGTGCAGAAGCCAAAGTAGAGG
CCTCCATAGGAACCTTGCAATTCGGCA
(SEQ ID NO: 1510)

Exon: 1001..1532
Exon: 2164..3645
Exon: 3701..4347
Start ATG: 1361

Transcript No. : CT29100
CCGAAGTATTATTAATCTTTGCCAAAGACCAGCTTTGGCATTACAATACAATTTTGGGGATAGATTAACTAGTGCAGCCCAGCAGGCAGCACCGT
GATTTGCAACAATTTGAGCCTCACTCATTCAAGAACCTTCCAGCAACTAGTTCGCCTAGTATATATACCTGCTCTCACCCAGCTGCACTTGTATA
CACAATCGAACGGCCGAACAAAAACTACGCAGTAGTCGAGAGCTCCAAATTAATAGAATCCGTCACATAAATTCGCCGCAACAAGTTAAACGAGA
ATAAAAGCGTCAGCATCGATATATATACATACATATATTCAAAAGTCTGTCGAAACTACAGAATACGTTGCGAAAATGCCGGAGAAGCTGTTGAA
AATCACCTACCAGGGCGCTGGACCCCAGAAAAAGATAAATGCATACCTGCGGATGCCCTCCCAGAATTACACCATATTGCGTCGCGAAATCGAGC
TGTATCTTTTCCAGGAGCGCCAGTTACCCAAATGCGACGTAAGGACCTTCTGGATCGACGCTGATAAAGATGAAATCGAAATAGTCAACCAAAAT
GACTATGAGATTTTCCTGGCCAAGTGCGAGAGCAATATGCACGTTCAGGTGGCTCCACTGGCGCCCGTAGAGGAGCCAAAGGCCACCAAGCAAGA
GGGTTCTTCGGCCAACGCTGAAGCTCCTTCTGTCGACGATCCGAGCAATTTCACCATCCACGACGCCGTTGAATGCGATGGCTGCGGCTTGGCTC
CCTTGATTGGGTTCCGCTACAAGTGCGTTCAGTGCAGCAACTATGATCTTTGCCAGAAATGCGAGTTGGCTCACAAGCATCCTGAGCACTTGATG
CTACGCATGCCGACCAACAATGGACCCGGTATGGTCGATGCCTGGTTCACAGGTCCAGGATTGGGACGCCGCAGTGGCCGGCGCTCCAGGGGACA
TTGCCCGTTTCAGGAGACGAACCAGGCAGATCCTGCTGGCGAACCCGCAAGGGATAGTCGCCGTGAACGGCGTCAGGCCCGCCGCCATGCCGGAG
TCTTGACTCAGTTTGTCGAGATGATGACCAACTTGCCGCTGAACACAACAACGGCCACGGCACCAGCCGAACCGCAGAAACCGAAGGCTGCAGAA
CAAACTGAAAGTCCTCCACAAGCTGAGCCCACTGTTACCGCTGAAAAGGCAGCTGAATCCGAGGCCAAACCAACTGAGCCGAAGAAGGTTAACAC
TGATCAAAGTGTCCCTAGAACCGAAGATCCAGTGACGACTCCACGTTCCACTCAGCCAACTACTCCAGTGATTAATCTGGATAACATTTCGCAGA
TTGTGCCACCCGAGTACATGAGTGCTGGCATCGAAATCCTTAATAACTTCAGCGAAATGTTTTCCAAGATTATCGATACCACTGAGGGCGGTGAT

FIGURE SHEET 822

TCGGGAATTTTTGCGCCCTCAACGACTCCCAGTGCTGAGAATAAGAAACCAGAAGAGCAGGGTCAATCCAGTGGCCAGTCGGGGGCATCCTCGGC
CAACCAGTCAGCTGTTCCCTCTGCCGCTCCATCGGCTAATCAGTCTAATGTCCCATCTGCTAACCAGTCGGCCACTCCATCAATTTCTGGTTCGA
TCCCTGATGCTCAGCTTGAGACAGAGCCCCTGAATCCTAAGCCATCGGAAACCACCACCGAAACAGAGCAGGAAAGACGCCGTTCAGACAGCTTG
GATCCAGAGTGGCAGCTTATTGACAATGCATACTCTGCAAACAATAGTAACTTGATCAATCTGGACACAACCAATCCCACTGCTGCTCCTCAGGA
GCCGGTGCGTGATTTTGGTCAGCTGGGCGAACTATTGCGTCAGCACATGAATGAGGAGGCTCGCGTGGAGCAGGCTTCGGCCAACACCCAGACTG
CTCAAGTTGATACGGTGAGTACATCGACCTCGACCACATCGGTGACCACCAATAGCGTCGGCACCTCCCCAGCAGCTCCCGACGACAAGCGCACG
GTCCCCGTCTACCACACTGATGAAAGCATCAATAAATCGATCCATGCCATGATGGCCATGGGTTTCAGCAACGAGGGCGCCTGGCTAACCCAGCT
CCTAGAGTCGGTTCAGGGCAATATCTCAGCTGCCTTGGACGTAATGAACGTATCGCAGAACCGCAACTAAATATTCATATTCAATATCGATATAT
CTACAATGTATCTTCAATATCTATAGAACCCAATGAAAAAGGGATTTTACTTTATCGTATCAGTTTACTACGTAGCTTAGTTTTTCTGTGGTGCT
AGATTTATCTCGTAGCCAAAATAAATGTGAAAATAGATATATGTTATGTTTTAAATAATCAACAAAATGTTATCGTATATATATGTATGTGTGAA
ATTGCAATAAAGGCACAAAGTAAAATGATTTAAAATGCCTGCTTTATACCTGATATGGTTTTGTTTAGTAGAGTACGATTGACAGACAACAAAAG
CCTCCTCCACTTAGATAATGTGTTTATACGTATGGTATAAATCGATTCTGGTTTTTCAGAGTTCAAATCCGCAAAGCACTCGAATTATTTCTTGA
GTGATACACAAATCCACAATACTGTGTTTCGGAATTCGATTCGTTTCCTGTAGTATTGATATTCCAGTGTGAACACTACTCGCTTGTCGAAAGAG
C
(SEQ ID NO: 1511)

Start ATG: 361

MPEKLLKITYQGAGPQKKINAYLRMPSQNYTILRREIELYLFQERQLPKCDVRTFWIDADKDEIEIVNQNDYEIFLAKCESNMHVQVAPLAPVEE
PKATKQEGSSANAEAPSVDDPSNFTIHDAVECDGCGLAPLIGFRYKCVQCSNYDLCQKCELAHKHPEHLMLRMPTNNGPGMVDAWFTGPGLGRRS
GRRSRGHCPFQETNQADPAGEPARDSRRERRQARRHAGVLTQFVEMMTNLPLNTTATAPAEPQKPKAAEQTESPPQAEPTVTAEKAAESEAKPT
EPKKVNTDQSVPRTEDPVTTPRSTQPTTPVINLDNISQIVPPEYMSAGIEILNNFSEMFSKIIDTTEGGDSGIFAPSTTPSAENKKPEEQGQSSG
QSGASSANQSAVPSAAPSANQSNVPSANQSATPSISGSIPDAQLETEPLNPKPSETTTETEQERRRSDSLDPEWQLIDNAYSANNSNLINLDTTN
PTAAPQEPVRDFGQLGELLRQHMNEEARVEQASANTQTAQVDTVSTSTSTTSVTTNSVGTSPAAPDDKRTVPVYHTDESINKSIHAMMAMGFSNE
GAWLTQLLESVQGNISAALDVMNVSQNRN*
(SEQ ID NO: 1512)

Classification: known_flybase_gene
Gene Symbol: ref(2)P
FlyBase ID: FBgn0003231

Celera Sequence No. : 142000013384598
ATGATTTAGATGTTGGCTTACAAAAAAACATGTTTTATTACGGACCCGGTTGGCCCCAATCCATTCTGTCTAAATTCCTCCGATGCGAATACACT
TTGTTTTCTTCTAAACCACTTTTAAGACTTCTTTTTAGTTTACATATATTAATTCTCCATATGACGCTTCTCAAGCTTAATATATTTGAGTGAAT
TTTAAATGAATGTTTTCCACTTATGAACACGCTAGTTACACACAAGGTGTTAGGATTGAATCACCTCCTCGCAGAGCCAATACCAAGTGAAGAAC
GGATCCACCTTGCACTTTGTAGTCCGCCGCGGTTTATCGTCATTCCTGGGGGGGATCGCATGCGAAATAAGCTAAAATCAATGACCAATAGCCA
GAAAGACTCACATTTGCTTGCCGGAGAAAATAAGACGCTGTTGCTGGGGCGGAATGCCTTCCTTTTCCTCCACGCGCTCCTTGATGCGATCTACC
TTGTCCGTGGGCTCAATGTCGATCTCGATTTCCTTGCCGGTCAGGGTCTAATGGAAAGATAATACATATTTACATTAATAATCCAGCCACACATA
TATTGACTGTAATATTCGACGATTTTGTTGTTGTTCAAAGTGCCCGCTGGGCACGATGGCTGTGATTTATCTTTATCCTACTTTTTTGCTACTCC
ATATCTTCCACACTAACCTTCACTTTGATCAACATTTTGTGTGTATTTAACTAGGCGCTCCTGTACAAATTCAAAATTGCCGAAATTTTTGCAAA
TCTCCACAGCTGGTTCTCTTTTTTGGCTGTCACTTTCGGCGTTGGTACGACTGGCAACTATCGATAGTACTGTCGATGACCATCGATTGTTTTCC
ACACTATTACAAATATAGTATTTTCTCCATCATTCCATCTCTACACAATTCACGTGTAAAAAAATACATTTCGAAAAAGGAGAACTTAATTTATG
TAAATTTTTTGTAGCTTGATTTATAGTGTGCCCATTACGGTTAGAAGTCTCACATATTTAGAATTCAAATTCTCCTTAAATTATTTTACTCATGA
GATGCAAAAATCCATTGAATGCCATTACTACATTTTTTAACTTTTGAAAAAAATGGAAGGCGTCACTTTTGAGGGATTTGAATTAAGAGCAATTT
GTTTATTAATGTTTTATCTCGGATCTTAGAAAATTAAAAAGTATTTTTTTGTCTTTTGTCTTTTCTGTTTTATTAAAATAAGTTGTATGCCTTAA
TAACTAAATACATTTATTTACAGTACTAAATGGATAACTACTTTGTTCTTTTCGAAGGTACTGAGATCCCCAGCTTAGAAGTTCATCCCTATGAG
AGCTTCTTCAGTTTGTTCCAGTCGCGAATGGCCTCCCCGATGTGGCGTATATCCCTCGCATAAGTGCGACAGCATCCCCCAATGACCTTGGCCCC
CAGTTGCGCCCACTCCGGAACGTAGTTCGCCAAGGGCACACAGTGCTCCCTTCCCTGCCAGCCGTTGACCACGTCGTATACCTCTCCGCTATTGG
GGTACACCACCAACGGTATCTGCTCACCCACTTCGCGGTCACCATTCAAACTCTTAAAGAGCGGGGTCACAAACTTCGGATGCACACAATTTACT
CCGATGGCCAGGCACTTATCCTGGGCATTTCGTTCAGCCAAGAGGTCCCAAATAGCATTCGCCGCGTCCGCAAAGGTTTCTCCATGCGCCAGGGT
ATTCTCATCCTTGCACTGGAAGGCCACCCAGAACTTCACATCCGGATAATCATCGCACAGCATCTCCACCAGGGCCTCCGCCTCCATTTGACAGG
GAATCGTCTCGATGGCCAGCGCATCCACACCAGCCTCCAAGCACGCTTCGATCCTCACGCGATGCCAGTCCGTAATCTCCTTGGCCGGCACAAAG
TCGGCATAGCTACCGGTGTACTCGGAGCCATCGTGCAGGTGGGCCCCAAAGGGTCCAATGGAGGCAATGATCAAAGGGTATCCTTTAAAAACAAT
AAATTGGAATATATAATTGGTAAATATTACTATATATAAAATAAAGTATTAAAGAAAGTATTAAAAGTAATGACCCTACCACATCATTCACTTGA
CCACAATCTAAATTAATCCCGCCCGAGCTGGACCTCATGGATGTCAACTTACCCTCCTGCACCGACAGCTGCGCCTGATAGCACTCGGTGAGATA
GCGTTCCTTGGCGATGTGGGCCAGGCGGACCGTGTTCTTTATCAGCTCGATGCTCTGCTCCTCGTCCAGCTCCAGGTACTCCATGTAACCATCGA
CACTGGACTGGTAGGTGTTGGTCAAAATGATATCGGCACCATCTGGTGTTGTCAAGGGGAAAATTCAGTTAGTATGTTGCCAATTGCTACCGGAA
AACAATTGCTTACTCTGCAAAAAGTCCAGGTGGGTGCTGATAATGGCCGCCGGATTGGTGGCATTGAAGCGGGCACTCCATAGCGGATCCCCATC
CACAGAGTCACCCACATGGACGGTCATCTGGGTGCCGAAACCGCCATCCTTCACCAGCACGCGCGTCAAACCCATGATTGAAAGATTACTAAGAG
GGGTGGAGGATGATCCGTTGAAAATTGATTATTAGTTACATTTCTACGTCAGCGGGCTGCGAGATAATTAAATATGTATATTGCGTCTGCCACCT
GGATTCCACTGCACTCAGGGCGATGTTATACAATGTATCGGAAGAACTAATCTCTATTTTTCAGTTCAACGAACTTGGCAGAACAAAAGACCAGT
GGCTTAATCTAAAAAACACACTGAGAAAAACAGCTCAAAGTTCTTTAGCTAAGATATATGTTATATGAGTCTTATGATTTATTATAAAAAAGATT
TAATTCTAGGAGTATTCAGCTTTCACTGAATAGTATACAAATTTAAAACCAAGGTCACATTTTTACGTATCTCAATAAATGGCGAGTTAAAAGCC
TGAAACATTTTATTCTGTATACGCTAAATTCAAAATATACATCAGCTCTTTAAAATTTGGCAACAATTTTTGAGAAATATATATCTTTTAAAGTG
AATCATTTATTACGTTTCAAGATCTATTCTTGTTCCAAATTAAAAAATATATTAATATTTAATATATGTAAGTATTCCAAGCATAACATTTTTAG
ATTGCTTATAAGATCCCTTTGTTGCACTTTTAAGCATACTCCTTGGATAGTGTATACACCGTCTGTCATCAAAATCTATCGGTAGGGAAGCGAAA
AACACACGATAAGGTCTCGCACTCACCTTGACAGCTTGTTTATGGATCTTGTAAATGGGCAAATTCAATAACAACTTTATTAGACACTAGACTGG
CTGGTTGGTTATCAAGTGGTTATCACAAATCTTTCGGAACGGTGGATATGATCAGTCGCAATGGACGCTCGACGAACGTTTAAATGTTTCACGTA
TCGTCGAGGGGCTTTTATACTTTCCGAAGGGCCACTCAGCTGTGCGGCTCGGCTTATCAGGGCGAAATTTATAATATTTATAATAATTTATAACA
AAACAAAACGGCAAACACAAACATGAGAGTGCCCCCACCAAGTGGGTGATAAGCCCGGTGCACAGCTGCCAGACGCTGGCCAGCCAGATTGGATT GTCCGGGTGGACTGCGACTCCCCCTCCACGAGGCTGATGAAGCTGATGAAATCGTCAAAGCGCCGCTGTGCGTGGTTCTGGCTTCCGAGTGACTC
TGCTCGGGATGTCGCATCTGCTAAGTCGACGCCGATAACCTCTGGACGCCGCCTAGGACCAACACTTCAAGATGTACTTGGTTGTTGACTCTGTC
CTCCTTAAAGGAAAATGGGTGAGCTTCCGACCGCACTCAATAGATTATGGTCCAAAAATAGGTCTACTGATGTCAAAGAGAAAAACAACATTTAA
CCCCTATTCTGGTAAACAAATCGCTAATGAACAGGAAATAAGACATAAGATATATCAAATAAAATCTCCTCTAAAAGAGATGAGCTTAAAGTGAT
GATTGTTATTAATATTTGGACAAAAAAAAAAATAAATAAATAAATAAATAAATAAAGTAAAATGTAAAGTAAGAGATTGACCGACAAAAGGCTTTC
AATTTGAAAATGGCCGTTAAAATCATGTTTTTTGAACGAAGTATCCGATTAGGCTGATTGCCAGATTGGGTCAGAGTGCAATAGGTGGACATGTG
GCTCCACCATCCTCAAAAGCTTCAACAGCCAAAAATGTAAGTACTCTTTTAAAAATGCGGTATGAAGTTCCAAAAAATTTTGAAATATCTTTCAT
AGTGATAAAGTCGAGAACCGCAAGAATAGAAGGGCATACCCTTCTCTATAAAGTACCTTGCGTACCAGAAGGCGTTTGCCTTGGTACATATGTAA
GAAGTGATTAGATTTGATGAATCT
(SEQ ID NO: 1513)

Exon: 3394..3257
Exon: 2558..2389
Exon: 2322..2143
Exon: 1982..1001
Start ATG: 2545 (Reverse strand: CAT)

Transcript No. : CT29750
AGCGTCCATTGCGACTGATCATATCCACCGTTCCGAAAGATTTGTGATAACCACTTGATAACCAACCAGCCAGTCTAGTGTCTAATAAAGTTGTT
ATTGAATTTGCCCATTTACAAGATCCATAAACAAGCTGTCAAGTAATCTTTCAATCATGGGTTTGACGCGCGTGCTGGTGAAGGATGGCGGTTTC
GGCACCCAGATGACCGTCCATGTGGGTGACTCTGTGGATGGGGATCCGCTATGGAGTGCCCGCTTCAATGCCACCAATCCGGCGGCCATTATCAG
CACCCACCTGGACTTTTTGCAGAATGGTGCCGATATCATTTTGACCAACACCTACCAGTCCAGTGTCGATGGTTACATGGAGTACCTGGAGCTGG
ACGAGGAGCAGAGCATCGAGCTGATAAAGAACACGGTCCGCCTGGCCCACATCGCCAAGGAACGCTATCTCACCGAGTGCTATCAGGCGCAGCTG
TCGGTGCAGGAGGGATACCCTTTGATCATTGCCTCCATTGGACCCTTTGGGGCCCACCTGCACGATGGCTCCGAGTACACCGGTAGCTATGCCGA
CTTTGTGCCGGCCAAGGAGATTACGGACTGGCATCGCGTGAGGATCGAAGCGTGCTTGGAGGCTGGTGTGGATGCGCTGGCCATCGAGACGATTC
CCTGTCAAATGGAGGCGGAGGCCCTGGTGGAGATGCTGTGCGATGATTATCCGGATGTGAAGTTCTGGGTGGCCTTCCAGTGCAAGGATGAGAAT
ACCCTGGCGCATGGAGAAACCTTTGCGGACGCGGCGAATGCTATTTGGGACCTCTTGGCTGAACGAAATGCCCAGGATAAGTGCCTGGCCATCGG
AGTAAATTGTGTGCATCCGAAGTTTGTGACCCCGCTCTTTAAGAGTTTGAATGGTGACCGCGAAGTGGGTGAGCAGATACCGTTGGTGGTGTACC
CCAATAGCGGAGAGGTATACGACGTGGTCAACGGCTGGCAGGGAAGGGAGCACTGTGTGCCCTTGGCGAACTACGTTCCGGAGTGGGCGCAACTG
GGGGCCAAGGTCATTGGGGGATGCTGTCGCACTTATGCGAGGGATATACGCCACATCGGGGAGGCCATTCGCGACTGGAACAAACTGAAGAAGCT
CTCATAGGGATGAACTTCTAAGCTGGGGATCTCAGTACCTTCGAAAAGAACAAAGTAGTTATCCATTTAGTACTGTAAATAAATGTATTTAGTTA
TTAAGGCATACAACTTATTTTAATAAAACAGAAAAGACAAAAGACAAAAAAATACTTTTTAATTTTCTAAGATCCGAGATAAAACATTAATAAAC
AAATTGCTCTTAATTCAAATCCCTCAAAAGTGACGCCTTCCATTTTTTTCAAAAGTTAAAAAATGTAGTAATGGCATTCAATGGATTTTTGCATC
TCATGAGTAAAATAATTTAAGGAGAATTTGAATTCTAAATATGTG
(SEQ ID NO: 1514)

Start ATG: 152 (Reverse strand: CAT)

MGLTRVLVKDGGFGTQMTVHVGDSVDGDPLWSARFNATNPAAIISTHLDFLQNGADIILTNTYQSSVDGYMEYLELDEEQSIELIKNTVRLAHIA
KERYLTECYQAQLSVQEGYPLIIASIGPFGAHLHDGSEYTGSYADFVPAKEITDWHRVRIEACLEAGVDALAIETIPCQMEAEALVEMLCDDYPD
VKFWVAFQCKDENTLAHGETFADAANAIWDLLAERNAQDKCLAIGVNCVHPKFVTPLFKSLNGDREVGEQIPLVVYPNSGEVYDVVNGWQGREHC
VPLANYVPEWAQLGAKVIGGCCRTYARDIRHIGEAIRDWNKLKKLS*
(SEQ ID NO: 1515)

Classification: hypothetical

Celera Sequence No. : 142000013384637
TGCGGCAGCAGGAGCAGGTGTTTCTGCAGTCTTTTAGCCTGGGCTTCCGTATCATCCTCGGCTTCCTCAGCCAAACTGCTACGCTGCGGCTGAA
CTTCGGCGTAAATGGCGGGAAACTGCGACTGTAGCTTCTGCTTGATGATCCGTATCTTGCGGAATATGTAATCCAGATCCTTCTTCATTTCGCTC
AGGCATTTCACGTGTCTTTTGAAATCCTCGCTGGCACTTTTCAAACGACTCTGCGATAAGGCATTGCAGTTGAGCAGCATCTCGTTGGTTTTCTC
AAAGCGTTGCAGCCTGTGGGATATATTTTGGATGTTTATTATAATCTCTGGTTAAATGAAATGGCTTACATTTGCTTTTGAGCCCGTATCATGGT
CTCCACATCGCCCTGATTCACCATTCCTGCGAGACTTTGAATGAAGGCCTCGGCGGCGGAGTTGCCGAAGCCAGTGAAGGATTCCAGGTCAGGAG
TGGCATCCTCGGACTGGTGCACATCCGCAAGGCCCAAGTGGCTCATTGTAGCCTAGAATTTATTTGTTTATAATAAGGGAGAACACAAAAATTGA
TTTGTTTACTTGCTTTTCAAGGTCTCAAGGTTTCTTTGCGACAACTTGAACTCTGCTTTGTGTGCGTTTGCTGGCAGTTTTAGTTTTTTCTATTT
TTATTTACGTTTTCAAATGGATCTCATGTTTCCATCTATTTTAAAAGTTCTTTTGTTTAGATTTCTTAAAAAAAAAGATATTTTCGTAACAGCTG
TTTAAGTACTAGTTATAAACCAGTGCTGCAAGCTGCCAAAATGCAAAAGCACTGCCGTAATTAAATTTGAACATTTTACTTTTTAACATAAAATT
AACACTGTTTTATGACAACATTTGTTCCTATTTAATATAAATCAAAGTTTCTTTAGCTATTTAAACACTTAAAAATATTTAAATAATAAAGCTTA
GCAGAATGGCATTGGGTATTTTTACGCAAAGCCGTTTTGGTCACACTATGCTCACCGGCTTTTTTTTTATTAAGCGATTGAATTTCCTTATTTAT
TCTTGATTTAAACGTGCAAAATGAAGCTCGCTCCGACTGTTAAGCTAAACAATGGCTACGAGATGCCAATTCTGGGCCTAGGAACCTACAATGTA
AGTCCTTATCATCGGCGATGCTAATAAATCAGCAGGCAGAAATTGTTTATGGAAATTTCTACCATTCAATTCCAATTAAGTGCAATTGTGAAATT
GAAAGTTAATTATGTTATCTGTAGTTAAAGAAGTCTCGCTGTGAGGCTGCCGTGTGCCACGCCCTCGAAATGGGCTATCGGCATATAGACACCGC
ATATCTGTACAGGAATGAAGGCATTATAGGCAAGGTTTTAGCTAAACTTATTGGCGACCAGAAACTGAAACGCGAACAGGTGTTTCTGGTCACAA
AGGTAGGATATAGTACAGATGGGTTATATATAGTTACCAGCACATGTAAATAGATCGAAAATCAATATCCAATTAGCTGTGGGACATATACCACG
AACCCAAGATGGTGAAATACGCCTGTGATATGCAATTAAAGCTACTGGGCGTGGACTATATAGATCTATATCTGATGCATTCGCCGGTGGGCGTG
GACTACATCTCTGATGAAGATCTGATGCCCCACGAGAATGGCCAGCTGAGGACCAAGTGAGTTTGGGATACAACTAAACATACATAGTTTAGATT
CAAGAAGCTTAAAGAAACTGATCTTTGGAACTTATAGCGATGTGGACTATGTGGACACCTACAGAAGTATGGAGCAACTGGTGCATCTGGGGCTG
GTGCGCAGCTTGGGATTGTCCAACTTTAATGCCAATCAGCTGAAGAGATTACTGGAAAACTGCCAAATCAAGCCGGCAAACCTACAAATAGAATG
TCATCCGGAATTGGTGCAAGTCCCATTAATTGAGCTCTGTAAATTTCACAATATCACCGTGGTTGCCTATTCGCCACTGGGGCGTCCCAAAGCCT
GCAATCCGCTGCCCGATTACTACACTGATTCCAAGCTACTGGCGTTGGCAGCGAAATACGGCAAGACACCAGCTCAAATCATCCTAAGATACTTG
GTATAAACGACCTTAGAATTGTAAAGTGATAAAGATATTTATTGGCTAAAAATCTACAGATCGATATTGGCACGGTACCTATTCCAAAAGCTGCC CAGCGAGCCCATCTCGTAGAGAATCTGGATATATTTGATTTCCACCTAACGCCGGAGGAGTTGCTCCAAATGAAGACCTTTAATACAGGGCGCAG
AATCTGGAAATTCGATAAAGCGAAGAATCATCAGTACTATCCGTACTAGCAAGAGATATTTAGTGTTCGGAAAAAAAGTGTAACTATGTAAATGT
ATAAGATAGAATCTCGTTAGATAGTTTAGTTTTTACGTTAGTTTTTTTTTAGTACAATATTACAATGTTATAAAATGTCATCATATCAATCGTTA
TCATATATAAATATACTATATTTTGTGCTAGATATGATCCTATTAACATTTTAAGTGCTCACCTGGGGAAATAATTATTTGTATCTCTCTAAATG
TCTCTATCAAAGTTTATCGAATCTTTCGTGTGCCTTGCGACGTTGATCAGTTGTATAATTTCGGATATTGTTTCGATTTGTCAATTCGCGGCTCT
CCGATATGCTCACAATTTCCTGGCCGAAACGAACGTGTTGCTGTGGTCGAAAATAACAATATACTGATCTCAAGAGTCGCATTATAAAACACATA
TTTGATTCTGTCAGAAAGGAGAAAGGTTAATGATGAATTTGATATTCTCTATTTGCAGTCGAAGGACAACGAAGGCGAAGCCGCTGTGAAACATG
CGATTGATGTGGGCTATCGTCATATAGATACGGCCTATTTCTACCAAAACGAGGCCGAAGTGGGCAAGGCGATTCGGGACAAGATCGCAGAAGGT
GTGGTCAAGCGAGAGGATATATTTTTGGTCACTAAGGTAAATGCCATGATGATATGTTCTAGATCTATCAATAAGATTATATTTTTGCGCAGCTT
TGGAACATTTTCCACGATCCAGAGCGCGTTGAGGGCATTTGCCGCAAGCAGTTAAGCAATTTTGGCTTGGACTATATCGATCTGTATCTGATGCA
TATGCCAGTGGGCTACAAATATGTAGATGACAACACCCTGCTGCCCAAAAATGAGGACGATGTGCTCCAACTGAGCGATGTCGACTATCTGGATA
CGTACAAAGCCATGGAAAAGCTGGTAAAACTGGGCCTGGTGCGCAGCATCGGAGTATCCAACTTCAACAGCGAGCAGCTGGCACGAGTTTTGGCC
AACTGCGAGATCAAACCCGTCACTAACCAGGTGGAGTGCTCGCCTGCGCTCAACCAGAAGGCTTTGACAGCCTTCTGCAAGAAGAACGACGTCAC
CTTGACGGGCTACACGCCTTTGGGAAAGCCCAAGCCGGATATTCAGAAGCCGGACTTTATCTATTCGCCGGAGGTGGCTGTTATTGCCAAAAAAT
ATGGCAAGACTACACCGCAGATTGTGCTGCGTTACCTGGTAATTGAGGCATCAACCTGACCTCAGCGACAGCATCTAATTAAAATCTCTCTTTTC
GCAGGTTGGTCTGGGTGTCATTCCCATTCCAAAGTCATCGAATACTAACCGAATTTCTGAGAACTTCGATATCTTCGATTTTGAGCTGACAGCCG
AGGAAATGGCCGTTCTCGATGGTTATCACACTGGCGAACGGGTGGTGCCATTAAATTTGATTAAGGGCCTCAACCACAAGTACTACCCCTTTTCA
ATTGAGTTTTAAACCAGATGAGCGCCTTGTTGCTGTATCACGAATATAATGTAATAAATTTGTCATTACATCAATCTCTATGACAACAAATTGAA
TGCACGAATGTATCTGCATACTTATTCCAAACCCAAATCCAACACAAAGCTCTTAGTGCCTTGATGTTCTCCATGAAATCCGTCCAGTTGCCAAC
GATCCGATCCGCACCCCACCGTGGAACTTATTCCCAGAAATGAGGAGCAAATGGAAGCATCGATCTTTGGCACGGCACGTTTGACATCCAAGCTA
AAAGGTGAAAATGTTTGAATAAGACCGAAATATTAAGTATTAAGCTTTTACGACCAATGGTAATGCGAAGTGCTCAAACTTGGAGATCACCAATG
GAGATTCAAATTTAAGTTACATGTGGAAAAAACTGTATACCTGCATTATTTCAATCATTTCAATAGTTGTTCAGCTTAGACATTGATTAATGAAC
TAGTGATATTTTTAGAAGGTGCTTCAAGCTTTTCTACAGTAACTTTAGATATAGAAAATAGAAAAAAGTTTAGTAAGTAAATAAGACGTAAAAAA
GCATATGGATTTAAGATGGATATGTGATTTAAAAAACGTTCTTTTAGAAGAACTTGTGCTGATTGCCAGCTGTTAGCCTAAATTGCTACATCAAT
TTTAAGGACGCATTTTTTGTTTGCCAACATTCTCTTATCAATGGATCTTCTATTCTGATGTATGGCCAAAAAATATCACGCGGAAGCTATTAGTT
GCGCCAACCGCAGAAATGAAGCATGAAAGTATTATGGCTATTAGTTGATGTACCTATTACGCCCGACAGGCTAATTATCTTTGGATTGTTGGGTA
CATTTTGGGTTAATCGCGCCGCCGTAGACCTTTGTAAATAGCACCTCGGCCTGTGGGGTGACGTCAGAGCCAGCCAAGATGAGCACGGGCTGAAT
GAAATTGGGGTCGTCTAGCCTTTGAGCTGCCCCAAAATAGTGCATGGATGAGTGAATTAAATAGCGGACCGGACTTGGACTTACGTGCTGCTCCA
CGAGTCGATTAGAGGAGAATCTGTGGC
(SEQ ID NO: 1516)

Exon: 1001..1137
Exon: 2814..2981
Exon: 3038..3553
Exon: 3615..3872
Start ATG: 1066

Transcript No. : CT29792
CTCACCGGCTTTTTTTTATTAAGCGATTGAATTTCCTTATTTATTCTTGATTTAAACGTGCAAAATGAAGCTCGCTCCGACTGTTAAGCTAAAC
AATGGCTACGAGATGCCAATTCTGGGCCTAGGAACCTACAATTCGAAGGACAACGAAGGCGAAGCCGCTGTGAAACATGCGATTGATGTGGGCTA
TCGTCATATAGATACGGCCTATTTCTACCAAAACGAGGCCGAAGTGGGCAAGGCGATTCGGGACAAGATCGCAGAAGGTGTGGTCAAGCGAGAGG
ATATATTTTTGGTCACTAAGCTTTGGAACATTTTCCACGATCCAGAGCGCGTTGAGGGCATTTGCCGCAAGCAGTTAAGCAATTTTGGCTTGGAC
TATATCGATCTGTATCTGATGCATATGCCAGTGGGCTACAAATATGTAGATGACAACACCCTGCTGCCCAAAAATGAGGACGATGTGCTCCAACT
GAGCGATGTCGACTATCTGGATACGTACAAAGCCATGGAAAAGCTGGTAAAACTGGGCCTGGTGCGCAGCATCGGAGTATCCAACTTCAACAGCG
AGCAGCTGGCACGAGTTTTGGCCAACTGCGAGATCAAACCCGTCACTAACCAGGTGGAGTGCTCGCCTGCGCTCAACCAGAAGGCTTTGACAGCC
TTCTGCAAGAAGAACGACGTCACCTTGACGGGCTACACGCCTTTGGGAAAGCCCAAGCCGGATATTCAGAAGCCGGACTTTATCTATTCGCCGGA
GGTGGCTGTTATTGCCAAAAAATATGGCAAGACTACACCGCAGATTGTGCTGCGTTACCTGGTTGGTCTGGGTGTCATTCCCATTCCAAAGTCAT
CGAATACTAACCGAATTTCTGAGAACTTCGATATCTTCGATTTTGAGCTGACAGCCGAGGAAATGGCCGTTCTCGATGGTTATCACACTGGCGAA
CGGGTGGTGCCATTAAATTTGATTAAGGGCCTCAACCACAAGTACTACCCCTTTTCAATTGAGTTTTAAACCAGATGAGCGCCTTGTTGCTGTAT
CACGAATATAATGTAATAAATTTGTCATTACATC
(SEQ ID NO: 1517)

Start ATG: 66

MKLAPTVKLNNGYEMPILGLGTYNSKDNEGEAAVKHAIDVGYRHIDTAYFYQNEAEVGKAIRDKIAEGVVKREDIFLVTKLWNIFHDPERVEGIC
RKQLSNFGLDYIDLYLMHMPVGYKYVDDNTLLPKNEDDVLQLSDVDYLDTYKAMEKLVKLGLVRSIGVSNFNSEQLARVLANCEIKPVTNQVECS
PALNQKALTAFCKKNDVTLTGYTPLGKPKPDIQKPDFIYSPEVAVIAKKYGKTTPQIVLRYLVGLGVIPIPKSSNTNRISENFDIFDFELTAEEM
AVLDGYHTGERVVPLNLIKGLNHKYYPFSIEF*
(SEQ ID NO: 1518)

Name: ALDOSE REDUCTASE LIKE
Classification: enzyme

Celera Sequence No. : 142000013384351
GTTGCAGTTGCTCTTCCTTGGTACACAACTGCTGGCTCTTTTCCGTTATCAGACCCTCCAGCTCGATAATCTTGTCCGCTTGTTCTGACACTCGT
TCCGCCAGCATCTGATACTGCAGGGCTAAGCCCTCCTTATCCCGTTGCAGGCGACGCATACGCTCGTCGGAATCCTGACGAGGTATGTGCGTCTC
CAGCCAGTCGCTGATAATGGCCGCCGTGACAGGATCCGGTGCTGGAGCAGCCAGTCCGACCTAAAGTGATAAGCGTAAGTGTAAGCCCTCCGTTT
CTAGACCTTATCATAGTCAGTGTGACTCACCTGTTGCAGGGCGAGAGCCAAAGTCTTAGCTGTTGACAAAACATTAGTGGCCGAAATTAAGTTGC
GTTCGCTGAGTGTCAGGGAAGACCCTGCTCCGGATATAGAAACGGATCCCGCCTGTGTCGCGGTACTCGATATAAGGCCGTCCATTTGCTGTAAT
GCTGCCTCGAGCATTTTGCTGCCCTCCGCCACAGTCGCCATGAAGTCCAAATCAAAGTCTCGCTAATCCCGGGTGATCGATGTGTGGTGTGCTTA TTGCGCGACTAGTGCATTGTTATGTAAGCAGGTCAGGCAGGGCACGTCATTTTGCACTGGTTTAGGGGAAAATGGCATTTATGGTTATTAATTTC
AGCACTAATTGGGGAAAACTATCACGAAAATAGAAGCTGCTGCACCGTTCTGCTTCTTCTTCTCGCACACCAGCCCAGCCACTTATCGATAGTCA
GCGAACGCAGAATTGTGTGTAGGAGCAACATCCGATAGTTTGCTAGATGGTCTAAAGTCTACAAAACAAATTTTAAAACAAAATTAATTTTAAGT
AACGTATAAAAATGCCTAAACACATTTTAATTACATTTTTTGGGGACAAAGTATGCAATATATCTAGATGTGTACAGCTATATTTGGTTTTCCAT
ACCCGATATCTACTGTACAAAAAAGATACCATCACTAATAAGCAGGTGGAACGGTGGAGTCACGAAAGATGTGTCATCTCCAGCCAGAGCCACAA
CAAAACAAATATTAAGGATAAAATAACAAATATCTGAAATGAATCGCTTCGCTTATGTGGAGGCCCGTCTGAGTCCCAATGAATCCTTCGTCAGC
CGCGACAACAGGGTAAAAATATACGATGGCGACCAAAAGGTGAGCAGCTAGTGAATTCGCACAATACGAAACCGGGTCTTTATTAGACTCAAATC
CTTTCAGACGGACTTTGAAGACGGCGAAGTGGTGCTCACCACACACCGACTGTTTTGGGGTCGCCCTGGAGAGATTGCCCGGGCCGCCGTAACAC
TTTGCCTGCCACTCAGCTATGTGATATCCGTCAGCGAAGAGACTACTGCCTCTAACTTCTTTGGCCGCAAGACTCGCATAATCATGCATCTGCAT
CCTCCAACGTCGGACAAAGGACCCGGCCCACTGGACACCAGTCGCGCCACCCACATCAAACTGTCGGGCAAGAATGGCCTGAGTGTCGAGTTCCA
CAGTGCCTTGCGGGAGACTCTAAATGCCCGCGTCTGGGAAATCCTCTTGACCAGCGAGATCATCATCAATGGCGTGGCCAGCAGTCCAACCTTGG
AGCCTGCCAACGACAGGCTGGCCCGCATTCAGAAGAGGACAGGAATTGGGGGCATCGAACGGCATTTGGAGGCAAAAGCCAAGGCCACGGATGAG
AACATAGCACTTGCCTTTCAGGATCTCAGTGTTCTAATGGCCATGGCCAAGGACATGGTAGGAGTGTCCAAGACAATAAGCAGCAAGATACGCGA
ACAGAAGGGAGAAATATCTGACGATGAAACGGTGCGTTTCAAATCCTACCTCATGAGCCTGGGCATCGATGATCCCGTCACGCGGGACAACTTTA
CCAGCAATTCTGCCTACTTCAGTAGCCTGGCCCGACAGATTTGCGAAATGCTGCTGGATCCTATCGAGGTAGGAACTGTATTAAAAAGTTATACT
TTGTATTGACACTTACTTTATTACCCCTTAGGAGCAAGGTGGCATGATGTCCTTGGCTGATGTCTACTGTCGTGTAAACCGCGCTCGTGGTCTGG
AACTGCTATCGCCTGAGGACTTGCTGCACGCCTGCGAGCAGCTTAGTGGTCCAATACGCCTGCGCAGCTTTCCCAGTGGCGCTAGAGTGCTACAA
CTGGAGTCCCACGATGATGCCCTAATTGCCGTTGACACATTGGAGAAGGTGGAGGCTGCCGAGTCTCTGGCTGTGGAGGAACTGGCCAAGCAGCT
GGGAATTTCACTCCTGCTGGCCAAGGAGCGATTGCTAGTGGCCGAACGTTTGGGCAAGGTGTGTCGCGACGAGTCCGTAGAGGGACTGCGGTTCT
ATCCAAATCTTCTGCTAGGCCGGGACTAATTTCAATGTGAATGTGTGCTTGTTGTTATGGTTAATAAAGATATTTGACTTTTTATTTAAAGCAGG
AGTTTTGAGTAGAAAGTGAATATCCTTTAAAGGTCCTTACCATTTTCAGTTCCATCGCAATGACAAGACTGAGTTCTTAATTTCATTTCACACTT
TATTGATTAACGGAGCTTCTGCTTTGACTTTGTCGGCGCTTCATTAAGTTATTTTGGTTTTGTCGTGATTATTTTCATTTTTGTTTAGTATTCTC
AAGAGTTTTATTCGTAATCAGTTTAATGAAAAGTTTCTACAGTCAGGTATTTTGATAAGCAGTTATTGAATTGAAATTACACATTTATATTAATA
GTGGTTTTCGTGTTTACATATATATAAATATATTATGCTGCTGCTTAGATTGCTCCGCATTACATTAATAAATCTTTGAATTACGTTTCAATAAC
CATTTGATCAGGCCACATTACCGCGCATGTATGTATATAACTTTCGTACTCAGGATTTTGGCCAATTGCTTGAGTAACATTTTCCCACTTCGTTA
TGCTTTCAATCATTCATTCGGTTTACGTAGTACCATGCTTTCATTTTCGTTTATTCATCTTAAATCACATTTATTAATTAATATTAACATTGAGT
AGTTTATGCTTGAGTGTGTGTTGGATACGGTAGGGAGTACGGGTAGTGGTGAGGTTAATTTGTGTTTTATTTCTTGCTGGCTGAAGAGGTTTATG
CAGAGGTTTACTTTAAGTGCTGCGCAGCTGAATCAAACAATGATAAACAAGTACAGCACTCTAGGCGGTAGTAACATAATAAAATCGTTACTTAA
ATAAATAATGTCCATCTACAAAAAAACTGGCTTAGGTGAAAAACAAATATGCTTTGTCGAAAGCGACACTTTTACACATTACTCGACTCGAGTTG
GCAACTTTTCCATCGTCCAAGCTCATTCAGCTGCTCCTGTCTCTAGTTTCATTGTACATTGAGCTATTACAAATAAATT
(SEQ ID NO: 1519)

Exon: 1001..1179
Exon: 1243..1968
Exon: 2027..2404
Start ATG: 1084

Transcript No. : CT30019
ACGGTGGAGTCACGAAAGATGTGTCATCTCCAGCCAGAGCCACAACAAAACAAATATTAAGGATAAAATAACAAATATCTGAAATGAATCGCTTC
GCTTATGTGGAGGCCCGTCTGAGTCCCAATGAATCCTTCGTCAGCCGCGACAACAGGGTAAAAATATACGATGGCGACCAAAAGACGGACTTTGA
AGACGGCGAAGTGGTGCTCACCACACACCGACTGTTTTGGGGTCGCCCTGGAGAGATTGCCCGGGCCGCCGTAACACTTTGCCTGCCACTCAGCT
ATGTGATATCCGTCAGCGAAGAGACTACTGCCTCTAACTTCTTTGGCCGCAAGACTCGCATAATCATGCATCTGCATCCTCCAACGTCGGACAAA
GGACCCGGCCCACTGGACACCAGTCGCGCCACCCACATCAAACTGTCGGGCAAGAATGGCCTGAGTGTCGAGTTCCACAGTGCCTTGCGGGAGAC
TCTAAATGCCCGCGTCTGGGAAATCCTCTTGACCAGCGAGATCATCATCAATGGCGTGGCCAGCAGTCCAACCTTGGAGCCTGCCAACGACAGGC
TGGCCCGCATTCAGAAGAGGACAGGAATTGGGGGCATCGAACGGCATTTGGAGGCAAAAGCCAAGGCCACGGATGAGAACATAGCACTTGCCTTT
CAGGATCTCAGTGTTCTAATGGCCATGGCCAAGGACATGGTAGGAGTGTCCAAGACAATAAGCAGCAAGATACGCGAACAGAAGGGAGAAATATC
TGACGATGAAACGGTGCGTTTCAAATCCTACCTCATGAGCCTGGGCATCGATGATCCCGTCACGCGGGACAACTTTACCAGCAATTCTGCCTACT
TCAGTAGCCTGGCCCGACAGATTTGCGAAATGCTGCTGGATCCTATCGAGGAGCAAGGTGGCATGATGTCCTTGGCTGATGTCTACTGTCGTGTA
AACCGCGCTCGTGGTCTGGAACTGCTATCGCCTGAGGACTTGCTGCACGCCTGCGAGCAGCTTAGTGGTCCAATACGCCTGCGCAGCTTTCCCAG
TGGCGCTAGAGTGCTACAACTGGAGTCCCACGATGATGCCCTAATTGCCGTTGACACATTGGAGAAGGTGGAGGCTGCCGAGTCTCTGGCTGTGG
AGGAACTGGCCAAGCAGCTGGGAATTTCACTCCTGCTGGCCAAGGAGCGATTGCTAGTGGCCGAACGTTTGGGCAAGGTGTGTCGCGACGAGTCC
GTAGAGGGACTGCGGTTCTATCCAAATCTTCTGCTAGGCCGGGACTAA
(SEQ ID NO: 1520)

Start ATG: 84

MNRFAYVEARLSPNESFVSRDNRVKIYDGDQKTDFEDGEVVLTTHRLFWGRPGEIARAAVTLCLPLSYVISVSEETTASNFFGRKTRIIMHLHPP
TSDKGPGPLDTSRATHIKLSGKNGLSVEFHSALRETLNARVWEILLTSEIIINGVASSPTLEPANDRLARIQKRTGIGGIERHLEAKAKATDENI
ALAFQDLSVLMAMAKDMVGVSKTISSKIREQKGEISDDETVRFKSYLMSLGIDDPVTRDNFTSNSAYFSSLARQICEMLLDPIEEQGGMMSLADV
YCRVNRARGLELLSPEDLLHACEQLSGPIRLRSFPSGARVLQLESHDDALIAVDTLEKVEAAESLAVEELAKQLGISLLLAKERLLVAERLGKVC
RDESVEGLRFYPNLLLGRD*
(SEQ ID NO: 1521)

Classification: hypothetical

Celera Sequence No. : 142000013384603
TATAGTTGTGTCCGTGGCCGTGGAAATTGTTGCACTTGCCGAAGACTTCCAGATTCTCGGCGTCGCTCAATTGGGGACTGAAGAGAAAATAGATG
CAGCAATCAATTTAAATCGAACTGAATTGGTTTGCCAGCCGTGATTGAATCAGGCAATTGAATGATTCAATTTGATTCAATCTAATTACCTATGG
AGACGATGGCAGGCGCTGAAAGTTTCGCGACGGGTTAAAAAGGCAACAGGTTGCTGCGACATTTCAAGTCCGATTTATACTATATATCTGGATCT
GTATCTGGATGTGGATTTATATATGCGGCTGATCAGCTGCGCGCTTTGGCAATGTTTTACAATGAATGCAAAACCTGCTTTTGAGCCGCGCTTAT TTATATGGTACTTGGATCGAGGGAACAAGGAAATATAAGCCACAAATGCGGCGACTGCGATATCAACACGCTCGGAACTAGTTTCTCTGAACTTT
TCGAGTGCGGCTAATTGCAGCTGATTAGCGATTGATGTTCCCTCGTTTTCTGTTGCAAGTGCCTATGCGTGCTGCAAAGACAGGGTGTGGTATGC
TATAGCCATGGTAACAAACTCAATTCAGCAAGGAACTCACCTTTAATTGCTATGGATTTTCAATAATATTTACTTTTGTCTACGTTGCTCGTCAA
CAGCTGCTCCCGATAACAAGGCAGCGCGTATCGGTTATCGGCCAGAGCTGAGCAGTTTGCCGCCACAACTGTTCTCAGTGATTTACAACTGCACA
AATAGACTATTGTATGGGTAGAAATCCTTACACTATTACAATTTCGCTATATATTTATTTATTTCATGTTAGTTCTTTGTCAATTATCTCATAAT
TTAAATGAGCTGATTAACAGAGTTAGCTAACAGAGTATGTAAGTGCTGTTCATCCCTGGCTCGTGGTGGCGTTGCCGGACCTCACGCCGCTCACT
GTAATCAACCCTGCTTTGCTATCGATCGCCGCCCTTCACTAGAAAAAAAATAACAAACGACGCCGCGCAATAATTCGAAACTCTTCGGCGTTATT
TAAAAAACGAGCAGAGATACCTAAATAATAATCTAGACATGAGCAACAAGAGCACTCCGGTGCGGCAGCGCATCCAGCAGTTCCAGACGCGAGGA
GTCCACAAATCCACGCCGGCATCCGAGATGCGCAAGAAGGTGCTGATGACGCGGGCGGAGGATCGGGAGCACCGGGATCGTCCCGAACAGCTGCT
GAACACTGCATTCAGCGGGAGCACGCCACAGCCGAAGCCCAAGCCCACGGCCCTGAATGCCTGCTACACACCCTCGTCGCTGTACAGGAATGCGA
ACTCTACTCCTGGAAGAGCAAAGACGCCCGGCACCGGGAAATCCAGCTGCAGCAGGACAAAGGAGCGGGACTCTCTGATGGAGTCCTGCCTCAGC
GTGTCCGAGGAGAGCAACATGATTGTGGCGGTGCGAGTGCGGCCACTGAATGCCCTGGAATGCACACGTGGTCAGGTCACCAATGTGGTCCAGGT
GCACGGAAACAGCAACGAGCTGACTGTCCAAGCGGGCAGCAGTGCTGATGCCTCCGCCGGCGTGACGCACTTCTTCAGCTACGACCAGGTCTACT
ACTCGTGCGATCCCGAACGAAAGAACTTCGCCTGCCAGGCCAAAGTCTTTGAGGGCACAGCGCGTCCCTTGATCGACACTGCCTTCGAGGGCTAC
AATGCCTGCTTGTTTGCCTACGGCCAGACGGGCTCGGGCAAATCGTACAGCATGATGGGCATTGAAGCATTGGATGACGCCGCTCTGGATGGCGG
ACCGCCGCACGATGAGGCGGGCATCATTCCACGCTTCTGCCACGAGCTATTCCGCCGCATAGAGGCTGTGAAAAGTCAGCAGCAGCTGCAGGTGG
AGGTGGAGGTCAGCTACTTTGAGATCTACAACGAGAAGATACACGATCTGCTGAGTGTCCAGCATGCGGCAGCTGCCACCGGGGAATCCACGCCC
ATCCAGCAGCAACAACAGCAGCAGCGTCCGGCTCTAAAGGTCAGGGAGCATCCCATCTTCGGGCCCTACGTAGTGGACTTGAGTGCCCACTCGGT
GGACTCGTACTCGGCACTCCGCAACTGGCTTGCCGTGGGCAACTCCCAGCGGGCCACTGCCTCCACGGCCATGAACGACAAGAGCTCGCGCTCAC
ACTCCATCTTCAACATTGTCCTAAACCTCACCGATCTGAGCAGTGACGATGGCCTGTCCTCGGATACGGACTCGAGCACGGCCTCCTCCCTGCGG
CAGACGCGGCGCAGCAAGATTAGCCTGGTGGACCTGGCGGGCAGCGAACGCATTAGCGTCTCCGGATCGAACGGCGAGCGGATCCGCGAGGGCGT
CAGCATCAACAAGAGCCTGCTGACGCTGGGGAAAGTAATTGCTGCTCTCGCCGATTCCCGCAAGGCGATCGCCAATGGACCCCTGGGCTCTGGGA
CGCCCAGCACCTTCGTTCCCTATCGCGAGAGCGTGCTCACCTGGCTGTTGCGGGTAAGTGTTACGAAATAGTTCTTAGCTGCGTTTGTACTTATC
AACCGGGTCAGTAGGTTGGTCTACTTTCGGCTAATGATAACTCTTTCTTATCCCCTTGGTTTTTGAAATCAATAATTGTACCCAGAAGTGATTGC
TAAGTATGTGTTTCGAATAAGTTCAGCTCAGTAAAACCTTATAACCTCATGTCTTCAATATAAATGCATATGTATATTCGCAATGCTTTCCGCAC
TTTTGCCACCACCGATAGGATTGCTTATCAACACTTTCGCTTCGATTAGGCAGTGGCCCACGGAATGGGGTCCCCTTGCAATCAGTAATTACCCG
GAAAGCAATCAGTACGTAGAACTGCACTGCAACATGCAAATGACACGTTGACCCCTGCGGAAAGTACCCACAAAATGTTCGTACGGTCAAATGTT
TACTTAACTGGCTGGCAGATATTCGTCTTTTCAACAGATCTCGTGATGAGCTATGAAGCCCACTGTCTACAGAGATATCATCTCGACTCGCGCGA
CACGCGAATTCTGTTTTAATGATGTCTGCACTGCGAGGAGCAGCTGCTAGACAGATTTATGTTGGCTCTATCAATTAACTGGGGTGCTAATTACT
TTAATTAAAATAAAGCGTCAAATTGTCCGAAAAAAACAAGGAAAAGAAGACGACAACATCAGCCAGAGATTAGATTGAGTTTATCTGCGCTTTAT
AGGACTAAATATGAGAGATCTCGAGTTCTAAACTCGAACCTTGTTATCATTCGTTTGTTTATTTTGTTTGCTAAGATTGCCAGCAGACTTAGTGT
ATTTTTTATTATTATTATTTCCTTATCATTTTCGATAGGAAAGCCTTTTATTAAGGTCTACCAAATCAAAGACCTCCCGCACCTCAATCAATTGA
GTGATTAAAATTTTGGCCTCTTATCATATCTATTTAATCTATTGTTGTTGCTTTTCCTATGTGACCATAAAATTTATGACCTGATACAAAGGCGC
ACGTGTAAACTTTCTAGAAATTTATTTTAAGAACGCGAATAAAAAGATAGCAGTGTCTTCACCCGGGTAATATAATTATTTTGTTATAAAACCTC
AGCAAATGCTTACATAGCATTAGCAGGAAAATTGTTATAAACTTGTCATGAGACTTGAATGTTGTGCATTAGTTAACATATTAGCTACTTGTTTC
ACGATTGTTTGAATTGAGTAACGACTGCGTTTCTTTAGCAATCAATGTAACATACTTATGTGTGCATTTTAAGTTAACAACTGCTCTTAAGCGA
ACGCCACACGTTCGTAATAACTTGATTGTTGGAATATTACCAGGCTAGTTAATCCGAAAGTGAGGGTTTTATATAATACAAGTATCTGGCTTCTA
AAAAAAGGCGCACTCGACATTTGCGACGTAATTTATAATCATTCGACTGCATTCAATGAGTAATTACATGGCGCCCACAAGTGAGAGGCTCTTGA
TCGAAAGTCCAAACACTTGTCTTTTTTCCCGAAACCCGTTCCACTGAGTGTTATTTAGTGTCCAGTGTCCACTTTGCTTTTCGTTACGGTAGTAC
GGCCCATAAAATGGCTCACATGATTTATTTCCGTACGCGGCCTTTGCCATAAAAGGTGAAGACAAATATTTCTTGGAATGGCGTCGTAGGTCCGT
AGGGGACTCTCGCAGCCAGCGTAGTGACGAAACGCACCAGATTGTGGTTGCCCAATCCATCTTTAAAATCATTGAAAGATTTAGATGGTTTAGAT
TTAGGGTTTGTATGTTGATTGTTACTAGTTGTTTTCACCCCTTTAAAAGGAGGGGGGTTTTGTTGTGTTTTTTTTTTATATATCAGCCGACCTTG
TTTTTTGCCTCTGATATTTTTGGGCTTCCATGGTTCCTATCTATCCGTGAAGTACTTTTCCTATCTTTGCATACGACACAAAAGTTCCATCTACA
TCTTCACTTGCCACCCCATAGATTTAAAAATACTTTGCAGATAATGCTTTATTTGGTATTTTTGTGCGGTACTTCGGCACTAAAACATTATAACA
CTTGATACGTTATCGCGTCTCCTAAGTTGCGACACCAACAATTTCAATTGTTGCTGTCGTTGTTGACGTTTTCCACATTTACACGCTGAAGGCTC
GCATTTGCAATTGCCCTTGCTCAGCTTTTTTCCATCCTTAAGAGCTGCAATAACAATTTGTACACAAAATGAATAATTTATATACAGATAGTTAG
GATGGTAACTAAACGTTTACGAAGTGTATACAAGCCAATAAAGGTAATTGATGGCAGAGTATGTTACAATTAGCAAATATGTTTAGGCCAAGTAA
AATCTAAAGTTAACCAGGATTTGGGTACAATGTAAGTAATGGGAGATGCTTTATAATCAAAATTGGTTGGTGTTTTATAACTTTAATTTTTAACA
TTAGTTGTGATTTGACATTTGCAGTCCGTTTTGTTTATTAGCACAGACTCGTCAATTTAAAGTCATATTTAAGTTCATTATCCAAAAAGCTCATT
ATTCGAAACAAAAAAAGAATACTGTTAATACTGTTATTTAACTGGCTTAATAACAGTCCACTTATATGAAAATGGTTTTGCACTACGGCTAGGTT
TTGTAAAAGAATAATTCAATTTTTGATAGGTAATTAGAATAGTTGACATATTTTGATGTAAGTATTTCACTTTAAATACCATGGCCTAGCTATTA
AGTTCACCTTGCGACTTGACTCCTCTGGAACTTTTCAGTTTTTGTAACAAGCGGTTCAGCATTTTTTGAAATGCAAAGGGATATATTCTGTTCTC
CAAGAAATAAGTCCTTTTTTATTCATTAAACTATAGTTTTTTCTCAATTTTTATTAGTTTTGAGAACTCGTTGCGACCTTCACATGACTGGGGGA
ACTTTGGAACTGGAAATGCGGAGTCCCAAGCCAGCTTTCTAAATAAATTCCAAATTAACTTGCTCGTGTGCAAAGCCCTAGAAACCGCACTGAGT
TCACAATCAGCATTTTCCGAGTTGGATTTGGAAAGCCACAAACACCGTTTAGATAGCCAGGGAATGTGGGATTTTGAATGAAATCCAGAAACATC
GAATTGAATGCAAATGACGTAGGTTCACACGATTTCAAATTCGATTGATCTGCTGTTTCTAATACGTGTCTAATACGAAAAGCGTGCCACTGAGG
ATACGTCAGTTAATTATTTTCGTAATTAGCAACAGGCGAGTTGTCTGTCGCCGTTATGAATTTTCAAATAAGCCACGTTTTCAGTTCACAAATGA
ATGCTAATTATGTGAACTGAAAAAATTTGACATACGAGTAGTAACCAGATTAATTATTCACAAGATTTCGACTAACTGAGCCATTCAATAATGTA
AATAGTAGTAGTTATAAATAGTATAGTATAGTATAGTAGTTATAAATTCAAAAGTTTGTATCTCTGACCCACGTTGGCATAACAAAATGCTTCGA
ACGTGTGCTCTCCGTTCCAGTTTCCCGCATAACAACAATTGTAATTTAAGCCACACTGTTTAATAATATATTTAGCCCCAACCAAGTGGTTAGCA
TTGGAATATAAAATGAGTCGAATTCGATGCACAAACAACTGAATATGTATATGGCTTCCTCCCCGCGAGTTGTTTCTCTCGAACATCGCTTTCCC
CGTCGCCCCATTGCACATATACCCTTTTGCACACTCATGAAAAAATATGCAAATGGAATGAATGGTTTTCGTGTGGGGGGATGCGCTCAGTTCTC
AGTTTGATCAGTTGAATTTTTTTGATTCGCCTTTCATGATTAAGGCACGGATGATCTCATCTACCCGTGCCAAACGTTCGTTGCTCTAATTCAAT
TCGGCTTAGTTGACTGGGGTTTCATTTGGATCACTTGGGAGCTGGCATCCCTGGACATTCGCTTGCAAGGTGGGATAGTGCATGGTCAAGTTCCA
GGTCGGTTTATTGGGGCTCGAGGTGCTTTCGCTTAGTTCCCAGTTTAGTGCCTAAAACCTGACCTTAGCCATCAAGTACTTACTTATCATATTTA
ACGTTTTCAAGCGGCGGAACATTTTGAGTTCAGACAGACAAAAGACAGATTAACTTCAATTAGTAAACTGGTGCGAGACGGAAAGATTTCCGTAA
AGATTTGCATAAGAAATTAAGACTTTTATTTGGAAAATTTAAGTCCAAACTGACCCACCTCAACGTATGTAATTGGAACAGGTGTCTAACTTTTA
GAAATCGTAGCAACTATGAATGATATCTCCTTTCTTTTAATCGTAATTTCCTCAAGTAACCCTCAAGATACAAGTACGCATTTTAACTTAAATTT
TTCAATCATTTGTCGTTTTATTCGGTTTACATATAATTTAAACTAACCATTAATATATAATATATATGATATATAACATTGTATAAATTGAAAAT
TTTCTTGGAACCTGCAAGCAAATTTTACACAAATCATTACATTTTGATCAATTACTTAAATGACTAATGCAATTGTTAAATCGTTTTTATAATAT
TTCCGTCCGTCTTTTTGCACAGCTGAGTCTGAACACCAAAAATTAATAACAATTTCTGTTCTGTAACGACAAGTTGAGTTAACAAAATGTAACCA

FIGURE SHEET 827

GGCATAAACTTTTGAACAATTTCAACTTTTACATACATATTTCGATTTGATTTCATTTTGACACTTGCTCGGACTGTGCAACGCTCAGTTGGTAT
TACAATAAATATAGGGGAATGTCTAATATAGACAAGGATACAATAAAAATCGGGGTCCAAAGTATGTACTACGCATATATCGAGAAAATAACAGT
TGCAAAACCTTGATTGATCGTTATAGTTTTCATTATTTCTTTCTTATATGGTAATACCTGTAACTGATCCAATTGGGTCCAAACTAAAGCAACGA
AAATAACAAAAATTTCGCTTAAAAATTTTCTACTGCAATTTACTCAGTCTCGTATGCAAAATAGAAAATTCAGTTTTTGCTTCCCTTGTGTTACA
TATATAATTTTTTTTTTTTTTTTTGCCTAAGGTCAAAAAATGCGTTGGTCAAGCGGGGCAGGTTTTCGTTACTTGATTTTTTCGTCGTGCGCTA
TTGTTTGTCGGTAAACAAAGTGCCGTTTGTAGTTGTACATAACTGCGAAGTTGGTGTAAAAACGAAGGGCTAGATAATGAAAAAGGTAGTTGTAA
ATTGGTATCAAGTGGTTCTGGCTTTTGTAAATGGTAGTGTATTCGCAACGCGGAAATGCTGGGCAACCATTTTAAAAAAAATAGGGGTACAGTTG
CCTTAGATTATTGTAGCTGCAGGCTGCTGTCTCGCTCTCTCGCGCAATCTTCGTCTTCGACAGCTTTTTCTCTTTTCTCCTCGGGTTTTCTTTGT
TTTTGTTTTTGTTCTTACTCTTTCAGGTTTCCTTTCTTCTGGGTTAGGTTACACATCTGTATACATATATGGCATTTCGCGAATGCTGCGGGCAC
CGTCCGCAGTAGATTCGTCTCGCTCCCACTCACACCTTGCAGCTTTGCGGGGCGGCAAGGACGGTCGACTGGCTGTGATTGTGGGTGTGCTCCAG
CTCATGCTCGTGCTCGTGCATGTCCTCCTCGTCCTCGCAGATGCTGTCATGGTGCTTCCTTTGCTCCCGCTTGCGCATGTAGTTGATGAGCGGCC
GCTTCTTGTGCTCCTTGCAGAATGGGCAGTCCTTGCGCATCTGCTTCTCGGACTTTATCTGCTTGCACTTTTCTGCAATGGGAGCAATGTGATAG
GTCACCGGTTAGTGAAGGTCGGCACTGAATGTTCACCCTCGTCTGTTGTTTCCCGCATTCGCTTCCACTCTGCCTTTTAGCCTACGTGCCCTTCT
GGGCCGTCGAACAGCTGATTTGACTACGTGACGTCGCTGCGTCTACGTTCACGACGTCACGTCGCCACCGATGGCGCCCCTCCCCACGCTCGCAC
AATTTTTCCCGCTACTCGACGTGTGACCCTGTGACGGAGGCAGCTATATATTTAATATTATCATGCACTGGATTTTAGAAACCTATTTTAAAAAG
TTGAATCTATCTAATCTTTGGTTTTAATGAAAACATTGTTGTCTTTCGACGACTGTAACACAACTACTACATTGAGCACAACTGTACTTACAGCT
TGTGTGCTTTTGTGACCTGCCTCCGTTAATTAAACCATTGCTTTGATTGCTCAATTGACCGTGTTAAAAGCTAAACGGTTATTATTGATTAAAGC
CCAGCCGATCCATGAGGAAAGTCTATTTATAGCCGCCGATAAGCGACCTTGCATAATCTCTAAATGTGTTCCACACTGGGGGAAAAAAGTGCTTT
ATAAACTGGATATTTACACACATATGCATGCTACCATTCAAATACGAATTGAGTTGTGTATGTACAGACATGTGAATCTAAAGTTTAAAGTAAGC
TAGATATTTGCCTTGCATAATTTTTCACTTGTTTTTTTTTTATTTCTCTGCAACCCGATAATGCACTACGCGTATATGTATACTATATGGACGAA
AACAGCACGAAGGTTTAACATTTACACACCTCAGTTTCGTTATTGCGCTTCAGTTTTGGCACTCAAACACAATGAAACCCTGCTTTGTTTGTTCT
TCCCTATAAAAGAATCCATTGTGCGACCACCTGCTTAACTTTTGAGAGCCGATTCTGGAGGTACAGCCAAGTCTTAGTGCTTGCTTAGTTGTCTG
TGTAATTAATAATCGTAAAGTATTCGAGTGCAGAGTGTGTCTTAATGGACTTGAGTAGTGACCTCGATAAGAGCGGGTTTAACCACCTCTGAAAT
TGCCACAAAAAGTATATCTTTGCCTTTTATGATTTTCCACGAGTGACAAAGTAACGATATACTCTTTTTGTATGCCCATCTGAATTGCGCTTTAA
CTTTGGAATGCCGGAAATTCGTAAGGAACCTTGTGGGCTTTTAGCCGCTTTGTGTGTGCAATTAAGCGCGAATATCTTTAGCACGTGGATTCAAG
CCGTAAATAAAAACAAAATCGAGGGGGTGTGGAACCTACTTGATAAGGTGACTTGCGCCGCGAAACTTTGGACACCCTGTGCTTGTGCGCAAAAA
TTAAGGCGTGTTCTACACACACACACACGCACACACACACTTATGCACATGGGGCTAAGAAATCAGGCTGGCTATTTATAAATGGTTGCAAAAAC
AACAAAACAACACACGCAATACACAAAAACAAGTGAGAAACGCGTCTGCTTTCAATCTCGCCCCTTTTTTGCCAGTGCATTCTGAGCGCTATCTG
TTTTTTCGCCAAAAATTACCTTGCACTCGACTGTAGCAGTCCTTGACCGCGTGTGAGGAAGTGGTGGACTCCAGGGTACCATAGGGGAACTCCTC
GTAGTCGCGGTAGTAGCCGCTGCGCATGGACCCGCCATATGCCATTGTGGTGTCGCTGACGCAGAATCCCCAAACATCCATGTCTGTGCTGTGCG
GTGTTTCGTTACTATTTTTGCGAACTGCAGTGCCAATCAACGGGATGTGAATTGTGTTTGTAATGTGGGTGTGTGTTTTTCTTTCTTTCTCTCTT
TTTGCGCGCGTTGTGCGAGGTCGTTTCACTTTGTCTCTCGATTGGCTCGGGCGTCCAATGAACCTGGCTTTTAAAATCACTTTGTTTTGTTTTTT
TAACAACGCTTTTTGGTGCACTTTTGCGTGGAGGTGACTCGCAGAGGTTTTCCTTCTTTCTTCTTCTTGAGCTGCAAATCTCTCGCCGAAATTCG
ATGTATTCTGTTGGAGGTCTCTCGTGAAACTGAAAGCCGAACACTAGAATTACTGCATTTTTGTAGCTCTCGTGCGCTGGCGATACTTCGGCTCT
TGTTTTGCTGCCCACTTCGGGTCTCCCCTATATTTACTTCTCATGTGCCTACGTGTGAATGTGTGTGGACAGTCGCGGGAAAACGTTTAGGGCAC
GTGTATATGAATGAATGGACTTTAATTTGTTTTAAATATTCTTTAATGTCTGTAGTACTTGGAATAGGTGTATATACTATGCTGCCCGCACTTGT
ACTAAAATATTTGTGTGCCTGGTTGTAAACACGTATGTGTGGCATTGTGTTTTGTTGTGTTTTCGCGTCTCGTGCTTTTGTCAGAGTTTCACCTT
CCACCCGACCCCTCCCCTTTCGAGTGCCACACACCTCTCGCTTGGGGCACATTGGTTCGCTACTCTCGAAATCACCTCTGCCGTGGAAGCAAGCA
TTTTCCAAGTGATTCACCCTGTGTTAGTTTGAAAATTTTTAATAAATATTAATTAGCCGGGGCATGAGGAATACTCTTGGAAGTTTTTCTTATTA
GCGGCGAATCGCTAATGCCGCGGAGATGACGAAAAAGTAATCATGAGAGTGATCGGACGGATGTTCGACGGCTGATCATCTGGAGGATGGATGG
ACATTTGTGTTTTTATAAGCTGCGCTAATCACGGTCTAGACTGCAGGCCGACCATGCCGTGATTTAGCCTTATTTCTGAAACCAAATTTGGTTGC
CAAGCGGATTGAACACTTTTGAGAGCCCAAATTGGAGTGTTCTTTTTTTTTATAAACTTTCCATGGTCAAAATGGACTGTATTTCCAGCGTGTGG
CATTCTAGGCGTGTAAACCACCAGCTGCACTTTTTCACTACTTTGCCTAGAGGTTTTTGAACATTTGAAAAATTTGTTTAAATCTAGTGTTAATT
GGCAGTCTACGTCATTTTAGCCGGTTCCGATCAAGGTTTTGCTGTTTTGGCTCAAAAAGCATACCGCCTATATTAGCGCCTTCCTGCGGTTTATG
TTTTGGTGCACGCTCATTTCAGTTACTTTTGAGGAGATCGTGACTGATTTCTAAAGGTGGGAGGACGTAGAGGGCTATATTTAGGAAAAAAGATT
TTTTTTAATGTGGTACGCTTTGGTACGTGAATGACTAACAGAGAGTGTCGCCATTAATTGTATTAATTTGCGGTTAACGGACCACGGACCCAGAT
TCTGACCAGACGACACTGACGGGCCCCTAAGGTCACCTATGGTAGCTGTTTTTCAAGGCATATTTCTGCACTTGCGACCACTGTGCACGCCTACG
CCGCTGCTGCTGCGCAGTTTGTGTAATCAACCATCCTCTTTTCGGTGCCCGCTCTTGTTTGGCCCACGGTGCTGACCTGCTTAATCAAACAAGTG
TCACTTACGCACACTGCCAAGAATGTGTGCTAACTAGCTAATACGAAGCTTTATTTGAATACATACATATATACATACGTATGCATACACTACAC
TACAAAAAAAAAAAAACTATCAGATAAAAATGCAACGGATGGCCAATGCATTTGTAATTAGGTAAACAAATATCTTACTAAACGAATATGTAACC
AACATTTTGAAAGCACTGCGATGCACCAATTAGTGAGTTTTATTTCTGAGCCTATTTCTTCCGTGTACTTGCATGTGGATGCATTTTGTTTGCAC
AACAACTTTTCGATTCCCGCACAGCGGTTGCTGATAACGACCATCAGTAGGTGCCTTTGTCACGGTAGCTTTACGCAAACAGTTGGGCGTTGTCT
TATCATTTCGTCCCTCCTTATCGCACCGAGTCCACAATCGAAGCACACACTCGAAGGTTTAGATTGTCAATTTTCCATTCCTTGAAATTTTCACA
CATCTGTTCTGAGTGCTTTCGAGTGCATTATAGTGTTCACCGATGATCGATAATCATCGTACCTCTTGCATAGTGGGGTATATTCCTTTTTGCCA
CATATGTATGCATATAGGGTTGGTGTGAAAAACCACTTTCCTTATCAACTTGGGTGCCCATCCAGTTCTTTAATTGATTGGAAAATATGTTTATT
GGGATTTCTGTTTTATTTTCTTCAGTCCATTAAATCATTATTATCACATTGAGATTAAATGGACCATTTCCAATAACAATTCCATACAGGAACCA
TTAGGATTATATATATCGGTTTATGTTGTTCCTTAAAAGATATTCAGCCGACTCTATAAGCTACTAAAAGTAGTGCATTCAAAATGCCTGATTTA
TTCATCAATGAAATGTTGTTTCGGTTTTACGTGCTAGATTAAAATAAAATAAAATGCATATAAAAATTATATTTAGGTTTATACTACTGTTACTG
ATTCACATGCCCTTGTTTGTGATTTATTTCATTTTAAAAGGTGTTAAAAAATATTGTTATGAATGTGAGAAAGCCAAGCTACACGTTGTATACCA
CAGCCATTTGCCATATTGACCCTGCCAATAATAAATAACTTGATTTACCCCAGATATTAACATCAAAACAATACAATTACTCACCCAATCCAAAG
ATGCATCACAGAGCTTTTAATATAACTGACGTTGTTCCTTCATTCCAGGAAAACCTCGGCGGGAACTCGAAGACGGTCATGTTGGCCACCATTTC
ACCGGCCAGCATCCATGCGGATGAGACCCTAGCCACTTTGCGTTACGCCTGCAAGGCGCGTTCCATCGTCAACCGGGTGAAGGTAAACGAATCCC
CCCACGACAAGATCATACGGGATCTGCGCGCCGAGGTGGATCGCCTGAAGTCGCTGAGGAACGAGTACGAGCGCCAGCGGCGCTTGTCCGGCAAT
AGTAACAATCCCGTGCCACGTAAGATCATCATTGAAACCTCCGTGGACGAGACCGAGGTGGAGGCACTGCGTCAGCAGCTGGCAGAACGGAAAG
GGAGCTGAGTCGAGCGCAAAAGTCATGGATGGAGAAGCTCAAGGAGGCGGAGGATCAGCGCAAATCGGAACTTCGTGTCCTGAAACGCCGGGGAT
TGGCTCTGGAACTAACTGCTGAGCAGAAGCAGGCCTGTCTGGTTAATTTAACAGCGGATCCCATACTAAGTGGCACCCTGTTCTATCTGTTGCCC
CAAGGACTAGTGCGGATAGGACGAGGTCGTCTGCCAGGAGGGAGTTCTAGTTCGCAGCCTGATATTGTACTGGATGGTCCACTGGTGGCCTTGCA
GCACTGCAGCATCGAGCATGAACGTGGTGGCAAGTTGTATGTCATCCCCGGCAGCGAGGACTTCGAGACCTACGTGAACGGAGAACTACTGAAGG
ATCGTCGCCAGCTGTTTCATGGCGACCGTCTCGTCATAGGTGGCTCCCACTACTTTCGCATTTCCAATCCCTTCTGCTCGCAAAGAGGCAAGGCC
GATCATCCGGTAGATTTCCAGCTGGCCCATCAGGAGATTTTGCAAAAGCAGGAGCAGCAACTTCGCTCCGAATTGGAGGCGGAAAAGCGAGCCGC
TCTCACGAAGATTGAACAGGAGCGGGCGCAGCATGCCCGGGACTTTGAGGAGCGTCTGCAGTGCCTCGAACTAGAGCAGTTCAAGTACAAATGCA

FIGURE SHEET 828

ACAGCGAGATGCTGGAGACGGAACGCCAGGCCTTGGCCTTGGCCCAACAACAGGAACACACTCCGCTAAGGCATGAAGATGCAGTATCAACTCCA
GCACAGAAGTCGACTATACTGGAGGACATTCAACGCATCATGCTGAATCCCTCGGAGGAGAGTCTTCACAAGACCCAGTTGATGGTCAAAGAGGC
CACCCAGCGTTGTCGCCAGTTGGACCTGCCATTGGAGTTCCGGCAAACTCAGACGCCAGATGAATTTGGTCTCCTGCGCACTGTTATCTTGATTC
TGGATAAGCAGCGGGGATTGAAGGCCGAGTGGCCCACAGCTAGACTGGGTGTGTGGTTGGATTTGGTCAGGGATAATGCTGAACAGCAGGAAAAG
CTGAACGCTACAACCATTTTCCAGAGTGTTGAGGTGGATTGGGAGCCACTGGACGCGGATCTCAATGAGACACTGAGTGACACACACAACTCCAG
TCGCATTGCCCTTAATCTGAGTGCCATGAAGGATGTTCTGTTGAATAAACCGCTGAAACGCCTGCTCAACGCATCCAGCAGCAAGAGCAATACAC
CGCGACAGACATCCACTCCCTCACCTGGAAGCCAGCTGGTGCACTTCACCAAACGCCTGCTGACCTACGATCCGGAGGAGATACCTGAAAGCCAG
AGTAGTTTCACAACGCTCGTCCAGCAGGAGCTGCAAATCATGCAGCGATCCGCCCAGCGTTTACGGCGACACTGCGAGGCTGCCCTACTCGAGCG
TGAAAACCATCAGGACAACGGCGTCCTGGCCGTCAGCCTGCAGGAGGCTCTGGCACGAATGGACACCGTGCTGAACGGGATGCACACTTCGTTGG
CGAGAGCGGAGGCCACTGCATGTGTCACCTCGCCGACGAAAACACAGAAGGCTGTGCGCTTTCTTATCGATTGACGGAGATTAGTTCGCACCTTG
GACTAGATTTTAATGCTGCAATGTGCTTTGTGTTGTTTTTATGTTTTTAAATATATATTTTTTGTATATTGATTTTTAACAATAAAATGTATTGA
TAGCACCTTCAAGTGAAACTGGCTTTTGGGAAATATTTTAAAGTGGCGGTACAAAAAAAGACTTTTCAATTAGTTTATCAAATAAATCACTAGCT
TTAGTTTGTTTTTGTAATGATTTTCTGGTCTTACATAACTTAATATCCAAATCATGCTTGTACGTAAGTGACATAATAGTTTGCTCTGGCATTAA
AATAATTATTTACTTCATTATCACCTCTTCGAAAGTTTATCACGGTTTTCGAACAACTTTGTGTCAACATCCAAATATTGGTTTATAAAAATATT
AAAAGTACCGCAGGCTAATAACCATGTGTTCCCTCTGCCTTTCTTGTGGAAATCTTCAACCTTGGGCCTCCTCCTCTTCCACGCCTTCAGTGGAC
TCCAGCTCCTTATCGCCAGCCAATTGCTCAAGTAGTTTTGTGTTCAGATCAACTACCCAATCGCAGAACTGTCCGCCCTTTAGGCTTACGAAGTC
GGCCAGGAACACGTTTACCCTTGGCTCGTCCTTTGGCTCGAAGGGACCTGGAATCTGTTCCTGAATCCAAGGCTGCAGCTTCTTGTCCACCCGTT
TGGCTGTGCTCTTCAGGGTGAAGAAGAGCCGGAAGGCGATATAGCGACCAGTGGGCGTGATAAGGCACTGGGAGACATAACCCTGTTGGGGCTGT
CGCGAGAGTAGGGAATCCTCCAGAAAGGACTGCAGCTTCTTGACACTCGCTTTATTGGCCACGGTGTGGGCCACGCATAACTGGGCCAGAATCT
CAGCGGCAGTGGAATGGGACATCGCCTGTAGATGATCACCACGCTGCGCTGCATTTCCAAGCATCTATTCAGAGTACAATCCTTGAGTGAACCAT
CCACTGTGGAGTACAGACGATGGGCGAAGAACTGGATCAGATCCTTGTGCAGCTTCTGGTGATGAGCCACTGTCATGGCGTAAAAGTGCTGCAGA
TCCAGGATTACCACCTCCTCTGGATGGGTGTCCACGAACTGGCGAATCTCCAGAAGTGGCTCAAAAAT
(SEQ ID NO: 1522)

Exon: 1001..2523
Exon: 12874..14933
Start ATG: 1084

Transcript No. : CT30035
TAACAAACGACGCCGCGCAATAATTCGAAACTCTTCGGCGTTATTTAAAAAACGAGCAGAGATACCTAAATAATAATCTAGACATGAGCAACAAG
AGCACTCCGGTGCGGCAGCGCATCCAGCAGTTCCAGACGCGAGGAGTCCACAAATCCACGCCGGCATCCGAGATGCGCAAGAAGGTGCTGATGAC
GCGGGCGGAGGATCGGGAGCACCGGGATCGTCCCGAACAGCTGCTGAACACTGCATTCAGCGGGAGCACGCCACAGCCGAAGCCCAAGCCCACGG
CCCTGAATGCCTGCTACACACCCTCGTCGCTGTACAGGAATGCGAACTCTACTCCTGGAAGAGCAAAGACGCCCGGCACCGGGAAATCCAGCTGC
AGCAGGACAAAGGAGCGGGACTCTCTGATGGAGTCCTGCCTCAGCGTGTCCGAGGAGAGCAACATGATTGTGGCGGTGCGAGTGCGGCCACTGAA
TGCCCTGGAATGCACACGTGGTCAGGTCACCAATGTGGTCCAGGTGCACGGAAACAGCAACGAGCTGACTGTCCAAGCGGGCAGCAGTGCTGATG
CCTCCGCCGGCGTGACGCACTTCTTCAGCTACGACCAGGTCTACTACTCGTGCGATCCCGAACGAAAGAACTTCGCCTGCCAGGCCAAAGTCTTT
GAGGGCACAGCGCGTCCCTTGATCGACACTGCCTTCGAGGGCTACAATGCCTGCTTGTTTGCCTACGGCCAGACGGGCTCGGGCAAATCGTACAG
CATGATGGGCATTGAAGCATTGGATGACGCCGCTCTGGATGGCGGACCGCCGCACGATGAGGCGGGCATCATTCCACGCTTCTGCCACGAGCTAT
TCCGCCGCATAGAGGCTGTGAAAAGTCAGCAGCAGCTGCAGGTGGAGGTGGAGGTCAGCTACTTTGAGATCTACAACGAGAAGATACACGATCTG
CTGAGTGTCCAGCATGCGGCAGCTGCCACCGGGGAATCCACGCCCATCCAGCAGCAACAACAGCAGCAGCGTCCGGCTCTAAAGGTCAGGGAGCA
TCCCATCTTCGGGCCCTACGTAGTGGACTTGAGTGCCCACTCGGTGGACTCGTACTCGGCACTCCGCAACTGGCTTGCCGTGGGCAACTCCCAGC
GGGCCACTGCCTCCACGGCCATGAACGACAAGAGCTCGCGCTCACACTCCATCTTCAACATTGTCCTAAACCTCACCGATCTGAGCAGTGACGAT
GGCCTGTCCTCGGATACGGACTCGAGCACGGCCTCCTCCCTGCGGCAGACGCGGCGCAGCAAGATTAGCCTGGTGGACCTGGCGGGCAGCGAACG
CATTAGCGTCTCCGGATCGAACGGCGAGCGGATCCGCGAGGGCGTCAGCATCAACAAGAGCCTGCTGACGCTGGGGAAAGTAATTGCTGCTCTCG
CCGATTCCCGCAAGGCGATCGCCAATGGACCCCTGGGCTCTGGGACGCCCAGCACCTTCGTTCCCTATCGCGAGAGCGTGCTCACCTGGCTGTTG
CGGGAAAACCTCGGCGGGAACTCGAAGACGGTCATGTTGGCCACCATTTCACCGGCCAGCATCCATGCGGATGAGACCCTAGCCACTTTGCGTTA
CGCCTGCAAGGCGCGTTCCATCGTCAACCGGGTGAAGGTAAACGAATCCCCCCACGACAAGATCATACGGGATCTGCGCGCCGAGGTGGATCGCC
TGAAGTCGCTGAGGAACGAGTACGAGCGCCAGCGGCGCTTGTCCGGCAATAGTAACAATCCCGTGCCACGTAAGATCATCATTGAAACCTCCGTG
GACGAGACCGAGGTGGAGGCACTGCGTCAGCAGCTGGCAGAACGGAAAGGGAGCTGAGTCGAGCGCAAAAGTCATGGATGGAGAAGCTCAAGGA
GGCGGAGGATCAGCGCAAATCGGAACTTCGTGTCCTGAAACGCCGGGGATTGGCTCTGGAACTAACTGCTGAGCAGAAGCAGGCCTGTCTGGTTA
ATTTAACAGCGGATCCCATACTAAGTGGCACCCTGTTCTATCTGTTGCCCCAAGGACTAGTGCGGATAGGACGAGGTCGTCTGCCAGGAGGGAGT
TCTAGTTCGCAGCCTGATATTGTACTGGATGGTCCACTGGTGGCCTTGCAGCACTGCAGCATCGAGCATGAACGTGGTGGCAAGTTGTATGTCAT
CCCCGGCAGCGAGGACTTCGAGACCTACGTGAACGGAGAACTACTGAAGGATCGTCGCCAGCTGTTTCATGGCGACCGTCTCGTCATAGGTGGCT
CCCACTACTTTCGCATTTCCAATCCCTTCTGCTCGCAAAGAGGCAAGGCCGATCATCCGGTAGATTTCCAGCTGGCCCATCAGGAGATTTTGCAA
AAGCAGGAGCAGCAACTTCGCTCCGAATTGGAGGCGGAAAAGCGAGCCGCTCTCACGAAGATTGAACAGGAGCGGGCGCAGCATGCCCGGGACTT
TGAGGAGCGTCTGCAGTGCCTCGAACTAGAGCAGTTCAAGTACAAATGCAACAGCGAGATGCTGGAGACGGAACGCCAGGCCTTGGCCTTGGCCC
AACAACAGGAACACACTCCGCTAAGGCATGAAGATGCAGTATCAACTCCAGCACAGAAGTCGACTATACTGGAGGACATTCAACGCATCATGCTG
AATCCCTCGGAGGAGAGTCTTCACAAGACCCAGTTGATGGTCAAAGAGGCCACCCAGCGTTGTCGCCAGTTGGACCTGCCATTGGAGTTCCGGCA
AACTCAGACGCCAGATGAATTTGGTCTCCTGCGCACTGTTATCTTGATTCTGGATAAGCAGCGGGGATTGAAGGCCGAGTGGCCCACAGCTAGAC
TGGGTGTGTGGTTGGATTTGGTCAGGGATAATGCTGAACAGCAGGAAAAGCTGAACGCTACAACCATTTTCCAGAGTGTTGAGGTGGATTGGGAG
CCACTGGACGCGGATCTCAATGAGACACTGAGTGACACACACAACTCCAGTCGCATTGCCCTTAATCTGAGTGCCATGAAGGATGTTCTGTTGAA
TAAACCGCTGAAACGCCTGCTCAACGCATCCAGCAGCAAGAGCAATACACCGCGACAGACATCCACTCCCTCACCTGGAAGCCAGCTGGTGCACT
TCACCAAACGCCTGCTGACCTACGATCCGGAGGAGATACCTGAAAGCCAGAGTAGTTTCACAACGCTCGTCCAGCAGGAGCTGCAAATCATGCAG
CGATCCGCCCAGCGTTTACGGCGACACTGCGAGGCTGCCCTACTCGAGCGTGAAAACCATCAGGACAACGGCGTCCTGGCCGTCAGCCTGCAGGA
GGCTCTGGCACGAATGGACACCGTGCTGAACGGGATGCACACTTCGTTGGCGAGAGCGGAGGCCACTGCATGTGTCACCTCGCCGACGAAAACAC
AGAAGGCTGTGCGCTTTCTTATCGATTGACGGAGATTAGTTCGCACCTTGGACTAGATTTTAATGCTGCAATGTGCTTTGTGTTGTTTTTATGTT
TTTAAATATATATTTTTTGTATATTGATTTTTAACAATAAAATGTATTGATAGCACCTTCAAGTGAAA
(SEQ ID NO: 1523)

Start ATG: 84

MSNKSTPVRQRIQQFQTRGVHKSTPASEMRKKVLMTRAEDREHRDRPEQLLNTAFSGSTPQPKPKPTALNACYTPSSLYRNANSTPGRAKTPGTG
KSSCSRTKERDSLMESCLSVSEESNMIVAVRVRPLNALECTRGQVTNVVQVHGNSNELTVQAGSSADASAGVTHFFSYDQVYYSCDPERKNFACQ
AKVFEGTARPLIDTAFEGYNACLFAYGQTGSGKSYSMMGIEALDDAALDGGPPHDEAGIIPRFCHELFRRIEAVKSQQQLQVEVEVSYFEIYNEK
IHDLLSVQHAAAATGESTPIQQQQQQQRPALKVREHPIFGPYVVDLSAHSVDSYSALRNWLAVGNSQRATASTAMNDKSSRSHSIFNIVLNLTDL
SSDDGLSSDTDSSTASSLRQTRRSKISLVDLAGSERISVSGSNGERIREGVSINKSLLTLGKVIAALADSRKAIANGPLGSGTPSTFVPYRESVL
TWLLRENLGGNSKTVMLATISPASIHADETLATLRYACKARSIVNRVKVNESPHDKIIRDLRAEVDRLKSLRNEYERQRRLSGNSNNPVPRKIII
ETSVDETEVEALRQQLAERERELSRAQKSWMEKLKEAEDQRKSELRVLKRRGLALELTAEQKQACLVNLTADPILSGTLFYLLPQGLVRIGRGRL
PGGSSSSQPDIVLDGPLVALQHCSIEHERGGKLYVIPGSEDFETYVNGELLKDRRQLFHGDRLVIGGSHYFRISNPFCSQRGKADHPVDFQLAHQ
EILQKQEQQLRSELEAEKRAALTKIEQERAQHARDFEERLQCLELEQFKYKCNSEMLETERQALALAQQQEHTPLRHEDAVSTPAQKSTILEDIQ
RIMLNPSEESLHKTQLMVKEATQRCRQLDLPLEFRQTQTPDEFGLLRTVILILDKQRGLKAEWPTARLGVWLDLVRDNAEQQEKLNATTIFQSVE
VDWEPLDADLNETLSDTHNSSRIALNLSAMKDVLLNKPLKRLLNASSSKSNTPRQTSTPSPGSQLVHFTKRLLTYDPEEIPESQSSFTTLVQQEL
QIMQRSAQRLRRHCEAALLERENHQDNGVLAVSLQEALARMDTVLNGMHTSLARAEATACVTSPTKTQKAVRFLID*
(SEQ ID NO: 1524)

Name: KINESIN MOTOR PROTEIN
Classification: motor_protein
Gene Symbol: neb
FlyBase ID: FBgn0004374

Celera Sequence No. : 142000013384351
AATGTTTTTTTGTATTGAAAGTATATTTAAAATATCTCAAGTTCAAACTTTGATTTTTGTAAGAAAGATTACGCTCTTCGTTATTTTTTGACATC
TAGCCCCATTATTTTACCACTAAGTATGATCGGATTTTTTAACAATGTCAGAGGAGCCAATTTTCATCACCCACTCATGAGGTGCCCAACATATG
AATATGTCAACTTTTAGTCCCACCGAAACCAACGTCTTAGACCCGGCTGTGATAATTAGCGCAATTCGTTTTTCGTCTTCTGCACTCGAGCGCCT
TTCTAGCTATCTTAATTTATGTACTTACGTTTAGCACAATTTACGTTTATTTTTTCTGAAACTTTAGCAACCTCCGAGGCTCTCAAACTGCAAGT
TACAAACACAATCCTTTCGCTTTCACGCTCTCTCACAAGCACACGTCCACACATTCTAGTAATCTAAGCCAAGTTTTTATAAATATTGTAATTAT
ACACCTGAACACGCACACACACTTGCACACAAAAAGACAGGGTGAAGACCTACCAAACCAAAAAAAAAAAAAAACACAATTTTCAAAGGAATAAA
TGTTTAAGAAGCCAAAGAAATTGTGCGTGTTTAGCTAATTTTCCCGATCGCAACCAAATGGAGAAAAGTAATCGGCGAGCTATGCAAAAACTAGT
ATATTTCATTTCATAATACAATAATTTATGTACGCTGGCGTACTTTACATATCTTTGTGTTTCCTTTCGTAGTTCGTAGTTCCAGTAGTATAAAA
ATTGTTCGAAAAACACATACGAAAATGATAGTGGGGCAAAGTAGTTGAATATCCATGATATGATGATTAGCAAACACTTTTGGCTTAAAATTAAA
GACATGACATGAGGTGTGCGGGGAGGGCGGGGAAAAAGACATAAATATCTAAATGTAAACTGTTGCACTTAAATGAAATGAAGCCAGGGCGCTGC
TGGCTGCTCTCCCTGGATAAGTATAAAAATATGCTTCACGGCCGGCGCATTTAAATGTTTTCCACGTGCCACACCTTGGTGTTGCAGTCCTGTCC
GGTGGAGATCACAGTGTTATTGTCCAGCCAGACCAACCGAGTGATTTGCGACTGCGGATGGGCATCTGGAGTGGGCAGAAAACAATATGTCAGAT
ATCGCTTAAAGCTTACTACTCTTTTTGAAATACTTACTCTTGATGATAGTATGTTTGGCCGGATTGGCCACGGACCAGATAATGATAGTAGTGTC
CAATGATCCACTAGCAACCAGCAGCGAGTTGGGCGACCAGGCCACCGTATTTACGCGAGCACTGTGGAAGCCCCACTCCTTGTTGTGTGCAGGCT
TTTAAAATACACTCGATTAGTAATGGAATTAAGACATTTATGATTCCTTAATACCTTGTACTCCTCCACTGAGTAGAGCACCACCTTGCGATGGG
CATCGCAAGCCACCAAATACTTCAAGTCCGGCGAATAAGAAACATCCGTGACAGCTCCCAAGTGATCCAGCTCCACTTTGGGCTCCAATACTCCG
CCCTTCAGGGTGTAGATGTGCAACTTTTGGTCATCCCCGCCGACAGCAACATCGGAAGTGTCCGCATTAACGGCAATCGAGCTAGCCTCGTACTT
AATGGGCAGCGAAAAGATCTTCTTCTGGTCCTGCACGAGAGTCAACTCTTTGATGCAAGCAAGTGCAATGATGTTCTCGTTGCGCAAAATGGCCA
AGCCACGTGGCTGGCAGTTAAGCTTCACCACATAGTCCGTGTAGGAGTTGCCCTCCACGCTGAACTGGCGTAGGCTGTCGTCGATGCCACAGGTA
TAGACAAAGTCACCCCAGGCGGCAATGCCGTTGATCTGGTTTCCGTGTCCAGTGCCCGTGATGCGATCGTTGGTGCCGCTGCCCGAGTTCCAGTT
GGTCACCACGCCATCGTGGCTACCCGTGTATATGGTGCTGCGGTCATCGCTCAGTCCCAGCACGGTGATGGGCTTATTGTGGCCCTTCACCACAC
GCAGCGGTTTCGAGGGATCCGCCACATTGAGGTAGGTGATCACGCCCGAAAGCGAGACGGTGATTAGGTTGTCTCCTTGCCACAAGCAGGACACC
TGCTGGTCGTCCACAGTGGTGCCCATCACAAACTCGCTAACCAGCTCGCGCGACTCCACTGTCCAAAGGCGGCACGTCTTGTCGCCGGAGCAGGT
TAGCAGTTGGGTGCTGTCTGGTTTCCAGGCCAATGCGTAAACGCCGCCCTTGTGGGCAGGAGATCCAAATTCGCCCACCAGTTCAGAGCTGGTGC
CATCGTACAGAAAGACTTTGCCATCAAAGCCGGCGGAGGCGAAGAATTTGCCATCGGGCGAGTAGCGCACAGCCTGGACGAAGCGAGAGTGATCC
TGCTTGGTCATCTTGAACTTGAACGGGGGTCCCTCGAACACGGCGATAGTATTGTCTTCGCTGCCTGTAATAACAAGTGTGTGTGTGTAAGTAAG
TTTATTGCATTTTGGGACTATTATGTGAACTCACCCGTAACAATGCGGAATGGCCTGGCTGGCCGGAAGTCCGCCGAGTTAATAGACTTGGACTG
GCCACTGATCTCGCCCACAGACGTGCCGGTTTCAGACATAAAGACATGACCGAAACGTTCGCGTCCTTCACCCACGGCAACGATGCGCTGATTGT
CTGGCGACCAGCTAATATCCTTGATGGGTCCTGCAATGGGCTGGAACTCATTTTTAAGCAGGTGCTCCTTGTTGACCGTGTCCCAAATGCGAATC
TTGCCGGAGGCGTCTGGTGAGAAGAGGAGAAAGCCAAATAAATAACATTGCTCGCTTCAAAACCGCAGATAAGATAAAGAAACCGCTCCAAATAA
GGAAATGCTAATCATGACCGTGGCGTGACTCATAGTGGTCACGATTTTTATGCTCTGTTGCCGAAAGCCGGGTGCTCCAAGTGTGAAATTGCTGG
GCGAGACTTACCACCAGATGCAATATAAAATCCGCTGGGCGAGTACTTGGCCACGTTCACTGCACACGAGTGCTCCGTGTAGACATCGGCAATGG
CTGGATTCTATGGTGCGGAAGAAAGGGAAAAGCATACATACATATTTAGAGACACTTTTAGCAAATTAAAACAAATTAATGGTAAATGGGATCC
TAATTATGAACATAGGTGTTTGGTTTTGAATTTGTTATGTATGTTTCCTTCATTAACATTTCATTTTCCAGAACCTGAATATCTTTTGGCGGAAG
ATTTTATTTCTTGATCATTAAAGATACCATAGAAGTGGCGGGATTATCGGGACAAAAGACAAAGAAACATGGAAATATTTTGAATTTATACCGAT
TCAATGGGTGAAAGATAGGCAAACACATAGCTGCTGTGAAGAATCACTTTGACCAGATGAAAACATCATAATGATGATGCGTGGGCGGCAAACAA
GAAATGTATCTATGTGCCAGTCTGTGTTTTGCCGGTTGGCCTGTGGAATGGGAATCTGTGTTTTGCGCCTTATATACTGTACATATATATATAAA
TAAATATAGAACAGCTGCCCGAAAGCCAGAAAGCACACACAAACTGGCAACAGAAACTGCAGCCTGTCCAAAAATAAAACACCATTTGGACGTAA
ATGCCATGGATTTATGGCAGGAACGGAGCAGCAGGCTGCAGCATATATCAGCTTACCTCGATGTTCCGGATGATCACAGAGTTTCCATTGGTGTA
CAGGAAGTTCTTGCCCTTGGGATCGGCACCCAAAACGATGGGTTGGCCGCGTTGGGTGCGCGGCAGAGTTGCGTAGATGTTTTCTGCAATTAAGC
GATTATTTCGATTAGAAATGGGCTGTGACTGCTGCTACTCAGATAACGCCGGCAAATTGGAGTGGGTGGAAAATAGGGTGCGGCTTCGTTTTTGG
GGAGCGAACGGGAACGGGGTCGCTCCAACGGCTCCACACGCGCCTCCTCTTACTGCTTAAAAAGGTCTTTCATATGCATCTATGCCCATTTATGG
GCATAATCACGGTGCTTCCGGCGATTGCTTTCTGCTTTTACCGTTTTCGCCTGTTGACTCATCCCCCTCTCTACGTATCACATTCGGAGTGGGA
TCGGATTCATGACTCCAGTTTATCTCTGTGGGATTCCAACTCACTGTTTTCGTACGCCGGTGGTTGGGGTTGTGCCATTCTGGTGATTTCTCGGT
GCTCCTGAAGCCTTTACTAATTAGTGCGAAATTCCGCGGATAAATGAAAACACCAAACTCAAGTTCGCCGACGATTAGTGGTGGGCTAAGATCGA
TGTTTTCACCATCGTCGTCATCGATGGTTTTTTCTTTGCTTTATATCGACTTTGCGCTGCGTTTACCCCTTTTTAACAGCGAAGTGAACTGGAAG
GAAATTAAAAATATATTGTTCTGTGTTTTATACTAACAGTAACTACTAATTGCTACCGTTTTTAATTATACACTAAAAAATTGTTTTTTTTTTTG
GGATTGAGTTTTCAATTTCCTATATTTGAAAAGGAAATATATAATCAAAATTGTATTTTTATCTAATTTAATAAAATGTATATTTTTCAAAAACT
ATCTAAATATCGATAAATTGCGCCAAATAAATTAATCGGTCTCTGTGGTTCCCCACCTCTACCATTGTTTATATTTTTCATTTTCCGCAAGAATG
ATGCAAAGATTTCCGACGCAGGCGACCGTGGAGAATCCACGTTATGGACAGCTAATCATAGGACCTCCTGGTTCTGGGAAAACCACCTATTGCGG TGAGGCCCTTAAGTTCTATCGCGAACTGGGCCGTCAGGTGGGCGTTGTGAATCTGGATCCAGCCAACGAAAACATGTCCTACGAACCGGTGCTAA
GTGTGATGGAGCTAATCACTGTGGAGGATTGCATGGAGCACCTGAAGCTGGGACCAAACGGAGCTCTAATGCACTGCGCTGAGTATCTGGCCGAC
CATTTGGAGGATTGGCTGTTGCCGGCACTGCGCAAACTAAGCGCCACTTACAACTACTTCCTGTTCGACTGTCCCGGCCAAGTTGAGCTATATAC
CCATCACAACGCTATGGCCCGGATTTTCGAGCGTTTGGAGCGTGAAAGATATAGCCTGGTCACCGTTAACCTTATAGATTCCCATTACTGCTCGG
AGCCTGCCAAATTCATTGCCACTTTGCTGATGGCATTGAACACCATGTTGCGGATGAGTCTACCCCACGTTAATGTGCTTTCCAAGGCCGATCTG
CTAAAGAAGCACGAGACCAAGT
(SEQ ID NO: 1525)

Exon: 4247..4130
Exon: 3788..3667
Exon: 3047..2957
Exon: 2768..2505
Exon: 2439..1385
Exon: 1328..1178
Exon: 1110..1001
Start ATG: 4163 (Reverse strand: CAT)

Transcript No. : CT30041
CGAACTTGAGTTTGGTGTTTTCATTTATCCGCGGAATTTCGCACTAATTAGTAAAGGCTTCAGGAGCACCGAGAAATCACCAGAATGGCACAACC
CCAACCACCGGCGTACGAAAACAAAAACATCTACGCAACTCTGCCGCGCACCCAACGCGGCCAACCCATCGTTTTGGGTGCCGATCCCAAGGGCA
AGAACTTCCTGTACACCAATGGAAACTCTGTGATCATCCGGAACATCGAGAATCCAGCCATTGCCGATGTCTACACGGAGCACTCGTGTGCAGTG
AACGTGGCCAAGTACTCGCCCAGCGGATTTTATATTGCATCTGGTGACGCCTCCGGCAAGATTCGCATTTGGGACACGGTCAACAAGGAGCACCT
GCTTAAAAATGAGTTCCAGCCCATTGCAGGACCCATCAAGGATATTAGCTGGTCGCCAGACAATCAGCGCATCGTTGCCGTGGGTGAAGGACGCG
AACGTTTCGGTCATGTCTTTATGTCTGAAACCGGCACGTCTGTGGGCGAGATCAGTGGCCAGTCCAAGTCTATTAACTCGGCGGACTTCCGGCCA
GCCAGGCCATTCCGCATTGTTACGGGCAGCGAAGACAATACTATCGCCGTGTTCGAGGGACCCCCGTTCAAGTTCAAGATGACCAAGCAGGATCA
CTCTCGCTTCGTCCAGGCTGTGCGCTACTCGCCCGATGGCAAATTCTTCGCCTCCGCCGGCTTTGATGGCAAAGTCTTTCTGTACGATGGCACCA
GCTCTGAACTGGTGGGCGAATTTGGATCTCCTGCCCACAAGGGCGGCGTTTACGCATTGGCCTGGAAACCAGACAGCACCCAACTGCTAACCTGC
TCCGGCGACAAGACGTGCCGCCTTTGGACAGTGGAGTCGCGCGAGCTGGTTAGCGAGTTTGTGATGGGCACCACTGTGGACGACCAGCAGGTGTC
CTGCTTGTGGCAAGGAGACAACCTAATCACCGTCTCGCTTTCGGGCGTGATCACCTACCTCAATGTGGCGGATCCCTCGAAACCGCTGCGTGTGG
TGAAGGGCCACAATAAGCCCATCACCGTGCTGGGACTGAGCGATGACCGCAGCACCATATACACGGGTAGCCACGATGGCGTGGTGACCAACTGG
AACTCGGGCAGCGGCACCAACGATCGCATCACGGGCACTGGACACGGAAACCAGATCAACGGCATTGCCGCCTGGGGTGACTTTGTCTATACCTG
TGGCATCGACGACAGCCTACGCCAGTTCAGCGTGGAGGGCAACTCCTACACGGACTATGTGGTGAAGCTTAACTGCCAGCCACGTGGCTTGGCCA
TTTTGCGCAACGAGAACATCATTGCACTTGCTTGCATCAAAGAGTTGACTCTCGTGCAGGACCAGAAGAAGATCTTTTCGCTGCCCATTAAGTAC
GAGGCTAGCTCGATTGCCGTTAATGCGGACACTTCCGATGTTGCTGTCGGCGGGGATGACCAAAAGTTGCACATCTACACCCTGAAGGGCGGAGT
ATTGGAGCCCAAAGTGGAGCTGGATCACTTGGGAGCTGTCACGGATGTTTCTTATTCGCCGGACTTGAAGTATTTGGTGGCTTGCGATGCCCATC
GCAAGGTGGTGCTCTACTCAGTGGAGGAGTACAAGCCTGCACACAACAAGGAGTGGGGCTTCCACAGTGCTCGCGTAAATACGGTGGCCTGGTCG
CCCAACTCGCTGCTGGTTGCTAGTGGATCATTGGACACTACTATCATTATCTGGTCCGTGGCCAATCCGGCCAAACATACTATCATCAAGAATGC
CCATCCGCAGTCGCAAATCACTCGGTTGGTCTGGCTGGACAATAACACTGTGATCTCCACCGGACAGGACTGCAACACCAAGGTGTGGCACGTGG
AAAACATTTAA
(SEQ ID NO: 1526)

Start ATG: 85 (Reverse strand: CAT)

MAQPQPPAYENKNIYATLPRTQRGQPIVLGADPKGKNFLYTNGNSVIIRNIENPAIADVYTEHSCAVNVAKYSPSGFYIASGDASGKIRIWDTVN
KEHLLKNEFQPIAGPIKDISWSPDNQRIVAVGEGRERFGHVFMSETGTSVGEISGQSKSINSADFRPARPFRIVTGSEDNTIAVFEGPPFKFKMT
KQDHSRFVQAVRYSPDGKFFASAGFDGKVFLYDGTSSELVGEFGSPAHKGGVYALAWKPDSTQLLTCSGDKTCRLWTVESRELVSEFVMGTTVDD
QQVSCLWQGDNLITVSLSGVITYLNVADPSKPLRVVKGHNKPITVLGLSDDRSTIYTGSHDGVVTNWNSGSGTNDRITGTGHGNQINGIAAWGDF
VYTCGIDDSLRQFSVEGNSYTDYVVKLNCQPRGLAILRNENIIALACIKELTLVQDQKKIFSLPIKYEASSIAVNADTSDVAVGGDDQKLHIYTL
KGGVLEPKVELDHLGAVTDVSYSPDLKYLVACDAHRKVVLYSVEEYKPAHNKEWGFHSARVNTVAWSPNSLLVASGSLDTTIIIWSVANPAKHTI
IKNAHPQSQITRLVWLDNNTVISTGQDCNTKVWHVENI*
(SEQ ID NO: 1527)

Name: ACTIN-INTERACTING PROTEIN?
Classification: actin_binding

Celera Sequence No. : 142000013384599
TCTAATTCGGCATACGCCAGTGATTTTTTAAATATAAACAATGGTTTCGTCTAGCTGAAACTAGCTTCCTTTCTGATTTTTAATTATACAAATTC
CAAAATTCATTGGAAAACAAAATGTTCCGAAACTCAAAAGAATGAAAATTTTGGAAGCCCATATTAAAAAAAAAAAACGAGACCTGTAATCATTTC
CAGTTCTGGTTCCCATTCAATTGATGACACTTGTGCGAAATCAGAGTTTATGCGAATACAAATAATCGTTTATTGCGAAACAAACCCGAAAATAA
ACGCGGATGATAATCTTTTGACTCACTGCACTGGTTCTATGCATGGGGCTTAGCCCCCAAAAAATGGCTAGATAGTACAAGTTACCCCACGACCA
GTGGCGCGGTTTCCACTGCTTCCGCTCTTTGTAGCCCTTTTTCGGGCTCTTCTGCTGCGCTTCGTTCTTCGTTCGTGCTTCTTCTTCTCCGACTT
CATCGCCGCCGTCTCCTTTGCCGCTCTCTTTGTAAGTGCAGCTCACTCCCACTCGCATATGTACATACAGAGCCCGGAATACTTGGAGTGCACTG
CTCCCTCGCGCAATTTATGTTCTGTTCGAGTACATATGCCGCATACATATGTACGTGTGCGAGTGTAGGAGGTTGTCAGAGGTCAGTCTCATCGC
CGCATGTATGTAGGTATGTACATGCATACAAACACCCGTTCCAATTGCCAATCCATTCCCCGTGGCGTTCTGCAGAAACTAGATTTCCCGCTCTC
TCTCGGTCCCGTTCGCTGGTTCTTTGTCTCTCTCGCTCTCCCGCTGGCTAAAACTGGTTGAGTGAGTTTTTTCGGCTGGCCGCTTTTGTCGGCTT
GGTTCGTTCGTTCCGTTCCCGTTCGTTTCGTTTCCGTTCCGCGTCTTGTAAAATTCTTCTTCGCCATGCTGGTTCATTCTCATTCAGTTCTTA
ACACTCGCCGGATAAACAACAGTTTGGCGCTTGTTCGCGTTCACTTCCCGTCGCGTTCAGAGAGAATACACTACTACTGCTGCTGCTAGTGTGTG
TGCGTGCGTGTGAACTGTGCGAAAAGAAGCAATATAAAGTATTAATACTAGTGGAATATTAAGTAAATCTAAGTGCAACAGAAACATACACATAC
CTAGCCTATGTACGTATGCTACAAGATATACATATCTGCAGCAAATAAATGTTAACTCAGTATACAAGCGAACAAAAGCACCAGAAACAAATTGT
TTAGTTTTGCTGCTCATTCTTCTTCTTCCACCGATGCCGTAGAGTTCATCAACTTGTTTAGAATCGCGTACGTGACTGTATGTATGCCTGTGTGA GTGAGTGACAGTGTGTTGGTGCTGCCTTTTTCCTGCTGCGCTTCCTCTTGCTCGTGCATCTATCTCTTTCTGGCGGCGCATCACTTGCATTGTTG
CTGTTGCTGTTTGTTGCAATGCAACAAAACATTTTATTCTTGCCTTTTCCCCCTCCTGGTCTTCGCCTCCTTTGGCGTTTGTTTATGAGCGTGTT
TGTGTATGTGTGTTTGTTCTTTTCGACGTCCGCGCGCATTGTTGTTATTTGCTTGCATTAACTTCTACGTTTCTACGCTTTTGTTATTATTATCT
CATTTCTTATTTAGCTCTGCGCCACAGTCTGCTCTCCACAGTCACGGCCAGCAGTTGGTGTAAAAGTGTAATGTTGATGCTCGCCAAAGACATAA
ATAAAATAAGAGTGAAAAATGTAGAAAATCTAAGATATTTTTTCAGTTTGTGCAATACTACAAATTCGCTTGTACATATCCCCTCGACCTTAACT
TTGCTTTCATATTCTCTTTCTGCGGAATACTATTCTGTATATTCCCCTGGTCAATAACCACTGTATTTGCAAGAGCAAACAATAATCTGATAATG
ATGAAATGGTTTATCAACCTCTGAAGCCTAGAGGTGTGCACACTTCCTTCAACTCCAATGCGCGACGACCTTCCCCCGGCCAAAAAGTCCGAAAG
TCGAGCCTATTTATCGCGACACAACTGTTCAAACAATTCCCCAACAACATTCGATTCGCGTCGGCAGCGACTGTGTTCATGGGTATTGTTGTGGA
TATCGTTATTGTTATTGCATTTGTTGTTGCTGTTGCCGCTGCGATGCGGAAGAATAAAACACGAGTTTGTTTTCTTGTTTCTGTGTGTATTTTAA
ACCAAAATTATTACGGCAATGTTCTTTAAACTTAATCACTGTAGACTGACAGACTGATCGACGTGCAAACCACGCTTGGGGCTTCTCATTAATAT
ACGAACTGCCGGTTCGAGTGAGTTAGTGAGTGCCTGTTTTATTTACGCCGAAAGCAAAAACACAAGAGGCGAAAACAAAACCGAAACCAAAATCT
AAAAACGTGTTTCAAATTTGTTCCTATCTGTGTTGTGTCTCTGGGTCCAGTATTTGGGGTTTGGCGTACAAGCATGTGGATATGGATACGAGCAG
AACGGAAAGACGAAACATAACATATCGAATGCTATTTACTCCATGTGTCTTGTTTCACGCTCGATTTGCGTCGCCAGCAGAGCTAAGAAATAAAA
AACTACGCTTACTGATTAAAAAAGCTGTCGCCGGGCTTTATATTTTGCGTCGAACTGATTGTGTGCAGTGATTACTCGGAAGCGGGAATTAGAAA
GGACCCCGGCCAGATATTTATTTGATTAAAAAATGCAAAAGCATGCTGCTAGCAACAGAAAAGAAGATTGTTTAAATTAATCATAAAATTGCACT
AGTTTTTGCACTAGTTTACACTTTATACTTTATCGTAAACACCAGCTCGGGCAACCTTTTTGAAAACTCGAGAATTTACTGTTTATAAATAGGTA
CAACTGTACCCTAAACAAACAGAAGGGTTGAACAATTATAATTTTATGTTTTTTTCCTTGTTTTTCTAGCTCGTTACTGTATTGTTTGGAGCAGT
CGAAAGTAATCTTCTTGGGTTTACCTAAAGACTTACAAGTCTGATCTAATTCACTTTTATTCGCATTCGCCCAGTGATCACTGTAGATTACCAGC
TGCTTTGAAGATTTTCTGATTTACAATTCAGATACAATTGACAACGATCCTTCTTTTATCAACAGCGATTTGGGCCATCTCCAATCGATTCGCCA
TCGCAACCCGAACGCCTTGTGTAAATGCGTTTCCTGTGCTGTTTTGTTACTTTCTGAGATTTTCTAGAACTCGGTCGGGGTCGTTCTTCTTCCCT
CTTCTGTCCCCGCCAATCTTTGTCGTACCAATTTCGTTGTGTTTTGCTCTGCTTTGTTTTGGGTTCATGTGCGAGTTTTCATTATCAGAGAGCGT
TGCTTACCACCACGTAATAGATAACGCAGGCAACCCGAAGTTGGTACATCTCTAATTGAAAATGTTAAAGTAGATAGCAAATATTTATCGAAAGT
TAACACGAAAATGAGGCGTACAGAGAACACGTTCCAATTGATTAGATGATGTTGCACCACAAGACGATGGCATGTGCATCTGCGTTTAAACTTCC
TTTATGAGGTGAAATATTTAGGGCCTATTTAAGCTTGTAGATACTTTTAGTTAATTTGATCTTTTGCACACTTGGAAATACAGTTTGCTCTCACA
TCTAACCTTGGAAAAAAACAAAGGAAGTGAGTTTGCTCTCGACTATTTTGAAGTAAAGAGTGCGCGAATCTACATAGAAAGTCCTTATATGGTAT
TTCGTTTTACTTGACCAAAATTCTGAATGGAATGGAATATTCCCAGCCGACACTGTACCTGTGCAAGGTTGCGTCGATATTTTCTACCACCACTG
TGCAGGACACACAGACACTTGCCATCTCGCTCGCCCTCGCTCACAGTGCAGCAGGAGAGTGGGGGAAGAAGCGGCAACTAACGAACCACAGACAC
TACAAAGCGCAGTAAGAAAGAAAAATGTTGTGCAGAATGAAAAAAAAAACAAGAACAGACAACAGAAACGAAAAAAGAACAAGAACTGCAATGAC
GACGCCGTTGACCTGCGGGGCCTTTGATGCGAGTGGGAAAGAGAAGGAGATGGATGGTCGTGGGAGAACGGCCCGTGGAGAAGAGCGAGCGGAGA
GTGTGAAAGAGGCAGAGGAGAGGAGCGTCTGGGATCTCGGGACCCTCTGCTAAATTGGATGCTGCTATTCTTCTTCTTCTGCTTTACCTCTTCCT
TCATTCCCTCGCCACCCATGCATCGCGCGACTACAATAAAACTCTCTTGTGCAGATTTTGTTGTTCTTGGATTTTCGCCCATTGTCTCCTTCAAT
AAAATGCGTCAAGTCAATTTCATTCACCAGCAGCTGCTGCTTTGGGGGTCGCTTCGCTGCTGACGCATCGCTGGCGTCGTCTGATAAAAAAAAAT
TCAACAAAAACCCAAAAACAAAAAAATACCAGAGAAGCAATCGTCGCAGAATTCGACGAAATTCACAAGGGAAAACAGTAAAATAGTTAGGCAAG
AACAGGAGATACATTCCAGTACCCCTTCCCTGTCACTTGTCTTGAGTCAACTTGTCTTACCTAGCTCACGAAACGCAAAACAATATAAAGACTGG
AGATATGAAATTACATCCGTTCAATAATAAAAGTTTACATATGCTAAGTTATAAGATGAAGACGAGGAGCAACGACATGATAAAGGATTAAAAGA
TTCTAATACCAACCAATGGTGGTATTAATCGGATTAGACTTTTTGAAATACTTTGTTCTTTCCAATCCTAACCGAATTTTCGTTCACAATGATTA
ACATCAAAAGAAGAAGATTCATGATAATATTGATATCCAGATCCTATCTTAAAAACATTTGCTCTTTGCCAATATCTACTGTAGCGTAATTTGCA
TCAAACCAAGGCAGCTGCGGTCGTGATGCTGGCGGTGCCTTTGCGATGAAATCGAGGATGCGAATGGAATGGGATGGTCGCTGTAGGATGGGATG
AAGATTGGAATTGGGATCGGGACGGATATTTTATCTGCCGAGCGACGGCATTTTTGCTGCTGTCTCGCTTAGAAGAGTGTGTGTATGTATTTGTG
GATTTGTGTGCCTGTCAAGCAGGTAAAGGTAGTTTCTTTGTTCTGTTTTATGGCTTGCTCTTTGTGCTGGGCTTCTTTTACTTTTCGCTGCATTT
GAGTACGTCTGTATCCTCGACATAAAGTTGCGGTCAGAATATTGGGACTAAATCACTGAATGATGTTTAAGTGGTTGCAAGAGCACCATATACAG
CTGAATGTTGCAAAGTAATTTATATATTATTTTAAAACGAGATTCGCTCTCATTAGCTTTTAATATTAAACATGTATAGAGACCATTCAACTGTT
CGATAAATCGTAAACAAGTGTAAATCTATTTTTCTATTAAAACTTGGGACTATTTTGCATTTTGACATACGCACCGCACAATATTATGCCCACCA
CTGTTGGCAGTGGGTGTGTGTGTCATGGTAATTGCCTTTGTTTTTGCTGCCGCTATTGCTGCTTTTGGTACCATTGAACTCTGCTGCAGTTGCAA
CCCCAAAAACATTCCGCAGGGGAATGCATGGAAGTTGAACACAGCCTTGTTTATTTTGCTGCACAACCAGAACGAACGCCCTGCCTCCTCTAGCC
CCATCTCTTTGTAGTTGTTTTTGTGGGTTTATGCATTTTTGCGGAATTACAGTGAAGCCTCATAAAATCGTCTAAAATTCTCATAAGTCTTTTCA
AAGATGTAAAGCACTGTACAGTAGGGTGCACCATCGATGACTGGTTCTAAGTTCACGATAGGAGCGTTCCACTGTTGTTTCACGTACAGTCAGCA
CCCCCTATTTTCTCCCACACACCATCTTGATTTGGCTTGAACTTGGTGCTGCGCGCTCTTGTTCCCGATCATTATTTTTTCCATAATCATCGTCA
TCAGCAGCACATCGCAATGCCTCGCTTTGTTTTCTCTTCAGTTCTTCTGAGCCATGAAATTTATAATCTTGTACAAATTGTTTTGCATTAGTAAT
GCCTGTGCGCAGTTTGTTCCACTTCTCACATGGGGTAACCACGTCGGTTCTTTAGCTCCGCTTCGCTTTGCTCCCTTTCTTGTATTCTTATTCGT
TCTTCCGCCGTCCCTCGGTTCTTCTTCTTTTCTTCTCGTGCTTAATTATGGTGGGAGGAGGGCGGCAGGGTGTTCGGGCACGCCCTCAGTGCACT
GCACTCGCATTTCTGATTATTAGCCCGCTCTATTTTTAAACACTTTTACAAGCGGTCTGGAATTTGTCCGTACACCCCCTGCTACACTTCCATCC
ATCCACCAAAAAAAAAAAAATACTGCTAAGTAAAACATATGGCACAGACATTGAGCTCCACTCCCTCTTCTCGAAAAGTGGAGGCGATTCCATTCT
TCTGATGGACTCGTGGCCCCAAATGATATTAATCTTGTCATGATATACAATACCAACTGTCAGTTTGATTTGGCCCGAACCGTTTTACCACTCTT
CCGTTTGTTCTCCGTCAACTAGTCAACTATCTCCCAAAATTTGCTAATCTAATCGATAGACAACTCGTTCATTATCAATTCCCCTCGTTCCCCCC
GCCAAGAAACGCTAAATTATTGTTTTTGATGCTCTAATTAGGGGTGTTGCACTTTTGACATGTTGGAAGTGTGTATTTTAGACGCCTAACTAAAT
ATAGTATAGCAGGTTTACTTACATAAAGATTATAATAACTTTATTAATCAATTATACTATAAATAAAATAATAGGTTAATATAATAGAATAAAGT
CAGAGTAAAGTGAATTTTTGTGATTCAAGGGTATTTCAGAAGTTCATGAAGAAAAAAACCCATGTTTATGTTTGGTTTCCACTTTGAACGGTGAC
GTTTTGGTGCTATTCTTGTATTTATTAACTAATTTGTTGAAATTACCGGTGGTAGATTTATGAGTCAGGTTTTTTTTTTATTCCTACGCTCATGT
ATGTGCGTTTCAGGTGTGATCGATACCTTTTGAAGATCACCGCTTGTTTTTTTGTTGCCCTCCCTCATTTTCCGCGATTCGCAACAGCTCGTAAT
GTTGCAGAAGCAACATTAAAATGCCGCTATTTTACACGTGTAAATTTGTATTTCTTTTGAATGTGTGTGTGCGAATTTATGTGCCTGTCGTCTGG
CTATTTTCCCCTCATCTCTTCCGCTCTTCGCCCTCTTGGGTCTTTTGTCTCTTTTCCGCTGCCGCCTTTGTCGGTATACAGAAATTTTCGCTATG
CAGTTATGTTGATGAGATGTGAATGCGATGATGCTGCTGCAACGTCATTTCTAGCATACTTGTCTCCTCTCTTCCTCTCGAAAGTTCTGCGGCAA
CATAGAACAGAGAAATGCTGAGTGAAAGGAATAGGCAAAGCAGAGGGAGAGAGGCTGGTGGCCGAGAGAACGTTTGGTTGTTATTGCTTTTGGAT
GCGGTCGTTGCCCAAATTGGAAAAAAACATGCGCACAGAGTACACTGAAAAGAACCAGTTTTGTAATATAAATAAAAGTCGATATTATTTGGCAT
AGAGAATATTTTGATTTTTGATTAGAGTATGGGAAAAAAATTTGCATTAAGATATACTCTCCTATTTTAATGTATCTTTTATCAACACGGATGAA
ATTTCTTTTCGCAAAGTCTGCTACGTTTTTGCTGTGTGTATTTATCGTTTATCGCTTCCTGCTTTTGTTGCGCTTTTCTCTTGACACTCGCTCTT
CGCTGCTCTCTCCACGCTCTCTTTCGTTCTCTCACGCAACCTGTAGCGCGCGCAAAAAAAAGTGTATTTTGGCGTGGAAAATTGTTGCTCTTTCT
GGGGGGAAGTTTCCTCTTTTTATTTATTTTGTTGTGGGTGACTCGCCGCCATATTGTTTTAGGGGTTGCTAAAACATAAGCGCAATGGGGGTGGT
GATGTGTGCAGTTGTATTGTTGCTTTTGCAGCCGGCATTCAACAGTTCGGCAAAAAGAGCGCTCATTTTGGGAATCGTCTCGCGTTGGTCGCTCT
CTTAGTAAACGTAAATAGGGTGTATTGATTTTTCCCGGGTTTTTCGCCACTTTGTTTTCCTGTCTTTCTGGAAGTTGCTCGGTTAACAGGCAGCC

FIGURE SHEET 832

AAAAAATTCTCAGACTGTCTGTGGAGTGTGACATTGCATTGCATGGCTGCAGTTGCGGAGTAGTTGTTGTTGCTGGGAGCTGGAAAATCCCCAGG
ACATTTGCAGCTCTCTGTCGCTCCGCTGTCGCGGCCACTGCCGGCGTCGCTGCTTTTGCGGGGACCTGAGCTTTACCCGGGTCGCTGCATTATGC
GCAGAGTTAGTTTTGCAGGGAGCCGCGTAGCATTCACGTCACGCAATTTGTACATAACTAGCGAAGATTTAACATTACATTAGTTTGCAGTGTC
CTTGCCGACGCACGACGTCACTGTAATGCATAAAATAAACCAAAAACAAGAGCTCTCAATTAACCTTGCATTCAATTATCCTTCCTAATAACCAT
TTTTCTCTCTCTTCCCATTGCAGCCTTTTGTGCGCGCGACGCAATTATCTGACAGCACTTGAAAGTATGCTACACAAATTTGTTTCAACTTGTTA
CTGCAACAATAACAACAACCAAAACAACGGCAACCATCCCACGCAATTTATCATATAGACTGCGTAGCAAGCAAGAGCGAGACAGCAACACGGCG
CAACCAGCAGCGAGAAACAACAACAACAAGCAGAAATCAGGAAACCAGGAAACGAACTGGAATATATAGAAAATTCTACAACAAACTACAACAAC
AAAGCAGTAAAGGTAAGTCGGCTTATCTCCGTTTAATGAGTTTTACGTTTAGTTTTCGTCGTTGCACAGTTTTCCCTTTGTTGGAAATTTACCGG
TAGATATATTTTACATACATACATTCATATATGCAGCTCTTTATCAGGGATTTCTCGCGCCCATATTTGGTATAGCTATTCAGATTAGGCGGCAA
CTAAACTGTAAATATAATTTAGCTTTATAATTTGAAGTCCCTAATTATTTGCACAGGAACTGGAAGTTGGAGATAAATGTTTTTATTCTTGTAAA
TTAAATAATTATTTACCTTTATTTACCGTTATTTACCTTTAATGGCCTTCCGTATTCTTCTTTTTATTTGTAACAAACTTACTATTCCAATGTTT
CTAAGAATGGATTAGCATACCTGTACCTACGCCTAGAGGGCTATTTTGGGCAACCCAATTAACCTCAAAGTTAAACAAAGTAATATCCTTCACGA
CGAAAAAGTGAATATTTGTGGAGCTAGAAAGGACTTTCTAGGGAGCATTGGGAAAAGGCATTAGGTCTGGGTGTATGTGCATGATAAATGTACAT
CCAGTCTAGACAGTTGCAGTCACCCTTCCCATCCCTCTGACATATACAACCTTCCCCCCTTGGGCGCATTTTTCGGGGTTGATTTTCAGCTGCCT
CTCTTTGCTTTCACTTGGATTGCCTTTATGTTGGCTTTCTTGTTGACGAAAGTTTCGCCTGGTCTGGAAATCTAGAGAAGTTTCTCCGGGGCTCC
ACAGTTTTCCTTATTTTGTTTTTTTTTTTGTTTACTTTTTGCGACGGGGGCTTGTTGTGAAACTCCCCGTTCGTTTTCCCTGCTTTTACTGCTC
GCATTCTACCCAACTTCAGATTCGCCGTCCTTCTCGAAGGCAACGAACCGCGAAGGCAGCGAAAAGGGGAAGTAAAATTATGATTACGGGGTGTC
CTGTCCTGTCCTGTCCTGTCCGTCTGTCTGTCTGTGCGTGCGTTTATTGCATTTGTGTCCGTCTCCGCGCAAAGGATAAAGGTTAGGGGGTAGTA
GATGTAGACGGGCAGCGATTTCCTCCCCGGTCAAAGTCCTTTTATCCAGGCGTACAGCTTCACTTTTAGCCCCGCTTCTTCACTCTGCCGTAAGA
AATTGGAATTGTGTTTAAAAGCATTCGGTGGGGGCGCGAATCCTAGTTTGATTCGATTCAGTCTGTTGGGCTGGGGAAATAGTAATACCAAGGGG
AATACACAAGCCACATACCTTTCAACTGTCGTCTTCGAAAATGTTTAATAAAACACGGTTCACAGCTGTCGCGCTTTGGGGGATTAGATGGAGCA
TGGAGCAGGATGAAAGCAGGATTGGAAGGAGGCAATTAACTACAAATTATGATAACAAAGGGGATGACTAAGGAAAAGGGGCCGTTGTTTGTGGG
GTGTGGCACATTTGTTTGTTTGGAGGGGCCATGGAAATGCCACAACGTTTTGGTTCAAGTGGAGGAAATGCTGACTCACAAGGATAAAAGACAAG
GACCGCAGGTGACTCATGGGTCAGTCGATTTGAGGGGCGAAAGTGGCGGAGAGTAGGCGAAAAAAAAACACGTGGTTGGCACAGGAAGCATTGAA
ACCATTGCTAAGATTATTCACCTTCGTTGTGGGGAACTTAAATCGATTAGATTATAAGTCCGTATTTTCCAATAAATGTATTCATTGTCTACATT
GTTTAATTAATCCCTCCACTTGTTCTTTCTCCTTGCAGCTGTTACTCCTAAAGGTAAACGGAGCCACCGACGGCACTTACAACATAAAGATGGCG
TCCTCACCGACACCATCTCTGGACTCGATGCGGGGCGGGGCGAACTCGATTGAATCGTACGAACACGCCGGCTATCTATCAGACTCTCCGCTCAC
GTTGAGCGGTTCATCGCCACCGGCAAGCGATTCGGCAATCTGCAGTGATGAGTACACGGGCGGCAGCAGCGTTAAATCACGCTCTGAGGTGACTG
TAATCAATGGCCATCATCCCATTTCGGCCTCCGTATCGTCCAGCTCTTCGGCCAGCTCTTCATCCTGCTCGTCGTCATCGTCCTCATCCTCGTCT
TCGTCATCGTCCAGCTCCTCGACCAGCGGCCTCAGCGGTTGCGGCAGTACCAGCAGCAGTGTGATCAGCGCCAACAACGTTGCGAGCAGCAATGG
ACCAGGCGTTATCGGCAGCAATCTTCAGTCCTCAAACAATGGCGGCAACTCGGGCATCAGCAGTCTGGTCGTGGGTGCGGGCAAGGGAAGCAACA
GCAGCAGCAACAGCTCCTCGAGCAACACATCCGCCAATGGATCTCCGCCACGTTGCACCGCCTGCAAGAGCAAGTGCAGCGATGCGGTGGCCAAG
TGCTTCGAATGCCAGAGCTACCTGTGCGCCAATTGTGTAACTGCTCATGAGTTCATGCACTGCTTCAACGGACACAATGTGTGCCTGATTAAGGG
TTTTGAGGCGAGCACCACTGGCACTCCGCTGTCGGTTGGATCGCCTAGCAACAATCCGGCGTCGAATGAGTTCAAGTACGCCAGTTCGCTGACCA
TGATGCTGCAGCAGCAGCAACAGCTCGACTCGCAACAACAGCAACAGCAGCAACAATTGCTGCCGGCGCAGCCTATGTCGCAACTCTCGAAGATT
GTACTGGCAGCCGCCGCGCAGGCAAATTCCCAGGAGCAACAGCGAGAGGATAGCATCTATGGTTCACTGCACCCACAACAACAACAACAGCAGCA
GCAACAGCAGCAGCGACAACTCTTCTGCCCCCGACACAAACAGGAGCTGCTCAAGTTCAGTTGCCGCACCTGCTGCATCCTGGTGTGCAAGGAGT
GCATTGTACTGGAGCACTCCACAGGTCTCCACGAACTGGAGAACGTGCAGTCCCCCGGAATGACAACCTCTACGGGATCCACAGCCAACGAGTCA
GCTTTGCAGACTCTGCTCGCCGATATGCGTGGCAAAATTGGCGAGATTGTCGGCATTGCTGGAAACTCGGACCAGAATCTCACCAAGGTGAAGCT
GCAGTACCAAAAGGCTCACAACGAGCTGAACGAGACGCACCAGTTCTTCGCTTCCATGCTGGACGAGCGCAAGACCGAATTGCTCAAGGAACTGG
AGACGCTGTACACGGCCAAGGTTAACAGCAACAATTCGTGGCAGCAACGCTCCCGCGACTTGATCGACAAGGGACTGGCCACCTGCGAGGCGGTC
GAGCGGAGTCCTGCTCCGCCATCATCCTTGCTGACAGAGGCCCTTCTCCTGCGCAAATCCCTGGAGCAACAACTACAGACGGGCATTCAGGAGAT
GCAGCTACCATTCGAGATCGAATTTATGTCCAACTATCAGTCGATTCAGGCCGGCGTGCGCAACACCTTTGGTTACATTCGGGCAAACAGCTCAG
ATGGTGGACCTACTGGCATGAGCCTGACGAGCAATGGCCACGGAAAGCAGCCGCCAATTGCCCGACCAACACAGAGCGCCAGCAACAGCAGTGCG
AGCAGCGCGGGCAGTGGTCACCATGGCCACCACCAACAGTCACACCATCATGGCCACCACAATCATCACCAGACGGCCCATCATCAACAGCTGCA
GGCGCAATCGTCGCTGCATGGCTTGGGTCTTGGATTGAGTGGCGCCAGTTTGTTGGATAGCAGCTCTAGCGCAGGCGGAGCAGTGGGAGCCTTCA
GCAACGGAGGACTTCTGCTGGGCGGTCGCGATCGGAACGCTCTGGCAGTGGAACAGCATTTCGGTGAGCTGATGCCCAAGCGAGGAGGAGGTGGC
TACACGGGCAGCAATGGATCGGCCACCAGTGCCGTGGCCCACTACAATCCCTACGAGAAGTGGAGCAACGGCGGTAGCGACAATCTGTTTTCATC
GGTGACAAGCGGCGTGTCCGGTAGCTCTGCAGTGGCCGATGCATTTGCCAGCCTGTCTGCTGTTGGAGGATCCGTGGTTAGTGGCGCTGGAGCTG
GCGGAAGTACTGTGAGCTCAGAGTCGTTGCTGGACCTCACCAACAAGCTGCTTTCGGCCACTATCTATCCGCCCAAGTCGCAGATCAAGCGACAG
AAGATGATTTACCACTGCAAGTTTGGCGAATTCGGCGTGATGGAGGGCCAGTTCACGGAGCCCAGCGGTGTGGCGGTAAATGCCCAGAATGACAT
CATTGTTGCGGATACGAACAACCATCGCATTCAGATCTTCGACAAGGAGGGACGCTTCAAGTTCCAGTTTGGCGAGTGCGGCAAGCGTGACTCGC
AGCTGCTCTATCCGAACCGCGTGGCCGTGGTGCGCAATTCCGGCGATATTATTGTCACCGAGCGCTCGCCCACACACCAGATACAGATCTACAAT
CAGTACGGCCAGTTTGTGAGGAAATTCGGGGCCACCATTCTGCAGCATCCTCGCGGCGTGACCGTGGACAACAAGGGACGGATCATTGTGGTGGA
ATGCAAGGTGATGCGTGTGATCATCTTTGATCAGAACGGCAATGTGCTGCACAAGTTCGGGTGCTCTAAGCACCTCGAGTTCCCCAACGGCGTGG
TGGTCAACGACAAGCAGGAGATCTTCATCAGCGACAATCGGGCGCACTGTGTCAAGGTGTTCAACTACGAGGGCCAGTATCTGCGGCAGATTGGC
GGCGAGGGTATTACCAACTACCCAATTGGCGTCGGGATCAACTCGAACGGGGAGATCCTCATCGCGGACAACCACAACAACTTCAACCTGACGAT
CTTCACGCAGGACGGGCAGCTGATCTCGGCGCTCGAGTCGAAGGTGAAGCACGCGCAGTGCTTCGATGTGGCGCTCATGGACGACGGCAGTGTGG
TGCTGGCCAGCAAGGACTATCGGCTCTACATATATCGCTATGTCCAACTGGCGCCAGTGGGTATGTAAACACACAGACACACACACTCCATGGAT
GTGAGTCCGGAAAGGAGGAGGATCTGTGGTCCGGCACTCACTACTTCTATAGGCTAAGTTCTCAATAGTCTGACTTGCTCGGTCTCTCCAGCTCT
AATTCTAAATCTACACAATCGAAGTTGAAATCGAAATCTATAAGATCCCTACTATCTCCCCCGATCTGTCATCTCTCATAGCCTTAGACTTTGCT
CGCTATGTAATAACACACACGCACACTGTTGGAATGATTTTTATTATCTTTTAAATTATTGTTGAATTTTGTTTTATTTTTTTATATATATTTA
CACTGTTAAGCTTAGTTTTTATTTGTGCGTACTTGTTTATGATAAATATATATTATGTGTATTCATGTTCATGTTCAAATCGGATAGTGCCGCCG
CCTCTCTATATCTTTGCACACTTCTCACTTCAAACCCTCGTATCTCTATCTCGCGTGCAAGTCGTATTTTCAACAAACACAAGCAAACAACCGAA
ACAAACAAAAAAAATGACACTTTTTAACTATATATAGTAGATACCAGAAGAAATCCCTCCACTTTTTTTATGTTCGTTGCCGACTGCAAGGAAAA
AAAAGGAAAAAAATTATGAAAAAAAGAAGTTGGTATAAAATAAACTTAACAAATAACCGCCAACAAAATGGAGCCGCGTATCGAGCATTAATTAA
TTAATAATTGATTGTAATTTTTAGATATATGATTGCGCAAATTGTTTGTTATTATTATTTTTGATTGCATAAACATTTGATACATTATATATTAT
ATAGCTGTTTTTTACGTTTATAAATTATTTTTGATTATACCACTTATTGATTACTGATTATTTATATTTATATACATTAATTAATTATCCTCTAA
GACATGTTTGCTACTTTTATACGAAATCAACCGAACCCAAAACCGAACCGCGACACAAACAACAATTCACAATTTTTATACTCGCTTAGAATTTA
TGTTTTCCATTGTTTTATTGTAACCACGACAGCGGAAAGAAAAGATGGAATTACCTACCTACACCGTAATAATAATGCAGACAAAAACCCACTGG
CGATTCTTTAATTTAATTTAAACAAAAACAACTGAACGCACTGAGAATAGTTGAAATTTTTGTTCTTGATTGTTGAACTATTTTTTGTTTAGGCA

FIGURE SHEET 833

TTTATATTTTAAAATAATTTCTTCGTTCGCAAGGAAGACGGACGAATTTGTTGTTTTGCCCCAAAATATATTACTATATTATATGCGAAAATTAT
TTGTTGTCAAATTGAATTTAAATAAACATGGAAAAATGTGTATATCAAACGAAAACAAGGCGATATTTATGTGCACCAAGTTAGTTAGTGGTAAC
TTCGAGTGCGAATTCAAAGTATCTTGAGGATGTGTGTGCATAGATCTAATTGAGTATTTAAAAGTAACATTTAACTAAAAGTTGGCAATCAGCGC
AGAAGACTTGAAACATTTATAACTATTATAATTATACAATTAAAGTATGTCTATTAATATACGATAAACACTTAAATCAGTAAATCAAAAATCTC
AAATAATTGAATAGTTATAAAGAGAAACCGCGAATAGGGAAACAACATCCCAGCCAAGCCAGACCAATCGCCCACTTATGTTTACTTCCTTGACA
GAAATAGGGACTAAATACGAAAGCCACACGGTGGGCAACAATCAGGATATGGTACTCGAAGGAATCGTCACATATCCTCTTGATCTGTTGCGCAC
CGTGTGCACATGGACTTCTAATTGCAATGATTTAGTTAAAGCATTTACTTGGATAGGCCTCAAATGATGATTGCAGAGCTAACAAAAGTGTTCTT
TAAGTAAGGGTTAGTTAAAAGCAGTTAGGACGTTAGATATTTAAAGTGAACATACTATTAAGGCAAGGAAACACAACTTTTTGAGACTACAAACG
CAACATTAACAGGAACAGCATTTAAAAAATGTTTATTTTGTAATTTTAAAAGTAATCACTATGTATTTTTGTTGGTTTTGCTTGGAACGCGACGC
GAACCCCGCCCCCTTGACCCCATTGACACGCCCACACGTAAGCAGGTATTAGATTTCTTGAATATAATTTAACAATATTGTATTAAACACGTAGT
ATTTAACTAATATAGTTTCCCCCCTTCCTCATCCTCTTTATATTCCCTTGTTTGTTTTGAAAAAACGCCTTGCTCTGTGTAATTTCTGATTTGCT
TGACCTATTATTTTAATTATTTGATAATTACCTATGTTTTGTGTGTATCTACTTAAGTGAGATTATTAAATATACGAAAATATATTTTTTAGTTC
TTTCTT
(SEQ ID NO: 1528)

Exon: 1001..1388
Exon: 8472..8752
Exon: 10540..14966
Start ATG: 10540

Transcript No. : CT30047
TCGCGTTCAGAGAGAATACACTACTACTGCTGCTGCTAGTGTGTGTGCGTGCGTGTGAACTGTGCGAAAAGAAGCAATATAAAGTATTAATACTA
GTGGAATATTAAGTAAATCTAAGTGCAACAGAAACATACACATACCTAGCCTATGTACGTATGCTACAAGATATACATATCTGCAGCAAATAAAT
GTTAACTCAGTATACAAGCGAACAAAAGCACCAGAAACAAATTGTTTAGTTTTGCTGCTCATTCTTCTTCTTCCACCGATGCCGTAGAGTTCATC
AACTTGTTTAGAATCGCGTACGTGACTGTATGTATGCCTGTGTGAGTGAGTGACAGTGTGTTGGTGCTGCCTTTTTCCTGCTGCGCTTCCTCTTG
CTCGTGCAATTGCAGCCTTTTGTGCGCGCGACGCAATTATCTGACAGCACTTGAAAGTATGCTACACAAATTTGTTTCAACTTGTTACTGCAACA
ATAACAACAACCAAAACAACGGCAACCATCCCACGCAATTTATCATATAGACTGCGTAGCAAGCAAGAGCGAGACAGCAACACGGCGCAACCAGC
AGCGAGAAACAACAACAACAAGCAGAAATCAGGAAACCAGGAAACGAACTGGAATATATAGAAAATTCTACAACAAACTACAACAACAAAGCAGT
AAAGATGGCGTCCTCACCGACACCATCTCTGGACTCGATGCGGGGCGGGGCGAACTCGATTGAATCGTACGAACACGCCGGCTATCTATCAGACT
CTCCGCTCACGTTGAGCGGTTCATCGCCACCGGCAAGCGATTCGGCAATCTGCAGTGATGAGTACACGGGCGGCAGCAGCGTTAAATCACGCTCT
GAGGTGACTGTAATCAATGGCCATCATCCCATTTCGGCCTCCGTATCGTCCAGCTCTTCGGCCAGCTCTTCATCCTGCTCGTCGTCATCGTCCTC
ATCCTCGTCTTCGTCATCGTCCAGCTCCTCGACCAGCGGCCTCAGCGGTTGCGGCAGTACCAGCAGCAGTGTGATCAGCGCCAACAACGTTGCGA
GCAGCAATGGACCAGGCGTTATCGGCAGCAATCTTCAGTCCTCAAACAATGGCGGCAACTCGGGCATCAGCAGTCTGGTCGTGGGTGCGGGCAAG
GGAAGCAACAGCAGCAGCAACAGCTCCTCGAGCAACACATCCGCCAATGGATCTCCGCCACGTTGCACCGCCTGCAAGAGCAAGTGCAGCGATGC
GGTGGCCAAGTGCTTCGAATGCCAGAGCTACCTGTGCGCCAATTGTGTAACTGCTCATGAGTTCATGCACTGCTTCAACGGACACAATGTGTGCC
TGATTAAGGGTTTTGAGGCGAGCACCACTGGCACTCCGCTGTCGGTTGGATCGCCTAGCAACAATCCGGCGTCGAATGAGTTCAAGTACGCCAGT
TCGCTGACCATGATGCTGCAGCAGCAGCAACAGCTCGACTCGCAACAACAGCAACAGCAGCAACAATTGCTGCCGGCGCAGCCTATGTCGCAACT
CTCGAAGATTGTACTGGCAGCCGCCGCGCAGGCAAATTCCCAGGAGCAACAGCGAGAGGATAGCATCTATGGTTCACTGCACCCACAACAACAAC
AACAGCAGCAGCAACAGCAGCAGCGACAACTCTTCTGCCCCCGACACAAACAGGAGCTGCTCAAGTTCAGTTGCCGCACCTGCTGCATCCTGGTG
TGCAAGGAGTGCATTGTACTGGAGCACTCCACAGGTCTCCACGAACTGGAGAACGTGCAGTCCCCCGGAATGACAACCTCTACGGGATCCACAGC
CAACGAGTCAGCTTTGCAGACTCTGCTCGCCGATATGCGTGGCAAAATTGGCGAGATTGTCGGCATTGCTGGAAACTCGGACCAGAATCTCACCA
AGGTGAAGCTGCAGTACCAAAAGGCTCACAACGAGCTGAACGAGACGCACCAGTTCTTCGCTTCCATGCTGGACGAGCGCAAGACCGAATTGCTC
AAGGAACTGGAGACGCTGTACACGGCCAAGGTTAACAGCAACAATTCGTGGCAGCAACGCTCCCGCGACTTGATCGACAAGGGACTGGCCACCTG
CGAGGCGGTCGAGCGGAGTCCTGCTCCGCCATCATCCTTGCTGACAGAGGCCCTTCTCCTGCGCAAATCCCTGGAGCAACAACTACAGACGGGCA
TTCAGGAGATGCAGCTACCATTCGAGATCGAATTTATGTCCAACTATCAGTCGATTCAGGCCGGCGTGCGCAACACCTTTGGTTACATTCGGGCA
AACAGCTCAGATGGTGGACCTACTGGCATGAGCCTGACGAGCAATGGCCACGGAAAGCAGCCGCCAATTGCCCGACCAACACAGAGCGCCAGCAA
CAGCAGTGCGAGCAGCGCGGGCAGTGGTCACCATGGCCACCACCAACAGTCACACCATCATGGCCACCACAATCATCACCAGACGGCCCATCATC
AACAGCTGCAGGCGCAATCGTCGCTGCATGGCTTGGGTCTTGGATTGAGTGGCGCCAGTTTGTTGGATAGCAGCTCTAGCGCAGGCGGAGCAGTG
GGAGCCTTCAGCAACGGAGGACTTCTGCTGGGCGGTCGCGATCGGAACGCTCTGGCAGTGGAACAGCATTTCGGTGAGCTGATGCCCAAGCGAGG
AGGAGGTGGCTACACGGGCAGCAATGGATCGGCCACCAGTGCCGTGGCCCACTACAATCCCTACGAGAAGTGGAGCAACGGCGGTAGCGACAATC
TGTTTTCATCGGTGACAAGCGGCGTGTCCGGTAGCTCTGCAGTGGCCGATGCATTTGCCAGCCTGTCTGCTGTTGGAGGATCCGTGGTTAGTGGC
GCTGGAGCTGGCGGAAGTACTGTGAGCTCAGAGTCGTTGCTGGACCTCACCAACAAGCTGCTTTCGGCCACTATCTATCCGCCCAAGTCGCAGAT
CAAGCGACAGAAGATGATTTACCACTGCAAGTTTGGCGAATTCGGCGTGATGGAGGGCCAGTTCACGGAGCCCAGCGGTGTGGCGGTAAATGCCC
AGAATGACATCATTGTTGCGGATACGAACAACCATCGCATTCAGATCTTCGACAAGGAGGGACGCTTCAAGTTCCAGTTTGGCGAGTGCGGCAAG
CGTGACTCGCAGCTGCTCTATCCGAACCGCGTGGCCGTGGTGCGCAATTCCGGCGATATTATTGTCACCGAGCGCTCGCCCACACACCAGATACA
GATCTACAATCAGTACGGCCAGTTTGTGAGGAAATTCGGGGCCACCATTCTGCAGCATCCTCGCGGCGTGACCGTGGACAACAAGGGACGGATCA
TTGTGGTGGAATGCAAGGTGATGCGTGTGATCATCTTTGATCAGAACGGCAATGTGCTGCACAAGTTCGGGTGCTCTAAGCACCTCGAGTTCCCC
AACGGCGTGGTGGTCAACGACAAGCAGGAGATCTTCATCAGCGACAATCGGGCGCACTGTGTCAAGGTGTTCAACTACGAGGGCCAGTATCTGCG
GCAGATTGGCGGCGAGGGTATTACCAACTACCCAATTGGCGTCGGGATCAACTCGAACGGGGAGATCCTCATCGCGGACAACCACAACAACTTCA
ACCTGACGATCTTCACGCAGGACGGGCAGCTGATCTCGGCGCTCGAGTCGAAGGTGAAGCACGCGCAGTGCTTCGATGTGGCGCTCATGGACGAC
GGCAGTGTGGTGCTGGCCAGCAAGGACTATCGGCTCTACATATATCGCTATGTCCAACTGGCGCCAGTGGGTATGTAAACACACAGACACACACA
CTCCATGGATGTGAGTCCGGAAAGGAGGAGGATCTGTGGTCCGGCACTCACTACTTCTATAGGCTAAGTTCTCAATAGTCTGACTTGCTCGGTCT
CTCCAGCTCTAATTCTAAATCTACACAATCGAAGTTGAAATCGAAATCTATAAGATCCCTACTATCTCCCCCGATCTGTCATCTCTCATAGCCTT
AGACTTTGCTCGCTATGTAATAACACACACGCACACTGTTGGAATGATTTTTATTATCTTTTAAATTATTGTTGAATTTTGTTTTATTTTTTTTA
TATATATTTACACTGTTAAGCTTAGTTTTTATTTGTGCGTACTTGTTTATGATAAATATATATTATGTGTATTCATGTTCATGTTCAAATCGGAT
AGTGCCGCCGCCTCTCTATATCTTTGCACACTTCTCACTTCAAACCCTCGTATCTCTATCTCGCGTGCAAGTCGTATTTTCAACAAACACAAGCA
AACAACCGAAACAAACAAAAAAAATGACACTTTTTAACTATATATAGTAGATACCAGAAGAAATCCCTCCACTTTTTTTATGTTCGTTGCCGACT
GCAAGGAAAAAAAAAGGAAAAAAATTATGAAAAAAAGAAGTTGGTATAAAATAAACTTAACAAATAACCGCCAACAAAATGGAGCCGCGTATCGAG
CATTAATTAATTAATAATTGATTGTAATTTTTAGATATATGATTGCGCAAATTGTTTGTTATTATTATTTTTGATTGCATAAACATTTGATACAT
TATATATTATATAGCTGTTTTTTACGTTTATAAATTATTTTTGATTATACCACTTATTGATTACTGATTATTTATATTTATATACATTAATTAAT
TATCCTCTAAGACATGTTTGCTACTTTTATACGAAATCAACCGAACCCAAAACCGAACCGCGACACAAACAACAATTCACAATTTTTATACTCGC TTAGAATTTATGTTTTCCATTGTTTTATTGTAACCACGACAGCGGAAAGAAAAGATGGAATTACCTACCTACACCGTAATAATAATGCAGACAAA
AACCCACTGGCGATTCTTTAATTTAATTTAAACAAAAACAACTGAACGCACTGAGAATAGTTGAAATTTTTGTTCTTGATTGTTGAACTATTTTT
TGTTTAGGCATTTATATTTTAAAATAATTTCTTCGTTCGCAAGGAAGACGGACGAATTTGTTGTTTTGCCCCAAAATATATTACTATATTATATG
CGAAAATTATTTGTTGTCAAATTGAATTTAAATAAACATGGAAAAATGTGTATATCAAACG
(SEQ ID NO: 1529)

Start ATG: 670

MASSPTPSLDSMRGGANSIESYEHAGYLSDSPLTLSGSSPPASDSAICSDEYTGGSSVKSRSEVTVINGHHPISASVSSSSSASSSSCSSSSSSS
SSSSSSSSSTSGLSGCGSTSSSVISANNVASSNGPGVIGSNLQSSNNGGNSGISSLVVGAGKGSNSSSNSSSSNTSANGSPPRCTACKSKCSDAV
AKCFECQSYLCANCVTAHEFMHCFNGHNVCLIKGFEASTTGTPLSVGSPSNNPASNEFKYASSLTMMLQQQQQLDSQQQQQQQQLLPAQPMSQLS
KIVLAAAAQANSQEQQREDSIYGSLHPQQQQQQQQQQQRQLFCPRHKQELLKFSCRTCCILVCKECIVLEHSTGLHELENVQSPGMTTSTGSTAN
ESALQTLLADMRGKIGEIVGIAGNSDQNLTKVKLQYQKAHNELNETHQFFASMLDERKTELLKELETLYTAKVNSNNSWQQRSRDLIDKGLATCE
AVERSPAPPSSLLTEALLLRKSLEQQLQTGIQEMQLPFEIEFMSNYQSIQAGVRNTFGYIRANSSDGGPTGMSLTSNGHGKQPPIARPTQSASNS
SASSAGSGHHGHHQQSHHHGHHNHHQTAHHQQLQAQSSLHGLGLGLSGASLLDSSSSAGGAVGAFSNGGLLLGGRDRNALAVEQHFGELMPKRGG
GGYTGSNGSATSAVAHYNPYEKWSNGGSDNLFSSVTSGVSGSSAVADAFASLSAVGGSVVSGAGAGGSTVSSESLLDLTNKLLSATIYPPKSQIK
RQKMIYHCKFGEFGVMEGQFTEPSGVAVNAQNDIIVADTNNHRIQIFDKEGRFKFQFGECGKRDSQLLYPNRVAVVRNSGDIIVTERSPTHQIQI
YNQYGQFVRKFGATILQHPRGVTVDNKGRIIVVECKVMRVIIFDQNGNVLHKFGCSKHLEFPNGVVVNDKQEIFISDNRAHCVKVFNYEGQYLRQ
IGGEGITNYPIGVGINSNGEILIADNHNNFNLTIFTQDGQLISALESKVKHAQCFDVALMDDGSVVLASKDYRLYIYRYVQLAPVGM*
(SEQ ID NO: 1530)

Name: BRAIN TUMOR
Classification: 'transcription_factor
Gene Symbol: brat
FlyBase ID: FBgn0010300

Celera Sequence No. : 142000013384351
AAAGCTGGAGAAAACCTTCAAAGAGAAAGGCTTTCTCATCCAAACCCAGCAGCTTCAATCCGCCGAAGGTGCTACCTATTGCAAATTTAGACAGC
TAAAGAAGTTCACGCGCTACCTTTTCCGCAACTGGAAGGATCACATACCCGAGAGCGATCTGGCCAAGCACCAAAATGCCTCGCGGGAGGATAGG
CTGCCAAATCTGGAAACCCAAACCGCCAACCAGACGACATAGAGCTGCGGCCAGGACATTCAGGAAACATCCACACACAGCACTGCCAAAGATTT
AAGTTTAAGATCAGCTAATGGCCGGCCCAGCTTCGGTTGCGGTTGCCAGTTGAGGGTGGAGAACAGCAACCCATGCCGATTCCGTCCATGCGGGC
TGTCCAACAACGCGATCAATGATCCTCAGCCACGCTTCCTAGTCGTTCATCAGTTTTTTAGTGCCTAATAAAATGTTATTGTTAACAAATAAAC
TCAATGTTTAACCATATGCAAATGTATATTGTTTGGTTGTAAAAGGCATCGTAGTATGTATTTTACAAAATATCCGTCAATACAGTTATGTGTTA
GTACAAAAGATAAACTCCAAAATGGGCGATAAGTCTATAGGGGTTATGCTCGCTCTCAAGGTCGTTTCAATGCCATTGCGAATACTTCTTGTTAT
CATCGTTATATGCTTATTTAGAAGATGTCATTACATCCCGTTTCCAGATTAGCCTAAATGTTAGTTACAGATAATATAAAAATTTCCAAAATGTT
TGCTGGTATGCTTAGGTCGACGAAAGAATTTTGACTCGAATTCATTCGAAAGATGTTTGGAAGTTTGGGCGTGGCCTTGATAAGATAAATTCTCA
CTAATATTGTCAATTTTGTGGATTTGGTTGCATAATTGGTTCAGGTGGCAGTTCATTCAGTTTGGGGATCCTTGGCCAGGTTTTGGGCTTACAAC
TAAAAAACATATTTGCTTTCAATCGATTTGTGCTCCTTTCGACTTCGTCTTTAGTTCGAACTCATGGAGCTCTCATGCTCCTTAGCCGTATCAGC
TAGATATGTCTCCGGCACACTGGCATTCATGGGACACACGTACTCCGTCCAGTCTACGTCACTCTGGCTCTTCGAGCTCTTGCGACGCTTTAACG
AAAACTGTGTGCGTTTCACCGGCTTCAGCTTAGCTGTAATGCTTAGCGGTTGGTACCCGGGTGCCGATTCGGCATCTCGCTTACTCAAGATCACT
GGCCGACCGACTAGCTCCTTAAAGTGCATGGCCAGGTGGCGACGCAGCAGGGACTTGCTCGGTGGTATCGACAGCAGGTCGGCAAGCAAGTCAGC
ATTGAAACGCGGTTCATAAAGCATCAGAGCCCCGTGGACACCAGCACCACGCAGATTGGGCGTGTATTCAGACAGGTCGATGGTCTGCAGCCATC
CCATAATGCGATGCGCTGTCCACAGCTCCACATTGTCTCTGTCGGGAGTGGCTGCGGCTTCATCTTCACTGACAACTTTAATGGAGCGTCGAATT
AGACCTTCCGCGTTCCACGATAAGCGGCGCATGCATAAGATTCCCGCTCGCAAGGAGGCTATGTGCAAACAAGAGCTGACGTGCAATTGGGAGAG
GTCCTCGAGGGTGAGACGATGCAGCATTCGACCGTCAATCTTGGCCTGCATAAAGTAATCTTTATACTGTGGCAAGCCGATGTCATCCAGCCAGC
GTAGAACCCATGTCACATCCAAGCTGGATGCCTTCAGTGTCAGGTCATCAAACTCCTTCCCAGTTAGGTCGTCGATGGCCAACAAGATTTTTTC
CGATGAAGTGGCATCTTTAGGTTTAGCTCTCGTTCGATGTCGACAGGCGAGGCGGTGAAGAACGACACTGATGGATTGGCATTCAACCACTTTCT
GTAGGCGGAAATTGTATTTAGTAACTGGGTTCTTCTTGGATTTTGATGACAAAACTTACCGGCAATTGTCCTCATAGCAGCCTAGACCCATGTAT
GCCAACCAATTGCACACCTCCTGCGCTCCCCAGGTTGTCCAATGTTTTTCATTCTCACCGAACAACGGAGTCTGAGCACTCCACTCAATTCGACC
GCCTGCCGTAGCTCGGGCTCCTCCTCGTCGAAACTCGGGCTCTGCCTGCTCCAAGGCGGTCAGCTCGCAGTTGCTGCTGTTGCTGCGTCGTAGCT
TACCAAGTATGTTGCGCAAGCCACGGGCAGATCTTTCCCTCAGCTTTGGTGAGGGTGTAAACTGCGACATAAAGCTGGAAGTCATTGCATCCTCC
GCTTGATGATGATTGTCATCAATCAAAATGTGTTCGTTCGAAGCAAAGGCCACGTTTCGCTGCTTGCCGCTGCTGTTGGCATTGACGTCTAAGGC
ACGATTGTTATTGTTGTTCACAAACTTGCCATGCGATCTTGGCAGGCTGTGGAACTGCGGTTTGATTTGGTGCCGCAGTGCAGAGGGCGGTGTCT
TGGGCGATCCCATAAAGGCCTTCTGATTAATGTTGCTCAAACTGCCGTAAGGAATATTGGCGGAAATGGCGCTACCTCCATCGTTAGCCTGCTCT
AATGCAGTACGGTGCAGTTTTAGTTCACTTAAGGCACTCATTAGCTCCAGCTTTTGCGTCTCGAGGGCGGAACTAGAAATCATCTGTCGTTGCAG
TTGCTCTTCCTTGGTACACAACTGCTGGCTCTTTTCCGTTATCAGACCCTCCAGCTCGATAATCTTGTCCGCTTGTTCTGACACTCGTTCCGCCA
GCATCTGATACTGCAGGGCTAAGCCCTCCTTATCCCGTTGCAGGCGACGCATACGCTCGTCGGAATCCTGACGAGGTATGTGCGTCTCCAGCCAG
TCGCTGATAATGGCCGCCGTGACAGGATCCGGTGCTGGAGCAGCCAGTCCGACCTAAAGTGATAAGCGTAAGTGTAAGCCCTCCGTTTCTAGACC
TTATCATAGTCAGTGTGACTCACCTGTTGCAGGGCGAGAGCCAAAGTCTTAGCTGTTGACAAAACATTAGTGGCCGAAATTAAGTTGCGTTCGCT
GAGTGTCAGGGAAGACCCTGCTCCGGATATAGAAACGGATCCCGCCTGTGTCGCGGTACTCGATATAAGGCCGTCCATTTGCTGTAATGCTGCCT
CGAGCATTTTGCTGCCCTCCGCCACAGTCGCCATGAAGTCCAAATCAAAGTCTCGCTAATCCCGGGTGATCGATGTGTGGTGTGCTTATTGCGCG
ACTAGTGCATTGTTATGTAAGCAGGTCAGGCAGGGCACGTCATTTTGCACTGGTTTAGGGGAAAATGGCATTTATGGTTATTAATTTCAGCACTA
ATTGGGGAAAACTATCACGAAAATAGAAGCTGCTGCACCGTTCTGCTTCTTCTTCTCGCACACCAGCCCAGCCACTTATCGATAGTCAGCGAACG
CAGAATTGTGTGTAGGAGCAACATCCGATAGTTTGCTAGATGGTCTAAAGTCTACAAAACAAATTTTAAAACAAAATTAATTTTAAGTAACGTAT
AAAAATGCCTAAACACATTTTAATTACATTTTTTGGGGACAAAGTATGCAATATATCTAGATGTGTACAGCTATATTTGGTTTTCCATACCCGAT
ATCTACTGTACAAAAAAGATACCATCACTAATAAGCAGGTGGAACGGTGGAGTCACGAAAGATGTGTCATCTCCAGCCAGAGCCACAACAAAAACA
AATATTAAGGATAAAATAACAAATATCTGAAATGAATCGCTTCGCTTATGTGGAGGCCCGTCTGAGTCCCAATGAATCCTTCGTCAGCCGCGACA
ACAGGGTAAAAATATACGATGGCGACCAAAAGGTGAGCAGCTAGTGAATTCGCACAATACGAAACCGGGTCTTTATTAGACTCAAATCCTTTCAG
ACGGACTTTGAAGACGGCGAAGTGGTGCTCACCACACACCGACTGTTTTGGGGTCGCCCTGGAGAGATTGCCCGGGCCGCCGTAACACTTTGCCT
GCCACTCAGCTATGTGATATCCGTCAGCGAAGAGACTACTGCCTCTAACTTCTTTGGCCGCAAGACTCGCATAATCATGCATCTGCATCCTCCAA CGTCGGACAAAGGACCCGGCCCACTGGACACCAGTCGCGCCACCCACATCAAACTGTCGGGCAAGAATGGCCTGAGTGTCGAGTTCCACAGTGCC
TTGCGGGAGACTCTAAATGCCCGCGTCTGGGAAATCCTCTTGACCAGCGAGATCATCATCAATGGCGTGGCCAGCAGTCCAACCTTGGAGCCTGC
CAACGACAGGCTGGCCCGCATTCAGAAGAGGACAGGAATTGGGGGCATCGAACGGCATTTGGAGGCAAAAGCCAAGGCCACGGATGAGAACATAG
CACTTGCCTTT
(SEQ ID NO: 1531)

Exon: 3381..2969
Exon: 2903..1960
Exon: 1898..1001
Start ATG: 3169 (Reverse strand: CAT)

Transcript No. : CT30105
AGAAGAAGAAGCAGAACGGTGCAGCAGCTTCTATTTTCGTGATAGTTTTCCCCAATTAGTGCTGAAATTAATAACCATAAATGCCATTTTCCCCT
AAACCAGTGCAAAATGACGTGCCCTGCCTGACCTGCTTACATAACAATGCACTAGTCGCGCAATAAGCACACCACACATCGATCACCCGGGATTA
GCGAGACTTTGATTTGGACTTCATGGCGACTGTGGCGGAGGGCAGCAAAATGCTCGAGGCAGCATTACAGCAAATGGACGGCCTTATATCGAGTA
CCGCGACACAGGCGGGATCCGTTTCTATATCCGGAGCAGGGTCTTCCCTGACACTCAGCGAACGCAACTTAATTTCGGCCACTAATGTTTTGTCA
ACAGCTAAGACTTTGGCTCTCGCCCTGCAACAGGTCGGACTGGCTGCTCCAGCACCGGATCCTGTCACGGCGGCCATTATCAGCGACTGGCTGGA
GACGCACATACCTCGTCAGGATTCCGACGAGCGTATGCGTCGCCTGCAACGGGATAAGGAGGGCTTAGCCCTGCAGTATCAGATGCTGGCGGAAC
GAGTGTCAGAACAAGCGGACAAGATTATCGAGCTGGAGGGTCTGATAACGGAAAAGAGCCAGCAGTTGTGTACCAAGGAAGAGCAACTGCAACGA
CAGATGATTTCTAGTTCCGCCCTCGAGACGCAAAAGCTGGAGCTAATGAGTGCCTTAAGTGAACTAAAACTGCACCGTACTGCATTAGAGCAGGC
TAACGATGGAGGTAGCGCCATTTCCGCCAATATTCCTTACGGCAGTTTGAGCAACATTAATCAGAAGGCCTTTATGGGATCGCCCAAGACACCGC
CCTCTGCACTGCGGCACCAAATCAAACCGCAGTTCCACAGCCTGCCAAGATCGCATGGCAAGTTTGTGAACAACAATAACAATCGTGCCTTAGAC
GTCAATGCCAACAGCAGCGGCAAGCAGCGAAACGTGGCCTTTGCTTCGAACGAACACATTTTGATTGATGACAATCATCATCAAGCGGAGGATGC
AATGACTTCCAGCTTTATGTCGCAGTTTACACCCTCACCAAAGCTGAGGGAAAGATCTGCCCGTGGCTTGCGCAACATACTTGGTAAGCTACGAC
GCAGCAACAGCAGCAACTGCGAGCTGACCGCCTTGGAGCAGGCAGAGCCCGAGTTTCGACGAGGAGGAGCCCGAGCTACGGCAGGCGGTCGAATT
GAGTGGAGTGCTCAGACTCCGTTGTTCGGTGAGAATGAAAAACATTGGACAACCTGGGGAGCGCAGGAGGTGTGCAATTGGTTGGCATACATGGG
TCTAGGCTGCTATGAGGACAATTGCCGAAAGTGGTTGAATGCCAATCCATCAGTGTCGTTCTTCACCGCCTCGCCTGTCGACATCGAACGAGAGC
TAAACCTAAAGATGCCACTTCATCGGAAAAAAATCTTGTTGGCCATCGACGACCTAACTGGGAAGGAGTTTGATGACCTGACACTGAAGGCATCC
AGCTTGGATGTGACATGGGTTCTACGCTGGCTGGATGACATCGGCTTGCCACAGTATAAAGATTACTTTATGCAGGCCAAGATTGACGGTCGAAT
GCTGCATCGTCTCACCCTCGAGGACCTCTCCCAATTGCACGTCAGCTCTTGTTTGCACATAGCCTCCTTGCGAGCGGGAATCTTATGCATGCGCC
GCTTATCGTGGAACGCGGAAGGTCTAATTCGACGCTCCATTAAAGTTGTCAGTGAAGATGAAGCCGCAGCCACTCCCGACAGAGACAATGTGGAG
CTGTGGACAGCGCATCGCATTATGGGATGGCTGCAGACCATCGACCTGTCTGAATACACGCCCAATCTGCGTGGTGCTGGTGTCCACGGGGCTCT
GATGCTTTATGAACCGCGTTTCAATGCTGACTTGCTTGCCGACCTGCTGTCGATACCACCGAGCAAGTCCCTGCTGCGTCGCCACCTGGCCATGC
ACTTTAAGGAGCTAGTCGGTCGGCCAGTGATCTTGAGTAAGCGAGATGCCGAATCGGCACCCGGGTACCAACCGCTAAGCATTACAGCTAAGCTG
AAGCCGGTGAAACGCACACAGTTTTCGTTAAAGCGTCGCAAGAGCTCGAAGAGCCAGAGTGACGTAGACTGGACGGAGTACGTGTGTCCCATGAA
TGCCAGTGTGCCGGAGACATATCTAGCTGATACGGCTAAGGAGCATGAGAGCTCCATGAGTTCGAACTAA
(SEQ ID NO: 1532)

Start ATG: 213 (Reverse strand: CAT)

MATVAEGSKMLEAALQQMDGLISSTATQAGSVSISGAGSSLTLSERNLISATNVLSTAKTLALALQQVGLAAPAPDPVTAAIISDWLETHIPRQD
SDERMRRLQRDKEGLALQYQMLAERVSEQADKIIELEGLITEKSQQLCTKEEQLQRQMISSSALETQKLELMSALSELKLHRTALEQANDGGSAI
SANIPYGSLSNINQKAFMGSPKTPPSALRHQIKPQFHSLPRSHGKFVNNNNNRALDVNANSSGKQRNVAFASNEHILIDDNHHQAEDAMTSSFMS
QFTPSPKLRERSARGLRNILGKLRRSNSSNCELTALEQAEPEFRRGGARATAGGRIEWSAQTPLFGENEKHWTTWGAQEVCNWLAYMGLGCYEDN
CRKWLNANPSVSFFTASPVDIERELNLKMPLHRKKILLAIDDLTGKEFDDLTLKASSLDVTWVLRWLDDIGLPQYKDYFMQAKIDGRMLHRLTLE
DLSQLHVSSCLHIASLRAGILCMRRLSWNAEGLIRRSIKVVSEDEAAATPDRDNVELWTAHRIMGWLQTIDLSEYTPNLRGAGVHGALMLYEPRF
NADLLADLLSIPPSKSLLRRHLAMHFKELVGRPVILSKRDAESAPGYQPLSITAKLKPVKRTQFSLKRRKSSKSQSDVDWTEYVCPMNASVPETY
LADTAKEHESSMSSN*
(SEQ ID NO: 1533)

Name: LIPRIN-BETA1
Classification: cell_adhesion

ISOLATED *DROSOPHILA* PROTEINS ESSENTIAL FOR SURVIVAL NUCLEIC ACID MOLECULES ENCODING ESSENTIAL *DROSOPHILA* PROTEINS, AND USES THEREOF AS INSECTICIDAL TARGETS

RELATED APPLICATIONS

The present application claims priority to U.S. Ser. Nos. 60/171,590 and 60/171,627, both filed Dec. 23, 1999; 06/175,763 and 60/175,685, both filed Jan. 12, 2000; and 60/6,663 and 60/187,241, both filed Mar. 3, 2000.

FIELD OF THE INVENTION

The present invention is in the field of *Drosophila* proteins that are essential for survival, recombinant DNA molecules and protein production. The present invention specifically provides novel *Drosophila* proteins and nucleic acid molecules encoding such protein molecules, for use in the development of insecticide and insecticide targets.

BACKGROUND OF THE INVENTION

*Drosophila melanogaster*

The *Drosophila melanogaster* genome is 165 Mb, with about 120 Mb of this being euchromatic. The genome is organized in 4 chromosome pairs and is estimated to contain 10–12,000 genes. Model organisms, such as *Drosophila melanogaster*, share many genes with humans whose sequences and functions have been conserved. In addition to myriad similarities in cellular structure and function, humans and *Drosophila* share pathways for intercellular signaling, developmental patterning, learning and behavior, as well as tumor formation and metastasis.

The genes involved in the development of *Drosophila*, with few exceptions, are the same as those involved in the development of higher organisms. Developmental biology studies the sequential activation and interaction of genes, in relation to developing morphology. Right now, *Drosophila* is the only organism for which one can begin with a list of genes active in the egg and follow the morphological changes and gene activations through to adulthood.

*Drosophila* studies have provided the widest knowledge base available for any single organism; accordingly, developmental biologists use the fly to ferret out the activity of genes with similar functions in higher organisms. Despite its small size, the fly is by no means a small developmental problem. If you know the genes involved in the development of the fly, you also know, to a reasonable approximation, the genes involved in the development of the worm, the fish, the mouse, and humans.

A major goal in insecticide development is to understand and elucidate the molecular mechanisms that govern cell signaling and cell—cell interactions in higher eukaryotes. Many proteins identified in *Drosophila* form major links in cellular communication/response systems. A complete list of proteins from *Drosophila* would therefore be invaluable in developing human therapeutic compounds and kinsecticidal agents. Not only will the proteins serve as models for human and invertebrate cellular signaling and response, such molecules will also serve as molecular keys in identifying therapeutically important human and other invertebrate orthologs.

Insecticides

About 10,000 species of the more than 1 million species of insects are crop-eating, and of these, approximately 700 species worldwide cause most of the insect damage to man's crops, in the field and in storage.

A detailed study of novel proteins from *Drosophila* and invertebrate orthologs thereof, will serve as targets for identifying new members of the known classes of insecticides as well as aiding in the identification of new classes of compounds.

SUMMARY OF THE INVENTION

The present invention is based in part on the identification of amino acid sequences of 511 proteins that are produced by *Drosophila melanogaster* and are essential for survival, many of which look to be insect specific having no knowN homolog in mammalian genomes (See SEQ ID NOs: 1–39). These unique protein sequences, and nucleic acid sequences that encode these proteins, can be used as targets for the development of insecticidal agents and to identify invertebrate and vertebrate orthologs thereof.

DESCRIPTION OF THE FIGURE SHEETS

FIGURE SHEETS 1–836 provide genomic nucleic acid sequences from *Drosophila melanogaster*, predicted transcript, and predicted amino acid sequences of the proteins of the present invention.

DETAILED DESCRIPTION OF THE INVENTION

General Description

The present invention is based on the sequencing of the *Drosophila melanogaster* genome. During the sequencing and assembly of the *Drosophila melanogaster* genome, analysis of the sequence information revealed previously unidentified peptides that do not share structural and/or sequence homology to any presently known proteins, peptides, or domains. In addition, the specific subset of genes, transcripts, and proteins of the present invention are essential for survival: when altered by way of a P-element insertion, it produces a lethal phenotype. Based on this analysis, the present invention provides amino acid sequences of proteins produced by *Drosophila melanogaster* and are essential for survival, nucleic acid sequences that encode these *Drosophila* proteins and methods of using these proteins for insecticidal development and gene target development.

In addition to being previously unknown, the proteins that are provided in the present invention are selected based on their ability to be used for the development of commercially important products and services. Specifically, the present proteins are selected based the need for the protein to be present to produce a viable insect. Some of the more specific features of the proteins of the present invention, and the uses thereof, are described in detail below.

Specific Embodiments

Protein Molecules

In Figure sheets 1–836, the present invention provides nucleic acid molecules, provided in the form of genomic sequences and transcript sequences, that encode 511 protein molecules that have been identified as being essential for *Drosophila* survival. The protein sequences provided herein will be referred to as the *Drosophila* proteins or proteins of the present invention, *Drosophila* proteins or peptides, or peptides/proteins of the present invention.

The present invention provides isolated peptide/protein and protein molecules that consist of, consist essentially of or are comprised of the amino acid sequences of the *Drosophila* proteins encoded by the nucleic acid sequences disclosed in the Figure Sheets (the amino acid sequences are provided in SEQ ID NOS: 3, 6, 9, . . . 1527, 1530 and 1533336, 339 and 342, the genomic sequences are provided in SEQ ID NOS: 1, 4, 7, . . . 334, 337 and 340 and the predicted transcript sequences are provided in SEQ ID NOS: 2, 5, 8, . . . 1526, 1529 and 1532335, 338 and 341), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The proteins of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the *Drosophila* protein having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated *Drosophila* protein can be purified from cells that naturally express it, purified from cells that have been altered to express it (recombinant), or synthesized using known protein synthesis methods. For example, a nucleic acid molecule encoding the *Drosophila* protein is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of one of the amino acid sequences encoded by the nucleic acid sequences shown in Figure sheets 1–836. The amino acid sequences of such proteins are provided in the SEQ ID NO:3, 6, 9, . . . 1527, 1530 and 1533, encoded by genomic sequences SEQ ID NO: 1, 4, 7, . . . 1525, 1528 and 1531, or transcript sequences SEQ ID NO: 2, 5, 8, . . . 1526, 1529 and 1532. A protein consists of an amino acid sequence when the amino acid sequence is the final amino acid sequence of the protein.

The present invention further provides proteins that consist essentially of one of the amino acid sequences encoded by the nucleic acid sequences shown in Figure sheets 1–836, SEQ ID NO:3, 6, 9, . . . 1527, 1530 and 1533. A protein consists essentially of an amino acid sequence when such an amino acid sequence is present with only a few additional amino acid residues in the final protein.

The present invention further provides proteins that are comprised of one of the amino acid sequences encoded by the nucleic acid sequences shown in Figure sheets 1–836, SEQ ID NO:3, 6, 9, . . . 1527, 1530 and 1533. A protein is comprised of an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the *Drosophila* proteins of the present invention are the naturally occurring mature proteins. A brief description of how various types of these proteins can be made/isolated is provided below.

The *Drosophila* proteins of the present invention can be attached to heterologous sequences to form chimeric or fusion proteins. Such chimeric and fusion proteins comprise a *Drosophila* protein operatively linked to a heterologous protein having an amino acid sequence not substantially homologous to the *Drosophila* protein. "Operatively linked" indicates that the *Drosophila* protein and the heterologous protein are fused in-frame. The heterologous protein can be fused to the N-terminus or C-terminus of the *Drosophila* protein.

In some uses, the fusion protein does not affect the activity of the *Drosophila* protein per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant *Drosophila* protein. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A *Drosophila* protein-encoding nucleic acid can be cloned into such an expression vector such that the fusion moiety is linked in-frame to the *Drosophila* protein.

As mentioned above, the present invention also provides and enables obvious variants of the amino acid sequence of the proteins of the present invention, such as naturally occurring mature forms of the proteins, allelic/sequence variants of the proteins, non-naturally occurring recombinantly derived variants of the proteins, and orthologs and paralogs of the proteins. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the *Drosophila* proteins of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al., (*J. Mol. Biol.* 215:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the proteins of the present invention can readily be identified as having complete sequence identity to one of the *Drosophila* proteins of the present invention as well as being encoded by the same genetic locus as the *Drosophila* protein provided herein.

Allelic variants of a *Drosophila* protein can readily be identified as having a high degree (significant) of sequence homology/identity to at least a portion of the *Drosophila* protein as well as being encoded by the same genetic locus as the *Drosophila* protein provided herein. As used herein, two proteins (or a region of the proteins) have significant homology when the amino acid sequences are typically at least about 70–75%, 80–85%, and more typically at least about 90–95% or more homologous. A significantly homologous amino acid sequence, according to the present invention, will be encoded by a nucleic acid sequence that will hybridize to a *Drosophila* protein encoding nucleic acid molecule under stringent conditions as more fully described below.

Paralogs of a *Drosophila* protein can readily be identified as having some degree of significant sequence homology/identity to at least a portion of the *Drosophila* protein, as being encoded by a gene from *Drosophila*, and as having similar activity or function. Two proteins will typically be considered paralogs when the amino acid sequences are typically at least about 70–75%, 80–85%, and more typically at least about 90–95% or more homologous through a given region or domain. Such paralogs will be encoded by a nucleic acid sequence that will hybridize to a *Drosophila* protein encoding nucleic acid molecule under stringent conditions as more fully described below.

Orthologs of a *Drosophila* protein can readily be identified as having some degree of significant sequence homology/identity to at least a portion of the *Drosophila* protein as well as being encoded by a gene from another organism. Preferred orthologs will be isolated from other invertebrates, particularly insects of economical/agriculture importance, e.g. members of the Lepidopteran and Coleopteran orders, for the development of insecticides and insecticidal targets, or vertebrate counterparts, such as from humans. Such orthologs will be encoded by a nucleic acid sequence that will hybridize to a *Drosophila* protein encoding nucleic acid molecule under moderate to stringent conditions, as more fully described below, depending on the degree of relatedness of the two organisms yielding the proteins.

Non-naturally occurring variants of the *Drosophila* proteins of the present invention can readily be generated using recombinant techniques. Such variants include, but are not limited to deletions, additions and substitutions in the amino acid sequence of the *Drosophila* protein. For example, one class of substitutions is conserved amino acid substitution. Such substitutions are those that substitute a given amino acid in a *Drosophila* protein by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

Variant *Drosophila* proteins can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

The present invention further provides fragments of the *Drosophila* proteins, in addition to proteins and peptides that comprise and consist of such fragments. The fragments to which the invention pertains, however, are not to be construed as encompassing fragments that may be disclosed publicly prior to the present invention.

As used herein, a fragment comprises at least 8 or more contiguous amino acid residues from a *Drosophila* protein. Such fragments can be chosen based on the ability to retain one or more of the biological activities of the *Drosophila* protein or could be chosen for the ability to perform a function, e.g. act as an immunogen. Particularly important fragments are biologically active fragments, peptides that are, for example about 8 or more amino acids in length. Such fragments will typically comprise a domain or motif of the *Drosophila* protein, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in *Drosophila* proteins are described in basic texts, detailed monographs, and the research literature, and they are well known to those of skill in the art.

Accordingly, the *Drosophila* proteins of the present invention also encompass derivatives or analogs in which a substituted amino acid residue is not one encoded by the genetic code, in which a substituent group is included, in which the mature *Drosophila* protein is fused with another compound, such as a compound to increase the half-life of the *Drosophila* protein (for example, polyethylene glycol), or in which the additional amino acids are fused to the mature *Drosophila* protein, such as a leader or secretory sequence or a sequence for purification of the mature *Drosophila* protein or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W.H. Freeman and Company, New York (1993). Many detailed reviews are available on this subject, such as by Wold, F., *Posttranslational Covalent Modification of proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Protein/Peptide Uses

The proteins of the present invention most importantly can be used as insecticide targets without even knowing the specific biology of the target. First, the proteins of the present invention are essential for *Drosophila* survival. P-element mutation has shown that these transcripts are essential for survival. Second, these proteins do not have known homologs. Such proteins can be routinely configured in assays to identify small molecule inhibitors of the target protein.

Further, the *Drosophila* proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its binding partner or receptor) in biological fluids; and as markers for tissues in which the corresponding protein is preferentially expressed (either constitutively or at a particular stage of tissue differentiation or development). Where the protein binds or potentially binds to another protein (such as, for example, in a receptor-ligand interaction), the protein can be used to identify the binding partner so as to develop a system to identify inhibitors of the binding interaction. Since the proteins of the present invention are selected base on the need for them for survival, such proteins serve as excellent targets for the development of insecticidal agents. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the proteins of the present invention are based primarily on the source of the protein as well as the class/action of the protein. For example, proteins isolated from *Drosophila* and other invertebrates serve as a target for identifying anti-invertebrate compounds, e.g. insecticides. A combination of the invertebrate and mammalian orthologs can be used in selective screening methods to find agents specific for invertebrates.

The *Drosophila* proteins of the present invention (excluding variants and fragments that may have been disclosed prior to the present invention) are useful for biological assays related to the class of proteins of which it is a member. Such assays involve any of the known protein functions or activities or properties mediated by the protein.

The *Drosophila* proteins are particularly useful in insecticide screening assays, in cell-based or cell-free systems. Cell-based systems can be native, i.e., cells that normally express the *Drosophila* protein, as cell of tissue sample or culture. In one embodiment, however, cell-based assays involve recombinant host cells expressing the *Drosophila* protein.

The proteins can be used to identify compounds that modulate the protein activity. Both the proteins of the present invention and appropriate variants and fragments can be used in high-throughput screens to assay candidate compounds for the ability to bind to the protein. These compounds can be further screened against a functional protein to determine the effect of the compound on the protein activity. Further, these compounds can be tested in animal or invertebrate systems to determine activity/effectiveness. Compounds can be identified that activate (agonist) or inactivate (antagonist) the protein to a desired degree.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the *Drosophila* protein that competes for ligand binding. Other candidate compounds include mutant *Drosophila* proteins or appropriate fragments containing mutations that affect protein function and thus compete for ligand and small molecules. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) protein *Drosophila* protein activity. The assays typically involve an assay of events in the signal transduction pathway that indicate *Drosophila* protein activity. Thus, the expression of genes that are up- or down-regulated in response to the *Drosophila* protein can be assayed. In one embodiment, the regulatory region of such genes can be operably linked to a marker that is easily detectable, such as luciferase. Alternatively, phosphorylation of the *Drosophila* protein, or a *Drosophila* protein target, could also be measured.

Any of the biological or biochemical functions mediated by the *Drosophila* protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric *Drosophila* proteins in which any of the protein's domains, or parts thereof, can be replaced by heterologous domains or subregions. Accordingly, a different set of signal transduction components is available as an end-point assay for activation. This allows for assays to be performed in other than the specific host cell from which the *Drosophila* protein is derived.

To perform cell free insecticide screening assays, it is sometimes desirable to immobilize either the *Drosophila* protein, or fragment, or its target molecule to facilitate separation of complexes from uncomplexed forms of one or both of the proteins, as well as to accommodate automation of the assay.

Techniques for immobilizing proteins on matrices can be used in the insecticide screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of *Drosophila*-binding protein found in the bead fraction quantitated from the gel using standard electrophoretic techniques. For example, either the polypeptide or its target molecule can be immobilized utilizing conjugation of biotin and streptavidin using techniques well known in the art.

Agents that modulate one of the *Drosophila* proteins of the present invention can be identified using one or more of the above assays, alone or in combination. It is generally preferable to use a cell-based or cell free system first and then confirm activity in an animal/insect model system. Such model systems are well known in the art and can readily be employed in this context.

In yet another aspect of the invention, the *Drosophila* proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–125696; and Brent WO94/10300), to identify other proteins, which bind to or interact with the *Drosophila* protein and are involved in *Drosophila* protein activity. Such *Drosophila*-binding proteins are also likely to be involved in the propagation of signals by the *Drosophila* proteins or *Drosophila* targets as, for example, downstream elements of a *Drosophila*-mediated signaling pathway. Alternatively, such *Drosophila*-binding proteins are likely to be *Drosophila* protein inhibitors.

The two-hybrid system is based on the modular nature of most transcription factors, which consist of separable DNA-binding and activation domains. Briefly, the assay utilizes two different DNA constructs. In one construct, the gene that codes for a *Drosophila* protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a *Drosophila* protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the *Drosophila* protein.

This invention further pertains to novel agents identified by the above-described screening assays. For example, an agent identified as described herein (e.g., a *Drosophila* protein modulating agent, an antisense *Drosophila* nucleic acid molecule, a *Drosophila* protein-specific antibody, or a *Drosophila* protein-binding partner) can be used in an insect model to determine the efficacy and toxicity of such an agent. Alternatively, an agent identified as described herein can be used in an insect model to determine the mechanism of action of such an agent. Furthermore, this invention pertains to uses of novel agents identified by the above-described screening assays for insecticidal use described herein.

Antibodies

The invention also provides antibodies that selectively bind to one of the proteins of the present invention, a fragment of such proteins, as well as variants thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. Either the full-length protein, an antigenic peptide fragment or a fusion protein can be used.

Antibodies are preferably prepared from regions or discrete fragments of the *Drosophila* proteins. Antibodies can be prepared from any region of the peptide as described herein. However, preferred regions will include those involved in function/activity and/or receptor/binding partner interaction.

An antigenic fragment will typically comprise at least 10 contiguous amino acid residues. The antigenic peptide can comprise, however, at least 12, 14, 20 or more amino acid residues. Such fragments can be selected on a physical property, such as fragments correspond to regions that are located on the surface of the protein, e.g., hydrophilic regions or can be selected based on sequence uniqueness.

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full length protein can be used to identify turnover.

The antibodies are also useful for inhibiting protein function, for example, blocking the binding of the *Drosophila* protein to a binding partner such as a receptor or ligand. These uses can also be applied in an insecticidal context in which treatment involves inhibiting the protein's function. An antibody can be used, for example, to block binding, thus modulating (agonizing or antagonizing) the peptides activity. Antibodies can be prepared against specific fragments containing sites required for function or against intact associated with a cell.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a *Drosophila* protein of the present invention. Such nucleic acid molecules will consist of, consist essentially of, or comprise a nucleotide sequence that encodes one of the *Drosophila* proteins of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of one of the nucleotide sequences shown in Figure sheets 1–836: genomic sequences SEQ ID NO: 1, 4, 7, . . . 1525, 1528 and 1531, and transcript sequences SEQ ID NO: 2, 5, 8, . . . 1526, 1529 and 1532 and/or encode a protein comprising of SEQ ID NO:3, 6, 9, . . . 1527, 1530 and 1533. A nucleic acid molecule consists of a nucleotide sequence when the nucleotide sequence is the complete nucleotide sequence of the nucleic acid molecule.

The present invention further provides nucleic acid molecules that consist essentially of one of the nucleotide sequences shown in Figure sheets 1–836, genomic sequences SEQ ID NO: 1, 4, 7, . . . 1525, 1528 and 1531, and transcript sequences SEQ ID NO: 2, 5, 8, . . . 1526, 1529 and 1532 and/or encode a protein comprising of SEQ ID NO:3, 6, 9, . . . 1527, 1530 and 1533. A nucleic acid molecule consists essentially of a nucleotide sequence when such a nucleotide sequence is present with only a few additional nucleic acid residues in the final nucleic acid molecule.

The present invention further provides nucleic acid molecules that are comprised of one of the nucleotide sequences shown in Figure sheets 1–836, genomic sequences SEQ ID NO: 1, 4, 7, . . . 1525, 1528 and 1531, and transcript sequences SEQ ID NO: 2, 5, 8, . . . 1526, 1529 and 1532 and/or encode a protein comprising of SEQ ID NO:3, 6, 9, . . . 1527, 1530 and 1533. A nucleic acid molecule is comprised of a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. The preferred classes of nucleic acid molecules that are comprised of the nucleotide sequences of the present are the naturally occurring full-length cDNA molecules and genes and genomic sequences. A brief description of how various types of these nucleic acid molecules can be readily made/isolated is provided below.

In the Figures, both coding and non-coding sequences are provided for each peptide encoding nucleic acid sequence (both genomic and transcript sequences). Because of the source of the present invention, *Drosophila* genomic sequences, the genomic nucleic acid molecules in the figures will contain genomic intronic sequences, 5' and 3' non-coding sequences, gene regulatory regions and non-coding intergenic sequences. In general such sequence features are either noted or can readily be identified using computational tools known in the art. As discussed below, some of the non-coding regions, particularly gene regulatory elements such as promoters, are useful for a variety of purposes, e.g.

control of heterologous gene expression, target for identifying gene activity modulating compounds.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the *Drosophila* protein alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the proteins of the present invention and that encode obvious variants of the *Drosophila* proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in the Figures. Preferred non-coding fragments include, but are not limited to, promoter sequences, enhancer sequences, gene modulating sequences and gene termination sequences. Such fragments are useful in controlling heterologous gene expression and in developing screens to identify gene modulating agents. Such regulatory sequences are readily identifiable using know methods as well as by isolating the non-coding sequences found 5' to the transcription start site identified in the Figures.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–65%, 70–75%, 80–85%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence.

As used herein, the term "hybridizes under stringent conditions" is intended to describe conditions for hybridization and washing under which nucleotide sequences encoding a peptide at least 50–55% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2 ×SSC, 0.1% SDS at 50–65C.

Nucleic Acid Molecule Uses

The nucleic acid molecules of the present invention are useful for probes, primers, chemical intermediates, and in biological assays. The nucleic acid molecules are useful as a hybridization probe for cDNA and genomic DNA to isolate full-length cDNA and genomic clones encoding the peptide described in the Figures and to isolate cDNA and genomic clones that correspond to variants (alleles, orthologs, etc.) producing the same or related peptides shown in the Figures.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for identifying insecticide susceptibility or tolerance involving an increase or decrease in *Drosophila* protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a *Drosophila* protein, such as by measuring a level of a receptor-encoding nucleic acid in a sample of cells from a subject e.g., mRNA or genomic DNA, or determining if a receptor gene has been mutated.

Nucleic acid expression assays are useful for insecticide screening to identify compounds that modulate *Drosophila* nucleic acid expression.

The invention thus provides a method for identifying a compound that can be used to alter (inhibit or enhance) expression of the *Drosophila* protein gene. The method typically includes assaying the ability of the compound to modulate the expression of the *Drosophila* nucleic acid and thus identifying a compound that can be used to kill an insect. The assays can be performed in cell-based and cell-free systems. Cell-based assays include cells naturally expressing the *Drosophila* nucleic acid or recombinant cells genetically engineered to express specific nucleic acid sequences.

The assay for *Drosophila* nucleic acid expression can involve direct assay of nucleic acid levels, such as mRNA levels, or on collateral compounds involved in the signal pathway. Further, the expression of genes that are up- or down-regulated in response to the *Drosophila* protein signal pathway can also be assayed. In this embodiment the regulatory regions of these genes can be operably linked to a reporter gene such as luciferase.

Thus, modulators of *Drosophila* protein gene expression can be identified in a method wherein a cell is contacted with a candidate compound and the expression of mRNA determined. The level of expression of *Drosophila* protein mRNA in the presence of the candidate compound is compared to the level of expression of *Drosophila* protein mRNA in the absence of the candidate compound. The candidate compound can then be identified as a modulator of nucleic acid expression based on this comparison and be used, for example to alter nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention also encompasses kits for detecting the presence of a *Drosophila* nucleic acid in a biological sample. For example, the kit can comprise reagents such as a labeled or labelable nucleic acid or agent capable of detecting *Drosophila* nucleic acid in a biological sample; means for determining the amount of *Drosophila* nucleic acid in the sample; and means for comparing the amount of *Drosophila* nucleic acid in the sample with a standard. The compound or agent can be packaged in a suitable container. The kit can further comprise instructions for using the kit to detect *Drosophila* mRNA or DNA.

Nucleic Acid Arrays

The present invention further provides arrays or microarrays of nucleic acid molecules that are based on the sequence information provided in the Figure Sheets, genomic sequences SEQ ID NO: 1, 4, 7, . . . 1525, 1528 and 1531, or transcript sequences SEQ ID NO: 2, 5, 8, . . . 1526, 1529 and 1532.

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–125680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, expression patterns, mutations, variants, or polymorphisms among samples.

Using such arrays, the present invention provides methods to identify the expression of one or more of the secreted proteins/proteins of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of all of the genes expressed provided herein.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified secreted protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd ed*., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd ed*., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, and thrombin. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185: 60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a *Drosophila* protein or peptide that can be further purified to produce desired amounts of *Drosophila* protein or fragments. Thus, host cells containing expression vectors are useful for peptide production.

Host cells are also useful for conducting cell-based assays involving the *Drosophila* protein or *Drosophila* protein fragments. Thus, a recombinant host cell expressing a native *Drosophila* protein is useful for assaying compounds that stimulate or inhibit *Drosophila* protein function.

Host cells are also useful for identifying *Drosophila* protein mutants in which these functions are affected. If the mutants naturally occur and give rise to a pathology, host cells containing the mutations are useful to assay compounds that have a desired effect on the mutant *Drosophila* protein (for example, stimulating or inhibiting function) which may not be indicated by their effect on the native *Drosophila* protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a *Drosophila* protein and identifying and evaluating modulators of *Drosophila* protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the *Drosophila* protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the *Drosophila* protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated nucleic acid molecule consisting of a nucleotide sequence selected from the group consisting of:

(a) a nucleotide sequence that encodes a protein comprising the amino acid sequence of SEQ ID NO:855;

(b) a nucleic acid molecule consisting of the nucleic acid sequence of SEQ ID NO:854;

(c) a nucleic acid molecule consisting of the nucleic acid sequence of SEQ ID NO:853; and (d) a nucleic acid molecule that is completely complementary to a nucleic acid molecule f(a)–(c).

2. A nucleic acid vector comprising the nucleic acid sequences of claim 1.

3. A host cell containing the vector of claim 2.

4. An isolated polynucleotide consisting of a nucleotide sequence set forth in SEQ ID NO:854.

5. An isolated polynucleotide consisting of a nucleotide sequence set forth in SEQ ID NO:853.

6. A vector according to claim 2, wherein said vector is selected from the group consisting of a plasmid, virus, and bacteriophage.

7. A vector according to claim 2, wherein said isolated nucleic acid molecule is inserted into said vector in proper orientation and correct reading frame such that the protein of SEQ D NO:855 may be expressed by a cell transformed with said vector.

8. A vector according to claim 7, wherein said isolated nucleic acid molecule is operatively linked to a promoter sequence.

* * * * *